US012304907B2

(12) United States Patent
Cottrell et al.

(10) Patent No.: US 12,304,907 B2
(45) Date of Patent: *May 20, 2025

(54) COMPOUNDS AND METHODS OF USE

(71) Applicant: Tango Therapeutics, Inc., Boston, MA (US)

(72) Inventors: Kevin M. Cottrell, Arlington, MA (US); John P. Maxwell, Hingham, MA (US)

(73) Assignee: Tango Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/430,429

(22) Filed: Feb. 1, 2024

(65) Prior Publication Data

US 2024/0279219 A1 Aug. 22, 2024

Related U.S. Application Data

(63) Continuation of application No. 17/732,846, filed on Apr. 29, 2022, now Pat. No. 11,999,727, which is a continuation of application No. 17/525,692, filed on Nov. 12, 2021, now Pat. No. 11,492,350, which is a continuation of application No. PCT/US2021/044004, filed on Jul. 30, 2021.

(60) Provisional application No. 63/059,959, filed on Jul. 31, 2020.

(51) Int. Cl.
C07D 417/14 (2006.01)
A61P 35/00 (2006.01)

(52) U.S. Cl.
CPC ............ C07D 417/14 (2013.01); A61P 35/00 (2018.01)

(58) Field of Classification Search
CPC .................................................. C07D 417/14
USPC ........................................................ 514/318
See application file for complete search history.

(56) References Cited

U.S. PATENT DOCUMENTS

| | | | |
|---|---|---|---|
| 5,814,631 A | 9/1998 | Fukami et al. | |
| 10,278,955 B1 | 5/2019 | Yao et al. | |
| 11,077,101 B1 | 8/2021 | Cottrell et al. | |
| 11,492,350 B2 * | 11/2022 | Cottrell | C07D 409/14 |
| 11,999,727 B2 * | 6/2024 | Cottrell | A61K 31/4709 |
| 2017/0027935 A1 | 2/2017 | Duncan et al. | |
| 2017/0210751 A1 | 7/2017 | Duncan et al. | |
| 2019/0071425 A1 | 3/2019 | Bergman et al. | |
| 2019/0083482 A1 | 3/2019 | Duncan et al. | |
| 2019/0175526 A1 | 6/2019 | Yao et al. | |
| 2019/0175553 A1 | 6/2019 | Yao et al. | |

FOREIGN PATENT DOCUMENTS

| | | |
|---|---|---|
| CN | 116462676 A | 7/2023 |
| CN | 116462677 A | 7/2023 |
| WO | 2004096774 A1 | 11/2004 |
| WO | 2014100716 A1 | 6/2014 |
| WO | 2014100719 A2 | 6/2014 |
| WO | 2016038550 A1 | 3/2016 |
| WO | 2016044585 A1 | 3/2016 |
| WO | 2016089883 A1 | 6/2016 |
| WO | 2018039972 A1 | 3/2018 |
| WO | 2019032859 A1 | 2/2019 |
| WO | 2019084470 A1 | 5/2019 |
| WO | 2019094311 A1 | 5/2019 |
| WO | 2019094312 A1 | 5/2019 |
| WO | 2019102494 A1 | 5/2019 |
| WO | 2019110734 A1 | 6/2019 |
| WO | 2019112719 A1 | 6/2019 |
| WO | 2019116302 A1 | 6/2019 |
| WO | 2019165189 A1 | 8/2019 |
| WO | 2019173804 A1 | 9/2019 |
| WO | 2019180628 A1 | 9/2019 |
| WO | 2019180631 A1 | 9/2019 |
| WO | 2019219805 A1 | 11/2019 |
| WO | 2019229614 A1 | 12/2019 |
| WO | 2020094712 A1 | 5/2020 |
| WO | 2020139991 A1 | 7/2020 |
| WO | 2020168125 A1 | 8/2020 |

(Continued)

OTHER PUBLICATIONS

Database Registry, Chemical Abstracts Services, CAS Registry No. 2194806-06-7 (Entered STN: Mar. 20, 2018).

(Continued)

*Primary Examiner* — Kahsay Habte
(74) *Attorney, Agent, or Firm* — GOODWIN PROCTER LLP

(57) ABSTRACT

Compounds are provided according to Formula (I):

and pharmaceutically acceptable salts thereof, and pharmaceutical compositions thereof; wherein $R^1$, $R^2$, $R^3$, $R^4$, $R^6$, $R^7$, $R^8$ and n are as defined herein. Compounds of the present invention are contemplated useful for the prevention and treatment of a variety of conditions.

24 Claims, 7 Drawing Sheets

Specification includes a Sequence Listing.

(56) References Cited

FOREIGN PATENT DOCUMENTS

| WO | 2020182018 A1 | 9/2020 |
|---|---|---|
| WO | 2020198323 A1 | 10/2020 |
| WO | 2020198601 A1 | 10/2020 |
| WO | 2020205660 A1 | 10/2020 |
| WO | 2020205867 A1 | 10/2020 |
| WO | 2020206289 A1 | 10/2020 |
| WO | 2020206299 A1 | 10/2020 |
| WO | 2020206308 A1 | 10/2020 |
| WO | 2020217070 A1 | 10/2020 |
| WO | 2021004547 A1 | 1/2021 |
| WO | 2021126731 A1 | 6/2021 |
| WO | 2021126999 A1 | 6/2021 |
| WO | 2021140427 A1 | 7/2021 |
| WO | 2021163344 A1 | 8/2021 |
| WO | 2022026892 A1 | 2/2022 |
| WO | 2022115377 A1 | 6/2022 |
| WO | 2022132914 A1 | 6/2022 |
| WO | 2022256806 A1 | 12/2022 |
| WO | 2023098439 A1 | 6/2023 |

OTHER PUBLICATIONS

Database Registry, Chemical Abstracts Services, CAS Registry No. 2194806-12-5 (Entered STN: Mar. 20, 2018).
Database Registry, Chemical Abstracts Services, CAS Registry No. 2194806-35-2 (Entered STN: Mar. 20, 2018).
Database Registry, Chemical Abstracts Services, CAS Registry No. 2194883-10-6 (Entered STN: Mar. 20, 2018).
Database Registry, Chemical Abstracts Services, CAS Registry No. 2194892-90-3 (Entered STN: Mar. 20, 2018).
Database Registry, Chemical Abstracts Services, CAS Registry No. 2195066-99-8 (Entered STN: Mar. 20, 2018).
Database Registry, Chemical Abstracts Services, CAS Registry No. 2195265-98-4 (Entered STN: Mar. 20, 2018).
Database Registry, Chemical Abstracts Services, CAS Registry No. 2195267-15-1 (Entered STN: Mar. 20, 2018).
Database Registry, Chemical Abstracts Services, CAS Registry No. 2195486-19-0 (Entered STN: Mar. 21, 2018).
Database Registry, Chemical Abstracts Services, CAS Registry No. 2196547-67-6 (Entered STN: Mar. 22, 2018).
Database Registry, Chemical Abstracts Services, CAS Registry No. 2197009-34-8 (Entered STN: Mar. 22, 2018).
Database Registry, Chemical Abstracts Services, CAS Registry No. 2197080-56-9 (Entered STN: Mar. 22, 2018).
Database Registry, Chemical Abstracts Services, CAS Registry No. 2210118-22-0 (Entered STN: Nov. 4, 2018).
Database Registry, Chemical Abstracts Services, CAS Registry No. 2210118-42-4 (Entered STN: Nov. 4, 2018).
Database Registry, Chemical Abstracts Services, CAS Registry No. 2210126-28-4 (Entered STN: Nov. 4, 2018).
Database Registry, Chemical Abstracts Services, CAS Registry No. 2224175-20-4 (Entered STN: May 20, 2018).
Database Registry, Chemical Abstracts Services, CAS Registry No. 2261526-30-9 (Entered STN: Jan. 30, 2019).
Database Registry, Chemical Abstracts Services, CAS Registry No. 2262124-60-5 (Entered STN: Jan. 30, 2019).
Database Registry, Chemical Abstracts Services, CAS Registry No. 2262309-67-9 (Entered STN: Jan. 30, 2019).
Database Registry, Chemical Abstracts Services, CAS Registry No. 2263579-56-0 (Entered STN: Jan. 31, 2019).
Database Registry, Chemical Abstracts Services, CAS Registry No. 2263600-01-5 (Entered STN: Jan. 31, 2019).
Database Registry, Chemical Abstracts Services, CAS Registry No. 2264166-31-4 (Entered STN: Jan. 2, 2019).
Database Registry, Chemical Abstracts Services, CAS Registry No. 2264323-74-0 (Entered STN: Jan. 2, 2019).
Database Registry, Chemical Abstracts Services, CAS Registry No. 2264359-72-8 (Entered STN: Jan. 2, 2019).
Database Registry, Chemical Abstracts Services, CAS Registry No. 2264381-91-9 (Entered STN: Jan. 2, 2019).
Database Registry, Chemical Abstracts Services, CAS Registry No. 2264422-68-4 (Entered STN: Jan. 2, 2019).
Database Registry, Chemical Abstracts Services, CAS Registry No. 2264560-91-8 (Entered STN: Jan. 2, 2019).
Database Registry, Chemical Abstracts Services, CAS Registry No. 2264661-25-6 (Entered STN: Jan. 2, 2019).
Database Registry, Chemical Abstracts Services, CAS Registry No. 2264914-90-9 (Entered STN: Jan. 2, 2019).
Database Registry, Chemical Abstracts Services, CAS Registry No. 2264946-72-5 (Entered STN: Jan. 2, 2019).
Database Registry, Chemical Abstracts Services, CAS Registry No. 2265002-54-6 (Entered STN: Jan. 2, 2019).
Database Registry, Chemical Abstracts Services, CAS Registry No. 2422597-62-2 (Entered STN: Nov. 6, 2020).
Database Registry, Chemical Abstracts Services, CAS Registry No. 2424394-29-4 (Entered STN: Jun. 14, 2020).
Database Registry, Chemical Abstracts Services, CAS Registry No. 2428277-85-2 (Entered STN: Jun. 18, 2020).
Duncan, et al., "Structure and Property Guided Design in the Identification of PRMT5 Tool Compound EPZ015666," ACS Med. Chem. Lett. vol. 7, pp. 162-166, 2015, DOI: 10.1021/acsmedchemlett.5b00380.
Mavrakis, et al., Disordered methionine metabolism in MTAP/CDKN2A-deleted cancers leads to dependence on PRMT5, Science vol. 351, Issue 6278, 2016.
Database Registry, Chemical Abstracts Services, CAS Registry No. 2418745-60-3 (Entered STN: Apr. 6, 2020).
Database Registry, Chemical Abstracts Services, CAS Registry No. 2418755-08-3 (Entered STN: Apr. 6, 2020).
Product ID Z4442559005, <https://enaminestore.com/search>, Screening compounds database search performed Jul. 13, 2020.
International Search Report and Written Opinion for International Patent Application No. PCT/US2021/044004 mailed on Dec. 1, 2021, 11 pages.
Cherkasov et al. Journal of Medicinal Chemistry (2011), 54(24), 8563-8573.
Bertino et al., "Targeting tumors that lack methylthioadenosine phosphorylase (MTAP) activity", Cancer Biology & Therapy, vol. 11, No. 7, pp. 627-632, Apr. 1, 2011.
Bogolubsky et al., "2,2,2-Trifluoroethyl Chlorooxoacetate-Universal Reagent for One-Pot Parallel Synthesis of N1-Aryl-N2-alkyl-Substituted Oxamides", ACS Combinational Science, vol. 17, No. 10, Oct. 12, 2015.
Wu et al., "Protein arginine methylation: from enigmatic functions to therapeutic targeting", Nature Reviews Drug Discovery, Nature Publishing Group, GB, vol. 20, No. 7, Mar. 19, 2021, pp. 509-530.
Chan-Penebre "A selective inhibitor of PRMT5 with in vivo and in vitro potency in MCL models," Nature: Chemical Biology, vol. 11 p. 432, 2015, DOI: 10.1038/NCHEMBIO. 1810.
Database Registry, Chemical Abstracts Services, CAS Registry No. 1333888-52-0 (Entered STN: Sep. 29, 2011).
Database Registry, Chemical Abstracts Services, CAS Registry No. 1333978-29-2 (Entered STN: Sep. 29, 2011).
Database Registry, Chemical Abstracts Services, CAS Registry No. 1436158-24-5 (Entered STN: Sep. 6, 2013).
Database Registry, Chemical Abstracts Services, CAS Registry No. 1808899-86-6 (Entered STN: Sep. 29, 2015).
Database Registry, Chemical Abstracts Services, CAS Registry No. 1825632-80-1 (Entered STN: Sep. 12, 2015).
Database Registry, Chemical Abstracts Services, CAS Registry No. 2127623-98-5 (Entered STN: Sep. 15, 2017).
Database Registry, Chemical Abstracts Services, CAS Registry No. 2127864-47-3 (Entered STN: Sep. 15, 2017).
Database Registry, Chemical Abstracts Services, CAS Registry No. 2128156-86-3 (Entered STN: Sep. 17, 2017).
Database Registry, Chemical Abstracts Services, CAS Registry No. 2128383-28-6 (Entered STN: Sep. 19, 2017).
Database Registry, Chemical Abstracts Services, CAS Registry No. 2128933-12-8 (Entered STN: Sep. 21, 2017).
Database Registry, Chemical Abstracts Services, CAS Registry No. 2129514-20-9 (Entered STN: Sep. 22, 2017).

(56) References Cited

OTHER PUBLICATIONS

Database Registry, Chemical Abstracts Services, CAS Registry No. 2129965-61-1 (Entered STN: Sep. 22, 2017).
Database Registry, Chemical Abstracts Services, CAS Registry No. 2130124-49-9 (Entered STN: Sep. 24, 2017).
Database Registry, Chemical Abstracts Services, CAS Registry No. 2133687-73-5 (Entered STN: Nov. 10, 2017).
Database Registry, Chemical Abstracts Services, CAS Registry No. 2133721-72-7 (Entered STN: Nov. 10, 2017).
Database Registry, Chemical Abstracts Services, CAS Registry No. 2133773-68-7 (Entered STN: Nov. 10, 2017).
Database Registry, Chemical Abstracts Services, CAS Registry No. 2134591-54-9 (Entered STN: Oct. 13, 2017).
Database Registry, Chemical Abstracts Services, CAS Registry No. 2135033-12-2 (Entered STN: Oct. 16, 2017).
Database Registry, Chemical Abstracts Services, CAS Registry No. 2174302-80-6 (Entered STN: Feb. 16, 2018).
Database Registry, Chemical Abstracts Services, CAS Registry No. 2174475-08-0 (Entered STN: Feb. 16, 2018).
Database Registry, Chemical Abstracts Services, CAS Registry No. 2174535-81-8 (Entered STN: Feb. 16, 2018).
Database Registry, Chemical Abstracts Services, CAS Registry No. 2174583-27-6 (Entered STN: Feb. 16, 2018).
Database Registry, Chemical Abstracts Services, CAS Registry No. 2174779-78-1 (Entered STN: Feb. 16, 2018).
Database Registry, Chemical Abstracts Services, CAS Registry No. 2177945-17-2 (Entered STN: Feb. 21, 2018).
Database Registry, Chemical Abstracts Services, CAS Registry No. 2177945-30-9 (Entered STN: Feb. 21, 2018).
Database Registry, Chemical Abstracts Services, CAS Registry No. 2179514-66-8 (Entered STN: Feb. 26, 2018).
Database Registry, Chemical Abstracts Services, CAS Registry No. 2179519-18-5 (Entered STN: Feb. 26, 2018).
Database Registry, Chemical Abstracts Services, CAS Registry No. 2179519-30-1 (Entered STN: Feb. 26, 2018).
Database Registry, Chemical Abstracts Services, CAS Registry No. 2179519-33-4 (Entered STN: Feb. 26, 2018).
Database Registry, Chemical Abstracts Services, CAS Registry No. 2187417-75-8 (Entered STN: Aug. 3, 2018).
Database Registry, Chemical Abstracts Services, CAS Registry No. 2188859-87-0 (Entered STN: Nov. 3, 2018).
Database Registry, Chemical Abstracts Services, CAS Registry No. 2188907-95-9 (Entered STN: Nov. 3, 2018).
Database Registry, Chemical Abstracts Services, CAS Registry No. 2188971-01-7 (Entered STN: Dec. 3, 2018).
Database Registry, Chemical Abstracts Services, CAS Registry No. 2189401-03-2 (Entered STN: Dec. 3, 2018).
Database Registry, Chemical Abstracts Services, CAS Registry No. 2189483-86-9 (Entered STN: Dec. 3, 2018).
Database Registry, Chemical Abstracts Services, CAS Registry No. 2189484-53-3 (Entered STN: Dec. 3, 2018).
Database Registry, Chemical Abstracts Services, CAS Registry No. 2189484-97-5 (Entered STN: Dec. 3, 2018).
Database Registry, Chemical Abstracts Services, CAS Registry No. 2189484-99-7 (Entered STN: Dec. 3, 2018).
Database Registry, Chemical Abstracts Services, CAS Registry No. 2189638-31-9 (Entered STN: Dec. 3, 2018).
Database Registry, Chemical Abstracts Services, CAS Registry No. 2190008-94-5 (Entered STN: Mar. 13, 2018).
Database Registry, Chemical Abstracts Services, CAS Registry No. 2190436-05-4 (Entered STN: Mar. 13, 2018).
Database Registry, Chemical Abstracts Services, CAS Registry No. 2191074-73-2 (Entered STN: Mar. 14, 2018).
Database Registry, Chemical Abstracts Services, CAS Registry No. 2191101-89-8 (Entered STN: Mar. 14, 2018).
Database Registry, Chemical Abstracts Services, CAS Registry No. 2191241-90-2 (Entered STN: Mar. 14, 2018).
Database Registry, Chemical Abstracts Services, CAS Registry No. 2191750-99-7 (Entered STN: Mar. 15, 2018).
Database Registry, Chemical Abstracts Services, CAS Registry No. 2192164-72-8 (Entered STN: Mar. 15, 2018).
Database Registry, Chemical Abstracts Services, CAS Registry No. 2192262-48-7 (Entered STN: Mar. 15, 2018).
Database Registry, Chemical Abstracts Services, CAS Registry No. 2192262-85-2 (Entered STN: Mar. 15, 2018).
Database Registry, Chemical Abstracts Services, CAS Registry No. 2192263-02-6 (Entered STN: Mar. 15, 2018).

* cited by examiner

SEQUENCE LISTING

```
Sequence total quantity: 2
SEQ ID NO: 1            moltype = AA  length = 22
FEATURE                 Location/Qualifiers
REGION                  1..22
                        note = Peptide Me0
SITE                    1
                        note = The amino acid at position 1 is attached to an (Ac)
                         group
SITE                    22
                        note = The amino acid at position 22 is attached to an
                         (NH2) group
SITE                    22
                        note = The amino acid at position 22 is attached to 5-TAMRA
                         (5-Carboxytetramethylrhodamine)
source                  1..22
                        mol_type = protein
                        organism = synthetic construct
SEQUENCE: 1
SGRGKGGKGL GKGGAKRHRK VK                                                   22

SEQ ID NO: 2            moltype = AA  length = 22
FEATURE                 Location/Qualifiers
REGION                  1..22
```

```
                          note = Me2 Peptide
SITE                      1
                          note = The amino acid at position 1 is attached to an (Ac)
                           group
SITE                      3
                          note = The amino acid at position 3 is dimethylated in a
                           symmetrical manner
SITE                      22
                          note = The amino acid at position 22 is attached to an
                           (NH2) group
SITE                      22
                          note = The amino acid at position 22 is attached to 5-TAMRA
                           (5-Carboxytetramethylrhodamine)
source                    1..22
                          mol_type = protein
                          organism = synthetic construct
SEQUENCE: 2
SGRGKGGKGL GKGGAKRHRK VK                                                           22
```

COMPOUNDS AND METHODS OF USE

CROSS-REFERENCE TO RELATED APPLICATIONS

This application is a continuation of U.S. application Ser. No. 17/732,846, filed Apr. 29, 2022, which is a continuation of U.S. application Ser. No. 17/525,692, filed Nov. 12, 2021, which is a continuation of International Application No. PCT/US2021/044004, filed Jul. 30, 2021, which claims priority to U.S. Provisional Application No. 63/059,959, filed Jul. 31, 2020, each of which are incorporated herein by reference in their entirety.

The instant application contains a Sequence Listing which has been submitted electronically in XML format and is hereby incorporated by reference in its entirety. Said XML file copy, created on Dec. 6, 2024, is named TGO-006WOC3_SL.xml and is 6,452 bytes in size.

BACKGROUND OF THE INVENTION

Cancer therapeutics can be broadly classified into two categories, cytotoxic and targeted therapies. While cytotoxic therapies are associated with widespread toxicities, targeted therapies have the advantage of selectively targeting the tumor cells that rely on the activity of their substrates. The clinical efficacy of targeted therapies has been demonstrated with BCR/ABL and EGFR inhibitors for the treatment of CML and non-small cell lung cancer, respectively. The success of these programs has furthered development of other therapies that specifically target amplified or mutation-activated oncogenes. The greater challenge is to develop selective therapies that target those tumors with loss-of-function mutations or deletion of tumor suppressor genes, the loss of which obviate traditional strategies for molecular targeted therapeutics. Efforts to characterize the cancer genome, led by groups like the Cancer Genome Atlas (TCGA), have made tremendous strides in elucidating the size and frequency of the deletion events that promote tumor growth by causing the loss of tumor suppressor genes. However, these events are often regional and cause the co-deletion of genes proximal to their intended targets. Though these passenger events are not known to cause a fitness advantage, they may cause collateral vulnerabilities that can be therapeutically leveraged. One example is the collateral vulnerability to PRMT5 inhibition conferred by loss of methylthioadenosine phosphorylase (MTAP), which is frequently co-deleted with the well-described tumor suppressor gene, CDKN2A (Kruykov et al., 2016; Marjon et al., 2016 and Markarov et al., 2016).

Loss of CDKN2A occurs in ~10-15% of all human cancers and with frequency in histologies such as malignant peripheral nerve sheath tumors, glioblastoma, mesothelioma, bladder urothelial carcinoma, esophageal squamous cell carcinoma, pancreatic adenocarcinoma, melanoma, non-small cell lung cancer, head and neck cancer and cholangiosarcoma (Gao et al. *Sci. Signal.* 2013; Cerami et al. *Cancer Discov.* 2012; and Marjon et al. *Cell Reports* 2016). Because of its proximity to CDKN2A on chromosome 9p21, MTAP is frequently included in the deletion. MTAP is a critical enzyme in the methionine salvage pathway, a six-step process that recycles methionine from the product of polyamine synthesis, methylthioadenosine (MTA). Loss of MTAP causes the accumulation of its substrate, MTA, which has been demonstrated by multiple groups to function as a SAM-competitive PRMT5 inhibitor (Kruykov et al., 2016; Marjon et al., 2016 and Markarov et al., 2016).

PRMT5 is a type II arginine methyltransferase that regulates essential cellular functions, including the regulation of cell cycle progression, apoptosis and the DNA-damage response, by symmetrically dimethylating proteins involved in transcription and signaling (Koh, Bezzi and Guccione *Curr Mol Bio Rep* 2015 and Wu et al *Nat Rev Drug Discovery* 2021). However, data from genome-wide genetic perturbation screens using shRNA has revealed a selective requirement for PRMT5 activity in MTAP-deleted cancer cell lines (Kruykov et al., 2016; Marjon et al., 2016 and Markarov et al., 2016). The accumulation of MTA caused by MTAP-deletion in these cell lines partially inhibits PRMT5, rendering those cells selectively sensitive to additional PRMT5 inhibition.

PRMT5 inhibitors have been developed, yet they do not demonstrate selectivity for MTAP-deleted cancer cell lines. This lack of selectivity can be explained by the mechanisms of action of the inhibitors, as they are either SAM-uncompetitive or SAM-competitive inhibitors and therefore, MTAP-agnostic (Kruykov et al., 2016; Marjon et al., 2016 and Markarov et al., 2016) However, if a PRMT5 inhibitor were developed that leverages the accumulation of MTA by binding in an MTA-uncompetitive, non-competitive or mixed mode manner or in a MTA-cooperative binding manner, it could demonstrate selectivity for MTAP-deleted tumor cells.

SUMMARY OF THE INVENTION

In one aspect of the invention, provided is a compound of Formula (I) or a pharmaceutically acceptable salt thereof; wherein:

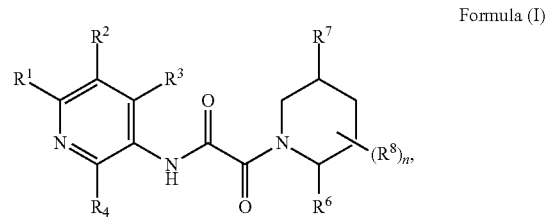

Formula (I)

each $R^1$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a1}$, —$N(R^{a1})_2$, —$C(=O)R^{a1}$, —$C(=O)OR^{a1}$, —$NR^{a1}C(=O)R^{a1}$, —$NR^{a1}C(=O)OR^{a1}$, —$C(=O)N(R^{a1})_2$, —$OC(=O)N(R^{a1})_2$, —$S(=O)R^{a1}$, —$S(=O)_2R^{a1}$, —$SR^{a1}$, —$S(=O)(=NR^{a1})R^{a1}$, —$Na^{a1}S(=O)_2R^{a1}$ and —$S(=O)_2N(R^{a1})_2$;

each $R^2$ is independently selected from halo, —CN, —$C_1$-$C_6$ alkyl, —$C_1$-$C_6$ heteroalkyl, —$C_1$-$C_6$ haloalkyl, —$C_1$-$C_6$ haloalkoxy, —$C_3$-$C_9$ cycloalkyl, 3-10 membered heterocyclyl, heterocyclylalkyl, heteroarylalkyl, arylalkyl, cycloalkylalkyl, —$OR^{a2}$, —$N(R^{a2})_2$, —$C(=O)R^{a2}$, —$C(=O)OR^{a2}$, —$NR^{a2}C(=O)R^{a2}$, —$NR^{a2}C(=O)OR^{a2}$, —$C(=O)N(R^{a2})_2$, —$C(=O)N(OR^{a2})(R^{a2})$—$OC(=O)N(R^{a2})_2$, —$S(=O)R^{a2}$, —$S(=O)_2R^{a2}$, —$SR^{a2}$, —$S(=O)(=NR^{a2})R^{a2}$, —$NR^{a2}S(=O)_2R^{a2}$ and —$S(=O)_2N(R^{a2})_2$;

each $R^3$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —OR$^{a3}$, —N(R$^{a3}$)$_2$, —C(=O)R$^{a3}$, —C(=O)OR$^{a3}$, NR$^{a3}$C(=O)R$^{a3}$, —NR$^{a3}$C(=O)OR$^{a3}$, —C(=O)N(R$^{a3}$)$_2$, —OC(=O)N(R$^{a3}$)$_2$, —S(=O)R$^{a3}$, —S(=O)$_2$R$^{a3}$, —SR$^{a3}$, —S(=O)(=NR$^{a3}$)R$^{a3}$, —NR$^{a3}$S(=O)$_2$R$^{a3}$ and —S(=O)$_2$N(R$^{a3}$)$_2$;

each R$^4$ is independently selected from H, -D, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, heterocyclylalkyl, heteroarylalkyl, arylalkyl, cycloalkylalkyl, —OR$^{a4}$, —N(R$^{a4}$)$_2$, —C(=O)R$^{a4}$, —C(=O)OR$^{a4}$—NR$^{a4}$C(=O)R$^{a4}$, —NR$^{a4}$C(=O)OR$^{a4}$, —C(=O)N(R$^{a4}$)$_2$, —OC(=O)N(R$^{a4}$)$_2$, —S(=O)R$^{a4}$, —S(=O)$_2$R$^{a4}$, —SR$^{a4}$, —S(=O)(=NR$^{a4}$)R$^{a4}$, —NR$^{a4}$S(=O)$_2$R$^{a4}$ and —S(=O)$_2$N(R$^{a4}$)$_2$;

each R$^6$ is independently absent or selected from H, -D, halo, —CN, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl, cycloalkylalkyl, —OR$^{a6}$, —N(R$^{a6}$)$_2$, —C(=O)R$^{a6}$, —C(=O)OR$^{a6}$, —NR$^{a6}$C(=O)R$^{a6}$, —NR$^{a6}$C(=O)OR$^{a6}$, —C(=O)N(R$^{a6}$)$_2$, —OC(=O)N(R$^{a6}$)$_2$, —S(=O)R$^{a6}$, —S(=O)$_2$R$^{a6}$, —SR$^{a6}$, —S(=O)(=NR$^{a6}$)R$^{a6}$—NR$^{a6}$S(=O)$_2$R$^{a6}$ and —S(=O)$_2$N(R$^{a6}$)$_2$, wherein each alkyl, carbocyclyl, heterocyclyl, cycloalkylalkyl, heterocyclylalkyl, aryl, heteroaryl, arylalkyl and heteroarylalkyl is optionally substituted at any available position;

each R$^7$ is independently absent or selected from H, -D, halo, —CN, —C$_1$-C$_6$ alkyl, —C$_1$-C$_6$ hydroxyalkyl, —C$_1$-C$_6$ haloalkyl, —C$_3$-C$_9$ cycloalkyl, 3-10 membered heterocyclyl, 5-6-membered monocyclic heteroaryl, heterocyclylalkyl, heteroarylalkyl, arylalkyl, cycloalkylalkyl, —OR$^{a7}$, —N(R$^{a7}$)$_2$, —C(=O)R$^{a7}$, —C(=O)OR$^{a7}$, —NR$^{a7}$C(=O)R$^{a7}$, —NR$^{a7}$C(=O)OR$^{a7}$, —C(=O)N(R$^{a7}$)$_2$, —OC(=O)N(R$^{a7}$)$_2$, —S(=O)R$^{a7}$, —S(=O)$_2$R$^{a7}$, —SR$^{a7}$, —S(=O)(=NR$^{a7}$)R$^{a7}$, —NR$^{a7}$S(=O)$_2$R$^{a7}$ and —S(=O)$_2$N(R$^{a7}$)$_2$;

each R$^8$ is independently selected from H, -D, =O, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, heterocyclylalkyl, heteroarylalkyl, arylalkyl, cycloalkylalkyl, —OR$^{a8}$, —N(R$^{a8}$)$_2$, —C(=O)R$^{a8}$, —C(=O)OR$^{a8}$, NR$^{a8}$C(=O)R$^{a8}$, —NR$^{a8}$C(=O)OR$^{a8}$, —CH$_2$C(=O)N(R$^{a8}$)$_2$—C(=O)N(R$^{a8}$)$_2$, —OC(=O)N(R$^{a8}$)$_2$, —CH$_2$C(=O)N(R$^{a8}$)$_2$, —S(=O)R$^{a8}$, —S(=O)$_2$R$^{a8}$, —SR$^{a8}$, —S(=O)(=NR$^{a8}$)R$^{a8}$, —NR$^{a8}$S(=O)$_2$R$^{a8}$ and —S(=O)$_2$N(R$^{a8}$)$_2$ wherein two instances of R$^8$ together with the atom or atoms to which they are attached can be taken together to form a 3-10 member cycloalkyl or heterocyclyl ring (e.g., a ring that together with the piperidine ring of Structure I can form a bridged, fused or spiro bicyclic heterocyclic ring)

each R$^{a1}$, R$^{a2}$, R$^{a3}$, R$^{a4}$, R$^{a6}$, R$^{a7}$ and R$^{a8}$ is independently selected from H, C$_1$-C$_6$ alkyl, —C$_1$-C$_6$ heteroalkyl, C$_3$-C$_9$ cycloalkyl, 3-7 membered heterocyclyl, cycloalkylalkyl, heterocyclylalkyl, aryl, 5-6 membered heteroaryl, arylalkyl and heteroarylalkyl wherein each alkyl, cycloalkyl, heterocyclyl, cycloalkylalkyl, heterocyclylalkyl, aryl, heteroaryl, arylalkyl and heteroarylalkyl is optionally substituted at any available position (e.g., substituted with 0, 1, 2 or 3 instances of R$^9$, wherein each R$^9$ is independently selected from =O, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, C$_6$-C$_{10}$ aryl, 5-10 membered heteroaryl, cycloalkylalkyl, heterocyclylalkyl, arylalkyl, heteroarylalkyl, —OR$^b$, —N(R$^b$)$_2$, —C(=O)R$^b$, —C(=O)OR$^b$, —NR$^b$C(=O)R$^b$, —NR$^b$C(=O)OR$^b$, —C(=O)N(R$^b$)$_2$, —OC(=O)N(R$^b$)$_2$, —S(=O)R$^b$, —S(=O)$_2$R$^b$, —SR$^b$, —S(=O)(=NR$^b$)R$^b$, —NR$^b$S(=O)$_2$R$^b$ and —S(=O)$_2$N(R$^b$)$_2$, wherein each R$^b$ is independently selected from H, —C$_1$-C$_6$ alkyl (e.g., -Me, -Et, —Pr, -$^i$Pr, -$^n$Bu, $^t$-Bu, -sec-Bu, -iso-Bu). and C$_3$-C$_9$ cycloalkyl (e.g., cyclopropyl, cyclobutyl, cyclopentyl, cyclohexyl); and n is 0, 1, 2 or 3 provided that:

(i) when R$^1$ is H, R$^2$ is not halo, —OPr, —N(CH$_3$)$_2$ or —CF$_3$;

(ii) when R$^1$ is OR$^{a1}$, R$^2$ is not —OR$^{a2}$;

(iii) when R$^1$ is H and R$^2$ is —CH$_3$, R$^8$ groups cannot be taken together to form a ring and R$^6$ is not absent or H, and is not thiazolyl, furanyl or pyrrolyl;

(iv) when R$^2$ is Me, R$^1$ is not optionally substituted piperidine (v) the compound is not:

(A) 5-(2-(5-methyl-2-(p-tolyl)piperidin-1-yl)-2-oxoacetamido)nicotinamide or any of its enantiomers or diastereomers;

(B)$_2$-(2-(4-(2H-tetrazol-5-yl)phenyl)-5-methylpiperidin-1-yl)-N-(5,6-dimethylpyridin-3-yl)-2-oxoacetamide or any of its enantiomers or diastereomers;

(C)$_2$-cyano-5-(2-(5-methyl-2-phenylpiperidin-1-yl)-2-oxoacetamido)nicotinamide or any of its enantiomers or diastereomers.

In certain embodiments, R$^6$ and R$^7$ are not H and are in a trans relative configuration. In some embodiments, R$^6$ and R$^7$ are not H and are in a cis relative configuration.

In some embodiments of Formula (I), the moiety represented as

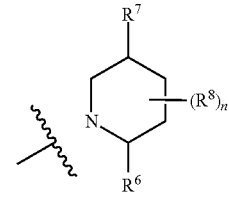

is selected from:

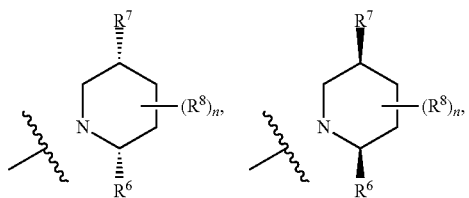

-continued

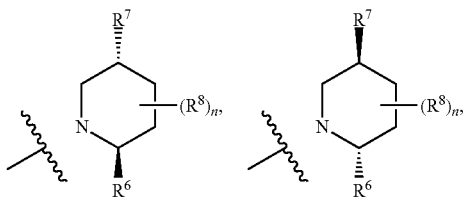

In some embodiments of Formula (I) the moiety represented as

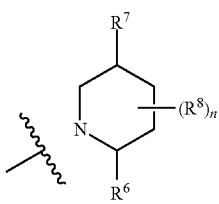

is selected from:

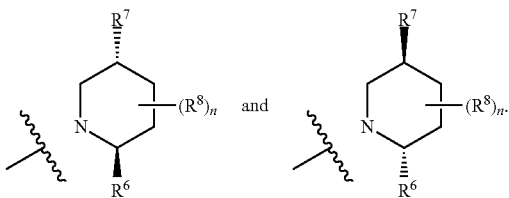

In other embodiments of Formula (I), the moiety represented as

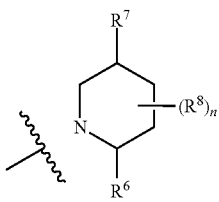

is selected from:

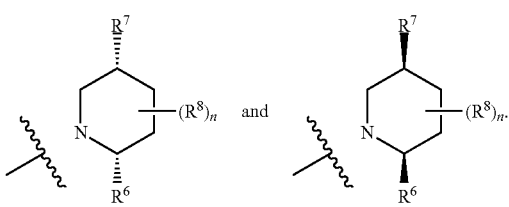

In some embodiments, the compound is of Formula (Ia)

Formula (Ia)

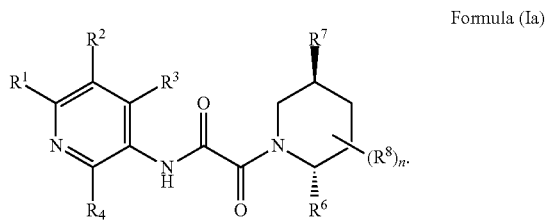

In other embodiments, the compound is of Formula (Ib)

Formula (Ib)

In some embodiments, the compound is of Formula (Ic)

Formula (Ic)

In other embodiments, the compound is of Formula (Id)

Formula (Id)

In some embodiments of Formula (I), (Ia), (Ib), (Ic) and (Id), each $R^8$ is independently selected from H, -D, =O, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —O$R^{a8}$, —N($R^{a8}$)$_2$, —C(=O)$R^{a8}$, —C(=O)O$R^{a8}$, —N$R^{a8}$C(=O)$R^{a8}$, —N$R^{a8}$C(=O)O$R^{a8}$—CH$_2$C(=O)N($R^{a8}$)$_2$—C(=O)N($R^{a8}$)$_2$, —OC(=O)N($R^{a8}$)$_2$, —CH$_2$C(=O)N($R^{a8}$)$_2$, —S(=O)$R^{a8}$, S(=O)$_2R^{a8}$, —S$R^{a8}$, —S(=O)(=N$R^{a8}$)$R^{a8}$, —N$R^{a8}$S(=O)$_2R^{a8}$ and —S(=O)$_2$N($R^{a8}$)$_2$.

In some embodiments of Formula (I), (Ia), (Ib), (Ic) and (Id), $R^1$ is selected from H, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, —O$R^{a1}$, —N($R^{a1}$)$_2$, —C(=O)$R^{a1}$, —C(=O)O$R^{a1}$, —N$R^{a1}$C(=O)$R^{a1}$— N$R^{a1}$C(=O)O$R^{a1}$, —C(=O)N($R^{a1}$)$_2$ and —OC(=O)N($R^{a1}$)$_2$. In some embodiments, $R^1$ is selected from H, halo, —CN, —$C_1$-$C_6$ alkyl, —$C_1$-$C_6$ haloalkyl, —$OR^{a1}$ and —$N(R^{a1})_2$. In some embodiments, $R^1$ is selected from H, —$C_1$-$C_6$ alkyl, —$C_1$-$C_6$ haloalkyl, —$OR^{a1}$ and —$N(R^{a1})_2$. In further embodiments, each $R^{a1}$ is independently selected from H, —$C_1$-$C_6$ alkyl (e.g., -Me, -Et, —Pr, -$^i$Pr, -$^n$Bu, —Bu, -sec-Bu, -iso-Bu) and —$C_1$-$C_6$ haloalkyl (e.g., —$CHF_2$, —$CF_3$).

In certain embodiments of Formula (I), (Ia), (Ib), (Ic) and (Id), $R^1$ is selected from H, —$C_1$-$C_6$ alkyl (e.g., -Me, -Et, —Pr, -$^i$Pr, -$^n$Bu, —Bu, -sec-Bu, -iso-Bu), —$C_1$-$C_6$ alkyl (e.g., —$CF_3$, —$CHF_2$), —OH, —O—($C_1$-$C_6$ alkyl) (e.g., —OMe, —OEt), —O—($C_1$-$C_6$ haloalkyl) (e.g., —$OCF_3$, —$OCHF_2$), —$NH_2$, —NH—($C_1$-$C_6$ alkyl) (e.g., —NHMe) and —N—($C_1$-$C_6$ alkyl)$_2$ (e.g., $NMe_2$). In some embodiments, $R^1$ is selected from H, -Me, -Et, —$CHF_2$, —OMe, —OEt, —$OCHF_2$, —$OCF_3$, —OH and —$NH_2$. In further embodiments, $R^1$ is selected from H, -Et, —OMe, —OEt, —$OCHF_2$, —$OCF_3$ and —OH. In certain embodiments, $R^1$ is selected from H and —OMe. In some embodiments, $R^1$ is H. In other embodiments, $R^1$ is —OMe.

In certain embodiments, $R^1$ is selected from H, -Me, —$CHF_2$ and —$NH_2$. In further embodiments, $R^1$ is selected from -Me and —$NH_2$. In certain embodiments, $R^1$ is -Me. In other embodiments, $R^1$ is —$NH_2$.

In some embodiments of Formula (I), (Ia), (Ib), (Ic) and (Id), $R^2$ is selected from halo, —CN, —$C_1$-$C_6$ alkyl, —$C_1$-$C_6$ heteroalkyl, —$C_1$-$C_6$ haloalkyl, —$C_1$-$C_6$ haloalkoxy, —$C_3$-$C_9$ cycloalkyl (e.g., cyclopropyl), 3-10 membered heterocyclyl (e.g., oxetanyl, tetrahydrofuranyl), —$OR^{a2}$, —$N(R^{a2})_2$, —$C(=O)R^{a2}$, —$C(=O)OR^{a2}$, —$NR^{a2}C(=O)R^{a2}$, —$NR^{a2}C(=O)OR^{a2}$, —$C(=O)N(R^{a2})_2$, —$C(=O)N(OR^{a2})(R^{a2})$ and —$OC(=O)N(R^{a2})_2$. In further embodiments, $R^2$ is selected from halo, —CN, —$C_1$-$C_6$ alkyl, —$C_1$-$C_6$ haloalkyl, —$C_1$-$C_6$ haloalkoxy, —$C_3$-$C_9$ cycloalkyl (e.g., cyclopropyl), 3-6 membered heterocyclyl (e.g., oxetanyl, tetrahydrofuranyl), —$OR^{a2}$, —$N(R^{a2})_2$, —$C(=O)N(OR^{a2})(R^{a2})$, —$C(=O)R^{a2}$ and —$C(=O)N(R^{a2})_2$. In certain embodiments, $R^2$ is selected from halo, —$C_1$-$C_6$ alkyl, —$C_1$-$C_6$ haloalkyl, —$C_1$-$C_6$ haloalkoxy, —$C_3$-$C_9$ cycloalkyl (e.g., cyclopropyl), 3-6 membered heterocyclyl (e.g., oxetanyl, tetrahydrofuranyl), —$OR^{a2}$, —$C(=O)R^{a2}$ and —$C(=O)N(R^{a2})_2$. In some embodiments, $R^2$ is selected from halo, —$C_1$-$C_6$ alkyl, —$C_3$-$C_9$ cycloalkyl (e.g., cyclopropyl), 3-6 membered heterocyclyl (e.g., oxetanyl, tetrahydrofuranyl), —$C_1$-$C_6$ haloalkyl, —$C_1$-$C_6$ haloalkoxy, —$OR^{a2}$, and —$C(=O)N(R^{a2})_2$. In further embodiments, each $R^{a2}$ is independently selected from H and —$C_1$-$C_6$ alkyl (e.g., -Me, -Et, —Pr, -$^i$Pr, -$^n$Bu, $^t$-Bu, -sec-Bu, -iso-Bu). In certain embodiments, $R^2$ is selected from halo (e.g., —$C_1$), —$C_1$-$C_6$ alkyl (e.g., -Me, -Et, —Pr, -$^i$Pr, -$^n$Bu, —Bu, -sec-Bu, -iso-Bu), —$C_1$-$C_6$ haloalkyl (e.g., —$CF_3$, $CHF_2$), —$C_3$-$C_9$ cycloalkyl (e.g., cyclopropyl), 3-6 membered heterocyclyl (e.g., oxetanyl, tetrahydrofuranyl), —$C_1$-$C_6$ haloalkoxy (e.g., —$OCF_3$, —$OCHF_2$), —OMe, —C(=O)H, —C(=O)NHOH, and —$C(=O)NH_2$. In further embodiments, $R^2$ is selected from —$C_1$, -Me, -Et, -$^i$Pr, —$CF_3$, $CHF_2$, —$OCHF_2$, —$OCF_3$, cyclopropyl, —C(=O)NHOH, —C(=O)H and —$C(=O)NH_2$. In certain embodiments, $R^2$ is selected from —$C(=O)NH_2$ and —C(=O)H. In some embodiments, $R^2$ is —$C(=O)NH_2$. In certain embodiments, $R^2$ is selected from —$C_1$, -Me, -Et, -$^i$Pr, —$CF_3$, —$CHF_2$, —$OCHF_2$, —$OCF_3$, oxetan-3-yl, tetrahydrofuran-3-yl, and cyclopropyl. In further embodiments, $R^2$ is selected from cyclopropyl, -Me and -Et.

In some embodiments, $R^1$ is selected from H, —OMe, —OEt, —$OCF_3$, —$OCHF_2$, —$CHF_2$, -Me, -Et, —OH and —$NH_2$ and $R^2$ is selected from —$C_1$, -Me, -Et, -$^i$Pr, —$CF_3$, —$CHF_2$, —$OCHF_2$, —$OCF_3$, cyclopropyl, —$C(=O)NH_2$, and —C(=O)H, provided that when $R^2$ is -Me, $R^1$ is $NH_2$. In some embodiments, $R^1$ is selected from H, —$CHF_2$, -Me and —$NH_2$ and $R^2$ is selected from —$C_1$, -Me, -Et, —$CF_3$, —$CHF_2$, —$OCHF_2$ and cyclopropyl, provided that when $R^2$ is -Me, $R^1$ is $NH_2$. In certain embodiments, $R^1$ is selected from —$NH_2$ and -Me and $R^2$ is selected from -Me, and -Et. In further embodiments, $R^1$ is —$NH_2$ and $R^2$ is selected from cyclopropyl, -Me, and -Et.

In some embodiments $R^1$ is selected from H, —OMe, —OEt, —$OCF_3$, —$OCHF_2$, -Et and —OH and $R^2$ is selected from —$C(=O)NH_2$ and —C(=O)H. In further embodiments, $R^1$ is selected from H and —OMe and $R^2$ is —$C(=O)NH_2$.

In some embodiments of Formula (I), (Ia), (Ib), (Ic) and (Id), $R^3$ is selected from H, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, —$OR^{a3}$, —$N(R^{a3})_2$, —$C(=O)R^{a3}$, —$C(=O)OR^{a3}$, —$Na^3C(=O)R^{a3}$—$NR^{a3}C(=O)OR^{a3}$, —$C(=O)N(R^{a3})_2$ and —$OC(=O)N(R^{a3})_2$. In some embodiments, $R^3$ is selected from H, halo, —CN, —$C_1$-$C_6$ alkyl, —$C_1$-$C_6$ haloalkyl and —$N(R^{a3})_2$. In further embodiments, $R^{a3}$ is selected from H and $C_1$-$C_6$ alkyl (e.g., -Me, -Et, —Pr, -$^i$Pr, -$^n$Bu, -$^t$Bu, -sec-Bu, -iso-Bu). In certain embodiments, $R^3$ is selected from —$C_1$-$C_6$ alkyl (e.g., -Me, -Et, —Pr, -$^i$Pr, -$^n$Bu, —$^t$Bu, -sec-Bu, -iso-Bu), —OH, —O—($C_1$-$C_6$ alkyl) (e.g., —OMe), —$NH_2$, —NH—($C_1$-$C_6$ alkyl) (e.g., —NHMe) and —N—($C_1$-$C_6$ alkyl)$_2$ (e.g., $NMe_2$). In further embodiments, $R^3$ is selected from H, -Me and —$NH_2$. In certain embodiments, $R^3$ is selected from H and -Me. In further embodiments, $R^3$ is -Me.

In some embodiments of Formula (I), (Ia), (Ib), (Ic) and (Id), $R^4$ is selected from H, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, —$OR^{a4}$, —$N(R^{a4})_2$, —$C(=O)R^{a4}$, —$C(=O)OR^{a4}$, —$NR^{a4}C(=O)R^{a4}$—$NR^{a4}C(=O)OR^{a4}$, —$C(=O)N(R^{a4})_2$ and —$OC(=O)N(R^{a4})_2$. In some embodiments, $R^4$ is selected from H, halo, —CN, —$C_1$-$C_6$ alkyl, —$C_1$-$C_6$ haloalkyl and —$N(R^{a4})_2$. In further embodiments, each $R^{a4}$ is independently selected from H and —$C_1$-$C_6$ alkyl (e.g., -Me, -Et, —Pr, -$^i$Pr, -$^n$Bu, $^t$-Bu, -sec-Bu, -iso-Bu). In certain embodiments, $R^4$ is selected from —$C_1$-$C_6$ alkyl (e.g., -Me, -Et, —Pr, -$^i$Pr, -$^n$Bu, -$^i$Bu, -sec-Bu, -iso-Bu), —OH, —O—($C_1$-$C_6$ alkyl) (e.g., —OMe), —$NH_2$, —NH—($C_1$-$C_6$ alkyl) (e.g., —NHMe) and —N—($C_1$-$C_6$ alkyl)$_2$ (e.g., $NMe_2$). In further embodiments, $R^4$ is H.

In some embodiments of Formula (I), (Ia), (Ib), (Ic) and (Id), each $R^6$ is independently selected from H, -D, halo, —CN, —$C_1$-$C_6$ alkyl, —$C_1$-$C_6$ heteroalkyl, —$C_1$-$C_6$ haloalkyl, —$C_3$-$C_{10}$ carbocyclyl, 3-10 membered heterocyclyl, heterocyclylalkyl, $C_6$-$C_{10}$ aryl, 5-10 member heteroaryl, heteroarylalkyl, arylalkyl, cycloalkylalkyl, —$OR^{a6}$, —$N(R^{a6})_2$, —$C(=O)R^{a6}$, —$C(=O)OR^{a6}$, —$NR^{a6}C(=O)R^{a6}$, —$NR^{a6}C(=O)OR^{a6}$, —$C(=O)N(R^{a6})_2$, —$OC(=O)N(R^{a6})_2$, —$S(=O)R^{a6}$, —$S(=O)_2R^{a6}$, —$SR^{a6}$, —$S(=O)(=NR^{a6})R^{a6}$, —$NR^{a6}S(=O)_2R^{a6}$ and —$S(=O)_2N(R^{a6})_2$, wherein each alkyl, carbocyclyl, heterocyclyl, aryl, heteroaryl, cycloalkylalkyl, heterocyclylalkyl, arylalkyl and heteroarylalkyl is substituted at any available position with 0, 1, 2 or 3 instances of $R^{10}$, wherein:

each $R^{10}$ is independently selected from -D, =O, —CN, halo, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, $C_6$-$C_{10}$ aryl, 5-10 membered heteroaryl, cycloalkylalkyl, heterocyclylalkyl, arylalkyl, het eroarylalkyl, heterocyclylalkoxy, —OR$^{b10}$, —N(R$^{b10}$)$_2$, —C(=O)R$^{b10}$, —C(=O)OR$^{b10}$, —NR$^{b10}$C(=O)R$^{b10}$, —NR$^{b10}$C(=O)OR$^{b10}$, —C(=O)N(R$^{b10}$)$_2$, —OC(=O)R$^{b10}$, —OC(=O)N(R$^{b10}$)$_2$, —S(=O)R$^{b10}$, —S(=O)$_2$R$^{b10}$, —SR$^{b10}$, —S(=O)(=NR$^{10}$)R$^{b10}$, —NR$^{b10}$S(=O)$_2$R$^{b10}$ and —S(=O)$_2$N(R$^{b10}$)$_2$ wherein each alkyl, cycloalkyl, heteroalkyl, heterocyclyl, aryl, heteroaryl, cycloalkylalkyl, heterocyclylalkyl, heterocyclylalkoxy, arylalkyl and heteroarylalkyl of R$^{10}$ is optionally substituted (e.g., substituted with 0, 1, 2 or 3 instances of -Me, —OH, C(=O)Me, —C(=O)NHMe, —NH$_2$, —NHC(=O)Me or a combination thereof);

each R$^{b10}$ is independently H; —C$_1$-C$_6$ alkyl; —C$_1$-C$_6$ haloalkyl; —C$_1$-C$_6$ heteroalkyl substituted with 0 or 1 instance of =O; C$_3$-C$_9$ cycloalkyl; or 3-10 member heterocyclyl substituted with 0 or 1 instances of =O, -Me or a combination thereof.

In some embodiments of Formula (I), (Ia), (Ib), (Ic) and (Id), each R$^6$ is independently selected from -D, halo, —CN, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl, cycloalkylalkyl, —OR$^{a6}$, —N(R$^{a6}$)$_2$, —C(=O)R$^{a6}$, —C(=O)OR$^{a6}$, —NR$^{a6}$C(=O)R$^{a6}$, —NR$^{a6}$C(=O)OR$^{a6}$, —C(=O)N(R$^{a6}$)$_2$, —OC(=O)N(R$^{a6}$)$_2$, —S(=O)R$^{a6}$, —S(=O)$_2$R$^{a6}$, —SR$^{a6}$, —S(=O)(=NR$^{a6}$)R$^{a6}$, —NR$^{a6}$S(=O)$_2$R$^{a6}$ and —S(=O)$_2$N(R$^{a6}$)$_2$, wherein each alkyl, carbocyclyl, heterocyclyl, aryl, heteroaryl, cycloalkylalkyl, heterocyclylalkyl, arylalkyl and heteroarylalkyl is substituted at any available position with 0, 1, 2 or 3 instances of R$^{10}$, wherein: each R$^{10}$ is independently selected from -D, =O, —CN, halo, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, C$_6$-C$_{10}$ aryl, 5-10 membered heteroaryl, cycloalkylalkyl, heterocyclylalkyl, arylalkyl, heteroarylalkyl, heterocyclylalkoxy, —OR$^{b10}$, —N(R$^{b10}$)$_2$, —C(=O)R$^{b10}$, —C(=O)OR$^{b10}$, —NR$^{b10}$C(=O)R$^{b10}$, —NR$^{b10}$C(=O)OR$^{b10}$, —C(=O)N(R$^{b10}$)$_2$, —OC(=O)R$^{b10}$, —OC(=O)N(R$^{b10}$)$_2$, —S(=O)R$^{b10}$, —S(=O)$_2$R$^{b10}$, —SR$^{b10}$, —S(=O)(=NR$^{b10}$)R$^{b10}$, —NR$^{b10}$S(=O)$_2$R$^{b10}$ and —S(=O)$_2$N(R$^{b10}$)$_2$ wherein each alkyl, cycloalkyl, heteroalkyl, heterocyclyl, aryl, heteroaryl, cycloalkylalkyl, heterocyclylalkyl, heterocyclylalkoxy, arylalkyl and heteroarylalkyl of R$^{10}$ is optionally substituted (e.g., substituted with 0, 1, 2 or 3 instances of -Me, —OH, C(=O)Me, —C(=O)NHMe, —NH$_2$, —NHC(=O)Me or a combination thereof);

each R$^{b10}$ is independently H; —C$_1$-C$_6$ alkyl; —C$_1$-C$_6$ haloalkyl; —C$_1$-C$_6$ heteroalkyl substituted with 0 or 1 instance of =O; C$_3$-C$_9$ cycloalkyl; or 3-10 member heterocyclyl substituted with 0 or 1 instances of =O, -Me or a combination thereof.

In some embodiments of Formula (I), (Ia), (Ib), (Ic) and (Id), each R$^6$ is independently selected from H, halo, —CN, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl, cycloalkylalkyl, —OR$^{a6}$, —N(R$^{a6}$)$_2$, —C(=O)R$^{a6}$, —C(=O)OR$^{a6}$, —NR$^{a6}$C(=O)R$^{a6}$, —NR$^{a6}$C(=O)OR$^{a6}$, —C(=O)N(R$^{a6}$)$_2$, —OC(=O)N(R$^{a6}$)$_2$, —S(=O)R$^{a6}$, —S(=O)$_2$R$^{a6}$, —SR$^{a6}$, —S(=O)(=NR$^{a6}$)R$^{a6}$, —NR$^{a6}$S(=O)$_2$R$^{a6}$ and —S(=O)$_2$N(R$^{a6}$)$_2$, wherein each alkyl, carbocyclyl, heterocyclyl, aryl, heteroaryl, cycloalkylalkyl, heterocyclylalkyl, arylalkyl and heteroarylalkyl is substituted at any available position with 0, 1, 2 or 3 instances of R$^{10}$, wherein:

each R$^{10}$ is independently selected from -D, =O, —CN, halo, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, C$_6$-C$_{10}$ aryl, 5-10 membered heteroaryl, cycloalkylalkyl, heterocyclylalkyl, arylalkyl, heteroarylalkyl, heterocyclylalkoxy, —OR$^{b10}$, —N(R$^{b10}$)$_2$, —C(=O)R$^{b10}$, —C(=O)OR$^{b10}$, —NR$^{b10}$C(=O)R$^{b10}$, —NR$^{b10}$C(=O)OR$^{b10}$, —C(=O)N(R$^{b10}$)$_2$, —OC(=O)R$^{b10}$, —OC(=O)N(R$^{b10}$)$_2$, —S(=O)R$^{b10}$, —S(=O)$_2$R$^{b10}$, —SR$^{b10}$, —S(=O)(=NR$^{b10}$)R$^{b10}$, —NR$^{b10}$S(=O)$_2$R$^{b10}$ and —S(=O)$_2$N(R$^{b10}$)$_2$ wherein each alkyl, cycloalkyl, heteroalkyl, heterocyclyl, aryl, heteroaryl, cycloalkylalkyl, heterocyclylalkyl, arylalkyl and heteroarylalkyl of R$^{10}$ is optionally substituted (e.g., substituted with 0, 1, 2 or 3 instances of -Me, —OH, C(=O)Me, —C(=O)NHMe, —NH$_2$, —NHC(=O)Me or a combination thereof);

each R$^{b10}$ is independently H; —C$_1$-C$_6$ alkyl; —C$_1$-C$_6$ haloalkyl; —C$_1$-C$_6$ heteroalkyl substituted with 0 or 1 instance of =O; C$_3$-C$_9$ cycloalkyl; or 3-10 member heterocyclyl substituted with 0 or 1 instances of =O, -Me or a combination thereof.

In some embodiments, each R$^{a6}$ is independently selected from H and —C$_1$-C$_6$ alkyl (e.g., -Me, -Et, —Pr, -$^i$Pr, -$^n$Bu, -$^t$Bu, -sec-Bu, -iso-Bu).

In some embodiments of Formula (I), (Ia), (Ib), (Ic) and (Id), each R$^6$ is independently selected from H, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, cycloalkyl, heterocyclyl, cycloalkylalkyl, heterocyclylalkyl, aryl, heteroaryl, arylalkyl and heteroarylalkyl is optionally substituted at any available position.

In some embodiments, each R$^6$ is independently selected from —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, cycloalkyl, heterocyclyl, cycloalkylalkyl, heterocyclylalkyl, aryl, heteroaryl, arylalkyl and heteroarylalkyl is optionally substituted at any available position. In some embodiments, each R$^6$ is independently selected from H, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, cycloalkyl, heterocyclyl, cycloalkylalkyl, heterocyclylalkyl, aryl, heteroaryl, arylalkyl and heteroarylalkyl is substituted at any available position with 0, 1, 2 or 3 instances of R$^{10}$ wherein:

each R$^{10}$ is independently selected from -D, =O, —CN, halo, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, C$_6$-C$_{10}$ aryl, 5-10 membered heteroaryl, cycloalkylalkyl, arylalkyl, heteroarylalkyl, heterocyclylalkoxy, heterocyclylalkyl, —OR$^{b10}$, —N(R$^{b10}$)$_2$, —C(=O)R$^{b10}$, —C(=O)OR$^{b10}$, —NR$^{b10}$C(=O)R$^{b10}$, —NR$^{b10}$C(=O)OR$^{b10}$, —C(=O)N(R$^{b10}$)$_2$, —OC(=O)R$^{b10}$, —OC(=O)N(R$^{b10}$)$_2$, —S(=O)R$^{b10}$, —S(=O)$_2$R$^{b10}$, —SR$^{b10}$, —S(=O)(=NR$^{10}$)R$^{b10}$, —NR$^{10}$S(=O)$_2$R$^{b10}$ and —S(=O)$_2$N(R$^{b10}$)$_2$, wherein each alkyl, cycloalkyl, heteroalkyl, heterocyclyl, aryl, heteroaryl, cycloalkylalkyl, heterocyclylalkyl, arylalkyl and heteroarylalkyl of R$^{10}$ is optionally substituted (e.g., with 0, 1, 2, 3, 4, or 5 instances of -Me, -Et, -$^i$Pr, cyclopropyl, oxetan-3-yl, —OH, =O, —F, —OMe, —CH$_2$CH$_2$F, —CH$_2$CHF$_2$, —CH$_2$CH$_2$CF$_3$, —C(=O)Me, —N(Me)$_2$, —CH$_2$N(CH$_3$)$_2$, —CH$_2$N(CH$_3$)CH$_2$CH$_3$, —N($^i$Pr)(Et), —N($^i$Pr)(Me), —N(Et)$_2$, —N(CH$_3$)(Et), —NHC(=O)Me, or a combination thereof); and each R$^{b10}$ is independently selected from H; —C$_1$-C$_6$ alkyl; —C$_1$-C$_6$ haloalkyl; —C$_1$-C$_6$ heteroalkyl substituted with 0 or 1 instance of =O; C$_3$-C$_9$ cycloalkyl; and a 3-10 member heterocyclyl substituted with 0 or 1 instances of =O, -Me or a combination thereof.

In some embodiments of Formula (I), (Ia), (Ib), (Ic) and (Id), each R$^6$ is independently selected from H, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, cycloalkyl, heterocyclyl, cycloalkylalkyl, heterocyclylalkyl, aryl, heteroaryl, arylalkyl and heteroarylalkyl is optionally substituted at any available position. In certain embodiments, each R$^6$ is independently selected from H, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, cycloalkyl, heterocyclyl, cycloalkylalkyl, heterocyclylalkyl, aryl, heteroaryl, arylalkyl and heteroarylalkyl is substituted at any available position with 0, 1, 2 or 3 instances of R$^{10}$ wherein:

each R$^{10}$ is independently selected from -D, =O, —CN, halo, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, C$_6$-C$_{10}$ aryl, 5-10 membered heteroaryl, cycloalkylalkyl, arylalkyl, heteroarylalkyl, heterocyclylalkoxy, heterocyclylalkyl, —OR$^{b10}$, —N(R$^{b10}$)$_2$, —C(=O)R$^{b10}$, —C(=O)OR$^{b10}$, —NR$^{b10}$C(=O)R$^{b10}$, —NR$^{b10}$C(=O)OR$^{b10}$, —C(=O)N(R$^{b10}$)$_2$, —OC(=O)R$^{b10}$, —OC(=O)N(R$^{b10}$)$_2$, —S(=O)R$^{b10}$, —S(=O)$_2$R$^{b10}$, —SR$^{b10}$, —S(=O)(=NR$^{b10}$)R$^{b10}$, —NR$^{b10}$S(=O)$_2$R$^{b10}$ and —S(=O)$_2$N(R$^{b10}$)$_2$, wherein each alkyl, cycloalkyl, heteroalkyl, heterocyclyl, aryl, heteroaryl, cycloalkylalkyl, heterocyclylalkyl, arylalkyl and heteroarylalkyl of R$^{10}$ is optionally substituted (e.g., with 0, 1, 2, 3, 4, or 5 instances of -Me, -Et, -$^i$Pr, cyclopropyl, oxetan-3-yl, —OH, =O, —F, —OMe, —CH$_2$CH$_2$F, —CH$_2$CHF$_2$, —CH$_2$CH$_2$CF$_3$, —C(=O)Me, —N(Me)$_2$, —CH$_2$N(CH$_3$)$_2$, —CH$_2$N(CH$_3$)CH$_2$CH$_3$, —N($^i$Pr)(Et), —N($^i$Pr)(Me), —N(Et)$_2$, —N(CH$_3$)(Et), —NHC(=O)Me, or a combination thereof); and each R$^{b10}$ is independently selected from H; —C$_1$-C$_6$ alkyl; —C$_1$-C$_6$ haloalkyl; —C$_1$-C$_6$ heteroalkyl substituted with 0 or 1 instance of =O; C$_3$-C$_9$ cycloalkyl; and a 3-10 member heterocyclyl substituted with 0 or 1 instances of =O, -Me or a combination thereof.

In some embodiments, each R$^6$ is independently selected from H, —C$_1$-C$_6$ alkyl (e.g., -Me, -Et, —Pr, -$^i$Pr, -$^n$Bu, sec-Bu, $^t$-Bu), —C$_3$-C$_{10}$ monocyclic or bicyclic carbocyclyl (e.g., cyclopropyl, cyclobutyl, cyclopentyl, cyclohexyl, cycloheptyl, bicyclo[1.1.1]pentan-yl, 4,5,6,7-tetrahydro-1H-indazolyl, spiro[3.3]heptanyl), 3-10 membered mono or bicyclic heterocyclyl (e.g., oxetanyl, azepanyl, piperidinyl, pyrorolidinyl, tetrahydrofuranyl, tetrahydropyranyl, 1,2-dihydropyridinyl, morpholinyl, isoindolinyl), C$_6$-C$_{10}$ mono or bicyclic aryl (e.g., phenyl, naphthyl, 1,2,3,4-tetrahydronaphthalenyl, 2,3-dihydro-1H-indenyl, 1,2,3,4 tetrahydroquinolinyl, 1,2 dihydroquinolinyl, 1,2-dihydroisoquinolinyl, 1,2,3,4 tetrahydroisoquinolinyl, chromanyl, indolinyl, isoindolinyl, 3,4-dihydro-2H-benzo[b][1,4]oxazinyl, 2,3-dihydrobenzofuranyl, benzo[d][1,3]dioxolyl, 2,3-dihydro-1H-benzo[d]imidazolyl), 5-6 member monocyclic heteroaryl (e.g., thiophenyl, thiazolyl, pyrazolyl, imidazolyl, oxazolyl, pyridinyl, pyrimidinyl), 8-10 member bicyclic heteroaryl (e.g., benzo[d]isothiazolyl, indolyl, benzofuranyl, 1H-indazolyl, 2H-indazolyl, benzo[b]thiophenyl, quinolinyl, 1,5-naphthyridinyl, 1,2-dihydro-1,5-naphthyridinyl, 1,2,3,4-tetrahydro-1,8-naphthyridinyl, isoquinolinyl, benzo[d]imidazolyl, benzo[d]thiazolyl, benzo[d]oxazolyl, [1,2,4]triazolo[4,3-a]pyridinyl, imidazo[1,2-a]pyridinyl, imidazo[1,5-a]pyridinyl, 1H-pyrazolo[4,3-b]pyridinyl), 1H-pyrazolo[3,4-b]pyridinyl, 1H-thieno[2,3-c]pyrazolyl, 1H-thieno[3,2-c]pyrazolyl, thiazolo[5,4-b]pyridinyl) wherein each alkyl, carbocyclyl, heterocyclyl, aryl and heteroaryl is optionally substituted (e.g., substituted with 0, 1, 2 or 3 instances of R$^{10}$). In some embodiments, each R$^6$ is independently selected from —C$_1$-C$_6$ alkyl (e.g., -Me, -Et, —Pr, -$^i$Pr, -$^n$Bu, sec-Bu, $^t$-Bu), —C$_3$-C$_{10}$ monocyclic or bicyclic carbocyclyl (e.g., cyclopropyl, cyclobutyl, cyclopentyl, cyclohexyl, cycloheptyl, bicyclo[1.1.1]pentan-yl, 4,5,6,7-tetrahydro-1H-indazolyl, spiro[3.3]heptanyl), 3-10 membered mono or bicyclic heterocyclyl (e.g., oxetanyl, azepanyl, piperidinyl, pyrorolidinyl, tetrahydrofuranyl, tetrahydropyranyl, 1,2-dihydropyridinyl, morpholinyl, isoindolinyl), C$_6$-C$_{10}$ mono or bicyclic aryl (e.g., phenyl, naphthyl, 1,2,3,4-tetrahydronaphthalenyl, 2,3-dihydro-1H-indenyl, 1,2,3,4 tetrahydroquinolinyl, 1,2 dihydroquinolinyl, 1,2-dihydroisoquinolinyl, 1,2,3,4 tetrahydroisoquinolinyl, chromanyl, indolinyl, isoindolinyl, 3,4-dihydro-2H-benzo[b][1,4]oxazinyl, 2,3-dihydrobenzofuranyl, benzo[d][1,3]dioxolyl, 2,3-dihydro-1H-benzo[d]imidazolyl), 5-6 member monocyclic heteroaryl (e.g., thiophenyl, thiazolyl, pyrazolyl, imidazolyl, oxazolyl, pyridinyl, pyrimidinyl), 8-10 member bicyclic heteroaryl (e.g., benzo[d]isothiazolyl, indolyl, benzofuranyl, 1H-indazolyl, 2H-indazolyl, benzo[b]thiophenyl, quinolinyl, 1,5-naphthyridinyl, 1,2-dihydro-1,5-naphthyridinyl, 1,2,3,4-tetrahydro-1,8-naphthyridinyl, isoquinolinyl, benzo[d]imidazolyl, benzo[d]thiazolyl, benzo[d]oxazolyl, [1,2,4]triazolo[4,3-a]pyridinyl, imidazo[1,2-a]pyridinyl, imidazo[1,5-a]pyridinyl, 1H-pyrazolo[4,3-b]pyridinyl), 1H-pyrazolo[3,4-b]pyridinyl, 1H-thieno[2,3-c]pyrazolyl, 1H-thieno[3,2-c]pyrazolyl, thiazolo[5,4-b]pyridinyl) wherein each alkyl, carbocyclyl, heterocyclyl, aryl and heteroaryl is optionally substituted (e.g., substituted with 0, 1, 2 or 3 instances of R$^{10}$). In certain embodiments, each R$^6$ is an 8-10 member bicyclic heteroaryl (e.g., indolyl, benzofuranyl, 1H-indazolyl, 2H-indazolyl, benzo[b]thiophenyl, quinolinyl, 1,5-naphthyridinyl, 1,2-dihydro-1,5-naphthyridinyl, 1,2,3,4-tetrahydro-1,8-naphthyridinyl, imidazo[1,2-a]pyridinyl, imidazo[1,5-a]pyridinyl, isoquinolinyl, benzo[d]imidazolyl, benzo[d]thiazolyl, benzo[d]isothiazolyl, benzo[d]oxazolyl, [1,2,4]triazolo[4,3-a]pyridinyl, imidazo[1,2-a]pyridinyl, 1H-pyrazolo[4,3-b]pyridinyl), 1H-pyrazolo[3,4-b]pyridinyl, 1H-thieno[2,3-c]pyrazolyl, 1H-thieno[3,2-c]pyrazolyl, thiazolo[5,4-b]pyridinyl, 1,2,3,4-tetrahydro-1,8-naphthyridinyl) wherein the bicyclic heteroaryl is optionally substituted (e.g., substituted with 0, 1, 2 or 3 instances of R$^{10}$). In some embodiments, each R$^6$ is independently selected from H, -Me, -$^i$Pr, -$^n$Bu, sec-Bu, cyclobutyl, cyclopentyl, cyclohexyl, bicyclo[1.1.1]pentan-1-yl, spiro[3.3]heptan-2-yl, 4,5,6,7-tetrahydro-1H-indazol-6-yl, piperidin-4-yl, piperidin-3-yl, pyrrolidin-3-yl, 1,2-dihydropyridin-4-yl, phenyl, naphthalen-2-yl, 1,2,3,4-tetrahydroquinolin-6-yl, 1,2,3,4-tetrahydronaphthalen-6-yl, chroman-6-yl, 1,5-naphthyridin-6-yl, 1,2,3,4-tetrahydro-1,8-naphthyridin-6-yl, 2,3-dihydro-1H- inden-5-yl, indolin-5-yl, indolin-4-yl, 2,3-dihydro-1H-benzo[d]imidazol-5-yl, 2,3-dihydrobenzofuran-5-yl, 2,3-dihydrobenzofuran-6-yl, benzo[d][1,3]dioxol-5-yl], isoindolin-5-yl, isoindolin-6-yl, 3,4-dihydro-2H-benzo[b][1,4]oxazin-7-yl, 1,2-dihydroquinolin-6-yl, 1,2-dihydroisoquinolin-7-yl, thiophen-2-yl, thiophen-3-yl, thiazol-2-yl, thiazol-4-yl, thiazol-5-yl, pyrazol-1-yl, pyrazol-5-yl, pyrazol-3-yl, pyrazol-4-yl, pyridin-2-yl, pyridin-3-yl, pyridin-4-yl, pyrimidin-5-yl, indol-4-yl, indol-5-yl, benzofuran-5-yl, benzofuran-6-yl, 1H indazol-5-yl, 1H indazol-4-yl, 2H-indazol-6-yl, 2H-indazol-5-yl, benzo[b]thiophen-3-yl, benzo[b]thiophen-5-yl, quinolin-6-yl, quinoline-3-yl, isoquinolin-6-yl, benzo[d]imidazo-5-yl, 1H-benzo[d]imidazol-4-yl, benzo[d]thiazol-5-yl, benzo[d]thiazol-6-yl, benzo[d]thiazol-4-yl, benzo[d]isothiazol-5-yl, benzo[d]oxazol-4-yl, benzo[d]oxazol-5-yl, [1,2,4]triazolo[4,3-a]pyridin-6-yl, imidazo[1,2-a]pyridin-6-yl, imidazo[1,2-a]pyridin-7-yl, imidazo[1,5-a]pyridin-6-yl, pyrazolo[4,3-b]pyridin-6-yl, 1H-pyrazolo[3,4-b]pyridin-5-yl, 1H-pyrazolo[3,4-b]pyridin-5-yl, 1H-pyrazolo[4,3-b]pyridin-5-yl, 1H-pyrazolo[4,3-b]pyridin-6-yl, 1H-thieno[2,3-c]pyrazol-5-yl, 1H-thieno[3,2-c]pyrazol-5-yl, thiazolo[5,4-b]pyridin-6-yl), each optionally substituted (e.g., substituted with 0, 1, 2 or 3 instances of $R^{10}$).

In some embodiments, each $R^6$ is independently selected from -Me, -$^{i}$Pr, -$^{n}$Bu, sec-Bu, cyclobutyl, cyclopentyl, cyclohexyl, bicyclo[1.1.1]pentan-1-yl, spiro[3.3]heptan-2-yl, 4,5,6,7-tetrahydro-1H-indazol-6-yl, piperidin-4-yl, piperidin-3-yl, pyrrolidin-3-yl, 1,2-dihydropyridin-4-yl, phenyl, naphthalen-2-yl, 1,2,3,4 tetrahydroquinolin-6-yl, 1,2,3,4-tetrahydronaphthalen-6-yl, chroman-6-yl, 1,5-naphthyridin-6-yl, 1,2,3,4-tetrahydro-1,8-naphthyridin-6-yl, 2,3-dihydro-1H-inden-5-yl, indolin-5-yl, indolin-4-yl, 2,3-dihydro-1H-benzo[d]imidazol-5-yl, 2,3-dihydrobenzofuran-5-yl, 2,3-dihydrobenzofuran-6-yl, benzo[d][1,3]dioxol-5-yl], isoindolin-5-yl, isoindolin-6-yl, 3,4-dihydro-2H-benzo[b][1,4]oxazin-7-yl, 1,2-dihydroquinolin-6-yl, 1,2-dihydroisoquinolin-7-yl, thiophen-2-yl, thiophen-3-yl, thiazol-2-yl, thiazol-4-yl, thiazol-5-yl, pyrazol-1-yl, pyrazol-5-yl, pyrazol-3-yl, pyrazol-4-yl, pyridin-2-yl, pyridin-3-yl, pyridin-4-yl, pyrimidin-5-yl, indol-4-yl, indol-5-yl, benzofuran-5-yl, benzofuran-6-yl, 1H indazol-5-yl, 1H indazol-4-yl, 2H-indazol-6-yl, 2H-indazol-5-yl, benzo[b]thiophen-3-yl, benzo[b]thiophen-5-yl, quinolin-6-yl, quinoline-3-yl, isoquinolin-6-yl, benzo[d]imidazo-5-yl, 1H-benzo[d]imidazol-4-yl, benzo[d]thiazol-5-yl, benzo[d]thiazol-6-yl, benzo[d]thiazol-4-yl, benzo[d]isothiazol-5-yl, benzo[d]oxazol-4-yl, benzo[d]oxazol-5-yl, [1,2,4]triazolo[4,3-a]pyridin-6-yl, imidazo[1,2-a]pyridin-6-yl, imidazo[1,2-a]pyridin-7-yl, imidazo[1,5-a]pyridin-6-yl, pyrazolo[4,3-b]pyridin-6-yl, 1H-pyrazolo[3,4-b]pyridin-5-yl, 1H-pyrazolo[3,4-b]pyridin-5-yl, 1H-pyrazolo[4,3-b]pyridin-5-yl, 1H-pyrazolo[4,3-b]pyridin-6-yl, 1H-thieno[2,3-c]pyrazol-5-yl, 1H-thieno[3,2-c]pyrazol-5-yl, thiazolo[5,4-b]pyridin-6-yl), each optionally substituted (e.g., substituted with 0, 1, 2 or 3 instances of $R^{10}$).

In some embodiments, $R^6$ is selected from optionally substituted phenyl, pyridin-2-yl, pyridin-3-yl, pyridin-4-yl, and pyrimidin-5-yl (e.g., substituted with 0, 1, 2 or 3 instances of $R^{10}$). In some embodiments, $R^6$ is selected from phenyl, pyridin-2-yl, pyridin-3-yl, pyridin-4-yl, pyrimidin-5-yl and phenyl substituted with one instance of $R^{10}$.

In some embodiments, $R^6$ is selected from:

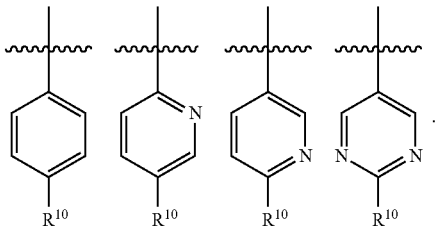

In further embodiments, $R^6$ is $R^6$ is

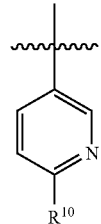

In some embodiments, $R^6$ is optionally substituted phenyl (e.g., substituted with 0, 1, 2 or 3 instances of $R^{10}$). In certain embodiments, $R^6$ is

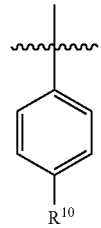

In some embodiments, $R^6$ is selected from optionally substituted bicyclic heteroaryl (e.g., substituted with 0, 1, 2 or 3 instances of $R^{10}$). In further embodiments, $R^6$ is selected from optionally substituted 1H-indazol-5-yl, 2H-indazol-5-yl, benzo[d]isothiazol-5-yl, benzo[d]thiazol-5-yl, benzo[b]thiophen-5-yl, benzo[d]oxazol-4-yl, benzo[d]oxazol-5-yl, quinoline-7-yl, 1H-thieno[2,3-c]pyrazol-5-yl, imidazo[1,2-a]pyridin-7-yl, and imidazo[1,5-a]pyridin-6-yl, (e.g., substituted with 0, 1, 2 or 3 instances of $R^{10}$).

In some embodiments, $R^6$ is

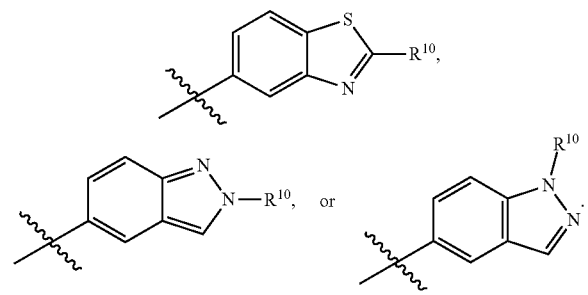

In further embodiments,

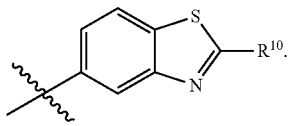

In certain embodiments of the invention, $R^{10}$ is independently selected from -D, =O, halo (e.g., F, Cl, Br), —CN, —$C_1$-$C_6$ alkyl (e.g., -Me, -Et, —Pr, -$^i$Pr, -sec-Bu, -$^t$Bu, $CH_2(CH_3)(^iPr)$), —$C_1$-$C_6$ heteroalkyl (e.g., —CH($CH_3$)(NMe$_2$), —CH$_2$CH$_2$N(Me)(oxetan-3-yl)), —CH$_2$CH(CH$_3$)(NMe$_2$), —CH$_2$OH, —CH(OH)(CH$_3$), —C(OH)(CH$_3$)$_2$, —CH$_2$NH$_2$), —$C_1$-$C_6$ haloalkyl (e.g., —CHF$_2$, —CH$_2$CF$_3$, —CF$_3$), —$C_3$-$C_9$ cycloalkyl (e.g., cyclopropyl, cyclobutyl, cyclopentyl, cyclohexyl), 3-10 membered heterocyclyl (e.g., tetrahydrofuranyl, tetrahydropyranyl, oxetanyl, morpholinyl, pyrolidinyl, piperidinyl, piperidin-2-onyl, piperazinyl, piperazin-2-only, azetidinyl, decahydro-1,6-naphthyridinyl, 2-azaspiro[3.3]heptanyl, 5-oxa-2,8-diazaspiro[3.5]nonanyl, 8-azabicyclo[3.2.1]octanyl, 2-azabicyclo[2.2.2]octanyl, 3-azabicyclo[3.2.0]heptanyl, 3-azabicyclo[3.1.1]heptanyl, 3-azabicyclo[3.1.0]hexanyl, 2-azabicyclo[2.1.1]hexanyl, 1-azabicyclo[2.2.1]heptanyl, 3-azabicyclo[3.2.0]heptanyl, 2,9-diazaspiro[5.5]undecanyl, bicyclo[1.1.1]pentanyl, octahydrocyclopenta[c]pyrrolyl, decahydro-1,6-naphthyridinyl, octahydro-1H-pyrrolo[3,4-c]pyridinyl, decahydro-2,7-naphthyridinyl, 2,9-diazaspiro[5.5]undecanyl), 5-10 membered heteroaryl (e.g., pyridinyl, imidazo[1,2-a]pyridinyl, imidazolyl, pyrazolyl, thiazolyl, thiophenyl), cycloalkylalkyl (e.g. —CH$_2$-cyclopropyl), heterocyclylalkyl (e.g., —CH$_2$-morpholinyl, —(CH$_2$)$_2$-pyrolidinyl-(CH$_2$)$_2$-pyrolidinyl-CH$_2$-imidazolyl, —CH$_2$-pyrazolyl, —CH$_2$-1,2,4-triazolyl, —CH$_2$-morpholinyl, —(CH$_2$)$_2$-morpholinyl), heterocyclylalkoxy (e.g., —O—(CH$_2$)$_2$-pyrolidinyl, —O—CH$_2$-piperidinyl, —O—CH$_2$-oxetanyl, —O—CH$_2$-tetrahydrofuranyl, —O—CH$_2$-tetrahydropyranyl), heteroarylalkyl (e.g., —CH$_2$-triazolyl, —CH$_2$-imidazolyl, —CH$_2$-pyrazolyl), —OR$^{b10}$ (e.g., —OH, —OMe, OEt, —O-tetrahydrofuranyl, —O-tetrahydropyran-4-yl, —OCF$_3$, —OCHF$_2$), —N(R$^{b10}$)$_2$, (e.g., —NH$_2$, —NHR$^{b10}$, —NHMe, —NMe$_2$, —NHCH$_2$CF$_3$, —NH-oxetan-3-yl, —NH—(N-Me-2-oxo-pyrolidin-3-yl), —NRb10C(=O)R$^{b10}$ (e.g., —NHC(=O)Me), —C(=O)N(R$^{b10}$)$_2$, (e.g., —C(=O)NH$_2$, C(=O)NHMe), —OC(=O)R$^{b10}$ (e.g., —OC(=O)Me), —S(=O)R$^{b10}$ (e.g., —SO$_2$Me), —NR$^{b10}$S(=O)$_2$R$^{b10}$ (e.g., NHSO$_2$Me) and —S(=O)$_2$N(R$^{b10}$)$_2$ (e.g., SO$_2$NH$_2$, SO$_2$NHMe), wherein each alkyl, cycloalkyl, heterocyclyl, aryl, heteroaryl, cycloalkylalkyl, heterocyclylalkyl, arylalkyl and heteroarylalkyl is optionally substituted (e.g., with 0, 1, 2,3,4, or 5 instances of -Me, -Et, -$^i$Pr, cyclopropyl, oxetan-3-yl, —OH, =O, —F, —OMe, —CH$_2$CH$_2$F, —CH$_2$CHF$_2$, —CH$_2$CH$_2$CF$_3$, —C(=O)Me, —N(Me)$_2$, —CH$_2$N(CH$_3$)$_2$, —CH$_2$N(CH$_3$)CH$_2$CH$_3$, —N($^i$Pr)(Et), —N($^i$Pr)(Me), —N(Et)$_2$, —N(CH$_3$)(Et), —NHC(=O)Me, or a combination thereof); and wherein:

each $R^{b10}$ is independently selected from H, —$C_1$-$C_6$ alkyl, (e.g., -Me, -Et, —Pr, -$^i$Pr, -sec-Bu, -$^t$Bu), —$C_1$-$C_6$ haloalkyl (e.g., —CF$_3$, —CHF$_2$, —CH$_2$CF$_3$), —$C_1$-$C_6$ heteroalkyl substituted with 0 or 1 instances of =O (e.g., —CH$_2$CH$_2$NMe$_2$, —CH$_2$C(=O)NMe$_2$, —CH(CH$_3$)CH$_2$NMe$_2$, —CH(CH$_3$)C(=O)NMe$_2$), $C_3$-$C_9$ cycloalkyl and 3-10 member heterocyclyl (e.g. tetrahydrofuran-3-yl, tetrahydropyran-4-yl, oxetan-3-yl, N-Me-2-oxo-pyrolidin-3-yl, piperidin-4-yl) substituted with 0 or 1 instances of =O, -Me or a combination thereof.

In certain embodiments, each $R^{b10}$ is independently selected from H, -Me, -Et, —Pr, -$^i$Pr, -sec-Bu, -$^t$Bu, —CF$_3$, —CHF$_2$, —CH$_2$CF$_3$, —CH$_2$CH$_2$NMe$_2$, —CH$_2$C(=O)NMe$_2$, —CH(CH$_3$)CH$_2$NMe$_2$, —CH(CH$_3$)C(=O)NMe$_2$), tetrahydrofuran-3-yl, tetrahydropyran-4-yl, oxetan-4-yl and N-Me-2-oxo-pyrolidin-3-yl.

In some embodiments, each $R^{10}$ is independently selected from the group consisting of -D, =O, —OH, —F, —Cl, —Br, —CN, -Me, -Et, —Pr, -$^i$Pr, -sec-Bu, -$^t$Bu, —OMe, —OEt, —CHF$_2$, —CH$_2$CF$_3$, —CF$_3$, —OCF$_3$, —OCHF$_2$, —CH$_2$OH, —CH(OH)(CH$_3$), —CH$_2$OMe, —C(OH)(CH$_3$)$_2$, —CH$_2$NH$_2$, —CH(CH$_3$)(NMe$_2$), —CH$_2$CH(CH$_3$)(NMe$_2$), —CH$_2$(CH$_3$)($^i$Pr), —NH$_2$, —NHMe, —NHCH$_2$CF$_3$, —NMe$_2$, cyclopropyl, cyclobutyl, cyclopentyl, cyclohexyl, thiazol-2-yl, thiazol-5-yl, thiophen-2-yl, tetrahydrofuran-3-yl, tetrahydropyran-4-yl, oxetan-3-yl, morpholin-2-yl, —CH$_2$-morpholin-4-yl, —(CH$_2$)$_2$-morpholin-4-yl, imidazol-2-yl, 1H-pyrazol-5-yl, 1H-imidazol-4-yl, imidazo[1,2-a]pyridin-7-yl, pyrolidin-1-yl, pyrolidin-3-yl, piperidin-4-yl, piperidin-3-yl, piperidin-2-one-4-yl, piperazin-4-yl, piperazin-4-yl, piperazin-2-on-5-yl pyridine-4-yl, pyridine-3-yl, pyrazol-1-yl, pyrazol-3-yl, pyrazol-4-yl, pyrazol-5-yl, 1H-pyrazol-5-yl, azetidin-3-yl, —(CH$_2$)$_2$-pyrolidin-1-yl-(CH$_2$)$_2$-pyrolidin-2-yl-CH$_2$-imidazol-1-yl, —CH$_2$-pyrazol-1-yl, —CH$_2$-1,2,4-triazol-1-yl, —CH$_2$-cyclopropyl, —O(CH$_2$)$_2$NMe$_2$, —O-tetrahydrofuran-3-yl, —O-tetrahydropyran-4-yl, —O—(N-Me-2-oxo-pyrolidin-3-yl), —O—(CH$_2$)$_2$-pyrolidin-2-yl-O—CH$_2$-piperidin-4-yl-O—CH$_2$-oxetan-3-yl, —NCH$_3$-piperidin-4-yl-NH-oxetan-3-yl, —NH—(N-Me-2-oxo-pyrolidin-3-yl), decahydro-1,6-naphthyridin-6-yl, 2-azaspiro[3.3]heptan-6-yl, 5-oxa-2,8-diazaspiro[3.5]nonan-8-yl, 8-azabicyclo[3.2.1]octan-3-yl, 2-azabicyclo[2.2.2]octan-4-yl, 3-azabicyclo[3.2.0]heptan-6-yl, 3-azabicyclo[3.1.1]heptan-1-yl, 3-azabicyclo[3.1.0]hexan-6-yl, 1-azabicyclo[2.2.1]heptan-4-yl, 3-azabicyclo[3.2.0]heptan-6-yl, 2-azabicyclo[2.1.1]hexan-4-yl, 2,9-diazaspiro[5.5]undecane-9-yl, bicyclo[1.1.1]pentan-2-yl, octahydrocyclopenta[c]pyrrol-5-yl, decahydro-1,6-naphthyridin-6-yl, octahydro-1H-pyrrolo[3,4-c]pyridine-5-yl, decahydro-2,7-naphthyridin-2-yl, 2,9-diazaspiro[5.5]undecan-2-yl, —NHC(=O)Me, —NHCH$_2$C(=O)NMe$_2$, —NHCH(CH$_3$)C(=O)NMe$_2$, —C(=O)NH$_2$, C(=O)NHMe, —OC(=O)Me, —SO$_2$Me, —NHSO$_2$Me, —SO$_2$NH$_2$ and —SO$_2$NHMe, wherein each —OMe, —OEt, -Me, -Et, —Pr, -$^i$Pr, cyclopropyl, cyclobutyl, cyclopentyl, cyclohexyl, tetrahydrofuran-3-yl, oxetan-3-yl, pyrolidin-1-yl, pyrolidin-3-yl, piperidin-4-yl, piperidin-3-yl, piperidin-2-one-4-yl piperazin-4-yl, pyrazol-1-yl, pyrazol-3-yl, pyrazol-4-yl, pyrazol-5-yl, thiazol-2-yl, thiophen-2-yl, —CH$_2$-cyclopropyl, —CH$_2$-morpholin-4-yl, —(CH$_2$)$_2$-morpholin-4-yl, -morpholin-2-yl, —(CH$_2$)$_2$-pyrolidin-1-yl, —CH$_2$-1,2,4-triazol-1-yl-CH$_2$-imidazol-1-yl, imidazol-2-yl, —CH$_2$-pyrazol-1-yl, —OCH$_2$-piperidin-4-yl, azetidin-3-yl, 2-azaspiro[3.3]heptan-6-yl, 2-methyl-5-oxa-2,8-diazaspiro[3.5]nonan-8-yl, 8-azabicyclo[3.2.1]octan-3-yl, and decahydro-1,6-naphthyridin-6-yl; and wherein each $R^{10}$ can be independently substituted with 0, 1, 2, 3, 4, or 5 instances of -Me, -Et, -$^i$Pr, cyclopropyl, oxetan-3-yl, —OH, =O, —F, —OMe, —CH$_2$CH$_2$F, —CH$_2$CHF$_2$, —CH$_2$CH$_2$CF$_3$, —C(=O)Me, —N(Me)$_2$, —CH$_2$N(CH$_3$)$_2$, —CH$_2$N(CH$_3$)CH$_2$CH$_3$, —N($^i$Pr)(Et), —N($^i$Pr)(Me), —N(Et)$_2$, —N(CH$_3$)(Et), —NHC(=O)Me, or a combination thereof.

In some embodiments, $R^{10}$ is optionally substituted 3-6 membered monocyclic heterocyclyl or optionally substituted 6-10 membered bicyclic heterocyclyl. In further embodiments, $R^{10}$ is -D, —Cl, —F, -Me, —CH$_2$—OH,
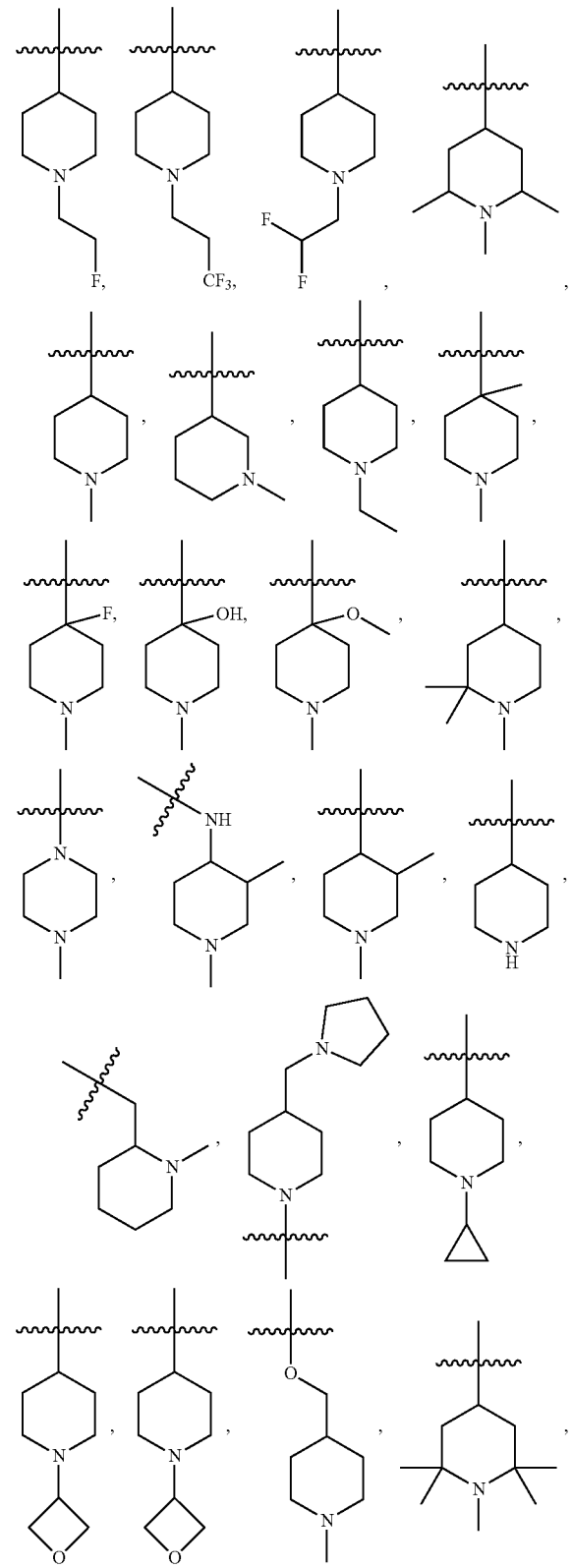
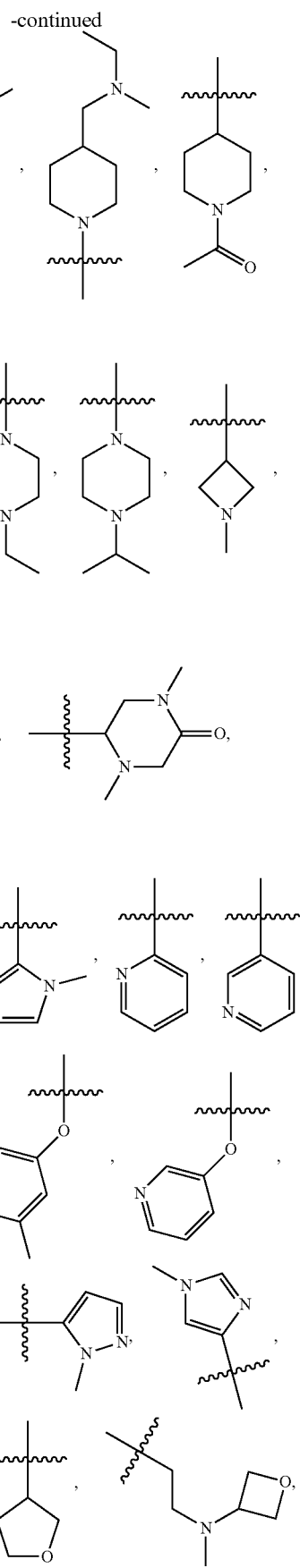

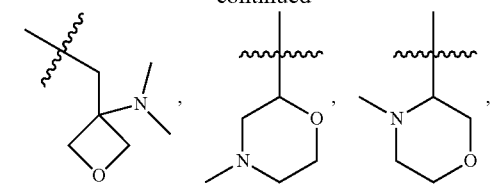
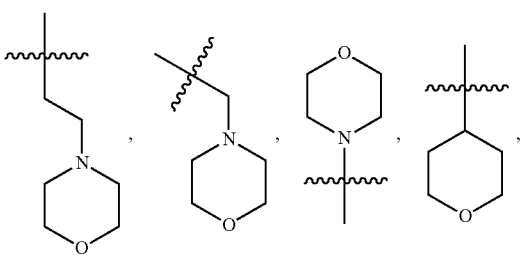
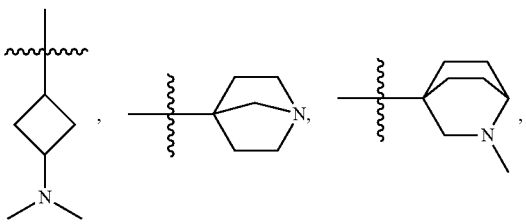
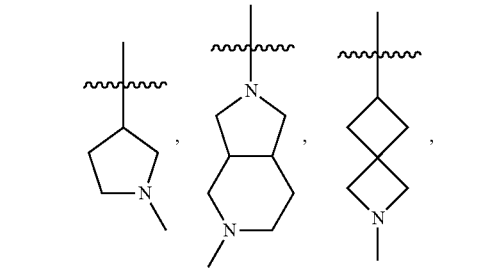
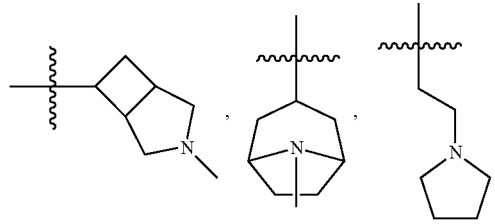
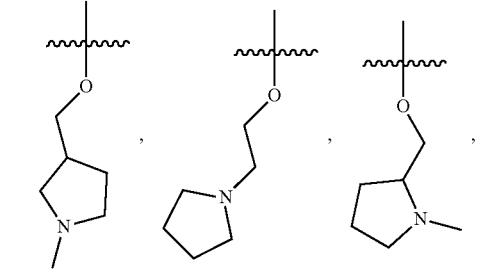
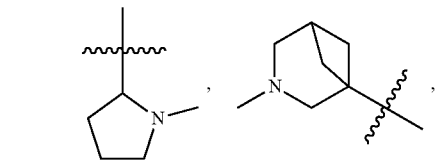
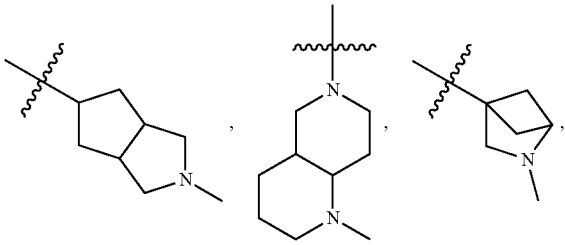
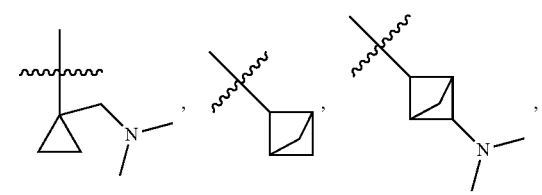
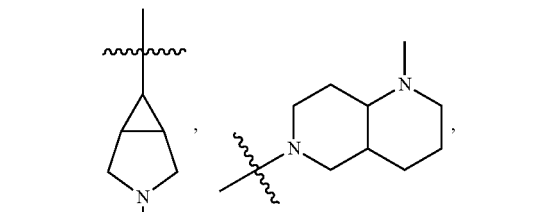
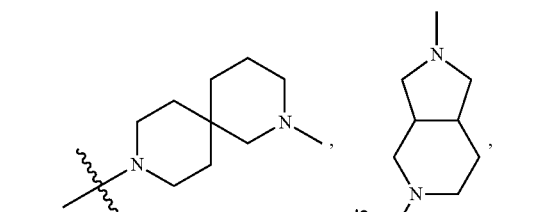
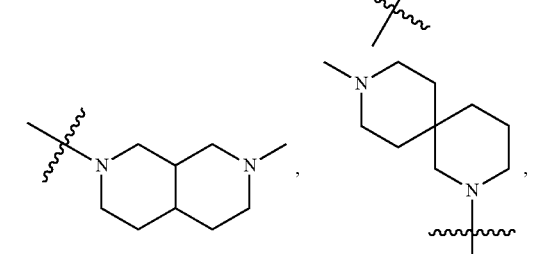
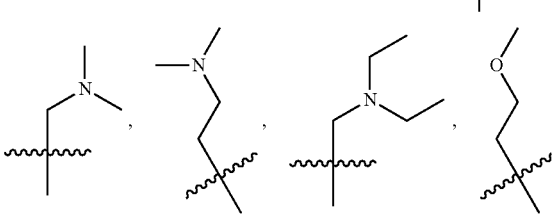
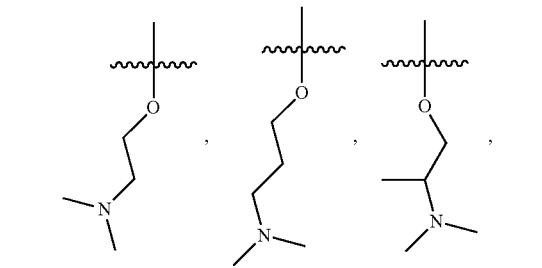

-continued

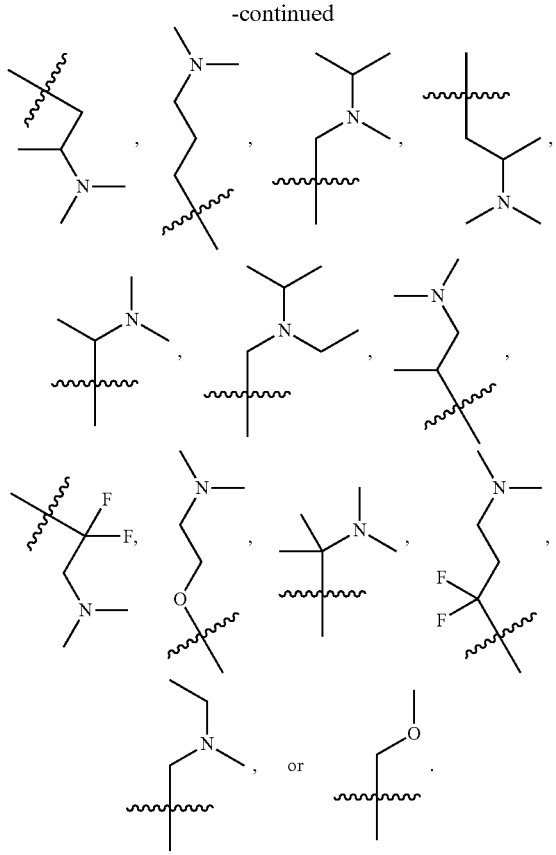

In some embodiments of Formula (I), (Ia), (Ib), (Ic) and (Id), n is 0. In other embodiments, n is 1. In certain embodiments, n is 2. In other embodiments, n is 3. In some embodiments of Formula (I), (Ia), (Ib), (Ic) and (Id), the moiety represented as

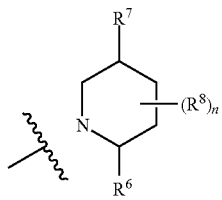

is selected from:

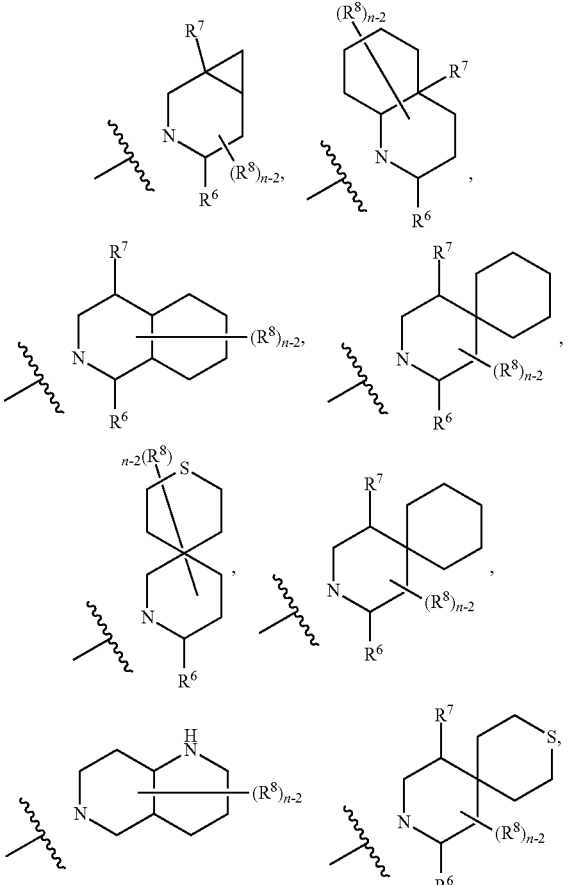

In some embodiments of Formula (I), (Ia), (Ib), (Ic) and (Id), each $R^7$ is independently selected from H, halo (e.g., F, Cl), —CN, —$C_1$-$C_6$ alkyl (e.g., -Me, -Et, —Pr, -$^i$Pr, -sec-Bu, -$^t$Bu), 5-membered heteroaryl (e.g., pyrazolyl), —$C_1$-$C_6$ haloalkyl (e.g., —$CF_3$, —$CHF_2$, —$CH_2CF_3$), —$C_1$-$C_6$ hydroxyalkyl (e.g., —$CH_2OH$), —$C_3$-$C_9$ cycloalkyl (e.g., cyclopropyl, cyclobutyl, cyclopentyl, cyclohexyl), —$OR^{a7}$ (e.g., —OH, —OMe, —$OCHF_2$), —$N(R^{a7})_2$ and —C(=O)$N(R^{a7})_2$ (e.g., —C(=O)$NH_2$, —C(=O)NHMe). In further embodiments, each $R^{a7}$ is independently selected from H and —$C_1$-$C_6$ alkyl (e.g., -Me, -Et, —Pr, -$^i$Pr, -$^n$Bu, -$^i$Bu, -sec-Bu, -iso-Bu). In some embodiments, each $R^7$ is independently selected from H and methyl. In certain embodiments, each $R^7$ is H. In other embodiments, each $R^7$ is methyl.

In some embodiments of Formula (I), (Ia), (Ib), (Ic) and (Id), each $R^8$ is independently selected from H, -D, halo (e.g., —F, —Cl), —CN, —$C_1$-$C_6$ alkyl (e.g., -Me, -Et, —Pr, -$^i$Pr, -sec-Bu, -$^t$Bu), arylalkyl, (e.g., benzyl), —C(=O)$R^{a8}$ (e.g., —C(=O)Me, —C(=O)Et, —C(=O)Pr, —C(=O)$^i$Pr), —$N(R^{a8})_2$ (e.g., —NHMe, $NH_2$, $NMe_2$), —$NR^{a8}$C(=O)$R^{a8}$ (e.g., —NHC(=O)Me), —$CH_2$C(=O)$N(R^{a8})_2$ (e.g., —$CH_2$C(=O)$NH_2$) and —$OR^{a8}$ (e.g., —OH, —OMe, —$O^i$Pr, —$OCF_3$). In further embodiments, each $R^{a8}$ is independently selected from H, —$CF_3$, and —$C_1$-$C_6$ alkyl (e.g., -Me, -Et, —Pr, -$^i$Pr, -$^n$Bu, -$^t$Bu, -sec-Bu, -iso-Bu). In some embodiments, each $R^8$ is independently selected from H, -D, —F, -Me, -Et, —CN, —OMe, —$O^i$Pr, —$OFC_3$, benzyl, —NHC(=O)Me, —$NMe_2$, —$CH_2$C(=O)$NH_2$, —C(=O)$^i$Pr and —OH. In certain embodiments, each $R^8$ is independently selected from H, -D, —F, -Me, -Et and —CN. In further embodiments, each $R^8$ is independently selected from H, -D, —F and -Me.

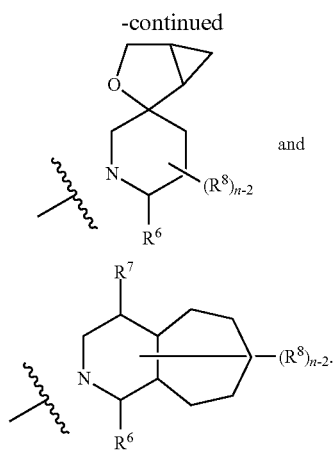
and
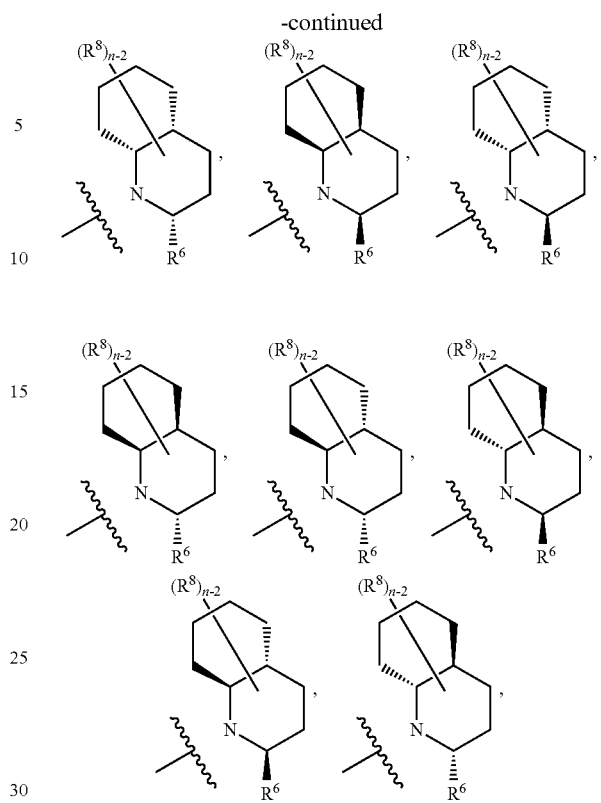
In some embodiments of Formula (I), (Ia), (Ib), (Ic) and (Id), the moiety represented as
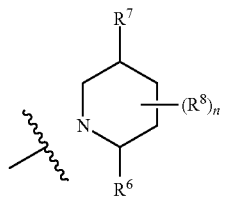
is selected from.
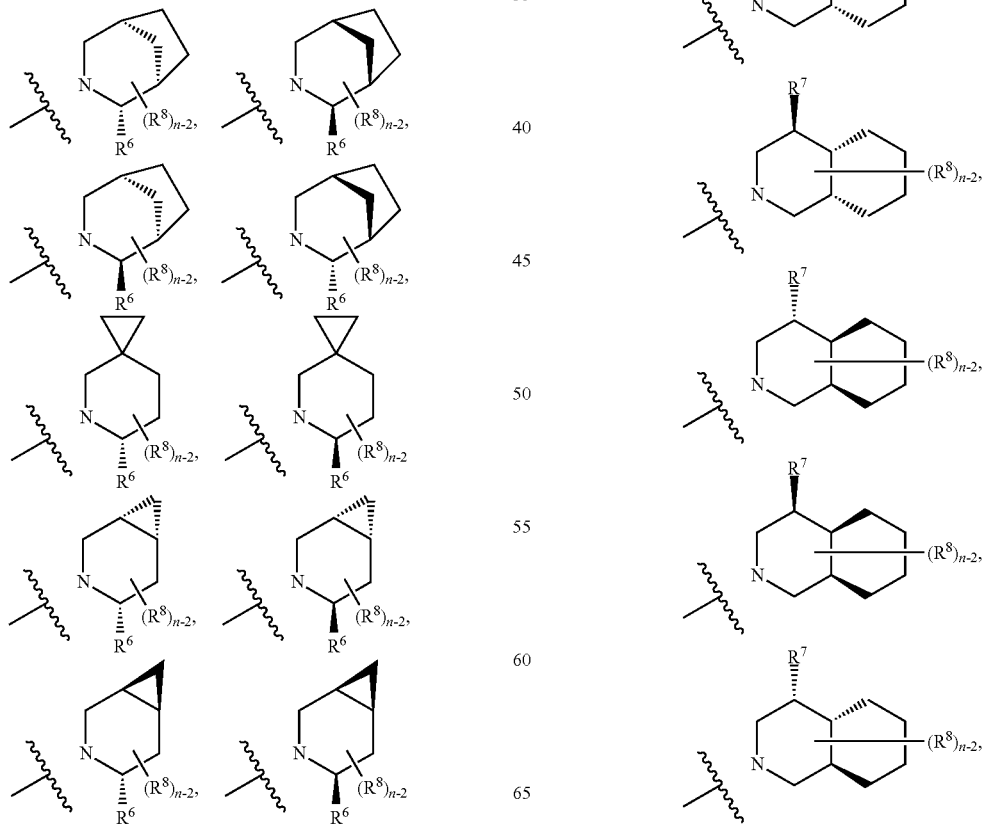

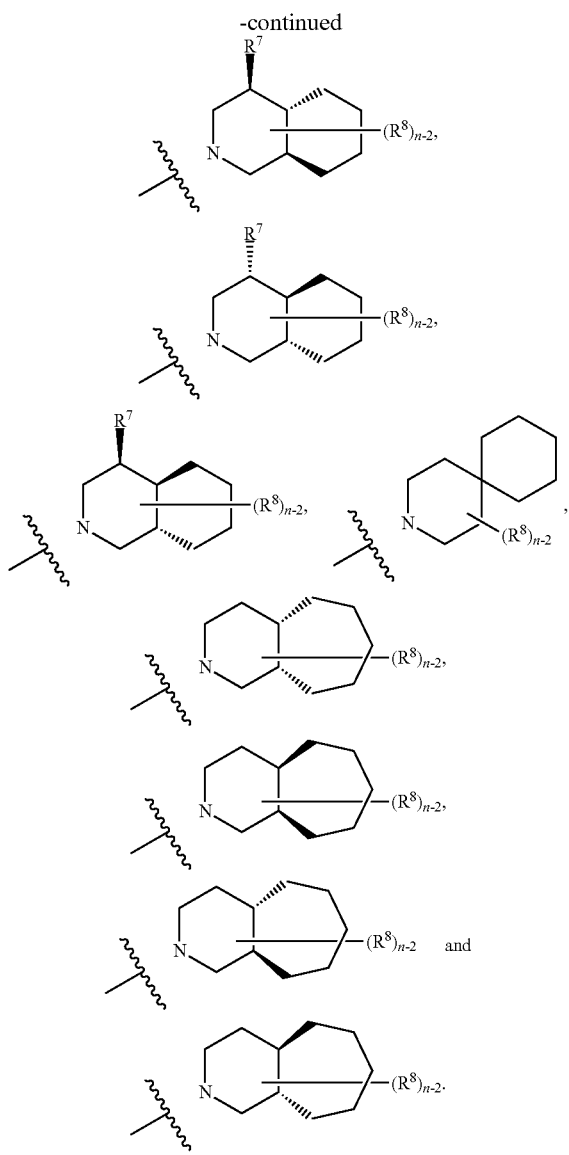

In some of the above embodiments wherein the piperidine is part of a larger ring, n is 2. In some embodiments, each $R^6$ and $R^7$ is independently selected from H and —$CH_3$. In further embodiments, $R^6$ is H. In other embodiments, $R^6$ is —$CH_3$. In certain embodiments, $R^7$ is H. In certain embodiments, $R^7$ is —$CH_3$.

In some embodiments, the compounds of Formula (I), (Ia), (Ib), (Ic) and (Id) are selected from Table 1.

In one aspect, provided is a pharmaceutical composition comprising a compound of Formula (I), (Ia), (Ib), (Ic) and (Id) as defined herein and a pharmaceutically acceptable carrier. In some embodiments, the pharmaceutical composition further comprises a second therapeutic agent.

In one aspect, provided is a method of treating an MTAP-deficient and/or an MTA-accumulating disease in a subject in need thereof by administering to the subject a therapeutically effective amount of a c or a pharmaceutically acceptable composition thereof. In some embodiments, the compound or composition is administered in combination with a second therapeutic agent.

In some embodiments, the disease is a proliferating disease. In one embodiment, the disease is an MTAP-deficient and/or MTA-accumulating cancer. In certain embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one aspect, provided is a method of treating a cancer in a subject in need thereof comprising the steps of:
a) assessing the level of MTAP and/or MTA in a test sample obtained from said subject, wherein the MTA level can be assessed directly (e.g., by ELISA or LC-MS/MS) or indirectly (e.g., by SDMA-modified protein ELISA or IHC, or by RNA splicing);
b) comparing the test sample with a reference, wherein MTAP deficiency and/or MTA accumulation in said test sample compared to the reference indicates the cancer in said subject will respond to therapeutic treatment with a PRMT5 inhibitor; and
c) administering a therapeutically effective amount of a compound of Formula (I), (Ia), (Ib), (Ic) and (Id) as defined herein or a pharmaceutical composition thereof to the subject identified in step b).

DEFINITIONS

MTAP

"MTAP" as used herein refers to methylthioadenosine phosphorylase, an enzyme in the methionine salvage pathway, also known as S-methyl-5'-thioadenosine phosphorylase; also known as BDMF; DMSFH; DMSMFH; LGMBF; MSAP; and c86fus. External IDs: OMIM: 156540 MGI: 1914152 HomoloGene: 1838 chEMBL: 4941 GeneCards: MTAP Gene; Entrez 4507; RefSeq (mRNA): NM_002451; location: Chr 9: 21.8-21.93 Mb. By "wild-type" MTAP is meant that encoded by NM_002451 or having the same amino acid sequence (NP_002442). (Schmid et al. *Oncogene* 2000, 19, pp 5747-54).

As used herein, the term "MTAP-deficient", "MTAP-deficiency", "MTAP-null" and the like refer to cells (including, but not limited to, cancer cells, cell lines, tissues, tissue types, tumors, etc.) that have a significant reduction in post-translational modification, production, expression, level, stability and/or activity of MTAP relative to that in a control, e.g., reference or normal or non-cancerous cells. The reduction can be at least about 20%, 30%, 40%, 50%, 60%, 70%, 80% or 90%. In some embodiments, the reduction is at least 20%. In some embodiments, the reduction is at least 50%. The terms "MTAP-deficient and/or MTA accumulating", "MTAP-deficient and/or MTA-accumulating", MTAP deficient and/or MTA upregulated" and the like, regarding a cell or cells, etc., indicate that the cell or cells, etc., either are deficient in MTAP and/or overproduce or accumulate MTA. MTAP-deficient cells include those wherein the MTAP gene has been mutated, deleted, or transcriptionally silenced. As a non-limiting example, MTAP-deficient cells can have a homozygous deletion. MTAP knockdown is not lethal. In some embodiments, the MTAP-deficient cells are also CDKN2A-deficient. The MTAP deficiency can be detected using any reagent or technique known in the art, for example: immunohistochemistry utilizing an antibody to MTAP, and/or genomic sequencing, and/or nucleic acid hybridization and/or amplification utilizing at least one probe or primer comprising a sequence of at least 12 contiguous nucleotides (nt) of the sequence of MTAP, wherein the primer is no longer than about 30 nt.

Figure 1:
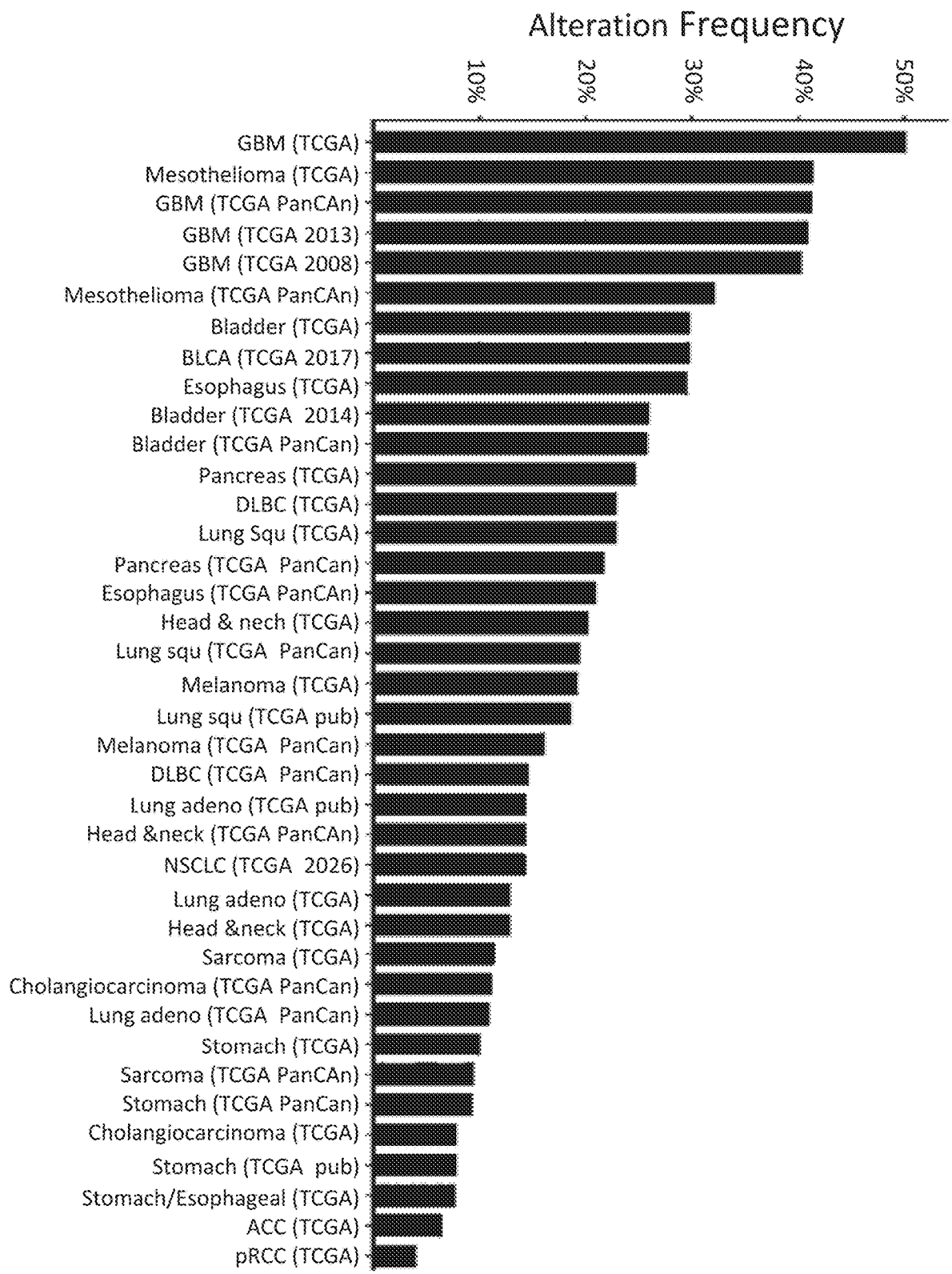
FIG. 1. Frequency of MTAP homozygous deletion in cell lines representing exemplary cancers according to The Cancer Genome Atlas (TCGA).

An "MTAP-deficiency-related" or "MTAP-deficiency" or "MTAP deficient" disease (for example, a proliferating disease, e.g., a cancer) or a disease (for example, a proliferating disease, e.g., a cancer) "associated with MTAP deficiency" or a disease (for example, a proliferating disease, e.g., a cancer) "characterized by MTAP deficiency" and the like refer to an ailment (for example, a proliferating disease, e.g., a cancer) wherein a significant number of cells are MTAP-deficient. For example, in a MTAP-deficiency-related disease, one or more disease cells can have a significantly reduced post-translational modification, production, expression, level, stability and/or activity of MTAP. Examples of MTAP-deficiency-related diseases include, but are not limited to, cancers, including but not limited to: glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma (See FIG. 1). In a patient afflicted with a MTAP-deficiency-related disease, it is possible that some disease cells (e.g., cancer cells) can be MTAP-deficient while others are not. Similarly, some disease cells may be MTA-accumulating while others are not. Thus, the present disclosure encompasses methods of treatment involving diseases of these tissues, or any other tissues, wherein the proliferation of MTAP-deficient and/or MTA-accumulating cells can be inhibited by administration of a PRMT5 inhibitor. Some cancer cells which are MTAP-deficient are also deficient in CDKN2A; the post-translational modification, production, expression, level, stability and/or activity of the CDKN2A gene or its product are decreased in these cells. The genes for MTAP and CDKN2A are in close proximity on chromosome 9p21; MTAP is located approximately 100 kb telomeric to CDKN2A.

Many cancer cell types harbor CDKN2A/MTAP loss (loss of both genes). Thus, in some embodiments, a MTAP-deficient cell is also deficient in CDKN2A.

MTA and MTA Accumulation

By "MTA" is meant the PRMT5 inhibitor also known as methyl-thioadenosine, S-methyl-5'-thioadenosine, [5'deoxy-5'-(methylthio)-f1-D-ribofuranosyl]adenine, 5'-methyl-thio-adenosine, 5'-deoxy, 5'-methyl thioadenosine, and the like. MTA selectively inhibits PRMT5 methyltransferase activity. MTA is the sole known catabolic substrate for MTAP. The terms "MTA accumulating", "MTA overproducing", "MTA upregulated" and the like refer to cells (including, but not limited to, cancer cells, cell lines, tissues, tissue types, tumors, etc.) that have a significantly increased production, level and/or stability of MTA. MTA-accumulating cells include those wherein the cells comprise at least about 20%, 30%, 40%, 50%, 60%, 70%, 80%, 90%, 100%, or greater than 100%, higher production, level and/or stability of MTA than that in normal or non-cancerous cells. In some embodiments, MTA-accumulating cells include those wherein the cells comprise at least 20% higher production, level and/or stability of MTA than that in normal or non-cancerous cells. In some embodiments, MTA-accumulating cells include those wherein the cells comprise at least 50% higher production, level and/or stability of MTA than that in normal or non-cancerous cells. Determination of MTA accumulation in test samples (e.g., cells such as cancer cells being tested for MTA accumulation) and reference samples, and other cells, tissues, samples, etc., can be performed using any method known in the art. Such methods for detecting MTA include, as a non-limiting example, liquid chromatography-electrospray ionization-tandem mass spectrometry (LC-ESI-MS/MS), as described in Stevens et al. *J. Chromatogr. A.* 2010, 1217, pp 3282-3288; and Kirovski et al. *Am. J. Pathol.* 2011, 178, pp 1145-1152; and references cited therein. Loss of MTAP is associated with accumulation of MTA (Williams-Ashman et al. *Biochem. Pharm.* 1982,31, pp 277-288; and Limm et al. *Eur. J. Cancer.* 2013, 49, Issue 6.

An "MTA-accumulation-related", "MTA-accumulation", "MTA-accumulating", "MTA overproducing", "MTA upregulated" disease (for example, a proliferating disease, e.g., a cancer) or a disease (for example, a proliferating disease, e.g., a cancer) "associated with MTA accumulation" or a disease (for example, a proliferating disease, e.g., a cancer) "characterized by MTA accumulation" and the like refer to an ailment (for example, a proliferating disease, e.g., a cancer) wherein a significant number of cells are MTA accumulating. Examples of MTA-accumulating diseases include, but are not limited to, cancers, including but not limited to: glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma (See FIG. 1). In a patient afflicted with a MTAP-deficiency-related disease, it is possible that some disease cells (e.g., cancer cells) can be MTAP-deficient while others are not.

In a patient having or having been diagnosed with an MTA-accumulating disease, some cells may be MTA-accumulating while others are not.

An increase in therapeutic window between normal cells and MTAP-deleted/MTA accumulating cells could be achieved by using an inhibitor that binds PRMT5 uncompetitively with MTA. As used herein, "uncompetitive binding" and "uncompetitive inhibition" and "cooperative binding" and "cooperative inhibition" (e.g., MTA-uncompetitive binding, MTA-uncompetitive inhibition, MTA-cooperative binding, MTA-cooperative inhibition) refers to binding of an inhibitor to a protein (e.g., PRMT5) that is increased in the presence of a co-factor (e.g., MTA) over the binding of the same inhibitor in the absence of the co-factor. The PRMT5 inhibitors known in the art are generally either SAM (S-adenosylmethionine) uncompetitive or SAM competitive. As the concentration of SAM in wild-type and MTAP-null cells is similar, these inhibitors are expected to bind with similar potency to both cell types. By contrast, an MTA-cooperative (and either SAM competitive or showing enhanced cooperativity with MTA relative to SAM) inhibitor would bind with apparent greater potency in the presence of high concentrations of MTA and would therefore result in preferential inhibition of PRMT5 in MTA-accumulating cells relative to normal cells.

As described further herein, a cancer cell, a cancer type, or a subject with cancer, is "PRMT5 inhibitor sensitive," sensitive to treatment with PRMT5 inhibitors," sensitive to PRMT5 therapeutic inhibition," or described in similar terms if it is amenable to treatment with a PRMT5 inhibitor, e.g., due to its MTAP deficiency and/or MTA accumulation character.

PRMT5

"PRMT5" as used herein is the gene or protein Protein Arginine Methyltransferase 5, also known as HRMT1L5; IBP72; JBP1; SKB1; or SKB1Hs External IDs: OMIM: 604045, MGI: 1351645, HomoloGene: 4454, ChEMBL: 1795116, GeneCards: PRMT5 Gene; EC number 2.1.1.125. Ensembl ENSG00000100462; UniProt O14744; Entrez Gene ID: 10419; RefSeq (mRNA): NM_001039619. The mouse homolog is NM_013768.

Methyltransferases such as PRMT5 catalyze the transfer of one to three methyl groups from the co-factor S-adenosylmethionine (also known as SAM or AdoMet) to lysine or arginine residues of histone proteins. Arginine methylation is carried out by 9 different protein arginine methyltransferases (PRMT) in humans. Three types of methylarginine species exist: (1) Monomethylarginine (MMA); (2) Asymmetric dimethyl arginine (ADMA), which is produced by Type I methyl transferases (PRMT1, PRMT2, PRMT3, CARM1, PRMT6 and PRMT8); and (3) Symmetrical dimethylarginine (SDMA), which is produced by Type II methyl transferases (PRMT5 and PRMT7). PRMT1 and PRMT5 are the major asymmetric and symmetric arginine methyltransferases, respectively. PRMT5 promotes symmetric dimethylation on histones at H3R8 and H4R3 (H4R3me2). Symmetric methylation of H4R3 is associated with transcriptional repression and can act as a binding site for DNMT3A. Loss of PRMT5 results in reduced DNMT3A binding and gene activation. Tumor suppressor gene ST7 and chemokines RNATES, IP10, CXCL11 are targeted and silenced by PRMT5. WO 2011/079236.

Additional substrates include E2F1, p53, EGFR and CRAF. PRMT5 is part of a multi-protein complex comprising the co-regulatory factor WDR77 (also known as MEP50, a CDK4 substrate) during G1/S transition. Phosphorylation increases PRMT5/WDR77 activity. WDR77 is the non-catalytic component of the complex and mediates interactions with binding partners and substrates. PRMT5 can also interact with pICln or $RioK_1$ adaptor proteins in a mutually exclusive fashion to modulate complex composition and substrate specificity.

PRMT5 has either a positive or negative effect on its substrates by arginine methylation when interacting with a number of complexes and is involved in a variety of cellular processes, including RNA processing, signal transduction, transcriptional regulation, and germ cell development. PRMT5 is a major pro-survival factor regulating eIF4E expression and p53 translation. PRMT5 triggers p53-dependent apoptosis and sensitized various cancer cells to Tumor necrosis factor (TNF)-related apoptosis-inducing ligand (TRAIL) without affecting TRAIL resistance in non-transformed cells.

The term "PRMT5 inhibitor" refers to any compound capable of inhibiting the production, level, activity, expression or presence of PRMT5. These include, as non-limiting examples, any compound inhibiting the transcription of the gene, the maturation of RNA, the translation of mRNA, the posttranslational modification of the protein, the enzymatic activity of the protein, the interaction of same with a substrate, etc. The term also refers to any agent that inhibits the cellular function of the PRMT5 protein, either by ATP-competitive inhibition of the active site, allosteric modulation of the protein structure, disruption of protein-protein interactions, or by inhibiting the transcription, translation, post-translational modification, or stability of PRMT5 protein.

In some embodiments, a PRMT5 inhibitor competes with another compound, protein or other molecule which interacts with PRMT5 and is necessary for PRMT5 function.

As a non-limiting example, a PRMT5 inhibitor can compete with the co-factor S-adenosylmethionine (also known as SAM or AdoMet).

In some embodiments, the PRMT5 inhibitor is uncompetitive with MTA. In further embodiments, the PRMT5 inhibitor is uncompetitive with MTA and competitive with SAM.

In some embodiments, the PRMT5 inhibitor is uncompetitive with MTA and uncompetitive with SAM but binds with a higher degree of potency for the MTA complex relative to the SAM complex.

Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

The "enantiomeric excess" ("e.e.") or "% enantiomeric excess" ("% e.e.") of a composition as used herein refers to an excess of one enantiomer relative to the other enantiomer present in the composition. For example, a composition can contain 90% of one enantiomer, e.g., the S enantiomer, and 10% of the other enantiomer, i.e., the R enantiomer.

$$e.e.=(90-10)/100=80\%.$$

Thus, a composition containing 90% of one enantiomer and 10% of the other enantiomer is said to have an enantiomeric excess of 80%.

The "diastereomeric excess" ("d.e.") or "% diastereomeric excess" ("% d.e.") of a composition as used herein refers to an excess of one diastereomer relative to one or more different diastereomers present in the composition. For example, a composition can contain 90% of one diastereomer, and 10% of one or more different diastereomers.

$$d.e.=(90-10)/100=80\%.$$

Thus, a composition containing 90% of one diastereomers and 10% of one or more different diastereomers is said to have a diastereomeric excess of 80%.

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, 180; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

In a formula, ⁓ is a single bond where the stereochemistry of the moieties immediately attached thereto is not specified.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

The term "azido" refers to the radical —$N_3$.

"Aliphatic" refers to an alkyl, alkenyl, alkynyl, or carbocyclyl group, as defined herein.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Aralkyl" or "arylalkyl" is a subset of alkyl and aryl, as defined herein, and refers to an optionally substituted alkyl group substituted by an optionally substituted aryl group.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_8$), amyl ($C_8$), neopentyl ($C_8$), 3-methyl-2-butanyl ($C_8$), tertiary amyl ($C_8$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), $^iPr$(—$CH(CH_3)_2$), $^nPr$(—$CH_2CH_2CH_3$), $^nBu$ (—$CH_2CH_2CH_2CH_3$), or $^iBu$ (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl(methyl) groups, include but are not limited to, substituted methylene (—$CH(CH_3)$—, (—$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2,3, or 4 carbon-carbon double bonds), and optionally one or more carbon-carbon triple bonds (e.g., 1, 2,3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_8$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2,3, or 4 carbon-carbon triple bonds), and optionally one or more carbon-carbon double bonds (e.g., 1, 2,3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2,3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl. Exemplary heteroalkyl groups include: —CH$_2$OH, —CH$_2$OCH$_3$, —CH$_2$NH$_2$, —CH$_2$NH(CH$_3$), —CH$_2$N(CH$_3$)$_2$, —CH$_2$CH$_2$OH, —CH$_2$CH$_2$OCH$_3$, —CH$_2$CH$_2$NH$_2$, —CH$_2$CH$_2$NH(CH$_3$), —CH$_2$CH$_2$N(CH$_3$)$_2$.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group is substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

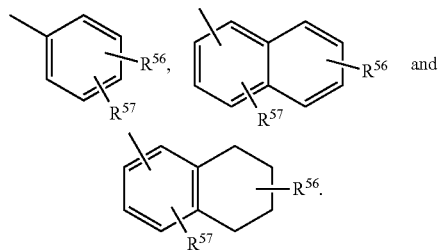

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl. "Fused aryl" refers to an aryl having two of its ring carbons in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl. In some embodiments, a heteroaryl group is a bicyclic 8-12 membered aromatic ring system having ring carbon atoms and 1-6 ring heteroatoms provided in the aromatic ring system, wherein each heteroatom is independently selected from nitrogen, oxygen, and sulfur ("8-12 membered bicyclic heteroaryl"). In some embodiments, a heteroaryl group is an 8-10 membered bicyclic aromatic ring system having ring carbon atoms and 1-6 ring heteroatoms provided in the aromatic ring system, wherein each heteroatom is independently selected from nitrogen, oxygen, and sulfur ("8-10 membered bicyclic heteroaryl"). In some embodiments, a heteroaryl group is a 9-10 membered bicyclic aromatic ring system having ring carbon atoms and 1-6 ring heteroatoms provided in the aromatic ring system, wherein each heteroatom is independently selected from nitrogen, oxygen, and sulfur ("9-10 membered bicyclic heteroaryl"). Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

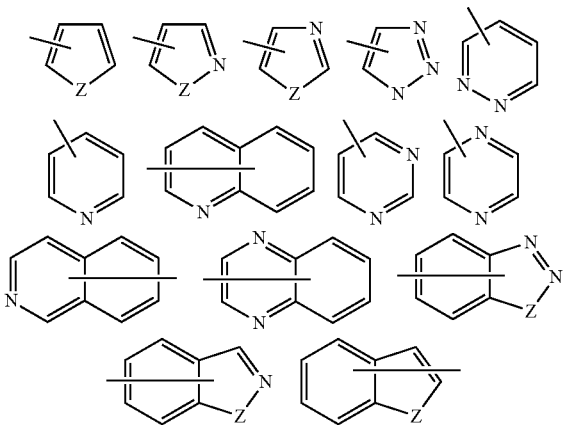

wherein each Z is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

In the structures described herein, a substituent attached to a polycyclic (e.g., bicyclic or tricyclic)cycloalkyl, heterocyclyl, aryl or heteroaryl with a bond that spans two or more rings is understood to mean that the substituent can be attached at any position in each of the rings. "Heteroaralkyl" or "heteroarylalkyl" is a subset of "alkyl" and refers to an alkyl group substituted by a heteroaryl group, wherein the point of attachment is on the alkyl moiety. The term "carbocyclyl" or "carbocyclic" refers to a radical of a non-aromatic monocyclic, bicyclic, or tricyclic or polycyclic hydrocarbon ring system having from 3 to 14 ring carbon atoms ("$C_{3-14}$ carbocyclyl") and zero heteroatoms in the non-aromatic ring system. Carbocyclyl groups include fully saturated ring systems (e.g., cycloalkyls), and partially saturated ring systems. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like.

As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

The term "cycloalkyl" as employed herein includes saturated cyclic, bicyclic, tricyclic, or polycyclic hydrocarbon groups having 3 to 14 carbons containing the indicated number of rings and carbon atoms (for example a $C_3$-$C_{14}$ monocyclic, $C_4$-$C_{14}$ bicyclic, $C_5$-$C_{14}$ tricyclic, or $C_6$-$C_{14}$ polycyclic cycloalkyl). In some embodiments "cycloalkyl" is a monocyclic cycloalkyl. In some embodiments, a monocyclic cycloalkyl has 3-14 ring carbon atoms. ("$C_{3-14}$ monocyclic cycloalkyl"). In some embodiments, a monocyclic cycloalkyl group has 3 to 10 ring carbon atoms ("$C_{3-10}$ monocyclic cycloalkyl"). In some embodiments, a monocyclic cycloalkyl group has 3 to 8 ring carbon atoms ("$C_{3-8}$ monocyclic cycloalkyl"). In some embodiments, a monocyclic cycloalkyl group has 3 to 6 ring carbon atoms ("$C_{3-6}$ monocyclic cycloalkyl"). In some embodiments, a monocyclic cycloalkyl group has 4 to 6 ring carbon atoms ("$C_{4-6}$ monocyclic cycloalkyl"). In some embodiments, a monocyclic cycloalkyl group has 5 to 6 ring carbon atoms ("$C_{5-6}$ monocyclic cycloalkyl"). In some embodiments, a monocyclic cycloalkyl group has 5 to 10 ring carbon atoms ("$C_{5-10}$ monocyclic cycloalkyl"). Examples of monocyclic $C_{5-6}$ cycloalkyl groups include cyclopentyl ($C_5$) and cyclohexyl ($C_8$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$).

In some embodiments "cycloalkyl" is a bicyclic cycloalkyl. In some embodiments, a bicyclic cycloalkyl has 4-14 ring carbon atoms. ("$C_{4-14}$ bicyclic cycloalkyl"). In some embodiments, a bicyclic cycloalkyl group has 4 to 12 ring carbon atoms ("$C_{4-12}$ bicyclic cycloalkyl"). In some embodiments, a bicyclic cycloalkyl group has 4 to 10 ring carbon atoms ("$C_{4-10}$ bicyclic cycloalkyl"). In some embodiments, a bicyclic cycloalkyl group has 5 to 10 ring carbon atoms ("$C_{5-10}$ bicyclic cycloalkyl"). In some embodiments, a bicyclic cycloalkyl group has 6 to 10 ring carbon atoms ("$C_{6-10}$ bicyclic cycloalkyl"). In some embodiments, a bicyclic cycloalkyl group has 8 to 10 ring carbon atoms ("$C_{8-10}$ bicyclic cycloalkyl"). In some embodiments, a bicyclic cycloalkyl group has 7 to 9 ring carbon atoms ("$C_{7-9}$ bicyclic cycloalkyl"). Examples of bicyclic cycloalkyls include bicyclo[1.1.0]butane ($C_4$), bicyclo[1.1.1]pentane ($C_5$), spiro[2.2]pentane ($C_5$), bicyclo[2.1.0]pentane ($C_8$), bicyclo[2.1.1] hexane ($C_6$), bicyclo[3.1.0]hexane ($C_6$), spiro[2.3]hexane ($C_6$), bicyclo[2.2.1]heptane (norbornane) ($C_7$), bicyclo[3.2.0]heptane ($C_7$), bicyclo[3.1.1]heptane ($C_7$), bicyclo[3.1.1]heptane ($C_7$), bicyclo[4.1.0]heptane ($C_7$), spiro[2.4] heptane ($C_7$), spiro[3.3]heptane ($C_7$), bicyclo[2.2.2]octane ($C_8$), bicyclo[4.1.1]octane ($C_8$)octahydropentalene ($C_8$), bicyclo[3.2.1]octane ($C_8$), bicyclo[4.2.0]octane ($C_8$), spiro [2.5]octane ($C_8$), spiro[3.4]octane ($C_8$), bicyclo[3.3.1] nonane ($C_9$), octahydro-1H-indene ($C_9$), bicyclo[4.2.1] nonane ($C_9$), spiro[3.5]nonane ($C_9$), spiro[4.4]nonane ($C_9$), bicyclo[3.3.2]decane ($C_{10}$), bicyclo[4.3.1]decane ($C_{10}$), spiro[4.5]decane ($C_{10}$), bicyclo[3.3.3]undecane ($C_{11}$), decahydronaphthalene ($C_{10}$), bicyclo[4.3.2]undecane ($C_{11}$), spiro[5.5]undecane ($C_{11}$) and bicyclo[4.3.3]dodecane ($C_{12}$).

In some embodiments "cycloalkyl" is a tricyclic cycloalkyl. In some embodiments, a tricyclic cycloalkyl has 6-14 ring carbon atoms. ("$C_{6-14}$ tricyclic cycloalkyl"). In some embodiments, a tricyclic cycloalkyl group has 8 to 12 ring carbon atoms ("$C_{8-12}$ tricyclic cycloalkyl"). In some embodiments, a tricyclic cycloalkyl group has 10 to 12 ring carbon atoms ("$C_{10-12}$ tricyclic cycloalkyl. Examples of tricyclic cycloalkyls include adamantine ($C_{12}$).

Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl "Heterocyclyl" or "heterocyclic" refers to a radical of a 3-to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary bicyclic heterocyclyl groups include, without limitation, indolinyl, isoindolinyl, dihydrobenzofuranyl, dihydrobenzothienyl, tetrahydrobenzo-thienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like. "Nitrogen-containing heterocyclyl" group means a 4- to 7-membered non-aromatic cyclic group containing at least one nitrogen atom, for example, but without limitation, morpholine, piperidine (e.g., 2-piperidinyl, 3-piperidinyl and 4-piperidinyl), pyrrolidine (e.g., 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(=O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)$CH_3$), cyclohexylcarbonyl, cyclohexylmethylcarbonyl, benzoyl (—C(=O)Ph), benzylcarbonyl (—C(=O)$CH_2$Ph), C(=O)—$C_1$-$C_8$ alkyl, —C(=O)—$(CH_2)_t$($C_6$-$C_{10}$ aryl), —C(=O)—$(CH_2)_t$(5-10 membered heteroaryl), —C(=O)—$(CH_2)_t$($C_3$-$C_{10}$ cycloalkyl), and —C(=O)—$(CH_2)_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

The term aminoalkyl refers to a substituted alkyl group wherein one or more of the hydrogen atoms are independently replaced by an —$NH_2$ group.

The term hydroxyalkyl refers to a substituted alkyl group wherein one or more of the hydrogen atoms are independently replaced by an —OH group.

The terms "alkylamino" and "dialkylamino" refer to —NH(alkyl) and —N(alkyl)$_2$ radicals respectively. In some embodiments the alkylamino is a —NH($C_1$-$C_4$ alkyl). In some embodiments the alkylamino is methylamino, ethylamino, propylamino, isopropylamino, n-butylamino, isobutylamino, sec-butylamino or tert-butylamino. In some embodiments the dialkylamino is —N($C_1$-$C_6$ alkyl)$_2$. In some embodiments the dialkylamino is a dimethylamino, a methylethylamino, a diethylamino, a methylpropylamino, a methylisopropylamino, a methylbutylamino, a methylisobutylamino or a methyltertbutylamino.

The term "aryloxy" refers to an —O-aryl radical. In some embodiments the aryloxy group is phenoxy.

The term "haloalkoxy" refers to alkoxy structures that are substituted with one or more halo groups or with combinations thereof. For example, the term "fluoroalkoxy" includes haloalkoxy groups, in which the halo is fluorine. In some embodiments haloalkoxy groups are difluoromethoxy and trifluoromethoxy.

"Alkoxy" refers to the group —O$R^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_5$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both R$^{38}$ groups are joined to form an alkylene group.

Exemplary "substituted amino" groups include, but are not limited to, —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocyclyl), wherein t is an integer from 0 to 4, for instance 1 or 2, each R$^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

In certain embodiments, the substituent present on the nitrogen atom is a nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —C$_{1-10}$ alkyl (e.g., aralkyl, heteroaralkyl), —C$_{2-10}$ alkenyl, —C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^b$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

each instance of R$^{aa}$ is, independently, selected from —C$_{1-10}$ alkyl, —C$_{1-10}$ perhaloalkyl, —C$_{2-10}$ alkenyl, —C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^b$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, —C$_{1-10}$ alkyl, —C$_{1-10}$ perhaloalkyl, —C$_{2-10}$ alkenyl, —C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^b$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X is a counterion.

each instance of R$^{cc}$ is, independently, selected from hydrogen, —C$_{1-10}$ alkyl, —C$_{1-10}$ perhaloalkyl, —C$_{2-10}$ alkenyl, —C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, —C$_{1-6}$ alkyl, —C$_{1-6}$ perhaloalkyl, —C$_{2-6}$ alkenyl, —C$_{2-6}$ alkynyl, heteroC$_{1-6}$ alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from —C$_{1-6}$ alkyl, —C$_{1-6}$ perhaloalkyl, —C$_{2-6}$ alkenyl, —C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, —C$_{1-6}$ alkyl, —C$_{1-6}$ perhaloalkyl, —C$_{2-6}$ alkenyl, —C$_{2-6}$ alkynyl, heteroC$_{1-6}$ alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$ X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, —C(=S)NH(C$_{1-6}$ alkyl), —C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, —C$_{1-6}$ alkyl, —C$_{1-6}$ perhaloalkyl, —C$_{2-6}$ alkenyl, —C$_{2-6}$ alkynyl, heteroC$_{1-6}$ alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-di-bromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^b$)$_2$, —C(=O)SR$^{aa}$, —C(=O)R$^{aa}$, —CO$_2$R$^{aa}$, —C(=O) N(R$^b$)$_2$, —C(=NR$^b$)R$^{aa}$, —C(=NR$^b$)OR$^{aa}$, —C(=NR$^b$)N (R$^b$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$^{cc}$)$_2$, and —P(=O)(N(R$^b$)$_2$)$_2$, wherein R$^{aa}$, R$^b$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In certain embodiments, the leaving group is halogen, alkanesulfonyloxy, arenesulfonyloxy, diazonium, alkyl diazenes, aryl diazenes, alkyl triazenes, aryl triazenes, nitro, alkyl nitrate, aryl nitrate, alkyl phosphate, aryl phosphate, alkyl carbonyl oxy, aryl carbonyl oxy, alkoxcarbonyl oxy, aryoxcarbonyl oxy ammonia, alkyl amines, aryl amines, hydroxyl group, alkyloxy group, or aryloxy. In some cases, the leaving group is a sulfonic acid ester, such as toluenesulfonate (tosylate, —OTs), methanesulfonate (mesylate, -OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such asp-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

"Carboxy" refers to the radical —C(=O)OH.
"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl (—CF$_3$), difluoromethyl (—CHF$_2$), fluoromethyl (—CH$_2$F), chloromethyl (—CH$_2$Cl), dichloromethyl (—CHCl$_2$), tribromomethyl (—CH$_2$Br), and the like.

"Hydroxy" refers to the radical —OH.
"Nitro" refers to the radical —NO$_2$.
"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3{}^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —S(=O)(=NR$^{bb}$)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =NN($R^b$)$_2$, NN$R^b$C(=O)$R^{aa}$, =NN$R^b$C(=O)O$R^{aa}$, =NN$R^b$S(=O)$_2$$R^{aa}$, =N$R^b$, or =NO$R^{cc}$;

- each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
- each instance of $R^b$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^b$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
- each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;
- each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;
- each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;
- each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and
- each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, SO$_4$$^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^b$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^b$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, the term "salt" refers to any and all salts and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^*(C_{1-4} \text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomologus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides compounds (e.g., compounds of Formula (I), (Ia), (Ib), (Ic) and (Id) or compounds of Table 1, or pharmaceutically acceptable salts thereof) that are MTA-uncompetitive PRMT5 inhibitors useful for treating proliferating disorders (e.g., cancers) associated with MTAP deficiencies and/or MTA accumulation.

In some embodiments, the present invention provides compounds (e.g., compounds of Formula (I), (Ia), (Ib), (Ic) and (Id) or compounds of Table 1, or pharmaceutically acceptable salts thereof) that are MTA-uncompetitive, non-competitive or mixed mode PRMT5 inhibitor or an MTA cooperative binding agent useful for treating proliferating disorders (e.g., cancers) associated with MTAP deficiencies and/or MTA accumulation.

Compounds

In one aspect, provided herein are compounds or pharmaceutically acceptable salts thereof according to Formula (I) wherein:

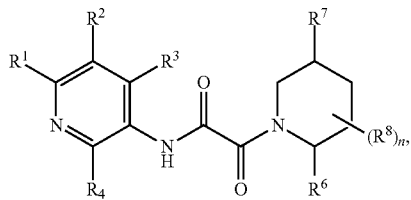

Formula (I)

each $R^1$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a1}$, —$N(R^{a1})_2$, —$C(=O)R^{a1}$, —$C(=O)OR^{a1}$, —$NR^{a1}C(=O)R^{a1}$, —$NR^{a1}C(=O)OR^{a1}$, —$C(=O)N(R^{a1})_2$, —$OC(=O)N(R^{a1})_2$, —$S(=O)R^{a1}$, —$S(=O)_2R^{a1}$, —$SR^{a1}$, —$S(=O)(=NR^{a1})R^{a1}$, —$NR^{a1}S(=O)_2R^{a1}$ and —$S(=O)_2N(R^{a1})_2$;

each $R^2$ is independently selected from halo, —CN, —$C_1$-$C_6$ alkyl, —$C_1$-$C_6$ heteroalkyl, —$C_1$-$C_6$ haloalkyl, —$C_1$-$C_6$ haloalkoxy, —$C_3$-$C_9$ cycloalkyl, 3-10 membered heterocyclyl, heterocyclylalkyl, heteroarylalkyl, arylalkyl, cycloalkylalkyl, —$OR^{a2}$, —$N(R^{a2})_2$, —$C(=O)R^{a2}$, —$C(=O)OR^{a2}$, —$NR^{a2}C(=O)R^{a2}$, —$NR^{a2}C(=O)OR^{a2}$, —$C(=O)N(R^{a2})_2$, —$C(=O)N(OR^{a2})(R^{a2})$—$OC(=O)N(R^{a2})_2$, —$S(=O)R^{a2}$, —$S(=O)_2R^{a2}$, —$SR^{a2}$, —$S(=O)(=NR^{a2})R^{a2}$, —$NR^{a2}S(=O)_2R^{a2}$ and —$S(=O)_2N(R^{a2})_2$;

each $R^3$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a3}$, —$N(R^{a3})_2$, —$C(=O)R^{a3}$, —$C(=O)OR^{a3}$, $NR^{a3}C(=O)R^{a3}$, —$NR^{a3}C(=O)OR^{a3}$, —$C(=O)N(R^{a3})_2$, —$OC(=O)N(R^{a3})_2$, —$S(=O)R^{a3}$, —$S(=O)_2R^{a3}$, —$SR^{a3}$, —$S(=O)(=NR^{a3})R^{a3}$, —$NR^{a3}S(=O)_2R^{a3}$ and —$S(=O)_2N(R^{a3})_2$;

each $R^4$ is independently selected from H, -D, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a4}$, —$N(R^{a4})_2$, —$C(=O)R^{a4}$, —$C(=O)OR^{a4}$, $NR^{a4}C(=O)R^{a4}$, —$NR^{a4}C(=O)OR^{a4}$, —$C(=O)N(R^{a4})_2$, —$OC(=O)N(R^{a4})_2$, —$S(=O)R^{a4}$, —$S(=O)_2R^{a4}$, —$SR^{a4}$, —$S(=O)(=NR^{a4})R^{a4}$, —$NR^{a4}S(=O)_2R^{a4}$ and —$S(=O)_2N(R^{a4})_2$;

each $R^6$ is independently absent or selected from H, -D, halo, —CN, —$C_1$-$C_6$ alkyl, —$C_1$-$C_6$ heteroalkyl, —$C_1$-$C_6$ haloalkyl, —$C_3$-$C_{10}$ carbocyclyl, 3-10 membered heterocyclyl, heterocyclylalkyl, $C_6$-$C_{10}$ aryl, 5-10 member heteroaryl, heteroarylalkyl, arylalkyl, cycloalkylalkyl, —$OR^{a6}$, —$N(R^{a6})_2$, —$C(=O)R^{a6}$, —$C(=O)OR^{a6}$, —$NR^{a6}C(=O)R^{a6}$, —$NR^{a6}C(=O)OR^{a6}$, —$C(=O)N(R^{a6})_2$, —$OC(=O)N(R^{a6})_2$, —$S(=O)R^{a6}$, —$S(=O)_2R^{a6}$, —$SR^{a6}$, —$S(=O)(=NR^{a6})R^{a6}$—$NR^{a6}S(=O)_2R^{a6}$ and —$S(=O)_2N(R^{a6})_2$, wherein each alkyl, carbocyclyl, heterocyclyl, cycloalkylalkyl, heterocyclylalkyl, aryl, heteroaryl, arylalkyl and heteroarylalkyl is optionally substituted at any available position;

each $R^7$ is independently absent or selected from H, -D, halo, —CN, —$C_1$-$C_6$ alkyl, —$C_1$-$C_6$ hydroxyalkyl, —$C_1$-$C_6$ haloalkyl, —$C_3$-$C_9$ cycloalkyl, 3-10 membered heterocyclyl, 5-6-membered monocyclic heteroaryl, heterocyclylalkyl, heteroarylalkyl, arylalkyl, cycloalkylalkyl, —$OR^{a7}$, —$N(R^{a7})_2$, —$C(=O)R^{a7}$, —$C(=O)OR^{a7}$, —$NR^{a7}C(=O)R^{a7}$, —$NR^{a7}C(=O)OR^{a7}$, —$C(=O)N(R^{a7})_2$, —$OC(=O)N(R^{a7})_2$, —$S(=O)R^{a7}$, —$S(=O)_2R^{a7}$, —$SR^{a7}$, —$S(=O)(=NR^{a7})R^{a7}$, —$NR^{a7}S(=O)_2R^{a7}$ and —$S(=O)_2N(R^{a7})_2$;

each $R^8$ is independently selected from H, -D, =O, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a8}$, —$N(R^{a8})_2$, —$C(=O)R^{a8}$, —$C(=O)OR^{a8}$, $NR^{a8}C(=O)R^{a8}$, —$NR^{a8}C(=O)OR^{a8}$, —$CH_2C(=O)N(R^{a8})_2$—$C(=O)N(R^{a8})_2$, —$OC(=O)N(R^{a8})_2$, —$CH_2C(=O)N(R^{a8})_2$, —$S(=O)R^{a8}$, —$S(=O)_2R^{a8}$, —$SR^{a8}$, —$S(=O)(=NR^{a8})R^{a8}$, —$NR^{a8}S(=O)_2R^{a8}$ and —$S(=O)_2N(R^{a8})_2$ wherein two instances of $R^8$ together with the atom or atoms to which they are attached can be taken together to form a 3-10 member cycloalkyl or heterocyclyl ring (e.g., a ring that together with the piperidine ring of Structure I can form a bridged, fused or spiro bicyclic heterocyclic ring)

each $R^{a1}$, $R^{a2}$, $R^{a3}$, $R^{a4}$, $R^{a6}$, $R^{a7}$ and $R^{a8}$ is independently selected from H, $C_1$-$C_6$ alkyl, —$C_1$-$C_6$ heteroalkyl, $C_3$-$C_9$ cycloalkyl, 3-7 membered heterocyclyl, cycloalkylalkyl, heterocyclylalkyl, aryl, 5-6 membered heteroaryl, arylalkyl and heteroarylalkyl wherein each alkyl, cycloalkyl, heterocyclyl, cycloalkylalkyl, heterocyclylalkyl, aryl, heteroaryl, arylalkyl and heteroarylalkyl is optionally substituted at any available position (e.g., substituted with 0, 1, 2 or 3 instances of $R^9$, wherein each $R^9$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^b$, —$N(R^b)_2$, —$C(=O)R^b$, —$C(=O)OR^b$, —$NR^bC(=O)R$, —$NR^bC(=O)OR^b$, —$C(=O)N(R^b)_2$, —$OC(=O)N(R^b)_2$, —$S(=O)R^b$, —$S(=O)_2R^b$, —$SR^b$, —$S(=O)(=NR^b)R^b$, —$NR^bS(=O)_2R^b$ and —$S(=O)_2N(R^b)_2$, wherein each $R^b$ is independently selected from H, —$C_1$-$C_6$ alkyl (e.g., -Me, -Et, —Pr, -$^iPr$, -$^nBu$, $^t$-Bu, -sec-Bu, -iso-Bu). and $C_3$-$C_9$ cycloalkyl (e.g., cyclopropyl, cyclobutyl, cyclopentyl, cyclohexyl); and n is 0, 1,2 or 3 provided that:

when $R^1$ is H, $R^2$ is not halo, —OPr, —$N(CH_3)_2$ or —$CF_3$;

when $R^1$ is $OR^{a1}$, $R^2$ is not —$OR^{a2}$;

when $R^1$ is H and $R^2$ is —$CH_3$, $R^8$ groups cannot be taken together to form a ring and $R^6$ is not absent or H, and is not thiazolyl, furanyl or pyrrolyl;

when $R^2$ is Me, $R^1$ is not optionally substituted piperidine the compound is not:

5-(2-(5-methyl-2-(p-tolyl)piperidin-1-yl)-2-oxoacetamido) nicotinamide or any of its enantiomers or diastereomers 2-(2-(4-(2H-tetrazol-5-yl)phenyl)-5-methylpiperidin-1-yl)-N-(5,6-dimethylpyridin-3-yl)-2-oxoacetamide 2-cyano-5-(2-(5-methyl-2-phenylpiperidin-1-yl)-2-oxoacetamido)nicotinamide.

In some embodiments, $R^6$ is absent (e.g., if a spiro ring formed by two $R^8$ groups is attached to the atom that would otherwise bear $R^6$).

In some embodiments, $R^7$ is absent (e.g., if a spiro ring formed by two $R^8$ groups is attached to the atom that would otherwise bear $R^7$).

In certain embodiments, $R^6$ and $R^7$ are not H and are in a trans relative configuration. In other embodiments, $R^6$ and $R^7$ are not H and are in a cis relative configuration.

In some embodiments, the moiety represented as

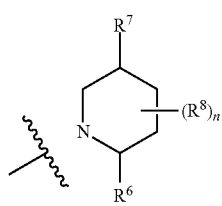

in Formula (I) is selected from:

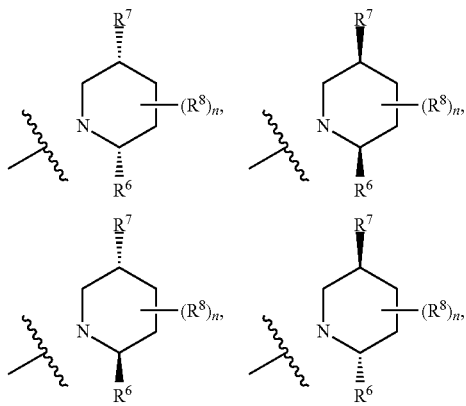

wherein $R^6$, $R^7$, $R^8$ and n are as described herein.

In certain embodiments, the moiety represented as

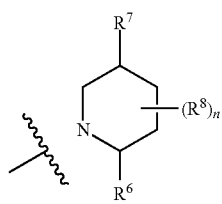

is selected from:

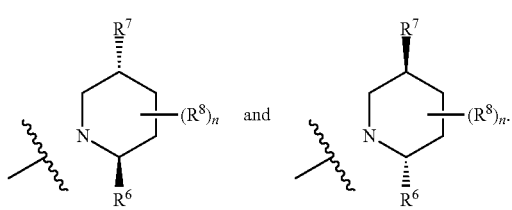

In other embodiments, the moiety represented as

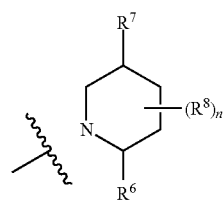

is selected from:

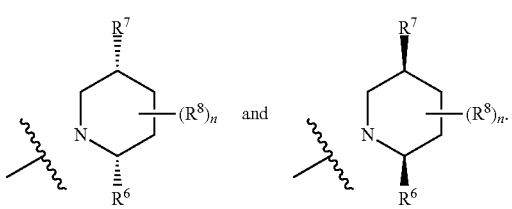

In some embodiments of the invention, the compound of Formula (I) is of Formula (Ia)

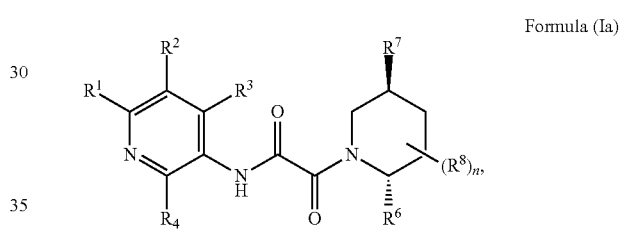

Formula (Ia)

wherein $R^1$, $R^2$, $R^3$, $R^4$, $R^6$, $R^7$, $R^8$ and n are as described herein.

In some embodiments of the invention, the compound of Formula (I) is of Formula (Ib)


Formula (Ib)

wherein $R^1$, $R^2$, $R^3$, $R^4$, $R^6$, $R^7$, $R^8$ and n are as described herein.

In some embodiments of the invention, the compound of Formula (I) is of Formula (Ic)

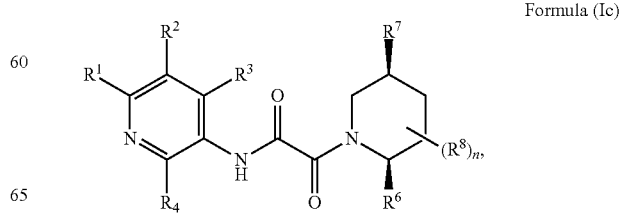

Formula (Ic)

wherein $R^1$, $R^2$, $R^3$, $R^4$, $R^6$, $R^7$, $R^8$ and n are as describing herein.

In some embodiments of the invention, the compound of Formula (I) is of Formula (Id)

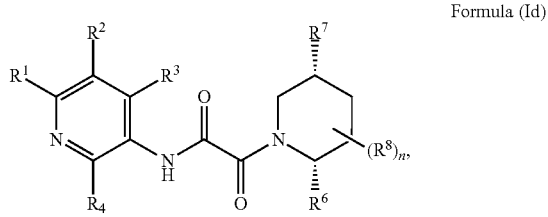

Formula (Id)

wherein $R^1$, $R^2$, $R^3$, $R^4$, $R^6$, $R^7$, $R^8$ and n are as described herein.

In some embodiments of Formula (I), (Ia), (Ib), (Ic) and (Id), when $R^2$ is Me, $R^1$ is not H.

As generally defined herein, each $R^1$ is independently selected from H, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, heterocyclylalkyl, heteroarylalkyl, arylalkyl, cycloalkylalkyl, —$OR^{a1}$, —$N(R^{a1})_2$, —$C(=O)R^{a1}$, —$C(=O)OR^{a1}$, —$NR^{a1}C(=O)R^{a1}$, —$NR^{a1}C(=O)OR^{a1}$, —$C(=O)N(R^{a1})_2$, —$OC(=O)N(R^{a1})_2$, —$S(=O)R^{a1}$, —$S(=O)_2R^{a1}$, —$SR^{a1}$, —$S(=O)(=NR^{a1})R^{a1}$, —$NR^{a1}S(=O)_2R^{a1}$ and —$S(=O)_2N(R^{a1})_2$, wherein $R^{a1}$ is as defined herein.

In some embodiments, $R^1$ is selected from H, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, —$OR^{a1}$, —$N(R^{a1})_2$, —$C(=O)R^{a1}$, —$C(=O)OR^{a1}$, —$NR^{a1}C(=O)R^{a1}$, $NR^{a1}C(=O)OR^{a1}$, —$C(=O)N(R^{a1})_2$ and —$OC(=O)N(R^{a1})_2$. In further embodiments, $R^1$ is selected from H, halo, —CN, —$C_1$-$C_6$ alkyl, —$C_1$-$C_6$ haloalkyl, —$OR^{a1}$ and —$N(R^{a1})_2$.

In certain embodiments, $R^1$ is selected from H, —$C_1$-$C_6$ alkyl, —$C_1$-$C_6$ haloalkyl, —$OR^{a1}$ and —$N(R^{a1})_2$ wherein $R^{a1}$ is as defined herein. In further embodiments, each $R^{a1}$ is independently selected from H, —$C_1$-$C_6$ alkyl (e.g., -Me, -Et, —Pr, -$^i$Pr, -$^n$Bu, -$^i$Bu, -sec-Bu, -iso-Bu) and —$C_1$-$C_6$ haloalkyl (e.g., —$CHF_2$, —$CF_3$).

In some embodiments, $R^1$ is selected from H, —$C_1$-$C_6$ alkyl (e.g., -Me, -Et, —Pr, -$^i$Pr, -$^i$Bu, —Bu, -sec-Bu, -iso-Bu), —$C_1$-$C_6$ haloalkyl (e.g., —$CF_3$, —$CHF_2$), —OH, —O—($C_1$-$C_6$ alkyl) (e.g., —OMe, —OEt), —O—($C_1$-$C_6$ haloalkyl) (e.g., —$OCF_3$, —$OCHF_2$), —$NH_2$, —NH—($C_1$-$C_6$ alkyl) (e.g., —NHMe) and —N—($C_1$-$C_6$ alkyl)$_2$ (e.g., $NMe_2$). In certain embodiments, $R^1$ is selected from H, -Me, -Et, —$CHF_2$, —OMe, —OEt, —$OCHF_2$, —$OCF_3$, —OH and —$NH_2$. In further embodiments, $R^1$ is selected from H, -Et, —OMe, —OEt, —$OCHF_2$, —$OCF_3$ and —OH.

In some embodiments, $R^1$ is selected from H and —OMe.

In other embodiments, $R^1$ is selected from H, -Me, —$CHF_2$ and —$NH_2$. In further embodiments, $R^1$ is selected from -Me and —$NH_2$.

In some embodiments, $R^1$ is H. In some embodiments $R^1$ is -D.

In certain embodiments, $R^1$ is halo (e.g., fluoro, chloro, bromo, iodo). In further embodiments, $R^1$ is —Cl. In some embodiments, $R^1$ is —F. In some embodiments, $R^1$ is —Br. In some embodiments, $R^1$ is —I.

In some embodiments, $R^1$ is —CN.

In certain embodiments, $R^1$ is —$C_1$-$C_6$ alkyl. In further embodiments, $R^1$ is -Me. In some embodiments, $R^1$ is -Et. In some embodiments $R^1$ is —Pr or -$^i$Pr.

In some embodiments, $R^1$ is —$C_1$-$C_6$ heteroalkyl. In further embodiments, $R^1$ is methoxymethyl (—$CH_2OCH_3$). In some embodiments, $R^1$ is hydroxymethyl (—$CH_2OH$). In some embodiments, $R^1$ is aminomethyl (e.g., —$CH_2NH_2$, —$CH_2NHCH_3$, —$CH_2N(CH_3)_2$. In some embodiments, R1 is —$C_1$-$C_6$ haloalkyl. In further embodiments, $R^1$ is trifluoromethyl (—$CF_3$). In other embodiments, $R^1$ is difluoromethyl (—$CHF_2$).

In some embodiments, $R^1$ is —$C_3$-$C_9$ carbocyclyl (e.g., cyclopropyl, cyclobutyl, cyclopentyl, cyclohexyl). In some embodiments, $R^1$ is cyclopropyl. In some embodiments $R^1$ is cyclobutyl. In some embodiments, $R^1$ is cyclopentyl. In some embodiments, $R^1$ is cyclohexyl.

In some embodiments, $R^1$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^1$ is oxetanyl. In some embodiments, $R^1$ is tetrahydropyranyl. In some embodiments, $R^1$ is tetrahydrofuranyl. In some embodiments, $R^1$ is azetidinyl. In some embodiments, $R^1$ is pyrrolidinyl. In some embodiments, $R^1$ is piperidinyl. In some embodiments, $R^1$ is piperazinyl. In some embodiments, $R^1$ is morpholinyl. In some embodiments, $R^1$ is azepanyl.

In some embodiments $R^1$ is cycloalkylalkyl (e.g., cyclopropylmethyl, cyclobutylmethyl, cyclopentylmethyl, cyclohexylmethyl, cycloheptylmethyl). In some embodiments, $R^1$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^1$ is arylalkyl. In some embodiments, $R^1$ is benzyl. In some embodiments, $R^1$ is heteroarylalkyl (e.g., pyridinylmethyl, thiazolylmethyl, triazolylmethyl, pyrazolylmethyl).

In some embodiments, $R^1$ is —$OR^{a1}$ (e.g., hydroxy (—OH), methoxy, difluoromethoxy (—$OCHF_2$), trifluoromethoxy (—$OCF_3$), ethoxy, propoxy, isopropoxy, cyclopropyloxy, cyclobutyloxy). In some embodiments, $R^1$ is hydroxy. In some embodiments, $R^1$ is methoxy. In some embodiments, $R^1$ is ethoxy. In some embodiments, $R^1$ is propoxy. In some embodiments, $R^1$ is isopropoxy. In some embodiments $R^1$ is difluoromethoxy. (—$OCHF_2$). In some embodiments, $R^1$ is trifluoromethoxy (—$OCF_3$).

In some embodiments, $R^1$ is —$N(R^{a1})_2$ (e.g., —$NH_2$, —$NHR^{a1}$, —$N(CH_3)R^{a1}$). In some embodiments, $R^1$ is —$NH_2$. In some embodiments, $R^1$ is —$NHR^{a1}$ (e.g., —NHMe, —NHEt, —NHPr, —NH$^i$Pr, —NHcyclopropyl, —NHcyclobutyl). In some embodiments, $R^1$ is —$N(CH_3)R^{a1}$ (e.g., —$NMe_2$, —$N(CH_3)Et$, —$N(CH_3)Pr$, —$N(CH_3)^i$Pr, —$N(CH_3)$cyclopropyl, —$N(CH_3)$cyclobutyl). In some embodiments, $R^1$ is —$C(=O)R^{a1}$ or —$C(=O)OR^{a1}$. In some embodiments, $R^1$ is —$C(=O)R^{a1}$ wherein $R^{a1}$ is as described herein. In some embodiments, $R^1$ is —$C(=O)$ alkyl. In some embodiments, $R^1$ is —$C(O)CH_3$, —$C(O)$ cyclopropyl, —$C(O)$cyclobutyl, —$C(O)^i$Bu, —$C(O)^i$Pr, —$C(O)Pr$, —$C(O)^i$Bu, or —$C(=O)$OMe. In some embodiments, $R^1$ is acetyl (—$C(=O)Me$). In some embodiments, $R^1$ is —$C(=O)OR^{a1}$. In some embodiments, $R^1$ is —COOH. In some embodiments, $R^1$ is COOMe.

In some embodiments, $R^1$ is —$NR^{a1}C(=O)Ra$. In certain embodiments, $R^1$ is —$NHC(=O)R^{a1}$ (e.g., NHC(=O)Me, NHC(=O)Et, NHC(=O)Pr, NHC(=O)$^i$Pr, NHC(=O)Bu, NHC(=O)$^i$Bu, NHC(=O)Cyclopropyl, NHC(=O)Cyclobutyl). In some embodiments, $R^1$ is —$N(CH_3)C(=O)R^{a1}$ (e.g., N(CH₃)C(=O)Me, N(CH₃)C(=O)Et, N(CH₃)C(=O)Pr, N(CH₃)C(=O)$^i$Pr, N(CH₃)C(=O)Bu, N(CH₃)C(=O)$^t$Bu, N(CH₃)C(=O)Cyclopropyl, N(CH₃)C(=O)Cyclobutyl). In some embodiments, R$^1$ is —NR$^{a1}$C(=O)OR$^{a1}$. In certain embodiments, R$^1$ is —NHC(=O)OR$^{a1}$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, R$^1$ is —N(CH₃)C(=O)OR$^{a1}$ (e.g., N(CH₃)C(=O)OMe, N(CH₃)C(=O)OEt, N(CH₃)C(=O)OPr, N(CH₃)C(=O)O$^i$Pr, N(CH₃)C(=O)OBu, N(CH₃)C(=O)O$^t$Bu, N(CH₃)C(=O)OCyclopropyl, N(CH₃)C(=O)OCyclobutyl).

In some embodiments, R$^1$ is —C(=O)N(R$^{a1}$)₂ (e.g., —C(=O)NH₂, —C(=O)NHR$^{a1}$, —C(=O)N(CH₃)R$^{a1}$). In some embodiments, R$^1$ is —C(=O)NH₂. In certain embodiments, R$^1$ is —C(=O)NHR$^{a1}$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, R$^1$ is —C(=O)N(CH₃)R$^{a1}$ (e.g., —C(=O)NMe₂, —C(=O)N(CH₃)Et, —C(=O)N(CH₃)Pr, —C(=O)N(CH₃)$^i$Pr, —C(=O)N(CH₃)Bu, —C(=O)N(CH₃)$^t$Bu, —C(=O)N(CH₃)Cyclopropyl, —C(=O)N(CH₃)Cyclobutyl). In some embodiments, R$^1$ is —OC(=O)N(R$^{a1}$)₂. In certain embodiments, R$^1$ is —OC(=O)NHR$^{a1}$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, R$^1$ is —OC(=O)N(CH₃)R$^{a1}$ (e.g., —OC(=O)NMe₂, —OC(=O)N(CH₃)Et, —OC(=O)N(CH₃)Pr, —OC(=O)N(CH₃)$^i$Pr, —OC(=O)N(CH₃)Bu, —OC(=O)N(CH₃)$^t$Bu, —OC(=O)N(CH₃)Cyclopropyl, —OC(=O)N(CH₃)Cyclobutyl).

In some embodiments, R$^1$ is —S(=O)R$^{a1}$. In certain embodiments, R$^1$ is —S(=O)alkyl (e.g., —S(=O)Me, —S(=O)Et, —S(=O)Pr, —S(=O)$^i$Pr). In certain embodiments, R$^1$ is —S(=O)cycloalkyl (e.g., —S(=O)cyclopropyl, —S(=O)cyclobutyl, —S(=O)cyclopentyl, —S(=O)cyclohexyl).

In some embodiments, R$^1$ is —S(=O)₂R$^{a1}$. In certain embodiments, R$^1$ is —S(=O)₂ alkyl (e.g., —S(=O)₂Me, —S(=O)₂Et, —S(=O)₂Pr, —S(=O)₂$^i$Pr). In certain embodiments, R$^1$ is —S(=O)₂cycloalkyl (e.g., —S(=O)₂cyclopropyl, —S(=O)₂cyclobutyl, —S(=O)₂cyclopentyl, —S(=O)₂cyclohexyl). In some embodiments, R$^1$ is S(=O)₂ aryl (e.g., S(=O)₂phenyl).

In some embodiments, R$^1$ is —SR$^{a1}$. In certain embodiments, R$^1$ is —Salkyl (e.g., —SMe, —SEt, —SPr, —S$^i$Pr). In certain embodiments, R$^1$ is —Scycloalkyl (e.g., —Scyclopropyl, —Scyclobutyl, —Scyclopentyl, —Scyclohexyl). In certain embodiments, R$^1$ is —Saryl (e.g., Sphenyl).

In some embodiments, R$^1$ is —S(=O)(=NR$^{a1}$)R$^{a1}$. In certain embodiments, R$^1$ is —S(=O)(=NH)R$^{a1}$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, R$^1$ is —S(=O)(=NCH₃)R$^{a1}$ (e.g., —S(=O)(=NCH₃)Me, —S(=O)(=NCH₃)Et, —S(=O)(=NCH₃)Pr, —S(=O)(=NCH₃)$^i$Pr, —S(=O)(=NCH₃)Bu, —S(=O)(=NCH₃)$^t$Bu, —S(=O)(=NCH₃)Cyclopropyl, —S(=O)(=NCH₃)Cyclobutyl).

In some embodiments, R$^1$ is —NR$^{a1}$S(=O)₂R$^{a1}$. In certain embodiments, R$^1$ is —NHS(=O)₂ alkyl (e.g., —NHS(=O)₂Me, —NHS(=O)₂Et, —NHS(=O)₂Pr, —NHS(=O)₂$^i$Pr). In certain embodiments, R$^1$ is —NHS(=O)₂cycloalkyl (e.g., —NHS(=O)₂cyclopropyl, —NHS(=O)₂cyclobutyl, —NHS(=O)₂cyclopentyl, —NHS(=O)₂cyclohexyl). In certain embodiments, R$^1$ is —N(CH₃)S(=O)₂ alkyl (e.g., —N(CH₃)S(=O)₂Me, —N(CH₃)S(=O)₂Et, —N(CH₃)S(=O)₂Pr, —N(CH₃)S(=O)₂$^i$Pr). In certain embodiments, R$^1$ is —N(CH₃)S(=O)₂cycloalkyl (e.g., —N(CH₃)S(=O)₂cyclopropyl, —N(CH₃)S(=O)₂cyclobutyl, —N(CH₃)S(=O)₂cyclopentyl, —N(CH₃)S(=O)₂cyclohexyl).

In some embodiments, R$^1$ is —S(=O)₂N(R$^{a1}$)₂. (e.g., —S(=O)₂NH₂, —S(=O)₂NHR$^{a1}$, —S(=O)₂N(CH₃)R$^{a1}$). In some embodiments, R$^1$ is —S(=O)₂NH₂. In some embodiments, R$^1$ is —S(=O)₂NHR$^{a1}$ (e.g., —S(=O)₂NHMe, —S(=O)₂NHEt, —S(=O)₂NHPr, —S(=O)₂NH$^i$Pr, —S(=O)₂NHcyclopropyl, —S(=O)₂NHcyclobutyl). In some embodiments, R$^1$ is —S(=O)₂N(CH₃)R$^{a1}$ (e.g., —S(=O)₂NMe₂, —S(=O)₂N(CH₃)Et, —S(=O)₂N(CH₃)Pr, —S(=O)₂N(CH₃)$^i$Pr, —S(=O)₂N(CH₃)cyclopropyl, —S(=O)₂N(CH₃)cyclobutyl).

As generally defined herein, each R$^2$ is independently selected from halo, —CN, —C₁-C₆ alkyl, —C₁-C₆ heteroalkyl, —C₁-C₆ haloalkyl, —C₁-C₆ haloalkoxy, —C₃-C₉ cycloalkyl, 3-6 membered heterocyclyl, heterocyclylalkyl, heteroarylalkyl, arylalkyl, cycloalkylalkyl, —OR$^{a2}$, —N(R$^{a2}$)₂, —C(=O)R$^{a2}$, —C(=O)OR$^{a2}$, —NR$^{a2}$C(=O)R$^{a2}$, —NR$^{a2}$C(=O)OR$^{a2}$, —C(=O)N(R$^{a2}$)₂, —C(=O)N(OR$^{a2}$)(R$^{a2}$), —OC(=O)N(R$^{a2}$)₂, —S(=O)R$^{a2}$, —S(=O)₂R$^{a2}$, —SR$^{a2}$, —S(=O)(=NR$^{a2}$)R$^{a2}$, NR$^{a2}$S(=O)₂R$^{a2}$ and —S(=O)₂N(R$^{a2}$)₂, wherein R$^{a2}$ is as defined herein.

In some embodiments, R$^2$ is selected from halo, —CN, —C₁-C₆ alkyl, —C₁-C₆ heteroalkyl, —C₁-C₆ haloalkyl, —C₁-C₆ haloalkoxy, —C₃-C₉ cycloalkyl (e.g., cyclopropyl), 3-6 membered heterocyclyl (e.g., oxetanyl, tetrahydrofuranyl), —OR$^{a2}$, —N(R$^{a2}$)₂, —C(=O)R$^{a2}$, —C(=O)OR$^{a2}$, —NR$^{a2}$C(=O)R$^{a2}$, —NR$^{a2}$C(=O)OR$^{a2}$, —C(=O)N(R$^{a2}$)₂, —C(=O)N(OR$^{a2}$)(R$^{a2}$), OC(=O)N(R$^{a2}$)₂.

In certain embodiments, R$^2$ is selected from halo, —CN, —C₁-C₆ alkyl, —C₁-C₆ haloalkyl, —C₁-C₆ haloalkoxy, —C₃-C₉ cycloalkyl (e.g., cyclopropyl), 3-6 membered heterocyclyl (e.g., oxetanyl, tetrahydrofuranyl), —OR$^{a2}$, —N(R$^{a2}$)₂, —C(=O)N(OR$^{a2}$)(R$^{a2}$), —C(=O)R$^{a2}$ and —C(=O)N(R$^{a2}$)₂.

In some embodiments, R$^2$ is selected from halo, —C₁-C₆ alkyl, —C₁-C₆ haloalkyl, —C₁-C₆ haloalkoxy, —C₃-C₉ cycloalkyl (e.g., cyclopropyl), 3-6 membered heterocyclyl (e.g., oxetanyl, tetrahydrofuranyl), —OR$^{a2}$, —C(=O)R$^{a2}$ and —C(=O)N(R$^{a2}$)₂.

In some embodiments, R$^2$ is selected from halo, —C₁-C₆ alkyl, —C₁-C₆ haloalkyl, —C₁-C₆ haloalkoxy, —C₃-C₉ cycloalkyl (e.g., cyclopropyl), 3-6 membered heterocyclyl (e.g., oxetanyl, tetrahydrofuranyl), —OR$^{a2}$, and —C(=O)N(R$^{a2}$)₂, wherein each R$^{a2}$ is as described herein. In further embodiments, each R$^{a2}$ is independently selected from H and —C₁-C₆ alkyl (e.g., -Me, -Et, —Pr, -$^i$Pr, -$^n$Bu, $^t$-Bu, -sec-Bu, -iso-Bu).

In certain embodiments, R$^2$ is selected from halo (e.g., —C₁), —C₁-C₆ alkyl (e.g., -Me, -Et, —Pr, -$^i$Pr, -$^n$Bu, $^t$-Bu, -sec-Bu, -iso-Bu), —C₁-C₆ haloalkyl (e.g., —CF₃, CHF₂), —C₁-C₆ haloalkoxy (e.g., —OCF₃, —OCHF₂)—C₃-C₉ cycloalkyl (e.g., cyclopropyl), 3-6 membered heterocyclyl (e.g., oxetanyl, tetrahydrofuranyl), —OR$^{a2}$ (e.g., —OMe), —C(=O)NHOH, —C(=O)H, and —C(=O)NH₂. In further embodiments, R$^2$ is selected from —C₁, -Me, -Et, -$^i$Pr, —CF₃, —CHF₂, —OCHF₂, —OCF₃, cyclopropyl, —OMe, oxetan-3-yl, tetrahydrofuran-3-yl, —C(=O)NHOH, —C(=O)H and —C(=O)NH₂.

In some embodiments, $R^2$ is selected from —C(=O)NH$_2$ and —C(=O)H. In some embodiments, $R^2$ is selected from —C$_1$, -Me, -Et, -$^i$Pr, —CF$_3$, CHF$_2$, —OCHF$_2$, —OCF$_3$, and cyclopropyl. In further embodiments, $R^2$ is selected from cyclopropyl, -Me and -Et. In certain embodiments, $R^2$ is halo (e.g., fluoro, chloro, bromo, iodo). In further embodiments, $R^2$ is —Cl. In some embodiments, $R^2$ is —F. In some embodiments, $R^2$ is —Br. In some embodiments, $R^2$ is —I.

In some embodiments, $R^2$ is —CN.

In certain embodiments, $R^2$ is —C$_1$-C$_6$ alkyl. In further embodiments, $R^2$ is -Me. In some embodiments, $R^2$ is -Et. In some embodiments $R^2$ is —Pr or -$^i$Pr.

In some embodiments, $R^2$ is —C$_1$-C$_6$ heteroalkyl. In further embodiments, $R^2$ is methoxymethyl (—CH$_2$OCH$_3$). In some embodiments, $R^2$ is hydroxymethyl (—CH$_2$OH). In some embodiments, $R^2$ is aminomethyl (e.g., —CH$_2$NH$_2$, —CH$_2$NHCH$_3$, —CH$_2$N(CH$_3$)$_2$.

In some embodiments, $R^2$ is —C$_1$-C$_6$ haloalkyl. In further embodiments, $R^2$ is trifluoromethyl (—CF$_3$). In other embodiments, $R^2$ is difluoromethyl (—CHF$_2$).

In some embodiments, $R^2$ is —C$_1$-C$_6$ haloalkoxy. In further embodiments, $R^2$ is trifluoromethoxy (—OCF$_3$), In other embodiments, $R^2$ is difluoromethoxy (—OCHF$_2$).

In some embodiments, $R^2$ is —C$_3$-C$_9$ carbocyclyl (e.g., cyclopropyl, cyclobutyl, cyclopentyl, cyclohexyl). In some embodiments, $R^2$ is cyclopropyl. In some embodiments $R^2$ is cyclobutyl. In some embodiments, $R^2$ is cyclopentyl. In some embodiments, $R^2$ is cyclohexyl.

In some embodiments, $R^2$ is 3-6 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^2$ is oxetanyl. In some embodiments, $R^2$ is tetrahydropyranyl. In some embodiments, $R^2$ is tetrahydrofuranyl. In some embodiments, $R^2$ is azetidinyl. In some embodiments, $R^2$ is pyrrolidinyl. In some embodiments, $R^2$ is piperidinyl. In some embodiments, $R^2$ is piperazinyl. In some embodiments, $R^2$ is morpholinyl. In some embodiments, $R^2$ is azepanyl.

In some embodiments $R^2$ is cycloalkylalkyl (e.g., cyclopropylmethyl, cyclobutylmethyl, cyclopentylmethyl, cyclohexylmethyl, cycloheptylmethyl). In some embodiments, $R^2$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^2$ is arylalkyl. In some embodiments, $R^2$ is benzyl.

In some embodiments, $R^2$ is heteroarylalkyl (e.g., pyridinylmethyl, thiazolylmethyl, triazolylmethyl, pyrazolylmethyl).

In some embodiments, $R^2$ is —OR$^{a2}$ (e.g., hydroxy (—OH), methoxy, ethoxy, propoxy, isopropoxy, cyclopropyloxy, cyclobutyloxy). In some embodiments, $R^2$ is hydroxy. In some embodiments, $R^2$ is methoxy. In some embodiments, $R^2$ is ethoxy. In some embodiments, $R^2$ is propoxy. In some embodiments, $R^2$ is isopropoxy.

In some embodiments, $R^2$ is —N(R$^{a2}$)$_2$ (e.g., —NH$_2$, —NHR$^{a2}$, —N(CH$_3$)R$^{a2}$). In some embodiments, $R^2$ is —NH$_2$. In some embodiments, $R^2$ is —NHR$^{a2}$ (e.g., —NHMe, —NHEt, —NHPr, —NH$^i$Pr, —NHcyclopropyl, —NHcyclobutyl). In some embodiments, $R^2$ is —N(CH$_3$)R$^{a2}$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl). In some embodiments, $R^2$ is —C(=O)R$^{a2}$ or —C(=O)OR$^{a2}$. In some embodiments, $R^2$ is —C(=O)R$^{a2}$ wherein R$^{a2}$ is as described herein. In some embodiments, $R^2$ is —C(=O) alkyl. In some embodiments, $R^2$ is —C(O)CH$_3$, —C(O) cyclopropyl, —C(O)cyclobutyl, —C(O)$^i$Bu, —C(O)$^i$Pr, —C(O)Pr, —C(O)$^i$Bu, or —C(=O)OMe. In some embodiments, $R^2$ is acetyl (—C(=O)Me). In some embodiments, $R^2$ is —C(=O)OR$^{a2}$. In some embodiments, $R^2$ is —COOH. In some embodiments, $R^2$ is COOMe.

In some embodiments, $R^2$ is —NR$^{a2}$C(=O)R$^{a2}$. In certain embodiments, $R^2$ is —NHC(=O)R$^{a2}$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, $R^2$ is —N(CH$_3$)C(=O)R$^{a2}$ (e.g., N(CH$_3$)C(=O)Me, N(CH$_3$)C(=O)Et, N(CH$_3$)C(=O)Pr, N(CH$_3$)C(=O)$^i$Pr, N(CH$_3$)C(=O)Bu, N(CH$_3$)C(=O)$^t$Bu, N(CH$_3$)C(=O)Cyclopropyl, N(CH$_3$)C(=O)Cyclobutyl).

In some embodiments, $R^2$ is —NR$^{a2}$C(=O)OR$^{a2}$. In certain embodiments, $R^2$ is —NHC(=O)OR$^{a2}$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, $R^2$ is —N(CH$_3$)C(=O)OR$^{a2}$ (e.g., N(CH$_3$)C(=O)OMe, N(CH$_3$)C(=O)OEt, N(CH$_3$)C(=O)OPr, N(CH$_3$)C(=O)O$^i$Pr, N(CH$_3$)C(=O)OBu, N(CH$_3$)C(=O)O$^t$Bu, N(CH$_3$)C(=O)OCyclopropyl, N(CH$_3$)C(=O)OCyclobutyl).

In some embodiments, $R^2$ is —C(=O)N(R$^{a2}$)$_2$ (e.g., —C(=O)NH$_2$, —C(=O)NHR$^{a2}$, C(=O)N(CH$_3$)R$^{a2}$). In some embodiments, $R^2$ is —C(=O)NH$_2$. In certain embodiments, $R^2$ is —C(=O)NHR$^{a2}$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, $R^2$ is —C(=O)N(CH$_3$)R$^{a2}$ (e.g., —C(=O)NMe$_2$, —C(=O)N(CH$_3$)Et, —C(=O)N(CH$_3$)Pr, —C(=O)N(CH$_3$)$^i$Pr, —C(=O)N(CH$_3$)Bu, —C(=O)N(CH$_3$)$^t$Bu, —C(=O)N(CH$_3$)Cyclopropyl, —C(=O)N(CH$_3$)Cyclobutyl). In some embodiments, $R^2$ is —C(=O)N(OR$^{a2}$)(R$^{a2}$). In certain embodiments, $R^2$ is —C(=O)NH(OR$^{a2}$) (e.g., —C(=O)NHOH, —C(=O)NHOMe). In some embodiments, $R^2$ is —C(=O)NHOH.

In some embodiments, $R^2$ is —OC(=O)N(R$^{a2}$)$_2$. In certain embodiments, $R^2$ is —OC(=O)NHR$^{a2}$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, $R^2$ is —OC(=O)N(CH$_3$)R$^{a2}$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)$^t$Bu, —OC(=O)N(CH$_3$)Cyclopropyl, —OC(=O)N(CH$_3$)Cyclobutyl).

In some embodiments, $R^2$ is —S(=O)R$^{a2}$. In certain embodiments, $R^2$ is —S(=O)alkyl (e.g., —S(=O)Me, —S(=O)Et, —S(=O)Pr, —S(=O)$^i$Pr). In certain embodiments, $R^2$ is —S(=O)cycloalkyl (e.g., —S(=O)cyclopropyl, —S(=O)cyclobutyl, —S(=O)cyclopentyl, —S(=O)cyclohexyl).

In some embodiments, $R^2$ is —S(=O)$_2$R$^{a2}$. In certain embodiments, $R^2$ is —S(=O)$_2$ alkyl (e.g., —S(=O)$_2$Me, —S(=O)$_2$Et, —S(=O)$_2$Pr, —S(=O)$_2^i$Pr). In certain embodiments, $R^2$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl). In some embodiments, $R^2$ is S(=O)$_2$ aryl (e.g., S(=O)$_2$phenyl).

In some embodiments, $R^2$ is —SR$^{a2}$. In certain embodiments, $R^2$ is —Salkyl (e.g., —SMe, —SEt, —SPr, —S$^i$Pr). In certain embodiments, $R^2$ is —Scycloalkyl (e.g., —Scyclopropyl, —Scyclobutyl, —Scyclopentyl, —Scyclohexyl). In certain embodiments, $R^2$ is —Saryl (e.g., Sphenyl).

In some embodiments, $R^2$ is —S(=O)(=NR$^{a2}$)R$^{a2}$. In certain embodiments, $R^2$ is —S(=O)(=NH)R$^{a2}$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, $R^2$ is —S(=O)(=NCH$_3$)R$^{a2}$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)$^t$Bu, —S(=O)(=NCH$_3$)Cyclopropyl, —S(=O)(=NCH$_3$)Cyclobutyl).

In some embodiments, $R^2$ is —NR$^{a2}$S(=O)$_2$R$^{a2}$. In certain embodiments, $R^2$ is —NHS(=O)$_2$ alkyl (e.g., —NHS(=O)$_2$Me, —NHS(=O)$_2$Et, —NHS(=O)$_2$Pr, —NHS(=O)$_2$$^i$Pr). In certain embodiments, $R^2$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, $R^2$ is —N(CH$_3$)S(=O)$_2$ alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, $R^2$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, $R^2$ is —S(=O)$_2$N(R$^{a2}$)$_2$. (e.g., —S(=O)$_2$NH$_2$, —S(=O)$_2$NHR$^{a2}$, —S(=O)$_2$N(CH$_3$)R$^{a2}$). In some embodiments, $R^2$ is —S(=O)$_2$NH$_2$. In some embodiments, $R^2$ is —S(=O)$_2$NHR$^{a2}$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, $R^2$ is —S(=O)$_2$N(CH$_3$)R$^{a2}$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

Some embodiments of Formula (I), (Ia), (Ib), (Ic) and (Id) feature certain combinations of $R^1$ and $R^2$. In one embodiment, $R^1$ is selected from H, —OMe, —OEt, —OCF$_3$, —OCHF$_2$, —CHF$_2$, -Me, -Et, —OH and —NH$_2$ and $R^2$ is selected from —C$_1$, -Me, -Et, -$^i$Pr, —CF$_3$, —CHF$_2$, —OCHF$_2$, cyclopropyl, —C(=O)NH$_2$, and —C(=O)H, provided that when $R^2$ is -Me, $R^1$ is N$_{12}$. In one embodiment, $R^1$ is selected from H, —CHF$_2$, -Me and —NH$_2$ and $R^2$ is selected from —C$_1$, -Me, -Et, —CF$_3$, —CHF$_2$, —OCHF$_2$ and cyclopropyl, provided that when $R^2$ is -Me, $R^1$ is NH$_2$. In a further embodiment, $R^1$ is selected from —NH$_2$ and -Me and $R^2$ is selected from -Me, and -Et. In one embodiment, $R^1$ is —NH$_2$ and $R^2$ is selected from -Me or -Et. In another embodiment, $R^1$ is selected from H, —OMe, —OEt, —OCF$_3$, —OCHF$_2$, -Et and —OH and $R^2$ is selected from —C(=O)NH$_2$ and —C(=O)H. In a further embodiment, $R^1$ is selected from H and —OMe and $R^2$ is —C(=O)NH$_2$.

As generally described herein, each $R^3$ is independently selected from H, -D, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, heterocyclylalkyl, heteroarylalkyl, arylalkyl, cycloalkylalkyl, —OR$^{a3}$, —N(R$^{a3}$)$_2$, —C(=O)R$^{a3}$, —C(=O)OR$^{a3}$, —NR$^{a3}$C(=O)R$^{a3}$, —NR$^{a3}$C(=O)OR$^{a3}$, —C(=O)N(R$^{a3}$)$_2$, —OC(=O)N(R3)$_2$, —S(=O)R$^{a3}$, —S(=O)$_2$R$^{a3}$, —SR$^{a3}$, —S(=O)(=NR$^{a3}$)R$^{a3}$, —NR$^{a3}$S(=O)$_2$R$^{a3}$ and —S(=O)$_2$N(R$^{a3}$)$_2$, wherein R$^{a3}$ is as described herein.

In some embodiments, $R^3$ is selected from H, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, —OR$^{a3}$, —N(R$^{a3}$)$_2$, —C(=O)R$^{a3}$, —C(=O)OR$^{a3}$, —NR$^{a3}$C(=O)R$^{a3}$, —NR$^{a3}$C(=O)OR$^{a3}$, —C(=O)N(R$^{a3}$)$_2$ and —OC(=O)N(R$^{a3}$)$_2$.

In certain embodiments, $R^3$ is selected from H, halo, —CN, —C$_1$-C$_6$ alkyl, —C$_1$-C$_6$ haloalkyl and —N(R$^{a3}$)$_2$ wherein R$^{a3}$ is as described herein. In further embodiments, R$^{a3}$ is selected from H and C$_1$-C$_6$ alkyl (e.g., -Me, -Et, —Pr, -$^i$Pr, -$^n$Bu, $^t$-Bu, -sec-Bu, -iso-Bu). In some embodiments, $R^3$ is selected from —C$_1$-C$_6$ alkyl (e.g., -Me, -Et, —Pr, -$^i$Pr, -$^n$Bu, —$^t$Bu, -sec-Bu, -iso-Bu), —OH, —O—(C$_1$-C$_6$ alkyl) (e.g., —OMe), —NH$_2$, —NH—(C$_1$-C$_6$ alkyl) (e.g., —NHMe) and —N—(C$_1$-C$_6$ alkyl)$_2$ (e.g., NMe$_2$). In further embodiments, $R^3$ is selected from H, -Me and —NH$_2$. In certain embodiments, $R^3$ is selected from H and -Me.

In some embodiments, $R^3$ is H. In some embodiments $R^3$ is -D.

In certain embodiments, $R^3$ is halo (e.g., fluoro, chloro, bromo, iodo). In further embodiments, $R^3$ is —Cl. In some embodiments, $R^3$ is —F. In some embodiments, $R^3$ is —Br. In some embodiments, $R^3$ is —I.

In some embodiments, $R^3$ is —CN.

In certain embodiments, $R^3$ is —C$_1$-C$_6$ alkyl. In further embodiments, $R^3$ is -Me. In some embodiments, $R^3$ is -Et. In some embodiments $R^3$ is —Pr or -iPr.

In some embodiments, $R^3$ is —C$_1$-C$_6$ heteroalkyl. In further embodiments, $R^3$ is methoxymethyl (—CH$_2$OCH$_3$). In some embodiments, $R^3$ is hydroxymethyl (—CH$_2$OH). In some embodiments, $R^3$ is aminomethyl (e.g., —CH$_2$NH$_2$, —CH$_2$NHCH$_3$, —CH$_2$N(CH$_3$)$_2$.

In some embodiments, $R^3$ is —C$_1$-C$_6$ haloalkyl. In further embodiments, $R^3$ is trifluoromethyl (—CF$_3$). In other embodiments, $R^3$ is difluoromethyl (—CHF$_2$).

In some embodiments, $R^3$ is —C$_3$-C$_9$ carbocyclyl (e.g., cyclopropyl, cyclobutyl, cyclopentyl, cyclohexyl). In some embodiments, $R^3$ is cyclopropyl. In some embodiments $R^3$ is cyclobutyl. In some embodiments, $R^3$ is cyclopentyl. In some embodiments, $R^3$ is cyclohexyl.

In some embodiments, $R^3$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^3$ is oxetanyl. In some embodiments, $R^3$ is tetrahydropyranyl. In some embodiments, $R^3$ is tetrahydrofuranyl. In some embodiments, $R^3$ is azetidinyl. In some embodiments, $R^3$ is pyrrolidinyl. In some embodiments, $R^3$ is piperidinyl. In some embodiments, $R^3$ is piperazinyl. In some embodiments, $R^3$ is morpholinyl. In some embodiments, $R^3$ is azepanyl.

In some embodiments $R^3$ is cycloalkylalkyl (e.g., cyclopropylmethyl, cyclobutylmethyl, cyclopentylmethyl, cyclohexylmethyl, cycloheptylmethyl). In some embodiments, $R^3$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^3$ is arylalkyl. In some embodiments, $R^3$ is benzyl. In some embodiments, $R^3$ is heteroarylalkyl (e.g., pyridinylmethyl, thiazolylmethyl, triazolylmethyl, pyrazolylmethyl).

In some embodiments, $R^3$ is —OR$^{a3}$ (e.g., hydroxy (—OH), methoxy, difluoromethoxy (—OCHF$_2$), trifluoromethoxy (—OCF$_3$), ethoxy, propoxy, isopropoxy, cyclopropyloxy, cyclobutyloxy). In some embodiments, $R^3$ is hydroxy. In some embodiments, $R^3$ is methoxy. In some embodiments, $R^3$ is ethoxy. In some embodiments, $R^3$ is propoxy. In some embodiments, $R^3$ is isopropoxy. In some embodiments $R^3$ is difluoromethoxy. (—OCHF$_2$). In some embodiments, $R^3$ is trifluoromethoxy (—OCF$_3$).

In some embodiments, $R^3$ is —N(R$^{a3}$)$_2$ (e.g., —NH$_2$, —NHR$^3$, —N(CH$_3$)R$^{a3}$). In some embodiments, $R^3$ is —NH$_2$. In some embodiments, $R^3$ is —NHR$^3$ (e.g., —NHMe, —NHEt, —NHPr, —NH$^i$Pr, —NHcyclopropyl, —NHcyclobutyl). In some embodiments, R$^3$ is —N(CH$_3$)R$^{a3}$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl). In some embodiments, R$^3$ is —C(=O)R$^{a3}$ or —C(=O)OR$^3$. In some embodiments, R$^3$ is —C(=O)R$^{a3}$ wherein R$^{a3}$ is as described herein. In some embodiments, R$^3$ is —C(=O)alkyl. In some embodiments, R$^3$ is —C(O)CH$_3$, —C(O)cyclopropyl, —C(O)cyclobutyl, —C(O)$^i$Bu, —C(O)$^i$Pr, —C(O)Pr, —C(O)$^t$Bu, or —C(=O)OMe. In some embodiments, R$^3$ is acetyl (—C(=O)Me). In some embodiments, R$^3$ is —C(=O)OR$^3$. In some embodiments, R$^3$ is —COOH. In some embodiments, R$^3$ is COOMe.

In some embodiments, R$^3$ is —NR$^{a3}$C(=O)R$^{a3}$. In certain embodiments, R$^3$ is —NHC(=O)R$^{a3}$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, R$^3$ is —N(CH$_3$)C(=O)R$^{a3}$ (e.g., N(CH$_3$)C(=O)Me, N(CH$_3$)C(=O)Et, N(CH$_3$)C(=O)Pr, N(CH$_3$)C(=O)$^i$Pr, N(CH$_3$)C(=O)Bu, N(CH$_3$)C(=O)$^t$Bu, N(CH$_3$)C(=O)Cyclopropyl, N(CH$_3$)C(=O)Cyclobutyl).

In some embodiments, R$^3$ is —NR$^{a3}$C(=O)OR$^{a3}$. In certain embodiments, R$^3$ is —NHC(=O)OR$^3$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, R$^3$ is —N(CH$_3$)C(=O)OR$^3$ (e.g., N(CH$_3$)C(=O)OMe, N(CH$_3$)C(=O)OEt, N(CH$_3$)C(=O)OPr, N(CH$_3$)C(=O)O$^i$Pr, N(CH$_3$)C(=O)OBu, N(CH$_3$)C(=O)O$^t$Bu, N(CH$_3$)C(=O)OCyclopropyl, N(CH$_3$)C(=O)OCyclobutyl).

In some embodiments, R$^3$ is —C(=O)N(R$^{a3}$)$_2$ (e.g., —C(=O)NH$_2$, —C(=O)NHR$^{a3}$, C(=O)N(CH$_3$)R$^{a3}$). In some embodiments, R$^3$ is —C(=O)NH$_2$. In certain embodiments, R$^3$ is —C(=O)NHR$^{a3}$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, R$^3$ is —C(=O)N(CH$_3$)R$^{a3}$ (e.g., —C(=O)NMe$_2$, —C(=O)N(CH$_3$)Et, —C(=O)N(CH$_3$)Pr, —C(=O)N(CH$_3$)$^i$Pr, —C(=O)N(CH$_3$)Bu, —C(=O)N(CH$_3$)$^t$Bu, —C(=O)N(CH$_3$)Cyclopropyl, —C(=O)N(CH$_3$)Cyclobutyl).

In some embodiments, R$^3$ is —OC(=O)N(R$^{a3}$)$_2$. In certain embodiments, R$^3$ is —OC(=O)NHR$^{a3}$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, R$^3$ is —OC(=O)N(CH$_3$)R$^{a3}$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)$^t$Bu, —OC(=O)N(CH$_3$)Cyclopropyl, —OC(=O)N(CH$_3$)Cyclobutyl).

In some embodiments, R$^3$ is —S(=O)R$^{a3}$. In certain embodiments, R$^3$ is —S(=O)alkyl (e.g., —S(=O)Me, —S(=O)Et, —S(=O)Pr, —S(=O)$^i$Pr). In certain embodiments, R$^3$ is —S(=O)cycloalkyl (e.g., —S(=O)cyclopropyl, —S(=O)cyclobutyl, —S(=O)cyclopentyl, —S(=O)cyclohexyl).

In some embodiments, R$^3$ is —S(=O)$_2$R$^{a3}$. In certain embodiments, R$^3$ is —S(=O)$_2$ alkyl (e.g., —S(=O)$_2$Me, —S(=O)$_2$Et, —S(=O)$_2$Pr, —S(=O)$_2$$^i$Pr). In certain embodiments, R$^3$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl). In some embodiments, R$^3$ is S(=O)$_2$ aryl (e.g., S(=O)$_2$phenyl).

In some embodiments, R$^3$ is —SR$^{a3}$. In certain embodiments, R$^3$ is —Salkyl (e.g., —SMe, —SEt, —SPr, —S$^i$Pr).

In certain embodiments, R$^3$ is —Scycloalkyl (e.g., —Scyclopropyl, —Scyclobutyl, —Scyclopentyl, —Scyclohexyl). In certain embodiments, R$^3$ is —Saryl (e.g., Sphenyl).

In some embodiments, R$^3$ is —S(=O)(=NR$^{a3}$)R$^{a3}$. In certain embodiments, R$^3$ is —S(=O)(=NH)R$^{a3}$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, R$^3$ is —S(=O)(=NCH$_3$)R$^{a3}$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)Bu, —S(=O)(=NCH$_3$)Cyclopropyl, —S(=O)(=NCH$_3$)Cyclobutyl).

In some embodiments, R$^3$ is —NR$^{a3}$S(=O)$_2$R$^{a3}$. In certain embodiments, R$^3$ is —NHS(=O)$_2$ alkyl (e.g., —NHS(=O)$_2$Me, —NHS(=O)$_2$Et, —NHS(=O)$_2$Pr, —NHS(=O)$_2$$^i$Pr). In certain embodiments, R$^3$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, R$^3$ is —N(CH$_3$)S(=O)$_2$ alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, R$^3$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, R$^3$ is —S(=O)$_2$N(R$^{a3}$)$_2$. (e.g., —S(=O)$_2$NH$_2$, —S(=O)$_2$NHR$^{a3}$, —S(=O)$_2$N(CH$_3$)R$^{a3}$). In some embodiments, R$^3$ is —S(=O)$_2$NH$_2$. In some embodiments, R$^3$ is —S(=O)$_2$NHR$^{a3}$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, R$^3$ is —S(=O)$_2$N(CH$_3$)R$^{a3}$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

As generally described herein, each R$^4$ is independently selected from H, -D, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, heterocyclylalkyl, heteroarylalkyl, arylalkyl, cycloalkylalkyl, —OR$^{a4}$, —N(R$^{a4}$)$_2$, —C(=O)R$^{a4}$, —C(=O)OR$^{a4}$, —NR$^{a4}$C(=O)R$^{a4}$, —NR$^{a4}$C(=O)OR$^{a4}$, —C(=O)N(R$^{a4}$)$_2$, —OC(=O)N(R$^{a4}$)$_2$, —S(=O)R$^{a4}$, —S(=O)$_2$R$^{a4}$, —SR$^{a4}$, —S(=O)(=NR$^{a4}$)R$^{a4}$, —NR$^{a4}$S(=O)$_2$R$^{a4}$ and —S(=O)$_2$N(R$^{a4}$)$_2$, wherein each R$^{a4}$ is as described herein.

In certain embodiments, R$^4$ is selected from H, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, —OR$^{a4}$, —N(R$^{a4}$)$_2$, —C(=O)R$^{a4}$, —C(=O)OR$^{a4}$, —NR$^{a4}$C(=O)R$^{a4}$, —NR$^{a4}$C(=O)OR$^{a4}$, —C(=O)N(R$^{a4}$)$_2$ and —OC(=O)N(R$^{a4}$)$_2$.

In some embodiments, R$^4$ is selected from H, halo, —CN, —C$_1$-C$_6$ alkyl, —C$_1$-C$_6$ haloalkyl and —N(R$^{a4}$)$_2$, wherein each R$^{a4}$ is as described herein. In further embodiments, each R$^{a4}$ is independently selected from H and —C$_1$-C$_6$ alkyl (e.g., -Me, -Et, —Pr, -$^i$Pr, -$^n$Bu, —Bu, -sec-Bu, -iso-Bu). In some embodiments, R$^4$ is selected from —C$_1$-C$_6$ alkyl (e.g., -Me, -Et, —Pr, -$^i$Pr, -$^n$Bu, -$^t$Bu, -sec-Bu, -iso-Bu), —OH, —O—(C$_1$-C$_6$ alkyl) (e.g., —OMe), —NH$_2$, —NH—(C$_1$-C$_6$ alkyl) (e.g., —NHMe) and —N—(C$_1$-C$_6$ alkyl)$_2$ (e.g., NMe$_2$).

In some embodiments, R$^4$ is H. In some embodiments R$^4$ is -D.

In certain embodiments, $R^4$ is halo (e.g., fluoro, chloro, bromo, iodo). In further embodiments, $R^4$ is —Cl. In some embodiments, $R^4$ is —F. In some embodiments, $R^4$ is —Br. In some embodiments, $R^4$ is —I.

In some embodiments, $R^4$ is —CN.

In certain embodiments, $R^4$ is —$C_1$-$C_6$ alkyl. In further embodiments, $R^4$ is -Me. In some embodiments, $R^4$ is -Et. In some embodiments $R^4$ is —Pr or -$^i$Pr.

In some embodiments, $R^4$ is —$C_1$-$C_6$ heteroalkyl. In further embodiments, $R^4$ is methoxymethyl (—$CH_2OCH_3$). In some embodiments, $R^4$ is hydroxymethyl (—$CH_2OH$). In some embodiments, $R^4$ is aminomethyl (e.g., —$CH_2NH_2$, —$CH_2NHCH_3$, —$CH_2N(CH_3)_2$.

In some embodiments, $R^4$ is —$C_1$-$C_6$ haloalkyl. In further embodiments, $R^4$ is trifluoromethyl (—$CF_3$). In other embodiments, $R^4$ is difluoromethyl (—$CHF_2$).

In some embodiments, $R^4$ is —$C_3$-$C_9$ carbocyclyl (e.g., cyclopropyl, cyclobutyl, cyclopentyl, cyclohexyl). In some embodiments, $R^4$ is cyclopropyl. In some embodiments $R^4$ is cyclobutyl. In some embodiments, $R^4$ is cyclopentyl. In some embodiments, $R^4$ is cyclohexyl.

In some embodiments, $R^4$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^4$ is oxetanyl. In some embodiments, $R^4$ is tetrahydropyranyl. In some embodiments, $R^4$ is tetrahydrofuranyl. In some embodiments, $R^4$ is azetidinyl. In some embodiments, $R^4$ is pyrrolidinyl. In some embodiments, $R^4$ is piperidinyl. In some embodiments, $R^4$ is piperazinyl. In some embodiments, $R^4$ is morpholinyl. In some embodiments, $R^4$ is azepanyl.

In some embodiments $R^4$ is cycloalkylalkyl (e.g., cyclopropylmethyl, cyclobutylmethyl, cyclopentylmethyl, cyclohexylmethyl, cycloheptylmethyl). In some embodiments, $R^4$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^4$ is arylalkyl. In some embodiments, $R^4$ is benzyl.

In some embodiments, $R^4$ is heteroarylalkyl (e.g., pyridinylmethyl, thiazolylmethyl, triazolylmethyl, pyrazolylmethyl).

In some embodiments, $R^4$ is —$OR^{a4}$ (e.g., hydroxy (—OH), methoxy, difluoromethoxy (—$OCHF_2$), trifluoromethoxy (—$OCF_3$), ethoxy, propoxy, isopropoxy, cyclopropyloxy, cyclobutyloxy). In some embodiments, $R^4$ is hydroxy. In some embodiments, $R^4$ is methoxy. In some embodiments, $R^4$ is ethoxy. In some embodiments, $R^4$ is propoxy. In some embodiments, $R^4$ is isopropoxy. In some embodiments $R^4$ is difluoromethoxy. (—$OCHF_2$). In some embodiments, $R^4$ is trifluoromethoxy (—$OCF_3$).

In some embodiments, $R^4$ is —$N(R^{a4})_2$ (e.g., —$NH_2$, —$NHR^{a4}$, —$N(CH_3)R^{a4}$). In some embodiments, $R^4$ is —$NH_2$. In some embodiments, $R^4$ is —$NHR^{a4}$ (e.g., —NHMe, —NHEt, —NHPr, —$NH^iPr$, —NHcyclopropyl, —NHcyclobutyl). In some embodiments, $R^4$ is —$N(CH_3)R^{a4}$ (e.g., —$NMe_2$, —$N(CH_3)Et$, —$N(CH_3)Pr$, —$N(CH_3)$$^iPr$, —$N(CH_3)$cyclopropyl, —$N(CH_3)$cyclobutyl). In some embodiments, $R^4$ is —$C(=O)R^{a4}$ or —$C(=O)OR^{a4}$. In some embodiments, $R^4$ is —$C(=O)R^{a4}$ wherein $R^{a4}$ is as described herein. In some embodiments, $R^4$ is —$C(=O)$alkyl. In some embodiments, $R^4$ is —$C(=O)CH_3$, —$C(O)$cyclopropyl, —$C(O)$cyclobutyl, —$C(O)^iBu$, —$C(O)Pr$, —$C(O)^tBu$, or —$C(=O)OMe$. In some embodiments, $R^4$ is acetyl (—$C(=O)Me$). In some embodiments, $R^4$ is —$C(=O)OR^{a4}$. In some embodiments, $R^4$ is —COOH. In some embodiments, $R^4$ is COOMe.

In some embodiments, $R^4$ is —$NR^{a4}C(=O)R^{a4}$. In certain embodiments, $R^4$ is —$NHC(=O)R^{a4}$ (e.g., NHC(=O)Me, NHC(=O)Et, NHC(=O)Pr, NHC(=O)$^iPr$, NHC(=O)Bu, NHC(=O)$^tBu$, NHC(=O)Cyclopropyl, NHC(=O)Cyclobutyl). In some embodiments, $R^4$ is —$N(CH_3)C(=O)R^{a4}$ (e.g., $N(CH_3)C(=O)Me$, $N(CH_3)C(=O)Et$, $N(CH_3)C(=O)Pr$, $N(CH_3)C(=O)^iPr$, $N(CH_3)C(=O)Bu$, $N(CH_3)C(=O)^tBu$, $N(CH_3)C(=O)Cyclopropyl$, $N(CH_3)C(=O)Cyclobutyl$). In some embodiments, $R^4$ is —$NR^{a4}C(=O)OR^{a4}$. In certain embodiments, $R^4$ is —$NHC(=O)OR^{a4}$ (e.g., NHC(=O)OMe, NHC(=O)OEt, NHC(=O)OPr, NHC(=O)O$^iPr$, NHC(=O)OBu, NHC(=O)O$^tBu$, NHC(=O)OCyclopropyl, NHC(=O)OCyclobutyl). In some embodiments, $R^4$ is —$N(CH_3)C(=O)OR^{a4}$ (e.g., $N(CH_3)C(=O)OMe$, $N(CH_3)C(=O)OEt$, $N(CH_3)C(=O)OPr$, $N(CH_3)C(=O)O^iPr$, $N(CH_3)C(=O)OBu$, $N(CH_3)C(=O)O^tBu$, $N(CH_3)C(=O)OCyclopropyl$, $N(CH_3)C(=O)OCyclobutyl$).

In some embodiments, $R^4$ is —$C(=O)N(R^{a4})_2$ (e.g., —$C(=O)NH_2$, —$C(=O)NHR^{a4}$, $C(=O)N(CH_3)R^{a4}$). In some embodiments, $R^4$ is —$C(=O)NH_2$. In certain embodiments, $R^4$ is —$C(=O)NHR^{a4}$ (e.g., —C(=O)NHMe, —C(=O)NHEt, —C(=O)NHPr, —C(=O)NH$^iPr$, —C(=O)NHBu, —C(=O)NH$^tBu$, —C(=O)NHCyclopropyl, —C(=O)NHCyclobutyl). In certain embodiments, $R^4$ is —$C(=O)N(CH_3)R^{a4}$ (e.g., —$C(=O)NMe_2$, —$C(=O)N(CH_3)Et$, —$C(=O)N(CH_3)Pr$, —$C(=O)N(CH_3)^iPr$, —$C(=O)N(CH_3)Bu$, —$C(=O)N(CH_3)^tBu$, —$C(=O)N(CH_3)Cyclopropyl$, —$C(=O)N(CH_3)Cyclobutyl$).

In some embodiments, $R^4$ is —$OC(=O)N(R^{a4})_2$. In certain embodiments, $R^4$ is —$OC(=O)NHR^{a4}$ (e.g., —OC(=O)NHMe, —OC(=O)NHEt, —OC(=O)NHPr, —OC(=O)NH$^iPr$, —OC(=O)NHBu, —OC(=O)NH$^tBu$, —OC(=O)NHCyclopropyl, —OC(=O)NHCyclobutyl). In certain embodiments, $R^4$ is —$OC(=O)N(CH_3)R^{a4}$ (e.g., —$OC(=O)NMe_2$, —$OC(=O)N(CH_3)Et$, —$OC(=O)N(CH_3)Pr$, —$OC(=O)N(CH_3)^iPr$, —$OC(=O)N(CH_3)Bu$, —$OC(=O)N(CH_3)^tBu$, —$OC(=O)N(CH_3)Cyclopropyl$, —$OC(=O)N(CH_3)Cyclobutyl$).

In some embodiments, $R^4$ is —$S(=O)R^{a4}$. In certain embodiments, $R^4$ is —$S(=O)$alkyl (e.g., —$S(=O)Me$, —$S(=O)Et$, —$S(=O)Pr$, —$S(=O)^iPr$). In certain embodiments, $R^4$ is —$S(=O)$cycloalkyl (e.g., —$S(=O)$cyclopropyl, —$S(=O)$cyclobutyl, —$S(=O)$cyclopentyl, —$S(=O)$cyclohexyl).

In some embodiments, $R^4$ is —$S(=O)_2R^{a4}$. In certain embodiments, $R^4$ is —$S(=O)_2$ alkyl (e.g., —$S(=O)_2Me$, —$S(=O)_2Et$, —$S(=O)_2Pr$, —$S(=O)_2^iPr$). In certain embodiments, $R^4$ is —$S(=O)_2$cycloalkyl (e.g., —$S(=O)_2$cyclopropyl, —$S(=O)_2$cyclobutyl, —$S(=O)_2$cyclopentyl, —$S(=O)_2$cyclohexyl). In some embodiments, $R^4$ is $S(=O)_2$ aryl (e.g., $S(=O)_2$phenyl).

In some embodiments, $R^4$ is —$SR^{a4}$. In certain embodiments, $R^4$ is —Salkyl (e.g., —SMe, —SEt, —SPr, —S$^iPr$). In certain embodiments, $R^4$ is —Scycloalkyl (e.g., —Scyclopropyl, —Scyclobutyl, —Scyclopentyl, —Scyclohexyl). In certain embodiments, $R^4$ is —Saryl (e.g., Sphenyl).

In some embodiments, $R^4$ is —$S(=O)(=NR^{a4})R^{a4}$. In certain embodiments, $R^4$ is —$S(=O)(=NH)R^{a4}$ (e.g., —S(=O)(=NH)Me, —S(=O)(=NH)Et, —S(=O)(=NH)Pr, —S(=O)(=NH)$^iPr$, —S(=O)(=NH)Bu, —S(=O)(=NH)$^tBu$, —S(=O)(=NH)Cyclopropyl, —S(=O)(=NH)Cyclobutyl). In some embodiments, $R^4$ is —$S(=O)(=NCH_3)R^{a4}$ (e.g., —$S(=O)(=NCH_3)Me$, —$S(=O)(=NCH_3)Et$, —$S(=O)(=NCH_3)Pr$, —S(=O)

(=NCH$_3$)$^i$Pr, —S(=O)(=NCH$_3$)Bu, —S(=O)(=NCH$_3$)$^t$Bu, —S(=O)(=NCH$_3$)Cyclopropyl, —S(=O)(=NCH$_3$)Cyclobutyl).

In some embodiments, R$^4$ is —NR$^{a4}$S(=O)$_2$R$^{a4}$. In certain embodiments, R$^4$ is —NHS(=O)$_2$ alkyl (e.g., —NHS(=O)$_2$Me, —NHS(=O)$_2$Et, —NHS(=O)$_2$Pr, —NHS(=O)$_2$$^i$Pr). In certain embodiments, R$^4$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, R$^4$ is —N(CH$_3$)S(=O)$_2$ alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, R$^4$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, R$^4$ is —S(=O)$_2$N(R$^{a4}$)$_2$. (e.g., —S(=O)$_2$NH$_2$, —S(=O)$_2$NHR$^{a4}$—S(=O)$_2$N(CH$_3$)R$^{a4}$). In some embodiments, R$^4$ is —S(=O)$_2$NH$_2$. In some embodiments, R$^4$ is —S(=O)$_2$NHR$^{a4}$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, R$^4$ is —S(=O)$_2$N(CH$_3$)R$^{a4}$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

As generally described herein, each R$^6$ is independently absent or selected from H, -D, halo, —CN, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl, cycloalkylalkyl, —OR$^{a6}$, —N(R$^{a6}$)$_2$, —C(=O)R$^{a6}$, —C(=O)OR$^{a6}$, —NR$^{a6}$C(=O)R$^{a6}$—NR$^{a6}$C(=O)OR$^{a6}$, —C(=O)N(R$^{a6}$)$_2$, —OC(=O)N(R$^{a6}$)$_2$, —S(=O)R$^{a6}$, —S(=O)$_2$R$^{a6}$, —SR$^{a6}$—S(=O)(=NR$^{a6}$)R$^{a6}$, —NR$^{a6}$S(=O)$_2$R$^{a6}$ and —S(=O)$_2$N(R$^{a6}$)$_2$, wherein each alkyl, carbocyclyl, heterocyclyl, cycloalkylalkyl, heterocyclylalkyl, aryl, heteroaryl, arylalkyl and heteroarylalkyl is optionally substituted at any available position, wherein each R$^{a6}$ is as described herein. In some embodiments, each R$^6$ is independently selected from halo, —CN, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl, cycloalkylalkyl, —OR$^{a6}$, —N(R$^{a6}$)$_2$, —C(=O)R$^{a6}$, —C(=O)OR$^{a6}$, —NR$^{a6}$C(=O)R$^{a6}$, —NR$^{a6}$C(=O)OR$^{a6}$, —C(=O)N(R$^{a6}$)$_2$, —OC(=O)N(R$^{a6}$)$_2$, —S(=O)R$^{a6}$, —S(=O)$_2$R$^{a6}$, —SR$^{a6}$, —S(=O)(=NR$^{a6}$)R$^{a6}$—NR$^{a6}$S(=O)$_2$R$^{a6}$ and —S(=O)$_2$N(R$^{a6}$)$_2$, wherein each alkyl, carbocyclyl, heterocyclyl, cycloalkylalkyl, heterocyclylalkyl, aryl, heteroaryl, arylalkyl and heteroarylalkyl is optionally substituted at any available position, wherein each R$^{a6}$ is as described herein. In some embodiments, each R$^{a6}$ is independently selected from H and —C$_1$-C$_6$ alkyl (e.g., -Me, -Et, -Pr, -$^i$Pr, -$^n$Bu, -$^i$Bu, -sec-Bu, -iso-Bu).

In some embodiments, each alkyl, carbocyclyl, heterocyclyl, aryl, heteroaryl, cycloalkylalkyl, heterocyclylalkyl, arylalkyl and heteroarylalkyl of R$^6$ is substituted at any available position with 0, 1, 2 or 3 instances of R$^{10}$, wherein each R$^{10}$ is as described herein. In some embodiments, each R$^6$ is independently selected from H, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, carbocyclyl, heterocyclyl, cycloalkylalkyl, heterocyclylalkyl, aryl, heteroaryl, arylalkyl and heteroarylalkyl is optionally substituted at any available position (e.g., substituted at any available position with 0, 1, 2 or 3 instances of R$^{10}$, wherein each R$^{10}$ is as described herein). In some embodiments, each R$^6$ is independently selected from —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, carbocyclyl, heterocyclyl, cycloalkylalkyl, heterocyclylalkyl, aryl, heteroaryl, arylalkyl and heteroarylalkyl is optionally substituted at any available position (e.g., substituted at any available position with 0, 1, 2 or 3 instances of R$^{10}$, wherein each R$^{10}$ is as described herein).

In some embodiments, R$^6$ is independently selected from H, —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, carbocyclyl, heterocyclyl, cycloalkylalkyl, heterocyclylalkyl, aryl, heteroaryl, arylalkyl and heteroarylalkyl is substituted at any available position with 0, 1, 2 or 3 instances of R$^{10}$ wherein R$^{10}$ is as described herein. In some embodiments, R$^6$ is independently selected from —C$_1$-C$_6$ alkyl, —C$_1$-C$_6$ heteroalkyl, —C$_1$-C$_6$ haloalkyl, —C$_3$-C$_{10}$ carbocyclyl, 3-10 membered heterocyclyl, heterocyclylalkyl, C$_6$-C$_{10}$ aryl, 5-10 member heteroaryl, heteroarylalkyl, arylalkyl and cycloalkylalkyl, wherein each alkyl, carbocyclyl, heterocyclyl, cycloalkylalkyl, heterocyclylalkyl, aryl, heteroaryl, arylalkyl and heteroarylalkyl is substituted at any available position with 0, 1, 2 or 3 instances of R$^{10}$ wherein R$^{10}$ is as described herein. In some embodiments, each R$^6$ is unsubstituted. In some embodiments, each R$^6$ is substituted with 1 instance of R$^{10}$. In some embodiments, each R$^6$ is substituted with 2 instances of R$^{10}$. In some embodiments, each R$^6$ is substituted with 3 instances of R$^{10}$.

In some embodiments, R$^6$ is independently selected from H, —C$_1$-C$_6$ alkyl, —C$_3$-C$_{10}$ monocyclic or bicyclic carbocyclyl (e.g., a —C$_3$-C$_{10}$ monocyclic or bicyclic cycloalkyl, a partially unsaturated —C$_3$-C$_{10}$ monocyclic or bicyclic carbocyclyl, a —C$_3$-C$_7$ monocyclic carbocyclyl fused with phenyl or a 5-6-member heterocyclyl or heteroaryl ring containing 1-3 atoms independently selected from N, O, S or oxidized forms thereof), 3-10 membered mono or bicyclic heterocyclyl (e.g., a 3-8 member monocyclic heterocyclyl containing 1-3 heteroatoms selected from N, O and S or oxidized forms thereof, a 4-10 member bicyclic heterocyclyl containing 1-3 heteroatoms independently selected from N, O and S or oxidized forms thereof), —C$_6$-C$_{10}$ mono or bicyclic aryl (e.g., phenyl, fully aromatic 9-10 member bicyclic aryl, bicyclic aryl containing a phenyl ring fused with a C$_5$-C$_6$ carbocycle, bicyclic aryl containing a phenyl ring fused with a 5-6 member heterocycle containing 1-3 heteroatoms independently selected from N, O and S or oxidized forms thereof), 5-6 member monocyclic heteroaryl (e.g., containing 1-4 heteroatoms independently selected from N, O and S), 8-10 member bicyclic heteroaryl (e.g., containing 1-4 heteroatoms independently selected from N, O and S) wherein each alkyl, carbocyclyl, heterocyclyl, aryl and heteroaryl is optionally substituted (e.g., substituted with 0, 1, 2 or 3 instances of R$^{10}$ wherein R$^{10}$ is as described herein). In some embodiments, R$^6$ is independently selected from —C$_1$-C$_6$ alkyl, —C$_3$-C$_{10}$ monocyclic or bicyclic carbocyclyl (e.g., a —C$_3$-C$_{10}$ monocyclic or bicyclic cycloalkyl, a partially unsaturated —C$_3$-C$_{10}$ monocyclic or bicyclic carbocyclyl, a —C$_3$-C$_7$ monocyclic carbocyclyl fused with phenyl or a 5-6-member heterocyclyl or heteroaryl ring containing 1-3 atoms independently selected from N, O, S or oxidized forms thereof), 3-10 membered mono or bicyclic heterocyclyl (e.g., a 3-8 member monocyclic heterocyclyl containing 1-3 heteroatoms selected from N, O and S or oxidized forms thereof, a 4-10 member bicyclic heterocyclyl containing 1-3 heteroatoms independently selected from N, O and S or oxidized forms thereof), —$C_6$-$C_{10}$ mono or bicyclic aryl (e.g., phenyl, fully aromatic 9-10 member bicyclic aryl, bicyclic aryl containing a phenyl ring fused with a $C_5$-$C_6$ carbocycle, bicyclic aryl containing a phenyl ring fused with a 5-6 member heterocycle containing 1-3 heteroatoms independently selected from N, O and S or oxidized forms thereof), 5-6 member monocyclic heteroaryl (e.g., containing 1-4 heteroatoms independently selected from N, O and S), 8-10 member bicyclic heteroaryl (e.g., containing 1-4 heteroatoms independently selected from N, O and S) wherein each alkyl, carbocyclyl, heterocyclyl, aryl and heteroaryl is optionally substituted (e.g., substituted with 0, 1, 2 or 3 instances of $R^{10}$ wherein $R^{10}$ is as described herein)

In some embodiments, each $R^6$ is independently selected from H, —$C_1$-$C_6$ alkyl (e.g., -Me, -Et, —Pr, -$^i$Pr, -$^n$Bu, sec-Bu, -$^t$Bu), —$C_3$-$C_{10}$ monocyclic or bicyclic carbocyclyl (e.g., cyclopropyl, cyclobutyl, cyclopentyl, cyclohexyl, cycloheptyl, bicyclo[1.1.1]pentan-yl, 4,5,6,7-tetrahydro-1H-indazolyl, spiro[3.3]heptanyl), 3-10 membered mono or bicyclic heterocyclyl (e.g., oxetanyl, azepanyl, piperidinyl, pyrorolidinyl, tetrahydrofuranyl, tetrahydropyranyl, 1,2-dihydropyridinyl, morpholinyl), $C_6$-$C_{10}$ mono or bicyclic aryl (e.g., phenyl, naphthyl, 1,2,3,4-tetrahydronaphthalenyl, 2,3-dihydro-1H-indenyl, 1,2,3,4 tetrahydroquinolinyl, 1,2 dihydroquinolinyl, 1,2-dihydroisoquinolinyl, 1,2,3,4 tetrahydroisoquinolinyl, chromanyl, indolinyl, isoindolinyl, 3,4-dihydro-2H-benzo[b][1,4]oxazinyl, 2,3-dihydrobenzofuranyl, benzo[d][1,3]dioxolyl, 2,3-dihydro-1H-benzo[d]imidazolyl), 5-6 member monocyclic heteroaryl (e.g., thiophenyl, thiazolyl, pyrazolyl, imidazolyl, oxazolyl, pyridinyl, pyrimidinyl), 8-10 member bicyclic heteroaryl (e.g., benzo[d]isothiazolyl, indolyl, benzofuranyl, 1H-indazolyl, 2-H-indazolyl, benzo[b]thiophenyl, quinolinyl, 1,5-naphthyridinyl, 1,2-dihydro-1,5-naphthyridinyl, 1,2,3,4-tetrahydro-1,8-naphthyridinyl, isoquinolinyl, benzo[d]imidazolyl, benzo[d]thiazolyl, benzo[d]oxazolyl, [1,2,4]triazolo[4,3-a]pyridinyl, imidazo[1,2-a]pyridinyl, imidazo[1,5-a]pyridinyl, 1H-pyrazolo[4,3-b]pyridinyl), 1H-pyrazolo[3,4-b]pyridinyl, 1H-thieno[2,3-c]pyrazolyl, 1H-thieno[3,2-c]pyrazolyl, thiazolo[5,4-b]pyridinyl) wherein each alkyl, cycloalkyl, heterocyclyl, aryl and heteroaryl is optionally substituted (e.g., substituted with 0, 1, 2 or 3 instances of $R^{10}$ wherein $R^{10}$ is as described herein).

In some embodiments, each $R^6$ is independently selected from —$C_1$-$C_6$ alkyl (e.g., -Me, -Et, —Pr, -$^i$Pr, -$^n$Bu, sec-Bu, -$^t$Bu), —$C_3$-$C_{10}$ monocyclic or bicyclic carbocyclyl (e.g., cyclopropyl, cyclobutyl, cyclopentyl, cyclohexyl, cycloheptyl, bicyclo[1.1.1]pentan-yl, 4,5,6,7-tetrahydro-1H-indazolyl, spiro[3.3]heptanyl), 3-10 membered mono or bicyclic heterocyclyl (e.g., oxetanyl, azepanyl, piperidinyl, pyrorolidinyl, tetrahydrofuranyl, tetrahydropyranyl, 1,2-dihydropyridinyl, morpholinyl), $C_6$-$C_{10}$ mono or bicyclic aryl (e.g., phenyl, naphthyl, 1,2,3,4-tetrahydronaphthalenyl, 2,3-dihydro-1H-indenyl, 1,2,3,4 tetrahydroquinolinyl, 1,2 dihydroquinolinyl, 1,2-dihydroisoquinolinyl, 1,2,3,4 tetrahydroisoquinolinyl, chromanyl, indolinyl, isoindolinyl, 3,4-dihydro-2H-benzo[b][1,4]oxazinyl, 2,3-dihydrobenzofuranyl, benzo[d][1,3]dioxolyl, 2,3-dihydro-1H-benzo[d]imidazolyl), 5-6 member monocyclic heteroaryl (e.g., thiophenyl, thiazolyl, pyrazolyl, imidazolyl, oxazolyl, pyridinyl, pyrimidinyl), 8-10 member bicyclic heteroaryl (e.g., benzo[d]isothiazolyl, indolyl, benzofuranyl, 1H-indazolyl, 2-H-indazolyl, benzo[b]thiophenyl, quinolinyl, 1,5-naphthyridinyl, 1,2-dihydro-1,5-naphthyridinyl, 1,2,3,4-tetrahydro-1,8-naphthyridinyl, isoquinolinyl, benzo[d]imidazolyl, benzo[d]thiazolyl, benzo[d]oxazolyl, [1,2,4]triazolo[4,3-a]pyridinyl, imidazo[1,2-a]pyridinyl, imidazo[1,5-a]pyridinyl, 1H-pyrazolo[4,3-b]pyridinyl), 1H-pyrazolo[3,4-b]pyridinyl, 1H-thieno[2,3-c]pyrazolyl, 1H-thieno[3,2-c]pyrazolyl, thiazolo[5,4-b]pyridinyl) wherein each alkyl, cycloalkyl, heterocyclyl, aryl and heteroaryl is optionally substituted (e.g., substituted with 0, 1, 2 or 3 instances of $R^{10}$ wherein $R^{10}$ is as described herein).

In some embodiments, each $R^6$ is independently selected from H, -Me, -$^i$Pr, -$^n$Bu, sec-Bu, cyclobutyl, cyclopentyl, cyclohexyl, bicyclo[1.1.1]pentan-1-yl, spiro[3.3]heptan-2-yl, 4,5,6,7-tetrahydro-1H-indazol-6-yl, piperidin-4-yl, piperidin-3-yl, pyrrolidin-3-yl, 1,2-dihydropyridin-4-yl, phenyl, naphthalen-2-yl, 1,2,3,4 tetrahydroquinolin-6-yl, 1,2,3,4-tetrahydronaphthalen-6-yl, chroman-6-yl, 1,5-naphthyridin-6-yl, 1,2,3,4-tetrahydro-1,8-naphthyridin-6-yl, 2,3-dihydro-1H-inden-5-yl, indolin-5-yl, indolin-4-yl, 2,3-dihydro-1H-benzo[d]imidazol-5-yl, 2,3-dihydrobenzofuran-5-yl, 2,3-dihydrobenzofuran-6-yl, benzo[d][1,3]dioxol-5-yl], isoindolin-5-yl, 3,4-dihydro-2H-benzo[b][1,4]oxazin-7-yl, 1,2-dihydroquinolin-6-yl, 1,2-dihydroisoquinolin-7-yl, thiophen-2-yl, thiophen-3-yl, thiazol-2-yl, thiazol-4-yl, thiazol-5-yl, pyrazol-1-yl, pyrazol-5-yl, pyrazol-3-yl, pyrazol-4-yl, pyridin-2-yl, pyridin-3-yl, pyridin-4-yl, pyrimidin-5-yl, indol-4-yl, indol-5-yl, benzofuran-5-yl, benzofuran-6-yl, 1H indazol-5-yl, 1H indazol-4-yl, 2H-indazol-6-yl, 2H-indazol-5-yl, isoindolin-6-yl, benzo[d]isothiazol-5-yl, imidazo[1,2-a]pyridin-7-yl, imidazo[1,5-a]pyridin-6-yl, benzo[b]thiophen-3-yl, benzo[b]thiophen-5-yl, quinolin-6-yl, quinoline-3-yl, isoquinolin-6-yl, benzo[d]imidazo-5-yl, 1H-benzo[d]imidazol-4-yl, benzo[d]thiazol-5-yl, benzo[d]thiazol-6-yl, benzo[d]thiazol-4-yl, benzo[d]oxazol-4-yl, benzo[d]oxazol-5-yl, [1,2,4]triazolo[4,3-a]pyridin-6-yl, imidazo[1,2-a]pyridin-6-yl, pyrazolo[4,3-b]pyridin-6-yl, 1H-pyrazolo[3,4-b]pyridin-5-yl, 1H-pyrazolo[3,4-b]pyridin-5-yl, 1H-pyrazolo[4,3-b]pyridin-5-yl, 1H-pyrazolo[4,3-b]pyridin-6-yl, 1H-thieno[2,3-c]pyrazol-5-yl, 1H-thieno[3,2-c]pyrazol-5-yl, thiazolo[5,4-b]pyridin-6-yl), each optionally substituted (e.g., substituted with 0, 1, 2 or 3 instances of $R^{10}$ wherein $R^{10}$ is as described herein). In some embodiments, each $R^6$ is independently selected from -Me, -$^i$Pr, -$^n$Bu, sec-Bu, cyclobutyl, cyclopentyl, cyclohexyl, bicyclo[1.1.1]pentan-1-yl, spiro[3.3]heptan-2-yl, 4,5,6,7-tetrahydro-1H-indazol-6-yl, piperidin-4-yl, piperidin-3-yl, pyrrolidin-3-yl, 1,2-dihydropyridin-4-yl, phenyl, naphthalen-2-yl, 1,2,3,4 tetrahydroquinolin-6-yl, 1,2,3,4-tetrahydronaphthalen-6-yl, chroman-6-yl, 1,5-naphthyridin-6-yl, 1,2,3,4-tetrahydro-1,8-naphthyridin-6-yl, 2,3-dihydro-1H-inden-5-yl, indolin-5-yl, indolin-4-yl, 2,3-dihydro-1H-benzo[d]imidazol-5-yl, 2,3-dihydrobenzofuran-5-yl, 2,3-dihydrobenzofuran-6-yl, benzo[d][1,3]dioxol-5-yl], isoindolin-5-yl, 3,4-dihydro-2H-benzo[b][1,4]oxazin-7-yl, 1,2-dihydroquinolin-6-yl, 1,2-dihydroisoquinolin-7-yl, thiophen-2-yl, thiophen-3-yl, thiazol-2-yl, thiazol-4-yl, thiazol-5-yl, pyrazol-1-yl, pyrazol-5-yl, pyrazol-3-yl, pyrazol-4-yl, pyridin-2-yl, pyridin-3-yl, pyridin-4-yl, pyrimidin-5-yl, indol-4-yl, indol-5-yl, benzofuran-5-yl, benzofuran-6-yl, 1H indazol-5-yl, 1H indazol-4-yl, 2H-indazol-6-yl, 2H-indazol-5-yl, isoindolin-6-yl, benzo[d]isothiazol-5-yl, imidazo[1,2-a]pyridin-7-yl, imidazo[1,5-a]pyridin-6-yl, benzo[b]thiophen-3-yl, benzo[b]thiophen-5-yl, quinolin-6-yl, quinoline-3-yl, isoquinolin-6-yl, benzo[d]imidazo-5-yl, 1H-benzo[d]imidazol-4-yl, benzo[d]thiazol-5-yl, benzo[d]thiazol-6-yl, benzo[d]thiazol-4-yl, benzo[d]oxazol-4-yl, benzo[d]oxazol-5-yl, [1,2,4]triazolo[4,3-a]pyridin-6-yl, imidazo[1,2-a]pyridin-6-yl, pyrazolo[4,3-b]pyridin-6-yl, 1H-pyrazolo[3,4-b]pyridin-5-yl, 1H-pyrazolo[3,4-b]pyridin-5-yl, 1H-pyrazolo[4,3-b]pyridin-5-yl, 1H-pyrazolo[4,3-b]pyridin-6-yl, 1H-thieno[2,3-c]pyrazol-5-yl, 1H-thieno[3,2-c]pyrazol-5-yl, thiazolo[5,4-b]pyridin-6-yl), each optionally substituted (e.g., substituted with 0, 1, 2 or 3 instances of $R^{10}$ wherein $R^{10}$ is as described herein).

In some embodiments, $R^6$ is H. In some embodiments $R^6$ is -D.

In certain embodiments, $R^6$ is halo (e.g., fluoro, chloro, bromo, iodo). In further embodiments, $R^6$ is —Cl. In some embodiments, $R^6$ is —F. In some embodiments, $R^6$ is —Br. In some embodiments, $R^6$ is —I.

In some embodiments, $R^6$ is —CN.

In certain embodiments, $R^6$ is —$C_1$-$C_6$ alkyl (e.g., -Me, -Et, —Pr, -$^i$Pr, -$^n$Bu, sec-Bu, -$^t$Bu). In further embodiments, $R^6$ is -Me. In some embodiments, $R^6$ is -Et. In some embodiments $R^6$ is propyl. In some embodiments, $R^6$ is isopropyl. In some embodiments $R^6$ is sec-Bu. In some embodiments, $R^6$ is -$^t$Bu.

In some embodiments, $R^6$ is —$C_1$-$C_6$ heteroalkyl. In further embodiments, $R^6$ is methoxymethyl (—$CH_2OCH_3$). In some embodiments, $R^6$ is hydroxymethyl (—$CH_2OH$). In some embodiments, $R^6$ is aminomethyl (e.g., —$CH_2NH_2$, —$CH_2NHCH_3$, —$CH_2N(CH_3)_2$.

In some embodiments, $R^6$ is —$C_1$-$C_6$ haloalkyl. In further embodiments, $R^6$ is trifluoromethyl (—$CF_3$). In other embodiments, $R^6$ is difluoromethyl (—$CHF_2$).

In some embodiments, $R^6$ is —$C_3$-$C_{10}$ carbocyclyl. In some embodiments, the carbocyclyl is not further substituted. In some embodiments, the carbocyclyl is substituted with 0, 1, 2 or 3 instances of $R^{10}$, wherein $R^{10}$ is as described herein. In some embodiments, the carbocyclyl is substituted with 1 or 2 instances of halo (e.g., —F, —Cl), -Me, -Et, -$^i$Pr, —OH, =O or —CN. In further embodiments, the carbocyclyl is a —$C_3$-$C_{10}$ mono or bicyclic cycloalkyl (e.g., a monocyclic cycloalkyl, a fused bicyclic cycloalkyl, a spiro cycloalkyl or a bridged cycloalkyl). In some embodiments, the carbocyclyl is a —$C_3$-$C_7$ monocyclic cycloalkyl (e.g., cyclopropyl, cyclobutyl, cyclopentyl, cyclohexyl). In some embodiments, $R^6$ is cyclopropyl. In some embodiments $R^6$ is cyclobutyl. In some embodiments, $R^6$ is cyclopentyl. In some embodiments, $R^6$ is cyclohexyl. In some embodiments, the carbocyclyl is a —$C_4$-$C_{10}$ bicyclic cycloalkyl. In some embodiments, $R^6$ is a —$C_4$-$C_{10}$ fused cycloalkyl (e.g., decahydronaphthyl, octahydroindenyl). In some embodiments, $R^6$ is a —$C_4$-$C_{10}$ spiro cycloalkyl (e.g., spiro[4.5]decanyl, spiro[4.4]nonanyl, spiro[3.3]heptanyl, spiro[3.4]octanyl). In further embodiments, $R^6$ is spiro[3.3]heptanyl. In some embodiments, $R^6$ is a bridged bicyclic cycloalkyl (e.g., bicyclo[1.1.1]pentanyl, bicyclo[2.2.1]heptanyl, bicyclo[3.3.1]heptanyl, bicyclo[2.1.1]hexanyl, bicyclo[3.2.1]octanyl, bicyclo[3.3.1]nonanyl. In some embodiments, $R^6$ is bicyclo[1.1.1]pentanyl.

In some embodiments, the carbocyclyl is a —$C_3$-$C_7$ monocyclic carbocyclyl fused with phenyl (e.g., 1,2,3,4-tetrahydronaphthalenyl, 2,3-dihydro-1H-indenyl wherein the attachment point is on the saturated ring). In some embodiments, $R^6$ is a —$C_3$-$C_7$ monocyclic carbocyclyl fused with a 5-6-member heterocyclyl ring containing 1-3 atoms independently selected from N, O, S or oxidized forms thereof (e.g., octahydrochromenyl, decahydroisoquinolinyl, decahydroquinolinyl, octahydroindolyl, octahydroisoindolyl hexahydro chromane, hexahydro isoquinoline, hexahydroquinoline, octahydrobenzofuran wherein the attachment point is on the carbocyclic ring). In some embodiments, $R^6$ is a —$C_3$-$C_7$ monocyclic carbocyclyl fused with a 5-6-member heteroaryl ring containing 1-3 atoms independently selected from N, O, S or oxidized forms thereof (e.g., 4,5,6,7-tetrahydro-1H-indazolyl). In one embodiment, $R^6$ is 4,5,6,7-tetrahydro-1H-indazol-6-yl.

In certain embodiments, $R^6$ is selected from:

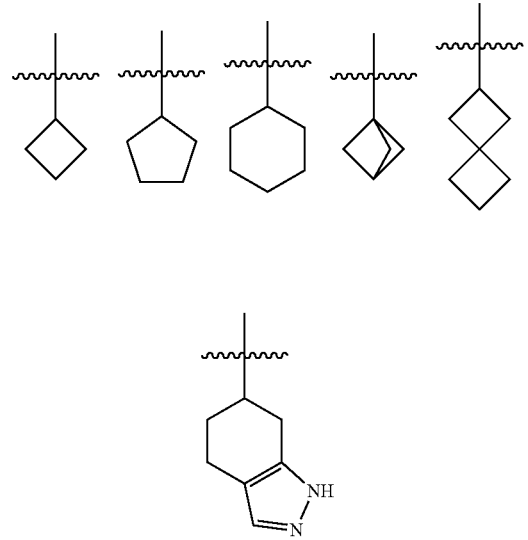

In some embodiments, $R^6$ is a 3-10 membered mono or bicyclic heterocyclyl. In some embodiments, $R^6$ is a 3-8 member monocyclic heterocyclyl containing 1-3 heteroatoms selected from N, O and S or oxidized forms thereof (e.g., oxetanyl, tetrahydropyranyl, tetrahydrofuranyl, azetidinyl, pyrrolidinyl, piperidinyl, piperazinyl, morpholinyl, azepanyl, tetrahydropyridinyl). In some embodiments, $R^6$ is oxetanyl. In some embodiments, $R^6$ is tetrahydropyranyl. In some embodiments, $R^6$ is tetrahydrofuranyl. In some embodiments, $R^6$ is azetidinyl. In some embodiments, $R^6$ is pyrrolidinyl. In some embodiments, $R^6$ is piperidinyl. In some embodiments, $R^6$ is piperazinyl. In some embodiments, $R^6$ is morpholinyl. In some embodiments, $R^6$ is azepanyl. In some embodiments, $R^6$ is tetrahydropyridinyl. In some embodiments, $R^6$ is a 4-10 member bicyclic heterocyclyl containing 1-3 heteroatoms independently selected from N, O and S or oxidized forms thereof. In some embodiments, the mono or bicyclic heterocyclyl is not further substituted. In some embodiments, the heterocyclyl is substituted with 1 or 2 instances of halo (e.g., —F, —Cl), -Me, -Et, -$^i$Pr, —OH, =O or —CN. In some instances, the heterocyclyl is substituted with =O (e.g., 2-oxo-1,2-dihydropyridin-4-yl). In some embodiments, $R^6$ is an optionally substituted 6-10 member mono or bicyclic aryl. In some embodiments, $R^6$ is substituted with 0, 1, 2 or 3 instances of $R^{10}$, wherein $R^{10}$ is as described herein.

In some embodiments, $R^6$ is optionally substituted phenyl. In some embodiments, $R^6$ is phenyl substituted with 0, 1, 2 or 3 instances of $R^{10}$, wherein each $R^{10}$ is independently as described herein. In some embodiments, the phenyl is unsubstituted. In some embodiments, the phenyl is substituted with one instance of $R^{10}$. In some embodiments, the phenyl is substituted with 1 instance of $R^{10}$ at the position para- to the attachment point to the piperidine.

In some embodiments, $R^6$ is

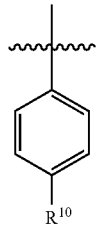

$R^{10}$. In some embodiments, the phenyl is substituted with 2 instances of $R^{10}$. In some embodiments, the phenyl is substituted with 3 instances of $R^{10}$. In some embodiments, $R^6$ is phenyl substituted with halo (e.g., fluoro, chloro, bromo).

In some embodiments, $R^6$ is an optionally substituted 9-10 member bicyclic aryl (e.g., naphthyl). In some embodiments, $R^6$ is an optionally substituted bicyclic aryl containing a phenyl ring fused with a $C_5$-$C_6$ carbocycle (e.g., tetrahydronaphthyl, dihydroindenyl). In some embodiments, $R^6$ is 1,2,3,4-tetrahydronaphthalenyl. In some embodiments, $R^6$ is 2,3-dihydro-1H-indenyl. In some embodiments, $R^6$ is an optionally substituted bicyclic aryl containing a phenyl ring fused with a 5-6 member heterocycle containing 1-3 heteroatoms independently selected from N, O and S or oxidized forms thereof (e.g., tetrahydronaphthalenyl, dihydroindenyl, 1,2,3,4 tetrahydroquinolinyl, 1,2 dihydroquinolinyl, 1,2-dihydroisoquinolinyl, tetrahydroisoquinolinyl, chromanyl, indolinyl, isoindolinyl, dihydrobenzoxazinyl, dihydrobenzofuranyl, benzodioxolyl, dihydrobenzimidazolyl. In some embodiments, $R^6$ is 1,2,3,4 tetrahydroquinolinyl. In some embodiments, $R^6$ is 1,2 dihydroquinolinyl. In some embodiments, $R^6$ is 1,2-dihydroisoquinolinyl. In some embodiments, $R^6$ is 1,2,3,4 tetrahydroisoquinolinyl. In some embodiments, $R^6$ is chromanyl. In some embodiments, $R^6$ is indolinyl. In some embodiments, $R^6$ is isoindolinyl. In some embodiments, $R^6$ is 3,4-dihydro-2H-benzo[b][1,4]oxazinyl. In some embodiments, $R^6$ is 2,3-dihydrobenzofuranyl. In some embodiments, $R^6$ is benzo[d][1,3]dioxolyl. In some embodiments, $R^6$ is 2,3-dihydro-1H-benzo[d]imidazolyl. In some embodiments, $R^6$ is selected from:

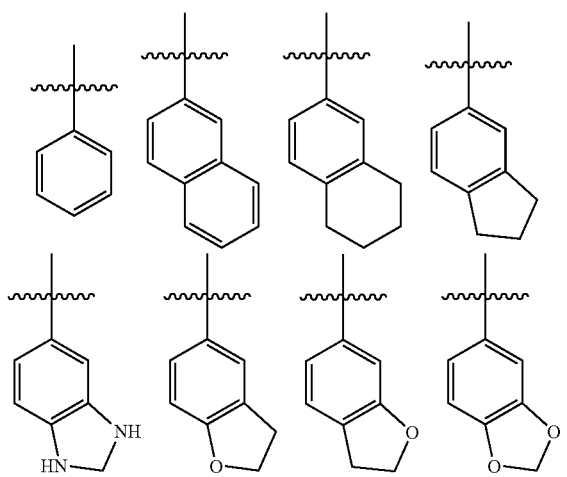

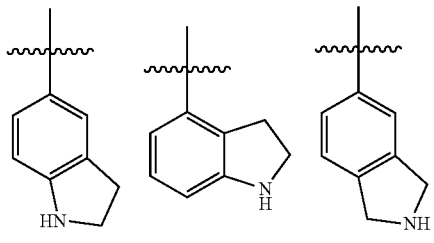

In some embodiments, the bicyclic aryl is unsubstituted. In some embodiments, the bicyclic aryl is substituted with 0, 1, 2 or 3 instances of $R^{10}$, wherein each $R^{10}$ is as described herein. In some embodiments, the bicyclic aryl is substituted with 1 instance of $R^{10}$. In further embodiments, the bicyclic aryl is substituted with one instance of $R^{10}$ wherein $R^{10}$ is selected from halo (e.g., F, Cl, Br), -Me, =O. In some embodiments, $R^{10}$ is =O and $R^6$ is selected from:

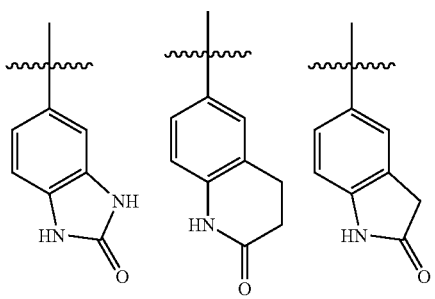

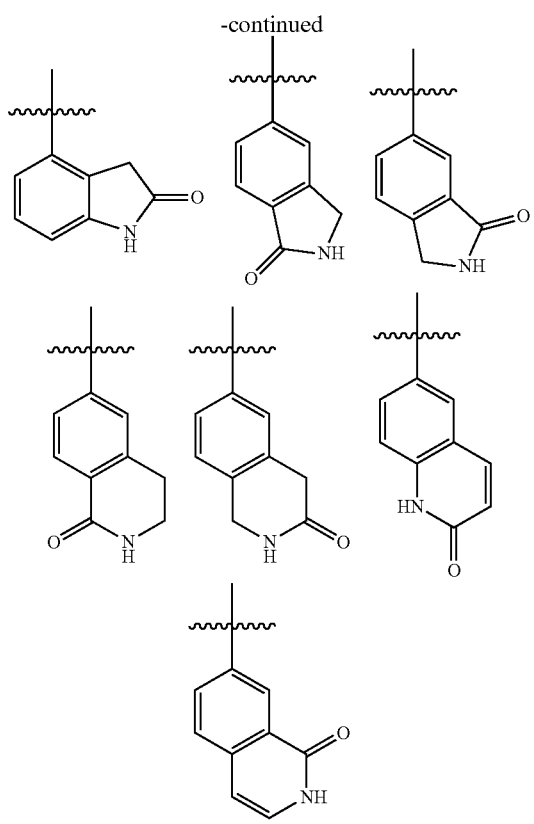

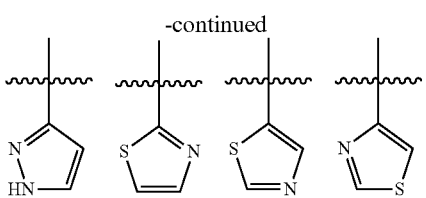

In some embodiments, R⁶ is a 6-member monocyclic heteroaryl (e.g., pyridyl, pyrimidinyl, triazinyl, pyrazinyl, pyridazinyl). In some embodiments, the 6-member monocyclic heteroaryl is unsubstituted. In some embodiments, the 6-member monocyclic heteroaryl is substituted with 0, 1, 2 or 3 instances of R¹⁰. In some embodiments, the 6-member monocyclic heteroaryl is substituted with 1 instance of R¹⁰. In some embodiments, the 6-member monocyclic heteroaryl is substituted with 1 instance of R¹⁰ at the position para to the attachment point to the piperidine. In some embodiments, the he 6-member monocyclic heteroaryl is substituted with 2 instances of R¹⁰. In some embodiments, the 6-member monocyclic heteroaryl is substituted with 3 instances of R¹⁰. In some embodiments, R⁶ is pyridinyl (e.g., pyridin-2-yl, pyridin-3-yl, pyridin-4-yl). In some embodiments, R⁶ is pyrimidinyl (e.g., pyrimidin-2-yl, pyrimidin-4-yl, pyrimidin-5-yl). In some embodiments, R⁶ is selected from:

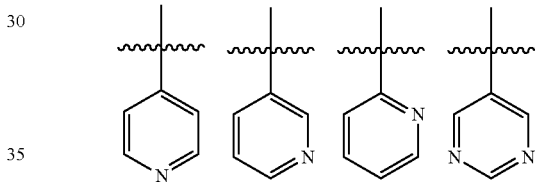

In some embodiments, R⁶ is selected from:

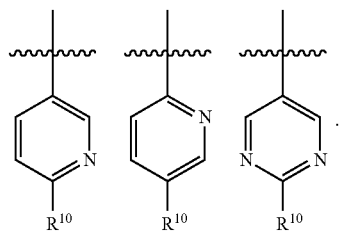

In further embodiments, R⁶ is

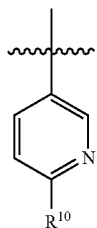

In some embodiments, R⁶ is an optionally substituted 5-6 member monocyclic heteroaryl (e.g., a 5-member monocyclic heteroaryl containing 1-3 heteroatoms independently selected from O, N and S, a 6-member monocyclic heteroaryl containing 1-3 N heteroatoms). In some embodiments, the 5-6 member monocyclic heteroaryl is unsubstituted. In some embodiments, the 5-6 member monocyclic heteroaryl is substituted with 0, 1, 2 or 3 instances of R¹⁰, wherein each R¹⁰ is as described herein. In some embodiments, the 5-6 member monocyclic heteroaryl is substituted with 1 instance of R¹⁰. In some embodiments, the 5-6 member monocyclic heteroaryl is substituted with 2 instances of R¹⁰. In some embodiments, the 5-6 member monocyclic heteroaryl is substituted with 2 instances of R¹⁰. In some embodiments, the 5-6 member monocyclic heteroaryl is substituted with 3 instances of R¹⁰.

In some embodiments, R⁶ is a 5-member monocyclic heteroaryl (e.g., pyrazolyl, pyrolyl, thiophenyl, furyl, thiazolyl, isothiazolyl, oxazolyl, isoxazolyl, imidazolyl, triazolyl, thiadiazolyl, oxadiazolyl). In some embodiments, R⁶ is thiophenyl (e.g., thiophen-2-yl, thiophen-3-yl). In some embodiments, R⁶ is pyrazolyl (e.g. pyrazol-1-yl, pyrazol-3-yl, pyrazol-5-yl). In some embodiments, R⁶ is thiazolyl (e.g., thiazol-2-yl, thiazol-4-yl, thiazol-5-yl). In some embodiments, R⁶ is selected from:

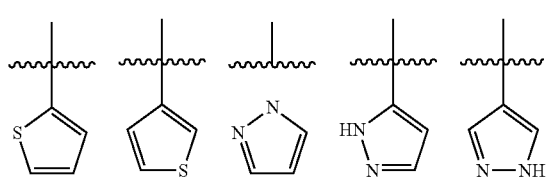

In some embodiments, R⁶ is an 8-10 member bicyclic heteroaryl (e.g., a 5,5 bicyclic heteroaryl (e.g. 1H-thieno[2,3-c]pyrazolyl, 1H-thieno[3,2-c]pyrazolyl), a 5,6 bicyclic heteroaryl (e.g., indolyl, benzofuranyl, 1H-indazolyl, 2H-indazolyl, benzo[b]thiophenyl, benzo[d]imidazolyl, benzo[d]thiazolyl, benzo[d]oxazolyl, [1,2,4]triazolo[4,3-a]pyridinyl, benzo[d]isothiazolyl, imidazo[1,2-a]pyridinyl, imidazo[1,2-a]pyridinyl, 1H-pyrazolo[4,3-b]pyridinyl), 1H-pyrazolo[3,4-b]pyridinyl, thiazolo[5,4-b]pyridinyl), or a 6,6 bicyclic heteroaryl (e.g., quinolinyl, 1,5-naphthyridinyl, 1,2-dihydro-1,5-naphthyridinyl, 1,2,3,4-tetrahydro-1,8-naphthyridinyl, isoquinolinyl), wherein each bicyclic heteroaryl contains 1-3 heteroatoms independently selected from O, N and S).

In some embodiments $R^6$ is selected from indolyl, benzofuranyl, 1H-indazolyl, 2H-indazolyl, benzo[b]thiophenyl, quinolinyl, 1,5-naphthyridinyl, 1,2-dihydro-1,5-naphthyridinyl, 1,2,3,4-tetrahydro-1,8-naphthyridinyl, isoquinolinyl, benzo[d]imidazolyl, benzo[d]thiazolyl, benzo[d]oxazolyl, [1,2,4]triazolo[4,3-a]pyridinyl, imidazo[1,2-a]pyridinyl, benzo[d]isothiazolyl, imidazo[1,2-a]pyridinyl, 1H-pyrazolo[4,3-b]pyridinyl), 1H-pyrazolo[3,4-b]pyridinyl, 1H-thieno[2,3-c]pyrazolyl, 1H-thieno[3,2-c]pyrazolyl, thiazolo[5,4-b]pyridinyl, 1,2,3,4-tetrahydro-1,8-naphthyridinyl) wherein the bicyclic heteroaryl is optionally substituted (e.g., substituted with 0, 1, 2 or 3 instances of $R^{10}$).

In some embodiments $R^6$ is an 8-10 member bicyclic heteroaryl selected from:

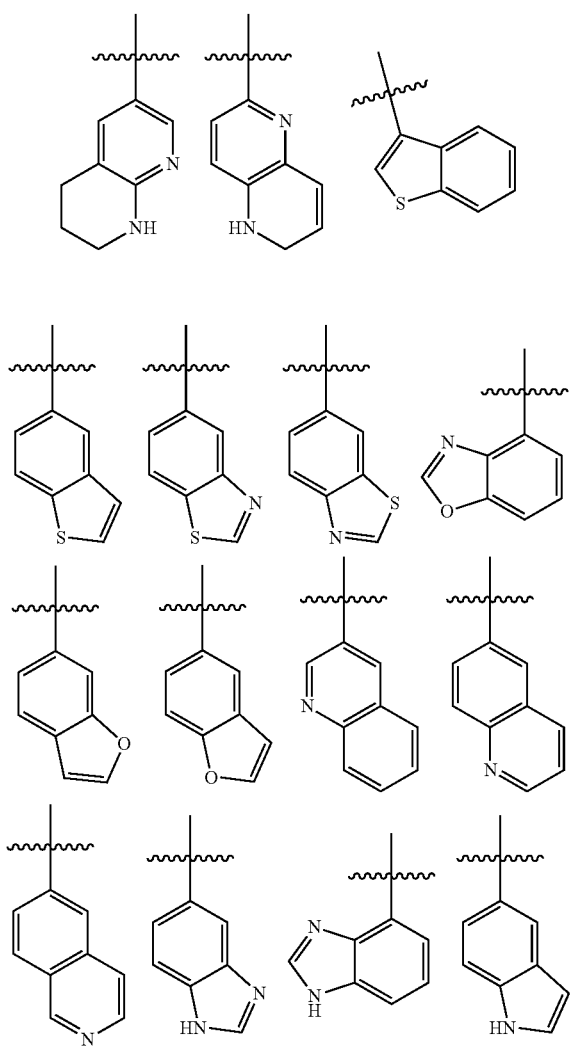

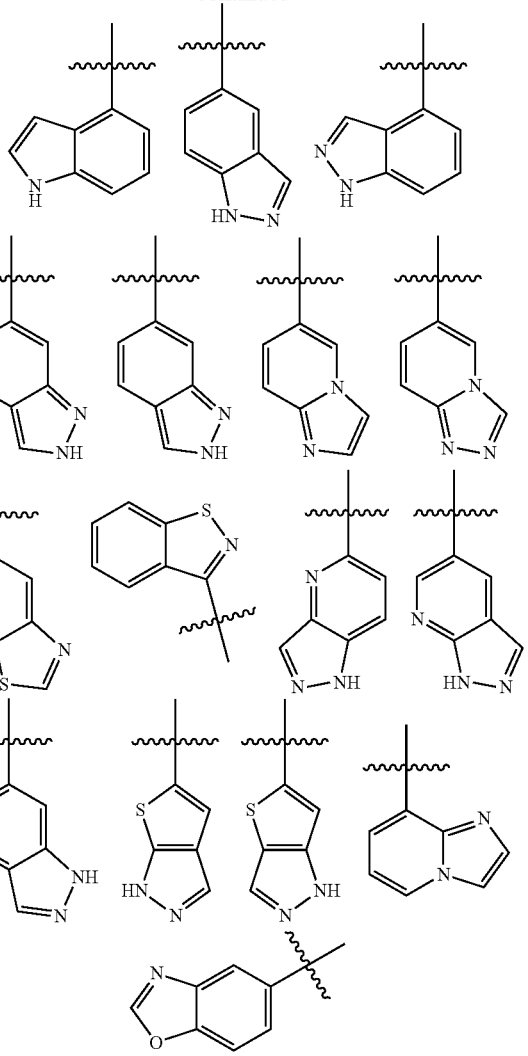

In some embodiments, the 8-10 member bicyclic heteroaryl is unsubstituted. In some embodiments, the 8-10 member bicyclic heteroaryl is substituted with 0, 1, 2 or 3 instances of $R^{10}$, wherein each $R^{10}$ is as described herein. In some embodiments, the 8-10 member bicyclic heteroaryl is substituted with 1 instance of $R^{10}$. In further embodiments, the 8-10 member bicyclic heteroaryl is substituted with one instance of $R^{10}$ wherein $R^{10}$ is selected from halo (e.g., F, Cl, Br), -Me, =O. In some embodiments, $R^{10}$ is =O and $R^6$ is selected from:

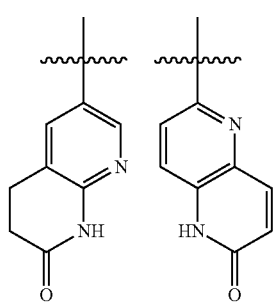

In some embodiments $R^6$ is cycloalkylalkyl (e.g., cyclopropylmethyl, cyclobutylmethyl, cyclopentylmethyl, cyclohexylmethyl, cycloheptylmethyl). In some embodiments, $R^6$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, $R^6$ is arylalkyl. In some embodiments, $R^6$ is benzyl.

In some embodiments, $R^6$ is heteroarylalkyl (e.g., pyridinylmethyl, thiazolylmethyl, triazolylmethyl, pyrazolylmethyl).

In some embodiments, $R^6$ is —$OR^{a6}$ (e.g., hydroxy (—OH), methoxy, difluoromethoxy (—$OCHF_2$), trifluoromethoxy (—$OCF_3$), ethoxy, propoxy, isopropoxy, cyclopropyloxy, cyclobutyloxy). In some embodiments, $R^6$ is hydroxy. In some embodiments, $R^6$ is methoxy. In some embodiments, $R^6$ is ethoxy. In some embodiments, $R^6$ is propoxy. In some embodiments, $R^6$ is isopropoxy. In some embodiments $R^6$ is difluoromethoxy. (—$OCHF_2$). In some embodiments, $R^6$ is trifluoromethoxy (—$OCF_3$).

In some embodiments, $R^6$ is —$N(R^{a6})_2$ (e.g., —$NH_2$, —N—$R^{a6}$, —$N(CH_3)R^{a6}$). In some embodiments, $R^6$ is —$NH_2$. In some embodiments, $R^6$ is —$NHR^{a6}$ (e.g., —NHMe, —NHEt, —NHPr, —$NH^iPr$, —NHcyclopropyl, —NHcyclobutyl). In some embodiments, $R^6$ is —$N(CH_3)R^{a6}$ (e.g., —$NMe_2$, —$N(CH_3)Et$, —$N(CH_3)Pr$, —$N(CH_3)^iPr$, —$N(CH_3)$cyclopropyl, —$N(CH_3)$cyclobutyl). In some embodiments, $R^6$ is —$C(=O)R^{a6}$ or —$C(=O)OR^{a6}$. In some embodiments, $R^6$ is —$C(=O)R^{a6}$ wherein $R^{a6}$ is as described herein. In some embodiments, $R^6$ is —$C(=O)$alkyl. In some embodiments, $R^6$ is —$C(O)CH_3$, —$C(O)$cyclopropyl, —$C(O)$cyclobutyl, —$C(O)^iBu$, —$C(O)^iPr$, —$C(O)Pr$, —$C(O)^tBu$, or —$C(=O)OMe$. In some embodiments, $R^6$ is acetyl (—$C(=O)Me$). In some embodiments, $R^6$ is —$C(=O)OR^{a6}$. In some embodiments, $R^6$ is —COOH. In some embodiments, $R^6$ is COOMe.

In some embodiments, $R^6$ is —$NR^{a6}C(=O)R^{a6}$. In certain embodiments, $R^6$ is —$NHC(=O)R^{a6}$ (e.g., NHC(=O)Me, NHC(=O)Et, NHC(=O)Pr, NHC(=O)$^iPr$, NHC(=O)Bu, NHC(=O)$^tBu$, NHC(=O)Cyclopropyl, NHC(=O)Cyclobutyl). In some embodiments, $R^6$ is —$N(CH_3)C(=O)R^{a6}$ (e.g., $N(CH_3)C(=O)Me$, $N(CH_3)C(=O)Et$, $N(CH_3)C(=O)Pr$, $N(CH_3)C(=O)^iPr$, $N(CH_3)C(=O)Bu$, $N(CH_3)C(=O)^tBu$, $N(CH_3)C(=O)$Cyclopropyl, $N(CH_3)C(=O)$Cyclobutyl). In some embodiments, $R^6$ is —$NR^{a6}C(=O)OR^{a6}$. In certain embodiments, $R^6$ is —NHC(=O)$OR^{a6}$ (e.g., NHC(=O)OMe, NHC(=O)OEt, NHC(=O)OPr, NHC(=O)O$^iPr$, NHC(=O)OBu, NHC(=O)O$^tBu$, NHC(=O)OCyclopropyl, NHC(=O)OCyclobutyl). In some embodiments, $R^6$ is —$N(CH_3)C(=O)OR^{a6}$ (e.g., $N(CH_3)C(=O)OMe$, $N(CH_3)C(=O)OEt$, $N(CH_3)C(=O)OPr$, $N(CH_3)C(=O)O^iPr$, $N(CH_3)C(=O)OBu$, $N(CH_3)C(=O)O^tBu$, $N(CH_3)C(=O)O$Cyclopropyl, $N(CH_3)C(=O)OC$yclobutyl).

In some embodiments, $R^6$ is —$C(=O)N(R^{a6})_2$ (e.g., —$C(=O)NH_2$, —$C(=O)NHR^{a6}$—$C(=O)N(CH_3)R^{a6}$). In some embodiments, $R^6$ is —$C(=O)NH_2$. In certain embodiments, $R^6$ is —$C(=O)NHR^{a6}$ (e.g., —$C(=O)NHMe$, —$C(=O)NHEt$, —$C(=O)NHPr$, —$C(=O)NH^iPr$, —$C(=O)NHBu$, —$C(=O)NH^tBu$, —$C(=O)NHC$yclopropyl, —$C(=O)NHC$yclobutyl). In certain embodiments, $R^6$ is —$C(=O)N(CH_3)R^{a6}$ (e.g., —$C(=O)NMe_2$, —$C(=O)N(CH_3)Et$, —$C(=O)N(CH_3)Pr$, —$C(=O)N(CH_3)^iPr$, —$C(=O)N(CH_3)Bu$, —$C(=O)N(CH_3)^tBu$, —$C(=O)N(CH_3)$Cyclopropyl, —$C(=O)N(CH_3)$Cyclobutyl).

In some embodiments, $R^6$ is —$OC(=O)N(R^{a6})_2$. In certain embodiments, $R^6$ is —$OC(=O)NHR^{a6}$ (e.g., —$OC(=O)NHMe$, —$OC(=O)NHEt$, —$OC(=O)NHPr$, —$OC(=O)NH^iPr$, —$OC(=O)NHBu$, —$OC(=O)NH^tBu$, —$OC(=O)NHC$yclopropyl, —$OC(=O)NHC$yclobutyl). In certain embodiments, $R^6$ is —$OC(=O)N(CH_3)R^{a6}$ (e.g., —$OC(=O)NMe_2$, —$OC(=O)N(CH_3)Et$, —$OC(=O)N(CH_3)Pr$, —$OC(=O)N(CH_3)^iPr$, —$OC(=O)N(CH_3)Bu$, —$OC(=O)N(CH_3)^tBu$, —$OC(=O)N(CH_3)$Cyclopropyl, —$OC(=O)N(CH_3)$Cyclobutyl).

In some embodiments, $R^6$ is —$S(=O)R^{a6}$. In certain embodiments, $R^6$ is —S(=O)alkyl (e.g., —S(=O)Me, —S(=O)Et, —S(=O)Pr, —S(=O)$^iPr$). In certain embodiments, $R^6$ is —S(=O)cycloalkyl (e.g., —S(=O)cyclopropyl, —S(=O)cyclobutyl, —S(=O)cyclopentyl, —S(=O)cyclohexyl).

In some embodiments, $R^6$ is —$S(=O)_2R^{a6}$. In certain embodiments, $R^6$ is —$S(=O)_2$ alkyl (e.g., —$S(=O)_2Me$, —$S(=O)_2Et$, —$S(=O)_2Pr$, —$S(=O)_2^iPr$). In certain embodiments, $R^6$ is —$S(=O)_2$cycloalkyl (e.g., —$S(=O)_2$cyclopropyl, —$S(=O)_2$cyclobutyl, —$S(=O)_2$cyclopentyl, —$S(=O)_2$cyclohexyl). In some embodiments, $R^6$ is $S(=O)_2$ aryl (e.g., $S(=O)_2$phenyl).

In some embodiments, $R^6$ is —$SR^{a6}$. In certain embodiments, $R^6$ is —Salkyl (e.g., —SMe, —SEt, —SPr, —S$^iPr$). In certain embodiments, $R^6$ is —Scycloalkyl (e.g., —Scyclopropyl, —Scyclobutyl, —Scyclopentyl, —Scyclohexyl). In certain embodiments, $R^6$ is —Saryl (e.g., Sphenyl).

In some embodiments, $R^6$ is —$S(=O)(=NR^{a6})R^{a6}$. In certain embodiments, $R^6$ is —S(=O)(=NH)$R^{a6}$ (e.g., —S(=O)(=NH)Me, —S(=O)(=NH)Et, —S(=O)(=NH)Pr, —S(=O)(=NH)$^iPr$, —S(=O)(=NH)Bu, —S(=O)(=NH)$^tBu$, —S(=O)(=NH)Cyclopropyl, —S(=O)(=NH)Cyclobutyl). In some embodiments, $R^6$ is —S(=O)(=$NCH_3$)$R^{a6}$ (e.g., —S(=O)(=$NCH_3$)Me, —S(=O)(=$NCH_3$)Et, —S(=O)(=$NCH_3$)Pr, —S(=O)(=$NCH_3$)$^iPr$, —S(=O)(=$NCH_3$)Bu, —S(=O)(=$NCH_3$)Bu, —S(=O)(=$NCH_3$)Cyclopropyl, —S(=O)(=$NCH_3$)Cyclobutyl).

In some embodiments, $R^6$ is —$NR^{a6}S(=O)_2R^{a6}$. In certain embodiments, $R^6$ is —$NHS(=O)_2$ alkyl (e.g., —$NHS(=O)_2Me$, —$NHS(=O)_2Et$, —$NHS(=O)_2Pr$, —$NHS(=O)_2^iPr$). In certain embodiments, $R^6$ is —$NHS(=O)_2$cycloalkyl (e.g., —$NHS(=O)_2$cyclopropyl, —$NHS(=O)_2$cyclobutyl, —$NHS(=O)_2$cyclopentyl, —$NHS(=O)_2$cyclohexyl). In certain embodiments, $R^6$ is —$N(CH_3)S(=O)_2$ alkyl (e.g., —$N(CH_3)S(=O)_2Me$, —$N(CH_3)S(=O)_2Et$, —$N(CH_3)S(=O)_2Pr$, —$N(CH_3)S(=O)_2^iPr$). In certain embodiments, $R^6$ is —$N(CH_3)S(=O)_2$cycloalkyl (e.g., —$N(CH_3)S(=O)_2$cyclopropyl, —$N(CH_3)S(=O)_2$cyclobutyl, —$N(CH_3)S(=O)_2$cyclopentyl, —$N(CH_3)S(=O)_2$cyclohexyl).

In some embodiments, $R^6$ is —$S(=O)_2N(R^{a6})_2$. (e.g., —$S(=O)_2NH_2$, —$S(=O)_2NHR^{a6}$, —$S(=O)_2N(CH_3)R^{a6}$). In some embodiments, $R^6$ is —$S(=O)_2NH_2$. In some embodiments, $R^6$ is —$S(=O)_2NHR^{a6}$ (e.g., —$S(=O)_2NHMe$, —$S(=O)_2NHEt$, —$S(=O)_2NHPr$, —$S(=O)_2NH^iPr$, —$S(=O)_2NH$cyclopropyl, —$S(=O)_2NH$cyclobutyl). In some embodiments, $R^6$ is —$S(=O)_2N(CH_3)R^{a6}$ (e.g., —$S(=O)_2NMe_2$, —$S(=O)_2N(CH_3)Et$, —$S(=O)_2N(CH_3)Pr$, —$S(=O)_2N(CH_3)^iPr$, —$S(=O)_2N(CH_3)$cyclopropyl, —$S(=O)_2N(CH_3)$cyclobutyl).

As generally defined herein, each $R^7$ is independently absent or selected from H, -D, halo, —CN, —$C_1$-$C_6$ alkyl, —$C_1$-$C_6$ hydroxyalkyl, —$C_1$-$C_6$ haloalkyl, —$C_3$-$C_9$ cycloalkyl, 3-10 membered heterocyclyl, 5-6-membered monocyclic heteroaryl, heterocyclylalkyl, heteroarylalkyl, arylalkyl, cycloalkylalkyl, —OR$^{a7}$, —N(R$^{a7}$)$_2$, —C(=O)R$^{a7}$, —C(=O)OR$^{a7}$, —NR$^{a7}$C(=O)R$^{a7}$, —NR$^{a7}$C(=O)OR$^{a7}$, —C(=O)N(R$^{a7}$)$_2$, —OC(=O)N(R$^{a7}$)$_2$, —S(=O)R$^{a7}$, —S(=O)$_2$R$^{a7}$, —SR$^{a7}$, —S(=O)(=NR$^{a7}$)R$^{a7}$, —NR$^{a7}$S(=O)$_2$R$^{a7}$ and —S(=O)$_2$N(R$^{a7}$)$_2$, wherein R$^{a7}$ is as defined herein.

In some embodiments, each R$^7$ is independently selected from H, halo (e.g., F, Cl), —CN, —C$_1$-C$_6$ alkyl (e.g., -Me, -Et, —Pr, -$^i$Pr, -sec-Bu, -$^t$Bu), 5-membered heteroaryl (e.g., pyrazolyl), —C$_1$-C$_6$ haloalkyl (e.g., —CF$_3$, —CHF$_2$, —CH$_2$CF$_3$), —C$_1$-C$_6$ hydroxyalkyl (e.g., —CH$_2$OH), —C$_3$-C$_9$ cycloalkyl (e.g., cyclopropyl, cyclobutyl, cyclopentyl, cyclohexyl), —OR$^{a7}$ (e.g., —OH, —OMe, —OCHF$_2$), —N(R$^{a7}$)$_2$ and —C(=O)N(R$^{a7}$)$_2$ (e.g., —C(=O)NH$_2$, —C(=O)NHMe), wherein each R$^{a7}$ is as defined herein. In further embodiments, each R$^{a7}$ is independently selected from H and —C$_1$-C$_6$ alkyl (e.g., -Me, -Et, —Pr, -$^i$Pr, -$^n$Bu, $^t$-Bu, -sec-Bu, -iso-Bu).

In certain embodiments, each R$^7$ is independently selected from H and methyl.

In some embodiments, R$^7$ is H. In some embodiments R$^7$ is -D.

In certain embodiments, R$^7$ is halo (e.g., fluoro, chloro, bromo, iodo). In further embodiments, R$^7$ is —Cl. In some embodiments, R$^7$ is —F. In some embodiments, R$^7$ is —Br. In some embodiments, R$^7$ is —I.

In some embodiments, R$^7$ is —CN.

In certain embodiments, R$^7$ is —C$_1$-C$_6$ alkyl. In further embodiments, R$^7$ is -Me. In some embodiments, R$^7$ is -Et. In some embodiments R$^7$ is —Pr or -$^i$Pr.

In some embodiments, R$^7$ is —C$_1$-C$_6$ heteroalkyl. In further embodiments, R$^7$ is methoxymethyl (—CH$_2$OCH$_3$). In some embodiments, R$^7$ is hydroxymethyl (—CH$_2$OH). In some embodiments, R$^7$ is aminomethyl (e.g., —CH$_2$NH$_2$, —CH$_2$NHCH$_3$, —CH$_2$N(CH$_3$)$_2$.

In some embodiments, R$^7$ is —C$_1$-C$_6$ haloalkyl. In further embodiments, R$^7$ is trifluoromethyl (—CF$_3$). In other embodiments, R$^7$ is difluoromethyl (—CHF$_2$).

In some embodiments, R$^7$ is —C$_3$-C$_9$ carbocyclyl (e.g., cyclopropyl, cyclobutyl, cyclopentyl, cyclohexyl). In some embodiments, R$^7$ is cyclopropyl. In some embodiments R$^7$ is cyclobutyl. In some embodiments, R$^7$ is cyclopentyl. In some embodiments, R$^7$ is cyclohexyl.

In some embodiments, R$^7$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, R$^7$ is oxetanyl. In some embodiments, R$^7$ is tetrahydropyranyl. In some embodiments, R$^7$ is tetrahydrofuranyl. In some embodiments, R$^7$ is azetidinyl. In some embodiments, R$^7$ is pyrrolidinyl. In some embodiments, R$^7$ is piperidinyl. In some embodiments, R$^7$ is piperazinyl. In some embodiments, R$^7$ is morpholinyl. In some embodiments, R$^7$ is azepanyl.

In some embodiments, R$^7$ is a 5-6 member monocyclic heteroaryl (e.g., a 5-member monocyclic heteroaryl containing 1-3 heteroatoms independently selected from O, N and S, a 6-member monocyclic heteroaryl containing 1-3 N heteroatoms). In some embodiments, R$^7$ is a 5-member monocyclic heteroaryl (e.g., pyrazolyl, pyrolyl, thiophenyl, furyl, thiazolyl, isothiazolyl, oxazolyl, isoxazolyl, imidazolyl, triazolyl, thiadiazolyl, oxadiazolyl). In some embodiments, R$^7$ is thiophenyl (e.g., thiophen-2-yl, thiophen-3-yl). In some embodiments, R$^7$ is pyrazolyl (e.g. pyrazol-1-yl, pyrazol-3-yl, pyrazol-5-yl). In some embodiments, R$^7$ is thiazolyl (e.g., thiazol-2-yl, thiazol-4-yl, thiazol-5-yl). In some embodiments, R$^7$ is a 6-member monocyclic heteroaryl (e.g., pyridyl, pyrimidinyl, triazinyl, pyrazinyl, pyridazinyl). In some embodiments, R$^7$ is pyridinyl (e.g., pyridin-2-yl, pyridin-3-yl, pyridin-4-yl). In some embodiments, R$^7$ is pyrimidinyl (e.g., pyrimidin-2-yl, pyrimidin-4-yl, pyrimidin-5-yl).

In some embodiments R$^7$ is cycloalkylalkyl (e.g., cyclopropylmethyl, cyclobutylmethyl, cyclopentylmethyl, cyclohexylmethyl, cycloheptylmethyl). In some embodiments, R$^7$ is heterocyclylalkyl (e.g., oxetanylmethyl, aziridinylmethyl, tetrahydrofuranylmethyl, pyrrolidinylmethyl, tetrahydropyranylmethyl, piperidinylmethyl, piperazinylmethyl, morpholinylmethyl, azepanylmethyl).

In some embodiments, R$^7$ is arylalkyl. In some embodiments, R$^7$ is benzyl.

In some embodiments, R$^7$ is heteroarylalkyl (e.g., pyridinylmethyl, thiazolylmethyl, triazolylmethyl, pyrazolylmethyl).

In some embodiments, R$^7$ is —OR$^{a7}$ (e.g., hydroxy (—OH), methoxy, difluoromethoxy (—OCHF$_2$), trifluoromethoxy (—OCF$_3$), ethoxy, propoxy, isopropoxy, cyclopropyloxy, cyclobutyloxy). In some embodiments, R$^7$ is hydroxy. In some embodiments, R$^7$ is methoxy. In some embodiments, R$^7$ is ethoxy. In some embodiments, R$^7$ is propoxy. In some embodiments, R$^7$ is isopropoxy. In some embodiments, R$^7$ is difluoromethoxy. (—OCHF$_2$). In some embodiments, R$^7$ is trifluoromethoxy (—OCF$_3$).

In some embodiments, R$^7$ is —N(R$^{a7}$)$_2$ (e.g., —NH$_2$, —NHR$^{a7}$, —N(CH$_3$)R$^{a7}$). In some embodiments, R$^7$ is —NH$_2$. In some embodiments, R$^7$ is —NHR$^{a7}$ (e.g., —NHMe, —NHEt, —NHPr, —NH$^i$Pr, —NHcyclopropyl, —NHcyclobutyl). In some embodiments, R$^7$ is —N(CH$_3$)R$^{a7}$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl). In some embodiments, R$^7$ is —C(=O)R$^{a7}$ or —C(=O)OR$^{a7}$. In some embodiments, R$^7$ is —C(=O)R$^{a7}$ wherein R$^{a7}$ is as described herein. In some embodiments, R$^7$ is —C(=O) alkyl. In some embodiments, R$^7$ is —C(O)CH$_3$, —C(O)cyclopropyl, —C(O)cyclobutyl, —C(O)$^i$Bu, —C(O)$^i$Pr, —C(O)Pr, —C(O)$^i$Bu, or —C(=O)OMe. In some embodiments, R$^7$ is acetyl (—C(=O)Me). In some embodiments, R$^7$ is —C(=O)OR$^{a7}$. In some embodiments, R$^7$ is —COOH. In some embodiments, R$^7$ is COOMe.

In some embodiments, R$^7$ is —NR$^{a7}$C(=O)R$^{a7}$. In certain embodiments, R$^7$ is —NHC(=O)R$^{a7}$ (e.g., NHC(=O)Me, NHC(=O)Et, NHC(=O)Pr, NHC(=O)$^i$Pr, NHC(=O)Bu, NHC(=O)$^t$Bu, NHC(=O)Cyclopropyl, NHC(=O)Cyclobutyl). In some embodiments, R$^7$ is —N(CH$_3$)C(=O)R$^{a7}$ (e.g., N(CH$_3$)C(=O)Me, N(CH$_3$)C(=O)Et, N(CH$_3$)C(=O)Pr, N(CH$_3$)C(=O)$^i$Pr, N(CH$_3$)C(=O)Bu, N(CH$_3$)C(=O)$^t$Bu, N(CH$_3$)C(=O)Cyclopropyl, N(CH$_3$)C(=O)Cyclobutyl).

In some embodiments, R$^7$ is —NR$^{a7}$C(=O)OR$^{a7}$. In certain embodiments, R$^7$ is —NHC(=O)OR$^{a7}$ (e.g., NHC(=O)OMe, NHC(=O)OEt, NHC(=O)OPr, NHC(=O)O$^i$Pr, NHC(=O)OBu, NHC(=O)O$^t$Bu, NHC(=O)OCyclopropyl, NHC(=O)OCyclobutyl). In some embodiments, R$^7$ is —N(CH$_3$)C(=O)OR$^{a7}$ (e.g., N(CH$_3$)C(=O)OMe, N(CH$_3$)C(=O)OEt, N(CH$_3$)C(=O)OPr, N(CH$_3$)C(=O)O$^i$Pr, N(CH$_3$)C(=O)OBu, N(CH$_3$)C(=O)O$^t$Bu, N(CH$_3$)C(=O)OCyclopropyl, N(CH$_3$)C(=O)OCyclobutyl).

In some embodiments, R$^7$ is —C(=O)N(R$^{a7}$)$_2$ (e.g., —C(=O)NH$_2$, —C(=O)NHR$^{a7}$, C(=O)N(CH$_3$)R$^{a7}$). In some embodiments, R$^7$ is —C(=O)NH$_2$. In certain embodiments, R$^7$ is —C(=O)NHR$^{a7}$ (e.g., —C(=O)NHMe, —C(=O)NHEt, —C(=O)NHPr, —C(=O)NH$^i$Pr, —C(=O)NHBu, —C(=O)NH$^t$Bu, —C(=O)NHCyclopropyl, —C(=O)NHCyclobutyl). In certain embodiments, R$^7$ is —C(=O)N(CH$_3$)R$^{a7}$ (e.g., —C(=O)NMe$_2$, —C(=O)N (CH$_3$)Et, —C(=O)N(CH$_3$)Pr, —C(=O)N(CH$_3$)$^i$Pr, —C(=O)N(CH$_3$)Bu, —C(=O)N(CH$_3$)$^t$Bu, —C(=O)N(CH$_3$)Cyclopropyl, —C(=O)N(CH$_3$)Cyclobutyl).

In some embodiments, R$^7$ is —OC(=O)N(R$^{a7}$)$_2$. In certain embodiments, R$^7$ is —OC(=O)NHR$^{a7}$ (e.g., —OC(=O)NHMe, —OC(=O)NHEt, —OC(=O)NHPr, —OC(=O)NH$^i$Pr, —OC(=O)NHBu, —OC(=O)NH$^t$Bu, —OC(=O)NHCyclopropyl, —OC(=O)NHCyclobutyl). In certain embodiments, R$^7$ is —OC(=O)N(CH$_3$)R$^{a7}$ (e.g., —OC(=O)NMe$_2$, —OC(=O)N(CH$_3$)Et, —OC(=O)N(CH$_3$)Pr, —OC(=O)N(CH$_3$)$^i$Pr, —OC(=O)N(CH$_3$)Bu, —OC(=O)N(CH$_3$)$^t$Bu, —OC(=O)N(CH$_3$)Cyclopropyl, —OC(=O)N(CH$_3$)Cyclobutyl).

In some embodiments, R$^7$ is —S(=O)R$^{a7}$. In certain embodiments, R$^7$ is —S(=O)alkyl (e.g., —S(=O)Me, —S(=O)Et, —S(=O)Pr, —S(=O)$^i$Pr). In certain embodiments, R$^7$ is —S(=O)cycloalkyl (e.g., —S(=O)cyclopropyl, —S(=O)cyclobutyl, —S(=O)cyclopentyl, —S(=O)cyclohexyl).

In some embodiments, R$^7$ is —S(=O)$_2$R$^{a7}$. In certain embodiments, R$^7$ is —S(=O)$_2$ alkyl (e.g., —S(=O)$_2$Me, —S(=O)$_2$Et, —S(=O)$_2$Pr, —S(=O)$_2$$^i$Pr). In certain embodiments, R$^7$ is —S(=O)$_2$cycloalkyl (e.g., —S(=O)$_2$cyclopropyl, —S(=O)$_2$cyclobutyl, —S(=O)$_2$cyclopentyl, —S(=O)$_2$cyclohexyl). In some embodiments, R$^7$ is S(=O)$_2$ aryl (e.g., S(=O)$_2$phenyl).

In some embodiments, R$^7$ is —SR$^{a7}$. In certain embodiments, R$^7$ is —Salkyl (e.g., —SMe, —SEt, —SPr, —S$^i$Pr). In certain embodiments, R$^7$ is —Scycloalkyl (e.g., —Scyclopropyl, —Scyclobutyl, —Scyclopentyl, —Scyclohexyl). In certain embodiments, R$^7$ is —Saryl (e.g., Sphenyl).

In some embodiments, R$^7$ is —S(=O)(=NR$^{a7}$)R$^{a7}$. In certain embodiments, R$^7$ is —S(=O)(=NH)R$^{a7}$ (e.g., —S(=O)(=NH)Me, —S(=O)(=NH)Et, —S(=O)(=NH)Pr, —S(=O)(=NH)$^i$Pr, —S(=O)(=NH)Bu, —S(=O)(=NH)$^t$Bu, —S(=O)(=NH)Cyclopropyl, —S(=O)(=NH)Cyclobutyl). In some embodiments, R$^7$ is —S(=O)(=NCH$_3$)R$^{a7}$ (e.g., —S(=O)(=NCH$_3$)Me, —S(=O)(=NCH$_3$)Et, —S(=O)(=NCH$_3$)Pr, —S(=O)(=NCH$_3$)$^i$Pr, —S(=O)(=NCH$_3$)Bu, —S(=O)(=NCH$_3$)$^t$Bu, —S(=O)(=NCH$_3$)Cyclopropyl, —S(=O)(=NCH$_3$)Cyclobutyl).

In some embodiments, R$^7$ is —NR$^{a7}$S(=O)$_2$R$^{a7}$. In certain embodiments, R$^7$ is —NHS(=O)$_2$ alkyl (e.g., —NHS(=O)$_2$Me, —NHS(=O)$_2$Et, —NHS(=O)$_2$Pr, —NHS(=O)$_2$$^i$Pr). In certain embodiments, R$^7$ is —NHS(=O)$_2$cycloalkyl (e.g., —NHS(=O)$_2$cyclopropyl, —NHS(=O)$_2$cyclobutyl, —NHS(=O)$_2$cyclopentyl, —NHS(=O)$_2$cyclohexyl). In certain embodiments, R$^7$ is —N(CH$_3$)S(=O)$_2$ alkyl (e.g., —N(CH$_3$)S(=O)$_2$Me, —N(CH$_3$)S(=O)$_2$Et, —N(CH$_3$)S(=O)$_2$Pr, —N(CH$_3$)S(=O)$_2$$^i$Pr). In certain embodiments, R$^7$ is —N(CH$_3$)S(=O)$_2$cycloalkyl (e.g., —N(CH$_3$)S(=O)$_2$cyclopropyl, —N(CH$_3$)S(=O)$_2$cyclobutyl, —N(CH$_3$)S(=O)$_2$cyclopentyl, —N(CH$_3$)S(=O)$_2$cyclohexyl).

In some embodiments, R$^7$ is —S(=O)$_2$N(R$^{a7}$)$_2$. (e.g., —S(=O)$_2$NH$_2$, —S(=O)$_2$NHR$^{a7}$, —S(=O)$_2$N(CH$_3$)R$^{a7}$). In some embodiments, R$^7$ is —S(=O)$_2$NH$_2$. In some embodiments, R$^7$ is —S(=O)$_2$NHR$^{a7}$ (e.g., —S(=O)$_2$NHMe, —S(=O)$_2$NHEt, —S(=O)$_2$NHPr, —S(=O)$_2$NH$^i$Pr, —S(=O)$_2$NHcyclopropyl, —S(=O)$_2$NHcyclobutyl). In some embodiments, R$^7$ is —S(=O)$_2$N(CH$_3$)R$^{a7}$ (e.g., —S(=O)$_2$NMe$_2$, —S(=O)$_2$N(CH$_3$)Et, —S(=O)$_2$N(CH$_3$)Pr, —S(=O)$_2$N(CH$_3$)$^i$Pr, —S(=O)$_2$N(CH$_3$)cyclopropyl, —S(=O)$_2$N(CH$_3$)cyclobutyl).

As generally defined herein, each R$^8$ is independently selected from H, -D, =O, halo, —CN, —C$_1$-C$_6$ alkyl, —C$_1$-C$_6$ heteroalkyl, —C$_1$-C$_6$ haloalkyl, —C$_3$-C$_9$ cycloalkyl, 3-10 membered heterocyclyl, heterocyclylalkyl, heteroarylalkyl, arylalkyl, cycloalkylalkyl, —OR$^{a8}$, —N(R$^{a8}$)$_2$, —C(=O)R$^{a8}$, —C(=O)OR$^{a8}$, —NR$^{a8}$C(=O)R$^{a8}$, —NR$^{a8}$C(=O)OR$^{a8}$, —CH$_2$C(=O)N(R$^{a8}$)$_2$—C(=O)N(R$^{a8}$)$_2$, —OC(=O)N(R$^{a8}$)$_2$, —CH$_2$C(=O)N(R$^{a8}$)$_2$, —S(=O)R$^{a8}$, —S(=O)$_2$R$^{a8}$, —SR$^{a8}$, —S(=O)(=NR$^{a8}$)R$^{a8}$, —NR$^{a8}$S(=O)$_2$R$^{a8}$ and —S(=O)$_2$N(R$^{a8}$)$_2$ wherein two instances of R$^8$ together with the atom or atoms to which they are attached can be taken together to form a 3-10 member carbocyclyl (e.g., cycloalkyl) or heterocyclyl ring (e.g., a ring that together with the piperidine ring of Structure I can form a bridged, fused or spiro bicyclic heterocyclic ring), wherein R$^{a8}$ is as defined herein.

In some embodiments of Formula (I), two R$^8$ groups are taken together with the atom to which they are attached to form a 3-10 member spiro cycloalkyl (e.g., cyclopropyl, cyclobutyl, cyclopentyl, cyclohexyl, cycloheptyl) or spiro heterocyclyl ring (e.g., oxetanyl, tetrahydrofuranyl, tetrahydropyranyl, azetidinyl, pyrolidinyl, piperidinyl, piperazinyl, morpholinyl, azepanyl, tetrahydrothiopyranyl, thiomorpholinyl).

In some embodiments of Formula (I), two R$^8$ groups are taken together with the adjacent atoms to which they are attached to form a 3-10 member fused cycloalkyl (e.g., cyclopropyl, cyclobutyl, cyclopentyl, cyclohexyl, cycloheptyl) or fused heterocyclyl ring (e.g., oxetanyl, tetrahydrofuranyl, tetrahydropyranyl, azetidinyl, pyrolidinyl, piperidinyl, piperazinyl, morpholinyl, azepanyl, tetrahydrothiopyranyl, thiomorpholinyl).

In some embodiments, the two R$^8$ groups taken together with the atoms to which they are attached form a bridged piperidine-containing carbocyclyl or heterocyclyl ring (e.g., 2-azabicyclo[2.2.1]heptane, 2-azabicyclo[2.2.2]octane, 3-azabicyclo[3.2.1]octane).

In certain embodiments, the moiety represented as

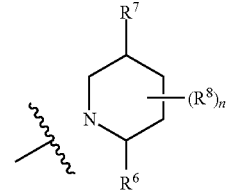

in Formula (I) is selected from:

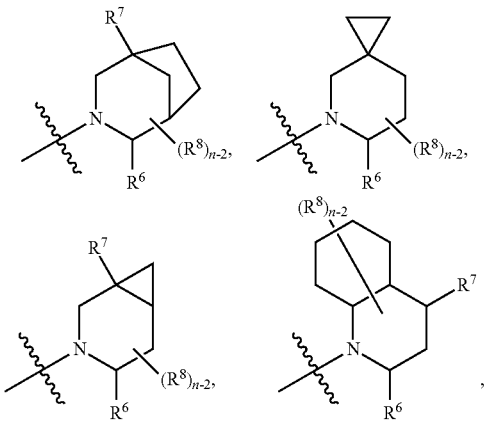

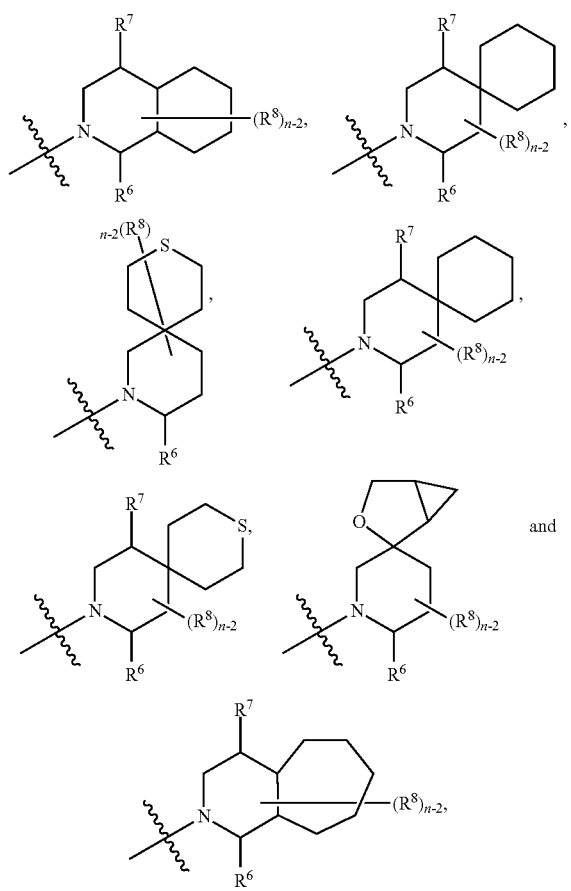
wherein R[6], R[7], R[8] and n are as defined herein.
In further embodiments, the moiety represented as
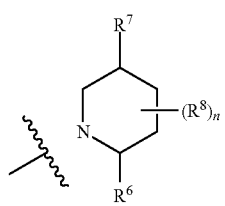
in Formula (I) is selected from:
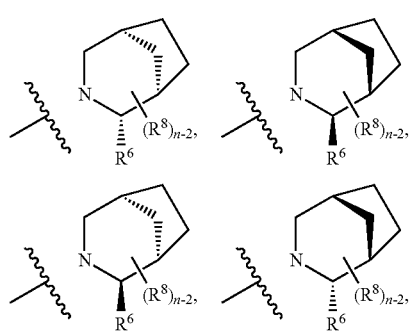
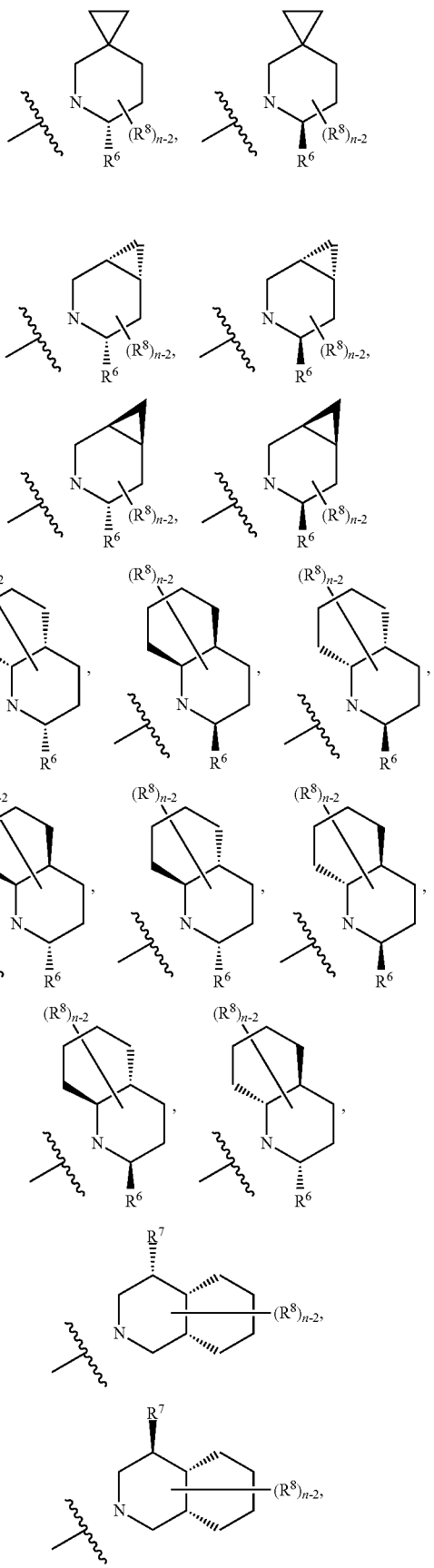

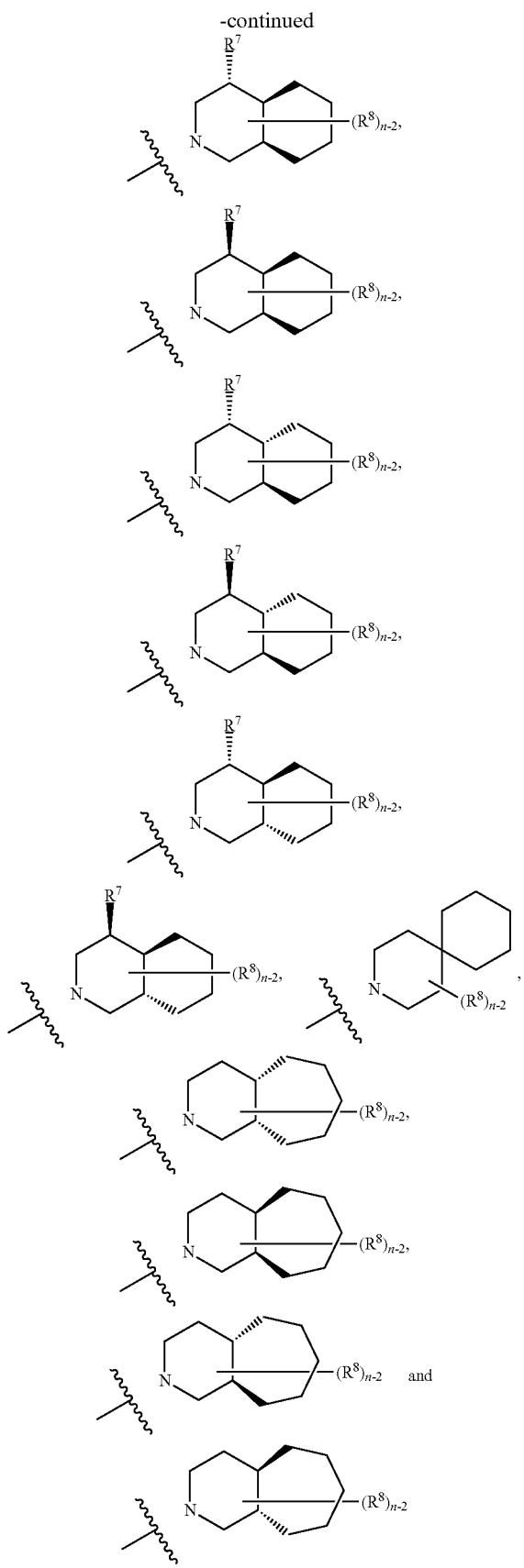

wherein R⁶, R⁷, R⁸ and n are as defined herein.

In certain embodiments of the bicyclic and polycyclic moieties described above, n is 2 (i.e., the rings do not bear any $R^8$ substituents). In some embodiments of the bicyclic and polycyclic moieties described above, each $R^6$ and $R^7$ is independently selected from H and —CH₃. In some embodiments, $R^6$ is H. In some embodiments, $R^6$ is —CH₃. In certain embodiments $R^7$ is H. In other embodiments, $R^7$ is —CH₃. In certain embodiments, both $R^6$ and $R^7$ are H.

In other embodiments, the $R^8$ groups are not taken together to form cycloalkyl or heterocyclyl rings (i.e., each $R^8$ is independently selected from H, -D, =O, halo, —CN, —C₁-C₆ alkyl, —C₁-C₆ heteroalkyl, —C₁-C₆ haloalkyl, —C₃-C₉ cycloalkyl, 3-10 membered heterocyclyl, heterocyclylalkyl, heteroarylalkyl, arylalkyl, cycloalkylalkyl, —OR$^{a8}$, —N(R$^{a8}$)₂, —C(=O)R$^{a8}$, —C(=O)OR$^{a8}$, —NR$^{a8}$C(=O)R$^{a8}$, —NR$^{a8}$C(=O)OR$^{a8}$, —CH₂C(=O)N(R$^{a8}$)₂—C(=O)N(R$^{a8}$)₂, —OC(=O)N(R$^{a8}$)₂, —CH₂C(=O)N(R$^{a8}$)₂, —S(=O)R$^{a8}$, —S(=O)₂R$^{a8}$, —SR$^{a8}$, —S(=O)(=NR$^{a8}$)R$^{a8}$, —NR$^{a8}$S(=O)₂R$^{a8}$ and —S(=O)₂N(R$^{a8}$)₂), wherein R$^{a8}$ is as defined herein.

In some embodiments, each $R^8$ is independently selected from H, -D, halo (e.g., —F, —Cl), —CN, —C₁-C₆ alkyl (e.g., -Me, -Et, —Pr, -$^i$Pr, -sec-Bu, —Bu), arylalkyl, (e.g., benzyl), —C(=O)R$^{a8}$ (e.g., —C(=O)Me, —C(=O)Et, —C(=O)Pr, —C(=O)$^i$Pr), —N(R$^{a8}$)₂ (e.g., —NHMe, NH₂, NMe₂), —NR$^{a8}$C(=O)R$^{a8}$ (e.g., —NHC(=O)Me), —CH₂C(=O)N(R$^{a8}$)₂ (e.g., —CH₂C(=O)NH₂) and —OR$^{a8}$ (e.g., —OH, —OMe, —O$^i$Pr, —OCF₃), wherein each R$^{a8}$ is as defined herein. In further embodiments, each R$^{a8}$ is independently selected from H, —CF₃, and —C₁-C₆ alkyl (e.g., -Me, -Et, —Pr, -$^i$Pr, -$^n$Bu, $^t$-Bu, -sec-Bu, -iso-Bu).

In some embodiments, each $R^8$ is independently selected from H, -D, —F, -Me, -Et, —CN, benzyl, —OMe, —O$^i$Pr, —OCF₃, —NHC(=O)Me, —NMe₂, —CH₂C(=O)NH₂, —C(=O)$^i$Pr and —OH. In some embodiments, $R^8$ is selected from H, -D, —F, -Me, -Et and —CN. In some embodiments, $R^8$ is selected from H, -D, —F and -Me.

In some embodiments, $R^8$ is H.
In some embodiments, $R^8$ is -D.
In certain embodiments, $R^8$ is =O.
In certain embodiments, $R^8$ is halo (e.g., fluoro, chloro, bromo, iodo). In further embodiments, $R^8$ is —Cl. In some embodiments, $R^8$ is —F. In some embodiments, $R^8$ is —Br. In some embodiments, $R^8$ is —I.
In some embodiments, $R^8$ is —CN.
In certain embodiments, $R^8$ is —C₁-C₆ alkyl. In further embodiments, $R^8$ is -Me. In some embodiments, $R^8$ is -Et. In some embodiments $R^8$ is —Pr or -$^i$Pr.
In some embodiments, $R^8$ is —C₁-C₆ heteroalkyl. In further embodiments, $R^8$ is methoxymethyl (—CH₂OCH₃). In some embodiments, $R^8$ is hydroxymethyl (—CH₂OH). In some embodiments, $R^8$ is aminomethyl (e.g., —CH₂NH₂, —CH₂NHCH₃, —CH₂N(CH₃)₂. In some embodiments, $R^8$ is —C₁-C₆ haloalkyl. In further embodiments, $R^8$ is trifluoromethyl (—CF₃).
In some embodiments, $R^8$ is —C₃-C₉ carbocyclyl (e.g., cyclopropyl, cyclobutyl, cyclopentyl, cyclohexyl). In some embodiments, $R^8$ is cyclopropyl. In some embodiments $R^8$ is cyclobutyl. In some embodiments, $R^8$ is cyclopentyl. In some embodiments, $R^8$ is cyclohexyl. In some embodiments, $R^8$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, $R^8$ is oxetanyl. In some embodiments, $R^8$ is tetrahydropyranyl. In some embodiments, $R^8$ is tetrahydrofuranyl. In some embodiments, $R^8$ is azetidinyl. In some embodiments, $R^8$ is pyrrolidinyl. In some embodiments, $R^8$ is piperidinyl. In some embodiments, $R^8$ is piperazinyl. In some embodiments, $R^8$ is morpholinyl. In some embodiments, $R^8$ is azepanyl.

In some embodiments $R^8$ is cycloalkylalkyl (e.g., cyclopropylmethyl, cyclobutylmethyl, cyclopentylmethyl, cyclohexylmethyl, cycloheptylmethyl). In some embodiments, $R^8$ is heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl). In some embodiments, $R^8$ is arylalkyl (e.g. benzyl). In some embodiments, $R^8$ is heteroarylalkyl (e.g., pyridinylmethyl, thiazolylmethyl, triazolylmethyl, pyrazolylmethyl).

In some embodiments, $R^8$ is —$CH_2C(=O)N(R^{a8})_2$ (e.g., —$CH_2C(=O)N(R^{a8})_2$).

In some embodiments, $R^8$ is —$OR^{a8}$ (e.g., —OH, methoxy, isopropoxy, difluoromethoxy (—$OCHF_2$), trifluoromethoxy (—$OCF_3$), ethoxy, propoxy, isopropoxy, cyclopropyloxy, cyclobutyloxy). In some embodiments $R^8$ is —OH. In some embodiments, $R^8$ is methoxy. In some embodiments, $R^8$ is ethoxy. In some embodiments, $R^8$ is propoxy. In some embodiments, $R^8$ is isopropoxy. In some embodiments $R^8$ is difluoromethoxy. (—$OCHF_2$). In some embodiments, $R^8$ is trifluoromethoxy (—$OCF_3$).

In some embodiments, $R^8$ is —$N(R^{a8})_2$ (e.g., —$NH_2$, —N—$R^{a8}$, —$N(CH_3)R^{a8}$). In some embodiments, $R^8$ is —$NH_2$. In some embodiments, $R^8$ is —$NHR^{a8}$ (e.g., —NHMe, —NHEt, —NHPr, —$NH^iPr$, —NHcyclopropyl, —NHcyclobutyl). In some embodiments, $R^8$ is —$N(CH_3)R^{a8}$ (e.g., —$NMe_2$, —$N(CH_3)Et$, —$N(CH_3)Pr$, —$N(CH_3)^iPr$, —$N(CH_3)$cyclopropyl, —$N(CH_3)$cyclobutyl). In some embodiments, $R^8$ is —$C(=O)R^{a8}$ wherein $R^{a8}$ is as described herein. In some embodiments $R^8$ is —$C(=O)R^{a8}$ wherein $R^{a8}$ is $C_1$-$C_6$ alkyl, $C_3$-$C_9$ carbocyclyl or 3-10 membered heterocyclyl (e.g. —C(=O)Me, —C(=O)Et, —$C(O)^iBu$, —$C(O)^iPr$, —C(O)Pr, —$C(O)^iBu$, —C(=O)cyclopropyl, —C(=O)cyclobutyl, —C(=O)oxetanyl, —C(=O)tetrahydropyranyl). In some embodiments, $R^8$ is —C(=O)Me, —C(=O)Et, —$C(O)^iBu$, —$C(O)^iPr$, —C(O)Pr or —$C(O)^iBu$. In some embodiments, $R^8$ is —$C(=O)^iPr$.

In some embodiments, $R^8$ is —$NR^{a8}C(=O)R^{a8}$. In certain embodiments, $R^8$ is —$NHC(=O)R^{a8}$ (e.g., NHC(=O)Me, NHC(=O)Et, NHC(=O)Pr, $NHC(=O)^iPr$, NHC(=O)Bu, $NHC(=O)^iBu$, NHC(=O)Cyclopropyl, NHC(=O)Cyclobutyl). In certain embodiments, $R^8$ is NHC(=O)Me. In some embodiments, $R^8$ is —$N(CH_3)C(=O)R^{a8}$ (e.g., $N(CH_3)C(=O)Me$, $N(CH_3)C(=O)Et$, $N(CH_3)C(=O)Pr$, $N(CH_3)C(=O)^iPr$, $N(CH_3)C(=O)Bu$, $N(CH_3)C(=O)^iBu$, $N(CH_3)C(=O)Cyclopropyl$, $N(CH_3)C(=O)Cyclobutyl$).

In some embodiments, $R^8$ is —$NR^{a8}C(=O)OR^{a8}$. In certain embodiments, $R^8$ is —$NHC(=O)OR^{a8}$ (e.g., NHC(=O)OMe, NHC(=O)OEt, NHC(=O)OPr, $NHC(=O)O^iPr$, NHC(=O)OBu, $NHC(=O)O^iBu$, NHC(=O)OCyclopropyl, NHC(=O)OCyclobutyl). In some embodiments, $R^8$ is —$N(CH_3)C(=O)OR^{a8}$ (e.g., $N(CH_3)C(=O)OMe$, $N(CH_3)C(=O)OEt$, $N(CH_3)C(=O)OPr$, $N(CH_3)C(=O)O^iPr$, $N(CH_3)C(=O)OBu$, $N(CH_3)C(=O)O^iBu$, $N(CH_3)C(=O)OCyclopropyl$, $N(CH_3)C(=O)OCyclobutyl$).

In some embodiments, $R^8$ is —$C(=O)N(Ra)_2$ (e.g., —$C(=O)NH_2$, —$C(=O)NHR^{a8}$, —$C(=O)N(CH_3)R^{a8}$). In some embodiments, $R^8$ is —$C(=O)NH_2$. In certain embodiments, $R^8$ is —$C(=O)NHR^{a8}$ (e.g., —C(=O)NHMe, —C(=O)NHEt, —C(=O)NHPr, —$C(=O)NH^iPr$, —C(=O)NHBu, —$C(=O)NH^iBu$, —C(=O)NHCyclopropyl, —C(=O)NHCyclobutyl). In certain embodiments, $R^8$ is —$C(=O)N(CH_3)R^{a8}$ (e.g., —$C(=O)NMe_2$, —$C(=O)N(CH_3)Et$, —$C(=O)N(CH_3)Pr$, —$C(=O)N(CH_3)^iPr$, —$C(=O)N(CH_3)Bu$, —$C(=O)N(CH_3)^iBu$, —$C(=O)N(CH_3)Cyclopropyl$, —$C(=O)N(CH_3)Cyclobutyl$).

In some embodiments, $R^8$ is —$OC(=O)N(R^{a8})_2$. In certain embodiments, $R^8$ is —$OC(=O)NHR^{a8}$ (e.g., —OC(=O)NHMe, —OC(=O)NHEt, —OC(=O)NHPr, —$OC(=O)NH^iPr$, —OC(=O)NHBu, —$OC(=O)NH^iBu$, —OC(=O)NHCyclopropyl, —OC(=O)NHCyclobutyl). In certain embodiments, $R^8$ is —$OC(=O)N(CH_3)R^{a8}$ (e.g., —$OC(=O)NMe_2$, —$OC(=O)N(CH_3)Et$, —$OC(=O)N(CH_3)Pr$, —$OC(=O)N(CH_3)^iPr$, —$OC(=O)N(CH_3)Bu$, —$OC(=O)N(CH_3)^iBu$, —$OC(=O)N(CH_3)Cyclopropyl$, —$OC(=O)N(CH_3)Cyclobutyl$).

In some embodiments, $R^8$ is —$S(=O)R^{a8}$. In certain embodiments, $R^8$ is —S(=O)alkyl (e.g., —S(=O)Me, —S(=O)Et, —S(=O)Pr, —$S(=O)^iPr$). In certain embodiments, $R^8$ is —S(=O)cycloalkyl (e.g., —S(=O)cyclopropyl, —S(=O)cyclobutyl, —S(=O)cyclopentyl, —S(=O)cyclohexyl).

In some embodiments, $R^8$ is —$S(=O)_2R^{a8}$. In certain embodiments, $R^8$ is —$S(=O)_2$ alkyl (e.g., —$S(=O)_2Me$, —$S(=O)_2Et$, —$S(=O)_2Pr$, —$S(=O)_2^iPr$). In certain embodiments, $R^8$ is —$S(=O)_2$cycloalkyl (e.g., —$S(=O)_2$cyclopropyl, —$S(=O)_2$cyclobutyl, —$S(=O)_2$cyclopentyl, —$S(=O)_2$cyclohexyl). In some embodiments, $R^8$ is $S(=O)_2$ aryl (e.g., $S(=O)_2$phenyl).

In some embodiments, $R^8$ is —$SR^{a8}$. In certain embodiments, $R^8$ is —Salkyl (e.g., —SMe, —SEt, —SPr, —$S^iPr$). In certain embodiments, $R^8$ is —Scycloalkyl (e.g., —Scyclopropyl, —Scyclobutyl, —Scyclopentyl, —Scyclohexyl). In certain embodiments, $R^8$ is —Saryl (e.g., Sphenyl).

In some embodiments, $R^8$ is —$S(=O)(=NR^{a8})R^{a8}$. In certain embodiments, $R^8$ is —$S(=O)(=NH)R^{a8}$ (e.g., —S(=O)(=NH)Me, —S(=O)(=NH)Et, —S(=O)(=NH)Pr, —$S(=O)(=NH)^iPr$, —S(=O)(=NH)Bu, —$S(=O)(=NH)^iBu$, —S(=O)(=NH)Cyclopropyl, —S(=O)(=NH)Cyclobutyl). In some embodiments, $R^8$ is —$S(=O)(=NCH_3)R^{a8}$ (e.g., —$S(=O)(=NCH_3)Me$, —$S(=O)(=NCH_3)Et$, —$S(=O)(=NCH_3)Pr$, —$S(=O)(=NCH_3)^iPr$, —$S(=O)(=NCH_3)Bu$, —$S(=O)(=NCH_3)^iBu$, —$S(=O)(=NCH_3)Cyclopropyl$, —$S(=O)(=NCH_3)Cyclobutyl$).

In some embodiments, $R^8$ is —$NR^{a8}S(=O)_2R^{a8}$. In certain embodiments, $R^8$ is —$NHS(=O)_2$ alkyl (e.g., —$NHS(=O)_2Me$, —$NHS(=O)_2Et$, —$NHS(=O)_2Pr$, —$NHS(=O)_2^iPr$). In certain embodiments, $R^8$ is —$NHS(=O)_2$cycloalkyl (e.g., —$NHS(=O)_2$cyclopropyl, —$NHS(=O)_2$cyclobutyl, —$NHS(=O)_2$cyclopentyl, —$NHS(=O)_2$cyclohexyl). In certain embodiments, $R^8$ is —$N(CH_3)S(=O)_2$ alkyl (e.g., —$N(CH_3)S(=O)_2Me$, —$N(CH_3)S(=O)_2Et$, —$N(CH_3)S(=O)_2Pr$, —$N(CH_3)S(=O)_2^iPr$). In certain embodiments, $R^8$ is —$N(CH_3)S(=O)_2$cycloalkyl (e.g., —$N(CH_3)S(=O)_2$cyclopropyl, —$N(CH_3)S(=O)_2$cyclobutyl, —$N(CH_3)S(=O)_2$cyclopentyl, —$N(CH_3)S(=O)_2$cyclohexyl).

In some embodiments, $R^8$ is —$S(=O)_2N(R^{a8})_2$. (e.g., —$S(=O)_2NH_2$, —$S(=O)_2NHR^{a8}$, —$S(=O)_2N(CH_3)R^{a8}$). In some embodiments, $R^8$ is —$S(=O)_2NH_2$. In some embodiments, $R^8$ is —$S(=O)_2NHR^{a8}$ (e.g., —$S(=O)_2NHMe$, —$S(=O)_2NHEt$, —$S(=O)_2NHPr$, —$S(=O)_2NH^iPr$, —$S(=O)_2NHcyclopropyl$, —$S(=O)_2NHcyclobutyl$). In some embodiments, $R^8$ is —$S(=O)_2N(CH_3)R^{a8}$ (e.g., —$S(=O)_2NMe_2$, —$S(=O)_2N(CH_3)Et$, —$S(=O)_2N(CH_3)Pr$, —$S(=O)_2N(CH_3)^iPr$, —$S(=O)_2N(CH_3)$cyclopropyl, —$S(=O)_2N(CH_3)$cyclobutyl).

As generally described herein, each $R^{10}$ is independently selected from -D, =O, —CN, halo, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, $C_6$-$C_{10}$ aryl, 5-10 membered heteroaryl, cycloalkylalkyl, heterocyclylalkyl, arylalkyl, heteroarylalkyl, heterocyclylalkoxy, —$OR^{b10}$—$N(R^{b10})_2$—$C(=O)OR^{b10}$—$C(=O)OR^{b10}$—$NR^{b10}C(=O)R^{b10}$, —$NR^{b10}C(=O)OR^{b10}$—$C(=O)N(R^{b10})_2$, —$OC(=O)R^{b10}$, —$OC(=O)N(R^{b10})_2$, —$S(=O)R^{b10}$, —$S(=O)_2R^{b10}$—$SR^{b10}$®—$S(=O)(=NR^{b10})R^{b10}$—$NR^{b10}S(=O)_2R^{b10}$ and —$S(=O)_2N(R^{b10})_2$ wherein each alkyl, cycloalkyl, heteroalkyl, heterocyclyl, aryl, heteroaryl, cycloalkylalkyl, heterocyclylalkyl, heterocyclylalkoxy, arylalkyl and heteroarylalkyl of $R^{10}$ is optionally substituted (e.g., with 0, 1, 2,3,4, or 5 instances of -Me, -Et, -$^iPr$, cyclopropyl, oxetan-3-yl, —OH, =O, —F, —OMe, —$CH_2CH_2F$, —$CH_2CHF_2$, —$CH_2CH_2CF_3$, —$C(=O)Me$, —$N(Me)_2$, —$CH_2N(CH_3)_2$, —$CH_2N(CH_3)CH_2CH_3$, —$N(^iPr)(Et)$, —$N(^iPr)(Me)$, —$N(Et)_2$, —$N(CH_3)(Et)$, —$NHC(=O)Me$, or a combination thereof).

In some embodiments, each alkyl, cycloalkyl, heterocyclyl, aryl, heteroaryl, cycloalkylalkyl, heterocyclylalkyl, arylalkyl and heteroarylalkyl of $R^{10}$ is unsubstituted. In some embodiments, each alkyl, cycloalkyl, heterocyclyl, aryl, heteroaryl, cycloalkylalkyl, heterocyclylalkyl, arylalkyl and heteroarylalkyl of $R^{10}$ is independently substituted with 1 instance of Me, -Et, -$^iPr$, cyclopropyl, oxetan-3-yl, —OH, =O, —F, —OMe, —$CH_2CH_2F$, —$CH_2CHF_2$, —$CH_2CH_2CF_3$, —$C(=O)Me$, —$N(Me)_2$, —$CH_2N(CH_3)_2$, —$CH_2N(CH_3)CH_2CH_3$, —$N(^iPr)(Et)$, —$N(^iPr)(Me)$, —$N(Et)_2$, —$N(CH_3)(Et)$, —$NHC(=O)Me$, or a combination thereof). or a combination thereof. In some embodiments, each alkyl, cycloalkyl, heterocyclyl, aryl, heteroaryl, cycloalkylalkyl, heterocyclylalkyl, arylalkyl and heteroarylalkyl of $R^{10}$ is independently substituted with 2 instances of Me, -Et, -$^iPr$, cyclopropyl, oxetan-3-yl, —OH, =O, —F, —OMe, —$CH_2CH_2F$, —$CH_2CHF_2$, —$CH_2CH_2CF_3$, —$C(=O)Me$, —$N(Me)_2$, —$CH_2N(CH_3)_2$, —$CH_2N(CH_3)CH_2CH_3$, —$N(^iPr)(Et)$, —$N(^iPr)(Me)$, —$N(Et)_2$, —$N(CH_3)(Et)$, —$NHC(=O)Me$, or a combination thereof). In some embodiments, each alkyl, cycloalkyl, heterocyclyl, aryl, heteroaryl, cycloalkylalkyl, heterocyclylalkyl, arylalkyl and heteroarylalkyl of $R^{10}$ is independently substituted with 3 instances of Me, -Et, -$^iPr$, cyclopropyl, oxetan-3-yl, —OH, =O, —F, —OMe, —$CH_2CH_2F$, —$CH_2CHF_2$, —$CH_2CH_2CF_3$, —$C(=O)Me$, —$N(Me)_2$, —$CH_2N(CH_3)_2$, —$CH_2N(CH_3)CH_2CH_3$, —$N(^iPr)(Et)$, —$N(^iPr)(Me)$, —$N(Et)_2$, —$N(CH_3)(Et)$, —$NHC(=O)Me$, or a combination thereof). In some embodiments, each alkyl, cycloalkyl, heterocyclyl, aryl, heteroaryl, cycloalkylalkyl, heterocyclylalkyl, arylalkyl and heteroarylalkyl of $R^{10}$ is independently substituted with 4 instances of Me, -Et, -$^iPr$, cyclopropyl, oxetan-3-yl, —OH, =O, —F, —OMe, —$CH_2CH_2F$, —$CH_2CHF_2$, —$CH_2CH_2CF_3$, —$C(=O)Me$, —$N(Me)_2$, —$CH_2N(CH_3)_2$, —$CH_2N(CH_3)CH_2CH_3$, —$N(^iPr)(Et)$, —$N(^iPr)(Me)$, —$N(Et)_2$, —$N(CH_3)(Et)$, —$NHC(=O)Me$, or a combination thereof).

In some embodiments, each alkyl, cycloalkyl, heterocyclyl, aryl, heteroaryl, cycloalkylalkyl, heterocyclylalkyl, arylalkyl and heteroarylalkyl of $R^{10}$ is independently substituted with 5 instances of Me, -Et, -$^iPr$, cyclopropyl, oxetan-3-yl, —OH, =O, —F, —OMe, —$CH_2CH_2F$, —$CH_2CHF_2$, —$CH_2CH_2CF_3$, —$C(=O)Me$, —$N(Me)_2$, —$CH_2N(CH_3)_2$, —$CH_2N(CH_3)CH_2CH_3$, —$N(^iPr)(Et)$, —$N(^iPr)(Me)$, —$N(Et)_2$, —$N(CH_3)(Et)$, —$NHC(=O)Me$, or a combination thereof).

In some embodiments, each $R^{10}$ is independently selected from -D, =O, halo (e.g., F, Cl, Br), —CN, —$C_1$-$C_6$ alkyl (e.g., -Me, -Et, —Pr, -$^iPr$, -sec-Bu, -$^iBu$, $CH_2(CH_3)(^iPr)$), —$C_1$-$C_6$ heteroalkyl (e.g., —$CH(CH_3)(NMe_2)$, —$CH_2CH_2N(Me)(oxetan-3-yl))$, —$CH_2CH(CH_3)(NMe_2)$, —$CH_2OH$, —$CH(OH)(CH_3)$, —$C(OH)(CH_3)_2$, —$CH_2NH_2$), —$C_1$-$C_6$ haloalkyl (e.g., —$CHF_2$, —$CH_2CF_3$, —$CF_3$), —$C_3$-$C_9$ cycloalkyl (e.g., cyclopropyl, cyclobutyl, cyclopentyl, cyclohexyl), 3-10 membered heterocyclyl (e.g., tetrahydrofuranyl, tetrahydropyranyl, oxetanyl, morpholinyl, pyrolidinyl, piperidinyl, piperidin-2-onyl, piperazinyl, piperazin-2-only, azetidinyl, decahydro-1,6-naphthyridinyl, 2-azaspiro[3.3]heptanyl, 5-oxa-2,8-diazaspiro[3.5]nonanyl, 8-azabicyclo[3.2.1]octanyl, 2-azabicyclo[2.2.2]octanyl, 3-azabicyclo[3.2.0]heptanyl, 3-azabicyclo[3.1.1]heptanyl, 3-azabicyclo[3.1.0]hexanyl, 2-azabicyclo[2.1.1]hexanyl, 1-azabicyclo[2.2.1]heptanyl, 3-azabicyclo[3.2.0]heptanyl, 2,9-diazaspiro[5.5]undecanyl, bicyclo[1.1.1]pentanyl, octahydrocyclopenta[c]pyrrolyl, decahydro-1,6-naphthyridinyl, octahydro-1H-pyrrolo[3,4-c]pyridinyl, decahydro-2,7-naphthyridinyl, 2,9-diazaspiro[5.5]undecanyl), 5-10 membered heteroaryl (e.g., pyridinyl, imidazo[1,2-a]pyridinyl, imidazolyl, pyrazolyl, thiazolyl, thiophenyl), cycloalkylalkyl (e.g. —$CH_2$-cyclopropyl), heterocyclylalkyl (e.g., —$CH_2$-morpholinyl, —$(CH_2)_2$-pyrolidinyl-$(CH_2)_2$-pyrolidinyl-$CH_2$-imidazolyl, —$CH_2$-pyrazolyl, —$CH_2$-1,2,4-triazolyl, —$CH_2$-morpholinyl, —$(CH_2)_2$-morpholinyl), heterocyclylalkoxy (e.g., —O—$(CH_2)_2$-pyrolidinyl, —O—$CH_2$-piperidinyl, —O—$CH_2$-oxetanyl, —O—$CH_2$-tetrahydrofuranyl, —O—$CH_2$-tetrahydropyranyl), heteroarylalkyl (e.g., —$CH_2$-triazolyl, —$CH_2$-imidazolyl, —$CH_2$-pyrazolyl), —$OR^{b10}$ (e.g., —OH, —OMe, OEt, —O-tetrahydrofuranyl, —O-tetrahydropyran-4-yl, —$OCF_3$, —$OCHF_2$), —$N(R^{b10})_2$, (e.g., —$NH_2$, —$NHR^{b10}$, —NHMe, —$NMe_2$, —$NHCH_2CF_3$, —NH-oxetan-3-yl, —NH—(N-Me-2-oxo-pyrolidin-3-yl), —$NR^{b10}C(=O)R^{b10}$ (e.g., —$NHC(=O)Me$), —$C(=O)N(R^{b10})_2$, (e.g., —$C(=O)NH_2$, $C(=O)NHMe$), —$OC(=O)R^{b10}$ (e.g., —$OC(=O)Me$), —$S(=O)R^{b10}$ (e.g., —$SO_2Me$), —$NR^{b10}S(=O)_2R^{b10}$ (e.g., $NHSO_2Me$) and —$S(=O)_2N(R^{b10})_2$ (e.g., $SO_2NH_2$, $SO_2NHMe$), wherein each alkyl, cycloalkyl, heterocyclyl, aryl, heteroaryl, cycloalkylalkyl, heterocyclylalkyl, arylalkyl and heteroarylalkyl is optionally substituted (e.g., with 0, 1, 2,3,4, or 5 instances of -Me, -Et, -$^iPr$, cyclopropyl, oxetan-3-yl, —OH, =O, —F, —OMe, —$CH_2CH_2F$, —$CH_2CHF_2$, —$CH_2CH_2CF_3$, —$C(=O)Me$, —$N(Me)_2$, —$CH_2N(CH_3)_2$, —$CH_2N(CH_3)CH_2CH_3$, —$N(^iPr)(Et)$, —$N(^iPr)(Me)$, —$N(Et)_2$, —$N(CH_3)(Et)$, —$NHC(=O)Me$, or a combination thereof), and wherein:

each $R^{b10}$ is independently selected from H, —$C_1$-$C_6$ alkyl, (e.g., -Me, -Et, —Pr, -$^iPr$, -sec-Bu, -$^iBu$), —$C_1$-$C_6$ haloalkyl (e.g., —$CF_3$, —$CHF_2$, —$CH_2CF_3$), —$C_1$-$C_6$ heteroalkyl substituted with 0 or 1 instances of =O (e.g., —$CH_2CH_2NMe_2$, —$CH_2C(=O)NMe_2$, —$CH(CH_3)CH_2NMe_2$, —$CH(CH_3)C(=O)NMe_2$), $C_3$-$C_9$ cycloalkyl, and 3-10 member heterocyclyl (e.g. tetrahydrofuran-3-yl, tetrahydropyran-4-yl, oxetan-3-yl, N-Me-2-oxo-pyrolidin-3-yl, piperidin-4-yl) substituted with 0 or 1 instances of =O, -Me or a combination thereof.

As generally defined herein, each $R^{b10}$ is independently H; —$C_1$-$C_6$ alkyl; —$C_1$-$C_6$ haloalkyl; —$C_1$-$C_6$ heteroalkyl substituted with 0 or 1 instance of =O (e.g., unsubstituted or substituted with one instance of =O); $C_3$-$C_9$ cycloalkyl; or 3-10 member heterocyclyl substituted with 0 or 1 instances of =O, -Me or a combination thereof (e.g., unsubstituted, substituted with one instance of =O, substituted with one instance of -Me or substituted with one instance of =O and one instance of -Me). In certain embodiments of $R^{10}$, each $R^{b10}$ is independently selected from H, -Me, -Et, —Pr, -$^iPr$, -sec-Bu, —$^iBu$, —$CF_3$, —CHF$_2$, —CH$_2$CF$_3$, —CH$_2$CH$_2$NMe$_2$, —CH$_2$C(=O)NMe$_2$, —CH(CH$_3$)CH$_2$NMe$_2$, —CH(CH$_3$)C(=O)NMe$_2$), tetrahydrofuran-3-yl, tetrahydropyran-4-yl, oxetan-4-yl and N-Me-2-oxo-pyrolidin-3-yl.

In some embodiments, R$^{10}$ is independently selected from -D, =O, —OH, —F, —Cl, —Br, —CN, -Me, -Et, —Pr, -$^i$Pr, -sec-Bu, -$^t$Bu, —OMe, —OEt, —CHF$_2$, —CH$_2$CF$_3$, —CF$_3$, —OCF$_3$, —OCHF$_2$, —CH$_2$OH, —CH(OH)(CH$_3$), —CH$_2$OMe, —C(OH)(CH$_3$)$_2$, —CH$_2$NH$_2$, —CH(CH$_3$)(NMe$_2$), —CH$_2$CH(CH$_3$)(NMe$_2$), —CH$_2$(CH$_3$)($^i$Pr), —NH$_2$, —NHMe, —NHCH$_2$CF$_3$, —NMe$_2$, cyclopropyl, cyclobutyl, cyclopentyl, cyclohexyl, thiazol-2-yl, thiazol-5-yl, thiophen-2-yl, tetrahydrofuran-3-yl, tetrahydropyran-4-yl, oxetan-3-yl, morpholin-2-yl, —CH$_2$-morpholin-4-yl, —(CH$_2$)$_2$-morpholin-4-yl, imidazol-2-yl, 1H-pyrazol-5-yl, 1H-imidazol-4-yl, imidazo[1,2-a]pyridin-7-yl, pyrolidin-1-yl, pyrolidin-3-yl, piperidin-4-yl, piperidin-3-yl, piperidin-2-one-4-yl, piperazin-4-yl, piperazin-4-yl, piperazin-2-on-5-yl pyridine-4-yl, pyridine-3-yl, pyrazol-1-yl, pyrazol-3-yl, pyrazol-4-yl, pyrazol-5-yl, 1H-pyrazol-5-yl, azetidin-3-yl, —(CH$_2$)$_2$-pyrolidin-1-yl-(CH$_2$)$_2$-pyrolidin-2-yl-CH$_2$-imidazol-1-yl, —CH$_2$-pyrazol-1-yl, —CH$_2$-1,2,4-triazol-1-yl, —CH$_2$-cyclopropyl, —O(CH$_2$)$_2$NMe$_2$, —O-tetrahydrofuran-3-yl, —O-tetrahydropyran-4-yl, —O—(N-Me-2-oxo-pyrolidin-3-yl), —O—(CH$_2$)$_2$-pyrolidin-2-yl-O—CH$_2$-piperidin-4-yl-O—CH$_2$-oxetan-3-yl-NCH$_3$-piperidin-4-yl, —NH-oxetan-3-yl, —NH—(N-Me-2-oxo-pyrolidin-3-yl), decahydro-1,6-naphthyridin-6-yl, 2-azaspiro[3.3]heptan-6-yl, 5-oxa-2,8-diazaspiro[3.5]nonan-8-yl, 8-azabicyclo[3.2.1]octan-3-yl, 2-azabicyclo[2.2.2]octan-4-yl, 3-azabicyclo[3.2.0]heptan-6-yl, 3-azabicyclo[3.1.1]heptan-1-yl, 3-azabicyclo[3.1.0]hexan-6-yl, 1-azabicyclo[2.2.1]heptan-4-yl, 3-azabicyclo[3.2.0]heptan-6-yl, 2-azabicyclo[2.1.1]hexan-4-yl, 2,9-diazaspiro[5.5]undecane-9-yl, bicyclo[1.1.1]pentan-2-yl, octahydrocyclopenta[c]pyrrol-5-yl, decahydro-1,6-naphthyridin-6-yl, octahydro-1H-pyrrolo[3,4-c]pyridine-5-yl, decahydro-2,7-naphthyridin-2-yl, 2,9-diazaspiro[5.5]undecan-2-yl, —NHC(=O)Me, —NHCH$_2$C(=O)NMe$_2$, —NHCH(CH$_3$)C(=O)NMe$_2$, —C(=O)NH$_2$, C(=O)NHMe, —OC(=O)Me, —SO$_2$Me, —NHSO$_2$Me, —SO$_2$NH$_2$ and —SO$_2$NHMe, wherein each —OMe, —OEt, -Me, -Et, —Pr, -$^i$Pr, cyclopropyl, cyclobutyl, cyclopentyl, cyclohexyl, tetrahydrofuran-3-yl, oxetan-3-yl, pyrolidin-1-yl, pyrolidin-3-yl, piperidin-4-yl, piperidin-3-yl, piperidin-2-one-4-yl piperazin-4-yl, pyrazol-1-yl, pyrazol-3-yl, pyrazol-4-yl, pyrazol-5-yl, thiazol-2-yl, thiophen-2-yl, —CH$_2$-cyclopropyl, —CH$_2$-morpholin-4-yl, —(CH$_2$)$_2$-morpholin-4-yl, -morpholin-2-yl, —(CH$_2$)$_2$-pyrolidin-1-yl, —CH$_2$-1,2,4-triazol-1-yl-CH$_2$-imidazol-1-yl, imidazol-2-yl, —CH$_2$-pyrazol-1-yl, —OCH$_2$-piperidin-4-yl, azetidin-3-yl, 2-azaspiro[3.3]heptan-6-yl, 2-methyl-5-oxa-2,8-diazaspiro[3.5]nonan-8-yl, 8-azabicyclo[3.2.1]octan-3-yl, and decahydro-1,6-naphthyridin-6-yl, wherein each R$^{10}$ can be independently substituted with 0, 1, 2, 3, 4, or 5 instances of -Me, -Et, -$^i$Pr, cyclopropyl, oxetan-3-yl, —OH, =O, —F, —OMe, —CH$_2$CH$_2$F, —CH$_2$CHF$_2$, —CH$_2$CH$_2$CF$_3$, —C(=O)Me, —N(Me)$_2$, —CH$_2$N(CH$_3$)$_2$, —CH$_2$N(CH$_3$)CH$_2$CH$_3$, —N($^i$Pr)(Et), —N($^i$Pr)(Me), —N(Et)$_2$, —N(CH$_3$)(Et), —NHC(=O)Me, or a combination thereof.

In some embodiments, R$^{10}$ is H. In some embodiments R$^{10}$ is -D.

In certain embodiments, R$^{10}$ is halo (e.g., fluoro, chloro, bromo, iodo). In further embodiments, R$^{10}$ is —Cl. In some embodiments, R$^{10}$ is —F. In some embodiments, R$^{10}$ is —Br. In some embodiments, R$^{10}$ is —I.

In some embodiments, R$^{10}$ is —CN.

In certain embodiments, R$^{10}$ is —C$_1$-C$_6$ alkyl. In further embodiments, R$^{10}$ is -Me. In some embodiments, R$^{10}$ is -Et. In some embodiments R$^{10}$ is —Pr or -$^i$Pr. In some embodiments R$^{10}$ is -$^t$Bu or -sec-Bu. In some embodiments R$^{10}$ is —CH$_2$(CH$_3$)($^i$Pr).

In some embodiments, R$^{10}$ is —C$_1$-C$_6$ heteroalkyl. In further embodiments, R$^{10}$ is methoxymethyl (—CH$_2$OCH$_3$). In some embodiments, R$^{10}$ is hydroxymethyl (—CH$_2$OH). In some embodiments, R$^{10}$ is —CH(OH)CH$_3$, C(OH)(CH$_3$)$_2$. In some embodiments, R$^{10}$ is aminomethyl (e.g., —CH$_2$NH$_2$, —CH$_2$NHCH$_3$, —CH$_2$NHCH$_2$CH$_3$—CH$_2$N(CH$_3$)$_2$, —CH(CH$_3$)(NMe$_2$), —CH$_2$CH$_2$N(Me)(oxetan-3-yl), —CH$_2$CH(CH$_3$)(NMe$_2$). In some embodiments, the heteroalkyl is further substituted with =O (e.g., —CH$_2$NHC(=O)CH$_3$). In some embodiments, R$^{10}$ is —C$_1$-C$_6$ haloalkyl. In further embodiments, R$^{10}$ is trifluoromethyl (—CF$_3$). In other embodiments, R$^{10}$ is difluoromethyl (—CHF$_2$). In some embodiments R$^{10}$ is trifluoroethyl (—CH$_2$CF$_3$) In some embodiments, R$^{10}$ is —C$_3$-C$_9$ carbocyclyl (e.g., cyclopropyl, cyclobutyl, cyclopentyl, cyclohexyl). In some embodiments, R$^{10}$ is cyclopropyl. In some embodiments R$^{10}$ is cyclobutyl. In some embodiments, R$^{10}$ is cyclopentyl. In some embodiments, R$^{10}$ is cyclohexyl. In some embodiments, the carbocyclyl is substituted with —OH (e.g., hydroxycyclobutyl)

In some embodiments, R$^{10}$ is 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl, piperidin-2-onyl, piperazin-2-onyl, decahydro-1,6-naphthyridinyl, 2-azaspiro[3.3]heptanyl, 5-oxa-2,8-diazaspiro[3.5]nonanyl, 8-azabicyclo[3.2.1]octanyl, 2-azabicyclo[2.2.2]octanyl, 3-azabicyclo[3.2.0]heptanyl, 3-azabicyclo[3.1.1]heptanyl, 3-azabicyclo[3.1.0]hexanyl, 2-azabicyclo[2.1.1]hexanyl, 1-azabicyclo[2.2.1]heptanyl, 3-azabicyclo[3.2.0]heptanyl, 2,9-diazaspiro[5.5]undecanyl, bicyclo[1.1.1]pentanyl, octahydrocyclopenta[c]pyrrolyl, decahydro-1,6-naphthyridinyl, octahydro-1H-pyrrolo[3,4-c]pyridinyl, decahydro-2,7-naphthyridinyl, 2,9-diazaspiro[5.5]undecanyl).

In some embodiments, R$^{10}$ is oxetanyl. In some embodiments, R$^{10}$ is tetrahydropyranyl. In some embodiments, R$^{10}$ is tetrahydrofuranyl. In some embodiments, R$^{10}$ is azetidinyl. In some embodiments, R$^{10}$ is pyrrolidinyl. In some embodiments, R$^{10}$ is piperidinyl. In some embodiments, R$^{10}$ is piperazinyl. In some embodiments, R$^{10}$ is morpholinyl. In some embodiments, R$^{10}$ is azepanyl. In some embodiments, R$^{10}$ is piperidinonyl.

In some embodiments, R$^{10}$ is piperidin-2-onyl. In some embodiments, R$^{10}$ is piperazin-2-only. In some embodiments, R$^{10}$ is decahydro-1,6-naphthyridinyl. In some embodiments, R$^{10}$ is 2-azaspiro[3.3]heptanyl. In some embodiments, R$^{10}$ is 5-oxa-2,8-diazaspiro[3.5]nonanyl. In some embodiments, R$^{10}$ is 8-azabicyclo[3.2.1]octanyl. In some embodiments, R$^{10}$ is 2-azabicyclo[2.2.2]octanyl. In some embodiments, R$^{10}$ is 3-azabicyclo[3.2.0]heptanyl. In some embodiments, R$^{10}$ is 3-azabicyclo[3.1.1]heptanyl. In some embodiments, R$^{10}$ is 3-azabicyclo[3.1.0]hexanyl. In some embodiments, R$^{10}$ is 2-azabicyclo[2.1.1]hexanyl. In some embodiments, R$^{10}$ is 1-azabicyclo[2.2.1]heptanyl. In some embodiments, R$^{10}$ is 3-azabicyclo[3.2.0]heptanyl. In some embodiments, R$^{10}$ is 2,9-diazaspiro[5.5]undecanyl. In some embodiments, R$^{10}$ is bicyclo[1.1.1]pentanyl. In some embodiments, R$^{10}$ is octahydrocyclopenta[c]pyrrolyl. In some embodiments, R$^{10}$ is decahydro-1,6-naphthyridinyl. In some embodiments, R$^{10}$ is octahydro-1H-pyrrolo[3,4-c]pyridinyl. In some embodiments, R$^{10}$ is decahydro-2,7-naphthyridinyl. In some embodiments, R$^{10}$ is 2,9-diazaspiro

[5.5]undecanyl) In some embodiments, the heterocyclyl is substituted with 0, 1, 2 or 3 instances of -D, =O, -Me, —C(=O)Me or —C(=O)NHCH$_3$.

In some embodiments, $R^{10}$ is a 5-10 member heteroaryl (e.g., a 5-6 member monocyclic heteroaryl or an 8-10 member bicyclic heteroaryl containing 1-3 heteroatoms independently selected from N, O and S).

In some embodiments, $R^{10}$ is a 5-6 member monocyclic heteroaryl (e.g., a 5-member monocyclic heteroaryl containing 1-3 heteroatoms independently selected from O, N and S, a 6-member monocyclic heteroaryl containing 1-3 N heteroatoms).

In some embodiments, $R^{10}$ is a 5-member monocyclic heteroaryl (e.g., pyrazolyl, pyrolyl, thiophenyl, furyl, thiazolyl, isothiazolyl, oxazolyl, isoxazolyl, imidazolyl, triazolyl, thiadiazolyl, oxadiazolyl).

In some embodiments, $R^{10}$ is thiophenyl (e.g., thiophen-2-yl, thiophen-3-yl). In some embodiments, $R^{10}$ is pyrazolyl (e.g. pyrazol-1-yl, pyrazol-3-yl, pyrazol-5-yl). In some embodiments, $R^{10}$ is thiazolyl (e.g., thiazol-2-yl, thiazol-4-yl, thiazol-5-yl).

In some embodiments, $R^{10}$ is a 6-member monocyclic heteroaryl (e.g., pyridyl, pyrimidinyl, triazinyl, pyrazinyl, pyridazinyl).

In some embodiments, $R^{10}$ is pyridinyl (e.g., pyridin-2-yl, pyridin-3-yl, pyridin-4-yl). In some embodiments, $R^{10}$ is pyrimidinyl (e.g., pyrimidin-2-yl, pyrimidin-4-yl, pyrimidin-5-yl). In some embodiments, the heteroaryl is substituted with 0, 1 or 2 instances of -Me.

In some embodiments, $R^{10}$ is monocyclic heterocyclyl. In some embodiments, $R^{10}$ is monocyclic heteroaryl. In some embodiments, $R^{10}$ is tetrahydrofuran-3-yl. In some embodiments, $R^{10}$ is tetrahydropyran-4-yl. In some embodiments, $R^{10}$ is oxetan-3-yl. In some embodiments, $R^{10}$ is morpholin-2-yl. In some embodiments, $R^{10}$ is -imidazol-2-yl. In some embodiments, $R^{10}$ is 1H-pyrazol-5-yl. In some embodiments, $R^{10}$ is 1H-imidazol-4-yl. In some embodiments, $R^{10}$ is imidazo[1,2-a]pyridin-7-yl. In some embodiments, $R^{10}$ is pyrolidin-1-yl. In some embodiments, $R^{10}$ is pyrolidin-3-yl. In some embodiments, $R^{10}$ is piperidin-4-yl. In some embodiments, $R^{10}$ is piperidin-3-yl. In some embodiments, $R^{10}$ is piperidin-2-one-4-yl. In some embodiments, $R^{10}$ is piperazin-4-yl. In some embodiments, $R^{10}$ is piperazin-4-yl. In some embodiments, $R^{10}$ is piperazin-2-on-5-yl. In some embodiments, $R^{10}$ is pyridine-4-yl. In some embodiments, $R^{10}$ is pyridine-3-yl. In some embodiments, $R^{10}$ is pyrazol-1-yl. In some embodiments, $R^{10}$ is pyrazol-3-yl. In some embodiments, $R^{10}$ is pyrazol-4-yl. In some embodiments, $R^{10}$ is pyrazol-5-yl. In some embodiments, $R^{10}$ is 1H-pyrazol-5-yl. In some embodiments, $R^{10}$ is azetidin-3-yl. In some embodiments, $R^{10}$ is heterocylylalkoxy. In some embodiments, $R^{10}$ is —O(CH$_2$)$_2$NMe$_2$. In some embodiments, $R^{10}$ is —O-tetrahydrofuran-3-yl. In some embodiments, $R^{10}$ is —O-tetrahydropyran-4-yl. In some embodiments, $R^{10}$ is —O—(N-Me-2-oxo-pyrolidin-3-yl). In some embodiments, $R^{10}$ is —O—(CH$_2$)$_2$-pyrolidin-2-yl. In some embodiments, $R^{10}$ is —O—CH$_2$-piperidin-4-yl. In some embodiments, $R^{10}$ is —O—CH$_2$-oxetan-3-yl.

In some embodiments, $R^{10}$ is monocyclic heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl). In some embodiments, $R^{10}$ is —CH$_2$-morpholin-4-yl. In some embodiments, $R^{10}$ is —(CH$_2$)$_2$-morpholin-4-yl. In some embodiments, $R^{10}$ is —(CH$_2$)$_2$-pyrolidin-1-yl. In some embodiments, $R^{10}$ is —(CH$_2$)$_2$-pyrolidin-2-yl.

In some embodiments, $R^{10}$ is bicyclic 3-10 membered heterocyclyl. In some embodiments, $R^{10}$ is decahydro-1,6-naphthyridin-6-yl. In some embodiments, $R^{10}$ is 2-azaspiro[3.3]heptan-6-yl. In some embodiments, $R^{10}$ is 5-oxa-2,8-diazaspiro[3.5]nonan-8-yl. In some embodiments, $R^{10}$ is 8-azabicyclo[3.2.1]octan-3-yl. In some embodiments, $R^{10}$ is 2-azabicyclo[2.2.2]octan-4-yl. In some embodiments, $R^{10}$ is 3-azabicyclo[3.2.0]heptan-6-yl. In some embodiments, $R^{10}$ is 3-azabicyclo[3.1.1]heptan-1-yl. In some embodiments, $R^{10}$ is 3-azabicyclo[3.1.0]hexan-6-yl. In some embodiments, $R^{10}$ is 1-azabicyclo[2.2.1]heptan-4-yl. In some embodiments, $R^{10}$ is 3-azabicyclo[3.2.0]heptan-6-yl. In some embodiments, $R^{10}$ is 2-azabicyclo[2.1.1]hexan-4-yl. In some embodiments, $R^{10}$ is 2,9-diazaspiro[5.5]undecane-9-yl. In some embodiments, $R^{10}$ is bicyclo[1.1.1]pentan-2-yl. In some embodiments, $R^{10}$ is octahydrocyclopenta[c]pyrrol-5-yl. In some embodiments, $R^{10}$ is decahydro-1,6-naphthyridin-6-yl. In some embodiments, $R^{10}$ is octahydro-1H-pyrrolo[3,4-c]pyridine-5-yl. In some embodiments, $R^{10}$ is decahydro-2,7-naphthyridin-2-yl, 2,9-diazaspiro[5.5]undecan-2-yl. In some embodiments $R^{10}$ is cycloalkylalkyl (e.g., cyclopropylmethyl, cyclobutylmethyl, cyclopentylmethyl, cyclohexylmethyl, cycloheptylmethyl). In some embodiments, $R^{10}$ is cyclopropylmethyl.

In some embodiments, $R^{10}$ is arylalkyl. In some embodiments, $R^{10}$ is benzyl. In some embodiments, $R^{10}$ is heteroarylalkyl (e.g., —CH$_2$-imidazole, —CH$_2$-pyrazole, —CH$_2$-pyridinyl). In some embodiments, $R^{10}$ is pyridinylmethyl (e.g., pyridinyl-4-methyl). In some embodiments, $R^{10}$ is —CH$_2$-1,2,4-triazol-1-yl. In some embodiments, $R^{10}$ is —CH$_2$-imidazol-1-yl. In some embodiments, $R^{10}$ is —CH$_2$-pyrazol-1-yl.

In some embodiments, $R^{10}$ is —OR$^{b10}$ (e.g., hydroxy (—OH), methoxy, difluoromethoxy (—OCHF$_2$), trifluoromethoxy (—OCF$_3$), ethoxy, propoxy, isopropoxy, cyclopropyloxy, cyclobutyloxy). In some embodiments, $R^{10}$ is hydroxy. In some embodiments, $R^{10}$ is methoxy. In some embodiments, $R^{10}$ is ethoxy. In some embodiments, $R^{10}$ is propoxy. In some embodiments, $R^{10}$ is isopropoxy. In some embodiments $R^{10}$ is difluoromethoxy. (—OCHF$_2$). In some embodiments, $R^{10}$ is trifluoromethoxy (—OCF$_3$).

In some embodiments, $R^{10}$ is —N(R$^{b10}$)$_2$ (e.g., —NH$_2$, —NHR$^{b10}$, —N(CH$_3$)R$^{b10}$). In some embodiments, $R^{10}$ is —NH$_2$. In some embodiments, $R^{10}$ is —NHR$^{b10}$ (e.g., —NHMe, —NHEt, —NHPr, —NHCH$_2$CF$_3$, —NH$^i$Pr, —NHcyclopropyl, —NHcyclobutyl). In some embodiments, $R^{10}$ is NHCH$_2$CF$_3$. In some embodiments, $R^{10}$ is —N(CH$_3$)R$^{b10}$ (e.g., —NMe$_2$, —N(CH$_3$)Et, —N(CH$_3$)Pr, —N(CH$_3$)$^i$Pr, —N(CH$_3$)cyclopropyl, —N(CH$_3$)cyclobutyl).

In some embodiments, $R^{10}$ is —C(=O)R$^{b10}$ or —C(=O)OR$^{b10}$. In some embodiments, $R^{10}$ is —C(=O)R$^{b10}$ wherein R$^{b10}$ is as described herein. In some embodiments, $R^{10}$ is —C(=O)alkyl. In some embodiments, $R^{10}$ is —C(O)CH$_3$, —C(O)cyclopropyl, —C(O)cyclobutyl, —C(O)$^i$Bu, —C(O)$^i$Pr, —C(O)Pr, —C(O)$^i$Bu, or —C(=O)OMe. In some embodiments, $R^{10}$ is acetyl (—C(=O)Me). In some embodiments, $R^{10}$ is —C(=O)OR$^{b10}$. In some embodiments, $R^{10}$ is —COOH. In some embodiments, $R^{10}$ is COOMe.

In some embodiments, $R^{10}$ is —NR$^{b10}$C(=O)R$^{b10}$. In certain embodiments, $R^{10}$ is NHC(=O)R$^{b10}$ (e.g., —NHC(=O)Me, —NHC(=O)Et, —NHC(=O)Pr, —NHC(=O)$^i$Pr, —NHC(=O)Bu, —NHC(=O)$^i$Bu, —NHC(=O)Cyclopropyl, —NHC(=O)Cyclobutyl). In some embodiments, $R^{10}$ is —NHC(=O)Me. In some embodiments, $R^{10}$ is —N(CH$_3$)C(=O)R$^{b10}$ (e.g., N(CH$_3$)C(=O)Me, N(CH$_3$)C (=O)Et, N(CH₃)C(=O)Pr, N(CH₃)C(=O)ⁱPr, N(CH₃)C(=O)Bu, N(CH₃)C(=O)ᵗBu, N(CH₃)C(=O)Cyclopropyl, N(CH₃)C(=O)Cyclobutyl).

In some embodiments, $R^{10}$ is —NR$^{b10}$C(=O)OR$^{b10}$. In certain embodiments, $R^{10}$ is —NHC(=O)OR$^{b10}$ (e.g., NHC(=O)OMe, NHC(=O)OEt, NHC(=O)OPr, NHC(=O)OⁱPr, NHC(=O)OBu, NHC(=O)OᵗBu, NHC(=O)OCyclopropyl, NHC(=O)OCyclobutyl). In some embodiments, $R^{10}$ is —N(CH₃)C(=O)OR$^{b10}$ (e.g., N(CH₃)C(=O)OMe, N(CH₃)C(=O)OEt, N(CH₃)C(=O)OPr, N(CH₃)C(=O)OⁱPr, N(CH₃)C(=O)OBu, N(CH₃)C(=O)OᵗBu, N(CH₃)C(=O)OCyclopropyl, N(CH₃)C(=O)OCyclobutyl).

In some embodiments, $R^{10}$ is —C(=O)N(R$^{b10}$)₂ (e.g., —C(=O)NH₂, —C(=O)NHR$^{b10}$, —C(=O)N(CH₃)R$^{b10}$). In some embodiments, $R^{10}$ is —C(=O)NH₂. In certain embodiments, $R^{10}$ is —C(=O)NHR$^{b10}$ (e.g., —C(=O)NHMe, —C(=O)NHEt, —C(=O)NHPr, —C(=O)NHⁱPr, —C(=O)NHBu, —C(=O)NHᵗBu, —C(=O)NHCyclopropyl, —C(=O)NHCyclobutyl). In some embodiments, $R^{10}$ is —C(=O)NHMe. In certain embodiments, $R^{10}$ is —C(=O)N(CH₃)R$^{b10}$ (e.g., —C(=O)NMe₂, —C(=O)N(CH₃)Et, —C(=O)N(CH₃)Pr, —C(=O)N(CH₃)ⁱPr, —C(=O)N(CH₃)Bu, —C(=O)N(CH₃)ᵗBu, —C(=O)N(CH₃)Cyclopropyl, —C(=O)N(CH₃)Cyclobutyl).

In some embodiments, $R^{10}$ is —OC(=O)N(R$^{b10}$)₂. In certain embodiments, $R^{10}$ is —OC(=O)NHR$^{b10}$ (e.g., —OC(=O)NHMe, —OC(=O)NHEt, —OC(=O)NHPr, —OC(=O)NHⁱPr, —OC(=O)NHBu, —OC(=O)NHᵗBu, —OC(=O)NHCyclopropyl, —OC(=O)NHCyclobutyl). In certain embodiments, $R^{10}$ is —OC(=O)N(CH₃)R$^{b10}$ (e.g., —OC(=O)NMe₂, —OC(=O)N(CH₃)Et, —OC(=O)N(CH₃)Pr, —OC(=O)N(CH₃)ⁱPr, —OC(=O)N(CH₃)Bu, —OC(=O)N(CH₃)ᵗBu, —OC(=O)N(CH₃)Cyclopropyl, —OC(=O)N(CH₃)Cyclobutyl).

In some embodiments, $R^{10}$ is —OC(=O)R$^{b10}$. (e.g., —OC(=O)Me, —OC(=O)Et, —OC(=O)Pr, —OC(=O)ⁱPr, —OC(=O)Bu, —OC(=O)Bu, —OC(=O)Cyclopropyl, —OC(=O)Cyclobutyl). In some embodiments, $R^{10}$ is —OC(=O)Me.

In some embodiments, $R^{10}$ is —S(=O)R$^{b10}$. In certain embodiments, $R^{10}$ is —S(=O)alkyl (e.g., —S(=O)Me, —S(=O)Et, —S(=O)Pr, —S(=O)ⁱPr). In some embodiments $R^{10}$ is —S(=O)Me. In certain embodiments, $R^{10}$ is —S(=O)cycloalkyl (e.g., —S(=O)cyclopropyl, —S(=O)cyclobutyl, —S(=O)cyclopentyl, —S(=O)cyclohexyl).

In some embodiments, $R^{10}$ is —S(=O)₂R$^{b10}$. In certain embodiments, $R^{10}$ is —S(=O)₂ alkyl (e.g., —S(=O)₂Me, —S(=O)₂Et, —S(=O)₂Pr, —S(=O)₂ⁱPr). In some embodiments $R^{10}$ is —S(=O)₂Me. In certain embodiments, $R^{10}$ is —S(=O)₂cycloalkyl (e.g., —S(=O)₂cyclopropyl, —S(=O)₂cyclobutyl, —S(=O)₂cyclopentyl, —S(=O)₂cyclohexyl). In some embodiments, $R^{10}$ is S(=O)₂ aryl (e.g., S(=O)₂phenyl).

In some embodiments, $R^{10}$ is —SR$^{b10}$. In certain embodiments, $R^{10}$ is —Salkyl (e.g., —SMe, —SEt, —SPr, —SⁱPr). In certain embodiments, $R^{10}$ is —Scycloalkyl (e.g., —Scyclopropyl, —Scyclobutyl, —Scyclopentyl, —Scyclohexyl). In certain embodiments, $R^{10}$ is —Saryl (e.g., Sphenyl).

In some embodiments, $R^{10}$ is —S(=O)(=NR$^{b10}$)R$^{b10}$. In certain embodiments, $R^{10}$ is —S(=O)(=NH)R$^{b10}$ (e.g., —S(=O)(=NH)Me, —S(=O)(=NH)Et, —S(=O)(=NH)Pr, —S(=O)(=NH)ⁱPr, —S(=O)(=NH)Bu, —S(=O)(=NH)ᵗBu, —S(=O)(=NH)Cyclopropyl, —S(=O)(=NH)Cyclobutyl). In some embodiments, $R^{10}$ is —S(=O)(=NCH₃)R$^{b10}$ (e.g., —S(=O)(=NCH₃)Me, —S(=O)(=NCH₃)Et, —S(=O)(=NCH₃)Pr, —S(=O)(=NCH₃)ⁱPr, —S(=O)(=NCH₃)Bu, —S(=O)(=NCH₃)ᵗBu, —S(=O)(=NCH₃)Cyclopropyl, —S(=O)(=NCH₃)Cyclobutyl).

In some embodiments, $R^{10}$ is —NR$^{b10}$S(=O)₂R$^{b10}$. In certain embodiments, $R^{10}$ is —NHS(=O)₂ alkyl (e.g., —NHS(=O)₂Me, —NHS(=O)₂Et, —NHS(=O)₂Pr, —NHS(=O)₂ⁱPr). In certain embodiments, $R^{10}$ is —NHS(=O)₂cycloalkyl (e.g., —NHS(=O)₂cyclopropyl, —NHS(=O)₂cyclobutyl, —NHS(=O)₂cyclopentyl, —NHS(=O)₂cyclohexyl). In certain embodiments, $R^{10}$ is —N(CH₃)S(=O)₂ alkyl (e.g., —N(CH₃)S(=O)₂Me, —N(CH₃)S(=O)₂Et, —N(CH₃)S(=O)₂Pr, —N(CH₃)S(=O)₂ⁱPr). In certain embodiments, $R^{10}$ is —N(CH₃)S(=O)₂cycloalkyl (e.g., —N(CH₃)S(=O)₂cyclopropyl, —N(CH₃)S(=O)₂cyclobutyl, —N(CH₃)S(=O)₂cyclopentyl, —N(CH₃)S(=O)₂cyclohexyl).

In some embodiments, $R^{10}$ is —S(=O)₂N(R$^{b10}$)₂. (e.g., —S(=O)₂NH₂, —S(=O)₂NHR$^{b10}$, —S(=O)₂N(CH₃)R$^{b10}$). In some embodiments, $R^{10}$ is —S(=O)₂NH₂. In some embodiments, $R^{10}$ is —S(=O)₂NR$^{10}$ (e.g., —S(=O)₂NHMe, —S(=O)₂NHEt, —S(=O)₂NHPr, —S(=O)₂NHⁱPr, —S(=O)₂NHcyclopropyl, —S(=O)₂NHcyclobutyl). In some embodiments, $R^{10}$ is —S(=O)₂N(CH₃)R$^{b10}$ (e.g., —S(=O)₂NMe₂, —S(=O)₂N(CH₃)Et, —S(=O)₂N(CH₃)Pr, —S(=O)₂N(CH₃)ⁱPr, —S(=O)₂N(CH₃)cyclopropyl, —S(=O)₂N(CH₃)cyclobutyl).

As generally defined herein, each $R^{a1}$, $R^{a2}$, $R^{a3}$, $R^{a4}$, $R^{a6}$, $R^{a7}$ and $R^{a8}$ is independently selected from H, $C_1$-$C_6$ alkyl, $C_1$-$C_6$ heteroalkyl, $C_3$-$C_9$ cycloalkyl, 3-7 membered heterocyclyl, cycloalkylalkyl, heterocyclylalkyl, aryl, 5-6 membered heteroaryl, arylalkyl and heteroarylalkyl wherein each alkyl, cycloalkyl, heterocyclyl, cycloalkylalkyl, heterocyclylalkyl, aryl, heteroaryl, arylalkyl and heteroarylalkyl is optionally substituted at any available position (e.g., substituted with 0, 1, 2 or 3 instances of $R^9$, wherein each $R^9$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —OR$^b$, —N(R$^b$)₂, —C(=O)R$^b$, —C(=O)OR$^b$, —NR$^b$C(=O)R$^b$, —NR$^b$C(=O)OR$^b$, —C(=O)N(R$^b$)₂, —OC(=O)N(R$^b$)₂, —S(=O)R$^b$, —S(=O)₂R$^b$, —SR$^b$, —S(=O)(=NR$^b$)R$^b$, —NR$^b$S(=O)₂R$^b$ and —S(=O)₂N(R$^b$)₂, wherein each $R^b$ is independently selected from H, —$C_1$-$C_6$ alkyl (e.g., -Me, -Et, —Pr, -ⁱPr, -ⁿBu, -ᵗBu, -sec-Bu, -iso-Bu). and $C_3$-$C_9$ cycloalkyl (e.g., cyclopropyl, cyclobutyl, cyclopentyl, cyclohexyl).

In some embodiments, each $R^{a1}$, $R^{a2}$, $R^{a3}$, $R^{a4}$, Ra, $R^{a7}$ and $R^{a8}$ is independently unsubstituted. In some embodiments, each $R^{a1}$, $R^{a2}$, $R^{a3}$, $R^{a4}$, $R^{a6}$, $R^{a7}$ and $R^{a8}$ is independently substituted with 1 instance of $R^9$. In some embodiments, each $R^{a1}$, $R^{a2}$, $R^{a3}$, $R^{a4}$, Ra, $R^{a7}$ and $R^{a8}$ is independently substituted with 2 instances of $R^9$. In some embodiments, each $R^{a1}$, $R^{a2}$, $R^{a3}$, $R^{a4}$, $R^{a6}$, $R^{a7}$ and $R^{a8}$ is independently substituted with 3 instances of $R^9$.

In some embodiments, each $R^{a1}$, $R^{a2}$, $R^{aa}$, $R^{a4}$, $R^{a6}$, $R^{a7}$ and $R^{a8}$ is independently selected from H, —$C_1$-$C_6$ alkyl (e.g., -Me, -Et, —Pr, -ⁱPr, -ⁿBu, —Bu, -sec-Bu, -iso-Bu) and —$C_1$-$C_6$ haloalkyl (e.g., —CHF₂, —CF₃). In some embodiments, each $R^{a1}$, $R^{a2}$, $R^{a3}$, $R^{a4}$, $R^{a6}$, $R^{a7}$ and $R^{a8}$ is independently selected from H and —$C_1$-$C_6$ alkyl (e.g., -Me, -Et, —Pr, -ⁱPr, -ⁿBu, ᵗ-Bu, -sec-Bu, -iso-Bu).

In some embodiments, each $R^{a1}$, $R^{a2}$, $R^{aa}$, $R^{a4}$, Ra, $R^{a7}$ and $R^{a8}$ is independently H. In some embodiments, each $R^{a1}$, $R^{a2}$, R, $R^{a4}$, $R^{a6}$, $R^{a7}$ and $R^{a8}$ is independently —$C_1$-$C_6$ alkyl (e.g., -Me, -Et, —Pr, -ⁱPr, -ⁿBu, ᵗ-Bu, -sec-Bu, -iso-Bu). In some embodiments, each $R^{a1}$, $R^{a2}$, $R^{a3}$, $R^{a4}$, $R^{a6}$, $R^{a7}$ and $R^{a8}$ is independently -Me. In some embodiments, each $R^{a1}$, $R^{a2}$, $R^{a3}$, $R^{a4}$, $R^{a6}$, $R^{a7}$ and $R^{a8}$ is independently -Et. In some embodiments, each $R^{a1}$, $R^{a2}$, $R^{a3}$, $R^{a4}$, $R^{a6}$, $R^{a7}$ and $R^{a8}$ is independently —Pr or -$^i$Pr.

In some embodiments, each $R^{a1}$, $R^{a2}$, $R^{aa}$, $R^{a4}$, Ra, $R^{a7}$ and $R^{a8}$ is independently —$C_1$-$C_6$ heteroalkyl. In further embodiments, each $R^{a1}$, $R^{a2}$, $R^{aa}$, $R^{a4}$, Ra, $R^{a7}$ and $R^{a8}$ is independently methoxymethyl (—$CH_2OCH_3$). In some embodiments, each $R^{a1}$, $R^{a2}$, $R^{a3}$, $R^{a4}$, $R^{a6}$, $R^{a7}$ and $R^{a8}$ is independently hydroxymethyl (—$CH_2OH$). In some embodiments, each $R^{a1}$, $R^{a2}$, $R^{aa}$, $R^{a4}$, Ra, $R^{a7}$ and $R^{a8}$ is independently is aminomethyl (e.g., —$CH_2NH_2$, —$CH_2NHCH_3$, —$CH_2N(CH_3)_2$. In some embodiments, each $R^{a1}$, $R^{a2}$, $R^{a3}$, $R^{a4}$, Ra, $R^{a7}$ and $R^{a8}$ is independently —$C_1$-$C_6$ haloalkyl. In further embodiments, each $R^{a1}$, $R^{a2}$, $R^{aa}$, $R^{a4}$, Ra, $R^{a7}$ and $R^{a8}$ is independently trifluoromethyl (—$CF_3$). In other embodiments, each $R^{a1}$, $R^{a2}$, $R^{a3}$, $R^{a4}$, $R^{a6}$, $R^{a7}$ and $R^{a8}$ is independently difluoromethyl (—$CHF_2$).

In some embodiments, each $R^{a1}$, $R^{a2}$, $R^{a3}$, $R^{a4}$, Ra, $R^{a7}$ and $R^{a8}$ is independently —$C_3$-$C_9$ carbocyclyl (e.g., cyclopropyl, cyclobutyl, cyclopentyl, cyclohexyl). In some embodiments, each $R^{a1}$, $R^{a2}$, $R^{a3}$, $R^{a4}$, $R^{a6}$, $R^{a7}$ and $R^{a8}$ is independently cyclopropyl. In some embodiments each $R^{a1}$, $R^{a2}$, $R^{a3}$, $R^{a4}$, $R^{a6}$, $R^{a7}$ and $R^{a8}$ is independently cyclobutyl. In some embodiments, each $R^{a1}$, $R^{a2}$, $R^{a3}$, $R^{a4}$, $R^{a6}$, $R^{a7}$ and $R^{a8}$ is independently cyclopentyl. In some embodiments, each $R^{a1}$, $R^{a2}$, $R^{a3}$, $R^{a4}$, $R^{a6}$, $R^{a7}$ and $R^{a8}$ is independently cyclohexyl.

In some embodiments, each $R^{a1}$, $R^{a2}$, $R^{a3}$, $R^{a4}$, Ra, $R^{a7}$ and $R^{a8}$ is independently 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl). In some embodiments, each $R^{a1}$, $R^{a2}$, $R^{a3}$, $R^{a4}$, $R^{a6}$, $R^{a7}$ and $R^{a8}$ is independently is oxetanyl. In some embodiments, each $R^{a1}$, $R^{a2}$, $R^{a3}$, $R^{a4}$, $R^{a6}$, $R^{a7}$ and $R^{a8}$ is independently tetrahydropyranyl. In some embodiments, each $R^{a1}$, $R^{a2}$, $R^{a3}$, $R^{a4}$, $R^{a6}$, $R^{a7}$ and $R^{a8}$ is independently tetrahydrofuranyl. In some embodiments, each $R^{a1}$, $R^{a2}$, $R^{a3}$, $R^{a4}$, $R^{a6}$, $R^{a7}$ and $R^{a8}$ is independently azetidinyl. In some embodiments, each $R^{a1}$, $R^{a2}$, $R^{a3}$, $R^{a4}$, $R^{a6}$, $R^{a7}$ and $R^{a8}$ is independently pyrrolidinyl. In some embodiments, each $R^{a1}$, $R^{a2}$, $R^{a3}$, $R^{a4}$, $R^{a6}$, $R^{a7}$ and $R^{a8}$ is independently piperidinyl. In some embodiments, each Rai $R^{a2}$, $R^{a3}$, $R^{a4}$, $R^{a6}$, $R^{a7}$ and $R^{a8}$ is independently piperazinyl. In some embodiments, each $R^{a1}$, $R^{a2}$, $R^{a3}$, $R^{a4}$, $R^{a6}$, $R^{a7}$ and $R^{a8}$ is independently morpholinyl. In some embodiments, each $R^{a1}$, $R^{a2}$, $R^{a3}$, $R^{a4}$, $R^{a6}$, $R^{a7}$ and $R^{a8}$ is independently azepanyl.

In some embodiments, $R^{a1}$, $R^{a2}$, $R^{a3}$, $R^{a4}$, $R^{a6}$, $R^{a7}$ and $R^{a8}$ is independently heteroaryl. In some embodiments, $R^{a1}$, $R^{a2}$, $R^{a3}$, $R^{a4}$, $R^{a6}$, $R^{a7}$ and $R^{a8}$ is independently a 5-10 member heteroaryl (e.g., a 5-6 member monocyclic heteroaryl or an 8-10 member bicyclic heteroaryl containing 1-3 heteroatoms independently selected from N, O and S). In some embodiments, $R^{a1}$, $R^{a2}$, $R^{a3}$, $R^{a4}$, $R^{a6}$, $R^{a7}$ and $R^{a8}$ is independently a 5-6 member monocyclic heteroaryl (e.g., a 5-member monocyclic heteroaryl containing 1-3 heteroatoms independently selected from O, N and S, a 6-member monocyclic heteroaryl containing 1-3 N heteroatoms). In some embodiments, $R^{a1}$, $R^{a2}$, $R^{a3}$, $R^{a4}$, $R^{a6}$, $R^{a7}$ and $R^{a8}$ is independently a 5-member monocyclic heteroaryl (e.g., pyrazolyl, pyrolyl, thiophenyl, furyl, thiazolyl, isothiazolyl, oxazolyl, isoxazolyl, imidazolyl, triazolyl, thiadiazolyl, oxadiazolyl). In some embodiments, $R^{a1}$, $R^{a2}$, $R^{a3}$, $R^{a4}$, $R^{a6}$, $R^{a7}$ and $R^{a8}$ is independently thiophenyl (e.g., thiophen-2-yl, thiophen-3-yl). In some embodiments, $R^{a1}$, $R^{a2}$, $R^{a3}$, $R^{a4}$, $R^{a6}$, $R^{a7}$ and $R^{a8}$ is independently pyrazolyl (e.g. pyrazol-1-yl, pyrazol-3-yl, pyrazol-5-yl). In some embodiments, $R^{a1}$, $R^{a2}$, $R^{a3}$, $R^{a4}$, $R^{a6}$, $R^{a7}$ and $R^{a8}$ is independently thiazolyl (e.g., thiazol-2-yl, thiazol-4-yl, thiazol-5-yl). In some embodiments, $R^{a1}$, $R^{a2}$, $R^{a3}$, $R^{a4}$, $R^{a6}$, $R^{a7}$ and $R^{a8}$ is independently a 6-member monocyclic heteroaryl (e.g., pyridyl, pyrimidinyl, triazinyl, pyrazinyl, pyridazinyl). In some embodiments, $R^{a1}$, $R^{a2}$, $R^{a3}$, $R^{a4}$, Ra, $R^{a7}$ and $R^{a8}$ is independently pyridinyl (e.g., pyridin-2-yl, pyridin-3-yl, pyridin-4-yl). In some embodiments, $R^{a1}$, $R^{a2}$, $R^{a3}$, $R^{a4}$, $R^{a6}$, $R^{a7}$ and $R^{a8}$ is independently pyrimidinyl (e.g., pyrimidin-2-yl, pyrimidin-4-yl, pyrimidin-5-yl).

In some embodiments, $R^{a1}$, $R^{a2}$, $R^{a3}$, $R^{a4}$, $R^{a6}$, $R^{a7}$ and $R^{a8}$ is independently aryl. In some embodiments, $R^{a1}$, $R^{a2}$, $R^{a3}$, $R^{a4}$, $R^{a6}$, $R^{a7}$ and $R^{a8}$ is independently 6-10 member mono or bicyclic aryl. In some embodiments, $R^{a1}$, $R^{a2}$, $R^{a3}$, $R^{a4}$, $R^{a6}$, $R^{a7}$ and $R^{a8}$ is independently phenyl. In some embodiments, the phenyl is substituted with 0, 1, 2 or 3 instances of $R^9$ as defined herein.

In some embodiments, each $R^{a1}$, $R^{a2}$, $R^{a3}$, $R^{a4}$, Ra, $R^{a7}$ and $R^{a8}$ is independently cycloalkylalkyl (e.g., cyclopropylmethyl, cyclobutylmethyl, cyclopentylmethyl, cyclohexylmethyl, cycloheptylmethyl). In some embodiments, each $R^{a1}$, $R^{a2}$, $R^{a3}$, $R^{a4}$, $R^{a6}$, $R^{a7}$ and $R^{a8}$ is independently heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl).

In some embodiments, each $R^{a1}$, $R^{a2}$, $R^{a3}$, $R^{a4}$, Ra, $R^{a7}$ and $R^{a8}$ is independently arylalkyl. In some embodiments, each $R^{a1}$, $R^{a2}$, $R^{a3}$, $R^{a4}$, $R^{a6}$, $R^{a7}$ and $R^{a8}$ is independently benzyl. In some embodiments, each $R^{a1}$, $R^{a2}$, $R^{a3}$, $R^{a4}$, Ra, $R^{a7}$ and $R^{a8}$ is independently heteroarylalkyl (e.g., pyridinylmethyl, thiazolylmethyl, triazolylmethyl, pyrazolylmethyl).

As generally defined herein, each $R^9$ is independently selected from =O, halo, —CN, —$C_1$-$C_6$ alkyl, —$C_1$-$C_6$ heteroalkyl, —$C_1$-$C_6$ haloalkyl, —$C_3$-$C_9$ cycloalkyl, 3-10 membered heterocyclyl, $C_6$-$C_{10}$ aryl, 5-10 membered heteroaryl, cycloalkylalkyl, heterocyclylalkyl, arylalkyl, heteroarylalkyl, —$OR^b$, —$N(R^b)_2$, —$C(=O)R^b$, —$C(=O)OR^b$, —$NR^bC(=O)R^b$, —$NR^bC(=O)OR^b$, —$C(=O)N(R^b)_2$, —$OC(=O)N(R^b)_2$, —$S(=O)R^b$, —$S(=O)_2R^b$, —$SR^b$, —$S(=O)(=NR^b)R^b$, —$NR^bS(=O)_2R^b$ and —$S(=O)_2N(R^b)_2$, wherein each $R^b$ is independently selected from H, —$C_1$-$C_6$ alkyl (e.g., -Me, -Et, —Pr, -$^i$Pr, -$^n$Bu, $^t$-Bu, -sec-Bu, -iso-Bu). and $C_3$-$C_9$ cycloalkyl (e.g., cyclopropyl, cyclobutyl, cyclopentyl, cyclohexyl).

In some embodiments, each $R^9$ is independently selected from =O, halo, —CN, —$C_1$-$C_6$ alkyl (e.g., -Me, -Et, —Pr, -$^i$Pr, -$^n$Bu, -$^t$Bu, -sec-Bu, -iso-Bu), —$C_1$-$C_6$ haloalkyl (e.g., —$CF_3$, —$CHF_2$), —$C_3$-$C_9$ cycloalkyl (e.g., cyclopropyl, cyclobutyl, cyclopentyl, cyclohexyl), 3-10 membered heterocyclyl (e.g., oxetanyl, tetrahydropyranyl, tetrahydrofuranyl, azetidinyl, pyrrolidinyl, piperidinyl, piperazinyl, morpholinyl, azepanyl), $C_6$-$C_{10}$ aryl (e.g., phenyl), 5-10 membered heteroaryl (e.g., pyrazolyl, pyrolyl, thiophenyl, furyl, thiazolyl, isothiazolyl, oxazolyl, isoxazolyl, imidazolyl, triazolyl, thiadiazolyl, oxadiazolyl), cycloalkylalkyl (e.g., cyclopropylmethyl, cyclobutylmethyl, cyclopentylmethyl, cyclohexylmethyl, cycloheptylmethyl), heterocyclylalkyl (e.g., oxetanylmethyl, aziridinylmethyl, tetrahydrofuranylmethyl, pyrolidinylmethyl, tetrahydropyranylmethyl, piperidinylmethyl, piperazinylmethyl, morpholinylmethyl, azepanylmethyl), arylalkyl (e.g., benzyl), heteroarylalkyl (e.g., pyridinylmethyl, thiazolylmethyl, triazolylmethyl, pyrazolylmethyl), —$OR^b$, —$N(R^b)_2$, —$C(=O)R^b$, —$C(=O)OR^b$, —$NR^bC(=O)R^b$, —$NR^bC(=O)OR^b$, —C(═O)N(R$^b$)$_2$, —OC(═O)N(R$^b$)$_2$, —S(═O)R$^b$, —S(═O)$_2$R$^b$, —SR$^b$, —S(═O)(═NR$^b$)R$^b$, —NR$^b$S(═O)$_2$R$^b$ and —S(═O)$_2$N(R$^b$)$_2$, wherein each R$^b$ is as defined herein. In further embodiments, each R$^b$ is H or -Me.

In one embodiment, the invention provides a compound selected from the compounds of Table 1, or pharmaceutically acceptable salts thereof.

Compounds described herein (e.g., a compound of Formula (I), (Ia), (Ib), (Ic) and (Id) or a compound of Table 1, or pharmaceutically acceptable salts thereof) are useful as inhibitors of PRMT5 (e.g., MTA uncompetitive PRMT5 inhibitors).

Table 1 indicates IC$_{50}$ values (μM) against PRMT5 for exemplary compounds in the presence of SAM as cofactor, with no cofactor, and with MTA as cofactor, respectively (columns 4-6). For Table 1, "a" "aa", and "aaa" indicates an IC$_{50}$ less than 50 nM in the assays with SAM, no cofactor, and MTA respectively; "b", "bb", and "bbb" indicates an IC$_{50}$ of 50 nM to less than 500 nM in the assays with SAM, no cofactor, and MTA, respectively; "c", "cc", and "ccc" indicates an IC$_{50}$ of greater than or equal to 500 nM in the assays with SAM, no cofactor, and MTA, respectively. Ki values can be calculated from the IC$_{50}$ values as described in the Examples section. As detailed in the Examples section, for the assay performed in the presence of SAM, IC$_{50}$=Ki×1.5 (Ki=IC$_{50}$/1.5). For the assay performed in the presence of MTA, IC$_{50}$=Ki×13.5 (Ki=IC$_{50}$/13.5).

Table 1 also indicates IC$_{50}$ values in an MTAP-isogenic cell line pair for exemplary compounds in an SDMA in-cell western assay (columns 7-8). HAP1 MTAP-intact is a cell line in which endogenous levels of MTAP are expressed, and HAP1 MTAP-deleted is an MTAP-null cell line. For Table 1, "a*" and "aa*" indicates an IC$_{50}$ of <100 nM, "b*" and "bb*" indicates an IC$_{50}$ equal to or greater than 100 nM but less than 1 μM, and "c*" and "cc*" indicates an IC$_{50}$ of greater than or equal to 1 μM in the HAP1 MTAP-intact and the HAP1 MTAP-deleted assays, respectively. In column 9, "A" indicates an IC$_{50}$ ratio greater than or equal to 10 fold between the IC$_{50}$ in the HAP1 MTAP-intact cell line and the HAP1 MTAP-deleted cell line; "B" indicates an IC$_{50}$ ratio greater than or equal to 3 fold but lower than 10 fold between the IC$_{50}$ in the HAP1 MTAP-intact cell line and the HAP1 MTAP-deleted cell line; "C" indicates an IC$_{50}$ ratio of less than 3 fold between the IC$_{50}$ in the HAP1 MTAP-intact cell line and the HAP1 MTAP-deleted cell line. Compounds with a ratio in the SDMA in-cell western assay of equal to or greater than 3 fold are considered MTAP-selective.

Table 1 additionally indicates IC$_{50}$ values in a viability assay for the MTAP-deleted cell line (column 10), indicating the effect of treatment with compound on cell survival. In column 10, a value of A* indicates an IC$_{50}$ of less than 1 μM, a value of B* indicates an IC$_{50}$ equal to or greater than 1 μM but less than 10 μM, and a value of C* indicates an IC$_{50}$ greater than or equal to 10 μM.

Unless otherwise indicated, the absolute stereochemistry of all chiral atoms is as depicted. Compounds marked with (or) or (rel) are single enantiomers wherein the absolute stereochemistry was arbitrarily assigned (e.g., based on chiral SFC elution as described in the Examples section). Compounds marked with (and) or (rac) are mixtures of enantiomers wherein the relative stereochemistry is as shown. Compounds marked with (abs) are single enantiomers wherein the absolute stereochemistry is as indicated.

TABLE 1

Exemplary compounds of the invention and biological data

| Structure | Nr | Stereo | SAM IC50 | No Cofactor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| [structure] | 1 |  | b | bb | bbb | c* | cc* | C |  |
| [structure] | 2 | or/rel | b | bb | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 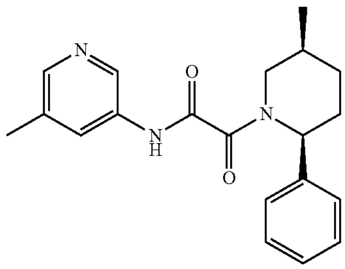 [SMILES: Cc1cncc(NC(=O)C(=O)N2C[C@@H](C)CC[C@H]2c2ccccc2)c1] | 3 | or/rel | c | cc | ccc | | | | |
| 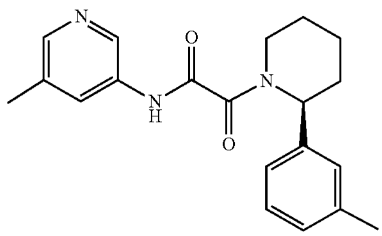 | 4 | or/rel | c | cc | bbb | c* | cc* | C | |
| 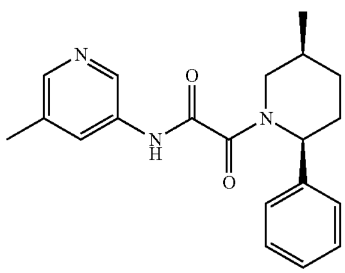 [SMILES: Cc1cncc(NC(=O)C(=O)N2C[C@@H](C)CC[C@H]2c2ccccc2)c1] | 5 | or/rel | c | cc | ccc | | | | |
| 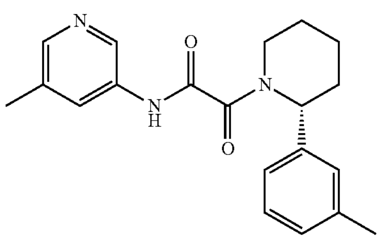 | 6 | and/rac | c | cc | ccc | c* | cc* | C | |
| 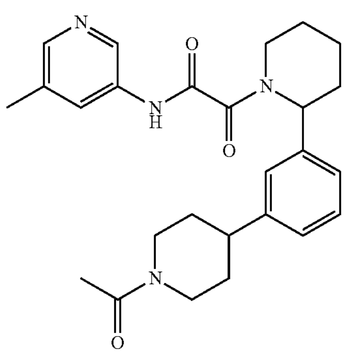 [SMILES: CC(=O)N1CCC(c2cccc(C3CCCCN3C(=O)C(=O)Nc3cncc(C)c3)c2)CC1] | 7 | | c | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 8 | and/rac | c | cc | bbb | c* | cc* | C | C* |
| | 9 | | b | bb | aaa | c* | bb* | A | C* |
| | 10 | or/rel | b | bb | bbb | c* | cc* | B | C* |
| | 11 | or/rel | c | cc | ccc | c* | cc* | C | C* |
| | 12 | or/rel | c | cc | ccc | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 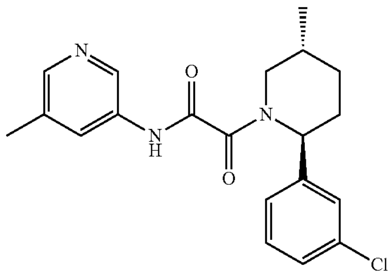 [SMILES: Cc1cncc(NC(=O)C(=O)N2C[C@H](C)CC[C@H]2c2cccc(Cl)c2)c1] | 13 | and/rac | c | cc | bbb | c* | cc* | C | C* |
| 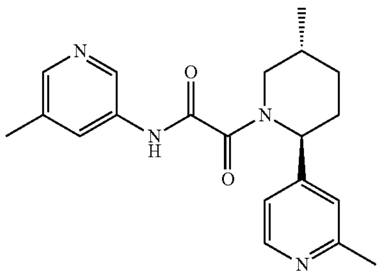 | 14 | and/rac | b | cc | bbb | c* | cc* | C | C* |
| 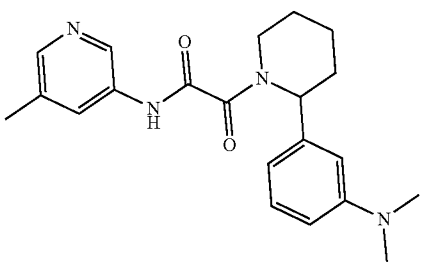 | 15 | | c | cc | bbb | c* | cc* | C | C* |
| 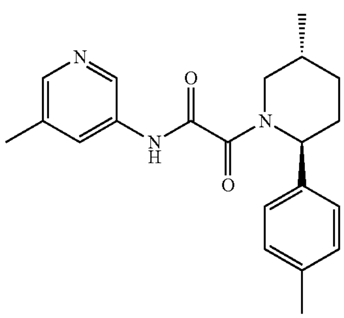 [SMILES: Cc1ccc([C@@H]2CC[C@@H](C)CN2C(=O)C(=O)Nc2cncc(C)c2)cc1] | 16 | or/rel | c | cc | bbb | c* | cc* | B | C* |
| 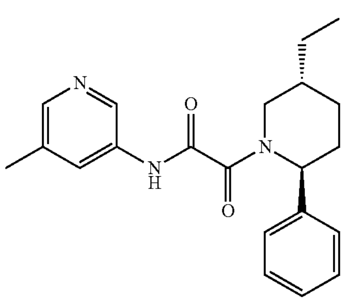 [SMILES: CC[C@@H]1CC[C@@H](c2ccccc2)N(C(=O)C(=O)Nc2cncc(C)c2)C1] | 17 | or/rel | c | cc | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure) | 18 | or/rel | c | cc | ccc | | | | |
| (structure) | 19 | or/rel | c | cc | ccc | | | | |
| (structure) | 20 | or/rel | c | cc | ccc | | | | |
| (structure) | 21 | or/rel | b | bb | bbb | c* | cc* | B | C* |
| (structure) | 22 | or/rel | c | cc | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 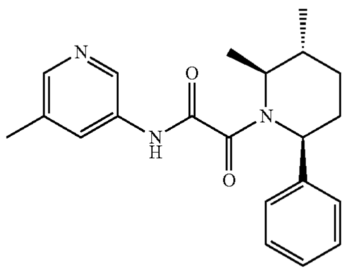 [SMILES: Cc1cncc(NC(=O)C(=O)N2[C@H](c3ccccc3)CC[C@@H](C)[C@@H]2C)c1] | 23 | and/rac | c | cc | bbb | c* | cc* | C | C* |
| 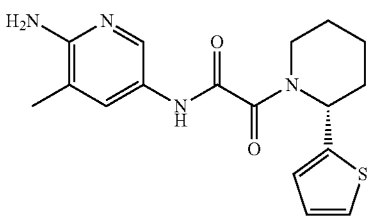 [SMILES: Cc1cc(NC(=O)C(=O)N2CCCC[C@@H]2c2cccs2)cnc1N] | 24 | or/rel | b | bb | aaa | c* | aa* | A | C* |
| 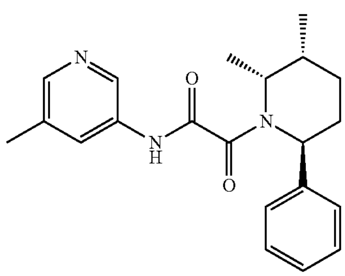 [SMILES: Cc1cncc(NC(=O)C(=O)N2[C@H](C)[C@H](C)CC[C@H]2c2ccccc2)c1] | 25 | and/rac | c | cc | bbb | | | | |
| 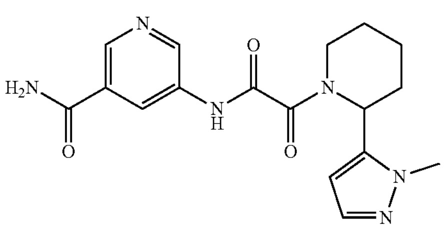 [SMILES: Cn1nccc1C1CCCCN1C(=O)C(=O)Nc1cncc(C(N)=O)c1] | 26 | | b | cc | bbb | c* | bb* | A | C* |
| 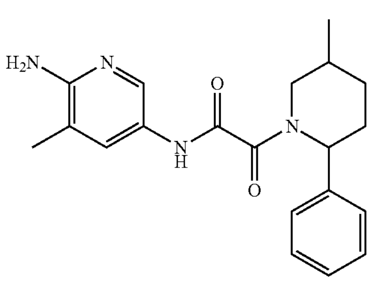 [SMILES: Cc1cc(NC(=O)C(=O)N2CC(C)CCC2c2ccccc2)cnc1N] | 27 | | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 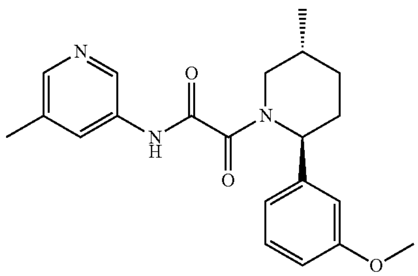 | 28 | and/rac | b | bb | bbb | c* | cc* | C | C* |
| 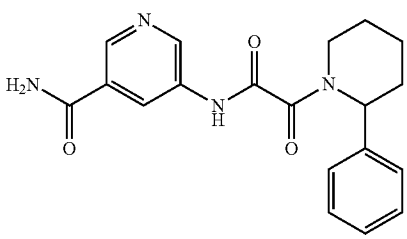 [SMILES: NC(=O)c1cncc(NC(=O)C(=O)N2CCCCC2c2ccccc2)c1] | 29 | | b | cc | bbb | c* | bb* | A | C* |
| 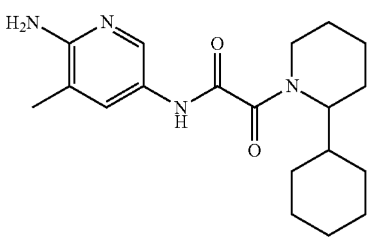 [SMILES: Cc1cc(NC(=O)C(=O)N2CCCCC2C2CCCCC2)cnc1N] | 30 | | b | bb | bbb | c* | bb* | A | C* |
| 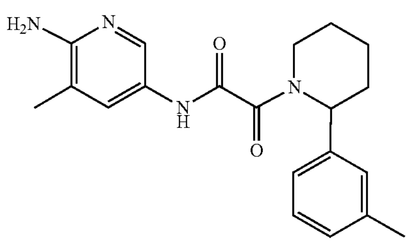 [SMILES: Cc1cccc(C2CCCCN2C(=O)C(=O)Nc2cnc(N)c(C)c2)c1] | 31 | | b | bb | aaa | c* | bb* | A | C* |
| 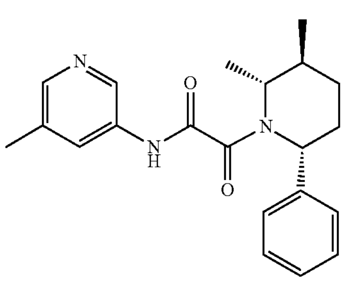 [SMILES: Cc1cncc(NC(=O)C(=O)N2[C@@H](c3ccccc3)CC[C@H](C)[C@H]2C)c1] | 32 | or/rel | c | cc | ccc | c* | cc* | C | C* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 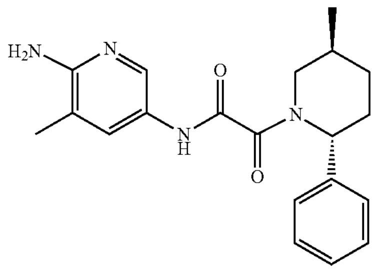 [SMILES: Cc1cc(NC(=O)C(=O)N2C[C@@H](C)CC[C@@H]2c2ccccc2)cnc1N] | 33 | or/rel | b | bb | aaa | b* | aa* | A | B* |
| 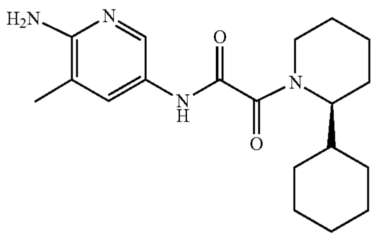 [SMILES: Cc1cc(NC(=O)C(=O)N2CCCC[C@H]2C2CCCCC2)cnc1N] | 34 | or/rel | c | cc | ccc | c* | cc* | C | C* |
| 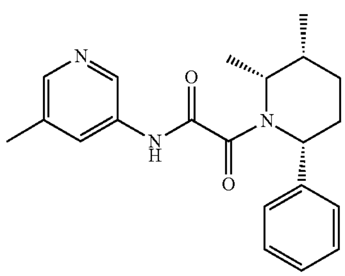 [SMILES: Cc1cncc(NC(=O)C(=O)N2[C@@H](c3ccccc3)CC[C@@H](C)[C@H]2C)c1] | 35 | or/rel | c | cc | bbb | c* | cc* | C | C* |
| 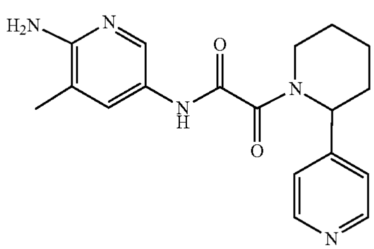 [SMILES: Cc1cc(NC(=O)C(=O)N2CCCCC2c2ccncc2)cnc1N] | 36 | | b | bb | aaa | c* | bb* | A | C* |
| 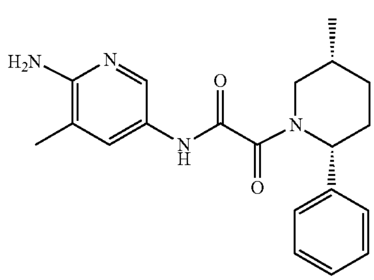 [SMILES: Cc1cc(NC(=O)C(=O)N2C[C@H](C)CC[C@@H]2c2ccccc2)cnc1N] | 37 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 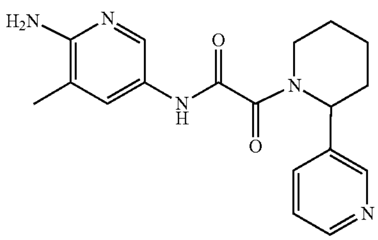 [SMILES: Cc1cc(NC(=O)C(=O)N2CCCCC2c2cccnc2)cnc1N] | 38 | | b | bb | bbb | c* | cc* | B | C* |
| 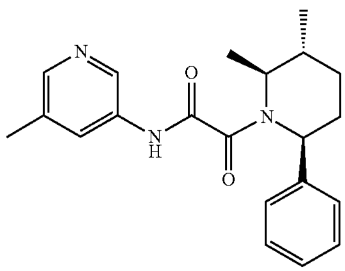 [SMILES: Cc1cncc(NC(=O)C(=O)N2[C@H](c3ccccc3)CC[C@@H](C)[C@@H]2C)c1] | 39 | or/rel | b | cc | bbb | c* | cc* | C | C* |
| 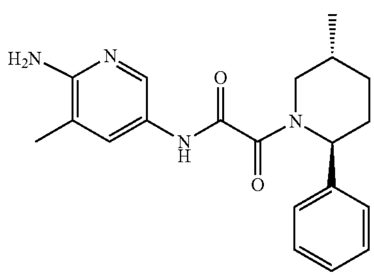 [SMILES: Cc1cc(NC(=O)C(=O)N2C[C@H](C)CC[C@H]2c2ccccc2)cnc1N] | 40 | or/rel | c | cc | ccc | | | | C* |
| 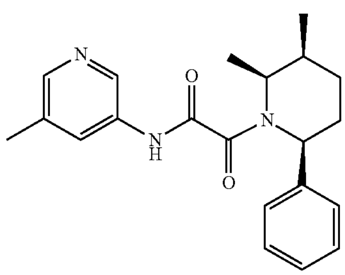 [SMILES: Cc1cncc(NC(=O)C(=O)N2[C@H](c3ccccc3)CC[C@H](C)[C@@H]2C)c1] | 41 | or/rel | c | cc | ccc | | | | C* |
| 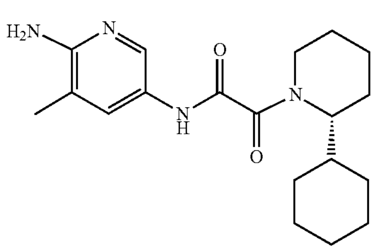 [SMILES: Cc1cc(NC(=O)C(=O)N2CCCC[C@@H]2C2CCCCC2)cnc1N] | 42 | or/rel | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 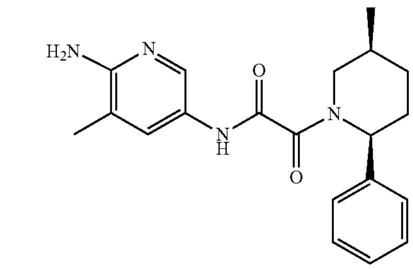 [SMILES: Cc1cc(NC(=O)C(=O)N2C[C@@H](C)CC[C@H]2c2ccccc2)cnc1N] | 43 | or/rel | c | cc | ccc | | | | |
| 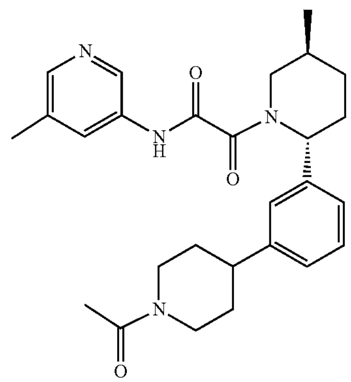 [SMILES: CC(=O)N1CCC(c2cccc([C@H]3CC[C@H](C)CN3C(=O)C(=O)Nc3cncc(C)c3)c2)CC1] | 44 | and/rac | c | cc | bbb | | | | C* |
| 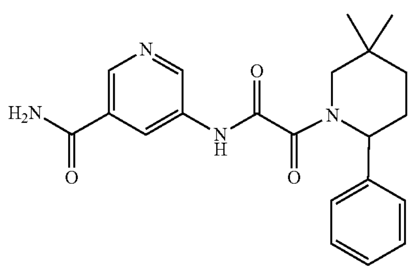 [SMILES: CC1(C)CCC(c2ccccc2)N(C(=O)C(=O)Nc2cncc(C(N)=O)c2)C1] | 45 | | c | cc | bbb | c* | bb* | A | C* |
| 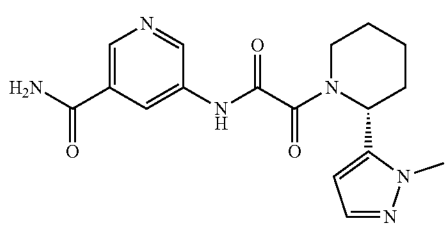 | 46 | or/rel | b | bb | aaa | c* | bb* | A | C* |
| 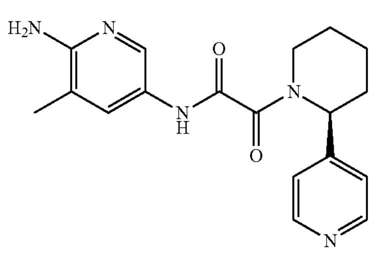 [SMILES: Cc1cc(NC(=O)C(=O)N2CCCC[C@H]2c2ccncc2)cnc1N] | 47 | or/rel | c | cc | ccc | c* | cc* | C | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 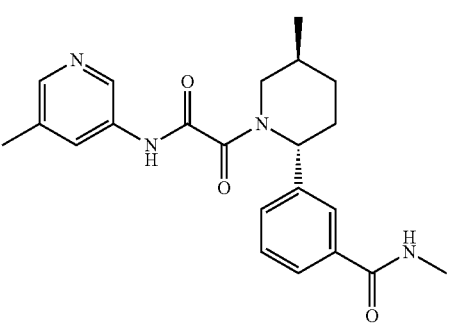 | 48 | and/rac | b | bb | bbb | c* | cc* | C | C* |
| 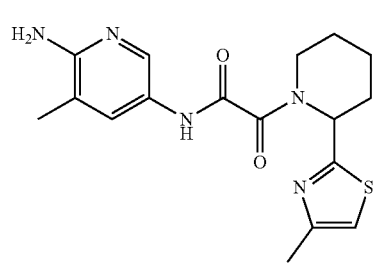 [SMILES: Cc1csc(C2CCCCN2C(=O)C(=O)Nc2cnc(N)c(C)c2)n1] | 49 | | b | bb | aaa | c* | bb* | A | C* |
| 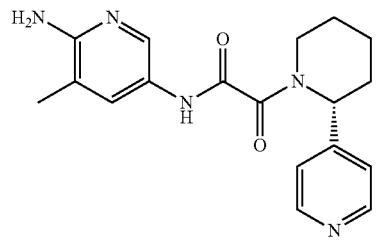 [SMILES: Cc1cc(NC(=O)C(=O)N2CCCC[C@@H]2c2ccncc2)cnc1N] | 50 | or/rel | b | bb | aaa | c* | bb* | B | C* |
| 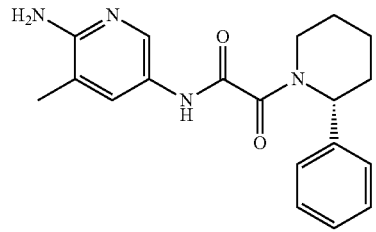 [SMILES: Cc1cc(NC(=O)C(=O)N2CCCC[C@@H]2c2ccccc2)cnc1N] | 51 | or/rel | b | bb | aaa | c* | bb* | B | C* |
| 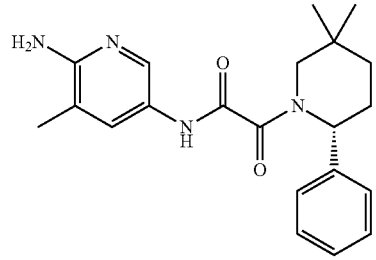 [SMILES: Cc1cc(NC(=O)C(=O)N2CC(C)(C)CC[C@@H]2c2ccccc2)cnc1N] | 52 | or/rel | b | bb | aaa | b* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| [structure] | 53 | | b | bb | aaa | c* | bb* | A | C* |
| [structure] | 54 | or/rel | b | bb | aaa | c* | bb* | A | B* |
| [structure] | 55 | or/rel | c | cc | bbb | c* | cc* | C | C* |
| [structure] | 56 | | b | bb | bbb | b* | aa* | B | B* |
| [structure] | 57 | or/rel | c | cc | bbb | c* | cc* | C | C* |
| [structure] | 58 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 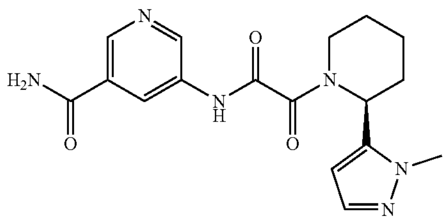 [SMILES: Cn1nccc1[C@@H]1CCCCN1C(=O)C(=O)Nc1cncc(C(N)=O)c1] | 59 | or/rel | c | cc | bbb | | | | C* |
| 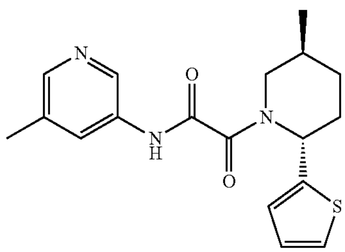 [SMILES: Cc1cncc(NC(=O)C(=O)N2C[C@@H](C)CC[C@@H]2c2cccs2)c1] | 60 | and/rac | c | cc | bbb | c* | cc* | C | C* |
| 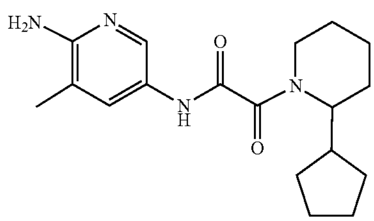 [SMILES: Cc1cc(NC(=O)C(=O)N2CCCCC2C2CCCC2)cnc1N] | 61 | | c | bb | bbb | c* | aa* | A | B* |
| 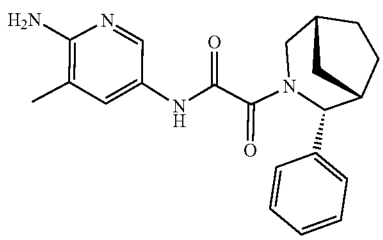 [SMILES: Cc1cc(NC(=O)C(=O)N2C[C@@H]3CC[C@@H](C3)[C@@H]2c2ccccc2)cnc1N] | 62 | or/rel | c | cc | bbb | | | | C* |
| 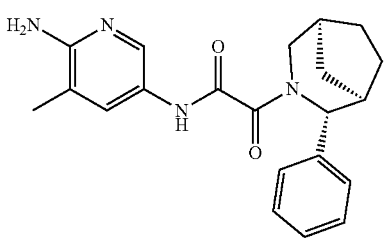 [SMILES: Cc1cc(NC(=O)C(=O)N2C[C@H]3CC[C@H](C3)[C@@H]2c2ccccc2)cnc1N] | 63 | or/rel | c | cc | ccc | c* | cc* | C | C* |
| 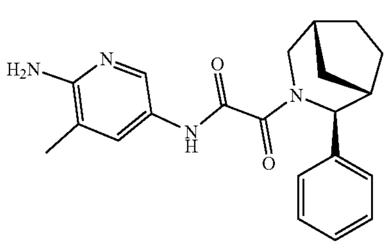 [SMILES: Cc1cc(NC(=O)C(=O)N2C[C@@H]3CC[C@@H](C3)[C@H]2c2ccccc2)cnc1N] | 64 | or/rel | b | bb | aaa | c* | aa* | A | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 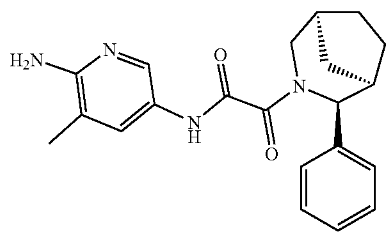 [SMILES: Cc1cc(NC(=O)C(=O)N2C[C@H]3CC[C@H](C3)[C@H]2c2ccccc2)cnc1N] | 65 | or/rel | b | bb | bbb | c* | aa* | A | B* |
| 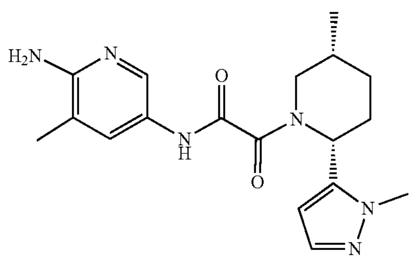 [SMILES: Cc1cc(NC(=O)C(=O)N2C[C@H](C)CC[C@@H]2c2ccnn2C)cnc1N] | 66 | and/rac | b | bb | aaa | c* | bb* | A | C* |
| 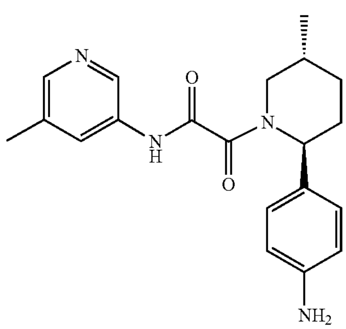 [SMILES: Cc1cncc(NC(=O)C(=O)N2C[C@H](C)CC[C@H]2c2ccc(N)cc2)c1] | 67 | or/rel | b | bb | bbb | c* | cc* | B | C* |
| 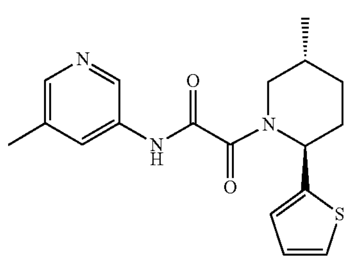 [SMILES: Cc1cncc(NC(=O)C(=O)N2C[C@H](C)CC[C@H]2c2cccs2)c1] | 68 | or/rel | b | bb | aaa | c* | bb* | A | C* |
| 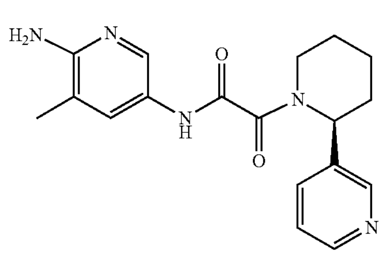 [SMILES: Cc1cc(NC(=O)C(=O)N2CCCC[C@H]2c2cccnc2)cnc1N] | 69 | or/rel | b | bb | aaa | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 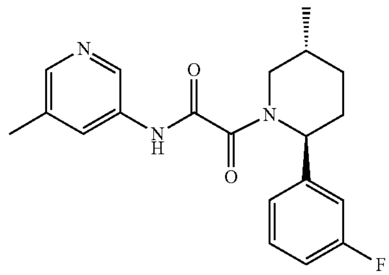 [SMILES: Cc1cncc(NC(=O)C(=O)N2C[C@H](C)CC[C@H]2c2cccc(F)c2)c1] | 70 | and/rac | c | cc | bbb | c* | cc* | C | C* |
| 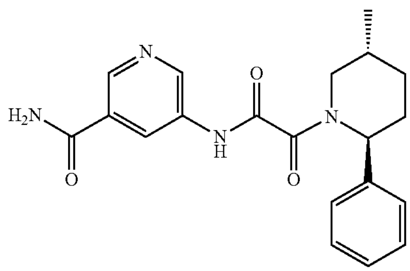 [SMILES: C[C@@H]1CC[C@@H](c2ccccc2)N(C(=O)C(=O)Nc2cncc(C(N)=O)c2)C1] | 71 | or/rel | c | cc | ccc | | cc* | C | C* |
| 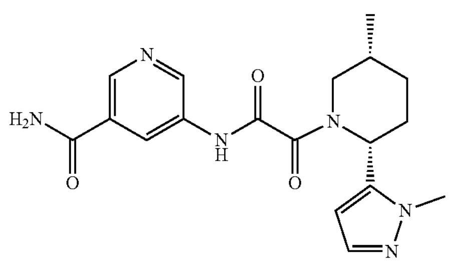 [SMILES: C[C@@H]1CC[C@H](c2ccnn2C)N(C(=O)C(=O)Nc2cncc(C(N)=O)c2)C1] | 72 | and/rac | b | bb | bbb | c* | bb* | A | C* |
| 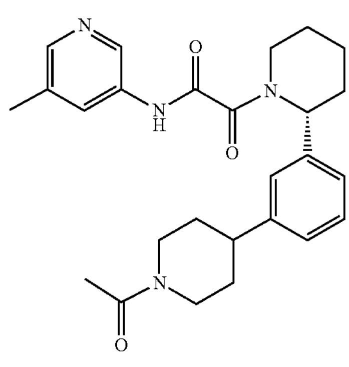 [SMILES: CC(=O)N1CCC(c2cccc([C@H]3CCCCN3C(=O)C(=O)Nc3cncc(C)c3)c2)CC1] | 73 | or/rel | c | cc | ccc | c* | cc* | C | C* |
| 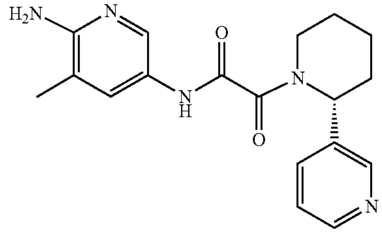 | 74 | or/rel | c | cc | bbb | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 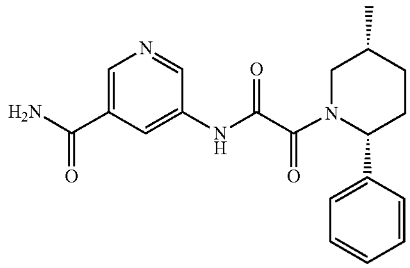 [SMILES: C[C@@H]1CC[C@H](c2ccccc2)N(C(=O)C(=O)Nc2cncc(C(N)=O)c2)C1] | 75 | or/rel | c | cc | bbb | c* | cc* | C | |
| 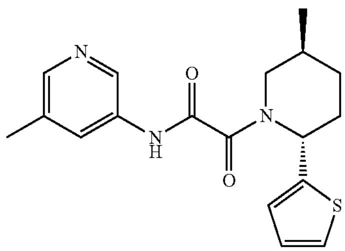 [SMILES: Cc1cncc(NC(=O)C(=O)N2C[C@@H](C)CC[C@@H]2c2cccs2)c1] | 76 | or/rel | c | cc | ccc | c* | | | C* |
| 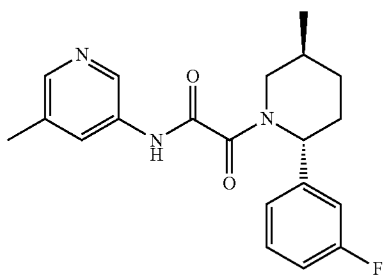 [SMILES: Cc1cncc(NC(=O)C(=O)N2C[C@@H](C)CC[C@@H]2c2cccc(F)c2)c1] | 77 | or/rel | | cc | ccc | c* | cc* | C | C* |
| 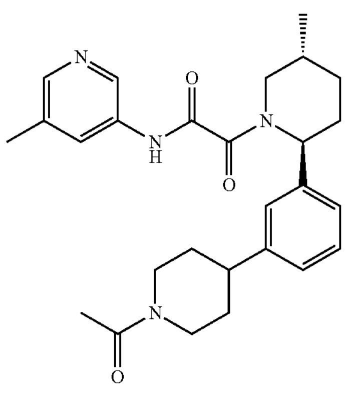 [SMILES: CC(=O)N1CCC(c2cccc([C@@H]3CC[C@@H](C)CN3C(=O)C(=O)Nc3cncc(C)c3)c2)CC1] | 78 | or/rel | c | cc | bbb | c* | cc* | C | C* |
| 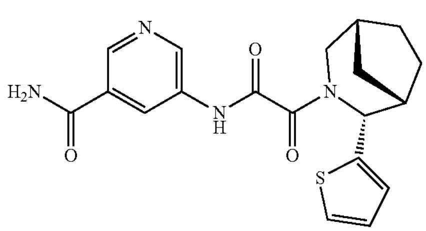 [SMILES: NC(=O)c1cncc(NC(=O)C(=O)N2C[C@@H]3CC[C@@H](C3)[C@@H]2c2cccs2)c1] | 79 | and/rac | b | cc | bbb | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 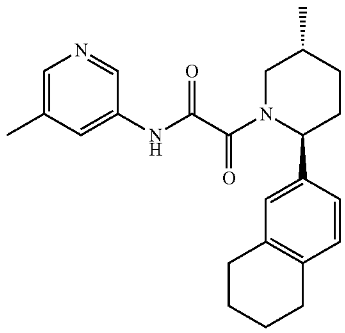 [SMILES: Cc1cncc(NC(=O)C(=O)N2C[C@H](C)CC[C@H]2c2ccc3c(c2)CCCC3)c1] | 80 | and/rac | c | cc | bbb | c* | cc* | C | C* |
| 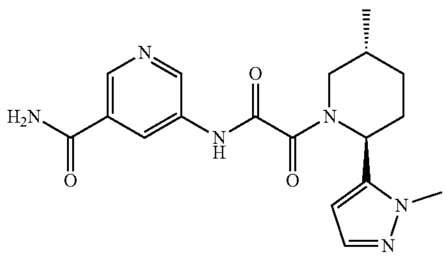 [SMILES: C[C@@H]1CC[C@@H](c2ccnn2C)N(C(=O)C(=O)Nc2cncc(C(N)=O)c2)C1] | 81 | and/rac | c | cc | bbb | c* | bb* | A | C* |
| 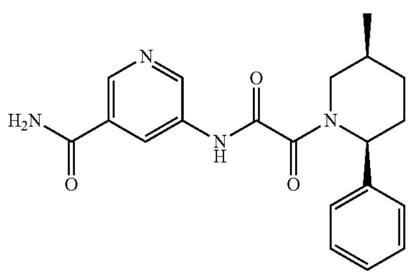 [SMILES: C[C@H]1CC[C@@H](c2ccccc2)N(C(=O)C(=O)Nc2cncc(C(N)=O)c2)C1] | 82 | or/rel | b | bb | aaa | c* | bb* | A | C* |
| 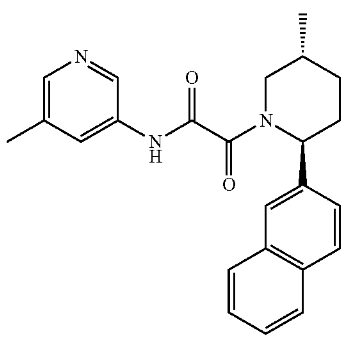 [SMILES: Cc1cncc(NC(=O)C(=O)N2C[C@H](C)CC[C@H]2c2ccc3ccccc3c2)c1] | 83 | and/rac | c | cc | bbb | c* | cc* | C | C* |
| 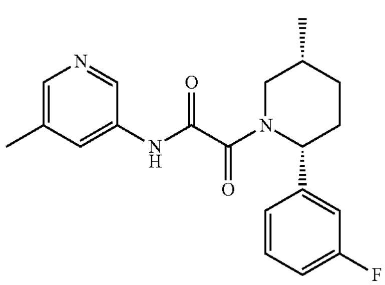 [SMILES: Cc1cncc(NC(=O)C(=O)N2C[C@H](C)CC[C@@H]2c2cccc(F)c2)c1] | 84 | or/rel | c | cc | ccc | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| (structure 85) | 85 | or/rel | b | bb | aaa | c* | bb* | A | C* |
| (structure 86) | 86 |  | b | bb | bbb | c* | bb* | A | C* |
| (structure 87) | 87 | or/rel | b | bb | bbb | c* | cc* | C | C* |
| (structure 88) | 88 | or/rel | b | bb | aaa | c* | aa* | A | B* |
| (structure 89) | 89 | and/rac | c | bb | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 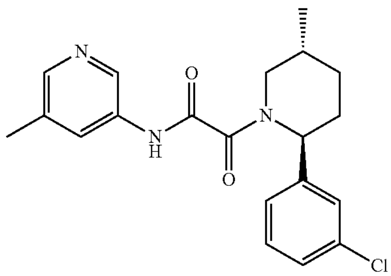 [SMILES: Cc1cncc(NC(=O)C(=O)N2C[C@H](C)CC[C@H]2c2cccc(Cl)c2)c1] | 90 | or/rel | c | cc | ccc | c* | cc* | C | C* |
| 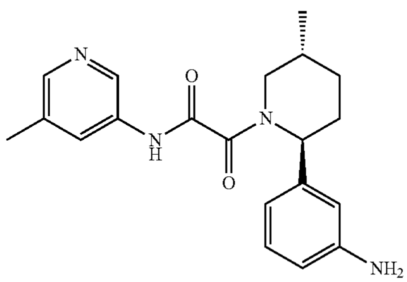 [SMILES: Cc1cncc(NC(=O)C(=O)N2C[C@H](C)CC[C@H]2c2cccc(N)c2)c1] | 91 | and/rac | c | cc | bbb | c* | cc* | C | C* |
| 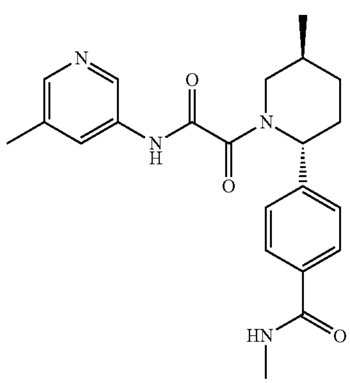 [SMILES: CNC(=O)c1ccc([C@H]2CC[C@H](C)CN2C(=O)C(=O)Nc2cncc(C)c2)cc1] | 92 | and/rac | c | cc | bbb | c* | cc* | C | C* |
| 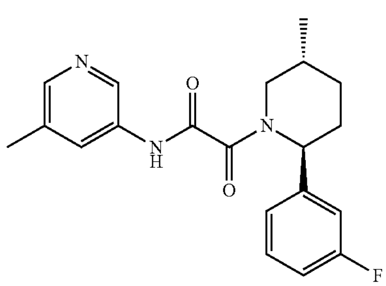 [SMILES: Cc1cncc(NC(=O)C(=O)N2C[C@H](C)CC[C@H]2c2cccc(F)c2)c1] | 93 | or/rel | b | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 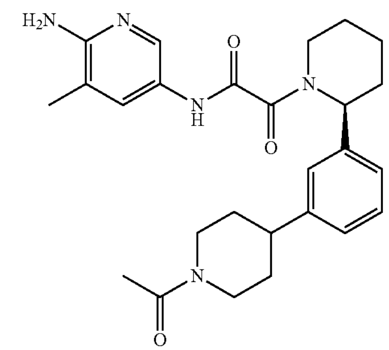 [SMILES: CC(=O)N1CCC(c2cccc([C@@H]3CCCCN3C(=O)C(=O)Nc3cnc(N)c(C)c3)c2)CC1] | 94 | or/rel | b | bb | aaa | b* | aa* | B | B* |
| 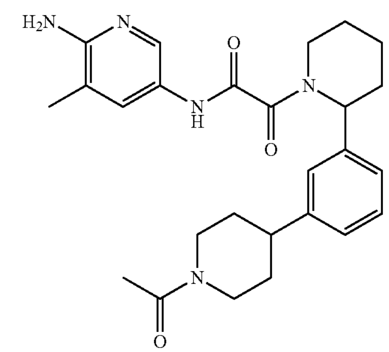 | 95 | | b | bb | aaa | c* | aa* | A | B* |
| 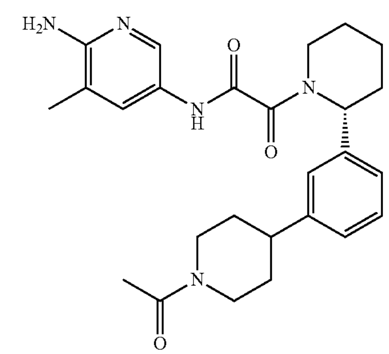 [SMILES: CC(=O)N1CCC(c2cccc([C@H]3CCCCN3C(=O)C(=O)Nc3cnc(N)c(C)c3)c2)CC1] | 96 | or/rel | b | bb | aaa | c* | bb* | A | C* |
| 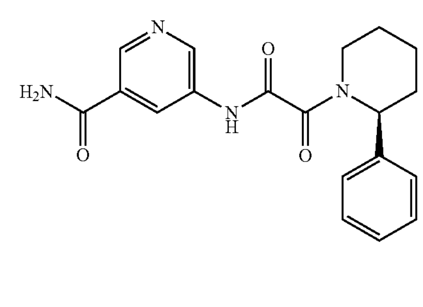 [SMILES: NC(=O)c1cncc(NC(=O)C(=O)N2CCCC[C@H]2c2ccccc2)c1] | 97 | or/rel | c | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 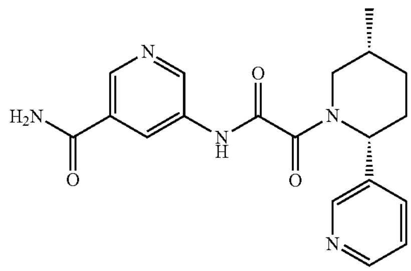 | 98 | or/rel | c | cc | ccc | | | | |
| 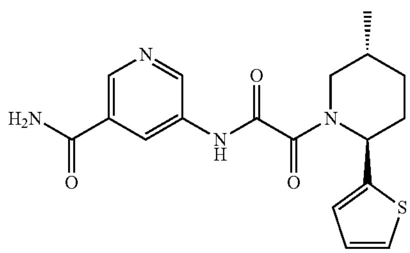 [SMILES: C[C@@H]1CC[C@@H](c2cccs2)N(C(=O)C(=O)Nc2cncc(C(N)=O)c2)C1] | 99 | and/rac | b | bb | aaa | c* | aa* | A | B* |
| 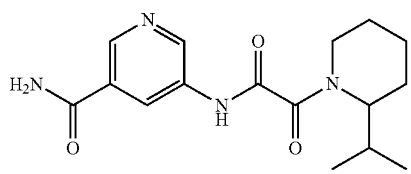 [SMILES: CC(C)C1CCCCN1C(=O)C(=O)Nc1cncc(C(N)=O)c1] | 100 | | b | cc | bbb | c* | bb* | A | C* |
| 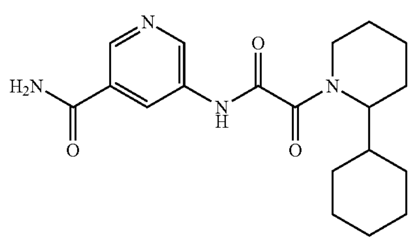 [SMILES: NC(=O)c1cncc(NC(=O)C(=O)N2CCCCC2C2CCCCC2)c1] | 101 | | b | bb | aaa | c* | aa* | A | C* |
| 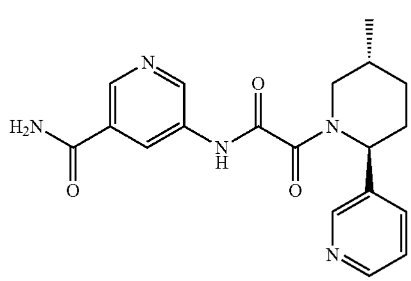 | 102 | and/rac | b | bb | aaa | c* | bb* | A | C* |
| 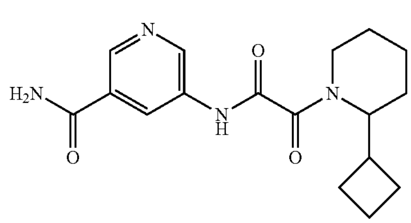 [SMILES: NC(=O)c1cncc(NC(=O)C(=O)N2CCCCC2C2CCC2)c1] | 103 | | b | bb | aaa | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 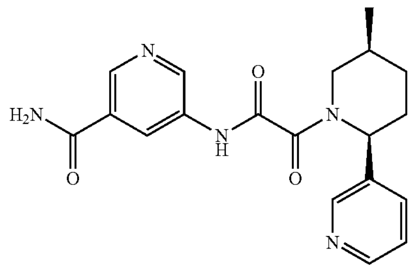 | 104 | or/rel | b | cc | bbb | c* | cc* | B | C* |
| 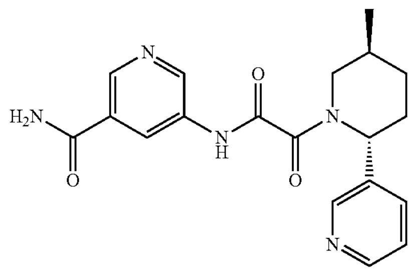 | 105 | or/rel | c | cc | ccc | c* | cc* | C | C* |
| 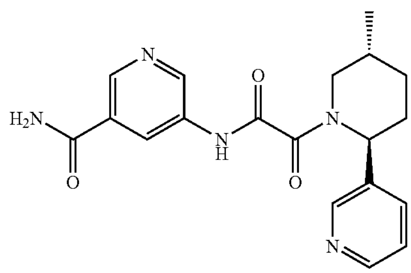 [SMILES: C[C@@H]1CC[C@@H](c2cccnc2)N(C(=O)C(=O)Nc2cncc(C(N)=O)c2)C1] | 106 | or/rel | a | bb | aaa | c* | aa* | A | B* |
| 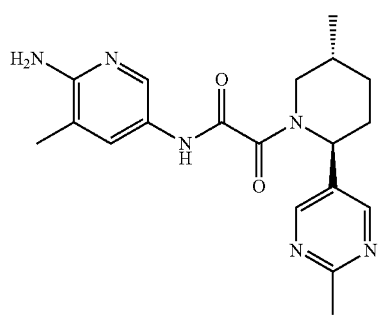 [SMILES: Cc1ncc([C@@H]2CC[C@@H](C)CN2C(=O)C(=O)Nc2cnc(N)c(C)c2)cn1] | 107 | and/rac | b | cc | bbb | c* | cc* | C | C* |
| 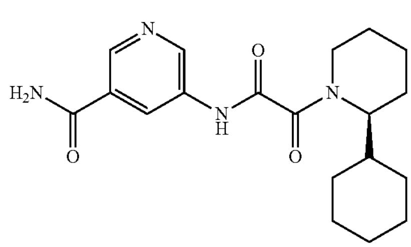 [SMILES: NC(=O)c1cncc(NC(=O)C(=O)N2CCCC[C@H]2C2CCCCC2)c1] | 108 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 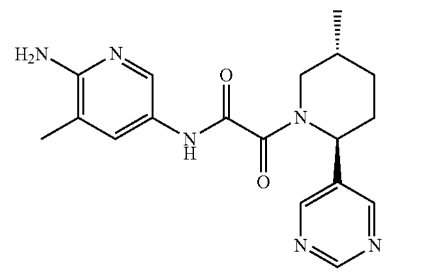 [SMILES: Cc1cc(NC(=O)C(=O)N2C[C@H](C)CC[C@H]2c2cncnc2)cnc1N] | 109 | and/rac | b | cc | bbb | c* | cc* | B | C* |
| 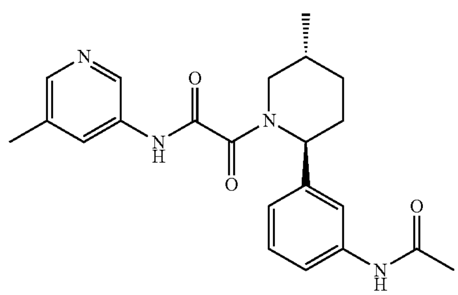 [SMILES: CC(=O)Nc1cccc([C@@H]2CC[C@@H](C)CN2C(=O)C(=O)Nc2cncc(C)c2)c1] | 110 | and/rac | b | bb | bbb | c* | cc* | B | C* |
| 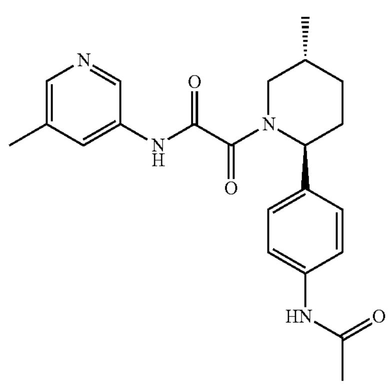 [SMILES: CC(=O)Nc1ccc([C@@H]2CC[C@@H](C)CN2C(=O)C(=O)Nc2cncc(C)c2)cc1] | 111 | and/rac | b | bb | bbb | c* | bb* | A | C* |
| 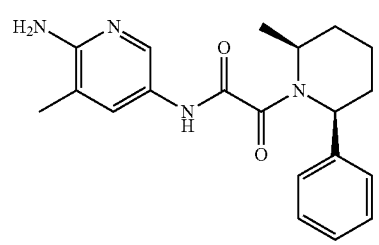 [SMILES: Cc1cc(NC(=O)C(=O)N2[C@@H](C)CCC[C@H]2c2ccccc2)cnc1N] | 112 | and/rac | b | bb | aaa | b* | aa* | B | B* |
| 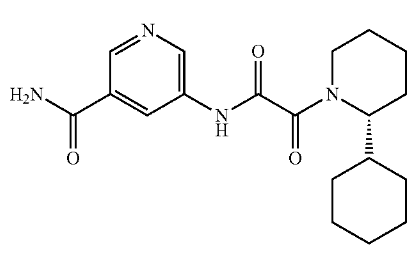 [SMILES: NC(=O)c1cncc(NC(=O)C(=O)N2CCCC[C@@H]2C2CCCCC2)c1] | 113 | or/rel | b | bb | aaa | c* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP1 MTAP deleted IC50 | MTAP intact/deleted ratio | HAP1 MTAP deleted viability |
|---|---|---|---|---|---|---|---|---|---|
| | 114 | and/rac | b | bb | aaa | c* | aa* | A | C* |
| | 115 | or/rel | b | aa | aaa | b* | aa* | A | A* |
| | 116 | | b | cc | bbb | c* | bb* | A | C* |
| | 117 | or/rel | c | cc | bbb | c* | bb* | A | C* |
| | 118 | and/rac | b | cc | aaa | c* | bb* | A | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| | 119 | | b | bb | bbb | c* | bb* | A | C* |
| | 120 | | b | bb | aaa | c* | bb* | A | C* |
| | 121 | or/rel | b | bb | aaa | c* | aa* | A | B* |
| | 122 | or/rel | c | cc | ccc | | | | |
| | 123 | | b | bb | aaa | c* | bb* | A | B* |
| | 124 | and/rac | c | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 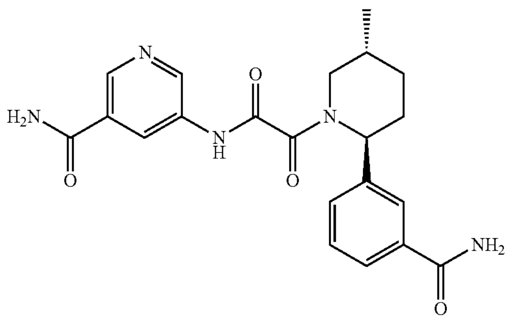 [SMILES: C[C@@H]1CC[C@@H](c2cccc(C(N)=O)c2)N(C(=O)C(=O)Nc2cncc(C(N)=O)c2)C1] | 125 | and/rac | b | bb | bbb | c* | cc* | B | C* |
| 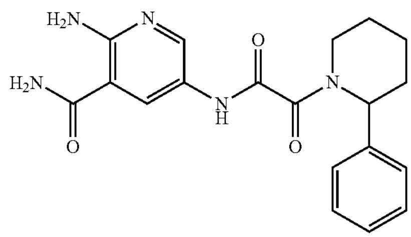 [SMILES: NC(=O)c1cc(NC(=O)C(=O)N2CCCCC2c2ccccc2)cnc1N] | 126 | | b | cc | bbb | c* | cc* | B | C* |
| 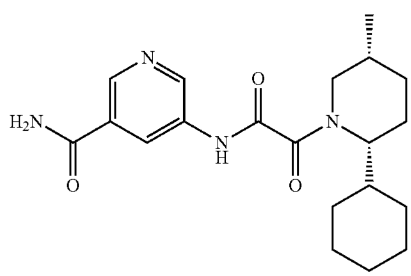 [SMILES: C[C@@H]1CC[C@H](C2CCCCC2)N(C(=O)C(=O)Nc2cncc(C(N)=O)c2)C1] | 127 | or/rel | c | cc | ccc | | | | |
| 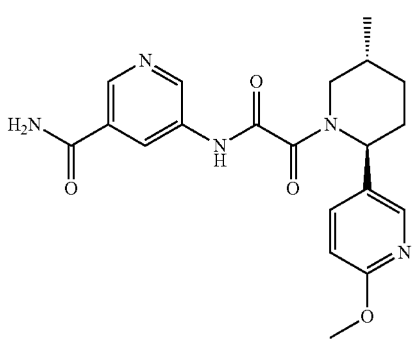 [SMILES: COc1ccc([C@@H]2CC[C@@H](C)CN2C(=O)C(=O)Nc2cncc(C(N)=O)c2)cn1] | 128 | and/rac | b | bb | aaa | c* | bb* | A | C* |
| 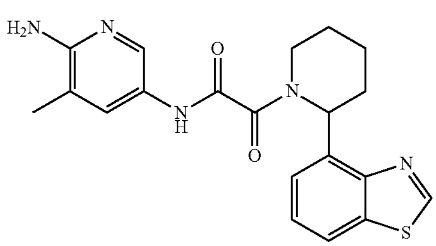 | 129 | | b | cc | bbb | c* | cc* | B | C* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 130 | or/rel | c | cc | ccc | | | | |
| | 131 | and/rac | c | bb | aaa | c* | aa* | A | B* |
| | 132 | | c | cc | bbb | c* | cc* | B | C* |
| | 133 | and/rac | b | cc | bbb | c* | cc* | B | C* |
| | 134 | or/rel | c | cc | ccc | c* | cc* | C | C* |
| | 135 | | b | bb | aaa | c* | bb* | A | C* |

TABLE 1-continued
Exemplary compounds of the invention and biological data
| Structure | Nr | Stereo | No Co-factor/ SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 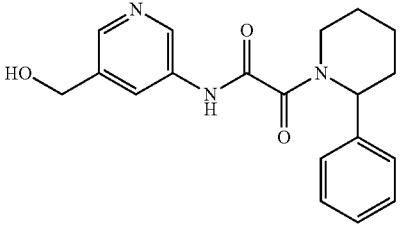 [SMILES: O=C(Nc1cncc(CO)c1)C(=O)N1CCCCC1c1ccccc1] | 136 | c | c | cc | ccc | c* | cc* | C | C* |
| 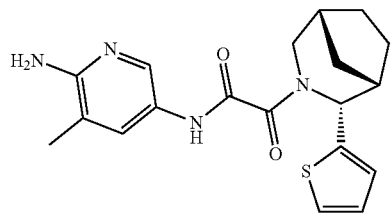 [SMILES: Cc1cc(NC(=O)C(=O)N2C[C@@H]3CC[C@@H](C3)[C@@H]2c2cccs2)cnc1N] | 137 | or/rel | b | bb | aaa | c* | aa* | A | C* |
| 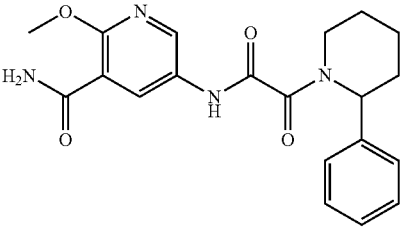 [SMILES: COc1ncc(NC(=O)C(=O)N2CCCCC2c2ccccc2)cc1C(N)=O] | 138 | | b | cc | aaa | c* | bb* | A | C* |
| 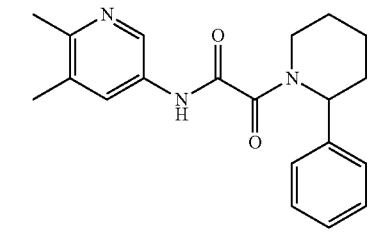 | 139 | | b | bb | bbb | c* | cc* | C | C* |
| 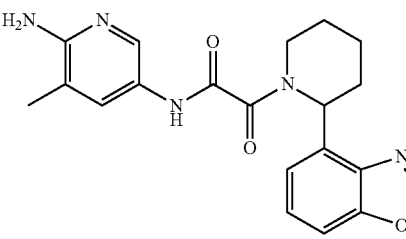 | 140 | c | c | cc | ccc | c* | bb* | A | C* |
| 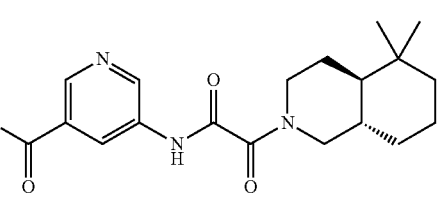 | 141 | and/rac | b | bb | aaa | c* | bb* | A | C* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 142 | b | cc | bbb | c* | cc* | B | C* |
| | 143 | and/rac c | cc | bbb | c* | cc* | C | C* |
| | 144 | b | bb | aaa | c* | bb* | A | C* |
| | 145 | and/rac b | bb | aaa | c* | bb* | C | C* |
| | 146 | and/rac b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 147 | | c | cc | bbb | c* | cc* | C | C* |
| | 148 | or/rel | b | bb | aaa | b* | aa* | A | B* |
| | 149 | | b | cc | bbb | c* | cc* | C | C* |
| | 150 | and/rac | b | bb | bbb | c* | bb* | C | B* |
| | 151 | and/rac | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 152 | or/rel | c | cc | ccc | | | | |
| | 153 | and/rac | b | bb | bbb | c* | aa* | A | B* |
| | 154 | And/rac | b | bb | aaa | c* | cc* | B | C* |
| | 155 | And/rac | b | bb | aaa | c* | bb* | A | C* |
| | 156 | and/rac | b | cc | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 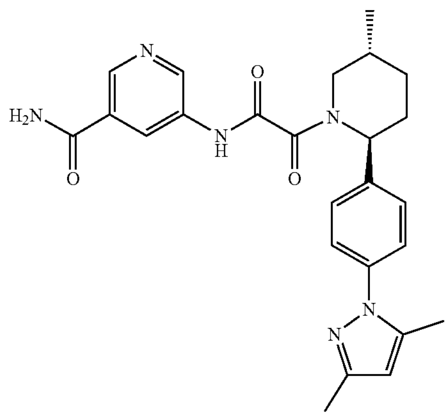 [SMILES: Cc1cc(C)n(-c2ccc([C@@H]3CC[C@@H](C)CN3C(=O)C(=O)Nc3cncc(C(N)=O)c3)cc2)n1] | 157 | and/rac | b | bb | bbb | c* | cc* | B | C* |
| 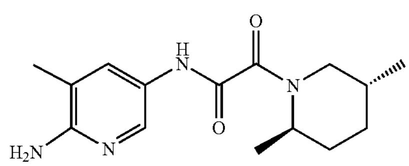 | 158 | and/rac | b | bb | bbb | c* | cc* | C | C* |
| 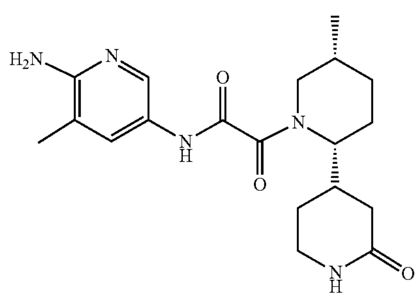 [SMILES: Cc1cc(NC(=O)C(=O)N2C[C@H](C)CC[C@@H]2C2CCNC(=O)C2)cnc1N] | 159 | and/rac | b | bb | bbb | c* | cc* | B | C* |
| 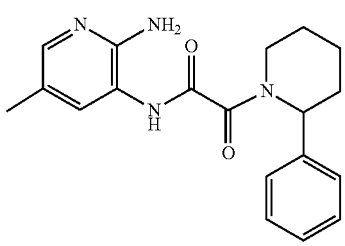 [SMILES: Cc1cnc(N)c(NC(=O)C(=O)N2CCCCC2c2ccccc2)c1] | 160 | | c | cc | ccc | c* | cc* | C | C* |
| 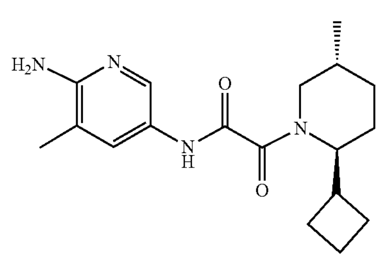 [SMILES: Cc1cc(NC(=O)C(=O)N2C[C@H](C)CC[C@H]2C2CCC2)cnc1N] | 161 | and/rac | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 162 | and/rac | b | bb | aaa | c* | aa* | A | B* |
| | 163 | and/rac | b | bb | aaa | c* | bb* | A | C* |
| | 164 | and/rac | b | bb | aaa | b* | aa* | A | A* |
| | 165 | and/rac | b | bb | aaa | c* | bb* | A | C* |
| | 166 | | c | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 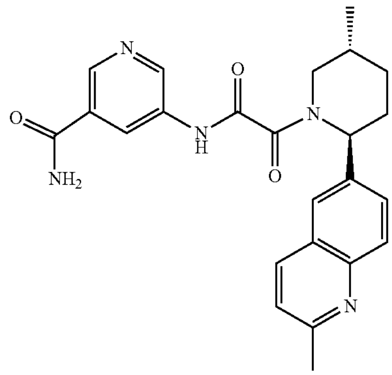 [SMILES: Cc1ccc2cc([C@@H]3CC[C@@H](C)CN3C(=O)C(=O)Nc3cncc(C(N)=O)c3)ccc2n1] | 167 | and/rac | b | bb | aaa | c* | bb* | A | B* |
| 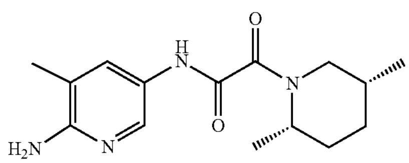 | 168 | and/rac | b | bb | bbb | c* | cc* | C | C* |
| 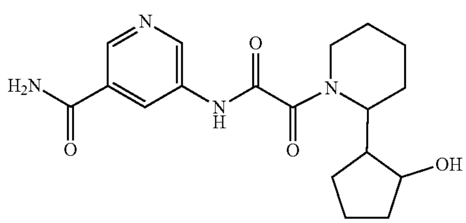 [SMILES: NC(=O)c1cncc(NC(=O)C(=O)N2CCCCC2C2CCCC2O)c1] | 169 | | b | cc | bbb | | | | C* |
| 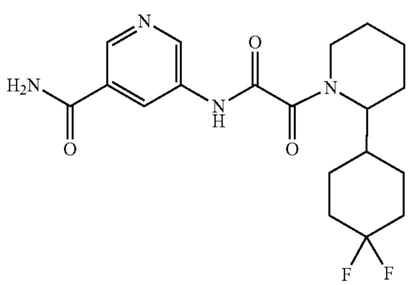 [SMILES: NC(=O)c1cncc(NC(=O)C(=O)N2CCCCC2C2CCC(F)(F)CC2)c1] | 170 | | b | cc | bbb | c* | bb* | A | C* |
| 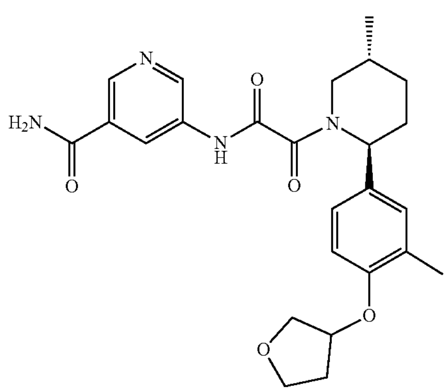 [SMILES: Cc1cc([C@@H]2CC[C@@H](C)CN2C(=O)C(=O)Nc2cncc(C(N)=O)c2)ccc1OC1CCOC1] | 171 | and/rac | b | bb | aaa | c* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 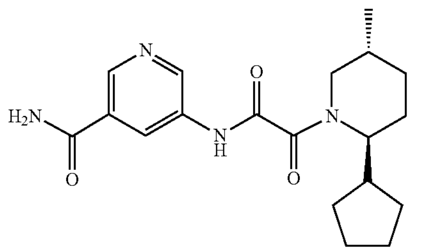 [SMILES: C[C@@H]1CC[C@@H](C2CCCC2)N(C(=O)C(=O)Nc2cncc(C(N)=O)c2)C1] | 172 | and/rac | b | bb | aaa | c* | bb* | A | C* |
| 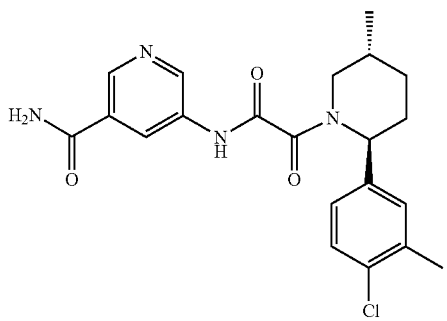 [SMILES: Cc1cc([C@@H]2CC[C@@H](C)CN2C(=O)C(=O)Nc2cncc(C(N)=O)c2)ccc1Cl] | 173 | and/rac | b | bb | aaa | c* | aa* | A | B* |
| 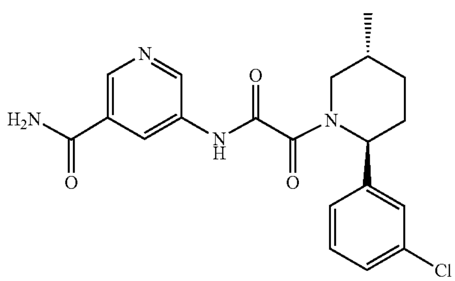 [SMILES: C[C@@H]1CC[C@@H](c2cccc(Cl)c2)N(C(=O)C(=O)Nc2cncc(C(N)=O)c2)C1] | 174 | and/rac | b | bb | aaa | c* | aa* | A | B* |
| 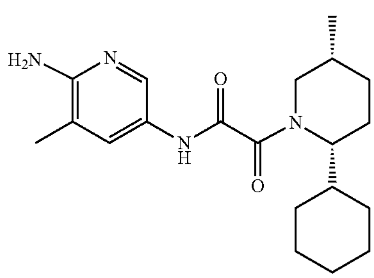 [SMILES: Cc1cc(NC(=O)C(=O)N2C[C@H](C)CC[C@@H]2C2CCCCC2)cnc1N] | 175 | and/rac | c | cc | bbb | c* | cc* | B | C* |
| 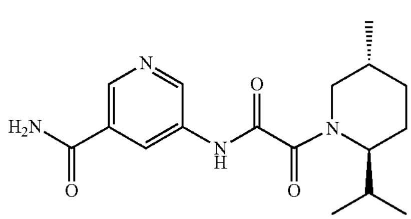 [SMILES: CC(C)[C@@H]1CC[C@@H](C)CN1C(=O)C(=O)Nc1cncc(C(N)=O)c1] | 176 | and/rac | b | bb | aaa | c* | bb* | A | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 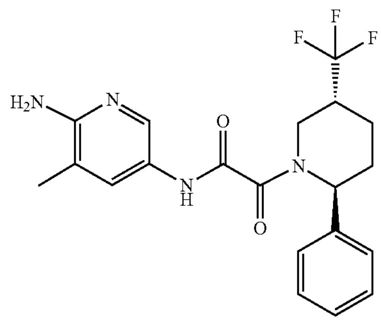 [SMILES: Cc1cc(NC(=O)C(=O)N2C[C@H](C(F)(F)F)CC[C@H]2c2ccccc2)cnc1N] | 177 | and/rac | b | bb | bbb | c* | cc* | B | C* |
| 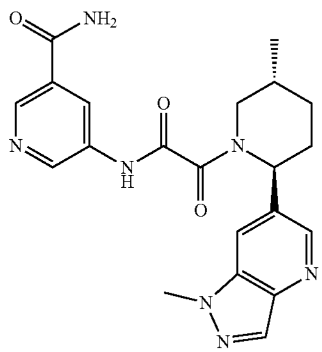 [SMILES: C[C@@H]1CC[C@@H](c2cnc3cnn(C)c3c2)N(C(=O)C(=O)Nc2cncc(C(N)=O)c2)C1] | 178 | and/rac | c | cc | bbb | | | | C* |
| 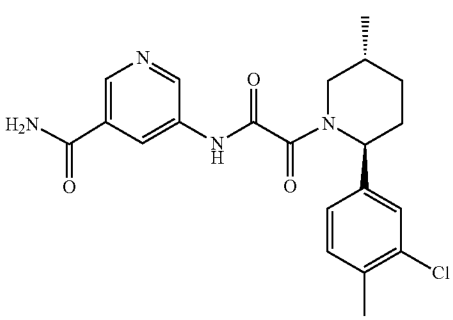 [SMILES: Cc1ccc([C@@H]2CC[C@@H](C)CN2C(=O)C(=O)Nc2cncc(C(N)=O)c2)cc1Cl] | 179 | and/rac | b | bb | aaa | c* | aa* | A | B* |
| 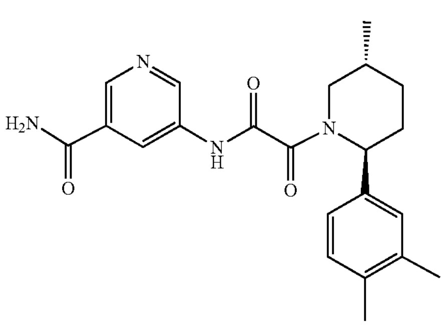 [SMILES: Cc1ccc([C@@H]2CC[C@@H](C)CN2C(=O)C(=O)Nc2cncc(C(N)=O)c2)cc1C] | 180 | and/rac | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 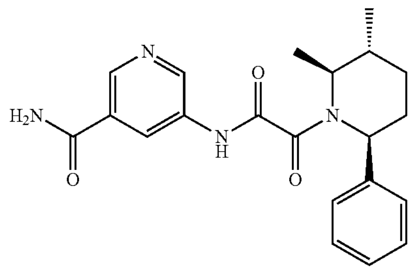 [SMILES: C[C@@H]1CC[C@@H](c2ccccc2)N(C(=O)C(=O)Nc2cncc(C(N)=O)c2)[C@H]1C] | 181 | and/rac | b | bb | aaa | c* | bb* | A | B* |
| 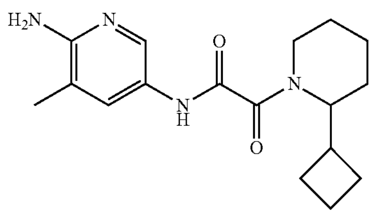 [SMILES: Cc1cc(NC(=O)C(=O)N2CCCCC2C2CCC2)cnc1N] | 182 | | b | bb | aaa | c* | bb* | A | C* |
| 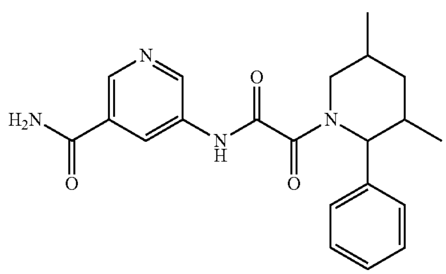 [SMILES: CC1CC(C)C(c2ccccc2)N(C(=O)C(=O)Nc2cncc(C(N)=O)c2)C1] | 183 | | c | cc | ccc | c* | cc* | C | C* |
| 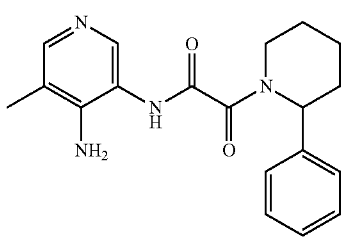 [SMILES: Cc1cncc(NC(=O)C(=O)N2CCCCC2c2ccccc2)c1N] | 184 | | c | cc | bbb | c* | cc* | C | C* |
| 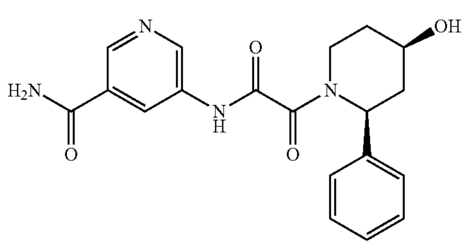 [SMILES: NC(=O)c1cncc(NC(=O)C(=O)N2CC[C@@H](O)C[C@H]2c2ccccc2)c1] | 185 | and/rac | b | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 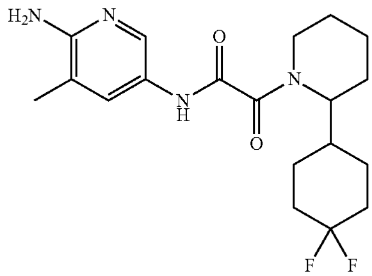 [SMILES: Cc1cc(NC(=O)C(=O)N2CCCCC2C2CCC(F)(F)CC2)cnc1N] | 186 |  | b | bb | bbb | c* | bb* | A | C* |
| 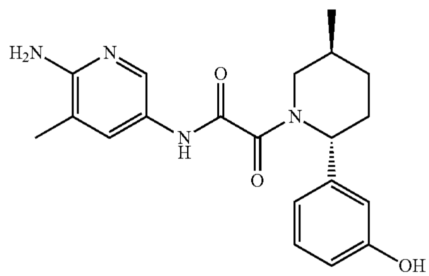 [SMILES: Cc1cc(NC(=O)C(=O)N2C[C@@H](C)CC[C@@H]2c2cccc(O)c2)cnc1N] | 187 | and/rac | b | bb | aaa | b* | aa* | A | B* |
| 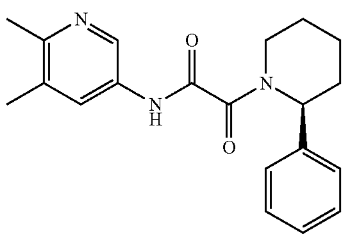 [SMILES: Cc1cc(NC(=O)C(=O)N2CCCC[C@H]2c2ccccc2)cnc1C] | 188 | or/rel | b | bb | bbb | c* | cc* | C | C* |
| 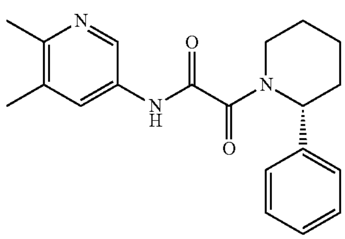 | 189 | or/rel | c | cc | ccc | c* | cc* | C | C* |
| 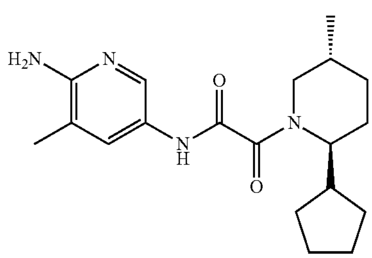 [SMILES: Cc1cc(NC(=O)C(=O)N2C[C@H](C)CC[C@H]2C2CCCC2)cnc1N] | 190 | and/rac | b | bb | aaa | c* | bb* | B | B* |
| 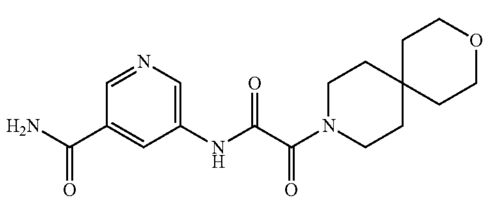 [SMILES: NC(=O)c1cncc(NC(=O)C(=O)N2CCC3(CCOCC3)CC2)c1] | 191 |  | c | cc | bbb | c* | cc* | C | C* |

TABLE 1-continued

Exemplary compounds of the invention and biological data

| Structure | Nr | Stereo | No Co-factor/ SAM IC50 | SAM rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| 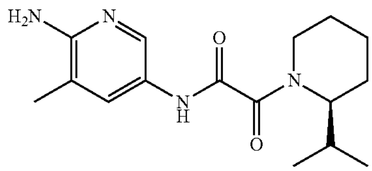 [SMILES: Cc1cc(NC(=O)C(=O)N2CCCC[C@H]2C(C)C)cnc1N] | 192 | or/rel | b | bb | aaa | c* | bb* | A | C* |
| 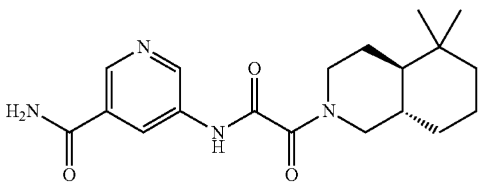 [SMILES: CC1(C)CCC[C@@H]2CN(C(=O)C(=O)Nc3cncc(C(N)=O)c3)CC[C@H]21] | 193 | or/rel | b | bb | aaa | c* | aa* | A | B* |
| 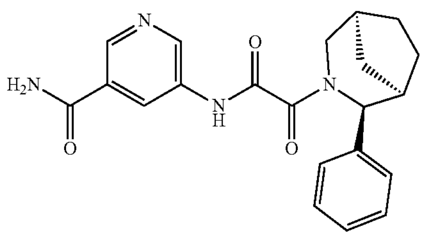 [SMILES: NC(=O)c1cncc(NC(=O)C(=O)N2C[C@H]3CC[C@H](C3)[C@H]2c2ccccc2)c1] | 194 | or/rel | c | cc | ccc | c* | cc* | C | C* |
| 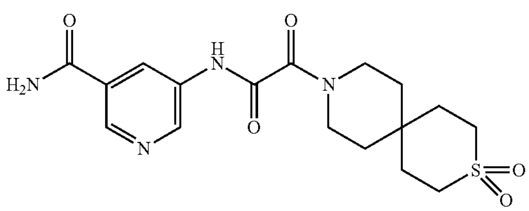 [SMILES: NC(=O)c1cncc(NC(=O)C(=O)N2CCC3(CC2)CCS(=O)(=O)CC3)c1] | 195 | | c | cc | bbb | c* | cc* | C | C* |
| 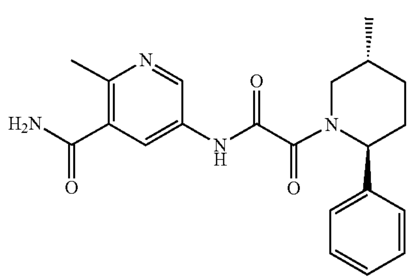 [SMILES: Cc1ncc(NC(=O)C(=O)N2C[C@H](C)CC[C@H]2c2ccccc2)cc1C(N)=O] | 196 | or/rel | c | cc | ccc | c* | cc* | C | C* |
| 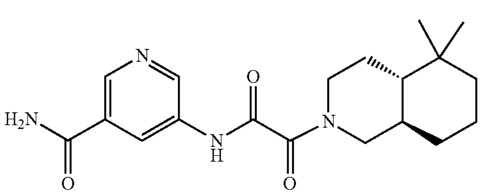 [SMILES: CC1(C)CCC[C@H]2CN(C(=O)C(=O)Nc3cncc(C(N)=O)c3)CC[C@@H]21] | 197 | or/rel | b | cc | bbb | c* | cc* | C | C* |

TABLE 1-continued
Exemplary compounds of the invention and biological data
| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 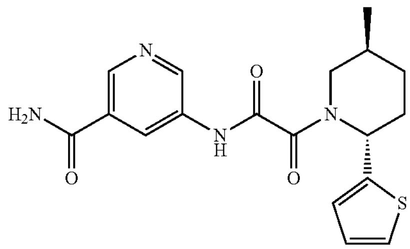 [SMILES: C[C@H]1CC[C@H](c2cccs2)N(C(=O)C(=O)Nc2cncc(C(N)=O)c2)C1] | 198 | or/rel | b | aa | aaa | b* | aa* | A | A* |
| 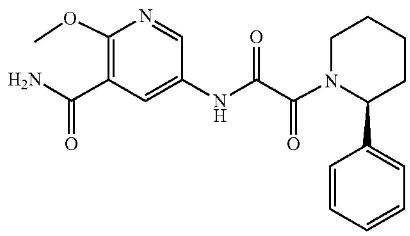 [SMILES: COc1ncc(NC(=O)C(=O)N2CCCC[C@H]2c2ccccc2)cc1C(N)=O] | 199 | or/rel | c | cc | bbb | c* | cc* | C | C* |
| 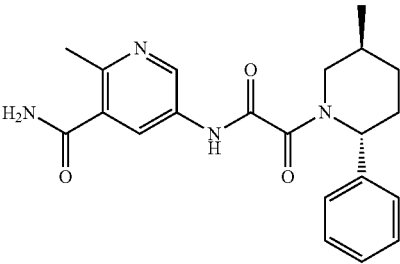 [SMILES: Cc1ncc(NC(=O)C(=O)N2C[C@@H](C)CC[C@@H]2c2ccccc2)cc1C(N)=O] | 200 | or/rel | b | bb | aaa | c* | aa* | A | B* |
| 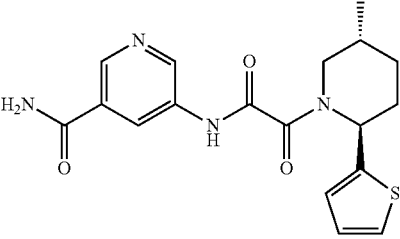 | 201 | or/rel | c | cc | ccc | c* | cc* | C | C* |
| 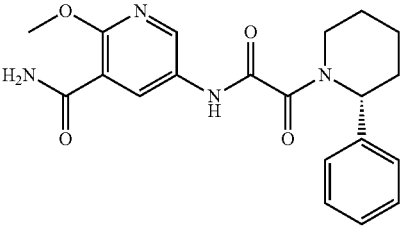 | 202 | or/rel | b | bb | aaa | c* | bb* | A | C* |
| 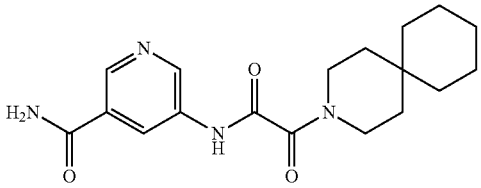 [SMILES: NC(=O)c1cncc(NC(=O)C(=O)N2CCC3(CCCCC3)CC2)c1] | 203 | | b | cc | aaa | c* | bb* | A | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| | 204 | or/rel | c | cc | bbb | c* | cc* | C | C* |
| | 205 | or/rel | b | cc | bbb | c* | cc* | B | C* |
| | 206 | and/rac | b | bb | aaa | c* | bb* | A | B* |
| | 207 | and/rac | c | bb | bbb | c* | bb* | A | B* |
| | 208 | and/rac | b | bb | aaa | c* | bb* | A | B* |

TABLE 1-continued

Exemplary compounds of the invention and biological data

| Structure | Nr | Stereo | SAM IC50 | No Co-factor/ rel MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|
| | 209 | and/rac | b | bb | aaa | c* | aa* | A | B* |
| | 210 | | c | bb | bbb | c* | cc* | B | C* |
| | 211 | or/rel | b | bb | aaa | c* | aa* | A | B* |
| | 212 | and/rac | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 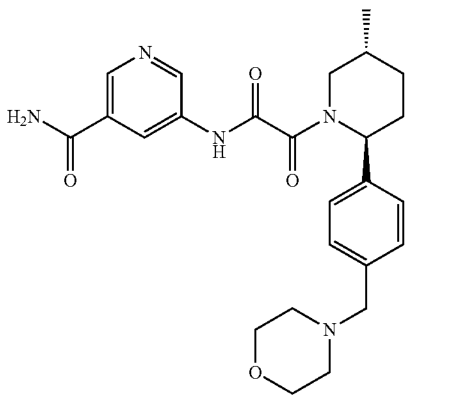 [SMILES: C[C@@H]1CC[C@@H](c2ccc(CN3CCOCC3)cc2)N(C(=O)C(=O)Nc2cncc(C(N)=O)c2)C1] | 213 | and/rac | b | bb | aaa | c* | bb* | A | C* |
| 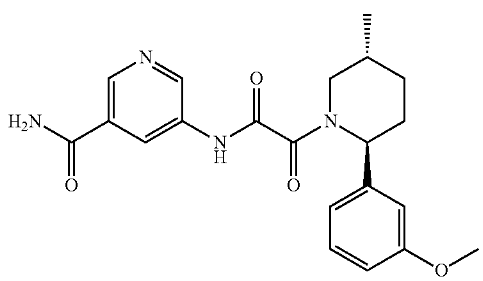 [SMILES: COc1cccc([C@@H]2CC[C@@H](C)CN2C(=O)C(=O)Nc2cncc(C(N)=O)c2)c1] | 214 | and/rac | b | bb | aaa | c* | aa* | A | B* |
| 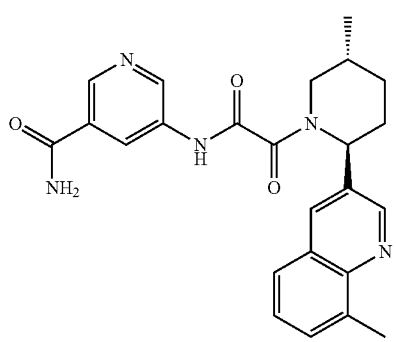 [SMILES: Cc1cccc2cc([C@@H]3CC[C@@H](C)CN3C(=O)C(=O)Nc3cncc(C(N)=O)c3)cnc12] | 215 | or/rel | c | cc | bbb | c* | cc* | B | C* |
| 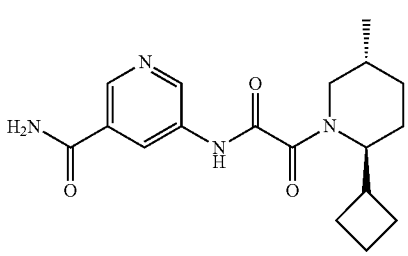 [SMILES: C[C@@H]1CC[C@@H](C2CCC2)N(C(=O)C(=O)Nc2cncc(C(N)=O)c2)C1] | 216 | or/rel | c | cc | ccc | c* | cc* | C | C* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 217 | b | cc | | bbb | c* | cc* | B | C* |
| | 218 | and/rac | b | bb | aaa | c* | aa* | A | B* |
| | 219 | or/rel | b | aa | aaa | c* | aa* | A | B* |
| | 220 | and/rac | b | bb | aaa | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 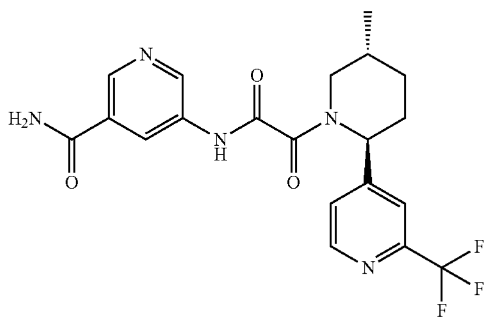 [SMILES: C[C@@H]1CC[C@@H](c2ccnc(C(F)(F)F)c2)N(C(=O)C(=O)Nc2cncc(C(N)=O)c2)C1] | 221 | and/rac | b | bb | bbb | c* | bb* | A | C* |
| 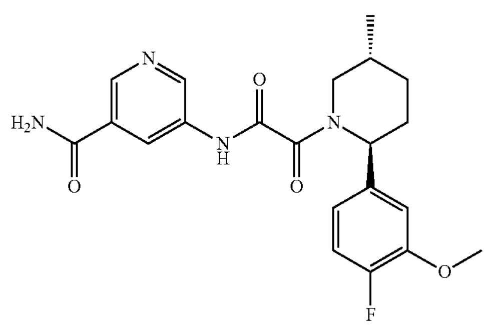 [SMILES: COc1cc([C@@H]2CC[C@@H](C)CN2C(=O)C(=O)Nc2cncc(C(N)=O)c2)ccc1F] | 222 | and/rac | b | bb | aaa | c* | bb* | A | B* |
| 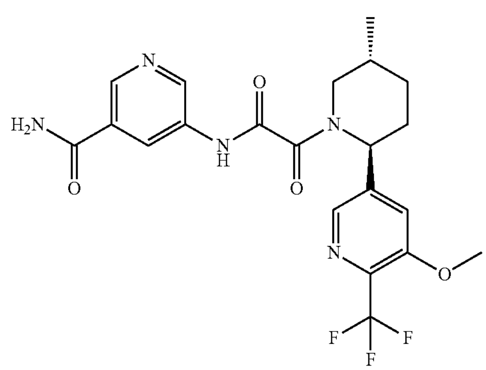 [SMILES: COc1cc([C@@H]2CC[C@@H](C)CN2C(=O)C(=O)Nc2cncc(C(N)=O)c2)cnc1C(F)(F)F] | 223 | and/rac | c | cc | bbb | c* | cc* | C | C* |
| 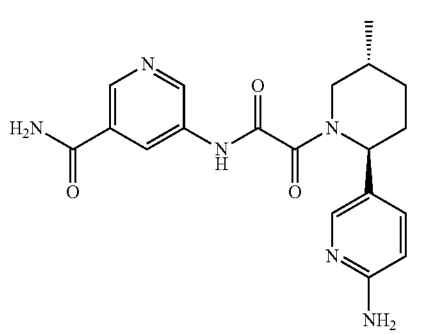 [SMILES: C[C@@H]1CC[C@@H](c2ccc(N)nc2)N(C(=O)C(=O)Nc2cncc(C(N)=O)c2)C1] | 224 | and/rac | b | bb | aaa | c* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| (structure 225) | 225 | and/rac | b | bb | bbb | c* | aa* | A | B* |
| (structure 226) | 226 | and/rac | b | cc | bbb | c* | cc* | C | C* |
| (structure 227) | 227 | or/rel | c | cc | ccc | c* | cc* | C | C* |
| (structure 228) | 228 | and/rac | b | bb | bbb | c* | bb* | A | B* |
| (structure 229) | 229 | and/rac | c | cc | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 230 | and/rac | b | bb | aaa | c* | bb* | A | B* |
| | 231 | and/rac | b | bb | aaa | c* | bb* | A | C* |
| | 232 | | c | cc | bbb | c* | cc* | B | C* |
| | 233 | or/rel | c | cc | ccc | c* | cc* | C | C* |
| | 234 | and/rac | b | bb | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 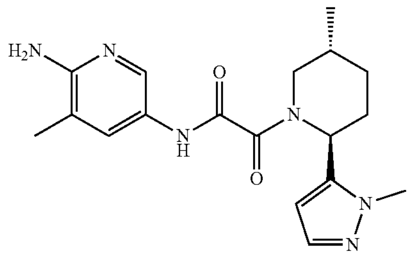 [SMILES: Cc1cc(NC(=O)C(=O)N2C[C@H](C)CC[C@H]2c2ccnn2C)cnc1N] | 235 | and/rac | b | bb | bbb | c* | cc* | B | C* |
| 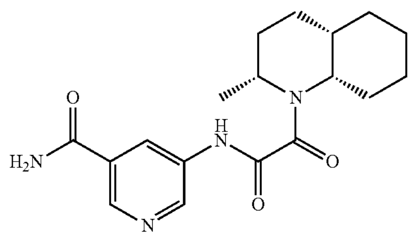 [SMILES: C[C@@H]1CC[C@@H]2CCCC[C@@H]2N1C(=O)C(=O)Nc1cncc(C(N)=O)c1] | 236 | or/rel | c | cc | bbb | c* | cc* | B | C* |
| 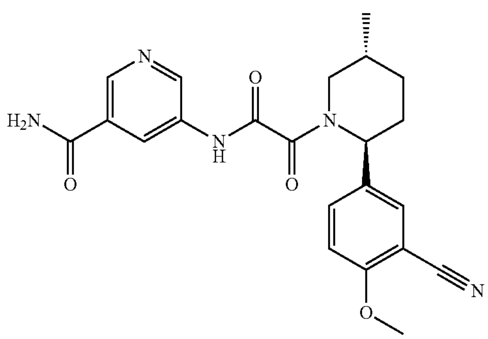 [SMILES: COc1ccc([C@@H]2CC[C@@H](C)CN2C(=O)C(=O)Nc2cncc(C(N)=O)c2)cc1C#N] | 237 | and/rac | b | bb | bbb | c* | cc* | B | C* |
| 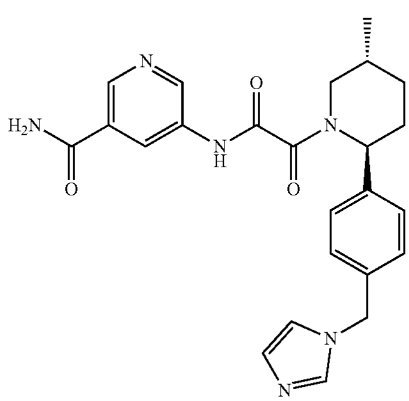 [SMILES: C[C@@H]1CC[C@@H](c2ccc(Cn3ccnc3)cc2)N(C(=O)C(=O)Nc2cncc(C(N)=O)c2)C1] | 238 | and/rac | b | bb | aaa | c* | bb* | A | B* |

TABLE 1-continued

Exemplary compounds of the invention and biological data

| Structure | Nr | Stereo | SAM IC50 | No Co-factor/ rel MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|
| | 239 | and/rac | b | bb | aaa | c* | aa* | A | B* |
| | 240 | | b | bb | aaa | c* | bb* | A | C* |
| | 241 | and/rac | b | bb | aaa | c* | aa* | A | B* |
| | 242 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 243 | and/rac | b | bb | aaa | c* | bb* | A | B* |
| | 244 | and/rac | b | bb | aaa | c* | aa* | A | B* |
| | 245 | or/rel | b | bb | aaa | c* | bb* | A | B* |
| | 246 | and/rac | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 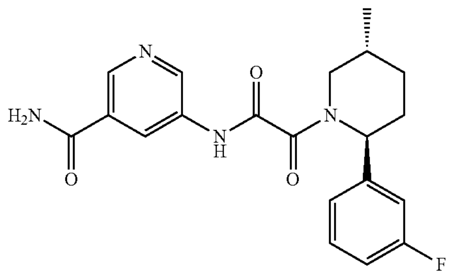 | 247 | and/rac | b | bb | aaa | c* | aa* | A | B* |
| 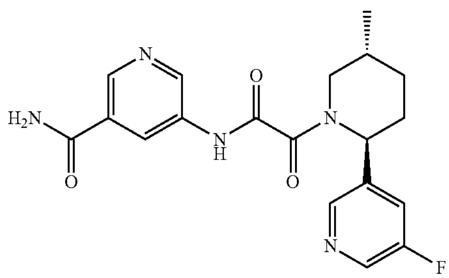 [SMILES: C[C@@H]1CC[C@@H](c2cncc(F)c2)N(C(=O)C(=O)Nc2cncc(C(N)=O)c2)C1] | 248 | and/rac | c | cc | bbb | c* | cc* | B | C* |
| 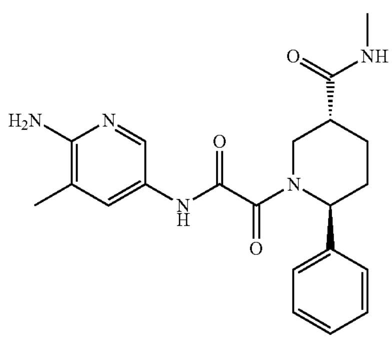 [SMILES: CNC(=O)[C@@H]1CC[C@@H](c2ccccc2)N(C(=O)C(=O)Nc2cnc(N)c(C)c2)C1] | 249 | and/rac | b | cc | bbb | c* | cc* | C | C* |
| 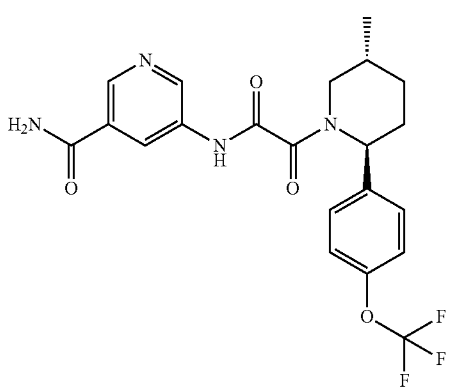 [SMILES: C[C@@H]1CC[C@@H](c2ccc(OC(F)(F)F)cc2)N(C(=O)C(=O)Nc2cncc(C(N)=O)c2)C1] | 250 | and/rac | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 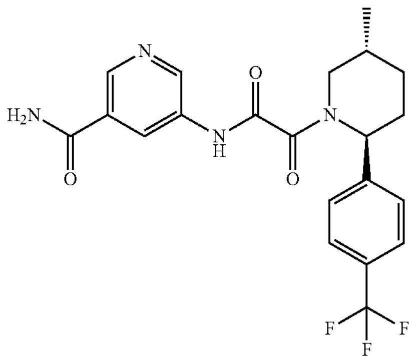 [SMILES: C[C@@H]1CC[C@@H](c2ccc(C(F)(F)F)cc2)N(C(=O)C(=O)Nc2cncc(C(N)=O)c2)C1] | 251 | and/rac | b | bb | aaa | c* | aa* | A | B* |
| 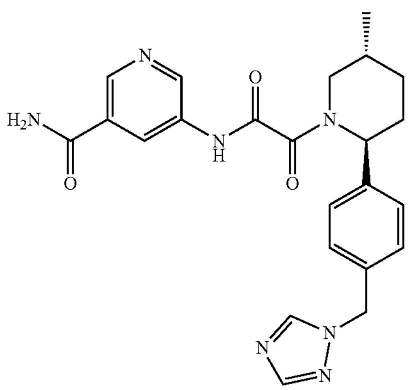 [SMILES: C[C@@H]1CC[C@@H](c2ccc(Cn3cncn3)cc2)N(C(=O)C(=O)Nc2cncc(C(N)=O)c2)C1] | 252 | and/rac | b | bb | aaa | c* | bb* | A | C* |
| 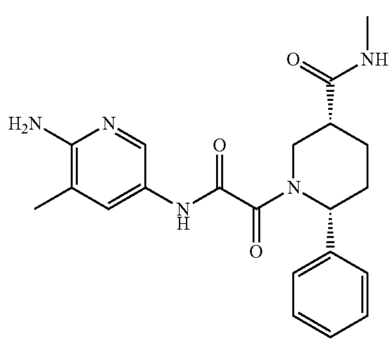 [SMILES: CNC(=O)[C@@H]1CC[C@H](c2ccccc2)N(C(=O)C(=O)Nc2cnc(N)c(C)c2)C1] | 253 | and/rac | b | cc | bbb | c* | cc* | C | C* |
| 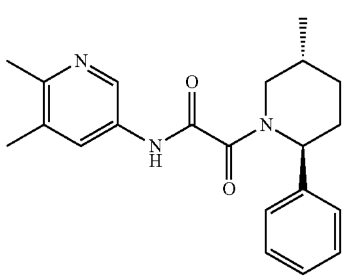 [SMILES: Cc1cc(NC(=O)C(=O)N2C[C@H](C)CC[C@H]2c2ccccc2)cnc1C] | 254 | or/rel | a | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 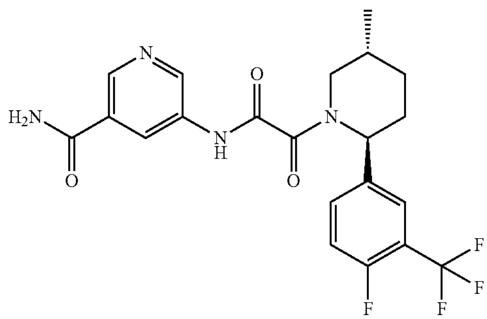 [SMILES: C[C@@H]1CC[C@@H](c2ccc(F)c(C(F)(F)F)c2)N(C(=O)C(=O)Nc2cncc(C(N)=O)c2)C1] | 255 | and/rac | b | bb | aaa | c* | bb* | A | B* |
| 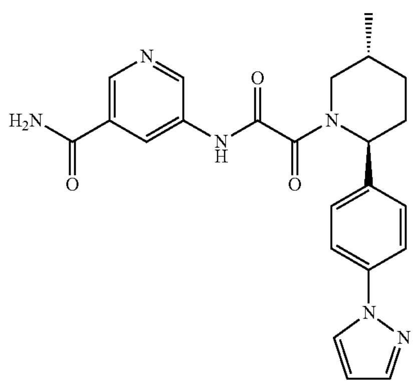 | 256 | and/rac | b | bb | aaa | c* | aa* | A | B* |
| 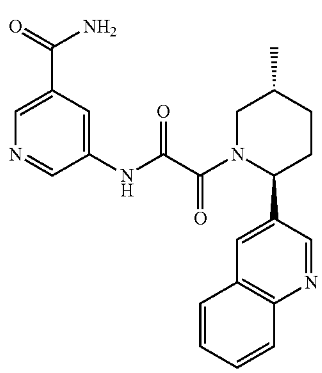 [SMILES: C[C@@H]1CC[C@@H](c2cnc3ccccc3c2)N(C(=O)C(=O)Nc2cncc(C(N)=O)c2)C1] | 257 | and/rac | c | cc | bbb | c* | cc* | B | C* |
| 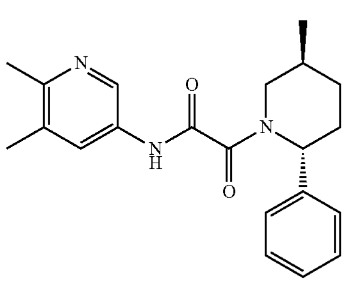 [SMILES: Cc1cc(NC(=O)C(=O)N2C[C@@H](C)CC[C@@H]2c2ccccc2)cnc1C] | 258 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 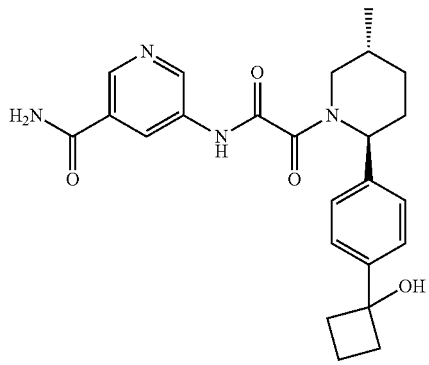 [SMILES: C[C@@H]1CC[C@@H](c2ccc(C3(O)CCC3)cc2)N(C(=O)C(=O)Nc2cncc(C(N)=O)c2)C1] | 259 | and/rac | b | bb | bbb | c* | bb* | A | C* |
| 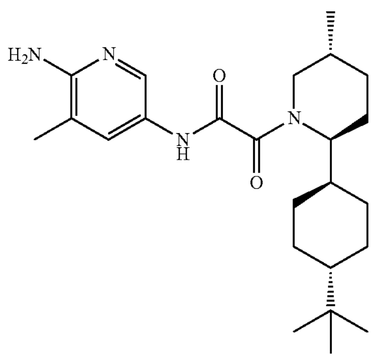 [SMILES: Cc1cc(NC(=O)C(=O)N2C[C@H](C)CC[C@H]2[C@H]2CC[C@H](C(C)(C)C)CC2)cnc1N] | 260 | or/rel | b | bb | aaa | c* | bb* | C | B* |
| 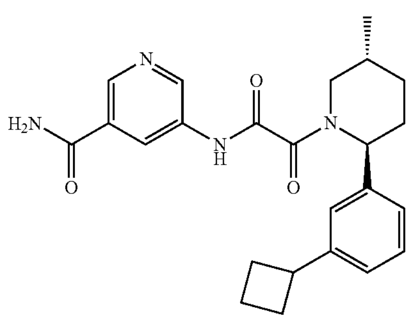 [SMILES: C[C@@H]1CC[C@@H](c2cccc(C3CCC3)c2)N(C(=O)C(=O)Nc2cncc(C(N)=O)c2)C1] | 261 | and/rac | b | bb | aaa | c* | aa* | A | B* |
| 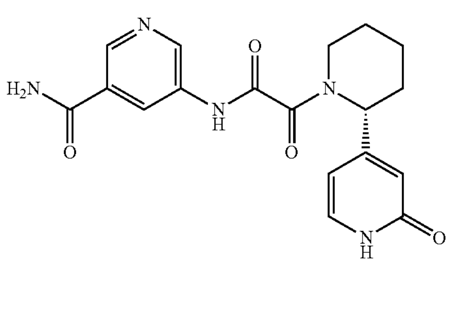 [SMILES: NC(=O)c1cncc(NC(=O)C(=O)N2CCCC[C@@H]2c2cc[nH]c(=O)c2)c1] | 262 | and/rac | c | cc | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 263 | and/rac | b | bb | aaa | c* | bb* | A | B* |
| | 264 | and/rac | b | bb | bbb | c* | aa* | A | B* |
| | 265 | and/rac | b | bb | aaa | c* | bb* | A | B* |
| | 266 | and/rac | b | cc | bbb | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 267 | or/rel | a | bb | aaa | c* | aa* | A | B* |
| | 268 | and/rac | b | bb | aaa | c* | bb* | A | B* |
| | 269 | and/rac | b | cc | bbb | | | | C* |
| | 270 | and/rac | b | bb | aaa | c* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 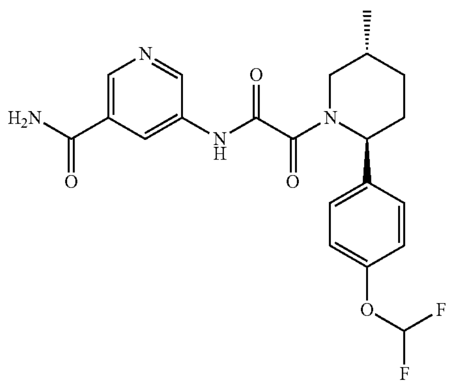 [SMILES: C[C@@H]1CC[C@@H](c2ccc(OC(F)F)cc2)N(C(=O)C(=O)Nc2cncc(C(N)=O)c2)C1] | 271 | and/rac | b | bb | aaa | c* | bb* | A | B* |
| 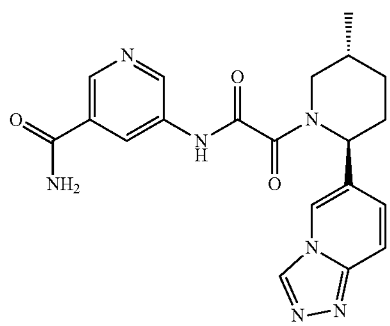 [SMILES: C[C@@H]1CC[C@@H](c2ccc3nncn3c2)N(C(=O)C(=O)Nc2cncc(C(N)=O)c2)C1] | 272 | and/rac | b | bb | bbb | c* | cc* | C | C* |
| 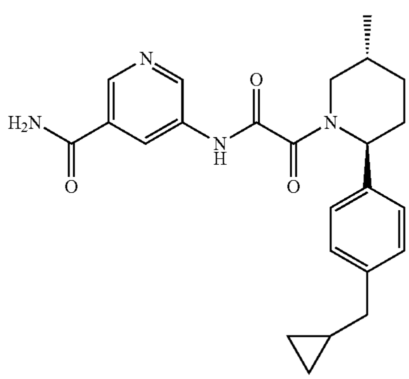 [SMILES: C[C@@H]1CC[C@@H](c2ccc(CC3CC3)cc2)N(C(=O)C(=O)Nc2cncc(C(N)=O)c2)C1] | 273 | and/rac | b | bb | aaa | c* | bb* | A | B* |
| 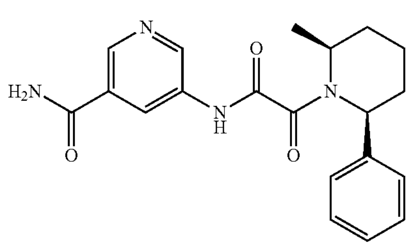 [SMILES: C[C@H]1CCC[C@@H](c2ccccc2)N1C(=O)C(=O)Nc1cncc(C(N)=O)c1] | 274 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 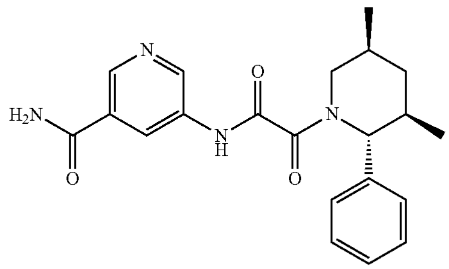 [SMILES: C[C@H]1C[C@@H](C)[C@H](c2ccccc2)N(C(=O)C(=O)Nc2cncc(C(N)=O)c2)C1] | 275 | or/rel | c | cc | ccc | | | | |
| 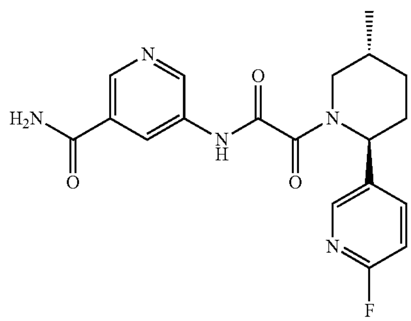 [SMILES: C[C@@H]1CC[C@@H](c2ccc(F)nc2)N(C(=O)C(=O)Nc2cncc(C(N)=O)c2)C1] | 276 | and/rac | b | bb | aaa | c* | bb* | A | C* |
| 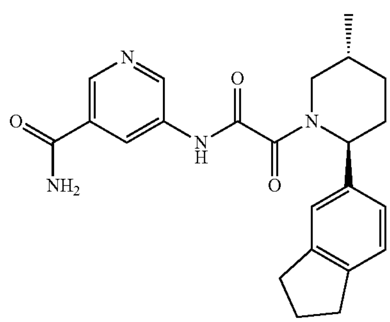 [SMILES: C[C@@H]1CC[C@@H](c2ccc3c(c2)CCC3)N(C(=O)C(=O)Nc2cncc(C(N)=O)c2)C1] | 277 | and/rac | b | bb | aaa | c* | bb* | A | B* |
| 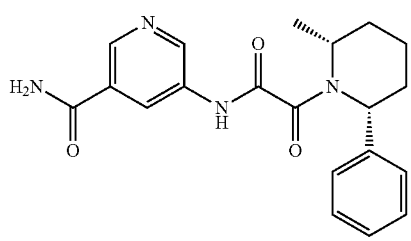 [SMILES: C[C@@H]1CCC[C@H](c2ccccc2)N1C(=O)C(=O)Nc1cncc(C(N)=O)c1] | 278 | or/rel | c | cc | bbb | | | | C* |
| 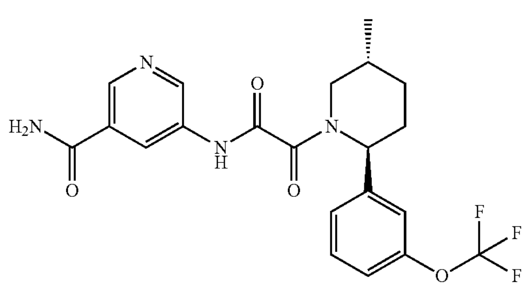 [SMILES: C[C@@H]1CC[C@@H](c2cccc(OC(F)(F)F)c2)N(C(=O)C(=O)Nc2cncc(C(N)=O)c2)C1] | 279 | and/rac | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 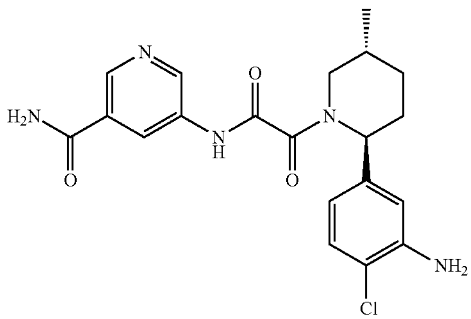 [SMILES: C[C@@H]1CC[C@@H](c2ccc(Cl)c(N)c2)N(C(=O)C(=O)Nc2cncc(C(N)=O)c2)C1] | 280 | and/rac | b | bb | aaa | c* | bb* | A | B* |
| 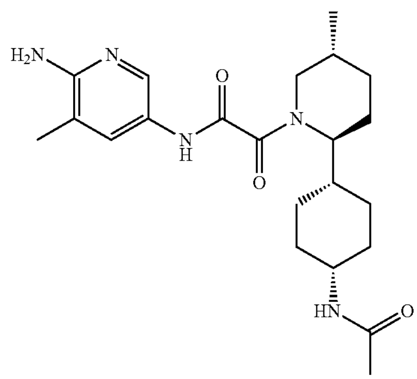 [SMILES: CC(=O)N[C@H]1CC[C@@H]([C@@H]2CC[C@@H](C)CN2C(=O)C(=O)Nc2cnc(N)c(C)c2)CC1] | 281 | or/rel | c | cc | bbb | c* | bb* | A | C* |
| 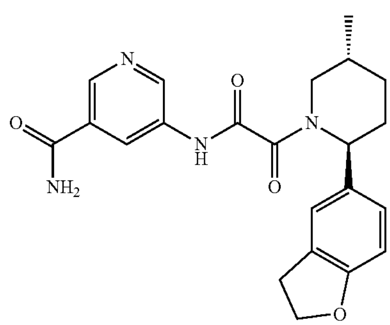 [SMILES: C[C@@H]1CC[C@@H](c2ccc3c(c2)CCO3)N(C(=O)C(=O)Nc2cncc(C(N)=O)c2)C1] | 282 | and/rac | c | cc | bbb | c* | bb* | A | C* |
| 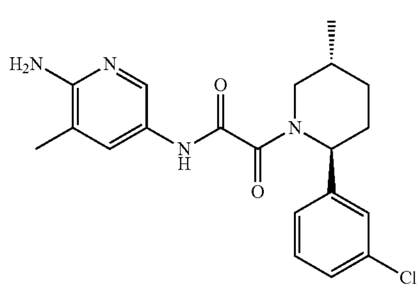 [SMILES: Cc1cc(NC(=O)C(=O)N2C[C@H](C)CC[C@H]2c2cccc(Cl)c2)cnc1N] | 283 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 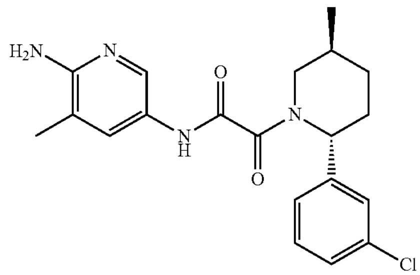 [SMILES: Cc1cc(NC(=O)C(=O)N2C[C@@H](C)CC[C@@H]2c2cccc(Cl)c2)cnc1N] | 284 | or/rel | b | aa | aaa | b* | aa* | A | A* |
| 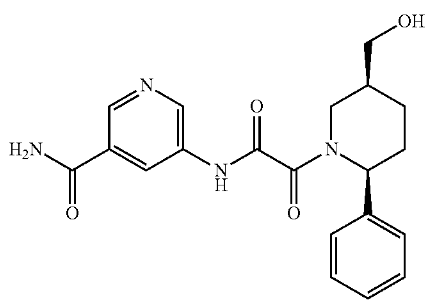 [SMILES: NC(=O)c1cncc(NC(=O)C(=O)N2C[C@@H](CO)CC[C@H]2c2ccccc2)c1] | 285 | and/rac | c | cc | bbb | | | | |
| 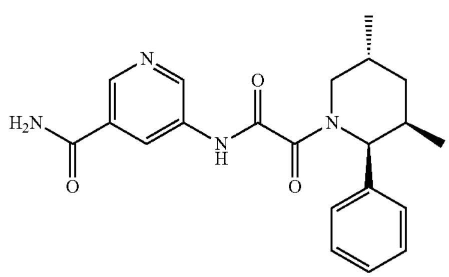 [SMILES: C[C@@H]1C[C@@H](C)[C@@H](c2ccccc2)N(C(=O)C(=O)Nc2cncc(C(N)=O)c2)C1] | 286 | or/rel | c | cc | ccc | | | | |
| 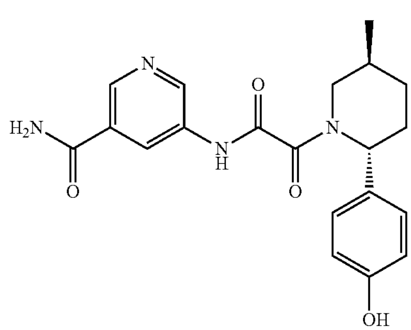 [SMILES: C[C@H]1CC[C@H](c2ccc(O)cc2)N(C(=O)C(=O)Nc2cncc(C(N)=O)c2)C1] | 287 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 288 | or/rel | b | aa | aaa | b* | aa* | A | A* |
| | 289 | or/rel | c | cc | ccc | | | | C* |
| | 290 | or/rel | c | cc | ccc | c* | cc* | C | C* |
| | 291 | or/rel | c | cc | ccc | c* | cc* | C | C* |
| | 292 | or/rel | c | cc | ccc | c* | cc* | C | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 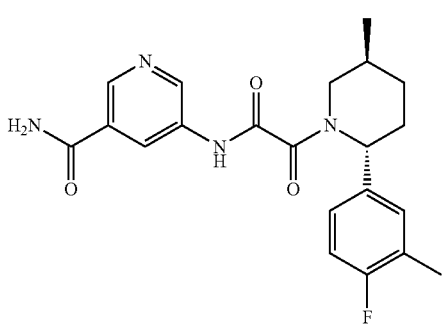 [SMILES: Cc1cc([C@H]2CC[C@H](C)CN2C(=O)C(=O)Nc2cncc(C(N)=O)c2)ccc1F] | 293 | or/rel | a | bb | aaa | c* | aa* | A | B* |
| 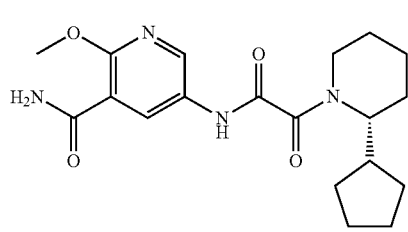 [SMILES: COc1ncc(NC(=O)C(=O)N2CCCC[C@@H]2C2CCCC2)cc1C(N)=O] | 294 | or/rel | b | bb | aaa | c* | aa* | A | B* |
| 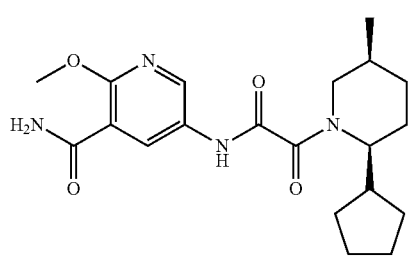 [SMILES: COc1ncc(NC(=O)C(=O)N2C[C@@H](C)CC[C@H]2C2CCCC2)cc1C(N)=O] | 295 | or/rel | c | cc | ccc | | | | C* |
| 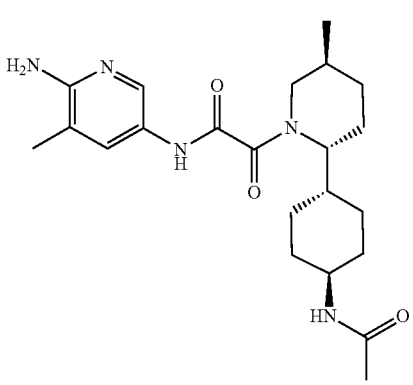 | 296 | or/rel | c | cc | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 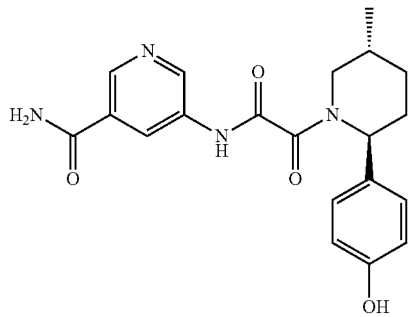 [SMILES: C[C@@H]1CC[C@@H](c2ccc(O)cc2)N(C(=O)C(=O)Nc2cncc(C(N)=O)c2)C1] | 297 | or/rel | c | cc | ccc | c* | cc* | C | C* |
| 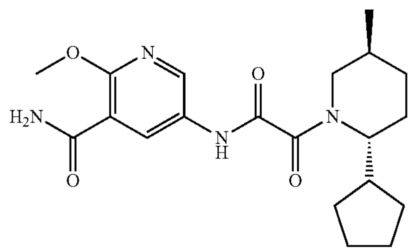 [SMILES: COc1ncc(NC(=O)C(=O)N2C[C@@H](C)CC[C@@H]2C2CCCC2)cc1C(N)=O] | 298 | or/rel | c | cc | ccc | | | | C* |
| 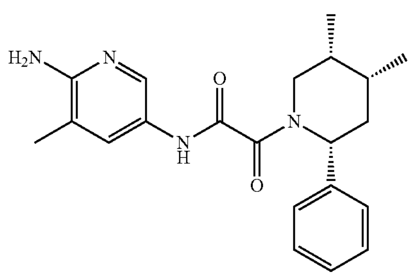 | 299 | or/rel | c | cc | ccc | | | | |
| 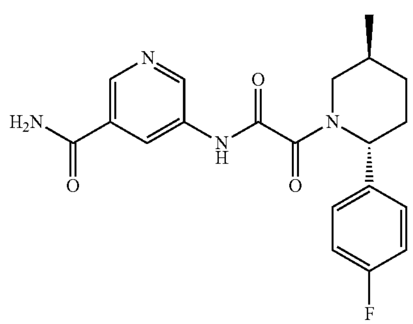 [SMILES: C[C@H]1CC[C@H](c2ccc(F)cc2)N(C(=O)C(=O)Nc2cncc(C(N)=O)c2)C1] | 300 | | b | bb | aaa | c* | aa* | A | B* |
| 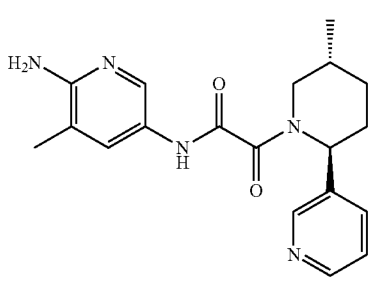 [SMILES: Cc1cc(NC(=O)C(=O)N2C[C@H](C)CC[C@H]2c2cccnc2)cnc1N] | 301 | or/rel | b | bb | aaa | b* | aa* | B | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| 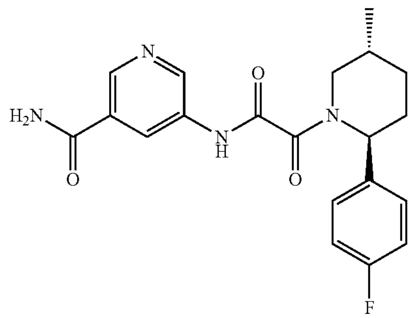 | 302 | | c | cc | ccc | c* | cc* | C | C* |
| 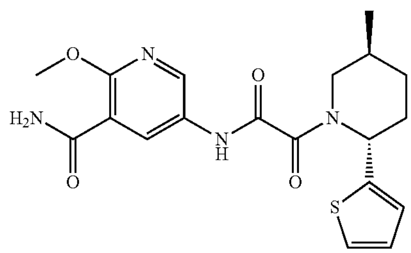 [SMILES: COc1ncc(NC(=O)C(=O)N2C[C@@H](C)CC[C@@H]2c2cccs2)cc1C(N)=O] | 303 | or/rel | b | aa | aaa | c* | aa* | A | A* |
| 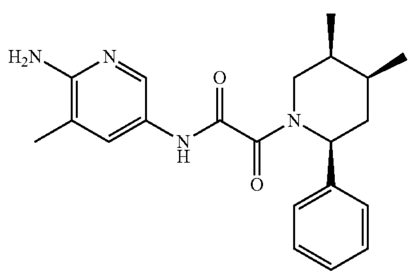 | 304 | or/rel | b | bb | bbb | | | | C* |
| 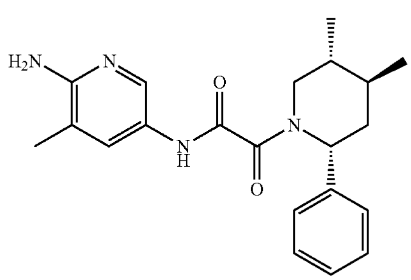 | 305 | or/rel | c | cc | ccc | | | | |
| 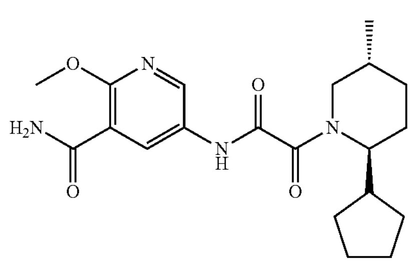 [SMILES: COc1ncc(NC(=O)C(=O)N2C[C@H](C)CC[C@H]2C2CCCC2)cc1C(N)=O] | 306 | or/rel | b | bb | aaa | c* | aa* | A | B* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 307 | or/rel | c | cc | ccc | c* | cc* | C | |
| | 308 | or/rel | b | cc | aaa | c* | bb* | A | C* |
| | 309 | or/rel | c | cc | ccc | | | | |
| | 310 | or/rel | c | cc | ccc | c* | cc* | C | |
| | 311 | or/rel | b | bb | aaa | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 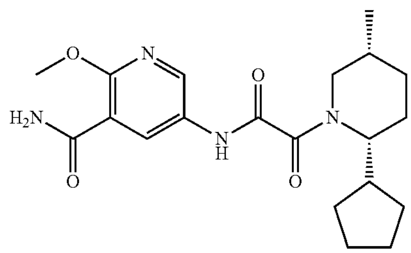 [SMILES: COc1ncc(NC(=O)C(=O)N2C[C@H](C)CC[C@@H]2C2CCCC2)cc1C(N)=O] | 312 | or/rel | b | cc | bbb | | | | C* |
| 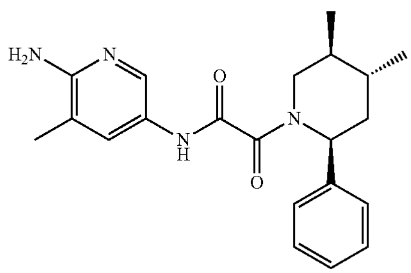 | 313 | or/rel | b | bb | aaa | c* | aa* | A | B* |
| 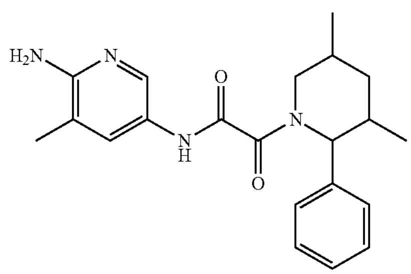 | 314 | | c | bb | bbb | c* | bb* | A | B* |
| 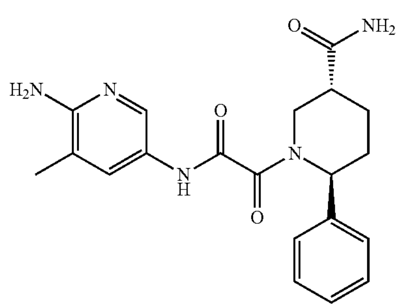 [SMILES: Cc1cc(NC(=O)C(=O)N2C[C@H](C(N)=O)CC[C@H]2c2ccccc2)cnc1N] | 315 | and/rac | b | bb | bbb | c* | bb* | A | C* |
| 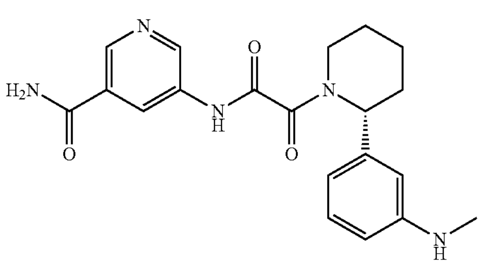 [SMILES: CNc1cccc([C@H]2CCCCN2C(=O)C(=O)Nc2cncc(C(N)=O)c2)c1] | 316 | or/rel | c | cc | bbb | c* | cc* | C | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 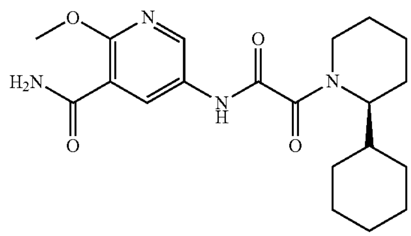 [SMILES: COc1ncc(NC(=O)C(=O)N2CCCC[C@H]2C2CCCCC2)cc1C(N)=O] | 317 | or/rel | c | cc | ccc | c* | cc* | C | |
| 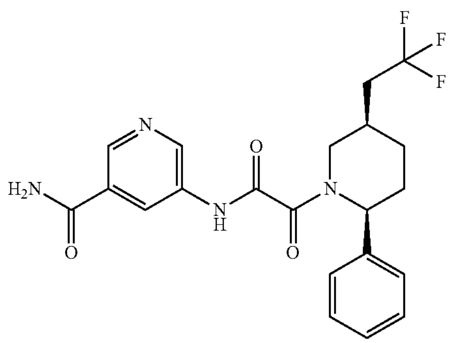 [SMILES: NC(=O)c1cncc(NC(=O)C(=O)N2C[C@@H](CC(F)(F)F)CC[C@H]2c2ccccc2)c1] | 318 | and/rac | c | cc | bbb | c* | cc* | C | C* |
| 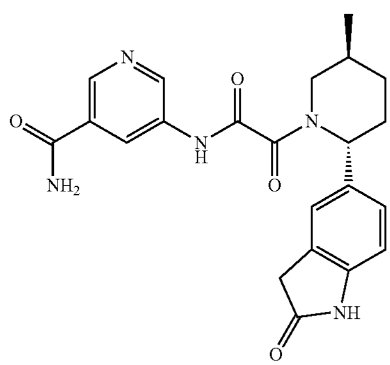 [SMILES: C[C@H]1CC[C@H](c2ccc3c(c2)CC(=O)N3)N(C(=O)C(=O)Nc2cncc(C(N)=O)c2)C1] | 319 | or/rel | b | aa | aaa | b* | aa* | B | B* |
| 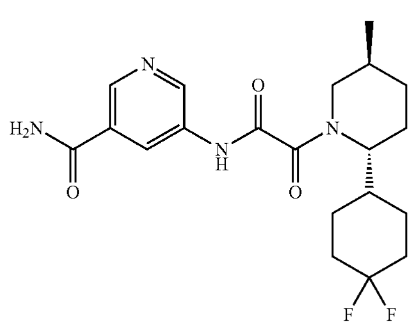 [SMILES: C[C@H]1CC[C@H](C2CCC(F)(F)CC2)N(C(=O)C(=O)Nc2cncc(C(N)=O)c2)C1] | 320 | or/rel | b | cc | bbb | c* | cc* | B | C* |

TABLE 1-continued

Exemplary compounds of the invention and biological data

| Structure | Nr | Stereo | No Co-factor/ SAM rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|
| 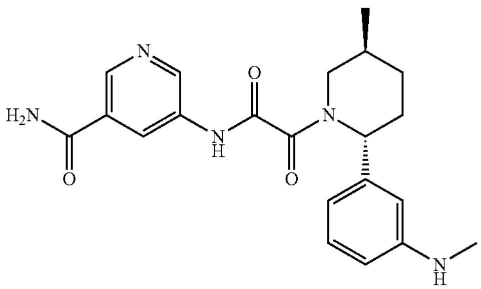 [SMILES: CNc1cccc([C@H]2CC[C@H](C)CN2C(=O)C(=O)Nc2cncc(C(N)=O)c2)c1] | 321 | or/rel | c | cc | ccc | c* | cc* | C |
| 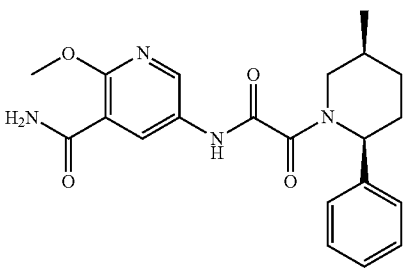 [SMILES: COc1ncc(NC(=O)C(=O)N2C[C@@H](C)CC[C@H]2c2ccccc2)cc1C(N)=O] | 322 | or/rel | c | cc | ccc | c* | cc* | B |
| | 323 | or/rel | b | aa | aaa | b* | aa* | A | A* |
| | 324 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 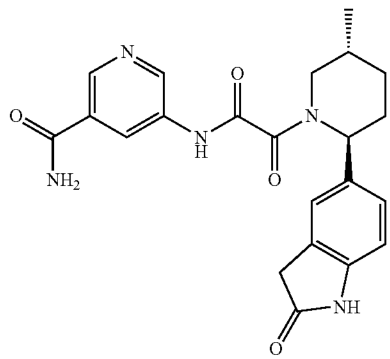 [SMILES: C[C@@H]1CC[C@@H](c2ccc3c(c2)CC(=O)N3)N(C(=O)C(=O)Nc2cncc(C(N)=O)c2)C1] | 325 | or/rel | c | cc | ccc | c* | cc* | C | |
| 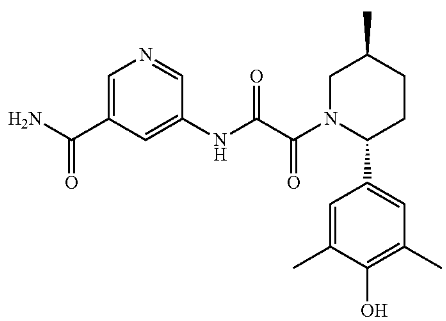 [SMILES: Cc1cc([C@H]2CC[C@H](C)CN2C(=O)C(=O)Nc2cncc(C(N)=O)c2)cc(C)c1O] | 326 | or/rel | c | cc | ccc | c* | cc* | C | |
| 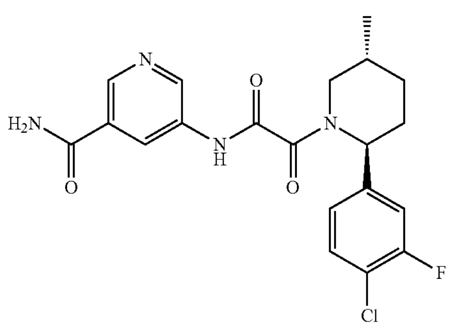 [SMILES: C[C@@H]1CC[C@@H](c2ccc(Cl)c(F)c2)N(C(=O)C(=O)Nc2cncc(C(N)=O)c2)C1] | 327 | and/rac | b | bb | bbb | c* | aa* | A | B* |
| 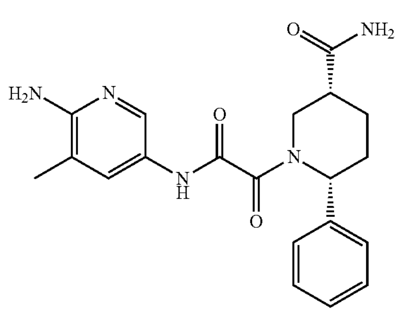 [SMILES: Cc1cc(NC(=O)C(=O)N2C[C@H](C(N)=O)CC[C@@H]2c2ccccc2)cnc1N] | 328 | and/rac | c | cc | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 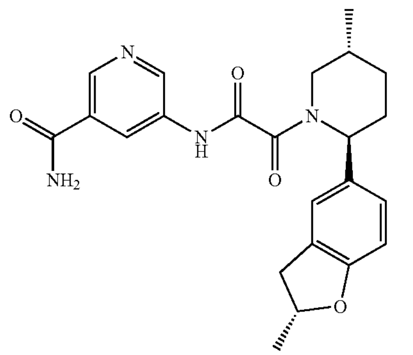 [SMILES: C[C@@H]1CC[C@@H](c2ccc3c(c2)C[C@@H](C)O3)N(C(=O)C(=O)Nc2cncc(C(N)=O)c2)C1] | 329 | or/rel | b | bb | aaa | c* | aa* | A | B* |
| 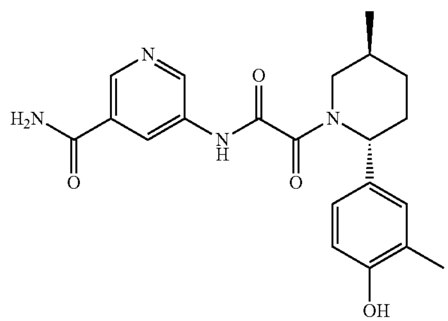 [SMILES: Cc1cc([C@H]2CC[C@H](C)CN2C(=O)C(=O)Nc2cncc(C(N)=O)c2)ccc1O] | 330 | or/rel | c | cc | ccc | | | | |
| 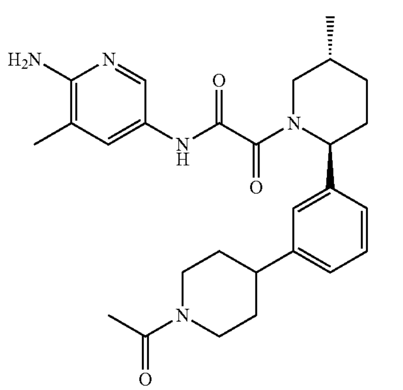 [SMILES: CC(=O)N1CCC(c2cccc([C@@H]3CC[C@@H](C)CN3C(=O)C(=O)Nc3cnc(N)c(C)c3)c2)CC1] | 331 | or/rel | c | cc | ccc | c* | cc* | C | |
| 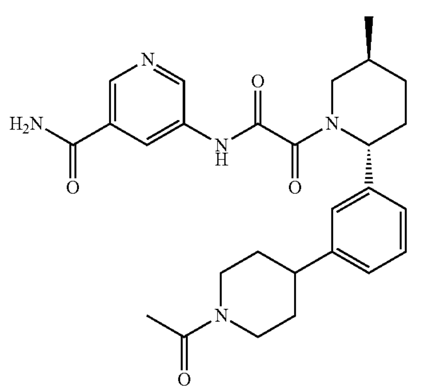 [SMILES: CC(=O)N1CCC(c2cccc([C@H]3CC[C@H](C)CN3C(=O)C(=O)Nc3cncc(C(N)=O)c3)c2)CC1] | 332 | or/rel | c | cc | ccc | c* | cc* | C | |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 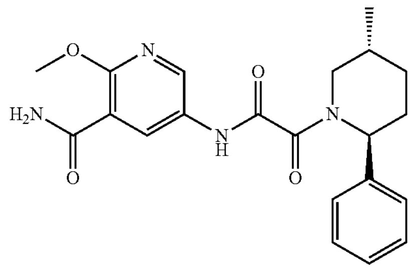 [SMILES: COc1ncc(NC(=O)C(=O)N2C[C@H](C)CC[C@H]2c2ccccc2)cc1C(N)=O] | 333 | or/rel | b | aa | aaa | c* | aa* | A | A* |
| 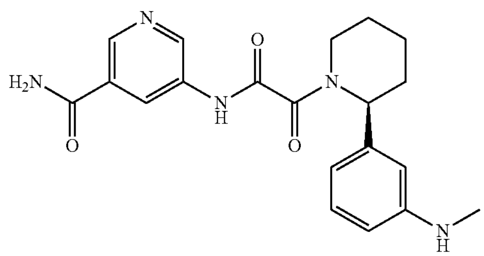 [SMILES: CNc1cccc([C@@H]2CCCCN2C(=O)C(=O)Nc2cncc(C(N)=O)c2)c1] | 334 | or/rel | b | bb | aaa | c* | aa* | A | B* |
| 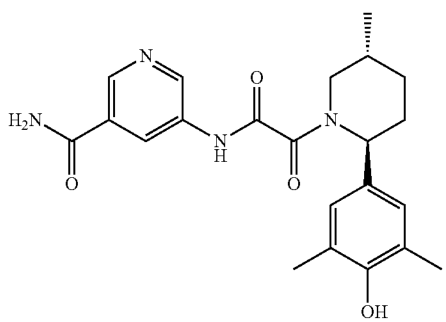 [SMILES: Cc1cc([C@@H]2CC[C@@H](C)CN2C(=O)C(=O)Nc2cncc(C(N)=O)c2)cc(C)c1O] | 335 | or/rel | b | bb | aaa | c* | aa* | A | B* |
| 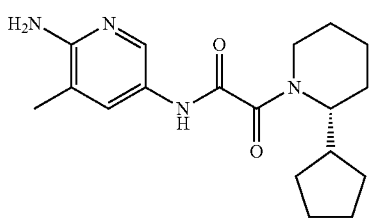 [SMILES: Cc1cc(NC(=O)C(=O)N2CCCC[C@@H]2C2CCCC2)cnc1N] | 336 | or/rel | c | cc | ccc | c* | cc* | C | |
| 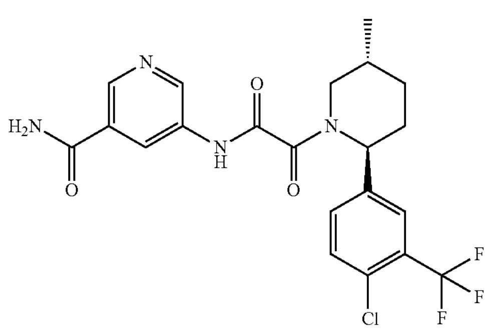 [SMILES: C[C@@H]1CC[C@@H](c2ccc(Cl)c(C(F)(F)F)c2)N(C(=O)C(=O)Nc2cncc(C(N)=O)c2)C1] | 337 | and/rac | c | bb | bbb | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 338 | and/rac | b | bb | bbb | c* | aa* | A | B* |
| | 339 | or/rel | b | bb | aaa | c* | bb* | A | C* |
| | 340 | or/rel | b | bb | aaa | c* | bb* | A | B* |
| | 341 | and/rac | b | bb | bbb | c* | aa* | A | B* |
| | 342 | and/rac | b | cc | bbb | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 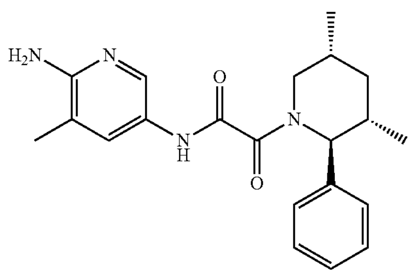 | 343 | or/rel | c | cc | ccc | c* | cc* | C | |
| 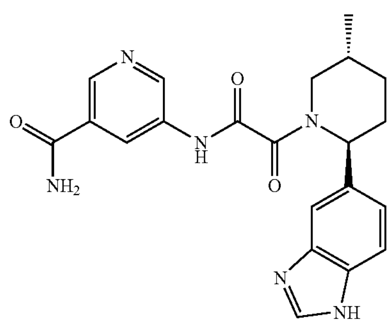 [SMILES: C[C@@H]1CC[C@@H](c2ccc3[nH]cnc3c2)N(C(=O)C(=O)Nc2cncc(C(N)=O)c2)C1] | 344 | or/rel | b | bb | aaa | c* | bb* | A | B* |
| 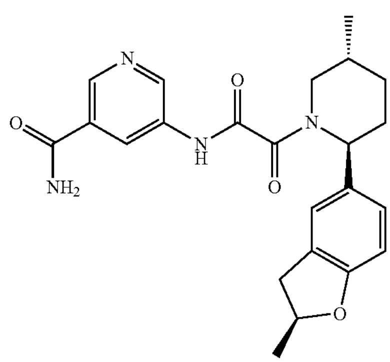 [SMILES: C[C@@H]1CC[C@@H](c2ccc3c(c2)C[C@H](C)O3)N(C(=O)C(=O)Nc2cncc(C(N)=O)c2)C1] | 345 | or/rel | b | bb | aaa | c* | bb* | A | B* |
| 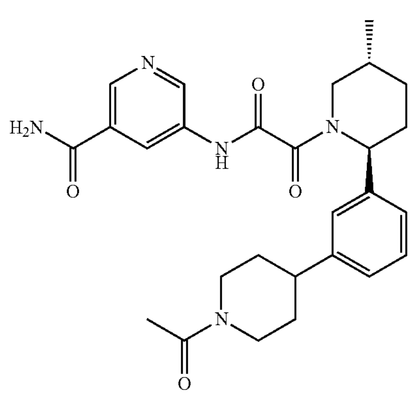 [SMILES: CC(=O)N1CCC(c2cccc([C@@H]3CC[C@@H](C)CN3C(=O)C(=O)Nc3cncc(C(N)=O)c3)c2)CC1] | 346 | or/rel | b | bb | aaa | c* | bb* | A | B* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| 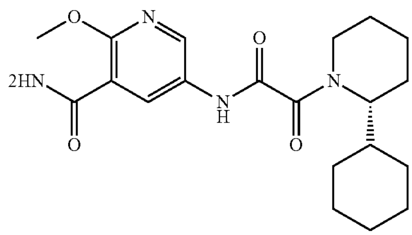 | 347 | or/rel | b | bb | aaa | c* | bb* | A | B* |
| 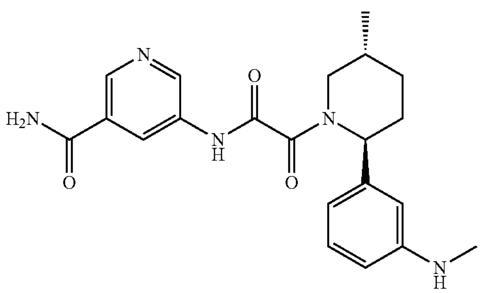 [SMILES: CNc1cccc([C@@H]2CC[C@@H](C)CN2C(=O)C(=O)Nc2cncc(C(N)=O)c2)c1] | 348 | or/rel | b | bb | aaa | c* | aa* | A | B* |
| 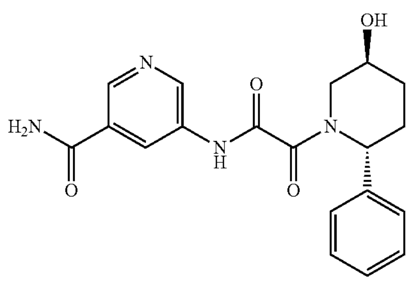 [SMILES: NC(=O)c1cncc(NC(=O)C(=O)N2C[C@@H](O)CC[C@@H]2c2ccccc2)c1] | 349 | and/rac | c | cc | bbb | c* | cc* | C | C* |
| 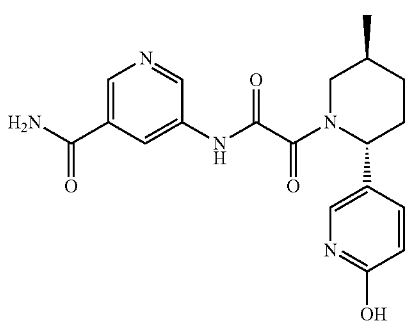 [SMILES: C[C@H]1CC[C@H](c2ccc(O)nc2)N(C(=O)C(=O)Nc2cncc(C(N)=O)c2)C1] | 350 | or/rel | b | bb | aaa | c* | cc* | C | C* |
| 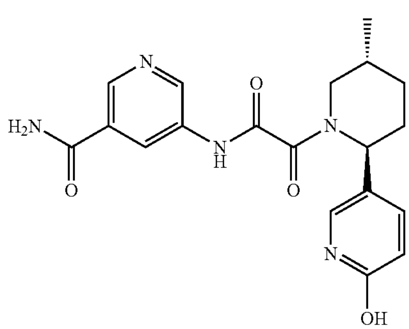 | 351 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 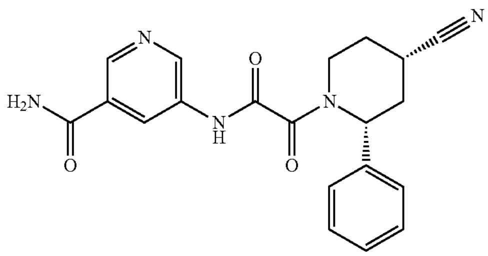 [SMILES: N#C[C@H]1CCN(C(=O)C(=O)Nc2cncc(C(N)=O)c2)[C@@H](c2ccccc2)C1] | 352 | or/rel | b | bb | aaa | c* | bb* | A | C* |
| 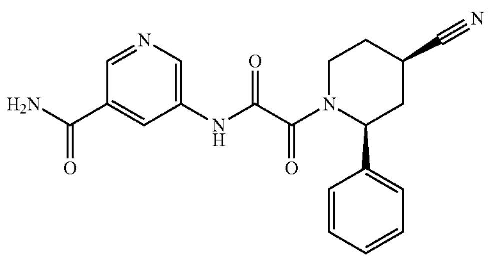 [SMILES: N#C[C@@H]1CCN(C(=O)C(=O)Nc2cncc(C(N)=O)c2)[C@H](c2ccccc2)C1] | 353 | or/rel | c | cc | ccc | c* | cc* | C | C* |
| 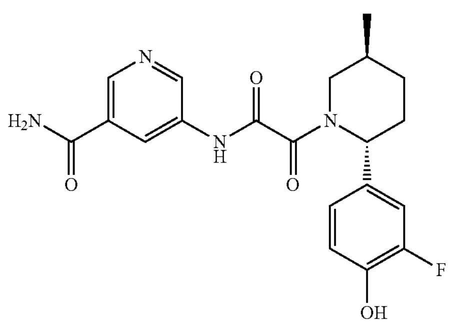 [SMILES: C[C@H]1CC[C@H](c2ccc(O)c(F)c2)N(C(=O)C(=O)Nc2cncc(C(N)=O)c2)C1] | 354 | or/rel | b | aa | aaa | b* | aa* | A | A* |
| 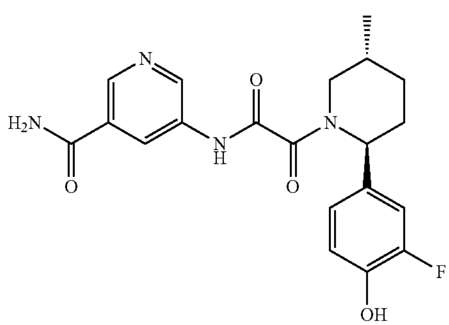 [SMILES: C[C@@H]1CC[C@@H](c2ccc(O)c(F)c2)N(C(=O)C(=O)Nc2cncc(C(N)=O)c2)C1] | 355 | or/rel | c | cc | ccc | c* | cc* | C | C* |
| 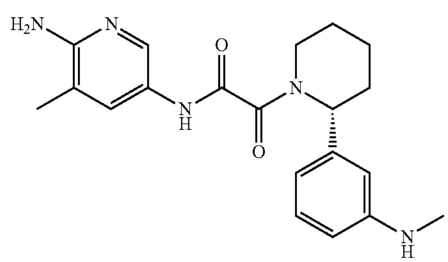 | 356 | or/rel | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 357 | or/rel | b | cc | bbb | c* | bb* | A | C* |
| | 358 | or/rel | c | cc | ccc | c* | cc* | C | C* |
| | 359 | or/rel | b | bb | aaa | c* | aa* | A | B* |
| | 360 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 361 | or/rel | b | aa | aaa | b* | aa* | A | A* |
| | 362 | or/rel | c | cc | ccc | c* | cc* | C | C* |
| | 363 | or/rel | b | aa | aaa | a* | aa* | A | A* |
| | 364 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 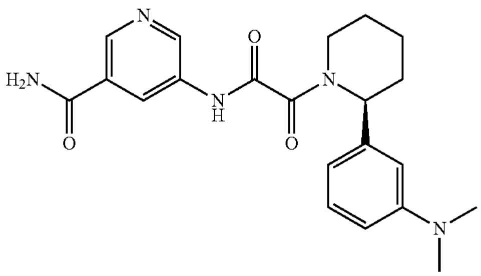 [SMILES: CN(C)c1cccc([C@@H]2CCCCN2C(=O)C(=O)Nc2cncc(C(N)=O)c2)c1] | 365 | or/rel | b | bb | aaa | c* | aa* | A | B* |
| 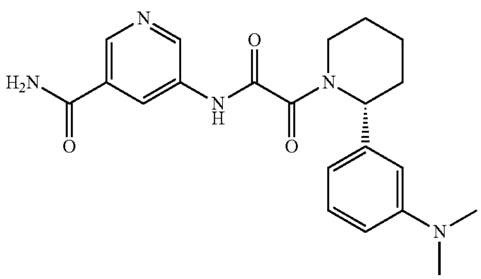 [SMILES: CN(C)c1cccc([C@H]2CCCCN2C(=O)C(=O)Nc2cncc(C(N)=O)c2)c1] | 366 | or/rel | c | cc | bbb | c* | cc* | C | C* |
| 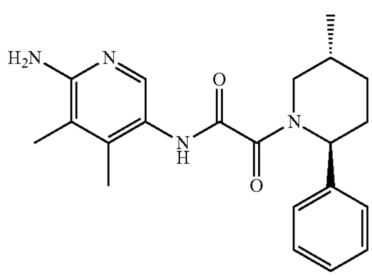 [SMILES: Cc1c(NC(=O)C(=O)N2C[C@H](C)CC[C@H]2c2ccccc2)cnc(N)c1C] | 367 | or/rel | c | cc | bbb | c* | cc* | C | C* |
| 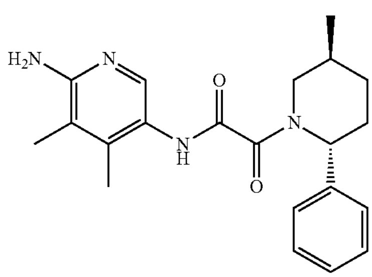 [SMILES: Cc1c(NC(=O)C(=O)N2C[C@@H](C)CC[C@@H]2c2ccccc2)cnc(N)c1C] | 368 | or/rel | b | bb | aaa | c* | aa* | A | B* |
| 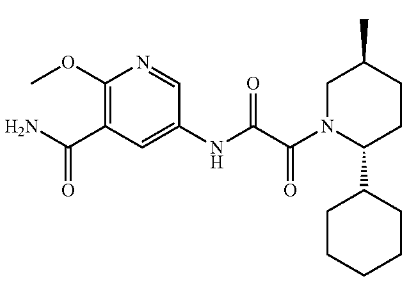 [SMILES: COc1ncc(NC(=O)C(=O)N2C[C@@H](C)CC[C@@H]2C2CCCCC2)cc1C(N)=O] | 369 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 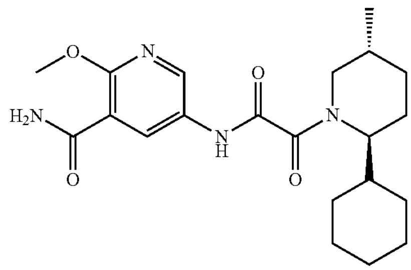 [SMILES: COc1ncc(NC(=O)C(=O)N2C[C@H](C)CC[C@H]2C2CCCCC2)cc1C(N)=O] | 370 | or/rel | c | cc | ccc | | | | |
| 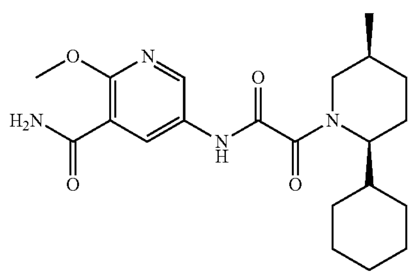 [SMILES: COc1ncc(NC(=O)C(=O)N2C[C@@H](C)CC[C@H]2C2CCCCC2)cc1C(N)=O] | 371 | or/rel | c | cc | ccc | c* | cc* | C | |
| 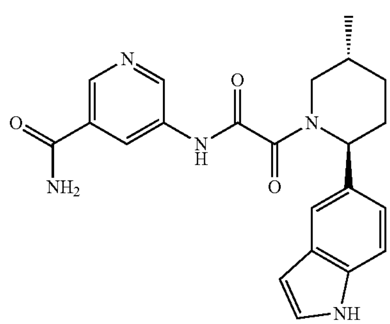 [SMILES: C[C@@H]1CC[C@@H](c2ccc3[nH]ccc3c2)N(C(=O)C(=O)Nc2cncc(C(N)=O)c2)C1] | 372 | or/rel | c | cc | ccc | c* | cc* | C | C* |
| 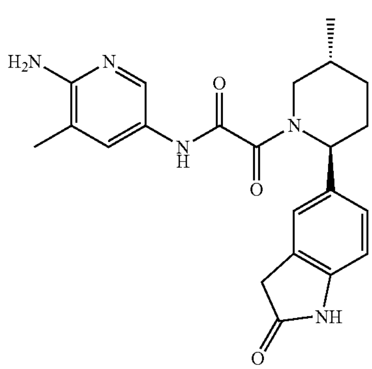 [SMILES: Cc1cc(NC(=O)C(=O)N2C[C@H](C)CC[C@H]2c2ccc3c(c2)CC(=O)N3)cnc1N] | 373 | and/rac | b | bb | aaa | b* | aa* | A | A* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 374 | or/rel | c | cc | ccc | c* | cc* | C | C* |
| | 375 | or/rel | b | bb | aaa | c* | aa* | A | B* |
| | 376 | or/rel | c | cc | ccc | c* | cc* | C | C* |
| | 377 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 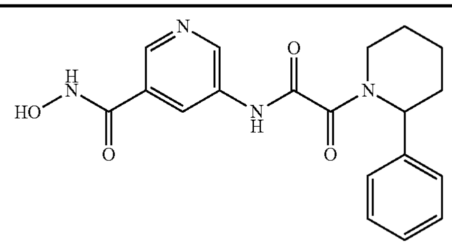 | 378 | | c | cc | bbb | | | | |
| 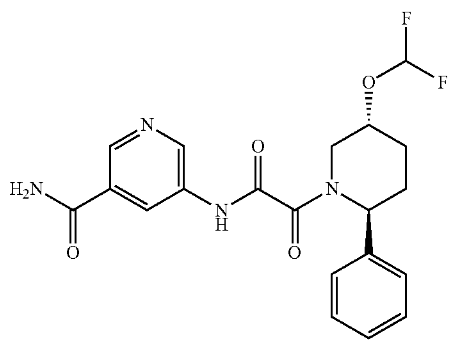 [SMILES: NC(=O)c1cncc(NC(=O)C(=O)N2C[C@H](OC(F)F)CC[C@H]2c2ccccc2)c1] | 379 | and/rac | b | cc | bbb | | | | C* |
| 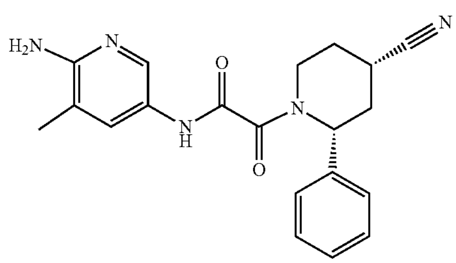 [SMILES: Cc1cc(NC(=O)C(=O)N2CC[C@H](C#N)C[C@@H]2c2ccccc2)cnc1N] | 380 | or/rel | c | cc | ccc | c* | cc* | C | C* |
| 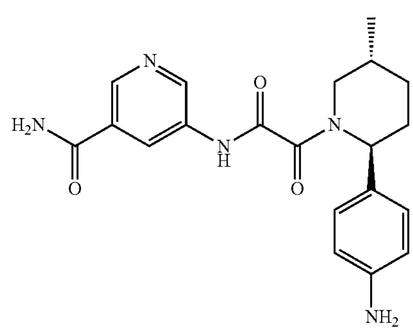 | 381 | or/rel | b | aa | aaa | c* | aa* | A | A* |
| 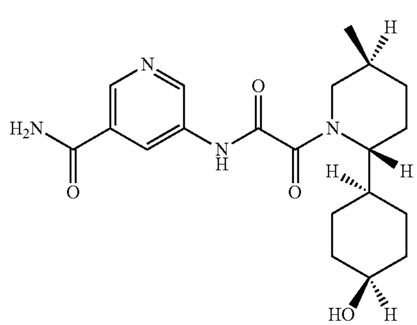 [SMILES: C[C@H]1CC[C@H]([C@H]2CC[C@@H](O)CC2)N(C(=O)C(=O)Nc2cncc(C(N)=O)c2)C1] | 382 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 383 | or/rel | b | bb | aaa | c* | aa* | A | A* |
| | 384 | or/rel | b | aa | aaa | c* | aa* | A | A* |
| | 385 | or/rel | b | aa | aaa | b* | aa* | A | A* |
| | 386 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 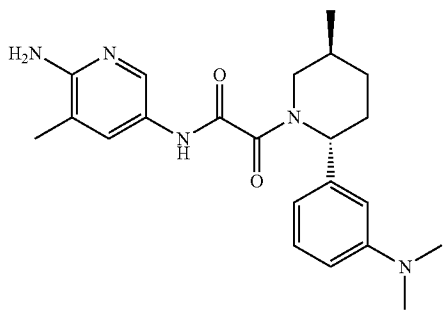 | 387 | or/rel | c | cc | ccc | | | | |
| 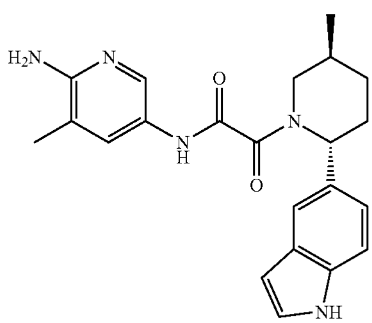 [SMILES: Cc1cc(NC(=O)C(=O)N2C[C@@H](C)CC[C@@H]2c2ccc3[nH]ccc3c2)cnc1N] | 388 | or/rel | c | cc | ccc | c* | cc* | C | C* |
| 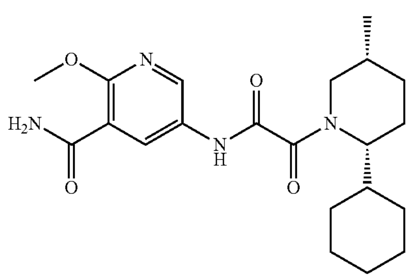 [SMILES: COc1ncc(NC(=O)C(=O)N2C[C@H](C)CC[C@@H]2C2CCCCC2)cc1C(N)=O] | 389 | or/rel | c | cc | bbb | | | | C* |
| 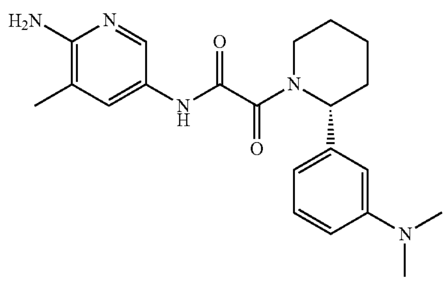 | 390 | or/rel | b | cc | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 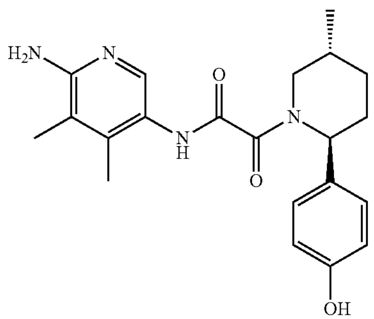 [SMILES: Cc1c(NC(=O)C(=O)N2C[C@H](C)CC[C@H]2c2ccc(O)cc2)cnc(N)c1C] | 391 | or/rel | c | cc | ccc | c* | cc* | C | C* |
| 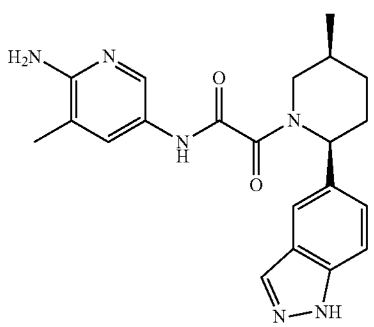 [SMILES: Cc1cc(NC(=O)C(=O)N2C[C@@H](C)CC[C@H]2c2ccc3[nH]ncc3c2)cnc1N] | 392 | or/rel | b | bb | aaa | c* | aa* | A | B* |
| 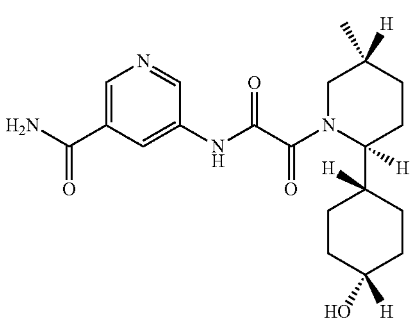 [SMILES: C[C@@H]1CC[C@@H]([C@H]2CC[C@@H](O)CC2)N(C(=O)C(=O)Nc2cncc(C(N)=O)c2)C1] | 393 | or/rel | b | cc | bbb | c* | cc* | B | C* |
| 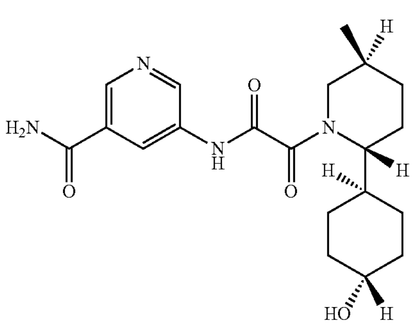 [SMILES: C[C@H]1CC[C@H]([C@H]2CC[C@H](O)CC2)N(C(=O)C(=O)Nc2cncc(C(N)=O)c2)C1] | 394 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 395 | or/rel | c | cc | ccc | c* | cc* | C | C* |
| | 396 | or/rel | c | cc | ccc | c* | cc* | C | C* |
| | 397 | or/rel | a | aa | aaa | b* | aa* | A | A* |
| | 398 | or/rel | c | cc | ccc | c* | cc* | B | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 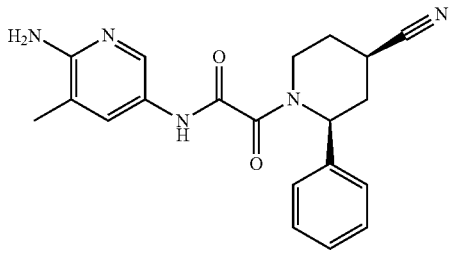 [SMILES: Cc1cc(NC(=O)C(=O)N2CC[C@@H](C#N)C[C@H]2c2ccccc2)cnc1N] | 399 | or/rel | b | bb | aaa | c* | aa* | A | B* |
| 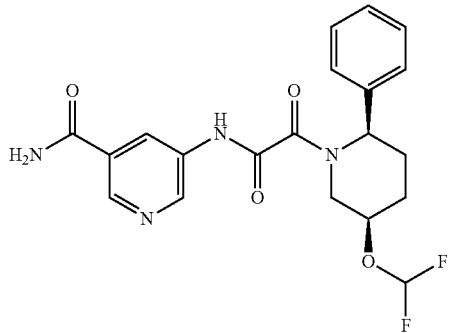 [SMILES: NC(=O)c1cncc(NC(=O)C(=O)N2C[C@H](OC(F)F)CC[C@@H]2c2ccccc2)c1] | 400 | and/rac | c | cc | bbb | | | | |
| 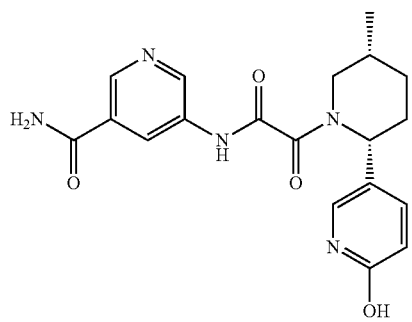 [SMILES: C[C@@H]1CC[C@H](c2ccc(O)nc2)N(C(=O)C(=O)Nc2cncc(C(N)=O)c2)C1] | 401 | or/rel | b | bb | aaa | | | | C* |
| 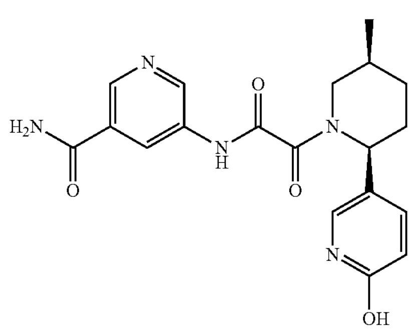 [SMILES: C[C@H]1CC[C@@H](c2ccc(O)nc2)N(C(=O)C(=O)Nc2cncc(C(N)=O)c2)C1] | 402 | or/rel | c | cc | ccc | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 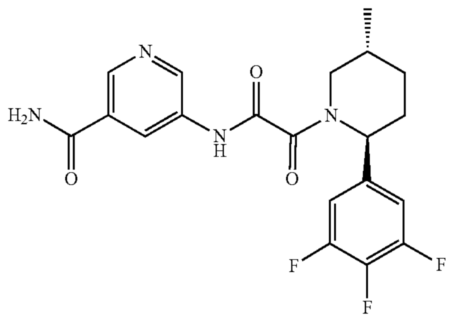 [SMILES: C[C@@H]1CC[C@@H](c2cc(F)c(F)c(F)c2)N(C(=O)C(=O)Nc2cncc(C(N)=O)c2)C1] | 403 | and/rac | b | cc | bbb | | | | C* |
| 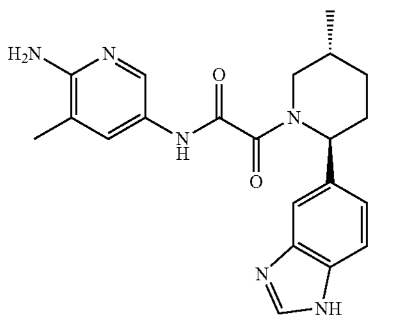 [SMILES: Cc1cc(NC(=O)C(=O)N2C[C@H](C)CC[C@H]2c2ccc3[nH]cnc3c2)cnc1N] | 404 | or/rel | c | cc | ccc | | | | |
| 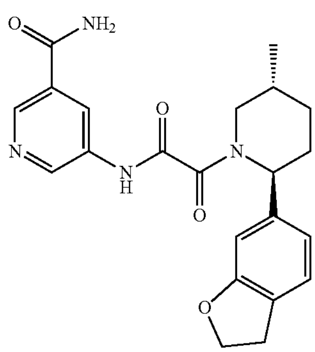 [SMILES: C[C@@H]1CC[C@@H](c2ccc3c(c2)OCC3)N(C(=O)C(=O)Nc2cncc(C(N)=O)c2)C1] | 405 | and/rac | b | bb | bbb | c* | aa* | A | B* |
| 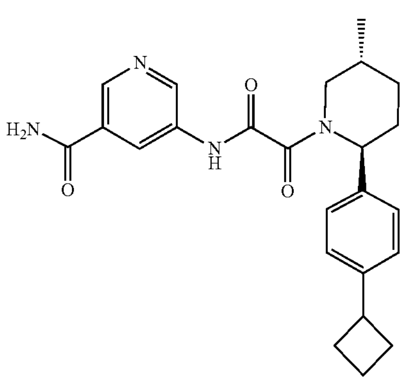 [SMILES: C[C@@H]1CC[C@@H](c2ccc(C3CCC3)cc2)N(C(=O)C(=O)Nc2cncc(C(N)=O)c2)C1] | 406 | and/rac | b | bb | bbb | | | | B* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 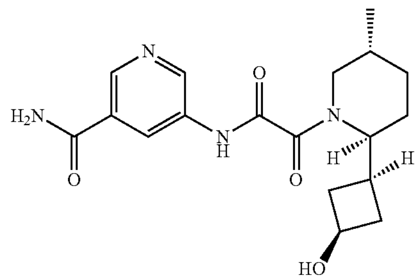 [SMILES: C[C@@H]1CC[C@@H]([C@H]2C[C@@H](O)C2)N(C(=O)C(=O)Nc2cncc(C(N)=O)c2)C1] | 407 | and/rac | b | cc | bbb |  |  |  | C* |
| 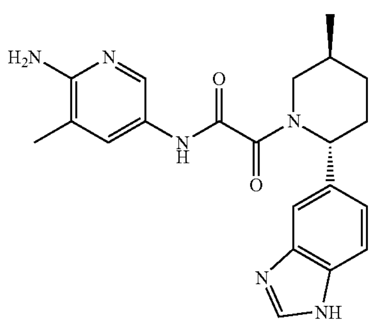 [SMILES: Cc1cc(NC(=O)C(=O)N2C[C@@H](C)CC[C@@H]2c2ccc3[nH]cnc3c2)cnc1N] | 408 | or/rel | b | aa | aaa | b* | aa* | A | A* |
| 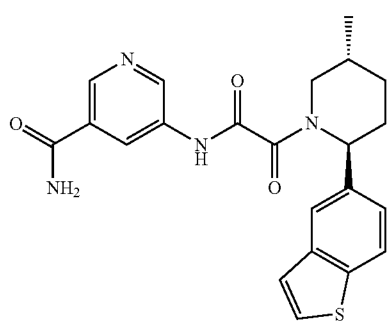 [SMILES: C[C@@H]1CC[C@@H](c2ccc3sccc3c2)N(C(=O)C(=O)Nc2cncc(C(N)=O)c2)C1] | 409 | and/rac | b | bb | aaa | c* | aa* | A | B* |
| 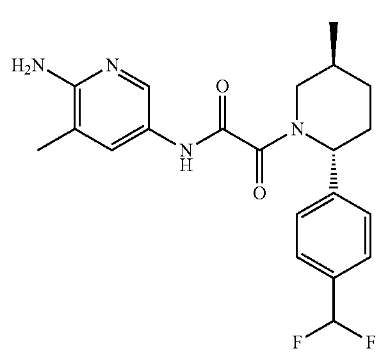 [SMILES: Cc1cc(NC(=O)C(=O)N2C[C@@H](C)CC[C@@H]2c2ccc(C(F)F)cc2)cnc1N] | 410 | or/rel | c | cc | ccc |  |  |  | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 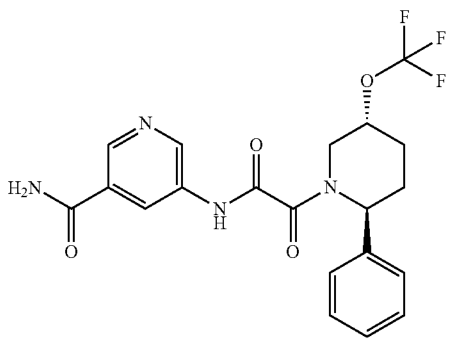 [SMILES: NC(=O)c1cncc(NC(=O)C(=O)N2C[C@H](OC(F)(F)F)CC[C@H]2c2ccccc2)c1] | 411 | and/rac | c | cc | bbb | | | | |
| 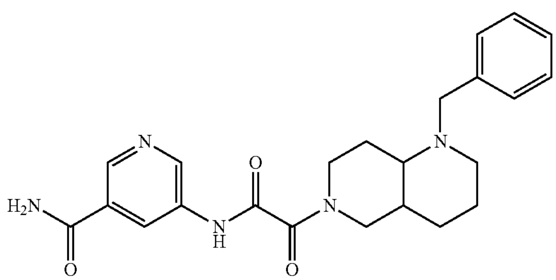 [SMILES: NC(=O)c1cncc(NC(=O)C(=O)N2CCC3C(CCCN3Cc3ccccc3)C2)c1] | 412 | | b | cc | bbb | | | | C* |
| 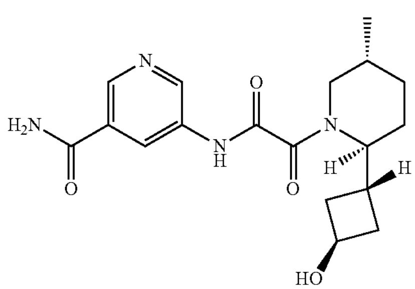 [SMILES: C[C@@H]1CC[C@@H]([C@H]2C[C@H](O)C2)N(C(=O)C(=O)Nc2cncc(C(N)=O)c2)C1] | 413 | and/rac | c | cc | bbb | | | | C* |
| 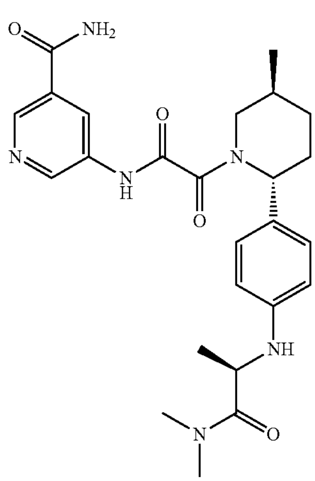 [SMILES: C[C@H]1CC[C@H](c2ccc(N[C@H](C)C(=O)N(C)C)cc2)N(C(=O)C(=O)Nc2cncc(C(N)=O)c2)C1] | 414 | and/rac | b | bb | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| (structure 415) | 415 | or/rel | b | bb | aaa | b* | aa* | A | B* |
| (structure 416) | 416 | and/rac | b | bb | bbb | | | | B* |
| (structure 417) | 417 | or/rel | b | cc | bbb | c* | bb* | B | C* |
| (structure 418) | 418 | and/rac | c | cc | bbb | | | | C* |
| (structure 419) | 419 | or/rel | b | bb | aaa | b* | aa* | A | B* |
| (structure 420) | 420 | | c | cc | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 421 | and/rac | c | cc | bbb | | | | C* |
| | 422 | and/rac | b | cc | bbb | c* | bb* | A | C* |
| | 423 | or/rel | c | cc | ccc | | | | C* |
| | 424 | or/rel | c | cc | ccc | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 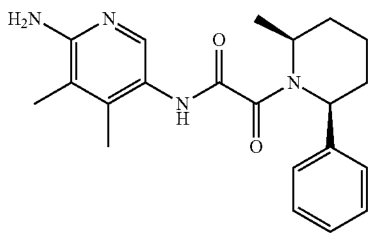 | 425 | or/rel | b | bb | aaa | c* | bb* | A | B* |
| 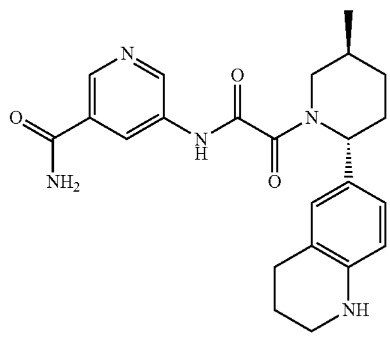 [SMILES: C[C@H]1CC[C@H](c2ccc3c(c2)CCCN3)N(C(=O)C(=O)Nc2cncc(C(N)=O)c2)C1] | 426 | or/rel | c | cc | ccc | | | | C* |
| 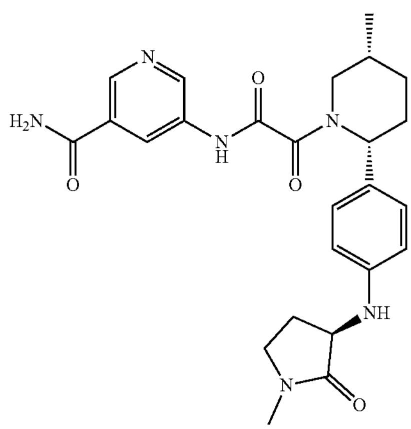 [SMILES: C[C@@H]1CC[C@H](c2ccc(N[C@@H]3CCN(C)C3=O)cc2)N(C(=O)C(=O)Nc2cncc(C(N)=O)c2)C1] | 427 | and/rac | b | bb | bbb | c* | bb* | A | C* |
| 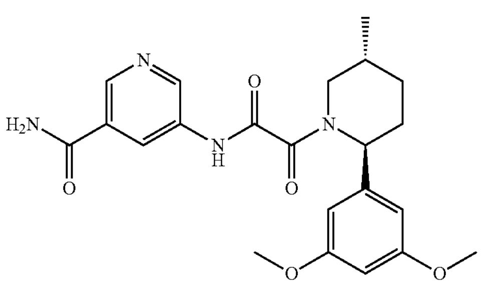 [SMILES: COc1cc(OC)cc([C@@H]2CC[C@@H](C)CN2C(=O)C(=O)Nc2cncc(C(N)=O)c2)c1] | 428 | and/rac | c | cc | bbb | c* | bb* | A | C* |
| 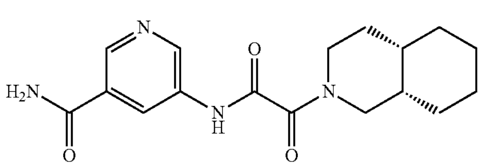 [SMILES: NC(=O)c1cncc(NC(=O)C(=O)N2CC[C@@H]3CCCC[C@@H]3C2)c1] | 429 | and/rac | b | cc | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 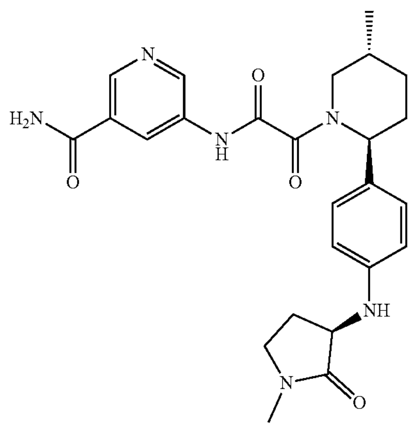 | 430 | and/rac | b | bb | bbb | c* | aa* | A | B* |
| 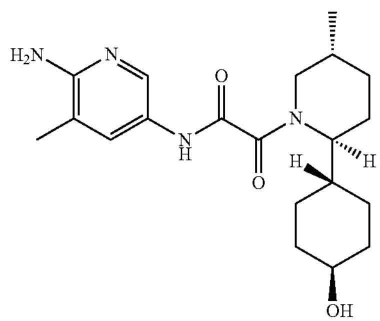 [SMILES: Cc1cc(NC(=O)C(=O)N2C[C@H](C)CC[C@H]2[C@H]2CC[C@H](O)CC2)cnc1N] | 431 | or/rel | b | bb | aaa | c* | aa* | A | B* |
| 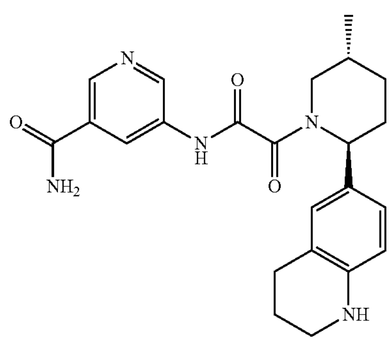 [SMILES: C[C@@H]1CC[C@@H](c2ccc3c(c2)CCCN3)N(C(=O)C(=O)Nc2cncc(C(N)=O)c2)C1] | 432 | or/rel | b | bb | aaa | c* | aa* | A | B* |
| 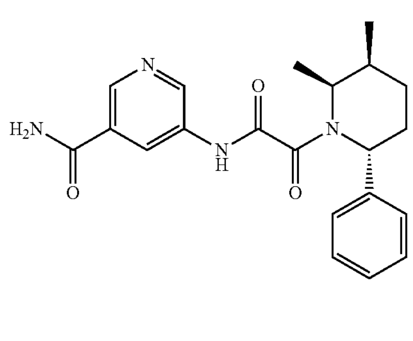 [SMILES: C[C@H]1CC[C@H](c2ccccc2)N(C(=O)C(=O)Nc2cncc(C(N)=O)c2)[C@H]1C] | 433 | or/rel | b | cc | aaa | c* | aa* | A | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 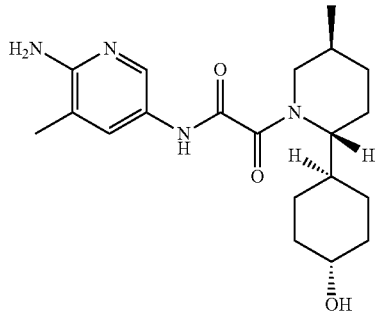 [SMILES: Cc1cc(NC(=O)C(=O)N2C[C@@H](C)CC[C@@H]2[C@H]2CC[C@H](O)CC2)cnc1N] | 434 | or/rel | c | cc | ccc | | | | C* |
| 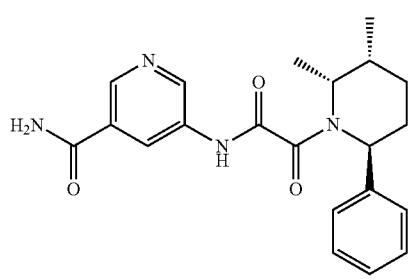 [SMILES: C[C@@H]1CC[C@@H](c2ccccc2)N(C(=O)C(=O)Nc2cncc(C(N)=O)c2)[C@@H]1C] | 435 | or/rel | c | cc | ccc | | | | C* |
| 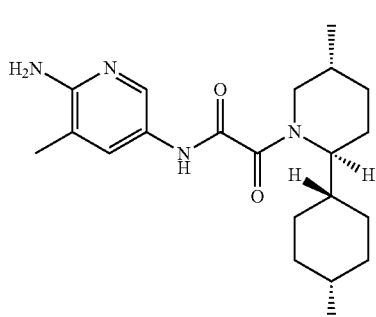 | 436 | or/rel | b | bb | bbb | c* | bb* | A | C* |
| 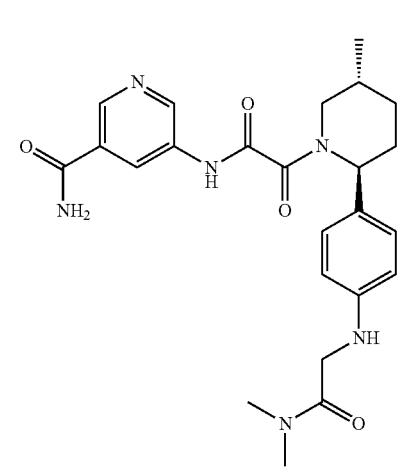 [SMILES: C[C@@H]1CC[C@@H](c2ccc(NCC(=O)N(C)C)cc2)N(C(=O)C(=O)Nc2cncc(C(N)=O)c2)C1] | 437 | or/rel | b | bb | aaa | c* | aa* | A | B* |

TABLE 1-continued

Exemplary compounds of the invention and biological data

| Structure | Nr | Stereo | No Co-factor/ SAM rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|
| (structure 438) | 438 | | a | aa | aaa | c* | aa* | A | A* |
| (structure 439) | 439 | or/rel | b | bb | aaa | c* | aa* | A | B* |
| (structure 440) | 440 | or/rel | b | bb | aaa | c* | aa* | A | B* |
| (structure 441) | 441 | or/rel | c | cc | ccc | | | | C* |
| (structure 442) | 442 | and/rac | b | bb | bbb | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 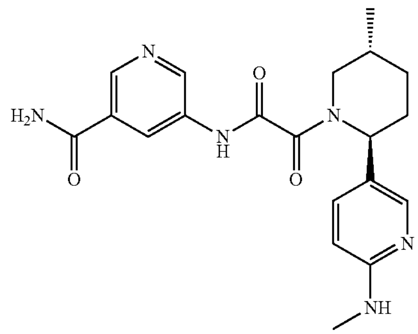 [SMILES: CNc1ccc([C@@H]2CC[C@@H](C)CN2C(=O)C(=O)Nc2cncc(C(N)=O)c2)cn1] | 443 | or/rel | b | aa | aaa | c* | aa* | A | A* |
| 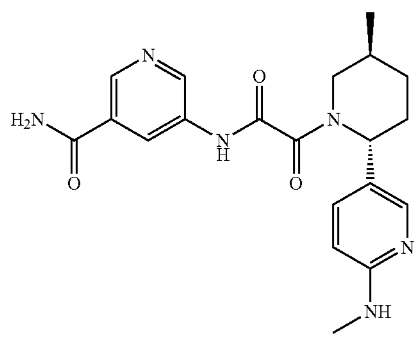 [SMILES: CNc1ccc([C@H]2CC[C@H](C)CN2C(=O)C(=O)Nc2cncc(C(N)=O)c2)cn1] | 444 | or/rel | c | cc | ccc | | | | C* |
| 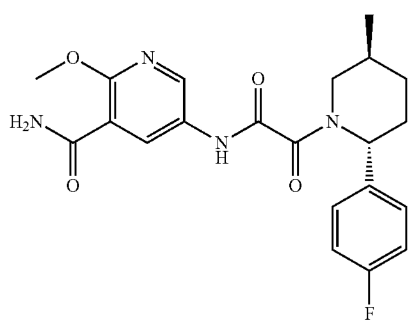 [SMILES: COc1ncc(NC(=O)C(=O)N2C[C@@H](C)CC[C@@H]2c2ccc(F)cc2)cc1C(N)=O] | 445 | or/rel | c | cc | ccc | | | | C* |
| 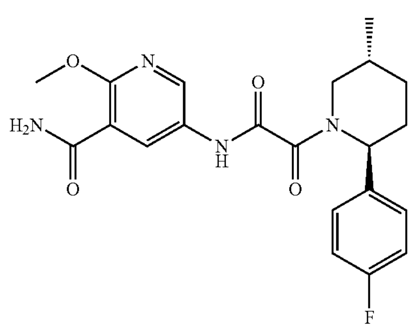 [SMILES: COc1ncc(NC(=O)C(=O)N2C[C@H](C)CC[C@H]2c2ccc(F)cc2)cc1C(N)=O] | 446 | or/rel | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 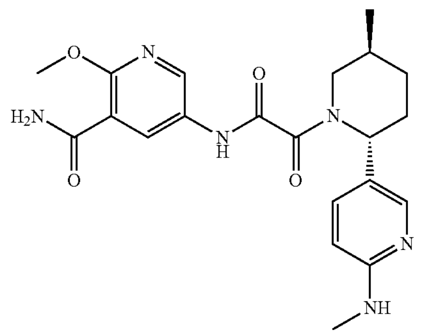 [SMILES: CNc1ccc([C@H]2CC[C@H](C)CN2C(=O)C(=O)Nc2cnc(OC)c(C(N)=O)c2)cn1] | 447 | or/rel | b | aa | aaa | c* | aa* | A | A* |
| 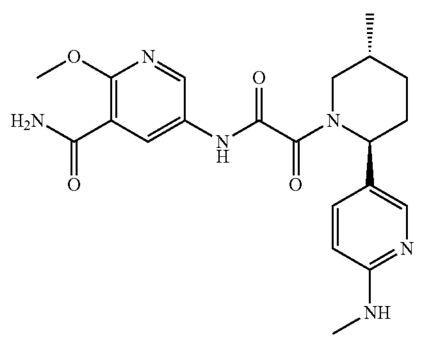 [SMILES: CNc1ccc([C@@H]2CC[C@@H](C)CN2C(=O)C(=O)Nc2cnc(OC)c(C(N)=O)c2)cn1] | 448 | or/rel | c | cc | ccc | c* | cc* | C | C* |
| 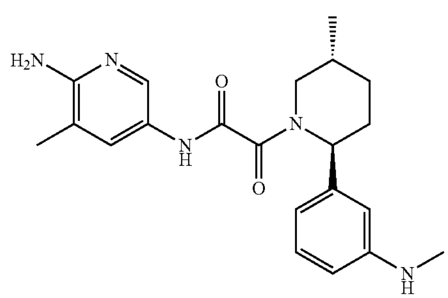 | 449 | or/rel | b | bb | aaa | b* | aa* | A | A* |
| 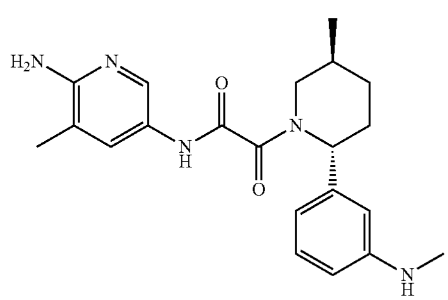 | 450 | or/rel | c | cc | ccc | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 451 | or/rel | b | bb | aaa | c* | aa* | A | B* |
| | 452 | or/rel | c | cc | ccc | | | | C* |
| | 453 | or/rel | c | cc | ccc | c* | cc* | C | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 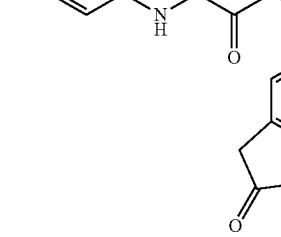 | 454 | or/rel | b | aa | aaa | b* | aa* | A | A* |
| 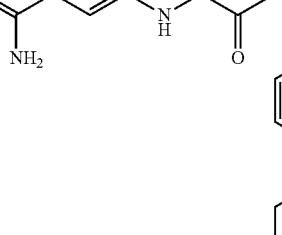 | 455 | or/rel | b | bb | aaa | c* | bb* | A | B* |
| 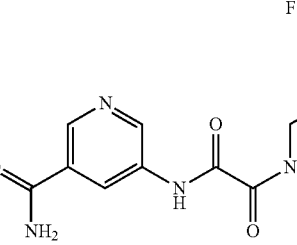 | 456 | or/rel | c | cc | ccc | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 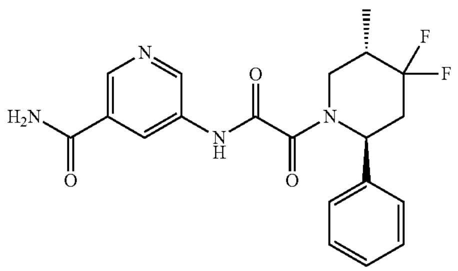 [SMILES: C[C@H]1CN(C(=O)C(=O)Nc2cncc(C(N)=O)c2)[C@H](c2ccccc2)CC1(F)F] | 457 | or/rel | b | bb | aaa | c* | aa* | A | A* |
| 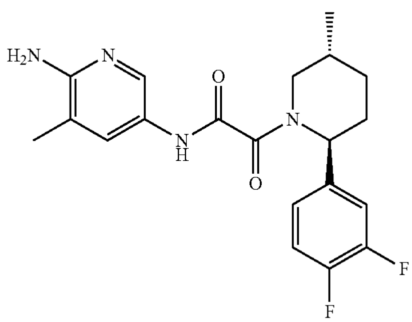 [SMILES: Cc1cc(NC(=O)C(=O)N2C[C@H](C)CC[C@H]2c2ccc(F)c(F)c2)cnc1N] | 458 | or/rel | b | aa | aaa | b* | aa* | A | B* |
| 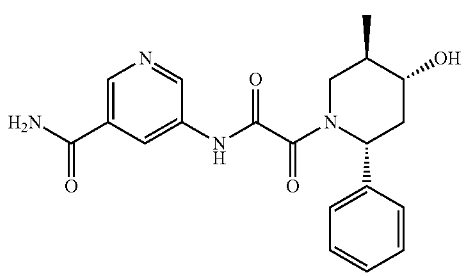 [SMILES: C[C@@H]1CN(C(=O)C(=O)Nc2cncc(C(N)=O)c2)[C@@H](c2ccccc2)C[C@H]1O] | 459 | and/rac | b | bb | bbb | c* | bb* | A | C* |
| 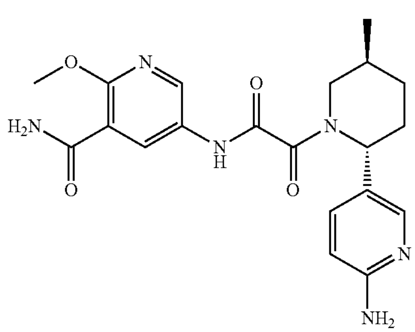 [SMILES: COc1ncc(NC(=O)C(=O)N2C[C@@H](C)CC[C@@H]2c2ccc(N)nc2)cc1C(N)=O] | 460 | or/rel | b | aa | aaa | c* | aa* | A | A* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 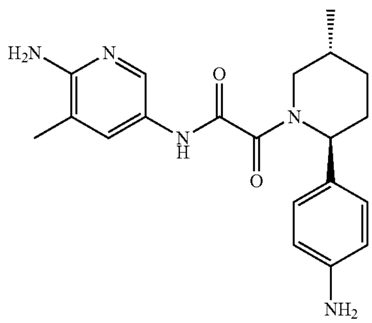 [SMILES: Cc1cc(NC(=O)C(=O)N2C[C@H](C)CC[C@H]2c2ccc(N)cc2)cnc1N] | 461 | or/rel | b | aa | aaa | b* | aa* | B | A* |
| 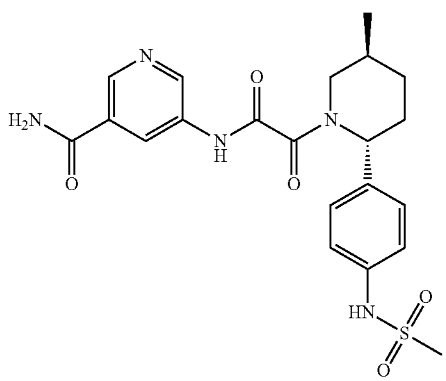 [SMILES: C[C@H]1CC[C@H](c2ccc(NS(C)(=O)=O)cc2)N(C(=O)C(=O)Nc2cncc(C(N)=O)c2)C1] | 462 | or/rel | b | bb | aaa | c* | bb* | A | B* |
| 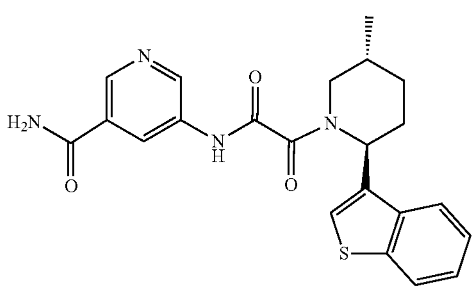 [SMILES: C[C@@H]1CC[C@@H](c2csc3ccccc23)N(C(=O)C(=O)Nc2cncc(C(N)=O)c2)C1] | 463 | or/rel | b | bb | aaa | c* | bb* | A | B* |
| 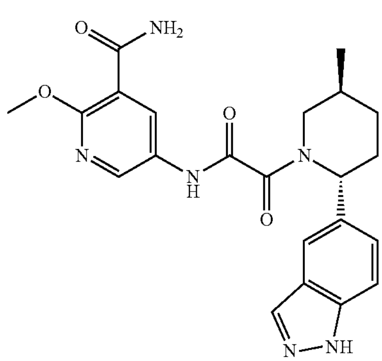 [SMILES: COc1ncc(NC(=O)C(=O)N2C[C@@H](C)CC[C@@H]2c2ccc3[nH]ncc3c2)cc1C(N)=O] | 464 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| [structure] | 465 | or/rel | c | cc | ccc | c* | cc* | B | C* |
| [structure] | 466 | or/rel | c | cc | ccc | c* | cc* | C | C* |
| [structure] | 467 | or/rel | c | cc | ccc | c* | cc* | C | C* |
| [structure] | 468 | or/rel | c | cc | ccc | c* | cc* | C | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 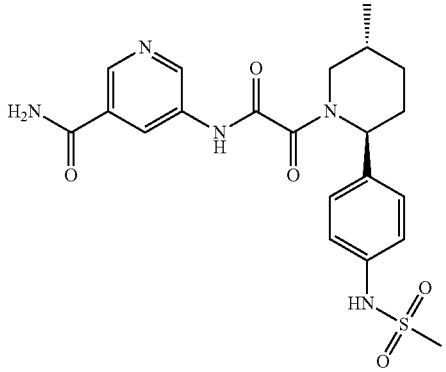 [SMILES: C[C@@H]1CC[C@@H](c2ccc(NS(C)(=O)=O)cc2)N(C(=O)C(=O)Nc2cncc(C(N)=O)c2)C1] | 469 | or/rel | c | cc | ccc | c* | cc* | C | C* |
| 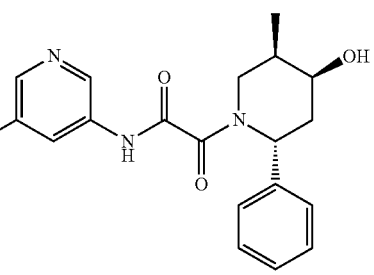 | 470 | and/rac | b | bb | bbb | c* | bb* | A | C* |
| 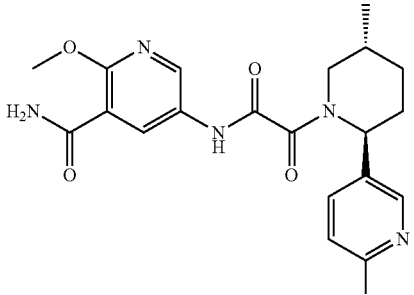 | 471 | or/rel | c | cc | ccc | c* | cc* | C | C* |
| 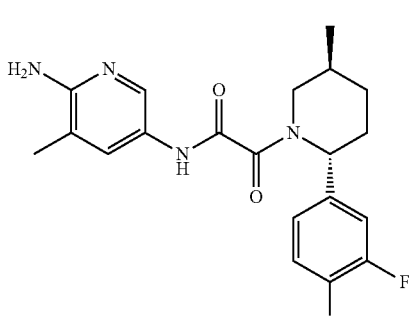 | 472 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 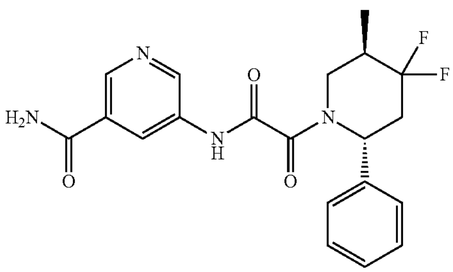 [SMILES: C[C@@H]1CN(C(=O)C(=O)Nc2cncc(C(N)=O)c2)[C@@H](c2ccccc2)CC1(F)F] | 473 | or/rel | c | cc | ccc | c* | cc* | C | C* |
| 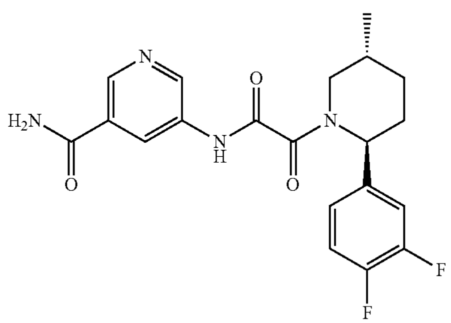 [SMILES: C[C@@H]1CC[C@@H](c2ccc(F)c(F)c2)N(C(=O)C(=O)Nc2cncc(C(N)=O)c2)C1] | 474 | or/rel | c | cc | ccc | c* | cc* | C | C* |
| 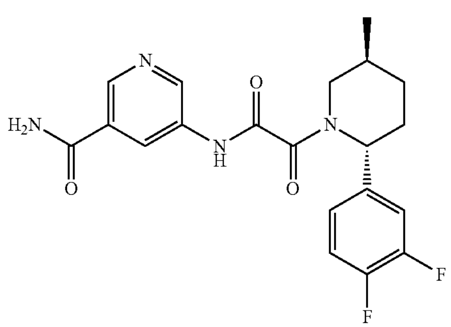 [SMILES: C[C@H]1CC[C@H](c2ccc(F)c(F)c2)N(C(=O)C(=O)Nc2cncc(C(N)=O)c2)C1] | 475 | or/rel | b | bb | aaa | c* | bb* | A | B* |
| 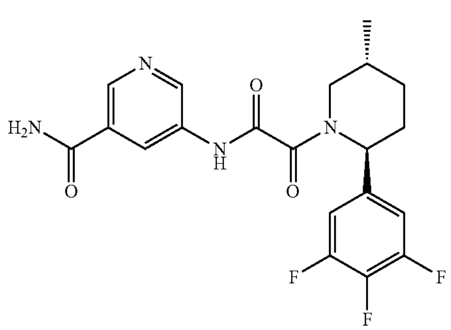 [SMILES: C[C@@H]1CC[C@@H](c2cc(F)c(F)c(F)c2)N(C(=O)C(=O)Nc2cncc(C(N)=O)c2)C1] | 476 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 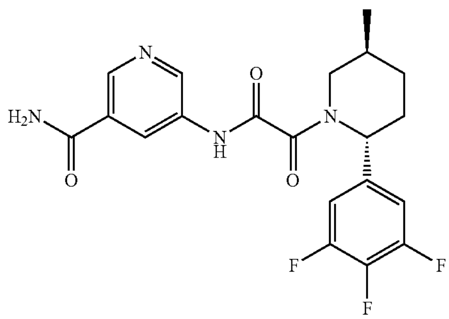 [SMILES: C[C@H]1CC[C@H](c2cc(F)c(F)c(F)c2)N(C(=O)C(=O)Nc2cncc(C(N)=O)c2)C1] | 477 | or/rel | b | bb | aaa | c* | aa* | A | B* |
| 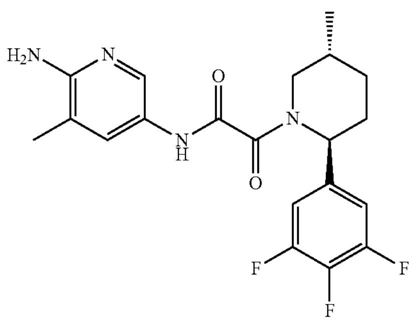 [SMILES: Cc1cc(NC(=O)C(=O)N2C[C@H](C)CC[C@H]2c2cc(F)c(F)c(F)c2)cnc1N] | 478 | or/rel | b | bb | aaa | c* | bb* | A | B* |
| 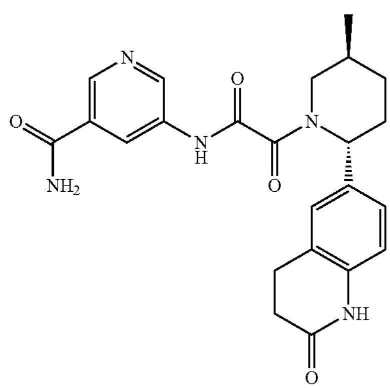 [SMILES: C[C@H]1CC[C@H](c2ccc3c(c2)CCC(=O)N3)N(C(=O)C(=O)Nc2cncc(C(N)=O)c2)C1] | 479 | or/rel | b | aa | aaa | c* | aa* | A | B* |
| 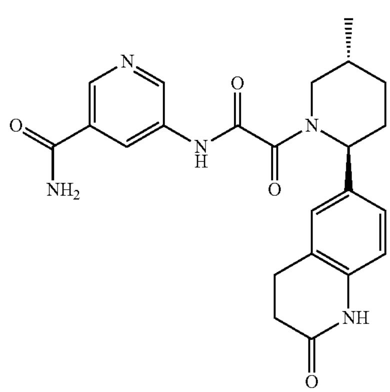 [SMILES: C[C@@H]1CC[C@@H](c2ccc3c(c2)CCC(=O)N3)N(C(=O)C(=O)Nc2cncc(C(N)=O)c2)C1] | 480 | or/rel | c | cc | ccc | c* | cc* | C | C* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 481 | or/rel | b | aa | aaa | b* | aa* | A | A* |
| | 482 | or/rel | b | bb | aaa | c* | aa* | A | A* |
| | 483 | or/rel | c | cc | ccc | c* | cc* | C | C* |
| | 484 | or/rel | b | bb | aaa | c* | aa* | A | B* |
| | 485 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 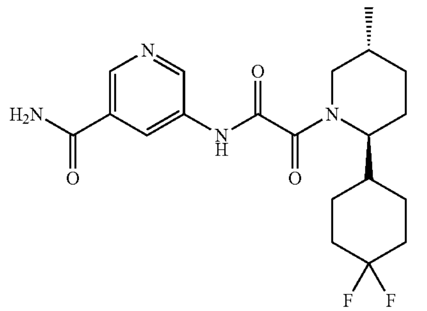 [SMILES: C[C@@H]1CC[C@@H](C2CCC(F)(F)CC2)N(C(=O)C(=O)Nc2cncc(C(N)=O)c2)C1] | 486 | or/rel | c | cc | ccc | c* | cc* | C | C* |
| 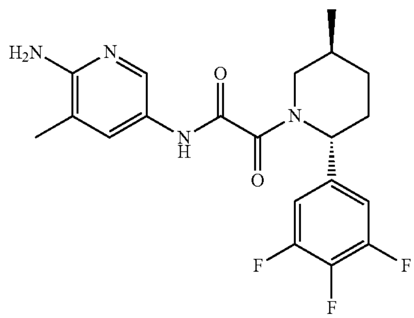 [SMILES: Cc1cc(NC(=O)C(=O)N2C[C@@H](C)CC[C@@H]2c2cc(F)c(F)c(F)c2)cnc1N] | 487 | or/rel | c | cc | ccc | c* | cc* | C | C* |
| 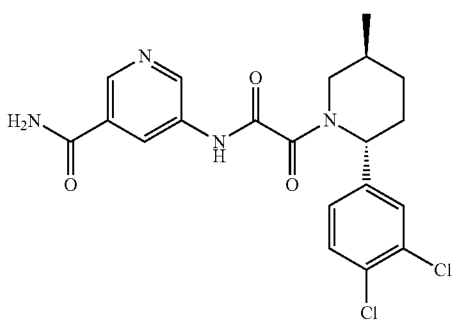 [SMILES: C[C@H]1CC[C@H](c2ccc(Cl)c(Cl)c2)N(C(=O)C(=O)Nc2cncc(C(N)=O)c2)C1] | 488 | or/rel | b | bb | aaa | c* | bb* | A | B* |
| 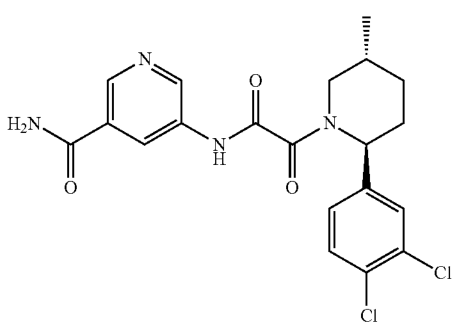 [SMILES: C[C@@H]1CC[C@@H](c2ccc(Cl)c(Cl)c2)N(C(=O)C(=O)Nc2cncc(C(N)=O)c2)C1] | 489 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure) | 490 | or/rel | c | cc | ccc | c* | cc* | C | C* |
| (structure) | 491 | or/rel | b | bb | aaa | c* | bb* | A | B* |
| (structure) | 492 | or/rel | b | aa | aaa | c* | aa* | A | B* |
| (structure) | 493 | or/rel | c | cc | ccc | c* | cc* | C | C* |
| (structure) | 494 | and/rac | c | bb | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 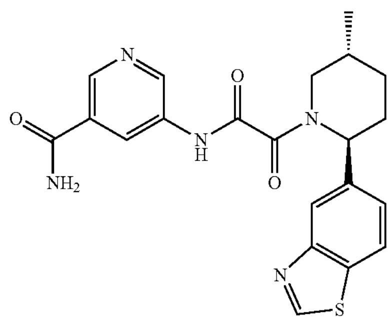 [SMILES: C[C@@H]1CC[C@@H](c2ccc3scnc3c2)N(C(=O)C(=O)Nc2cncc(C(N)=O)c2)C1] | 495 | and/rac | b | bb | aaa | c* | aa* | A | A* |
| 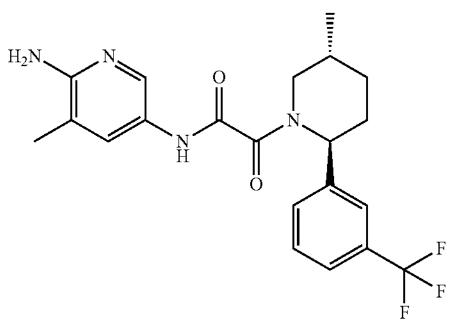 [SMILES: Cc1cc(NC(=O)C(=O)N2C[C@H](C)CC[C@H]2c2cccc(C(F)(F)F)c2)cnc1N] | 496 | or/rel | b | aa | aaa | c* | aa* | A | B* |
| 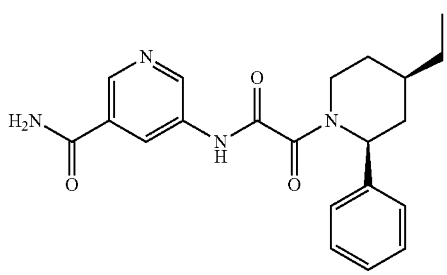 [SMILES: CC[C@@H]1CCN(C(=O)C(=O)Nc2cncc(C(N)=O)c2)[C@H](c2ccccc2)C1] | 497 | and/rac | b | bb | aaa | c* | bb* | A | B* |
| 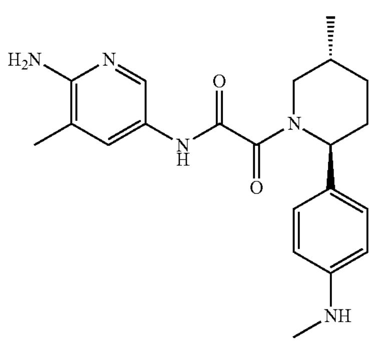 [SMILES: CNc1ccc([C@@H]2CC[C@@H](C)CN2C(=O)C(=O)Nc2cnc(N)c(C)c2)cc1] | 498 | and/rac | b | bb | bbb | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure) | 499 | or/rel | b | aa | aaa | c* | bb* | A | A* |
| (structure) | 500 | and/rac | b | bb | bbb | c* | bb* | A | B* |
| (structure) | 501 | and/rac | c | cc | bbb | c* | cc* | B | C* |
| (structure) | 502 | or/rel | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 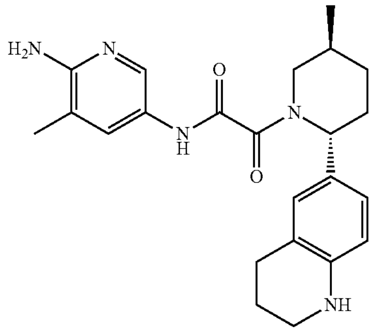 [SMILES: Cc1cc(NC(=O)C(=O)N2C[C@@H](C)CC[C@@H]2c2ccc3c(c2)CCCN3)cnc1N] | 503 | or/rel | c | cc | ccc | c* | cc* | C | C* |
| 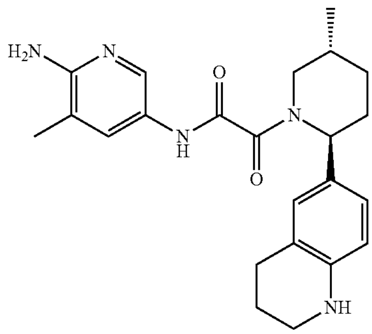 [SMILES: Cc1cc(NC(=O)C(=O)N2C[C@H](C)CC[C@H]2c2ccc3c(c2)CCCN3)cnc1N] | 504 | or/rel | b | aa | aaa | b* | aa* | A | A* |
| 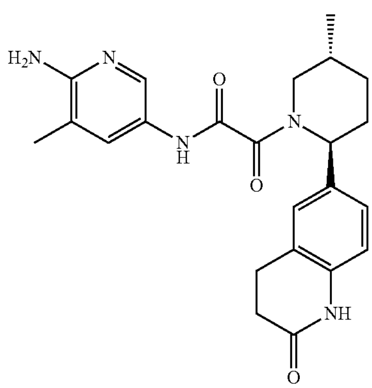 [SMILES: Cc1cc(NC(=O)C(=O)N2C[C@H](C)CC[C@H]2c2ccc3c(c2)CCC(=O)N3)cnc1N] | 505 | or/rel | c | bb | bbb | b* | aa* | A | A* |
| 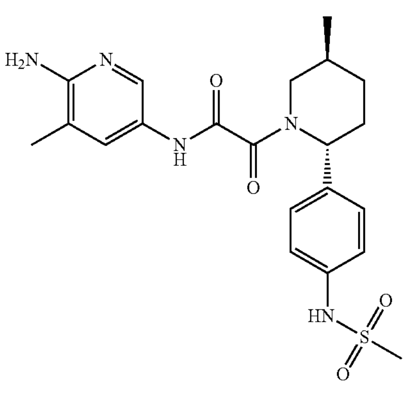 | 506 | or/rel | c | cc | ccc | c* | cc* | B | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 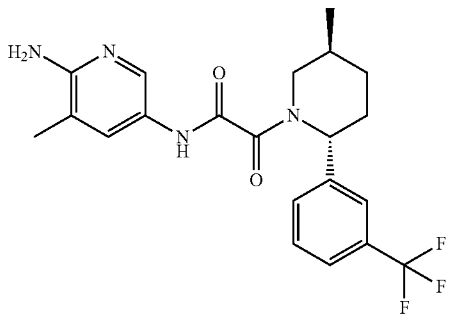 [SMILES: Cc1cc(NC(=O)C(=O)N2C[C@@H](C)CC[C@@H]2c2cccc(C(F)(F)F)c2)cnc1N] | 507 | or/rel | c | cc | ccc | c* | cc* | C | C* |
| 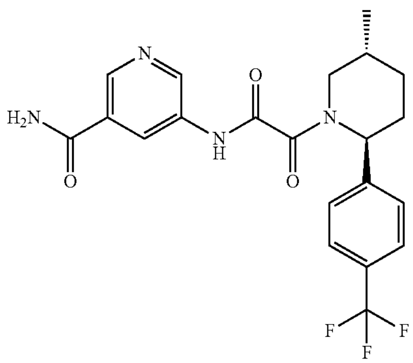 [SMILES: C[C@@H]1CC[C@@H](c2ccc(C(F)(F)F)cc2)N(C(=O)C(=O)Nc2cncc(C(N)=O)c2)C1] | 508 | or/rel | c | cc | ccc | c* | cc* | C | C* |
| 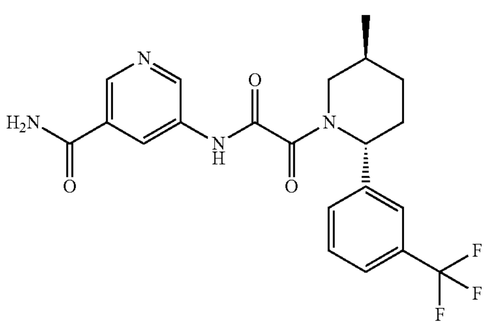 [SMILES: C[C@H]1CC[C@H](c2cccc(C(F)(F)F)c2)N(C(=O)C(=O)Nc2cncc(C(N)=O)c2)C1] | 509 | or/rel | b | bb | aaa | c* | aa* | A | B* |
| 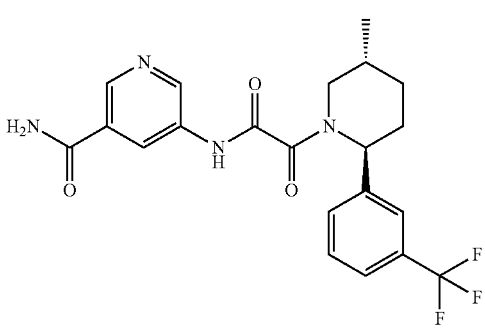 [SMILES: C[C@@H]1CC[C@@H](c2cccc(C(F)(F)F)c2)N(C(=O)C(=O)Nc2cncc(C(N)=O)c2)C1] | 510 | or/rel | c | cc | ccc | c* | cc* | C | C* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 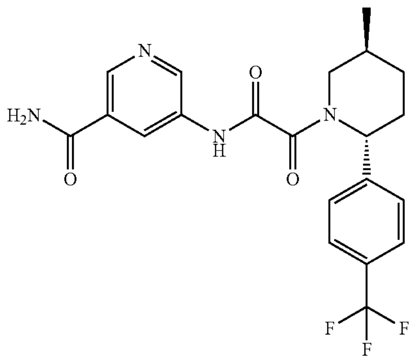 [SMILES: C[C@H]1CC[C@H](c2ccc(C(F)(F)F)cc2)N(C(=O)C(=O)Nc2cncc(C(N)=O)c2)C1] | 511 | or/rel | b | bb | aaa | c* | bb* | A | B* |
| 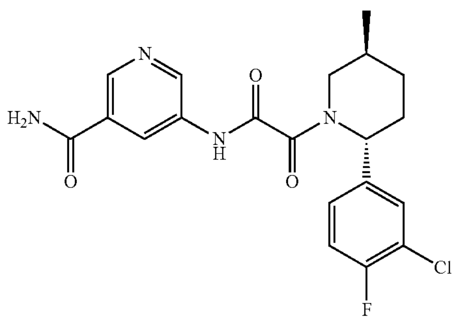 [SMILES: C[C@H]1CC[C@H](c2ccc(F)c(Cl)c2)N(C(=O)C(=O)Nc2cncc(C(N)=O)c2)C1] | 512 | or/rel | b | bb | aaa | c* | aa* | A | B* |
| 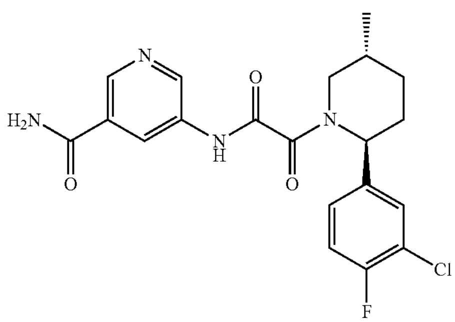 [SMILES: C[C@@H]1CC[C@@H](c2ccc(F)c(Cl)c2)N(C(=O)C(=O)Nc2cncc(C(N)=O)c2)C1] | 513 | or/rel | c | cc | ccc | c* | cc* | C | C* |
| 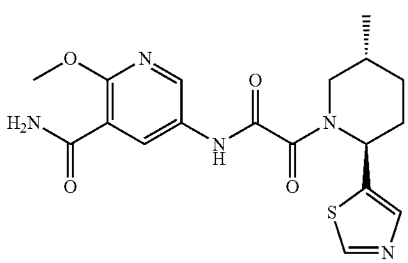 [SMILES: COc1ncc(NC(=O)C(=O)N2C[C@H](C)CC[C@H]2c2cncs2)cc1C(N)=O] | 514 | or/rel | c | cc | ccc | c* | cc* | C | C* |
| 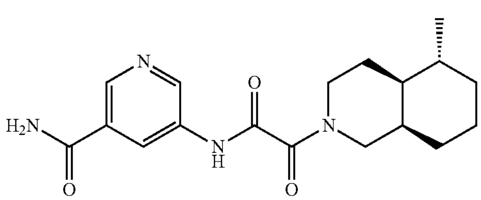 [SMILES: C[C@@H]1CCC[C@H]2CN(C(=O)C(=O)Nc3cncc(C(N)=O)c3)CC[C@H]21] | 515 | and/rac | b | cc | bbb | c* | cc* | B | C* |

TABLE 1-continued

Exemplary compounds of the invention and biological data

| Structure | Nr | Stereo | No Co-factor/ SAM rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|
| | 516 | or/rel | a | aa | aaa | c* | aa* | A | A* |
| | 517 | and/rac | c | cc | bbb | c* | cc* | C | C* |
| | 518 | or/rel | b | bb | aaa | c* | aa* | A | A* |
| | 519 | or/rel | c | cc | ccc | c* | cc* | C | C* |
| | 520 | or/rel | b | bb | bbb | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 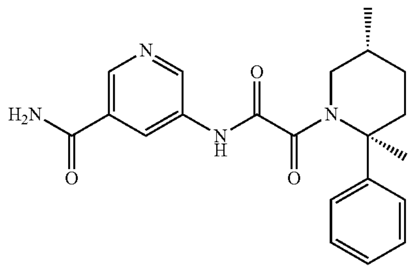 [SMILES: C[C@@H]1CC[C@@](C)(c2ccccc2)N(C(=O)C(=O)Nc2cncc(C(N)=O)c2)C1] | 521 | and/rac | c | cc | bbb | c* | cc* | B | C* |
| 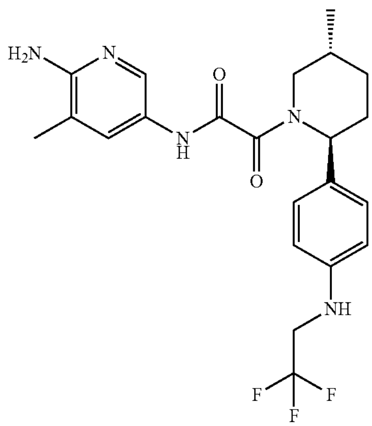 [SMILES: Cc1cc(NC(=O)C(=O)N2C[C@H](C)CC[C@H]2c2ccc(NCC(F)(F)F)cc2)cnc1N] | 522 | or/rel | b | bb | aaa | c* | bb* | A | B* |
| 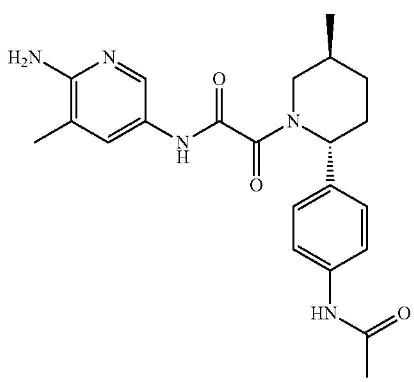 [SMILES: CC(=O)Nc1ccc([C@H]2CC[C@H](C)CN2C(=O)C(=O)Nc2cnc(N)c(C)c2)cc1] | 523 | or/rel | c | cc | ccc | c* | cc* | C | C* |
| 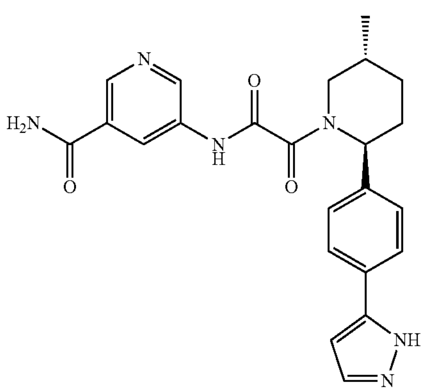 [SMILES: C[C@@H]1CC[C@@H](c2ccc(-c3ccn[nH]3)cc2)N(C(=O)C(=O)Nc2cncc(C(N)=O)c2)C1] | 524 | and/rac | b | bb | bbb | c* | bb* | A | B* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 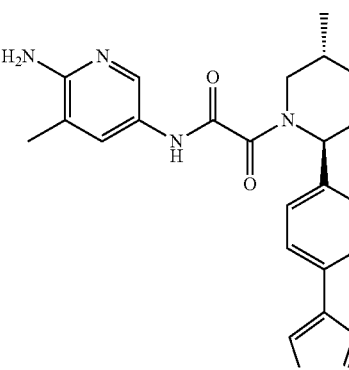 | 525 | and/rac | c | bb | bbb | b* | aa* | A | A* |
| 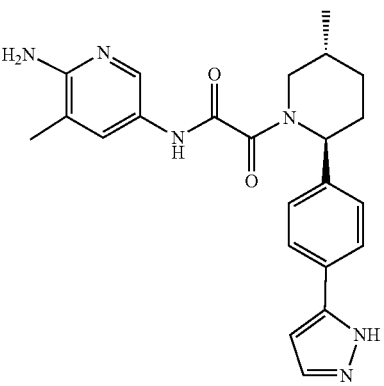 [SMILES: Cc1cc(NC(=O)C(=O)N2C[C@H](C)CC[C@H]2c2ccc(-c3ccn[nH]3)cc2)cnc1N] | 526 | and/rac | b | bb | bbb | b* | aa* | A | A* |
| 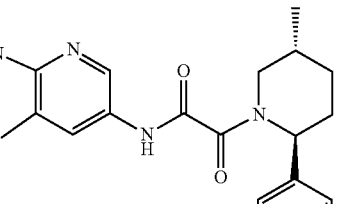 | 527 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 528 | or/rel | c | cc | ccc | c* | cc* | B | B* |
| | 529 | or/rel | c | cc | ccc | c* | cc* | C | C* |
| | 530 | or/rel | c | cc | ccc | c* | cc* | C | C* |
| | 531 | or/rel | b | cc | bbb | c* | cc* | B | C* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 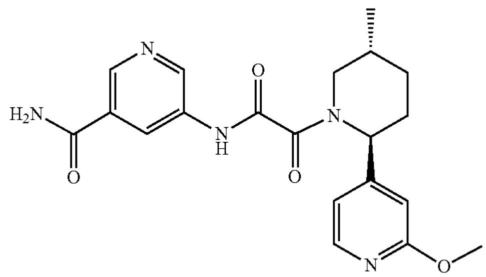 [SMILES: COc1cc([C@@H]2CC[C@@H](C)CN2C(=O)C(=O)Nc2cncc(C(N)=O)c2)ccn1] | 532 | or/rel | b | aa | aaa | c* | aa* | A | A* |
| 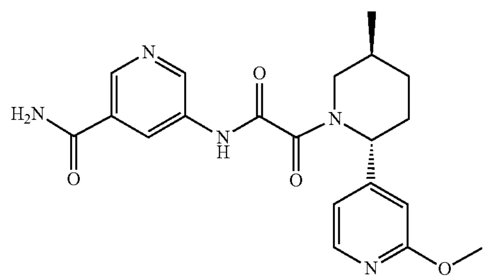 [SMILES: COc1cc([C@H]2CC[C@H](C)CN2C(=O)C(=O)Nc2cncc(C(N)=O)c2)ccn1] | 533 | or/rel | c | cc | ccc | c* | cc* | C | C* |
| 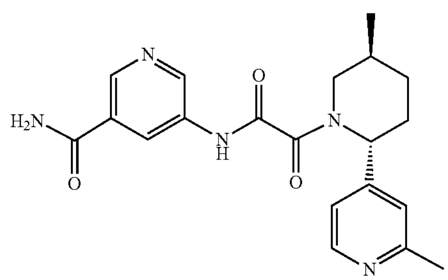 [SMILES: Cc1cc([C@H]2CC[C@H](C)CN2C(=O)C(=O)Nc2cncc(C(N)=O)c2)ccn1] | 534 | or/rel | b | bb | aaa | c* | bb* | A | B* |
| 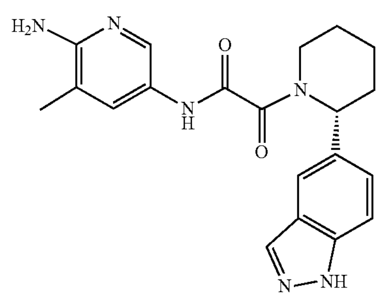 [SMILES: Cc1cc(NC(=O)C(=O)N2CCCC[C@@H]2c2ccc3[nH]ncc3c2)cnc1N] | 535 | or/rel | c | cc | ccc | c* | cc* | B | C* |
| 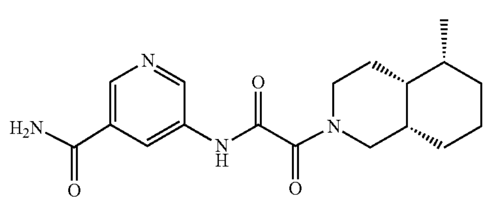 [SMILES: C[C@@H]1CCC[C@@H]2CN(C(=O)C(=O)Nc3cncc(C(N)=O)c3)CC[C@@H]21] | 536 | and/rac | b | cc | bbb | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 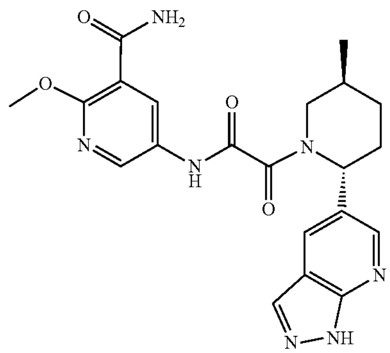 [SMILES: COc1ncc(NC(=O)C(=O)N2C[C@@H](C)CC[C@@H]2c2cnc3[nH]ncc3c2)cc1C(N)=O] | 537 | or/rel | c | cc | ccc | c* | cc* | C | C* |
| 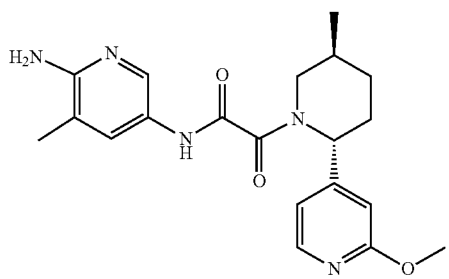 [SMILES: COc1cc([C@H]2CC[C@H](C)CN2C(=O)C(=O)Nc2cnc(N)c(C)c2)ccn1] | 538 | or/rel | c | cc | ccc | c* | cc* | B | C* |
| 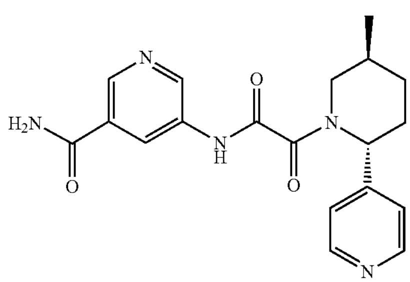 [SMILES: C[C@H]1CC[C@H](c2ccncc2)N(C(=O)C(=O)Nc2cncc(C(N)=O)c2)C1] | 539 | or/rel | b | bb | aaa | c* | aa* | A | B* |
| 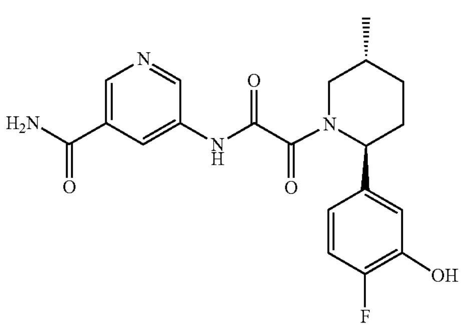 [SMILES: C[C@@H]1CC[C@@H](c2ccc(F)c(O)c2)N(C(=O)C(=O)Nc2cncc(C(N)=O)c2)C1] | 540 | and/rac | b | bb | aaa | c* | aa* | A | A* |
| 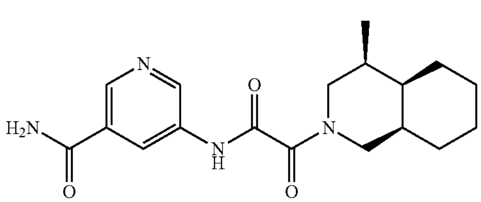 [SMILES: C[C@@H]1CN(C(=O)C(=O)Nc2cncc(C(N)=O)c2)C[C@@H]2CCCC[C@@H]21] | 541 | and/rac | b | cc | bbb | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 542 | and/rac | b | cc | bbb | c* | cc* | B | C* |
| | 543 | and/rac | b | bb | bbb | c* | bb* | A | B* |
| | 544 | or/rel | c | cc | ccc | c* | cc* | C | C* |
| | 545 | or/rel | b | aa | aaa | b* | aa* | B | A* |
| | 546 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 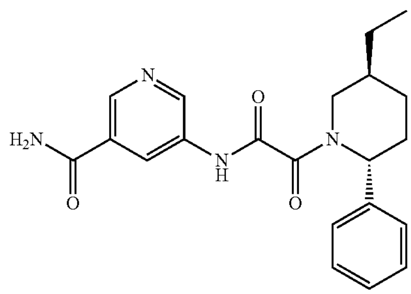 [SMILES: CC[C@H]1CC[C@H](c2ccccc2)N(C(=O)C(=O)Nc2cncc(C(N)=O)c2)C1] | 547 | or/rel | b | bb | aaa | c* | aa* | A | B* |
| 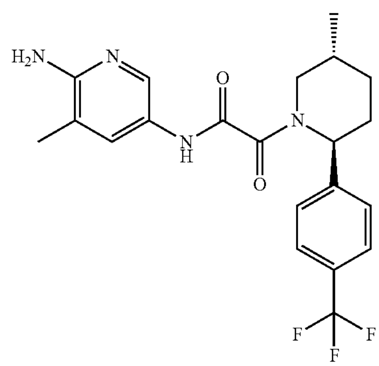 [SMILES: Cc1cc(NC(=O)C(=O)N2C[C@H](C)CC[C@H]2c2ccc(C(F)(F)F)cc2)cnc1N] | 548 | or/rel | b | bb | aaa | a* | aa* | C | A* |
| 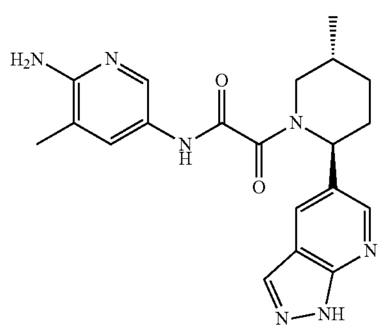 [SMILES: Cc1cc(NC(=O)C(=O)N2C[C@H](C)CC[C@H]2c2cnc3[nH]ncc3c2)cnc1N] | 549 | or/rel | b | bb | aaa | b* | aa* | A | B* |
| 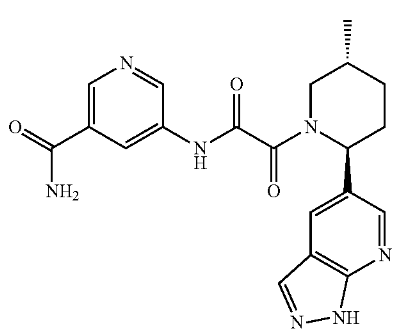 [SMILES: C[C@@H]1CC[C@@H](c2cnc3[nH]ncc3c2)N(C(=O)C(=O)Nc2cncc(C(N)=O)c2)C1] | 550 | or/rel | c | cc | ccc | c* | cc* | C | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 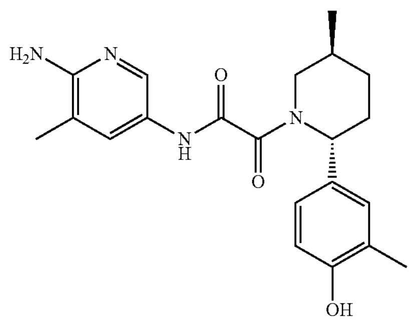 | 551 | or/rel | c | cc | ccc | c* | cc* | C | C* |
| 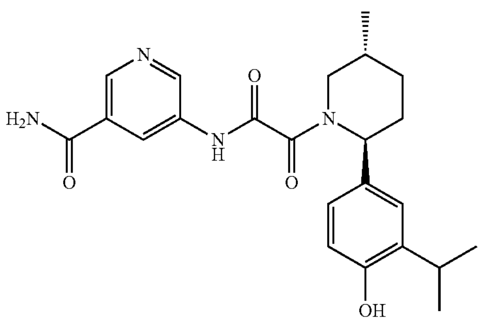 [SMILES: CC(C)c1cc([C@@H]2CC[C@@H](C)CN2C(=O)C(=O)Nc2cncc(C(N)=O)c2)ccc1O] | 552 | and/rac | b | bb | aaa | c* | aa* | A | A* |
| 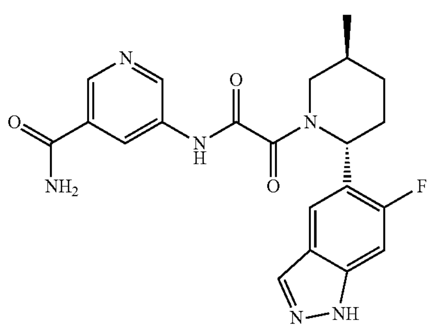 [SMILES: C[C@H]1CC[C@H](c2cc3cn[nH]c3cc2F)N(C(=O)C(=O)Nc2cncc(C(N)=O)c2)C1] | 553 | or/rel | b | bb | aaa | c* | bb* | A | B* |
| 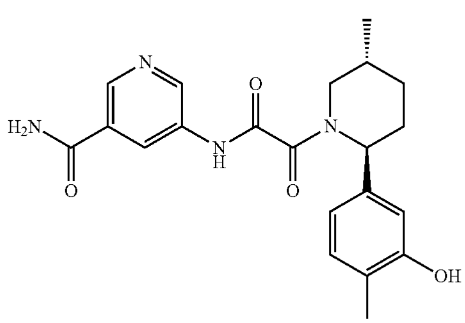 [SMILES: Cc1ccc([C@@H]2CC[C@@H](C)CN2C(=O)C(=O)Nc2cncc(C(N)=O)c2)cc1O] | 554 | and/rac | b | bb | aaa | c* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 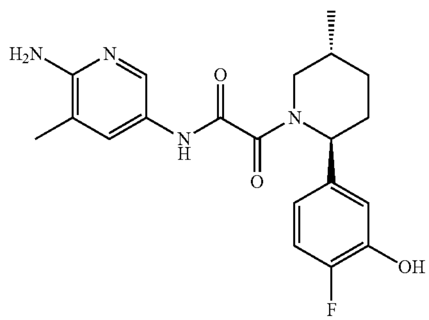 [SMILES: Cc1cc(NC(=O)C(=O)N2C[C@H](C)CC[C@H]2c2ccc(F)c(O)c2)cnc1N] | 555 | and/rac | b | bb | aaa | b* | aa* | A | A* |
| 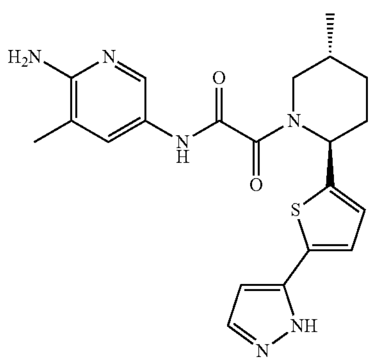 [SMILES: Cc1cc(NC(=O)C(=O)N2C[C@H](C)CC[C@H]2c2ccc(-c3ccn[nH]3)s2)cnc1N] | 556 | and/rac | b | bb | bbb | b* | aa* | A | A* |
| 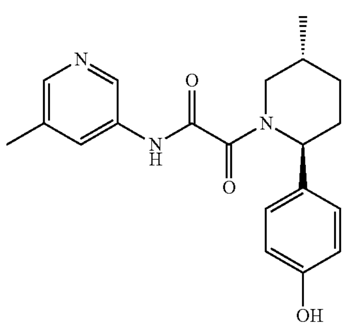 [SMILES: Cc1cncc(NC(=O)C(=O)N2C[C@H](C)CC[C@H]2c2ccc(O)cc2)c1] | 557 | and/rac | b | bb | bbb | c* | bb* | A | C* |
| 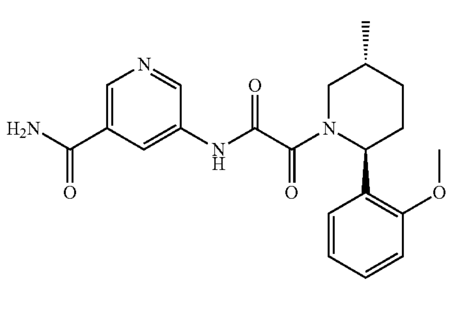 [SMILES: COc1ccccc1[C@@H]1CC[C@@H](C)CN1C(=O)C(=O)Nc1cncc(C(N)=O)c1] | 558 | and/rac | b | cc | bbb | c* | bb* | A | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 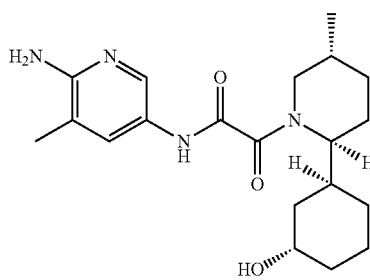 | 559 | rel | b | bb | aaa | c* | bb* | A | B* |
| 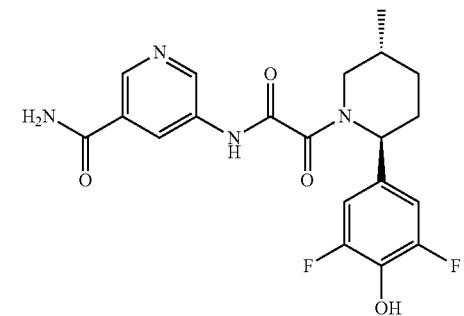 [SMILES: C[C@@H]1CC[C@@H](c2cc(F)c(O)c(F)c2)N(C(=O)C(=O)Nc2cncc(C(N)=O)c2)C1] | 560 | and/rac | b | bb | bbb | c* | bb* | A | C* |
| 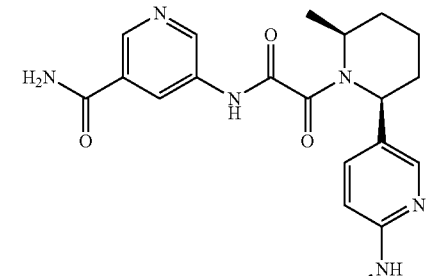 | 561 | and/rac | b | bb | bbb | c* | bb* | A | C* |
| 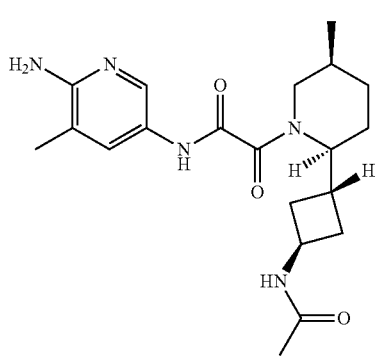 [SMILES: CC(=O)N[C@H]1C[C@H]([C@@H]2CC[C@H](C)CN2C(=O)C(=O)Nc2cnc(N)c(C)c2)C1] | 562 | or/rel | c | cc | ccc | c* | cc* | C | C* |

TABLE 1-continued

Exemplary compounds of the invention and biological data

| Structure | Nr | Stereo | No Co-factor/ SAM rel IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 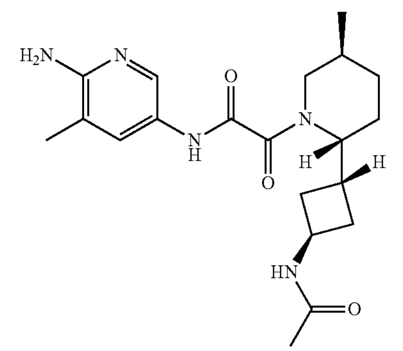 [SMILES: CC(=O)N[C@H]1C[C@H]([C@H]2CC[C@H](C)CN2C(=O)C(=O)Nc2cnc(N)c(C)c2)C1] | 563 | or/rel | c | cc | ccc | c* | cc* | C | C* |
| 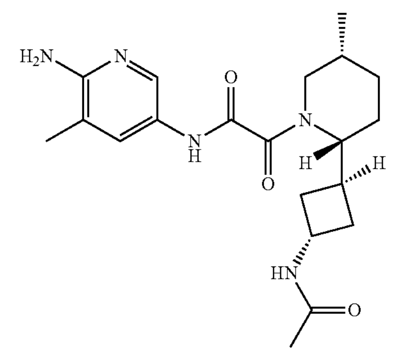 [SMILES: CC(=O)N[C@H]1C[C@H]([C@H]2CC[C@@H](C)CN2C(=O)C(=O)Nc2cnc(N)c(C)c2)C1] | 564 | or/rel | b | cc | bbb | c* | cc* | B | C* |
| 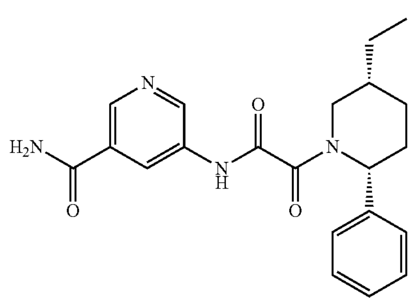 [SMILES: CC[C@@H]1CC[C@H](c2ccccc2)N(C(=O)C(=O)Nc2cncc(C(N)=O)c2)C1] | 565 | or/rel | b | cc | bbb | c* | bb* | A | C* |
| 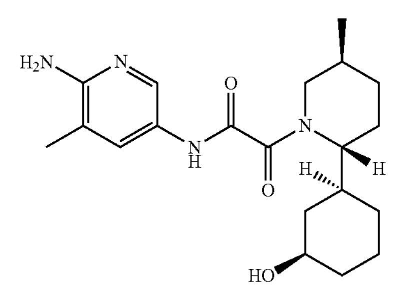 [SMILES: Cc1cc(NC(=O)C(=O)N2C[C@@H](C)CC[C@@H]2[C@H]2CCC[C@@H](O)C2)cnc1N] | 566 | or/rel | c | bb | bbb | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 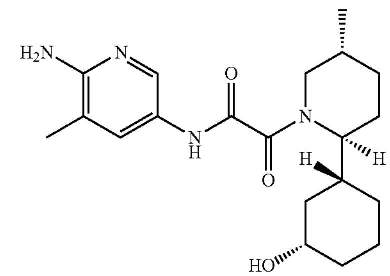 [SMILES: Cc1cc(NC(=O)C(=O)N2C[C@H](C)CC[C@H]2[C@@H]2CCC[C@H](O)C2)cnc1N] | 567 | or/rel | c | cc | ccc | c* | cc* | C | C* |
| 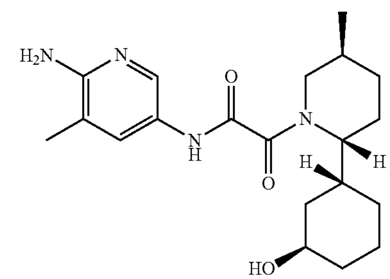 [SMILES: Cc1cc(NC(=O)C(=O)N2C[C@@H](C)CC[C@@H]2[C@@H]2CCC[C@@H](O)C2)cnc1N] | 568 | or/rel | c | cc | ccc | c* | cc* | C | C* |
| 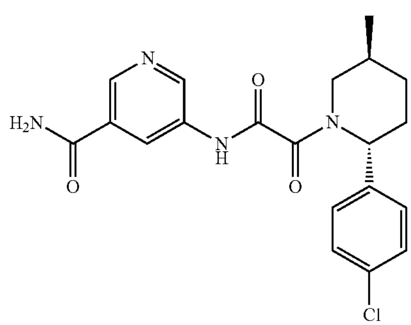 | 569 | or/rel | c | cc | ccc | c* | cc* | C | C* |
| 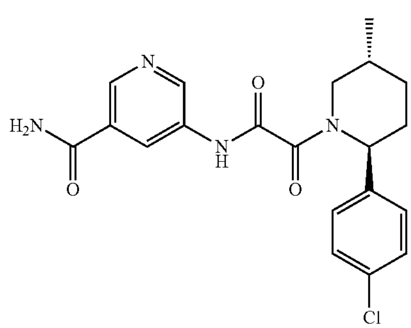 | 570 | or/rel | b | bb | aaa | c* | aa* | A | B* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 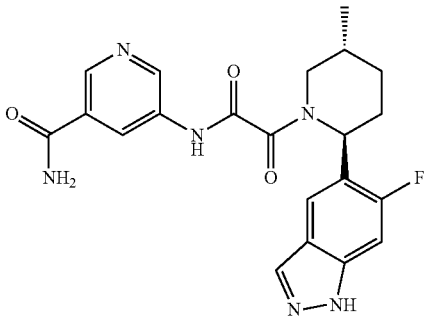 [SMILES: C[C@@H]1CC[C@@H](c2cc3cn[nH]c3cc2F)N(C(=O)C(=O)Nc2cncc(C(N)=O)c2)C1] | 571 | or/rel | c | cc | ccc | c* | cc* | C | C* |
| 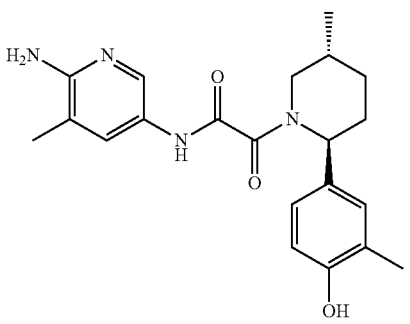 | 572 | or/rel | a | bb | bbb | a* | aa* | A | A* |
|  | 573 | or/rel | c | cc | ccc | c* | cc* | C | C* |
| 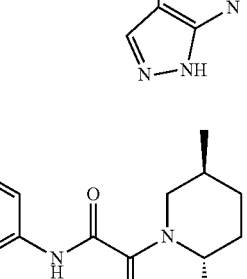 | 574 | or/rel | b | bb | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 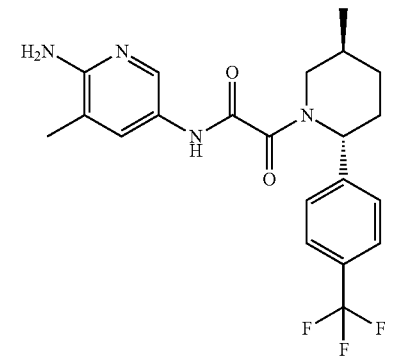 [SMILES: Cc1cc(NC(=O)C(=O)N2C[C@@H](C)CC[C@@H]2c2ccc(C(F)(F)F)cc2)cnc1N] | 575 | or/rel | c | cc | ccc | c* | cc* | C | C* |
| 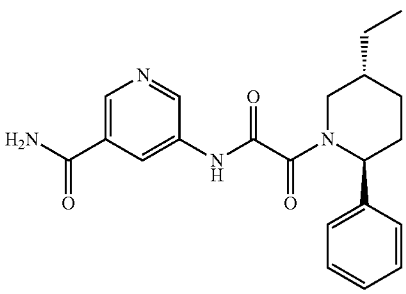 [SMILES: CC[C@@H]1CC[C@@H](c2ccccc2)N(C(=O)C(=O)Nc2cncc(C(N)=O)c2)C1] | 576 | or/rel | c | cc | ccc | c* | cc* | C | C* |
| 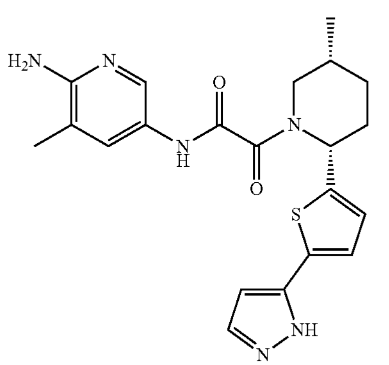 [SMILES: Cc1cc(NC(=O)C(=O)N2C[C@H](C)CC[C@@H]2c2ccc(-c3ccn[nH]3)s2)cnc1N] | 577 | and/rac | | | | c* | cc* | B | B* |
| 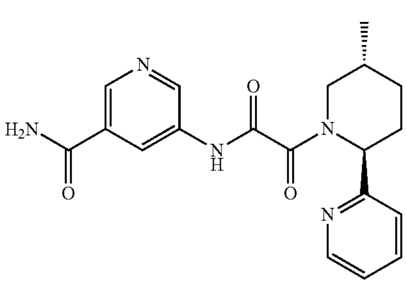 [SMILES: C[C@@H]1CC[C@@H](c2ccccn2)N(C(=O)C(=O)Nc2cncc(C(N)=O)c2)C1] | 578 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure with aminopyridine, ethyl, indazole) | 579 | or/rel | c | cc | ccc | c* | cc* | B | C* |
| (structure with aminopyridine, methyl, methylphenol) | 580 | and/rac | b | bb | bbb | b* | aa* | A | A* |
| (structure with aminopyridine, methyl, isoindolinone) | 581 | or/rel | a | bb | bbb | b* | aa* | A | B* |
| (structure with aminopyridine, methyl, isoindolinone) | 582 | and/rac | b | bb | bbb | b* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 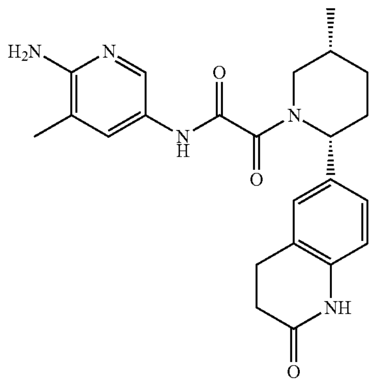 [SMILES: Cc1cc(NC(=O)C(=O)N2C[C@H](C)CC[C@@H]2c2ccc3c(c2)CCC(=O)N3)cnc1N] | 583 | and/rac | | | | a* | aa* | B | A* |
| 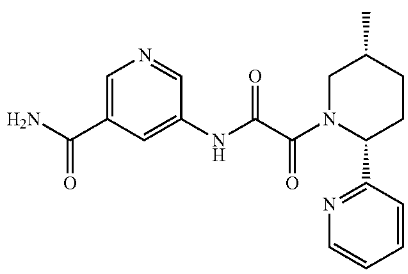 [SMILES: C[C@@H]1CC[C@H](c2ccccn2)N(C(=O)C(=O)Nc2cncc(C(N)=O)c2)C1] | 584 | and/rac | c | cc | bbb | c* | bb* | A | C* |
| 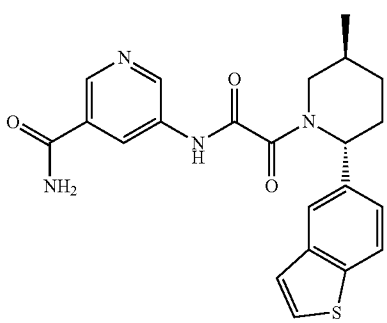 [SMILES: C[C@H]1CC[C@H](c2ccc3sccc3c2)N(C(=O)C(=O)Nc2cncc(C(N)=O)c2)C1] | 585 | or/rel | a | aa | aaa | b* | aa* | A | A* |
| 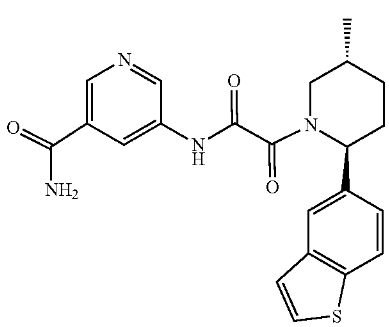 [SMILES: C[C@@H]1CC[C@@H](c2ccc3sccc3c2)N(C(=O)C(=O)Nc2cncc(C(N)=O)c2)C1] | 586 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 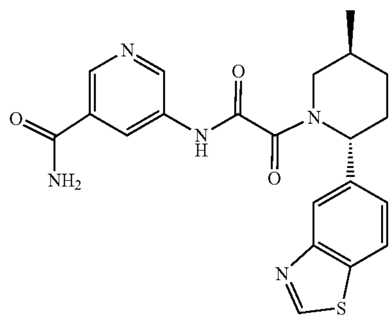 [SMILES: C[C@H]1CC[C@H](c2ccc3scnc3c2)N(C(=O)C(=O)Nc2cncc(C(N)=O)c2)C1] | 587 | or/rel | b | aa | aaa | b* | aa* | A | A* |
| 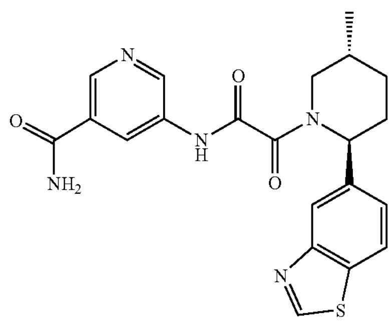 [SMILES: C[C@@H]1CC[C@@H](c2ccc3scnc3c2)N(C(=O)C(=O)Nc2cncc(C(N)=O)c2)C1] | 588 | or/rel | c | cc | ccc | c* | cc* | C | C* |
| 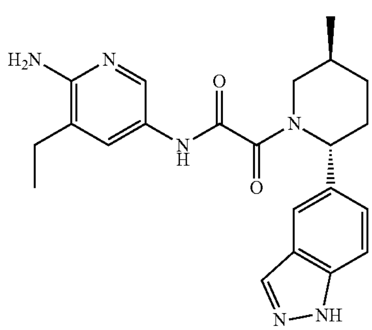 [SMILES: CCc1cc(NC(=O)C(=O)N2C[C@@H](C)CC[C@@H]2c2ccc3[nH]ncc3c2)cnc1N] | 589 | or/rel | a | aa | aaa | b* | aa* | A | A* |
| 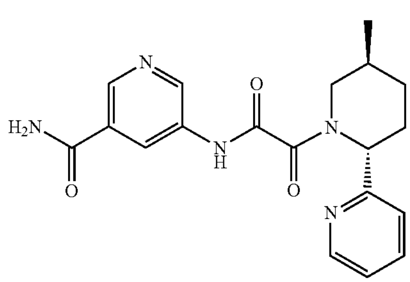 [SMILES: C[C@H]1CC[C@H](c2ccccn2)N(C(=O)C(=O)Nc2cncc(C(N)=O)c2)C1] | 590 | or/rel | a | bb | aaa | c* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 591 | or/rel | c | cc | ccc | c* | cc* | C | C* |
| | 592 | or/rel | b | aa | bbb | b* | aa* | A | B* |
| | 593 | or/rel | c | cc | ccc | c* | cc* | B | C* |
| | 594 | or/rel | | | | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| (structure 595) | 595 | and/rac | b | bb | bbb | c* | aa* | A | B* |
| (structure 596) | 596 | or/rel | b | aa | aaa | b* | aa* | A | A* |
| (structure 597) | 597 | or/rel | c | cc | ccc | c* | cc* | B | C* |
| (structure 598) | 598 | or/rel | a | bb | aaa | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 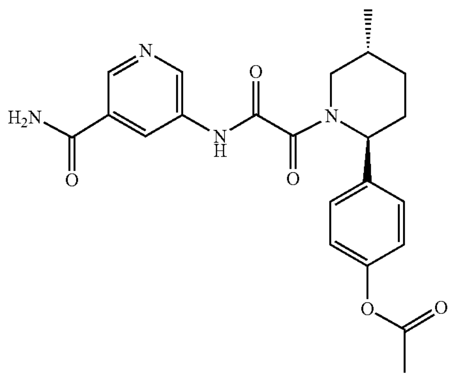 [SMILES: CC(=O)Oc1ccc([C@@H]2CC[C@@H](C)CN2C(=O)C(=O)Nc2cncc(C(N)=O)c2)cc1] | 599 | or/rel | c | cc | ccc | c* | cc* | B | C* |
| 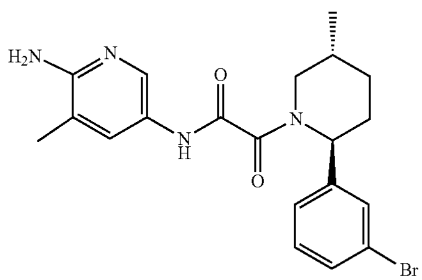 [SMILES: Cc1cc(NC(=O)C(=O)N2C[C@H](C)CC[C@H]2c2cccc(Br)c2)cnc1N] | 600 | and/rac | b | bb | bbb | b* | aa* | A | A* |
| 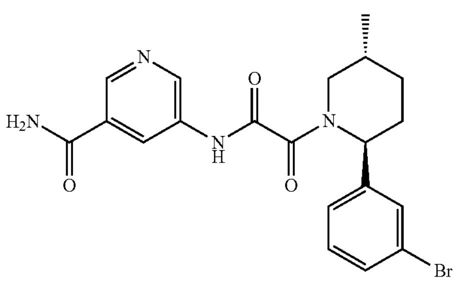 [SMILES: C[C@@H]1CC[C@@H](c2cccc(Br)c2)N(C(=O)C(=O)Nc2cncc(C(N)=O)c2)C1] | 601 | and/rac | b | bb | bbb | c* | aa* | A | B* |
| 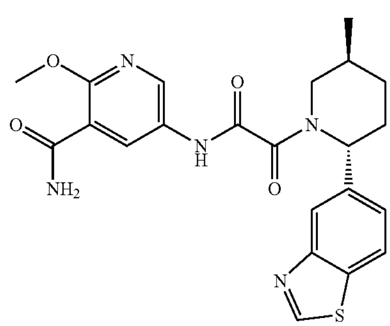 [SMILES: COc1ncc(NC(=O)C(=O)N2C[C@@H](C)CC[C@@H]2c2ccc3scnc3c2)cc1C(N)=O] | 602 | or/rel | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 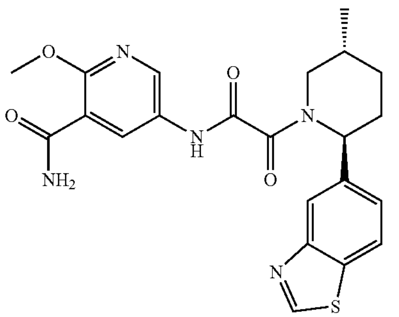 [SMILES: COc1ncc(NC(=O)C(=O)N2C[C@H](C)CC[C@H]2c2ccc3scnc3c2)cc1C(N)=O] | 603 | or/rel | c | cc | ccc | c* | cc* | C | C* |
| 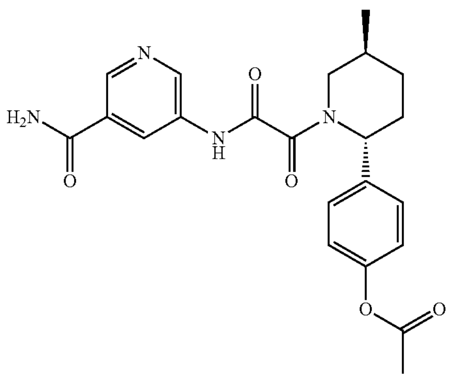 [SMILES: CC(=O)Oc1ccc([C@H]2CC[C@H](C)CN2C(=O)C(=O)Nc2cncc(C(N)=O)c2)cc1] | 604 | or/rel | a | bb | bbb | b* | aa* | A | A* |
| 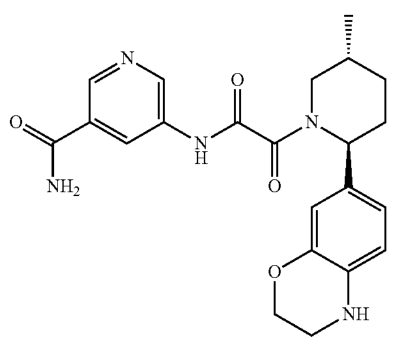 [SMILES: C[C@@H]1CC[C@@H](c2ccc3c(c2)OCCN3)N(C(=O)C(=O)Nc2cncc(C(N)=O)c2)C1] | 605 | or/rel | c | cc | ccc | c* | cc* | B | C* |
| 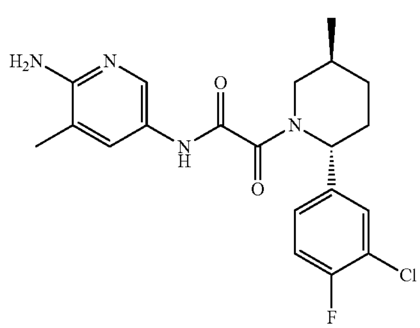 [SMILES: Cc1cc(NC(=O)C(=O)N2C[C@@H](C)CC[C@@H]2c2ccc(F)c(Cl)c2)cnc1N] | 606 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 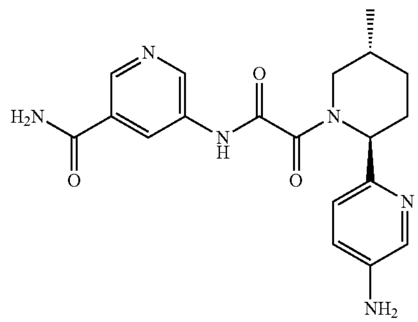 [SMILES: C[C@@H]1CC[C@@H](c2ccc(N)cn2)N(C(=O)C(=O)Nc2cncc(C(N)=O)c2)C1] | 607 | or/rel | b | cc | bbb | c* | cc* | B | C* |
| 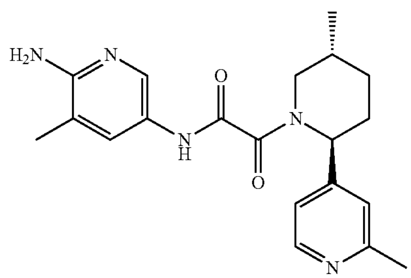 [SMILES: Cc1cc([C@@H]2CC[C@@H](C)CN2C(=O)C(=O)Nc2cnc(N)c(C)c2)ccn1] | 608 | or/rel | a | aa | aaa | b* | aa* | A | A* |
| 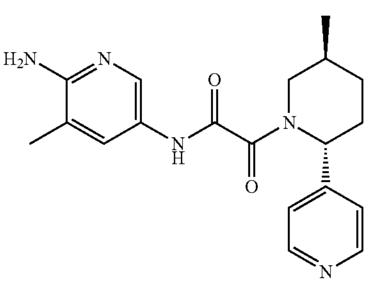 [SMILES: Cc1cc(NC(=O)C(=O)N2C[C@@H](C)CC[C@@H]2c2ccncc2)cnc1N] | 609 | or/rel | c | cc | ccc | | cc* | C | C* |
| 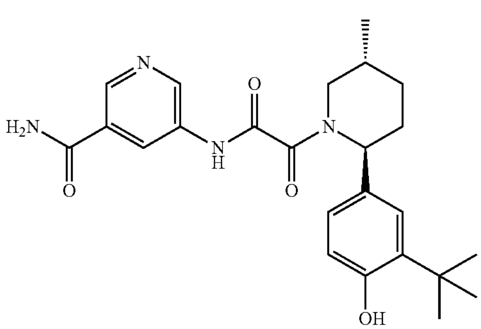 [SMILES: C[C@@H]1CC[C@@H](c2ccc(O)c(C(C)(C)C)c2)N(C(=O)C(=O)Nc2cncc(C(N)=O)c2)C1] | 610 | and/rac | b | bb | bbb | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 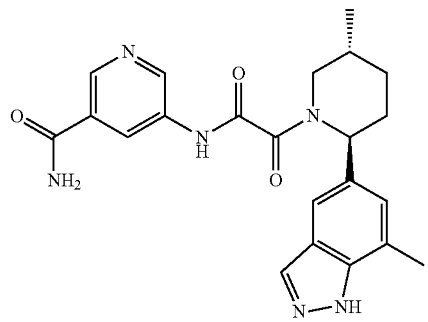 [SMILES: Cc1cc([C@@H]2CC[C@@H](C)CN2C(=O)C(=O)Nc2cncc(C(N)=O)c2)cc2cn[nH]c12] | 611 | or/rel | | | | c* | cc* | C | C* |
| 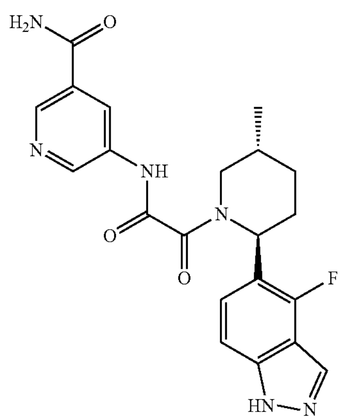 [SMILES: C[C@@H]1CC[C@@H](c2ccc3[nH]ncc3c2F)N(C(=O)C(=O)Nc2cncc(C(N)=O)c2)C1] | 612 | or/rel | b | bb | aaa | c* | aa* | A | B* |
| 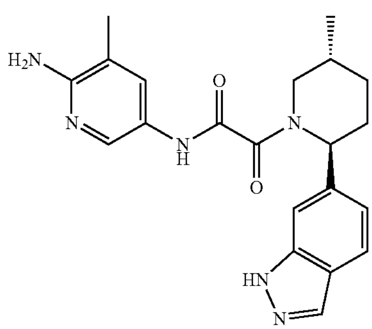 [SMILES: Cc1cc(NC(=O)C(=O)N2C[C@H](C)CC[C@H]2c2ccc3cn[nH]c3c2)cnc1N] | 613 | or/rel | | | | c* | cc* | C | C* |
| 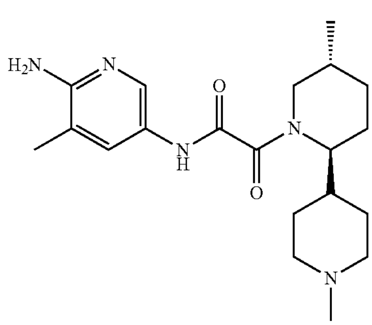 [SMILES: Cc1cc(NC(=O)C(=O)N2C[C@H](C)CC[C@H]2C2CCN(C)CC2)cnc1N] | 614 | and/rac | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 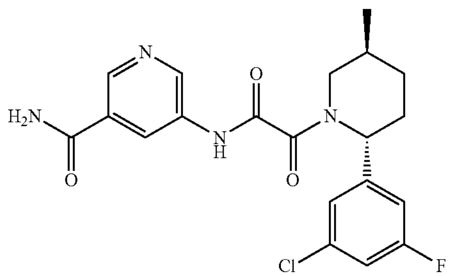 [SMILES: C[C@H]1CC[C@H](c2cc(F)cc(Cl)c2)N(C(=O)C(=O)Nc2cncc(C(N)=O)c2)C1] | 615 | or/rel | b | bb | aaa | c* | aa* | A | B* |
| 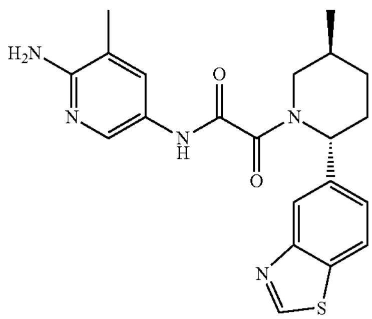 [SMILES: Cc1cc(NC(=O)C(=O)N2C[C@@H](C)CC[C@@H]2c2ccc3scnc3c2)cnc1N] | 616 | abs | a | aa | aaa | b* | aa* | A | A* |
| 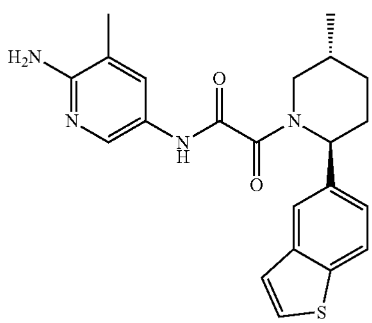 [SMILES: Cc1cc(NC(=O)C(=O)N2C[C@H](C)CC[C@H]2c2ccc3sccc3c2)cnc1N] | 617 | or/rel | c | cc | ccc | c* | bb* | A | C* |
| 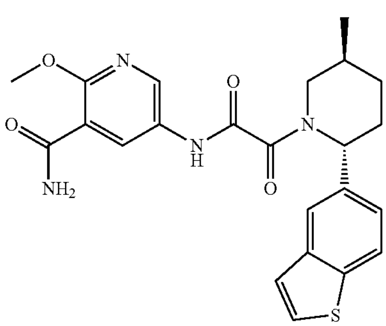 [SMILES: COc1ncc(NC(=O)C(=O)N2C[C@@H](C)CC[C@@H]2c2ccc3sccc3c2)cc1C(N)=O] | 618 | or/rel | a | aa | aaa | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 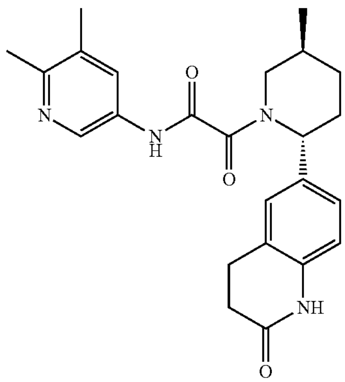 [SMILES: Cc1cc(NC(=O)C(=O)N2C[C@@H](C)CC[C@@H]2c2ccc3c(c2)CCC(=O)N3)cnc1C] | 619 | or/rel | c | cc | ccc | c* | bb* | A | B* |
| 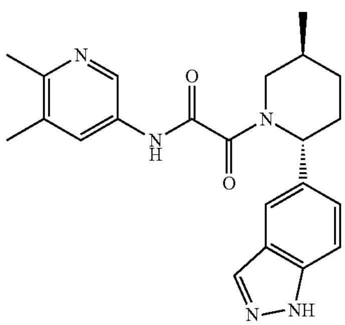 [SMILES: Cc1cc(NC(=O)C(=O)N2C[C@@H](C)CC[C@@H]2c2ccc3[nH]ncc3c2)cnc1C] | 620 | or/rel | b | aa | aaa | b* | aa* | A | A* |
| 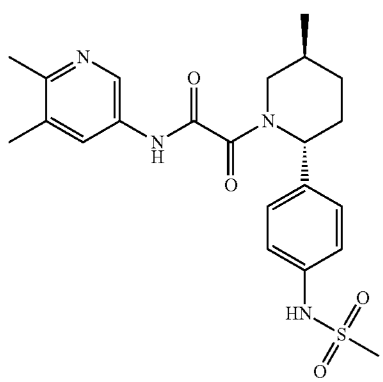 | 621 | or/rel | b | aa | aaa | b* | aa* | A | B* |
| 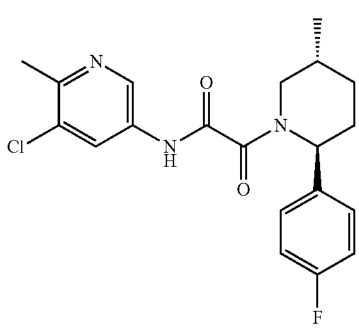 [SMILES: Cc1ncc(NC(=O)C(=O)N2C[C@H](C)CC[C@H]2c2ccc(F)cc2)cc1Cl] | 622 | and/rac | b | bb | bbb | c* | cc* | B | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| (structure) | 623 | and/rac | b | bb | bbb | c* | bb* | A | C* |
| (structure) | 624 | or/rel | c | cc | ccc | c* | cc* | B | C* |
| (structure) | 625 | or/rel | b | cc | bbb | c* | bb* | A | C* |
| (structure) | 626 | or/rel | b | bb | bbb | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 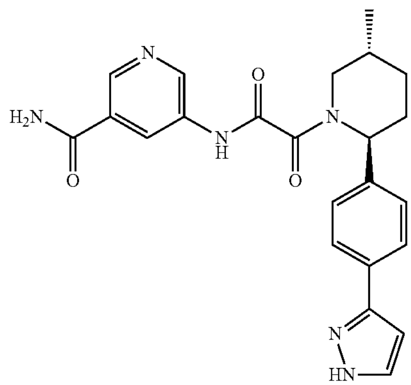 [SMILES: C[C@@H]1CC[C@@H](c2ccc(-c3cc[nH]n3)cc2)N(C(=O)C(=O)Nc2cncc(C(N)=O)c2)C1] | 627 | or/rel | c | cc | ccc | c* | bb* | A | C* |
| 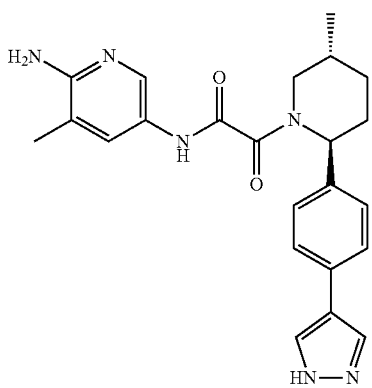 [SMILES: Cc1cc(NC(=O)C(=O)N2C[C@H](C)CC[C@H]2c2ccc(-c3cn[nH]c3)cc2)cnc1N] | 628 | or/rel | b | aa | bbb | b* | aa* | A | A* |
| 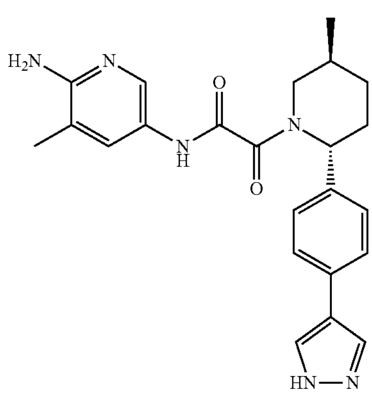 [SMILES: Cc1cc(NC(=O)C(=O)N2C[C@@H](C)CC[C@@H]2c2ccc(-c3cn[nH]c3)cc2)cnc1N] | 629 | or/rel | c | cc | ccc | c* | cc* | B | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 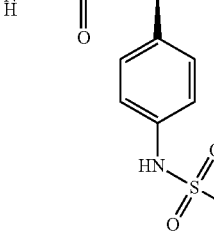 | 630 | or/rel | c | cc | ccc | c* | bb* | A | C* |
| 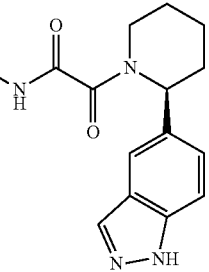 | 631 | or/rel | c | cc | ccc | c* | cc* | C | C* |
| 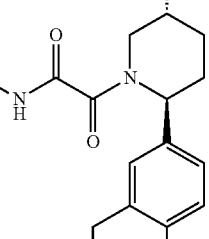 | 632 | or/rel | b | aa | aaa | b* | aa* | A | A* |
| 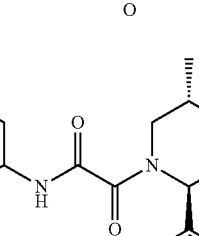 | 633 | or/rel | | | | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 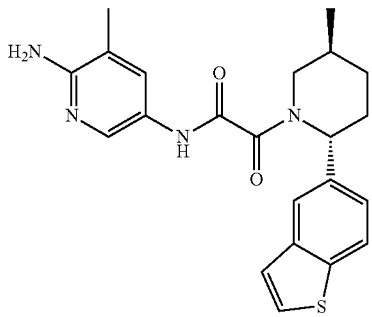 [SMILES: Cc1cc(NC(=O)C(=O)N2C[C@@H](C)CC[C@@H]2c2ccc3sccc3c2)cnc1N] | 634 | or/rel | a | aa | aaa | b* | aa* | A | A* |
| 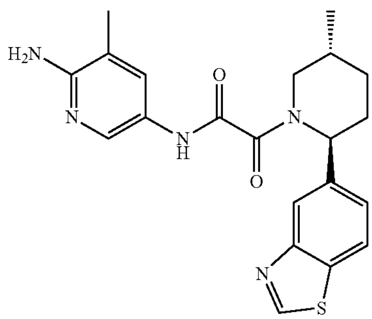 [SMILES: Cc1cc(NC(=O)C(=O)N2C[C@H](C)CC[C@H]2c2ccc3scnc3c2)cnc1N] | 635 | or/rel | c | cc | ccc | c* | cc* | C | C* |
| 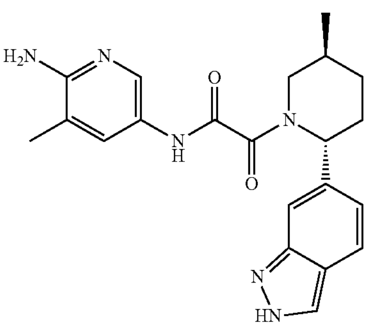 [SMILES: Cc1cc(NC(=O)C(=O)N2C[C@@H](C)CC[C@@H]2c2ccc3c[nH]nc3c2)cnc1N] | 636 | and/rac | | | | b* | aa* | A | A* |
| 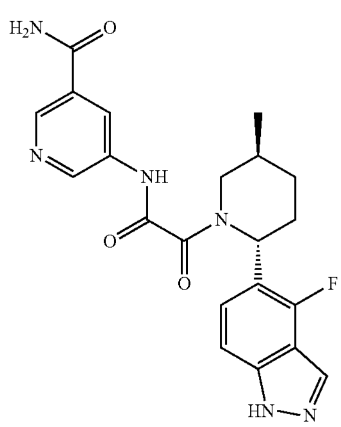 [SMILES: C[C@H]1CC[C@H](c2ccc3[nH]ncc3c2F)N(C(=O)C(=O)Nc2cncc(C(N)=O)c2)C1] | 637 | or/rel | c | cc | ccc | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 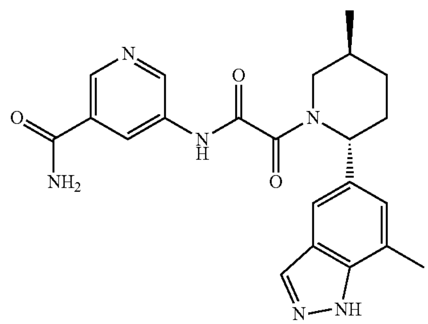 [SMILES: Cc1cc([C@H]2CC[C@H](C)CN2C(=O)C(=O)Nc2cncc(C(N)=O)c2)cc2cn[nH]c12] | 638 | or/rel | | | | c* | aa* | A | B* |
| 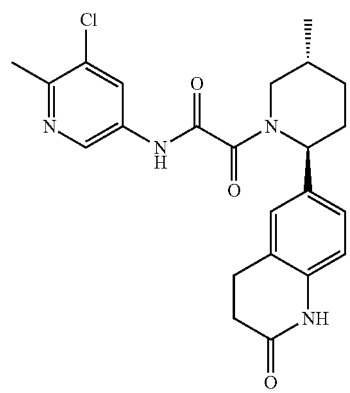 [SMILES: Cc1ncc(NC(=O)C(=O)N2C[C@H](C)CC[C@H]2c2ccc3c(c2)CCC(=O)N3)cc1Cl] | 639 | and/rac | b | bb | bbb | c* | aa* | A | B* |
| 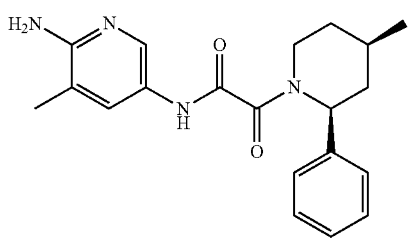 [SMILES: Cc1cc(NC(=O)C(=O)N2CC[C@@H](C)C[C@H]2c2ccccc2)cnc1N] | 640 | and/rac | b | bb | bbb | c* | bb* | A | B* |
| 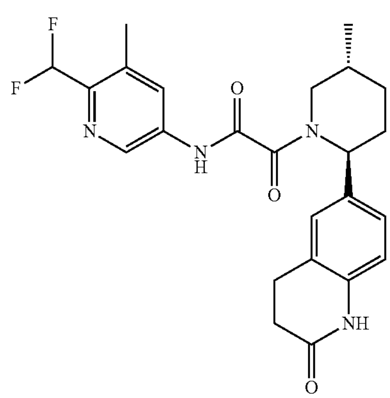 [SMILES: Cc1cc(NC(=O)C(=O)N2C[C@H](C)CC[C@H]2c2ccc3c(c2)CCC(=O)N3)cnc1C(F)F] | 641 | and/rac | b | bb | bbb | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 642 | and/rac | b | bb | bbb | c* | aa* | A | A* |
| | 643 | and/rac | b | bb | bbb | c* | bb* | C | B* |
| | 644 | and/rac | b | bb | bbb | b* | aa* | A | A* |
| | 645 | or/rel | c | cc | ccc | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via- bility |
|---|---|---|---|---|---|---|---|---|---|
| 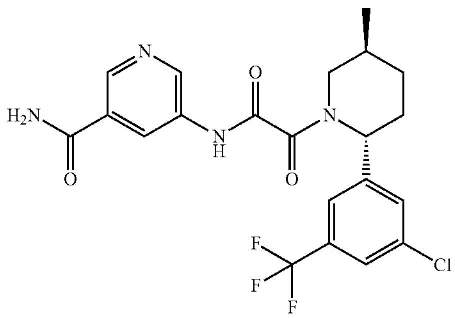 [SMILES: C[C@H]1CC[C@H](c2cc(Cl)cc(C(F)(F)F)c2)N(C(=O)C(=O)Nc2cncc(C(N)=O)c2)C1] | 646 | or/rel | a | bb | aaa | c* | bb* | A | B* |
| 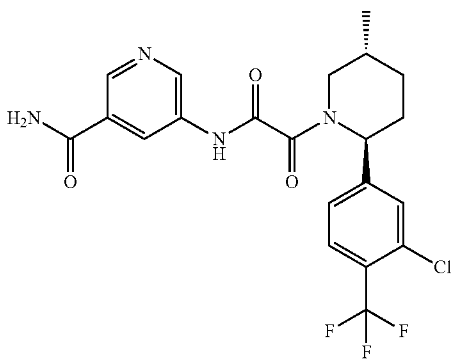 [SMILES: C[C@@H]1CC[C@@H](c2ccc(C(F)(F)F)c(Cl)c2)N(C(=O)C(=O)Nc2cncc(C(N)=O)c2)C1] | 647 | or/rel | c | cc | ccc | | | | |
| 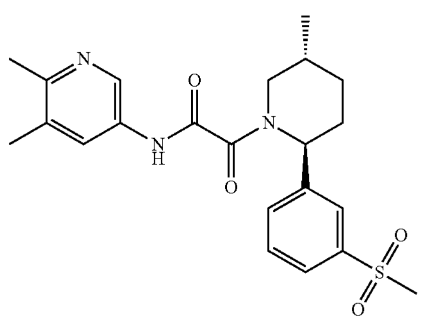 | 648 | and/rac | b | bb | bbb | c* | cc* | B | C* |
| 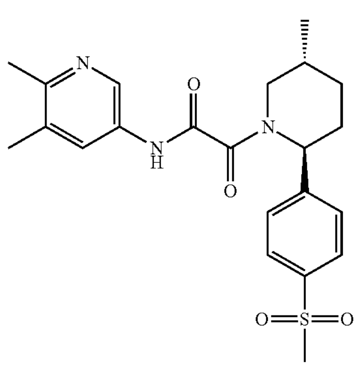 [SMILES: Cc1cc(NC(=O)C(=O)N2C[C@H](C)CC[C@H]2c2ccc(S(C)(=O)=O)cc2)cnc1C] | 649 | and/rac | c | bb | bbb | c* | cc* | B | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 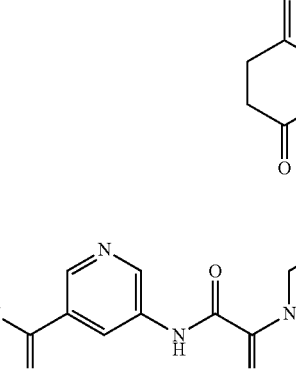 | 650 | and/rac | b | bb | bbb | | | | |
| 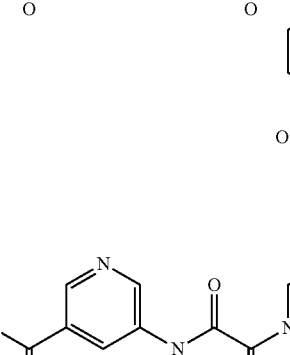 | 651 | and/rac | b | bb | bbb | c* | cc* | C | C* |
| 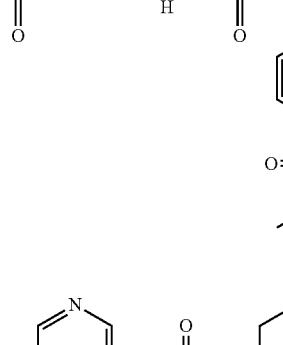 | 652 | and/rac | b | bb | bbb | c* | cc* | C | C* |
| 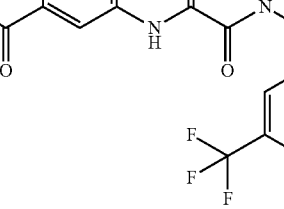 | 653 | or/rel | c | cc | ccc | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 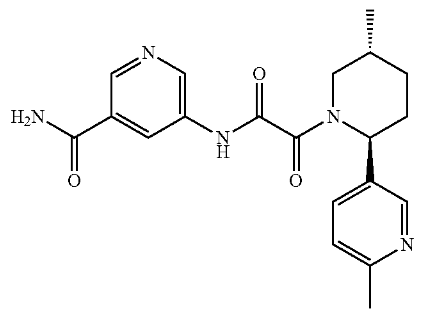 [SMILES: Cc1ccc([C@@H]2CC[C@@H](C)CN2C(=O)C(=O)Nc2cncc(C(N)=O)c2)cn1] | 654 | or/rel | b | bb | aaa | c* | bb* | A | B* |
| 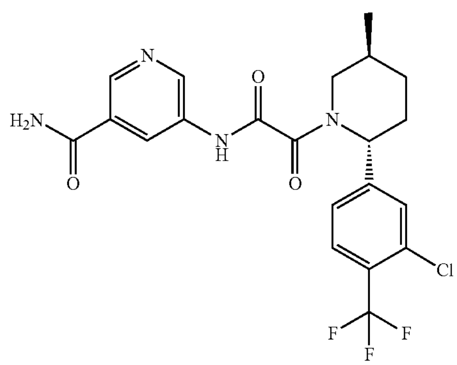 [SMILES: C[C@H]1CC[C@H](c2ccc(C(F)(F)F)c(Cl)c2)N(C(=O)C(=O)Nc2cncc(C(N)=O)c2)C1] | 655 | or/rel | a | bb | aaa | c* | bb* | A | B* |
| 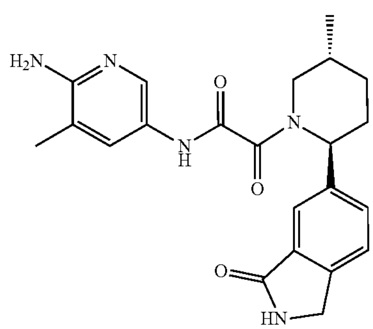 [SMILES: Cc1cc(NC(=O)C(=O)N2C[C@H](C)CC[C@H]2c2ccc3c(c2)C(=O)NC3)cnc1N] | 656 | or/rel | c | cc | ccc | | | | |
| 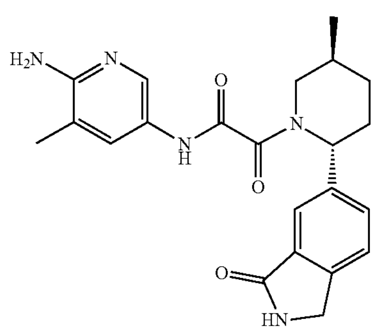 [SMILES: Cc1cc(NC(=O)C(=O)N2C[C@@H](C)CC[C@@H]2c2ccc3c(c2)C(=O)NC3)cnc1N] | 657 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 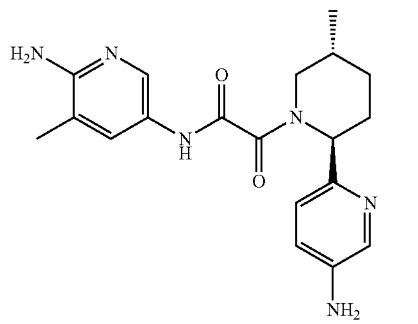 [SMILES: Cc1cc(NC(=O)C(=O)N2C[C@H](C)CC[C@H]2c2ccc(N)cn2)cnc1N] | 658 | and/rac | b | bb | bbb | c* | bb* | A | C* |
| 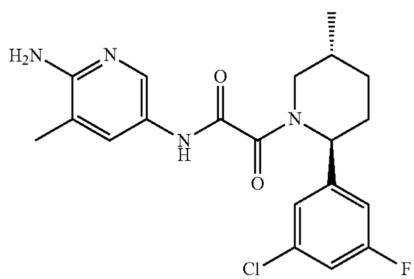 [SMILES: Cc1cc(NC(=O)C(=O)N2C[C@H](C)CC[C@H]2c2cc(F)cc(Cl)c2)cnc1N] | 659 | or/rel | b | aa | aaa | b* | aa* | A | A* |
| 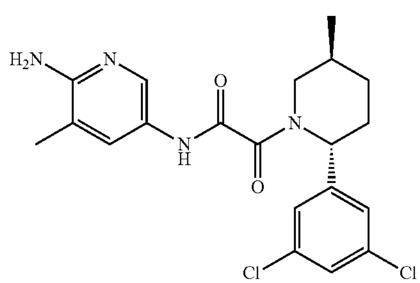 [SMILES: Cc1cc(NC(=O)C(=O)N2C[C@@H](C)CC[C@@H]2c2cc(Cl)cc(Cl)c2)cnc1N] | 660 | or/rel | c | cc | bbb | c* | cc* | B | C* |
| 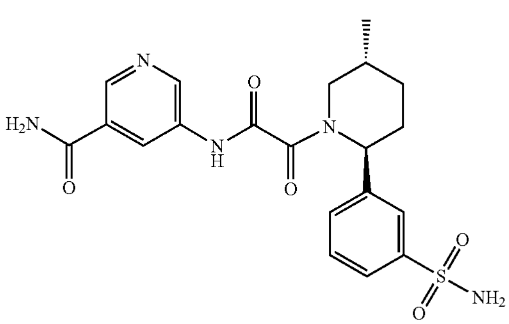 [SMILES: C[C@@H]1CC[C@@H](c2cccc(S(N)(=O)=O)c2)N(C(=O)C(=O)Nc2cncc(C(N)=O)c2)C1] | 661 | and/rac | b | bb | aaa | c* | cc* | B | C* |

TABLE 1-continued

Exemplary compounds of the invention and biological data

| Structure | Nr | Stereo | No Co-factor/SAM rel IC50 | MTA IC50 | HAP1 MTAP intact IC50 | HAP1 MTAP deleted IC50 | MTAP intact/deleted ratio | HAP1 MTAP deleted viability |
|---|---|---|---|---|---|---|---|---|
| | 662 | and/rac | b | bb | bbb | c* | bb* | A | C* |
| | 663 | or/rel | b | aa | aaa | c* | aa* | A | B* |
| | 664 | and/rac | c | cc | bbb | c* | cc* | B | C* |
| | 665 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 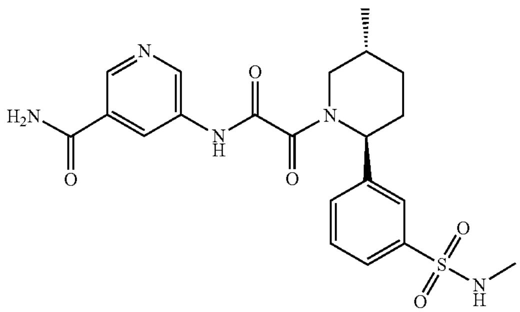 [SMILES: CNS(=O)(=O)c1cccc([C@@H]2CC[C@@H](C)CN2C(=O)C(=O)Nc2cncc(C(N)=O)c2)c1] | 666 | and/rac | b | bb | aaa | c* | cc* | B | C* |
| 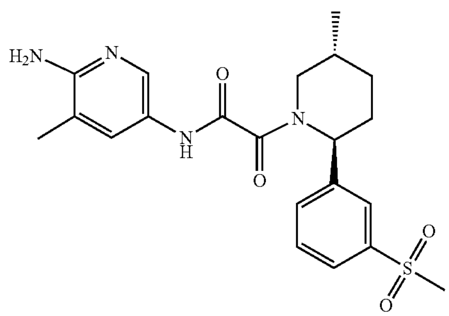 [SMILES: Cc1cc(NC(=O)C(=O)N2C[C@H](C)CC[C@H]2c2cccc(S(C)(=O)=O)c2)cnc1N] | 667 | and/rac | b | bb | bbb | c* | bb* | A | B* |
| 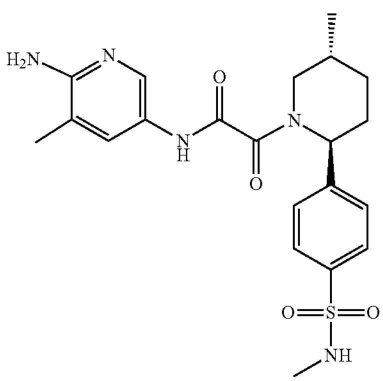 [SMILES: CNS(=O)(=O)c1ccc([C@@H]2CC[C@@H](C)CN2C(=O)C(=O)Nc2cnc(N)c(C)c2)cc1] | 668 | and/rac | b | bb | aaa | b* | bb* | B | B* |
| 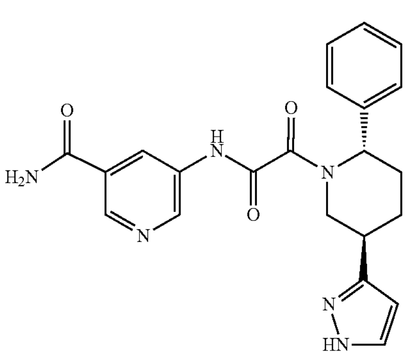 [SMILES: NC(=O)c1cncc(NC(=O)C(=O)N2C[C@H](c3cc[nH]n3)CC[C@H]2c2ccccc2)c1] | 669 | and/rac | c | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 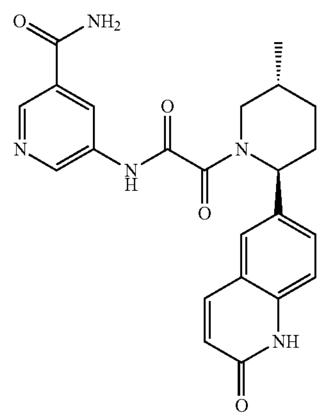 [SMILES: C[C@@H]1CC[C@@H](c2ccc3[nH]c(=O)ccc3c2)N(C(=O)C(=O)Nc2cncc(C(N)=O)c2)C1] | 670 | and/rac | b | bb | aaa | c* | bb* | A | B* |
| 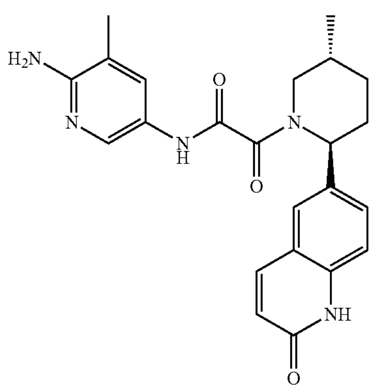 [SMILES: Cc1cc(NC(=O)C(=O)N2C[C@H](C)CC[C@H]2c2ccc3[nH]c(=O)ccc3c2)cnc1N] | 671 | and/rac | b | bb | aaa | b* | aa* | B | A* |
| 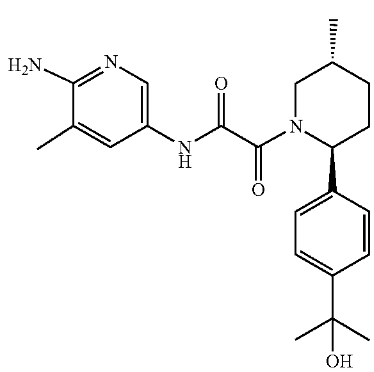 [SMILES: Cc1cc(NC(=O)C(=O)N2C[C@H](C)CC[C@H]2c2ccc(C(C)(C)O)cc2)cnc1N] | 672 | and/rac | b | bb | bbb | c* | bb* | B | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 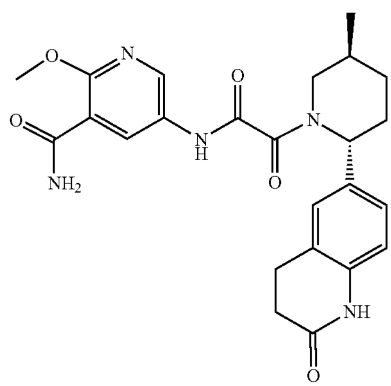 [SMILES: COc1ncc(NC(=O)C(=O)N2C[C@@H](C)CC[C@@H]2c2ccc3c(c2)CCC(=O)N3)cc1C(N)=O] | 673 | or/rel | c | cc | ccc | | | | C* |
| 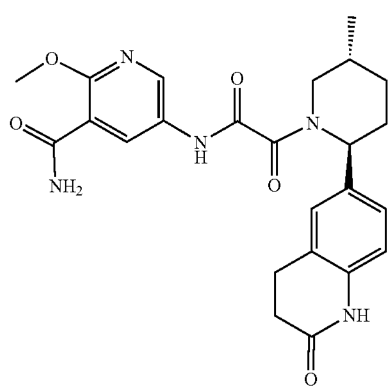 [SMILES: COc1ncc(NC(=O)C(=O)N2C[C@H](C)CC[C@H]2c2ccc3c(c2)CCC(=O)N3)cc1C(N)=O] | 674 | or/rel | b | aa | aaa | b* | aa* | A | A* |
| 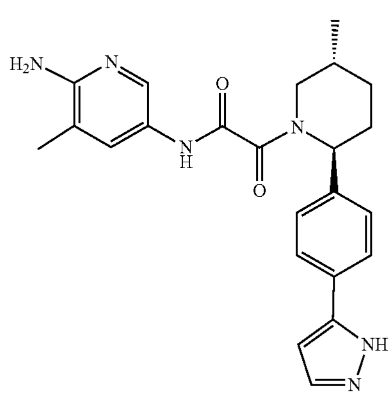 [SMILES: Cc1cc(NC(=O)C(=O)N2C[C@H](C)CC[C@H]2c2ccc(-c3ccn[nH]3)cc2)cnc1N] | 675 | or/rel | c | cc | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 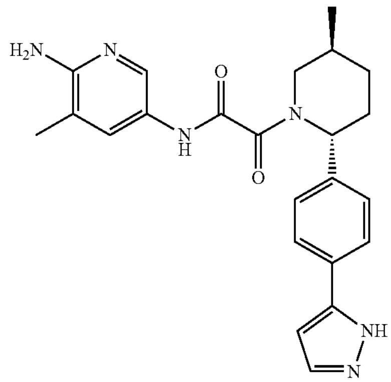 [SMILES: Cc1cc(NC(=O)C(=O)N2C[C@@H](C)CC[C@@H]2c2ccc(-c3ccn[nH]3)cc2)cnc1N] | 676 | or/rel | b | aa | aaa | b* | aa* | B | A* |
| 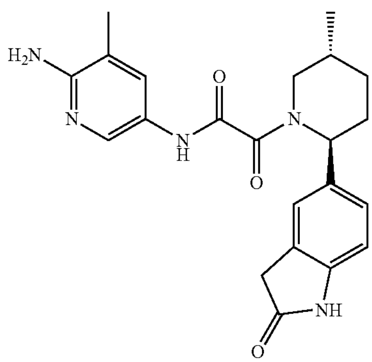 [SMILES: Cc1cc(NC(=O)C(=O)N2C[C@H](C)CC[C@H]2c2ccc3c(c2)CC(=O)N3)cnc1N] | 677 | or/rel | c | cc | bbb | | | | C* |
| 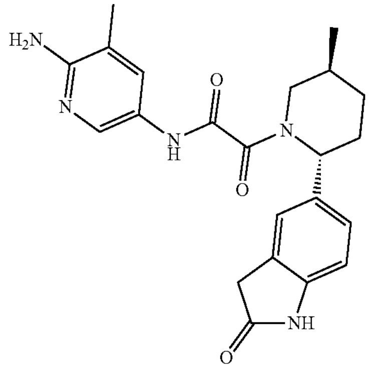 [SMILES: Cc1cc(NC(=O)C(=O)N2C[C@@H](C)CC[C@@H]2c2ccc3c(c2)CC(=O)N3)cnc1N] | 678 | or/rel | b | aa | aaa | a* | aa* | B | A* |
| 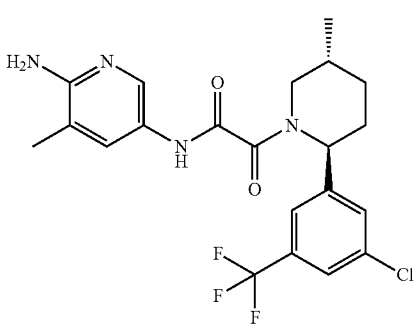 [SMILES: Cc1cc(NC(=O)C(=O)N2C[C@H](C)CC[C@H]2c2cc(Cl)cc(C(F)(F)F)c2)cnc1N] | 679 | or/rel | c | cc | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 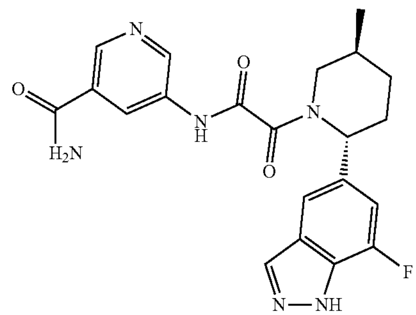 [SMILES: C[C@H]1CC[C@H](c2cc(F)c3[nH]ncc3c2)N(C(=O)C(=O)Nc2cncc(C(N)=O)c2)C1] | 680 | or/rel | c | cc | ccc | | | | C* |
| 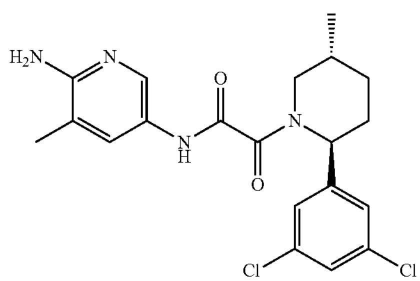 [SMILES: Cc1cc(NC(=O)C(=O)N2C[C@H](C)CC[C@H]2c2cc(Cl)cc(Cl)c2)cnc1N] | 681 | or/rel | b | aa | aaa | c* | aa* | A | B* |
| 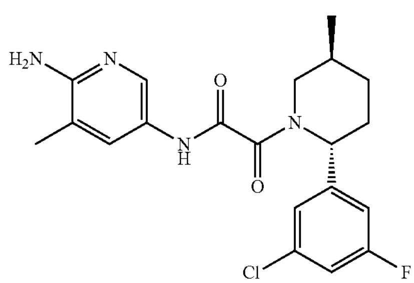 [SMILES: Cc1cc(NC(=O)C(=O)N2C[C@@H](C)CC[C@@H]2c2cc(F)cc(Cl)c2)cnc1N] | 682 | or/rel | c | cc | bbb | | | | C* |
| 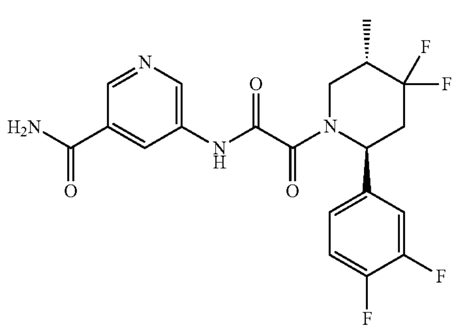 [SMILES: C[C@H]1CN(C(=O)C(=O)Nc2cncc(C(N)=O)c2)[C@H](c2ccc(F)c(F)c2)CC1(F)F] | 683 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 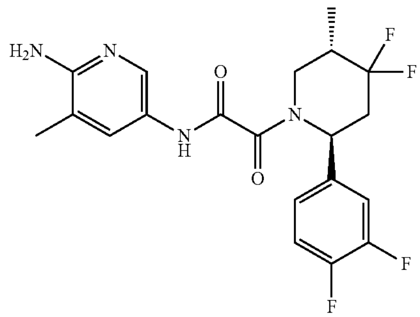 [SMILES: Cc1cc(NC(=O)C(=O)N2C[C@H](C)C(F)(F)C[C@H]2c2ccc(F)c(F)c2)cnc1N] | 684 | or/rel | c | cc | ccc | c* | cc* | C | C* |
| 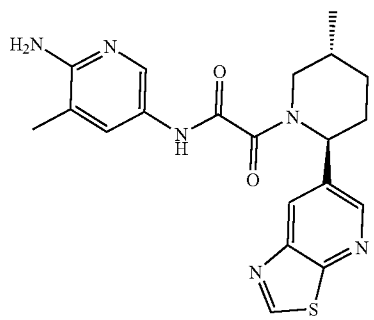 [SMILES: Cc1cc(NC(=O)C(=O)N2C[C@H](C)CC[C@H]2c2cnc3scnc3c2)cnc1N] | 685 | and/rac | c | bb | bbb | c* | bb* | A | C* |
| 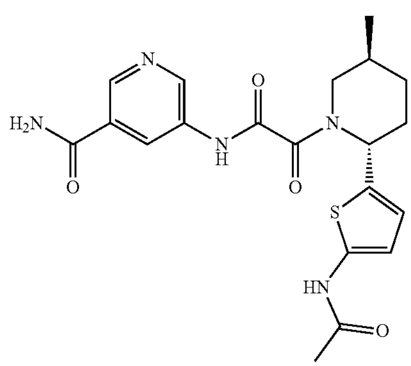 [SMILES: CC(=O)Nc1ccc([C@H]2CC[C@H](C)CN2C(=O)C(=O)Nc2cncc(C(N)=O)c2)s1] | 686 | or/rel | c | cc | ccc | c* | cc* | C | C* |
| 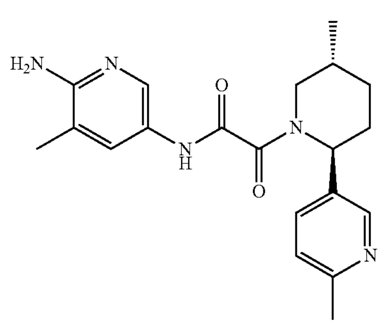 [SMILES: Cc1ccc([C@@H]2CC[C@@H](C)CN2C(=O)C(=O)Nc2cnc(N)c(C)c2)cn1] | 687 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 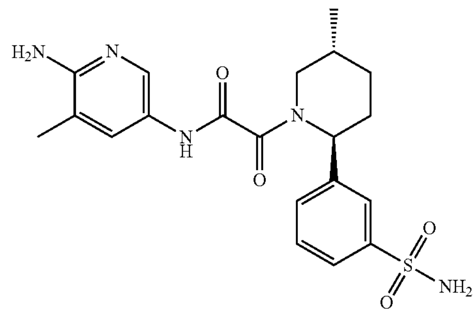 [SMILES: Cc1cc(NC(=O)C(=O)N2C[C@H](C)CC[C@H]2c2cccc(S(N)(=O)=O)c2)cnc1N] | 688 | and/rac | b | bb | aaa | c* | bb* | A | B* |
| 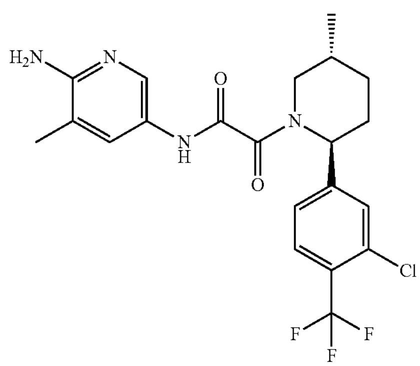 [SMILES: Cc1cc(NC(=O)C(=O)N2C[C@H](C)CC[C@H]2c2ccc(C(F)(F)F)c(Cl)c2)cnc1N] | 689 | or/rel | c | cc | ccc | c* | cc* | C | C* |
| 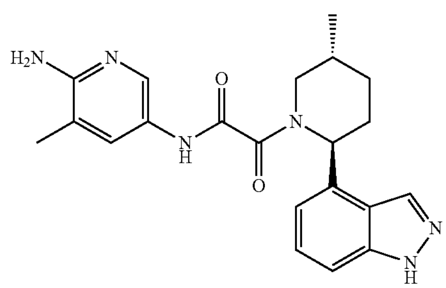 [SMILES: Cc1cc(NC(=O)C(=O)N2C[C@H](C)CC[C@H]2c2cccc3[nH]ncc23)cnc1N] | 690 | and/rac | b | bb | aaa | c* | bb* | A | B* |
| 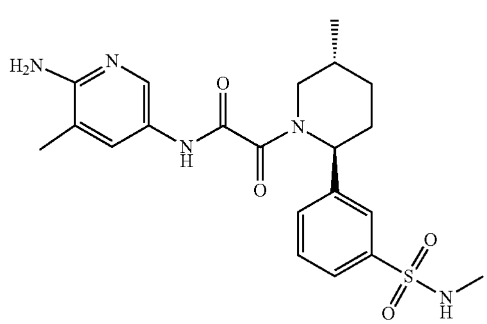 [SMILES: CNS(=O)(=O)c1cccc([C@@H]2CC[C@@H](C)CN2C(=O)C(=O)Nc2cnc(N)c(C)c2)c1] | 691 | and/rac | b | bb | aaa | c* | bb* | A | B* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 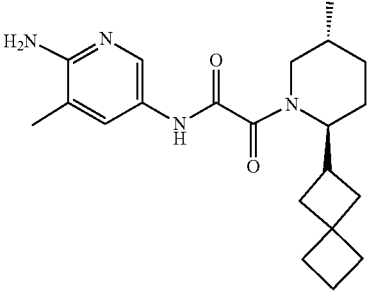 | 692 | and/rac | c | cc | bbb | c* | cc* | C | C* |
| 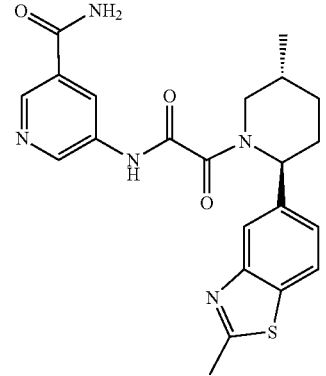 [SMILES: Cc1nc2cc([C@@H]3CC[C@@H](C)CN3C(=O)C(=O)Nc3cncc(C(N)=O)c3)ccc2s1] | 693 | or/rel | b | aa | aaa | b* | aa* | A | A* |
| 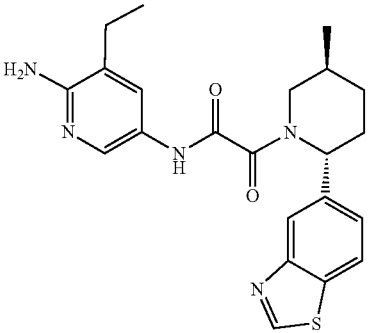 [SMILES: CCc1cc(NC(=O)C(=O)N2C[C@@H](C)CC[C@@H]2c2ccc3scnc3c2)cnc1N] | 694 | | c | cc | ccc | c* | bb* | A | B* |
| 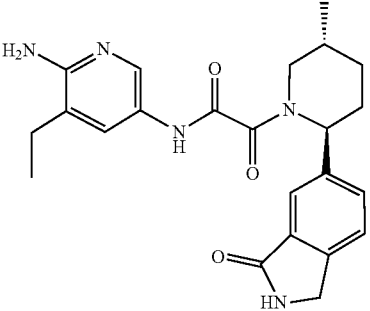 [SMILES: CCc1cc(NC(=O)C(=O)N2C[C@H](C)CC[C@H]2c2ccc3c(c2)C(=O)NC3)cnc1N] | 695 | or/rel | c | cc | ccc | | | | C* |

TABLE 1-continued

Exemplary compounds of the invention and biological data

| Structure | Nr | Stereo | No Co-factor/ SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 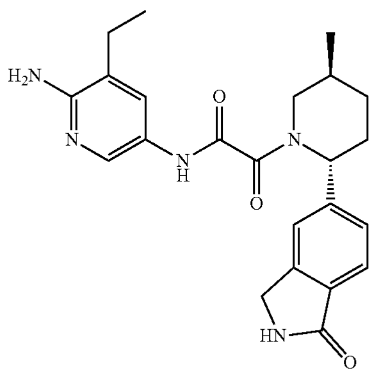 [SMILES: CCc1cc(NC(=O)C(=O)N2C[C@@H](C)CC[C@@H]2c2ccc3c(c2)CNC3=O)cnc1N] | 696 | or/rel | b | aa | aaa | c* | aa* | A | B* |
| 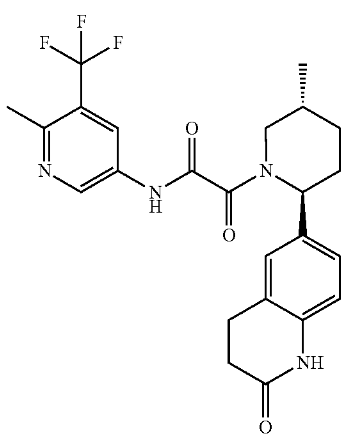 [SMILES: Cc1ncc(NC(=O)C(=O)N2C[C@H](C)CC[C@H]2c2ccc3c(c2)CCC(=O)N3)cc1C(F)(F)F] | 697 | or/rel | b | aa | aaa | c* | aa* | A | A* |
| 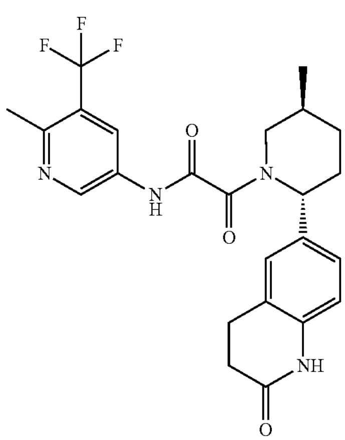 [SMILES: Cc1ncc(NC(=O)C(=O)N2C[C@@H](C)CC[C@@H]2c2ccc3c(c2)CCC(=O)N3)cc1C(F)(F)F] | 698 | or/rel | c | cc | ccc | | | | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 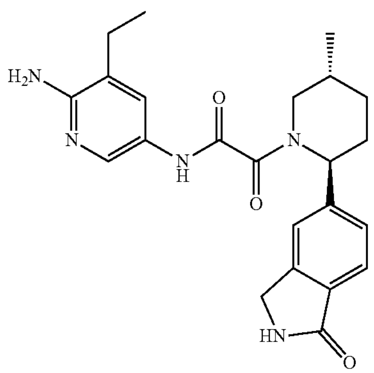 [SMILES: CCc1cc(NC(=O)C(=O)N2C[C@H](C)CC[C@H]2c2ccc3c(c2)CNC3=O)cnc1N] | 699 | or/rel | c | cc | ccc | | | | C* |
| 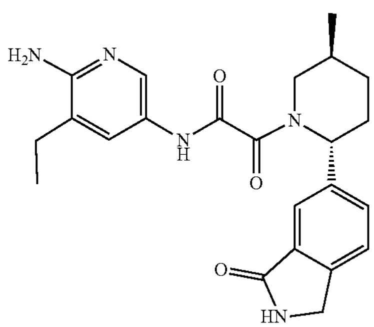 [SMILES: CCc1cc(NC(=O)C(=O)N2C[C@@H](C)CC[C@@H]2c2ccc3c(c2)C(=O)NC3)cnc1N] | 700 | or/rel | b | aa | aaa | c* | aa* | A | A* |
| 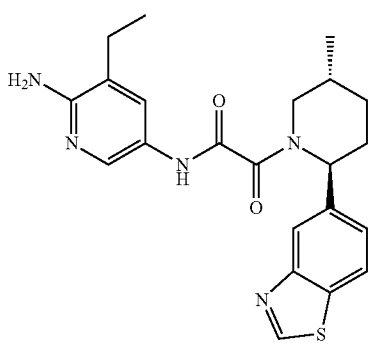 [SMILES: CCc1cc(NC(=O)C(=O)N2C[C@H](C)CC[C@H]2c2ccc3scnc3c2)cnc1N] | 701 | | b | aa | aaa | b* | aa* | A | A* |
| 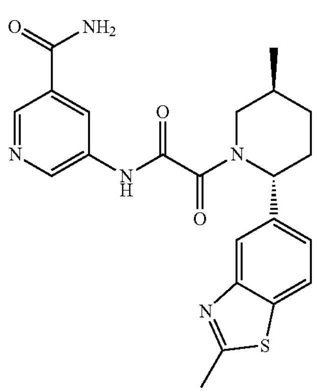 [SMILES: Cc1nc2cc([C@H]3CC[C@H](C)CN3C(=O)C(=O)Nc3cncc(C(N)=O)c3)ccc2s1] | 702 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 703 | or/rel | b | bb | aaa | b* | bb* | C | B* |
| | 704 | or/rel | c | bb | aaa | c* | cc* | C | C* |
| | 705 | or/rel | b | aa | aaa | b* | aa* | B | A* |
| | 706 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 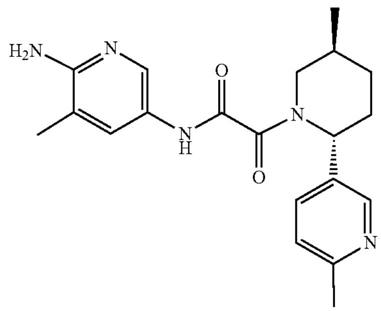 [SMILES: Cc1ccc([C@H]2CC[C@H](C)CN2C(=O)C(=O)Nc2cnc(N)c(C)c2)cn1] | 707 | or/rel | c | cc | ccc | c* | cc* | B | C* |
| 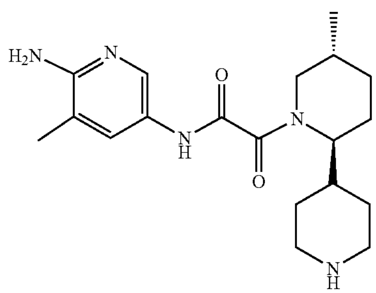 [SMILES: Cc1cc(NC(=O)C(=O)N2C[C@H](C)CC[C@H]2C2CCNCC2)cnc1N] | 708 | and/rac | c | cc | ccc | | | | C* |
| 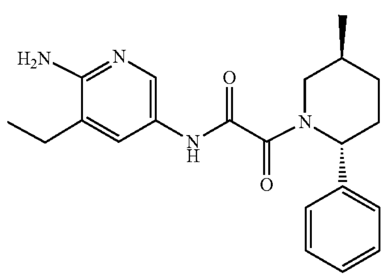 [SMILES: CCc1cc(NC(=O)C(=O)N2C[C@@H](C)CC[C@@H]2c2ccccc2)cnc1N] | 709 | or/rel | c | cc | bbb | c* | cc* | C | C* |
| 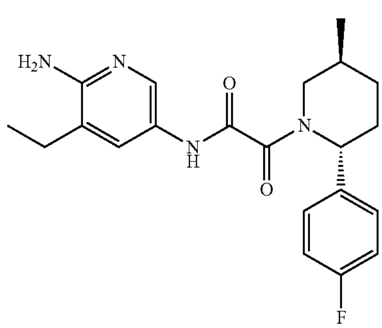 [SMILES: CCc1cc(NC(=O)C(=O)N2C[C@@H](C)CC[C@@H]2c2ccc(F)cc2)cnc1N] | 710 | and/rac | b | aa | aaa | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 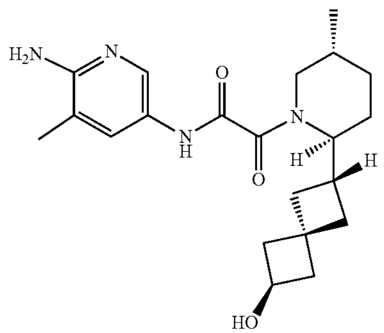 | 711 | and/rac | c | cc | bbb | c* | cc* | B | C* |
| 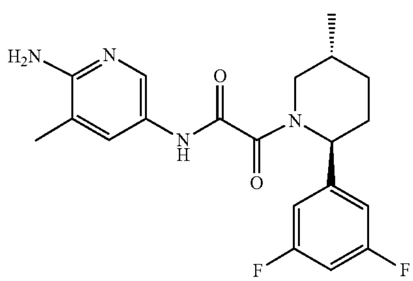 [SMILES: Cc1cc(NC(=O)C(=O)N2C[C@H](C)CC[C@H]2c2cc(F)cc(F)c2)cnc1N] | 712 | or/rel | c | cc | ccc | | | | C* |
| 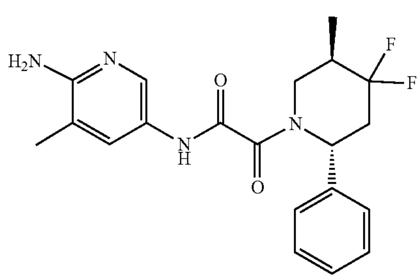 [SMILES: Cc1cc(NC(=O)C(=O)N2C[C@@H](C)C(F)(F)C[C@@H]2c2ccccc2)cnc1N] | 713 | or/rel | c | cc | ccc | | | | C* |
| 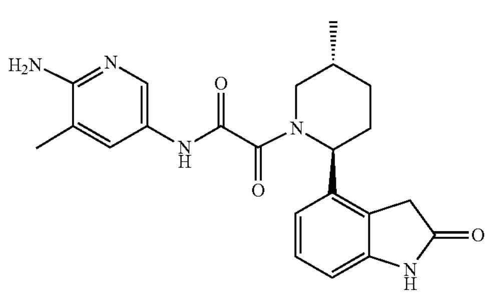 [SMILES: Cc1cc(NC(=O)C(=O)N2C[C@H](C)CC[C@H]2c2cccc3c2CC(=O)N3)cnc1N] | 714 | and/rac | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 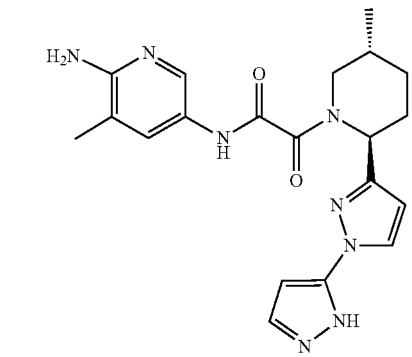 | 715 | and/rac | c | bb | bbb | c* | aa* | A | B* |
| 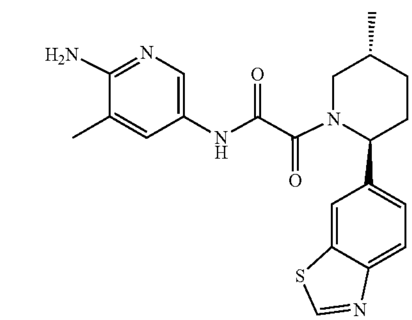 [SMILES: Cc1cc(NC(=O)C(=O)N2C[C@H](C)CC[C@H]2c2ccc3ncsc3c2)cnc1N] | 716 | and/rac | b | bb | aaa | c* | aa* | A | A* |
| 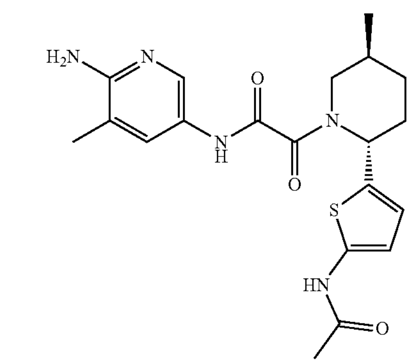 [SMILES: CC(=O)Nc1ccc([C@H]2CC[C@H](C)CN2C(=O)C(=O)Nc2cnc(N)c(C)c2)s1] | 717 | or/rel | c | cc | ccc | c* | cc* | C | C* |
| 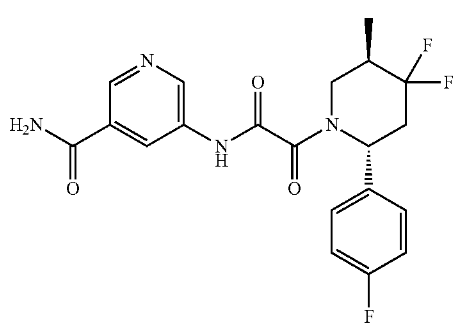 [SMILES: C[C@@H]1CN(C(=O)C(=O)Nc2cncc(C(N)=O)c2)[C@@H](c2ccc(F)cc2)CC1(F)F] | 718 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 719 | or/rel | b | aa | aaa | b* | aa* | A | A* |
| | 720 | or/rel | b | aa | aaa | b* | aa* | A | A* |
| | 721 | or/rel | b | aa | aaa | c* | aa* | A | A* |
| | 722 | or/rel | b | bb | aaa | c* | cc* | C | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure) | 723 | or/rel | c | cc | ccc | | | | C* |
| (structure) | 724 | or/rel | c | cc | ccc | c* | cc* | C | C* |
| (structure) | 725 | or/rel | b | bb | aaa | c* | cc* | C | C* |
| (structure) | 726 | or/rel | b | aa | aaa | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 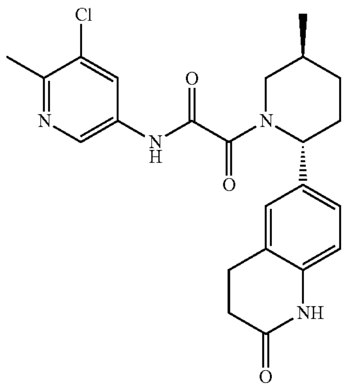 [SMILES: Cc1ncc(NC(=O)C(=O)N2C[C@@H](C)CC[C@@H]2c2ccc3c(c2)CCC(=O)N3)cc1Cl] | 727 | or/rel | c | cc | ccc | c* | cc* | C | C* |
| 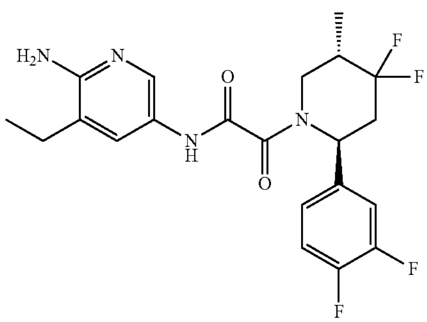 [SMILES: CCc1cc(NC(=O)C(=O)N2C[C@H](C)C(F)(F)C[C@H]2c2ccc(F)c(F)c2)cnc1N] | 728 | or/rel | c | cc | ccc | c* | cc* | C | C* |
| 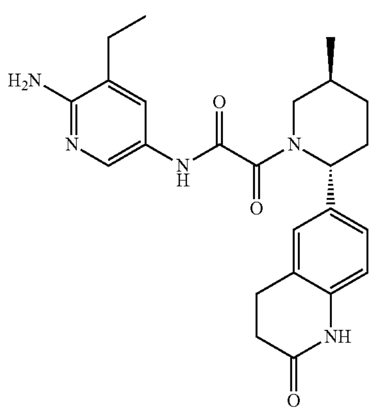 [SMILES: CCc1cc(NC(=O)C(=O)N2C[C@@H](C)CC[C@@H]2c2ccc3c(c2)CCC(=O)N3)cnc1N] | 729 | or/rel | c | cc | ccc | c* | bb* | A | B* |
| 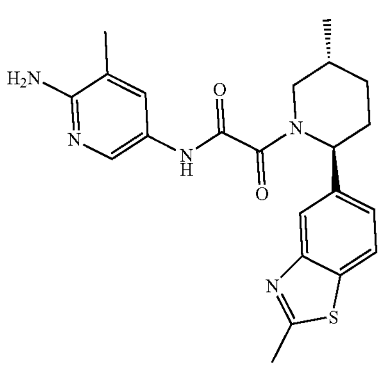 [SMILES: Cc1nc2cc([C@@H]3CC[C@@H](C)CN3C(=O)C(=O)Nc3cnc(N)c(C)c3)ccc2s1] | 730 | or/rel | c | cc | ccc | c* | cc* | C | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 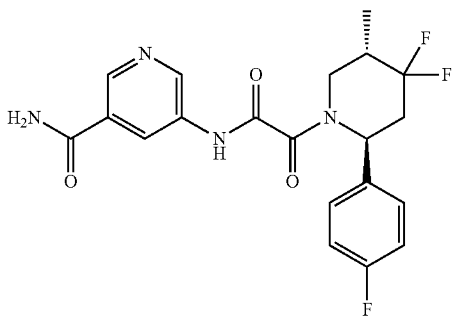 [SMILES: C[C@H]1CN(C(=O)C(=O)Nc2cncc(C(N)=O)c2)[C@H](c2ccc(F)cc2)CC1(F)F] | 731 | or/rel | b | bb | aaa | c* | aa* | A | B* |
| 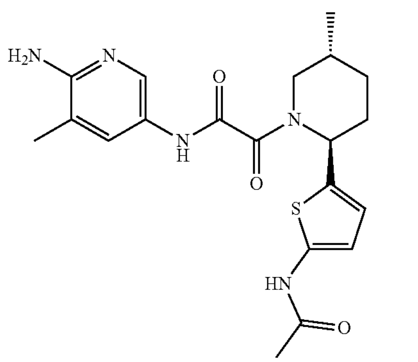 [SMILES: CC(=O)Nc1ccc([C@@H]2CC[C@@H](C)CN2C(=O)C(=O)Nc2cnc(N)c(C)c2)s1] | 732 | or/rel | b | bb | aaa | c* | bb* | A | B* |
| 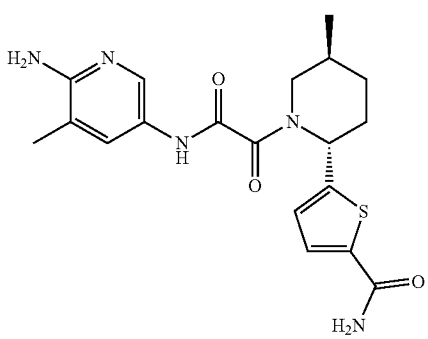 [SMILES: Cc1cc(NC(=O)C(=O)N2C[C@@H](C)CC[C@@H]2c2ccc(C(N)=O)s2)cnc1N] | 733 | or/rel | b | aa | aaa | b* | aa* | A | A* |
| 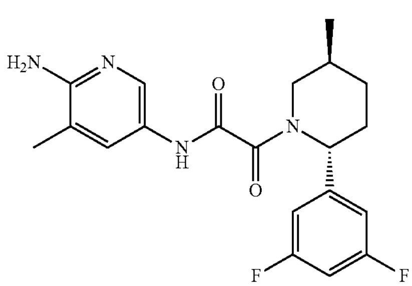 [SMILES: Cc1cc(NC(=O)C(=O)N2C[C@@H](C)CC[C@@H]2c2cc(F)cc(F)c2)cnc1N] | 734 | or/rel | b | aa | aaa | c* | aa* | A | B* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| [structure] | 735 | or/rel | a | aa | aaa | b* | aa* | A | A* |
| [structure] | 736 | or/rel | b | aa | aaa | c* | aa* | A | A* |
| [structure] | 737 | and/rac | c | bb | bbb | c* | cc* | B | C* |
| [structure] | 738 | and/rac | b | bb | bbb | c* | cc* | B | C* |
| [structure] | 739 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure) | 740 | or/rel | b | bb | aaa | c* | cc* | B | B* |
| (structure) | 741 | or/rel | c | cc | ccc | c* | cc* | C | C* |
| (structure) | 742 | or/rel | b | bb | aaa | c* | bb* | A | B* |
| (structure) | 743 | and/rac | b | bb | bbb | b* | aa* | A | A* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 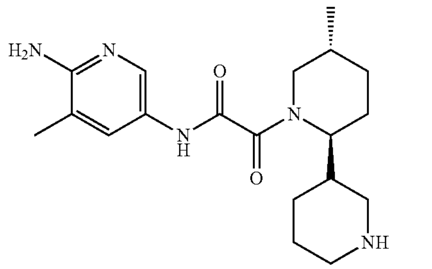 [SMILES: Cc1cc(NC(=O)C(=O)N2C[C@H](C)CC[C@H]2C2CCCNC2)cnc1N] | 744 | and/rac | c | cc | bbb | c* | cc* | C | C* |
| 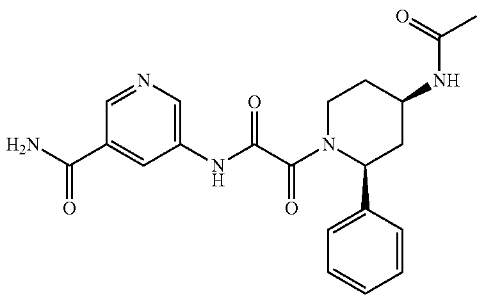 [SMILES: CC(=O)N[C@@H]1CCN(C(=O)C(=O)Nc2cncc(C(N)=O)c2)[C@H](c2ccccc2)C1] | 745 | and/rac | c | cc | bbb | c* | cc* | C | C* |
| 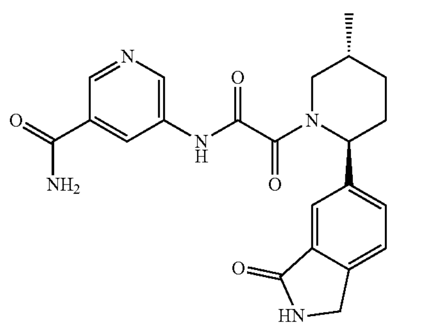 [SMILES: C[C@@H]1CC[C@@H](c2ccc3c(c2)C(=O)NC3)N(C(=O)C(=O)Nc2cncc(C(N)=O)c2)C1] | 746 | or/rel | b | aa | aaa | c* | bb* | A | B* |
| 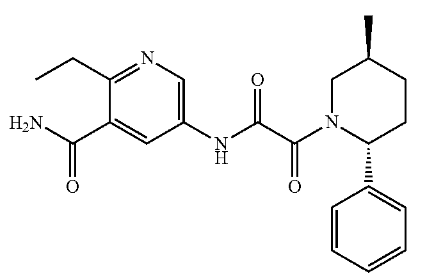 [SMILES: CCc1ncc(NC(=O)C(=O)N2C[C@@H](C)CC[C@@H]2c2ccccc2)cc1C(N)=O] | 747 | and/rac | b | bb | bbb | c* | cc* | B | C* |
| 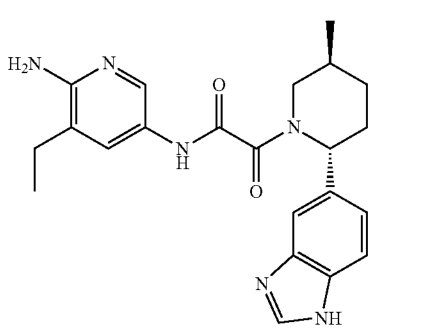 [SMILES: CCc1cc(NC(=O)C(=O)N2C[C@@H](C)CC[C@@H]2c2ccc3[nH]cnc3c2)cnc1N] | 748 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 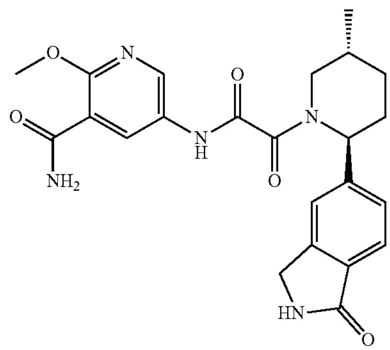 [SMILES: COc1ncc(NC(=O)C(=O)N2C[C@H](C)CC[C@H]2c2ccc3c(c2)CNC3=O)cc1C(N)=O] | 749 | or/rel | b | bb | aaa | c* | bb* | A | B* |
| 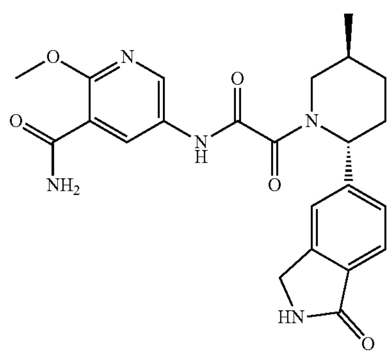 [SMILES: COc1ncc(NC(=O)C(=O)N2C[C@@H](C)CC[C@@H]2c2ccc3c(c2)CNC3=O)cc1C(N)=O] | 750 | or/rel | c | cc | ccc | c* | cc* | C | C* |
| 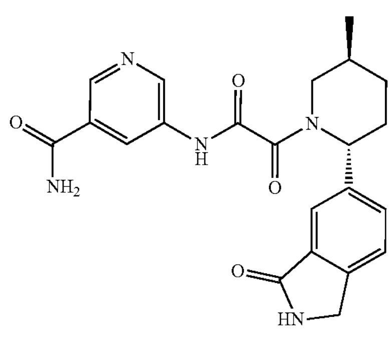 [SMILES: C[C@H]1CC[C@H](c2ccc3c(c2)C(=O)NC3)N(C(=O)C(=O)Nc2cncc(C(N)=O)c2)C1] | 751 | or/rel | c | cc | ccc | c* | cc* | C | C* |
| 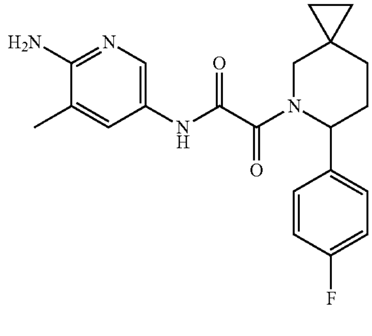 [SMILES: Cc1cc(NC(=O)C(=O)N2CC3(CCC2c2ccc(F)cc2)CC3)cnc1N] | 753 | | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 754 | or/rel | b | bb | aaa | c* | aa* | A | B* |
| | 755 | and/rac | b | bb | aaa | c* | bb* | A | B* |
| | 756 | or/rel | c | cc | ccc | c* | cc* | B | C* |
| | 757 | and/rac | b | bb | bbb | c* | bb* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 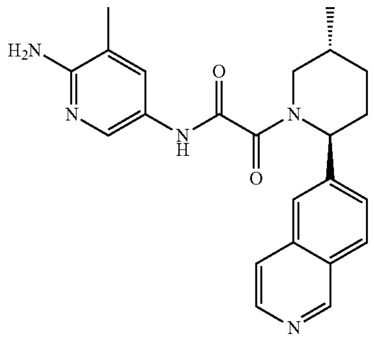 [SMILES: Cc1cc(NC(=O)C(=O)N2C[C@H](C)CC[C@H]2c2ccc3cnccc3c2)cnc1N] | 758 | and/rac | b | bb | bbb | b* | aa* | A | A* |
| 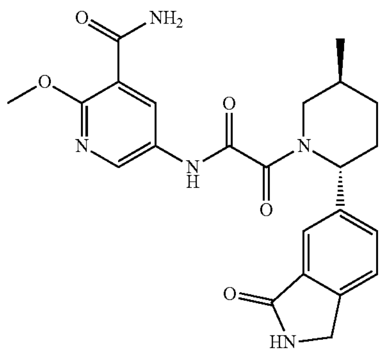 [SMILES: COc1ncc(NC(=O)C(=O)N2C[C@@H](C)CC[C@@H]2c2ccc3c(c2)C(=O)NC3)cc1C(N)=O] | 759 | and/rac | b | bb | aaa | c* | bb* | A | B* |
| 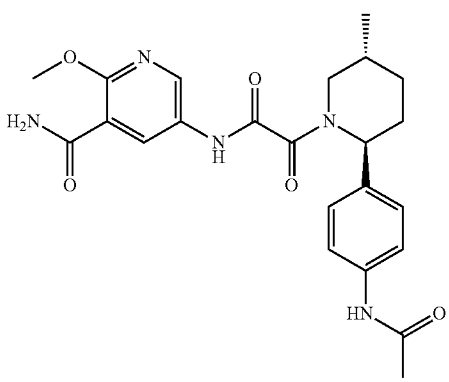 [SMILES: COc1ncc(NC(=O)C(=O)N2C[C@H](C)CC[C@H]2c2ccc(NC(C)=O)cc2)cc1C(N)=O] | 760 | or/rel | b | aa | aaa | c* | aa* | A | A* |
| 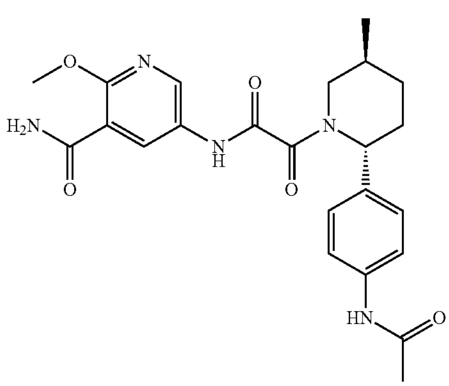 [SMILES: COc1ncc(NC(=O)C(=O)N2C[C@@H](C)CC[C@@H]2c2ccc(NC(C)=O)cc2)cc1C(N)=O] | 761 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 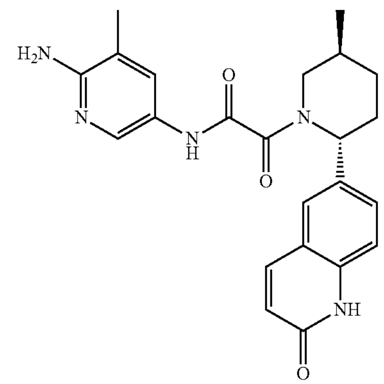 [SMILES: Cc1cc(NC(=O)C(=O)N2C[C@@H](C)CC[C@@H]2c2ccc3[nH]c(=O)ccc3c2)cnc1N] | 762 | or/rel | a | aa | aaa | a* | aa* | B | A* |
| 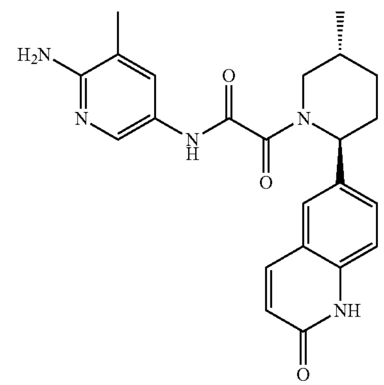 [SMILES: Cc1cc(NC(=O)C(=O)N2C[C@H](C)CC[C@H]2c2ccc3[nH]c(=O)ccc3c2)cnc1N] | 763 | or/rel | c | cc | ccc | c* | cc* | B | C* |
| 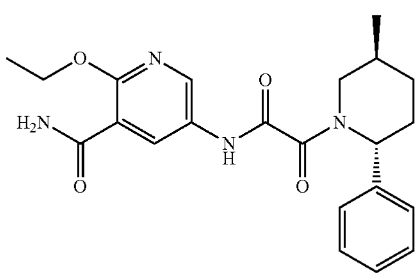 [SMILES: CCOc1ncc(NC(=O)C(=O)N2C[C@@H](C)CC[C@@H]2c2ccccc2)cc1C(N)=O] | 764 | or/rel | b | bb | aaa | c* | bb* | A | B* |
| 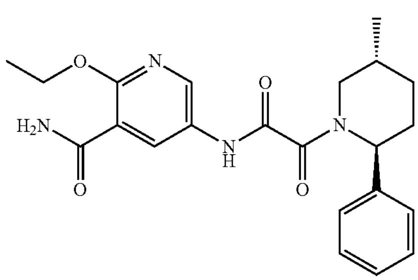 [SMILES: CCOc1ncc(NC(=O)C(=O)N2C[C@H](C)CC[C@H]2c2ccccc2)cc1C(N)=O] | 765 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| | 766 | or/rel | c | cc | ccc | c* | cc* | C | C* |
| | 767 | or/rel | b | cc | bbb | c* | cc* | B | C* |
| | 768 | or/rel | b | bb | bbb | c* | bb* | B | C* |
| | 769 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 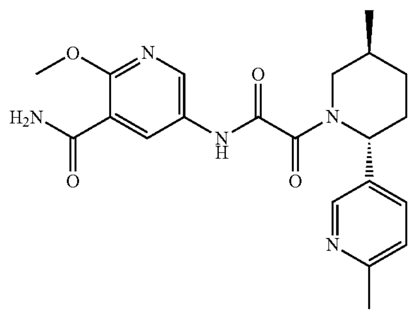 [SMILES: COc1ncc(NC(=O)C(=O)N2C[C@@H](C)CC[C@@H]2c2ccc(C)nc2)cc1C(N)=O] | 770 | or/rel | c | cc | ccc | c* | cc* | C | C* |
| 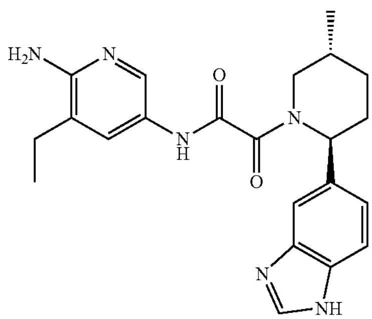 [SMILES: CCc1cc(NC(=O)C(=O)N2C[C@H](C)CC[C@H]2c2ccc3[nH]cnc3c2)cnc1N] | 771 | or/rel | c | cc | ccc | c* | cc* | C | C* |
| 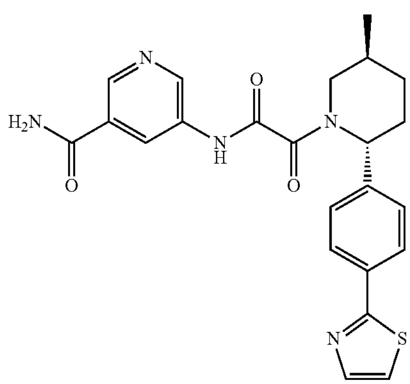 [SMILES: C[C@H]1CC[C@H](c2ccc(-c3nccs3)cc2)N(C(=O)C(=O)Nc2cncc(C(N)=O)c2)C1] | 772 | or/rel | c | cc | ccc | c* | cc* | B | C* |
| 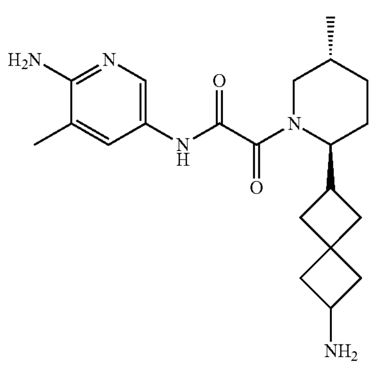 [SMILES: Cc1cc(NC(=O)C(=O)N2C[C@H](C)CC[C@H]2C2CC3(CC(N)C3)C2)cnc1N] | 773 | and/rac | b | bb | bbb | c* | bb* | B | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure) | 774 | and/rac | c | cc | bbb | c* | cc* | B | C* |
| (structure) | 776 | | b | bb | bbb | c* | bb* | A | B* |
| (structure) | 777 | or/rel | c | cc | ccc | c* | cc* | B | C* |
| (structure) | 778 | or/rel | b | aa | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 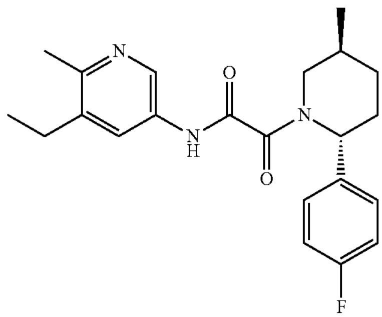 [SMILES: CCc1cc(NC(=O)C(=O)N2C[C@@H](C)CC[C@@H]2c2ccc(F)cc2)cnc1C] | 779 | abs | b | bb | aaa | c* | bb* | A | B* |
| 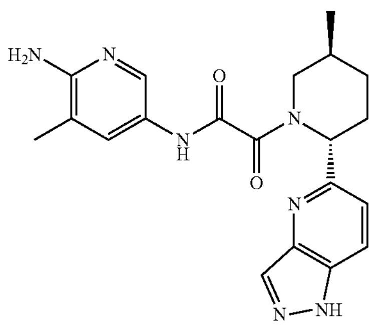 [SMILES: Cc1cc(NC(=O)C(=O)N2C[C@@H](C)CC[C@@H]2c2ccc3[nH]ncc3n2)cnc1N] | 780 | or/rel | c | cc | ccc | c* | bb* | A | C* |
| 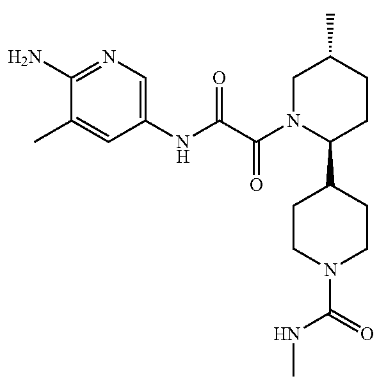 [SMILES: CNC(=O)N1CCC([C@@H]2CC[C@@H](C)CN2C(=O)C(=O)Nc2cnc(N)c(C)c2)CC1] | 781 | and/rac | b | bb | bbb | c* | aa* | A | B* |
| 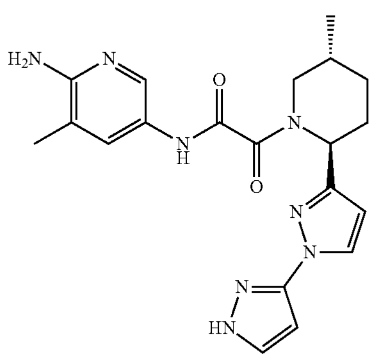 [SMILES: Cc1cc(NC(=O)C(=O)N2C[C@H](C)CC[C@H]2c2ccn(-c3cc[nH]n3)n2)cnc1N] | 782 | or/rel | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 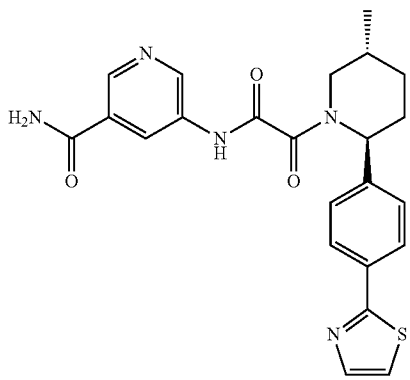 [SMILES: C[C@@H]1CC[C@@H](c2ccc(-c3nccs3)cc2)N(C(=O)C(=O)Nc2cncc(C(N)=O)c2)C1] | 783 | or/rel | b | bb | aaa | c* | aa* | A | B* |
| 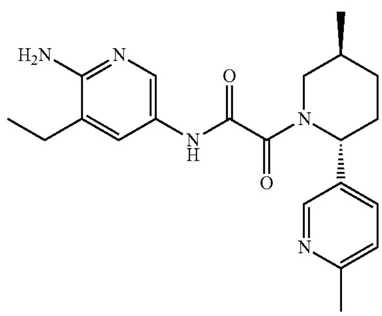 [SMILES: CCc1cc(NC(=O)C(=O)N2C[C@@H](C)CC[C@@H]2c2ccc(C)nc2)cnc1N] | 784 | or/rel | b | aa | aaa | c* | aa* | A | A* |
| 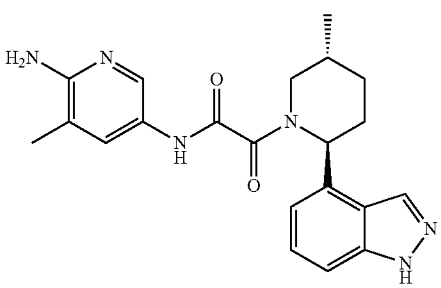 [SMILES: Cc1cc(NC(=O)C(=O)N2C[C@H](C)CC[C@H]2c2cccc3[nH]ncc23)cnc1N] | 785 | or/rel | b | aa | aaa | b* | aa* | A | A* |
| 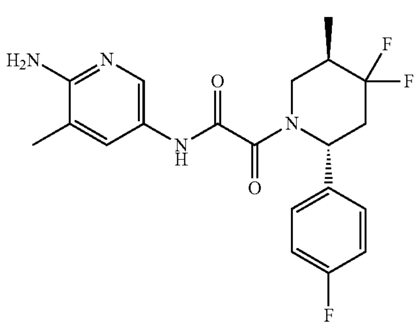 [SMILES: Cc1cc(NC(=O)C(=O)N2C[C@@H](C)C(F)(F)C[C@@H]2c2ccc(F)cc2)cnc1N] | 786 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 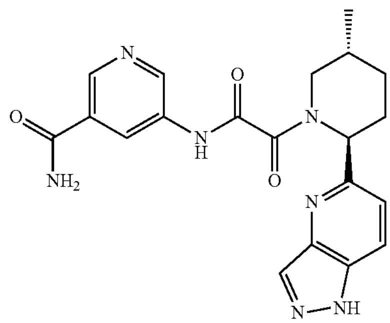 [SMILES: C[C@@H]1CC[C@@H](c2ccc3[nH]ncc3n2)N(C(=O)C(=O)Nc2cncc(C(N)=O)c2)C1] | 787 | or/rel | c | cc | ccc | c* | cc* | C | C* |
| 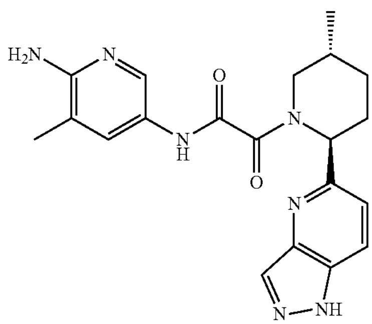 [SMILES: Cc1cc(NC(=O)C(=O)N2C[C@H](C)CC[C@H]2c2ccc3[nH]ncc3n2)cnc1N] | 788 | or/rel | b | aa | aaa | b* | aa* | A | A* |
| 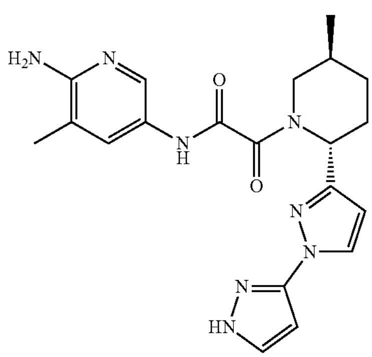 [SMILES: Cc1cc(NC(=O)C(=O)N2C[C@@H](C)CC[C@@H]2c2ccn(-c3cc[nH]n3)n2)cnc1N] | 789 | or/rel | c | cc | ccc | c* | cc* | B | C* |
| 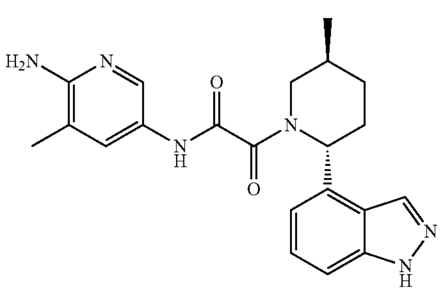 [SMILES: Cc1cc(NC(=O)C(=O)N2C[C@@H](C)CC[C@@H]2c2cccc3[nH]ncc23)cnc1N] | 790 | or/rel | c | cc | ccc | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 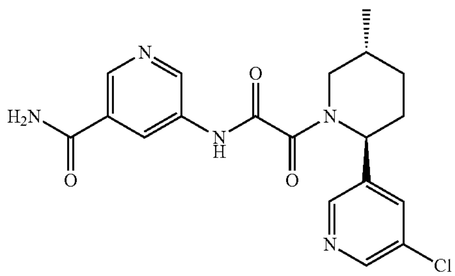 [SMILES: C[C@@H]1CC[C@@H](c2cncc(Cl)c2)N(C(=O)C(=O)Nc2cncc(C(N)=O)c2)C1] | 791 | and/rac | b | bb | aaa | c* | bb* | A | B* |
| 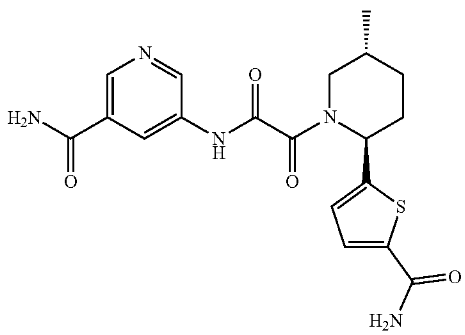 [SMILES: C[C@@H]1CC[C@@H](c2ccc(C(N)=O)s2)N(C(=O)C(=O)Nc2cncc(C(N)=O)c2)C1] | 792 | or/rel | b | aa | aaa | c* | aa* | A | B* |
| 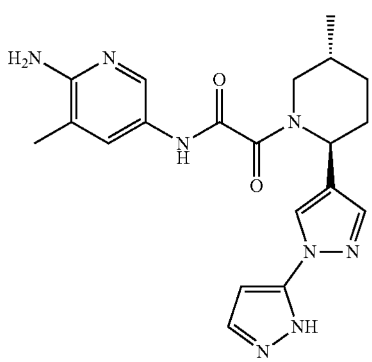 [SMILES: Cc1cc(NC(=O)C(=O)N2C[C@H](C)CC[C@H]2c2cnn(-c3ccn[nH]3)c2)cnc1N] | 793 | and/rac | b | bb | bbb | c* | bb* | A | B* |
| 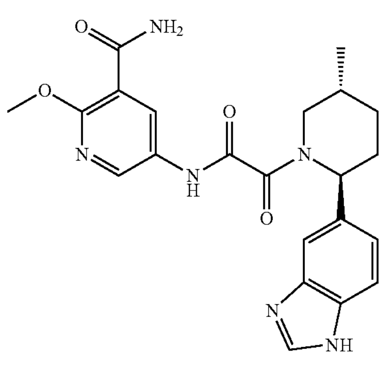 [SMILES: COc1ncc(NC(=O)C(=O)N2C[C@H](C)CC[C@H]2c2ccc3[nH]cnc3c2)cc1C(N)=O] | 794 | or/rel | b | aa | aaa | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 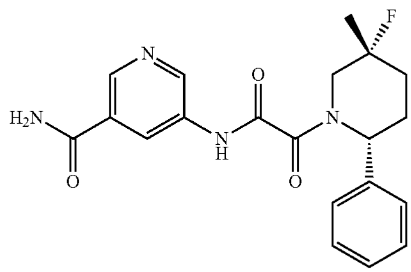 [SMILES: C[C@@]1(F)CC[C@H](c2ccccc2)N(C(=O)C(=O)Nc2cncc(C(N)=O)c2)C1] | 795 | or/rel | b | bb | aaa | c* | aa* | A | B* |
| 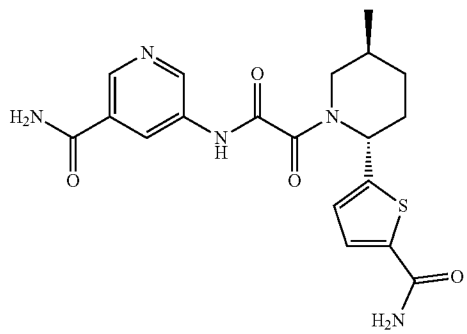 [SMILES: C[C@H]1CC[C@H](c2ccc(C(N)=O)s2)N(C(=O)C(=O)Nc2cncc(C(N)=O)c2)C1] | 796 | or/rel | c | cc | ccc | c* | cc* | C | C* |
| 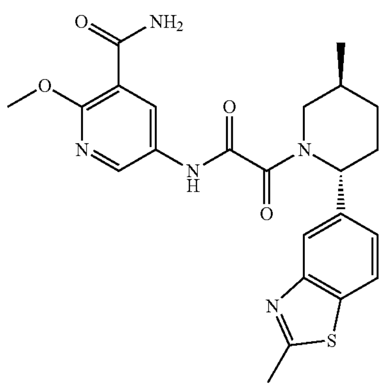 [SMILES: COc1ncc(NC(=O)C(=O)N2C[C@@H](C)CC[C@@H]2c2ccc3sc(C)nc3c2)cc1C(N)=O] | 797 | or/rel | b | aa | aaa | c* | aa* | A | A* |
| 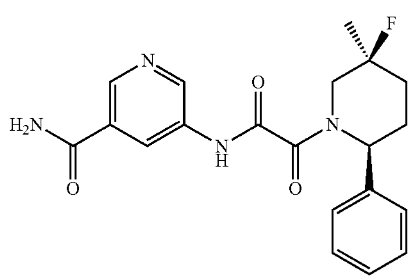 [SMILES: C[C@]1(F)CC[C@@H](c2ccccc2)N(C(=O)C(=O)Nc2cncc(C(N)=O)c2)C1] | 798 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 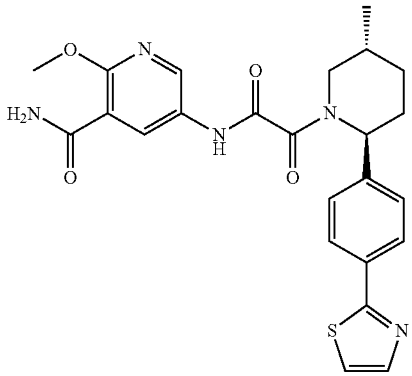 [SMILES: COc1ncc(NC(=O)C(=O)N2C[C@H](C)CC[C@H]2c2ccc(-c3nccs3)cc2)cc1C(N)=O] | 799 | or/rel | c | cc | ccc | c* | cc* | C | C* |
| 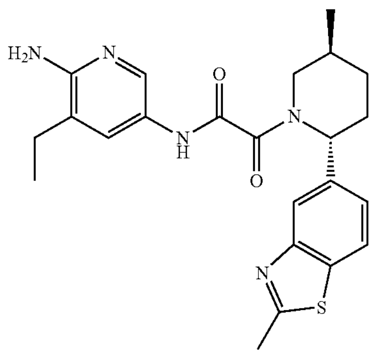 [SMILES: CCc1cc(NC(=O)C(=O)N2C[C@@H](C)CC[C@@H]2c2ccc3sc(C)nc3c2)cnc1N] | 800 | or/rel | b | aa | aaa | b* | aa* | A | A* |
| 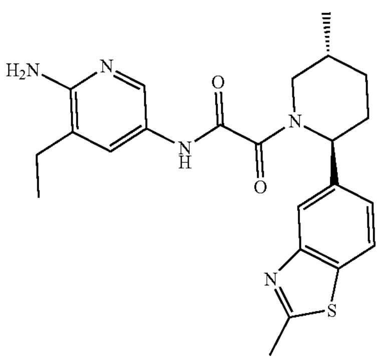 [SMILES: CCc1cc(NC(=O)C(=O)N2C[C@H](C)CC[C@H]2c2ccc3sc(C)nc3c2)cnc1N] | 801 | or/rel | c | cc | ccc | c* | cc* | B | C* |
| 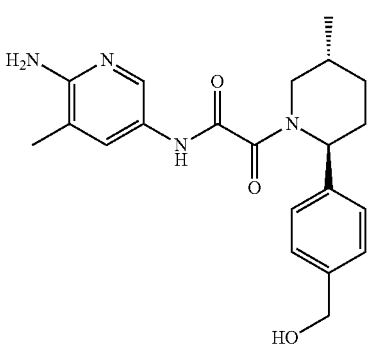 [SMILES: Cc1cc(NC(=O)C(=O)N2C[C@H](C)CC[C@H]2c2ccc(CO)cc2)cnc1N] | 802 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 803 | and/rac | b | bb | aaa | c* | aa* | A | A* |
| | 804 | or/rel | c | cc | ccc | c* | cc* | C | C* |
| | 805 | or/rel | c | cc | ccc | c* | bb* | A | C* |
| | 806 | or/rel | b | aa | aaa | b* | aa* | A | A* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 807 | or/rel | b | aa | aaa | b* | aa* | A | A* |
| | 808 | or/rel | c | cc | ccc | c* | cc* | C | C* |
| | 809 | or/rel | b | aa | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 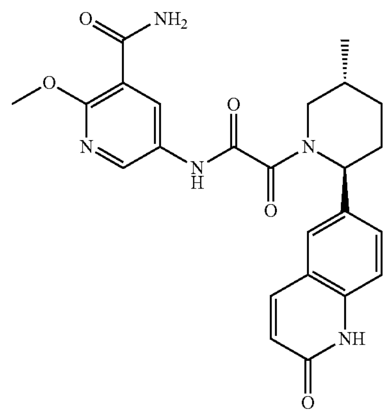 [SMILES: COc1ncc(NC(=O)C(=O)N2C[C@H](C)CC[C@H]2c2ccc3[nH]c(=O)ccc3c2)cc1C(N)=O] | 810 | or/rel | c | cc | ccc | c* | cc* | B | C* |
| 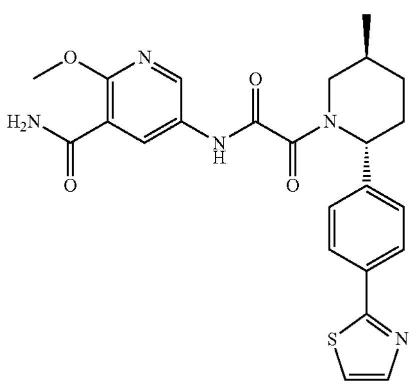 [SMILES: COc1ncc(NC(=O)C(=O)N2C[C@@H](C)CC[C@@H]2c2ccc(-c3nccs3)cc2)cc1C(N)=O] | 811 | or/rel | b | bb | aaa | c* | bb* | A | B* |
| 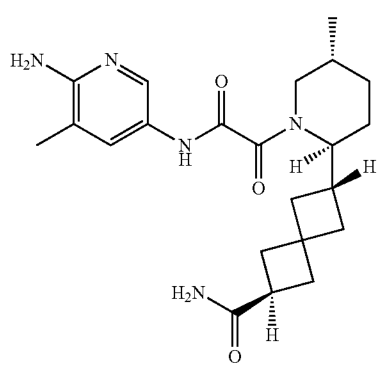 [SMILES: Cc1cc(NC(=O)C(=O)N2C[C@H](C)CC[C@H]2[C@H]2CC3(C[C@H](C(N)=O)C3)C2)cnc1N] | 812 | and/rac | c | cc | bbb | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 813 | or/rel | b | bb | aaa | c* | bb* | A | A* |
| | 814 | and/rac | b | bb | bbb | c* | bb* | A | C* |
| | 815 | and/rac | b | bb | aaa | b* | aa* | A | A* |
| | 816 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 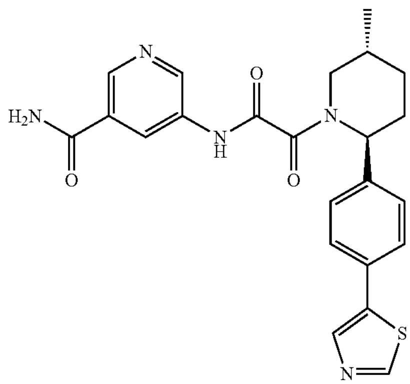 [SMILES: C[C@@H]1CC[C@@H](c2ccc(-c3cncs3)cc2)N(C(=O)C(=O)Nc2cncc(C(N)=O)c2)C1] | 817 | or/rel | c | cc | ccc | c* | cc* | C | C* |
| 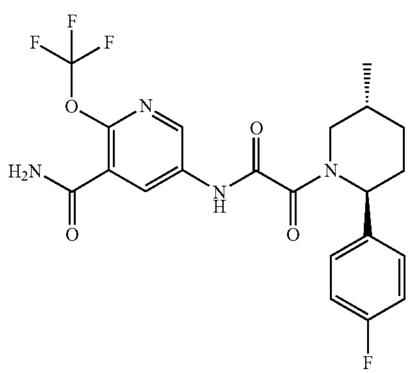 [SMILES: C[C@@H]1CC[C@@H](c2ccc(F)cc2)N(C(=O)C(=O)Nc2cnc(OC(F)(F)F)c(C(N)=O)c2)C1] | 818 | and/rac | b | bb | bbb | c* | bb* | A | C* |
| 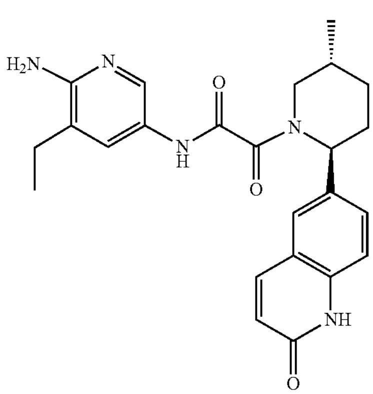 [SMILES: CCc1cc(NC(=O)C(=O)N2C[C@H](C)CC[C@H]2c2ccc3[nH]c(=O)ccc3c2)cnc1N] | 819 | or/rel | c | cc | ccc | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 820 | or/rel | b | bb | aaa | b* | aa* | B | A* |
| | 821 | or/rel | b | bb | aaa | c* | aa* | A | B* |
| | 822 | or/rel | c | cc | ccc | c* | cc* | C | C* |
| | 823 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 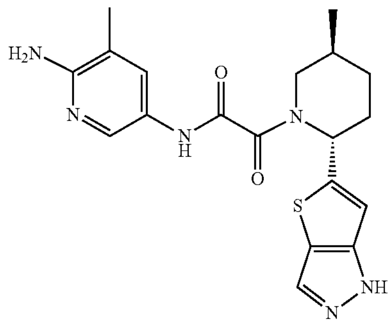 | 824 | or/rel | b | aa | aaa | b* | aa* | A | A* |
| 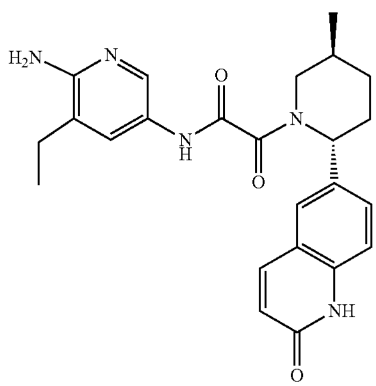 [SMILES: CCc1cc(NC(=O)C(=O)N2C[C@@H](C)CC[C@@H]2c2ccc3[nH]c(=O)ccc3c2)cnc1N] | 825 | or/rel | b | aa | aaa | b* | aa* | A | A* |
| 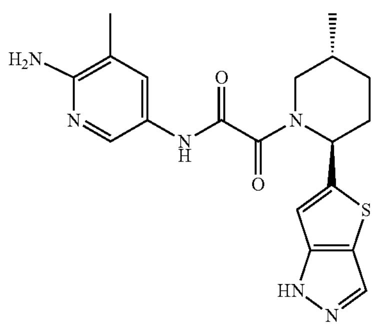 [SMILES: Cc1cc(NC(=O)C(=O)N2C[C@H](C)CC[C@H]2c2cc3[nH]ncc3s2)cnc1N] | 826 | or/rel | c | cc | bbb | c* | cc* | B | C* |
| 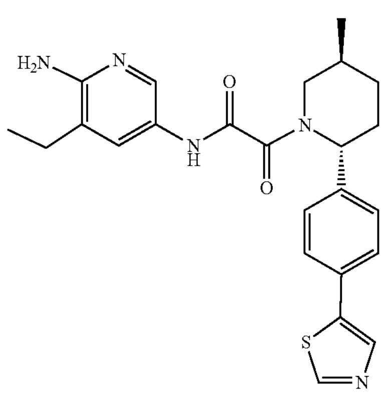 [SMILES: CCc1cc(NC(=O)C(=O)N2C[C@@H](C)CC[C@@H]2c2ccc(-c3cncs3)cc2)cnc1N] | 827 | or/rel | c | cc | bbb | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 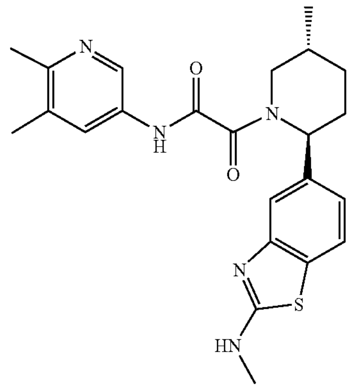 [SMILES: CNc1nc2cc([C@@H]3CC[C@@H](C)CN3C(=O)C(=O)Nc3cnc(C)c(C)c3)ccc2s1] | 828 | and/rac | b | bb | bbb | c* | aa* | A | B* |
| 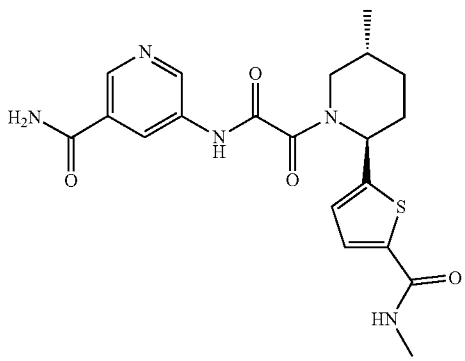 [SMILES: CNC(=O)c1ccc([C@@H]2CC[C@@H](C)CN2C(=O)C(=O)Nc2cncc(C(N)=O)c2)s1] | 829 | or/rel | b | aa | aaa | c* | aa* | A | B* |
| 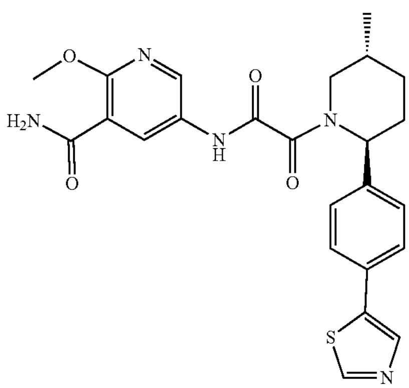 [SMILES: COc1ncc(NC(=O)C(=O)N2C[C@H](C)CC[C@H]2c2ccc(-c3cncs3)cc2)cc1C(N)=O] | 830 | or/rel | b | bb | aaa | c* | aa* | A | A* |
| 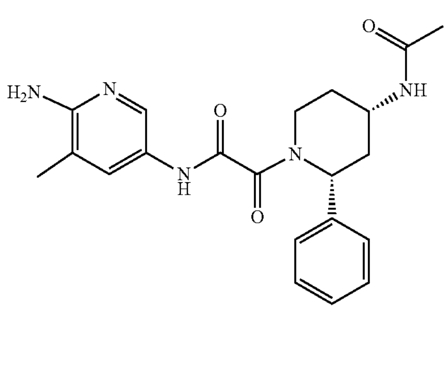 [SMILES: CC(=O)N[C@H]1CCN(C(=O)C(=O)Nc2cnc(N)c(C)c2)[C@@H](c2ccccc2)C1] | 831 | and/rac | c | cc | bbb | c* | cc* | B | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 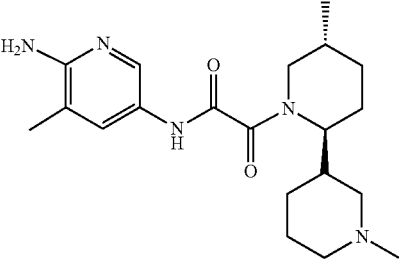 [SMILES: Cc1cc(NC(=O)C(=O)N2C[C@H](C)CC[C@H]2C2CCCN(C)C2)cnc1N] | 832 | and/rac | c | cc | bbb | c* | cc* | C | |
| 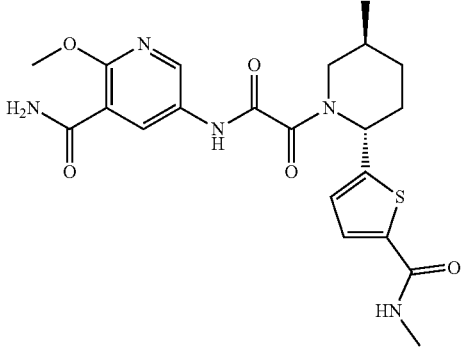 [SMILES: CNC(=O)c1ccc([C@H]2CC[C@H](C)CN2C(=O)C(=O)Nc2cnc(OC)c(C(N)=O)c2)s1] | 833 | or/rel | b | bb | aaa | b* | aa* | A | A* |
| 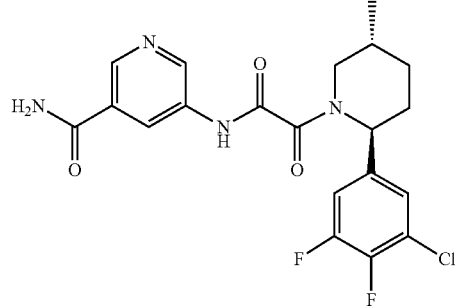 [SMILES: C[C@@H]1CC[C@@H](c2cc(F)c(F)c(Cl)c2)N(C(=O)C(=O)Nc2cncc(C(N)=O)c2)C1] | 834 | or/rel | b | bb | aaa | c* | bb* | A | B* |
| 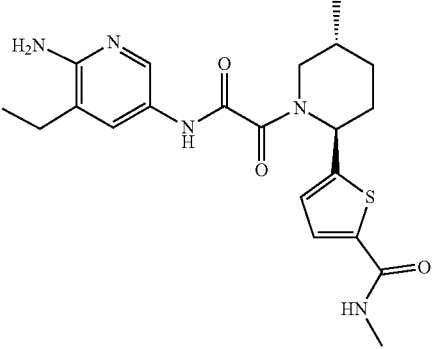 [SMILES: CCc1cc(NC(=O)C(=O)N2C[C@H](C)CC[C@H]2c2ccc(C(=O)NC)s2)cnc1N] | 835 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 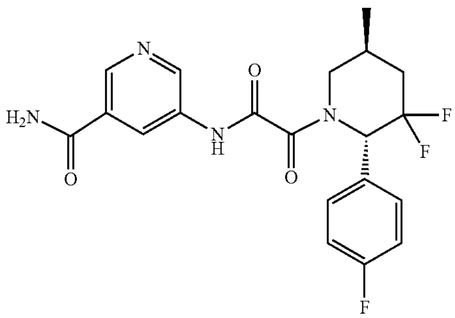 [SMILES: C[C@@H]1CN(C(=O)C(=O)Nc2cncc(C(N)=O)c2)[C@@H](c2ccc(F)cc2)C(F)(F)C1] | 836 | and/rac | b | bb | aaa | c* | bb* | A | B* |
| 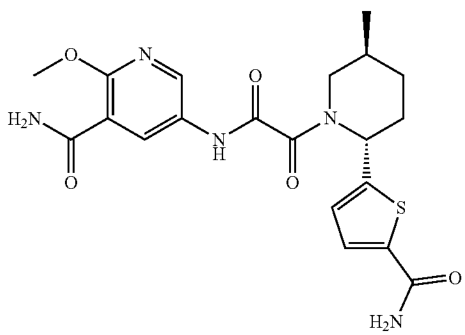 [SMILES: COc1ncc(NC(=O)C(=O)N2C[C@@H](C)CC[C@@H]2c2ccc(C(N)=O)s2)cc1C(N)=O] | 837 | or/rel | b | aa | aaa | c* | aa* | A | A* |
| 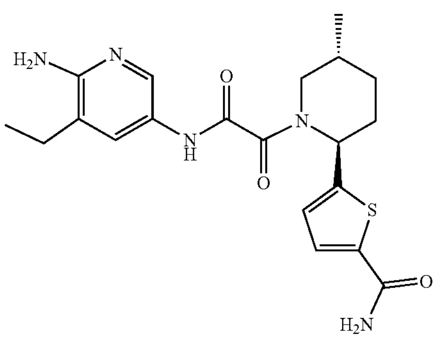 [SMILES: CCc1cc(NC(=O)C(=O)N2C[C@H](C)CC[C@H]2c2ccc(C(N)=O)s2)cnc1N] | 838 | or/rel | b | aa | aaa | b* | aa* | A | A* |
| 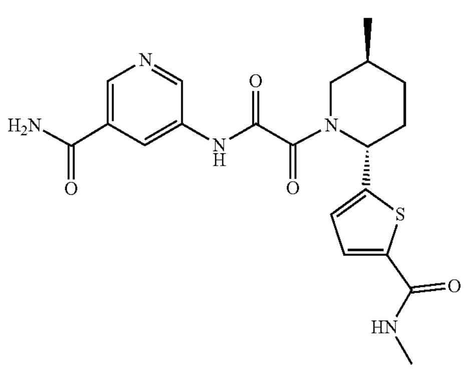 [SMILES: CNC(=O)c1ccc([C@H]2CC[C@H](C)CN2C(=O)C(=O)Nc2cncc(C(N)=O)c2)s1] | 839 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 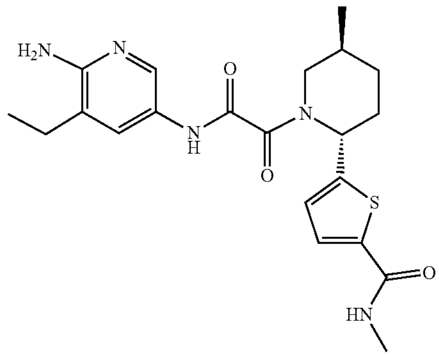 [SMILES: CCc1cc(NC(=O)C(=O)N2C[C@@H](C)CC[C@@H]2c2ccc(C(=O)NC)s2)cnc1N] | 840 | or/rel | b | aa | aaa | b* | aa* | A | A* |
| 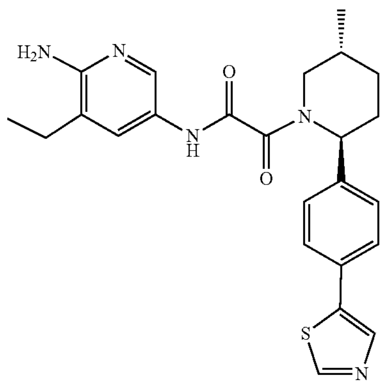 [SMILES: CCc1cc(NC(=O)C(=O)N2C[C@H](C)CC[C@H]2c2ccc(-c3cncs3)cc2)cnc1N] | 841 | or/rel | b | aa | aaa | b* | aa* | A | A* |
| 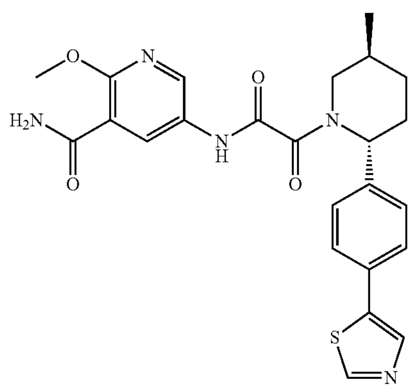 [SMILES: COc1ncc(NC(=O)C(=O)N2C[C@@H](C)CC[C@@H]2c2ccc(-c3cncs3)cc2)cc1C(N)=O] | 842 | or/rel | c | cc | ccc | c* | cc* | B | C* |
| 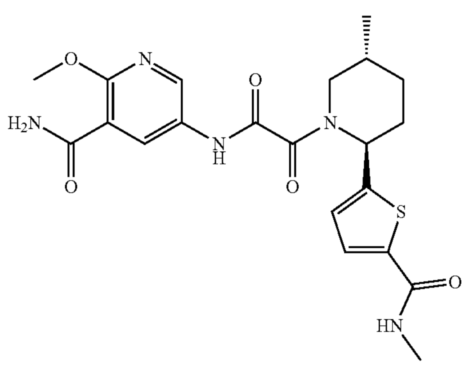 [SMILES: CNC(=O)c1ccc([C@@H]2CC[C@@H](C)CN2C(=O)C(=O)Nc2cnc(OC)c(C(N)=O)c2)s1] | 843 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 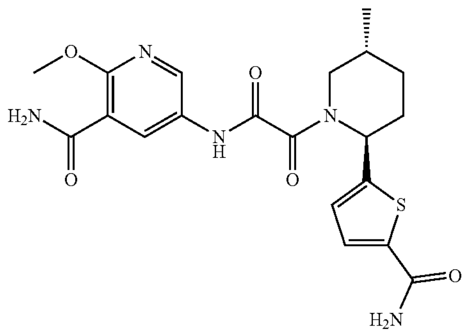 [SMILES: COc1ncc(NC(=O)C(=O)N2C[C@H](C)CC[C@H]2c2ccc(C(N)=O)s2)cc1C(N)=O] | 844 | or/rel | c | cc | ccc | c* | cc* | C | C* |
| 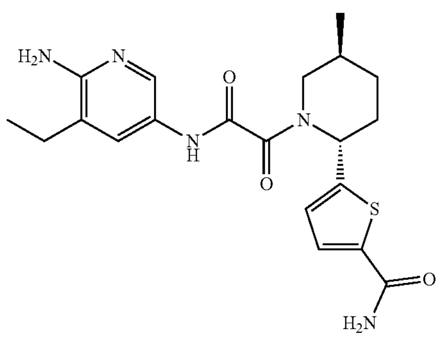 [SMILES: CCc1cc(NC(=O)C(=O)N2C[C@@H](C)CC[C@@H]2c2ccc(C(N)=O)s2)cnc1N] | 845 | or/rel | c | cc | ccc | c* | cc* | B | C* |
| 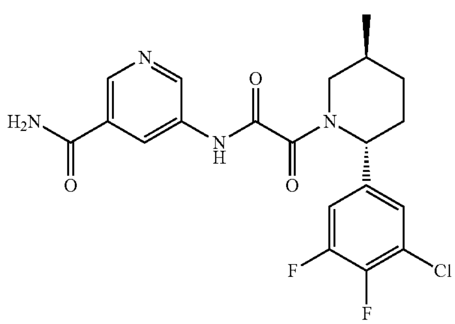 [SMILES: C[C@H]1CC[C@H](c2cc(F)c(F)c(Cl)c2)N(C(=O)C(=O)Nc2cncc(C(N)=O)c2)C1] | 846 | or/rel | c | cc | ccc | c* | cc* | C | |
| 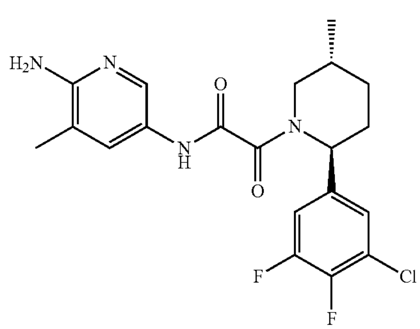 [SMILES: Cc1cc(NC(=O)C(=O)N2C[C@H](C)CC[C@H]2c2cc(F)c(F)c(Cl)c2)cnc1N] | 847 | or/rel | c | cc | ccc | c* | cc* | C | C* |

TABLE 1-continued

Exemplary compounds of the invention and biological data

| Structure | Nr | Stereo | SAM IC50 | No Co-factor/rel MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|
| (structure) | 848 | or/rel | b | aa | aaa | b* | aa* | A | A* |
| (structure) | 849 | or/rel | c | cc | ccc | c* | cc* | C | C* |
| (structure) | 850 | or/rel | c | cc | ccc | c* | cc* | C | C* |
| (structure) | 851 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 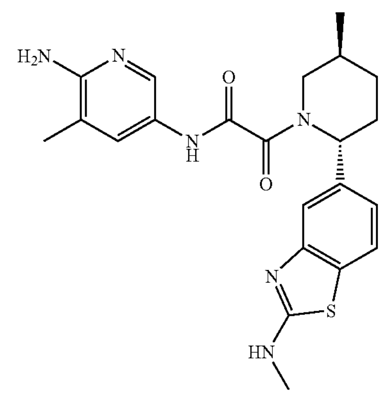 [SMILES: CNc1nc2cc([C@H]3CC[C@H](C)CN3C(=O)C(=O)Nc3cnc(N)c(C)c3)ccc2s1] | 852 | or/rel | b | aa | aaa | b* | aa* | A | A* |
| 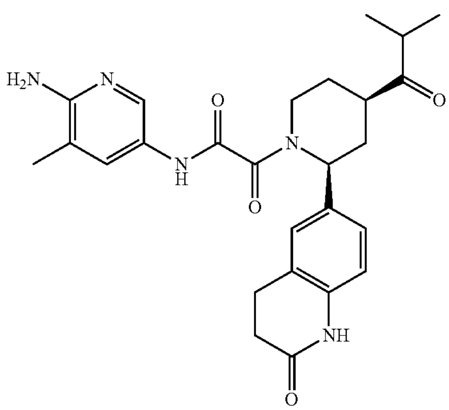 [SMILES: Cc1cc(NC(=O)C(=O)N2CC[C@@H](C(=O)C(C)C)C[C@H]2c2ccc3c(c2)CCC(=O)N3)cnc1N] | 853 | and/rac | b | bb | bbb | c* | bb* | A | B* |
| 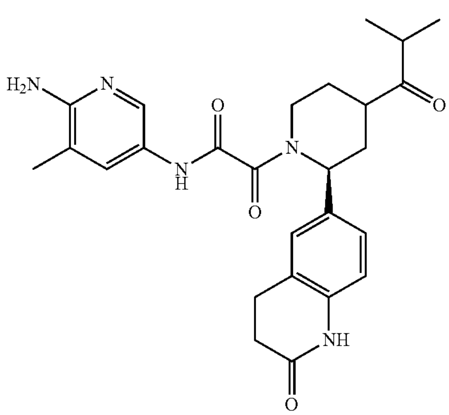 [SMILES: Cc1cc(NC(=O)C(=O)N2CCC(C(=O)C(C)C)C[C@H]2c2ccc3c(c2)CCC(=O)N3)cnc1N] | 854 | and/rac | b | bb | bbb | c* | bb* | A | B* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 855 | or/rel | c | cc | ccc | c* | cc* | C | C* |
| | 856 | or/rel | c | cc | ccc | c* | cc* | B | C* |
| | 857 | or/rel | b | bb | aaa | c* | aa* | A | B* |
| | 858 | or/rel | b | aa | aaa | c* | aa* | A | B* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 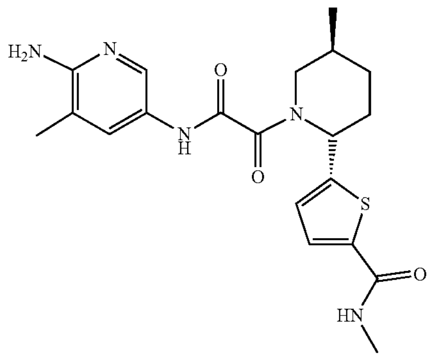 | 859 | or/rel | b | aa | aaa | b* | aa* | A | A* |
| 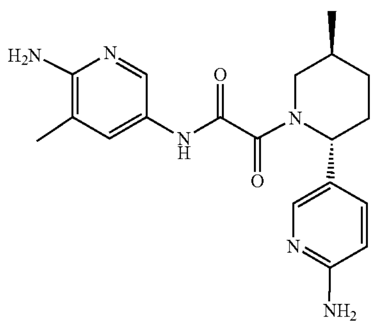 [SMILES: Cc1cc(NC(=O)C(=O)N2C[C@@H](C)CC[C@@H]2c2ccc(N)nc2)cnc1N] | 860 | or/rel | c | cc | ccc | c* | cc* | B | C* |
| 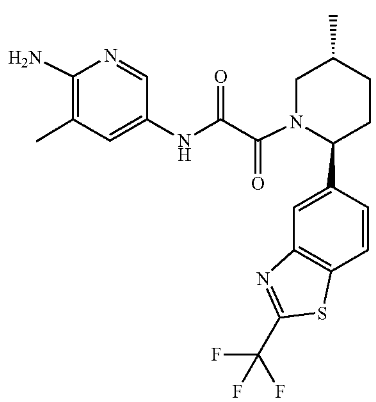 [SMILES: Cc1cc(NC(=O)C(=O)N2C[C@H](C)CC[C@H]2c2ccc3sc(C(F)(F)F)nc3c2)cnc1N] | 861 | and/rac | b | bb | bbb | b* | aa* | A | A* |
| 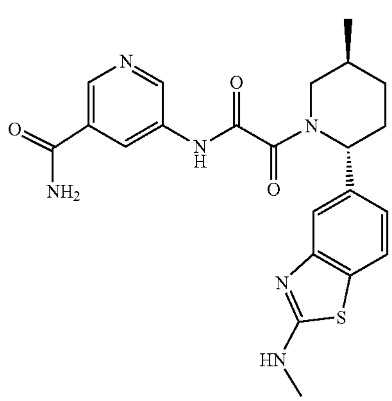 [SMILES: CNc1nc2cc([C@H]3CC[C@H](C)CN3C(=O)C(=O)Nc3cncc(C(N)=O)c3)ccc2s1] | 862 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 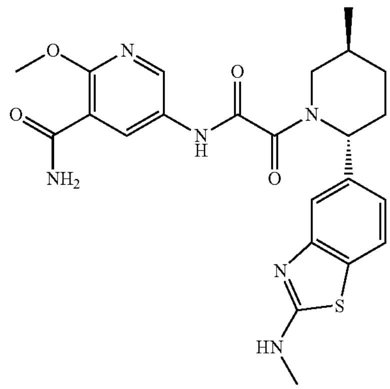 [SMILES: CNc1nc2cc([C@H]3CC[C@H](C)CN3C(=O)C(=O)Nc3cnc(OC)c(C(N)=O)c3)ccc2s1] | 863 | or/rel | b | aa | aaa | c* | aa* | A | A* |
| 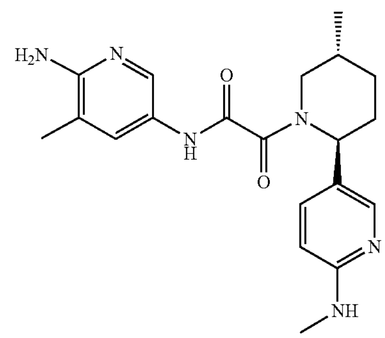 [SMILES: CNc1ccc([C@@H]2CC[C@@H](C)CN2C(=O)C(=O)Nc2cnc(N)c(C)c2)cn1] | 864 | or/rel | b | aa | aaa | b* | aa* | B | A* |
| 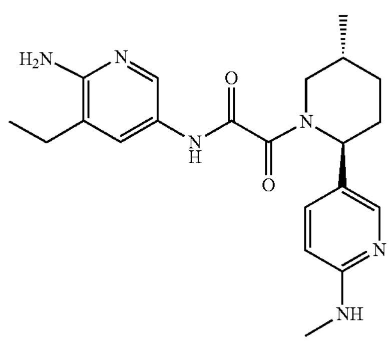 [SMILES: CCc1cc(NC(=O)C(=O)N2C[C@H](C)CC[C@H]2c2ccc(NC)nc2)cnc1N] | 865 | or/rel | b | aa | aaa | b* | aa* | A | A* |
| 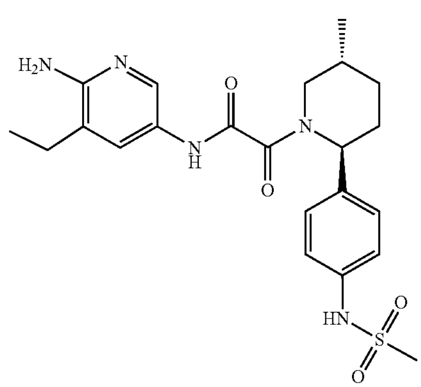 [SMILES: CCc1cc(NC(=O)C(=O)N2C[C@H](C)CC[C@H]2c2ccc(NS(C)(=O)=O)cc2)cnc1N] | 866 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 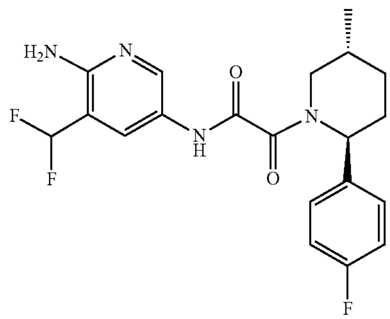 [SMILES: C[C@@H]1CC[C@@H](c2ccc(F)cc2)N(C(=O)C(=O)Nc2cnc(N)c(C(F)F)c2)C1] | 867 | and/rac | b | bb | bbb | c* | bb* | A | B* |
| 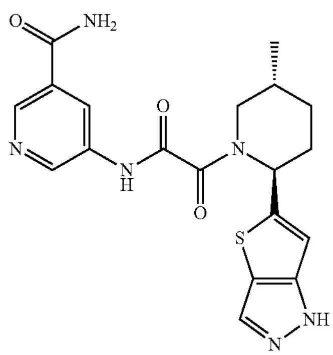 [SMILES: C[C@@H]1CC[C@@H](c2cc3[nH]ncc3s2)N(C(=O)C(=O)Nc2cncc(C(N)=O)c2)C1] | 868 | or/rel | c | cc | ccc | c* | cc* | C | C* |
| 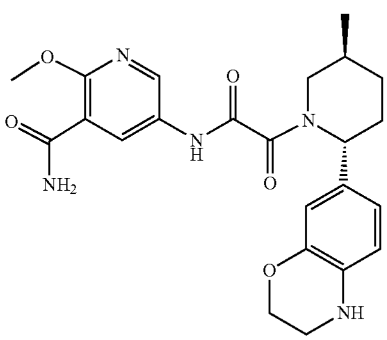 [SMILES: COc1ncc(NC(=O)C(=O)N2C[C@@H](C)CC[C@@H]2c2ccc3c(c2)OCCN3)cc1C(N)=O] | 869 | and/rac | b | bb | bbb | c* | aa* | A | A* |
| 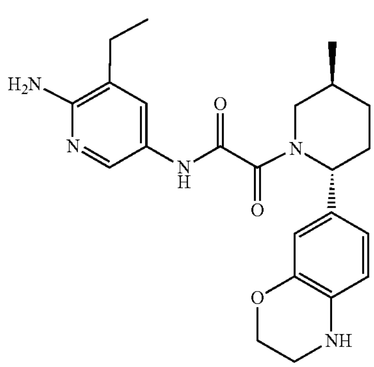 [SMILES: CCc1cc(NC(=O)C(=O)N2C[C@@H](C)CC[C@@H]2c2ccc3c(c2)OCCN3)cnc1N] | 870 | and/rac | b | bb | bbb | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 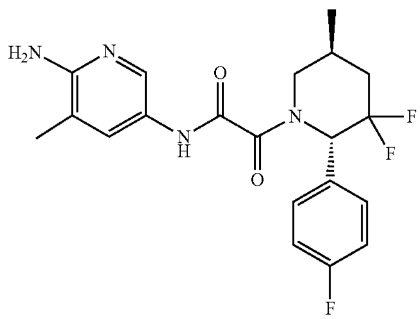 [SMILES: Cc1cc(NC(=O)C(=O)N2C[C@@H](C)CC(F)(F)[C@@H]2c2ccc(F)cc2)cnc1N] | 871 | and/rac | b | bb | aaa | b* | aa* | B | B* |
| 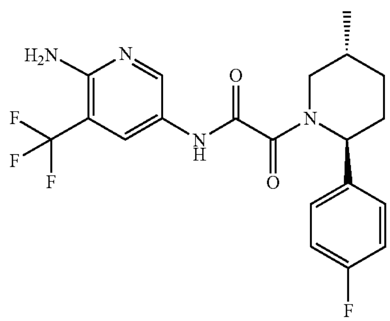 [SMILES: C[C@@H]1CC[C@@H](c2ccc(F)cc2)N(C(=O)C(=O)Nc2cnc(N)c(C(F)(F)F)c2)C1] | 872 | and/rac | c | bb | bbb | c* | bb* | A | B* |
| 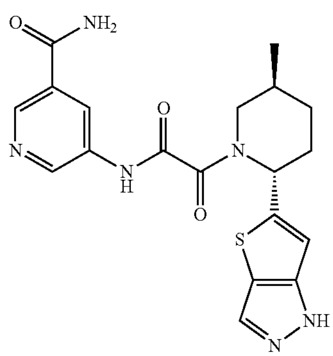 [SMILES: C[C@H]1CC[C@H](c2cc3[nH]ncc3s2)N(C(=O)C(=O)Nc2cncc(C(N)=O)c2)C1] | 873 | or/rel | b | bb | aaa | c* | aa* | A | A* |
| 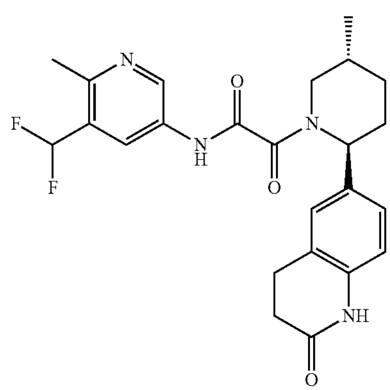 [SMILES: Cc1ncc(NC(=O)C(=O)N2C[C@H](C)CC[C@H]2c2ccc3c(c2)CCC(=O)N3)cc1C(F)F] | 874 | or/rel | b | bb | aaa | b* | aa* | A | A* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 875 | or/rel | c | cc | ccc | c* | cc* | B | C* |
| | 876 | or/rel | c | cc | ccc | c* | cc* | B | C* |
| | 877 | or/rel | b | bb | aaa | c* | aa* | A | A* |
| | 878 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 879 | and/rac | b | bb | aaa | c* | bb* | A | B* |
| | 880 | and/rac | c | cc | bbb | c* | bb* | A | C* |
| | 881 | or/rel | c | cc | ccc | c* | cc* | B | C* |
| | 882 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 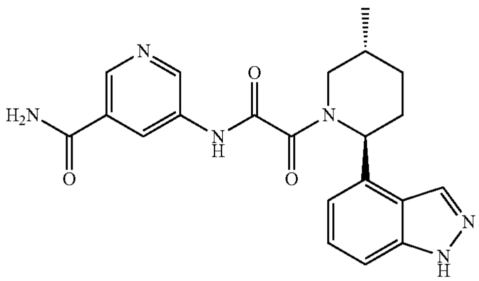 [SMILES: C[C@@H]1CC[C@@H](c2cccc3[nH]ncc23)N(C(=O)C(=O)Nc2cncc(C(N)=O)c2)C1] | 883 | or/rel | c | cc | ccc | c* | cc* | C | C* |
| 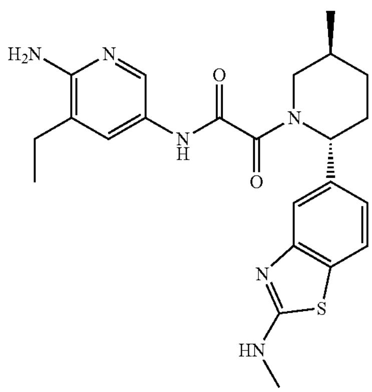 [SMILES: CCc1cc(NC(=O)C(=O)N2C[C@@H](C)CC[C@@H]2c2ccc3sc(NC)nc3c2)cnc1N] | 884 | or/rel | b | aa | aaa | b* | aa* | A | A* |
| 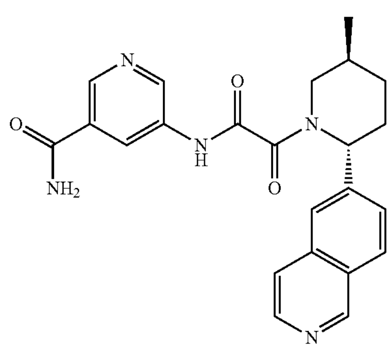 [SMILES: C[C@H]1CC[C@H](c2ccc3cnccc3c2)N(C(=O)C(=O)Nc2cncc(C(N)=O)c2)C1] | 885 | or/rel | c | cc | ccc | c* | cc* | C | C* |
| 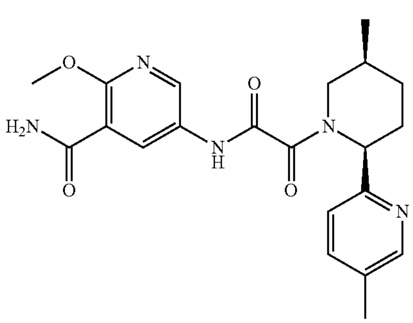 [SMILES: COc1ncc(NC(=O)C(=O)N2C[C@@H](C)CC[C@H]2c2ccc(C)cn2)cc1C(N)=O] | 886 | and/rac | c | cc | bbb | c* | cc* | B | C* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 887 | or/rel | b | bb | aaa | a* | aa* | B | A* |
| | 888 | and/rac | b | bb | bbb | c* | cc* | C | C* |
| | 889 | and/rac | c | bb | bbb | c* | cc* | B | C* |
| | 890 | or/rel | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 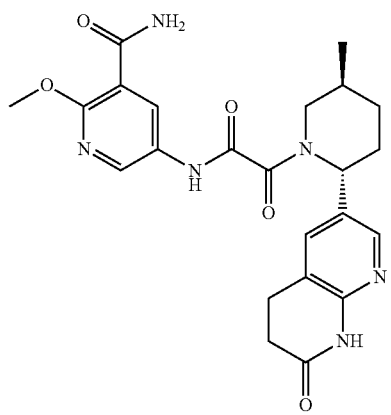 [SMILES: COc1ncc(NC(=O)C(=O)N2C[C@@H](C)CC[C@@H]2c2cnc3c(c2)CCC(=O)N3)cc1C(N)=O] | 891 | and/rac | b | bb | bb1 | c* | bb* | A | C* |
| 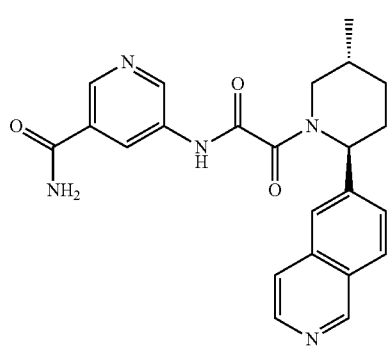 [SMILES: C[C@@H]1CC[C@@H](c2ccc3cnccc3c2)N(C(=O)C(=O)Nc2cncc(C(N)=O)c2)C1] | 892 | or/rel | b | bb | aaa | c* | aa* | A | A* |
| 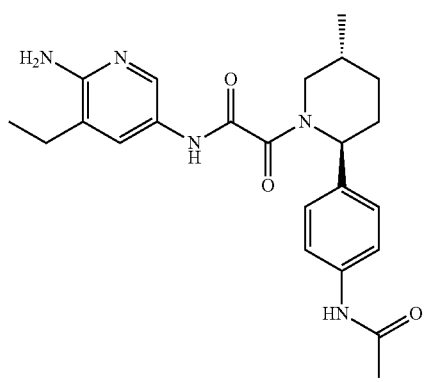 [SMILES: CCc1cc(NC(=O)C(=O)N2C[C@H](C)CC[C@H]2c2ccc(NC(C)=O)cc2)cnc1N] | 893 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 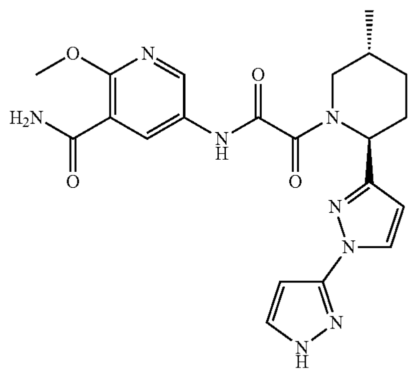 [SMILES: COc1ncc(NC(=O)C(=O)N2C[C@H](C)CC[C@H]2c2ccn(-c3cc[nH]n3)n2)cc1C(N)=O] | 894 | or/rel | b | bb | aaa | c* | aa* | A | B* |
| 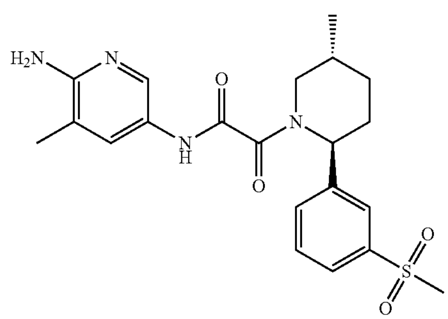 | 895 | or/rel | b | bb | aaa | b* | aa* | B | B* |
| 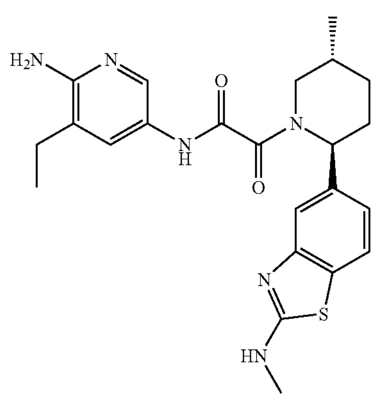 [SMILES: CCc1cc(NC(=O)C(=O)N2C[C@H](C)CC[C@H]2c2ccc3sc(NC)nc3c2)cnc1N] | 896 | or/rel | c | cc | ccc | c* | cc* | B | C* |
| 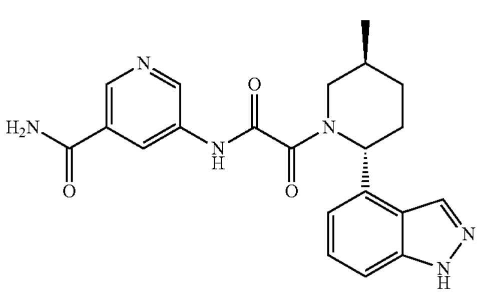 [SMILES: C[C@H]1CC[C@H](c2cccc3[nH]ncc23)N(C(=O)C(=O)Nc2cncc(C(N)=O)c2)C1] | 897 | or/rel | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 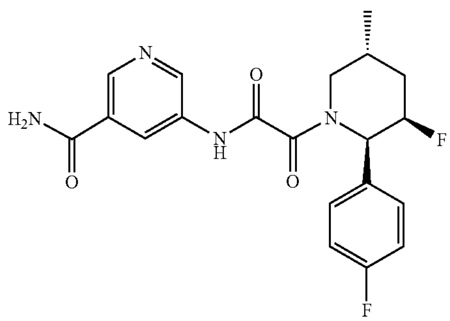 [SMILES: C[C@@H]1C[C@@H](F)[C@@H](c2ccc(F)cc2)N(C(=O)C(=O)Nc2cncc(C(N)=O)c2)C1] | 898 | and/rac | c | bb | bbb | c* | bb* | A | B* |
| 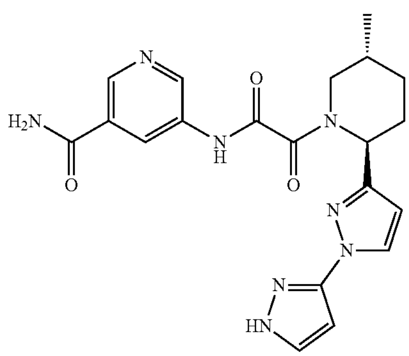 [SMILES: C[C@@H]1CC[C@@H](c2ccn(-c3cc[nH]n3)n2)N(C(=O)C(=O)Nc2cncc(C(N)=O)c2)C1] | 899 | or/rel | b | bb | aaa | c* | bb* | A | B* |
| 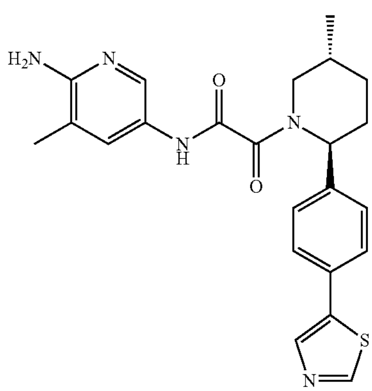 [SMILES: Cc1cc(NC(=O)C(=O)N2C[C@H](C)CC[C@H]2c2ccc(-c3cncs3)cc2)cnc1N] | 900 | or/rel | c | cc | ccc | c* | cc* | C | C* |
| 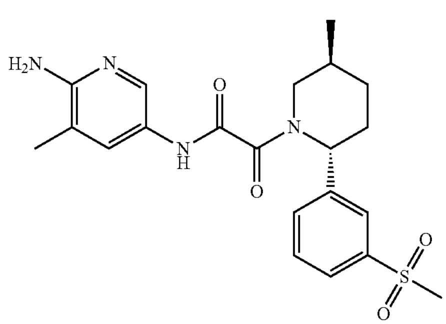 | 901 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 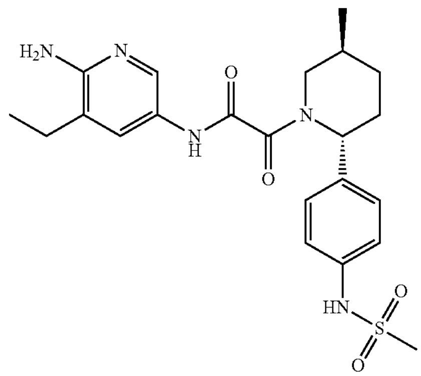 [SMILES: CCc1cc(NC(=O)C(=O)N2C[C@@H](C)CC[C@@H]2c2ccc(NS(C)(=O)=O)cc2)cnc1N] | 902 | or/rel | b | aa | aaa | b* | aa* | A | A* |
| 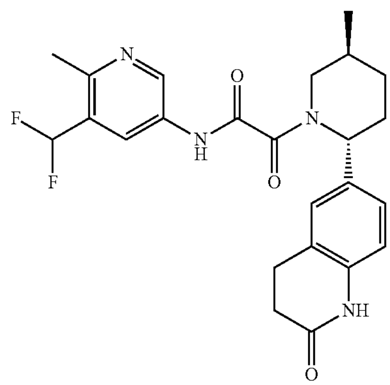 [SMILES: Cc1ncc(NC(=O)C(=O)N2C[C@@H](C)CC[C@@H]2c2ccc3c(c2)CCC(=O)N3)cc1C(F)F] | 903 | or/rel | c | cc | ccc | c* | cc* | B | C* |
| 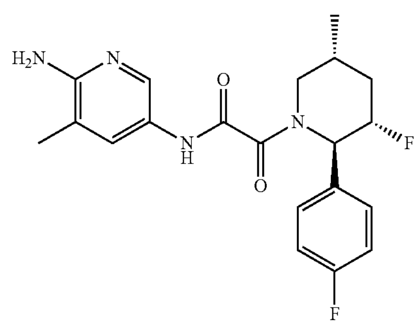 [SMILES: Cc1cc(NC(=O)C(=O)N2C[C@H](C)C[C@H](F)[C@H]2c2ccc(F)cc2)cnc1N] | 904 | and/rac | c | bb | bbb | b* | aa* | A | B* |
| 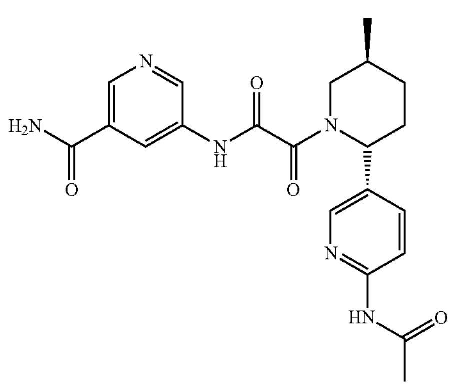 | 905 | or/rel | c | cc | ccc | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 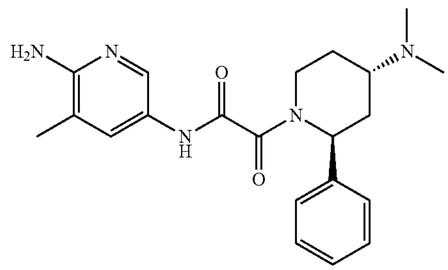 [SMILES: Cc1cc(NC(=O)C(=O)N2CC[C@H](N(C)C)C[C@H]2c2ccccc2)cnc1N] | 906 | and/rac | b | cc | bbb | c* | cc* | C | C* |
| 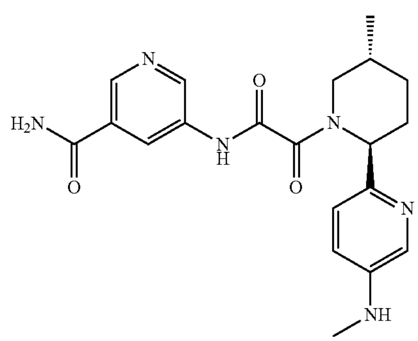 [SMILES: CNc1ccc([C@@H]2CC[C@@H](C)CN2C(=O)C(=O)Nc2cncc(C(N)=O)c2)nc1] | 907 | and/rac | b | bb | bbb | c* | aa* | A | B* |
| 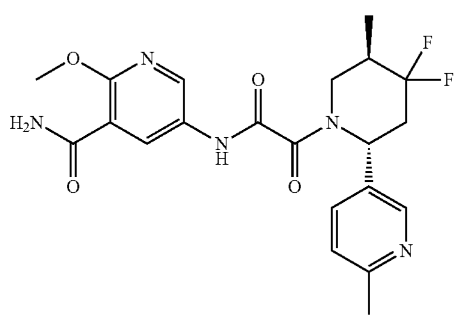 [SMILES: COc1ncc(NC(=O)C(=O)N2C[C@@H](C)C(F)(F)C[C@@H]2c2ccc(C)nc2)cc1C(N)=O] | 908 | or/rel | b | bb | aaa | c* | aa* | A | B* |
| 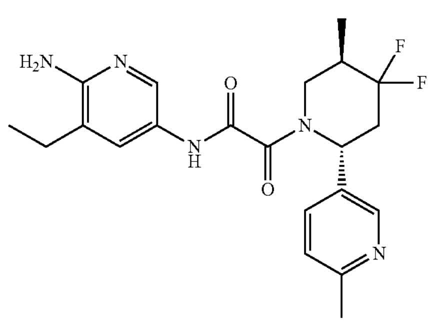 [SMILES: CCc1cc(NC(=O)C(=O)N2C[C@@H](C)C(F)(F)C[C@@H]2c2ccc(C)nc2)cnc1N] | 909 | or/rel | b | aa | aaa | b* | aa* | A | A* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| | 910 | or/rel | c | cc | ccc | c* | cc* | B | C* |
| | 911 | and/rac | c | cc | ccc | c* | cc* | C | C* |
| | 912 | and/rac | b | bb | bbb | b* | aa* | A | A* |
| | 913 | or/rel | c | cc | ccc | c* | cc* | C | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 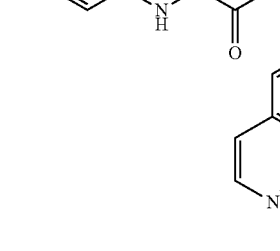 | 914 | or/rel | b | aa | aaa | b* | aa* | A | A* |
| 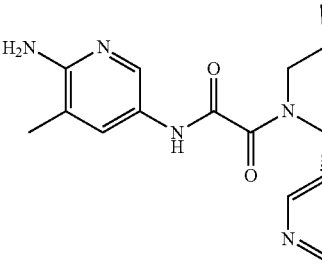 | 915 | or/rel | b | aa | aaa | b* | aa* | A | B* |
| 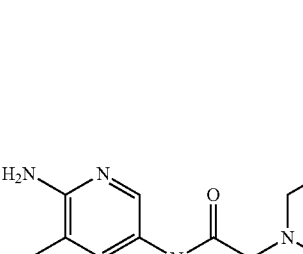 | 916 | and/rac | c | bb | bbb | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 917 | or/rel | b | aa | aaa | c* | aa* | A | B* |
| | 918 | or/rel | b | bb | aaa | c* | aa* | A | A* |
| | 919 | or/rel | b | aa | aaa | b* | aa* | A | A* |
| | 920 | and/rac | b | bb | bbb | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 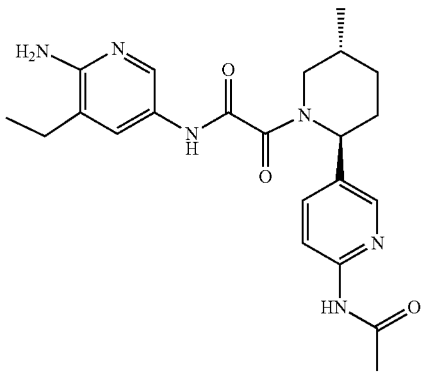 [SMILES: CCc1cc(NC(=O)C(=O)N2C[C@H](C)CC[C@H]2c2ccc(NC(C)=O)nc2)cnc1N] | 921 | or/rel | c | cc | ccc | c* | cc* | B | C* |
| 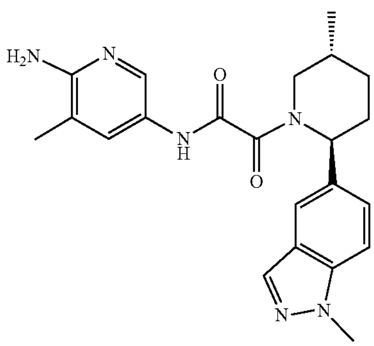 [SMILES: Cc1cc(NC(=O)C(=O)N2C[C@H](C)CC[C@H]2c2ccc3c(cnn3C)c2)cnc1N] | 922 | and/rac | b | bb | aaa | | | | A* |
| 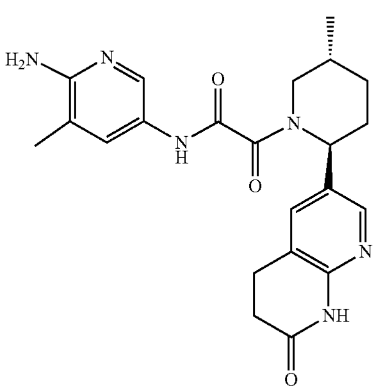 [SMILES: Cc1cc(NC(=O)C(=O)N2C[C@H](C)CC[C@H]2c2cnc3c(c2)CCC(=O)N3)cnc1N] | 923 | and/rac | b | bb | bbb | c* | bb* | A | B* |
| 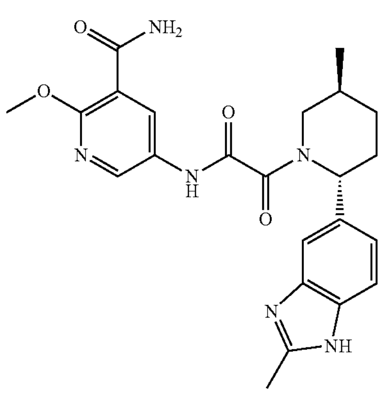 [SMILES: COc1ncc(NC(=O)C(=O)N2C[C@@H](C)CC[C@@H]2c2ccc3[nH]c(C)nc3c2)cc1C(N)=O] | 924 | or/rel | c | cc | ccc | c* | cc* | B | C* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 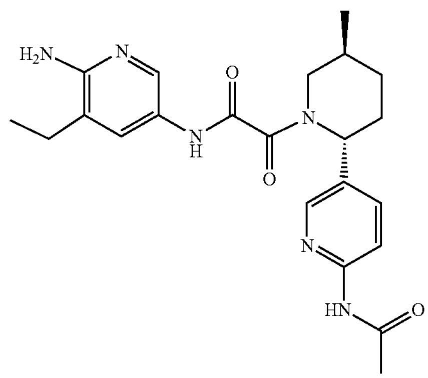 [SMILES: CCc1cc(NC(=O)C(=O)N2C[C@@H](C)CC[C@@H]2c2ccc(NC(C)=O)nc2)cnc1N] | 925 | or/rel | b | aa | aaa | b* | aa* | A | A* |
| 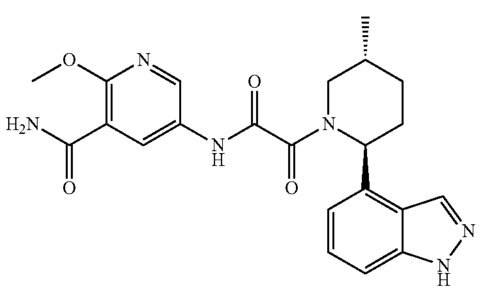 [SMILES: COc1ncc(NC(=O)C(=O)N2C[C@H](C)CC[C@H]2c2cccc3[nH]ncc23)cc1C(N)=O] | 926 | or/rel | c | cc | ccc | c* | cc* | C | C* |
| 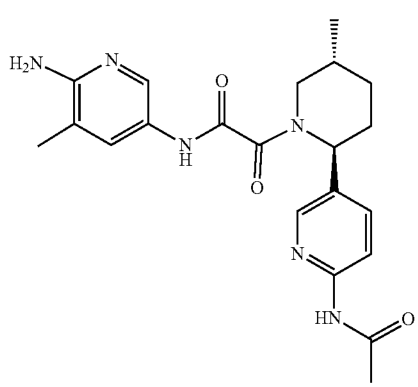 [SMILES: CC(=O)Nc1ccc([C@@H]2CC[C@@H](C)CN2C(=O)C(=O)Nc2cnc(N)c(C)c2)cn1] | 927 | or/rel | c | cc | ccc | c* | cc* | C | C* |
| 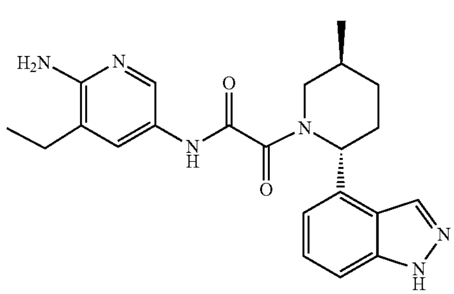 [SMILES: CCc1cc(NC(=O)C(=O)N2C[C@@H](C)CC[C@@H]2c2cccc3[nH]ncc23)cnc1N] | 928 | or/rel | b | aa | aaa | c* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 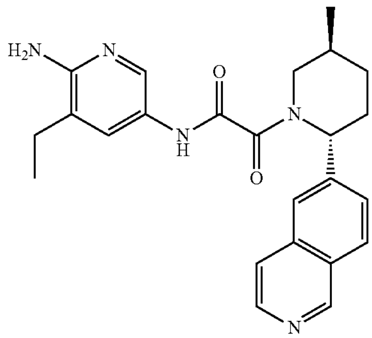 [SMILES: CCc1cc(NC(=O)C(=O)N2C[C@@H](C)CC[C@@H]2c2ccc3cnccc3c2)cnc1N] | 929 | or/rel | c | cc | ccc | c* | bb* | A | B* |
| 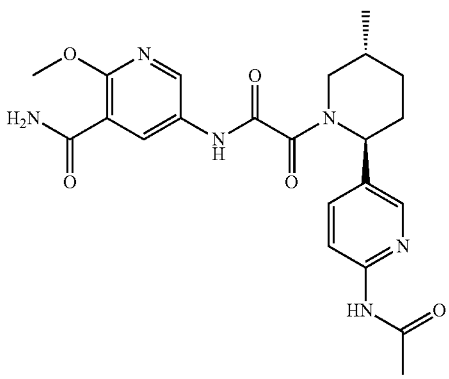 [SMILES: COc1ncc(NC(=O)C(=O)N2C[C@H](C)CC[C@H]2c2ccc(NC(C)=O)nc2)cc1C(N)=O] | 930 | or/rel | b | bb | aaa | c* | aa* | A | B* |
| 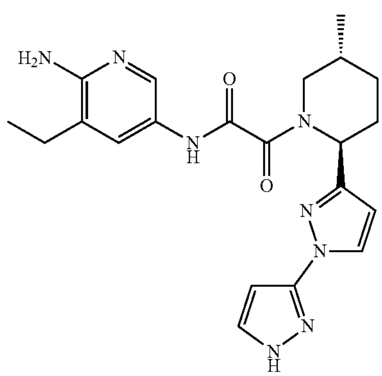 [SMILES: CCc1cc(NC(=O)C(=O)N2C[C@H](C)CC[C@H]2c2ccn(-c3cc[nH]n3)n2)cnc1N] | 931 | or/rel | b | bb | aaa | b* | aa* | A | A* |
| 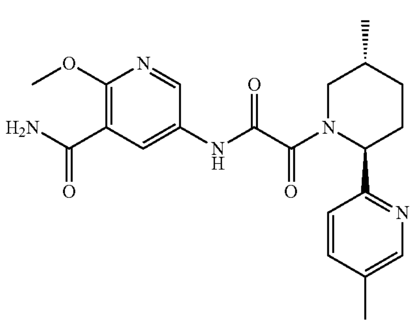 [SMILES: COc1ncc(NC(=O)C(=O)N2C[C@H](C)CC[C@H]2c2ccc(C)cn2)cc1C(N)=O] | 932 | and/rac | b | bb | bbb | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| (structure 933) | 933 | or/rel | c | cc | ccc | c* | cc* | B | C* |
| (structure 934) | 934 | or/rel | b | bb | aaa | c* | bb* | A | C* |
| (structure 935) | 935 | or/rel | c | cc | ccc | c* | cc* | C | C* |
| (structure 936) | 936 | or/rel | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 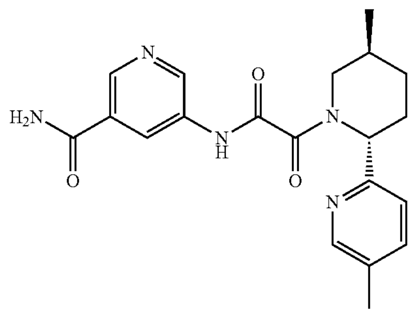 [SMILES: Cc1ccc([C@H]2CC[C@H](C)CN2C(=O)C(=O)Nc2cncc(C(N)=O)c2)nc1] | 937 | and/rac | b | bb | bbb | c* | bb* | A | B* |
| 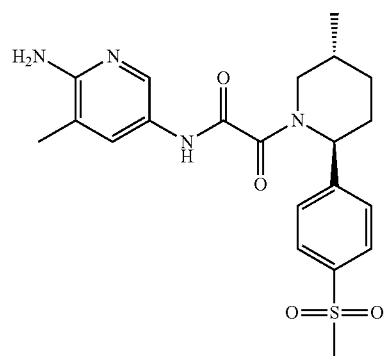 [SMILES: Cc1cc(NC(=O)C(=O)N2C[C@H](C)CC[C@H]2c2ccc(S(C)(=O)=O)cc2)cnc1N] | 938 | or/rel | c | cc | ccc | | | | C* |
| 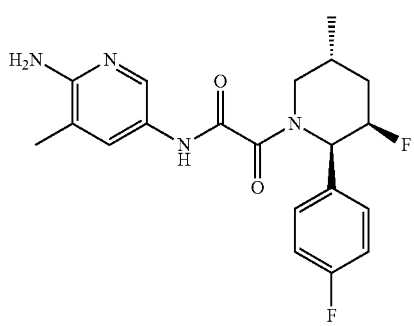 [SMILES: Cc1cc(NC(=O)C(=O)N2C[C@H](C)C[C@@H](F)[C@H]2c2ccc(F)cc2)cnc1N] | 939 | and/rac | b | bb | bbb | c* | bb* | A | B* |
| 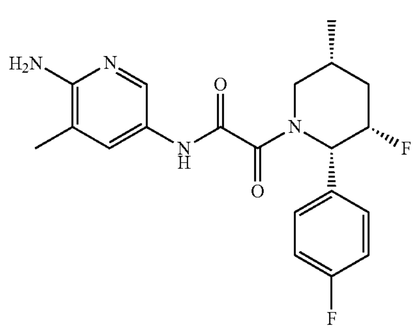 [SMILES: Cc1cc(NC(=O)C(=O)N2C[C@H](C)C[C@H](F)[C@@H]2c2ccc(F)cc2)cnc1N] | 940 | and/rac | b | bb | bbb | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 941 | or/rel | b | aa | aaa | b* | aa* | B | B* |
| | 942 | or/rel | b | bb | aaa | c* | bb* | A | C* |
| | 943 | or/rel | b | aa | aaa | b* | aa* | A | A* |
| | 944 | or/rel | c | cc | ccc | c* | cc* | C | C* |
| | 945 | or/rel | b | bb | aaa | c* | aa* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 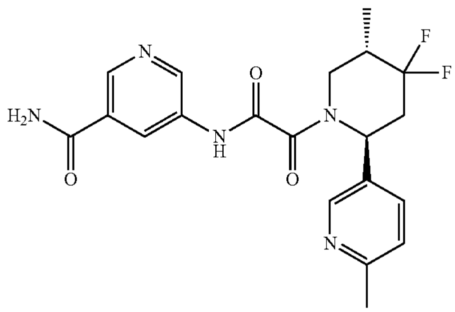 [SMILES: Cc1ccc([C@@H]2CC(F)(F)[C@@H](C)CN2C(=O)C(=O)Nc2cncc(C(N)=O)c2)cn1] | 946 | or/rel | c | cc | ccc | c* | cc* | B | C* |
| 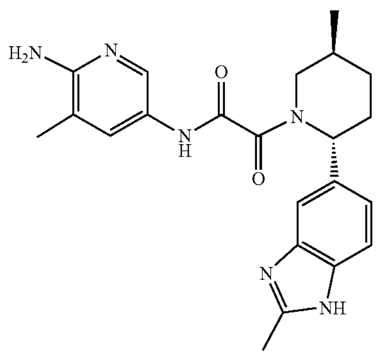 [SMILES: Cc1nc2cc([C@H]3CC[C@H](C)CN3C(=O)C(=O)Nc3cnc(N)c(C)c3)ccc2[nH]1] | 947 | or/rel | b | bb | aaa | b* | aa* | A | A* |
| 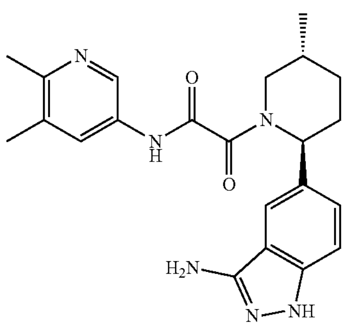 [SMILES: Cc1cc(NC(=O)C(=O)N2C[C@H](C)CC[C@H]2c2ccc3[nH]nc(N)c3c2)cnc1C] | 948 | or/rel | b | bb | aaa | c* | aa* | A | A* |
| 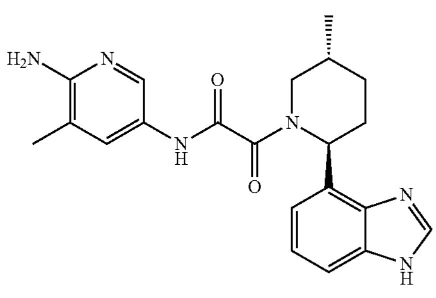 [SMILES: Cc1cc(NC(=O)C(=O)N2C[C@H](C)CC[C@H]2c2cccc3[nH]cnc23)cnc1N] | 949 | or/rel | b | bb | aaa | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 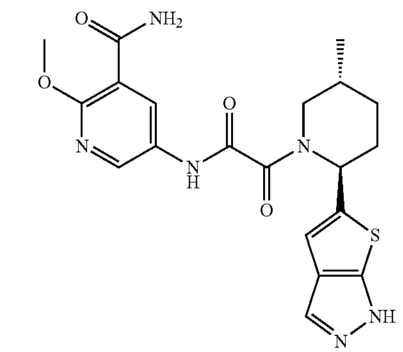 [SMILES: COc1ncc(NC(=O)C(=O)N2C[C@H](C)CC[C@H]2c2cc3cn[nH]c3s2)cc1C(N)=O] | 950 | or/rel | c | cc | ccc | c* | cc* | B | C* |
| 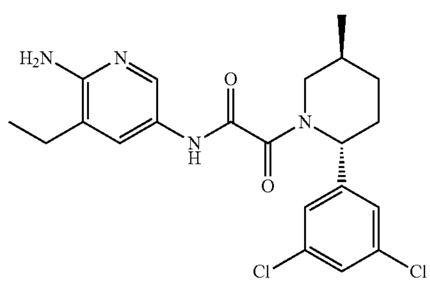 [SMILES: CCc1cc(NC(=O)C(=O)N2C[C@@H](C)CC[C@@H]2c2cc(Cl)cc(Cl)c2)cnc1N] | 951 | or/rel | b | aa | aaa | c* | aa* | A | B* |
| 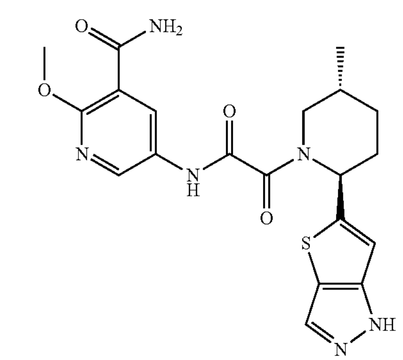 [SMILES: COc1ncc(NC(=O)C(=O)N2C[C@H](C)CC[C@H]2c2cc3[nH]ncc3s2)cc1C(N)=O] | 952 | or/rel | c | cc | ccc | c* | cc* | B | C* |
| 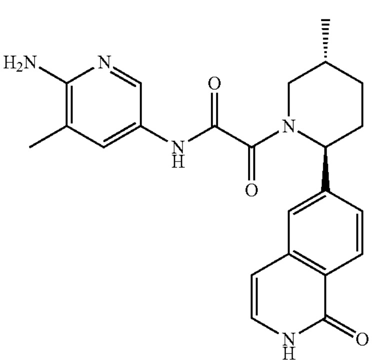 [SMILES: Cc1cc(NC(=O)C(=O)N2C[C@H](C)CC[C@H]2c2ccc3c(=O)[nH]ccc3c2)cnc1N] | 953 | or/rel | c | cc | bbb | c* | bb* | A | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 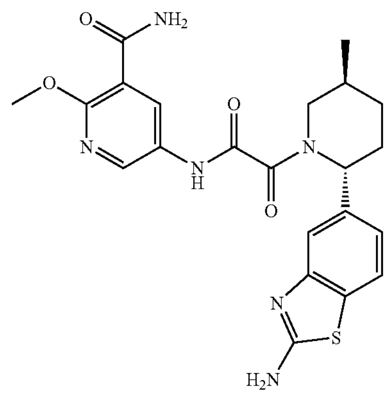 [SMILES: COc1ncc(NC(=O)C(=O)N2C[C@@H](C)CC[C@@H]2c2ccc3sc(N)nc3c2)cc1C(N)=O] | 954 | and/rac | b | bb | bbb | | | | A* |
| 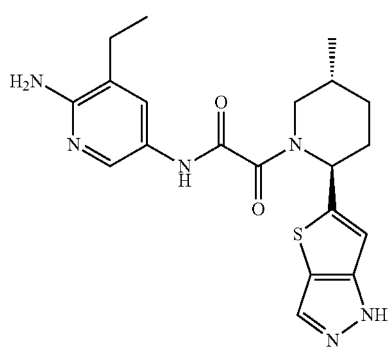 [SMILES: CCc1cc(NC(=O)C(=O)N2C[C@H](C)CC[C@H]2c2cc3[nH]ncc3s2)cnc1N] | 955 | or/rel | b | aa | aaa | b* | aa* | A | A* |
| 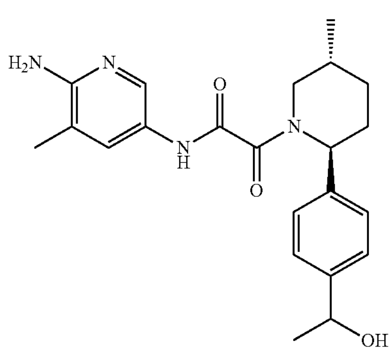 [SMILES: Cc1cc(NC(=O)C(=O)N2C[C@H](C)CC[C@H]2c2ccc(C(C)O)cc2)cnc1N] | 956 | and/rac | b | bb | bbb | | | | B* |
| 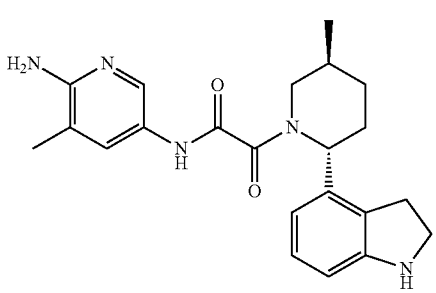 | 957 | or/rel | c | cc | ccc | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| | 958 | or/rel | c | cc | ccc | | | | C* |
| | 959 | or/rel | c | cc | ccc | c* | cc* | B | C* |
| | 960 | or/rel | b | bb | aaa | c* | bb* | A | B* |
| | 961 | or/rel | c | bb | aaa | c* | aa* | A | B* |

TABLE 1-continued

Exemplary compounds of the invention and biological data

| Structure | Nr | Stereo | SAM IC50 | No Cofactor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 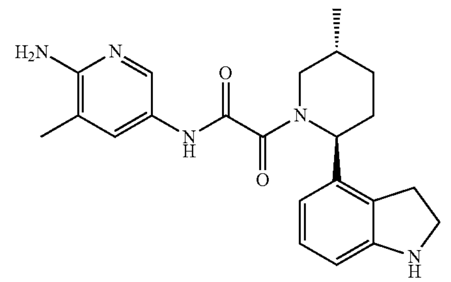 [SMILES: Cc1cc(NC(=O)C(=O)N2C[C@H](C)CC[C@H]2c2cccc3c2CCN3)cnc1N] | 962 | or/rel | b | bb | aaa | c* | bb* | A | B* |
| 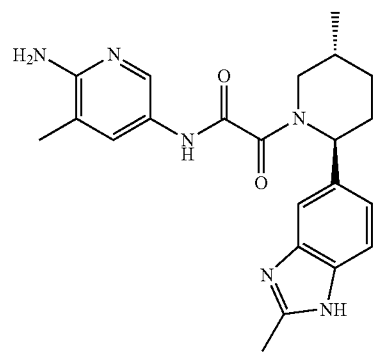 [SMILES: Cc1nc2cc([C@@H]3CC[C@@H](C)CN3C(=O)C(=O)Nc3cnc(N)c(C)c3)ccc2[nH]1] | 963 | or/rel | c | cc | ccc | c* | cc* | B | C* |
| 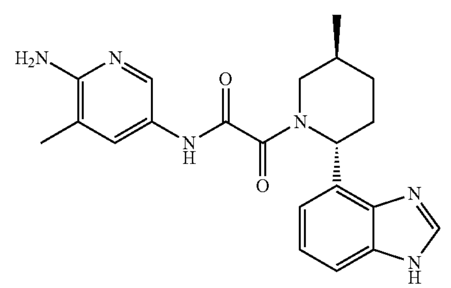 [SMILES: Cc1cc(NC(=O)C(=O)N2C[C@@H](C)CC[C@@H]2c2cccc3[nH]cnc23)cnc1N] | 964 | or/rel | c | cc | ccc | c* | cc* | C | C* |
| 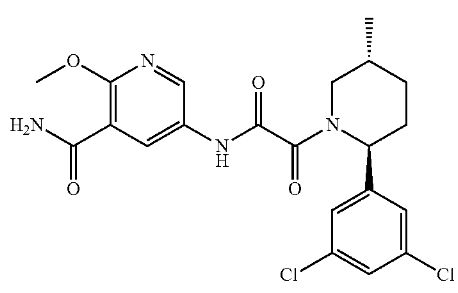 [SMILES: COc1ncc(NC(=O)C(=O)N2C[C@H](C)CC[C@H]2c2cc(Cl)cc(Cl)c2)cc1C(N)=O] | 965 | or/rel | c | cc | ccc | c* | cc* | B | C* |
| 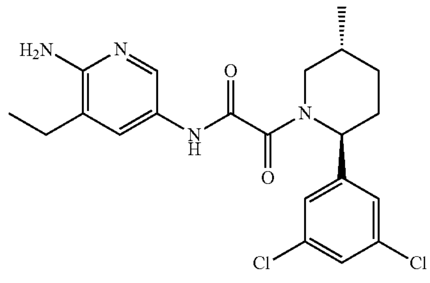 [SMILES: CCc1cc(NC(=O)C(=O)N2C[C@H](C)CC[C@H]2c2cc(Cl)cc(Cl)c2)cnc1N] | 966 | or/rel | c | cc | bbb | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 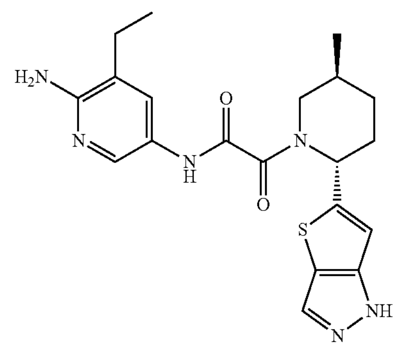 [SMILES: CCc1cc(NC(=O)C(=O)N2C[C@@H](C)CC[C@@H]2c2cc3[nH]ncc3s2)cnc1N] | 967 | or/rel | c | cc | ccc | c* | cc* | B | C* |
| 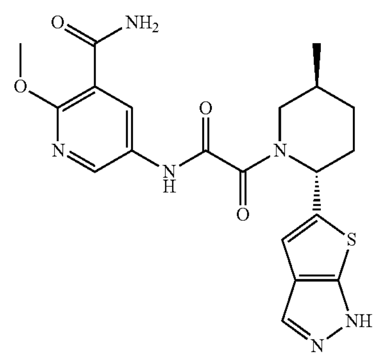 [SMILES: COc1ncc(NC(=O)C(=O)N2C[C@@H](C)CC[C@@H]2c2cc3cn[nH]c3s2)cc1C(N)=O] | 968 | or/rel | b | aa | aaa | b* | aa* | A | A* |
| 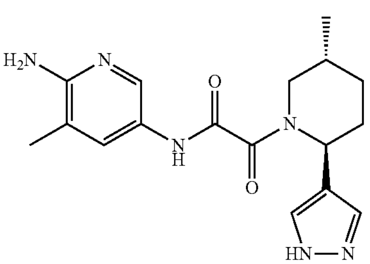 [SMILES: Cc1cc(NC(=O)C(=O)N2C[C@H](C)CC[C@H]2c2cn[nH]c2)cnc1N] | 969 | or/rel | c | cc | ccc | c* | cc* | C | C* |
| 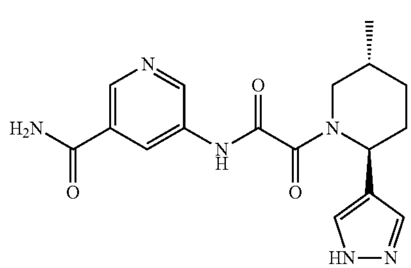 [SMILES: C[C@@H]1CC[C@@H](c2cn[nH]c2)N(C(=O)C(=O)Nc2cncc(C(N)=O)c2)C1] | 970 | or/rel | c | cc | ccc | c* | cc* | C | C* |

TABLE 1-continued

Exemplary compounds of the invention and biological data

| Structure | Nr | Stereo | No Co-factor/ SAM rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|
| [structure] | 971 | or/rel | c | cc | ccc | | | C* |
| [structure] | 972 | or/rel | b | bb | aaa | a* | aa* | B | A* |
| [structure] | 973 | or/rel | b | bb | aaa | b* | aa* | A | B* |
| [structure] | 974 | or/rel | b | bb | aaa | c* | aa* | A | B* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure 975) | 975 | and/rac | c | cc | ccc | | | | C* |
| (structure 976) | 976 | or/rel | b | bb | aaa | | | | B* |
| (structure 977) | 977 | and/rac | b | bb | bbb | b* | aa* | B | B* |
| (structure 978) | 978 | or/rel | c | bb | bbb | c* | cc* | C | C* |
| (structure 979) | 979 | abs | b | bb | aaa | c* | bb* | A | B* |

TABLE 1-continued

Exemplary compounds of the invention and biological data

| Structure | Nr | Stereo | No Co-factor/ SAM rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|
| | 980 | or/rel | b | bb | bbb | c* | cc* | B | C* |
| | 981 | or/rel | c | cc | ccc | | | | C* |
| | 982 | and/rac | c | bb | bbb | c* | bb* | B | C* |
| | 983 | or/rel | c | cc | ccc | | | | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 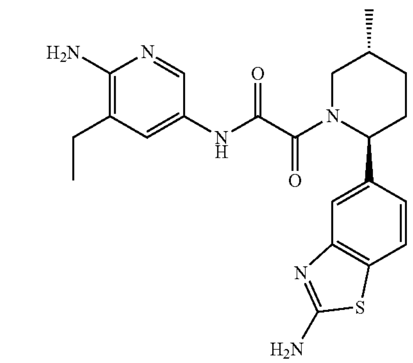 [SMILES: CCc1cc(NC(=O)C(=O)N2C[C@H](C)CC[C@H]2c2ccc3sc(N)nc3c2)cnc1N] | 984 | or/rel | c | cc | ccc | | | | C* |
| 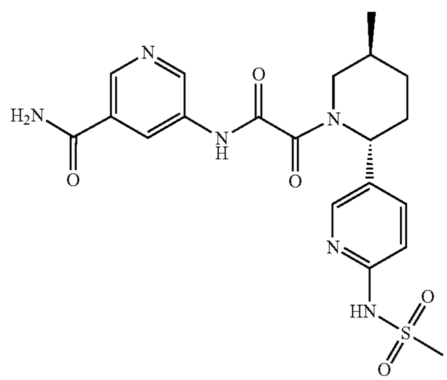 [SMILES: C[C@H]1CC[C@H](c2ccc(NS(C)(=O)=O)nc2)N(C(=O)C(=O)Nc2cncc(C(N)=O)c2)C1] | 985 | or/rel | c | cc | ccc | | | | C* |
| 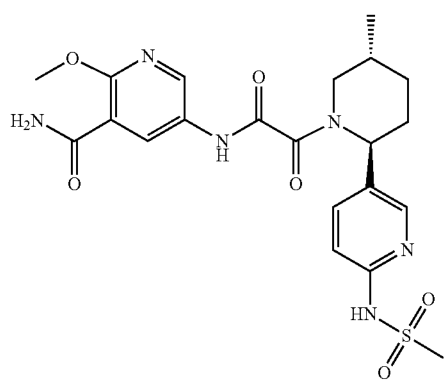 | 986 | or/rel | c | bb | aaa | c* | bb* | A | B* |
| 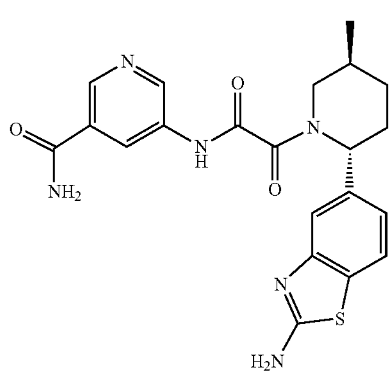 [SMILES: C[C@H]1CC[C@H](c2ccc3sc(N)nc3c2)N(C(=O)C(=O)Nc2cncc(C(N)=O)c2)C1] | 987 | or/rel | b | bb | aaa | | | | B* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 988 | or/rel | c | bb | aaa | c* | bb* | A | B* |
| | 989 | abs | b | bb | aaa | c* | aa* | A | A* |
| | 990 | and/rac | b | bb | aaa | | | | B* |
| | 991 | and/rac | b | bb | bbb | c* | bb* | C | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 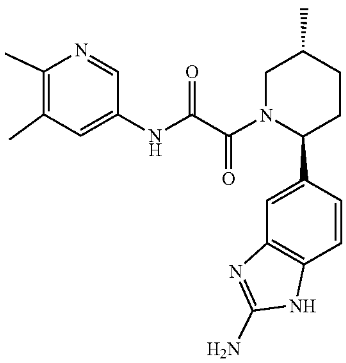 [SMILES: Cc1cc(NC(=O)C(=O)N2C[C@H](C)CC[C@H]2c2ccc3[nH]c(N)nc3c2)cnc1C] | 992 | and/rac | b | bb | aaa | c* | aa* | A | B* |
| 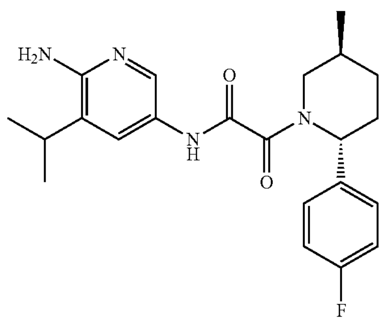 [SMILES: CC(C)c1cc(NC(=O)C(=O)N2C[C@@H](C)CC[C@@H]2c2ccc(F)cc2)cnc1N] | 993 | abs | b | aa | aaa | c* | bb* | A | B* |
| 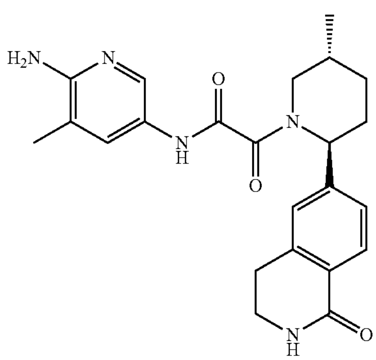 | 994 | or/rel | c | cc | ccc | | | | C* |
| 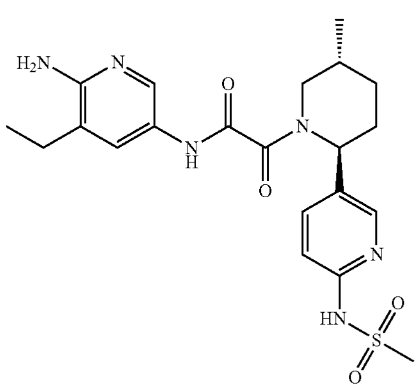 [SMILES: CCc1cc(NC(=O)C(=O)N2C[C@H](C)CC[C@H]2c2ccc(NS(C)(=O)=O)nc2)cnc1N] | 995 | or/rel | b | bb | bbb | c* | bb* | A | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| (structure) | 996 | or/rel | b | aa | aaa | | | | A* |
| (structure) | 997 | or/rel | b | aa | aaa | a* | aa* | B | A* |
| (structure) | 998 | or/rel | c | cc | ccc | c* | cc* | C | C* |
| (structure) | 999 | or/rel | c | cc | ccc | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 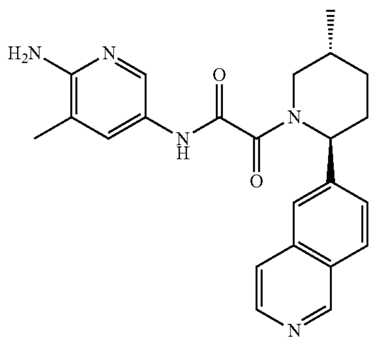 [SMILES: Cc1cc(NC(=O)C(=O)N2C[C@H](C)CC[C@H]2c2ccc3cnccc3c2)cnc1N] | 1000 | or/rel | b | aa | aaa | b* | aa* | B | A* |
| 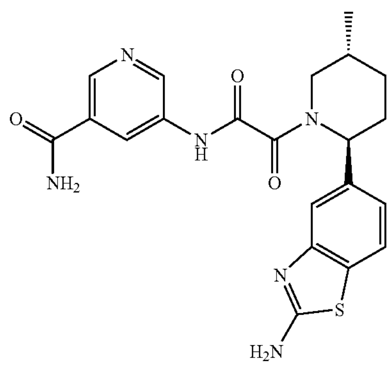 [SMILES: C[C@@H]1CC[C@@H](c2ccc3sc(N)nc3c2)N(C(=O)C(=O)Nc2cncc(C(N)=O)c2)C1] | 1001 | or/rel | c | cc | ccc | | | | C* |
| 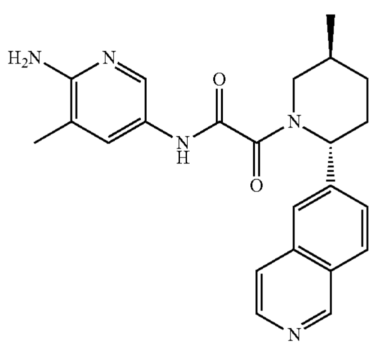 [SMILES: Cc1cc(NC(=O)C(=O)N2C[C@@H](C)CC[C@@H]2c2ccc3cnccc3c2)cnc1N] | 1002 | or/rel | c | cc | ccc | c* | bb* | B | C* |
| 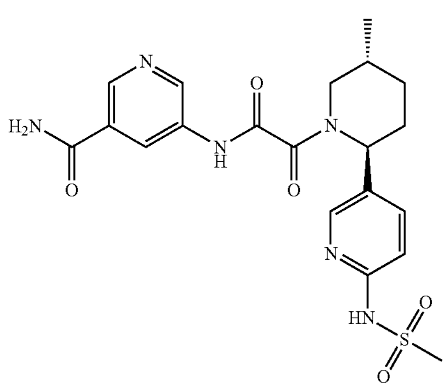 [SMILES: C[C@@H]1CC[C@@H](c2ccc(NS(C)(=O)=O)nc2)N(C(=O)C(=O)Nc2cncc(C(N)=O)c2)C1] | 1003 | or/rel | b | bb | aaa | c* | cc* | C | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 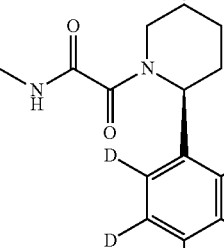 | 1004 | and/rac | b | bb | bbb | c* | bb* | A | B* |
| 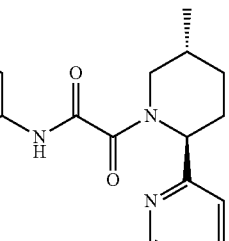 | 1005 | and/rac | c | bb | bbb | c* | bb* | A | B* |
| 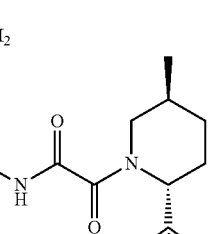 | 1006 | or/rel | b | bb | aaa | c* | aa* | A | A* |
| 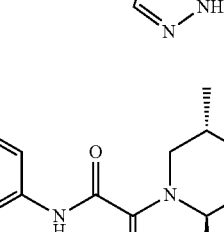 | 1007 | or/rel | c | cc | ccc | c* | cc* | B | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 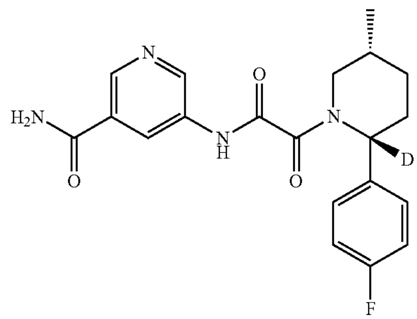 [SMILES: [2H][C@]1(c2ccc(F)cc2)CC[C@@H](C)CN1C(=O)C(=O)Nc1cncc(C(N)=O)c1] | 1008 | and/rac | b | bb | bbb | c* | bb* | A | B* |
| 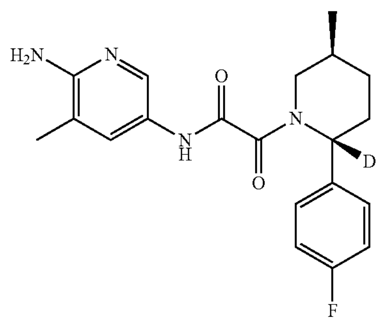 [SMILES: [2H][C@]1(c2ccc(F)cc2)CC[C@H](C)CN1C(=O)C(=O)Nc1cnc(N)c(C)c1] | 1009 | and/rac | b | bb | aaa | b* | aa* | B | B* |
| 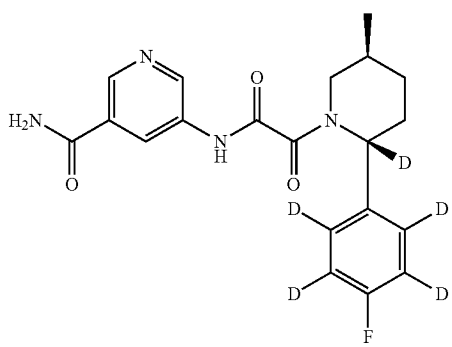 [SMILES: [2H]c1c([2H])c([C@@]2([2H])CC[C@H](C)CN2C(=O)C(=O)Nc2cncc(C(N)=O)c2)c([2H])c([2H])c1F] | 1010 | and/rac | b | bb | bbb | c* | bb* | A | B* |
| 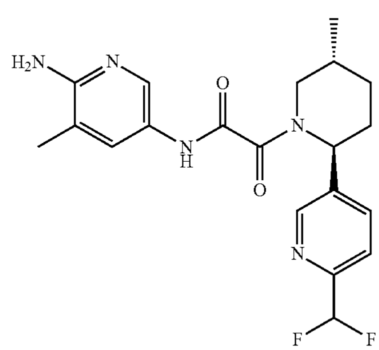 [SMILES: Cc1cc(NC(=O)C(=O)N2C[C@H](C)CC[C@H]2c2ccc(C(F)F)nc2)cnc1N] | 1011 | abs | c | cc | ccc | c* | cc* | C | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 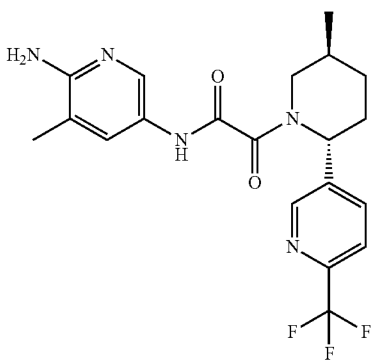 [SMILES: Cc1cc(NC(=O)C(=O)N2C[C@@H](C)CC[C@@H]2c2ccc(C(F)(F)F)nc2)cnc1N] | 1012 | abs | b | bb | aaa | b* | bb* | C | B* |
| 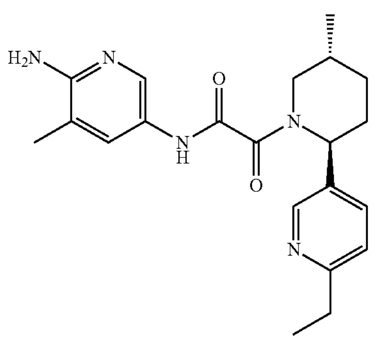 [SMILES: CCc1ccc([C@@H]2CC[C@@H](C)CN2C(=O)C(=O)Nc2cnc(N)c(C)c2)cn1] | 1013 | abs | b | bb | aaa | b* | aa* | B | B* |
| 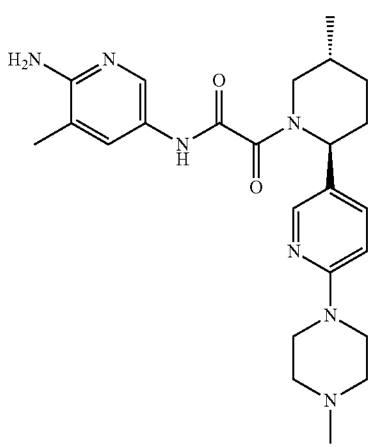 [SMILES: Cc1cc(NC(=O)C(=O)N2C[C@H](C)CC[C@H]2c2ccc(N3CCN(C)CC3)nc2)cnc1N] | 1014 | abs | b | aa | aaa | a* | aa* | B | A* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 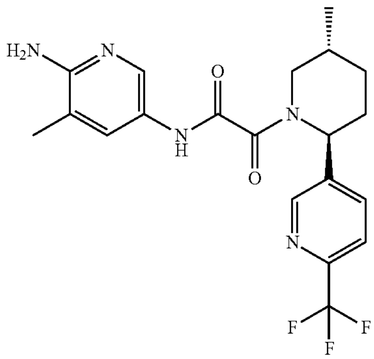 [SMILES: Cc1cc(NC(=O)C(=O)N2C[C@H](C)CC[C@H]2c2ccc(C(F)(F)F)nc2)cnc1N] | 1015 | abs | c | cc | ccc | c* | cc* | C | C* |
| 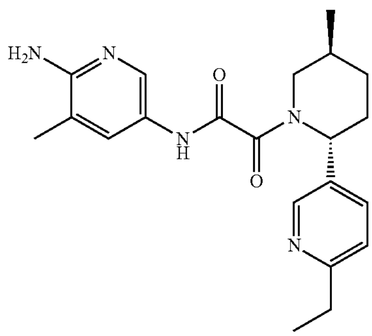 [SMILES: CCc1ccc([C@H]2CC[C@H](C)CN2C(=O)C(=O)Nc2cnc(N)c(C)c2)cn1] | 1016 | abs | c | cc | ccc | c* | cc* | C | C* |
| 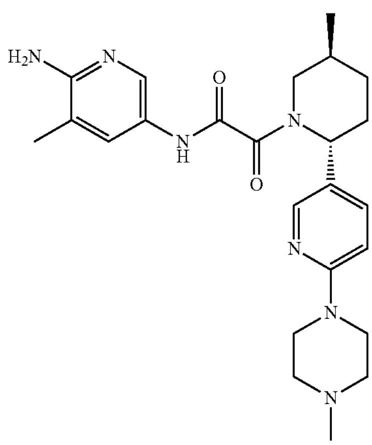 [SMILES: Cc1cc(NC(=O)C(=O)N2C[C@@H](C)CC[C@@H]2c2ccc(N3CCN(C)CC3)nc2)cnc1N] | 1017 | abs | c | cc | ccc | c* | cc* | C | A* |
| 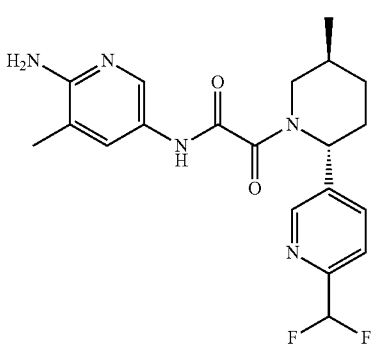 [SMILES: Cc1cc(NC(=O)C(=O)N2C[C@@H](C)CC[C@@H]2c2ccc(C(F)F)nc2)cnc1N] | 1018 | abs | b | bb | aaa | b* | bb* | B | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 1019 | and/rac | b | bb | bbb | c* | aa* | A | B* |
| | 1020 | or/rel | c | bb | aaa | c* | bb* | A | B* |
| | 1021 | or/rel | c | cc | ccc | | | | C* |
| | 1022 | or/rel | b | aa | aaa | | | | A* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 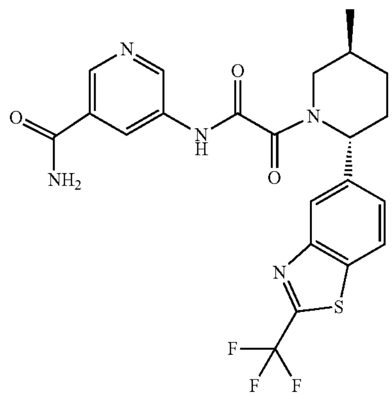 [SMILES: C[C@H]1CC[C@H](c2ccc3sc(C(F)(F)F)nc3c2)N(C(=O)C(=O)Nc2cncc(C(N)=O)c2)C1] | 1023 | or/rel | b | aa | aaa | b* | aa* | A | A* |
| 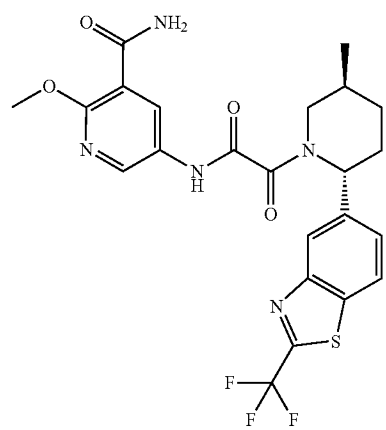 [SMILES: COc1ncc(NC(=O)C(=O)N2C[C@@H](C)CC[C@@H]2c2ccc3sc(C(F)(F)F)nc3c2)cc1C(N)=O] | 1024 | or/rel | b | aa | aaa | b* | aa* | A | A* |
| 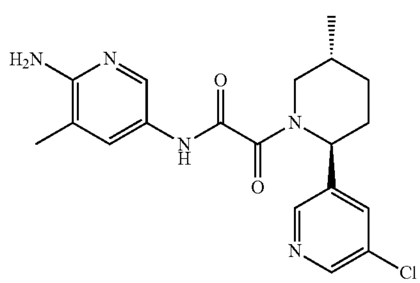 | 1025 | and/rac | c | bb | bbb | c* | aa* | A | B* |
| 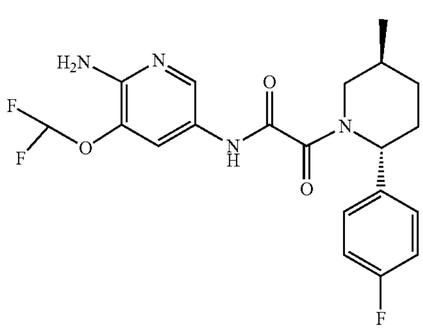 [SMILES: C[C@H]1CC[C@H](c2ccc(F)cc2)N(C(=O)C(=O)Nc2cnc(N)c(OC(F)F)c2)C1] | 1026 | abs | b | bb | aaa | c* | bb* | A | B* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| 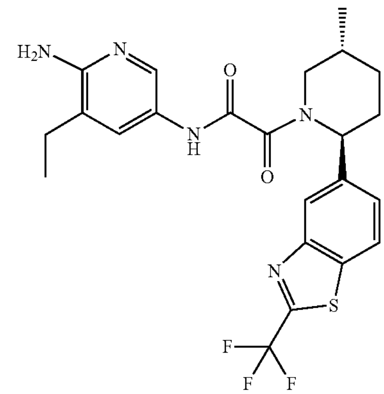 [SMILES: CCc1cc(NC(=O)C(=O)N2C[C@H](C)CC[C@H]2c2ccc3sc(C(F)(F)F)nc3c2)cnc1N] | 1027 | or/rel | c | cc | ccc |  |  |  | C* |
| 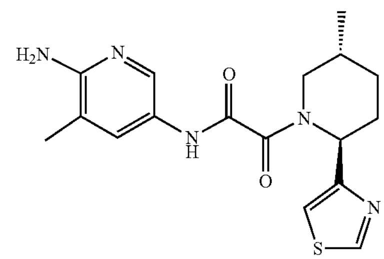 [SMILES: Cc1cc(NC(=O)C(=O)N2C[C@H](C)CC[C@H]2c2cscn2)cnc1N] | 1028 | or/rel | c | cc | ccc | c* | cc* | C | C* |
| 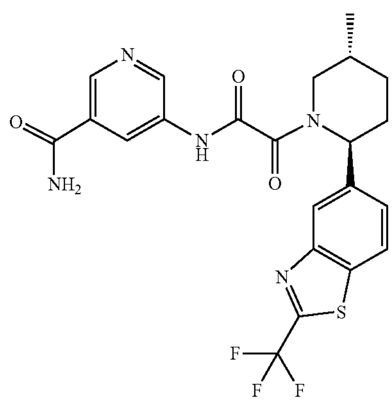 [SMILES: C[C@@H]1CC[C@@H](c2ccc3sc(C(F)(F)F)nc3c2)N(C(=O)C(=O)Nc2cncc(C(N)=O)c2)C1] | 1029 | or/rel | c | cc | ccc | c* | cc* | B | C* |
| 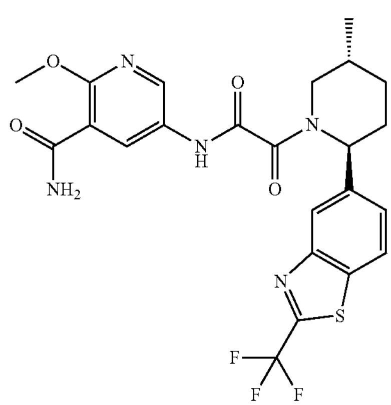 [SMILES: COc1ncc(NC(=O)C(=O)N2C[C@H](C)CC[C@H]2c2ccc3sc(C(F)(F)F)nc3c2)cc1C(N)=O] | 1030 | or/rel | c | cc | ccc |  |  |  | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 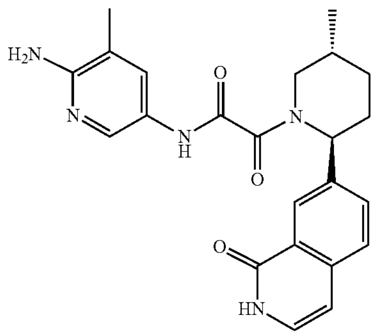 [SMILES: Cc1cc(NC(=O)C(=O)N2C[C@H](C)CC[C@H]2c2ccc3cc[nH]c(=O)c3c2)cnc1N] | 1031 | or/rel | a | aa | aaa | | | | A* |
| 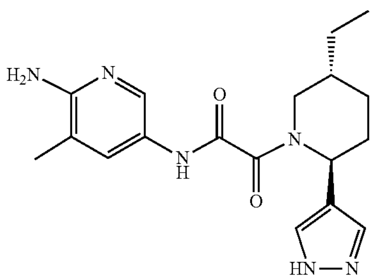 [SMILES: CC[C@@H]1CC[C@@H](c2cn[nH]c2)N(C(=O)C(=O)Nc2cnc(N)c(C)c2)C1] | 1032 | and/rac | b | bb | bbb | b* | aa* | B | B* |
| 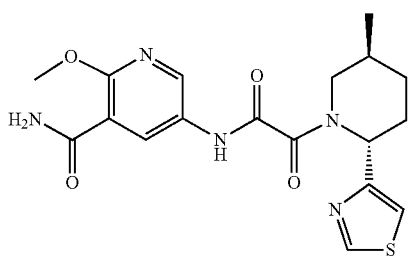 [SMILES: COc1ncc(NC(=O)C(=O)N2C[C@@H](C)CC[C@@H]2c2cscn2)cc1C(N)=O] | 1033 | or/rel | c | cc | ccc | c* | cc* | B | C* |
| 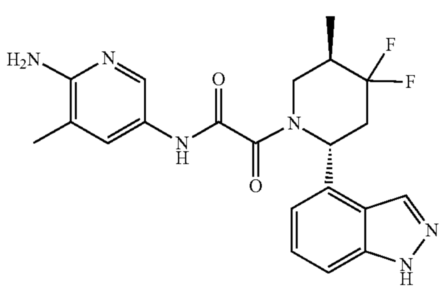 [SMILES: Cc1cc(NC(=O)C(=O)N2C[C@@H](C)C(F)(F)C[C@@H]2c2cccc3[nH]ncc23)cnc1N] | 1034 | or/rel | c | cc | ccc | | | | C* |
| 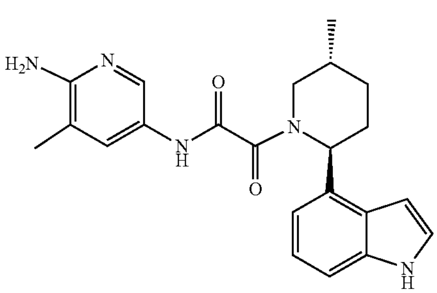 [SMILES: Cc1cc(NC(=O)C(=O)N2C[C@H](C)CC[C@H]2c2cccc3[nH]ccc23)cnc1N] | 1035 | or/rel | b | bb | aaa | | | | A* |

TABLE 1-continued

Exemplary compounds of the invention and biological data

| Structure | Nr | Stereo | No Co-factor/ SAM rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|
| 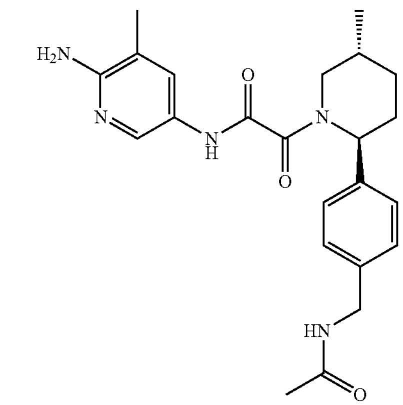 | 1036 | and/rac | b | bb | bbb | | | B* |
| | 1037 | or/rel | c | cc | ccc | c* | bb* | A | C* |
| | 1038 | or/rel | c | cc | ccc | | | | C* |
| | 1039 | abs | b | bb | bbb | b* | bb* | C | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1040 | or/rel | c | cc | ccc | c* | bb* | A | C* |
| | 1041 | or/rel | b | aa | aaa | | | | A* |
| | 1042 | or/rel | b | bb | aaa | c* | aa* | A | B* |
| | 1043 | or/rel | b | bb | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 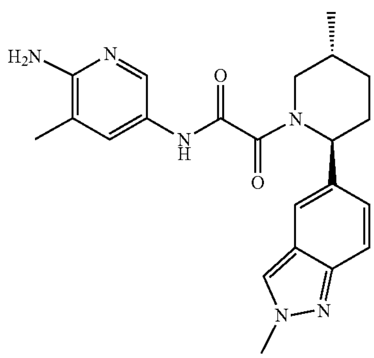 [SMILES: Cc1cc(NC(=O)C(=O)N2C[C@H](C)CC[C@H]2c2ccc3nn(C)cc3c2)cnc1N] | 1044 | or/rel | b | aa | aaa | b* | aa* | A | A* |
| 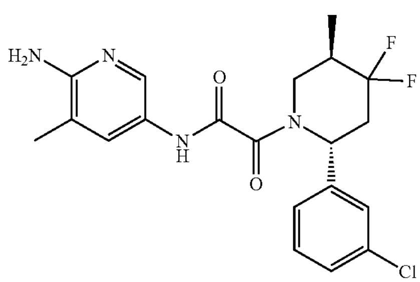 [SMILES: Cc1cc(NC(=O)C(=O)N2C[C@@H](C)C(F)(F)C[C@@H]2c2cccc(Cl)c2)cnc1N] | 1045 | or/rel | c | cc | ccc | | | | |
| 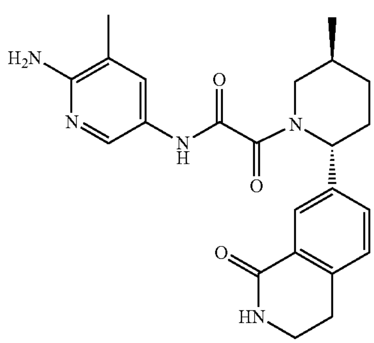 [SMILES: Cc1cc(NC(=O)C(=O)N2C[C@@H](C)CC[C@@H]2c2ccc3c(c2)C(=O)NCC3)cnc1N] | 1046 | or/rel | c | cc | ccc | | | | |
| 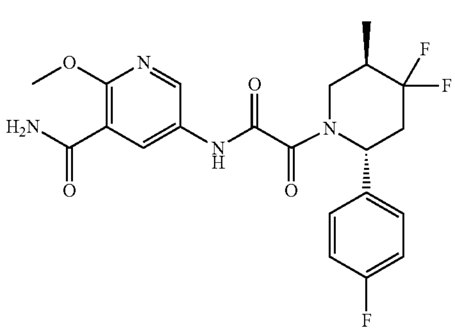 [SMILES: COc1ncc(NC(=O)C(=O)N2C[C@@H](C)C(F)(F)C[C@@H]2c2ccc(F)cc2)cc1C(N)=O] | 1047 | or/rel | c | cc | ccc | c* | cc* | C | |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 1048 | and/rac | b | bb | bbb | b* | aa* | | B |
| | 1049 | or/rel | b | bb | bbb | | | | |
| | 1050 | or/rel | c | cc | ccc | c* | cc* | | C |
| | 1051 | or/rel | c | cc | ccc | c* | cc* | | B |

TABLE 1-continued

Exemplary compounds of the invention and biological data

| Structure | Nr | Stereo | SAM IC50 | No Cofactor/rel IC50 | MTA IC50 | HAP1 MTAP intact IC50 | HAP1 MTAP deleted IC50 | MTAP intact/deleted ratio | HAP1 MTAP deleted viability |
|---|---|---|---|---|---|---|---|---|---|
| | 1052 | or/rel | c | cc | bbb | | | | |
| | 1053 | or/rel | c | cc | bbb | c* | bb* | | A |
| | 1054 | and/rac | b | bb | bbb | | | | |
| | 1055 | or/rel | c | cc | ccc | c* | cc* | | B |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1056 | and/rac | b | bb | aaa | b* | bb* | C | |
| | 1057 | abs | c | bb | bbb | c* | cc* | B | |
| | 1058 | abs | c | cc | bbb | | | | |
| | 1059 | or/rel | b | bb | aaa | c* | aa* | A | |

TABLE 1-continued

Exemplary compounds of the invention and biological data

| Structure | Nr | Stereo | No Co-factor/ SAM IC50 | SAM rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| 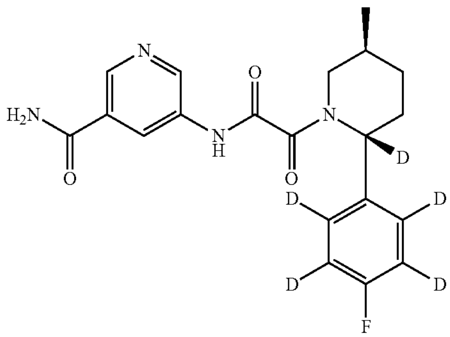 [SMILES: [2H]c1c([2H])c([C@@]2([2H])CC[C@H](C)CN2C(=O)C(=O)Nc2cncc(C(N)=O)c2)c([2H])c([2H])c1F] | 1060 | abs | b | bb | aaa | | | | |
| 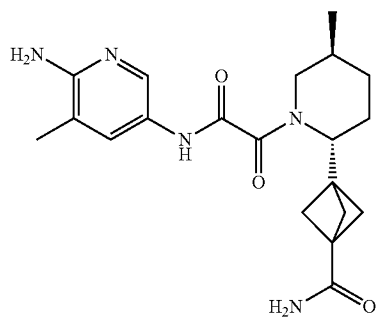 [SMILES: Cc1cc(NC(=O)C(=O)N2C[C@@H](C)CC[C@@H]2C23CC(C(N)=O)(C2)C3)cnc1N] | 1061 | or/rel | c | cc | ccc | c* | cc* | B | |
| 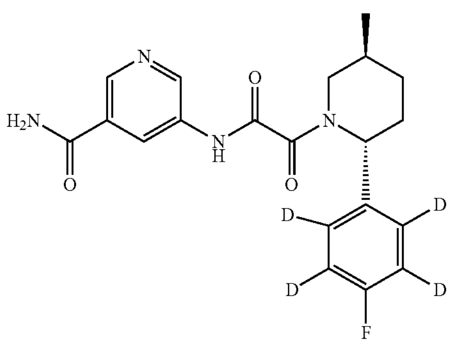 [SMILES: [2H]c1c([2H])c([C@H]2CC[C@H](C)CN2C(=O)C(=O)Nc2cncc(C(N)=O)c2)c([2H])c([2H])c1F] | 1062 | abs | b | bb | aaa | | | | |
| 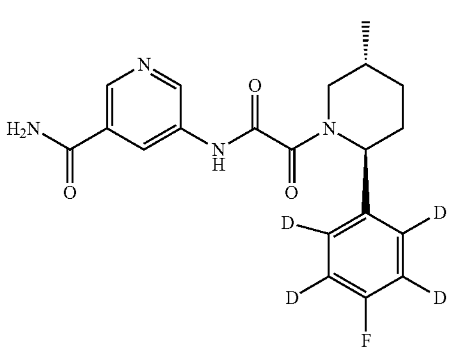 [SMILES: [2H]c1c([2H])c([C@@H]2CC[C@@H](C)CN2C(=O)C(=O)Nc2cncc(C(N)=O)c2)c([2H])c([2H])c1F] | 1063 | abs | c | cc | ccc | | | | |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1064 | abs | c | cc | ccc | | | | |
| | 1065 | abs | b | bb | aaa | | | | |
| | 1066 | abs | c | cc | ccc | | | | |
| | 1067 | or/rel | b | bb | bbb | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 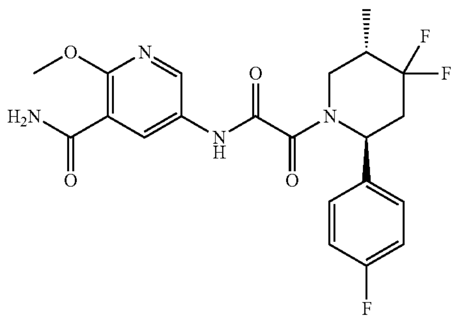 [SMILES: COc1ncc(NC(=O)C(=O)N2C[C@H](C)C(F)(F)C[C@H]2c2ccc(F)cc2)cc1C(N)=O] | 1068 | or/rel | b | bb | aaa | c* | aa* | | A |
| 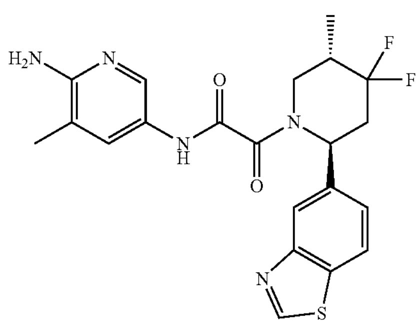 [SMILES: Cc1cc(NC(=O)C(=O)N2C[C@H](C)C(F)(F)C[C@H]2c2ccc3scnc3c2)cnc1N] | 1069 | or/rel | c | cc | ccc | | | | |
| 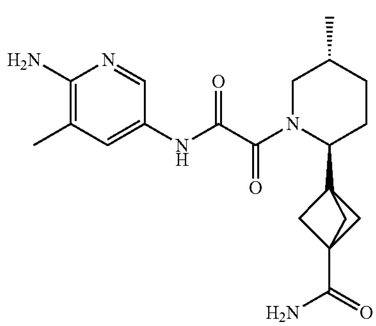 [SMILES: Cc1cc(NC(=O)C(=O)N2C[C@H](C)CC[C@H]2C23CC(C(N)=O)(C2)C3)cnc1N] | 1070 | or/rel | c | cc | ccc | c* | cc* | | B |
| 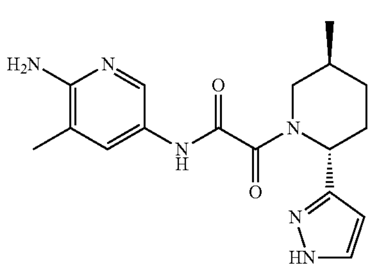 | 1071 | or/rel | b | bb | aaa | c* | cc* | | C |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 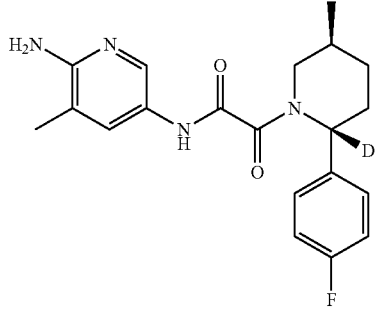 [SMILES: [2H][C@]1(c2ccc(F)cc2)CC[C@H](C)CN1C(=O)C(=O)Nc1cnc(N)c(C)c1] | 1072 | abs | b | bb | aaa | | | | |
| 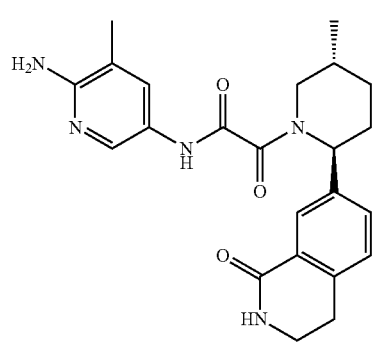 [SMILES: Cc1cc(NC(=O)C(=O)N2C[C@H](C)CC[C@H]2c2ccc3c(c2)C(=O)NCC3)cnc1N] | 1073 | or/rel | b | bb | aaa | | | | |
| 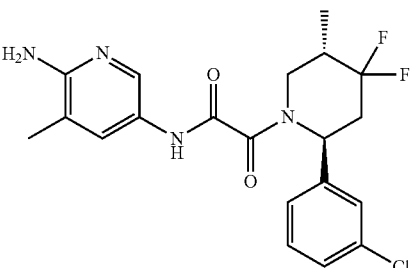 | 1074 | or/rel | b | aa | aaa | | | | |
| 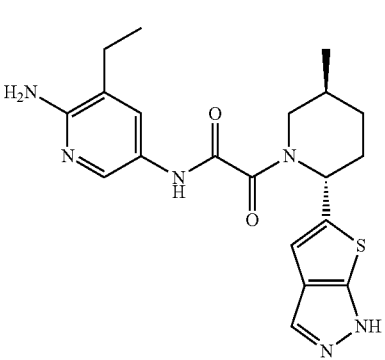 [SMILES: CCc1cc(NC(=O)C(=O)N2C[C@@H](C)CC[C@@H]2c2cc3cn[nH]c3s2)cnc1N] | 1075 | or/rel | b | aa | aaa | b* | aa* | A | |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 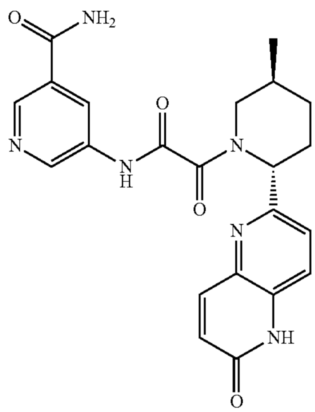 [SMILES: C[C@H]1CC[C@H](c2ccc3[nH]c(=O)ccc3n2)N(C(=O)C(=O)Nc2cncc(C(N)=O)c2)C1] | 1076 | abs | c | cc | ccc | | | | |
| 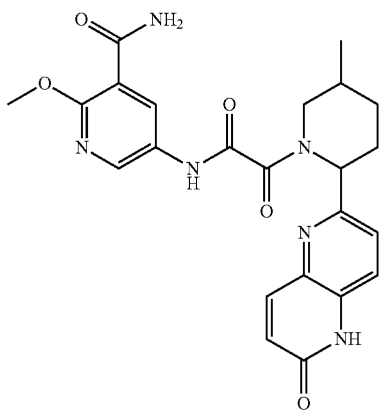 [SMILES: COc1ncc(NC(=O)C(=O)N2CC(C)CCC2c2ccc3[nH]c(=O)ccc3n2)cc1C(N)=O] | 1077 | | b | bb | bbb | | | | |
| 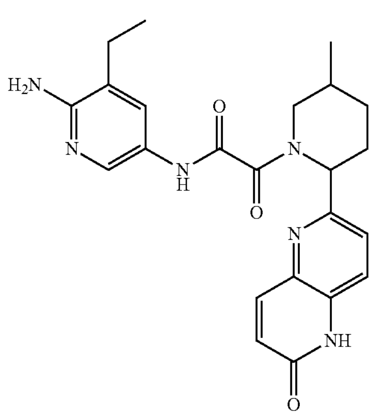 [SMILES: CCc1cc(NC(=O)C(=O)N2CC(C)CCC2c2ccc3[nH]c(=O)ccc3n2)cnc1N] | 1078 | | b | bb | bbb | | | | |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP1 MTAP deleted IC50 | MTAP intact/deleted ratio | HAP1 MTAP deleted viability |
|---|---|---|---|---|---|---|---|---|---|
| | 1079 | abs | b | aa | aaa | | | | |
| | 1080 | or/rel | c | cc | ccc | c* | cc* | C | C* |
| | 1081 | or/rel | c | cc | ccc | c* | cc* | B | C* |
| | 1082 | or/rel | c | cc | ccc | | | | C* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| | 1083 | or/rel | c | cc | ccc | | | | |
| | 1084 | or/rel | c | cc | ccc | c* | cc* | C | C* |
| | 1085 | or/rel | | | | | | | |
| | 1086 | or/rel | | | | | | | |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 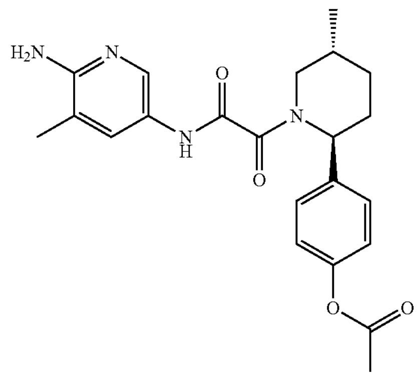 [SMILES: CC(=O)Oc1ccc([C@@H]2CC[C@@H](C)CN2C(=O)C(=O)Nc2cnc(N)c(C)c2)cc1] | 1087 | or/rel |  |  |  |  |  |  |  |
| 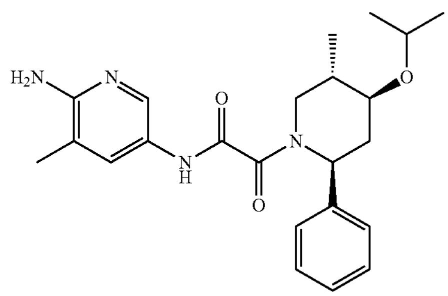 [SMILES: Cc1cc(NC(=O)C(=O)N2C[C@H](C)[C@@H](OC(C)C)C[C@H]2c2ccccc2)cnc1N] | 1088 | or/rel | b | aa | aaa | b* | aa* | A | A* |
| 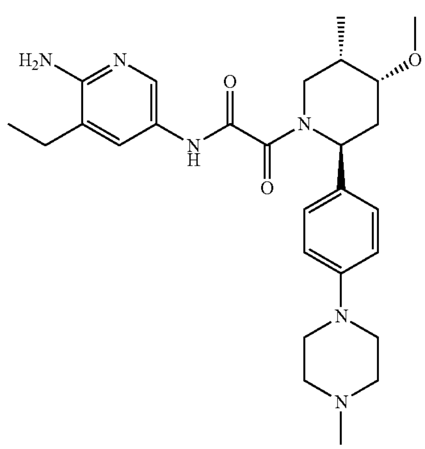 [SMILES: CCc1cc(NC(=O)C(=O)N2C[C@H](C)[C@H](OC)C[C@H]2c2ccc(N3CCN(C)CC3)cc2)cnc1N] | 1089 | or/rel | b | bb | aaa | b* | aa* | A | A* |
| 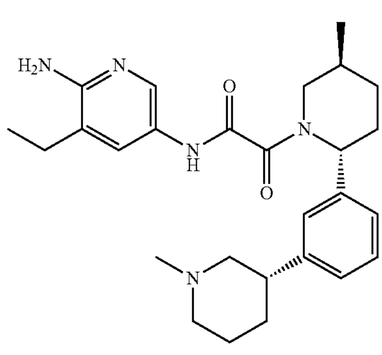 [SMILES: CCc1cc(NC(=O)C(=O)N2C[C@@H](C)CC[C@@H]2c2cccc([C@@H]3CCCN(C)C3)c2)cnc1N] | 1090 | abs | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 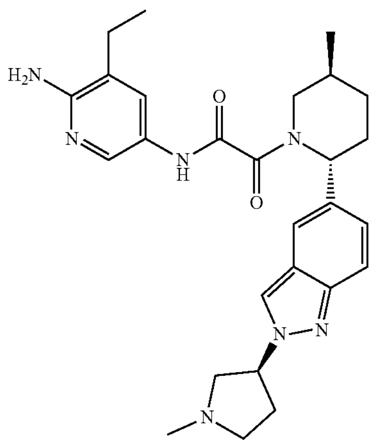 [SMILES: CCc1cc(NC(=O)C(=O)N2C[C@@H](C)CC[C@@H]2c2ccc3nn([C@H]4CCN(C)C4)cc3c2)cnc1N] | 1091 | | b | aa | aaa | b* | aa* | A | A* |
| 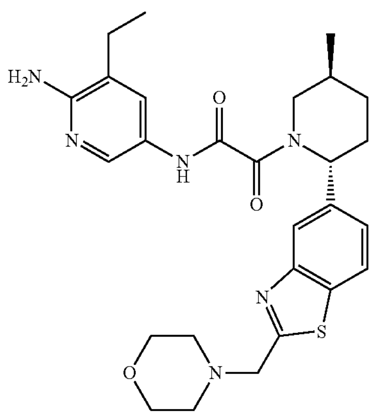 [SMILES: CCc1cc(NC(=O)C(=O)N2C[C@@H](C)CC[C@@H]2c2ccc3sc(CN4CCOCC4)nc3c2)cnc1N] | 1092 | abs | b | aa | aaa | b* | aa* | A | A* |
| 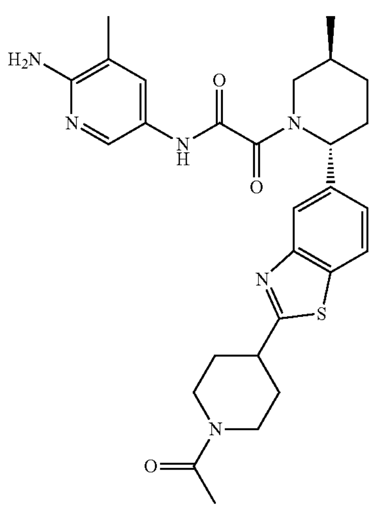 [SMILES: CC(=O)N1CCC(c2nc3cc([C@H]4CC[C@H](C)CN4C(=O)C(=O)Nc4cnc(N)c(C)c4)ccc3s2)CC1] | 1093 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1094 | and/rac | b | bb | bbb | b* | aa* | A | A* |
| | 1095 | abs | a | aa | aaa | a* | aa* | A | A* |
| | 1096 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 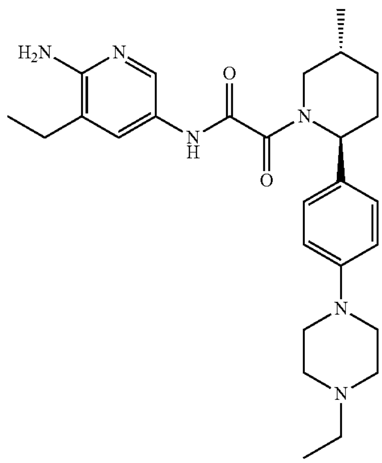 [SMILES: CCc1cc(NC(=O)C(=O)N2C[C@H](C)CC[C@H]2c2ccc(N3CCN(CC)CC3)cc2)cnc1N] | 1097 | or/rel | b | aa | aaa | b* | aa* | A | A* |
| 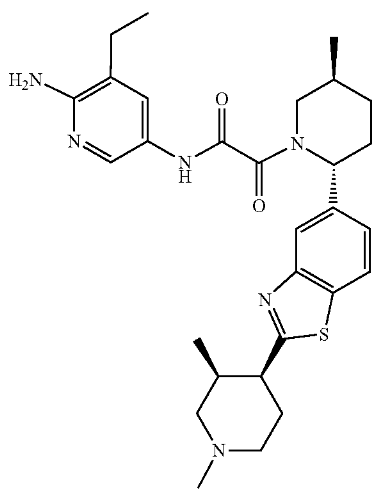 [SMILES: CCc1cc(NC(=O)C(=O)N2C[C@@H](C)CC[C@@H]2c2ccc3sc([C@H]4CCN(C)C[C@H]4C)nc3c2)cnc1N] | 1098 | abs | a | aa | aaa | a* | aa* | B | A* |
| 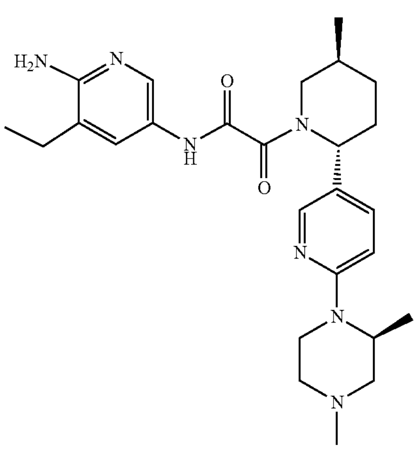 [SMILES: CCc1cc(NC(=O)C(=O)N2C[C@@H](C)CC[C@@H]2c2ccc(N3CCN(C)C[C@@H]3C)nc2)cnc1N] | 1099 | and/rac | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1100 | abs | a | aa | aaa | b* | aa* | A | A* |
| | 1101 | abs | a | aa | aaa | a* | aa* | A | A* |
| | 1102 | abs | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 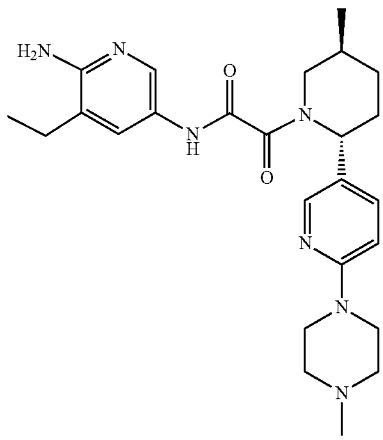 [SMILES: CCc1cc(NC(=O)C(=O)N2C[C@@H](C)CC[C@@H]2c2ccc(N3CCN(C)CC3)nc2)cnc1N] | 1103 | abs | b | aa | aaa | b* | aa* | A | A* |
| 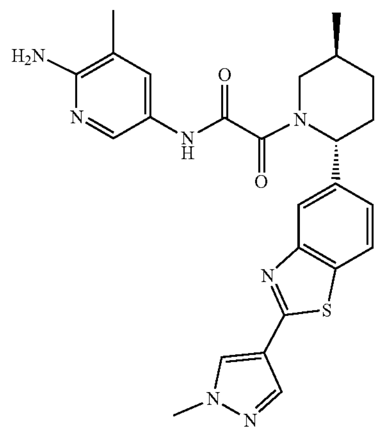 [SMILES: Cc1cc(NC(=O)C(=O)N2C[C@@H](C)CC[C@@H]2c2ccc3sc(-c4cnn(C)c4)nc3c2)cnc1N] | 1104 | and/rac | b | aa | aaa | a* | aa* | B | A* |
| 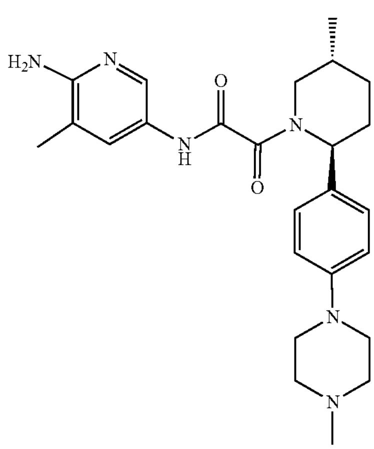 [SMILES: Cc1cc(NC(=O)C(=O)N2C[C@H](C)CC[C@H]2c2ccc(N3CCN(C)CC3)cc2)cnc1N] | 1105 | and/rac | b | bb | bbb | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1106 | and/rac | b | bb | aaa | a* | aa* | B | A* |
| | 1107 | abs | a | | | aaa | a* | aa* | B | A* |
| | 1108 | or/rel | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 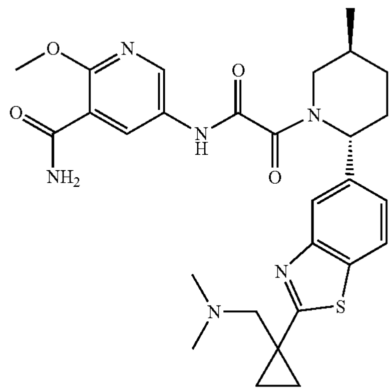 [SMILES: COc1ncc(NC(=O)C(=O)N2C[C@@H](C)CC[C@@H]2c2ccc3sc(C4(CN(C)C)CC4)nc3c2)cc1C(N)=O] | 1109 | or/rel | a | aa | aaa | b* | aa* | A | A* |
| 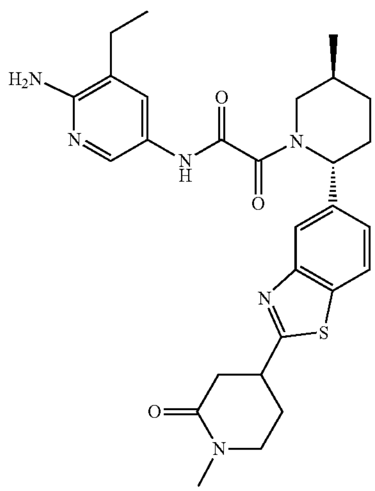 [SMILES: CCc1cc(NC(=O)C(=O)N2C[C@@H](C)CC[C@@H]2c2ccc3sc(C4CCN(C)C(=O)C4)nc3c2)cnc1N] | 1110 | and/rac | b | aa | aaa | b* | aa* | A | A* |
| 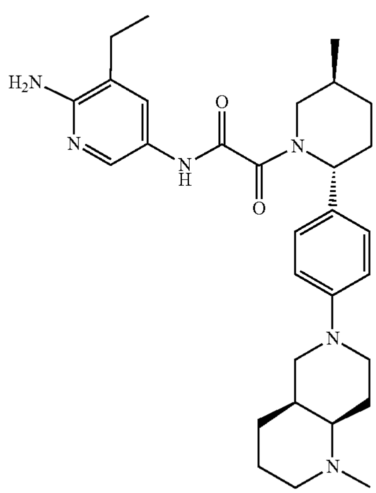 [SMILES: CCc1cc(NC(=O)C(=O)N2C[C@@H](C)CC[C@@H]2c2ccc(N3CC[C@@H]4[C@@H](CCCN4C)C3)cc2)cnc1N] | 1111 | abs | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 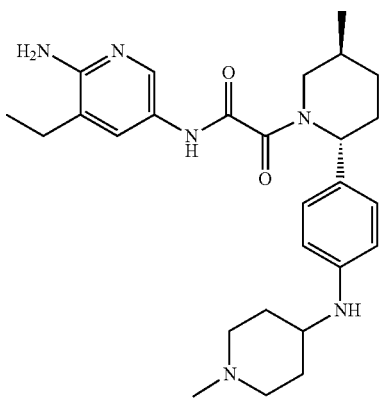 [SMILES: CCc1cc(NC(=O)C(=O)N2C[C@@H](C)CC[C@@H]2c2ccc(NC3CCN(C)CC3)cc2)cnc1N] | 1112 | abs | b | aa | aaa | b* | aa* | A | A* |
| 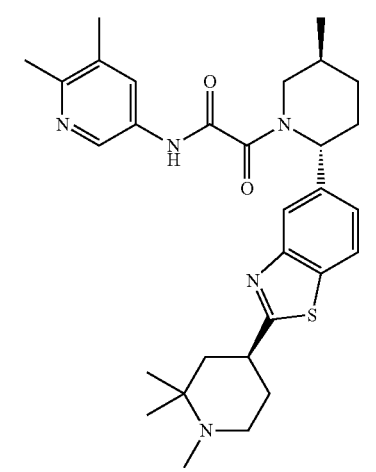 [SMILES: Cc1cc(NC(=O)C(=O)N2C[C@@H](C)CC[C@@H]2c2ccc3sc([C@H]4CCN(C)C(C)(C)C4)nc3c2)cnc1C] | 1113 | and/rac | a | aa | aaa | b* | aa* | A | A* |
| 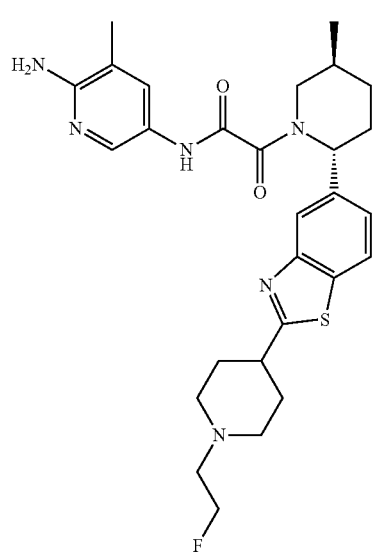 [SMILES: Cc1cc(NC(=O)C(=O)N2C[C@@H](C)CC[C@@H]2c2ccc3sc(C4CCN(CCF)CC4)nc3c2)cnc1N] | 1114 | abs | a | aa | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 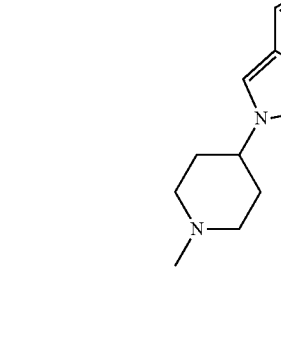 | 1115 | a | a | aa | aaa | b* | aa* | A | A* |
| 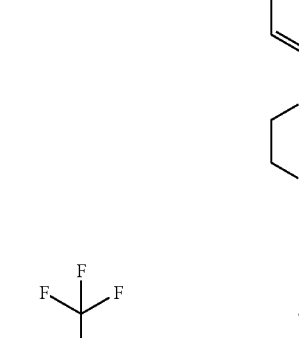 | 1116 | or/rel | c | cc | ccc | c* | cc* | | C* |
| 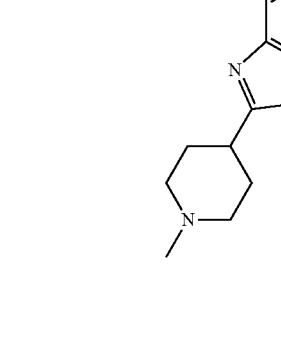 | 1117 | abs | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 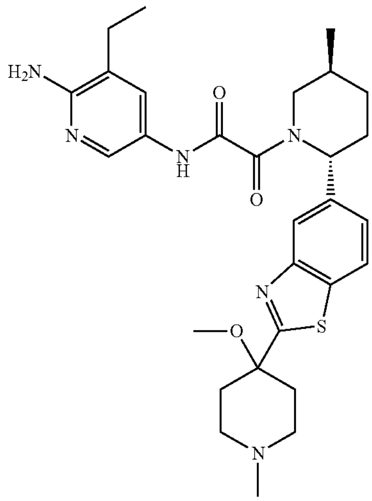 [SMILES: CCc1cc(NC(=O)C(=O)N2C[C@@H](C)CC[C@@H]2c2ccc3sc(C4(OC)CCN(C)CC4)nc3c2)cnc1N] | 1118 |  | a | aa | aaa | a* | aa* | A | A* |
| 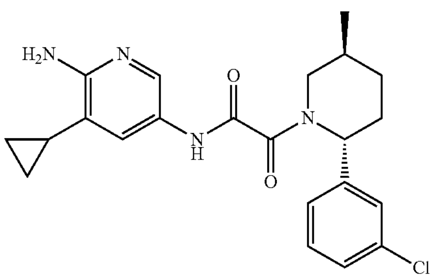 [SMILES: C[C@H]1CC[C@H](c2cccc(Cl)c2)N(C(=O)C(=O)Nc2cnc(N)c(C3CC3)c2)C1] | 1119 | or/rel | b | aa | aaa | b* | aa* | A | A* |
| 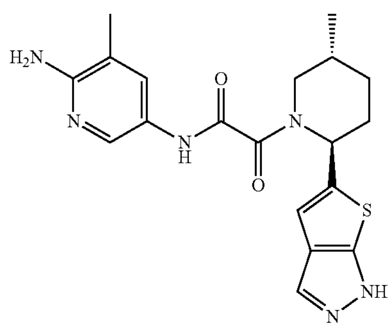 [SMILES: Cc1cc(NC(=O)C(=O)N2C[C@H](C)CC[C@H]2c2cc3cn[nH]c3s2)cnc1N] | 1120 | or/rel | c | cc | ccc | c* | cc* |  | C* |
| 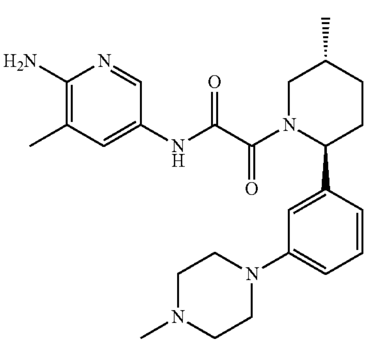 [SMILES: Cc1cc(NC(=O)C(=O)N2C[C@H](C)CC[C@H]2c2cccc(N3CCN(C)CC3)c2)cnc1N] | 1121 | or/rel | c | cc | ccc | c* | cc* |  | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 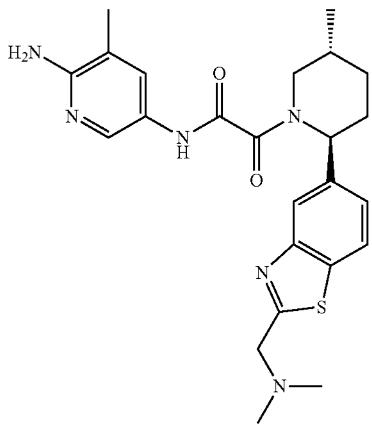 [SMILES: Cc1cc(NC(=O)C(=O)N2C[C@H](C)CC[C@H]2c2ccc3sc(CN(C)C)nc3c2)cnc1N] | 1122 | or/rel | b | aa | aaa | a* | aa* | B | A* |
| 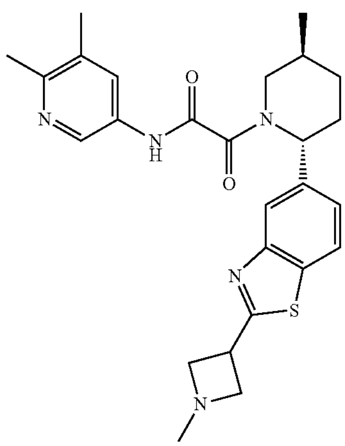 [SMILES: Cc1cc(NC(=O)C(=O)N2C[C@@H](C)CC[C@@H]2c2ccc3sc(C4CN(C)C4)nc3c2)cnc1C] | 1123 | abs | a | aa | aaa | b* | aa* | A | A* |
| 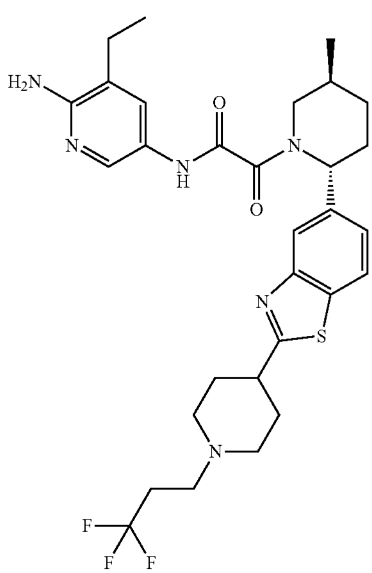 [SMILES: CCc1cc(NC(=O)C(=O)N2C[C@@H](C)CC[C@@H]2c2ccc3sc(C4CCN(CCC(F)(F)F)CC4)nc3c2)cnc1N] | 1124 | abs | b | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 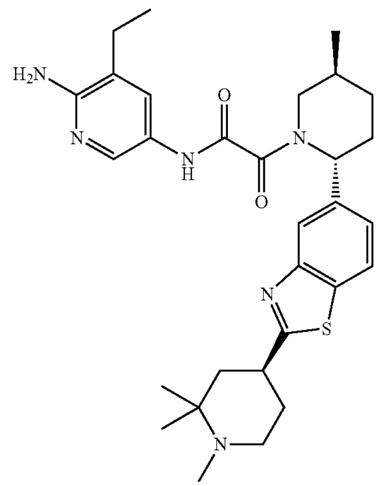 [SMILES: CCc1cc(NC(=O)C(=O)N2C[C@@H](C)CC[C@@H]2c2ccc3sc([C@H]4CCN(C)C(C)(C)C4)nc3c2)cnc1N] | 1125 | abs | a | aa | aaa | a* | aa* | A | A* |
| 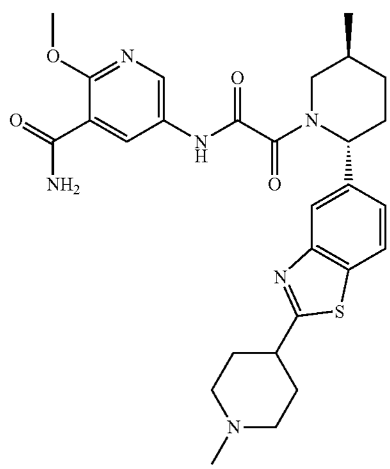 [SMILES: COc1ncc(NC(=O)C(=O)N2C[C@@H](C)CC[C@@H]2c2ccc3sc(C4CCN(C)CC4)nc3c2)cc1C(N)=O] | 1126 | abs | b | aa | aaa | a* | aa* | A | A* |
| 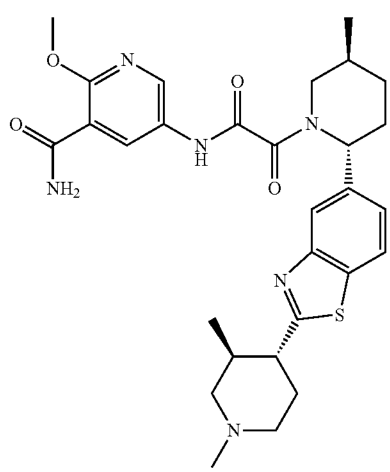 [SMILES: COc1ncc(NC(=O)C(=O)N2C[C@@H](C)CC[C@@H]2c2ccc3sc([C@@H]4CCN(C)C[C@H]4C)nc3c2)cc1C(N)=O] | 1127 | | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 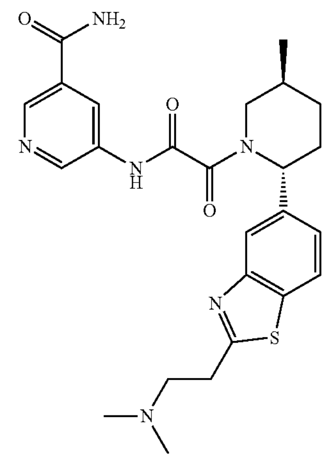 [SMILES: C[C@H]1CC[C@H](c2ccc3sc(CCN(C)C)nc3c2)N(C(=O)C(=O)Nc2cncc(C(N)=O)c2)C1] | 1128 | or/rel | c | cc | ccc | c* | bb* | | B* |
| 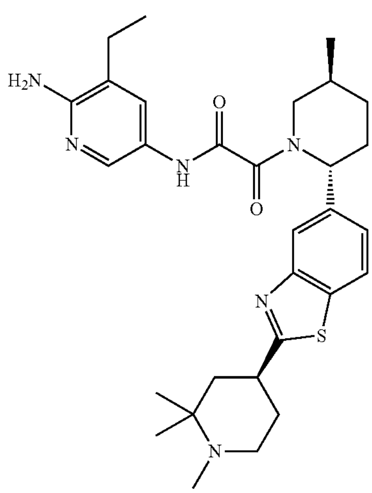 [SMILES: CCc1cc(NC(=O)C(=O)N2C[C@@H](C)CC[C@@H]2c2ccc3sc([C@H]4CCN(C)C(C)(C)C4)nc3c2)cnc1N] | 1129 | abs | b | aa | aaa | a* | aa* | B | A* |
| 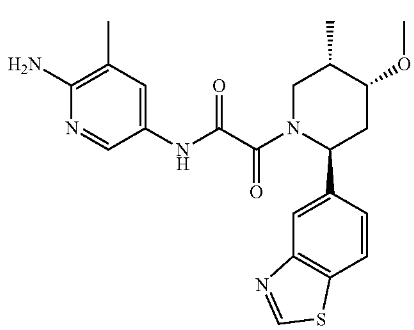 [SMILES: CO[C@@H]1C[C@@H](c2ccc3scnc3c2)N(C(=O)C(=O)Nc2cnc(N)c(C)c2)C[C@@H]1C] | 1130 | or/rel | c | cc | ccc | c* | cc* | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 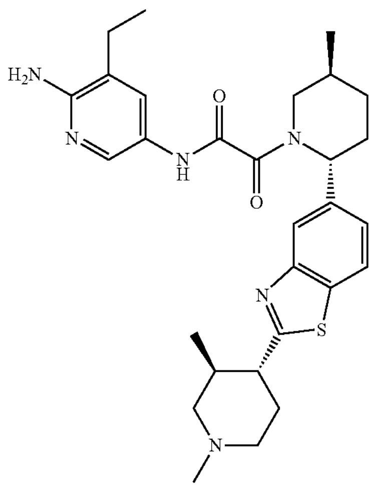 [SMILES: CCc1cc(NC(=O)C(=O)N2C[C@@H](C)CC[C@@H]2c2ccc3sc([C@@H]4CCN(C)C[C@H]4C)nc3c2)cnc1N] | 1131 | abs | a | aa | aaa | a* | aa* | B | A* |
| 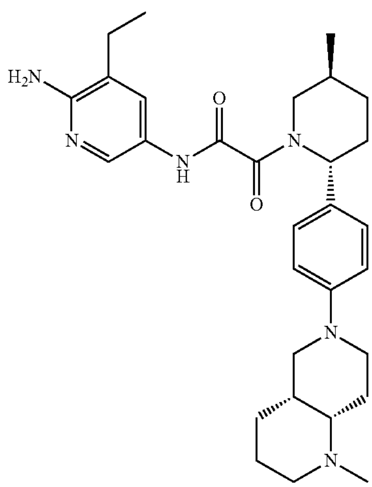 [SMILES: CCc1cc(NC(=O)C(=O)N2C[C@@H](C)CC[C@@H]2c2ccc(N3CC[C@H]4[C@H](CCCN4C)C3)cc2)cnc1N] | 1132 | abs | b | aa | aaa | b* | aa* | A | A* |
| 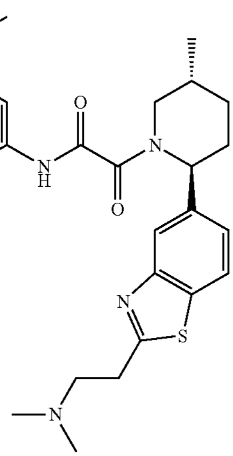 | 1133 | or/rel | c | cc | ccc | c* | cc* | | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1134 | abs | b | aa | aaa | a* | aa* | A | A* |
| | 1135 | or/rel | a | aa | aaa | b* | aa* | A | A* |
| | 1136 | abs | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 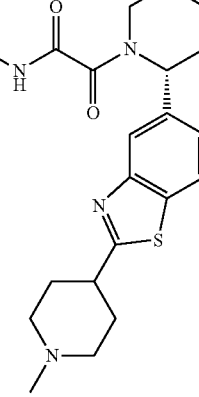 | 1137 | abs | a | aa | aaa | a* | aa* | A | A* |
| 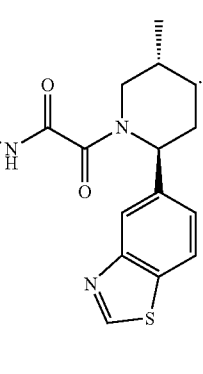 | 1138 | or/rel | c | cc | ccc | c* | bb* | | B* |
| 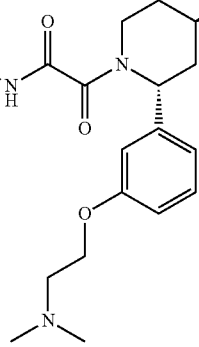 | 1139 | and/rac | b | bb | bbb | a* | aa* | B | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 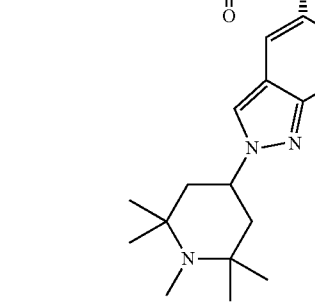 | 1140 | a | aa | aaa | a* | aa* | A | A* |
| 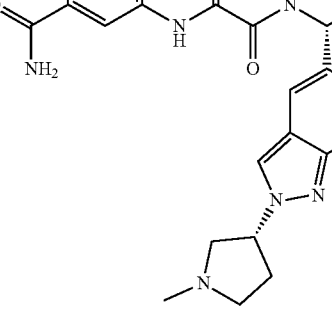 | 1141 | b | aa | aaa | b* | aa* | A | A* |
| 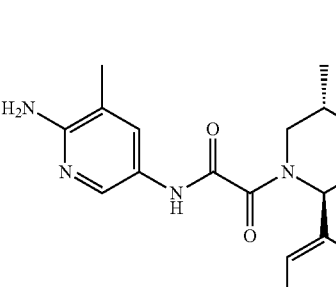 | 1142 and/rac | b | bb | aaa | a* | aa* | B | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 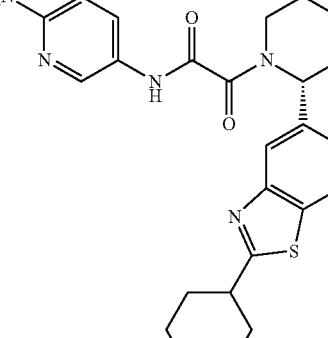 | 1143 | abs | a | aa | aaa | a* | aa* | B | A* |
| 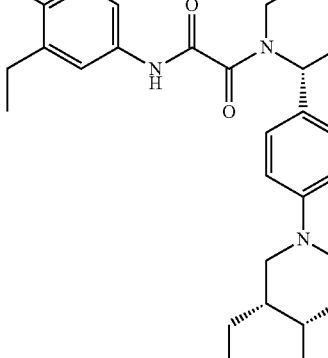 | 1144 | abs | b | aa | aaa | b* | aa* | A | A* |
| 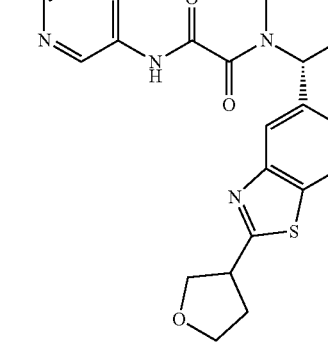 | 1145 | abs | b | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 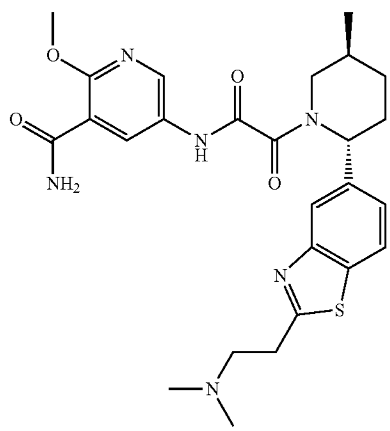 [SMILES: COc1ncc(NC(=O)C(=O)N2C[C@@H](C)CC[C@@H]2c2ccc3sc(CCN(C)C)nc3c2)cc1C(N)=O] | 1146 | or/rel | a | aa | aaa | a* | aa* | A | A* |
| 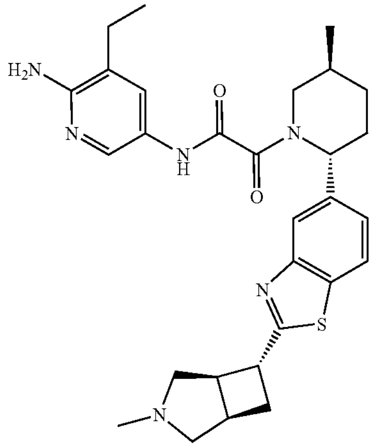 [SMILES: CCc1cc(NC(=O)C(=O)N2C[C@@H](C)CC[C@@H]2c2ccc3sc([C@@H]4C[C@H]5CN(C)C[C@H]54)nc3c2)cnc1N] | 1147 | | a | aa | aaa | a* | aa* | A | A* |
| 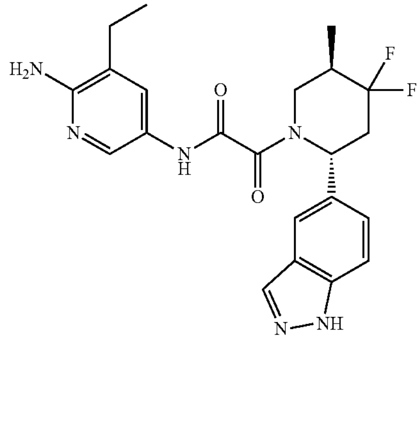 [SMILES: CCc1cc(NC(=O)C(=O)N2C[C@@H](C)C(F)(F)C[C@@H]2c2ccc3[nH]ncc3c2)cnc1N] | 1148 | or/rel | c | cc | ccc | c* | bb* | A | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 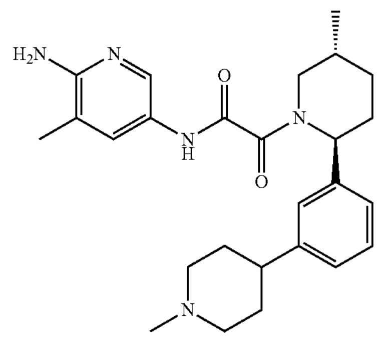 [SMILES: Cc1cc(NC(=O)C(=O)N2C[C@H](C)CC[C@H]2c2cccc(C3CCN(C)CC3)c2)cnc1N] | 1149 | and/rac | b | bb | aaa | b* | aa* | A | A* |
| 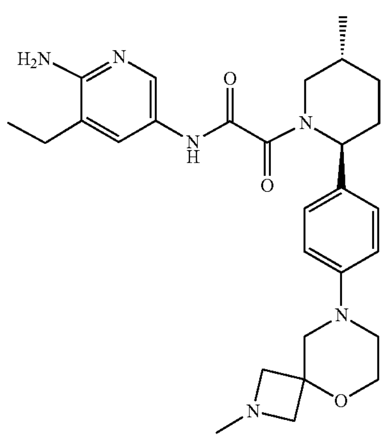 [SMILES: CCc1cc(NC(=O)C(=O)N2C[C@H](C)CC[C@H]2c2ccc(N3CCOC4(CN(C)C4)C3)cc2)cnc1N] | 1150 | or/rel | c | cc | ccc | c* | cc* | | C* |
| 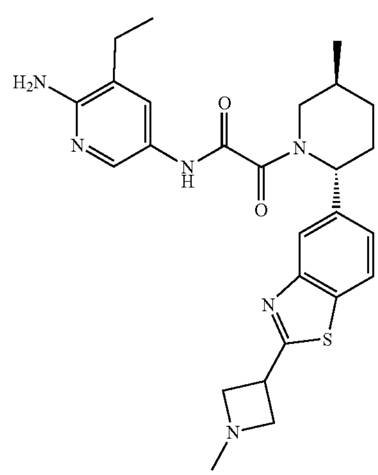 [SMILES: CCc1cc(NC(=O)C(=O)N2C[C@@H](C)CC[C@@H]2c2ccc3sc(C4CN(C)C4)nc3c2)cnc1N] | 1151 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 1152 | abs | b | aa | aaa | b* | aa* | A | A* |
| | 1153 | or/rel | b | aa | aaa | b* | aa* | A | A* |
| | 1154 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 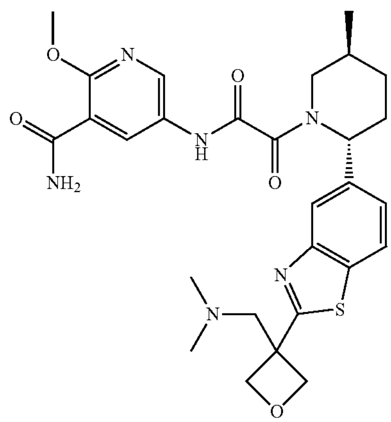 [SMILES: COc1ncc(NC(=O)C(=O)N2C[C@@H](C)CC[C@@H]2c2ccc3sc(C4(CN(C)C)COC4)nc3c2)cc1C(N)=O] | 1155 | | a | aa | aaa | b* | aa* | A | A* |
| 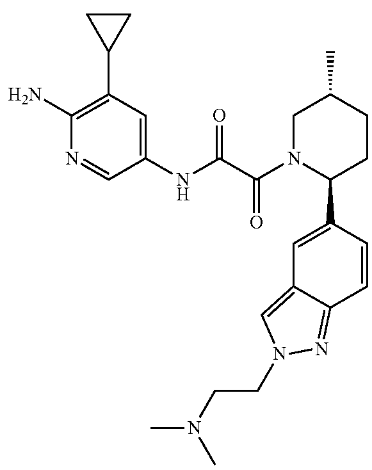 [SMILES: C[C@@H]1CC[C@@H](c2ccc3nn(CCN(C)C)cc3c2)N(C(=O)C(=O)Nc2cnc(N)c(C3CC3)c2)C1] | 1156 | or/rel | a | aa | aaa | a* | aa* | A | A* |
| 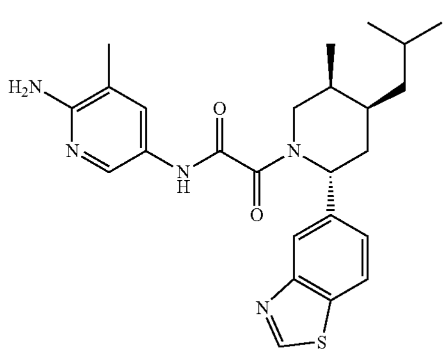 [SMILES: Cc1cc(NC(=O)C(=O)N2C[C@@H](C)[C@@H](CC(C)C)C[C@@H]2c2ccc3scnc3c2)cnc1N] | 1157 | | c | cc | ccc | c* | cc* | | C* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 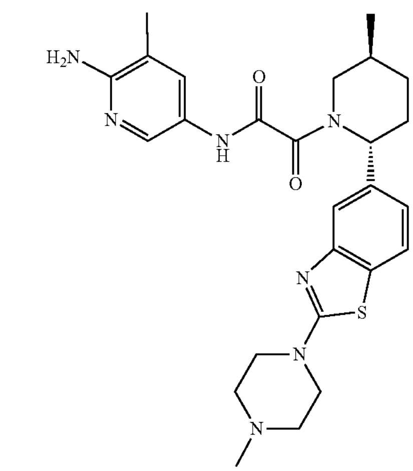 [SMILES: Cc1cc(NC(=O)C(=O)N2C[C@@H](C)CC[C@@H]2c2ccc3sc(N4CCN(C)CC4)nc3c2)cnc1N] | 1158 | abs | a | aa | aaa | a* | aa* | A | A* |
| 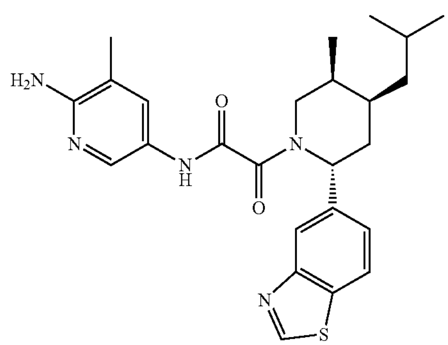 [SMILES: Cc1cc(NC(=O)C(=O)N2C[C@@H](C)[C@@H](CC(C)C)C[C@@H]2c2ccc3scnc3c2)cnc1N] | 1159 | or/rel | | | | | | | |
| 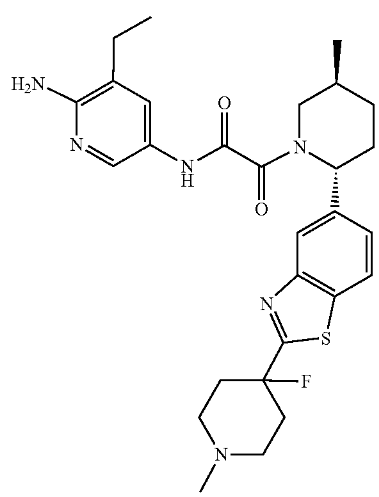 [SMILES: CCc1cc(NC(=O)C(=O)N2C[C@@H](C)CC[C@@H]2c2ccc3sc(C4(F)CCN(C)CC4)nc3c2)cnc1N] | 1160 | | a | aa | aaa | a* | aa* | A | A* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 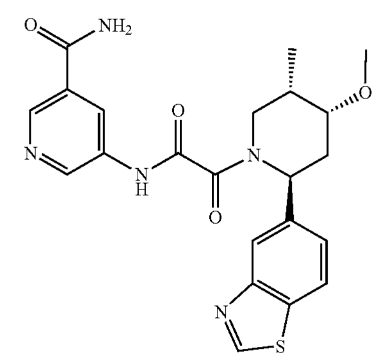 [SMILES: CO[C@@H]1C[C@@H](c2ccc3scnc3c2)N(C(=O)C(=O)Nc2cncc(C(N)=O)c2)C[C@@H]1C] | 1161 | or/rel | b | aa | aaa | b* | aa* | A | A* |
| 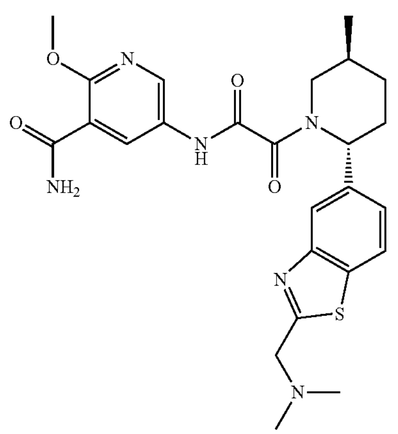 [SMILES: COc1ncc(NC(=O)C(=O)N2C[C@@H](C)CC[C@@H]2c2ccc3sc(CN(C)C)nc3c2)cc1C(N)=O] | 1162 | abs | b | aa | aaa | b* | aa* | A | A* |
| 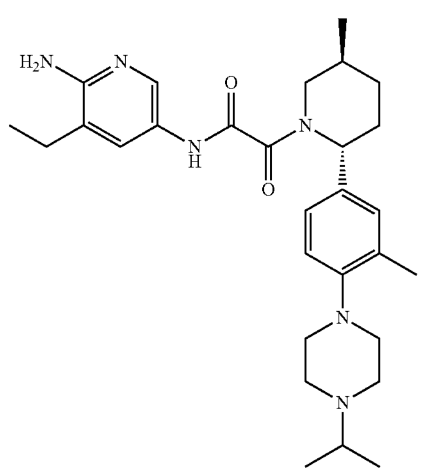 [SMILES: CCc1cc(NC(=O)C(=O)N2C[C@@H](C)CC[C@@H]2c2ccc(N3CCN(C(C)C)CC3)c(C)c2)cnc1N] | 1163 | | a | aa | aaa | b* | aa* | A | A* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 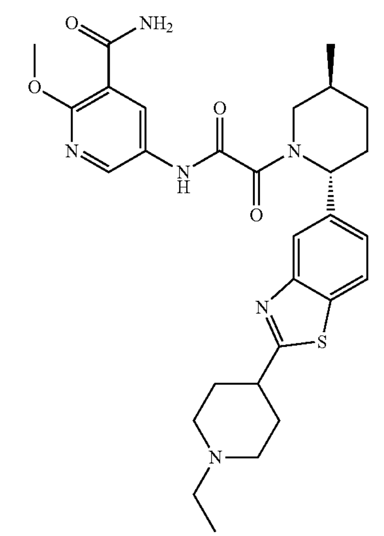 [SMILES: CCN1CCC(c2nc3cc([C@H]4CC[C@H](C)CN4C(=O)C(=O)Nc4cnc(OC)c(C(N)=O)c4)ccc3s2)CC1] | 1164 | abs | a | aa | aaa | b* | aa* | A | A* |
| 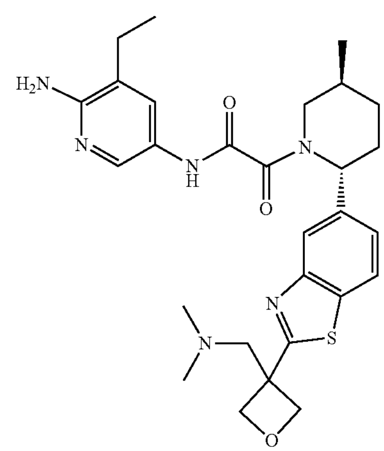 [SMILES: CCc1cc(NC(=O)C(=O)N2C[C@@H](C)CC[C@@H]2c2ccc3sc(C4(CN(C)C)COC4)nc3c2)cnc1N] | 1165 | abs | b | aa | aaa | a* | aa* | B | A* |
| 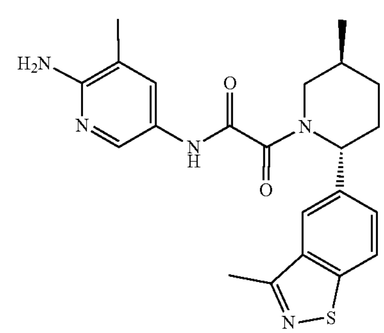 [SMILES: Cc1cc(NC(=O)C(=O)N2C[C@@H](C)CC[C@@H]2c2ccc3snc(C)c3c2)cnc1N] | 1166 | or/rel | b | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 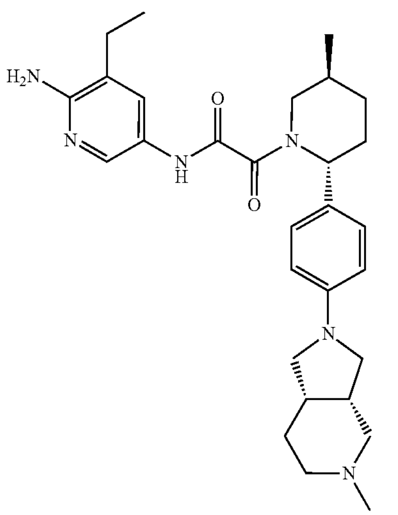 [SMILES: CCc1cc(NC(=O)C(=O)N2C[C@@H](C)CC[C@@H]2c2ccc(N3C[C@H]4CCN(C)C[C@H]4C3)cc2)cnc1N] | 1167 | abs | a | aa | aaa | b* | aa* | A | A* |
| 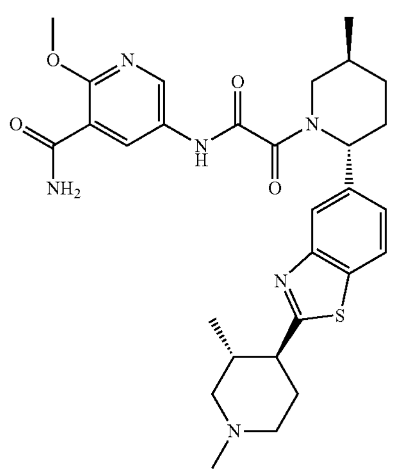 [SMILES: COc1ncc(NC(=O)C(=O)N2C[C@@H](C)CC[C@@H]2c2ccc3sc([C@H]4CCN(C)C[C@@H]4C)nc3c2)cc1C(N)=O] | 1168 | | a | aa | aaa | a* | aa* | A | A* |
| 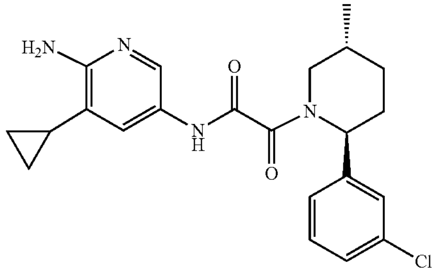 [SMILES: C[C@@H]1CC[C@@H](c2cccc(Cl)c2)N(C(=O)C(=O)Nc2cnc(N)c(C3CC3)c2)C1] | 1169 | or/rel | c | cc | bbb | | | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 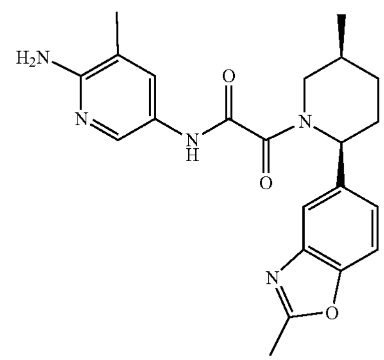 [SMILES: Cc1nc2cc([C@@H]3CC[C@H](C)CN3C(=O)C(=O)Nc3cnc(N)c(C)c3)ccc2o1] | 1170 | abs | b | aa | aaa | b* | aa* | A | A* |
| 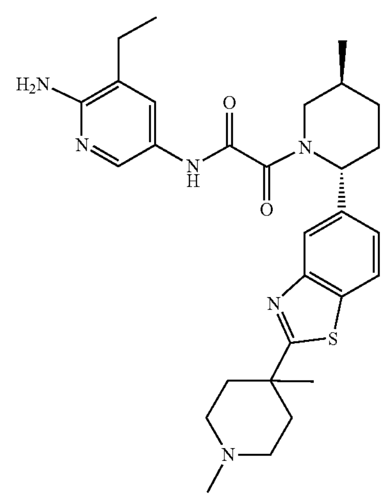 [SMILES: CCc1cc(NC(=O)C(=O)N2C[C@@H](C)CC[C@@H]2c2ccc3sc(C4(C)CCN(C)CC4)nc3c2)cnc1N] | 1171 | abs | a | aa | aaa | a* | aa* | A | A* |
| 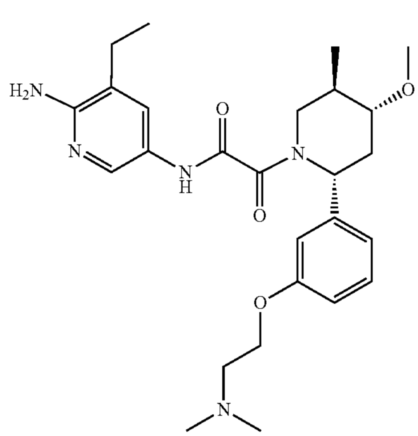 [SMILES: CCc1cc(NC(=O)C(=O)N2C[C@@H](C)[C@H](OC)C[C@@H]2c2cccc(OCCN(C)C)c2)cnc1N] | 1172 | and/rac | b | bb | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| (structure) | 1173 | or/rel | b | aa | aaa | a* | aa* | A | A* |
| (structure) | 1174 | abs | a | aa | aaa | a* | aa* | A | A* |
| (structure) | 1175 | abs | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 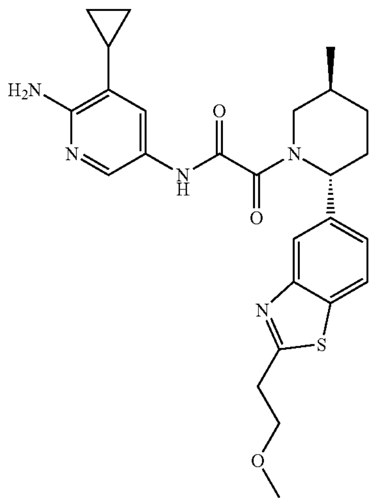 [SMILES: COCCc1nc2cc([C@H]3CC[C@H](C)CN3C(=O)C(=O)Nc3cnc(N)c(C4CC4)c3)ccc2s1] | 1176 | or/rel | c | cc | ccc | c* | cc* | | C* |
| 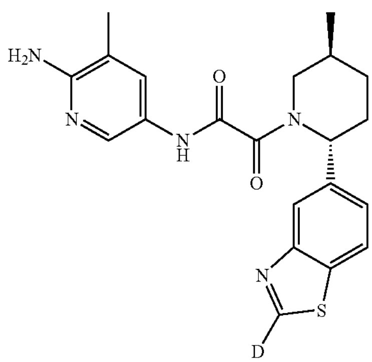 [SMILES: [2H]c1nc2cc([C@H]3CC[C@H](C)CN3C(=O)C(=O)Nc3cnc(N)c(C)c3)ccc2s1] | 1177 | abs | a | aa | aaa | b* | aa* | A | A* |
| 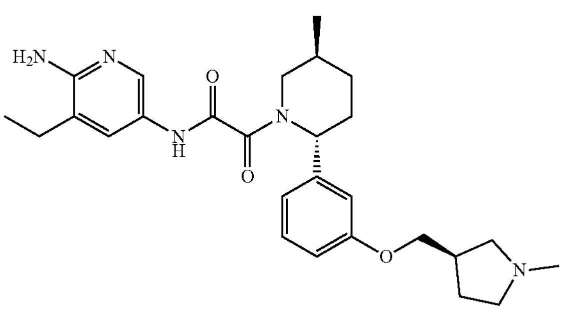 [SMILES: CCc1cc(NC(=O)C(=O)N2C[C@@H](C)CC[C@@H]2c2cccc(OC[C@@H]3CCN(C)C3)c2)cnc1N] | 1178 | abs | a | aa | aaa | a* | aa* | A | A* |
| 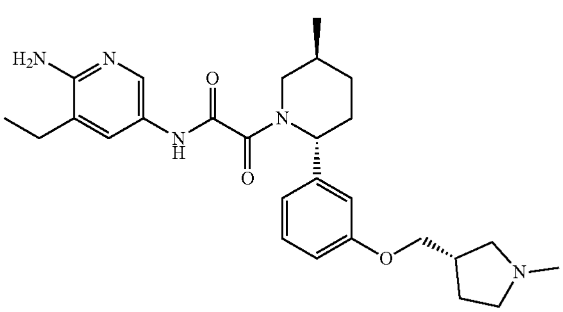 [SMILES: CCc1cc(NC(=O)C(=O)N2C[C@@H](C)CC[C@@H]2c2cccc(OC[C@H]3CCN(C)C3)c2)cnc1N] | 1179 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 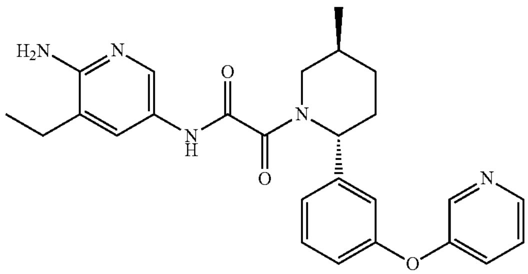 [SMILES: CCc1cc(NC(=O)C(=O)N2C[C@@H](C)CC[C@@H]2c2cccc(Oc3cccnc3)c2)cnc1N] | 1180 | abs | b | | aaa | b* | aa* | A | A* |
| 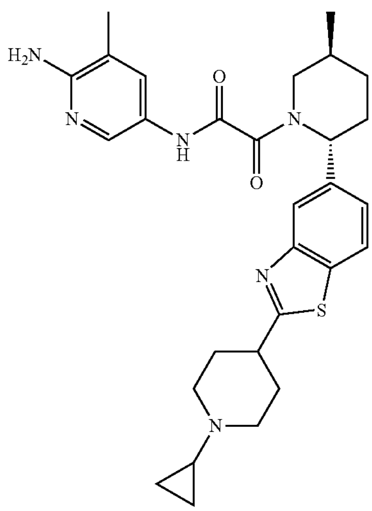 [SMILES: Cc1cc(NC(=O)C(=O)N2C[C@@H](C)CC[C@@H]2c2ccc3sc(C4CCN(C5CC5)CC4)nc3c2)cnc1N] | 1181 | abs | a | aa | aaa | a* | aa* | B | A* |
| 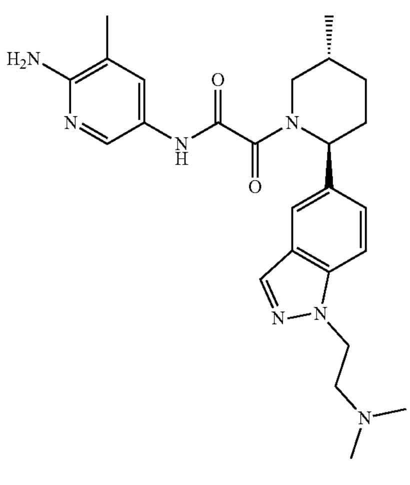 [SMILES: Cc1cc(NC(=O)C(=O)N2C[C@H](C)CC[C@H]2c2ccc3c(cnn3CCN(C)C)c2)cnc1N] | 1182 | or/rel | a | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1183 | abs | | | | | | | |
| | 1184 | and/rac | b | bb | bbb | b* | aa* | A | A* |
| | 1185 | | a | aa | aaa | a* | aa* | A | A* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1186 | abs | b | aa | aaa | a* | aa* | A | A* |
| | 1187 | abs | a | aa | aaa | a* | aa* | A | A* |
| | 1188 | abs | b | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 1190 | or/rel | b | aa | aaa | b* | aa* | A | A* |
| | 1191 | or/rel | c | cc | ccc | c* | cc* | | C* |
| | 1192 | abs | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 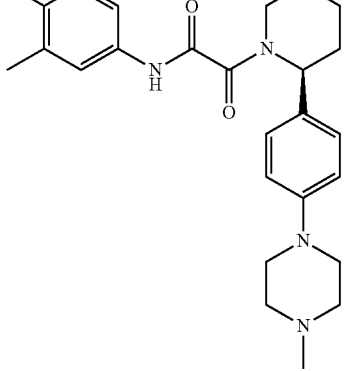 | 1193 | or/rel | c | cc | ccc | c* | cc* | | C* |
| 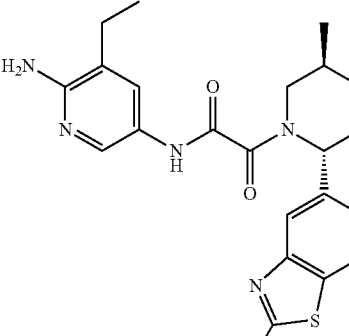 | 1194 | abs | b | aa | aaa | b* | aa* | A | A* |
| 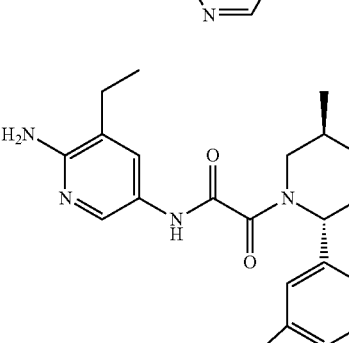 | 1195 | abs | b | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 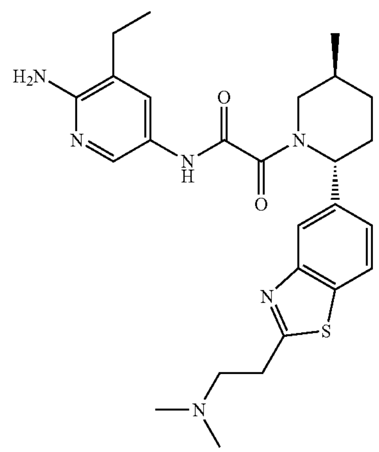 [SMILES: CCc1cc(NC(=O)C(=O)N2C[C@@H](C)CC[C@@H]2c2ccc3sc(CCN(C)C)nc3c2)cnc1N] | 1196 | or/rel | a | aa | aaa | a* | aa* | A | A* |
| 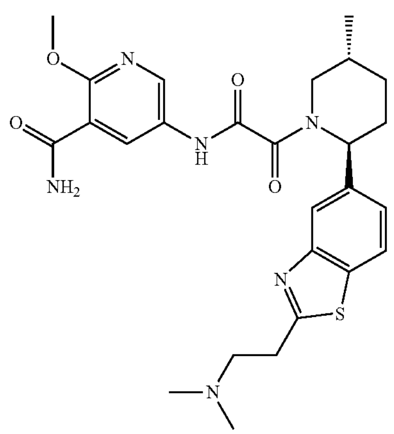 [SMILES: COc1ncc(NC(=O)C(=O)N2C[C@H](C)CC[C@H]2c2ccc3sc(CCN(C)C)nc3c2)cc1C(N)=O] | 1197 | or/rel | c | cc | ccc | | | | B* |
| 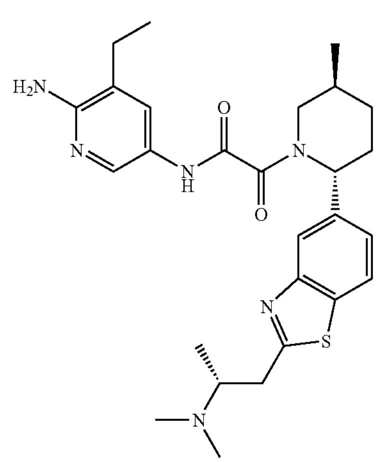 [SMILES: CCc1cc(NC(=O)C(=O)N2C[C@@H](C)CC[C@@H]2c2ccc3sc(C[C@@H](C)N(C)C)nc3c2)cnc1N] | 1198 | abs | b | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 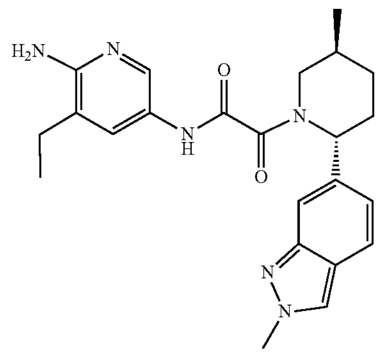 [SMILES: CCc1cc(NC(=O)C(=O)N2C[C@@H](C)CC[C@@H]2c2ccc3cn(C)nc3c2)cnc1N] | 1199 | abs | b | aa | aaa | b* | aa* | A | A* |
| 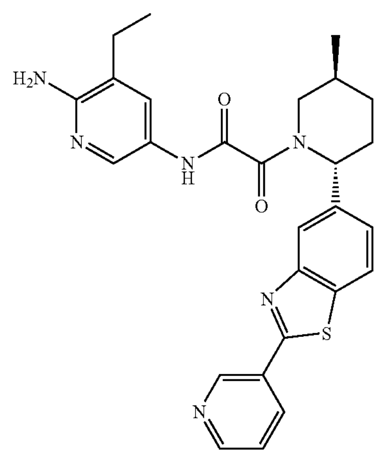 [SMILES: CCc1cc(NC(=O)C(=O)N2C[C@@H](C)CC[C@@H]2c2ccc3sc(-c4cccnc4)nc3c2)cnc1N] | 1200 | abs | b | aa | aaa | b* | aa* | A | A* |
| 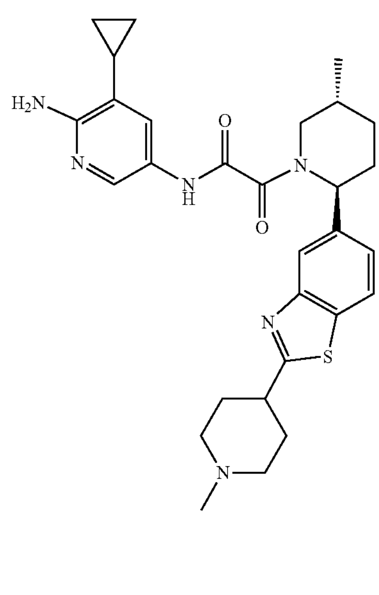 [SMILES: C[C@@H]1CC[C@@H](c2ccc3sc(C4CCN(C)CC4)nc3c2)N(C(=O)C(=O)Nc2cnc(N)c(C3CC3)c2)C1] | 1201 | abs | c | cc | bbb | c* | bb* | B | A* |

TABLE 1-continued
Exemplary compounds of the invention and biological data
| Structure | Nr | Stereo | No Co-factor/ SAM rel IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 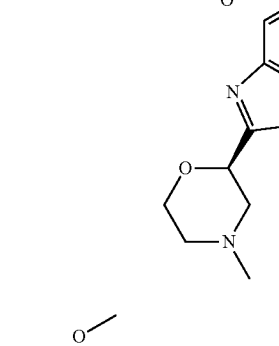 | 1202 | abs | b | aa | aaa | a* | aa* | A | A* |
| 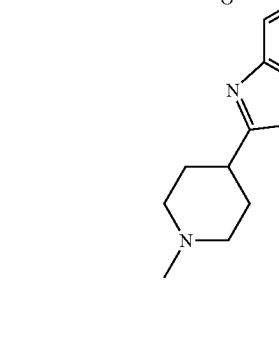 | 1203 | abs | a | aa | aaa | a* | aa* | A | A* |
| 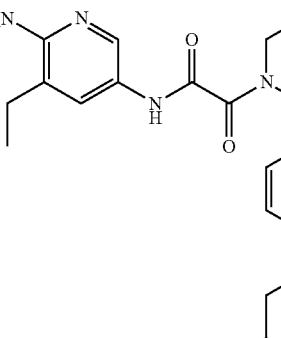 | 1204 | abs | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1205 | or/rel | a | aa | aaa | b* | aa* | A | A* |
| | 1206 | abs | b | aa | aaa | b* | aa* | A | A* |
| | 1207 | or/rel | b | bb | bbb | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 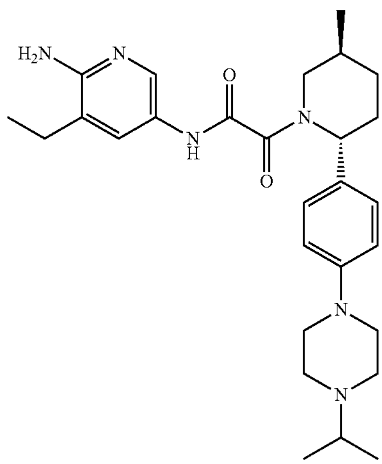 [SMILES: CCc1cc(NC(=O)C(=O)N2C[C@@H](C)CC[C@@H]2c2ccc(N3CCN(C(C)C)CC3)cc2)cnc1N] | 1208 | or/rel | b | aa | aaa | b* | aa* | A | A* |
| 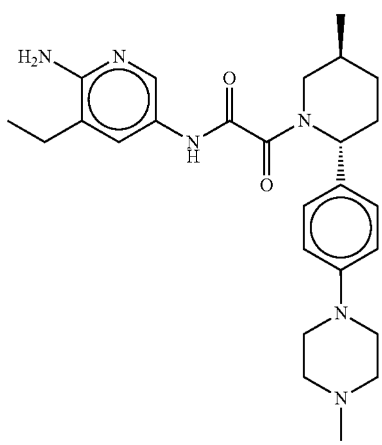 | 1209 | and/rac | b | bb | aaa | b* | aa* | A | A* |
| 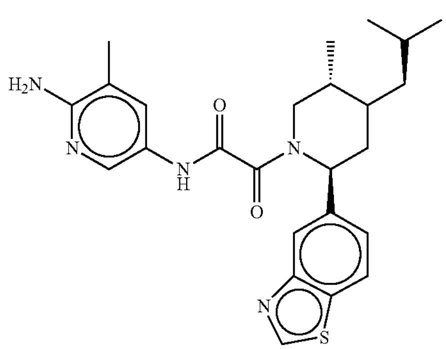 | 1210 | or/rel | b | bb | aaa | c* | bb* | | B* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 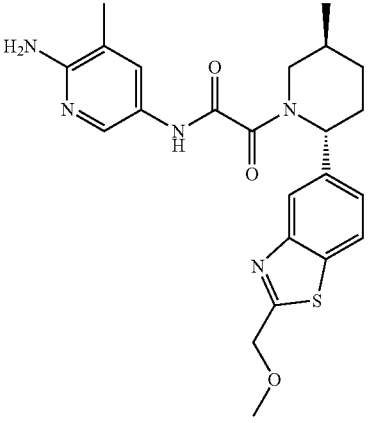 [SMILES: COCc1nc2cc([C@H]3CC[C@H](C)CN3C(=O)C(=O)Nc3cnc(N)c(C)c3)ccc2s1] | 1211 | or/rel | b | bb | aaa | a* | aa* | A | A* |
| 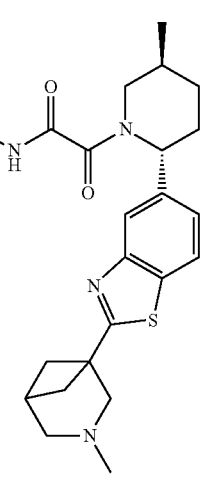 | 1212 | | a | aa | aaa | a* | aa* | B | A* |
| 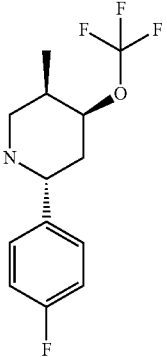 | 1213 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 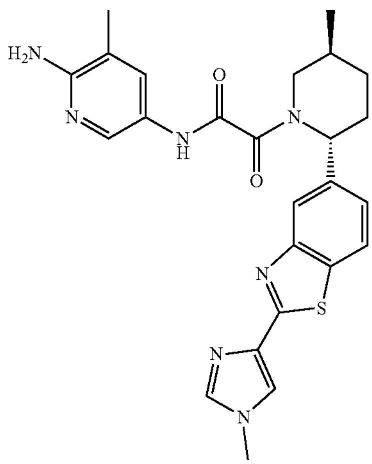 [SMILES: Cc1cc(NC(=O)C(=O)N2C[C@@H](C)CC[C@@H]2c2ccc3sc(-c4cn(C)cn4)nc3c2)cnc1N] | 1214 | abs | b | aa | aaa | b* | aa* | A | A* |
| 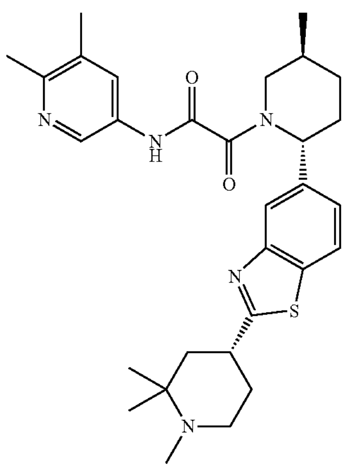 [SMILES: Cc1cc(NC(=O)C(=O)N2C[C@@H](C)CC[C@@H]2c2ccc3sc([C@@H]4CCN(C)C(C)(C)C4)nc3c2)cnc1C] | 1215 | abs | a | aa | aaa | b* | aa* | A | A* |
| 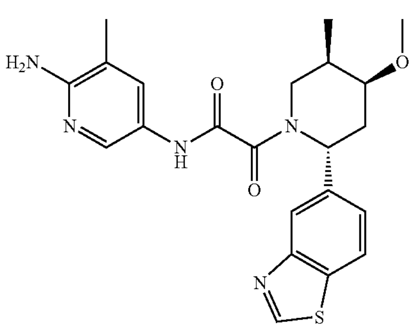 [SMILES: CO[C@H]1C[C@H](c2ccc3scnc3c2)N(C(=O)C(=O)Nc2cnc(N)c(C)c2)C[C@H]1C] | 1216 | or/rel | b | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 1217 | a | a | aa | aaa | a* | aa* | B | A* |
| | 1218 | or/rel | a | aa | aaa | a* | aa* | A | A* |
| | 1219 | abs | b | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 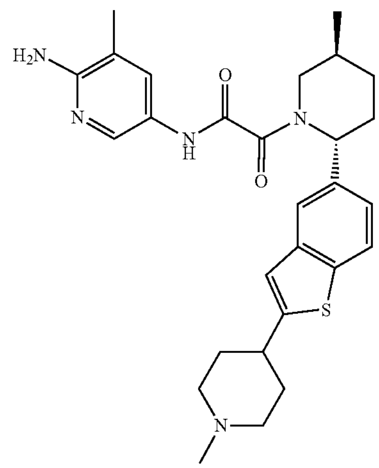 [SMILES: Cc1cc(NC(=O)C(=O)N2C[C@@H](C)CC[C@@H]2c2ccc3sc(C4CCN(C)CC4)cc3c2)cnc1N] | 1220 | abs | a | aa | aaa | a* | aa* | B | A* |
| 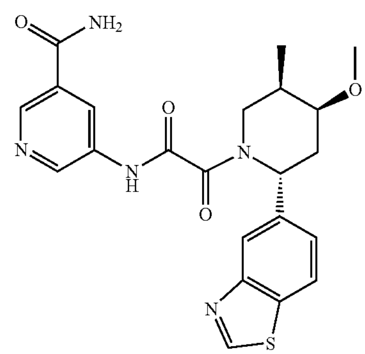 [SMILES: CO[C@H]1C[C@H](c2ccc3scnc3c2)N(C(=O)C(=O)Nc2cncc(C(N)=O)c2)C[C@H]1C] | 1221 | or/rel | c | | bbb | c* | bb* | A | B* |
| 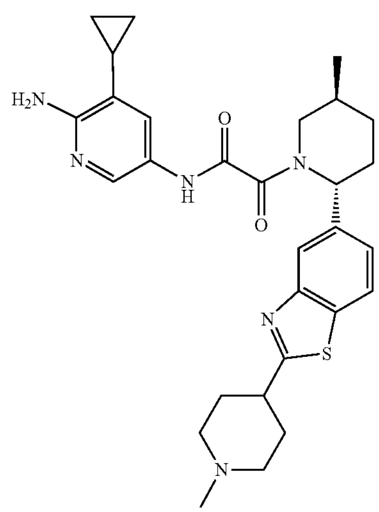 [SMILES: C[C@H]1CC[C@H](c2ccc3sc(C4CCN(C)CC4)nc3c2)N(C(=O)C(=O)Nc2cnc(N)c(C3CC3)c2)C1] | 1222 | or/rel | a | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 1223 | and/rac | b | bb | aaa | b* | aa* | A | A* |
| | 1224 | abs | b | aa | aaa | a* | aa* | A | A* |
| | 1225 | abs | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 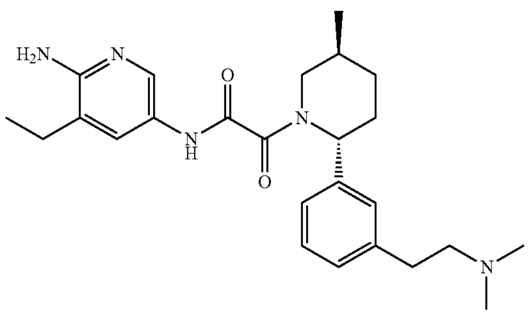 [SMILES: CCc1cc(NC(=O)C(=O)N2C[C@@H](C)CC[C@@H]2c2cccc(CCN(C)C)c2)cnc1N] | 1226 | abs | b | aa | aaa | b* | aa* | A | A* |
| 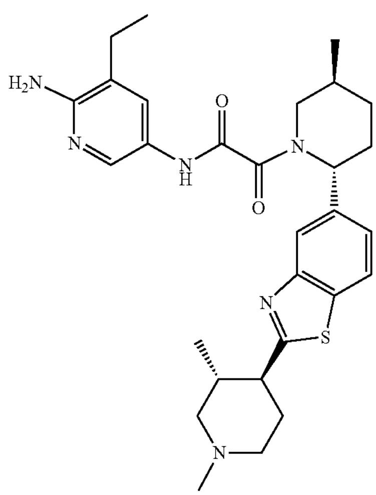 [SMILES: CCc1cc(NC(=O)C(=O)N2C[C@@H](C)CC[C@@H]2c2ccc3sc([C@H]4CCN(C)C[C@@H]4C)nc3c2)cnc1N] | 1227 | abs | a | aa | aaa | a* | aa* | A | A* |
| 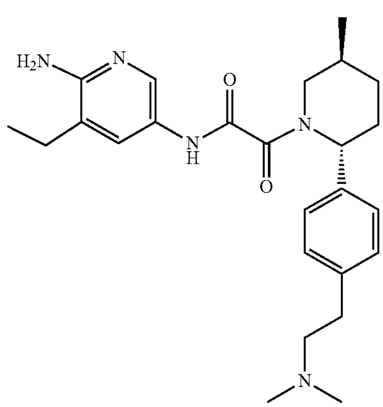 [SMILES: CCc1cc(NC(=O)C(=O)N2C[C@@H](C)CC[C@@H]2c2ccc(CCN(C)C)cc2)cnc1N] | 1228 | abs | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 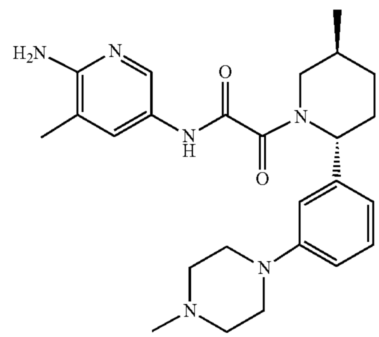 [SMILES: Cc1cc(NC(=O)C(=O)N2C[C@@H](C)CC[C@@H]2c2cccc(N3CCN(C)CC3)c2)cnc1N] | 1229 | or/rel | a | aa | aaa | a* | aa* | B | A* |
| 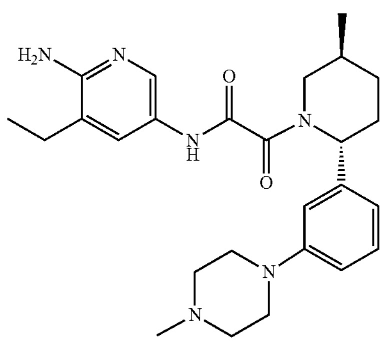 [SMILES: CCc1cc(NC(=O)C(=O)N2C[C@@H](C)CC[C@@H]2c2cccc(N3CCN(C)CC3)c2)cnc1N] | 1230 | rac | | | | | | | |
| 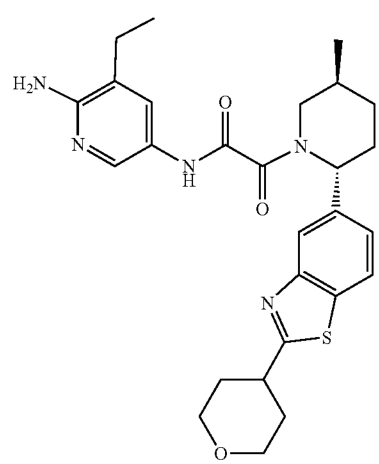 [SMILES: CCc1cc(NC(=O)C(=O)N2C[C@@H](C)CC[C@@H]2c2ccc3sc(C4CCOCC4)nc3c2)cnc1N] | 1231 | abs | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 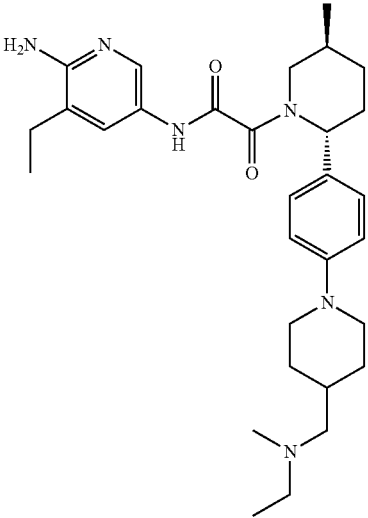 [SMILES: CCc1cc(NC(=O)C(=O)N2C[C@@H](C)CC[C@@H]2c2ccc(N3CCC(CN(C)CC)CC3)cc2)cnc1N] | 1232 | abs | b | aa | aaa | b* | aa* | A | A* |
| 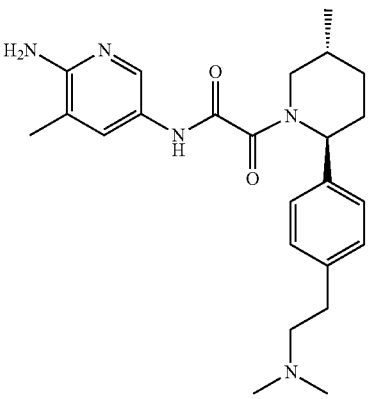 [SMILES: Cc1cc(NC(=O)C(=O)N2C[C@H](C)CC[C@H]2c2ccc(CCN(C)C)cc2)cnc1N] | 1233 | and/rac | b | bb | aaa | b* | aa* | B | A* |
| 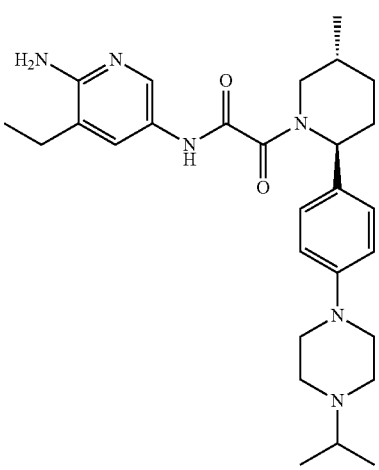 [SMILES: CCc1cc(NC(=O)C(=O)N2C[C@H](C)CC[C@H]2c2ccc(N3CCN(C(C)C)CC3)cc2)cnc1N] | 1234 | or/rel | c | cc | ccc | c* | cc* | | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 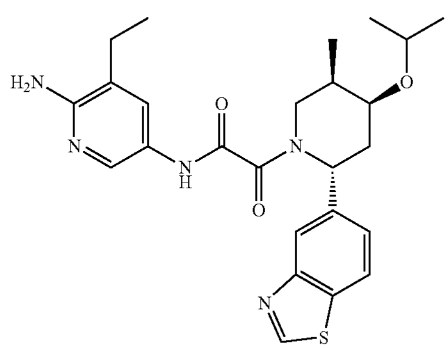 [SMILES: CCc1cc(NC(=O)C(=O)N2C[C@@H](C)[C@@H](OC(C)C)C[C@@H]2c2ccc3scnc3c2)cnc1N] | 1235 | and/rac | b | bb | bbb | b* | aa* | A | A* |
| 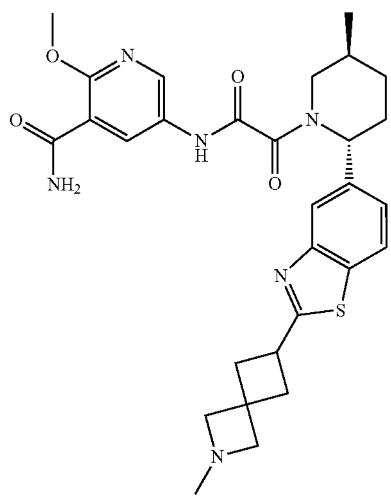 [SMILES: COc1ncc(NC(=O)C(=O)N2C[C@@H](C)CC[C@@H]2c2ccc3sc(C4CC5(C4)CN(C)C5)nc3c2)cc1C(N)=O] | 1236 | abs | a | aa | aaa | a* | aa* | A | A* |
| 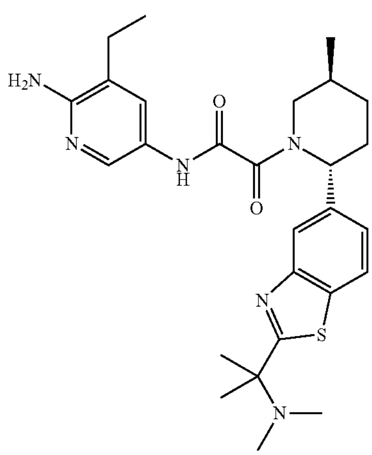 [SMILES: CCc1cc(NC(=O)C(=O)N2C[C@@H](C)CC[C@@H]2c2ccc3sc(C(C)(C)N(C)C)nc3c2)cnc1N] | 1237 | abs | b | aa | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 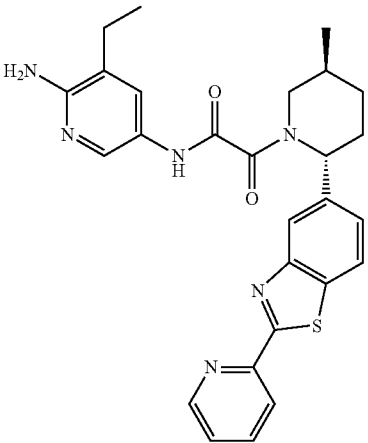 [SMILES: CCc1cc(NC(=O)C(=O)N2C[C@@H](C)CC[C@@H]2c2ccc3sc(-c4ccccn4)nc3c2)cnc1N] | 1238 | abs | b | bb | aaa | b* | aa* | A | A* |
| 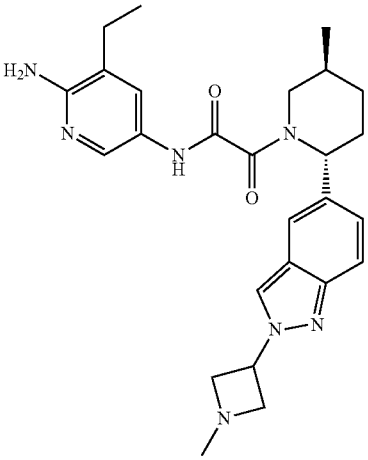 [SMILES: CCc1cc(NC(=O)C(=O)N2C[C@@H](C)CC[C@@H]2c2ccc3nn(C4CN(C)C4)cc3c2)cnc1N] | 1239 | | b | aa | aaa | b* | aa* | A | A* |
| 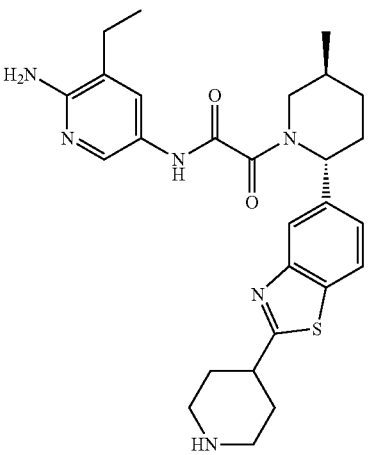 [SMILES: CCc1cc(NC(=O)C(=O)N2C[C@@H](C)CC[C@@H]2c2ccc3sc(C4CCNCC4)nc3c2)cnc1N] | 1240 | abs | a | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 1241 | or/rel | c | cc | ccc | c* | cc* | | B* |
| | 1242 | abs | b | aa | aaa | b* | aa* | A | A* |
| | 1243 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 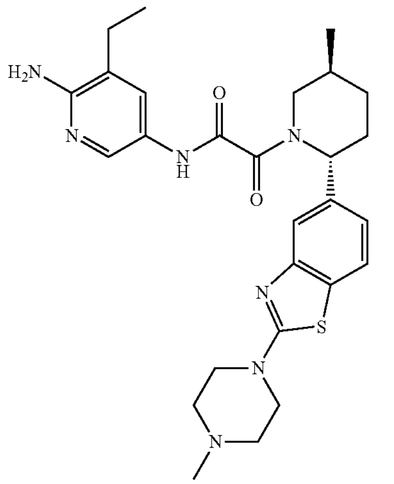 [SMILES: CCc1cc(NC(=O)C(=O)N2C[C@@H](C)CC[C@@H]2c2ccc3sc(N4CCN(C)CC4)nc3c2)cnc1N] | 1244 | abs | b | aa | aaa | a* | aa* | A | A* |
| 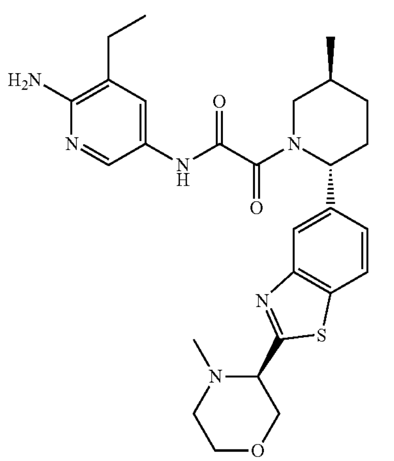 [SMILES: CCc1cc(NC(=O)C(=O)N2C[C@@H](C)CC[C@@H]2c2ccc3sc([C@H]4COCCN4C)nc3c2)cnc1N] | 1245 | abs | b | aa | aaa | b* | aa* | A | A* |
| 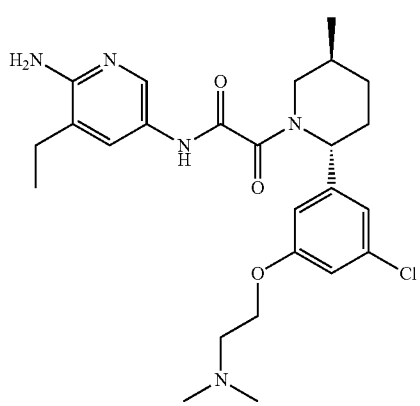 [SMILES: CCc1cc(NC(=O)C(=O)N2C[C@@H](C)CC[C@@H]2c2cc(Cl)cc(OCCN(C)C)c2)cnc1N] | 1247 | abs | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 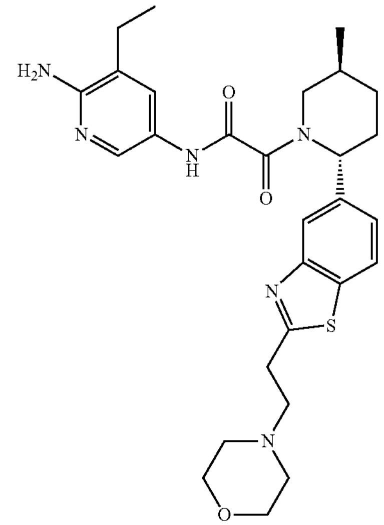 [SMILES: CCc1cc(NC(=O)C(=O)N2C[C@@H](C)CC[C@@H]2c2ccc3sc(CCN4CCOCC4)nc3c2)cnc1N] | 1248 | abs | a | aa | aaa | b* | aa* | A | A* |
| 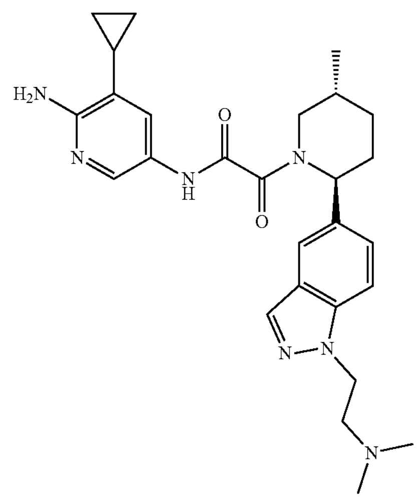 [SMILES: C[C@@H]1CC[C@@H](c2ccc3c(cnn3CCN(C)C)c2)N(C(=O)C(=O)Nc2cnc(N)c(C3CC3)c2)C1] | 1249 | or/rel | b | aa | aaa | b* | aa* | A | A* |
| 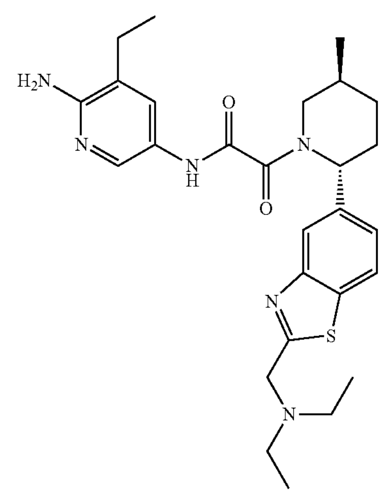 [SMILES: CCc1cc(NC(=O)C(=O)N2C[C@@H](C)CC[C@@H]2c2ccc3sc(CN(CC)CC)nc3c2)cnc1N] | 1250 | abs | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 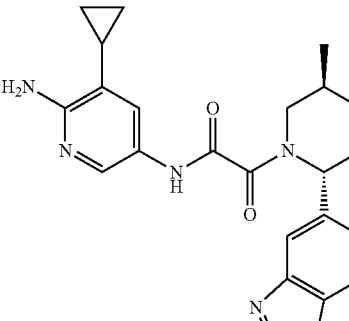 | 1251 | or/rel | a | aa | aaa | a* | aa* | A | A* |
| 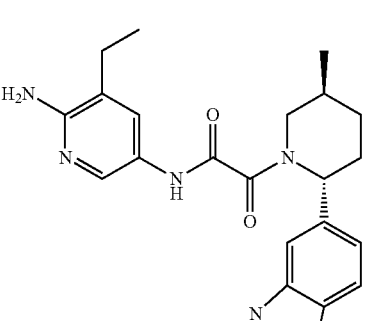 | 1252 | abs | b | aa | aaa | a* | aa* | A | A* |
| 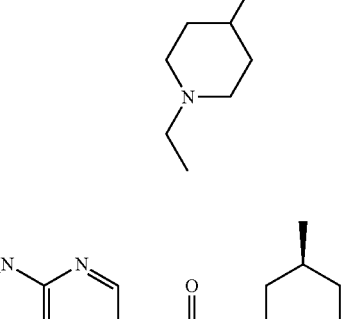 | 1253 | or/rel | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1254 | or/rel | a | aa | aaa | b* | aa* | A | A* |
| | 1255 | abs | b | aa | aaa | a* | aa* | A | A* |
| | 1256 | abs | b | aa | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 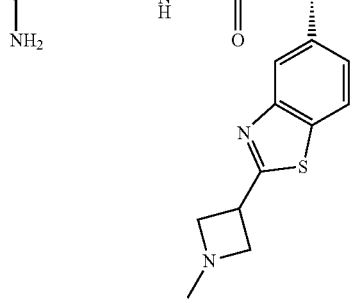 | 1257 |  | a | aa | aaa | b* | aa* | A | A* |
| 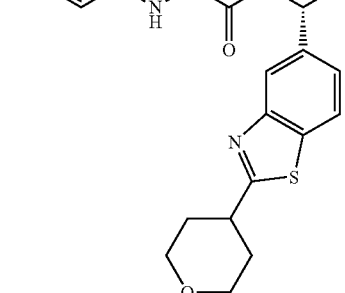 | 1258 | abs | b | aa | aaa | b* | aa* | A | A* |
| 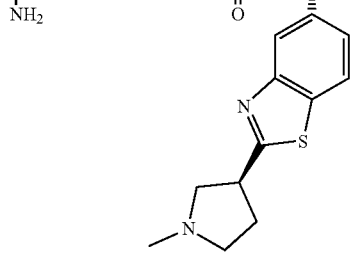 | 1260 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 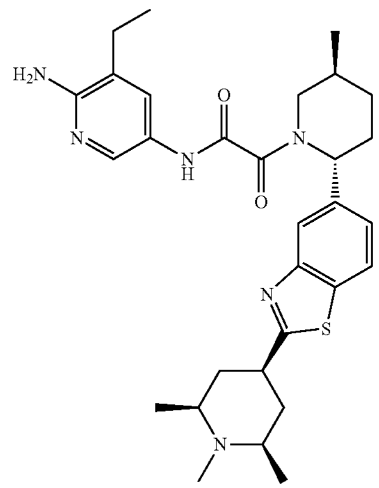 [SMILES: CCc1cc(NC(=O)C(=O)N2C[C@@H](C)CC[C@@H]2c2ccc3sc([C@H]4C[C@@H](C)N(C)[C@@H](C)C4)nc3c2)cnc1N] | 1261 | abs | a | aa | aaa | a* | aa* | A | A* |
| 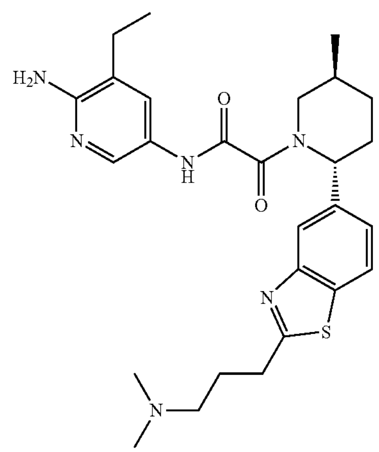 [SMILES: CCc1cc(NC(=O)C(=O)N2C[C@@H](C)CC[C@@H]2c2ccc3sc(CCCN(C)C)nc3c2)cnc1N] | 1262 | abs | a | aa | aaa | a* | aa* | A | A* |
| 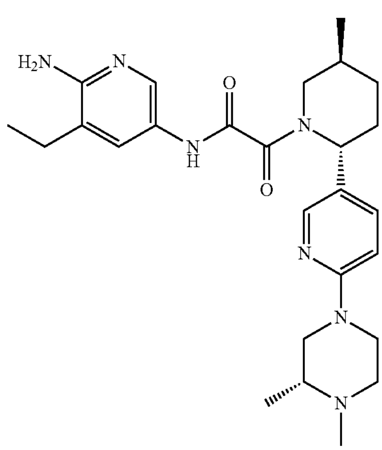 [SMILES: CCc1cc(NC(=O)C(=O)N2C[C@@H](C)CC[C@@H]2c2ccc(N3CCN(C)[C@H](C)C3)nc2)cnc1N] | 1263 | abs | b | cc | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted viability |
|---|---|---|---|---|---|---|---|---|---|
| | 1264 | abs | b | aa | aaa | b* | aa* | A | A* |
| | 1265 | and/rac | b | | bbb | b* | aa* | A | A* |
| | 1266 | abs | b | aa | aaa | a* | aa* | A | A* |

TABLE 1-continued
Exemplary compounds of the invention and biological data
| Structure | Nr | Stereo | SAM IC50 | No Cofactor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 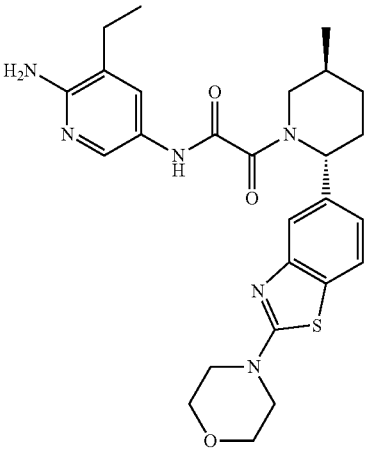 [SMILES: CCc1cc(NC(=O)C(=O)N2C[C@@H](C)CC[C@@H]2c2ccc3sc(N4CCOCC4)nc3c2)cnc1N] | 1267 | abs | b | aa | aaa | b* | aa* | A | A* |
| 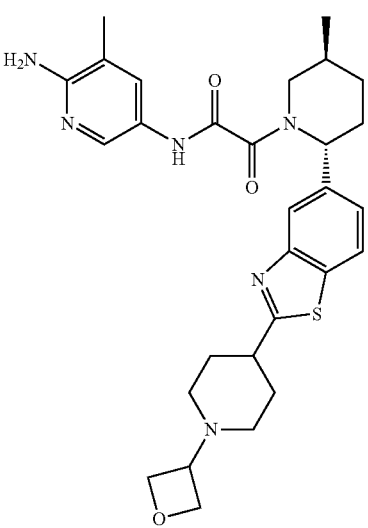 [SMILES: Cc1cc(NC(=O)C(=O)N2C[C@@H](C)CC[C@@H]2c2ccc3sc(C4CCN(C5COC5)CC4)nc3c2)cnc1N] | 1268 | abs | a | aa | aaa | b* | aa* | A | A* |
| 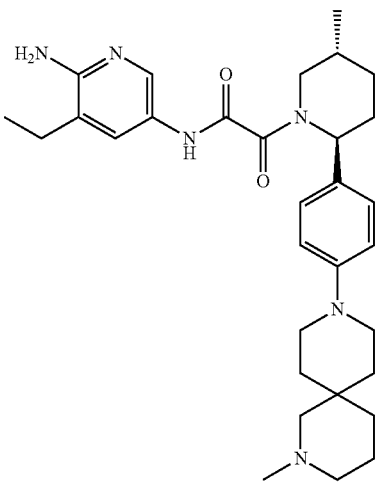 [SMILES: CCc1cc(NC(=O)C(=O)N2C[C@H](C)CC[C@H]2c2ccc(N3CCC4(CCCN(C)C4)CC3)cc2)cnc1N] | 1269 | or/rel | c | cc | bbb | c* | bb* | | B* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1270 | or/rel | b | bb | aaa | b* | aa* | A | A* |
| | 1271 | or/rel | b | aa | aaa | a* | aa* | B | A* |
| | 1272 | abs | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 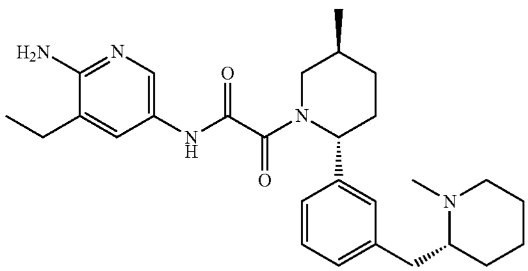 [SMILES: CCc1cc(NC(=O)C(=O)N2C[C@@H](C)CC[C@@H]2c2cccc(C[C@H]3CCCCN3C)c2)cnc1N] | 1273 | or/rel | b | aa | aaa | b* | aa* | A | A* |
| 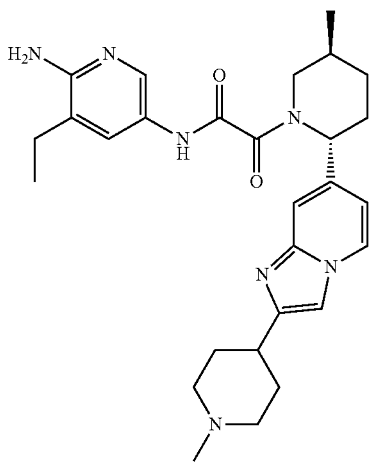 [SMILES: CCc1cc(NC(=O)C(=O)N2C[C@@H](C)CC[C@@H]2c2ccn3cc(C4CCN(C)CC4)nc3c2)cnc1N] | 1274 | abs | b | aa | aaa | b* | aa* | A | A* |
| 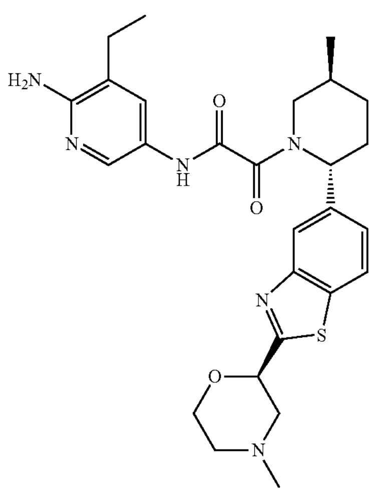 [SMILES: CCc1cc(NC(=O)C(=O)N2C[C@@H](C)CC[C@@H]2c2ccc3sc([C@H]4CN(C)CCO4)nc3c2)cnc1N] | 1275 | abs | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 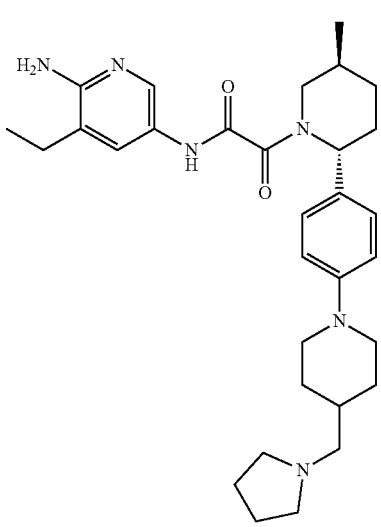 [SMILES: CCc1cc(NC(=O)C(=O)N2C[C@@H](C)CC[C@@H]2c2ccc(N3CCC(CN4CCCC4)CC3)cc2)cnc1N] | 1276 | abs | a | aa | aaa | b* | aa* | A | A* |
| 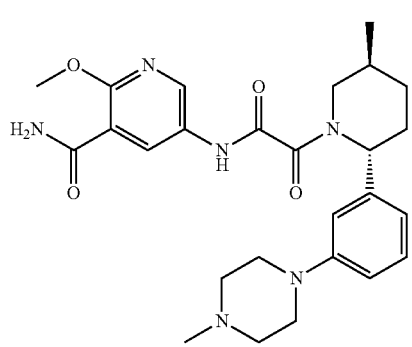 [SMILES: COc1ncc(NC(=O)C(=O)N2C[C@@H](C)CC[C@@H]2c2cccc(N3CCN(C)CC3)c2)cc1C(N)=O] | 1277 | abs | b | | aaa | b* | aa* | A | A* |
| 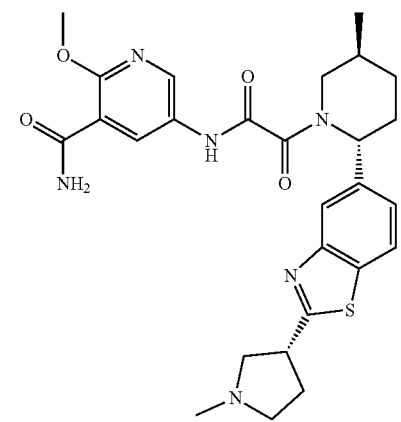 [SMILES: COc1ncc(NC(=O)C(=O)N2C[C@@H](C)CC[C@@H]2c2ccc3sc([C@@H]4CCN(C)C4)nc3c2)cc1C(N)=O] | 1278 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 1279 | or/rel | a | aa | aaa | a* | aa* | C | A* |
| | 1280 | or/rel | b | aa | aaa | b* | aa* | A | A* |
| | 1281 | and/rac | b | bb | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 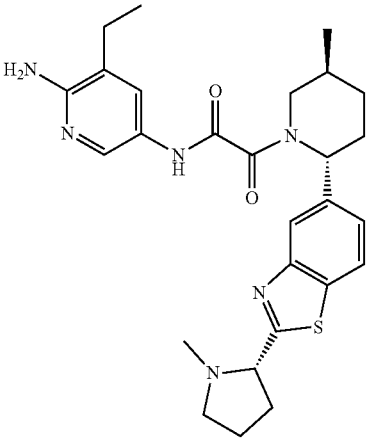 [SMILES: CCc1cc(NC(=O)C(=O)N2C[C@@H](C)CC[C@@H]2c2ccc3sc([C@@H]4CCCN4C)nc3c2)cnc1N] | 1282 | abs | b | aa | aaa | b* | aa* | A | A* |
| 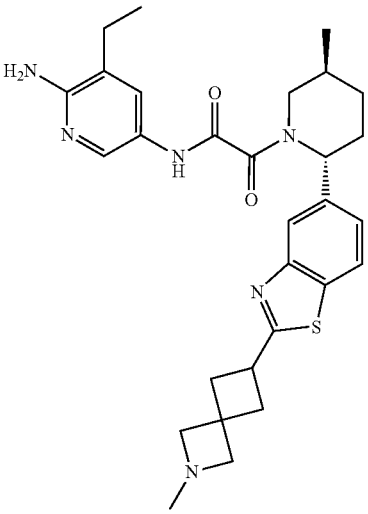 [SMILES: CCc1cc(NC(=O)C(=O)N2C[C@@H](C)CC[C@@H]2c2ccc3sc(C4CC5(C4)CN(C)C5)nc3c2)cnc1N] | 1283 | abs | a | aa | aaa | a* | aa* | A | A* |
| 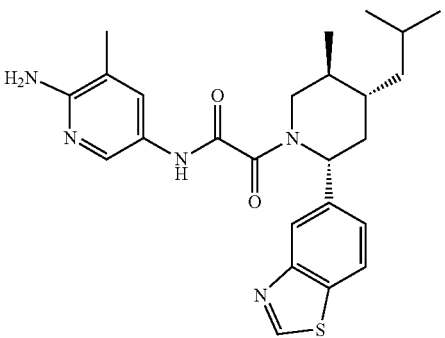 [SMILES: Cc1cc(NC(=O)C(=O)N2C[C@@H](C)[C@H](CC(C)C)C[C@@H]2c2ccc3scnc3c2)cnc1N] | 1284 | or/rel | c | cc | ccc | c* | cc* | | C* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1285 | or/rel | b | aa | aaa | b* | aa* | A | A* |
| | 1286 | or/rel | b | aa | aaa | b* | aa* | A | A* |
| | 1287 | abs | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 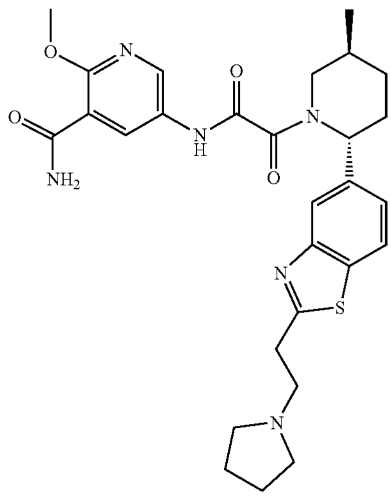 [SMILES: COc1ncc(NC(=O)C(=O)N2C[C@@H](C)CC[C@@H]2c2ccc3sc(CCN4CCCC4)nc3c2)cc1C(N)=O] | 1288 | abs | b | bb | aaa | b* | aa* | A | A* |
| 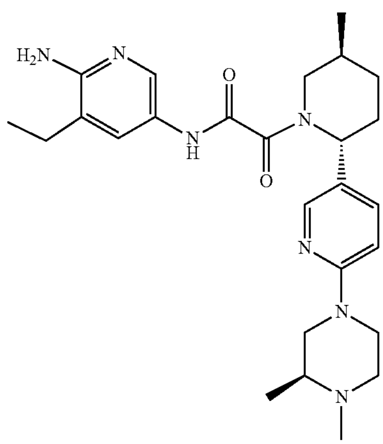 [SMILES: CCc1cc(NC(=O)C(=O)N2C[C@@H](C)CC[C@@H]2c2ccc(N3CCN(C)[C@@H](C)C3)nc2)cnc1N] | 1289 | abs | b | aa | aaa | b* | aa* | A | A* |
| 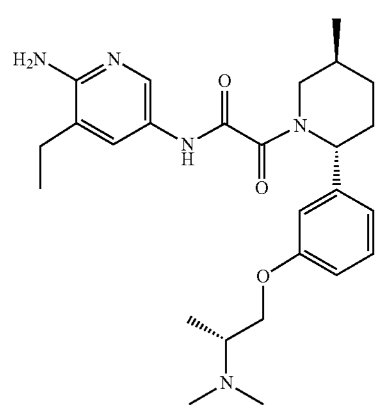 [SMILES: CCc1cc(NC(=O)C(=O)N2C[C@@H](C)CC[C@@H]2c2cccc(OC[C@@H](C)N(C)C)c2)cnc1N] | 1290 | | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| | 1291 | or/rel | c | cc | ccc | c* | bb* | | C* |
| | 1292 | abs | b | aa | aaa | b* | aa* | A | A* |
| | 1293 | or/rel | 0 | | 0 | b* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 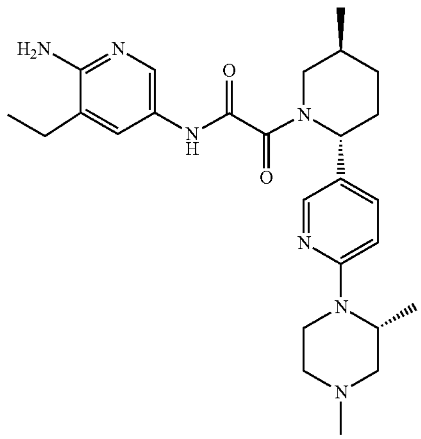 [SMILES: CCc1cc(NC(=O)C(=O)N2C[C@@H](C)CC[C@@H]2c2ccc(N3CCN(C)C[C@H]3C)nc2)cnc1N] | 1294 | abs | b | aa | aaa | b* | aa* | A | A* |
| 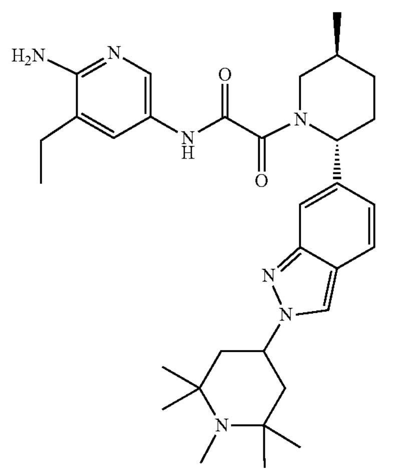 [SMILES: CCc1cc(NC(=O)C(=O)N2C[C@@H](C)CC[C@@H]2c2ccc3cn(C4CC(C)(C)N(C)C(C)(C)C4)nc3c2)cnc1N] | 1295 | abs | a | aa | aaa | a* | aa* | A | A* |
| 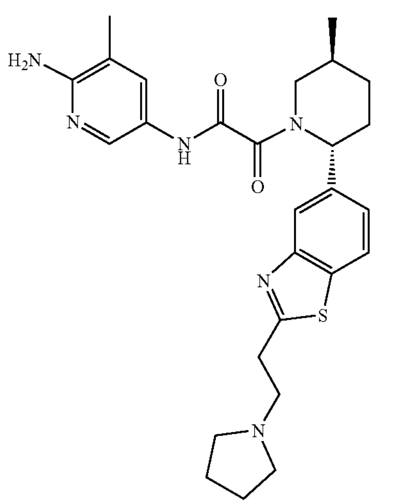 [SMILES: Cc1cc(NC(=O)C(=O)N2C[C@@H](C)CC[C@@H]2c2ccc3sc(CCN4CCCC4)nc3c2)cnc1N] | 1296 | abs | a | aa | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 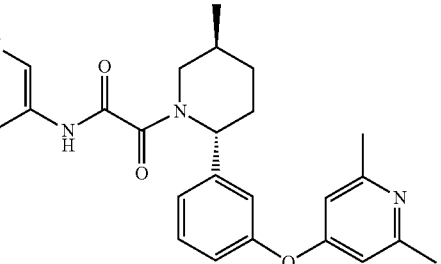 | 1297 | abs | b | | aaa | b* | aa* | A | A* |
| 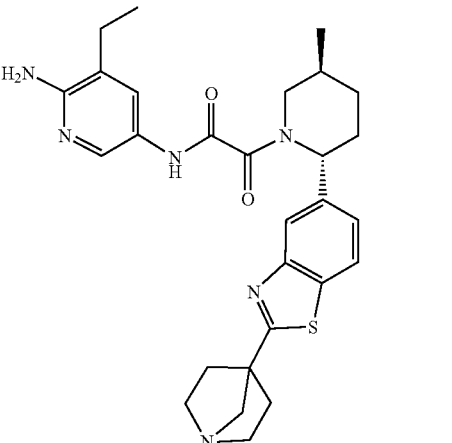 | 1298 | | b | aa | aaa | a* | aa* | B | A* |
| 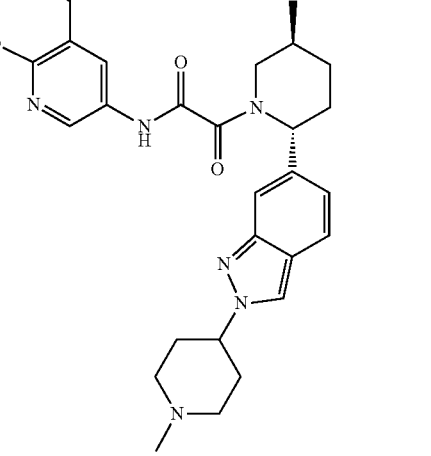 | 1299 | | a | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 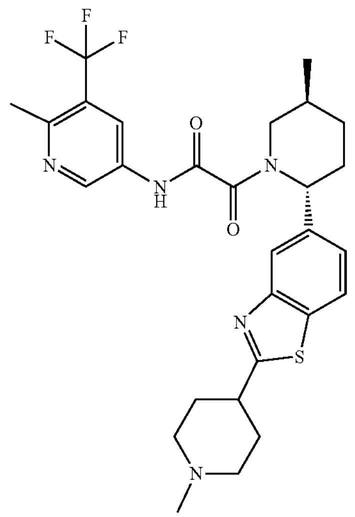 [SMILES: Cc1ncc(NC(=O)C(=O)N2C[C@@H](C)CC[C@@H]2c2ccc3sc(C4CCN(C)CC4)nc3c2)cc1C(F)(F)F] | 1300 | abs | b | aa | aaa | b* | aa* | A | A* |
| 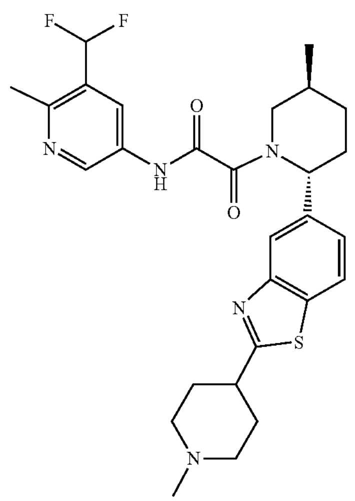 [SMILES: Cc1ncc(NC(=O)C(=O)N2C[C@@H](C)CC[C@@H]2c2ccc3sc(C4CCN(C)CC4)nc3c2)cc1C(F)F] | 1301 | abs | a | aa | aaa | a* | aa* | A | A* |
| 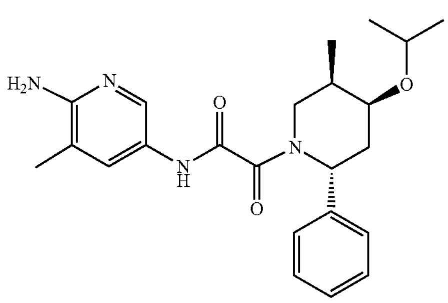 [SMILES: Cc1cc(NC(=O)C(=O)N2C[C@@H](C)[C@@H](OC(C)C)C[C@@H]2c2ccccc2)cnc1N] | 1302 | or/rel | c | cc | ccc | c* | cc* | | C* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 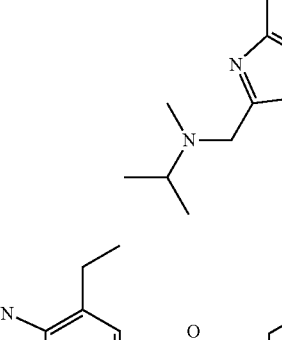 | 1303 | abs | b | aa | aaa | b* | aa* | A | A* |
| 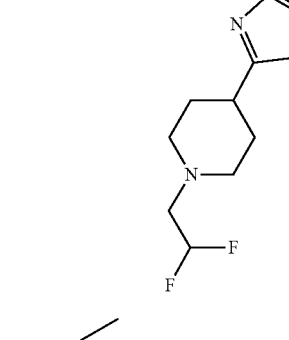 | 1304 | abs | a | aa | aaa | b* | aa* | A | A* |
| 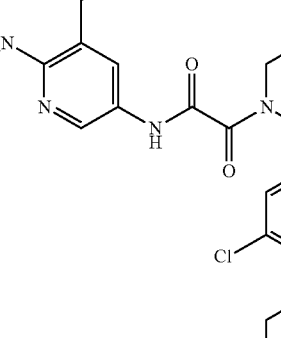 | 1305 | abs | b | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 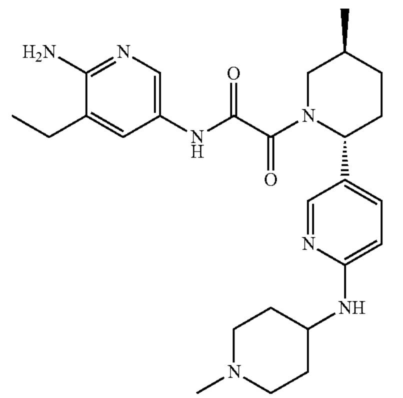 [SMILES: CCc1cc(NC(=O)C(=O)N2C[C@@H](C)CC[C@@H]2c2ccc(NC3CCN(C)CC3)nc2)cnc1N] | 1306 | abs | b | aa | aaa | b* | aa* | A | A* |
| 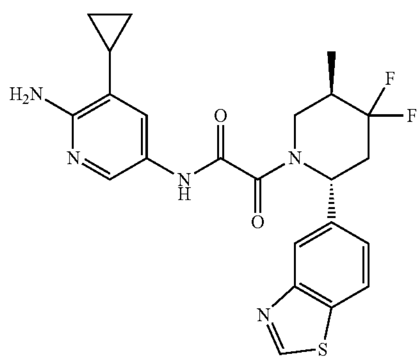 [SMILES: C[C@@H]1CN(C(=O)C(=O)Nc2cnc(N)c(C3CC3)c2)[C@@H](c2ccc3scnc3c2)CC1(F)F] | 1307 | or/rel | c | bb | bbb | c* | aa* | A | A* |
| 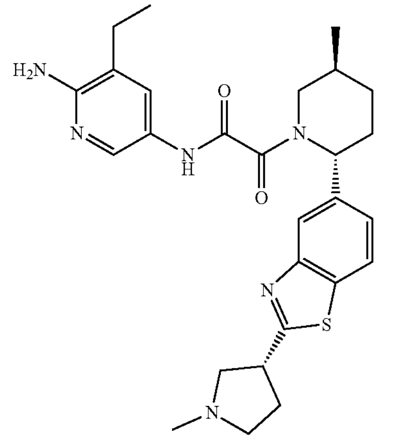 | 1308 | abs | b | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 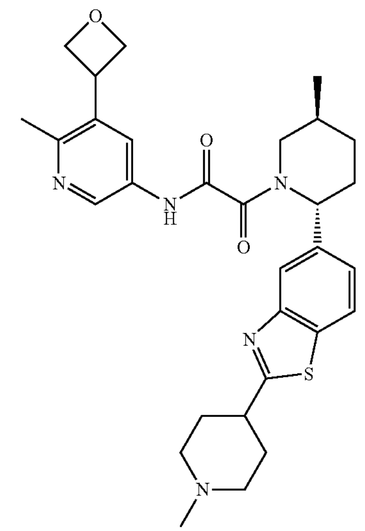 [SMILES: Cc1ncc(NC(=O)C(=O)N2C[C@@H](C)CC[C@@H]2c2ccc3sc(C4CCN(C)CC4)nc3c2)cc1C1COC1] | 1309 | abs | a | aa | aaa | a* | aa* | A | A* |
| 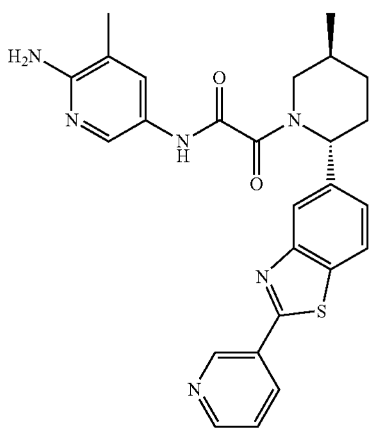 [SMILES: Cc1cc(NC(=O)C(=O)N2C[C@@H](C)CC[C@@H]2c2ccc3sc(-c4cccnc4)nc3c2)cnc1N] | 1310 | abs | b | aa | aaa | a* | aa* | A | A* |
| 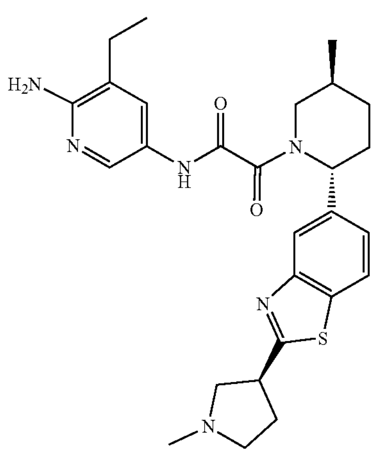 [SMILES: CCc1cc(NC(=O)C(=O)N2C[C@@H](C)CC[C@@H]2c2ccc3sc([C@H]4CCN(C)C4)nc3c2)cnc1N] | 1311 | abs | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 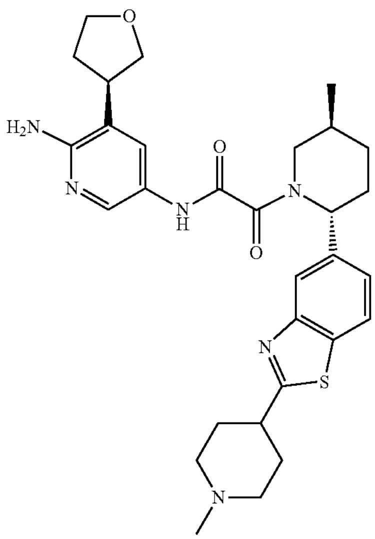 [SMILES: C[C@H]1CC[C@H](c2ccc3sc(C4CCN(C)CC4)nc3c2)N(C(=O)C(=O)Nc2cnc(N)c([C@H]3CCOC3)c2)C1] | 1312 | abs | a | aa | aaa | c* | aa* | | A* |
| 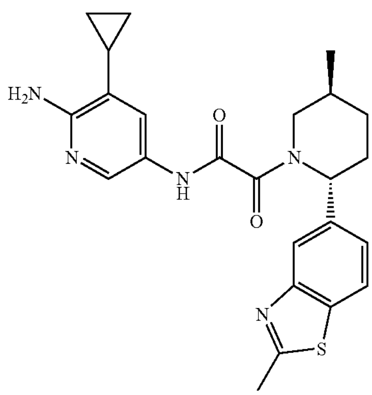 [SMILES: Cc1nc2cc([C@H]3CC[C@H](C)CN3C(=O)C(=O)Nc3cnc(N)c(C4CC4)c3)ccc2s1] | 1313 | or/rel | b | aa | aaa | b* | aa* | A | A* |
| 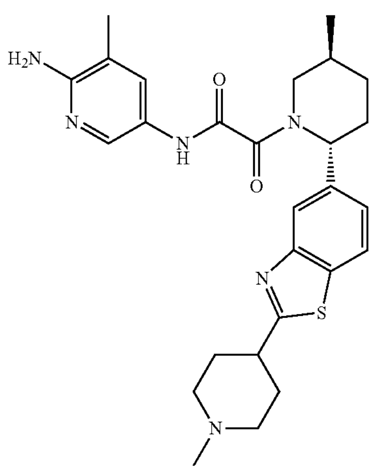 [SMILES: Cc1cc(NC(=O)C(=O)N2C[C@@H](C)CC[C@@H]2c2ccc3sc(C4CCN(C)CC4)nc3c2)cnc1N] | 1314 | or/rel | a | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1315 | abs | a | aa | aaa | b* | aa* | A | A* |
| | 1316 | abs | b | aa | aaa | a* | aa* | A | A* |
| | 1317 | abs | b | aa | aaa | a* | aa* | A | A* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted viability |
|---|---|---|---|---|---|---|---|---|---|
| 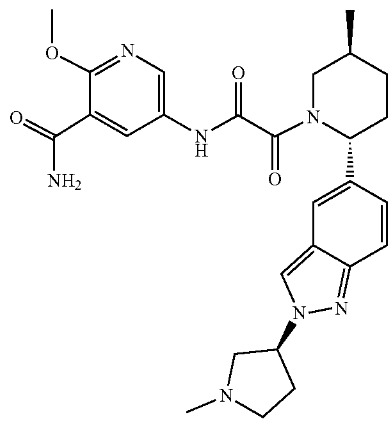 [SMILES: COc1ncc(NC(=O)C(=O)N2C[C@@H](C)CC[C@@H]2c2ccc3nn([C@H]4CCN(C)C4)cc3c2)cc1C(N)=O] | 1318 | | b | aa | aaa | b* | aa* | A | A* |
| 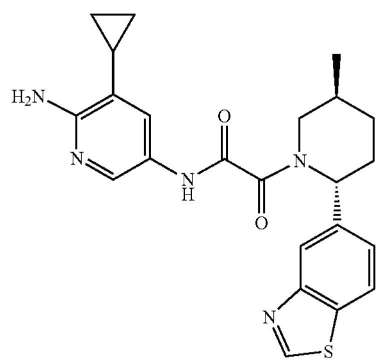 [SMILES: C[C@H]1CC[C@H](c2ccc3scnc3c2)N(C(=O)C(=O)Nc2cnc(N)c(C3CC3)c2)C1] | 1319 | abs | b | aa | aaa | b* | aa* | A | A* |
| 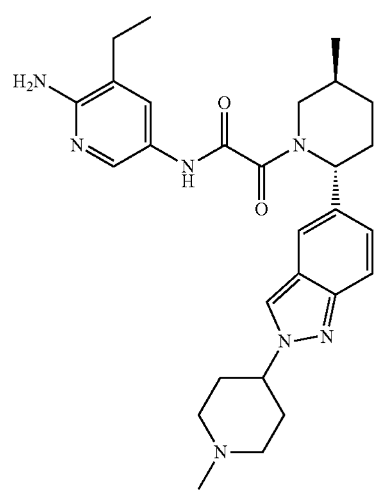 [SMILES: CCc1cc(NC(=O)C(=O)N2C[C@@H](C)CC[C@@H]2c2ccc3nn(C4CCN(C)CC4)cc3c2)cnc1N] | 1321 | | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 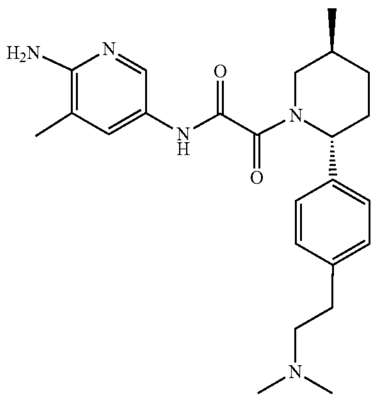 [SMILES: Cc1cc(NC(=O)C(=O)N2C[C@@H](C)CC[C@@H]2c2ccc(CCN(C)C)cc2)cnc1N] | 1322 | or/rel | c | cc | ccc | c* | cc* | | C* |
| 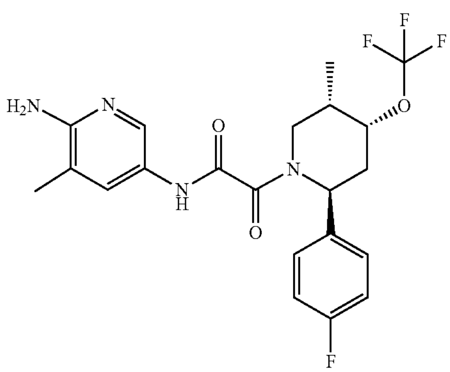 [SMILES: Cc1cc(NC(=O)C(=O)N2C[C@H](C)[C@H](OC(F)(F)F)C[C@H]2c2ccc(F)cc2)cnc1N] | 1323 | or/rel | c | cc | ccc | c* | cc* | | C* |
| 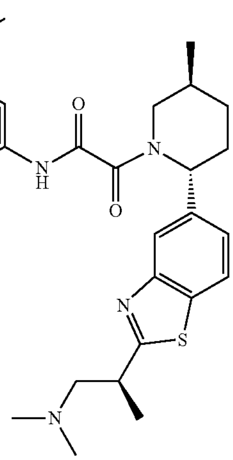 | 1324 | abs | a | aa | aaa | a* | aa* | A | A* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| | 1325 | abs | b | aa | aaa | a* | aa* | A | A* |
| | 1326 | abs | a | aa | aaa | b* | aa* | A | A* |
| | 1327 | or/rel | c | cc | ccc | c* | cc* | | B* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 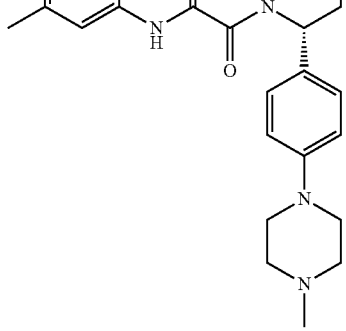 | 1328 | or/rel | b | aa | aaa | a* | aa* | B | A* |
| 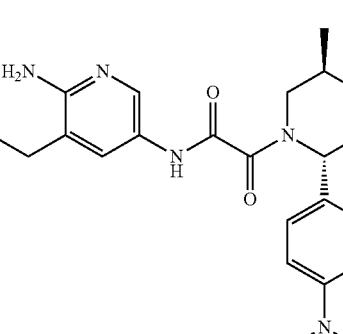 | 1329 | and/rac | b | bb | bbb | c* | aa* | | A* |
| 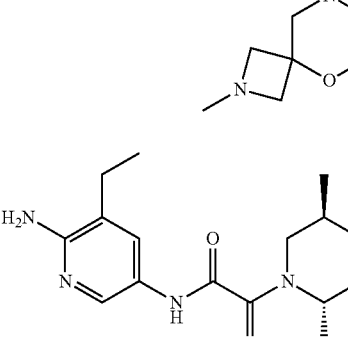 | 1330 | abs | a | aa | aaa | a* | aa* | A | A* |

TABLE 1-continued
Exemplary compounds of the invention and biological data
| Structure | Nr | Stereo | No Co-factor/ SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 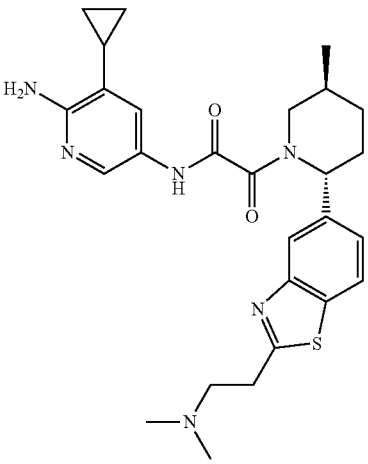 [SMILES: C[C@H]1CC[C@H](c2ccc3sc(CCN(C)C)nc3c2)N(C(=O)C(=O)Nc2cnc(N)c(C3CC3)c2)C1] | 1331 | or/rel | c | cc | ccc | c* | bb* | | B* |
| 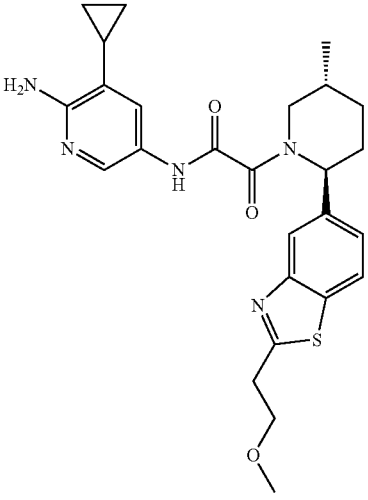 [SMILES: COCCc1nc2cc([C@@H]3CC[C@@H](C)CN3C(=O)C(=O)Nc3cnc(N)c(C4CC4)c3)ccc2s1] | 1332 | or/rel | b | bb | aaa | b* | aa* | A | A* |
| 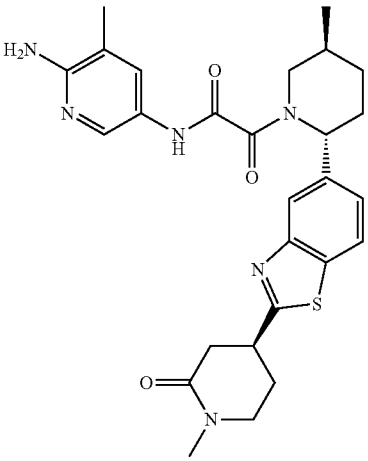 [SMILES: Cc1cc(NC(=O)C(=O)N2C[C@@H](C)CC[C@@H]2c2ccc3sc([C@H]4CCN(C)C(=O)C4)nc3c2)cnc1N] | 1333 | abs | a | aa | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 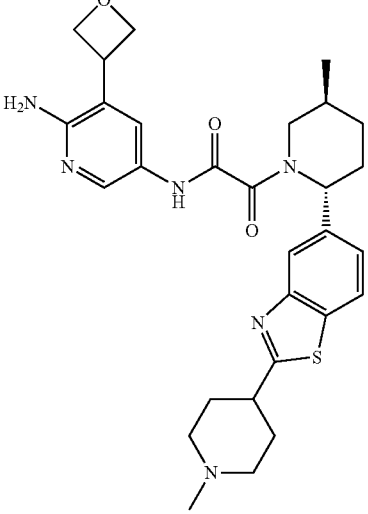 | 1334 | or/rel | a | aa | aaa | a* | aa* | B | A* |
| 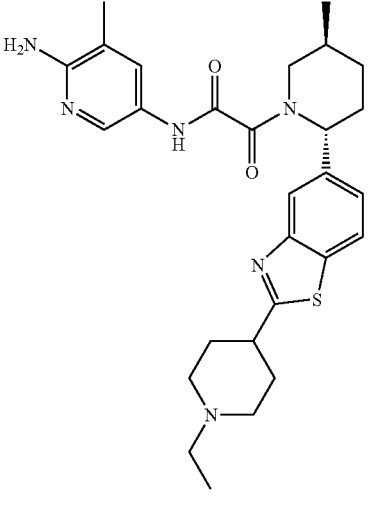 [SMILES: CCN1CCC(c2nc3cc([C@H]4CC[C@H](C)CN4C(=O)C(=O)Nc4cnc(N)c(C)c4)ccc3s2)CC1] | 1335 | abs | a | aa | aaa | a* | aa* | A | A* |
| 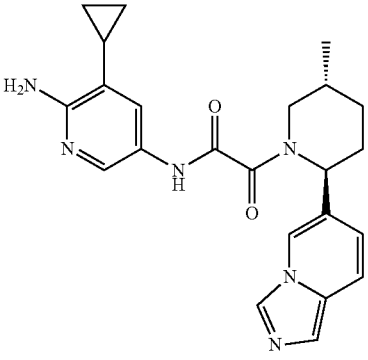 [SMILES: C[C@@H]1CC[C@@H](c2ccc3cncn3c2)N(C(=O)C(=O)Nc2cnc(N)c(C3CC3)c2)C1] | 1336 | or/rel | c | cc | ccc | c* | bb* | | B* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 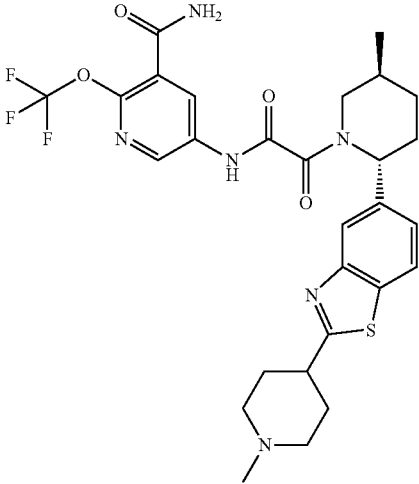 [SMILES: C[C@H]1CC[C@H](c2ccc3sc(C4CCN(C)CC4)nc3c2)N(C(=O)C(=O)Nc2cnc(OC(F)(F)F)c(C(N)=O)c2)C1] | 1337 | or/rel | a | aa | aaa | a* | aa* | B | A* |
| 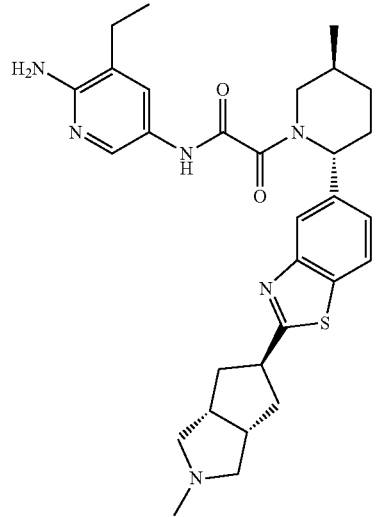 [SMILES: CCc1cc(NC(=O)C(=O)N2C[C@@H](C)CC[C@@H]2c2ccc3sc([C@H]4C[C@@H]5CN(C)C[C@@H]5C4)nc3c2)cnc1N] | 1338 | abs | a | aa | aaa | a* | aa* | A | A* |
| 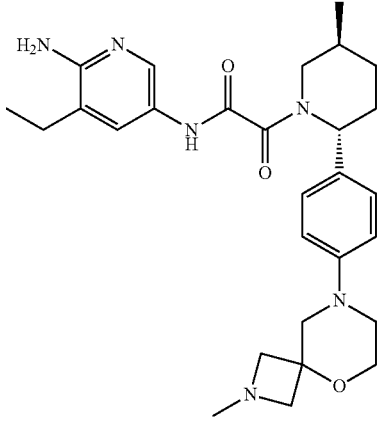 [SMILES: CCc1cc(NC(=O)C(=O)N2C[C@@H](C)CC[C@@H]2c2ccc(N3CCOC4(CN(C)C4)C3)cc2)cnc1N] | 1339 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 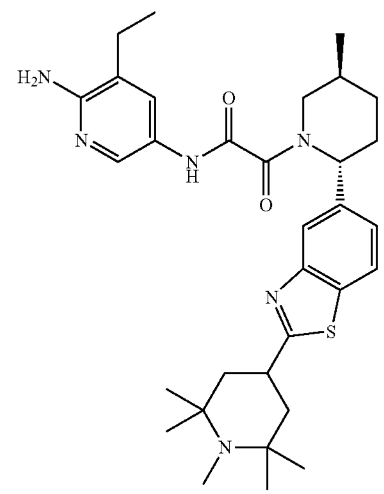 [SMILES: CCc1cc(NC(=O)C(=O)N2C[C@@H](C)CC[C@@H]2c2ccc3sc(C4CC(C)(C)N(C)C(C)(C)C4)nc3c2)cnc1N] | 1340 | abs | b | aa | aaa | a* | aa* | A | A* |
| 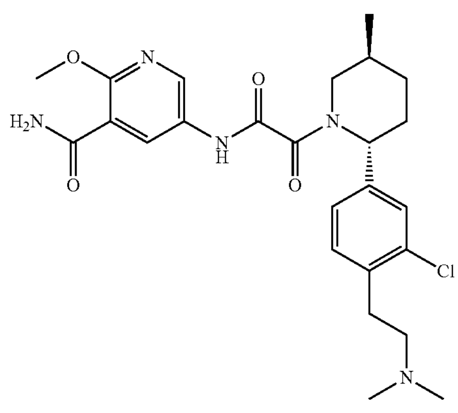 [SMILES: COc1ncc(NC(=O)C(=O)N2C[C@@H](C)CC[C@@H]2c2ccc(CCN(C)C)c(Cl)c2)cc1C(N)=O] | 1341 | abs | b | aa | aaa | c* | aa* | | A* |
| 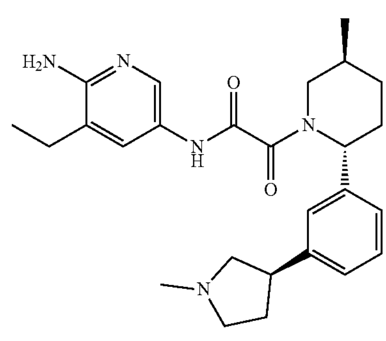 [SMILES: CCc1cc(NC(=O)C(=O)N2C[C@@H](C)CC[C@@H]2c2cccc([C@H]3CCN(C)C3)c2)cnc1N] | 1342 | abs | a | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 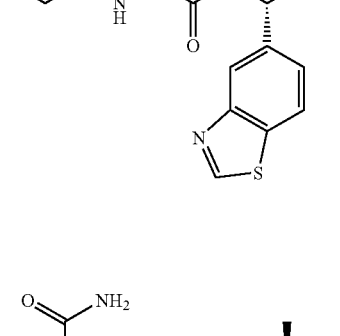 | 1343 | and/rac | b | bb | bbb | b* | aa* | A | A* |
| 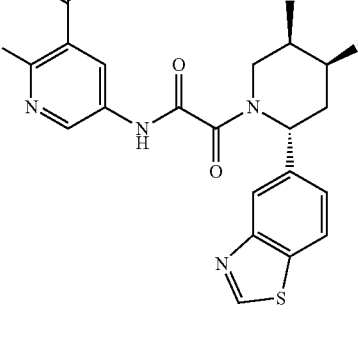 | 1344 | or/rel | c | cc | ccc | c* | bb* | | B* |
| 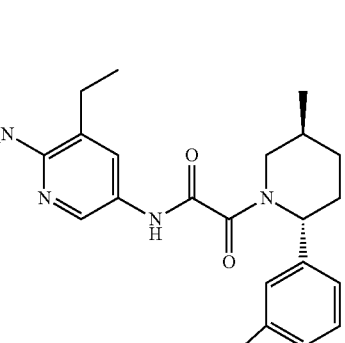 | 1345 | abs | b | aa | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 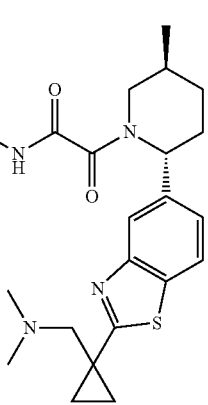 | 1347 | b | aa | aaa | a* | aa* | A | A* |
| 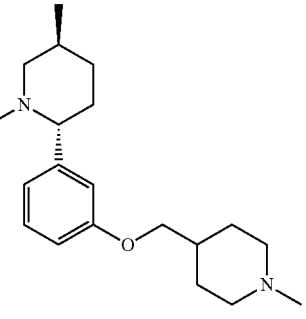 | 1348 | abs | a | aa | aaa | a* | aa* | A | A* |
| 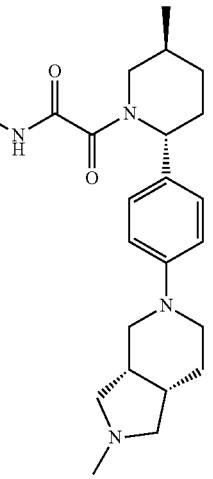 | 1349 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via- bility |
|---|---|---|---|---|---|---|---|---|---|
| 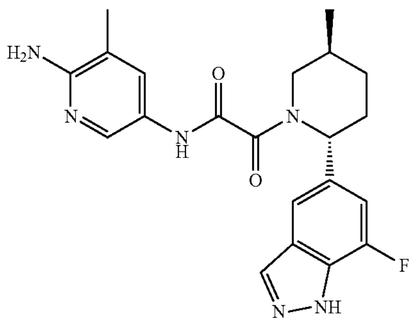 [SMILES: Cc1cc(NC(=O)C(=O)N2C[C@@H](C)CC[C@@H]2c2cc(F)c3[nH]ncc3c2)cnc1N] | 1350 | or/rel | b | aa | aaa | b* | aa* | A | A* |
| 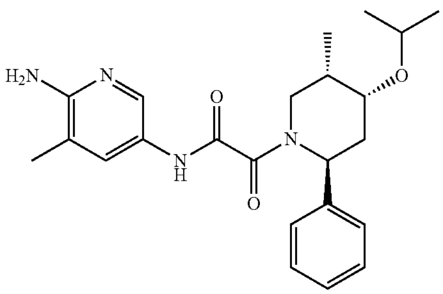 [SMILES: Cc1cc(NC(=O)C(=O)N2C[C@H](C)[C@H](OC(C)C)C[C@H]2c2ccccc2)cnc1N] | 1351 | or/rel | a | aa | aaa | a* | aa* | B | A* |
| 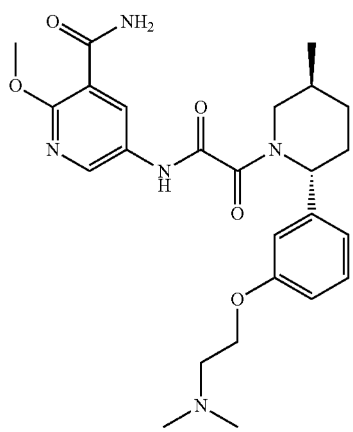 [SMILES: COc1ncc(NC(=O)C(=O)N2C[C@@H](C)CC[C@@H]2c2cccc(OCCN(C)C)c2)cc1C(N)=O] | 1352 | abs | a | aa | aaa | c* | aa* | | A* |
| 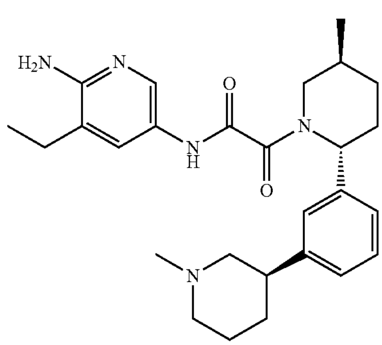 [SMILES: CCc1cc(NC(=O)C(=O)N2C[C@@H](C)CC[C@@H]2c2cccc([C@H]3CCCN(C)C3)c2)cnc1N] | 1353 | or/rel | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 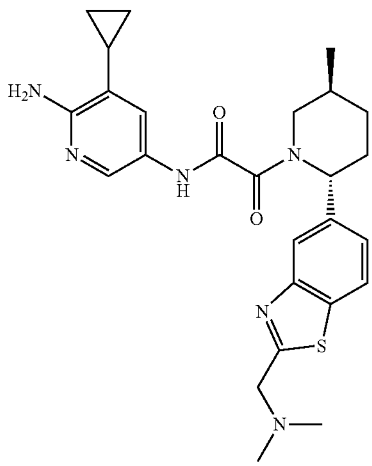 [SMILES: C[C@H]1CC[C@H](c2ccc3sc(CN(C)C)nc3c2)N(C(=O)C(=O)Nc2cnc(N)c(C3CC3)c2)C1] | 1354 | abs | b | aa | aaa | a* | aa* | A | A* |
| 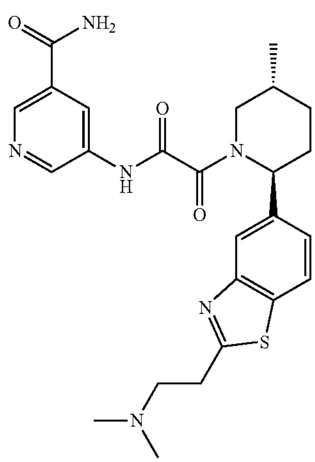 [SMILES: C[C@@H]1CC[C@@H](c2ccc3sc(CCN(C)C)nc3c2)N(C(=O)C(=O)Nc2cncc(C(N)=O)c2)C1] | 1355 | and/rac | b | bb | aaa | b* | aa* | A | A* |
| 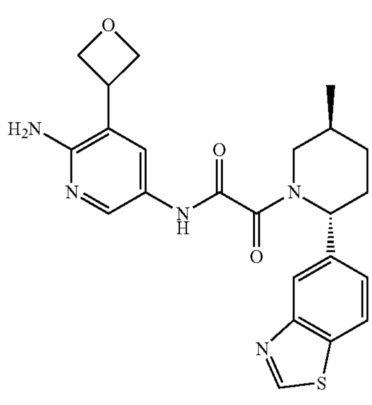 [SMILES: C[C@H]1CC[C@H](c2ccc3scnc3c2)N(C(=O)C(=O)Nc2cnc(N)c(C3COC3)c2)C1] | 1356 | abs | b | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1357 | or/rel | b | bb | aaa | a* | aa* | A | A* |
| | 1358 | or/rel | b | aa | aaa | a* | aa* | A | A* |
| | 1359 | a | aa | aaa | a* | aa* | A | A* |

TABLE 1-continued

Exemplary compounds of the invention and biological data

| Structure | Nr | Stereo | SAM IC50 | No Co-factor/rel IC50 | MTA IC50 | HAP1 MTAP intact IC50 | HAP 1 MTAP deleted IC50 | MTAP intact/deleted ratio | HAP1 MTAP deleted via-bility |
|---|---|---|---|---|---|---|---|---|---|
| | 1360 | or/rel | c | cc | ccc | c* | cc* | | C* |
| | 1361 | or/rel | c | cc | ccc | c* | cc* | | C* |
| | 1362 | abs | b | aa | aaa | b* | aa* | A | A* |
| | 1363 | abs | a | aa | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1364 | or/rel | b | aa | aaa | b* | aa* | A | A* |
| | 1365 | | b | aa | aaa | a* | aa* | A | A* |
| | 1366 | | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 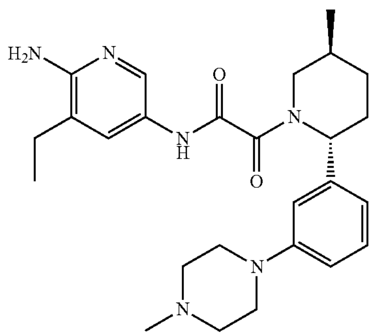 [SMILES: CCc1cc(NC(=O)C(=O)N2C[C@@H](C)CC[C@@H]2c2cccc(N3CCN(C)CC3)c2)cnc1N] | 1367 | abs | a | aa | aaa | b* | aa* | A | A* |
| 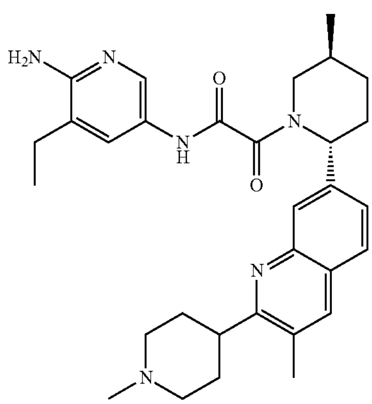 [SMILES: CCc1cc(NC(=O)C(=O)N2C[C@@H](C)CC[C@@H]2c2ccc3cc(C)c(C4CCN(C)CC4)nc3c2)cnc1N] | 1368 |  | b | aa | aaa | a* | aa* | A | A* |
| 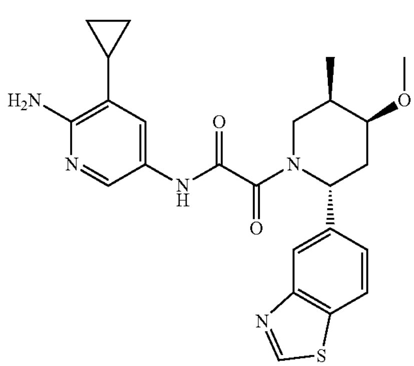 [SMILES: CO[C@H]1C[C@H](c2ccc3scnc3c2)N(C(=O)C(=O)Nc2cnc(N)c(C3CC3)c2)C[C@H]1C] | 1370 | or/rel | b | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| (structure) | 1371 | or/rel | b | aa | aaa | b* | aa* | A | A* |
| (structure) | 1372 | | a | aa | aaa | a* | aa* | A | A* |
| (structure) | 1373 | abs | a | aa | aaa | a* | aa* | B | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP1 MTAP deleted IC50 | MTAP intact/ deleted ratio | HAP1 MTAP deleted via-bility |
|---|---|---|---|---|---|---|---|---|---|
| 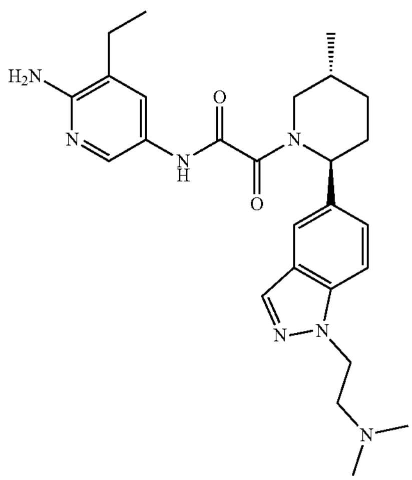 [SMILES: CCc1cc(NC(=O)C(=O)N2C[C@H](C)CC[C@H]2c2ccc3c(cnn3CCN(C)C)c2)cnc1N] | 1374 | or/rel | b | aa | aaa | b* | aa* | A | A* |
| 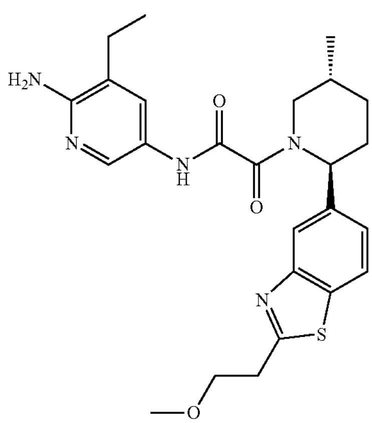 [SMILES: CCc1cc(NC(=O)C(=O)N2C[C@H](C)CC[C@H]2c2ccc3sc(CCOC)nc3c2)cnc1N] | 1375 | or/rel | c | cc | ccc | c* | cc* | | C* |
| 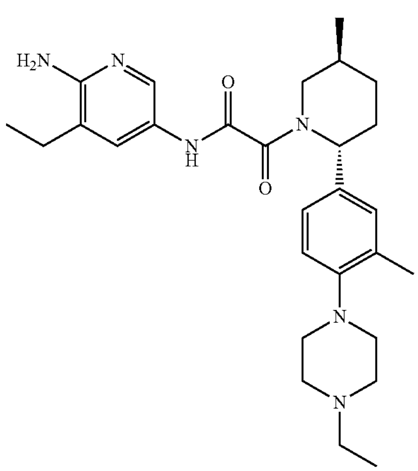 [SMILES: CCc1cc(NC(=O)C(=O)N2C[C@@H](C)CC[C@@H]2c2ccc(N3CCN(CC)CC3)c(C)c2)cnc1N] | 1376 | | b | aa | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 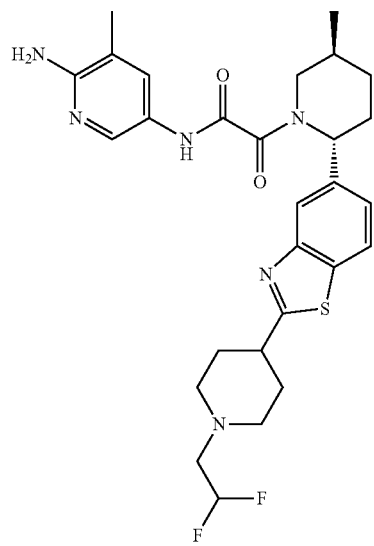 | 1377 | abs | b | aa | aaa | b* | aa* | A | A* |
| 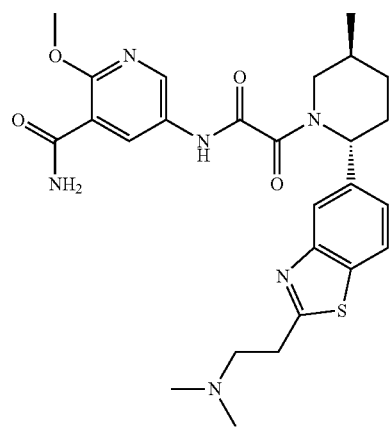 [SMILES: COc1ncc(NC(=O)C(=O)N2C[C@@H](C)CC[C@@H]2c2ccc3sc(CCN(C)C)nc3c2)cc1C(N)=O] | 1378 | or/rel | a | aa | aaa | a* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 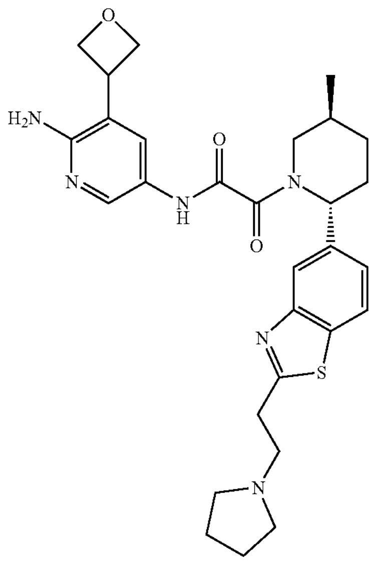 [SMILES: C[C@H]1CC[C@H](c2ccc3sc(CCN4CCCC4)nc3c2)N(C(=O)C(=O)Nc2cnc(N)c(C3COC3)c2)C1] | 1379 | abs | b | bb | aaa | a* | aa* | A | A* |
| 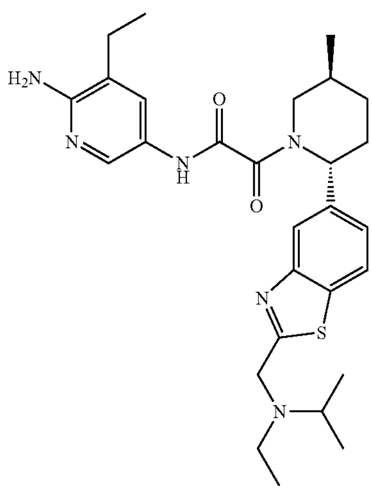 [SMILES: CCc1cc(NC(=O)C(=O)N2C[C@@H](C)CC[C@@H]2c2ccc3sc(CN(CC)C(C)C)nc3c2)cnc1N] | 1380 | abs | b | aa | aaa | b* | aa* | A | A* |
| 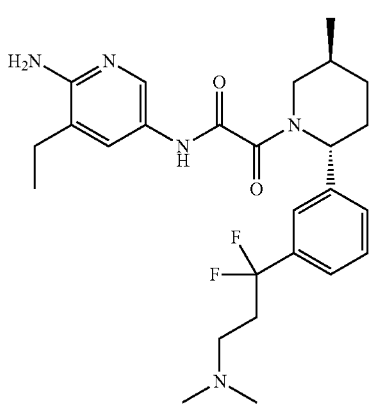 [SMILES: CCc1cc(NC(=O)C(=O)N2C[C@@H](C)CC[C@@H]2c2cccc(C(F)(F)CCN(C)C)c2)cnc1N] | 1381 | abs | a | | aaa | b* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 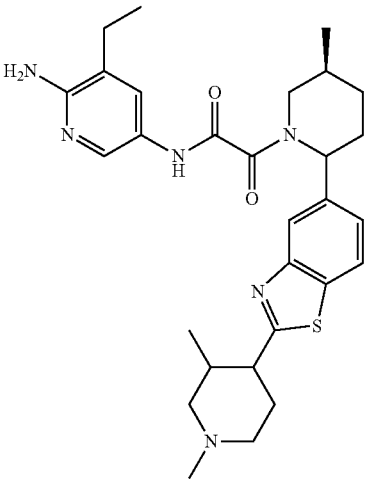 | 1382 | abs | a | aa | aaa | a* | aa* | A | A* |
| 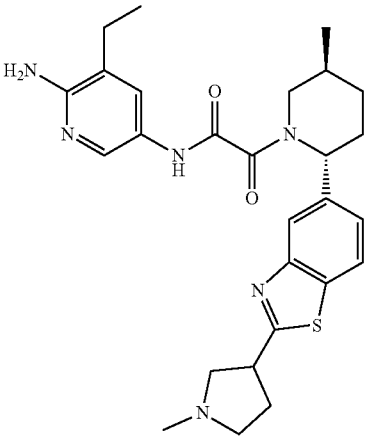 [SMILES: CCc1cc(NC(=O)C(=O)N2C[C@@H](C)CC[C@@H]2c2ccc3sc(C4CCN(C)C4)nc3c2)cnc1N] | 1383 | abs | a | aa | aaa | a* | aa* | A | A* |
| 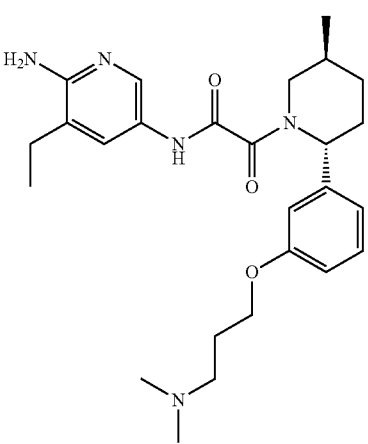 [SMILES: CCc1cc(NC(=O)C(=O)N2C[C@@H](C)CC[C@@H]2c2cccc(OCCCN(C)C)c2)cnc1N] | 1384 | abs | b | | aaa | a* | aa* | A | A* |

TABLE 1-continued

Exemplary compounds of the invention and biological data

| Structure | Nr | Stereo | SAM IC50 | No Cofactor/ rel IC50 | MTA IC50 | HAP1 MTAP intact IC50 | HAP 1 MTAP deleted IC50 | MTAP intact/ deleted ratio | HAP1 MTAP deleted viability |
|---|---|---|---|---|---|---|---|---|---|
| 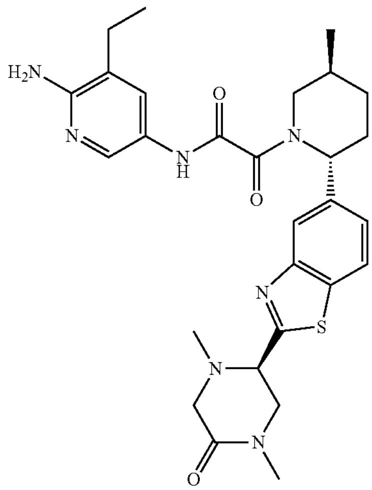 [SMILES: CCc1cc(NC(=O)C(=O)N2C[C@@H](C)CC[C@@H]2c2ccc3sc([C@H]4CN(C)C(=O)CN4C)nc3c2)cnc1N] | 1385 | abs | b | aa | aaa | a* | aa* | A | A* |
| 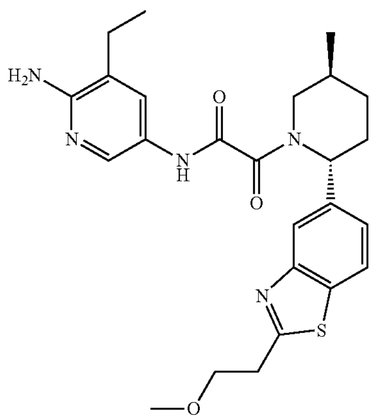 [SMILES: CCc1cc(NC(=O)C(=O)N2C[C@@H](C)CC[C@@H]2c2ccc3sc(CCOC)nc3c2)cnc1N] | 1386 | or/rel | b | aa | aaa | b* | aa* | A | A* |
| 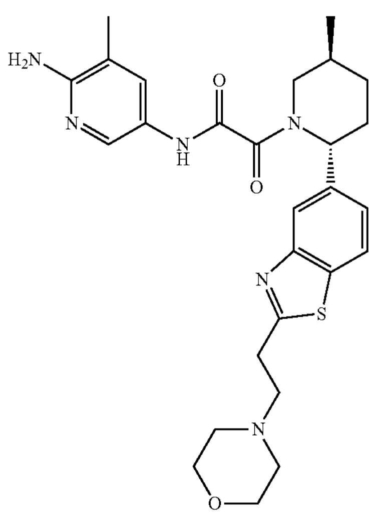 [SMILES: Cc1cc(NC(=O)C(=O)N2C[C@@H](C)CC[C@@H]2c2ccc3sc(CCN4CCOCC4)nc3c2)cnc1N] | 1387 | abs | b | aa | aaa | a* | aa* | B | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 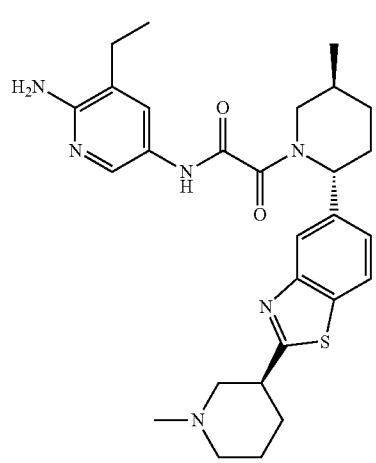 [SMILES: CCc1cc(NC(=O)C(=O)N2C[C@@H](C)CC[C@@H]2c2ccc3sc([C@H]4CCCN(C)C4)nc3c2)cnc1N] | 1388 | abs | a | aa | aaa | a* | aa* | A | A* |
| 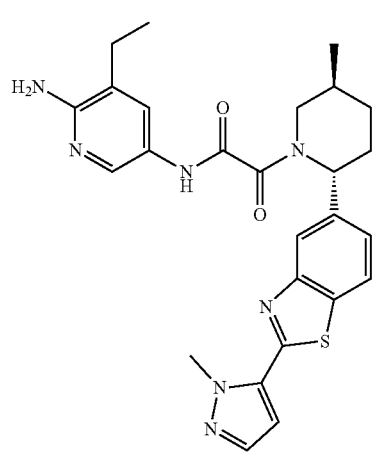 [SMILES: CCc1cc(NC(=O)C(=O)N2C[C@@H](C)CC[C@@H]2c2ccc3sc(-c4ccnn4C)nc3c2)cnc1N] | 1389 | abs | b | aa | aaa | b* | aa* | A | A* |
| 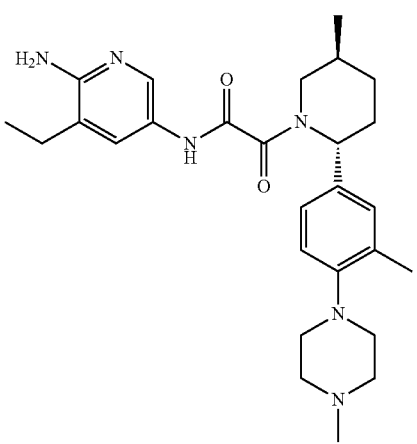 [SMILES: CCc1cc(NC(=O)C(=O)N2C[C@@H](C)CC[C@@H]2c2ccc(N3CCN(C)CC3)c(C)c2)cnc1N] | 1390 | | b | bb | aaa | b* | aa* | A | A* |

TABLE 1-continued

Exemplary compounds of the invention and biological data

| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| 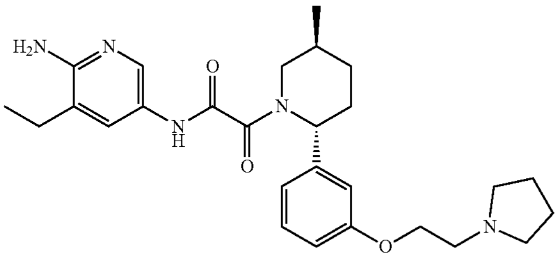 [SMILES: CCc1cc(NC(=O)C(=O)N2C[C@@H](C)CC[C@@H]2c2cccc(OCCN3CCCC3)c2)cnc1N] | 1391 | abs | a | aa | aaa | b* | aa* | A | A* |
| 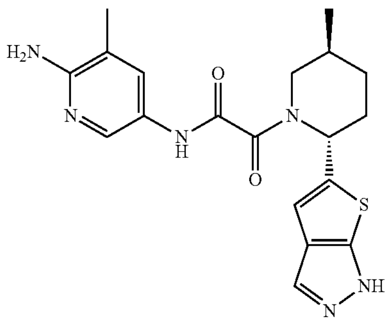 [SMILES: Cc1cc(NC(=O)C(=O)N2C[C@@H](C)CC[C@@H]2c2cc3cn[nH]c3s2)cnc1N] | 1392 | or/rel | b | bb | aaa | b* | aa* | A | A* |
| 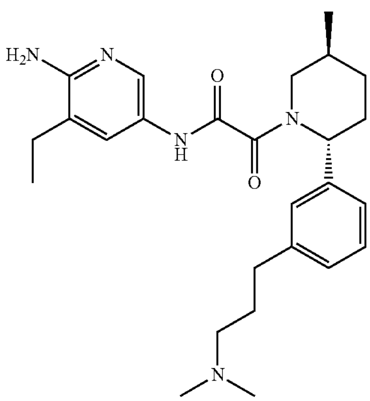 [SMILES: CCc1cc(NC(=O)C(=O)N2C[C@@H](C)CC[C@@H]2c2cccc(CCCN(C)C)c2)cnc1N] | 1393 | abs | b |  | aaa | b* | aa* | A | A* |
| 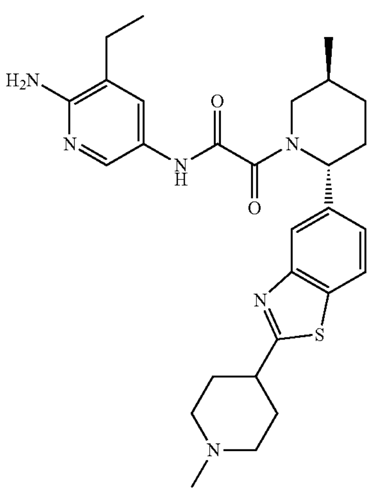 [SMILES: CCc1cc(NC(=O)C(=O)N2C[C@@H](C)CC[C@@H]2c2ccc3sc(C4CCN(C)CC4)nc3c2)cnc1N] | 1395 |  | b | aa | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 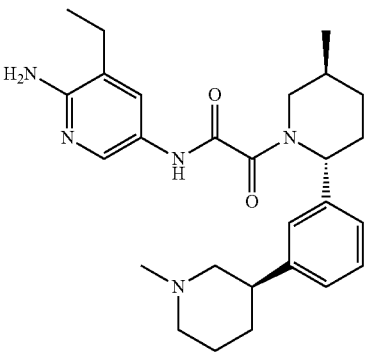 [SMILES: CCc1cc(NC(=O)C(=O)N2C[C@@H](C)CC[C@@H]2c2cccc([C@H]3CCCN(C)C3)c2)cnc1N] | 1396 | abs | | | | | | | |
| 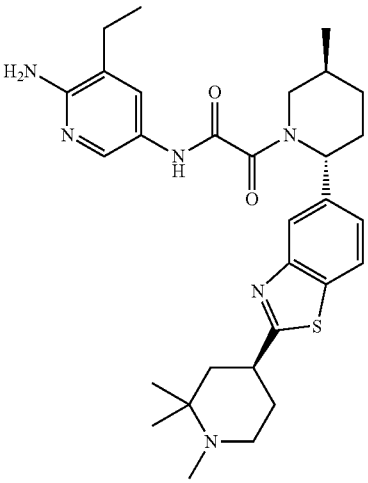 [SMILES: CCc1cc(NC(=O)C(=O)N2C[C@@H](C)CC[C@@H]2c2ccc3sc([C@H]4CCN(C)C(C)(C)C4)nc3c2)cnc1N] | 1397 | abs | b | aa | aaa | a* | aa* | A | A* |
| 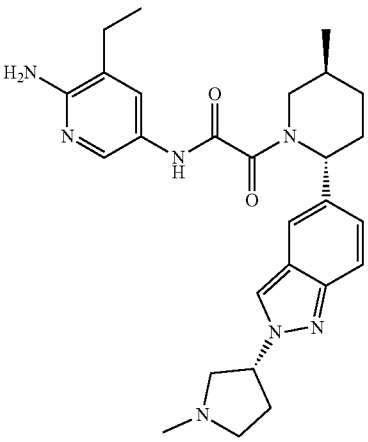 [SMILES: CCc1cc(NC(=O)C(=O)N2C[C@@H](C)CC[C@@H]2c2ccc3nn([C@@H]4CCN(C)C4)cc3c2)cnc1N] | 1398 | | b | bb | aaa | a* | aa* | A | A* |

TABLE 1-continued
Exemplary compounds of the invention and biological data
| Structure | Nr | Stereo | SAM IC50 | No Co-factor/ rel IC50 | MTA IC50 | HAP1 MTAP intact IC50 | HAP 1 MTAP deleted IC50 | MTAP intact/ deleted ratio | HAP1 MTAP deleted via- bility |
|---|---|---|---|---|---|---|---|---|---|
| 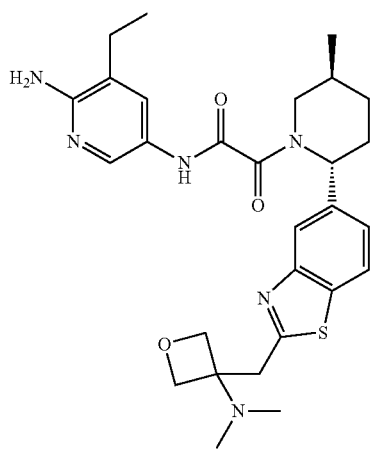 [SMILES: CCc1cc(NC(=O)C(=O)N2C[C@@H](C)CC[C@@H]2c2ccc3sc(CC4(N(C)C)COC4)nc3c2)cnc1N] | 1399 | abs | b | aa | aaa | b* | aa* | A | A* |
| 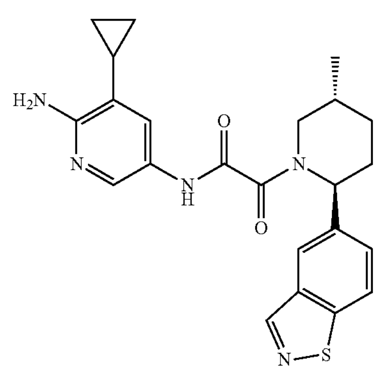 [SMILES: C[C@@H]1CC[C@@H](c2ccc3sncc3c2)N(C(=O)C(=O)Nc2cnc(N)c(C3CC3)c2)C1] | 1400 | or/rel | c | cc | ccc | c* | cc* |  | C* |
| 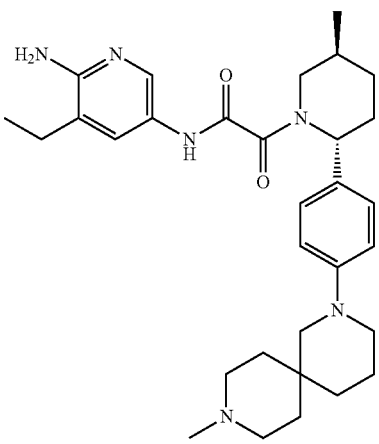 [SMILES: CCc1cc(NC(=O)C(=O)N2C[C@@H](C)CC[C@@H]2c2ccc(N3CCCC4(CCN(C)CC4)C3)cc2)cnc1N] | 1401 | abs | b | aa | aaa | b* | aa* | A | A* |

TABLE 1-continued

Exemplary compounds of the invention and biological data

| Structure | Nr | Stereo | No Co-factor/ SAM IC50 | rel IC50 | MTA IC50 | HAP1 MTAP intact IC50 | HAP 1 MTAP deleted IC50 | MTAP intact/ deleted ratio | HAP1 MTAP deleted via-bility |
|---|---|---|---|---|---|---|---|---|---|
| | 1402 | abs | b | aa | aaa | b* | aa* | A | A* |
| | 1403 | or/rel | b | aa | aaa | b* | aa* | A | A* |
| | 1404 | | a | aa | aaa | a* | aa* | A | A* |

In some embodiments, compounds of Formula (I) and (Ia) described herein can be prepared using methods illustrated in Scheme 1.
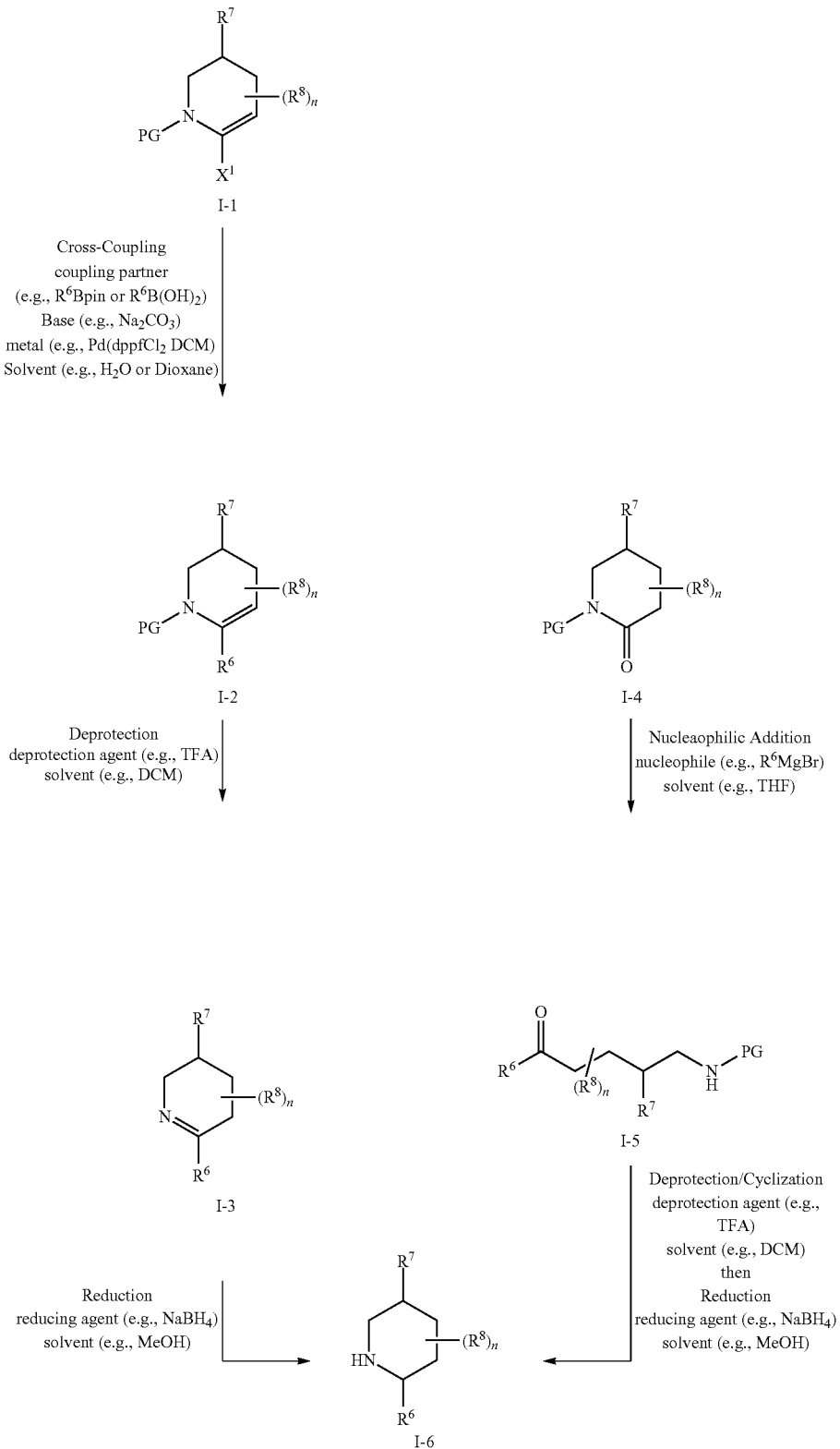
Scheme 1.

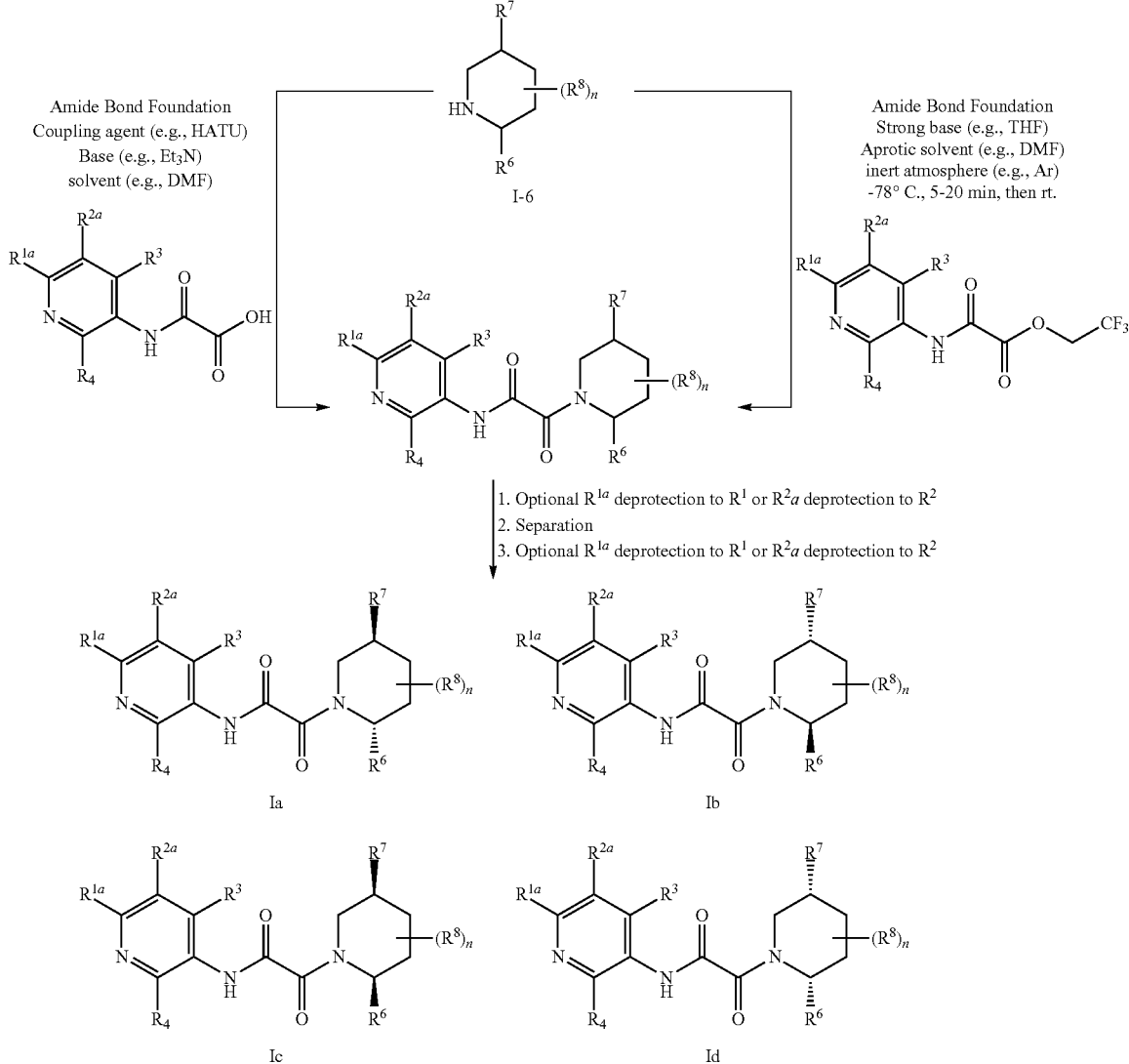

As shown in Scheme 1, compounds of Formula (Ia), (Ib), (Ic), and (Id) can be separated from a mixture of compounds of Formula (I), wherein $R^1$, $R^2$, $R^3$, $R^4$, $R^6$, $R^7$, $R^8$, and n are as described herein, $R^{1a}$ is selected from $R^1$ and —NH-PG and $R^{2a}$ is selected from $R^2$ and —NH-PG, wherein PG is a nitrogen protecting group as defined herein (e.g., -Boc). In certain embodiments (e.g., when $R^{1a}$ is NH-PG and $R^1$ is —$NH_2$ or $R^{2a}$ is NH-PG and $R^2$ is —$NH_2$), a deprotection step is employed to convert $R^{1a}$ to $R^1$ or $R^{2a}$ to $R^2$. A deprotection step can take place before or after a separation step. Conditions for removing a protecting group -PG (e.g., -Boc) can employ, for example, acidic conditions, (e.g., water/dioxane, hydrochoric acid in a protic solvent (e.g., methanol), hydrochloric acid in an aprotic solvent (e.g., dioxane), TFA in an an aprotic solvent (e.g., dichloromethane, chloroform, etc)).

Compounds of Formula (I) can be prepared by subjecting compounds of formula I-6 to amide bond coupling conditions. In some embodiments, compounds of formula (I) are prepared through amide bond coupling of a compound of formula I-6 with a compound of formula I-7. Examples of conditions known to generate a compound of formula I from a compound of formula I-6 and formula I-7 include but are not limited to adding a coupling agent such as CDI, HATU, HOBT, HBTU or PyBOP, a base such as a hydride base e.g., NaH, or KH, an amine base such as DBU, $NEt_3$, and $NEt(^iPr)_2$ or a carbonate base e.g., $Na_2CO_3$, $K_2CO_3$, or $Cs_2CO_3$, and in one embodiment stirring a reaction at 0° C. to room temperature or another embodiment at a temperature of 70° C. or higher, for example at a temperature in a range of 70° C. to 110° C., or in a range of 70° C. to 80° C., or at 80° C. A reaction may be carried out in solvents such as but not limited to DMF, and MTBE. In some embodiments, a compound of formula (I) is prepared through amide bond coupling of a compound of formula I-6 with a compound of formula I-8. Examples of conditions known to generate a compound of formula I from a compound of formula I-6 and formula I-8 include but are not limited to adding a base such as an organolithium base, e.g., n-BuLi, t-BuLi, lithium diisopropylamide (LDA), lithium bis(trimethylsilyl)amide (LiHMDS), a hydride base e.g., NaH, or KH, an amine base such as DBU, $NEt_3$, and $NEt(^iPr)_2$ or a carbonate base e.g., $Na_2CO_3$, $K_2CO_3$, or $Cs_2CO_3$, and in one embodiment stirring a reaction at 0° C. to room temperature or another embodiment at a temperature of 70° C. or higher, for example at a temperature in a range of 70° C. to 110° C., or in a range of 70° C. to 80° C., or at 80° C. A reaction may be carried out in solvents such as but not limited to THF, Et$_2$O, TMEDA, DME and MTBE or mixtures thereof.

In some embodiments, a compound of formula I-5 undergoes a sequence of deprotection, cyclization and reduction to prepare a compound of formula I-6. Conditions for the removal of a protecting group (PG), e.g., MoM or Boc are known to a person of ordinary skill in the art. For example, Boc deprotection may comprise treatment with an acid. Exemplary acids include TFA, and HCl, and exemplary solvents include protic solvents such as methanol, halogenated solvents such as DCM and hexafluoroisopropanol or ether solvents such as dioxane and dimethylether. In some embodiments, upon deprotection of a compound of formula I-5 can undergo spontaneous cyclization to form a cyclic imine. Reduction of a cyclic imine can be accomplished using a reducing agent such as a hydride reducing agent, e.g., NaBH$_4$, or LiAlH$_4$, silicon reducing agent, e.g., Cl$_3$SiH, or H$_2$ reduction in the presence of a catalyst, e.g. a Ir catalyst, a Ru catalyst, a Pd catalyst (e.g., Pd/C, Pd(OAc)$_2$).

A compound of formula I-5 can be prepared by nucleophilic addition to a compound of formula I-4. Nucleophilic addition can be accomplished using a Grignard reagent, e.g. R$^6$MgBr. A nucleophilic addition reaction may be carried out in solvents such as but not limited to THF, Et$_2$O, TMEDA, DME and MTBE or mixtures thereof.

Alternatively, a compound of formula I-6 can be prepared via a reduction of a compound of formula I-3. Reduction of a compound of formula I-3 can be accomplished using a reducing agent such as a hydride reducing agent, e.g., NaBH$_4$, or LiAlH$_4$, silicon reducing agent, e.g., Cl$_3$SiH, or H$_2$ reduction in the presence of a catalyst, e.g. a Ir catalyst, a Ru catalyst, a Pd catalyst (e.g., Pd/C, Pd(OAc)$_2$).

In some embodiments, a compound of formula I-2 can undergo deprotection/double bond migration, to afford a compound of formula I-3. Conditions for the removal of a protecting group (PG), e.g., MoM or Boc are known to a person of ordinary skill in the art. For example, Boc deprotection may comprise treatment with an acid. Exemplary acids include TFA, and HCl, and exemplary solvents include protic solvents such as methanol, halogenated solvents such as DCM and hexafluoroisopropanol or ether solvents such as dioxane and dimethylether.

In some embodiments, a compound of I-2 can be prepared through the cross-coupling of a compound of formula I-1 (wherein X is a leaving group, e.g., a halogen or —OSO$_2$CF$_3$) with a suitable cross-coupling partner. In some embodiments, a suitable cross-coupling partner includes, but is not limited to, a boron-containing cross-coupling partner, e.g., R$^6$B(OH)$_2$, or R$^6$Bpin.

Alternative Embodiments

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, 18O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In another aspect, the invention provides a pharmaceutical composition comprising a pharmaceutically acceptable carrier and an effective amount of a compound described herein (e.g., a compound of Formula (I), (Ia), (Ib), (Ic) and (Id) or a compound of Table 1), or a pharmaceutically acceptable salt thereof.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat. Cyclodextrins such as α-, β-, and γ-cyclodextrin, or chemically modified derivatives such as hydroxyalkylcyclodextrins, including 2 and 3 hydroxypropyl-β-cyclodextrins, or other solubilized derivatives may also be advantageously used to enhance delivery of compounds of the formulae described herein.

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound described herein (e.g., a compound of Formula (I), (Ia), (Ib), (Ic) and (Id) or a compound of Table 1, or pharmaceutically acceptable salts thereof) (or pharmaceutical composition thereof) for use as a pharmaceutical or a medicament (e.g., a medicament for the treatment of an MTAP-deficient and/or an MTA-accumulating disease in a subject in need thereof). In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The present invention also relates to a compound described herein (e.g., a compound of Formula (I), (Ia), (Ib), (Ic) and (Id) or a compound of Table 1, or pharmaceutically acceptable salts thereof) (or pharmaceutical composition thereof) for use in the treatment of an MTAP-deficient and/or an MTA-accumulating disease in a subject in need thereof. In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The present invention also relates to a compound described herein (e.g., a compound of Formula (I), (Ia), (Ib), (Ic) and (Id) or a compound of Table 1, or pharmaceutically acceptable salts thereof) (or pharmaceutical composition thereof) for use in the manufacturing of a medicament (e.g., a medicament for the treatment of an MTAP-deficient and/or an MTA-accumulating disease in a subject in need thereof). In one embodiment, the disease is a proliferating disease. In a further embodiment, the disease is an MTAP-deficient and/or MTA-accumulating cancer. In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The pharmaceutical compositions provided herewith may also be administered in the form of suppositories for rectal administration. These compositions can be prepared by mixing a compound provided herewith with a suitable non irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions provided herewith may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The above-described components for orally administrable, injectable or topically administrable, rectally administrable and nasally administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of this invention can also be administered in sustained release forms or from sustained release drug delivery systems. A description of representative sustained release materials can be found in *Remington's Pharmaceutical Sciences.*

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The present invention also relates to the pharmaceutically acceptable acid addition salt of a compound described herein (e.g., compound of Formula (I), (Ia), (Ib), (Ic) and (Id) or a compound of Table 1).

The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long term basis upon any recurrence of disease symptoms.

Methods of Treatment and Use

Treatment of MTAP-Deficient and/or MTA-Accumulating Proliferation Disorders

In one embodiment, the present invention provides methods of treating human or animal subjects having or having been diagnosed with an MTAP-deficiency-related and/or MTA-accumulating proliferative disorder (e.g., cancer) comprising administering to the subject in need thereof a therapeutically effective amount of a compound of the present invention (e.g., a compound of Formula (I), (Ia), (Ib), (Ic) and (Id) or a compound of Table 1) or a pharmaceutically acceptable salt thereof.

In one embodiment, the present invention provides methods of an MTAP-deficiency-related and/or MTA-accumulating proliferative disorder (e.g., cancer) in a subject in need thereof comprising administering to the subject a therapeutically effective amount of a compound of the present invention (e.g., compound of Formula (I), (Ia), (Ib), (Ic) and (Id) or a compound of Table 1) or a pharmaceutically acceptable salt thereof.

In one embodiment, the present invention provides methods of treating human or animal subjects having or having been diagnosed with an MTAP-deficiency-related and/or MTA-accumulating proliferative disorder (e.g., cancer) comprising administering to the subject in need thereof a therapeutically effective amount of pharmaceutical composition of the present invention (e.g., a composition comprising a compound of Formula (I), (Ia), (Ib), (Ic) and (Id) or a compound of Table 1, or pharmaceutically acceptable salts thereof and a pharmaceutically acceptable carrier). In one embodiment, the compound or composition is administered in combination with a second therapeutic agent.

In one embodiment, the present invention provides methods of treating an MTAP-deficiency-related and/or MTA-accumulating proliferative disorder (e.g., cancer) in a subject in need thereof comprising administering to the subject a therapeutically effective amount of pharmaceutical composition of the present invention (e.g., a composition comprising a compound of Formula (I), (Ia), (Ib), (Ic) and (Id) or a compound of Table 1, or pharmaceutically acceptable salts thereof and a pharmaceutically acceptable carrier). In one embodiment, the compound or composition is administered in combination with a second therapeutic agent.

In certain embodiments, the disease is an MTAP-deficient and/or MTA-accumulating cancer.

In one embodiment, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one embodiment, the cancer is an MTAP-deficient and/or MTA-accumulating glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive, non-competitive or mixed mode PRMT5 inhibitor or an MTA cooperative binding agent, e.g., a compound of Formula (I), (Ia), (Ib), (Ic) and (Id) or a compound of Table 1, or pharmaceutically acceptable salts thereof) described herein can be used in a method of inhibiting proliferation of MTAP-deficient cells in a subject in need thereof, the method comprising the step of administering to the subject, a PRMT5 inhibitor (e.g., an MTA-uncompetitive, non-competitive or mixed mode PRMT5 inhibitor or an MTA cooperative binding agent, e.g., a compound of Formula (I), (Ia), (Ib), (Ic) and (Id) or a compound of Table 1, or pharmaceutically acceptable salts thereof) in an amount that is effective to inhibit proliferation of the MTAP-deficient cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive, non-competitive or mixed mode PRMT5 inhibitor or an MTA cooperative binding agent, e.g., a compound of Formula (I), (Ia), (Ib), (Ic) and (Id) or a compound of Table 1, or pharmaceutically acceptable salts thereof) described herein can be used in a method of inhibiting proliferation of MTA-accumulating cells in a subject in need thereof, the method comprising the step of administering to the subject, a PRMT5 inhibitor (e.g., an MTA-uncompetitive, non-competitive or mixed mode PRMT5 inhibitor or an MTA cooperative binding agent, e.g., a compound of Formula (I), (Ia), (Ib), (Ic) and (Id) or a compound of Table 1, or pharmaceutically acceptable salts thereof) in an amount that is effective to inhibit proliferation of the MTA-accumulating cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

The PRMT5 inhibitors (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) described herein can be used in a method of inhibiting proliferation of MTAP deficient and/or MTA-accumulating cells in a subject in need thereof, the method comprising the step of administering to the subject, a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) in an amount that is effective to inhibit proliferation of the MTAP deficient and/or MTA-accumulating cells. In one embodiment, the subject in need thereof suffers from a cancer selected from glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

Combination Therapies

The present invention provides methods of treatment of MTAP-deficient and/or MTA accumulating proliferative disorders (e.g., cancers) with a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) in combination with a second therapeutic agent.

The term "Combination" refers to either a fixed combination in one dosage unit form, or a combined administration where a compound of the present invention (e.g., a compound of Formula (I), (Ia), (Ib), (Ic) and (Id) or a compound of Table 1, or pharmaceutically acceptable salts thereof) and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g., a compound of the present invention (e.g., a compound of Formula (I), (Ia), (Ib), (Ic) and (Id) or a compound of Table 1, or pharmaceutically acceptable salts thereof) and a combination partner, are both administered to a patient simultaneously in the form of a single entity or dosage. The term "non-fixed combination" means that the therapeutic agents, e.g., a compound of the present invention (e.g., a compound of Formula (I), (Ia), (Ib), (Ic) and (Id) or a compound of Table 1, or pharmaceutically acceptable salts thereof) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more therapeutic agent.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times.

In certain embodiments, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), $N_4$-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), nab-paclitaxel (Abraxane®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Further compounds of particular interest for combinations with the compounds of the present invention include: EGFR-inhibitors, such as cetuximab, panitumimab, erlotinib, gefitinib and EGFRi NOS; MAPK-pathway inhibitors, such as BRAFi, panRAFi, MEKi, ERKi; PI3K-mTOR pathway inhibitors, such as alpha-specific PI3Ki, pan-class I PI3Ki and mTOR/PI3Ki, particularly everolimus and analogues thereof.

Specific compounds and classes of compounds acting via specific mechanisms can be particularly effective in conjunction with PRMT5 inhibitors (e.g., an MTA-uncompetitive, non-competitive, or mixed mode PRMT5 inhibitor or an MTA-cooperative binding agent, e.g., compounds of Formula (I), (Ia), (Ib), (Ic) and (Id) or a compound of Table 1, or pharmaceutically acceptable salts thereof). For example, PRMT5 is known to associate with SWI/SNF chromatin remodeling complexes along with other co-repressor molecules like $HDAC_2$. PRMT5 activity on target H4R3 and H3R8 is enhanced when lysine residues become deacetylated by HDAC enzymes. Thus, HDAC inhibitors can be effective (e.g., synergistic) when used in conjunction with PRMT5 inhibitors (WO 011/079236).

Thus, PRMT5 inhibitors of the present disclosure can be used in combination with other compounds, for example: HDAC inhibitor or DNA methyltransferase inhibitor. In some embodiments, the HDAC inhibitor is Trichostatin A. In some embodiments, the DNA methyltransferase inhibitor is 5-azacytidine.

A PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can also be administered or co-administered in any order with a MAT2A inhibitor.

A PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can also be administered or co-administered in any order with an inhibitor of a protein which interacts with or is required for PRMT5 function, including, but not limited to, pICIN, WDR77 or RIOK1.

A PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can be administered in combination with a HDM2 inhibitor and/or with 5-FU. The loss has been observed of wild-type p53 as a consequence of HDM2 activation resulting from CDKN2A deletion. This relates to the inability of MTAP deleted cells to salvage ATP and methionine from endogenous methylthioadenosine (MTA). As a consequence, tumor cells become differentially sensitive towards 5-FU and other purine analogues (e.g., 6-thioguanine, 6-mercaptopurine).

Given that CDKN2A/MTAP loss also leads to deregulation of p16/CDK4/6 pathway, PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can be administered in combination with a CDK4 inhibitor, including, but not limited to, LEE011 or a CDK4/6 inhibitor (e.g., palbociclib (Ibrance®), ribociclib (Kisqali®), and abemaciclib (Verzenio®).

A PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can be administered in combination with targeted treatments contingent on the dependency of individual target tumors on relevant pathways as determined by suitable predictive markers, including but not limited to: inhibitors of HDM2i, PI3K/mTOR-I, MAPKi, RTKi (EGFRi, FGFRi, METi, IGFiRi, JAKi, and WNTi.

A PRMT5 inhibitor (e.g., MTA-uncompetitive PRMT5 inhibitors, e.g., a compound of Formula (I), (Ia), (Ib), (Ic) and (Id) or a compound of Table 1, or pharmaceutically acceptable salts thereof) can be administered in combination with immunotherapy.

In some embodiments, the compounds described herein are used with a cancer immunotherapy (e.g., a checkpoint blocking antibody) to treat a subject (e.g., a human subject), e.g., having a disease or disorder described herein (e.g., a cancer described herein)).

In some embodiments, the immunotherapeutic agent is an anti-CTLA-4 antibody (e.g., ipilimumab, tremelimumab).

In some embodiments, the immunotherapeutic agent is an anti-PD-1 ligand (e.g., PD-LI (e.g., B7-HI or CD274); or PD-L2 (e.g., B7-DC or CD273)). In some embodiments, the immunotherapeutic agent is an anti-PD-1 antibody (e.g., anti-PD-1 or anti-PD-L1, e.g., nivolumab (i.e., MDX-1106, BMS-936558, ONO-4538); CT-011; AMP-224; pembrolizumab; pidilizumab; or MK-3475). In some embodiments, the immunotherapeutic agent is an anti-PD-L1 antibody (e.g., BMS936559 (i.e., MDX-1105); MEDI4736; MSB0010718C (avelumab); or MPDL-3280A).

In some embodiments, the immunotherapeutic agent is a checkpoint blocking antibody (e.g., anti-TIM3, anti-LAG3, anti-TIGIT including IMP321 and MGA271).

In some embodiments, the immunotherapeutic agent is a cell-based therapy. In some embodiments, the cell-based therapy is a CAR-T therapy.

In some embodiments, the immunotherapeutic agent is a co-stimulatory antibody (e.g., anti-4-1BB, anti-OX40, anti-GITR, anti-CD27, anti-CD40).

In some embodiments, the immunotherapeutic agent is a cancer vaccine such as a neoantigen. These vaccines can be developed using peptides or RNA, e.g., In some embodiments, the immunotherapeutic agent is an oncolytic virus.

In some embodiments, the immunotherapeutic agent is a STING pathway agonist. Exemplary STING agonists include MK-1454 and ADU-S100.

A PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can be administered in combination with disease-specific huMABs (e.g., an anti-HER3 huMAB)

A PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can be administered in combination with ADCs/ADCCs contingent on the expression of relevant surface targets on target tumors of interest.

Some patients may experience allergic reactions to the compounds of the present invention and/or other anti-cancer agent(s) during or after administration; therefore, anti-allergic agents are often administered to minimize the risk of an allergic reaction. Suitable anti-allergic agents include corticosteroids, including, but not limited to, dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of the compound of the present invention and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs including, but not limited to, hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include Amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g., Patents International (e.g., IMS World Publications).

The above-mentioned compounds, which can be used in combination with a compound of the present invention, can be prepared and administered as described in the art, including, but not limited to, in the documents cited above.

In one embodiment, the present invention provides pharmaceutical compositions comprising at least one compound of the present invention (e.g., a PRMT5 inhibitor, e.g., a compound of Formula (I), (Ia), (Ib), (Ic) and (Id) or a compound of Table 1) or a pharmaceutically acceptable salt thereof together with a pharmaceutically acceptable carrier suitable for administration to a human or animal subject, either alone or together with other anti-cancer agents.

In one embodiment, the present invention provides methods of treating human or animal subjects having or having been diagnosed with an MTAP-deficient and/or MTA accumulating proliferative disorder (e.g., cancer) comprising administering to the subject in need thereof a therapeutically effective amount of a compound of the present invention (e.g., a compound of Formula (I), (Ia), (Ib), (Ic) and (Id) or a compound of Table 1) or a pharmaceutically acceptable salt thereof in combination with a second therapeutic agent.

In one embodiment, the present invention provides methods of an MTAP-deficient and/or MTA accumulating proliferative disorder (e.g., cancer) in a subject in need thereof comprising administering to the subject a therapeutically effective amount of a compound of the present invention (e.g., a compound of Formula (I), (Ia), (Ib), (Ic) and (Id) or a compound of Table 1) or a pharmaceutically acceptable salt thereof in combination with a second therapeutic agent.

In particular, compositions will either be formulated together as a combination therapeutic or administered separately.

In combination therapy, the compound of the present invention and other anti-cancer agent(s) may be administered either simultaneously, concurrently or sequentially with no specific time limits, wherein such administration provides therapeutically effective levels of the two compounds in the body of the patient.

In a preferred embodiment, the compound of the present invention (e.g., a compound of Formula (I), (Ia), (Ib), (Ic) and (Id) or a compound of Table 1, or pharmaceutically acceptable salts thereof) and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In another aspect of the present invention, kits that include one or more compound of the present invention (e.g., a compound of Formula (I), (Ia), (Ib), (Ic) and (Id) or a compound of Table 1, or pharmaceutically acceptable salts thereof) and a second therapeutic agent as disclosed herein are provided. Representative kits include (a) a compound of the present invention or a pharmaceutically acceptable salt thereof (e.g., a compound of Formula (I), (Ia), (Ib), (Ic) and (Id) or a compound of Table 1, or pharmaceutically acceptable salts thereof), (b) at least one other therapeutic agent, e.g., as indicated above, whereby such kit may comprise a package insert or other labeling including directions for administration.

A compound of the present invention (e.g., a compound of Formula (I), (Ia), (Ib), (Ic) and (Id) or a compound of Table 1, or pharmaceutically acceptable salts thereof) may also be used in combination with known therapeutic processes, for example, the administration of hormones or especially radiation. A compound of the present invention may in particular be used as a radiosensitizer, especially for the treatment of tumors which exhibit poor sensitivity to radiotherapy.

In certain instances, compounds of the present invention are combined with other therapeutic agents, including, but not limited to, other anti-cancer agents, anti-allergic agents, anti-nausea agents (or anti-emetics), pain relievers, cytoprotective agents, and combinations thereof.

A PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) can also be administered or co-administered in any order with one or more DNA damage pathway inhibitor. In some embodiments, a DNA damage pathway inhibitor is selected from the group consisting of bleomycin, an ATM inhibitor (e.g., AZD1390), a USP1 inhibitor, a WEE1 inhibitor (e.g., AZD1775), and a Chk1 inhibitor (e.g., AZD7762). In some embodiments, a DNA damage pathway inhibitor is a DNA alkylating agent.

In one embodiment, the present invention provides pharmaceutical compositions comprising at least one compound of the present invention (e.g., a PRMT5 inhibitor, e.g., a compound of Formula (I), (Ia), (Ib), (Ic) and (Id) or a compound of Table 1) or a pharmaceutically acceptable salt thereof together with a pharmaceutically acceptable carrier suitable for administration to a human or animal subject, either alone or together with a PARP inhibitor. In some embodiments, a PARP inhibitor is selected from the group consisting of olaprib, rucaparib, niraparib, talazoparib, veliparib, pamiparib, CEP 9722, E7016, iniparib, and 3-aminobenzamide.

Patient Selection and Monitoring

In one aspect, the present invention provides a method of determining if a subject having or having been diagnosed with a cancer (e.g., a cancer patient) will respond to therapeutic treatment with a PRMT5 inhibitor (e.g., an MTA-uncompetitive PRMT5 inhibitor, e.g., a compound of Formula (I), (Ia), (Ib), (Ic) and (Id) or a compound of Table 1, or pharmaceutically acceptable salts thereof), comprising the steps of:
  a) contacting a test sample obtained from said subject with a reagent capable of detecting human cancer cells that have MTAP deficiency and/or MTA accumulation; and
  b) comparing the test sample with a reference (e.g., a reference sample taken from a non-cancerous or normal control subject),
    wherein the presence of MTAP deficiency and/or MTA accumulation in said test sample indicates that the subject will respond to therapeutic treatment with a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof).

In one aspect, the present invention provides a method of determining if a cancer will respond to therapeutic treatment with a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof), comprising the steps of:
  a) contacting a test sample obtained from a subject having or having been diagnosed with said cancer with a reagent capable of detecting human cancer cells that have MTAP deficiency and/or MTA accumulation; and
  b) comparing the test sample with a reference (e.g., a reference sample taken from a non-cancerous or normal control subject),
wherein the presence of MTAP deficiency and/or MTA accumulation in said test sample indicates that the cancer will respond to therapeutic treatment with a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof). In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma. In some embodiments, the method further comprises the step of determining the level of PRMT5 in the cancer cells. The level of expression of PRMT5 can be considered when determining the therapeutically effective dosage of a PRMT5 inhibitor.

In one aspect, the present invention provides a method of determining the sensitivity of a cancer cell to PRMT5 inhibition (e.g., inhibition with an MTA-uncompetitive PRMT5 inhibitor, e.g., a compound of Formula (I), (Ia), (Ib), (Ic) and (Id) or a compound of Table 1, or pharmaceutically acceptable salts thereof), comprising the steps of:
  a) assaying the production, level, activity, expression or presence of MTAP), in said cancer cell;
  b) comparing the production, level, activity, expression or presence of MTAP in the cancer cell with the production, level, activity, expression or presence of MTAP, respectively, in a non-cancerous or normal control cell,
wherein a decreased level, activity or expression in the cancer cell indicates MTAP deficiency and wherein MTAP deficiency indicates that said cancer cell is sensitive to the PRMT5 inhibitor. In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one embodiment, the present invention provides a method of determining the sensitivity of a cancer cell to a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof), comprising the steps of:
  a) assaying for level, activity or expression of the MTAP gene or its gene product in both the cancer cell and a normal control cell, wherein a decreased level, activity or expression in the cancer cell indicates MTAP deficiency; b) assaying for PRMT5 expression in said cancer cell; c) comparing the PRMT5 expression with PRMT5 expression in the cancer cell and a normal control cell; wherein the similarity in PRMT5 expression, and the presence of said MTAP deficiency in said cancer cell, indicates said cell is sensitive to a PRMT5 inhibitor.

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In one aspect the present invention provides a therapeutic method of treating a subject having or having been diagnosed with a cancer (e.g., a cancer associated with MTAP deficiency and/or MTA accumulation) comprising the steps of:
  a) assessing the level of MTAP and/or MTA in a test sample obtained from said subject (e.g., by contacting the sample with a reagent capable of detecting human MTAP-deficient and/or MTA-accumulating cancer cells in a test sample obtained from said subject), wherein the MTA level can be assessed directly (e.g., by ELISA or LC-MS/MS) or indirectly (e.g., by SDMA-modified protein ELISA or IHC, or by RNA splicing);
  b) comparing the test sample with a reference (e.g., a reference sample taken from a non-cancerous or normal control subject), wherein MTAP deficiency and/or MTA accumulation in said test sample indicates said subject will respond to therapeutic treatment with a PRMT5 inhibitor; and
  c) administering a therapeutically effective amount of PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) to the subject identified in step b).

In one aspect the present invention provides a therapeutic method of treating a cancer (e.g., a cancer associated with MTAP deficiency and/or MTA accumulation) in a subject in need thereof comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive, non-competitive, or mixed mode PRMT5 inhibitor or an MTA-cooperative binding agent); and
  c) administering a therapeutically effective amount of PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) to the subject identified in step b).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

In one aspect the present invention provides a therapeutic method of treating a subject having or having been diagnosed with a cancer associated with MTAP deficiency and/or MTA accumulation comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference sample (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive, non-competitive, or mixed mode PRMT5 inhibitor or an MTA-cooperative binding agent); and
  c) administering a therapeutically effective amount of a composition comprising a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) to the subject identified in step b).

In one aspect the present invention provides a therapeutic method of treating cancer associated with MTAP deficiency and/or MTA accumulation in a subject in need thereof comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference sample (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive, non-competitive, or mixed mode PRMT5 inhibitor or an MTA-cooperative binding agent); and
  c) administering a therapeutically effective amount of a composition comprising a PRMT5 inhibitor (e.g., an MTA-uncompetitive PRMT5 inhibitor e.g., a compound of Formula (I), (Ia), (Ib), (Ic) and (Id) or a compound of Table 1, or pharmaceutically acceptable salts thereof) to the subject identified in step b).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

In one aspect the present invention provides a method of determining if a subject having or having been diagnosed with a cancer associated with MTAP deficiency and/or MTA accumulation will respond to treatment with a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) comprising the steps of:
  a) assessing the level of MTAP and/or MTA in a test sample obtained from said subject (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference (e.g., a reference sample taken from a non-cancerous or normal control subject), wherein MTAP deficiency and/or MTA accumulation in said test sample indicates said subject will respond to therapeutic treatment with a PRMT5 inhibitor (e.g., an MTA-uncompetitive, non-competitive, or mixed mode PRMT5 inhibitor or an MTA-cooperative binding agent).

In one aspect the present invention provides a method of determining if a cancer associated with MTAP deficiency and/or MTA accumulation will respond to treatment with a PRMT5 inhibitor (e.g., an MTA-uncompetitive PRMT5 inhibitor, e.g., a compound of Formula (I), (Ia), (Ib), (Ic) and (Id) or a compound of Table 1, or pharmaceutically acceptable salts thereof) comprising the steps of:
  a) assessing the level of MTAP and/or MTA in a test sample obtained from a subject having or having been diagnosed with said cancer (e.g., by contacting the sample with a reagent capable of detecting human MTAP-deficient and/or MTA-accumulating cancer cells), wherein the MTA level can be assessed directly (e.g., by ELISA or LC-MS/MS) or indirectly (e.g., by SDMA-modified protein ELISA or IHC, or by RNA splicing);
  b) comparing the test sample with a reference (e.g., a reference sample taken from a non-cancerous or normal control subject), wherein MTAP deficiency and/or MTA accumulation in said test sample indicates said cancer will respond to therapeutic treatment with a PRMT5 inhibitor (e.g., an MTA-uncompetitive, non-competitive, or mixed mode PRMT5 inhibitor or an MTA-cooperative binding agent).

In some embodiments, the cancer is glioblastoma, malignant peripheral nerve sheath tumors (MPNST), esophageal cancer (e.g., esophageal squamous cell carcinoma or esophageal adenocarcinoma), bladder cancer (e.g., bladder urothelial carcinoma), pancreatic cancer (e.g., pancreatic adenocarcinoma), mesothelioma, melanoma, non-small cell lung cancer (NSCLC; e.g., lung squamous or lung adenocarcinoma), astrocytoma, undifferentiated pleiomorphic sarcoma, diffuse large B-cell lymphoma (DLBCL), leukemia, head and neck cancer, stomach adenocarcinoma, myxofibrosarcoma, cholangiosarcoma, cancer of the brain, stomach, kidney, breast, endometrium, urinary tract, liver, soft tissue, pleura and large intestine or sarcoma.

In some embodiments, the method further comprises the step of determining the level of PRMT5 in the cancer cells.

Sample Preparation

The invention further provides assays for the detection of MTAP deficiency and/or MTA accumulation. They can include detecting a mutation related to MTAP deficiency and/or MTA accumulation, e.g., in a body fluid such as blood (e.g., serum or plasma) bone marrow, cerebral spinal fluid, peritoneal/pleural fluid, lymph fluid, ascites, serous fluid, sputum, lacrimal fluid, stool, and urine, or in a tissue such as a tumor tissue. The tumor tissue can be fresh tissue or preserved tissue (e.g., formalin fixed tissue, e.g., paraffin-embedded tissue).

Body fluid samples can be obtained from a subject using any of the methods known in the art. Methods for extracting cellular DNA from body fluid samples are well known in the art. Typically, cells are lysed with detergents. After cell lysis, proteins are removed from DNA using various proteases. DNA is then extracted with phenol, precipitated in alcohol, and dissolved in an aqueous solution. Methods for extracting acellular DNA from body fluid samples are also known in the art. Commonly, a cellular DNA in a body fluid sample is separated from cells, precipitated in alcohol, and dissolved in an aqueous solution.

Detection of PRMT5 Selectivity

Samples, once prepared, can be tested for MTAP deficiency and/or MTA accumulation, either or both of which indicates that the sample is sensitive to treatment with a PRMT5 inhibitor. Cells can be determined to be MTA accumulating by techniques known in the art; methods for detecting MTA include, as a non-limiting example, liquid chromatography-electrospray ionization-tandem mass spectrometry (LC-ESI-MS/MS), as described in Stevens et al. 2010. J. Chromatogr. A. 1217: 3282-3288; and Kirovski et al. 2011 Am. J. Pathol. 178: 1145-1152; and references cited therein. The detection of MTAP deficiency can be done by any number of ways, for example: DNA sequencing, PCR based methods, including RT-PCR, microarray analysis, Southern blotting, Northern blotting, Next Generation Sequencing, and dip stick analysis. In some embodiments, MTAP deficiency is evaluated by any technique known in the art, for example, immunohistochemistry utilizing an anti-MTAP antibody or derivative thereof, and/or genomic sequencing, or nucleic acid hybridization, or amplification utilizing at least one probe or primer comprising a sequence of at least 12 contiguous nucleotides (nt) of the sequence of MTAP wherein the primer is no longer than about 30 nt.

The polymerase chain reaction (PCR) can be used to amplify and identify MTAP deficiency from either genomic DNA or RNA extracted from tumor tissue. PCR is well known in the art and is described in detail in Saiki et al., Science 1988, 239:487.

Methods of detecting MTAP deficiency by hybridization are provided. The method comprises identifying MTAP deficiency in a sample by its inability to hybridize to MTAP nucleic acid. The nucleic acid probe is detectably labeled with a label such as a radioisotope, a fluorescent agent or a chromogenic agent. Radioisotopes can include without limitation; 3H, 32P, 33P and 35S etc. Fluorescent agents can include without limitation: FITC, texas red, rhodamine, etc.

The probe used in detection that is capable of hybridizing to MTAP nucleic acid can be from about 8 nucleotides to about 100 nucleotides, from about 10 nucleotides to about 75 nucleotides, from about 15 nucleotides to about 50 nucleotides, or about 20 to about 30 nucleotides. The kit can also provide instructions for analysis of patient cancer samples, wherein the presence or absence of MTAP deficiency indicates if the subject is sensitive or insensitive to treatment with a PRMT5 inhibitor.

Single stranded conformational polymorphism (SSCP) can also be used to detect MTAP deficiency. This technique is well described in Orita et al., PNAS 1989, 86:2766-2770.

Measurement of Gene Expression

Evaluation of MTAP deficiency and measurement of MTAP gene expression, and measurement of PRMT5 gene expression can be performed using any method or reagent known in the art.

Detection of gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

In one aspect, gene expression is detected and quantitated by hybridization to a probe that specifically hybridizes to the appropriate probe for that biomarker. The probes also can be attached to a solid support for use in high throughput screening assays using methods known in the art.

In one aspect, the expression level of a gene is determined through exposure of a nucleic acid sample to the probe-modified chip. Extracted nucleic acid is labeled, for example, with a fluorescent tag, preferably during an amplification step.

Hybridization of the labeled sample is performed at an appropriate stringency level. The degree of probe-nucleic acid hybridization is quantitatively measured using a detection device.

Alternatively, any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, Mg 2+ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination. In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g., fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g., with a labeled RNA) by kinasing of the nucleic acid and subsequent attachment (ligation) of a nucleic acid linker joining the sample nucleic acid to a label (e.g., a fluorophore).

In one example, the gene expression can be measured through an in-situ hybridization protocol that can detect RNA molecules on a slide containing tissue sections or cells (e.g., through RNAscope®).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3H, 125I, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

Detection of labels is well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

Detection of Polypeptides

Protein levels of MTAP can be determined by examining protein expression or the protein product. Determining the protein level involves measuring the amount of any immunospecific binding that occurs between an antibody that selectively recognizes and binds to the polypeptide of the biomarker in a sample obtained from a subject and comparing this to the amount of immunospecific binding of at least one biomarker in a control sample.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), Western blot analysis, immunoprecipitation assays, immunofluorescent assays, flow cytometry, immunohistochemistry, HPLC, mass spectrometry, confocal microscopy, enzymatic assays, surface plasmon resonance and PAGE-SDS.

Adjacent Biomarkers

Near or adjacent to MTAP on chromosome 9 are several other biomarkers. CDKN2A is often, if not usually, deleted along with MTAP. Additional genes or pseudogenes in this region include: $C_9$orf53, ERVFRD-3, TUBB8P1, KHSRPP1, MIR31, and MIR31HG.

In some embodiments of the methods, the cell that is MTAP-deficient is also deficient in CDKN2A. In some embodiments, the cell that is MTAP-deficient is also deficient in one or more of: CDKN2A, C$_9$orf53, ERVFRD-3, TUBB8P1, KHSRPP1, MIR31, and MIR31HG.

Thus, in various methods involving a step of evaluating a cell for MTAP deficiency or determining if a cell is MTAP-deficient, this step can comprise the step of determining if the cell is deficient for one or more of these markers: CDKN2A, C$_9$orf53, ERVFRD-3, TUBB8P1, KHSRPP1, MIR31, and MIR31HG.

Thus, in some embodiments, the disclosure encompasses: A method of determining if a subject having or having been diagnosed with a cancer will respond to therapeutic treatment with a PRMT5 inhibitor (e.g., an MTA-uncompetitive, non-competitive, or mixed mode PRMT5 inhibitor or an MTA-cooperative binding agent), comprising the steps of:
  a) evaluating a test sample obtained from said subject for MTAP deficiency, and evaluating a reference sample from a non-cancerous or normal control subject for MTAP deficiency, wherein MTAP deficiency in the test sample relative to the reference sample indicates that the subject will respond to therapeutic treatment with a PRMT5 inhibitor (e.g., an MTA-uncompetitive PRMT5 inhibitor, e.g., a compound of Formula (I), (Ia), (Ib), (Ic) and (Id) or a compound of Table 1, or pharmaceutically acceptable salts thereof); wherein MTAP deficiency is evaluated by evaluating the deficiency of one or more of the following biomarkers: CDKN2A, C$_9$orf53, ERVFRD-3, TUBB8P1, KHSRPP1, MIR31, and MIR31HG, and wherein the method can further comprise the following steps:
  b) determining the level of MTAP in the subject, wherein steps a) and b) can be performed in any order;
  c) administering a therapeutically effective amount of a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) to the subject; and
  d) determining the level of PRMT5 activity in the subject following step c), wherein a decrease in the level of PRMT5 activity is correlated with the inhibition of the proliferation of the cancer, and wherein steps c) and d) are performed after steps a) and b).

In some embodiments, the disclosure encompasses: A method of determining if a cancer will respond to therapeutic treatment with a PRMT5 inhibitor (e.g., an MTA-uncompetitive, non-competitive, or mixed mode PRMT5 inhibitor or an MTA-cooperative binding agent), comprising the steps of:
  a) evaluating a test sample obtained from a subject having or having been diagnosed with said cancer for MTAP deficiency, and evaluating a reference sample from a non-cancerous or normal control subject for MTAP deficiency, wherein MTAP deficiency in the test sample relative to the reference sample indicates that the cancer will respond to therapeutic treatment with a PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof); wherein MTAP deficiency is evaluated by evaluating the deficiency of one or more of the following biomarkers: CDKN2A, C$_9$orf53, ERVFRD-3, TUBB8P1, KHSRPP1, MIR31, and MIR31HG, and wherein the method can further comprise the following steps:
  b) determining the level of MTAP in the subject, wherein steps a) and b) can be performed in any order;
  c) administering a therapeutically effective amount of a PRMT5 inhibitor (e.g., an MTA-uncompetitive PRMT5 inhibitor, e.g., a compound of Formula (I), (Ia), (Ib), (Ic) and (Id) or a compound of Table 1, or pharmaceutically acceptable salts thereof) to the subject; and
  d) determining the level of PRMT5 activity in the subject following step c), wherein a decrease in the level of PRMT5 activity is correlated with the inhibition of the proliferation of the cancer, and wherein steps c) and d) are performed after steps a) and b).

Assaying for Biomarkers and PRMT5 Inhibitor Treatment

A number of patient stratification strategies could be employed to find patients likely to be sensitive to PRMT5 inhibition with an MTA-uncompetitive, non-competitive, or mixed mode PRMT5 inhibitor or an MTA-cooperative binding agent (e.g., a PRMT5 inhibitor of the present invention, e.g., a compound of Formula (I), (Ia), (Ib), (Ic) and (Id) or a compound of Table 1, or pharmaceutically acceptable salts thereof), including but not limited to, testing for MTAP deficiency and/or MTA accumulation.

Once a patient has been assayed for MTAP deficiency and/or MTA accumulation and predicted to be sensitive to treatment with a PRMT5 inhibitor, administration of any PRMT5 inhibitor (e.g., an MTA-uncompetitive, non-competitive, or mixed mode PRMT5 inhibitor or an MTA-cooperative binding agent, e.g., a compound of Formula (I), (Ia), (Ib), (Ic) and (Id) or a compound of Table 1, or pharmaceutically acceptable salts thereof) to a patient can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents may be empirically adjusted.

Kits

In some embodiments kits related to methods of the invention are provided.

In one embodiment, a for predicting the sensitivity of a subject having or having been diagnosed with an MTAP-deficiency-related cancer for treatment with a PRMT5 inhibitor is provided. The kit comprises: i) reagents capable of detecting human MTAP-deficient and/or MTA-accumulating cancer cells; and ii) instructions for how to use said kit.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope. In the synthetic examples below, the descriptions of experimental procedures within a reaction sequence are listed in numerical order.

Abbreviations

General
ADDP 1,1'-(azodicarbonyl)dipiperidine
anhy. anhydrous
aq. aqueous
satd. saturated
min(s) minute(s)
hr(s) hour(s)
mL milliliter
mmol millimole(s)
mol mole(s)
MS mass spectrometry
NMR nuclear magnetic resonance
TLC thin layer chromatography
HPLC high-performance liquid chromatography
Me methyl
i-Pr iso-propyl
t-Bu tert-butyl
$^t$BuXPhos 2-di-tert-butylphosphino-2',4',6'-triisopropyl-biphenyl
Ph phenyl
Et ethyl
Bz benzoyl
RuPhos 2-dicyclohexylphosphino-2',6'-diisopropoxybi-phenyl Spectrum
Hz hertz
δ chemical shift
J coupling constant
s singlet
d doublet
t triplet
q quartet
m multiplet
br broad
qd quartet of doublets
dquin doublet of quintets
dd doublet of doublets
dt doublet of triplets Solvents and Reagents
DAST Diethylaminosulfurtrifluoride
$CHCl_3$ chloroform
DCM dichloromethane
DMF dimethylformamide
$Et_2O$ diethyl ether
EtOH ethyl alcohol
EtOAc ethyl acetate
MeOH methyl alcohol
MeCN acetonitrile
PE petroleum ether
THF tetrahydrofuran
DMSO dimethyl sulfoxide
t-BuOK potassium tert-butoxide
9-BBN 9-borabicyclo[3.3.1]nonane
AcOH acetic acid
HCl hydrochloric acid
$H_2SO_4$ sulfuric acid
$NH_4Cl$ ammonium chloride
KOH potassium hydroxide
NaOH sodium hydroxide
$K_2CO_3$ potassium carbonate
$Na_2CO_3$ sodium carbonate
TFA trifluoroacetic acid
$Na_2SO_4$ sodium sulfate
$NaBH_4$ sodium borohydride
$NaHCO_3$ sodium bicarbonate
LiHMDS lithium hexamethyldisilylamide
$NaBH_4$ sodium borohydride
$Et_3N$ triethylamine
Py pyridine
PCC pyridinium chlorochromate
DMAP 4-(dimethylamino)pyridine
DIPEA N,N-diisopropylethylamine
BINAP 2,2'-bis(diphenylphosphanyl)-1,1'-binaphthyl
dppf 1,1'-bis(diphenylphosphino)ferrocene
PEP Phospho(enol)pyruvic acid
LDH Lactate Dehydrogenase
DTT DL-Dithiothreitol
BSA Bovine Serum Albumin
NADH β-Nicotinamide adenine dinucleotide, reduced
$Pd(t-Bu_3P)_2$ bis(tri-tert-butylphosphine)palladium(O)
AcCl acetyl chloride
i-PrMgCl Isopropylmagnesium chloride
TBSCl tert-butyl(chloro)dimethylsilane
$(i-PrO)_4Ti$ titanium tetraisopropoxide
BHT 2,6-di-t-butyl-4-methylphenoxide
BzCl benzoyl chloride
CsF cesium fluoride
DCC dicyclohexylcarbodiimide
DMP Dess-Martin periodinane
EtMgBr ethylmagnesium bromide
EtOAc ethyl acetate
TEA triethylamine
AlaOH alanine
TBAF tetra-n-butylammonium fluoride
TBS t-butyldimethylsilyl
TMS trimethylsilyl
$TMSCF_3$ (Trifluoromethyl)trimethylsilane
Ts p-toluenesulfonyl
Bu butyl
$Ti(O^iPr)_4$ tetraisopropoxytitanium
LAH Lithium Aluminium Hydride
LDA lithium diisopropylamide
$LiOH \cdot H_2O$ lithium hydroxide hydrates
MAD methyl aluminum bis(2,6-di-t-butyl-4-methylphenoxide)
NBS N-bromosuccinimide
$Na_2SO_4$ sodium sulfate
$Na_2S_2O_3$ sodium thiosulfate
PE petroleum ether
MeCN acetonitrile
Boc t-butoxycarbonyl
MTBE methyl tert-butyl ether
DIAD diisopropyl azodicarboxylate General Experimental Notes:

In the following examples, the chemical reagents were purchased from commercial sources (such as Alfa, Acros, Sigma Aldrich, TCI and Shanghai Chemical Reagent Company), and used without further purification.

In some examples, purification of intermediates and final compounds was performed using HPLC ($H_2O$-MeOH; Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated under the $N_2$ flow upon heating to 80° C. On the basis of post-chromatography LCMS analysis fractions were united. Solid fractions were dissolved in 0.5 mL MeOH and transferred into pre-weighted marked vials.

Obtained solutions were again evaporated under the N₂ flow upon heating to 80° C. After drying, products were subjected to lyophilization using acetonitrile-water mixtures and finally characterized by LCMS and ¹H NMR.

Nuclear magnetic resonance (NMR) spectra were recorded using Brucker AVANCE DRX 500, Bruker 400 spectrometer or Varian UNITYplus 400. Chemical shifts for protons were reported as parts per million in δ scale using solvent residual peak (CHCl₃: 7.27 ppm) (methanol-d₄: 3.31 ppm) (DMSO-d₆: 2.50 ppm) or tetramethylsilane (0.00 ppm) as internal standards. Chemical shifts of ¹³C NMR spectra were reported in ppm from the central peak of CDCl₃ (77.00 ppm) (methanol-d₄: 49.15 ppm) (DMSO-d₆: 39.51 ppm) on the δ scale. Data are represented as follows: chemical shift, multiplicity (s=singlet, d=doublet, t=triplet, q=quartet, qn=quintuplet, sx=sextet, sp=septuplet, m=multiplet, br=broad), coupling constant (J, Hz) and integration.

In certain examples, mass spectra were recorded on an Agilent 1100 Series LC/MSD system with DAD\ELSD and Agilent LC\MSD VL (G1956A), SL (G1956B) mass-spectrometer or an Agilent 1200 Series LC/MSD system with DAD\ELSD and Agilent LC\MSD SL (G6130A), SL (G6140A) mass-spectrometer.

All the LC/MS data were obtained using positive/negative mode switching.

Column Zorbax SB-C18 1.8 μm 4.6×15 mm Rapid Resolution cartridge (PN 821975-932)
    Mobile phase A—acetonitrile, 0.1% formic acid
    B—water (0.1% formic acid)
    Flow rate 3 ml/min
    Gradient 0 min—100% B
    0.01 min—100% B
    1.5 min—0% B
    1.8 min—0% B
    1.81 min—100% B
    Injection volume 1 μl
    Ionization mode atmospheric pressure chemical ionization (APCI)
    Scan range m/z 80-1000.

Other Exemplary Analytical LC/MS Instruments and Conditions are Described Below:

Instrument: Agilent LC1100-MS6100 series G1956B; Column: Xbridge Shield RP-18, 50*2.1 mm*5 μm; Mobile Phase A: H₂O with 0.05% NH₃—H₂O (v %); Mobile Phase B: MeCN; Flow rate: 1.0 mL/min; Wavelength: UV 220 nm, 254 nm; Column temperature: 30° C.; MS ionization: ESI.

0-30CD: Gradient: B from 0%~30% over 2 minutes and holding at 30% for 0.48 minutes;
        0-60CD: Gradient: B from 0%~60% over 2 minutes and holding at 60% for 0.48 minutes;
        10-80CD: Gradient: B from 10%~80% over 2 minutes and holding at 80% for 0.48 minutes;
        30-90CD: Gradient: B from 30%~90% over 2 minutes and holding at 90% for 0.48 minutes;
        50-100CD: Gradient: B from 50%~100% over 2 minutes and holding at 100% for 0.48 minutes.

Instrument: Agilent LC1100-MS6100 series G1956B; Column: Xtimate C18, 30*2.1 mm*3 μm; Mobile Phase A: H₂O with 0.0375% TFA (v %); Mobile Phase B: MeCN with 0.01875% TFA (v %): Flow rate: 0.8 mL/min; Wavelength: UV 220 nm, 254 nm; Column temperature: 50° C.; MS ionization: ESI.

0-30AB: Gradient: B from 0%~30% over 3 minutes and holding at 30% for 0.5 minutes;
        0-60AB: Gradient: B from 0%~60% over 3 minutes and holding at 30% for 0.5 minutes;
        10-80AB: Gradient: B from 10%~80% over 3 minutes and holding at 30% for 0.5 minutes;
        30-90AB: Gradient: B from 0%~30% over 3 minutes and holding at 30% for 0.5 minutes;
        50-100AB: Gradient: B from 50%~100% over 3 minutes and holding at 100% for 0.5 minutes.

Instrument: Shimadzu LC20-MS2010; Column: Agilent Pursit 5 C18 20*2.0 mm; Mobile Phase A: H₂O with 0.0375% of TFA (v %); Mobile Phase B: MeCN with 0.01875% of TFA (v %); Gradient: B from 5~95% over 0.7 minutes and holding at 95% for 0.4 minutes; Flow Rate: 1.5 mL/min; Wavelength: UV 220 nm, 254 nm, 215 nm; Column temperature: 50° C.; MS ionization: ESI.

Instrument: Shimadzu LC20-MS2020; Column: Agilent Pursit 5 C18 20*2.0 mm; Mobile Phase A: H₂O with 0.0375% of TFA (v %); Mobile Phase B: MeCN with 0.01875% of TFA (v %); Gradient: B from 5~95% over 0.7 minutes and holding at 95% for 0.4 minutes; Flow Rate: 1.5 mL/min; Wavelength: UV 220 nm, 254 nm; Column temperature: 50° C.; MS ionization: ESI.

Exemplary HPLC Instruments and Conditions

Instrument: Shimadzu LC20; Column: YMC-Pack ODS-A 150*4.6 mm; Mobile Phase A: H₂O with 0.06875% TFA (v %); Mobile Phase B: MeCN with 0.0625% TFA (v %); Flow rate: 1.5 mL/min; Wavelength: UV 220 nm, 215 nm, 254 nm; Column temperature: 40° C.

0-30: Gradient: B from 0~30% over 10 minutes and holding at 30% for 5 minutes;
        0-60: Gradient: B from 0~60% over 10 minutes and holding at 60% for 5 minutes;
        0-95: Gradient: B from 0~95% over 10 minutes and holding at 95% for 5 minutes;
        10-80: Gradient: B from 10~80% over 10 minutes and holding at 80% for 5 minutes;
        30-90: Gradient: B from 30~90% over 10 minutes and holding at 90% for 5 minutes;
        50-100: Gradient: B from 10~100% over 10 minutes and holding at 100% for 5 minutes.

Instrument: Shimadzu LC20; Column: Xbridge Shield RP-18 50*2.1 mm, 5 μm; Mobile Phase A: H₂O with 0.01% NH₃—H₂O; Mobile Phase B: MeCN; Flow Rate: 1.2 mL/min; Wavelength: UV 220 nm, 215 nm, 254 nm; Column temperature: 40° C.

0-30CD: Gradient: B from 0~30% over 6 minutes and holding at 30% for 2 minutes;
        0-60CD: Gradient: B from 0~60% over 6 minutes and holding at 60% for 2 minutes;
        10-80CD: Gradient: B from 10~80% over 6 minutes and holding at 80% for 2 minutes;
        30-90CD: Gradient: B from 30~90% over 6 minutes and holding at 90% for 2 minutes;
        50-100CD: Gradient: B from 10~80% over 6 minutes and holding at 100% for 2 minutes.

Instrument: Shimadzu LC20; Column: Ultimate C18 50*3 mm, 3 μm; Mobile Phase A: H₂O with 0.06875% TFA (v %); Mobile Phase B: MeCN with 0.0625% TFA (v %); Flow Rate: 1.2 mL/min; Wavelength: UV 220 nm, 215 nm, 254 nm; Column temperature: 40° C.

0-30AB: Gradient: B from 0~30% over 2.5 minutes and holding at 30% for 0.75 minutes;
        0-60AB: Gradient: B from 0~60% over 2.5 minutes and holding at 60% for 0.75 minutes;
        5-95AB: Gradient: B from 5~95% over 2.5 minutes and holding at 95% for 0.75 minutes.

Instrument: Shimadzu LC20; Column: Ultimate C18 50*3 mm, 3 μm; Mobile Phase A: H₂O with 0.06875% TFA (v %); Mobile Phase B: MeCN with 0.0625% TFA (v %);

Flow Rate: 1.2 mL/min; Wavelength: UV 220 nm, 215 nm, 254 nm; Column temperature: 40° C. 10-80AB: Gradient: B from 10~80% over 4 minutes and holding at 80% for 2 minutes.

Exemplary TLC, Concentration and Normal Phase Chromatography.

Analytical thin layer chromatography (TLC) was performed with silica gel 60 F254 aluminum plates. Visualization was done under a UV lamp (254 nm) and by iodine or immersion in ethanolic phosphomolybdic acid (PMA) or potassium permanganate ($KMnO_4$), followed by heating using a heat gun. Organic solutions were concentrated by rotary evaporation at 20-40° C. Purification of reaction products were generally done by flash column chromatography with 230-400 mesh silica gel or Agela flash silica column.

Exemplary Chiral SFC Analytical Methods

Column: Chiralpak AD-3 150×4.6 mm I.D., 3 µm; Mobile phase: A: supercritical $CO_2$; Mobile phase B: EtOH (0.05% DEA); Gradient: from 5% to 40% of B in 5 min and hold 40% for 2.5 min, then 5% of B for 2.5 min; Flow rate: 2.5 mL/min; Column temperature: 35° C.; ABPR: 1500 psi.

Column: Chiralpak AD-3 100×4.6 mm I.D., 3 µm; Mobile phase: A: supercritical $CO_2$ Mobile phase B: EtOH (0.1% ethanolamine); Gradient: from 5% to 40% of B in 4.5 min and hold 40% for 2.5 min, then 5% of B for 1 min; Flow rate: 2.8 mL/min; Column temperature: 40° C.

Exemplary Preparative HPLC Separation Methods

Basic condition ($NH_3$—$H_2O$): Instrument: Gilson GX-281 Liquid Handler, Gilson 322 Pump, Gilson 156 UV Detector; Column: Waters Xbridge 150×25 mm×5 µm; Mobile phase A: $H_2O$ with 0.05% $NH_3$—$H_2O$ (v %); Mobile phase B: MeCN; Gradient: B from 22% to 52% in 9.5 min, hold 100% B for 1 min; Flow Rate: 25 mL/min; Column Temperature: 30° C.; Wavelength: 220 nm, 254 nm.

Acid condition (HCOOH): Instrument: Gilson GX-281 Liquid Handler, Gilson 322 Pump, Gilson 156 UV Detector; Column: Agela Durashell C18 150*25 mm 5 µm; Mobile phase A: $H_2O$ (0.0225% HCOOH); Mobile phase B: MeCN; Gradient: B from 7% to 37% in 9 min, hold 100% B for 0 min; Flow Rate: 25 mL/min; Column Temperature: 30° C.; Wavelength: 220 nm, 254 nm.

Acid condition (HCl): Gilson GX-281 Liquid Handler, Gilson 322 Pump, Gilson 156 UV Detector; Column: Xtimate C18 150*25 mm*5 µm; Mobile phase A: $H_2O$ with 0.05% HCl (v %); Mobile phase B: MeCN; Gradient: B from 0% to 30% in 6.5 min, hold 100% B for 2.5 min; Flow Rate: 25 mL/min; Column Temperature: 30° C.; Wavelength: 220 nm, 254 nm).

Neutral condition ($NH_4HCG_3$): (Instrument: Gilson GX-281 Liquid Handler, Gilson 322 Pump, Gilson 156 UV Detector; Column: Waters Xbridge 150×25 mm×5 µm; Mobile phase A: $H_2O$ with 10 mmol $NH_4HCO_3$; Mobile phase B: MeCN; Gradient: B from 39% to 69% in 10 min, hold 100% B for 2.5 min; Flow Rate: 25 mL/min; Column Temperature: 30° C.; Wavelength: 220 nm, 254 nm).

Exemplary Large-Scale Separation

Basic condition: Instrument: Shimadzu LC-8A Pumps, Shimadzu SCL-10A VP System Controller, Shimadzu SPD-20AV UV/VIS Detector; Column: Phenomenex Gemini C18 250*50 mm*10 µm; Mobile phase A: water (0.04% $NH_3$—$H_2O$+10 mM $NH_4HCO_3$); Mobile phase B: MeCN; Gradient: B from 65% to 95% in 26 min, hold 100% B for 3 min; Flow Rate: 110 mL/min; Column Temperature: 30° C.; Wavelength: 220 nm, 254 nm.

Acid condition (TFA): Instrument: Shimadzu LC-20AP Pumps, Shimadzu CBM-20A System Controller Shimadzu SPD-20AV UV/VIS Detector; Column: Phenomenex luna C18 250×50 mm×10 µm; Mobile phase A: $H_2O$ with 0.1% TFA (v %); Mobile phase B: MeCN; Gradient: B from 0% to 25% in 15 min, hold 100% B for 4 min; Flow Rate: 120 mL/min; Column Temperature: 30° C.; Wavelength: 220 nm, 254 nm.

Exemplary Preparative Chiral SFC Method:

Exemplary chiral columns available for use in the separation/purification of the enantiomers/diastereomers provided herein include, but are not limited to, CHIRALPAK® AD-10, CHIRALCEL® OB, CHIRALCEL® OB—H, CHIRALCEL® OD, CHIRALCEL® OD-H, CHIRALCEL® OF, CHIRALCEL® OG, CHIRALCEL® OJ and CHIRALCEL® OK.

In certain examples, the chiral separation was performed under the following conditions: Instrument: Thar 80; Column: Daicel Chiralpak AD. 250×30 mm I.D. 10 µm; Mobile phase: supercritical $CO_2$/MeOH (0.1% $NH_3$—$H_2O$, v %)=60/40; Flow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis.

Exemplary general method for preparative HPLC: Column: Waters RBridge prep 10 µm C18, 19*250 mm. Mobile phase: acetonitrile, water ($NH_4HCO_3$) (30 L water, 24 g $NH_4HCO_3$, 30 mL $NH_3 \cdot H_2O$). Flow rate: 25 mL/min Exemplary general method for analytical HPLC: Mobile phase: A: water (10 mM $NH_4HCO_3$), B: acetonitrile Gradient: 5%~95% B in 1.6 or 2 min Flow rate: 1.8 or 2 mL/min; Column: XBridge C18, 4.6*50 mm, 3.5 µm at 45° C.

1. Synthesis of Common Intermediates

1A. The Synthesis of (S)-tert-butyl 5-methyl-2-oxopiperidine-1-carboxylate

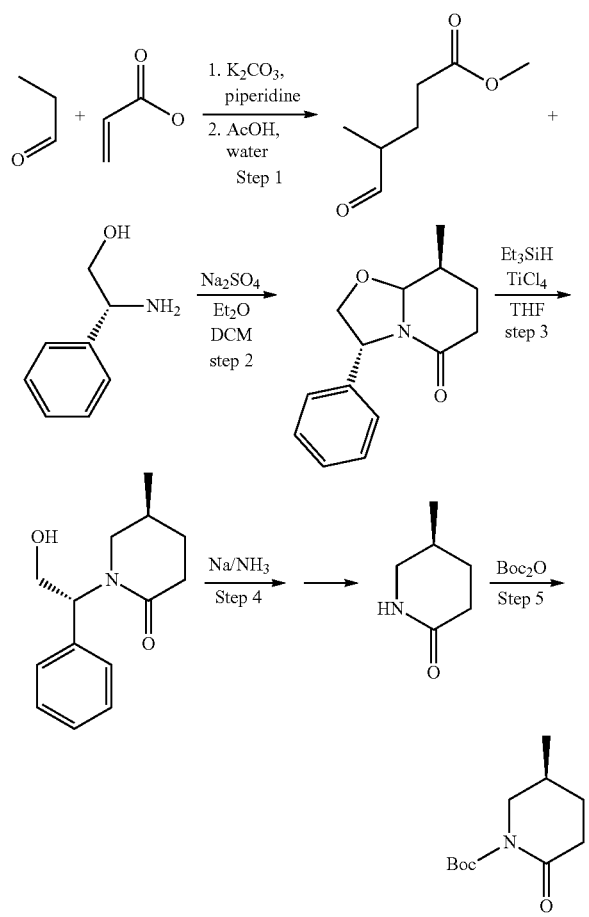

Step 1: Synthesis of Methyl 4-methyl-5-oxopentanoate

To a stirring mixture of Piperidine, 99% (293.22 g, 3.44 mol, 340.16 mL) and Potassium carbonate—granular (95.19 g, 688.72 mmol, 41.57 mL), propanal (100 g, 1.72 mol, 123.46 mL) was added drop wise. The reaction mixture was stirred at room temperature for 18 hours. After 18 hours, the reaction mixture was filtered through a pad of Na₂SO₄ and washed with MTBE (1000 mL). The filtrate was dried over Na₂SO₄, filtered and concentrated under reduced pressure. The obtained crude enamine was dissolved in MeCN (1000 mL) and methyl prop-2-enoate (296.46 g, 3.44 mol, 310.10 mL) was added dropwise to the solution at room temperature. The resulting reaction mixture was refluxed for 16 hours. After 16 hours, Acetic acid (206.79 g, 3.44 mol, 196.94 mL) was added (carefully), followed by water (1000 mL) and the resulting solution was heated at reflux for an additional 16 hours. Then, the mixture was cooled to room temperature, saturated with NaCl and extracted with MTBE (2×1000 mL). The combined organic phase was dried over Na₂SO₄, filtered and concentrated under reduced pressure to obtain crude product methyl 4-methyl-5-oxo-pentanoate (264 g, crude). The crude product was used for the next step without any further purification.

¹H NMR (CDCl₃, 500 MHz): δ 1.09 (d, 3H), 1.60-1.72 (m, 1H), 1.94-2.00 (m, 1H), 2.29-2.42 (m, 3H), 3.64 (s, 3H), 9.59 (s, 1H).

Step 2: Synthesis of (3R,8S,8aR)-8-methyl-3-phenyltetrahydro-2H-oxazolo[3,2-a]pyridin-5(3H)-one A mixture of methyl 4-methyl-5-oxo-pentanoate (67.8 g, 470.28 mmol), (2R)-2-amino-2-phenyl-ethanol (64.51 g, 470.28 mmol) and Sodium sulfate, anhydrous (66.80 g, 470.28 mmol) in DCM (800 mL) and Ether (200 mL) was stirred at 0° C. for 5 hours. After 5 hours, the resulting suspension was filtered, and the filtrate was concentrated under reduced pressure. The residue was purified by column chromatography (Interchim; 800 g SiO₂; chloroform/acetonitrile with acetonitrile from 0 to 15%, flow rate=120 ml/min, Rv=4-10 cv.) to give product (3R,8S,8aR)-8-methyl-3-phenyltetrahydro-2H-oxazolo[3,2-a]pyridin-5 (3H)-one (59.8 g, 258.55 mmol, 54.98% yield) as a light-yellow gum.

¹H NMR (CDCl₃, 500 MHz): δ 1.20 (d, J=6.3 Hz, 3H), 1.42-1.56 (m, 1H), 1.86-2.00 (m, 2H), 2.22-2.44 (m, 2H), 4.00 (dd, J=8.8, 1.2 Hz, 1H), 4.07-4.17 (m, 1H), 4.42 (dd, J=8.9, 3.2 Hz, 1H), 4.87-4.95 (m, 1H), 7.17-7.32 (m, 5H).

LCMS(ESI): [M+H]⁺ m/z: calcd 231.1; found 232.2; Rt=1.12 min.

Step 3: Synthesis of (S)-1-((R)-2-hydroxy-1-phenylethyl)-5-methylpiperidin-2-one Triethylsilane (1.51 g, 12.97 mmol, 2.07 mL) and titanium tetrachloride (3.69 g, 19.46 mmol) were added to a solution of (3R,8S,8aR)-8-methyl-3-phenyltetrahydro-2H-oxazolo[3,2-a]pyridin-5(3H)-one (1 g, 4.32 mmol) in anhydrous DCM (25 mL) and the mixture was stirred at 40° C. for 24 hours. Then, additional titanium tetrachloride (3.69 g, 19.46 mmol, 764.36 µL) and Triethylsilane (1.51 g, 12.97 mmol, 2.07 mL) were added, and the stirring was continued at 50° C. for 24 hours. The mixture was poured into saturated aqueous NaHCO₃ (100 mL) solution. The aqueous phase was filtered over Celite and extracted with CH₂C₂. The combined organic extracts were dried over Na₂SO₄, filtered, and concentrated under reduced pressure to give a residue, which was purified by column chromatography (Companion Combiflash; 40 g SiO₂; MTBE/methanol with methanol from 0 to 8%, flow rate=40 mL/min, Rv=9-11 cv.) to give product (S)-1-((R)-2-hydroxy-1-phenylethyl)-5-methylpiperidin-2-one (0.51 g, 2.19 mmol, 50.56% yield) as a colorless oil.

¹H NMR (CDCl₃, 400 MHz): δ 0.93 (d, J=6.4 Hz, 3H), 1.44-1.54 (m, 1H), 1.77-1.86 (m, 2H), 2.40-2.62 (m, 2H), 2.83 (t, J=11.0 Hz, 1H), 2.92-2.99 (m, 1H), 4.04-4.21 (m, 2H), 5.71-5.79 (m, 2H), 7.17-7.37 (m, 5H)

LCMS(ESI): [M+H]⁺ m/z: calcd 233.1; found 234.2; Rt=0.98 min.

Step 4: Synthesis of (S)-5-methylpiperidin-2-one

Into a three-necked, 1000 mL, round-bottomed flask equipped with a coldfinger condenser charged with dry ice acetone were condensed ammonia (500 mL) at −78° C. A solution of (S)-1-((R)-2-hydroxy-1-phenylethyl)-5-methylpiperidin-2-one (17.2 g, 73.72 mmol) in dry THF (100 mL) was added and the temperature was raised to −33° C. Sodium (5.08 g, 221.17 mmol) was added in small portions until the blue color persisted, and the mixture was stirred at −33° C. for 3 minutes. The reaction was quenched by the addition of solid NH₄Cl until the blue color disappeared, and then the mixture was stirred at room temperature for 5 hours. CH₂C₁₂ was added, the solid was filtered, and the solvent was removed under reduced pressure to give (S)-5-methylpiperidin-2-one (15 g, crude) as a light-yellow oil. The residue was used for the next step without any further purification.

$^1$H NMR (DMSO-d₆, 400 MHz): δ 1.01 (d, J=6.6 Hz, 3H, CH₃), 1.45-1.51 (m, 1H, H-4), 1.83-1.99 (m, 2H, H-4, H-5), 2.34 (ddd, J=17.8, 10.8, 6.4 Hz, 1H, H-3), 2.43 (ddd, J=17.8, 6.4, 3.5 Hz, 1H, H-3), 2.92 (t, J=10.8 Hz, 1H, H-6), 3.26-3.33 (m, 1H, H-6), 6.10 (br.s, 1H, NH)

Step 5: Synthesis of (S)-tert-butyl 5-methyl-2-oxopiperidine-1-carboxylate

To a solution of (S)-5-methylpiperidin-2-one (15 g, 79.54 mmol, crude) and DMAP (971.67 mg, 7.95 mmol) in DCM (500 mL) was added Di-tert-butyl dicarbonate (17.36 g, 79.54 mmol, 18.25 mL) dropwise at 21° C. The resulting reaction mixture was stirred at the same temperature for 1 hour. After 1 hour, the resulting solution was diluted with 10% aq. HCl and brine, dried over Na₂SO₄ and concentrated under reduced pressure to obtain crude product, which was purified by column chromatography (Companion Combiflash, 330 g SiO₂, petroleum ether/MTBE with MTBE from 10~25%, flow rate=100 mL/min, Rv=6 CV) to give product (S)-tert-butyl 5-methyl-2-oxopiperidine-1-carboxylate (9 g, 42.20 mmol, 53.06% yield) as a yellow solid.

$^1$H NMR (400 MHz, DMSO-d₆) δ 0.96 (d, J=6.6 Hz, 3H), 1.42 (s, 9H), 1.74-1.86 (m, 1H), 1.87-1.97 (m, 1H), 2.30-2.39 (m, 2H), 2.98-3.11 (m, 1H), 3.12 (s, 1H), 3.60-3.68 (m, 1H).

LCMS(ESI): [M+H]⁺ m/z: calcd 213.2; found 158.2; Rt=1.24 min (t-Bu cleavage).

1B. The Synthesis of tert-butyl 3-methyl-6-(((trifluoromethyl)sulfonyl)oxy)-3,4-dihydropyridine-1(2H)-carboxylate

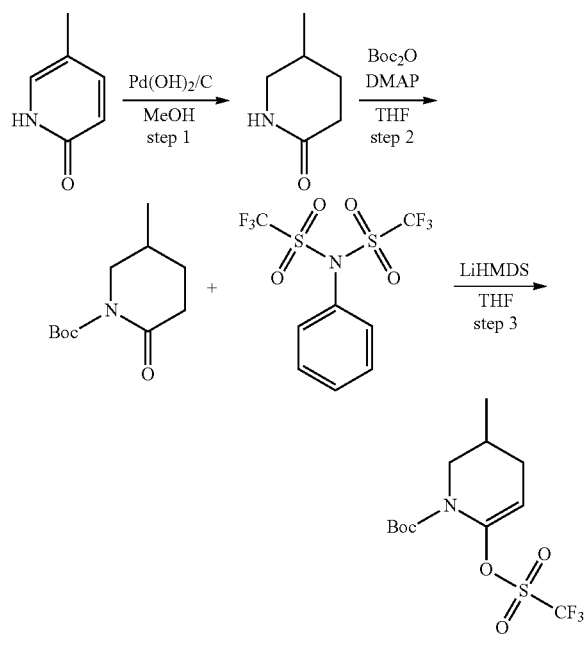

Step 1: Synthesis of 5-methylpiperidin-2-one

A solution of 5-methyl-1H-pyridin-2-one (102 g, 934.70 mmol) in MeOH (1000 mL) was hydrogenated in autoclave in the presence of palladium hydroxide on carbon 5% (15 g, 106.81 mmol) at 50° C. under 100 atm pressure of hydrogen for 12 hr. The reaction mixture was cooled, the catalyst was filtered off, the filtrate was evaporated in vacuo to afford 5-methylpiperidin-2-one (105 g, 927.91 mmol, 99.27% yield) as white solid.

$^1$H NMR (500 MHz, DMSO-d₆) δ (ppm) 0.94 (d, 3H), 1.38 (m, 1H), 1.77 (m, 2H), 2.12 (d, 2H), 2.74 (m, 1H), 3.12 (m, 1H), 7.37 (m, 1H).

LCMS(ESI): [M]⁺ m/z: calcd 113.2; found 114.2; Rt=0.701 min.

Step 2: Synthesis of tert-butyl 5-methyl-2-oxopiperidine-1-carboxylate

Di-tert-butyl dicarbonate (212.64 g, 974.31 mmol, 223.60 mL) was added to a stirred mixture of 5-methylpiperidin-2-one (105 g, 927.91 mmol) and N,N-dimethylpyridin-4-amine (11.34 g, 92.79 mmol) in THF (1000 mL) at 25° C. The reaction mixture was stirred at 25° C. for 24 hr, and then evaporated in vacuo. The residue was dissolved in dichloromethane (1500 ml) and washed successively with 5% aqueous sodium hydrogen sulphate solution (400 ml), and water (400 ml). The organic layer was separated, dried over sodium sulphate and evaporated in vacuo to afford crude tert-butyl 5-methyl-2-oxo-piperidine-1-carboxylate (199 g, crude) as light-yellow oil, which was used directly in the next step.

$^1$H NMR (500 MHz, CDCl₃) δ (ppm) 1.03 (d, 3H), 1.48 (m, 1H), 1.58 (s, 9H), 1.92 (m, 2H), 2.56 (m, 2H), 3.11 (t, 1H), 3.80 (d, 1H).

LCMS(ESI): [M-Boc]⁺ m/z: calcd 113.2; found 114.2; Rt=1.275 min.

Step 3: Synthesis of tert-butyl 3-methyl-6-(((trifluoromethyl)sulfonyl)oxy)-3,4-dihydropyridine-1(2H)-carboxylate LiHMDS (588.42 g, 703.32 mmol, 653.80 mL, 20% purity) (1.08 M in THF/ethylbenzene) was added dropwise under argon to a cooled to −78° C. solution of tert-butyl 5-methyl-2-oxo-piperidine-1-carboxylate (100 g, 468.88 mmol) in THF (1000 mL). The resulting solution was stirred at −78° C. for 1.5 hr, then 1,1,1-trifluoro-N-phenyl-N-(trifluoromethylsulfonyl)methanesulfonamide (209.39 g, 586.10 mmol) was added in one portion. The reaction mixture was allowed to warm to 25° C. and stirred for 12 hr, then diluted with water (300 ml) and MTBE (1500 ml). The organic layer was separated, the aqueous layer was additionally extracted with MTBE (300 ml). The combined organic extracts were washed with 10% aqueous sodium hydroxide solution (3*500 ml), dried over potassium carbonate and evaporated in vacuo. The residue was diluted with hexane/MTBE mixture (4/1, 1500 ml, repeated three times) and stirred for 0.5 hr. The resulting cloudy solution was decanted from oily residue, filtered through a short pad of silica gel and evaporated in vacuo to afford tert-butyl 3-methyl-6-(trifluoromethylsulfonyloxy)-3,4-dihydro-2H-pyridine-1-carboxylate (147 g, 425.67 mmol, 90.78% yield) as light-yellow oil.

$^1$H NMR (500 MHz, CDCl₃) δ (ppm) 1.01 (d, 3H), 1.49 (s, 9H), 1.87 (m, 2H), 2.38 (d, 1H), 3.01 (d, 1H), 3.89 (d, 1H), 5.26 (m, 1H).

LCMS(ESI): [M-Boc]⁺ m/z: calcd 245.3; found 246.2; Rt=1.719 min.

2. Synthesis of Common Pyridyl Oxo-acetate Intermediates

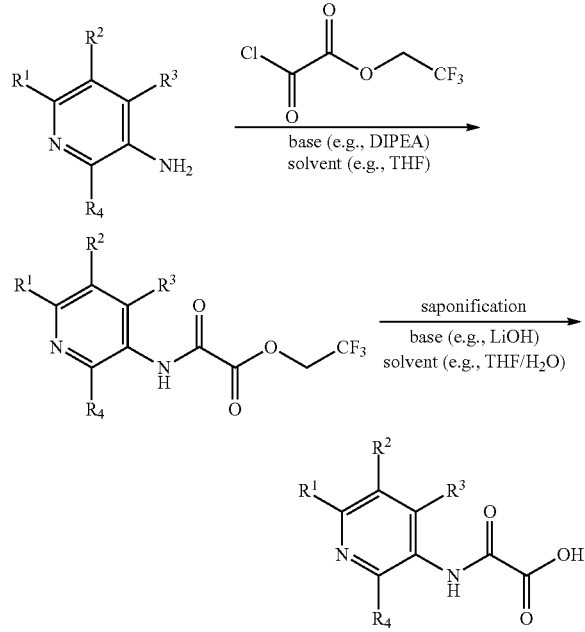

2A. The Synthesis of 2,2,2-trifluoroethyl 2-[(5-carbamoyl-3-pyridyl)amino]-2-oxo-acetate and 2-((5-carbamoylpyridin-3-yl)amino)-2-oxoacetic Acid Lithium Salt

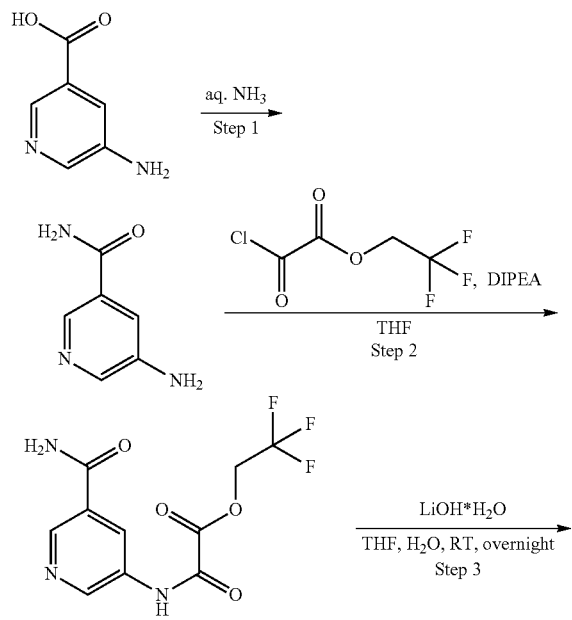

-continued

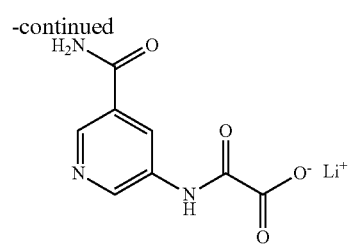

Step 1: Synthesis of 5-aminopyridine-3-carboxamide

Methyl 5-aminopyridine-3-carboxylate (HCl salt) (5 g, 32.86 mmol) was dissolved in 25% NH₃ (aq) (50 mL) and the resulting reaction mixture was stirred at room temperature for 18 hours. After 18 hours, the reaction mixture was concentrated under reduced pressure and the obtained residue was washed with water (20 mL), dried at 70° C. for 10 hours to obtain 5-aminopyridine-3-carboxamide (2.8 g, 20.42 mmol, 62.13% yield) as a white powder.

$^1$H NMR (DMSO-$d_6$, 400 MHz): δ (ppm) 5.49 (brs, 2H), 7.30 (t, 1H), 7.36 (brs, 1H), 7.93 (brs, 1H), 8.02 (d, 1H), 8.18 (s, 1H)

LCMS(ESI): [M+H]⁺ m/z: calcd 137.1; found 138.2; Rt=0.139 min.

Step 2: Synthesis of 2,2,2-trifluoroethyl 2-[(5-carbamoyl-3-pyridyl)amino]-2-oxo-acetate To a stirring solution of 5-aminopyridine-3-carboxamide (0.65 g, 4.74 mmol) and DIPEA (918.84 mg, 7.11 mmol, 1.24 mL) in dry THF (15 mL), 2,2,2-trifluoroethyl 2-chloro-2-oxo-acetate (993.23 mg, 5.21 mmol) was added dropwise at 0° C. The reaction mixture was stirred for 12 hours at room tTemperature and then filtered. The filtrate was concentrated under vacuo to obtain 2,2,2-trifluoroethyl 2-[(5-carbamoyl-3-pyridyl)amino]-2-oxo-acetate (1.7 g, crude). The crude product was used for the next step reaction without any further purification.

LCMS(ESI): [M+H]⁺ m z: calcd 291.0; found 292.2; Rt=0.815 min.

Step 3: The Synthesis of 2-((5-carbamoylpyridin-3-yl)amino)-2-oxoacetic Acid Lithium Salt 2,2,2-trifluoroethyl 2-[(5-carbamoyl-3-pyridyl)amino]-2-oxo-acetate (1.1 g, 3.78 mmol) and Lithium hydroxide monohydrate, 98% (174.38 mg, 4.16 mmol) were mixed together in THF (10 mL) and H₂O (2.5 mL). The resulting mixture was stirred overnight. The resulting mixture was diluted 10 mL THF. The precipitate was filtered on and air-dried to afford 2-((5-carbamoylpyridin-3-yl)amino)-2-oxoacetic acid lithium salt (0.74 g, 3.44 mmol, 91.07% yield) as a white powder.

$^1$H NMR (400 MHz, DMSO-$d_6$) δ 7.56 (s, 1H), 8.12 (s, 1H), 8.66 (m, 2H), 8.98 (s, 1H), 10.58 (m, 1H).

2B. The Synthesis of 2,2,2-trifluoroethyl 2-[[6-(tert-butoxycarbonylamino)-5-methyl-3-pyridyl]amino]-2-oxo-acetate and 2-[[6-(tert-butoxycarbonylamino)-5-methyl-3-pyridyl]amino]-2-oxo-acetic acid

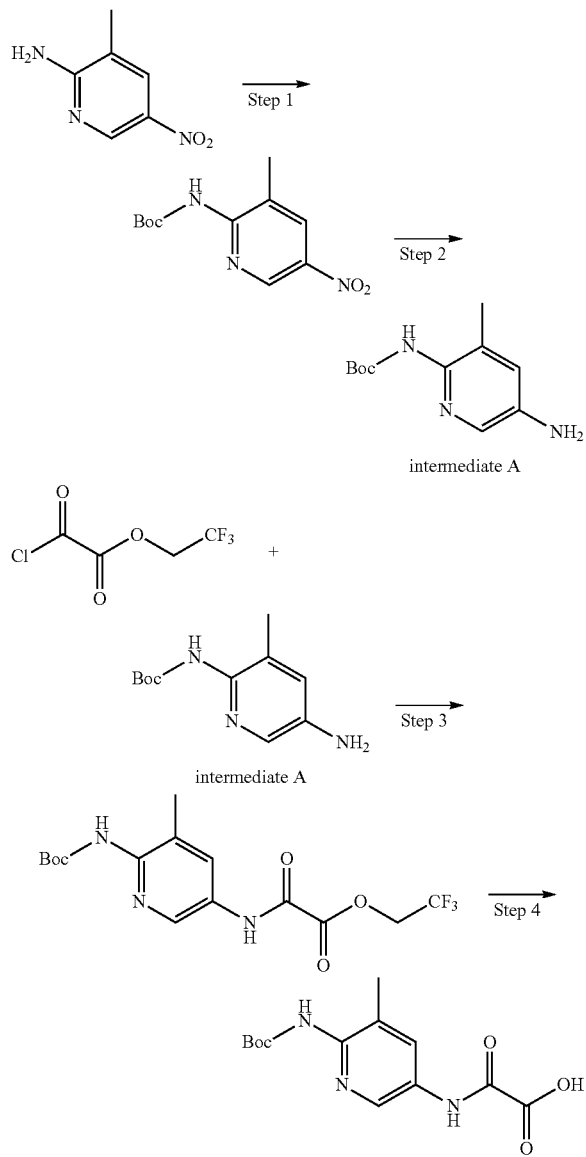

Step 1: Synthesis of tert-butyl N-(3-methyl-5-nitro-2-pyridyl)carbamate

To a solution of 3-methyl-5-nitro-pyridin-2-amine (60 g, 391.80 mmol) in DMF (525 mL), Sodium hydride (in oil dispersion) 60% dispersion in mineral oil (16.51 g, 412.88 mmol, 60% purity) was added portionwise at 0° C. The resulting mixture was stirred for 0.5 h (to the end of gas evolution) and a solution of Di-tert-butyl dicarbonate (89.79 g, 411.39 mmol, 94.41 mL) in DMF (75 mL) was added dropwise. The resulting mixture was stirred at 25° C. for 18 hr. The mixture was quenched with water (1000 mL), the precipitate formed was filtered off and dried in vacuo to obtain crude product (100 g). This material was purified by gradient chromatography on silica gel (CHCl$_3$-MTBE as eluent) to obtain tert-butyl N-(3-methyl-5-nitro-2-pyridyl) carbamate (46 g, 181.64 mmol, 46.36% yield).

$^1$H NMR (DMSO-d$_6$, 400 MHz): δ 1.49 (s, 9H), 2.32 (s, 3H), 8.37 (s, 1H), 8.97 (s, 1H), 9.59 (s, 1H)

LCMS(ESI): [M-CH$_2$C(CH$_3$)+H]$^+$ m/z: calcd 253.26; found 198.2; Rt=1.272 min.

Step 2: Synthesis of tert-butyl N-(5-amino-3-methyl-2-pyridyl)carbamate

To a solution of tert-butyl N-(3-methyl-5-nitro-2-pyridyl) carbamate (46 g, 181.64 mmol) in MeOH (600 mL) was added Palladium on activated carbon 10% (4.60 g, 43.22 mmol). The resulting mixture was stirred under hydrogen atmosphere for 24 hr. The catalyst was filtered and the solvent was evaporated in vacuo, the residue was dissolved in DCM (500 ml), dried over Na$_2$SO$_4$ and evaporated in vacuo to obtain tert-butyl N-(5-amino-3-methyl-2-pyridyl) carbamate (38 g, 170.20 mmol, 93.70% yield).

$^1$H NMR (DMSO-d$_6$, 400 MHz): δ 1.40 (s, 9H), 2.03 (s, 3H), 3.30 (brs, 2H), 6.80 (s, 1H), 7.54 (s, 1H), 8.52 (s, 1H)

LCMS(ESI): [M+H]$^+$ m/z: calcd 223.2; found 224.2; Rt=0.67 min.

Step 3: Synthesis of 2,2,2-trifluoroethyl 2-[[6-(tert-butoxycarbonylamino)-5-methyl-3-pyridyl]amino]-2-oxo-acetate To a solution of tert-butyl N-(5-amino-3-methyl-2-pyridyl)carbamate (17.6 g, 78.83 mmol) and DIPEA (15.28 g, 118.24 mmol, 20.60 mL) in ACN (250 mL) was added 2,2,2-trifluoroethyl 2-chloro-2-oxo-acetate (17.27 g, 90.65 mmol) dropwise at 0° C. under argon. The reaction mixture was then stirred for 24 hr at r.t., then evaporated in vacuo, the residue was diluted with water (575 mL). The precipitate formed was filtered off, washed with water and dried in vacuo to provide the product 2,2,2-trifluoroethyl 2-[[6-(tert-butoxycarbonylamino)-5-methyl-3-pyridyl]amino]-2-oxo-acetate (30 g, crude).

$^1$H NMR (DMSO-d$_6$, 400 MHz): δ 1.42 (s, 9H), 2.15 (s, 3H), 4.96 (q, 2H), 7.93 (s, 1H), 8.49 (s, 1H), 9.03 (s, 1H), 11.06 (s, 1H)

LCMS(ESI): [M-CH$_2$C(CH$_3$)+H]$^+$ m/z: calcd 377.32; found 322.0; Rt=1.274 min.

Step 4: Synthesis of 2-[[6-(tert-butoxycarbonylamino)-5-methyl-3-pyridyl]amino]-2-oxo-acetic acid A mixture of 2,2,2-trifluoroethyl 2-[[6-(tert-butoxycarbonylamino)-5-methyl-3-pyridyl]amino]-2-oxo-acetate (30 g, 79.51 mmol) and lithium hydroxide, monohydrate (6.67 g, 159.02 mmol, 4.42 mL) in THF (120 mL)—methanol (120 mL)—water (120 mL) was stirred at 5° C. with TLC control (DCM-MeOH 5:1 as eluent). Upon complete consumption of the starting material (2 hr) the volatile organic solvents were rotoevaporated. The residue was acidified with sodium hydrogen sulfate, monohydrate (21.96 g, 159.02 mmol) to pH 5 and the precipitate formed was filtered off, washed with water and dried in vacuo to provide the product 2-[[6-(tert-butoxycarbonylamino)-5-methyl-3-pyridyl] amino]-2-oxo-acetic acid (23 g, 77.89 mmol, 97.96% yield).

$^1$H NMR (DMSO-d$_6$, 400 MHz): δ 1.44 (s, 9H), 2.16 (s, 3H), 7.97 (s, 1H), 8.51 (s, 1H), 8.98 (s, 1H), 10.70 (s, 1H)

LCMS(ESI): [M-CH$_2$C(CH$_3$)+H]$^+$ m/z: calcd 295.29; found 240.0; Rt=0.829 min.

2C. The Synthesis of 2,2,2-trifluoroethyl 2-[(5-carbamoyl-6-methoxy-3-pyridyl)amino]-2-oxo-acetate and 2-[(5-carbamoyl-6-methoxy-3-pyridyl)amino]-2-oxo-acetic acid

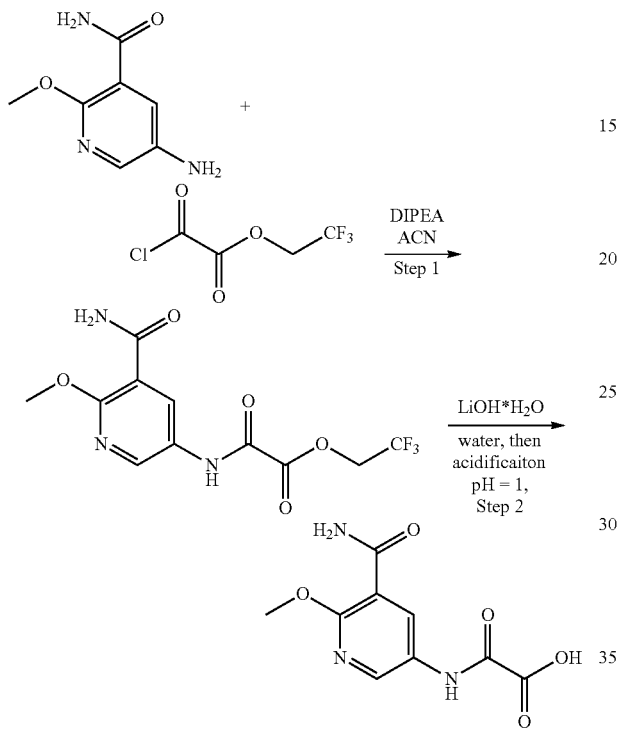

Step 1: Synthesis of 2,2,2-trifluoroethyl 2-[(5-carbamoyl-6-methoxy-3-pyridyl)amino]-2-oxo-acetate To a solution of 5-amino-2-methoxy-pyridine-3-carboxamide (10.06 g, 60.18 mmol) and triethylamine (6.09 g, 60.18 mmol, 8.39 mL) in dry THF (250 mL) was added 2,2,2-trifluoroethyl 2-chloro-2-oxo-acetate (12.04 g, 63.19 mmol) in 50 ml dry THF at 0° C. After stirring at rt for 12 hr the resulting mixture were evaporated to dryness to give 2,2,2-trifluoroethyl 2-[(5-carbamoyl-6-methoxy-3-pyridyl)amino]-2-oxo-acetate (29 g, crude) as a light-pink solid, which was used in the next step without further purification.
$^1$H NMR (DMSO-d$_6$, 500 MHz): δ 1.47 (s, 9H), 3.3 (s, 2H), 8.81 (s, 1H), 9.15 (s, 1H), 9.88 (s, 1H)
$^1$H NMR (DMSO-d$_6$, 400 MHz): δ 3.97 (s, 3H), 5.00 (q, 2H), 7.75 (brs, 2H), 8.55 (s, 1H), 8.63 (s, 1H), 11.21 (s, 1H)

Step 2: Synthesis of 2-[(5-carbamoyl-6-methoxy-3-pyridyl)amino]-2-oxo-acetic acid To a solution of 2,2,2-trifluoroethyl 2-[(5-carbamoyl-6-methoxy-3-pyridyl)amino]-2-oxo-acetate (15 g, 46.70 mmol) in MeOH (400 mL) was added Lithium hydroxide monohydrate, 98% (3.92 g, 93.40 mmol, 2.60 mL) and the resulting mixture was left to stir at rt for 1 hr. Then the resulting mixture was evaporated to dryness, dissolved in water. Water was acidified to pH=1 with water solution of hydrochloric acid and precipitate filtered. The precipitate was suspended in MeOH and Triethylamine (9.45 g, 93.40 mmol, 13.02 mL) was added until the solution became clear. The resulting mixture was evaporated to dryness to give 2-[(5-carbamoyl-6-methoxy-3-pyridyl)amino]-2-oxo-acetic acid (10.35 g, 30.41 mmol, 65.12% yield, Et$_3$N) as a beige solid.
$^1$H NMR (DMSO-d$_6$, 400 MHz): δ 1.17 (s, 12H), 3.06 (q, 6H), 3.92 (s, 3H), 7.70 (d, 2H), 8.60 (s, 1H), 10.34 (s, 1H), 10.34 (brs, 1H)

2D. The Synthesis of 2-[(5-chloro-6-methyl-3-pyridyl)amino]-2-oxo-acetic acid

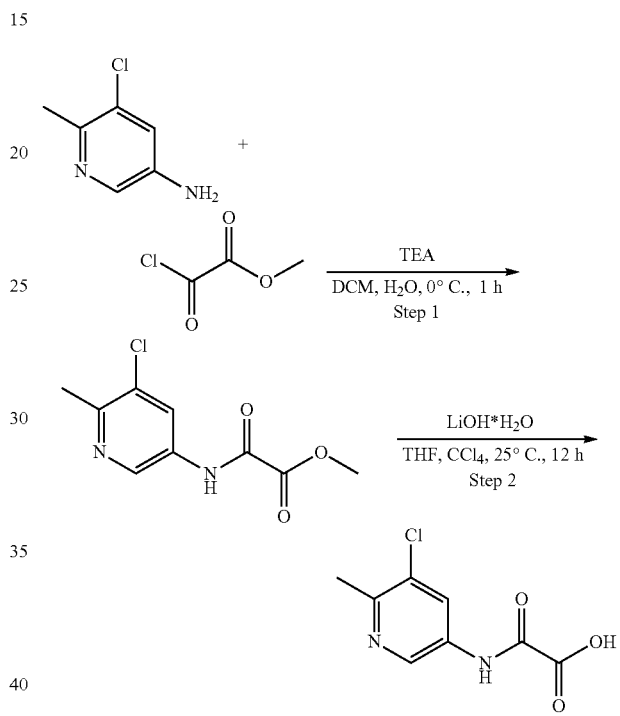

Step 1: The Synthesis of Methyl 2-[(5-chloro-6-methyl-3-pyridyl)amino]-2-oxo-acetate 5-chloro-6-methyl-pyridin-3-amine (3 g, 21.04 mmol) and TEA (2.13 g, 21.04 mmol, 2.93 mL) were dissolved in DCM (50 mL) and cooled to 0° C., following by the dropwise addition of methyl 2-chloro-2-oxo-acetate (2.84 g, 23.14 mmol, 2.13 mL). After the reaction was complete, the mixture was diluted with DCM (50 mL), washed with H$_2$O (40 mL) and brine (50 mL). Organic layer was dried over Na$_2$SO$_4$ and evaporated under reduced pressure to give methyl 2-[(5-chloro-6-methyl-3-pyridyl)amino]-2-oxo-acetate (3.5 g, 15.31 mmol, 72.76% yield).
$^1$H NMR (500 MHz, DMSO-d$_6$) δ 2.52 (s, 3H), 3.86 (s, 3H), 8.24 (s, 1H), 8.79 (s, 1H), 11.14 (s, 1H).

Step 2: The Synthesis of 2-[(5-chloro-6-methyl-3-pyridyl)amino]-2-oxo-acetic acid Methyl 2-[(5-chloro-6-methyl-3-pyridyl)amino]-2-oxoacetate (3.49 g, 15.26 mmol) was dissolved in THF (50 mL), followed by the addition of Lithium hydroxide monohydrate, 98% (768.26 mg, 18.31 mmol, 508.78 µL) and additional stirring overnight. After the reaction was complete, the mixture was filtered; the obtained solids was dried on air and re-evaporated to dryness with CCl4 (200 mL) to give 2-[(5-chloro-6-methyl-3-pyridyl)amino]-2-oxo-acetic acid (2.5 g, 11.28 mmol, 73.96% yield, Li+).

$^1$H NMR (400 MHz, DMSO-d$_6$) δ 2.43 (s, 3H), 8.28 (s, 1H), 8.73 (s, 1H), 10.47 (s, 1H).

LCMS(ESI): [M+H]$^+$ m/z: calcd 214.0; found 215.0; Rt=0.751 min.

2E. The Synthesis of 2,2,2-trifluoroethyl 2-[[6-(tert-butoxycarbonylamino)-5-ethyl-3-pyridyl]amino]-2-oxo-acetate and 2-[(6-amino-5-ethyl-3-pyridyl)amino]-2-oxo-acetic acid

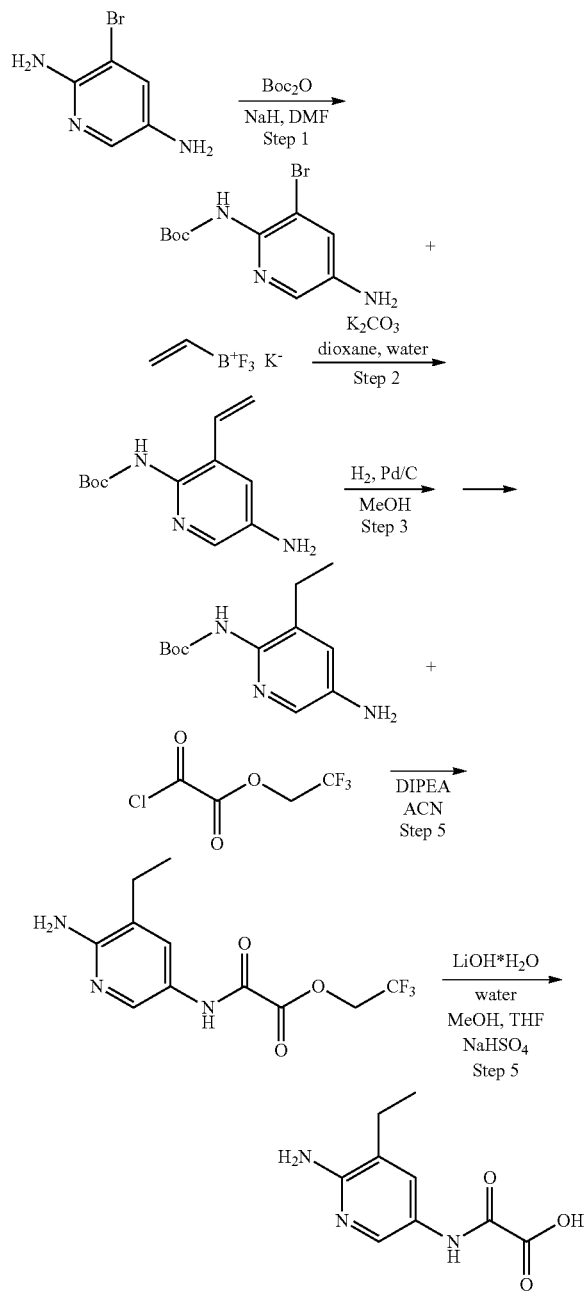

Step 1: Synthesis of tert-butyl N-(3-bromo-5-nitro-2-pyridyl)carbamate

To a solution of 3-bromo-5-nitro-pyridin-2-amine (30 g, 137.61 mmol) in DMF (200 mL), Sodium hydride (in oil dispersion) 60% dispersion in mineral oil (5.54 g, 138.42 mmol, 60% purity) was added portionwise at 0° C. The resulting mixture was stirred for 0.5 h (to the end of gas evolution) and a solution of Di-tert-butyl dicarbonate (31.53 g, 144.49 mmol, 33.16 mL) in DMF (50 mL) was added dropwise. The resulting mixture was stirred at 25° C. for 12 hr. The mixture was quenched with water (1000 ml), the precipitate was filtered and dissolved in EtOAc (900 ml)+ THF (100 ml), washed with brine (2*300 ml), dried over Na$_2$SO$_4$ and evaporated in vacuo to obtain precipitate of white crystals. This precipitate was filtered, washed with EtOAc (30 ml), MTBE (2*50 ml) and dried to obtain tert-butyl N-(3-bromo-5-nitro-2-pyridyl)carbamate (32 g, 100.59 mmol, 73.10% yield).

$^1$H NMR (DMSO-d6, 500 MHz): δ 1.47 (s, 9H), 3.3 (s, 2H), 8.81 (s, 1H), 9.15 (s, 1H), 9.88 (s, 1H)

LCMS(ESI): [M-CH2C(CH3)+H]$^+$ m/z: calcd 318.1; found 264.0; Rt=1.152 min.

Step 2: Synthesis of tert-butyl N-(5-nitro-3-vinyl-2-pyridyl)carbamate

A solution of tert-butyl N-(3-bromo-5-nitro-2-pyridyl)carbamate (27 g, 84.87 mmol), Potassium vinyltrifluoroborate (13.64 g, 101.85 mmol) and Potassium carbonate (58.65 g, 424.36 mmol, 25.61 mL) in Dioxane (400 mL) and Water (100 mL) was evacuated and refiled with argon three time. To this solution was added [1,1'-Bis(diphenylphosphino)ferrocene]dichloropalladium(II), complex with dichloromethane (3.47 g, 4.24 mmol) and resulting mixture was stirred at 80° C. for 2 hr. The resulting mixture was cooled, filtered, the solvent was removed. The residue was taken up with water (350 ml) and extracted with EtOAc-THF 9:1 (3*300 ml). The organic layer was dried over Na$_2$SO$_4$. 90% of the solvent was removed and formed precipitate was filtered, washed with MTBE and dried to give tert-butyl N-(5-nitro-3-vinyl-2-pyridyl)carbamate (13.5 g, 50.89 mmol, 59.96% yield).

$^1$H NMR (DMSO-d6, 400 MHz): δ 1.45 (s, 9H), 3.3 (s, 2H), 5.54 (d, 1H), 6.06 (d, 1H), 6.75 (dd, 1H), 8.07 (s, 1H), 9.08 (s, 1H), 9.93 (s, 1H)

LCMS(ESI): [M-CH2C(CH3)+H]$^+$ m/z: calcd 265.1; found 210.0; Rt=1.311 min.

Step 3: Synthesis of tert-butyl N-(5-amino-3-ethyl-2-pyridyl)carbamate

To a solution of tert-butyl N-(5-nitro-3-vinyl-2-pyridyl)carbamate (13 g, 49.01 mmol) in Methanol (400 mL), Palladium, 10% on carbon (52.15 g, 49.01 mmol, 10% purity) was added. The resulting mixture was stirred under hydrogen atmosphere at 25° C. for 24 hr. The catalyst was filtered and the solvent was evaporated in vacuo, the residue was dissolved in ACN (150 ml) and evaporated in vacuo to obtain tert-butyl N-(5-amino-3-ethyl-2-pyridyl)carbamate (11 g, 46.36 mmol, 94.59% yield).

$^1$H NMR (DMSO-d6, 400 MHz): δ 1.03 (t, 3H), 1.36 (s, 9H), 2.37 (q, 2H), 3.3 (s, 2H), 6.76 (s, 1H), 7.52 (s, 1H), 8.40 (s, 1H)

LCMS(ESI): [M+H]$^+$ m/z: calcd 237.3; found 238.2; Rt=0.901 min.

Step 4: Synthesis of 2,2,2-trifluoroethyl 2-[[6-(tert-butoxycarbonylamino)-5-ethyl-3-pyridyl]amino]-2-oxo-acetate To a solution of tert-butyl N-(5-amino-3-ethyl-2-pyridyl) carbamate (11 g, 46.36 mmol) and DIPEA (8.99 g, 69.53 mmol, 12.11 mL) in ACN (350 mL) was added 2,2,2-trifluoroethyl 2-chloro-2-oxo-acetate (10.16 g, 53.31 mmol) dropwise at 0° C. under argon. The reaction mixture was then stirred for 24 hr at r.t., then evaporated in vacuo, the residue was diluted with water (575 mL). The precipitate was triturated for 24 h, formed was filtered off, washed with water, EtOAc and dried in vacuo to provide the product 2,2,2-trifluoroethyl 2-[[6-(tert-butoxycarbonylamino)-5-ethyl-3-pyridyl]amino]-2-oxo-acetate (13 g, crude).
LCMS spectra showed mixture desired product and Boc-deprotected product.
This product was used for the next step without purification.

Step 4: Synthesis of 2-[(6-amino-5-ethyl-3-pyridyl)amino]-2-oxo-acetic acid

Starting material was partially Boc-deprotected according to LCMS.
To a solution of 2,2,2-trifluoroethyl 2-[[6-(tert-butoxycarbonylamino)-5-ethyl-3-pyridyl]amino]-2-oxo-acetate (13 g, 33.22 mmol) in Methanol (100 mL) and THF (100 mL), a solution of Lithium hydroxide, monohydrate (2.79 g, 66.44 mmol, 1.85 mL) in Water (200 mL) was added. The resulting mixture was stirred at 0° C. for 3 hr, organic solvents were removed, aqueous solution was acidified with solution of Sodium bisulfate monohydrate (9.63 g, 69.76 mmol) in Water (50 mL). Formed precipitate was filtered and dried to obtain 2-[(6-amino-5-ethyl-3-pyridyl)amino]-2-oxo-acetic acid (8.7 g, crude).
NMR spectra was taken in CD30D as solvent with adding $Et_3N$. This compound was used for the next step without purification.
$^1$H NMR (CD30D, 400 MHz): δ 1.22 (t, 3H), 2.47 (q, 2H), 7.65 (s, 1H), 8.19 (s, 1H)

2F. The Synthesis of 2-[[6-methyl-5-(trifluoromethyl)-3-pyridyl]amino]-2-oxo-acetic acid

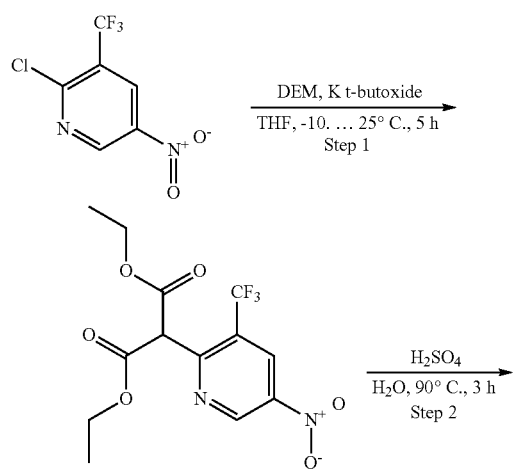

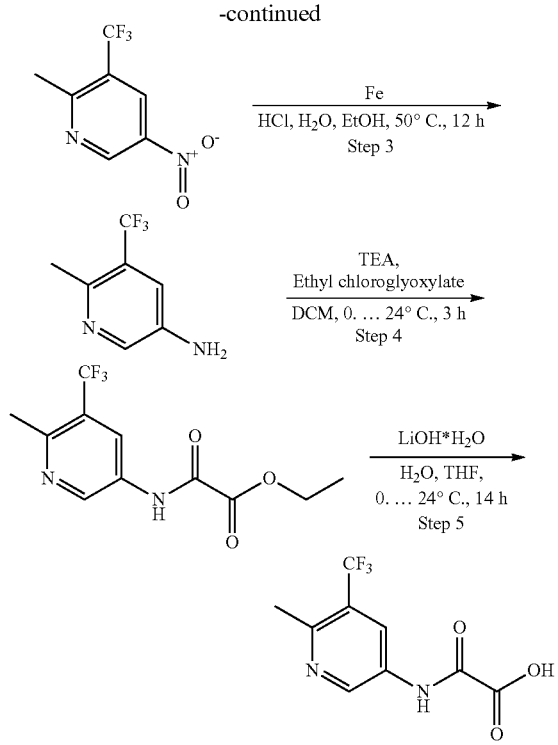

Step 1: The Synthesis of Diethyl 2-[5-nitro-3-(trifluoromethyl)-2-pyridyl]propanedioate To a stirred solution of diethyl propanedioate (1.41 g, 8.83 mmol, 1.33 mL) in THF (50 mL) was added potassium tert-butoxide (2.97 g, 26.49 mmol) at −10° C. and the mixture was stirred 10 min at the same temperature followed by 30 min at rt. 2-chloro-5-nitro-3-(trifluoromethyl)pyridine (2 g, 8.83 mmol) was added slowly to the mixture at 0° C. and the resultant mixture was stirred for 4 hr at rt. The mixture was quenched with aqueous ammonium chloride solution and extracted twice with ethyl acetate. The combined organic layers were washed with water followed by brine and dried over anhydrous sodium sulfate. The solution was filtered, concentrated to afford to diethyl 2-[5-nitro-3-(trifluoromethyl)-2-pyridyl]propanedioate (2.3 g, 6.57 mmol, 74.38% yield). The crude amine was as such carried forward to the next step.
$^1$H NMR (500 MHz, DMSO-$d_6$) δ 1.15 (m, 6H), 4.18 (m, 4H), 5.37 (s, 1H), 8.87 (s, 1H), 9.63 (s, 1H).
LCMS(ESI): [M+H]$^+$ m/z: calcd 350.1; found 351.0; Rt=1.379 min.

Step 2: The Synthesis of 2-methyl-5-nitro-3-(trifluoromethyl)pyridine

A solution of diethyl 2-[5-nitro-3-(trifluoromethyl)-2-pyridyl]propanedioate (2.3 g, 6.57 mmol) in water (23 mL) and $H_2SO_4$ (23 mL) was heated at 90° C. for 2-3 hr. The mixture was cooled to 0° C. and basified with 3N NaOH solution. The aqueous solution was extracted twice with DCM. The combined organic layers were washed with brine and dried over anhydrous sodium sulfate. The solution was filtered, concentrated to afford to 2-methyl-5-nitro-3-(trifluoromethyl)pyridine (0.6 g, 2.91 mmol, 44.33% yield).

$^1$H NMR (500 MHz, DMSO-d$_6$) δ 2.77 (s, 3H), 8.71 (s, 1H), 9.48 (s, 1H).
GCMS(EI): [M+H]$^+$ m/z: calcd 206.0; found 206.0; Rt=5.223 min.

Step 3: The Synthesis of 6-methyl-5-(trifluoromethyl)pyridin-3-amine

To a solution of 2-methyl-5-nitro-3-(trifluoromethyl)pyridine (0.6 g, 2.91 mmol) in HCl (0.1 mL), water (1 mL) and EtOH (10 mL) iron (1.30 g, 23.29 mmol, 165.45 µL) was added at 50° C. by portions. After that resulting mixture was stirred overnight. The solution was filtered through silica gel and evaporated to afford to 6-methyl-5-(trifluoromethyl)pyridin-3-amine (0.5 g, 2.84 mmol, 97.52% yield).
$^1$H NMR (400 MHz, DMSO-d$_6$) δ 2.37 (s, 3H), 5.52 (s, 2H), 7.15 (s, 1H), 7.99 (s, 1H).
LCMS(ESI): [M+H]$^+$ m/z: calcd 176.1; found 177.2; Rt=0.711 min.

Step 4: The Synthesis of ethyl 2-[[6-methyl-5-(trifluoromethyl)-3-pyridyl]amino]-2-oxo-acetate To solution 6-methyl-5-(trifluoromethyl)pyridin-3-amine (0.5 g, 2.84 mmol) in DCM (10 mL) TEA (344.69 mg, 3.41 mmol, 474.79 µL) was added. After that the solution was cooled at 0° C. and ethyl 2-chloro-2-oxoacetate (465.09 mg, 3.41 mmol, 381.22 µL) was added dropwise. The resulting mixture was stirred at rt 3 hr. The reaction mixture was washed with water and brine, dried over anhydrous sodium sulfate. The solution was filtered, concentrated to afford to ethyl 2-[[6-methyl-5-(trifluoromethyl)-3-pyridyl]amino]-2-oxo-acetate (0.68 g, 2.46 mmol, 86.73% yield).
$^1$H NMR (500 MHz, DMSO-d$_6$) δ 1.30 (t, 3H), 2.58 (s, 3H), 4.32 (q, 2H), 8.46 (s, 1H), 9.04 (s, 1H), 11.23 (s, 1H).
LCMS(ESI): [M+H]$^+$ m/z: calcd 276.1; found 277.2; Rt=1.045 min.

Step 5: The Synthesis of 2-[[6-methyl-5-(trifluoromethyl)-3-pyridyl]amino]-2-oxo-acetic acid A solution of ethyl 2-[[6-methyl-5-(trifluoromethyl)-3-pyridyl]amino]-2-oxo-acetate (0.68 g, 2.46 mmol) in water (5 mL) and THF (5 mL) was cooled. Lithium hydroxide, monohydrate (123.97 mg, 2.95 mmol, 82.10 µL) was added at 0° C. Then reaction mixture was stirred at rt overnight. The organic solvent was roto-evaporated. The residue was acidified with HCl to pH 2 and filtered on to afford 2-[[6-methyl-5-(trifluoromethyl)-3-pyridyl]amino]-2-oxo-acetic acid (2.5 g, 10.72 mmol, 56.01% yield).
$^1$H NMR (400 MHz, DMSO-d$_6$) δ 2.58 (s, 3H), 8.51 (s, 1H), 9.06 (s, 1H), 11.14 (s, 1H).
LCMS(ESI): [M+H]$^+$ m/z: calcd 248.0; found 249.2; Rt=0.729 min.

2G. The Synthesis of 2-[[5-methyl-6-(trifluoromethyl)-3-pyridyl]amino]-2-oxo-acetic acid

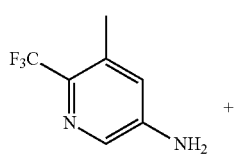
+

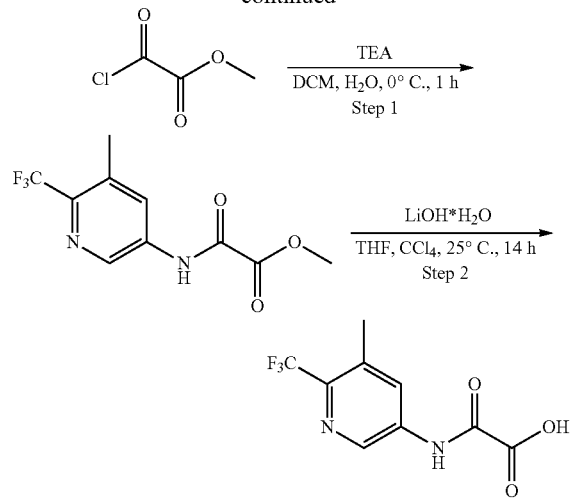

Step 1: The Synthesis of Methyl 2-[[5-methyl-6-(trifluoromethyl)-3-pyridyl]amino]-2-oxo-acetate 5-methyl-6-(trifluoromethyl)pyridin-3-amine (3.00 g, 17.03 mmol) and TEA (1.72 g, 17.03 mmol, 2.37 mL) were dissolved in DCM (50 mL) and cooled to 0° C., following by the dropwise addition of methyl 2-chloro-2-oxo-acetate (2.30 g, 18.74 mmol, 1.73 mL). After the reaction was complete, the mixture was diluted with DCM (50 mL), washed with H$_2$O (40 mL) and brine (50 mL). Organic layer was dried over Na$_2$SO$_4$ and evaporated under reduced pressure to give methyl 2-[[5-methyl-6-(trifluoromethyl)-3-pyridyl]amino]-2-oxo-acetate (4 g, 15.26 mmol, 89.57% yield).
$^1$H NMR (500 MHz, DMSO-d$_6$) δ 2.49 (s, 3H), 3.87 (s, 3H), 8.28 (s, 1H), 8.86 (s, 1H), 11.20 (s, 1H).

Step 2: The Synthesis of 2-[[5-methyl-6-(trifluoromethyl)-3-pyridyl]amino]-2-oxo-acetic acid Methyl 2-[[5-methyl-6-(trifluoromethyl)-3-pyridyl]amino]-2-oxo-acetate (4 g, 15.26 mmol) was dissolved in THF (50 mL), followed by the addition of Lithium hydroxide monohydrate, 98% (768.26 mg, 18.31 mmol, 508.78 µL) and additional stirring overnight. After the reaction was complete, the mixture was filtered; the obtained solids was dried on air and re-evaporated to dryness with CCl$_4$ (200 mL) to give 2-[[5-methyl-6-(trifluoromethyl)-3-pyridyl]amino]-2-oxo-acetic acid (3.4 g, 13.33 mmol, 87.36% yield, Li+).
$^1$H NMR (400 MHz, DMSO-d$_6$) δ 2.38 (s, 3H), 8.25 (s, 1H), 8.82 (s, 1H), 10.56 (s, 1H).
LCMS(ESI): [M+H]$^+$ m/z: calcd 248.0; found 249.0; Rt=0.948 min.

2H. The Synthesis of 2-[[6-(difluoromethyl)-5-methyl-3-pyridyl]amino]-2-oxo-acetic acid

+

-continued

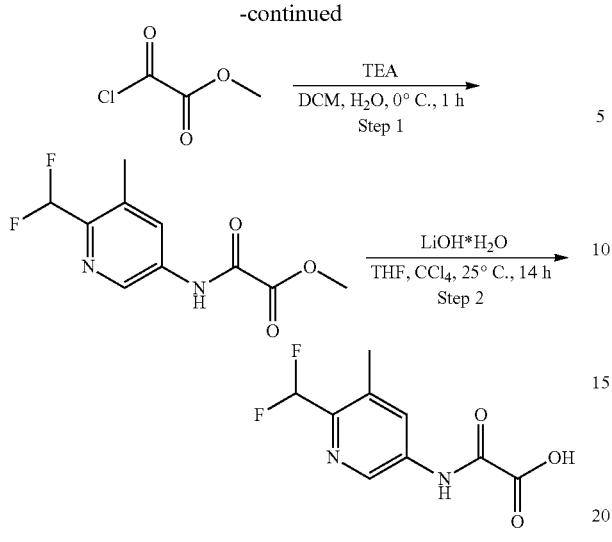

Step 1: The Synthesis of Methyl 2-[[6-(difluoromethyl)-5-methyl-3-pyridyl]amino]-2-oxo-acetate 6-(difluoromethyl)-5-methyl-pyridin-3-amine (3 g, 18.97 mmol) and TEA (1.92 g, 18.97 mmol, 2.64 mL) were dissolved in DCM (50 mL) and cooled to 0° C., following by the dropwise addition of methyl 2-chloro-2-oxo-acetate (2.56 g, 20.87 mmol, 1.92 mL). After the reaction was complete, the mixture was diluted with DCM (50 mL), washed with H$_2$O (40 mL) and brine (50 mL). Organic layer was dried over Na$_2$SO$_4$ and evaporated under reduced pressure to give methyl 2-[[6-(difluoromethyl)-5-methyl-3-pyridyl]amino]-2-oxo-acetate (3.3 g, 13.51 mmol, 71.24% yield).

$^1$H NMR (500 MHz, DMSO-d$_6$) δ 2.43 (s, 3H), 3.87 (s, 3H), 6.98 (t, 1H), 8.16 (s, 1H), 8.80 (s, 1H), 11.19 (s, 1H).

Step 2: The Synthesis of 2-[[6-(difluoromethyl)-5-methyl-3-pyridyl]amino]-2-oxo-acetic acid Methyl 2-[[6-(difluoromethyl)-5-methyl-3-pyridyl]amino]-2-oxo-acetate (3.3 g, 13.51 mmol) was dissolved in THF (50 mL), followed by the addition of Lithium hydroxide monohydrate, 98% (680.45 mg, 16.22 mmol, 450.63 µL) and additional stirring overnight. After the reaction was complete, the mixture was filtered; the obtained solids was dried on air and re-evaporated to dryness with CCl$_4$ (200 mL) to give 2-[[6-(difluoromethyl)-5-methyl-3-pyridyl]amino]-2-oxo-acetic acid (2.2 g, 9.28 mmol, 68.66% yield, Li$^+$).

$^1$H NMR (400 MHz, DMSO-d$_6$) δ 2.28 (s, 3H), 6.75 (t, 1H), 8.02 (s, 1H), 8.34 (s, 1H), NH and OH aren't observed.

LCMS(ESI): [M+H]$^+$ m/z: calcd 230.0; found 231.0; Rt=0.807 min.

2I. The Synthesis of 2-[[5-(difluoromethyl)-6-methyl-3-pyridyl]amino]-2-oxo-acetic acid

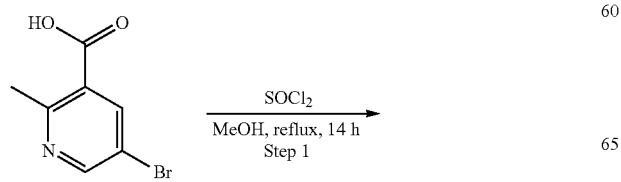

-continued

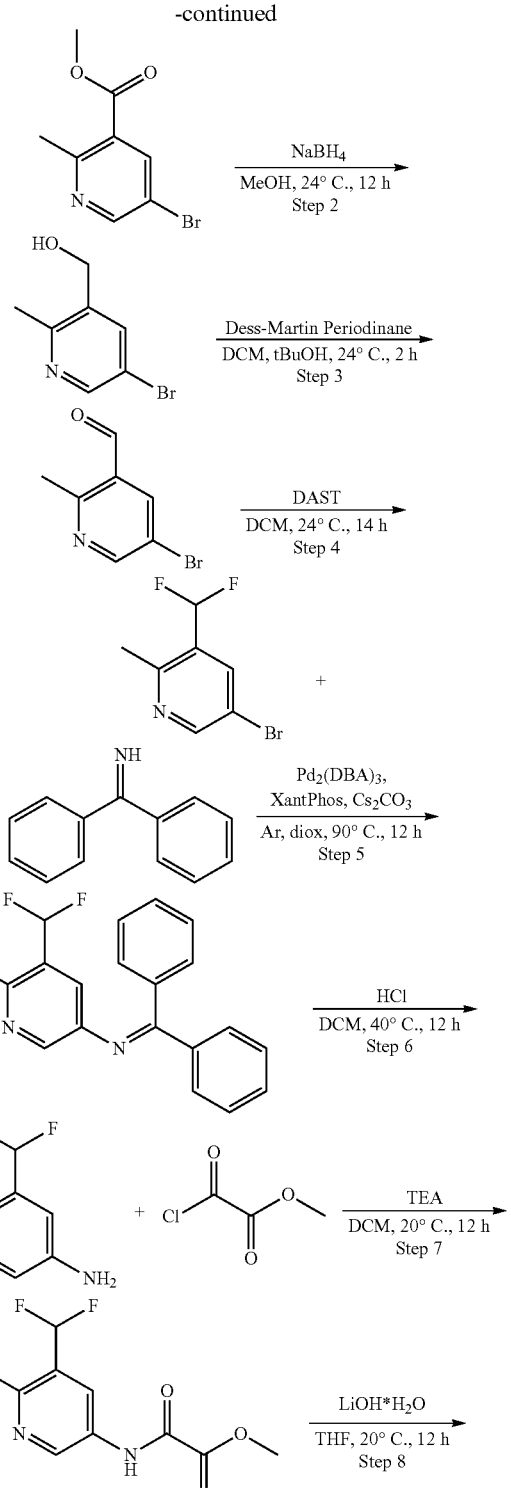

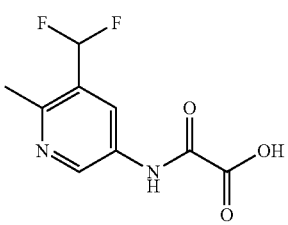

Step 1: The Synthesis of Methyl 5-bromo-2-methyl-pyridine-3-carboxylate 5-bromo-2-methyl-pyridine-3-carboxylic acid (4 g, 18.52 mmol) was dissolved in MeOH (100 mL) and thionyl chloride (6.61 g, 55.55 mmol, 4 mL) was added dropwise, the reaction mixture was refluxed overnight. The reaction mixture was concentrated on vacuo, obtained residue was dissolved in DCM and washed with $Na_2CO_3$(aq), water, dried over $Na_2SO_4$, filtered and evaporated on vacuo to give methyl 5-bromo-2-methyl-pyridine-3-carboxylate (3.54 g, 15.39 mmol, 83.10% yield) which was used in the next step without further purification.

$^1$H NMR (500 MHz, $CDCl_3$) δ 2.78 (s, 3H), 3.92 (s, 3H), 8.32 (s, 1H), 8.66 (s, 1H).

LCMS(ESI): $[M+H]^+$ m/z: calcd 229.0; found 230.0; Rt=1.231 min.

Step 2: The Synthesis of (5-bromo-2-methyl-3-pyridyl)methanol

Methyl 5-bromo-2-methyl-pyridine-3-carboxylate (3.54 g, 15.39 mmol) was dissolved in MeOH (60 mL) and sodium borohydride (1.75 g, 46.16 mmol, 1.63 mL) was added portionwise under cooling with icewater. The reaction mixture was heated to RT and stirred for 12 hr. $NH_4Cl$ (aq.) was added and methanol was evaporated, aqueous layer was extracted with DCM (3*30 ml) and combined organic layer was dried over $Na_2SO_4$, filtered and evaporated on vacuo at 45° C. to give (5-bromo-2-methyl-3-pyridyl)methanol (2.5 g, 12.37 mmol, 80.41% yield) which was used in the next step without further purification.

$^1$H NMR (500 MHz, $CDCl_3$) δ 2.41 (s, 3H), 4.72 (s, 2H), 7.86 (s, 1H), 8.32 (s, 1H).

LCMS(ESI): $[M+2H]^+$ m/z: calcd 202.0; found 204.0; Rt=0.678 min.

Step 3: The Synthesis of 5-bromo-2-methyl-pyridine-3-carbaldehyde

A slurry of Dess-Martin Periodinane (8.79 g, 20.71 mmol) in DCM (15 mL) was treated with $^t$BuOH (2 mL), and the mixture was stirred at room temperature for 15 min then a solution of (5-bromo-2-methyl-3-pyridyl)methanol (3.1 g, 15.34 mmol) in DCM (15 mL) was added over 5 min. The mixture was stirred at room temperature for 2 hr then diluted with ethyl acetate and 1 N NaOH solution, and stirred for 10 min. The layers were separated and the organic layer was washed with water, brine, dried over $Na_2SO_4$, filtered and concentrated to give 5-bromo-2-methyl-pyridine-3-carbaldehyde (3.1 g, crude) which was used in the next step without further purification.

$^1$H NMR (500 MHz, $CDCl_3$) δ 2.83 (s, 3H), 8.17 (s, 1H), 8.72 (s, 1H), 10.27 (s, 1H).

Step 4: The Synthesis of 5-bromo-3-(difluoromethyl)-2-methyl-pyridine

To a solution of 5-bromo-2-methyl-pyridine-3-carbaldehyde (3.1 g, 15.50 mmol) in diethylaminosulfur trifluoride (19.98 g, 123.98 mmol, 16.38 mL)DCM (120 mL) at room temperature was added diethylaminosulfur trifluoride (19.98 g, 123.98 mmol, 16.38 mL). The resulting reaction mixture was stirred at room temperature overnight then concentrated to give 5-bromo-3-(difluoromethyl)-2-methyl-pyridine (1.90 g, 8.57 mmol, 55.28% yield) which was used in the next step without further purification.

$^1$H NMR (400 MHz, $CDCl_3$) δ 2.55 (s, 3H), 6.71 (t, 1H), 7.91 (s, 1H), 8.77 (s, 1H).

Step 5: The Synthesis of N-[5-(difluoromethyl)-6-methyl-3-pyridyl]-1,1-diphenyl-methanimine A mixture of 5-bromo-3-(difluoromethyl)-2-methyl-pyridine (1.55 g, 6.98 mmol), diphenylmethanimine (1.39 g, 7.68 mmol, 1.29 mL), Xantphos (1.21 g, 2.09 mmol), $Pd_2(dba)_3$ (319.64 mg, 349.05 μmol) and cesium carbonate (6.82 g, 20.94 mmol) in dioxane (100 mL) was degassed by bubbling argon into the mixture for several minutes. The reaction mixture was stirred at 90° C. for 12 hr under Ar atmosphere. The reaction mixture was cooled to room temperature and filtered. The filtrate was concentrated in vacuo and the residue was diluted with water. The mixture was extracted with ethyl acetate. The combined organic layers were washed with water, dried over $Na_2SO_4$, filtered and concentrated to give N-[5-(difluoromethyl)-6-methyl-3-pyridyl]-1,1-diphenyl-methanimine (3.8 g, crude) which was used in the next step without further purification.

$^1$H NMR (500 MHz, $CDCl_3$) δ 2.52 (s, 3H), 6.64 (t, 1H), 6.75 (s, 1H), 7.36 (m, 10H), 7.98 (s, 1H)

LCMS(ESI): $[M+H]^+$ m/z: calcd 322.1; found 323.2; Rt=1.358 min.

Step 6: The Synthesis of 5-(difluoromethyl)-6-methyl-pyridin-3-amine

N-[5-(difluoromethyl)-6-methyl-3-pyridyl]-1,1-diphenyl-methanimine (3.8 g, 11.79 mmol) was dissolved in DCM (20 mL) and HCl (1 M) (20 mL) and stirred at 40° C. for 12 hr. The DCM layer was separated, water was washed with additional DCM, the aqueous layer was basified with $Na_2CO_3$ and extracted with DCM twice, the combined DCM after basification was dried over $Na_2SO_4$, filtered and evaporated to give 5-(difluoromethyl)-6-methyl-pyridin-3-amine (0.715 g, 4.52 mmol, 38.35% yield) which was used in the next step without further purification.

$^1$H NMR (400 MHz, $CDCl_3$) δ 2.48 (s, 3H), 3.65 (s, 2H), 6.69 (t, 1H), 7.11 (s, 1H), 8.06 (s, 1H).

LCMS(ESI): $[M+H]^+$ m/z: calcd 158.1; found 159.0; Rt=0.346 min.

Step 7: The Synthesis of Methyl 2-[[5-(difluoromethyl)-6-methyl-3-pyridyl]amino]-2-oxo-acetate 5-(difluoromethyl)-6-methyl-pyridin-3-amine (0.79 g, 5.00 mmol) and TEA (505.48 mg, 5.00 mmol, 696.25 μL) were dissolved in DCM (15 mL) and cooled to 20° C., following by the dropwise addition of methyl 2-chloro-2-oxo-acetate (673.16 mg, 5.49 mmol) and the reaction mixture was stirred for 12 hr at 20° C. The mixture was diluted with DCM, washed with water and brine (50 mL). Organic layer was dried over $Na_2SO_4$ and evaporated under reduced pressure to give methyl 2-[[5-(difluoromethyl)-6-methyl-3-pyridyl]amino]-2-oxo-acetate (1.22 g, 5.00 mmol, 100.00% yield).

$^1$H NMR (400 MHz, $CDCl_3$) δ 2.66 (s, 3H), 3.99 (s, 3H), 6.79 (t, 1H), 8.30 (s, 1H), 8.78 (s, 1H), 9.09 (s, 1H).

LCMS(ESI): $[M+H]^+$ m/z: calcd 244.1; found 245.0; Rt=0.777 min.

Step 8: The Synthesis of 2-[[5-(difluoromethyl)-6-methyl-3-pyridyl]amino]-2-oxo-acetic acid Methyl 2-[[5-(difluoromethyl)-6-methyl-3-pyridyl]amino]-2-oxo-acetate (1.22 g, 5.00 mmol) was dissolved in THF (20 mL), followed by the addition of Lithium hydroxide monohydrate, 98% (251.56 mg, 6.00 mmol, 166.60 µL) and the reaction mixture was stirred for 12 hr at 20° C. The reaction mixture was filtered, the obtained solids were dried on air and re-evaporated to dryness with CCl$_4$ to give 2-[[5-(difluoromethyl)-6-methyl-3-pyridyl]amino]-2-oxo-acetic acid (1.09 g, 4.60 mmol, 92.01% yield, Li)

LCMS(ESI): [M+H]$^+$ m/z: calcd 230.0; found 231.0; Rt=0.558 min.

LCMS(ESI): [M+H]$^+$ m/z: calcd 456.2; found 457.2; Rt=1.022 min.

2J. The Synthesis of 5-iodo-3-(oxetan-3-yl)pyridin-2-amine

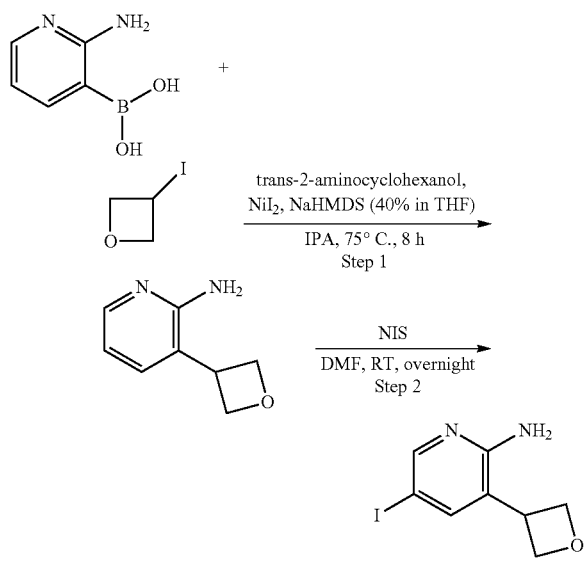

Step 1: The Synthesis of 3-(oxetan-3-yl)pyridin-2-amine trans-2-aminocyclohexanol (198.13 mg, 1.72 mmol) and Nickel (II) iodide (537.58 mg, 1.72 mmol) were added to a solution of (2-amino-3-pyridyl)boronic acid (5 g, 28.67 mmol, HCl) in isopropyl alcohol (50 mL). Then, Sodium bis(trimethylsilyl)amide (40% in THF) (39.43 g, 86.01 mmol, 44.11 mL, 40% purity) was added dropwise followed by 3-iodooxetane (7.91 g, 43.01 mmol, 3.70 mL). The reaction flask was purged with argon and the resulting mixture was stirred at 75° C. for 8 hr. The volatiles were removed under reduced pressure and residue was purified by gradient column chromatography. Companion combiflash; 80 g SiO$_2$, CHCl$_3$-MeOH from 0~100%, flow rate=60 mL/min, cv=5

3-(oxetan-3-yl)pyridin-2-amine (1 g, 6.66 mmol, 23.22% yield) was obtained as yellow oil.

$^1$H NMR (400 MHz, DMSO-d$_6$) δ 4.12 (q, 1H), 4.62 (dd, 2H), 4.90 (dd, 2H), 5.69 (s, 2H), 6.62 (dd, 1H), 7.45 (s, 1H), 7.83 (s, 1H).

LCMS(ESI): [M+H]$^+$ m/z: calcd 150.2; found 151.0; Rt=0.166 min.

Step 2: The Synthesis of 5-iodo-3-(oxetan-3-yl)pyridin-2-amine 3-(oxetan-3-yl)pyridin-2-amine (0.8 g, 5.33 mmol) was dissolved in DMFA (15 mL) followed by portion-wise addition of 1-iodopyrrolidine-2,5-dione (1.60 g, 7.11 mmol). The reaction mixture was stirred overnight and concentrated under reduced pressure. The residue was dissolved in DCM and the organic layer was washed with Na$_2$S$_2$O$_3$ aqueous solution and water multiple times. DCM layer was separated, dried over Na$_2$SO$_4$ and concentrated under reduced pressure. Pure 5-iodo-3-(oxetan-3-yl)pyridin-2-amine (0.6 g, 2.17 mmol, 40.80% yield) was obtained as yellow solid.

$^1$H NMR (400 MHz, DMSO-d$_6$) δ 4.15 (q, 1H), 4.56 (dd, 2H), 4.87 (dd, 2H), 5.87 (s, 1H), 7.66 (s, 1H), 7.98 (s, 1H).

LCMS(ESI): [M+H]$^+$ m/z: calcd 277.0; found 277.0; Rt=0.563 min.

2K. The Synthesis of 2-[(5-carbamoyl-6-methyl-3-pyridyl)amino]-2-oxo-acetic acid Step 1. Synthesis of 2-benzyloxy-5-bromo-pyridine

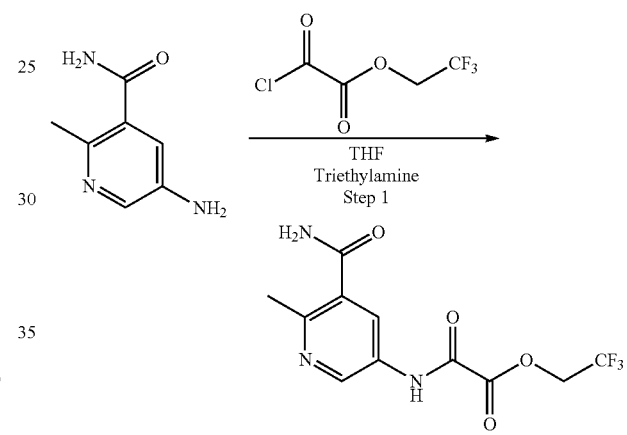

To a solution of 5-amino-2-methyl-pyridine-3-carboxamide (975 mg, 6.45 mmol) and triethylamine (652.66 mg, 6.45 mmol, 898.99 µL) in THF (25 mL) was added 2,2,2-trifluoroethyl 2-chloro-2-oxo-acetate (1.23 g, 6.45 mmol) at 0° C. After stirring at 20° C. for 18 hr the resulting mixture were evaporated to dryness to give 2,2,2-trifluoroethyl 2-[(5-carbamoyl-6-methyl-3-pyridyl)amino]-2-oxo-acetate (2.21 g, crude) as a yellow solid, which was used in the next step without further purification.

LCMS(ESI): [M+1]+m/z: calcd 305.2; found 306.0; Rt=0.714 min.

Step 2. Synthesis of 2-[(5-carbamoyl-6-methyl-3-pyridyl)amino]-2-oxo-acetic acid

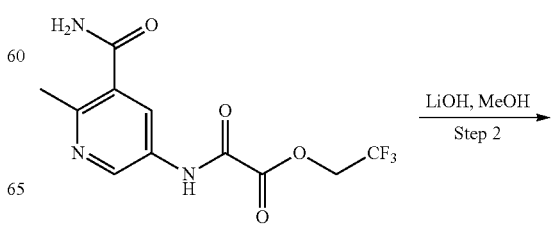

-continued

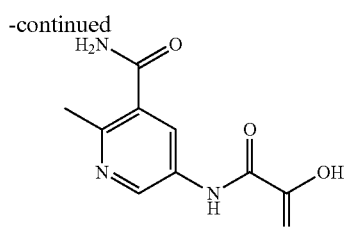

To a solution of 2,2,2-trifluoroethyl 2-[(5-carbamoyl-6-methyl-3-pyridyl)amino]-2-oxo-acetate (440 mg, 1.44 mmol) in MeOH (10 mL) was added Lithium hydroxide monohydrate, 98% (120.98 mg, 2.88 mmol, 80.12 μL) and the resulting mixture was left to stir at rt for 1 hr. Then the resulting mixture was evaporated to dryness, dissolved in water, washed with DCM three times. Water was acidified to pH=1 and precipitate filtered and rinsed with water (2*10 ml), EA (25 ml), and air-dried to obtain 2-[(5-carbamoyl-6-methyl-3-pyridyl)amino]-2-oxo-acetic acid (96 mg, crude)

$^1$H NMR (400 MHz, DMSO-$d_6$) δ (ppm) 7.56 (s, 1H), 7.99 (s, 1H), 8.12 (s, 1H), 8.83 (s, 1H), 10.97 (s, 1H).

LCMS(ESI): [M+1]$^+$ m/z: calcd 223.2; found 224.0; Rt=0.174 min.

2L. The Synthesis of 2-[[5-carbamoyl-6-(trifluoromethoxy)-3-pyridyl]amino]-2-oxo-acetic acid The Synthesis of 2-[[5-carbamoyl-6-(trifluoromethoxy)-3-pyridyl]amino]-2-oxo-acetic acid

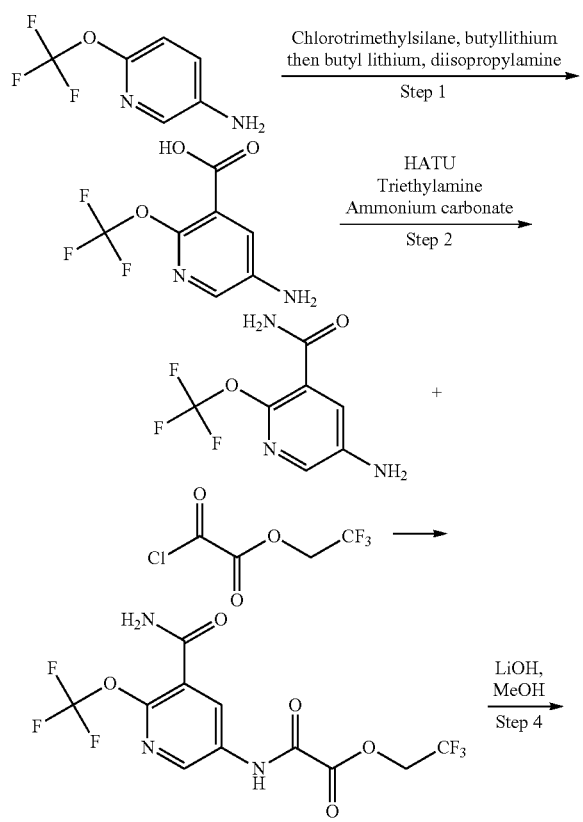

-continued

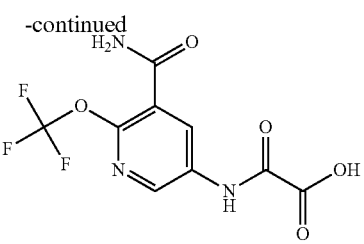

Step 1-2. Synthesis of 2-benzyloxy-5-bromo-pyridine

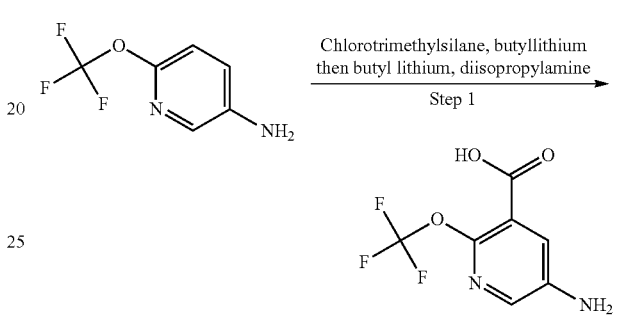

At −78° C., butyllithium (1.20 g, 18.75 mmol, 7.51 mL) was added dropwise to a solution of 6-(trifluoromethoxy)pyridin-3-amine (1.67 g, 9.38 mmol) in THF (20 mL) followed after 1 min by Chlorotrimethylsilane (2.14 g, 19.69 mmol, 2.50 mL). The reaction mixture was allowed to reach 25 OC for 2 hr before being filtrated onto a pad of celite. The solvent was removed and the crude oil was distilled under vacuum (101-103° C./1 mbar) to afford 6-(trifluoromethoxy)-N,N-bis(trimethylsilyl)pyridin-3-amine (2.93 g, crude). At 0° C. butyl lithium (1.18 g, 18.43 mmol, 7.38 mL) was added dropwise to a solution of diisopropylamine (1.95 g, 19.31 mmol, 2.72 mL) in THF (56 mL). At −78 0° C., a solution of 6-(trifluoromethoxy)-N,N-bis(trimethylsilyl)pyridin-3-amine (2.83 g, 8.78 mmol) in THF (2 mL) was added dropwise and the reaction mixture was stirred for 1 h at this temperature. Then $CO_2$ was sparged into solution through drying vessel with sulfuric acid for 15 min. After 30 min at −78° C. the solution was allowed to rt. The solvent was evaporated. Resulting crude material was purified by column chromatography (MTBE/Methanol) to obtain 5-amino-2-(trifluoromethoxy)pyridine-3-carboxylic acid (0.1 g, 450.20 umol, 5.13% yield)

$^1$H NMR (500 MHz, DMSO-$d_6$) δ (ppm) 5.20-5.30 (brs, 2H), 7.35 (s, 1H), 7.65 (s, 1H).

LCMS(ESI): [M+1]$^+$ m/z: calcd 222.0; found 223.0; Rt=0.641 min.

Step 2. Synthesis of 5-amino-2-(trifluoromethoxy)pyridine-3-carboxamide

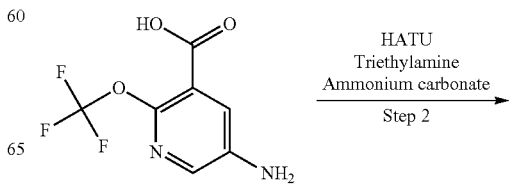

-continued

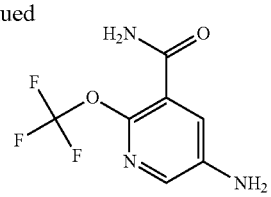

5-amino-2-(trifluoromethoxy)pyridine-3-carboxylic acid (90 mg, 405.18 umol), Ammonium carbonate (116.80 mg, 1.22 mmol), Triethylamine (205.00 mg, 2.03 mmol, 282.37 uL) were mixed in DMF (2 mL) and then HATU (231.09 mg, 607.78 umol) were added. Resulting mixture were stirred at 25° C. for 13 hr. The solvent was evaporated to obtain crude product that was purified by HPLC (35-55% (Methanol)—2-10 min Flow rate: 30 ml/min) to obtain 5-amino-2-(trifluoromethoxy)pyridine-3-carboxamide (18.9 mg, 85.47 umol, 21.09% yield)

$^1$H NMR (400 MHz, CDCl$_3$) δ (ppm) 5.19 (d, 1H), 5.37 (s, 2H), 5.65 (d, 1H), 6.63 (m, 1H), 6.78 (d, 1H), 7.24-7.63 (m, 5), 7.71 (d, 1H), 8.19 (s, 1H).

LCMS(ESI): [M+1]$^+$ m/z: calcd 221.0; found 222.0; Rt=0.727 min.

Step 3. 2,2,2-trifluoroethyl 2-[[5-carbamoyl-6-(trifluoromethoxy)-3-pyridyl]amino]-2-oxo-acetate

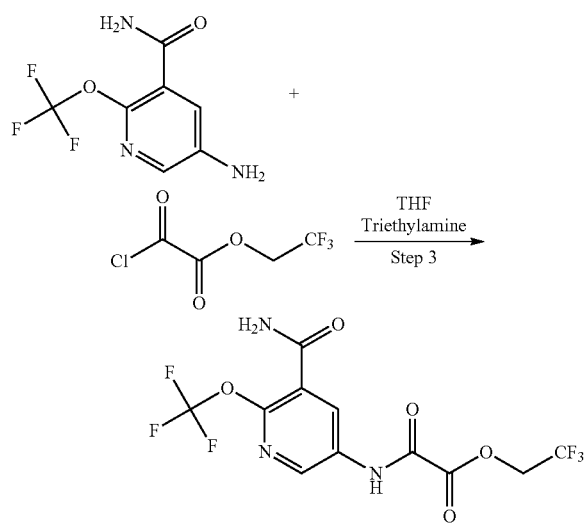

5-amino-2-(trifluoromethoxy)pyridine-3-carboxamide (318 mg, 1.44 mmol) and Triethylamine (145.51 mg, 1.44 mmol, 200.43 μL) were dissolved in THF (7 mL) and the resulting solution was cooled to 0° C. in an ice/methanol bath. A solution of 2,2,2-trifluoroethyl 2-chloro-2-oxo-acetate (273.95 mg, 1.44 mmol) in THF (0.5 mL) was added dropwise at 0° C. After addition completed, the reaction mixture was allowed to warm to room temperature and stirred overnight. The reaction mixture was concentrated in vacuo. The residue was transferred to a filter and rinsed with water (2*25 ml), DCM (25 ml), and air-dried to obtain 2,2,2-trifluoroethyl 2-[[5-carbamoyl-6-(trifluoromethoxy)-3-pyridyl]amino]-2-oxo-acetate (355 mg, 946.21 μmol, 65.80% yield).

$^1$H NMR (400 MHz, DMSO-d$_6$) δ (ppm) 4.97 (q, 2H), 7.74 (s, 1H), 7.92 (s, 1H), 8.42 (s, 1H), 8.72 (s, 1H), 11.36 (s, 1H).

LCMS(ESI): [M+1]$^+$ m/z: calcd 375.2; found 376.2; Rt=1.054 min.

Step 4. 2-[[5-carbamoyl-6-(trifluoromethoxy)-3-pyridyl]amino]-2-oxo-acetic acid

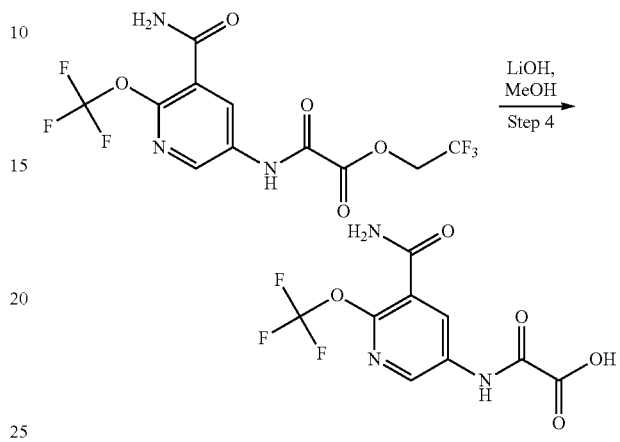

2,2,2-trifluoroethyl 2-[[5-carbamoyl-6-(trifluoromethoxy)-3-pyridyl]amino]-2-oxo-acetate (473.7 mg, 1.26 mmol) was dissolved in MeOH (15 mL) and Lithium hydroxide monohydrate, 98% (105.97 mg, 2.53 mmol, 70.18 μL) was added thereto. The resulting mixture was stirred for 1 hr. The reaction mixture was concentrated in vacuo and the residue was dissolved in water (10 ml). The resulting mixture was acidified with HCl and the precipitation was filtered, rinsed with water (10 ml), and air-dried to obtain 2-[[5-carbamoyl-6-(trifluoromethoxy)-3-pyridyl]amino]-2-oxo-acetic acid (232 mg, 791.39 μmol, 62.68% yield)

$^1$H NMR (400 MHz, DMSO-d$_6$) δ (ppm) 7.80 (s, 1H), 7.99 (s, 1H), 8.44 (s, 1H), 8.72 (s, 1H), 11.19 (s, 1H).

LCMS(ESI): [M+1]$^+$ m/z: calcd 293.2; found 294.2; Rt=0.728 min.

3. Miscellaneous Piperidine Intermediates Syntheses

3A. Synthesis of 5-methyl-2-(1-methyl-1H-pyrazol-5-yl)piperidine

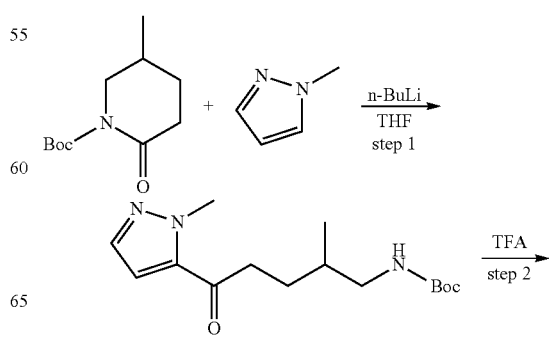

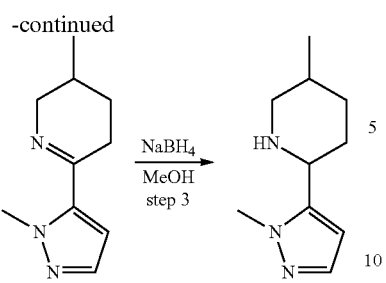

Step 1: Synthesis of tert-butyl (2-methyl-5-(1-methyl-1H-pyrazol-5-yl)-5-oxopentyl)carbamate n-Butyllithium (10.19 g, 36.57 mmol, 14.98 mL, 23% purity) (2.5 M in hexane) was added dropwise at −75° C. to a stirred solution of 1-methylpyrazole (3.00 g, 36.57 mmol, 3.04 mL) in THF (60 mL). The resulting heavy suspension was stirred at −75° C. for 1 hr, then tert-butyl 5-methyl-2-oxo-piperidine-1-carboxylate (7.8 g, 36.57 mmol) was added dropwise at −75° C. and the reaction mixture was allowed to warm to 0° C. and stirred for 1 hr. The resulting suspension was diluted with water (50 ml) and MTBE (100 ml), transferred to a separatory funnel, and the upper organic layer was separated. The aqueous layer was additionally extracted with MTBE (50 ml). The combined organic extracts were washed with water (20 ml), dried over sodium sulphate and evaporated in vacuo to afford tert-butyl N-[2-methyl-5-(2-methylpyrazol-3-yl)-5-oxo-pentyl]carbamate (9 g, 30.47 mmol, 83.31% yield) as yellow oil, which was used directly in the next step.

$^1$H NMR (400 MHz, CDCl$_3$) δ (ppm) 0.95 (d, 3H), 1.44 (s, 9H), 1.78 (m, 2H), 2.88 (m, 2H), 3.05 (m, 2H), 3.98 (m, 1H), 4.15 (s, 3H), 4.68 (m, 1H), 6.85 (d, 1H), 7.45 (d, 1H).

LCMS(ESI): [M-Boc]$^+$ m/z: calcd 195.3; found 196.2; Rt=1.351 min.

Step 2: Synthesis of 3-methyl-6-(1-methyl-1H-pyrazol-5-yl)-2,3,4,5-tetrahydropyridine The solution of tert-butyl N-[2-methyl-5-(2-methylpyrazol-3-yl)-5-oxo-pentyl]carbamate (3 g, 10.16 mmol) in trifluoroacetic acid (23.16 g, 203.13 mmol, 15.65 mL) was stirred at 25° C. for 1 hr, and then evaporated in vacuo. Crushed ice (20 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 3-methyl-6-(2-methylpyrazol-3-yl)-2,3,4,5-tetrahydropyridine (1.7 g, 9.59 mmol, 94.43% yield) as yellow oil, which was used directly in the next step.

$^1$H NMR (400 MHz, CDCl$_3$) δ (ppm) 1.14 (d, 3H), 1.38 (m, 1H), 1.68 (m, 1H), 1.88 (m, 1H), 2.49 (m, 1H), 2.67 (m, 1H), 3.25 (m, 1H), 3.97 (m, 1H), 4.13 (s, 3H), 6.44 (d, 1H), 7.41 (d, 1H).

LCMS(ESI): [M+1] m/z: calcd 177.2; found 178.2; Rt=0.624 min.

Step 3: Synthesis of 5-methyl-2-(1-methyl-1H-pyrazol-5-yl)piperidine

Sodium borohydride (725.67 mg, 19.18 mmol, 678.20 μL) was added in one portion to a stirred solution of 3-methyl-6-(2-methylpyrazol-3-yl)-2,3,4,5-tetrahydropyridine (1.7 g, 9.59 mmol) in methanol (20 mL) at 0° C. The resulting mixture was stirred at 0° C. for 1 hr, and then evaporated in vacuo. The residue was diluted with water (20 ml) and extracted with dichloromethane (2*40 ml). The combined organic extracts were dried over sodium sulphate and evaporated in vacuo to afford 5-methyl-2-(2-methylpyrazol-3-yl)piperidine (1.3 g, 7.25 mmol, 75.61% yield) as yellow oil, which was used directly in the next step.

$^1$H NMR (400 MHz, CDCl$_3$) δ (ppm) 0.89 (d, 3H), 1.15 (m, 2H), 1.58 (m, 2H), 1.88 (m, 2H), 2.37 (m, 1H), 3.11 (m, 1H), 3.64 (m, 1H), 3.88 (s, 3H), 6.14 (d, 1H), 7.37 (d, 1H).

LCMS(ESI): [M+1] m/z: calcd 179.2; found 180.2; Rt=0.749 min.

3B. Synthesis of 5-methyl-2-(1-methyl-1H-pyrazol-5-yl)piperidine

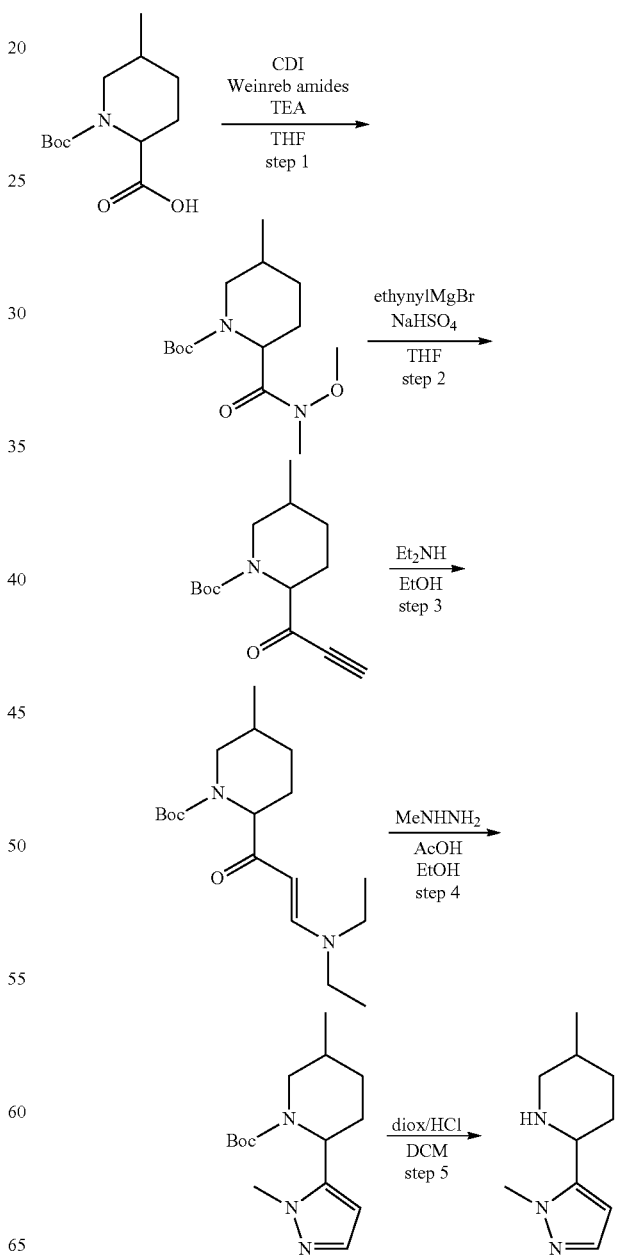

Step 1: Synthesis of tert-butyl 2-(methoxy(methyl)carbamoyl)-5-methylpiperidine-1-carboxylate CDI (8.80 g, 54.25 mmol) was added in one portion to a stirred solution of 1-tert-butoxycarbonyl-5-methyl-piperidine-2-carboxylic acid (11 g, 45.21 mmol) in THF (200 mL) at 25° C. The resulting mixture was stirred at 25° C. until carbon dioxide evolution was completed, then methoxy (methyl)amine hydrochloride (8.82 g, 90.42 mmol) and triethyl amine (9.15 g, 90.42 mmol, 12.60 mL) were added. The reaction mixture was stirred at 50° C. for 12 hr, then cooled and evaporated in vacuo. The residue was diluted with 5% aqueous sodium hydrogen sulphate solution (200 ml) and extracted with dichloromethane (2*100 ml). The combined organic extracts were washed with water (100 ml), dried over sodium sulphate and evaporated in vacuo to afford tert-butyl 2-[methoxy(methyl)carbamoyl]-5-methyl-piperidine-1-carboxylate (11.2 g, 39.11 mmol, 86.51% yield) as white solid, which was used directly in the next step.

$^1$H NMR (500 MHz, CDCl$_3$) δ (ppm) 0.88 (d, 3H), 1.17 (m, 2H), 1.46 (s, 9H), 1.74 (m, 2H), 2.03 (m, 1H), 3.09 (m, 1H), 3.18 (s, 3H), 3.84 (s, 3H), 3.99 (m, 1H), 5.03 (m, 1H).

LCMS(ESI): [M-Boc]$^+$ m/z: calcd 186.3; found 187.2; Rt=1.443 min.

Step 2: Synthesis of tert-butyl 5-methyl-2-propioloylpiperidine-1-carboxylate A solution of tert-butyl 2-[methoxy(methyl)carbamoyl]-5-methyl-piperidine-1-carboxylate (11.2 g, 39.11 mmol) in THF (200 mL) was added dropwise at −40° C. to a stirred solution of ethynylmagnesium bromide (25.08 g, 195.55 mmol, 400 mL). The resulting mixture was allowed to warm to 25° C. and stirred at this temperature for 12 hr, then poured into aqueous sodium hydrogen sulphate (46.96 g, 391.11 mmol) solution (500 g). The resulting mixture was stirred for 0.5 hr, then transferred into a separatory funnel. The upper organic layer was separated, the aqueous layer was additionally extracted with ethyl acetate (2*200 ml). The combined organic extracts were washed with brine (2*200 ml), dried over sodium sulphate and evaporated in vacuo to afford tert-butyl 5-methyl-2-prop-2-ynoyl-piperidine-1-carboxylate (9.6 g, 38.20 mmol, 97.67% yield) as red oil, which was used directly in the next step.

$^1$H NMR (500 MHz, CDCl$_3$) δ (ppm) 0.88 (d, 3H), 1.07 (m, 2H), 1.46 (s, 9H), 1.62 (m, 2H), 2.51 (m, 2H), 3.30 (d, 1H), 4.07 (m, 1H), 4.91 (m, 1H).

LCMS(ESI): [M-Boc]$^+$ m/z: calcd 151.3; found 152.2; Rt=1.501 min.

Step 3: Synthesis of (E)-tert-butyl 2-(3-(diethylamino)acryloyl)-5-methylpiperidine-1-carboxylate tert-butyl 5-methyl-2-prop-2-ynoyl-piperidine-1-carboxylate (9.6 g, 38.20 mmol) was diluted with a solution of diethylamine (4.47 g, 61.12 mmol, 6.33 mL) in ethanol (100 mL). The resulting solution was stirred at 25° C. for 1 hr, and then evaporated in vacuo to afford tert-butyl 2-[(E)-3-(diethylamino)prop-2-enoyl]-5-methyl-piperidine-1-carboxylate (12.2 g, 37.60 mmol, 98.44% yield) as red gum, which was used directly in the next step.

$^1$H NMR (500 MHz, CDCl$_3$) δ (ppm) 0.88 (d, 3H), 1.22 (m, 8H), 1.48 (s, 9H), 2.11 (m, 1H), 2.52 (m, 2H), 3.27 (m, 5H), 4.07 (m, 1H), 4.59 (m, 1H), 5.21 (d, 1H), 7.67 (d, 1H).

LCMS(ESI): [M+1] m/z: calcd 324.4; found 325.2; Rt=1.506 min.

Step 4: Synthesis of tert-butyl 5-methyl-2-(1-methyl-1H-pyrazol-5-yl)piperidine-1-carboxylate Methylhydrazine (795.18 mg, 17.26 mmol) was added to a stirred solution of tert-butyl 2-[(E)-3-(diethylamino)prop-2-enoyl]-5-methyl-piperidine-1-carboxylate (3.5 g, 10.79 mmol) and acetic acid (1.04 g, 17.26 mmol, 987.12 μL) in ethanol (50 mL). The reaction mixture was stirred with reflux condenser at 80° C. for 12 hr, then cooled and evaporated in vacuo. The residue was diluted with water (30 ml) and extracted with MTBE (2*30 ml). The combined organic extracts were washed with water (30 ml), dried over sodium sulphate and evaporated in vacuo to afford crude tert-butyl 5-methyl-2-(2-methylpyrazol-3-yl)piperidine-1-carboxylate (2.7 g, 9.66 mmol, 89.59% yield) as red oil, which was used directly in the next step.

$^1$H NMR (500 MHz, CDCl$_3$) δ (ppm) 0.88 (d, 3H), 1.22 (m, 2H), 1.44 (s, 9H), 1.56 (m, 2H), 1.74 (m, 1H), 1.92 (m, 1H), 2.08 (m, 1H), 2.26 (m, 1H), 3.86 (s, 3H), 6.24 (d, 1H), 7.39 (d, 1H). LCMS(ESI): [M+1] m/z: calcd 279.3; found 280.2; Rt=1.378 min.

Step 5: Synthesis of 5-methyl-2-(1-methyl-1H-pyrazol-5-yl)piperidine

Hydrogen chloride solution 40 M in dioxane (42.00 g, 160.12 mmol, 40 mL, 13.9% purity) was added to a stirred solution of tert-butyl 5-methyl-2-(2-methylpyrazol-3-yl)piperidine-1-carboxylate (2.7 g, 9.66 mmol) in dichloromethane (30 mL). The reaction mixture was stirred at 25° C. for 2 hr, and then evaporated in vacuo. The residue was diluted with chloroform (30 ml) and stirred for 1 hr. The precipitate was filtered, washed with chloroform (5 ml) and dried in vacuo to afford 5-methyl-2-(2-methylpyrazol-3-yl)piperidine (1.9 g, 7.53 mmol, 77.96% yield, 2HCl) as white solid.

$^1$H NMR (400 MHz, DMSO-d$_6$) δ (ppm) 1.13 (d, 3H), 1.22 (m, 1H), 1.96 (m, 3H), 2.05 (m, 1H), 2.91 (m, 1H), 3.17 (m, 1H), 3.91 (s, 3H), 4.55 (m, 1H), 6.63 (d, 1H), 8.97 (d, 1H), 10.13 (m, 1H).

LCMS(ESI): [M+1] m/z: calcd 179.2; found 180.2; Rt=0.654 min.

3C. The Synthesis of N-[5-(5-methyl-2-piperidyl)-2-thienyl]acetamide

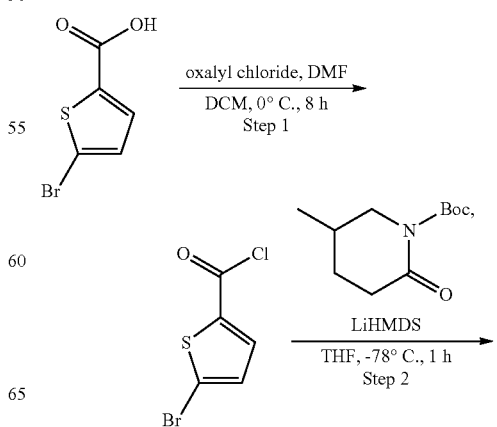

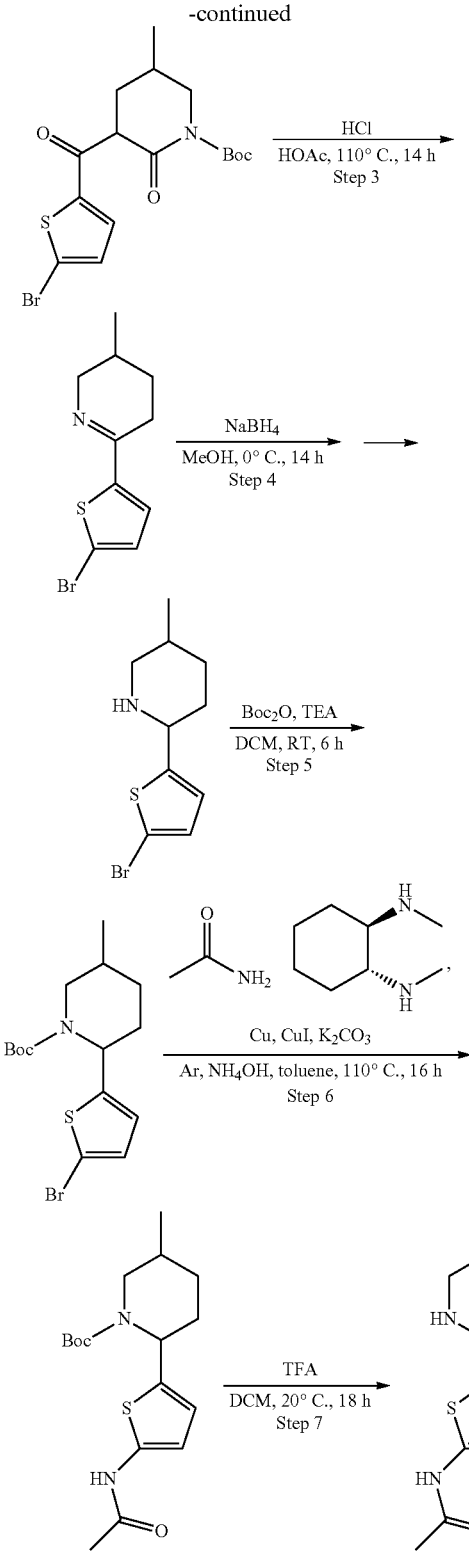

Step 1: The Synthesis of
5-bromothiophene-2-carbonyl chloride 5-bromothiophene-2-carboxylic acid (8 g, 38.64 mmol) and dimethylformamide (282.41 mg, 3.86 mmol, 299.17 µL) were suspended in dichloromethane (100 mL) and was added dropwise oxalyl chloride (9.81 g, 77.28 mmol, 6.72 mL) in dichloromethane (100 mL) at 0° C. The resulting mixture was stirred at 0° C. for 8 hr. When gas evolution ceased, resulting clear solution was concentrated under reduced pressure. Residue was redissolved in hexane (150 ml), filtered and evaporated in vacuo, to afford product 5-bromothiophene-2-carbonyl chloride (7.8 g, 34.59 mmol, 89.52% yield).

$^1$H NMR (500 MHz, CDCl$_3$) δ 7.1 (d, 1H), 7.74 (d, 1H).

Step 2: The Synthesis of tert-butyl 3-(5-bromothiophene-2-carbonyl)-5-methyl-2-oxo-piperidine-1-carboxylate Lithium bis(trimethylsilyl)amide, stab. with hexane (12.73 g, 76.10 mmol, 33 mL) was added dropwise to a precooled solution of tert-butyl 5-methyl-2-oxo-piperidine-1-carboxylate (7.38 g, 34.59 mmol) in THF (100 mL) at −78° C. After addition was complete, it was stirred at the same temperature for 1 h. After that, 5-bromothiophene-2-carbonyl chloride (7.8 g, 34.59 mmol) was added in one portion and cooling bath was removed. Resulting mixture was slowly warmed up to 0° C. and stirred at this temperature for 2 hr. Then, it was quenched with 15% aq. NaHSO$_4$ (250 ml) and extracted with ethyl acetate (300 ml). Organic layer was washed with 20% aq. NaCl (2*250 ml), dried over Na$_2$SO$_4$ and evaporated under reduced pressure, affording tert-butyl 3-(5-bromothiophene-2-carbonyl)-5-methyl-2-oxo-piperidine-1-carboxylate (9.8 g, 24.36 mmol, 70.42% yield).

$^1$H NMR (500 MHz, CDCl$_3$) δ 1.20 (m, 4H), 1.56 (s, 9H), 2.04 (m, 2H), 3.23 (m, 1H), 3.88 (m, 1H), 4.27 (m, 1H), 7.13 (m, 2H).

LCMS(ESI): [M-Boc]$^+$ m/z: calcd 302.2; found 304.0; Rt=1.429 min.

Step 3: The Synthesis of 6-(5-bromo-2-thienyl)-3-methyl-2,3,4,5-tetrahydropyridine CH$_3$COOH (100 mL) and Hydrochloric acid ACS grade 36-38% (80.00 g, 2.19 mol, 100 mL) were suspended and resulting mixture was stirred at 110° C. and was added dropwise tert-butyl 3-(5-bromothiophene-2-carbonyl)-5-methyl-2-oxo-piperidine-1-carboxylate (8.6 g, 21.38 mmol). Resulting mixture was stirred at 110° C. for 14 hr. Then, solvents were removed under reduced pressure and residue was partitioned between 1 N HCl (50 ml) and DCM (2*40 ml). Organic layer was separated and discarded. Aqueous layer was basified to pH≈10 with 10% NaOH and extracted with DCM (2*50 ml). DCM solution was separated, dried over K$_2$CO$_3$ and evaporated under reduced pressure, affording 6-(5-bromo-2-thienyl)-3-methyl-2,3,4,5-tetrahydropyridine (4.5 g, 17.43 mmol, 81.54% yield).

$^1$H NMR (500 MHz, CDCl$_3$) δ 0.98 (d, 3H), 1.37 (m, 1H), 1.71 (m, 2H), 2.71 (m, 2H), 3.19 (m, 1H), 3.88 (m, 1H), 6.99 (m, 2H).

LCMS(ESI): [M+2H]$^+$ m/z: calcd 258.2; found 260.0; Rt=0.835 min.

Step 4: The Synthesis of 2-(5-bromo-2-thienyl)-5-methyl-piperidine

Sodium Borohydride (989.06 mg, 26.14 mmol, 924.35 µL) was added portionwise to a solution of 6-(5-bromo-2-thienyl)-3-methyl-2,3,4,5-tetrahydropyridine (4.5 g, 17.43 mmol) in Methanol (100 mL) during 15 minutes. Resulting solution was stirred at 0° C. for 14 hr. Then, solvent was removed under reduced pressure and residue was partitioned between water (40 ml) and DCM (80 ml). Organic layer was separated, dried over Na₂SO₄ and evaporated in vacuo, affording 2-(5-bromo-2-thienyl)-5-methyl-piperidine (3.1 g, 11.91 mmol, 68.36% yield).

¹H NMR (400 MHz, CDCl₃) δ 0.97 (d, 3H), 1.16 (m, 2H), 1.56 (m, 2H), 1.85 (m, 2H), 2.35 (t, 1H), 3.08 (m, 1H), 3.74 (m, 1H), 6.65 (d, 1H), 6.84 (d, 1H).

LCMS(ESI): [M+H]⁺ m/z: calcd 259.2; found 260.0; Rt=0.911 min.

Step 5: The Synthesis of tert-butyl 2-(5-bromo-2-thienyl)-5-methyl-piperidine-1-carboxylate di-tert-butyl dicarbonate (1.37 g, 6.27 mmol, 1.44 mL) was added dropwise to a stirred suspension of 2-(5-bromo-2-thienyl)-5-methyl-piperidine (1.6 g, 6.15 mmol) and TEA (684.47 mg, 6.76 mmol, 942.80 µL) in DCM (20 mL) at 0° C. The resulting mixture was stirred at room temperature for 6 hr, then evaporated in vacuo poured into water (100 ml) and extracted with DCM (2*50 ml). The combined organic extracts were washed with water (2*30 ml), dried over sodium sulphate and evaporated in vacuo to afford product tert-butyl 2-(5-bromo-2-thienyl)-5-methyl-piperidine-1-carboxylate (1.8 g, 5.00 mmol, 81.24% yield).

¹H NMR (400 MHz, CDCl₃) δ 0.99 (m, 2H), 1.46 (m, 2H), 1.50 (d, 9H), 1.84 (m, 3H), 2.32 (m, 1H), 2.99 (m, 1H), 3.71 (m, 1H), 5.47 (m, 1H), 6.58 (d, 1H), 6.87 (d, 1H).

LCMS(ESI): [M-Boc]⁺ m/z: calcd 259.2; found 260.0; Rt=1.660 min.

Step 6: The Synthesis of tert-butyl 2-(5-acetamido-2-thienyl)-5-methyl-piperidine-1-carboxylate tert-butyl 2-(5-bromo-2-thienyl)-5-methyl-piperidine-1-carboxylate (2.8 g, 7.77 mmol), acetamide (918.03 mg, 15.54 mmol), Cu (246.91 mg, 3.89 mmol), CuI (148.00 mg, 777.11 µmol, 26.33 µL), Potassium carbonate (2.15 g, 15.54 mmol, 938.03 µL) and (1R,2R)—N1,N2-dimethylcyclohexane-1,2-diamine (110.54 mg, 777.11 µmol) were mixed in Ammonium hydroxide, 28% solution (40 mL) purged with Ar for 15 minutes and then heated in the sealed tube at 110° C. for 16 hr. The reaction mixture was evaporated in vacuo and poured into water (40 ml) and extracted with EtOAc (2*10 ml). The combined organic extracts were washed with Ammonium hydroxide, 28% solution (40 mL), dried over sodium sulphate and evaporated in vacuo to afford product tert-butyl 2-(5-acetamido-2-thienyl)-5-methyl-piperidine-1-carboxylate (2.2 g, 6.50 mmol, 83.64% yield).

¹H NMR (400 MHz, CDCl₃) δ 1.00 (d, 3H), 1.45 (s, 9H), 1.83 (m, 3H), 2.13 (m, 2H), 3.07 (m, 2H), 3.70 (m, 2H), 5.49 (m, 2H), 6.48 (d, 1H), 6.53 (d, 1H), 8.12 (m, 1H).

LCMS(ESI): [M-Boc]⁺ m/z: calcd 238.2; found 239.0; Rt=1.366 min.

Step 7: The Synthesis of N-[5-(5-methyl-2-piperidyl)-2-thienyl]acetamide tert-butyl 2-(5-acetamido-2-thienyl)-5-methyl-piperidine-1-carboxylate (1.05 g, 3.10 mmol) in DCM (10 mL) was added to Trifluoroacetic acid, 99% (10 g, 87.70 mmol, 6.76 mL). The reaction mixture was stirred at 20° C. for 8 hr, then evaporated in vacuo to afford N-[5-(5-methyl-2-piperidyl)-2-thienyl]acetamide (1.4 g, crude, CF₃COOH).

LCMS(ESI): [M+H]⁺ m/z: calcd 238.2; found 239.0; Rt=0.708 min.

3D. Synthesis of rac-5-((2R,5S)-5-methylpiperidin-2-yl)thiophene-2-carboxamide

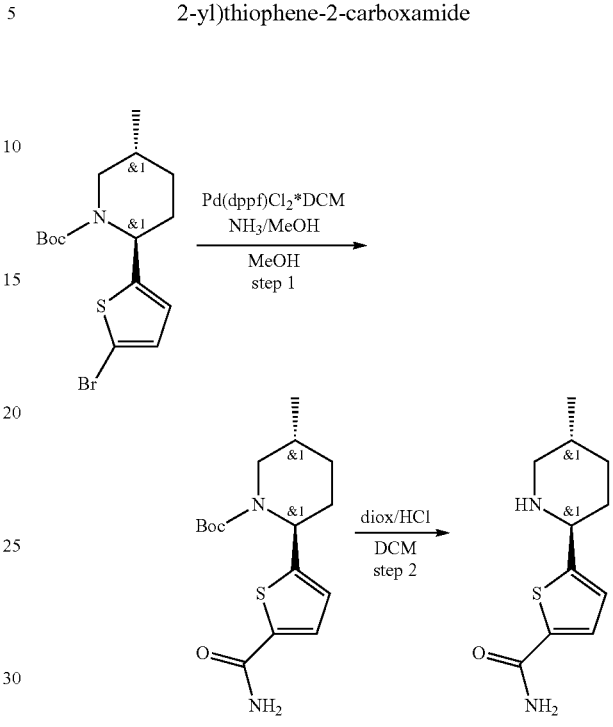

Step 1: Synthesis of rac-(2R,5S)-tert-butyl 2-(5-carbamoylthiophen-2-yl)-5-methylpiperidine-1-carboxylate tert-butyl (2R,5S)-2-(5-bromo-2-thienyl)-5-methyl-piperidine-1-carboxylate (800 mg, 2.22 mmol) (prepared as above) was dissolved in ammonia, 2 M in MeOH (15.74 g, 39.74 mmol, 20 mL, 4.3% purity) and Pd(dppf)Cl₂*DCM (90.66 mg, 111.02 µmol) was added. Resulting mixture was stirred at 130° C. for 48 hr under an atmosphere of CO (30 Bar). Solvent was removed under reduced pressure and residue was taken up in ethyl acetate (40 ml). Insoluble solids were filtered off through a short pad of silicagel and filtrate was concentrated under reduced pressure. Obtained mixture (approx. 50/50 amide/methyl ester) was redissolved in MeOH (30 mL), saturated with dry ammonia at 0-5° C. and stirred at 130° C. for 24 hr in autoclave. Then, it was concentrated in vacuo, affording tert-butyl (2R,5S)-2-(5-carbamoyl-2-thienyl)-5-methyl-piperidine-1-carboxylate (800 mg, crude).

¹H NMR (400 MHz, DMSO-d₆) δ (ppm) 0.91 (d, 3H), 1.31 (m, 1H), 1.38 (s, 9H), 1.49 (m, 1H), 1.91 (m, 3H), 2.91 (m, 1H), 3.31 (m, 1H), 5.38 (m, 1H), 6.86 (d, 1H), 7.59 (m, 2H), 7.91 (d, 1H).

LCMS(ESI): [M-Boc]⁺ m/z: calcd 224.2; found 225.2; Rt=1.400 min.

Step 2: Synthesis of rac-5-((2R,5S)-5-methylpiperidin-2-yl)thiophene-2-carboxamide Hydrogen chloride, 4 M in 1,4-dioxane, 99% (10.10 g, 27.70 mmol, 12.62 mL, 10% purity) was added to a solution of tert-butyl (2R,5S)-2-(5-carbamoyl-2-thienyl)-5-methylpiperidine-1-carboxylate (800 mg, 2.47 mmol) in DCM (15 mL) and resulting mixture was stirred at 20° C. for 5 hr. Then, solvents were removed under reduced pressure and residue was redissolved in water (20 ml). Insoluble tar was filtered off through a cotton wool plug. Filtrate was basified to pH≈10 with solid $K_2CO_3$ and extracted with ethyl acetate (2×15 ml). Combined organic layers were dried over $Na_2SO_4$ and concentrated under reduced pressure, affording 5-[(2R,5S)-5-methyl-2-piperidyl]thiophene-2-carboxamide (370 mg, 1.65 mmol, 66.89% yield).

$^1$H NMR (400 MHz, CDCl$_3$) δ (ppm) 0.82 (d, 3H), 1.11 (m, 1H), 1.34 (m, 1H), 1.48 (m, 1H), 1.78 (d, 1H), 1.86 (d, 1H), 2.23 (t, 1H), 2.95 (m, 1H), 3.70 (d, 1H), 6.94 (d, 1H), 7.54 (d, 1H), 7.70 (m, 2H).

LCMS(ESI): [M]$^+$ m/z: calcd 224.2; found 225.2; Rt=0.523 min.

3E. The Synthesis of rac-N-methyl-5-((2R,5S)-5-methylpiperidin-2-yl)thiophene-2-carboxamide

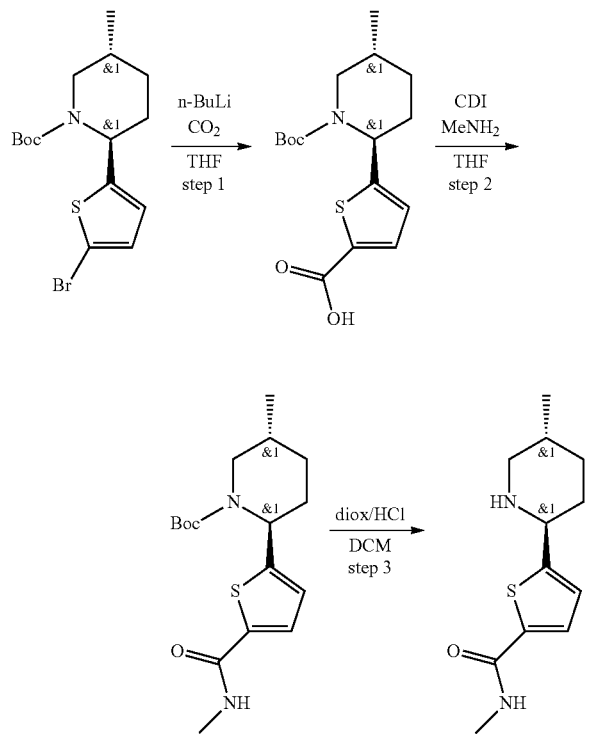

Step 1: Synthesis of rac-5-((2R,5S)-1-(tert-butoxycarbonyl)-5-methylpiperidin-2-yl)thiophene-2-carboxylic acid To a stirred solution of tert-butyl (2R,5S)-2-(5-bromo-2-thienyl)-5-methyl-piperidine-1-carboxylate (5 g, 13.88 mmol) (prepared as described above) in THF (50 mL) at −75° C., n-butyl lithium, 23% (2.5M) in hexanes (4.25 g, 15.26 mmol, 6.13 mL, 23% purity) was added dropwise under argon atmosphere. The resulting solution was stirred at the same temperature for 15 minutes. After 15 minutes, balloon filled with carbon dioxide (3.66 g, 83.26 mmol) was attached to reaction vessel and residual argon was blown out with $CO_2$. After that, reaction flask was closed and resulting solution was stirred at −75° C. for 40 min. Then, it was allowed to warm to rt and partitioned between 10% aq·NaHSO$_4$ (100 ml) and MTBE (100 ml). Organic layer was washed with brine (50 ml), dried over $Na_2SO_4$ and concentrated under reduced pressure, affording 5-[(2R,5S)-1-tert-butoxycarbonyl-5-methyl-2-piperidyl]thiophene-2-carboxylic acid (4.6 g, crude).

$^1$H NMR (400 MHz, DMSO-d$_6$) δ (ppm) 0.79 (m, 1H), 0.96 (d, 3H), 1.39 (s, 9H), 1.69 (m, 1H), 1.82 (m, 1H), 1.96 (m, 1H), 2.07 (m, 1H), 2.92 (d, 1H), 3.65 (d, 1H), 5.44 (m, 1H), 6.95 (d, 1H), 7.61 (d, 1H), 12.96 (m, 1H).

LCMS(ESI): [M-Boc]$^+$ m/z: calcd 225.2; found 226.2; Rt=1.487 min.

Step 2: Synthesis of rac-(2R,5S)-tert-butyl 5-methyl-2-(5-(methylcarbamoyl)thiophen-2-yl)piperidine-1-carboxylate Carbonyldiimidazole (934.26 mg, 5.76 mmol) was added to a solution of 5-[(2R,5S)-1-tert-butoxycarbonyl-5-methyl-2-piperidyl]thiophene-2-carboxylic acid (1.5 g, 4.61 mmol) in THF (20 mL). Resulting solution was briefly heated to 50° C. for 10 minutes. Then, it was cooled to rt and methylamine 2 M in THF (19.88 g, 46.09 mmol, 23.09 mL, 7.2% purity) was added. Resulting mixture was stirred at 20° C. for 4 hr. After that, solvent was removed under reduced pressure and residue was redissolved in ethyl acetate (30 ml) and washed with 10% aq·NaHSO$_4$ (2×10 ml). EA solution was dried over $Na_2SO_4$ and concentrated in vacuum, affording tert-butyl (2R,5S)-5-methyl-2-[5-(methylcarbamoyl)-2-thienyl]piperidine-1-carboxylate (1.4 g, 4.14 mmol, 89.74% yield).

$^1$H NMR (400 MHz, DMSO-d$_6$) δ (ppm) 0.96 (d, 3H), 1.32 (m, 1H), 1.42 (s, 9H), 1.70 (m, 1H), 1.82 (m, 1H), 1.98 (m, 1H), 2.05 (m, 1H), 2.72 (d, 3H), 2.93 (d, 1H), 3.61 (d, 1H), 5.43 (m, 1H), 6.91 (d, 1H), 7.55 (d, 1H), 8.37 (m, 1H).

LCMS(ESI): [M-Boc]$^+$ m/z: calcd 238.2; found 239.2; Rt=1.279 min.

Step 3: Synthesis of rac-N-methyl-5-((2R,5S)-5-methylpiperidin-2-yl)thiophene-2-carboxamide Hydrogen chloride, 4 M in 1,4-dioxane, 99% (15.15 g, 41.55 mmol, 18.94 mL, 10% purity) was added to a solution of tert-butyl (2R,5S)-5-methyl-2-[5-(methylcarbamoyl)-2-thienyl]piperidine-1-carboxylate (1.4 g, 4.14 mmol) in DCM (20 mL). Resulting mixture was stirred at 20° C. for 15 hr. Then, volatiles were removed under reduced pressure and residue was partitioned between 20% aq. $K_2CO_3$ solution (20 ml) and ethyl acetate (40 ml). Organic layer was separated, dried over $Na_2SO_4$ and concentrated in vacuum, affording N-methyl-5-[(2R,5S)-5-methyl-2-piperidyl]thiophene-2-carboxamide (760 mg, 3.19 mmol, 77.09% yield).

$^1$H NMR (500 MHz, DMSO-d$_6$) δ (ppm) 0.80 (d, 3H), 0.88 (m, 1H), 1.05 (m, 1H), 1.32 (m, 1H), 1.48 (m, 1H), 1.73 (m, 1H), 1.84 (m, 1H), 2.21 (t, 1H), 2.71 (d, 3H), 2.93 (d, 1H), 3.70 (d, 1H), 6.92 (d, 1H), 7.47 (d, 1H), 8.26 (m, 1H).

LCMS(ESI): [M]$^+$ m/z: calcd 238.2; found 239.2; Rt=0.569 min.

3F. The Synthesis of 2-cyclohexyl-5-methyl-piperidine

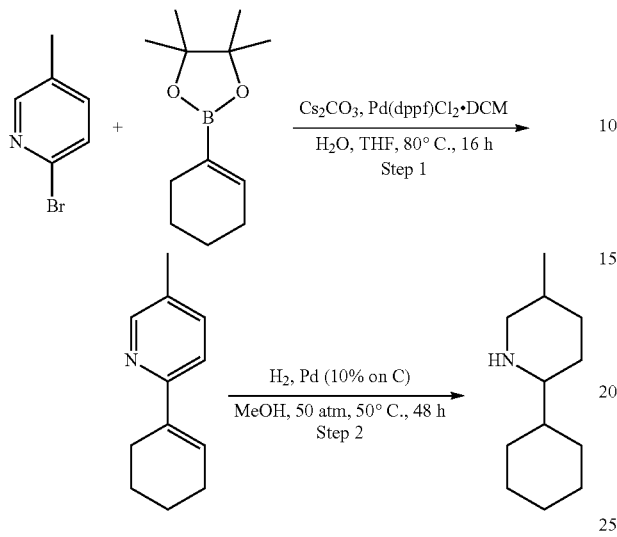

Step 1: The Synthesis of 2-(cyclohexen-1-yl)-5-methyl-pyridine 2-bromo-5-methyl-pyridine (2.86 g, 16.63 mmol) and 2-(cyclohexen-1-yl)-4,4,5,5-tetramethyl-1,3,2-dioxaborolane (4.15 g, 19.95 mmol, 4.32 mL) were dissolved in THF (50 mL). Solution of caesium carbonate (13.54 g, 41.56 mmol) in Water (5 mL) was added. Then, $PdCl_2*dppf*CH_2Cl_2$ (83.13 µmol) was added and the reaction flask was quickly evacuated and refilled with argon. The resulting mixture was stirred at 80° C. for 16 h. After that, it was cooled and evaporated. The residue was partitioned between EtOAc and water. The organic layer was washed with brine, dried over $Na_2SO_4$ and evaporated. The residue was subjected to column chromatography ($SiO_2$ (80 g) column, Hex-MTBE as a mobile phase) to obtain 2-(cyclohexen-1-yl)-5-methyl-pyridine (2 g, 11.54 mmol, 69.43% yield).

$^1$H NMR (DMSO-$d_6$, 400 MHz) δ (ppm) 1.59 (m, 2H), 1.68 (m, 2H), 2.18 (t, 2H), 2.25 (s, 3H), 2.41 (t, 2H), 6.62 (s, 1H), 7.38 (d, 1H), 7.51 (d, 1H), 8.32 (s, 1H).

LCMS(ESI): $[M+H]^+$ m/z: calcd 173.2; found 174.2; Rt=0.899 min.

Step 2: The Synthesis of 2-cyclohexyl-5-methyl-piperidine

Palladium, 10% on carbon, type 487, dry (24.57 mg, 230.88 µmol) was added to the solution of 2-(cyclohexen-1-yl)-5-methyl-pyridine (2 g, 11.54 mmol) in MeOH (50 mL) and the resulting mixture was hydrogenated at 50 atm. pressure and 50° C. for 48 h. After consumption of starting material (HNMR control), the resulting mixture was cooled to r.t. and filtered. The filtrate was evaporated to dryness. The residue was subjected to HPLC (Agilent 1260 Infinity systems equipped with DAD and mass-detector; Waters SunFire C18 OBD Prep Column, 100 A, 5 mkm, 19*100 mm with SunFire C18 Prep Guard Cartridge, 100 A, 10 mkm, 19*100 mm; 1-30% 1.5-5 min; water-acetonitrile as a mobile phase; flow 30 mL/min; (loading pump 4 mL/min water); target mass 181) to obtain 2-cyclohexyl-5-methyl-piperidine (1.5 g, 6.89 mmol, 59.67% yield, HCl).

$^1$H NMR (DMSO-$d_6$, 400 MHz) δ (ppm) 0.95 (s, 3H), 1.12 (m, 6H), 1.51 (m, 4H), 1.84 (m, 6H), 2.77 (m, 2H), 3.09 (m, 2H), 8.88 (s, 1H).

LCMS(ESI): $[M+H]^+$ m/z: calcd 181.2; found 182.4; Rt=2.315 min.

3G. The Synthesis of Rac N-methyl-4-[(2S,5R)-5-methyl-2-piperidyl]aniline

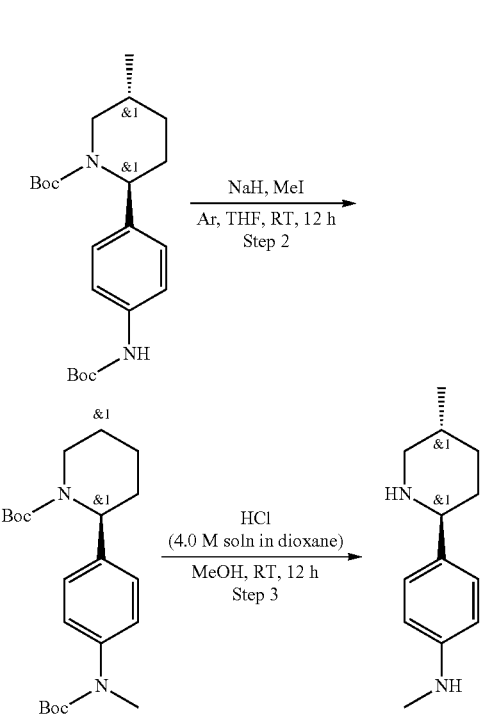

Step 1: The Synthesis of Rac Tert-butyl (2S,5R)-2-[4-(tert-butoxycarbonylamino)phenyl]-5-methyl-piperidine-1-carboxylate rac 4-[(2S,5R)-5-methyl-2-piperidyl]aniline (1 g, 3.80 mmol, 2HCl) was dissolved in DCM (30 mL). The resulting mixture was stirred for 5 min at room temperature and TEA (1.54 g, 15.20 mmol, 2.12 mL) was added. The reaction mixture was cooled with ice-water bath followed by the dropwise addition of tert-butoxycarbonyl tert-butyl carbonate (3.32 g, 15.20 mmol, 3.49 mL). Crude compound was flashed on $SiO_2$ with MTBE-Hex (50/50%) affording rac tert-butyl (2S,5R)-2-[4-(tert-butoxycarbonylamino)phenyl]-5-methyl-piperidine-1-carboxylate (1.1 g, 2.82 mmol, 74.14% yield).

LCMS(ESI): [M-Boc]⁺ m/z: calcd 290.2; found 291.2; Rt=1.615 min.

Step 2: The Synthesis of Rac Tert-butyl (2S,5R)-2-[4-[tert-butoxycarbonyl(methyl)amino]phenyl]-5-methyl-piperidine-1-carboxylate rac tert-butyl (2S,5R)-2-[4-(tert-butoxycarbonylamino)phenyl]-5-methyl-piperidine-1-carboxylate (1.1 g, 2.82 mmol) was dissolved in THF (30 mL). The flask was purged with Ar and NaH (129.52 mg, 3.38 mmol, 60% purity) was carefully added in small quantities. After 1 h of vigorous stirring, MeI (439.79 mg, 3.10 mmol) was added dropwise via syringe and then stirred overnight. Final mixture was quenched with 1 mL of water and then concentrated. The crude product was treated with water and extracted with MTBE, dried over Na$_2$SO$_4$ and evaporated in vacuo to afford tert-butyl (2S,5R)-2-[4-[tert-butoxycarbonyl(methyl)amino]phenyl]-5-methyl-piperidine-1-carboxylate (1.3 g, crude).

¹H NMR (400 MHz, CDCl$_3$) δ 7.01 (d, 3H), 1.43 (s, 18H), 1.60 (m, 3H), 2.01 (m, 2H), 2.96 (m, 1H), 3.23 (s, 3H), 3.70 (m, 1H), 5.28 (m, 1H), 7.16 (m, 4H).

LCMS(ESI): [M-Boc]⁺ m/z: calcd 304.2; found 305.2; Rt=1.784 min.

Step 3: The Synthesis of Rac N-methyl-4-[(2S,5R)-5-methyl-2-piperidyl]aniline rac tert-butyl (2S,5R)-2-[4-[tert-butoxycarbonyl(methyl)amino]phenyl]-5-methyl-piperidine-1-carboxylate (1.3 g, 3.21 mmol) was dissolved in 10 mL of methanol and then 10 mL of HCl in dioxane (40 M solution) was added. The mixture was stirred overnight, and then concentrated in vacuo. The crude product was treated with MTBE and filtered on. The obtained precipitate was air-dried to give rac N-methyl-4-[(2S,5R)-5-methyl-2-piperidyl]aniline (0.65 g, 2.34 mmol, 72.96% yield, 2HCl).

LCMS(ESI): [M+H]⁺ m/z: calcd 204.1; found 205.2; Rt=0.608 min.

3H. The Synthesis of rac-(2R,5R)-2-(3,4-difluorophenyl)-4,4-difluoro-5-methylpiperidine

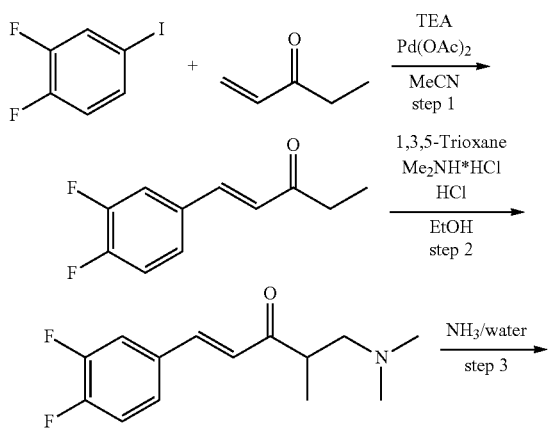

Step 1: Synthesis of (E)-1-(3,4-difluorophenyl)pent-1-en-3-one

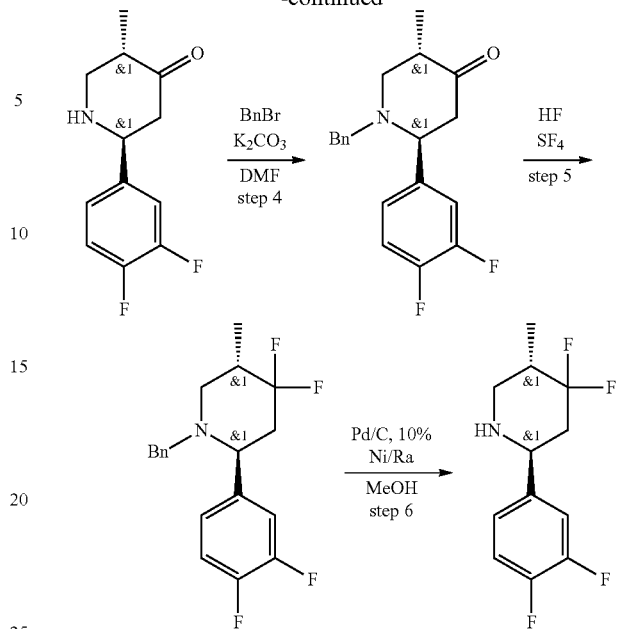

To a mixture of 1,2-difluoro-4-iodo-benzene (20 g, 83.34 mmol) and TEA (12.23 g, 120.84 mmol, 16.84 mL) was added pent-1-en-3-one (14.02 g, 166.67 mmol), followed by palladium (II) acetate (935.49 mg, 4.17 mmol) and MeCN (100 mL) under Ar atmosphere. The mixture was refluxed for 12 hr. The solvent was removed and the residue was taken up with water (150 ml) and extracted with MTBE (3*100 ml). The organic layer was washed with brine, dried over anhydrous sodium sulphate, filtered and concentrated in vacuum to give (E)-1-(3,4-difluorophenyl)pent-1-en-3-one (18 g, crude), which was used in the next step without further purification.

¹H NMR (400 MHz, CDCl$_3$) δ (ppm) 1.18 (t, 3H), 2.69 (m, 2H), 6.65 (d, 1H), 7.18 (d, 1H), 7.27 (s, 1H), 7.36 (d, 1H), 7.45 (d, 1H).

LCMS(ESI): [M]⁺ m/z: calcd 196.2; found 197.2; Rt=1.449 min.

Step 2: Synthesis of (E)-1-(3,4-difluorophenyl)-5-(dimethylamino)-4-methylpent-1-en-3-one A solution of (E)-1-(3,4-difluorophenyl)pent-1-en-3-one (18 g, 91.75 mmol), 1,3,5-trioxane (5.51 g, 183.49 mmol, 4.71 mL, 300% purity), dimethylamine hydrochloride (7.48 g, 91.75 mmol) and hydrochloric acid, 36% w/w aq. soln. (9.16 g, 91.75 mmol, 11.46 mL, 36.5% purity) in EtOH (150 mL) was stirred at 80° C. for 12 hr. The solvent was removed in vacuo to give (E)-1-(3,4-difluorophenyl)-5-(dimethylamino)-4-methyl-pent-1-en-3-one (30 g, crude, HCl), which was used for the next step without further purification.

¹H NMR (400 MHz, DMSO-d$_6$) δ (ppm) 1.17 (d, 3H), 2.68 (s, 6H), 3.45 (m, 1H), 4.47 (m, 2H), 6.85 (d, 1H), 7.10 (d, 1H), 7.62 (s, 1H), 7.83 (d, 1H), 7.92 (d, 1H).

LCMS(ESI): [M]⁺ m/z: calcd 253.2; found 254.2; Rt=0.795 min.

Step 3: Synthesis of rac-(2R,5R)-2-(3,4-difluorophenyl)-5-methylpiperidin-4-one (E)-1-(3,4-difluorophenyl)-5-(dimethylamino)-4-methyl-pent-1-en-3-one (30 g, 118.44 mmol) was dissolved in water (150 mL) and NH₃ aq (150 mL) then the reaction mixture was stirred at 80° C. for 12 hr. The reaction mixture was acidified with 1 N HCl, extracted with MTBE (2*150 ml) then aqueous layer was basified with 1 N NaOH and extracted with DCM (3*100 ml). DCM layer was dried over Na₂SO₄, filtered and evaporated on vacuum to give (2S,5S)-2-(3,4-difluorophenyl)-5-methyl-piperidin-4-one (5.5 g, crude), which was used in the next step without further purification.

¹H NMR (400 MHz, CDCl₃) δ (ppm) 1.03 (d, 3H), 1.26 (m, 1H), 2.48 (m, 2H), 2.65 (m, 2H), 3.45 (m, 1H), 3.88 (d, 1H), 7.07 (m, 2H), 7.24 (d, 1H).

LCMS(ESI): [M]⁺ m/z: calcd 225.2; found 226.2; Rt=0.570 min.

Step 4: Synthesis of rac-(2R,5R)-1-benzyl-2-(3,4-difluorophenyl)-5-methylpiperidin-4-one (2S,5S)-2-(3,4-difluorophenyl)-5-methyl-piperidin-4-one (5.5 g, 24.42 mmol), potassium carbonate, anhydrous, 99% (10.12 g, 73.26 mmol, 4.42 mL) and bromomethylbenzene (4.59 g, 26.86 mmol, 3.19 mL) was dissolved in DMF (25 mL) and stirred at 60° C. for 12 hr. The reaction mixture was taken up with water (150 ml) and extracted with MTBE (3*50 ml). The organic phase was washed with brine (3*50 ml). Organic phase was dried over Na₂SO₄, filtered and concentrated in vacuo to give crude product (7 g) which was purified by flash column chromatography (Hexane-MTBE) to give (2S,5S)-1-benzyl-2-(3,4-difluorophenyl)-5-methyl-piperidin-4-one (2.0 g, 6.34 mmol, 25.97% yield). The structure of title compound was proved by 2D-NMR experiment.

¹H NMR (500 MHz, CDCl₃) δ (ppm) 0.94 (d, 3H), 2.02 (m, 1H), 2.48 (m, 1H), 2.62 (m, 1H), 2.75 (m, 1H), 2.90 (m, 1H), 3.17 (m, 1H), 3.53 (m, 1H), 3.79 (m, 1H), 7.17 (m, 1H), 7.32 (m, 7H).

LCMS(ESI): [M]⁺ m/z: calcd 315.2; found 316.2; Rt=1.428 min.

Step 5: Synthesis of rac-(2R,5R)-1-benzyl-2-(3,4-difluorophenyl)-4,4-difluoro-5-methylpiperidine (2S,5S)-1-benzyl-2-(3,4-difluorophenyl)-5-methyl-piperidin-4-one (2 g, 6.34 mmol), HF (1.27 g, 63.42 mmol) and SF₄ (1.37 g, 12.68 mmol) were heated in a stainless steel autoclave at 70° C. for 12 hr. After completion of the reaction, the gaseous products were vented off, the reaction mixture was poured onto ice and neutralized with a 10% aqueous solution of K₂CO₃. The product was extracted with MTBE (3×100 mL). Combined organic extracts were washed with brine, dried over Na₂SO₄, and concentrated under reduced pressure to give (2S,5S)-1-benzyl-2-(3,4-difluorophenyl)-4,4-difluoro-5-methyl-piperidine (2 g, 5.93 mmol, 93.48% yield) which was used in the next step without further purification.

¹H NMR (500 MHz, CDCl₃) δ (ppm) 0.97 (d, 3H), 2.02 (m, 2H), 2.22 (m, 2H), 2.85 (m, 2H), 3.45 (d, 1H), 3.72 (d, 1H), 7.14 (m, 2H), 7.25 (m, 3H), 7.31 (m, 3H).

LCMS(ESI): [M]⁺ m/z: calcd 337.2; found 338.2; Rt=1.718 min.

Step 6: Synthesis of rac-(2R,5R)-2-(3,4-difluorophenyl)-4,4-difluoro-5-methylpiperidine A solution of (2S,5S)-1-benzyl-2-(3,4-difluorophenyl)-4,4-difluoro-5-methyl-piperidine (2 g, 5.93 mmol) in MeOH (60 mL) in a presence of Raney Nickel 2800, slurry, in H₂O, active catalyst (507.92 mg, 5.93 mmol) was refluxed for 4 hr and filtered through a thin layer of SiO₂. To the solution, palladium, 10% on carbon, Type 487, dry (630.91 mg, 5.93 mmol) was added and hydrogenated with H₂ (40 atm) at rt for 48 hr. The reaction mixture was filtered through celite and filtrate was concentrated in vacuum to give (2S,5S)-2-(3,4-difluorophenyl)-4,4-difluoro-5-methyl-piperidine (0.9 g, 3.64 mmol, 61.40% yield) which was used in the next step without further purification.

¹H NMR (400 MHz, DMSO-d₆) δ (ppm) 0.90 (d, 3H), 1.72 (m, 1H), 1.97 (m, 1H), 2.16 (m, 1H), 2.39 (t, 1H), 2.69 (bds, 1H), 2.98 (d, 1H), 3.71 (d, 1H), 7.21 (s, 1H), 7.35 (d, 1H), 7.45 (d, 1H).

LCMS(ESI): [M]⁻ m/z: calcd 247.2; found 248.2; Rt=0.981 min.

3I. The Synthesis of Rac 4,4-difluoro-5-methyl-2-phenyl-piperidine

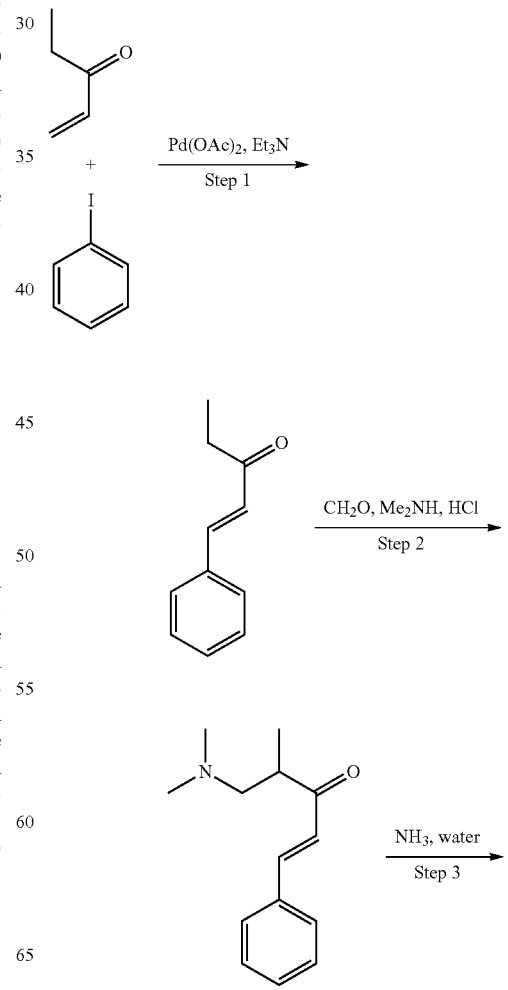

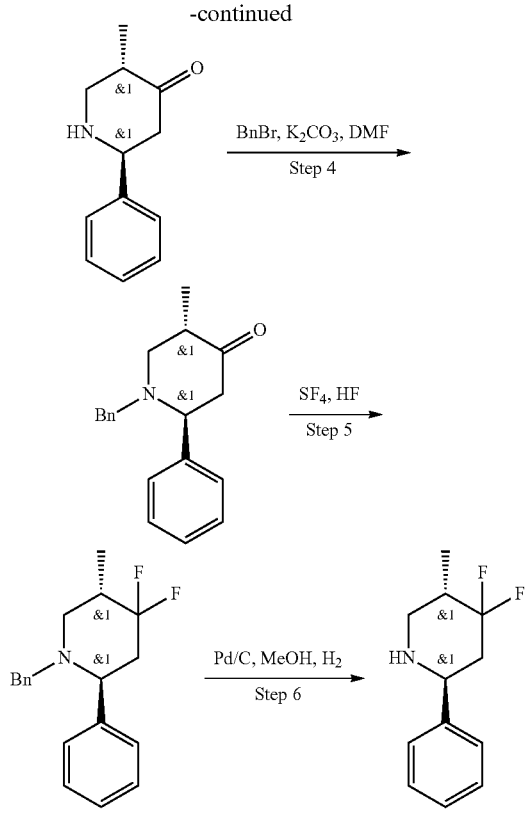

Step 1: Synthesis of (E)-1-phenylpent-1-en-3-one

To a mixture of iodobenzene (30 g, 147.05 mmol, 16.39 mL) and TEA (21.58 g, 213.23 mmol, 29.72 mL) was added pent-1-en-3-one (24.74 g, 294.11 mmol), followed by Palladium (II) acetate (1.65 g, 7.35 mmol) and MeCN (150 mL) at rt. The mixture was refluxed for 12 hr then ethyl acetate (30 mL) and water (30 mL) were added. The organic layer was washed with water, dried over anhydrous sodium sulphate, filtered and concentrated in vacuo to give (E)-1-phenylpent-1-en-3-one (27.66 g, crude) which was used in the next step without further purification.

LCMS(ESI): [M-$^t$Bu]$^+$ m/z: calcd 160.2; found 161.4; Rt=3.422 min.

Step 2: Synthesis of (E)-5-(dimethylamino)-4-methyl-1-phenyl-pent-1-en-3-one (E)-1-phenylpent-1-en-3-one (27 g, 168.53 mmol), N-methylmethanamine (13.74 g, 168.53 mmol, 17.73 mL, HCl) and Formaldehyde, 37% w/w aq. soln., stab. with 7-8% methanol (10.63 g, 353.91 mmol, 9.84 mL) was heated at reflux in Ethanol (300 mL)+HCl (aq) (30 mL) for 4 hours.

The reaction mixture was concentrated in vacuo to give (E)-5-(dimethylamino)-4-methyl-1-phenyl-pent-1-en-3-one (41 g, crude) which was used in the next step without further purification.

LCMS(ESI): [M+1]$^+$ m/z: calcd 217.1; found 218.4; Rt=2.136 min.

Step 3: Synthesis of 5-methyl-2-phenyl-piperidin-4-one (E)-5-(dimethylamino)-4-methyl-1-phenyl-pent-1-en-3-one (46 g, 181.27 mmol, HCl) was dissolved in water (150 mL) and NH$_3$(aq) (150 mL) then the reaction mixture was stirred at 80° C. for 20 hr. The reaction mixture was acidified with 1 N HCl, extracted with MTBE (2*20 ml) then aqueous layer was basified with 1 N NaOH and extracted with DCM (2*20 ml). DCM layer was dried over Na$_2$SO$_4$, filtered and evaporated on vacuo to give 5-methyl-2-phenyl-piperidin-4-one (8.15 g, 43.06 mmol, 23.76% yield) which was used in the next step without further purification.

LCMS(ESI): [M+1]$^+$ m/z: calcd 190.2; found 190.4; Rt=1.152 min.

Step 4: Synthesis of 1-benzyl-5-methyl-2-phenyl-piperidin-4-one 5-methyl-2-phenyl-piperidin-4-one (1.15 g, 6.08 mmol), Benzyl bromide, 99% (1.14 g, 6.68 mmol, 793.88 µL) and Potassium carbonate, anhydrous, 99% (2.52 g, 18.23 mmol, 1.10 mL) was dissolved in DMF (3 mL) and stirred at 60° C. for 12 hr. Ethyl acetate was added and organic phase was washed with brine three times. Organic phase was dried over Na$_2$SO$_4$, filtered and concentrated in vacuo at 45° C. to give crude product which was purified by flash column chromatography to give 1-benzyl-5-methyl-2-phenyl-piperidin-4-one (0.52 g, 1.86 mmol, 30.63% yield)

$^1$H NMR (CDCl$_3$, 400 MHz): δ (ppm) 0.93 (m, 3H), 1.53 (s, 1H), 2.00 (t, 1H), 2.51 (d, 1H), 2.71 (m, 1H), 2.84 (m, 1H), 3.17 (m, 1H), 3.51 (d, 1H), 3.79 (d, 1H), 7.23-7.45 (m, 10H).

LCMS(ESI): [M+1]$^+$ m/z: calcd 279.2; found 280.4; Rt=2.905 min.

Step 5: Synthesis of 1-benzyl-4,4-difluoro-5-methyl-2-phenyl-piperidine 1-benzyl-5-methyl-2-phenyl-piperidin-4-one (0.52 g, 1.86 mmol), HF (372.38 mg, 18.61 mmol) and SF$_4$ (402.41 mg, 3.72 mmol) were heated in a stainless steel autoclave at 70° C. for 12 h. After completion of the reaction, the gaseous products were vented off, the reaction mixture was poured onto ice and neutralized with a 10% aqueous solution of K$_2$CO$_3$. The product was extracted with MTBE (3×100 mL). Combined organic extracts were washed with brine, dried over Na$_2$SO$_4$, and concentrated under reduced pressure to give 1-benzyl-4,4-difluoro-5-methyl-2-phenyl-piperidine (0.4 g, 1.33 mmol, 71.31% yield) which was used in the next step without further purification.

$^1$H NMR (400 MHz, CDCl$_3$) δ 0.96 (m, 3H), 1.99 (m, 1H), 2.10 (m, 2H), 2.23 (m, 1H), 2.83 (m, 2H), 3.46 (d, 1H), 3.76 (d, 1H), 7.23-7.46 (m, 10H)

LCMS(ESI): [M+1]$^+$ m/z: calcd 301.4; found 302.2; Rt=1.356 min.

Step 6: Synthesis of 4,4-difluoro-5-methyl-2-phenyl-piperidine 1-benzyl-4,4-difluoro-5-methyl-2-phenyl-piperidine (0.4 g, 1.33 mmol) was dissolved in MeOH (10 mL) and Pd/C 10% (0.1 g, 53.09 µmol) was added and hydrogenated with H$_2$ (30 atm) at RT for 60 hr. The reaction mixture was filtered through celite and filtrate was concentrated in vacuo at 45° C. to give 4,4-difluoro-5-methyl-2-phenyl-piperidine (0.2 g, 946.75 µmol, 71.33% yield) which was used in the next step without further purification.

$^1$H NMR (500 MHz, CDCl$_3$) δ 1.06 (m, 3H), 1.83-2.30 (m, 3H), 2.71 (t, 1H), 3.13 (m, 1H), 3.92 (d, 2H), 7.23-7.46 (m, 5H)

LCMS(ESI): [M+1]⁺ m/z: calcd 211.2; found 212.2; Rt=0.714 min.

3J. The Synthesis of (2R,5R)-5-methyl-2-phenyl-piperidin-4-ol

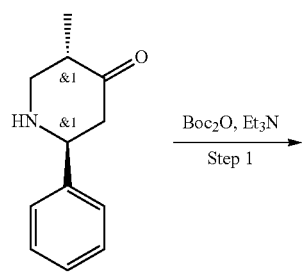

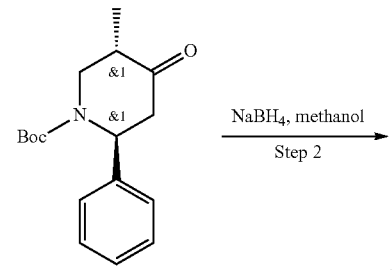

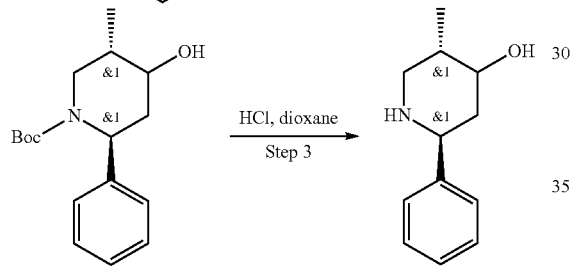

Step 1: Synthesis of tert-butyl (2R,5R)-5-methyl-4-oxo-2-phenyl-piperidine-1-carboxylate 5-methyl-2-phenyl-piperidin-4-one (2.8 g, 14.80 mmol) (prepared as described above) and Di-tert-butyl dicarbonate (3.23 g, 14.80 mmol, 3.40 mL)TEA (2.25 g, 22.19 mmol, 3.09 mL) was dissolved in DCM (40 mL) and Di-tert-butyl dicarbonate (3.23 g, 14.80 mmol, 3.40 mL) was added dropwise then the reaction mixture was stirred for 12 hr at RT. The reaction mixture was washed with NaHSO₄ (aq), the organic layer was dried over Na₂SO₄, filtered and evaporated on vacuo to give crude product which was purified by HPLC (2-10 min 10-50% MeCN+NH₃, 30 ml/min, (loading pump 4 ml MeCN) column: TRIART C18 100*20 mm) to give tert-butyl (2R,5R)-5-methyl-4-oxo-2-phenyl-piperidine-1-carboxylate (0.317 g, 1.10 mmol, 7.40% yield).

LCMS(ESI): [M-ᵗBu+1]⁺ m/z: calcd 289.2; found 234.2; Rt=3.784 min.

Step 2: Synthesis of tert-butyl (2R,5R)-4-hydroxy-5-methyl-2-phenyl-piperidine-1-carboxylate tert-butyl (2R,5R)-5-methyl-4-oxo-2-phenyl-piperidine-1-carboxylate (0.31 g, 1.07 mmol) was dissolved in MeOH (7 mL). The reaction mixture was cooled with cold water and Sodium Borohydride (60.79 mg, 1.61 mmol, 56.82 µL) was added. The reaction mixture was stirred overnight at RT. Solvent was removed on vacuo. The residue was diluted with NH₄Cl (aq) and extracted with DCM (2×20 ml), DCM was dried over Na₂SO₄, filtered and concentrated on vacuo to give tert-butyl (2R,5R)-4-hydroxy-5-methyl-2-phenyl-piperidine-1-carboxylate (0.244 g, 837.38 µmol, 78.17% yield) as DM which was used in the next step without further purification.

¹H NMR (400 MHz, CDCl₃) δ 1.50 (m, 3H), 1.35 (m, 9H), 1.71-2.50 (m, 4H), 3.50 (m, 1H), 3.67 (m, 1H), 3.87 (m, 1H), 5.12-5.55 (m, 1H), 7.31 (m, 5H).

LCMS(ESI): [M+Na]⁺ m/z: calcd 314.2; found 291.2; Rt=3.635 min.

Step 3: Synthesis of (2R,5R)-5-methyl-2-phenyl-piperidin-4-ol tert-butyl (2R,5R)-4-hydroxy-5-methyl-2-phenyl-piperidine-1-carboxylate (0.244 g, 837.38 µmol) was dissolved in Dioxane/HCl (7 mL) and was stirred for 4 hr. The reaction mixture was concentrated on vacuo to give (2R,5R)-5-methyl-2-phenyl-piperidin-4-ol (0.19 g, 834.32 µmol, 99.63% yield, HCl) as DM which was used in the next step without further purification.

¹H NMR (500 MHz, DMSO) δ 0.91-1.02 (m, 3H), 1.83-2.30 (m, 3H), 2.73 (q, 1H), 2.97-3.21 (m, 2H), 4.39 (m, 1H), 7.40-7.50 (m, 5H), 9.13-9.47 (m, 2H)

LCMS(ESI): [M+1]⁺ m/z: calcd 191.2; found 192.4; Rt=1.023 min.

3K. The Synthesis of rac-(2R,5R)-5-fluoro-5-methyl-2-phenylpiperidine

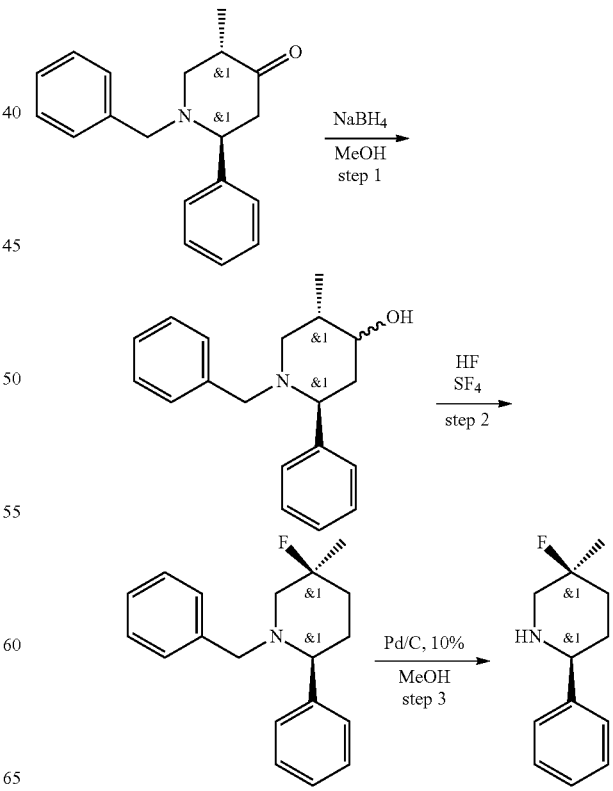

901
Preparation of 1-benzyl-5-methyl-2-phenyl-piperidin-4-on is Given Above

Step 1: Synthesis of rac-(2R,5R)-1-benzyl-5-methyl-2-phenylpiperidin-4-ol (2R,5R)-1-benzyl-5-methyl-2-phenyl-piperidin-4-one (350.00 mg, 1.25 mmol) was dissolved in MeOH (7 mL). The reaction mixture was cooled with cold water and sodium borohydride (71.09 mg, 1.88 mmol, 66.44 µL) was added. The reaction mixture was stirred overnight at rt. Solvent was removed on vacuo. The residue was diluted with $NH_4Cl$ (aq) and extracted with DCM (2×20 ml), DCM was dried over $Na_2SO_4$, filtered and concentrated on vacuo to give (2R,5R)-1-benzyl-5-methyl-2-phenyl-piperidin-4-ol (0.28 g, 995.06 µmol, 79.43% yield) as DM which was used in the next step without further purification.

$^1$H NMR (500 MHz, $CDCl_3$) δ (ppm) 0.94 (d, 3H), 1.47 (m, 1H), 1.70 (m, 2H), 1.96 (m, 1H), 2.09 (m, 1H), 2.76 (m, 1H), 2.88 (m, 1H), 3.24 (m, 1H), 3.76 (m, 1H), 7.25 (m, 10H), 7.45 (m, 1H).

LCMS(ESI): [M]$^+$ m/z: calcd 281.2; found 282.2; Rt=1.327 min.

Step 2: Synthesis of rac-(2R,5R)-1-benzyl-5-fluoro-5-methyl-2-phenylpiperidine (2R,5R)-1-benzyl-5-methyl-2-phenyl-piperidin-4-ol (0.28 g, 995.06 µmol), HF (199.07 mg, 9.95 mmol) and $SF_4$ (215.13 mg, 1.99 mmol) were heated in a stainless steel autoclave at 70° C. for 12 h. After completion of the reaction, the gaseous products were vented off, the reaction mixture was poured onto ice and neutralized with a 10% aqueous solution of $K_2CO_3$. The product was extracted with MTBE (3×100 mL). Combined organic extracts were washed with brine, dried over $Na_2SO_4$, and concentrated under reduced pressure to give crude product which was purified by HPLC (2-10 min 50-60% MeOH/$H_2O$ 30 ml/min (loading pump 4 mlMeOH) column: SunFire 100*19 mm, 5 microM) to give (2R,4S,5R)-1-benzyl-4-fluoro-5-methyl-2-phenyl-piperidine (0.065 g, 229.37 µmol, 23.05% yield) and (2R,5R)-1-benzyl-5-fluoro-5-methyl-2-phenyl-piperidine (0.044 g, 155.27 µmol, 15.60% yield).

$^1$H NMR (400 MHz, DMSO-$d_6$) δ (ppm) 1.23 (d, 3H), 1.68 (m, 2H), 1.78 (m, 2H), 2.12 (m, 1H), 2.88 (m, 2H), 3.18 (m, 1H), 3.68 (m, 1H), 7.23 (m, 6H), 7.36 (m, 2H), 7.48 (m, 2H).

LCMS(ESI): [M]$^+$ m/z: calcd 283.2; found 284.2; Rt=1.011 min.

Step 3: Synthesis of rac-(2R,5R)-5-fluoro-5-methyl-2-phenylpiperidine (2R,5R)-1-benzyl-5-fluoro-5-methyl-2-phenyl-piperidine (0.044 g, 155.27 µmol) was dissolved in MeOH (4 mL) and Pd/C 10% (0.006 g, 155.27 µmol) was added and hydrogenated with $H_2$ (1 atm) at rt for 36 hr. The reaction mixture was filtered through celite and filtrate was concentrated in vacuo at 45° C. to give (2R,5R)-5-fluoro-5-methyl-2-phenyl-piperidine (0.014 g, 72.44 µmol, 46.66% yield) which was used in the next step without further purification.

$^1$H NMR (400 MHz, $CDCl_3$) δ (ppm) 1.29 (d, 3H), 1.98 (m, 4H), 2.86 (m, 1H), 3.18 (m, 1H), 3.66 (m, 1H), 7.35 (m, 5H). LCMS(ESI): [M]$^+$ m/z: calcd 193.2; found 194.2; Rt=1.143 min.

902
3L. Synthesis of rac-(2R,5S)-2-(3-chloro-4,5-difluorophenyl)-5-methylpiperidine

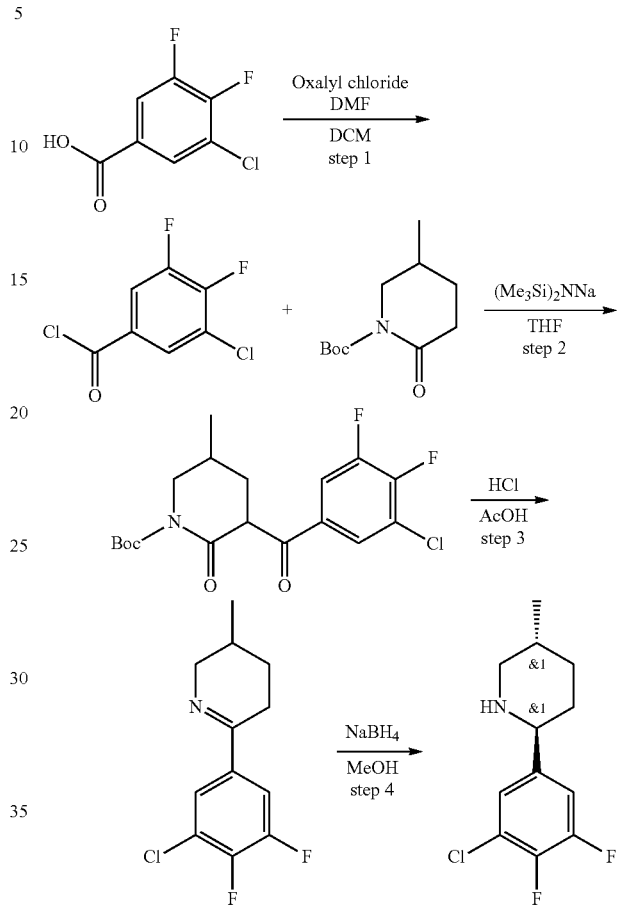

Step 1: Synthesis of 3-chloro-4,5-difluorobenzoyl chloride

Oxalyl chloride (1.98 g, 15.58 mmol, 1.35 mL) was added dropwise to a stirred suspension of 3-chloro-4,5-difluorobenzoic acid (2 g, 10.39 mmol) in DCM (20 mL). Then, DMF (94.40 mg, 1.29 mmol, 0.1 mL) was added thereto and resulting mixture was stirred at 20° C. for 3 hr. Volatiles were removed under reduced pressure. Residue was redissolved in hexane (40 mL), filtered and concentrated in vacuo, affording 3-chloro-4,5-difluoro-benzoyl chloride (2.1 g, 9.95 mmol, 95.82% yield).

$^1$H NMR (500 MHz, $CDCl_3$) δ (ppm) 7.88 (s, 1H), 8.02 (s, 1H).

GCMS: calcd 210.2; found 210.2; Rt=5.122 min.

Step 2: Synthesis of tert-butyl 3-(3-chloro-4,5-difluorobenzoyl)-5-methyl-2-oxopiperidine-1-carboxylate Sodium bis(trimethylsilyl)amide (40% in THF) (9.58 g, 20.90 mmol, 10.72 mL, 40% purity) was added dropwise to a precooled solution of tert-butyl 5-methyl-2-oxo-piperidine-1-carboxylate (2.12 g, 9.95 mmol) in THF (30 mL) at −78° C. After addition was complete, it was stirred at the same temperature for 1 hr. After that, 3-chloro-4,5-difluorobenzoyl chloride (2.1 g, 9.95 mmol) solution in hexane (8 mL) was added dropwise and cooling bath was removed. Resulting mixture was slowly warmed up to 20° C. and stirred at this temperature for 1 hr. Then, it was quenched with 15% aq·NaHSO₄ solution (40 ml) and extracted with ethyl acetate (40 ml). Organic layer was washed with 20% aq·NaCl solution (2×30 ml), dried over Na₂SO₄ and evaporated under reduced pressure, affording tert-butyl 3-(3-chloro-4,5-difluoro-benzoyl)-5-methyl-2-oxo-piperidine-1-carboxylate (3.8 g, 9.80 mmol, 98.45% yield).

¹H NMR (500 MHz, CDCl₃) δ (ppm) 0.96 (d, 3H), 1.56 (s, 9H), 2.22 (m, 4H), 3.17 (m, 1H), 3.86 (m, 1H), 7.57 (s, 1H), 7.85 (s, 1H).

LCMS(ESI): [M-Boc]⁺ m/z: calcd 287.2; found 288.2; Rt=1.596 min.

Step 3: Synthesis of 6-(3-chloro-4,5-difluorophenyl)-3-methyl-2,3,4,5-tetrahydropyridine tert-butyl 3-(3-chloro-4,5-difluoro-benzoyl)-5-methyl-2-oxo-piperidine-1-carboxylate (3.8 g, 9.80 mmol) was dissolved in acetic acid (20 mL) and hydrochloric acid, 30% aq. soln. (23.00 g, 189.24 mmol, 20 mL, 30% purity) was added portion wise. After addition was complete, resulting mixture was stirred at 100° C. for 5 hr. Then, solvents were removed under reduced pressure and residue was partitioned between 1 N HCl (50 ml) and EA (20 ml). Organic layer was separated and discarded. Aqueous layer was basified to ph≈10 with 10% NaOH and extracted with DCM (2×30 ml). DCM solution was separated, dried over K₂CO₃ and evaporated under reduced pressure, affording 6-(3-chloro-4,5-difluoro-phenyl)-3-methyl-2,3,4,5-tetrahydropyridine (1.5 g, 6.16 mmol, 62.82% yield).

¹H NMR (400 MHz, CDCl₃) δ (ppm) 0.96 (d, 3H), 1.36 (m, 1H), 1.68 (m, 1H), 1.91 (m, 1H), 2.48 (m, 1H), 2.68 (m, 1H), 3.26 (m, 1H), 3.99 (m, 1H), 7.54 (s, 1H), 7.61 (s, 1H).

LCMS(ESI): [M]⁺ m/z: calcd 243.2; found 244.2; Rt=1.026 min.

Step 4: Synthesis of rac-(2R,5S)-2-(3-chloro-4,5-difluorophenyl)-5-methylpiperidine Sodium borohydride (349.30 mg, 9.23 mmol, 326.45 μL) was added portion wise to a solution of 6-(3-chloro-4,5-difluoro-phenyl)-3-methyl-2,3,4,5-tetrahydropyridine (1.5 g, 6.16 mmol) in MeOH (30 mL) during 15 minutes. Resulting solution was stirred at 20° C. for 2 hr. Then, solvent was removed under reduced pressure and residue was partitioned between water (30 ml) and DCM (30 ml). Organic layer was separated, dried over K₂CO₃ and evaporated in vacuo, affording (2R,5S)-2-(3-chloro-4,5-difluoro-phenyl)-5-methyl-piperidine (1.48 g, 6.02 mmol, 97.86% yield).

¹H NMR (400 MHz, CDCl₃) δ (ppm) 0.86 (d, 3H), 1.12 (m, 1H), 1.41 (m, 1H), 1.82 (m, 4H), 2.36 (t, 1H), 3.11 (d, 1H), 3.56 (d, 1H), 7.08 (s, 1H), 7.19 (s, 1H).

LCMS(ESI): [M]⁺ m/z: calcd 245.2; found 246.2; Rt=0.921 min.

3M. Synthesis of rac-2-methyl-5-((2R,5S)-5-methylpiperidin-2-yl)phenol

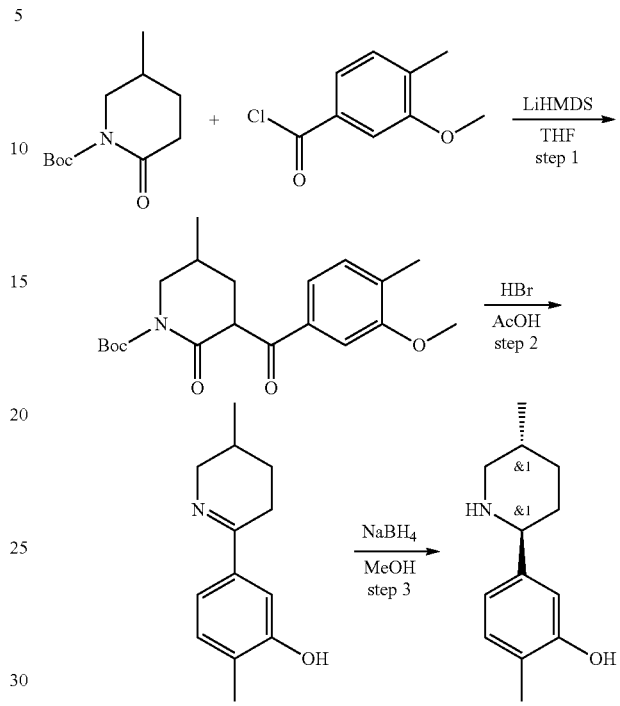

Step 1: Synthesis of tert-butyl 3-(3-methoxy-4-methylbenzoyl)-5-methyl-2-oxopiperidine-1-carboxylate To the pre-cooled (−78° C.) solution of tert-butyl 5-methyl-2-oxo-piperidine-1-carboxylate (19 g, 89.09 mmol) in THF (350 mL) LiHMDS (189 mmol, 178 mL) was added dropwise. The resulting mixture was stirred at −78° C. for 1 hr. The solution of 3-methoxy-4-methyl-benzoyl chloride (16.45 g, 89.09 mmol) was added in one portion. The reaction mixture was allowed to warm to room temperature and stirred at that temperature for 4 hr. The reaction mixture was quenched with NaHSO₄ (45 g; 10% solution) and extracted with DCM (3*150 ml). Organic layers was washed with water, dried over Na₂SO₄. DCM was evaporated to give tert-butyl 3-(3-methoxy-4-methyl-benzoyl)-5-methyl-2-oxo-piperidine-1-carboxylate (38 g, crude).

¹H NMR (400 MHz, CDCl₃) δ (ppm) 0.96 (d, 3H), 1.18 (m, 1H), 1.49 (s, 9H), 1.98 (m, 2H), 2.24 (s, 3H), 2.56 (m, 1H), 3.23 (m, 1H), 3.86 (s, 3H), 4.54 (m, 1H), 7.24 (m, 2H), 7.44 (m, 1H).

LCMS(ESI): [M-Boc]⁺ m/z: calcd 261.4; found 262.2; Rt=1.443 min.

Step 2: Synthesis of 2-methyl-5-(5-methyl-3,4,5,6-tetrahydropyridin-2-yl)phenol tert-butyl 3-(3-methoxy-4-methyl-benzoyl)-5-methyl-2-oxo-piperidine-1-carboxylate (2 g, 5.53 mmol) was dissolved in acetic acid (20 mL) and hydrogen bromide water solution (48 wt. %) (20 mL) was added portion wise. After addition was complete, resulting mixture was stirred at 100° C. for 14 hr. Then, solvents were removed under reduced pressure and residue was partitioned between 1 N HCl (5 ml)

and DCM (20 ml). Organic layer was separated and discarded. Aqueous layer was basified to ph≈10 with 10% NaOH and extracted with EtOAc (3×30 ml). EtOAc solution was separated, dried over Na₂SO₄ and evaporated under reduced pressure, affording 2-methyl-5-(3-methyl-2,3,4,5-tetrahydropyridin-6-yl)phenol (400 mg, 1.97 mmol, 35.56% yield).

¹H NMR (400 MHz, CDCl₃) δ (ppm) 0.96 (d, 3H), 1.38 (m, 2H), 1.69 (m, 1H), 1.86 (m, 1H), 2.24 (s, 3H), 2.51 (m, 1H), 2.70 (m, 1H), 3.19 (m, 1H), 3.94 (m, 1H), 7.02 (m, 2H), 7.33 (m, 1H).

LCMS(ESI): [M]⁺ m/z: calcd 203.4; found 204.2; Rt=0.893 min.

Step 3: Synthesis of rac-2-methyl-5-((2R,5S)-5-methylpiperidin-2-yl)phenol

To a solution of 2-methyl-5-(3-methyl-2,3,4,5-tetrahydropyridin-6-yl)phenol (400 mg, 1.97 mmol) in MeOH (20 mL), sodium borohydride (74.44 mg, 1.97 mmol, 69.57 μL) was added portionwise at 25° C. The resulting mixture was stirred at 25° C. for 2 hr and evaporated in vacuo. The residue was treated with hydrogen chloride dioxane solution. Then dioxane was evaporated. Precipitate was washed with THF, dried in vacuo to give 2-methyl-5-[(2S,5R)-5-methyl-2-piperidyl]phenol (450 mg, 1.86 mmol, 94.60% yield, HCl).

¹H NMR (500 MHz, CDCl₃) δ (ppm) 0.96 (d, 3H), 1.22 (m, 1H), 1.86 (m, 4H), 2.14 (s, 3H), 2.48 (m, 1H), 2.56 (m, 1H), 3.14 (m, 1H), 5.74 (m, 1H), 6.81 (m, 1H), 7.01 (m, 1H), 7.18 (m, 1H), 9.01 (bds, 1H).

LCMS(ESI): [M]⁺ m/z: calcd 205.4; found 206.2; Rt=0.895 min.

3N. The Synthesis of 4-[(2S,5R)-5-methyl-2-piperidyl]-N-(2,2,2-trifluoroethyl)aniline

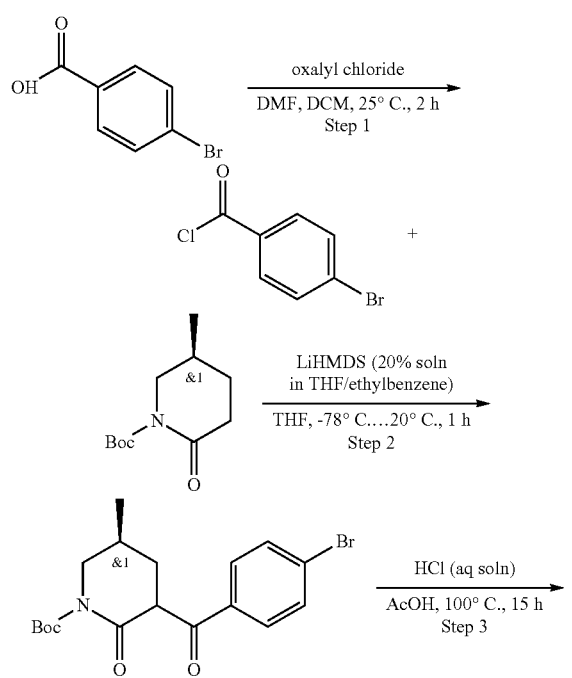

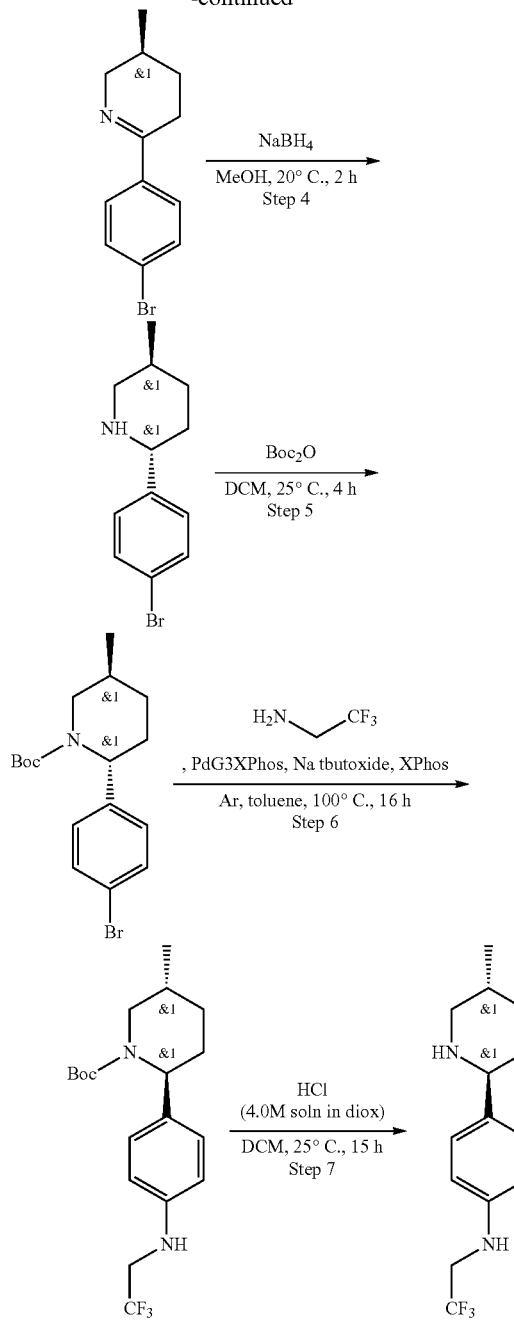

Step 1: The Synthesis of 4-bromobenzoyl chloride 4-bromobenzoic acid (20 g, 99.49 mmol) and oxalyl chloride (18.94 g, 149.24 mmol, 12.97 mL) were suspended in dichloromethane (200 mL). Then, dimethylformamide (94.40 mg, 1.29 mmol, 0.1 mL) was added thereto in 3 portions. The resulting mixture was stirred at 25° C. for 2 hr. When gas evolution ceased, the resulting clear solution was concentrated under reduced pressure. The residue was redissolved in hexane (150 mL), filtered and evaporated in vacuo, affording 4-bromobenzoyl chloride (21.5 g, 97.97 mmol, 98.46% yield).

¹H NMR (500 MHz, CDCl₃) δ 7.66 (d, 2H), 7.97 (d, 2H).
GCMS: [M+H]⁺ m/z: calcd 219.2; found 219.9; Rt=5.646 min.

Step 2: The Synthesis of tert-butyl 3-(4-bromobenzoyl)-5-methyl-2-oxo-piperidine-1-carboxylate LiHMDS (20% in THF/Ethylbenzene) (172.12 g, 205.73 mmol, 194.05 mL, 20% purity) was added dropwise to a precooled solution of tert-butyl 5-methyl-2-oxo-piperidine-1-carboxylate (20.89 g, 97.97 mmol) in tetrahydrofuran (150 mL) at −78° C. After addition was complete, it was stirred at the same temperature for 1 h. After that, 4-bromobenzoyl chloride (21.5 g, 97.97 mmol) was added in one portion and cooling bath was removed. The resulting mixture was slowly warmed up to 20° C. and stirred at this temperature for 1 hr. Then, it was quenched with 15% aq·NaHSO$_4$ (250 mL) and extracted with ethyl acetate (300 mL). The organic layer was washed with 20% aq·NaCl (2*250 mL), dried over Na$_2$SO$_4$ and evaporated under reduced pressure, affording tert-butyl 3-(4-bromobenzoyl)-5-methyl-2-oxo-piperidine-1-carboxylate (41.7 g, crude).

$^1$H NMR (400 MHz, CDCl$_3$) δ 1.12 (m, 3H), 1.62 (s, 9H), 1.87 (m, 3H), 3.14 (m, 1H), 3.82 (m, 1H), 4.46 (m, 1H), 7.18 (d, 1H), 7.54 (d, 1H), 7.66 (d, 1H), 7.82 (d, 1H).

LCMS(ESI): [M+H]$^+$ m/z: calcd 395.1; found 396.0; Rt=1.363 min.

Step 3: The Synthesis of 6-(4-bromophenyl)-3-methyl-2,3,4,5-tetrahydropyridine tert-butyl 3-(4-bromobenzoyl)-5-methyl-2-oxo-piperidine-1-carboxylate (40.4 g, 101.95 mmol) was dissolved in Acetic Acid (300 mL) and Hydrochloric acid, 30% w/w aq. soln. (345.00 g, 2.84 mol, 300 mL, 30% purity) was added portionwise (caution! foam is formed). After addition was complete, the resulting mixture was stirred at 100° C. for 15 hr. Then, solvents were removed under reduced pressure and the residue was partitioned between 1 N HCl (500 mL) and DCM (400 mL). The organic layer was separated and discarded. Aqueous layer was basified to pH 10 with 10% NaOH and extracted with DCM (2*200 mL). DCM solution was separated, dried over K$_2$CO$_3$ and evaporated under reduced pressure, affording 6-(4-bromophenyl)-3-methyl-2,3,4,5-tetrahydropyridine (17.2 g, 68.21 mmol, 66.91% yield).

$^1$H NMR (400 MHz, CDCl$_3$) δ 0.97 (m, 3H), 1.35 (m, 1H), 1.69 (m, 1H), 1.89 (m, 1H), 2.52 (m, 1H), 2.70 (m, 1H), 3.22 (m, 1H), 3.96 (m, 1H), 7.48 (d, 2H), 7.62 (d, 2H).

LCMS(ESI): [M+3H]$^+$ m/z: calcd 251.1; found 254.0; Rt=0.864 min.

Step 4: The Synthesis of rac-(2R,5S)-2-(4-bromophenyl)-5-methyl-piperidine

Sodium borohydride (2.58 g, 68.21 mmol, 2.41 mL) was added portionwise to a solution of 6-(4-bromophenyl)-3-methyl-2,3,4,5-tetrahydropyridine (17.2 g, 68.21 mmol) in methanol (250 mL) during 15 minutes. The resulting solution was stirred at 20° C. for 2 hr. Then, solvent was removed under reduced pressure and residue was partitioned between water (100 mL) and DCM (200 mL). The organic layer was separated, dried over Na$_2$SO$_4$ and evaporated in vacuo, affording rac-(2R,5S)-2-(4-bromophenyl)-5-methyl-piperidine (17.3 g, 68.07 mmol, 99.78% yield). It contains 12% of cis-impurity.

$^1$H NMR (500 MHz, CDCl$_3$) δ 0.90 (m, 3H), 1.15 (m, 2H), 1.48 (m, 1H), 1.59 (m, 1H), 1.65 (m, 1H), 1.86 (m, 1H), 2.41 (t, 1H), 3.13 (m, 1H), 3.51 (m, 1H), 7.24 (m, 2H), 7.43 (d, 2H).

LCMS(ESI): [M+3H]$^+$ m/z: calcd 253.1; found 256.0; Rt=0.821 min.

Step 5: The Synthesis of tert-butyl (2R,5S)-2-(4-bromophenyl)-5-methyl-piperidine-1-carboxylate (2R,5S)-2-(4-bromophenyl)-5-methyl-piperidine (17.3 g, 68.07 mmol) was dissolved in dichloromethane (250 mL) and di-tert-butyl dicarbonate (15.15 g, 69.43 mmol, 15.93 mL) was added dropwise (vigorous gas evolution!). Resulting mixture was stirred at 25° C. for 4 hr. Then, volatiles were removed under reduced pressure, affording tert-butyl (2R,5S)-2-(4-bromophenyl)-5-methyl-piperidine-1-carboxylate (24.3 g, crude).

$^1$H NMR (500 MHz, CDCl$_3$) δ 1.05 (d, 3H), 1.29 (m, 1H), 1.45 (s, 9H), 1.58 (m, 1H), 1.83 (m, 1H), 1.97 (m, 1H), 2.12 (m, 1H), 2.97 (d, 1H), 3.72 (d, 1H), 5.26 (m, 1H), 7.12 (d, 2H), 7.45 (d, 2H).

LCMS(ESI): [M-Boc]$^+$ m/z: calcd 253.2; found 256.0; Rt=1.691 min.

Step 6: The Synthesis of tert-butyl (2S,5R)-5-methyl-2-[4-(2,2,2-trifluoroethylamino)phenyl]piperidine-1-carboxylate tert-butyl (2S,5R)-2-(4-bromophenyl)-5-methyl-piperidine-1-carboxylate (1.6 g, 4.52 mmol), 2,2,2-trifluoroethanamine (1.57 g, 15.81 mmol, 1.25 mL) and sodium tert-butoxide (651.01 mg, 6.77 mmol) were mixed together in Toluene (15 mL). Reaction flask was briefly evacuated and refilled with argon and PdG3XPhos (191.14 mg, 225.81 µmol) with XPhos (107.65 mg, 225.81 µmol) were added under stream of argon. Resulting mixture was stirred at 100° C. for 16 hr in a sealed vessel. Then, it was cooled to r.t. and poured into 10% aq. NH$_4$Cl (10 ml). Obtained mixture was extracted with ethyl acetate (20 ml). Organic layer was separated and treated with Pd-scavenger (0.5 g) for 3 h. After drying over Na$_2$SO$_4$, solvent was removed under reduced pressure affording tert-butyl (2S,5R)-5-methyl-2-[4-(2,2,2-trifluoroethylamino)phenyl]piperidine-1-carboxylate (1.85 g, crude).

$^1$H NMR (400 MHz, CDCl$_3$) δ 0.75 (m, 1H), 1.01 (d, 3H), 1.26 (m, 2H), 1.44 (s, 9H), 1.76 (m, 2H), 2.04 (m, 2H), 2.90 (m, 1H), 3.72 (m, 2H), 5.25 (m, 1H), 6.64 (d, 2H), 7.04 (m, 2H).

LCMS(ESI): [M-Boc]$^+$ m/z: calcd 272.2; found 273.2; Rt=1.621 min.

Step 7: The Synthesis of 4-[(2S,5R)-5-methyl-2-piperidyl]-N-(2,2,2-trifluoroethyl)aniline tert-butyl (2S,5R)-5-methyl-2-[4-(2,2,2-trifluoroethylamino)phenyl]piperidine-1-carboxylate (1.85 g, 4.97 mmol) was dissolved in dichloromethane (20 mL) and hydrogen chloride solution 40 M in dioxane (18.11 g, 49.67 mmol, 17.93 mL, 10% purity was added. Resulting mixture was stirred at 25° C. for 15 hr and concentrated under reduced pressure. Residue was triturated with ethyl acetate (25 ml). Obtained gray precipitate was filtered and dried affording 4-[(2S,5R)-5-methyl-2-piperidyl]-N-(2,2,2-trifluoroethyl)aniline (1.2 g, 3.48 mmol, 69.97% yield, 2HCl).

$^1$H NMR (400 MHz, DMSO-d$_6$) δ 0.87 (m, 1H), 1.05 (d, 3H), 1.49 (m, 1H), 1.75 (m, 2H), 1.97 (m, 2H), 2.83 (m, 1H), 3.09 (m, 1H), 3.88 (m, 2H), 4.04 (m, 1H), 5.74 (s, 1H), 6.71 (d, 2H), 7.26 (d, 2H), 8.53 (m, 1H), 9.43 (m, 1H).

LCMS(ESI): [M+H]$^+$ m/z: calcd 272.2; found 273.2; Rt=0.967 min.

3O. The Synthesis of N,N-dimethyl-2-[4-[(2S,5R)-5-methyl-2-piperidyl]anilino]acetamide

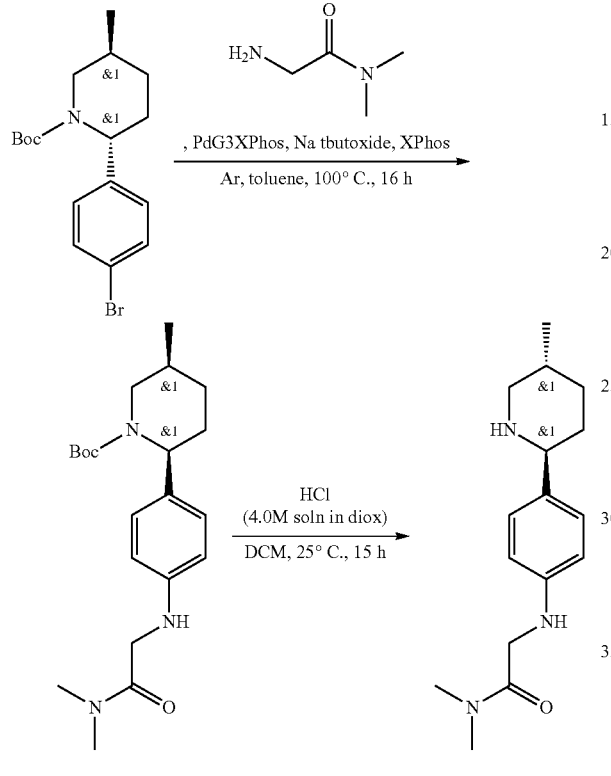

Step 1: The Synthesis of tert-butyl (2S,5R)-2-[4-[[2-(dimethylamino)-2-oxo-ethyl]amino]phenyl]-5-methyl-piperidine-1-carboxylate tert-butyl (2S,5R)-2-(4-bromophenyl)-5-methyl-piperidine-1-carboxylate (1.5 g, 4.23 mmol)(prepared as shown above), 2-amino-N,N-dimethyl-acetamide (475.68 mg, 4.66 mmol, HCl) and sodium tert-butoxide (1.02 g, 10.58 mmol) were mixed together in toluene (20 mL). Reaction flask was evacuated and refilled with argon for 3 times and PdG3XPhos (179.19 mg, 211.70 μmol) with XPhos (100.92 mg, 211.70 μmol) were added under stream of argon. Resulting mixture was stirred at 100° C. for 16 hr. Then, it was cooled to r.t. and poured into 10% aq. NH$_4$Cl (15 ml). Obtained mixture was extracted with ethyl acetate (25 ml). Organic layer was separated and treated with Pd-scavenger (0.5 g) for 3 h. After drying over Na$_2$SO$_4$, solvent was removed under reduced pressure, affording tert-butyl (2S,5R)-2-[4-[[2-(dimethylamino)-2-oxo-ethyl]amino]phenyl]-5-methyl-piperidine-1-carboxylate (1.58 g, 4.21 mmol, 99.38% yield).

$^1$H NMR (400 MHz, CDCl$_3$) δ 1.01 (m, 4H), 1.28 (m, 3H), 1.44 (s, 9H), 1.77 (m, 3H), 2.35 (m, 1H), 2.95 (m, 2H), 3.01 (s, 3H), 3.67 (m, 1H), 3.84 (m, 2H), 5.26 (m, 1H), 6.62 (d, 1H), 7.03 (m, 1H), 7.14 (m, 1H), 7.22 (m, 1H).

LCMS(ESI): [M-Boc]$^+$ m/z: calcd 275.2; found 276.2; Rt=1.392 min.

Step 2: The Synthesis of N,N-dimethyl-2-[4-[(2S,5R)-5-methyl-2-piperidyl]anilino]acetamide tert-butyl (2S,5R)-2-[4-[[2-(dimethylamino)-2-oxo-ethyl]amino]phenyl]-5-methyl-piperidine-1-carboxylate (1.58 g, 4.21 mmol) was dissolved in dichloromethane (15 mL) and hydrogen chloride solution 40 M in dioxane (15.34 g, 42.08 mmol, 15.19 mL, 10% purity) was added. Resulting mixture was stirred at 25° C. for 15 hr and concentrated under reduced pressure. Residue was triturated with ethyl acetate (20 ml). Obtained gray precipitate was filtered and dried, affording N,N-dimethyl-2-[4-[(2S,5R)-5-methyl-2-piperidyl]anilino]acetamide (1.2 g, 3.45 mmol, 81.88% yield, 2HCl).

$^1$H NMR (400 MHz, DMSO-d$_6$) δ 0.93 (d, 3H), 1.17 (m, 2H), 1.98 (m, 2H), 2.65 (m, 1H), 2.87 (s, 3H), 3.14 (s, 3H), 3.98 (m, 2H), 4.52 (m, 1H), 6.82 (d, 2H), 7.35 (d, 2H), 7.71 (m, 1H), 9.13 (m, 1H), 9.35 (m, 1H).

LCMS(ESI): [M+H]$^+$ m/z: calcd 275.2; found 276.2; Rt=0.842 min.

3P. The Synthesis of 1-methyl-3-[4-[(2S,5R)-5-methyl-2-piperidyl]anilino]pyrrolidin-2-one

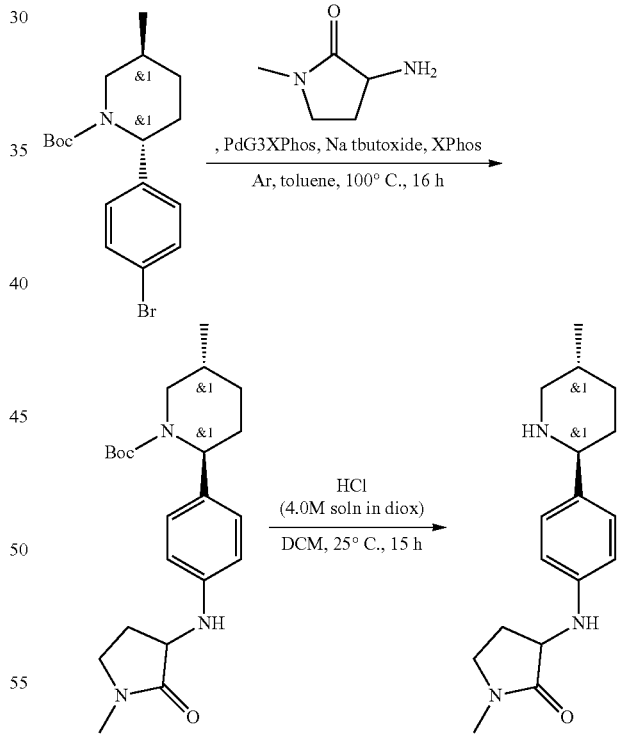

Step 1: The Synthesis of tert-butyl (2S,5R)-5-methyl-2-[4-[(1-methyl-2-oxo-pyrrolidin-3-yl)amino]phenyl]piperidine-1-carboxylate tert-butyl (2S,5R)-2-(4-bromophenyl)-5-methyl-piperidine-1-carboxylate (1.5 g, 4.23 mmol) (prepared as described above), 3-amino-1-methyl-pyrrolidin-2-one (531.61 mg, 4.66 mmol, HCl) and sodium tert-butoxide (1.02 g, 10.58 mmol) were mixed together in toluene (20 mL). Reaction flask was evacuated and refilled with argon for 3 times and PdG3XPhos (179.19 mg, 211.70 μmol) with XPhos (100.92 mg, 211.70 μmol) were added under stream of argon. Resulting mixture was stirred at 100° C. for 16 hr. Then, it was cooled to r.t. and poured into 10% aq. NH₄Cl (15 ml). Obtained mixture was extracted with ethyl acetate (25 ml). Organic layer was separated and treated with Pd-scavenger (0.5 g) for 3 h. After drying over Na₂SO₄, solvent was removed under reduced pressure, affording tert-butyl (2S,5R)-5-methyl-2-[4-[(1-methyl-2-oxo-pyrrolidin-3-yl)amino]phenyl]piperidine-1-carboxylate (1.66 g, crude).

¹H NMR (400 MHz, CDCl₃) δ 1.01 (m, 4H), 1.28 (m, 4H), 1.44 (s, 9H), 2.02 (m, 4H), 2.66 (m, 1H), 2.92 (s, 3H), 3.39 (m, 1H), 3.69 (m, 1H), 3.90 (m, 1H), 5.22 (m, 1H), 6.64 (d, 1H), 7.05 (m, 2H), 7.15 (m, 1H).

LCMS(ESI): [M-Boc]⁺ m/z: calcd 287.2; found 288.2; Rt=1.381 min.

Step 2: The Synthesis of 1-methyl-3-[4-[(2S,5R)-5-methyl-2-piperidyl]anilino]pyrrolidin-2-one tert-butyl (2S,5R)-5-methyl-2-[4-[(1-methyl-2-oxo-pyrrolidin-3-yl)amino]phenyl]piperidine-1-carboxylate (1.66 g, 4.28 mmol) was dissolved in dichloromethane (20 mL) and hydrogen chloride solution 40 M in dioxane (15.62 g, 42.84 mmol, 15.46 mL, 10% purity) was added. Resulting mixture was stirred at 25° C. for 15 hr and concentrated under reduced pressure. Residue was triturated with ethyl acetate (25 ml). Obtained gray precipitate was filtered and dried, affording 1-methyl-3-[4-[(2S,5R)-5-methyl-2-piperidyl]anilino]pyrrolidin-2-one (1.24 g, 3.44 mmol, 80.34% yield, 2HCl).

¹H NMR (400 MHz, DMSO-d₆) δ 0.87 (d, 3H), 1.07 (m, 2H), 1.94 (m, 2H), 2.56 (m, 2H), 2.73 (s, 3H), 3.09 (m, 2H), 3.27 (m, 2H), 3.52 (s, 2H), 4.08 (m, 1H), 5.62 (m, 1H), 6.72 (d, 2H), 7.39 (d, 2H), 9.10 (m, 1H), 9.38 (m, 1H), 9.78 (m, 1H).

LCMS(ESI): [M+H]⁺ m/z: calcd 287.2; found 288.2; Rt=0.847 min.

3Q. The Synthesis of N,N-dimethyl-2-[4-[(2S,5R)-5-methyl-2-piperidyl]anilino]propanamide

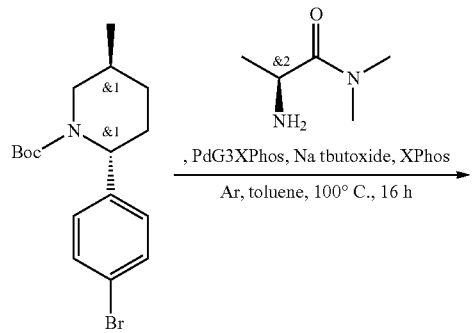

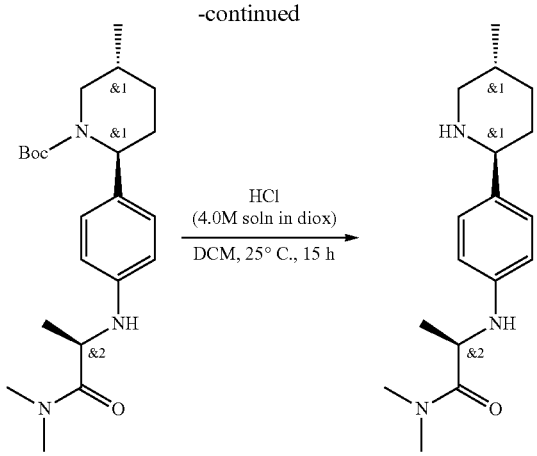

Step 1: The Synthesis of tert-butyl (2S,5R)-2-[4-[[2-(dimethylamino)-1-methyl-2-oxo-ethyl]amino]phenyl]-5-methyl-piperidine-1-carboxylate tert-butyl (2S,5R)-2-(4-bromophenyl)-5-methyl-piperidine-1-carboxylate (820 mg, 2.31 mmol) (prepared as described above), (2S)-2-amino-N,N-dimethyl-propanamide (388.58 mg, 2.55 mmol, HCl) and sodium tert-butoxide (556.07 mg, 5.79 mmol) were mixed together in toluene (15 mL). Reaction flask was evacuated and refilled with argon for 3 times and PdG3XPhos (97.96 mg, 115.73 μmol) with XPhos (55.17 mg, 115.73 μmol) were added under stream of argon. Resulting mixture was stirred at 100° C. for 16 hr. Then, it was cooled to r.t. and poured into 10% aq. NH₄Cl (10 ml). Obtained mixture was extracted with ethyl acetate (20 ml). Organic layer was separated and treated with Pd-scavenger (0.5 g) for 3 h. After drying over Na₂SO₄, solvent was removed under reduced pressure, affording tert-butyl (2S,5R)-2-[4-[[2-(dimethylamino)-1-methyl-2-oxo-ethyl]amino]phenyl]-5-methyl-piperidine-1-carboxylate (940 mg, crude).

¹H NMR (400 MHz, CDCl₃) δ 1.00 (d, 3H), 1.27 (m, 2H), 1.35 (m, 3H), 1.43 (s, 9H), 1.75 (m, 2H), 1.97 (m, 2H), 2.96 (m, 3H), 3.08 (s, 3H), 3.65 (m, 1H), 4.40 (m, 1H), 5.24 (m, 1H), 6.63 (d, 2H), 7.02 (d, 2H), 7.24 (m, 1H).

LCMS(ESI): [M-ᵗBu]⁺ m/z: calcd 333.2; found 334.2; Rt=1.477 min.

Step 2: The Synthesis of N,N-dimethyl-2-[4-[(2S,5R)-5-methyl-2-piperidyl]anilino]propanamide tert-butyl (2S,5R)-2-[4-[[2-(dimethylamino)-1-methyl-2-oxo-ethyl]amino]phenyl]-5-methyl-piperidine-1-carboxylate (0.94 g, 2.41 mmol) was dissolved in dichloromethane (10 mL) and hydrogen chloride solution 4.0 M in dioxane (8.80 g, 24.13 mmol, 8.71 mL, 10% purity) was added. Resulting mixture was stirred at 25° C. for 15 hr and concentrated under reduced pressure. Residue was triturated with ethyl acetate (10 ml). Obtained gray precipitate was filtered and dried, affording N,N-dimethyl-2-[4-[(2S,5R)-5-methyl-2-piperidyl]anilino]propanamide (0.69 g, 1.90 mmol, 78.91% yield, 2HCl).

¹H NMR (400 MHz, DMSO-d₆) δ 0.91 (d, 3H), 1.10 (m, 1H), 1.25 (m, 4H), 1.82 (m, 3H), 2.01 (m, 2H), 2.65 (m, 1H), 2.82 (s, 3H), 3.07 (s, 3H), 3.17 (m, 1H), 3.56 (m, 1H), 4.55 (m, 1H), 6.78 (d, 2H), 7.34 (d, 2H), 9.05 (m, 1H), 9.28 (m, 1H).

LCMS(ESI): [M+H]⁺ m/z: calcd 289.2; found 290.2; Rt=0.765 min.

3R. The Synthesis of 5-[[2-[(2S,5R)-5-methyl-2-[4-(1H-pyrazol-5-yl)phenyl]-1-piperidyl]-2-oxo-acetyl]amino]pyridine-3-carboxamide

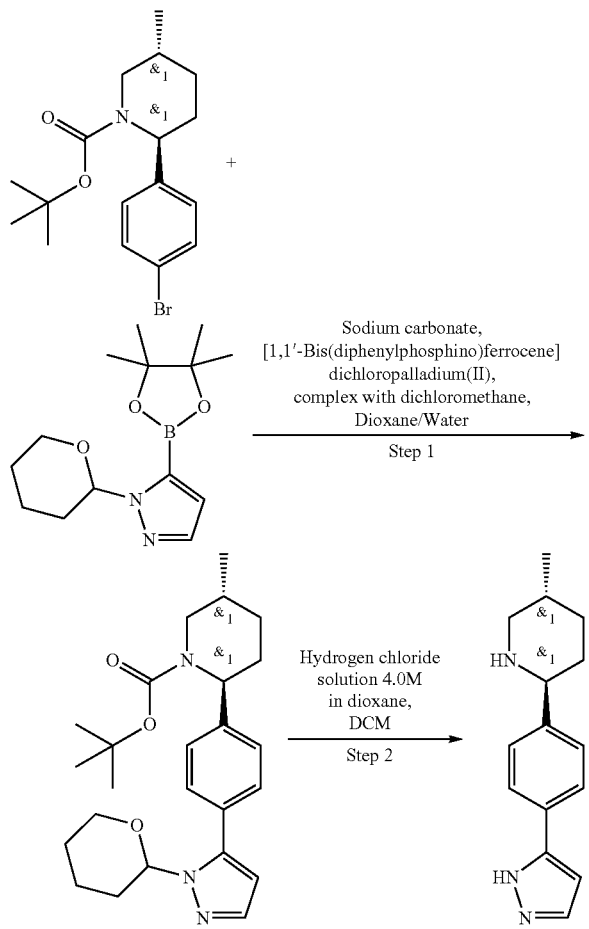

Step 1: Synthesis of tert-butyl (2S,5R)-5-methyl-2-[4-(2-tetrahydropyran-2-ylpyrazol-3-yl)phenyl]piperidine-1-carboxylate A suspension of tert-butyl (2S,5R)-2-(4-bromophenyl)-5-methyl-piperidine-1-carboxylate (1.5 g, 4.23 mmol)(prepared as described above), 1-tetrahydropyran-2-yl-5-(4,4,5,5-tetramethyl-1,3,2-dioxaborolan-2-yl)pyrazole (1.30 g, 4.66 mmol), Sodium carbonate (1.35 g, 12.70 mmol, 532.11 µL) in Dioxane (30 mL) and Water (5 mL) was degassed and refilled with Ar three time. To this solution, [1,1'-Bis(diphenylphosphino)ferrocene]dichloropalladium(II), complex with dichloromethane (172.88 mg, 211.70 µmol) was added. The resulting mixture was degassed, refilled with Ar and stirred at 90° C. for 12 hr. The precipitate was filtered off, washed with dioxane (50 ml). The solvent was evaporated in vacuo and residue was taken up with water 50 ml and extracted with EtOAc (2*50 ml). The combined organic layer was washed with brine (50 ml), dried over Na₂SO₄ and evaporated to obtain crude product (2.5 g). The crude product was purified by gradient chromatography (Hexane-MTBE) to obtain tert-butyl (2S,5R)-5-methyl-2-[4-(2-tetrahydropyran-2-ylpyrazol-3-yl)phenyl]piperidine-1-carboxylate (0.4 g, 939.93 µmol, 22.20% yield).

¹H NMR (DMSO-d₆, 500 MHz): 0.91 (d, 3H), 1.31 (s, 9H), 1.47 (m, 4H), 1.72 (m, 2H), 1.99 (m, 4H), 2.31 (m, 1H), 2.90 (m, 1H), 3.47 (m, 2H), 3.90 (m, 1H), 5.07 (m, 1H), 5.13 (m, 1H), 6.24 (d, 1H), 7.21 (m, 2H), 7.38 (m, 3H),

LCMS(ESI): [M+Na]⁺ m/z: calcd 425.3; found 448.2; Rt=1.736 min.

Step 2: Synthesis of (2S,5R)-5-methyl-2-[4-(1H-pyrazol-5-yl)phenyl]piperidine

To a solution of tert-butyl (2S,5R)-5-methyl-2-[4-(2-tetrahydropyran-2-ylpyrazol-3-yl)phenyl]piperidine-1-carboxylate (0.4 g, 939.93 µmol) in DCM (10 mL), Hydrogen chloride solution 40 M in dioxane (8.00 g, 219.41 mmol, 10 mL) was added. The resulting mixture was stirred at 25° C. for 24 hr and evaporated under reduced pressure. The residue was triturated with EtOH and MTBE 1:1 (3 ml) and the precipitate was filtered to give (2S,5R)-5-methyl-2-[4-(1H-pyrazol-5-yl)phenyl]piperidine (0.25 g, 795.54 µmol, 84.64% yield, 2HCl).

¹H NMR (DMSO-d₆, 400 MHz): 0.91 (d, 3H), 1.32 (m, 2H), 1.90 (m, 3H), 2.01 (m, 2H), 2.67 (m, 1H), 3.22 (m, 1H), 4.13 (m, 2H), 6.73 (d, 1H), 7.56 (d, 1H), 7.71 (d, 1H), 7.84 (d, 1H).

LCMS(ESI): [M+H]⁺ m/z: calcd 241.2; found 242.2; Rt=0.919 min.

3S. Synthesis of Rac (2S,5R)-5-methyl-2-[4-(1H-pyrazol-4-yl)phenyl]piperidine

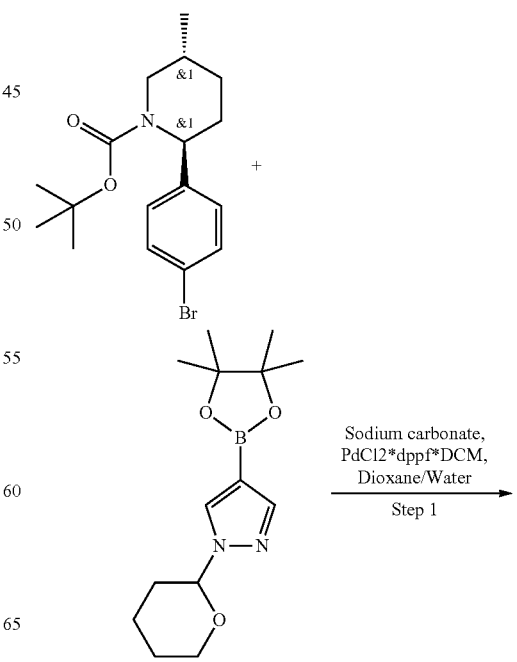

-continued

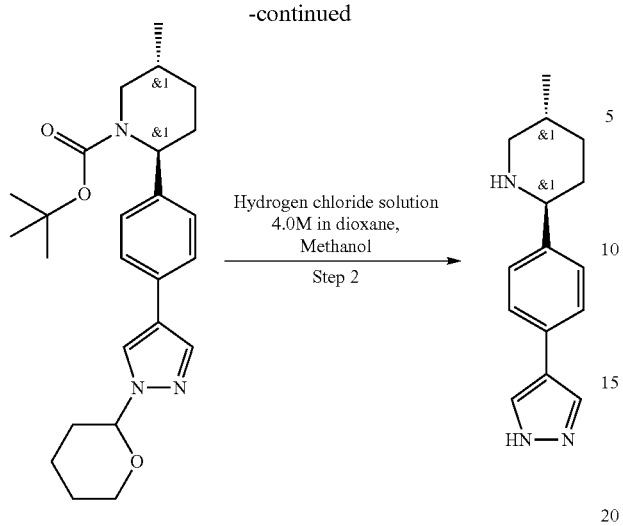

Step 1: Synthesis of tert-butyl (2S,5R)-5-methyl-2-[4-(1-tetrahydropyran-2-ylpyrazol-4-yl)phenyl]piperidine-1-carboxylate tert-butyl (2S,5R)-2-(4-bromophenyl)-5-methyl-piperidine-1-carboxylate (1 g, 2.82 mmol) (prepared as described above), 1-tetrahydropyran-2-yl-4-(4,4,5,5-tetramethyl-1,3,2-dioxaborolan-2-yl)pyrazole (785.13 mg, 2.82 mmol) and Sodium carbonate (448.75 mg, 4.23 mmol, 177.37 µL) were mixed together in Dioxane (8 mL) and Water (2 mL). Reaction flask was evacuated and refilled with argon 3 times and PdCl$_2$*dppf*DCM (92.20 mg, 112.90 µmol) was added under stream of argon. Resulting mixture was stirred at 90° C. for 20 hr. Then, solvents were removed under reduced pressure and residue was redissolved in MTBE (30 ml). This solution was filtered through a short pad of silicagel and residue was evaporated in vacuo, affording tert-butyl (2S,5R)-5-methyl-2-[4-(1-tetrahydropyran-2-ylpyrazol-4-yl)phenyl]piperidine-1-carboxylate (1.49 g, crude).

$^1$H NMR (CDCl$_3$, 400 MHz): 1.02 (d, 3H), 1.04 (m, 1H), 1.17 (s, 9H), 1.43 (m, 2H), 1.61 (m, 2H), 1.69 (m, 2H), 1.81 (m, 1H), 2.03 (m, 4H), 2.99 (m, 1H), 3.71 (m, 2H), 4.06 (m, 1H), 5.40 (m, 1H), 7.22 (m, 2H), 7.43 (m, 2H), 7.79 (s, 1H), 7.82 (s, 1H).
LCMS(ESI): [M+Na]$^+$ m/z: calcd 425.3; found 448.2; Rt=1.679 min.

Step 2: Synthesis of (2S,5R)-5-methyl-2-[4-(1H-pyrazol-4-yl)phenyl]piperidine

Hydrogen chloride solution 40 M in dioxane (12.75 g, 34.97 mmol, 12.62 mL, 10% purity) was added to a solution of tert-butyl (2S,5R)-5-methyl-2-[4-(1-tetrahydropyran-2-ylpyrazol-4-yl)phenyl]piperidine-1-carboxylate (1.49 g, 3.50 mmol) in Methanol (15 mL). Resulting mixture was stirred at 20° C. for 15 hr and concentrated under reduced pressure. Residue was triturated with ethyl acetate (25 ml). Resulting precipitate was filtered, rinsed with ice-cold ethanol (15 ml) and dried, affording (2S,5R)-5-methyl-2-[4-(1H-pyrazol-4-yl)phenyl]piperidine (580 mg, 1.85 mmol, 52.78% yield, 2HCl).

$^1$H NMR (DMSO-d$_6$, 400 MHz): 0.91 (d, 3H), 1.08 (m, 1H), 1.29 (m, 1H), 1.89 (m, 3H), 2.02 (m, 2H), 2.63 (m, 1H), 3.18 (m, 1H), 4.17 (m, 2H), 7.52 (d, 1H), 7.62 (d, 1H), 8.08 (s, 2H), 9.23 (s, 1H), 9.42 (s, 1H).

LCMS(ESI): [M+H]$^+$ m/z: calcd 241.19 found 242.2; Rt=0.819 min.

3T. The Synthesis of Rac Methyl 4-[(2R,5S)-5-methyl-2-piperidyl]benzoate

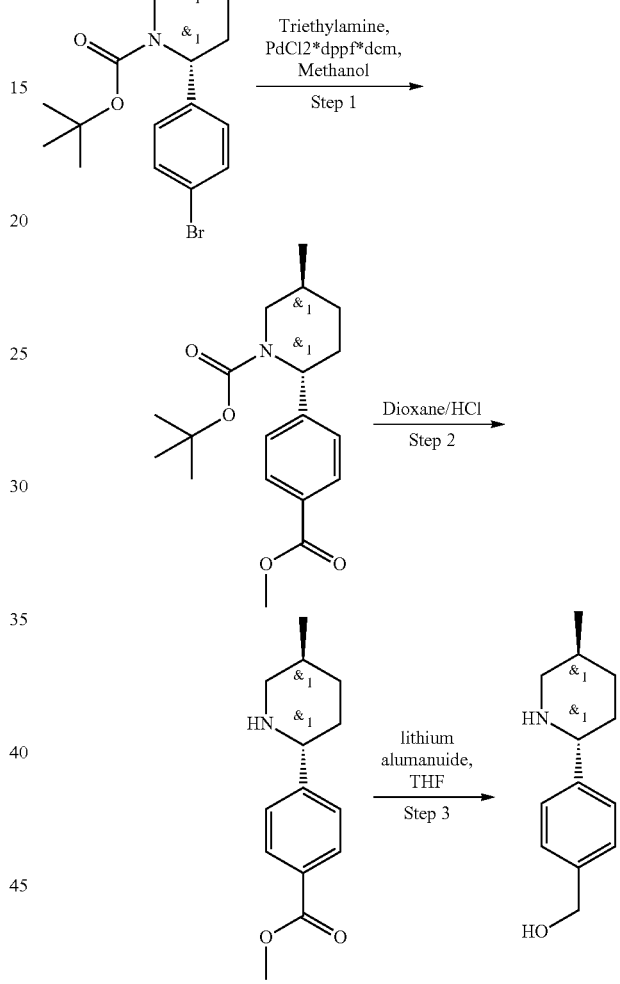

Step 1: Synthesis of tert-butyl (2R,5S)-2-(4-methoxycarbonylphenyl)-5-methyl-piperidine-1-carboxylate tert-butyl (2R,5S)-2-(4-bromophenyl)-5-methyl-piperidine-1-carboxylate (1.00 g, 2.82 mmol) was dissolved in Methanol (30 mL). Triethylamine (285.62 mg, 2.82 mmol, 393.42 µL) and PdCl$_2$*dppf*dcm (141.13 µmol) were added thereto. Resulting mixture was stirred at 135° C. for 16 hr under an atmosphere of CO (30 Bar). Then, solvent was evaporated under reduced pressure. Residue was diluted with MTBE (50 ml) and filtered through a short pad of silicagel. Filtrate was concentrated in vacuo, affording tert-butyl (2R,5S)-2-(4-methoxycarbonylphenyl)-5-methyl-piperidine-1-carboxylate.

917

¹H NMR (DMSO-d₆, 500 MHz): 0.97 (d, 3H), 1.15 (m, 1H), 1.37 (s, 9H), 1.53 (m, 1H), 1.81 (m, 1H), 2.07 (m, 2H), 2.98 (m, 1H), 3.62 (m, 1H), 3.84 (s, 3H), 5.18 (m, 1H), 7.37 (m, 2H), 7.95 (m, 2H).

Step 2: Synthesis of Methyl 4-[(2R,5S)-5-methyl-2-piperidyl]benzoate

The solution of tert-butyl (2R,5S)-2-(4-methoxycarbonylphenyl)-5-methyl-piperidine-1-carboxylate (800.00 mg, 2.40 mmol) in Dioxane/HCl (10 mL) was stirred at 20° C. for 12 hr. The resulting mixture evaporated to dryness. The residue was diluted with potassium carbonate and extracted with DCM (2*20 ml). The combined organic extracts was dried over sodium sulfate and evaporated to obtain crude methyl 4-[(2R,5S)-5-methyl-2-piperidyl]benzoate which was used in next step without purification.

Step 3: Synthesis of Methyl 4-[(2R,5S)-5-methyl-2-piperidyl]benzoate lithium alumanuide (97.61 mg, 2.57 mmol) was added to a stirred solution of methyl 4-[(2R,5S)-5-methyl-2-piperidyl]benzoate (300.00 mg, 1.29 mmol) in dry THF at 0° C. and allowed to warm to room temperature then stirred for 12 hr. The reaction mixture was quenched with saturated sodium sulfate solution and stirred for 30 min. The reaction mixture was filtered through celite, the organic layer was separated and concentrated in vacuo to obtain [4-[(2R,5S)-5-methyl-2-piperidyl]phenyl]methanol (0.1 g, 487.10 μmol, 37.88% yield).

¹H NMR (CDCl₃, 400 MHz): 0.89 (d, 3H), 1.06 (m, 2H), 1.62 (m, 2H), 1.82 (m, 2H), 2.49 (t, 1H), 3.13 (m, 1H), 3.52 (m, 1H), 3.75 (m, 1H), 4.52 (s, 2H), 7.37 (m, 2H), 7.42 (m, 2H).

3U. The Synthesis of 2-oxo-2-(2-phenyl-1-piperidyl)acetic acid

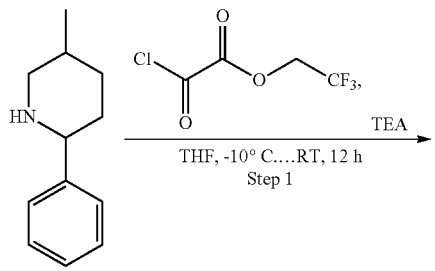

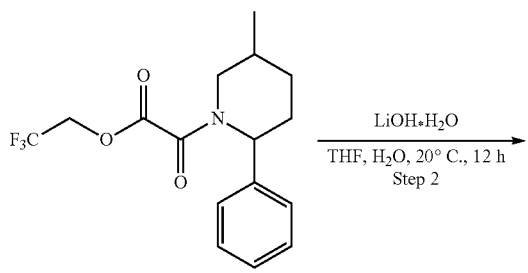

Step 1: The Synthesis of 2,2,2-trifluoroethyl 2-(5-methyl-2-phenyl-1-piperidyl)-2-oxo-acetate 2,2,2-trifluoroethyl 2-chloro-2-oxo-acetate (5.43 g, 28.53 mmol) was added dropwise to the solution of 5-methyl-2-phenyl-piperidine (5 g, 28.53 mmol) and triethylamine (2.89 g, 28.53 mmol, 3.98 mL) in THF (50 mL) at −10° C. The resulting mixture was left to warm to r.t. and stirred for 12 hr. The resulting precipitate was filtered off. The filtrate was evaporated to obtain 2,2,2-trifluoroethyl 2-(5-methyl-2-phenyl-1-piperidyl)-2-oxo-acetate (9 g, 27.33 mmol, 95.80% yield) which was used in next step without purification.

¹H NMR (400 MHz, DMSO-d₆) δ 1.19 (m, 3H), 1.33 (m, 1H), 1.91 (m, 4H), 3.10 (m, 2H), 5.10 (m, 3H), 7.19 (d, 1H), 7.21 (d, 1H), 7.40 (m, 3H).

LCMS(ESI): [M+H]⁺ m/z: calcd 329.1; found 330.1; Rt=1.496 min.

Step 2: The Synthesis of 2-(5-methyl-2-phenyl-1-piperidyl)-2-oxo-acetic acid

Lithium hydroxide (654.50 mg, 27.33 mmol) was added to the solution of 2,2,2-trifluoroethyl 2-(5-methyl-2-phenyl-1-piperidyl)-2-oxo-acetate (9 g, 27.33 mmol) in THF (100 mL) and water (10 mL). The resulting mixture was stirred at 20° C. for 12 hr. Then, the mixture was evaporated to dryness to obtain 2-(5-methyl-2-phenyl-1-piperidyl)-2-oxo-acetic acid (5 g, 19.67 mmol, 71.96% yield, Li⁺) which was used in next step without purification.

¹H NMR (400 MHz, DMSO-d₆) δ 1.13 (m, 3H), 1.30 (m, 1H), 1.63 (m, 2H), 2.01 (m, 2H), 3.56 (m, 2H), 5.04 (m, 1H), 7.16 (m, 3H), 7.32 (m, 2H).

LCMS(ESI): Acid[M+H]⁺ m/z: calcd 247.1.1; found 248.2; Rt=1.133 min.

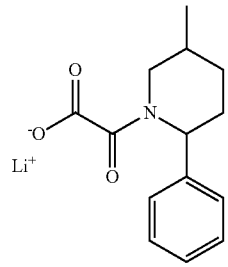

3V. The Synthesis of N-(6-amino-5-methyl-3-pyridyl)-2-[(2R,5S)-5-methyl-2-(6-oxo-5H-1,5-naphthyridin-2-yl)-1-piperidyl]-2-oxo-acetamide and N-(6-amino-5-methyl-3-pyridyl)-2-[(2S,5R)-5-methyl-2-(6-oxo-5H-1,5-naphthyridin-2-yl)-1-piperidyl]-2-oxo-acetamide

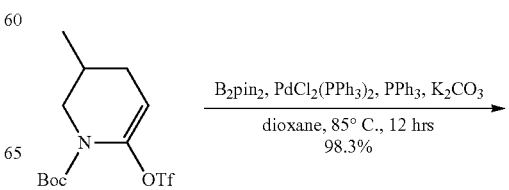

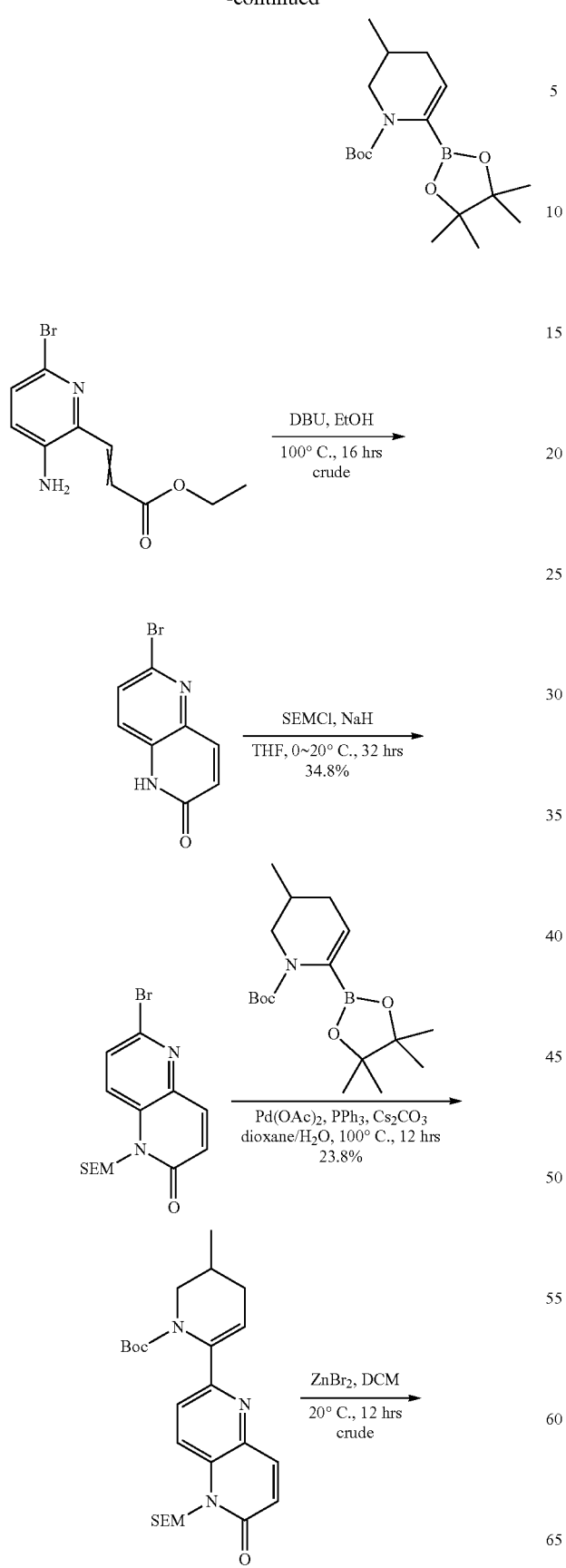

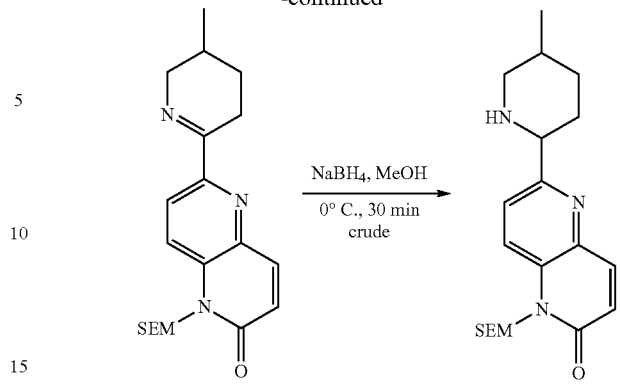

Step 1: Synthesis of tert-butyl 3-methyl-6-(4,4,5,5-tetramethyl-1,3,2-dioxaborolan-2-yl)-3,4-dihydro-2H-pyridine-1-carboxylate To a mixture of tert-butyl 3-methyl-6-(trifluoromethylsulfonyloxy)-3,4-dihydro-2H-pyridine-1-carboxylate (5 g, 14.5 mmol) in dioxane (30 mL) were added B₂pin₂ (5.5 g, 21.7 mmol), PdCl₂(PPh₃)₂ (305 mg, 0.435 mmol), PPh₃ (228 mg, 0.869 mmol) and K₂CO₃ (3 g, 21.7 mmol). The resulting mixture was stirred at 85° C. for 12 hours under nitrogen. The reaction mixture was diluted with H₂O (50 mL), extracted with EtOAc (50 mL*3). The combined organic layers were washed with brine (100 mL*2), dried over anhydrous Na₂SO₄, filtered and concentrated under reduced pressure to give a crude product, which was purified by flash chromatography (ISCO®; 80 g AgelaFlash® Silica Flash Column, petroleum ether/EtOAc with EtOAc from 0~10%, flow rate=45 mL/min, I₂) to afford tert-butyl 3-methyl-6-(4,4,5,5-tetramethyl-1,3,2-dioxaborolan-2-yl)-3,4-dihydro-2H-pyridine-1-carboxylate (4.6 g, 98.3% yield) as colorless oil. LCMS (ESI) [M+H]⁺ m/z: calcd 324.2, found 324.1.

Step 2: Synthesis of 6-bromo-1H-1,5-naphthyridin-2-one

To a solution of ethyl 3-(3-amino-6-bromo-2-pyridyl)prop-2-enoate (2.2 g, 8.11 mmol) in EtOH (20 mL) was added DBU (6.1 mL, 40.9 mmol). Then the mixture was stirred at 100° C. for 16 hours under nitrogen. The mixture was concentrated under reduced pressure to give a crude product, which was purified by flash chromatography (ISCO®; 40 g AgelaFlash® Silica Flash Column, DCM/MeOH with MeOH from 0~0.5%, flow rate=50 mL/min, 254 nm) to afford 6-bromo-1H-1,5-naphthyridin-2-one (3.5 g, crude) as brown solid. LCMS (ESI) [M+H]⁺ m/z: calcd 227.0, found 227.0.

Step 3: Synthesis of 6-bromo-1-(2-trimethylsilylethoxymethyl)-1,5-naphthyridin-2-one To a solution of 6-bromo-1H-1,5-naphthyridin-2-one (3.5 g, 15.6 mmol) in THF (30 mL) was added NaH (1.3 g, 32.5 mmol, 60 wt % in mineral oil) at 0° C. The mixture was stirred at 20° C. for 0.5 hour. SEMCl (3.3 mL, 18.7 mmol) was added, and the mixture was stirred at 20° C. for 12 hours. The reaction didn't get full conversion on LCMS. NaH (1.3 g, 32.5 mmol, 60 wt % in mineral oil) was added at 0° C. and the mixture was stirred at 20° C. for 30 minutes. SEMCl (3.3 mL, 18.7 mmol) was added, and the mixture was stirred at 20° C. for 14 hours. SEMCl (3.3 mL, 18.7 mmol) was added, and the mixture was stirred at 20° C. for 5 hours. The resulting mixture was quenched by addition of water (50 mL) and extracted with EtOAc (50 mL*3). The combined organic layer was dried over anhydrous $Na_2SO_4$, filtered and concentrated under reduced pressure to give a crude product, which was purified by flash chromatography (ISCO®; 24 g SepaFlash® Silica Flash Column, petroleum ether/EtOAc with EtOAc from 0~13%, 35 mL/min, 254 nm) to afford 6-bromo-1-(2-trimethylsilylethoxymethyl)-1,5-naphthyridin-2-one (1.92 g, 34.8% yield) as a white solid. $^1$H NMR (400 MHz, methanol-$d_4$) δ ppm 7.97 (d, J=8.4 Hz, 1H), 7.91 (d, J=9.8 Hz, 1H), 7.74 (d, J=8.9 Hz, 1H), 6.92 (d, J=9.8 Hz, 1H), 5.76 (s, 2H), 3.65-3.68 (m, 2H), 0.90-0.93 (m, 2H), 0.02 (s, 9H); LCMS (ESI) [M+H]$^+$ m/z: calcd 357.0, found 356.9.

Step 4: Synthesis of tert-butyl 3-methyl-6-[6-oxo-5-(2-trimethylsilylethoxymethyl)-1,5-naphthyridin-2-yl]-3,4-dihydro-2H-pyridine-1-carboxylate A mixture of tert-butyl 3-methyl-6-(4,4,5,5-tetramethyl-1,3,2-dioxaborolan-2-yl)-3,4-dihydro-2H-pyridine-1-carboxylate (2.3 g, 7.12 mmol), 6-bromo-1-(2-trimethylsilylethoxymethyl)-1,5-naphthyridin-2-one (1.9 g, 5.35 mmol), Pd(OAc)$_2$ (240 mg, 1.07 mmol), PPh$_3$ (561 mg, 2.14 mmol), Cs$_2$CO$_3$ (3.5 g, 10.7 mmol), dioxane (20 mL) and H$_2$O (2 mL) was stirred at 100° C. for 12 hours. The resulting mixture was quenched by addition of water (50 mL) and extracted with EtOAc (50 mL*3). The combined organic layer was washed with brine (100 mL*2), dried over anhydrous Na$_2$SO$_4$, filtered and concentrated under reduced pressure to give a crude product, which was purified by flash chromatography (ISCO®; 80 g SepaFlash® Silica Flash Column, petroleum ether/EtOAc with EtOAc from 0~45%, 45 mL/min, 254 nm) to afford tert-butyl 3-methyl-6-[6-oxo-5-(2-trimethylsilylethoxymethyl)-1,5-naphthyridin-2-yl]-3,4-dihydro-2H-pyridine-1-carboxylate (600 mg, 23.8% yield) as a yellow oil. $^1$H NMR (400 MHz, methanol-$d_4$) δ ppm 7.95-8.09 (m, 2H), 7.60 (d, J=8.8 Hz, 1H), 6.91 (d, J=9.8 Hz, 1H), 5.81 (s, 2H), 5.75 (s, 1H), 3.99 (d, J=9.5 Hz, 1H), 3.71-3.77 (m, 1H), 3.63-3.70 (m, 2H), 2.46-2.57 (m, 1H), 2.02-2.11 (m, 1H), 1.91-2.00 (m, 1H), 1.20 (s, 9H), 1.06 (d, J=6.8 Hz, 3H), 0.87-0.92 (m, 2H), −0.04 (s, 9H); LCMS (ESI) [M+H]$^+$ m/z: calcd 472.3, found 472.4.

Step 5: Synthesis of 6-(3-methyl-2,3,4,5-tetrahydropyridin-6-yl)-1-(2-trimethylsilylethoxymethyl)-1,5-naphthyridin-2-one To a solution of tert-butyl 3-methyl-6-[6-oxo-5-(2-trimethylsilylethoxymethyl)-1,5-naphthyridin-2-yl]-3,4-dihydro-2H-pyridine-1-carboxylate (580 mg, 1.23 mmol) in DCM (30 mL) was added ZnBr$_2$ (554 mg, 2.46 mmol). The mixture was stirred at 20° C. for 12 hours under nitrogen. The resulting mixture was quenched by addition of water (30 mL) and extracted with DCM (30 mL*3). The combined organic layer was dried over anhydrous Na$_2$SO$_4$, filtered and concentrated under reduced pressure to give 6-(3-methyl-2,3,4,5-tetrahydropyridin-6-yl)-1-(2-trimethylsilylethoxymethyl)-1,5-naphthyridin-2-one (650 mg, crude) as a yellow solid, which was directly used without further purification. LCMS (ESI) [M+H]$^+$ m/z: calcd 372.2, found 372.2.

Step 6: Synthesis of 6-(5-methyl-2-piperidyl)-1-(2-trimethylsilylethoxymethyl)-1,5-naphthyridin-2-one To a solution of 6-(3-methyl-2,3,4,5-tetrahydropyridin-6-yl)-1-(2-trimethylsilylethoxymethyl)-1,5-naphthyridin-2-one (600 mg, 1.61 mmol) in MeOH (10 mL) was added NaBH$_4$ (92 mg, 2.43 mmol) at 0° C. The mixture was stirred at 0° C. for 30 minutes. The resulting mixture was concentrated under reduced pressure to give 6-(5-methyl-2-piperidyl)-1-(2-trimethylsilylethoxymethyl)-1,5-naphthyridin-2-one (800 mg, crude) as a brown solid, which was directly used without further purification. LCMS (ESI) [M+H]$^+$ m/z: calcd 374.2, found 374.2.

3W. The Synthesis of 2-cyclopentyl-5-methylpiperidine

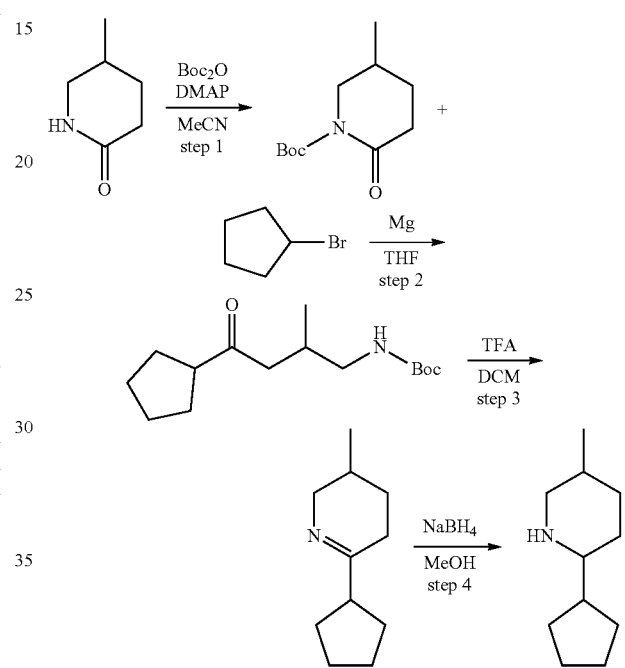

Step 1: Synthesis of tert-butyl 5-methyl-2-oxopiperidine-1-carboxylate

Di-tert-butyl dicarbonate (21.22 g, 97.21 mmol, 22.31 mL) was added dropwise to a solution of 5-methylpiperidin-2-one (10 g, 88.37 mmol) and 4-dimethylaminopyridine (539.82 mg, 4.42 mmol) in MeCN (100 mL). Resulting solution was stirred for 12 hr at 25° C. Then the solvent was evaporated and resulting crude material was diluted with DCM (50 ml) and washed with saturated sodium hydro carbonate solution (2×100 ml). Organic phase was dried over sodium sulfate and evaporated under reduced pressure to obtain tert-butyl 5-methyl-2-oxo-piperidine-1-carboxylate (16.5 g, 77.37 mmol, 87.54% yield).

$^1$H NMR (400 MHz, CDCl$_3$) δ (ppm) 0.99 (d, 3H), 1.39 (m, 1H), 1.49 (s, 9H), 1.89 (m, 2H), 2.48 (m, 2H), 3.09 (t, 1H), 3.75 (d, 1H).

LCMS(ESI): [M-Boc]$^+$ m/z: calcd 113.2; found 114.2; Rt=1.223 min.

Step 2: Synthesis of tert-butyl (4-cyclopentyl-2-methyl-4-oxobutyl)carbamate

To a suspension of magnesium (2.26 g, 92.84 mmol, 1.30 mL) in THF (100 mL) was added cyclopentyl bromide (14.99 g, 100.58 mmol, 10.78 mL). The reaction mixture was stirred for 45 min to give a grey solution. This solution was transferred dropwise to a cold (−78° C.) suspension of tert-butyl 5-methyl-2-oxo-piperidine-1-carboxylate (16.5 g, 77.37 mmol) in THF (200 mL). The reaction mixture was stirred at −78° C. for 1 hr before being warmed to rt and stirred for 12 hr. The reaction was diluted with MTBE (500 ml) and slowly quenched with 100 mL of saturated ammonium chloride aqueous solution. The organic phase was washed with a saturated aqueous solution of sodium bicarbonate (2×200 ml). The combined aqueous fractions were back extracted two times with MTBE. The combined organic fractions were dried over sodium sulfate, and concentrated by rotary evaporation to obtain crude material that was purified with column chromatography (120 g SiO$_2$, hexane/MTBE with MTBE from 0~15%, flow rate=80 mL/min) to obtain tert-butyl N-(4-cyclopentyl-2-methyl-4-oxo-butyl)carbamate (3.55 g, 13.18 mmol, 17.03% yield).

$^1$H NMR (400 MHz, CDCl$_3$) δ (ppm) 0.86 (s, 3H), 1.41 (s, 9H), 1.63 (m, 9H), 2.45 (m, 2H), 2.84 (m, 1H), 2.98 (m, 2H), 4.64 (m, 1H).

LCMS(ESI): [M-Boc]$^+$ m/z: calcd 183.4; found 184.2; Rt=1.457 min.

Step 3: Synthesis of 6-cyclopentyl-3-methyl-2,3,4,5-tetrahydropyridine

A solution of tert-butyl N-(4-cyclopentyl-2-methyl-4-oxo-butyl)carbamate (3.55 g, 13.18 mmol) in TFA (20 mL) and DCM (20 mL) was stirred at 25° C. for 11 hr. Sodium sulfate saturated aq. solution was added to the solution (50 ml) and then extracted with DCM (2×50 ml). Organic phase was dried over sodium sulfate, filtered and evaporated to obtain 6-cyclopentyl-3-methyl-2,3,4,5-tetrahydropyridine (1.6 g, 9.68 mmol, 73.46% yield).

$^1$H NMR (500 MHz, CDCl$_3$) δ (ppm) 0.91 (s, 3H), 1.22 (m, 1H), 1.60 (m, 7H), 1.81 (m, 3H), 2.14 (m, 1H), 2.24 (m, 1H), 2.55 (m, 1H), 2.99 (m, 1H), 3.69 (m, 1H).

Step 4: Synthesis of 2-cyclopentyl-5-methylpiperidine

Sodium borohydride (732.50 mg, 19.36 mmol, 684.58 μL) was added portion wise to a solution of 6-cyclopentyl-3-methyl-2,3,4,5-tetrahydropyridine (1.6 g, 9.68 mmol) in MeOH (20 mL). The mixture was stirred at rt for 12 hr. Water (50 ml) was added and resulting mixture was extracted with EtOAc (2×50 ml). Organic phase was dried over sodium sulfate, filtered and evaporated to obtain 2-cyclopentyl-5-methyl-piperidine (1.55 g, crude).

$^1$H NMR (400 MHz, CDCl$_3$) δ (ppm) 0.78 (s, 3H), 1.03 (m, 4H), 1.62 (m, 11H), 2.16 (m, 2H), 2.96 (m, 1H).

GCMS: [M]$^+$ m/z: calcd 167.4; found 168.2; Rt=6.657 min.

3X. The Synthesis of (2S,4R)-2-phenylpiperidine-4-carbonitrile

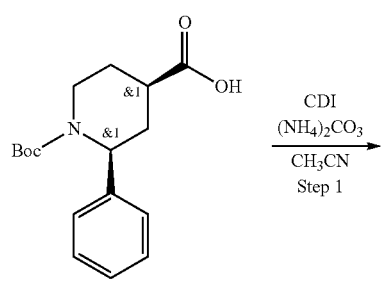

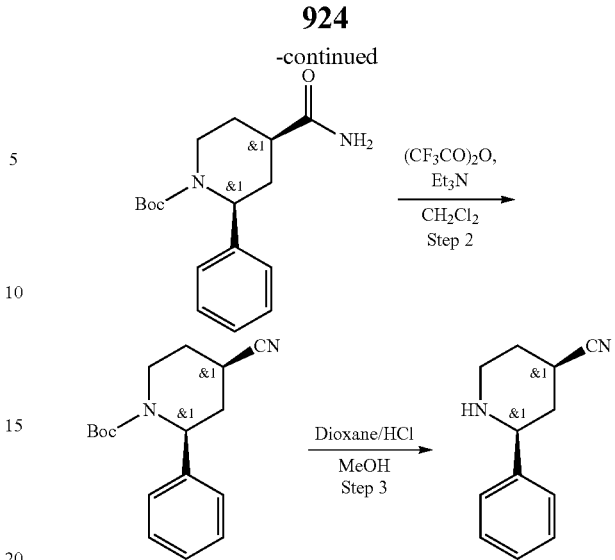

Step 1: Synthesis of tert-butyl (2S,4R)-4-carbamoyl-2-phenyl-piperidine-1-carboxylate To a stirred solution of (2S,4R)-1-tert-butoxycarbonyl-2-phenyl-piperidine-4-carboxylic acid (1 g, 3.27 mmol) in CH$_3$CN (100 mL) was added carbonyldiimidazol (690.29 mg, 4.26 mmol). The reaction mixture was then stirred for 1 hour. After 1 hour, ammonium carbonate (1.43 g, 8.19 mmol) was added in portions and the resulting reaction mixture was stirred for overnight at room temperature. Then reaction mixture was then evaporated in vacuo, water was added and extracted with DCM (2×40 mL). The combined organic phase was dried over Na$_2$SO$_4$ and concentrated under reduced pressure to afford tert-butyl (2S,4R)-4-carbamoyl-2-phenyl-piperidine-1-carboxylate (0.7 g, 2.30 mmol, 70.23% yield) as a yellow oil.

LCMS(ESI): [M+Boc]$^+$ m/z: calcd 304.2; found 249.2 (t-Bu cleaved product mass); Rt=1.313 min.

Step 2: Synthesis of tert-butyl (2S,4R)-4-cyano-2-phenyl-piperidine-1-carboxylate To a stirred solution of tert-butyl (2S,4R)-4-carbamoyl-2-phenyl-piperidine-1-carboxylate (0.7 g, 2.30 mmol) in DCM (10 mL) was added Et$_3$N (1.05 g, 10.35 mmol, 1.44 mL) and the resulting yellow solution was cooled to 0° C. Trifluoroacetic anhydride (724.52 mg, 3.45 mmol, 486.26 μL) was added dropwise over 5 minutes to the reaction mixture and the resulting reaction mixture was stirred for 30 minutes. After 30 minutes, the crude reaction mixture was diluted with saturated sodium bicarbonate solution and dichloromethane. Both layers were separated. The aqueous layer was extracted with dichloromethane and the combined organic phase was washed with saturated sodium bicarbonate solution, brine, dried over Na$_2$SO$_4$ and concentrated under reduced pressure to afford tert-butyl (2S,4R)-4-cyano-2-phenyl-piperidine-1-carboxylate (0.6 g, 2.10 mmol, 91.11% yield) as yellow oil.

LCMS(ESI): [M+Boc]$^+$ m/z: calcd 286.2; found 231.2 (t-Bu cleaved product mass); Rt=1.411 min.

Step 3: Synthesis of (2S,4R)-2-phenylpiperidine-4-carbonitrile

To a stirred solution tert-butyl (2S,4R)-4-cyano-2-phenyl-piperidine-1-carboxylate (0.6 g, 2.10 mmol) in MeOH (10 mL) was added HCl in dioxane (2.10 mmol, 5 mL). The resulting reaction mixture was stirred for overnight at room temperature. The reaction was then evaporated in vacuo to afford (2S,4R)-2-phenylpiperidine-4-carbonitrile (0.36 g, 1.93 mmol, 92.25% yield). The crude product was used in next step reaction without any further purification.

LCMS(ESI): [M+H]$^+$ m/z: calcd 186.1; found 187.1; Rt=0.558 min.

3Y. Synthesis of rac-(2R,5S)-2-(3-bromophenyl)-5-methylpiperidine

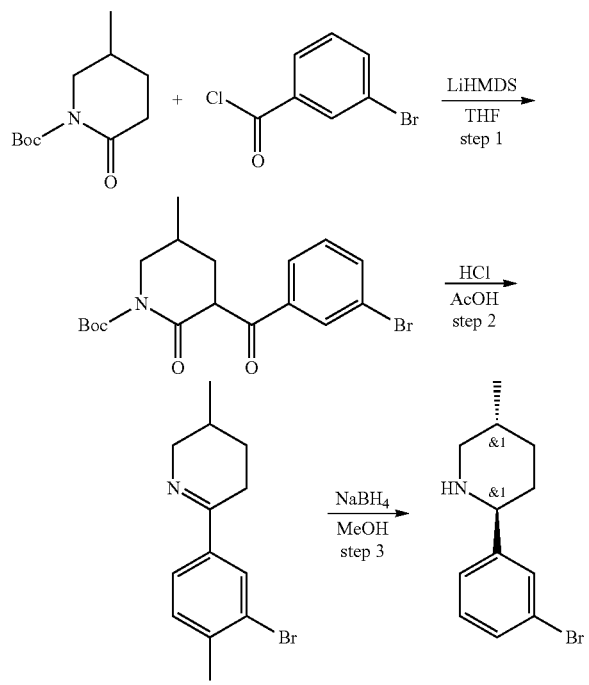

Step 1: Synthesis of tert-butyl 3-(3-bromobenzoyl)-5-methyl-2-oxopiperidine-1-carboxylate To the pre-cooled (−78° C.) solution of tert-butyl 5-methyl-2-oxo-piperidine-1-carboxylate (13 g, 60.95 mmol) in THF (250 mL) LiHMDS (115 mL) was added dropwise. The resulting mixture was stirred at −78° C. for 1 hr. The solution of 3-bromobenzoyl chloride (13.38 g, 60.95 mmol, 8.06 mL) was added in one portion. The reaction mixture was allowed to warm to rt and stirred at that temperature for 5 hr. The reaction mixture was quenched with NaHSO$_4$ (35 g; 10% solution) and extracted with DCM (3*150 ml). Organic layers were washed with water, dried over Na$_2$SO$_4$. DCM was evaporated to give tert-butyl 3-(3-bromobenzoyl)-5-methyl-2-oxo-piperidine-1-carboxylate (29 g, crude).

$^1$H NMR (400 MHz, CDCl$_3$) δ (ppm) 1.08 (d, 3H), 1.28 (m, 1H), 1.48 (s, 9H), 1.98 (m, 2H), 2.14 (m, 1H), 2.41 (m, 1H), 4.51 (m, 1H), 7.31 (m, 3H), 7.65 (m, 1H).

LCMS(ESI): [M-Boc]$^+$ m/z: calcd 296.4; found 297.2; Rt=1.563 min.

Step 2: Synthesis of 6-(3-bromo-4-methylphenyl)-3-methyl-2,3,4,5-tetrahydropyridine tert-butyl 3-(3-bromobenzoyl)-5-methyl-2-oxo-piperidine-1-carboxylate (29 g, 73.18 mmol) was dissolved in acetic acid (150 mL) and hydrogen chloride water solution (250 mL, 30% purity) was added portion wise. After addition was complete, resulting mixture was stirred at 100° C. for 15 hr. Then, solvents were removed under reduced pressure and residue was partitioned between 1 N HCl (150 ml) and DCM (100 ml). Organic layer was separated and discarded. Aqueous layer was basified to ph≈10 with 10% NaOH and extracted with EtOAc (3×150 ml). EtOAc solution was separated, dried over Na$_2$SO$_4$ and evaporated under reduced pressure, affording 6-(3-bromophenyl)-3-methyl-2,3,4,5-tetrahydropyridine (10 g, 39.66 mmol, 54.19% yield).

$^1$H NMR (500 MHz, CDCl$_3$) δ (ppm) 0.98 (d, 3H), 1.38 (m, 1H), 1.69 (m, 1H), 1.93 (m, 1H), 2.55 (m, 1H), 2.73 (m, 1H), 3.27 (m, 1H), 4.01 (m, 1H), 7.22 (t, 1H), 7.49 (d, 1H), 7.65 (d, 1H), 7.93 (s, 1H).

LCMS(ESI): [M]$^+$ m/z: calcd 252.4; found 253.2; Rt=0.886 min.

Step 3: Synthesis of rac-(2R,5S)-2-(3-bromophenyl)-5-methylpiperidine

To a solution of 6-(3-bromophenyl)-3-methyl-2,3,4,5-tetrahydropyridine (10 g, 39.66 mmol) in MeOH (100 mL), sodium borohydride (1.73 g, 45.61 mmol, 1.61 mL) was added portion wise at 0° C. The resulting mixture was stirred at 25° C. for 2 hr and evaporated in vacuo. The residue was dissolved in MeOH (50 mL) and treated with hydrogen chloride solution 40 M in dioxane (14.46 g, 396.59 mmol, 18.08 mL) and the reaction mixture was stirred for 15 min. Solvents were evaporated. Precipitate was washed with THF, dried in vacuo to give (2S,5R)-2-(3-bromophenyl)-5-methyl-piperidine (10 g, 34.41 mmol, 86.76% yield, HCl). Product contains 2.78 g (about 30%) of NaCl.

$^1$H NMR (500 MHz, DMSO-d$_6$) δ (ppm) 0.96 (d, 3H), 1.22 (m, 1H), 1.95 (m, 3H), 2.16 (m, 1H), 2.63 (m, 1H), 3.19 (m, 1H), 4.15 (m, 1H), 7.37 (t, 1H), 7.57 (d, 1H), 7.67 (d, 1H), 7.91 (s, 1H), 9.69 (bds, 1H).

LCMS(ESI): [M]$^+$ m/z: calcd 253.4; found 254.2; Rt=0.815 min.

3Z. Synthesis of rac-6-((2R,5S)-5-methylpiperidin-2-yl)spiro[3.3]heptan-2-ol

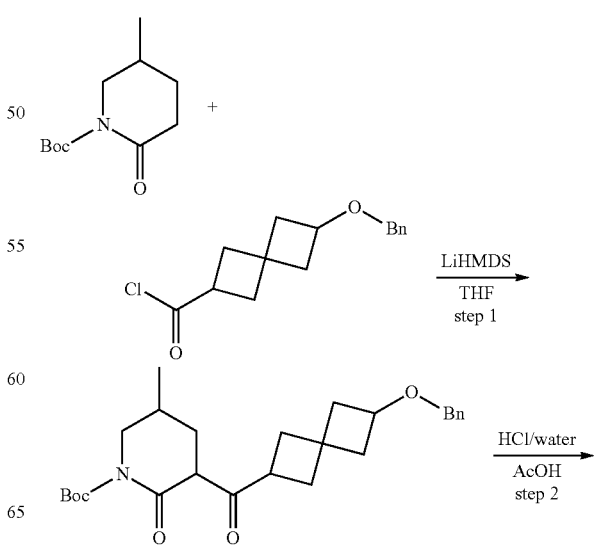

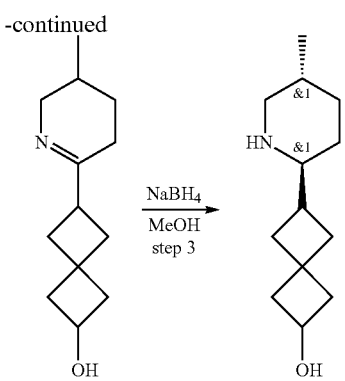

Step 1: Synthesis of tert-butyl 3-(6-(benzyloxy)spiro[3.3]heptane-2-carbonyl)-5-methyl-2-oxopiperidine-1-carboxylate To the pre-cooled (−78° C.) solution of tert-butyl 5-methyl-2-oxo-piperidine-1-carboxylate (8.65 g, 40.56 mmol) in THF (200 mL) LiHMDS (80.4 mL) was added dropwise. The resulting mixture was stirred at −78° C. for 1 hr. The solution of 2-benzyloxyspiro[3.3]heptane-6-carbonyl chloride (10.74 g, 40.56 mmol, 8.06 mL) was added in one portion. The reaction mixture was allowed to warm to rt and stirred at that temperature for 5 hr. The reaction mixture was quenched with NaHSO$_4$ (30 g; 10% solution) and extracted with DCM (3*150 ml). Organic layers was washed with water, dried over Na$_2$SO$_4$. DCM was evaporated to give tert-butyl 3-(2-benzyloxyspiro[3.3]heptane-6-carbonyl)-5-methyl-2-oxo-piperidine-1-carboxylate (33 g, crude).

$^1$H NMR (500 MHz, CDCl$_3$) δ (ppm) 1.05 (d, 3H), 1.53 (s, 9H), 2.11 (m, 10H), 2.65 (m, 2H), 3.12 (m, 2H), 3.76 (m, 1H), 3.96 (m, 1H), 4.38 (s, 2H), 7.31 (m, 5H).

LCMS(ESI): [M]$^+$ m/z: calcd 341.2; found 342.2; Rt=1.625 min.

Step 2: Synthesis of 6-(5-methyl-3,4,5,6-tetrahydropyridin-2-yl)spiro[3.3]heptan-2-ol tert-butyl 3-(2-benzyloxyspiro[3.3]heptane-6-carbonyl)-5-methyl-2-oxo-piperidine-1-carboxylate (33 g, 74.74 mmol) was dissolved in acetic acid (150 mL) and hydrogen chloride water solution (250 mL, 30% purity) was added portion wise. After addition was complete, resulting mixture was stirred at 100° C. for 15 hr. Then, solvents were removed under reduced pressure and residue was partitioned between 1 N HCl (150 ml) and DCM (100 ml). Organic layer was separated and discarded. Aqueous layer was basified to ph≈10 with 10% NaOH and extracted with EtOAc (3×150 ml). EtOAc solution was separated, dried over Na$_2$SO$_4$ and evaporated under reduced pressure, affording 6-(3-methyl-2,3,4,5-tetrahydropyridin-6-yl)spiro[3.3]heptan-2-ol (4.5 g, 21.71 mmol, 29.04% yield).

$^1$H NMR (500 MHz, DMSO-d$_6$) δ (ppm) 0.86 (d, 3H), 1.23 (m, 2H), 1.54 (m, 1H), 1.70 (m, 1H), 1.80 (m, 1H), 1.92 (m, 1H), 2.02 (m, 5H), 2.22 (m, 1H), 2.48 (m, 1H), 2.95 (m, 2H), 3.67 (m, 1H), 4.15 (m, 1H).

LCMS(ESI): [M]$^+$ m/z: calcd 207.2; found 208.2; Rt=0.628 min.

Step 3: Synthesis of rac-6-((2R,5S)-5-methylpiperidin-2-yl)spiro[3.3]heptan-2-ol To a solution of 6-(3-methyl-2,3,4,5-tetrahydropyridin-6-yl)spiro[3.3]heptan-2-ol (4.5 g, 21.71 mmol) in MeOH (50 mL), sodium borohydride (944.33 mg, 24.96 mmol, 882.55 µL) was added portionwise at 0° C. The resulting mixture was stirred at 25° C. for 2 hr and evaporated in vacuo. The residue was diluted with water (100 ml) and product was extracted with EtOAc (3*30 ml). Combined organic layers were dried over Na$_2$SO$_4$. EtOAc was evaporated to give 6-[(2S,5R)-5-methyl-2-piperidyl]spiro[3.3]heptan-2-ol (3.5 g, 16.72 mmol, 77.03% yield).

$^1$H NMR (400 MHz, CDCl$_3$) δ (ppm) 0.81 (d, 3H), 0.95 (m, 2H), 1.22 (m, 1H), 1.52 (m, 3H), 1.95 (m, 7H), 2.21 (m, 3H), 2.44 (m, 2H), 2.95 (m, 1H), 4.22 (m, 1H).

LCMS(ESI): [M]$^+$ m/z: calcd 209.2; found 210.2; Rt=0.600 min.

3AA. Synthesis of (2R,4S)—N-benzyl-2-phenyl-piperidin-4-amine

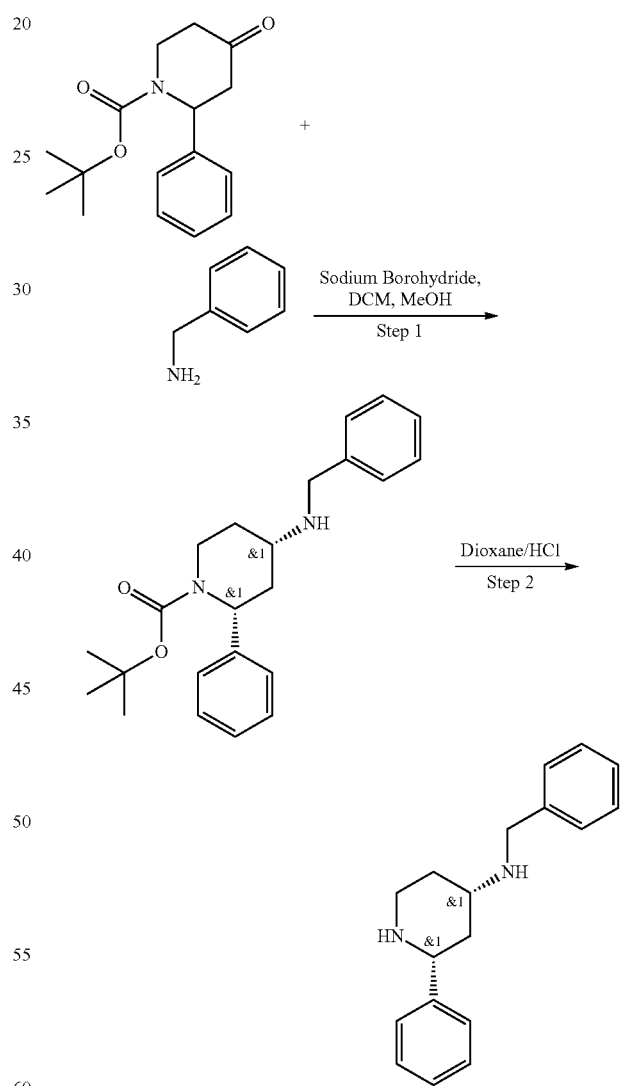

Step 1: Synthesis of tert-butyl (2R,4S)-4-(benzylamino)-2-phenyl-piperidine-1-carboxylate tert-butyl 4-oxo-2-phenyl-piperidine-1-carboxylate (3 g, 10.90 mmol) and phenylmethanamine (1.17 g, 10.90 mmol)

were mixed in DCM (30 mL). 4A molecular sieves (10 g) were added thereto and the resulting mixture was reacted at 20° C. without stirring. After 12 hr HNMR shoved formation of imine. The resulting mixture was filtered. All volatiles were removed in vacuo. The residue was dissolved in dry MeOH (30 mL). Sodium Borohydride (412.21 mg, 10.90 mmol, 385.24 µL) was added in portions with intensive stirring and the resulting mixture was stirred at 20° C. for 3 Hours. The resulting mixture was evaporated. The residue was partitioned between EtOAc (30 ml) and water (30 ml). The aqueous layer was extracted with DCM (2×20 ml). The combined organic extracts were dried over sodium sulfate and evaporated to obtain tert-butyl (2R,4S)-4-(benzylamino)-2-phenyl-piperidine-1-carboxylate (4.5 g, crude), which was used in next step without purification.

$^1$H NMR (DMSO-$d_6$, 400 MHz): 1.20 (s, 9H), 1.29 (m, 2H), 1.49 (m, 1H), 1.89 (m, 1H), 2.12 (m, 1H), 2.81 (m, 1H), 3.35 (m, 1H), 3.57 (s, 2H), 3.85 (m, 1H), 4.82 (m, 1H), 7.16 (m, 10H).

LCMS(ESI): [M+H]$^+$ m/z: calcd 366.3; found 367.2; Rt=1.148 min.

Step 2: Synthesis of (2R,4S)—N-benzyl-2-phenyl-piperidin-4-amine

The solution of tert-butyl (2R,4S)-4-(benzylamino)-2-phenyl-piperidine-1-carboxylate (4.5 g, 12.28 mmol) in Dioxane/HCl (25 mL) was stirred at 20° C. for 12 hr. The resulting mixture evaporated to dryness to obtain crude (2R,4S)—N-benzyl-2-phenyl-piperidin-4-amine (3.7 g, 10.90 mmol, 88.81% yield, 2HCl) which was used in next step without purification.

LCMS(ESI): [M+H]$^+$ m/z: calcd 266.22; found 267.2; Rt=0.703 min.

3BB. The Synthesis of 4-(5-methyl-2-piperidyl)benzenesulfonamide

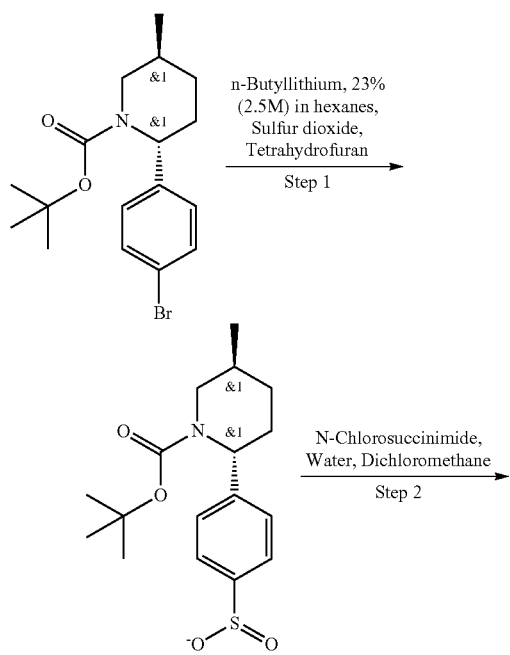

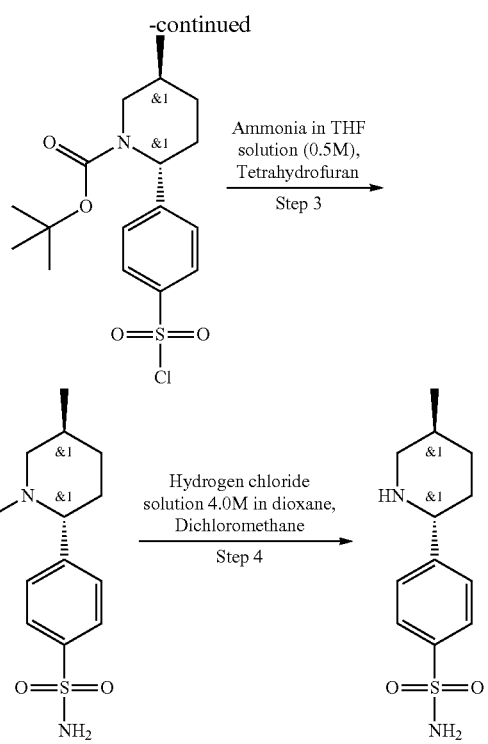

Step 1: Synthesis of 4-(1-tert-butoxycarbonyl-5-methyl-2-piperidyl)benzenesulfinate n-Butyllithium, 23% (2.5M) in hexanes (1.73 g, 6.21 mmol, 2.50 mL, 23% purity) was added dropwise to a cooled to −75° C. solution of tert-butyl 2-(4-bromophenyl)-5-methyl-piperidine-1-carboxylate (2 g, 5.65 mmol) in Tetrahydrofuran (30 mL). After addition was complete, mixture was stirred for 30 minutes at −75° C. Then, Sulfur dioxide (1.81 g, 28.23 mmol) was bubbled into solution and resulting solution was stirred at −60° C. for 1 hr. After that, volatiles were removed under reduced pressure, leaving 4-(1-tert-butoxycarbonyl-5-methyl-2-piperidyl)benzenesulfinate (1.9 g, 5.50 mmol, 97.45% yield, Li$^+$).

LCMS(ESI): [M+H-Boc]$^+$ m/z: calcd 339.2; found 239.2; Rt=1.248 min.

Step 2: Synthesis of tert-butyl 2-(4-chlorosulfonylphenyl)-5-methyl-piperidine-1-carboxylate N-chlorosuccinimide (771.32 mg, 5.78 mmol, 467.46 µL) was added portionwise to an ice-cooled solution of 4-(1-tert-butoxycarbonyl-5-methyl-2-piperidyl)benzenesulfinate (1.9 g, 5.50 mmol, Li$^+$) in Water (30 mL) and Dichloromethane (30 mL). After addition was complete, resulting mixture was stirred at 5° C. for 1 hr. Then, DCM layer was separated, dried over Na$_2$SO$_4$ and concentrated under reduced pressure, affording tert-butyl 2-(4-chlorosulfonylphenyl)-5-methylpiperidine-1-carboxylate (2 g, 5.35 mmol, 97.24% yield).

LCMS(ESI): [M-Boc]$^+$ m/z: calcd 373.1; found 272.0; Rt=1.206 min.

Step 3: Synthesis of tert-butyl 5-methyl-2-(4-sulfamoylphenyl)piperidine-1-carboxylate Ammonia in THF solution (0.5M) (13.66 g, 8.02 mmol, 16.08 mL, 1% purity) was added dropwise to a solution of tert-butyl 2-(4-chlorosulfonylphenyl)-5-methyl-piperidine-1-carboxylate (1 g, 2.67 mmol) in Tetrahydrofuran (20 mL). After addition was complete, resulting mixture was stirred at 20° C. for 1 hr. Then, it was filtered through a short pad of silicagel and filtrate was concentrated under reduced pressure, affording tert-butyl 5-methyl-2-(4-sulfamoylphenyl)piperidine-1-carboxylate (0.87 g, 2.45 mmol, 91.77% yield).

LCMS(ESI): [M+Na]+ m/z: calcd 354.2; found 377.0; Rt=1.319 min.

Step 4: Synthesis of 4-(5-methyl-2-piperidyl)benzenesulfonamide

Hydrogen chloride solution 40 M in dioxane (10.10 g, 27.70 mmol, 10 mL, 10% purity) was added to a solution of tert-butyl 5-methyl-2-(4-sulfamoylphenyl)piperidine-1-carboxylate (870 mg, 2.45 mmol) in Dichloromethane (20 mL). Resulting mixture was stirred at 20° C. for 4 hr. Then, solvents were removed under reduced pressure, leaving 4-(5-methyl-2-piperidyl)benzenesulfonamide (700 mg, 2.41 mmol, 98.07% yield, HCl).

LCMS(ESI): [M+H]+ m/z: calcd 254.1; found 255.2; Rt=0754 min.

3CC. Synthesis of N-methyl-4-(5-methyl-2-piperidyl)benzenesulfonamide resulting mixture was stirred at 20° C. for 1 hr. Then, it was filtered through a short pad of silicagel and filtrate was concentrated under reduced pressure, affording tert-butyl 5-methyl-2-[4-(methylsulfamoyl)phenyl]piperidine-1-carboxylate (0.92 g, 2.50 mmol, 93.35% yield).

LCMS(ESI): [M+H-Boc]+ m/z: calcd 368.2; found 269.0; Rt=1.411 min.

Step 2: Synthesis of N-methyl-4-(5-methyl-2-piperidyl)benzenesulfonamide

Hydrogen chloride solution 40 M in dioxane (10.10 g, 27.70 mmol, 10 mL, 10% purity) was added to a solution of tert-butyl 5-methyl-2-[4-(methylsulfamoyl)phenyl]piperidine-1-carboxylate (920 mg, 2.50 mmol) in Dichloromethane (20 mL). Resulting mixture was stirred at 20° C. for 4 hr. Then, solvents were removed under reduced pressure, leaving N-methyl-4-(5-methyl-2-piperidyl)benzenesulfonamide (740 mg, 2.43 mmol, 97.23% yield, HCl).

LCMS(ESI): [M+H]+ m/z: calcd 268.2; found 269.1; Rt=0.774 min.

3DD. Synthesis of (2S,5S)-3,3-difluoro-2-(4-fluorophenyl)-5-methyl-piperidine

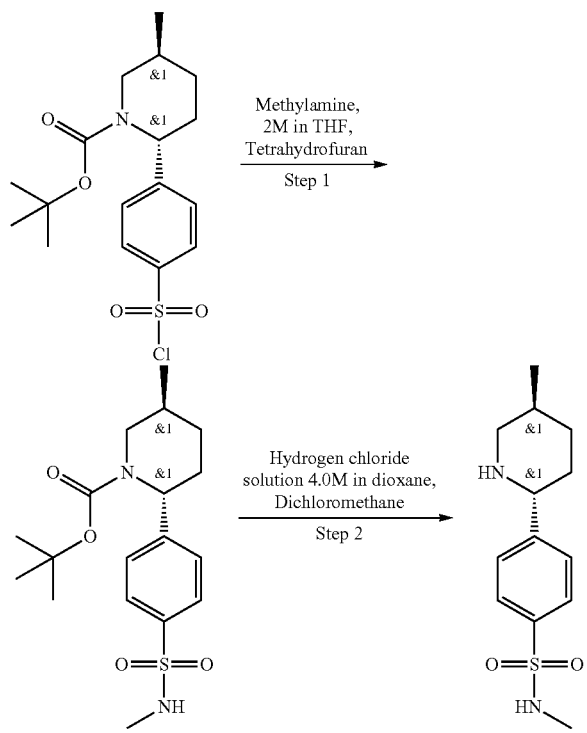

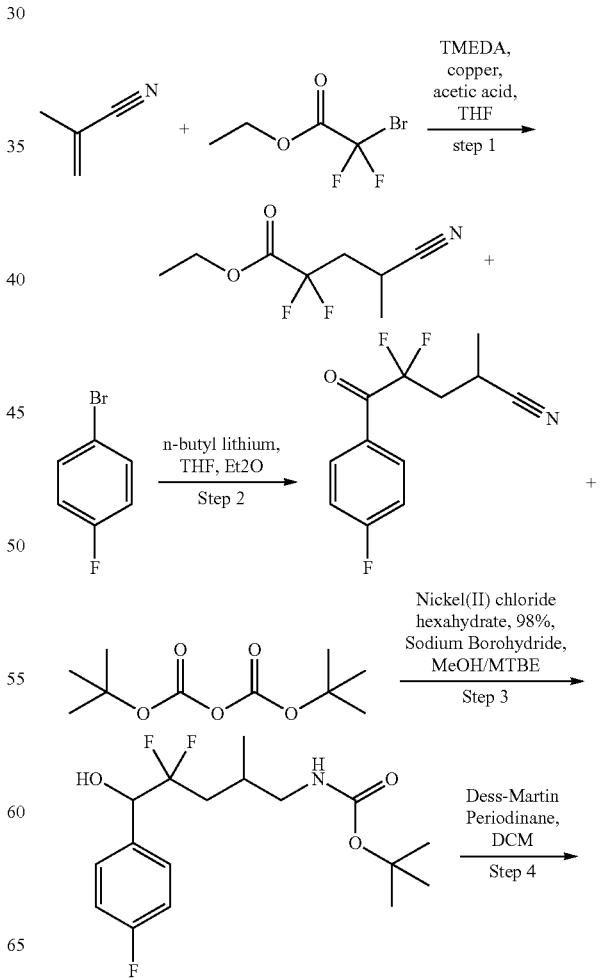

Step 1: Synthesis of tert-butyl 5-methyl-2-[4-(methylsulfamoyl)phenyl]piperidine-1-carboxylate Methylamine, 2 M in THF (5.77 g, 13.37 mmol, 6.70 mL, 7.2% purity) was added dropwise to a solution of tert-butyl 2-(4-chlorosulfonylphenyl)-5-methyl-piperidine-1-carboxylate (1 g, 2.67 mmol) (prepared as described above) in Tetrahydrofuran (20 mL). After addition was complete,

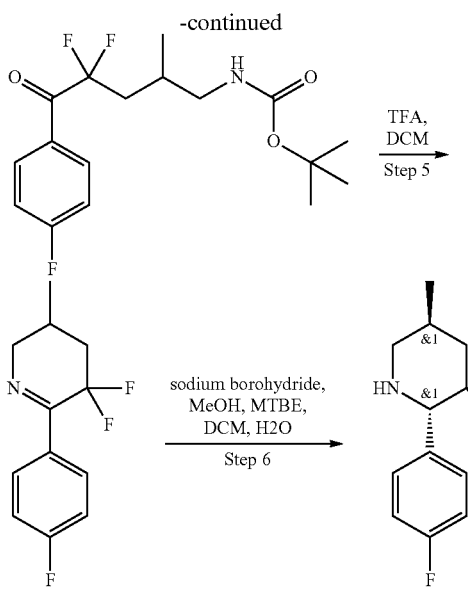

Step 1: Synthesis of Ethyl 4-cyano-2,2-difluoro-pentanoate

To a stirred mixture of copper (9.47 g, 149.06 mmol), 2-methylprop-2-enenitrile (5 g, 74.53 mmol), and ethyl 2-bromo-2,2-difluoro-acetate (27.23 g, 134.15 mmol, 17.23 mL) in THF (64 mL) was added at 20° C. TMEDA (4.33 g, 37.26 mmol, 5.59 mL) and acetic acid (4.48 g, 74.53 mmol, 4.26 mL) in sequence. The mixture was stirred for 1 hour at room temperature, and then was filtered over celite using $Et_2O$ as eluent. Saturated ammonium chloride solution was added to the mixture and the product was extracted with $Et_2O$ (50 ml). The organic phase was washed several times with a saturated solution in water of ammonium chloride and bicarbonate to remove the last traces of copper salts. Then the organic layer was evaporated and the crude residue was purificated with CC (OK. Interchim, 330 g $SiO_2$, petroleum ether/MtBE with MtBE from 5~35%, flow rate=130 mL/min, Rv=6 CV) to obtain ethyl 4-cyano-2,2-difluoro-pentanoate (10 g, 52.31 mmol, 70.19% yield).

$^1$H NMR ($CDCl_3$, 500 MHz): 1.32 (d, 3H), 1.45 (t, 3H), 2.28 (q, 1H), 2.54 (q, 1H), 2.98 (m, 1H), 4.37 (q, 2H).

Step 2: Synthesis of 4,4-difluoro-5-(4-fluorophenyl)-2-methyl-5-oxo-pentanenitrile ethyl 4-cyano-2,2-difluoro-pentanoate (9.5 g, 49.69 mmol) To a solution of 1-bromo-4-fluoro-benzene (8.70 g, 49.69 mmol, 5.47 mL) in $Et_2O$ (50 mL) and THF (50 mL) at −10° C. was added dropwise n-butyl lithium (2.5 M, 19.88 mL) 2.5 M in hexane. The formation of the organolithium species is followed by 1H-NMR. To the resulting solution, compound ethyl 4-cyano-2,2-difluoro-pentanoate (9.5 g, 49.69 mmol) in $Et_2O$ (50 mL) was added dropwise at −10° C. The mixture stirred at −10° C. for 2 hr. The reaction was quenched with a aqueous saturated solution of ammonium chloride, EtOAc was added and the phases were separated. The aqueous phase was further extracted with EtOAc (2×5 mL). The combined organic phases were dried over $MgSO_4$, filtered, concentrated in vacuo to provide 4,4-difluoro-5-(4-fluorophenyl)-2-methyl-5-oxo-pentanenitrile (8.5 g, 35.24 mmol, 70.91% yield) which was used in the next step without purification.

$^1$H NMR ($CDCl_3$, 400 MHz): 1.52 (d, 3H), 2.42 (m, 1H), 2.61 (m, 1H), 3.18 (m, 1H), 7.19 (m, 2H), 8.20 (m, 2H).

Step 3: Synthesis of tert-butyl N-[4,4-difluoro-5-(4-fluorophenyl)-5-hydroxy-2-methyl-pentyl]carbamate 4,4-difluoro-5-(4-fluorophenyl)-2-methyl-5-oxo-pentanenitrile (8.5 g, 35.24 mmol) and tert-butoxycarbonyl tert-butyl carbonate (23.07 g, 105.72 mmol, 24.26 mL) were dissolved in MeOH (20 mL) and cooled to −10° C., followed by the addition of Nickel(II) chloride hexahydrate, 98% (2.00 g, 7.05 mmol, 1.04 mL) and Sodium Borohydride (13.33 g, 352.39 mmol, 12.46 mL) in many portions, keeping temperature below −5° C. After gas evolution stopped, the mixture was filtered off and evaporated under reduced pressure. Combined organic solvents was evaporated under reduced pressure; crude product was dissolved in MTBE (20 mL) and washed with sat aq $NH_4Cl$, dried over $Na_2SO_4$ and evaporated under reduced pressure to give tert-butyl N-[4,4-difluoro-5-(4-fluorophenyl)-5-hydroxy-2-methyl-pentyl] carbamate (6.5 g, 18.71 mmol, 53.10% yield) which was used in the next step without purification.

LCMS(ESI): $[M+Na]^+$ m/z: calcd 347.2; found 370.2; Rt=1.291 min.

Step 4: Synthesis of tert-butyl N-[4,4-difluoro-5-(4-fluorophenyl)-2-methyl-5-oxo-pentyl]carbamate tert-butyl N-[4,4-difluoro-5-(4-fluorophenyl)-5-hydroxy-2-methyl-pentyl]carbamate (6.5 g, 18.71 mmol) was dissolved in DCM (20 mL), followed by the addition of Dess-Martin Periodinane (9.52 g, 22.45 mmol). After the reaction was complete, the mixture was filtered off and evaporated under reduced pressure. The crude mixture was purified with CC (Hexane/EtOAc 9:1) to give tert-butyl N-[4,4-difluoro-5-(4-fluorophenyl)-2-methyl-5-oxo-pentyl] carbamate (1.2 g, 3.47 mmol, 18.57% yield).

$^1$H NMR (400 MHz, $CDCl_3$) 1.12 (d, 3H), 1.48 (s, 9H), 2.08 (m, 2H), 2.31 (m, 1H), 3.12 (m, 2H), 4.89 (m, 1H), 7.18 (m, 2H), 8.16 (m, 2H).

LCMS(ESI): $[M+Na]^+$ m/z: calcd 345.2; found 368.2; Rt=1.437 min.

Step 5: Synthesis of 5,5-difluoro-6-(4-fluorophenyl)-3-methyl-3,4-dihydro-2H-pyridine tert-butyl N-[4,4-difluoro-5-(4-fluorophenyl)-2-methyl-5-oxo-pentyl]carbamate (1.1 g, 3.19 mmol) was dissolved in DCM (20 mL), followed by the addition of TFA (1.82 g, 15.93 mmol, 1.23 mL). After the reaction was complete (gas evolution stopped) the mixture was basified with 10% aq $K_2CO_3$ to pH 10, dried over $Na_2SO_4$ and evaporated under reduced pressure to give 5,5-difluoro-6-(4-fluorophenyl)-3-methyl-3,4-dihydro-2H-pyridine (0.8 g, crude) which was used in the next step without purification.

$^1$H NMR (400 MHz, $CDCl_3$) 1.02 (d, 3H), 1.67 (m, 1H), 2.10 (m, 1H), 2.42 (m, 1H), 3.24 (m, 1H), 4.17 (m, 1H), 7.08 (m, 2H), 7.89 (m, 2H).

LCMS(ESI): $[M+H]^+$ m/z: calcd 227.1; found 228.2; Rt=1.269 min.

Step 6: Synthesis of (2S,5S)-3,3-difluoro-2-(4-fluorophenyl)-5-methyl-piperidine 5,5-difluoro-6-(4-fluorophenyl)-3-methyl-3,4-dihydro-2H-pyridine (0.8 g, 3.52 mmol) was dissolved in MeOH (20 mL) and cooled to 0° C., followed by the addition of sodium borohydride (399.60 mg, 10.56 mmol, 373.45 µL) in few portions. After the reaction was complete, the reaction mixture was acidified to pH=2 with 10% aq HCl and the organic solvents was evaporated under reduced pressure. The crude mixture was dissolved in H₂O (10 mL), washed with MTBE (10 mL), basified with 10% aq K₂CO₃ to pH=10 and extracted with DCM (20 mL) 3 times. Evaporation of the organic solvents result in (2S,5S)-3,3-difluoro-2-(4-fluorophenyl)-5-methyl-piperidine which was used in the next step without purification.

LCMS(ESI): [M+H]⁺ m/z: calcd 229.1; found 230.0; Rt=0.733 min.

3EE. Synthesis of 2S,5S)-3-fluoro-2-(4-fluorophenyl-5-methyl-piperidine

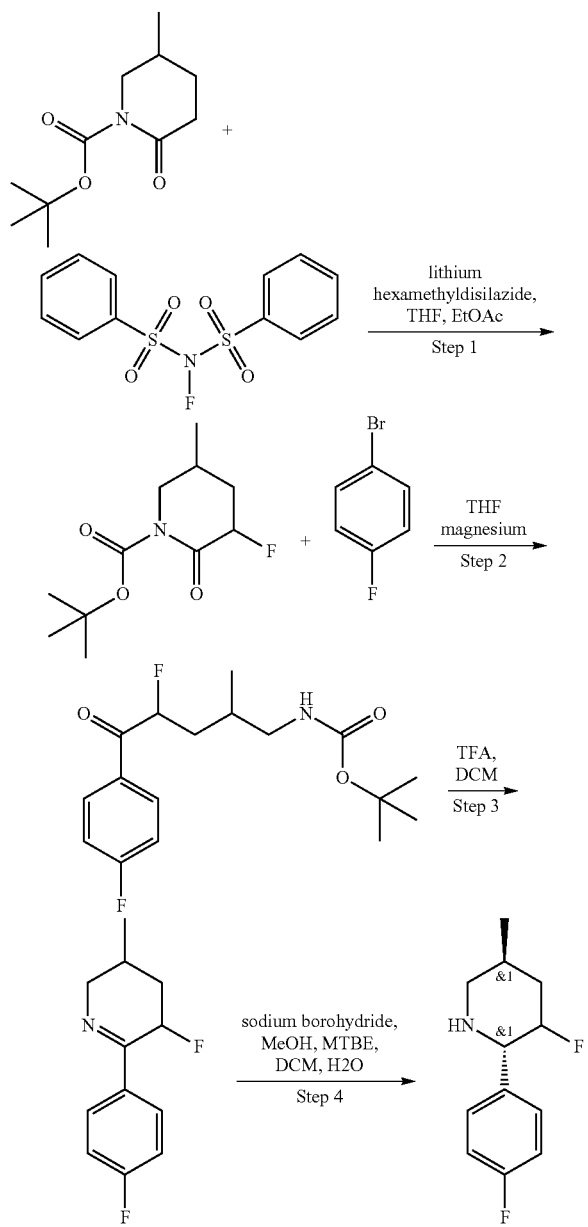

Step 1: Synthesis of tert-butyl 3-fluoro-5-methyl-2-oxo-piperidine-1-carboxylate tert-butyl 5-methyl-2-oxo-piperidine-1-carboxylate (5 g, 23.44 mmol) was dissolved in THF (5 mL) and cooled to −78° C., following by the addition of lithium hexamethyldisilazide (1.1 M, 23.44 mL) in a dropwise manner. After 10 min, N-(benzenesulfonyl)-N-fluoro-benzenesulfonamide (7.39 g, 23.44 mmol) was added in one portion and the reaction mixture was warmed to −10C. After the reaction was complete, the mixture was poured on sat aq NH₄Cl and extracted with EtOAc (10 mL). Evaporation of the solvent results in crude product. Purification with CC (Companion combiflash, 220 g SiO₂, petroleum ether/MtBE with MtBE from 10~35%, flow rate=100 mL/min, Rv=7 CV) results in tert-butyl 3-fluoro-5-methyl-2-oxo-piperidine-1-carboxylate (1.5 g, 6.49 mmol, 27.67% yield)

¹H NMR (CDCl₃, 500 MHz): 1.02 (d, 3H), 1.41 (s, 9H), 1.79 (m, 1H), 2.22 (m, 2H), 3.22 (m, 1H), 3.75 (m, 1H), 4.91 (m, 1H),

Step 2: Synthesis of tert-butyl N-[4-fluoro-5-(4-fluorophenyl)-2-methyl-5-oxo-pentyl]carbamate 1-bromo-4-fluoro-benzene (1.36 g, 7.78 mmol) and magnesium (315.35 mg, 12.97 mmol, 181.24 µL) was refluxed in THF (20 mL) in the presence of catalytic amount of I2 for 2 hr. The obtained dark solution was cooled to rt and transferred to the dropping funnel.

tert-butyl 3-fluoro-5-methyl-2-oxo-piperidine-1-carboxylate (1.5 g, 6.49 mmol) was dissolved in THE (20 mL) and cooled to −78° C. under Ar. The obtained Grignard reagent was added slowly at the same temperature. After the reaction was complete, the mixture was quenched with sat aq NH₄Cl and extracted with EtOAc (3*100 mL). Combined organic layers was washed with brine (3*30 mL), dried over Na₂SO₄ and evaporated under reduced pressure to give crude product, which was purificated by CC (Ok. Companion combiflash; 40 g SiO₂; petroleum ether/MtBE with MtBE from 0 to 38%, flow rate=40 ml/min, Rv=11-12 cv.) to give tert-butyl N-[4-fluoro-5-(4-fluorophenyl)-2-methyl-5-oxo-pentyl]carbamate (1.1 g, 3.36 mmol, 51.81% yield).

LCMS(ESI): [M+Na]⁺ m/z: calcd 327.2; found 350.2; Rt=1.322 min.

Step 3: Synthesis of 5-fluoro-6-(4-fluorophenyl)-3-methyl-2,3,4,5-tetrahydropyridine tert-butyl N-[4-fluoro-5-(4-fluorophenyl)-2-methyl-5-oxo-pentyl]carbamate (1.1 g, 3.36 mmol) was dissolved in DCM (20 mL), followed by the addition of TFA (1.92 g, 16.80 mmol, 1.29 mL). After the reaction was complete (gas evolution stopped) the mixture was basified with 10% aq K₂CO₃ to pH=10, dried over Na₂SO₄ and evaporated under reduced pressure to give 5-fluoro-6-(4-fluorophenyl)-3-methyl-2,3,4,5-tetrahydropyridine which was used in the next step without purification.

LCMS(ESI): [M+H]⁺ m/z: calcd 209.1; found 210.2; Rt=0.728 min.

Step 4: Synthesis of (2S,5S)-3-fluoro-2-(4-fluorophenyl)-5-methyl-piperidine 5-fluoro-6-(4-fluorophenyl)-3-methyl-2,3,4,5-tetrahydropyridine (736.66 mg, 3.52 mmol) was dissolved in MeOH (20 mL) and cooled to 0° C., followed by the addition of sodium borohydride (399.60 mg, 10.56 mmol, 373.45 µL) in few portions. After the reaction was complete, the reaction mixture was acidified to pH=2 with 10% aq HCl and the organic solvents was evaporated under reduced pressure. The crude mixture was dissolved in H₂O (10 mL), washed with MTBE (10 mL), basified with 10% aq K₂CO₃ to pH=10 and extracted with DCM (20 mL) 3 times. Evaporation of the organic solvents result in (2S,5S)-3-fluoro-2-(4-fluorophenyl)-5-methyl-piperidine (0.5 g, 2.37 mmol, 67.23% yield) which was used in the next step without purification.

LCMS(ESI): [M+H]⁺ m/z: calcd 211.2; found 212.0; Rt=0.726 min.

3FF. 410 Min. The Synthesis of tert-butyl (2R,5S)-5-methyl-2-[1-(1H-pyrazol-3-yl)pyrazol-4-yl]piperidine and (2R,5S)-5-methyl-2-(1H-pyrazol-4-yl)piperidine

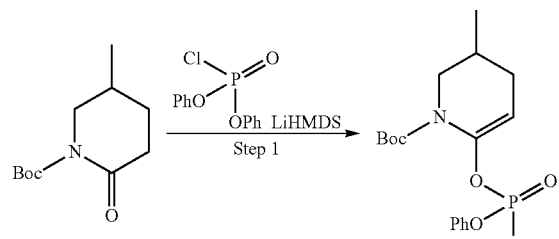

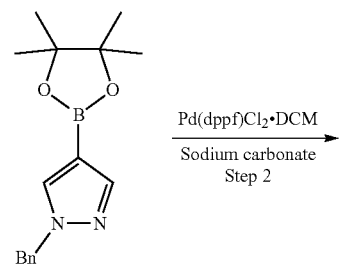

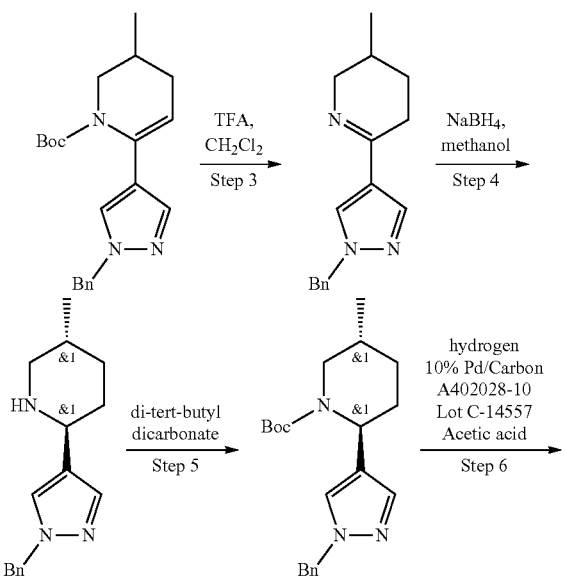

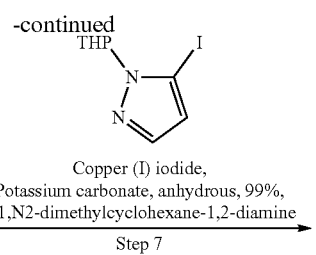

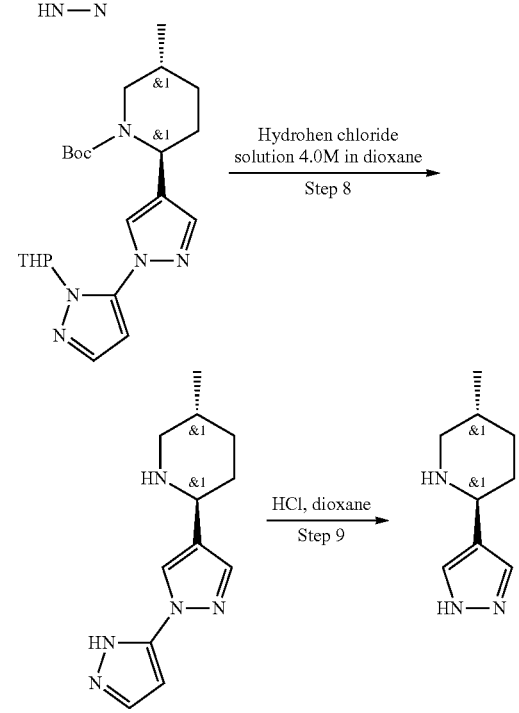

Step 1. Tert-butyl 6-diphenoxyphosphoryloxy-3-methyl-3,4-dihydro-2H-pyridine-1-carboxylate Lithium bis(trimethylsilyl)amide (49.04 g, 58.61 mmol, 54.48 mL, 20% purity) (1.08 M in THF/ethylbenzene) was added dropwise under argon to a cooled to −78° C. solution of tert-butyl 5-methyl-2-oxo-piperidine-1-carboxylate (10 g, 46.89 mmol) in THF (100 mL). The resulting solution was stirred at −78° C. for 1.5 hr, then [chloro(phenoxy)phosphoryl]oxybenzene (12.60 g, 46.89 mmol, 9.69 mL) was added dropwise maintaining temperature below −70° C. The reaction mixture was allowed to warm (cooling bath was removed) to 0° C. and then diluted with water (20 ml) and MTBE (100 ml). The organic layer was separated, the aqueous layer was additionally extracted with MTBE (50 ml). The combined organic extracts were washed with 10% aqueous sodium hydroxide solution (2*100 ml), dried over potassium carbonate and concentrated in vacuo. The residue was dissolved in hexane/MTBE mixture (1/1, 400 ml) and the resulting cloudy solution was filtered through a short pad of silica gel and evaporated in vacuo to afford crude tert-butyl 6-diphenoxyphosphoryloxy-3-methyl-3,4-dihydro-2H-pyridine-1-carboxylate (21 g, crude) as light-yellow oil, which was used directly in the next step.

¹H NMR (500 MHz, DMSO-d₆) δ (ppm) 0.95 (d, 3H), 1.41 (s, 9H), 1.69 (m, 1H), 1.87 (m, 1H), 2.25 (m, 1H), 2.97 (dd, 1H), 5.05 (t, 1H), 7.17-7.33 (m, 10H).

LCMS(ESI): [M-Boc]⁺ m/z: calcd 445.4; found 346.2; Rt=1.517 min.

Step 2. Tert-butyl 6-(1-benzylpyrazol-4-yl)-3-methyl-3,4-dihydro-2H-pyridine-1-carboxylate tert-butyl 6-diphenoxyphosphoryloxy-3-methyl-3,4-dihydro-2H-pyridine-1-carboxylate (17 g, 38.16 mmol), 1-benzyl-4-(4,4,5,5-tetramethyl-1,3,2-dioxaborolan-2-yl) pyrazole (11.93 g, 41.98 mmol) and Sodium carbonate (12.14 g, 114.49 mmol, 4.80 mL) were added to a mixture of 1,4-dioxane (150 mL) and water (50 mL). The resulting mixture was evacuated and then backfilled with argon, this operation was repeated three times, then Pd(dppf)Cl₂ DCM (1.56 g, 1.91 mmol) was added under argon. The reaction mixture was stirred under argon at 80° C. for 18 hr, then cooled and filtered. The filtercake was washed with dioxane (2*50 ml) and discarded. The filtrate was evaporated in vacuo, and the residue was purified by column chromatography on silica gel using hexane/MTBE gradient (0-35% MTBE) to afford tert-butyl 6-(1-benzylpyrazol-4-yl)-3-methyl-3,4-dihydro-2H-pyridine-1-carboxylate (9.6 g, 27.16 mmol, 71.17% yield) as light-yellow gum, which was used directly in the next step.

¹H NMR (500 MHz, DMSO-d₆) δ (ppm) 0.95 (d, 3H), 1.04 (s, 9H), 1.72 (m, 1H), 1.84 (m, 1H), 2.22 (m, 1H), 2.85 (dd, 1H), 3.78 (d, 1H), 5.19 (brs, 2H), 7.23-7.26 (m, 5H), 7.51 (s, 1H).

LCMS(ESI): [M-Boc]⁺ m/z: calcd 353.4; found 354.4; Rt=1.428 min.

Step 3. 6-(1-benzylpyrazol-4-yl)-3-methyl-2,3,4,5-tetrahydropyridine

A solution of tert-butyl 6-(1-benzylpyrazol-4-yl)-3-methyl-3,4-dihydro-2H-pyridine-1-carboxylate (9.6 g, 27.16 mmol) in Trifluoroacetic acid (111.00 g, 973.51 mmol, 75 mL) was stirred at 25° C. for 1 hr. After 1 hour, the reaction mixture was concentrated under reduced pressure. The obtained residue was diluted with ice cold water (100 mL) and neutralized with aqueous 10% NaOH solution till pH=10. The resulting mixture was extracted with dichloromethane (2×100 mL). The combined organic phase was dried over sodium sulphate and concentrated under reduced pressure to afford 6-(1-benzylpyrazol-4-yl)-3-methyl-2,3,4,5-tetrahydropyridine (6.3 g, 24.87 mmol, 91.56% yield) as light-yellow gum, which was used directly in the next step.

¹H NMR (500 MHz, CDCl₃) δ (ppm) 1.05 (s, 3H), 1.30 (m, 1H), 1.60 (m, 1H), 1.84 (m, 1H), 2.45 (m, 1H), 2.65 (dd, 1H), 3.15 (m, 1H), 3.95 (d, 1H), 5.32 (s, 2H), 7.23-7.34 (m, 5H), 7.68 (s, 1H), 7.79 (s, 1H).

LCMS(ESI): [M-Boc]⁺ m/z: calcd 253.3; found 254.2; Rt=0.715 min.

Step 4. (2R,5S)-2-(1-benzylpyrazol-4-yl)-5-methyl-piperidine

A solution of tert-butyl 6-(1-benzylpyrazol-4-yl)-3-methyl-3,4-dihydro-2H-pyridine-1-carboxylate (9.6 g, 27.16 mmol) in Trifluoroacetic acid (111.00 g, 973.51 mmol, 75 mL) was stirred at 25° C. for 1 hr. After 1 hour, the reaction mixture was concentrated under reduced pressure. The obtained residue was diluted with ice cold water (100 mL) and neutralized with aqueous 10% NaOH solution till pH=10. The resulting mixture was extracted with dichloromethane (2×100 mL). The combined organic phase was dried over sodium sulphate and concentrated under reduced pressure to afford 6-(1-benzylpyrazol-4-yl)-3-methyl-2,3,4, 5-tetrahydropyridine (6.3 g, 24.87 mmol, 91.56% yield) as light-yellow gum, which was used directly in the next step.

¹H NMR (500 MHz, CDCl₃) δ (ppm) 0.75 (s, 3H), 1.10 (dd, 1H), 1.40 (m, 1H), 1.50-1.70 (brs, 1H), 1.87 (t, 2H), 2.33 (t, 1H), 3.03 (d, 1H), 3.59 (d, 1H), 5.25 (s, 2H), 7.20 (s, 1H), 7.29-7.32 (m, 5H), 7.46 (s, 1H).

LCMS(ESI): [M-Boc]⁺ m/z: calcd 255.3; found 256.2; Rt=0.733 min.

Step 5. Tert-butyl (2R,5S)-2-(1-benzylpyrazol-4-yl)-5-methyl-piperidine-1-carboxylate di-tert-butyl dicarbonate (5.47 g, 25.08 mmol, 5.76 mL) was added in one portion to a stirred solution of (2R,5S)-2-(1-benzylpyrazol-4-yl)-5-methyl-piperidine (6.1 g, 23.89 mmol) in dichloromethane (100 mL) at 25° C. The reaction mixture was stirred at 25° C. for 1 hr, and then concentrated in vacuo to afford crude tert-butyl (2R,5S)-2-(1-benzylpyrazol-4-yl)-5-methyl-piperidine-1-carboxylate (8.4 g, 23.63 mmol, 98.92% yield) as light-yellow gum, which was used directly in the next step.

¹H NMR (500 MHz, CDCl₃) δ (ppm) 0.95 (s, 3H), 1.10-1.40 (m, 12H), 1.40-1.80 (m, 4H), 2.10 (t, 1H), 2.95 (d, 1H), 3.75 (d, 1H), 5.20 (s, 2H), 5.40 (s, 1H), 7.20-7.38 (m, 7H).

LCMS(ESI): [M+1]⁺ m/z: calcd 355.5; found 356.2; Rt=1.567 min.

Step 6. Tert-butyl (2R,5S)-5-methyl-2-(1H-pyrazol-4-yl)piperidine-1-carboxylate

To a solution of tert-butyl (2R,5S)-2-(1-benzylpyrazol-4-yl)-5-methyl-piperidine-1-carboxylate (8.4 g, 23.63 mmol) in a methanol (150 mL) was added 10% Palladium on carbon wet (2.51 g, 23.63 mmol) and Acetic acid (2.13 g, 35.45 mmol, 2.03 mL). The resulting mixture was evacuated and then backfilled with hydrogen. The reaction mixture was stirred under atmosphere of hydrogen (balloon pressure) at 55° C. for 96 hr. The HNMR of the aliquot showed 50% conversion. 10% Pd/Carbon A402028-10 Lot C-14557 (1.5 g, 23.63 mmol) was added to the reaction mixture, and it was again evacuated and then backfilled with hydrogen; and then stirred under atmosphere of hydrogen (balloon pressure) at 55° C. for 48 hr. The HNMR of the aliquot showed that reaction was complete. The catalyst was filtered off, the filtrate was concentrated in vacuo. The residue was dissolved in dichloromethane (100 ml) and washed with a solution of sodium hydrogen carbonate (3 g) in water (50 ml). The organic layer was separated, dried over sodium sulphate and concentrated in vacuo to afford tert-butyl (2R,5S)-5-methyl-2-(1H-pyrazol-4-yl)piperidine-1-carboxylate (6 g, 22.61 mmol, 95.69% yield) as light-yellow gum, which was used directly in the next step.

¹H NMR (500 MHz, CDCl₃) δ (ppm) 1.03 (d, 3H), 1.37 (m, 1H), 1.48 (s, 9H), 1.82 (m, 3H), 2.13 (m, 1H), 2.98 (d, 1H), 3.72 (d, 1H), 5.42 (d, 1H), 7.43 (s, 2H).

LCMS(ESI): [M+1]⁺ m/z: calcd 265.2; found 266.2; Rt=1.315 min.

Step 7. Tert-butyl (2R,5S)-5-methyl-2-[1-(1-tetrahydropyran-2-ylpyrazol-3-yl)pyrazol-4-yl]piperidine-1-carboxylate A mixture of tert-butyl (2R,5S)-5-methyl-2-(1H-pyrazol-4-yl)piperidine-1-carboxylate (3 g, 11.31 mmol), 3-iodo-1- tetrahydropyran-2-yl-pyrazole (4.3 g, 15.46 mmol), Copper (I) iodide (1.50 g, 7.88 mmol, 266.90 µL), Potassium carbonate, anhydrous, 99% (3.8 g, 27.49 mmol, 1.66 mL), N1,N2-dimethylcyclohexane-1,2-diamine (959.99 mg, 6.75 mmol), copper (400 mg, 6.29 mmol) and toluene (100 mL) in 100 ml single-neck round bottom flask equipped with a reflux condenser and glass stopper was evacuated and then backfilled with argon. The reaction mixture was then stirred with a reflux condenser under argon at 110° C. for 20 hr. The reaction mixture was cooled down, and 50 ml of 25% aqueous ammonia were added. The resulting mixture was stirred for 10 min., and then filtered through a short pad of magnesium silicate. The filtercake was additionally washed with ethyl acetate (2*50 ml) and discarded. The filtrate was transferred to a separatory funnel, layers were separated, the organic layer was additionally washed with water (50 ml), dried over sodium sulphate and concentrated in vacuo to afford crude tert-butyl (2R,5S)-5-methyl-2-[1-(1-tetrahydropyran-2-ylpyrazol-3-yl)pyrazol-4-yl]piperidine-1-carboxylate (4.9 g, crude) as light-yellow gum, which was used directly in the next step.

$^1$H NMR (500 MHz, CDCl$_3$) δ (ppm) 1.02 (d, 3H), 1.47 (s, 9H), 1.50-1.70 (m, 6H), 1.70-1.90 (m, 3H), 1.95-2.40 (m, 6H), 3.00 (d, 1H), 3.60-3.72 (m, 2.5H), 4.10 (m, 1.50), 5.28 (d, 1H), 5.42 (d, 1H), 6.54 (s, 1H), 7.43 (m, 1H), 7.40 (s, 1H), 7.50 (s, 1H), 7.90 (s, 1H).

LCMS(ESI): [M+1]$^+$ m/z: calcd 415.2; found 416.2; Rt=1.554 min.

Step 8. Tert-butyl (2R,5S)-5-methyl-2-[1-(1H-pyrazol-3-yl)pyrazol-4-yl]piperidine Hydrogen chloride solution 40 M in dioxane (26.25 g, 100.08 mmol, 25 mL, 13.9% purity) was added at 25° C. to a stirred solution of tert-butyl (2R,5S)-5-methyl-2-[1-(1-tetrahydropyran-2-ylpyrazol-3-yl)pyrazol-4-yl]piperidine-1-carboxylate (1.1 g, 2.65 mmol) in methanol (25 mL). The reaction mixture was stirred at 25° C. for 12 hr, and then concentrated in vacuo to afford crude (2R,5S)-5-methyl-2-[1-(1H-pyrazol-3-yl)pyrazol-4-yl]piperidine (1.1 g, crude, 3HCl) as light-yellow foam, which was used directly in the next step.

$^1$H NMR (500 MHz, DMSO) δ(ppm) 0.87 (d, 3H), 1.22 (m, 1H), 1.26 (m, 1H), 1.91 (m, 3H), 2.60 (m, 2H), 3.12 (m, 1H), 4.13 (t, 1H), 6.14 (s, 2H), 7.79-7.87 (m, 2H), 8.40 (s, 1H), 9.49 (m, 3H).

LCMS(ESI): [M+1]$^+$ m/z: calcd 232.2; found 231.2; Rt=0.672 min.

Step 9. Synthesis of (2R,5S)-5-methyl-2-(1H-pyrazol-4-yl)piperidine

3GG. Synthesis of tert-butyl 6-(5-methyl-2-piperidyl)pyridin-3-amine

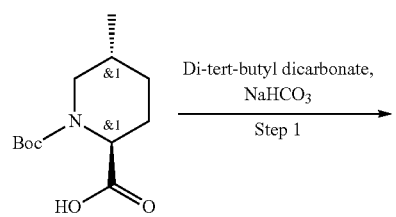

Step 1. Synthesis of (2S,5R)-1-tert-butoxycarbonyl-5-methyl-piperidine-2-carboxylic acid (2S,5R)-5-methylpiperidine-2-carboxylic acid (14 g, 77.93 mmol, HCl) was dissolved in water (150 mL) and Sodium bicarbonate (19.64 g, 233.80 mmol, 9.09 mL) was added thereto. The resulting mixture was diluted with THF (150 mL) and Di-tert-butyl dicarbonate (20.41 g, 93.52 mmol, 21.46 mL) was added dropwise to the previous mixture. The resulting mixture was stirred at room temperature for 18 hr. The reaction mixture was concentrated under reduced pressure and the residue was re-dissolved in water (50 ml). The resulting mixture was extracted with MTBE (3*50 ml) and the aqueous layer was acidified with NaHSO₄. The resulting mixture was extracted with DCM (2*50 ml) and combined organic layers were dried over Na₂SO₄, filtered and evaporated to obtain (2S,5R)-1-tert-butoxycarbonyl-5-methyl-piperidine-2-carboxylic acid (14 g, 57.54 mmol, 73.84% yield) as white solid.

$^1$H NMR (400 MHz, DMSO-d₆) δ (ppm) 0.88 (d, 3H), 1.32 (s, 9H), 1.31-1.42 (m, 2H), 1.79 (m, 3H), 3.04 (m, 1H), 3.28 (m, 1H), 3.47 (d, 1H), 4.50 (m, 1H), 12.65 (brs, 1H).

LCMS(ESI): [M-Boc]⁺ m/z: calcd 243.3; found 144.0; Rt=1.140 min.

Step 2. Synthesis of tert-butyl (2S,5R)-2-[methoxy(methyl)carbamoyl]-5-methyl-piperidine-1-carboxylate Carbonyldiimidazole (8.00 g, 49.32 mmol) was added in one portion to a stirred solution of (2S,5R)-1-tert-butoxycarbonyl-5-methyl-piperidine-2-carboxylic acid (10 g, 41.10 mmol) in THF (200 mL) at 25° C. The resulting mixture was stirred at 25° C. until carbon dioxide evolution was completed, then methoxy(methyl)amine hydrochloride (8.02 g, 82.20 mmol) and TEA (8.32 g, 82.20 mmol, 11.46 mL) were added. The reaction mixture was stirred at 50° C. for 12 hr, then cooled and evaporated in vacuo. The residue was diluted with 5% aqueous sodium hydrogen sulphate solution (200 ml) and extracted with dichloromethane (2*100 ml). The combined organic extracts were washed with water (100 ml), dried over sodium sulphate and evaporated in vacuo to afford tert-butyl (2S,5R)-2-[methoxy(methyl)carbamoyl]-5-methyl-piperidine-1-carboxylate (9 g, 31.43 mmol, 76.46% yield) as white solid, which was used directly in the next step.

$^1$H NMR (500 MHz, DMSO-d₆) δ (ppm) 0.87 (d, 3H), 1.33 (s, 9H), 1.56 (m, 3H), 1.72 (m, 1H), 1.84 (m, 1H), 3.05 (s, 3H), 3.39 (m, 2H), 3.65 (s, 3H), 4.71 (m, 1H).

LCMS(ESI): [M-Boc]⁺ m/z: calcd 286.4; found 187.2; Rt=1.380 min.

Step 4. Synthesis of tert-butyl (2S,5R)-5-methyl-2-(5-nitro-2-pyridyl)piperidine-1-carboxylate tert-butyl (2S,5R)-2-acetyl-5-methyl-piperidine-1-carboxylate (3.1 g, 12.85 mmol) and 1-methyl-3,5-dinitro-pyridin-2-one (3.84 g, 19.27 mmol) were dissolved in MeOH/NH₃ (50 mL). The reaction mixture was stirred at 90° C. overnight under high pressure. Then it was cooled and evaporated in vacuo to afford crude tert-butyl (2S,5R)-5-methyl-2-(5-nitro-2-pyridyl)piperidine-1-carboxylate (4 g, 12.45 mmol, 96.89% yield), which was used in next step without purification.

LCMS(ESI): [M-Boc]⁺ m/z: calcd 321.2; found 222.2; Rt=1.328 min.

Step 5. Synthesis of tert-butyl (2S,5R)-2-(5-amino-2-pyridyl)-5-methyl-piperidine-1-carboxylate tert-butyl (2S,5R)-5-methyl-2-(5-nitro-2-pyridyl)piperidine-1-carboxylate (4 g, 12.45 mmol) was dissolved in MeOH (50 mL) and Palladium on carbon, 10% (662.29 mg, 622.33 µmol, 10% purity) was added. Then reaction mixture was stirred at 25° C. for 24 hr. Catalyst was filtered on. Solution was evaporated in vacuo to afford crude tert-butyl (2S,5R)-2-(5-amino-2-pyridyl)-5-methyl-piperidine-1-carboxylate (3.6 g, 12.35 mmol, 99.26% yield), which was used in next step without purification.

LCMS(ESI): [M-Boc]⁺ m/z: calcd 291.2; found 292.2; Rt=0.908 min.

Step 6. Synthesis of tert-butyl 6-(5-methyl-2-piperidyl)pyridin-3-amine tert-butyl (2S,5R)-2-(5-amino-2-pyridyl)-5-methyl-piperidine-1-carboxylate (1.9 g, 6.52 mmol) was dissolved in diox/HCl (15 mL) and was stirred at room temperature overnight. Then reaction mixture was concentrated under reduced pressure. The obtained solid was subjected to HPLC (Waters Sunfire C18 20*100 5 mkm column and H₂O -MeOH with NH₃ as an eluent mixture) to afford pure 6-(5-methyl-2-piperidyl)pyridin-3-amine (0.5 g, 2.61 mmol, 40.09% yield).

LCMS(ESI): [M+1]⁺ m/z: calcd 191.2; found 192.2; Rt=0.707 min.

3HH. Synthesis of 2-(5-methyl-2-piperidyl)pyridine

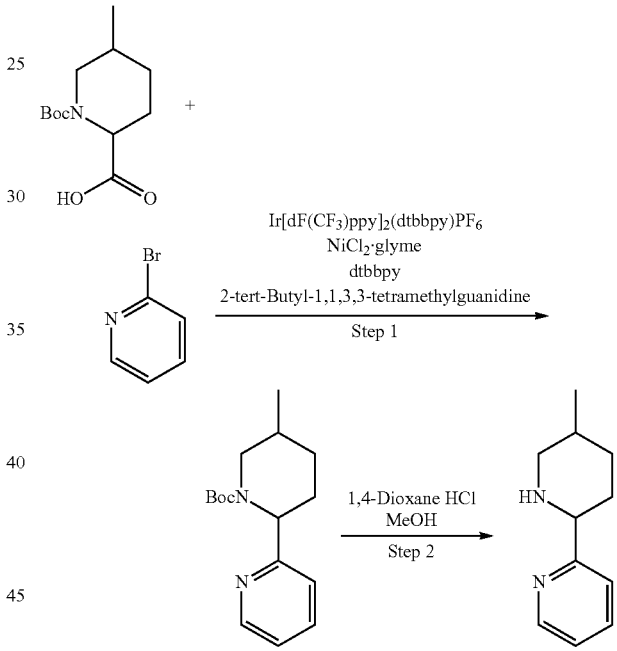

Step 1. Synthesis of tert-butyl 5-methyl-2-(2-pyridyl)piperidine-1-carboxylate r[dF(CF₃)ppy]2(dtbbpy)PF6 (101.45 mg, 90.42 µmol), NiCl2·glyme (198.68 mg, 904.24 µmol) and dtbbpy (242.69 mg, 904.24 µmol) were mixed together in DMF (110 mL). 1-tert-butoxycarbonyl-5-methyl-piperidine-2-carboxylic acid (2.2 g, 9.04 mmol), 2-tert-butyl-1,1,3,3-tetramethylguanidine (1.55 g, 9.04 mmol, 1.82 mL) and 2-bromopyridine (1.43 g, 9.04 mmol, 876.48 µL) were added to the previous mixture and the resulting mixture was degassed for 15 min by spurging with argon. The vial was sealed, wrapped with parafilm and placed into blue LED photoreactor. The reaction mixture was stirred at 25° C. for 36 hr. The reaction mixture was concentrated in vacuo and water (50 ml) was added to the residue. The resulting mixture was extracted with EtOAc (2*50 ml). Combined organic layers were washed with water (3*50 ml), brine, dried over Na₂SO₄, filtered and evaporated. The residue was purified by column chromatography to obtain tert-butyl 5-methyl-2-(2-pyridyl)piperidine-1-carboxylate (1.45 g, 5.25 mmol, 58.02% yield) as mixture of cis- and trans-isomers (~1:1).

$^1$H NMR (400 MHz, CDCl$_3$) δ (ppm) 0.77 (d, 1.5H for 1 isomer) and 1.04 (d, 1.5H for 2 isomer), 1.40 (s, 9H), 1.40-1.60 (m, 2H), 1.60 (m, 1H), 1.83 (m, 1H), 2.13 (m, 0.5H for 1 isomer), 2.34 (m, 1H), 2.68 (m, 0.5H for 1 isomer), 3.12 (m, 0.5H for 2 isomer), 3.66 (m, 0.5H for 2 isomer), 5.29 (m, 1H), 7.15 (m, 2H), 7.65 (m, 1H), 8.88 (m, 1H).

LCMS(ESI): [M+1]$^+$ m/z: calcd 276.2; found 277.0; Rt(isomer 1)=1.277 min, Rt(isomer 2)=1.406 min.

Step 2. Synthesis of 2-(5-methyl-2-piperidyl)pyridine

To a solution of tert-butyl 5-methyl-2-(2-pyridyl)piperidine-1-carboxylate (1.4 g, 5.07 mmol) in MeOH (10 mL) was added 1,4-dioxane HCl (7 mL) and the mixture was stirred at rt overnight. The solvent was evaporated to obtain 2-(5-methyl-2-piperidyl)pyridine (1.2 g, crude)

LCMS(ESI): [M+1]$^+$ m/z: calcd 176.2; found 177.2; Rt(isomer 1)=0.737 min, Rt(isomer 2)=0.767 min.

3II. Synthesis of rac-(2R,5R)-4,4-difluoro-2-(4-fluorophenyl)-5-methyl-piperidine

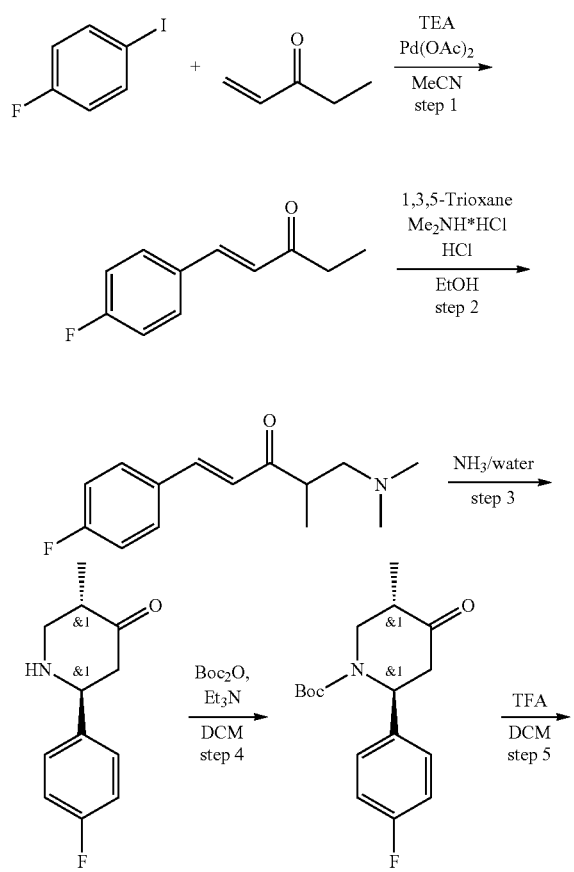

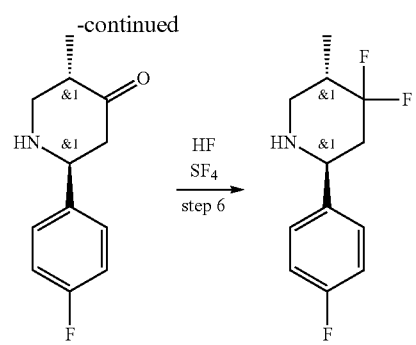

Step 1: Synthesis of (E)-1-(4-fluorophenyl)pent-1-en-3-one

To a mixture of 1-fluoro-4-iodo-benzene (40 g, 180.18 mmol, 20.73 mL) and TEA (18.23 g, 180.18 mmol, 25.11 mL) was added pent-1-en-3-one (30.31 g, 360.36 mmol), followed by Pd(dppf)C$_{12}$DCM (7.36 g, 9.01 mmol) and MeCN (200 mL) at rt. The mixture was refluxed for 12 hr The reaction mixture was concentrated on vacuo. The obtained residue was diluted with MTBE and water, the organic layer was separated and the aqueous layer was washed with additional MTBE, the combined organic layers was dried over anhydrous sodium sulphate, filtered and concentrated in vacuo. (E)-1-(4-fluorophenyl)pent-1-en-3-one (25.1 g, 140.85 mmol, 78.17% yield) was used in the next step without further purification. $^1$H NMR (400 MHz, CDCl$_3$) δ (ppm) 1.18 (t, 3H), 2.69 (m, 2H), 6.65 (d, 1H), 7.18 (d, 1H), 7.27 (s, 1H), 7.36 (d, 1H), 7.45 (d, 1H).

$^1$H NMR (400 MHz, DMSO-d$_6$) δ (ppm) 1.17 (d, 3H), 2.68 (s, 2H), 6.69 (d, 1H), 7.08 (m, 2H), 7.54 (m, 3H).

LCMS(ESI): [M+1]$^+$ m/z: calcd 178.2; found 179.0; Rt=1.330 min.

Step 2: Synthesis of (E)-5-(dimethylamino)-1-(4-fluorophenyl)-4-methyl-pent-1-en-3-one (E)-1-(4-fluorophenyl)pent-1-en-3-one (41.7 g, 234.00 mmol), N-methylmethanamine (19.08 g, 234.00 mmol, 24.62 mL, HCl) and Formaldehyde, 37% w/w aq. soln., stab. with 7-8% methanol (14.76 g, 491.41 mmol, 13.66 mL) was in the mixture of Ethanol (500 mL) and HCl (aq) (50 mL) then stirred at 80° C. for 12 hr. The reaction mixture was concentrated in vacuo. (E)-5-(dimethylamino)-1-(4-fluorophenyl)-4-methyl-pent-1-en-3-one (72.67 g, crude, HCl) was used in the next step without further purification.

$^1$H NMR (400 MHz, DMSO-d$_6$) δ (ppm) 1.21 (d, 3H), 2.68 (s, 6H), 3.06 (m, 1H), 3.44-3.55 (m, 1H), 7.04 (d, 1H), 7.26 (m, 1H), 7.74 (d, 1H), 7.84 (m, 2H).

LCMS(ESI): [M+1]$^+$ m/z: calcd 235.2; found 236.2; Rt=0.876 min.

Step 3: Synthesis of rac-(2R,5R)-2-(4-fluorophenyl)-5-methyl-piperidin-4-one (E)-5-(dimethylamino)-1-(4-fluorophenyl)-4-methyl-pent-1-en-3-one (72.67 g, 267.41 mmol, HCl) was dissolved in water (250 mL) and NH$_3$(aq) (250 mL) then the reaction mixture was stirred at 80° C. for 12 hr. The reaction mixture was acidified with 1 N HCl, extracted with MTBE then aqueous layer was basified with 1 N NaOH and extracted with DCM. The DCM layer was dried over Na$_2$SO$_4$, filtered and evaporated on vacuo to give (2R,5R)-2-(4-fluorophenyl)-5-methyl-piperidin-4-one (22.9 g, 110.50 mmol, 41.32% yield) which was used in the next step without further purification.

$^1$H NMR (400 MHz, CDCl$_3$) δ (ppm) 1.03 (d, 3H), 1.26 (m, 1H), 2.17 (m, 1H), 2.51 (m, 2H), 2.64 (m, 2H), 3.44 (m, 1H), 3.88 (d, 1H), 7.07 (m, 2H), 7.33 (m, 2H).

LCMS(ESI): [M+1]$^+$ m/z: calcd 207.2; found 208.4; Rt=0.591 min.

Step 4: Synthesis of rac-tert-butyl (2R,5R)-2-(4-fluorophenyl)-5-methyl-4-oxo-piperidine-1-carboxylate (2R,5R)-2-(4-fluorophenyl)-5-methyl-piperidin-4-one (22.9 g, 110.50 mmol) and TEA (16.77 g, 165.75 mmol, 23.10 mL) was dissolved in DCM (330 mL), then Di-tert-butyl dicarbonate (27.73 g, 127.07 mmol, 29.16 mL) was added dropwise under ice/water cooling, after that the reaction mixture was stirred at 20° C. for 12 hr. The reaction mixture was washed with NaHSO$_4$(aq) three times, the DCM layer was dried over Na$_2$SO$_4$, filtered and concentrated on vacuo. The crude product was purified by FCC (Companion combiflash; 120 g SiO$_2$, Hex-MTBE from 0~100%, flow rate=60 mL/min, cv=12). The desired product (tert-butyl (2R,5R)-2-(4-fluorophenyl)-5-methyl-4-oxo-piperidine-1-carboxylate (13 g, 42.30 mmol, 38.28% yield) was obtained as brown gum.

$^1$H NMR (400 MHz, CDCl$_3$) δ (ppm) 1.01 (d, 3H), 1.31 (s, 9H), 2.35 (m, 1H), 2.81 (d, 1H), 2.81 (d, 1H), 3.69 (m, 2H), 5.28 (m, 1H), 7.05 (m, 2H), 7.23 (m, 2H).

LCMS(ESI): [M+Na]*m/z: calcd 307.2; found 330.2; Rt=1.346 min.

Step 5: Synthesis of rac-(2R,5R)-2-(4-fluorophenyl)-5-methyl-piperidin-4-one tert-butyl (2R,5R)-2-(4-fluorophenyl)-5-methyl-4-oxo-piperidine-1-carboxylate (1.7 g, 5.53 mmol) was dissolved in DCM (17 mL) and TFA (17 mL) was added in one portion. The reaction mixture was stirred at 20° C. for 1 hr. The reaction mixture was concentrated on vacuo. The obtained product was used in the next step without further purification. The desired product ((2R,5R)-2-(4-fluorophenyl)-5-methyl-piperidin-4-one (2.6 g, crude, CF$_3$COOH)) was obtained as a brown gum.

$^1$H NMR (400 MHz, DMSO) δ(ppm) 0.99 (d, 3H), 2.59 (m, 1H), 2.91 (m, 2H), 3.12 (m, 2H), 3.62 (m, 1H), 4.80 (m, 1H), 7.14 (m, 2H), 7.25 (m, 3H), 7.31 (m, 3H).

LCMS(ESI): [M+1]$^+$ m/z: calcd 207.2; found 208.2; Rt=0.689 min.

Step 6: Synthesis of rac-(2R,5R)-4,4-difluoro-2-(4-fluorophenyl)-5-methyl-piperidine (2R,5R)-2-(4-fluorophenyl)-5-methyl-piperidin-4-one (2.6 g, 8.09 mmol, CF$_3$COOH), HF (1.62 g, 80.93 mmol) and SF$_4$ (1.75 g, 16.19 mmol) were heated in a stainless steel autoclave at 70° C. for 12 h. After completion of the reaction, the gaseous products were vented off, the reaction mixture was poured onto ice and neutralized with a 10% aqueous solution of K$_2$CO$_3$. The product was extracted with MTBE. Combined organic extracts were washed with brine, dried over Na$_2$SO$_4$, and concentrated under reduced pressure to give (2R,5R)-4,4-difluoro-2-(4-fluorophenyl)-5-methyl-piperidine (1.2 g, 5.23 mmol, 64.68% yield) which was used in the next step without further purification.

$^1$H NMR (400 MHz, CDCl$_3$) δ (ppm) 1.02 (d, 3H), 1.80 (m, 2H), 1.86 (m, 1H), 2.01 (m, 1H), 2.67 (dd, 1H), 3.06 (m, 1H), 3.86 (d, 1H), 7.00 (m, 1H), 7.32 (m, 1H).

LCMS(ESI): [M+1]$^+$ m/z: calcd 229.2; found 230.2; Rt=0.863 min.

3JJ. Synthesis of 5-(5-methyl-2-piperidyl)-1H-pyrazolo[4,3-b]pyridine

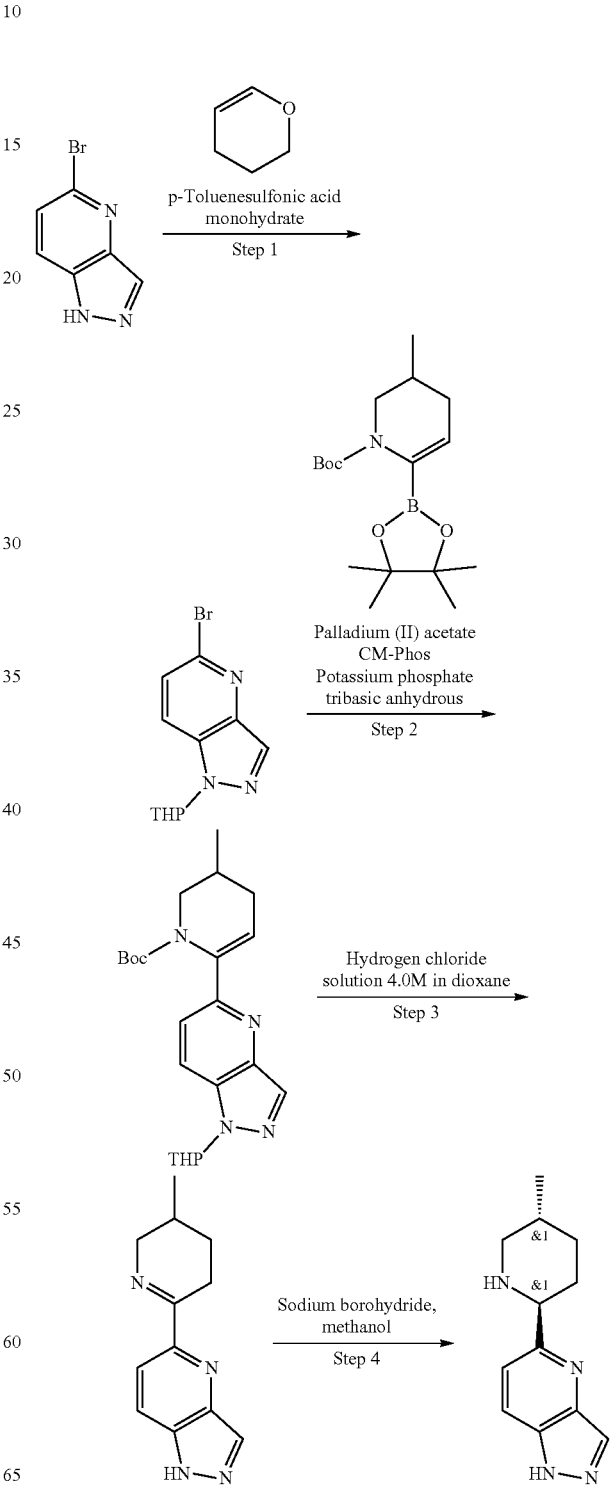

Step 1. Synthesis of 5-bromo-1-tetrahydropyran-2-yl-pyrazolo[4,3-b]pyridine 5-bromo-1H-pyrazolo[4,3-b]pyridine (10 g, 50.50 mmol) and 3,4-dihydro-2H-pyran (12.74 g, 151.50 mmol, 13.76 mL) were dissolved in CH₃CN (200 mL) and p-Toluenesulfonic acid monohydrate (1.92 g, 10.10 mmol, 1.55 mL) was added thereto. The reaction mixture was stirred for 12 hr. The resulting mixture was evaporated in vacuo, poured into aqeuous NaHCO₃(conc.) solution (150 ml) and extracted with EtOAc (2×100 ml). The combined organic extracts were washed with water (2*40 ml), dried over sodium sulphate and evaporated in vacuo to leave 25 g of crude product, 25 g of which was purification by column chromatography on silica gel using hexane/MTBE gradient (10-100% MTBE) to afford 5-bromo-1-tetrahydropyran-2-yl-pyrazolo[4,3-b]pyridine (6.4 g, 22.68 mmol, 44.92% yield).

$^1$H NMR (500 MHz, CDCl₃) δ (ppm) 1.66 (m, 4H), 1.75 (m, 2H), 2.43 (m, 1H), 3.69 (m, 1H), 3.95 (m, 1H), 5.71 (d, 1H), 7.38 (d, 1H), 7.58 (d, 1H), 8.13 (s, 1H).

LCMS(ESI): [M]⁺ m/z: calcd 282.0; found 282.0; Rt=1.218 min.

Step 2. Synthesis of tert-butyl 3-methyl-6-(1-tetrahydropyran-2-ylpyrazolo[4,3-b]pyridin-5-yl)-3,4-dihydro-2H-pyridine-1-carboxylate tert-butyl 3-methyl-6-(4,4,5,5-tetramethyl-1,3,2-dioxaborolan-2-yl)-3,4-dihydro-2H-pyridine-1-carboxylate (10.79 g, 33.39 mmol) and 5-bromo-1-tetrahydropyran-2-yl-pyrazolo[4,3-b]pyridine (4.71 g, 16.69 mmol) were mixed together in t-BuOH (80 mL). The resulting mixture was evacuated and then backfilled with argon, this operation was repeated three times, then Palladium (II) acetate (187.40 mg, 834.70 μmol) in t-BuOH (80 mL) and CM-Phos (673.67 mg, 1.67 mmol) were added under argon. The reaction mixture was stirred under argon at 115° C. for 17 hr, then cooled and evaporated in vacuo poured into water (150 ml) and extracted with EtOAc (2×80 ml). The combined organic extracts were washed with water (2*30 ml), dried over sodium sulphate and evaporated in vacuo to leave 10.5 g of crude product, 10.5 g of which was purification by column chromatography on silica gel using hexane/MTBE gradient (10-100% MTBE) to afford product tert-butyl 3-methyl-6-(1-tetrahydropyran-2-ylpyrazolo[4,3-b]pyridin-5-yl)-3,4-dihydro-2H-pyridine-1-carboxylate (0.6 g, 1.51 mmol, 9.02% yield)

LCMS(ESI): [M-$^t$Bu]⁺ m/z: calcd 398.0; found 399.2; Rt=1.405 min.

Step 3. Synthesis of 5-(3-methyl-2,3,4,5-tetrahydropyridin-6-yl)-1H-pyrazolo[4,3-b]pyridine The solution of tert-butyl 3-methyl-6-(1-tetrahydropyran-2-ylpyrazolo[4,3-b]pyridin-5-yl)-3,4-dihydro-2H-pyridine-1-carboxylate (0.6 g, 1.51 mmol) in MeOH (20 mL) and Hydrogen chloride solution 40 M in dioxane (800.00 mg, 21.94 mmol, 1 mL) was stirred at 115° C. for 17 hr, and then evaporated and was added water (20 ml) to the residue and pH was adjusted to 8 with a 10% aqueous solution of sodium hydrocarbonate. The resulting mixture was extracted with EtOAc (2*20 mL). The combined organic extracts were dried over sodium sulphate and evaporated in vacuo to afford 5-(3-methyl-2,3,4,5-tetrahydropyridin-6-yl)-1H-pyrazolo[4,3-b]pyridine (0.32 g, 1.49 mmol, 99.19% yield)

LCMS(ESI): [M+H]⁺ m/z: calcd 214.1; found 215.2; Rt=0.743 min.

Step 4. Synthesis of 5-(5-methyl-2-piperidyl)-1H-pyrazolo[4,3-b]pyridine

Sodium Borohydride (113.00 mg, 2.99 mmol, 105.61 μL) was added in one portion to a stirred solution of 5-(3-methyl-2,3,4,5-tetrahydropyridin-6-yl)-1H-pyrazolo[4,3-b]pyridine (0.32 g, 1.49 mmol) in MeOH (15 mL) at 0° C. The resulting mixture was stirred at 0° C. for 5 hr, and then evaporated in vacuo. The residue was diluted with water (20 mL) and extracted with dichloromethane (2*30 mL). The combined organic extracts were dried over sodium sulphate and evaporated in vacuo to afford 5-(5-methyl-2-piperidyl)-1H-pyrazolo[4,3-b]pyridine (0.24 g, 1.11 mmol, 74.30% yield).

LCMS(ESI): [M+H]⁺ m/z: calcd 216.2; found 217.2; Rt=0.578 min.

3KK. Synthesis of rac-N-methyl-3-[(2R,5S)-5-methyl-2-piperidyl]piperidine-1-carboxamide, rac-1-[3-[(2R,5S)-5-methyl-2-piperidyl]-1-piperidyl]ethanone and rac-1-methyl-3-[(2R,5S)-5-methyl-2-piperidyl]piperidine

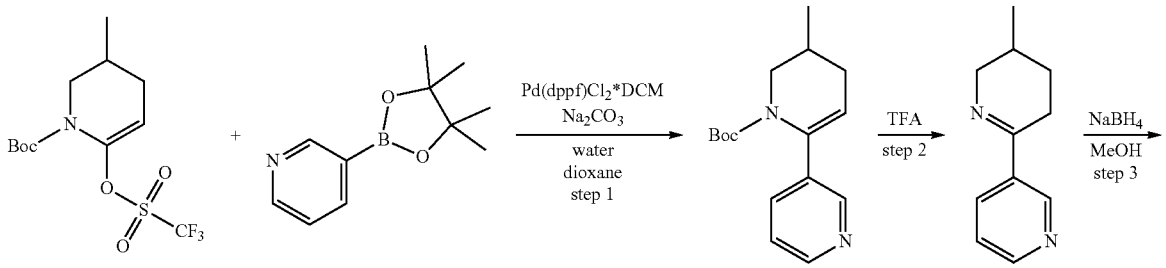

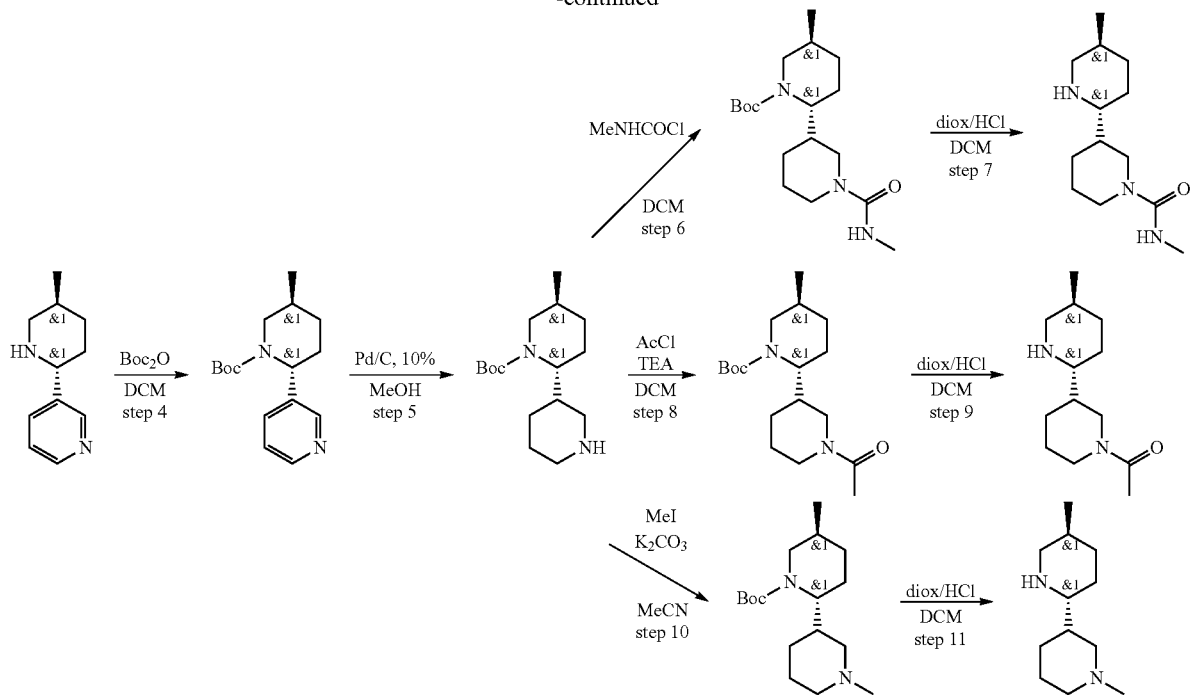

Step 1: Synthesis of tert-butyl 5-methyl, 6-dihydro-[2,3'-bipyridine]-e(4H)-carboxylate A solution of tert-butyl 3-methyl-6-(trifluoromethylsulfonyloxy)-3,4-dihydro-2H-pyridine-1-carboxylate (19 g, 55.02 mmol), 3-(4,4,5,5-tetramethyl-1,3,2-dioxaborolan-2-yl)pyridine (10.26 g, 50.02 mmol), sodium carbonate (15.90 g, 150.05 mmol, 6.29 mL) in dioxane (100 mL) and water (50 mL) was evacuated and refiled with Ar three time. To this mixture, [1,1'-bis(diphenylphosphino)ferrocene]dichloropalladium(II), complex with DCM (2.04 g, 2.50 mmol) was added and resulting mixture was stirred at 95° C. for 12 hr, cooled, filtered and evaporated. The residue was taken up with water (200 ml) and extracted with MTBE (3*200 ml). The organic layer was washed with brine (150 ml), dried over $Na_2SO_4$, filtered through a thin layer of $SiO_2$ and evaporated in vacuum to give tert-butyl 3-methyl-6-(3-pyridyl)-3,4-dihydro-2H-pyridine-m-carboxylate (10 g, 36.45 mmol, 72.875 yield). This compound was used for the next step without further purification.

$^1$H NMR (400 z, $CDCl_3$) δ(ppm) 1.01 (s, 12H), 1.86 (m, 1H), 2.00 (m, 1H), 2.41 (m, 1H), 2.98 (t, 1H), 4.06 (d, 1H), 5.32 (m, 1H), 7.20 (m, 1H), 7.55 (m, 1H), 8.45 (m, 1H), 8.53 (s, 1H).

LCMS(ESI): [M]$^+$ m/z: calcd 274.2; found 275.2; Rt 1.121 min.

Step 2: Synthesis of 5-methyl-3,4,5,6-tetrahydro-2,3'-bipyridine

A solution of tert-butyl 3-methyl-6-(3-pyridyl)-3,4-dihydro-2H-pyridine-1-carboxylate (10 g, 36.45 mmol) in TFA (60 g, 526.21 mmol, 40.54 mL) was stirred at 25° C. for 2 hr. The solvent was removed, the residue was cooled, taken up with 100 ml 10-% NaOH solution and extracted with DCM (3*100 ml). The organic layer was washed with brine (100 ml), dried over $Na_2SO_4$ and evaporated in vacuum to give 3-(3-methyl-2,3,4,5-tetrahydropyridin-6-yl)pyridine (6.2 g, 35.58 mmol, 97.62% yield).

$^1$H NMR (400 MHz, $CDCl_3$) δ (ppm) 0.98 (d, 3H), 1.36 (m, 1H), 1.70 (m, 1H), 1.91 (m, 1H), 2.57 (m, 1H), 2.77 (m, 1H), 3.22 (m, 1H), 4.00 (m, 1H), 7.26 (t, 1H), 8.07 (d, 1H), 8.57 (d, 1H), 8.93 (s, 1H).

LCMS(ESI): [M]$^+$ m/z: calcd 174.2; found 175.2; Rt=0.388 min.

Step 3: Synthesis of rac-3-((2R,5S)-5-methylpiperidin-2-yl)pyridine

Sodium borohydride (1.35 g, 35.58 mmol, 1.26 mL) was added portion wise to a stirred solution of 3-(3-methyl-2,3,4,5-tetrahydropyridin-6-yl)pyridine (6.2 g, 35.58 mmol) in MeOH (70 mL) at 0° C. The resulting mixture was stirred for 2 hr, and then evaporated in vacuum. The residue was diluted with water (80 ml) and extracted with dichloromethane (2*80 ml). The combined organic extracts were dried over sodium sulphate and evaporated in vacuum to obtain 3-[(2R,5S)-5-methyl-2-piperidyl]pyridine (6.2 g, 35.18 mmol, 98.86% yield).

$^1$H NMR (500 MHz, $CDCl_3$) δ (ppm) 0.90 (d, 3H), 1.12 (m, 1H), 1.51 (m, 1H), 1.65 (m, 1H), 1.86 (m, 3H), 2.41 (m, 1H), 3.14 (m, 1H), 3.58 (m, 1H), 7.26 (t, 1H), 7.69 (d, 1H), 8.47 (d, 1H), 8.57 (s, 1H).

LCMS(ESI): [M]$^+$ m/z: calcd 176.2; found 177.2; Rt=0.331 min.

Step 4: Synthesis of rac-(2R,5S)-tert-butyl 5-methyl-2-(pyridin-3-yl)piperidine-1-carboxylate To a solution of 3-[(2R,5S)-5-methyl-2-piperidyl]pyridine (6.20 g, 35.18 mmol) in DCM (70 mL), di-tert-butyl dicarbonate (7.68 g, 35.18 mmol, 8.07 mL) was added. The resulting mixture was stirred at 25° C. for 12 hr, the solvent was removed and crude product (12 g) was purified by gradient chromatography (Hexane-EtOAc) to obtain tert-butyl (2R,5S)-5-methyl-2-(3-pyridyl)piperidine-1-carboxylate (6 g, 21.71 mmol, 61.72% yield). Also was obtained second fraction (2 g) with impurities of cis-isomer. For the next step was used only pure fraction.

$^1$H NMR (400 MHz, CDCl$_3$) δ (ppm) 1.07 (d, 3H), 1.37 (m, 1H), 1.46 (s, 9H), 1.68 (m, 1H), 1.72 (m, 1H), 2.04 (m, 1H), 2.18 (m, 1H), 3.02 (m, 1H), 3.75 (m, 1H), 5.36 (m, 1H), 7.26 (m, 1H), 7.57 (d, 1H), 8.49 (d, 1H), 8.54 (s, 1H).

Step 5: Synthesis of rac-tert-butyl (2R,5S)-5-methyl-2-(3-piperidyl)piperidine-1-carboxylate To a solution of tert-butyl (2R,5S)-5-methyl-2-(3-pyridyl)piperidine-1-carboxylate (6 g, 21.71 mmol) in MeOH (100 mL), palladium, 10% on carbon, Type 487, dry (0.8 g, 7.52 mmol) was added. The resulting mixture was stirred in autoclave under hydrogen atmosphere (100 atm) at 45° C. for 96 hr. The progress of reaction was monitored by NMR. When full conversion was obtained, catalyst was filtered, solvent was removed in vacuum. The residue was dissolved in DCM (50 ml), dried over Na$_2$SO$_4$ and solvent was removed to afford tert-butyl (2R,5S)-5-methyl-2-(3-piperidyl)piperidine-1-carboxylate (5.7 g, 20.18 mmol, 92.97% yield). The structure of the product was proved by 2D-NMR as trans-.

$^1$H NMR (400 MHz, DMSO-d$_6$) δ (ppm) 0.86 (d, 3H), 0.94 (m, 1H), 1.18 (m, 1H), 1.34 (s, 9H), 1.49 (m, 1H), 1.58 (m, 2H), 1.77 (m, 2H), 1.91 (m, 1H), 2.19 (m, 1H), 2.41 (m, 1H), 2.90 (m, 3H), 3.59 (m, 5H).

LCMS(ESI): [M]$^+$ m/z: calcd 282.2; found 283.2; Rt=0.932 min.

Step 6: Synthesis of rac-tert-butyl (2R,5S)-5-methyl-2-[1-(methylcarbamoyl)-3-piperidyl]piperidine-1-carboxylate To a solution of tert-butyl (2R,5S)-5-methyl-2-(3-piperidyl)piperidine-1-carboxylate (0.85 g, 3.01 mmol) and TEA (456.83 mg, 4.51 mmol, 629.24 μL) in DCM (50 mL), N-methylcarbamoyl chloride (337.73 mg, 3.61 mmol) was added portion wise at 0° C. The resulting mixture was stirred for 3 hr, washed with brine (3*40 ml), dried over Na$_2$SO$_4$ and the solvent was removed in vacuum to obtain tert-butyl (2R,5S)-5-methyl-2-[1-(methylcarbamoyl)-3-piperidyl]piperidine-1-carboxylate (0.9 g, 2.65 mmol, 88.09% yield).

$^1$H NMR (400 MHz, CDCl$_3$) δ (ppm) 0.95 (d, 3H), 1.09 (m, 3H), 1.25 (m, 1H), 1.41 (s, 9H), 1.66 (m, 4H), 1.78 (m, 1H), 2.47 (m, 1H), 2.66 (m, 1H), 2.75 (s, 3H), 2.84 (m, 1H), 3.12 (m, 1H), 3.57 (m, 1H), 3.71 (m, 1H), 3.86 (m, 1H), 3.99 (m, 1H), 4.45 (m, 1H).

LCMS(ESI): [M]$^+$ m/z: calcd 339.2; found 340.2; Rt=1.213 min.

Step 7: Synthesis of rac-N-methyl-3-[(2R,5S)-5-methyl-2-piperidyl]piperidine-1-carboxamide A solution of tert-butyl (2R,5S)-5-methyl-2-[1-(methylcarbamoyl)-3-piperidyl]piperidine-1-carboxylate (0.95 g, 2.80 mmol) and hydrogen chloride solution 40 M in dioxane (5 g, 137.13 mmol, 6.25 mL) in DCM (20 mL) was stirred at 25° C. for 12 hr. The solvent was removed in vacuum to obtain N-methyl-3-[(2R,5S)-5-methyl-2-piperidyl]piperidine-1-carboxamide (0.75 g, crude, HCl). This product was used for the next step without further purification.

$^1$H NMR (500 MHz, DMSO-d$_6$) δ (ppm) 0.85 (d, 3H), 1.09 (m, 1H), 1.18 (m, 2H), 1.28 (m, 2H), 1.42 (m, 1H), 1.61 (m, 2H), 1.81 (m, 3H), 2.49 (s, 3H), 2.78 (m, 2H), 3.11 (m, 2H), 3.82 (m, 1H), 4.11 (m, 1H), 6.33 (m, 1H), 8.97 (m, 1H).

Step 8: Synthesis of rac-tert-butyl (2R,5S)-2-(1-acetyl-3-piperidyl)-5-methyl-piperidine-1-carboxylate To a solution of tert-butyl (2R,5S)-5-methyl-2-(3-piperidyl)piperidine-1-carboxylate (0.8 g, 2.83 mmol) and TEA (429.95 mg, 4.25 mmol, 592.22 μL) in DCM (30 mL), acetyl chloride (266.83 mg, 3.40 mmol, 206.84 μL) was added at 0° C. The resulting mixture was stirred for 2 hr, washed with water (3*20 ml), dried over Na$_2$SO$_4$ and the solvent was removed to obtain tert-butyl (2R,5S)-2-(1-acetyl-3-piperidyl)-5-methyl-piperidine-1-carboxylate (0.9 g, 2.77 mmol, 97.92% yield).

$^1$H NMR (400 MHz, DMSO-d$_6$) δ (ppm) 0.87 (d, 3H), 1.18 (m, 2H), 1.34 (s, 9H), 1.58 (m, 4H), 1.75 (m, 2H), 1.94 (s, 3H), 2.22 (m, 1H), 2.82 (m, 2H), 3.32 (m, 2H), 3.58 (m, 3H), 4.01 (m, 1H).

LCMS(ESI): [M]$^+$ m/z: calcd 324.2; found 325.2; Rt=1.263 min.

Step 9: Synthesis of rac-1-[3-[(2R,5S)-5-methyl-2-piperidyl]-1-piperidyl]ethanone A solution of tert-butyl (2R,5S)-2-(1-acetyl-3-piperidyl)-5-methyl-piperidine-1-carboxylate (0.9 g, 2.77 mmol) and hydrogen chloride solution 40 M in dioxane (4.00 g, 109.71 mmol, 5 mL) in DCM (10 mL). The resulting mixture was stirred at 25° C. for 4 hr. The solvent was evaporated in vacuum to afford 1-[3-[(2R,5S)-5-methyl-2-piperidyl]-1-piperidyl]ethanone (0.7 g, 2.68 mmol, 96.76% yield, HCl) as light-yellow solid.

$^1$H NMR (500 MHz, DMSO-d$_6$) δ (ppm) 0.86 (d, 3H), 1.08 (m, 2H), 1.36 (m, 2H), 1.76 (m, 6H), 1.99 (s, 3H), 2.82 (m, 2H), 2.98 (m, 1H), 3.11 (m, 1H), 3.66 (m, 1H), 4.28 (m, 1H), 4.75 (m, 2H).

LCMS(ESI): [M]$^+$ m/z: calcd 224.2; found 225.2; Rt=0.547 min.

LCMS(ESI): [M]$^-$ m/z: calcd 239.2; found 240.2; Rt=0.634 min.

Step 10: Synthesis of rac-tert-butyl (2R,5S)-5-methyl-2-(1-methyl-3-piperidyl)piperidine-1-carboxylate To a mixture of tert-butyl (2R,5S)-5-methyl-2-(3-piperidyl)piperidine-1-carboxylate (0.8 g, 2.83 mmol) and potassium carbonate (1.17 g, 8.50 mmol, 512.87 μL) in ACN (30 mL), methyl iodide (442.27 mg, 3.12 mmol, 193.98 μL) was added. The resulting mixture was stirred at 25° C. for 8 hr, the precipitate was filtered off and solvent was removed. The residue was taken up with DCM (30 ml), the precipitate was filtered and solvent was evaporated in vacuum to give tert-butyl (2R,5S)-5-methyl-2-(1-methyl-3-piperidyl)piperidine-1-carboxylate (0.8 g, 2.70 mmol, 95.27% yield).

$^1$H NMR (400 MHz, CDCl$_3$) δ (ppm) 0.96 (d, 3H), 1.26 (m, 2H), 1.42 (s, 9H), 1.81 (m, 9H), 2.26 (s, 3H), 2.86 (m, 2H), 3.50 (m, 3H), 3.56 (m, 1H).

LCMS(ESI): [M]$^+$ m/z: calcd 296.2; found 297.2; Rt=1.008 min.

Step 11: Synthesis of rac-1-methyl-3-[(2R,5S)-5-methyl-2-piperidyl]piperidine A solution of tert-butyl (2R,5S)-5-methyl-2-(1-methyl-3-piperidyl)piperidine-1-carboxylate (0.8 g, 2.70 mmol) and hydrogen chloride solution 40 M in dioxane (5 g, 137.13 mmol, 6.25 mL) in DCM (15 mL) was stirred at 25° C. for 5 hr. The solvent was removed in vacuum to obtain 1-methyl-3-[(2R,5S)-5-methyl-2-piperidyl]piperidine (0.7 g, crude, 2HCl). This product was used for the next step without further purification.

$^1$H NMR (400 MHz, DMSO-d$_6$) δ (ppm) 0.84 (d, 3H), 1.09 (m, 3H), 1.85 (m, 6H), 2.65 (s, 3H), 2.86 (m, 2H), 3.11 (m, 3H), 3.36 (m, 2H), 4.28 (m, 2H).

LCMS(ESI): [M]$^+$ m/z: calcd 196.2; found 197.2; Rt=0.159 min.

3LL. Synthesis of rac-5-[(2R,5R)-4,4-difluoro-5-methyl-2-piperidyl]-1,3-benzothiazole

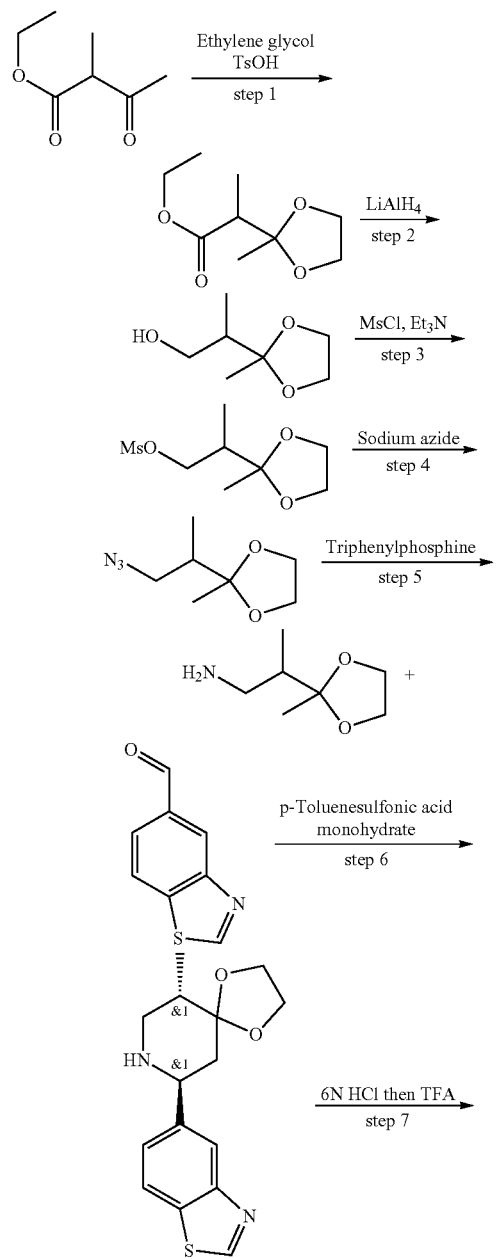

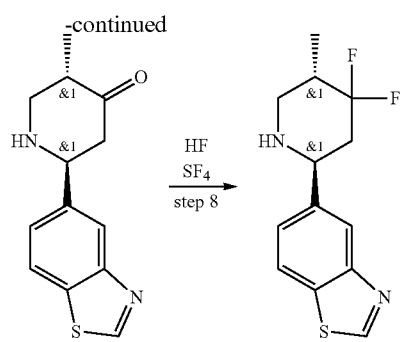

Step 1. Synthesis of ethyl 2-(2-methyl-1,3-dioxolan-2-yl)propanoate ethyl 2-methyl-3-oxo-butanoate (24.72 g, 171.47 mmol, 24.24 mL) was dissolved in Toluene (250 mL) and Ethylene glycol (11.71 g, 188.61 mmol, 10.55 mL) was added thereto followed by addition of p-Toluenesulfonic acid monohydrate (3.26 g, 17.15 mmol, 2.63 mL). The resulting mixture was refluxed for 3 hr. The reaction mixture was washed with aq·NaHCO$_3$ solution (2*100 ml) and an organic layer was separated, dried over Na$_2$SO$_4$, filtered and evaporated. The residue was purified by fractional distillation (bp=60° C., 1 mm Hg) to obtain ethyl 2-(2-methyl-1,3-dioxolan-2-yl)propanoate (13.45 g, 71.44 mmol, 41.67% yield)

$^1$H NMR (CDCl$_3$, 400 MHz): δ (ppm) 1.20 (d, 3H), 1.25 (t, 3H), 1.38 (s, 3H), 2.72 (m, 1H), 3.90-3.97 (m, 4H), 4.14 (q, 2H).

Step 2. Synthesis of 2-(2-methyl-4,3-dioxolan-2-yl)propan-1-ol lithium aluminium hydride (5.42 g, 142.89 mmol) was suspended in THF (150 mL) and a solution of ethyl 2-(2-methyl-1,3-dioxolan-2-yl)propanoate (13.45 g, 71.44 mmol) in THF (20 mL) was added dropwise. The reaction mixture was stirred for 1 hr. Water (5.4 ml) was carefully added to the reaction mixture followed by addition of 20% aq·KOH solution (5.4 ml) and water (10.8 ml). The resulting suspension was filtered and the filtrate was evaporated in vacuo. The residue was purified by flash chromatography (Hexane-EtOAc 2:1) to obtain 2-(2-methyl-1,3-dioxolan-2-yl)propan-1-ol (6.79 g, 46.43 mmol, 65.00% yield)

$^1$H NMR (CDCl$_3$, 400 MHz): δ (ppm) 0.95 (d, 3H), 1.27 (s, 3H), 2.00 (m, 1H), 2.90 (s, 1H), 3.45 (dd, 1H), 3.70 (dd, 1H), 3.90-3.97 (m, 4H),

Step 3. Synthesis of 2-(2-methyl-1,3-dioxolan-2-yl)propyl methanesulfonate 2-(2-methyl-1,3-dioxolan-2-yl)propan-1-ol (6.79 g, 46.45 mmol) was dissolved in DCM (60 mL) and Triethylamine (5.17 g, 51.09 mmol, 7.12 mL) was added thereto. The resulting solution was cooled to −5° C. in an ice bath and a solution of Methanesulfonyl chloride (5.59 g, 48.77 mmol, 3.77 mL) in DCM (10 mL) was added dropwise. The resulting mixture was allowed to warm to room temperature and stirred overnight. Water (25 ml) was added to the reaction mixture and the resulting mixture was transferred to a separation funnel and an organic layer was separated. The organic layer was washed with aq·NaHSO$_4$ solution (25 ml), water (25 ml), dried over Na$_2$SO$_4$, filtered and evaporated to obtain 2-(2-methyl-1,3-dioxolan-2-yl)propyl methanesulfonate (10.36 g, 46.18 mmol, 99.41% yield)

$^1$H NMR (CDCl$_3$, 500 MHz): δ (ppm) 1.10 (d, 3H), 1.27 (s, 3H), 2.17 (m, 1H), 3.00 (s, 3H), 3.90-3.97 (m, 4H), 4.04 (dd, 1H), 4.41 (dd, 1H), Step 4. Synthesis of 2-(2-azido-1-methyl-ethyl)-2-methyl-1,3-dioxolane 2-(2-methyl-1,3-dioxolan-2-yl)propyl methanesulfonate (10.36 g, 46.18 mmol) was dissolved in DMF (100 mL) and Sodium azide (9.01 g, 138.53 mmol, 4.87 mL) was added thereto. The resulting mixture was heated at 75° C. for 24 hr. The reaction mixture was poured into water (150 ml) and the resulting mixture was extracted with MTBE (2*100 ml). Combined organic layers were washed with water (3*75 ml), brine (75 ml), dried over Na$_2$SO$_4$, filtered and evaporated to obtain 2-(2-azido-1-methyl-ethyl)-2-methyl-1,3-dioxolane (6.59 g, 38.51 mmol, 83.40% yield)

$^1$H NMR (CDCl$_3$, 500 MHz): δ (ppm) 1.07 (d, 3H), 1.26 (s, 3H), 1.97 (m, 1H), 3.07 (dd, 1H), 3.58 (dd, 1H), 3.90-3.97 (m, 4H).

Step 5. Synthesis of 2-(2-methyl-1,3-dioxolan-2-yl)propan-1-amine 2-(2-azido-1-methyl-ethyl)-2-methyl-1,3-dioxolane (6.59 g, 38.51 mmol) was dissolved in THF (100 mL) and Triphenylphosphine (10.61 g, 40.44 mmol) was added portionwise. The resulting mixture was stirred for 1 hour and Water (10.6 mL) was added to the previous mixture. The resulting mixture was stirred overnight. The reaction mixture was concentrated in vacuo and the residue was dissolved in DCM (100 ml). The resulting solution was extracted with aq·NaHSO$_4$ solution (2*75 ml) and combined aqueous layers were washed with DCM (2*75 ml). The aqueous layer was basified with NaOH and the resulting mixture was extracted with MTBE (2*75 ml). Combined organic layers were washed with brine, dried over Na$_2$SO$_4$, filtered and evaporated to obtain 2-(2-methyl-1,3-dioxolan-2-yl)propan-1-amine (4.89 g, 33.65 mmol, 87.38% yield)

$^1$H NMR (CDCl$_3$, 600 MHz): δ (ppm) 0.97 (d, 3H), 1.22 (s, 3H), 1.42 (brs, 2H), 1.72 (m, 1H), 2.49 (dd, 1H), 2.87 (dd, 1H), 3.89-3.91 (m, 4H).

Step 6. Synthesis of 9-(1,3-benzothiazol-5-yl)-6-methyl-1,4-dioxa-8-azaspiro[4.5]decane 2-(2-methyl-1,3-dioxolan-2-yl)propan-1-amine (2.14 g, 14.71 mmol) was dissolved in Benzene (30 mL) and 1,3-benzothiazole-5-carbaldehyde (2.4 g, 14.71 mmol) was added thereto followed by addition of p-Toluenesulfonic acid monohydrate (8.39 g, 44.12 mmol, 6.77 mL). The resulting mixture was heated to reflux and refluxed under Dean-Stark trap overnight. The reaction mixture was cooled and aq·K$_2$CO$_3$ solution (15 ml) was added. The resulting mixture was transferred to a separation funnel and an organic layer was separated. The aqueous layer was extracted with EtOAc (35 ml) and combined organic layers were dried over Na$_2$SO$_4$, filtered and evaporated. The residue was dissolved in CHCl$_3$ (25 ml) and the resulting mixture was extracted with aq·NaHSO$_4$ (1 g in 10 ml of water, 2*10 ml). Combined aqueous layers were washed with CHCl$_3$ (2*30 ml) and then basified with K$_2$CO$_3$ (6 g). The resulting mixture was extracted with CHCl$_3$ (2*40 ml) and combined organic layers were dried over Na$_2$SO$_4$, filtered and evaporated to obtain 9-(1,3-benzothiazol-5-yl)-6-methyl-1,4-dioxa-8-azaspiro[4.5]decane (1.7 g, crude)

$^1$H NMR (CDCl$_3$, 400 MHz): δ (ppm) 0.89 (d, 3H), 1.73 (dd, 1H), 1.99 (m, 2H), 2.80 (t, 1H), 3.07 (dd, 1H), 3.75 (m, 1H), 3.96 (m, 5H), 7.48 (d, 1H), 7.88 (d, 1H), 8.09 (s, 1H), 8.97 (s, 1H).

LCMS(ESI): [M+1]$^+$ m/z: calcd 290.1; found 291.0; Rt=0.783 min.

Step 7. Synthesis of rac-(2R,5R)-2-(benzo[d]thiazol-5-yl)-5-methylpiperidin-4-one 9-(1,3-benzothiazol-5-yl)-6-methyl-1,4-dioxa-8-azaspiro[4.5]decane (1.65 g, 5.68 mmol) was dissolved in 6N HCl (30 mL) and the resulting mixture was heated at 80° C. (in an oil bath) overnight. The reaction mixture was cooled and basified with K$_2$CO$_3$. The resulting mixture was extracted with CHCl$_3$ (2*50 ml) and combined organic layers were dried over Na$_2$SO$_4$, filtered and evaporated. The residue was dissolved in MTBE and TFA (0.1 ml) was added thereto. The resulting suspension was filtered, a filter cake was rinsed with MTBE and dried in vacuo to obtain rac-(2R,5R)-2-(benzo[d]thiazol-5-yl)-5-methylpiperidin-4-one as TFA salt (1.1 g, 3.05 mmol, 53.72% yield, CF$_3$COOH)

$^1$H NMR (DMSO-d$_6$, 500 MHz): δ (ppm) 1.04 (d, 3H), 2.68 (d, 1H), 2.98 (m, 1H), 3.23 (m, 4H), 3.75 (m, 1H), 4.98 (m, 1H), 7.61 (m, 1H), 9.63 (brs, 2H).

LCMS(ESI): [M+1]$^+$ m/z: calcd 246.1; found 247.0; Rt=0.717 min.

Step 8. Synthesis of rac-5-[(2R,5R)-4,4-difluoro-5-methyl-2-piperidyl]-1,3-benzothiazole 2-(1,3-benzothiazol-5-yl)-5-methyl-piperidin-4-one (1.1 g, 4.47 mmol) was dissolved in HF (anhydrous) (3.3 mL) and the resulting mixture was sealed in a stainless steel vessel, cooled in a liquid N$_2$ and SF$_4$ (3.3 mL) was added thereto. The resulting mixture was allowed to warm to room temperature and stirred at room temperature overnight. After reaction completed, the reaction mixture was poured onto ice and neutralized with NaHCO$_3$. The resulting mixture was extracted with EtOAc (2*75 ml) and combined organic layers were washed with brine, dried over Na$_2$SO$_4$, filtered and evaporated to obtain 5-[(2R,5R)-4,4-difluoro-5-methyl-2-piperidyl]-1,3-benzothiazole (480 mg, crude)

$^1$H NMR (CDCl$_3$, 400 MHz): δ (ppm) 1.06 (d, 3H), 2.03-2.20 (m, 3H), 2.30 (m, 1H), 2.72 (t, 1H), 3.12 (m, 1H), 4.04 (d, 1H), 7.46 (d, 1H), 7.89 (d, 1H), 8.12 (s, 1H), 8.97 (s, 1H).

LCMS(ESI): [M+1]$^+$ m/z: calcd 268.1; found 269.0; Rt=0.837 min.

3MM. Synthesis of rac-(2R,5R)-2-(3-chlorophenyl)-4,4-difluoro-5-methylpiperidine

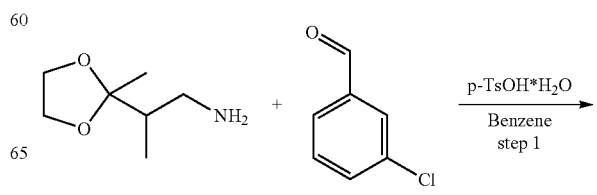

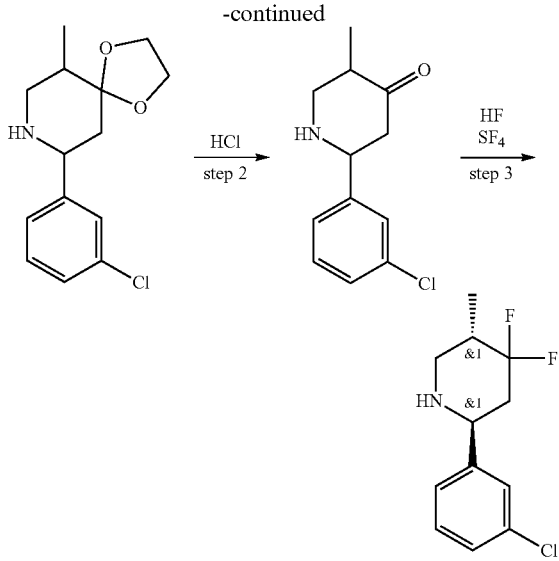

Step 1: Synthesis of 9-(3-chlorophenyl)-6-methyl-1,4-dioxa-8-azaspiro[4.5]decane 2-(2-methyl-1,3-dioxolan-2-yl)propan-1-amine (2.76 g, 18.99 mmol) (prepared as above) was dissolved in benzene (60 mL) and 3-chlorobenzaldehyde (2.67 g, 18.99 mmol, 2.15 mL) was added thereto followed by addition of p-toluenesulfonic acid monohydrate (10.84 g, 56.98 mmol, 8.74 mL). The resulting mixture was heated to reflux and refluxed under Dean-Stark trap overnight. The reaction mixture was cooled and aq·K$_2$CO$_3$ solution (15 ml) was added. The resulting mixture was transferred to a separation funnel and an organic layer was separated. The aqueous layer was extracted with EtOAc (35 ml) and combined organic layers were dried over Na$_2$SO$_4$, filtered and evaporated. The residue was dissolved in CHCl$_3$ (25 ml) and the resulting mixture was extracted with aq·NaHSO$_4$ (1 g in 10 ml of water, 2*10 ml). Combined aqueous layers were washed with CHCl$_3$ (2*30 ml) and then basified with K$_2$CO$_3$ (6 g). The resulting mixture was extracted with CHCl$_3$ (2*40 ml) and combined organic layers were dried over Na$_2$SO$_4$, filtered and evaporated to obtain 9-(3-chlorophenyl)-6-methyl-1,4-dioxa-8-azaspiro[4.5]decane (1.51 g, crude).

$^1$H NMR (500 MHz, CDCl$_3$) δ (ppm) 1.08 (d, 3H), 1.26 (m, 2H), 1.64 (m, 1H), 2.54 (m, 2H), 2.67 (m, 2H), 3.07 (m, 1H), 3.48 (m, 1H), 3.92 (m, 2H), 7.26 (m, 4H).

LCMS(ESI): [M]$^+$ m/z: calcd 267.2; found 268.2; Rt=0.915 min.

Step 2: Synthesis of 2-(3-chlorophenyl)-5-methylpiperidin-4-one 9-(3-chlorophenyl)-6-methyl-1,4-dioxa-8-azaspiro[4.5]decane (1.51 g, 5.64 mmol) was dissolved in 6N HCl (30 mL) and the resulting mixture was heated at 80° C. (in an oil bath) overnight. The reaction mixture was cooled and basified with K$_2$CO$_3$. The resulting mixture was extracted with CHCl$_3$ (2*50 ml) and combined organic layers were dried over Na$_2$SO$_4$, filtered and evaporated. The residue was dissolved in MTBE and TFA (0.1 ml) was added thereto. The resulting suspension was filtered, a filter cake was rinsed with MTBE and dried in vacuum to obtain 2-(3-chlorophenyl)-5-methyl-piperidin-4-one (1.3 g, 3.85 mmol, 68.26% yield, CF$_3$COOH).

$^1$H NMR (500 MHz, DMSO-d$_6$) δ (ppm) 1.01 (d, 3H), 2.62 (m, 2H), 2.89 (m, 1H), 3.02 (m, 1H), 3.67 (m, 1H), 4.78 (m, 1H), 7.52 (m, 3H), 7.63 (m, 1H), 9.56 (m, 1H).

LCMS(ESI): [M]$^+$ m/z: calcd 223.2; found 224.2; Rt=0.729 min.

Step 3: Synthesis of rac-(2R,5R)-2-(3-chlorophenyl)-4,4-difluoro-5-methylpiperidine 2-(3-chlorophenyl)-5-methyl-piperidin-4-one (1.3 g, 3.85 mmol, CF$_3$COOH), was dissolved in HF (anhydrous) (3.9 mL) and the resulting mixture was sealed in a stainless steel vessel, cooled in a liquid N$_2$ and SF$_4$ (3.9 mL) was added thereto. The resulting mixture was allowed to warm to rt and stirred overnight. After reaction completed, the reaction mixture was poured onto ice and neutralized with NaHCO$_3$. The resulting mixture was extracted with EtOAc (2*75 ml) and combined organic layers were washed with brine, dried over Na$_2$SO$_4$, filtered and evaporated to obtain (2R,5R)-2-(3-chlorophenyl)-4,4-difluoro-5-methyl-piperidine (0.79 g, 3.22 mmol, 83.53% yield).

$^1$H NMR (400 MHz, CDCl$_3$) δ (ppm) 1.05 (d, 3H), 2.03 (m, 3H), 2.69 (m, 1H), 3.05 (m, 1H), 3.84 (m, 1H), 7.28 (m, 5H).

LCMS(ESI): [M]$^+$ m/z: calcd 245.2; found 246.2; Rt=0.933 min.

3NN. Synthesis of (2R,5S)-5-ethyl-2-(1H-pyrazol-4-yl)piperidine

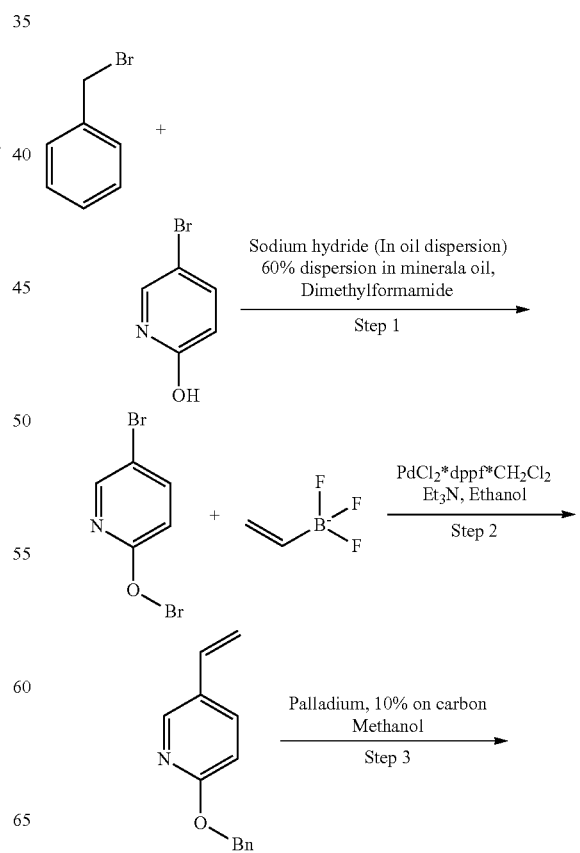

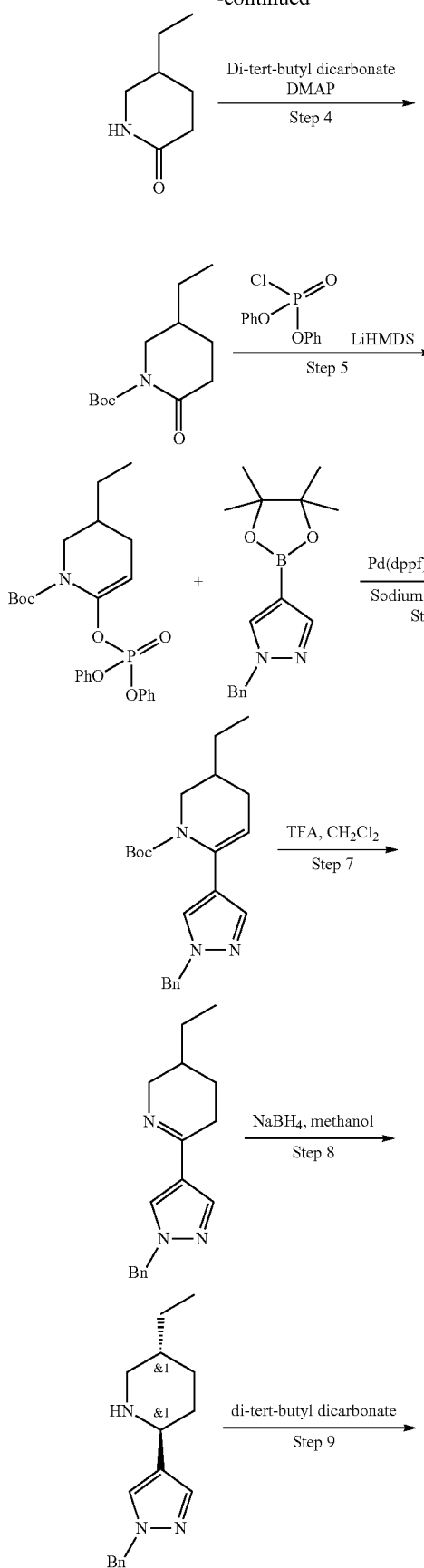

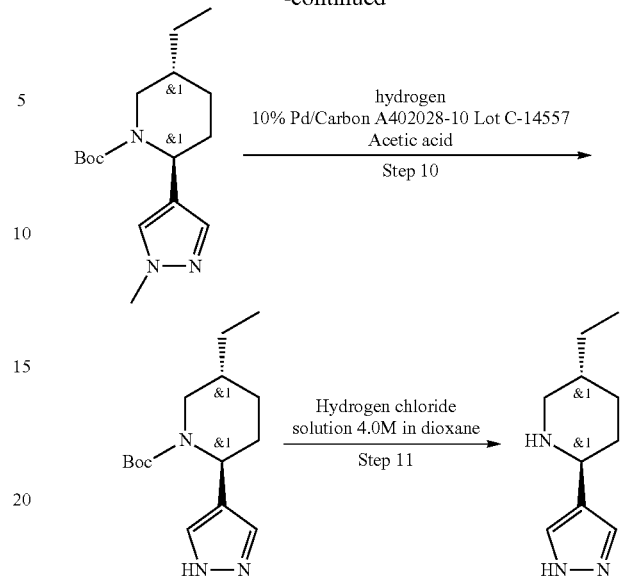

Step 1. Synthesis of 2-benzyloxy-5-bromo-pyridine

Sodium hydride (in oil dispersion) 60% dispersion in mineral oil (11.48 g, 286.95 mmol, 6000 purity) was added in small portions to a solution of 5-bromo-2-chloro-pyridine (50.2 g, 260.86 mmol) and phenylmethanol (31.03 g, 286.95 mmol, 29.55 mL) in Dimethylformamide (500 mL). After $H_2$ evolution ceased, resulting mixture was stirred at 20° C. for 18 hr. Then, it was poured into ice-cooled water (2000 ml) and extracted with MTBE (2×800 ml). Combined organic layers were washed successively with water (2×300 ml), brine (300 ml), dried over $Na_2SO_4$ and concentrated under reduced pressure, affording 2-benzyloxy-5-bromo-pyridine (72.1 g, crude).

$^1$H NMR (400 MHz, $CDCl_3$) δ (ppm) 5.33 (s, 2H), 6.71 (d, 1H), 7.36-7.42 (m, 5H), 7.65 (d, 1H), 8.19 (s, 1H).

LCMS(ESI): [M-Boc]$^+$ m/z: calcd 263.0; found 264.2; Rt=1.498 min.

Step 2. Synthesis of 2-benzyloxy-5-vinyl-pyridine

Triethylamine (49.72 g, 491.37 mmol, 68.49 mL) was added to a solution of 2-benzyloxy-5-bromo-pyridine (72.1 g, 245.69 mmol) and trifluoro(vinyl)boranuide (30.29 g, 319.39 mmol) in ethanol (700 mL). Reaction flask was evacuated and refilled with argon 3 times. Then, $PdCl_2$*dppf*dcm (2.01 g, 2.46 mmol) was added under stream of argon. Resulting mixture was stirred at 78° C. for 20 hr under inert atmosphere. Then, it was concentrated under reduced pressure and residue was extracted with Hexane/MTBE 1:1 mixture (700 ml). Obtained solution was filtered through a short pad of silicagel and evaporated under reduced pressure. Crude product was crystallized from Hexanes (350 ml) at −30° C. and filtered (product is liquid at r.t.), affording 2-benzyloxy-5-vinyl-pyridine (27.8 g, 131.59 mmol, 53.56% yield).

$^1$H NMR (400 MHz, $CDCl_3$) δ (ppm) 5.19 (d, 1H), 5.37 (s, 2H), 5.65 (d, 1H), 6.63 (m, 1H), 6.78 (d, 1H), 7.24-7.63 (m, 5), 7.71 (d, 1H), 8.19 (s, 1H).

Step 3. Synthesis of 5-ethylpiperidin-2-one

Palladium, 10% on carbon (2 g, 1.88 mmol, 10% purity) was added to a solution of 2-benzyloxy-5-vinyl-pyridine (27.8 g, 131.59 mmol) in Methanol (350 mL). Resulting mixture was stirred under hydrogen atmosphere at 20° C. and balloon pressure for 18 hours, and then at 70° C. and 40 bar for another 18 hours. After that, catalyst was filtered off and filtrate was concentrated under reduced pressure. Residue was redissolved in ethyl acetate (300 ml) and washed with 20% aq. $K_2CO_3$ soln. (50 ml), dried over $Na_2SO_4$ and evaporated in vacuo, affording 5-ethylpiperidin-2-one (15.3 g, 120.30 mmol, 91.42% yield).

$^1$H NMR (400 MHz, DMSO-d$_6$) δ (ppm) 0.87 (m, 3H), 1.27 (m, 3H), 1.53 (m, 1H), 1.76 (m, 1H), 2.12 (m, 2H), 2.74 (m, 1H), 3.13 (m, 1H), 7.37 (s, 1H).

GCMS(EI): [M-Boc]$^+$ m/z: calcd 127.2; found 127; Rt=7.4 min.

Step 4. Synthesis of tert-butyl 5-ethyl-2-oxo-piperidine-1-carboxylate

Di-tert-butyl dicarbonate (36.76 g, 168.42 mmol, 38.65 mL) was added dropwise to a solution of 5-ethylpiperidin-2-one (15.3 g, 120.30 mmol) and 4-dimethylaminopyridine (1.47 g, 12.03 mmol) in Tetrahydrofuran (200 mL). The resulting solution was stirred at 40° C. for 15 hr. Then, water (30 ml) was added and mixture was stirred for 20 minutes. When $CO_2$ evolution ceased, it was partitioned between 5% aq·NaHSO$_4$ solution (150 ml) and MTBE (250 ml). Organic layer was separated, dried over $Na_2SO_4$ and concentrated under reduced pressure. Residue was dried for 1 hour at 1 mbar and 90° C., affording tert-butyl 5-ethyl-2-oxo-piperidine-1-carboxylate (18.2 g, 80.07 mmol, 66.56% yield).

$^1$H NMR (500 MHz, CDCl$_3$) δ (ppm) 0.97 (m, 3H), 1.35-1.45 (m, 3H), 1.53 (s, 9H), 1.73 (m, 1H), 1.93 (m, 1H), 2.47-2.55 (m, 2H), 3.18 (m, 1H), 3.85 (m, 1H).

LCMS(ESI): [M-Boc]$^+$ m/z: calcd 227.3; found 228.2; Rt=1.299 min.

Step 5. Synthesis of tert-butyl 6-diphenoxyphosphoryloxy-3-ethyl-3,4-dihydro-2H-pyridine-1-carboxylate Lithium bis(trimethylsilyl)amide (20% in THF/ethylbenzene)) (80.39 g, 96.08 mmol, 89.32 mL, 20% purity) was added dropwise under argon to a cooled to −78° C. solution of tert-butyl 5-ethyl-2-oxo-piperidine-1-carboxylate (18.2 g, 80.07 mmol) in Tetrahydrofuran (150 mL). The resulting solution was stirred at −70° C. for 1 hr, then [chloro(phenoxy)phosphoryl]oxybenzene (22.59 g, 84.07 mmol, 17.37 mL) was added dropwise maintaining temperature below −70° C. The reaction mixture was allowed to warm (cooling bath was removed) to 0° C. and then diluted with water (100 ml) and MTBE (200 ml). The organic layer was separated, the aqueous layer was additionally extracted with MTBE (100 ml). The combined organic extracts were washed with 10% aqueous $K_2CO_3$ solution (2*100 ml), dried over potassium carbonate and concentrated in vacuo. The residue was dissolved in hexane and the resulting cloudy solution was filtered through a short pad of silica gel. Filtrate was evaporated in vacuo to afford crude tert-butyl 6-diphenoxyphosphoryloxy-3-ethyl-3,4-dihydro-2H-pyridine-1-carboxylate (33.4 g, 72.69 mmol, 90.79% yield) as light-yellow oil, which was used directly in the next step.

$^1$H NMR (500 MHz, CDCl$_3$) δ (ppm) 0.94 (s, 3H), 1.24 (m, 1H), 1.25 (m, 1H), 1.43 (s, 9H), 1.73 (m, 1H), 1.76 (m, 1H), 2.31 (m, 1H), 2.94 (dd, 1H), 3.95 (dd, 1H), 5.07 (s, 1H), 7.18-7.33 (m, 10H).

LCMS(ESI): [M+1]$^+$ m/z: calcd 459.2; found 460.2; Rt=1.723 min.

Step 6. Synthesis of tert-butyl 6-(1-benzylpyrazol-4-yl)-3-ethyl-3,4-dihydro-2H-pyridine-1-carboxylate Potassium carbonate (2.92 g, 21.11 mmol, 1.27 mL) was added to a solution of tert-butyl 6-diphenoxyphosphoryloxy-3-ethyl-3,4-dihydro-2H-pyridine-1-carboxylate (5.09 g, 11.09 mmol) and 1-benzyl-4-(4,4,5,5-tetramethyl-1,3,2-dioxaborolan-2-yl)pyrazole (3 g, 10.56 mmol) in Dioxane (40 mL) and Water (15 mL). Reaction flask was evacuated and refilled with argon 3 times. Then, PdCl$_2$*dppf*dcm (344.86 mg, 422.30 μmol) was added under stream of argon. Resulting mixture was stirred at 90° C. for 18 hr under inert atmosphere. Then, it was concentrated under reduced pressure and residue was extracted with MTBE (60 ml). Obtained solution was filtered through a short pad of silicagel and evaporated under reduced pressure, affording tert-butyl 6-(1-benzylpyrazol-4-yl)-3-ethyl-3,4-dihydro-2H-pyridine-1-carboxylate (4.68 g, crude).

$^1$H NMR (500 MHz, CDCl$_3$) δ (ppm) 0.96 (m, 3H), 1.17 (s, 9H), 1.39 (m, 1H), 1.74 (m, 2H), 2.09 (m, 2H), 2.36 (m, 1H), 2.90 (dd, 1H), 4.06 (d, 1H), 5.25 (s, 2H), 7.26-7.32 (m, 6H), 7.47 (s, 1H).

LCMS(ESI): [M+1]$^+$ m/z: calcd 367.2; found 368.3; Rt=1.657 min.

Step 7. Synthesis of 6-(1-benzylpyrazol-4-yl)-3-ethyl-2,3,4,5-tetrahydropyridine Hydrochloric acid, 30% w/w aq. soln. (17.25 g, 141.93 mmol, 15 mL, 30% purity) was added to a solution of tert-butyl 6-(1-benzylpyrazol-4-yl)-3-ethyl-3,4-dihydro-2H-pyridine-1-carboxylate (4.68 g, 12.74 mmol) in Dioxane (20 mL). Resulting mixture was stirred at 40° C. for 15 hr. Then, volatiles were removed under reduced pressure and residue was partitioned between water (50 ml) and ethyl acetate (35 ml). Organic layer was separated and discarded. Aqueous layer was basified with solid $K_2CO_3$ and extracted with DCM (3×20 ml). Combined organic layers were dried over $K_2CO_3$ and concentrated in vacuo, affording 6-(1-benzylpyrazol-4-yl)-3-ethyl-2,3,4,5-tetrahydropyridine (2.13 g, 7.97 mmol, 62.56% yield).

$^1$H NMR (400 MHz, CDCl$_3$) δ (ppm) 0.92 (m, 3H), 1.21-1.32 (m, 3H), 1.45 (m, 1H), 1.88 (m, 1H), 2.43 (m, 1H), 2.60 (dd, 1H), 3.17 (dd, 1H), 3.87 (dd, 1H), 5.26 (s, 2H), 7.20-7.32 (m, 5H), 7.69 (s, 1H), 7.77 (s, 1H).

LCMS(ESI): [M+1]$^+$ m/z: calcd 267.2; found 268.2; Rt=0.863 min.

Step 8. Synthesis of (2R,5S)-2-(1-benzylpyrazol-4-yl)-5-ethyl-piperidine

To a stirring solution of 6-(1-benzylpyrazol-4-yl)-3-ethyl-2,3,4,5-tetrahydropyridine (2.13 g, 7.97 mmol) in Methanol (40 mL) was added Sodium Borohydride (452.09 mg, 11.95 mmol, 422.52 μL) in portions. Resulting mixture was stirred at 20° C. for 2 hr. Then, solvent was removed under reduced pressure and residue was partitioned between water (20 ml) and ethyl acetate (30 ml). Organic layer was separated, dried over $Na_2SO_4$ and concentrated in vacuo, affording (2R,5S)-2-(1-benzylpyrazol-4-yl)-5-ethyl-piperidine (1.98 g, 7.35 mmol, 92.26% yield).

$^1$H NMR (500 MHz, DMSO) δ(ppm) 0.88 (m, 3H), 1.19 (m, 1H), 1.36 (m, 2H), 1.36 (m, 1H), 1.57 (m, 1H), 1.90 (m, 3H), 2.34 (dd, 1H), 3.15 (d, 1H), 3.56 (d, 1H), 5.24 (s, 2H), 7.20-7.32 (m, 6H), 7.48 (s, 1H).

LCMS(ESI): [M+1]$^+$ m/z: calcd 269.2; found 270.1; Rt=0.944 min.

Step 9. Synthesis of (2R,5S)-2-(1-benzylpyrazol-4-yl)-5-ethyl-piperidine

Di-tert-butyl dicarbonate (1.76 g, 8.09 mmol, 1.86 mL) was added to a solution of (2R,5S)-2-(1-benzylpyrazol-4-yl)-5-ethyl-piperidine (1.98 g, 7.35 mmol) in Dichloromethane (30 mL). Resulting mixture was stirred at 20° C. for 4 hr. Then, volatiles were removed under reduced pressure and residue was purified by gradient column chromatography (Hex-MTBE), affording tert-butyl (2R,5S)-2-(1-benzylpyrazol-4-yl)-5-ethyl-piperidine-1-carboxylate (2.2 g, 5.95 mmol, 81.01% yield).

$^1$H NMR (dmso, 600 MHz): δ (ppm) 0.87-0.90 (m, 4H), 1.31 (m, 1H), 1.44 (m, 10H), 1.74 (m, 3H), 1.98 (m, 1H), 2.90 (d, 1H), 3.83 (d, 1H), 5.26 (s, 2H), 5.33 (s, 1H), 7.18 (m, 2H), 7.33-7.38 (m, 5H).

LCMS(ESI): [M+1]$^+$ m/z: calcd 369.2; found 370.2; Rt=1.687 min.

Step 10. Synthesis of tert-butyl (2R,5S)-2-(1-benzylpyrazol-4-yl)-5-ethyl-piperidine-1-carboxylate To a solution of tert-butyl (2R,5S)-2-(1-benzylpyrazol-4-yl)-5-ethyl-piperidine-1-carboxylate (2.2 g, 5.95 mmol) in a methanol (40 mL) was added 10% Pd/Carbon A402028-10 Lot C-14557 (0.5 g, 469.84 µmol, 10% purity) and Acetic acid (5.05 g, 84.11 mmol, 4.81 mL). The resulting mixture was evacuated and then backfilled with hydrogen. The reaction mixture was stirred under atmosphere of hydrogen (balloon pressure) at 55° C. for 18 hr. Then, catalyst was filtered off and filtrate was concentrated in vacuo, affording tert-butyl (2R,5S)-5-ethyl-2-(1H-pyrazol-4-yl)piperidine-1-carboxylate (1.75 g, crude).

$^1$H NMR (dmso, 400 MHz): δ (ppm) 0.93 (m, 3H), 1.34 (m, 1H), 1.48 (m, 12H), 1.77 (m, 2H), 2.04 (m, 1H), 2.90 (d, 1H), 3.85 (d, 1H), 5.39 (s, 1H), 7.26 (m, 2H), 7.44 (s, 1H).

LCMS(ESI): [M+1]$^+$ m/z: calcd 279.2; found 280.2; Rt=1.278 min.

Step 11. Synthesis of (2R,5S)-5-ethyl-2-(1H-pyrazol-4-yl)piperidine

Hydrogen chloride solution 40 M in dioxane (15.15 g, 41.55 mmol, 15 mL, 10% purity) was added to a solution of tert-butyl (2R,5S)-5-ethyl-2-(1H-pyrazol-4-yl)piperidine-1-carboxylate (1.6 g, 5.73 mmol) in Methanol (10 mL). Resulting mixture was stirred at 25° C. for 16 hr. Then, volatiles were removed under reduced pressure, affording (2R,5S)-5-ethyl-2-(1H-pyrazol-4-yl)piperidine (1.44 g, 5.71 mmol, 100.00% yield, 2HCl).

$^1$H NMR (dmso, 400 MHz): δ (ppm) 0.84 (m, 3H), 1.19 (m, 3H), 1.70 (m, 1H), 1.86 (m, 1H), 1.96 (m, 1H), 2.60 (dd, 1H), 3.12 (m, 1H), 4.07 (t, 1H), 5.93 (brs, 2H), 7.88 (s, 2H), 9.47 (s, 1H).

LCMS(ESI): [M+1]$^+$ m/z: calcd 279.2; found 280.2; Rt=1.278 min.

3OO. The Synthesis of 7-fluoro-5-(5-methyl-2-piperidyl)-1H-indazole

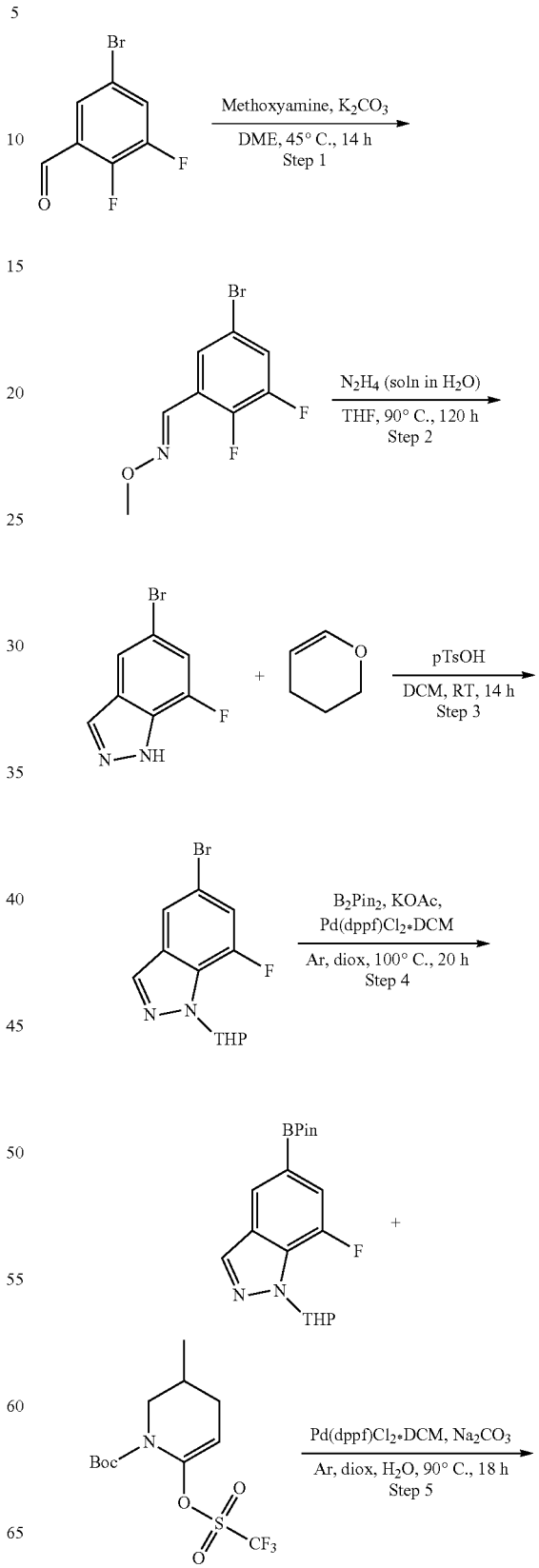

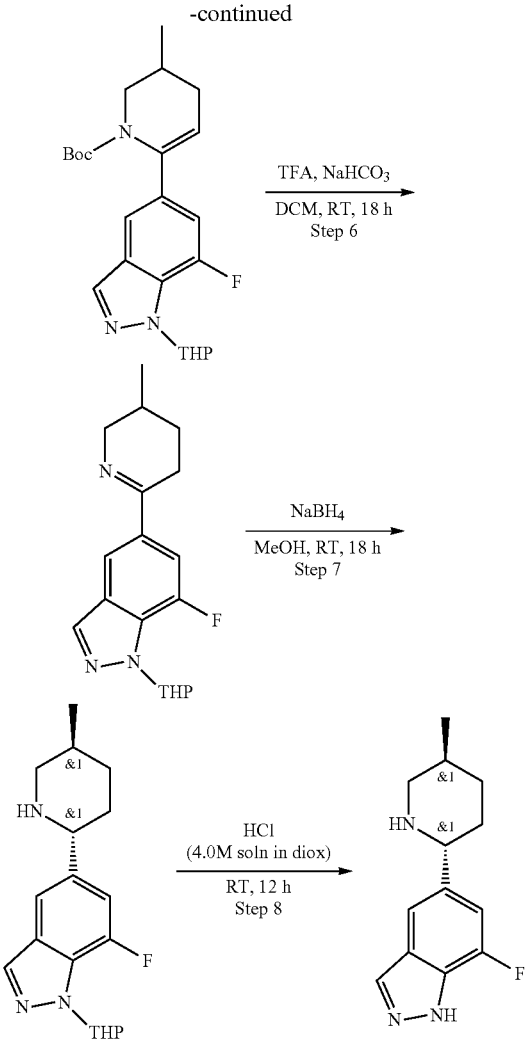

Step 1: The Synthesis of (Z)-1-(5-bromo-2,3-difluoro-phenyl)-N-methoxy-methanimine Potassium carbonate (7.50 g, 54.30 mmol, 3.28 mL) was added into the solution of 5-bromo-2,3-difluoro-benzaldehyde (10 g, 45.25 mmol) and O-methylhydroxylamine (4.16 g, 49.77 mmol, HCl) in DME (115 mL), and the reaction was reacted at 45° C. overnight. After cooling to room temperature, it was filtered, washed with ethyl acetate, and evaporated.

$^1$H NMR (400 MHz, CDCl$_3$) δ 3.99 (s, 3H), 7.30 (m, 1H), 7.73 (s, 1H), 8.18 (s, 1H).

Step 2: The Synthesis of 5-bromo-7-fluoro-1H-indazole

A solution of (Z)-1-(5-bromo-2,3-difluoro-phenyl)-N-methoxy-methanimine (10.7 g, 42.79 mmol), Hydrazine hydrate solution (45 mL) in THF (45 mL) was heated to 90° C. for 120 h. The solvent was evaporated and the resulting mixture was diluted with EtOAc, washed with water, dried over Na$_2$SO$_4$ and concentrated under vacuum to give crude product. The residue was purified via flash column chromatography to give 1.95 g $^1$H NMR (400 MHz, DMSO-d$_6$) δ 7.30 (s, 1H), 7.76 (s, 1H), 8.06 (s, 1H), 13.72 (s, 1H).

LCMS(ESI): [M+2H]$^+$ m/z: calcd 215.0; found 217.0; Rt=0.959 min.

Step 3: The Synthesis of 5-bromo-7-fluoro-1-tetrahydropyran-2-yl-indazole

To a solution of 5-bromo-7-fluoro-1H-indazole (1.95 g, 9.07 mmol) and 3,4-dihydro-2H-pyran (915.40 mg, 10.88 mmol, 988.56 µL) in CH$_2$C$_2$ (40 mL) was added p-Toluenesulfonic acid monohydrate (172.51 mg, 906.88 µmol, 139.12 µL). The mixture was stirred at rt overnight. The mixture was diluted with DCM (250 mL) and washed with water (3×80 mL). The organic layer was dried (Na$_2$SO$_4$), filtered, and concentrated under reduced pressure.

$^1$H NMR (400 MHz, CDCl$_3$) δ 1.71 (m, 2H), 3.29 (m, 2H), 3.71 (m, 2H), 3.81 (m, 1H), 4.50 (m, 1H), 5.71 (m, 1H), 7.50 (d, 1H), 7.89 (s, 1H), 8.36 (s, 1H).

LCMS(ESI): [M+H]$^+$ m/z: calcd; found; Rt=min.

Step 4: The Synthesis of 7-fluoro-1-tetrahydropyran-2-yl-5-(4,4,5,5-tetramethyl-1,3,2-dioxaborolan-2-yl)indazole 5-bromo-7-fluoro-1-tetrahydropyran-2-yl-indazole (2.7 g, 9.03 mmol), 4,4,5,5-tetramethyl-2-(4,4,5,5-tetramethyl-1,3,2-dioxaborolan-2-yl)-1,3,2-dioxaborolane (2.29 g, 9.03 mmol) and potassium Acetate (1.77 g, 18.05 mmol, 1.13 mL) were mixed in Dioxane (60 mL) and the resulting mixture was evacuated and backfilled three times with argon. [1,1'-Bis(diphenylphosphino)ferrocene]dichloropalladium(II), complex with dichloromethane (368.54 mg, 451.30 µmol) was added thereto and the reaction mixture was heated at 100° C. for 20 hr. The reaction mixture was cooled and filtered. The filtrate was concentrated in vacuo and purified by column chromatography to obtain 7-fluoro-1-tetrahydropyran-2-yl-5-(4,4,5,5-tetramethyl-1,3,2-dioxaborolan-2-yl)indazole (1.87 g, 5.40 mmol, 59.84% yield).

$^1$H NMR (400 MHz, CDCl$_3$) δ 1.20 (m, 2H), 1.42 (s, 12H), 1.70 (m, 2H), 2.12 (m, 2H), 2.60 (m, 1H), 3.72 (m, 1H), 5.91 (m, 1H), 7.49 (d, 1H), 8.08 (s, 1H), 8.19 (s, 1H).

Step 5: The Synthesis of tert-butyl 6-(7-fluoro-1-tetrahydropyran-2-yl-indazol-5-yl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (1.70 g, 4.91 mmol), 7-fluoro-1-tetrahydropyran-2-yl-5-(4,4,5,5-tetramethyl-1,3,2-dioxaborolan-2-yl)indazole (1.87 g, 5.40 mmol) and Sodium carbonate (1.04 g, 9.82 mmol, 411.43 µL) were mixed together in a mixture of Dioxane (15 mL) and Water (5 mL). The resulting mixture was evacuated and backfilled three times with argon and [1,1'-Bis(diphenylphosphino)ferrocene]dichloropalladium(II), complex with dichloromethane (200.50 mg, 245.52 µmol) was added thereto. The reaction mixture was heated at 90° C. for 18 hr. The reaction mixture was cooled and poured into water (50 ml). The resulting mixture was extracted with EtOAc (2*50 ml) and combined organic layers were washed with brine, dried over Na$_2$SO$_4$, filtered and evaporated.

LCMS(ESI): [M-THP]$^+$ m/z: calcd 331.2; found 332.2; Rt=1.407 min.

Step 6: The Synthesis of 7-fluoro-5-(3-methyl-2,3,4,5-tetrahydropyridin-6-yl)-1-tetrahydropyran-2-yl-indazole Trifluoroacetic acid (3.02 g, 26.47 mmol, 2.04 mL) was added to tert-butyl 6-(7-fluoro-1-tetrahydropyran-2-yl-indazol-5-yl)-3-methyl-3,4-dihydro-2H-pyridine-1-carboxylate (2.2 g, 5.29 mmol) in $CH_2Cl_2$ (2 mL). The reaction mixture was stirred at 25° C. for 18 hr, then evaporated in vacuo and poured into water (80 ml) with Sodium bicarbonate (4.45 g, 52.95 mmol, 2.06 mL) and extracted with EtOAc (2×30 ml). The combined organic extracts were washed with water (2*20 ml), dried over sodium sulphate and evaporated in vacuo.

LCMS(ESI): [M+H]+ m/z: calcd 315.2; found 316.2; Rt=0.867 min.

Step 7: The Synthesis of 7-fluoro-5-(5-methyl-2-piperidyl)-1-tetrahydropyran-2-yl-indazole 7-fluoro-5-(3-methyl-2,3,4,5-tetrahydropyridin-6-yl)-1-tetrahydropyran-2-yl-indazole (1.45 g, 4.60 mmol) was dissolved in MeOH (20 mL) and Sodium Borohydride (521.78 mg, 13.79 mmol, 487.64 µL) was added portionwise. The reaction mixture was stirred for 18 hr. The reaction mixture was evaporated to dryness. The residue was dissolved in DCM (50 ml) and the resulting mixture was extracted with aq·$NaHSO_4$ solution (2*50 ml). Combined aqueous layers were washed with DCM (3*50 ml) and then basified with $K_2CO_3$. The resulting mixture was extracted with DCM (2*100 ml) and combined organic layers were dried over $Na_2SO_4$, filtered and evaporated.

LCMS(ESI): [M+H]+ m/z: calcd 317.2; found 318.2; Rt=0.757 min.

Step 8: The Synthesis of 7-fluoro-5-(5-methyl-2-piperidyl)-1H-indazole 7-fluoro-5-(5-methyl-2-piperidyl)-1-tetrahydropyran-2-yl-indazole (0.74 g, 2.33 mmol) was dissolved in Hydrogen chloride solution 40 M in dioxane (1.70 g, 2.13 mL) and solution was stirred for 12 h. The reaction mixture was evaporated to dryness.

LCMS(ESI): [M+H]+ m/z: calcd 233.2; found 234.2; Rt=0.619 min.

3PP. The Synthesis of 5-methyl-2-(5-methyl-2-piperidyl)pyridine

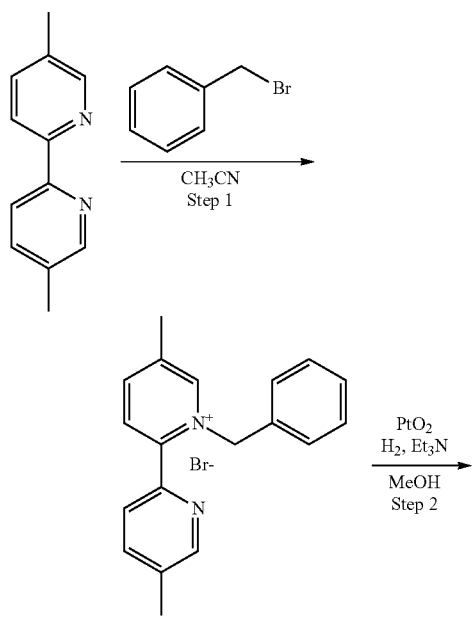

Step 1: Synthesis of 2-(1-benzyl-5-methyl-2-pyridyl)-5-methyl-pyridine bromide

A mixture of 5-methyl-2-(5-methyl-2-pyridyl)pyridine (1 g, 5.43 mmol) and benzyl bromide (2.48 g, 14.48 mmol, 1.72 mL) in Acetonitrile (10 mL) was heated in a sealed tube for 18 hours at 85° C. After 18 hours, the reaction mixture was concentrated under reduced pressure. The obtained crude product was triturated with MTBE, the precipitate was filtered, washed with MTBE and dried under vacuum to give 2-(1-benzyl-5-methyl-2-pyridyl)-5-methyl-pyridine bromide (1.95 g, crude) as a light pink powder.

$^1$H NMR ($CDCl_3$, 400 MHz): δ (ppm) 2.44 (s, 3H), 2.63 (s, 3H), 6.24 (s, 2H), 7.21 (m, 5H), 7.59 (d, 1H), 7.66 (d, 1H), 7.91 (d, 1H), 8.34 (m, 1H), 8.60 (s, 1H), 9.75 (s, 1H).

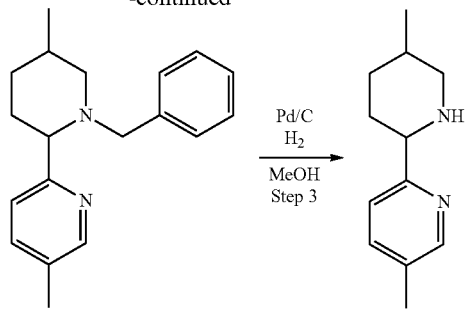

Step 2: Synthesis of 2-(1-benzyl-5-methyl-2-piperidyl)-5-methyl-pyridine

In an autoclave, a solution of 2-(1-benzyl-5-methyl-2-pyridyl)-5-methyl-pyridine bromide (1.9 g, 4.92 mmol) and TEA (0.5 g, 4.94 mmol, 688.71 µL) in Methanol (50 mL) was hydrogenated over $PtO_2$ (0.05 g, 220.19 µmol) under 20 atm $H_2$ pressure at 40° C. for 18 hours. Upon completion, the reaction mixture was filtered through Celite pad and the filtrate was concentrated under reduced pressure. The obtained crude product was triturated with MTBE. The precipitate was filtered and the filtrate was concentrated under reduced pressure to obtain 2-(1-benzyl-5-methyl-2-piperidyl)-5-methyl-pyridine (1.3 g, crude) as a mixture of diastereoisomers (~1:3).

LCMS(ESI): [M+H]+ m/z: calcd 280.2; found 281.2; Rt=1.010 min.

Step 3: Synthesis of 5-methyl-2-(5-methyl-2-piperidyl)pyridine

In an autoclave, a solution of 2-(1-benzyl-5-methyl-2-piperidyl)-5-methyl-pyridine (0.5 g, 1.78 mmol) in Methanol (80 mL) was hydrogenated over 10% Pd/C (1.78 mmol) under 10 atm $H_2$ pressure at 100° C. for 12 hours. Upon completion, the reaction mixture was filtered through Celite pad and the filtrate was concentrated in vacuo to obtain 5-methyl-2-(5-methyl-2-piperidyl)pyridine (0.33 g, crude). The crude product was used for the next step reaction.

LCMS(ESI): [M+H]+ m/z: calcd 190.2; found 191.2; Rt=0.806-1.099 min.

3QQ. The Synthesis of rac-5-((2R,5S)-5-methylpiperidin-2-yl)-1H-thieno[3,2-C]pyrazole

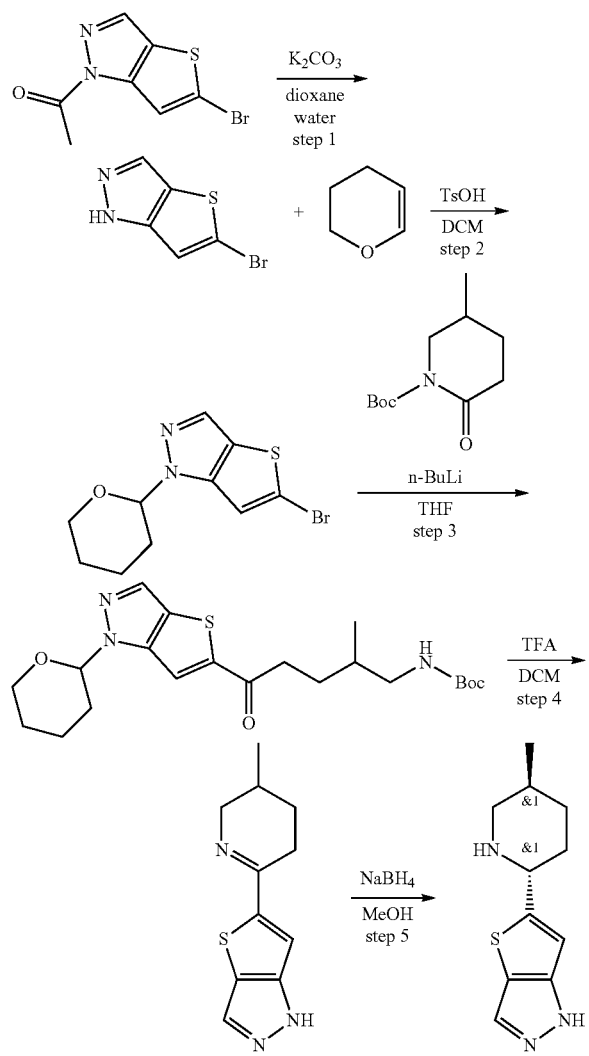

Step 1: Synthesis of 5-bromo-1H-thieno[3,2-c]pyrazole 1-(5-bromothieno[3,2-c]pyrazol-1-yl)ethanone (10 g, 40.80 mmol) was dissolved in dioxane (50 mL) and mixed with potassium carbonate (8.46 g, 61.20 mmol, 8.46 mL) in H$_2$O (10 mL). The reaction mixture was heated to 70° C. and stirred for 48 hr (completion of the reaction was controlled by H-NMR). After the reaction was complete, the solvents was evaporated under reduced pressure; the oily residue was triturated with H$_2$O (100 mL) and filtered. Obtained solid was dried on air to give 5-bromo-1H-thieno[3,2-c]pyrazole (7.5 g, 36.93 mmol, 90.53% yield).

$^1$H NMR (400 MHz, DMSO-d$_6$) δ (ppm) 7.43 (s, 1H), 7.83 (s, 1H), 13.11 (bds, 1H).

Step 2: Synthesis of 5-bromo-1-(tetrahydro-2H-pyran-2-yl)-1H-thieno[3,2-c]pyrazole 5-bromo-1H-thieno[3,2-c]pyrazole (7.5 g, 36.93 mmol) was suspended in 3,4-dihydro-2H-pyran (31.07 g, 369.35 mmol, 33.55 mL) followed by the addition of toluenesulfonic acid (636.02 mg, 3.69 mmol) (Caution! Exotherm was observed). After the reaction was complete, the mixture was evaporated to dryness and subjected to CC (OOK. Interchim, 330 g SiO$_2$, petroleum ether/MTBE with MTBE from 5~15%, flow rate=135 mL/min, Rv=6-10 CV) to give 5-bromo-1-tetrahydropyran-2-yl-thieno[3,2-c]pyrazole (6 g, 20.89 mmol, 56.57% yield).

$^1$H NMR (400 MHz, CDCl$_3$) δ (ppm) 1.65 (m, 4H), 2.15 (m, 2H), 3.71 (m, 1H), 4.07 (m, 1H), 5.48 (m, 1H), 7.13 (s, 1H), 7.68 (s, 1H).

LCMS(ESI): [M]$^+$ m/z: calcd 287.2; found 288.2; Rt=1.239 min.

Step 3: Synthesis of tert-butyl (2-methyl-5-oxo-5-(1-(tetrahydro-2H-pyran-2-yl)-1H-thieno[3,2-c]pyrazol-5-yl)pentyl)carbamate 5-bromo-1-tetrahydropyran-2-yl-thieno[3,2-c]pyrazole (6 g, 20.89 mmol) was dissolved in THF (30 mL) and cooled to −78° C. under Ar. Butyl lithium (2.5 M, 9.19 mL) was added dropwise, keeping temperature at the same point. After additional stirring for 10 min., the solution of tert-butyl 5-methyl-2-oxo-piperidine-1-carboxylate (6.68 g, 31.34 mmol) in THF (20 mL) was added. After additional stirring for 10 min, the reaction was warmed to −10° C. and quenched with sat aq NH$_4$Cl (30 mL). The crude reaction mixture was partitioned between EtOAc (50 mL) and H$_2$O (30 mL), the organic layer was dried over Na$_2$SO$_4$, evaporated to dryness and purified with CC (OK. Companion combiflash; 330 g SiO$_2$, chloroform/MeCN with MeCN from 0~10%, flow rate=100 mL/min, Rv=6.5 CV) to give tert-butyl N-[2-methyl-5-oxo-5-(1-tetrahydropyran-2-ylthieno[3,2-c]pyrazol-5-yl)pentyl]carbamate (1.5 g, 3.56 mmol, 17.03% yield).

$^1$H NMR (400 MHz, CDCl$_3$) δ (ppm) 0.92 (d, 3H), 1.42 (s, 9H), 1.78 (m, 7H), 2.13 (m, 2H), 2.31 (m, 1H), 3.07 (m, 3H), 3.75 (m, 1H), 4.02 (m, 1H), 4.66 (m, 1H), 5.61 (m, 1H), 7.69 (s, 1H), 7.75 (s, 1H).

LCMS(ESI): [M]$^+$ m/z: calcd 421.2; found 422.2; Rt=1.525 min.

Step 4: Synthesis of 5-(5-methyl-3,4,5,6-tetrahydropyridin-2-yl)-1H-thieno[3,2-c]pyrazole tert-butyl N-[2-methyl-5-oxo-5-(1-tetrahydropyran-2-ylthieno[3,2-c]pyrazol-5-yl)pentyl]carbamate (1.5 g, 3.56 mmol) was dissolved in DCM (10 mL) followed by the addition of TFA (2.03 g, 17.79 mmol, 1.37 mL) and stirring overnight. After the reaction was complete, the mixture was washed with 10% aq NaOH, and the organic solvent was evaporated to give 5-(3-methyl-2,3,4,5-tetrahydropyridin-6-yl)-1H-thieno[3,2-c]pyrazole (0.8 g, crude) which was used in the next step without purification.

$^1$H NMR (600 MHz, CDCl$_3$) δ (ppm) 1.02 (d, 3H), 1.56 (m, 1H), 1.76 (m, 1H), 1.95 (m, 1H), 2.56 (m, 1H), 2.86 (m, 1H), 3.26 (m, 1H), 3.96 (m, 1H), 4.36 (m, 1H), 7.28 (s, 1H), 7.76 (s, 1H).

Step 5: Synthesis of rac-5-((2R,5S)-5-methylpiperidin-2-yl)-1H-thieno[3,2-c]pyrazole 5-(3-methyl-2,3,4,5-tetrahydropyridin-6-yl)-1H-thieno[3,2-c]pyrazole (0.8 g, 3.65 mmol) was dissolved in MeOH (5 mL) and cooled to 0° C. Sodium borohydride (138.01 mg, 3.65 mmol, 128.98 μL) was added in portions to obtained mixture and additionally stirred overnight. After the reaction was complete, the reaction mixture was acidified with 10% aq HCl to pH=2, washed with MTBE (2*10 mL), basified with 10% aq NaOH to pH=10 and extracted with DCM (10 mL). Combined organic layers were dried over Na₂SO₄ and evaporated to give 5-[(2S,5R)-5-methyl-2-piperidyl]-1H-thieno[3,2-c]pyrazole (0.9 g, crude) which was used in the next step without purification.

¹H NMR (600 MHz, CDCl₃) δ (ppm) 0.98 (d, 3H), 1.65 (m, 4H), 1.95 (m, 2H), 2.38 (m, 1H), 3.16 (m, 1H), 3.82 (m, 1H), 6.82 (s, 1H), 7.71 (s, 1H).

3RR. Synthesis of rac-5-((2R,5S)-5-methylpiperidin-2-yl)-1H-thieno[2,3-C]pyrazole

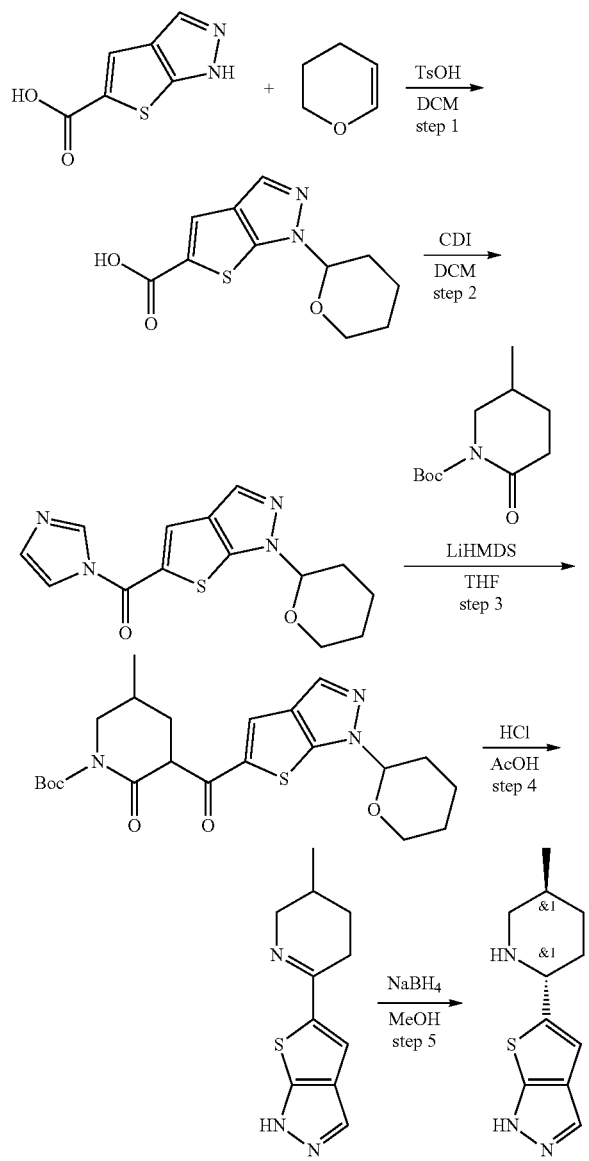

Step 1: Synthesis of 1-(tetrahydro-2H-pyran-2-yl)-1H-thieno[2,3-c]pyrazole-5-carboxylic acid 1H-thieno[2,3-c]pyrazole-5-carboxylic acid (5 g, 29.73 mmol) was suspended in 3,4-dihydro-2H-pyran (25.01 g, 297.31 mmol, 27.01 mL), followed by the addition of toluenesulfonic acid (255.99 mg, 1.49 mmol). After 0.5 hr of intensive stirring all solids were dissolved; clear solution was evaporated to dryness and the crude residue was dissolved in 50% aq KOH. Obtained milky suspension was washed with DCM (30 mL) five times and with MTBE (30 mL)₂ times. The clear light-yellow solution was acidified with 10% aq NaHSO₄ to pH=2 and extracted with DCM (30 mL)₂ times. Evaporation of the combined organic solvents results in 1-tetrahydropyran-2-ylthieno[2,3-c]pyrazole-5-carboxylic acid (7.2 g, 28.54 mmol, 95.99% yield) as mixture of regioisomers.

¹H NMR (500 MHz, DMSO-d₆) δ (ppm) 1.95 (m, 6H), 3.86 (m, 2H), 5.56 (m, 1H), 7.68 (s, 1H), 8.28 (s, 1H), 13.25 (bds, 1H).

LCMS(ESI): [M]⁺ m/z: calcd 252.2; found 253.2; Rt=1.089 min.

Step 2: Synthesis of (1H-imidazol-1-yl)(1-(tetrahydro-2H-pyran-2-yl)-1H-thieno[2,3-c]pyrazol-5-yl)methanone 1-tetrahydropyran-2-ylthieno[2,3-c]pyrazole-5-carboxylic acid (7.2 g, 28.54 mmol) was dissolved in DCM (100 mL), followed by the addition of CDI (6.94 g, 42.81 mmol) in one portions. After the reaction was complete (concluded by finished evolution of gaseous by-products and by H-NMR) the mixture was diluted with DCM (100 mL) and washed with 0.1 M aq HCl (three times). Evaporation of the organic solvent under reduced pressure results in imidazol-1-yl-(1-tetrahydropyran-2-ylthieno[2,3-c]pyrazol-5-yl)methanone (5.8 g, 19.18 mmol, 67.22% yield) which was used in the next step immediately.

¹H NMR (500 MHz, DMSO-d₆) δ (ppm) 1.95 (m, 6H), 3.82 (m, 1H), 4.08 (m, 1H), 5.62 (m, 1H), 7.19 (s, 1H), 7.69 (s, 1H), 7.82 (s, 1H), 8.12 (s, 1H), 8.32 (s, 1H).

Step 3: Synthesis of tert-butyl 5-methyl-2-oxo-3-(1-(tetrahydro-2H-pyran-2-yl)-1H-thieno[2,3-c]pyrazole-5-carbonyl)piperidine-1-carboxylate tert-butyl 5-methyl-2-oxo-piperidine-1-carboxylate (4.50 g, 21.10 mmol) was dissolved in THF (40 mL) and cooled to −78° C. under Ar, followed by the addition of lithium hexamethyldisilazide (1.03 M, 22.35 mL) in a dropwise manner. After additional stirring for 10 min, the solution of imidazol-1-yl-(1-(tetrahydropyran-2-ylthieno[2,3-c]pyrazol-5-yl)methanone (5.8 g, 19.18 mmol) in THF (40 mL) was added and the reaction mixture was warmed to rt. After the reaction was complete, the mixture was poured on sat aq NH₄Cl and extracted with EtOAc (100 mL) three times. Evaporation of the organic solvents and purification with CC (OK. Interchim; 220 g SiO₂, petroleum ether/ethyl acetate with ethyl acetate from 10~75%, flow rate=100 mL/min, Rv=7.7 CV) results in tert-butyl 5-methyl-2-oxo-3-(1-tetrahydropyran-2-ylthieno[2,3-c]pyrazole-5-carbonyl)piperidine-1-carboxylate (4.5 g, 10.05 mmol, 52.42% yield) as mixture of isomers. Separate fractions were combined and used in the next step.

¹H NMR (500 MHz, CDCl₃) δ (ppm) 1.08 (d, 3H), 1.53 (s, 9H), 1.62 (m, 4H), 2.15 (m, 6H), 3.23 (m, 1H), 3.85 (m, 2H), 4.39 (m, 1H), 5.55 (m, 1H), 7.86 (m, 2H).

LCMS(ESI): [M-Boc]⁺ m/z: calcd 347.2; found 348.2; Rt=1.384 min.

Step 4: Synthesis of 5-(5-methyl-3,4,5,6-tetrahydropyridin-2-yl)-1H-thieno[2,3-c]pyrazole tert-butyl 5-methyl-2-oxo-3-(1-tetrahydropyran-2-ylthieno[2,3-c]pyrazole-5-carbonyl)piperidine-1-carboxylate (4.5 g, 10.05 mmol) was dissolved in acetic acid (50 mL) and heated to reflux. HCl (10 M, 10.05 mL) was added dropwise (Caution! Intensive foaming was observed!). After gas evolution was stopped, the mixture was evaporated to dryness, dissolved in H₂O (50 mL) and basified to pH=10 with 10% aq K₂CO₃; obtained opaque solution was extracted with DCM (150 mL), which was dried over Na₂SO₄ and evaporated under reduced pressure to give 5-(3-methyl-2,3,4,5-tetrahydropyridin-6-yl)-1H-thieno[2,3-c]pyrazole (1.6 g, 7.30 mmol, 72.56% yield).

$^1$H NMR (400 MHz, CDCl₃) δ (ppm) 1.02 (d, 3H), 1.86 (m, 1H), 1.95 (m, 2H), 2.48 (m, 1H), 2.86 (m, 1H), 3.26 (m, 1H), 4.02 (m, 1H), 7.42 (m, 1H), 7.82 (m, 2H).

LCMS(ESI): [M]⁺ m/z: calcd 219.2; found 220.2; Rt=0.802 min.

Step 5: Synthesis of rac-5-((2R,5S)-5-methylpiperidin-2-yl)-1H-thieno[2,3-c]pyrazole 5-(3-methyl-2,3,4,5-tetrahydropyridin-6-yl)-1H-thieno[2,3-c]pyrazole (1.6 g, 7.30 mmol) was dissolved in MeOH (20 mL) and cooled to 0° C. Sodium borohydride (552.00 mg, 14.59 mmol, 515.89 µL) was added in portions to obtained mixture and additionally stirred overnight. After the reaction was complete, the reaction mixture was acidified with 10% aq HCl to pH=2, washed with MTBE (2*10 mL), basified with 10% aq NaOH to pH=10 and extracted with DCM (50 mL). Evaporation of the solvent result in pure 5-[(2S,5R)-5-methyl-2-piperidyl]-2H-thieno[2,3-c]pyrazole (1.3 g, 5.87 mmol, 80.51% yield).

$^1$H NMR (500 MHz, CDCl₃) δ (ppm) 0.98 (d, 3H), 1.56 (m, 2H), 1.68 (m, 2H), 1.92 (m, 1H), 2.02 (m, 1H), 2.44 (m, 1H), 3.20 (m, 1H), 3.86 (m, 1H), 6.83 (s, 1H), 7.61 (s, 1H).

LCMS(ESI): [M]⁻ m/z: calcd 221.2; found 222.2; Rt=0.711 min.

3SS. Synthesis of rac-(2R,5S)-5-methyl-2-(1H-pyrazol-3-yl)piperidine

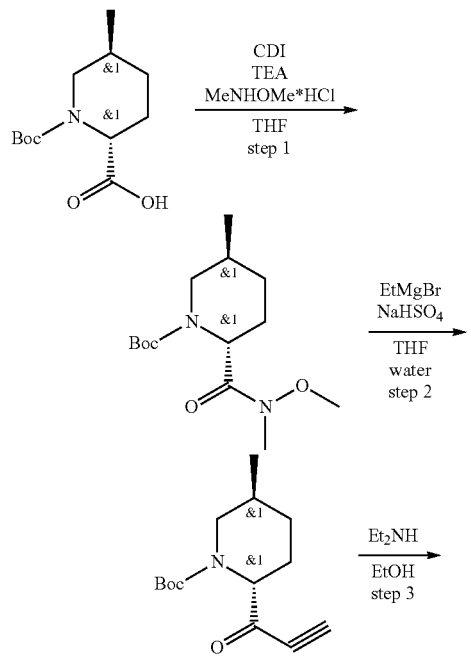

Step 1: Synthesis of rac-(2R,5S)-tert-butyl 2-(methoxy(methyl)carbamoyl)-5-methylpiperidine-1-carboxylate CDI (14.08 g, 86.81 mmol) was added in one portion to a stirred solution of (2R,5S)-1-tert-butoxycarbonyl-5-methyl-piperidine-2-carboxylic acid (17.6 g, 72.34 mmol) in THF (200 mL) at 25° C. The resulting mixture was stirred at 45° C. until carbon dioxide evolution was completed, then methoxy(methyl)amine hydrochloride (14.11 g, 144.68 mmol) and TEA (14.64 g, 144.68 mmol, 20.17 mL) were added. The reaction mixture was stirred at 50° C. for 12 hr, then cooled and evaporated in vacuum. The residue was diluted with 5% aqueous sodium hydrogen sulphate solution (200 ml) and extracted with DCM (2*100 ml). The combined organic extracts were washed with water (100 ml), dried over sodium sulphate and evaporated in vacuum to afford tert-butyl (2R,5S)-2-[methoxy(methyl)carbamoyl]-5-methyl-piperidine-1-carboxylate (18 g, 62.86 mmol, 86.89% yield) as colorless gum, which was used directly in the next step.

$^1$H NMR (500 MHz, CDCl₃) δ (ppm) 1.02 (d, 3H), 1.36 (m, 1H), 1.49 (s, 9H), 1.72 (m, 1H), 1.80 (m, 1H), 1.97 (m, 2H), 3.17 (s, 3H), 3.66 (m, 2H), 3.73 (s, 3H), 4.91 (m, 1H).

LCMS(ESI): [M-Boc]⁺ m/z: calcd 186.2; found 187.2; Rt=1.381 min.

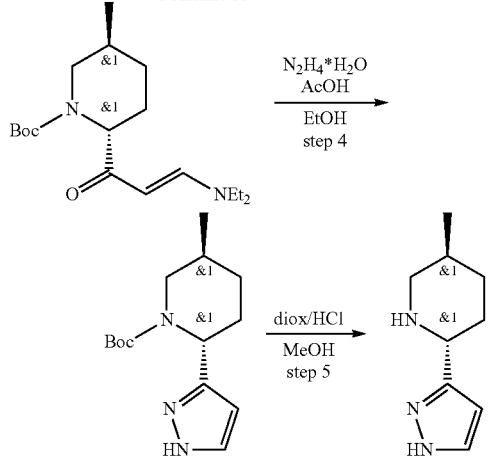

Step 2: Synthesis of rac-(2R,5S)-tert-butyl 5-methyl-2-propioloylpiperidine-1-carboxylate A solution of tert-butyl (2R,5S)-2-[methoxy(methyl)carbamoyl]-5-methyl-piperidine-1-carboxylate (18 g, 62.86 mmol) in THF (200 mL) was added dropwise at −40° C. to a stirred solution of ethynylmagnesium bromide (587.50 g, 314.85 mmol, 625 mL, 6.872% purity) (0.5M in THF solution). The resulting mixture was allowed to warm to 25° C. and stirred at this temperature for 12 hr, then poured into sodium hydrogen sulphate (75.47 g, 628.57 mmol) in water (675 mL). The resulting mixture was stirred for 30 min., then transferred into a separatory funnel. The upper organic layer was separated; the aqueous layer was additionally extracted with ethyl acetate (2*300 ml). The combined organic extracts were washed with brine (2*200 ml), dried over sodium sulphate and evaporated in vacuum to afford tert-butyl (2R,5S)-5-methyl-2-prop-2-ynoyl-piperidine-1-carboxylate (15 g, 59.68 mmol, 94.95% yield) as red oil, which was used directly in the next step.

$^1$H NMR (500 MHz, CDCl$_3$) δ (ppm) 0.88 (m, 1H), 0.96 (d, 3H), 1.36 (m, 1H), 1.49 (s, 9H), 1.57 (m, 1H), 1.95 (m, 2H), 2.08 (m, 1H), 3.24 (m, 1H), 3.52 (m, 1H), 4.58 (m, 1H).

LCMS(ESI): [M-Boc]$^+$ m/z: calcd 151.2; found 152.2; Rt=1.467 min.

Step 3: Synthesis of rac-(2R,5S)-tert-butyl 2-((E)-3-(diethylamino)acryloyl)-5-methylpiperidine-1-carboxylate tert-butyl (2R,5S)-5-methyl-2-prop-2-ynoyl-piperidine-1-carboxylate (15.00 g, 59.68 mmol) was diluted with a solution of diethyl amine (6.98 g, 95.50 mmol, 9.89 mL) in ethanol (200 mL). The resulting solution was stirred at 25° C. for 1 hr, and then evaporated in vacuum to afford tert-butyl (2R,5S)-2-[(E)-3-(diethylamino)prop-2-enoyl]-5-methyl-piperidine-1-carboxylate (19.8 g, crude) as red gum, which was used directly in the next step.

$^1$H NMR (500 MHz, CDCl$_3$) δ (ppm) 0.98 (d, 3H), 1.15 (m, 6H), 1.36 (m, 1H), 1.45 (s, 9H), 1.56 (m, 1H), 1.80 (m, 2H), 2.10 (m, 1H), 3.09 (m, 1H), 3.25 (m, 4H), 3.69 (m, 1H), 4.57 (m, 1H), 5.20 (d, 1H), 7.65 (d, 1H).

LCMS(ESI): [M]$^+$ m/z: calcd 324.2; found 325.2; Rt=1.372 min.

Step 4: Synthesis of rac-(2R,5S)-tert-butyl 5-methyl-2-(1H-pyrazol-3-yl)piperidine-1-carboxylate Hydrazine monohydrate (6.89 g, 88.15 mmol, 6.69 mL) was added to a stirred solution of tert-butyl (2R,5S)-2-[(E)-3-(diethylamino)prop-2-enoyl]-5-methyl-piperidine-1-carboxylate (14.3 g, 44.07 mmol) and acetic acid (5.29 g, 88.15 mmol, 5.04 mL) in ethanol (300 mL). The reaction mixture was stirred with reflux condenser at 80° C. for 36 hr, then cooled and evaporated in vacuum. The residue was diluted with water (100 ml) and extracted with MTBE (2*100 ml). The combined organic extracts were washed with water (50 ml), dried over sodium sulphate and evaporated in vacuum to afford crude tert-butyl (2R,5S)-5-methyl-2-(1H-pyrazol-3-yl)piperidine-1-carboxylate (10 g, 37.69 mmol, 85.51% yield) as red gum, which was used directly in the next step.

$^1$H NMR (500 MHz, CDCl$_3$) δ (ppm) 1.03 (d, 3H), 1.47 (s, 9H), 1.83 (m, 2H), 2.00 (m, 1H), 2.12 (m, 2H), 2.91 (m, 1H), 3.71 (m, 1H), 5.42 (m, 1H), 6.18 (d, 1H), 7.51 (d, 1H), 8.89 (m, 1H).

LCMS(ESI): [M-Boc]$^+$ m/z: calcd 165.2; found 166.2; Rt=1.293 min.

Step 5: Synthesis of rac-(2R,5S)-5-methyl-2-(1H-pyrazol-3-yl)piperidine

Hydrogen chloride solution 40 M in dioxane (7.35 g, 28.02 mmol, 7.00 mL, 13.9% purity) was added at 25° C. to a stirred solution of tert-butyl (2R,5S)-5-methyl-2-(1H-pyrazol-3-yl)piperidine-1-carboxylate (700 mg, 2.64 mmol) in MeOH (30 mL). The reaction mixture was stirred at 25° C. for 3 hr, and then concentrated in vacuum to afford (2R,5S)-5-methyl-2-(1H-pyrazol-3-yl)piperidine (530 mg, 2.63 mmol, 99.61% yield, HCl) as beige solid, which was used in the next step without further purification.

$^1$H NMR (500 MHz, DMSO-d$_6$) δ (ppm) 0.96 (d, 3H) 1.36 (m, 1H), 1.95 (m, 4H), 2.67 (m, 1H), 3.13 (m, 1H), 4.19 (m, 1H), 6.49 (d, 1H), 7.74 (d, 1H), 9.43 (m, 2H).

LCMS(ESI): [M]$^+$ m/z: calcd 165.2; found 166.2; Rt=0.653 min.

3TT. Synthesis of rac-3-((2R,5S)-5-methylpiperidin-2-yl)-1'H-1,3'-bipyrazole

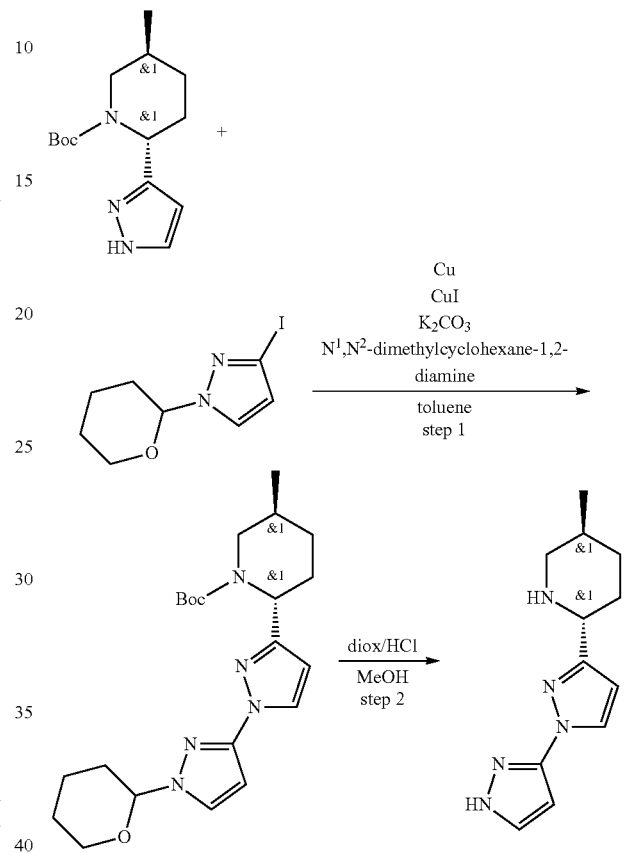

Step 1: Synthesis of rac-(2R,5S)-tert-butyl 5-methyl-2-(1'-(tetrahydro-2H-pyran-2-yl)-1'H-[1,3'-Bipyrazol]-3-yl)piperidine-1-carboxylate A mixture of tert-butyl (2R,5S)-5-methyl-2-(1H-pyrazol-3-yl)piperidine-1-carboxylate (3.7 g, 13.94 mmol), 3-iodo-1-tetrahydropyran-2-yl-pyrazole (4.74 g, 17.03 mmol), copper (I) iodide (1.85 g, 9.71 mmol, 329.18 µL), potassium carbonate, anhydrous, 99% (4.44 g, 32.13 mmol, 1.94 mL), N$^1$,N$^2$-dimethylcyclohexane-1,2-diamine (1.18 g, 8.32 mmol), copper (444.00 mg, 6.99 mmol) and toluene (100 mL) in 100 ml single-neck round bottom flask equipped with a reflux condenser and glass stopper was evacuated and then backfilled with argon. The reaction mixture was then stirred with a reflux condenser under argon at 110° C. for 72 hr. The LCMS of the aliquot showed 25.67% of the target compound. The reaction mixture was cooled down, and 50 ml of 25% aqueous ammonia were added. The resulting mixture was stirred for 0.5 hr, and then filtered through a short pad of magnesium silicate. The filter cake was additionally washed with ethyl acetate (2*25 ml) and discarded. The filtrate was transferred to a separatory funnel, the organic layer was separated, dried over sodium sulphate and evaporated in vacuum. The residue was purified by column chromatography on silica gel using hexane/ethyl acetate gradient (0-100% ethyl acetate) to afford crude tert-butyl (2R,5S)-5-methyl-2-[1-(1-tetrahydropyran-2-ylpyrazol-3-yl)pyrazol-3-yl]piperidine-1-carboxylate (3.5 g, 8.42 mmol, 60.41% yield) as light-yellow oil, which was used directly in the next step.

$^1$H NMR (400 MHz, CDCl$_3$) δ (ppm) 1.02 (d, 3H), 1.36 (m, 1H), 1.49 (s, 9H), 1.96 (m, 5H), 2.22 (m, 6H), 3.72 (m, 2H), 4.09 (m, 2H), 5.42 (m, 1H), 6.18 (d, 1H), 6.32 (d, 1H), 6.55 (d, 1H), 8.04 (d, 1H).

LCMS(ESI): [M]$^+$ m/z: calcd 415.2; found 416.2; Rt=1.696 min.

Step 2: Synthesis of rac-3-((2R,5S)-5-methylpiperidin-2-yl)-1'H-1,3'-bipyrazole Hydrogen chloride solution 4.0 M in dioxane (52.50 g, 200.15 mmol, 50 mL, 13.9% purity) was added at 25° C. to a stirred solution of tert-butyl (2R,5S)-5-methyl-2-[1-(1-tetrahydropyran-2-ylpyrazol-3-yl)pyrazol-3-yl]piperidine-1-carboxylate (2.5 g, 6.02 mmol) in MeOH (50 mL). The reaction mixture was stirred at 25° C. for 48 hr, and then concentrated in vacuum. The residue was evaporated with DCM (50 ml) to afford crude (2R,5S)-5-methyl-2-[1-(1H-pyrazol-3-yl)pyrazol-3-yl]piperidine (2 g, 5.87 mmol, 97.58% yield, 3HCl) as light-yellow gum, which was used directly in the next step.

$^1$H NMR (400 MHz, DMSO-d$_6$) δ (ppm) 0.96 (d, 3H), 1.36 (m, 1H), 2.07 (m, 4H), 2.36 (m, 1H), 2.59 (m, 1H), 4.16 (m, 1H), 6.44 (d, 1H), 6.79 (d, 1H), 7.82 (d, 1H), 8.26 (d, 1H), 9.58 (m, 2H).

LCMS(ESI): [M]$^+$ m/z: calcd 231.2; found 232.2; Rt=0.629 min.

3UU. The Synthesis of rac-5-[(2S,5S)-4,4-difluoro-5-methyl-2-piperidyl]-2-methyl-pyridine

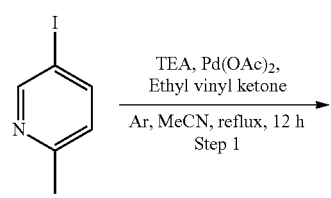

Step 1: The Synthesis of (E)-1-(6-methylpyridin-3-yl)pent-1-en-3-one

To a mixture of 5-iodo-2-methyl-pyridine (15 g, 68.49 mmol) and triethylamine (10.05 g, 99.30 mmol, 13.84 mL) was added pent-1-en-3-one (11.52 g, 136.97 mmol, 13.54 mL), followed by Palladium (II) acetate (768.79 mg, 3.42 mmol) and MeCN (300 mL) under Argon atmosphere. The mixture was refluxed for 12 hr. The solvent was removed and the residue was taken up with water (150 mL) and extracted with MTBE (3*100 mL). The organic layer was washed with brine, dried over anhydrous sodium sulphate, filtered and concentrated in vacuo to give (E)-1-(6-methyl-3-pyridyl)pent-1-en-3-one (12 g, 68.48 mmol, 100.00% yield), which was used in the next step without further purification.

¹H NMR (400 MHz, CDCl₃) δ 1.14 (t, 3H), 2.47 (s, 3H), 2.66 (q, 2H), 6.71 (m, 1H), 7.16 (m, 1H), 7.47 (m, 1H), 7.72 (m, 1H), 8.80 (s, 1H).
LCMS(ESI): [M+H]⁺ m/z: calcd 175.2; found 176.2; Rt=0.721 min.

Step 2: The Synthesis of (E)-5-(dimethylamino)-4-methyl-1-(6-methyl-3-pyridyl)pent-1-en-3-one A solution of (E)-1-(6-methyl-3-pyridyl)pent-1-en-3-one (12 g, 68.48 mmol), 1,3,5-trioxane, 98% (4.11 g, 136.97 mmol, 3.51 mL, 300% purity), dimethylamine hydrochloride (5.58 g, 68.48 mmol) and Hydrochloric acid, 36% w/w aq. soln. (6.94 g, 68.48 mmol, 5.78 mL, 36% purity) in ethanol (120 mL) was stirred at 80° C. for 12 hr. The solvent was removed in vacuo to give (E)-5-(dimethylamino)-4-methyl-1-(6-methyl-3-pyridyl)pent-1-en-3-one (22 g, crude, 2HCl), which was used for the next step without further purification.
LCMS(ESI): [M+H]⁺ m/z: calcd 232.2; found 233.2; Rt=0.164 min.

Step 3: The Synthesis of rac-(2S,5S)-5-methyl-2-(6-methyl-3-pyridyl)piperidin-4-one (E)-5-(dimethylamino)-4-methyl-1-(6-methyl-3-pyridyl) pent-1-en-3-one (22 g, 94.70 mmol) was dissolved in Water (120 mL) and NH₃ aq (120 mL) then the reaction mixture was stirred at 80° C. for 12 hr. The reaction mixture was acidified with 1 N HCl, extracted with MTBE (3*150 mL) then aqueous layer was basified with 1 N NaOH and extracted with DCM (3*100 ml). DCM layer was dried over Na₂SO₄, filtered and evaporated on vacuo to give (2S,5S)-5-methyl-2-(6-methyl-3-pyridyl)piperidin-4-one (14 g, crude), which was used in the next step without further purification.
LCMS(ESI): [M+H]⁺ m/z: calcd 204.2; found 205.2; Rt=0.196 min.

Step 4: The Synthesis of rac-tert-butyl (2S,5S)-5-methyl-2-(6-methyl-3-pyridyl)-4-oxo-piperidine-1-carboxylate A solution of (2S,5S)-5-methyl-2-(6-methyl-3-pyridyl)piperidin-4-one (14 g, 68.54 mmol) and di-tert-butyl dicarbonate (14.96 g, 68.54 mmol, 15.73 mL) in DCM (150 mL) was stirred at 25° C. for 12 hr. The solvent was removed in vacuo and the residue (20 g) was purified by gradient chromatography (DCM-MeCN) and repuried (MTBE-MeCN) to obtain tert-butyl (2S,5S)-5-methyl-2-(6-methyl-3-pyridyl)-4-oxo-piperidine-1-carboxylate (1.9 g, 6.24 mmol, 9.11% yield) and fraction 0.5 g 70% purity.
¹H NMR (400 MHz, CDCl₃) δ 1.16 (m, 3H), 1.42 (s, 9H), 2.52 (m, 1H), 2.55 (s, 3H), 2.80 (m, 1H), 2.99 (m, 1H), 3.56 (m, 1H), 3.77 (m, 1H), 5.57 (m, 1H), 7.10 (d, 1H), 7.42 (d, 1H), 8.39 (s, 1H).
LCMS(ESI): [M+H]⁺ m/z: calcd 304.2; found 305.2; Rt=0.935 min.

Step 5: The Synthesis of rac-(2S,5S)-5-methyl-2-(6-methyl-3-pyridyl)piperidin-4-one A solution of tert-butyl (2S,5S)-5-methyl-2-(6-methyl-3-pyridyl)-4-oxo-piperidine-1-carboxylate (1.9 g, 6.24 mmol) and trifluoroacetic acid (15 g, 131.55 mmol, 10.14 mL) in DCM (10 mL) was stirred at 25° C. for 3 hr to give (2S,5S)-5-methyl-2-(6-methyl-3-pyridyl)piperidin-4-one (3 g, crude, 2TFA).
¹H NMR (500 MHz, DMSO-d₆) δ 1.01 (d, 3H), 2.63 (s, 3H), 2.92 (m, 1H), 3.19 (m, 2H), 3.71 (m, 1H), 4.92 (m, 1H), 7.73 (d, 1H), 8.24 (d, 1H), 8.74 (s, 1H).
LCMS(ESI): [M+H]⁺ m/z: calcd 204.2; found 205.2; Rt=0.311 min.

Step 6: The Synthesis of rac-5-[(2S,5S)-4,4-difluoro-5-methyl-2-piperidyl]-2-methyl-pyridine rac-(2S,5S)-5-methyl-2-(6-methyl-3-pyridyl)piperidin-4-one (3 g, 6.97 mmol, 2TFA), HF (1.39 g, 69.72 mmol) and Sulfur tetrafluoride (1.51 g, 13.94 mmol) were heated in a stainless steel autoclave at 70° C. for 12 hr. After completion of the reaction, the gaseous products were vented off, the reaction mixture was poured onto ice and neutralized with a 10% aqueous solution of K₂CO₃. The product was extracted with MTBE (3×100 mL). Combined organic extracts were washed with brine, dried over Na₂SO₄, and concentrated under reduced pressure to give 5-[(2S,5S)-4,4-difluoro-5-methyl-2-piperidyl]-2-methyl-pyridine (1.5 g, 6.63 mmol, 95.09% yield) which was used in the next step without further purification.
The structure was confirmed by 2D NMR.
¹H NMR (400 MHz, CDCl₃) δ 1.02 (d, 3H), 1.79 (m, 1H), 1.88 (m, 2H), 2.52 (s, 3H), 2.67 (t, 1H), 3.07 (m, 1H), 3.86 (m, 1H), 7.11 (d, 1H), 7.58 (d, 1H), 8.45 (s, 1H).
LCMS(ESI): [M+H]⁺ m/z: calcd 226.2; found 227.0; Rt=0.540 min.

3VV. The Synthesis of 6-(4-fluorophenyl)-5-azaspiro 2.5 octane

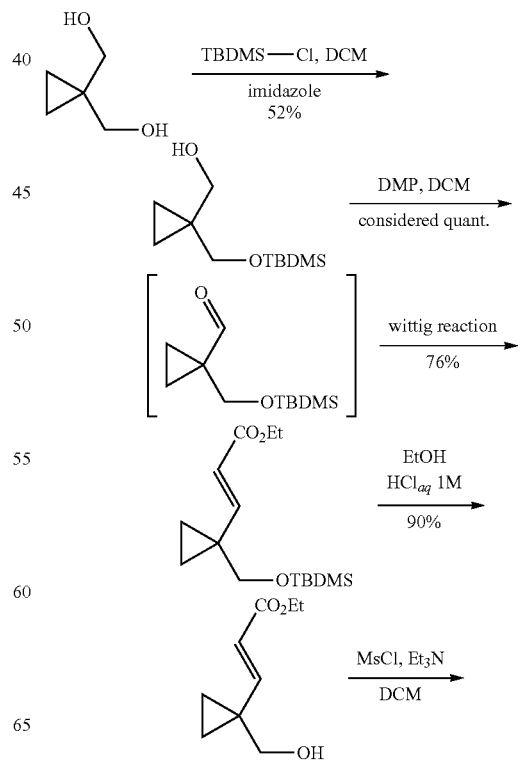

983

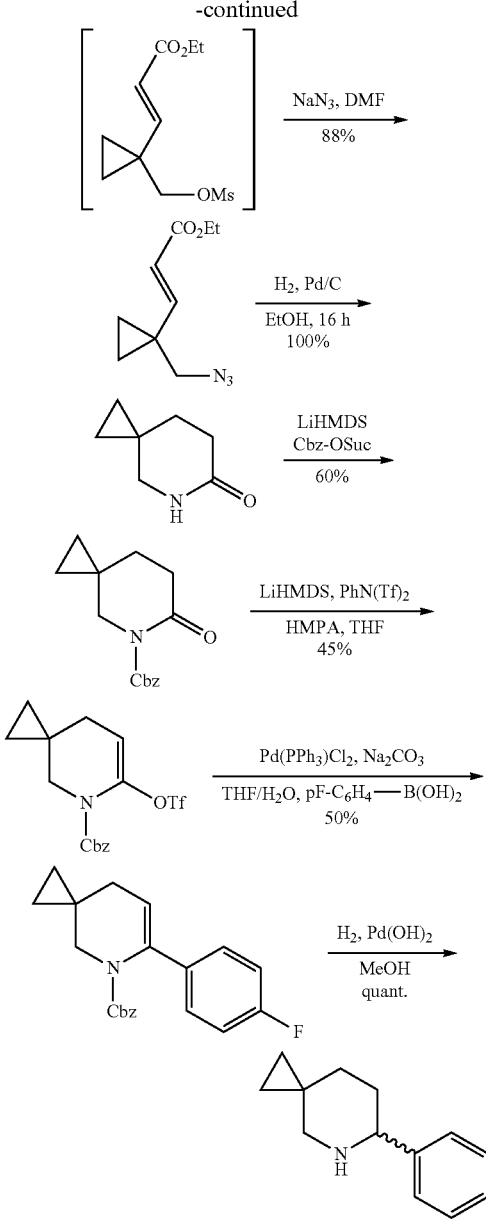

Step 1: Synthesis of (1-(((tert-butyldimethylsilyl)oxy)methyl)cyclopropyl)methanol t-butyldimethylsilyl chloride (15.50 g, 102.81 mmol) was added to a stirred solution of compound 1 (10.00 g, 97.92 mmol) and imidazole (10.00 g, 146.90 mmol) in $CH_2Cl_2$ (816 mL) at 0-C. The mixture was stirred at rt (16 hours). The reaction mixture was quenched by adding a saturated aqueous $NaHCO_3$ solution (250 mL). The mixture was extracted using an EtOAc (3×), dried over $MgSO_4$, filtered, and then concentrated. The residue was purified by silica gel column chromatography (EtOAc/hexane, 1:5) to give compound 3 (11.00 g, 52%) as a colorless oil.

$^1$H NMR (CDCl$_3$, 400 MHz) δ 3.61 (s, 2H), 3.56 (d, J=5.3 Hz, 2H), 2.75 (t, J=5.3 Hz, 1H), 0.90 (s, 9H), 0.51-044 (m, 4H), 0.05 (s, 6H).

984

Step 2: Synthesis of 1-(((tert-butyldimethylsilyl)oxy)methyl)cyclopropane-1-carbaldehyde Dess-Martin periodinane (13.80 g, 32.5 mmol) is added to an ice-cold solution of (1-(((tert-butyldimethylsilyl)oxy)methyl)cyclopropyl)methanol (2) (6.40 g, 29.60 mmol) in $CH_2C_2$ (296 mL). The reaction mixture is stirred at room temperature for 1 h, diluted with a mixed saturated aqueous $Na_2S_2O_3$ solution (200 mL) and saturated aqueous $NaHCO_3$ solution (200 mL) then extracted with ether (3×200 mL). The combined organic phases are washed with brine, dried ($Na_2SO_4$), filtered and concentrated under reduced pressure. The residue was used with no further purification.

Step 3: Synthesis of ethyl (E)-3-(1-(((Tert-butyldimethylsilyl)oxy)methyl)cyclopropyl)acrylate To a solution of sodium hydride (1.54 mg, 38.50 mmol, 60% in oil) in tetrahydrofuran (75 mL), triethylphosphoric acid ethyl ester (7.96 g, 35.50 mmol) was added dropwise, and the mixture was warmed to room temperature for 20 min. A solution of 1-(((tert-butyldimethylsilyl)oxy)methyl)cyclopropane-1-carbaldehyde (3) (6.35 g, 29.60 mmol) in tetrahydrofuran (39 mL) was added dropwise to the previous solution. After the addition was completed, the reaction was carried out for 2 hours at room temperature. Water (150 mL) was added to the reaction mixture, and the volatiles were evaporated. The mixture was extracted using an $CH_2C_2$ (3×), dried over $MgSO_4$, filtered, and then concentrated. The residue was purified by silica gel column chromatography (EtOAc/hexane, 0/1 to 1:3) to give ethyl (E)-3-(1-(((tert-butyldimethylsilyl)oxy)methyl)cyclopropyl)acrylate (4) (6.700 g, 80%) as a colorless oil.

$^1$H NMR (CDCl$_3$, 400 MHz) δ 6.66 (d, J=15.9 Hz, 1H), 5.82 (d, J=15.9 Hz, 1H), 4.17 (q, J=7.2 Hz, CH$_3$CH$_2$O), 3.66 (s, 2H), 1.28 (t, J=7.2 Hz, CH$_3$CH$_2$O), 0.97-0.93 (m, 2H), 0.88 (s, 9H), 0.80-0.76 (m, 2H), 0.05 (s, 3H).

Step 4: Synthesis of ethyl (E)-3-(1-(hydroxymethyl)cyclopropyl)acrylate

1 M aqueous HCl solution (1.18 mL, 1.18 mmol) was added to an ethanol (62 mL, 1 M) solution of ethyl (E)-3-(1-(((tert-butyldimethylsilyl)oxy)methyl)cyclopropyl)acrylate (4) (6.70 g, 23.55 mmol). The solution was stirred at room temperature (4 h). The volatiles were evaporated and the residue was purified by silica gel column chromatography (EtOAc/hexane, 0/1 to 5/5) to give ethyl (E)-3-(1-(hydroxymethyl)cyclopropyl)acrylate (5) (6.700 g, 80%) as a colorless oil.

$^1$H NMR (CDCl$_3$, 400 MHz) δ 6.62 (d, J=15.9 Hz, 1H), 5.96 (d, J=15.9 Hz, 1H), 4.17 (q, J=7.1 Hz, CH$_3$CH$_2$O), 3.66 (s, 2H), 1.28 (t, J=7.1 Hz, CH$_3$CH$_2$O), 0.97-0.92 (m, 2H), 0.91-0.87 (m, 2H).

Step 5: Synthesis of ethyl (E)-3-(1-(((methylsulfonyl)oxy)methyl)cyclopropyl)acrylate Mesyl chloride (1.81 mL, 23.30 mmol) was added dropwise to a $CH_2C_2$ (39 mL, 0.5 M) solution of DMAP (237 mg, 1.94 mmol), triethylamine (7.57 mL, 54.30 mmol) and ethyl (E)-3-(1-(hydroxymethyl)cyclopropyl)acrylate (5) (3.30 g, 19.40 mmol) at 0° C. The reaction was stirred at room temperature (2 h). A saturated aqueous solution of NaHCO$_3$ (30 mL) was added. The layers were separated and the aqueous layer was washed with $CH_2C_2$ (×2). The organic

Step 6: Synthesis of ethyl (E)-3-(1-(azidomethyl)cyclopropyl)acrylate

The crude (E)-3-(1-(methylsulfonyloxymethyl)cyclopropyl)prop-2-enoate (6) (4.54 g, 19.4 mmol) obtained in the previous step was added to the reaction flask, dimethylformamide (16.2 mL) and sodium azide (2.52 g, 38.8 mmol). The mixture was stirred at RT (o/n). The DMF was concentrated under vacuum and Ethyl acetate and water were added. The layers were separated and the aqueous layer was washed with Ethyl acetate (2×). The organic layers were combined, dried ($Na_2SO_4$) and concentrated under vacuum. The residue was purified by silica gel column chromatography (EtOAc/Cyclohexane) to give ethyl (E)-3-(1-(azidomethyl)cyclopropyl)acrylate (7) yellow oil (18.0 g, yield 92.3%).

$^1$H NMR ($CDCl_3$, 400 MHz) δ 6.56 (d, J=15.9 Hz, 1H), 5.90 (d, J=15.9 Hz, 1H), 4.19 (q, J=7.1 Hz, $CH_3CH_2O$, 2H), 3.36 (s, 2H), 1.29 (t, J=7.1 Hz, $CH_3CH_2O$), 1.03-1.00 (m, 2H), 0.97-0.94 (m, 2H).

Step 7: Synthesis of 5-azaspiro[2.5]octan-6-one

To an ethanol (48 mL) solution of ethyl (E)-3-(1-(azidomethyl)cyclopropyl)prop-2-enoate (7) (2.6 g, 14.0 mmol) was added Pd/c (260 mg). The reaction mixture was stirred under $H_2$ atmosphere (balloon) (16 h). The reaction mixture was filtered trough a seringue filter and the filtrate was concentrated under vacuum. 5-azaspiro[2.5]octan-6-one (8) was obtained as a wax white solid (1.60 g, 89%).

$^1$H NMR ($CDCl_3$, 400 MHz) δ 6.69-6.57 (br s, 1H), 3.09 (d J=1.9 Hz, 2H), 2.43 (t, J=6.6 Hz, 2H), 1.61 (t, J=6.6 Hz, 2H), 0.49 (s, 4H).

Step 8: Synthesis of Benzyl 6-oxo-5-azaspiro[2.5]octane-5-carboxylate 5-azaspiro[2.5]octan-6-one (8) (1.0 g, 8.0 mmol) was dissolved in THF (100 mL) and LiHMDS (10.4 mL of a 1 M solution in THF, 10.4 mmol) was added at 78° C. After stirring for 30 min, Cbz-OSu (2.6 g, 10.4 mmol) was added and the resulting mixture was stirred overnight at room temperature. The reaction was quenched with water (30 mL) and $CH_2C_2$ (30 mL). The layers were separated and the aqueous layer was washed with $CH_2C_2$ (2*30 mL). The combined organic layers were dried ($Na_2SO_4$), filtered, and concentrated in vacuo. The residue was purified by silica gel column chromatography (10/0 Cyclohexane/Ethylacetate to 6/4) to give benzyl 6-oxo-5-azaspiro[2.5]octane-5-carboxylate (9) as a colorless oil (400 mg, 20%)

$^1$H NMR ($CDCl_3$, 400 MHz) δ 7.46-7.29 (m, 5H), 5.27 (s, 2H), 3.51 (s, 2H), 2.65 (t, J=6.9 Hz, 2H), 1.69 (t, J=6.9 Hz, 2H), 0.62-0.57 (m, 2H), 0.55-0.51 (m, 2H).

Step 9: Synthesis of Benzyl 6-(((trifluoromethyl)sulfonyl)oxy)-5-azaspiro[2.5]oct-6-ene-5-carboxylate A solution of benzyl 6-oxo-5-azaspiro[2.5]octane-5-carboxylate (9) (200 mg, 0.83 mmol) in anhydrous THE (4.8 mL) was cooled to −78° C. A 1 M solution of LiHMDS (1.04 mL of a 1 M solution in THF, 1.04 mmol) was added over 5 min, and the mixture was stirred for 70 min. Distilled HMPA (288 μL, 1.66 mmol) was added, the solution was stirred for an additional 30 min, and then a solution of $PhNTf_2$ (370 mg, 1.04 mmol) in anhydrous THE (0.5 mL) was added and the mixture allowed to warm to room temperature and left to react for 15 h. Water (10 mL) and ether (10 mL) were added, and the layers were separated. The aqueous layer was washed with ether (2*30 mL). The combined organic layers were dried ($Na_2SO_4$), filtered, and concentrated in vacuo. The residue was purified by silica gel column chromatography (10/0 Cyclohexane/Ethylacetate to 6/4) to give benzyl 6-(((trifluoromethyl)sulfonyl)oxy)-5-azaspiro[2.5]oct-6-ene-5-carboxylate (10) as a colorless oil ( ).

$^1$H NMR ($CDCl_3$, 400 MHz) δ 7.40-7.32 (m, 5H), 5.38 (d, J=3.8 Hz, 1H), 5.22 (s, 2H), 3.47 (s, 2H), 2.16 (d, J=3.8 Hz, 2H), 0.62-0.56 (m, 2H), 0.44-0.40 (m, 2H).

Step 10: Synthesis of benzyl 6-(4-fluorophenyl)-5-azaspiro[2.5]oct-6-ene-5-carboxylate To a solution of -(((trifluoromethyl)sulfonyl)oxy)-5-azaspiro[2.5]oct-6-ene-5-carboxylate (140 mg, 0.36 mmol) in THF (6 mL) was added, under a nitrogen atmosphere, $(Ph_3P)_2PdCl_2$ (13 mg, 17.9 μmol), (4-fluorophenyl)boronic acid (65 mg, 0.46 mmol), and a 2 M aqueous $Na_2CO_3$ solution (3.58 mL). The mixture was stirring for 16 h at 40° C. Water (10 mL) was then added and the mixture was extracted with diethylether and dried ($Na_2SO_4$). The residue was purified by silica gel column chromatography (10/0 Cyclohexane/Ethylacetate to 1/9) to give benzyl 6-(4-fluorophenyl)-5-azaspiro[2.5]oct-6-ene-5-carboxylate (11) as colorless oil (60 mg, 50%)

$^1$H NMR ($CDCl_3$, 400 MHz) δ 7.47-7.15 (m, 7H), 6.93 (d, J=8.6 Hz, 2H), 5.40 (d, J=3.7 Hz, 1H), 4.94 (s, 2H), 3.57 (s, 2H), 2.19 (d, J=3.7 Hz, 2H), 0.66-0.59 (m, 2H), 0.45-0.40 (m, 2H).

Step 11: Synthesis of 6-(4-fluorophenyl)-5-azaspiro[2.5]octane $Pd(OH)_2$ on charcoal (10%, 6 mg) was added to a (2,2,2)-trifluoroethanol (1.2 mL) solution of 6-(4-fluorophenyl)-5-azaspiro[2.5]oct-6-ene-5-carboxylate (11) (60 mg, 0.18 mmol). the solution was stirred at Room temperature under $H_2$ atm (1 atm) (16 h). The reaction mixture was filtered trough a seringue filter. The filter was washed with (2,2,2)-trifluoroethanol. The volatiles were evaporated to give 6-(4-fluorophenyl)-5-azaspiro[2.5]octane as colorless oil (35 mg, 96%)

$^1$H NMR ($CDCl_3$, 400 MHz) δ 7.34 (dd, J=5.6, 8.7 Hz, 7H), 7.00 (d, J=8.7 Hz, 2H), 3.64 (dd, J=2.6, 11.3 Hz, 1H), 3.24 (dd, J=1.1 12.3 Hz, 1H), 2.25 (dd, J=2.1, 12.3 Hz, 1H), 2.05-1.98 (m, 1H), 1.89-1.81 (m, 1H), 1.75-1.64 (m, 1H), 1.12-1.03 (m, 1H), 0.53-0.45 (m, 1H), 0.40-0.30 (m, 3H).

3WW. 1-methyl-6-(5-methyl-2-piperidyl)-3,4-dihydroquinolin-2-one

Step 1: The Synthesis of 1-methyl-6-(4,4,5,5-tetramethyl-1,3,2-dioxaborolan-2-yl)-3,4-dihydroquinolin-2-one

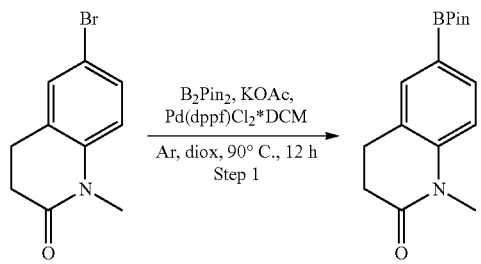

A mixture of 6-bromo-1-methyl-3,4-dihydroquinolin-2-one (5.18 g, 21.57 mmol), bis(pinacolato)diboron (6.57 g, 25.89 mmol) and Potassium Acetate (6.35 g, 64.72 mmol, 4.05 mL) in Dioxane (50 mL) was degassed with argon for 10 min. Pd(dppf)Cl$_2$*DCM (880.93 mg, 1.08 mmol) was next added and the reaction mixture was heated at 90° C. for 12 hr. Reaction mixture was cooled to RT and filtered, then evaporated. Crude product was treated with mixture of hexane:mtbe (8:2), and subjected to flash column chromatography (eluent chloroform). 1-methyl-6-(4,4,5,5-tetramethyl-1,3,2-dioxaborolan-2-yl)-3,4-dihydroquinolin-2-one (4.6 g, 16.02 mmol, 74.25% yield) was obtained.

LCMS(ESI): [M+H]$^+$ m/z: calcd 288.2; found 288.2; Rt=1.321 min.

Step 2: The Synthesis of tert-butyl 3-methyl-6-(1-methyl-2-oxo-3,4-dihydroquinolin-6-yl)-3,4-dihydro-2H-pyridine-1-carboxylate

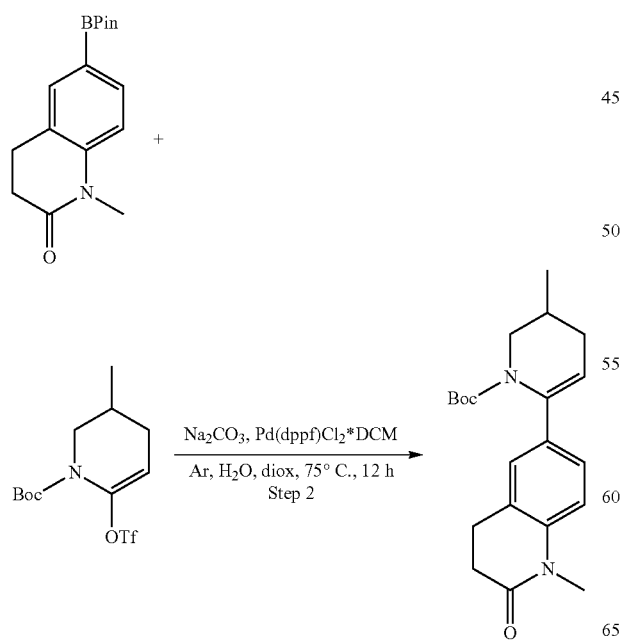

1-methyl-6-(4,4,5,5-tetramethyl-1,3,2dioxaborolan-2-yl)-3,4-dihydroquinolin-2-one (4.2 g, 14.63 mmol), tert-butyl 3-methyl-6-(trifluoromethylsulfonoxy)-3,4-dihydro-2H-pyridine-1-carboxylate (7.07 g, 20.48 mmol), Sodium carbonate (4.65 g, 43.88 mmol, 1.84 mL) and Pd(dppf)Cl$_2$*DCM (1.19 g, 1.46 mmol) were mixed in H$_2$O (20 mL) and dioxane (60 mL), purged with argon and stirred at 75° C. for 12 hr. Reaction mixture was diluted with water and needed product was extracted with DCM, dried over Na$_2$SO$_4$ and concentrated in vacuo. tert-butyl 3-methyl-6-(1-methyl-2-oxo-3,4-dihydroquinolin-6-yl)-3,4-dihydro-2H-pyridine-1-carboxylate, (8 g, crude), was obtained.

LCMS(ESI): [M+H]$^+$ m/z: calcd 357.2; found 357.4; Rt=1.437 min.

Step 3: The Synthesis of 1-methyl-6-(3-methyl-2,3,4,5-tetrahydropyridin-6-yl)-3,4-dihydroquinolin-2-one

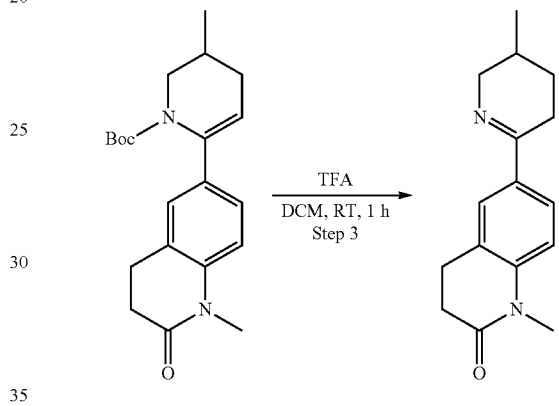

tert-butyl 3-methyl-6-(1-methyl-2-oxo-3,4-dihydroquinolin-6-yl)-3,4-dihydro-2H-pyridine-1-carboxylate (8 g, 11.22 mmol) was dissolved in CF$_3$COOH (10 g, 11.22 mmol) and stirred for 1 hr at 20° C. Then reaction mixture was concentrated, treated with aq. solution of NaHCO$_3$ and extracted with DCM, then evaporated to give 1-methyl-6-(3-methyl-2,3,4,5-tetrahydropyridin-6-yl)-3,4-dihydroquinolin-2-one (4 g, crude).

LCMS(ESI): [M+H]$^+$ m/z: calcd 257.2; found 257.2; Rt=0.674 min.

Step 4: The Synthesis of 1-methyl-6-(5-methyl-2-piperidyl)-3,4-dihydroquinolin-2-one

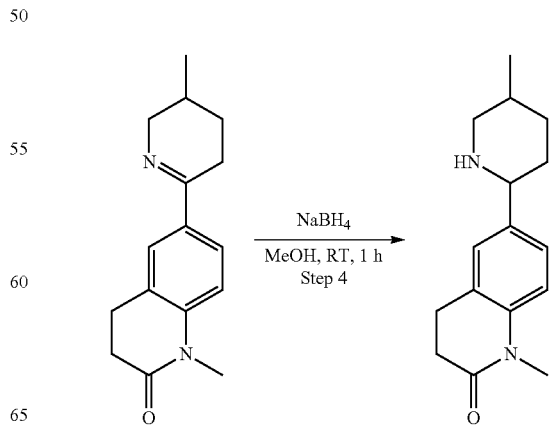

1-methyl-6-(3-methyl-2,3,4,5-tetrahydropyridin-6-yl)-3,4-dihydroquinolin-2-one (4 g, 7.33 mmol) was dissolved in methanol (40 mL) and Sodium Borohydride (554.92 mg, 14.67 mmol, 518.62 uL) was added. After 1 hr, the reaction mixture was concentrated, treated with aq. solution of NaHCO$_3$ and extracted with DCM. Organic phase was evaporated to give 1-methyl-6-(5-methyl-2-piperidyl)-3,4-dihydroquinolin-2-one (2.9 g, crude).

LCMS(ESI): [M+H]$^+$ m/z: calcd 259.2; found 259.2; Rt=0.717 min.

3XX. rac-6-((2R,5S)-5-methylpiperidin-2-yl)imidazo[1,5-a]pyridine

Step 1: Synthesis of tert-butyl 6-(imidazo[1,5-a]pyridin-6-yl)-3-methyl-3,4-dihydropyridine-1(2H)-carboxylate

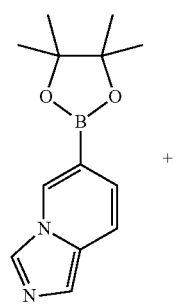

+

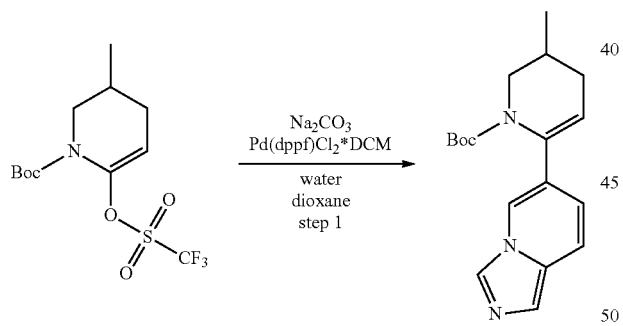

tert-butyl 3-methyl-6-(trifluoromethylsulfonyloxy)-3,4-dihydro-2H-pyridine-1-carboxylate (100 mg, 289.57 umol), 6-(4,4,5,5-tetramethyl-1,3,2-dioxaborolan-2-yl)imidazo[1,5-a]pyridine (70.68 mg, 289.57 umol) and sodium carbonate (92.08 mg, 868.72 umol, 36.39 uL) were added to a mixture of 1,4-dioxane (3 mL) and water (1 mL). The resulting mixture was evacuated and then backfilled with argon, then Pd(dppf)Cl$_2$*DCM (11.81 mg, 14.48 umol) was added under argon. The reaction mixture was stirred at 80° C. for 16 hr, then treated with water and needed product was extracted with DCM, then evaporated. tert-butyl 6-imidazo[1,5-a]pyridin-6-yl-3-methyl-3,4-dihydro-2H-pyridine-1-carboxylate (150 mg, crude) was obtained.

LCMS(ESI): [M]$^+$ m/z: calcd 313.2; found 314.2; Rt=1.044 min.

Step 2: Synthesis of 6-(5-methyl-3,4,5,6-tetrahydropyridin-2-yl)imidazo[1,5-a]pyridine

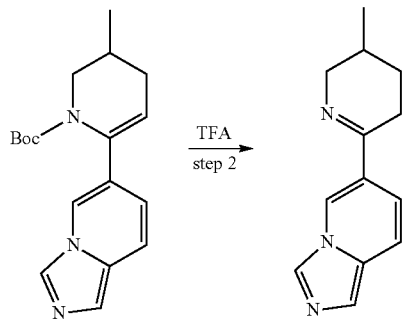 [SMILES: CC1CC=C(c2ccc3cncn3c2)N(C(=O)OC(C)(C)C)C1 ; CC1CCC(c2ccc3cncn3c2)=NC1]

tert-butyl 6-imidazo[1,5-a]pyridin-6-yl-3-methyl-3,4-dihydro-2H-pyridine-1-carboxylate (3 g, 9.57 mmol) was dissolved in TFA (20 mL) and stirred for 1 hr at 25° C. Reaction mixture was concentrated in vacuum, crude product was dissolved in aqueous NaHCO$_3$ and extracted with DCM (50 ml). Organic phase was washed with water, dried over Na$_2$SO$_4$ and evaporated to give 6-(3-methyl-2,3,4,5-tetrahydropyridin-6-yl)imidazo[1,5-a]pyridine (3 g, crude).

LCMS(ESI): [M]$^+$ m/z: calcd 213.2; found 214.2; Rt=0.520 min.

Step 3: Synthesis of rac-6-((2R,5S)-5-methylpiperidin-2-yl)imidazo[1,5-a]pyridine

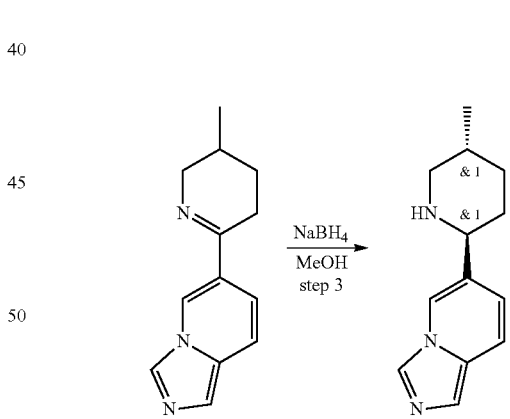

6-(3-methyl-2,3,4,5-tetrahydropyridin-6-yl)imidazo[1,5-a]pyridine (3 g, 14.07 mmol) crude from previous stage was dissolved in methanol (40 mL) and then sodium borohydride (800.00 mg, 21.15 mmol, 747.66 uL) was added. Reaction mixture was stirred overnight and then evaporated. Crude product was dissolved in DCM (100 ml) washed with water twice, dried over Na$_2$SO$_4$ and then concentrated in vacuum to give 6-[(2R,5S)-5-methyl-2-piperidyl]imidazo[1,5-a]pyridine (2.25 g, crude).

LCMS(ESI): [M]$^+$ m/z: calcd 215.2; found 216.2; Rt=0.465 min.

3YY. rac-5-((2R,5S)-5-methylpiperidin-2-yl)-1H-thieno[2,3-c]pyrazole

Step 1: Synthesis of 1-(tetrahydro-2H-pyran-2-yl)-1H-thieno[2,3-c]pyrazole-5-carboxylic acid

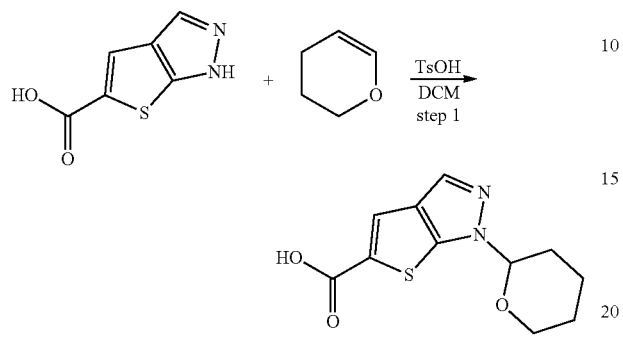

1H-thieno[2,3-c]pyrazole-5-carboxylic acid (5 g, 29.73 mmol) was suspended in 3,4-dihydro-2H-pyran (25.01 g, 297.31 mmol, 27.01 mL), followed by the addition of toluenesulfonic acid (255.99 mg, 1.49 mmol). After 0.5 hr of intensive stirring all solids were dissolved; clear solution was evaporated to dryness and the crude residue was dissolved in 50% aq KOH. Obtained milky suspension was washed with DCM (30 mL) five times and with MTBE (30 mL)$_2$ times. The clear light-yellow solution was acidified with 10% aq NaHSO$_4$ to pH=2 and extracted with DCM (30 mL)$_2$ times. Evaporation of the combined organic solvents results in 1-tetrahydropyran-2-ylthieno[2,3-c]pyrazole-5-carboxylic acid (7.2 g, 28.54 mmol, 95.99% yield) as mixture of regioisomers.

$^1$H NMR (500 MHz, DMSO-d$_6$) δ (ppm) 1.95 (m, 6H), 3.86 (m, 2H), 5.56 (m, 1H), 7.68 (s, 1H), 8.28 (s, 1H), 13.25 (bds, 1H).

LCMS(ESI): [M]$^+$ m/z: calcd 252.2; found 253.2; Rt=1.089 min.

Step 2: Synthesis of (1H-imidazol-1-yl)(1-(tetrahydro-2H-pyran-2-yl)-1H-thieno[2,3-c]pyrazol-5-yl)methanone

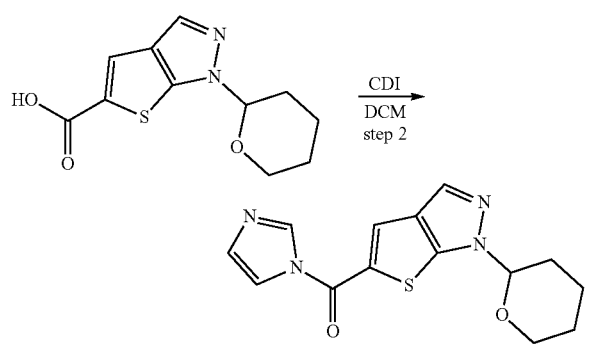

1-tetrahydropyran-2-ylthieno[2,3-c]pyrazole-5-carboxylic acid (7.2 g, 28.54 mmol) was dissolved in DCM (100 mL), followed by the addition of CDI (6.94 g, 42.81 mmol) in one portions. After the reaction was complete (concluded by finished evolution of gaseous by-products and by H-NMR) the mixture was diluted with DCM (100 mL) and washed with 0.1 M aq HCl (three times). Evaporation of the organic solvent under reduced pressure results in imidazol-1-yl-(1-tetrahydropyran-2-ylthieno[2,3-c]pyrazol-5-yl)methanone (5.8 g, 19.18 mmol, 67.22% yield) which was used in the next step immediately.

$^1$H NMR (500 MHz, DMSO-d$_6$) δ (ppm) 1.95 (m, 6H), 3.82 (m, 1H), 4.08 (m, 1H), 5.62 (m, 1H), 7.19 (s, 1H), 7.69 (s, 1H), 7.82 (s, 1H), 8.12 (s, 1H), 8.32 (s, 1H).

Step 3: Synthesis of tert-butyl 5-methyl-2-oxo-3-(1-(tetrahydro-2H-pyran-2-yl)-1H-thieno[2,3-c]pyrrazole-5-carbonyl)piperidine-1-carboxylate

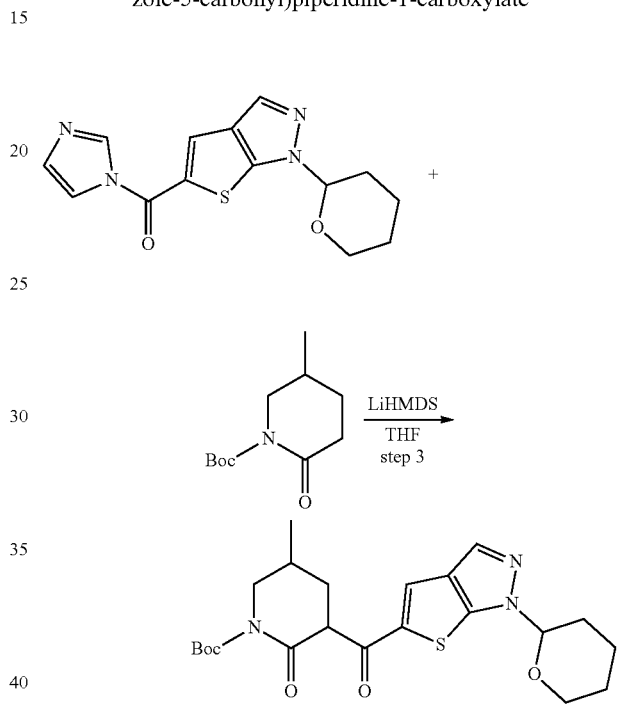

tert-butyl 5-methyl-2-oxo-piperidine-1-carboxylate (4.50 g, 21.10 mmol) was dissolved in THF (40 mL) and cooled to −78° C. under Ar, followed by the addition of lithium hexamethyldisilazide (1.03 M, 22.35 mL) in a dropwise manner. After additional stirring for 10 min, the solution of imidazol-1-yl-(1-tetrahydropyran-2-ylthieno[2,3-c]pyrazol-5-yl)methanone (5.8 g, 19.18 mmol) in THF (40 mL) was added and the reaction mixture was warmed to rt. After the reaction was complete, the mixture was poured on sat aq NH$_4$Cl and extracted with EtOAc (100 mL) three times. Evaporation of the organic solvents and purification with CC (OK. Interchim; 220 g SiO$_2$, petroleum ether/ethyl acetate with ethyl acetate from 10~75%, flow rate=100 mL/min, Rv=7.7 CV) results in tert-butyl 5-methyl-2-oxo-3-(1-tetrahydropyran-2-ylthieno[2,3-c]pyrazole-5-carbonyl)piperidine-1-carboxylate (4.5 g, 10.05 mmol, 52.42% yield) as mixture of isomers. Separate fractions were combined and used in the next step.

$^1$H NMR (500 MHz, CDCl$_3$) δ (ppm) 1.08 (d, 3H), 1.53 (s, 9H), 1.62 (m, 4H), 2.15 (m, 6H), 3.23 (m, 1H), 3.85 (m, 2H), 4.39 (m, 1H), 5.55 (m, 1H), 7.86 (m, 2H).

LCMS(ESI): [M-Boc]$^+$ m/z: calcd 347.2; found 348.2; Rt=1.384 min.

Step 4: Synthesis of 5-(5-methyl-3,4,5,6-tetrahydropyridin-2-yl)-1H-thieno[2,3-c]pyrazole

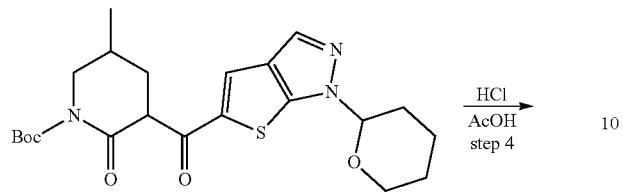

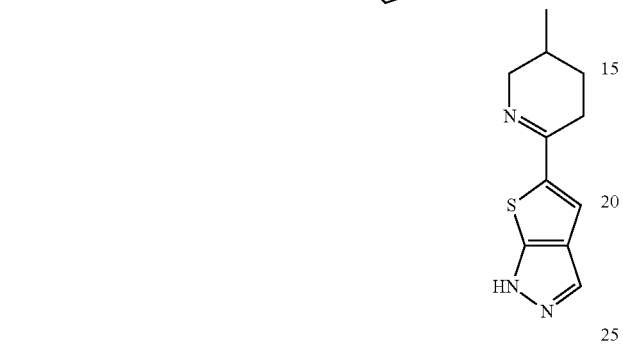

tert-butyl 5-methyl-2-oxo-3-(1-tetrahydropyran-2-ylthieno[2,3-c]pyrazole-5-carbonyl)piperidine-1-carboxylate (4.5 g, 10.05 mmol) was dissolved in acetic acid (50 mL) and heated to reflux. HCl (10 M, 10.05 mL) was added dropwise (Caution! Intensive foaming was observed!). After gas evolution was stopped, the mixture was evaporated to dryness, dissolved in $H_2O$ (50 mL) and basified to pH=10 with 10% aq $K_2CO_3$; obtained opaque solution was extracted with DCM (150 mL), which was dried over $Na_2SO_4$ and evaporated under reduced pressure to give 5-(3-methyl-2,3,4,5-tetrahydropyridin-6-yl)-1H-thieno[2,3-c]pyrazole (1.6 g, 7.30 mmol, 72.56% yield).

$^1$H NMR (400 MHz, CDCl$_3$) δ (ppm) 1.02 (d, 3H), 1.86 (m, 1H), 1.95 (m, 2H), 2.48 (m, 1H), 2.86 (m, 1H), 3.26 (m, 1H), 4.02 (m, 1H), 7.42 (m, 1H), 7.82 (m, 2H).

LCMS(ESI): [M]$^+$ m/z: calcd 219.2; found 220.2; Rt=0.802 min.

Step 5: Synthesis of rac-5-((2R,5S)-5-methylpiperidin-2-yl)-1H-thieno[2,3-c]pyrazole

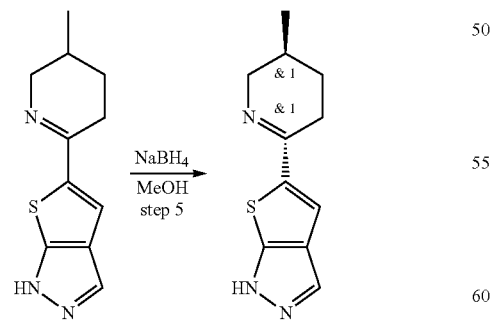

5-(3-methyl-2,3,4,5-tetrahydropyridin-6-yl)-1H-thieno[2,3-c]pyrazole (1.6 g, 7.30 mmol) was dissolved in MeOH (20 mL) and cooled to 0° C. Sodium borohydride (552.00 mg, 14.59 mmol, 515.89 uL) was added in portions to obtained mixture and additionally stirred overnight. After the reaction was complete, the reaction mixture was acidified with 10% aq HCl to pH=2, washed with MTBE (2*10 mL), basified with 10% aq NaOH to pH=10 and extracted with DCM (50 mL). Evaporation of the solvent result in pure 5-[(2S,5R)-5-methyl-2-piperidyl]-2H-thieno[2,3-c]pyrazole (1.3 g, 5.87 mmol, 80.511% yield).

$^1$H NMR (500 MHz, CDCl$_3$) δ (ppm) 0.98 (d, 3H), 1.56 (m, 2H), 1.68 (m, 2H), 1.92 (m, 1H), 2.02 (m, 1H), 2.44 (m, 1H), 3.20 (m, 1H), 3.86 (m, 1H), 6.83 (s, 1H), 7.61 (s, 1H).

LCMS(ESI): [M]$^+$ m/z: calcd 221.2; found 222.2; Rt=0.711 min.

3ZZ. N,N-dimethyl-2-(3-((SS)-5-methylpiperidin-2-yl)phenoxy)ethanamine

Step 1: Synthesis of (S)-tert-butyl 6-(3-(2-(dimethylamino)ethoxy)phenyl)-3-methyl-3,4-dihydropyridine-1(2H)-carboxylate

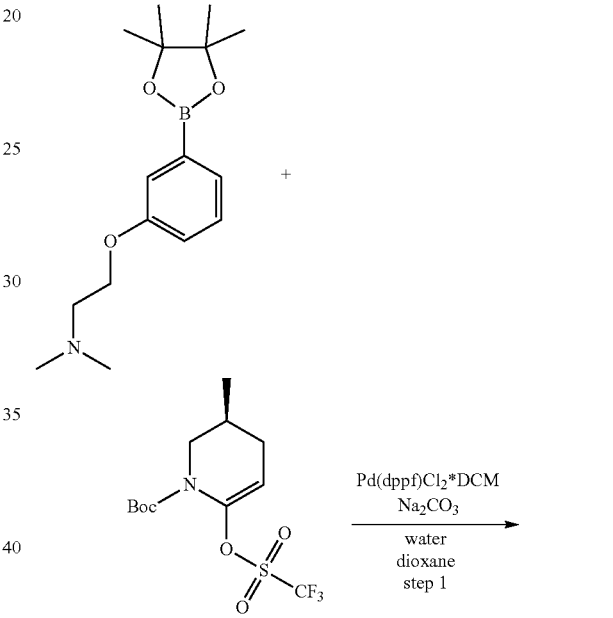

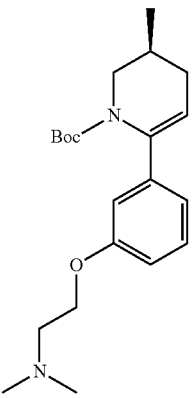

tert-butyl (3S)-3-methyl-6-(trifluoromethylsulfonyloxy)-3,4-dihydro-2H-pyridine-1-carboxylate (8 g, 23.17 mmol), N,N-dimethyl-2-[3-(4,4,5,5-tetramethyl-1,3,2-dioxaborolan-2-yl)phenoxy]ethanamine (5.62 g, 19.30 mmol) and sodium carbonate (4.09 g, 38.61 mmol, 1.62 mL) were mixed in a mixture of dioxane (45 mL) and water (15 mL). The resulting mixture was evacuated and backfilled three times with argon. Pd(dppf)Cl$_2$*DCM (788.26 mg, 965.25 μmol) was added to the previous mixture and the resulting mixture was heated at 90° C. overnight. The resulting mixture was cooled and diluted with water (100 ml). The resulting mixture was extracted with EtOAc (2*100 ml) and combined organic layers were washed with brine (60 ml), dried over Na₂SO₄, filtered, and concentrated in vacuum. The residue (10.8 g of crude product) was combined with the residue (200 mg of crude product) and purified by column chromatography to obtain tert-butyl (3S)-6-[3-[2-(dimethyl-amino)ethoxy]phenyl]-3-methyl-3,4-dihydro-2H-pyridine-1-carboxylate (4.5 g, 12.48 mmol, 64.66% yield).

LCMS(ESI): [M]⁺ m/z: calcd 360.2; found 361.2; Rt=1.077 min.

Step 2: Synthesis of (S)—N,N-dimethyl-2-(3-(5-methyl-3,4,5,6-tetrahydropyridin-2-yl)phenoxy)ethanamine

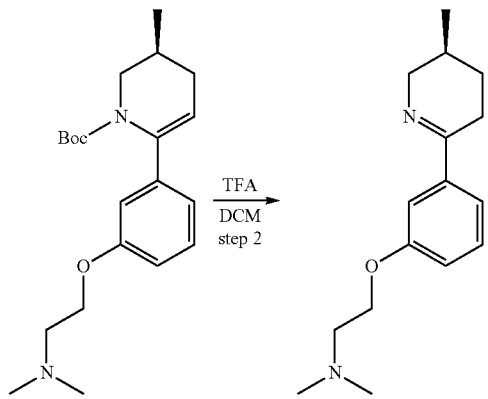 [SMILES: C[C@H]1CC=C(c2cccc(OCCN(C)C)c2)N(C(=O)OC(C)(C)C)C1 ; C[C@H]1CCC(c2cccc(OCCN(C)C)c2)=NC1]

tert-butyl (3S)-6-[3-[2-(dimethylamino)ethoxy]phenyl]-3-methyl-3,4-dihydro-2H-pyridine-1-carboxylate (4.5 g, 12.48 mmol) was dissolved in DCM (18 mL) and TFA (18 mL) was added thereto. The resulting mixture was stirred for 1 hr. The reaction mixture was carefully poured into aq·NaHCO₃ solution (20 g in 100 ml of water) and the resulting mixture was extracted with DCM (2*50 ml). Combined organic layers were dried over sodium sulfate, filtered, and concentrated in vacuum to obtain N,N-dimethyl-2-[3-[(3S)-3-methyl-2,3,4,5-tetrahydropyridin-6-yl]phenoxy]ethanamine (2.36 g, 9.04 mmol, 72.46% yield).

LCMS(ESI): [M]⁺ m/z: calcd 260.2; found 261.2; Rt=0.245 min.

Step 3: Synthesis of N,N-dimethyl-2-(3-((5S)-5-methylpiperidin-2-yl)phenoxy)ethanamine

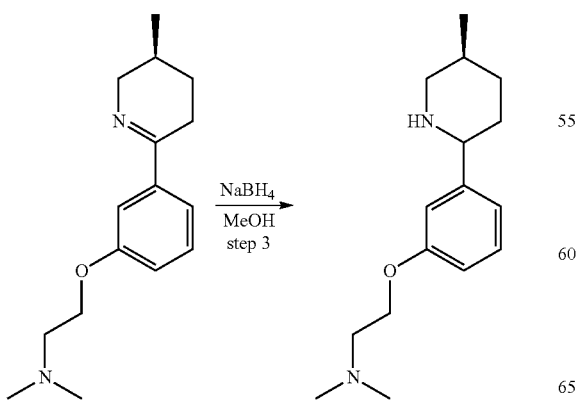

N,N-dimethyl-2-[3-[(3S)-3-methyl-2,3,4,5-tetrahydropyridin-6-yl]phenoxy]ethanamine (2.36 g, 9.06 mmol) was dissolved in MeOH (45 mL) and sodium borohydride (685.82 mg, 18.13 mmol, 638.57 µL) was added portion wise. The resulting mixture was stirred overnight.

Water (20 ml) was added to the reaction mixture and the resulting mixture was concentrated in vacuum. The residue was diluted with water (30 ml) and the resulting mixture was extracted with DCM (2*50 ml). Combined organic layers were dried over Na₂SO₄, filtered, and concentrated in vacuum to obtain N,N-dimethyl-2-[3-[(2R,5S)-5-methyl-2-piperidyl]phenoxy]ethanamine (2.02 g, 7.70 mmol, 84.94% yield).

LCMS(ESI): [M]⁺ m/z: calcd 262.2; found 263.2; Rt=0.498 min.

3AAA. 5-((2R,5S)-5-methylpiperidin-2-yl)-2-(2-(pyrrolidin-1-yl)ethyl)benzo[d]thiazole

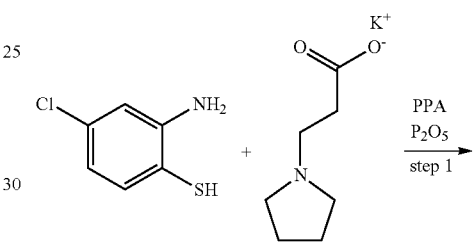

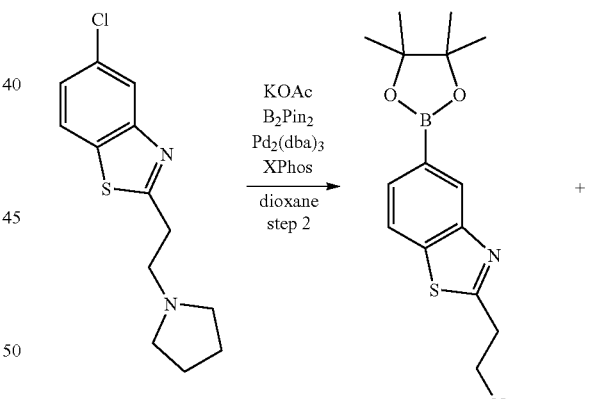

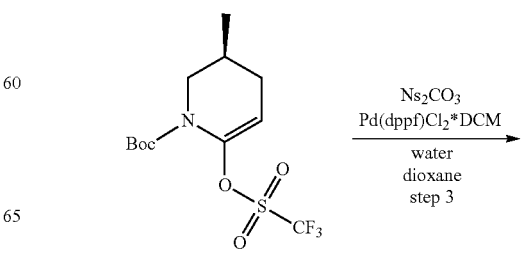

997

-continued

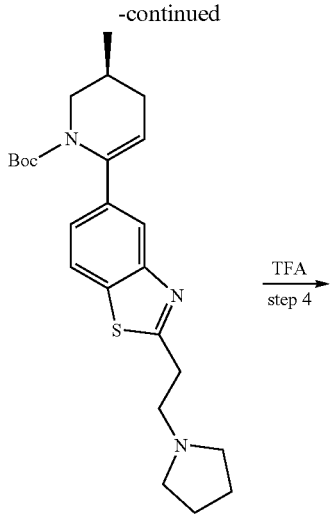

TFA
step 4

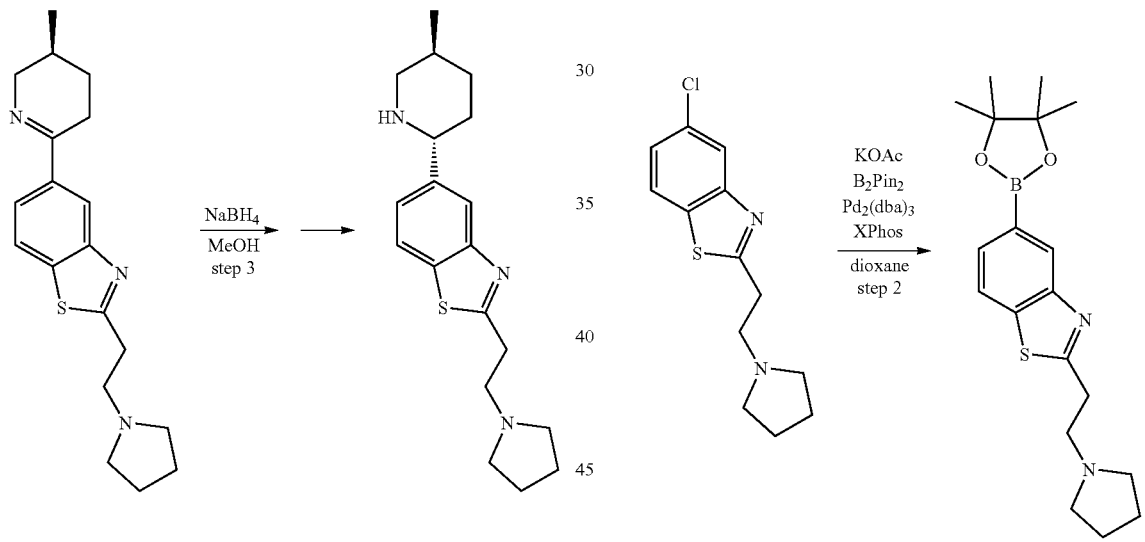

Step 1: Synthesis of 5-chloro-2-(2-(pyrrolidin-1-yl)ethyl)benzo[d]thiazole

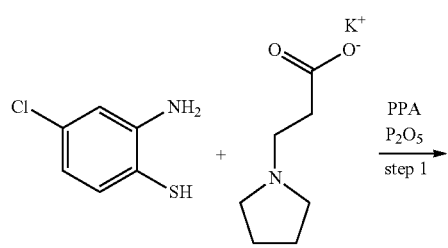

998

-continued

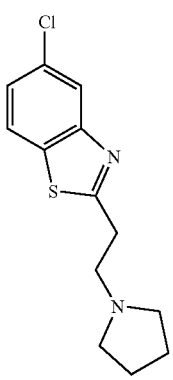

Prepared by general procedure Scheme J step 1A. Yield: 4.3 g (51.46%).

CC conditions: The crude product was purified by silica gel with MTBE/MeOH as an eluent mixture.

LCMS(ESI): [M]+ m/z: calcd 266.2; found 267.2; Rt=1.014 min.

Step 2: Synthesis of 2-(2-(pyrrolidin-1-yl)ethyl)-5-(4,4,5,5-tetramethyl-1,3,2-dioxaborolan-2-yl)benzo[d]thiazole Potassium acetate (3.16 g, 32.23 mmol, 2.01 mL) was added to a solution of 5-chloro-2-(2-pyrrolidin-1-ylethyl)-1,3-benzothiazole (4.30 g, 16.12 mmol) and 4,4,5,5-tetramethyl-2-(4,4,5,5-tetramethyl-1,3,2-dioxaborolan-2-yl)-1,3,2-dioxaborolane (4.50 g, 17.73 mmol) in dioxane (50 mL). Reaction flask was evacuated and refilled with argon 3 times. Then tris(dibenzylideneacetone)dipalladium(0) (737.96 mg, 805.88 umol) and XPhos (1.54 g, 3.22 mmol) was added under stream of argon. Resulting mixture was stirred at 90° C. for 18 hr under inert atmosphere. Then pyrrolidine 40% aqueous solution (0.5 eq.) was added and the reaction mixture was stirred at 60° C. another 12 hr. Then, it was cooled, diluted with EtOAc (200 mL) and washed with Na2CO3 (50 mL, sat. aq.). Organic layer was dried over Na2SO4, concentrated under reduced pressure and the residue was purified by silica gel flash chromatography eluting with a 0 to 100 percent CHCl3-MeCN-MeOH gradient to afford product 2-(2-pyrrolidin-1-ylethyl)-5-(4,4, 5,5-tetramethyl-1,3,2-dioxaborolan-2-yl)-1,3-benzothiazole (2.2 g, 6.14 mmol, 38.10% yield).

LCMS(ESI): [M]⁺ m/z: calcd 358.2; found 359.2; Rt=1.001 min.

Step 3: Synthesis of (S)-tert-butyl 3-methyl-6-(2-(2-(pyrrolidin-1-yl)ethyl)benzo[d]thiazol-5-yl)-3,4-dihydropyridine-1(2H)-carboxylate

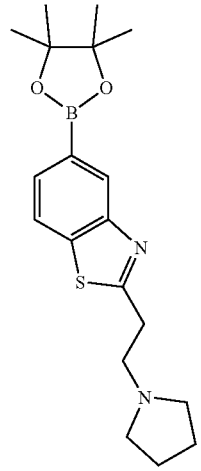

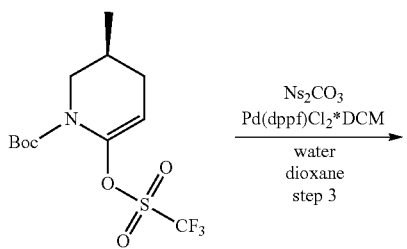

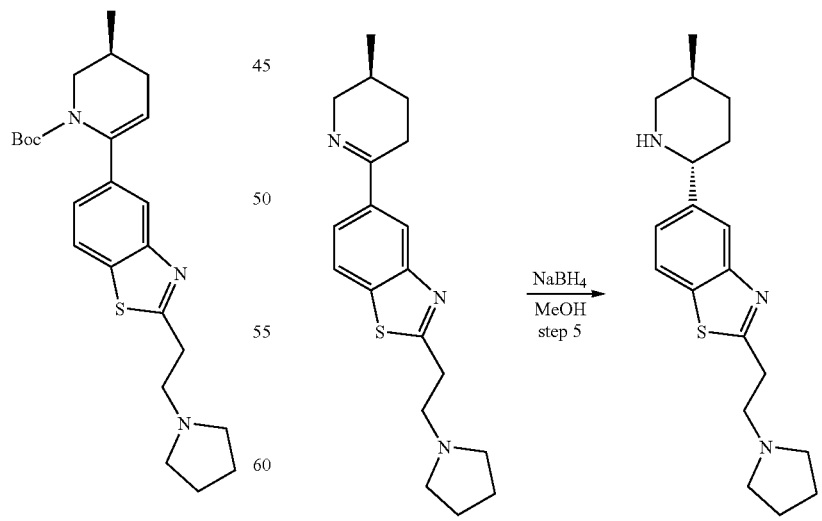

Prepared by general procedure Scheme J step 3. Yield: 3 g of crude.

LCMS(ESI): [M]⁺ m/z: calcd 427.2; found 428.2; Rt=1.251 min.

Step 4: Synthesis of (S)-5-(5-methyl-3,4,5,6-tetra-hydropyridin-2-yl)-2-(2-(pyrrolidin-1-yl)ethyl)benzo[d]thiazole

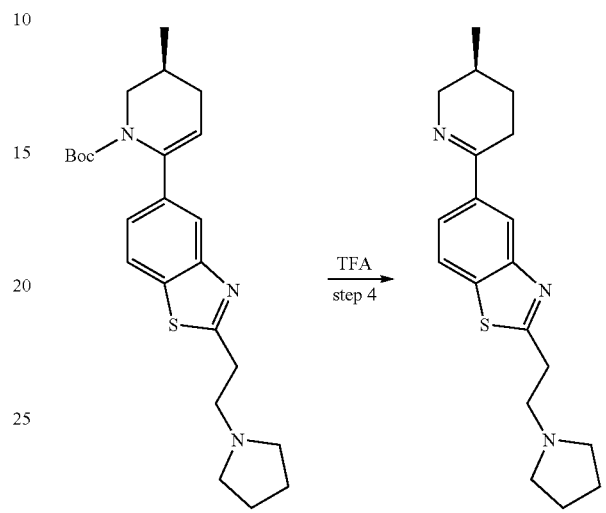

Prepared by general procedure Scheme J step 4. Yield: 1.2 g of crude.

LCMS(ESI): [M]⁺ m/z: calcd 327.2; found 328.2; Rt=0.681 min.

Step 5: Synthesis of 5-((2R,5S)-5-methylpiperidin-2-yl)-2-(2-(pyrrolidin-1-yl)ethyl)benzo[d]thiazole Prepared by general procedure Scheme J step 5. Yield: 1 g of crude.

LCMS(ESI): [M]⁺ m/z: calcd 329.2; found 330.2; Rt=0.720 min.

1001
3BBB. ((2R,5S)-5-methyl-2-(2-(1-methylpiperidin-4-yl)benzo[d]thiazol-5-yl)piperidin-1-yl)-2-oxoacetamide
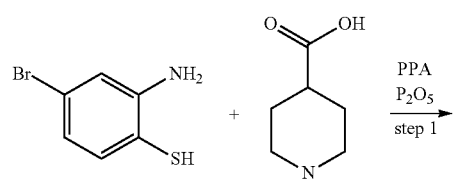
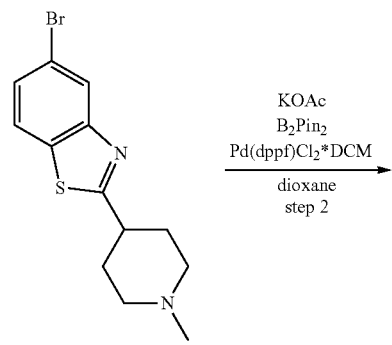
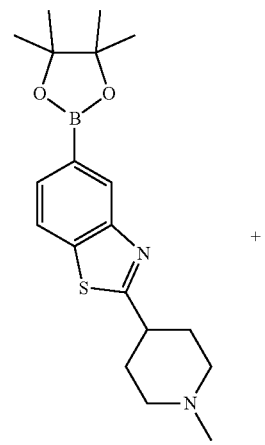
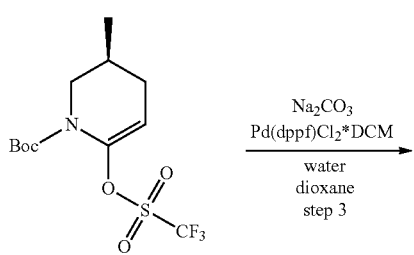
1002
-continued
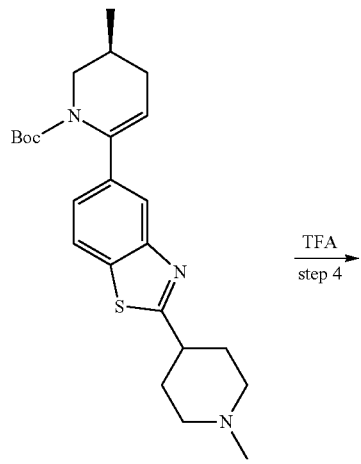
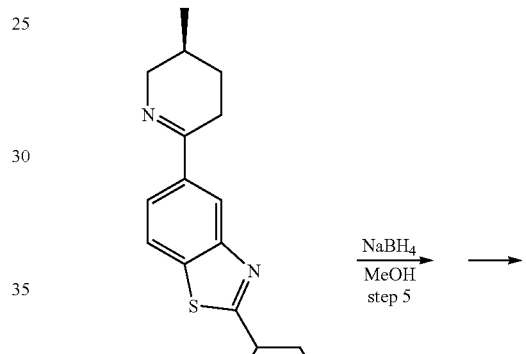

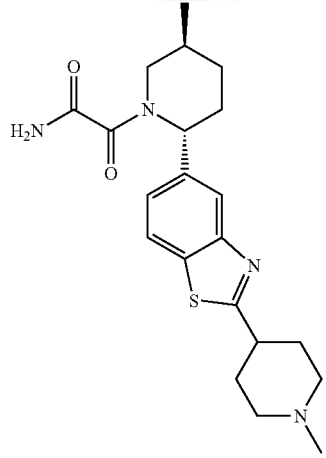
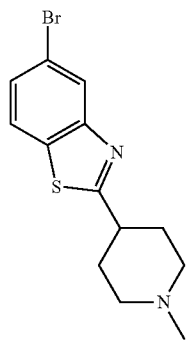
Prepared by general procedure Scheme J step 1A. Yield: 14 g (92.88%).
LCMS(ESI): [M]+ m/z: calcd 311.2; found 312.2; Rt=0.742 min.
Step 2: Synthesis of 2-(1-methylpiperidin-4-yl)-5-(4,4,5,5-tetramethyl-1,3,2-dioxaborolan-2-yl)benzo[d]thiazole
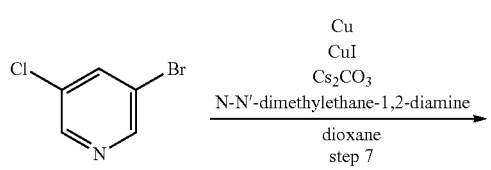
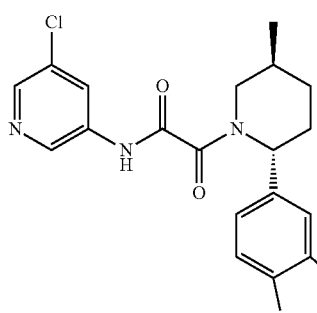
EN-TG2-6913
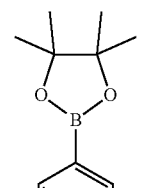
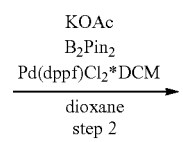
Step 1: Synthesis of 5-bromo-2-(1-methylpiperidin-4-yl)benzo[d]thiazole
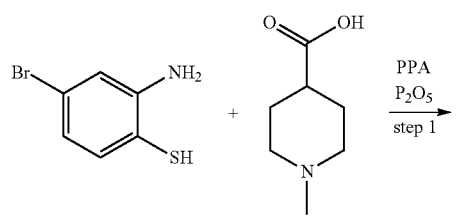
Prepared by general procedure Scheme J step 2. Yield: 8.5 g (92.29%).
LCMS(ESI): [M]+ m/z: calcd 358.2; found 359.2; Rt=0.978 min.

1005

Step 3: Synthesis of (S)-tert-butyl 3-methyl-6-(2-(1-methylpiperidin-4-yl)benzo[d]thiazol-5-yl)-3,4-dihydropyridine-1(2H)-carboxylate

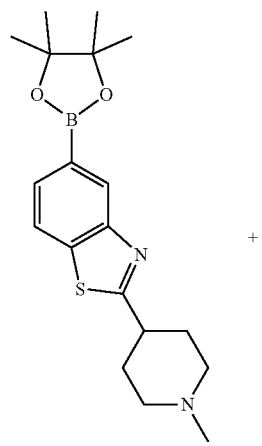

+

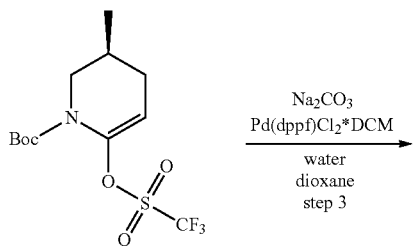

$\xrightarrow[\text{step 3}]{\substack{\text{Na}_2\text{CO}_3 \\ \text{Pd(dppf)Cl}_2\text{*DCM} \\ \text{water} \\ \text{dioxane}}}$ Prepared by general procedure Scheme J step 3. Yield: 15 g of crude.

LCMS(ESI): [M]⁺ m/z: calcd 427.2; found 428.2; Rt=1.274 min.

1006

Step 4: Synthesis of (S)-5-(5-methyl-3,4,5,6-tetrahydropyridin-2-yl)-2-(1-methylpiperidin-4-yl)benzo[d]thiazole

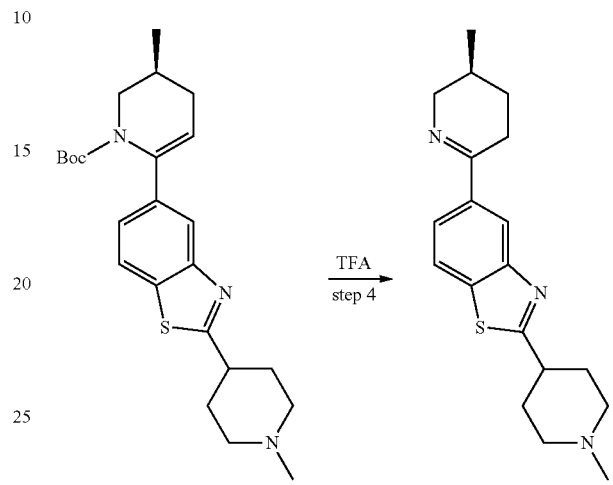

Prepared by general procedure Scheme J step 4. Yield: 6 g (94.96%).

LCMS(ESI): [M]⁺ m/z: calcd 327.2; found 328.2; Rt=0.670 min.

Step 5: Synthesis of 5-((2R,5S)-5-methylpiperidin-2-yl)-2-(1-methylpiperidin-4-yl)benzo[d]thiazole

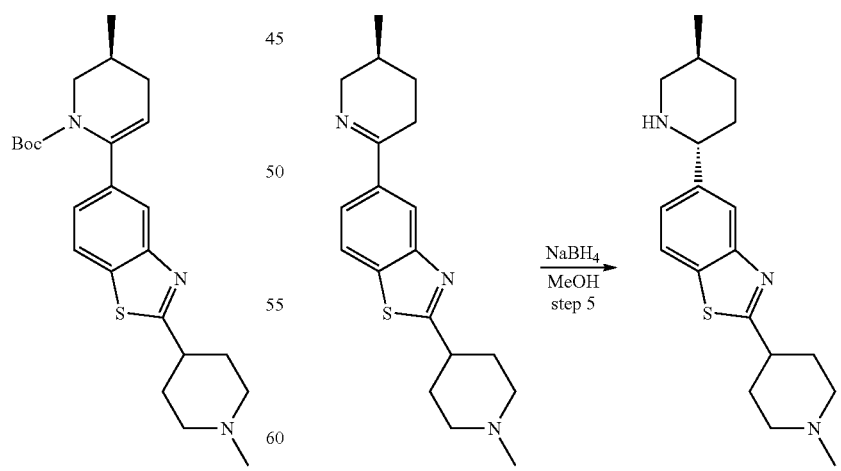

Prepared by general procedure Scheme J step 5. Yield: 4 g (66.26%).

LCMS(ESI): [M]⁺ m/z: calcd 329.2; found 330.2; Rt=0.703 min.

1007

Step 6: Synthesis of 2-((2R,5S)-5-methyl-2-(2-(1-methylpiperidin-4-yl)benzo[d]thiazol-5-yl)piperidin-1-yl)-2-oxoacetamide

1008

2-((2R,5S)-5-methyl-2-(2-(1-methylpiperidin-4-yl)benzo[d]thiazol-5-yl)piperidin-1-yl)-2-oxoacetamide

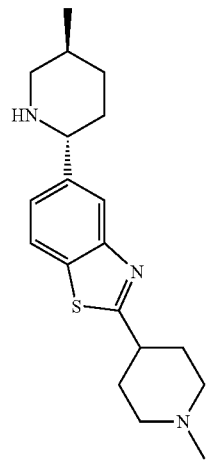

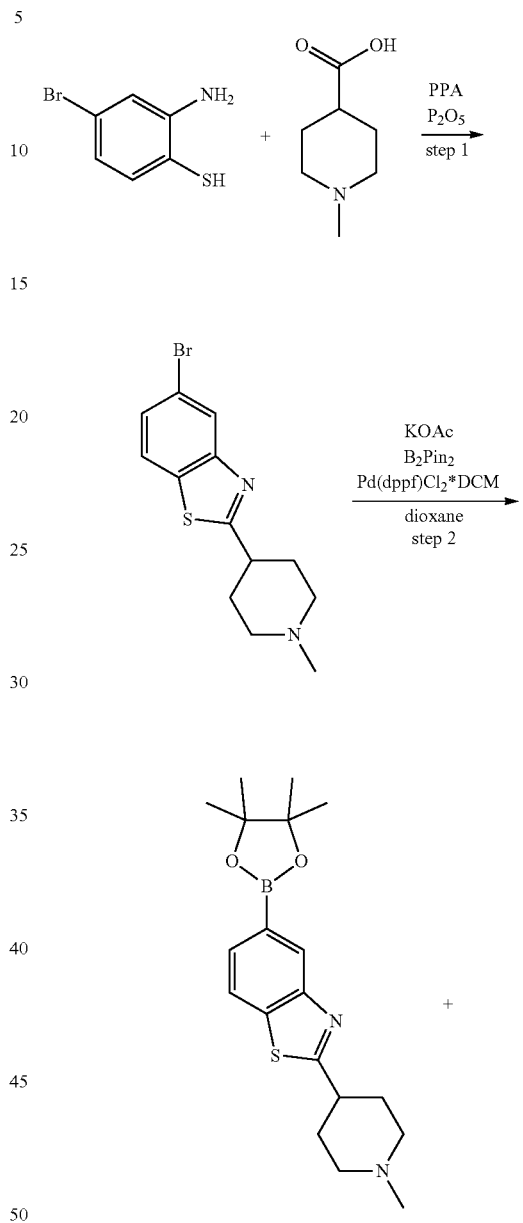

2,2,2-trifluoroethyl 2-chloro-2-oxo-acetate (1.04 g, 5.46 mmol) was slowly added to a stirred solution of 2-(1-methyl-4-piperidyl)-5-[(2R,5S)-5-methyl-2-piperidyl]-1,3-benzothiazole (1.5 g, 4.55 mmol) and TEA (921.30 mg, 9.10 mmol, 1.27 mL) in dry THF (50 mL) at 25° C. The resulting mixture was stirred at 25° C. for 0.5 hr, Then gaseous ammonia was bubbled through the reaction mixture at 25° C. for 0.5 hr. The resulting ammonium chloride precipitate was filtered and discarded, the filtrate was concentrated in vacuum to afford crude 2-[(2R,5S)-5-methyl-2-[2-(1-methyl-4-piperidyl)-1,3-benzothiazol-5-yl]-1-piperidyl]-2-oxo-acetamide (1.6 g, 3.99 mmol, 87.75% yield) as yellow solid, which was used directly in the next step.

LCMS(ESI): [M]+ m/z: calcd 400.2; found 401.2; Rt=0.867 min.

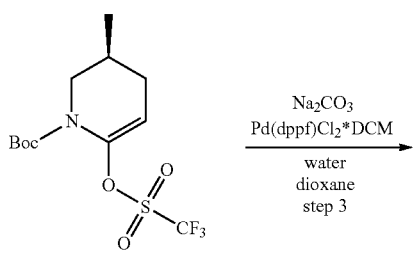

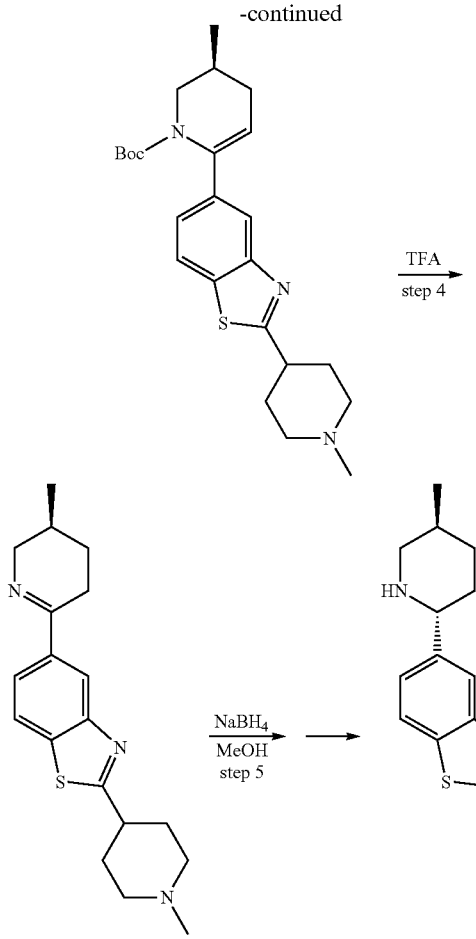

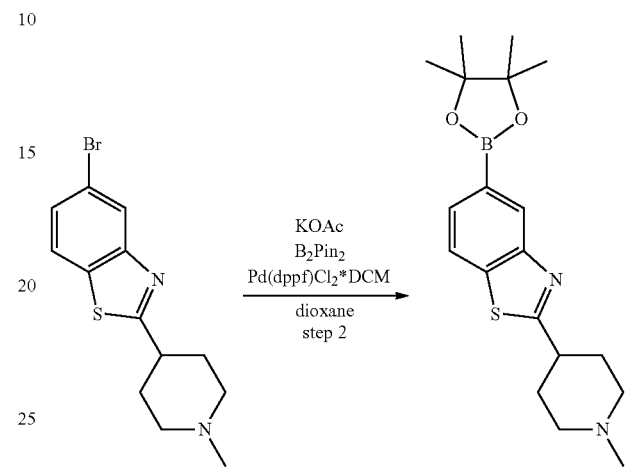

LCMS(ESI): [M]$^+$ m/z: calcd 311.2; found 312.2; Rt=0.742 min.

Step 2: Synthesis of 2-(1-methylpiperidin-4-yl)-5-(4,4,5,5-tetramethyl-1,3,2-dioxaborolan-2-yl)benzo[d]thiazole Prepared by general procedure Scheme J step 2. Yield: 8.5 g (92.29%).

LCMS(ESI): [M]$^+$ m/z: calcd 358.2; found 359.2; Rt=0.978 min.

Step 3: Synthesis of (S)-tert-butyl 3-methyl-6-(2-(1-methylpiperidin-4-yl)benzo[d]thiazol-5-yl)-3,4-dihydropyridine-1(2H)-carboxylate Step 1: Synthesis of 5-bromo-2-(1-methylpiperidin-4-yl)benzo[d]thiazole

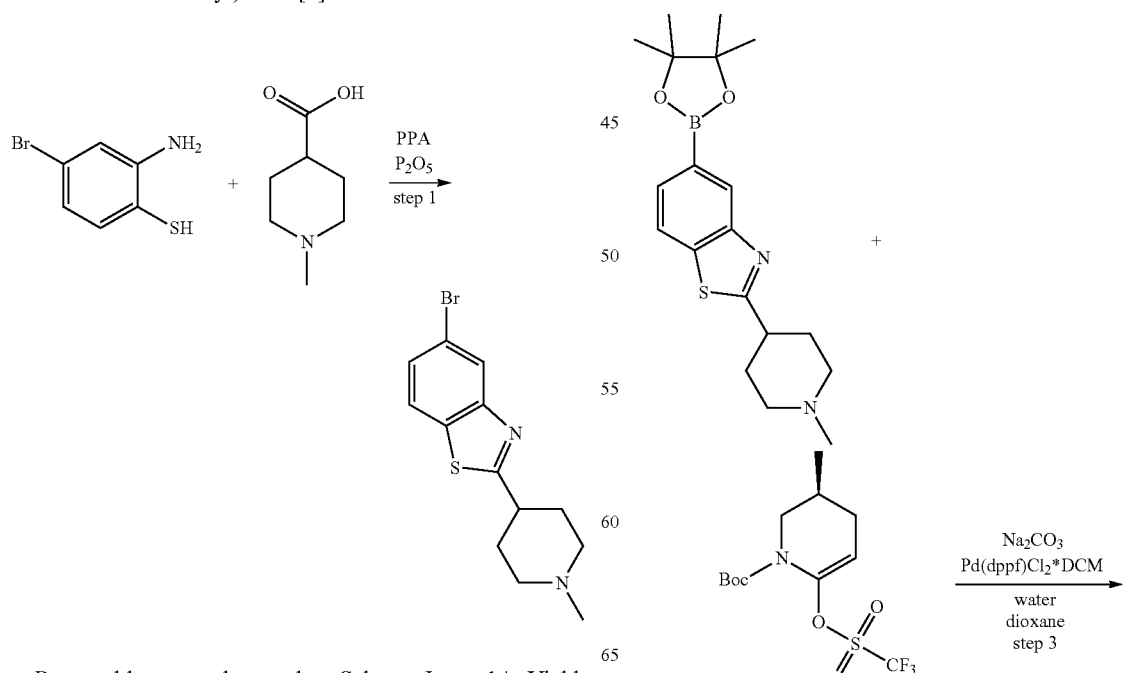

Prepared by general procedure Scheme J step 1A. Yield: 14 g (92.88%).

-continued

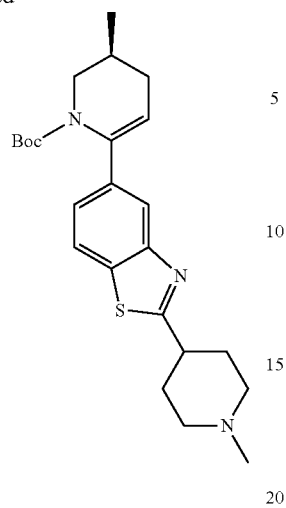

Prepared by general procedure Scheme J step 3. Yield: 15 g of crude.

LCMS(ESI): [M]+ m/z: calcd 427.2; found 428.2; Rt=1.274 min.

Step 4: Synthesis of (S)-5-(5-methyl-3,4,5,6-tetra-hydropyridin-2-yl)-2-(1-methylpiperidin-4-yl)benzo[d]thiazole

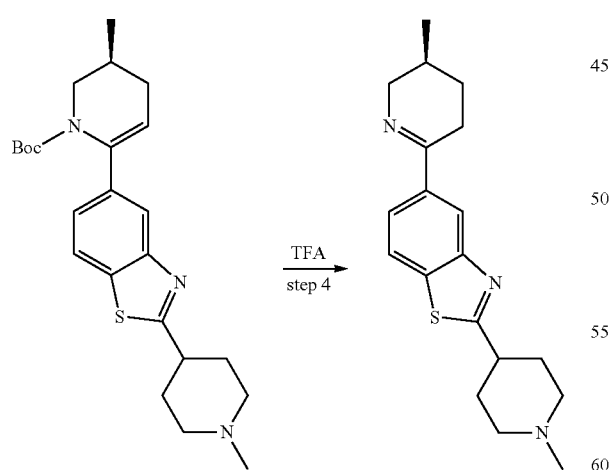

Prepared by general procedure Scheme J step 4. Yield: 6 g (94.96%).

LCMS(ESI): [M]+ m/z: calcd 327.2; found 328.2; Rt=0.670 min.

Step 5: Synthesis of 5-((2R,5S)-5-methylpiperidin-2-yl)-2-(1-methylpiperidin-4-yl)benzo[d]thiazole

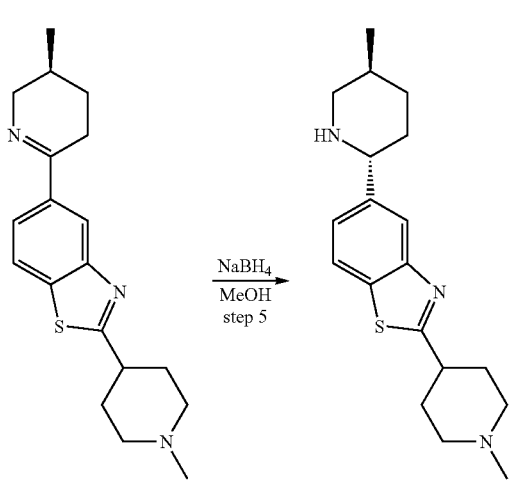 [SMILES: C[C@H]1CCC(c2ccc3sc(C4CCN(C)CC4)nc3c2)=NC1 ; "NaBH4" ; C[C@H]1CC[C@H](c2ccc3sc(C4CCN(C)CC4)nc3c2)NC1]

Prepared by general procedure Scheme J step 5. Yield: 4 g (66.26%).

LCMS(ESI): [M]+ m/z: calcd 329.2; found 330.2; Rt=0.703 min.

Step 6: Synthesis of 2-((2R,5S)-5-methyl-2-(2-(1-methylpiperidin-4-yl)benzo[d]thiazol-5-yl)piperidin-1-yl)-2-oxoacetamide 1-methyl-4-(3-((2R,5S)-5-methylpiperidin-2-yl)phenyl)piperazine Step 1: Synthesis of (2R,5S)-tert-butyl 5-methyl-2-(3-(4-methylpiperazin-1-yl)phenyl)piperidine-1-carboxylate

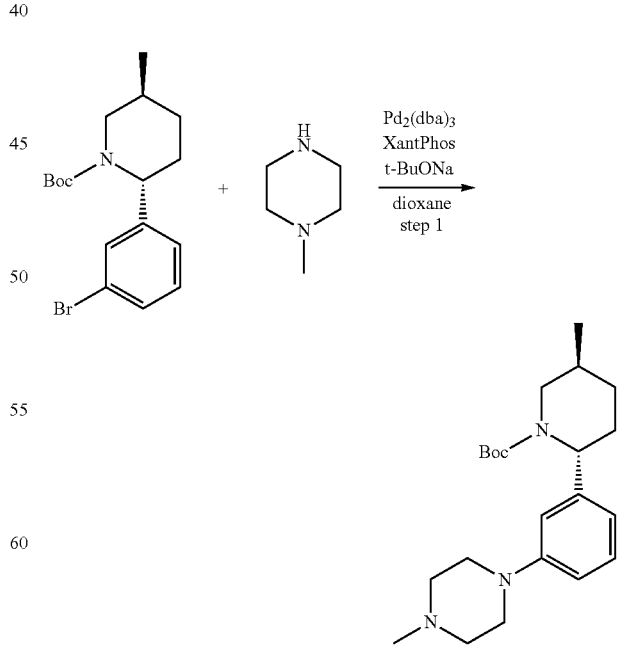

tert-butyl (2R,5S)-2-(3-bromophenyl)-5-methyl-piperidine-1-carboxylate (1.03 g, 2.91 mmol), 1-methylpiperazine (291.20 mg, 2.91 mmol, 322.48 µL), 4,5-bis(diphenylphosphino)-9,9-dimethylxanthene (168.22 mg, 290.73 µmol) and sodium tert-butoxide (419.09 mg, 4.36 mmol) were mixed together in dioxane (15 mL) and the resulting mixture was evacuated and backfilled three times with argon. tris(Dibenzylideneacetone)dipalladium (0) (133.11 mg, 145.36 mol) was added to the previous mixture and the resulting mixture was heated at 100° C. (oil bath) overnight. The reaction mixture was cooled and diluted with water (50 ml). The resulting mixture was extracted with EtOAc (3*50 ml). Combined organic layers were washed with brine (2*50 ml), dried over $Na_2SO_4$, filtered and evaporated to obtain tert-butyl (2R,5S)-5-methyl-2-[3-(4-methylpiperazin-1-yl)phenyl]piperidine-1-carboxylate (1.1 g, crude).

LCMS(ESI): $[M]^+$ m/z: calcd 373.2; found 374.2; Rt=0.991 min.

Step 2: Synthesis of 1-methyl-4-(3-((2R,5S)-5-methylpiperidin-2-yl)phenyl)piperazine

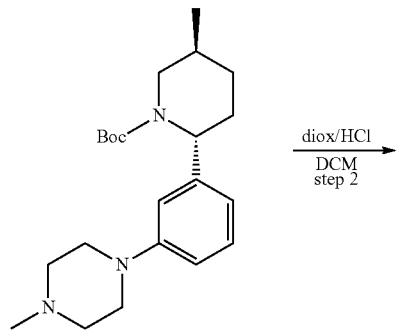

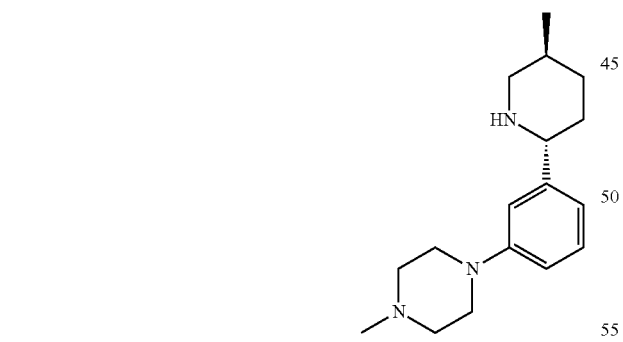

tert-butyl (2R,5S)-5-methyl-2-[3-(4-methylpiperazin-1-yl)phenyl]piperidine-1-carboxylate (1.1 g, 2.94 mmol) was dissolved in DCM (15 mL), then dioxane/HCl (2.94 mmol, 5 mL) was added and it was stirred 16 hr at rt. Insoluble material was collected by filtration, filter cake was washed with additional amount of MTBE and dried on air to afford 1-methyl-4-[3-[(2R,5S)-5-methyl-2-piperidyl]phenyl]piperazine (750 mg, 2.42 mmol, 82.19% yield, HCl).

LCMS(ESI): $[M]^+$ m/z: calcd 273.2; found 274.2; Rt=0.675 min.

4. Syntheses Via Ring Opening of Piperidones with Nucleophiles

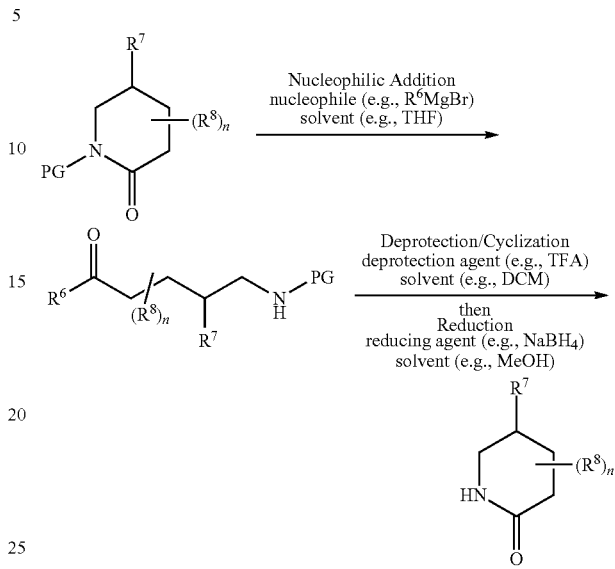

In some embodiments, a secondary amine can be prepared by nucleophilic addition to a 2-piperidone. Nucleophilic addition/ring-opening can be accomplished using a Grignard reagent, e.g. $R^6MgBr$. A nucleophilic addition reaction may be carried out in solvents such as but not limited to THF, $Et_2O$, TMEDA, DME and MTBE or mixtures thereof. In some embodiments, nucleophilic addition is accomplished through conditions comprising $R^6Br$, Mg. $I_2$ and THF.

In some embodiments, a secondary amine undergoes a sequence of deprotection, cyclization and reduction to prepare a substituted piperidine. Conditions for the removal of a protecting group (PG), e.g., MoM or Boc are known to a person of ordinary skill in the art. Conditions for removing a protecting group -PG (e.g., -Boc) can employ, for example, acidic conditions, (e.g., water/dioxane, hydrochloric acid in a protic solvent (e.g., methanol), hydrochloric acid in an aprotic solvent (e.g., dioxane), TFA in an aprotic solvent (e.g., dichloromethane, chloroform, etc)). In some embodiments, a deproction step employs HCl (40 M) in dioxane. In some embodiments, a deproction step employs HCl (40 M) in DCM.

In some embodiments, upon deprotection of a compound of formula I-5 can undergo spontaneous cyclization to form a cyclic imine. Reduction of a cyclic imine can be accomplished using a reducing agent such as a hydride reducing agent, e.g., $NaBH_4$, or $LiAlH_4$, silicon reducing agent, e.g., $Cl_3SiH$, or $H_2$ reduction in the presence of a catalyst, e.g. a Ir catalyst, a Ru catalyst, a Pd catalyst (e.g., Pd/C, Pd(OAc)$_2$). In some embodiments, reduction can be accomplished using conditions comprising, $NaBH_4$ in MeOH. In some embodiments, reduction can be accomplished using conditions comprising, $NaBH_4$ in MeOH and $H_2O$. In some embodiments, deprotection, cyclization and reduction occur in a single synethic step. In some embodiments, deprotection/cyclization/reduction can be accomplished using conditions comprising, $NaBH_4$, TFA, MeOH and $H_2O$.

4A. Synthesis of (2R,5S)-2-(4-fluorophenyl)-5-methyl-piperidine

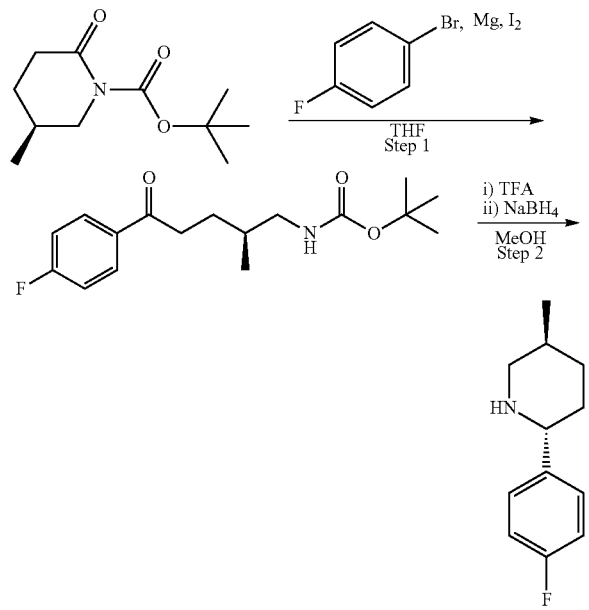

Step 1: Synthesis of tert-butyl N-[(2S)-5-(4-fluorophenyl)-2-methyl-5-oxo-pentyl]carbamate A dry 2 necked round bottomed flask, fitted with a magnetic stir bar was charged with magnesium (1.44 g, 59.08 mmol) under argon atmosphere. Dry THF (125 mL) and 1-bromo-4-fluoro-benzene (10.34 g, 59.08 mmol, 6.50 mL) were added. Iodine (107.11 mg, 421.99 μmol) was added to the stirred solution and the resulting reaction mixture was heated gently until it maintained its own reflux. When reflux had subsided, external heating was applied to maintain reflux for an additional 1 hour. A separate dry 3 necked round bottomed flask fitted with a thermometer and a magnetic stir bar was charged with (S)-tert-butyl 5-methyl-2-oxopiperidine-1-carboxylate (9 g, 42.20 mmol). Dry THF (125 mL) was added under argon atmosphere and the solution was cooled to −78° C. Freshly prepared Grignard reagent was added to the resulting mixture dropwise during 1 hour, maintaining the internal temperature below −70° C. The resulting reaction mixture was allowed to warm to room temperature, quenched with saturated NH$_4$Cl solution and extracted with DCM (3×50 mL). The combined organic layer was dried over Na$_2$SO$_4$, filtered and concentrated under reduced pressure to obtain product tert-butyl N-[(2S)-5-(4-fluorophenyl)-2-methyl-5-oxo-pentyl]carbamate (13.2 g, crude) as a light-yellow oil, which was used in the next step reaction without any further purification LCMS(ESI): [M+Boc]$^+$ m/z: calcd 309.2; found 210.2; Rt=1.386 min.

$^1$H NMR (CDCl$_3$, 400 MHz): δ (ppm) 0.93 (m, 3H), 1.42 (s, 9H), 1.54-1.79 (m, 4H), 2.90-3.10 (m, 3H), 4.66 (brs, 1H), 7.08 (m, 2H), 7.97 (m, 2H).

Step 2: Synthesis of (2R,5S)-2-(4-fluorophenyl)-5-methyl-piperidine tert-butyl N-[(2S)-5-(4-fluorophenyl)-2-methyl-5-oxo-pentyl]carbamate (13.2 g, 42.67 mmol) was dissolved in Trifluoroacetic acid (19.46 g, 170.67 mmol, 13.15 mL) and the resulting reaction mixture was stirred for 1 hour. After 1 hour, 50% aq·NaOH solution was added to the reaction mixture till pH=13-14. The resulting mixture was extracted with DCM (4×20 mL). The combined organic phase was dried over MgSO$_4$ and concentrated under reduced pressure. The obtained residue was dissolved in Methanol (125 mL) and water (25 mL). Sodium Borohydride (1.61 g, 42.67 mmol) was added portionwise to it. The resulting reaction mixture was stirred under argon atmosphere at 21° C. for 16 hours. After 16 hours, the reaction mixture was acidified with 1-2 M HCl until the pH was 1-3 and stirred for 30 minutes. Then, 50% aq. NaOH solution was added till pH=13-14. The resulting mixture was extracted with DCM (4×100 mL). The combined organic phase was dried over Na$_2$SO$_4$ and concentrated under reduced pressure to obtain (2R,5S)-2-(4-fluorophenyl)-5-methyl-piperidine (6.6 g, 34.15 mmol, 80.04% yield) as a light-yellow solid. The crude product was used for the next step reaction without any further purification.

LCMS(ESI): [M+H]$^+$ m/z: calcd 193.2; found 194.2; Rt=0.704 min.

$^1$H NMR (CDCl$_3$, 500 MHz): δ (ppm) 0.88 (m, 3H), 1.14 (m, 1H), 1.51 (m, 1H), 1.64 (m, 2H), 1.764 (m, 1H), 1.87 (m, 1H), 2.41 (t, 0.9H), 2.87 (d, 0.1H, cis-impurity), 2.97 (d, 0.1H, cis-impurity) 3.14 (d, 0.9H), 3.52 (d, 0.9H), 3.60 (m, 0.1H, cis-impurity), 6.99 (m, 2H), 7.32 (m, 2H).

4B. Synthesis of 2-(4-fluorophenyl)-5-methylpiperidine

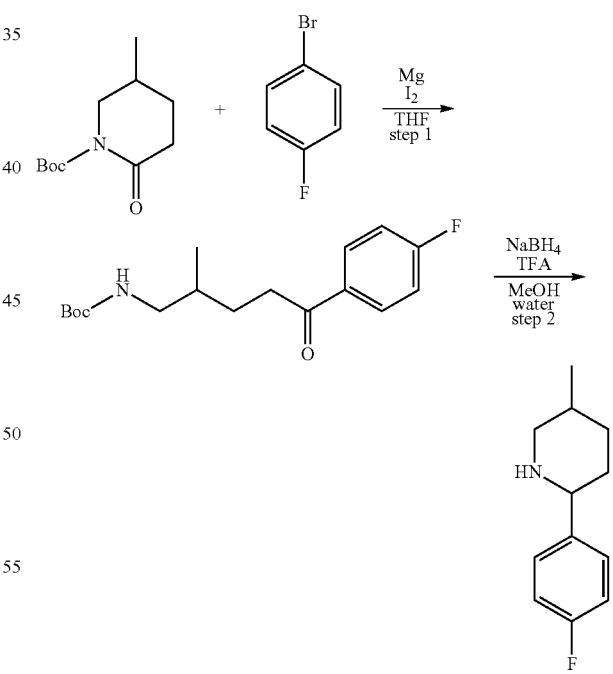

Step 1: Synthesis of tert-butyl (5-(4-fluorophenyl)-2-methyl-5-oxopentyl)carbamate To a dry 2 necked flask was added magnesium (1.04 g, 42.86 mmol, 598.65 μL), dry THF (50 mL) and 1-bromo-4-fluoro-benzene (5 g, 28.57 mmol, 3.14 mL) with stirring under Ar. Iodine (72.52 mg, 285.72 µmol) was added and the mixture was heated gently until it maintained its own reflux. When reflux had subsided external heating was applied to maintain reflux for a further 1 hour. tert-butyl 5-methyl-2-oxo-piperidine-1-carboxylate (6.09 g, 28.57 mmol) was added to a dry 3 necked round bottomed flask with a thermometer. Dry THF (50 mL) was added with stirring under Ar and the solution was cooled to −78° C. The Grignard reagent was added to the t-boc-lactam over 1 hour, maintaining the internal temperature below −70° C. The solution was warmed to room temperature and sat. NH$_4$Cl was added. The aqueous layer was extracted 3×50 mL with DCM and the organic layers combined, dried over Na$_2$SO$_4$, filtered and concentrated in vacuo. tert-butyl N-[5-(4-fluorophenyl)-2-methyl-5-oxo-pentyl]carbamate (6.7 g, crude) was obtained as a light-yellow oil and was used in the next step without further purification.

$^1$H NMR (500 MHz, CDCl$_3$) δ (ppm) 0.95 (d, 3H), 1.44 (s, 9H), 1.82 (m, 3H), 3.05 (m, 4H), 4.71 (bds, 1H), 7.13 (d, 2H), 7.99 (d, 2H).

LCMS(ESI): [M-Boc]$^+$ m/z: calcd 209.2; found 210.2; Rt=1.508 min.

Step 2: Synthesis of 2-(4-fluorophenyl)-5-methylpiperidine

The tert-butyl N-[5-(4-fluorophenyl)-2-methyl-5-oxo-pentyl]carbamate (6.7 g, 21.66 mmol) was stirred in trifluoroacetic acid (12.35 g, 108.28 mmol, 8.34 mL) for 1 hr. TLC was used to check the reaction progress. 50% w/v NaOH solution was added to the mixture until the pH was 13-14. The product was extracted 4×20 mL with DCM and the organic layers combined, dried with MgSO$_4$ and evaporated. The product was dissolved in mixture methanol (50 mL)/water (10 mL) and added to a flask followed by sodium borohydride (819.32 mg, 21.66 mmol, 765.72 µL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na$_2$SO$_4$, filtered and evaporated to give 2-(4-fluorophenyl)-5-methylpiperidine (1.4 g, 7.24 mmol, 33.45% yield) as a colorless oil.

$^1$H NMR (400 MHz, CDCl$_3$) δ (ppm) 0.86 (d, 3H), 1.13 (m, 1H), 1.50 (m, 1H), 1.62 (m, 1H), 1.82 (m, 3H), 2.38 (t, 1H), 3.09 (d, 1H), 3.51 (d, 1H), 6.96 (d, 2H), 7.30 (d, 2H).

LCMS(ESI): [M]$^+$ m/z: calcd 193.3; found 194.2; Rt=1.985 min.

4C. The Synthesis of 5-methyl-2-(m-tolyl)piperidine

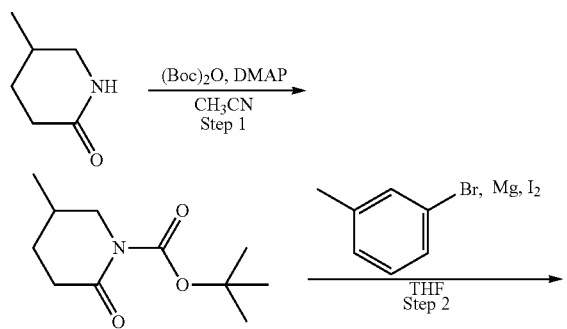

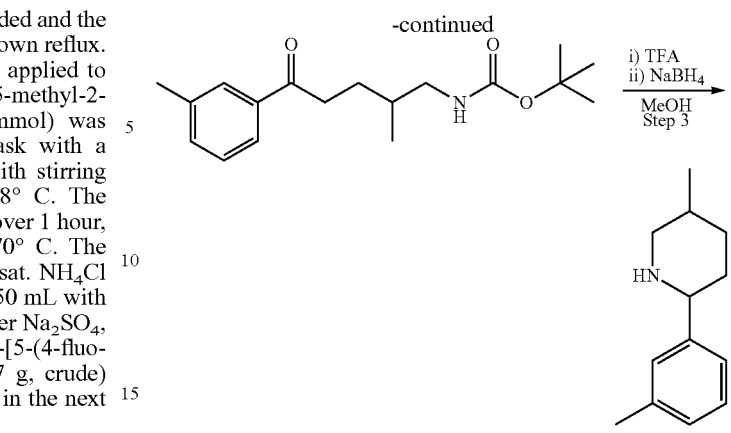

Step 1: Synthesis of tert-butyl 5-methyl-2-oxo-piperidine-1-carboxylate

To a stirred solution of 5-methylpiperidin-2-one (1 g, 8.84 mmol) and 4-dimethylaminopyridine (10.80 mg, 88.37 µmol) in CH$_3$CN (20 mL) was added Di-tert-butyl dicarbonate (1.93 g, 8.84 mmol, 2.03 mL). The resulting reaction mixture was stirred at room temperature for 12 hours. Upon completion, the reaction mixture was concentrated under reduced pressure to obtain tert-butyl 5-methyl-2-oxo-piperidine-1-carboxylate (1.5 g, 7.03 mmol, 79.59% yield). The crude product was used for the next step reaction without any further purification.

$^1$H NMR (DMSO-d$_6$, 500 MHz): δ (ppm) 0.93 (d, 3H), 1.43 (m, 10H), 1.83 (m, 2H), 2.38 (m, 2H), 3.08 (m, 1H), 3.66 (m, 1H)

Step 2: Synthesis of tert-butyl N-[2-methyl-5-(m-tolyl)-5-oxo-pentyl]carbamate

A dry 2 necked round bottomed flask (100 mL), fitted with a magnetic stir bar was charged with magnesium (170.94 mg, 7.03 mmol) under argon atmosphere. Dry THF (20 mL) and 1-bromo-3-methyl-benzene (1.20 g, 7.03 mmol) were added. Iodine (7.85 mg, 70.33 µmol) was added to the stirred solution and the resulting reaction mixture was heated gently until it maintained its own reflux. When reflux had subsided, external heating was applied to maintain reflux for an additional 1 hour. A separate dry 3 necked round bottomed flask (100 mL) fitted with a thermometer and a magnetic stir bar was charged with tert-butyl 5-methyl-2-oxo-piperidine-1-carboxylate (2.14 g, 7.03 mmol). Dry THF (20 mL) was added under argon atmosphere and the solution was cooled to −78° C. Freshly prepared Grignard reagent was added to the resulting mixture dropwise during 30 minutes, maintaining the internal temperature below −70° C. The resulting reaction mixture was allowed to warm to room temperature and stirred at the same temperature for 1 hour. After 1 hour, the reaction mixture was quenched with saturated NH$_4$Cl solution and extracted with EtOAc (2*40 mL). The combined organic layer was dried over Na$_2$SO$_4$, filtered and concentrated under reduced pressure to obtain product tert-butyl N-[2-methyl-5-(m-tolyl)-5-oxo-pentyl]carbamate (1.5 g, crude), which was used in the next step reaction without any further purification LCMS(ESI): [M+Boc]$^+$ m/z: calcd 305.2; found 206.2; Rt=1.517 min.

Step 3: Synthesis of 5-methyl-2-(m-tolyl)piperidine tert-butyl N-[2-methyl-5-(m-tolyl)-5-oxo-pentyl]carbamate (3.19 g, 4.91 mmol) was dissolved in Trifluoroacetic acid (5.60 g, 49.11 mmol, 3.78 mL) and the resulting reaction mixture was stirred for 1 hour. After 1 hour, 50% aq·NaOH solution was added to the reaction mixture till pH=11-12. The resulting mixture was extracted with DCM (4×20 mL). The combined organic phase was dried over $Na_2SO_4$ and concentrated under reduced pressure. The obtained residue was dissolved in Methanol (20 mL) and Sodium Borohydride (185.81 mg, 4.91 mmol) was added portionwise at 0° C. The resulting reaction mixture was stirred at 20° C. for 1 hour. After 1 hour, the reaction mixture was concentrated under reduced pressure and the obtained residue was diluted with 50% aq·NaOH solution. The resulting mixture was extracted with DCM (4×20 mL). The combined organic phase was dried over $Na_2SO_4$ and concentrated under reduced pressure to obtain 5-methyl-2-(m-tolyl)piperidine (0.2 g, 1.06 mmol, 21.51% yield). The crude product was used for the next step reaction without any further purification.

LCMS(ESI): [M+H]$^+$ m/z: calcd 189.2; found 190.2; Rt=0.838 min.

4D. The Synthesis of 2-(3-chlorophenyl)-5-methyl-piperidine

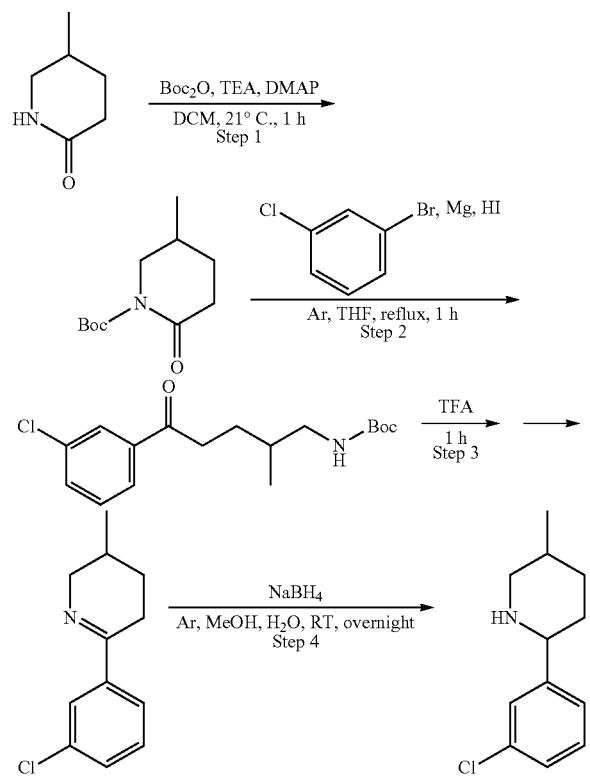

Step 1: The Synthesis of tert-butyl 5-methyl-2-oxo-piperidine-1-carboxylate

To a solution of 5-methylpiperidin-2-one (5 g, 44.19 mmol), triethylamine (4.47 g, 44.19 mmol, 6.16 mL) and DMAP (539.83 mg, 4.42 mmol) in DCM was added portionwise tert-butoxycarbonyl tert-butyl carbonate (9.64 g, 44.19 mmol, 10.14 mL) at 21° C. The resulting solution was washed with 10% aq. HCl and brine, dried over $Na_2SO_4$ and evaporated to dryness to give tert-butyl 5-methyl-2-oxo-piperidine-1-carboxylate (7.7 g, 36.10 mmol, 81.71% yield) as an orange oil.

$^1$H NMR (500 MHz, DMSO-$d_6$) δ (ppm) 0.94 (d, 3H), 1.42 (s, 10H), 1.76 (m, 1H), 1.92 (m, 1H), 2.38 (m, 2H), 3.07 (t, 1H), 3.65 (m, 1H).

LCMS(ESI): [M+H]$^+$ m/z: calcd 213.1; found 214.2; Rt=1.227 min.

Step 2: The Synthesis of tert-butyl N-[5-(3-chlorophenyl)-2-methyl-5-oxo-pentyl]carbamate To a dry 2 necked flask was added magnesium (253.90 mg, 10.45 mmol, 145.92 µL), dry THF (25 mL) and tert-butyl 5-methyl-2-oxo-piperidine-1-carboxylate (2.23 g, 10.45 mmol) with stirring under Ar, iodine (13.36 mg, 104.46 µmol) was added. The mixture was heated gently until it maintained its own reflux. When reflux had subsided external, heating was applied to maintain reflux for a further 1 hour. 1-bromo-3-chlorobenzene (2 g, 10.45 mmol, 1.23 mL) was added to a dry 3 necked round bottomed flask with a thermometer. Dry THF (25 mL) was added with stirring under Ar and the solution was cooled to −78° C. The Grignard reagent was added to the t-Boc-lactam over 1 hour, maintaining the internal temperature below −70° C. The solution was warmed to room temperature and sat. $NH_4Cl$ was added. The aqueous layer was extracted 3*50 mL with DCM and the organic layers combined, dried over $Na_2SO_4$, filtered and concentrated in vacuo. tert-butyl N-[5-(3-chlorophenyl)-2-methyl-5-oxo-pentyl]carbamate (3.3 g, crude) was obtained as a light-yellow oil and was used in the next step without further purification.

$^1$H NMR (400 MHz, CDCl$_3$) δ (ppm) 1.01 (d, 3H), 1.49 (m, 10H), 2.43 (m, 2H), 3.07 (m, 2H), 3.77 (m, 3H), 7.27 (m, 4H).

LCMS(ESI): [M+H]$^+$ m/z: calcd 325.2; found 326.2; Rt=1.24 min.

Step 3: The Synthesis of 6-(3-chlorophenyl)-3-methyl-2,3,4,5-tetrahydropyridine

The tert-butyl N-[5-(3-chlorophenyl)-2-methyl-5-oxo-pentyl]carbamate (3.3 g, 10.13 mmol) was stirred in trifluoroacetic acid (1.15 g, 10.13 mmol, 780.29 µL) for 1 hr. TLC was used to check the reaction progress. 50% w/v NaOH solution was added to the mixture until the pH was 13-14. The product was extracted 4*20 mL with DCM and the organic layers combined, dried with $MgSO_4$ and evaporated. 6-(3-chlorophenyl)-3-methyl-2,3,4,5-tetrahydropyridine (1.5 g, crude) was obtained as light-yellow oil which was used in the next step without further purification.

$^1$H NMR (400 MHz, CDCl$_3$) δ (ppm) 1.21 (d, 3H), 1.79 (m, 3H), 2.84 (m, 2H), 3.23 (m, 2H), 7.25 (s, 1H), 7.27 (m, 3H).

LCMS(ESI): [M+H]$^+$ m/z: calcd 207.2; found 208.2; Rt=0.858 min.

Step 4: The synthesis of 2-(3-chlorophenyl)-5-methyl-piperidine 6-(3-chlorophenyl)-3-methyl-2,3,4,5-tetrahydropyridine (1.5 g, 7.22 mmol) was dissolved in the mixture of MeOH (25 mL)/water (5 mL) and added to a flask followed by sodium borohydride (273.23 mg, 7.22 mmol, 255.35 μL). The mixture was stirred under Ar overnight. The reaction mixture was acidified with 1-2 M HCl until the pH was 1-3 and left for 30 minutes. NaOH aqueous solution was then added until the pH was 13-14 and the product was extracted with DCM (4*100 mL), the organic layers were combined, dried with Na₂SO₄, filtered and evaporated to give 2-(3-chlorophenyl)-5-methyl-piperidine (0.9 g, crude) as an light-yellow oil.

$^1$H NMR (400 MHz, CDCl₃) δ 1.02 (d, 3H), 1.89 (m, 4H), 2.91 (t, 2H), 3.27 (m, 2H), 3.68 (m, 1H), 7.25 (m, 3H), 7.27 (s, 1H).

LCMS(ESI): [M+H]⁺ m/z: calcd 209.2; found 210.2; Rt=0.869 min.

4E. Synthesis of 2-methyl-4-(5-methyl-2-piperidyl)pyridine

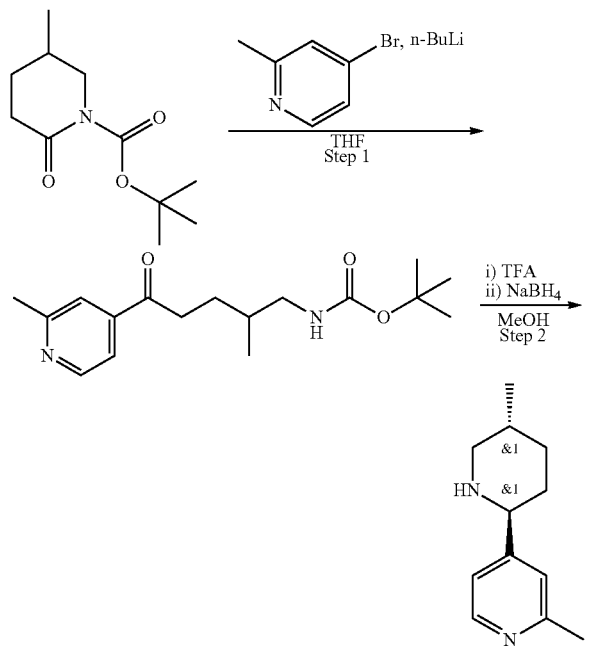

Step 1: Synthesis of tert-butyl N-[2-methyl-5-(2-methyl-4-pyridyl)-5-oxo-pentyl]carbamate To a stirred solution of 4-bromo-2-methyl-pyridine (2 g, 11.63 mmol, 1.38 mL) in THF (20 mL) at −78° C., n-butyllithium (2.5 M in Hexane, 819.21 mg, 12.79 mmol, 5.11 mL) was added under argon atmosphere. The resulting solution was stirred at the same temperature for 30 minutes. After 30 minutes, the resulting solution was added to a stirred solution of tert-butyl 5-methyl-2-oxo-piperidine-1-carboxylate (2.48 g, 11.63 mmol) in THF (20 mL) at −78° C. The resulting reaction mixture was allowed to warm to room temperature and stirred for 12 hours at the same temperature. After 12 hours, the reaction mixture was quenched with saturated NH₄Cl aq solution and extracted with EtOAc (2×100 mL). The combined organic phase was washed with brine, dried over Na₂SO₄ and concentrated under reduced pressure to obtain tert-butyl N-[2-methyl-5-(2-methyl-4-pyridyl)-5-oxo-pentyl]carbamate (5 g, crude). The crude product was used for the next step reaction without any further purification.

LCMS(ESI): [M+Boc]⁺ m/z: calcd 306.2; found 251.2 (t-Bu cleaved product mass); Rt=1.215 min.

Step 2: Synthesis of 2-methyl-4-(5-methyl-2-piperidyl)pyridine tert-butyl N-[2-methyl-5-(2-methyl-4-pyridyl)-5-oxo-pentyl]carbamate (5 g, 16.32 mmol) was dissolved in Trifluoroacetic acid (18.61 g, 163.19 mmol, 12.57 mL) and the resulting reaction mixture was stirred for 1 hour at room temperature. After 1 hour, 50% aq·NaOH solution was added to the reaction mixture till pH=11-12. The resulting mixture was extracted with DCM (4×40 mL). The combined organic phase was dried over Na₂SO₄ and evaporated to dryness. The obtained residue was dissolved in MeOH (100 mL) and Sodium Borohydride (617.37 mg, 16.32 mmol) was added portionwise. The resulting mixture was stirred at 20° C. for 12 hours. After 12 hours, the reaction mixture was concentrated and the obtained residue was diluted with 50% aq·NaOH solution. The resulting mixture was extracted with DCM (4×40 mL). The combined organic phase was dried over Na₂SO₄, filtered and concentrated under reduced pressure. The obtained residue was purified by HPLC to obtain 2-methyl-4-(5-methyl-2-piperidyl)pyridine (0.187 g, 982.74 μmol, 6.02% yield).

LCMS(ESI): [M+H]⁺ m/z: calcd 190.2; found 191.2; Rt=0.756 min.

4F. The Synthesis of 5-methyl-2-(p-tolyl)piperidine

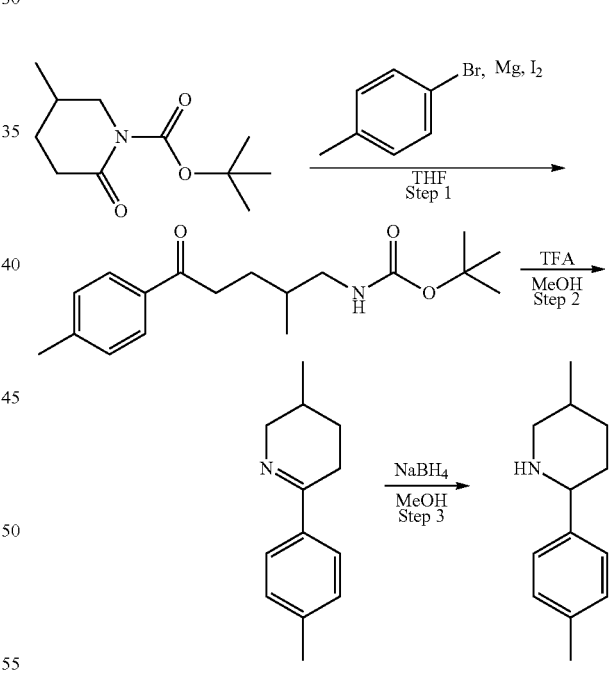

Step 1: Synthesis of tert-butyl N-[2-methyl-5-oxo-5-(p-tolyl)pentyl]carbamate A dry 2 necked round bottomed flask (100 mL), fitted with a magnetic stir bar was charged with Magnesium (284.21 mg, 11.69 mmol) under argon atmosphere. Dry THF (25 mL) and 1-bromo-4-methyl-benzene (2 g, 11.69 mmol, 1.42 mL) were added. Iodine (29.68 mg, 116.94 μmol) was added to the stirred solution and the resulting reaction mixture was heated gently until it maintained its own reflux. When reflux had subsided, external heating was applied to maintain reflux for an additional 1 hour. A separate dry 3 necked round bottomed flask (100 mL) fitted with a thermometer and a magnetic stir bar was charged with tert-butyl 5-methyl-2-oxo-piperidine-1-carboxylate (2.49 g, 11.69 mmol). Dry THF (25 mL) was added under argon atmosphere and the solution was cooled to −78° C. Freshly prepared Grignard reagent was added to the resulting mixture dropwise during 1 hour, maintaining the internal temperature below −70° C. The resulting reaction mixture was allowed to warm to room temperature and the reaction mixture was quenched with saturated NH$_4$Cl solution and extracted with DCM (3×50 mL). The combined organic layer was dried over Na$_2$SO$_4$, filtered and concentrated under reduced pressure to obtain product tert-butyl N-[2-methyl-5-oxo-5-(p-tolyl)pentyl]carbamate (3.2 g, crude) as a pale yellow oil, which was used in the next step reaction without any further purification LCMS(ESI): [M+Boc]$^+$ m/z: calcd 305.2; found 206.2; Rt=1.345 min.

Step 2: Synthesis of 3-methyl-6-(p-tolyl)-2,3,4,5-tetrahydropyridine tert-butyl N-[2-methyl-5-oxo-5-(p-tolyl)pentyl]carbamate (3.2 g, 10.48 mmol) was dissolved in Trifluoroacetic acid (7.40 g, 64.90 mmol, 5 mL). The resulting reaction mixture was stirred for 1 hour. Upon completion, 50% aq·NaOH solution was added to the reaction mixture till pH=13-14. The resulting mixture was extracted with DCM (4×20 mL). The combined organic phase was dried over MgSO$_4$ and concentrated under reduced pressure to obtain 3-methyl-6-(p-tolyl)-2,3,4,5-tetrahydropyridine (1.5 g, crude) as light-yellow oil. The crude product was used for the next step reaction without any further purification.

LCMS(ESI): [M+H]$^+$ m/z: calcd 187.2; found 188.2; Rt=0.867 min.

Step 3: Synthesis of 5-methyl-2-(p-tolyl)piperidine 3-methyl-6-(p-tolyl)-2,3,4,5-tetrahydropyridine (1.5 g, 8.01 mmol) was dissolved in MeOH (25 mL) and water (5 mL). Sodium Borohydride (303.04 mg, 8.01 mmol) was added portionwise at 0° C. The resulting reaction mixture was stirred under argon atmosphere for overnight. Upon completion, the reaction mixture was acidified with 1-2 M HCl until the pH=1-3 and stirred for 30 minutes. After 30 minutes, 50% aq NaOH solution was added to the resulting mixture till pH=13-14 and extracted with DCM (4×100 mL). The combined organic layer was dried over Na$_2$SO$_4$, filtered and evaporated under reduced pressure to obtain 5-methyl-2-(p-tolyl)piperidine (1 g, crude) as a light-yellow oil. The crude product was used for the next step reaction without any further purification.

LCMS(ESI): [M+H]$^+$ m/z: calcd 189.2; found 190.2; Rt=0.919 min.

4G. The Synthesis of 2-(3-fluorophenyl)-5-methyl-piperidine

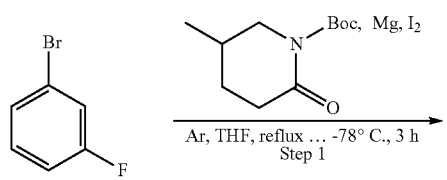

Step 1: The Synthesis of tert-butyl N-[5-(3-fluorophenyl)-2-methyl-5-oxo-pentyl]carbamate

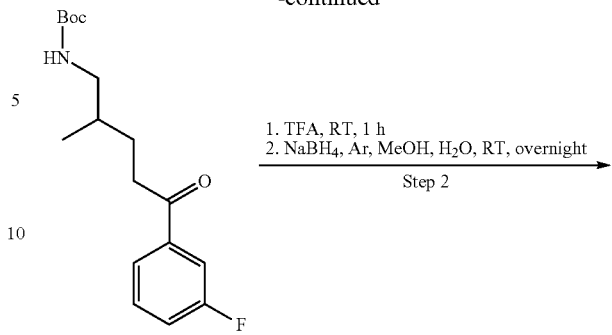

To a dry 2 necked flask was added magnesium (854.71 mg, 35.17 mmol, 491.22 μL), dry THF (25 mL) and 1-bromo-3-fluoro-benzene (6.15 g, 35.17 mmol, 3.92 mL) with stirring under Ar, iodine (297.52 mg, 1.17 mmol) was added and the mixture was heated gently until it maintained its own reflux. When reflux had subsided external heating was applied to maintain reflux for a further 1 hour. tert-butyl 5-methyl-2-oxo-piperidine-1-carboxylate (5 g, 23.44 mmol) was added to a dry 3 necked round bottomed flask with a thermometer. Dry THF (25 mL) was added with stirring under Ar and the solution was cooled to −78° C. The Grignard reagent was added to the t-Boc-lactam over 1 hour, maintaining the internal temperature below −70° C. The solution was warmed to room temperature and sat. NH$_4$Cl was added. The aqueous layer was extracted 3×50 mL with DCM and the organic layers combined, dried over Na$_2$SO$_4$, filtered and concentrated in vacuo. tert-butyl N-[5-(3-fluorophenyl)-2-methyl-5-oxo-pentyl]carbamate (8.5 g, crude) was obtained as a light-yellow oil and was used in the next step without further purification.

$^1$H NMR (400 MHz, CDCl$_3$) δ 0.94 (d, 3H), 1.41 (s, 9H), 1.72 (m, 3H), 3.01 (m, 4H), 7.24 (m, 2H), 7.42 (m, 1H), 7.60 (d, 1H), 7.71 (d, 1H).

LCMS(ESI): [M-Boc]$^+$ m/z: calcd 209.2; found 210.2; Rt=1.467 min.

Step 2: The Synthesis of 2-(3-fluorophenyl)-5-methyl-piperidine

The tert-butyl N-[5-(3-fluorophenyl)-2-methyl-5-oxo-pentyl]carbamate (8.5 g, 27.47 mmol) was stirred in trifluoroacetic acid (15.66 g, 137.37 mmol, 10.58 mL) for 1 hr. TLC was used to check the reaction progress. 50% w/v NaOH solution was added to the mixture until the pH was 13-14. The product was extracted 4×20 mL with DCM and the organic layers combined, dried with MgSO$_4$ and evaporated. The product was dissolved in mixture MeOH (40 mL)/water (10 mL) and added to a flask followed by Sodium Borohydride (1.04 g, 27.47 mmol, 971.44 µL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na$_2$SO$_4$, filtered and evaporated to give 2-(3-fluorophenyl)-5-methyl-piperidine (2.3 g, 11.90 mmol, 43.32% yield) as a light-yellow oil.

$^1$H NMR (500 MHz, CDCl$_3$) δ 0.90 (d, 3H), 1.49 (m, 1H), 1.65 (m, 1H), 1.87 (m, 4H), 3.16 (m, 1H), 3.54 (m, 1H), 6.93 (m, 1H), 7.13 (m, 2H), 7.27 (m, 1H).

LCMS(ESI): [M+H]$^+$ m/z: calcd 193.2; found 194.2; Rt=0.878 min.

4H. Synthesis of 5-methyl-2-(Thiophen-2-yl)piperidine

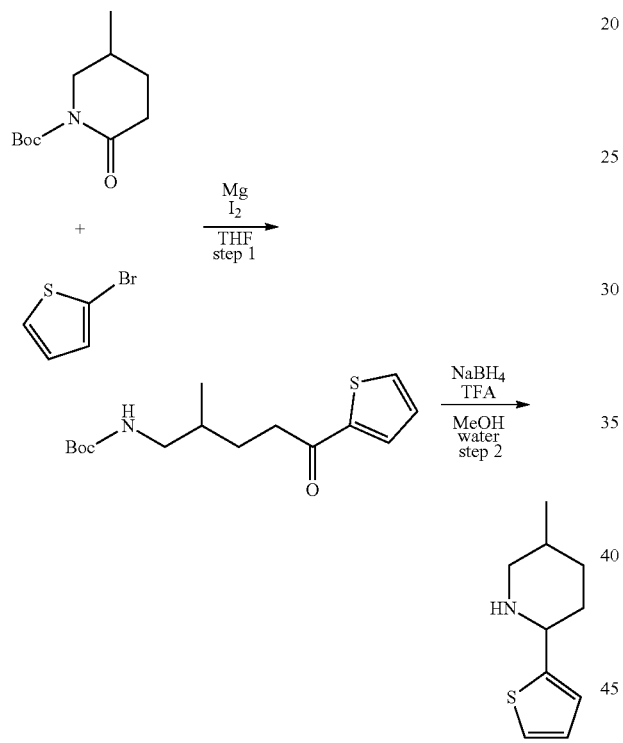

Step 1: Synthesis of tert-butyl (2-methyl-5-oxo-5-(thiophen-2-yl)pentyl)carbamate To a dry 2 necked flask was added magnesium (854.72 mg, 35.17 mmol, 491.22 µL), dry THF (50 mL) and 2-bromothiophene (5.73 g, 35.17 mmol, 3.41 mL) with stirring under Ar. Iodine (29.99 mg, 234.44 µmol) was added and the mixture was heated gently until it maintained its own reflux. When reflux had subsided external heating was applied to maintain reflux for a further 1 hour. tert-butyl 5-methyl-2-oxo-piperidine-1-carboxylate (5 g, 23.44 mmol) was added to a dry 3 necked round bottomed flask with a thermometer. Dry THF (50 mL) was added with stirring under Ar and the solution was cooled to −78° C. The Grignard reagent was added to the boc-lactam over 1 hour, maintaining the internal temperature below −70° C. The solution was warmed to room temperature and sat. NH$_4$Cl was added. The aqueous layer was extracted 3×50 mL with DCM and the organic layers combined, dried over Na$_2$SO$_4$, filtered and concentrated in vacuo. tert-butyl N-[2-methyl-5-oxo-5-(2-thienyl)pentyl]carbamate (5.1 g, crude) was obtained as a light-yellow oil and was used in the next step without further purification.

$^1$H NMR (500 MHz, CDCl$_3$) δ (ppm) 0.94 (d, 3H), 1.43 (s, 9H), 1.56 (m, 1H), 1.69 (m, 1H), 1.81 (m, 1H), 2.94 (m, 2H), 3.06 (m, 2H), 4.69 (m, 1H), 7.12 (t, 1H), 7.62 (d, 1H), 7.74 (d, 1H).

LCMS(ESI): [M-Boc]$^+$ m/z: calcd 197.4; found 198.2; Rt=1.421 min.

Step 2: Synthesis of 5-methyl-2-(thiophen-2-yl)piperidine

The tert-butyl N-[2-methyl-5-oxo-5-(2-thienyl)pentyl]carbamate (5.1 g, 17.15 mmol) was stirred in trifluoroacetic acid (9.78 g, 85.74 mmol, 6.61 mL) for 1 hr. TLC was used to check the reaction progress. 50% w/v NaOH solution was added to the mixture until the pH was 13-14. The product was extracted 4×20 mL with DCM and the organic layers combined, dried with MgSO$_4$ and evaporated. The product was dissolved in mixture MeOH (40 mL)/water (10 mL) and added to a flask followed by sodium borohydride (648.75 mg, 17.15 mmol, 606.31 µL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na$_2$SO$_4$, filtered and evaporated to give 5-methyl-2-(2-thienyl)piperidine (2.24 g, 12.36 mmol, 72.05% yield) as an light-yellow oil.

$^1$H NMR (400 MHz, CDCl$_3$) δ (ppm) 0.85 (d, 3H), 1.16 (m, 1H), 1.62 (m, 3H), 1.84 (d, 1H), 1.94 (d, 1H), 2.39 (t, 1H), 3.09 (d, 1H), 3.85 (d, 1H), 6.91 (m, 2H), 7.16 (m, 1H).

LCMS(ESI): [M]$^+$ m/z: calcd 181.3; found 182.2; Rt=1.579 min.

4I. The Synthesis of rac-(1S,4S,5R)-4-(2-thienyl)-3-azabicyclo[3.2.1]octane

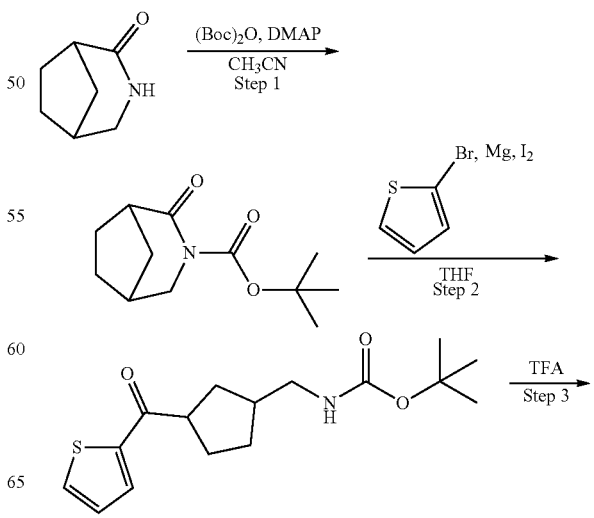

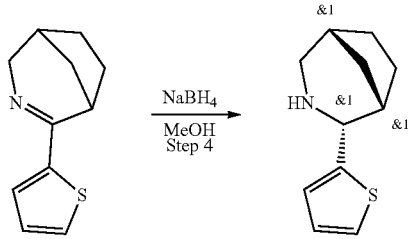

Step 1: Synthesis of tert-butyl 4-oxo-3-azabicyclo [3.2.]octane-3-carboxylate To a stirred solution of 3-azabicyclo[3.2.1]octan-4-one (2.00 g, 15.98 mmol) in CH$_3$CN (50 mL), Di-tert-butyl dicarbonate (3.84 g, 17.58 mmol, 4.03 mL) and DMAP (97.60 mg, 798.93 μmol) were added. The resulting reaction mixture was stirred at 25° C. for 12 hours. After 12 hours, the reaction mixture was concentrated under reduced pressure. Water (50 mL) was added to the residue and extracted with DCM (2*40 mL). The combined organic layer was washed with brine (50 mL), dried over Na$_2$SO$_4$ and evaporated in vacuo to obtain tert-butyl 4-oxo-3-azabicyclo[3.2.1]octane-3-carboxylate (3.45 g, 15.31 mmol, 95.84% yield) as yellow solid.

$^1$H NMR (CDCl$_3$, 500 MHz): δ (ppm) 1.51 (s, 9H), 1.63 (m, 2H), 1.91 (m, 3H), 2.00 (m, 1H), 2.56 (s, 1H), 2.85 (s, 1H), 3.39 (d, 1H), 3.55 (d, 1H). LCMS(ESI): [M+H]$^+$ m/z: calcd 225.2; found 170.2 (t-Bu cleaved product mass); Rt=1.053 min.

Step 2: Synthesis of tert-butyl N-[[3-(thiophene-2-carbonyl)Cyclopentyl]methyl]carbamate A dry 2 necked round bottomed flask (100 mL), fitted with a magnetic stir bar was charged with Magnesium (372.21 mg, 15.31 mmol) under argon atmosphere. Dry THF (50 mL) and 2-bromothiophene (2.50 g, 15.31 mmol, 1.49 mL) were added. Iodine (19.59 mg, 153.14 μmol) was added to the stirred solution and the resulting reaction mixture was heated gently until it maintained its own reflux. When reflux had subsided, external heating was applied to maintain reflux for an additional 1 hour. A separate dry 3 necked round bottomed flask (250 mL) fitted with a thermometer and a magnetic stir bar was charged with tert-butyl 4-oxo-3-azabicyclo[3.2.1]octane-3-carboxylate (3.45 g, 15.31 mmol). Dry THF (50 mL) was added under argon atmosphere and the solution was cooled to −78° C. Freshly prepared Grignard reagent was added to the resulting mixture dropwise during 30 minutes, maintaining the internal temperature below −70° C. The resulting reaction mixture was allowed to warm to room temperature and stirred at the same temperature for 1 hour. After 1 hour, the reaction mixture was quenched with saturated NH$_4$Cl solution and extracted with DCM (2*50 mL). The combined organic layer was dried over Na$_2$SO$_4$, filtered and concentrated under reduced pressure to obtain product tert-butyl N-[[3-(thiophene-2-carbonyl)cyclopentyl]methyl]carbamate (4.2 g, 13.57 mmol, 88.64% yield) as a pale yellow oil, which was used in the next step reaction without any further purification LCMS(ESI): [M+Boc]$^+$ m/z: calcd 309.2; found 210.2; Rt=1.454 min.

Step 3: Synthesis of 4-(2-thienyl)-3-azabicyclo [3.2.1]oct-3-ene tert-butyl N-[[3-(thiophene-2-carbonyl)cyclopentyl] methyl]carbamate (4.20 g, 13.57 mmol) was dissolved in Trifluoroacetic acid (15 g, 131.55 mmol, 10.14 mL). The resulting reaction mixture was stirred at 25° C. for 12 hours. After 12 hours, the reaction mixture was concentrated under reduced pressure and the obtained residue was dissolved in ice cold water. 5N aqueous solution of NaOH solution was added till pH=9 and extracted with DCM (3*50 mL). The organic layer was washed with brine (50 mL), dried over Na$_2$SO$_4$ and evaporated in vacuo to obtain 4-(2-thienyl)-3-azabicyclo[3.2.1]oct-3-ene (2.3 g, 12.02 mmol, 88.58% yield) as a red oil. The crude product was used for the next step reaction without any further purification.

$^1$H NMR (CDCl$_3$, 400 MHz): δ (ppm) 1.62 (s, 2H), 1.88 (m, 4H), 2.29 (s, 1H), 3.18 (s, 1H), 3.65 (d, 1H), 3.92 (d, 1H), 7.01 (t, 1H), 7.32 (m, 2H). LCMS(ESI): [M+H]$^+$ m/z: calcd 191.1; found 192.0; Rt=0.724 min.

Step 4: Synthesis of rac-(1S,4S,5R)-4-(2-thienyl)-3-azabicyclo[3.2.1]octane

To a stirred solution of 4-(2-thienyl)-3-azabicyclo[3.2.1] oct-3-ene (2.30 g, 12.02 mmol) in MeOH (50 mL) was added Sodium Borohydride (909.76 mg, 24.05 mmol) portionwise at 0° C. The resulting mixture was stirred at 25° C. for 2 hours. After 2 hours, the reaction mixture was concentrated under reduced pressure. The obtained residue was diluted with water (50 mL) and extracted with DCM (2*50 mL). The combined organic layer was washed with brine, dried over Na$_2$SO$_4$ and evaporated in vacuo to obtain crude product. MTBE (30 mL) was added to the crude product and the suspension was filtered. The filtrate was evaporated in vacuo to obtain rac-(1S,4S,5R)-4-(2-thienyl)-3-azabicyclo [3.2.1]octane (1.9 g, 9.83 mmol, 81.75% yield) as a red oil.

$^1$H NMR (CDCl$_3$, 500 MHz): δ (ppm) 1.49 (m, 1H), 1.68 (m, 5H), 2.14 (s, 1H), 2.31 (s, 1H), 2.82 (dd, 1H), 2.95 (d, 1H), 4.13 (s, 1H), 6.91 (d, 1H), 6.97 (m, 1H), 7.18 (d, 1H). LCMS(ESI): [M+H]$^+$ m/z: calcd 193.1; found 194.2; Rt=0.780 min.

4J. The Synthesis of rac-(1R,4R,5S)-4-phenyl-3-azabicyclo[3.2.1]octane

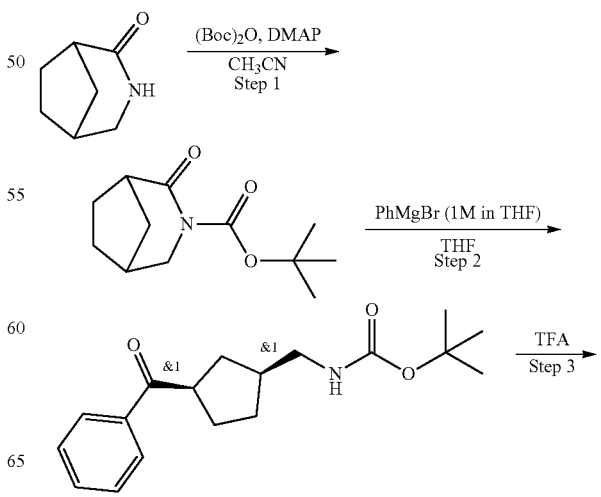

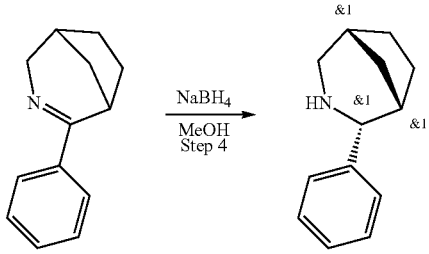

Step 1 Preparation of Tert-butyl 4-oxo-3-azabicyclo[3.2.]octane-3-carboxylate is Given in the Synthesis of Intermediate 41

Step 2: Synthesis of tert-butyl N-[(3-benzylcyclopentyl)methyl]carbamate

A dry 3 necked round bottomed flask (250 mL) fitted with a thermometer and a magnetic stir bar was charged with tert-butyl 4-oxo-3-azabicyclo[3.2.1]octane-3-carboxylate (4.5 g, 19.97 mmol). Dry THF (80 mL) was added under Argon atmosphere and the resulting solution was cooled to −78° C. Grignard reagent Phenylmagnesium bromide (1 M in THF, 20.12 g, 19.97 mmol, 20.12 mL) was added dropwise, maintaining the internal temperature below −70° C. The resulting reaction mixture was allowed to warm to room temperature and stirred at the same temperature for 1 hour. After 1 hour, the reaction mixture was quenched with saturated NH₄Cl solution and extracted with DCM (2*50 mL). The combined organic layers was dried over Na₂SO₄, filtered and concentrated in vacuo to give tert-butyl N-[(3-benzylcyclopentyl)methyl]carbamate (5.5 g, 18.13 mmol, 90.76% yield) as a pale yellow oil. The crude product was used for the next step without any further purification.

LCMS(ESI): [M+Boc]⁺ m/z: calcd 303.2; found 204.2; Rt=1.388 min.

Step 3: Synthesis of 4-phenyl-3-azabicyclo[3.2.1]oct-3-ene tert-butyl N-[(3-benzylcyclopentyl)methyl]carbamate (5.5 g, 18.13 mmol) was dissolved in Trifluoroacetic acid (2.07 g, 18.13 mmol, 1.40 mL). The resulting mixture was stirred at 25° C. for 2 hours. After 2 hours, the reaction mixture was concentrated under reduced pressure and the obtained residue was dissolved in ice cold water. pH was adjusted to 9 with 5N aqueous NaOH solution and extracted with DCM (3*50 mL). The combined organic layer was washed with brine (50 mL), dried over Na₂SO₄ and evaporated in vacuo to obtain 4-phenyl-3-azabicyclo[3.2.1]oct-3-ene (2.5 g, 13.49 mmol, 74.44% yield) as a yellow oil. This product was used for the next step reaction without any further purification.

¹H NMR (CDCl₃, 500 MHz): δ (ppm) 1.67 (m, 2H), 1.84 (d, 1H), 1.98 (m, 3H), 2.33 (m, 1H), 3.24 (m, 1H), 3.74 (d, 1H), 3.99 (dd, 1H), 7.39 (m, 3H), 7.77 (m, 2H). LCMS(ESI): [M+H]⁺ m/z: calcd 185.1; found 186.2; Rt=0.709 min.

Step 4: Synthesis of rac-(1R,4R,5S)-4-phenyl-3-azabicyclo[3.2]octane

To a stirred solution of 4-phenyl-3-azabicyclo[3.2.1]oct-3-ene (2.5 g, 13.49 mmol) in MeOH (40 mL) was added Sodium Borohydride (1.02 g, 26.99 mmol) portionwise at 0° C. The resulting reaction mixture was stirred at 25° C. for 2 hours. After 2 hours, the reaction mixture was concentrated under reduced pressure. The obtained residue was diluted with water (50 mL) and extracted with DCM (2*50 mL). The combined organic phase was washed with brine, dried over Na₂SO₄, filtered and evaporated in vacuo to obtain crude product. MTBE (30 mL) was added to the crude product and the suspension was filtered. The filtrate was evaporated in vacuo to obtain rac-(1R,4R,5S)-4-phenyl-3-azabicyclo[3.2.1]octane (2.1 g, 11.21 mmol, 83.10% yield) as a light-yellow solid. The structure was confirmed by 2D NMR.

¹H NMR (CDCl₃, 500 MHz): δ (ppm) 1.32 (m, 2H), 1.66 (m, 3H), 1.73 (m, 2H), 2.17 (s, 1H), 2.21 (t, 1H), 2.89 (dd, 1H), 2.96 (d, 1H), 3.91 (s, 1H), 7.23 (t, 1H), 7.33 (t, 2H), 7.40 (d, 2H).

LCMS(ESI): [M+H]⁺ m/z: calcd 187.2; found 188.2; Rt=0.832 min.

4K. Synthesis of (2R,6R)-2-methyl-6-phenyl-piperidine and methyl 2-[(2R,6R)-2-methyl-6-phenyl-1-piperidyl]-2-oxo-acetate

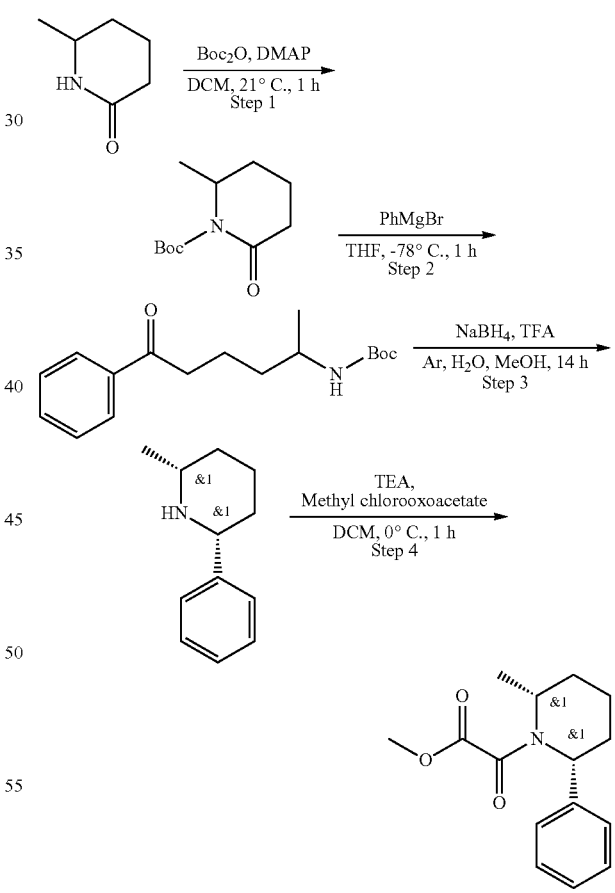

Step 1: The Synthesis of tert-butyl 2-methyl-6-oxo-piperidine-1-carboxylate

To the mixture of 6-methylpiperidin-2-one (7.3 g, 64.51 mmol) and DMAP (394.07 mg, 3.23 mmol) in DCM (150 mL), di-tert-butyl dicarbonate (14.78 g, 67.74 mmol, 15.55 mL) was added portionwise at 21° C. The obtained mixture was stirred for 1 h. Then, the resulting solution was washed with 10% aq. HCl and brine, dried over $Na_2SO_4$ and evaporated to dryness to afford tert-butyl 2-methyl-6-oxo-piperidine-1-carboxylate (13 g, crude, 94.47% yield) as a yellow oil. $^1$H NMR (400 MHz, $CDCl_3$) δ 1.25 (d, 3H), 1.50 (s, 9H), 1.65 (m, 2H), 1.89 (m, 2H), 2.46 (m, 2H), 4.26 (m, 1H). LCMS(ESI): [M-Boc]$^+$ m/z: calcd 113.1; found 114.2; Rt=0.765 min.

Step 2: Synthesis of tert-butyl N-(1-methyl-5-oxo-5-phenyl-pentyl)carbamate

Phenyl magnesium bromide (132.62 g, 109.72 mmol, 135.33 mL) was portionwise added to the solution of tert-butyl 2-methyl-6-oxo-piperidine-1-carboxylate (13 g, 60.95 mmol) in THF (20 mL) over 1 hour at −78° C., maintaining the internal temperature below −70° C. The resulting solution was warmed to room temperature and sat. $NH_4Cl$ was added. The aqueous layer was extracted 3*50 mL with DCM and the organic layers combined, dried over $Na_2SO_4$, filtered and concentrated in vacuo. tert-butyl N-(1-methyl-5-oxo-5-phenyl-pentyl)carbamate (16.2 g, 55.60 mmol, 91.21% yield) was obtained as a light-yellow oil and was used in the next step without further purification. $^1$H NMR (500 MHz, $CDCl_3$) δ 1.14 (d, 3H), 1.53 (s, 9H), 1.80 (m, 4H), 3.01 (m, 2H), 3.70 (m, 2H), 7.45 (m, 2H), 7.56 (m, 1H), 7.96 (d, 2H). LCMS(ESI): [M-Boc]$^+$ m/z: calcd 191.2; found 192.2; Rt=1.492 min.

Step 3: Synthesis of (2R,6R)-2-methyl-6-phenyl-piperidine

The tert-butyl N-(1-methyl-5-oxo-5-phenyl-pentyl)carbamate (16.2 g, 55.60 mmol) was stirred in trifluoroacetic acid (31.70 g, 277.98 mmol, 21.42 mL) for 1 hr. TLC was used to check the reaction progress. 50% w/v NaOH solution was added to the mixture until the pH was 13-14. The product was extracted 4*20 mL with DCM and the organic layers combined, dried with $MgSO_4$ and evaporated. The product was dissolved in mixture Water (10 mL)/MeOH (50 mL) and added to a flask followed by Sodium Borohydride (2.10 g, 55.60 mmol, 1.97 mL). The mixture was stirred under Ar overnight. The mixture was acidified with 1-2 M HCl until the pH was 1-3 and left for 30 minutes. NaOH solution was then added until the pH was 13-14 and the product was extracted with DCM (4*100 mL), the organic layers were combined, dried with $Na_2SO_4$, filtered and evaporated. The residue was purified by CC (Companion combiflash; 120 g $SiO_2$; chloroform/acetonitrile with acetonitrile from 0 to 18%, flow rate=85 mL/min, Rv=5-8 cv.) to give (2R,6R)-2-methyl-6-phenyl-piperidine (2.4 g, 13.69 mmol, 24.63% yield) as a light-yellow oil. $^1$H NMR (500 MHz, $CDCl_3$) δ 1.11 (d, 3H), 1.12 (m, 1H), 1.50 (m, 2H), 1.64 (m, 2H), 1.76 (m, 1H), 1.88 (m, 1H), 2.82 (m, 1H), 3.66 (m, 1H), 7.23 (m, 2H), 7.31 (m, 1H), 7.39 (m, 2H). LCMS(ESI): [M+H]$^+$ m/z: calcd 175.1; found 176.2; Rt=0.660 min.

Step 4: Synthesis of Methyl 2-[(2R,6R)-2-methyl-6-phenyl-1-piperidyl]-2-oxo-acetate To a solution of (2R,6R)-2-methyl-6-phenyl-piperidine (0.5 g, 2.85 mmol) and triethylamine (346.40 mg, 3.42 mmol, 477.14 μL) in DCM (25 mL), methyl 2-chloro-2-oxo-acetate (384.43 mg, 3.14 mmol) was added at 0° C. After stirring at room temperature for 1 hr, the resulting mixture were filtered and evaporated to dryness to afford methyl 2-[(2R,6R)-2-methyl-6-phenyl-1-piperidyl]-2-oxo-acetate (0.74 g, 2.83 mmol, 99.27% yield) as a yellow solid, which was used in the next step without further purification. $^1$H NMR (500 MHz, $CDCl_3$) δ 0.83 (m, 3H), 1.62 (m, 2H), 1.88 (m, 2H), 2.56 (m, 1H), 3.86 (m, 1H), 3.92 (s, 3H), 4.87 (m, 1H), 5.90 (m, 1H), 7.37 (m, 5H). LCMS(ESI): [M+H]$^+$ m/z: calcd 261.1; found 262.2; Rt=1.374 min.

4L. The Synthesis of Synthesis of N,N-dimethyl-3-(piperidin-2-yl)aniline

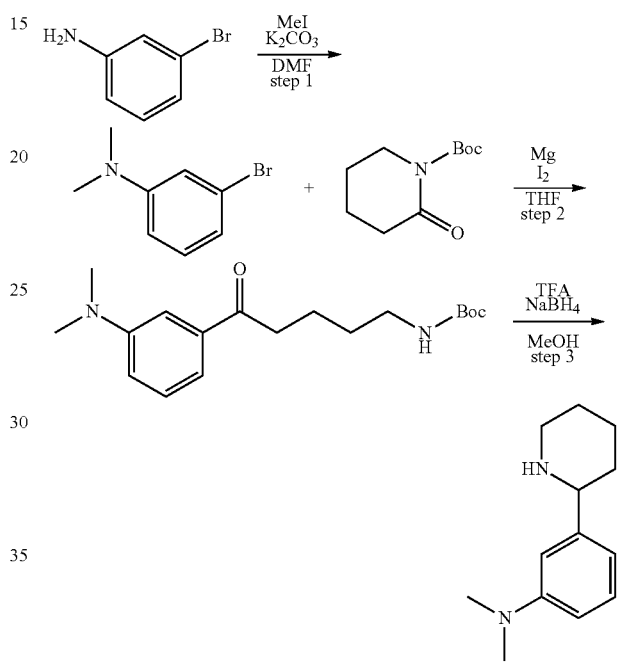

Step 1: Synthesis of 3-bromo-N,N-dimethylaniline

Iodomethane (3.63 g, 25.58 mmol, 1.59 mL) was added to the mixture of 3-bromoaniline (2 g, 11.63 mmol, 1.27 mL), potassium carbonate—granular (3.54 g, 25.58 mmol, 1.54 mL), and DMF (10 mL) and the resulting mixture was heated at 75° C. for 12 hr. The mixture was poured into aqueous $NaHCO_3$ solution and extracted with ethyl acetate. The organic layer was washed with brine, dried over sodium sulfate and concentrated in vacuo to obtain 3-bromo-N,N-dimethyl-aniline (2 g, 10.00 mmol, 85.98% yield).
$^1$H NMR (400 MHz, $CDCl_3$) δ (ppm) 2.96 (s, 6H), 6.60 (d, 1H), 6.79 (d, 1H), 6.81 (s, 1H), 7.06 (t, 1H).
LCMS(ESI): [M]$^+$ m/z: calcd 200.1; found 201.2; Rt=1.486 min.

Step 2: Synthesis of tert-butyl (5-(3-(dimethylamino)phenyl)-5-oxopentyl)carbamate 3-bromo-N,N-dimethyl-aniline (2 g, 10.00 mmol) was added to the mixture of THF (20 mL) and Mg (242.96 mg, 10.00 mmol, 139.63 μL) under argon atmosphere. Iodine (2.54 mg, 10.00 μmol) was added thereto and the resulting mixture was heated to reflux for 1 h. The resulting mixture was cooled to rt and added dropwise to the solution of tert-butyl 2-oxopiperidine-1-carboxylate (1.99 g, 10.00 mmol) in THF (20 mL) at −78° C. The resulting mixture was left to warm to rt and then poured into aq. NH₄Cl solution. The resulting mixture was extracted with EtOAc (2×40 ml). The combined organic extracts were washed with brine, dried over Na₂SO₄ and evaporated to obtain tert-butyl N-[5-[3-(dimethylamino)phenyl]-5-oxo-pentyl]carbamate (1.8 g, crude), which was used in next step without purification.

¹H NMR (500 MHz, DMSO-d₆) δ (ppm) 1.19 (m, 2H), 1.42 (s, 9H), 1.97 (m, 2H), 2.92 (s, 6H), 2.98 (m, 4H), 6.68 (m, 2H), 7.21 (m, 2H).

LCMS(ESI): [M]⁺ m/z: calcd 320.4; found 321.2; Rt=1.470 min.

Step 3: Synthesis of N,N-dimethyl-3-(piperidin-2-yl)aniline tert-butyl N-[5-[3-(dimethylamino)phenyl]-5-oxo-pentyl] carbamate (1.8 g, 5.62 mmol) was dissolved in trifluoroacetic acid (12.81 g, 112.35 mmol, 8.66 mL) and the resulting mixture was stirred for 1 hr. 50% aq·NaOH solution was added thereto to pH 11-12. The resulting mixture was extracted with DCM (4×40 ml) the combined organic layer was evaporated to dryness. The residue was redissolved in MeOH (15 mL) and sodium borohydride (212.53 mg, 5.62 mmol, 198.62 μL) was added. The resulting mixture was stirred at 20° C. for 12 hr and evaporated. 50% aq·NaOH solution was added to the residue. The resulting mixture was extracted with DCM (4×40 ml) the combined organic layer was evaporated to dryness to obtain N,N-dimethyl-3-(2-piperidyl)aniline (0.4 g, crude), which was used in next step without purification.

¹H NMR (400 MHz, DMSO-d₆) δ (ppm) 1.32 (m, 3H), 1.53 (m, 1H), 1.66 (m, 1H), 1.78 (m, 1H), 2.67 (m, 1H), 2.86 (s, 6H), 3.04 (m, 1H), 3.44 (m, 1H), 6.68 (m, 2H), 7.21 (m, 2H).

LCMS(ESI): [M]⁻ m/z: calcd 204.3; found 205.2; Rt=0.744 min.

4M. Synthesis of 5,5-dimethyl-2-phenyl-piperidine

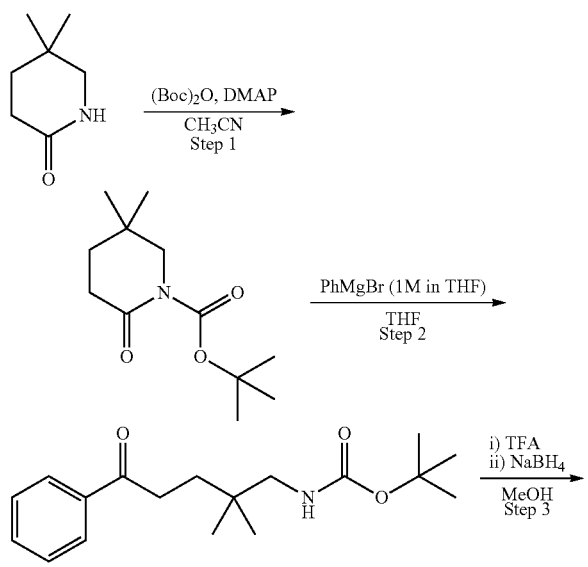

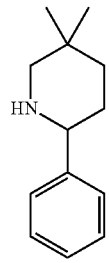

Step 1: Synthesis of tert-butyl 5,5-dimethyl-2-oxo-piperidine-1-carboxylate

To a stirred solution of 5,5-dimethylpiperidin-2-one (1 g, 7.86 mmol) and 4-dimethylaminopyridine (9.61 mg, 78.63 μmol) in CH₃CN (20 mL) was added Di-tert-butyl dicarbonate (1.89 g, 8.65 mmol, 1.98 mL). The resulting reaction mixture was stirred at 20° C. for 12 hours. After 12 hours, the reaction mixture was concentrated under reduced pressure to obtain tert-butyl 5,5-dimethyl-2-oxo-piperidine-1-carboxylate (1.5 g, 6.60 mmol, 83.93% yield). The crude product was used for the next step reaction without any further purification.

¹H NMR (CDCl₃, 400 MHz): δ (ppm) 1.03 (s, 6H), 1.50 (s, 9H), 1.57 (t, 2H), 2.46 (t, 2H), 3.35 (s, 2H). LCMS(ESI): [M+H]⁺ m/z: calcd 227.2; found 172.2 (t-Bu cleaved product mass); Rt=1.314 min.

Step 2: Synthesis of tert-butyl N-(2,2-dimethyl-5-oxo-5-phenyl-pentyl)carbamate To a stirred solution of tert-butyl 5,5-dimethyl-2-oxo-piperidine-1-carboxylate (1.5 g, 6.60 mmol) in THF (20 mL) at −78° C., Phenylmagnesium bromide (1 M in THF, 1.20 g, 6.60 mmol, 6.6 mL) was added dropwise under argon atmosphere. The resulting reaction mixture was allowed to warm to room temperature and stirred for 12 hours at the same temperature. After 12 hours, the reaction mixture was quenched with saturated aq NH₄Cl solution and extracted with EtOAc (2×50 mL). The combined organic phase was dried over Na₂SO₄, filtered and evaporated in vacuo to obtain tert-butyl N-(2,2-dimethyl-5-oxo-5-phenyl-pentyl) carbamate (1.3 g, 4.26 mmol, 64.50% yield). The crude product was used for the next step reaction without any further purification.

¹H NMR (DMSO-d₆, 400 MHz): δ (ppm) 0.82 (s, 6H), 1.35 (s, 9H), 1.47 (m, 2H), 2.81 (d, 2H), 2.97 (t, 2H), 3.30 (brs, 1H), 7.51 (t, 2H), 7.62 (m, 1H), 7.96 (d, 2H). LCMS (ESI): [M+Boc]⁺ m/z: calcd 305.2; found 206.2; Rt=1.541 min.

Step 3: Synthesis of 5,5-dimethyl-2-phenyl-piperidine tert-butyl N-(2,2-dimethyl-5-oxo-5-phenyl-pentyl)carbamate (1.3 g, 4.26 mmol) was dissolved in Trifluoroacetic acid (4.85 g, 42.57 mmol, 3.28 mL) and the resulting reaction mixture was stirred for 1 hour at room temperature. After 1 hour, 50% aq·NaOH solution was added to the reaction mixture till pH=11-12. The resulting mixture was extracted with DCM (4×20 mL). The combined organic phase was dried over Na₂SO₄ and evaporated to dryness. The obtained residue was dissolved in MeOH (20 mL) and Sodium Borohydride (161.04 mg, 4.26 mmol) was added portionwise. The resulting mixture was stirred at 20° C. for 1 hour. After 1 hour, the reaction mixture was concentrated and the obtained residue was diluted with 50% aq·NaOH solution. The resulting mixture was extracted with DCM (4×20 mL). The combined organic phase was dried over Na$_2$SO$_4$, filtered and concentrated under reduced pressure obtain 5,5-dimethyl-2-phenyl-piperidine (0.1 g, 528.27 µmol, 12.41% yield). The crude product was used for the next step reaction without any further purification.

LCMS(ESI): [M+H]$^+$ m/z: calcd 189.2; found 190.2; Rt=0.817 min.

4N. The Synthesis of 3,5-dimethyl-6-phenyl-2,3,4,5-tetrahydropyridine

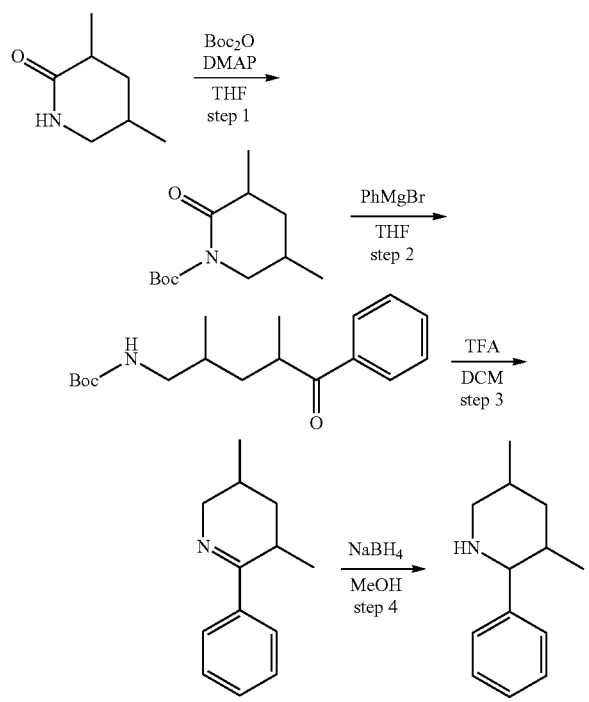

Step 1: Synthesis of tert-butyl 3,5-dimethyl-2-oxopiperidine-1-carboxylate

Di-tert-butyl dicarbonate (20.59 g, 94.35 mmol, 21.65 mL) was added to a solution of 3,5-dimethylpiperidin-2-one (10 g, 78.63 mmol) and 4-dimethylamino-pyridine (480.29 mg, 3.93 mmol) in THF (100 mL). Resulting mixture was stirred at 40° C. for 3 hr. Then, water (10 ml) was added. When CO$_2$ evolution ceased, mixture was diluted with MTBE (100 ml) and washed successively with 2% NaHSO$_4$ (80 ml) and brine (100 ml). Then, it was dried over Na$_2$SO$_4$ and evaporated under reduced pressure, affording tert-butyl 3,5-dimethyl-2-oxo-piperidine-1-carboxylate (17.15 g, 75.45 mmol, 95.96% yield).

$^1$H NMR (500 MHz, CDCl$_3$) δ (ppm) 1.01 (d, 3H), 1.20 (d, 3H), 1.52 (s, 9H), 1.64 (m, 1H), 1.98 (m, 1H), 2.04 (m, 1H), 2.48 (m, 1H), 3.18 (m, 1H), 3.85 (m, 1H). GCMS: [M]: calcd 227.2; found 227.2; Rt=7.992 min.

Step 2: Synthesis of tert-butyl (2,4-dimethyl-5-oxo-5-phenylpentyl)carbamate Bromo(phenyl)magnesium (100.32 g, 83.00 mmol, 102.37 mL) was added dropwise to a cooled to −75° C. solution of tert-butyl 3,5-dimethyl-2-oxo-piperidine-1-carboxylate (17.15 g, 75.45 mmol) in THF (150 mL) under argon. After addition was complete, cooling bath was removed and mixture was slowly warmed up to 20° C. Then, saturated NH$_4$Cl (60 ml) and MTBE (150 ml) were added. Organic layer was separated and washed successively with water (100 ml) and brine (100 ml), dried over Na$_2$SO$_4$ and concentrated under reduced pressure, affording tert-butyl N-(2,4-dimethyl-5-oxo-5-phenyl-pentyl)carbamate (20.7 g, 67.78 mmol, 89.83% yield).

$^1$H NMR (500 MHz, CDCl$_3$) δ (ppm) 0.87 (d, 3H), 0.95 (m, 1H), 1.22 (d, 3H), 1.49 (s, 9H), 1.61 (m, 1H), 1.77 (m, 1H), 1.96 (m, 1H), 3.02 (m, 1H), 3.53 (m, 1H), 4.64 (m, 1H), 7.48 (t, 2H), 7.57 (t, 1H), 7.97 (d, 2H). L CMS(ESI): [M-Boc]$^+$ m/z: calcd 205.2; found 206.2; Rt=1.479 min.

Step 3: Synthesis of 3,5-dimethyl-6-phenyl-2,3,4,5-tetrahydropyridine

Trifluoroacetic acid (77.28 g, 677.78 mmol, 52.22 mL) was added to a solution of tert-butyl N-(2,4-dimethyl-5-oxo-5-phenyl-pentyl)carbamate (20.7 g, 67.78 mmol) in DCM (50 mL). Resulting mixture was stirred at 20° C. for 2 hr. Then, solvents were removed under reduced pressure and residue was partitioned between 5% aq·NaOH (150 ml) and DCM (250 ml). DCM layer was separated, dried over Na$_2$SO$_4$ and evaporated in vacuo, affording 3,5-dimethyl-6-phenyl-2,3,4,5-tetrahydropyridine (12.1 g, 64.61 mmol, 95.33% yield).

$^1$H NMR (500 MHz, CDCl$_3$) δ (ppm) 0.94 (d, 3H), 1.11 (d, 3H), 1.59 (m, 1H), 1.74 (m, 1H), 1.94 (m, 1H), 3.12 (m, 1H), 3.25 (m, 1H), 3.99 (m, 1H), 7.37 (t, 2H), 7.52 (t, 1H), 7.87 (d, 2H). LCMS(ESI): [M]$^+$ m/z: calcd 187.2; found 188.2; Rt=0.863 min.

Step 4: Synthesis of 3,5-dimethyl-2-phenylpiperidine

Sodium borohydride (4.89 g, 129.22 mmol, 4.57 mL) was added to a solution of 3,5-dimethyl-6-phenyl-2,3,4,5-tetra-hydropyridine (12.1 g, 64.61 mmol) in methanol (150 mL) portionwise during 15 minutes. Resulting solution was stirred at 20° C. for 1 hr. Then, solvent was removed under reduced pressure and residue was partitioned between water (100 ml) and MTBE (200 ml). Organic layer was separated, dried over Na$_2$SO$_4$ and evaporated in vacuo, affording 3,5-dimethyl-2-phenyl-piperidine (11.2 g, 59.17 mmol, 91.58% yield). Obtained material was used in next steps without purification. Residue (10.5 g) was purified by column chromatography (80 g SiO$_2$, hexane-MTBE), affording 1.9 g 85% single-isomer fraction with proved configuration.

$^1$H NMR (500 MHz, CDCl$_3$) δ (ppm) 0.76 (d, 3H), 0.87 (d, 3H), 1.25 (m, 1H), 1.45 (m, 1H), 1.75 (m, 1H), 1.88 (m, 1H), 2.03 (m, 1H), 2.39 (t, 1H), 3.18 (d, 1H), 3.86 (m, 1H), 7.30 (m, 5H).

LCMS(ESI): [M]$^+$ m/z: calcd 189.3; found 190.2; Rt=0.913 min.

4O. The Synthesis of Synthesis of 2-(Benzothiophen-3-yl)piperidine

Step 1: The Synthesis of tert-butyl 6-(benzothiophen-3-yl)-3,4-dihydro-2H-pyridine-1-carboxylate A suspension of tert-butyl 6-(trifluoromethylsulfonyloxy)-3,4-dihydro-2H-pyridine-1-carboxylate (9 g, 27.17 mmol), benzothiophen-3-ylboronic acid (4.84 g, 27.17 mmol), and Sodium carbonate (8.64 g, 81.50 mmol, 3.41 mL) in Dioxane (100 mL) and Water (20 mL) was degassed and refilled with Ar three time. To this solution, [1,1'-Bis(diphenylphosphino)ferrocene]dichloropalladium(II), complex with dichloromethane (1.11 g, 1.36 mmol) was added. The resulting mixture was degassed, refilled with Ar and stirred at 60° C. for 12 hr. The precipitate was filtered off, washed with dioxane (50 ml). The solvent was evaporated in vacuo and residue was taken up with water 150 ml and extracted with EtOAc (2*100 ml). The combined organic layer was washed with brine (100 ml), dried over $Na_2SO_4$ and evaporated to obtain crude product (9 g). The crude product was purified by gradient chromatography ($SiO_2$, hexane-MTBE) to obtain tert-butyl 6-(benzothiophen-3-yl)-3,4-dihydro-2H-pyridine-1-carboxylate (5.0 g, 15.85 mmol, 58.35% yield).

$^1$H NMR (500 MHz, DMSO-$d_6$) δ 077 (s, 9H), 1.90 (m, 2H), 2.30 (m, 2H), 3.76 (m, 2H), 5.35 (m, 1H), 7.32 (m, 3H), 7.69 (d, 1H), 7.85 (d, 1H).

LCMS(ESI): [M-$^t$Bu]$^+$ m/z: calcd 259.0; found 260.0; Rt=1.711 min.

Step 2: The Synthesis of 6-(Benzothiophen-3-yl)-2,3,4,5-tetrahydropyridine tert-butyl 6-(benzothiophen-3-yl)-3,4-dihydro-2H-pyridine-1-carboxylate (5 g, 15.85 mmol) was dissolved in trifluoroacetic acid (18.07 g, 158.51 mmol, 12.21 mL). The resulting mixture was stirred at 25° C. for 2 hr (to the end of gas evolution). The pH of the solution was adjusted to 8 with 10% NaOH solution and extracted with DCM (3*70 ml). The combined organic layer was washed with brine (50 ml), dried over $Na_2SO_4$ and evaporated in vacuo to obtain 6-(benzothiophen-3-yl)-2,3,4,5-tetrahydropyridine (3 g, 13.93 mmol, 87.90% yield).

$^1$H NMR (400 MHz, DMSO-$d_6$) δ 1.60 (m, 2H), 1.76 (m, 2H), 2.66 (m, 2H), 3.79 (m, 2H), 7.36 (m, 2H), 7.95 (m, 1H), 8.15 (s, 1H), 8.82 (d, 1H).

LCMS(ESI): [M+H]$^+$ m/z: calcd 215.1; found 216.0; Rt=0.866 min.

Step 3: The Synthesis of 2-(Benzothiophen-3-yl)piperidine

To a solution of 6-(benzothiophen-3-yl)-2,3,4,5-tetrahydropyridine (3 g, 13.93 mmol) in MeOH (60 mL), Sodium Borohydride (1.05 g, 27.87 mmol, 985.29 µL) was added portionwise at 0° C. The resulting mixture was stirred at ambient temperature for 2 hr and evaporated. The residue was taken up with water (50 ml) and extracted with DCM (3*50 ml). The combined organic layer was washed with brine (2*40 ml), dried over $Na_2SO_4$ and evaporated in vacuo to obtain 2-(benzothiophen-3-yl)piperidine (2.8 g, 12.88 mmol, 92.47% yield).

$^1$H NMR (400 MHz, DMSO-$d_6$) δ 1.45 (m, 4H), 1.85 (m, 2H), 2.33 (m, 1H), 2.71 (m, 1H), 3.06 (m, 1H), 3.95 (m, 1H), 7.35 (m, 2H), 7.50 (s, 1H), 7.95 (m, 2H).

LCMS(ESI): [M+H]$^+$ m/z: calcd 217.1; found 218.2; Rt=0.854 min.

4P. The Synthesis of Synthesis of 5-methyl-2-(naphthalen-2-yl)piperidine

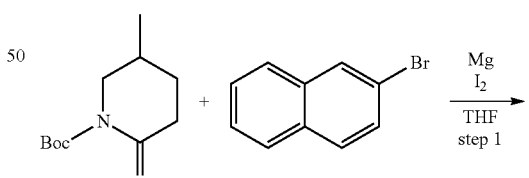

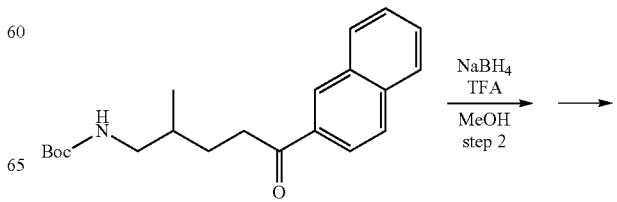

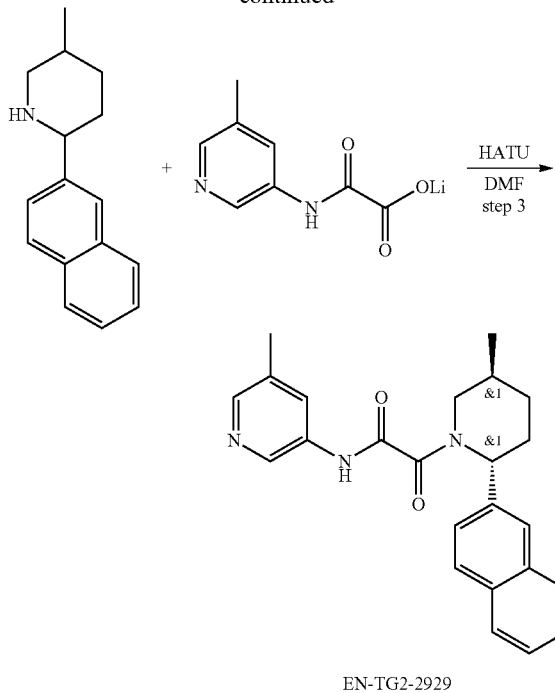

EN-TG2-2929

Step 1: Synthesis of tert-butyl (2-methyl-5-(naphthalen-2-yl)-5-oxopentyl)carbamate tert-butyl 5-methyl-2-oxo-piperidine-1-carboxylate (3 g, 14.07 mmol) was added to the mixture of THF (50 mL) and magnesium (341.89 mg, 14.07 mmol, 196.49 μL) under argon atmosphere. Iodine (17.85 mg, 70.33 μmol) was added thereto and the resulting mixture was heated to reflux for 1 h. The resulting mixture was cooled to rt and added dropwise to the solution of 2-bromonaphthalene (2.91 g, 14.07 mmol) in THF (50 mL) at −78° C. The resulting mixture was left to warm to rt and then poured into aq. NH$_4$Cl solution. The resulting mixture was extracted with EtOAc (2×40 ml). The combined organic extracts were washed with brine, dried over Na$_2$SO$_4$ and evaporated to obtain tert-butyl N-[2-methyl-5-(2-naphthyl)-5-oxo-pentyl]carbamate (5 g, crude), which was used in next step without purification.

$^1$H NMR (400 MHz, DMSO-d$_6$) δ (ppm) 0.86 (d, 3H), 1.44 (s, 9H), 1.78 (m, 3H), 2.89 (m, 2H), 3.15 (m, 3H), 7.51 (m, 2H), 7.89 (m, 2H), 7.99 (m, 2H), 8.69 (m, 1H).

LCMS(ESI): [M-Boc]$^+$ m/z: calcd 241.2; found 242.2; Rt=1.524 min.

Step 2: Synthesis of 5-methyl-2-(naphthalen-2-yl)piperidine tert-butyl N-[2-methyl-5-(2-naphthyl)-5-oxo-pentyl]carbamate (5 g, 14.64 mmol) was dissolved in trifluoroacetic acid (16.70 g, 146.44 mmol, 11.28 mL) and the resulting mixture was stirred for 1 hr. 50% aq·NaOH solution was added thereto to pH 11-12. The resulting mixture was extracted with DCM (4×40 ml). The combined organic layer was evaporated to dryness. The residue was redissolved in MeOH (50 mL) and sodium borohydride (554.01 mg, 14.64 mmol, 517.77 μL) was added. The resulting mixture was stirred at 20° C. for 12 hr and evaporated. 50% aq·NaOH solution was added to the residue. The resulting mixture was extracted with DCM (4×40 ml) the combined organic layer was evaporated to dryness to obtain 5-methyl-2-(2-naphthyl)piperidine (0.5 g, 2.22 mmol, 15.15% yield) which was used in next step without purification.

$^1$H NMR (500 MHz, DMSO-d$_6$) δ (ppm) 0.86 (d, 3H), 1.15 (m, 1H), 1.41 (m, 1H), 1.62 (m, 1H), 1.75 (m, 2H), 2.31 (t, 1H), 2.40 (m, 1H), 3.05 (d, 1H), 3.62 (d, 1H), 7.51 (m, 3H), 7.91 (m, 4H).

LCMS(ESI): [M]$^+$ m/z: calcd 225.3; found 226.2; Rt=1.473 min.

4Q. The Synthesis of rac-2-[(2R,3R,6S)-2,3-dimethyl-6-phenyl-1-piperidyl]-N-(5-methyl-3-pyridyl)-2-oxo-acetamide and rac-2-[(2S,3R,6S)-2,3-dimethyl-6-phenyl-1-piperidyl]-N-(5-methyl-3-pyridyl)-2-oxo-acetamide

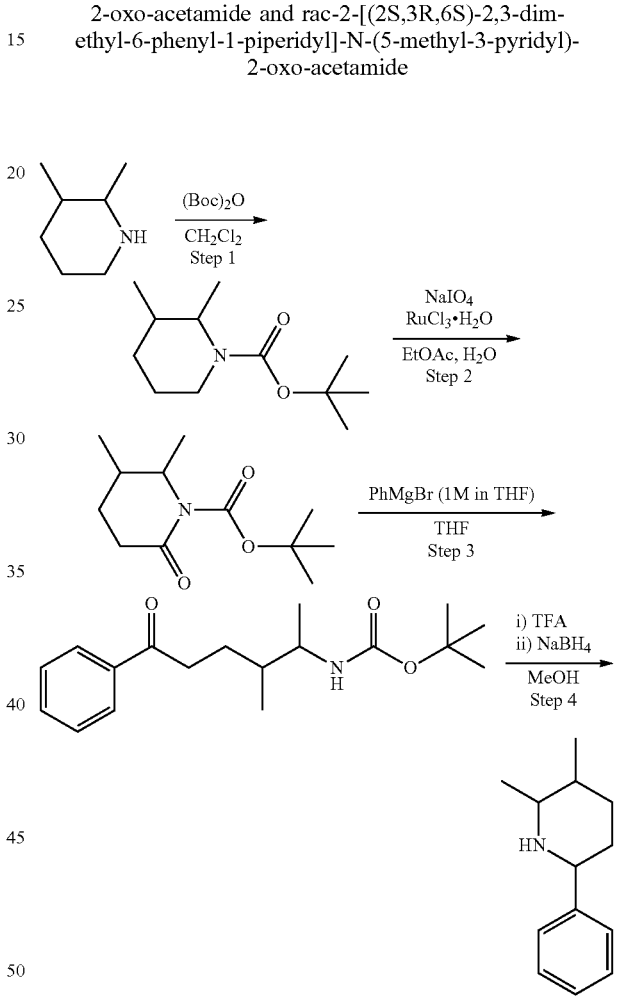

Step 1: Synthesis of tert-butyl 2,3-dimethylpiperidine-1-carboxylate

To a stirred solution of 2,3-dimethylpiperidine (5 g, 44.17 mmol) in CH$_2$Cl$_{12}$ (50 mL) was added Di-tert-butyl dicarbonate (10.12 g, 46.38 mmol, 10.64 mL) dropwise. The resulting reaction mixture was stirred at 20° C. for 12 hours. After 12 hours, the resulting reaction mixture was concentrated under reduced pressure to obtain tert-butyl 2,3-dimethylpiperidine-1-carboxylate (9.2 g, 43.13 mmol, 97.64% yield).

$^1$H NMR (CDCl$_3$, 400 MHz): δ (ppm) 0.81 (dd, 1H), 0.96 (m, 3H), 1.13 (dd, 2H), 1.27 (m, 2H), 1.41 (s, 9H), 1.66 (m, 3H), 2.75 (m, 1H), 3.93 (m, 2H).

LCMS(ESI): [M+Boc]⁺ m/z: calcd 213.2; found 158.2 (t-Bu cleaved product mass); Rt=1.509 min.

Step 2: Synthesis of tert-butyl
2,3-dimethyl-6-oxo-piperidine-1-carboxylate

A solution of tert-butyl 2,3-dimethylpiperidine-1-carboxylate (8.2 g, 38.44 mmol) in EtOAc (80 mL) was added to a stirred solution of sodium periodate (32.89 g, 153.76 mmol) in Water (80 mL). Ruthenium(III) chloride, monohydrate (43.33 mg, 192.20 µmol) was added to the reaction mixture and the resulting biphasic mixture was stirred at 20° C. for 12 hours. After 12 hours, the reaction mixture was filtered. The filter cake was washed with EtOAc (2×15 mL). The filtrate was washed with brine, dried over Na₂SO₄ and evaporated under reduced pressure to obtain tert-butyl 2,3-dimethyl-6-oxo-piperidine-1-carboxylate (8.25 g, crude). The crude product was used for the next step reaction without any further purification.

¹H NMR (DMSO-d₆, 400 MHz): δ (ppm) 0.93 (d, 1.4H), 1.00 (d, 1.6H), 1.06 (d, 1.4H), 1.19 (d, 1.6H), 1.43 (m, 9H), 1.60 (m, 1H), 1.85 (m, 2H), 2.35 (m, 2H), 3.70 (m, 0.5H), 4.00 (m, 0.5H).

LCMS(ESI): [M+Boc]⁺ m/z: calcd 227.2; found 172.2 (t-Bu cleaved product mass); Rt=1.312 min.

Step 3: Synthesis of tert-butyl
N-(1,2-dimethyl-5-oxo-5-phenyl-pentyl)carbamate

To a stirred solution of tert-butyl 2,3-dimethyl-6-oxo-piperidine-1-carboxylate (9 g, 39.60 mmol) in THF (100 mL) at −78° C., phenylmagnesium bromide (1 M in THF, 7.18 g, 39.60 mmol, 39.6 mL) was added dropwise under argon atmosphere. The resulting reaction mixture was allowed to warm to room temperature and stirred at the same temperature for 12 hours. After 12 hours, the reaction mixture was quenched with saturated. aq. NH₄Cl solution and extracted with EtOAc (2×150 mL). The combined organic phase was washed with brine, dried over Na₂SO₄ and evaporated in vacuo to obtain tert-butyl N-(1,2-dimethyl-5-oxo-5-phenyl-pentyl)carbamate (10 g, 32.74 mmol, 82.69% yield). The crude product was used for the next step reaction without any further purification.

LCMS(ESI): [M+Boc]⁺ m/z: calcd 305.2; found 206.2; Rt=1.542 min.

Step 4: Synthesis of
2,3-dimethyl-6-phenyl-piperidine tert-butyl N-(1,2-dimethyl-5-oxo-5-phenyl-pentyl)carbamate (10 g, 32.74 mmol) was dissolved in Trifluoroacetic acid (18.67 g, 163.71 mmol, 12.61 mL) and the resulting reaction mixture was stirred for 1 hour. After 1 hour, 50% aq·NaOH solution was added to the reaction mixture till pH=11-12. The resulting mixture was extracted with DCM (4×40 mL). The combined organic phase was dried over Na₂SO₄ and concentrated under reduced pressure. The obtained residue was dissolved in MeOH (100 mL) and Sodium Borohydride (1.24 g, 32.74 mmol) was added portionwise at 0° C. The resulting mixture was stirred at 20° C. for 1 hour. After 1 hour, the reaction mixture was concentrated under reduced pressure and the obtained residue was diluted with 50% aq·NaOH solution. The resulting mixture was extracted with DCM (4×40 mL). The combined organic phase was dried over Na₂SO₄ and concentrated under reduced pressure to obtain 2,3-dimethyl-6-phenyl-piperidine (3 g, 15.85 mmol, 48.40% yield). The crude product was used for the next step reaction without any further purification.

LCMS(ESI): [M+H]⁺ m/z: calcd 189.2; found 190.2; Rt=0.854 min.

4R. The Synthesis of
3-(5-methyl-2-piperidyl)pyridine

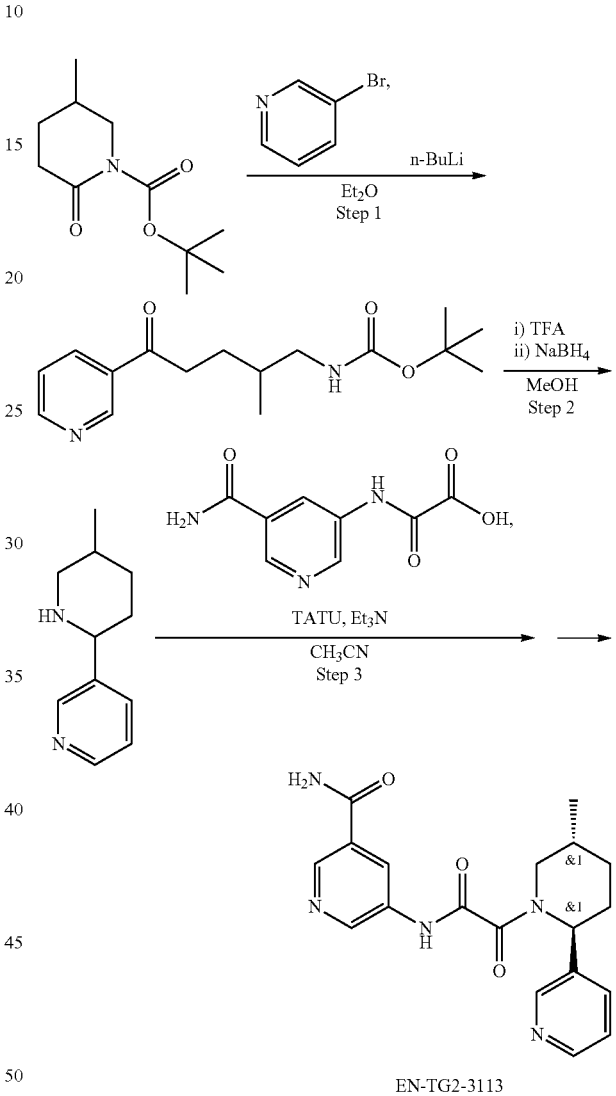

EN-TG2-3113

Step 1: Synthesis of tert-butyl N-[2-methyl-5-oxo-5-(3-pyridyl)pentyl]carbamate

To a stirred solution of 3-bromopyridine (10 g, 63.29 mmol, 6.17 mL) in Et₂O (100 mL) at −78° C., n-butyllithium (2.5 M in Hexane, 24.05 g, 63.29 mmol, 25.3 mL) was added drop wise under argon atmosphere. The resulting mixture was stirred for 1 hour (solution 1). A separate dry 3 necked round bottomed flask fitted with a magnetic stir bar and thermometer was charged with tert-butyl 5-methyl-2-oxo-piperidine-1-carboxylate (11.25 g, 52.74 mmol) and Dry Et₂O (100 mL) under argon atmosphere. The solution was cooled to −78° C. and solution 1 was added drop wise during 1 hour, maintaining the internal temperature below −70° C.

The resulting reaction mixture was allowed to warm to room temperature and quenched with sat. NH₄Cl solution. The aqueous layer was extracted with DCM (3×50 mL) and the combined organic layers was dried over Na₂SO₄, filtered and concentrated under reduced pressure to get tert-butyl N-[2-methyl-5-oxo-5-(3-pyridyl)pentyl]carbamate (12.5 g, 42.75 mmol, 81.06% yield) as a light-yellow oil. The crude product was used in the next step reaction without any further purification.

LCMS(ESI): [M+Boc]⁺ m/z: calcd 292.2; found 237.2 (t-Bu cleaved product mass); Rt=1.174 min.

Step 2: Synthesis of 3-(5-methyl-2-piperidyl)pyridine

The tert-butyl N-[2-methyl-5-oxo-5-(3-pyridyl)pentyl] carbamate (12.5 g, 42.75 mmol) was stirred in Trifluoroacetic acid (24.37 g, 213.77 mmol, 16.47 mL) for 1 hour. Completion of the reaction was confirmed by TLC. 50% w/v NaOH solution was added to the mixture until the pH was 13-14. The resulting mixture was extracted with DCM (4×20 mL). The combined organic layers was dried over MgSO₄ and concentrated under reduced pressure. The obtained crude product was dissolved in MeOH (125 mL) and sodium borohydride (1.62 g, 42.75 mmol) was added portionwise at 0° C. The resulting reaction mixture was stirred for overnight. The reaction mixture was then acidified with 1-2 M HCl until pH was 1-3 and stirred for additional 30 minutes. After 30 minutes, NaOH solution was added until the pH was 13-14 and the resulting mixture was extracted with DCM (4×100 mL). The combined organic layers were dried over Na₂SO₄, filtered and concentrated under reduced pressure. The obtained residue was purified by column chromatography (Combiflash; 120 g SiO₂, Eluent: 0-30% methanol+2% TEA in MTBE; flow rate=85 mL/min, Rv=7.8 CV) to give 3-(5-methyl-2-piperidyl)pyridine (1.5 g, 8.51 mmol, 19.91% yield) as a light-yellow oil.

LCMS(ESI): [M+H]⁺ m/z: calcd 176.2; found 177.2; Rt=0.537 min.

4S. The Synthesis of 2-(3-chlorophenyl)-5-methyl-piperidine

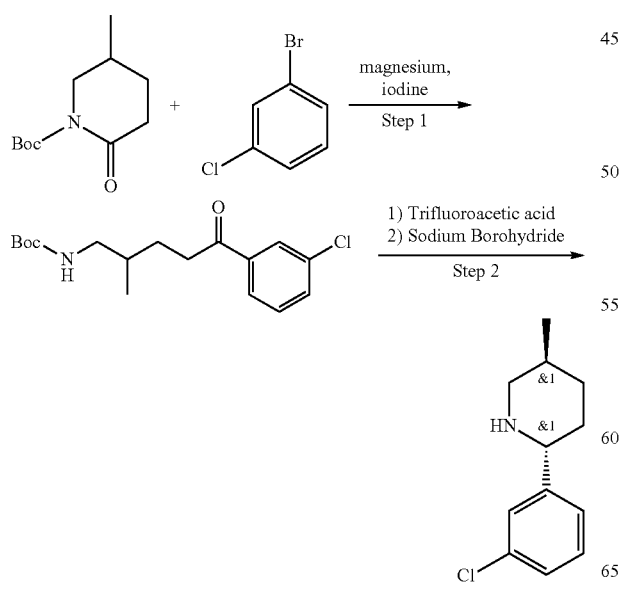

Step 1: Synthesis of tert-butyl N-[5-(3-chlorophenyl)-2-methyl-5-oxo-pentyl]carbamate To a dry 2 necked flask was added magnesium (1.27 g, 52.23 mmol, 729.75 μL), dry THF (25 mL) and tert-butyl 5-methyl-2-oxo-piperidine-1-carboxylate (7.43 g, 34.82 mmol) with stirring under Ar. iodine (88.38 mg, 348.21 μmol) was added and the mixture was heated gently until it maintained its own reflux. When reflux had subsided, external heating was applied to maintain reflux for a further 1 hour. 1-bromo-3-chloro-benzene (10 g, 52.23 mmol, 6.13 mL) was added to a dry 3 necked round bottomed flask with a thermometer. Dry THF (25 mL) was added with stirring under Ar and the solution was cooled to −78° C. The Grignard reagent was added to the t-Boc-lactam over 1 hour, maintaining the internal temperature below −70° C. The solution was warmed to room temperature and sat. NH₄Cl was added. The aqueous layer was extracted 3×50 mL with DCM and the organic layers combined, dried over Na₂SO₄, filtered and concentrated in vacuo. tert-butyl N-[5-(3-chlorophenyl)-2-methyl-5-oxo-pentyl]carbamate (10.9 g, crude) was obtained as a light-yellow oil and was used in the next step without further purification.

¹H NMR (400 MHz, CDCl₃) δ 0.93 (d, 3H), 1.42 (m, 9H), 1.50-1.60 (m, 1H), 1.65-1.77 (m, 2H), 2.97-3.05 (m, 4H), 4.66 (brs, 1H), 7.38 (t, 1H), 7.50 (d, 1H), 7.79 (d, 1H), 7.90 (s, 1H).

LCMS(ESI): [M+H]⁺ m/z: calcd 325.2; found 326.2; Rt=1.601 min.

Step 2: Synthesis of 2-(3-chlorophenyl)-5-methyl-piperidine

The tert-butyl N-[5-(3-chlorophenyl)-2-methyl-5-oxo-pentyl]carbamate (10.9 g, 33.45 mmol) was stirred in Trifluoroacetic acid (13.35 g, 117.09 mmol, 9.02 mL) for 1 hr. TLC was used to check the reaction progress. 50% w/v NaOH solution was added to the mixture until the pH was 13-14. The product was extracted 4×20 mL with DCM and the organic layers combined, dried with MgSO₄ and evaporated. The product was dissolved in mixture water (15 mL)/MeOH (150 mL) and added to a flask followed by Sodium Borohydride (1.27 g, 33.45 mmol, 1.18 mL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na₂SO₄, filtered and evaporated to give 2-(3-chlorophenyl)-5-methyl-piperidine (6.05 g, 28.85 mmol, 86.24% yield) as a light-yellow oil.

¹H NMR (400 MHz, CDCl₃) δ 0.88-1.12 (m, 3H), 1.12 (m, 1H), 1.48-1.83 (m, 5H), 2.37 (t, 1H), 3.10 (d, 1H), 3.60 (d, 1H), 7.20 (brs, 3H), 7.35 (s, 1H).

LCMS(ESI): [M+H]⁺ m/z: calcd 209.1; found 210.2; Rt=0.590 min.

4T. The Synthesis of 4,5-dimethyl-2-phenyl-piperidine

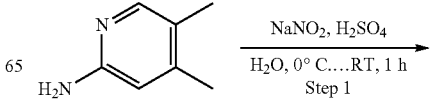

Step 1

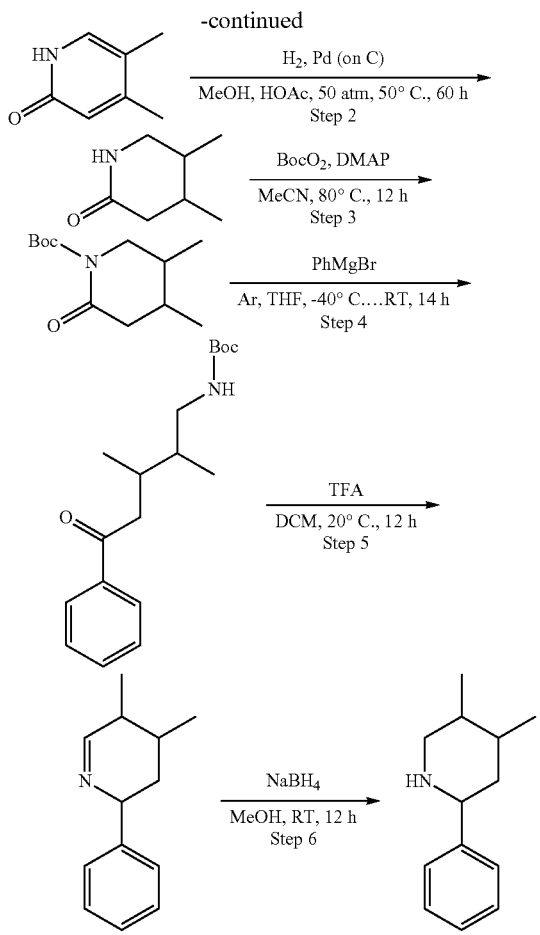

Step 1: The Synthesis of 4,5-dimethyl-4H-pyridin-2-one

To a stirred solution of sulfuric acid (2.41 g, 24.56 mmol) in water (8 mL), 4,5-dimethylpyridin-2-amine (1 g, 8.19 mmol) was added. The resulting solution was cooled to 0° C. and the solution of sodium nitrite (1.69 g, 24.56 mmol, 780.78 μL) in water (7 mL) was added dropwise using addition funnel at 0° C. The reaction mixture was warmed to room temperature and stirred for additional 30 min at room temperature. Then, the resulting mixture was extracted with DCM (2*30 ml. The combined organic layer was dried over $Na_2SO_4$, filtered off, and evaporated to give 4,5-dimethyl-1H-pyridin-2-one (0.561 g, 4.56 mmol, 55.65% yield) which was used in the next step without further purification.

$^1$H NMR (400 MHz, DMSO-$d_6$) δ 1.91 (s, 3H), 2.05 (s, 3H), 6.13 (s, 1H), 7.05 (s, 1H), 11.14 (s, 1H).

LCMS(ESI): [M+H]$^+$ m/z: calcd 123.2; found 124.2; Rt=1.688 min.

Step 2: The Synthesis of 4,5-dimethylpiperidin-2-one 4,5-dimethyl-1H-pyridin-2-one (0.561 g, 4.56 mmol) was dissolved in MeOH (5 mL) with AcOH (1 mL) and Pd/C JM A402028-10 (0.06 g, 4.56 mmol) was added. The resulting mixture was hydrogenated with $H_2$ (50 atm) at 50° C. for 60 hr. The reaction mixture was filtered through celite and filtrate was concentrated in vacuo at 45° C. The residue was dissolved in DCM (25 ml) and washed with aqueous $NaHCO_3$. The organic layer was dried over $Na_2SO_4$, filtered off, and concentrated in vacuo at 40° C. to give 4,5-dimethylpiperidin-2-one (0.45 g, 3.54 mmol, 77.67% yield).

$^1$H NMR (500 MHz, CDCl$_3$) δ 0.96 (s, 6H), 1.59 (m, 1H), 2.16 (m, 2H), 2.43 (m, 1H), 2.95 (m, 1H), 3.30 (m, 1H), 6.00 (m, 1H).

LCMS(ESI): [M+2H]$^+$ m/z: calcd 127.2; found 129.2; Rt=0.467 min.

Step 3: The Synthesis of tert-butyl 4,5-dimethyl-2-oxo-piperidine-1-carboxylate 4,5-dimethylpiperidin-2-one (0.45 g, 3.54 mmol), di-tert-butyl dicarbonate (888.03 mg, 4.07 mmol, 933.78 μL), and DMAP (43.23 mg, 353.82 μmol) were dissolved in MeCN (10 mL). The reaction mixture was stirred at 80° C. for 12 hr. The resulting mixture was concentrated in vacuo. The residue was dissolved in DCM and washed with aq·$NaHSO_4$. The organic phase was dried over $Na_2SO_4$, filtered off, and evaporated in vacuo to give tert-butyl 4,5-dimethyl-2-oxo-piperidine-1-carboxylate (0.656 g, 2.89 mmol, 81.57% yield).

$^1$H NMR (400 MHz, CDCl$_3$) δ 0.92 (m, 6H), 1.50 (m, 9H), 1.60 (m, 1H), 2.12 (m, 2H), 2.53 (m, 1H), 3.10 (m, 1H), 3.75 (m, 1H).

LCMS(ESI): [M-$^t$Bu]$^+$ m/z: calcd 171.2; found 172.2; Rt=3.31 min.

Step 4: The Synthesis of tert-butyl N-(2,3-dimethyl-5-oxo-5-phenyl-pentyl)carbamate Bromo(phenyl)magnesium (601.77 mg, 3.32 mmol) was added dropwise to a solution of tert-butyl 4,5-dimethyl-2-oxo-piperidine-1-carboxylate (0.656 g, 2.89 mmol) in THF (15 mL) at −40° C. under an argon atmosphere. After addition completed, the resulting mixture was stirred at −40° C. for 30 min and then allowed to warm to room temperature and stirred for 12 hr. Sat. aqueous solution of Ammonium Chloride was added to the reaction mixture and the resulting mixture was stirred for 15 min. An organic layer was separated and an aqueous layer was extracted with EtOAc (3*30 ml). The combined organic layers was washed with brine, dried over $Na_2SO_4$, filtered off, and evaporated to give tert-butyl N-(2,3-dimethyl-5-oxo-5-phenyl-pentyl)carbamate (648 mg, 2.12 mmol, 73.52% yield) which was used in the next step without further purification.

$^1$H NMR (500 MHz, CDCl$_3$) δ 0.96 (m, 6H), 1.44 (s, 9H), 1.71 (m, 1H), 2.33 (m, 1H), 2.85 (m, 1H), 3.13 (m, 3H), 4.74 (m, 1H), 7.46 (m, 2H), 7.56 (dd, 1H), 7.97 (m, 2H).

LCMS(ESI): [M-Boc]$^+$ m/z: calcd 205.2; found 206.4; Rt=4.039 min.

Step 5: The Synthesis of 3,4-dimethyl-6-phenyl-2,3,4,5-tetrahydropyridine tert-butyl N-(2,3-dimethyl-5-oxo-5-phenyl-pentyl)carbamate (0.648 g, 2.12 mmol) was dissolved in DCM (6 mL) and TFA (6 mL) was added dropwise. The reaction mixture was stirred for 20° C. overnight. Then, sat. aqueous solution of potassium carbonate was added carefully and the mixture was stirred for 30 min. The mixture was diluted with DCM. The aqueous layer was washed with DCM (2*25 ml), organic phase was dried over $Na_2SO_4$, filtered off, and concentrated in vacuo at 40° C. to give 3,4-dimethyl-6- phenyl-2,3,4,5-tetrahydropyridine (0.388 g, 2.07 mmol, 97.64% yield) which was used in the next step without further purification.

$^1$H NMR (500 MHz, CDCl$_3$) δ 0.90 (d, 3H), 0.94 (m, 3H), 0.98 (m, 1H), 1.06 (m, 1H), 1.87 (m, 1H), 2.84 (m, 1H), 3.31 (m, 1H), 4.03 (m, 1H), 7.37 (s, 3H), 7.77 (s, 2H).

LCMS(ESI): [M+H]$^+$ m/z: calcd 187.2; found 188.2; Rt=1.490 min.

Step 6: The Synthesis of 4,5-dimethyl-2-phenyl-piperidine 3,4-dimethyl-6-phenyl-2,3,4,5-tetrahydropyridine (0.388 g, 2.07 mmol) was dissolved in MeOH (5 mL) and Sodium Borohydride (627.04 mg, 16.57 mmol, 586.02 μL) was added portionwise under cooling with ice-water. The reaction mixture was heated to room temperature and stirred for 12 hr. Then, NH$_4$Cl (aq.) was added and methanol was evaporated, aqueous layer was extracted with DCM (3*30 ml) and combined organic layer was dried over Na$_2$SO$_4$. The suspension was filtered off and evaporated on vacuo at 45° C. to give 4,5-dimethyl-2-phenyl-piperidine (0.23 g, 1.22 mmol, 58.65% yield) which was used in the next step without further purification. 4,5-dimethyl-2-phenyl-piperidine (0.23 g, 1.22 mmol, 58.65% yield).

$^1$H NMR (400 MHz, CDCl$_3$) δ 0.89 (m, 6H), 1.24 (m, 2H), 1.76 (m, 2H), 2.43 (m, 1H), 2.98 (m, 1H), 3.10 (m, 1H), 3.61 (m, 1H), 7.31 (m, 5H).

LCMS(ESI): [M+H]$^+$ m/z: calcd 189.2; found 190.4; Rt=2.024 min.

4U. The Synthesis of 2-[4-(difluoromethyl)phenyl]-5-methyl-piperidine

Step 1: The Synthesis of tert-butyl N-[5-[4-(difluoromethyl)phenyl]-2-methyl-5-oxo-pentyl]carbamate To a solution of 1-bromo-4-(difluoromethyl)benzene (4.6 g, 22.22 mmol) in THF (25 mL), n-butyllithium (6.19 g, 22.22 mmol, 8.93 mL, 23% purity) was added dropwise over a period of 30 min at −78° C. The reaction mass was stirred for 1 h at −78° C. and tert-butyl 5-methyl-2-oxo-piperidine-1-carboxylate (4.74 g, 22.22 mmol) was added at same temperature and the reaction was further stirred at −78° C. for 1 h. After completion, the reaction mixture was brought to 0° C. and treated with saturated ammonium chloride solution and extracted with ethyl acetate. The organic layer was dried over anhydrous sodium sulfate, filtered and concentrated under reduced pressure to get the crude tert-butyl N-[5-[4-(difluoromethyl)phenyl]-2-methyl-5-oxo-pentyl]carbamate (7.2 g, 21.09 mmol, 94.91% yield) which was used in the next step without further purification.

$^1$H NMR (500 MHz, DMSO-d$_6$) δ 0.94 (m, 3H), 1.43 (m, 9H), 1.69 (m, 2H), 2.35 (m, 2H), 3.04 (m, 2H), 4.71 (m, 2H), 7.50 (m, 2H), 7.59 (m, 2H), 8.04 (m, 1H).

LCMS(ESI): [M-Boc]$^+$ m/z: calcd 241.2; found 242.2; Rt=1.564 min.

Step 2: The Synthesis of 2-[4-(difluoromethyl)phenyl]-5-methyl-piperidine

The tert-butyl N-[5-[4-(difluoromethyl)phenyl]-2-methyl-5-oxo-pentyl]carbamate (8.8 g, 25.78 mmol) was stirred in trifluoroacetic acid (14.70 g, 128.88 mmol, 9.93 mL) for 1 hr. TLC was used to check the reaction progress. 50% w/v NaOH solution was added to the mixture until the pH was 13-14. The product was extracted 4×20 mL with DCM and the organic layers combined, dried with MgSO$_4$ and evaporated. The product was dissolved in mixture MeOH (50 mL)/water (50 mL) and added to a flask followed by Sodium Borohydride (975.20 mg, 25.78 mmol, 911.40 μL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na$_2$SO$_4$, filtered and evaporated. The residue was purified by CC (Companion combiflash, 120 g SiO$_2$, acetonitrile/methanol with methanol from 0~5%, flow rate=85 mL/min, Rv=4 CV) to give 2-[4-(difluoromethyl)phenyl]-5-methyl-piperidine (0.63 g, 2.80 mmol, 10.85% yield) as an light-yellow oil.

$^1$H NMR (500 MHz, CDCl$_3$) δ 0.92 (d, 3H), 1.17 (m, 1H), 1.84 (m, 5H), 2.43 (m, 1H), 3.16 (m, 1H), 3.62 (m, 1H), 7.47 (s, 4H).

LCMS(ESI): [M+H]$^+$ m/z: calcd 225.2; found 226.2; Rt=0.890 min.

4V. The Synthesis of 5-methyl-2-phenylpiperidine

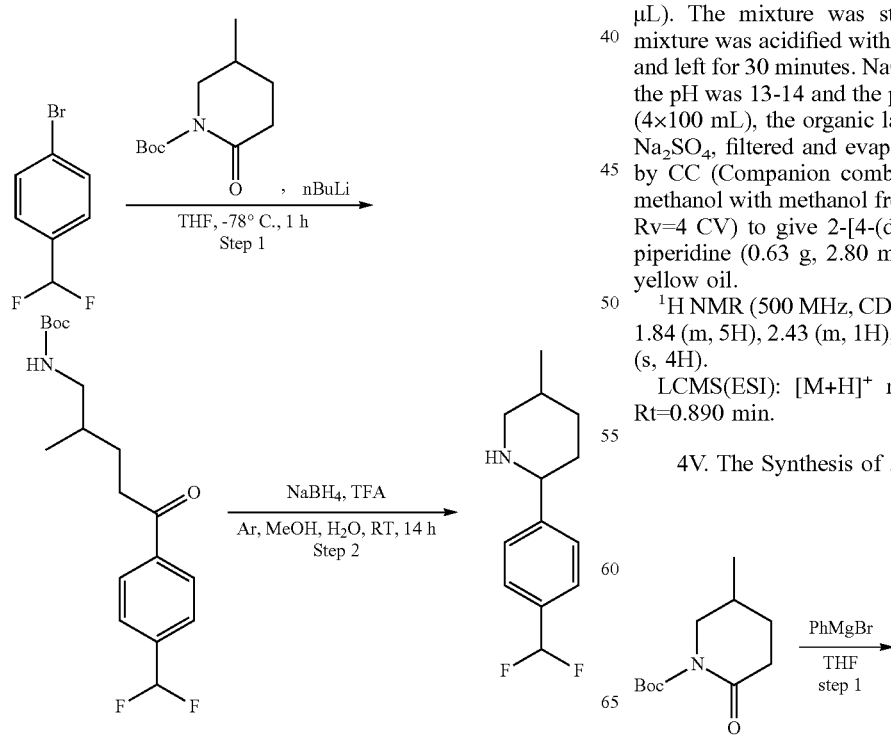

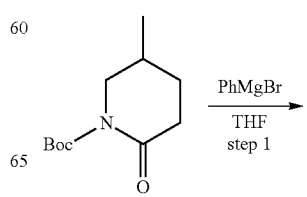

-continued

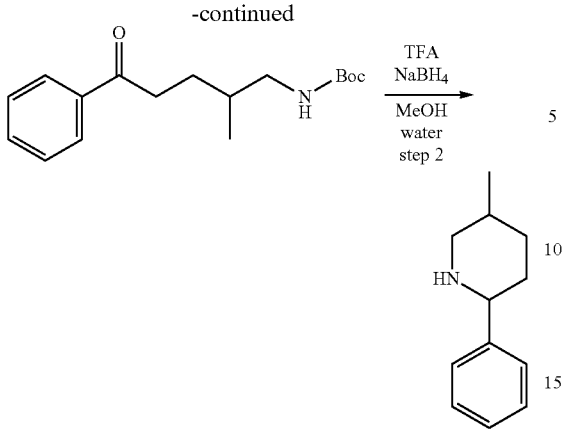

Step 1: Synthesis of tert-butyl (2-methyl-5-oxo-5-phenylpentyl)carbamate

To a dry 2 necked flask was added THF (300 mL) and tert-butyl 5-methyl-2-oxo-piperidine-1-carboxylate (30 g, 140.66 mmol) with stirring and the solution was cooled to −78° C. Phenyl magnesium bromide (255.04 g, 211.00 mmol, 260.25 mL) reagent was added to the t-boc-lactam over 1 hour, maintaining the internal temperature below −70° C. The solution was warmed to room temperature and sat. NH$_4$Cl was added. The aqueous layer was extracted 3×50 mL with DCM and the organic layers combined, dried over Na$_2$SO$_4$, filtered and concentrated in vacuo. tert-butyl N-(2-methyl-5-oxo-5-phenyl-pentyl)carbamate (41 g, crude) was obtained as a light-yellow oil and was used in the next step without further purification.

$^1$H NMR (500 MHz, CDCl$_3$) δ (ppm) 0.96 (d, 3H), 1.45 (s, 9H), 1.68 (m, 1H), 1.72 (m, 1H), 1.85 (m, 1H), 3.05 (m, 4H), 4.71 (m, 1H), 7.45 (t, 2H), 7.55 (t, 1H), 7.96 (d, 2H).

LCMS(ESI): [M-Boc]$^+$ m/z: calcd 191.2; found 192.2; Rt=1.486 min.

Step 2: Synthesis of 5-methyl-2-phenylpiperidine

The tert-butyl N-(2-methyl-5-oxo-5-phenyl-pentyl)carbamate (41 g, 140.71 mmol) was stirred in trifluoroacetic acid (80.22 g, 703.54 mmol, 54.20 mL) for 1 hr. TLC was used to check the reaction progress. 50% w/v NaOH solution was added to the mixture until the pH was 13-14. The product was extracted 4×20 mL with DCM and the organic layers combined, dried with MgSO$_4$ and evaporated. The product was dissolved in mixture MeOH (500 mL)/water (100 mL) and added to a flask followed by sodium borohydride (5.32 g, 140.71 mmol, 4.98 mL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na$_2$SO$_4$, filtered and evaporated to give 5-methyl-2-phenyl-piperidine (21.2 g, crude) as a light-yellow oil.

$^1$H NMR (400 MHz, CDCl$_3$) δ (ppm) 0.87 (d, 3H), 1.14 (m, 1H), 1.56 (m, 2H), 1.81 (m, 3H), 2.40 (t, 2H), 3.11 (d, 1H), 3.53 (d, 1H), 7.29 (m, 5H).

LCMS(ESI): [M+1] m/z: calcd 175.2; found 176.2; Rt=0.779 min.

4W. Synthesis of 2-(5-methyl-2-(4-(trifluoromethyl)phenyl)piperidin-1-yl)-2-oxoacetic acid

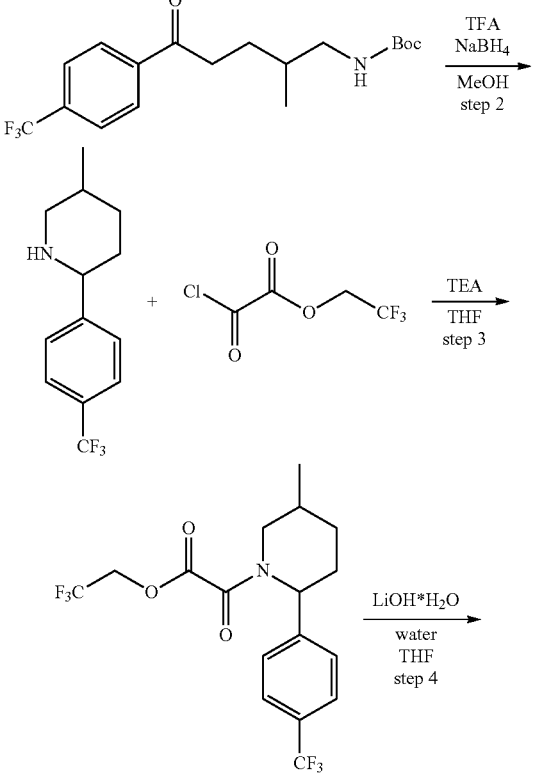

Step 1: Synthesis of tert-butyl (2-methyl-5-oxo-5-(4-(trifluoromethyl)phenyl)pentyl)carbamate To a dry 2 necked flask was added magnesium (1.08 g, 44.44 mmol, 620.80 μL), dry THF (50 mL) and 1-bromo-4-(trifluoromethyl)benzene (10 g, 44.44 mmol, 6.21 mL) with stirring under Ar. Iodine (433.85 mg, 1.71 mmol) was added and the mixture was heated gently until it maintained its own reflux. When reflux had subsided external heating was applied to maintain reflux for a further 1 hr. tert-butyl 5-methyl-2-oxo-piperidine-1-carboxylate (7.29 g, 34.19 mmol) was added to a dry 3 necked round bottomed flask with a thermometer. Dry THF (50 mL) was added with stirring under Ar and the solution was cooled to −78° C. The Grignard reagent was added to the t-boc-lactam over 1 hr, maintaining the internal temperature below −70° C. The solution was warmed to rt and sat. NH₄Cl was added. The aqueous layer was extracted 3×50 mL with DCM and the organic layers combined, dried over Na₂SO₄, filtered and concentrated in vacuo. tert-butyl N-[2-methyl-5-oxo-5-[4-(trifluoromethyl)phenyl]pentyl]carbamate (13 g, crude) was obtained as a light-yellow oil and was used in the next step without further purification.

¹H NMR (400 MHz, CDCl₃) δ (ppm) 0.93 (d, 3H), 1.43 (s, 9H), 1.80 (m, 3H), 3.05 (m, 3H), 4.12 (m, 1H), 5.12 (m, 1H), 7.71 (m, 2H), 8.05 (m, 2H).

LCMS(ESI): [M-Boc]⁺ m/z: calcd 259.2; found 260.2; Rt=1.605 min.

Step 2: Synthesis of
5-methyl-2-(4-(trifluoromethyl)phenyl)piperidine

The tert-butyl N-[2-methyl-5-oxo-5-[4-(trifluoromethyl) phenyl]pentyl]carbamate (13 g, 36.17 mmol) was stirred in trifluoroacetic acid (20.62 g, 180.87 mmol, 13.93 mL) for 1 hr. TLC was used to check the reaction progress. 50% w/v NaOH solution was added to the mixture until the pH was 13-14. The product was extracted 4×20 mL with DCM and the organic layers combined, dried with MgSO₄ and evaporated. The product was dissolved in mixture water (50 mL)/MeOH (125 mL) and added to a flask followed by sodium borohydride (1.37 g, 36.17 mmol, 1.28 mL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na₂SO₄, filtered and evaporated. The residue was purified by CC (Interchim, 120 g SiO₂, hexane/MTBE with MTBE from 15~55%, flow rate=85 ml/min, RV=5,5 CV.) to give 5-methyl-2-[4-(trifluoromethyl)phenyl]piperidine (3.4 g, 13.98 mmol, 38.64% yield) as a light-yellow oil.

¹H NMR (500 MHz, CDCl₃) δ (ppm) 0.91 (d, 3H), 1.16 (m, 1H), 1.79 (m, 5H), 2.43 (m, 1H), 3.15 (m, 1H), 3.70 (m, 1H), 7.48 (m, 2H), 7.58 (m, 2H).

LCMS(ESI): [M]⁺ m/z: calcd 243.2; found 244.2; Rt=1.082 min.

Step 3: Synthesis of 2,2,2-trifluoroethyl 2-(5-methyl-2-(4-(trifluoromethyl)phenyl)piperidin-1-yl)-2-oxoacetate 2,2,2-trifluoroethyl 2-chloro-2-oxo-acetate (783.11 mg, 4.11 mmol) was added dropwise to the solution of 5-methyl-2-[4-(trifluoromethyl)phenyl]piperidine (1 g, 4.11 mmol) and TEA (415.96 mg, 4.11 mmol, 572.95 µL) in THF (20 mL) at −10° C. The resulting mixture was left to warm to rt and stirred for 12 hr. The resulting precipitate was filtered off. The filtrate was evaporated to obtain 2,2,2-trifluoroethyl 2-[5-methyl-2-[4-(trifluoromethyl)phenyl]-1-piperidyl]-2-oxo-acetate (1.3 g, 3.27 mmol, 79.60% yield) which was used in next step without purification.

¹H NMR (500 MHz, DMSO-d₆) δ (ppm) 0.96 (d, 3H), 1.48 (m, 1H), 1.56 (m, 2H), 1.98 (m, 2H), 2.12 (m, 2H), 3.21 (m, 1H), 3.98 (m, 1H), 5.12 (s, 2H), 7.48 (m, 2H), 7.78 (m, 2H).

LCMS(ESI): [M]⁺ m/z: calcd 397.2; found 398.2; Rt=1.600 min.

Step 4: Synthesis of 2-(5-methyl-2-(4-(trifluoromethyl)phenyl)piperidin-1-yl)-2-oxoacetic acid Lithium hydroxide monohydrate, 98% (137.30 mg, 3.27 mmol, 90.93 µL) was added to the solution of 2,2,2-trifluoroethyl 2-[5-methyl-2-[4-(trifluoromethyl)phenyl]-1-piperidyl]-2-oxo-acetate (1.3 g, 3.27 mmol) in THF (20 mL) and water (2 mL) and the resulting mixture was stirred at 20° C. for 12 hr. The resulting mixture was evaporated to dryness to obtain 2-[5-methyl-2-[4-(trifluoromethyl)phenyl]-1-piperidyl]-2-oxo-acetic acid (0.9 g, 2.79 mmol, 85.36% yield, Li⁺) which was used in next step without purification.

¹H NMR (400 MHz, DMSO-d₆) δ (ppm) 0.96 (d, 3H), 1.36 (m, 1H), 1.52 (m, 1H), 1.86 (m, 1H), 2.12 (m, 2H), 2.38 (m, 1H), 2.98 (m, 1H), 3.76 (m, 1H), 5.36 (m, 1H), 7.48 (m, 1H), 7.68 (m, 3H).

LCMS(ESI): [M]⁺ m/z: calcd 315.2; found 316.2; Rt=1.384 min.

4X. Synthesis of 2-(5-methyl-2-(3-(trifluoromethyl)phenyl)piperidin-1-yl)-2-oxoacetic acid

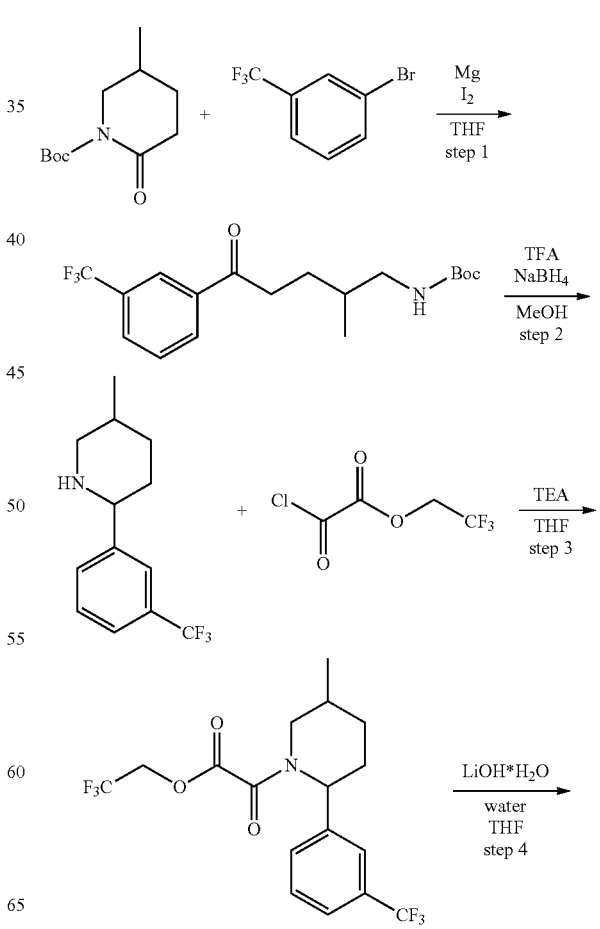

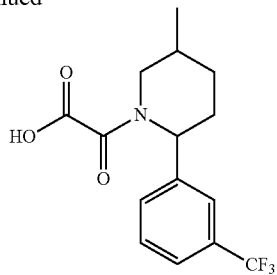

1: Synthesis of tert-butyl (2-methyl-5-oxo-5-(3-(trifluoromethyl)phenyl)pentyl)carbamate 1-bromo-3-(trifluoromethyl)benzene (10 g, 44.44 mmol, 6.21 mL) was added to the mixture of THF (100 mL) and Mg (1.19 g, 48.89 mmol, 682.88 µL) under argon atmosphere. Iodine (112.80 mg, 444.43 µmol) was added thereto and the resulting mixture was heated to reflux for 1 hr. The resulting mixture was cooled to rt and added dropwise to the solution of tert-butyl 5-methyl-2-oxo-piperidine-1-carboxylate (9.48 g, 44.44 mmol) in THF (100 mL) at −78° C. The resulting mixture was left to warm to rt and then poured into aq. NH$_4$Cl solution. The resulting mixture was extracted with EtOAc (2×40 ml). The combined organic extracts were washed with brine, dried over Na$_2$SO$_4$ and evaporated to obtain tert-butyl N-[2-methyl-5-oxo-5-[3-(trifluoromethyl)phenyl]pentyl]carbamate (10 g, 27.83 mmol, 62.61% yield), which was used in next step without purification.

$^1$H NMR (400 MHz, DMSO-d$_6$) δ (ppm) 0.86 (d, 3H), 1.42 (s, 9H), 1.62 (m, 1H), 1.78 (m, 1H), 2.06 (m, 1H), 2.82 (m, 1H), 3.12 (m, 2H), 3.78 (m, 1H), 5.55 (m, 1H), 7.57 (m, 4H).

LCMS(ESI): [M-Boc]$^+$ m/z: calcd 259.2; found 260.2; Rt=1.585 min.

Step 2: Synthesis of 5-methyl-2-(3-(trifluoromethyl)phenyl)piperidine tert-butyl N-[2-methyl-5-oxo-5-[3-(trifluoromethyl)phenyl]pentyl]carbamate (10 g, 27.83 mmol) was dissolved in TFA (31.73 g, 278.26 mmol, 21.44 mL) and the resulting mixture was stirred for 1 hr. 50% aq·NaOH solution was added thereto to pH 11-12. The resulting mixture was extracted with DCM (4×401) the combined organic layer was evaporated to dryness. The residue was dissolved in MeOH (50 mL) and sodium borohydride (1.05 g, 27.83 mmol, 983.84 µL) was added. The resulting mixture was stirred at 20° C. for 12 hr and evaporated. 50% aq. NaOH solution was added to the residue. The resulting mixture was extracted with DCM (4×40 ml) the combined organic layer was evaporated to dryness to obtain 5-methyl-2-[3-(trifluoromethyl)phenyl]piperidine (2 g, 8.22 mmol, 29.55% yield) which was used in next step without purification.

$^1$H NMR (500 MHz, DMSO-d$_6$) δ (ppm) 0.86 (d, 3H), 1.12 (m, 1H), 1.26 (m, 1H), 1.52 (m, 1H), 1.78 (m, 2H), 2.24 (t, 1H), 2.98 (d, 1H), 3.56 (d, 1H), 7.53 (m, 2H), 7.68 (m, 2H).

LCMS(ESI): [M]$^+$ m/z: calcd 243.2; found 244.2; Rt=0.969 min.

Step 3: Synthesis of 2,2,2-trifluoroethyl 2-(5-methyl-2-(3-(trifluoromethyl)phenyl)piperidin-1-yl)-2-oxoacetate 2,2,2-trifluoroethyl 2-chloro-2-oxo-acetate (783.11 mg, 4.11 mmol) was added dropwise to the solution of 5-methyl-2-[3-(trifluoromethyl)phenyl]piperidine (1 g, 4.11 mmol) and TEA (415.96 mg, 4.11 mmol, 572.95 µL) in THF (20 mL) at −10° C. The resulting mixture was left to warm to rt and stirred for 12 hr. The resulting precipitate was filtered off. The filtrate was evaporated to obtain 2,2,2-trifluoroethyl 2-[5-methyl-2-[3-(trifluoromethyl)phenyl]-1-piperidyl]-2-oxo-acetate (1.3 g, 3.27 mmol, 79.60% yield) which was used in next step without purification.

$^1$H NMR (500 MHz, DMSO-d$_6$) δ (ppm) 0.96 (d, 3H), 1.48 (m, 1H), 1.68 (m, 1H), 1.98 (m, 1H), 2.12 (m, 2H), 3.36 (m, 3H), 5.52 (s, 2H), 7.68 (m, 4H).

LCMS(ESI): [M]$^+$ m/z: calcd 397.2; found 398.2; Rt=1.502 min.

Step 4: Synthesis of 2-(5-methyl-2-(3-(trifluoromethyl)phenyl)piperidin-1-yl)-2-oxoacetic acid Lithium hydroxide monohydrate, 98% (137.30 mg, 3.27 mmol, 90.93 µL) was added to the solution of 2,2,2-trifluoroethyl 2-[5-methyl-2-[3-(trifluoromethyl)phenyl]-1-piperidyl]-2-oxo-acetate (1.3, 3.27 mmol) in water (2 mL) and THF (20 mL) and the resulting mixture was stirred at 20° C. for 12 hr. The resulting mixture was evaporated to dryness to obtain 2-[5-methyl-2-[3-(trifluoromethyl)phenyl]-1-piperidyl]-2-oxo-acetic acid (0.9, 2.79 mmol, 85.36% yield, Li$^+$) which was used in next step without purification.

$^1$H NMR (400 MHz, DMSO-d$_6$) δ (ppm) 0.96 (d, 3H), 1.48 (m, 2H), 2.12 (m, 2H), 2.48 (m, 1H), 3.02 (m, 1H), 3.36 (m, 2H), 5.25 (m, 1H), 7.56 (m, 4H).

LCMS(ESI): [M]$^+$ m/z: calcd 315.2; found 316.2; Rt=1.165 min.

4Y. The Synthesis of 2-isopropyl-5-methyl-piperidine

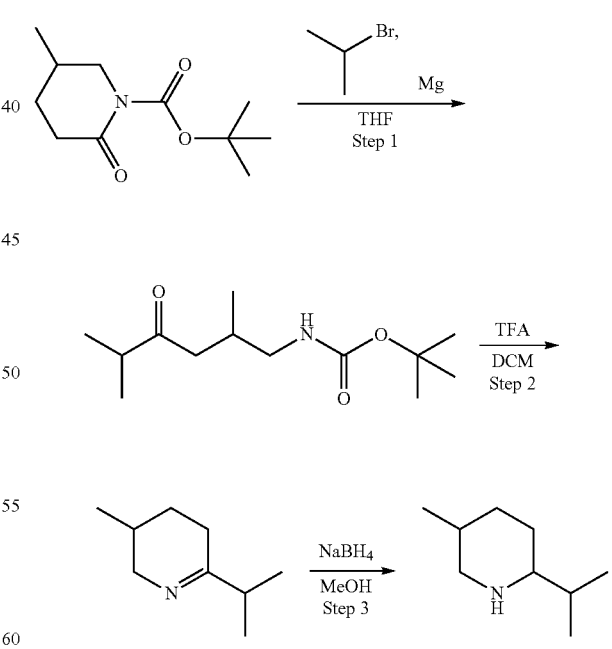

Step 1: Synthesis of tert-butyl N-(2,5-dimethyl-4-oxo-hexyl)carbamate

To a suspension of Magnesium (2.56 g, 105.22 mmol, 1.47 mL) in THF (100 mL) was added 2-bromopropane (12.94 g, 105.22 mmol). The reaction mixture was stirred for 45 minutes to give a grey solution. The freshly prepared Grignard reagent was added dropwise to a precooled suspension of tert-butyl 5-methyl-2-oxo-piperidine-1-carboxylate (20.4 g, 95.65 mmol) in THF (200 mL) at −78° C. The reaction mixture was stirred at −78° C. for 1 hour. After 1 hour, the reaction mixture was allowed to warm to room temperature and stirred for 12 hours. After 12 hours, the reaction was diluted with MTBE (500 mL) and slowly quenched with 100 mL of saturated ammonium chloride aqueous solution. The organic phase was washed with a saturated sodium bicarbonate solution (2×200 mL). The combined aqueous fractions were back extracted with MTBE. The combined organic phase was dried over $Na_2SO_4$ and concentrated under reduced pressure. The crude product was purified by column chromatography to obtain tert-butyl N-(2,5-dimethyl-4-oxo-hexyl)carbamate (6.79 g, 27.91 mmol, 29.18% yield) as a light-yellow liquid.

$^1$H NMR (CDCl$_3$, 400 MHz): δ (ppm) 0.88 (m, 3H), 1.07 (m, 6H), 1.42 (m, 10H), 1.62 (m, 3H), 2.46 (m, 2H), 2.58 (m, 1H), 2.97 (m, 2H), 4.63 (brs, 1H).

Step 2: Synthesis of 6-isopropyl-3-methyl-2,3,4,5-tetrahydropyridine

A solution of tert-butyl N-(2,5-dimethyl-4-oxo-hexyl)carbamate (6.79 g, 27.91 mmol) in TFA (30 mL) and DCM (30 mL) was stirred at 25° C. for 12 hours. After 12 hours, saturated aq. Sodium sulfate solution was added (50 mL) and then extracted with DCM (2×50 mL). The combined organic phase was dried over $Na_2SO_4$, filtered and concentrated under reduced pressure to obtain 6-isopropyl-3-methyl-2,3,4,5-tetrahydropyridine (3.6 g, 25.86 mmol, 92.65% yield) as a light-yellow oil. The crude product was used for the next step reaction without any further purification.

$^1$H NMR (CDCl$_3$, 400 MHz): δ (ppm) 0.88 (m, 3H), 1.19 (m, 6H), 1.40 (m, 1H), 1.53 (m, 1H), 1.72 (m, 1H), 2.07 (m, 2H), 2.21 (m, 1H), 2.98 (m, 1H), 3.65 (d, 1H).

Step 3: Synthesis of 2-isopropyl-5-methyl-piperidine

Sodium Borohydride (1.96 g, 51.71 mmol) was added portionwise to a solution of 6-isopropyl-3-methyl-2,3,4,5-tetrahydropyridine (3.6 g, 25.86 mmol) in Methanol (72 mL). The mixture was stirred at room temperature for 12 hours. After 12 hours, Water (50 mL) was added and the resulting mixture was extracted with EtOAc (2×50 mL). The combined organic phase was dried over sodium sulfate, filtered. HCl in Dioxane (50 mL) was added and the resulting solution was concentrated under reduced pressure to obtain 2-isopropyl-5-methyl-piperidine (4 g, crude, HCl salt) as a yellow oil. The crude product was used for the next step reaction without any further purification.

$^1$H NMR (DMSO-d$_6$, 400 MHz): δ (ppm) 0.93 (m, 9H), 1.08 (m, 1H), 1.34 (m, 1H), 1.84 (m, 4H), 2.45 (m, 1H), 2.68 (m, 1H), 3.07 (m, 1H), 8.90 (brs, 2H).

4Z. The Synthesis of 2-(4-tert-butylcyclohexyl)-5-methyl-piperidine

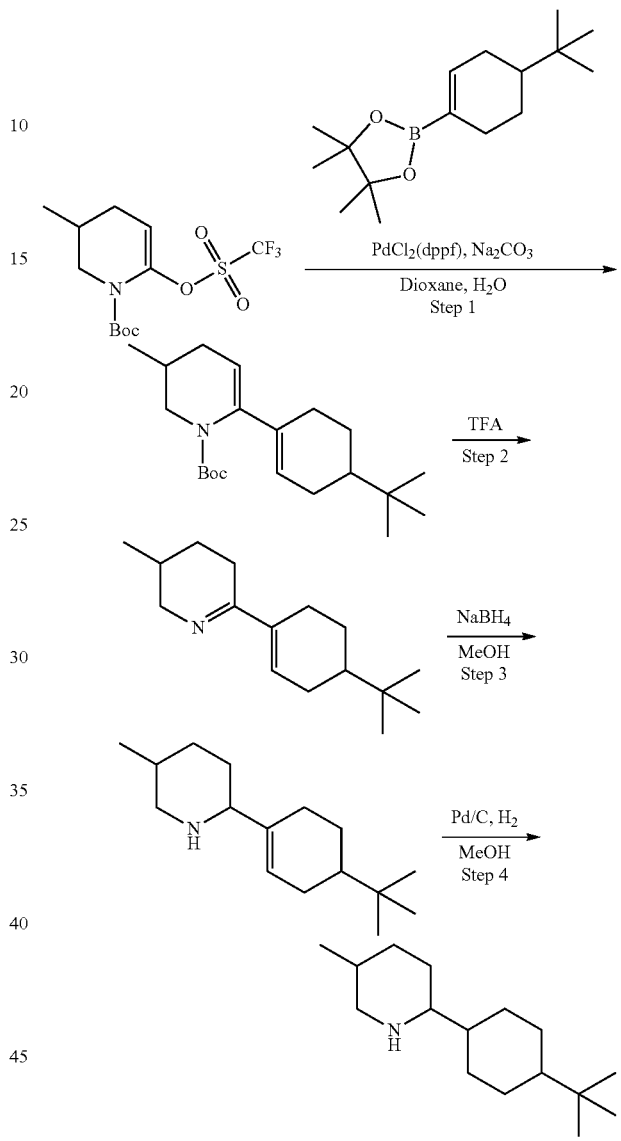

Step 1: Synthesis of tert-butyl 6-(4-tert-butylcyclohexan-1-yl)-3-methyl-3,4-dihydro-2H-pyridine-1-carboxylate A stirring solution of tert-butyl 3-methyl-6-(trifluoromethylsulfonyloxy)-3,4-dihydro-2H-pyridine-1-carboxylate (7.19 g, 20.82 mmol), 2-(4-tert-butylcyclohexan-1-yl)-4,4,5,5-tetramethyl-1,3,2-dioxaborolane (5 g, 18.92 mmol)) and Sodium carbonate (6.02 g, 56.77 mmol) in 1,4-dioxane (90 mL) and Water (30 mL) was purged with argon. Then, Pd(dppf)C$_{12}$ (772.71 mg, 946.22 μmol) was added under argon. The reaction mixture was stirred under argon at 80° C. for 14 hours After 14 hours, the reaction mixture was cooled and filtered. The filter cake was washed with 1,4-dioxane (2×20 mL) and discarded. The filtrate was evaporated in vacuo and the residue was purified by column chromatography to afford tert-butyl 6-(4-tert-butylcyclohexan-1-yl)-3-methyl-3,4-dihydro-2H-pyridine-1-carboxylate (3.10 g, 9.30 mmol, 49.12% yield) as colorless oil.

LCMS(ESI): [M+Boc]⁺ m/z: calcd 333.3; found 278.2 (t-Bu cleaved product mass); Rt=1.903 min.

Step 2: Synthesis of 6-(4-tert-butylcyclohexan-1-yl)-3-methyl-2,3,4,5-tetrahydropyridine tert-butyl 6-(4-tert-butylcyclohexan-1-yl)-3-methyl-3,4-dihydro-2H-pyridine-1-carboxylate (3.1 g, 9.30 mmol) was dissolved in Trifluoroacetic acid (30 g, 263.10 mmol, 20.27 mL). The resulting reaction mixture was stirred at 25° C. for 3 hours. After 3 hours, the reaction mixture was cooled to 0° C. and 20% aqueous NaOH solution was added dropwise. The resulting suspension was extracted with dichloromethane (2×100 mL). The combined organic phase was washed with water (100 mL), dried over Na₂SO₄ and evaporated under reduced pressure to afford 6-(4-tert-butylcyclohexan-1-yl)-3-methyl-2,3,4,5-tetrahydropyridine (2.1 g, 9.00 mmol, 96.80% yield) as colorless oil. The crude product was used in the next step reaction without any further purification.

LCMS(ESI): [M+H]⁺ m/z: calcd 233.2; found 234.2; Rt=1.045 min.

Step 3: Synthesis of 2-(4-tert-butylcyclohexan-1-yl)-5-methyl-piperidine

To a stirred solution of 6-(4-tert-butylcyclohexan-1-yl)-3-methyl-2,3,4,5-tetrahydropyridine (2.1 g, 9.00 mmol) in MeOH (30 mL) was added Sodium Borohydride (1.02 g, 26.99 mmol, 954.42 μL) portionwise at 0° C. The resulting reaction mixture was stirred at 25° C. for 4 hours. After 4 hours, the reaction mixture was concentrated under reduced pressure. The obtained residue was diluted with water (80 mL) and extracted with DCM (2×100 mL). The combined organic phase was washed with brine, dried over Na₂SO₄ and concentrated under reduced pressure to give 2-(4-tert-butylcyclohexan-1-yl)-5-methyl-piperidine (2 g, 8.50 mmol, 94.42% yield) as a colorless oil. The crude product was used in the next step reaction without any further purification.

LCMS(ESI): [M+H]⁺ m/z: calcd 235.2; found 236.2; Rt=1.222 min.

Step 4: Synthesis of 2-(4-tert-butylcyclohexyl)-5-methyl-piperidine

A solution of 2-(4-tert-butylcyclohexan-1-yl)-5-methyl-piperidine (2 g, 8.50 mmol) in methanol (50 mL) was hydrogenated over Palladium, 10% on carbon (0.2 g) under hydrogen atmosphere at 25° C. for 72 hours. Upon completion, the reaction mixture was filtered, the filter cake was washed with methanol and the filtrate was concentrated under reduced pressure to afford 2-(4-tert-butylcyclohexyl)-5-methyl-piperidine (1.5 g, 6.32 mmol, 74.36% yield) as light-yellow gum. The crude product was used in the next step reaction without any further purification.

LCMS(ESI): [M+H]⁺ m/z: calcd 237.3; found 238.2; Rt=1.267 min.

4AA. Synthesis of 2-cyclobutyl-5-methyl-piperidine

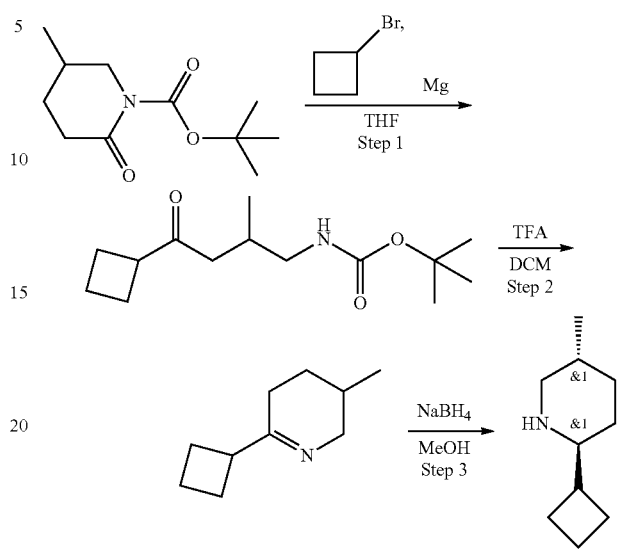

Step 1: Synthesis of tert-butyl N-(4-cyclobutyl-2-methyl-4-oxo-butyl)carbamate

To a suspension of Magnesium (3.13 g, 128.94 mmol, 1.80 mL) in THF (200 mL) was added cyclobutylbromide (17.41 g, 128.94 mmol). The reaction mixture was stirred for 45 minutes to give a grey solution. The freshly prepared Grignard reagent was added dropwise to a precooled suspension of tert-butyl 5-methyl-2-oxo-piperidine-1-carboxylate (25 g, 117.22 mmol) in THF (100 mL) at −78° C. The reaction mixture was stirred at −78° C. for 1 hour. After 1 hour, the reaction mixture was allowed to warm to room temperature and stirred for 12 hours. After 12 hours, the reaction was diluted with MTBE (500 mL) and slowly quenched with 100 mL of saturated ammonium chloride aqueous solution. The organic phase was washed with a saturated sodium bicarbonate solution (2×200 mL). The combined aqueous fractions were back extracted MTBE. The combined organic phase was dried over Na₂SO₄ and concentrated under reduced pressure. The crude product was purified by column chromatography to obtain tert-butyl N-(4-cyclobutyl-2-methyl-4-oxo-butyl)carbamate (3.9 g, 15.27 mmol, 13.03% yield) as a colorless liquid.

¹H NMR (CDCl₃, 400 MHz): δ (ppm) 0.85 (m, 3H), 1.42 (m, 10H), 1.59 (m, 3H), 1.86 (m, 2H), 2.16 (m, 4H), 2.34 (m, 2H), 2.98 (m, 2H), 3.23 (m, 1H), 4.61 (brs, 1H).

Step 2: Synthesis of 6-cyclobutyl-3-methyl-2,3,4,5-tetrahydropyridine

A solution of tert-butyl N-(4-cyclobutyl-2-methyl-4-oxo-butyl)carbamate (3.9 g, 15.27 mmol) in TFA (20 mL) and DCM (20 mL) was stirred at 25° C. for 12 hours. After 12 hours, saturated aq. Sodium sulfate solution was added (50 mL) and then extracted with DCM (2×50 mL). The combined organic phase was dried over Na₂SO₄, filtered and concentrated under reduced pressure to obtain 6-cyclobutyl-3-methyl-2,3,4,5-tetrahydropyridine (2.6 g, crude) as a light-yellow oil. The crude product was used for the next step reaction without any further purification.

¹H NMR (CDCl₃, 400 MHz): δ (ppm) 0.89 (m, 3H), 1.19 (m, 1H), 1.54 (m, 1H), 1.72 (m, 2H), 1.88 (m, 1H), 2.09 (m, 6H), 2.96 (m, 2H), 3.72 (d, 1H).

Step 3: Synthesis of 2-cyclobutyl-5-methyl-piperidine

Sodium Borohydride (1.30 g, 34.38 mmol, 1.22 mL) was added portionwise to a solution of 6-cyclobutyl-3-methyl-2,3,4,5-tetrahydropyridine (2.6 g, 17.19 mmol) in Methanol (30 mL). The mixture was stirred at room temperature for 12 hours. After 12 hours, Water (50 mL) was added and the resulting mixture was extracted with EtOAc (2×50 mL). The combined organic phase was dried over sodium sulfate, filtered and concentrated under reduced pressure to obtain 2-cyclobutyl-5-methyl-piperidine (1.56 g, crude) as a light-yellow liquid. The crude product was used for the next step reaction without any further purification.

¹H NMR (CDCl₃, 400 MHz): δ (ppm) 0.81 (m, 3H), 0.92 (m, 2H), 1.43 (m, 2H), 1.68 (m, 7H), 1.92 (m, 4H), 2.17 (m, 4H), 2.98 (d, 1H).

4BB. The Synthesis of rac-3-chloro-5-((2R,5S)-5-methylpiperidin-2-yl)pyridine

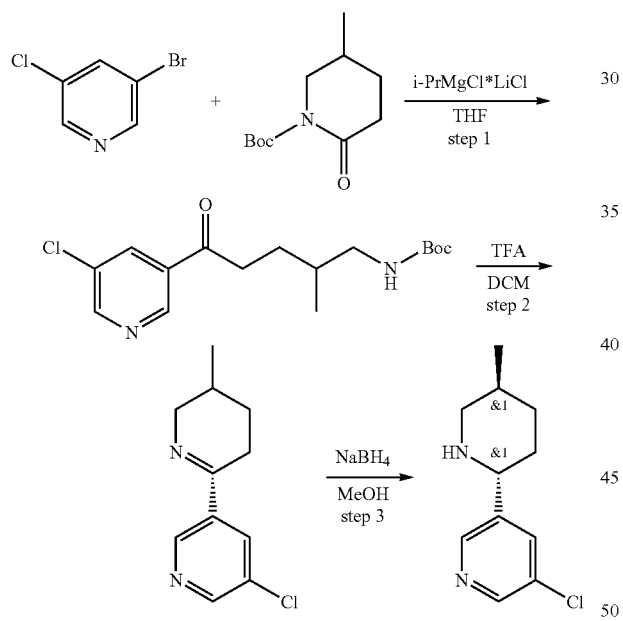

Step 1: Synthesis of tert-butyl (5-(5-chloropyridin-3-yl)-2-methyl-5-oxopentyl)carbamate 3-bromo-5-chloro-pyridine (5 g, 25.98 mmol) was dissolved in THF (30 mL) and cooled to −78° C. under Ar. Isopropyl magnesium chloride lithium chloride (1.3 M, 9.70 mL) was added in a dropwise manner, keeping temperature near −78° C. After the reagent was added, the reaction mixture was warmed to rt and stirred for 3 hr at the same temperature, following by the slow addition of the solution of tert-butyl 5-methyl-2-oxo-piperidine-1-carboxylate (5.54 g, 25.98 mmol) in EtOAc (50 mL) and slow warming of the reaction mixture to rt. After the reaction was complete, the mixture was poured on 10% aq NH₄Cl, and extracted with EtOAc (30 mL) three times. Evaporation of the combined organic solvents and purification with CC (OK. Interchim, 330 g SiO₂, petroleum ether/MTBE with MTBE from 10~100%, flow rate=135 mL/min, Rv=11-12 CV) results in tert-butyl N-[5-(5-chloro-3-pyridyl)-2-methyl-5-oxo-pentyl]carbamate (4.5 g, 13.77 mmol, 52.99% yield).

¹H NMR (400 MHz, CDCl₃) δ (ppm) 0.98 (d, 3H), 1.42 (s, 9H), 1.77 (m, 3H), 3.02 (m, 4H), 4.67 (m, 1H), 8.17 (s, 1H), 8.71 (s, 1H), 9.00 (s, 1H). LCMS(ESI): [M-Boc]⁺ m/z: calcd 226.2; found 227.2; Rt=1.316 min.

Step 2: Synthesis of 5'-chloro-5-methyl-3,4,5,6-tetrahydro-2,3'-bipyridine tert-butyl N-[5-(5-chloro-3-pyridyl)-2-methyl-5-oxo-pentyl]carbamate (4.5 g, 13.77 mmol) was dissolved in DCM (40 mL) following by the addition of TFA (3.14 g, 27.54 mmol, 2.12 mL) and stirring for 3 hr. After the reaction was complete (gas evolution has stopped) the mixture was basified with 50% aq NaOH to pH=14. The layers were separated, and the upper layer was additionally extracted with DCM (3*20 mL). Combined organic layers was dried over Na₂SO₄ and evaporated under reduced pressure to give 3-chloro-5-(3-methyl-2,3,4,5-tetrahydropyridin-6-yl)pyridine (2.5 g, 11.98 mmol, 87.00% yield) which was used in the next step without purification.

LCMS(ESI): [M]⁺ m/z: calcd 208.2; found 209.2; Rt=0.493 min.

Step 3: Synthesis of rac-3-chloro-5-((2R,5S)-5-methylpiperidin-2-yl)pyridine 3-chloro-5-(3-methyl-2,3,4,5-tetrahydropyridin-6-yl)pyridine (2.5 g, 11.98 mmol) was dissolved in MeOH (5 mL) and cooled to 0° C. Sodium borohydride (906.44 mg, 23.96 mmol, 847.14 μL) was added in portions to obtained mixture and additionally stirred overnight. After the reaction was complete, the reaction mixture was acidified with 10% aq HCl to pH=2, washed with MTBE (2*10 mL), basified with 10% aq NaOH to pH=10 and extracted with DCM (20 mL). Evaporation of the solvent result in pure 3-chloro-5-[(2R,5S)-5-methyl-2-piperidyl]pyridine (2.2 g, 10.44 mmol, 87.16% yield).

¹H NMR (500 MHz, DMSO-d₆) δ (ppm) 0.96 (d, 3H), 1.12 (m, 1H), 1.78 (m, 5H), 2.42 (m, 1H), 3.12 (m, 1H), 3.61 (m, 1H), 7.72 (s, 1H), 8.48 (s, 2H). LCMS(ESI): [M]⁻ m/z: calcd 210.2; found 211.2; Rt=0.631 min.

4CC. Synthesis of 2-(3,5-dichlorophenyl)-5-methyl-piperidine

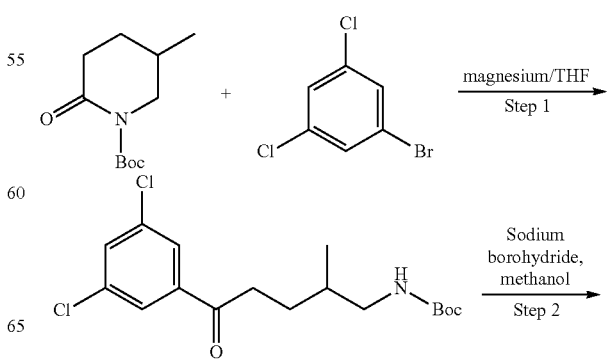

-continued

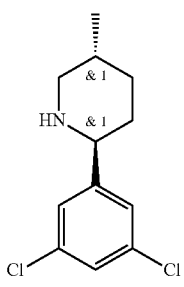

Step 1. Synthesis of tert-butyl N-[5-(3,5-dichloro-phenyl)-2-methyl-5-oxo-pentyl]carbamate 2-[(5-carbamoyl-3-pyridyl)amino]-2-oxo-acetic acid (241.77 mg, 1.16 mmol) and 5-(5-methyl-2-piperidyl)-1H-pyrazolo[4,3-b]pyridine (0.25 g, 1.16 mmol) were mixed in DMF (20 mL). The reaction suspension was cooled to 0° C. and HATU (439.51 mg, 1.16 mmol) followed by TEA (116.97 mg, 1.16 mmol, 161.11 μL) were added and stirred at ambient temperature for 12 hr. The reaction mixture was evaporated in vacuo and obtained crude product 0.48 g was purified by preparative 25-45% 1-6 min water-methanol (NH$_3$ 0.1%), flow 30 ml/min to afford product 5-[[2-[(2R,5S)-5-methyl-2-(1H-pyrazolo[4,3-b]pyridin-5-yl)-1-piperidyl]-2-oxo-acetyl]amino]pyridine-3-carboxamide (0.14 g, 343.62 μmol, 29.73% yield).

$^1$H NMR (400 MHz, CDCl$_3$) δ 0.92 (m, 3H), 1.42 (s, 13H), 1.67-1.82 (m, 2H), 2.95 (m, 2H), 4.68 (m, 1H), 7.21 (m, 1H), 7.82 (m, 2H).

LCMS(ESI): [M]$^+$ m/z: calcd 360.0; found 360.2; Rt=1.683 min.

Step 2. Synthesis of 2-(3,5-Dichlorophenyl)-5-methyl-piperidine

The tert-butyl N-[5-(3,5-dichlorophenyl)-2-methyl-5-oxo-pentyl]carbamate (12 g, 33.31 mmol) was stirred in Trifluoroacetic acid (18.99 g, 166.54 mmol, 12.83 mL) for 1 hr. TLC was used to check the reaction progress. 50% w/v NaOH solution was added to the mixture until the pH was 13-14. The product was extracted 4×20 mL with DCM and the organic layers combined, dried with MgSO$_4$ and evaporated. The product was dissolved in mixture water (25 mL)/MeOH (150 mL) and added to a flask followed by Sodium Borohydride (1.26 g, 33.31 mmol, 1.18 mL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na$_2$SO$_4$, filtered and evaporated. The residue was purified by CC (Interchim, 120 g SiO$_2$, hexane/MTBE with MTBE from 0~100%, flow rate=85 ml/min, RV=6,9 CV.) to give 2-(3,5-dichlorophenyl)-5-methyl-piperidine (2.9 g, 11.88 mmol, 35.66% yield) as a light-yellow oil.

$^1$H NMR (400 MHz, CDCl$_3$) δ 0.88 (d, 3H), 1.13 (m, 1H), 1.45 (dd, 1H), 1.63 (m, 2H), 1.77 (d, 1H), 1.85 (d, 1H), 2.38 (dd, 1H), 3.11 (d, 1H), 3.60 (d, 1H), 7.21 (s, 1H), 7.26 (s, 2H).

LCMS(ESI): [M+1]$^+$ m/z: calcd 243.0; found 244.2; Rt=0.978 min.

4DD. The Synthesis of 2-methyl-5-[(2R,5S)-5-methyl-2-piperidyl]pyridine

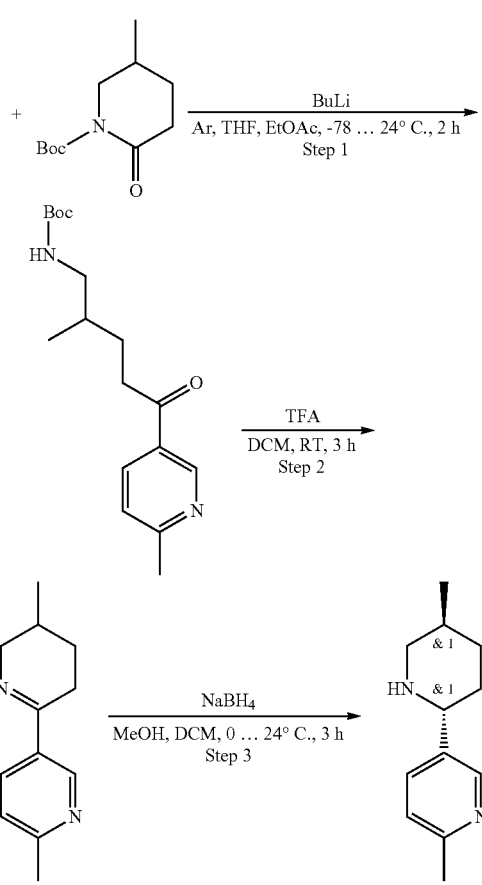

Step 1: The Synthesis of tert-butyl N-[2-methyl-5-(6-methyl-3-pyridyl)-5-oxo-pentyl]carbamate 5-bromo-2-methyl-pyridine (3 g, 17.44 mmol) was dissolved in THF (30 mL) and cooled to −78° C. under Ar. butyl lithium (2.5 M, 7.67 mL) was added in a dropwise manner, keeping temperature near −78° C. After the reagent was added, the reaction mixture was stirred for 0.5 hr at the same temperature, following by the slow addition of the solution of tert-butyl 5-methyl-2-oxo-piperidine-1-carboxylate (3.72 g, 17.44 mmol) in THF (10 mL) and slow warming of the reaction mixture to rt. After the reaction was complete, the mixture was poured on 10% aq NH$_4$Cl, and extracted with EtOAc (50 mL) three times. Evaporation of the combined organic solvents results in crude tert-butyl N-[2-methyl-5-(6-methyl-3-pyridyl)-5-oxo-pentyl]carbamate (7 g, crude) which was used in the next step without purification.

$^1$H NMR (400 MHz, CDCl$_3$) δ 1.02 (m, 3H), 1.24 (s, 9H), 1.46 (m, 2H), 1.86 (m, 2H), 2.59 (m, 3H), 2.67 (m, 3H), 4.72 (m, 1H), 7.24 (s, 1H), 8.09 (s, 1H), 9.02 (s, 1H).

Step 2: The Synthesis of 2-methyl-5-(3-methyl-2,3,4,5-tetrahydropyridin-6-yl)pyridine tert-butyl N-[2-methyl-5-(6-methyl-3-pyridyl)-5-oxo-pentyl]carbamate (7 g, 22.85 mmol) was dissolved in DCM (30 mL) following by the addition of TFA (5.21 g, 45.69 mmol, 3.52 mL) and stirring for 3 hr. After the reaction was complete (gas evolution has stopped) the mixture was basified with 50% aq NaOH to pH 14. The layers were separated, and the upper layer was additionally extracted with DCM (3*20 mL). Combined organic layers was dried over $Na_2SO_4$ and evaporated under reduced pressure to give 2-methyl-5-(3-methyl-2,3,4,5-tetrahydropyridin-6-yl)pyridine (3.5 g, crude).

$^1$H NMR (400 MHz, $CDCl_3$) δ 1.04 (m, 3H), 1.21 (m, 2H), 1.91 (m, 2H), 3.71 (m, 3H), 3.21 (m, 2H), 4.01 (m, 1H), 7.12 (s, 1H), 7.98 (s, 1H), 8.78 (s, 1H).

Step 3: The Synthesis of 2-methyl-5-[(2R,5S)-5-methyl-2-piperidyl]pyridine 2-methyl-5-(3-methyl-2,3,4,5-tetrahydropyridin-6-yl)pyridine (2.92 g, 15.51 mmol) was dissolved in Methanol (20 mL) and cooled to 0° C. Sodium Borohydride (1.17 g, 31.02 mmol, 1.10 mL) was added in portions to obtained mixture and additionally stirred overnight. After the reaction was complete, the reaction mixture was acidified with 10% aq HCl to pH 2, washed with MTBE (2*10 mL), basified with 10% aq NaOH to pH 10 and extracted with DCM (40 mL). Evaporation of the solvent and purification with silica gel column chromatography (Companion; 120 g $SiO_2$; MtBE/methanol with methanol from 0 to 20%, flow rate=85 ml/min, Rv=10-11 cv.) result in pure 2-methyl-5-[(2R,5S)-5-methyl-2-piperidyl]pyridine (0.7 g, 3.68 mmol, 23.72% yield).

$^1$H NMR (500 MHz, $CDCl_3$) δ 0.94 (m, 3H), 1.07 (m, 1H), 1.72 (m, 5H), 2.41 (m, 1H), 2.55 (s, 3H), 3.05 (m, 1H), 3.55 (m, 1H), 7.03 (s, 1H), 7.56 (s, 1H), 8.41 (s, 1H).

LCMS(ESI): $[M+H]^+$ m/z: calcd 190.2; found 191.2; Rt=0.458 min.

4EE. Synthesis of rac-(2S,4R)-4-ethyl-2-phenyl-piperidine

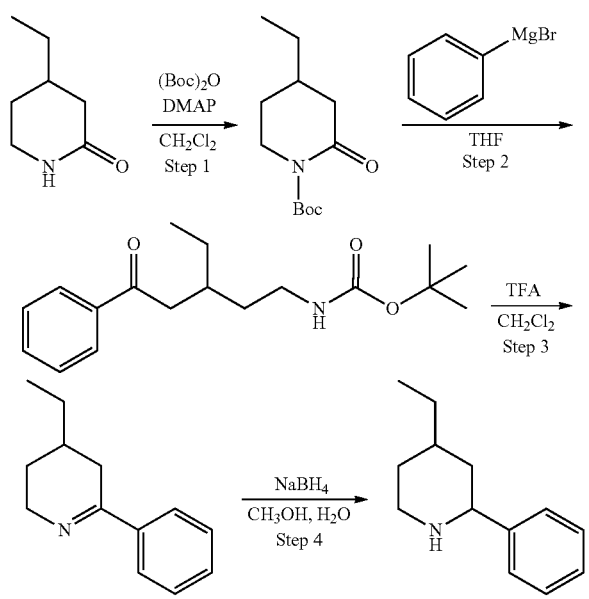

Step 1: Synthesis of tert-butyl 4-ethyl-2-oxo-piperidine-1-carboxylate

To a stirred solution of 4-ethylpiperidin-2-one (5 g, 39.31 mmol) in DCM (1000 mL) was added DMAP (48.03 mg, 393.13 μmol). The resulting reaction mixture was heated to reflux. Di-tert-butyl dicarbonate (17.16 g, 78.63 mmol, 18.04 mL) was added drop wise over 48 hours. Upon completion, the reaction mixture was concentrated under reduced pressure to give tert-butyl 4-ethyl-2-oxo-piperidine-1-carboxylate (10 g, crude). The crude product was used in the next step reaction without any further purification.

Step 2: Synthesis of tert-butyl N-[6-oxo-6-(2-thienyl)hexyl]carbamate

To a stirred solution of tert-butyl 4-ethyl-2-oxo-piperidine-1-carboxylate (5 g, 22.00 mmol) in THF (50 mL) was added phenyl magnesiumbromide (1 M in THF, 3.99 g, 22.00 mmol, 22 mL) drop wise at −78° C. under argon atmosphere. The reaction mixture was slowly allowed to warm to room temperature. Upon completion, the reaction mixture was quenched with sat aq $NH_4Cl$ solution and extracted with EtOAc (3×100 mL). The combined organic phase was washed with brine (3×30 mL), dried over $Na_2SO_4$ and evaporated under reduced pressure to give tert-butyl N-(3-ethyl-5-oxo-5-phenyl-pentyl)carbamate (2.5 g, 8.19 mmol, 37.21% yield). The crude product was used in the next step reaction without any further purification.

Step 3: Synthesis of 4-ethyl-6-phenyl-2,3,4,5-tetrahydropyridine

To a stirred solution of tert-butyl N-(3-ethyl-5-oxo-5-phenyl-pentyl)carbamate (2.5 g, 8.19 mmol) in DCM (20 mL) was added TFA (1.87 g, 16.37 mmol, 1.26 mL). The resulting reaction mixture was stirred at room temperature for 3 hours. Upon completion, the reaction mixture was basified with 50% aq NaOH solution to pH=14. The resulting suspension was extracted with DCM (3×20 mL). The combined organic phase was dried over $Na_2SO_4$ and concentrated under reduced pressure to give 4-ethyl-6-phenyl-2,3,4,5-tetrahydropyridine (1.4 g, 7.48 mmol, 91.32% yield). The crude product was used in the next step reaction without any further purification.

Step 4: Synthesis of rac-(2S,4R)-4-ethyl-2-phenyl-piperidine

Sodium borohydride (282.80 mg, 7.48 mmol, 264.30 μL) was added portion wise, to a stirred solution of 4-ethyl-6-phenyl-2,3,4,5-tetrahydropyridine (1.4 g, 7.48 mmol) in MeOH and $H_2O$ at 0° C. The resulting reaction mixture was stirred at the room temperature for overnight. Upon completion, the reaction mixture was acidified with 10% aq HCl to pH=2, washed with MTBE (2×10 mL). The aqueous layer was basified with 10% aq NaOH solution to pH=10 and extracted with DCM. The organic layer was dried over $Na_2SO_4$ and concentrated under reduced pressure to obtain rac-(2S,4R)-4-ethyl-2-phenyl-piperidine (0.8 g, 4.23 mmol, 56.53% yield).

5. Syntheses from Pyridines

5A. The Synthesis of 2-(3,4-dimethylphenyl)-5-methyl-piperidine

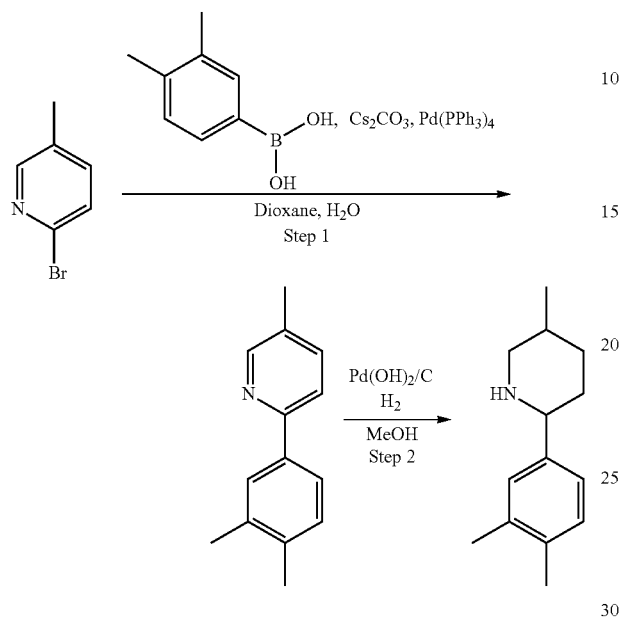

Step 1: Synthesis of 2-(3,4-dimethylphenyl)-5-methyl-pyridine

To a stirred solution of 2-bromo-5-methyl-pyridine (1 g, 5.81 mmol) and (3,4-dimethylphenyl)boronic acid (1.05 g, 6.98 mmol) in dioxane (20 mL) was added cesium carbonate (7.58 g, 23.25 mmol). The resulting suspension was degassed with argon. Tetrakis(triphenylphosphine)palladium(0), 99.8% (metals basis) (335.87 mg, 290.66 µmol) was added. The reaction mixture was stirred at 65° C. for overnight. Upon completion, the reaction mixture was filtered and the filtrate was evaporated in vacuo to get an oily residue. The residue was purified by reverse phase HPLC (49%, water-acetonitrile, 0.5-8.5 min; flow rate: 30 mL/min; loading pump: 4 mL/min, acetonitrile; column: SunFire 100*19 mm, 5 um) to give 2-(3,4-dimethylphenyl)-5-methyl-pyridine (0.78 g, 3.95 mmol, 68.02% yield).

$^1$H NMR (DMSO-d$_6$, 400 MHz): δ (ppm) 2.25 (s, 3H), 2.29 (s, 3H), 2.30 (s, 3H), 7.21 (d, 1H), 7.64 (dd, 1H), 7.77 (m, 2H), 7.85 (s, 1H), 8.46 (s, 1H).

LCMS(ESI): [M+H]$^+$ m/z: calcd 197.2; found 198.2; Rt=2.588 min.

Step 2: Synthesis of 2-(3,4-dimethylphenyl)-5-methyl-piperidine

A solution of 2-(3,4-dimethylphenyl)-5-methyl-pyridine (0.78 g, 3.95 mmol) in MeOH (20 mL) was hydrogenated over 5% Pd(OH)$_2$/C (488.01 mg, 3.95 mmol) under 100 atm H$_2$ pressure at 50° C. for 18 hours. Upon completion, the reaction mixture was filtered, the residue was washed with MeOH (10 mL) and the filtrate was concentrated under reduced pressure to obtain 2-(3,4-dimethylphenyl)-5-methyl-piperidine (0.7 g, 3.44 mmol, 87.07% yield). The crude product was used for the next step reaction without any further purification.

LCMS(ESI): [M+H]$^+$ m/z: calcd 203.2; found 204.2; Rt=0.901 min.

5B. Synthesis of 1-(4-(3-(Piperidin-2-yl)phenyl)piperidin-1-yl)ethanone

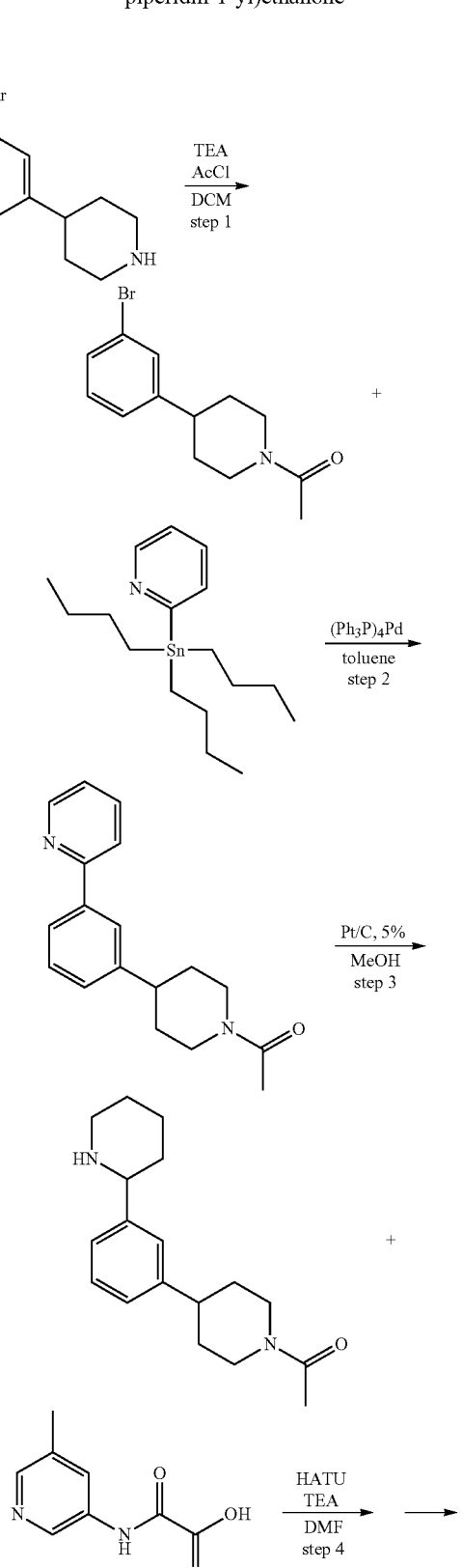

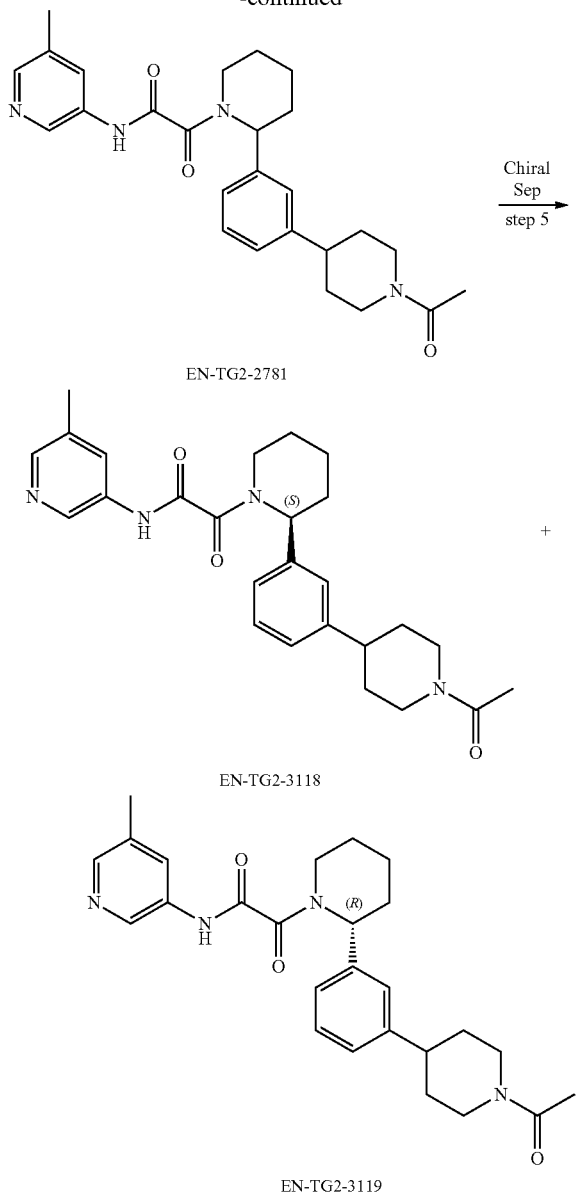

EN-TG2-2781

EN-TG2-3118

EN-TG2-3119

Step 1: Synthesis of 1-(4-(3-bromophenyl)piperidin-1-yl)ethanone

To a solution of 4-(3-bromophenyl)piperidine (20 g, 72.31 mmol, HCl) and triethylamine (18.29 g, 180.77 mmol, 25.20 mL) in DCM (250 mL), acetyl chloride (6.81 g, 86.77 mmol, 5.28 mL) was added dropwise at 0° C. The resulting mixture was stirred at 25° C. for 12 hr and diluted with water (70 ml). The organic layer was separated, washed with brine (3*50 ml), dried over Na₂SO₄ and evaporated in vacuo obtain 1-[4-(3-bromophenyl)-1-piperidyl]ethanone (19.3 g, 68.40 mmol, 94.59% yield).

¹H NMR (500 MHz, CDCl₃) δ (ppm) 1.59 (m, 2H), 1.88 (m, 2H), 2.13 (s, 3H), 2.59 (t, 1H), 2.71 (t, 1H), 3.15 (t, 1H), 3.92 (d, 1H), 4.78 (d, 1H), 7.12 (d, 1H), 7.18 (t, 1H), 7.34 (m, 2H).

LCMS(ESI): [M]⁺ m/z: calcd 282.2; found 283.2; Rt=1.277 min.

Step 2: Synthesis of 1-(4-(3-(pyridin-2-yl)phenyl)piperidin-1-yl)ethanone

A solution of 1-[4-(3-bromophenyl)-1-piperidyl]ethanone (8 g, 28.35 mmol), tributyl(2-pyridyl)stannane (11.48 g, 31.19 mmol, 10.07 mL) and tetrakis(triphenylphosphine)palladium(0), 99.8% (metals basis), Pd 9% min (1.64 g, 1.42 mmol) in toluene (150 mL) was heated under Ar atmosphere at 100° C. for 18 hr. The solvent was evaporated in vacuo and the residue was purified by gradient chromatography (DCM-ACN) to obtain 1-[4-[3-(2-pyridyl)phenyl]-1-piperidyl]ethanone (7.3 g, 26.04 mmol, 91.84% yield).

¹H NMR (400 MHz, DMSO-d₆) δ (ppm) 1.51 (m, 1H), 1.67 (m, 1H), 1.83 (m, 2H), 2.03 (s, 3H), 2.62 (t, 1H), 2.86 (t, 1H), 3.14 (t, 1H), 3.92 (d, 1H), 4.55 (d, 1H), 7.32 (m, 2H), 7.41 (m, 1H), 7.86 (m, 2H), 7.95 (m, 2H), 8.65 (d, 1H). LCMS(ESI): [M]⁺ m/z: calcd 280.4; found 281.2; Rt=0.949 min.

Step 3: Synthesis of 1-(4-(3-(piperidin-2-yl)phenyl)piperidin-1-yl)ethanone

1-[4-[3-(2-pyridyl)phenyl]-1-piperidyl]ethanone (7.3 g, 26.04 mmol) were dissolved in MeOH (350 mL) and platinum, 5% on carbon, dry (1.02 g, 5.21 mmol) was added. The reaction mixture was heated at 100° C. in high pressure vessel at 50 atm H₂ pressure for 96 hr. The catalyst was filtered off, washed with MeOH and the solvent was evaporated, the residue was dried to give 1-[4-[3-(2-piperidyl)phenyl]-1-piperidyl]ethanone (6 g, 20.95 mmol, 80.46% yield).

¹H NMR (400 MHz, DMSO-d₆) δ (ppm) 1.47 (m, 1H), 1.62 (m, 2H), 1.83 (m, 6H), 2.02 (s, 3H), 2.61 (t, 1H), 2.74 (t, 1H), 2.98 (t, 1H), 3.15 (t, 1H), 3.26 (d, 1H), 3.91 (d, 1H), 4.15 (bds, 1H), 4.52 (d, 1H), 7.24 (m, 1H), 7.32 (m, 2H), 7.41 (m, 1H), 7.52 (s, 1H), 9.41 (bds, 1H). LCMS(ESI): [M]⁻ m/z: calcd 286.4; found 287.2; Rt=0.786 min.

5C. The Synthesis of 3-(5-methyl-2-piperidyl)aniline

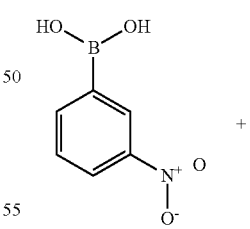

+

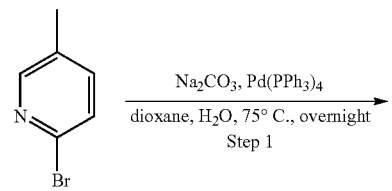

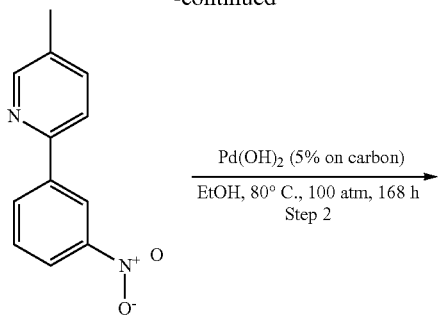

Step 1: The Synthesis of 5-methyl-2-(3-nitrophenyl)pyridine (3-nitrophenyl)boronic acid (10.19 g, 61.04 mmol) and 2-bromo-5-methyl-pyridine (10 g, 58.13 mmol) were dissolved in dioxane (50 mL) and $H_2O$ (1 mL), following by the addition of sodium carbonate (24.65 g, 232.53 mmol, 9.74 mL). The resulting suspension was thoroughly degassed and tetrakis(triphenylphosphine)palladium(0), 99.8% (metals basis), Pd 9% min (1.34 g, 1.16 mmol) was added. The reaction mixture was stirred at 75° C. overnight. After the completion of the reaction (as showed by LCMS), the reaction mixture was filtered and concentrated in vacuo to give oily residue, which was purificated by flash chromatography (OK. $1^{st}$ run: Companion combiflash, 330 g $SiO_2$, petroleum ether/ethyl acetate with ethyl acetate from 0~25%, flow rate 100 mL/min, Rv=8 CV; $2^{nd}$ run: Companion combiflash, 120 g $SiO_2$, chloroform/acetonitrile with acetonitrile from 0-5%, flow rate 85 mL/min, Rv=5 CV) to afford 5-methyl-2-(3-nitrophenyl)pyridine (3.8 g, 17.74 mmol, 30.51% yield).

$^1$H NMR (500 MHz, DMSO-$d_6$) δ 2.31 (s, 3H), 7.62 (m, 2H), 7.91 (m, 1H), 8.12 (m, 1H), 8.32 (m, 1H), 8.45 (d, 1H), 9.82 (t, 1H)

LCMS(ESI): [M+H]$^+$ m/z: calcd 214.1; found 215.0; Rt=1.416 min.

Step 2: The Synthesis of 3-(5-methyl-2-piperidyl)aniline 5-methyl-2-(3-nitrophenyl)pyridine (2.1 g, 9.80 mmol) was added to the suspension of palladium hydroxide on carbon 5% (1.21 g) in EtOH (20 mL). The mixture was hydrogenated at 80° C. (100 atm) for 168 hr in autoclave. After the reaction was complete, the solids were filtered and the organic solvent was evaporated. The obtained crude residue was purified by HPLC (1-20% 0.5-6.5 min; water-acetonitrile+TFA; flow 30 mL/min; (loading pump 4 mL/min—water); target mass 190; column SunFire 100*19 mm 5 um) to afford 3-(5-methyl-2-piperidyl)aniline (1.2 g, 5.29 mmol, 53.99% yield, HCl).

$^1$H NMR (400 MHz, DMSO-$d_6$) δ 0.95 (m, 3H), 1.38 (m, 1H), 1.81 (m, 4H), 2.08 (m, 1H), 2.71 (m, 1H), 3.20 (m, 1H), 4.01 (m, 1H), 6.78 (m, 3H), 7.18 (dd, 1H), 8.87 (m, 1H), 9.08 (m, 1H).

LCMS(ESI): [M+H]$^+$ m/z: calcd 190.1; found 191.4; Rt=1.497 min.

5D. The Synthesis of 2-(3-methoxyphenyl)-5-methylpiperidine

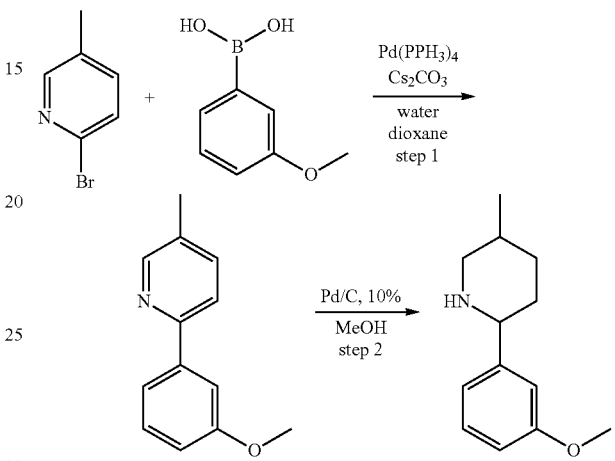

Step 1: Synthesis of 2-(3-methoxyphenyl)-5-methylpyridine 2-bromo-5-methyl-pyridine (3 g, 17.44 mmol) and (3-methoxyphenyl)boronic acid (3.18 g, 20.93 mmol) were dissolved in dioxane (40 mL) and water (4 mL). Cesium carbonate (14.21 g, 43.60 mmol) was added thereto. Then, tetrakis(triphenylphosphane)palladium(0) (87.20 μmol) was added and reaction flask was quickly evacuated and refilled with argon. Resulting mixture was stirred at 65° C. for 12 hr. After that, it was cooled and evaporated. The residue was partitioned between EtOAc (100 ml) and water (100 ml). The organic phase was collected, dried over $Na_2SO_4$ and evaporated. The residue was subjected to column chromatography to obtain 2-(3-methoxyphenyl)-5-methyl-pyridine (2 g, 10.04 mmol, 57.56% yield).

$^1$H NMR (400 MHz, DMSO-$d_6$) δ (ppm) 3.32 (s, 3H), 3.82 (s, 3H), 6.96 (m, 1H), 7.37 (m, 1H), 7.61 (m, 2H), 7.66 (m, 1H), 7.87 (m, 1H), 8.49 (s, 1H).

LCMS(ESI): [M]$^+$ m/z: calcd 199.2; found 200.2; Rt=1.024 min.

Step 2: Synthesis of 2-(3-methoxyphenyl)-5-methylpiperidine

Palladium, 10% on carbon, Type 487, dry (106.82 mg, 1.00 mmol) was added to the solution of 2-(3-methoxyphenyl)-5-methyl-pyridine (2 g, 10.04 mmol) in MeOH (20 mL) and the resulting mixture was hydrogenated at 50 atm. pressure and 80° C. for 72 hr. After consumption of starting material (H-NMR control) the resulting mixture was cooled to r.t., filtered. The filtrate was evaporated to dryness to obtain 2-(3-methoxyphenyl)-5-methyl-piperidine (1.3 g, 6.33 mmol, 63.09% yield).

¹H NMR (400 MHz, DMSO-d₆) δ (ppm) 0.82 (d, 3H), 1.12 (m, 1H), 1.36 (m, 1H), 1.51 (m, 1H), 1.72 (m, 2H), 2.23 (t, 1H), 2.96 (d, 1H), 3.22 (m, 1H), 3.41 (d, 1H), 3.72 (s, 3H), 6.76 (d, 1H), 6.89 (m, 2H), 7.19 (t, 1H).

LCMS(ESI): [M]⁺ m/z: calcd 205.3; found 206.2; Rt=0.833 min.

5E. Synthesis of N-methyl-6-(5-methyl-2-piperidyl)pyridin-3-amine

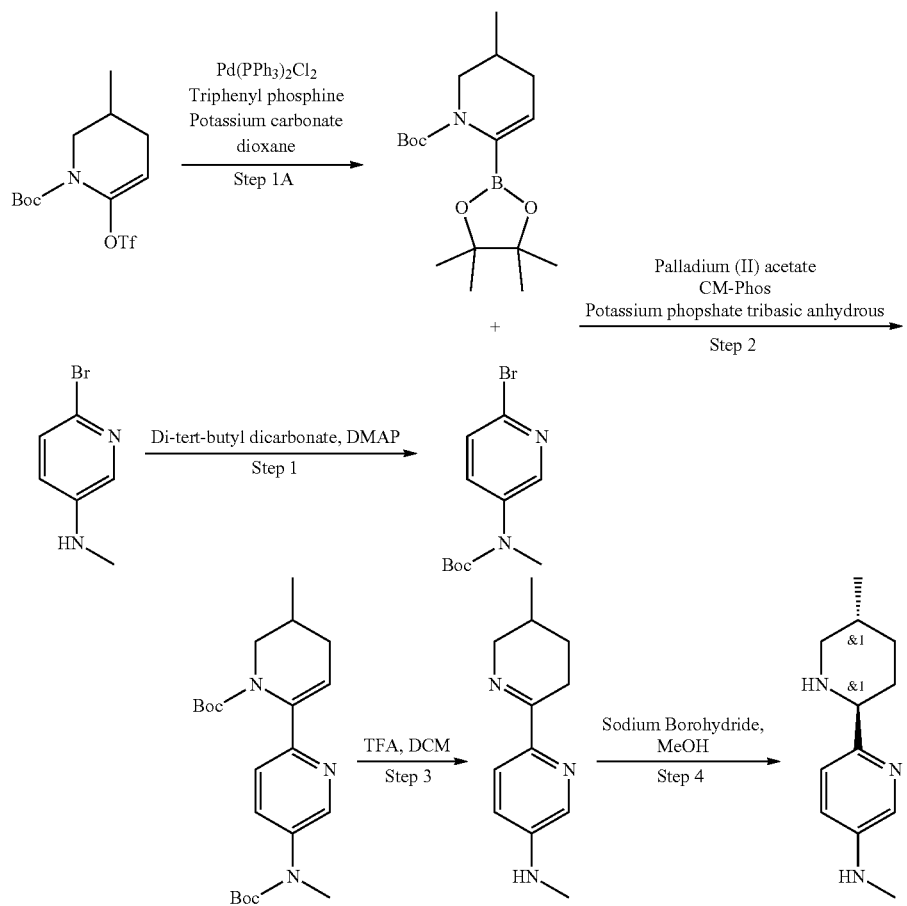

Step A. Synthesis of tert-butyl 3-methyl-6-(4,4,5,5-tetramethyl-1,3,2-dioxaborolan-2-yl)-3,4-dihydro-2H-pyridine-1-carboxylate tert-butyl 3-methyl-6-(trifluoromethylsulfonyloxy)-3,4-dihydro-2H-pyridine-1-carboxylate (3.5 g, 10.14 mmol) and 4,4,5,5-tetramethyl-2-(4,4,5,5-tetramethyl-1,3,2-dioxaborolan-2-yl)-1,3,2-dioxaborolane (3.86 g, 15.20 mmol) and Potassium carbonate, anhydrous, 99% (2.80 g, 20.27 mmol, 1.22 mL) were mixed together in dioxane (60 mL). The resulting mixture was evacuated and then backfilled with argon, this operation was repeated three times, then Bis (Triphenylphosphine)palladium (II) chloride (355.69 mg, 506.76 µmol) and Triphenyl phosphine (265.83 mg, 1.01 mmol) were added under argon. The reaction mixture was stirred under argon at 90° C. for 12 hr, then cooled and evaporated in vacuo poured into water (150 ml) and extracted with EtOAc (2×80 ml). The combined organic extracts were washed with water (2*40 ml), dried over sodium sulphate and evaporated in vacuo to leave 4.3 g of crude product, 4.3 g of which was purification by column chromatography on silica gel using hexane/MTBE gradient (10-100% EtOAc) to afford product tert-butyl 3-methyl-6-(4,4,5,5-tetramethyl-1,3,2-dioxaborolan-2-yl)-3,4-dihydro-2H-pyridine-1-carboxylate (2.2 g, 6.81 mmol, 67.15% yield)

¹H NMR (500 MHz, CDCl₃) δ (ppm) 0.90 (d, 3H), 1.25 (s, 12H), 1.50 (s, 9H), 1.50-1.75 (m, 2H), 2.15 (m, 1H), 2.75 (t, 1H), 3.56 (d, 1H), 5.22 (s, 1H).

Step 1. Synthesis of tert-butyl N-(6-bromo-3-pyridyl)-N-methyl-carbamate 6-bromo-N-methyl-pyridin-3-amine (8 g, 42.77 mmol) and DMAP (104.51 mg, 855.45 µmol) were dissolved in THF (40 mL) and Di-tert-butyl dicarbonate (28.00 g, 128.32 mmol, 29.45 mL) was added dropwise. The reaction mixture was stirred for 48 hr at 80° C. The resulting mixture was evaporated in vacuo, poured into aqeuous NaHCO₃(conc.) solution (50 ml) and extracted with EtOAc (2×30 ml). The combined organic extracts were washed with water (2*40 ml), dried over sodium sulphate and evaporated in vacuo to afford tert-butyl N-(6-bromo-3-pyridyl)-N-methyl-carbamate (10 g, 34.82 mmol, 81.42% yield)

¹H NMR (500 MHz, CDCl₃) δ (ppm) 1.46 (s, 9H), 3.27 (s, 3H), 7.25 (s, 1H), 7.41 (d, 1H), 7.49 (m, 1H), 8.29 (s, 1H).

LCMS(ESI): [M-Boc]⁺ m/z: calcd 287.2; found 289.0; Rt=1.276 min.

Step 2. Synthesis of tert-butyl 6-[5-[tert-butoxycarbonyl(methyl)amino]-2-pyridyl]-3-methyl-3,4-dihydro-2H-pyridine-1-carboxylate tert-butyl 3-methyl-6-(4,4,5,5-tetramethyl-1,3,2-dioxaborolan-2-yl)-3,4-dihydro-2H-pyridine-1-carboxylate (4.37 g, 13.52 mmol) and tert-butyl N-(6-bromo-3-pyridyl)-N-methyl-carbamate (2.59 g, 9.01 mmol) were mixed together in t-BuOH (100 mL). The resulting mixture was evacuated and then backfilled with argon, this operation was repeated three times, then Palladium (II) acetate (202.35 mg, 901.31 μmol) in t-BuOH (100 mL) and CM-Phos (727.42 mg, 1.80 mmol) were added under argon. The reaction mixture was stirred under argon at 115° C. for 17 hr, then cooled and evaporated in vacuo poured into water (150 ml) and extracted with EtOAc (2×50 ml). The combined organic extracts were washed with water (2*10 ml), dried over sodium sulphate and evaporated in vacuo to leave 3.6 g of crude product, 3.6 g of which was purification by column chromatography on silica gel using hexane/MTBE gradient (10-100% MTBE) and obtained crude product 1.1 g was purified by preparative 70-70-80% 0-1-6 min $H_2O$/MeOH/ 0.1% NH4OH, flow: 30 ml/min target mass to afford product tert-butyl 6-[5-[tert-butoxycarbonyl(methyl)amino]-2-pyridyl]-3-methyl-3,4-dihydro-2H-pyridine-1-carboxylate (0.022 g, 54.52 μmol, 6.05e-1% yield) and crude fraction 17 mg 66.23% by LCMS.

LCMS(ESI): $[M+1]^+$ m/z: calcd 403.3; found 404.4; Rt=3.854 min.

Step 4. Synthesis of N-methyl-6-(3-methyl-2,3,4,5-tetrahydropyridin-6-yl)pyridin-3-amine The solution of tert-butyl 6-[5-[tert-butoxycarbonyl (methyl)amino]-2-pyridyl]-3-methyl-3,4-dihydro-2H-pyridine-1-carboxylate (0.017 g, 42.13 μmol) in DCM (2 mL) and Trifluoroacetic acid (2 g, 17.54 mmol, 1.35 mL) was stirred at 0° C. for 5 hr, and then evaporated in vacuo. Crushed ice (10 g) was added to the residue and pH was adjusted to 8 with a 10% aqueous solution of sodium hydrocarbonate. The resulting mixture was extracted with ethylacetate (2*10 mL). The combined organic extracts were dried over sodium sulphate and evaporated in vacuo to afford N-methyl-6-(3-methyl-2,3,4,5-tetrahydropyridin-6-yl)pyridin-3-amine (0.011 g, crude)

LCMS(ESI): $[M+1]^+$ m/z: calcd 203.3; found 204.1; Rt=0.853 min.

Step 5. Synthesis of N-methyl-6-(5-methyl-2-piperidyl)pyridin-3-amine

Sodium Borohydride (4.09 mg, 108.22 μmol, 3.83 μL) was added in one portion to a stirred solution of N-methyl-6-(3-methyl-2,3,4,5-tetrahydropyridin-6-yl)pyridin-3-amine (0.011 g, 54.11 μmol) in MeOH at 0° C. The resulting mixture was stirred at 0° C. for 5 hr, and then evaporated in vacuo. The residue was diluted with water (10 mL) and extracted with dichloromethane (2*10 mL). The combined organic extracts were dried over sodium sulphate and evaporated in vacuo to afford N-methyl-6-(5-methyl-2-piperidyl) pyridin-3-amine (0.009 g, 43.84 μmol, 81.01% yield).

LCMS(ESI): $[M+1]^+$ m/z: calcd 205.3; found 206.2; Rt=0.527 min.

5F. The Synthesis of 4-methyl-2-phenyl-piperidine

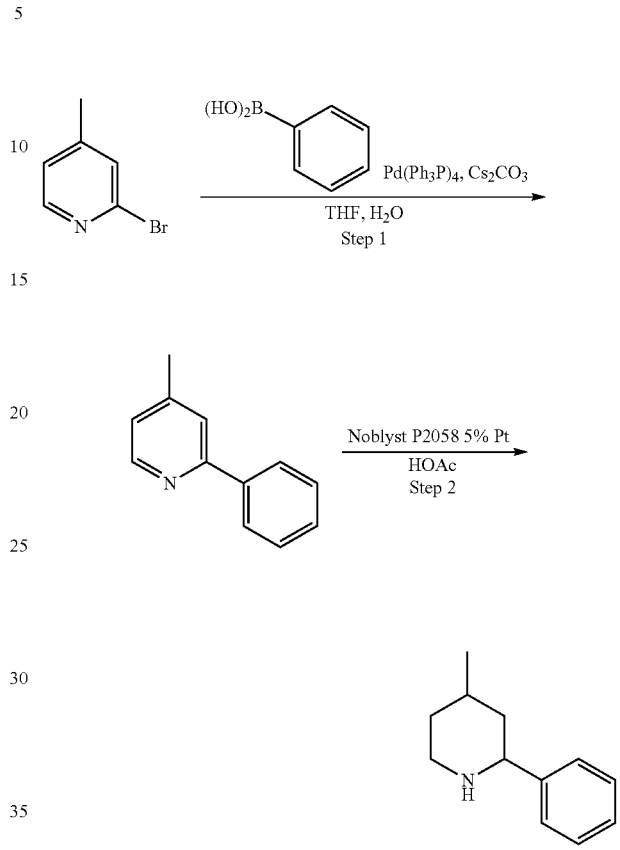

Step 1: Synthesis of 4-methyl-2-phenyl-pyridine

A stirring suspension of 2-bromo-4-methyl-pyridine (5 g, 29.07 mmol, 3.23 mL) and phenylboronic acid (4.25 g, 34.88 mmol) in THF (100 mL) and water (10 mL) was purged with argon for 10 minutes. After 10 minutes, Pd(PPh$_3$)$_4$ (1.68 g, 1.45 mmol) and Cs$_2$CO$_3$ (23.68 g, 72.66 mmol) were added under argon. The reaction mixture was stirred under argon at 65° C. for 12 hours. After 12 hours, the reaction mixture was cooled to room temperature and concentrated. The obtained residue was partitioned between EtOAc (100 mL) and water (100 mL). The organic layer was dried over Na$_2$SO$_4$ and concentrated under reduced pressure. The crude product was purified by column chromatography to obtain 4-methyl-2-phenyl-pyridine (1.5 g, 8.86 mmol, 30.50% yield).

LCMS(ESI): $[M+H]^+$ m/z: calcd 169.1; found 170.2; Rt=0.675 min.

Step 2: Synthesis of 4-methyl-2-phenyl-piperidine

A solution of 4-methyl-2-phenyl-pyridine in AcOH (30 mL) was hydrogenated over Noblyst P2058, 5% Pt under 50 atm pressure at 50° C. for 48 hours. Upon completion, the reaction mixture was filtered and the filtrate was evaporated under reduced pressure to obtain 4-methyl-2-phenyl-piperidine (0.8 g, 4.56 mmol). The crude product was used in next step reaction without any further purification.

LCMS(ESI): [M+H]+ m/z: calcd 175.2; found 176.2; Rt=0.702 min.

6. Boronate Couplings with Piperidine Vinyl Triflate

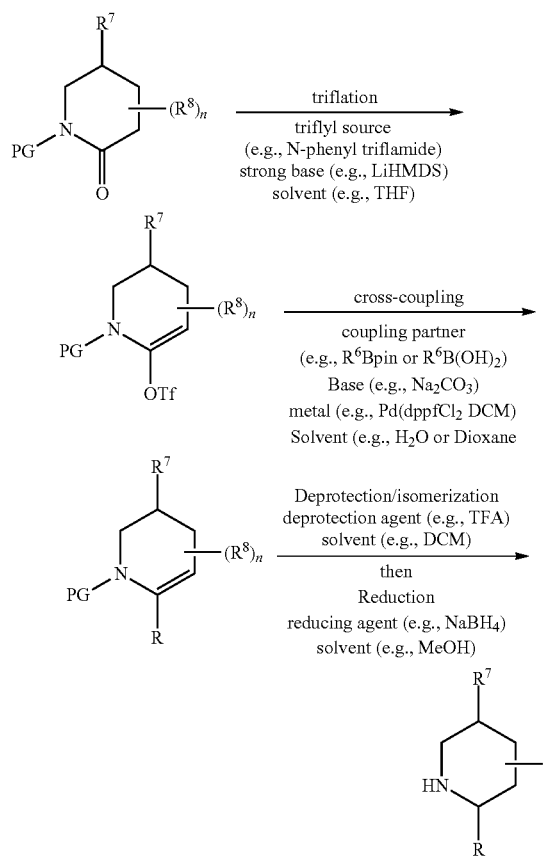

In some embodiments, a vinyl triflate can be prepared through basic enolate formation followed by quenching with a triflate source. In some embodiments, triflation can occur through use of a strong base (e.g. organolithium base, e.g., n-BuLi, t-BuLi, lithium diisopropylamide (LDA), lithium bis(trimethylsilyl)amide (LiHMDS), a hydride base e.g., NaH, or KH). In some embodiment, a triflate source is N-phenyltriflamide or Tf$_2$O. In some embodiments, triflation can be accomplished through the exposure of a piperidone to LiHMDS in THE followed by quenching with N-phenyltriflamide.

In some embodiments, a substituted tetrahydropyridine can be prepared through the cross-coupling of vinyl triflate with a suitable cross-coupling partner. In some embodiments, a suitable cross-coupling partner includes, but is not limited to, a boron-containing cross-coupling partner, e.g., R$^6$B(OH)$_2$, R$^6$Bpin. In some embodiments, cross-coupling can be facilitated by a metal catalyst (e.g. a Pd catalyst). In some embodiments, a Pd catalyst is Pd(dppf)$_2$ DCM, Pd(PPh$_3$)$_4$, Pd(dppf)Cl$_2$ DCM, PdCl$_2$(PPh$_3$)$_2$ or Pd(OAc)$_2$. In some embodiments, a cross-coupling reaction can be accomplished through employment of conditions which comprise Pd(dppf)Cl$_2$ DCM, Na$_2$CO$_3$, dioxane and water. In some embodiments, a cross-coupling reaction can be accomplished through employment of conditions which comprise PdCl$_2$(PPh$_3$)$_2$, Na$_2$CO$_3$, dioxane and water.

Conditions for the removal of a protecting group (PG), e.g., MoM or Boc are known to a person of ordinary skill in the art. Conditions for removing a protecting group -PG (e.g., -Boc) can employ, for example, acidic conditions, (e.g., water/dioxane, hydrochoric acid in a protic solvent (e.g., methanol), hydrochloric acid in an aprotic solvent (e.g., dioxane), TFA in an aprotic solvent (e.g., dichloromethane, chloroform, etc)). In some embodiments, a deproction step employs HCl (40 M) in dioxane. In some embodiments, a deproction step employs HCl (40 M) in DCM. In some embodiments, a deproction step employs TFA in DCM.

Reduction of a cyclic imine can be accomplished using a reducing agent such as a hydride reducing agent, e.g., NaBH$_4$, or LiAlH$_4$, silicon reducing agent, e.g., Cl$_3$SiH, or H$_2$ reduction in the presence of a catalyst, e.g. a Ir catalyst, a Ru catalyst, a Pd catalyst (e.g., Pd/C, Pd(OAc)$_2$). In some embodiments, reduction can be accomplished using conditions comprising, NaBH$_4$ in MeOH. In some embodiments, reduction can be accomplished using conditions comprising, NaBH$_4$ in MeOH and H$_2$O. In some embodiments, deprotection, cyclization and reduction occur in a single synethic step. In some embodiments, deprotection/cyclization/reduction can be accomplished using conditions comprising, NaBH$_4$, TFA, MeOH and H$_2$O.

6A. The Synthesis of 1-(4-(3-(5-methylpiperidin-2-yl)phenyl)piperidin-1-yl)ethanone

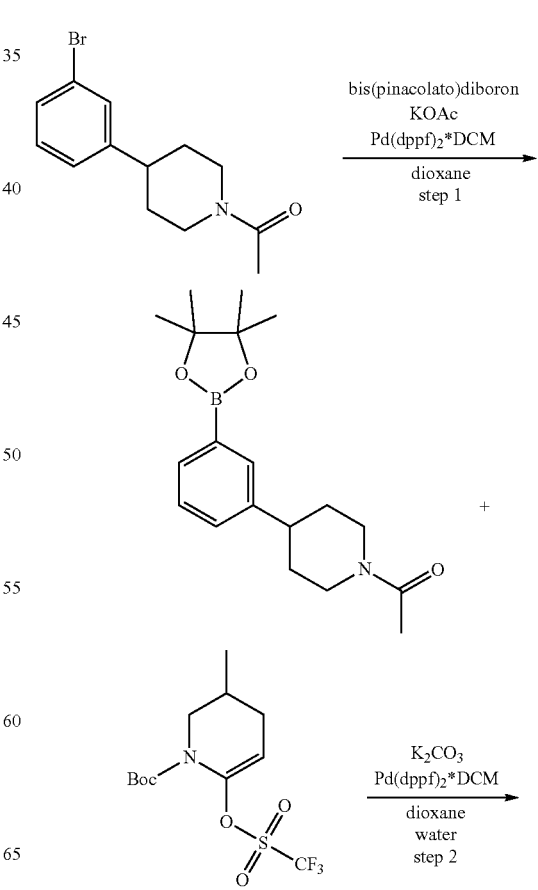

-continued

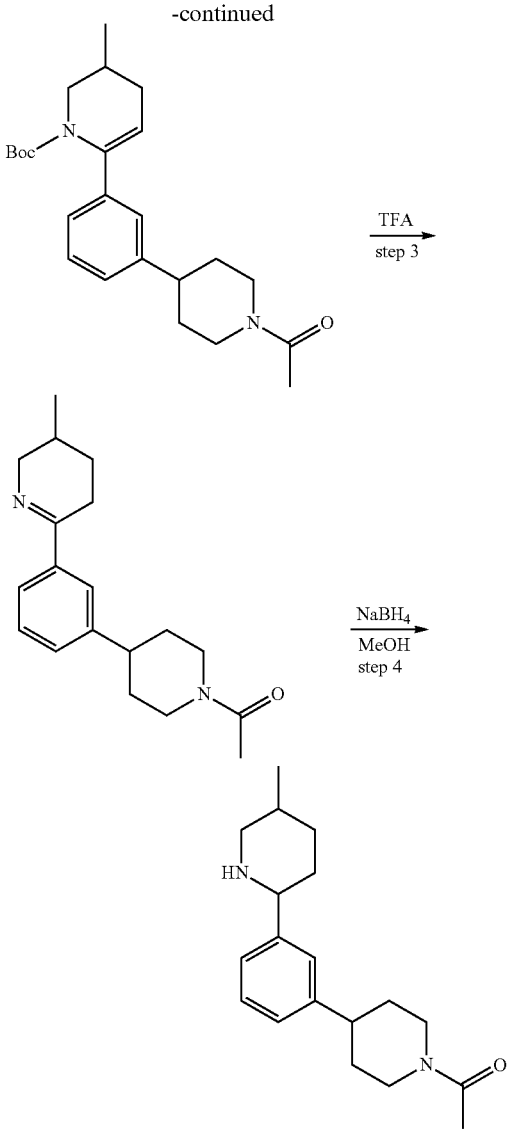

Step 1: Synthesis of 1-(4-(3-(4,4,5,5-tetramethyl-1,3,2-dioxaborolan-2-yl)phenyl)piperidin-1-yl)ethanone To a solution of 1-[4-(3-bromophenyl)-1-piperidyl]ethanone (9.1 g, 32.25 mmol), 4,4,4',4',5,5,5',5'-octamethyl-2,2'-bi-1,3,2-dioxaborolane (9.01 g, 35.47 mmol) and potassium acetate (7.91 g, 80.62 mmol, 5.04 mL) in dioxane (100 mL), [1,1'-bis(diphenylphosphino)ferrocene]dichloropalladium (II), complex with dichloromethane (1.32 g, 1.61 mmol) was added under an Ar atmosphere. The resulting mixture was heated at 80° C. for 12 hr and cooled to room temperature. The precipitate was filtered and the solvent was evaporated in vacuo. The residue was dissolved in DCM (100 ml), the resulting solution was washed with brine (2*50 ml), dried over Na₂SO₄ and the solvent was evaporated in vacuo to obtain crude product (17 g). The crude product was purified by gradient chromatography (CHCl₃—CH₃CN) to give 1-[4-[3-(4,4,5,5-tetramethyl-1,3,2-dioxaborolan-2-yl)phenyl]-1-piperidyl]ethanone (10.2 g, 30.98 mmol, 96.06% yield).

$^1$H NMR (400 MHz, CDCl₃) δ (ppm) 1.32 (s, 12H), 1.65 (m, 2H), 1.88 (m, 2H), 2.11 (s, 3H), 2.59 (t, 1H), 2.73 (t, 1H), 3.13 (t, 1H), 3.91 (d, 1H), 4.76 (d, 1H), 7.29 (m, 2H), 7.62 (m, 2H).

LCMS(ESI): [M]⁺ m/z: calcd 329.2; found 330.2; Rt=1.553 min.

Step 2: Synthesis of tert-butyl 6-(3-(1-acetylpiperidin-4-yl)phenyl)-3-methyl-3,4-dihydropyridine-1(2H)-carboxylate A suspension of 1-[4-[3-(4,4,5,5-tetramethyl-1,3,2-dioxaborolan-2-yl)phenyl]-1-piperidyl]ethanone (6 g, 18.22 mmol), tert-butyl 3-methyl-6-(trifluoromethylsulfonyloxy)-3,4-dihydro-2H-pyridine-1-carboxylate (6.29 g, 18.22 mmol), and sodium carbonate (5.79 g, 54.67 mmol, 2.29 mL) in dioxane (30 mL) and water (120 mL) was degassed and refilled with Ar three time. To this solution, [1,1'-bis(diphenylphosphino)ferrocene]dichloropalladium(II), complex with dichloromethane (744.11 mg, 911.19 µmol) was added. The resulting mixture was degassed, refilled with Ar and stirred at 80° C. for 24 hr. The precipitate was filtered off, washed with dioxane (50 ml). The solvent was evaporated in vacuo and residue was taken up with water 150 ml and extracted with DCM (2*100 ml). The combined organic layer was washed with brine (100 ml), dried over Na₂SO₄ and evaporated to obtain crude product (10 g). The crude product was purified by gradient chromatography (CHCl₃-ACN) to obtain tert-butyl 6-[3-(1-acetyl-4-piperidyl)phenyl]-3-methyl-3,4-dihydro-2H-pyridine-1-carboxylate (3.8 g, 9.53 mmol, 52.32% yield).

$^1$H NMR (400 MHz, CDCl₃) δ (ppm) 1.03 (m, 11H), 1.61 (m, 3H), 1.85 (m, 3H), 1.98 (m, 1H), 2.12 (s, 3H), 2.38 (m, 1H), 2.59 (t, 1H), 2.69 (t, 1H), 2.96 (t, 1H), 3.13 (t, 1H), 3.90 (d, 1H), 4.05 (d, 1H), 4.76 (d, 1H), 5.25 (m, 1H), 7.02 (d, 1H), 7.10 (m, 2H), 7.21 (m, 1H).

LCMS(ESI): [M-Boc]⁺ m/z: calcd 298.4; found 299.2; Rt=1.624 min.

Step 3: Synthesis of 1-(4-(3-(5-methyl-3,4,5,6-tetrahydropyridin-2-yl)phenyl)piperidin-1-yl)ethanone tert-butyl 6-[3-(1-acetyl-4-piperidyl)phenyl]-3-methyl-3,4-dihydro-2H-pyridine-1-carboxylate (3.8 g, 9.53 mmol) was dissolved in trifluoroacetic acid (22.20 g, 194.70 mmol, 15 mL). The resulting mixture was stirred at 25° C. for 1 hr (to the end of gas evolution) and the solvent was removed in vacuo. The obtained residue was diluted with water. The pH of the solution was adjusted to 8 with 10% NaOH solution and extracted with DCM (3*70 ml). The combined organic layer was washed with brine (50 ml), dried over Na₂SO₄ and evaporated in vacuo to obtain 1-[4-[3-(3-methyl-2,3,4,5-tetrahydropyridin-6-yl)phenyl]-1-piperidyl]ethanone (2.8 g, 9.38 mmol, 98.40% yield). This compound was used for the next step without purification.

$^1$H NMR (400 MHz, CDCl₃) δ (ppm) 0.97 (d, 3H), 1.37 (m, 1H), 1.64 (m, 3H), 1.88 (m, 3H), 2.11 (s, 3H), 2.58 (m, 2H), 2.74 (m, 2H), 3.13 (m, 1H), 3.24 (m, 1H), 3.95 (m, 2H), 4.75 (d, 1H), 7.18 (m, 1H), 7.30 (m, 1H), 7.54 (m, 1H), 7.65 (s, 1H). LCMS(ESI): [M]⁺ m/z: calcd 298.2; found 299.2; Rt=0.812 min.

Step 4: Synthesis of 1-(4-(3-(5-methylpiperidin-2-yl)phenyl)piperidin-1-yl)ethanone To a solution of 1-[4-[3-(3-methyl-2,3,4,5-tetrahydropyridin-6-yl)phenyl]-1-piperidyl]ethanone (2.8 g, 9.38 mmol) in MeOH (50 mL), sodium borohydride (532.46 mg, 14.07 mmol, 497.62 µL) was added portionwise at 0° C. The resulting mixture was stirred at 25° C. for 1 hr and the solvent was evaporated in vacuo, the residue was taken up with water (50 ml) and extracted with DCM (3*50 ml). The combined organic extract was washed with brine (2*50 ml), dried over Na₂SO₄ and evaporated to give 1-[4-[3-(5-methyl-2-piperidyl)phenyl]-1-piperidyl]ethanone (2.3 g, crude). This compound was used for the next step without purification.

$^1$H NMR (400 MHz, DMSO-d₆) δ (ppm) 0.82 (d, 3H), 1.08 (m, 1H), 1.42 (m, 3H), 1.58 (m, 2H), 1.74 (m, 3H), 2.02 (s, 3H), 2.24 (t, 1H), 2.59 (t, 1H), 2.72 (t, 1H), 2.99 (d, 1H), 3.10 (t, 1H), 3.43 (m, 2H), 3.91 (d, 1H), 4.51 (d, 1H), 7.01 (d, 1H), 7.20 (m, 3H). LCMS(ESI): [M]⁺ m/z: calcd 300.2; found 301.2; Rt=0.975 min.

6B. The Synthesis of/N-methyl-3-(2-piperidyl)aniline

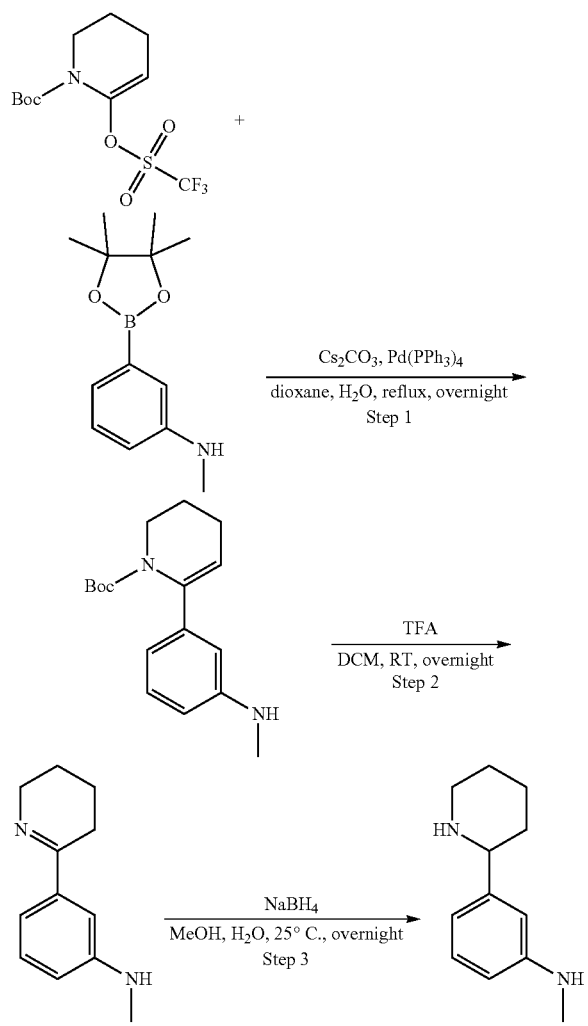

Step 1: The Synthesis of tert-butyl 6-[3-(methylamino)phenyl]-3,4-dihydro-2H-pyridine-1-carboxylate tert-butyl 6-(trifluoromethylsulfonyloxy)-3,4-dihydro-2H-pyridine-1-carboxylate (5 g, 15.09 mmol) and N-methyl-3-(4,4,5,5-tetramethyl-1,3,2-dioxaborolan-2-yl) aniline (4.07 g, 15.09 mmol, HCl) was dissolved in dioxane (50 mL). The reaction mixture was thoroughly degassed, following by the subsequent addition of caesium carbonate (4.92 g, 15.09 mmol), H₂O (5 mL) and Palladium (0) tetrakis(triphenylphosphine) (17.44 g, 15.09 mmol). Then, the resulting reaction mixture was stirred under reflux overnight. After the completion of the reaction (concluded by LCMS of the reaction mixture), the organic solvent was evaporated, and the crude mixture was partitioned between EtOAc (50 mL) and H₂O (15 mL). The organic layer was dried over Na₂SO₄ and evaporated under reduced pressure to give crude tert-butyl 6-[3-(methylamino)phenyl]-3,4-dihydro-2H-pyridine-1-carboxylate (5.5 g, crude). The obtained product was used in the next step without purification.

$^1$H NMR (500 MHz, CDCl₃) δ 1.11 (s, 9H), 1.85 (m, 2H), 2.25 (m, 2H), 2.81 (s, 3H), 3.69 (m, 2H), 5.33 (m, 1H), 6.49 (d, 1H), 6.54 (s, 1H), 6.65 (d, 1H), 7.08 (dd, 1H), NH is not observed.

LCMS(ESI): [M-t-Bu]⁺ m/z: calcd 232.1; found 233.2; Rt=1.297 min.

Step 2: The Synthesis of N-methyl-3-(2,3,4,5-tetrahydropyridin-6-yl)aniline tert-butyl 6-[3-(methylamino)phenyl]-3,4-dihydro-2H-pyridine-1-carboxylate (2 g, 4.85 mmol) was dissolved in DCM followed by the addition of TFA (1.11 g, 9.71 mmol, 748.03 µL). The reaction mixture was stirred overnight. After the completion of the reaction, the mixture was washed with 10% aq NaOH, and the organic solvent was evaporated to give N-methyl-3-(2,3,4,5-tetrahydropyridin-6-yl)aniline (1.2 g, crude) which was used in the next step without purification.

$^1$H NMR (500 MHz, CDCl₃) δ 1.65 (m, 2H), 1.84 (m, 2H), 2.61 (m, 1H), 2.79 (s, 3H), 3.43 (m, 2H), 3.87 (m, 2H), 6.59 (m, 1H), 7.18 (m, 2H), 7.21 (m, 1H).

Step 3: The Synthesis of N-methyl-3-(2-piperidyl)aniline

N-methyl-3-(2,3,4,5-tetrahydropyridin-6-yl)aniline (1.2 g, 6.37 mmol) and N-methyl-3-(2,3,4,5-tetrahydropyridin-6-yl)aniline (1.2 g, 6.37 mmol) were dissolved in MeOH (20 mL) and H₂O (20 mL). The resulting mixture was cooled to 25° C. and sodium borohydride (482.28 mg, 12.75 mmol, 450.73 µL) was added in portions. Then, the reaction mixture was additionally stirred overnight. After the completion of the reaction, the mixture was acidified with 10% aq HCl to pH 2. The obtained mixture was washed with MTBE (2*10 mL), basified with 10% aq NaOH to pH 10 and extracted with DCM (50 mL). Evaporation of the solvent resulted in pure N-methyl-3-(2-piperidyl)aniline (0.9 g, 4.73 mmol, 74.21% yield).

$^1$H NMR (400 MHz, CDCl₃) δ 1.74 (m, 8H), 2.82 (m, 4H), 3.12 (m, 1H), 3.51 (m, 1H), 6.47 (d, 1H), 6.65 (s, 1H), 6.68 (d, 1H), 7.11 (dd, 1H).

LCMS(ESI): [M+H]⁺ m/z: calcd 190.1; found 191.2; Rt=0.539 min.

6C. The Synthesis of N,N-dimethyl-3-(2-piperidyl)aniline

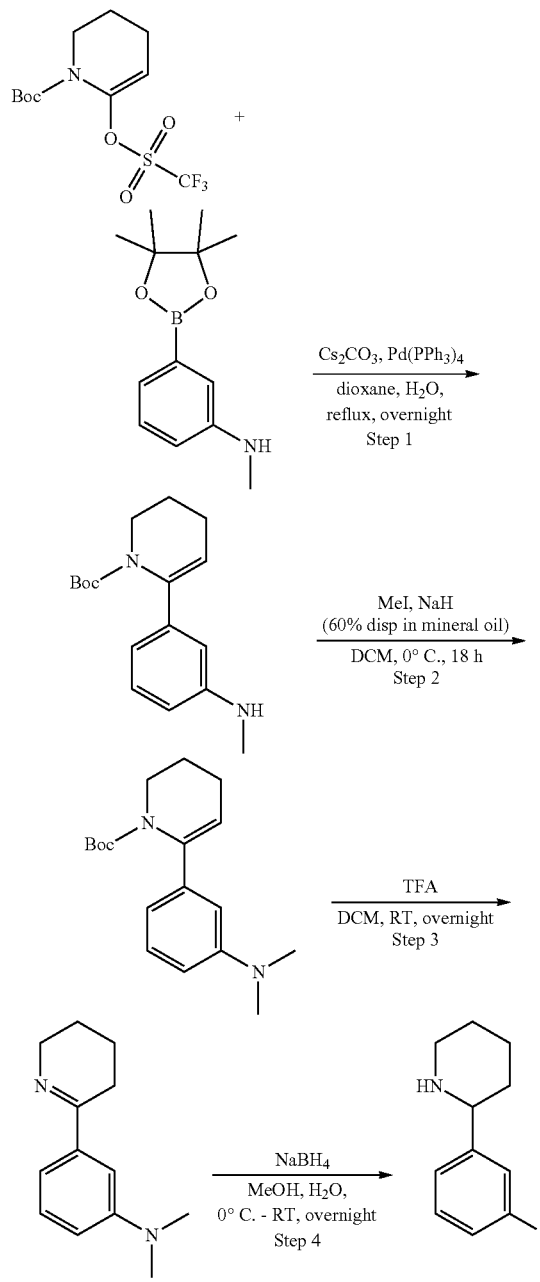

Step 1 is the Same as for Intermediate 6B

Step 2: The Synthesis of tert-butyl 6-[3-(dimethylamino)phenyl]-3,4-dihydro-2H-pyridine-1-carboxylate tert-butyl 6-[3-(methylamino)phenyl]-3,4-dihydro-2H-pyridine-1-carboxylate (1.5 g, 5.20 mmol) was dissolved in DMF (10 mL). The resulting mixture was cooled to 0° C. and sodium hydride (in oil dispersion) 60% dispersion in mineral oil (119.58 mg, 5.20 mmol) followed iodomethane (738.28 mg, 5.20 mmol, 323.81 μL) were added. After stirring for 18 hr, the mixture was poured on conc aq NH₄Cl (30 mL) and extracted with EtOAc (50 mL). Evaporation of organic solvents results in crude tert-butyl 6-[3-(dimethylamino)phenyl]-3,4-dihydro-2H-pyridine-1-carboxylate (1.1 g, 3.64 mmol, 69.93% yield) which was used in the next step without purification.

LCMS(ESI): [M+H]⁺ m/z: calcd 302.1; found 303.2; Rt=1.256 min.

Step 3: The Synthesis of N,N-dimethyl-3-(2,3,4,5-tetrahydropyridin-6-yl)aniline tert-butyl 6-[3-(dimethylamino)phenyl]-3,4-dihydro-2H-pyridine-1-carboxylate (1.1 g, 3.64 mmol) was dissolved in DCM (10 mL) followed by the addition of TFA (2.07 g, 18.19 mmol, 1.40 mL) and stirring overnight. After the reaction was complete, the mixture was washed with 10% aq NaOH, and the organic solvent was evaporated to give N,N-dimethyl-3-(2,3,4,5-tetrahydropyridin-6-yl)aniline (0.7 g, 3.46 mmol, 95.13% yield) which was used in the next step without purification.

¹H NMR (500 MHz, CDCl₃) δ 1.80 (m, 2H), 1.84 (m, 2H), 2.62 (m, 2H), 2.98 (s, 6H), 3.83 (m, 2H), 7.07 (s, 1H), 7.20 (m, 3H)

Step 4: The Synthesis of N,N-dimethyl-3-(2-piperidyl)aniline

N,N-dimethyl-3-(2,3,4,5-tetrahydropyridin-6-yl)aniline (0.7 g, 3.46 mmol)N,N-dimethyl-3-(2,3,4,5-tetrahydropyridin-6-yl)aniline (0.7 g, 3.46 mmol) was dissolved in MeOH (10 mL) and H₂O (2 mL) and cooled to 0° C. Sodium borohydride (392.74 mg, 10.38 mmol, 367.04 μL) was added in portions to obtained mixture and additionally stirred overnight. After the reaction was complete, the reaction mixture was acidified with 10% aq HCl to pH 2, washed with MTBE (2*10 mL), basified with 10% aq NaOH to pH 10 and extracted with DCM (20 mL). Evaporation of the solvent result in pure N,N-dimethyl-3-(2-piperidyl)aniline (0.5 g, 2.45 mmol, 70.72% yield).

¹H NMR (500 MHz, CDCl₃) δ 1.82 (m, 4H), 2.61 (m, 2H), 2.2.90 (s, 6H), 3.42 (m, 2H), 3.61 (m, 1H), 3.84 (m, 1H), 6.69 (m, 1H), 6.72 (m, 1H), 6.81 (m, 1H), 7.30 (m, 1H).

6D. The Synthesis of N-methyl-3-(5-methyl-2-piperidyl)aniline

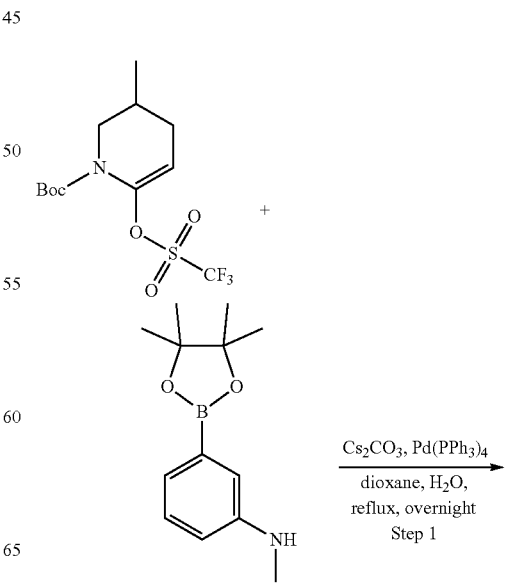

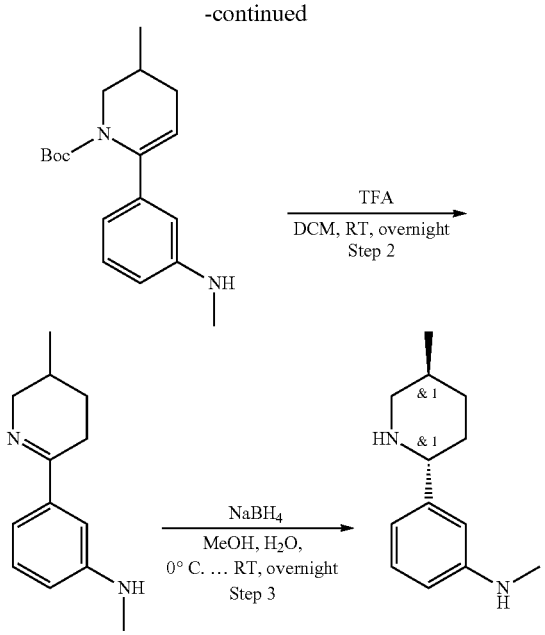

Step 1: The Synthesis of tert-butyl 3-methyl-6-[3-(methylamino)phenyl]-3,4-dihydro-2H-pyridine-1-carboxylate tert-butyl 3-methyl-6-(trifluoromethylsulfonyloxy)-3,4-dihydro-2H-pyridine-1-carboxylate (5, 14.48 mmol) and N-methyl-3-(4,4,5,5-tetramethyl-1,3,2-dioxaborolan-2-yl)aniline (3.38 g, 12.52 mmol, HCl) was dissolved in diox (50 mL) and the reaction mixture was thoroughly degassed, following by the subsequent addition of caesium carbonate (4.72 g, 14.48 mmol), H₂O (5 mL) and Palladium (0) tetrakis(triphenylphosphine) (16.73 g, 14.48 mmol). Obtained reaction mixture was stirred at reflux overnight. After the reaction was complete (concluded by LCMS of the reaction mixture) the organic solvent was evaporated, and the crude mixture was partitioned between EtOAc (50 mL) and H₂O (30 mL). The organic layer was dried over Na₂SO₄ and evaporated under reduced pressure to give crude tert-butyl 3-methyl-6-[3-(methylamino)phenyl]-3,4-dihydro-2H-pyridine-1-carboxylate (5.5 g, crude) which was used in the next step without purification.

¹H NMR (500 MHz, CDCl₃) δ 0.98 (d, 3H), 1.15 (s, 9H), 1.79 (m, 1H), 1.97 (m, 2H), 2.38 (m, 1H), 2.84 (s, 3H), 2.96 (m, 1H), 4.06 (m, 1H), 5.30 (m, 1H), 6.49 (d, 1H), 6.54 (s, 1H), 6.66 (d, 1H), 7.08 (dd, 1H).

LCMS(ESI): [M+H]⁺ m/z: calcd 302.2; found 303.2; Rt=1.406 min.

Step 2: The Synthesis of N-methyl-3-(3-methyl-2,3,4,5-tetrahydropyridin-6-yl)aniline tert-butyl 3-methyl-6-[3-(methylamino)phenyl]-3,4-dihydro-2H-pyridine-1-carboxylate (2, 6.61 mmol) was dissolved in DCM (30 mL) followed by the addition of TFA (500.41 mg, 4.39 mmol, 338.12 µL) and stirring overnight. After the reaction was complete, the mixture was washed with 10% aq NaOH, and the organic solvent was evaporated to give N-methyl-3-(3-methyl-2,3,4,5-tetrahydropyridin-6-yl)aniline (1.5 g, crude) which was used in the next step without purification.

¹H NMR (500 MHz, CDCl₃) δ 1.02 (m, 3H), 1.42 (m, 1H), 1.73 (m, 1H), 1.87 (m, 1H), 2.52 (m, 1H), 2.73 (m, 1H), 2.89 (s, 3H), 3.20 (m, 1H), 4.01 (m, 1H), 6.64 (d, 1H), 7.05 (d, 1H), 7.08 (s, 1H), 7.19 (dd, 1H).

Step 3: The Synthesis of N-methyl-3-(5-methyl-2-piperidyl)aniline

N-methyl-3-(3-methyl-2,3,4,5-tetrahydropyridin-6-yl)aniline (1.34 g, 6.61 mmol)N-methyl-3-(3-methyl-2,3,4,5-tetrahydropyridin-6-yl)aniline (1.34 g, 6.61 mmol) was dissolved in MeOH (25.00 mL) and H₂O (5.00 mL) and cooled to 0° C. Sodium Borohydride (500.15 mg, 13.22 mmol, 467.43 µL) was added in portions to obtained mixture and additionally stirred overnight. After the reaction was complete, the reaction mixture was acidified with 10% aq HCl to pH 2, diluted with water, washed with MTBE (2*10 mL), basified with 10% aq NaOH to pH 10 and extracted with DCM (30.00 mL). Evaporation of the solvent result in pure N-methyl-3-(5-methyl-2-piperidyl)aniline (0.92 g, 4.50 mmol, 68.12% yield).

¹H NMR (400 MHz, CDCl₃) δ 0.89 (m, 3H), 1.52 (m, 6H), 2.41 (m, 1H), 2.81 (s, 3H), 3.10 (m, 1H), 3.48 (m, 1H), 3.71 (m, 1H), 6.47 (d, 1H), 6.68 (m, 2H), 7.11 (m, 1H).

LCMS(ESI): [M+H]⁺ m/z: calcd 204.2; found 205.2; Rt=0.579 min.

6E. The Synthesis of N,N-dimethyl-3-(5-methyl-2-piperidyl)aniline

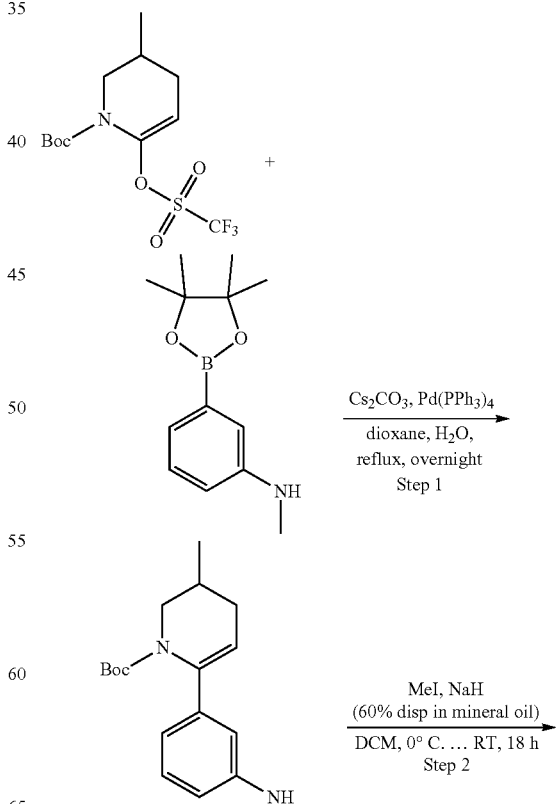

-continued

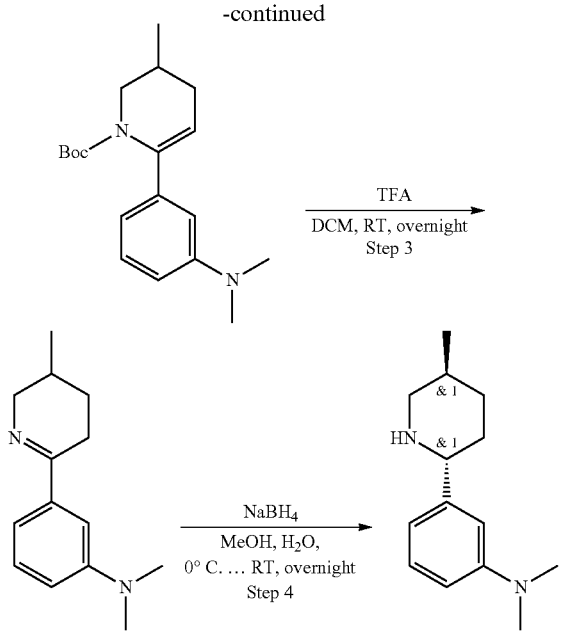

Step 1 is the Same as for Intermediate 6D

Step 2: The Synthesis of tert-butyl 6-[3-(dimethylamino)phenyl]-3-methyl-3,4-dihydro-2H-pyridine-1-carboxylate tert-butyl 3-methyl-6-[3-(methylamino)phenyl]-3,4-dihydro-2H-pyridine-1-carboxylate (1.5 g, 4.96 mmol) was dissolved in dmf (10 mL) and cooled to 0° C., following by the addition of Sodium hydride (in oil dispersion) 60% dispersion in mineral oil (114.03 mg, 4.96 mmol) and iodomethane (704.04 mg, 4.96 mmol, 308.79 μL). After stirring for 18 hr, the mixture was poured on conc aq NH$_4$Cl (30 mL) and extracted with EtOAc (20 mL). Evaporation of organic solvents results in crude tert-butyl 6-[3-(dimethylamino)phenyl]-3-methyl-3,4-dihydro-2H-pyridine-1-carboxylate (1.3 g, 4.11 mmol, 82.83% yield) which was used in the next step without purification.

LCMS(ESI): [M-t-Bu]$^+$ m/z: calcd 260.2; found 260.2; Rt=1.572 min.

Step 3: The Synthesis of N,N-dimethyl-3-(3-methyl-2,3,4,5-tetrahydropyridin-6-yl)aniline tert-butyl 6-[3-(dimethylamino)phenyl]-3-methyl-3,4-dihydro-2H-pyridine-1-carboxylate (1.3 g, 4.11 mmol) was dissolved in DCM (10 mL) followed by the addition of TFA (468.43 mg, 4.11 mmol, 316.51 μL) and stirring overnight. After the reaction was complete, the mixture was washed with 10% aq NaOH, and the organic solvent was evaporated to give N,N-dimethyl-3-(3-methyl-2,3,4,5-tetrahydropyridin-6-yl)aniline (0.75 g, 3.47 mmol, 84.39% yield) which was used in the next step without purification.

$^1$H NMR (500 MHz, CDCl$_3$) δ 1.08 (d, 3H), 1.74 (m, 2H), 1.88 (m, 1H), 2.62 (m, 1H), 2.98 (m, 6H), 3.21 (m, 1H), 4.01 (m, 1H), 7.07 (s, 1H), 7.20 (m, 3H).

Step 4: The Synthesis of N,N-dimethyl-3-(5-methyl-2-piperidyl)aniline

N,N-dimethyl-3-(3-methyl-2,3,4,5-tetrahydropyridin-6-yl)aniline (0.75 g, 3.47 mmol)N,N-dimethyl-3-(3-methyl-2,3,4,5-tetrahydropyridin-6-yl)aniline (0.75 g, 3.47 mmol) was dissolved in MeOH (10 mL) and H$_2$O (2 mL) and cooled to 0° C. Sodium Borohydride (131.17 mg, 3.47 mmol, 122.59 μL) was added in portions to obtained mixture and additionally stirred overnight. After the reaction was complete, the reaction mixture was acidified with 10% aq HCl to pH 2, washed with MTBE (2*10 mL), basified with 10% aq NaOH to pH 10 and extracted with DCM (20 mL). Evaporation of the solvent result in pure N,N-dimethyl-3-(5-methyl-2-piperidyl)aniline (0.55 g, 2.52 mmol, 72.66% yield).

$^1$H NMR (500 MHz, CDCl$_3$) δ 0.91 (m, 3H), 1.62 (m, 2H), 1.82 (m, 2H), 2.38 (m, 1H), 2.85 (s, 6H), 3.14 (m, 1H), 3.52 (m, 1H), 6.63 (m, 1H), 6.71 (m, 1H), 6.78 (s, 1H), 7.18 (m, 1H).

LCMS(ESI): [M+H]$^+$ m/z: calcd 218.2; found 219.2; Rt=0.823 min.

6F. The Synthesis of 4-(5-methyl-2-piperidyl)aniline

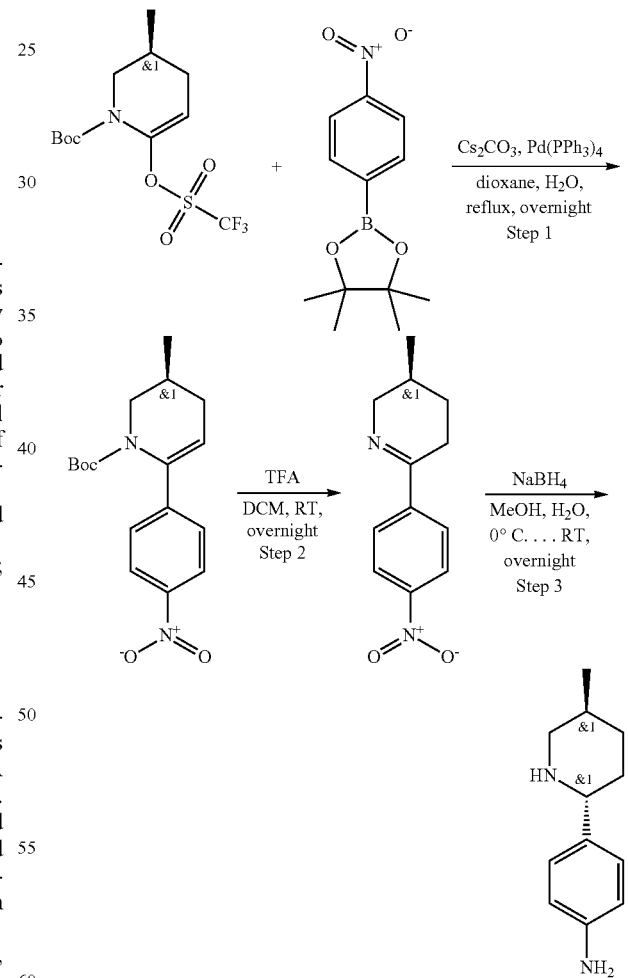

Step 1: The Synthesis of tert-butyl 3-methyl-6-(4-nitrophenyl)-3,4-dihydro-2H-pyridine-1-carboxylate tert-butyl 3-methyl-6-(trifluoromethylsulfonyloxy)-3,4-dihydro-2H-pyridine-1-carboxylate (10.3 g, 29.83 mmol)

and 4,4,5,5-tetramethyl-2-(4-nitrophenyl)-1,3,2-dioxaborolane (7.43 g, 29.83 mmol) were dissolved in dioxane (50 mL). The reaction mixture was thoroughly degassed, following by the addition of caesium carbonate (48.59 g, 149.13 mmol, 1.01 mL), H₂O (10 mL) and Pd(PPh₃)₄ (3.45 g, 2.98 mmol). The obtained reaction mixture was stirred under reflux overnight. After the completion of the reaction (concluded by HNMR of the reaction mixture), the organic solvent was evaporated and the crude mixture was partitioned between EtOAc (250 mL) and H₂O (200 mL). The organic layer was dried over Na₂SO₄ and evaporated under reduced pressure to afford tert-butyl 3-methyl-6-(4-nitrophenyl)-3,4-dihydro-2H-pyridine-1-carboxylate (10 g, crude) which was used in the next step without purification.

¹H NMR (400 MHz, CDCl₃) δ 1.37 (m, 11H), 2.03 (m, 3H), 2.45 (m, 1H), 3.00 (m, 1H), 4.04 (m, 1H), 5.45 (s, 1H), 7.43 (m, 2H), 8.14 (m, 2H).

Step 2: The Synthesis of 3-methyl-6-(4-nitrophenyl)-2,3,4,5-tetrahydropyridine tert-butyl 3-methyl-6-(4-nitrophenyl)-3,4-dihydro-2H-pyridine-1-carboxylate (10 g, 25.13 mmol) was dissolved in DCM (30 mL). The resulting mixture was stirred for 5 min followed by the addition of TFA (14.33 g, 125.64 mmol, 9.68 mL). Then, the reaction mixture was stirred overnight. After the completion of the reaction, the mixture was washed with 10% aq NaOH, and the organic solvent was evaporated to give 3-methyl-6-(4-nitrophenyl)-2,3,4,5-tetrahydropyridine (7 g, crude), which was used in the next step without purification.

¹H NMR (400 MHz, CDCl₃) δ 1.01 (d, 3H), 1.31 (m, 1H), 1.62 (m, 1H), 1.92 (m, 1H), 2.52 (m, 1H), 2.78 (m, 1H), 3.25 (m, 1H), 4.04 (m, 1H), 7.94 (m, 2H), 8.20 (m, 2H).

LCMS(ESI): [M+H]⁺ m/z: calcd 218.1; found 219.2; Rt=0.789 min.

Step 3: The Synthesis of 4-(5-methyl-2-piperidyl)aniline 3-methyl-6-(4-nitrophenyl)-2,3,4,5-tetrahydropyridine (7 g, 25.66 mmol)3-methyl-6-(4-nitrophenyl)-2,3,4,5-tetrahydropyridine (7 g, 25.66 mmol) were dissolved in the mixture of MeOH (20 mL) and H₂O (5 mL). The resulting mixture was cooled to 0° C. followed by the portionwise addition of sodium borohydride (3.88 g, 102.63 mmol, 3.63 mL). The reaction mixture was stirred overnight. After the completion of the reaction, the mixture was acidified with 10% aq HCl to pH 2, diluted with water, washed with MTBE (2*10 mL), basified with 10% aq NaOH to pH 10 and extracted with DCM (50 mL). The organic layer was evaporated under reduced pressure to afford pure 4-(5-methyl-2-piperidyl)aniline (5.1 g, crude).

¹H NMR (400 MHz, CDCl₃) δ 0.75 (d, 3H), 1.05 (m, 1H), 1.23 (m, 2H), 1.42 (m, 1H), 1.73 (m, 1H), 1.94 (m, 1H), 2.38 (m, 1H), 3.07 (m, 1H), 3.40 (m, 1H), 3.57 (m, 2H), 6.61 (d, 2H), 7.12 (d, 2H).

LCMS(ESI): [M+H]⁺ m/z: calcd 190.1; found 191.2; Rt=0.413 min.

6G. The Synthesis of -(5-methyl-3,4,5,6-tetrahydropyridin-2-yl)phenol

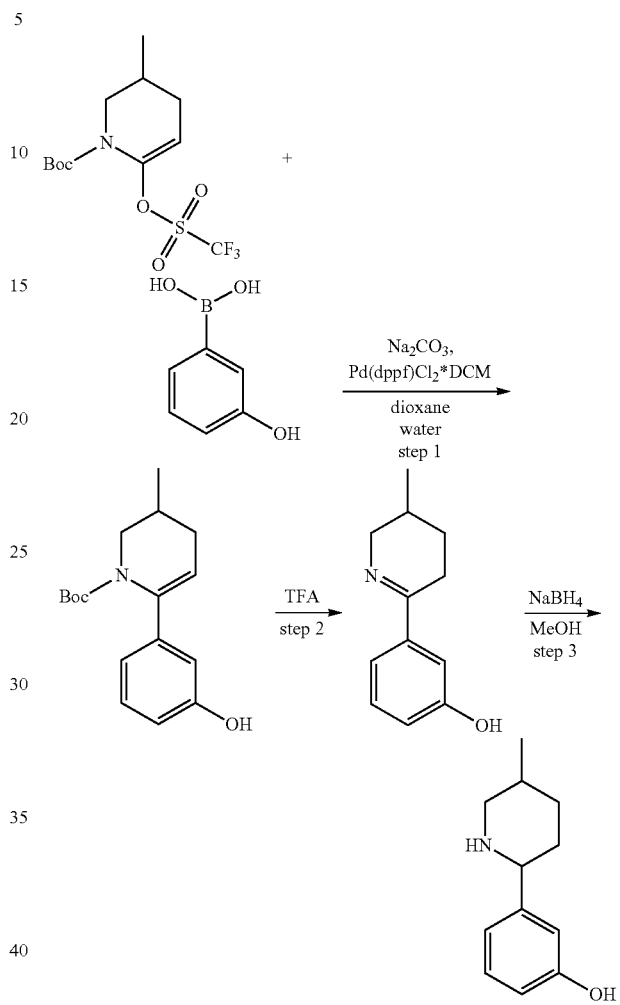

Step 1: Synthesis of tert-butyl 6-(3-hydroxyphenyl)-3-methyl-3,4-dihydropyridine-1(2H)-carboxylate tert-butyl 3-methyl-6-(trifluoromethylsulfonyloxy)-3,4-dihydro-2H-pyridine-1-carboxylate (7 g, 20.27 mmol), (3-hydroxyphenyl)boronic acid (3.63 g, 26.35 mmol) and sodium carbonate (6.45 g, 60.81 mmol, 2.55 mL) were added to a mixture of 1,4-dioxane (90 mL) and water (30 mL). The resulting mixture was evacuated and then backfilled with argon, this operation was repeated three times, then Pd(dppf)C₁₂ DCM (661.62 mg, 810.81 μmol) was added under argon. The reaction mixture was stirred under argon at 70° C. for 12 hr, then cooled and filtered. The filtercake was washed with 1,4-dioxane (2*20 ml) and discarded. The filtrate was evaporated in vacuo, and the residue was purified by column chromatography on silica gel using hexane/MTBE gradient (0-100% MTBE) to afford tert-butyl 6-(3-hydroxyphenyl)-3-methyl-3,4-dihydro-2H-pyridine-1-carboxylate (2.7 g, 9.33 mmol, 46.03% yield) as white solid.

¹H NMR (500 MHz, CDCl₃) δ (ppm) 1.00 (d, 3H), 1.12 (s, 9H), 1.87 (m, 1H), 2.02 (m, 1H), 2.41 (m, 1H), 2.98 (t, 1H), 4.03 (d, 1H), 5.33 (m, 1H), 5.78 (bds, 1H), 6.75 (m, 2H), 6.88 (d, 1H), 7.15 (t, 1H).

LCMS(ESI): [M-Boc]+ m/z: calcd 189.2; found 190.2; Rt=1.473 min.

Step 2: Synthesis of 3-(5-methyl-3,4,5,6-tetrahydropyridin-2-yl)phenol tert-butyl 6-(3-hydroxyphenyl)-3-methyl-3,4-dihydro-2H-pyridine-1-carboxylate (0.5 g, 1.73 mmol) was dissolved in trifluoroacetic acid (3.75 g, 32.89 mmol, 2.53 mL). The resulting solution was stirred at 25° C. for 1 hr, then evaporated in vacuo to afford crude 3-(3-methyl-2,3,4,5-tetrahydropyridin-6-yl)phenol (1.1 g, crude) as yellow gum, which was used directly in the next step.

1H NMR (500 MHz, CDCl3) δ (ppm) 1.18 (d, 3H), 1.68 (m, 1H), 2.12 (m, 2H), 3.15 (m, 1H), 3.38 (m, 2H), 4.01 (m, 1H), 7.25 (m, 2H), 7.41 (m, 2H), 12.45 (bds, 1H).

LCMS(ESI): [M]+ m/z: calcd 189.2; found 190.2; Rt=0.788 min.

Step 3: Synthesis of 3-(5-methylpiperidin-2-yl)phenol

Sodium borohydride (1.76 g, 46.50 mmol, 1.64 mL) was added portionwise over 1 hr to a stirred solution of 3-(3-methyl-2,3,4,5-tetrahydropyridin-6-yl)phenol (1.1 g, 5.81 mmol) in methanol (30 mL) at 0° C. The resulting mixture was allowed to warm and stirred at 25° C. for 12 hr, and then evaporated in vacuo. The residue was diluted with chloroform (50 ml), stirred for 0.1 hr and filtered. The filtercake was additionally washed with chloroform (2*10 ml) and discarded. The combined filtrate was evaporated in vacuo to afford crude 3-(5-methyl-2-piperidyl)phenol (0.47 g, 2.46 mmol, 42.28% yield) as yellow solid, which was used directly in the next step.

1H NMR (400 MHz, CDCl3) δ (ppm) 0.98 (d, 3H), 1.05 (m, 1H), 1.69 (m, 3H), 2.34 (m, 1H), 3.30 (m, 2H), 3.44 (m, 3H), 6.64 (m, 3H), 7.07 (m, 1H).

LCMS(ESI): [M]+ m/z: calcd 191.2; found 192.2; Rt=0.708 min.

6H. The Synthesis of 4-(5-methylpiperidin-2-yl)phenol and rac-4-((2R,5S)-5-methylpiperidin-2-yl)phenyl acetate

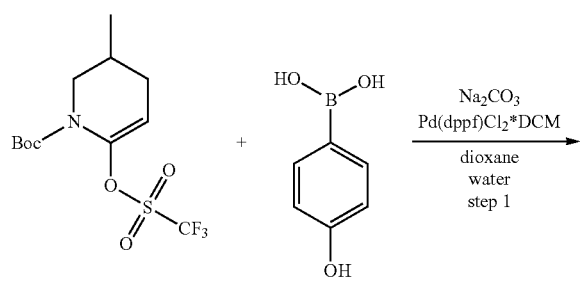

Step 1: Synthesis of tert-butyl 6-(4-hydroxyphenyl)-3-methyl-3,4-dihydropyridine-1(2H)-carboxylate tert-butyl 3-methyl-6-(trifluoromethylsulfonyloxy)-3,4-dihydro-2H-pyridine-1-carboxylate (32 g, 92.66 mmol), (4-hydroxyphenyl)boronic acid (15.98 g, 115.83 mmol) and sodium carbonate (29.46 g, 277.99 mmol, 11.65 mL) were added to a mixture of 1,4-dioxane (360 mL) and water (120 mL). The resulting mixture was evacuated and then back-filled with argon, this operation was repeated three times, then Pd(dppf)Cl2 DCM (3.02 g, 3.71 mmol) was added under argon. The reaction mixture was stirred under argon at 90° C. for 18 hr, then cooled and filtered. The filtercake was washed with 1,4-dioxane (2*20 ml) and discarded. The

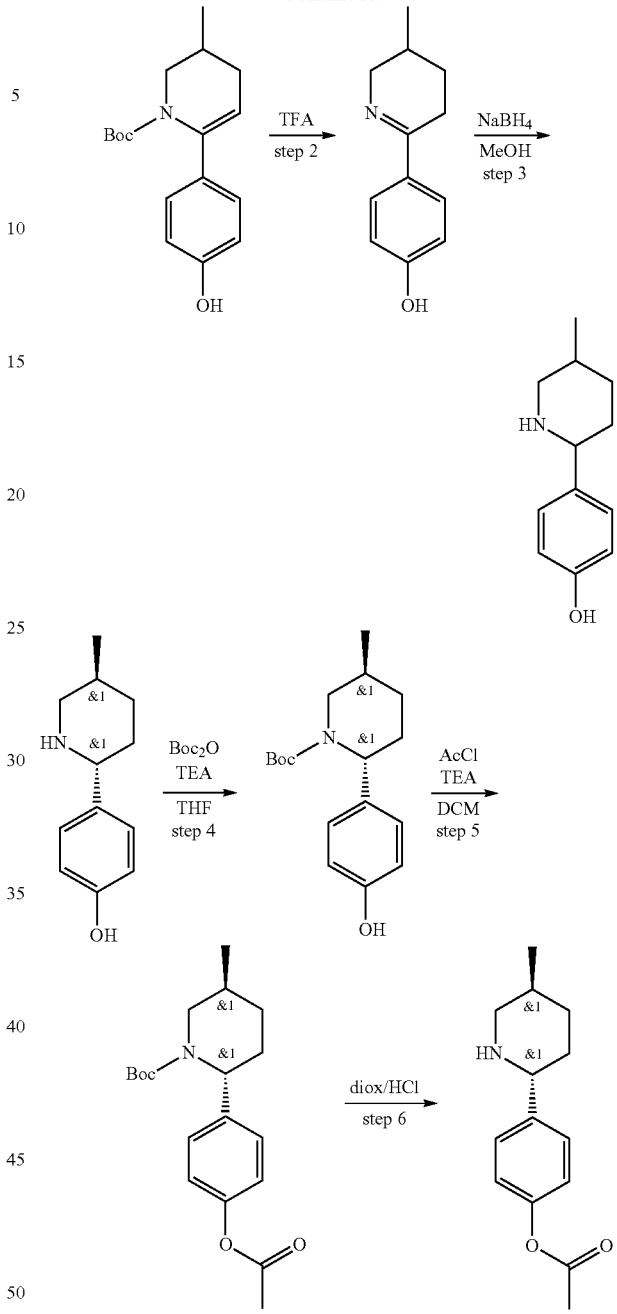

filtrate was evaporated in vacuo, and the residue was purified by column chromatography on silica gel using hexane/ethyl acetate gradient (0-100% ethyl acetate) to afford tert-butyl 6-(4-hydroxyphenyl)-3-methyl-3,4-dihydro-2H-pyridine-1-carboxylate (12 g, 41.47 mmol, 44.75% yield) as white solid, which was used directly in the next step.

$^1$H NMR (500 MHz, CDCl$_3$) δ (ppm) 0.99 (d, 3H), 1.12 (s, 9H), 1.99 (m, 1H), 2.00 (m, 1H), 2.36 (d, 1H), 2.96 (t, 1H), 4.06 (d, 1H), 5.22 (m, 1H), 6.77 (m, 2H), 7.15 (m, 2H).

LCMS(ESI): [M-Boc]$^+$ m/z: calcd 189.2; found 190.2; Rt=1.395 min.

Step 2: Synthesis of 4-(5-methyl-3,4,5,6-tetrahydropyridin-2-yl)phenol tert-butyl 6-(4-hydroxyphenyl)-3-methyl-3,4-dihydro-2H-pyridine-1-carboxylate (12 g, 41.47 mmol) was dissolved in trifluoroacetic acid (141.85 g, 1.24 mol, 95.85 mL). The resulting solution was stirred at 25° C. for 1 hr, and then evaporated in vacuo. Crushed ice (100 g) was added to the residue and the pH was adjusted to 9 with 10% aqueous solution of sodium carbonate. The resulting mixture was extracted with dichloromethane (2*300 ml). The combined organic extracts were dried over sodium sulphate and evaporated in vacuo to afford 4-(3-methyl-2,3,4,5-tetrahydropyridin-6-yl)phenol (8.5 g, crude) as beige solid, which was used directly in the next step.

$^1$H NMR (400 MHz, CDCl$_3$) δ (ppm) 0.98 (d, 3H), 1.32 (m, 1H), 1.67 (m, 1H), 1.83 (m, 1H), 2.56 (m, 1H), 2.74 (m, 1H), 3.11 (m, 1H), 3.80 (m, 1H), 6.50 (m, 2H), 7.42 (m, 2H), 10.89 (bds, 1H).

LCMS(ESI): [M]$^+$ m/z: calcd 189.2; found 190.2; Rt=0.730 min.

Step 3: Synthesis of 4-(5-methylpiperidin-2-yl)phenol

Sodium borohydride (2 g, 52.87 mmol, 1.87 mL) was added in one portion to a stirred solution of 4-(3-methyl-2,3,4,5-tetrahydropyridin-6-yl)phenol (8.5 g, 44.91 mmol) in methanol (100 mL) at 0° C. The resulting mixture was stirred at 0° C. for 1 hr, and then evaporated in vacuo. The residue was dissolved in methanol (150 ml) and hydrogen chloride solution 40 M in dioxane (117.81 g, 449.13 mmol, 112.20 mL, 13.9% purity) was added. The resulting cloudy solution was evaporated in vacuo, the residue was diluted with THE (150 ml) and stirred for 0.5 hr. The precipitate was filtered, washed with THE (2*50 ml), and dried in vacuo to afford crude 70% purity, contaminated with sodium chloride (approximately 3 g) 4-(5-methyl-2-piperidyl)phenol (10.5 g, crude, HCl) as light-yellow solid, which was used directly in the next step.

$^1$H NMR (500 MHz, DMSO-d$_6$) δ (ppm) 0.92 (d, 3H), 1.28 (m, 1H), 1.95 (m, 3H), 2.11 (m, 1H), 2.65 (m, 1H), 3.12 (m, 1H), 3.99 (m, 1H), 6.81 (m, 2H), 7.40 (m, 2H), 9.30 (m, 1H), 9.70 (m, 2H).

LCMS(ESI): [M]$^+$ m/z: calcd 191.2; found 192.2; Rt=0.732 min.

Step 4: Synthesis of rac-(2R,5S)-tert-butyl 2-(4-hydroxyphenyl)-5-methylpiperidine-1-carboxylate 4-[(2S,5R)-5-methyl-2-piperidyl]phenol (2 g, 10.46 mmol) and TEA (3.17 g, 31.37 mmol, 4.37 mL) was dissolved in THE (30 mL). The solution was stirred for 15 min before di-tert-butyl dicarbonate (2.51 g, 11.50 mmol, 2.64 mL) was added dropwise. After that the reaction mixture was stirred overnight at room temperature and then it was diluted with EtOAc, washed with NaHSO$_4$(aq), brine, dried over Na$_2$SO$_4$, filtered and evaporated on vacuum to give tert-butyl (2S,5R)-2-(4-hydroxyphenyl)-5-methyl-piperidine-1-carboxylate (2.86 g, 9.82 mmol, 93.87% yield) which was used in the next step without further purification.

$^1$H NMR (400 MHz, CDCl$_3$) δ (ppm) 1.00 (d, 3H), 1.28 (m, 2H), 1.49 (s, 9H), 1.78 (m, 2H), 2.07 (m, 2H), 2.97 (m, 1H), 3.71 (m, 1H), 5.24 (m, 1H), 6.78 (d, 2H), 7.05 (d, 2H).

Step 5: Synthesis of rac-(2R,5S)-tert-butyl 2-(4-acetoxyphenyl)-5-methylpiperidine-1-carboxylate tert-butyl (2S,5R)-2-(4-hydroxyphenyl)-5-methyl-piperidine-1-carboxylate (2.86 g, 9.82 mmol) and acetyl chloride (847.54 mg, 10.80 mmol, 657.01 µL)TEA (2.98 g, 29.45 mmol, 4.10 mL) was dissolved in anhydrous DCM (36 mL) and cooled to 0° C. Acetyl chloride (847.54 mg, 10.80 mmol, 657.01 µL) was added dropwise, then the reaction mixture was allowed to warm to rt and stirred overnight, then washed with NaHSO$_4$(aq), NaHCO$_3$(aq) and brine. The organic phase was dried over Na$_2$SO$_4$, filtered and evaporated on vacuum to give tert-butyl (2S,5R)-2-(4-acetoxyphenyl)-5-methyl-piperidine-1-carboxylate (3.11 g, 9.33 mmol, 95.03% yield) which was used in the next step without further purification tert-butyl (2S,5R)-2-(4-acetoxyphenyl)-5-methyl-piperidine-1-carboxylate (3.11 g, 9.33 mmol, 95.03% yield).

$^1$H NMR (500 MHz, CDCl$_3$) δ (ppm) 1.04 (d, 3H), 1.31 (m, 1H), 1.53 (s, 9H), 1.80 (m, 2H), 2.12 (m, 2H), 2.29 (s, 3H), 2.99 (m, 1H), 3.73 (m, 1H), 5.31 (m, 1H), 7.05 (d, 2H), 7.23 (d, 2H)

Step 6: Synthesis of rac-4-((2R,5S)-5-methylpiperidin-2-yl)phenyl acetate tert-butyl (2S,5R)-2-(4-acetoxyphenyl)-5-methyl-piperidine-1-carboxylate (3.11 g, 9.33 mmol) was dissolved in hydrogen chloride solution 40 M in dioxane (6.80 g, 186.55 mmol, 8.50 mL) and was stirred for 3 hr at 20° C. The reaction mixture was concentrated on vacuum to give [4-[(2S,5R)-5-methyl-2-piperidyl]phenyl]acetate (2.38 g, 8.82 mmol, 94.51% yield, HCl) which was used in the next step without further purification.

$^1$H NMR (400 MHz, DMSO-d$_6$) δ (ppm) 0.90 (d, 3H), 1.27 (m, 1H), 2.05 (m, 3H), 2.22 (s, 3H), 2.63 (m, 2H), 3.17 (m, 1H), 3.96 (m, 1H), 7.16 (d, 2H), 7.62 (d, 2H), 9.26 (m, 1H).

6I. The Synthesis of 5-(5-methylpiperidin-2-yl)-1H-indole

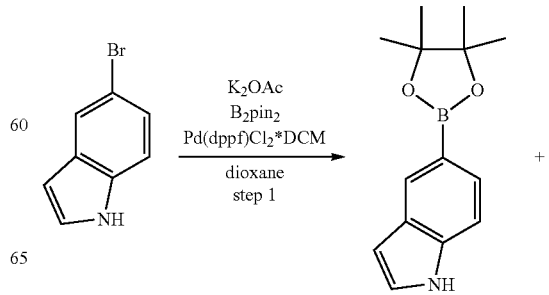

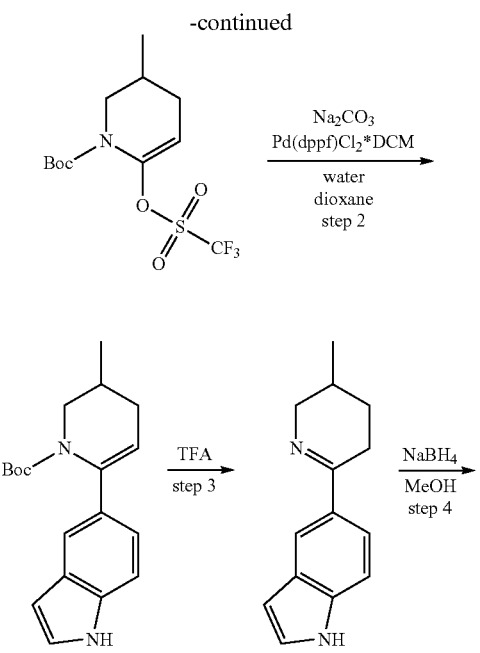

Step 1: Synthesis of 5-(4,4,5,5-tetramethyl-1,3,2-dioxaborolan-2-yl)-1H-indole

Potassium acetate (15.02 g, 153.03 mmol, 9.57 mL) was added to a solution of 5-bromo-1H-indole (15 g, 76.51 mmol) and 4,4,5,5-tetramethyl-2-(4,4,5,5-tetramethyl-1,3,2-dioxaborolan-2-yl)-1,3,2-dioxaborolane (22.34 g, 87.99 mmol) in dioxane (400 mL). Reaction flask was evacuated and refilled with argon 3 times. Then Pd(dppf)Cl$_2$*DCM (3.12 g, 3.83 mmol) was added under stream of argon. Resulting mixture was stirred at 90° C. for 28 hr under inert atmosphere. Then, it was cooled, diluted with MTBE (700 mL) and filtered. Filtrate was concentrated under reduced pressure and the residue was purified by silica gel flash chromatography eluting with a 0 to 100 percent MTBE-hexane gradient to give 5-(4,4,5,5-tetramethyl-1,3,2-dioxaborolan-2-yl)-1H-indole (7.2 g, 29.62 mmol, 38.71% yield).

$^1$H NMR (400 MHz, CDCl$_3$) δ (ppm) 1.35 (s, 12H), 6.55 (d, 1H), 7.17 (s, 1H), 7.36 (d, 1H), 7.63 (d, 1H), 8.17 (m, 2H).

GCMS: calcd 243.2; found 243.2; Rt=11.341 min.

Step 2: Synthesis of tert-butyl 6-(1H-indol-5-yl)-3-methyl-3,4-dihydropyridine-1(2H)-carboxylate A mixture of tert-butyl 3-methyl-6-(trifluoromethylsulfonyloxy)-3,4-dihydro-2H-pyridine-1-carboxylate (4.73 g, 13.70 mmol), 5-(4,4,5,5-tetramethyl-1,3,2-dioxaborolan-2-yl)-1H-indole (4.16 g, 17.12 mmol), cyclopentyl(diphenyl)phosphane; dichloromethane; dichloropalladium; iron (559.27 mg, 684.84 μmol) and sodium carbonate (4.36 g, 41.09 mmol, 1.72 mL) in dioxane (75 mL) and water (25 mL) was stirred at 80° C. under argon atmosphere for 28 hr. After cooling to room temperature, the reaction mixture was filtered off. The filtercake was washed with dioxane (100 mL) and discarded. Filtrate was concentrated under reduced pressure and the residue was purified by silica gel flash chromatography eluting with a 0 to 100 percent MTBE-Hexane gradient to give tert-butyl 6-(1H-indol-5-yl)-3-methyl-3,4-dihydro-2H-pyridine-1-carboxylate (1.2 g, 3.84 mmol, 28.04% yield).

$^1$H NMR (400 MHz, DMSO-d$_6$) δ (ppm) 0.87 (s, 9H), 0.97 (m, 2H), 1.24 (m, 2H), 1.85 (m, 2H), 2.38 (m, 1H), 3.02 (m, 1H), 3.92 (d, 1H), 5.20 (m, 1H), 6.37 (m, 1H), 6.99 (d, 1H), 7.29 (d, 1H), 7.38 (m, 1H), 10.97 (m, 1H).

LCMS(ESI): [M-Boc]$^+$ m/z: calcd 212.2; found 213.2; Rt=1.591 min.

Step 3: Synthesis of 5-(5-methyl-3,4,5,6-tetrahydropyridin-2-yl)-1H-indole

The solution of tert-butyl 6-(1H-indol-5-yl)-3-methyl-3,4-dihydro-2H-pyridine-1-carboxylate (1.2 g, 3.84 mmol) in TFA (7.01 g, 61.46 mmol, 4.73 mL) was stirred at 20° C. for 1 hr, and then evaporated in vacuo. Crushed ice (10 g) was added to the residue and pH was adjusted to 8 with a 10% aqueous solution of sodium hydroxide. The resulting mixture was extracted with ethylacetate (2*30 mL). The combined organic extracts were dried over sodium sulphate and evaporated in vacuo to afford 5-(3-methyl-2,3,4,5-tetrahydropyridin-6-yl)-1H-indole (0.8 g, crude) as yellow solid, which was used directly in the next step.

$^1$H NMR (400 MHz, DMSO-d$_6$) δ (ppm) 0.96 (m, 3H), 1.17 (m, 2H), 1.98 (m, 2H), 3.04 (m, 1H), 3.22 (m, 2H), 3.87 (m, 1H), 6.58 (m, 1H), 7.32 (m, 1H), 7.46 (m, 1H), 8.24 (m, 1H), 11.05 (m, 1H).

LCMS(ESI): [M]$^+$ m/z: calcd 212.2; found 213.2; Rt=0.940 min.

Step 4: Synthesis of 5-(5-methylpiperidin-2-yl)-1H-indole

Sodium borohydride (285.12 mg, 7.54 mmol, 266.47 μL) was added in one portion to a stirred solution of 5-(3-methyl-2,3,4,5-tetrahydropyridin-6-yl)-1H-indole (0.8 g, 3.77 mmol) in MeOH (20 mL) at 0° C. The resulting mixture was stirred at 0° C. for 1 hr, and then evaporated in vacuo. The residue was diluted with water (10 mL) and extracted with dichloromethane (2*20 mL). The combined organic extracts were dried over sodium sulphate and evaporated in vacuo to afford 5-(5-methyl-2-piperidyl)-1H-indole (0.8 g, crude) as yellow solid, which was used directly in the next step.

$^1$H NMR (400 MHz, DMSO-d$_6$) δ (ppm) 0.79 (d, 3H), 1.06 (m, 1H), 1.34 (m, 2H), 1.74 (m, 2H), 2.25 (m, 1H), 2.98 (m, 1H), 3.29 (m, 1H), 5.28 (m, 1H), 6.30 (m, 1H), 7.23 (m, 4H), 10.90 (m, 1H).

LCMS(ESI): [M]$^+$ m/z: calcd 214.2; found 215.2; Rt=0.950 min.

6J. The Synthesis of 5-(5-methylpiperidin-2-yl)-1H-benzo[d]imidazole

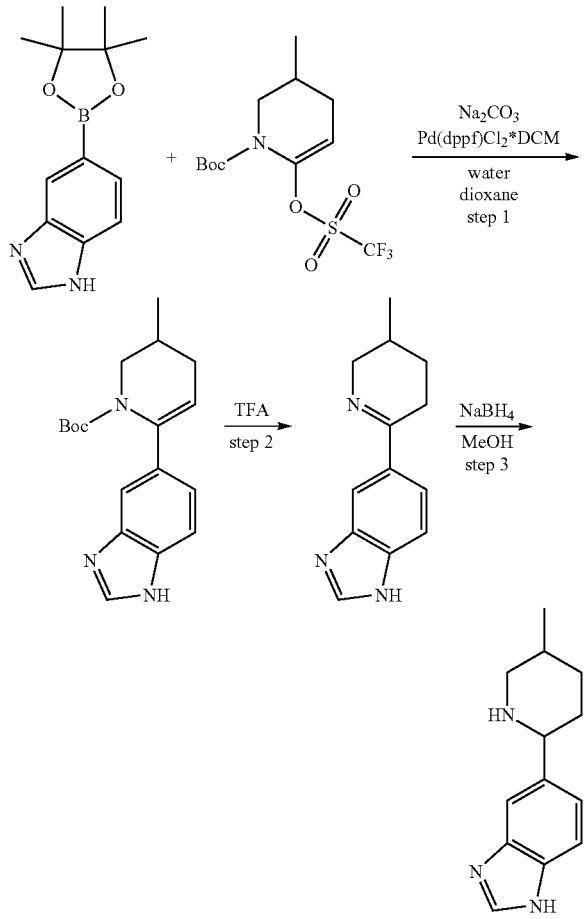

Step 1: Synthesis of tert-butyl 6-(1H-benzo[d]imidazol-5-yl)-3-methyl-3,4-dihydropyridine-1(2H)-carboxylate A mixture of tert-butyl 3-methyl-6-(trifluoromethylsulfonyloxy)-3,4-dihydro-2H-pyridine-1-carboxylate (4 g, 11.58 mmol), 5-(4,4,5,5-tetramethyl-1,3,2-dioxaborolan-2-yl)-1H-benzimidazole (4.06 g, 14.48 mmol, HCl), Pd(dppf)Cl$_2$*DCM (472.95 mg, 579.15 μmol) and sodium carbonate (4.91 g, 46.33 mmol, 1.94 mL) in dioxane (75 mL) and water (25 mL) was stirred at 80° C. under argon atmosphere for 48 hr. After cooling to room temperature, the reaction mixture was filtered off. The filtercake was washed with dioxane (100 mL) and discarded. Filtrate was concentrated under reduced pressure and the residue was purified by silica gel flash chromatography eluting with a 0 to 100 percent MeCN—CHCl$_3$ gradient to give the tert-butyl 6-(1H-benzimidazol-5-yl)-3-methyl-3,4-dihydro-2H-pyridine-1-carboxylate (1.5 g, 4.79 mmol, 41.32% yield).

$^1$H NMR (500 MHz, CDCl$_3$) δ (ppm) 1.03 (d, 3H), 1.25 (s, 9H), 1.86 (m, 1H), 2.04 (m, 1H), 2.44 (d, 1H), 3.06 (t, 1H), 4.11 (d, 1H), 5.35 (s, 1H), 7.25 (m, 1H), 7.58 (m, 3H), 8.01 (m, 1H).

LCMS(ESI): [M]$^+$ m/z: calcd 313.2; found 314.2; Rt=1.015 min.

Step 2: Synthesis of 5-(5-methyl-3,4,5,6-tetrahydropyridin-2-yl)-1H-benzo[d]imidazole The solution of tert-butyl 6-(1H-benzimidazol-5-yl)-3-methyl-3,4-dihydro-2H-pyridine-1-carboxylate (1.50 g, 4.79 mmol) in TFA (8.73 g, 76.58 mmol, 5.90 mL) was stirred at 20° C. for 1 hr, and then evaporated in vacuo. Crushed ice (10 g) was added to the residue and pH was adjusted to 8 with a 10% aqueous solution of sodium hydroxide. The resulting mixture was extracted with EtOAc (2*30 mL). The combined organic extracts were dried over sodium sulphate and evaporated in vacuo to afford 5-(3-methyl-2,3,4,5-tetrahydropyridin-6-yl)-1H-benzimidazole (1 g, crude) as brown gum, which was used directly in the next step.

$^1$H NMR (500 MHz, DMSO-d$_6$) δ (ppm) 0.96 (d, 3H), 1.37 (m, 1H), 1.71 (m, 1H), 1.88 (m, 1H), 2.75 (m, 1H), 2.99 (m, 1H), 3.23 (m, 1H), 3.93 (m, 1H), 7.55 (m, 1H), 7.77 (m, 1H), 8.05 (m, 1H), 8.28 (m, 1H), 12.56 (m, 1H).

LCMS(ESI): [M]$^+$ m/z: calcd 213.2; found 214.2; Rt=0.693 min.

Step 3: Synthesis of 5-(5-methylpiperidin-2-yl)-1H-benzo[d]imidazole

Sodium borohydride (266.08 mg, 7.03 mmol, 248.67 μL) was added in one portion to a stirred solution of 5-(3-methyl-2,3,4,5-tetrahydropyridin-6-yl)-1H-benzimidazole (1.00 g, 4.69 mmol) in MeOH (20 mL) at 0° C. The resulting mixture was stirred at 0° C. for 1 hr, and then evaporated in vacuo. The residue was diluted with water (10 mL) and extracted with dichloromethane (2*20 mL). The combined organic extracts were dried over sodium sulphate and evaporated in vacuo to afford 5-(5-methyl-2-piperidyl)-1H-benzimidazole (0.82 g, crude) as brown solid, which was used directly in the next step.

$^1$H NMR (500 MHz, DMSO-d$_6$) δ (ppm) 0.84 (m, 3H), 1.11 (m, 1H), 1.53 (m, 2H), 1.79 (m, 2H), 2.31 (m, 1H), 3.02 (m, 1H), 3.56 (m, 1H), 7.17 (m, 1H), 7.49 (m, 3H), 8.13 (m, 1H), 12.36 (m, 1H).

LCMS(ESI): [M]$^+$ m/z: calcd 215.2; found 216.2; Rt=0.627 min.

6K. The Synthesis of 5-[(2S,5R)-5-methyl-2-piperidyl]-1H-indazole

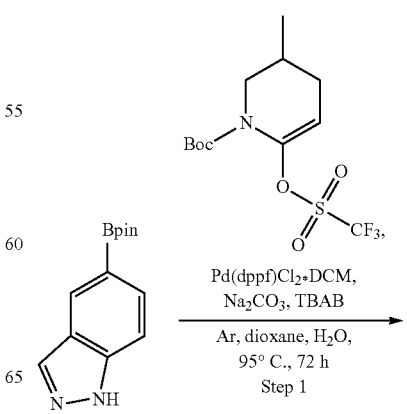

Pd(dppf)Cl$_2$*DCM, Na$_2$CO$_3$, TBAB

Ar, dioxane, H$_2$O, 95° C., 72 h

Step 1

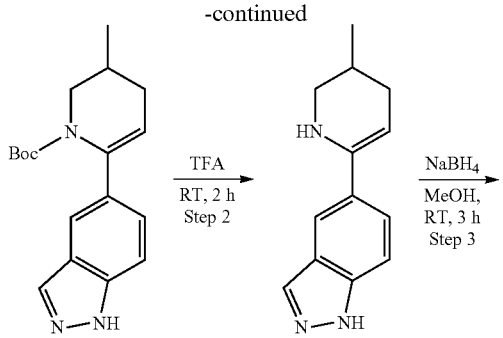

Step 1: The Synthesis of tert-butyl 6-(1H-indazol-5-yl)-3-methyl-3,4-dihydro-2H-pyridine-1-carboxylate A suspension of 5-(4,4,5,5-tetramethyl-1,3,2-dioxaborolan-2-yl)-1H-indazole (3 g, 12.29 mmol), tert-butyl 3-methyl-6-(trifluoromethylsulfonyloxy)-3,4-dihydro-2H-pyridine-1-carboxylate (4.24 g, 12.29 mmol), sodium carbonate (5.21 g, 49.16 mmol, 2.06 mL) and tetrabutylammonium bromide (198.10 mg, 614.51 μmol) in Dioxane (60 mL) and Water (12 mL) was degassed and refilled with Ar three time. To this solution Pd(dppf)Cl$_2$*DCM (501.83 mg, 614.51 μmol) was added. The resulting mixture was degassed, refilled with Ar and stirred at 95° C. for 72 hr. The precipitate was filtered off, washed with dioxane (50 ml). The solvent was evaporated in vacuo and the residue was taken up with water 150 ml and extracted with EtOAc (2*100 ml). The combined organic layer was washed with brine (100 ml), dried over Na$_2$SO$_4$ and evaporated to obtain crude product (7 g). The crude product was purified by gradient chromatography (SiO$_2$, CHCl$_3$-MeOH) to obtain tert-butyl 6-(1H-indazol-5-yl)-3-methyl-3,4-dihydro-2H-pyridine-1-carboxylate (1.5 g, 4.79 mmol, 38.94% yield).

$^1$H NMR (500 MHz, DMSO-d$_6$): δ (ppm) 0.96 (s, 9H), 0.97 (d, 3H), 1.85 (m, 2H), 2.40 (m, 1H), 3.02 (m, 1H), 3.91 (m, 1H), 5.29 (s, 1H), 7.24 (d, 1H), 7.44 (d, 1H), 7.58 (s, 1H), 8.01 (s, 1H), NH is not observed.

LCMS(ESI): [M+H]$^+$ m/z: calcd 313.2; found 314.2; Rt=1.321 min.

Step 2: The Synthesis of 5-(3-methyl-2,3,4,5-tetrahydropyridin-6-yl)-1H-indazole tert-butyl 6-(1H-indazol-5-yl)-3-methyl-3,4-dihydro-2H-pyridine-1-carboxylate (1.5 g, 4.79 mmol) was dissolved in trifluoroacetic acid (14.80 g, 129.80 mmol, 10 mL). The resulting mixture was stirred at 25° C. for 2 hr (to the end of gas evolution) and the solvent was evaporated in vacuo. The pH of the solution was adjusted to 8 with 10% NaHCO$_3$ solution and extracted with DCM (3*70 ml). The combined organic layer was washed with brine (50 ml), dried over Na$_2$SO$_4$ and evaporated in vacuo to obtain 5-(3-methyl-2,3,4,5-tetrahydropyridin-6-yl)-1H-indazole (0.8 g, 3.75 mmol, 780.37% yield). This compound was used for the next step without purification.

$^1$H NMR (400 MHz, CDCl$_3$): δ(ppm) 1.00 (d, 3H), 1.42 (m, 1H), 1.74 (m, 1H), 1.95 (m, 1H), 2.67 (m, 1H), 2.86 (m, 1H), 3.29 (m, 1H), 4.05 (m, 1H), 7.40 (d, 1H), 7.96 (d, 1H), 8.08 (s, 2H), 10.73 (m, 1H).

LCMS(ESI): [M+H]$^+$ m/z: calcd 213.2; found 214.2; Rt=0.727 min.

Step 3: The Synthesis of 5-[(2S,5R)-5-methyl-2-piperidyl]-1H-indazole

To a solution of 5-(3-methyl-2,3,4,5-tetrahydropyridin-6-yl)-1H-indazole (0.8 g, 3.75 mmol) in MeOH (20 mL), sodium borohydride (283.82 mg, 7.50 mmol, 265.25 μL) was added portionwise at 0° C. The resulting mixture was stirred at 25° C. for 3 hr and the solvent was evaporated in vacuo, the residue was taken up with water (30 ml) and extracted with EtOAc (3*30 ml). The combined organic extract was washed with brine (2*50 ml), dried over Na$_2$SO$_4$ and evaporated to give 5-[(2S,5R)-5-methyl-2-piperidyl]-1H-indazole (0.73 g, 3.39 mmol, 90.40% yield). This compound was used for the next step without purification.

$^1$H NMR (400 MHz, DMSO-d$_6$): δ (ppm) 0.80 (d, 3H), 1.07 (m, 2H), 1.35 (m, 1H), 1.49 (m, 1H), 1.73 (m, 2H), 2.25 (m, 1H), 2.96 (m, 1H), 3.50 (m, 1H), 7.31 (d, 1H), 7.39 (d, 1H), 7.64 (s, 1H), 7.95 (s, 1H), 12.89 (m, 1H).

LCMS(ESI): [M+H]$^+$ m/z: calcd 215.1; found 216.2; Rt=0.645 min.

6L. The Synthesis of 5-(2-piperidyl)-1H-indazole

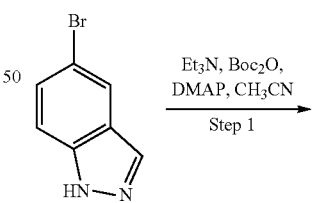

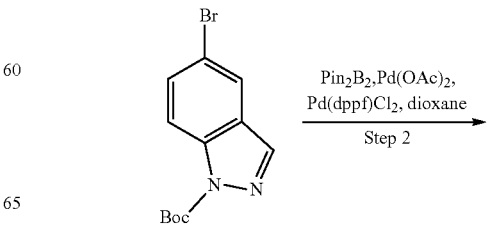

-continued

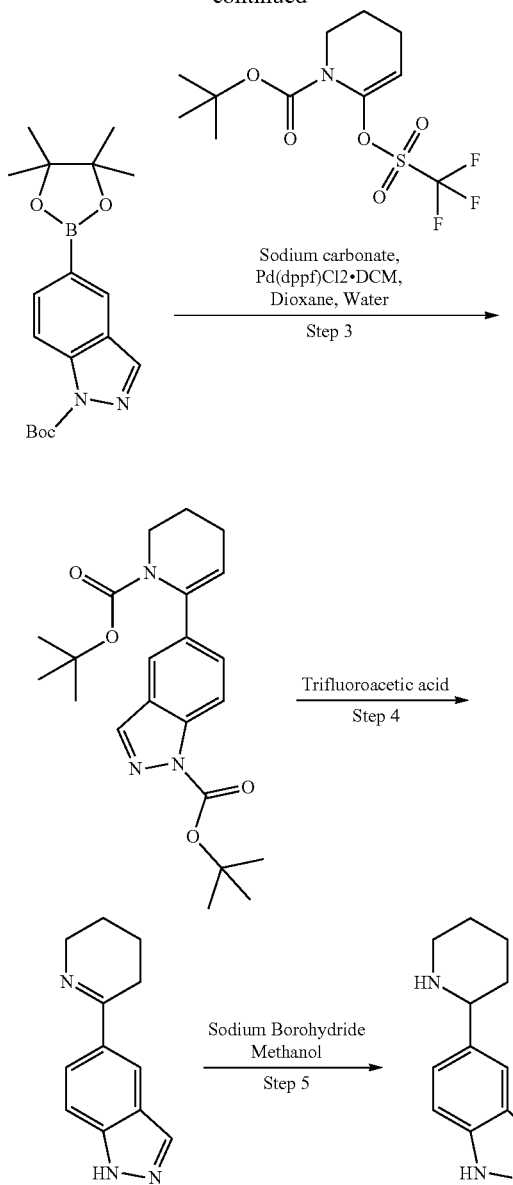

Step 1: Synthesis of tert-butyl 5-bromoindazole-1-carboxylate

To a stirring solution of 5-bromo-1H-indazole (20.5 g, 104.04 mmol) in Acetonitrile (300 mL) was added Triethylamine (10.53 g, 104.04 mmol, 14.50 mL), Di-tert-butyl dicarbonate (34.06 g, 156.07 mmol, 35.82 mL) and DMAP (1.27 g, 10.40 mmol) at 0° C. The resulting reaction mixture was stirred at 25° C. for 16 hr. After 16 hours, the reaction mixture was concentrated under reduced pressure to obtain crude product as dark orange gum. The crude product was purified by column chromatography (0-100% MTBE in Hexane) to obtain product tert-butyl 5-bromoindazole-1-carboxylate (30.0 g, 100.96 mmol, 97.04% yield) as a light orange liquid.

$^1$H NMR (CDCl$_3$, 400 MHz): δ 1.69 (s, 9H), 7.60 (d, 1H), 7.85 (s, 1H), 8.08 (m, 2H).

Step 2: Synthesis of tert-butyl 5-(4,4,5,5-tetramethyl-1,3,2-dioxaborolan-2-yl)indazole-1-carboxylate To suspension of tert-butyl 5-bromoindazole-1-carboxylate (30 g, 100.96 mmol), 4,4,4',4',5,5,5',5'-Octamethyl-2,2'-bi-1,3,2-dioxaborolane (28.20 g, 111.06 mmol) and Potassium Acetate (19.82 g, 201.92 mmol, 12.62 mL) in Dioxane (700 mL) was degassed and refilled with Ar three time. To this solution, [1,1'-Bis(diphenylphosphino)ferrocene]dichloropalladium(II), complex with dichloromethane (4.12 g, 5.05 mmol) was added, the resulting mixture was stirred at 90° C. for 48 hr, cooled, filtered, evaporated in vacuo. The residue (50 g) was purified by gradient chromatography (Hexane-EA) to give tert-butyl 5-(4,4,5,5-tetramethyl-1,3,2-dioxaborolan-2-yl)indazole-1-carboxylate (29 g, 84.25 mmol, 83.45% yield).

$^1$H NMR (CDCl$_3$, 400 MHz): δ 1.35 (m, 12H), 1.71 (s, 9H), 7.92 (d, 1H), 8.14 (m, 1H), 8.21 (s, 1H).

Step 3: Synthesis of tert-butyl 5-(1-tert-butoxycarbonyl-3,4-dihydro-2H-pyridin-6-yl)indazole-1-carboxylate To a stirring solution of tert-butyl 6-(trifluoromethylsulfonyloxy)-3,4-dihydro-2H-pyridine-1-carboxylate (2.00 g, 5.55 mmol), tert-butyl 5-(4,4,5,5-tetramethyl-1,3,2-dioxaborolan-2-yl)indazole-1-carboxylate (2.12 g, 5.55 mmol) and Sodium carbonate (1.77 g, 16.66 mmol, 697.99 μL) in Dioxane (24 mL) and Water (8 mL) was added Pd(dppf)Cl$_2$DCM (226.77 mg, 277.69 μmol) under nitrogen at room temperature. The resulting reaction mixture was stirred at 90° C. for 16 hr under nitrogen. After 16 hours, the reaction mixture was allowed to cool to room temperature and filtered through silica pad. The silica pad was washed with ethyl acetate (100 mL). The filtrate was concentrated under reduced pressure to obtain dark brown crude product. The crude product was purified by column chromatography on silica gel (0-100% MTBE in Hexane) to get product tert-butyl 5-(1-tert-butoxycarbonyl-3,4-dihydro-2H-pyridin-6-yl)indazole-1-carboxylate (550 mg, 1.38 mmol, 24.79% yield) as an off-white solid.

$^1$H NMR (500 MHz, CDCl$_3$) δ 0.99 (s, 9H), 1.22 (s, 9H), 1.87 (m, 2H), 2.27 (m, 2H), 5.33 (s, 1H), 7.35 (s, 1H), 7.40 (s, 1H), 7.66 (s, 1H), 8.04 (s, 1H).

LCMS(ESI): [M-Boc+H]$^+$ m/z: calcd 300.0; found 300; Rt=1.369 min.

Step 4: Synthesis of 5-(2,3,4,5-tetrahydropyridin-6-yl)-1H-indazole tert-butyl 5-(1-tert-butoxycarbonyl-3,4-dihydro-2H-pyridin-6-yl)indazole-1-carboxylate (0.53 g, 1.33 mmol) in Trifluoroacetic acid (3.03 g, 26.53 mmol, 2.04 mL) was stirred at 25° C. for 1 hr. After 1 hour, the reaction mixture was concentrated under reduced pressure to obtain light orange gum crude product. Water (10 mL) was added to the crude product and the aqueous phase was basified with 10% NaOH solution till pH=10. The obtained suspension was extracted with dichloromethane (3×20 mL). The combined organic phase was washed with water (10 mL), dried over sodium sulpate, filtered and concentrated under reduced pressure to obtain crude product 5-(2,3,4,5-tetrahydropyridin-6-yl)-1H-indazole (300 mg, crude) as an off-white solid. The crude product was used for the next step reaction.

$^1$H NMR (500 MHz, CDCl$_3$) δ 1.69 (m, 2H), 1.87 (m, 2H), 2.74 (m, 2H), 3.88 (m, 2H), 7.42 (d, 1H), 7.99 (d, 1H), 8.10 (s, 2H), 10.71 (brs, 1H).

LCMS(ESI): [M+H]$^+$ m/z: calcd 199.1; found 200.2; Rt=0.644 min.

Step 5: Synthesis of 5-(2-piperidyl)-1H-indazole

To a stirring solution of 5-(2,3,4,5-tetrahydropyridin-6-yl)-1H-indazole (300 mg, 1.51 mmol) in Methanol (8 mL) was added Sodium Borohydride (85.44 mg, 2.26 mmol, 79.85 μL) at 25° C. The resulting reaction mixture was stirred at the same temperature for 1 hr. After 1 hour, the reaction mixture was concentrated under reduced pressure and the crude product was quenched with water (20 mL). The obtained mixture was extracted with dichloromethane (3×30 mL), washed with water (20 mL), dried over sodium sulphate, filtered and concentrated under reduced pressure to obtain crude product 5-(2-piperidyl)-1H-indazole (200 mg, crude) as an off-white solid. The crude product was used for the next step reaction.

$^1$H NMR (DMSO, 400 MHz): δ 1.33-1.43 (m, 3H), 1.55 (m, 1H), 1.68 (m, 1H), 1.71 (m, 1H), 2.27 (m, 1H), 2.64 (m, 1H), 3.04 (m, 1H), 3.60 (m, 1H), 7.34 (d, 1H), 7.43 (d, 1H), 7.67 (s, 1H), 7.98 (s, 1H).

LCMS(ESI): [M+H]$^+$ m/z: calcd 201.2; found 202.2; Rt=0.668 min.

6M. Synthesis of 2-methyl-4-(5-methyl-2-piperidyl)phenol

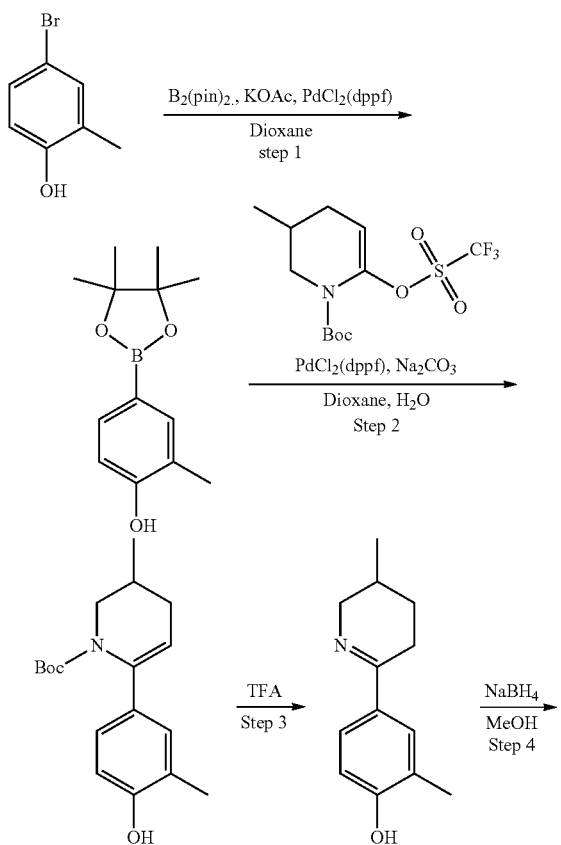

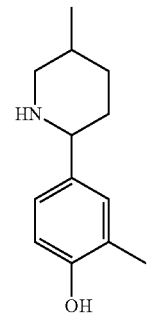

Step 1: Synthesis of 2-methyl-4-(4,4,5,5-tetramethyl-1,3,2-dioxaborolan-2-yl)phenol A stirring solution of 4-bromo-2-methyl-phenol (18.8 g, 100.52 mmol), 4,4,5,5-tetramethyl-2-(4,4,5,5-tetramethyl-1,3,2-dioxaborolan-2-yl)-1,3,2-dioxaborolane (30.63 g, 120.62 mmol) and KOAc (29.59 g, 301.55 mmol, 18.85 mL) in 1,4-dioxane (400 mL) was purged with argon for 10 minutes. After 10 minutes, Pd(dppf)C$_{12}$CH$_2$Cl$_2$ (1.5 g, 1.84 mmol) was added under argon. The reaction mixture was stirred under argon at 100° C. for 16 hours. The reaction mixture was then cooled to room temperature, filtered and the filtrate was concentrated under reduced pressure. The obtained crude product was purified by flash chromatography (SiO$_2$, Eluent: CHCl$_3$:acetonitrile) to give 2-methyl-4-(4,4,5,5-tetramethyl-1,3,2-dioxaborolan-2-yl)phenol (11.4 g, 48.70 mmol, 48.45% yield) as a white solid.

LCMS(ESI): [M+H]$^+$ m/z: calcd 234.2; found 235.4; Rt=1.386 min.

Step 2: Synthesis of tert-butyl 6-(4-hydroxy-3-methyl-phenyl)-3-methyl-3,4-dihydro-2H-pyridine-1-carboxylate A stirring solution of tert-butyl 3-methyl-6-(trifluoromethylsulfonyloxy)-3,4-dihydro-2H-pyridine-1-carboxylate (3.54 g, 10.25 mmol), 2-methyl-4-(4,4,5,5-tetramethyl-1,3,2-dioxaborolan-2-yl)phenol (3 g, 12.82 mmol) and Sodium carbonate (3.26 g, 30.76 mmol, 1.29 mL) in 1,4-dioxane (15 mL) and water (5 mL) was purged with argon. Then, Pd(dppf)Cl$_2$CH$_2$Cl$_2$ (418.29 mg, 512.60 μmol) was added under argon. The reaction mixture was stirred under argon at 75° C. for 16 hours. After 16 hours, the reaction mixture was allowed to cool to room temperature and filtered. The filter cake was washed with 1,4-dioxane (10 mL) and discarded. The filtrate was washed with water and extracted with DCM. The combined organic phase was dried over Na$_2$SO$_4$ and concentrated under reduced pressure. The obtained crude product was purified by column chromatography (SiO$_2$; Eluent: MTBE in Hexane) to get tert-butyl 6-(4-hydroxy-3-methyl-phenyl)-3-methyl-3,4-dihydro-2H-pyridine-1-carboxylate (2 g, crude).

LCMS(ESI): [M+H]$^+$ m/z: calcd 303.2; found 304.2; Rt=1.498 min.

Step 3: Synthesis of 2-methyl-4-(3-methyl-2,3,4,5-tetrahydropyridin-6-yl)phenol tert-butyl 6-(4-hydroxy-3-methyl-phenyl)-3-methyl-3,4-dihydro-2H-pyridine-1-carboxylate (2 g, crude) was dissolved in Trifluoroacetic acid (29.60 g, 259.60 mmol, 20 mL) and stirred for 16 hours at room temperature. After 16 hours, the reaction mixture was concentrated under reduced pressure to get dark-brown oil. The obtained crude product was treated with MTBE, washed with water and concentrated in vacuo to give 2-methyl-4-(3-methyl-2,3,4,5-tetrahydropyridin-6-yl)phenol (2.4 g, crude). The crude product was used in the next step reaction without any further purification.

LCMS(ESI): [M+H]⁺ m/z: calcd 203.2; found 204.2; Rt=0.680 min.

Step 4: Synthesis of
2-methyl-4-(5-methyl-2-piperidyl)phenol

Sodium Borohydride (446.66 mg, 11.81 mmol) was added portion wise at 0° C. to a stirred solution of 2-methyl-4-(3-methyl-2,3,4,5-tetrahydropyridin-6-yl)phenol (2.4 g, 11.81 mmol) in methanol (20 mL). The reaction mixture was stirred at the room temperature for 1 hour. After 1 hour, the reaction mixture was concentrated under reduced pressure, the residue was diluted with water and extracted with DCM (2×25 mL). The combined organic phase was dried over Na$_2$SO$_4$ and evaporated in vacuo. The crude product was purified by reverse phase HPLC (Eluent: 40-70% CH$_3$CN+ formic acid/H$_2$O; flow rate: 30 mL/min; loading pump: 4 mL, CH$_3$CN; column: SunFire 100×19 mm, 5 µM) to obtain 2-methyl-4-(5-methyl-2-piperidyl)phenol (0.21 g, 1.02 mmol, 8.66% yield).

LCMS(ESI): [M+H]⁺ m/z: calcd 205.2; found 206.4; Rt=1.881 min.

6N. The Synthesis of
5-(5-methyl-2-piperidyl)indolin-2-one

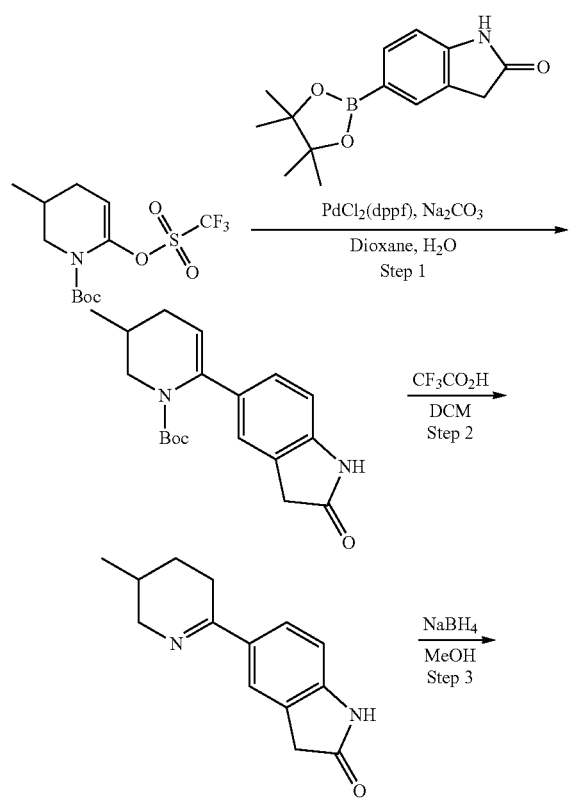

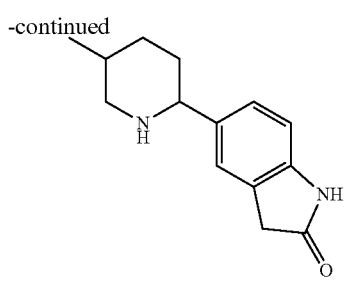

Step 1: Synthesis of tert-butyl 3-methyl-6-(2-oxoindolin-5-yl)-3,4-dihydro-2H-pyridine-1-carboxylate A stirring suspension of tert-butyl 3-methyl-6-(trifluoromethylsulfonyloxy)-3,4-dihydro-2H-pyridine-1-carboxylate (10 g, 28.96 mmol), 5-(4,4,5,5-tetramethyl-1,3,2-dioxaborolan-2-yl)indolin-2-one (8.25 g, 31.85 mmol) and Sodium carbonate (6.14 g, 57.91 mmol) in 1,4-dioxane (90 mL) and Water (30 mL) was purged with argon. Then, Pd(dppf)C$_{12}$ (1.18 g, 1.45 mmol) was added under argon. The reaction mixture was stirred under argon at 75° C. for 18 hours After 18 hours, the reaction mixture was cooled and filtered. The filtrate was evaporated in vacuo and the residue was diluted with water (100 mL) and MTBE (150 mL). Both layers were separated. The aqueous layer was extracted with MTBE (100 mL). The combined organic layer was dried over Na$_2$SO$_4$, filtered and concentrated under reduced pressure. The residue was washed with MTBE (3×50 mL) and dried under vacuo to obtain tert-butyl 3-methyl-6-(2-oxoindolin-5-yl)-3,4-dihydro-2H-pyridine-1-carboxylate (7.84 g, crude) as brown solid.

LCMS(ESI): [M+H]⁺ m/z: calcd 328.2; found 329.2; Rt=1.336 min.

Step 2: Synthesis of 5-(3-methyl-2,3,4,5-tetrahydropyridin-6-yl)indolin-2-one

To a stirred solution of tert-butyl 3-methyl-6-(2-oxoindolin-5-yl)-3,4-dihydro-2H-pyridine-1-carboxylate (7.84 g, 23.86 mmol) in DCM (40 mL) was added CF$_3$CO$_2$H (20 mL) dropwise at 0° C. The resulting reaction mixture was stirred for 1 hour at 0° C. After 1 hour, the reaction mixture was carefully poured into K$_2$CO$_3$ solution and extracted with DCM (2×75 mL). The combined organic phase was dried over Na$_2$SO$_4$, filtered and concentrated under reduced pressure to obtain 5-(3-methyl-2,3,4,5-tetrahydropyridin-6-yl) indolin-2-one (5.54 g, crude). The crude product was used in the next step reaction without any further purification.

LCMS(ESI): [M+H]⁺ m/z: calcd 228.2; found 229.2; Rt=0.727 min.

Step 3: Synthesis of
5-(5-methyl-2-piperidyl)indolin-2-one

Sodium Borohydride (2.75 g, 72.80 mmol) was added portion wise at 0° C., to a stirred solution of 5-(3-methyl-2,3,4,5-tetrahydropyridin-6-yl)indolin-2-one (5.54 g, 24.27 mmol) in MeOH (120 mL). The reaction mixture was stirred at 20° C. for 18 hours. After 18 hours, the reaction mixture was concentrated under reduced pressure. The obtained residue was diluted with water (100 mL). The resulting mixture was extracted with DCM (3×50 mL). The combined organic layer was dried over Na$_2$SO$_4$, filtered and concentrated under reduced pressure. The obtained residue was dissolved in DCM (50 mL) and washed with aqueous NaHSO₄ solution. The aqueous layer was washed with DCM (3×50 mL) and then basified with K₂CO₃. The resulting mixture was once again extracted with DCM (3×50 mL). The combined organic phase was dried over Na₂SO₄, filtered and concentrated under reduced pressure to obtain 5-(5-methyl-2-piperidyl)indolin-2-one (2.5 g, 10.86 mmol, 44.73% yield).

LCMS(ESI): [M+H]⁺ m/z: calcd 230.1; found 231.2; Rt=0.664 min.

6O. The Synthesis of Synthesis of 6-[(2R,5S)-5-methyl-2-piperidyl]-1,2,3,4-tetrahydroquinoline

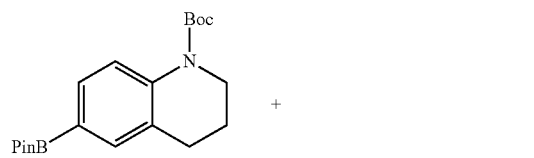

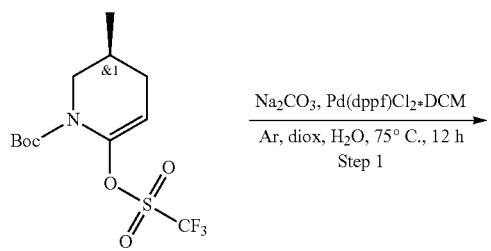

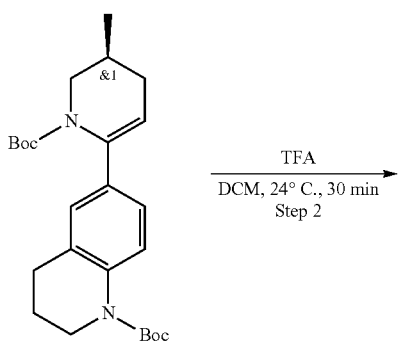

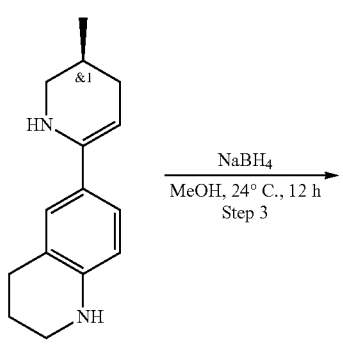

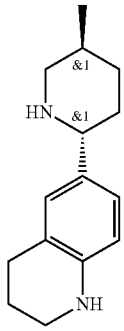

Step 1: The Synthesis of tert-butyl 6-(1-tert-butoxycarbonyl-3-methyl-3,4-dihydro-2H-pyridin-6-yl)-3,4-dihydro-2H-Quinoline-1-carboxylate tert-butyl 6-(4,4,5,5-tetramethyl-1,3,2-dioxaborolan-2-yl)-3,4-dihydro-2H-quinoline-1-carboxylate (2.24 g, 6.23 mmol), tert-butyl 3-methyl-6-(trifluoromethylsulfonyloxy)-3,4-dihydro-2H-pyridine-1-carboxylate (1.79 g, 5.20 mmol), sodium carbonate (1.65 g, 15.59 mmol, 653.00 μL) and Pd(dppf)Cl₂ DCM (169.74 mg, 207.83 μmol) were added to a mixture of 1,4-dioxane (15 mL) and water (5 mL). The reaction mixture was stirred under inert atmosphere at 75° C. for 12 hr, then cooled to RT and filtered. The filtercake was washed with dioxane and discarded. The filtrate was evaporated in vacuo and the residue was purified by column chromatography to afford tert-butyl 6-(1-tert-butoxycarbonyl-3-methyl-3,4-dihydro-2H-pyridin-6-yl)-3,4-dihydro-2H-quinoline-1-carboxylate (0.9 g, 2.10 mmol, 40.42% yield).

LCMS(ESI): [M+H]⁺ m/z: calcd 428.2; found 429.2; Rt=1.835 min.

Step 2: The Synthesis of 6-(3-methyl-2,3,4,5-tetrahydropyridin-6-yl)-1,2,3,4-tetrahydroquinoline tert-butyl 6-(1-tert-butoxycarbonyl-3-methyl-3,4-dihydro-2H-pyridin-6-yl)-3,4-dihydro-2H-quinoline-1-carboxylate (0.9 g, 2.10 mmol) was dissolved in a mixture of TFA (2.96 g, 25.96 mmol, 2 mL) and DCM (2 mL) and stirred at 24° C. for 0.5 hr. After completion of the reaction, the reaction mixture was evaporated in vacuo. The residue was dissolved in DCM (5 mL) and washed with water (3*5 mL). An organic layer was dried over Na₂SO₄ and evaporated in vacuo to afford 6-(3-methyl-2,3,4,5-tetrahydropyridin-6-yl)-1,2,3,4-tetrahydroquinoline (0.38 g, 1.66 mmol, 79.25% yield).

LCMS(ESI): [M+H]⁺ m/z: calcd 228.2; found 229.2; Rt=0.878 min.

Step 3: The Synthesis of 6-[(2R,5S)-5-methyl-2-piperidyl]-1,2,3,4-tetrahydroquinoline 6-(3-methyl-2,3,4,5-tetrahydropyridin-6-yl)-1,2,3,4-tetrahydroquinoline (0.38 g, 1.66 mmol) was dissolved in methanol (2 mL) and sodium borohydride (75.56 mg, 2.00 mmol, 70.61 μL) was added in one portion with stirring. After 12 hr, the reaction mixture was evaporated. A residue was dissolved in DCM (5 mL) and washed with water (2*5 mL). An organic layer was dried over Na₂SO₄ and evaporated under reduced pressure to afford 6-[(2R,5S)-5-methyl-2- piperidyl]-1,2,3,4-tetrahydroquinoline (0.2 g, crude) which was used in the next step without purification.

LCMS(ESI): [M+H]⁺ m/z: calcd 230.2; found 231.2; Rt=0.73 min.

6P. The Synthesis of 6-(5-methyl-2-piperidyl)-3,4-dihydro-1H-quinolin-2-one

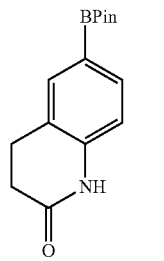

+

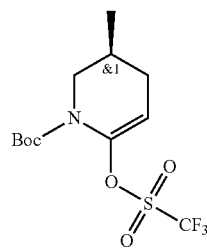

Na₂CO₃, Pd(dppf)Cl₂·DCM
Ar, diox, H₂O, 75° C., 12 h
Step 1

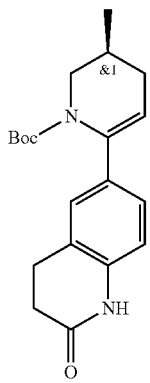

TFA
DCM, 24° C., 30 min
Step 2

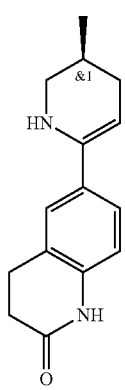

NaBH₄
MeOH, 24° C., 12 h
Step 3

-continued

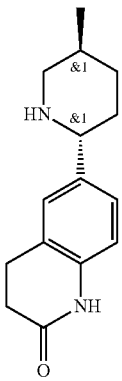

Step 1: The Synthesis of tert-butyl 3-methyl-6-(2-oxo-3,4-dihydro-1H-quinolin-6-yl)-3,4-dihydro-2H-pyridine-1-carboxylate 6-(4,4,5,5-tetramethyl-1,3,2-dioxaborolan-2-yl)-3,4-dihydro-1H-quinolin-2-one (2.5 g, 9.15 mmol), tert-butyl 3-methyl-6-(trifluoromethylsulfonyloxy)-3,4-dihydro-2H-pyridine-1-carboxylate (2.63 g, 7.63 mmol), sodium carbonate (2.43 g, 22.88 mmol, 958.62 µL) and Pd(dppf)Cl₂ DCM (249.18 mg, 305.10 µmol) were added to a mixture of 1,4-dioxane (15 mL) and water (5 mL). The reaction mixture was stirred under inert atmosphere at 75° C. for 12 hr, then cooled to RT and filtered. The filtercake was washed with dioxane and discarded. The filtrate was evaporated in vacuo and the residue was purified by column chromatography to afford tert-butyl 3-methyl-6-(2-oxo-3,4-dihydro-1H-quinolin-6-yl)-3,4-dihydro-2H-pyridine-1-carboxylate (1 g, 2.92 mmol, 38.29% yield).

LCMS(ESI): [M+H]⁺ m/z: calcd 342.2; found 343.2; Rt=1.405 min.

Step 2: The Synthesis of 6-(3-methyl-2,3,4,5-tetrahydropyridin-6-yl)-3,4-dihydro-1H-quinolin-2-one tert-butyl 3-methyl-6-(2-oxo-3,4-dihydro-1H-quinolin-6-yl)-3,4-dihydro-2H-pyridine-1-carboxylate (1 g, 2.92 mmol) was dissolved in a mixture of TFA (4.12 g, 36.10 mmol, 2.78 mL) and DCM (2 mL) and stirred at 24° C. for 0.5 hr. After completion of the reaction, the reaction mixture was evaporated in vacuo. The residue was dissolved in DCM (25 mL) and washed with water (3*5 mL). An organic layer was dried over Na₂SO₄ and evaporated in vacuo to afford 6-(3-methyl-2,3,4,5-tetrahydropyridin-6-yl)-3,4-dihydro-1H-quinolin-2-one (0.67 g, crude).

LCMS(ESI): [M+H]⁺ m/z: calcd 242.2; found 243.2; Rt=0.751 min.

Step 3: The Synthesis of 6-(5-methyl-2-piperidyl)-3,4-dihydro-1H-quinolin-2-one 6-(3-methyl-2,3,4,5-tetrahydropyridin-6-yl)-3,4-dihydro-1H-quinolin-2-one (0.7 g, 2.89 mmol) was dissolved in methanol (8 mL) and sodium borohydride (131.14 mg, 3.47 mmol, 122.56 µL) was added in one portion with stirring. After 12 hr, the reaction mixture was evaporated. A residue was dissolved in HCl/dioxane solution and evaporated to afford 6-(5-methyl-2-piperidyl)-3,4-dihydro-1H-quinolin-2-one (0.9 g, crude, HCl) which was used in the next step without purification.

LCMS(ESI): [M+H]+ m/z: calcd 230.2; found 231.2; Rt=0.730 min.

6Q. The 5-(5-methylpiperidin-2-yl)pyridin-2-amine

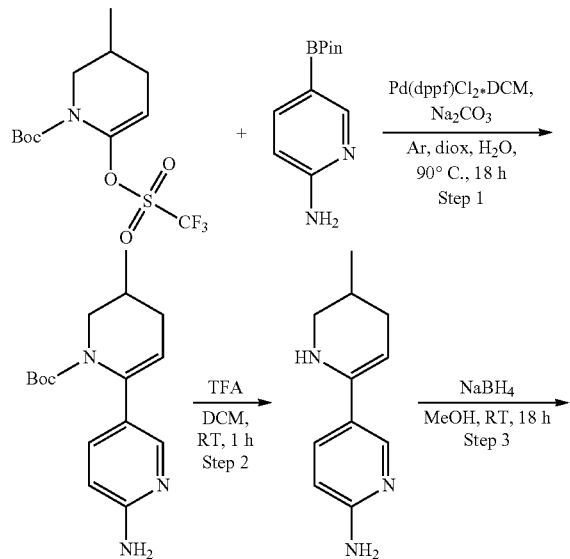

Step 1: The Synthesis of tert-butyl 6-(6-amino-3-pyridyl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (4 g, 11.58 mmol), 5-(4,4,5,5-tetramethyl-1,3,2-dioxaborolan-2-yl)pyridin-2-amine (2.55 g, 11.58 mmol) and sodium carbonate (2.46 g, 23.17 mmol, 970.50 µL) were mixed together in a mixture of Dioxane (48 mL) and Water (16 mL). The resulting mixture was evacuated and backfilled three times with argon and [1,1'-Bis(diphenylphosphino)ferrocene]dichloropalladium (II), complex with dichloromethane (945.91 mg, 1.16 mmol) was added thereto. The reaction mixture was heated at 90° C. for 18 hr. The reaction mixture was cooled to room temperature and diluted with water (100 mL). The resulting mixture was extracted with EtOAc (3*150 mL) and combined organic layers were washed with brine, dried over Na$_2$SO$_4$, filtered and evaporated. The residue was purified by column chromatography (SiO$_2$, Hexane-MTBE-MeOH as a mobile phase) to obtain tert-butyl 6-(6-amino-3-pyridyl)-3-methyl-3,4-dihydro-2H-pyridine-1-carboxylate (1.98 g, 6.83 mmol, 58.95% yield).

$^1$H NMR (500 MHz, CDCl$_3$) δ 1.02 (d, 3H), 1.18 (s, 9H), 1.81 (m, 1H), 1.86 (m, 1H), 2.36 (m, 1H), 2.97 (t, 1H), 4.07 (m, 1H), 4.47 (m, 2H), 5.21 (s, 1H), 6.46 (d, 1H), 7.37 (d, 1H), 8.02 (s, 1H).

LCMS(ESI): [M+H]+ m/z: calcd 289.2; found 290.2; Rt=0.957 min.

Step 2: The Synthesis of 5-(3-methyl-2,3,4,5-tetrahydropyridin-6-yl)pyridin-2-amine tert-butyl 6-(6-amino-3-pyridyl)-3-methyl-3,4-dihydro-2H-pyridine-1-carboxylate (1.98 g, 6.84 mmol) was dissolved in DCM (10 mL) and CF$_3$COOH (10 mL) was added. The resulting mixture was stirred for 1 hr. The reaction mixture was carefully poured into an aqueous solution of K$_2$CO$_3$ (20 g) and the resulting mixture was extracted with DCM (2*50 mL). Combined organic layers were dried over Na$_2$SO$_4$, filtered off and evaporated to obtain 5-(3-methyl-2,3,4,5-tetrahydropyridin-6-yl)pyridin-2-amine (1.28 g, 6.75 mmol, 98.69% yield).

$^1$H NMR (500 MHz, CDCl$_3$) δ 1.00 (d, 3H), 1.37 (m, 1H), 1.71 (m, 1H), 1.92 (m, 1H), 2.55 (m, 1H), 2.72 (m, 1H), 3.22 (m, 1H), 3.93 (m, 1H), 4.60 (s, 2H), 6.49 (d, 1H), 7.98 (d, 1H), 8.44 (s, 1H).

LCMS(ESI): [M+H]+ m/z: calcd 189.2; found 190.2; Rt=0.669 min.

Step 3: The Synthesis of 5-(5-methylpiperidin-2-yl)pyridin-2-amine 5-(3-methyl-2,3,4,5-tetrahydropyridin-6-yl)pyridin-2-amine (1.28 g, 6.76 mmol) was dissolved in MeOH (25 mL) and Sodium Borohydride (767.62 mg, 20.29 mmol, 717.40 µL) was added portionwise. The resulting mixture was stirred for 18 hr. The reaction mixture was concentrated under reduced pressure and water (20 mL) was added. The resulting slurry was extracted with DCM (2*50 mL). The combined organic layers were dried over Na$_2$SO$_4$, filtered off and evaporated to obtain C$_{11}$H$_{17}$N$_3$ (1.23 g, 6.43 mmol, 95.08% yield).

$^1$H NMR (400 MHz, CDCl$_3$) δ 0.86 (d, 3H), 1.09 (m, 1H), 1.61 (m, 5H), 2.36 (t, 1H), 3.07 (m, 1H), 3.40 (m, 1H), 4.33 (s, 2H), 6.46 (d, 1H), 7.44 (d, 1H), 7.99 (s, 1H).

LCMS(ESI): [M+H]+ m/z: calcd 191.2; found 192.2; Rt=0.299 min.

6R. The Synthesis of N-methyl-5-(5-methyl-2-piperidyl)pyridin-2-amine

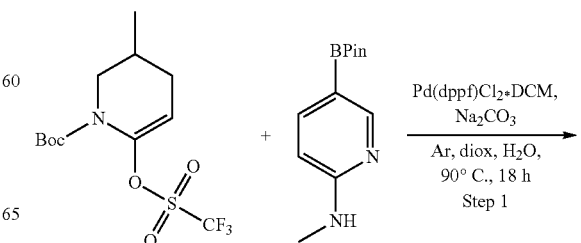

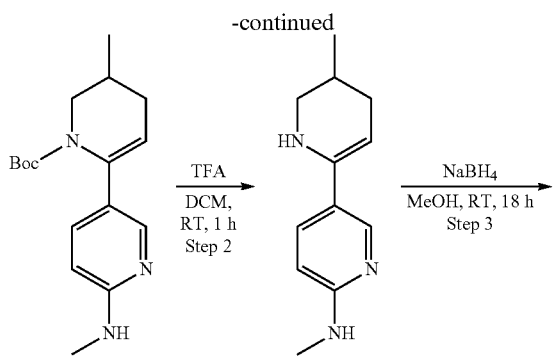

Step 1: The Synthesis of tert-butyl 3-methyl-6-[6-(methylamino)-3-pyridyl]-3,4-dihydro-2H-pyridine-1-carboxylate tert-butyl 3-methyl-6-(trifluoromethylsulfonyloxy)-3,4-dihydro-2H-pyridine-1-carboxylate (1.95 g, 5.64 mmol), N-methyl-5-(4,4,5,5-tetramethyl-1,3,2-dioxaborolan-2-yl)pyridin-2-amine (1.68 g, 6.21 mmol, HCl) and sodium carbonate (1.79 g, 16.93 mmol, 709.44 µL) were mixed together in a mixture of Dioxane (24 mL) and Water (8 mL). The resulting mixture was evacuated and backfilled three times with argon and [1,1'-Bis(diphenylphosphino)ferrocene]dichloropalladium(II), complex with dichloromethane (460.97 mg, 564.48 µmol) was added thereto. The reaction mixture was heated at 90° C. for 18 hr.

The reaction mixture was cooled to room temperature and diluted with water (50 mL). The resulting mixture was extracted with EtOAc (3*100 mL) and combined organic layers were washed with brine, dried over Na$_2$SO$_4$, filtered and evaporated. The residue was purified by column chromatography (SiO$_2$, Hexane-MTBE as a mobile phase) to obtain tert-butyl 3-methyl-6-[6-(methylamino)-3-pyridyl]-3,4-dihydro-2H-pyridine-1-carboxylate (1.28 g, 4.22 mmol, 74.68% yield).

$^1$H NMR (500 MHz, CDCl$_3$) δ 1.02 (d, 3H), 1.18 (s, 9H), 1.82 (m, 1H), 2.01 (m, 1H), 2.37 (m, 1H), 2.93 (d, 3H), 2.97 (m, 1H), 4.07 (m, 1H), 4.62 (m, 1H), 5.20 (m, 1H), 6.37 (d, 1H), 7.41 (d, 1H), 8.05 (s, 1H).

LCMS(ESI): [M+H]$^+$ m/z: calcd 303.2; found 304.2; Rt=0.988 min.

Step 2: The Synthesis of N-methyl-5-(3-methyl-2,3,4,5-tetrahydropyridin-6-yl)pyridin-2-amine tert-butyl 3-methyl-6-[6-(methylamino)-3-pyridyl]-3,4-dihydro-2H-pyridine-1-carboxylate (1.28 g, 4.22 mmol) was dissolved in DCM (6.5 mL) and CF$_3$COOH (6.5 mL) was added. The resulting mixture was stirred for 1 hr. The reaction mixture was poured into an aqueous solution of K$_2$CO$_3$ (12 g) and the resulting mixture was extracted with DCM (2*50 mL). The combined organic layers were dried over Na$_2$SO$_4$, filtered off and evaporated to obtain N-methyl-5-(3-methyl-2,3,4,5-tetrahydropyridin-6-yl)pyridin-2-amine (0.883 g, crude).

$^1$H NMR (500 MHz, CDCl$_3$) δ 0.99 (d, 3H), 1.38 (m, 1H), 1.72 (m, 1H), 1.92 (m, 2H), 2.53 (m, 1H), 2.73 (m, 1H), 2.97 (d, 3H), 3.21 (m, 1H), 4.76 (m, 1H), 6.39 (d, 1H), 8.00 (d, 1H), 8.46 (s, 1H).

LCMS(ESI): [M+H]$^+$ m/z: calcd 203.2; found 204.2; Rt=0.785 min.

Step 3: The Synthesis of N-methyl-5-(5-methyl-2-piperidyl)pyridin-2-amine

N-methyl-5-(3-methyl-2,3,4,5-tetrahydropyridin-6-yl)pyridin-2-amine (0.883 g, 4.34 mmol) was dissolved in MeOH (15 mL) and sodium borohydride (493.00 mg, 13.03 mmol, 460.75 µL) was added portionwise. The resulting mixture was stirred for 18 hr. The reaction mixture was concentrated under reduced pressure and water (10 mL) was added to the residue. The resulting slurry was extracted with DCM (2*40 mL) and combined organic layers were dried over Na$_2$SO$_4$, filtered and evaporated to obtain N-methyl-5-(5-methyl-2-piperidyl)pyridin-2-amine (0.957 g, crude).

$^1$H NMR (400 MHz, CDCl$_3$) δ 0.86 (d, 3H), 1.10 (m, 1H), 1.62 (m, 4H), 2.38 (m, 1H), 2.88 (m, 4H), 3.07 (m, 1H), 3.39 (m, 1H), 4.44 (m, 1H), 6.33 (d, 1H), 7.49 (d, 1H), 8.00 (s, 1H).

LCMS(ESI): [M+H]$^+$ m/z: calcd 205.2; found 206.2; Rt=0.448 min.

6S. The Synthesis of (2S,5R)-2-(Benzothiophen-5-yl)-5-methyl-piperidine

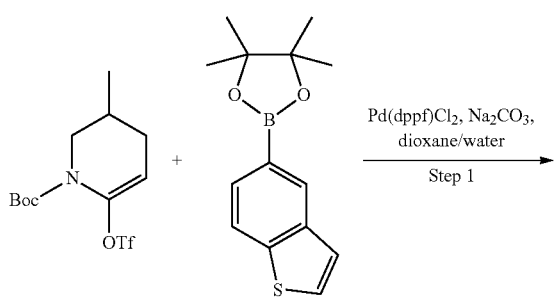

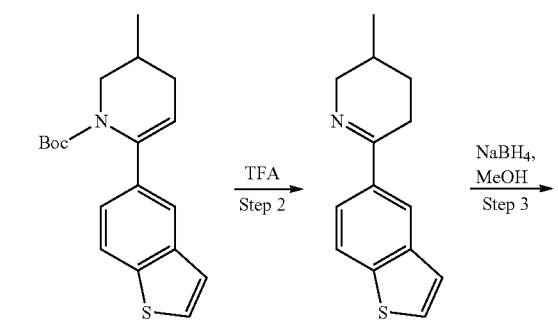

-continued

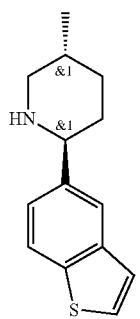

Step 1: Synthesis of tert-butyl 6-(Benzothiophen-5-yl)-3-methyl-3,4-dihydro-2H-pyridine-1-carboxylate A suspension of 2-(benzothiophen-5-yl)-4,4,5,5-tetramethyl-1,3,2-dioxaborolane (5.3 g, 20.37 mmol), tert-butyl 3-methyl-6-(trifluoromethylsulfonyloxy)-3,4-dihydro-2H-pyridine-1-carboxylate (7.74 g, 22.41 mmol), and Sodium carbonate (6.48 g, 61.12 mmol, 2.56 mL) in Dioxane (60 mL) and Water (20 mL) was degassed and refilled with Ar three time. To this solution, [1,1'-Bis(diphenylphosphino)ferrocene]dichloropalladium(II), complex with dichloromethane (831.83 mg, 1.02 mmol) was added. The resulting mixture was degassed, refilled with Ar and stirred at 65° C. for 12 hr. The precipitate was filtered off, washed with dioxane (50 ml). The solvent was evaporated in vacuo and residue was teken up with water 150 ml and extracted with EtOAc (2*100 ml). The combined organic layer was washed with brine (100 ml), dried over $Na_2SO_4$ and evaporated to obtain crude product (7.5 g). The crude product was purified by gradient chromatography (Hexane-MTBE) to obtain tert-butyl 6-(benzothiophen-5-yl)-3-methyl-3,4-dihydro-2H-pyridine-1-carboxylate (4.1 g, 12.44 mmol, 61.09% yield).

$^1$H NMR (CDCl$_3$, 400 MHz): δ 0.885 (s, 9H), 0.929 (m, 3H), 1.838 (m, 2H), 2.33 (m, 1H), 3.00 (m, 1H), 3.86 (d, 1H), 5.34 (m, 1H), 7.21 (m, 1H), 7.38 (m, 1H), 7.68 (m, 2H), 7.88 (m, 1H).

LCMS(ESI): [M-Boc+1]$^+$ m/z: calcd 329.2; found 231.0; Rt=1.774 min.

Step 2: Synthesis of 6-(benzothiophen-5-yl)-3-methyl-2,3,4,5-tetrahydropyridine tert-butyl 6-(benzothiophen-5-yl)-3-methyl-3,4-dihydro-2H-pyridine-1-carboxylate (4.1 g, 12.44 mmol) was dissolved in Trifluoroacetic acid (29.60 g, 259.60 mmol, 20 mL). The resulting mixture was stirred at 25° C. for 1 hr (to the end of gas evolution). The pH of the solution was adjusted to 8 with 10% NaOH solution and extracted with DCM (3*70 ml). The combined organic layer was washed with brine (50 ml), dried over $Na_2SO_4$ and evaporated in vacuo to obtain 6-(benzothiophen-5-yl)-3-methyl-2,3,4,5-tetrahydropyridine (2.5 g, 10.90 mmol, 87.59% yield).

$^1$H NMR (CDCl$_3$, 500 MHz): δ 1.03 (d, 3H), 1.44 (m, 1H), 1.75 (m, 1H), 1.96 (m, 1H), 2.67 (m, 1H), 2.88 (dd, 1H), 3.29 (dd, 1H), 4.03 (d, 1H), 7.36 (d, 1H)m 7.45 (d, 1H), 7.86 (m, 2H), 8.21 (s, 1H).

LCMS(ESI): [M+1]$^+$ m/z: calcd 229.2; found 230.0; Rt=0.923 min.

Step 3: Synthesis of (2S,5R)-2-(benzothiophen-5-yl)-5-methyl-piperidine

To a solution of 6-(benzothiophen-5-yl)-3-methyl-2,3,4,5-tetrahydropyridine (2.5 g, 10.90 mmol) in MeOH (50 mL), Sodium Borohydride (824.81 mg, 21.80 mmol, 770.85 µL) was added portionwise at 0° C. The resulting mixture was stirred at 25° C. for 2 hr and the solvent was evaporated in vacuo, the residue was taken up with water (30 ml) and extracted with DCM (3*30 ml). The combined organic extract was washed with brine (2*50 ml), dried over $Na_2SO_4$ and evaporated to give rac (2S,5R)-2-(benzothiophen-5-yl)-5-methyl-piperidine (2.1 g, 9.08 mmol, 83.27% yield).

$^1$H NMR (DMSO, 400 MHz): δ 0.82 (d, 3H), 1.07 (m, 1H), 1.36 (dd, 1H), 1.51 (m, 1H), 1.68-1.72 (m, 2H), 2.25 (dd, 1H), 2.97 (d, 1H), 3.25 (brs, 1H), 3.54 (d, 1H), 7.33-7.37 (m, 2H), 7.66 (d, 1H), 7.81-7.85 (m, 2H).

LCMS(ESI): [M+1]$^+$ m/z: calcd 231.1; found 232.0; Rt=0.790 min.

6T. The Synthesis of 2-methyl-5-(5-methylpiperidin-2-yl)benzo[d]thiazole

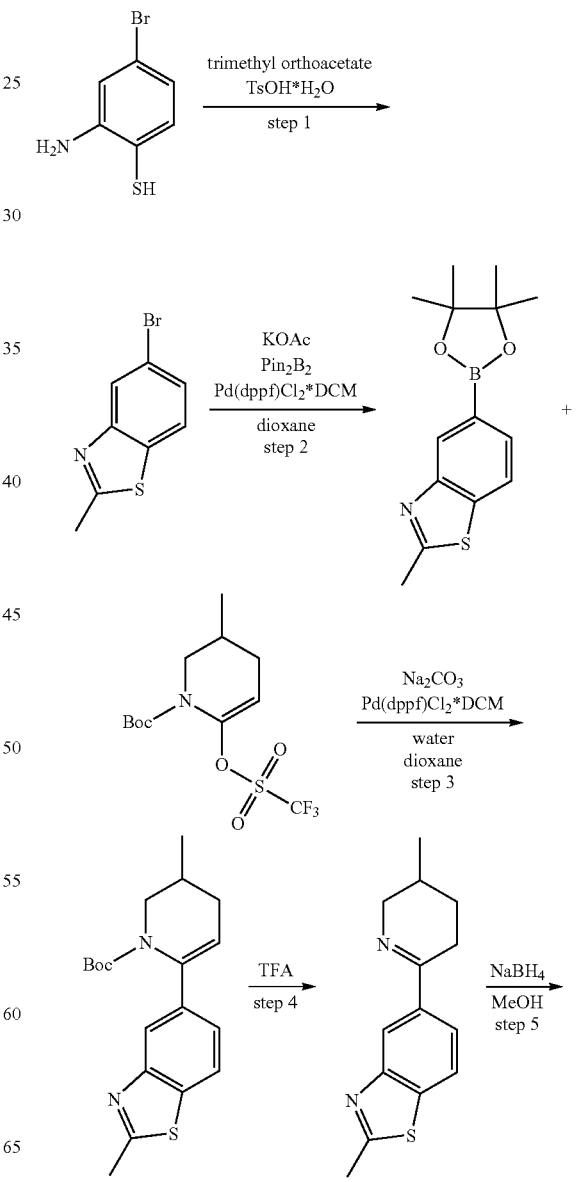

-continued

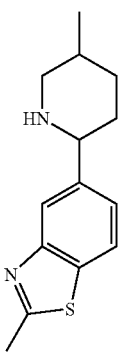

Step 1: Synthesis of 5-bromo-2-methylbenzo[d]thiazole 2-amino-4-bromo-benzenethiol (19 g, 93.10 mmol) and 4-methylbenzenesulfonic acid; hydrate (106.25 mg, 558.58 μmol, 85.69 μL) were dissolved in trimethyl orthoacetate (38.03 g, 316.53 mmol, 3.49 mL). The resulting solution was stirred at 100° C. for an additional 6 hr. Then the mixture was concentrated directly to afford the desired product 5-bromo-2-methyl-1,3-benzothiazole (20 g, 87.68 mmol, 94.18% yield).

$^1$H NMR (500 MHz, DMSO-$d_6$) δ (ppm) 2.79 (s, 3H), 7.55 (d, 1H), 8.00 (d, 1H), 8.11 (s, 1H).

LCMS(ESI): [M]$^+$ m/z: calcd 228.2; found 229.2; Rt=1.267 min.

Step 2: Synthesis of 2-methyl-5-(4,4,5,5-tetramethyl-1,3,2-dioxaborolan-2-yl)benzo[d]thiazole Potassium acetate (18.93 g, 192.89 mmol, 12.06 mL) was added to a solution of 5-bromo-2-methyl-1,3-benzothiazole (22 g, 96.45 mmol) and 4,4,5,5-tetramethyl-2-(4,4,5,5-tetramethyl-1,3,2-dioxaborolan-2-yl)-1,3,2-dioxaborolane (28.16 g, 110.91 mmol) in DMSO (200 mL). Reaction flask was evacuated and refilled with argon 3 times. Then PddppfCl$_2$*DCM (3.94 g, 4.82 mmol) was added under stream of argon. Resulting mixture was stirred at 90° C. for 28 hr under inert atmosphere. Then, it was cooled, diluted with EA (400 mL) and washed with water (2×200 mL). Organic layer was dried over Na$_2$SO$_4$ and concentrated under reduced pressure. The residue was purified by silica gel flash chromatography eluting with a 0 to 100 percent hexane-EA gradient to give 2-methyl-5-(4,4,5,5-tetramethyl-1,3,2-dioxaborolan-2-yl)-1,3-benzothiazole (22 g, 79.95 mmol, 82.90% yield).

$^1$H NMR (400 MHz, CDCl$_3$) δ (ppm) 1.35 (s, 12H), 2.81 (s, 3H), 7.78 (m, 2H), 8.36 (s, 1H).

LCMS(ESI): [M]$^+$ m/z: calcd 275.2; found 276.2; Rt=1.531 min.

Step 3: Synthesis of tert-butyl 3-methyl-6-(2-methylbenzo[d]thiazol-5-yl)-3,4-dihydropyridine-1(2H)-carboxylate A mixture of tert-butyl 3-methyl-6-(trifluoromethylsulfonyloxy)-3,4-dihydro-2H-pyridine-1-carboxylate (16.73 g, 48.45 mmol), 2-methyl-5-(4,4,5,5-tetramethyl-1,3,2-dioxaborolan-2-yl)-1,3-benzothiazole (16 g, 58.15 mmol), [1,1'-bis(diphenylphosphino)ferrocene]dichloropalladium(II), complex with DCM (1.98 g, 2.42 mmol) and sodium carbonate (15.41 g, 145.36 mmol, 6.09 mL) in dioxane (300 mL) and water (100 mL) was stirred at 80° C. under argon atmosphere for 18 hr. After cooling to rt, the reaction mixture was filtered off. The filter cake was washed with dioxane (500 mL) and discarded. Filtrate was concentrated under reduced pressure and the residue was purified by silica gel flash chromatography eluting with a 0 to 100 percent MTBE-Hexane gradient to give tert-butyl 3-methyl-6-(2-methyl-1,3-benzothiazol-5-yl)-3,4-dihydro-2H-pyridine-1-carboxylate (12 g, 34.84 mmol, 71.89% yield).

$^1$H NMR (400 MHz, CDCl$_3$) δ (ppm) 1.01 (s, 12H), 1.85 (m, 1H), 2.02 (m, 1H), 2.43 (m, 1H), 2.80 (s, 3H), 3.01 (t, 1H), 4.10 (d, 1H), 5.36 (m, 1H), 7.29 (d, 1H), 7.69 (d, 1H), 7.86 (s, 1H).

LCMS(ESI): [M]$^+$ m/z: calcd 344.2; found 345.2; Rt=1.654 min.

Step 4: Synthesis of 2-methyl-5-(5-methyl-3,4,5,6-tetrahydropyridin-2-yl)benzo[d]thiazole The solution of tert-butyl 3-methyl-6-(2-methyl-1,3-benzothiazol-5-yl)-3,4-dihydro-2H-pyridine-1-carboxylate (12.51 g, 36.31 mmol) in TFA (66.25 g, 581.04 mmol, 44.76 mL) was stirred at 20° C. for 1 hr, and then evaporated in vacuo. Crushed ice (50 g) was added to the residue and pH was adjusted to 8 with a 10% aqueous solution of sodium hydroxide. The resulting mixture was extracted with ethylacetate (2*100 mL). The combined organic extracts were dried over sodium sulphate and evaporated in vacuo to afford 2-methyl-5-(3-methyl-2,3,4,5-tetrahydropyridin-6-yl)-1,3-benzothiazole (8.8 g, 36.01 mmol, 99.17% yield) as yellow solid, which was used directly in the next step.

$^1$H NMR (500 MHz, DMSO-$d_6$) δ (ppm) 0.92 (d, 3H), 1.33 (m, 1H), 1.63 (m, 1H), 1.86 (m, 1H), 2.48 (m, 1H), 2.81 (s, 3H), 3.19 (m, 1H), 3.92 (m, 1H), 7.88 (d, 1H), 7.97 (d, 1H), 8.23 (s, 1H).

LCMS(ESI): [M]$^+$ m/z: calcd 244.2; found 245.2; Rt=0.871 min.

Step 5: Synthesis of 2-methyl-5-(5-methylpiperidin-2-yl)benzo[d]thiazole

Sodium borohydride (2.04 g, 54.02 mmol, 1.91 mL) was added in one portion to a stirred solution of 2-methyl-5-(3-methyl-2,3,4,5-tetrahydropyridin-6-yl)-1,3-benzothiazole (8.8 g, 36.01 mmol) in MeOH (200 mL) at 0° C. The resulting mixture was stirred at 0° C. for 1 hr, and then evaporated in vacuo. The residue was diluted with water (150 mL) and extracted with dichloromethane (2*150 mL). The combined organic extracts were dried over sodium sulphate and evaporated in vacuo to afford 2-methyl-5-(5-methyl-2-piperidyl)-1,3-benzothiazole (8 g, 32.47 mmol, 90.17% yield) as yellow solid, which was used directly in the next step.

$^1$H NMR (500 MHz, DMSO-$d_6$) δ (ppm) 0.83 (d, 3H), 1.34 (m, 1H), 1.36 (m, 1H), 1.52 (m, 1H), 1.75 (m, 2H), 2.26 (m, 1H), 2.38 (m, 1H), 2.75 (s, 3H), 3.01 (m, 1H), 3.55 (m, 1H), 7.38 (d, 1H), 7.83 (s, 1H), 7.89 (d, 1H).

LCMS(ESI): [M]$^+$ m/z: calcd 246.2; found 247.2; Rt=0.696 min.

6U. The Synthesis of 2-(3,4-difluorophenyl)-5-methylpiperidine

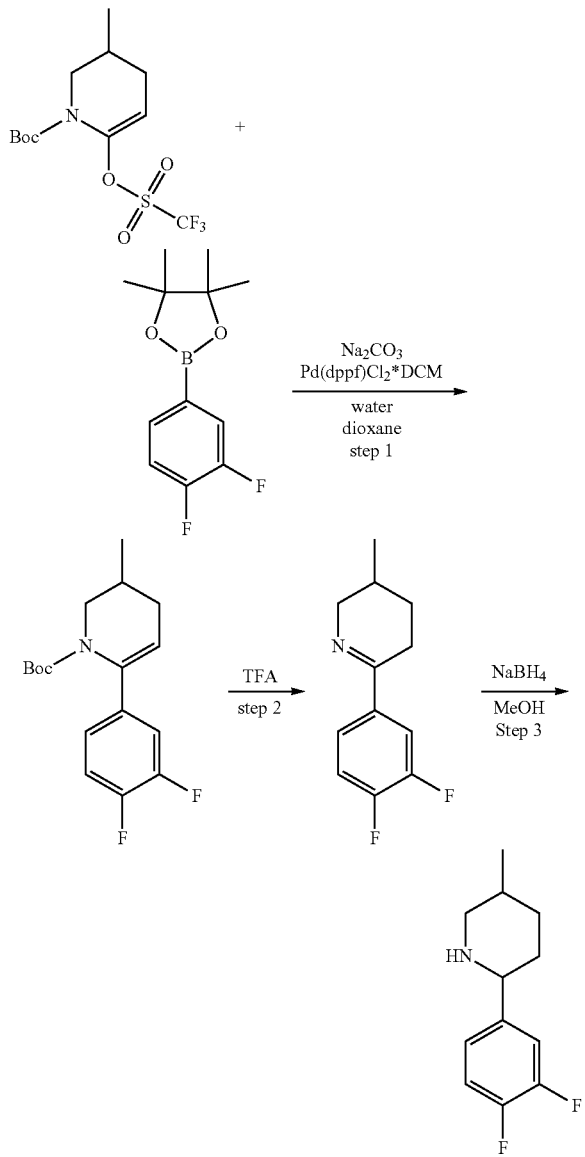

Step 1: Synthesis of tert-butyl 6-(3,4-difluorophenyl)-3-methyl-3,4-dihydropyridine-1(2H)-carboxylate tert-butyl 3-methyl-6-(trifluoromethylsulfonyloxy)-3,4-dihydro-2H-pyridine-1-carboxylate (5 g, 14.48 mmol), (3,4-difluorophenyl)boronic acid (2.29 g, 14.48 mmol) and sodium carbonate (4.60 g, 43.44 mmol, 1.82 mL) were added to a mixture of dioxane (45 mL) and water (15 mL). The resulting mixture was evacuated and then backfilled with argon, this operation was repeated three times, then Pd(dppf)$_2$Cl$_2$*DCM (723.93 μmol) was added under argon. The reaction mixture was stirred under argon at 70° C. for 14 hr, then cooled and filtered. The filtercake was washed with 1,4-dioxane (2*20 ml) and discarded. The filtrate was evaporated in vacuo to afford tert-butyl 6-(3,4-difluorophenyl)-3-methyl-3,4-dihydro-2H-pyridine-1-carboxylate (4 g, 12.93 mmol, 89.31% yield) as brown oil, which was used in next step without purification.

$^1$H NMR (400 MHz, CDCl$_3$) δ(ppm)

LCMS(ESI): [M-Boc]$^+$ m/z: calcd 209.2; found 210.2; Rt=0.683 min.

Step 2: Synthesis of 6-(3,4-difluorophenyl)-3-methyl-2,3,4,5-tetrahydropyridine The solution of tert-butyl 6-(3,4-difluorophenyl)-3-methyl-3,4-dihydro-2H-pyridine-1-carboxylate (4 g, 12.93 mmol) in trifluoroacetic acid (29.49 g, 258.61 mmol, 19.92 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with DCM (2*30 ml). The combined organic extracts were dried over sodium sulphate and evaporated in vacuo to afford 6-(3,4-difluorophenyl)-3-methyl-2,3,4,5-tetrahydropyridine (2 g, 9.56 mmol, 73.92% yield) as brown solid, which was used directly in the next step.

$^1$H NMR (400 MHz, DMSO-d$_6$) δ(ppm) LCMS(ESI): [M]$^+$ m/z: calcd 209.2; found 210.2; Rt=0.671 min.

Step 3: Synthesis of 2-(3,4-difluorophenyl)-5-methylpiperidine

Sodium borohydride (723.26 mg, 19.12 mmol, 675.94 μL) was added in one portion to a stirred solution of 6-(3,4-difluorophenyl)-3-methyl-2,3,4,5-tetrahydropyridine (2 g, 9.56 mmol) in MeOH (50 mL) at 0° C. The resulting mixture was stirred at 0° C. for 1 hr, and then evaporated in vacuo. The residue was diluted with water (20 ml) and extracted with DCM (2*40 ml). The combined organic extracts were dried over sodium sulphate and evaporated in vacuo. The obtained oil was subjected to CC to afford 2-(3,4-difluorophenyl)-5-methyl-piperidine (0.528 g, 2.50 mmol, 26.15% yield).

$^1$H NMR (400 MHz, DMSO-d$_6$) δ (ppm) 0.86 (d, 3H), 1.24 (m, 1H), 1.86 (m, 3H), 2.08 (m, 1H), 2.48 (m, 1H), 2.58 (m, 1H), 3.18 (m, 1H), 7.48 (m, 2H), 7.84 (s, 1H), 9.61 (m, 1H).

LCMS(ESI): [M]$^+$ m/z: calcd 211.2; found 212.2; Rt=0.969 min.

6V. Synthesis of 5-methyl-2-(3,4,5-trifluorophenyl)piperidine

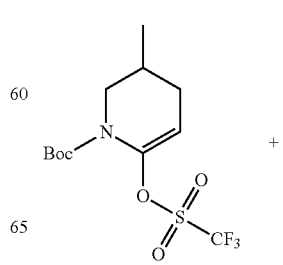

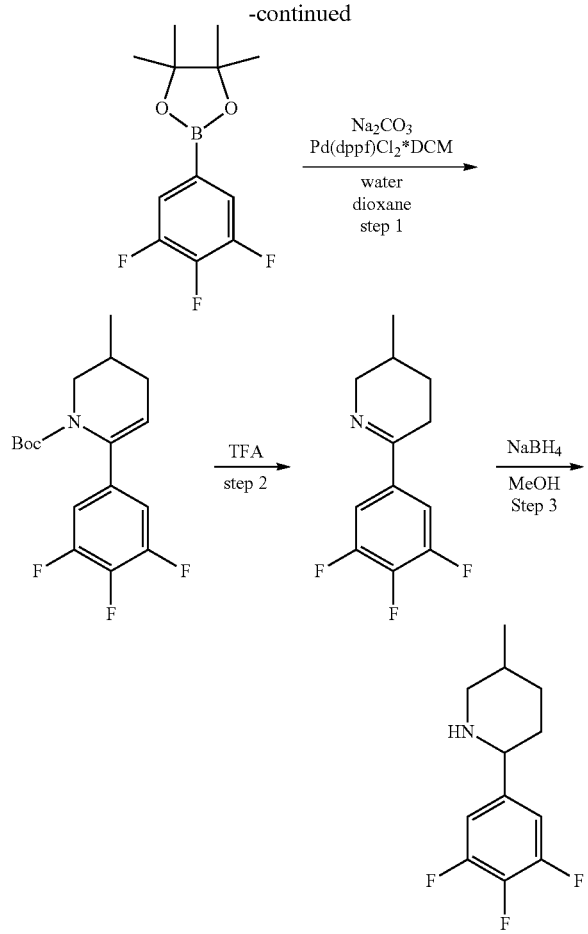

Step 1: Synthesis of tert-butyl 3-methyl-6-(3,4,5-trifluorophenyl)-3,4-dihydropyridine-1(2H)-carboxylate tert-butyl 3-methyl-6-(trifluoromethylsulfonyloxy)-3,4-dihydro-2H-pyridine-1-carboxylate (5 g, 14.48 mmol), (3,4,5-trifluorophenyl)boronic acid (2.55 g, 14.48 mmol) and sodium carbonate (4.60 g, 43.44 mmol, 1.82 mL) were added to a mixture of dioxane (45 mL) and water (15 mL). The resulting mixture was evacuated and then backfilled with argon, this operation was repeated three times, then Pd(dppf)$_2$Cl$_2$*DCM (723.94 μmol) was added under argon. The reaction mixture was stirred under argon at 70° C. for 12 hr, then cooled and filtered. The filtercake was washed with 1,4-dioxane (2*20 ml) and discarded. The filtrate was evaporated in vacuo to afford tert-butyl 3-methyl-6-(3,4,5-trifluorophenyl)-3,4-dihydro-2H-pyridine-1-carboxylate (4.5 g, 13.75 mmol, 94.95% yield) as brown oil, which was used in next step without purification.

LCMS(ESI): [M-Boc]$^+$ m/z: calcd 227.2; found 228.2; Rt=1.586 min.

Step 2: Synthesis of 3-methyl-6-(3,4,5-trifluorophenyl)-2,3,4,5-tetrahydropyridine The solution of tert-butyl 3-methyl-6-(3,4,5-trifluorophenyl)-3,4-dihydro-2H-pyridine-1-carboxylate (4.5 g, 13.75 mmol) in trifluoroacetic acid (31.35 g, 274.94 mmol, 21.18 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with DCM (2*30 ml). The combined organic extracts were dried over sodium sulphate and evaporated in vacuo to afford 3-methyl-6-(3,4,5-trifluorophenyl)-2,3,4,5-tetrahydropyridine (2.5 g, 11.00 mmol, 80.03% yield) as brown solid, which was used directly in the next step.

$^1$H NMR (400 MHz, DMSO-d$_6$) δ(ppm) LCMS(ESI): [M]$^+$ m/z: calcd 227.2; found 228.2; Rt=0.887 min.

Step 3: Synthesis of 5-methyl-2-(3,4,5-trifluorophenyl)piperidine

Sodium borohydride (832.49 mg, 22.00 mmol, 778.03 μL) was added in one portion to a stirred solution of 3-methyl-6-(3,4,5-trifluorophenyl)-2,3,4,5-tetrahydropyridine (2.5 g, 11.00 mmol) in MeOH (50 mL) at 0° C. The resulting mixture was stirred at 0° C. for 1 hr, and then evaporated in vacuo. The residue was diluted with water (20 ml) and extracted with dichloromethane (2*40 ml). The combined organic extracts were dried over sodium sulphate and evaporated in vacuo. The obtained oil was subjected to CC to afford 5-methyl-2-(3,4,5-trifluorophenyl)piperidine (0.45 g, 1.96 mmol, 17.84% yield).

$^1$H NMR (400 MHz, CDCl$_3$) δ (ppm) 0.86 (d, 3H), 1.12 (m, 1H), 1.28 (m, 1H), 1.46 (m, 1H), 1.63 (m, 1H), 1.82 (m, 2H), 2.36 (m, 1H), 3.18 (m, 1H), 3.48 (m, 1H), 7.02 (m, 2H).

LCMS(ESI): [M]$^-$ m/z: calcd 229.2; found 230.2; Rt=0.773 min.

6W. The Synthesis of 4-(5-methylpiperidin-2-yl)Cyclohexanol

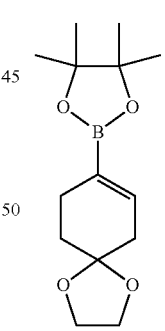

+

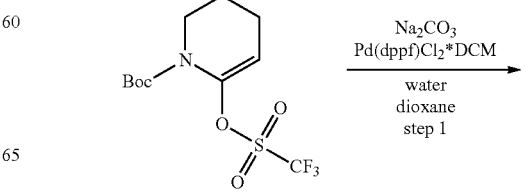

-continued

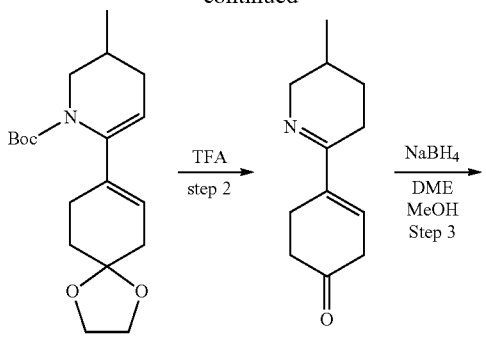

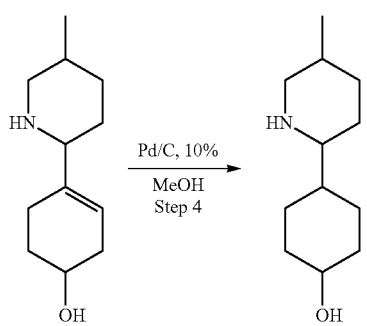

Step 1: Synthesis of tert-butyl 3-methyl-6-(1,4-dioxaspiro[4.5]dec-7-en-8-yl)-3,4-dihydropyridine-1(2H)-carboxylate tert-butyl 3-methyl-6-(trifluoromethylsulfonyloxy)-3,4-dihydro-2H-pyridine-1-carboxylate (7.22 g, 18.82 mmol), 2-(1,4-dioxaspiro[4.5]dec-7-en-8-yl)-4,4,5,5-tetramethyl-1,3,2-dioxaborolane (5.01 g, 18.82 mmol) and sodium carbonate (5.98 g, 56.45 mmol) were added to a mixture of dioxane (120 mL) and water (40 mL). The resulting mixture was evacuated and then backfilled with argon, this operation was repeated three times, then Pd(dppf)Cl$_2$ (688.40 mg, 940.83 μmol) was added under argon. The reaction mixture was stirred under argon at 90° C. for 16 hr, then cooled and filtered. The filtercake was washed with ethyl acetate (200 ml) and discarded. The filtrate was evaporated in vacuo, and the residue was purified by column chromatography on silica gel using hexane/MTBE gradient (0-100% MTBE) to afford tert-butyl 6-(1,4-dioxaspiro[4.5]dec-7-en-8-yl)-3-methyl-3,4-dihydro-2H-pyridine-1-carboxylate (2.00 g, 5.96 mmol, 31.69% yield) as light-yellow gum.

$^1$H NMR (500 MHz, CDCl$_3$) δ (ppm) 0.96 (d, 3H), 1.48 (s, 9H), 1.68 (m, 1H), 1.82 (m, 2H), 1.96 (m, 1H), 2.26 (m, 2H), 2.38 (m, 3H), 2.76 (m, 1H), 3.82 (m, 1H), 3.96 (d, 4H), 5.21 (m, 1H), 5.68 (m, 1H).

LCMS(ESI): [M-Boc]$^+$ m/z: calcd 235.2; found 236.2; Rt=1.392 min.

Step 2: Synthesis of 4-(5-methyl-3,4,5,6-tetrahydropyridin-2-yl)cyclohex-3-enone Trifluoroacetic acid (40.79 g, 357.74 mmol, 27.56 mL) was added to tert-butyl 6-(1,4-dioxaspiro[4.5]dec-7-en-8-yl)-3-methyl-3,4-dihydro-2H-pyridine-1-carboxylate (1.2 g, 3.58 mmol) at 25° C. The resulting reaction mixture was stirred at 25° C. for 18 hr, then evaporated in vacuo to afford crude 4-(3-methyl-2,3,4,5-tetrahydropyridin-6-yl)cyclohex-3-en-1-one (3 g, crude) as orange gum, which was used directly in the next step.

$^1$H NMR (500 MHz, CDCl$_3$) δ (ppm) 1.08 (d, 3H), 1.56 (m, 1H), 2.12 (m, 2H), 2.62 (m, 2H), 2.89 (m, 2H), 3.32 (m, 3H), 4.02 (m, 1H), 4.66 (m, 2H), 7.27 (m, 1H).

LCMS(ESI): [M]$^-$ m/z: calcd 191.2; found 192.2; Rt=1.648 min.

Step 3: Synthesis of 4-(5-methylpiperidin-2-yl)Cyclohex-3-Enol

Sodium borohydride (2.5 g, 66.09 mmol, 2.34 mL) was added portionwise over 0.2 hr to a stirred solution of 4-(3-methyl-2,3,4,5-tetrahydropyridin-6-yl)cyclohex-3-en-1-one (3 g, 15.68 mmol) in DME (100 mL). The reaction mixture was stirred at 0° C. for 2 hr, then MeOH (50 mL) was added at 0° C. slowly to quench the reaction (foaming!). The resulting mixture was allowed to warm to 25° C., stirred for 0.5 hr, and then evaporated in vacuo. The residue was diluted with water (50 ml) and pH was adjusted to 10 with 10% aqueous sodium hydroxide solution. The resulting cloudy solution was extracted with dichloromethane (2*70 ml). The combined organic extracts were dried over sodium sulphate and evaporated in vacuo to afford crude 4-(5-methyl-2-piperidyl)cyclohex-3-en-1-ol (0.65 g, 3.33 mmol, 21.22% yield) as light-yellow gum, which was used directly in the next step.

$^1$H NMR (400 MHz, CDCl$_3$) δ (ppm) 0.96 (d, 3H), 1.22 (m, 1H), 1.96 (m, 8H), 2.36 (m, 3H), 2.86 (m, 1H), 3.42 (m, 1H), 3.52 (m, 1H), 3.85 (m, 1H), 3.96 (m, 1H), 5.57 (m, 1H).

LCMS(ESI): [M]$^+$ m/z: calcd 195.2; found 196.2; Rt=0.598 min.

Step 4: Synthesis of 4-(5-methylpiperidin-2-yl)cyclohexanol

A mixture of 4-(5-methyl-2-piperidyl)cyclohex-3-en-1-ol (0.65 g, 3.33 mmol) and palladium, 10% on carbon (0.5 g, 3.33 mmol) in MeOH (40 mL) was stirred under atmosphere of hydrogen at 45° C. for 12 hr. The catalyst was filtered off, the filtrate was evaporated in vacuo to afford 4-(5-methyl-2-piperidyl)cyclohexanol (0.4 g, 2.03 mmol, 60.91% yield) as light-yellow gum, which was used directly in the next step.

$^1$H NMR (500 MHz, CDCl$_3$) δ (ppm) 0.86 (d, 3H), 1.12 (m, 2H), 1.36 (m, 2H), 1.54 (m, 5H), 1.86 (m, 4H), 2.08 (m, 2H), 2.28 (m, 2H), 3.12 (m, 1H), 3.55 (m, 1H), 4.02 (m, 1H).

LCMS(ESI): [M]$^+$ m/z: calcd 197.2; found 198.2; Rt=0.719 min.

6X. Synthesis of 5-(5-methyl-2-piperidyl)-1H-pyrazolo[3,4-b]pyridine

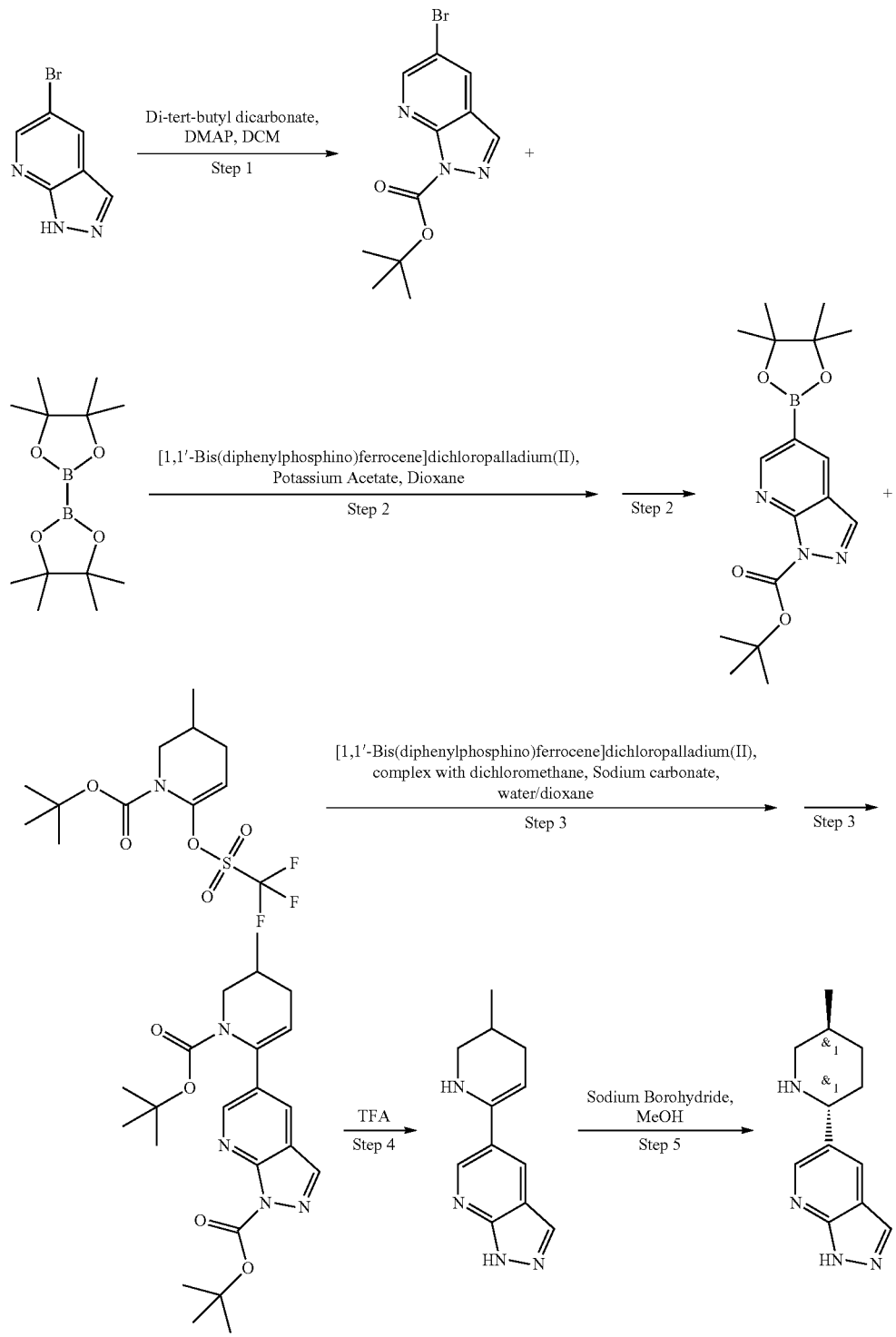

Step 1: Synthesis of tert-butyl 5-bromopyrazolo[3,4-b]pyridine-1-carboxylate

Di-tert-butyl dicarbonate (8.99 g, 41.21 mmol, 9.46 mL) was added dropwise to a stirred suspension of 5-bromo-1H-pyrazolo[3,4-b]pyridine (8 g, 40.40 mmol) and DMAP (49.36 mg, 404.00 μmol) in DCM (80 mL) at 0° C. The resulting mixture was stirred at room temperature for 12 hr, then evaporated in vacuo poured into water (100 ml) and extracted with DCM (2×50 ml). The combined organic extracts were washed with water (2*30 ml), dried over sodium sulphate and evaporated in vacuo to afford product tert-butyl 5-bromopyrazolo[3,4-b]pyridine-1-carboxylate (9.3 g, 31.19 mmol, 77.21% yield)

$^1$H NMR (CDCl$_3$, 500 MHz): 1.73 (s, 9H), 8.13 (s, 1H), 8.23 (s, 1H), 8.78 (s, 1H).

LCMS(ESI): [M-Boc+H]$^+$ m/z: calcd 298.1; found 200.0; Rt=1.243 min.

Step 2: Synthesis of tert-butyl 5-(4,4,5,5-tetramethyl-1,3,2-dioxaborolan-2-yl)pyrazolo[3,4-b]pyridine-1-carboxylate (P1) and 5-(4,4,5,5-tetramethyl-1,3,2-dioxaborolan-2-yl)-1H-pyrazolo[3,4-b]pyridine (P2)

tert-butyl 5-bromopyrazolo[3,4-b]pyridine-1-carboxylate (9.3 g, 31.19 mmol) and 4,4,5,5-tetramethyl-2-(4,4,5,5-tetramethyl-1,3,2-dioxaborolan-2-yl)-1,3,2-dioxaborolane (7.92 g, 31.19 mmol) were mixed together in Dioxane (100 mL). The resulting mixture was evacuated and then backfilled with argon, this operation was repeated three times, then [1,1'-Bis(diphenylphosphino)ferrocene]dichloropalladium(II) (1.14 g, 1.56 mmol) were added under argon. The reaction mixture was stirred under argon at 100° C. for 8 hr, then cooled and evaporated in vacuo poured into water (150 ml) and extracted with EtOAc (2×80 ml). The combined organic extracts were washed with water (2*40 ml), dried over sodium sulphate and evaporated in vacuo to leave 13 g of crude product, 13 g of which was purification by column chromatography on silica gel using hexane/MTBE gradient (10-100% MTBE) to afford tert-butyl 5-(4,4,5,5-tetramethyl-1,3,2-dioxaborolan-2-yl)pyrazolo[3,4-b]pyridine-1-carboxylate (2.5 g, 7.24 mmol, 23.22% yield) and 5-(4,4,5,5-tetramethyl-1,3,2-dioxaborolan-2-yl)-1H-pyrazolo[3,4-b]pyridine (2 g, 8.16 mmol, 26.16% yield) P1-1: $^1$H NMR (CDCl$_3$, 500 MHz): 1.36 (s, 12H), 1.73 (s, 9H), 8.15 (s, 1H), 8.51 (s, 1H), 9.07 (s, 1H).

LCMS(ESI): [M-Boc+H]$^+$ m/z: calcd 345.2; found 246.2; Rt=0.940 min.

P1-2: $^1$H NMR (CDCl$_3$, 500 MHz): 1.32 (s, 12H), 8.13 (s, 1H), 8.61 (s, 1H), 8.95 (s, 1H), NH is not observed.

LCMS(ESI): [M+H]$^+$ m/z: calcd 245.1; found 246.2; Rt=0.555 min.

Step 3: Synthesis of tert-butyl 5-(1-tert-butoxycarbonyl-3-methyl-3,4-dihydro-2H-pyridin-6-yl)pyrazolo[3,4-b]pyridine-1-carboxylate tert-butyl 5-(4,4,5,5-tetramethyl-1,3,2-dioxaborolan-2-yl)pyrazolo[3,4-b]pyridine-1-carboxylate (4 g, 11.59 mmol) and tert-butyl 3-methyl-6-(trifluoromethylsulfonyloxy)-3,4-dihydro-2H-pyridine-1-carboxylate (4.00 g, 11.59 mmol) were mixed together in water (8 mL). The resulting mixture was evacuated and then backfilled with argon, this operation was repeated three times, then Sodium carbonate (2.46 g, 23.17 mmol, 970.88 µL) in water (8 mL) and [1,1'-Bis(diphenylphosphino)ferrocene]dichloropalladium(II), complex with dichloromethane (473.14 mg, 579.37 µmol) were added under argon. The reaction mixture was stirred under argon at 80° C. for 12 hr, then cooled and evaporated in vacuo poured into water (120 ml) and extracted with EtOAc (2×60 ml). The combined organic extracts were washed with water (2*40 ml), dried over sodium sulphate and evaporated in vacuo to leave 3.6 g of crude product, 3.6 g of which was purification by column chromatography on silica gel using hexane/MTBE gradient (10-100% MTBE) to afford product tert-butyl 5-(1-tert-butoxycarbonyl-3-methyl-3,4-dihydro-2H-pyridin-6-yl)pyrazolo[3,4-b]pyridine-1-carboxylate (2.4 g, 5.79 mmol, 49.97% yield).

$^1$H NMR (DMSO, 400 MHz): 1.04 (s, 9H), 1.91 (m, 6H), 3.05 (m, 1H), 4.07 (m, 1H), 5.33 (m, 1H), 7.97 (s, 1H), 8.05 (s, 1H), 8.57 (s, 1H), 11.78 (s, 1H) (only one Boc-group is present in structure)

LCMS(ESI): [M-Boc+H]$^+$ m/z: calcd 414.5; found 315.2; Rt=1.367 min.

Step 4: Synthesis of 5-(3-methyl-1,2,3,4-tetrahydropyridin-6-yl)-1H-pyrazolo[3,4-b]pyridine The solution of tert-butyl 3-methyl-6-(1H-pyrazolo[3,4-b]pyridin-5-yl)-3,4-dihydro-2H-pyridine-1-carboxylate (2.4 g, 7.63 mmol) in TFA (26.11 g, 229.02 mmol, 17.64 mL) was stirred at 0° C. for 1 hr, and then evaporated in vacuo. Crushed ice (20 g) was added to the residue and pH was adjusted to 8 with a 10% aqueous solution of sodium hydrocarbonate. The resulting mixture was extracted with ethylacetate (2*40 mL). The combined organic extracts were dried over sodium sulphate and evaporated in vacuo to afford 5-(3-methyl-1,2,3,4-tetrahydropyridin-6-yl)-1H-pyrazolo[3,4-b]pyridine (1.3 g, 6.07 mmol, 79.48% yield) as yellow solid, which was used directly in the next step.

$^1$H NMR (500 MHz, CDCl$_3$) 1.03 (d, 3H), 1.46 (m, 1H), 1.61 (m, 1H), 1.77 (m, 1H), 2.82 (m, 1H), 2.86 (m, 1H), 3.32 (m, 1H), 4.07 (m, 1H), 8.08 (s, 1H), 8.47 (s, 1H), 9.11 (s, 1H), 11.35 (m, 1H).

LCMS(ESI): [M+H]$^+$ m/z: calcd 214.27; found 215.2; Rt=0.722 min.

Step 5: Synthesis of 5-(5-methyl-2-piperidyl)-1H-pyrazolo[3,4-b]pyridine

Sodium Borohydride (344.31 mg, 9.10 mmol, 321.78 µL) was added in one portion to a stirred solution of 5-(3-methyl-1,2,3,4-tetrahydropyridin-6-yl)-1H-pyrazolo[3,4-b]pyridine (1.3 g, 6.07 mmol) in MeOH (25 mL) at 0° C. The resulting mixture was stirred at 0° C. for 2 hr, and then evaporated in vacuo. The residue was diluted with water (20 mL) and extracted with dichloromethane (2*30 mL). The combined organic extracts were dried over sodium sulphate and evaporated in vacuo to afford 5-(5-methyl-2-piperidyl)-1H-pyrazolo[3,4-b]pyridine (1.2 g, 5.55 mmol, 91.45% yield) as brown solid, which was used directly in the next step.

$^1$H NMR (500 MHz, CDCl$_3$) 1.08 (d, 3H), 1.62 (m, 2H), 1.73 (m, 2H), 1.93 (m, 2H), 2.48 (t, 1H), 3.18 (m, 1H), 3.76 (m, 1H), 8.06 (s, 1H), 8.15 (s, 1H), 8.63 (s, 1H), 11.78 (m, 1H).

LCMS(ESI): [M+H]$^+$ m/z: calcd 216.2; found 217.2; Rt=0.728 min.

6Y. Synthesis of 2-(3-chloro-4-fluoro-phenyl)-5-methyl-piperidine

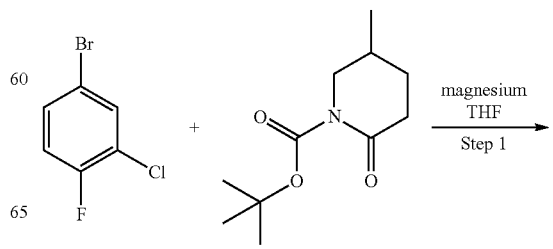

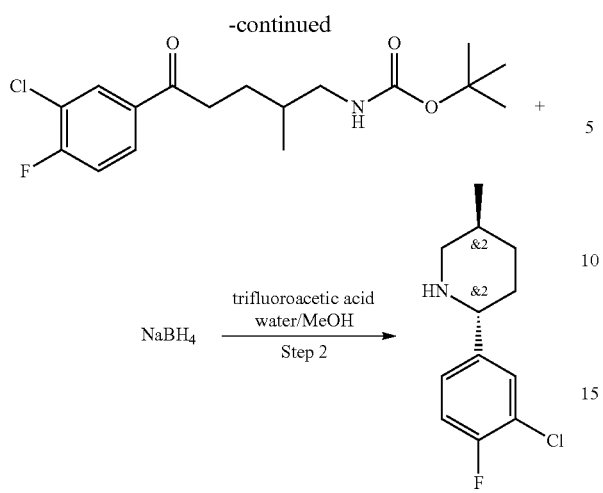

Step 1: Synthesis of tert-butyl N-[5-(3-chloro-4-fluoro-phenyl)-2-methyl-5-oxo-pentyl]carbamate To a dry 2 necked flask was added magnesium (1.16 g, 47.75 mmol, 666.93 µL), dry THF (75 mL) and 4-bromo-2-chloro-1-fluoro-benzene (10 g, 47.75 mmol, 5.78 mL) with stirring under Ar. The mixture was heated gently until it maintained its own reflux. When reflux had subsided external heating was applied to maintain reflux for a further 1 hour. tert-butyl 5-methyl-2-oxo-piperidine-1-carboxylate (7.83 g, 36.73 mmol) was added to a dry 3 necked round bottomed flask with a thermometer. Dry THF (75 mL) was added with stirring under Ar and the solution was cooled to −78° C. The Grignard reagent was added to the t-Boc-lactam over 1 hour, maintaining the internal temperature below −70° C. The solution was warmed to room temperature and sat. NH₄Cl was added. The aqueous layer was extracted 3×50 mL with DCM and the organic layers combined, dried over Na₂SO₄, filtered and concentrated in vacuo. tert-butyl N-[5-(3-chloro-4-fluoro-phenyl)-2-methyl-5-oxo-pentyl]carbamate (13 g, crude) was obtained as a light-yellow oil and was used in the next step without further purification.

$^1$H NMR (CDCl$_3$, 500 MHz): δ 0.95 (d, 3H), 1.44 (s, 9H), 1.71-1.80 (m, 4H), 2.98 (t, 2H), 4.02 (t, 1H), 4.68 (brs, 1H), 7.20 (t, 1H), 7.87 (dd, 1H), 8.03 (d, 1H).

LCMS(ESI): [M+Na]⁺ m/z: calcd 343.2; found 366.2; Rt=1.622 min.

Step 2: Synthesis of 2-(3-chloro-4-fluoro-phenyl)-5-methyl-piperidine

The tert-butyl N-[5-(3-chloro-4-fluoro-phenyl)-2-methyl-5-oxo-pentyl]carbamate (13 g, 37.81 mmol) was stirred in trifluoroacetic acid (17.25 g, 151.24 mmol, 11.65 mL) for 1 hr. TLC was used to check the reaction progress. 50% w/v NaOH solution was added to the mixture until the pH was 13-14. The product was extracted 4×20 mL with DCM and the organic layers combined, dried with MgSO₄ and evaporated. The product was dissolved in mixture water (25 mL)/MeOH (150 mL) and added to a flask followed by Sodium Borohydride (1.43 g, 37.81 mmol, 1.34 mL). The mixture was stirred under Ar overnight. The mixture was acidified with 1-2 M HCl until the pH was 1-3 and left for 30 minutes. NaOH solution was then added until the pH was 13-14 and the product was extracted with DCM (4×100 mL), the organic layers were combined, dried with Na₂SO₄, filtered and evaporated. The residue was purified by CC (Companion combiflash; 120 g SiO₂; chloroform/acetonitrile with acetonitrile from 0 to 17%, flow rate=85 ml/min, Rv=7-11 cv.) to give 2-(3-chloro-4-fluoro-phenyl)-5-methyl-piperidine (2.2 g, 9.66 mmol, 25.55% yield) as a light-yellow oil.

$^1$H NMR (CDCl$_3$, 400 MHz): δ 0.86 (d, 3H), 1.12 (m, 1H), 1.42 (m, 1H), 1.61-1.84 (m, 4H), 2.37 (t, 1H), 3.10 (d, 1H), 3.48 (d, 1H), 7.04 (t, 1H), 7.18 (dd, 1H), 7.42 (d, 1H)

LCMS(ESI): [M+H]⁺ m/z: calcd 227.1; found 228.2; Rt=0.895 min.

6Z. Synthesis of 2-(3,4-Dichlorophenyl)-5-methyl-piperidine

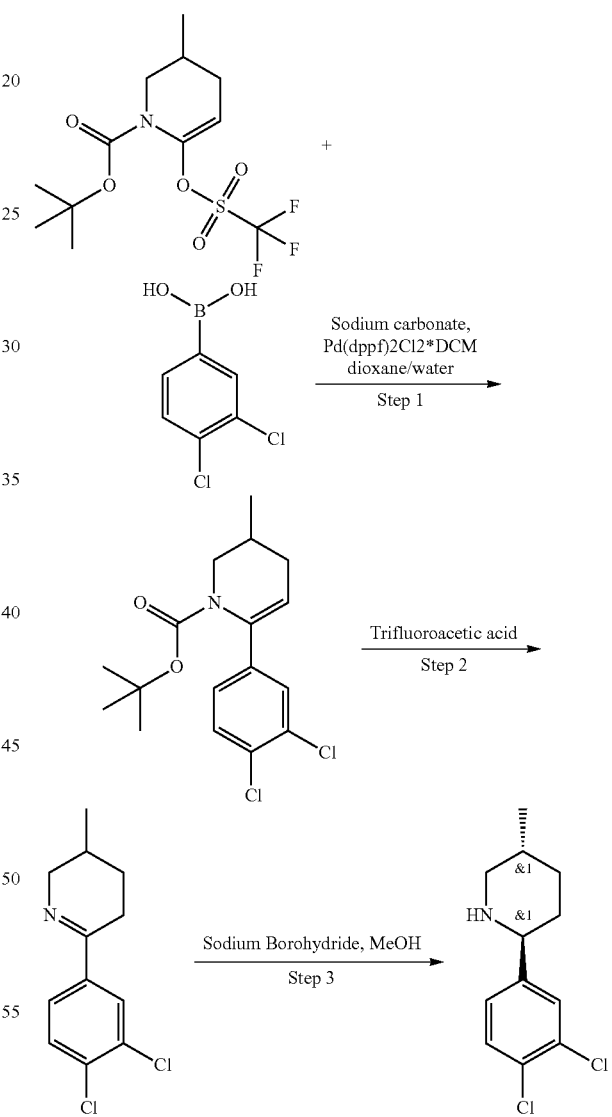

Step 1: Synthesis Tert-butyl 6-(3,4-dichlorophenyl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (5 g, 14.48 mmol), (3,4-dichlorophenyl)boronic acid (2.76 g, 14.48 mmol) and Sodium carbonate (4.60 g, 43.44 mmol, 1.82 mL) were added to a mixture of dioxane (45 mL) and water (15 mL). The resulting mixture was evacuated and then backfilled with argon, this operation was repeated three times, then Pd(dppf)$_2$Cl$_2$*DCM (723.93 μmol) was added under argon. The reaction mixture was stirred under argon at 70° C. for 15 hr, then cooled and filtered. The filtercake was washed with 1,4-dioxane (2*20 ml) and discarded. The filtrate was evaporated in vacuo to afford tert-butyl 6-(3,4-dichlorophenyl)-3-methyl-3,4-dihydro-2H-pyridine-1-carboxylate (4.5 g, 13.15 mmol, 90.81% yield) as brown oil, which was used in next step without purification.

Step 2: Synthesis of 6-(3,4-dichlorophenyl)-3-methyl-2,3,4,5-tetrahydropyridine The solution of tert-butyl 6-(3,4-dichlorophenyl)-3-methyl-3,4-dihydro-2H-pyridine-1-carboxylate (4.5 g, 13.15 mmol) in Trifluoroacetic acid (29.98 g, 262.96 mmol, 20.26 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 6-(3,4-dichlorophenyl)-3-methyl-2,3,4,5-tetrahydropyridine (3 g, 12.39 mmol, 94.23% yield) as brown solid, which was used directly in the next step.

LCMS(ESI): [M+H]$^+$ m/z: calcd 241.1; found 242.2; Rt=0.793 min.

Step 3: Synthesis of 2-(3,4-dichlorophenyl)-5-methyl-piperidine

Sodium Borohydride (937.44 mg, 24.78 mmol, 876.11 μL) was added in one portion to a stirred solution of 6-(3,4-dichlorophenyl)-3-methyl-2,3,4,5-tetrahydropyridine (3 g, 12.39 mmol) in MeOH (50 mL) at 0° C. The resulting mixture was stirred at 0° C. for 1 hr, and then evaporated in vacuo. The residue was diluted with water (20 ml) and extracted with dichloromethane (2*40 ml). The combined organic extracts were dried over sodium sulphate and evaporated in vacuo. The obtained oil was subjected to HPLC (2-10 min 50-70% ACN+HCL/H$_2$O 30 ml/min (loading pump 4 ml ACN+HCL column: SunFire 100*19 mm, 5 microM) to afford 2-(3,4-dichlorophenyl)-5-methyl-piperidine (1.43 g, 5.86 mmol, 47.27% yield).

$^1$H NMR (DMSO, 400 MHz): 0.88 (d, 3H), 1.22 (m, 1H), 1.85 (m, 2H), 2.05 (m, 1H), 2.67 (m, 1H), 4.22 (m, 1H), 7.52 (d, 1H), 7.69 (d, 1H), 8.02 (s, 1H), 9.62 (m, 1H).

LCMS(ESI): [M+H]$^+$ m/z: calcd 243.1; found 244.2; Rt=2.063 min.

6AA. The Synthesis of 2-(3-chloro-4-methyl-phenyl)-5-methyl-piperidine

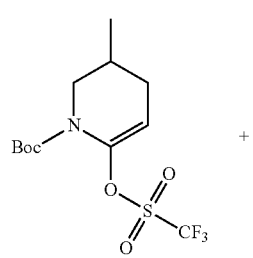

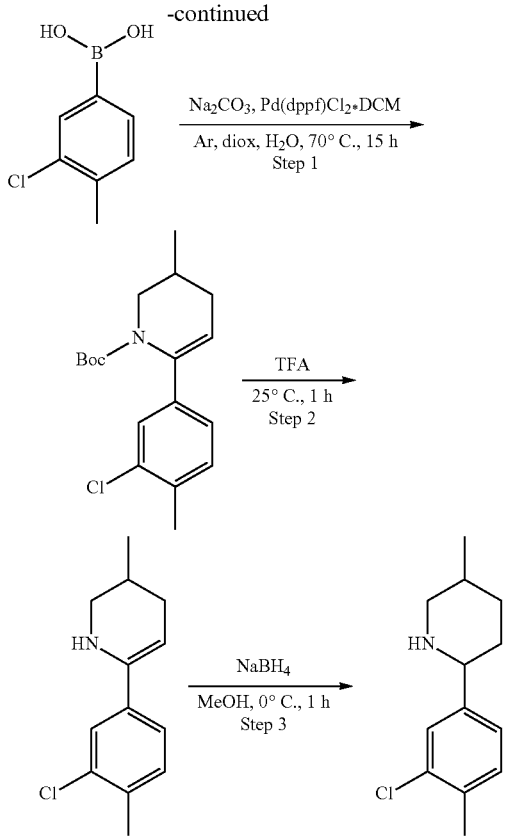

Step 1: The Synthesis of tert-butyl 6-(3-chloro-4-methyl-phenyl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (5 g, 14.48 mmol), (3-chloro-4-methyl-phenyl)boronic acid (2.47 g, 14.48 mmol) and Sodium carbonate (4.60 g, 43.44 mmol, 1.82 mL) were added to a mixture of dioxane (45 mL) and water (15 mL). The resulting mixture was evacuated and then backfilled with argon, this operation was repeated three times, then Pd(dppf)$_2$Cl$_2$*DCM (723.93 μmol) was added under argon. The reaction mixture was stirred under argon at 70° C. for 15 hr, then cooled and filtered. The filtercake was washed with 1,4-dioxane (2*20 ml) and discarded. The filtrate was evaporated in vacuo to afford tert-butyl 6-(3-chloro-4-methyl-phenyl)-3-methyl-3,4-dihydro-2H-pyridine-1-carboxylate (4 g, 12.43 mmol, 85.84% yield) as brown oil, which was used in next step without purification.

LCMS(ESI): [M-$^t$Bu]$^+$ m/z: calcd 265.1; found 266.2; Rt=1.827 min.

Step 2: The Synthesis of 6-(3-chloro-4-methyl-phenyl)-3-methyl-2,3,4,5-tetrahydropyridine The solution of tert-butyl 6-(3-chloro-4-methyl-phenyl)-3-methyl-3,4-dihydro-2H-pyridine-1-carboxylate (4 g, 12.43 mmol) in trifluoroacetic acid (28.34 g, 248.57 mmol, 19.15 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 6-(3-chloro-4-methyl-phenyl)-3-methyl-2,3,4,5-tetrahydropyridine (2 g, 9.02 mmol, 72.58% yield) as brown solid, which was used directly in the next step.

LCMS(ESI): [M+H]⁺ m/z: calcd 221.1; found 222.0; Rt=0.999 min.

Step 3: The Synthesis of 2-(3-chloro-4-methyl-phenyl)-5-methyl-piperidine

Sodium Borohydride (682.51 mg, 18.04 mmol, 637.86 µL) was added in one portion to a stirred solution of 6-(3-chloro-4-methyl-phenyl)-3-methyl-2,3,4,5-tetrahydropyridine (2 g, 9.02 mmol) in MeOH (50 mL) at 0° C. The resulting mixture was stirred at 0° C. for 1 hr, and then evaporated in vacuo. The residue was diluted with water (20 ml) and extracted with dichloromethane (2*40 ml). The combined organic extracts were dried over sodium sulphate and evaporated in vacuo. The obtained oil was subjected to HPLC (Waters SunFire C18 19*100 mm 5 mkm column, Hexane-MeOH 50-50 as an mobile phase, Flow 12 mL/min) to afford 2-(3-chloro-4-methyl-phenyl)-5-methyl-piperidine (513.6 mg, 2.30 mmol, 25.45% yield).

LCMS(ESI): [M+H]⁺ m/z: calcd 223.1; found 224.4; Rt=2.606 min.

6BB. Synthesis of 4-[(2S,5R)-5-methyl-2-piperidyl]-1H-indazole

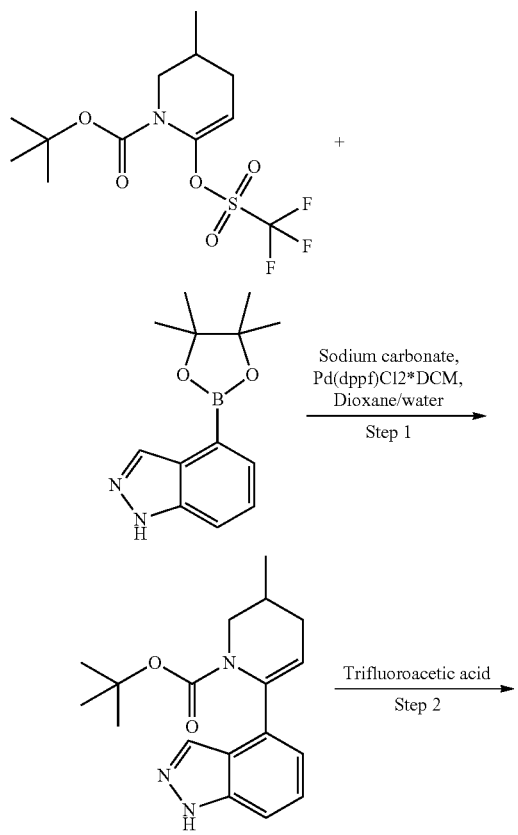

Step 1: Synthesis of tert-butyl 6-(1H-indazol-4-yl)-3-methyl-3,4-dihydro-2H-pyridine-1-carboxylate Sodium carbonate (7.82 g, 73.74 mmol, 3.09 mL) was added to a solution of tert-butyl 3-methyl-6-(trifluoromethylsulfonyloxy)-3,4-dihydro-2H-pyridine-1-carboxylate (9.34 g, 27.04 mmol) and 4-(4,4,5,5-tetramethyl-1,3,2-dioxaborolan-2-yl)-1H-indazole (6 g, 24.58 mmol) in Dioxane (90 mL) and Water (30 mL). Reaction flask was evacuated and refilled with argon 3 times. Then, Pd(dppf)Cl₂*DCM (1.00 g, 1.23 mmol) was added under stream of argon. Resulting mixture was stirred at 90° C. for 14 hr under inert atmosphere. Reaction mixture was evaporated to give crude product (25 g) which was purified by gradient column chromatography to give tert-butyl 6-(1H-indazol-4-yl)-3-methyl-3,4-dihydro-2H-pyridine-1-carboxylate (4.2 g, 13.40 mmol, 54.52% yield)

LCMS(ESI): [M+H]⁺ m/z: calcd 313.2; found 314.2; Rt=1.337 min.

Step 2: Synthesis of 4-(3-methyl-2,3,4,5-tetrahydropyridin-6-yl)-1H-indazole

To the tert-butyl 6-(1H-indazol-4-yl)-3-methyl-3,4-dihydro-2H-pyridine-1-carboxylate (2 g, 6.38 mmol) Trifluoroacetic acid (7.28 g, 63.82 mmol, 4.92 mL) was added and the reaction mixture was stirred at 25° C. for 1 hr. TFA was evaporated. The residue was diluted with chloroform and evaporated to dryness to give 4-(3-methyl-2,3,4,5-tetrahydropyridin-6-yl)-1H-indazole (0.9 g, 4.22 mmol, 66.12% yield) 1 hr.

¹H NMR (CDCl₃, 400 MHz): 1.53 (d, 3H), 1.73 (m, 1H), 2.22 (m, 2H), 3.45 (m, 1H), 3.49 (m, 2H), 4.14 (m, 1H), 7.58 (d, 1H), 7.65 (dd, 1H), 7.90 (d, 1H), 8.35 (s, 1H), 12.55 (s, 1H).

LCMS(ESI): [M+H]⁺ m/z: calcd 213.2; found 214.2; Rt=0.608 min.

Step 3: Synthesis of 4-[(2S,5R)-5-methyl-2-piperidyl]-1H-indazole

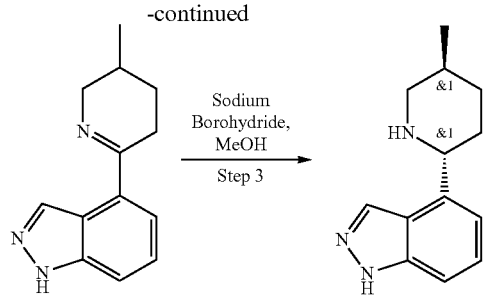

To the pre-cooled (0° C.) solution of 4-(3-methyl-2,3,4,5-tetrahydropyridin-6-yl)-1H-indazole (0.9 g, 4.22 mmol) in MeOH (10 mL) Sodium Borohydride (191.56 mg, 5.06 mmol, 179.03 µL) was added portionwise. The reaction mixture was then stirred at 25° C. for 1 hr. MeOH was evaporated, the residue was dissolved in MeOH (5 ml) and dioxane*HCl (5 ml) was added. The mixture was stirred for 15 min. Solvents were evaporated to give crude solid product which was washed with THF (2*10 ml), dried in vacuo to give 4-[(2S,5R)-5-methyl-2-piperidyl]-1H-indazole (1.7 g, crude, HCl).

LCMS(ESI): [M+H]⁺ m/z: calcd 215.2; found 216.0; Rt=0.773 min.

6CC. The Synthesis of 6-(5-methylpiperidin-2-yl)isoindolin-1-one

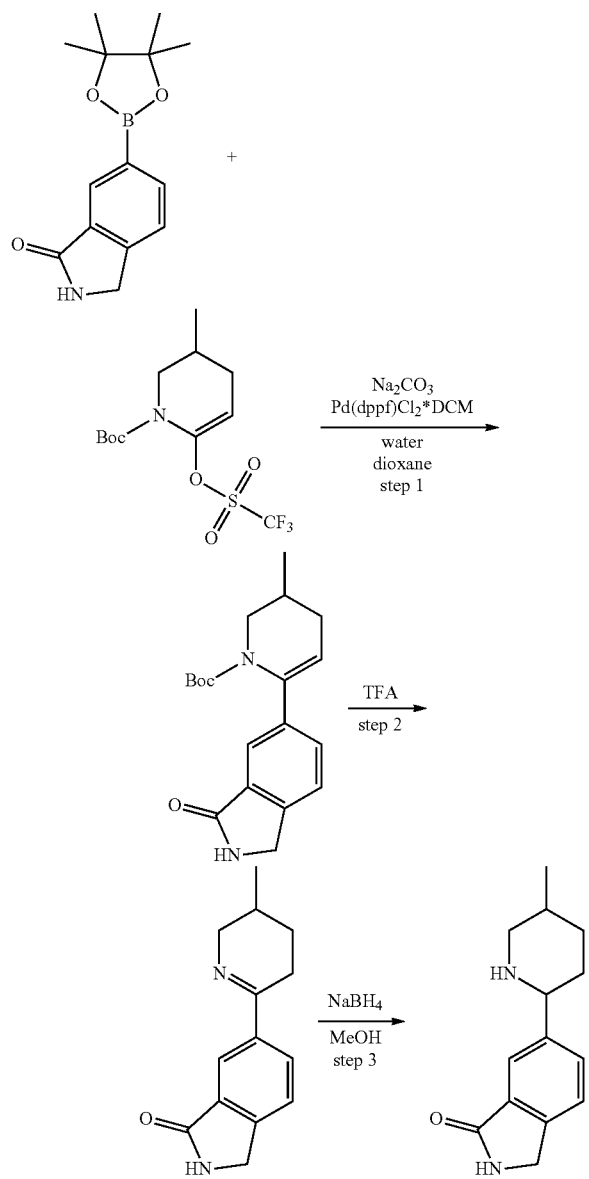

Step 1: Synthesis of tert-butyl 3-methyl-6-(3-oxoisoindolin-5-yl)-3,4-dihydropyridine-1(2H)-carboxylate tert-butyl 3-methyl-6-(trifluoromethylsulfonyloxy)-3,4-dihydro-2H-pyridine-1-carboxylate (10.00 g, 28.96 mmol), 6-(4,4,5,5-tetramethyl-1,3,2-dioxaborolan-2-yl)isoindolin-1-one (7.50 g, 28.96 mmol) and sodium carbonate (9.21 g, 86.87 mmol, 3.64 mL) were added to a mixture of dioxane (90 mL) and water (30 mL). The resulting mixture was evacuated and then backfilled with argon, this operation was repeated three times, then Pd(dppf)Cl₂ DCM (1.18 g, 1.45 mmol) was added under argon. The reaction mixture was stirred under argon at 70° C. for 12 hr, then cooled and filtered. The filter cake was washed with 1,4-dioxane (2*20 ml) and discarded. The filtrate was evaporated in vacuo to afford tert-butyl 3-methyl-6-(3-oxoisoindolin-5-yl)-3,4-dihydro-2H-pyridine-1-carboxylate (9 g, 27.41 mmol, 94.64% yield) as brown oil, which was used in next step without purification.

¹H NMR (500 MHz, DMSO-d₆) δ (ppm) 0.96 (d, 3H), 1.12 (s, 9H), 1.42 (m, 1H), 1.96 (m, 2H), 2.48 (m, 1H), 3.06 (m, 1H), 3.54 (s, 2H), 5.38 (m, 1H), 7.49 (m, 2H), 8.51 (s, 1H).

LCMS(ESI): [M-Boc]⁺ m/z: calcd 228.2; found 229.2; Rt=1.375 min.

Step 2: Synthesis of 6-(5-methyl-3,4,5,6-tetrahydropyridin-2-yl)isoindolin-1-one The solution of tert-butyl 3-methyl-6-(3-oxoisoindolin-5-yl)-3,4-dihydro-2H-pyridine-1-carboxylate (9 g, 27.41 mmol) in TFA (31.25 g, 274.05 mmol, 21.11 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with DCM (2*30 ml). The combined organic extracts were dried over sodium sulphate and evaporated in vacuo to afford 6-(3-methyl-2,3,4,5-tetrahydropyridin-6-yl)isoindolin-1-one (6 g, 26.28 mmol, 95.90% yield) as brown oil, which was used directly in the next step.

¹H NMR (500 MHz, DMSO-d₆) δ (ppm) 0.97 (d, 3H), 1.31 (m, 1H), 1.72 (m, 1H), 1.89 (m, 1H), 2.72 (m, 1H), 2.96 (m, 1H), 3.33 (m, 2H), 3.92 (m, 1H), 4.42 (s, 2H), 6.98 (d, 1H), 7.12 (d, 1H), 8.07 (s, 1H).

LCMS(ESI): [M]⁺ m/z: calcd 228.2; found 229.2; Rt=0.514 min.

Step 3: Synthesis of 6-(5-methylpiperidin-2-yl)isoindolin-1-one

Sodium borohydride (1.99 g, 52.56 mmol, 1.86 mL) was added portion wise to a stirred solution of 6-(3-methyl-2,3,4,5-tetrahydropyridin-6-yl)isoindolin-1-one (6 g, 26.28 mmol) in MeOH (60 mL) at 0° C. The resulting mixture was stirred at 0° C. for 1 hr, then the solution was warmed to rt. Arter 10 hr it was evaporated in vacuo. To the residue water (20 ml) was added and filtered on. The obtained 6-(5-methyl-2-piperidyl)isoindolin-1-one (1 g, 4.34 mmol, 16.52% yield) as grey solid was used in next step without purification.

¹H NMR (500 MHz, DMSO-d₆) δ (ppm) 0.86 (d, 3H), 1.12 (m, 1H), 1.32 (m, 1H), 1.56 (m, 1H), 1.74 (m, 2H), 2.22 (m, 1H), 2.38 (m, 1H), 3.01 (m, 1H), 3.58 (m, 1H), 4.38 (s, 2H), 7.48 (d, 1H), 7.55 (d, 1H), 7.67 (s, 1H), 8.49 (m, 1H).

LCMS(ESI): [M]⁺ m/z: calcd 230.2; found 231.2; Rt=0.761 min.

6DD. The Synthesis of rac-(2R,5S)-2-(3-chloro-5-(trifluoromethyl)phenyl)-5-methylpiperidine

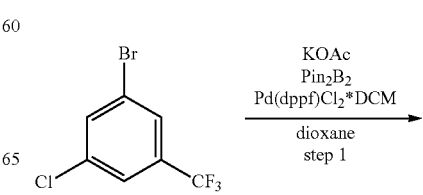

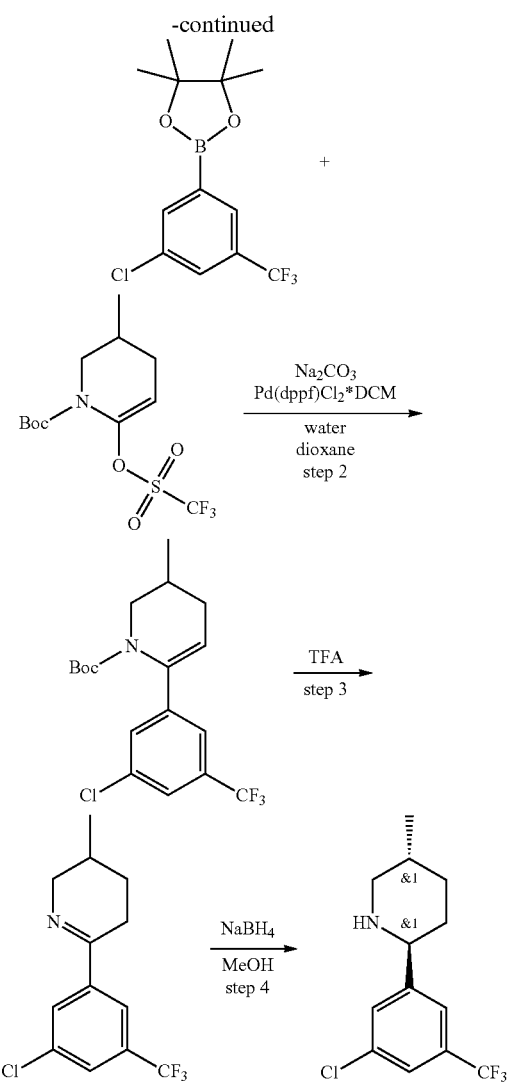

Step 1: Synthesis of 2-(3-chloro-5-(trifluoromethyl)phenyl)-4,4,5,5-tetramethyl-1,3,2-dioxaborolane A mixture of 1-bromo-3-chloro-5-(trifluoromethyl)benzene (19.9 g, 76.70 mmol), 4,4,5,5-tetramethyl-2-(4,4,5,5-tetramethyl-1,3,2-dioxaborolan-2-yl)-1,3,2-dioxaborolane (29.22 g, 115.05 mmol) and KOAc (22.58 g, 230.10 mmol, 14.38 mL) in dioxane (300 mL) was degassed with argon for 10 min. Pd(dppf)Cl$_2$*DCM (1 g, 1.22 mmol) was next added and the reaction mixture was heated to 90° C. for 16 hr. The reaction mixture was cooled to rt, filtered and concentrated under reduced pressure. The residue was treated with hexane, filtered through thin layer of SiO$_2$ and evaporated to dryness. Crude product was purified by flash chromatography on SiO$_2$ (Hexane:CHCl$_3$) to give 2-[3-chloro-5-(trifluoromethyl)phenyl]-4,4,5,5-tetramethyl-1,3,2-dioxaborolane (8.1 g, 26.43 mmol, 34.45% yield).

$^1$H NMR (400 MHz, DMSO-d$_6$) δ (ppm) 1.12 (s, 12H), 7.92 (m, 3H).

GCMS: calcd 306.2; found 306.2; Rt=7.597 min.

Step 2: Synthesis of tert-butyl 6-(3-chloro-5-(trifluoromethyl)phenyl)-3-methyl-3,4-dihydropyridine-1(2H)-carboxylate tert-butyl 3-methyl-6-(trifluoromethylsulfonyloxy)-3,4-dihydro-2H-pyridine-1-carboxylate (6.76 g, 19.57 mmol), 2-[3-chloro-5-(trifluoromethyl)phenyl]-4,4,5,5-tetramethyl-1,3,2-dioxaborolane (7.5 g, 24.47 mmol) and sodium carbonate (6.22 g, 58.72 mmol, 2.46 mL) were added to a mixture of 1,4-dioxane (22.5 mL) and water (7.5 mL). The resulting mixture was evacuated and then backfilled with argon, then Pd(dppf)Cl$_2$*DCM (798.65 mg, 978.74 μmol) was added under argon. The reaction mixture was stirred at 75° C. for 16 hr, then treated with water and needed product was extracted with DCM, then evaporated. tert-butyl 6-[3-chloro-5-(trifluoromethyl)phenyl]-3-methyl-3,4-dihydro-2H-pyridine-1-carboxylate (7 g, crude) was obtained.

$^1$H NMR (500 MHz, DMSO-d$_6$) δ (ppm) 0.93 (d, 3H), 1.01 (s, 9H), 1.36 (m, 1H), 1.81 (m, 1H), 2.36 (m, 1H), 3.05 (m, 1H), 3.87 (m, 1H), 5.58 (m, 1H), 7.47 (s, 1H), 7.59 (s, 1H), 7.72 (s, 1H).

LCMS(ESI): [M-Boc]$^+$ m/z: calcd 275.2; found 276.2; Rt=1.752 min.

Step 3: Synthesis of 6-(3-chloro-5-(trifluoromethyl)phenyl)-3-methyl-2,3,4,5-tetrahydropyridine tert-butyl 6-[3-chloro-5-(trifluoromethyl)phenyl]-3-methyl-3,4-dihydro-2H-pyridine-1-carboxylate (7 g, 18.63 mmol) (crude product from previous stage) was dissolved in trifluoroacetic acid, 99% (22.20 g, 194.70 mmol, 15 mL) and stirred for 1 hr and then evaporated to dryness to give 6-[3-chloro-5-(trifluoromethyl)phenyl]-3-methyl-2,3,4,5-tetrahydropyridine (10 g, crude).

$^1$H NMR (500 MHz, DMSO-d$_6$) δ (ppm) 1.06 (d, 3H), 1.53 (m, 1H), 1.98 (m, 2H), 3.36 (m, 3H), 3.95 (m, 1H), 8.25 (m, 3H).

LCMS(ESI): [M]$^+$ m/z: calcd 275.2; found 276.2; Rt=0.958 min.

Step 4: Synthesis of rac-(2R,5S)-2-(3-chloro-5-(trifluoromethyl)phenyl)-5-methylpiperidine 6-[3-chloro-5-(trifluoromethyl)phenyl]-3-methyl-2,3,4,5-tetrahydropyridine (10 g, 36.27 mmol) was dissolved in methanol (20 mL) and then sodium borohydride (2.5 g, 66.08 mmol, 2.34 mL) was added. After 1 hr of vigorous stirring (pH>7) the solvent was evaporated, crude product was treated with water, then extracted with DCM (2*75 ml) and concentrated in vacuo. Crude product was purified by silica gel flash chromatography (CHCl$_3$:MeOH, gradient). (2R,5S)-2-[3-chloro-5-(trifluoromethyl)phenyl]-5-methylpiperidine (1 g, 3.60 mmol, 9.93% yield) was obtained.

$^1$H NMR (500 MHz, DMSO-d$_6$) δ (ppm) 0.88 (d, 3H), 1.12 (m, 1H), 1.32 (m, 1H), 1.55 (m, 1H), 1.81 (m, 2H), 2.28 (t, 1H), 3.02 (d, 1H), 3.57 (d, 1H), 7.53 (s, 1H), 7.61 (s, 1H), 7.66 (s, 1H).

LCMS(ESI): [M]$^+$ m/z: calcd 277.2; found 278.2; Rt=0.929 min.

6EE. The Synthesis of 2-(3-chloro-5-fluorophenyl)-5-methylpiperidine

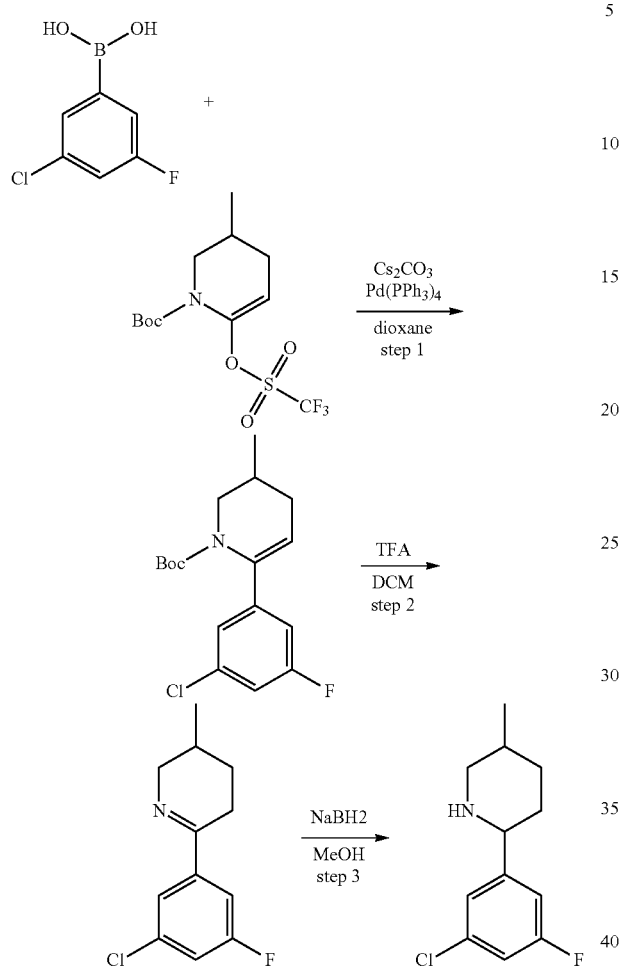

Step 1: Synthesis of tert-butyl 6-(3-chloro-5-fluoro-phenyl)-3-methyl-3,4-dihydropyridine-1(2H)-carboxylate

(3-chloro-5-fluoro-phenyl)boronic acid (3 g, 17.21 mmol) and tert-butyl 3-methyl-6-(trifluoromethylsulfonyloxy)-3,4-dihydro-2H-pyridine-1-carboxylate (5.94 g, 17.21 mmol) was dissolved in dioxane (30 mL) and the reaction mixture was thoroughly degassed, following by the subsequent addition of caesium carbonate (22.42 g, 68.82 mmol) and Palladium (0) tetrakis(triphenylphosphine) (198.82 mg, 172.05 μmol). Obtained reaction mixture was stirred at reflux overnight; after reaction was complete the organic solvent was evaporated under reduced pressure and the crude mixture was partitioned between EtOAc and H$_2$O. Water layer was additionally extracted with EtOAc twice; combined organic layers was washed with brine, dried over Na$_2$SO$_4$ and evaporated to give tert-butyl 6-(3-chloro-5-fluoro-phenyl)-3-methyl-3,4-dihydro-2H-pyridine-1-carboxylate (7 g, crude) which was used in the next step without purification.

$^1$H NMR (400 MHz, CDCl$_3$) δ (ppm) 0.96 (d, 3H), 1.25 (s, 9H), 1.95 (m, 2H), 2.38 (m, 1H), 2.93 (t, 1H), 4.01 (d, 1H), 5.32 (m, 1H), 6.88 (s, 2H), 7.05 (s, 1H).

LCMS(ESI): [M]$^+$ m/z: calcd 325.2; found 326.2; Rt=1.815 min.

Step 2: Synthesis of 6-(3-chloro-5-fluorophenyl)-3-methyl-2,3,4,5-tetrahydropyridine tert-butyl 6-(3-chloro-5-fluoro-phenyl)-3-methyl-3,4-dihydro-2H-pyridine-1-carboxylate (7 g, 17.19 mmol) was dissolved in DCM (50 mL) followed by the addition of TFA (9.80 g, 85.94 mmol, 6.62 mL) and stirring overnight. After the reaction was complete, the mixture was washed with 10% aq NaOH, and the organic solvent was evaporated to give 6-(3-chloro-5-fluoro-phenyl)-3-methyl-2,3,4,5-tetrahydropyridine (3.5 g, 15.51 mmol, 90.22% yield) which was used in the next step without purification.

$^1$H NMR (500 MHz, CDCl$_3$) δ (ppm) 0.96 (d, 3H), 1.36 (m, 1H), 1.68 (m, 1H), 1.91 (m, 1H), 2.50 (m, 1H), 2.68 (m, 1H), 3.24 (m, 1H), 3.96 (m, 1H), 7.08 (s, 1H), 7.38 (s, 1H), 7.54 (s, 1H).

Step 3: Synthesis of 2-(3-chloro-5-fluorophenyl)-5-methylpiperidine

6-(3-chloro-5-fluoro-phenyl)-3-methyl-2,3,4,5-tetrahydropyridine (3.5 g, 15.51 mmol) was dissolved in MeOH (20 mL) and cooled to 0° C. Sodium borohydride (1.17 g, 31.02 mmol, 1.10 mL) was added in portions to obtained mixture and additionally stirred overnight. After the reaction was complete, the reaction mixture was acidified with 10% aq HCl to pH=2, washed with MTBE (2*10 mL), basified with 10% aq NaOH to pH=10 and extracted with DCM (40 mL). Evaporation of the solvent result in pure (2R,5S)-2-(3-chloro-5-fluoro-phenyl)-5-methyl-piperidine.

$^1$H NMR (500 MHz, CDCl$_3$) δ (ppm) 0.88 (d, 3H), 1.12 (m, 1H), 1.48 (m, 1H), 1.86 (m, 4H), 2.39 (m, 1H), 3.12 (m, 1H), 3.52 (m, 1H), 6.95 (s, 1H), 7.00 (s, 1H), 7.16 (s, 1H).

LCMS(ESI): [M]$^-$ m/z: calcd 227.2; found 228.2; Rt=0.752 min.

6FF. The Synthesis of 2-(3-chloro-4-(trifluoromethyl)phenyl)-5-methylpiperidine

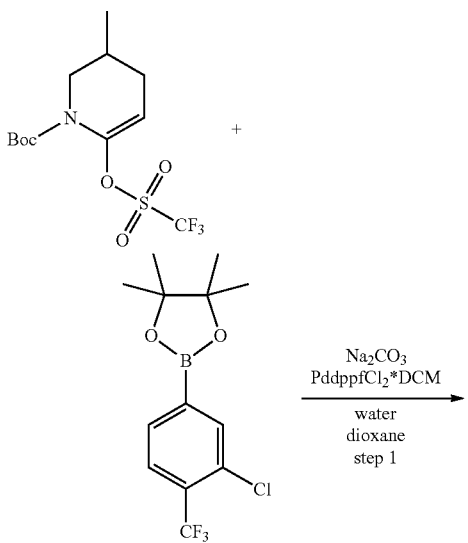

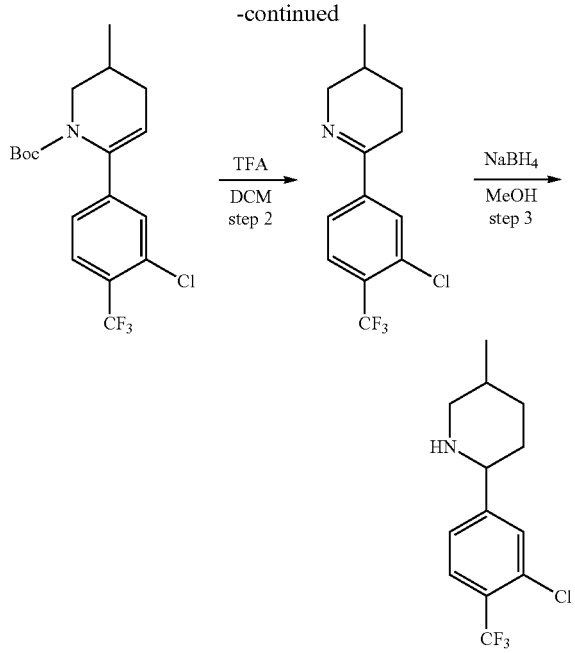

Step 1: Synthesis of tert-butyl 6-(3-chloro-4-(trifluoromethyl)phenyl)-3-methyl-3,4-dihydropyridine-1(2H)-carboxylate 2-[3-chloro-4-(trifluoromethyl)phenyl]-4,4,5,5-tetramethyl-1,3,2-dioxaborolane (9 g, 29.36 mmol), tert-butyl 3-methyl-6-(trifluoromethylsulfonyloxy)-3,4-dihydro-2H-pyridine-1-carboxylate (8.11 g, 23.49 mmol), sodium carbonate (9.34 g, 88.09 mmol, 3.69 mL) and Pd(dppf)Cl₂ DCM (23.98 g, 29.36 mmol) were added to a mixture of 1,4-dioxane (100 mL) and water (50 mL) and the reaction mixture was stirred under argon atmosphere at 80° C. for 15 hr. After cooling down, the reaction mixture was diluted with water and extracted with DCM. The organic layer was separated, dried over Na₂SO₄, concentrated under reduced pressure and submitted to flash chromatography (Hexane-MTBE as an eluent mixture) to afford tert-butyl 6-[3-chloro-4-(trifluoromethyl)phenyl]-3-methyl-3,4-dihydro-2H-pyridine-1-carboxylate (5 g, crude) which had not right purity but was used in the next step without additional purification.

¹H NMR (400 MHz, DMSO-d₆) δ (ppm) 0.98 (d, 3H), 1.12 (s, 9H), 1.98 (m, 2H), 2.41 (m, 1H), 3.02 (m, 1H), 3.98 (m, 1H), 5.42 (m, 1H), 7.38 (m, 2H), 7.76 (d, 1H).

LCMS(ESI): [M-Boc]⁺ m/z: calcd 275.2; found 276.2; Rt=1.826 min.

Step 2: Synthesis of 6-(3-chloro-4-(trifluoromethyl)phenyl)-3-methyl-2,3,4,5-tetrahydropyridine To a stirred solution of crude tert-butyl 6-[3-chloro-4-(trifluoromethyl)phenyl]-3-methyl-3,4-dihydro-2H-pyridine-1-carboxylate (2 g, 5.32 mmol) in DCM (5 mL) were added TFA (7.40 g, 64.90 mmol, 5 mL) at rt. The resulting reaction mixture was stirred at rt for 0.5 hr. Upon completion, the reaction mixture was concentrated under reduced pressure and the residue was treated with NaOH solution and extracted with DCM. The combined organic phase was washed with water, brine, dried over Na₂SO₄ and concentrated under reduced pressure to obtain crude 6-[3-chloro-4-(trifluoromethyl)phenyl]-3-methyl-2,3,4,5-tetrahydropyridine (1.4 g, crude) which was used directly in the next step without purification.

LCMS(ESI): [M]⁺ m/z: calcd 275.2; found 276.2; Rt=0.953 min.

Step 3: Synthesis of 2-(3-chloro-4-(trifluoromethyl)phenyl)-5-methylpiperidine To a stirred solution of 6-[3-chloro-4-(trifluoromethyl)phenyl]-3-methyl-2,3,4,5-tetrahydropyridine (1.4 g, 4.72 mmol) in MeOH (15 mL) sodium borohydride (232.27 mg, 6.14 mmol, 217.07 µL) was added in 3 portions at rt. The resulting reaction mixture was stirred at rt for 12 hr and then concentrated under reduced pressure. The residue was dissolved in DCM (15 mL) washed with water, dried over Na₂SO₄ and concentrated on a rotary evaporator to afford 2-[3-chloro-4-(trifluoromethyl)phenyl]-5-methyl-piperidine (1.8 g, crude) which was used in the next steps without purification.

LCMS(ESI): [M]⁺ m/z: calcd 277.2; found 278.2; Rt=0.748 min.

6GG. The Synthesis of rac-3-((2R,5S)-5-methylpiperidin-2-yl)benzenesulfonamide

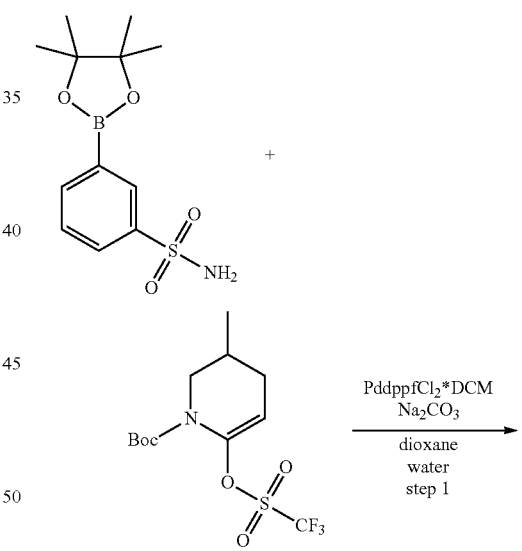

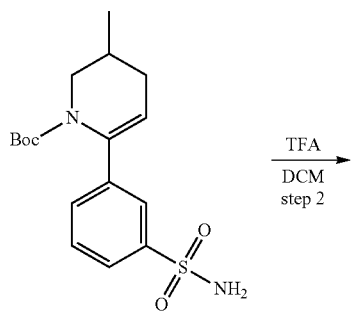

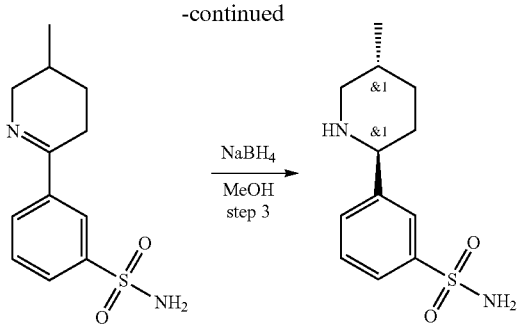

Step 1: Synthesis of tert-butyl 3-methyl-6-(3-Sulfamoylphenyl)-3,4-dihydropyridine-1(2H)-carboxylate Sodium carbonate (1.87 g, 17.66 mmol, 739.77 μL) was added to a solution of 3-(4,4,5,5-tetramethyl-1,3,2-dioxaborolan-2-yl)benzenesulfonamide (2 g, 7.06 mmol) and tert-butyl 3-methyl-6-(trifluoromethylsulfonyloxy)-3,4-dihydro-2H-pyridine-1-carboxylate (2.56 g, 7.42 mmol) in dioxane (20 mL) and water (7.5 mL). Reaction flask was evacuated and refilled with argon 3 times. Then, PdCl$_2$dppf*DCM (230.73 mg, 282.53 μmol) was added under stream of argon. Resulting mixture was stirred at 90° C. for 15 hr under inert atmosphere. Then, it was concentrated under reduced pressure and residue was extracted with ethyl acetate (50 ml). Obtained solution was filtered through a short pad of silicagel and evaporated under reduced pressure, affording tert-butyl 3-methyl-6-(3-sulfamoylphenyl)-3,4-dihydro-2H-pyridine-1-carboxylate (4.58 g, crude).

$^1$H NMR (500 MHz, DMSO-d$_6$) δ (ppm) 0.91 (d, 3H), 1.44 (s, 9H), 1.87 (m, 2H), 2.42 (m, 1H), 3.04 (m, 1H), 3.88 (m, 1H), 5.40 (m, 1H), 7.34 (m, 2H), 7.58 (m, 2H), 7.68 (m, 2H).

LCMS(ESI): [M-Boc]$^+$ m/z: calcd 252.4; found 253.2; Rt=1.354 min.

Step 2: Synthesis of 3-(5-methyl-3,4,5,6-tetrahydropyridin-2-yl)benzenesulfonamide Trifluoroacetic acid (22.20 g, 194.70 mmol, 15 mL) was added to a solution of tert-butyl 3-methyl-6-(3-sulfamoylphenyl)-3,4-dihydro-2H-pyridine-1-carboxylate (4.58 g, 12.99 mmol) in DCM (30 mL). Resulting mixture was stirred at 20° C. for 2 hr. Then, volatiles were removed under reduced pressure and residue was diluted with water (40 ml). Insoluble tar was filtered off through a pad of cotton wool. Filtrate was basified to pH≈10-11 with 20% aq. K$_2$CO$_3$ solution. Precipitated white solid was filtered and dried, affording 3-(3-methyl-2,3,4,5-tetrahydropyridin-6-yl)benzenesulfonamide (968 mg, 3.84 mmol, 29.52% yield).

$^1$H NMR (500 MHz, DMSO-d$_6$) δ (ppm) 0.95 (d, 3H), 1.34 (m, 1H), 1.65 (m, 1H), 1.88 (m, 1H), 2.58 (m, 1H), 2.79 (m, 1H), 3.22 (m, 1H), 3.94 (m, 1H), 7.36 (m, 2H), 7.58 (t, 1H), 7.83 (d, 1H), 7.96 (d, 1H), 8.31 (s, 1H).

LCMS(ESI): [M]$^+$ m/z: calcd 252.4; found 253.2; Rt=0.593 min.

Step 3: Synthesis of rac-3-((2R,5S)-5-methylpiperidin-2-yl)benzenesulfonamide Sodium borohydride (217.69 mg, 5.75 mmol, 203.44 μL) was added portion wise to a solution of 3-(3-methyl-2,3,4,5-tetrahydropyridin-6-yl)benzenesulfonamide (968 mg, 3.84 mmol) in MeOH (20 mL) during 15 minutes. Resulting solution was stirred at 20° C. for 1 hr. Then, solvent was removed under reduced pressure and residue was partitioned between water (20 ml) and ethyl acetate (40 ml). Organic layer was separated, dried over Na$_2$SO$_4$ and evaporated in vacuo, affording 3-[(2S,5R)-5-methyl-2-piperidyl]benzenesulfonamide (980 mg, crude).

$^1$H NMR (500 MHz, DMSO-d$_6$) δ (ppm) 0.85 (d, 3H), 1.12 (m, 2H), 1.31 (m, 1H), 1.53 (m, 1H), 1.77 (m, 2H), 2.26 (m, 1H), 3.01 (m, 1H), 3.54 (t, 1H), 7.30 (m, 2H), 7.47 (t, 1H), 7.54 (d, 1H), 7.66 (d, 1H), 7.85 (s, 1H).

LCMS(ESI): [M]$^+$ m/z: calcd 254.4; found 255.2; Rt=0.766 min.

6HH. The Synthesis of rac-(2R,5S)-5-methyl-2-(3-(methylsulfonyl)phenyl)piperidine

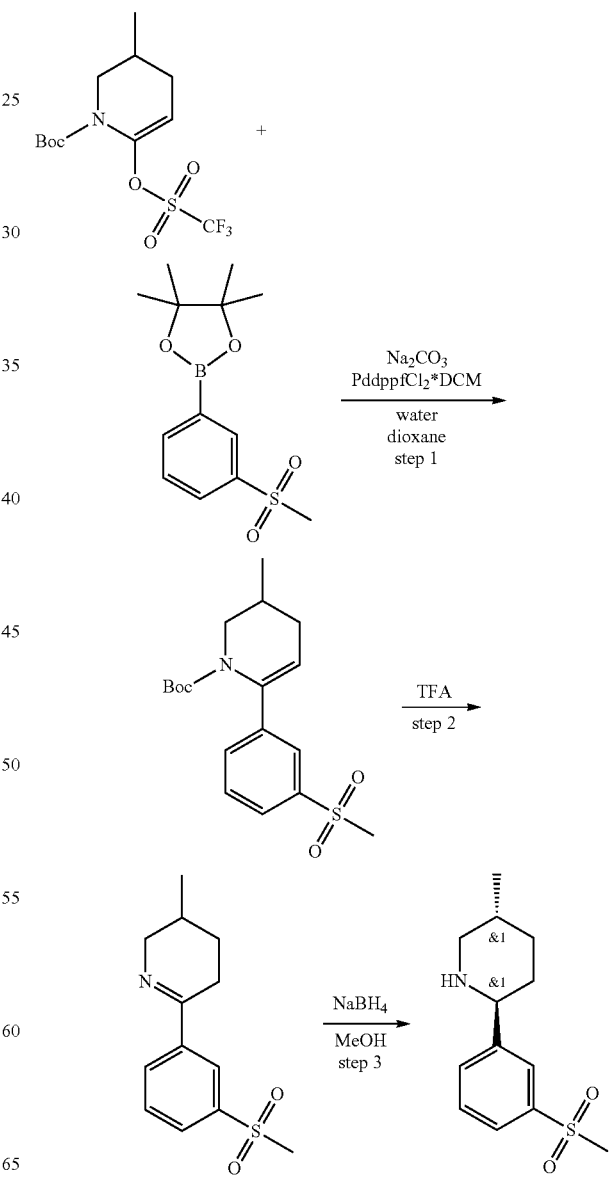

Step 1: Synthesis of tert-butyl 3-methyl-6-(3-(methylsulfonyl)phenyl)-3,4-dihydropyridine-1(2H)-carboxylate tert-butyl 3-methyl-6-(trifluoromethylsulfonyloxy)-3,4-dihydro-2H-pyridine-1-carboxylate (18 g, 52.12 mmol), 4,4,5,5-tetramethyl-2-(3-methylsulfonylphenyl)-1,3,2-dioxaborolane (15 g, 53.16 mmol) and sodium carbonate (17 g, 160.39 mmol, 6.72 mL) were added to a mixture of 1,4-dioxane (270 mL) and water (90 mL). The resulting mixture was evacuated and then backfilled with argon, this operation was repeated three times, then Pd(dppf)Cl$_2$*DCM (2.13 g, 2.61 mmol) was added under argon. The reaction mixture was stirred under argon at 90° C. for 18 hr, then cooled and filtered. The filtercake was washed with dioxane (2*50 ml) and discarded. The filtrate was evaporated in vacuo, and the residue was purified by column chromatography on silica gel using chloroform/ethyl acetate gradient (0-100% ethyl acetate) to afford tert-butyl 3-methyl-6-(3-methylsulfonylphenyl)-3,4-dihydro-2H-pyridine-1-carboxylate (8.5 g, 24.18 mmol, 46.40% yield) as yellow gum, which was used directly in the next step.

$^1$H NMR (500 MHz, CDCl$_3$) δ (ppm) 1.02 (d, 3H), 1.03 (m, 1H), 1.09 (s, 9H), 1.89 (d, 1H), 2.04 (m, 2H), 2.44 (d, 1H), 3.02 (s, 3H), 4.12 (m, 1H), 7.49 (t, 1H), 7.57 (d, 1H), 7.80 (d, 1H), 7.86 (s, 1H).

LCMS(ESI): [M-Boc]$^+$ m/z: calcd 251.4; found 252.2; Rt=1.360 min.

Step 2: Synthesis of 3-methyl-6-(3-(methylsulfonyl)phenyl)-2,3,4,5-tetrahydropyridine A solution of tert-butyl 3-methyl-6-(3-methylsulfonylphenyl)-3,4-dihydro-2H-pyridine-1-carboxylate (3 g, 8.54 mmol) in trifluoroacetic acid (29.20 g, 256.08 mmol, 19.73 mL) was stirred at 25° C. for 1 hr. After 1 hour, the reaction mixture was concentrated under reduced pressure. The obtained residue was diluted with ice cold water (50 mL) and neutralized with aqueous 10% NaOH solution till pH=10. The resulting mixture was extracted with dichloromethane (2×50 mL). The combined organic phase was dried over sodium sulphate and concentrated under reduce pressure to afford 3-methyl-6-(3-methylsulfonylphenyl)-2,3,4,5-tetrahydropyridine (2 g, 7.96 mmol, 93.22% yield) as light-yellow gum.

$^1$H NMR (500 MHz, CDCl$_3$) δ (ppm) 1.02 (d, 3H), 1.46 (m, 1H), 1.72 (m, 1H), 1.94 (m, 1H), 2.59 (m, 1H), 2.79 (m, 1H), 3.06 (s, 3H), 3.27 (m, 1H), 4.04 (d, 1H), 7.58 (t, 1H), 7.93 (d, 1H), 8.05 (d, 1H), 8.32 (s, 1H).

LCMS(ESI): [M]$^+$ m/z: calcd 251.4; found 252.2; Rt=0.584 min.

Step 3: Synthesis of rac-(2R,5S)-5-methyl-2-(3-(methylsulfonyl)phenyl)piperidine To a stirring solution of 3-methyl-6-(3-methylsulfonylphenyl)-2,3,4,5-tetrahydropyridine (2 g, 7.96 mmol) in MeOH (50 mL) was added sodium borohydride (0.9 g, 23.79 mmol, 841.12 μL) portion wise at 0° C. The resulting reaction mixture was stirred at 0° C. for 1 hr, then was allowed to warm to 25° C. and stirred for 12 hr, and then concentrated under reduced pressure. The residue was diluted with water (50 mL) and extracted with dichloromethane (2×50 mL). The combined organic extracts were dried over sodium sulphate and concentrated under vacuum to obtain crude product (2R,5S)-5-methyl-2-(3-methylsulfo- nylphenyl)piperidine (1.8 g, 7.10 mmol, 89.28% yield) as light-yellow solid, which was used directly in the next step.

$^1$H NMR (400 MHz, CDCl$_3$) δ (ppm) 0.98 (d, 3H), 1.07 (m, 1H), 1.87 (m, 5H), 2.39 (m, 1H), 3.06 (s, 3H), 3.17 (d, 1H), 3.67 (d, 1H), 7.53 (t, 1H), 7.68 (d, 1H), 7.82 (d, 1H), 7.95 (s, 1H).

LCMS(ESI): [M]$^-$ m/z: calcd 253.4; found 254.2; Rt=0.626 min.

6II. The Synthesis of rac-N-methyl-3-((2R,5S)-5-methylpiperidin-2-yl)benzenesulfonamide

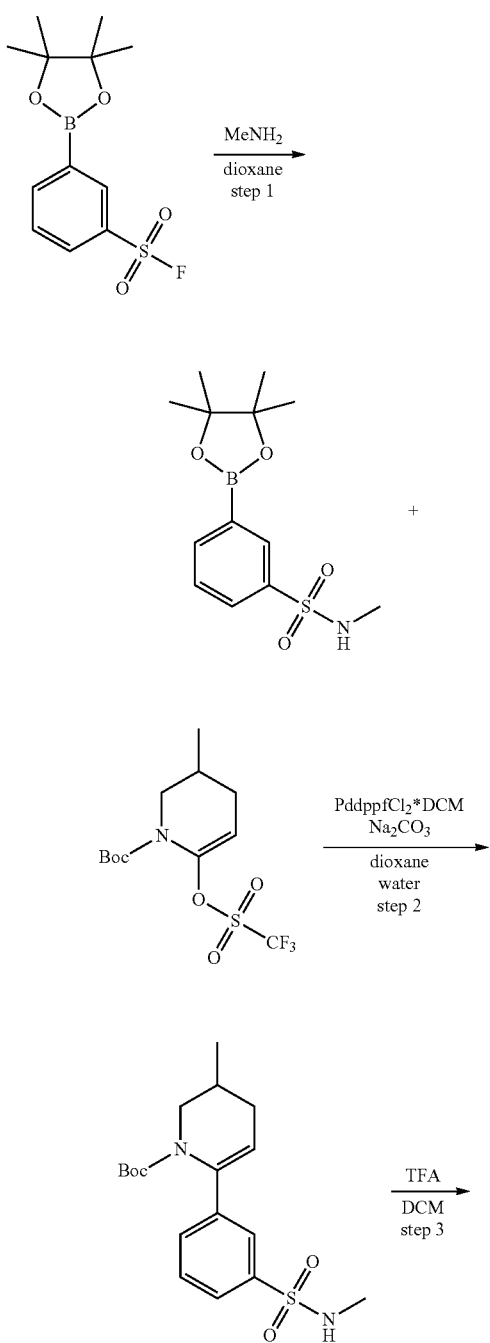

-continued

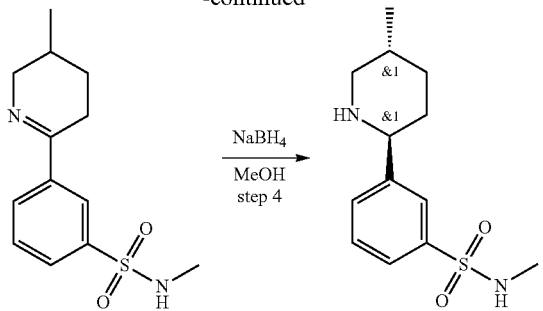

Step 1: Synthesis of N-methyl-3-(4,4,5,5-tetramethyl-1,3,2-dioxaborolan-2-yl)benzenesulfonamide Methylamine, 40% w/w aq. soln. (2.71 g, 34.95 mmol, 3.02 mL, 40% purity) was added to a solution of 3-(4,4,5,5-tetramethyl-1,3,2-dioxaborolan-2-yl)benzenesulfonyl fluoride (2 g, 6.99 mmol) in dioxane (10 mL). Resulting mixture was stirred at 20° C. for 15 hr. Then, volatiles were removed under reduced pressure and residue was diluted with water (15 ml). Resulting white precipitate was collected by filtration and dried, affording N-methyl-3-(4,4,5,5-tetramethyl-1,3,2-dioxaborolan-2-yl)benzenesulfonamide (1.75 g, 5.89 mmol, 84.25% yield).

$^1$H NMR (500 MHz, DMSO-$d_6$) δ (ppm) 1.32 (s, 12H), 2.62 (d, 3H), 4.48 (m, 1H), 7.51 (t, 1H), 7.91 (d, 1H), 7.96 (d, 1H), 8.25 (s, 1H).

LCMS(ESI): [M]$^+$ m/z: calcd 297.4; found 298.2; Rt=1.323 min.

Step 2: Synthesis of tert-butyl 3-methyl-6-(3-(N-methylsulfamoyl)phenyl)-3,4-dihydropyridine-1(2H)-carboxylate Sodium carbonate (1.56 g, 14.72 mmol, 616.74 µL) was added to a solution of N-methyl-3-(4,4,5,5-tetramethyl-1,3,2-dioxaborolan-2-yl)benzenesulfonamide (1.75 g, 5.89 mmol) and tert-butyl 3-methyl-6-(trifluoromethylsulfonyloxy)-3,4-dihydro-2H-pyridine-1-carboxylate (2.14 g, 6.18 mmol) in dioxane (17 mL) and water (6.5 mL). Reaction flask was evacuated and refilled with argon 3 times. Then, PdCl$_2$dppf*DCM (192.36 mg, 235.55 µmol) was added under stream of argon. Resulting mixture was stirred at 90° C. for 15 hr under inert atmosphere. Then, it was concentrated under reduced pressure and residue was extracted with ethyl acetate (50 ml). Obtained solution was filtered through a short pad of silica gel and evaporated under reduced pressure, affording tert-butyl 3-methyl-6-[3-(methylsulfamoyl)phenyl]-3,4-dihydro-2H-pyridine-1-carboxylate (3.98 g, crude).

$^1$H NMR (500 MHz, DMSO-$d_6$) δ (ppm) 0.89 (d, 3H), 1.01 (s, 9H), 1.36 (m, 2H), 1.91 (m, 1H), 2.38 (d, 3H), 3.07 (m, 1H), 3.56 (m, 2H), 3.92 (m, 1H), 7.53 (m, 2H), 7.64 (m, 2H).

LCMS(ESI): [M-Boc]$^+$ m/z: calcd 266.4; found 267.2; Rt=1.302 min.

Step 3: Synthesis of N-methyl-3-(5-methyl-3,4,5,6-tetrahydropyridin-2-yl)benzenesulfonamide Trifluoroacetic acid (22.20 g, 194.70 mmol, 15 mL) was added to a solution of tert-butyl 3-methyl-6-[3-(methylsulfamoyl)phenyl]-3,4-dihydro-2H-pyridine-1-carboxylate (3.97 g, 10.83 mmol) in DCM (20 mL). Resulting mixture was stirred at 20° C. for 2 hr. Then, volatiles were removed under reduced pressure and residue was diluted with water (40 ml). Insoluble tar was filtered off through a pad of cotton wool. Filtrate was basified to pH≈10-11 with 20% aq. K$_2$CO$_3$ solution and extracted with ethyl acetate (2×25 ml). Combined organic layers were dried over Na$_2$SO$_4$ and concentrated under reduced pressure, affording N-methyl-3-(3-methyl-2,3,4,5-tetrahydropyridin-6-yl)benzenesulfonamide (1.34 g, 5.03 mmol, 46.44% yield).

$^1$H NMR (500 MHz, DMSO-$d_6$) δ (ppm) 0.92 (d, 3H), 1.31 (m, 1H), 1.53 (m, 1H), 1.96 (m, 1H), 2.38 (d, 3H), 2.56 (m, 1H), 2.78 (m, 1H), 3.20 (m, 1H), 3.88 (m, 1H), 7.45 (m, 1H), 7.61 (t, 1H), 7.78 (d, 1H), 7.99 (d, 1H), 8.23 (s, 1H).

LCMS(ESI): [M]$^+$ m/z: calcd 266.4; found 267.2; Rt=0.693 min.

Step 4: Synthesis of rac-N-methyl-3-((2R,5S)-5-methylpiperidin-2-yl)benzenesulfonamide Sodium borohydride (285.49 mg, 7.55 mmol, 266.82 µL) was added portionwise to a solution of N-methyl-3-(3-methyl-2,3,4,5-tetrahydropyridin-6-yl)benzenesulfonamide (1.34 g, 5.03 mmol) in MeOH (20 mL) during 15 minutes. Resulting solution was stirred at 20° C. for 1 hr. Then, solvent was removed under reduced pressure and residue was partitioned between water (20 ml) and ethyl acetate (40 ml). Organic layer was separated, dried over Na$_2$SO$_4$ and evaporated in vacuo, affording N-methyl-3-[(2S,5R)-5-methyl-2-piperidyl]benzenesulfonamide (1.07 g, 3.99 mmol, 79.25% yield).

$^1$H NMR (500 MHz, DMSO-$d_6$) δ (ppm) 0.85 (d, 3H), 1.17 (m, 2H), 1.32 (m, 1H), 1.52 (m, 1H), 1.77 (m, 2H), 2.26 (m, 1H), 2.38 (d, 3H), 3.01 (m, 1H), 3.55 (t, 1H), 7.39 (m, 1H), 7.49 (t, 1H), 7.61 (m, 2H), 7.79 (s, 1H).

LCMS(ESI): [M]$^+$ m/z: calcd 268.4; found 269.2; Rt=0.848 min.

6JJ. Synthesis of N-methyl-5-(5-methylpiperidin-2-yl)benzo[d]thiazol-2-amine

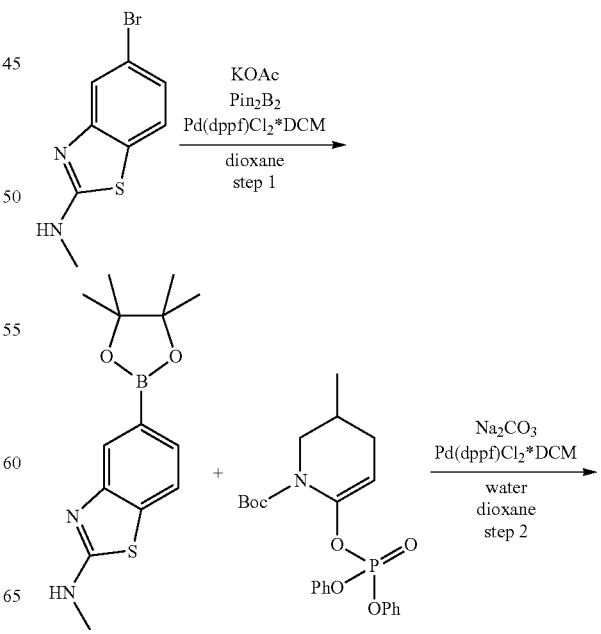

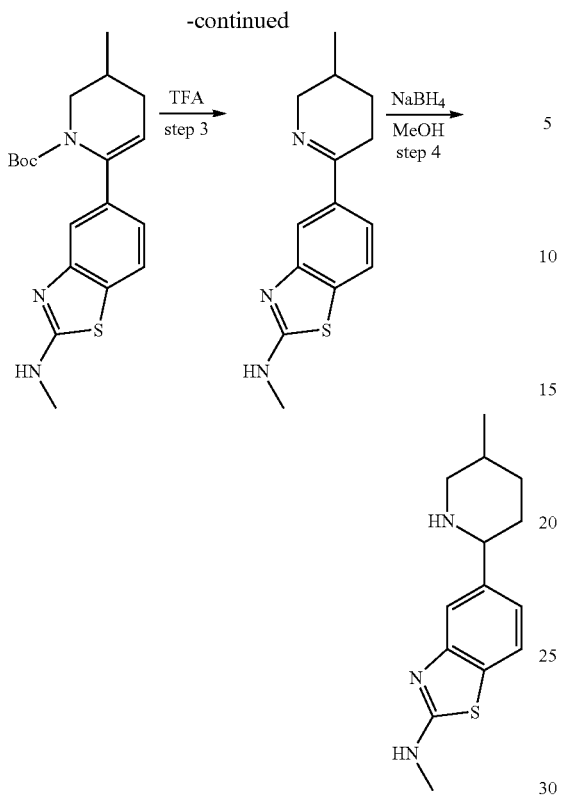

Step 1: Synthesis of N-methyl-5-(4,4,5,5-tetramethyl-1,3,2-dioxaborolan-2-yl)benzo[d]thiazol-2-amine Potassium acetate (8.88 g, 90.49 mmol, 5.66 mL) was added to a solution of 5-bromo-N-methyl-1,3-benzothiazol-2-amine (11 g, 45.24 mmol) and 4,4,5,5-tetramethyl-2-(4,4,5,5-tetramethyl-1,3,2-dioxaborolan-2-yl)-1,3,2-dioxaborolane (13.21 g, 52.03 mmol) in dioxane (150 mL). Reaction flask was evacuated and refilled with argon 3 times. Then Pd(dppf)Cl$_2$*DCM (1.85 g, 2.26 mmol) was added under stream of argon. Resulting mixture was stirred at 100° C. for 28 hr under inert atmosphere. Then, it was cooled, diluted with dioxane (700 mL) and filtered. Filtrate was concentrated under reduced pressure and the residue was purified by silica gel flash chromatography eluting with a 0 to 100 percent MTBE-chloroform gradient to give N-methyl-5-(4,4,5,5-tetramethyl-1,3,2-dioxaborolan-2-yl)-1,3-benzothiazol-2-amine (3.5 g, 12.06 mmol, 26.66% yield).

$^1$H NMR (500 MHz, DMSO-d$_6$) δ (ppm) 1.29 (s, 12H), 2.96 (d, 3H), 7.32 (d, 1H), 7.58 (d, 1H), 7.65 (s, 1H), 7.89 (bds, 1H).

LCMS(ESI): [M]$^+$ m/z: calcd 290.2; found 291.2; Rt=1.201 min.

Step 2: Synthesis of tert-butyl 3-methyl-6-(2-(methylamino)benzo[d]thiazol-5-yl)-3,4-dihydropyridine-1(2H)-carboxylate A mixture of tert-butyl 6-diphenoxyphosphoryloxy-3-methyl-3,4-dihydro-2H-pyridine-1-carboxylate (4.76 g, 9.09 mmol), N-methyl-5-(4,4,5,5-tetramethyl-1,3,2-dioxaborolan-2-yl)-1,3-benzothiazol-2-amine (2.9 g, 9.99 mmol), cyclopentyl(diphenyl)phosphane; dichloromethane; dichloropalladium; iron (370.96 mg, 454.25 μmol) and sodium carbonate (2.89 g, 27.26 mmol, 1.14 mL) in dioxane (45 mL) and water (15 mL) was stirred at 90° C. under argon atmosphere for 24 hr. After cooling to rt, the reaction mixture was filtered off. The filter cake was washed with dioxane (300 mL) and discarded. Filtrate was concentrated under reduced pressure and the residue was purified by silica gel flash chromatography eluting with a 0 to 100 percent MTBE-Hexane gradient to give the tert-butyl 3-methyl-6-[2-(methylamino)-1,3-benzothiazol-5-yl]-3,4-dihydro-2H-pyridine-1-carboxylate (1.5 g, 4.17 mmol, 45.93% yield).

$^1$H NMR (400 MHz, DMSO-d$_6$) δ (ppm) 1.02 (s, 9H), 1.12 (d, 3H), 1.78 (m, 1H), 1.94 (m, 1H), 2.32 (m, 1H), 2.96 (d, 3H), 3.11 (m, 1H), 3.91 (d, 1H), 5.22 (m, 1H), 6.88 (d, 1H), 7.18 (s, 1H), 7.42 (d, 1H), 7.76 (m, 1H).

LCMS(ESI): [M]$^+$ m/z: calcd 359.2; found 360.2; Rt=1.341 min.

Step 3: Synthesis of N-methyl-5-(5-methyl-3,4,5,6-tetrahydropyridin-2-yl)benzo[d]thiazol-2-amine The solution of tert-butyl 3-methyl-6-[2-(methylamino)-1,3-benzothiazol-5-yl]-3,4-dihydro-2H-pyridine-1-carboxylate (2 g, 5.56 mmol) in TFA (10.15 g, 89.02 mmol, 6.86 mL) was stirred at 20° C. for 1 hr, and then evaporated in vacuum. Crushed ice (20 g) was added to the residue and pH was adjusted to 8 with a 10% aqueous solution of sodium hydroxide. The resulting mixture was extracted with ethyl acetate (2*30 mL). The combined organic extracts were dried over sodium sulphate and evaporated in vacuum to afford N-methyl-5-(3-methyl-2,3,4,5-tetrahydropyridin-6-yl)-1,3-benzothiazol-2-amine (1.5 g, crude) as yellow gum, which was used directly in the next step.

$^1$H NMR (400 MHz, DMSO-d$_6$) δ (ppm) 0.94 (d, 3H), 1.32 (m, 1H), 1.62 (m, 1H), 1.85 (m, 1H), 2.49 (m, 1H), 2.74 (m, 1H), 2.94 (d, 3H), 3.33 (m, 1H), 4.02 (m, 1H), 7.52 (d, 1H), 7.64 (d, 1H), 7.77 (s, 1H), 7.96 (m, 1H).

LCMS(ESI): [M]$^+$ m/z: calcd 259.2; found 260.2; Rt=0.803 min.

Step 4: Synthesis of N-methyl-5-(5-methylpiperidin-2-yl)benzo[d]thiazol-2-amine

Sodium borohydride (328.17 mg, 8.67 mmol, 306.70 μL) was added in one portion to a stirred solution of N-methyl-5-(3-methyl-2,3,4,5-tetrahydropyridin-6-yl)-1,3-benzothiazol-2-amine (1.5 g, 5.78 mmol) in MeOH (40 mL) at 0° C. The resulting mixture was stirred at 0° C. for 1 hr, and then evaporated in vacuum. The residue was diluted with water (20 mL) and extracted with DCM (2*30 mL). The combined organic extracts were dried over sodium sulphate and evaporated in vacuum to afford N-methyl-5-[(2R,5S)-5-methyl-2-piperidyl]-1,3-benzothiazol-2-amine (1.5 g, 5.74 mmol, 99.23% yield) as yellow solid, which was used directly in the next step.

$^1$H NMR (500 MHz, DMSO-d$_6$) δ (ppm) 0.84 (d, 3H), 1.07 (m, 2H), 1.34 (m, 1H), 1.51 (m, 1H), 1.70 (m, 2H), 2.26 (m, 1H), 2.91 (d, 3H), 3.00 (m, 1H), 3.47 (d, 1H), 7.00 (d, 1H), 7.36 (s, 1H), 7.54 (d, 1H), 7.85 (m, 1H).

LCMS(ESI): [M]$^+$ m/z: calcd 261.2; found 262.2; Rt=0.787 min.

6KK. The Synthesis of 5-(5-methyl-2-piperidyl)-1,3-benzothiazole

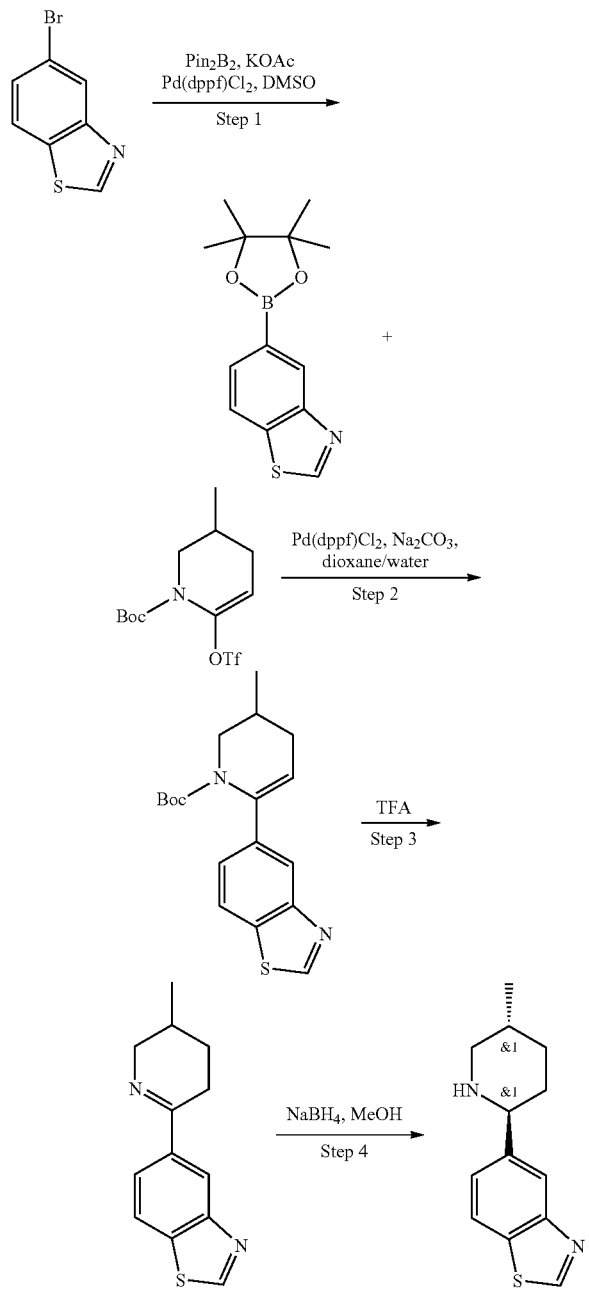

Step 1: Synthesis of 5-(4,4,5,5-tetramethyl-1,3,2-dioxaborolan-2-yl)-1,3-benzothiazole Potassium Acetate (13.75 g, 140.13 mmol, 8.76 mL) was added to a solution of 5-bromo-1,3-benzothiazole (15 g, 70.07 mmol) and 4,4,5,5-tetramethyl-2-(4,4,5,5-tetramethyl-1,3,2-dioxaborolan-2-yl)-1,3,2-dioxaborolane (20.46 g, 80.58 mmol) in DMSO (100 mL). Reaction flask was evacuated and refilled with argon 3 times. Then PdCl$_2$DPPF*CH$_2$Cl$_2$ (2.86 g, 3.50 mmol) was added under stream of argon. Resulting mixture was stirred at 90° C. for 28 hr under inert atmosphere. Then, it was cooled, diluted with MTBE (100 mL) and washed with water (2×40 mL). Organic layer was dried over Na$_2$SO$_4$ and concentrated under reduced pressure. The residue was purified by silica gel flash chromatography eluting with a 0 to 100 percent CHCl$_3$-EA gradient to give 5-(4,4,5,5-tetramethyl-1,3,2-dioxaborolan-2-yl)-1,3-benzothiazole (8.6 g, 32.93 mmol, 47.00% yield).

$^1$H NMR (CDCl$_3$, 400 MHz): δ 1.36 (s, 12H), 7.82 (d, 1H), 7.94 (d, 1H), 8.57 (s, 1H), 8.98 (s, 1H)

LCMS(ESI): [M+H]$^+$ m/z: calcd 261.1; found 261.2; Rt=1.375 min.

Step 2: Synthesis of tert-butyl 6-(1,3-benzothiazol-5-yl)-3-methyl-3,4-dihydro-2H-pyridine-1-carboxylate A mixture of tert-butyl 3-methyl-6-(trifluoromethylsulfonyloxy)-3,4-dihydro-2H-pyridine-1-carboxylate (7.72 g, 22.36 mmol), 5-(4,4,5,5-tetramethyl-1,3,2-dioxaborolan-2-yl)-1,3-benzothiazole (7.3 g, 27.95 mmol), [1,1'-Bis(diphenylphosphino)ferrocene]dichloropalladium(II), complex with dichloromethane (913.12 mg, 1.12 mmol) and sodium carbonate (7.11 g, 67.09 mmol, 2.81 mL) in dioxane (120 mL) and water (40 mL) was stirred at 80° C. under argon atmosphere for 18 hr. After cooling to room temperature, the reaction mixture was filtered off. The filtercake was washed with dioxane (500 mL) and discarded. Filtrate was concentrated under reduced pressure and the residue was purified by silica gel flash chromatography eluting with a 0 to 100 percent MTBE-Hexane gradient to give tert-butyl 6-(1,3-benzothiazol-5-yl)-3-methyl-3,4-dihydro-2H-pyridine-1-carboxylate (5.9 g, 17.85 mmol, 79.84% yield).

$^1$H NMR (DMSO-d$_6$, 500 MHz): δ 0.95-1.03 (m, 12H), 1.86 (m, 1H), 1.90 (s, 1H), 2.50 (m, 1H), 3.0 (t, 1H), 3.97 (d, 1H), 5.41 (s, 1H). 7.37 (d, 1H), 7.78 (s, 1H), 7.99 (d, 1H), 9.27 (s, 1H)

LCMS(ESI): [M+H]$^+$ m/z: calcd 330.2; found 331.2; Rt=1.435 min.

Step 3: Synthesis of 5-(3-methyl-2,3,4,5-tetrahydropyridin-6-yl)-1,3-benzothiazole The solution of tert-butyl 6-(1,3-benzothiazol-5-yl)-3-methyl-3,4-dihydro-2H-pyridine-1-carboxylate (5.9 g, 17.85 mmol) in TFA (32.57 g, 285.68 mmol, 22.01 mL) was stirred at 20° C. for 1 hr, and then evaporated in vacuo. Crushed ice (10 g) was added to the residue and pH was adjusted to 8 with a 10% aqueous solution of sodium hydroxide. The resulting mixture was extracted with ethylacetate (2*30 mL). The combined organic extracts were dried over sodium sulphate and evaporated in vacuo to afford 5-(3-methyl-2,3,4,5-tetrahydropyridin-6-yl)-1,3-benzothiazole (4.1 g, 17.80 mmol, 99.70% yield) as yellow solid, which was used directly in the next step.

$^1$H NMR (DMSO-d$_6$, 500 MHz): δ 0.95 (m, 3H), 1.35 (m, 1H), 1.65 (m, 1H), 1.89 (m, 1H), 2.67 (m, 1H), 2.87 (d, 1H), 3.19 (t, 1H). 3.95 (d, 1H), 8.02 (d, 1H), 8.14 (d, 1H), 8.43 (s, 1H), 9.41 (s, 1H)

LCMS(ESI): [M+H]$^+$ m/z: calcd 230.1; found 231.2; Rt=0.828 min.

Step 4: Synthesis of 5-(5-methyl-2-piperidyl)-1,3-benzothiazole

Sodium borohydride (1.01 g, 26.70 mmol, 944.02 µL) was added in one portion to a stirred solution of 5-(3-methyl- 2,3,4,5-tetrahydropyridin-6-yl)-1,3-benzothiazole (4.1 g, 17.80 mmol) in methanol (90 mL) at 0° C. The resulting mixture was stirred at 0° C. for 1 hr, and then evaporated in vacuo. The residue was diluted with water (50 mL) and extracted with dichloromethane (2*75 mL). The combined organic extracts were dried over sodium sulphate and evaporated in vacuo to afford 5-(5-methyl-2-piperidyl)-1,3-benzothiazole (4.1 g, 17.65 mmol, 99.13% yield) as yellow oil, which was used directly in the next step.

$^1$H NMR (DMSO-$d_6$, 400 MHz): δ 0.82 (d, 3H), 1.05 (m, 1H), 1.34 (m, 1H), 1.52 (m, 1H), 1.75 (m, 2H), 2.26 (t, 1H), 3.00 (d, 1H). 3.61 (d, 1H), 7.46 (d, 1H), 8.03 (m, 2H), 9.31 (s, 1H)

LCMS(ESI): [M+H]$^+$ m/z: calcd 232.1; found 233.0; Rt=0.691 min.

6LL. The Synthesis of 5-[(2R,5S)-5-methyl-2-piperidyl]-1,3-benzothiazole

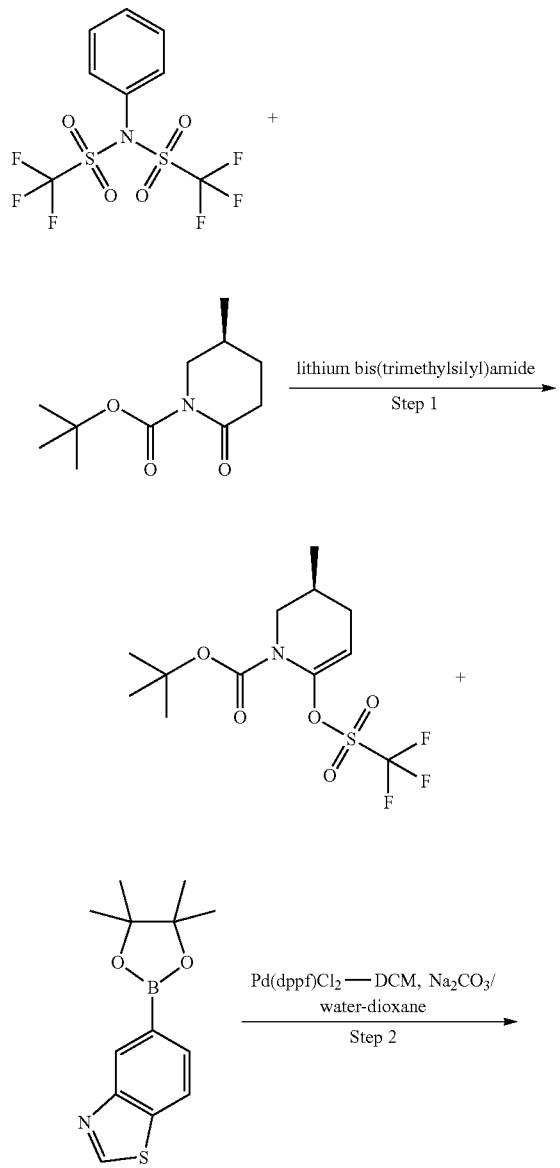

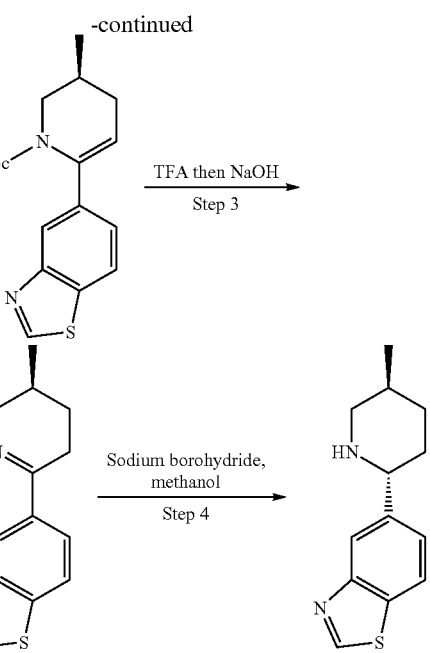

Step 1. Synthesis of tert-butyl (3S)-3-methyl-6-(trifluoromethylsulfonyloxy)-3,4-dihydro-2H-pyridine-1-carboxylate lithium bis(trimethylsilyl)amide (102.00 g, 121.91 mmol, 113.33 mL, 20% purity) (1.08 M in THF/ethylbenzene) was added for 0.5 hr dropwise under argon to a cooled to −78° C. solution of tert-butyl (5S)-5-methyl-2-oxo-piperidine-1-carboxylate (20 g, 93.78 mmol) in THF (200 mL). The resulting solution was stirred at −78° C. for 1.5 hr, then 1,1,1-trifluoro-N-phenyl-N-(trifluoromethylsulfonyl)methanesulfonamide (41.88 g, 117.22 mmol) was added in one portion. The reaction mixture was allowed to warm slowly (cooling bath was not removed!) to 25° C. and stirred for 12 hr, then diluted with water (50 ml) and MTBE (250 ml). The organic layer was separated, the aqueous layer was additionally extracted with MTBE (50 ml). The combined organic extracts were washed with 10% aqueous sodium hydroxide solution (3*15 ml), dried over potassium carbonate and concentrated in vacuo. The residue was diluted with hexane/MTBE mixture (3/1, 200 ml, repeated 8 times) and stirred for 0.5 hr. The resulting cloudy solution was decanted from oily residue, filtered through a short pad of silica gel (40 ml of dry silica gel) and evaporated in vacuo to afford crude tert-butyl (3S)-3-methyl-6-(trifluoromethylsulfonyloxy)-3,4-dihydro-2H-pyridine-1-carboxylate (32 g, 92.66 mmol, 98.81% yield) as light-yellow oil, which was used directly in the next step.

$^1$H NMR (500 MHz, CDCl$_3$) δ (ppm) 0.99 (d, 1H), 1.49 (s, 9H), 1.80-1.90 (m, 2H), 2.40 (m, 1H), 2.99 (dd, 1H), 3.88 (d, 1H), 5.25 (t, 1H).

LCMS(ESI): [M-$^t$Bu]$^+$ m/z: calcd 345.0; found 290.0; Rt=1.710 min.

Step 2. Synthesis of tert-butyl (3S)-6-(1,3-benzothiazol-5-yl)-3-methyl-3,4-dihydro-2H-pyridine-1-carboxylate A mixture of tert-butyl (3 S)-3-methyl-6-(trifluoromethylsulfonyloxy)-3,4-dihydro-2H-pyridine-1-carboxylate (32 g, 83.40 mmol), 5-(4,4,5,5-tetramethyl-1,3,2-dioxaborolan-2-yl)-1,3-benzothiazole (23.96 g, 91.74 mmol), cyclopentyl(diphenyl)phosphane; dichloromethane; dichloropalladium; iron (3.41 g, 4.17 mmol) and sodium carbonate (26.52 g, 250.19 mmol, 10.48 mL) in dioxane (525 mL) and water (175 mL) was stirred at 90° C. under argon atmosphere for 18 hr. After cooling to room temperature, the reaction mixture was filtered off. The filtercake was washed with dioxane (300 mL) and discarded. Filtrate was concentrated under reduced pressure and the residue was purified by silica gel flash chromatography eluting with a 0 to 100 percent hexane-MTBE gradient to give the tert-butyl (3S)-6-(1,3-benzothiazol-5-yl)-3-methyl-3,4-dihydro-2H-pyridine-1-carboxylate (14 g, 42.37 mmol, 50.80% yield).

$^1$H NMR (CDCl$_3$, 500 MHz): δ 1.03 (s, 9H), 1.35 (m, 1H), 1.92 (m, 1H), 2.05 (m, 1H), 2.42 (m, 1H), 3.03 (t, 1H), 4.13 (d, 1H). 5.42 (s, 1H), 7.26 (d, 1H), 7.42 (d, 1H), 8.07 (s, 1H), 8.98 (s, 1H)

LCMS(ESI): [M+H]$^+$ m/z: calcd 330.1; found 331.2; Rt=1.596 min.

Step 3. Synthesis of 5-[(3S)-3-methyl-2,3,4,5-tetrahydropyridin-6-yl]-1,3-benzothiazole The solution of tert-butyl (3S)-6-(1,3-benzothiazol-5-yl)-3-methyl-3,4-dihydro-2H-pyridine-1-carboxylate (14.35 g, 43.43 mmol) in TFA (79.22 g, 694.82 mmol, 53.53 mL) was stirred at 20° C. for 1 hr, and then evaporated in vacuo. Crushed ice (70 g) was added to the residue and pH was adjusted to 8 with a 10% aqueous solution of sodium hydroxide. The resulting mixture was extracted with ethylacetate (2*100 mL). The combined organic extracts were dried over sodium sulphate and evaporated in vacuo to afford 5-[(3S)-3-methyl-2,3,4,5-tetrahydropyridin-6-yl]-1,3-benzothiazole (10 g, 43.42 mmol, 99.98% yield) as yellow solid, which was used directly in the next step.

$^1$H NMR (DMSO-d$_6$, 500 MHz): δ 0.95 (m, 3H), 1.35 (m, 1H), 1.65 (m, 1H), 1.89 (m, 1H), 2.67 (m, 1H), 2.87 (d, 1H), 3.19 (t, 1H). 3.95 (d, 1H), 8.02 (d, 1H), 8.14 (d, 1H), 8.43 (s, 1H), 9.41 (s, 1H)

LCMS(ESI): [M+H]$^+$ m/z: calcd 230.1; found 231.2; Rt=0.828 min.

Step 4. The Synthesis of 5-[(2R,5S)-5-methyl-2-piperidyl]-1,3-benzothiazole

Sodium borohydride (2.46 g, 65.12 mmol, 2.30 mL) was added in one portion to a stirred solution of 5-[(3S)-3-methyl-2,3,4,5-tetrahydropyridin-6-yl]-1,3-benzothiazole (10.00 g, 43.42 mmol) in methanol (200 mL) at 0° C. The resulting mixture was stirred at 0° C. for 1 hr, and then evaporated in vacuo. The residue was diluted with water (100 mL) and extracted with dichloromethane (2*80 mL). The combined organic extracts were dried over sodium sulphate and evaporated in vacuo to afford 5-[(2R,5S)-5-methyl-2-piperidyl]-1,3-benzothiazole (10 g, 43.04 mmol, 99.13% yield) as yellow oil, which was used directly in the next step.

$^1$H NMR (DMSO-d$_6$, 400 MHz): δ 0.91 (d, 3H), 1.18 (m, 1H), 1.30-1.60 (m, 6H), 2.47 (t, 1H), 3.17 (d, 1H), 3.73 (d, 1H), 7.52 (d, 1H). 7.88 (d, 1H), 8.12 (s, 1H), 8.98 (s, 1H).

LCMS(ESI): [M+H]$^+$ m/z: calcd 232.1; found 233.0; Rt=0.691 min.

6MM. Synthesis of 2-(4,4-difluorocyclohexyl)piperidine

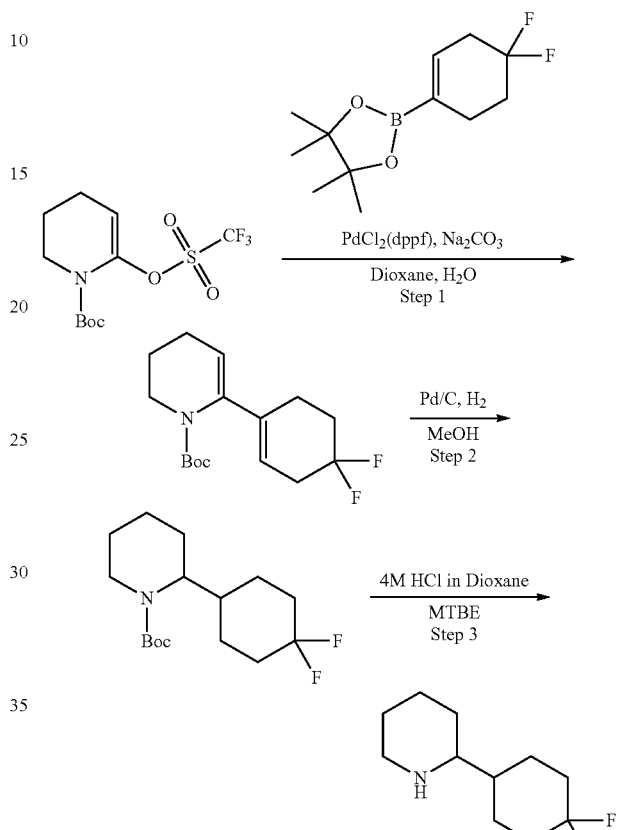

Step 1: Synthesis of tert-butyl 6-(4,4-difluorocyclohexan-1-yl)-3,4-dihydro-2H-pyridine-1-carboxylate A stirring solution of tert-butyl 6-(trifluoromethylsulfonyloxy)-3,4-dihydro-2H-pyridine-1-carboxylate (8 g, 24.15 mmol), 2-(4,4-difluorocyclohexan-1-yl)-4,4,5,5-tetramethyl-1,3,2-dioxaborolane (6.48 g, 26.56 mmol) and Sodium carbonate (5.12 g, 48.29 mmol, 2.02 mL) in 1,4-dioxane (75 mL) and Water (25 mL) was purged with argon. Then, Pd(dppf)C$_{12}$ (985.95 mg, 1.21 mmol) was added under argon. The reaction mixture was stirred under argon at 75° C. for 18 hours After 18 hours, the reaction mixture was filtered. The filter cake was washed with 1,4-dioxane (2×25 mL) and discarded. The filtrate was evaporated in vacuo, and the residue was taken up in a mixture of water (100 mL) and MTBE (150 mL). The organic layer was separated. The aqueous layer was extracted with MTBE (100 mL). The combined organic layer were dried over Na$_2$SO$_4$, filtered and evaporated under reduced pressure. The residue was purified by column chromatography to obtain tert-butyl 6-(4,4-difluorocyclohexan-1-yl)-3,4-dihydro-2H-pyridine-1-carboxylate (3.40 g, 11.36 mmol, 47.04% yield) as a yellow oil.

LCMS(ESI): [M+Boc]+ m/z: calcd 299.2; found 244.0 (t-Bu cleaved product mass); Rt=1.668 min.

Step 2: Synthesis of tert-butyl 2-(4,4-difluorocyclohexyl)piperidine-1-carboxylate A solution of tert-butyl 6-(4,4-difluorocyclohexan-1-yl)-3,4-dihydro-2H-pyridine-1-carboxylate (3.40 g, 11.36 mmol) in methanol (120 mL) was hydrogenated over Palladium, 10% on carbon, Type 487 (483.48 mg, 4.54 mmol) under hydrogen atmosphere (30 atm) at room temperature for 48 hours. Upon completion, the reaction mixture was filtered and the filtrate was evaporated under reduced pressure to afford tert-butyl 2-(4,4-difluorocyclohexyl)piperidine-1-carboxylate (2.83 g, 9.33 mmol, 82.13% yield) as light-yellow gum. The crude product was used directly in the next step.

GCMS: m/z: calcd 303.2; found 246.1; Rt=9.752 min.

Step 3: Synthesis of 2-(4,4-difluorocyclohexyl)piperidine

To a stirred solution of tert-butyl 2-(4,4-difluorocyclohexyl)piperidine-1-carboxylate (2.83 g, 9.33 mmol) in MTBE (50 mL) was added 4.0 M HCl in dioxane (1.36 g, 37.31 mmol, 1.70 mL). The resulting reaction mixture was stirred for overnight at room temperature. The reaction mixture was then concentrated under reduced pressure. LCMS indicated no progress of the reaction. The residue was dissolved in MeOH (15 mL) and 4.0 M HCl in dioxane (15 mL) was added. The resulting reaction mixture was stirred for 2 hours and then concentrated under reduced pressure to obtain 2-(4,4-difluorocyclohexyl)piperidine (2.6 g, crude, HCl) as a red gum. The crude product was used in the next step reaction without any further purification.

6NN. The Synthesis of 2-(Benzothiophen-3-yl)-5-methyl-piperidine

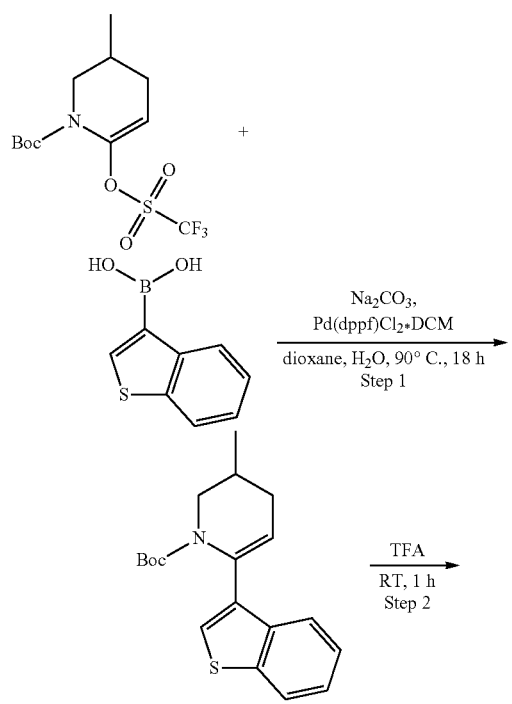

Step 1: The Synthesis of tert-butyl 6-(Benzothiophen-3-yl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (8 g, 20.85 mmol), benzothiophen-3-ylboronic acid (4.45 g, 25.02 mmol) and sodium carbonate (7.29 g, 68.80 mmol, 2.88 mL) were added to a mixture of 1,4-dioxane (100 mL) and water (30 mL). The resulting mixture was evacuated and then backfilled with argon, this operation was repeated three times, then Pd(dppf)Cl₂*DCM (851.32 mg, 1.04 mmol) was added under argon. The reaction mixture was stirred under argon at 90° C. for 18 hr, then cooled and filtered. The filtercake was washed with dioxane (2*30 mL) and discarded. The filtrate was evaporated in vacuo, and the residue was purified by column chromatography on silica gel using hexane/MTBE gradient (0-100% MTBE) to afford tert-butyl 6-(benzothiophen-3-yl)-3-methyl-3,4-dihydro-2H-pyridine-1-carboxylate (4.2 g, 12.75 mmol, 61.14% yield) as red gum.

¹H NMR (500 MHz, CDCl₃) δ 0.87 (s, 9H), 1.22 (m, 3H), 1.90 (m, 1H), 2.10 (m, 1H), 2.44 (m, 1H), 3.13 (m, 1H), 4.19 (m, 1H), 5.38 (m, 1H), 7.22 (s, 1H), 7.35 (m, 2H), 7.80 (m, 2H).

LCMS(ESI): [M-t-Bu]+ m/z: calcd 273.0; found 274.1; Rt=1.608 min.

Step 2: The Synthesis of 6-(Benzothiophen-3-yl)-3-methyl-2,3,4,5-tetrahydropyridine The mixture of tert-butyl 6-(benzothiophen-3-yl)-3-methyl-3,4-dihydro-2H-pyridine-1-carboxylate (4.20 g, 12.75 mmol) in trifluoroacetic acid (29.60 g, 259.60 mmol, 20 mL) was stirred at 25° C. for 1 hr. After 1 hour, the reaction mixture was concentrated under reduced pressure. The obtained residue was diluted with ice cold water (50 mL) and neutralized with aqueous 10% NaOH solution till pH 10. The resulting suspension was extracted with dichloromethane (3*30 mL). The combined organic phase was washed with water (30 mL), dried over sodium sulphate, filtered and concentrated under reduce pressure to obtain product 6-(benzothiophen-3-yl)-3-methyl-2,3,4,5-tetrahydropyridine (2.20 g, 9.59 mmol, 75.25% yield) as an off-white solid. The crude product was used for the next step reaction.

¹H NMR (400 MHz, CDCl₃) δ 1.04 (m, 3H), 1.44 (m, 1H), 1.79 (m, 1H), 1.95 (m, 1H), 2.68 (m, 1H), 2.85 (m, 1H), 3.36 (m, 1H), 4.10 (d, 1H), 7.40 (m, 2H), 7.71 (s, 1H), 7.84 (d, 1H), 8.80 (m, 1H).

LCMS(ESI): [M+H]+ m/z: calcd 229.1; found 230.2; Rt=0.839 min.

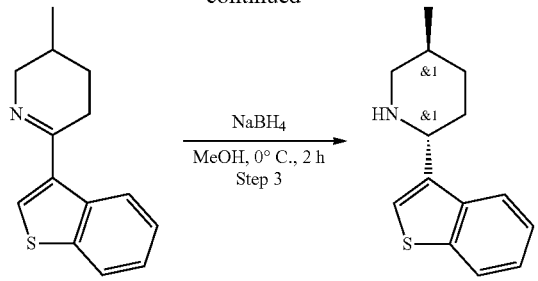

Step 3: The Synthesis of 2-(Benzothiophen-3-yl)-5-methyl-piperidine

To a stirring solution of 6-(benzothiophen-3-yl)-3-methyl-2,3,4,5-tetrahydropyridine (2.20 g, 9.59 mmol) in methanol (60 mL), sodium borohydride (544.38 mg, 14.39 mmol) was added portionwise at 0° C. The resulting reaction mixture was stirred at the same temperature for 2 hr. Then, the reaction mixture was concentrated under reduced pressure to obtain red gum residue. The obtained residue was diluted with water (30 mL) and extracted with dichloromethane (3*30 mL). The combined organic phase was washed with water (30 mL), dried over sodium sulphate, filtered and concentrated under vacuum to obtain crude product 2-(benzothiophen-3-yl)-5-methyl-piperidine (2.20 g, crude) as a red gum. The crude product was used for the next step reaction. The crude product contains ~10-11% of cis-impurity.

$^1$H NMR (400 MHz, CDCl$_3$) δ 0.94 (m, 3H), 1.30 (m, 1H), 1.69 (m, 2H), 1.73 (m, 2H), 2.01 (m, 1H), 2.61 (m, 1H), 3.21 (m, 1H), 3.98 (m, 1H), 7.36 (m, 3H), 7.87 (m, 2H).

LCMS(ESI): [M+H]$^+$ m/z: calcd 231.1; found 232.2; Rt=0.977 min.

6OO. The Synthesis of 3-(5-methyl-2-piperidyl)Cyclohexanol

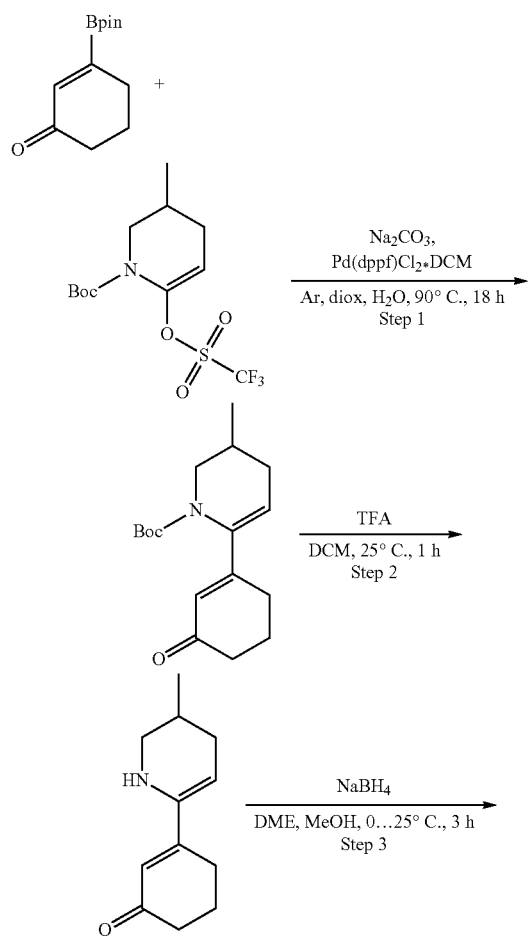

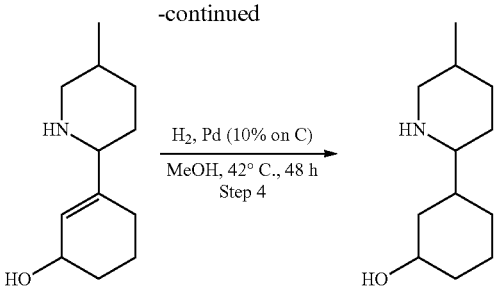

Step 1: The Synthesis of tert-butyl 3-methyl-6-(3-oxocyclohexen-1-yl)-3,4-dihydro-2H-pyridine-1-carboxylate tert-butyl 3-methyl-6-(trifluoromethylsulfonyloxy)-3,4-dihydro-2H-pyridine-1-carboxylate (16.5 g, 47.78 mmol), 3-(4,4,5,5-tetramethyl-1,3,2-dioxaborolan-2-yl)cyclohex-2-en-1-one (10.61 g, 47.78 mmol) and Sodium carbonate (15.19 g, 143.34 mmol, 6.00 mL) were added to a mixture of 1,4-dioxane (180 mL) and water (60 mL). The resulting mixture was evacuated and then backfilled with argon, this operation was repeated three times, then Pd(dppf)Cl$_2$*DCM (1.56 g, 1.91 mmol) was added under argon. The reaction mixture was stirred under argon at 90° C. for 18 hr, then cooled and filtered. The filtercake was washed with 1,4-dioxane (2*20 ml) and discarded. The filtrate was evaporated in vacuo, and the residue was purified by column chromatography on silica gel using hexane/MTBE gradient (5-100% MTBE) to afford tert-butyl 3-methyl-6-(3-oxocyclohexen-1-yl)-3,4-dihydro-2H-pyridine-1-carboxylate (9 g, 30.89 mmol, 64.64% yield) as light-yellow gum.

$^1$H NMR (400 MHz, CDCl$_3$) δ 0.99 (d, 3H), 1.42 (s, 9H), 1.80 (m, 1H), 2.02 (m, 3H), 2.39 (m, 2H), 2.86 (m, 3H), 2.89 (m, 1H), 3.92 (m, 1H), 5.51 (m, 1H), 6.06 (s, 1H).

LCMS(ESI): [M-$^t$Bu]$^+$ m/z: calcd 235.2; found 236.2; Rt=1.358 min.

Step 2: The Synthesis of 3-(3-methyl-2,3,4,5-tetrahydropyridin-6-yl)Cyclohex-2-en-1-one Trifluoroacetic acid (150 g, 1.32 mol, 101.35 mL) was added to tert-butyl 3-methyl-6-(3-oxocyclohexen-1-yl)-3,4-dihydro-2H-pyridine-1-carboxylate (9 g, 30.89 mmol) at 25° C. The resulting reaction mixture was stirred at 25° C. for 1 hr, then evaporated in vacuo to afford crude 3-(3-methyl-2,3,4,5-tetrahydropyridin-6-yl)cyclohex-2-en-1-one (15 g, crude) as orange gum, which was used directly in the next step.

$^1$H NMR (500 MHz, CDCl$_3$) δ 1.11 (s, 3H), 1.56 (m, 1H), 2.11 (m, 4H), 3.16 (m, 4H), 3.36 (m, 1H), 3.38 (m, 1H), 3.40 (m, 1H), 4.01 (m, 1H), 6.73 (s, 1H).

LCMS(ESI): [M+H]$^+$ m/z: calcd 191.1; found 192.2; Rt=0.535 min.

Step 3: The Synthesis of 3-(5-methyl-2-piperidyl)Cyclohex-2-en-1-ol

Sodium Borohydride (6 g, 158.60 mmol, 5.61 mL) was added portionwise over 0.2 hr to a stirred solution of 3-(3-methyl-2,3,4,5-tetrahydropyridin-6-yl)cyclohex-2-en-1-one (15 g, 78.42 mmol) in DME (300 mL) at 0° C. The reaction mixture was stirred at 0° C. for 2 hr, then methanol (100 mL) was added at 0° C. slowly to quench the reaction (foaming!). The resulting mixture was allowed to warm to 25° C., stirred for 0.5 hr, and then evaporated in vacuo. The residue was diluted with water (200 ml) and pH was adjusted to 10 with 10% aqueous sodium hydroxide solution. The resulting cloudy solution was extracted with dichloromethane (2*150 ml). The combined organic extracts were dried over sodium sulphate and evaporated in vacuo. The residue was reevaporated with 100 ml of MTBE to afford crude 3-(5-methyl-2-piperidyl)cyclohex-2-en-1-ol (4.5 g, 23.04 mmol, 29.38% yield) as light-yellow foam, which was used directly in the next step.

¹H NMR (400 MHz, CDCl₃) δ 0.91 (m, 3H), 1.77 (m, 10H), 1.79 (m, 1H), 2.35 (m, 1H), 3.29 (m, 1H), 4.16 (m, 1H), 5.71 (m, 1H).

LCMS(ESI): [M+H]⁺ m/z: calcd 195.2; found 196.2; Rt=0.327 min.

Step 4: The Synthesis of 3-(5-methyl-2-piperidyl)Cyclohexanol

A mixture of 3-(5-methyl-2-piperidyl)cyclohex-2-en-1-ol (4.5 g, 23.04 mmol) and Palladium, 10% on carbon (0.5 g, 23.04 mmol) in methanol (100 mL) was stirred under atmosphere of hydrogen at 42° C. for 48 hr. The catalyst was filtered off, the filtrate was evaporated in vacuo to afford 3-(5-methyl-2-piperidyl)cyclohexanol (4 g, 20.27 mmol, 87.98% yield) as light-yellow gum, which was used directly in the next step.

¹H NMR (400 MHz, CDCl₃) δ 0.95 (d, 3H), 1.14 (m, 6H), 1.68 (m, 5H), 1.93 (m, 2H), 2.21 (m, 2H), 3.01 (m, 1H), 3.54 (m, 1H), 4.08 (m, 1H).

LCMS(ESI): [M+H]⁺ m/z: calcd 197.2; found 198.2; Rt=0.512 min.

6PP. The Synthesis of 2-methoxy-4-(5-methyl-2-piperidyl)pyridine

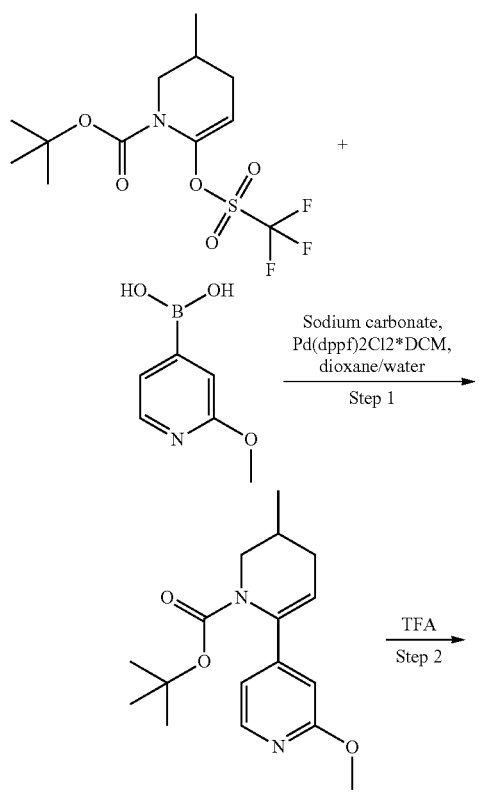

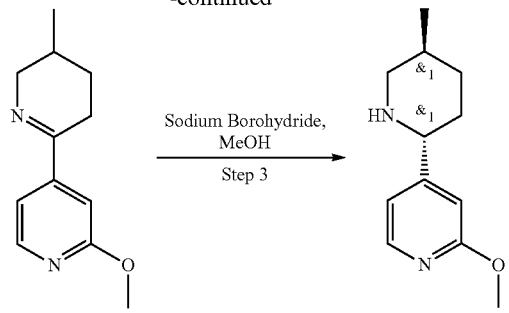

Step 1: Synthesis of tert-butyl 6-(2-methoxy-4-pyridyl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (5 g, 14.48 mmol), (2-methoxy-4-pyridyl)boronic acid (2.21 g, 14.48 mmol) and Sodium carbonate (4.60 g, 43.44 mmol, 1.82 mL) were added to a mixture of water (15 mL) and dioxane (45 mL). The resulting mixture was evacuated and then backfilled with argon, this operation was repeated three times, then Pd(dppf)₂Cl₂*DCM (723.93 μmol) was added under argon. The reaction mixture was stirred under argon at 70° C. for 16 hr, then cooled and filtered. The filtercake was washed with 1,4-dioxane (2*20 ml) and discarded. The filtrate was evaporated in vacuo to afford tert-butyl 6-(2-methoxy-4-pyridyl)-3-methyl-3,4-dihydro-2H-pyridine-1-carboxylate (3 g, 9.86 mmol, 68.07% yield) as brown oil, which was used in next step without purification.

LCMS(ESI): [M+H]⁺ m/z: calcd 304.2; found 305.2; Rt=1.437 min.

Step 2: Synthesis of 2-methoxy-4-(3-methyl-2,3,4,5-tetrahydropyridin-6-yl)pyridine The solution of tert-butyl 6-(2-methoxy-4-pyridyl)-3-methyl-3,4-dihydro-2H-pyridine-1-carboxylate (3 g, 9.86 mmol) in TFA (11.24 g, 98.56 mmol, 7.59 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 2-methoxy-4-(3-methyl-2,3,4,5-tetrahydropyridin-6-yl)pyridine (2 g, 9.79 mmol, 99.34% yield) as brown solid, which was used directly in the next step.

LCMS(ESI): [M+H]⁺ m/z: calcd 206.2; found 207.2; Rt=0.628 min.

Step 3: Synthesis of 2-methoxy-4-(5-methyl-2-piperidyl)pyridine

Sodium Borohydride (740.84 mg, 19.58 mmol, 692.38 μL) was added in one portion to a stirred solution of 2-methoxy-4-(3-methyl-2,3,4,5-tetrahydropyridin-6-yl)pyridine (2 g, 9.79 mmol) in MeOH (50 mL) at 0° C. The resulting mixture was stirred at 0° C. for 2 hr, and then evaporated in vacuo. The residue was diluted with water (20 ml) and extracted with dichloromethane (2*40 ml). The combined organic extracts were dried over sodium sulphate and evaporated in vacuo. The obtained oil was subjected to HPLC to afford 2-methoxy-4-(5-methyl-2-piperidyl)pyridine (720.2 mg, 3.49 mmol, 35.66% yield).

LCMS(ESI): [M+H]$^+$ m/z: calcd 206.2; found 207.4; Rt=1.697 min.

6QQ. The Synthesis of rac-3-methyl-5-(5-methyl-2-piperidyl)-1H-indazole

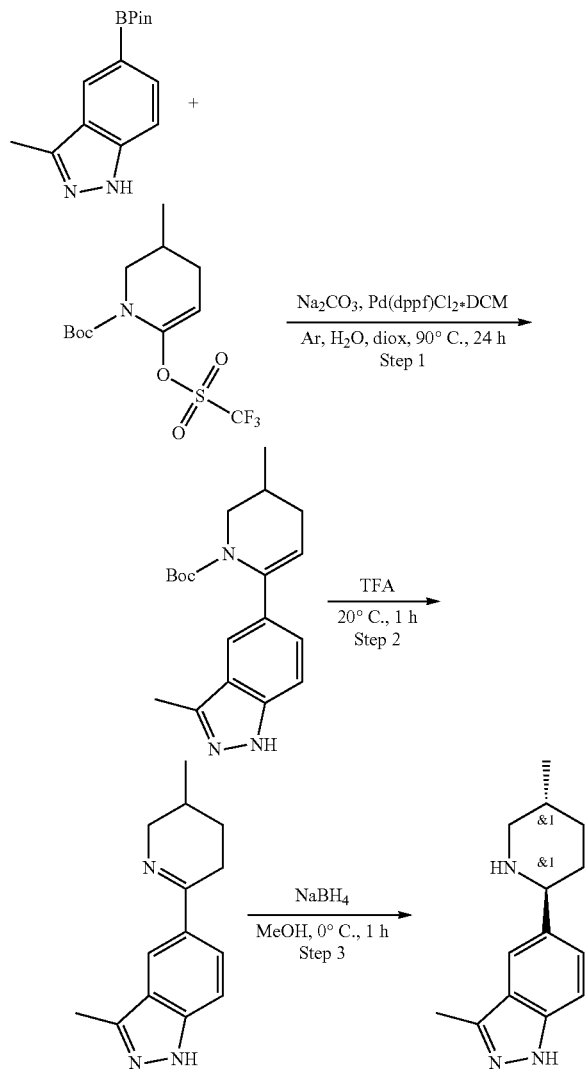

Step 1: The Synthesis of tert-butyl 3-methyl-6-(3-methyl-1H-indazol-5-yl)-3,4-dihydropyridine-1(2H)-carboxylate A mixture of tert-butyl 3-methyl-6-(trifluoromethylsulfonyloxy)-3,4-dihydro-2H-pyridine-1-carboxylate (9.86 g, 28.55 mmol), $C_{14}H_{19}BN_2O_2 \cdot HCl$ (9.25 g, 31.40 mmol, HCl), [1,1'-Bis(diphenylphosphino)ferrocene]dichloropalladium(II), complex with dichloromethane (1.17 g, 1.43 mmol) and sodium carbonate (9.08 g, 85.64 mmol, 3.59 mL) in dioxane (150 mL) and water (50 mL) was stirred at 90° C. under argon atmosphere for 24 hr. After cooling to room temperature, the reaction mixture was filtered off. The filtercake was washed with dioxane (400 mL) and discarded. Filtrate was concentrated under reduced pressure and the residue was purified by silica gel flash chromatography eluting with a 0 to 100 percent $CHCl_3$-EtOAc gradient to give tert-butyl 3-methyl-6-(3-methyl-1H-indazol-5-yl)-3,4-dihydropyridine-1(2H)-carboxylate (10 g, crude).

LCMS(ESI): [M+H]$^+$ m/z: calcd 327.2; found 328.2; Rt=1.133 min.

Step 2: The Synthesis of 3-methyl-5-(3-methyl-2,3,4,5-tetrahydropyridin-6-yl)-1H-indazole The solution of tert-butyl 3-methyl-6-(3-methyl-1H-indazol-5-yl)-3,4-dihydro-2H-pyridine-1-carboxylate (10 g, 30.54 mmol) in TFA (55.72 g, 488.67 mmol, 37.65 mL) was stirred at 20° C. for 1 hr, and then evaporated in vacuo. Crushed ice (10 g) was added to the residue and pH was adjusted to 8 with a 10% aqueous solution of sodium hydroxide. The resulting mixture was extracted with ethylacetate (2*40 mL). The combined organic extracts were dried over sodium sulphate and evaporated in vacuo to afford 3-methyl-5-(3-methyl-2,3,4,5-tetrahydropyridin-6-yl)-1H-indazole (8 g, crude) as yellow solid, which was used directly in the next step.

$^1$H NMR (400 MHz, DMSO-d$_6$) δ 0.89 (d, 3H), 1.26 (m, 2H), 1.32 (m, 1H), 1.46 (m, 1H), 2.43 (s, 3H), 2.67 (m, 1H), 2.93 (m, 1H), 3.72 (m, 1H), 7.53 (d, 1H), 7.90 (d, 1H), 8.04 (s, 1H).

LCMS(ESI): [M+H]$^+$ m/z: calcd 227.2; found 228.2; Rt=0.801 min.

Step 3: The Synthesis of rac-3-methyl-5-(5-methyl-2-piperidyl)-1H-indazole

Sodium borohydride (2.00 g, 52.79 mmol, 1.87 mL) was added in one portion to a stirred solution of 3-methyl-5-(3-methyl-2,3,4,5-tetrahydropyridin-6-yl)-1H-indazole (8 g, 35.20 mmol) in methanol (200 mL) at 0° C. The resulting mixture was stirred at 0° C. for 1 hr, and then evaporated in vacuo. The residue was diluted with water (20 mL) and extracted with dichloromethane (2*30 mL). The combined organic extracts were dried over sodium sulphate and evaporated in vacuo to afford rac-3-methyl-5-(5-methyl-2-piperidyl)-1H-indazole (4 g, 17.44 mmol, 49.56% yield) as brown solid, which was used directly in the next step.

$^1$H NMR (400 MHz, CDCl$_3$) δ 0.84 (d, 3H), 1.07 (m, 2H), 1.41 (m, 2H), 1.77 (m, 1H), 2.27 (m, 2H), 2.45 (s, 3H), 3.00 (m, 1H), 3.53 (m, 1H), 7.32 (m, 2H), 7.61 (s, 1H), 12.47 (s, 1H).

LCMS(ESI): [M+H]$^+$ m/z: calcd 229.2; found 230.2; Rt=0.830 min.

6RR. The Synthesis of 7-methyl-5-(5-methyl-2-piperidyl)-1H-indazole

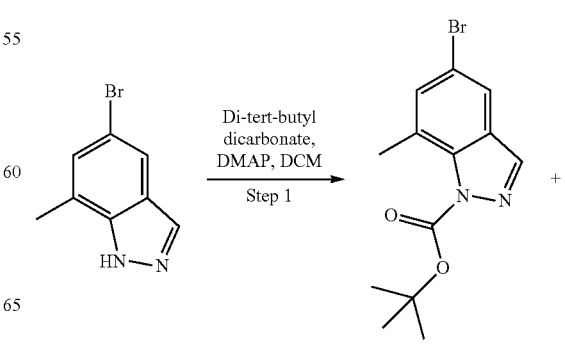

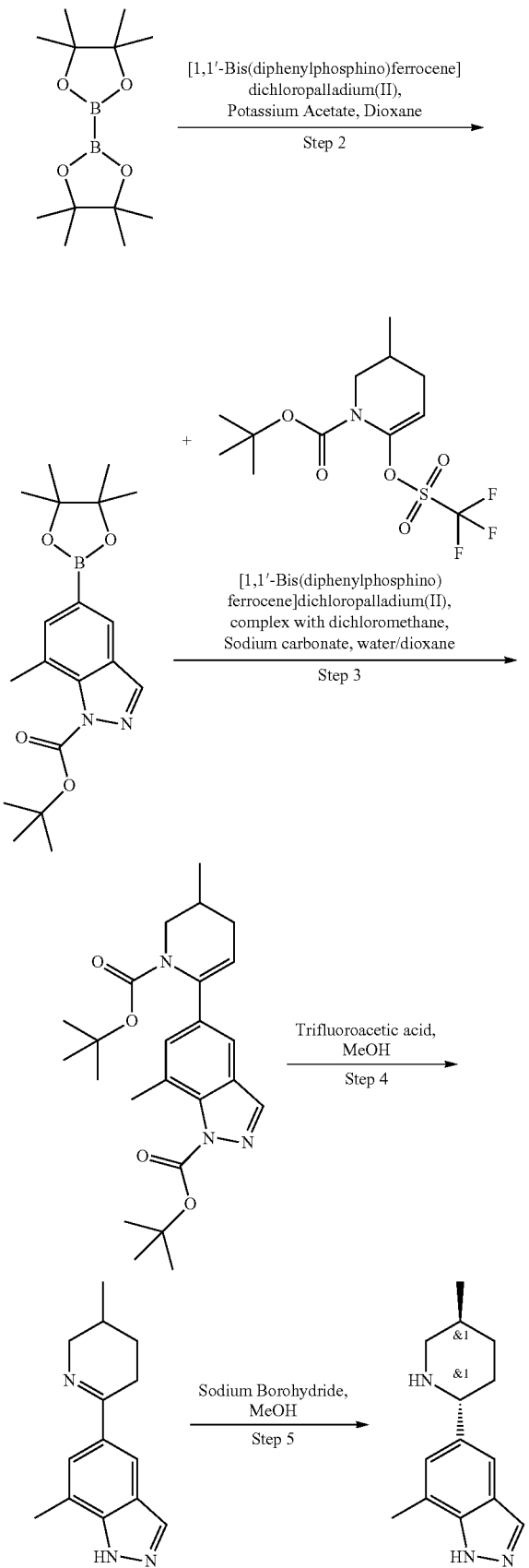

Step 1: Synthesis of tert-butyl 5-bromo-7-methyl-Indazole-1-carboxylate

Di-tert-butyl dicarbonate (8.99 g, 41.21 mmol, 9.46 mL) was added dropwise to a stirred suspension of 5-bromo-7-methyl-1H-indazole (8.53 g, 40.40 mmol) and DMAP (49.36 mg, 404.00 μmol) in DCM (100 mL) at 0° C. The resulting mixture was stirred at room temperature for 12 hr, then evaporated in vacuo poured into water (100 ml) and extracted with DCM (2×50 ml). The combined organic extracts were washed with water (2*30 ml), dried over sodium sulphate and evaporated in vacuo to afford product tert-butyl 5-bromo-7-methyl-indazole-1-carboxylate (12 g, 38.56 mmol, 95.45% yield)

$^1$H NMR (CDCl$_3$, 400 MHz): 1.69 (s, 9H), 2.59 (s, 3H), 7.12 (s, 1H), 7.60 (s, 1H), 8.46 (s, 1H).

LCMS(ESI): [M-Boc+H]$^+$ m/z: calcd 311.2; found 211.0; Rt=1.487 min.

Step 2: Synthesis of tert-butyl 7-methyl-5-(4,4,5,5-tetramethyl-1,3,2-dioxaborolan-2-yl)indazole-1-carboxylate tert-butyl 5-bromo-7-methyl-indazole-1-carboxylate (10.3 g, 33.10 mmol) and 4,4,5,5-tetramethyl-2-(4,4,5,5-tetramethyl-1,3,2-dioxaborolan-2-yl)-1,3,2-dioxaborolane (8.41 g, 33.10 mmol) were mixed together in Dioxane (150 mL). The resulting mixture was evacuated and then backfilled with argon, this operation was repeated three times, then [1,1′-Bis(diphenylphosphino)ferrocene]dichloropalladium(II) (1.35 g, 1.66 mmol) were added under argon. The reaction mixture was stirred under argon at 100° C. for 17 hr, then cooled and evaporated in vacuo poured into water (150 ml) and extracted with EtOAc (2×80 ml). The combined organic extracts were washed with water (2*40 ml), dried over sodium sulphate and evaporated in vacuo to leave 13 g of crude product, 13 g of which was purification by column chromatography on silica gel using hexane/EtOAc gradient (10-100% EtOAc) to afford product tert-butyl 7-methyl-5-(4,4,5,5-tetramethyl-1,3,2-dioxaborolan-2-yl)indazole-1-carboxylate (4.3 g, 12.00 mmol, 36.26% yield)

$^1$H NMR (CDCl$_3$, 500 MHz): 1.34 (s, 12H), 1.70 (s, 9H), 2.60 (s, 3H), 7.40 (s, 1H), 8.01 (s, 1H), 8.54 (s, 1H).

LCMS(ESI): [M-C$_4$H$_8$]$^+$ m/z: calcd 358.2; found 302.2; Rt=1.727 min.

Step 3: Synthesis of tert-butyl 5-(1-tert-butoxycarbonyl-3-methyl-3,4-dihydro-2H-pyridin-6-yl)-7-methyl-Indazole-1-carboxylate tert-butyl 7-methyl-5-(4,4,5,5-tetramethyl-1,3,2-dioxaborolan-2-yl)indazole-1-carboxylate (4.3 g, 12.00 mmol) and tert-butyl 3-methyl-6-(trifluoromethylsulfonyloxy)-3,4-dihydro-2H-pyridine-1-carboxylate (4.15 g, 12.00 mmol) were mixed together in water (1 mL). The resulting mixture was evacuated and then backfilled with argon, this operation was repeated three times, then Sodium carbonate (1.27 g, 12.00 mmol, 502.85 μL) in water (1 mL) and [1,1′-Bis(diphenylphosphino)ferrocene]dichloropalladium(II), complex with dichloromethane (439.14 mg, 600.16 μmol) were added under argon. The reaction mixture was stirred under argon at 100° C. for 80 hr, then cooled and evaporated in vacuo poured into water (120 ml) and extracted with EtOAc (2×90 ml). The combined organic extracts were washed with water (2*40 ml), dried over sodium sulphate and evaporated in vacuo to leave 8 g of crude product, 8 g of which was purification by column chromatography on silica gel using hexane/IPA gradient (10-100% IPA) to afford product tert-butyl 5-(1-tert-butoxycarbonyl-3-methyl-3,4-dihydro-2H-pyridin-6-yl)-7-methyl-indazole-1-carboxylate (3.4 g, 7.95 mmol, 66.25% yield).

LCMS(ESI): [M+H-Boc]⁺ m/z: calcd 427.5; found 328.2; Rt=1.478 min.

Step 4: Synthesis of 7-methyl-5-(3-methyl-2,3,4,5-tetrahydropyridin-6-yl)-1H-indazole The solution of tert-butyl 5-(1-tert-butoxycarbonyl-3-methyl-3,4-dihydro-2H-pyridin-6-yl)-7-methyl-indazole-1-carboxylate (3 g, 7.02 mmol) in MeOH (30 mL) and Trifluoroacetic acid (24.00 g, 210.51 mmol, 16.22 mL) was stirred at 25° C. for 8 hr, and then evaporated in vacuo. Crushed ice (20 g) was added to the residue and pH was adjusted to 8 with a 10% aqueous solution of sodium hydrocarbonate. The resulting mixture was extracted with ethylacetate (2*60 mL). The combined organic extracts were dried over sodium sulphate and evaporated in vacuo to afford 7-methyl-5-(3-methyl-2,3,4,5-tetrahydropyridin-6-yl)-1H-indazole (1 g, 4.40 mmol, 62.70% yield) as yellow solid, which was used directly in the next step.

LCMS(ESI): [M+H]⁺ m/z: calcd 227.3; found 228.2; Rt=1.207 min.

Step 5: Synthesis of 7-methyl-5-(5-methyl-2-piperidyl)-1H-indazole

Sodium Borohydride (366.17 mg, 9.68 mmol, 342.21 µL) was added in one portion to a stirred solution of 7-methyl-5-(3-methyl-2,3,4,5-tetrahydropyridin-6-yl)-1H-indazole (1.1 g, 4.84 mmol) in MeOH (20 mL) at 0° C. The resulting mixture was stirred at 0° C. for 4 hr, and then evaporated in vacuo. The residue was diluted with water (20 mL) and extracted with dichloromethane (2*50 mL). The combined organic extracts were dried over sodium sulphate and evaporated in vacuo to afford 7-methyl-5-(5-methyl-2-piperidyl)-1H-indazole (0.7 g, 3.05 mmol, 63.08% yield).

LCMS(ESI): [M+H]⁺ m/z: calcd 229.3; found 230.2; Rt=1.263 min.

6SS. Synthesis of 4-fluoro-5-(3-methyl-2,3,4,5-tetrahydropyridin-6-yl)-1H-indazole

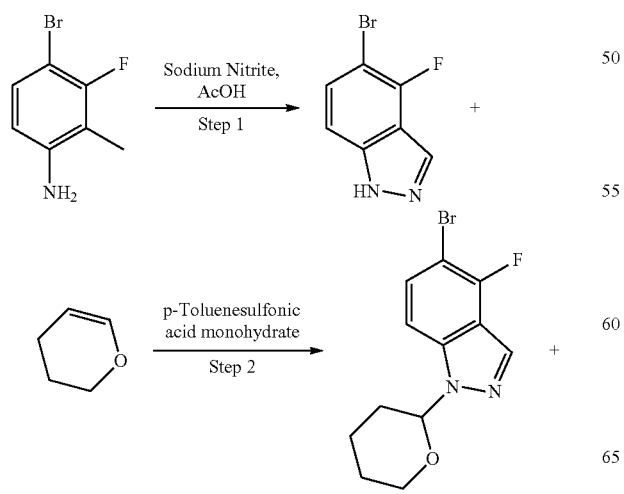

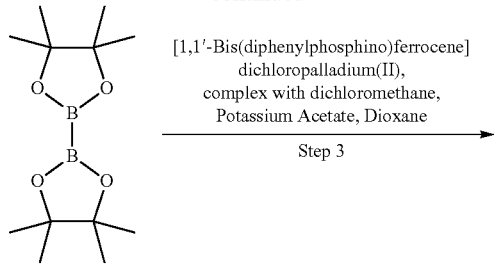

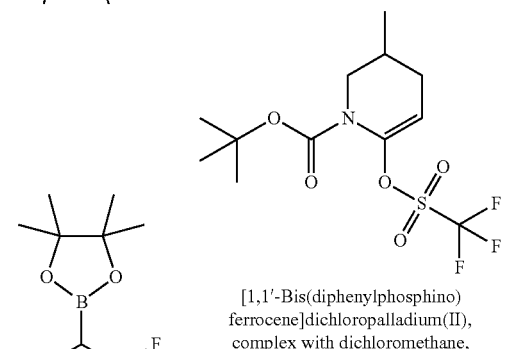

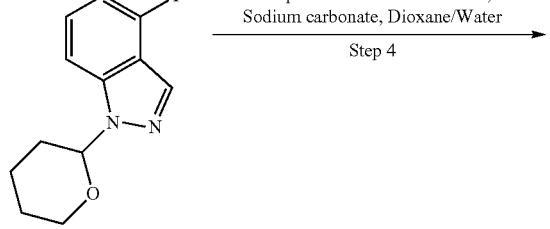

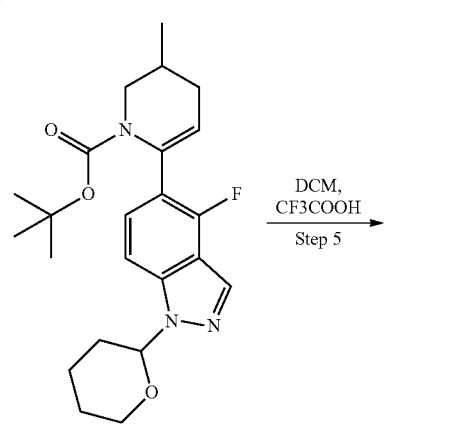

Step 1: Synthesis of 5-bromo-4-fluoro-1H-indazole 4-bromo-3-fluoro-2-methyl-aniline (10 g, 49.01 mmol) was dissolved in AcOH (200 mL) and Sodium Nitrite (4.06 g, 58.81 mmol, 1.87 mL) was added portionwise at room temperature. The resulting mixture was stirred for 18 hr. The reaction mixture was poured in water (500 ml) and the precipitation, which was formed, was filtered off, washed with water (2*200 ml). The precipitation was dissolved in DCM (400 ml), dried over $Na_2SO_4$, filtered and evaporated to obtain 5-bromo-4-fluoro-1H-indazole (8.54 g, 39.71 mmol, 81.02% yield).

LCMS(ESI): $[M+H]^+$ m/z: calcd 213.9; found 215.0; Rt=1.086 min.

Step 2: Synthesis of 5-bromo-4-fluoro-1-tetrahydropyran-2-yl-indazole 5-bromo-4-fluoro-1H-indazole (8.54 g, 39.72 mmol) and 3,4-dihydro-2H-pyran (4.18 g, 49.65 mmol, 4.51 mL) were dissolved in DCM (170 mL) and p-Toluenesulfonic acid monohydrate (377.74 mg, 1.99 mmol, 304.63 µL) was added. The reaction mixture was stirred for 20 hr. The reaction mixture was poured into aqueous $NaHCO_3$(conc.) solution and the organic layer was separated, dried over $Na_2SO_4$, filtered and evaporated to obtain 5-bromo-4-fluoro-1-tetrahydropyran-2-yl-indazole (11.76 g, 39.30 mmol, 98.95% yield).

$^1$H NMR ($CDCl_3$, 500 MHz): 1.43 (m, 2H), 1.53 (m, 1H), 1.69 (m, 2H), 1.96 (m, 1H), 3.70 (m, 1H), 3.81 (m, 1H), 5.85 (m, 1H), 7.56 (m, 2H), 8.23 (s, 1H).

LCMS(ESI): $[M+2H]^+$ m/z: calcd 298.03; found 300.8; Rt=1.244 min.

Step 3: Synthesis of 4-fluoro-1-tetrahydropyran-2-yl-5-(4,4,5,5-tetramethyl-1,3,2-dioxaborolan-2-yl)indazole 5-bromo-4-fluoro-1-tetrahydropyran-2-yl-indazole (11.25 g, 37.62 mmol), 4,4,5,5-tetramethyl-2-(4,4,5,5-tetramethyl-1,3,2-dioxaborolan-2-yl)-1,3,2-dioxaborolane (9.55 g, 37.62 mmol) and Potassium Acetate (7.38 g, 75.24 mmol, 4.70 mL) were mixed together in Dioxane (225 mL) and the resulting mixture was evacuated and backfilled three times with argon. [1,1'-Bis(diphenylphosphino)ferrocene]dichloropalladium(II), complex with dichloromethane (1.54 g, 1.88 mmol) was added thereto and the reaction mixture was heated at 100° C. for 20 hr. The reaction mixture was cooled and filtered. The filtrate was concentrated in vacuo and purified by column chromatography to obtain 4-fluoro-1-tetrahydropyran-2-yl-5-(4,4,5,5-tetramethyl-1,3,2-dioxaborolan-2-yl)indazole (9.22 g, 26.63 mmol, 70.79% yield).

$^1$H NMR (DMSO, 500 MHz): 1.31 (s, 12H), 1.60 (m, 2H), 1.74 (m, 1H), 1.95 (m, 1H), 2.04 (m, 1H), 2.38 (m, 1H), 3.72 (m, 1H), 3.85 (m, 1H), 5.81 (m, 1H), 7.46 (d, 1H), 7.55 (d, 1H), 8.11 (s, 1H).

LCMS(ESI): $[M+H]^+$ m/z: calcd 346.2; found 347.0; Rt=1.505 min.

Step 4: Synthesis of tert-butyl 6-(4-fluoro-1-tetrahydropyran-2-yl-indazol-5-yl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (5.02 g, 14.55 mmol), 4-fluoro-1-tetrahydropyran-2-yl-5-(4,4,5,5-tetramethyl-1,3,2-dioxaborolan-2-yl)indazole (5.54 g, 16.00 mmol) and Sodium carbonate (3.08 g, 29.09 mmol, 1.22 mL) were mixed together in a mixture of Dioxane (60 mL) and Water (20 mL). The resulting mixture was evacuated and backfilled three times with argon and [1,1'-Bis(diphenylphosphino)ferrocene]dichloropalladium(II), complex with dichloromethane (594.00 mg, 727.37 µmol) was added thereto. The reaction mixture was heated at 90° C. for 18 hr. The reaction mixture was cooled and diluted with water (120 ml). The resulting mixture was extracted with EtOAc (2*100 ml) and combined organic layers were washed with brine, dried over $Na_2SO_4$, filtered and evaporated to obtain tert-butyl 6-(4-fluoro-1-tetrahydropyran-2-yl-indazol-5-yl)-3-methyl-3,4-dihydro-2H-pyridine-1-carboxylate (7.92 g, crude).

$^1$H NMR (400 MHz, DMSO) 0.92 (m, 12H), 1.54 (m, 3H), 1.94 (m, 2H), 2.35 (m, 3H), 3.03 (m, 1H), 3.69 (m, 2H), 3.85 (m, 2H), 5.21 (m, 1H), 5.82 (m, 1H), 7.23 (d, 1H), 7.45 (d, 1H), 8.14 (s, 1H).

LCMS(ESI): $[M+H]^+$ m/z: calcd 415.3; found 416.2; Rt=1.745 min.

Step 5: Synthesis of 4-fluoro-5-(3-methyl-2,3,4,5-tetrahydropyridin-6-yl)-1H-indazole tert-butyl 6-(4-fluoro-1-tetrahydropyran-2-yl-indazol-5-yl)-3-methyl-3,4-dihydro-2H-pyridine-1-carboxylate (7.92 g, 19.06 mmol) was dissolved in DCM (30 mL) and $CF_3COOH$ (30 mL) was added thereto. The reaction mixture was stirred for 18 hr. The reaction mixture was evaporated to dryness and the residue was basified with aq. $K_2CO_3$ solution. The resulting mixture was extracted with DCM (3*50 ml). Combined organic layers were dried over $Na_2SO_4$, filtered and evaporated to obtain 4-fluoro-5-(3-methyl-2,3,4,5-tetrahydropyridin-6-yl)-1H-indazole (6.75 g, crude).

$^1$H NMR (500 MHz, DMSO) 0.94 (d, 3H), 1.81 (m, 2H), 2.70 (m, 2H), 3.16 (m, 1H), 3.87 (m, 2H), 7.31 (d, 1H), 7.67 (d, 1H), 8.19 (s, 1H), 13.42 (s, 1H).

LCMS(ESI): $[M+H]^+$ m/z: calcd 231.1; found 232.2; Rt=0.482 min.

Step 6: Synthesis of 4-fluoro-5-(5-methyl-2-piperidyl)-1H-indazole 4-fluoro-5-(3-methyl-2,3,4,5-tetrahydropyridin-6-yl)-1H-indazole (6.75 g, 29.19 mmol) was dissolved in MeOH (50 mL) and Sodium Borohydride (3.31 g, 87.56 mmol, 3.10 mL) was added portionwise. The reaction mixture was stirred for 18 hr. The reaction mixture was evaporated to dryness. The residue was dissolved in DCM (100 ml) and the resulting mixture was extracted with aq·$NaHSO_4$ solution (2*50 ml). Combined aqueous layers were washed with DCM (3*100 ml) and then basified with $K_2CO_3$. The resulting mixture was extracted with DCM (2*100 ml) and combined organic layers were dried over $Na_2SO_4$, filtered and evaporated to obtain 4-fluoro-5-(5-methyl-2-piperidyl)-1H-indazole (2.13 g, 9.13 mmol, 31.28% yield).

$^1$H NMR (400 MHz, DMSO) 0.81 (d, 3H), 1.12 (m, 2H), 1.39 (m, 1H), 1.51 (m, 1H), 1.62 (m, 1H), 1.77 (m, 1H), 2.25 (m, 1H), 2.97 (m, 1H), 3.85 (m, 1H), 7.26 (d, 1H), 7.47 (d, 1H), 8.06 (s, 1H), 13.23 (s, 1H).

LCMS(ESI): $[M+H]^+$ m/z: calcd 233.2; found 234.2; Rt=0.642 min.

6TT. Synthesis of 2-fluoro-5-[(2R,5S)-5-methyl-2-piperidyl]phenol

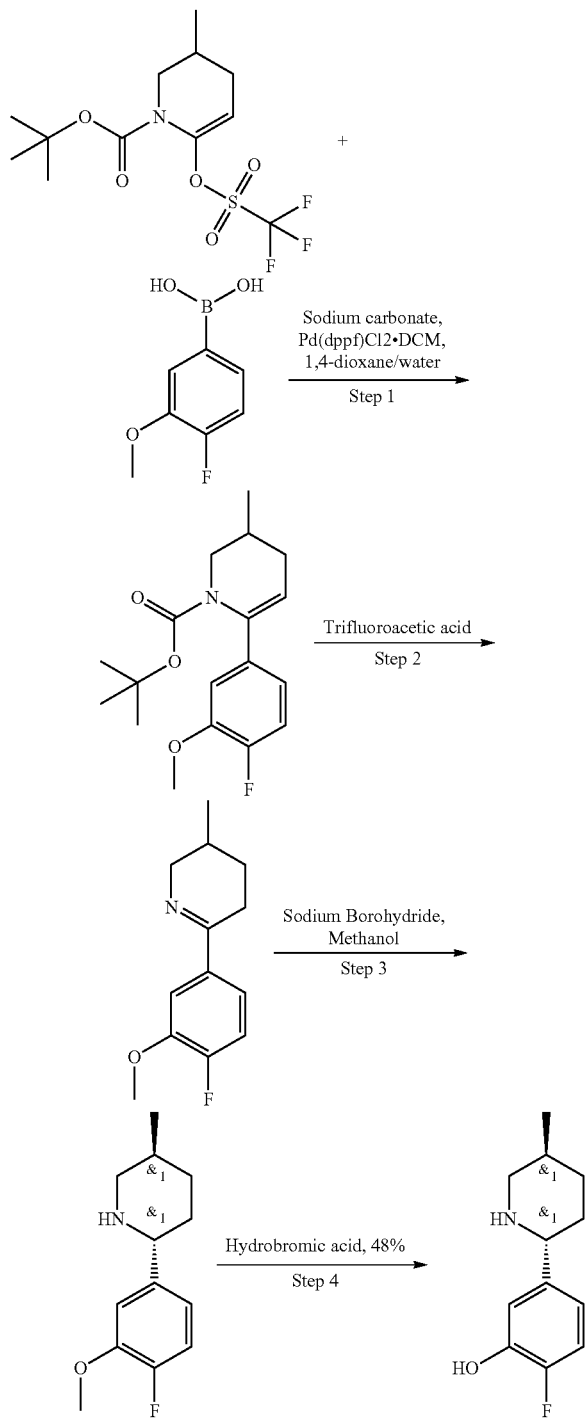

Step 1: Synthesis of tert-butyl 6-(4-fluoro-3-methoxy-phenyl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (20 g, 52.12 mmol), (4-fluoro-3-methoxy-phenyl)boronic acid (9.74 g, 57.34 mmol) and Sodium carbonate (18.23 g, 172.01 mmol, 7.21 mL) were added to a mixture of 1,4-dioxane (240 mL) and water (80 mL). The resulting mixture was evacuated and then backfilled with argon, this operation was repeated three times, then Pd(dppf)Cl$_2$ DCM (2.13 g, 2.61 mmol) was added under argon. The reaction mixture was stirred under argon at 90° C. for 18 hr, then cooled and filtered. The filtercake was washed with dioxane (2*50 ml) and discarded. The filtrate was evaporated in vacuo, and the residue was twice purified by column chromatography on silica gel using hexane/MTBE gradient (0-100% MTBE) for first purification, and hexane/chloroform gradient (5-100% chloroform) for second purification to afford tert-butyl 6-(4-fluoro-3-methoxy-phenyl)-3-methyl-3,4-dihydro-2H-pyridine-1-carboxylate (6.2 g, 19.29 mmol, 37.01% yield) as light-yellow gum.

$^1$H NMR (CDCl$_3$, 400 MHz): 0.92 (d, 3H), 1.10 (s, 9H), 1.81 (m, 1H), 2.01 (m, 1H), 2.41 (m, 1H), 2.99 (m, 1H), 3.87 (s, 3H), 4.07 (m, 1H), 5.28 (s, 1H), 6.84 (m, 1H), 6.89 (d, 1H), 7.00 (dd, 1H).

LCMS(ESI): [M+Na]$^+$ m/z: calcd 321.4; found 344.0; Rt=1.659 min.

Step 2: Synthesis of 6-(4-fluoro-3-methoxy-phenyl)-3-methyl-2,3,4,5-tetrahydropyridine A solution of tert-butyl 6-(4-fluoro-3-methoxy-phenyl)-3-methyl-3,4-dihydro-2H-pyridine-1-carboxylate (6.2 g, 19.29 mmol) in Trifluoroacetic acid (65.99 g, 578.74 mmol, 44.59 mL) was stirred at 25° C. for 1 hr. After 1 hour, the reaction mixture was concentrated under reduced pressure. The obtained residue was diluted with ice cold water (50 mL) and neutralized with aqueous 10% NaOH solution till pH=10. The resulting mixture was extracted with dichloromethane (2×100 mL). The combined organic phase was washed with water (30 mL), dried over sodium sulphate, filtered and concentrated under reduce pressure to obtain product 6-(4-fluoro-3-methoxy-phenyl)-3-methyl-2,3,4,5-tetrahydropyridine (3.5 g, 15.82 mmol, 81.99% yield) as light-yellow gum.

$^1$H NMR (CDCl$_3$, 500 MHz): 1.10 (d, 1H), 1.70 (m, 1H), 1.92 (m, 1H), 2.10 (m, 1H), 2.55 (m, 1H), 2.78 (m, 1H), 3.25 (m, 1H), 3.94 (s, 3H), 4.01 (m, 1H), 7.05 (dd, 1H), 7.21 (m, 1H), 7.56 (d, 1H).

LCMS(ESI): [M+H]$^+$ m/z: calcd 221.3; found 222.0; Rt=0.699 min.

Step 3: Synthesis of (2R,5S)-2-(4-fluoro-3-methoxy-phenyl)-5-methyl-piperidine To a stirring solution of 6-(4-fluoro-3-methoxy-phenyl)-3-methyl-2,3,4,5-tetrahydropyridine (3.5 g, 15.82 mmol) in Methanol (60 mL) was added Sodium Borohydride (897.58 mg, 23.73 mmol, 838.86 µL) portionwise at 0° C. The resulting reaction mixture was stirred at 0° C. for 1 hr, and then concentrated under reduced pressure. The residue was diluted with water (50 mL) and extracted with dichloromethane (2×100 mL). The combined organic extracts were dried over sodium sulphate and concentrated under vacuum to obtain crude product (2R,5S)-2-(4-fluoro-3-methoxy-phenyl)-5-methyl-piperidine (3.3 g, 14.78 mmol, 93.43% yield) as light-yellow gum, which was used directly in the next step.

$^1$H NMR (CDCl$_3$, 500 MHz): 0.92 (d, 3H), 1.14 (m, 1H), 1.50 (m, 1H), 1.77 (m, 4H), 2.42 (m, 1H), 3.13 (m, 1H), 3.50 (m, 1H), 3.90 (s, 3H), 6.85 (m, 1H), 7.00 (m, 2H).

LCMS(ESI): [M+H]⁺ m/z: calcd 223.3; found 224.2; Rt=0.687 min.

Step 4: Synthesis of 2-fluoro-5-[(2R,5S)-5-methyl-2-piperidyl]phenol

A solution of (2R,5S)-2-(4-fluoro-3-methoxy-phenyl)-5-methyl-piperidine (1.60 g, 7.17 mmol) in Hydrobromic acid, 48% (35 g, 432.57 mmol, 23.49 mL) was stirred with a reflux condenser at 110° C. for 48 hr, then cooled down and evaporated in vacuo. The residue was additionally dried in vacuo (1 mm. Hg) to afford 2-fluoro-5-[(2R,5S)-5-methyl-2-piperidyl]phenol (2.2 g, crude, HBr) as brown solid, which was used directly in the next step.

¹H NMR (500 MHz, DMSO) 0.92 (d, 3H), 1.32 (m, 1H), 1.90 (m, 4H), 2.70 (m, 1H), 3.23 (m, 1H), 4.11 (m, 1H), 6.95 (m, 1H), 7.07 (d, 1H), 7.21 (dd, 1H), 9.00 (m, 2H), 10.09 (s, 1H).

LCMS(ESI): [M+H]⁺ m/z: calcd 209.2; found 210.2; Rt=0.783 min.

6UU. Synthesis of 5-(5-methyl-2-piperidyl)-1H-indazol-3-amine

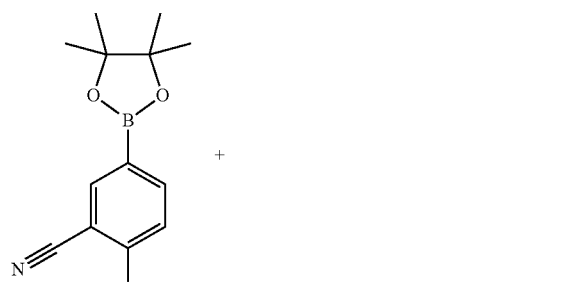

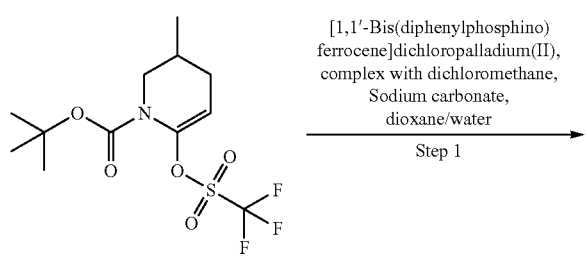

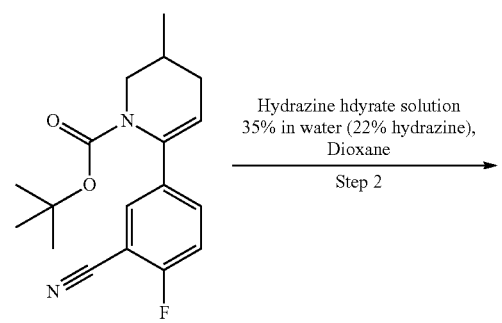

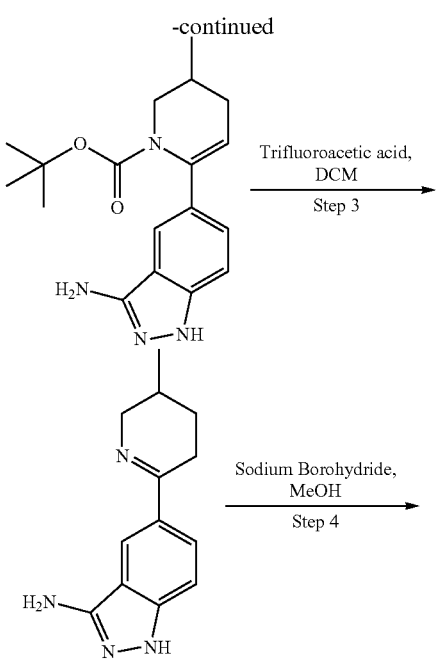

Step 1: Synthesis of tert-butyl 6-(3-Cyano-4-fluoro-phenyl)-3-methyl-3,4-dihydro-2H-pyridine-1-carboxylate 2-fluoro-5-(4,4,5,5-tetramethyl-1,3,2-dioxaborolan-2-yl)benzonitrile (5 g, 20.24 mmol) and tert-butyl 3-methyl-6-(trifluoromethylsulfonyloxy)-3,4-dihydro-2H-pyridine-1-carboxylate (8.39 g, 24.28 mmol) were mixed together in water (5 mL). The resulting mixture was evacuated and then backfilled with argon, this operation was repeated three times, then Sodium carbonate (4.29 g, 40.47 mmol, 1.70 mL) in water (5 mL) and [1,1'-Bis(diphenylphosphino)ferrocene]dichloropalladium(II), complex with dichloromethane (826.31 mg, 1.01 mmol) were added under argon. The reaction mixture was stirred under argon at 90° C. for 48 hr, then cooled and evaporated in vacuo poured into water (120 ml) and extracted with EtOAc (2×60 ml). The combined organic extracts were washed with water (2*40 ml), dried over sodium sulphate and evaporated in vacuo to leave 6 g of crude product, 6 of which was purification by column chromatography on silica gel using Hexane/MTBE gradient (10-100% MTBE) to afford product tert-butyl 6-(3-cyano-4-fluoro-phenyl)-3-methyl-3,4-dihydro-2H-pyridine-1-carboxylate (5.7 g, 18.02 mmol, 89.03% yield).

LCMS(ESI): [M+H]⁺ m/z: calcd 316.4; found 317.2; Rt=1.586 min.

Step 2: Synthesis of tert-butyl 6-(3-amino-1H-indazol-5-yl)-3-methyl-3,4-dihydro-2H-pyridine-1-carboxylate Hydrazine hydrate solution 35% in water (22% hydrazine) (2.56 g, 51.21 mmol, 2.49 mL) was added in one portion to a stirred solution of tert-butyl 6-(3-cyano-4-fluoro-phenyl)-3-methyl-3,4-dihydro-2H-pyridine-1-carboxylate (2.7 g, 8.53 mmol) in dioxane (50 mL) at 100° C. The resulting mixture was stirred at 100° C. for 48 hr, and then evaporated in vacuo. The residue was diluted with water (20 mL) and extracted with dichloromethane (2*40 mL). The combined organic extracts were dried over sodium sulphate and evaporated in vacuo to afford tert-butyl 6-(3-amino-1H-indazol-5-yl)-3-methyl-3,4-dihydro-2H-pyridine-1-carboxylate (2 g, 6.09 mmol, 71.36% yield).

LCMS(ESI): [M+H]$^+$ m/z: calcd 328.4; found 329.2; Rt=1.262 min.

Step 3: Synthesis of 5-(3-methyl-2,3,4,5-tetrahydropyridin-6-yl)-1H-indazol-3-amine The solution of tert-butyl 6-(3-amino-1H-indazol-5-yl)-3-methyl-3,4-dihydro-2H-pyridine-1-carboxylate (0.7 g, 2.13 mmol) in DCM (10 mL) and Trifluoroacetic acid (10 g, 87.70 mmol, 6.76 mL) was stirred at 0° C. for 5 hr, and then evaporated in vacuo. Crushed ice (30 g) was added to the residue and pH was adjusted to 8 with a 10% aqueous solution of sodium hydrocarbonate. The resulting mixture was extracted with ethylacetate (2*50 mL). The combined organic extracts were dried over sodium sulphate and evaporated in vacuo to afford 5-(3-methyl-2,3,4,5-tetrahydropyridin-6-yl)-1H-indazol-3-amine (0.3 g, 1.31 mmol, 61.65% yield).

LCMS(ESI): [M+H]$^+$ m/z: calcd 228.3; found 229.2; Rt=0.528 min.

Step 4: Synthesis of 5-(5-methyl-2-piperidyl)-1H-indazol-3-amine

Sodium Borohydride (139.20 mg, 3.68 mmol, 130.10 μL) was added in one portion to a stirred solution of 5-(3-methyl-2,3,4,5-tetrahydropyridin-6-yl)-1H-indazol-3-amine (0.42 g, 1.84 mmol) in MeOH (20 mL) at 0° C. The resulting mixture was stirred at 0° C. for 6 hr, and then evaporated in vacuo. The residue was diluted with water (30 mL) and extracted with dichloromethane (2*50 mL). The combined organic extracts were dried over sodium sulphate and evaporated in vacuo to afford 5-(5-methyl-2-piperidyl)-1H-indazol-3-amine (0.34 g, 1.48 mmol, 80.24% yield).

LCMS(ESI): [M+H]$^+$ m/z: calcd 230.3; found 231.0; Rt=0.776 min.

6VV. Synthesis of (2R,5S)-5-methyl-2-(4-methylsulfonylphenyl)piperidine

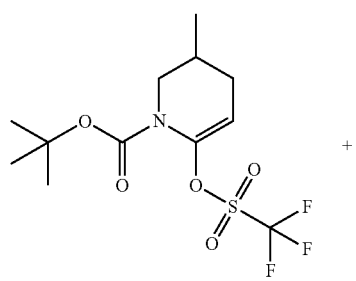

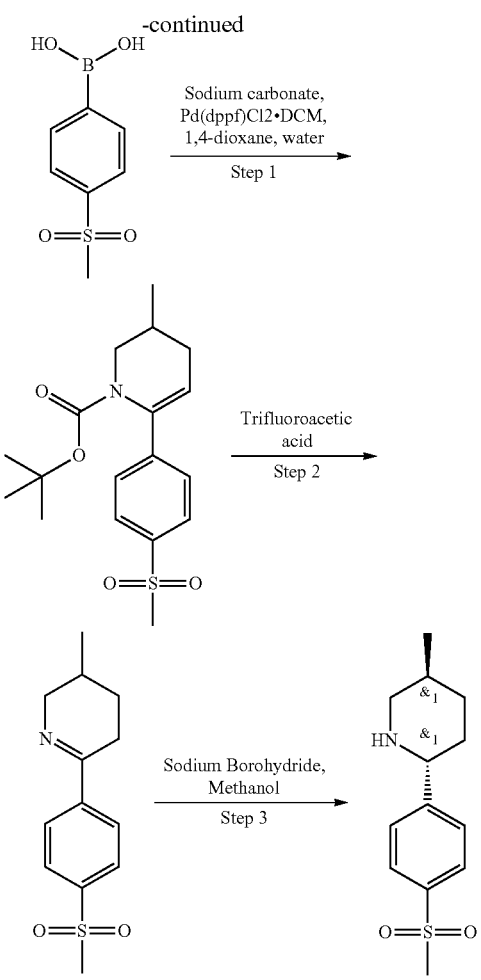

Step 1: Synthesis of tert-butyl 3-methyl-6-(4-methylsulfonylphenyl)-3,4-dihydro-2H-pyridine-1-carboxylate tert-butyl 3-methyl-6-(trifluoromethylsulfonyloxy)-3,4-dihydro-2H-pyridine-1-carboxylate (20 g, 57.91 mmol), (4-methylsulfonylphenyl)boronic acid (15.8 g, 78.99 mmol) and Sodium carbonate (24.55 g, 231.66 mmol, 9.70 mL) were added to a mixture of 1,4-dioxane (350 mL) and water (110 mL). The resulting mixture was evacuated and then backfilled with argon, this operation was repeated three times, then Pd(dppf)C$_{12}$ DCM (2.36 g, 2.90 mmol) was added under argon. The reaction mixture was stirred under argon at 90° C. for 18 hr, then cooled and filtered. The filtercake was washed with dioxane (2*50 ml) and discarded. The filtrate was evaporated in vacuo, and the residue was purified by column chromatography on silica gel using chloroform/ethyl acetate gradient (0-100% ethyl acetate) to afford tert-butyl 3-methyl-6-(4-methylsulfonylphenyl)-3,4-dihydro-2H-pyridine-1-carboxylate (11.3 g, 32.15 mmol, 55.52% yield) as beige solid, which was used directly in the next step.

$^1$H NMR (CDCl$_3$, 400 MHz): 0.92 (d, 3H), 1.18 (m, 9H), 1.93 (m, 1H), 2.02 (m, 1H), 2.46 (m, 1H), 3.05 (m, 4H), 4.05 (m, 1H), 5.44 (s, 1H), 7.49 (d, 2H), 7.87 (d, 2H).

LCMS(ESI): [M+Na]$^+$ m/z: calcd 351.5; found 374.2; Rt=1.345 min.

Step 2: Synthesis of 3-methyl-6-(4-methylsulfonylphenyl)-2,3,4,5-tetrahydropyridine A solution of tert-butyl 3-methyl-6-(4-methylsulfonylphenyl)-3,4-dihydro-2H-pyridine-1-carboxylate (3 g, 8.54 mmol) in Trifluoroacetic acid (29.20 g, 256.08 mmol, 19.73 mL) was stirred at 25° C. for 1 hr. After 1 hour, the reaction mixture was concentrated under reduced pressure. The obtained residue was diluted with ice cold water (50 mL) and neutralized with aqueous 10% NaOH solution till pH 10. The resulting mixture was extracted with dichloromethane (2×50 mL). The combined organic phase was dried over sodium sulphate and concentrated under reduced pressure to afford 3-methyl-6-(4-methylsulfonylphenyl)-2,3,4,5-tetrahydropyridine (2.05 g, 8.16 mmol, 95.55% yield) as white solid.

$^1$H NMR (CDCl$_3$, 500 MHz): 1.01 (d, 3H), 1.42 (m, 1H), 1.62 (m, 1H), 1.97 (m, 1H), 2.60 (m, 1H), 2.75 (m, 1H), 2.80 (s, 3H), 3.30 (m, 1H), 4.08 (m, 1H), 7.95 (m, 4H).

LCMS(ESI): [M+H]$^+$ m/z: calcd 251.3; found 252.0; Rt=0.746 min.

Step 3: Synthesis of (2R,5S)-5-methyl-2-(4-methylsulfonylphenyl)piperidine

To a stirring suspension of 3-methyl-6-(4-methylsulfonylphenyl)-2,3,4,5-tetrahydropyridine (2.05 g, 8.16 mmol) in Methanol (50 mL) was added Sodium Borohydride (900 mg, 23.79 mmol, 841.12 μL) portionwise at 0° C. The resulting reaction mixture was stirred at 0° C. for 1 hr, then was allowed to warm to 25° C. and stirred for 12 hr, and then concentrated under reduced pressure. The residue was diluted with water (50 mL) and extracted with dichloromethane (2×50 mL). The combined organic extracts were dried over sodium sulphate and concentrated under vacuum to obtain crude product (2R,5S)-5-methyl-2-(4-methylsulfonylphenyl)piperidine (1.9 g, 7.50 mmol, 91.95% yield) as white solid, which was used directly in the next step.

$^1$H NMR (CDCl$_3$, 400 MHz): 1.01 (d, 3H), 1.42 (m, 1H), 1.62 (m, 1H), 1.87 (m, 2H), 1.90 (m, 2H), 2.40 (m, 1H), 3.05 (s, 3H), 3.15 (m, 1H), 3.66 (m, 1H), 7.58 (d, 2H), 7.88 (d, 2H).

LCMS(ESI): [M+H]$^+$ m/z: calcd 253.4; found 254.0; Rt=0.610 min.

6WW. Synthesis of 6-[(2S,5R)-5-methyl-2-piperidyl]thiazolo[5,4-b]pyridine

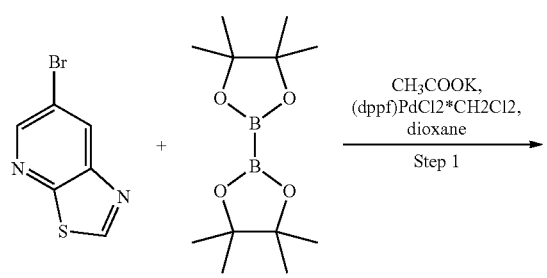

Step 1: Synthesis of 6-(4,4,5,5-tetramethyl-1,3,2-dioxaborolan-2-yl)thiazolo[5,4-b]pyridine A mixture of 6-bromothiazolo[5,4-b]pyridine (3 g, 13.95 mmol), 4,4,5,5-tetramethyl-2-(4,4,5,5-tetramethyl-1,3,2-dioxaborolan-2-yl)-1,3,2-dioxaborolane (5.31 g, 20.92 mmol) and CH$_3$COOK (4.11 g, 41.85 mmol, 2.62 mL) in dioxane (10 mL) was degassed with argon for 10 min. (dppf)PdCl$_2$*CH$_2$C$_{12}$ (1.14 g, 1.39 mmol) was next added and the reaction mixture was heated to 90° C. for 16 hr. The reaction mixture was cooled to RT, filtered and concentrated under reduced pressure. Crude product was purified by flash chromatography on SiO$_2$ (gradient CHCl$_3$:acetonitrile) to give 6-(4,4,5,5-tetramethyl-1,3,2-dioxaborolan-2-yl)thiazolo[5,4-b]pyridine (2.6 g, 9.92 mmol, 71.11% yield).

LCMS(ESI): [M−4Me]$^+$ m/z: calcd 180.2; found 181.2; Rt=0.698 min.

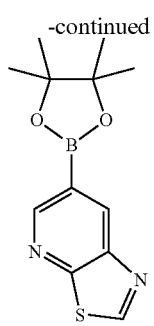

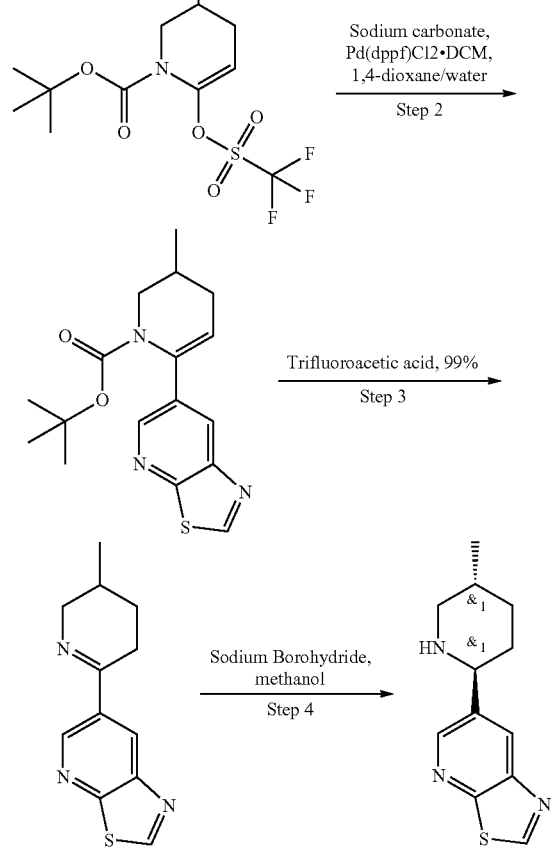

Step 2: Synthesis of tert-butyl 3-methyl-6-thiazolo[5,4-b]pyridin-6-yl-3,4-dihydro-2H-pyridine-1-carboxylate tert-butyl 3-methyl-6-(trifluoromethylsulfonyloxy)-3,4-dihydro-2H-pyridine-1-carboxylate (2.54 g, 7.35 mmol), 6-(4,4,5,5-tetramethyl-1,3,2-dioxaborolan-2-yl)thiazolo[5,4-b]pyridine (2.41 g, 9.19 mmol) and Sodium carbonate (2.34 g, 22.06 mmol, 924.02 µL) were added to a mixture of 1,4-dioxane (30 mL) and water (10 mL). The resulting mixture was evacuated and then backfilled with argon, then Pd(dppf)C$_{12}$ DCM (299.97 mg, 367.61 µmol) was added under argon. The reaction mixture was stirred under argon at 75° C. for 16 hr, then treated with water and needed product was extracted with DCM, then evaporated. Crude product was purified by flash chromatography on SiO$_2$ (gradient MTBE:methanol) to give tert-butyl 3-methyl-6-thiazolo[5,4-b]pyridin-6-yl-3,4-dihydro-2H-pyridine-1-carboxylate (1.55 g, 4.68 mmol, 63.61% yield) was obtained.

$^1$H NMR (DMSO-d$_6$, 500 MHz): 0.96 (s, 11H), 1.85 (m, 2H), 3.10 (m, 2H), 3.90 (m, 2H), 5.56 (s, 1H), 8.23 (s, 1H), 8.56 (s, 1H), 9.52 (s, 1H).

LCMS(ESI): [M+H]$^+$ m/z: calcd 331.2; found 332.2; Rt=1.493 min.

Step 3: Synthesis of 6-(3-methyl-2,3,4,5-tetrahydropyridin-6-yl)thiazolo[5,4-b]pyridine tert-butyl 3-methyl-6-thiazolo[5,4-b]pyridin-6-yl-3,4-dihydro-2H-pyridine-1-carboxylate (1.55 g, 4.68 mmol) was dissolved in Trifluoroacetic acid, 99% (22.20 g, 194.70 mmol, 15 mL) and stirred for 1 hr. Reaction mixture was evaporated to dryness, residue was dissolved in 40 ml of DCM, washed with saturated solution of NaHCO$_3$, dried over Na$_2$SO$_4$ and concentrated in vacuo to give 6-(3-methyl-2,3,4,5-tetrahydropyridin-6-yl)thiazolo[5,4-b]pyridine (0.8 g, 3.46 mmol, 73.95% yield).

$^1$H NMR (CDCl$_3$, 400 MHz): 1.01 (d, 3H), 1.44 (m, 1H), 1.75 (m, 1H), 1.97 (m, 1H), 2.68 (m, 1H), 2.87 (m, 1H), 3.29 (m, 1H), 4.06 (m, 1H), 8.65 (s, 1H), 9.11 (s, 2H).

LCMS(ESI): [M+H]$^+$ m/z: calcd 231.1; found 232.2; Rt=0.582 min.

Step 4: Synthesis of 6-[(2S,5R)-5-methyl-2-piperidyl]thiazolo[5,4-b]pyridine 6-(3-methyl-2,3,4,5-tetrahydropyridin-6-yl)thiazolo[5,4-b]pyridine (0.8 g, 3.46 mmol) was dissolved in methanol (20 mL) and Sodium Borohydride (196.26 mg, 5.19 mmol, 183.42 µL) was added in several portions. After 1 hr reaction mixture was concentrated in vacuo, then dissolved in DCM, washed with water, dried over Na$_2$SO$_4$ and concentrated in vacuo to give 6-[(2S,5R)-5-methyl-2-piperidyl]thiazolo[5,4-b]pyridine (0.65 g, 2.79 mmol, 80.55% yield)

$^1$H NMR (500 MHz, DMSO) 0.93 (d, 3H), 1.18 (m, 1H), 1.59 (m, 1H), 1.62 (m, 1H), 1.90 (m, 3H), 2.47 (m, 1H), 3.19 (m, 1H), 3.77 (m, 1H), 8.39 (s, 1H), 8.69 (s, 1H), 9.10 (s, 1H).

LCMS(ESI): [M+H]$^+$ m/z: calcd 233.1; found 234.2; Rt=0.561 min.

6XX. The Synthesis of rac-6-(5-methyl-2-piperidyl)-1H-Quinolin-2-one

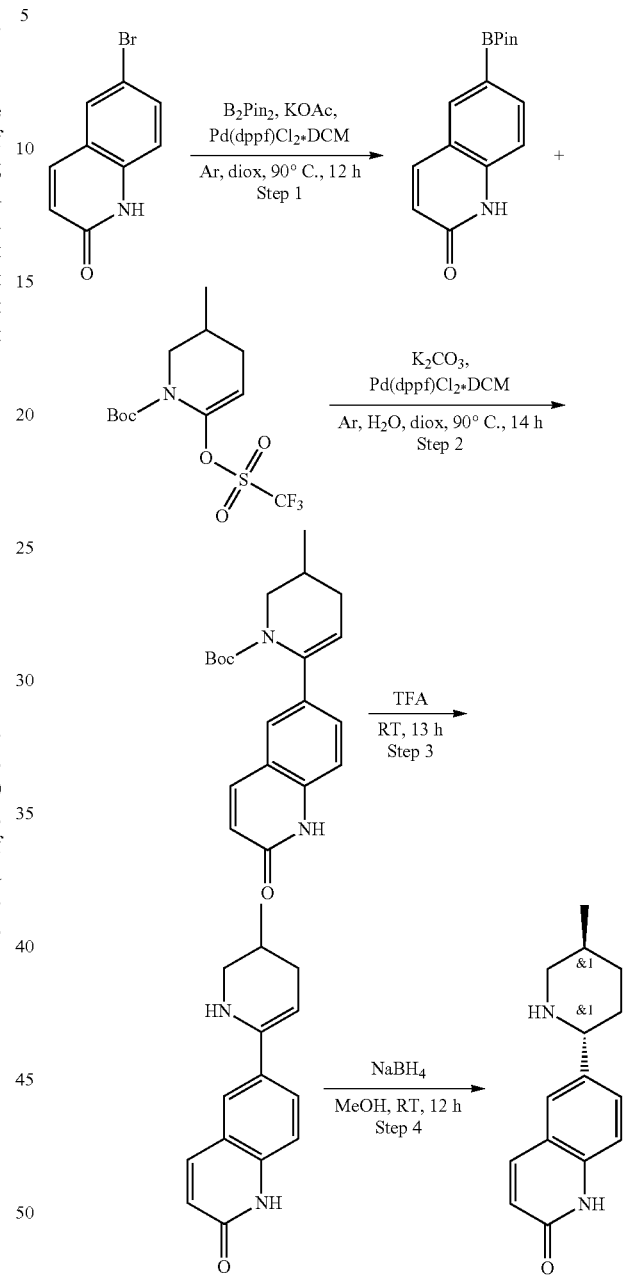

Step 1: The Synthesis of 6-(4,4,5,5-tetramethyl-1,3,2-dioxaborolan-2-yl)-1H-Quinolin-2-one Potassium Acetate (7.88 g, 80.34 mmol, 5.02 mL) was added a solution of 6-bromo-1H-quinolin-2-one (9 g, 40.17 mmol) in Dioxane (200 mL), followed by addition of 4,4,5,5-tetramethyl-2-(4,4,5,5-tetramethyl-1,3,2-dioxaborolan-2-yl)-1,3,2-dioxaborolane (10.20 g, 40.17 mmol) and Pd(dppf)Cl$_2$*DCM (1.64 g, 2.01 mmol). The solution was stirred overnight at 90° C. under Ar. Resulting mixture was concentrated under vacuum, diluted with EtOAc, filtered and evaporated. Resulting crude precipitate was purified by column chromatography (Hexane/MTBE) to obtain 6-(4,4,5,5-tetramethyl-1,3,2-dioxaborolan-2-yl)-1H-quinolin-2-one (10.54 g, crude).

$^1$H NMR (400 MHz, DMSO-d$_6$) δ 1.30 (s, 12H), 6.48 (d, 1H), 7.27 (d, 1H), 7.72 (d, 1H), 7.97 (s, 1H), 7.99 (d, 1H).

LCMS(ESI): [M+H]$^+$ m/z: calcd 271.2; found 272.2; Rt=1.106 min.

Step 2: The Synthesis of tert-butyl 3-methyl-6-(2-oxo-1H-Quinolin-6-yl)-3,4-dihydro-2H-pyridine-1-carboxylate To a solution of Potassium carbonate (7.65 g, 55.33 mmol, 3.34 mL)Pd(dppf)Cl$_2$*DCM (753.02 mg, 922.11 µmol) in water (5 mL) was added to a solution of 6-(4,4,5,5-tetramethyl-1,3,2-dioxaborolan-2-yl)-1H-quinolin-2-one (5 g, 18.44 mmol) in dioxane (5 mL), followed by addition of tert-butyl 3-methyl-6-(trifluoromethylsulfonyloxy)-3,4-dihydro-2H-pyridine-1-carboxylate (7.01 g, 20.29 mmol) and Pd(dppf)Cl$_2$*DCM (753.02 mg, 922.11 µmol). Resulting mixture was stirred overnight at 90° C. under Ar. Resulting mixture was concentrated under vacuum, diluted with EtOAc and washed with water (2×40 ml). Organic phase was dried over sodium sulfate, filtered and evaporated to obtain tert-butyl 3-methyl-6-(2-oxo-1H-quinolin-6-yl)-3,4-dihydro-2H-pyridine-1-carboxylate (8.3 g, crude).

LCMS(ESI): [M+H]$^+$ m/z: calcd 340.2; found 341.2; Rt=1.239 min.

Step 3: The Synthesis of 6-(3-methyl-2,3,4,5-tetrahydropyridin-6-yl)-1H-Quinolin-2-one A solution of tert-butyl 3-methyl-6-(2-oxo-1H-quinolin-6-yl)-3,4-dihydro-2H-pyridine-1-carboxylate (8.3 g, 24.38 mmol) in TFA (40 mL) was stirred at 25° C. for 13 hr. Potassium carbonate saturated aq. solution was added to the solution (50 ml) and then extracted with DCM (2×50 ml). Organic phase was dried over sodium sulfate, filtered off and evaporated to obtain 6-(3-methyl-2,3,4,5-tetrahydropyridin-6-yl)-1H-quinolin-2-one (6.3 g, crude).

LCMS(ESI): [M+H]$^+$ m/z: calcd 240.2; found 241.2; Rt=0.593 min.

Step 4: The Synthesis of rac-6-(5-methyl-2-piperidyl)-1H-Quinolin-2-one

Sodium borohydride (1.98 g, 52.43 mmol, 1.85 mL) was added portionwise to a solution of 6-(3-methyl-2,3,4,5-tetrahydropyridin-6-yl)-1H-quinolin-2-one (6.3 g, 26.22 mmol) in Methanol (100 mL). The mixture was stirred at rt for 12 hr. Water (50 ml) was added and resulting mixture was extracted with EtOAc (2×50 ml). Organic phase was dried over sodium sulfate, filtered and evaporated. Resulting crude product was purified by column chromatography to obtain rac-6-(5-methyl-2-piperidyl)-1H-quinolin-2-one (1.1 g, 4.54 mmol, 17.32% yield).

$^1$H NMR (500 MHz, DMSO-d$_6$) δ 0.89 (d, 3H), 1.16 (m, 2H), 1.63 (m, 2H), 1.82 (m, 1H), 2.38 (m, 1H), 3.05 (m, 1H), 3.63 (m, 2H), 6.44 (d, 1H), 7.24 (d, 1H), 7.30 (d, 1H), 7.58 (s, 1H), 7.78 (d, 1H), 11.64 (m, 1H).

LCMS(ESI): [M+H]$^+$ m/z: calcd 242.2; found 243.0; Rt=0.714 min.

6YY. The Synthesis of 6-(5-methyl-2-piperidyl)isoquinoline

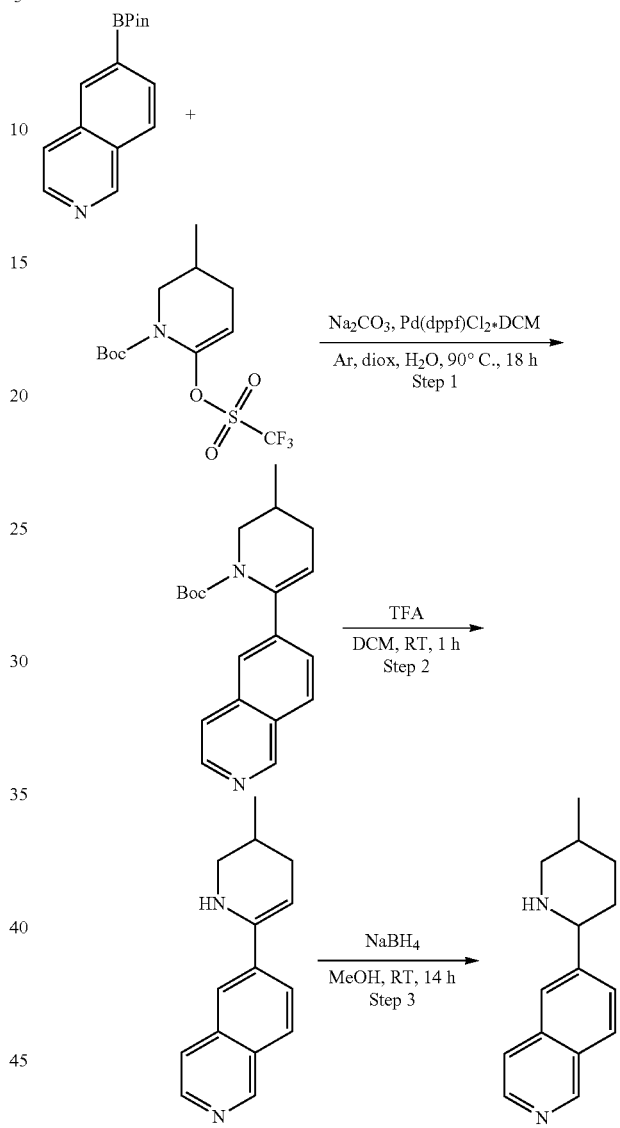

Step 1: The Synthesis of tert-butyl 6-(6-isoquinolyl)-3-methyl-3,4-dihydro-2H-pyridine-1-carboxylate 6-(4,4,5,5-tetramethyl-1,3,2-dioxaborolan-2-yl)isoquinoline (5.3 g, 20.77 mmol), tert-butyl 3-methyl-6-(trifluoromethylsulfonyloxy)-3,4-dihydro-2H-pyridine-1-carboxylate (7.17 g, 20.77 mmol) and Sodium carbonate (2.20 g, 20.77 mmol, 870.32 µL) were mixed together in dioxane (45 mL) and H$_2$O (15 mL) was added thereto. The resulting mixture was evacuated and backfield three times with argon. Pd(dppf)C$_{12}$ DCM (20.77 mmol) was added to the previous mixture and the resulting mixture was heated at 90° C. for 18 hr. The reaction mixture was cooled and diluted with water (150 ml). The resulting mixture was filtered and rinsed with water (100 ml) and EtOAc (200 ml). The filtrated was transferred to a separating funnel and an organic layer was separated. An aqueous layer was extracted with EtOAc (2*200 ml). Combined organic layers were washed with brine, dried over $Na_2SO_4$ and evaporated to obtain crude product which was purified by CC to obtain tert-butyl 6-(6-isoquinolyl)-3-methyl-3,4-dihydro-2H-pyridine-1-carboxylate (5.3 g, 16.34 mmol, 78.64% yield).

LCMS(ESI): $[M+H]^+$ m/z: calcd 324.2; found 325.4; Rt=1.189 min.

Step 2: The Synthesis of 6-(3-methyl-2,3,4,5-tetrahydropyridin-6-yl)isoquinoline tert-butyl 6-(6-isoquinolyl)-3-methyl-3,4-dihydro-2H-pyridine-1-carboxylate (5.3 g, 16.34 mmol) and Trifluoroacetic acid (18.63 g, 163.37 mmol, 12.59 mL) was dissolved in DCM (18 mL) and stirred for 1 hr at room temperature and then evaporated in vacuo. The residue was dissolved in aqueous $Na_2CO_3$ and DCM was added. The organic phase was separated, washed with brine, dried and evaporated to obtain 6-(3-methyl-2,3,4,5-tetrahydropyridin-6-yl)isoquinoline (2.3 g, 10.25 mmol, 62.77% yield).

$^1$H NMR (400 MHz, $CDCl_3$) δ 1.02 (d, 3H), 1.43 (m, 1H), 1.78 (m, 1H), 1.97 (m, 1H), 2.69 (m, 1H), 2.88 (m, 1H), 3.30 (m, 1H), 4.06 (m, 1H), 7.67 (d, 1H), 7.95 (d, 1H), 8.10 (s, 1H), 8.12 (d, 1H), 8.51 (d, 1H), 9.23 (s, 1H).

LCMS(ESI): $[M+H]^+$ m/z: calcd 224.2; found 225.2; Rt=0.676 min.

Step 3: The Synthesis of 6-(5-methyl-2-piperidyl)isoquinoline 6-(3-methyl-2,3,4,5-tetrahydropyridin-6-yl)isoquinoline (2.3 g, 10.25 mmol) was dissolved in Methanol (25 mL) and Sodium Borohydride (775.88 mg, 20.51 mmol, 725.12 μL) was added dropwise. The reaction mixture was stirred overnight at room temperature. The reaction mixture was evaporated to dryness. The residue was dissolved in DCM (150 ml) and the resulting mixture was extracted with citric acid solution (2*100 mL). Combined aqueous layers were washed with DCM (3*50 mL) and then basified with $K_2CO_3$. The resulting mixture was extracted with DCM (2*200 mL) and combined organic layers were dried over $Na_2SO_4$, filtered and evaporated.

$^1$H NMR (400 MHz, $CDCl_3$) δ 0.89 (d, 3H), 1.18 (m, 2H), 1.71 (m, 1H), 1.88 (m, 2H), 2.12 (m, 1H), 2.45 (m, 1H), 3.18 (m, 1H), 3.73 (m, 1H), 7.60 (m, 2H), 7.81 (s, 1H), 7.88 (d, 1H), 8.46 (d, 1H), 8.18 (s, 1H).

LCMS(ESI): $[M+H]^+$ m/z: calcd 226.2; found 227.2; Rt=0.607 min. 6ZZ. Synthesis of rac-(2R,5S)-1',5-dimethyl-2,4'-bipiperidine

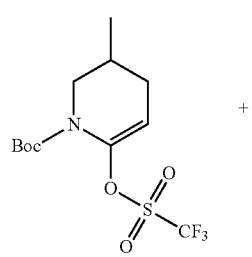

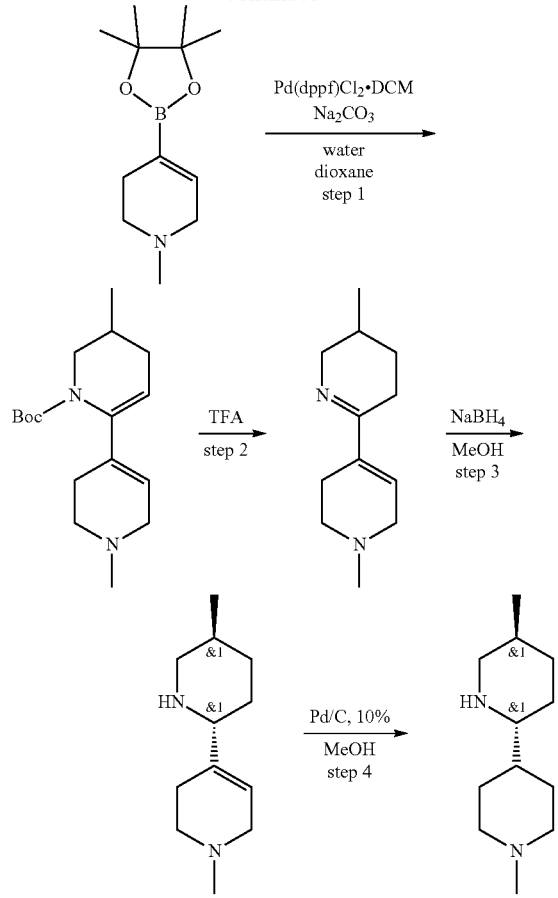

Step 1: Synthesis of tert-butyl 1',5-dimethyl-1',2',3',5,6,6'-Hexahydro-[2,4'-Bipyridine]-1(4H)-carboxylate A mixture of tert-butyl 3-methyl-6-(trifluoromethylsulfonyloxy)-3,4-dihydro-2H-pyridine-1-carboxylate (22.17 g, 54.56 mmol), 1-methyl-4-(4,4,5,5-tetramethyl-1,3,2-dioxaborolan-2-yl)-3,6-dihydro-2H-pyridine (14 g, 62.75 mmol), [1,1'-bis(diphenylphosphino)ferrocene]dichloropalladium (II), complex with DCM (2.23 g, 2.73 mmol) and sodium carbonate (17.35 g, 163.69 mmol, 6.86 mL) in dioxane (225 mL) and water (75 mL) was stirred at 90° C. under argon atmosphere for 28 hr. After cooling to rt, the reaction mixture was filtered off. The filter cake was washed with dioxane (500 mL) and discarded. Filtrate was concentrated under reduced pressure and the residue was purified by silica gel flash chromatography eluting with a 0 to 100 percent MeOH-MTBE gradient to give tert-butyl 3-methyl-6-(1-methyl-3,6-dihydro-2H-pyridin-4-yl)-3,4-dihydro-2H-pyridine-1-carboxylate (6 g, 20.52 mmol, 37.61% yield).

$^1$H NMR (400 MHz, DMSO-$d_6$) δ (ppm) 0.85 (d, 3H), 1.31 (s, 9H), 1.73 (m, 2H), 2.01 (m, 1H), 2.10 (m, 2H), 2.18 (s, 3H), 2.46 (m, 2H), 2.75 (m, 1H), 2.83 (m, 2H), 3.69 (m, 1H), 5.09 (m, 1H), 5.48 (m, 1H).

LCMS(ESI): $[M]^+$ m/z: calcd 292.2; found 293.2; Rt=1.118 min.

Step 2: Synthesis of 1',5-dimethyl-1',2',3,3',4,5,6,6'-Octahydro-2,4'-Bipyridine The solution of tert-butyl 3-methyl-6-(1-methyl-3,6-dihydro-2H-pyridin-4-yl)-3,4-dihydro-2H-pyridine-1-carboxylate (6 g, 20.52 mmol) in TFA (37.43 g, 328.30 mmol, 25.29 mL) was stirred at 20° C. for 1 hr, and then evaporated in vacuum. Crushed ice (10 g) was added to the residue and pH was adjusted to 10 with a 10% aqueous solution of sodium hydroxide. The resulting mixture was extracted with ethyl acetate (2*30 mL). The combined organic extracts were dried over sodium sulphate and evaporated in vacuum to afford 1-methyl-4-(3-methyl-2,3,4,5-tetrahydropyridin-6-yl)-3,6-dihydro-2H-pyridine (3 g, 15.60 mmol, 76.03% yield) as brown solid, which was used directly in the next step.

$^1$H NMR (500 MHz, DMSO-d$_6$) δ (ppm) 0.85 (d, 3H), 1.15 (m, 2H), 1.71 (m, 2H), 2.26 (s, 3H), 2.37 (m, 2H), 2.48 (m, 2H), 2.94 (m, 3H), 3.72 (m, 1H), 3.90 (m, 1H), 6.19 (m, 1H).

LCMS(ESI): [M]$^-$ m/z: calcd 192.2; found 193.2; Rt=0.198 min.

Step 3: Synthesis of rac-1-methyl-4-((2R,5S)-5-methylpiperidin-2-yl)-1,2,3,6-tetrahydropyridine Sodium borohydride (885.26 mg, 23.40 mmol, 827.34 µL) was added in one portion to a stirred solution of 1-methyl-4-(3-methyl-2,3,4,5-tetrahydropyridin-6-yl)-3,6-dihydro-2H-pyridine (3 g, 15.60 mmol) in MeOH (90 mL) at 0° C. The resulting mixture was stirred at 0° C. for 1 hr, and then evaporated in vacuum. The residue was diluted with water (100 mL) and extracted with DCM (2*200 mL). The combined organic extracts were dried over sodium sulphate and evaporated in vacuum to afford 1-methyl-4-[(2R,5S)-5-methyl-2-piperidyl]-3,6-dihydro-2H-pyridine (2.6 g, 13.38 mmol, 85.77% yield) as yellow oil, which was used directly in the next step.

$^1$H NMR (500 MHz, DMSO-d$_6$) δ (ppm) 0.75 (d, 3H), 1.06 (m, 4H), 1.37 (m, 1H), 1.54 (m, 1H), 1.70 (m, 1H), 2.09 (m, 3H), 2.16 (s, 3H), 2.36 (m, 2H), 2.75 (m, 2H), 2.86 (m, 1H), 5.47 (m, 1H).

LCMS(ESI): [M]$^+$ m/z: calcd 194.2; found 195.2; Rt=0.151 min.

Step 4: Synthesis of rac-(2R,5S)-1',5-dimethyl-2,4'-Bipiperidine

To a solution of 1-methyl-4-[(2R,5S)-5-methyl-2-piperidyl]-3,6-dihydro-2H-pyridine (2.60 g, 13.38 mmol) in MeOH (300 mL) was added palladium, 10% on carbon (1.42 g, 13.38 mmol). The reaction was put under an atmosphere of hydrogen (1 bar) and stirred vigorously at 45° C. After 24 hr, the catalyst was removed by filtration, and the filtrate was concentrated in vacuum to give 1-methyl-4-[(2R,5S)-5-methyl-2-piperidyl]piperidine (2.6 g, 13.24 mmol, 98.97% yield).

$^1$H NMR (400 MHz, DMSO-d$_6$) δ (ppm) 0.73 (d, 3H), 0.78 (m, 1H), 0.89 (m, 1H), 1.15 (m, 3H), 1.32 (m, 2H), 1.71 (m, 7H), 2.09 (s, 3H), 2.27 (m, 1H), 2.72 (m, 2H), 2.86 (m, 1H).

LCMS(ESI): [M]$^+$ m/z: calcd 196.2; found 197.2; Rt=0.112 min.

6AAA. Synthesis of rac-benzyl 4-((2R,5S)-5-methylpiperidin-2-yl)-5,6-dihydropyridine-1(2H)-carboxylate

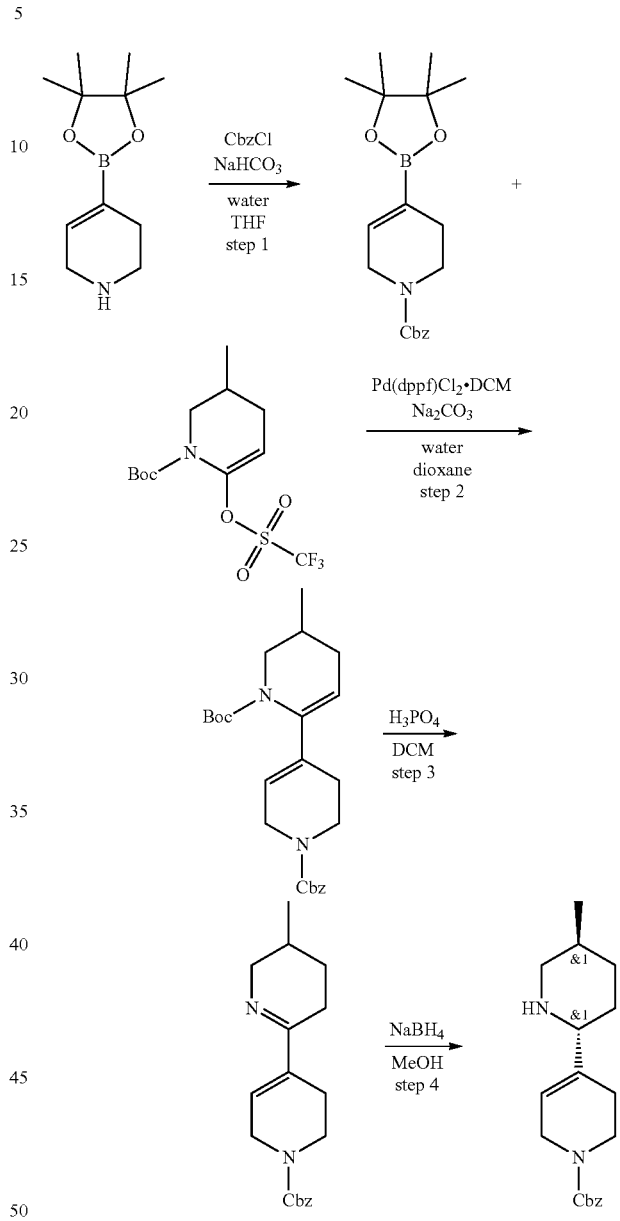

Step 1: Synthesis of benzyl 4-(4,4,5,5-tetramethyl-1,3,2-dioxaborolan-2-yl)-5,6-dihydropyridine-1(2H)-carboxylate To a solution of 4-(4,4,5,5-tetramethyl-1,3,2-dioxaborolan-2-yl)-1,2,3,6-tetrahydropyridine (36 g, 146.61 mmol, HCl) and sodium hydrogen carbonate (30.79 g, 366.53 mmol, 14.26 mL) in THF (700 mL) and water (350 mL), benzyl carbonochloridate (32.51 g, 190.59 mmol) was added dropwise at 10° C. The reaction mixture was stirred at rt for 12 hr, and the solvents were evaporated in vacuum. The residue was treated with water (300 mL) and extracted with EtOAc (2×200 mL). The combined organic layers were washed with brine, dried over Na$_2$SO$_4$ and concentrated in vacuum to provide the product benzyl 4-(4,4,5,5-tetramethyl-1,3,2-dioxaborolan-2-yl)-3,6-dihydro-2H-pyridine-1-carboxylate (45 g, 131.11 mmol, 89.43% yield) as a yellow solid.

$^1$H NMR (400 MHz, DMSO-d$_6$) δ (ppm) 1.15 (s, 12H), 2.06 (m, 2H), 3.36 (m, 2H), 3.92 (m, 2H), 5.04 (s, 2H), 6.35 (m, 1H), 7.32 (m, 5H).

LCMS(ESI): [M]$^+$ m/z: calcd 343.2; found 344.2; Rt=1.676 min.

Step 2: Synthesis of 1'-benzyl 1-tert-butyl 5-methyl-5,5',6,6'-tetrahydro-[2,4'-Bipyridine]-1,1'(2'H,4H)-Dicarboxylate A mixture of tert-butyl 3-methyl-6-(trifluoromethylsulfonyloxy)-3,4-dihydro-2H-pyridine-1-carboxylate (30.79 g, 89.15 mmol), benzyl 4-(4,4,5,5-tetramethyl-1,3,2-dioxaborolan-2-yl)-3,6-dihydro-2H-pyridine-1-carboxylate (45 g, 111.44 mmol), [1,1'-bis(diphenylphosphino)ferrocene]dichloropalladium(II), complex with DCM (3.64 g, 4.46 mmol) and sodium carbonate (28.35 g, 267.46 mmol, 11.20 mL) in dioxane (420 mL) and water (140 mL) was stirred at 90° C. under argon atmosphere for 28 hr. After cooling to rt, the reaction mixture was filtered off. The filter cake was washed with dioxane (600 mL) and discarded. Filtrate was concentrated under reduced pressure and the residue was purified by silica gel flash chromatography eluting with a 0 to 100 percent EtOAc-hexane gradient to give tert-butyl 6-(1-benzyloxycarbonyl-3,6-dihydro-2H-pyridin-4-yl)-3-methyl-3,4-dihydro-2H-pyridine-1-carboxylate (9.1 g, 22.06 mmol, 24.74% yield).

$^1$H NMR (500 MHz, CDCl$_3$) δ (ppm) 0.94 (d, 3H), 1.26 (m, 2H), 1.42 (s, 9H), 1.71 (m, 1H), 1.89 (m, 1H), 2.27 (m, 2H), 2.83 (m, 1H), 3.70 (m, 2H), 3.88 (m, 1H), 4.03 (m, 2H), 5.16 (s, 2H), 5.67 (m, 1H), 7.35 (m, 5H).

LCMS(ESI): [M-Boc]$^+$ m/z: calcd 312.2; found 313.2; Rt=1.634 min.

Step 3: Synthesis of benzyl 5-methyl-3,4,5,5',6,6'-Hexahydro-[2,4'-Bipyridine]-1'(2'H)-carboxylate Phosphoric acid (21.38 g, 218.17 mmol, 12.58 mL) was carefully added at r.t. to a solution of tert-butyl 6-(1-benzyloxycarbonyl-3,6-dihydro-2H-pyridin-4-yl)-3-methyl-3,4-dihydro-2H-pyridine-1-carboxylate (9 g, 21.82 mmol) in DCM (100 mL). The reaction mixture was then stirred for 12 hr at rt Crushed ice (25 g) was added to the residue and pH was adjusted to 8 with a 5% aqueous solution of Na$_2$CO$_3$. The resulting mixture was extracted with DCM (2*150 mL). The combined organic extracts were dried over sodium sulphate and evaporated in vacuum to afford benzyl 4-(3-methyl-2,3,4,5-tetrahydropyridin-6-yl)-3,6-dihydro-2H-pyridine-1-carboxylate (7 g, crude) as brown oil, which was used directly in the next step.

$^1$H NMR (400 MHz, DMSO-d$_6$) δ (ppm) 0.84 (d, 3H), 1.29 (m, 5H), 2.12 (m, 4H), 2.86 (m, 2H), 3.48 (m, 1H), 4.12 (m, 2H), 5.05 (s, 2H), 7.29 (m, 5H).

LCMS(ESI): [M]$^+$ m/z: calcd 312.2; found 313.2; Rt=1.039 min.

Step 4: Synthesis of rac-benzyl 4-((2R,5S)-5-methylpiperidin-2-yl)-5,6-dihydropyridine-1(2H)-carboxylate Sodium borohydride (1.27 g, 33.61 mmol, 1.19 mL) was added in one portion to a stirred solution of benzyl 4-(3-methyl-2,3,4,5-tetrahydropyridin-6-yl)-3,6-dihydro-2H-pyridine-1-carboxylate (7 g, 22.41 mmol) in MeOH (150 mL) at 0° C. The resulting mixture was stirred at 0° C. for 1 hr, and then evaporated in vacuum. The residue was diluted with water (150 mL) and extracted with DCM (2*200 mL). The combined organic extracts were dried over sodium sulphate and evaporated in vacuum to afford benzyl 4-[(2R,5S)-5-methyl-2-piperidyl]-3,6-dihydro-2H-pyridine-1-carboxylate (7 g, crude) as brown oil, which was used directly in the next step.

$^1$H NMR (400 MHz, DMSO-d$_6$) δ (ppm) 0.74 (d, 3H), 0.96 (m, 1H), 1.06 (m, 5H), 1.56 (m, 2H), 2.12 (m, 3H), 2.86 (m, 2H), 3.29 (m, 1H), 4.12 (m, 1H), 4.46 (m, 1H), 5.04 (s, 2H), 7.29 (m, 5H).

LCMS(ESI): [M]$^+$ m/z: calcd 314.2; found 315.2; Rt=1.076 min.

6BBB. Synthesis of rac-benzyl 3-((2R,5S)-5-methylpiperidin-2-yl)-5,6-dihydropyridine-1(2H)-carboxylate

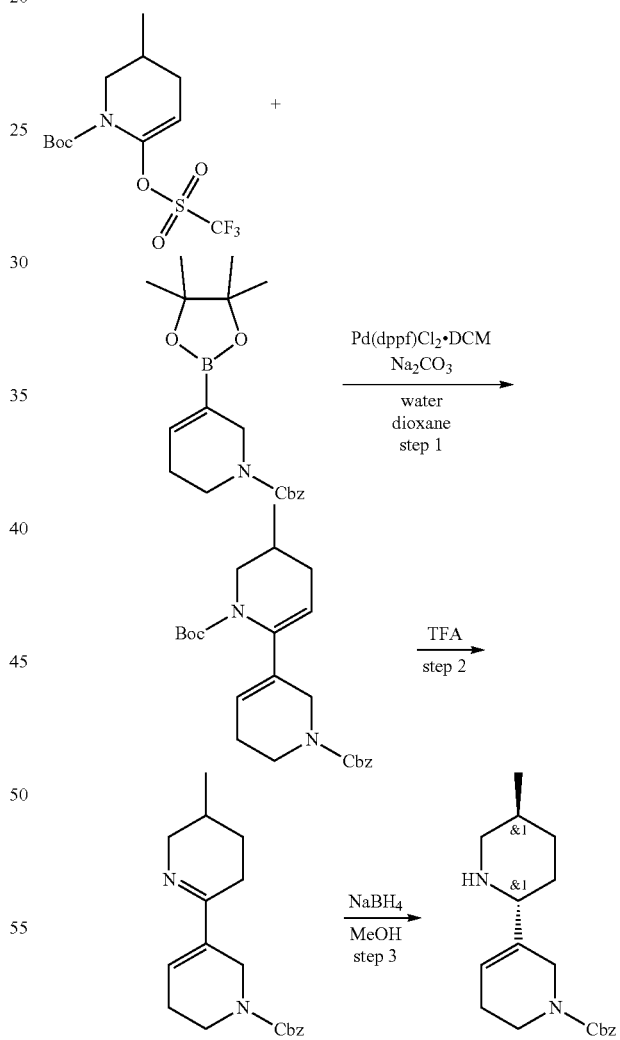

Step 1: Synthesis of 1'-benzyl 1-tert-butyl 5-methyl-5,5',6,6'-tetrahydro-[2,3'-Bipyridine]-1,1'(2'H,4H)-Dicarboxylate A solution of benzyl 5-(4,4,5,5-tetramethyl-1,3,2-dioxaborolan-2-yl)-3,6-dihydro-2H-pyridine-1-carboxylate (12 g, 34.96 mmol), tert-butyl 3-methyl-6-(trifluoromethylsulfonyloxy)-3,4-dihydro-2H-pyridine-1-carboxylate (14.49 g, 41.96 mmol), sodium carbonate (11.12 g, 104.89 mmol, 4.39 mL) in dioxane (100 mL) and water (30 mL) was evacuated and refiled with Ar three time. To this mixture, [1,1'-bis(diphenylphosphino)ferrocene]dichloropalladium(II), complex with DCM (1.43 g, 1.75 mmol) was added and resulting mixture was stirred at 95° C. for 12 hr, cooled, filtered and evaporated. The residue was taken up with water (200 ml) and extracted with MTBE (3*200 ml). The organic layer was washed with brine (150 ml), dried over $Na_2SO_4$, filtered through a thin layer of $SiO_2$ and evaporated in vacuum to give tert-butyl 6-(1-benzyloxycarbonyl-3,6-dihydro-2H-pyridin-5-yl)-3-methyl-3,4-dihydro-2H-pyridine-1-carboxylate (15 g, crude). This compound was used for the next step without further purification.

$^1$H NMR (400 MHz, $CDCl_3$) δ (ppm) 0.93 (d, 3H), 1.21 (s, 9H), 2.16 (m, 4H), 2.77 (m, 1H), 3.48 (m, 3H), 3.86 (m, 2H), 4.06 (m, 1H), 4.25 (m, 1H), 5.11 (s, 2H), 5.77 (m, 1H), 7.32 (m, 5H).

LCMS(ESI): [M-Boc]$^+$ m/z: calcd 312.2; found 313.2; Rt=1.749 min.

Step 2: Synthesis of benzyl 5-methyl-3,4,5,5',6,6'-Hexahydro-[2,3'-Bipyridine]-1'(2'H)-carboxylate A solution of tert-butyl 6-(1-benzyloxycarbonyl-3,6-dihydro-2H-pyridin-5-yl)-3-methyl-3,4-dihydro-2H-pyridine-1-carboxylate (15 g, 36.36 mmol) in TFA (62.19 g, 545.43 mmol, 42.02 mL) was stirred at 25° C. for 2 hr and solvent was removed in vacuum. The residue was taken up with water (150 ml) and pH was adjusted to 8-9 with NaOH solution, extracted with DCM (3*100). The organic layer was washed with brine (100 ml), dried over $Na_2SO_4$ and the solvent was removed in vacuum to give benzyl 5-(3-methyl-2,3,4,5-tetrahydropyridin-6-yl)-3,6-dihydro-2H-pyridine-1-carboxylate (11 g, crude) as brown gum. This compound was used for the next step without further purification.

$^1$H NMR (500 MHz, $CDCl_3$) δ (ppm) 0.88 (d, 3H), 1.23 (m, 2H), 1.68 (m, 2H), 1.96 (m, 2H), 2.24 (m, 4H), 2.78 (m, 1H), 3.54 (m, 1H), 4.25 (m, 1H), 4.57 (m, 1H), 5.15 (s, 2H), 7.35 (m, 5H).

LCMS(ESI): [M]$^+$ m/z: calcd 312.2; found 313.2; Rt=0.901 min.

Step 3: Synthesis of rac-benzyl 3-((2R,5S)-5-methylpiperidin-2-yl)-5,6-dihydropyridine-1(2H)-carboxylate To solution of benzyl 5-(3-methyl-2,3,4,5-tetrahydropyridin-6-yl)-3,6-dihydro-2H-pyridine-1-carboxylate (11 g, 35.21 mmol) in MeOH (100 mL), sodium borohydride (2.00 g, 52.82 mmol, 1.87 mL) was added portion wise at 0° C. The resulting mixture was stirred for 2 hr and the solvent was evaporated in vacuum and residue was taken up with water (150 ml) and extracted with DCM (3*100 ml), washed with brine (100 ml), dried over $Na_2SO_4$ and evaporated in vacuum to give crude benzyl 5-[(2R,5S)-5-methyl-2-piperidyl]-3,6-dihydro-2H-pyridine-1-carboxylate (10 g, crude). This compound was used for the next step without purification.

$^1$H NMR (400 MHz, $CDCl_3$) δ (ppm) 0.82 (m, 1H), 0.98 (d, 3H), 1.69 (m, 3H), 1.95 (m, 1H), 2.10 (m, 2H), 2.62 (m, 2H), 3.17 (m, 2H), 3.54 (m, 1H), 3.95 (m, 2H), 4.55 (m, 1H), 4.78 (m, 1H), 5.12 (s, 2H), 7.33 (m, 5H).

LCMS(ESI): [M]$^+$ m/z: calcd 314.2; found 315.2; Rt=0.941 min.

6CCC. Synthesis of 7-(5-methylpiperidin-2-yl)-3,4-dihydro-2H-benzo[b][1,4]oxazine

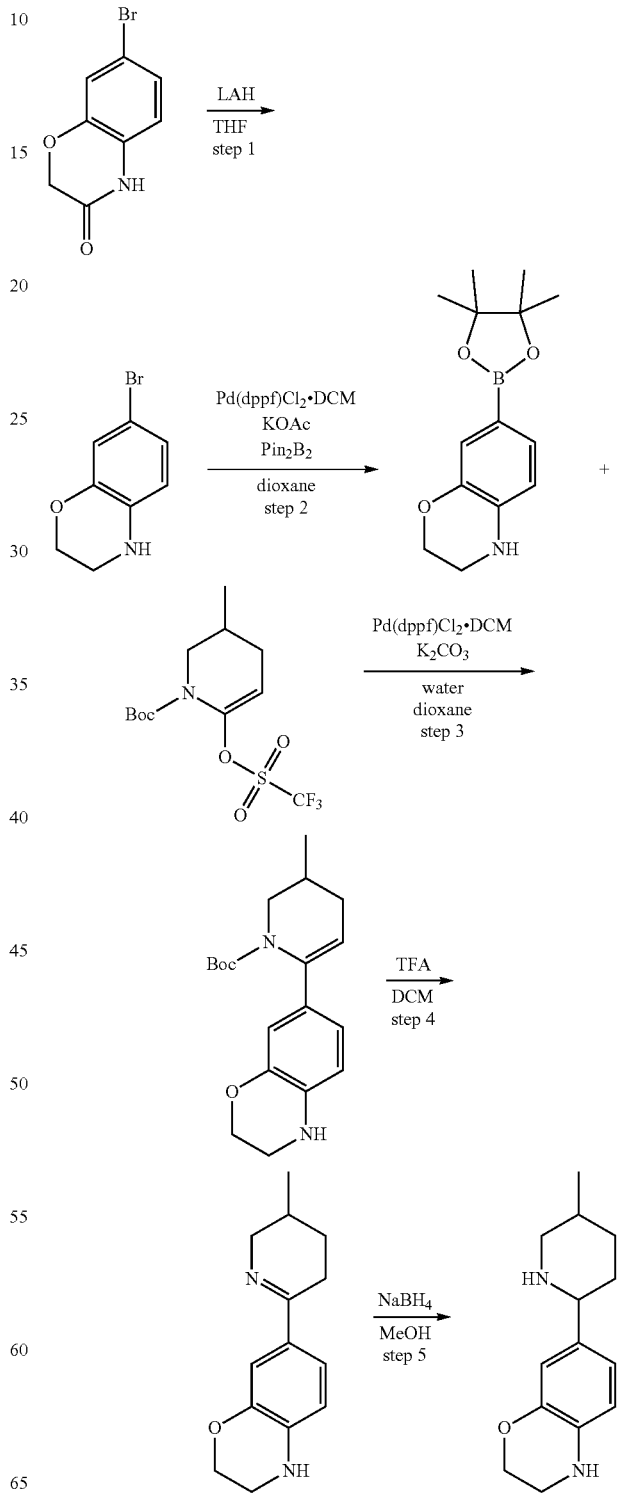

Step 1: Synthesis of 7-bromo-3,4-dihydro-2H-benzo[b][1,4]oxazine

To a suspension of LAH (1.21 g, 31.85 mmol) in THF (10 mL) was carefully added dropwise 7-bromo-4H-1,4-benzoxazin-3-one (6.05 g, 26.54 mmol) in THF (100 mL) under argon. Resulting mixture was heated at 70° C. for 12 hr. After cooling to rt 1 ml of 50% solution KOH in water was added dropwise. Resulting precipitate was filtered, washed with THF (2×5 ml) and discarded. Obtained solvent were combined, dried with sodium sulfate and evaporated to obtain 7-bromo-3,4-dihydro-2H-1,4-benzoxazine (5.9 g, crude) that was used in the next step without further purification.

$^1$H NMR (400 MHz, CDCl$_3$) δ (ppm) 3.38 (t, 2H), 4.22 (t, 2H), 5.28 (m, 1H), 6.46 (d, 1H), 6.82 (d, 1H), 6.89 (s, 1H).

GCMS: calcd 214.2; found 214.2; Rt=9.248 min.

Step 2: Synthesis of 7-(4,4,5,5-tetramethyl-1,3,2-dioxaborolan-2-yl)-3,4-dihydro-2H-benzo[b][1,4]oxazine Potassium acetate (3.97 g, 40.46 mmol, 2.53 mL) was added a solution of 7-bromo-3,4-dihydro-2H-1,4-benzoxazine (3.94 g, 18.39 mmol) in dioxane (40 mL), followed by addition of bis(pinacolato)diboron (4.67 g, 18.39 mmol) and Pd(dppf)C$_{12}$ (672.76 mg, 919.44 µmol). The resulting solution was stirred overnight at 90° C. under Ar. The resulting mixture was concentrated under vacuum, diluted with EtOAc, filtered and evaporated. Resulting crude precipitate was purified by column chromatography (Hexane/MTBE) to obtain 7-(4,4,5,5-tetramethyl-1,3,2-dioxaborolan-2-yl)-3,4-dihydro-2H-1,4-benzoxazine (710 mg, 2.72 mmol, 14.79% yield).

$^1$H NMR (400 MHz, CDCl$_3$) δ (ppm) 1.29 (s, 12), 3.42 (t, 2H), 4.20 (t, 2H), 6.52 (d, 1H), 7.21 (m, 2H).

LCMS(ESI): [M]$^+$ m/z: calcd 261.2; found 262.2; Rt=1.369 min.

Step 3: Synthesis of tert-butyl 6-(3,4-dihydro-2H-benzo[b][1,4]Oxazin-7-yl)-3-methyl-3,4-dihydropyridine-1(2H)-carboxylate To a solution of potassium carbonate (1.13 g, 8.16 mmol, 492.31 µL) in water (10 mL) was added to a solution of 7-(4,4,5,5-tetramethyl-1,3,2-dioxaborolan-2-yl)-3,4-dihydro-2H-1,4-benzoxazine (710 mg, 2.72 mmol) in dioxane (10 mL), followed by addition of tert-butyl 3-methyl-6-(trifluoromethylsulfonyloxy)-3,4-dihydro-2H-pyridine-1-carboxylate (1.03 g, 2.99 mmol) and Pd(dppf)C$_{12}$ (99.48 mg, 135.95 µmol). The resulting mixture was stirred overnight at 90° C. under Ar. The resulting mixture was concentrated under vacuum, diluted with EtOAc and washed with water (2×40 ml). Organic phase was dried over sodium sulfate, filtered and evaporated to obtain tert-butyl 6-(3,4-dihydro-2H-1,4-benzoxazin-7-yl)-3-methyl-3,4-dihydro-2H-pyridine-1-carboxylate (900 mg, crude).

$^1$H NMR (400 MHz, CDCl$_3$) δ (ppm) 1.01 (d, 3H), 1.17 (m, 3H), 1.29 (s, 9H), 1.81 (m, 1H), 1.99 (m, 1H), 2.38 (m, 1H), 2.93 (m, 1H), 3.43 (m, 2H), 3.98 (m, 1H), 4.24 (m, 1H), 6.64 (m, 3H).

LCMS(ESI): [M]$^+$ m/z: calcd 330.2; found 331.2; Rt=1.394 min.

Step 4: Synthesis of 7-(5-methyl-3,4,5,6-tetrahydropyridin-2-yl)-3,4-dihydro-2H-benzo[b][1,4]oxazine A solution of tert-butyl 6-(3,4-dihydro-2H-1,4-benzoxazin-7-yl)-3-methyl-3,4-dihydro-2H-pyridine-1-carboxylate (1.25 g, 3.78 mmol) in TFA (5 mL) and DCM (5 mL) was stirred at 25° C. for 12 hr. Potassium carbonate saturated aq. solution was added to the solution (50 ml) and then extracted with DCM (2×50 ml). Organic phase was dried over sodium sulfate, filtered and evaporated to obtain 7-(3-methyl-2,3,4,5-tetrahydropyridin-6-yl)-3,4-dihydro-2H-1,4-benzoxazine (882 mg, crude).

$^1$H NMR (400 MHz, CDCl$_3$) δ (ppm) 0.94 (d, 3H), 1.72 (m, 4H), 2.49 (m, 1H), 3.02 (m, 1H), 3.22 (m, 1H), 3.40 (m, 2H), 3.89 (m, 1H), 4.21 (m, 1H), 6.58 (m, 2H), 6.74 (m, 1H), 6.98 (m, 1H).

Step 5: Synthesis of 7-(5-methylpiperidin-2-yl)-3,4-dihydro-2H-benzo[b][1,4]oxazine Sodium borohydride (173.87 mg, 4.60 mmol, 162.49 µL) was added portion wise to a solution of 7-(3-methyl-2,3,4,5-tetrahydropyridin-6-yl)-3,4-dihydro-2H-1,4-benzoxazine (882 mg, 3.83 mmol) in MeOH (10 mL). The mixture was stirred at rt for 2 hr. Water (50 ml) was added and resulting mixture was extracted with EtOAc (2×30 ml). Organic phase was dried over sodium sulfate, filtered and evaporated to obtain 7-(5-methyl-2-piperidyl)-3,4-dihydro-2H-1,4-benzoxazine (0.68 g, crude).

$^1$H NMR (400 MHz, CDCl$_3$) δ (ppm) 0.84 (d, 3H), 1.48 (m, 2H), 1.76 (m, 5H), 2.36 (m, 1H), 3.09 (m, 1H), 3.40 (m, 2H), 4.22 (m, 2H), 6.58 (m, 2H), 6.75 (m, 2H).

LCMS(ESI): [M]$^+$ m/z: calcd 232.2; found 233.2; Rt=0.789 min.

6DDD. Synthesis of rac-5-((2R,5S)-5-methylpiperidin-2-yl)isoindolin-1-one

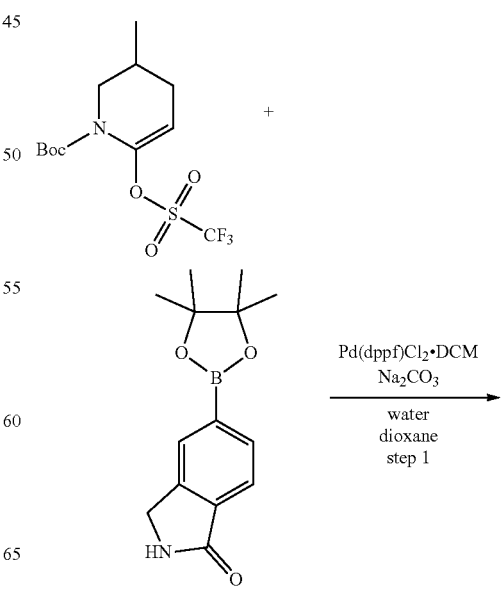

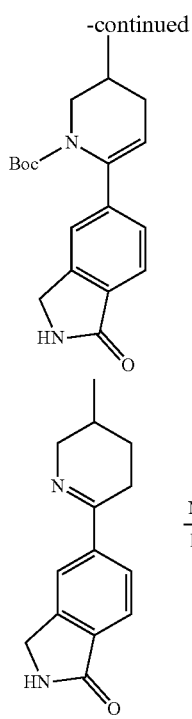

Step 1: Synthesis of tert-butyl 3-methyl-6-(1-oxoisoindolin-5-yl)-3,4-dihydropyridine-1(2H)-carboxylate 5-(4,4,5,5-tetramethyl-1,3,2-dioxaborolan-2-yl)isoindolin-1-one (4 g, 15.44 mmol), tert-butyl 3-methyl-6-(trifluoromethylsulfonyloxy)-3,4-dihydro-2H-pyridine-1-carboxylate (5.86 g, 16.98 mmol) and sodium carbonate (3.27 g, 30.88 mmol, 1.29 mL) were mixed together in a mixture of dioxane (60 mL) and water (20 mL). The flask was evacuated and backfilled three times with argon and dichloro(1,1'-bis(diphenylphosphanyl)ferrocene)palladium(II)*DCM (630.12 mg, 771.88 µmol) was added thereto. The reaction mixture was heated at 75° C. for 12 hr. The reaction mixture was diluted with EtOAc, the solid which was formed was filtered off, washed with addition EtOAc and dried on vacuum to give tert-butyl 3-methyl-6-(1-oxoisoindolin-5-yl)-3,4-dihydro-2H-pyridine-1-carboxylate (3.7 g, 11.27 mmol, 72.98% yield) which was used in the next step without further purification.

$^1$H NMR (500 MHz, DMSO-d$_6$) δ (ppm) 0.98 (s, 12H), 1.87 (m, 2H), 2.41 (m, 1H), 3.03 (m, 1H), 3.88 (m, 1H), 4.32 (m, 2H), 5.43 (m, 1H), 7.42 (m, 3H), 8.46 (s, 1H).

LCMS(ESI): [M]$^+$ m/z: calcd 328.2; found 329.2; Rt=3.610 min.

Step 2: Synthesis of 5-(5-methyl-3,4,5,6-tetrahydropyridin-2-yl)isoindolin-1-one tert-butyl 3-methyl-6-(1-oxoisoindolin-5-yl)-3,4-dihydro-2H-pyridine-1-carboxylate (3.67 g, 11.18 mmol) was dissolved in a mixture of DCM (11 mL) and TFA (11 mL) then stirred at rt for 1 hr. The reaction mixture was neutralized with 20% aq. solution of NaOH, obtained solution was diluted with DCM, the organic phase was separated and the aqueous layer was washed with additional DCM. The organic phase was dried over Na$_2$SO$_4$, filtered and concentrated on vacuum to give 5-(3-methyl-2,3,4,5-tetrahydropyridin-6-yl)isoindolin-1-one (1.77 g, 7.73 mmol, 69.18% yield) which was used in the next step without further purification.

$^1$H NMR (500 MHz, CDCl$_3$) δ (ppm) 1.03 (d, 3H), 1.41 (m, 1H), 1.75 (m, 2H), 1.97 (m, 1H), 2.65 (m, 1H), 2.83 (m, 1H), 3.31 (m, 1H), 4.07 (m, 1H), 4.46 (m, 1H), 6.88 (m, 1H), 7.88 (m, 3H).

Step 3: Synthesis of rac-5-((2R,5S)-5-methylpiperidin-2-yl)isoindolin-1-one 5-(3-methyl-2,3,4,5-tetrahydropyridin-6-yl)isoindolin-1-one (1.77 g, 7.73 mmol) was dissolved in MeOH (20 mL) and sodium borohydride (877.50 mg, 23.19 mmol, 820.09 µL) was added portion wise under cooling with ice water. The reaction mixture was heated to rt and stirred for 12 hr. NH$_4$Cl (aq.) was added and MeOH was evaporated, aqueous layer was extracted with DCM (3*30 ml) and combined organic layer was dried over Na$_2$SO$_4$, filtered and evaporated on vacuum at 45° C. to give 5-[(2R,5S)-5-methyl-2-piperidyl]isoindolin-1-one (1.24 g, 5.38 mmol, 69.64% yield) which was used in the next step without further purification. 5-[(2R,5S)-5-methyl-2-piperidyl]isoindolin-1-one (1.24 g, 5.38 mmol, 69.64% yield).

$^1$H NMR (400 MHz, CDCl$_3$) δ (ppm) 0.89 (d, 3H), 1.17 (m, 2H), 1.85 (m, 4H), 2.42 (m, 1H), 3.15 (m, 1H), 3.64 (m, 1H), 4.40 (m, 2H), 6.96 (m, 1H), 7.50 (m, 2H), 7.78 (m, 1H).

LCMS(ESI): [M]$^+$ m/z: calcd 230.2; found 231.2; Rt=0.889 min.

6EEE. Synthesis of 5-(4-(5-methylpiperidin-2-yl)phenyl)thiazole

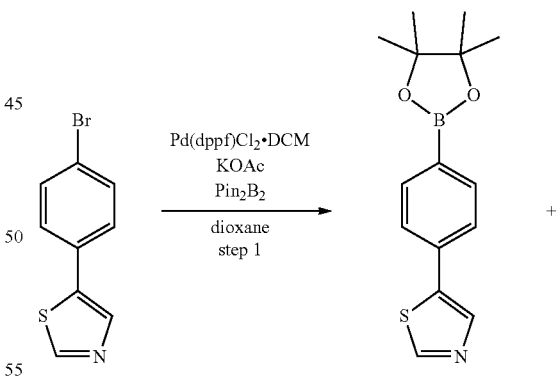

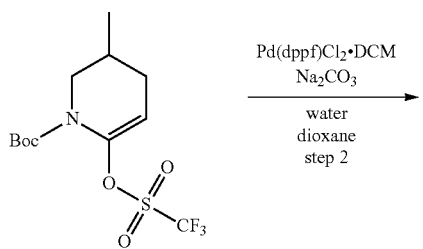

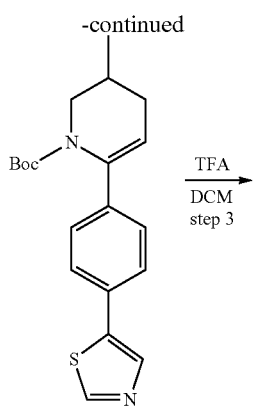

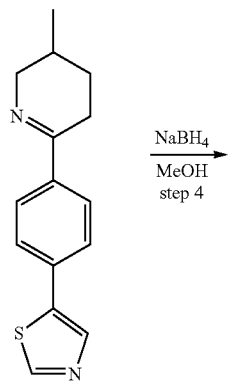

Step 1: Synthesis of 5-(4-(4,4,5,5-tetramethyl-1,3,2-dioxaborolan-2-yl)phenyl)thiazole Potassium acetate (11.44 g, 116.61 mmol, 7.29 mL) was added to a solution of 5-(4-bromophenyl)thiazole (14 g, 58.30 mmol) and 4,4,5,5-tetramethyl-2-(4,4,5,5-tetramethyl-1,3,2-dioxaborolan-2-yl)-1,3,2-dioxaborolane (16.29 g, 64.13 mmol) in dioxane (150 mL). Reaction flask was evacuated and refilled with Ar 3 times. Then Pd(dppf)Cl$_2$*DCM (2.38 g, 2.92 mmol) was added under stream of argon. Resulting mixture was stirred at 90° C. for 14 hr under inert atmosphere. Then, it was cooled, diluted with EtOAc (400 mL) and washed with water (2×200 mL). Organic layer was dried over Na$_2$SO$_4$ and concentrated under reduced pressure. The residue was purified by silica gel flash chromatography eluting with a 0 to 100 percent hexane-MTBE gradient to give 5-[4-(4,4,5,5-tetramethyl-1,3,2-dioxaborolan-2-yl)phenyl]thiazole (10 g, 34.82 mmol, 59.72% yield).

$^1$H NMR (400 MHz, CDCl$_3$) δ (ppm) 1.32 (s, 12H), 7.58 (d, 2H), 7.68 (d, 2H), 8.12 (s, 1H), 8.82 (s, 1H).

LCMS(ESI): [M]$^+$ m/z: calcd 287.2; found 288.2; Rt=1.546 min.

Step 2: Synthesis of tert-butyl 3-methyl-6-(4-(Thiazol-5-yl)phenyl)-3,4-dihydropyridine-1(2H)-carboxylate tert-butyl 3-methyl-6-(trifluoromethylsulfonyloxy)-3,4-dihydro-2H-pyridine-1-carboxylate (4.81 g, 13.93 mmol), 5-[4-(4,4,5,5-tetramethyl-1,3,2-dioxaborolan-2-yl)phenyl]thiazole (4 g, 13.93 mmol) and sodium carbonate (4.43 g, 41.79 mmol, 1.75 mL) were added to a mixture of water (15 mL) and dioxane (45 mL). The resulting mixture was evacuated and then backfilled with argon, this operation was repeated three times, then Pd(dppf)Cl$_2$*DCM (568.72 mg, 696.42 µmol) was added under argon. The reaction mixture was stirred under argon at 70° C. for 14 hr, then cooled and filtered. The filter cake was washed with 1,4-dioxane (2*20 ml) and discarded. The filtrate was evaporated in vacuum to afford tert-butyl 3-methyl-6-(4-thiazol-5-ylphenyl)-3,4-dihydro-2H-pyridine-1-carboxylate (4 g, 11.22 mmol, 80.56% yield) as brown oil, which was used in next step without purification.

$^1$H NMR (500 MHz, DMSO-d$_6$) δ (ppm) 0.95 (d, 3H), 1.06 (s, 9H), 1.86 (m, 1H), 2.46 (m, 1H), 3.12 (m, 1H), 3.26 (m, 1H), 4.42 (m, 1H), 5.72 (m, 1H), 7.28 (d, 2H), 7.67 (d, 2H), 8.29 (s, 1H), 9.06 (s, 1H).

LCMS(ESI): [M]$^+$ m/z: calcd 356.2; found 357.2; Rt=1.654 min.

Step 3: Synthesis of 5-(4-(5-methyl-3,4,5,6-tetrahydropyridin-2-yl)phenyl)thiazole The solution of tert-butyl 3-methyl-6-(4-thiazol-5-ylphenyl)-3,4-dihydro-2H-pyridine-1-carboxylate (4 g, 11.22 mmol) in TFA (19.19 g, 168.31 mmol, 12.97 mL) was stirred at 25° C. for 1 hr, and then evaporated in vacuum. Crushed ice (15 g) was added to the residue and pH was adjusted to 10 with a 10% aqueous solution of sodium hydroxide. The resulting mixture was extracted with DCM (2*30 ml). The combined organic extracts were dried over sodium sulphate and evaporated in vacuum to afford 5-[4-(3-methyl-2,3,4,5-tetrahydropyridin-6-yl)phenyl]thiazole (2.8 g, 10.92 mmol, 97.34% yield) as brown oil, which was used directly in the next step.

$^1$H NMR (400 MHz, DMSO-d$_6$) δ (ppm) 0.89 (d, 3H), 1.28 (m, 1H), 1.58 (m, 1H), 1.82 (m, 1H), 2.71 (m, 1H), 3.15 (m, 1H), 3.86 (m, 1H), 4.30 (m, 1H), 7.41 (d, 2H), 7.64 (d, 2H), 8.32 (s, 1H), 9.05 (s, 1H).

LCMS(ESI): [M]$^+$ m/z: calcd 256.2; found 257.2; Rt=0.945 min.

Step 4: Synthesis of 5-(4-(5-methylpiperidin-2-yl)phenyl)thiazole

Sodium borohydride (826.41 mg, 21.84 mmol, 772.34 µL) was added in one portion to a stirred solution of 5-[4-(3-methyl-2,3,4,5-tetrahydropyridin-6-yl)phenyl]thiazole (2.8 g, 10.92 mmol) in MeOH (50 mL) at 0° C. The resulting mixture was stirred at 25° C. for 12 hr, and then evaporated in vacuum. The residue was diluted with water (20 ml) and extracted with DCM (2*40 ml). The combined organic extracts were dried over sodium sulphate and evaporated in vacuum. The obtained oil was subjected to HPLC (Waters Sunfire C18 19*100 5 mkm column and MeOH as an eluent mixture) to afford 5-[4-(5-methyl-2-piperidyl)phenyl]thiazole (0.37 g, 1.43 mmol, 13.11% yield).

$^1$H NMR (400 MHz, DMSO-d$_6$) δ (ppm) 0.81 (d, 3H), 1.08 (m, 1H), 1.22 (m, 1H), 1.48 (m, 1H), 1.71 (m, 2H), 2.22 (m, 1H), 2.96 (m, 1H), 3.46 (m, 1H), 4.36 (m, 1H), 7.39 (d, 2H), 7.54 (d, 2H), 8.28 (s, 1H), 9.05 (s, 1H).

LCMS(ESI): [M]$^+$ m/z: calcd 258.2; found 259.2; Rt=1.410 min.

6FFF. Synthesis of 6-[(2S,5R)-5-methyl-2-piperidyl]-1,3-benzothiazole

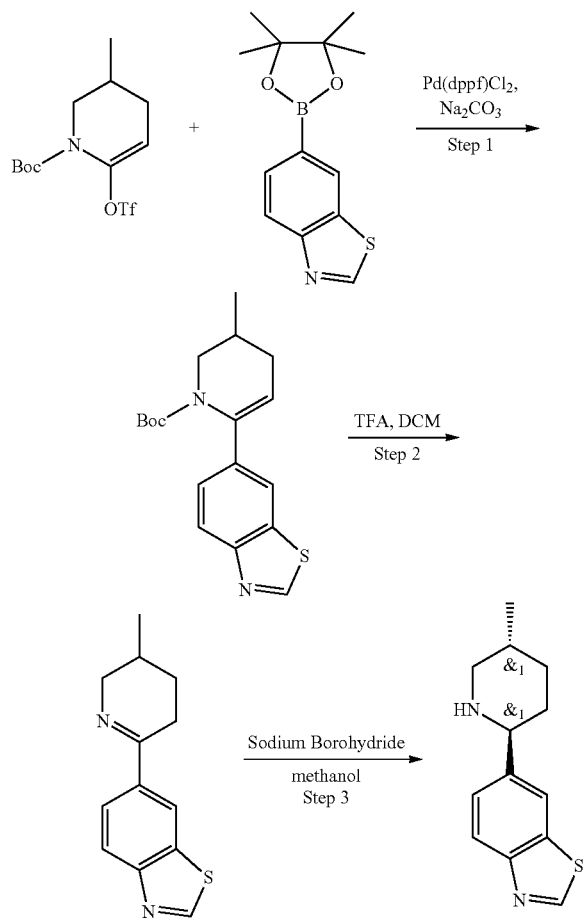

Step 1. Synthesis of tert-butyl 6-(1,3-benzothiazol-6-yl)-3-methyl-3,4-dihydro-2H-pyridine-1-carboxylate Sodium carbonate (4.06 g, 38.29 mmol, 1.60 mL) was added to a solution of 6-(4,4,5,5-tetramethyl-1,3,2-dioxaborolan-2-yl)-1,3-benzothiazole (5 g, 19.15 mmol) and tert-butyl 3-methyl-6-(trifluoromethylsulfonyloxy)-3,4-dihydro-2H-pyridine-1-carboxylate (7.27 g, 21.06 mmol) in dioxane (60 mL) and water (20 mL). Reaction flask was evacuated and refilled with argon 3 times. Then, dichloro(1,1'-bis(diphenylphosphanyl)ferrocene)palladium(II)*CH$_2$Cl$_2$ (781.50 mg, 957.32 µmol) was added under stream of argon. Resulting mixture was stirred at 90° C. for 12 hr under inert atmosphere. Solvents were removed under reduced pressure and residue was redissolved in EA. Insoluble solids were filtered off through a short pad of silicagel and filtrate was concentrated in vacuo, affording tert-butyl 6-(1,3-benzothiazol-6-yl)-3-methyl-3,4-dihydro-2H-pyridine-1-carboxylate (6.11 g, 18.49 mmol, 96.57% yield).

$^1$H NMR (500 MHz, CDCl$_3$) δ (ppm) 0.99 (m, 13H), 1.46 (m, 1H), 1.85 (m, 1H), 2.02 (m, 1H), 2.40 (m, 3H), 3.04 (m, 1H), 4.07 (m, 1H), 5.37 (m, 1H), 7.46 (d, 1H), 7.84 (s, 1H), 7.99 (d, 1H), 8.92 (s, 1H).

LCMS(ESI): [M+1]$^+$ m/z: calcd 330.2; found 331.0; Rt=1.542 min.

Step 2. Synthesis of 6-(3-methyl-2,3,4,5-tetrahydropyridin-6-yl)-1,3-benzothiazole tert-butyl 6-(1,3-benzothiazol-6-yl)-3-methyl-3,4-dihydro-2H-pyridine-1-carboxylate (6.11 g, 18.49 mmol) was dissolved in a mixture of DCM (18 mL) and TFA (18 mL) then stirred ar RT for 1 hr. The reaction mixture was neutralized with 20% aq. solution of NaOH, obtained solution was diluted with DCM, the organic phase was separated and the aqueous layer was washed with additional DCM. The organic phase was dried over Na$_2$SO$_4$, filtered and concentrated on vacuo to give 6-(3-methyl-2,3,4,5-tetrahydropyridin-6-yl)-1,3-benzothiazole (4.1 g, 17.80 mmol, 96.27% yield) which was used in the next step without further purification.

$^1$H NMR (500 MHz, CDCl$_3$) δ (ppm) 1.00 (m, 3H), 1.42 (m, 1H), 1.74 (m, 1H), 1.96 (m, 1H), 2.65 (m, 1H), 2.84 (m, 1H), 3.29 (m, 1H), 4.02 (d, 1H), 7.96 (d, 1H), 8.10 (d, 1H), 8.39 (s, 1H), 9.01 (s, 1H).

LCMS(ESI): [M+1]$^+$ m/z: calcd 230.1; found 231.2; Rt=0.581 min.

Step 3. Synthesis of 6-[(2S,5R)-5-methyl-2-piperidyl]-1,3-benzothiazole 6-(3-methyl-2,3,4,5-tetrahydropyridin-6-yl)-1,3-benzothiazole (4.1 g, 17.80 mmol) was dissolved in methanol (40 mL) and Sodium Borohydride (2.02 g, 53.40 mmol, 1.89 mL) was added portionwise under cooling with icewater. The reaction mixture was heated to RT and stirred for 12 hr. NH$_4$Cl (aq.) was added and methanol was evaporated, aqueous layer was extracted with DCM (3*30 ml) and combined organic layer was dried over Na$_2$SO$_4$, filtered and evaporated on vacuo at 45° C. to give 6-[(2S,5R)-5-methyl-2-piperidyl]-1,3-benzothiazole (4 g, 17.22 mmol, 96.71% yield) which was used in the next step without further purification.

$^1$H NMR (400 MHz, CDCl$_3$) δ (ppm) 0.90 (m, 3H), 1.16 (m, 2H), 1.57-1.65 (m, 3H), 1.85 (m, 2H), 2.43 (t, 1H), 3.15 (d, 1H), 3.67 (d, 1H), 7.49 (d, 1H), 7.98 (s, 1H), 8.02 (d, 1H), 8.92 (s, 1H).

LCMS(ESI): [M+1]$^+$ m/z: calcd 232.1; found 233.2; Rt=0.837 min.

6GGG. Synthesis of rac-5-[(2S,5R)-5-methyl-2-piperidyl]-1,3-dihydrobenzimidazol-2-one

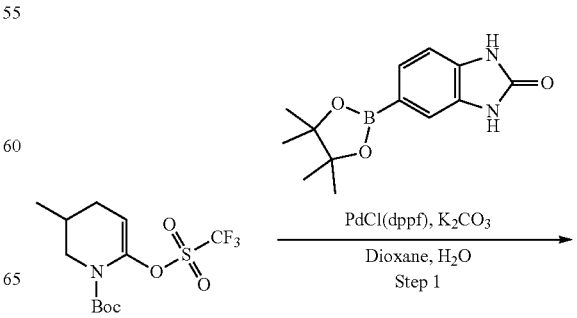

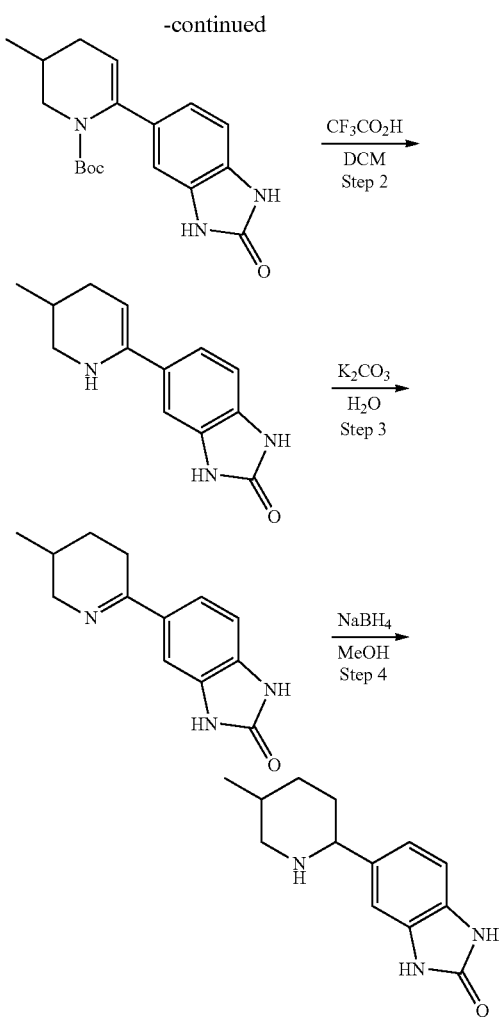

Step 1: Synthesis of tert-butyl 3-methyl-6-(2-oxo-1,3-dihydrobenzimidazol-5-yl)-3,4-dihydro-2H-pyridine-1-carboxylate A stirring suspension of tert-butyl 3-methyl-6-(trifluoromethylsulfonyloxy)-3,4-dihydro-2H-pyridine-1-carboxylate (3.98 g, 11.53 mmol), 5-(4,4,5,5-tetramethyl-1,3,2-dioxaborolan-2-yl)-1,3-dihydrobenzimidazol-2-one (3 g, 11.53 mmol) and Potassium carbonate (4.78 g, 34.60 mmol, 2.09 mL) in 1,4-dioxane (50 mL) and Water (50 mL) was purged with argon. Then, Pd(dppf)Cl₂ (421.98 mg, 576.71 µmol) was added under argon. The reaction mixture was stirred under argon at 90° C. for 12 hours After 12 hours, the reaction mixture was cooled and filtered. The filtrate was evaporated in vacuo and the residue was diluted with water (80 mL) and EtOAc. Both layers were separated. The organic layer was dried over Na₂SO₄, filtered and concentrated under reduced pressure to obtain tert-butyl 3-methyl-6-(2-oxo-1,3-dihydrobenzimidazol-5-yl)-3,4-dihydro-2H-pyridine-1-carboxylate (2.01 g, crude) as a black gum.

LCMS(ESI): [M+H]⁺ m/z: calcd 329.2; found 330.2; Rt=1.231 min.

Step 2: Synthesis of 5-(3-methyl-4,2,3,4-tetrahydro-pyridin-6-yl)-1,3-dihydrobenzimidazol-2-one To a stirred solution of tert-butyl 3-methyl-6-(2-oxo-1,3-dihydrobenzimidazol-5-yl)-3,4-dihydro-2H-pyridine-1-carboxylate (1.8 g, 5.46 mmol) in DCM (20 mL) was added CF₃CO₂H (20 mL) dropwise at 0° C. The resulting reaction mixture was stirred for 2 hours at 25° C. After 2 hours, the reaction mixture was carefully poured into K₂CO₃ solution (50 mL) and extracted with DCM (2×50 mL). The combined organic phase was dried over Na₂SO₄, filtered and concentrated under reduced pressure to obtain 5-(3-methyl-1,2,3,4-tetrahydropyridin-6-yl)-1,3-dihydrobenzimidazol-2-one (1.92 g, crude). The crude product was used in the next step reaction without any further purification.

LCMS(ESI): [M+H]⁺ m/z: calcd 229.1; found 230.2; Rt=0.697 min.

Step 3: Synthesis of 5-(3-methyl-2,3,4,5-tetrahydro-pyridin-6-yl)-1,3-dihydrobenzimidazol-2-one A solution of Potassium carbonate (1.74 g, 12.56 mmol) in Water (40 mL) was added to 5-(3-methyl-1,2,3,4-tetrahydropyridin-6-yl)-1,3-dihydrobenzimidazol-2-one (1.92 g, 8.37 mmol). The resulting mixture was stirred for 30 minutes and then evaporated to dryness. DCM (50 mL) was added and the resulting mixture was filtered. The obtained residue was washed with DCM and dried under vacuum to obtain 5-(3-methyl-2,3,4,5-tetrahydropyridin-6-yl)-1,3-dihydrobenzimidazol-2-one (1.8 g, crude) as a brown solid.

¹H NMR (DMSO-d₆, 500 MHz): δ (ppm) 0.92 (s, 3H), 1.26 (m, 1H), 1.60 (m, 1H), 1.83 (m, 1H), 2.70 (m, 1H), 3.14 (m, 2H), 3.82 (m, 1H), 6.91 (m, 2H), 7.41 (m, 2H).

Step 4: Synthesis of rac-5-[(2S,5R)-5-methyl-2-piperidyl]-1,3-dihydrobenzimidazol-2-one Sodium Borohydride (593.99 mg, 15.70 mmol) was added portion wise at 0° C., to a stirred solution of 5-(3-methyl-2,3,4,5-tetrahydropyridin-6-yl)-1,3-dihydrobenzimidazol-2-one (1.8 g, 7.85 mmol) in MeOH (20 mL). The reaction mixture was stirred at 20° C. for 3 hours. After 3 hours, the reaction mixture was concentrated under reduced pressure. The obtained residue was diluted with water (50 mL). The resulting mixture was extracted with EtOAc (2×50 mL). The combined organic layer was dried over Na₂SO₄, filtered and concentrated under reduced pressure. The obtained residue was purified by HPLC to obtain rac-5-[(2S,5R)-5-methyl-2-piperidyl]-1,3-dihydrobenzimidazol-2-one (50.4 mg, 217.91 µmol, 2.78% yield) as a white solid.

LCMS(ESI): [M+H]⁺ m/z: calcd 231.2; found 232.2; Rt=0.754 min.

6HHH. The Synthesis of N-[4-(5-methyl-2-piperidyl)cyclohexyl]acetamide

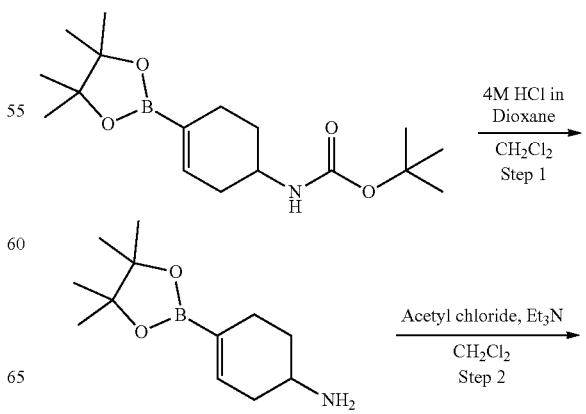

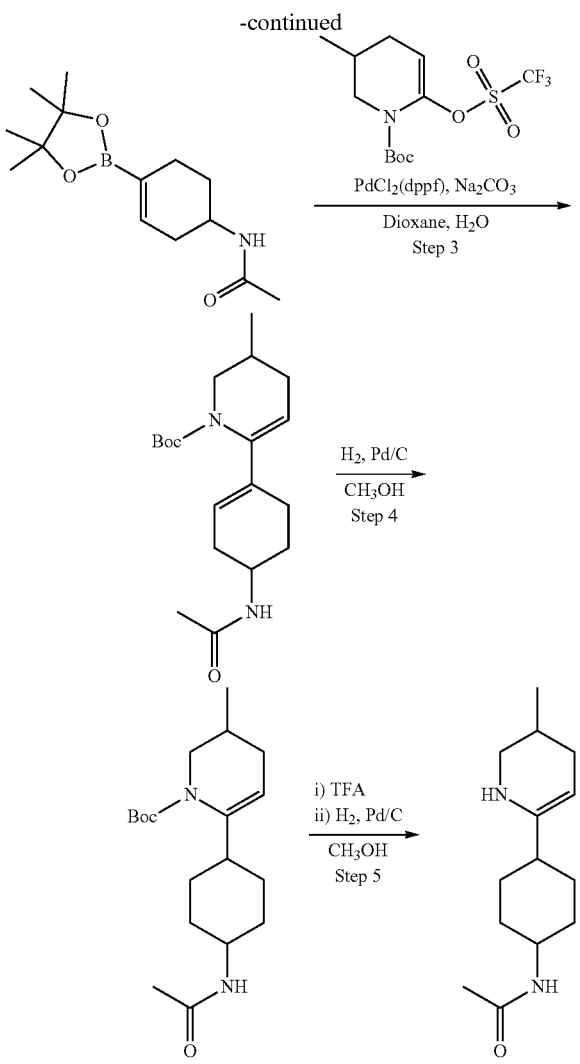

Step 1: Synthesis of 4-(4,4,5,5-tetramethyl-1,3,2-dioxaborolan-2-yl)cyclohex-3-en-1-amine To a stirred solution of tert-butyl N-[4-(4,4,5,5-tetramethyl-1,3,2-dioxaborolan-2-yl)cyclohex-3-en-1-yl]carbamate (7.5 g, 23.20 mmol) in DCM (50 mL), was added 4.0M Hydrogen chloride solution in dioxane (8.00 g, 219.41 mmol, 10 mL). The resulting mixture was stirred at 25° C. for 12 hours. After 12 hours, the reaction mixture was concentrated under reduced pressure to obtain 4-(4,4,5,5-tetramethyl-1,3,2-dioxaborolan-2-yl)cyclohex-3-en-1-amine (5.9 g, 22.73 mmol, 97.96% yield, HCl salt) as a white solid.

LCMS(ESI): [M+H]$^+$ m/z: calcd 223.2; found 224.2; Rt=0.840 min.

Step 2: Synthesis of N-[4-(4,4,5,5-tetramethyl-1,3,2-dioxaborolan-2-yl)cyclohex-3-en-1-yl]acetamide To a stirred suspension of 4-(4,4,5,5-tetramethyl-1,3,2-dioxaborolan-2-yl)cyclohex-3-en-1-amine (5.9 g, 22.73 mmol, HCl salt) and Triethylamine (6.90 g, 68.19 mmol, 9.50 mL) in DCM (100 mL), was added Acetyl chloride (2.14 g, 27.27 mmol, 1.66 mL) drop wise at 0° C. The resulting reaction mixture was stirred at the room temperature for 3 hours. After 3 hours, water (50 mL) was added. Both layers were separated. The organic layer was washed with brine (2×40 mL), dried over Na$_2$SO$_4$ and concentrated under reduced pressure to obtain N-[4-(4,4,5,5-tetramethyl-1,3,2-dioxaborolan-2-yl)cyclohex-3-en-1-yl]acetamide (5.5 g, 20.74 mmol, 91.26% yield) as a white solid.

LCMS(ESI): [M+H]$^+$ m/z: calcd 265.2; found 266.2; Rt=1.109 min.

Step 3: Synthesis of tert-butyl 6-(4-acetamidocyclohexen-1-yl)-3-methyl-3,4-dihydro-2H-pyridine-1-carboxylate A stirred suspension of N-[4-(4,4,5,5-tetramethyl-1,3,2-dioxaborolan-2-yl)cyclohex-3-en-1-yl]acetamide (5.5 g, 20.74 mmol), tert-butyl 3-methyl-6-(trifluoromethylsulfonyloxy)-3,4-dihydro-2H-pyridine-1-carboxylate (7.16 g, 20.74 mmol), and Sodium carbonate (6.60 g, 62.23 mmol, 2.61 mL) in Dioxane (100 mL) and Water (20 mL) was purged with Argon for 10 minutes. After 10 minutes, [1,1'-Bis(diphenylphosphino)ferrocene]dichloropalladium(II), complex with dichloromethane (846.96 mg, 1.04 mmol) was added. The resulting reaction mixture was stirred under argon at 55° C. for 12 hours. After 12 hours, the reaction mixture was allowed to cool to room temperature and filtered. The filter cake was washed with Dioxane (50 mL). The filtrate was concentrated under reduced pressure. Water (150 mL) was added to the obtained residue and extracted with EtOAc (2×100 mL). The combined organic phase was washed with brine (100 mL), dried over Na$_2$SO$_4$ and evaporated in vacuo to obtain crude product (9 g), which was purified by column chromatography to obtain tert-butyl 6-(4-acetamidocyclohexen-1-yl)-3-methyl-3,4-dihydro-2H-pyridine-1-carboxylate (2.4 g, 7.18 mmol, 34.60% yield) as a light-yellow solid.

LCMS(ESI): [M+Boc]$^+$ m/z: calcd 334.2; found 279.4 (t-Bu cleaved product mass); Rt=1.374 min.

Step 4: Synthesis of tert-butyl 2-(4-acetamidocyclohexyl)-5-methyl-piperidine-1-carboxylate A solution of tert-butyl 6-(4-acetamidocyclohexen-1-yl)-3-methyl-3,4-dihydro-2H-pyridine-1-carboxylate (2.4 g, 7.18 mmol) in MeOH (60 mL) was hydrogenated over Palladium, 10% on carbon, Type 487, dry (305.46 mg, 2.87 mmol) under hydrogen atmosphere at 25° C. for 120 hours. After 120 hours, the reaction mixture was filtered and the filtrate was concentrated under reduced pressure to obtain tert-butyl 2-(4-acetamidocyclohexyl)-5-methyl-piperidine-1-carboxylate (2.3 g, 6.80 mmol, 94.69% yield) as a white solid. The product was used for the next step reaction without any further purification.

LCMS(ESI): [M+Boc]$^+$ m/z: calcd 336.2; found 337.2; Rt=1.346 min.

Step 5: Synthesis of N-[4-(5-methyl-2-piperidyl)Cyclohexyl]acetamide tert-butyl 2-(4-acetamidocyclohexyl)-5-methyl-piperidine-1-carboxylate (2.3 g, 6.80 mmol) was dissolved in Trifluoroacetic acid (14.80 g, 129.80 mmol, 10 mL) and stirred at 25° C. for 2 hours. After 2 hours, NaOH solution was added to the reaction mixture to adjust the pH=9, then extracted with DCM (3×30 mL). The combined organic phase was washed with brine (40 mL), dried over Na$_2$SO$_4$ and evaporated in vacuo. The obtained crude product was dissolved in MeOH (50 mL), and the resulting solution was hydrogenated over Palladium, 10% on carbon, Type 487, dry (144.63 mg, 1.36 mmol) under hydrogen atmosphere at 25° C. for additional 24 hours. The reaction mixture was then filtered and the filtrate was evaporated in vacuo to give N-[4-(5-methyl-2-piperidyl)cyclohexyl]acetamide (0.9 g, 3.78 mmol, 55.57% yield) as a white solid.

GCMS: m/z: calcd 238.2; found 238.2; Rt=10.371 min.

6III. The Synthesis of rac-2,6-difluoro-4-[(2R,5S)-5-methyl-2-piperidyl]phenol

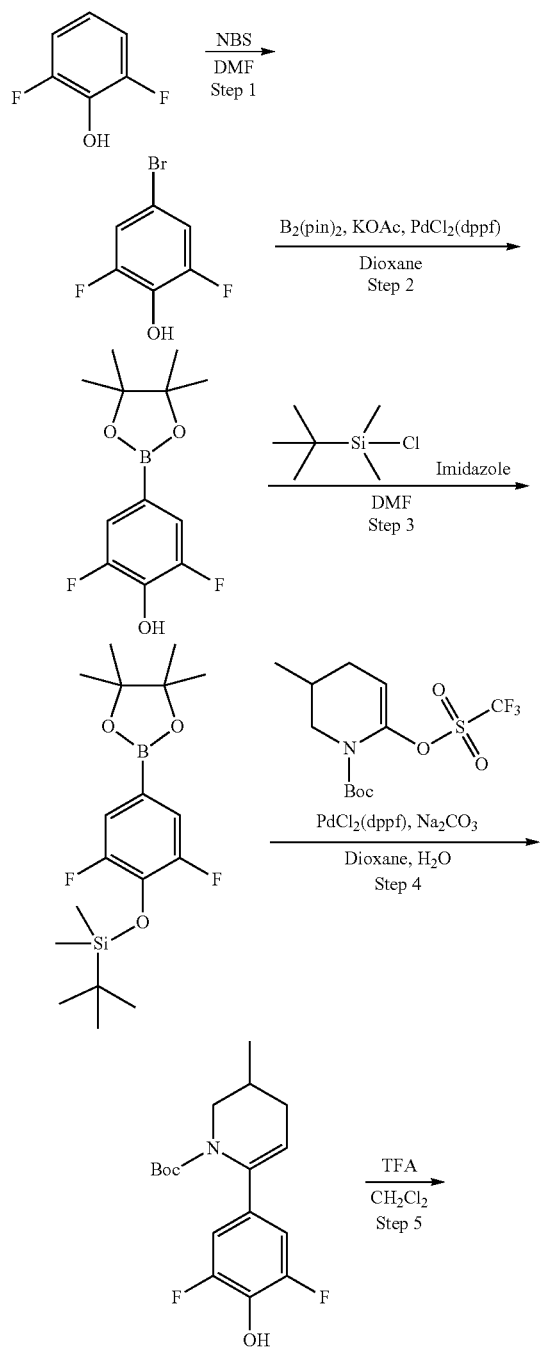

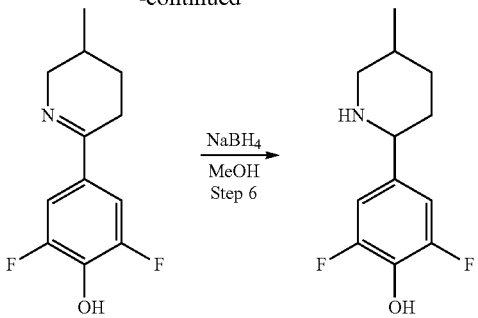

Step 1: Synthesis of 4-bromo-2,6-difluoro-phenol

To a stirred solution of 2,6-difluorophenol (10 g, 76.87 mmol) in DMF (60 mL) was added NBS (13.68 g, 76.87 mmol, 6.51 mL) at 0° C. The resulting reaction mixture was stirred at room temperature for 16 hours. The resulting reaction mixture was concentrated in vacuo, water was added to the obtained residue and extracted with ethyl acetate. The organic phase was dried over $Na_2SO_4$ and concentrated under reduced pressure to afford 4-bromo-2,6-difluoro-phenol (13 g, 62.20 mmol, 80.92% yield) as a yellow solid.

$^1$H NMR (DMSO-$d_6$, 400 MHz): δ (ppm) 7.32 (s, 2H), 10.41 (s, 1H).

Step 2: Synthesis of 2,6-difluoro-4-(4,4,5,5-tetramethyl-1,3,2-dioxaborolan-2-yl)phenol A stirring solution of 4-bromo-2,6-difluoro-phenol (9 g, 43.06 mmol), 4,4,5,5-tetramethyl-2-(4,4,5,5-tetramethyl-1,3,2-dioxaborolan-2-yl)-1,3,2-dioxaborolane (12.03 g, 47.37 mmol) and KOAc (16.91 g, 172.26 mmol) in 1,4-dioxane (200 mL) was purged with argon for 10 minutes. After 10 minutes, Pd(dppf)$C_{12}CH_2Cl_2$ (1.78 g, 2.15 mmol) was added under argon. The reaction mixture was stirred under argon at 80° C. for 24 hours. The reaction mixture was then cooled to room temperature, filtered through celite and the filtrate was concentrated under reduced pressure. The obtained crude product was purified by flash chromatography to give 2,6-difluoro-4-(4,4,5,5-tetramethyl-1,3,2-dioxaborolan-2-yl)phenol (4 g, 15.62 mmol, 36.28% yield) as a white solid.

$^1$H NMR (DMSO-$d_6$, 500 MHz): δ (ppm) 1.25 (s, 12H), 7.20 (s, 2H), 10.30 (s, 1H).

Step 3: Synthesis of tert-butyl-[2,6-difluoro-4-(4,4,5,5-tetramethyl-1,3,2-dioxaborolan-2-yl)phenoxy]-dimethyl-Silane To a stirred solution of 2,6-difluoro-4-(4,4,5,5-tetramethyl-1,3,2-dioxaborolan-2-yl)phenol (2.88 g, 11.25 mmol) and Imidazole (1.44 g, 21.15 mmol) in DMF (42 mL) was added tert-butyl-chloro-dimethyl-silane (2 g, 13.27 mmol, 2.47 mL) portion wise at 0° C. The reaction mixture was allowed to warm to room temperature and stirred at the same temperature for 18 hours. After 18 hours, the reaction mixture was concentrated in vacuo and the obtained residue was partitioned between water (100 mL) and DCM (100 mL). The organic layer was dried over $Na_2SO_4$ and concentrated under reduced pressure to afford tert-butyl-[2,6-difluoro-4-(4,4,5,5-tetramethyl-1,3,2-dioxaborolan-2-yl)phenoxy]-dimethyl-silane (2.4 g, crude). The crude product was used in the next step reaction without any further purification.

$^1$H NMR (DMSO-d$_6$, 500 MHz): δ (ppm) 0.16 (s, 6H), 0.96 (s, 9H), 1.27 (s, 12H), 7.24 (s, 2H).

Step 4: Synthesis of tert-butyl 6-(3,5-difluoro-4-hydroxy-phenyl)-3-methyl-3,4-dihydro-2H-pyridine-1-carboxylate A stirring solution of tert-butyl 3-methyl-6-(trifluoromethylsulfonyloxy)-3,4-dihydro-2H-pyridine-1-carboxylate (2.01 g, 5.83 mmol), tert-butyl-[2,6-difluoro-4-(4,4,5,5-tetramethyl-1,3,2-dioxaborolan-2-yl)phenoxy]-dimethyl-silane (2.4 g, 6.48 mmol) and Sodium carbonate (2.06 g, 19.44 mmol) in 1,4-dioxane (20 mL) and water (10 mL) was purged with argon. Then, Pd(dppf)Cl$_2$CH$_2$Cl$_2$ (267.90 mg, 324.05 μmol) was added under argon. The reaction mixture was stirred under argon at 75° C. for 14 hours. After 14 hours, the reaction mixture was diluted with water and extracted with DCM. The organic layer was dried over Na$_2$SO$_4$ and concentrated under reduced pressure. The obtained crude material was purified by column chromatography (SiO$_2$, Eluent: 0-100% CHCl$_3$ in methanol) to afford tert-butyl 6-(3,5-difluoro-4-hydroxy-phenyl)-3-methyl-3,4-dihydro-2H-pyridine-1-carboxylate (1.15 g, 3.53 mmol, 54.54% yield).

Step 5: Synthesis of 2,6-difluoro-4-(3-methyl-2,3,4,5-tetrahydropyridin-6-yl)phenol TFA (2.98 g, 26.14 mmol, 2 mL) was added to a stirred solution of tert-butyl 6-(3,5-difluoro-4-hydroxy-phenyl)-3-methyl-3,4-dihydro-2H-pyridine-1-carboxylate (0.65 g, 2.00 mmol) in DCM (2 mL). The resulting reaction mixture was stirred for 30 minutes and then concentrated in vacuo to afford 2,6-difluoro-4-(3-methyl-2,3,4,5-tetrahydropyridin-6-yl)phenol (0.2 g, crude) as a brown oil. The crude product was used directly in the next step reaction without any further purification.

LCMS(ESI): [M+H]$^+$ m/z: calcd 225.1; found 226.2; Rt=0.741 min.

Step 6: Synthesis of rac-2,6-difluoro-4-[(2R,5S)-5-methyl-2-piperidyl]phenol Sodium Borohydride (24.02 mg, 634.90 μmol) was added in one portion to a stirred solution of 2,6-difluoro-4-(3-methyl-2,3,4,5-tetrahydropyridin-6-yl)phenol (0.2 g, 488.38 μmol) in methanol (4 mL). The reaction mixture was stirred at the room temperature for 14 hours. After 14 hours, the reaction mixture was concentrated under reduced pressure, the residue was purified by reverse phase HPLC (Eluent: 2-10 min, 80-95% water-MeOH+NH$_3$; flow rate: 30 mL/min; loading pump: 4 mL/min, MeOH+NH$_3$; column: TRIART C18, 100×20 mm, 5 μM) to obtain rac-2,6-difluoro-4-[(2R,5S)-5-methyl-2-piperidyl]phenol (0.05 g, 220.02 μmol, 45.05% yield).

LCMS(ESI): [M+H]$^+$ m/z: calcd 227.1; found 228.2; Rt=0.849 min.

6JJJ. The Synthesis of rac-2-[4-[(2R,5S)-5-methyl-2-piperidyl]phenyl]thiazole

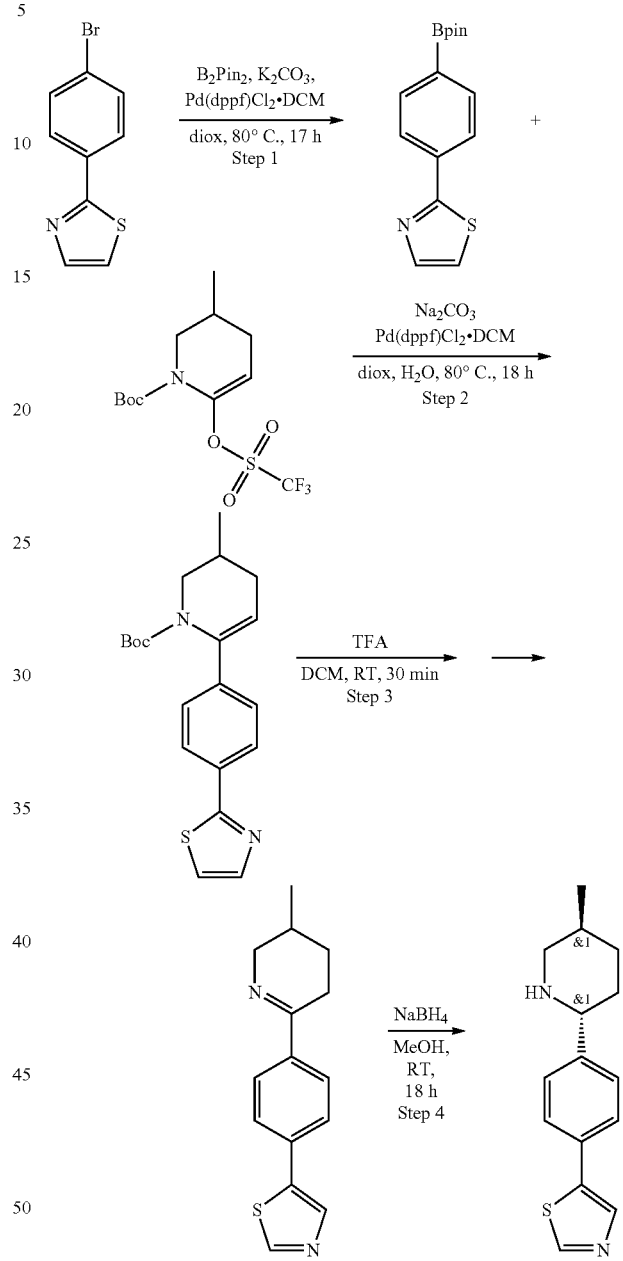

Step 1: The Synthesis of 2-[4-(4,4,5,5-tetramethyl-1,3,2-dioxaborolan-2-yl)phenyl]thiazole 2-(4-bromophenyl)thiazole (10 g, 41.65 mmol), 4,4,5,5-tetramethyl-2-(4,4,5,5-tetramethyl-1,3,2-dioxaborolan-2-yl)-1,3,2-dioxaborolane (11.32 g, 44.56 mmol), Potassium Acetate (16.35 g, 166.58 mmol, 10.41 mL) and Pd(dppf)C$_{12}$ DCM (1.70 g, 2.08 mmol) were mixed in 1,4-dioxane (300 mL) and the mixture was stirred at 80° C. for 17 hr. After cooling down, the reaction mixture was diluted with water and extracted with DCM several times. Combined extracts were concentrated under reduced pressure and the residue was submitted to flash column chromatography to afford 2-[4-(4,4,5,5-tetramethyl-1,3,2-dioxaborolan-2-yl)phenyl]thiazole (10 g, 34.82 mmol, 83.61% yield).

Chromatography data: 120 g SiO$_2$, CHCl$_3$-MeCN from 0~100%, flow rate=100 mL/min, cv=7

LCMS(ESI): [M+H]$^+$ m/z: calcd 287.2; found 288.2; Rt=1.585 min.

Step 2: The Synthesis of tert-butyl 3-methyl-6-(4-thiazol-2-ylphenyl)-3,4-dihydro-2H-pyridine-1-carboxylate 2-[4-(4,4,5,5-tetramethyl-1,3,2-dioxaborolan-2-yl)phenyl]thiazole (9 g, 31.34 mmol), tert-butyl 3-methyl-6-(trifluoromethylsulfonyloxy)-3,4-dihydro-2H-pyridine-1-carboxylate (8.66 g, 25.07 mmol), Pd(dppf)C$_{12}$ DCM (1.02 g, 1.25 mmol) and sodium carbonate (9.96 g, 94.02 mmol, 3.94 mL) were added to a mixture of 1,4-dioxane (105 mL) and water (35 mL) and the resulting mixture was stirred at 80° C. for 15 hr. After cooling down, the reaction mixture was diluted with water and extracted with DCM. The organic layer was separated, dried over Na$_2$SO$_4$ and concentrated under reduced pressure. The residue was submitted to flash column chromatography to afford tert-butyl 3-methyl-6-(4-thiazol-2-ylphenyl)-3,4-dihydro-2H-pyridine-1-carboxylate (5.5 g, 15.43 mmol, 49.23% yield).

Chromatography data: Companion combiflash; 120 g SiO$_2$, HEX-MTBE from 0~100%, flow rate=85 mL/min, cv=7

LCMS(ESI): [M+H]$^+$ m/z: calcd 356.2; found 357.2; Rt=1.673 min.

Step 3: The Synthesis of 2-[4-(3-methyl-2,3,4,5-tetrahydropyridin-6-yl)phenyl]thiazole To a stirred solution of tert-butyl 3-methyl-6-(4-thiazol-2-ylphenyl)-3,4-dihydro-2H-pyridine-1-carboxylate (5.5 g, 15.43 mmol) in DCM (15 mL) was added TFA (10 g, 87.70 mmol, 6.76 mL) at RT. The resulting reaction mixture was stirred at RT for 0.5 hr. The reaction mixture was concentrated under reduced pressure, treated with aqueous NaOH solution and extracted with DCM. The organic layer was dried over Na$_2$SO$_4$ and concentrated under reduced pressure to afford 2-[4-(3-methyl-2,3,4,5-tetrahydropyridin-6-yl)phenyl]thiazole (3.9 g, crude), which was used directly in the next step without purification.

LCMS(ESI): [M+H]$^+$ m/z: calcd 256.2; found 257.0; Rt=0.961 min.

Step 4: The Synthesis of rac-2-[4-[(2R,5S)-5-methyl-2-piperidyl]phenyl]thiazole

2-[4-(3-methyl-2,3,4,5-tetrahydropyridin-6-yl)phenyl]thiazole (3.9 g, 15.21 mmol) was dissolved in methanol (50 mL) and Sodium Borohydride (805.75 mg, 21.30 mmol, 753.04 µL) was added in one portion. The reaction mixture was stirred at 25° C. for 16 hr and then was concentrated under reduced pressure. The residue was dissolved in DCM, washed with aqueous NaOH solution, brine and concentrated on a rotary evaporator to afford 2-[4-[(2R,5S)-5-methyl-2-piperidyl]phenyl]thiazole (2 g, crude) which was used in the next steps without further purification.

LCMS(ESI): [M+H]$^+$ m/z: calcd 258.2; found 259.2; Rt=0.874 min.

6KKK. Synthesis of rac-5-(5-methyl-2-piperidyl)-2-(trifluoromethyl)-1,3-benzothiazole

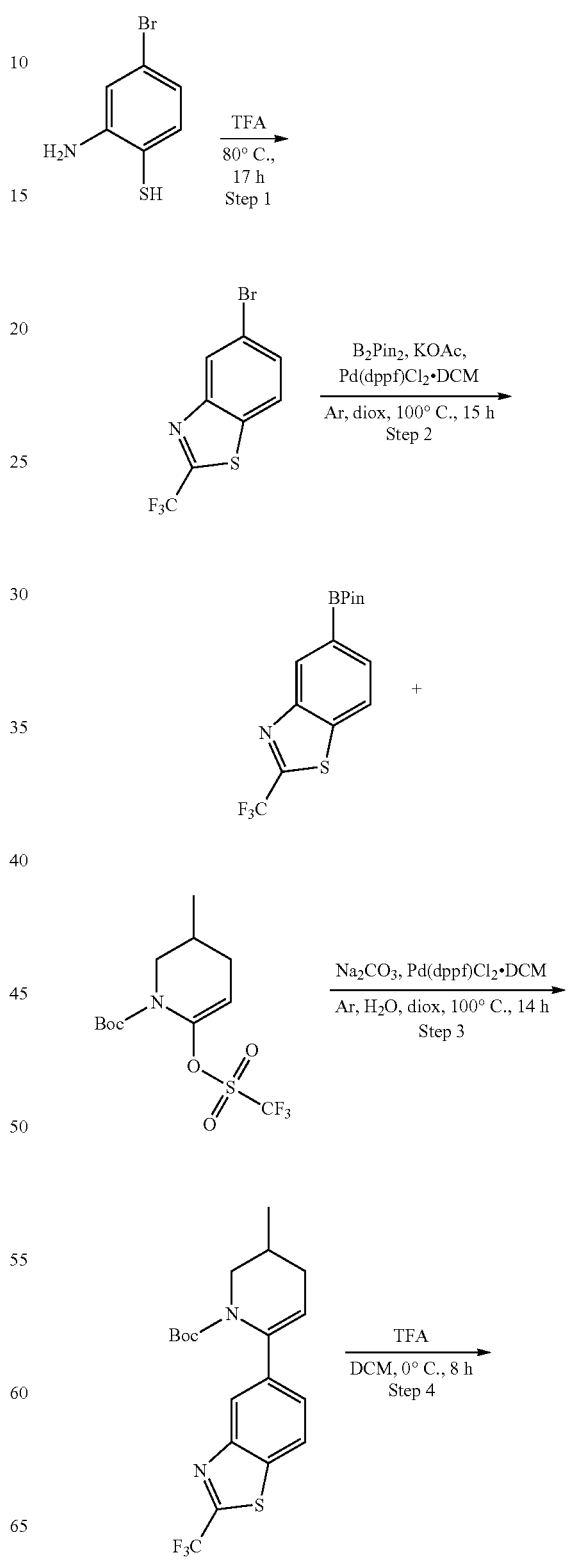

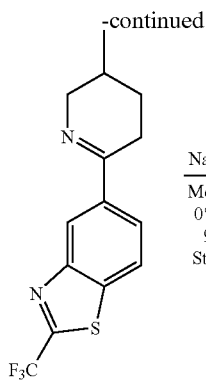

Step 1: The Synthesis of 5-bromo-2-(trifluoromethyl)-1,3-benzothiazole 2-amino-4-bromo-benzenethiol (9.5 g, 46.55 mmol) was added in one portion to a stirred solution of Trifluoroacetic acid (70 g, 613.93 mmol, 47.30 mL) at 80° C. The resulting mixture was stirred at 80° C. for 17 hr, and then evaporated in vacuo. The residue was diluted with water (200 mL) and extracted with EtOAc (2*90 mL). The combined organic extracts were dried over sodium sulphate and evaporated in vacuo to afford 5-bromo-2-(trifluoromethyl)-1,3-benzothiazole (9 g, 31.91 mmol, 68.54% yield).

$^1$H NMR (400 MHz, CDCl$_3$) δ 7.66 (d, 1H), 7.84 (d, 1H), 8.35 (s, 1H).

Step 2: The Synthesis of 5-(4,4,5,5-tetramethyl-1,3,2-dioxaborolan-2-yl)-2-(trifluoromethyl)-1,3-benzothiazole Potassium Acetate (6.26 g, 63.81 mmol, 3.99 mL) was added to a solution of 5-bromo-2-(trifluoromethyl)-1,3-benzothiazole (9 g, 31.91 mmol) and 4,4,5,5-tetramethyl-2-(4,4,5,5-tetramethyl-1,3,2-dioxaborolan-2-yl)-1,3,2-dioxaborolane (9.72 g, 38.29 mmol) in dioxane (250 mL). Reaction flask was evacuated and refilled with argon 3 times. Then Pd(dppf)Cl$_2$*DCM (1.30 g, 1.60 mmol) was added under stream of argon. Resulting mixture was stirred at 100° C. for 15 hr under inert atmosphere. Then, it was cooled, diluted with MTBE (600 mL) and filtered. Filtrate was concentrated under reduced pressure to leave 14.5 g of crude product, 14.5 g of which was purification by column chromatography on silica gel using hexane/MTBE gradient (10-100% MTBE) to afford product 5-(4,4,5,5-tetramethyl-1,3,2-dioxaborolan-2-yl)-2-(trifluoromethyl)-1,3-benzothiazole (7.5 g, 22.79 mmol, 71.42% yield).

$^1$H NMR (500 MHz, DMSO-d$_6$) δ 1.38 (s, 12H), 7.96 (m, 2H), 8.67 (s, 1H).

LCMS(ESI): [M+H]$^+$ m/z: calcd 329.0; found 330.0; Rt=1.609 min.

Step 3: The Synthesis of tert-butyl 3-methyl-6-[2-(trifluoromethyl)-1,3-benzothiazol-5-yl]-3,4-dihydro-2H-pyridine-1-carboxylate 5-(4,4,5,5-tetramethyl-1,3,2-dioxaborolan-2-yl)-2-(trifluoromethyl)-1,3-benzothiazole (4.52 g, 13.73 mmol) and tert-butyl 3-methyl-6-(trifluoromethylsulfonyloxy)-3,4-dihydro-2H-pyridine-1-carboxylate (5.69 g, 16.48 mmol) were mixed together in water (2 mL). The resulting mixture was evacuated and then backfilled with argon, this operation was repeated three times, then Sodium carbonate (2.91 g, 27.47 mmol, 1.15 mL) in water (2 mL) and [1,1'-Bis(diphenylphosphino)ferrocene]dichloropalladium(II), complex with dichloromethane (502.41 mg, 686.63 µmol) were added under argon. The reaction mixture was stirred under argon at 100° C. for 14 hr, then cooled and evaporated in vacuo poured into water (120 ml) and extracted with EtOAc (2×90 ml). The combined organic extracts were washed with water (2*40 ml), dried over sodium sulphate and evaporated in vacuo to leave 8 g of crude product, 8 g of which was purification by column chromatography on silica gel using hexane/MTBE gradient (10-100% MTBE) to afford product tert-butyl 3-methyl-6-[2-(trifluoromethyl)-1,3-benzothiazol-5-yl]-3,4-dihydro-2H-pyridine-1-carboxylate (4 g, 10.04 mmol, 73.10% yield).

$^1$H NMR (400 MHz, CDCl$_3$) δ 1.02 (s, 9H), 1.54 (d, 3H), 2.01 (m, 2H), 2.42 (m, 1H), 3.02 (m, 1H), 4.07 (m, 1H), 5.42 (m, 1H), 7.50 (d, 1H), 7.86 (d, 1H), 8.11 (s, 1H).

LCMS(ESI): [M-$^t$Bu]$^+$ m/z: calcd 342.2; found 343.0; Rt=1.685 min.

Step 4: The Synthesis of 5-(3-methyl-2,3,4,5-tetrahydropyridin-6-yl)-2-(trifluoromethyl)-1,3-benzothiazole The solution of tert-butyl 3-methyl-6-[2-(trifluoromethyl)-1,3-benzothiazol-5-yl]-3,4-dihydro-2H-pyridine-1-carboxylate (4 g, 10.04 mmol) in DCM (20 mL) and Trifluoroacetic acid (22.89 g, 200.78 mmol, 15.47 mL) was stirred at 0° C. for 8 hr, and then evaporated in vacuo. Crushed ice (50 g) was added to the residue and pH was adjusted to 8 with a 10% aqueous solution of sodium hydrocarbonate. The resulting mixture was extracted with ethylacetate (2*50 mL). The combined organic extracts were dried over sodium sulphate and evaporated in vacuo to afford 5-(3-methyl-2,3,4,5-tetrahydropyridin-6-yl)-2-(trifluoromethyl)-1,3-benzothiazole (2.3 g, 7.71 mmol, 76.80% yield).

$^1$H NMR (400 MHz, CDCl$_3$) δ 1.02 (d, 3H), 1.24 (m, 1H), 1.48 (m, 1H), 1.96 (m, 1H), 2.90 (m, 2H), 3.33 (m, 1H), 4.04 (m, 1H), 7.96 (d, 1H), 8.19 (d, 1H), 8.47 (s, 1H).

LCMS(ESI): [M+H]$^+$ m/z: calcd 298.2; found 299.2; Rt=0.965 min.

Step 5: The Synthesis of rac-5-(5-methyl-2-piperidyl)-2-(trifluoromethyl)-1,3-benzothiazole Sodium Borohydride (583.35 mg, 15.42 mmol, 545.19 µL) was added in one portion to a stirred solution of 5-(3-methyl-2,3,4,5-tetrahydropyridin-6-yl)-2-(trifluoromethyl)-1,3-benzothiazole (2.3 g, 7.71 mmol) in MeOH (30 mL) at 0° C. The resulting mixture was stirred at 0° C. for 9 hr, and then evaporated in vacuo. The residue was diluted with water (40 mL) and extracted with dichloromethane (2*50 mL). The combined organic extracts were dried over sodium sulphate and evaporated in vacuo to afford rac-5-(5-methyl-2-piperidyl)-2-(trifluoromethyl)-1,3-benzothiazole (1.8 g, 5.99 mmol, 77.74% yield).

$^1$H NMR (400 MHz, CDCl$_3$) δ 1.01 (d, 3H), 1.14 (m, 2H), 1.68 (m, 3H), 2.45 (m, 1H), 3.19 (m, 1H), 3.73 (m, 1H), 5.28 (s, 1H), 7.62 (d, 1H), 7.90 (d, 1H), 8.16 (s, 1H).

LCMS(ESI): [M+H]+ m/z: calcd 300.2; found 301.2; Rt=0.977 min.

6LLL. The Synthesis of rac-6-[(2S,5R)-5-methyl-2-piperidyl]-3,4-dihydro-1H-1,8-naphthyridin-2-one

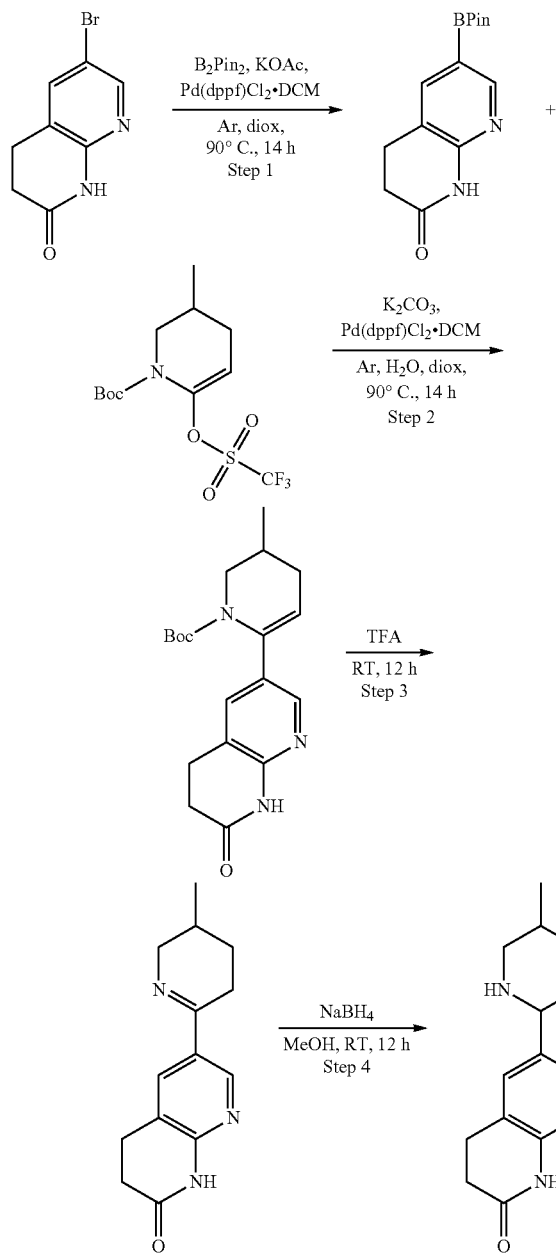

Step 1: The Synthesis of 6-(4,4,5,5-tetramethyl-1,3,2-dioxaborolan-2-yl)-3,4-dihydro-1H-1,8-naphthyridin-2-one Potassium Acetate (12.53 g, 127.72 mmol, 7.98 mL) was added a solution of 6-bromo-3,4-dihydro-1H-1,8-naphthyridin-2-one (14.5 g, 63.86 mmol) in Dioxane (250 mL), followed by addition of Bis(pinacolato)diboron (17.84 g, 70.25 mmol) and Pd(dppf)C$_{12}$DCM (2.61 g, 3.19 mmol). The resulting solution was stirred overnight at 90° C. under Ar. The resulting mixture was concentrated under vacuum, diluted with EtOAc, filtered and evaporated. Resulting precipitate was crystallized in MTBE to obtain 6-(4,4,5,5-tetramethyl-1,3,2-dioxaborolan-2-yl)-3,4-dihydro-1H-1,8-naphthyridin-2-one (14.7 g, 53.63 mmol, 83.97% yield).

$^1$H NMR (600 MHz, CDCl$_3$) δ 1.33 (s, 12H), 2.67 (t, 2H), 2.94 (t 2H), 7.84 (s, 1H), 8.56 (s, 1H), 9.16 (s, 1H).

Step 2: The Synthesis of tert-butyl 3-methyl-6-(7-oxo-6,8-dihydro-5H-1,8-naphthyridin-3-yl)-3,4-dihydro-2H-pyridine-1-carboxylate To a solution of tert-butyl 3-methyl-6-(trifluoromethylsulfonyloxy)-3,4-dihydro-2H-pyridine-1-carboxylate (9.70 g, 28.09 mmol) in Dioxane (200 mL) was added a solution of Sodium carbonate (8.12 g, 76.61 mmol, 3.21 mL) in water (50 mL), followed by addition of 6-(4,4,5,5-tetramethyl-1,3,2-dioxaborolan-2-yl)-3,4-dihydro-1H-1,8-naphthyridin-2-one (7 g, 25.54 mmol) and Pd(dppf)Cl$_2$*DCM (1.04 g, 1.28 mmol). Resulting mixture was stirred overnight at 90° C. under Ar. Resulting mixture was concentrated under vacuum, diluted with EtOAc and washed with water (2×40 mL). Organic phase was dried over sodium sulfate, filtered and evaporated to obtain tert-butyl 3-methyl-6-(7-oxo-6,8-dihydro-5H-1,8-naphthyridin-3-yl)-3,4-dihydro-2H-pyridine-1-carboxylate (9.5 g, crude).

LCMS(ESI): [M+H]+ m/z: calcd 343.2; found 344.2; Rt=1.231 min.

Step 3: The Synthesis of 6-(3-methyl-2,3,4,5-tetrahydropyridin-6-yl)-3,4-dihydro-1H-1,8-naphthyridin-2-one A solution of tert-butyl 3-methyl-6-(7-oxo-6,8-dihydro-5H-1,8-naphthyridin-3-yl)-3,4-dihydro-2H-pyridine-1-carboxylate (9.5 g, 27.66 mmol) in TFA (50 mL) was stirred at 25° C. for 12 hr. Potassium carbonate saturated aq. solution was added to the solution (200 ml) and then extracted with DCM (2×300 mL). Organic phase was dried over sodium sulfate, filtered and evaporated to obtain 6-(3-methyl-2,3,4,5-tetrahydropyridin-6-yl)-3,4-dihydro-1H-1,8-naphthyridin-2-one (7.1 g, crude).

$^1$H NMR (400 MHz, CDCl$_3$) δ 0.94 (d, 3H), 1.01 (m, 2H), 1.32 (m, 2H), 2.02 (m, 2H), 2.62 (m, 2H), 2.94 (m, 2H), 4.05 (m, 1H), 8.01 (s, 1H), 8.21 (s, 1H), 9.12 (s, 1H).

Step 4: The Synthesis of rac-6-[(2S,5R)-5-methyl-2-piperidyl]-3,4-dihydro-1H-1,8-naphthyridin-2-one Sodium Borohydride (2.21 g, 58.36 mmol, 2.06 mL) was added portionwise to a solution of 6-(3-methyl-2,3,4,5-tetrahydropyridin-6-yl)-3,4-dihydro-1H-1,8-naphthyridin-2-one (7.1 g, 29.18 mmol) in Methanol (100 mL). The mixture was stirred at rt for 12 hr. Water (50 mL) was added and resulting mixture was extracted with EtOAc (2×50 mL). Organic phase was dried over sodium sulfate, filtered and evaporated. Resulting crude product was purified by column chromatography to obtain 6-[(2S,5R)-5-methyl-2-piperidyl]-3,4-dihydro-1H-1,8-naphthyridin-2-one (1.2 g, 4.89 mmol, 16.76% yield).

LCMS(ESI): [M+H]+ m/z: calcd 245.2; found 246.2; Rt=0.791 min.

6MMM. Synthesis of rac-5-((2R,5S)-5-methylpiperidin-2-yl)benzo[d]thiazol-2-amine

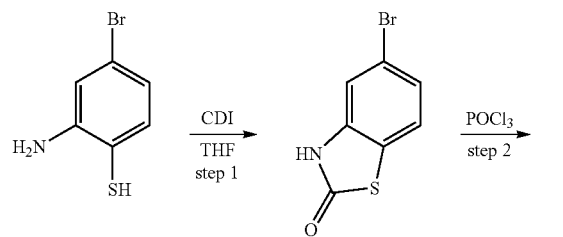

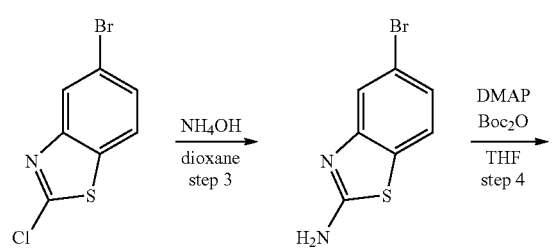

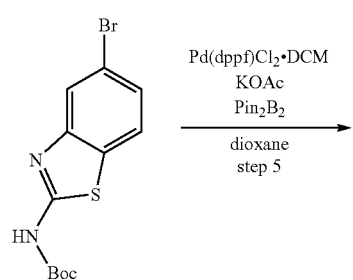

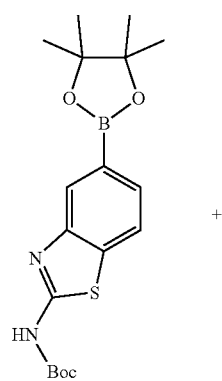

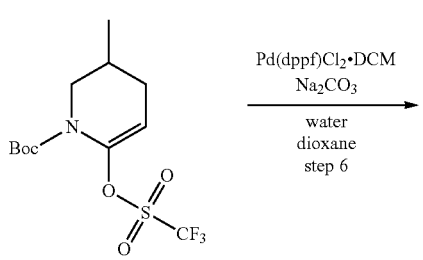

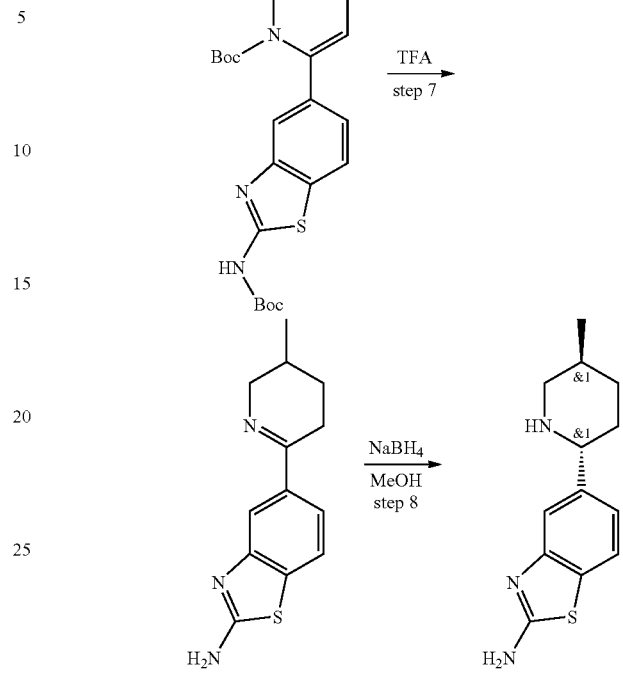

Step 1: Synthesis of 5-bromobenzo[d]thiazol-2(3H)-one 2-amino-4-bromo-benzenethiol (30 g, 147.00 mmol) was dissolved in dry THF (500 mL) under argon. To the above solution di(imidazol-1-yl)methanone (26.5 g, 163.43 mmol) was added in one portion under argon and the reaction mixture was stirred under argon at 25° C. for 1 hr (slightly exothermic reaction observed). Then the reaction mixture was stirred at 50° C. for 1 hr (after the exothermic reaction passed), and then cooled down and concentrated in vacuum. The residue was diluted with water (300 ml), the precipitate was filtered, washed with water (3*50 ml) and dried in vacuum to afford 5-bromo-3H-1,3-benzothiazol-2-one (33.5 g, 145.60 mmol, 99.05% yield) as white solid.

$^1$H NMR (500 MHz, DMSO-d$_6$) δ (ppm) 7.23 (s, 1H), 7.31 (d, 1H), 7.55 (s, 1H), 12.05 (bds, 1H).

LCMS(ESI): [M]$^+$ m/z: calcd 230.2; found 231.2; Rt=1.083 min.

Step 2: Synthesis of 5-bromo-2-chlorobenzo[d]thiazole

A suspension of 5-bromo-3H-1,3-benzothiazol-2-one (33.5 g, 145.60 mmol) in phosphoryl chloride (431.84 g, 2.82 mol, 261.72 mL) was stirred with reflux condenser at 110° C. for 32 hr (after 8 hr clear solution formed). The reaction mixture was cooled down and concentrated in vacuum. Crushed ice (300 g) was added to the residue, and the precipitate was filtered, washed with water (4*50 ml) and air dried to afford 5-bromo-2-chloro-1,3-benzothiazole (34 g, 136.81 mmol, 93.96% yield) as beige solid.

$^1$H NMR (500 MHz, DMSO-d$_6$) δ (ppm) 7.68 (d, 1H), 8.08 (d, 1H), 8.20 (s, 1H).

LCMS(ESI): [M]+ m/z: calcd 248.2; found 249.2; Rt=1.159 min.

Step 3: Synthesis of 5-bromobenzo[d]thiazol-2-amine

A mixture of 5-bromo-2-chloro-1,3-benzothiazole (30 g, 120.71 mmol) and ammonium hydroxide, 25% NH$_3$ (136.50 g, 150 mL) in 1,4-dioxane (150 mL) was stirred at 135° C. (internal temperature of reaction mixture) for 40 hr in autoclave. After cooling, autoclave was opened and resulting suspension was concentrated to dryness in vacuum. The residue was diluted with water (250 ml), the precipitate was filtered, washed successively with water (3*50 ml), 50% aqueous ethanol (20 ml) and hexane (3*50 ml), and then dried in vacuum to afford 5-bromo-1,3-benzothiazol-2-amine (25 g, 109.12 mmol, 90.40% yield) as light-yellow solid.

$^1$H NMR (500 MHz, DMSO-d$_6$) δ (ppm) 7.12 (d, 1H), 7.48 (s, 1H), 7.60 (d, 1H), 7.69 (s, 2H).

LCMS(ESI): [M]+ m/z: calcd 229.2; found 230.2; Rt=1.023 min.

Step 4: Synthesis of tert-butyl (5-bromobenzo[d]thiazol-2-yl)carbamate

Di-tert-butyl dicarbonate (5.24 g, 24.01 mmol, 5.51 mL) was added in one portion to a stirred solution of 5-bromo-1,3-benzothiazol-2-amine (5 g, 21.82 mmol) and N,N-dimethylpyridin-4-amine (266.63 mg, 2.18 mmol) in THF (75 mL) at 25° C. The reaction mixture was stirred at 25° C. for 3 hr. The resulting suspension was concentrated in vacuum to approximately 20 ml, and then diluted with hexane (50 ml). The precipitate was filtered, washed with hexane (2*20 ml) and air dried to afford crude tert-butyl N-(5-bromo-1,3-benzothiazol-2-yl)carbamate (6.2 g, 18.83 mmol, 86.29% yield) as white solid, which was used directly in the next step.

$^1$H NMR (400 MHz, DMSO-d$_6$) δ (ppm) 1.51 (s, 9H), 7.42 (d, 1H), 7.85 (s, 1H), 7.91 (d, 1H), 12.02 (bds, 1H).

LCMS(ESI): [M-Boc]+ m/z: calcd 229.2; found 230.2; Rt=1.588 min.

Step 5: Synthesis of tert-butyl (5-(4,4,5,5-tetramethyl-1,3,2-dioxaborolan-2-yl)benzo[d]thiazol-2-yl)carbamate A mixture of tert-butyl N-(5-bromo-1,3-benzothiazol-2-yl)carbamate (6.2 g, 18.83 mmol), 4,4,5,5-tetramethyl-2-(4,4,5,5-tetramethyl-1,3,2-dioxaborolan-2-yl)-1,3,2-dioxaborolane (5.26 g, 20.72 mmol) and potassium acetate (3.70 g, 37.67 mmol, 2.35 mL) in 1,4-dioxane (120 mL) was evacuated and then backfilled with argon. This operation was repeated two times, then Pd(dppf)Cl$_2$*DCM (1.54 g, 1.88 mmol) was added and the reaction mixture was stirred under argon at 90° C. for 48 hr, then cooled down, diluted with MTBE (120 ml) and filtered through a short pad of silica gel. The filter cake was washed with MTBE (2*50 ml) and discarded. The filtrate was concentrated in vacuum to afford crude tert-butyl N-[5-(4,4,5,5-tetramethyl-1,3,2-dioxaborolan-2-yl)-1,3-benzothiazol-2-yl]carbamate (12 g, crude) as brown gum, which was used directly in the next step.

$^1$H NMR (400 MHz, DMSO-d$_6$) δ (ppm) 1.12 (s, 12H), 1.46 (s, 9H), 7.48 (d, 1H), 7.93 (m, 3H).

LCMS(ESI): [M]+ m/z: calcd 376.2; found 377.2; Rt=1.601 min.

Step 6: Synthesis of tert-butyl 6-(2-((Tert-butoxycarbonyl)amino)benzo[d]thiazol-5-yl)-3-methyl-3,4-dihydropyridine-1(2H)-carboxylate tert-butyl N-[5-(4,4,5,5-tetramethyl-1,3,2-dioxaborolan-2-yl)-1,3-benzothiazol-2-yl]carbamate (12 g, 19.13 mmol), tert-butyl 3-methyl-6-(trifluoromethylsulfonyloxy)-3,4-dihydro-2H-pyridine-1-carboxylate (6.5 g, 18.82 mmol) and sodium carbonate (6.08 g, 57.40 mmol, 2.40 mL) were added to a mixture of 1,4-dioxane (100 mL) and water (25 mL). The resulting mixture was evacuated and then back-filled with argon, this operation was repeated three times, then Pd(dppf)Cl$_2$*DCM (781.31 mg, 956.74 μmol) was added under argon. The reaction mixture was stirred under argon at 90° C. for 15 hr. The reaction mixture was cooled down and filtered through a short pad of silica gel. The filter cake was additionally washed with 1,4-dioxane (2*25 ml) and discarded. The filtrate was concentrated in vacuum, and the residue (16 g) was purified by column chromatography on silica gel using hexane/MTBE gradient (0-100% MTBE) to afford tert-butyl 6-[2-(tert-butoxycarbonylamino)-1,3-benzothiazol-5-yl]-3-methyl-3,4-dihydro-2H-pyridine-1-carboxylate (1.8 g, 4.04 mmol, 21.11% yield) as light-yellow solid.

$^1$H NMR (500 MHz, CDCl$_3$) δ (ppm) 1.02 (d, 3H), 1.12 (s, 9H), 1.51 (s, 9H), 1.98 (m, 1H), 2.04 (m, 1H), 2.42 (m, 1H), 3.05 (m, 1H), 4.08 (d, 1H), 5.37 (m, 1H), 7.23 (d, 1H), 7.68 (d, 1H), 7.77 (s, 1H), 10.25 (m, 1H).

LCMS(ESI): [M]+ m/z: calcd 445.2; found 446.2; Rt=1.714 min.

Step 7: Synthesis of 5-(5-methyl-3,4,5,6-tetrahydropyridin-2-yl)benzo[d]thiazol-2-amine A solution of tert-butyl 6-[2-(tert-butoxycarbonylamino)-1,3-benzothiazol-5-yl]-3-methyl-3,4-dihydro-2H-pyridine-1-carboxylate (1.8 g, 4.04 mmol) in trifluoroacetic acid (44.40 g, 389.41 mmol, 30 mL) was stirred at 25° C. for 1 hr. After 1 hr, the reaction mixture was concentrated under reduced pressure. The obtained residue was diluted with ice cold water (30 mL) and neutralized with aqueous 10% NaOH solution till pH=10. The precipitate was filtered, washed with water (2*10 ml) and air-dried to afford 5-(3-methyl-2,3,4,5-tetrahydropyridin-6-yl)-1,3-benzothiazol-2-amine (0.8 g, 3.26 mmol, 80.72% yield) as light-yellow solid, which was used directly in the next step.

$^1$H NMR (500 MHz, DMSO-d$_6$) δ (ppm) 0.96 (d, 3H), 1.36 (m, 1H), 1.65 (m, 1H), 1.86 (m, 1H), 2.78 (m, 3H), 3.17 (m, 1H), 3.87 (m, 1H), 7.47 (m, 2H), 7.61 (d, 1H), 7.71 (s, 1H).

LCMS(ESI): [M]+ m/z: calcd 245.2; found 246.2; Rt=0.734 min.

Step 8: Synthesis of rac-5-((2R,5S)-5-methylpiperidin-2-yl)benzo[d]thiazol-2-amine To a stirring suspension of 5-(3-methyl-2,3,4,5-tetrahydropyridin-6-yl)-1,3-benzothiazol-2-amine (0.8 g, 3.26 mmol) in MeOH (30 mL) was added sodium borohydride (370.06 mg, 9.78 mmol, 345.85 μL) portion wise at 0° C. The resulting reaction mixture was stirred at 0° C. for 1 hr, then was allowed to warm to 25° C. and stirred for 12 hr, and then concentrated under reduced pressure. The residue was diluted with water (20 mL) and extracted with dichloromethane (80 mL). The organic extract was dried over sodium sulphate and concentrated under vacuum to obtain crude product 5-[(2R,5S)-5-methyl-2-piperidyl]-1,3-benzothiazol-2-amine (700 mg, 2.83 mmol, 86.79% yield) as light-yellow solid, which was used directly in the next step.

$^1$H NMR (500 MHz, CDCl$_3$) δ (ppm) 0.86 (d, 3H), 1.22 (m, 2H), 1.86 (m, 4H), 2.44 (m, 1H), 3.16 (m, 1H), 3.62 (m, 1H), 5.28 (s, 2H), 7.18 (d, 1H), 7.50 (d, 1H), 7.53 (s, 1H).

LCMS(ESI): [M]$^+$ m/z: calcd 247.2; found 248.2; Rt=0.766 min.

6NNN. The Synthesis of 6-(5-methyl-2-piperidyl)isoquinolin-1-ol

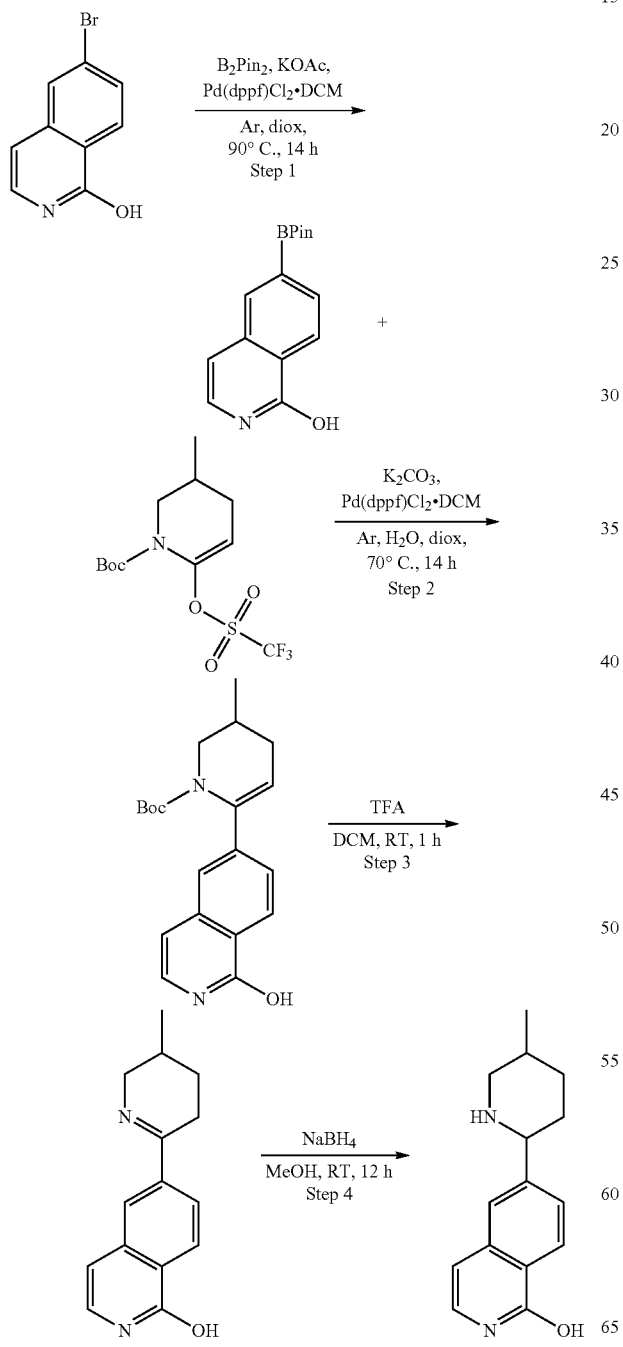

Step 1: The Synthesis of 6-(4,4,5,5-tetramethyl-1,3,2-dioxaborolan-2-yl)isoquinolin-1-ol Potassium Acetate (8.76 g, 89.26 mmol, 5.58 mL) was added to a solution of 6-bromoisoquinolin-1-ol (10 g, 44.63 mmol) and 4,4,5,5-tetramethyl-2-(4,4,5,5-tetramethyl-1,3,2-dioxaborolan-2-yl)-1,3,2-dioxaborolane (12.47 g, 49.10 mmol) in dioxane (150 mL). Reaction flask was evacuated and refilled with Ar 3 times. Then Pd(dppf)Cl$_2$ DCM (1.82 g, 2.23 mmol) was added under stream of argon. Resulting mixture was stirred at 90° C. for 14 hr under inert atmosphere. Then, it was cooled, diluted with EtOAc (400 mL) and washed with water (2×200 mL). Organic layer was dried over Na$_2$SO$_4$ and concentrated under reduced pressure. The residue was purified by silica gel flash chromatography eluting with CHCl$_3$-MeCN system to give 6-(4,4,5,5-tetramethyl-1,3,2-dioxaborolan-2-yl)isoquinolin-1-ol (9.3 g, 34.30 mmol, 76.86% yield).

LCMS(ESI): [M+H]$^+$ m/z: calcd 271.2; found 272.2; Rt=1.133 min.

Step 2: The Synthesis of tert-butyl 6-(1-hydroxy-6-isoquinolyl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (1.66 g, 4.79 mmol), 6-(4,4,5,5-tetramethyl-1,3,2-dioxaborolan-2-yl)isoquinolin-1-ol (1.3 g, 4.79 mmol) and Sodium carbonate (1.52 g, 14.38 mmol, 602.62 µL) were added to a mixture of water (5 mL) and dioxane (15 mL). The resulting mixture was evacuated and then backfilled with argon, this operation was repeated three times, then Pd(dppf)Cl$_2$ DCM (195.79 mg, 239.75 µmol) was added under argon. The reaction mixture was stirred under argon at 70° C. for 14 hr, then cooled and filtered. The filtercake was washed with 1,4-dioxane (2*20 mL) and discarded. The filtrate was evaporated in vacuo to afford tert-butyl 6-(1-hydroxy-6-isoquinolyl)-3-methyl-3,4-dihydro-2H-pyridine-1-carboxylate (0.5 g, 1.47 mmol, 30.63% yield) as brown oil, which was used in next step without purification.

LCMS(ESI): [M+H]$^+$ m/z: calcd 340.2; found 341.2; Rt=1.377 min.

Step 3: The Synthesis of 6-(3-methyl-2,3,4,5-tetrahydropyridin-6-yl)isoquinolin-1-ol The solution of tert-butyl 6-(1-hydroxy-6-isoquinolyl)-3-methyl-3,4-dihydro-2H-pyridine-1-carboxylate (0.5 g, 1.47 mmol) in TFA (2.51 g, 22.03 mmol, 1.70 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 6-(3-methyl-2,3,4,5-tetrahydropyridin-6-yl)isoquinolin-1-ol (0.35 g, 1.46 mmol, 99.16% yield) as brown oil, which was used directly in the next step.

LCMS(ESI): [M+H]$^+$ m/z: calcd 240.2; found 241.2; Rt=0.684 min.

Step 4: The Synthesis of 6-(5-methyl-2-piperidyl)isoquinolin-1-ol

Sodium Borohydride (110.21 mg, 2.91 mmol, 103.00 µL) was added in one portion to a stirred solution of 6-(3-methyl- 2,3,4,5-tetrahydropyridin-6-yl)isoquinolin-1-ol (0.35 g, 1.46 mmol) in MeOH (15 mL) at 0° C. The resulting mixture was stirred at 25° C. for 12 hr, and then evaporated in vacuo. The residue was diluted with water (20 ml) and extracted with dichloromethane (2*40 mL). The combined organic extracts were dried over sodium sulphate and evaporated in vacuo. The obtained oil was subjected to HPLC (Waters Sunfire C18 19*100 5 mkm column and MeOH as an eluent mixture) to afford 6-(5-methyl-2-piperidyl)isoquinolin-1-ol (0.1 g, 412.68 µmol, 28.33% yield).

LCMS(ESI): [M+H]$^+$ m/z: calcd 242.2; found 243.2; Rt=0.988 min.

6OOO. The Synthesis of 6-(5-methyl-2-piperidyl)-1-(2-trimethylsilylethoxymethyl)-1,5-naphthyridin-2-one

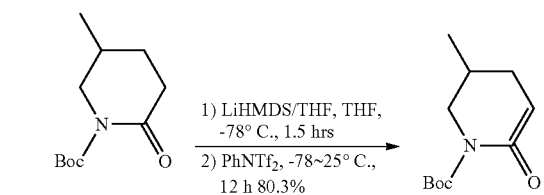

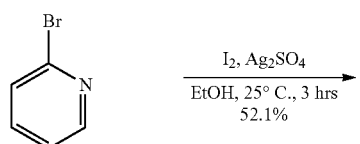

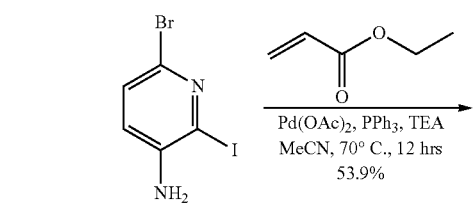

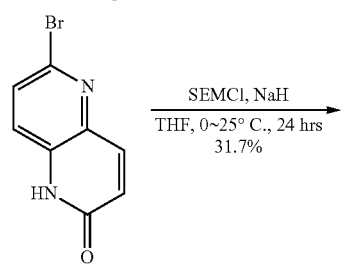

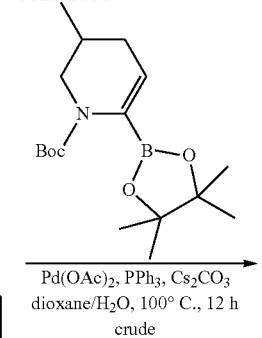

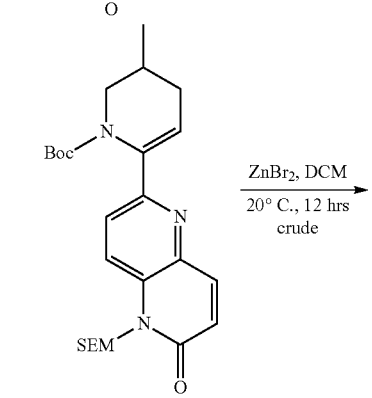

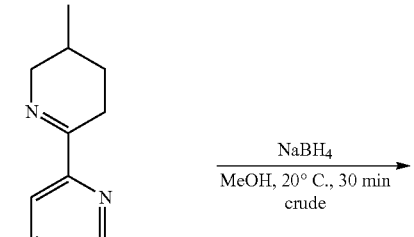

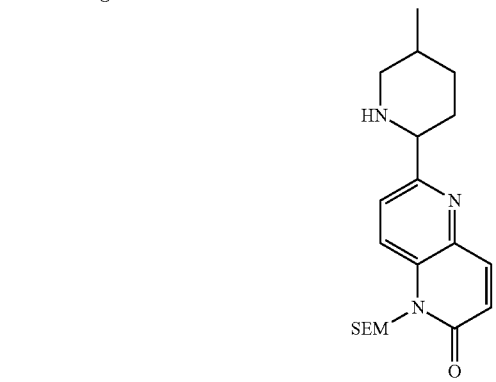

Step 1: Synthesis of tert-butyl 3-methyl-6-(trifluoromethylsulfonyloxy)-3,4-dihydro-2H-pyridine-1-carboxylate To a mixture of tert-butyl 5-methyl-2-oxo-piperidine-1-carboxylate (10 g, 46.9 mmol) in THF (200 mL) was sealed and degassed under vacuum and purged with nitrogen for three times, and then 1 M LiHMDS/THF (85 mL, 85 mmol) was added at −78° C. dropwise, the mixture was stirred 1.5 hours at −78° C., then a solution PhNTf$_2$ (26 g, 72.8 mmol) in THF (50 mL) was added. The solution was stirred at 25° C. for 12 hours. The resulting mixture was quenched by addition of saturated NH$_4$Cl aqueous solution (100 mL) and extracted with EtOAc (200 mL*3). The combined organic layer was washed with saturated NH$_4$Cl aqueous solution (100 mL), brine (100 mL), dried over anhydrous Na$_2$SO$_4$, filtered and concentrated under reduced pressure. The residue was purified by flash chromatography (ISCO®; 80 g AgelaFlash® Silica Flash Column, petroleum ether/EtOAc with EtOAc from 0~1%, flow rate=60 mL/min, I$_2$) to afford tert-butyl 3-methyl-6-(trifluoromethylsulfonyloxy)-3,4-dihydro-2H-pyridine-1-carboxylate (13 g, 80.3% yield) as yellow oil. $^1$H NMR (400 MHz, chloroform-d) δ ppm 5.25 (t, J=3.8 Hz, 1H), 3.87 (dd, J=12.7, 3.2 Hz, 1H), 3.00 (dd, J=12.8, 9.1 Hz, 1H), 2.29-2.49 (m, 1H), 1.77-2.00 (m, 2H), 1.49 (s, 9H), 0.99 (d, J=6.6 Hz, 3H); LCMS (ESI) [M+H]$^+$ m/z: calcd 346.1, found 290.0 (t-Bu cleaved mass).

Step 2: Synthesis of
6-bromo-2-iodo-pyridin-3-amine

To a solution of 6-bromopyridin-3-amine (10 g, 57.8 mmol) in EtOH (100 mL) was added Ag$_2$SO$_4$ (18 g, 57.7 mmol) and I2 (16 g, 63.0 mmol), Then the mixture was stirred at 25° C. for 3 hours. The resulting mixture was concentrated under reduced pressure to remove EtOH, then the crude was quenched by addition of water (100 mL) and extracted with DCM (100 mL*3). The combined organic layer was washed with brine (100 mL), dried over anhydrous Na$_2$SO$_4$, filtered and concentrated under reduced pressure. The residue was purified by flash chromatography (ISCO®; 40 g AgelaFlash® Silica Flash Column, petroleum ether/ EtOAc with EtOAc from 0~20%, flow rate=30 mL/min, 254 nm) to afford 6-bromo-2-iodo-pyridin-3-amine (9 g, 52.1% yield) as red solid. $^1$H NMR (400 MHz, chloroform-d) δ ppm 7.18 (d, J=8.3 Hz, 1H), 6.82 (d, J=8.3 Hz, 1H); LCMS (ESI) [M+H]$^+$ m/z: calcd 298.9, found 298.8.

Step 3: Synthesis of ethyl (E)-3-(3-amino-6-bromo-2-pyridyl)prop-2-enoate

To a solution of 6-bromo-2-iodo-pyridin-3-amine (9 g, 30.1 mmol) in MeCN (100 mL) were added Pd(OAc)$_2$ (1.3 g, 5.79 mmol), TEA (16.5 mL, 0.118 mol), PPh$_3$ (1.50 g, 5.72 mmol) and ethyl prop-2-enoate (3.2 mL, 29.5 mmol). The resulting mixture was sealed and degassed under vacuum and purged with nitrogen for three times, and then stirred at 70° C. for 12 hours under nitrogen atmosphere. The resulting mixture was concentrated under reduced pressure to give a crude product, which was purified by flash chromatography (ISCO®; 40 g AgelaFlash® Silica Flash Column, petroleum ether/EtOAc with EtOAc from 0~20%, flow rate=30 mL/min, 254 nm) to afford ethyl (E)-3-(3-amino-6-bromo-2-pyridyl)prop-2-enoate (4.4 g, 53.9% yield) as light-yellow solid. $^1$H NMR (400 MHz, chloroform-d) δ ppm 7.67 (d, J=15.1 Hz, 1H), 7.21 (d, J=8.3 Hz, 1H), 6.86-7.03 (m, 2H), 4.27 (q, J=7.0 Hz, 2H), 1.33 (t, J=7.2 Hz, 3H); LCMS (ESI) [M+H]$^+$ m/z: calcd 273.0, found 273.0.

Step 4: Synthesis of
6-bromo-1H-1,5-naphthyridin-2-one

To a solution of ethyl (E)-3-(3-amino-6-bromo-2-pyridyl)prop-2-enoate (2.2 g, 8.11 mmol) in EtOH (20 mL) was added a solution of DBU (6.1 mL, 40.9 mmol) in EtOH (5 mL) under 20° C. Then the mixture was stirred at 100° C. for 36 hours under nitrogen. The resulting mixture was concentrated under reduced pressure to give a crude product, which was purified by flash chromatography (ISCO®; 40 g AgelaFlash® Silica Flash Column, petroleum ether/EtOAc with EtOAc from 0~100%, flow rate=50 mL/min, 254 nm) to afford 6-bromo-1H-1,5-naphthyridin-2-one (2 g, crude) as brown solid. LCMS (ESI) [M+H]$^+$ m/z: calcd 225.0, found 225.0.

Step 6: Synthesis of tert-butyl 3-methyl-6-[6-oxo-5-(2-trimethylsilylethoxymethyl)-1,5-naphthyridin-2-yl]-3,4-dihydro-2H-pyridine-1-carboxylate To a mixture of 6-bromo-1-(2-trimethylsilylethoxymethyl)-1,5-naphthyridin-2-one (900 mg, 2.53 mmol) and tert-butyl 3-methyl-6-(4,4,5,5-tetramethyl-1,3,2-dioxaborolan-2-yl)-3,4-dihydro-2H-pyridine-1-carboxylate (1.3 g, 4.02 mmol) in dioxane (10 mL) and H$_2$O (1 mL) were added Pd(OAc)$_2$ (114 mg, 0.508 mmol), PPh$_3$ (265 mg, 1.01 mmol) and Cs$_2$CO$_3$ (1.6 g, 4.91 mmol). The resulting mixture was sealed and degassed under vacuum and purged with nitrogen for three times, and then stirred at 100° C. for 12 hours under nitrogen atmosphere. The resulting mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 25 g AgelaFlash® Silica Flash Column, petroleum ether/EtOAc with EtOAc from 0-20%, flow rate=30 mL/min, 254 nm) to afford tert-butyl 3-methyl-6-[6-oxo-5-(2-trimethylsilylethoxymethyl)-1,5-naphthyridin-2-yl]-3,4-dihydro-2H-pyridine-1-carboxylate (800 mg, crude) as yellow oil. LCMS (ESI) [M+H]$^+$ m/z: calcd 472.3, found 472.2.

Step 7: Synthesis of 6-(3-methyl-2,3,4,5-tetrahydropyridin-6-yl)-1-(2-trimethylsilylethoxymethyl)-1,5-naphthyridin-2-one To a solution of tert-butyl 3-methyl-6-[6-oxo-5-(2-trimethylsilylethoxymethyl)-1,5-naphthyridin-2-yl]-3,4-dihydro-2H-pyridine-1-carboxylate (800 mg, 1.70 mmol) in DCM (20 mL) was added ZnBr$_2$ (764 mg, 3.39 mmol). The mixture was stirred at 20° C. for 12 hours under nitrogen. The mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 25 g AgelaFlash® Silica Flash Column, petroleum ether/EtOAc with EtOAc from 0~50%, flow rate=30 mL/min, 245 nm) to afford 6-(3-methyl-2,3,4,5-tetrahydropyridin-6-yl)-1-(2-trimethylsilylethoxymethyl)-1,5-naphthyridin-2-one (600 mg, crude) as yellow solid. LCMS (ESI) [M+H]$^+$ m/z: calcd 372.3, found 372.2.

Step 8: Synthesis of 6-(5-methyl-2-piperidyl)-1-(2-trimethylsilylethoxymethyl)-1,5-naphthyridin-2-one To a solution of 6-(3-methyl-2,3,4,5-tetrahydropyridin-6-yl)-1-(2-trimethylsilylethoxymethyl)-1,5-naphthyridin-2-one (600 mg, 1.61 mmol) in MeOH (10 mL) was added NaBH$_4$ (93.0 mg, 2.46 mmol) at 0° C. The mixture was stirred at 20° C. for 30 minutes. The resulting mixture was quenched by addition of water (10 mL) and extracted with DCM (50 mL*3). The combined organic layer was dried over anhydrous $Na_2SO_4$, filtered and concentrated under reduced pressure to give 6-(5-methyl-2-piperidyl)-1-(2-trimethylsilylethoxymethyl)-1,5-naphthyridin-2-one (800 mg, crude) as yellow solid, which was used to the next step without further purification. 6PPP. Synthesis of 2-(4-fluorophenyl)-5-methylpiperidine-2-d

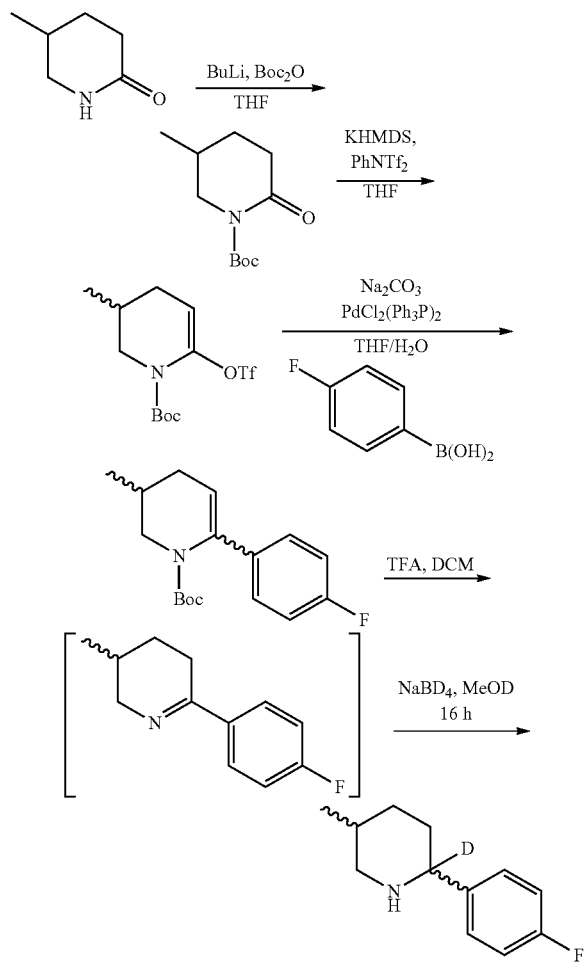

Step 1: Tert-butyl 5-methyl-2-oxopiperidine-1-carboxylate 5-methylpiperidin-2-one (1) (3.0 g, 26.51 mmol) was dissolved in THF (75 mL) and n-BuLi (17.7 mL of a 1.5 M solution in hexanes, 26.51 mmol) was added at −78° C. After stirring for 30 min, a THF (37.5 mL) solution of $Boc_2O$ (8.7 g, 9.14 mmol) was added dropwise and the resulting mixture was stirred overnight at room temperature. The reaction was quenched with a saturated $NH_4Cl$ aqueous solution (30 mL) and EtOAc (30 mL). The layers were separated and the aqueous layer was washed with $CH_2Cl_2$ (2*30 mL). The combined organic layers were dried ($Na_2SO_4$), filtered, and concentrated in vacuo. The residue was purified by silica gel column chromatography (10/0 Cyclohexane/Ethylacetate to 95/5) to give benzyl 6-tert-butyl 5-methyl-2-oxopiperidine-1-carboxylate (2) as a colorless oil (3.20 mg, 56%)

$^1$H NMR (CDCl$_3$, 400 MHz) δ 3.72 (ddd, J=1.9, 4.7, 12.6 Hz, 1H), 3.04 (dd, J=10.4, 12.6 Hz, 1H), 2.54-2.35 (m, 2H), 1.97-1.76 (m, 2H), 1.46 (s, 9H), 1.40-1.31 (m, 1H) 0.97 (d, J=6.6 Hz, 2.8H), 0.83 (d, J=6.6 Hz, 0.2H)

Step 2: Synthesis of tert-butyl 3-methyl-6-(((trifluoromethyl)sulfonyl)oxy)-3,4-dihydropyridine-1(2H)-carboxylate A solution of tert-butyl 5-methyl-2-oxopiperidine-1-carboxylate (2) (660 mg, 3.09 mmol) in anhydrous THF (23 mL) was cooled to −78° C. A 1 M solution of KHMDS (4.64 mL of a 1 M solution in THF, 4.64 mmol) was added over 5 min, and the mixture was stirred for 70 min. Then an anhydrous THF (6.8 mL) solution of PhNTf$_2$ (1.1 g, 3.09 mmol) was added and the mixture stirred at −78° C. (2 h). A saturated aqueous $Na_2CO_3$ solution (30 mL) and $CH_2Cl_2$ (30 mL) were added, and the layers were separated. The aqueous layer was washed with $CH_2Cl_2$ (2*30 mL). The combined organic layers were dried ($Na_2SO_4$), filtered, and concentrated in vacuo. The residue was purified by silica gel column chromatography (10/0 Cyclohexane/Ethylacetate to 85/15) to give tert-butyl 3-methyl-6-(((trifluoromethyl)sulfonyl)oxy)-3,4-dihydropyridine-1(2H)-carboxylate (3) as a colorless oil ( ).

$^1$H NMR (CDCl$_3$, 400 MHz) δ 5.27 (t, J=3.8 Hz, 1H), 3.87 (dd, J=3.3, 12.7 Hz, 1H), 3.00 (dd, J=9.2, 12.7 Hz, 1H), 2.39 (ddd, J=3.7, 6.1, 18.0 Hz, 1H), 1.98-1.78 (m, 2H), 1.49 (s, 9H), 0.99 (d, J=6.6 Hz, 3H)

Step 3: Synthesis of tert-butyl 6-(4-fluorophenyl)-3-methyl-3,4-dihydropyridine-1(2H)-carboxylate To a solution of tert-butyl 3-methyl-6-(((trifluoromethyl)sulfonyl)oxy)-3,4-dihydropyridine-1(2H)-carboxylate (400 mg, 1.16 mmol) in THF (11.6 mL) was added, under a nitrogen atmosphere, $(Ph_3P)_2PdCl_2$ (41 mg, 57.9 μmol), (4-fluorophenyl)boronic acid (243 mg, 1.74 mmol), and a 2 M aqueous $Na_2CO_3$ solution (9.3 mL). The mixture was stirring for 16 h at 40° C. Water (10 mL) was then added and the mixture was extracted with diethylether and dried ($Na_2SO_4$). The residue was purified by silica gel column chromatography (10/0 Cyclohexane/Ethylacetate to ⅛) to give tert-butyl 6-(4-fluorophenyl)-3-methyl-3,4-dihydropyridine-1(2H)-carboxylate (4) as colorless oil (200 mg, 60%)

$^1$H NMR (CDCl$_3$, 400 MHz) δ 7.28-7.23 (m, 2H), 6.97 (d, J=8.7 Hz, 2H), 5.24 (t, J=3.7 Hz, 1H), 4.06 (dd, J=3.4, 12.7 Hz, 1H), 3.00 (dd, J=9.2, 12.7 Hz, 1H), 2.39 (ddd, J=3.8, 6.4, 18.6 Hz, 1H), 2.05-1.94 (m, 1H), 1.84 (ddd, J=3.7, 8.6, 18.6 Hz, 1H), 1.10 (s, 9H), 1.01 (d, J=6.6 Hz, 3H).

Step 4: Synthesis of 2-(4-fluorophenyl)-5-methylpiperidine-2-d

TFA (0.86 mL) was added to a $CH_2Cl_2$ (0.86 mL) solution of tert-butyl 6-(4-fluorophenyl)-3-methyl-3,4-dihydropyridine-1(2H)-carboxylate (50 mg, 0.17 mmol). The solution was stirred 1 h at Room temperature and concentrated under vacuum. A saturated aqueous $Na_2CO_3$ solution (3 mL) and $CH_2Cl_2$ (3 mL) were added and the layers were separated. The aqueous layer was washed with $CH_2Cl_2$ (2×5 mL) All the organic layers were combined, dried and concentrated under vacuum. Methanol-d$_4$ (1.7 mL) was added to the residue followed by NaBD$_4$ (11 mg, 0.26 mmol). The mixture was stirred overnight at room temperature. The volatiles were evaporated and water was added. The aqueous layer was washed with CH$_2$Cl$_2$ (3×5 mL). All the organic layers were combined, dried and concentrated under vacuum to obtain 2-(4-fluorophenyl)-5-methylpiperidine-2-d as a white solid (23 mg, 69%)

$^1$H NMR (CDCl$_3$, 400 MHz) δ 7.35-7.29 (m, 2H), 6.98 (d, J=8.8 Hz, 2H), 3.15-3.08 (m, 1H), 2.40 (t, J=11.3 Hz, 1H), 1.90-1.46 (m, 3H), 1.14 (d, J=7.1 Hz, 1H), 0.89 (d, J=6.6 Hz, 3H).

6QQQ. The Synthesis of 2-(4-Fluorophenyl-2,3,5,6-d4)-5-methylpiperidine-2-d and 2-(4-Fluorophenyl-2,3,5,6-d4)-5-methylpiperidine-2-d

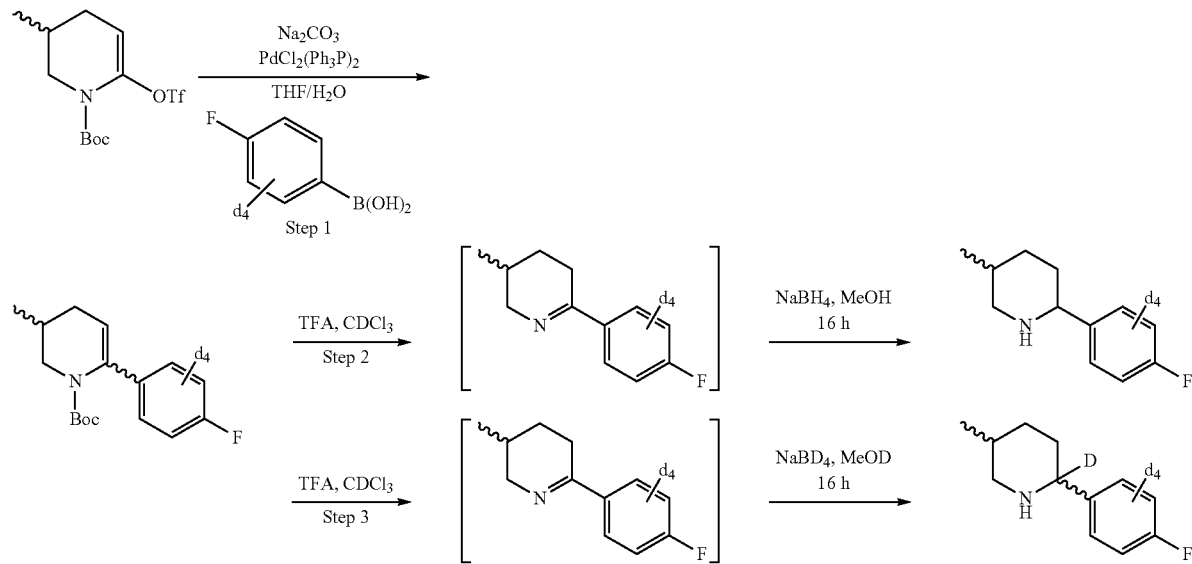

Step 1: Synthesis of tert-butyl 6-(4-Fluorophenyl-2,3,5,6-d4)-3-methyl-3,4-dihydropyridine-1(2H)-carboxylate (5)

To a solution of tert-butyl 3-methyl-6-(((trifluoromethyl)sulfonyl)oxy)-3,4-dihydropyridine-1(2H)-carboxylate (200 mg, 0.58 mmol) in THF (3.9 mL) was added, under a nitrogen atmosphere, (Ph$_3$P)$_2$PdCl$_2$ (20 mg, 29.0 μmol), (4-fluorophenyl-2,3,5,6-d4)boronic acid (243 mg, 0.58 mmol), and a 2 M aqueous Na$_2$CO$_3$ solution (2.3 mL). The mixture was stirring for 16 h at 80° C. Water (10 mL) was then added and the mixture was extracted with diethyl ether and dried (Na$_2$SO$_4$). The residue was purified by silica gel column chromatography (10/0 Cyclohexane/Ethyl acetate to 1/9) to give tert-butyl 6-(4-fluorophenyl-2,3,5,6-d4)-3-methyl-3,4-dihydropyridine-1(2H)-carboxylate (5) as yellow oil (80 mg, 47%)

$^1$H NMR (CDCl$_3$, 400 MHz) 5.24 (t, J=3.8 Hz, 1H), 4.06 (dd, J=3.4, 12.6 Hz, 1H), 2.97 (dd, J=9.4, 12.2 Hz, 1H), 2.39 (ddd, J=3.9, 6.4, 18.6 Hz, 1H), 2.06-1.95 (m, 1H), 1.84 (ddd, J=3.7, 8.6, 18.6 Hz, 1H), 1.10 (s, 9H), 1.01 (d, J=6.7 Hz, 3H).

Step 2: Synthesis of 2-(4-Fluorophenyl-2,3,5,6-d4)-5-methylpiperidine-2-d

TFA (0.4 mL) was added to a CH$_2$Cl$_2$ (0.4 mL) solution of tert-butyl 6-(4-fluorophenyl-2,3,5,6-d4)-3-methyl-3,4-dihydropyridine-1(2H)-carboxylate (5) (23 mg, 78 μmol). The solution was stirred 1 h at room temperature and concentrated under vacuum. A saturated aqueous Na$_2$CO$_3$ solution (2 mL) and CH$_2$Cl$_2$ (2 mL) were added and the layers were separated. The aqueous layer was washed with CH$_2$Cl$_2$ (2×2 mL) All the organic layers were combined, dried and concentrated under vacuum. Methanol (0.4 mL) was added to the residue followed by NaBH$_4$ (4 mg, 0.1 mmol). The mixture was stirred overnight at room temperature. The volatiles were evaporated and water was added. The aqueous layer was washed with CH$_2$Cl$_2$ (3×5 mL).

All the organic layers were combined, dried and concentrated under vacuum to obtain 2-(4-fluorophenyl-2,3,5,6-d4)-5-methylpiperidine as a white solid (15 mg, 100%)

$^1$H NMR (CDCl$_3$, 400 MHz) δ 3.53 (dd, J=2.2, 11.3 Hz, 1H), 3.13 (ddd, J=1.9, 3.9, 11.5 Hz, 1H), 2.41 (t, J=11.2 Hz, 1H), 1.90-1.46 (m, 3H), 1.16-1.12 (m, 1H), 0.90 (d, J=6.6 Hz, 3H).

Step 3: Synthesis of 2-(4-Fluorophenyl-2,3,5,6-d4)-5-methylpiperidine-2-d

TFA (2.0 mL) was added to a CH$_2$Cl$_2$ (2.0 mL) solution of tert-butyl 6-(4-fluorophenyl-2,3,5,6-d4)-3-methyl-3,4-dihydropyridine-1(2H)-carboxylate (5) (120 mg, 0.41 mmol). The solution was stirred 1 h at room temperature and concentrated under vacuum. A saturated aqueous Na$_2$CO$_3$ solution (10 mL) and CH$_2$Cl$_2$ (10 mL) were added and the layers were separated. The aqueous layer was washed with CH$_2$Cl$_2$ (2×10 mL) All the organic layers were combined, dried and concentrated under vacuum. Methanol-d$_4$ (2.0 mL) was added to the residue followed by NaBD$_4$ (22 mg, 0.53 mmol). The mixture was stirred overnight at room temperature. The volatiles were evaporated and water was added. The aqueous layer was washed with CH$_2$Cl$_2$ (3×5 mL). All the organic layers were combined, dried and concentrated under vacuum to obtain 2-(4-fluorophenyl-2,3,5,6-d4)-5-methylpiperidine-2-d as a white solid (81 mg, 100%)

$^1$H NMR (CDCl$_3$, 400 MHz) δ 3.13 (ddd, J=2.0, 3.9, 11.5 Hz, 1H), 2.40 (t, J=11.2 Hz, 1H), 1.90-1.46 (m, 3H), 1.19-1.12 (m, 1H), 0.90 (d, J=6.6 Hz, 3H).

6RRR. Synthesis of 5-[(2S,5R)-5-methyl-2-piperidyl]thiazole

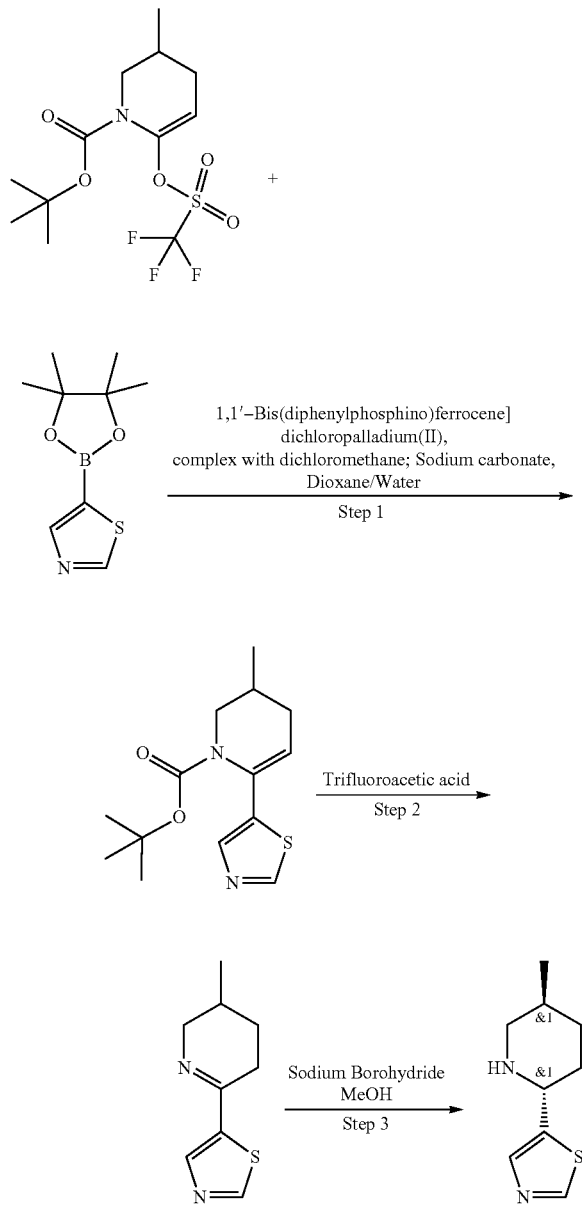

Step 1: Synthesis of tert-butyl 3-methyl-6-thiazol-5-yl-3,4-dihydro-2H-pyridine-1-carboxylate To a solution of tert-butyl 3-methyl-6-thiazol-5-yl-3,4-dihydro-2H-pyridine-1-carboxylate (14.61 g, 52.11 mmol), 5-(4,4,5,5-tetramethyl-1,3,2-dioxaborolan-2-yl)thiazole (10 g, 47.37 mmol), Sodium carbonate (15.06 g, 142.12 mmol, 5.95 mL) in Dioxane (150 mL) and Water (50 mL), 1,1′-Bis(diphenylphosphino)ferrocene]dichloropalladium(II), complex with dichloromethane (1.55 g, 1.89 mmol) was added under argon atmosphere. The resulting mixture was stirred at 90° C. for 48 hr, cooled, filtered and evaporated. The residue was dissolved in EtOAc and dried over Na₂SO₄, evaporated in vacuo and purified by gradient chromatography (Hexane-MTBE) to give tert-butyl 3-methyl-6-thiazol-5-yl-3,4-dihydro-2H-pyridine-1-carboxylate (0.4 g, 1.43 mmol, 3.01% yield).

$^1$H NMR (CDCl$_3$, 400 MHz): δ 1.01 (d, 3H), 1.19 (s, 9H), 1.41 (m, 1H), 1.86 (m, 1H), 1.97 (m, 1H), 2.37 (d, 1H), 2.96 (dd, 1H), 4.01 (d, 1H), 5.47 (t, 1H), 7.74 (s, 1H), 8.63 (s, 1H).

LCMS(ESI): [M+H]$^+$ m/z: calcd 280.15; found 281.2; Rt=1.29 min.

Step 2: Synthesis of 5-(3-methyl-2,3,4,5-tetrahydropyridin-6-yl)Thiazole

A solution of tert-butyl 3-methyl-6-thiazol-5-yl-3,4-dihydro-2H-pyridine-1-carboxylate (0.4 g, 1.43 mmol) in Trifluoroacetic acid (8 g, 70.16 mmol, 5.41 mL) was stirred at 25° C. for 2 hr and evaporated in vacuo. The residue was diluted with saturated solution of NaHCO$_3$ (50 ml), extracted with DCM (3*30 ml), washed with brine, dried over Na$_2$SO$_4$ and evaporated in vacuo to obtain 5-(3-methyl-2,3,4,5-tetrahydropyridin-6-yl)thiazole (0.25 g, 1.39 mmol, 97.21% yield).

$^1$H NMR (CDCl$_3$, 500 MHz): δ 1.00 (d, 3H), 1.41 (m, 1H), 1.73 (m, 1H), 1.93 (m, 1H), 2.59 (m, 1H), 2.80 (dd, 1H), 3.23 (m, 1H), 3.94 (d, 1H), 8.03 (s, 1H), 8.77 (s, 1H).

LCMS(ESI): [M+H]$^+$ m/z: calcd 180.1; found 181.2; Rt=0.466 min.

Step 3: Synthesis of 5-[(2S,5R)-5-methyl-2-piperidyl]thiazole

To a solution of 5-(3-methyl-2,3,4,5-tetrahydropyridin-6-yl)thiazole (0.25 g, 1.39 mmol) in MeOH (30 mL), Sodium Borohydride (104.93 mg, 2.77 mmol, 98.07 μL) was added at 0° C. The resulting mixture was stirred for 2 hr and evaporated vacuo. The residue was diluted with water (20 ml) and extracted with DCM (3*20 ml). The combined organic layer was washed with brine (20 ml), dried over Na$_2$SO$_4$ and evaporated in vacuo to obtain 5-[(2S,5R)-5-methyl-2-piperidyl]thiazole (0.25 g, 1.37 mmol, 98.89% yield).

$^1$H NMR (DMSO, 400 MHz): δ 0.87 (d, 3H), 1.13-1.20 (m, 2H), 1.55-1.60 (m, 2H), 1.60-1.84 (m, 2H), 1.87 (d, 1H), 1.97 (d, 1H), 2.42 (t, 1H), 3.11 (d, 1H), 3.93 (d, 1H), 7.72 (s, 1H), 8.67 (s, 1H).

LCMS(ESI): [M+H]$^+$ m/z: calcd 182.1; found 183.0; Rt=0.684 min.

6SSS. The Synthesis of rac-4-((2R,5S)-5-methylpiperidin-2-yl)pyridine

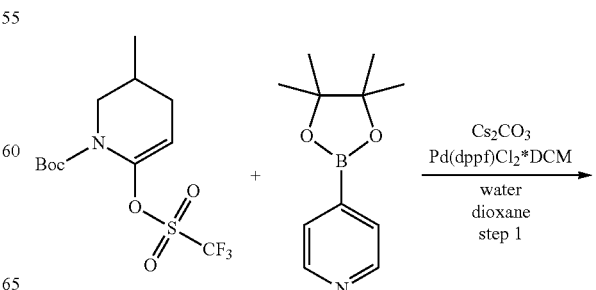

-continued

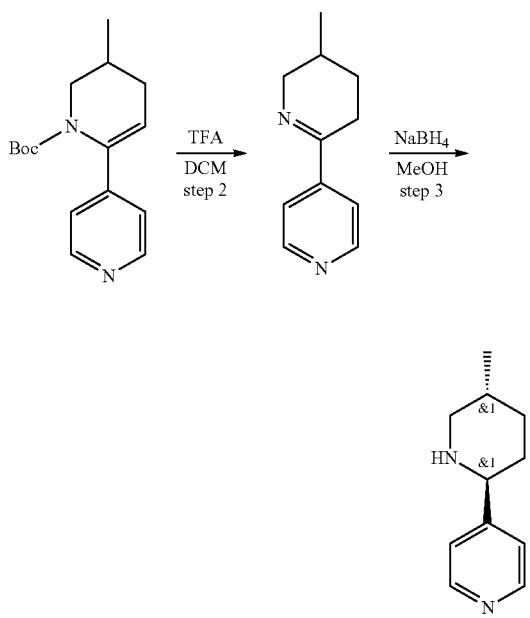

Step 1: Synthesis of tert-butyl 5-methyl-5,6-dihydro-[2,4'-Bipyridine]-1(4H)-carboxylate tert-butyl 3-methyl-6-(trifluoromethylsulfonyloxy)-3,4-dihydro-2H-pyridine-1-carboxylate (5.62 g, 16.27 mmol) and 4-pyridylboronic acid (2 g, 16.27 mmol) was dissolved in dioxane and the reaction mixture was thoroughly degassed, following by the subsequent addition of cesium carbonate (26.51 g, 81.36 mmol), H$_2$O and Pd(dppf)Cl$_2$*DCM (1.63 mmol). Obtained reaction mixture was stirred at reflux overnight; after reaction was complete the organic solvent was evaporated under reduced pressure and the crude mixture was partitioned between EtOAc and H$_2$O. Water layer was additionally extracted with EtOAc twice; combined organic layers was washed with brine, dried over Na$_2$SO$_4$ and evaporated to give tert-butyl 3-methyl-6-(4-pyridyl)-3,4-dihydro-2H-pyridine-1-carboxylate (7 g, crude), which was used in the next step without purification.

$^1$H NMR (400 MHz, DMSO-d$_6$) δ (ppm) 0.96 (d, 3H), 1.08 (s, 9H), 1.85 (m, 2H), 2.32 (m, 1H), 2.98 (m, 1H), 3.83 (d, 1H), 5.52 (m, 1H), 7.18 (d, 2H), 8.42 (d, 2H).

Step 2: Synthesis of 5-methyl-3,4,5,6-tetrahydro-2,4'-Bipyridine tert-butyl 3-methyl-6-(4-pyridyl)-3,4-dihydro-2H-pyridine-1-carboxylate (7 g, 25.51 mmol) was dissolved in DCM (200 mL) followed by the addition of TFA (2.91 g, 25.51 mmol, 1.97 mL) and stirring overnight. After the reaction was complete, the mixture was washed with 10% aq NaOH, and the organic solvent was evaporated to give 4-(3-methyl-2,3,4,5-tetrahydropyridin-6-yl)pyridine (3.5 g, 20.09 mmol, 78.73% yield) which was used in the next step without purification.

$^1$H NMR (500 MHz, CDCl$_3$) δ (ppm) 1.02 (d, 3H), 1.22 (m, 1H), 1.73 (m, 1H), 1.98 (m, 1H), 2.45 (m, 1H), 2.77 (m, 1H), 3.27 (m, 1H), 4.03 (m, 1H), 7.62 (d, 2H), 8.64 (d, 2H).

Step 3: Synthesis of rac-4-((2R,5S)-5-methylpiperidin-2-yl)pyridine 4-(3-methyl-2,3,4,5-tetrahydropyridin-6-yl)pyridine (3.5 g, 20.09 mmol) was dissolved in MeOH (50 mL) and H$_2$O (10 mL) and cooled to 0° C. Sodium borohydride (759.89 mg, 20.09 mmol, 710.18 μL) was added in portions to obtained mixture and additionally stirred overnight. After the reaction was complete, the reaction mixture was acidified with 10% aq HCl to pH=2, washed with MTBE (2*10 mL), basified with 10% aq NaOH to pH=10 and extracted with DCM (50 mL). Evaporation of the solvent result in pure 4-[(2S,5R)-5-methyl-2-piperidyl]pyridine (2.5 g, 14.18 mmol, 70.61% yield).

$^1$H NMR (500 MHz, CDCl$_3$) δ (ppm) 0.86 (d, 3H), 1.18 (m, 2H), 1.75 (m, 4H), 2.40 (m, 1H), 3.14 (m, 1H), 3.56 (m, 1H), 7.28 (d, 2H), 8.53 (d, 2H).

LCMS(ESI): [M]$^+$ m/z: calcd 176.2; found 177.2; Rt=0.226 min.

Scheme A. Synthesis of Compounds of Formula 1

Compounds of Formula 1, 1a, 1b, 1c and 1d are compounds of Formula (I), (Ia), (Ib), (Ic) and (Id) wherein R$^1$, R$^2$, R$^3$, R$^4$, R$^6$, R$^7$ and R$^8$ are as defined herein, and at least one of R$^1$ or R$^2$ are —NH$_2$, R$^{1a}$ is R$^1$ or —NH-PG, R$^{2a}$ is R$^2$ or —NH-PG. PG is a nitrogen protecting groups as described herein (e.g., -Boc).

General Procedure 1

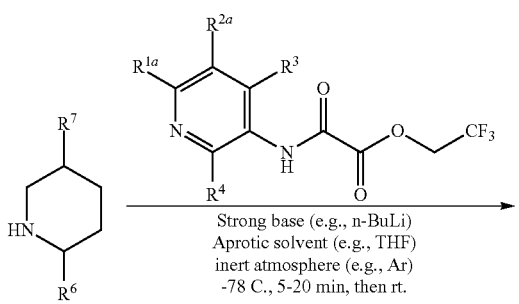

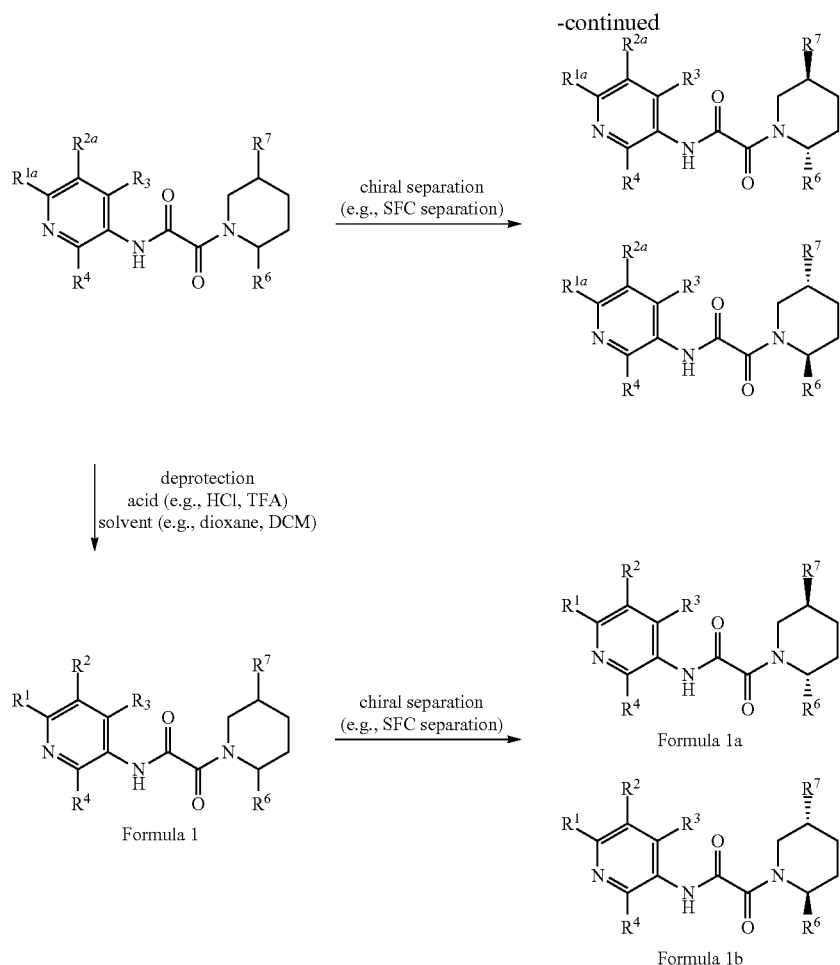

Note that in certain instances the starting piperidine is already in a cis or trans configuration. In those cases, the chiral separation step only results in two of the four enantiomers depicted.

As shown in Scheme A, compounds of Formula (Ia), (Ib), (Ic), and (Id) can be separated from a mixture of compounds of Formula (I), wherein $R^1$, $R^2$, $R^3$, $R^4$, $R^6$, $R^7$, $R^8$, and n are as described herein. Alternatively, compounds of Formula (Ia), (Ib), (Ic), and (Id) can be prepared from their protected precursors. In some embodiments, $R^{1a}$ is selected from $R^1$ and —NH-PG and $R^{2a}$ is selected from $R^2$ and —NH-PG, wherein PG is a nitrogen protecting group as defined herein (e.g., -Boc). In certain embodiments (e.g., when $R^{1a}$ is NH-PG and $R^1$ is —NH$_2$ or $R^{2a}$ is NH-PG and $R^2$ is —NH$_2$), a deprotection step is employed to convert $R^{1a}$ to $R^1$ or $R^{2a}$ to $R^2$. In some embodiments, deprotection can take place before or after chiral separation. Conditions for removing a protecting group -PG (e.g, -Boc) can employ, for example, acidic conditions, (e.g., water/dioxane, hydrochoric acid in a protic solvent (e.g., methanol), hydrochloric acid in an aprotic solvent (e.g., dioxane), TFA in an aprotic solvent (e.g., dichloromethane, chloroform, etc)). In some embodiments, a deproction step employs HCl (40 M) in dioxane. In some embodiments, a deproction step employs HCl (40 M) in DCM.

Methods of chiral separation are known to persons of ordinary skill in the art. For example, in some embodiments, chiral separation can be accomplished through the use of chiral HPLC purification (Column: AD-H III (250*20 mm, 5 m). Exemplary eluents include, but are not limited to, hexane, IPA, MeOH, MeCN, and H$_2$O, and mixtures thereof.

As shown in Scheme A, preparation of compounds describe herein can include an amide bond coupling step. In some embodiments, an amide bond coupling comprises the coupling of a piperidine to a 2,2,2-trifluoroethyl ester in the presence of a strong base (e.g., an alkyl lithium base) in an aprotic solvent (e.g., THF) under an inert atmosphere (e.g., under Argon). In some embodiments, the reaction takes place at temperatures between −100° C. and −60° C. In some embodiments, the reaction takes place at temperatures of around −78° C. In some embodiments an amide bond coupling comprises use of n-BuLi in THF at −78° C.

Example 1. Synthesis of N-(6-amino-5-methylpyridin-3-yl)-2-oxo-2-(2-phenyl-3-azabicyclo[3.2.1]octan-3-yl)acetamide (Compound 63, Compound 62, Compound 64, Compound 65

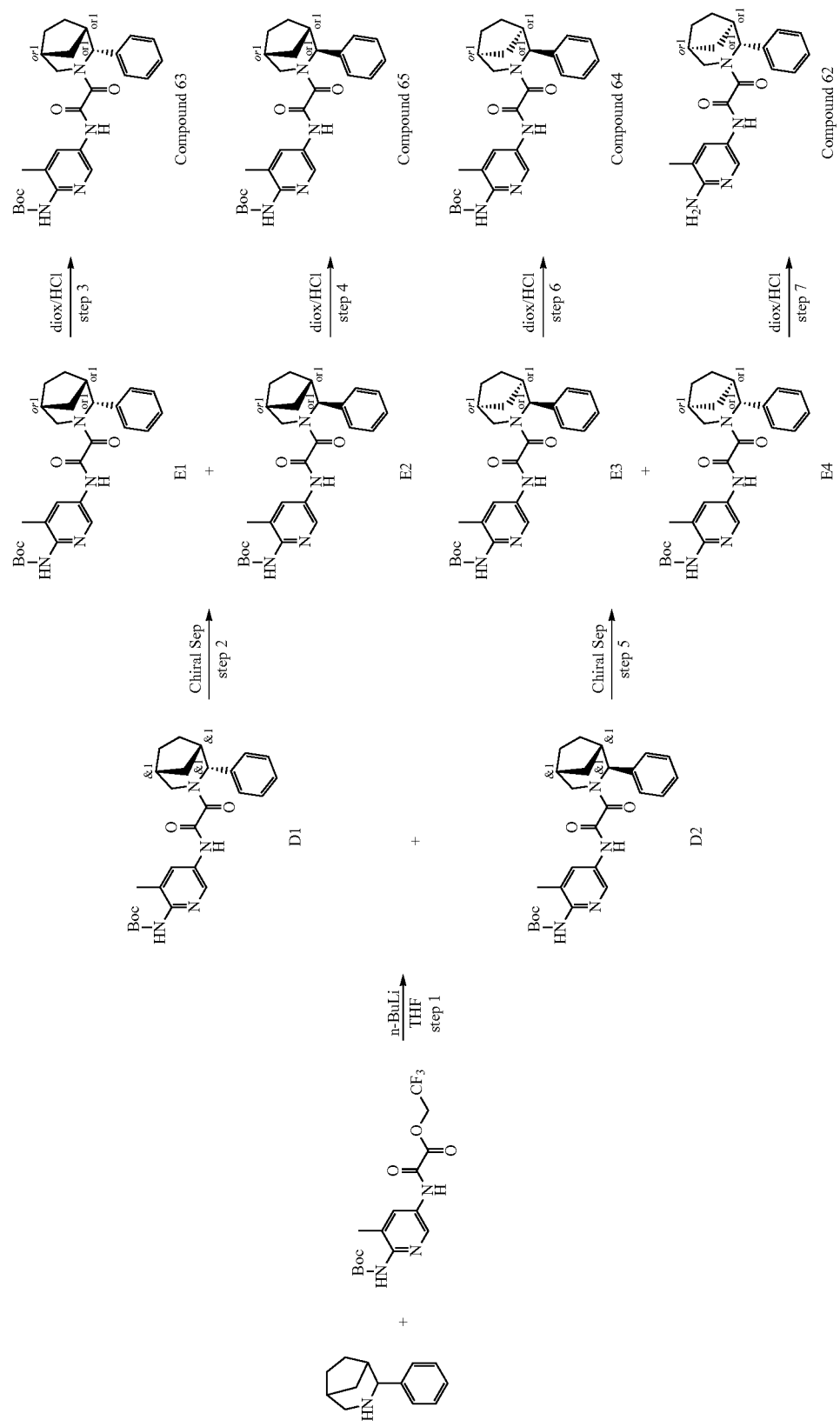

Step 1: Synthesis of tert-butyl (3-methyl-5-(2-oxo-2-(2-phenyl-3-azabicyclo[3.2.]octan-3-yl)acetamido) pyridin-2-yl)carbamate To a solution of 4-phenyl-3-azabicyclo[3.2.]octane (0.5 g, 2.67 mmol) and 2,2,2-trifluoroethyl 2-[[6-(tert-butoxycarbonylamino)-5-methyl-3-pyridyl]amino]-2-oxo-acetate (1.01 g, 2.67 mmol) in THF (50 mL) was added n-butyllithium (2.60 g, 9.34 mmol, 3.76 mL, 23% purity) at −78° C. under Ar atmosphere. The resulting mixture was stirred for 15 min and warmed to rt, quenched with NH$_4$Cl aq solution, extracted with EtOAc, dried over Na$_2$SO$_4$, evaporated and subjected to HPLC (LC 11 60-60-70% 0-1-6 min water-methanol, flow: 30 ml/min (loading pump 4 ml/min methanol), target mass 464 column: SunFire C18 100×19 mm, 5 um). After purification was observed 3 fractions: 1-st (pair of diastereomers): 181 mg, 2-nd (mixture): 127 mg, 3-rd (pair of diastereomers): 65 mg. The configuration is assigned arbitrarily. Fractions 1 and 3 was subjected to chiral separation. D1: LCMS(ESI): [M]$^+$ m/z: calcd 464.5; found 465.2; Rt=4.122 min D2: LCMS(ESI): [M]$^+$ m/z: calcd 464.5; found 465.2; Rt=4.326 min.

Step 2: Chiral Separation (E1 and E2)

Purification on the chiral column was taken in the system Hex-IPA-MeOH, 80-10-10, 12 mL/min. Number of injections: 1, injection volume: 700 mkl. From 181 mg of racemate, 79 mg and 76 mg of the individual enantiomers were obtained.

E1: Retention time: 33.56 min LCMS(ESI): [M]$^+$ m/z: calcd 364.5; found 365.2; Rt=5.463 min.

E2: Retention time: 18.49 min. LCMS(ESI): [M]$^+$ m/z: calcd 364.5; found 365.2; Rt=5.462 min.

Step 3: Synthesis of N-(6-amino-5-methyl-3-pyridyl)-2-oxo-2-[(1S,4R,5R)-4-phenyl-3-azabicyclo[3.2.1]octan-3-yl]acetamide (Compound 63)

tert-butyl N-[3-methyl-5-[[2-oxo-2-[(1S,4R,5R)-4-phenyl-3-azabicyclo[3.2.1]octan-3-yl]acetyl]amino]-2-pyridyl]carbamate (79 mg, 170.06 µmol) was dissolved in hydrogen chloride solution 40 M in dioxane (1.60 g, 43.88 mmol, 2 mL), stirred at 25° C. for 12 hr, evaporated and dried to obtain crude product. The crude product was purified by HPLC (LC 11 40-40-70% 0-1-6 min 0.1% NH$_3$-methanol, flow: 30 ml/min (loading pump 4 ml/min methanol), target mass 364 column: YMC Actus Triart C18 100×20 mm, 5 um) to obtain N-(6-amino-5-methyl-3-pyridyl)-2-oxo-2-[(1S,4R,5R)-4-phenyl-3-azabicyclo[3.2.1]octan-3-yl]acetamide (23 mg, 63.11 µmol, 37.11% yield). LCMS(ESI): [M]$^+$ m/z: calcd 364.4; found 365.2; Rt=2.661 min.

Step 4: Synthesis of N-(6-amino-5-methyl-3-pyridyl)-2-oxo-2-[(1S,4S,5R)-4-phenyl-3-azabicyclo[3.2.1]octan-3-yl]acetamide (Compound 65)

tert-butyl N-[3-methyl-5-[[2-oxo-2-[(1S,4S,5R)-4-phenyl-3-azabicyclo[3.2.1]octan-3-yl]acetyl]amino]-2-pyridyl]carbamate (76 mg, 163.60 µmol) was dissolved in hydrogen chloride solution 4.0 M in dioxane (1.60 g, 43.88 mmol, 2 mL), stirred at 25° C. for 12 hr, evaporated and dried to obtain crude product. The crude product was purified by HPLC (LC 11 40-40-70% 0-1-6 min 0.1% NH$_3$-methanol, flow: 30 ml/min (loading pump 4 ml/min methanol), target mass 364 column: YMC Actus Triart C18 100×20 mm, 5 um) to obtain N-(6-amino-5-methyl-3-pyridyl)-2-oxo-2-[(1S,4S,5R)-4-phenyl-3-azabicyclo[3.2.1]octan-3-yl]acetamide (21 mg, 57.62 µmol, 35.22% yield). $^1$H NMR (500 MHz, CDCl$_3$) δ (ppm) 1.36 (m, 1H), 1.62 (m, 3H), 1.76 (m, 2H), 1.95 (m, 1H), 2.15 (m, 3H), 2.30 (m, 1H), 2.78 (m, 1H), 3.38 (m, 1H), 4.47 (m, 1H), 4.81 (m, 2H), 5.88 (m, 1H), 7.21 (m, 2H), 7.35 (m, 2H), 7.72 (m, 1H), 8.06 (m, 1H), 8.97 (m, 1H).

LCMS(ESI): [M]$^+$ m/z: calcd 364.4; found 365.2; Rt=2.640 min.

Step 5: Chiral Separation (E3 and E4

Purification on the chiral column was taken in the system Hex-IPA-MeOH, 60-20-20, 12 mL/min. Number of injections: 1, injection volume: 40 mkl. From 65 mg of racemate, 14 mg and 12 mg of the individual enantiomers were obtained.

E3: Retention time: 27.78 min. LCMS(ESI): [M]$^+$ m/z: calcd 364.5; found 365.2; Rt=5.640 min.

E4: Retention time: 14.46 min. LCMS(ESI): [M]$^+$ m/z: calcd 364.5; found 365.2; Rt=5.753 min.

Step 6: Synthesis of N-(6-amino-5-methyl-3-pyridyl)-2-oxo-2-[(1R,4S,5S)-4-phenyl-3-azabicyclo[3.2.1]octan-3-yl]acetamide (Compound 64)

tert-butyl N-[3-methyl-5-[[2-oxo-2-[(1R,4S,5S)-4-phenyl-3-azabicyclo[3.2.1]octan-3-yl]acetyl]amino]-2-pyridyl]carbamate (14 mg, 30.14 µmol) was dissolved in hydrogen chloride solution 4.0 M in dioxane (800.00 mg, 21.94 mmol, 1 mL), stirred at 25° C. for 12 hr, evaporated and dried to obtain crude product. The crude product was purified by HPLC (LC 11 40-40-70% 0-1-6 min 0.1% NH$_3$-methanol, flow: 30 ml/min (loading pump 4 ml/min methanol), target mass 364 column: YMC Actus Triart C18 100×20 mm, 5 um) to obtain N-(6-amino-5-methyl-3-pyridyl)-2-oxo-2-[(1R,4S,5S)-4-phenyl-3-azabicyclo[3.2.]octan-3-yl]acetamide (8 mg, 21.95 µmol, 72.84% yield). LCMS(ESI): [M]$^+$ m/z: calcd 364.4; found 365.2; Rt=2.619 min.

Step 7: Synthesis of N-(6-amino-5-methyl-3-pyridyl)-2-oxo-2-[(1R,4R,5S)-4-phenyl-3-azabicyclo[3.2.1]octan-3-yl]acetamide (Compound 62)

tert-butyl N-[3-methyl-5-[[2-oxo-2-[(1R,4R,5S)-4-phenyl-3-azabicyclo[3.2.1]octan-3-yl]acetyl]amino]-2-pyridyl]carbamate (12 mg, 25.83 µmol) was dissolved in hydrogen chloride solution 40 M in dioxane (800.00 mg, 21.94 mmol, 1 mL), stirred at 25° C. for 12 hr, evaporated and dried to obtain crude product. The crude product was purified by HPLC (LC 11 40-40-70% 0-1-6 min 0.1% NH$_3$-methanol, flow: 30 ml/min (loading pump 4 ml/min methanol), target mass 364 column: YMC Actus Triart C18 100×20 mm, 5 um) to obtain N-(6-amino-5-methyl-3-pyridyl)-2-oxo-2-[(1R,4R,5S)-4-phenyl-3-azabicyclo[3.2.1]octan-3-yl]acetamide (7 mg, 19.21 µmol, 74.36% yield). $^1$H NMR (500 MHz, CDCl$_3$) δ (ppm) 1.36 (m, 1H), 1.64 (d, 2H), 1.75 (d, 3H), 1.93 (d, 1H), 2.16 (m, 3H), 2.27 (m, 1H), 2.78 (m, 1H), 3.31 (m, 1H), 4.54 (m, 1H), 5.03 (m, 2H), 5.87 (m, 1H), 7.22 (m, 2H), 7.36 (m, 2H), 7.77 (m, 1H), 8.08 (m, 1H), 9.00 (m, 1H).

LCMS(ESI): [M]⁺ m/z: calcd 364.4; found 365.2; Rt=2.608 min.

Example 2. The Synthesis of N-(6-amino-5-methyl-3-pyridyl)-2-[(2S,5R)-2-(4-fluorophenyl)-5-methyl-1-piperidyl]-2-oxo-acetamide (Compound 233) and N-(6-amino-5-methyl-3-pyridyl)-2-[(2S,5R)-2-(4-fluorophenyl)-5-methyl-1-piperidyl]-2-oxo-acetamide(Compound 242

Step 1. Synthesis of tert-butyl N-[5-[[2-[2-(4-fluorophenyl)-5-methyl-1-piperidyl]-2-oxo-acetyl]amino]-3-methyl-2-pyridyl]carbamate To a solution of 2,2,2-trifluoroethyl 2-[[6-(tert-butoxycarbonylamino)-5-methyl-3-pyridyl]amino]-2-oxo-acetate (585.71 mg, 1.55 mmol)2-(4-fluorophenyl)-5-methyl-piperidine (0.3 g, 1.55 mmol) in THF (15 mL) was added n-butyllithium (1.30 g, 4.66 mmol, 1.87 mL, 23% purity) at −78° C. under Ar atmosphere. After 15 min, 2,2,2-trifluoroethyl 2-[[6-(tert-butoxycarbonylamino)-5-methyl-3-pyridyl]amino]-2-oxo-acetate (585.71 mg, 1.55 mmol) was added in one portion. The resulting mixture was warmed to rt, quenched with NH$_4$Cl aq solution, extracted with EtOAc, dried over Na$_2$SO$_4$, evaporated and subjected to HPLC (50-75% ACN, 30 ml/min, sunfire C18 19*100, 5 uM). tert-butyl N-[5-[[2-[2-(4-fluorophenyl)-5-methyl-1-piperidyl]-2-oxo-acetyl]amino]-3-methyl-2-pyridyl]carbamate (181.7 mg, 386.16 μmol, 24.88% yield) was obtained as a pale yellow solid.

$^1$H NMR (400 MHz, CDCl$_3$) δ (ppm) 1.07 (d, 3H), 1.39 (m, 1H), 1.48 (s, 9H), 1.65-1.97 (m, 4H), 2.17-2.31 (m, 4H), 2.92-3.33 (m, 1H, two separate signals of rotamers), 4.19-4.76 (m, 1H, two separate signals of rotamers), 5.73-6.39 (m, 1H, two separate signals of rotamers), 6.83 (brs, 1H), 7.04 (m, 2H), 8.05 (s, 1H), 8.41 (s, 1H), 8.40 (m, 1H), 9.39 (s, 1H).

LCMS(ESI): [M+1]$^+$ m/z: calcd 470.5; found 471.2; Rt=1.495 min.

Step 2. Synthesis of tert-butyl N-[5-[[2-[(2S,5S)-2-(4-fluorophenyl)-5-methyl-1-piperidyl]-2-oxo-acetyl]amino]-3-methyl-2-pyridyl]carbamate, Tert-butyl N-[5-[[2-[(2R,5S)-2-(4-fluorophenyl)-5-methyl-1-piperidyl]-2-oxo-acetyl]amino]-3-methyl-2-pyridyl]carbamate, Tert-butyl N-[5-[[2-[(2R,5R)-2-(4-fluorophenyl)-5-methyl-1-piperidyl]-2-oxo-acetyl]amino]-3-methyl-2-pyridyl]carbamate and Tert-butyl N-[5-[[2-[(2S,5R)-2-(4-fluorophenyl)-5-methyl-1-piperidyl]-2-oxo-acetyl]amino]-3-methyl-2-pyridyl]carbamate A mixture of stereoisomer was separated in the following conditions: IC (250*30, 5 mkm), Hexane-IPA-MeOH, 70-15-15, 13 ml/min.

RT for tert-butyl N-[5-[[2-[(2R,5S)-2-(4-fluorophenyl)-5-methyl-1-piperidyl]-2-oxo-acetyl]amino]-3-methyl-2-pyridyl]carbamate peak 1 (P1)=23.601 min RT for tert-butyl N-[5-[[2-[(2S,5R)-2-(4-fluorophenyl)-5-methyl-1-piperidyl]-2-oxo-acetyl]amino]-3-methyl-2-pyridyl]carbamate peak 2 (P2)=30.270 min Minor cis fractions are at RT 20.5 min and 28.5 min.

tert-butyl N-[5-[[2-[(2R,5S)-2-(4-fluorophenyl)-5-methyl-1-piperidyl]-2-oxo-acetyl]amino]-3-methyl-2-pyridyl]carbamate peak 1(P1) was used for preparation of Compound 242. Analytical data for this fraction are given below:

LCMS(ESI): [M+1]$^+$ m/z: calcd 470.5; found 472.0; Rt=5.536 min.

RT (IC, Hexane-IPA-MeOH, 70-15-15, 0.6 ml/min) =27.123 min tert-butyl N-[5-[[2-[(2S,5R)-2-(4-fluorophenyl)-5-methyl-1-piperidyl]-2-oxo-acetyl]amino]-3-methyl-2-pyridyl]carbamate Peak 2(P2) was used for preparation of Compound 233

LCMS(ESI): [M+1]$^+$ m/z: calcd 470.5; found 472.0; Rt=5.529 min.

RT (IC, Hexane-IPA-MeOH, 70-15-15, 0.6 ml/min)=36.392 min.

Step 3. Synthesis of N-(6-amino-5-methyl-3-pyridyl)-2-[(2S,5R)-2-(4-fluorophenyl)-5-methyl-1-piperidyl]-2-oxo-acetamide (Compound 233)

To a solution of tert-butyl N-[5-[[2-[(2S,5R)-2-(4-fluorophenyl)-5-methyl-1-piperidyl]-2-oxo-acetyl]amino]-3-methyl-2-pyridyl]carbamate (32.43 mg, 68.92 μmol) in dioxane (1 mL) was added Hydrogen chloride solution 40 M in dioxane (12.56 mg, 344.61 μmol, 15.71 μL) at 21° C. The resulting mixture was left to stir for 2 hr. The resulting mixture was evaporated to dryness and subjected to HPLC (C18, H$_2$O-ACN, 33-50% ACN, 30 ml/min). N-(6-amino-5-methyl-3-pyridyl)-2-[(2S,5R)-2-(4-fluorophenyl)-5-methyl-1-piperidyl]-2-oxo-acetamide (13.7 mg, 36.99 μmol, 53.66% yield) was obtained as a beige solid.

$^1$NMR (600 MHz, DMSO-d$_6$) δ 0.97-1.04 (m, 3H), 1.24-1.37 (m, 1H), 1.58-1.71 (m, 1H), 1.82-1.91 (m, 1H), 1.95-2.03 (m, 4H), 2.12-2.26 (m, 1H), 2.67-3.19 (m, 1H), 3.41-4.02 (m, 1H), 5.10-5.56 (m, 1H), 5.57-5.65 (m, 2H), 7.17-7.22 (m, 2H), 7.30-7.39 (m, 2H), 7.43-7.51 (m, 1H), 7.92-8.04 (m, 1H), 10.43-10.53 (m, 1H).

LCMS(ESI): [M+1]$^+$ m/z: calcd 370.2; found 371.2; Rt=2.774 min.

Step 3. Synthesis of N-(6-amino-5-methyl-3-pyridyl)-2-[(2R,5S)-2-(4-fluorophenyl)-5-methyl-1-piperidyl]-2-oxo-acetamide (Compound 242)

To a solution of tert-butyl N-[5-[[2-[(2R,5S)-2-(4-fluorophenyl)-5-methyl-1-piperidyl]-2-oxo-acetyl]amino]-3-methyl-2-pyridyl]carbamate (34.38 mg, 73.07 μmol) in dioxane (1 mL) was added Hydrogen chloride solution 40 M in dioxane (13.32 mg, 365.33 μmol, 16.65 μL) at 21° C. The resulting mixture was left to stir for 2 hr. The resulting mixture was evaporated to dryness and subjected to HPLC (C18, H$_2$O-ACN, 34-51% ACN, 30 ml/min). N-(6-amino-5-methyl-3-pyridyl)-2-[(2R,5S)-2-(4-fluorophenyl)-5-methyl-1-piperidyl]-2-oxo-acetamide (16.5 mg, 44.54 μmol, 60.96% yield) was obtained as a beige solid.

$^1$H NMR (600 MHz, DMSO-d$_6$) δ 0.92-1.05 (m, 3H), 1.26-1.38 (m, 1H), 1.60-1.69 (m, 1H), 1.80-1.90 (m, 1H), 1.95-2.10 (m, 4H), 2.12-2.25 (m, 1H), 2.66-3.18 (m, 1H), 3.41-4.03 (m, 1H), 5.05-5.56 (m, 1H), 5.57-6.08 (m, 2H), 6.94-7.24 (m, 2H), 7.28-7.40 (m, 2H), 7.42-7.50 (m, 1H), 7.62-8.08 (m, 1H), 9.69-10.55 (m, 1H).

LCMS(ESI): [M+1]$^+$ m/z: calcd 368.4; found 369.2; Rt=2.787 min.

Example 3. The Synthesis of 2-(5,5-dimethyl-2-phenyl-1-piperidyl)-N-(5-methyl-3-pyridyl)-2-oxo-acetamide (Compound 146), N-(6-amino-5-methyl-3-pyridyl)-2-[(2S,5R)-5-methyl-2-(3-pyridyl)-1-piperidyl]-2-oxo-acetamide (Compound 301) and Step 5: Synthesis of N-(6-amino-5-methyl-3-pyridyl)-2-[(2S,5R)-5-methyl-2-(3-pyridyl)-1-piperidyl]-2-oxo-acetamide (Compound 309)
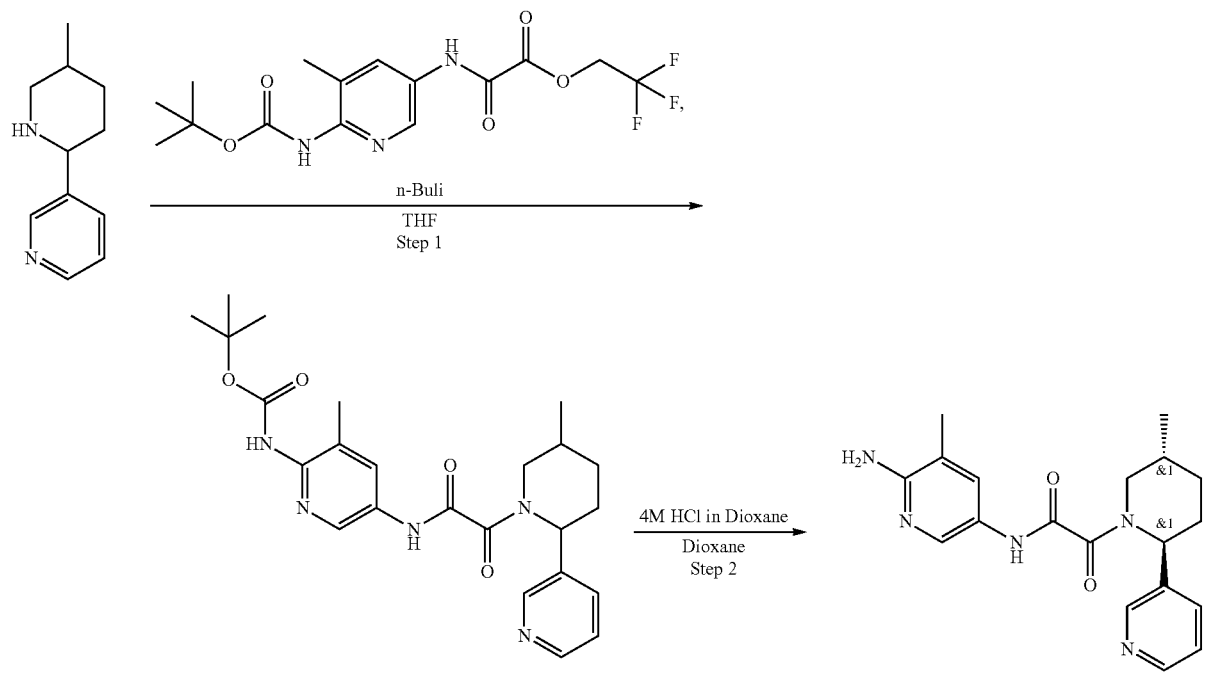
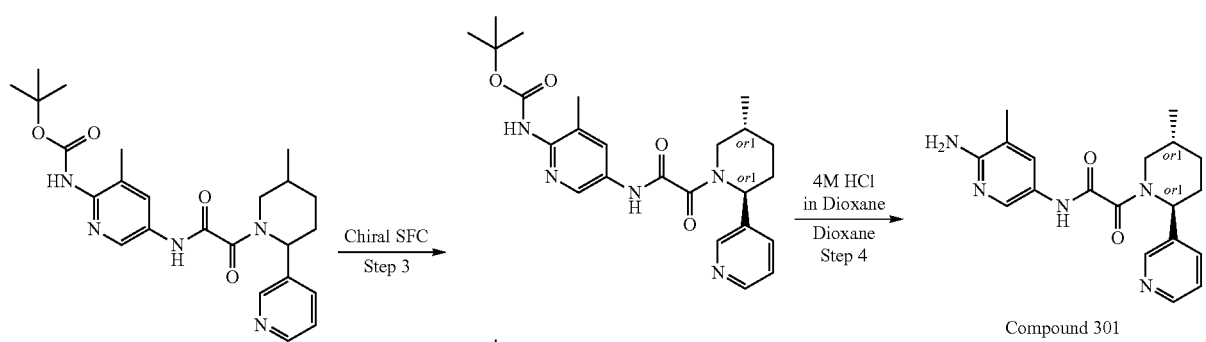
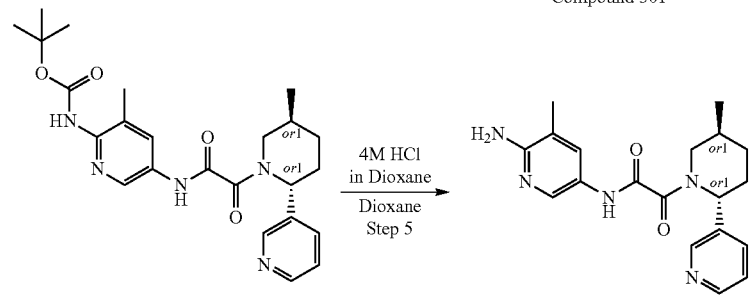

Step 1: Synthesis of tert-butyl N-[3-methyl-5-[[2-[5-methyl-2-(3-pyridyl)-1-piperidyl]-2-oxo-acetyl]amino]-2-pyridyl]carbamate To a solution of 3-(5-methyl-2-piperidyl)pyridine (0.2 g, 1.13 mmol) in THF (10 mL) was added n-butyllithium (948.04 mg, 3.40 mmol, 1.37 mL, 23% purity) at −78° C. under Ar atmosphere. After 15 min, 2,2,2-trifluoroethyl 2-[[6-(tert-butoxycarbonylamino)-5-methyl-3-pyridyl]amino]-2-oxo-acetate (428.14 mg, 1.13 mmol) was added in one portion. The resulting mixture was warmed to rt, quenched with NH$_4$Cl aq solution, extracted with EtOAc, dried over Na$_2$SO$_4$, evaporated and subjected to HPLC (2-7 30-55% ACN, 30 ML/MIN; SUNFIRE C18, 100*19). tert-butyl N-[3-methyl-5-[[2-[5-methyl-2-(3-pyridyl)-1-piperidyl]-2-oxo-acetyl]amino]-2-pyridyl]carbamate (0.1277 g, 281.57 μmol, 24.81% yield) was obtained as an off-white solid.

LCMS(ESI): [M+H]$^+$ m/z: calcd 453.2; found 454.2; Rt=1.063 min.

Step 2: Synthesis of tert-butyl N-[3-methyl-5-[[2-[5-methyl-2-(3-pyridyl)-1-piperidyl]-2-oxo-acetyl]amino]-2-pyridyl]carbamate (Compound 146)

To a solution of tert-butyl N-[3-methyl-5-[[2-[5-methyl-2-(3-pyridyl)-1-piperidyl]-2-oxo-acetyl]amino]-2-pyridyl]carbamate (97.7 mg, 215.42 μmol) in dioxane (1 mL) was added Hydrogen chloride solution 40 M in dioxane (78.54 mg, 2.15 mmol, 98.18 μL) at 21° C. The resulting mixture was left to stir for 1 hr. The reaction progress was monitored by HNMR. The precipitate was filtered off, washed with MTBE and dried under high vacuum (0.3 mbar) to give N-(6-amino-5-methyl-3-pyridyl)-2-[(2S,5R)-5-methyl-2-(3-pyridyl)-1-piperidyl]-2-oxo-acetamide (8 mg, 22.64 μmol, 10.51% yield) as a yellow solid.

$^1$H NMR (Chloroform-d, 400 MHz): δ (ppm) 0.84 (m, 1H), 1.08 (m, 3H), 1.42 (m, 1H), 1.79 (m, 2H), 2.00 (m, 1H), 2.11 (m, 3H), 2.19 (m, 1H), 3.10 (dd, 1H), 4.60 (m, 3H), 6.15 (m, 1H), 7.29 (m, 1H), 7.60 (dd, 1H), 7.71 (s, 1H), 8.03 (m, 1H), 8.51 (m, 1H), 8.57 (m, 1H), 9.18 (m, 1H)

LCMS(ESI): [M+H]$^+$ m/z: calcd 353.4; found 354.4; Rt=0.710 min.

Step 3: Chiral Purification of Tert-butyl N-[3-methy-5-[[2-[(2S,5R)-5-methyl-2-(3-pyridyl)-1-piperidyl]-2-oxo-acetyl]amino]-2-pyridyl]carbamate and Tert-butyl N-[3-methy-5-[[2-[(2R,5S)-5-methyl-2-(3-pyridyl)-1-piperidyl]-2-oxo-acetyl]amino]-2-pyridyl]carbamate tert-butyl N-[3-methyl-5-[[2-[5-methyl-2-(3-pyridyl)-1-piperidyl]-2-oxo-acetyl]amino]-2-pyridyl]carbamate (Compound 146, 75.8 mg) was subjected to chiral HPLC (Column: AD, 250×30 mm, 20 um; eluent: MeOH; flow rate: 32 mL/min) to get tert-butyl N-[3-methyl-5-[[2-[(2S,5R)-5-methyl-2-(3-pyridyl)-1-piperidyl]-2-oxo-acetyl]amino]-2-pyridyl]carbamate (17.25 mg) and tert-butyl N-[3-methyl-5-[[2-[(2R,5S)-5-methyl-2-(3-pyridyl)-1-piperidyl]-2-oxo-acetyl]amino]-2-pyridyl]carbamate (17.9 mg) as white solids.

tert-butyl N-[3-methyl-5-[[2-[(2S,5R)-5-methyl-2-(3-pyridyl)-1-piperidyl]-2-oxo-acetyl]amino]-2-pyridyl]carbamate LCMS(ESI): [M+Boc]$^+$ m/z: calcd 453.2; found 354.2; Rt=3.905 min.

Chiral HPLC: Rt=10.33 min (Column: IC; eluent: CO$_2$/MeOH, 60/40; flow rate: 2 mL/min).

tert-butyl N-[3-methyl-5-[[2-[(2R,5S)-5-methyl-2-(3-pyridyl)-1-piperidyl]-2-oxo-acetyl]amino]-2-pyridyl]carbamate LCMS(ESI): [M+Boc]$^+$ m/z: calcd 453.2; found 354.2; Rt=3.908 min.

Chiral HPLC: Rt=12.42 min (Column: IC; eluent: CO$_2$/MeOH, 60/40; flow rate: 2 mL/min).

Step 4: Synthesis of N-(6-amino-5-methyl-3-pyridyl)-2-[(2S,5R)-5-methyl-2-(3-pyridyl)-1-piperidyl]-2-oxo-acetamide (Compound 301)

To a stirring solution of tert-butyl N-[3-methyl-5-[[2-[(2S,5R)-5-methyl-2-(3-pyridyl)-1-piperidyl]-2-oxo-acetyl]amino]-2-pyridyl]carbamate (17.25 mg, 38.03 μmol) in dioxane (2 mL) was added 4 M Hydrogen chloride in dioxane (6.93 mg, 190.17 μmol, 8.67 μL) at 21° C. The resulting reaction mixture was allowed to stir at the same temperature for 2 hours. Upon completion, the reaction mixture was concentrated under reduced pressure and the crude product was purified by HPLC (Eluent: 30-80%, water—MeOH (NH$_3$); flow rate: 30 mL/min; loading pump: 4 mL/min, MeOH; column: X-Bridge 19*100 mm, 5 um) to get N-(6-amino-5-methyl-3-pyridyl)-2-[(2S,5R)-5-methyl-2-(3-pyridyl)-1-piperidyl]-2-oxo-acetamide (Compound 301, 6.9 mg, 19.52 μmol, 51.33% yield) as a beige solid.

$^1$H NMR (DMSO-d$_6$, 500 MHz): δ (ppm) 0.98-1.10 (m, 3H), 1.29-1.40 (m, 1H), 1.62-1.72 (m, 1H), 1.85-1.96 (m, 1H), 1.98-2.05 (m, 3H), 2.05-2.17 (m, 1H), 2.17-2.32 (m, 1H), 2.73-3.25 (m, 1H), 3.48-4.08 (m, 1H), 5.22-5.68 (m, 3H), 7.38-7.52 (m, 2H), 7.66-7.81 (m, 1H), 7.95-8.09 (m, 1H), 8.46-8.53 (m, 1H), 8.53-8.61 (m, 1H), 10.48-10.61 (m, 1H).

LCMS(ESI): [M+H]$^+$ m/z: calcd 353.2; found 354.2; Rt=0.783 min.

Step 5: Synthesis of N-(6-amino-5-methyl-3-pyridyl)-2-[(2S,5R)-5-methyl-2-(3-pyridyl)-1-piperidyl]-2-oxo-acetamide (Compound 309)

To a stirring solution of tert-butyl N-[3-methyl-5-[[2-[(2R,5S)-5-methyl-2-(3-pyridyl)-1-piperidyl]-2-oxo-acetyl]amino]-2-pyridyl]carbamate (17.9 mg, 39.47 μmol) in dioxane (2 mL) was added 4 M Hydrogen chloride in dioxane (7.20 mg, 197.34 μmol, 8.99 μL) at 21° C. The resulting reaction mixture was allowed to stir at the same temperature for 2 hours. Upon completion, the reaction mixture was concentrated under reduced pressure and the crude product was purified by HPLC (Eluent: 30-80%, water—MeOH (NH$_3$); flow rate: 30 mL/min; loading pump: 4 mL/min, MeOH; column: X-Bridge 19*100 mm, 5 um) to get N-(6-amino-5-methyl-3-pyridyl)-2-[(2S,5R)-5-methyl-2-(3-pyridyl)-1-piperidyl]-2-oxo-acetamide (Compound 309, 6.8 mg, 19.24 μmol, 48.75% yield) as a beige solid.

$^1$H NMR (DMSO-d$_6$, 500 MHz): δ (ppm) 1.01-1.05 (m, 3H), 1.31-1.40 (m, 1H), 1.62-1.70 (m, 1H), 1.84-1.91 (m, 1H), 1.99-2.05 (m, 3H), 2.13-2.32 (m, 2H), 2.72-3.20 (m, 1H), 3.38-4.10 (m, 1H), 5.24-5.67 (m, 3H), 7.38-7.44 (m, 1H), 7.44-7.52 (m, 1H), 7.69-7.78 (m, 1H), 7.95-8.06 (m, 1H), 8.46-8.53 (m, 1H), 8.53-8.60 (m, 1H), 10.40-10.60 (m, 1H).

LCMS(ESI): [M+H]$^+$ m/z: calcd 353.2; found 354.2; Rt=0.783 min.

Example 4. The Synthesis of 5-[[2-[2-(2-methylpyrazol-3-yl)-1-piperidyl]-2-oxo-acetyl]amino]pyridine-3-carboxamide (Compound 26)

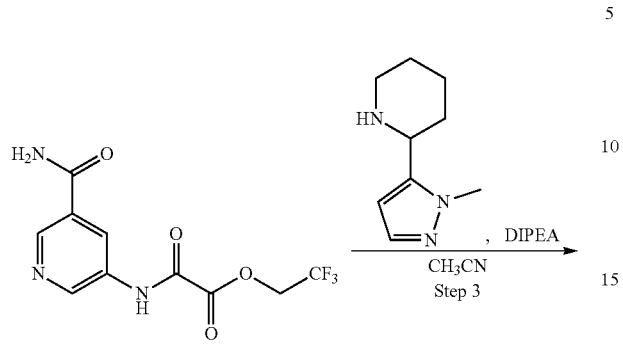

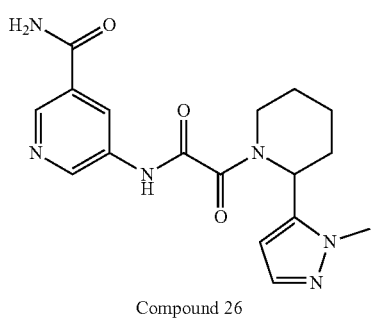

Compound 26

Step 1: Synthesis of 5-[[2-[2-(2-methylpyrazol-3-yl)-1-piperidyl]-2-oxo-acetyl]amino]pyridine-3-carboxamide (Compound 26)

2,2,2-trifluoroethyl 2-[(5-carbamoyl-3-pyridyl)amino]-2-oxo-acetate (0.2 g, 549.48 μmol), 2-(2-methylpyrazol-3-yl)piperidine (55.41 mg, 274.74 μmol, HCl) and DIPEA (53.26 mg, 412.11 μmol, 71.78 μL) were mixed together in CH$_3$CN (2 mL). The resulting reaction mixture was heated in a sealed tube at 100° C. for 12 hours. After 12 hours, the reaction mixture was concentrated under reduced pressure and the obtained crude product was purified by reverse phase HPLC (Eluent: CH$_3$CN 10-30%, 0-5 min, water-CH$_3$CN, flow rate: 30 mL/min, loading pump: 4 mL/min CH$_3$CN; column: SunFire C18 100*19 mm, 5 um) and freeze dried to obtain pure product 5-[[2-[2-(2-methylpyrazol-3-yl)-1-piperidyl]-2-oxo-acetyl]amino]pyridine-3-carboxamide (3.9 mg, 10.94 μmol, 3.98% yield) as light-yellow solid.

$^1$H NMR (CDCl$_3$, 400 MHz): δ (ppm) 1.82 (m, 3H), 2.03 (m, 2H), 2.20 (m, 1H), 3.03 (m, 1H), 3.85 (m, 3H), 4.68 (m, 1H), 5.94 (m, 2H), 6.34 (m, 2H), 7.43 (m, 1H), 8.62 (m, 1H), 8.81 (m, 1H), 8.97 (m, 1H), 9.69 (m, 1H).

LCMS(ESI): [M+H]$^+$ m/z: calcd 356.2; found 357.2; Rt=0.858 min.

Example 5. The Synthesis of 5-[[2-oxo-2-(2-phenyl-1-piperidyl)acetyl]amino]pyridine-3-carboxamide (Compound 29)

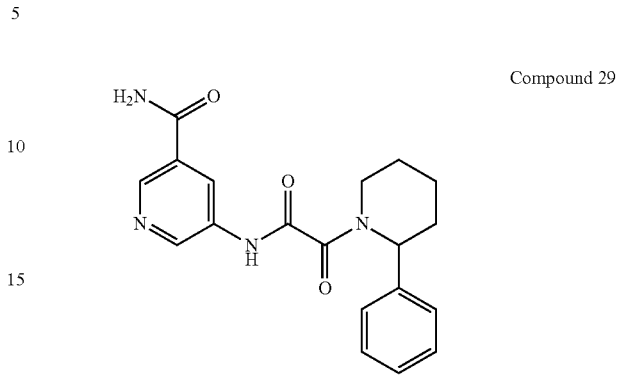

Compound 29

The compound was prepared in a similar manner to Example 4

$^1$H NMR (600 MHz, DMSO-d$_6$) δ 1.44 (m, 2H), 1.61 (m, 2H), 1.86 (m, 1H), 2.47 (m, 1H), 2.89 (m, 1H), 4.06 (m, 1H), 5.48 (m, 1H), 7.28 (m, 1H), 7.34 (m, 2H), 7.39 (m, 2H), 7.59 (m, 1H), 8.15 (m, 1H), 8.49 (m, 1H), 8.76 (m, 1H), 8.87 (m, 1H), 11.26 (m, 1H).

LCMS(ESI): [M+H]$^+$ m/z: calcd 352.3; found 353.2; Rt=1.147 min.

Example 6. Synthesis of rac-2-[(2r,5s)-5-methyl-2-(m-tolyl)-1-piperidyl]-N-(5-methyl-3-pyridyl)-2-oxo-acetamide (Compound 8) and Separation to 2-[(2S,5R)-5-methyl-2-(m-tolyl)-1-piperidyl]-N-(5-methyl-3-pyridyl)-2-oxo-acetamide (Compound 11) and 2-[(2R,5S)-5-methyl-2-(m-tolyl)-1-piperidyl]-N-(5-methyl-3-pyridyl)-2-oxo-acetamide Compound 10

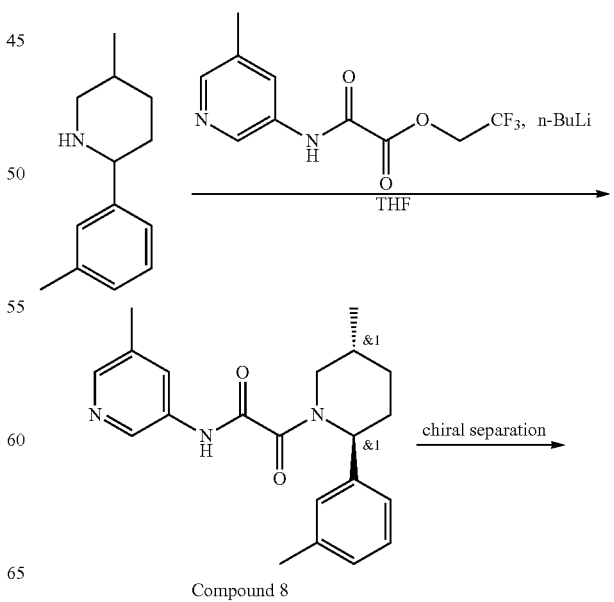

Compound 8

-continued

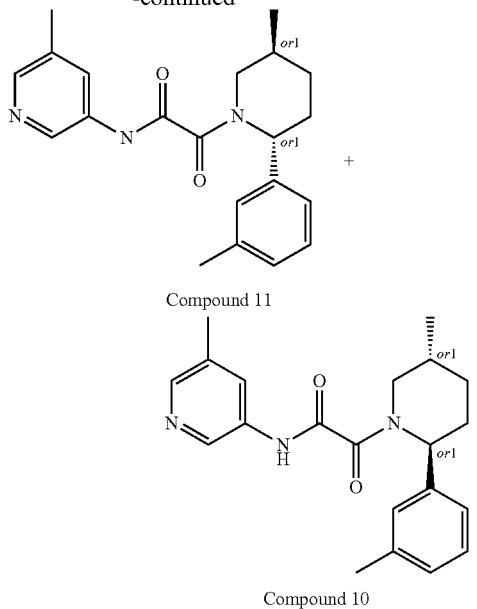

Compound 11

Compound 10

Step 1. Synthesis of rac-2-[(2R,5S)-5-methyl-2-(m-tolyl)-1-piperidyl]-N-(5-methyl-3-pyridyl)-2-oxo-acetamide (Compound 8)

To a stirred solution of 5-methyl-2-(m-tolyl)piperidine (0.2 g, 1.06 mmol) in THF (20 mL) at −78° C., n-butyllithium (2.5 M in Hexane, 135.35 mg, 2.11 mmol, 0.84 mL) was added dropwise under argon atmosphere. The resulting solution was stirred at the same temperature for 5 minutes. After 5 minutes, 2,2,2-trifluoroethyl 2-[(5-methyl-3-pyridyl)amino]-2-oxo-acetate (277.01 mg, 1.06 mmol) was added to the solution in one portion. The resulting reaction mixture was allowed to warm to room temperature and stirred for 12 hours at the same temperature. After 12 hours, the reaction mixture was quenched with saturated NH$_4$Cl aq. solution. The resulting mixture was evaporated to dryness. The obtained residue (0.8 g) was purified by HPLC to obtain rac-2-[(2R,5S)-5-methyl-2-(m-tolyl)-1-piperidyl]-N-(5-methyl-3-pyridyl)-2-oxo-acetamide (Compound 8, 0.045 g, 128.04 μmol, 12.12% yield) as yellow solid.

$^1$H NMR (DMSO-d$_6$, 400 MHz): δ (ppm) 1.21 (m, 3H), 1.46 (m, 1H), 1.63 (m, 2H), 1.87 (m, 1H), 2.26 (s, 1H), 2.31 (s, 2H), 2.62 (m, 7.6H), 2.98 (t, 0.4H), 3.63 (d, 0.6H), 4.30 (d, 0.4H), 5.10 (s, 0.4H), 5.64 (s, 0.6H), 7.24 (m, 4H), 7.89 (s, 0.4H), 7.97 (s, 0.6H), 8.15 (s, 0.4H), 8.20 (s, 0.6H), 8.55 (s, 0.4H), 8.64 (s, 0.6H), 11.06 (s, 0.4H), 11.08 (s, 0.6H).

LCMS(ESI): [M+H]$^+$ m/z: calcd 351.2; found 352.4; Rt=3.361 min.

Step 2: Chiral Separation of 2-[(2S,5R)-5-methyl-2-(m-tolyl)-1-piperidyl]-N-(5-methyl-3-pyridyl)-2-oxo-acetamide and 2-[(2R,5S)-5-methyl-2-(m-tolyl)-1-piperidyl]-N-(5-methyl-3-pyridyl)-2-oxo-acetamide (Compound 11 and Compound 10 rac-2-[(2R,5S)-5-methyl-2-(m-tolyl)-1-piperidyl]-N-(5-methyl-3-pyridyl)-2-oxo-acetamide (Compound 8) was subjected to chiral chromatography (Column: OJ-H 250*20 mm, 5 um, Eluent: Hexane-MeOH-IPA, 70-15-15, flow rate: 12 mL/min) to give 2-[(2S,5R)-5-methyl-2-(m-tolyl)-1-piperidyl]-N-(5-methyl-3-pyridyl)-2-oxo-acetamide (Compound 11) and 2-[(2R,5S)-5-methyl-2-(m-tolyl)-1-piperidyl]-N-(5-methyl-3-pyridyl)-2-oxo-acetamide (Compound 10) as yellow solid.

2-[(2S,5R)-5-methyl-2-(m-tolyl)-1-piperidyl]-N-(5-methyl-3-pyridyl)-2-oxo-acetamide (Compound 11

$^1$H NMR (DMSO-d$_6$, 400 MHz): δ (ppm) 1.10 (m, 3H), 1.41 (t, 1H), 1.77 (m, 1H), 1.91 (m, 1H), 2.13 (m, 1H), 2.22 (m, 1H), 2.35 (m, 6H), 2.82 (d, 0.35H), 3.29 (d, 0.65H), 3.60 (d, 0.65H), 4.09 (d, 0.35H), 5.21 (s, 0.35H), 5.65 (s, 0.65H), 7.03 (m, 1H), 7.10 (m, 2H), 7.23 (m, 1H), 7.94 (s, 0.35H), 7.99 (s, 0.65H), 8.05 (s, 0.35H), 8.09 (s, 0.65H), 8.52 (s, 0.35H), 8.59 (s, 0.65H), 10.86 (s, 0.35H), 10.91 (s, 0.65H).

LCMS(ESI): [M+H]$^+$ m/z: calcd 351.2; found 352.0; Rt=4.962 min.

Chiral HPLC: Rt=23.37 min (Column: OJ-H; Eluent: Hexane-MeOH-IPA, 70-15-15; Flow Rate: 0.6 mL/min).

2-[(2R,5S)-5-methyl-2-(m-tolyl)-1-piperidyl]-N-(5-methyl-3-pyridyl)-2-oxo-acetamide (Compound 10)

$^1$H NMR (DMSO-d$_6$, 400 MHz): δ (ppm) 1.11 (m, 3H), 1.44 (m, 1H), 1.72 (m, 1H), 1.91 (m, 1H), 2.11 (m, 1H), 2.22 (m, 1H), 2.35 (m, 6H), 2.83 (d, 0.35H), 3.28 (d, 0.65H), 3.60 (d, 0.65H), 4.10 (d, 0.35H), 5.21 (s, 0.35H), 5.65 (s, 0.65H), 7.03 (m, 1H), 7.10 (m, 2H), 7.23 (m, 1H), 7.94 (s, 0.35H), 7.99 (s, 0.65H), 8.05 (s, 0.35H), 8.09 (s, 0.65H), 8.52 (s, 0.35H), 8.59 (s, 0.65H), 10.86 (s, 0.35H), 10.91 (s, 0.65H).

LCMS(ESI): [M+H]$^+$ m/z: calcd 351.2; found 352.0; Rt=4.966 min.

Chiral HPLC: Rt=9.77 min (Column: OJ-H; Eluent: Hexane-MeOH-IPA, 70-15-15; Flow Rate: 0.6 mL/min).

Example 7. Synthesis of 2-[(2S,5R)-2-(3,4-dimethylphenyl)-5-methyl-1-piperidyl]-N-(5-methyl-3-pyridyl)-2-oxo-acetamide and 2-[(2R,5S)-2-(3,4-dimethylphenyl)-5-methyl-1-piperidyl]-N-(5-methyl-3-pyridyl)-2-oxo-acetamide (Compound 21 and Compound 19

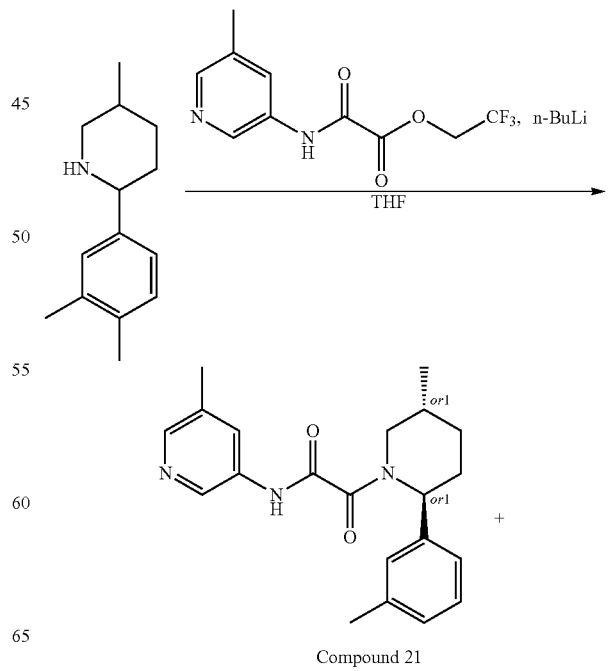

Compound 21

-continued

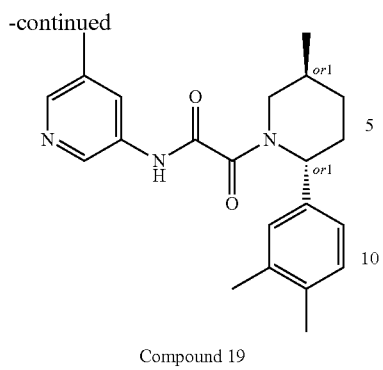

Compound 19

To a stirred solution of 2-(3,4-dimethylphenyl)-5-methyl-piperidine (0.7 g, 3.44 mmol) in THF (10 mL) at −78° C., n-butyllithium (2.5 M in Hexane 661.59 mg, 10.33 mmol, 4.13 mL) was added under argon atmosphere. The resulting mixture was stirred at the same temperature for 5 minutes. After 5 minutes, 2,2,2-trifluoroethyl 2-[(5-methyl-3-pyridyl)amino]-2-oxo-acetate (902.65 mg, 3.44 mmol) in THF (10 mL) was added to the reaction mixture. The resulting mixture was allowed to warm to room temperature and stirred for overnight at the same temperature. Upon completion, MeOH (5 mL) was added and the reaction mixture was evaporated in vacuo. The obtained crude residue was purified by reverse phase HPLC (50%, water-acetonitrile, 0.5-6.5 min; flow rate: 30 mL/min; loading pump: 4 mL/min acetonitrile; column: SunFire 100*19 mm, 5 um) and chiral column chromatography (Column: OJ-H 250*20 mm, Sum, Eluent: Hexane-MeOH-IPA, 70-15-15, flow rate: 15 mL/min) to give 2-[(2S,5R)-2-(3,4-dimethylphenyl)-5-methyl-1-piperidyl]-N-(5-methyl-3-pyridyl)-2-oxo-acetamide (Compound 21, 48 mg, 131.34 μmol, 3.81% yield) and 2-[(2R,5S)-2-(3,4-dimethylphenyl)-5-methyl-1-piperidyl]-N-(5-methyl-3-pyridyl)-2-oxo-acetamide (Compound 19, 55 mg, 150.49 μmol, 4.37% yield) as yellow solid.

[(2S,5R)-2-(3,4-dimethylphenyl)-5-methyl-1-piperidyl]-N-(5-methyl-3-pyridyl)-2-oxo-acetamide (Compound 21

$^1$H NMR (CDCl$_3$, 400 MHz): δ (ppm) 1.07 (m, 3H), 1.34 (m, 1H), 1.89 (m, 2H), 2.15 (m, 2H), 2.22 (m, 6H), 2.29 (m, 3H), 3.20 (m, 1H), 4.62 (m, 1H), 5.95 (m, 1H), 7.00 (m, 2H), 7.09 (m, 1H), 7.99 (s, 1H), 8.19 (m, 1H), 8.49 (m, 1H), 9.65 (m, 1H).
LCMS(ESI): [M+H]$^+$ m/z: calcd 365.2; found 366.2; Rt=1.397 min.
Chiral HPLC: Rt=6.57 min (Column: OJ-3; Eluent: Hexane-MeOH-IPA, 70-15-15; Flow Rate: 0.155 mL/min).

2-[(2R,5S)-2-(3,4-dimethylphenyl)-5-methyl-1-piperidyl]-N-(5-methyl-3-pyridyl)-2-oxo-acetamide Compound 19

$^1$H NMR (CDCl$_3$, 400 MHz): δ (ppm) 1.07 (m, 3H), 1.34 (m, 1H), 1.88 (m, 2H), 2.15 (m, 2H), 2.22 (m, 6H), 2.30 (m, 3H), 3.24 (m, 1H), 4.40 (m, 1H), 5.95 (m, 1H), 7.00 (m, 2H), 7.09 (m, 1H), 7.99 (s, 1H), 8.19 (m, 1H), 8.50 (m, 1H), 9.65 (m, 1H).
LCMS(ESI): [M+H]$^+$ m/z: calcd 365.2; found 366.2; Rt=1.397 min.
Chiral HPLC: Rt=33.27 min (Column: OJ-3; Eluent: Hexane-MeOH-IPA, 70-15-15; Flow Rate: 0.155 mL/min Example 8. The Synthesis of 2-[(2R,5S)-2-(3-chlorophenyl)-5-methyl-1-piperidyl]-N-(5-methyl-3-pyridyl)-2-oxo-acetamide (Compound 13 Compound 13), 2-((2R,5S)-2-(3-chlorophenyl)-5-methylpiperidin-1-yl)-N-(5-methylpyridin-3-yl)-2-oxoacetamide (Compound 90) and 2-((2S,5R)-2-(3-chlorophenyl)-5-methylpiperidin-1-yl)-N-(5-methylpyridin-3-yl)-2-oxoacetamide (Compound 87

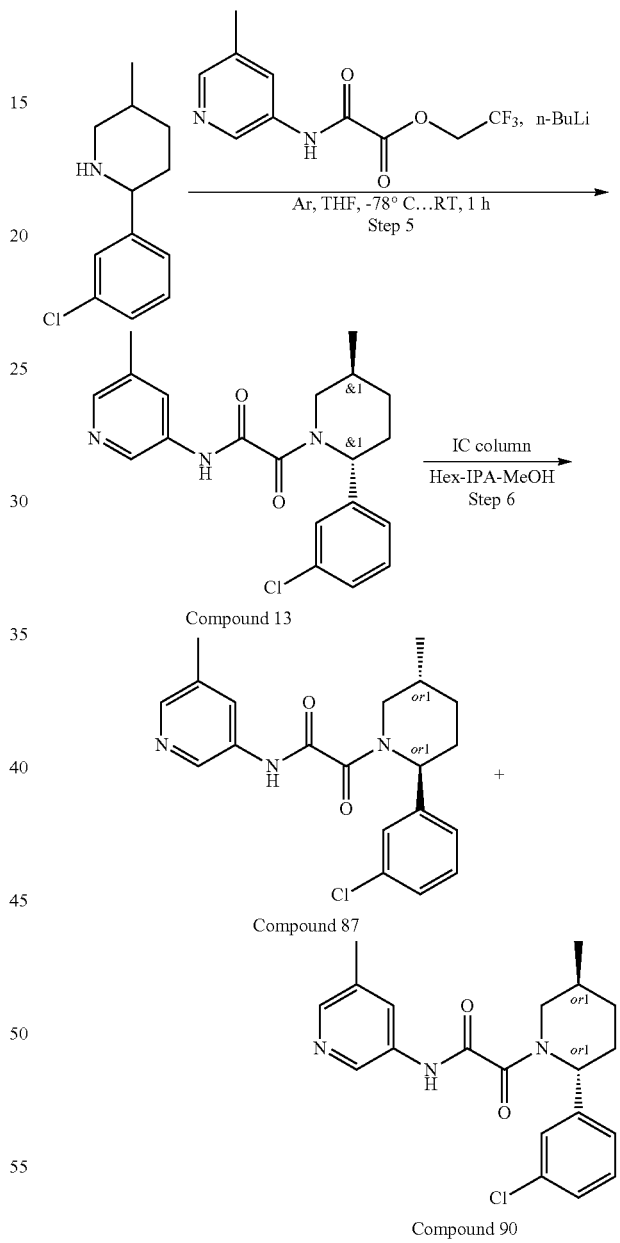

To a solution of 2,2,2-trifluoroethyl [(5-methylpyridin-3-yl)amino](oxo)acetate (625.10 mg, 2.38 mmol) in THF (10 mL) was added n-butyllithium (1.33 g, 4.77 mmol, 1.92 mL, 23% purity) at −78° C. under Ar atmosphere. After 15 min, 2-(3-chlorophenyl)-5-methyl-piperidine (0.5 g, 2.38 mmol) was added in one portion. The resulting mixture was warmed to rt, quenched with NH$_4$Cl aq solution, extracted with EtOAc, dried over Na$_2$SO$_4$, evaporated and subjected to HPLC (2-7 min 50-100% MeOH (0.1% ammonium hydroxide), 30 mL/min; column: YMC-ACTUS TRIAT C18 100*20 5 microM). 2-[(2R,5S)-2-(3-chlorophenyl)-5-methyl-1-piperidyl]-N-(5-methyl-3-pyridyl)-2-oxo-acetamide (6.7 mg, 18.02 μmol, 7.56e-1% yield) was obtained as light-yellow gum which slowly crystallized.

$^1$H NMR (400 MHz, CDCl$_3$) δ 0.81 (m, 1H), 1.09 (m, 3H), 1.37 (m, 1H), 1.84 (m, 1H), 1.97 (m, 1H), 2.20 (m, 2H), 2.33 (m, 3H), 3.15 (m, 1H), 4.53 (m, 1H), 6.09 (m, 1H), 7.16 (m, 1H), 7.22 (m, 1H), 7.29 (m, 2H), 8.00 (s, 1H), 8.22 (m, 1H), 8.48 (m, 1H).

LCMS(ESI): [M+H]$^+$ m/z: calcd 371.2; found 372.2; Rt=1.236 min.

Chiral separation was performed using IC chiralpak (250*20, 5 mkm) column; Hex-IPA-MeOH as a mobile phase, 70-15-15, 0.6 mL/min; Injection volume 5 mkL) affording 2-((2R,5S)-2-(3-chlorophenyl)-5-methylpiperidin-1-yl)-N-(5-methylpyridin-3-yl)-2-oxoacetamide (Compound 90) (56.84 mg, 152.85 μmol, 32.80% yield) and 2-((2S,5R)-2-(3-chlorophenyl)-5-methylpiperidin-1-yl)-N-(5-methylpyridin-3-yl)-2-oxoacetamide (Compound 87) (40.55 mg, 109.05 μmol, 23.40% yield).

2-((2S,5R)-2-(3-chlorophenyl)-5-methylpiperidin-1-yl)-N-(5-methylpyridin-3-yl)-2-oxoacetamide Compound 87

$^1$H NMR (600 MHz, DMSO-d$_6$) δ 1.02 (m, 3H), 1.33 (m, 1H), 1.64 (m, 1H), 1.89 (m, 1H), 2.04 (m, 1H), 2.19 (m, 1H), 2.27 (m, 3H), 3.02 (m, 1H), 3.74 (m, 1H), 5.35 (m, 1H), 7.33 (m, 3H), 7.43 (m, 1H), 7.90 (m, 1H), 8.16 (m, 1H), 8.57 (m, 1H), 11.06 (m, 1H).

LCMS(ESI): [M+4H]$^+$ m/z: calcd 371.2; found 375.3; Rt=5.04 min.

RT (IC, Hex-IPA-MeOH, 70-15-15, 0.6 mL/min)=30.688 min.

2-((2R,5S)-2-(3-chlorophenyl)-5-methylpiperidin-1-yl)-N-(5-methylpyridin-3-yl)-2-oxoacetamide Compound 90

$^1$H NMR (600 MHz, DMSO-d$_6$) δ 1.02 (m, 3H), 1.32 (m, 1H), 1.64 (m, 1H), 1.89 (m, 1H), 2.08 (m, 1H), 2.19 (m, 1H), 2.27 (m, 3H), 2.94 (m, 1H), 3.84 (m, 1H), 5.35 (m, 1H), 7.33 (m, 3H), 7.43 (m, 1H), 7.90 (m, 1H), 8.16 (m, 1H), 8.57 (m, 1H), 11.06 (m, 1H).

LCMS(ESI): [M+H]$^+$ m/z: calcd 371.2; found 372.3; Rt=5.03 min.

RT (IC, Hex-IPA-MeOH, 70-15-15, 0.6 mL/min)=20.398 min.

Example 9. Synthesis of 2-[(2S,5R)-5-methyl-2-(2-methyl-4-pyridyl)-1-piperidyl]-N-(5-methyl-3-pyridyl)-2-oxo-acetamide (Compound 14

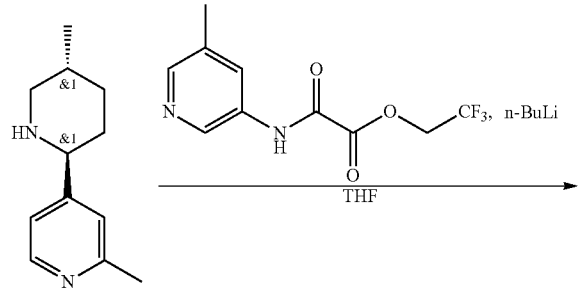

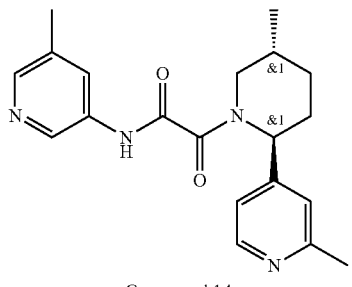

Compound 14

To a stirred solution of 2-methyl-4-(5-methyl-2-piperidyl)pyridine (0.187 g, 982.74 μmol) in THF (20 mL) at −78° C., n-butyllithium (2.5 M in Hexane, 125.90 mg, 1.97 mmol, 0.78 mL) was added under argon atmosphere. The resulting mixture was stirred at the same temperature for 5 minutes. After 5 minutes, 2,2,2-trifluoroethyl 2-[(5-methyl-3-pyridyl)amino]-2-oxo-acetate (257.66 mg, 982.74 μmol) was added in one portion. The resulting mixture was allowed to warm to room temperature and stirred for 12 hours at the same temperature. After 12 hours, the reaction mixture was quenched with saturated NH$_4$Cl aq solution and evaporated in vacuo. The crude product (1 g) was purified by reverse phase HPLC to obtain product 2-[(2S,5R)-5-methyl-2-(2-methyl-4-pyridyl)-1-piperidyl]-N-(5-methyl-3-pyridyl)-2-oxo-acetamide (0.058 g, 164.57 μmol, 16.75% yield) as a white solid.

$^1$H NMR (DMSO-d$_6$+CCl$_4$, 400 MHz): δ (ppm) 1.11 (d, 3H), 1.41 (m, 1H), 1.69 (m, 1H), 1.92 (m, 1H), 2.19 (m, 2H), 2.34 (m, 3H), 2.53 (m, 3H), 2.79 (m, 0.4H), 3.25 (m, 0.6H), 3.89 (m, 1H), 5.42 (m, 1H), 7.07 (m, 1H), 7.13 (m, 1H), 7.94 (m, 1H), 8.08 (m, 1H), 8.38 (m, 1H), 8.57 (m, 1H), 10.93 (m, 1H).

LCMS(ESI): [M+H]$^+$ m/z: calcd 352.2; found 353.2; Rt=1.923 min.

Example 10. The Synthesis of 2-[(2s,5r)-5-methyl-2-(p-tolyl)-1-piperidyl]-N-(5-methyl-3-pyridyl)-2-oxo-acetamide Compound 16 and 2-[(2R,53)-5-methyl-2-(p-tolyl)-1-piperidyl]-N-(5-methyl-3-pyridyl)-2-oxo-acetamide (Compound 12

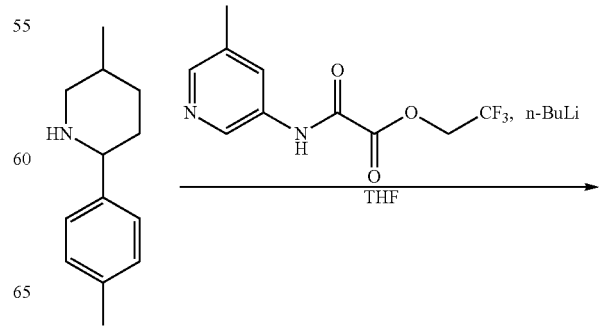

-continued

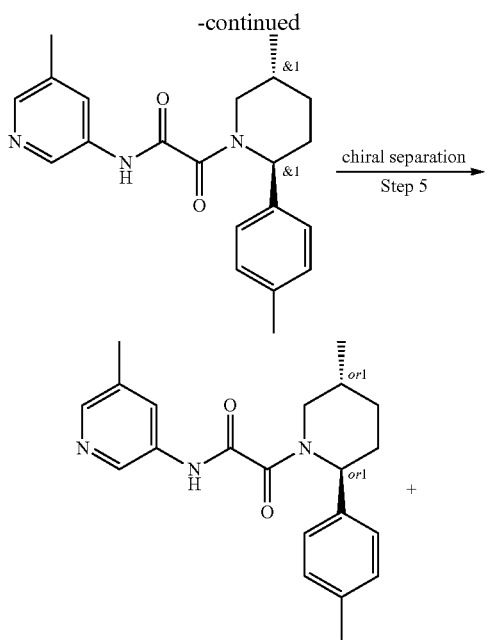

Compound 16

Compound 12

Step 1: Synthesis of rac-2-[(2S,5R)-5-methyl-2-(p-tolyl)-1-piperidyl]-N-(5-methyl-3-pyridyl)-2-oxo-acetamide To a stirred solution of 2,2,2-trifluoroethyl [(5-methylpyridin-3-yl)amino](oxo)acetate (1.39 g, 5.28 mmol) in THF (25 mL) at −78° C., n-butyllithium (2.5 M in Hexane, 2.94 g, 10.57 mmol, 4.25 mL) was added dropwise under argon atmosphere. The resulting solution was stirred at the same temperature for 15 minutes. After 15 minutes, 5-methyl-2-(p-tolyl)piperidine (1 g, 5.28 mmol) was added to the solution in one portion. The resulting reaction mixture was allowed to warm to room temperature and stirred for 1 hour at the same temperature. After 1 hour, the reaction mixture was quenched with saturated NH₄Cl aq. Solution and extracted with EtOAc. The organic layer was dried over Na₂SO₄, filtered and evaporated under reduced pressure. The crude product was purified by reverse phase HPLC (Eluent: CH₃CN, 50-55%, 2-7 min, flow rate: 30 mL/min; column: SunFire C18 100*19 mm, 5 uM) to obtain rac-2-[(2S,5R)-5-methyl-2-(p-tolyl)-1-piperidyl]-N-(5-methyl-3-pyridyl)-2-oxo-acetamide (0.0731 g, 208.00 μmol, 3.94% yield) as a light-yellow gum.

LCMS(ESI): [M+H]⁺ m/z: calcd 351.2; found 352.2; Rt=3.269 min.

Step 2: Chiral Separation of 2-[(2S,5R)-5-methyl-2-(p-tolyl)-1-piperidyl]-N-(5-methyl-3-pyridyl)-2-oxo-acetamide and 2-[(2R,5S)-5-methyl-2-(p-tolyl)-1-piperidyl]-N-(5-methyl-3-pyridyl)-2-oxo-acetamide (Compound 16 and Compound 12 rac-2-[(2S,5R)-5-methyl-2-(p-tolyl)-1-piperidyl]-N-(5-methyl-3-pyridyl)-2-oxo-acetamide (0.0621 g, 176.70 μmol) was subjected to chiral chromatography (Column: Chiralcel OJ-H 250*20 mm, 5 um, Eluent: Hexane-MeOH-IPA, 70-15-15, flow rate: 15 mL/min) to give 2-[(2S,5R)-5-methyl-2-(p-tolyl)-1-piperidyl]-N-(5-methyl-3-pyridyl)-2-oxo-acetamide (Compound 16, 30.5 mg) and 2-[(2R,5S)-5-methyl-2-(p-tolyl)-1-piperidyl]-N-(5-methyl-3-pyridyl)-2-oxo-acetamide (Compound 12, 23.4 mg) as an off-white solid.

2-[(2S,5R)-5-methyl-2-(p-tolyl)-1-piperidyl]-N-(5-methyl-3-pyridyl)-2-oxo-acetamide Compound 16

¹H NMR (CD₃OD, 400 MHz): δ (ppm) 1.12 (m, 6H), 1.40 (m, 1H), 1.87 (m, 2H), 2.28 (m, 3H), 2.37 (m, 3H), 3.52 (m, 1H), 3.96 (m, 1H), 5.47 (m, 1H), 7.20 (m, 4H), 7.90 (m, 1H), 8.17 (m, 1H), 8.57 (m, 1H).
LCMS(ESI): [M+H]⁺ m/z: calcd 351.2; found 352.2; Rt=1.218 min.
Chiral HPLC: Rt=13.72 min (Column: OJ-3; Eluent: Hexane-MeOH-IPA, 70-15-15; Flow Rate: 0.15 mL/min).

2-[(2R,5S)-5-methyl-2-(p-tolyl)-1-piperidyl]-N-(5-methyl-3-pyridyl)-2-oxo-acetamide Compound 12

¹H NMR (CD₃OD, 400 MHz): δ (ppm) 1.12 (m, 6H), 1.41 (m, 1H), 1.87 (m, 2H), 2.25 (m, 3H), 2.37 (m, 3H), 3.51 (m, 1H), 3.95 (m, 1H), 5.47 (m, 1H), 7.21 (m, 4H), 7.90 (m, 1H), 8.18 (m, 1H), 8.57 (m, 1H).
LCMS(ESI): [M+H]⁺ m/z: calcd 351.2; found 352.0; Rt=1.218 min.
Chiral HPLC: Rt=40.48 min (Column: OJ-3; Eluent: Hexane-MeOH-IPA, 70-15-15; Flow Rate: 0.15 mL/min).

Example 11. The Synthesis of rac-2-[(2S,5R)-2-(3-fluorophenyl)-5-methyl-1-piperidyl]-N-(5-methyl-3-pyridyl)-2-oxo-acetamide (Compound 70), 2-[(2S,5S)-2-(3-fluorophenyl)-5-methyl-1-piperidyl]-N-(5-methyl-3-pyridyl)-2-oxo-acetamide (Compound 1080), 2-[(2S,5R)-2-(3-fluorophenyl)-5-methyl-1-piperidyl]-N-(5-methyl-3-pyridyl)-2-oxo-acetamide (Compound 77), 2-[(2R,5S)-2-(3-fluorophenyl)-5-methyl-1-piperidyl]-N-(5-methyl-3-pyridyl)-2-oxo-acetamide (Compound 84), and 2-[(2R,5R)-2-(3-fluorophenyl)-5-methyl-1-piperidyl]-N-(5-methyl-3-pyridyl)-2-oxo-acetamide (Compound 93

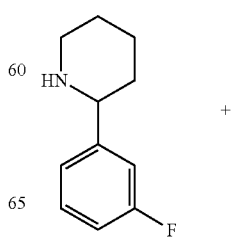

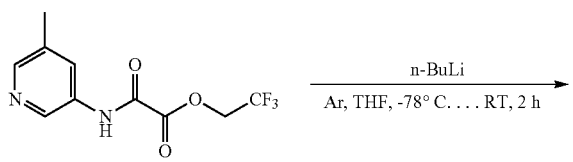

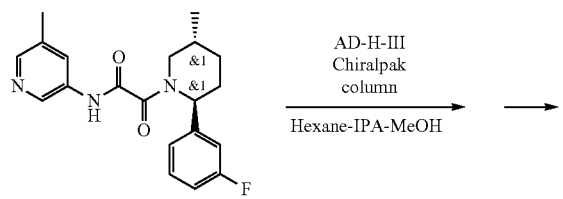

Compound 70

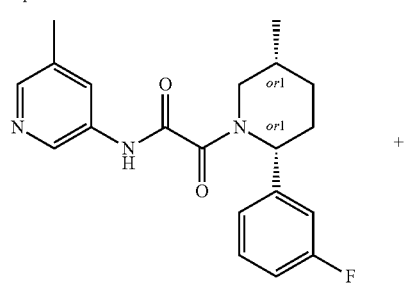

Compound 1080

+

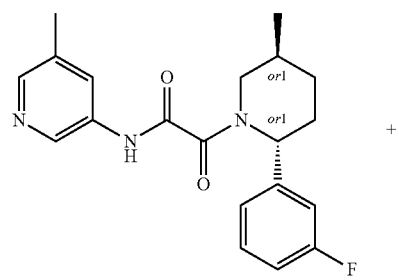

Compound 77

+

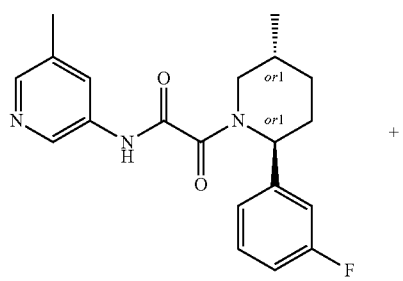

Compound 84

+

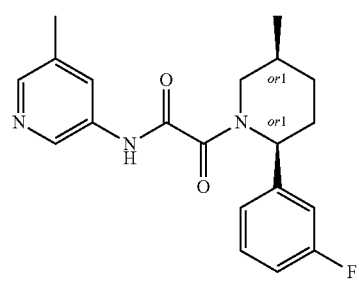

Compound 93

Step 1: The Synthesis of rac-2-[(2S,5R)-2-(3-fluorophenyl)-5-methyl-1-piperidyl]-N-(5-methyl-3-pyridyl)-2-oxo-acetamide (Compound 70

To a solution of 2,2,2-trifluoroethyl [(5-methylpyridin-3-yl)amino](oxo)acetate (406.99 mg, 1.55 mmol) in THF (50 mL) was added n-butyllithium (864.64 mg, 3.10 mmol, 1.25 mL, 23% purity) at −78° C. under Ar atmosphere. After 15 min, 2-(3-fluorophenyl)-5-methyl-piperidine (0.3 g, 1.55 mmol) was added in one portion. The resulting mixture was warmed to rt, quenched with NH$_4$Cl aq solution, extracted with EtOAc, dried over Na$_2$SO$_4$, evaporated and subjected to HPLC (SunFire C18 19*100 mm 5 mkm column; 2-7 min 40-65% MeCN, Flow 30 ml/min). After HPLC two fraction were obtained: 2-[2-(3-fluorophenyl)-5-methyl-1-piperidyl]-N-(5-methyl-3-pyridyl)-2-oxo-acetamide (81.6 mg, 229.60 μmol, 14.79% yield) as a mixture of diastereomers and 2-[(2S,5R)-2-(3-fluorophenyl)-5-methyl-1-piperidyl]-N-(5-methyl-3-pyridyl)-2-oxo-acetamide (9.9 mg, 27.86 μmol, 1.79% yield).

$^1$H NMR (500 MHz, DMSO-d$_6$) δ 1.02 (m, 3H), 1.31 (m, 1H), 1.63 (m, 1H), 1.88 (m, 1H), 2.06 (m, 1H), 2.20 (m, 1H), 2.27 (m, 3H), 3.24 (m, 1H), 3.84 (m, 1H), 5.36 (m, 1H), 7.15 (m, 3H), 7.44 (m, 1H), 7.90 (m, 1H), 8.16 (m, 1H), 8.62 (m, 1H), 11.04 (m, 1H).

LCMS(ESI): [M+H]$^+$ m/z: calcd 355.1; found 356.4; Rt=3.052 min.

Step 2: Chiral Separation of 2-[(2S,5R)-2-(3-fluorophenyl)-5-methyl-1-piperidyl]-N-(5-methyl-3-pyridyl)-2-oxo-acetamide Chiral separation of 2-[(2S,5R)-2-(3-fluorophenyl)-5-methyl-1-piperidyl]-N-(5-methyl-3-pyridyl)-2-oxo-acetamide was performed using AD-H—III (250*20, 5 mkm) Chiralpak column; Hexane-IPA-MeOH, 60-20-20 as a mobile phase; Flow 12 ml/min affording Compound 1080—2-[(2S,5S)-2-(3-fluorophenyl)-5-methyl-1-piperidyl]-N-(5-methyl-3-pyridyl)-2-oxo-acetamide (4.77 mg, 5.85%; RT=21.76 min), Compound 77—2-[(2S,5R)-2-(3-fluorophenyl)-5-methyl-1-piperidyl]-N-(5-methyl-3-pyridyl)-2-oxo-acetamide (27.41 mg, 33.62%; RT=33.70 min), Compound 84—2-[(2R,5S)-2-(3-fluorophenyl)-5-methyl-1-piperidyl]-N-(5-methyl-3-pyridyl)-2-oxo-acetamide (3.18 mg, 3.90%; RT=39.42 min), and Compound 93—2-[(2R,5R)-2-(3-fluorophenyl)-5-methyl-1-piperidyl]-N-(5-methyl-3-pyridyl)-2-oxo-acetamide (32.62 mg, 39.98%; RT=27.90 min).

2-[(2S,5S)-2-(3-fluorophenyl)-5-methyl-1-piperidyl]-N-(5-methyl-3-pyridyl)-2-oxo-acetamide Compound 1080

RT (OJ-H, Hexane-IPA-MeOH, 90-5-5, 0.6 ml/min)=21.760 min.

$^1$H NMR (500 MHz, CDCl$_3$) δ 0.88 (m, 3H), 1.27 (m, 1H), 1.75 (m, 2H), 1.88 (m, 1H), 2.06 (m, 1H), 2.43 (m, 3H), 2.61 (m, 1H), 4.67 (m, 1H), 6.17 (m, 1H), 6.99 (m, 2H), 7.09 (m, 1H), 7.37 (m, 1H), 8.21 (m, 1H), 8.28 (m, 1H), 8.73 (m, 1H), 9.63 (m, 1H).

LCMS(ESI): [M+H]$^+$ m/z: calcd 355.2; found 356.2; Rt=4.859 min.

2-[(2S,5R)-2-(3-fluorophenyl)-5-methyl-1-piperidyl]-N-(5-methyl-3-pyridyl)-2-oxo-acetamide Compound 77

RT (OJ-H, Hexane-IPA-MeOH, 90-5-5, 0.6 ml/min)=33.704 min.

¹H NMR (DMSO-d₆, 500 MHz): δ (ppm) 1.11 (m, 3H), 1.40 (m, 1H), 1.76 (m, 1H), 1.92 (m, 1H), 2.18 (m, 2H), 2.33 (m, 3H), 3.27 (m, 1H), 3.87 (m, 1H), 5.45 (m, 1H), 6.99 (m, 1H), 7.12 (m, 2H), 7.38 (m, 1H), 7.97 (m, 1H), 8.08 (m, 1H), 8.56 (m, 1H), 10.91 (m, 1H).

LCMS(ESI): [M+H]⁺ m/z: calcd 355.2; found 356.2; Rt=4.808 min.

2-[(2R,5S)-2-(3-fluorophenyl)-5-methyl-1-piperidyl]-N-(5-methyl-3-pyridyl)-2-oxo-acetamide Compound 84

RT (OJ-H, Hexane-IPA-MeOH, 90-5-5, 0.6 ml/min)=39.426 min.

¹H NMR (Chloroform-d, 500 MHz): δ (ppm) 0.88 (m, 3H), 1.27 (m, 1H), 1.75 (m, 2H), 2.06 (m, 1H), 2.34 (m, 1H), 2.43 (m, 3H), 2.60 (m, 1H), 4.60 (m, 1H), 6.17 (m, 1H), 6.99 (m, 2H), 7.08 (m, 1H), 7.37 (m, 1H), 8.22 (m, 1H), 8.29 (m, 1H), 8.75 (m, 1H), 9.66 (m, 1H).

LCMS(ESI): [M+H]⁺ m/z: calcd 355.2; found 356.0; Rt=4.705 min.

2-[(2R,5R)-2-(3-fluorophenyl)-5-methyl-1-piperidyl]-N-(5-methyl-3-pyridyl)-2-oxo-acetamide Compound 93

RT (OJ-H, Hexane-IPA-MeOH, 90-5-5, 0.6 ml/min)=27.991 min.

¹H NMR (500 MHz, DMSO-d₆) δ 1.10 (m, 3H), 1.41 (m, 1H), 1.78 (m, 1H), 1.92 (m, 1H), 2.22 (m, 2H), 2.33 (m, 3H), 2.80 (m, OH), 3.28 (m, 1H), 3.87 (m, 1H), 5.46 (m, 1H), 6.99 (m, 1H), 7.12 (m, 2H), 7.38 (m, 1H), 7.97 (m, 1H), 8.08 (m, 1H), 8.56 (m, 1H), 10.91 (m, 1H).

LCMS(ESI): [M+H]⁺ m/z: calcd 355.2; found 356.2; Rt=4.821 min.

Example 12. The Synthesis of 2-(5-methyl-2-(Thiophen-2-yl)piperidin-1-yl)-N-(5-methylpyridin-3-yl)-2-oxoacetamide (Compound 60, Compound 68, Compound 76

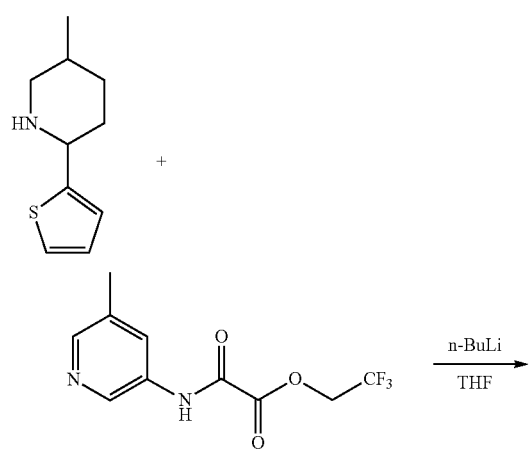

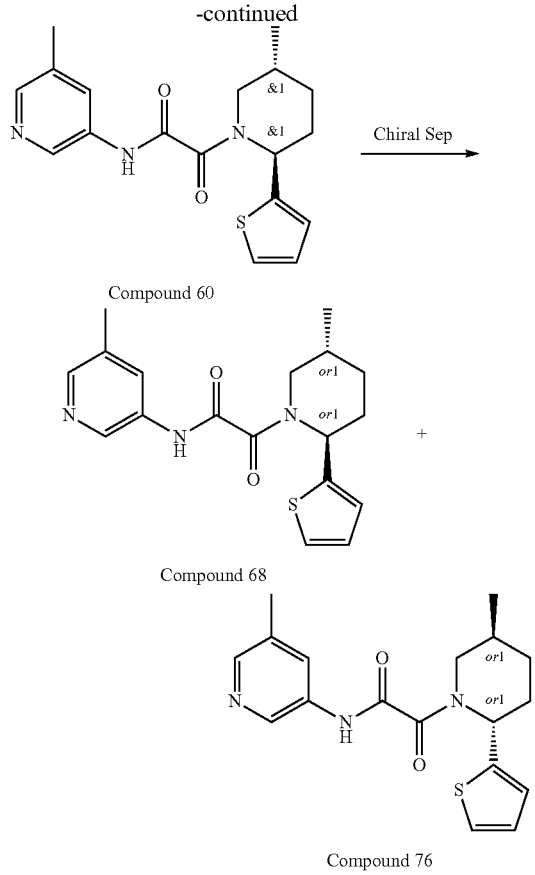

Step 1: Synthesis of rac-2-((2R,5S)-5-methyl-2-(Thiophen-2-yl)piperidin-1-yl)-N-(5-methylpyridin-3-yl)-2-oxoacetamide (Compound 60

To a solution of 2,2,2-trifluoroethyl [(5-methylpyridin-3-yl)amino](oxo)acetate (433.85 mg, 1.65 mmol) in THF (15 mL) n-butyllithium (921.70 mg, 3.31 mmol, 1.33 mL, 23% purity) was added at −78° C. under Ar atmosphere. After 15 min, 5-methyl-2-(2-thienyl)piperidine (0.3 g, 1.65 mmol) was added in one portion. The resulting mixture was warmed to rt, quenched with NH₄Cl aq solution, extracted with EtOAc, dried over Na₂SO₄, evaporated and subjected to HPLC (2-7 35-60% acn, 30 ml/min; sunfire C18 100*19, 5 uM). After HPLC 2 fraction of N-(5-methyl-3-pyridyl)-2-[(2S,5R)-5-methyl-2-(2-thienyl)-1-piperidyl]-2-oxo-acetamide (84.5 mg, 246.04 μmol, 14.87% yield) were obtained: 49.8 mg (98.98% purity) and 34.7 mg (96.38% purity).

¹H NMR (400 MHz, DMSO-d₆) δ (ppm) 1.02 (t, 3H), 1.45 (m, 1H), 1.89 (m, 2H), 2.06 (m, 2H), 2.29 (m, 3H), 2.78 (m, 1H), 3.65 (m, 1H), 5.64 (m, 1H), 7.05 (m, 2H), 7.50 (m, 1H), 7.94 (m, 1H), 8.18 (m, 1H), 8.62 (s, 1H), 11.05 (s, 1H).

LCMS(ESI): [M]⁺ m/z: calcd 343.4; found 344.2; Rt=3.273 min.

Step 2: Chiral Separation (Compound 68 and Compound 76

Purification on the chiral column was taken in the system Hex-IPA-MeOH, 70-15-15, 0.6 mL/min. Number of injections: 1, injection volume: 5 mkl. From 39 mg of racemate, 17.01 mg and 17.38 mg of the individual enantiomers were obtained.

2-((2R,5S)-5-methyl-2-(Thiophen-2-yl)piperidin-1-yl)-N-(5-methylpyridin-3-yl)-2-oxoacetamide Compound 68

Retention time: 17.81 min $^1$H NMR (500 MHz, DMSO-$d_6$) δ (ppm) 1.02 (m, 3H), 1.43 (m, 1H), 1.89 (m, 2H), 2.05 (m, 2H), 2.29 (m, 3H), 3.28 (m, 1H), 3.46 (m, 1H), 5.84 (m, 1H), 7.04 (m, 2H), 7.50 (m, 1H), 7.94 (m, 1H), 8.18 (m, 1H), 8.61 (m, 1H), 11.03 (s, 1H).

LCMS(ESI): [M]$^+$ m/z: calcd 343.4; found 344.2; Rt=4.460 min.

2-((2S,5R)-5-methyl-2-(Thiophen-2-yl)piperidin-1-yl)-N-(5-methylpyridin-3-yl)-2-oxoacetamide Compound 76

Retention time: 22.70 min $^1$H NMR (500 MHz, DMSO-$d_6$) δ (ppm) 1.02 (m, 3H), 1.43 (m, 1H), 1.88 (m, 2H), 2.05 (m, 2H), 2.29 (m, 3H), 3.36 (m, 1H), 3.44 (m, 1H), 5.83 (m, 1H), 7.04 (m, 2H), 7.49 (m, 1H), 7.94 (m, 1H), 8.18 (m, 1H), 8.61 (m, 1H), 11.03 (m, 1H).

LCMS(ESI): [M]$^+$ m/z: calcd 343.4; found 344.2; Rt=4.475 min.

Example 13. The Synthesis of rac-2-((2R,5)-2-(3-(1-acetylpiperidin-4-yl)phenyl)-5-methylpiperidin-1-yl)-N-(5-methylpyridin-3-yl)-2-oxoacetamide (Compound 44)

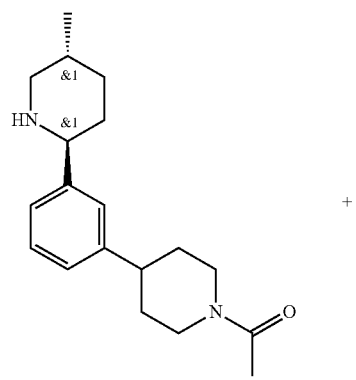

+

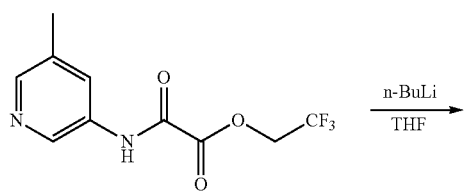

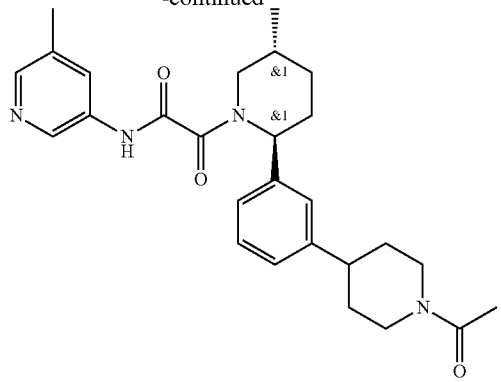

Compound 44

To a solution of 1-[4-[3-[(2S,5R)-5-methyl-2-piperidyl]phenyl]-1-piperidyl]ethanone (500.00 mg, 1.66 mmol) and 2,2,2-trifluoroethyl 2-[(5-methyl-3-pyridyl)amino]-2-oxoacetate (479.97 mg, 1.83 mmol) in THF (50 mL) was added n-butyllithium (1.16 g, 4.16 mmol, 1.67 mL, 23% purity) at −78° C. under Ar atmosphere. The resulting mixture was stirred for 15 min and warmed to rt, quenched with NH$_4$Cl aq solution, extracted with EtOAc, dried over Na$_2$SO$_4$, evaporated and subjected to HPLC (19_R1+FA 1-6 min 55-55% water-MeOH+FA, flow 30 ml/min (loading pump 4 ml/min MeOH+FA)) to obtain 2-[(2S,5R)-2-[3-(1-acetyl-4-piperidyl)phenyl]-5-methyl-1-piperidyl]-N-(5-methyl-3-pyridyl)-2-oxo-acetamide (7 mg, 15.13 μmol, 9.09e-1% yield).

$^1$H NMR (400 MHz, DMSO-$d_6$) δ (ppm) 1.12 (d, 3H), 1.41 (m, 1H), 1.54 (m, 2H), 1.82 (m, 4H), 2.04 (s, 3H), 2.26 (m, 2H), 2.36 (m, 3H), 2.78 (m, 2H), 3.15 (m, 2H), 3.61 (m, 1H), 3.93 (m, 1H), 4.61 (d, 1H), 5.55 (m, 1H), 7.27 (m, 4H), 8.06 (m, 1H), 8.11 (m, 1H), 8.61 (m, 1H), 10.91 (m, 1H).

LCMS(ESI): [M]$^+$ m/z: calcd 462.6; found 463.2; Rt=1.206 min.

Example 14. Synthesis of Rel-(R)-5-(2-(2-(1-methyl-1H-pyrazol-5-yl)piperidin-1-yl)-2-oxoacetamido)Nicotinamide (Compound 59) and Rel-(S)-5-(2-(2-(1-methyl-1H-pyrazol-5-yl)piperidin-1-yl)-2-oxoacetamido)Nicotinamide (Compound 46

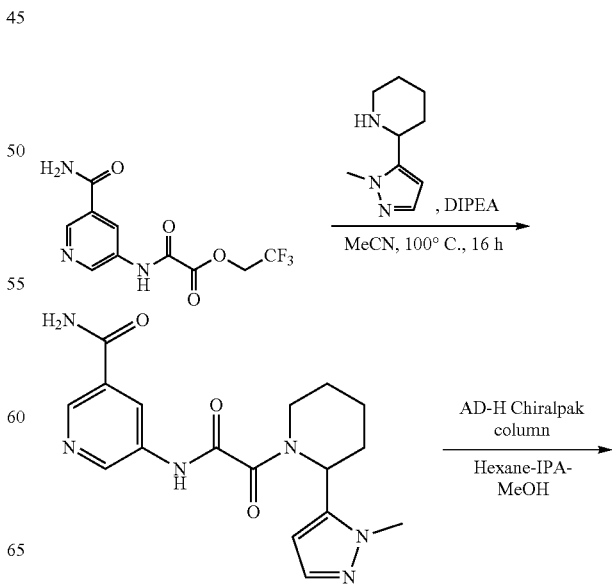

-continued

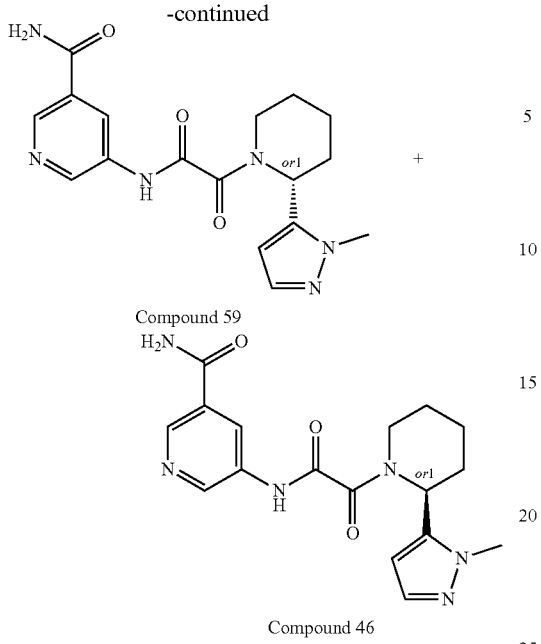

Compound 59

Compound 46

Step 1: Synthesis of 5-[[2-[2-(2-methylpyrazol-3-yl)-1-piperidyl]-2-oxo-acetyl]amino]pyridine-3-carboxamide 2,2,2-trifluoroethyl 2-[(5-carbamoyl-3-pyridyl)amino]-2-oxo-acetate (0.5 g, 1.72 mmol), 2-(2-methylpyrazol-3-yl)piperidine (283.73 mg, 1.41 mmol, HCl) and dipea (443.85 mg, 3.43 mmol, 598.19 μL) were mixed in acetonitrile (5 mL) and heated in the sealed tube at 100° C. with vigorous stirring. After 16 h the mixture was filtered, the solvent was evaporated and crude product was subjected to HPLC (H₂O/MeOH+NH₃ as a solvent mixture; YMC-ACTUS TRIART C18, 100*20 mm, 5 um column) to afford 5-[[2-[2-(2-methylpyrazol-3-yl)-1-piperidyl]-2-oxo-acetyl]amino]pyridine-3-carboxamide (24 mg, 67.34 μmol, 3.92% yield). ¹H NMR (400 MHz, CD₃OD) δ 1.82 (m, 3H), 2.12 (m, 3H), 2.65 (m, 1H), 3.19 (m, 1H), 3.80 (s, 3H), 3.85 (m, 1H), 5.91 (m, 1H), 6.52 (d, 1H), 7.40 (d, 1H), 8.55 (s, 1H), 8.77 (s, 1H), 8.89 (s, 1H), NH₂ is not observed. LCMS(ESI): [M+H]⁺ m/z: calcd 356.2; found 357.2; Rt=2.056 min.

Step 2: Synthesis of Rel-(R)-5-(2-(2-(1-methyl-1H-pyrazol-5-yl)piperidin-1-yl)-2-oxoacetamido)Nicotinamide (Compound 59) and Rel-(S)-5-(2-(2-(1-methyl-1H-pyrazol-5-yl)piperidin-1-yl)-2-oxoacetamido)Nicotinamide (Compound 46)

5-[[2-[2-(2-methylpyrazol-3-yl)-1-piperidyl]-2-oxo-acetyl]amino]pyridine-3-carboxamide (24.0 mg, 67.34 μmol) was chirally separated using AD-HII Chiralpak column and 50-25-25 Hexane-IPA-MeOH as a mobile phase, Flow 12 mL/min affording Compound 59-rel-(R)-5-(2-(2-(1-methyl-1H-pyrazol-5-yl)piperidin-1-yl)-2-oxoacetamido)nicotinamide (8.04 mg, 22.56 μmol; 33.5% yield; RT (AD-HII, Hexane-IPA-MeOH, 50-25-25, Flow 12 mL/min)=32.552 min) and Compound 46—rel-(S)-5-(2-(2-(1-methyl-1H-pyrazol-5-yl)piperidin-1-yl)-2-oxoacetamido)nicotinamide (8.8 mg, 24.69 μmol; 36.67% yield; RT (AD-HII, Hexane-IPA-MeOH, 50-25-25, 12 mL/min)=18.482 min).

Compound 46: RT (AD-H, Hexane-IPA-MeOH, 50-25-25, 0.6 mL/min)=22.757 min. ¹H NMR (500 MHz, CDCl₃) δ 1.86 (m, 3H), 2.12 (m, 3H), 3.10 (m, 1H), 3.86 (m, 3H), 4.61 (m, 1H), 6.11 (m, 2H), 6.40 (m, 2H), 7.44 (m, 1H), 8.68 (m, 1H), 8.92 (m, 1H), 9.01 (m, 1H), 9.83 (m, 1H). LCMS (ESI): [M+H]⁺ m/z: calcd 356.2; found 356.9; Rt=3.484 min.

Compound 59: RT (AD-H, Hexane-IPA-MeOH, 50-25-25, 0.6 mL/min)=38.353 min. ¹H NMR (500 MHz, CDCl₃) δ 1.83 (m, 3H), 2.12 (m, 3H), 3.01 (m, 1H), 3.86 (m, 3H), 4.62 (m, 1H), 6.12 (m, 2H), 6.40 (m, 2H), 7.45 (m, 1H), 8.67 (m, 1H), 8.91 (m, 1H), 9.02 (m, 1H), 9.75 (m, 1H). LCMS (ESI): [M+H]⁺ m/z: calcd 356.2; found 356.9; Rt=3.480 min.

Example 15. The Synthesis of 5-(2-(5,5-dimethyl-2-phenylpiperidin-1-yl)-2-oxoacetamido)Nicotinamide (Compound 45

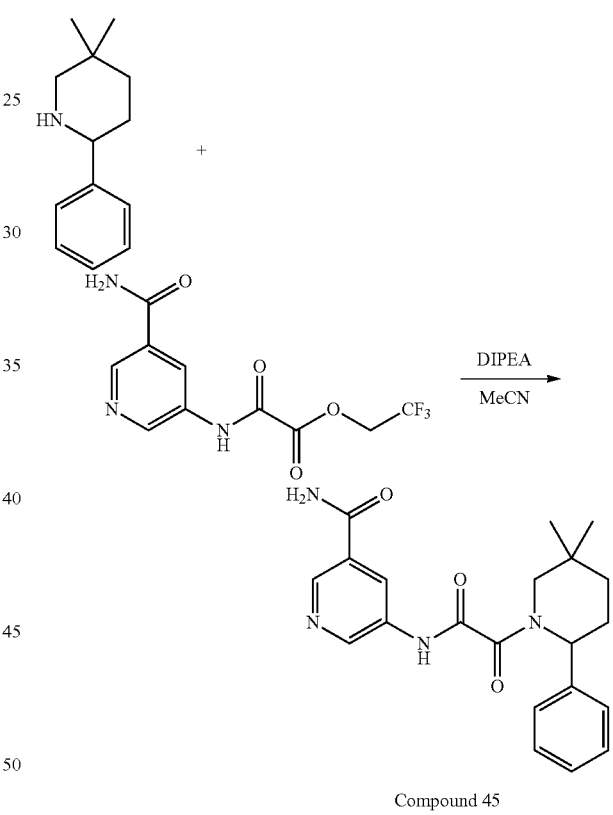

Compound 45

2,2,2-trifluoroethyl 2-[(5-carbamoyl-3-pyridyl)amino]-2-oxo-acetate (150 mg, 515.14 μmol), 5,5-dimethyl-2-phenyl-piperidine (97.51 mg, 515.14 μmol) and DIPEA (66.58 mg, 515.14 μmol, 89.73 μL) were mixed in acetonitrile (1 mL) and heated at 100° C. with vigorous stirring for 16 h. After cooling to RT the mixture was filtered, evaporated in vacuo and subjected to HPLC (column: YMC Actus Triart C18 100×20 mm, 5 um and MeOH+NH₃ as a mobile phase) 5-[[2-(5,5-dimethyl-2-phenyl-1-piperidyl)-2-oxo-acetyl]amino]pyridine-3-carboxamide (3.9 mg, 10.25 μmol, 1.99% yield) was obtained.

¹H NMR (400 MHz, CDCl₃) δ (ppm) 0.86 (m, 3H), 1.03 (m, 3H), 1.37 (m, 1H), 1.50 (m, 1H), 2.16 (m, 1H), 2.31 (m, 1H), 2.87 (m, 1H), 4.34 (m, 1H), 6.11 (m, 3H), 7.26 (m, 4H), 7.35 (m, 2H), 8.62 (m, 1H), 8.79 (m, 1H), 8.95 (m, 1H).
LCMS(ESI): [M]⁺ m/z: calcd 380.4; found 381.2; Rt=1.192 min.

Example 16. The Synthesis of rac-2-((2R,5S)-2-(4-fluorophenyl)-5-methylpiperidin-1-yl)-N-(5-methylpyridin-3-yl)-2-oxoacetamide (Compound 89

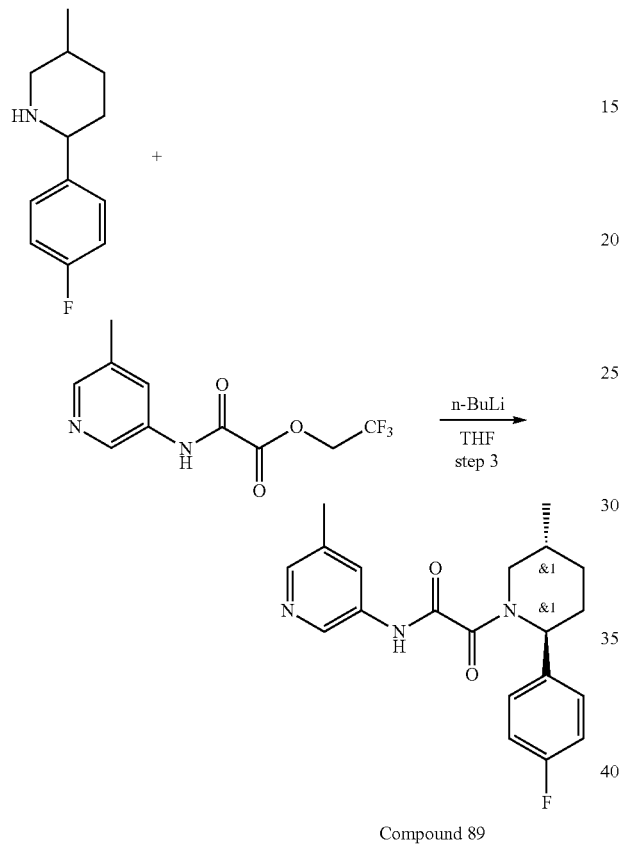

Compound 89

To a solution of 2,2,2-trifluoroethyl [(5-methylpyridin-3-yl)amino](oxo)acetate (406.99 mg, 1.55 mmol) in THF (15 mL) was added n-butyllithium (864.64 mg, 3.10 mmol, 1.25 mL, 23% purity) at −78° C. under Ar atmosphere. After 15 min, 2-(4-fluorophenyl)-5-methyl-piperidine (0.3 g, 1.55 mmol) was added in one portion. The resulting mixture was warmed to rt, quenched with NH₄Cl aq solution, extracted with EtOAc, dried over Na₂SO₄, evaporated and subjected to HPLC (column SunFire 100*19 mm 5 um, ACN+FA (0.01%) as eluent mixture). 2-[(2S,5R)-2-(4-fluorophenyl)-5-methyl-1-piperidyl]-N-(5-methyl-3-pyridyl)-2-oxo-acetamide (13.1 mg, 36.86 μmol, 2.37% yield) was obtained in two fraction: 7.4 mg (98.21% by LCMS, single diastereomer) and 5.7 mg (100% by LCMS, mixture of diastereomers). Pale yellow gum, which slowly crystalize.

¹H NMR (600 MHz, DMSO-d₆) δ (ppm) 1.02 (d, 3H), 1.33 (m, 1H), 1.66 (m, 1H), 1.87 (m, 1H), 2.11 (m, 2H), 2.27 (m, 3H), 2.99 (m, 1H), 3.82 (m, 1H), 5.34 (m, 1H), 7.21 (m, 2H), 7.38 (m, 2H), 7.90 (m, 1H), 8.16 (m, 1H), 8.58 (m, 1H), 11.02 (m, 1H).

LCMS(ESI): [M]⁺ m/z: calcd 355.4; found 356.2; Rt=3.033 min.

Example 17. The Synthesis of N-(6-amino-5-methylpyridin-3-yl)-2-(2-cyclohexylpiperidin-1-yl)-2-oxoacetamide (Compound 30, Compound 42, Compound 34

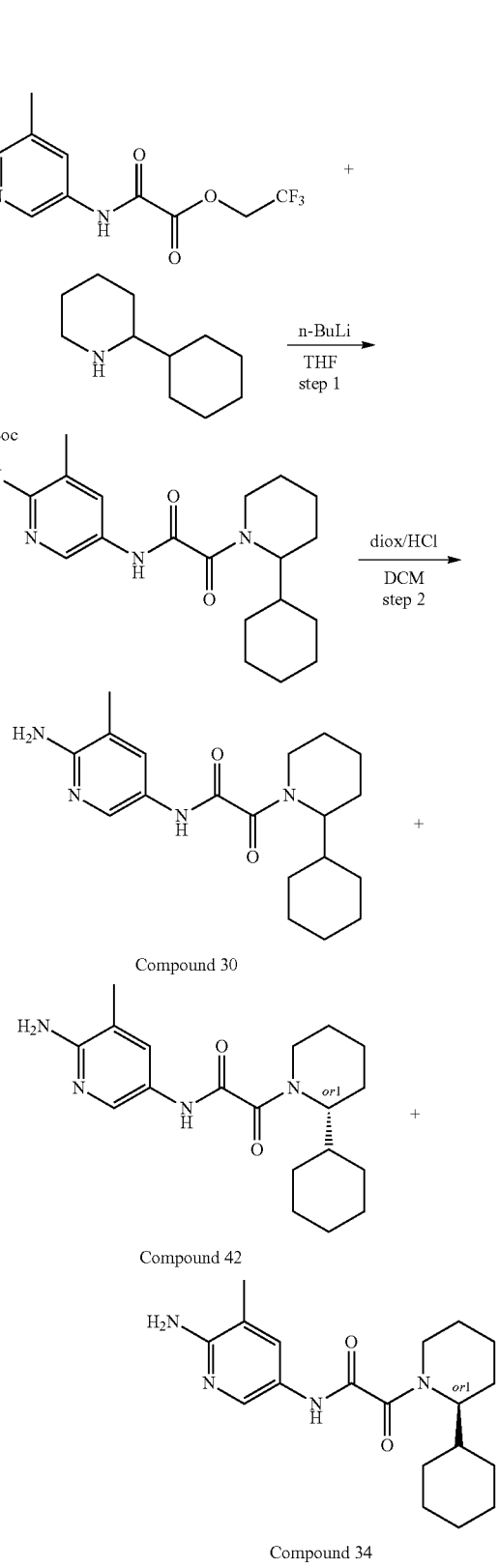

Compound 30

Compound 42

Compound 34

Step 1: Synthesis of tert-butyl (5-(2-(2-cyclohexylpiperidin-1-yl)-2-oxoacetamido)-3-methylpyridin-2-yl)carbamate To a solution of 2-cyclohexylpiperidine (306.90 mg, 1.19 mmol) in THF (15 mL) was added n-butyllithium solution 2.5 M in hexanes (458.37 mg, 7.16 mmol, 3 mL) dropwise at −70° C. under Ar. The reaction mixture was stirred at −70° C. for 20 min., then 2,2,2-trifluoroethyl 2-[[6-(tert-butoxycarbonylamino)-5-methyl-3-pyridyl]amino]-2-oxo-acetate (0.45 g, 1.19 mmol) was added portionwise. The resulting solution was stirred at −70° C. for 30 min. and at room temperature for 1 hr. The resulting solution was cooled to −50° C. and quenched with sat. $NH_4Cl$ (aq) (50 ml). The organic layer was separated and the aqueous layer was extracted with EtOAc (20 mL×2). The combined organic layers were washed with brine, dried over $Na_2SO_4$ and concentrated to dryness to give tert-butyl N-[5-[[2-(2-cyclohexyl-1-piperidyl)-2-oxo-acetyl]amino]-3-methyl-2-pyridyl]carbamate (0.5 g, crude).

$^1$H NMR (500 MHz, DMSO-$d_6$) δ (ppm) 0.85 (m, 6H), 1.26 (m, 6H), 1.45 (s, 9H), 1.69 (m, 6H), 2.14 (s, 3H), 2.22 (m, 1H), 2.98 (d, 1H), 8.02 (m, 1H), 8.49 (m, 1H), 9.06 (m, 1H), 9.65 (m, 1H).

LCMS(ESI): [M+1]$^+$ m/z: calcd 444.5; found 445.2; Rt=1.572 min.

Step 2: Synthesis of N-(6-amino-5-methylpyridin-3-yl)-2-(2-cyclohexylpiperidin-1-yl)-2-oxoacetamide (Compound 30, Compound 42, Compound 34

Hydrogen chloride solution 40 M in dioxane (732.27 mg, 2.81 mmol, 697.40 µL, 14% purity) was carefully added at rt to a solution of tert-butyl N-[5-[[2-(2-cyclohexyl-1-piperidyl)-2-oxo-acetyl]amino]-3-methyl-2-pyridyl]carbamate (0.5 g, 281.17 µmol) in DCM (20 mL). The reaction mixture was then stirred for 12 hr at rt and the solvents were evaporated in vacuo to give 0.5 g of crude material. It was subjected to RP-HPLC (column: YMC Actus Triart C18 100×20 mm, 5 um; 55%; 0-5 min 0.1% $NH_3$-methanol as mobile phase) to give Compound 30 N-(6-amino-5-methyl-3-pyridyl)-2-[2-cyclohexyl-1-piperidyl]-2-oxo-acetamide (33 mg). The enantiomers were separated by chiral HPLC (column: OJ-H (250*20, 5 mkm), Hexane-IPA-MeOH, 90-5-5% as mobile phase) to give the two individual enantiomers Compound 34 N-(6-amino-5-methyl-3-pyridyl)-2-[(2S)-2-cyclohexyl-1-piperidyl]-2-oxo-acetamide (12 mg, 34.84 µmol, 24.78% yield) and Compound 42 N-(6-amino-5-methyl-3-pyridyl)-2-[(2R)-2-cyclohexyl-1-piperidyl]-2-oxo-acetamide (12.1 mg, 35.13 µmol, 24.99% yield).

Compound 30: $^1$H NMR (500 MHz, DMSO-$d_6$) δ (ppm) 0.94 (m, 3H), 1.20 (m, 4H), 1.52 (m, 2H), 1.64 (m, 5H), 1.80 (m, 4H), 2.08 (s, 3H), 3.68 (dd, 1H), 4.23 (dd, 1H), 5.20 (s, 2H), 7.53 (s, 1H), 8.01 (s, 1H), 10.13 (s, 1H). LCMS(ESI): [M+1]$^+$ m/z: calcd 344.2; found 345.2; Rt=2.912 min.

Compound 42: Retention time: 32.70 min $^1$H NMR (500 MHz, DMSO-$d_6$) δ (ppm) 0.94 (m, 3H), 1.19 (m, 3H), 1.48 (m, 2H), 1.65 (m, 5H), 1.78 (m, 4H), 2.08 (m, 3H), 3.05 (m, 1H), 3.68 (m, 1H), 4.22 (m, 1H), 5.20 (s, 2H), 7.53 (m, 1H), 8.01 (m, 1H), 10.13 (s, 1H). LCMS(ESI): [M+1]$^+$ m/z: calcd 344.2; found 345.2; Rt=1.103 min.

Compound 34: Retention time: 24.50 min $^1$H NMR (500 MHz, DMSO-$d_6$) δ (ppm) 0.92 (m, 3H), 1.20 (m, 3H), 1.48 (m, 2H), 1.63 (m, 5H), 1.78 (m, 4H), 2.08 (m, 3H), 3.05 (m, 1H), 3.68 (m, 1H), 4.23 (m, 1H), 5.20 (s, 2H), 7.52 (m, 1H), 8.01 (m, 1H), 10.13 (s, 1H). LCMS(ESI): [M+1]$^+$ m/z: calcd 344.2; found 345.2; Rt=4.052 min.

Example 18. The Synthesis of N-(6-amino-5-methyl-3-pyridyl)-2-oxo-2-[(2R)-2-(3-pyridyl)-1-piperidyl]acetamide (Compound 74) and N-(6-amino-5-methyl-3-pyridyl)-2-oxo-2-[(2S)-2-(3-pyridyl)-1-piperidyl]acetamide (Compound 69

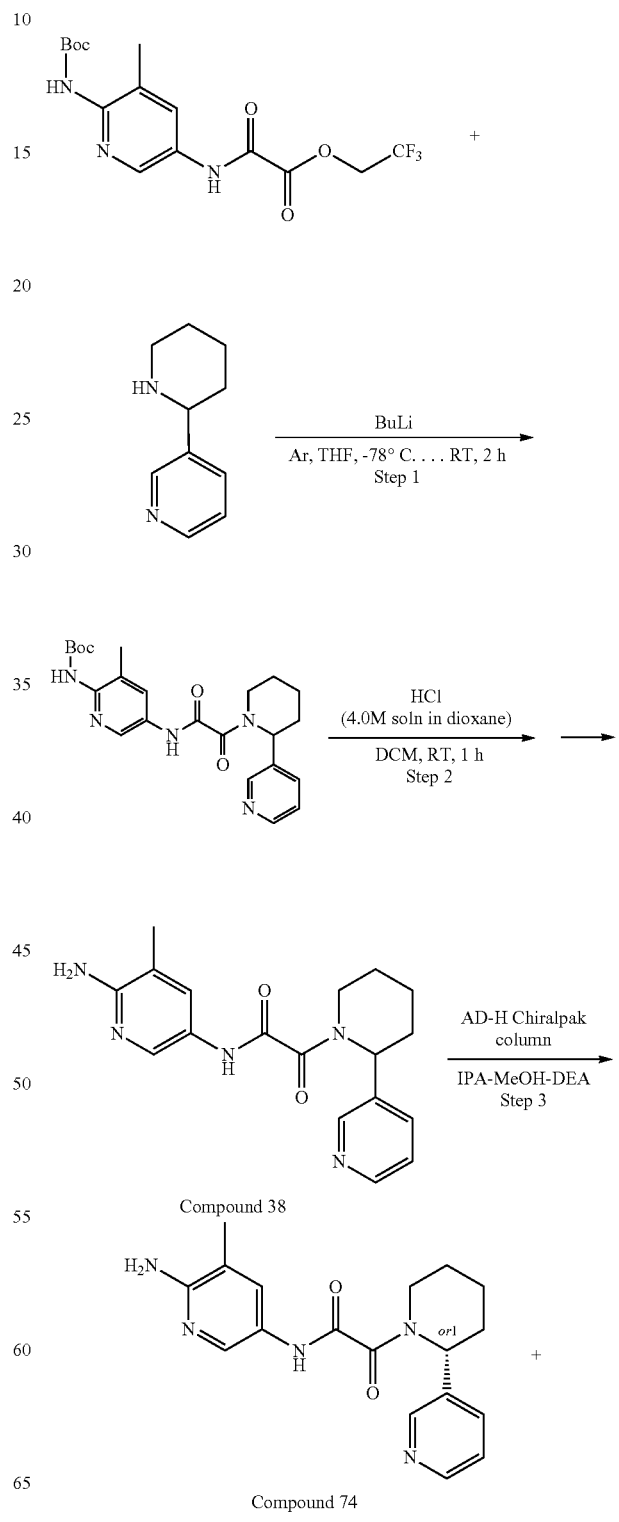

Compound 38

Compound 74

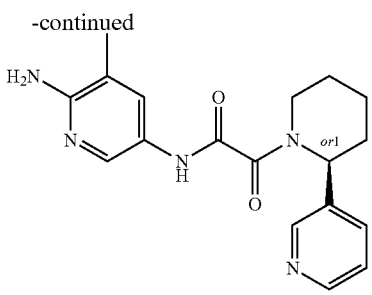

Compound 69

Step 1: The Synthesis of tert-butyl N-[3-methyl-5-[[2-oxo-2-[2-(3-pyridyl)-1-piperidyl]acetyl]amino]-2-pyridyl]carbamate To a solution of 3-(2-piperidyl)pyridine (300.97 mg, 1.86 mmol) in THF (29 mL) was added butyllithium (392.19 mg, 6.12 mmol, 2.45 mL) dropwise at −78° C. under Ar. The reaction mixture was stirred at −78° C. for 20 min., then 2,2,2-trifluoroethyl 2-[[6-(tert-butoxycarbonylamino)-5-methyl-3-pyridyl]amino]-2-oxo-acetate (0.7 g, 1.86 mmol) was added portionwise. The resulting solution was stirred at −78° C. for 30 min. and at room temperature for 1 hr. The resulting solution was cooled to −50° C. and quenched with sat. NH$_4$Cl(aq) (30 ml). The organic layer was separated and the aqueous layer was extracted with EtOAc (20 mL×2). The combined organic layers were washed with brine, dried over Na$_2$SO$_4$ and concentrated to dryness to give tert-butyl N-[3-methyl-5-[[2-oxo-2-[2-(3-pyridyl)-1-piperidyl]acetyl]amino]-2-pyridyl]carbamate (0.51 g, 1.16 mmol, 62.55% yield).

LCMS(ESI): [M+H]$^+$ m/z: calcd 439.2; found 440.2; Rt=1.058 min.

Step 2: The Synthesis of N-(6-amino-5-methyl-3-pyridyl)-2-oxo-2-[2-(3-pyridyl)-1-piperidyl]acetamide (Compound 38

Hydrogen chloride solution 40 M in dioxane (800.00 mg, 21.94 mmol, 1 mL) was added to a solution of tert-butyl N-[3-methyl-5-[[2-oxo-2-[2-(3-pyridyl)-1-piperidyl]acetyl]amino]-2-pyridyl]carbamate (0.51 g, 1.16 mmol) in DCM (5 mL). The reaction mixture was stirred at 25° C. for 1 hr, then evaporated in vacuo and obtained crude product 0.3 g was purified by preparative HPLC (100% methanol-water, flow 30 ml/min) to afford product N-(6-amino-5-methyl-3-pyridyl)-2-oxo-2-[2-(3-pyridyl)-1-piperidyl]acetamide (0.0381 g, 101.37 μmol, 8.74% yield, HCl)

$^1$H NMR (500 MHz, DMSO-d$_6$) δ 1.53 (m, 2H), 1.66 (m, 2H), 1.74 (m, 1H), 1.96 (m, 1H), 2.08 (m, 3H), 2.40 (m, 1H), 4.10 (m, 1H), 5.28 (m, 2H), 5.57 (m, 1H), 7.35 (m, 1H), 7.55 (m, 1H), 7.70 (m, 1H), 8.03 (m, 1H), 8.45 (m, 1H), 8.54 (m, 1H), 10.43 (s, 1H).

LCMS(ESI): [M+H]$^+$ m/z: calcd 339.2; found 340.2; Rt=0.622 min.

Step 3: The Synthesis of N-(6-amino-5-methyl-3-pyridyl)-2-oxo-2-[(2R)-2-(3-pyridyl)-1-piperidyl]acetamide (Compound 74) and N-(6-amino-5-methyl-3-pyridyl)-2-oxo-2-[(2S)-2-(3-pyridyl)-1-piperidyl]acetamide (Compound 69

The enantiomers were separated by chiral HPLC (column: AD-H (250*20, 5 mkm) Chiralpak column, IPA-MeOH-DEA, 50-50-0.2, 0.5 ml/min as mobile phase) to give the two individual enantiomers Compound 74—N-(6-amino-5-methyl-3-pyridyl)-2-oxo-2-[(2R)-2-(3-pyridyl)-1-piperidyl]acetamide (0.01467 g, 39.03 μmol, 36.67% yield, HCl; RT=80.477 min) and Compound 69—N-(6-amino-5-methyl-3-pyridyl)-2-oxo-2-[(2S)-2-(3-pyridyl)-1-piperidyl]acetamide (8.15 mg, 21.68 μmol, 20.37% yield, HCl; RT=51.702 min).

Compound 74 RT (AD-H, IPA-MeOH-DEA, 50-50-0.2, 0.5 ml/min)=80.789 min.

$^1$H NMR (DMSO-d$_6$, 500 MHz): δ (ppm) 1.41 (m, 1H), 1.62 (m, 2H), 1.88 (m, 1H), 2.03 (m, 3H), 2.41 (m, 2H), 2.97 (m, 1H), 4.00 (m, 1H), 5.66 (m, 3H), 7.43 (m, 1H), 7.50 (m, 1H), 7.75 (m, 1H), 8.02 (m, 1H), 8.51 (m, 1H), 8.57 (m, 1H), 10.59 (s, 1H)

LCMS(ESI): [M+H]$^+$ m/z: calcd 339.2; found 340.2; Rt=2.562 min.

Compound 74 RT (AD-H, IPA-MeOH-DEA, 50-50-0.2, 0.5 ml/min)=51.702 min.

$^1$H NMR (DMSO-d$_6$, 500 MHz): δ (ppm) 1.41 (m, 1H), 1.60 (m, 3H), 1.89 (m, 1H), 2.03 (m, 3H), 2.94 (m, 1H), 4.00 (m, 1H), 5.49 (m, 3H), 7.44 (m, 1H), 7.51 (m, 1H), 7.75 (m, 1H), 8.02 (m, 1H), 8.51 (m, 1H), 8.57 (m, 1H), 10.59 (s, 1H)

LCMS(ESI): [M+H]$^+$ m/z: calcd 339.2; found 340.2; Rt=2.570 min.

Example 19. The Synthesis of 2-(2-(3-(dimethylamino)phenyl)piperidin-1-yl)-N-(5-methylpyridin-3-yl)-2-oxoacetamide (Compound 15

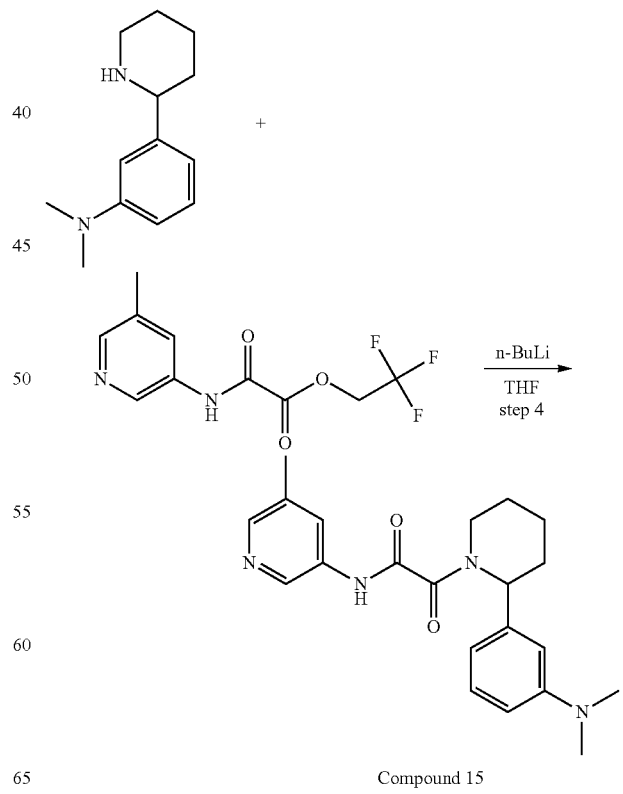

Compound 15

Step 1: Synthesis of 2-(2-(3-(dimethylamino)phenyl)piperidin-1-yl)-N-(5-methylpyridin-3-yl)-2-oxoacetamide (Compound 15 n-Butyllithium (250.82 mg, 3.92 mmol) (2.5 M in hexane) was added dropwise to the solution of N,N-dimethyl-3-(2-piperidyl)aniline (0.4 g, 1.96 mmol) in THF (20 mL) at −78° C. The resulting mixture was stirred for 5 min, followed by addition of 2,2,2-trifluoroethyl 2-[(5-methyl-3-pyridyl)amino]-2-oxo-acetate (513.31 mg, 1.96 mmol). The resulting mixture was left to warm to rt and stirred at that temperature for 12 hr. $NH_4Cl$(0.6 g) aq. solution was added thereto. The resulting mixture was evaporated to dryness. The residue (1 g) was subjected to HPLC (Mobile Phase, Column): 16_ACN 36% 0.5-6.5 min; water-acetonitrile; flow 30 ml/min; (loading pump 4 ml/min acetonitrile); target mass 366; column SunFire 100*19 mm 5 um) to obtain 2-[2-[3-(dimethylamino)phenyl]-1-piperidyl]-N-(5-methyl-3-pyridyl)-2-oxo-acetamide (0.054 g, 147.36 μmol, 7.53% yield).

$^1$H NMR (400 MHz, DMSO-$d_6$) δ (ppm) 1.50 (m, 2H), 1.60 (m, 2H), 1.80 (m, 1H), 2.29 (m, 3H), 2.89 (m, 6H), 3.08 (m, 1H), 3.42 (m, 1H), 3.97 (m, 1H), 5.35 (m, 1H), 6.62 (m, 3H), 7.21 (m, 1H), 7.94 (m, 1H), 8.18 (m, 1H), 8.59 (m, 1H), 11.09 (m, 1H). LCMS(ESI): [M]$^+$ m/z: calcd 366.5; found 367.2; Rt=2.518 min.

Example 20. The Synthesis of rac-2-((2R,5S)-2-(3-methoxyphenyl)-5-methylpiperidin-1-yl)-N-(5-methylpyridin-3-yl)-2-oxoacetamide (Compound 28

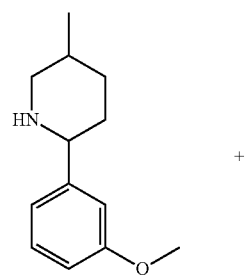

+

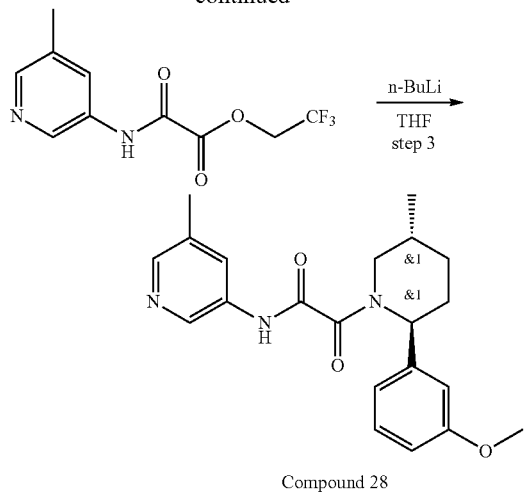

Compound 28

Butyllithium (187.21 mg, 2.92 mmol) (2.5 M in Hexane) was added dropwise to the solution of 2-(3-methoxyphenyl)-5-methyl-piperidine (0.3 g, 1.46 mmol) in THF (20 mL) at −78° C. The resulting mixture was stirred for 5 min, followed by addition of 2,2,2-trifluoroethyl 2-[(5-methyl-3-pyridyl)amino]-2-oxo-acetate (383.13 mg, 1.46 mmol). The resulting mixture was left to warm to r.t. and stirred at that temperature for 12 hr. $NH_4Cl$(0.6 g) aq. solution was added thereto. The resulting mixture was evaporated to dryness. The residue (4 g) was purified by HPLC (column SunFire 100*19 mm 5 um, water-MeCN as eluent mixture) to obtain 2-[(2S,5R)-2-(3-methoxyphenyl)-5-methyl-1-piperidyl]-N-(5-methyl-3-pyridyl)-2-oxo-acetamide (130.90 mg, 356.25 μmol, 24.38% yield).

$^1$H NMR (400 MHz, DMSO-$d_6$) δ (ppm) 1.03 (m, 3H), 1.34 (m, 1H), 1.67 (m, 1H), 1.91 (m, 1H), 2.15 (m, 3H), 2.29 (m, 3H), 3.45 (m, 1H), 3.75 (m, 3H), 5.35 (m, 1H), 6.88 (m, 3H), 7.33 (m, 1H), 7.92 (m, 1H), 8.17 (m, 1H), 8.59 (m, 1H), 11.06 (m, 1H).

LCMS(ESI): [M]$^+$ m/z: calcd 367.4; found 368.2; Rt=1.193 min.

Scheme B. Synthesis of Compounds of Formula 2

Compounds of Formula 2, 2a, 2b, 2c and 2d are compounds of Formula (I), (Ia), (Ib), (Ic) and (Id) wherein $R^1$, $R^2$, $R^3$, $R^4$, $R^6$, $R^7$, and $R^8$ are as described herein
General Procedure 2

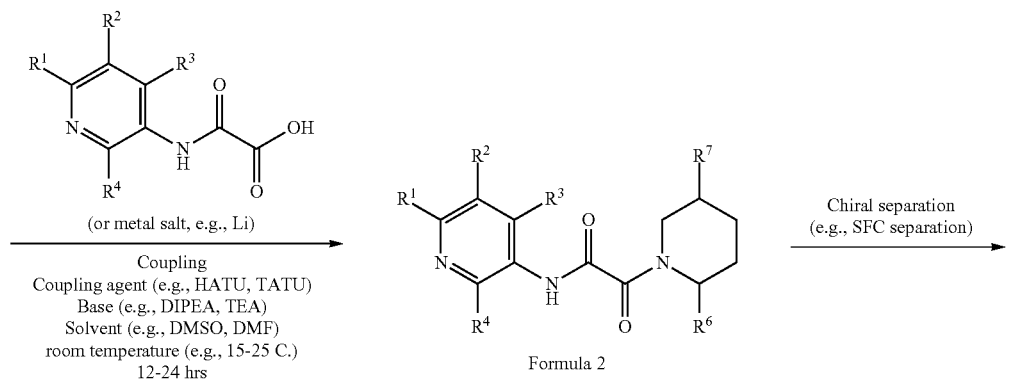

-continued

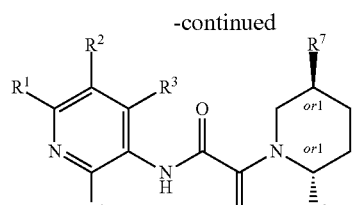

2a

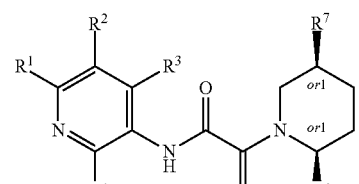

2c

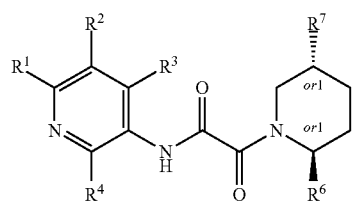

2b

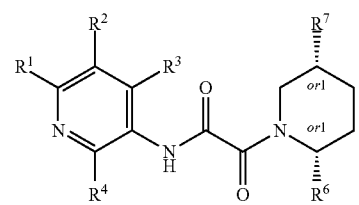

2d

Note that the separation step is optional, and is used in certain cases to separate the cis/trans diastereomers, and in certain cases to separate distinct enantiomers, as described in the detailed procedures. In certain instances, the starting piperidine is in a defined cis or trans configuration—in those instances, the chiral separation step results only in two of the four enantiomers depicted.

Methods of chiral separation are known to persons of ordinary skill in the art. For example, in some embodiments, chiral separation can be accomplished through the use of chiral HPLC purification (Column: AD-H III (250*20 mm, 5 m). Exemplary eluents include, but are not limited to, hexane, IPA, MeOH, MeCN, and H$_2$O, and mixtures thereof.

In some embodiments, compounds of the present disclosure can be prepared through a method that comprises an amide bond coupling. In some embodiments, an amide bond coupling employs a piperidine and a carboxylic acid. Examples of conditions known to facilitate an amide bond coupling include but are not limited to adding a coupling agent such as CDI, HATU, HOBT, HBTU or PyBOP, a base such as a hydride base e.g., NaH, or KH, an amine base such as DBU, NEt$_3$, and NEt($^i$Pr)$_2$ or a carbonate base e.g., Na$_2$CO$_3$, K$_2$CO$_3$, or Cs$_2$CO$_3$, and in one embodiment stirring a reaction at 0° C. to room temperature or another embodiment at a temperature of 70° C. or higher, for example at a temperature in a range of 70° C. to 110° C., or in a range of 70° C. to 80° C., or at 80° C. A reaction may be carried out in solvents such as but not limited to DMF, and MTBE. In some embodiments, a reaction comprises of HATU, Et$_3$N, and DMF. In some embodiments, a reaction comprises employment of HATU, Et$_3$N, and MeCN. In some embodiments, a reaction comprises of TATU, Et$_3$N, and DMF. In some embodiments, a reaction comprises of HATU, DIPEA, and DMSO. In some embodiments, a reaction comprises of HATU, DIPEA, and DMF. In some embodiments, a reaction comprises of HATU, TEA, and DMSO.

Example 21. The Synthesis of 5-[[2-[(2R,5S)-2-(4-fluorophenyl)-5-methyl-1-piperidyl]-2-oxo-acetyl]amino]pyridine-3-carboxamide (Compound 300

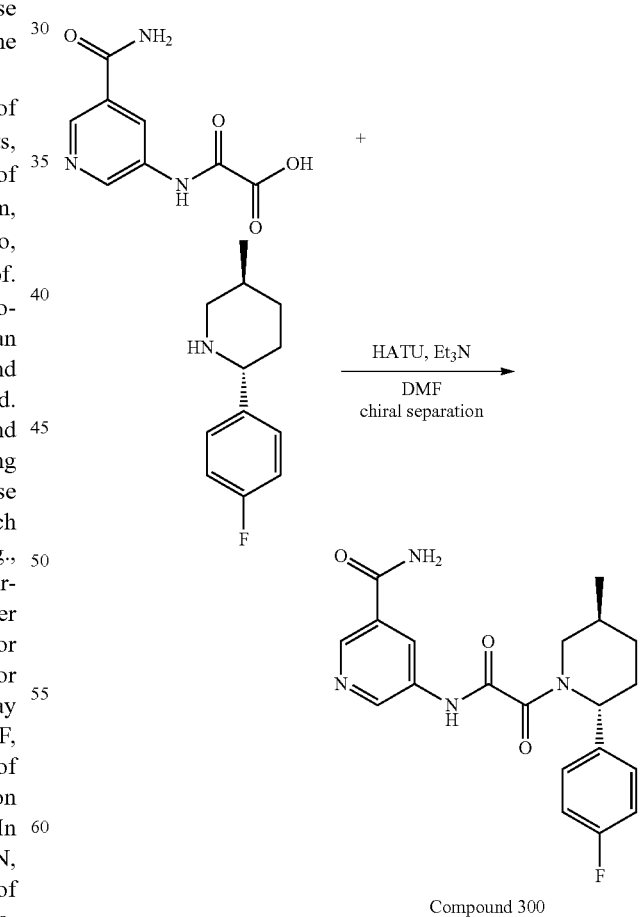

Compound 300

To a stirred solution of 2-[(5-carbamoyl-3-pyridyl)amino]-2-oxo-acetic acid (HCl salt, 5.34 g, 21.73 mmol) and (2R,5S)-2-(4-fluorophenyl)-5-methyl-piperidine (4.2 g, 21.73 mmol)(intermediate 4A) in DMF (70 mL) were added HATU (8.26 g, 21.73 mmol) and Et₃N (8.80 g, 86.93 mmol, 12.12 mL) at 0° C. respectively. The resulting reaction mixture was stirred at ambient temperature for 9 hours. After 9 hours, the reaction mixture was concentrated under reduced pressure and poured into water (300 mL). The aqueous layer was extracted with EtOAc (2×150 mL). The combined organic phase was washed with water (2×40 mL), dried over Na₂SO₄ and concentrated under reduced pressure to obtain crude product (8 g). The crude product was purified by column chromatography (SiO₂, Eluent: 10-100% CH₃OH in MTBE) to obtain (5.2 g, 13.53 mmol, 62.25% yield) product. The product was subjected to chiral HPLC purification (Column: AD-H III (250*20 mm, 5 um), Eluent: Hexane-IPA-MeOH, 70-15-15, flow rate: 12 mL/min). 2 different fractions were mixed, diluted with MeOH, evaporated in rotary evaporator at 30° C. and then dried under oil pump (0.5 mm Hg) at 35° C. for 8 hours to obtain pure product 5-[[2-[(2R,5S)-2-(4-fluorophenyl)-5-methyl-1-piperidyl]-2-oxo-acetyl]amino]pyridine-3-carboxamide (Compound 3003, 3.6 g, 9.37 mmol, 52.94% yield) as a white solid. ¹H NMR (DMSO-d₆, 600 MHz): δ (ppm) 1.01 (m, 3H), 1.33 (m, 1H), 1.65 (m, 1H), 1.88 (m, 1H), 2.02 (m, 1H), 2.19 (m, 1H), 2.99 (m, 1H), 3.73 (m, 1H), 5.35 (m, 1H), 7.22 (m, 2H), 7.36 (m, 2H), 7.59 (m, 1H), 8.14 (m, 1H), 8.46 (m, 1H), 8.75 (m, 1H), 8.86 (m, 1H), 11.22 (m, 1H).

LCMS(ESI): [M+H]⁺ m/z: calcd 384.2; found 385.0; Rt=3.021 min.

Chiral HPLC: Rt=35.17 min (Column: AD-H; Eluent: Hexane-MeOH-IPA, 70-15-15; Flow Rate: 0.6 mL/min).

$\alpha^{21}D$=+98.75 (EtOH, 0.25 M)

mp=100-122° C.

Example 22. The Synthesis of 5-(2-(5-methyl-2-(1-methyl-1H-pyrazol-5-yl)piperidin-1-yl)-2-oxoacetamido)Nicotinamide (Compound 72, Compound 81

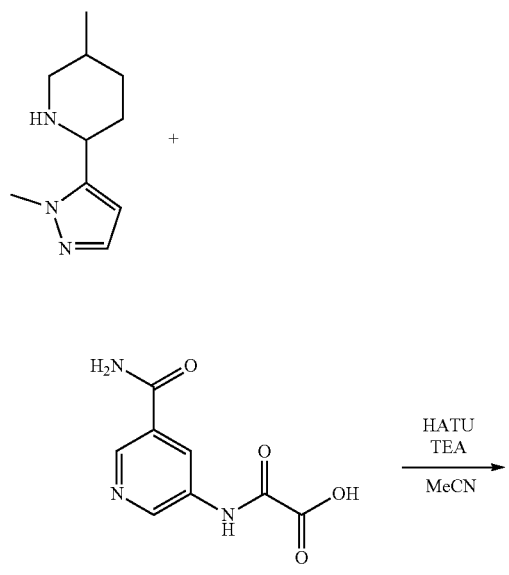

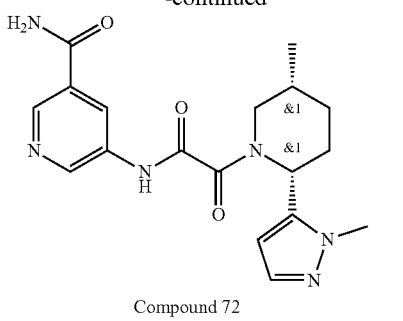

Compound 72

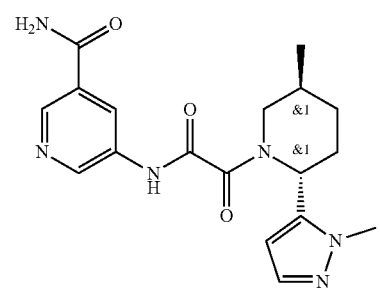

Compound 81

2-[(5-carbamoyl-3-pyridyl)amino]-2-oxo-acetate; triethylammonium (0.25 g, 805.55 μmol), HATU (336.92 mg, 886.10 μmol) and triethylamine (244.54 mg, 2.42 mmol, 336.83 μL) were mixed in dry ACN (20 mL) at 21° C. and the resulting mixture was stirred for 6 hr. 5-methyl-2-(1-methyl-1H-pyrazol-5-yl)piperidine (203.15 mg, 805.55 μmol, 2HCl) was added thereto and the resulting mixture was stirred at 21° C. overnight. The resulting mixture was evaporated to dryness and subjected to HPLC (2-7 min 15-30% acn, 30 ml/min; column: SunFire C18 100*19 5 microM). 3 fractions were obtained: 7.5 mg (95.65% by LCMS) of 5-[[2-[(2R,5S)-5-methyl-2-(2-methylpyrazol-3-yl)-1-piperidyl]-2-oxo-acetyl]amino]pyridine-3-carboxamide (7.5 mg, 20.25 μmol, 2.51% yield) and 23 mg (100% by LCMS)+99 mg (95.17% by LCMS) of 5-[[2-[(2S,5S)-5-methyl-2-(2-methylpyrazol-3-yl)-1-piperidyl]-2-oxo-acetyl]amino]pyridine-3-carboxamide (122.9 mg, 331.80 μmol, 41.19% yield).

Compound 72: ¹H NMR (500 MHz, CDCl₃) δ (ppm) 0.98 (m, 3H), 1.83 (m, 5H), 2.08 (m, 1H), 2.23 (m, 1H), 2.66 (m, 1H), 3.86 (m, 3H), 4.57 (m, 1H), 6.11 (m, 1H), 6.37 (m, 1H), 7.46 (m, 1H), 8.66 (m, 1H), 8.93 (m, 2H), 9.68 (m, 1H).

LCMS(ESI): [M+1]⁺ m/z: calcd 370.4; found 371.2; Rt=2.432 min.

Compound 81: ¹H NMR (500 MHz, CDCl₃) δ (ppm) 1.08 (m, 3H), 1.52 (m, 2H), 2.15 (m, 5H), 3.40 (m, 1H), 3.86 (m, 3H), 4.60 (m, 1H), 6.07 (m, 1H), 6.39 (m, 1H), 7.43 (m, 1H), 8.67 (m, 1H), 8.89 (m, 2H), 9.60 (m, 1H).

LCMS(ESI): [M+1]⁺ m/z: calcd 370.4; found 371.2; Rt=2.432 min.

Example 23. The Synthesis of 5-[[2-oxo-2-[2-(2-thienyl)-1-piperidyl]acetyl]amino]pyridine-3-carboxamide (Compound 120

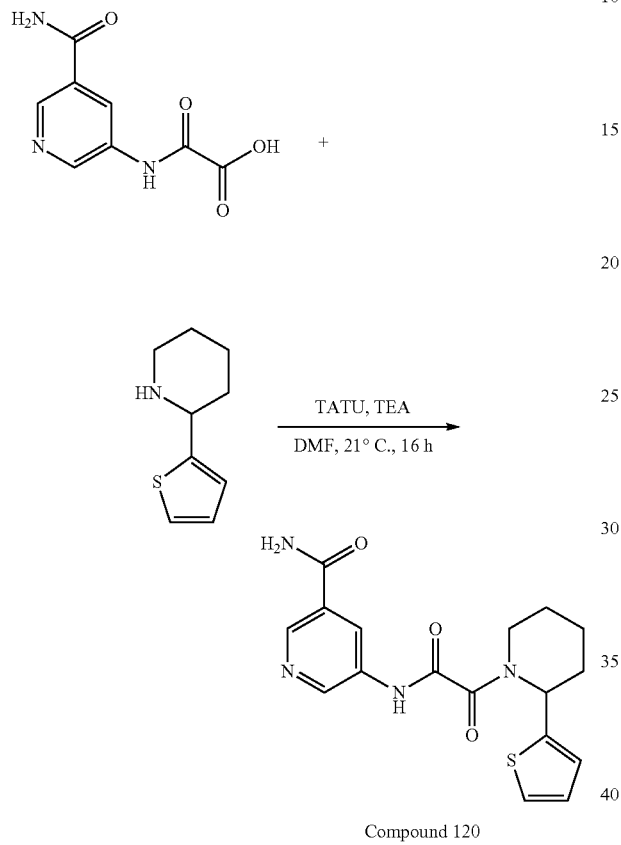

Compound 120

2-[(5-carbamoyl-3-pyridyl)amino]-2-oxo-acetic acid (991.96 mg, 4.74 mmol, Et₃N), TATU (1.68 g, 5.22 mmol) and triethylamine (959.81 mg, 9.49 mmol, 1.32 mL) were mixed in dry DMF (50 mL) at 21° C. and the resulting mixture was stirred for 16 hr. 2-(2-thienyl)piperidine (1.06 g, 5.22 mmol, HCl) was added thereto and the resulting mixture was stirred at 21° C. overnight. The resulting mixture was poured into the water, extracted with EtOAc three times, combined organics were washed with water, brine, dried and evaporated. The residue was purified by CC (SiO₂, Hex-EtOAc as a mobile phase) to give two fractions of 5-[[2-oxo-2-[2-(2-thienyl)-1-piperidyl]acetyl]amino]pyridine-3-carboxamide (0.26 g, 725.42 μmol, 15.30% yield): 0.26 g (96.9% by LCMS) and 0.6 g (84.77% by LCMS).

$^1$H NMR (500 MHz, DMSO-$d_6$+CCl$_4$) δ1.51 (m, 1H), 1.67 (m, 3H), 1.95 (m, 1H), 2.26 (m, 1H), 2.94 (m, 1H), 4.01 (m, 1H), 5.66 (m, 1H), 7.05 (m, 2H), 7.51 (m, 1H), 7.61 (m, 1H), 8.17 (m, 1H), 8.52 (m, 1H), 8.79 (m, 1H), 8.90 (m, 1H), 11.26 (m, 1H).

LCMS(ESI): [M+H]⁺ m/z: calcd 358.1; found 359.2; Rt=1.029 min.

Example 24. The Synthesis of 5-(2-(5-methyl-2-(Thiophen-2-yl)piperidin-1-yl)-2-oxoacetamido) Nicotinamide (Compound 99, Compound 198, Compound 201

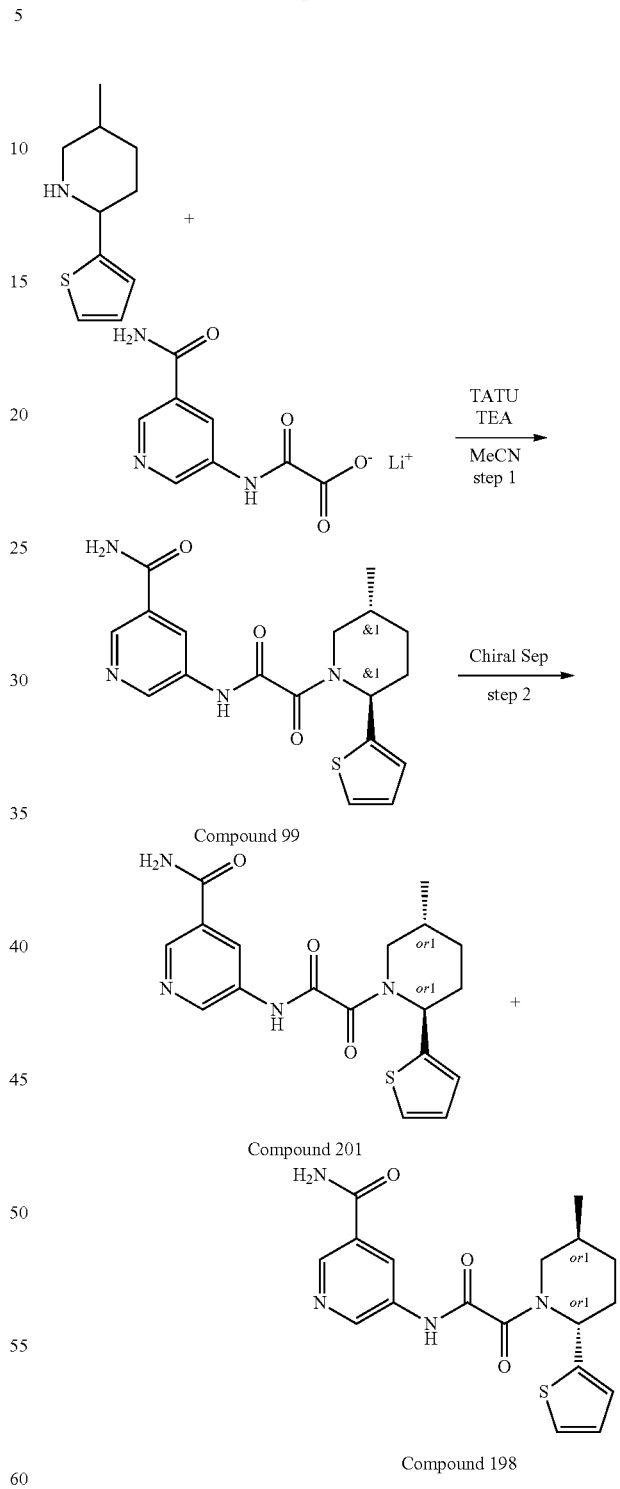

Compound 99

Compound 201

Compound 198

Step 1: Synthesis of 5-(2-(5-methyl-2-(thiophen-2-yl)piperidin-1-yl)-2-oxoacetamido)nicotinamide 5-methyl-2-(2-thienyl)piperidine (0.3 g, 1.65 mmol), 2-(7-Azabenzotriazole-1-yl)-1,1,3,3-tetramethyluronium tetrafluoroborate (532.94 mg, 1.65 mmol) and triethylamine (334.89 mg, 3.31 mmol, 461.28 µL) were mixed in dry MeCN (25 mL) at 21° C. and the resulting mixture was stirred for 6 hr. Lithium [(5-carbamoylpyridin-3-yl)amino](oxo)acetate (355.92 mg, 1.65 mmol) was added thereto and the resulting mixture was stirred at 21° C. overnight. The reaction mixture was evaporated and subjected to HPLC (20-45% MeCN, 30 ml/min; SUNFIRE C18, 100*19.5 µM). 5-[[2-[(2R,5S)-5-methyl-2-(2-thienyl)-1-piperidyl]-2-oxo-acetyl]amino]pyridine-3-carboxamide (10.5 mg, 28.19 µmol, 1.70% yield) was obtained as a pale-yellow solid.

$^1$H NMR (400 MHz, CDCl$_3$) δ (ppm) 1.09 (m, 3H), 1.46 (m, 1H), 2.06 (m, 4H), 2.27 (m, 1H), 3.35 (m, 1H), 4.41 (m, 1H), 6.24 (m, 3H), 6.96 (m, 2H), 8.62 (s, 1H), 8.79 (s, 1H), 8.98 (m, 1H), 9.90 (s, 1H).

LCMS(ESI): [M]$^+$ m/z: calcd 372.4; found 373.2; Rt=1.213 min.

Step 2: Chiral Separation (Compound 198 and Compound 201

Purification on the chiral column was taken in the system Hex-IPA-MeOH, 60-20-20, 0.6 mL/min. Number of injections: 1, injection volume: 2 mkl. From 46 mg of racemate, 23 mg and 23 mg of the individual enantiomers were obtained.

Rel-5-(2-((2R,5S)-5-methyl-2-(Thiophen-2-yl)piperidin-1-yl)-2-oxoacetamido)Nicotinamide Compound 198

Retention time: 31.34 min
$^1$H NMR (600 MHz, DMSO-d$_6$) δ (ppm) 1.00 (m, 3H), 1.41 (m, 1H), 1.89 (m, 2H), 2.03 (m, 1H), 2.13 (m, 1H), 3.34 (m, 1H), 3.75 (m, 1H), 5.63 (m, 1H), 7.02 (m, 2H), 7.47 (m, 1H), 7.59 (m, 1H), 8.14 (m, 1H), 8.49 (m, 1H), 8.76 (m, 1H), 8.88 (s, 1H), 11.21 (m, 1H).

LCMS(ESI): [M]$^+$ m/z: calcd 372.4; found 373.2; Rt=4.479 min.

Rel-5-(2-((2S,5R)-5-methyl-2-(Thiophen-2-yl)piperidin-1-yl)-2-oxoacetamido)Nicotinamide Compound 201

Retention time: 21.28 min
$^1$H NMR (600 MHz, DMSO-d$_6$) δ (ppm) 1.00 (m, 3H), 1.41 (m, 1H), 1.88 (m, 2H), 2.03 (m, 1H), 2.14 (m, 1H), 3.34 (m, 1H), 3.74 (m, 1H), 5.63 (m, 1H), 7.02 (m, 2H), 7.47 (m, 1H), 7.59 (m, 1H), 8.14 (m, 1H), 8.49 (m, 1H), 8.76 (m, 1H), 8.88 (s, 1H), 11.21 (m, 1H).

LCMS(ESI): [M]$^+$ m/z: calcd 372.4; found 373.2; Rt=4.478 min.

Example 25. The Synthesis of 2-methoxy-5-(2-(5-methyl-2-(Thiophen-2-yl)piperidin-1-yl)-2-oxoacetamido)Nicotinamide (Compound 310, Compound 303

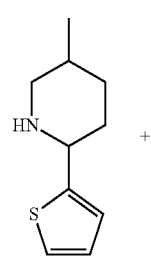

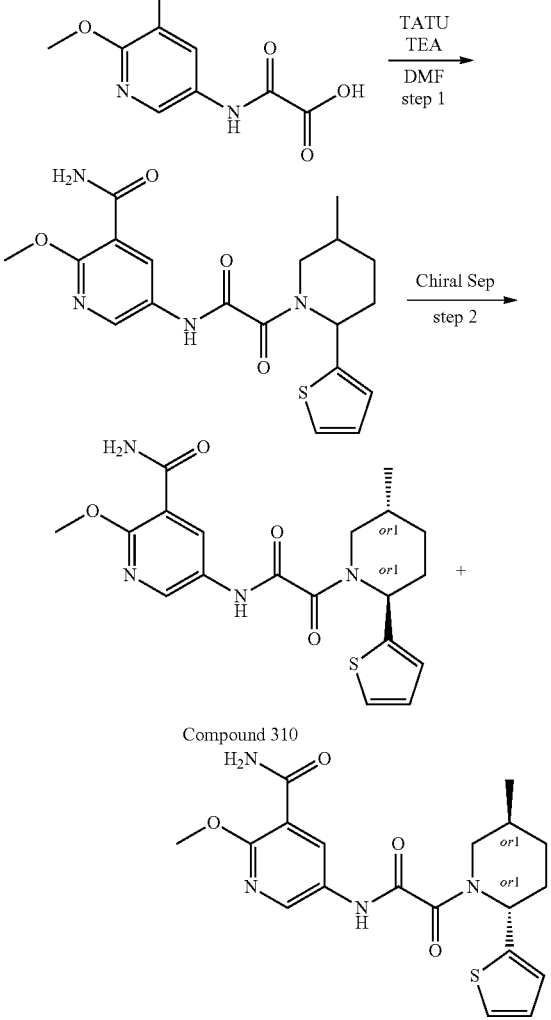

Compound 310

Compound 303

Step 1: Synthesis of 2-methoxy-5-(2-(5-methyl-2-(Thiophen-2-yl)piperidin-1-yl)-2-oxoacetamido)Nicotinamide 2-[(5-carbamoyl-6-methoxy-3-pyridyl)amino]-2-oxo-acetic acid (0.5 g, 1.47 mmol, Et$_3$N), TATU (567.73 mg, 1.76 mmol) and triethylamine (148.64 mg, 1.47 mmol, 204.74 µL) were mixed in dry DMF (25 mL) at 21° C. and the resulting mixture was stirred for 1 hr. 5-methyl-2-(2-thienyl)piperidine (266.32 mg, 1.47 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (40-40-80% 0-1-6 min 0.1% NH$_3$-methanol, flow: 30 ml/min (loading pump 4 ml/min methanol); column: XBridge C18 100×20 mm, 5 um). 2-methoxy-5-[[2-[5-methyl-2-(2-thienyl)-1-piperidyl]-2-oxo-acetyl]amino]pyridine-3-carboxamide (258.7 mg, 642.79 µmol, 43.76% yield) was obtained as a white solid.

$^1$H NMR (400 MHz, CDCl$_3$) δ (ppm) 1.07 (m, 1H), 1.28 (d, 3H), 1.64 (m, 1H), 2.19 (m, 2H), 2.49 (m, 1H), 3.64 (m, 1H), 4.28 (s, 3H), 4.43 (m, 1H), 6.40 (m, 1H), 7.15 (m, 2H), 7.42 (m, 2H), 7.93 (m, 1H), 8.94 (m, 1H), 9.09 (m, 1H), 10.07 (m, 1H).
LCMS(ESI): [M]⁺ m/z: calcd 402.4; found 403.2; Rt=3.394 min.

Step 2: Chiral Separation (Compound 310 and Compound 303

Purification on the chiral column was taken in the system Hex-IPA-MeOH, 80-10-10, 25 mL/min. Number of injections: 1, injection volume: 5 mkl. From 250 mg of racemate, 107.68 mg and 111.65 mg of the individual enantiomers were obtained.

Rel-2-methoxy-5-(2-((2R,5S)-5-methyl-2-(Thiophen-2-yl)piperidin-1-yl)-2-oxoacetamido)Nicotinamide Compound 310

Retention time: 23.85 min
$^1$H NMR (500 MHz, DMSO-d$_6$) δ (ppm) 0.99-1.08 (m, 3H), 1.29-1.48 (m, 1H), 1.82-2.00 (m, 2H), 2.01-2.22 (m, 2H), 2.87-3.27 (m, 1H), 3.50-4.07 (m, 4H), 5.42-5.89 (m, 1H), 6.99-7.08 (m, 2H), 7.43-7.54 (m, 1H), 7.70-7.79 (m, 2H), 8.44-8.52 (m, 1H), 8.53-8.61 (m, 1H), 11.00-11.07 (m, 1H).
LCMS(ESI): [M]⁺ m/z: calcd 402.4; found 403.2; Rt=3.297 min.

Rel-2-methoxy-5-(2-((2S,5R)-5-methyl-2-(Thiophen-2-yl)piperidin-1-yl)-2-oxoacetamido)Nicotinamide Compound 303

Retention time: 29.57 min
$^1$H NMR (500 MHz, DMSO-d$_6$) δ (ppm) 0.96-1.11 (m, 3H), 1.26-1.46 (m, 1H), 1.66-2.00 (m, 2H), 2.00-2.34 (m, 2H), 2.87-3.28 (m, 1H), 3.48-4.06 (m, 4H), 5.44-5.89 (m, 1H), 6.95-7.11 (m, 2H), 7.42-7.55 (m, 1H), 7.70-7.81 (m, 2H), 8.44-8.51 (m, 1H), 8.53-8.64 (m, 1H), 11.03 (s, 1H).
LCMS(ESI): [M]⁺ m/z: calcd 402.4; found 403.2; Rt=3.295 min.

Example 26. The Synthesis of 2-(2-(3-(1-acetylpiperidin-4-yl)phenyl)piperidin-1-yl)-N-(5-methylpyridin-3-yl)-2-oxoacetamide (Compound 7, Compound 78, Compound 73

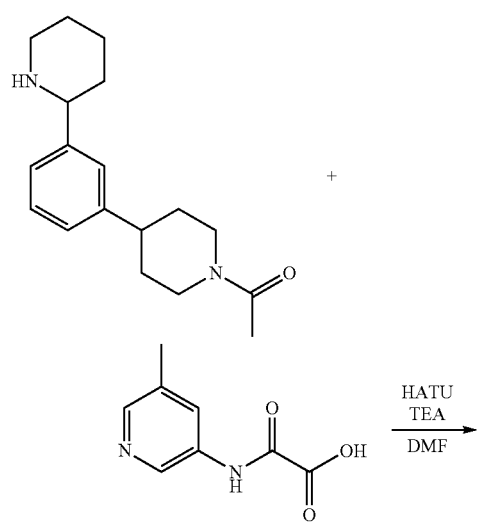

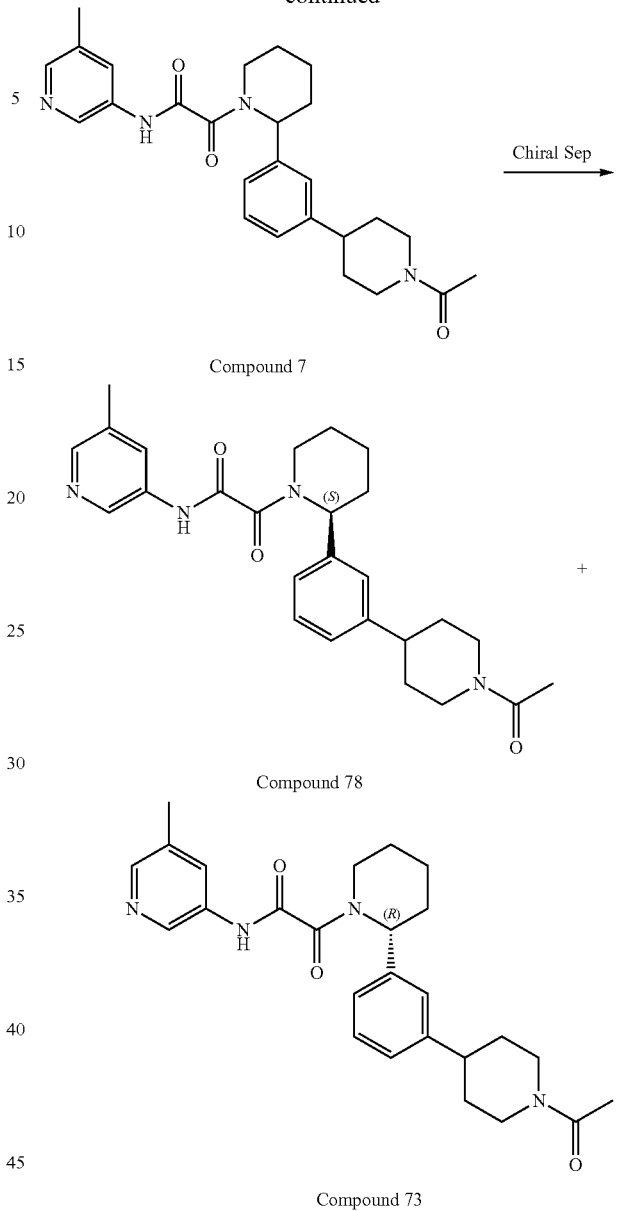

Compound 7

Compound 78

Compound 73

Step 1 Synthesis of 2-(2-(3-(1-acetylpiperidin-4-yl)phenyl)piperidin-1-yl)-N-(5-methylpyridin-3-yl)-2-oxoacetamide (Compound 7

To a suspension of 1-[4-[3-(2-piperidyl)phenyl]-1-piperidyl]ethanone (0.4 g, 1.40 mmol), 2-[(5-methyl-3-pyridyl)amino]-2-oxo-acetic acid (392.93 mg, 1.40 mmol, Et$_3$N) and HATU (584.13 mg, 1.54 mmol) in DMF (3 mL), triethylamine (423.96 mg, 4.19 mmol, 583.97 μL) was added. The resulting mixture was stirred at 25° C. for 3 hr. The resulting mixture was purified by HPLC (LC 09 40-40-75% 0-1-6 min 0.1% NH$_3$-methanol, flow: 30 ml/min (loading pump 4 ml/min methanol) target mass 448 column: YMC Triart C18 100×20 mm, 5 um) to obtain 2-[2-[3-(1-acetyl-4-piperidyl)phenyl]-1-piperidyl]-N-(5-methyl-3-pyridyl)-2-oxo-acetamide (0.395 g, 880.60 μmol, 63.05% yield).
$^1$H NMR (500 MHz, CDCl$_3$) δ (ppm) 1.63 (m, 4H), 1.71 (m, 2H), 1.91 (m, 4H), 2.13 (m, 3H), 2.34 (m, 3H), 2.49 (m, 1H), 2.61 (m, 1H), 2.98 (m, 3H), 4.29 (m, 1H), 4.84 (m, 1H), 6.14 (m, 1H), 7.11 (m, 3H), 7.32 (m, 1H), 8.03 (m, 1H), 8.23 (m, 1H), 8.53 (m, 1H), 9.46 (m, 1H).

LCMS(ESI): [M]⁺ m/z: calcd 448.6; found 449.2; Rt=3.090 min.

Step 2: Chiral Separation (Compound 78 and Compound 73

Purification on the chiral column was taken in the system Hex-IPA-MeOH, 60-20-20, 0.6 mL/min. Number of injections: 1, injection volume: 40 mkl. From 38.82 mg of racemate, 15.34 mg and 14.79 mg of the individual enantiomers were obtained.

Rel-(R)-2-(2-(3-(1-acetylpiperidin-4-yl)phenyl)piperidin-1-yl)-N-(5-methylpyridin-3-yl)-2-oxoacetamide Peak 2 Compound 78

Retention time: 38.02 min $^1$H NMR (600 MHz, DMSO-d$_6$) δ (ppm) 1.41 (m, 2H), 1.55 (m, 2H), 1.62 (m, 2H), 1.80 (m, 3H), 2.01 (m, 3H), 2.27 (m, 3H), 2.66 (m, 3H), 3.05 (m, 2H), 3.78 (m, 2H), 4.51 (m, 1H), 5.47 (m, 1H), 7.15 (m, 3H), 7.33 (m, 1H), 7.92 (m, 1H), 8.16 (m, 1H), 8.57 (m, 1H), 11.08 (m, 1H).

LCMS(ESI): [M]⁺ m/z: calcd 448.6; found 449.2; Rt=3.909 min.

Rel-(S)-2-(2-(3-(1-acetylpiperidin-4-yl)phenyl)piperidin-1-yl)-N-(5-methylpyridin-3-yl)-2-oxoacetamide Peak 1 Compound 73

Retention time: 27.22 min $^1$H NMR (600 MHz, DMSO-d$_6$) δ (ppm) 1.41 (m, 2H), 1.57 (m, 2H), 1.62 (m, 2H), 1.75 (m, 3H), 2.01 (m, 3H), 2.27 (m, 3H), 2.69 (m, 3H), 3.05 (m, 2H), 3.78 (m, 2H), 4.51 (m, 1H), 5.65 (m, 1H), 7.15 (m, 3H), 7.33 (m, 1H), 7.95 (m, 1H), 8.18 (m, 1H), 8.62 (m, 1H), 11.08 (m, 1H).

LCMS(ESI): [M]⁺ m/z: calcd 448.6; found 449.2; Rt=3.910 min.

Example 27. The Synthesis of 5-(2-(2-(3-(1-acetylpiperidin-4-yl)phenyl)-5-methylpiperidin-1-yl)-2-oxoacetamido)Nicotinamide (Compound 346, Compound 332

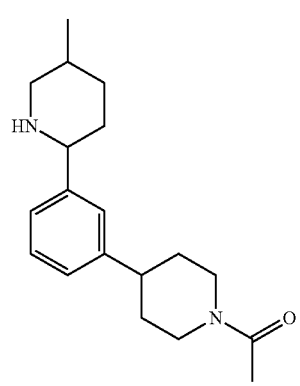 [SMILES: CC(=O)N1CCC(c2cccc(C3CCC(C)CN3)c2)CC1]

+

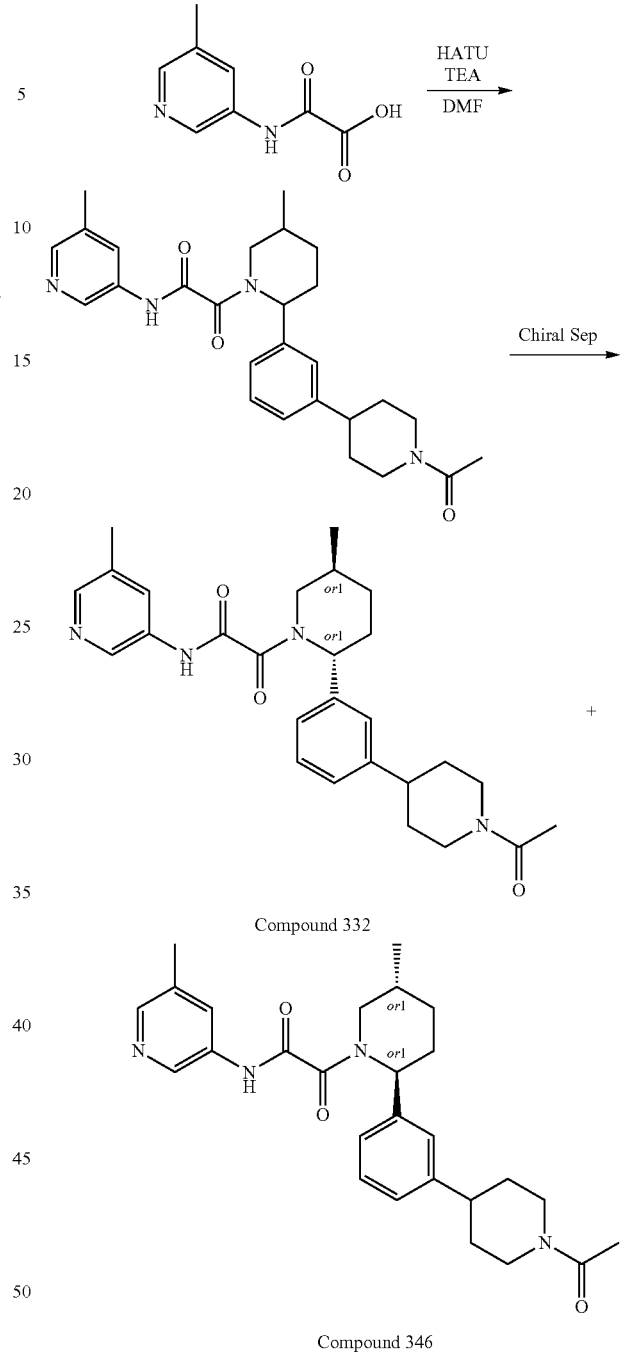

Step 1: Synthesis of 2-(2-(3-(1-acetylpiperidin-4-yl)phenyl)-5-methylpiperidin-1-yl)-N-(5-methylpyridin-3-yl)-2-oxoacetamide To a suspension of 1-[4-[3-(5-methyl-2-piperidyl)phenyl]-1-piperidyl]ethanone (0.3 g, 998.54 μmol), 2-[(5-carbamoyl-3-pyridyl)amino]-2-oxo-acetic acid (245.26 mg, 998.54 μmol, HCl) and triethylamine (101.04 mg, 998.54 μmol, 139.18 μL) in DMF (5 mL), HATU (379.68 mg, 998.54 μmol) was added. The reaction mixture was stirred at 40° C. for 24 hr and subjected to HPLC: 20-20-65% 0-1-6 min 0.10% NH$_3$-methanol, flow: 30 ml/min (loading pump 4 ml/min methanol) target mass 491 column: XBridge C18 100×20 mm, 5 um) to obtain 5-[[2-[2-[3-(1-acetyl-4-piperidyl)phenyl]-5-methyl-1-piperidyl]-2-oxo-acetyl]amino]pyridine-3-carboxamide (0.150 g, 305.14 µmol, 30.56% yield).

$^1$H NMR (500 MHz, DMSO-$d_6$) δ (ppm) 1.03 (m, 3H), 1.34 (m, 2H), 1.75 (m, 6H), 2.02 (s, 3H), 2.24 (m, 1H), 2.58 (m, 1H), 2.77 (m, 1H), 3.12 (m, 1H), 3.27 (m, 1H), 3.47 (m, 1H), 3.90 (m, 1H), 4.01 (m, 1H), 4.52 (m, 1H), 5.52 (m, 1H), 7.21 (m, 2H), 7.34 (m, 1H), 7.61 (m, 1H), 8.18 (m, 1H), 8.49 (m, 1H), 8.79 (m, 1H), 8.92 (m, 1H), 11.31 (m, 1H).

LCMS(ESI): [M]$^+$ m/z: calcd 491.6; found 492.2; Rt=3.016 min.

Step 2: Chiral Separation (Compound 332 and Compound 346

Purification on the chiral column was taken in the system Hex-IPA-MeOH, 70-5-15, 12 mL/min. Number of injections: 1, injection volume: 900 mkl. From 150 mg of racemate, 57 mg and 69 mg of the individual enantiomers were obtained.

Rel-5-(2-((2R,5S)-2-(3-(1-acetylpiperidin-4-yl)phenyl)-5-methylpiperidin-1-yl)-2-oxoacetamido)Nicotinamide Peak 1

Retention time: 18.32 min
$^1$H NMR (600 MHz, DMSO-$d_6$) δ (ppm) 1.02 (m, 3H), 1.32 (m, 1H), 1.42 (m, 1H), 1.67 (m, 4H), 1.87 (m, 1H), 1.99 (m, 3H), 2.08 (m, 1H), 2.22 (m, 1H), 2.54 (m, 1H), 2.82 (m, 2H), 3.15 (m, 1H), 3.78 (m, 2H), 4.50 (m, 1H), 5.35 (m, 1H), 7.15 (m, 3H), 7.31 (m, 1H), 7.60 (m, 1H), 8.15 (m, 1H), 8.47 (m, 1H), 8.75 (m, 1H), 8.85 (m, 1H), 11.23 (m, 1H).

LCMS(ESI): [M]$^+$ m/z: calcd 491.6; found 492.2; Rt=2.867 min.

Rel-5-(2-((2R,5S)-2-(3-(1-acetylpiperidin-4-yl)phenyl)-5-methylpiperidin-1-yl)-2-oxoacetamido)Nicotinamide Peak 2 Compound 346

Retention time: 31.56 min
$^1$H NMR (600 MHz, DMSO-$d_6$) δ (ppm) 1.02 (m, 3H), 1.32 (m, 1H), 1.42 (m, 1H), 1.66 (m, 4H), 1.87 (m, 1H), 1.99 (m, 3H), 2.04 (m, 1H), 2.22 (m, 1H), 2.54 (m, 1H), 2.77 (m, 2H), 3.17 (m, 1H), 3.78 (m, 2H), 4.50 (m, 1H), 5.35 (m, 1H), 7.14 (m, 3H), 7.31 (m, 1H), 7.60 (m, 1H), 8.15 (m, 1H), 8.47 (m, 1H), 8.75 (m, 1H), 8.85 (m, 1H), 11.23 (m, 1H).

LCMS(ESI): [M]$^+$ m/z: calcd 491.6; found 492.2; Rt=2.865 min.

Example 28. The Synthesis of rac-5-[[2-oxo-2-[(1R,4R,5S)-4-phenyl-3-azabicyclo[3.2.1]octan-3-yl]acetyl]amino]pyridine-3-carboxamide (Compound 86), 5-[[2-oxo-2-[(1R,4R,5S)-4-phenyl-3-azabicyclo[3.2.1]octan-3-yl]acetyl]amino]pyridine-3-carboxamide and 5-[[2-oxo-2-[(1S,4S,5R)-4-phenyl-3-azabicyclo[3.2.1]octan-3-yl]acetyl]amino]pyridine-3-carboxamide (Compound 205 and Compound 194

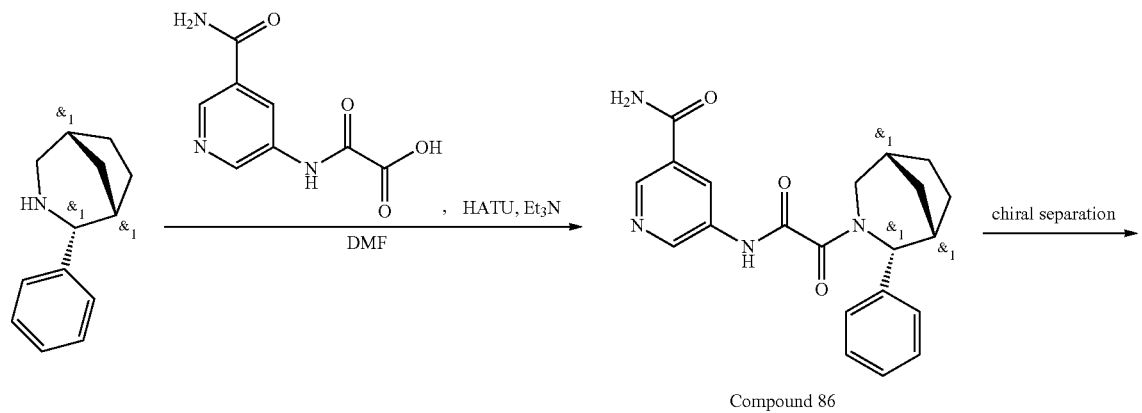

Compound 86

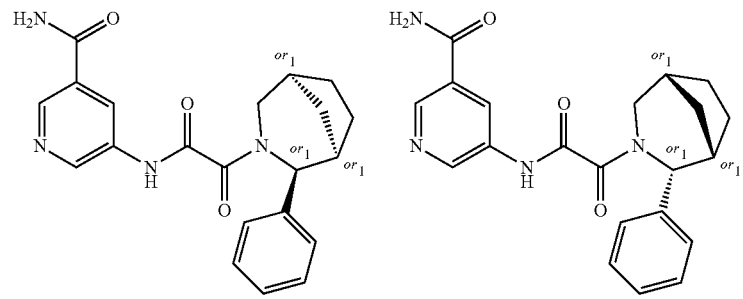

Compound 194        Compound 205

Step 1: Synthesis of rac-5-[[2-oxo-2-[(1R,4R,5S)-4-phenyl-3-azabicyclo[3.2.1]octan-3-yl]acetyl]amino]pyridine-3-carboxamide (Compound 86

To a stirred suspension of rac-(1R,4R,5S)-4-phenyl-3-azabicyclo[3.2.1]octane (200.00 mg, 1.07 mmol), 2-[(5-carbamoyl-3-pyridyl)amino]-2-oxo-acetic acid (Et₃N salt, 331.43 mg, 1.07 mmol) and HATU (446.66 mg, 1.17 mmol) in DMF (3 mL) was added, Triethylamine (540.31 mg, 5.34 mmol, 744.23 µL). The resulting reaction mixture was stirred at 40° C. for 5 hours. After 5 hours, the crude reaction mixture was purified by reverse phase HPLC (Mobile Phase: water—MeOH+0.1% NH₃, 0-5 min, 15-65%, flow rate: 30 mL/min; loading pump: 4 mL/min, MeOH+0.1% NH₃; column: YMC-Actus Triart C18 100*20 mm, 5 um) to give product rac-5-[[2-oxo-2-[(1R,4R,5S)-4-phenyl-3-azabicyclo[3.2.1]octan-3-yl]acetyl]amino]pyridine-3-carboxamide (150 mg, 396.38 µmol, 37.12% yield) as a white solid.

LCMS(ESI): [M+H]⁺ m/z: calcd 378.2; found 379.2; Rt=2.755 min.

Step 2: Chiral Separation of 5-[[2-oxo-2-[(1R,4R,5S)-4-phenyl-3-azabicyclo[3.2.]octan-3-yl]acetyl]amino]pyridine-3-carboxamide and 5-[[2-oxo-2-[(1S,4S,5R)-4-phenyl-3-azabicyclo[3.2.1]octan-3-yl]acetyl]amino]pyridine-3-carboxamide (Compound 205 and Compound 194 rac-5-[[2-oxo-2-[(1R,4R,5S)-4-phenyl-3-azabicyclo[3.2.1]octan-3-yl]acetyl]amino]pyridine-3-carboxamide (100 mg, 264.25 µmol) was subjected to chiral chromatography (Column: YMC 250*20 mm, 5 um, Eluent: Hexane-IPA-MeOH, 40-30-30; flow rate: 12 mL/min) to obtain 5-[[2-oxo-2-[(1R,4R,5S)-4-phenyl-3-azabicyclo[3.2.1]octan-3-yl]acetyl]amino]pyridine-3-carboxamide (46 mg, Compound 205) and 5-[[2-oxo-2-[(1S,4S,5R)-4-phenyl-3-azabicyclo[3.2.1]octan-3-yl]acetyl]amino]pyridine-3-carboxamide (48 mg, Compound 194

Compound 205: ¹H NMR (DMSO, 600 MHz): δ (ppm) 1.24 (m, 2H), 1.53 (m, 3H), 1.78 (m, 1H), 2.40 (m, 1H), 2.61 (m, 1H), 3.49 (m, 1H), 3.85 (m, 1H), 5.27 (m, 1H), 7.12 (m, 4H), 7.31 (t, 1H), 7.55 (m, 1H), 7.99 (m, 1H), 8.23 (m, 1H), 8.53 (m, 1H), 8.82 (m, 1H), 10.73 (m, 1H).

LCMS(ESI): [M+H]⁺ m/z: calcd 378.2; found 379.0; Rt=4.240 min. Chiral HPLC: Rt=16.26 min (Column: IC; Mobile phase: Hexane-MeOH-IPA, 40-30-30; Flow Rate: 0.6 mL/min).

Compound 194: ¹H NMR (DMSO-d₆, 600 MHz): δ (ppm) 1.24 (m, 2H), 1.53 (m, 3H), 1.76 (m, 1H), 2.36 (m, 1H), 2.62 (m, 1H), 3.49 (m, 1H), 3.85 (m, 1H), 5.27 (m, 1H), 7.00 (m, 3H), 7.28 (m, 2H), 7.55 (m, 1H), 7.99 (m, 1H), 8.23 (m, 1H), 8.53 (m, 1H), 8.82 (m, 1H), 10.74 (m, 1H).

LCMS(ESI): [M+H]⁺ m/z: calcd 378.2; found 379.0; Rt=4.237 min. Chiral HPLC: Rt=38.56 min (Column: IC; Mobile phase: Hexane-MeOH-IPA, 40-30-30; Flow Rate: 0.6 mL/min).

Example 29. The Synthesis of 5-(2-(2-cyclopentylpiperidin-1-yl)-2-oxoacetamido)-2-methoxynicotinamide (Compound 289, Compound 294

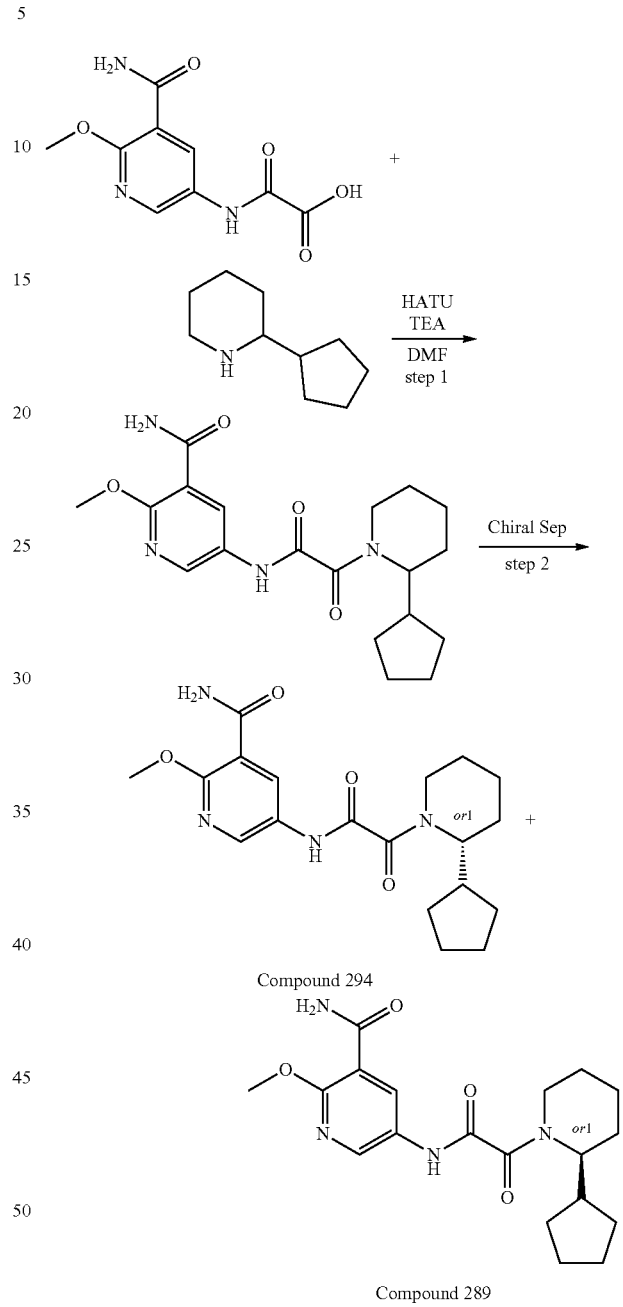

Compound 294

Compound 289

Step 1: Synthesis of 5-(2-(2-cyclopentylpiperidin-1-yl)-2-oxoacetamido)-2-methoxynicotinamide 2-[(5-carbamoyl-6-methoxy-3-pyridyl)amino]-2-oxo-acetic acid (0.5 g, 1.47 mmol, Et₃N), TATU (567.73 mg, 1.76 mmol) and TEA (148.65 mg, 1.47 mmol, 204.75 µL) were mixed in dry DMF (15 mL) at 21° C. and the resulting mixture was stirred for 1 hr. 2-cyclopentylpiperidine (225.14 mg, 1.47 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (40-90% 0.5-5 min; water-MeOH (+NH₃); 30 ml/min; loading pump 4 ml/min; column xbridge 20*100 mm). 5-[[2-(2-cyclopentyl-1-piperidyl)-2-oxo-acetyl]amino]-2-methoxy-pyridine-3-carboxamide (251.3 mg, 671.15 μmol, 45.69% yield) was obtained as a yellow gum.

$^1$H NMR (400 MHz, DMSO-d$_6$) δ (ppm) 1.61 (m, 15H), 3.21 (t, 1H), 3.56 (t, 1H), 3.96 (s, 3H), 4.22 (d, 1H), 7.75 (m, 2H), 8.46 (m, 1H), 8.56 (m, 1H), 10.89 (m, 1H). LCMS (ESI): [M+1]$^+$ m/z: calcd 374.4; found 375.2; Rt=1.257 min.

Step 2: Chiral Separation (Compound 289, Compound 294

Purification on the chiral column was taken in the system Hexane-IPA-MeOH, 60-20-20, 0.6 mL/min. Number of injections: 1, injection volume: 1 mkl. From 251.3 mg of racemate, 112.88 mg and 109.48 mg of the individual enantiomers were obtained.

Compound 289: Retention time: 22.02 min $^1$H NMR (500 MHz, DMSO-d$_6$) δ (ppm) 1.03-1.26 (m, 2H), 1.37-1.80 (m, 13H), 2.78-3.19 (m, 1H), 3.57 (t, 1H), 3.95 (s, 3H), 4.19-4.27 (m, 1H), 7.74 (s, 2H), 8.42-8.49 (m, 1H), 8.50-8.58 (m, 1H), 10.81-10.93 (m, 1H).

LCMS(ESI): [M+1]$^+$ m/z: calcd 374.2; found 375.2; Rt=3.305 min.

Compound 294: Retention time: 30.45 min $^1$H NMR (500 MHz, DMSO-d$_6$) δ (ppm) 0.99-1.23 (m, 2H), 1.31-1.80 (m, 13H), 2.77-3.17 (m, 1H), 3.56 (t, 1H), 3.95 (s, 3H), 4.16-4.27 (m, 1H), 7.70-7.85 (m, 2H), 8.43-8.48 (m, 1H), 8.50-8.58 (m, 1H), 10.80-10.93 (m, 1H).

LCMS(ESI): [M+1]$^+$ m/z: calcd 374.2; found 375.2; Rt=3.313 min.

Example 30. The Synthesis of 5-(2-(3,5-dimethyl-2-phenylpiperidin-1-yl)-2-oxoacetamido)Nicotinamide (Compound 183, Compound 275, Compound 311, Compound 267, Compound 286

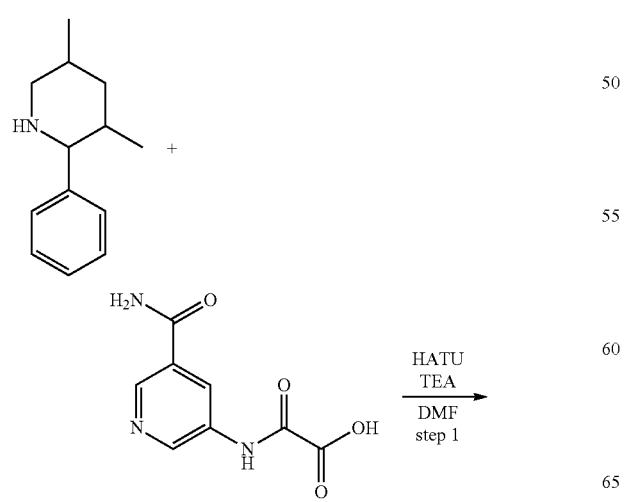

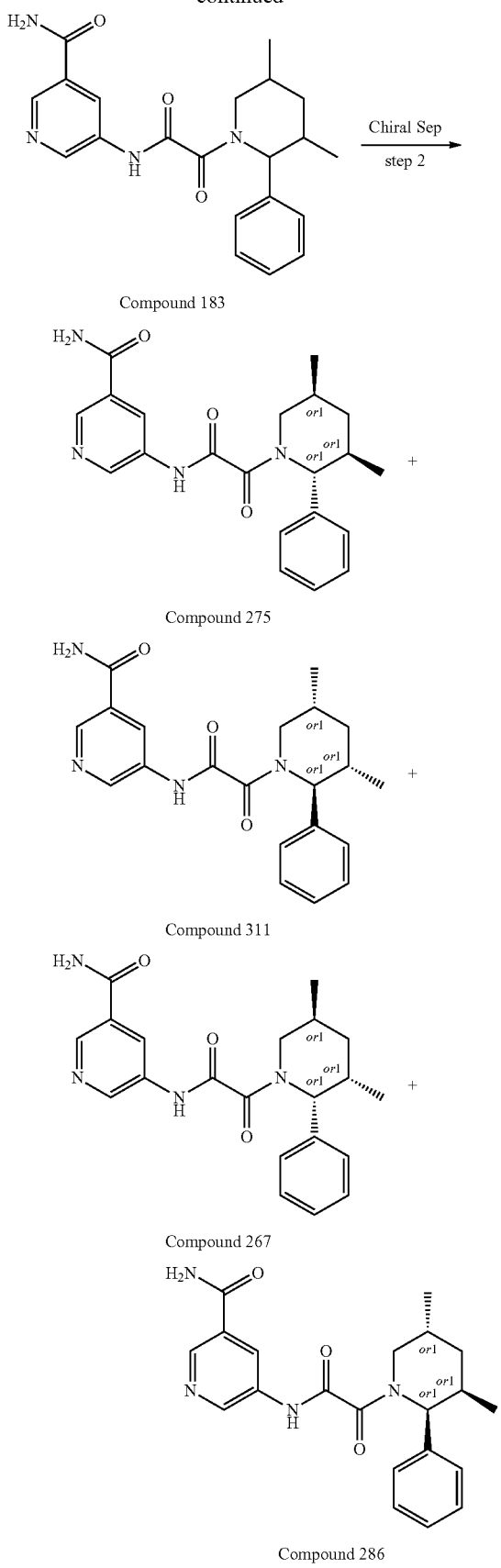

Compound 183

Compound 275

Compound 311

Compound 267

Compound 286

Step 1: Synthesis of 5-(2-(3,5-dimethyl-2-phenylpiperidin-1-yl)-2-oxoacetamido)Nicotinamide (Compound 183

To a suspension of 2-[(5-carbamoyl-3-pyridyl)amino]-2-oxo-acetic acid (0.4 g, 1.29 mmol, Et₃N), 3,5-dimethyl-2-phenyl-piperidine (268.38 mg, 1.42 mmol) and HATU (539.08 mg, 1.42 mmol) in DMF (4 mL), TEA (652.11 mg, 6.44 mmol, 898.22 µL) was added. The resulting mixture was stirred at 40° C. for 3 hr and subjected to HPLC: 20-45% 0-5 min water-0.1% FA-ACN flow 30 ml/min (loading pump 4 ml/min 0.1% FA-ACN); target mass 380.45 column: SunFire C18 100×18 mm 5 um) to give 5-[[2-(3,5-dimethyl-2-phenyl-1-piperidyl)-2-oxo-acetyl]amino]pyridine-3-carboxamide (120 mg, 315.42 µmol, 24.47% yield).

¹H NMR (500 MHz, DMSO-d₆) δ (ppm) 0.86 (d, 3H), 0.96 (d, 3H), 1.07 (m, 1H), 1.91 (m, 1H), 2.06 (m, 1H), 2.16 (m, 1H), 3.84 (m, 2H), 4.52 (m, 1H), 7.42 (m, 4H), 7.62 (m, 1H), 8.17 (m, 1H), 8.42 (m, 1H), 8.82 (m, 1H). LCMS(ESI): [M]⁺ m/z: calcd 380.4; found 381.2; Rt=4.616 min.

Step 2: Chiral Separation (Compound 275, Compound 311, Compound 267 and Compound 286

Purification on the chiral column was taken in the system Hex-IPA-MeOH, 70-15-15, 0.6 mL/min. Number of injections: 1, injection volume: 2 mkl. From 120 mg of racemate, 8.5 mg, 14 mg, 37 mg and 40 mg of the individual enantiomers were obtained.

Compound 275: Retention time: 26.07 min LCMS(ESI): [M]⁺ m/z: calcd 380.4; found 381.2; Rt=4.834 min.

Compound 311: Retention time: 38.08 min ¹H NMR (500 MHz, DMSO-d₆) δ (ppm) 0.83-0.87 (m, 3H), 0.94-0.99 (m, 3H), 1.85-1.95 (m, 1H), 1.99-2.10 (m, 1H), 2.09-2.25 (m, 1H), 3.45-3.61 (m, 1H), 3.79-3.92 (m, 1H), 4.46-4.66 (m, 1H), 7.11-7.43 (m, 6H), 7.59 (s, 1H), 8.12-8.29 (m, 1H), 8.38-8.62 (m, 1H), 8.67-8.88 (m, 2H), 10.61-11.17 (m, 1H).
LCMS(ESI): [M]⁺ m/z: calcd 380.4; found 381.2; Rt=4.838 min.

Compound 267: Retention time: 32.12 min ¹H NMR (500 MHz, DMSO-d₆) δ (ppm) 0.64-0.76 (m, 3H), 1.00-1.10 (m, 3H), 1.35-1.43 (m, 1H), 1.87-2.00 (m, 1H), 2.11-2.24 (m, 1H), 2.25-2.36 (m, 1H), 3.37-3.96 (m, 2H), 4.97-5.43 (m, 1H), 7.25-7.29 (m, 1H), 7.29-7.36 (m, 2H), 7.36-7.48 (m, 2H), 7.55-7.64 (m, 1H), 8.10-8.20 (m, 1H), 8.41-8.51 (m, 1H), 8.71-8.77 (m, 1H), 8.79-8.86 (m, 1H), 10.89-11.23 (m, 1H). LCMS(ESI): [M]⁺ m/z: calcd 380.4; found 381.2; Rt=4.841 min.

Compound 286: Retention time: 23.06 min LCMS(ESI): [M]⁺ m/z: calcd 380.4; found 381.2; Rt=4.840 min.

Example 31. The Synthesis of 5-(2-(2-cyclohexylpiperidin-1-yl)-2-oxoacetamido)Nicotinamide (Compound 101, Compound 113, Compound 108

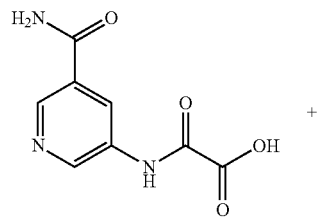

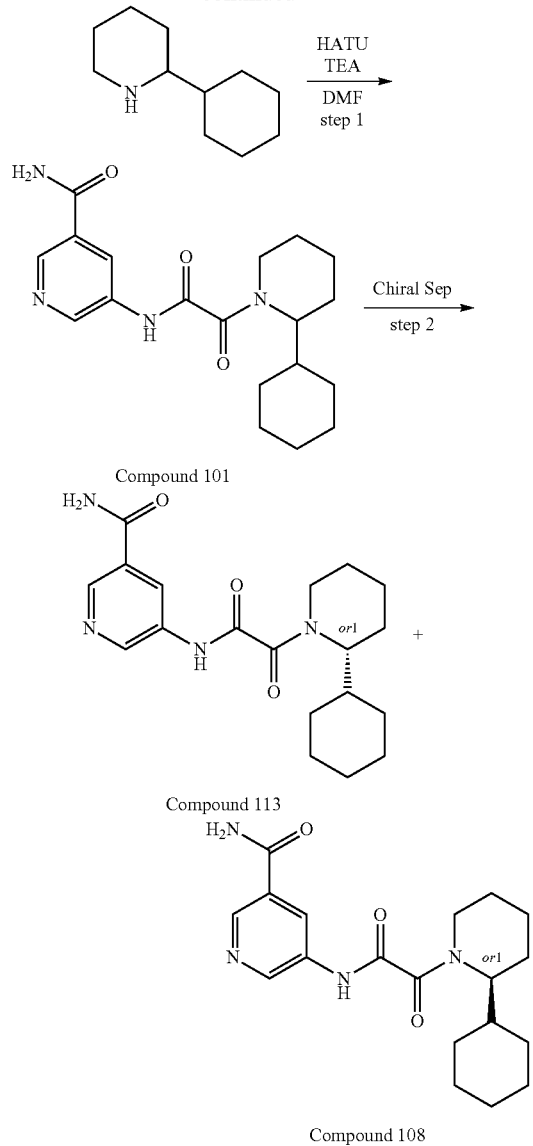

Step 1: Synthesis of 5-(2-(2-cyclohexylpiperidin-1-yl)-2-oxoacetamido)Nicotinamide (Compound 101)

2-[(5-carbamoyl-3-pyridyl)amino]-2-oxo-acetic acid (507.49 mg, 1.39 mmol) and 2-cyclohexylpiperidine (246.67 mg, 958.59 µmol) were mixed in DMF (10 mL). The reaction suspension was cooled to 0° C. and HATU (728.97 mg, 1.92 mmol) followed by TEA (582.00 mg, 5.75 mmol, 801.65 µL) were added. The clear solution was stirred at ambient temperature for 36 hr then volatiles were evaporated under reduced pressure and residue (1.5 g) was subjected to RP-HPLC (column: YMC Actus Triart C18 100×20 mm, 5 um; 40-70%, 0-5 min, 0.1% NH₃-methanol as mobile phase) to give Compound 101 5-[[2-(2-cyclohexyl-1-piperidyl)-2-oxo-acetyl]amino]pyridine-3-carboxamide (68.5 mg, 191.11 µmol, 19.94% yield).

¹H NMR (400 MHz, CDCl₃) δ (ppm) 0.93 (m, 2H), 1.17 (m, 3H), 1.59 (m, 8H), 1.77 (m, 4H), 1.93 (m, 1H), 2.89 (m, 1H), 4.49 (m, 2H), 6.13 (m, 1H), 8.60 (m, 1H), 8.79 (s, 1H), 8.93 (m, 1H), 9.68 (m, 1H). LCMS(ESI): [M+1]⁺ m/z: calcd 358.4; found 359.2; Rt=3.222 min.

Step 2: Chiral Separation (Compound 113, Compound 108)

Purification on the chiral column was taken in the system Hex-IPA-MeOH, 60-20-20, 0.6 mL/min. Number of injections: 1, injection volume: 1 mkl. From 30 mg of racemate, 14.2 mg and 14.5 mg of the individual enantiomers were obtained.

Compound 113: Retention time: 15.27 min ¹H NMR (500 MHz, DMSO-d₆) δ (ppm) 0.85 (m, 2H), 1.20 (m, 4H), 1.43 (m, 2H), 1.64 (m, 7H), 1.86 (m, 2H), 3.00 (m, 1H), 3.49 (m, 1H), 4.18 (m, 1H), 7.61 (m, 1H), 8.17 (m, 1H), 8.49 (s, 1H), 8.77 (s, 1H), 8.88 (m, 1H), 11.06 (m, 1H). LCMS(ESI): [M+1]⁺ m/z: calcd 358.2; found 359.2; Rt=4.677 min.

Compound 108: Retention time: 11.84 min ¹H NMR (500 MHz, DMSO-d₆) δ (ppm) 0.84 (m, 2H), 1.24 (m, 4H), 1.68 (m, 11H), 2.86 (m, 1H), 3.51 (m, 1H), 4.18 (m, 1H), 7.61 (m, 1H), 8.17 (m, 1H), 8.49 (s, 1H), 8.77 (s, 1H), 8.88 (m, 1H), 11.06 (s, 1H). LCMS(ESI): [M+1]+m/z: calcd 358.2; found 359.2; Rt=4.676 min.

Example 32. The Synthesis of 5-(2-(2-cyclohexylpiperidin-1-yl)-2-oxoacetamido)-2-methoxynicotinamide (Compound 347, Compound 317)

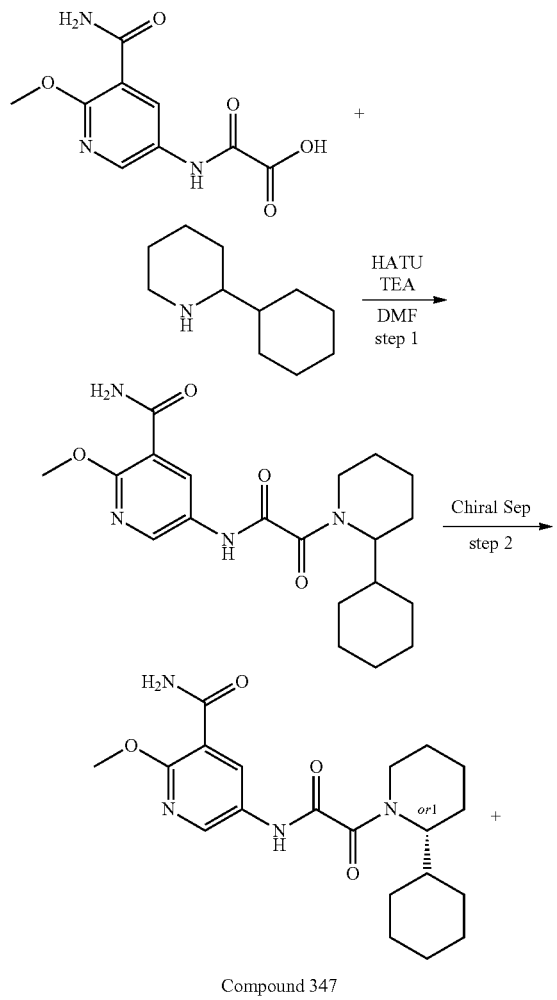

Compound 347

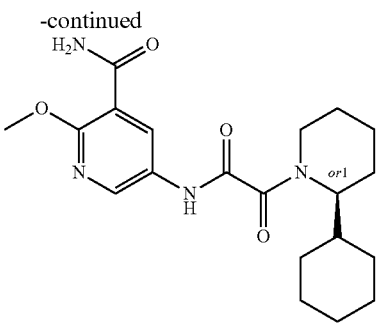

Compound 317

Step 1: Synthesis of 5-(2-(2-cyclohexylpiperidin-1-yl)-2-oxoacetamido)-2-methoxynicotinamide 2-cyclohexylpiperidine (0.25 g, 1.49 mmol), 2-[(5-carbamoyl-6-methoxy-3-pyridyl)amino]-2-oxo-acetic acid (508.66 mg, 1.49 mmol, Et₃N) and TEA (1.51 g, 14.94 mmol, 2.08 mL) were mixed together in DMF (5 mL) and HATU (852.33 mg, 2.24 mmol) was added thereto. The resulting mixture was stirred for 18 hr. The reaction mixture was poured into water (20 ml) and the resulting mixture was extracted with EtOAc (2*40 ml). Combined organic layers were washed with water (3*20 ml), brine, dried over Na₂SO₄, filtered and evaporated. The residue was purified by HPLC(2-10 min 60-85% MeOH/H₂O, 30 ml/min (loading pump 4 ml MeOH), column: SunFire 100*19 mm, 5 microM) to obtain 5-[[2-(2-cyclohexyl-1-piperidyl)-2-oxoacetyl]amino]-2-methoxy-pyridine-3-carboxamide (76.90 mg, 197.96 μmol, 13.25% yield).

¹H NMR (400 MHz, DMSO-d₆) δ (ppm) 0.86 (m, 2H), 1.08 (m, 3H), 1.23 (m, 2H), 1.58 (m, 8H), 1.86 (m, 2H), 2.66 (m, 1H), 3.57 (m, 1H), 3.98 (s, 3H), 4.22 (m, 1H), 7.75 (m, 2H), 8.53 (m, 2H), 10.86 (m, 1H). LCMS(ESI): [M+1]⁺ m/z: calcd 388.4; found 389.2; Rt=1.436 min.

Step 2: Chiral Separation (Compound 347, Compound 317)

Purification on the chiral column was taken in the system CO₂-MeOH, 50-50, 2 mL/min. Number of injections: 1, injection volume: 1 mkl. From 76.9 mg of racemate, 28.47 mg and 27.6 mg of the individual enantiomers were obtained.

Compound 347: Retention time: 6.93 min ¹H NMR (500 MHz, DMSO-d₆) δ (ppm) 0.83 (m, 2H), 1.17 (m, 3H), 1.41 (m, 1H), 1.62 (m, 9H), 1.84 (m, 2H), 3.07 (m, 1H), 3.56 (m, 1H), 3.95 (s, 3H), 4.19 (m, 1H), 7.74 (m, 2H), 8.46 (s, 1H), 8.54 (m, 1H), 10.85 (s, 1H). LCMS(ESI): [M+1]⁺ m/z: calcd 388.2; found 389.2; Rt=5.449 min.

Compound 317: Retention time: 5.78 min ¹H NMR (600 MHz, DMSO-d₆) δ (ppm) 0.83 (m, 2H), 1.14 (m, 3H), 1.39 (m, 1H), 1.65 (m, 9H), 1.83 (m, 2H), 2.85 (m, 1H), 3.48 (m, 1H), 3.93 (s, 3H), 4.13 (m, 1H), 7.73 (m, 2H), 8.44 (m, 1H), 8.51 (m, 1H), 10.84 (m, 1H). LCMS(ESI): [M]⁺ m/z: calcd 388.2; found 389.2; Rt=5.454 min.

Example 33. The Synthesis of 2-[(2R,5S)-2-(3-aminophenyl)-5-methyl-1-piperidyl]-N-(5-methyl-3-pyridyl)-2-oxo-acetamide (Compound 91) and 2-[(2S,5R)-2-(3-acetamidophenyl)-5-methyl-1-piperidyl]-N-(5-methyl-3-pyridyl)-2-oxo-acetamide (Compound 110

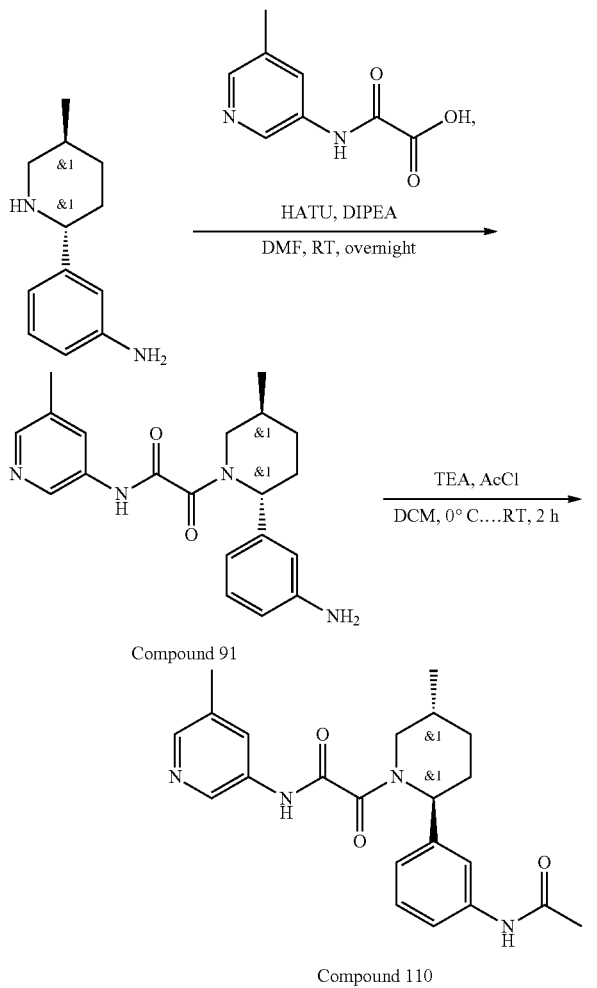

Compound 91

Compound 110

Step 1: The Synthesis of 2-[(2R,5S)-2-(3-aminophenyl)-5-methyl-1-piperidyl]-N-(5-methyl-3-pyridyl)-2-oxo-acetamide (Compound 91

2-[(5-methyl-3-pyridyl)amino]-2-oxo-acetic acid (297.00 mg, 1.37 mmol, HCl) was dissolved in DMF (5 mL), following by the addition of DIPEA (1.07 g, 8.24 mmol, 1.44 mL) and HATU (626.82 mg, 1.65 mmol). The resulting mixture was stirred for 10 min (change of color was observed) and 3-(5-methyl-2-piperidyl)aniline (0.5 g, 1.65 mmol, TFA) was added in one portion. The reaction mixture was stirred overnight. Evaporation of the solvent and purification by HPLC (27% 0.5-6.5 min; water-acetonitrile; flow 30 mL/min; (loading pump 4 mL/min acetonitrile); target mass 352; column SunFire 100*19 mm 5 um) gave 2-[(2R,5S)-2-(3-aminophenyl)-5-methyl-1-piperidyl]-N-(5-methyl-3-pyridyl)-2-oxo-acetamide (0.035 g, 99.31 μmol, 6.02% yield). Trans-configuration was confirmed by 2D NMR.

$^1$H NMR (400 MHz, DMSO-d$_6$) δ 0.99 (m, 3H), 1.30 (m, 1H), 1.69 (m, 1H), 1.81 (m, 1H), 1.95 (m, 1H), 2.08 (m, 1H), 2.25 (m, 3H), 3.22 (m, 1H), 3.42 (m, 1H), 5.17 (m, 3H), 6.44 (m, 3H), 6.98 (m, 1H), 7.89 (m, 1H), 8.14 (m, 1H), 8.60 (m, 1H), 10.99 (m, 1H).

LCMS(ESI): [M+H]$^+$ m/z: calcd 352.2; found 353.2; Rt=2.214 min.

Step 2: The Synthesis of 2-[(2S,5R)-2-(3-acetamidophenyl)-5-methyl-1-piperidyl]-N-(5-methyl-3-pyridyl)-2-oxo-acetamide (Compound 110

2-[(2S,5R)-2-(3-aminophenyl)-5-methyl-1-piperidyl]-N-(5-methyl-3-pyridyl)-2-oxo-acetamide (15.00 mg, 42.56 μmol) was dissolved in DCM and TEA (4.31 mg, 42.56 μmol, 5.93 μL) was added. The resulting mixture was cooled to 0° C. and acetyl chloride (3.34 mg, 42.56 μmol, 2.59 μL) was added dropwise. The reaction mixture was stirred for 2 h. Then, the solvent was removed under reduced pressure. The obtained residue was purified using HPLC (40-90% 0.5-6.5 min; water-MeOH; flow 30 mL/min; (loading pump 4 mL/min MeOH); target mass 394; column SunFire 100*19 mm 5 um) to afford 2-[(2S,5R)-2-(3-acetamidophenyl)-5-methyl-1-piperidyl]-N-(5-methyl-3-pyridyl)-2-oxo-acetamide (13 mg, 32.96 μmol, 77.43% yield).

$^1$H NMR (DMSO-d$_6$, 500 MHz): δ (ppm) 1.03 (dd, 3H), 1.34 (m, 1H), 1.71 (m, 1H), 1.91 (m, 1H), 2.03 (m, 3H), 2.12 (m, 2H), 2.28 (d, 3H), 3.05 (m, 1H), 3.77 (m, 1H), 5.36 (m, 1H), 7.00 (dd, 1H), 7.31 (m, 1H), 7.49 (m, 1H), 7.57 (d, 1H), 7.92 (m, 1H), 8.17 (m, 1H), 8.60 (m, 1H), 9.95 (m, 1H), 10.98 (m, 1H).

LCMS(ESI): [M+H]$^+$ m/z: calcd 394.2; found 395.2; Rt=2.671 min.

Example 34. The Synthesis of 5-[[2-[(2R)-2-[3-(methylamino)phenyl]-1-piperidyl]-2-oxo-acetyl]amino]pyridine-3-carboxamide (Compound 316) and 5-[[2-[(2S)-2-[3-(methylamino)phenyl]-1-piperidyl]-2-oxo-acetyl]amino]pyridine-3-carboxamide (Compound 334

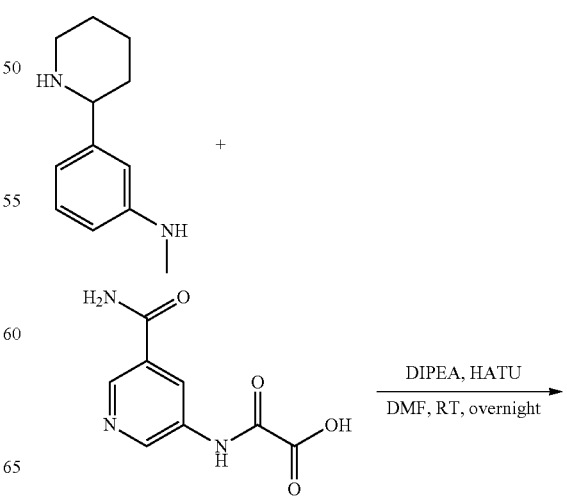

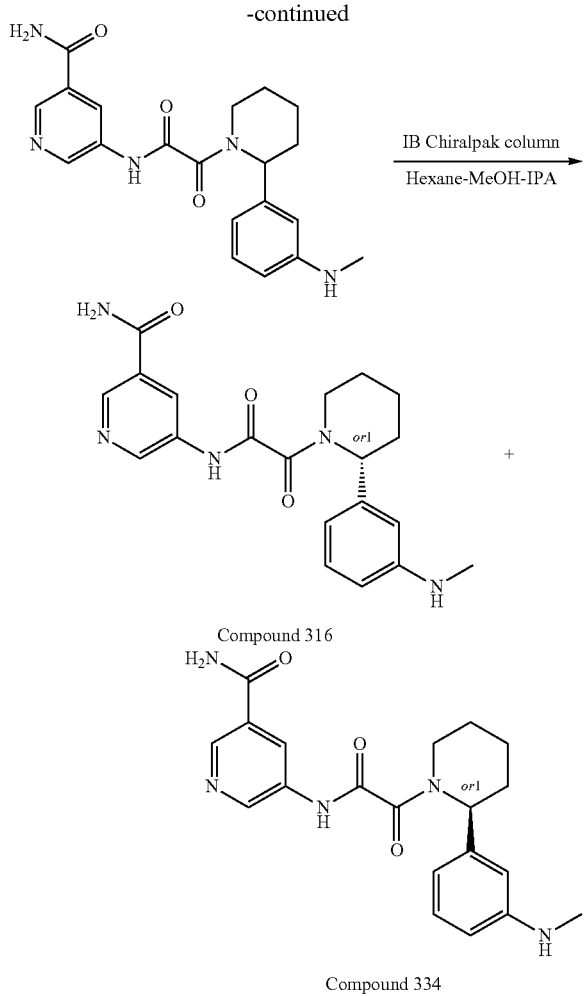

Compound 316

Compound 334

N-methyl-3-(2,3,4,5-tetrahydropyridin-6-yl)aniline (1.2 g, 6.37 mmol) and N-methyl-3-(2,3,4,5-tetrahydropyridin-6-yl)aniline (1.2 g, 6.37 mmol) were dissolved in MeOH (20 mL) and H₂O (20 mL). The resulting mixture was cooled to 25° C. and sodium borohydride (482.28 mg, 12.75 mmol, 450.73 µL) was added in portions. Then, the reaction mixture was additionally stirred overnight. After the completion of the reaction, the mixture was acidified with 10% aq HCl to pH 2. The obtained mixture was washed with MTBE (2*10 mL), basified with 10% aq NaOH to pH 10 and extracted with DCM (50 mL). Evaporation of the solvent resulted in pure N-methyl-3-(2-piperidyl)aniline (0.9 g, 4.73 mmol, 74.21% yield).

$^1$H NMR (400 MHz, CDCl$_3$) δ 1.74 (m, 8H), 2.82 (m, 4H), 3.12 (m, 1H), 3.51 (m, 1H), 6.47 (d, 1H), 6.65 (s, 1H), 6.68 (d, 1H), 7.11 (dd, 1H).

LCMS(ESI): [M+H]$^+$ m/z: calcd 190.1; found 191.2; Rt=0.539 min.

Step 1: The Synthesis of 5-[[2-[2-[3-(methylamino)phenyl]-1-piperidyl]-2-oxo-acetyl]amino]pyridine-3-carboxamide DIPEA (368.33 mg, 2.85 mmol, 496.41 µL) was added to the solution of respective 2-[(5-carbamoyl-3-pyridyl)amino]-2-oxo-acetic acid (0.2 g, 814.27 µmol, HCl) and N-methyl-3-(2-piperidyl)aniline (154.94 mg, 814.27 µmol) in DMF (10 mL). The resulting mixture was stirred for 5 min followed by the addition of the solution of HATU (340.57 mg, 895.69 µmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC (2-10 min 0-85% MeOH—H₂O; flow rate 30 mL/min; loading pump 4 mL MeOH; SunFire 100*19 mm, 5 mkm column) to afford pure 5-[[2-[2-[3-(methylamino)phenyl]-1-piperidyl]-2-oxo-acetyl]amino]pyridine-3-carboxamide (0.15 g, 393.26 µmol, 48.30% yield).

$^1$H NMR (400 MHz, CDCl$_3$) δ 1.55 (m, 4H), 1.87 (m, 1H), 2.47 (m, 1H), 2.81 (m, 3H), 3.12 (m, 1H), 3.52 (s, 3H), 4.52 (m, 1H), 6.15 (m, 2H), 6.62 (m, 2H), 7.20 (m, 1H), 8.52 (m, 1H), 8.78 (s, 1H), 9.02 (m, 1H), 10.05 (m, 1H).

LCMS(ESI): [M+H]$^+$ m/z: calcd 381.2; found 382.2; Rt=2.061 min.

Step 2: The Synthesis of 5-[[2-[(2R)-2-[3-(methylamino)phenyl]-1-piperidyl]-2-oxo-acetyl]amino]pyridine-3-carboxamide (Compound 316) and 5-[[2-[(2S)-2-[3-(methylamino)phenyl]-1-piperidyl]-2-oxo-acetyl]amino]pyridine-3-carboxamide (Compound 334)

Chiral separation of 5-[[2-[2-[3-(methylamino)phenyl]-1-piperidyl]-2-oxo-acetyl]amino]pyridine-3-carboxamide was performed using IB (250*20, 5 mkm) Chiralpak column; Hexane-MeOH-IPA, 60-20-20 as a mobile phase; flow rate 12 mL/min affording Compound 316—5-[[2-[(2R)-2-[3-(methylamino)phenyl]-1-piperidyl]-2-oxo-acetyl]amino]pyridine-3-carboxamide (61.9 mg, 41.27% yield; RT=11.456 min) and Compound 334—5-[[2-[(2S)-2-[3-(methylamino)phenyl]-1-piperidyl]-2-oxo-acetyl]amino]pyridine-3-carboxamide (58.4 mg, 38.93% yield; RT=15.476 min).

Compound 316:

RT (IB, Hexane-IPA-MeOH, 50-25-25, 0.6 mL/min)=16.409 min.

$^1$H NMR (400 MHz, CDCl$_3$) δ 1.60 (m, 1H), 1.90 (m, 2H), 2.42 (m, 1H), 2.63 (m, 1H), 2.80 (m, 3H), 3.03 (m, 2H), 4.48 (m, 1H), 5.98 (m, 2H), 6.42 (m, 1H), 6.55 (m, 2H), 6.63 (m, 1H), 7.18 (t, 1H), 8.57 (m, 1H), 8.78 (m, 1H), 8.96 (m, 1H), 9.88 (m, 1H).

LCMS(ESI): [M+H]$^+$ m/z: calcd 381.2; found 382.2; Rt=3.376 min.

Compound 334:

RT (IB, Hexane-IPA-MeOH, 50-25-25, 0.6 mL/min)=11.846 min.

$^1$H NMR (400 MHz, CDCl$_3$) δ1.55 (m, 1H), 1.96 (m, 2H), 2.43 (m, 1H), 2.61 (m, 1H), 2.80 (s, 3H), 2.95 (m, 2H), 4.49 (m, 1H), 5.97 (m, 2H), 6.42 (m, 1H), 6.55 (m, 2H), 6.63 (m, 1H), 7.18 (t, 1H), 8.57 (m, 1H), 8.78 (m, 1H), 8.97 (m, 1H), 9.91 (m, 1H).

LCMS(ESI): [M+H]$^+$ m/z: calcd 381.2; found 382.2; Rt=3.375 min.

Example 35. The Synthesis of 5-[[2-[(2R)-2-[3-(dimethylamino)phenyl]-1-piperidyl]-2-oxo-acetyl]amino]pyridine-3-carboxamide (Compound 366) and 5-[[2-[(2S)-2-[3-(dimethylamino)phenyl]-1-piperidyl]-2-oxo-acetyl]amino]pyridine-3-carboxamide (Compound 365

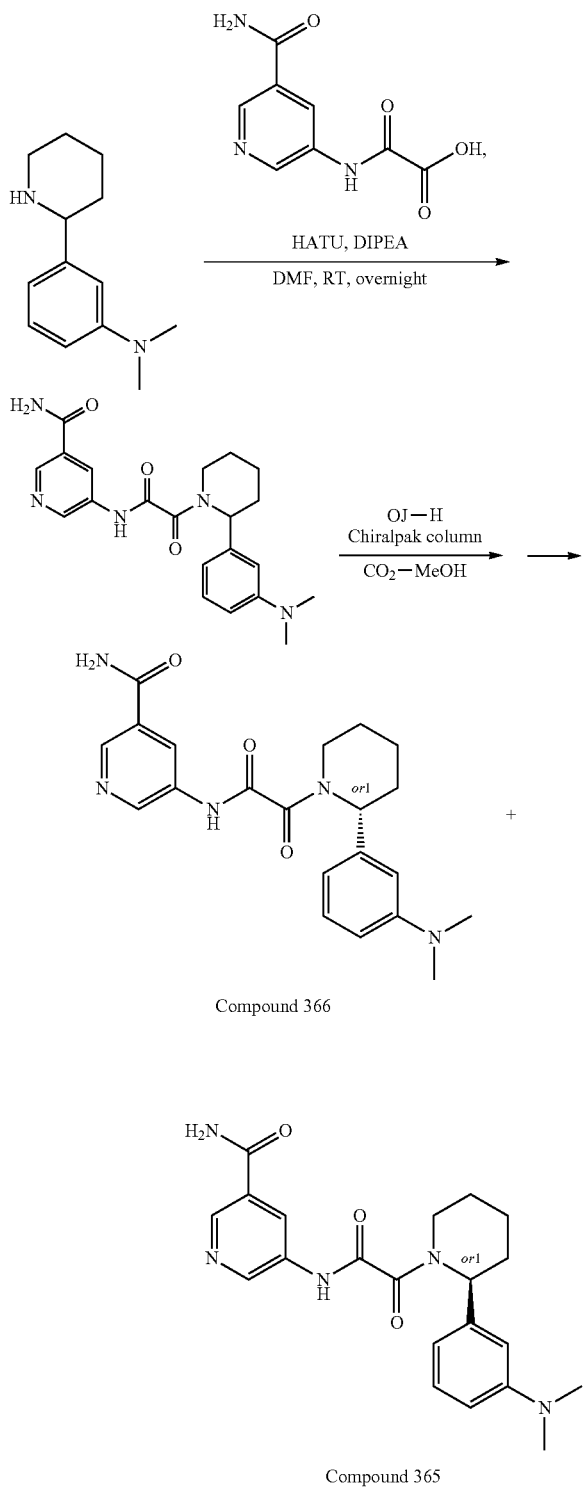

Compound 366

Compound 365

Step 1: The Synthesis of 5-[[2-[2-[3-(dimethylamino)phenyl]-1-piperidyl]-2-oxo-acetyl]amino]pyridine-3-carboxamide DIPEA (336.76 mg, 2.61 mmol, 453.86 µL) was added to the solution of respective 2-[(5-carbamoyl-3-pyridyl)amino]-2-oxo-acetic acid (0.16 g, 651.41 µmol, HCl) and N,N-dimethyl-3-(2-piperidyl)aniline (133.09 mg, 651.41 µmol) in DMF (5 mL). The resulting mixture was stirred for 5 min followed by the addition of the solution of HATU (272.46 mg, 716.56 µmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC (2-10 min, 35-60% $H_2O$-MeCN; loading pump 4 mL MeCN; Triart C18 100*20 5 mkm column) to afford pure 5-[[2-[2-[3-(dimethylamino)phenyl]-1-piperidyl]-2-oxo-acetyl]amino]pyridine-3-carboxamide (0.12 g, 303.45 µmol, 46.58% yield).

$^1$H NMR (400 MHz, $CDCl_3$) δ 1.42 (m, 3H), 1.96 (m, 2H), 2.40 (m, 1H), 2.92 (s, 6H), 3.18 (m, 1H), 3.47 (s, 2H), 4.49 (m, 1H), 6.08 (m, 2H), 6.72 (m, 3H), 8.54 (d, 1H), 8.81 (s, 1H), 9.01 (m, 1H), 9.87 (m, 1H).

LCMS(ESI): [M+H]$^+$ m/z: calcd 395.2; found 396.2; Rt=0.993 min.

Step 2: The Synthesis of 5-[[2-[(2R)-2-[3-(dimethylamino)phenyl]-1-piperidyl]-2-oxo-acetyl]amino]pyridine-3-carboxamide (Compound 366) and 5-[[2-[(2S)-2-[3-(dimethylamino)phenyl]-1-piperidyl]-2-oxo-acetyl]amino]pyridine-3-carboxamide (Compound 365)

Chiral separation of 5-[[2-[2-[3-(dimethylamino)phenyl]-1-piperidyl]-2-oxo-acetyl]amino]pyridine-3-carboxamide was preformed using OJ-H (250*30, 20 mkm) Chiralpak column; $CO_2$-MeOH, 60-40 as a mobile phase; flow rate 80 mL/min affording Compound 366-5-[[2-[(2R)-2-[3-(dimethylamino)phenyl]-1-piperidyl]-2-oxo-acetyl]amino]pyridine-3-carboxamide (40.3 mg, 33.58% yield; RT=10.140 min) and Compound 365—5-[[2-[(2S)-2-[3-(dimethylamino)phenyl]-1-piperidyl]-2-oxo-acetyl]amino]pyridine-3-carboxamide (41.1 mg, 34.25% yield; RT=4.335 min).

Compound 366:RT (OJ-H, $CO_2$-MeOH, 60-40, 2.0 mL/min)=7.26 min.

$^1$H NMR (600 MHz, DMSO-$d_6$) δ 1.40-1.56 (m, 2H), 1.57-1.68 (m, 2H), 1.76-1.94 (m, 1H), 2.41-2.44 (m, 1H), 2.61-2.67 (m, OH), 2.84-2.88 (m, 6H), 3.03-3.10 (m, 1H), 3.63-4.29 (m, 1H), 5.08-5.63 (m, 1H), 6.59-6.64 (m, 3H), 7.15-7.21 (m, 1H), 7.53-7.65 (m, 1H), 8.09-8.20 (m, 1H), 8.44-8.54 (m, 1H), 8.72-8.79 (m, 1H), 8.80-8.90 (m, 1H), 11.23-11.39 (m, 1H).

LCMS(ESI): [M+H]$^+$ m/z: calcd 395.2; found 396.2; Rt=0.932 min.

Compound 365:RT (OJ-H, $CO_2$-MeOH, 60-40, 2.0 mL/min)=4.07 min.

$^1$H NMR (600 MHz, DMSO-$d_6$) δ 1.37-1.54 (m, 2H), 1.56-1.68 (m, 2H), 1.77-1.94 (m, 1H), 2.41-2.44 (m, 1H), 2.59-2.67 (m, 0.3H), 2.84-2.89 (m, 6H), 3.02-3.12 (m, 0.7H), 3.64-4.33 (m, 1H), 5.07-5.64 (m, 1H), 6.58-6.67 (m, 3H), 7.15-7.22 (m, 1H), 7.53-7.66 (m, 1H), 8.11-8.23 (m, 1H), 8.43-8.54 (m, 1H), 8.70-8.79 (m, 1H), 8.80-8.91 (m, 1H), 11.22-11.35 (m, 1H).

LCMS(ESI): [M+H]⁺ m/z: calcd 395.2; found 396.2; Rt=0.931 min.

Example 36. The Synthesis of 5-[[2-[(2R,5S)-5-methyl-2-[3-(methylamino)phenyl]-1-piperidyl]-2-oxo-acetyl]amino]pyridine-3-carboxamide (Compound 321) and 5-[[2-[(2S,5R)-5-methyl-2-[3-(methylamino)phenyl]-1-piperidyl]-2-oxo-acetyl]amino]pyridine-3-carboxamide (Compound 348

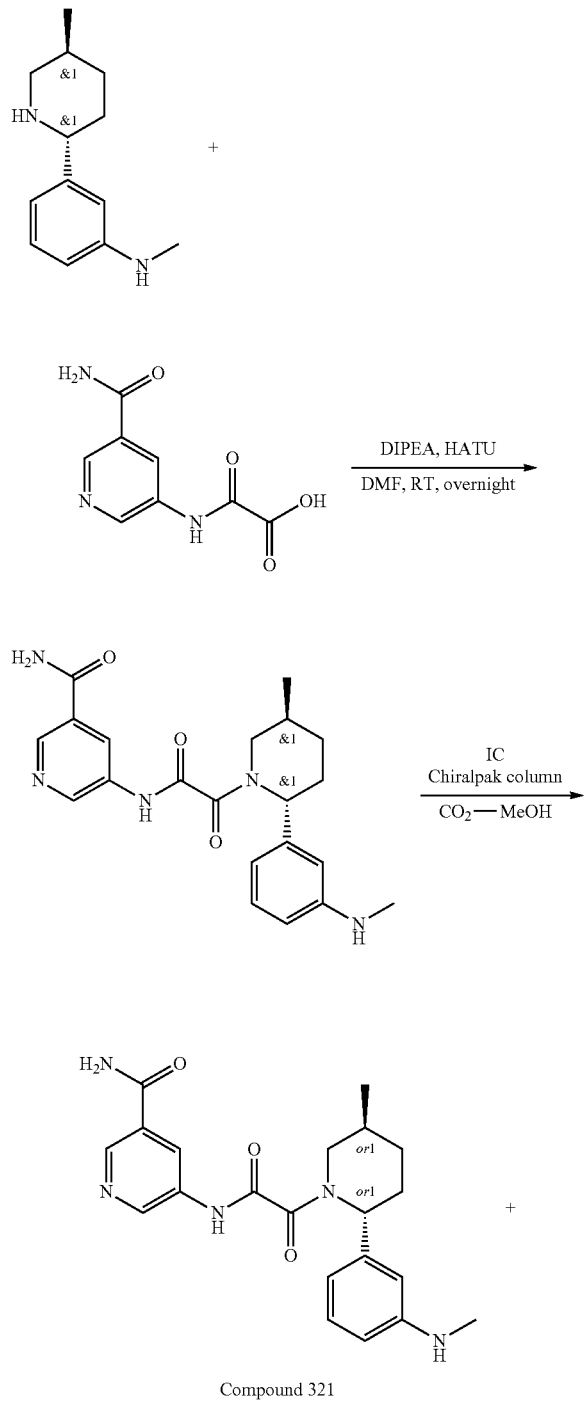

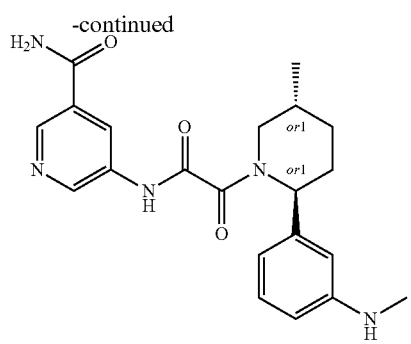

Compound 348

Step 1: The Synthesis of 5-[[2-[(2R,5S)-5-methyl-2-[3-(methylamino)phenyl]-1-piperidyl]-2-oxo-acetyl]amino]pyridine-3-carboxamide DIPEA (331.50 mg, 2.56 mmol, 446.77 µL) was added to the solution of respective 2-[(5-carbamoyl-3-pyridyl)amino]-2-oxo-acetic acid (0.18 g, 732.84 µmol, HCl) and N-methyl-3-[(2S,5R)-5-methyl-2-piperidyl]aniline (149.73 mg, 732.84 µmol) in DMF (10 mL). The resulting mixture was stirred for 5 min followed by the addition of the solution of HATU (306.51 mg, 806.12 µmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC (2-10 min 0-85% MeCN—H₂O as a mobile phase, flow rate 30 mL/min; loading pump 4 mL MeCN; SunFire C18 19*100 mm 5 mkm column) to afford pure 5-[[2-[(2R,5S)-5-methyl-2-[3-(methylamino)phenyl]-1-piperidyl]-2-oxo-acetyl]amino]pyridine-3-carboxamide (0.17 g, 429.89 µmol, 58.66% yield).

¹H NMR (400 MHz, CDCl₃) δ 1.08 (m, 3H), 1.37 (m, 1H), 1.94 (m, 3H), 2.21 (m, 2H), 2.77 (s, 3H), 3.41 (m, 1H), 3.49 (m, 1H), 4.34 (m, 1H), 6.28 (m, 3H), 7.22 (m, 1H), 8.58 (m, 1H), 8.72 (s, 1H), 8.99 (m, 1H), 9.89 (m, 1H).

LCMS(ESI): [M+H]⁺ m/z: calcd 395.2; found 396.2; Rt=2.354 min.

Step 2: The Synthesis of 5-[[2-[(2R,5S)-5-methyl-2-[3-(methylamino)phenyl]-1-piperidyl]-2-oxo-acetyl]amino]pyridine-3-carboxamide (Compound 321) and 5-[[2-[(2S,5R)-5-methyl-2-[3-(methylamino)phenyl]-1-piperidyl]-2-oxo-acetyl]amino]pyridine-3-carboxamide (Compound 348

Chiral separation of 5-[[2-[(2R,5S)-5-methyl-2-[3-(methylamino)phenyl]-1-piperidyl]-2-oxo-acetyl]amino]pyridine-3-carboxamide was performed using IC (250*20, 5 mkm) column, CO₂-MeOH, 55-45 as a mobile phase; flow rate 40 mL/min affording Compound 321—5-[[2-[(2R,5S)-5-methyl-2-[3-(methylamino)phenyl]-1-piperidyl]-2-oxo-acetyl]amino]pyridine-3-carboxamide (65.2 mg, 38.35% yield; RT=16.522 min) and Compound 348—5-[[2-[(2S,5R)-5-methyl-2-[3-(methylamino)phenyl]-1-piperidyl]-2-oxo-acetyl]amino]pyridine-3-carboxamide (59.8 mg, 35.18% yield; RT=10.591 min).

Compound 321:RT (IC, CO₂-MeOH, 50-50, 2.0 mL/min) =7.03 min.

¹H NMR (600 MHz, DMSO-d₆) δ 1.01 (m, 3H), 1.32 (m, 1H), 1.70 (m, 1H), 1.87 (m, 1H), 2.06 (m, 2H), 2.63 (m, 3H), 2.83 (m, 1H), 3.73 (m, 1H), 5.28 (m, 1H), 5.59 (m, 1H), 6.40 (m, 1H), 6.48 (m, 2H), 7.07 (m, 1H), 7.59 (m, 1H), 8.15 (m, 1H), 8.47 (m, 1H), 8.75 (m, 1H), 8.87 (m, 1H), 11.19 (m, 1H).

LCMS(ESI): [M+H]+ m/z: calcd 395.2; found 396.2; Rt=3.582 min.

Compound 348 RT (IC, $CO_2$-MeOH, 50-50, 2.0 mL/min) =5.40 min.

$^1$H NMR (600 MHz, DMSO-$d_6$) δ 1.01 (m, 3H), 1.32 (m, 1H), 1.70 (m, 1H), 1.87 (m, 1H), 2.06 (m, 2H), 2.63 (m, 3H), 2.83 (m, 1H), 3.73 (m, 1H), 5.29 (m, 1H), 5.62 (m, 1H), 6.40 (m, 1H), 6.49 (m, 2H), 7.07 (m, 1H), 7.59 (m, 1H), 8.15 (m, 1H), 8.48 (m, 1H), 8.75 (m, 1H), 8.88 (m, 1H), 11.19 (m, 1H).

LCMS(ESI): [M+H]+ m/z: calcd 395.2; found 396.2; Rt=3.575 min.

Example 37. The Synthesis of 5-[[2-[(2R,5S)-2-[3-(dimethylamino)phenyl]-5-methyl-1-piperidyl]-2-oxo-acetyl]amino]pyridine-3-carboxamide (Compound 374) and 5-[[2-[(2S,5R)-2-[3-(dimethylamino)phenyl]-5-methyl-1-piperidyl]-2-oxo-acetyl]amino]pyridine-3-carboxamide (Compound 375

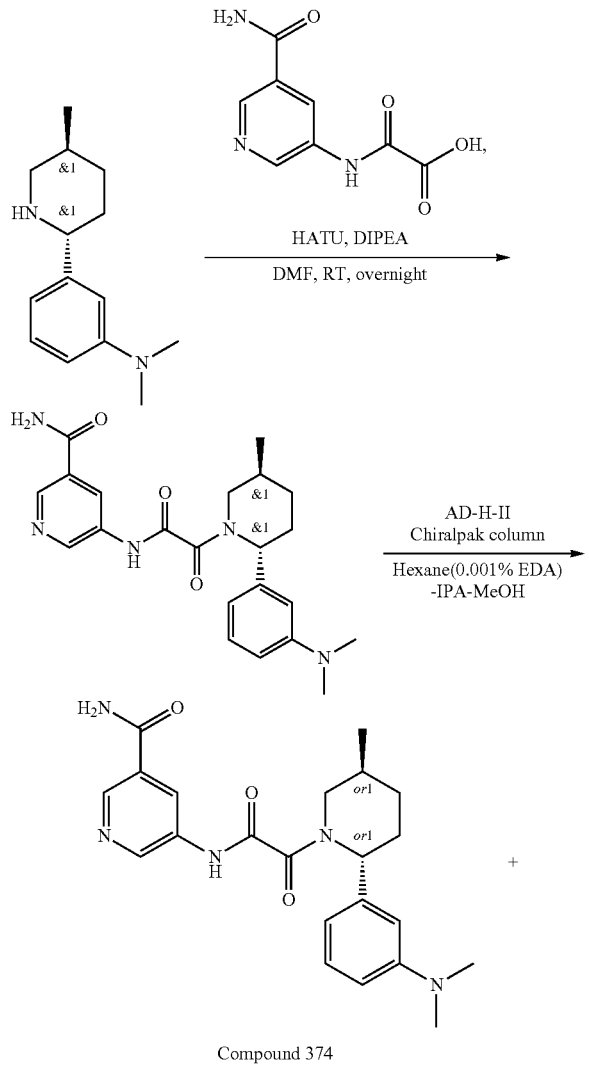

Compound 374

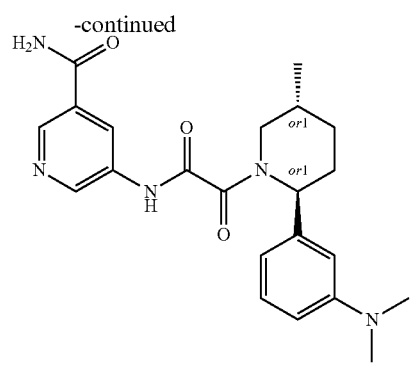

Compound 375

Step 1: The Synthesis of 5-[[2-[(2R,5S)-2-[3-(dimethylamino)phenyl]-5-methyl-1-piperidyl]-2-oxo-acetyl]amino]pyridine-3-carboxamide DIPEA (315.72 mg, 2.44 mmol, 425.49 µL) was added to the solution of respective 2-[(5-carbamoyl-3-pyridyl)amino]-2-oxo-acetic acid (0.15 g, 610.70 µmol, HCl) and N,N-dimethyl-3-[(2S,5R)-5-methyl-2-piperidyl]aniline (133.34 mg, 610.70 µmol) in DMF (5 mL). The resulting mixture was stirred for 5 min followed by the addition of the solution of HATU (255.43 mg, 671.77 µmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC (2-10 min 85-100% $H_2O$-MeOH—$NH_3$ as a mobile phase; loading pump 4 mL MeOH; Triart C18 100*20 mm 5 mkm column) to afford pure 5-[[2-[(2R,5S)-2-[3-(dimethylamino)phenyl]-5-methyl-1-piperidyl]-2-oxo-acetyl]amino]pyridine-3-carboxamide (0.1 g, 244.21 µmol, 39.99% yield).

$^1$H NMR (400 MHz, $CDCl_3$) δ 1.04 (m, 2H), 1.41 (m, 1H), 1.82 (m, 2H), 2.21 (m, 2H), 2.84 (m, 6H), 3.14 (m, 1H), 3.71 (m, 2H), 4.32 (m, 1H), 5.87 (m, 1H), 6.37 (m, 1H), 6.68 (m, 3H), 7.21 (m, 1H), 8.03 (m, 1H), 8.82 (m, 2H), 10.12 (m, 1H).

LCMS(ESI): [M+H]+ m/z: calcd 409.2; found 410.2; Rt=2.354 min.

Step 2: The Synthesis of 5-[[2-[(2R,5S)-2-[3-(dimethylamino)phenyl]-5-methyl-1-piperidyl]-2-oxo-acetyl]amino]pyridine-3-carboxamide (Compound 374) and 5-[[2-[(2S,5R)-2-[3-(dimethylamino)phenyl]-5-methyl-1-piperidyl]-2-oxo-acetyl]amino]pyridine-3-carboxamide (Compound 375

Chiral separation of 5-[[2-[(2R,5S)-2-[3-(dimethylamino)phenyl]-5-methyl-1-piperidyl]-2-oxo-acetyl]amino]pyridine-3-carboxamide was performed using AD-H-II (250*20, 5 mkm) column, Hexane (0.001% EDA)-IPA-MeOH, 60-20-20 as a mobile phase; flow rate 12 mL/min affording Compound 374—5-[[2-[(2R,5S)-2-[3-(dimethylamino)phenyl]-5-methyl-1-piperidyl]-2-oxo-acetyl]amino]pyridine-3-carboxamide (42.8 mg, 42.8% yield; RT=14.388 min) and Compound 375—5-[[2-[(2S,5R)-2-[3-(dimethylamino)phenyl]-5-methyl-1-piperidyl]-2-oxo-acetyl]amino]pyridine-3-carboxamide (47.2 mg, 47.20% yield; RT=19.902 min).

Compound 374: RT (AD-H, Hexane-IPA-MeOH, 60-20-20, 0.6 mL/min)=14.74 min.

¹H NMR (600 MHz, DMSO-d₆) δ 0.96-1.06 (m, 3H), 1.26-1.40 (m, 1H), 1.66-1.80 (m, 1H), 1.83-1.95 (m, 1H), 1.98-2.13 (m, 1H), 2.15-2.25 (m, 1H), 2.78-3.06 (m, 7H), 3.41-4.05 (m, 1H), 5.06-5.57 (m, 1H), 6.52-6.66 (m, 3H), 7.12-7.22 (m, 1H), 7.52-7.67 (m, 1H), 8.09-8.22 (m, 1H), 8.44-8.54 (m, 1H), 8.70-8.80 (m, 1H), 8.81-8.92 (m, 1H), 11.06-11.35 (m, 1H).

LCMS(ESI): [M+H]⁺ m/z: calcd 409.2; found 410.2; Rt=3.721 min.

Compound 375: RT (AD-H, Hexane-IPA-MeOH, 60-20-20, 0.6 mL/min)=21.07 min.

¹H NMR (600 MHz, DMSO-d₆) δ 0.99-1.05 (m, 3H), 1.20-1.39 (m, 2H), 1.65-1.78 (m, 1H), 1.81-1.95 (m, 1H), 1.98-2.14 (m, 1H), 2.15-2.26 (m, 1H), 2.83-2.88 (m, 6H), 3.43-4.04 (m, 1H), 5.04-5.60 (m, 1H), 6.58-6.66 (m, 3H), 7.09-7.21 (m, 1H), 7.51-7.69 (m, 1H), 8.10-8.21 (m, 1H), 8.42-8.53 (m, 1H), 8.69-8.80 (m, 1H), 8.80-8.92 (m, 1H), 10.92-11.59 (m, 1H).

LCMS(ESI): [M+H]⁺ m/z: calcd 409.2; found 410.2; Rt=3.718 min.

Example 38. The Synthesis of 5-[[2-[(2R,5S)-2-(4-fluorophenyl)-5-methyl-1-piperidyl]-2-oxo-acetyl]amino]pyridine-3-carboxamide (Compound 300) and 5-[[2-[(2S,5R)-2-(4-fluorophenyl)-5-methyl-1-piperidyl]-2-oxo-acetyl]amino]pyridine-3-carboxamide (Compound 302

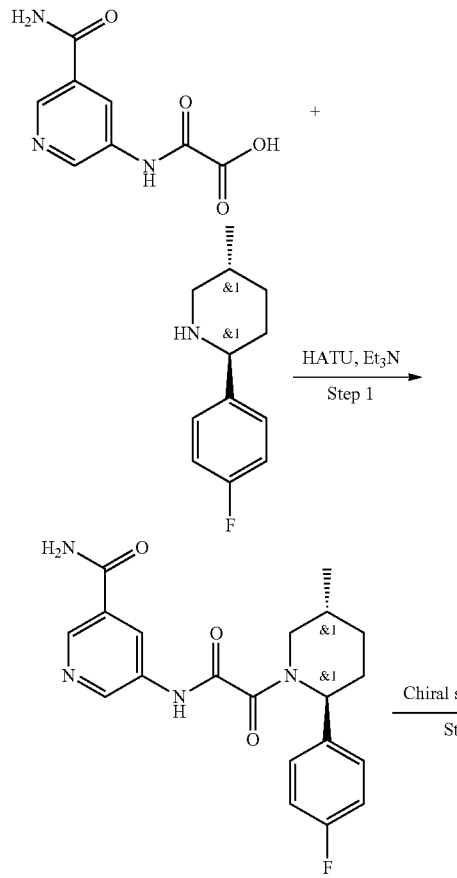

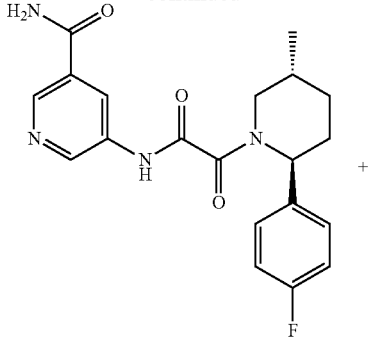

Compound 302

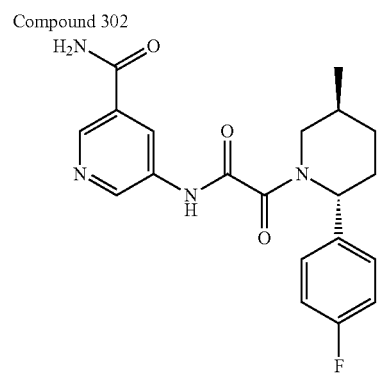

Compound 300

Step 1. Synthesis of 5-[[2-[2-(4-fluorophenyl)-5-methyl-1-piperidyl]-2-oxo-acetyl]amino]pyridine-3-carboxamide 2-[(5-carbamoyl-3-pyridyl)amino]-2-oxo-acetic acid (0.5 g, 2.04 mmol, HCl), HATU (837.98 mg, 2.44 mmol) and Triethylamine (617.97 mg, 6.11 mmol, 851.20 μL) were mixed in dry DMF (25 mL) at 21° C. and the resulting mixture was stirred for 12 hr. 2-(4-fluorophenyl)-5-methyl-piperidine (393.41 mg, 2.04 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (0-5 min 20-70% water-methanol (NH₃ 0.1%), flow 30 ml/min (loading pump 4 ml/min methanol (NH₃ 0.1%)), column: YMC-Actus Triart C18 100*20 mml.D. S-5 um). 5-[[2-[2-(4-fluorophenyl)-5-methyl-1-piperidyl]-2-oxo-acetyl]amino]pyridine-3-carboxamide (151.4 mg, 393.86 μmol, 19.35% yield) was obtained as an off-white solid.

LCMS(ESI): [M+1]⁺ m/z: calcd 384.4; found 385.2; Rt=3.156 min.

Step 2. Synthesis of 5-[[2-[(2R,5S)-2-(4-fluorophenyl)-5-methyl-1-piperidyl]-2-oxo-acetyl]amino]pyridine-3-carboxamide (Compound 300) and 5-[[2-[(2S,5R)-2-(4-fluorophenyl)-5-methyl-1-piperidyl]-2-oxo-acetyl]amino]pyridine-3-carboxamide (Compound 302

Racemate was separated into enantiomers in the flowing conditions: AD-H I (250*20, 5 mkm), Hexane-IPA-MeOH, 70-15-15, 12 ml/min, to give 5-[[2-[(2R,5S)-2-(4-fluorophenyl)-5-methyl-1-piperidyl]-2-oxo-acetyl]amino]pyridine-3-carboxamide (50.04 mg, 130.18 μmol, 33.05% yield) Compound 300 with RT=31.416 min and 5-[[2-[(2S,5R)-2-(4-fluorophenyl)-5-methyl-1-piperidyl]-2-oxo-acetyl]amino]pyridine-3-carboxamide (53.89 mg, 140.19 µmol, 35.59% yield) Compound 302 with RT=23.788 min. The samples were freeze-dried in water-acetonitrile solution to give white powders Compound 300

$^1$H NMR (500 MHz, DMSO-$d_6$) δ 1.00-1.07 (m, 3H), 1.29-1.42 (m, 1H), 1.62-1.74 (m, 1H), 1.84-1.98 (m, 1H), 2.03-2.15 (m, 1H), 2.17-2.29 (m, 1H), 2.76-3.25 (m, 1H), 3.45-4.09 (m, 1H), 5.12-5.62 (m, 1H), 7.16-7.30 (m, 2H), 7.34-7.49 (m, 2H), 7.57-7.66 (m, 1H), 8.10-8.24 (m, 1H), 8.42-8.57 (m, 1H), 8.74-8.84 (m, 1H), 8.84-8.99 (m, 1H), 11.17-11.34 (m, 1H).

RT of 5-[[2-[(2R,5S)-2-(4-fluorophenyl)-5-methyl-1-piperidyl]-2-oxo-acetyl]amino]pyridine-3-carboxamide (50.04 mg, 130.18 µmol, 33.05% yield)=34.379 min (AD-H, Hexane-IPA-MeOH, 70-15-15, 0.6 ml/min)

LCMS(ESI): [M+1]$^+$ m/z: calcd 384.2; found 385.4; Rt=3.034 min.

Compound 302

$^1$H NMR (500 MHz, DMSO-$d_6$) δ 1.01-1.06 (m, 3H), 1.29-1.44 (m, 1H), 1.61-1.76 (m, 1H), 1.81-1.97 (m, 1H), 2.05-2.28 (m, 2H), 2.77-3.25 (m, 1H), 3.47-4.06 (m, 1H), 5.08-5.66 (m, 1H), 7.15-7.30 (m, 2H), 7.32-7.47 (m, 2H), 7.56-7.69 (m, 1H), 8.11-8.22 (m, 1H), 8.44-8.55 (m, 1H), 8.72-8.82 (m, 1H), 8.84-9.01 (m, 1H), 11.10-11.38 (m, 1H).

RT of 5-[[2-[(2S,5R)-2-(4-fluorophenyl)-5-methyl-1-piperidyl]-2-oxo-acetyl]amino]pyridine-3-carboxamide (53.89 mg, 140.19 µmol, 35.59% yield)=26.492 min (AD-H, Hexane-IPA-MeOH, 70-15-15, 0.6 ml/min)

LCMS(ESI): [M+1]$^+$ m/z: calcd 384.2; found 385.4; Rt=3.04 min.

Example 39. The Synthesis of 5-[[2-[(2S,5R)-2-(4-fluorophenyl)-5-methyl-1-piperidyl]-2-oxo-acetyl]amino]-2-methoxy-pyridine-3-carboxamide (Compound 446) and 5-[[2-[(2R,5S)-2-(4-fluorophenyl)-5-methyl-1-piperidyl]-2-oxo-acetyl]amino]-2-methoxy-pyridine-3-carboxamide (Compound 445

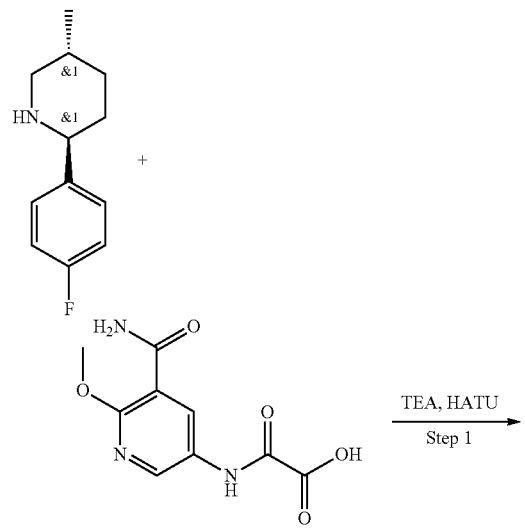

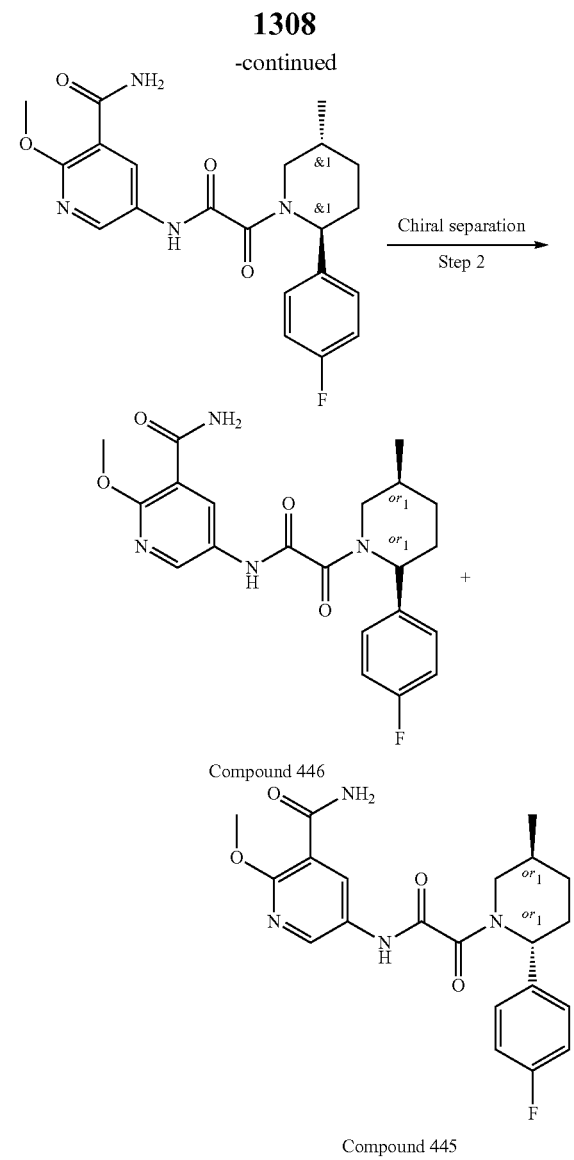

Step 1. Synthesis of 5-[[2-[2-(4-fluorophenyl)-5-methyl-1-piperidyl]-2-oxo-acetyl]amino]-2-methoxy-pyridine-3-carboxamide 2-[(5-carbamoyl-6-methoxy-3-pyridyl)amino]-2-oxo-acetic acid (0.3, 881.38 µmol, Et$_3$N), HATU (335.13 mg, 881.38 µmol) and triethylamine (89.19 mg, 881.38 µmol, 122.85 µL) were mixed in dry DMF (5 mL) at 21° C. and the resulting mixture was stirred for 15 min. 2-(4-fluorophenyl)-5-methyl-piperidine (170.34 mg, 881.38 µmol) was added thereto and the resulting mixture was stirred at 21° C. overnight. The resulting mixture was poured into water, extracted 3 times with EtOAc, combined organics were washed with water, brine and evaporated. The residue was subjected to HPLC (2-7 min; water-r1(+NH$_3$); 30 ml/min; loading pump 4 ml/min R1+NH$_3$; column YMC-ACTUS TRIAT 20*100 mm). 5-[[2-[2-(4-fluorophenyl)-5-methyl-1-piperidyl]-2-oxo-acetyl]amino]-2-methoxy-pyridine-3-carboxamide (129.1 mg, 311.51 µmol, 35.34% yield) was obtained as a white solid.

LCMS(ESI): [M+1]$^+$ m/z: calcd 414.2; found 415.2; Rt=1.195 min.

Step 2. Separation for 5-[[2-[(2S,5R)-2-(4-fluorophenyl)-5-methyl-1-piperidyl]-2-oxo-acetyl]amino]-2-methoxy-pyridine-3-carboxamide (Compound 446) and 5-[[2-[(2R,5S)-2-(4-fluorophenyl)-5-methyl-1-piperidyl]-2-oxo-acetyl]amino]-2-methoxy-pyridine-3-carboxamide (Compound 445

Chiral separation was done in the following conditions: IA (250*20 mm, 5 mkm) Hexane-IPA-MeOH, 50-25-25, 13 ml/min, RT Compound 445=34.429 min, RT Compound 446=26.540 min.

RT of 5-[[2-[(2S,5R)-2-(4-fluorophenyl)-5-methyl-1-piperidyl]-2-oxo-acetyl]amino]-2-methoxy-pyridine-3-carboxamide (48.42 mg, 116.84 µmol, 40.35% yield)=14.6942 min (IA, Hexane-IPA-MeOH, 50-25-25, 0.15 ml/min)

RT of 5-[[2-[(2R,5S)-2-(4-fluorophenyl)-5-methyl-1-piperidyl]-2-oxo-acetyl]amino]-2-methoxy-pyridine-3-carboxamide (43.64 mg, 105.30 µmol, 36.37% yield)=18.7292 min (IA, Hexane-IPA-MeOH, 50-25-25, 0.15 ml/min)

Compound 445: $^1$H NMR (DMSO-$d_6$, 600 MHz): δ (ppm) 1.01 (m, 3H), 1.33 (m, 1H), 1.64 (t, 1H), 1.88 (m, 1H), 2.13 (m, 2H), 2.97 (m, 1H), 3.93 (m, 4H), 5.34 (m, 1H), 7.20 (m, 2H), 7.34 (m, 2H), 7.72 (dd, 2H), 8.43 (m, 1H), 8.52 (m, 1H), 11.01 (m, 1H).

LCMS(ESI): [M+H]$^+$ m/z: calcd 414.2; found 415.2; Rt=3.291 min.

Compound 446: $^1$H NMR (DMSO-$d_6$, 600 MHz): δ (ppm) 1.01 (m, 3H), 1.33 (m, 1H), 1.64 (t, 1H), 1.88 (m, 1H), 2.13 (m, 2H), 2.97 (m, 1H), 3.93 (m, 4H), 5.34 (m, 1H), 7.20 (m, 2H), 7.34 (m, 2H), 7.72 (dd, 2H), 8.43 (m, 1H), 8.52 (m, 1H), 11.01 (m, 1H).

LCMS(ESI): [M+H]$^+$ m/z: calcd 414.2; found 415.2; Rt=3.291 min.

Example 40. The Synthesis of N-(6-amino-5-ethylpyridin-3-yl)-2-(2-(4-fluorophenyl)-5-methylpiperidin-1-yl)-2-oxoacetamide (Compound 710

2-[(6-amino-5-ethyl-3-pyridyl)amino]-2-oxo-acetic acid (234.90 mg, 1.12 mmol) and TEA (340.86 mg, 3.37 mmol, 469.50 µL) were mixed in dry DMF (5 mL) at 21° C. and the resulting mixture was stirred for 15 min. HATU (426.94 mg, 1.12 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (50-90% 0.5-6.5 min; water-MeOH+NH$_3$; flow 30 ml/min (loading pump 4 ml/min MeOH—NH$_3$); column: YMS-actus triat 100×19 mm 5 um (R)). N-(6-amino-5-ethyl-3-pyridyl)-2-[(2R,5S)-2-(4-fluorophenyl)-5-methyl-1-piperidyl]-2-oxo-acetamide (185.6 mg, 482.77 µmol, 43.00% yield) was obtained in two fraction: 1st-24.7 mg (96.16% by LCMS, no cis-impurity); 2nd—160.9 mg (92.1% of trans; 7.9% of cis-impurity); ee 94-95%.

Compound 710: $^1$H NMR (600 MHz, DMSO-$d_6$) δ (ppm) 0.98 (d, 3H), 1.07 (m, 3H), 1.28 (m, 1H), 1.65 (m, 1H), 1.88 (m, 1H), 2.01 (m, 1H), 2.14 (m, 1H), 2.39 (m, 2H), 3.02 (m, 1H), 3.98 (m, 1H), 5.12 (m, 1H), 5.63 (m, 2H), 7.20 (m, 2H), 7.32 (m, 2H), 7.48 (m, 1H), 8.04 (m, 1H), 10.50 (m, 1H).

LCMS(ESI): [M]$^+$ m/z: calcd 384.2; found 385.2; Rt=1.724 min.

Example 41. The Synthesis of 5-(2-((2S,5R)-2-(4-aminophenyl)-5-methylpiperidin-1-yl)-2-oxoacetamido)Nicotinamide (Compound 398) and 5-(2-((2R,5S)-2-(4-aminophenyl)-5-methylpiperidin-1-yl)-2-oxoacetamido)Nicotinamide (Compound 381

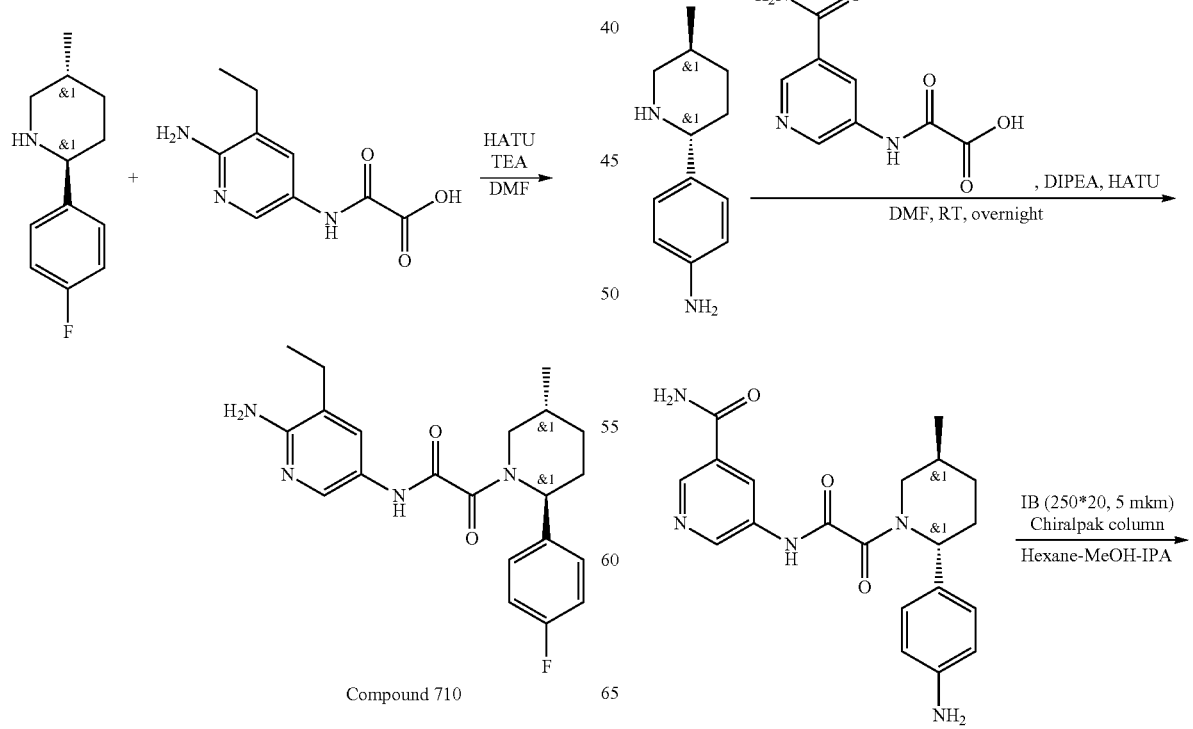

Compound 710

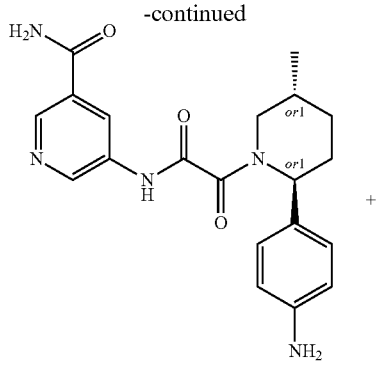

Compound 398

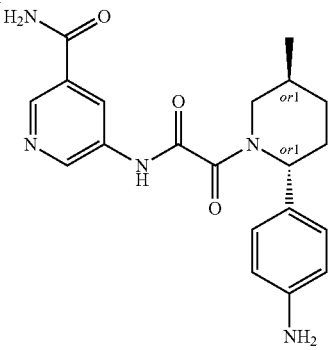

Compound 381

Step 1: The Synthesis of 5-[[2-[2-(4-aminophenyl)-5-methyl-1-piperidyl]-2-oxo-acetyl]amino]pyridine-3-carboxamide DIPEA (644.58 mg, 4.99 mmol, 868.71 μL) was added to the solution of 2-[(5-carbamoyl-3-pyridyl)amino]-2-oxo-acetic acid (0.35 g, 1.42 mmol, HCl) and 4-(5-methyl-2-piperidyl)aniline (271.15 mg, 1.42 mmol) in DMF (10 mL). The resulting mixture was stirred for 5 min followed by the addition of the solution of HATU (596.00 mg, 1.57 mmol) in DMF (5 mL). Then, the reaction mixture was stirred overnight at room temperature. After the completion of the reaction, monitored by LCMS, the resulting suspension was concentrated under reduced pressure. The obtained solid was subjected to HPLC (SunFire C18 100*18 mm, 5 mkm column; 2-10 min 30-55% MeCN—H$_2$O as a mobile phase; Flow rate 30 mL/min (loading pump 4 mL, MeCN)) to afford pure 5-[[2-[2-(4-aminophenyl)-5-methyl-1-piperidyl]-2-oxo-acetyl]amino]pyridine-3-carboxamide (0.13 g, 340.83 μmol, 23.92% yield).

$^1$H NMR (400 MHz, DMSO-d$_6$) δ 1.05 (m, 2H), 1.31 (m, 1H), 1.85 (m, 2H), 3.09 (d, 3H), 3.23 (m, 1H), 3.34 (m, 1H), 4.05 (m, 2H), 5.21 (m, 2H), 6.61 (m, 2H), 7.82 (m, 2H), 7.71 (m, 1H), 8.36 (m, 1H), 8.49 (m, 1H), 8.77 (m, 2H).

LCMS(ESI): [M+H]$^+$ m/z: calcd 381.1; found 382.2; Rt=2.033 min.

Step 2: Chiral Resolution of 5-[[2-[2-(4-aminophenyl)-5-methyl-1-piperidyl]-2-oxo-acetyl]amino]pyridine-3-carboxamide Chiral separation was performed using OJ-H (250*20, 5 mkm) Chiralpak column; Hexane-MeOH-IPA, 50-25-25 as a mobile phase; Flow rate 15 mL/min; Injection volume 900 mkL to afford Compound 398—5-(2-((2S,5R)-2-(4-amino-phenyl)-5-methylpiperidin-1-yl)-2-oxoacetamido)nicotinamide (8.9 mg, 6.85% yield) as an yellow oil and Compound 381—5-(2-((2R,5 S)-2-(4-aminophenyl)-5-methylpiperidin-1-yl)-2-oxoacetamido)nicotinamide (60.1 mg, 46.23% yield) as an yellow oil.

Compound 398: RT (TB (250*20, 5 mkm) column; Hexane-MeOH-IPA, 50-25-25, 15 mL/min)=26.42 min.

$^1$H NMR (600 MHz, DMSO-d$_6$) δ 0.97-1.04 (m, 3H), 1.25-1.36 (m, 1H), 1.66-1.78 (m, 1H), 1.79-1.90 (m, 1H), 1.91-2.07 (m, 1H), 2.08-2.17 (m, 1H), 2.74-3.16 (m, 1H), 3.38-3.99 (m, 1H), 4.93-5.58 (m, 3H), 6.51-6.60 (m, 2H), 6.92-7.03 (m, 2H), 7.54-7.64 (m, 1H), 8.09-8.22 (m, 1H), 8.41-8.50 (m, 1H), 8.71-8.79 (m, 1H), 8.80-8.90 (m, 1H), 11.05-11.38 (m, 1H).

LCMS(ESI): [M+H]$^+$ m/z: calcd 381.1; found 382.0; Rt=3.265 min.

Compound 381: RT (TB (250*20, 5 mkm) column; Hexane-MeOH-IPA, 50-25-25, 15 mL/min)=14.61 min.

$^1$H NMR (600 MHz, DMSO-d$_6$) δ 0.97-1.02 (m, 3H), 1.25-1.35 (m, 1H), 1.66-1.78 (m, 1H), 1.79-1.90 (m, 1H), 1.92-2.05 (m, 1H), 2.09-2.17 (m, 1H), 2.73-3.19 (m, 1H), 3.36-3.97 (m, 1H), 4.87-5.55 (m, 3H), 6.48-6.62 (m, 2H), 6.90-7.04 (m, 2H), 7.51-7.68 (m, 1H), 8.07-8.22 (m, 1H), 8.42-8.52 (m, 1H), 8.70-8.80 (m, 1H), 8.82-8.94 (m, 1H), 11.05-11.34 (m, 1H).

LCMS(ESI): [M+H]$^+$ m/z: calcd 381.1; found 382.0; Rt=3.265 min.

Example 42. The Synthesis of 5-(2-((2R,5S)-2-(4-acetamidophenyl)-5-methylpiperidin-1-yl)-2-oxoacetamido)Nicotinamide (Compound 451) and 5-(2-((2S,5R)-2-(4-acetamidophenyl)-5-methylpiperidin-1-yl)-2-oxoacetamido)Nicotinamide (Compound 452)

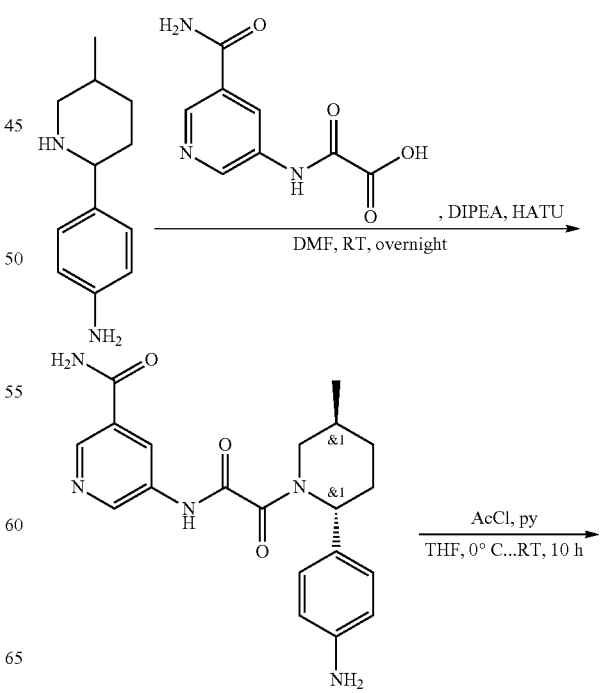

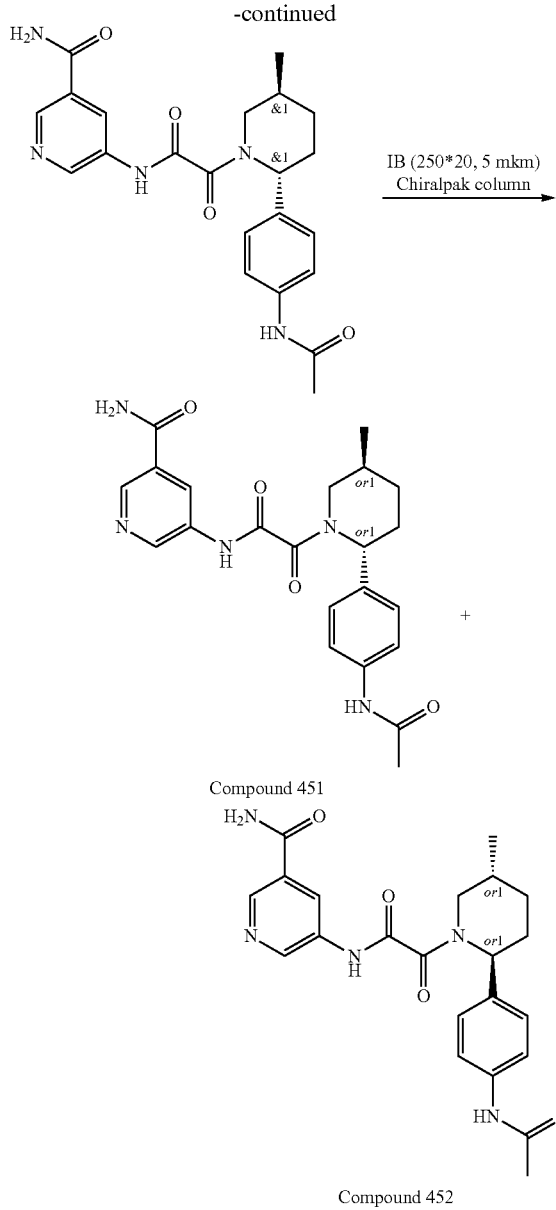

Compound 451

Compound 452

Step 1 is the Same as Above

Step 2: The Synthesis of 5-(2-(2-(4-acetamidophenyl)-5-methylpiperidin-1-yl)-2-oxoacetamido)nicotinamide To a pre-cooled solution of 5-(2-(2-(4-aminophenyl)-5-methylpiperidin-1-yl)-2-oxoacetamido)nicotinamide (0.15 g, 393.26 μmol) in THF (10 mL), Pyridine (77.77 mg, 983.15 μmol, 79.52 μL) was added. The resulting mixture was stirred for 5 min followed by the dropwise addition of Acetyl chloride (33.96 mg, 432.59 μmol, 26.32 μL) at 0° C. Then, the reaction mixture was stirred for 10 hr at room temperature. After the completion of the reaction, monitored by LCMS, the resulting suspension was concentrated under reduced pressure. The obtained solid was subjected to HPLC (2-10 min 40-60% water/MeCN+NH₃ as a mobile phase; loading pump 4 mL MeCN+NH₃; TRIART 100*20 5 microM column; injection volume: 1500.0 mL) to afford pure 5-[[2-[(2R,5S)-2-(4-acetamidophenyl)-5-methyl-1-piperidyl]-2-oxo-acetyl]amino]pyridine-3-carboxamide (76.3 mg, 180.18 μmol, 45.82% yield).

LCMS(ESI): [M+H]⁺ m/z: calcd 423.2; found 424.2; Rt=0.939 min.

Step 3: Chiral Separation of 5-(2-(2-(4-acetamidophenyl)-5-methylpiperidin-1-yl)-2-oxoacetamido) Nicotinamide Chiral separation was performed using IB (250*20, 5 mkm) Chiralpak column; Hexane-MeOH-IPA, 50-25-25 as a mobile phase; Flow rate 12 mL/min to afford Compound 451-5-(2-((2R,5S)-2-(4-acetamidophenyl)-5-methylpiperidin-1-yl)-2-oxoacetamido)nicotinamide (25.37 mg; 33.25% yield) and Compound 452—5-(2-((2S,5R)-2-(4-acetamidophenyl)-5-methylpiperidin-1-yl)-2-oxoacetamido)nicotinamide (25.56 mg; 33.50% yield).

Compound 451: RT (IB column, Hexane-IPA-MeOH, 50-25-25, 0.6 mL/min)=10.74 min

¹H NMR (DMSO-d₆, 500 MHz): δ (ppm) 1.04 (m, 3H), 1.35 (m, 1H), 1.74 (m, 1H), 2.03 (m, 3H), 2.22 (m, 1H), 2.64 (s, 2H), 3.08 (m, 1H), 3.74 (m, 1H), 5.40 (m, 1H), 7.27 (m, 2H), 7.60 (m, 3H), 8.17 (m, 1H), 8.50 (m, 1H), 8.78 (m, 1H), 8.89 (m, 1H), 9.95 (m, 1H), 11.21 (m, 1H).

LCMS(ESI): [M+H]⁺ m/z: calcd 423.2; found 424.0; Rt=2.447 min.

Compound 452: RT (IB column, Hexane-IPA-MeOH, 50-25-25, 0.6 mL/min)=24.15 min

¹H NMR (DMSO-d₆, 500 MHz): δ (ppm) 1.04 (m, 3H), 1.36 (m, 1H), 1.69 (m, 1H), 1.89 (m, 1H), 2.03 (m, 4H), 2.19 (m, 1H), 2.93 (m, 1H), 3.66 (m, 1H), 5.35 (m, 1H), 7.27 (dd, 2H), 7.58 (m, 3H), 8.17 (m, 1H), 8.49 (m, 1H), 8.78 (m, 1H), 8.90 (m, 1H), 9.95 (m, 1H), 11.21 (m, 1H).

LCMS(ESI): [M+H]⁺ m/z: calcd 423.2; found 424.0; Rt=2.446 min.

Example 43. The Synthesis of 5-[[2-[(2R,5S)-2-[4-(methanesulfonamido)phenyl]-5-methyl-1-piperidyl]-2-oxo-acetyl]amino]pyridine-3-carboxamide (Compound 469) and 5-[[2-[(2S,5R)-2-[4-(methanesulfonamido)phenyl]-5-methyl-1-piperidyl]-2-oxo-acetyl]amino]pyridine-3-carboxamide (Compound 462

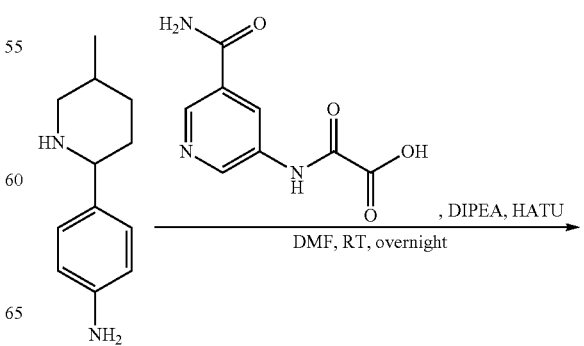

1315

-continued

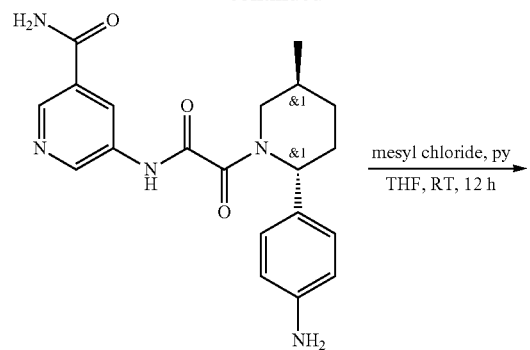

mesyl chloride, py
THF, RT, 12 h

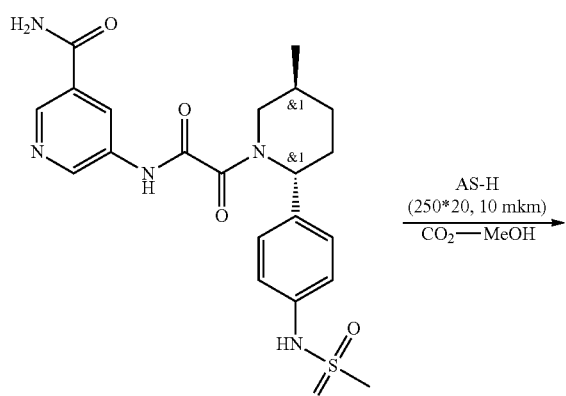

AS-H
(250*20, 10 mkm)
CO₂—MeOH

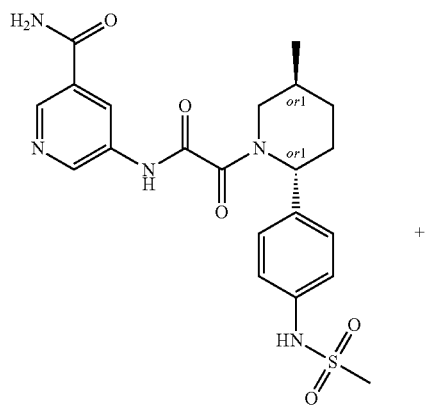

Compound 469

+

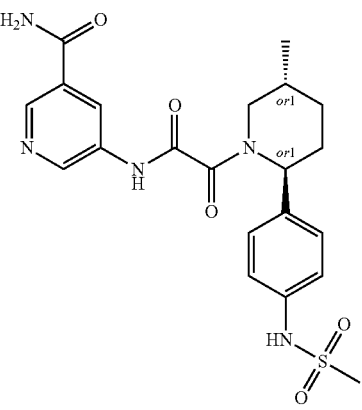

Compound 462

1316

Step 1 is the Same as Above

Step 2: The Synthesis of 5-[[2-[(2R,5S)-2-[4-(methanesulfonamido)phenyl]-5-methyl-1-piperidyl]-2-oxo-acetyl]amino]pyridine-3-carboxamide To a pre-cooled solution of 5-[[2-[(2R,5S)-2-(4-aminophenyl)-5-methyl-1-piperidyl]-2-oxo-acetyl]amino]pyridine-3-carboxamide (0.26 g, 681.65 µmol) in THF (5 mL), pyridine (134.80 mg, 1.70 mmol, 137.83 µL) was added. After that, methanesulfonyl chloride (85.89 mg, 749.82 µmol, 58.04 µL) was added dropwise at 0° C. Then, the reaction mixture was stirred for 12 hr at room temperature. After the completion of the reaction, monitored by LCMS, the resulting suspension was concentrated under reduced pressure. The obtained solid was subjected to HPLC (2-10 min 40-60% water/MeOH+NH₃ as a mobile phase; loading pump 4 ml MeOH+NH₃; TRIART 100*20 5 microM column) to afford pure 5-[[2-[(2R,5S)-2-[4-(methanesulfonamido)phenyl]-5-methyl-1-piperidyl]-2-oxo-acetyl]amino]pyridine-3-carboxamide (0.19 g, 413.48 µmol, 60.66% yield).

LCMS(ESI): [M+H]⁺ m/z: calcd 459.2; found 460.2; Rt=2.760 min.

Step 3: The Synthesis of 5-[[2-[(2R,5S)-2-[4-(methanesulfonamido)phenyl]-5-methyl-1-piperidyl]-2-oxo-acetyl]amino]pyridine-3-carboxamide (Compound 469) and 5-[[2-[(2S,5R)-2-[4-(methanesulfonamido)phenyl]-5-methyl-1-piperidyl]-2-oxo-acetyl]amino]pyridine-3-carboxamide (Compound 462

Chiral separation of 5-[[2-[(2R,5S)-2-[4-(methanesulfonamido)phenyl]-5-methyl-1-piperidyl]-2-oxo-acetyl]amino]pyridine-3-carboxamide was performed using AS-H (250*20, 10 mkm) column; CO₂-MeOH, 60-40 as a mobile phase; flow rate 40 mL/min affording Compound 469—5-[[2-[(2R,5S)-2-[4-(methanesulfonamido)phenyl]-5-methyl-1-piperidyl]-2-oxo-acetyl]amino]pyridine-3-carboxamide (73.14 mg, 38.49% yield; RT (AS-H, CO₂-MeOH, 15 mL/min)=8.44 min) as light yellow oil and Compound 462—5-[[2-[(2S,5R)-2-[4-(methanesulfonamido)phenyl]-5-methyl-1-piperidyl]-2-oxo-acetyl]amino]pyridine-3-carboxamide (76.84 min; 40.44% yield; RT (AS-H, CO₂-MeOH, 15 mL/min)=6.62 min) as light yellow oil.

Compound 469: RT (AS-H, CO₂-MeOH, 60-40, 2.0 mL/min)=5.22 min

¹H NMR (600 MHz, DMSO-d₆) δ 0.97-1.05 (m, 3H), 1.28-1.39 (m, 1H), 1.63-1.74 (m, 1H), 1.80-1.94 (m, 1H), 2.00-2.13 (m, 1H), 2.13-2.23 (m, 1H), 2.72-3.28 (m, 4H), 3.41-4.04 (m, 1H), 5.05-5.68 (m, 1H), 7.14-7.24 (m, 2H), 7.24-7.32 (m, 2H), 7.52-7.65 (m, 1H), 8.10-8.21 (m, 1H), 8.41-8.53 (m, 1H), 8.72-8.80 (m, 1H), 8.82-8.93 (m, 1H), 9.71 (s, 1H), 11.11-11.37 (m, 1H).

LCMS(ESI): [M+3H]⁺ m/z: calcd 459.2; found 462.2; Rt=4.067 min.

Compound 462: RT (AS-H, CO₂-MeOH, 60-40, 2.0 mL/min)=3.77 min

¹H NMR (600 MHz, DMSO-d₆) δ 0.97-1.05 (m, 3H), 1.27-1.39 (m, 1H), 1.62-1.72 (m, 1H), 1.81-1.94 (m, 1H), 2.01-2.13 (m, 1H), 2.14-2.23 (m, 1H), 2.76-3.21 (m, 4H), 3.43-4.03 (m, 1H), 5.07-5.57 (m, 1H), 7.17-7.24 (m, 2H), 7.24-7.32 (m, 2H), 7.54-7.63 (m, 1H), 8.11-8.19 (m, 1H), 8.41-8.51 (m, 1H), 8.71-8.79 (m, 1H), 8.83-8.92 (m, 1H), 9.71 (s, 1H), 11.09-11.28 (m, 1H).

LCMS(ESI): [M+3H]+ m/z: calcd 459.2; found 462.2; Rt=4.067 min.

Example 44. The Synthesis of 2-[(2R,5S)-2-(4-aminophenyl)-5-methyl-1-piperidyl]-N-(5-methyl-3-pyridyl)-2-oxo-acetamide (Compound 67) and 2-[(2R,5S)-2-(4-acetamidophenyl)-5-methyl-1-piperidyl]-N-(5-methyl-3-pyridyl)-2-oxo-acetamide (Compound 111

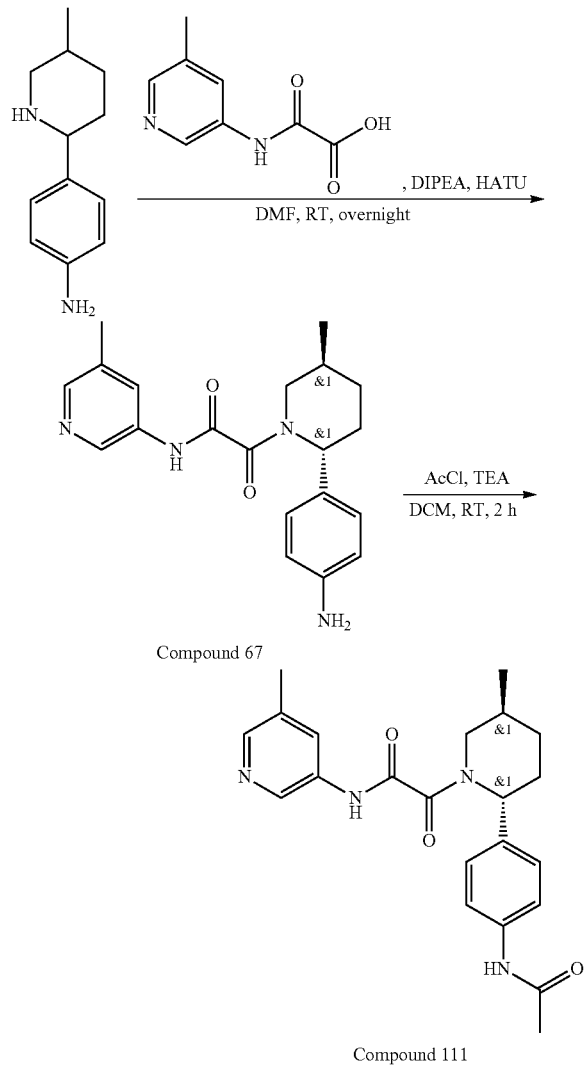

Compound 67

Compound 111

Step 1: The Synthesis of 2-[(2R,5S)-2-(4-aminophenyl)-5-methyl-1-piperidyl]-N-(5-methyl-3-pyridyl)-2-oxo-acetamide (Compound 67)

2-[(5-methyl-3-pyridyl)amino]-2-oxo-acetic acid (446.39 mg, 1.65 mmol, HCl) was dissolved in DMF (5 mL). The resulting mixture was stirred for 5 min following by the addition of DIPEA (1.07 g, 8.24 mmol, 1.44 mL) and HATU (626.82 mg, 1.65 mmol). After stirring for 10 min (change of color was observed), 4-(5-methyl-2-piperidyl)aniline (0.5 g, 1.65 mmol, TFA) was added in one portion and the reaction mixture was stirred overnight. Evaporation of the solvent and purification by HPLC (27% 0.5-6.5 min; water-acetonitrile; flow 30 mL/min; (loading pump 4 mL/min acetonitrile); column SunFire 100*19 mm 5 um) results in 2-[(2R,5S)-2-(4-aminophenyl)-5-methyl-1-piperidyl]-N-(5-methyl-3-pyridyl)-2-oxo-acetamide (0.017 g, 48.24 μmol, 2.93% yield).

$^1$H NMR (400 MHz, DMSO-d$_6$) δ 0.98 (m, 3H), 1.26 (m, 1H), 1.70 (m, 1H), 1.81 (m, 1H), 1.92 (m, 1H), 2.09 (m, 1H), 2.25 (m, 3H), 3.02 (m, 1H), 3.35 (m, 1H), 5.23 (m, 3H), 6.53 (m, 2H), 6.94 (m, 2H), 7.88 (m, 1H), 8.14 (m, 1H), 8.59 (m, 1H), 10.95 (m, 1H).

LCMS(ESI): [M+H]+ m/z: calcd 352.2; found 353.2; Rt=2.420 min.

Step 2: The Synthesis of 2-[(2R,5S)-2-(4-acetamidophenyl)-5-methyl-1-piperidyl]-N-(5-methyl-3-pyridyl)-2-oxo-acetamide (Compound 111

2-[(2R,5S)-2-(4-aminophenyl)-5-methyl-1-piperidyl]-N-(5-methyl-3-pyridyl)-2-oxo-acetamide (10.00 mg, 25.54 μmol) was dissolved in DCM (1 mL). The resulting mixture was stirred for 5 min followed by the addition of TEA (2.58 mg, 25.54 μmol, 3.56 μL) and acetyl chloride (2.00 mg, 25.54 μmol, 1.55 μL). Evaporation of the solvent and purification with HPLC (50% 0.5-6.5 min; water-MeOH; flow 30 mL/min; loading pump 4 mL/min MeOH; column SunFire 100*19 mm 5 um) to give 2-[(2R,5S)-2-(4-acetamidophenyl)-5-methyl-1-piperidyl]-N-(5-methyl-3-pyridyl)-2-oxo-acetamide (0.005 g, 12.68 μmol, 49.64% yield).

$^1$H NMR (Chloroform-d, 600 MHz): δ (ppm) 0.92 (m, 3H), 1.17 (m, 1H), 1.68 (m, 4H), 1.83 (m, 5H), 1.97 (m, 3H), 2.67 (m, 1H), 3.75 (m, 1H), 5.06 (m, 1H), 6.04 (m, 2H), 6.26 (m, 2H), 6.72 (m, 1H), 6.87 (m, 1H), 7.11 (m, 1H), 7.83 (m, 1H).

LCMS(ESI): [M+H]+ m/z: calcd 394.2; found 395.4; Rt=2.464 min.

Example 45. The Synthesis of 5-[[2-[(2S,5R)-5-methyl-2-[4-(methylamino)phenyl]-1-piperidyl]-2-oxo-acetyl]amino]pyridine-3-carboxamide (Compound 424) and 5-[[2-[(2R,5S)-5-methyl-2-[4-(methylamino)phenyl]-1-piperidyl]-2-oxo-acetyl]amino]pyridine-3-carboxamide Compound 438

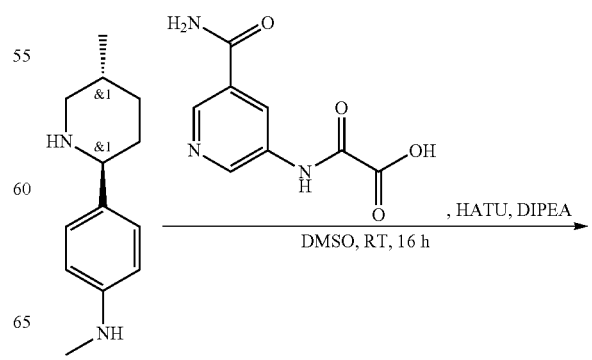

1319

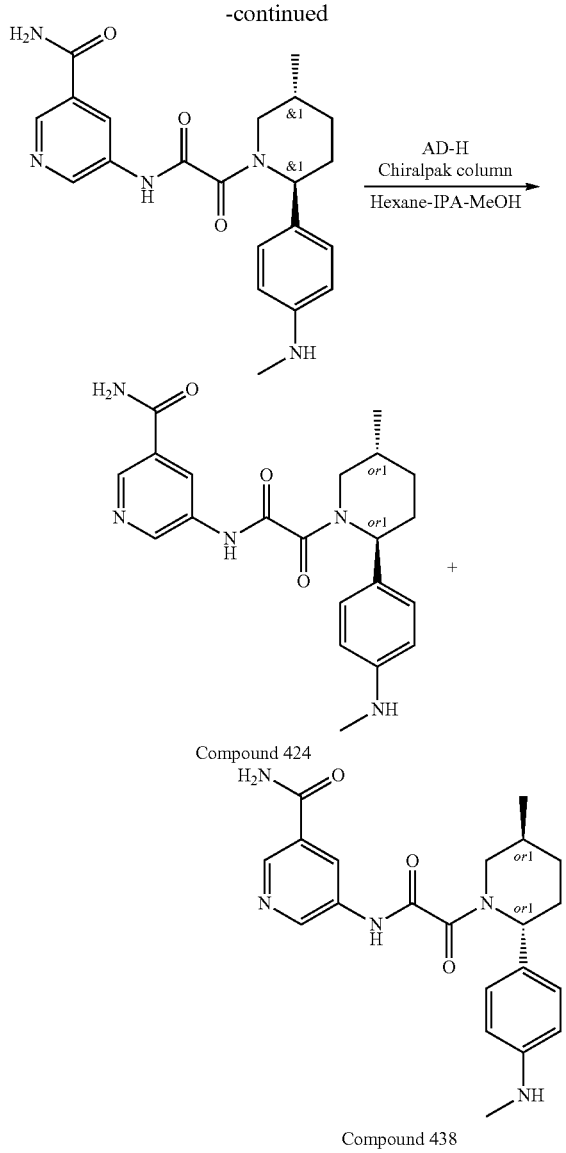

Compound 424

Compound 438

Step 1: The Synthesis of 5-[[2-[(2S,5R)-5-methyl-2-[4-(methylamino)phenyl]-1-piperidyl]-2-oxo-acetyl]amino]pyridine-3-carboxamide 2-[(5-carbamoyl-3-pyridyl)amino]-2-oxo-acetic acid (223.89 mg, 721.42 μmol, N(C2H5)3), N-methyl-4-[(2S,5R)-5-methyl-2-piperidyl]aniline (0.2 g, 721.42 μmol, 2HCl), HATU (301.73 mg, 793.56 μmol) and DIPEA (279.71 mg, 2.16 mmol, 376.96 μL) were mixed together in DMSO (4 mL). The resulting mixture was stirred at RT for 16 hr. Then, the obtained solution in DMSO was subjected to HPLC (2-10 min 35-100% MeOH/H2O as a mobile phase; 30 mL/min; loading pump 4 mL MeOH; SunFire 100*19 mm, 5 microM column) to afford 5-[[2-[(2S,5R)-5-methyl-2-[4-(methylamino)phenyl]-1-piperidyl]-2-oxo-acetyl]amino]pyridine-3-carboxamide (0.086 g, 217.47 μmol, 30.15% yield).

LCMS(ESI): [M+H]+ m/z: calcd 395.2; found 396.2; Rt=2.233 min.

1320

Step 2: The Synthesis of 5-[[2-[(2S,5R)-5-methyl-2-[4-(methylamino)phenyl]-1-piperidyl]-2-oxo-acetyl]amino]pyridine-3-carboxamide (Compound 424) and 5-[[2-[(2R,5S)-5-methyl-2-[4-(methylamino)phenyl]-1-piperidyl]-2-oxo-acetyl]amino]pyridine-3-carboxamide (Compound 438

Chiral separation of 5-[[2-[(2S,5R)-5-methyl-2-[4-(methylamino)phenyl]-1-piperidyl]-2-oxo-acetyl]amino]pyridine-3-carboxamide was performed using Chiralpak AD-HIII (250*20 mm, 5 mkm) column; Hexane-IPA-MeOH, 50-25-25 as a mobile phase; Flow Rate: 12 mL/min; (m=0.085 g, 3 injections, Vph=3 L, 4.5 hr) affording Compound 424— 5-[[2-[(2S,5R)-5-methyl-2-[4-(methylamino)phenyl]-1-piperidyl]-2-oxo-acetyl]amino]pyridine-3-carboxamide (17.7 mg, 20.58% yield; RT=22.230 min) as a light yellow solid and Compound 438—5-[[2-[(2R,5S)-5-methyl-2-[4-(methylamino)phenyl]-1-piperidyl]-2-oxo-acetyl]amino]pyridine-3-carboxamide (22.1 mg, 25.70% yield, RT=54.618 min) as a light yellow solid.

Compound 438: RT (AD-H, Hexane-IPA-MeOH, 50-25-25, 0.6 mL/min=59.935 min $^1$H NMR (500 MHz, DMSO-$d_6$) δ 0.90-1.16 (m, 3H), 1.28-1.38 (m, 1H), 1.68-1.93 (m, 2H), 1.93-2.11 (m, 1H), 2.12-2.22 (m, 1H), 2.63-2.75 (m, 3H), 2.77-3.25 (m, 1H), 3.36-4.02 (m, 1H), 5.00-5.59 (m, 1H), 5.59-5.65 (m, 1H), 6.46-6.66 (m, 2H), 6.97-7.13 (m, 2H), 7.51-7.73 (m, 1H), 8.11-8.27 (m, 1H), 8.41-8.58 (m, 1H), 8.69-8.85 (m, 1H), 8.85-8.97 (m, 1H), 11.10-11.30 (m, 1H).

LCMS(ESI): [M+H]+ m/z: calcd 395.2; found 396.2; Rt=1.975 min.

Compound 424: RT (AD-H, Hexane-IPA-MeOH, 50-25-25, 0.6 mL/min=20.107 min $^1$H NMR (500 MHz, DMSO-$d_6$) δ 0.95-1.14 (m, 3H), 1.26-1.40 (m, 1H), 1.65-1.94 (m, 2H), 1.94-2.11 (m, 1H), 2.13-2.24 (m, 1H), 2.64-2.69 (m, 3H), 2.74-3.27 (m, 1H), 3.36-4.01 (m, 1H), 4.98-5.58 (m, 1H), 5.58-5.67 (m, 1H), 6.44-6.67 (m, 2H), 6.99-7.14 (m, 2H), 7.52-7.70 (m, 1H), 8.08-8.27 (m, 1H), 8.40-8.56 (m, 1H), 8.69-8.84 (m, 1H), 8.84-8.98 (m, 1H), 11.12-11.31 (m, 1H).

LCMS(ESI): [M+H]+ m/z: calcd 395.2; found 396.2; Rt=1.976 min.

Example 46. The Synthesis of N-(5,6-dimethyl-3-pyridyl)-2-[(2S,5R)-2-[4-(methanesulfonamido)phenyl]-5-methyl-1-piperidyl]-2-oxo-acetamide (Compound 630) and N-(5,6-dimethyl-3-pyridyl)-2-[(2R,5S)-2-[4-(methanesulfonamido)phenyl]-5-methyl-1-piperidyl]-2-oxo-acetamide (Compound 621

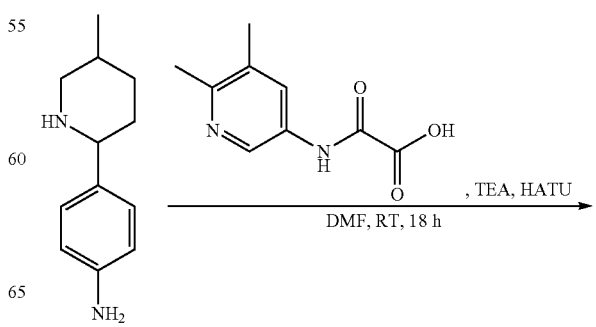

-continued

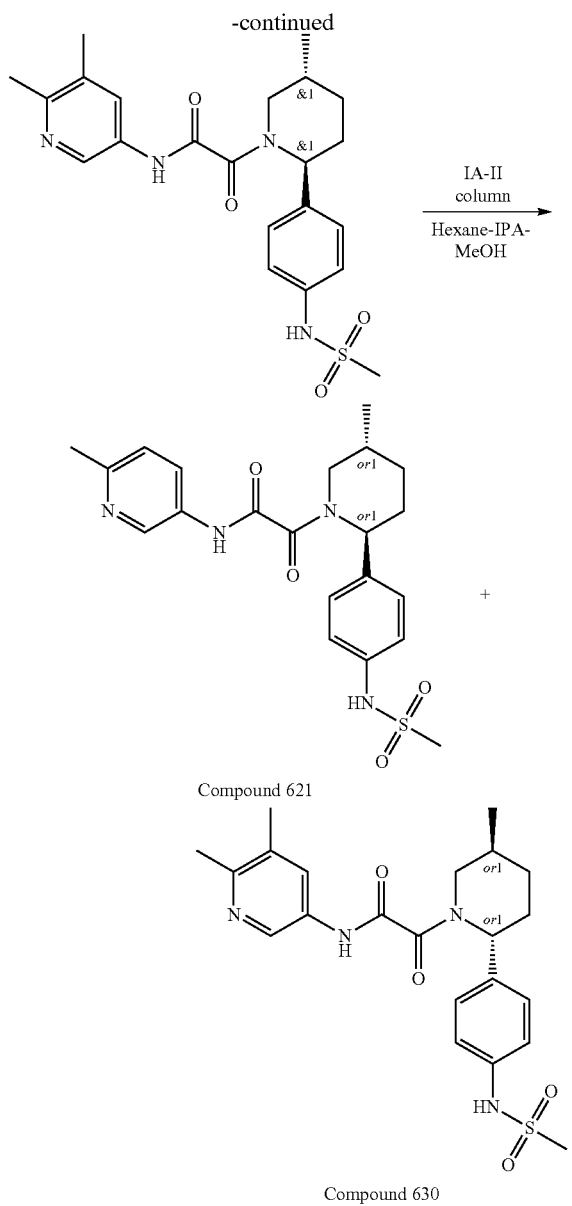

Compound 621

Compound 630

Step 1: The Synthesis of N-(5,6-dimethyl-3-pyridyl)-2-[(2S,5R)-2-[4-(methanesulfonamido)phenyl]-5-methyl-1-piperidyl]-2-oxo-acetamide To a stirring solution of 4-[(2S,5R)-5-methyl-2-piperidyl]aniline (250 mg, 1.31 mmol), 2-[(5,6-dimethyl-3-pyridyl)amino]-2-oxo-acetic acid (388.07 mg, 1.31 mmol, N(C2H$_5$)$_3$) and triethyl amine (1.33 g, 13.14 mmol, 1.83 mL) in DMF (5 mL) was added HATU (549.51 mg, 1.45 mmol) at 25° C. in small portions over 0.5 hr. The resulting reaction mixture was stirred at 25° C. for 18 hr. The reaction mixture sample was submitted for LCMS analysis. LCMS indicated 26.88% of desired product mass under the curve area at RT=0.862 min. Then, methanesulfonyl chloride (180.60 mg, 1.58 mmol, 122.03 μL) was added dropwise, and the reaction mixture was stirred 25° C. for further 3 hr. The crude reaction mixture was purified by reverse phase HPLC (column: YMC Triart C18 100*20 mm, 5 um, Mobile Phase: 40-90% 1-6 min water-methanol (NH$_3$ 0.1%), flow: 30 mL/min, (loading pump 4 mL/min methanol (NH$_3$0.1%)) to afford N-(5,6-dimethyl-3-pyridyl)-2-[(2S,5R)-2-[4-(methanesulfonamido)phenyl]-5-methyl-1-piperidyl]-2-oxo-acetamide (65 mg, 146.22 μmol, 11.13% yield) as yellow gum, which was directly used in the next step (chiral separation).

LCMS(ESI): [M+H]$^+$ m/z: calcd 444.2; found 445.2; Rt=2.092 min.

Step 2: The Synthesis of N-(5,6-dimethyl-3-pyridyl)-2-[(2S,5R)-2-[4-(methanesulfonamido)phenyl]-5-methyl-1-piperidyl]-2-oxo-acetamide (Compound 630) and N-(5,6-dimethyl-3-pyridyl)-2-[(2R,5S)-2-[4-(methanesulfonamido)phenyl]-5-methyl-1-piperidyl]-2-oxo-acetamide (Compound 621

Racemic N-(5,6-dimethyl-3-pyridyl)-2-[(2S,5R)-2-[4-(methanesulfonamido)phenyl]-5-methyl-1-piperidyl]-2-oxo-acetamide (65 mg, 146.22 μmol) was submitted to preparative chiral HPLC (Column: Chiralpak IA-II (250*20 mm, 5 mkm); Mobile phase: Hexane-IPA-MeOH 50-25-25 Flow Rate: 12 mL/min;) to afford Compound 630—N-(5,6-dimethyl-3-pyridyl)-2-[(2S,5R)-2-[4-(methanesulfonamido)phenyl]-5-methyl-1-piperidyl]-2-oxo-acetamide (21.2 mg, 47.69 μmol, 32.62% yield) (RT=31.713 min.) and Compound 621—N-(5,6-dimethyl-3-pyridyl)-2-[(2R,5S)-2-[4-(methanesulfonamido)phenyl]-5-methyl-1-piperidyl]-2-oxo-acetamide (21.7 mg, 48.81 μmol, 33.38% yield) (RT=46.866 min.) as white solids.

Compound 630: RT (IA, Hexane-IPA-MeOH, 50-25-25, 0.6 mL/min)=33.389 min.

$^1$H NMR (600 MHz, DMSO-d$_6$) δ 0.98 (m, 3H), 1.23 (m, 1H), 1.54 (m, 1H), 1.69 (m, 1H), 2.12 (s, 3H), 2.24 (s, 3H), 2.87 (m, 6H), 3.21 (dd, 1H), 3.41 (dd, 1H), 4.01 (m, 2H), 7.19 (m, 4H), 7.79 (d, 1H), 8.42 (d, 1H).

LCMS(ESI): [M+H]$^+$ m/z: calcd 444.2; found 445.2; Rt=1.963 min.

Compound 621: RT (IA, Hexane-IPA-MeOH, 50-25-25, 0.6 mL/min)=50.039 min.

$^1$H NMR (600 MHz, DMSO-d$_6$) δ 0.98 (m, 3H), 1.23 (m, 1H), 1.54 (m, 1H), 1.69 (m, 1H), 2.14 (s, 3H), 2.20 (s, 3H), 2.87 (m, 6H), 3.17 (m, 1H), 3.40 (m, 1H), 4.01 (m, 2H), 7.21 (m, 4H), 7.80 (d, 1H), 8.42 (d, 1H).

LCMS(ESI): [M+H]$^+$ m/z: calcd 444.2; found 445.2; Rt=1.969 min.

Example 47. The Synthesis of rac-2-((2R,5S)-2-(4-hydroxyphenyl)-5-methylpiperidin-1-yl)-N-(5-methylpyridin-3-yl)-2-oxoacetamide (Compound 557

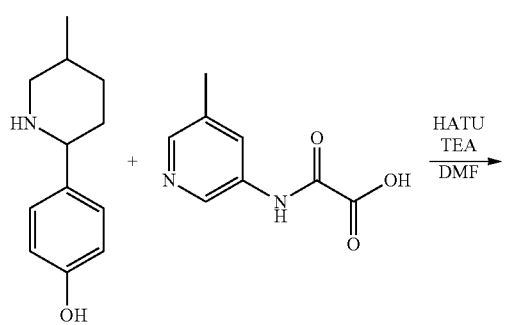

-continued

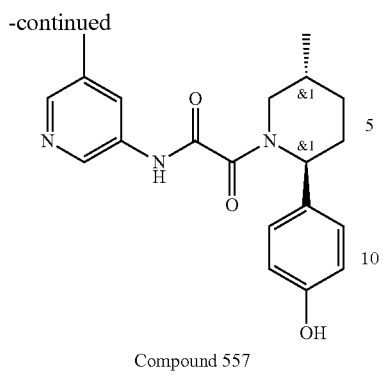

Compound 557

HATU (283.88 mg, 746.59 μmol) was added portionwise at rt to a suspension of 2-[(5-methyl-3-pyridyl)amino]-2-oxo-acetic acid (210.05 mg, 746.59 μmol), 4-(5-methyl-2-piperidyl)phenol (0.21 g, 746.59 μmol) and TEA (453.29 mg, 4.48 mmol, 624.36 μL) in DMF (10 mL). The clear solution was stirred at 25° C. for 32 hr and the solvents were evaporated in vacuo to give 1 g of crude material. It was subjected to RP-HPLC (column: SunFire C18 100×19 mm 5 um; 38-60% 0-5 min water-MeOH 30 ml/min as mobile phase) to give Compound 557 2-[(2S,5R)-2-(4-hydroxyphenyl)-5-methyl-1-piperidyl]-N-(5-methyl-3-pyridyl)-2-oxo-acetamide (42 mg, 118.84 μmol, 15.92% yield).

$^1$H NMR (600 MHz, DMSO-d$_6$) δ (ppm) 0.95-1.05 (m, 3H), 1.25-1.37 (m, 1H), 1.63-1.77 (m, 1H), 1.78-1.93 (m, 1H), 1.93-2.10 (m, 1H), 2.10-2.20 (m, 1H), 2.22-2.32 (m, 3H), 2.71-3.21 (m, 1H), 3.39-4.03 (m, 1H), 4.98-5.63 (m, 1H), 6.71-6.78 (m, 2H), 7.05-7.17 (m, 2H), 7.86-7.97 (m, 1H), 8.09-8.22 (m, 1H), 8.51-8.63 (m, 1H), 9.35 (s, 1H), 10.79-11.13 (m, 1H).

LCMS(ESI): [M]$^+$ m/z: calcd 353.4; found 354.2; Rt=1.781 min.

Example 48. The Synthesis of 5-(2-(2-(4-hydroxyphenyl)-5-methylpiperidin-1-yl)-2-oxoacetamido)-2-methoxynicotinamide (Compound 288, Compound 292

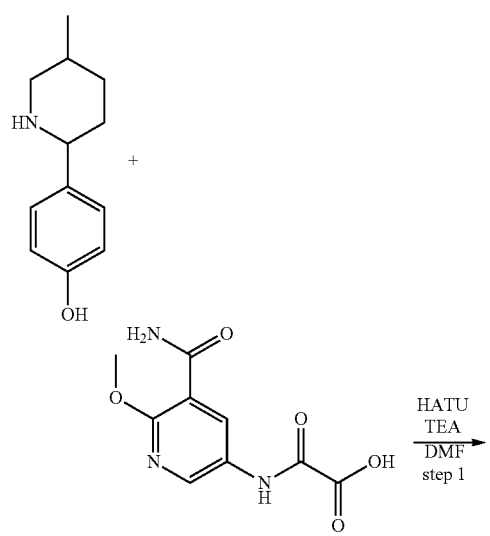

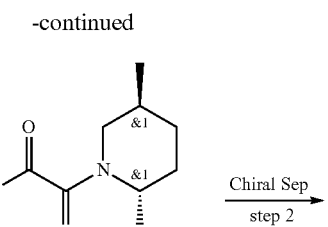

Chiral Sep
step 2

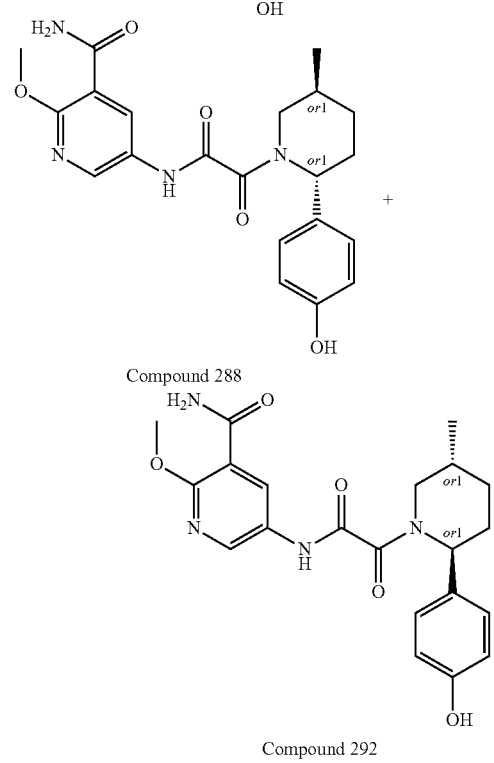

Compound 288

Compound 292

Step 1: Synthesis of 5-(2-(2-(4-hydroxyphenyl)-5-methylpiperidin-1-yl)-2-oxoacetamido)-2-methoxynicotinamide 4-[(2R,5S)-5-methyl-2-piperidyl]phenol (200 mg, 597.20 μmol, HCl), 2-[(5-carbamoyl-6-methoxy-3-pyridyl)amino]-2-oxo-acetic acid (203.27 mg, 597.20 μmol, Et$_3$N) and TEA (151.08 mg, 1.49 mmol, 208.09 μL) were dissolved in DMF (3 mL). HATU (249.78 mg, 656.92 μmol) was added portionwise during 5 min. Resulting solution was stirred at 25° C. for 12 hr. Then it was subjected to HPLC (Column: SunFire C18 100*19 mm, 5 um; 0-5 min 20-45% water-MeCN, flow 30 ml/min), affording 5-[[2-[(2R,5S)-2-(4-hydroxyphenyl)-5-methyl-1-piperidyl]-2-oxo-acetyl]amino]-2-methoxy-pyridine-3-carboxamide (40 mg, 96.98 μmol, 16.24% yield).

$^1$H NMR (500 MHz, DMSO-d$_6$) δ (ppm) LCMS(ESI): [M]$^+$ m/z: calcd 412.4; found 413.2; Rt=2.814 min.

Step 2: Chiral Separation (Compound 288 and Compound 292

Racemate was subjected to chiral HPLC (Column: Chiralpak IA 11 (250*20 mm, 5um); Mobile phase: Hexane- IPA-MeOH, 60-20-20 Flow Rate: 12 mL/min; m=0.04 g, 3 inj., 12 mg/inj. V=2.2 L. time=3.5 h.), affording 5-[[2-[(2S,5R)-2-(4-hydroxyphenyl)-5-methyl-1-piperidyl]-2-oxo-acetyl]amino]-2-methoxy-pyridine-3-carboxamide (13 mg, 31.52 μmol, 63.41% yield) ret.time=33.85 min and 5-[[2-[(2R,5S)-2-(4-hydroxyphenyl)-5-methyl-1-piperidyl]-2-oxo-acetyl]amino]-2-methoxy-pyridine-3-carboxamide (12 mg, 29.10 μmol, 58.54% yield) ret.time=47.087 min. Ret time for Compound 288 in analytical conditions (column: IA, Hexane-IPA-MeOH, 60-20-20, 0.6 ml/min as mobile phase) 44.81 min and for Compound 292 32.41 min.

Compound 288: Retention time: 44.81 min $^1$H NMR (500 MHz, DMSO-$d_6$) δ (ppm) 0.98-1.06 (m, 3H), 1.27-1.40 (m, 1H), 1.63-1.77 (m, 1H), 1.80-1.93 (m, 1H), 1.96-2.12 (m, 1H), 2.12-2.25 (m, 1H), 2.72-3.20 (m, 1H), 3.39-3.47 (m, 1H), 3.93-4.01 (m, 3H), 4.95-5.66 (m, 1H), 6.68-6.81 (m, 2H), 7.06-7.21 (m, 2H), 7.68-7.82 (m, 2H), 8.41-8.49 (m, 1H), 8.50-8.60 (m, 1H), 9.37 (s, 1H), 10.86-11.11 (m, 1H).

LCMS(ESI): [M]$^+$ m/z: calcd 412.4; found 413.2; Rt=2.861 min.

Compound 292: Retention time: 32.41 min $^1$H NMR (500 MHz, DMSO-$d_6$) δ (ppm) 0.99-1.06 (m, 3H), 1.28-1.42 (m, 1H), 1.66-1.81 (m, 1H), 1.82-1.94 (m, 1H), 1.97-2.11 (m, 1H), 2.12-2.22 (m, 1H), 2.75-3.20 (m, 1H), 3.39-3.48 (m, 1H), 3.94-4.04 (m, 3H), 5.01-5.61 (m, 1H), 6.69-6.87 (m, 2H), 7.07-7.18 (m, 2H), 7.67-7.79 (m, 2H), 8.42-8.51 (m, 1H), 8.50-8.60 (m, 1H), 9.37 (s, 1H), 10.91-11.13 (m, 1H).

LCMS(ESI): [M]$^+$ m/z: calcd 412.4; found 413.2; Rt=2.859 min.

Example 49. The Synthesis of 5-(2-(2-(4-hydroxyphenyl)-5-methylpiperidin-1-yl)-2-oxoacetamido) Nicotinamide (Compound 287, Compound 297

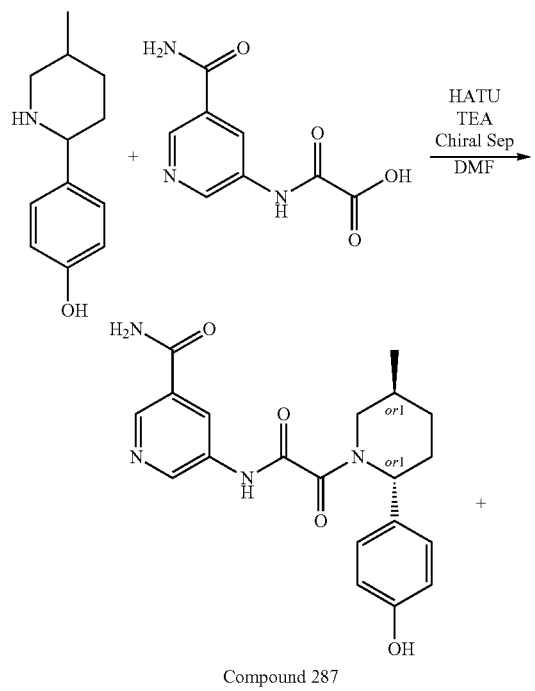

Compound 287

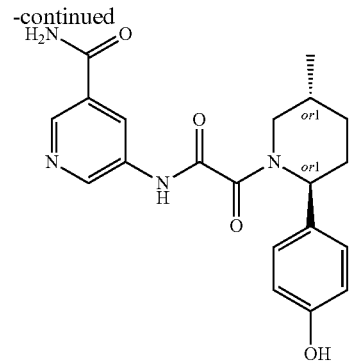

Compound 297

TEA (1.76 g, 17.41 mmol, 2.43 mL) was added to a stirred mixture of 4-(5-methyl-2-piperidyl)phenol (0.65 g, 1.74 mmol, HCl), 2-[(5-carbamoyl-3-pyridyl)amino]-2-oxo-acetic acid (540.35 mg, 1.74 mmol) and HATU (662.02 mg, 1.74 mmol) in DMF (10 mL). The reaction mixture was stirred at 25° C. for 2 hr, and then submitted to reverse phase HPLC (column: XBridge C18 100×19 mm, Sum, mobile phase 10-10-40% 0—2-6 min 0.10% NH$_3$-MeOH) to afford 95 mg of racemic amide as light-yellow solid. It was then submitted to chiral HPLC (column: Chiralpak AD-H I, (250*20 mm, 5 mkm); Mobile phase: Hexane-IPA-MeOH 70-15-15 Flow Rate: 12 mL/min) to afford Compound 287 5-[[2-[(2R,5S)-2-(4-hydroxyphenyl)-5-methyl-1-piperidyl]-2-oxo-acetyl]amino]pyridine-3-carboxamide (28 mg, 73.22 μmol, 4.21% yield) (RT=29.61) and Compound 297 5-[[2-[(2S,5R)-2-(4-hydroxyphenyl)-5-methyl-1-piperidyl]-2-oxo-acetyl]amino]pyridine-3-carboxamide (24 mg, 62.76 μmol, 3.60% yield) (RT=20.32). Ret time for Compound 287 in analytical conditions (column: AD-H, Hexane-IPA-MeOH 70-15-15, 0.6 ml/min as mobile phase) 31.37 min and for Compound 297 22.48 min.

Compound 287: Retention time: 31.37 min $^1$H NMR (600 MHz, DMSO-$d_6$) δ (ppm) 0.98-1.04 (m, 3H), 1.27-1.38 (m, 1H), 1.65-1.77 (m, 1H), 1.80-1.91 (m, 1H), 1.96-2.11 (m, 1H), 2.12-2.20 (m, 1H), 2.74-3.21 (m, 1H), 3.37-4.02 (m, 1H), 5.01-5.56 (m, 1H), 6.70-6.78 (m, 2H), 7.04-7.15 (m, 2H), 7.53-7.68 (m, 1H), 8.10-8.22 (m, 1H), 8.41-8.51 (m, 1H), 8.69-8.81 (m, 1H), 8.82-8.93 (m, 1H), 9.36 (s, 1H), 11.11-11.28 (m, 1H).

LCMS(ESI): [M]$^+$ m/z: calcd 382.5; found 383.2; Rt=2.558 min.

Compound 297: Retention time: 22.48 min $^1$H NMR (600 MHz, DMSO-$d_6$) δ (ppm) 0.98-1.05 (m, 3H), 1.24-1.37 (m, 1H), 1.61-1.76 (m, 1H), 1.79-1.92 (m, 1H), 1.94-2.10 (m, 1H), 2.12-2.19 (m, 1H), 2.73-3.21 (m, 1H), 3.38-4.01 (m, 1H), 5.01-5.59 (m, 1H), 6.71-6.81 (m, 2H), 7.05-7.20 (m, 2H), 7.52-7.69 (m, 1H), 8.07-8.21 (m, 1H), 8.42-8.59 (m, 1H), 8.70-8.80 (m, 1H), 8.82-8.95 (m, 1H), 9.35 (s, 1H), 11.11-11.27 (m, 1H).

LCMS(ESI): [M]$^+$ m/z: calcd 382.5; found 383.2; Rt=2.560 min.

Example 50. The Synthesis of 5-[[2-[(2R,5R)-4,4-difluoro-5-methyl-2-phenyl-1-piperidyl]-2-oxo-acetyl]amino]pyridine-3-carboxamide (Compound 473), 5-[[2-[(2S,5S)-4,4-difluoro-5-methyl-2-phenyl-1-piperidyl]-2-oxo-acetyl]amino]pyridine-3-carboxamide (Compound 457

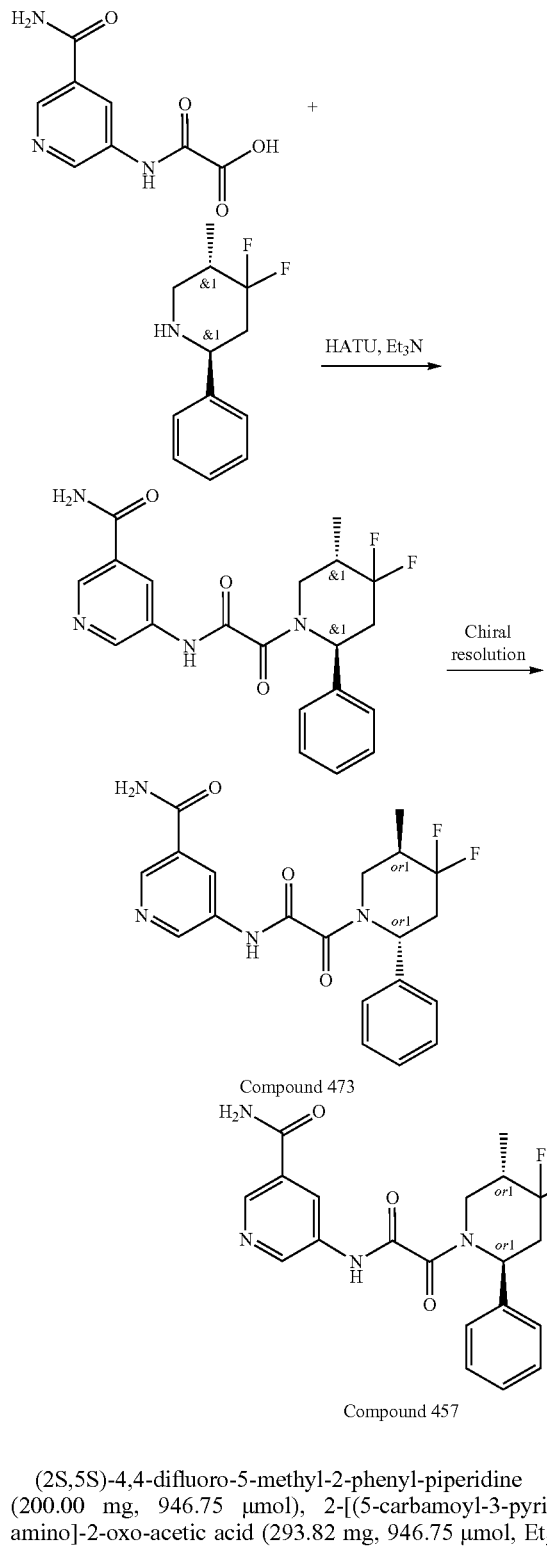

Compound 473

Compound 457

(2S,5S)-4,4-difluoro-5-methyl-2-phenyl-piperidine (200.00 mg, 946.75 μmol), 2-[(5-carbamoyl-3-pyridyl)amino]-2-oxo-acetic acid (293.82 mg, 946.75 μmol, Et₃N), TEA (958.01 mg, 9.47 mmol, 1.32 mL) and HATU (539.97 mg, 1.42 mmol) was dissolved in DMF (7 mL) and stirred at 20° C. for 3 hr. Reaction mixture was diluted with water end extracted three times with EA, then EA was extracted three times with brine. Organic phase was dried over Na$_2$SO$_4$, filtered and evaporated at 40° C. to give crude product which was purified by HPLC (40-60% water/MeCN+NH$_3$, 2-10 min, flow 30 ml/min (loading pump 4 ml/min MeCN+NH$_3$) column: TRIART 100*20 5 mM) to give pure mixture of 2 enantiomers.

Chiral separation was performed using Column: Chiralpak 1B(250*20 mm, 5 mkm); Injection Volume 900 mkl; Mobile phase: Hexane-IPA-MeOH 60-20-20 Flow Rate: 15 mL/min to give 5-[[2-[(2S,5S)-4,4-difluoro-5-methyl-2-phenyl-1-piperidyl]-2-oxo-acetyl]amino]pyridine-3-carboxamide (0.034 g, 84.49 μmol, 8.92% yield) as single enantiomer and 5-[[2-[(2R,5R)-4,4-difluoro-5-methyl-2-phenyl-1-piperidyl]-2-oxo-acetyl]amino]pyridine-3-carboxamide (0.035 g, 86.98 μmol, 9.19% yield) as single enantiomer.

Compound 473: RT (IB, Hex-IPA-MeOH, 50-25-25, 0.6 ml/min)=14.870 min $^1$H NMR (600 MHz, DMSO-d$_6$) δ 1.09 (d, 3H), 2.09-2.28 (m, 1H), 2.42-2.46 (m, 1H), 2.80-2.91 (m, 1H), 3.02-3.09 (m, 0.4H), 3.44-3.52 (m, 0.6H), 3.78-4.35 (m, 1H), 5.53-5.96 (m, 1H), 7.21-7.30 (m, 1H), 7.30-7.37 (m, 3H), 7.37-7.41 (m, 1H), 7.55-7.67 (m, 1H), 8.09-8.21 (m, 1H), 8.41-8.56 (m, 1H), 8.69-8.81 (m, 1H), 8.81-8.96 (m, 1H), 11.13-11.49 (m, 1H).

LCMS(ESI): [M+1]$^+$ m/z: calcd 402.2; found 403.2; Rt=2.994 min.

Compound 457: RT (IB, Hex-IPA-MeOH, 50-25-25, 0.6 ml/min)=10.108 min $^1$H NMR (600 MHz, DMSO-d$_6$) δ 1.09 (d, 3H), 2.09-2.28 (m, 1H), 2.42-2.46 (m, 1H), 2.80-2.91 (m, 1H), 3.02-3.09 (m, 0.4H), 3.44-3.52 (m, 0.6H), 3.78-4.35 (m, 1H), 5.53-5.96 (m, 1H), 7.21-7.30 (m, 1H), 7.30-7.37 (m, 3H), 7.37-7.41 (m, 1H), 7.55-7.67 (m, 1H), 8.09-8.21 (m, 1H), 8.41-8.56 (m, 1H), 8.69-8.81 (m, 1H), 8.81-8.96 (m, 1H), 11.13-11.49 (m, 1H).

LCMS(ESI): [M+1]$^+$ m/z: calcd 402.2; found 403.2; Rt=2.996 min.

The Synthesis of 5-(2-(5-fluoro-5-methyl-2-phenylpiperidin-1-yl)-2-oxoacetamido)nicotinamide (Compound 795, Compound 798

1329

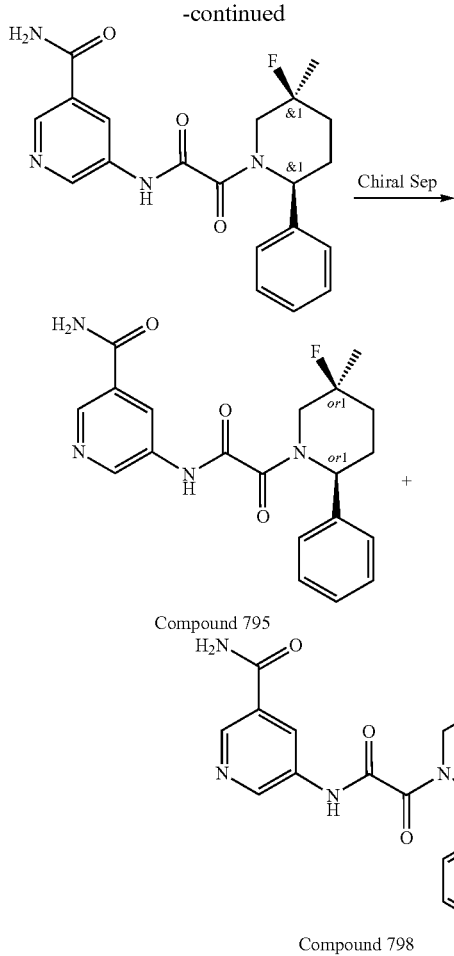

Compound 795

Compound 798

Step 1: Synthesis of 5-(2-(5-fluoro-5-methyl-2-phenylpiperidin-1-yl)-2-oxoacetamido)nicotinamide 2-[(5-carbamoyl-3-pyridyl)amino]-2-oxo-acetic acid (17.79 mg, 72.44 μmol, HCl) and TEA (73.30 mg, 724.41 μmol, 100.97 μL) were dissolved in DMF (2 mL) and cooled to 0° C., HATU (41.32 mg, 108.66 μmol) was added and the mixture was stirred for 15 min at 0° C. (2R,5R)-5-fluoro-5-methyl-2-phenyl-piperidine (0.014 g, 72.44 μmol) was added and the mixture was warmed to rt and stirred for 3 hr. 10 ml of ethyl acetate was added and organic phase was washed with brine three times. Organic phase was dried over $Na_2SO_4$, filtered and concentrated in vacuo at 45° C. to give crude product which was purified by HPLC (5-95% MeCN 6 min. Poroshell 120 EC-C18 4, 6*100 mm) to give 5-[[2-[(2R,5R)-5-fluoro-5-methyl-2-phenyl-1-piperidyl]-2-oxo-acetyl]amino]pyridine-3-carboxamide (0.013 g, 33.82 μmol, 46.68% yield).

$^1$H NMR (400 MHz, CDCl$_3$) δ (ppm)

LCMS(ESI): [M]$^+$ m/z: calcd 384.2; found 385.2; Rt=3.852 min.

Step 2: Chiral Separation (Compound 795 and Compound 798

The mixture of diastereomers was separated by chiral chromatography (IA-II(250*20.5 mkm), IPA-MeOH, 50-50, 12 ml/min) to obtain tert-butyl N-[5-[[2-[(2S,5R)-2-(6-amino-3-pyridyl)-5-methyl-1-piperidyl]-2-oxo-acetyl]amino]-3-ethyl-2-pyridyl]carbamate (21.02 mg, 43.56 μmol, 34.12% yield) (RT=19.23).

Chiral separation was performed using Column: Chiralpak AD-H—III (250*20, 5 mkm), Hexane-MeOH-IPA, 60-20-20, 12 ml/min to give 5-[[2-[(2R,5R)-5-fluoro-5-methyl-2-phenyl-1-piperidyl]-2-oxo-acetyl]amino]pyridine-3-carboxamide (0.0044 g, 11.45 μmol, 33.85% yield) (RT=42.39).

Ret time for Compound 795 in analytical conditions (column: IA, IPA-MeOH, 50-50, 0.6 ml/min as mobile phase) 17.48 min and for Compound 798 11.91 min.

Compound 795: Retention time: 17.48 min $^1$H NMR (600 MHz, DMSO-d$_6$) δ (ppm)

LCMS(ESI): [M]$^+$ m/z: calcd 384.2; found 385.2; Rt=3.859 min.

Compound 798: Retention time: 11.91 min $^1$H NMR (600 MHz, DMSO-d$_6$) δ (ppm)

LCMS(ESI): [M]$^+$ m/z: calcd 384.2; found 385.2; Rt=3.858 min.

Example 51. The Synthesis of rac-2-[(2R,3R,6S)-2,3-dimethyl-6-phenyl-1-piperidyl]-N-(5-methyl-3-pyridyl)-2-oxo-acetamide and rac-2-[(2S,3R,6S)-2,3-dimethyl-6-phenyl-1-piperidyl]-N-(5-methyl-3-pyridyl)-2-oxo-acetamide (Compound 25 and Compound 23); Chiral Separation to 2-[(2S,3R,6S)-2,3-dimethyl-6-phenyl-1-piperidyl]-N-(5-methyl-3-pyridyl)-2-oxo-acetamide, 2-[(2R,3S,6R)-2,3-dimethyl-6-phenyl-1-piperidyl]-N-(5-methyl-3-pyridyl)-2-oxo-acetamide (Compound 39 and Compound 32), 2-[(2R,3R,6S)-2,3-dimethyl-6-phenyl-1-piperidyl]-N-(5-methyl-3-pyridyl)-2-oxo-acetamide and 2-[(2S,3S,6R)-2,3-dimethyl-6-phenyl-1-piperidyl]-N-(5-methyl-3-pyridyl)-2-oxo-acetamide (Compound 41 and Compound 35

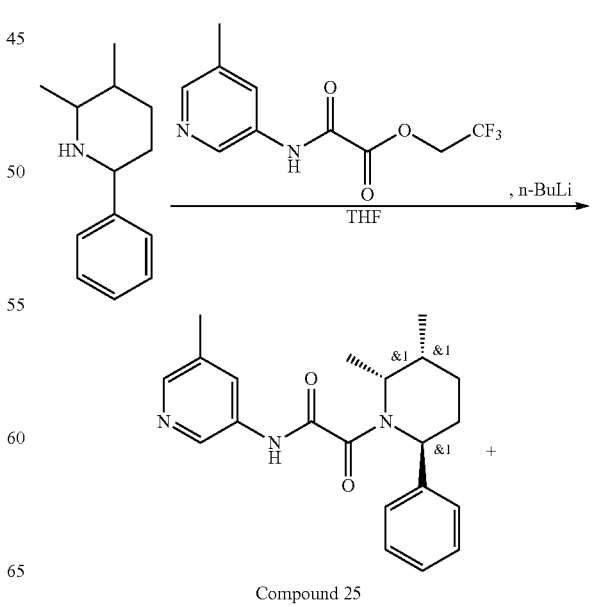

Compound 25

-continued

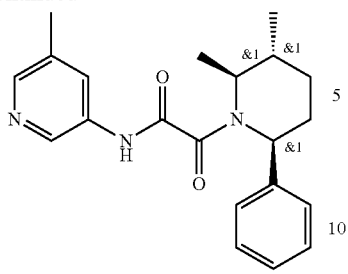

Compound 61

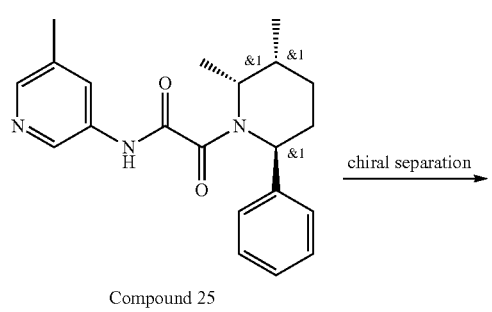 chiral separation →

Compound 25

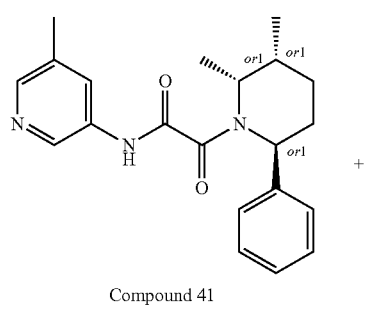 +

Compound 41

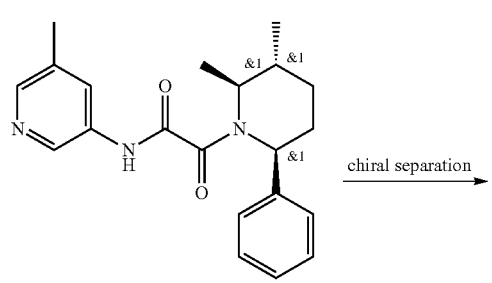

Compound 35

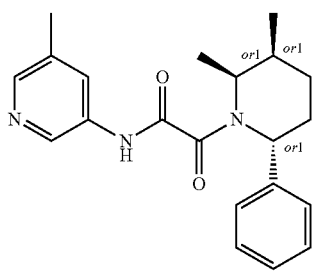 chiral separation →

Compound 61

-continued

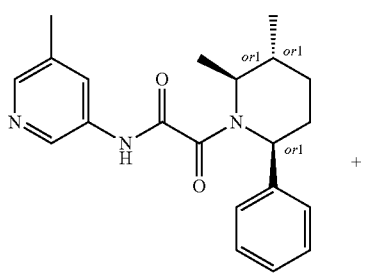 +

Compound 39

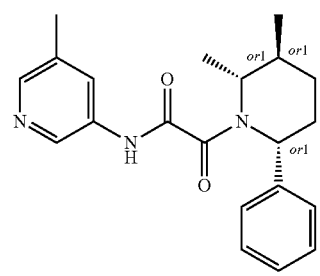

Compound 32

Step 1—Synthesis of rac-2-[(2R,3R,6S)-2,3-dimethyl-6-phenyl-1-piperidyl]-N-(5-methyl-3-pyridyl)-2-oxo-acetamide and rac-2-[(2S,3R,6S)-2,3-dimethyl-6-phenyl-1-piperidyl]-N-(5-methyl-3-pyridyl)-2-oxo-acetamide To a stirred solution of 2,3-dimethyl-6-phenyl-piperidine (1.7 g, 8.98 mmol) in THF (20 mL) at −78° C., n-butyllithium (2.5 M in Hexane, 1.15 g, 17.96 mmol, 7.18 mL) was added dropwise under argon atmosphere. The resulting mixture was stirred at the same temperature for 5 minutes. After 5 minutes, 2,2,2-trifluoroethyl 2-[(5-methyl-3-pyridyl)amino]-2-oxo-acetate (2.35 g, 8.98 mmol) was added. The resulting mixture was allowed to warm to room temperature and stirred for 12 hours at the same temperature. Upon completion, the reaction mixture was quenched with saturated aq NH$_4$Cl solution. The resulting mixture was evaporated to dryness. The obtained residue (1 g) was purified by reverse phase HPLC (Eluent: 0.5-6.5 min; water—acetonitrile; flow rate: 30 mL/min; loading pump: 4 mL/min, acetonitrile; column: SunFire 100*19 mm, 5 um) to obtain rac-2-[(2R,3R,6S)-2,3-dimethyl-6-phenyl-1-piperidyl]-N-(5-methyl-3-pyridyl)-2-oxo-acetamide (Compound 25, 41.30 mg) and rac-2-[(2S,3R,6S)-2,3-dimethyl-6-phenyl-1-piperidyl]-N-(5-methyl-3-pyridyl)-2-oxo-acetamide (Compound 23, 35.9 mg) as yellow solid.

Compound 25: $^1$H NMR (DMSO-d$_6$+CCl$_4$, 400 MHz): δ (ppm) 0.66 (m, 3H), 0.98 (m, 3H), 1.65 (m, 2H), 1.99 (m, 2H), 2.34 (m, 3H), 2.61 (m, 1H), 4.30 (m, 1H), 5.49 (m, 1H), 7.21 (m, 1H), 7.31 (m, 2H), 7.43 (m, 2H), 7.99 (m, 1H), 8.08 (m, 1H), 8.55 (m, 1H), 10.90 (m, 1H).

LCMS(ESI): [M+H]+ m/z: calcd 351.2; found 352.2; Rt=3.380 min.

Compound 23: $^1$H NMR (DMSO-$d_6$+CCl$_4$, 400 MHz): δ (ppm) 0.76 (m, 3H), 1.11 (m, 3H), 1.51 (m, 1H), 1.71 (m, 1H), 1.98 (m, 1H), 2.12 (m, 1H), 2.34 (m, 3H), 2.61 (m, 1H), 3.84 (m, 1H), 5.57 (m, 1H), 7.21 (m, 1H), 7.31 (m, 2H), 7.43 (m, 2H), 7.97 (m, 1H), 8.10 (m, 1H), 8.57 (m, 1H), 10.89 (m, 1H).

LCMS(ESI): [M+H]+ m/z: calcd 351.2; found 352.2; Rt=3.365 min.

Step 2. Chiral Separation of 2-[(2R,3R,6S)-2,3-dimethyl-6-phenyl-1-piperidyl]-N-(5-methyl-3-pyridyl)-2-oxo-acetamide and 2-[(2S,3S,6R)-2,3-dimethyl-6-phenyl-1-piperidyl]-N-(5-methyl-3-pyridyl)-2-oxo-acetamide rac-2-[(2R,3R,6S)-2,3-dimethyl-6-phenyl-1-piperidyl]-N-(5-methyl-3-pyridyl)-2-oxo-acetamide (Compound 25.41 mg) was subjected to chiral separation (Chiralcel OJ-H (250*20 mm, 5 um; Mobile phase: Hexane-IPA-MeOH 90-5-5; Flow Rate: 12 mL/min) to obtain (Compound 35, 10 mg) and (Compound 41, 10 mg) as yellow solid.

Compound 41: LCMS(ESI): [M+H]+ m/z: calcd 351.2; found 352.2; Rt=1.270 min.

Chiral HPLC: Rt=28.22 min (Column: Chiralcel OJ-H; Mobile phase: Hexane-MeOH-IPA, 70-15-15; Flow Rate: 0.6 mL/min).

Compound 35: LCMS(ESI): [M+H]+ m/z: calcd 351.2; found 352.2; Rt=1.270 min.

Chiral HPLC: Rt=8.69 min (Column: Chiralcel OJ-H; Mobile phase: Hexane-MeOH-IPA, 70-15-15; Flow Rate: 0.6 mL/min).

Step 3. Chiral Separation of 2-[(2S,3R,6S)-2,3-dimethyl-6-phenyl-1-piperidyl]-N-(5-methyl-3-pyridyl)-2-oxo-acetamide and 2-[(2R,3S,6R)-2,3-dimethyl-6-phenyl-1-piperidyl]-N-(5-methyl-3-pyridyl)-2-oxo-acetamide rac-2-[(2S,3R,6S)-2,3-dimethyl-6-phenyl-1-piperidyl]-N-(5-methyl-3-pyridyl)-2-oxo-acetamide (Compound 23, 35.9 mg) was subjected to chiral separation (Chiralcel OJ-H (250*20 mm, 5 um; Mobile phase: Hexane-IPA-MeOH 90-5-5; Flow Rate: 12 mL/min) to obtain (Compound 39, 12 mg) and (Compound 32, 10 mg) as yellow solid.

Compound 39: LCMS(ESI): [M+H]+ m/z: calcd 351.2; found 352.2; Rt=1.202 min.

Chiral HPLC: Rt=14.78 min (Column: Chiralcel OJ-H; Mobile phase: Hexane-MeOH-IPA, 70-15-15; Flow Rate: 0.6 mL/min).

Compound 32: LCMS(ESI): [M+H]+ m/z: calcd 351.2; found 352.2; Rt=1.266 min.

Chiral HPLC: Rt=23.10 min (Column: Chiralcel OJ-H; Mobile phase: Hexane-MeOH-IPA, 70-15-15; Flow Rate: 0.6 mL/min).

Example 52. The Synthesis of 5-[[2-[5-methyl-2-(3-pyridyl)-1-piperidyl]-2-oxo-acetyl]amino]pyridine-3-carboxamide (Compound 102), 5-[[2-[(2S,5S)-5-methyl-2-(3-pyridyl)-1-piperidyl]-2-oxo-acetyl]amino]pyridine-3-carboxamide, 5-[[2-[(2R,5S)-5-methyl-2-(3-pyridyl)-1-piperidyl]-2-oxo-acetyl]amino]pyridine-3-carboxamide, 5-[[2-[(2S,5R)-5-methyl-2-(3-pyridyl)-1-piperidyl]-2-oxo-acetyl]amino]pyridine-3-carboxamide and 5-[[2-[(2R,5R)-5-methyl-2-(3-pyridyl)-1-piperidyl]-2-oxo-acetyl]amino]pyridine-3-carboxamide (+—*Compound 104, Compound 105, Compound 106 and Compound 98

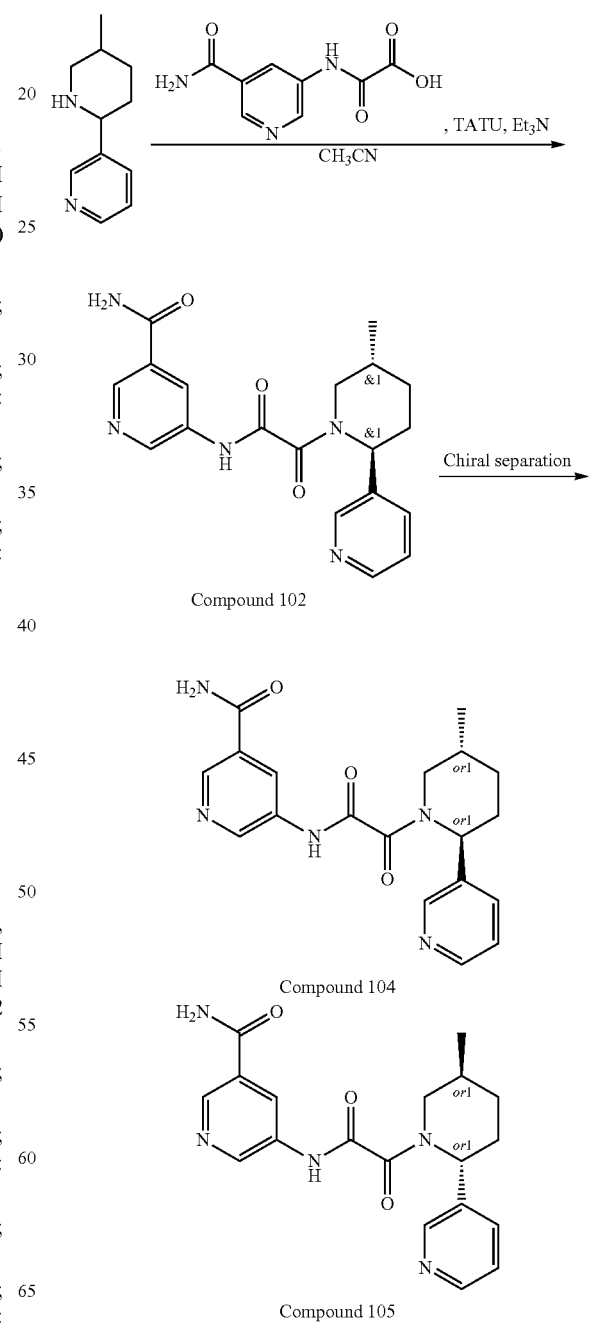

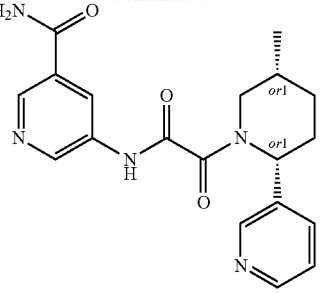

Compound 106

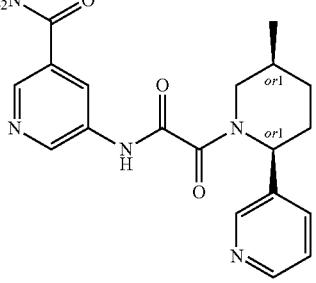

Compound 98

Step 1: Synthesis of 5-[[2-[5-methyl-2-(3-pyridyl)-1-piperidyl]-2-oxo-acetyl]amino]pyridine-3-carboxamide (Compound 102

To a stirred solution of 2-[(5-carbamoyl-3-pyridyl)amino]-2-oxo-acetic acid (0.4, 1.29 mmol, Et₃N salt), TATU (622.66 mg, 1.93 mmol) and triethylamine (130.42 mg, 1.29 mmol, 179.64 μL) in dry CH₃CN (25 mL) at 21° C. was added 3-(5-methyl-2-piperidyl)pyridine (272.61 mg, 1.55 mmol). The resulting reaction mixture was stirred at 21° C. for overnight. The resulting reaction mixture was evaporated to dryness and subjected to HPLC (Eluent: 20-70%, 0-11.5 min, water—methanol; flow rate: 30 mL/min; loading pump 4 mL/min, methanol; column: SunFire C18 100*19 mm, 5 um) to give 5-[[2-[5-methyl-2-(3-pyridyl)-1-piperidyl]-2-oxo-acetyl]amino]pyridine-3-carboxamide (Compound 102, 37.2 mg, 101.25 μmol, 7.86% yield).

¹H NMR (CDCl₃, 400 MHz): δ (ppm) 1.10 (m, 3H), 1.42 (m, 1H), 1.86 (m, 2H), 2.01 (m, 1H), 2.24 (m, 1H), 3.14 (m, 1H), 4.50 (m, 1H), 6.35 (m, 1H), 7.32 (m, 1H), 7.63 (m, 1H), 8.52 (m, 1H), 8.60 (m, 3H), 8.80 (m, 1H), 8.95 (m, 1H), 9.84 (s, 1H).

LCMS(ESI): [M+H]⁺ m/z: calcd 367.2; found 368.2; Rt=1.699 min.

Step 2: Chiral Separation of 5-[[2-[(2S,5S)-5-methyl-2-(3-pyridyl)-1-piperidyl]-2-oxo-acetyl]amino]pyridine-3-carboxamide, 5-[[2-[(2R,5S)-5-methyl-2-(3-pyridyl)-1-piperidyl]-2-oxo-acetyl]amino]pyridine-3-carboxamide, 5-[[2-[(2S,5R)-5-methyl-2-(3-pyridyl)-1-piperidyl]-2-oxo-acetyl]amino]pyridine-3-carboxamide and 5-[[2-[(2R,5R)-5-methyl-2-(3-pyridyl)-1-piperidyl]-2-oxo-acetyl]amino]pyridine-3-carboxamide (Compound 104, Compound 105, Compound 106 and Compound 98

5-[[2-[5-methyl-2-(3-pyridyl)-1-piperidyl]-2-oxo-acetyl]amino]pyridine-3-carboxamide (Compound 102, 37.2 mg, 101.25 μmol) was subjected to chiral HPLC purification to get 5-[[2-[(2S,5S)-5-methyl-2-(3-pyridyl)-1-piperidyl]-2-oxo-acetyl]amino]pyridine-3-carboxamide (Compound 104, 3.72 mg), 5-[[2-[(2R,5S)-5-methyl-2-(3-pyridyl)-1-piperidyl]-2-oxo-acetyl]amino]pyridine-3-carboxamide (Compound 105, 9.15 mg), 5-[[2-[(2S,5R)-5-methyl-2-(3-pyridyl)-1-piperidyl]-2-oxo-acetyl]amino]pyridine-3-carboxamide (Compound 106, 8.49 mg) and 5-[[2-[(2R,5R)-5-methyl-2-(3-pyridyl)-1-piperidyl]-2-oxo-acetyl]amino]pyridine-3-carboxamide (Compound 98, 3.72 mg) as white solids.

Compound 104:
¹H NMR (CDCl₃, 400 MHz): δ (ppm) 0.90 (m, 3H), 1.29 (m, 2H), 1.83 (m, 2H), 2.10 (m, 1H), 2.52 (m, 2H), 4.63 (m, 1H), 6.26 (m, 1H), 7.37 (m, 1H), 7.66 (m, 1H), 8.61 (m, 3H), 8.84 (m, 1H), 8.94 (m, 1H), 9.63 (m, 1H).

LCMS(ESI): [M+H]⁺ m/z: calcd 367.2; found 368.2; Rt=2.889 min.

Chiral HPLC: Rt=21.83 min (Column: AD-H; Eluent: Hexane-MeOH-IPA, 50-25-25; Flow Rate: 0.6 mL/min).

Compound 105:
¹H NMR (CDCl₃, 500 MHz): δ (ppm) 1.14 (m, 3H), 1.46 (m, 1H), 1.90 (d, 1H), 2.05 (m, 1H), 2.27 (m, 2H), 3.25 (m, 1H), 4.54 (m, 1H), 6.16 (m, 2H), 7.35 (m, 1H), 7.66 (m, 1H), 8.59 (m, 3H), 8.84 (m, 1H), 8.92 (m, 1H), 9.67 (s, 1H).

LCMS(ESI): [M+H]⁺ m/z: calcd 367.2; found 368.2; Rt=2.844 min.

Chiral HPLC: Rt=47.00 min (Column: AD-H; Eluent: Hexane-MeOH-IPA, 50-25-25; Flow Rate: 0.6 mL/min).

Compound 106:
¹H NMR (CDCl₃, 600 MHz): δ (ppm) 0.95 (m, 3H), 1.22 (m, 1H), 1.58 (m, 1H), 1.70 (m, 1H), 1.91 (m, 2H), 2.65 (m, 1H), 3.77 (m, 1H), 5.16 (m, 2H), 6.13 (m, 1H), 6.38 (m, 1H), 7.15 (m, 3H), 7.36 (s, 1H), 7.44 (m, 1H), 8.09 (s, 1H).

LCMS(ESI): [M+H]⁺ m/z: calcd 367.2; found 368.2; Rt=2.843 min.

Chiral HPLC: Rt=36.06 min (Column: AD-H; Eluent: Hexane-MeOH-IPA, 50-25-25; Flow Rate: 0.6 mL/min).

Compound 98:
¹H NMR (CDCl₃, 500 MHz): δ (ppm) 0.90 (m, 3H), 1.27 (m, 1H), 1.81 (m, 2H), 1.91 (m, 1H), 2.10 (m, 1H), 2.52 (m, 2H), 4.63 (m, 1H), 6.27 (m, 1H), 7.38 (m, 1H), 7.67 (m, 1H), 8.62 (m, 3H), 8.85 (m, 1H), 8.97 (m, 1H), 9.62 (m, 1H).

LCMS(ESI): [M+H]⁺ m/z: calcd 367.2; found 368.2; Rt=2.890 min.

Chiral HPLC: Rt=24.08 min (Column: AD-H; Eluent: Hexane-MeOH-IPA, 50-25-25; Flow Rate: 0.6 mL/min).

Example 53. The Synthesis of Compound 369, Compound 370, Compound 371 and Compound 389

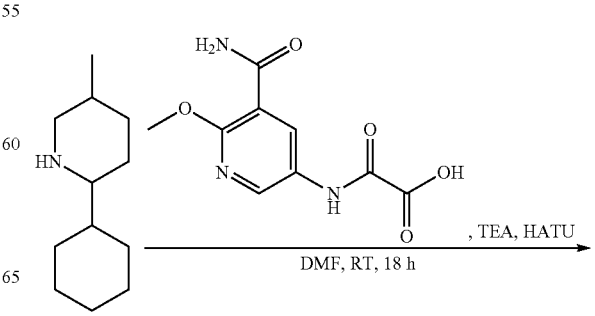

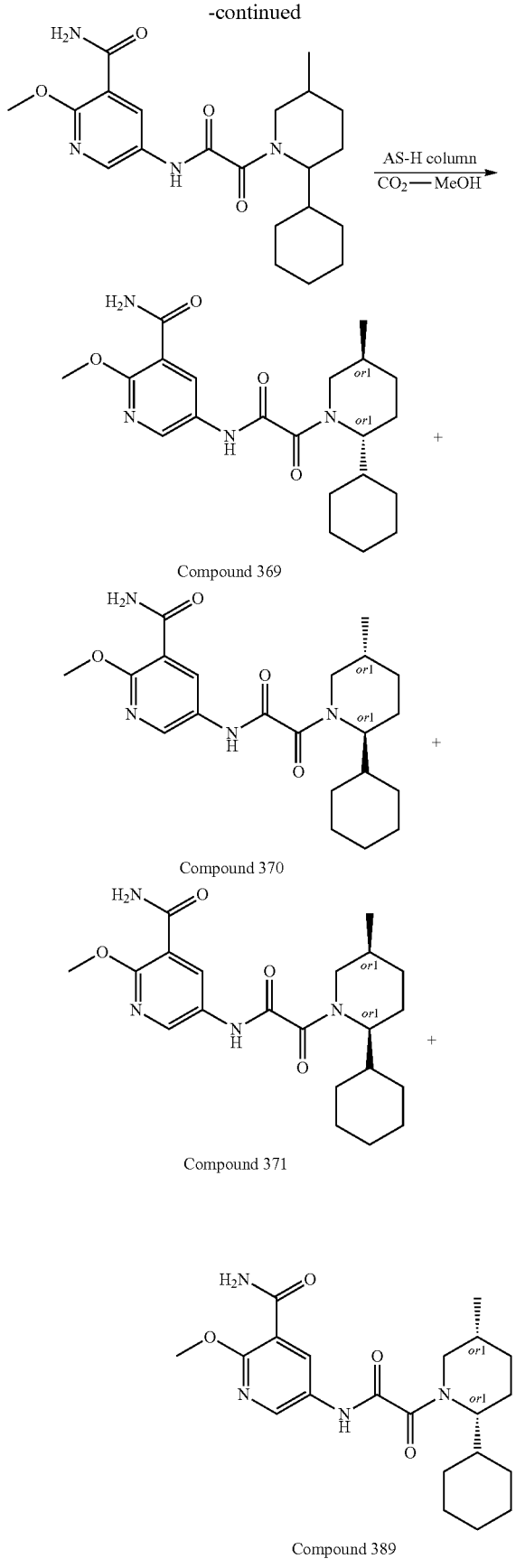

Compound 369

Compound 370

Compound 371

Compound 389

Step 1: The Synthesis of 5-[[2-(2-cyclohexyl-5-methyl-1-piperidyl)-2-oxo-acetyl]amino]-2-methoxy-pyridine-3-carboxamide 2-cyclohexyl-5-methyl-piperidine (0.219 g, 1.01 mmol, HCl), 2-[(5-carbamoyl-6-methoxy-3-pyridyl)amino]-2-oxo-acetic acid (342.28 mg, 1.01 mmol) and triethylamine (1.02 g, 10.06 mmol, 1.40 mL) were mixed together in DMF (5 mL) and HATU (573.55 mg, 1.51 mmol) was added thereto. The reaction mixture was stirred for 18 h. Then, the reaction mixture was poured into water (20 mL) and the resulting mixture was extracted with EtOAc (2*30 mL). The combined organic layers were washed with water (3*25 mL), brine, dried over $Na_2SO_4$, filtered and evaporated. The residue was purified by HPLC (2-10 min 60-85% MeOH/$H_2O$+formic acid, 30 mL/min (loading pump 4 mL+formic acid), column: SunFire 100*19 mm, 5 microM) to obtain 5-[[2-(2-cyclohexyl-5-methyl-1-piperidyl)-2-oxo-acetyl]amino]-2-methoxy-pyridine-3-carboxamide (0.0428 g, 106.34 μmol, 10.57% yield).

$^1$H NMR (400 MHz, DMSO-$d_6$) δ 0.82 (m, 2H), 0.94 (m, 3H), 1.19 (m, 4H), 1.64 (m, 10H), 2.85 (m, 1H), 3.47 (m, 1H), 3.96 (s, 3H), 4.13 (m, 1H), 7.75 (s, 1H), 8.53 (m, 1H), 8.55 (s, 1H), 10.87 (m, 1H).

LCMS(ESI): [M+H]$^+$ m/z: calcd 402.2; found 403.2; Rt=1.475 min.

Step 2: The Synthesis of 5-[[2-[(2R,5S)-2-cyclohexyl-5-methyl-1-piperidyl]-2-oxo-acetyl]amino]-2-methoxy-pyridine-3-carboxamide (Compound 369), 5-[[2-[(2S,5R)-2-cyclohexyl-5-methyl-1-piperidyl]-2-oxo-acetyl]amino]-2-methoxy-pyridine-3-carboxamide (Compound 370), 5-[[2-[(2S,5S)-2-cyclohexyl-5-methyl-1-piperidyl]-2-oxo-acetyl]amino]-2-methoxy-pyridine-3-carboxamide (Compound 371) and 5-[[2-[(2R,5R)-2-cyclohexyl-5-methyl-1-piperidyl]-2-oxo-acetyl]amino]-2-methoxy-pyridine-3-carboxamide (Compound 389

5-[[2-(2-cyclohexyl-5-methyl-1-piperidyl)-2-oxo-acetyl]amino]-2-methoxy-pyridine-3-carboxamide (0.0428 g, 106.34 μmol) was chirally separated (IC column (250*20, 5 mkm), $CO_2$-MeOH, 50-50, 2.0 mL/min and AS-H, $CO_2$-MeOH, 80-20, 3.0 mL/min) to obtain Compound 369—5-[[2-[(2R,5S)-2-cyclohexyl-5-methyl-1-piperidyl]-2-oxo-acetyl]amino]-2-methoxy-pyridine-3-carboxamide (0.01316 g, 32.70 μmol, 30.75% yield), Compound 370—5-[[2-[(2S,5R)-2-cyclohexyl-5-methyl-1-piperidyl]-2-oxo-acetyl]amino]-2-methoxy-pyridine-3-carboxamide (0.00924 g, 22.96 μmol, 21.59% yield), Compound 371—5-[[2-[(2S,5S)-2-cyclohexyl-5-methyl-1-piperidyl]-2-oxo-acetyl]amino]-2-methoxy-pyridine-3-carboxamide (0.00277 g, 6.88 μmol, 6.47% yield) and Compound 389—5-[[2-[(2R,5R)-2-cyclohexyl-5-methyl-1-piperidyl]-2-oxo-acetyl]amino]-2-methoxy-pyridine-3-carboxamide (0.009 g, 22.36 μmol, 21.03% yield).

Compound 369:

$^1$H NMR (600 MHz, DMSO-$d_6$) δ 0.67-0.87 (m, 2H), 0.91-0.96 (m, 3H), 1.04-1.28 (m, 4H), 1.52-1.63 (m, 4H), 1.65-1.71 (m, 2H), 1.74-1.79 (m, 1H), 1.80-1.98 (m, 3H), 2.82-3.25 (m, 1H), 3.32-3.48 (m, 1H), 3.93-3.95 (m, 3H), 3.98-4.13 (m, 1H), 7.68-7.76 (m, 2H), 8.40-8.48 (m, 1H), 8.50-8.56 (m, 1H), 10.78-10.88 (m, 1H).

LCMS(ESI): [M+2H]$^+$ m/z: calcd 402.2; found 404.2; Rt=5.763 min.

RT (IC, $CO_2$-MeOH, 50-50, 2.0 mL/min)=6.246 min.

Compound 370:

¹H NMR (600 MHz, DMSO-d₆) δ 0.68-0.90 (m, 2H), 0.91-0.98 (m, 3H), 1.04-1.28 (m, 4H), 1.53-1.65 (m, 4H), 1.65-1.72 (m, 2H), 1.73-1.78 (m, 1H), 1.80-1.99 (m, 3H), 2.51-2.88 (m, 1H), 3.32-3.48 (m, 1H), 3.92-3.96 (m, 3H), 3.97-4.15 (m, 1H), 7.67-7.78 (m, 2H), 8.39-8.47 (m, 1H), 8.50-8.56 (m, 1H), 10.76-10.89 (m, 1H).

LCMS(ESI): [M+2H]⁺ m/z: calcd 402.2; found 404.2; Rt=5.759 min.

RT (IC, CO₂-MeOH, 50-50, 2.0 mL/min)=5.387 min.

Compound 371:

LCMS(ESI): [M+2H]⁺ m/z: calcd 402.2; found 404.2; Rt=5.811 min.

RT (AS-H, CO₂-MeOH, 80-20, 3.0 mL/min)=3.657 and 5.686 min.

Compound 389:

¹H NMR (600 MHz, DMSO-d₆) δ 0.66-1.03 (m, 6H), 1.05-1.22 (m, 3H), 1.26-1.45 (m, 1H), 1.52-1.60 (m, 3H), 1.61-1.72 (m, 3H), 1.73-1.90 (m, 3H), 2.25—2.31 (m, 0.4H), 2.63-2.88 (m, 0.6H), 3.33-3.52 (m, 1H), 3.91-3.95 (m, 3H), 3.98-4.17 (m, 1H), 7.66-7.78 (m, 2H), 8.39-8.46 (m, 1H), 8.48-8.55 (m, 1H), 10.77-10.87 (m, 1H).

LCMS(ESI): [M+H]⁺ m/z: calcd 402.2; found 404.2; Rt=5.802 min.

RT (AS-H, CO₂-MeOH, 80-20, 3.0 mL/min)=3.295 and 3.932 min.

Example 54. The Synthesis of Compound 130, Compound 127, Compound 121 and Compound 117

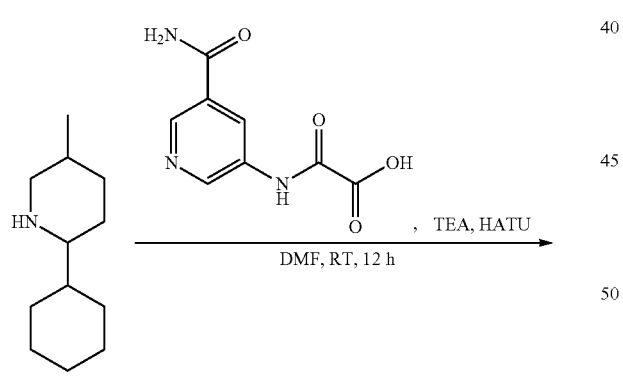

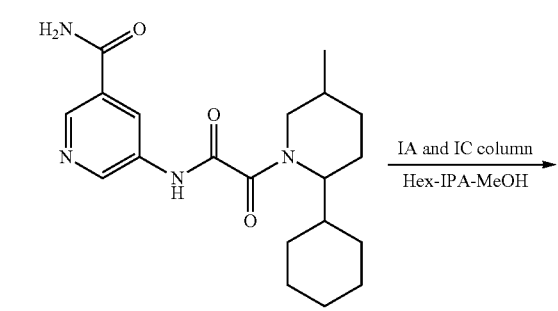

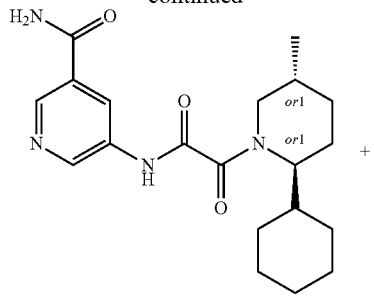

Compound 121

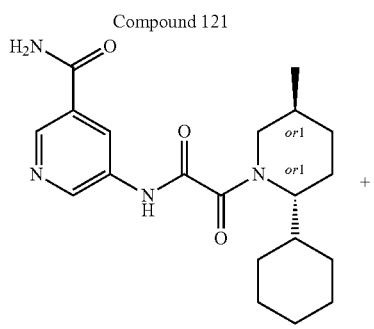

Compound 127

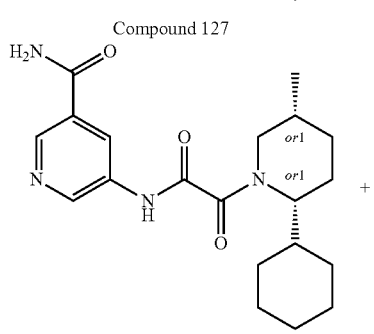

Compound 117

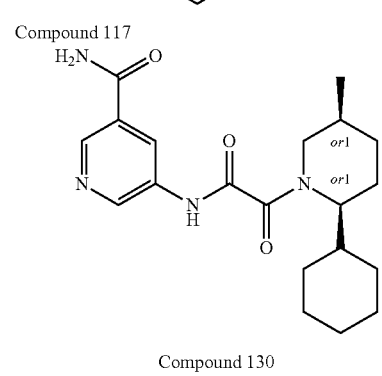

Compound 130

Step 1: The Synthesis of 5-[[2-(2-cyclohexyl-5-methyl-1-piperidyl)-2-oxo-acetyl]amino]pyridine-3-carboxamide 2-[(5-carbamoyl-3-pyridyl)amino]-2-oxo-acetic acid (402.37 mg, 1.10 mmol, C₆H₁₅N) and 2-cyclohexyl-5-methyl-piperidine (300 mg, 1.10 mmol, HCl) were mixed in DMF (10 mL). The reaction suspension was cooled to 0° C. and HATU (419.03 mg, 1.10 mmol) followed by TEA (557.58 mg, 5.51 mmol, 768.01 μL) were added. The clear solution was stirred at ambient temperature for 12 h. Then, volatiles were evaporated under reduced pressure and residue (1 g) was subjected to RP-HPLC (column: YMC Triart C18 100*20 mm, 5 um; 50-50-85% 0-1-5 min 0.1% NH₃- methanol as mobile phase) to give 5-[[2-(2-cyclohexyl-5-methyl-1-piperidyl]-2-oxo-acetyl]amino]pyridine-3-carboxamide (202 mg, 542.34 μmol, 49.21% yield) as three fractions 20, 141 and 41 mg of diastereomeric mixtures.
 $^1$H NMR (500 MHz, DMSO-d$_6$+CCl$_4$) δ 0.83 (m, 2H), 0.98 (m, 3H), 1.24 (m, 4H), 1.67 (m, 6H), 1.88 (m, 4H), 2.81 (m, 1H), 3.49 (m, 1H), 4.08 (m, 1H), 7.62 (m, 1H), 8.17 (m, 1H), 8.48 (m, 1H), 8.78 (m, 1H), 8.90 (m, 1H), 11.05 (m, 1H).
LCMS(ESI): [M+H]$^+$ m/z: calcd 372.4; found 373.2; Rt=3.461 min.

Step 2: The Synthesis of 5-[[2-[(2S,5S)-2-cyclohexyl-5-methyl-1-piperidyl]-2-oxo-acetyl]amino]pyridine-3-carboxamide (Compound 121), 5-[[2-[(2R,5R)-2-cyclohexyl-5-methyl-1-piperidyl]-2-oxoacetyl]amino]pyridine-3-carboxamide (Compound 127), 5-[[2-[(2R,5S)-2-cyclohexyl-5-methyl-1-piperidyl]-2-oxo-acetyl]amino]pyridine-3-carboxamide (Compound 117) and 5-[[2-[(2S,5R)-2-cyclohexyl-5-methyl-1-piperidyl]-2-oxo-acetyl]amino]pyridine-3-carboxamide (Compound 130

The enantiomers were separated by chiral HPLC (column: IA (250*20, 5 mkm), Hexane-IPA-MeOH, 80-10-10, 14 mL/min as mobile phase, then another column for first two: IC (250*20, 5 mkm), Hexane-IPA-MeOH, 60-20-20, 12 mL/min as mobile phase) to give the two individual cis-enantiomers Compound 121 5-[[2-[(2S,5S)-2-cyclohexyl-5-methyl-1-piperidyl]-2-oxo-acetyl]amino]pyridine-3-carboxamide (15 mg, 40.27 μmol, 42.55% yield) and Compound 127 5-[[2-[(2R,5R)-2-cyclohexyl-5-methyl-1-piperidyl]-2-oxo-acetyl]amino]pyridine-3-carboxamide (15 mg, 40.27 μmol, 42.55% yield), and the two individual trans-enantiomers Compound 117 5-[[2-[(2R,5S)-2-cyclohexyl-5-methyl-1-piperidyl]-2-oxo-acetyl]amino]pyridine-3-carboxamide (30 mg, 80.55 μmol, 85.11% yield) and Compound 130 5-[[2-[(2S,5R)-2-cyclohexyl-5-methyl-1-piperidyl]-2-oxo-acetyl]amino]pyridine-3-carboxamide (28 mg, 75.18 μmol, 79.43% yield).

Compound 121:
 $^1$H NMR (500 MHz, DMSO-d$_6$+CCl$_4$) δ0.83 (m, 2H), 0.98 (m, 3H), 1.24 (m, 4H), 1.67 (m, 6H), 1.88 (m, 4H), 2.81 (m, 1H), 3.49 (m, 1H), 4.08 (m, 1H), 7.62 (m, 1H), 8.17 (m, 1H), 8.48 (m, 1H), 8.78 (m, 1H), 8.90 (m, 1H), 11.05 (m, 1H).
LCMS(ESI): [M+2H]$^+$ m/z: calcd 372.2; found 374.2; Rt=5.022 min.
RT (IC, Hex-IPA-MeOH, 60-20-20, 0.6 mL/min)=15.851 min.

Compound 127:
 $^1$H NMR (500 MHz, DMSO-d$_6$+CCl$_4$) δ0.83 (m, 2H), 0.98 (m, 3H), 1.19 (m, 4H), 1.67 (m, 6H), 1.83 (m, 4H), 2.58 (m, 1H), 3.40 (m, 1H), 4.08 (m, 1H), 7.62 (m, 1H), 8.17 (m, 1H), 8.49 (m, 1H), 8.78 (m, 1H), 8.90 (m, 1H), 11.05 (m, 1H).
LCMS(ESI): [M+2H]$^+$ m/z: calcd 372.2; found 374.2; Rt=5.019 min.
RT (IC, Hex-IPA-MeOH, 60-20-20, 0.6 mL/min)=28.529 min.

Compound 117:
 $^1$H NMR (400 MHz, CDCl$_3$) δ 0.93 (m, 5H), 1.18 (m, 8H), 1.57 (m, 4H), 1.94 (m, 1H), 2.66 (m, 1H), 3.65 (m, 1H), 4.32 (m, 1H), 4.58 (m, 1H), 6.24 (m, 2H), 8.62 (s, 1H), 8.81 (s, 1H), 8.96 (s, 1H), 9.70 (m, 1H).
LCMS(ESI): [M+2H]$^+$ m/z: calcd 372.2; found 374.2; Rt=4.930 min.
RT (IC, Hex-IPA-MeOH, 60-20-20, 0.6 mL/min)=19.507 min.

Compound 130:
 $^1$H NMR (400 MHz, CDCl$_3$) δ 0.93 (m, 5H), 1.21 (m, 8H), 1.64 (m, 4H), 1.94 (m, 1H), 2.55 (m, 1H), 4.00 (m, 1H), 4.33 (m, 1H), 4.57 (m, 1H), 6.44 (m, 2H), 8.61 (s, 1H), 8.81 (s, 1H), 8.96 (s, 1H), 9.76 (m, 1H).
LCMS(ESI): [M+2H]$^+$ m/z: calcd 372.2; found 374.2; Rt=4.929 min.
RT (IC, Hex-IPA-MeOH, 60-20-20, 0.6 mL/min)=24.368 min.

Example 55. The Synthesis of 5-(2-(2-(1H-Indol-5-yl)-5-methylpiperidin-1-yl)-2-oxoacetamido)Nicotinamide (Compound 372, Compound 481

-continued

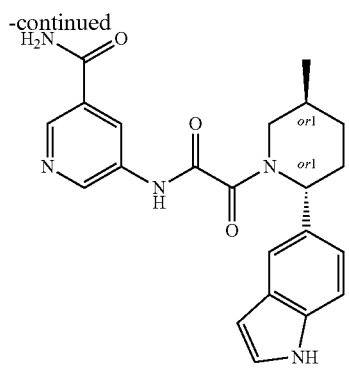

Compound 481

Step 1: Synthesis of 5-(2-(2-(1H-indol-5-yl)-5-methylpiperidin-1-yl)-2-oxoacetamido)nicotinamide HATU (603.24 mg, 1.59 mmol) was added portionwise at rt to a suspension of 2-[(5-carbamoyl-3-pyridyl)amino]-2-oxo-acetic acid (389.68 mg, 1.59 mmol, HCl), 5-(5-methyl-2-piperidyl)-1H-indole (400 mg, 1.59 mmol) and TEA (963.24 mg, 9.52 mmol, 1.33 mL) in DMF (5 mL). The clear solution was stirred at 30° C. for 32 hr and the solvents were evaporated in vacuo to give 1 g of crude material. It was subjected to RP-HPLC (column: SunFire C18 100×19 mm 5 um; 20-20-45% 0-1-6 min 0.2% FA-MeCN as mobile phase) to give 5-[[2-[2-(1H-indol-5-yl)-5-methyl-1-piperidyl]-2-oxo-acetyl]amino]pyridine-3-carboxamide (84 mg, 207.18 μmol, 13.06% yield).

$^1$H NMR (400 MHz, DMSO-d$_6$) δ (ppm)
LCMS(ESI): [M]$^+$ m/z: calcd 405.2; found 406.2; Rt=1.141 min.

Step 2: Chiral Separation (Compound 372 and Compound 481

The enantiomers were separated by chiral HPLC (column: IA-I (250*20, 5 mkm), Hexane-IPA-MeOH, 50-25-25, 12 ml/min as mobile phase) to give the two individual enantiomers Compound 372 5-[[2-[(2S,5R)-2-(1H-indol-5-yl)-5-methyl-1-piperidyl]-2-oxo-acetyl]amino]pyridine-3-carboxamide (21 mg, 51.79 μmol, 50.00% yield) RetTime=23.35 min and Compound 481 (35 mg) RetTime=45.08 min which was additionally purified in the following conditions—Column: Chiralpak IB (250*20 mm, 5 m); Mobile phase: Hexane-IPA-MeOH, 50-25-25 Flow Rate: 10 mL/min; Column Temperature: 24° C.; Wavelength: 205 nm, 225 nm, 260 nm), RetTime (isomer A)=10.33 min) to give (18 mg, 44.40 μmol, 42.86% yield) of Compound 481 5-[[2-[(2R,5S)-2-(1H-indol-5-yl)-5-methyl-1-piperidyl]-2-oxo-acetyl]amino]pyridine-3-carboxamide (18 mg, 44.40 μmol, 42.86% yield). Ret time for Compound 372 in analytical conditions (column: IA, Hexane-IPA-MeOH, 50-25-25, 0.6 ml/min as mobile phase) 17.31 min and for Compound 481 38.68 min.

Compound 372: Retention time: 17.31 min
$^1$H NMR (600 MHz, DMSO-d$_6$) δ (ppm) 0.99-1.08 (m, 3H), 1.29-1.42 (m, 1H), 1.74-1.93 (m, 2H), 2.04-2.21 (m, 1H), 2.25-2.34 (m, 1H), 2.78-3.25 (m, 1H), 3.42-4.07 (m, 1H), 5.20-5.73 (m, 1H), 6.36-6.43 (m, 1H), 7.00-7.13 (m, 1H), 7.28-7.34 (m, 1H), 7.34-7.42 (m, 1H), 7.45-7.54 (m, 1H), 7.54-7.66 (m, 1H), 8.04-8.22 (m, 1H), 8.41-8.54 (m, 1H), 8.70-8.80 (m, 1H), 8.80-8.94 (m, 1H), 10.97-11.15 (m, 1H), 11.15-11.39 (m, 1H).

LCMS(ESI): [M]$^+$ m/z: calcd 405.2; found 406.2; Rt=2.865 min.

Compound 481: Retention time: 38.68 min
$^1$H NMR (500 MHz, DMSO-d$_6$) δ (ppm) 1.00-1.14 (m, 3H), 1.32-1.47 (m, 1H), 1.69-2.07 (m, 2H), 2.07-2.30 (m, 1H), 2.30-2.38 (m, 1H), 2.82-3.25 (m, 1H), 3.43-4.07 (m, 1H), 5.21-5.80 (m, 1H), 6.36-6.47 (m, 1H), 7.01-7.16 (m, 1H), 7.26-7.46 (m, 2H), 7.47-7.68 (m, 2H), 8.08-8.27 (m, 1H), 8.43-8.60 (m, 1H), 8.70-8.84 (m, 1H), 8.84-9.02 (m, 1H), 10.99-11.16 (m, 1H), 11.16-11.34 (m, 1H).

LCMS(ESI): [M]$^+$ m/z: calcd 405.2; found 406.2; Rt=2.811 min.

Example 56. The Synthesis of 5-(2-(2-(1H-benzo[d]imidazol-5-yl)-5-methylpiperidin-1-yl)-2-oxoacetamido)nicotinamide (Compound 344, Compound 362

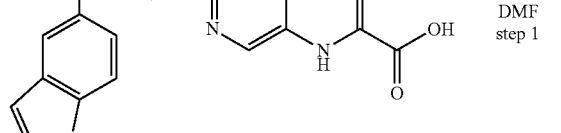

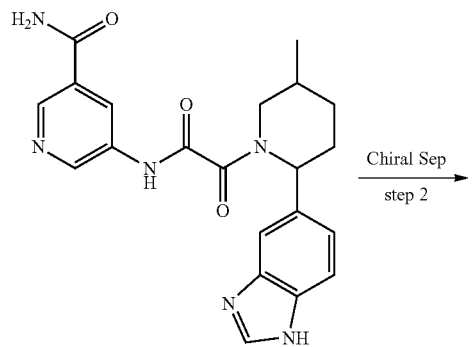

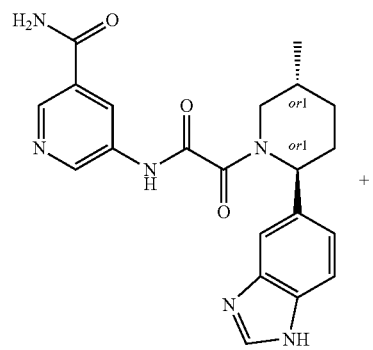

Compound 344

-continued

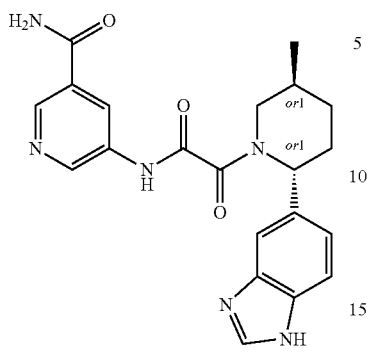

Compound 462

Step 1: Synthesis of 5-(2-(2-(1H-benzo[d]imidazol-5-yl)-5-methylpiperidin-1-yl)-2-oxoacetamido)Nicotinamide 2-[(5-carbamoyl-3-pyridyl)amino]-2-oxo-acetic acid (342.26 mg, 1.39 mmol, HCl) and 5-(5-methyl-2-piperidyl)-1H-benzimidazole (400.00 mg, 1.39 mmol) were mixed in DMF (5 mL). The reaction suspension was cooled to 0° C. and HATU (529.83 mg, 1.39 mmol) followed by TEA (846.02 mg, 8.36 mmol, 1.17 mL) were added. The clear solution was stirred at 30° C. for 72 hr then volatiles were evaporated under reduced pressure and residue (1 g) was subjected to RP-HPLC (column: XBridge C18 100×19 mm, 5 um; 20-20-70% 0-1-6 min 0.1% NH$_3$-MeOH as mobile phase) to give 5-[[2-[2-(1H-benzimidazol-5-yl)-5-methyl-1-piperidyl]-2-oxo-acetyl]amino]pyridine-3-carboxamide (55 mg, 135.32 μmol, 9.71% yield) and 250 mg of reactant impurity 5-(5-methyl-2-piperidyl)-1H-benzimidazole.

$^1$H NMR (400 MHz, DMSO-d$_6$) δ (ppm)
LCMS(ESI): [M]$^+$ m/z: calcd 406.2; found 407.2; Rt=1.877 min.

Step 2: Chiral Separation (Compound 344 and Compound 362

The enantiomers were separated by chiral HPLC (column: Chiralcel OJ-H (250*20, 5 mkm), Hexane-IPA-MeOH, 70-15-15, 12 ml/min as mobile phase) to give the two individual enantiomers Compound 344 5-[[2-[(2S,5R)-2-(1H-benzimidazol-5-yl)-5-methyl-1-piperidyl]-2-oxo-acetyl]amino]pyridine-3-carboxamide (22 mg, 54.13 μmol, 80.00% yield) RetTime=16.21 min and Compound 362 5-[[2-[(2R,5S)-2-(1H-benzimidazol-5-yl)-5-methyl-1-piperidyl]-2-oxo-acetyl]amino]pyridine-3-carboxamide (18.5 mg, 45.52 μmol, 67.27% yield) RetTime=43.90 min. The last one was repurified by HPLC (column: C18, H$_2$O-ACN, 15-40% ACN, 30 ml/min as mobile phase).

Compound 344: Retention time: 16.21 min
$^1$H NMR (600 MHz, DMSO-d$_6$) δ (ppm) 1.04 (m, 3H), 1.36 (m, 1H), 1.74 (m, 1H), 1.87 (m, 1H), 2.13 (m, 1H), 2.29 (m, 1H), 2.94 (m, 1H), 3.75 (m, 1H), 5.49 (m, 1H), 7.17 (m, 1H), 7.49 (m, 1H), 7.63 (m, 2H), 8.19 (m, 2H), 8.47 (m, 1H), 8.75 (m, 1H), 8.87 (m, 1H), 11.26 (m, 1H), 12.38 (m, 1H).
LCMS(ESI): [M]$^+$ m/z: calcd 406.2; found 407.2; Rt=1.688 min.

Compound 362: Retention time: 43.90 min
$^1$H NMR (600 MHz, DMSO-d$_6$) δ (ppm) 1.01-1.08 (m, 3H), 1.30-1.42 (m, 1H), 1.71-1.81 (m, 1H), 1.83-1.94 (m, 1H), 2.03-2.22 (m, 1H), 2.25-2.35 (m, 1H), 2.79-3.24 (m, 1H), 3.43-4.07 (m, 1H), 5.23-5.78 (m, 1H), 7.11-7.26 (m, 1H), 7.41-7.54 (m, 1H), 7.54-7.69 (m, 2H), 8.07-8.22 (m, 2H), 8.40-8.53 (m, 1H), 8.68-8.79 (m, 1H), 8.81-8.95 (m, 1H), 11.11-11.39 (m, 1H), 12.26-12.49 (m, 1H).
LCMS(ESI): [M]$^+$ m/z: calcd 406.2; found 407.2; Rt=1.947 min.

Example 57. The Synthesis of 2-(2-(JH-benzo[d]imidazol-5-yl)-5-methylpiperidin-1-yl)-N-(6-amino-5-ethylpyridin-3-yl)-2-oxoacetamide (Compound 771, Compound 748

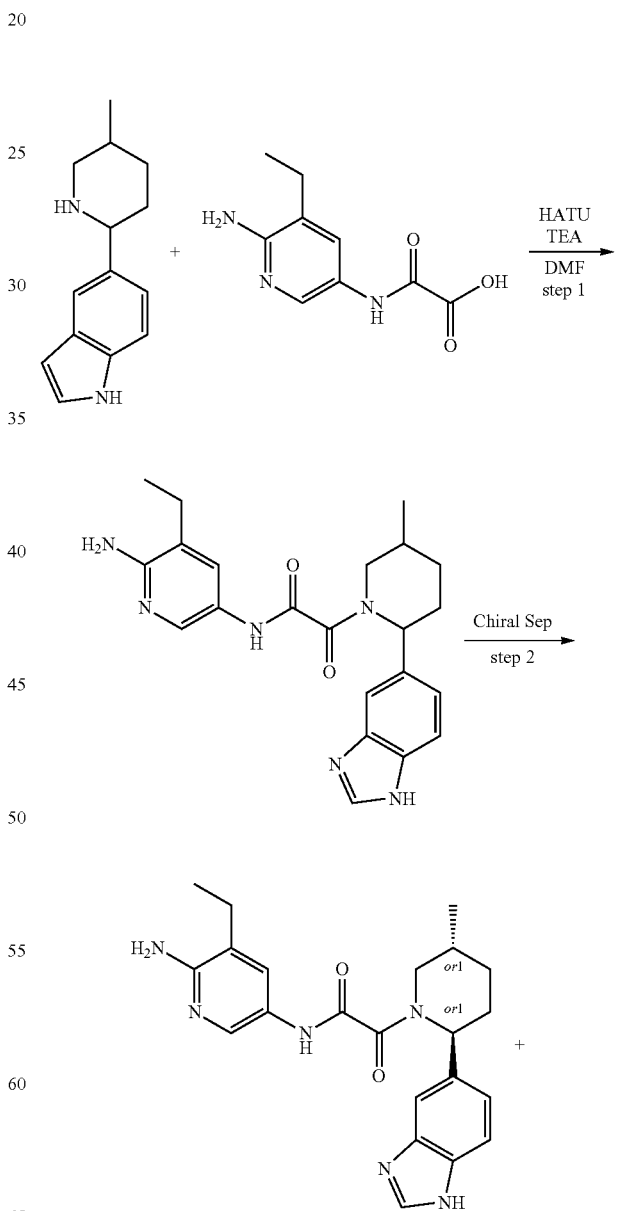

Compound 771

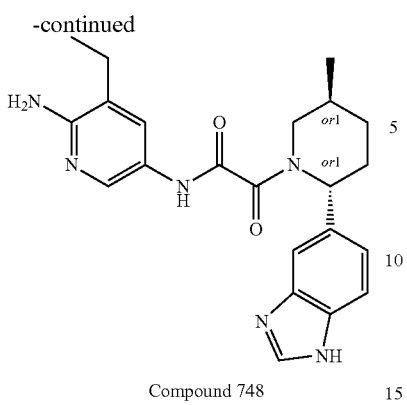

Compound 748

Step 1: Synthesis of 2-(2-(1H-benzo[d]imidazol-5-yl)-5-methylpiperidin-1-yl)-N-(6-amino-5-ethylpyridin-3-yl)-2-oxoacetamide HATU (353.22 mg, 928.96 μmol) was added portionwise at rt to a suspension of 2-[(6-amino-5-ethyl-3-pyridyl)amino]-2-oxo-acetic acid (194.34 mg, 928.96 μmol), 5-(5-methyl-2-piperidyl)-1H-benzimidazole (200.00 mg, 928.96 μmol) and TEA (564.01 mg, 5.57 mmol, 776.88 μL) in DMF (13 mL). The clear solution was stirred at ambient temperature for 32 hr and the solvents were evaporated in vacuo to give 1 g of crude material. It was subjected to RP-HPLC (column: YMC-Actus Triart C18 100×20 mm, 5 um; 15-70% 0-5 min water-MeOH (0.1% NH$_3$) as mobile phase) to give N-(6-amino-5-ethyl-3-pyridyl)-2-[2-(1H-benzimidazol-5-yl)-5-methyl-1-piperidyl]-2-oxo-acetamide (69 mg, 169.75 μmol, 18.27% yield).

$^1$H NMR (400 MHz, DMSO-d$_6$) δ (ppm)

LCMS(ESI): [M]$^+$ m/z: calcd 406.2; found 407.2; Rt=0.952 min.

Step 2: Chiral Separation (Compound 771 and Compound 748

The enantiomers were separated by chiral HPLC (column: IA-II, (250*20, 5 mkm), Hexane-IPA-MeOH, 60-20-20, 12 ml/min as mobile phase) to give the two individual enantiomers Compound 771 N-(6-amino-5-ethyl-3-pyridyl)-2-[(2S,5R)-2-(1H-benzimidazol-5-yl)-5-methyl-1-piperidyl]-2-oxo-acetamide (23.8 mg, 58.55 μmol, 68.99% yield) RetTime=27.2 min and Compound 748 N-(6-amino-5-ethyl-3-pyridyl)-2-[(2R,5S)-2-(1H-benzimidazol-5-yl)-5-methyl-1-piperidyl]-2-oxo-acetamide (26.2 mg, 64.46 μmol, 75.94% yield) RetTime=38.7 min.

Compound 771: Retention time: 27.20 min $^1$H NMR (600 MHz, DMSO-d$_6$) δ (ppm) 1.00-1.04 (m, 3H), 1.05-1.16 (m, 3H), 1.28-1.41 (m, 1H), 1.68-1.80 (m, 1H), 1.81-1.92 (m, 1H), 2.01-2.18 (m, 1H), 2.21-2.30 (m, 1H), 2.36-2.43 (m, 2H), 2.74-3.27 (m, 1H), 3.44-4.05 (m, 1H), 5.22-5.60 (m, 1H), 5.61-5.74 (m, 2H), 7.10-7.26 (m, 1H), 7.35-7.54 (m, 2H), 7.54-7.68 (m, 1H), 7.96-8.09 (m, 1H), 8.18 (s, 1H), 10.44-10.60 (m, 1H), 12.27-12.49 (m, 1H).

LCMS(ESI): [M]$^+$ m/z: calcd 406.2; found 407.2; Rt=1.400 min.

Compound 748: Retention time: 38.70 min $^1$H NMR (600 MHz, DMSO-d$_6$) δ (ppm) 0.99-1.04 (m, 3H), 1.05-1.15 (m, 3H), 1.29-1.41 (m, 1H), 1.70-1.80 (m, 1H), 1.81-1.92 (m, 1H), 2.01-2.19 (m, 1H), 2.19-2.31 (m, 1H), 2.36-2.43 (m, 2H), 2.75-3.26 (m, 1H), 3.41-4.05 (m, 1H), 5.24-5.60 (m, 1H), 5.60-5.74 (m, 2H), 7.07-7.26 (m, 1H), 7.37-7.55 (m, 2H), 7.55-7.67 (m, 1H), 7.96-8.23 (m, 2H), 10.43-10.60 (m, 1H), 12.30-12.47 (m, 1H).

LCMS(ESI): [M]$^+$ m/z: calcd 406.2; found 407.2; Rt=1.385 min.

Example 58. The Synthesis of 5-(2-(2-(JH-benzo[d]imidazol-5-yl)-5-methylpiperidin-1-yl)-2-oxoacetamido)-2-methoxynicotinamide (Compound 805, Compound 794

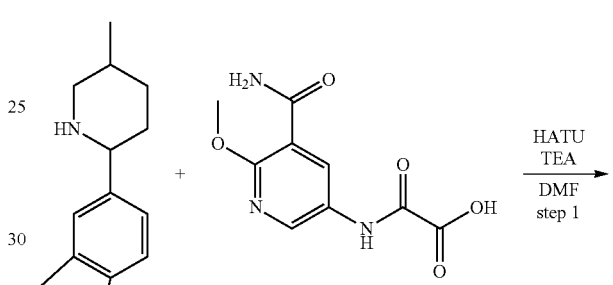

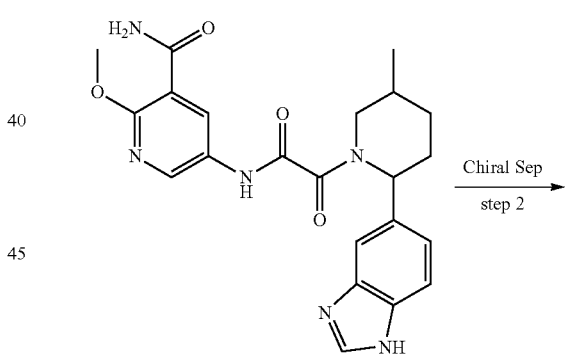

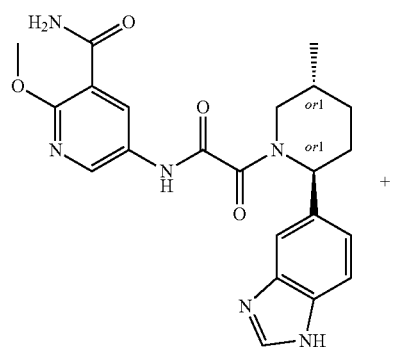

Compound 794

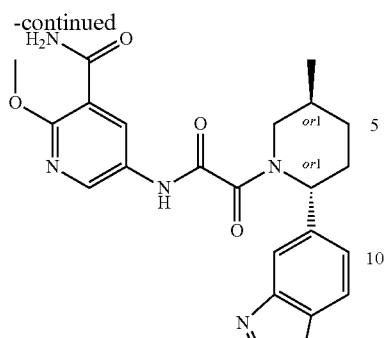

Compound 805

Step 1: Synthesis of 5-(2-(2-(1H-benzo[d]imidazol-5-yl)-5-methylpiperidin-1-yl)-2-oxoacetamido)-2-methoxynicotinamide HATU (392.76 mg, 1.03 mmol) was added portionwise at rt to a suspension of 2-[(5-carbamoyl-6-methoxy-3-pyridyl)amino]-2-oxo-acetic acid (351.59 mg, 1.03 mmol), 5-(5-methyl-2-piperidyl)-1H-benzimidazole (222.39 mg, 1.03 mmol) and TEA (627.15 mg, 6.20 mmol, 863.84 μL) in DMF (10 mL). The clear solution was stirred at 20° C. for 48 hr and the solvents were evaporated in vacuo to give 1 g of crude material. It was subjected to RP-HPLC (column: YMC-Actus Triart C18 100*20 mmI.D. S-5 um; 0-5 min 5-30% water-MeCN—NH$_4$OH, flow: 30 ml/min as mobile phase) to give 5-[[2-[2-(1H-benzimidazol-5-yl)-5-methyl-1-piperidyl]-2-oxo-acetyl]amino]-2-methoxy-pyridine-3-carboxamide (130 mg, 297.85 μmol, 28.83% yield).

$^1$H NMR (400 MHz, DMSO-d$_6$) δ (ppm)
LCMS(ESI): [M]$^+$ m/z: calcd 436.2; found 437.2; Rt=1.267 min.

Step 2: Chiral Separation (Compound 805 and Compound 794

The enantiomers were separated by chiral HPLC (column: IC-II (250*20, 5 mkm), Hexane-IPA-MeOH, 70-15-15, 12 ml/min as mobile phase) to give the two individual enantiomers Compound 794 5-[[2-[(2S,5R)-2-(1H-benzimidazol-5-yl)-5-methyl-1-piperidyl]-2-oxo-acetyl]amino]-2-methoxy-pyridine-3-carboxamide (56 mg, 128.30 μmol, 86.15% yield) RetTime=85.1 min and Compound 805 5-[[2-[(2R,5S)-2-(1H-benzimidazol-5-yl)-5-methyl-1-piperidyl]-2-oxo-acetyl]amino]-2-methoxy-pyridine-3-carboxamide (57 mg, 130.60 μmol, 87.69% yield) RetTime=115.5 min. Ret time for Compound 805 in analytical conditions (column: IC, Hexane-IPA-MeOH, 60-20-20, 0.6 ml/min as mobile phase) 45.22 min and for Compound 794 58.76 min.

Compound 805: Retention time: 45.22 min
$^1$H NMR (600 MHz, DMSO-d$_6$) δ (ppm) 1.05 (d, 3H), 1.38 (m, 1H), 1.96 (m, 2H), 2.25 (m, 2H), 3.48 (m, 1H), 3.56 (m, 1H), 3.96 (s, 3H), 5.52 (m, 1H), 7.56 (m, 5H), 8.46 (m, 3H), 11.05 (m, 1H), 12.41 (m, 1H).
LCMS(ESI): [M]$^+$ m/z: calcd 436.2; found 437.2; Rt=0.942 min.

Compound 794: Retention time: 58.76 min
$^1$H NMR (600 MHz, DMSO-d$_6$) δ (ppm) 1.05 (d, 3H), 1.38 (m, 1H), 1.94 (m, 2H), 2.18 (m, 2H), 3.48 (m, 1H), 3.56 (m, 1H), 3.96 (s, 3H), 5.52 (m, 1H), 7.56 (m, 5H), 8.09 (m, 1H), 8.26 (m, 2H), 11.05 (m, 1H), 12.41 (m, 1H).

LCMS(ESI): [M]$^+$ m/z: calcd 436.2; found 437.2; Rt=0.942 min.

Example 59. The Synthesis of 5-[[2-[(2R,5S)-2-(1H-indazol-5-yl)-5-methyl-1-piperidyl]-2-oxo-acetyl]amino]pyridine-3-carboxamide (Compound 360) and 5-[[2-[(2S,5R)-2-(1H-indazol-5-yl)-5-methyl-1-piperidyl]-2-oxo-acetyl]amino]pyridine-3-carboxamide (Compound 361

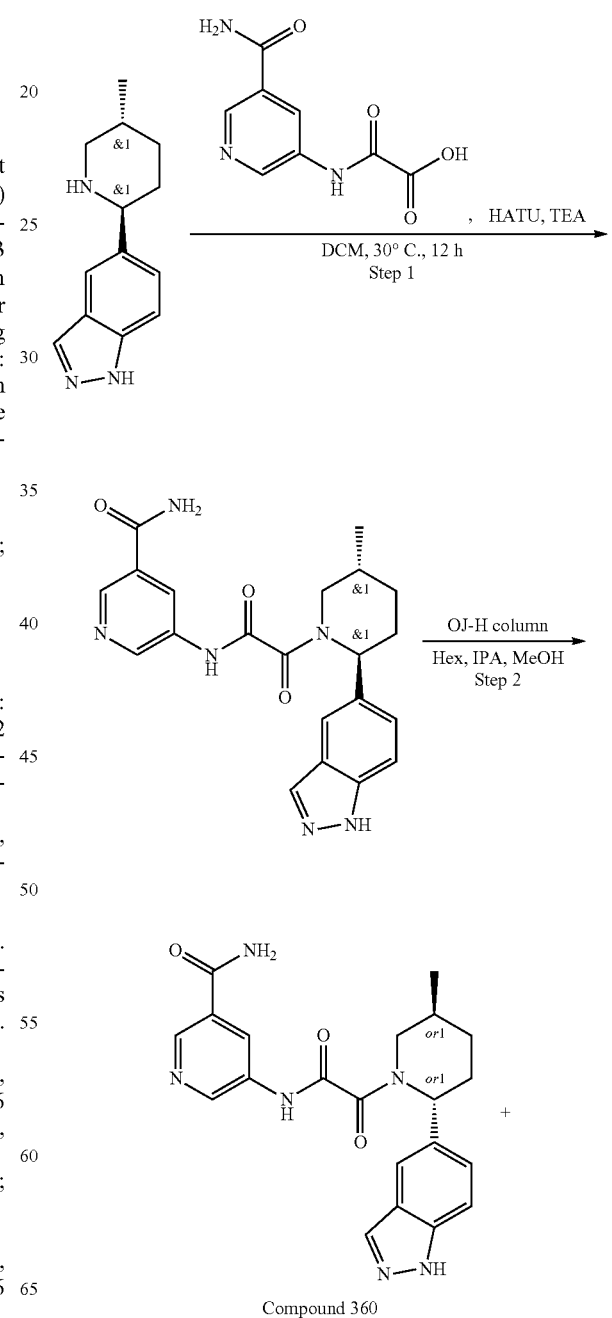

Compound 360

-continued

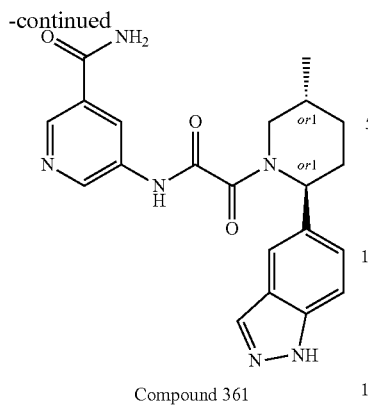

Compound 361

Step 1: The Synthesis of 5-[[2-[2-(H-indazol-5-yl)-5-methyl-1-piperidyl]-2-oxo-acetyl]amino]pyridine-3-carboxamide To a suspension of 5-(5-methyl-2-piperidyl)-1H-indazole (0.23 g, 1.07 mmol), 2-[(5-carbamoyl-3-pyridyl)amino]-2-oxo-acetic acid (262.40 mg, 1.07 mmol, HCl) and triethylamine (540.51 mg, 5.34 mmol, 744.51 µL) in DMF (5 mL), HATU (446.82 mg, 1.18 mmol) was added. The reaction mixture was stirred at 30° C. for 12 hr and subjected to HPLC (10-10-30% 0-1-6 min 0.2% TFA-acetonitrile, flow: 30 ml/min (loading pump 4 ml/min acetonitrile) target mass 406 column: SunFire C18 100*19 mm 5 um) to obtain 5-[[2-[2-(1H-indazol-5-yl)-5-methyl-1-piperidyl]-2-oxo-acetyl]amino]pyridine-3-carboxamide (110 mg, 270.64 µmol, 25.33% yield).

LCMS(ESI): [M+H]⁺ m/z: calcd 406.2; found 407.2; Rt=2.559 min.

Step 2: The Synthesis of 5-[[2-[(2R,5S)-2-(1H-indazol-5-yl)-5-methyl-1-piperidyl]-2-oxo-acetyl]amino]pyridine-3-carboxamide (Compound 360) and 5-[[2-[(2S,5R)-2-(JH-indazol-5-yl)-5-methyl-1-piperidyl]-2-oxo-acetyl]amino]pyridine-3-carboxamide (Compound 361

5-[[2-[2-(1H-indazol-5-yl)-5-methyl-1-piperidyl]-2-oxo-acetyl]amino]pyridine-3-carboxamide (110 mg, 270.64 µmol) was subjected to HPLC (OJ-H (250*20, 5 mkm) column; Hexane-IPA-MeOH, 60-20-20 as a mobile phase; Flow 15 ml/min) to afford Compound 360-5-[[2-[(2R,5S)-2-(1H-indazol-5-yl)-5-methyl-1-piperidyl]-2-oxo-acetyl]amino]pyridine-3-carboxamide (39.0 mg, 70.91% yield; RT=31.364 min) and Compound 361—5-[[2-[(2S,5R)-2-(1H-indazol-5-yl)-5-methyl-1-piperidyl]-2-oxo-acetyl]amino]pyridine-3-carboxamide (38.0 mg, 69.09% yield; RT=12.133 min).

Compound 360: RT (OJ-3, Hexane-IPA-MeOH, 50-25-25, 0.15 ml/min)=16.677 min.

¹H NMR (600 MHz, DMSO-d₆) δ 1.01-1.06 (m, 3H), 1.32-1.40 (m, 1H), 1.75-1.83 (m, 1H), 1.83-1.94 (m, 1H), 2.09-2.23 (m, 1H), 2.26-2.34 (m, 1H), 2.78-3.26 (m, 1H), 3.40-4.05 (m, 1H), 5.20-5.71 (m, 1H), 7.26-7.39 (m, 1H), 7.47-7.64 (m, 2H), 7.67-7.76 (m, 1H), 8.01-8.08 (m, 1H), 8.10-8.21 (m, 1H), 8.40-8.53 (m, 1H), 8.70-8.80 (m, 1H), 8.82-8.95 (m, 1H), 11.18-11.33 (m, 1H), 12.98-13.07 (m, 1H).

LCMS(ESI): [M+H]⁺ m/z: calcd 406.2; found 407.2; Rt=3.992 min.

Compound 361: RT (OJ-3, Hexane-IPA-MeOH, 50-25-25, 0.15 ml/min)=¹H NMR (600 MHz, DMSO-d₆) δ 1.00-1.06 (m, 3H), 1.30-1.43 (m, 1H), 1.73-1.83 (m, 1H), 1.83-1.93 (m, 1H), 2.07-2.23 (m, 1H), 2.25-2.35 (m, 1H), 2.78-3.26 (m, 1H), 3.44-4.06 (m, 1H), 5.20-5.74 (m, 1H), 7.27-7.39 (m, 1H), 7.49-7.64 (m, 2H), 7.69-7.75 (m, 1H), 8.00-8.07 (m, 1H), 8.08-8.21 (m, 1H), 8.42-8.55 (m, 1H), 8.71-8.80 (m, 1H), 8.80-8.96 (m, 1H), 11.16-11.33 (m, 1H), 12.96-13.07 (m, 1H).

LCMS(ESI): [M+H]⁺ m/z: calcd 406.2; found 407.2; Rt=4.010 min.

Example 60. The Synthesis of 5-[[2-[(2S,5R)-2-(1H-indazol-5-yl)-5-methyl-1-piperidyl]-2-oxo-acetyl]amino]-2-methoxy-pyridine-3-carboxamide (Compound 465) and 5-[[2-[(2R,5S)-2-(1H-indazol-5-yl)-5-methyl-1-piperidyl]-2-oxo-acetyl]amino]-2-methoxy-pyridine-3-carboxamide (Compound 464

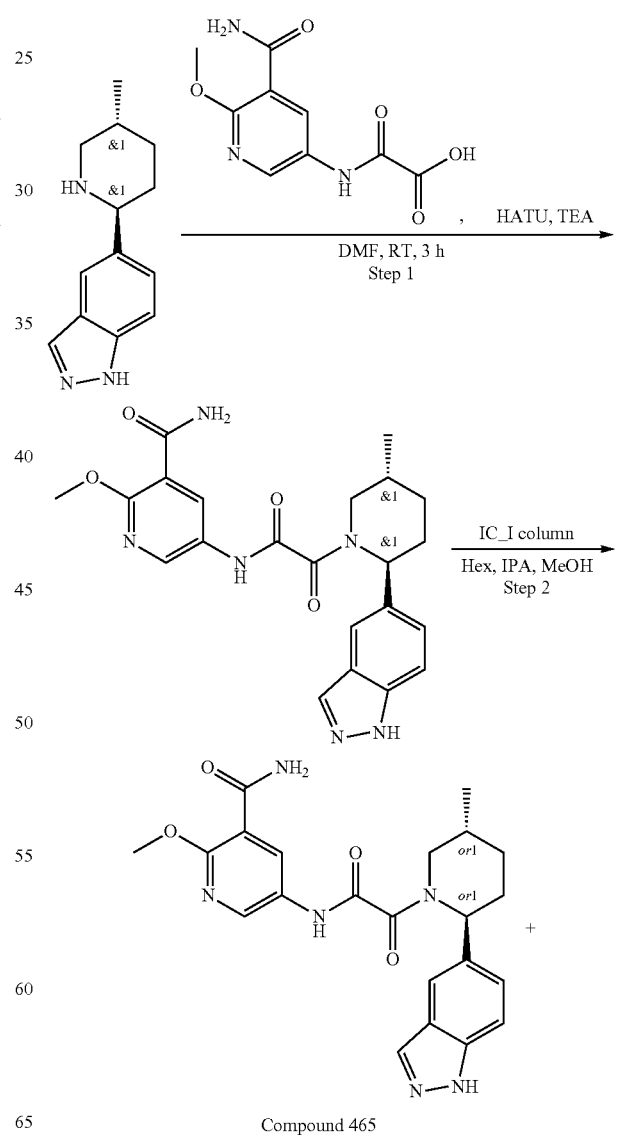

Compound 465

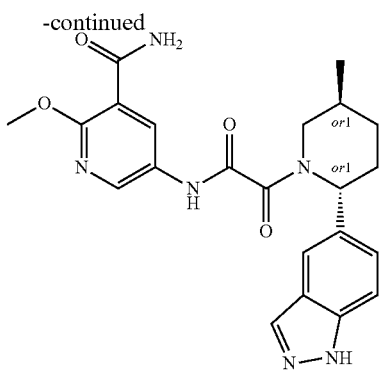

Compound 464

Step 1: The Synthesis of 5-[[2-[(2S,5R)-2-(1H-indazol-5-yl)-5-methyl-1-piperidyl]-2-oxo-acetyl]amino]-2-methoxy-pyridine-3-carboxamide To a solution of 5-[(2S,5R)-5-methyl-2-piperidyl]-1H-indazole (0.3 g, 975.41 μmol), 2-[(5-carbamoyl-6-methoxy-3-pyridyl)amino]-2-oxo-acetic acid (332.00 mg, 975.41 μmol, Et₃N) and triethylamine (493.51 mg, 4.88 mmol, 679.77 μL), HATU (407.97 mg, 1.07 mmol) was added portionwise. The resulting mixture was stirred at 25° C. for 3 hr and subjected to HPLC (0-5 min 20-70% water-methanol (NH₃ 0.1%), flow 30 ml/min (loading pump 4 ml/min methanol (NH₃ 0.1%)), column: YMC-Actus Triart C18 100*20 mmI.D. S-5 um) to give 5-[[2-[(2S,5R)-2-(1H-indazol-5-yl)-5-methyl-1-piperidyl]-2-oxo-acetyl]amino]-2-methoxy-pyridine-3-carboxamide (150 mg, 343.67 μmol, 35.23% yield). LCMS(ESI): [M+H]⁺ m/z: calcd 436.2; found 437.2; Rt=2.886 min.

Step 2: The Synthesis of 5-[[2-[(2S,5R)-2-(1H-indazol-5-yl)-5-methyl-1-piperidyl]-2-oxo-acetyl]amino]-2-methoxy-pyridine-3-carboxamide (Compound 465) and 5-[[2-[(2R,5S)-2-(1H-indazol-5-yl)-5-methyl-1-piperidyl]-2-oxo-acetyl]amino]-2-methoxy-pyridine-3-carboxamide (Compound 464

5-[[2-[(2S,5R)-2-(1H-indazol-5-yl)-5-methyl-1-piperidyl]-2-oxo-acetyl]amino]-2-methoxy-pyridine-3-carboxamide (150 mg, 343.67 μmol) was chirally separated (IC_I (250*20, 5 mkm), Hexane-IPA-MeOH, 40-30-30, 10 ml/min) to obtain Compound 465—5-[[2-[(2S,5R)-2-(1H-indazol-5-yl)-5-methyl-1-piperidyl]-2-oxo-acetyl]amino]-2-methoxy-pyridine-3-carboxamide (45 mg, 103.10 μmol, 60.00% yield; RT=30.290 min) and Compound 464—5-[[2-[(2R,5S)-2-(1H-indazol-5-yl)-5-methyl-1-piperidyl]-2-oxo-acetyl]amino]-2-methoxy-pyridine-3-carboxamide (44 mg, 100.81 μmol, 58.67% yield; RT=23.440 min).

Compound 465: RT (IA, Hexane-IPA-MeOH, 50-25-25, 0.6 ml/min)=49.555 min.

¹H NMR (600 MHz, DMSO-d₆) δ 1.01-1.06 (m, 3H), 1.30-1.42 (m, 1H), 1.66-1.81 (m, 1H), 1.81-1.96 (m, 1H), 2.02-2.23 (m, 1H), 2.24-2.35 (m, 1H), 2.74-3.28 (m, 1H), 3.48-4.04 (m, 4H), 5.24-5.73 (m, 1H), 7.26-7.39 (m, 1H), 7.49-7.55 (m, 1H), 7.67-7.75 (m, 3H), 8.01-8.06 (m, 1H), 8.42-8.61 (m, 2H), 10.98-11.11 (m, 1H), 13.00-13.04 (m, 1H).

LCMS(ESI): [M+H]⁺ m/z: calcd 436.2; found 437.2; Rt=2.909 min.

Compound 464: RT (IA, Hexane-IPA-MeOH, 50-25-25, 0.6 ml/min)=45.171 min.

¹H NMR (600 MHz, DMSO-d₆) δ 1.00-1.05 (m, 3H), 1.28-1.42 (m, 1H), 1.71-1.82 (m, 1H), 1.83-1.94 (m, 1H), 2.02-2.23 (m, 1H), 2.24-2.34 (m, 1H), 2.76-3.26 (m, 1H), 3.48-4.03 (m, 4H), 5.18-5.76 (m, 1H), 7.25-7.38 (m, 1H), 7.49-7.57 (m, 1H), 7.67-7.76 (m, 3H), 8.01-8.08 (m, 1H), 8.42-8.47 (m, 1H), 8.47-8.60 (m, 1H), 10.91-11.17 (m, 1H), 12.95-13.12 (m, 1H).

LCMS(ESI): [M+H]⁺ m/z: calcd 436.2; found 437.2; Rt=2.907 min.

Example 61. The Synthesis of N-(5,6-dimethyl-3-pyridyl)-2-[(2S,5R)-2-(1H-indazol-5-yl)-5-methyl-1-piperidyl]-2-oxo-acetamide (Compound 631) and N-(5,6-dimethyl-3-pyridyl)-2-[(2R,5S)-2-(1H-indazol-5-yl)-5-methyl-1-piperidyl]-2-oxo-acetamide

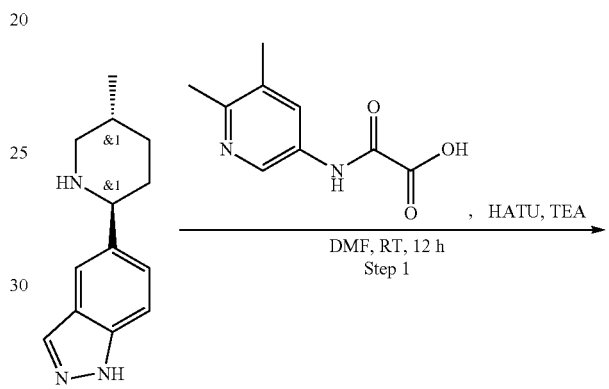

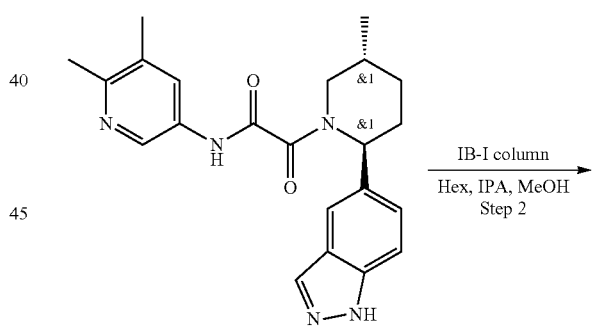

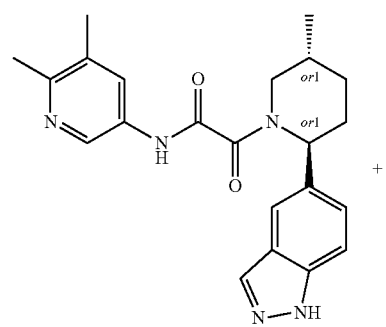

Compound 631

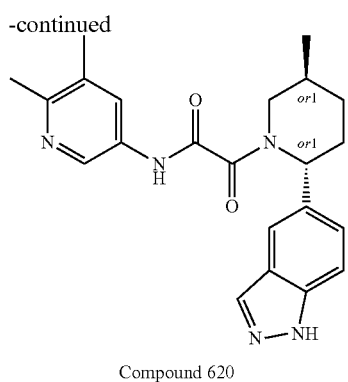

Compound 620

Step 1: The Synthesis of N-(5,6-dimethyl-3-pyridyl)-2-[(2S,5R)-2-(1H-indazol-5-yl)-5-methyl-1-piperidyl]-2-oxo-acetamide To a stirring solution of 5-[(2S,5R)-5-methyl-2-piperidyl]-1H-indazole (250 mg, 1.16 mmol), 2-[(5,6-dimethyl-3-pyridyl)amino]-2-oxo-acetic acid (342.99 mg, 1.16 mmol, N(C2H$_5$)$_3$) and triethyl amine (1.18 g, 11.61 mmol, 1.62 mL) in DMF (8 mL) was added HATU (485.68 mg, 1.28 mmol) at 25° C. in small portions over 0.5 hr. The resulting reaction mixture was stirred at 25° C. for 12 hr. The crude reaction mixture was purified by reverse phase HPLC (column: YMC Triart C18 100*20 mm, 5 um, Mobile Phase: 50-50-80% 0-1-5 min 0.1% NH$_3$-methanol, flow: 30 ml/min, loading pump 4 ml/min methanol) to afford N-(5,6-dimethyl-3-pyridyl)-2-[(2S,5R)-2-(1H-indazol-5-yl)-5-methyl-1-piperidyl]-2-oxo-acetamide (240 mg, 613.08 μmol, 52.80% yield) as a light-yellow solid.

$^1$H NMR (400 MHz, DMSO-d$_6$) δ 1.03 (d, 3H), 1.32 (m, 1H), 1.49 (s, 3H), 1.78 (m, 2H), 2.26 (s, 5H), 3.28 (s, 3H), 7.28 (d, 1H), 7.52 (d, 1H), 7.69 (s, 1H), 7.83 (s, 1H), 8.05 (s, 1H), 8.52 (s, 1H), 10.90 (m, 1H), 13.03 (m, 1H).

LCMS(ESI): [M+H]$^+$ m/z: calcd 391.2; found 392.2; Rt=1.468 min.

Step 2: The Synthesis of N-(5,6-dimethyl-3-pyridyl)-2-[(2S,5R)-2-(1H-indazol-5-yl)-5-methyl-1-piperidyl]-2-oxo-acetamide (Compound 631) and N-(5,6-dimethyl-3-pyridyl)-2-[(2R,5S)-2-(1H-indazol-5-yl)-5-methyl-1-piperidyl]-2-oxo-acetamide Racemic N-(5,6-dimethyl-3-pyridyl)-2-[(2S,5R)-2-(1H-indazol-5-yl)-5-methyl-1-piperidyl]-2-oxo-acetamide (240 mg, 613.08 μmol) was submitted to preparative chiral HPLC (Column: Chiralpak IB—I (250*20 mm, 5 mkm); Mobile phase: Hexane-IPA-MeOH, 50-25-25. Flow Rate: 10 mL/min; Column Temperature: 23° C.; Wavelength: 205 nm.) to afford Compound 631—N-(5,6-dimethyl-3-pyridyl)-2-[(2S,5R)-2-(1H-indazol-5-yl)-5-methyl-1-piperidyl]-2-oxo-acetamide (111 mg, 283.55 μmol, 46.25% yield) (RetTime=12.32 min); and Compound 620—N-(5,6-dimethyl-3-pyridyl)-2-[(2R,5S)-2-(1H-indazol-5-yl)-5-methyl-1-piperidyl]-2-oxo-acetamide (112 mg, 286.10 μmol, 46.67% yield) (RetTime=20.73 min) as white solids.

Compound 631: RT (IB, Hexane-IPA-MeOH, 50-25-25, 0.6 ml/min)=7.939 min.

$^1$H NMR (600 MHz, DMSO-d$_6$) δ 0.98-1.06 (m, 3H), 1.30-1.40 (m, 1H), 1.70-1.80 (m, 1H), 1.82-1.93 (m, 1H), 2.04-2.14 (m, 1H), 2.15-2.25 (m, 3H), 2.25-2.31 (m, 1H), 2.31-2.38 (m, 3H), 2.77-3.25 (m, 1H), 3.37-4.05 (m, 1H), 5.14-5.76 (m, 1H), 7.25-7.39 (m, 1H), 7.45-7.56 (m, 1H), 7.66-7.72 (m, 1H), 7.72-7.85 (m, 1H), 7.98-8.08 (m, 1H), 8.38-8.55 (m, 1H), 10.73-11.11 (m, 1H), 12.95-13.14 (m, 1H).

LCMS(ESI): [M+H]$^+$ m/z: calcd 391.2; found 392.2; Rt=1.918 min.

Compound 620: RT (IB, Hexane-IPA-MeOH, 50-25-25, 0.6 ml/min)=12.720 min.

$^1$H NMR (600 MHz, DMSO-d$_6$) δ 0.99-1.05 (m, 3H), 1.29-1.41 (m, 1H), 1.71-1.80 (m, 1H), 1.81-1.92 (m, 1H), 2.04-2.14 (m, 1H), 2.16-2.24 (m, 3H), 2.24-2.30 (m, 1H), 2.31-2.37 (m, 3H), 2.77-3.26 (m, 1H), 3.42-4.06 (m, 1H), 5.16-5.73 (m, 1H), 7.24-7.40 (m, 1H), 7.47-7.57 (m, 1H), 7.66-7.72 (m, 1H), 7.72-7.85 (m, 1H), 8.00-8.06 (m, 1H), 8.38-8.53 (m, 1H), 10.79-11.01 (m, 1H), 12.93-13.12 (m, 1H).

LCMS(ESI): [M+H]$^+$ m/z: calcd 391.2; found 392.2; Rt=1.946 min.

Example 62. The Synthesis of 5-[[2-[(2R,5S)-2-(3-chlorophenyl)-5-methyl-1-piperidyl]-2-oxo-acetyl]amino]pyridine-3-carboxamide (Compound 440) and 5-[[2-[(2S,5R)-2-(3-chlorophenyl)-5-methyl-1-piperidyl]-2-oxo-acetyl]amino]pyridine-3-carboxamide (Compound 441

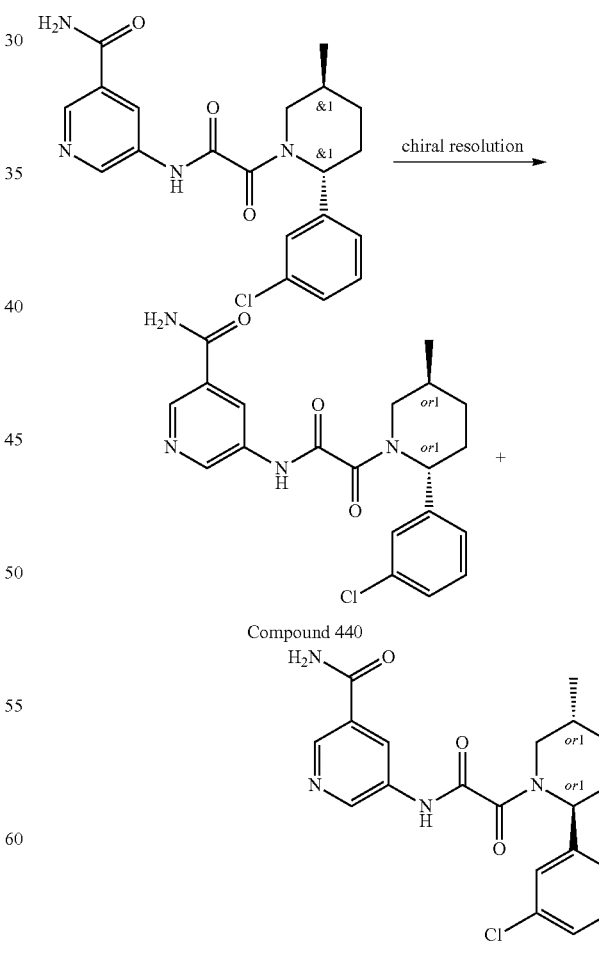

Compound 440

Compound 441

1357

Rel 5-[[2-[(2R,5S)-2-(3-chlorophenyl)-5-methyl-1-piperidyl]-2-oxo-acetyl]amino]pyridine-3-carboxamide was prepared in a manner similar to compounds described above.

Chiral separation was performed using Chiralpak IA-II (250*20 mm, 5 mkm) column, Hexane-IPA-MeOH as a mobile phase, 70-15-15 Flow Rate: 12 mL/min fording Compound 440—5-[[2-[(2R,5S)-2-(3-chlorophenyl)-5-methyl-1-piperidyl]-2-oxo-acetyl]amino]pyridine-3-carboxamide (46.05 mg, 114.88 µmol, 35.78% yield) as white solid and Compound 441—5-[[2-[(2S,5R)-2-(3-chlorophenyl)-5-methyl-1-piperidyl]-2-oxo-acetyl]amino]pyridine-3-carboxamide (48.11 mg, 120.02 µmol, 37.38% yield) as white solid.

Compound 440: $^1$H NMR (DMSO-$d_6$, 600 MHz): δ (ppm) 1.01 (m, 3H), 1.33 (m, 1H), 1.64 (m, 1H), 1.89 (m, 1H), 2.14 (m, 2H), 3.01 (m, 1H), 3.76 (m, 1H), 5.36 (m, 1H), 7.32 (m, 3H), 7.42 (m, 1H), 7.59 (m, 1H), 8.14 (m, 1H), 8.47 (m, 1H), 8.76 (m, 1H), 8.86 (m, 1H), 11.26 (m, 1H)

LCMS(ESI): [M+H]$^+$ m/z: calcd 400.1; found 401.1; Rt=3.179 min.

Compound 441: $^1$H NMR (DMSO-$d_6$, 600 MHz): δ (ppm) 1.01 (m, 3H), 1.34 (m, 1H), 1.63 (m, 1H), 1.89 (m, 1H), 2.14 (m, 2H), 2.96 (m, 1H), 3.66 (m, 1H), 5.37 (d, 1H), 7.32 (m, 3H), 7.43 (m, 1H), 7.59 (m, 1H), 8.14 (m, 1H), 8.47 (m, 1H), 8.76 (m, 1H), 8.86 (m, 1H), 11.26 (m, 1H)

LCMS(ESI): [M+H]$^+$ m/z: calcd 400.1; found 401.1; Rt=3.179 min.

Example 63. The Synthesis of 5-[[2-[(2R,5S)-2-(4-hydroxy-3-methyl-phenyl)-5-methyl-1-piperidyl]-2-oxo-acetyl]amino]pyridine-3-carboxamide and 5-[[2-[(2S,5R)-2-(4-hydroxy-3-methyl-phenyl)-5-methyl-1-piperidyl]-2-oxo-acetyl]amino]pyridine-3-carboxamide (Compound 330 and Compound 323

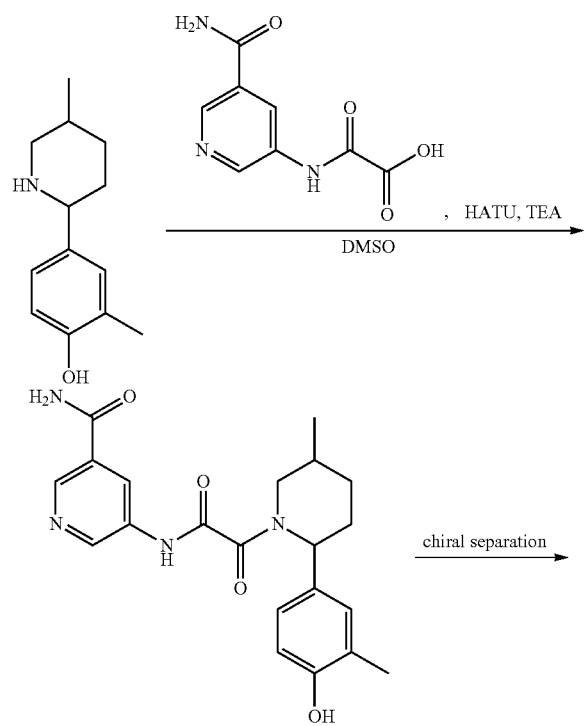

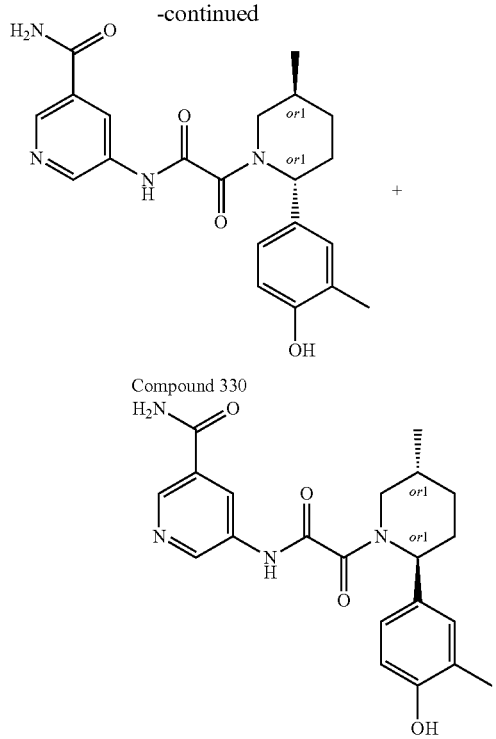

Compound 330

Compound 323

Step 1: Synthesis of 5-[[2-[2-(4-hydroxy-3-methyl-phenyl)-5-methyl-1-piperidyl]-2-oxo-acetyl]amino]pyridine-3-carboxamide To a stirred solution of 2-methyl-4-(5-methyl-2-piperidyl)phenol (0.21 g, 1.02 mmol), 2-[(5-carbamoyl-3-pyridyl)amino]-2-oxo-acetic acid (317.46 mg, 1.02 mmol, Et$_3$N salt) and HATU (427.84 mg, 1.13 mmol) in DMSO (4 mL) was added DIPEA (264.40 mg, 2.05 mmol, 356.34 µL). The reaction mixture was stirred at 25° C. for 16 hours. After 16 hours, the reaction mixture was purified by reverse phase HPLC (Eluent: 2-10 min, 35-100%, CH$_3$CN+Formic acid/H$_2$O; flow rate: 30 mL/min; loading pump: 4 mL, CH$_3$CN+ formic acid; column: SunFire C18 100×19 mm, 5 um) to obtain 5-[[2-[2-(4-hydroxy-3-methyl-phenyl)-5-methyl-1-piperidyl]-2-oxo-acetyl]amino]pyridine-3-carboxamide (100 mg, 252.25 µmol, 24.66% yield) as a white solid.

LCMS(ESI): [M+H]$^+$ m/z: calcd 396.2; found 397.0; Rt=1.165 min.

Step 2: Chiral Separation of 5-[[2-[(2R,5S)-2-(4-hydroxy-3-methyl-phenyl)-5-methyl-1-piperidyl]-2-oxo-acetyl]amino]pyridine-3-carboxamide and 5-[[2-[(2S,5R)-2-(4-hydroxy-3-methyl-phenyl)-5-methyl-1-piperidyl]-2-oxo-acetyl]amino]pyridine-3-carboxamide (Compound 330 and Compound 323

5-[[2-[2-(4-hydroxy-3-methyl-phenyl)-5-methyl-1-piperidyl]-2-oxo-acetyl]amino]pyridine-3-carboxamide (100 mg, 252.25 µmol) was subjected to chiral HPLC purification (Column: Chiralpak IC—I (250×20 mm, 5 um); Mobile phase: Hexane-IPA-MeOH, 60-20-20; Flow Rate: 12 mL/min) to get 5-[[2-[(2R,5S)-2-(4-hydroxy-3-methyl-phenyl)-5-methyl-1-piperidyl]-2-oxo-acetyl]amino]pyridine-3-carboxamide (Compound 330, 28.37 mg) and 5-[[2-[(2S, 5R)-2-(4-hydroxy-3-methyl-phenyl)-5-methyl-1-piperidyl]-2-oxo-acetyl]amino]pyridine-3-carboxamide (Compound 323, 28.46 mg) as light-yellow solids.

Compound 330: $^1$H NMR (DMSO-d$_6$, 500 MHz): δ (ppm) 0.95-1.10 (m, 3H), 1.27-1.38 (m, 1H), 1.66-1.79 (m, 1H), 1.81-1.94 (m, 1H), 1.95-2.21 (m, 5H), 2.77-3.21 (m, 1H), 3.45-4.01 (m, 1H), 4.99-5.57 (m, 1H), 6.69-6.83 (m, 1H), 6.90-6.99 (m, 1H), 6.99-7.08 (m, 1H), 7.54-7.67 (m, 1H), 8.10-8.24 (m, 1H), 8.41-8.55 (m, 1H), 8.71-8.82 (m, 1H), 8.82-8.94 (m, 1H), 9.20-9.29 (s, 1H), 11.12-11.29 (m, 1H).

LCMS(ESI): [M+H]$^+$ m/z: calcd 396.2; found 397.2; Rt=2.862 min.

Chiral HPLC: Rt=30.96 min (Column: IC; Mobile phase: Hexane-IPA-MeOH, 50-25-25; Flow Rate: 0.6 mL/min).

Compound 323: $^1$H NMR (DMSO-d$_6$, 500 MHz): δ (ppm) 0.94-1.10 (m, 3H), 1.26-1.40 (m, 1H), 1.66-1.79 (m, 1H), 1.80-1.94 (m, 1H), 1.93-2.23 (m, 5H), 2.78-3.22 (m, 1H), 3.44-4.01 (m, 1H), 4.98-5.57 (m, 1H), 6.68-6.82 (m, 1H), 6.86-6.98 (m, 1H), 6.98-7.07 (m, 1H), 7.51-7.72 (m, 1H), 8.06-8.28 (m, 1H), 8.37-8.61 (m, 1H), 8.69-8.82 (m, 1H), 8.82-8.97 (m, 1H), 9.16-9.32 (s, 1H), 11.09-11.32 (m, 1H).

LCMS(ESI): [M+H]$^+$ m/z: calcd 396.2; found 397.2; Rt=2.863 min.

Chiral HPLC: Rt=19.20 min (Column: IC; Mobile phase: Hexane-IPA-MeOH, 50-25-25; Flow Rate: 0.6 mL/min).

Example 64. The Synthesis of 5-[[2-[(2S,5R)-5-methyl-2-(2-oxoindolin-5-yl)-1-piperidyl]-2-oxo-acetyl]amino]pyridine-3-carboxamide and 5-[[2-[(2R,5S)-5-methyl-2-(2-oxoindolin-5-yl)-1-piperidyl]-2-oxo-acetyl]amino]pyridine-3-carboxamide (Compound 325 and Compound 319

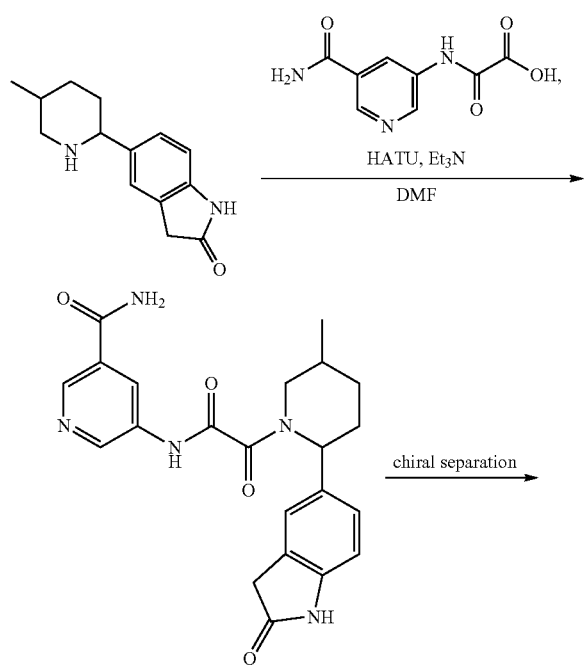

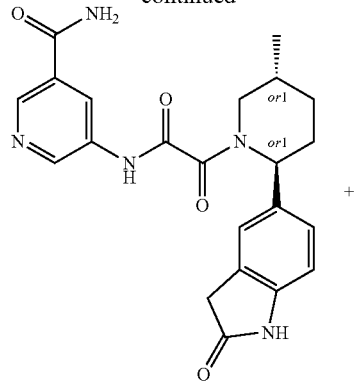

Compound 325

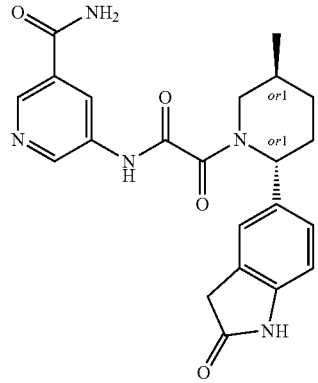

Compound 319

Step 1: Synthesis of 5-[[2-[5-methyl-2-(2-oxoindolin-5-yl)-1-piperidyl]-2-oxo-acetyl]amino]pyridine-3-carboxamide To a stirred solution of 5-(5-methyl-2-piperidyl)indolin-2-one (0.4 g, 1.74 mmol), 2-[(5-carbamoyl-3-pyridyl)amino]-2-oxo-acetic acid (426.60 mg, 1.74 mmol, HCl salt) and Triethylamine (1.76 g, 17.37 mmol, 2.42 mL) in DMF (5 mL) was added HATU (990.59 mg, 2.61 mmol) at the room temperature. The resulting reaction mixture was stirred for 18 hours at the same temperature. After 18 hours, the reaction mixture was concentrated under reduced pressure. The obtained residue was purified by HPLC (Eluent: 2-10 min, 60-85%, MeOH/H$_2$O; flow rate: 30 mL/min; loading pump: 4 mL, MeOH; column: SunFire 100×19 mm, 5 μM) to get 5-[[2-[5-methyl-2-(2-oxoindolin-5-yl)-1-piperidyl]-2-oxo-acetyl]amino]pyridine-3-carboxamide (0.09 g, 213.55 μmol, 12.30% yield) as a red solid.

LCMS(ESI): [M+H]$^+$ m/z: calcd 421.2; found 422.2; Rt=1.067 min.

Step 2: Chiral Separation of 5-[[2-[(2S,5R)-5-methyl-2-(2-oxoindolin-5-yl)-1-piperidyl]-2-oxo-acetyl]amino]pyridine-3-carboxamide and 5-[[2-[(2R,5S)-5-methyl-2-(2-oxoindolin-5-yl)-1-piperidyl]-2-oxo-acetyl]amino]pyridine-3-carboxamide (Compound 325 and Compound 319

5-[[2-[5-methyl-2-(2-oxoindolin-5-yl)-1-piperidyl]-2-oxo-acetyl]amino]pyridine-3-carboxamide (0.09 g, 213.55 μmol) was subjected to chiral HPLC (Column: IC (250×20 mm, 5 um), Eluent: CO$_2$-MeOH, 50-50; flow rate: 40 mL/min) to get 5-[[2-[(2S,5R)-5-methyl-2-(2-oxoindolin-5-yl)-1-piperidyl]-2-oxo-acetyl]amino]pyridine-3-carboxamide (Compound 325, 26.54 mg, 62.97 µmol, 29.49% yield) and 5-[[2-[(2R,5S)-5-methyl-2-(2-oxoindolin-5-yl)-1-piperidyl]-2-oxo-acetyl]amino]pyridine-3-carboxamide (Compound 319, 0.0312 g, 74.03 µmol, 34.67% yield) as light-red solids.

Compound 319:

$^1$H NMR (DMSO-$d_6$, 500 MHz): δ (ppm) 1.03 (m, 3H), 1.33 (m, 1H), 1.72 (m, 1H), 1.89 (m, 1H), 2.02 (m, 1H), 2.18 (m, 1H), 2.83 (m, 1H), 3.64 (m, 3H), 5.33 (m, 1H), 6.81 (m, 1H), 7.16 (m, 2H), 7.60 (m, 1H), 8.15 (m, 1H), 8.47 (m, 1H), 8.75 (m, 1H), 8.90 (m, 1H), 10.35 (m, 1H), 11.26 (m, 1H).

LCMS(ESI): [M+H]$^+$ m/z: calcd 421.2; found 422.2; Rt=2.467 min.

Chiral HPLC: Rt=17.33 min (column: IC; Eluent: $CO_2$-MeOH, 60-40; flow rate: 3.0 mL/min).

Compound 325:

$^1$H NMR (DMSO-$d_6$, 500 MHz): δ (ppm) 1.03 (m, 3H), 1.33 (m, 1H), 1.72 (m, 1H), 1.88 (m, 1H), 2.04 (m, 1H), 2.19 (m, 1H), 3.09 (m, 1H), 3.64 (m, 3H), 5.33 (m, 1H), 6.81 (m, 1H), 7.16 (m, 2H), 7.61 (m, 1H), 8.16 (m, 1H), 8.48 (m, 1H), 8.76 (m, 1H), 8.86 (m, 1H), 10.36 (m, 1H), 11.26 (m, 1H).

LCMS(ESI): [M+H]$^+$ m/z: calcd 421.2; found 422.2; Rt=2.486 min.

Chiral HPLC: Rt=12.75 min (column: IC; Eluent: $CO_2$-MeOH, 60-40; flow rate: 3.0 mL/min).

Example 65. The Synthesis of 2-methoxy-5-[[2-[(2S,5R)-5-methyl-2-(2-oxoindolin-5-yl)-1-piperidyl]-2-oxo-acetyl]amino]pyridine-3-carboxamide and 2-methoxy-5-[[2-[(2R,5S)-5-methyl-2-(2-oxoindolin-5-yl)-1-piperidyl]-2-oxo-acetyl]amino]pyridine-3-carboxamide (Compound 453 and Compound 454

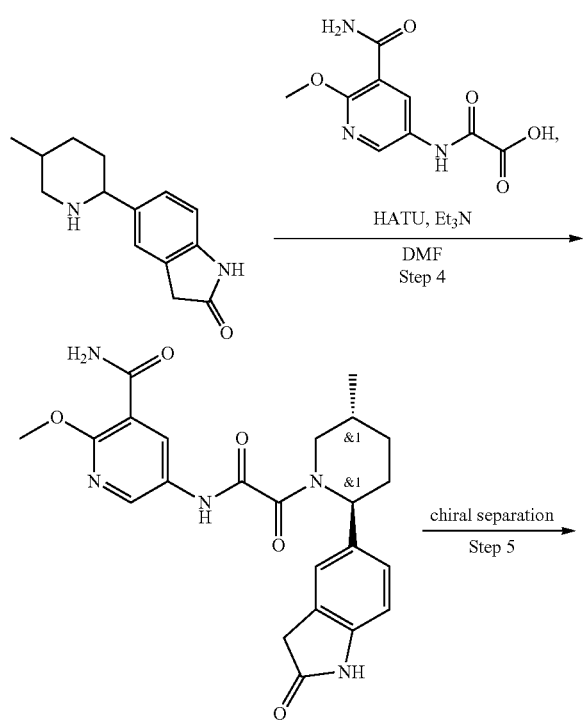

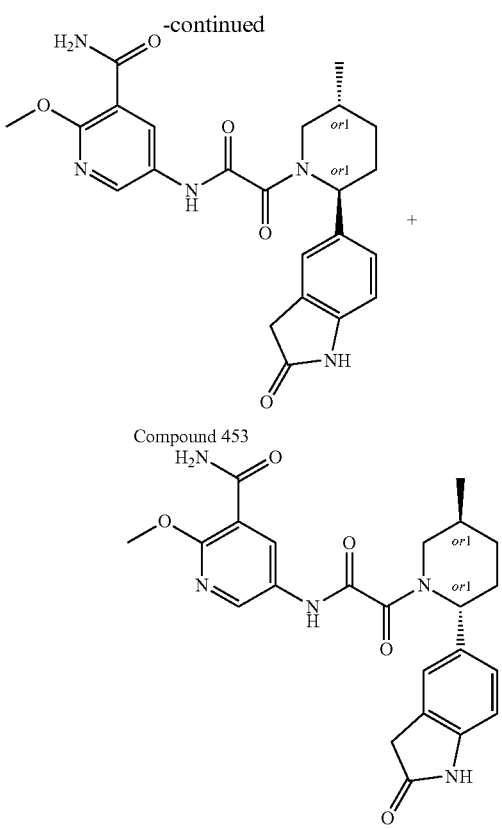

Compound 453

Compound 454

Step 1: Synthesis of 2-methoxy-5-(5-methyl-2-(2-oxoindolin-5-yl)-1-piperidyl]-2-oxo-acetyl]amino]pyridine-3-carboxamide To a stirred solution of 5-(5-methyl-2-piperidyl)indolin-2-one (200 mg, 868.41 µmol), 2-[(5-carbamoyl-6-methoxy-3-pyridyl)amino]-2-oxo-acetic acid (295.58 mg, 868.41 µmol, Et$_3$N salt) and Triethylamine (439.37 mg, 4.34 mmol, 605.19 µL) in DMF (4 mL) was added HATU (495.30 mg, 1.30 mmol) at the room temperature. The resulting reaction mixture was stirred for 12 hours at the same temperature. After 12 hours, the reaction mixture was concentrated under reduced pressure. The obtained residue was purified by HPLC to get 2-methoxy-5-(5-methyl-2-(2-oxoindolin-5-yl)-1-piperidyl]-2-oxo-acetyl]amino]pyridine-3-carboxamide (67.3 mg, 149.07 µmol, 17.17% yield) as a light-yellow solid.

LCMS(ESI): [M+H]$^+$ m/z: calcd 451.2; found 452.2; Rt=1.158 min.

Step 2: Chiral Separation of 2-methoxy-5-[[2-[(2S,5R)-5-methyl-2-(2-oxoindolin-5-yl)-1-piperidyl]-2-oxo-acetyl]amino]pyridine-3-carboxamide and 2-methoxy-5-[[2-[(2R,5S)-5-methyl-2-(2-oxoindolin-5-yl)-1-piperidyl]-2-oxo-acetyl]amino]pyridine-3-carboxamide (Compound 453 and Compound 454

2-methoxy-5-(5-methyl-2-(2-oxoindolin-5-yl)-1-piperidyl]-2-oxo-acetyl]amino]pyridine-3-carboxamide (67.3 mg, 149.07 µmol) was subjected to chiral HPLC (column: Chiralpak IB (250×30 mm, 5 um); Mobile phase: $CO_2$-MeOH, 70-30; Flow Rate: 80 mL/min) to get 2-methoxy- 5-[[2-[(2S,5R)-5-methyl-2-(2-oxoindolin-5-yl)-1-piperidyl]-2-oxo-acetyl]amino]pyridine-3-carboxamide (Compound 453, 17.04 mg, 37.74 μmol, 25.32% yield) and 2-methoxy-5-[[2-[(2R,5S)-5-methyl-2-(2-oxoindolin-5-yl)-1-piperidyl]-2-oxo-acetyl]amino]pyridine-3-carboxamide (Compound 454, 18.37 mg, 40.69 μmol, 27.30% yield) as white solids.

Compound 453:

¹H NMR (DMSO-d₆, 600 MHz): δ (ppm) 1.00 (m, 3H), 1.31 (m, 1H), 1.83 (m, 3H), 2.14 (m, 1H), 3.01 (m, 1H), 3.45 (m, 3H), 3.93 (m, 3H), 5.30 (m, 1H), 6.78 (d, 1H), 7.14 (m, 2H), 7.71 (m, 2H), 8.48 (m, 2H), 10.33 (m, 1H), 10.98 (m, 1H).

LCMS(ESI): [M+H]⁺ m/z: calcd 451.2; found 452.2; Rt=2.688 min.

Chiral HPLC: Rt=13.46 min (column: IB; Eluent: CO₂-MeOH, 75-25; flow rate: 2.0 mL/min).

Compound 454:

¹H NMR (DMSO-d₆, 600 MHz): δ (ppm) 1.00 (m, 3H), 1.32 (m, 1H), 1.71 (m, 1H), 1.87 (m, 1H), 2.07 (m, 2H), 3.01 (m, 1H), 3.45 (m, 2H), 3.93 (m, 3H), 5.30 (m, 1H), 6.79 (dd, 1H), 7.13 (m, 2H), 7.72 (m, 2H), 8.48 (m, 2H), 10.33 (m, 1H), 10.98 (m, 1H).

LCMS(ESI): [M+H]⁺ m/z: calcd 451.2; found 452.2; Rt=2.687 min.

Chiral HPLC: Rt=16.19 min (column: IB; Eluent: CO₂-MeOH, 75-25; flow rate: 2.0 mL/min).

Example 66. The Synthesis of 5-[[2-[(2R,4R,5S)-4,5-dimethyl-2-phenyl-1-piperidyl]-2-oxo-acetyl]amino]pyridine-3-carboxamide (Compound 231) and 5-[[2-[(2S,4S,5S)-4,5-dimethyl-2-phenyl-1-piperidyl]-2-oxo-acetyl]amino]pyridine-3-carboxamide Compound 229

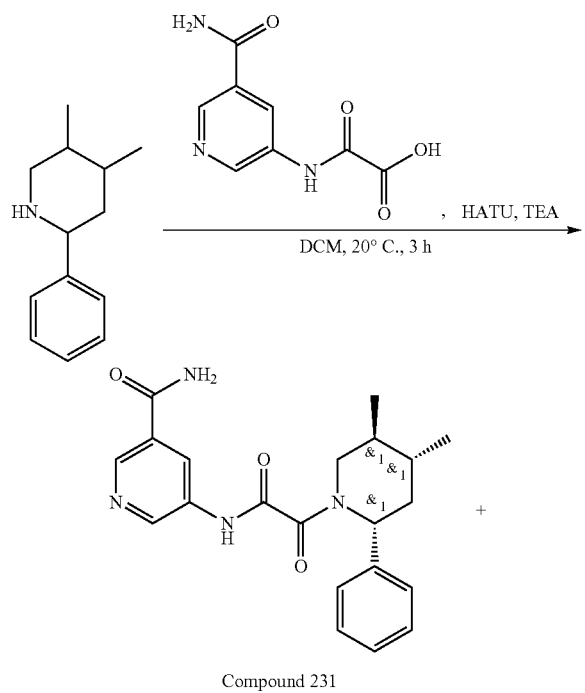

Compound 231

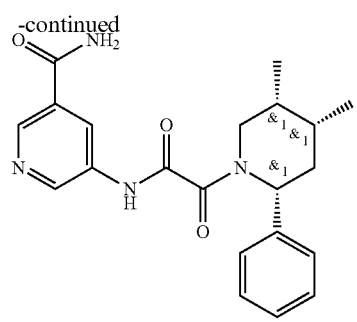

Compound 229

4,5-dimethyl-2-phenyl-piperidine (0.076 g, 401.49 μmol), 2-[(5-carbamoyl-3-pyridyl)amino]-2-oxo-acetic acid (83.97 mg, 401.49 μmol), TEA (406.27 mg, 4.01 mmol, 559.59 μL), and HATU (228.99 mg, 602.23 μmol) were dissolved in DMF (2 mL). The reaction mixture was stirred at 20° C. for 3 hr. The resulting mixture was diluted with water end extracted three times with EtOAc. Then, EtOAc was extracted three times with brine. The organic phase was dried over Na₂SO₄, filtered off, and evaporated at 40° C. to give crude product. The obtained residue was purified by HPLC (0-50% methanol, 2-10 min, flow 30 ml/min (loading pump 4 ml/min methanol) column: SunFire C18 100×20 mm) to give Compound 229—5-[[2-[(2S,4S,5S)-4,5-dimethyl-2-phenyl-1-piperidyl]-2-oxo-acetyl]amino]pyridine-3-carboxamide (0.017 g, 44.69 μmol, 11.13% yield) and Compound 231—5-[[2-[(2R,4R,5S)-4,5-dimethyl-2-phenyl-1-piperidyl]-2-oxo-acetyl]amino]pyridine-3-carboxamide (0.035 g, 92.00 μmol, 22.91% yield)5-[[2-[(2R,4R,5S)-4,5-dimethyl-2-phenyl-1-piperidyl]-2-oxo-acetyl]amino]pyridine-3-carboxamide (0.035 g, 92.00 μmol, 22.91% yield).

Compound 231: ¹H NMR (Methanol-d₄, 400 MHz): δ (ppm) 1.05 (dd, 6H), 1.64 (m, 3H), 2.07 (m, 1H), 3.80 (m, 2H), 5.19 (m, 1H), 7.26 (m, 5H), 8.70 (m, 3H).

LCMS(ESI): [M+H]⁺ m/z: calcd 380.2; found 381.2; Rt=1.167 min.

Compound 229: ¹H NMR (Chloroform-d, 400 MHz): δ (ppm) 0.77 (m, 6H), 2.04 (m, 6H), 2.88 (m, 1H), 4.52 (m, 1H), 6.24 (m, 2H), 7.27 (m, 4H), 8.52 (m, 1H), 8.84 (m, 2H), 9.90 (m, 1H).

LCMS(ESI): [M+H]⁺ m/z: calcd 380.2; found 381.2; Rt=1.180 min.

Example 67. The Synthesis of 5-[[2-[(2S,5R)-5-methyl-2-[4-(2,2,2-trifluoroethylamino)phenyl]-1-piperidyl]-2-oxo-acetyl]amino]pyridine-3-carboxamide (Compound 455) and 5-[[2-[(2R,5S)-5-methyl-2-[4-(2,2,2-trifluoroethylamino)phenyl]-1-piperidyl]-2-oxo-acetyl]amino]pyridine-3-carboxamide (Compound 456

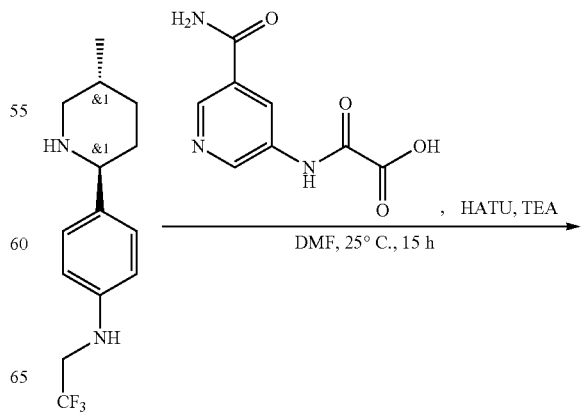

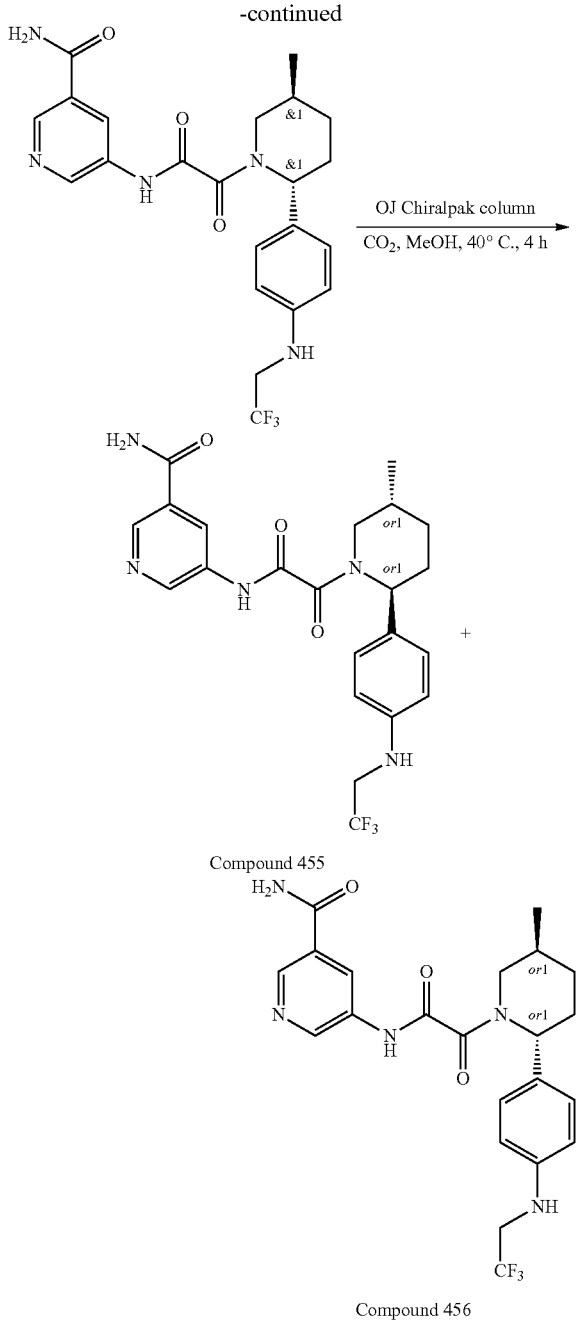

Compound 455

Compound 456

Step 1: The Synthesis of 4-[(2S,5R)-5-methyl-2-piperidyl]-N-(2,2,2-trifluoroethyl)aniline tert-butyl (2S,5R)-5-methyl-2-[4-(2,2,2-trifluoroethylamino)phenyl]piperidine-1-carboxylate (1.85 g, 4.97 mmol) was dissolved in dichloromethane (20 mL) and hydrogen chloride solution 40 M in dioxane (18.11 g, 49.67 mmol, 17.93 mL, 10% purity) was added. Resulting mixture was stirred at 25° C. for 15 hr and concentrated under reduced pressure. Residue was triturated with ethyl acetate (25 ml). Obtained gray precipitate was filtered and dried affording 4-[(2S,5R)-5-methyl-2-piperidyl]-N-(2,2,2-trifluoroethyl)aniline (1.2 g, 3.48 mmol, 69.97% yield, 2HCl).

$^1$H NMR (400 MHz, DMSO-d$_6$) δ 0.87 (m, 1H), 1.05 (d, 3H), 1.49 (m, 1H), 1.75 (m, 2H), 1.97 (m, 2H), 2.83 (m, 1H), 3.09 (m, 1H), 3.88 (m, 2H), 4.04 (m, 1H), 5.74 (s, 1H), 6.71 (d, 2H), 7.26 (d, 2H), 8.53 (m, 1H), 9.43 (m, 1H).

LCMS(ESI): [M+H]$^+$ m/z: calcd 272.2; found 273.2; Rt=0.967 min.

Step 2: The Synthesis of 5-[[2-[(2R,5S)-5-methyl-2-[4-(2,2,2-trifluoroethylamino)phenyl]-1-piperidyl]-2-oxo-acetyl]amino]pyridine-3-carboxamide 4-[(2R,5S)-5-methyl-2-piperidyl]-N-(2,2,2-trifluoroethyl)aniline (300 mg, 1.10 mmol, 2HCl), 2-[(5-carbamoyl-3-pyridyl)amino]-2-oxo-acetic acid (270.60 mg, 1.10 mmol, HCl) and triethylamine (557.40 mg, 5.51 mmol, 767.77 μL) were mixed together in dimethylformamide (3 mL). Obtained mixture was briefly heated to 60-70° C. until clear solution was formed. After cooling to 5-10° C., HATU (460.78 mg, 1.21 mmol) was added portionwise during 5 min. Resulting solution was stirred at 25° C. for 15 hr. Then it was subjected to HPLC (Column: YMC-Triart C18 100*20 mm, 5 um; 30-85% 0-5 min 0.1% NH$_3$-methanol, flow rate 30 ml/min), affording 5-[[2-[(2R,5S)-5-methyl-2-[4-(2,2,2-trifluoroethylamino)phenyl]-1-piperidyl]-2-oxo-acetyl]amino]pyridine-3-carboxamide (274 mg, 591.22 μmol, 53.66% yield).

LCMS(ESI): [M+H]$^+$ m/z: calcd 463.2; found 464.2; Rt=3.207 min.

Step 3: The Synthesis of 5-[[2-[(2S,5R)-5-methyl-2-[4-(2,2,2-trifluoroethylamino)phenyl]-1-piperidyl]-2-oxo-acetyl]amino]pyridine-3-carboxamide (Compound 455) and 5-[[2-[(2R,5S)-5-methyl-2-[4-(2,2,2-trifluoroethylamino)phenyl]-1-piperidyl]-2-oxo-acetyl]amino]pyridine-3-carboxamide (Compound 456

5-[[2-[(2R,5S)-5-methyl-2-[4-(2,2,2-trifluoroethylamino)phenyl]-1-piperidyl]-2-oxo-acetyl]amino]pyridine-3-carboxamide (226 mg, 487.64 μmol) was divided into enantiomers by Chiral HPLC (Column:Chiralpak OJ (250*30 mm, 20 mkm); Mobile phase: CO$_2$-MeOH, 60-40%. Flow Rate: 90 mL/min; 40° C.; Wavelength: 215 nm.), affording: Compound 455—5-[[2-[(2S,5R)-5-methyl-2-[4-(2,2,2-trifluoroethylamino)phenyl]-1-piperidyl]-2-oxo-acetyl]amino]pyridine-3-carboxamide (61 mg, 131.62 μmol, 53.98% yield) RetTime=2.92 min and Compound 456—5-[[2-[(2R,5S)-5-methyl-2-[4-(2,2,2-trifluoroethylamino)phenyl]-1-piperidyl]-2-oxo-acetyl]amino]pyridine-3-carboxamide (61 mg, 131.62 μmol, 53.98% yield) RetTime=8,11 min Compound 455: RT (OJ-H, CO$_2$-MeOH, 50-50, 2.0 mL/min)=2.786 min.

$^1$H NMR (DMSO-d$_6$, 600 MHz): δ (ppm) 0.74 (m, 3H), 1.13 (m, 1H), 1.63 (m, 2H), 1.83 (m, 1H), 2.37 (m, 2H), 3.76 (m, 3H), 5.27 (d, 1H), 6.20 (t, 1H), 6.72 (m, 2H), 7.03 (d, 1H), 7.07 (d, 1H), 7.58 (m, 1H), 8.14 (m, 1H), 8.47 (m, 1H), 8.75 (m, 1H), 8.86 (m, 1H), 11.22 (m, 1H)

LCMS(ESI): [M+H]$^+$ m/z: calcd 463.2; found 464.2; Rt=3.067 min.

Compound 456: RT (OJ-H, CO$_2$-MeOH, 50-50, 2.0 mL/min)=8.110 min.

$^1$H NMR (DMSO-d$_6$, 600 MHz): δ (ppm) 0.74 (m, 3H), 1.12 (m, 1H), 1.64 (m, 2H), 1.81 (m, 1H), 2.37 (m, 2H), 3.76 (m, 3H), 5.27 (m, 1H), 6.20 (t, 1H), 6.72 (m, 2H), 7.03 (d, 1H), 7.07 (d, 1H), 7.58 (m, 1H), 8.14 (m, 1H), 8.47 (m, 1H), 8.75 (m, 1H), 8.86 (m, 1H), 11.23 (m, 1H)

LCMS(ESI): [M+H]$^+$ m/z: calcd 463.2; found 464.2; Rt=3.064 min.

Example 68. The Synthesis of 5-[[2-[(2R,5R)-2-[4-[[2-(dimethylamino)-2-oxo-ethyl]amino]phenyl]-5-methyl-1-piperidyl]-2-oxo-acetyl]amino]pyridine-3-carboxamide (Compound 422), 5-[[2-[(2S,5R)-2-[4-[[2-(dimethylamino)-2-oxo-ethyl]amino]phenyl]-5-methyl-1-piperidyl]-2-oxo-acetyl]amino]pyridine-3-carboxamide (Compound 437) and 5-[[2-[(2R,5S)-2-[4-[[2-(dimethylamino)-2-oxo-ethyl]amino]phenyl]-5-methyl-1-piperidyl]-2-oxo-acetyl]amino]pyridine-3-carboxamide (Compound 1082

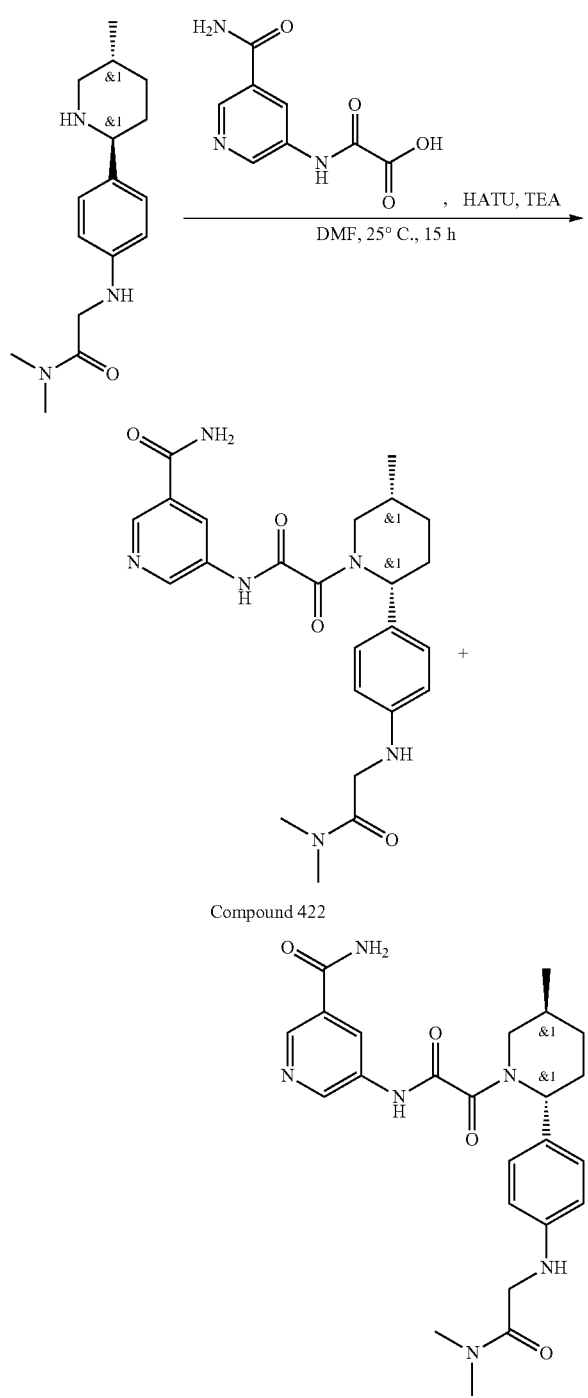

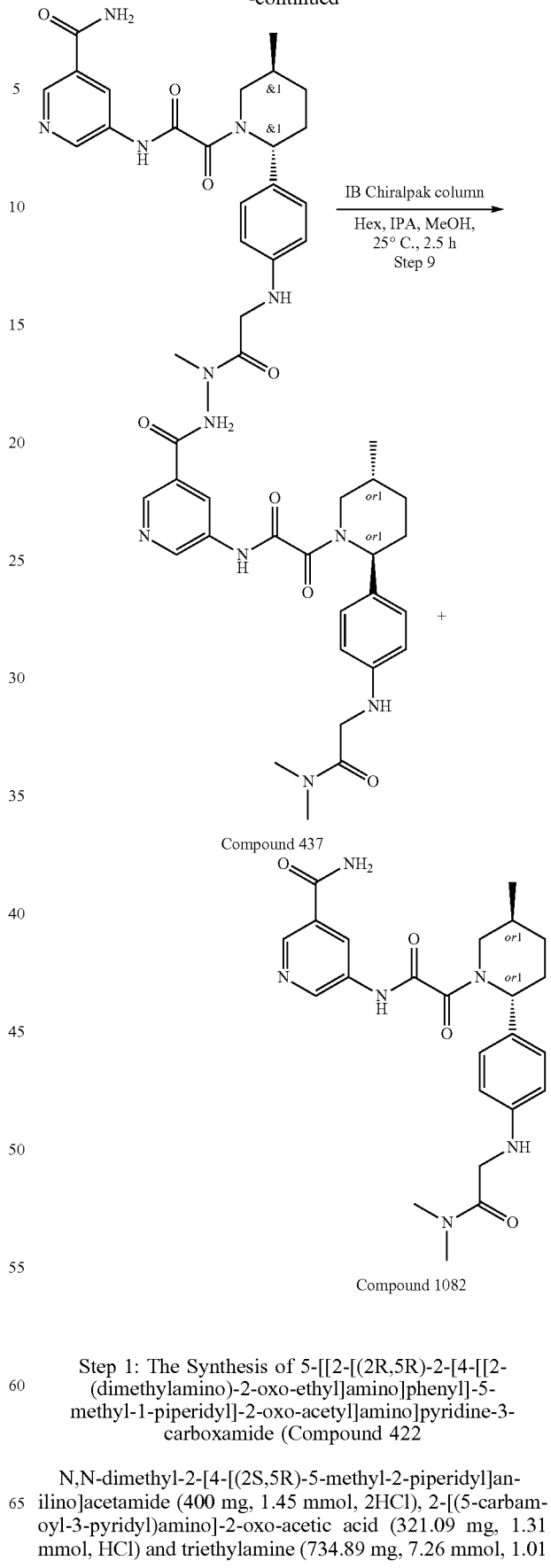

Step 1: The Synthesis of 5-[[2-[(2R,5R)-2-[4-[[2-(dimethylamino)-2-oxo-ethyl]amino]phenyl]-5-methyl-1-piperidyl]-2-oxo-acetyl]amino]pyridine-3-carboxamide (Compound 422

N,N-dimethyl-2-[4-[(2S,5R)-5-methyl-2-piperidyl]anilino]acetamide (400 mg, 1.45 mmol, 2HCl), 2-[(5-carbamoyl-3-pyridyl)amino]-2-oxo-acetic acid (321.09 mg, 1.31 mmol, HCl) and triethylamine (734.89 mg, 7.26 mmol, 1.01 mL) were mixed together in dimethylformamide (4 mL). Obtained mixture was briefly heated to 60-70° C. until clear solution was formed. After cooling to 5-10° C., HATU (552.28 mg, 1.45 mmol) was added portionwise during 5 min. Resulting solution was stirred at 25° C. for 15 hr. Then, it was subjected to HPLC (Column: YMC-Triart C18 100*20 mm, 5 um; 30-30-60% 0-1-6 min 0.10% NH$_3$-methanol, flow rate 30 ml/min.), affording 5-[[2-[(2S,5R)-2-[4-[[2-(dimethylamino)-2-oxo-ethyl]amino]phenyl]-5-methyl-1-piperidyl]-2-oxo-acetyl]amino]pyridine-3-carboxamide (227 mg, 486.57 μmol, 33.50% yield) and 5-[[2-[(2R,5R)-2-[4-[[2-(dimethylamino)-2-oxo-ethyl]amino]phenyl]-5-methyl-1-piperidyl]-2-oxo-acetyl]amino]pyridine-3-carboxamide (19 mg, 40.73 μmol, 2.80% yield).

$^1$H NMR (500 MHz, DMSO-d$_6$) δ 0.71-0.91 (m, 3H), 1.10-1.23 (m, 1H), 1.57-1.74 (m, 2H), 1.77-1.95 (m, 1H), 2.40-2.44 (m, 1H), 2.57-2.60 (m, 1H), 2.79-2.94 (m, 3H), 2.93-3.09 (m, 3H), 3.53-4.23 (m, 3H), 5.00-5.61 (m, 2H), 6.60-6.78 (m, 2H), 6.99-7.14 (m, 2H), 7.57-7.68 (m, 1H), 8.12-8.23 (m, 1H), 8.44-8.57 (m, 1H), 8.73-8.84 (m, 1H), 8.84-8.96 (m, 1H), 11.23-11.30 (m, 1H).

LCMS(ESI): [M+H]$^+$ m/z: calcd 466.2; found 467.2; Rt=2.659 min.

Step 2: The Synthesis of Synthesis of 5-[[2-[(2S,5R)-2-[4-[[2-(dimethylamino)-2-oxo-ethyl]amino]phenyl]-5-methyl-1-piperidyl]-2-oxo-acetyl]amino]pyridine-3-carboxamide (Compound 437) and 5-[[2-[(2R,5S)-2-[4-[[2-(dimethylamino)-2-oxo-ethyl]amino]phenyl]-5-methyl-1-piperidyl]-2-oxo-acetyl]amino]pyridine-3-carboxamide (Compound 1082

5-[[2-[(2S,5R)-2-[4-[[2-(dimethylamino)-2-oxo-ethyl]amino]phenyl]-5-methyl-1-piperidyl]-2-oxo-acetyl]amino]pyridine-3-carboxamide (200 mg, 428.70 μmol) was divided into enantiomers by Chiral HPLC (Column: Chiralpak IB (250*20 mm, 5 mkm); Mobile phase: Hexane-IPA-MeOH, 50-25-25 Flow Rate: 12 mL/min; m 200 mg, 2 inj., 100 mg/inj, V=21, time 2,5 h.)), affording: Compound 437—5-[[2-[(2S,5R)-2-[4-[[2-(dimethylamino)-2-oxo-ethyl]amino]phenyl]-5-methyl-1-piperidyl]-2-oxo-acetyl]amino]pyridine-3-carboxamide (78 mg, 167.19 μmol, 78.00% yield) with ret. time 26.49 min and Compound 1082—5-[[2-[(2R,5S)-2-[4-[[2-(dimethylamino)-2-oxo-ethyl]amino]phenyl]-5-methyl-1-piperidyl]-2-oxo-acetyl]amino]pyridine-3-carboxamide (78 mg, 167.19 μmol, 78.00% yield) with ret. time 42.74 min.

Compound 437: RT (IB, Hexane-IPA-MeOH, 50-25-25, 0.6 mL/min)=25.532 min.

$^1$H NMR (500 MHz, DMSO-d$_6$) δ 1.01-1.06 (m, 3H), 1.28-1.42 (m, 1H), 1.67-1.94 (m, 2H), 1.94-2.12 (m, 1H), 2.12-2.22 (m, 1H), 2.76—2.82 (m, 0.3H), 2.82-2.93 (m, 3H), 2.96-3.07 (m, 3H), 3.21-3.26 (m, 0.7H), 3.41-3.97 (m, 3H), 4.98-5.58 (m, 2H), 6.57-6.77 (m, 2H), 6.97-7.13 (m, 2H), 7.46-7.73 (m, 1H), 8.11-8.26 (m, 1H), 8.41-8.57 (m, 1H), 8.70-8.85 (m, 1H), 8.85-8.98 (m, 1H), 11.08-11.33 (m, 1H).

LCMS(ESI): [M+H]$^+$ m/z: calcd 466.2; found 467.2; Rt=2.595 min.

Compound 1082: RT (IB, Hexane-IPA-MeOH, 50-25-25, 0.6 mL/min)=50.919 min.

$^1$H NMR (500 MHz, DMSO-d$_6$) δ 1.01-1.05 (m, 3H), 1.28-1.41 (m, 1H), 1.66-1.94 (m, 2H), 1.94-2.11 (m, 1H), 2.11-2.21 (m, 1H), 2.76-2.82 (m, 0.4H), 2.85-2.89 (m, 3H), 2.98-3.03 (m, 3H), 3.17-3.23 (m, 0.6H), 3.43-3.98 (m, 3H), 4.95-5.60 (m, 2H), 6.54-6.75 (m, 2H), 6.98-7.14 (m, 2H), 7.52-7.74 (m, 1H), 8.09-8.27 (m, 1H), 8.39-8.57 (m, 1H), 8.70-8.82 (m, 1H), 8.82-8.97 (m, 1H), 11.15-11.29 (m, 1H).

LCMS(ESI): [M+H]$^+$ m/z: calcd 466.2; found 467.2; Rt=2.593 min.

Example 69. The Synthesis of 5-[[2-[(2S,5R)-5-methyl-2-[4-[[(3R)-1-methyl-2-oxo-pyrrolidin-3-yl]amino]phenyl]-1-piperidyl]-2-oxo-acetyl]amino]pyridine-3-carboxamide (Compound 430) and 5-[[2-[(2R,5R)-5-methyl-2-[4-[[(3R)-1-methyl-2-oxo-pyrrolidin-3-yl]amino]phenyl]-1-piperidyl]-2-oxo-acetyl]amino]pyridine-3-carboxamide (Compound 427)

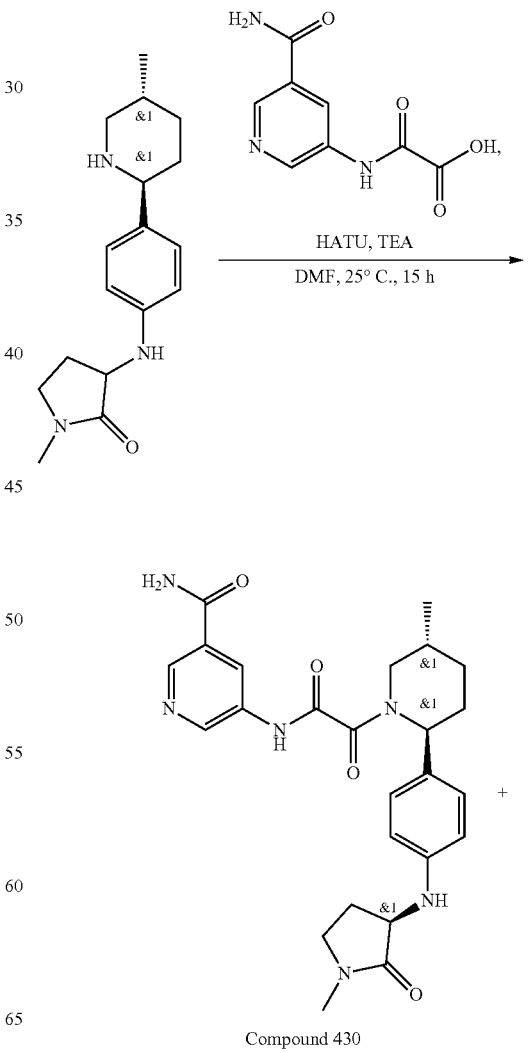

Compound 430

-continued

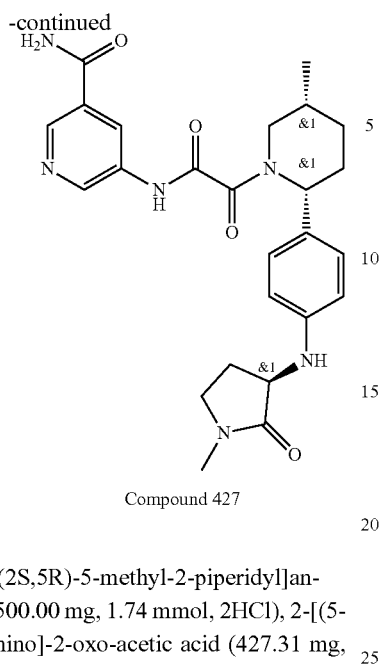

Compound 427

(3R)-1-methyl-3-[4-[(2S,5R)-5-methyl-2-piperidyl]anilino]pyrrolidin-2-one (500.00 mg, 1.74 mmol, 2HCl), 2-[(5-carbamoyl-3-pyridyl)amino]-2-oxo-acetic acid (427.31 mg, 1.74 mmol, HCl) and triethylamine (880.22 mg, 8.70 mmol, 1.21 mL) were mixed together in dimethylformamide (5 mL). Obtained mixture was briefly heated to 60-70° C. until clear solution was formed. After cooling to 5-10° C., HATU (727.65 mg, 1.91 mmol) was added portionwise during 5 min. Resulting solution was stirred at 25° C. for 15 hr. Then it was subjected to HPLC (Column: YMC Triart C18 100*20 mm, 5 um; 30-30-65% 0-1-5 min 0.1% NH$_3$-methanol, flow: 30 ml/min), affording 5-[[2-[(2S,5R)-5-methyl-2-[4-[[(3R)-1-methyl-2-oxo-pyrrolidin-3-yl]amino]phenyl]-1-piperidyl]-2-oxo-acetyl]amino]pyridine-3-carboxamide (180 mg, 376.14 μmol, 21.62% yield) and 5-[[2-[(2R,5R)-5-methyl-2-[4-[[(3R)-1-methyl-2-oxo-pyrrolidin-3-yl]amino]phenyl]-1-piperidyl]-2-oxo-acetyl]amino]pyridine-3-carboxamide (28 mg, 58.51 μmol, 3.36% yield).

Compound 430:

$^1$H NMR (500 MHz, DMSO-d$_6$) δ 0.96-1.07 (m, 3H), 1.27-1.41 (m, 1H), 1.65-1.79 (m, 2H), 1.79-2.02 (m, 2H), 2.07-2.24 (m, 2H), 2.56-2.61 (m, 1H), 2.75-3.27 (m, 4H), 3.34-3.99 (m, 2H), 4.00-4.07 (m, 1H), 5.00-5.55 (m, 1H), 5.63-5.78 (m, 1H), 6.60-6.78 (m, 2H), 6.96-7.13 (m, 2H), 7.53-7.68 (m, 1H), 8.10-8.25 (m, 1H), 8.38-8.57 (m, 1H), 8.68-8.84 (m, 1H), 8.84-8.97 (m, 1H), 11.06-11.32 (m, 1H).

LCMS(ESI): [M+H]$^+$ m/z: calcd 478.2; found 479.2; Rt=2.707 min.

Compound 427:

$^1$H NMR (500 MHz, DMSO-d$_6$) δ 0.72-0.82 (m, 3H), 1.09-1.25 (m, 1H), 1.56-1.70 (m, 2H), 1.70-1.84 (m, 2H), 1.84-2.23 (m, 1H), 2.39-2.44 (m, 1H), 2.58-2.61 (m, 1H), 2.77-2.79 (m, 3H), 3.30-3.31 (m, 1H), 3.35-3.37 (m, 1H), 3.53-4.21 (m, 2H), 4.98-5.61 (m, 1H), 5.70-5.84 (m, 1H), 6.67-6.72 (m, 2H), 7.01-7.10 (m, 2H), 7.57-7.66 (m, 1H), 8.14-8.21 (m, 1H), 8.47-8.55 (m, 1H), 8.76-8.81 (m, 1H), 8.86-8.94 (m, 1H), 11.24-11.28 (m, 1H).

LCMS(ESI): [M+H]$^+$ m/z: calcd 478.2; found 479.2; Rt=2.636 min.

Example 70. The Synthesis of 5-[[2-[(2R,5S)-2-[4-[[(1R)-2-(dimethylamino)-1-methyl-2-oxo-ethyl]amino]phenyl]-5-methyl-1-piperidyl]-2-oxo-acetyl]amino]pyridine-3-carboxamide (Compound 414

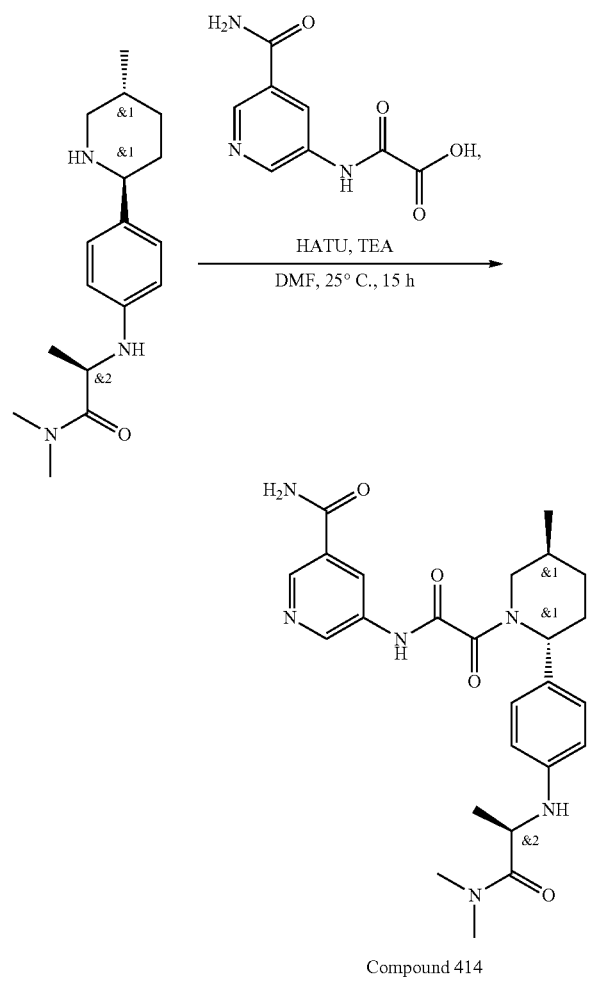

Compound 414

(2R)—N,N-dimethyl-2-[4-[(2R,5S)-5-methyl-2-piperidyl]anilino]propanamide (0.69 g, 2.38 mmol, 2HCl), 2-[(5-carbamoyl-3-pyridyl)amino]-2-oxo-acetic acid (585.59 mg, 2.38 mmol, HCl) and triethylamine (1.21 g, 11.92 mmol, 1.66 mL) were mixed together in dimethylformamide (8 mL). Obtained mixture was briefly heated to 60-70° C. until clear solution was formed. After cooling to 5-10° C., HATU (997.17 mg, 2.62 mmol) was added portionwise during 5 min. Resulting solution was stirred at 25° C. for 15 hr. Then it was subjected to HPLC (Column: YMC-Triart C18 100*20 mm, 5 um; 10-10-50% 0-1-6 min 0.1% NH$_3$-methanol, flow rate 30 ml/min.), affording 5-[[2-[(2R,5S)-2-[4-[[(1R)-2-(dimethylamino)-1-methyl-2-oxo-ethyl]amino]phenyl]-5-methyl-1-piperidyl]-2-oxo-acetyl]amino]pyridine-3-carboxamide (467 mg, 971.79 μmol, 40.76% yield).

$^1$H NMR (500 MHz, DMSO-d$_6$) δ 1.00-1.19 (m, 3H), 1.20-1.31 (m, 3H), 1.34-1.45 (m, 1H), 1.78-1.98 (m, 2H), 2.00-2.22 (m, 2H), 2.86-2.92 (m, 3H), 3.10-3.15 (m, 3H), 3.19-3.32 (m, 1H), 3.55-4.10 (m, 1H), 4.32-4.47 (m, 1H), 5.08-5.65 (m, 2H), 6.48-6.65 (m, 2H), 6.94-7.10 (m, 2H), 7.25-7.43 (m, 1H), 7.95-8.12 (m, 1H), 8.46-8.56 (m, 1H), 8.63-8.77 (m, 1H), 8.81-9.04 (m, 1H), 10.99-11.17 (m, 1H).

LCMS(ESI): [M+H]+ m/z: calcd 480.2; found 481.2; Rt=2.687 min.

Example 71. The Synthesis of 5-[[2-[(2R,5S)-5-methyl-2-(1,2,3,4-tetrahydroquinolin-6-yl)-1-piperidyl]-2-oxo-acetyl]amino]pyridine-3-carboxamide (Compound 426) and 5-[[2-[(2S,5R)-5-methyl-2-(1,2,3,4-tetrahydroquinolin-6-yl)-1-piperidyl]-2-oxo-acetyl]amino]pyridine-3-carboxamide (Compound 432

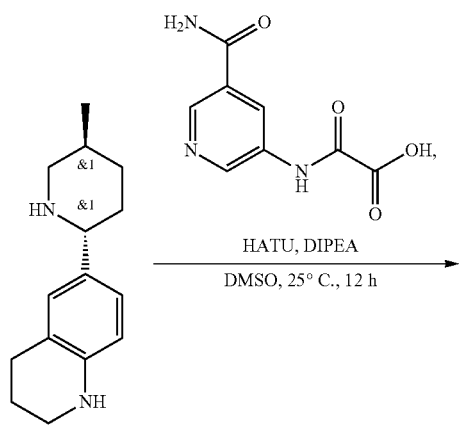

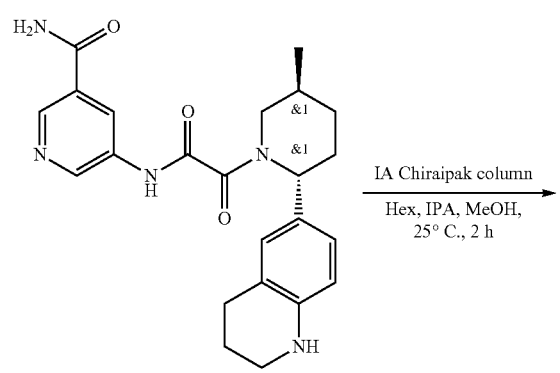

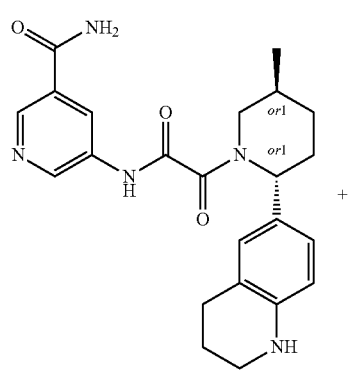

Compound 426

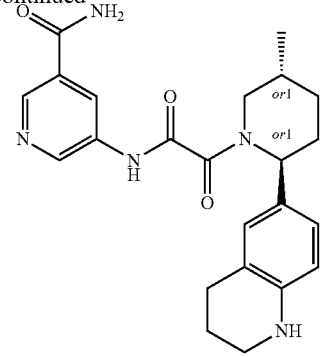

Compound 432

Step 1: The Synthesis of 5-[[2-[(2R,5S)-5-methyl-2-(1,2,3,4-tetrahydroquinolin-6-yl)-1-piperidyl]-2-oxo-acetyl]amino]pyridine-3-carboxamide 6-[(2R,5S)-5-methyl-2-piperidyl]-1,2,3,4-tetrahydroquinoline (0.1 g, 377.69 μmol), 2-[(5-carbamoyl-3-pyridyl)amino]-2-oxo-acetic acid (0.148 g, 707.60 μmol, TEA), HATU (0.217 g, 570.71 μmol), DIPEA (0.086 g, 665.41 μmol, 115.90 μL) were placed in 8 mL vial and stirred in DMSO (1 mL) at 25° C. for 12 hr. LCMS spectra of the reaction mixture showed 38% of desired product. The reaction mixture was submitted to HPLC to afford 5-[[2-[(2R,5S)-5-methyl-2-(1,2,3,4-tetrahydroquinolin-6-yl)-1-piperidyl]-2-oxo-acetyl]amino]pyridine-3-carboxamide (0.048 g, 113.88 μmol, 30.15% yield).

LCMS(ESI): [M+H]+ m/z: calcd 421.2; found 422.2; Rt=0.959 min.

Step 2: The Synthesis of 5-[[2-[(2R,5S)-5-methyl-2-(1,2,3,4-tetrahydroquinolin-6-yl)-1-piperidyl]-2-oxo-acetyl]amino]pyridine-3-carboxamide (Compound 426) and 5-[[2-[(2S,5R)-5-methyl-2-(1,2,3,4-tetrahydroquinolin-6-yl)-1-piperidyl]-2-oxo-acetyl]amino]pyridine-3-carboxamide (Compound 432

Initial racemate was submitted to chiral separation to afford 5-[[2-[(2R,5S)-5-methyl-2-(1,2,3,4-tetrahydroquinolin-6-yl)-1-piperidyl]-2-oxo-acetyl]amino]pyridine-3-carboxamide (0.04 g, 94.90 μmol, 42.11% yield, Compound 426) and 5-[[2-[(2S,5R)-5-methyl-2-(1,2,3,4-tetrahydroquinolin-6-yl)-1-piperidyl]-2-oxo-acetyl]amino]pyridine-3-carboxamide (0.03 g, 71.18 μmol, 31.58% yield, Compound 432).

Preparatory Sample Info: IA (250*30, 5 mkm), Hexane-IPA-MeOH, 50-25-25, 12 ml/min and HPLC Sample Info: Inj Volume 900.000 μl, C18, H2O-MeCN, 15-45% MeCN, 30 ml/min Compound 426:

RT (IA, Hexane-IPA-MeOH, 50-25-25, 0.6 mL/min)=21.419 min.

1H NMR (500 MHz, DMSO-d6) δ 1.00-1.05 (m, 3H), 1.27-1.38 (m, 1H), 1.72-1.85 (m, 4H), 1.93-2.06 (m, 1H), 2.10-2.18 (m, 1H), 2.64-2.70 (m, 2H), 2.86-3.23 (m, 3H), 3.37-4.00 (m, 1H), 4.92-5.51 (m, 1H), 5.58-5.63 (m, 1H), 6.39-6.46 (m, 1H), 6.78-6.86 (m, 2H), 7.58-7.66 (m, 1H), 8.13-8.20 (m, 1H), 8.45-8.53 (m, 1H), 8.75-8.81 (m, 1H), 8.83-8.93 (m, 1H), 11.12-11.30 (m, 1H).

LCMS(ESI): [M+H]⁺ m/z: calcd 421.2; found 422.2; Rt=3.526 min.

Compound 432:

RT (IA, Hexane-IPA-MeOH, 50-25-25, 0.6 mL/min)=47.532 min.

¹H NMR (500 MHz, DMSO-d₆) δ 1.00-1.06 (m, 3H), 1.25-1.37 (m, 1H), 1.69-1.90 (m, 4H), 1.92-2.06 (m, 1H), 2.08-2.18 (m, 1H), 2.63-2.72 (m, 2H), 2.84-3.25 (m, 3H), 3.36-3.97 (m, 1H), 4.91-5.56 (m, 1H), 5.57-5.67 (m, 1H), 6.35-6.49 (m, 1H), 6.72-6.90 (m, 2H), 7.50-7.73 (m, 1H), 8.07-8.24 (m, 1H), 8.41-8.60 (m, 1H), 8.70-8.83 (m, 1H), 8.83-8.97 (m, 1H), 11.08-11.29 (m, 1H).

LCMS(ESI): [M+H]⁺ m/z: calcd 421.2; found 422.2; Rt=3.582 min.

Example 72. The Synthesis of 5-[[2-[(2R,5S)-5-methyl-2-(2-oxo-3,4-dihydro-1H-Quinolin-6-yl)-1-piperidyl]-2-oxo-acetyl]amino]pyridine-3-carboxamide (Compound 479) and 5-[[2-[(2S,5R)-5-methyl-2-(2-oxo-3,4-dihydro-1H-Quinolin-6-yl)-1-piperidyl]-2-oxo-acetyl]amino]pyridine-3-carboxamide (Compound 480

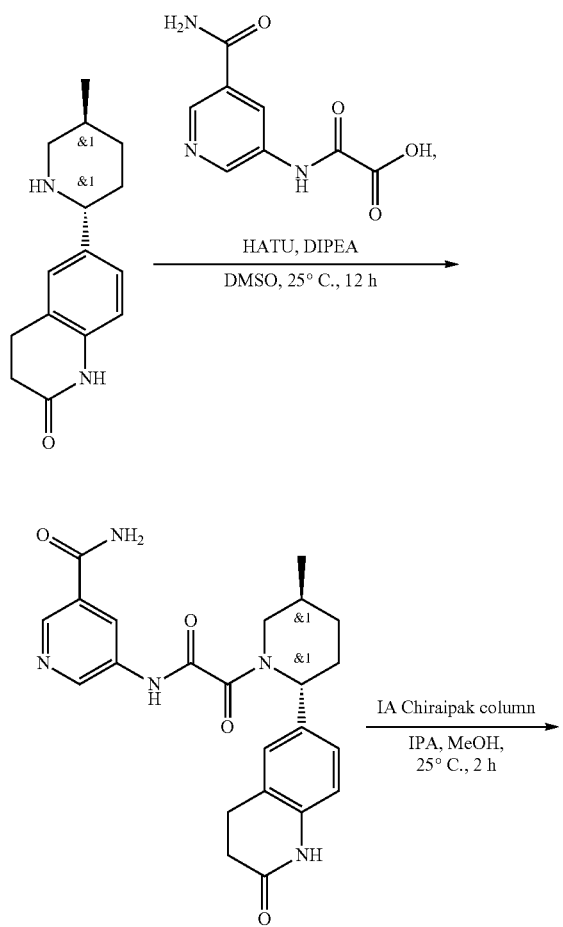

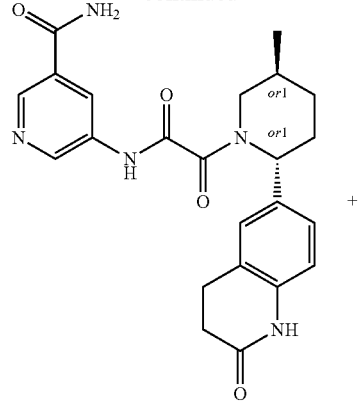

Compound 479

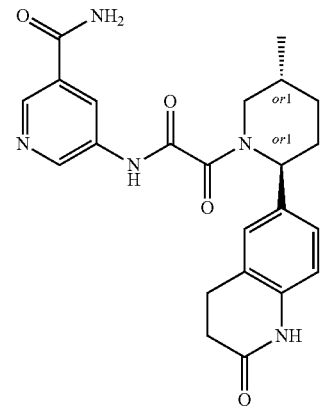

Compound 480

Step 1: The Synthesis of 5-(2-((2R,5S)-5-methyl-2-(2-oxo-1, 2, 3,4-tetrahydroquinolin-6-yl)piperidin-1-yl)-2-oxoacetamido)Nicotinamide A mixture of 6-(5-methyl-2-piperidyl)-3,4-dihydro-1H-quinolin-2-one (0.4 g, 1.24 mmol, HCl), C8H7N3O4 (311.06 mg, 1.49 mmol, TEA), HATU (612.61 mg, 1.61 mmol) and DIPEA (742.00 mg, 5.74 mmol, 1 mL) were stirred in DMSO (5 mL) overnight. LCMS analysis of a reaction mixture showed 24% of desired product. After that the reaction mixture was submitted to HPLC (2-10 min 40-60% water/MeCN+NH₃ (loading pump 4 ml MeCN+NH₃)) column: TRIART 100*20 mm 5 microM) to afford 5-(2-((2R,5S)-5-methyl-2-(2-oxo-1,2,3,4-tetrahydroquinolin-6-yl)piperidin-1-yl)-2-oxoacetamido)nicotinamide (0.084 g, 192.89 μmol, 15.56% yield).

LCMS(ESI): [M+H]⁺ m/z: calcd 435.2; found 436.2; Rt=2.416 min.

Step 2: The Synthesis of 5-[[2-[(2R,5S)-5-methyl-2-(2-oxo-3,4-dihydro-1H-Quinolin-6-yl)-1-piperidyl]-2-oxo-acetyl]amino]pyridine-3-carboxamide (Compound 479) and 5-[[2-[(2S,5R)-5-methyl-2-(2-oxo-3,4-dihydro-1H-Quinolin-6-yl)-1-piperidyl]-2-oxo-acetyl]amino]pyridine-3-carboxamide (Compound 480

5-[[2-[(2R,5S)-5-methyl-2-(2-oxo-3,4-dihydro-1H-quinolin-6-yl)-1-piperidyl]-2-oxo-acetyl]amino]pyridine-3-carboxamide (0.084 g, 192.89 μmol) was submitted to chiral separation (Injection Volume: 100 mkl; Sample Info: IC—I (250*20, 5 mic), IPA-MeOH, 50-50, 10 ml/min) to afford pure Compound 479—5-[[2-[(2R,5S)-5-methyl-2-(2-oxo-3,4-dihydro-1H-quinolin-6-yl)-1-piperidyl]-2-oxo-acetyl]amino]pyridine-3-carboxamide (0.038 g, 87.26 μmol, 45.24% yield) and Compound 480—5-[[2-[(2S,5R)-5-methyl-2-(2-oxo-3,4-dihydro-1H-quinolin-6-yl)-1-piperidyl]-2-oxo-acetyl]amino]pyridine-3-carboxamide (0.035 g, 80.37 μmol, 41.67% yield).

Compound 479: RT (IC, MeOH-IPA, 50-50, 0.6 mL/min)=26.004 min.

$^1$H NMR (600 MHz, DMSO-$d_6$) δ 0.98-1.04 (m, 3H), 1.27-1.37 (m, 1H), 1.59-1.77 (m, 1H), 1.80-1.94 (m, 1H), 1.95-2.11 (m, 1H), 2.12-2.23 (m, 1H), 2.37-2.44 (m, 2H), 2.83-3.25 (m, 3H), 3.43-4.00 (m, 1H), 5.01-5.57 (m, 1H), 6.78-6.94 (m, 1H), 7.04-7.17 (m, 2H), 7.53-7.63 (m, 1H), 8.06-8.20 (m, 1H), 8.41-8.53 (m, 1H), 8.69-8.79 (m, 1H), 8.79-8.93 (m, 1H), 10.00-10.06 (m, 1H), 11.09-11.40 (m, 1H).

LCMS(ESI): [M+H]$^+$ m/z: calcd 435.2; found 436.2; Rt=2.215 min.

Compound 480: RT (IC, MeOH-IPA, 50-50, 0.6 mL/min)=17.820 min.

$^1$H NMR (600 MHz, DMSO-$d_6$) δ 0.97-1.06 (m, 3H), 1.27-1.39 (m, 1H), 1.65-1.76 (m, 1H), 1.81-1.94 (m, 1H), 1.94-2.12 (m, 1H), 2.13-2.21 (m, 1H), 2.38-2.44 (m, 2H), 2.81-3.26 (m, 3H), 3.42-4.00 (m, 1H), 5.02-5.60 (m, 1H), 6.79-6.89 (m, 1H), 7.05-7.19 (m, 2H), 7.54-7.67 (m, 1H), 8.08-8.20 (m, 1H), 8.41-8.53 (m, 1H), 8.68-8.79 (m, 1H), 8.79-8.93 (m, 1H), 10.00-10.11 (m, 1H), 11.12-11.30 (m, 1H).

LCMS(ESI): [M+H]$^+$ m/z: calcd 435.2; found 436.2; Rt=2.213 min.

Example 73. The Synthesis of 2-methoxy-5-[[2-[(2R,5S)-5-methyl-2-(2-oxo-3,4-dihydro-1H-Quinolin-6-yl)-1-piperidyl]-2-oxo-acetyl]amino]pyridine-3-carboxamide (Compound 673) and 2-methoxy-5-[[2-[(2S,5R)-5-methyl-2-(2-oxo-3,4-dihydro-1H-Quinolin-6-yl)-1-piperidyl]-2-oxo-acetyl]amino]pyridine-3-carboxamide (Compound 674

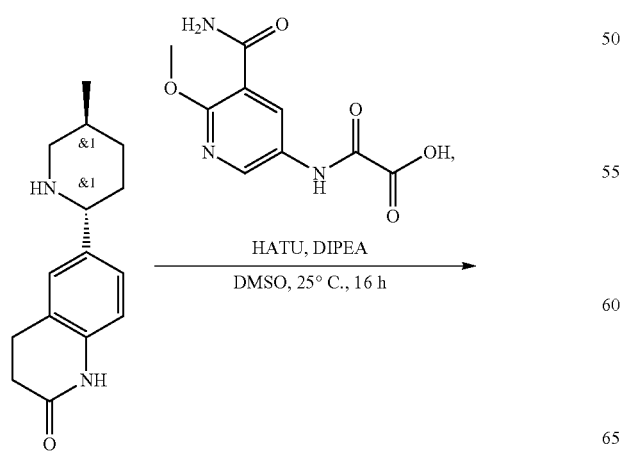

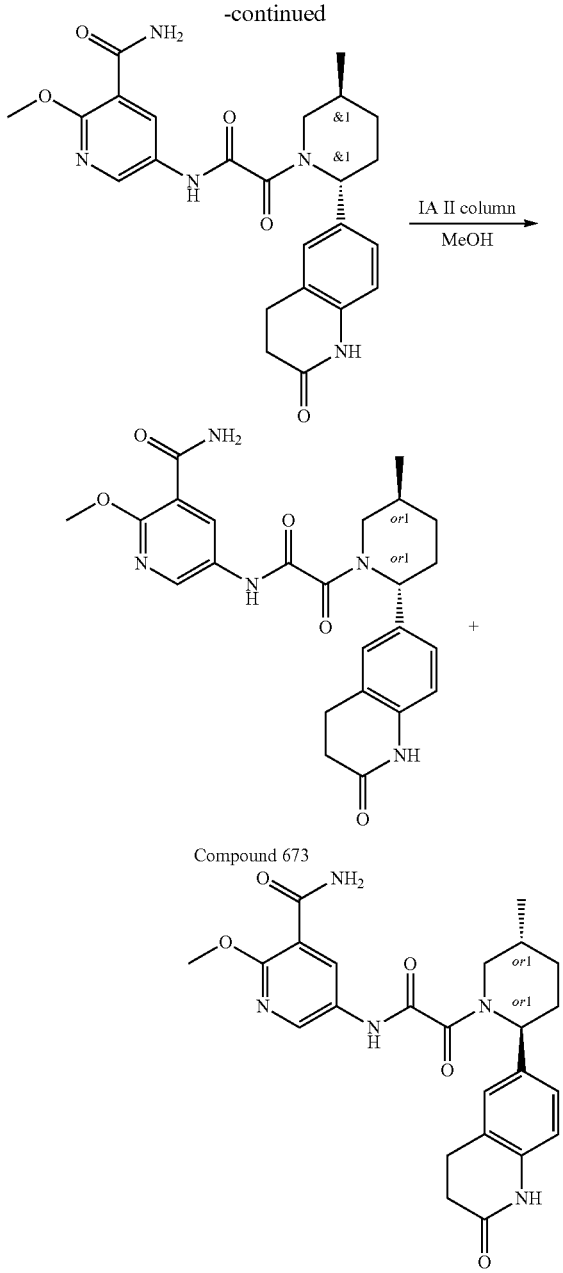

Compound 673

Compound 674

Step 1: The Synthesis of 2-methoxy-5-[[2-[(2R,5S)-5-methyl-2-(2-oxo-3,4-dihydro-1H-Quinolin-6-yl)-1-piperidyl]-2-oxo-acetyl]amino]pyridine-3-carboxamide To a stirred solution of 6-[(2R,5S)-5-methyl-2-piperidyl]-3,4-dihydro-1H-quinolin-2-one (0.4 g, 1.64 mmol) 2-[(5-carbamoyl-6-methoxy-3-pyridyl)amino]-2-oxo-acetic acid (469.89 mg, 1.96 mmol, TEA) and DIPEA (1.06 g, 8.19 mmol, 1.43 mL) in DMSO (5 mL) was added HATU (746.98 mg, 1.96 mmol). The resulting reaction mixture was stirred at 25° C. for 16 hr. Upon completion, the reaction mixture was submitted to reverse phase HPLC (2-10 min 50-60% water/MeOH (loading pump 4 mL MeOH) column: TRIART 100*20 5 microM) to afford 2-methoxy-5-[[2-[(2R, 5S)-5-methyl-2-(2-oxo-3,4-dihydro-1H-quinolin-6-yl)-1-piperidyl]-2-oxo-acetyl]amino]pyridine-3-carboxamide (0.228 g, 489.79 μmol, 29.92% yield) as a light-yellow solid.

LCMS(ESI): [M+H]⁺ m/z: calcd 465.2; found 466.4; Rt=0.934 min.

Step 2: The Synthesis of 2-methoxy-5-[[2-[(2R,5S)-5-methyl-2-(2-oxo-3,4-dihydro-1H-Quinolin-6-yl)-1-piperidyl]-2-oxo-acetyl]amino]pyridine-3-carboxamide (Compound 673) and 2-methoxy-5-[[2-[(2S,5R)-5-methyl-2-(2-oxo-3,4-dihydro-1H-Quinolin-6-yl)-1-piperidyl]-2-oxo-acetyl]amino]pyridine-3-carboxamide (Compound 674

2-methoxy-5-[[2-[(2R,5S)-5-methyl-2-(2-oxo-3,4-dihydro-1H-quinolin-6-yl)-1-piperidyl]-2-oxo-acetyl]amino]pyridine-3-carboxamide (0.228 g, 489.80 μmol) was submitted to chiral separation (IA-II (250*20, 5 mkm), MeOH, 100, 16 mL/min) to afford Compound 673-2-methoxy-5-[[2-[(2R,5S)-5-methyl-2-(2-oxo-3,4-dihydro-1H-quinolin-6-yl)-1-piperidyl]-2-oxo-acetyl]amino]pyridine-3-carboxamide (0.063 g, 135.34 μmol, 27.63% yield) and Compound 674—2-methoxy-5-[[2-[(2S,5R)-5-methyl-2-(2-oxo-3,4-dihydro-1H-quinolin-6-yl)-1-piperidyl]-2-oxo-acetyl]amino]pyridine-3-carboxamide (0.066 g, 141.78 μmol, 28.95% yield).

Compound 673: RT (IC, CO₂-MeOH, 50-50, 2.0 mL/min)=22.191 min.

¹H NMR (DMSO-d₆, 600 MHz): δ (ppm) 1.00 (m, 3H), 1.32 (m, 1H), 1.92 (m, 5H), 2.95 (m, 4H), 3.93 (m, 4H), 5.27 (m, 1H), 6.86 (m, 1H), 7.09 (m, 2H), 7.72 (m, 2H), 8.47 (m, 2H), 10.03 (m, 1H), 10.98 (m, 1H).

LCMS(ESI): [M+H]⁺ m/z: calcd 465.2; found 466.0; Rt=2.279 min.

Compound 674: RT (IC, CO₂-MeOH, 50-50, 2.0 mL/min)=28.266 min.

¹H NMR (DMSO-d₆, 600 MHz): δ (ppm) 1.00 (m, 3H), 1.32 (m, 1H), 1.68 (m, 1H), 1.86 (m, 1H), 2.09 (m, 2H), 2.43 (m, 2H), 2.86 (m, 3H), 3.93 (m, 4H), 5.28 (m, 1H), 6.84 (m, 1H), 7.09 (m, 2H), 7.72 (m, 2H), 8.47 (m, 2H), 10.03 (m, 1H), 10.99 (m, 1H).

LCMS(ESI): [M+H]⁺ m/z: calcd 465.2; found 466.0; Rt=2.279 min.

Example 74. The Synthesis of N-(5,6-dimethyl-3-pyridyl)-2-[(2S,5R)-5-methyl-2-(2-oxo-3,4,4a,8a-tetrahydro-1H-Quinolin-6-yl)-1-piperidyl]-2-oxo-acetamide (Compound 632) and N-(5,6-dimethyl-3-pyridyl)-2-[(2R,5S)-5-methyl-2-(2-oxo-3,4,4a,8a-tetrahydro-H-Quinolin-6-yl)-1-piperidyl]-2-oxo-acetamide (Compound 619

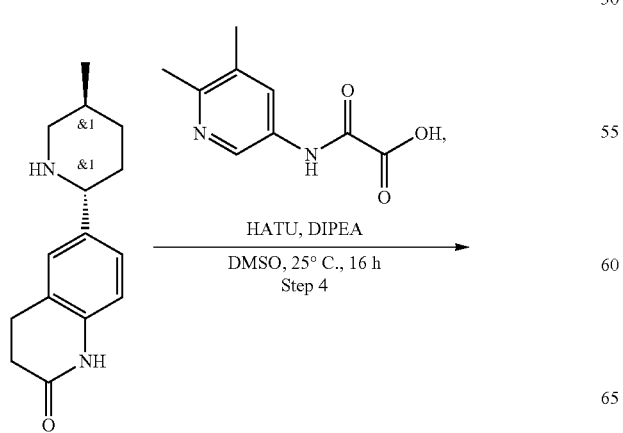

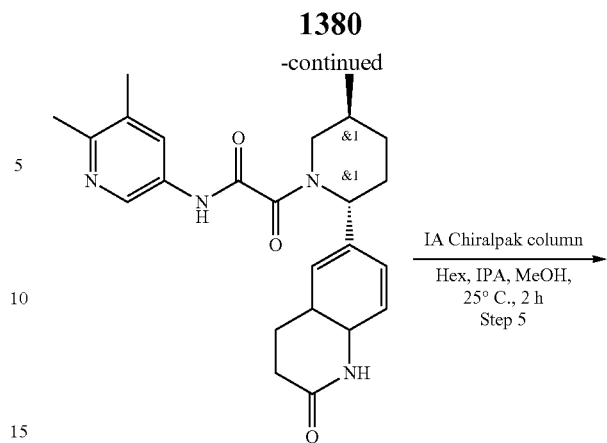

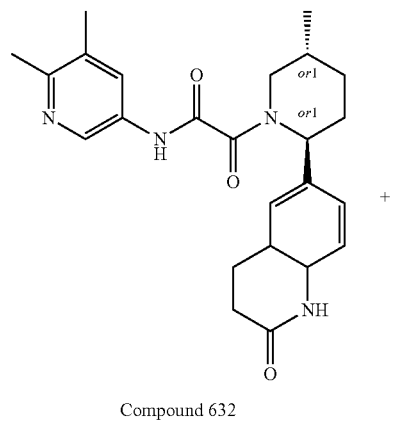

Compound 632

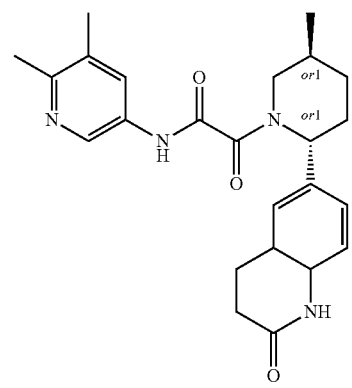

Compound 619

Step 1: The Synthesis of N-(5,6-dimethyl-3-pyridyl)-2-[(2R,5S)-5-methyl-2-(2-oxo-3,4,4a,8a-tetrahydro-1H-Quinolin-6-yl)-1-piperidyl]-2-oxo-acetamide To the solution of 6-[(2R,5S)-5-methyl-2-piperidyl]-3,4,4a,8a-tetrahydro-1H-quinolin-2-one (300 mg, 1.22 mmol), 2-[(5,6-dimethyl-3-pyridyl)amino]-2-oxo-acetic acid (359.71 mg, 1.22 mmol, Et₃N) and triethylamine (123.23 mg, 1.22 mmol, 169.74 μL) in DMF (3 mL), HATU (463.04 mg, 1.22 mmol) was added portionwise. Mixture was stirred at 25° C. for 3 hr. The reaction mixture was then purified by reverse phase HPLC (40-40-65% 0-1-5 min 0.2% TFA-methanol, flow: 30 ml/min (loading pump 4 ml/min methanol) target mass 420 column: YMC Triart C18 100*20 mm, 5 um) to give N-(5,6-dimethyl-3-pyridyl)-2-[(2R,5S)-5-methyl-2-(2-oxo-3,4,4a,8a-tetrahydro-1H-quinolin-6-yl)-1-piperidyl]-2-oxo-acetamide (320 mg, 757.36 μmol, 62.19% yield) as 2 fractions: 1ˢᵗ: 120 mg (96% LCMS; contains 4% of cis-isomer). (1st fraction was submitted for chiral separation) 2ⁿᵈ: 200 mg (91% LCMS; contains 9% of cis-isomer).

LCMS(ESI): [M+H]⁺ m/z: calcd 422.2; found 421.2; Rt=1.894 min.

Step 2: The Synthesis of N-(5,6-dimethyl-3-pyridyl)-2-[(2S,5R)-5-methyl-2-(2-oxo-3,4,4a,8a-tetrahydro-1H-Quinolin-6-yl)-1-piperidyl]-2-oxo-acetamide (Compound 632) and N-(5,6-dimethyl-3-pyridyl)-2-[(2R,5S)-5-methyl-2-(2-oxo-3,4,4a,8a-tetrahydro-1H-Quinolin-6-yl)-1-piperidyl]-2-oxo-acetamide (Compound 619

Racemic N-(5,6-dimethyl-3-pyridyl)-2-[(2R,5S)-5-methyl-2-(2-oxo-3,4,4a,8a-tetrahydro-1H-quinolin-6-yl)-1-piperidyl]-2-oxo-acetamide (120 mg, 284.01 μmol) was subjected to chiral HPLC (Chiralpak IA 250*20 mm, 5 mkm; Hexane-IPA-MeOH, 50-25-25, 15 ml/min) to give Compound 632—N-(5,6-dimethyl-3-pyridyl)-2-[(2S,5R)-5-methyl-2-(2-oxo-3,4,4a,8a-tetrahydro-1H-quinolin-6-yl)-1-piperidyl]-2-oxo-acetamide (34 mg, 80.47 μmol, 56.67% yield) (Ret Time: 23.778 min) and Compound 619—N-(5,6-dimethyl-3-pyridyl)-2-[(2R,5S)-5-methyl-2-(2-oxo-3,4,4a,8a-tetrahydro-1H-quinolin-6-yl)-1-piperidyl]-2-oxo-acetamide (36 mg, 85.20 μmol, 60.00% yield) (Ret. time: 35.085 min) as white solids.

Compound 632: RT (IA, Hexane-IPA-MeOH, 50-25-25, 0.6 mL/min)=23.778 min.

¹H NMR (600 MHz, DMSO-d₆) δ 0.95-1.04 (m, 3H), 1.27-1.37 (m, 1H), 1.62-1.74 (m, 1H), 1.81-1.92 (m, 1H), 1.95-2.12 (m, 1H), 2.12-2.17 (m, 1H), 2.17-2.24 (m, 3H), 2.32-2.36 (m, 3H), 2.39-2.45 (m, 2H), 2.78-3.22 (m, 3H), 3.38-3.98 (m, 1H), 4.98-5.54 (m, 1H), 6.78-6.88 (m, 1H), 7.03-7.16 (m, 2H), 7.70-7.85 (m, 1H), 8.38-8.53 (m, 1H), 10.00-10.07 (m, 1H), 10.80-10.95 (m, 1H).

LCMS(ESI): [M+H]⁺ m/z: calcd 420.2; found 421.2; Rt=1.959 min.

Compound 619: RT (IA, Hexane-IPA-MeOH, 50-25-25, 0.6 mL/min)=35.085 min.

¹H NMR (600 MHz, DMSO-d₆) δ 0.96-1.04 (m, 3H), 1.26-1.36 (m, 1H), 1.63-1.74 (m, 1H), 1.79-1.92 (m, 1H), 1.95-2.10 (m, 1H), 2.10-2.17 (m, 1H), 2.17-2.23 (m, 3H), 2.32-2.36 (m, 3H), 2.41-2.46 (m, 2H), 2.81-3.23 (m, 3H), 3.36-3.99 (m, 1H), 4.98-5.56 (m, 1H), 6.79-6.88 (m, 1H), 7.04-7.14 (m, 2H), 7.71-7.83 (m, 1H), 8.39-8.51 (m, 1H), 9.94-10.14 (m, 1H), 10.73-11.07 (m, 1H).

LCMS(ESI): [M+H]⁺ m/z: calcd 420.2; found 421.2; Rt=1.960 min.

Example 75. The Synthesis of N-(5-chloro-6-methyl-3-pyridyl)-2-[(2R,5S)-5-methyl-2-(2-oxo-3,4-dihydro-1H-Quinolin-6-yl)-1-piperidyl]-2-oxo-acetamide (Compound 639), N-(5-chloro-6-methyl-3-pyridyl)-2-[(2R,5S)-5-methyl-2-(2-oxo-3,4-dihydro-1H-Quinolin-6-yl)-1-piperidyl]-2-oxo-acetamide (Compound 727) and N-(5-chloro-6-methyl-3-pyridyl)-2-[(2S,5R)-5-methyl-2-(2-oxo-3,4-dihydro-1H-Quinolin-6-yl)-1-piperidyl]-2-oxo-acetamide (Compound 726

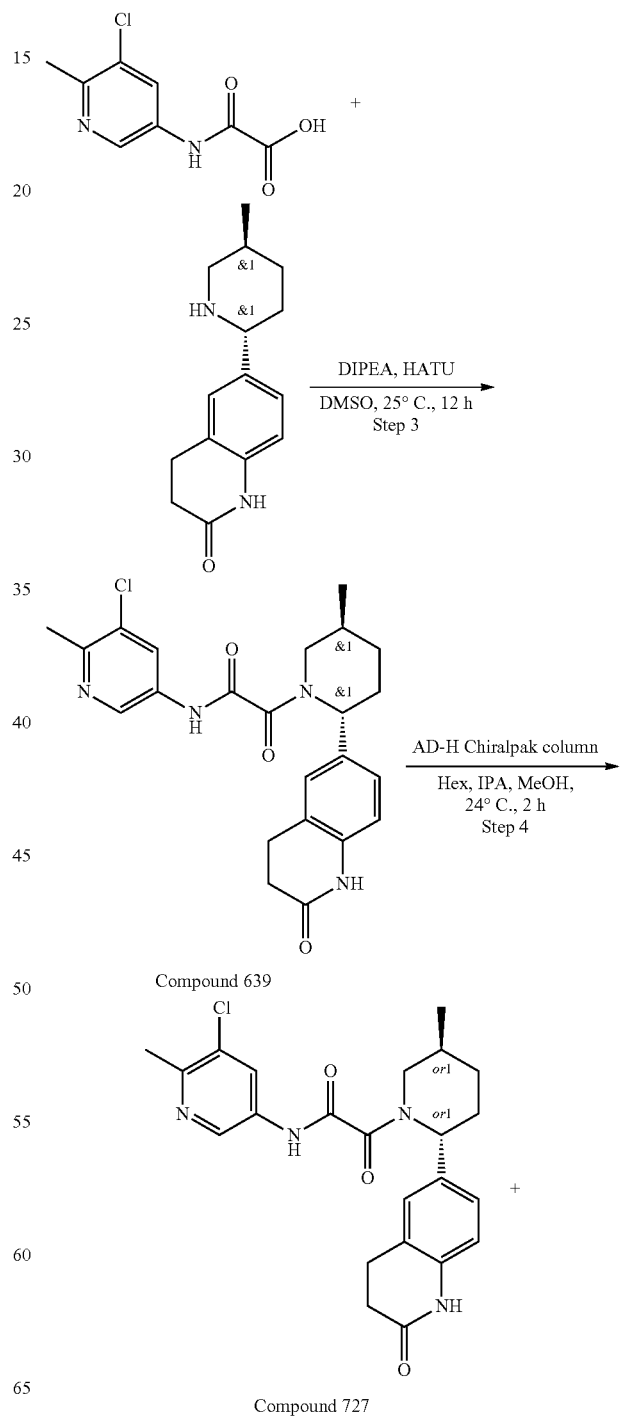

Compound 639

Compound 727

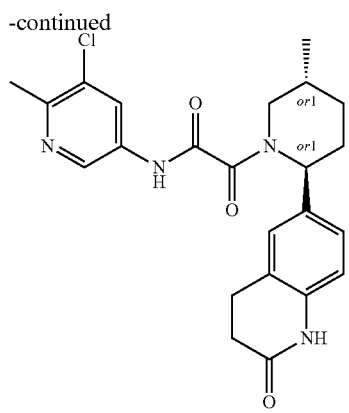

Compound 726

Step 1: N-(5-chloro-6-methyl-3-pyridyl)-2-[(2R,5S)-5-methyl-2-(2-oxo-3,4-dihydro-1H-Quinolin-6-yl)-1-piperidyl]-2-oxo-acetamide (Compound 639

2-[(5-chloro-6-methyl-3-pyridyl)amino]-2-oxo-acetic acid (250 mg, 1.13 mmol, Li+), 6-[(2R,5S)-5-methyl-2-piperidyl]-3,4-dihydro-1H-quinolin-2-one (275.71 mg, 1.13 mmol) and DIPEA (175.01 mg, 1.35 mmol, 235.86 μL) were dissolved in DMSO (3 mL) under gentle heating. HATU (643.60 mg, 1.69 mmol) was added in small portions under vigorous stirring and occasional heating. LCMS of the reaction mixture shows formation of the product; crude reaction mixture was subjected for HPLC (28% 0.5-6.5 min water-acetonitrile; flow 30 ml/min (loading pump 4 ml/min acetonitrile); target mass 440; column SunFire C18 100×19 mm 5 um (R)) and re-purification (61% 0.5-6.5 min water-MeOH; flow: 30 ml/min; (loading pump 4 ml/min MeOH); target mass 440; column SunFire 100×19 mm 5 um (L)) to give N-(5-chloro-6-methyl-3-pyridyl)-2-[(2R,5S)-5-methyl-2-(2-oxo-3,4-dihydro-1H-quinolin-6-yl)-1-piperidyl]-2-oxo-acetamide (50 mg, 113.40 μmol, 10.05% yield) with 2% impurity of N-(5-chloro-6-methyl-3-pyridyl)-N',N'-dimethyl-oxamide.

$^1$H NMR (DMSO-$d_6$, 600 MHz): δ (ppm) 1.00 (m, 3H), 1.32 (m, 1H), 1.70 (m, 1H), 1.86 (m, 1H), 2.01 (m, 1H), 2.15 (m, 1H), 2.39 (m, 4H), 2.60 (m, 1H), 3.03 (m, 3H), 3.61 (m, 1H), 5.28 (m, 1H), 6.83 (m, 1H), 7.08 (m, 2H), 8.15 (m, 1H), 8.58 (m, 1H), 10.02 (m, 1H), 11.15 (m, 1H).

LCMS(ESI): [M+H]$^+$ m/z: calcd 440.2; found 441.4; Rt=2.971 min.

Step 2: The Synthesis of N-(5-chloro-6-methyl-3-pyridyl)-2-[(2R,5S)-5-methyl-2-(2-oxo-3,4-dihydro-1H-Quinolin-6-yl)-1-piperidyl]-2-oxo-acetamide (Compound 727) and N-(5-chloro-6-methyl-3-pyridyl)-2-[(2S,5R)-5-methyl-2-(2-oxo-3,4-dihydro-1H-Quinolin-6-yl)-1-piperidyl]-2-oxo-acetamide (Compound 726

Chiral separation of N-(5-chloro-6-methyl-3-pyridyl)-2-[(2R,5S)-5-methyl-2-(2-oxo-3,4-dihydro-1H-quinolin-6-yl)-1-piperidyl]-2-oxo-acetamide (29.8 mg, 67.59 μmol) was performed using Chiralpak AD-H—III (250*20 mm, 5 mkm) column, Hexane-IPA-MeOH, 50-25-25 as a mobile phase, Rate: 12 mL/min; Column Temperature: 24° C.; Wavelength: 210 nm, 254 nm affording Compound 727—N-(5-chloro-6-methyl-3-pyridyl)-2-[(2R,5S)-5-methyl-2-(2-oxo-3,4-dihydro-1H-quinolin-6-yl)-1-piperidyl]-2-oxo-acetamide (18.63 mg, 42.25 μmol, 62.52% yield) (RT=55.148 min) as yellow solid and Compound 726—N-(5-chloro-6-methyl-3-pyridyl)-2-[(2S,5R)-5-methyl-2-(2-oxo-3,4-dihydro-1H-quinolin-6-yl)-1-piperidyl]-2-oxo-acetamide (19.71 mg, 44.70 μmol, 66.14% yield) (RT=39.309 min) as yellow solid.

Compound 727: RT (AD-H, Hexane-IPA-MeOH, 50-25-25, 0.6 ml/min)=66.902 min $^1$H NMR (DMSO-$d_6$, 600 MHz): δ (ppm) 1.01 (m, 3H), 1.30 (m, 1H), 1.68 (m, 1H), 1.86 (m, 1H), 1.98 (s, 1H), 2.07 (m, 1H), 2.15 (m, 1H), 2.40 (m, 3H), 2.94 (m, 3H), 3.42 (m, 2H), 4.18 (m, 1H), 5.27 (m, 1H), 6.82 (m, 1H), 7.08 (m, 2H), 8.15 (m, 1H), 8.57 (m, 1H), 10.02 (m, 1H), 11.16 (m, 1H).

LCMS(ESI): [M+H]$^+$ m/z: calcd 440.1; found 441.2; Rt=1.129 min.

Compound 726: RT (AD-H, Hexane-IPA-MeOH, 50-25-25, 0.6 ml/min)=47.393 min $^1$H NMR (DMSO-$d_6$, 600 MHz): δ (ppm) 1.03 (m, 3H), 1.31 (m, 1H), 1.69 (m, 1H), 1.86 (m, 1H), 2.03 (m, 1H), 2.15 (m, 1H), 2.41 (m, 3H), 2.86 (m, 3H), 3.43 (m, 2H), 4.18 (m, 1H), 5.28 (m, 1H), 6.82 (m, 1H), 7.08 (m, 2H), 8.15 (m, 1H), 8.58 (m, 1H), 10.02 (m, 1H), 11.15 (m, 1H).

LCMS(ESI): [M+H]$^+$ m/z: calcd 440.1; found 441.2; Rt=1.129 min.

Example 76. The Synthesis of 2-[(2S,5R)-5-methyl-2-(2-oxo-3,4-dihydro-1H-Quinolin-6-yl)-1-piperidyl]-N-[6-methyl-5-(trifluoromethyl)-3-pyridyl]-2-oxo-acetamide (Compound 697) and 2-[(2R,5S)-5-methyl-2-(2-oxo-3,4-dihydro-1H-Quinolin-6-yl)-1-piperidyl]-N-[6-methyl-5-(trifluoromethyl)-3-pyridyl]-2-oxo-acetamide (Compound 698)

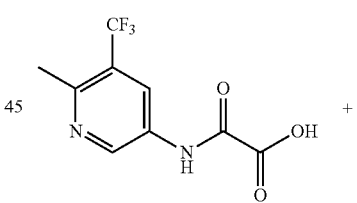

+

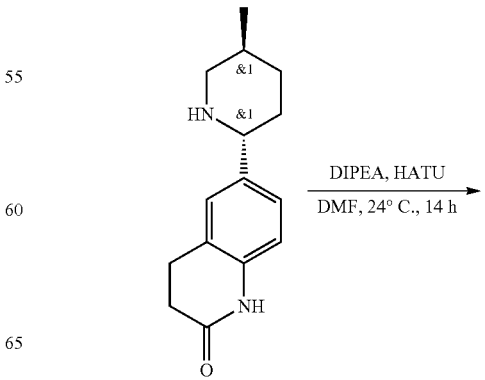

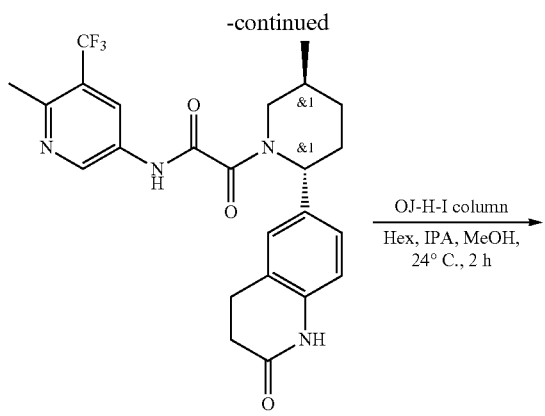

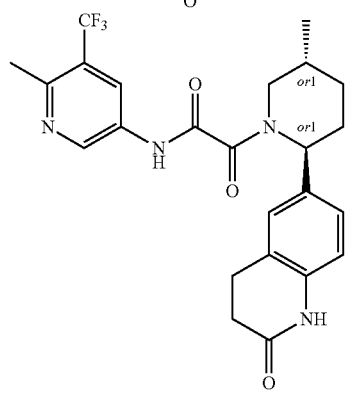

Compound 697

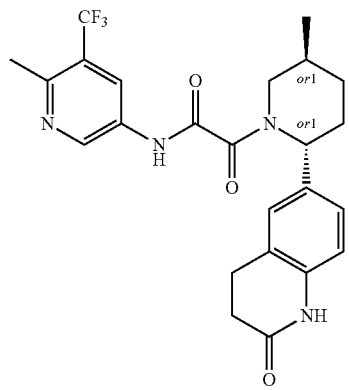

Compound 698

Step 1: The Synthesis of 2-[5-methyl-2-(2-oxo-3,4-dihydro-1H-Quinolin-6-yl)-1-piperidyl]-N-[6-methyl-5-(trifluoromethyl)-3-pyridyl]-2-oxo-acetamide DIPEA (203.12 mg, 1.57 mmol, 273.74 µL) was added to the solution of respective 2-[[6-methyl-5-(trifluoromethyl)-3-pyridyl]amino]-2-oxo-acetic acid (0.13 g, 523.86 µmol) and 6-[(2R,5S)-5-methyl-2-piperidyl]-3,4-dihydro-1H-quinolin-2-one (127.99 mg, 523.86 µmol) in DMF (5 mL). The resulting mixture was stirred for 5 min followed by the addition of HATU (219.11 mg, 576.24 µmol). Then, the reaction mixture was stirred overnight at room temperature. After the completion of the reaction, monitored by LCMS, the resulting suspension was concentrated under reduced pressure. The obtained solid was subjected to HPLC (Waters SunFire C18 20*100 5 mkm column and H₂O-MeCN as an eluent mixture) to afford 2-[5-methyl-2-(2-oxo-3,4-dihydro-1H-quinolin-6-yl)-1-piperidyl]-N-[6-methyl-5-(trifluoromethyl)-3-pyridyl]-2-oxo-acetamide (0.11 g, 231.84 µmol, 44.26% yield).

LCMS(ESI): [M+H]⁺ m/z: calcd 474.2; found 475.2; Rt=3.264 min.

Step 2: The Synthesis of 2-[(2S,5R)-5-methyl-2-(2-oxo-3,4-dihydro-1H-Quinolin-6-yl)-1-piperidyl]-N-[6-methyl-5-(trifluoromethyl)-3-pyridyl]-2-oxo-acetamide (Compound 697) and 2-[(2R,5S)-5-methyl-2-(2-oxo-3,4-dihydro-1H-Quinolin-6-yl)-1-piperidyl]-N-[6-methyl-5-(trifluoromethyl)-3-pyridyl]-2-oxo-acetamide (Compound 698

2-[5-methyl-2-(2-oxo-3,4-dihydro-1H-quinolin-6-yl)-1-piperidyl]-N-[6-methyl-5-(trifluoromethyl)-3-pyridyl]-2-oxo-acetamide (110 mg) was chirally separated using OJ-H—I (250*20, 5 mkm) column, Hexane-IPA-MeOH 60-20-20 as a mobile phase, Flow 13 mL/min affording Compound 697—2-[(2S,5R)-5-methyl-2-(2-oxo-3,4-dihydro-1H-quinolin-6-yl)-1-piperidyl]-N-[6-methyl-5-(trifluoromethyl)-3-pyridyl]-2-oxo-acetamide (32.87 mg, 29.88% yield; RT=9.077 min) and Compound 698—2-[(2R,5S)-5-methyl-2-(2-oxo-3,4-dihydro-1H-quinolin-6-yl)-1-piperidyl]-N-[6-methyl-5-(trifluoromethyl)-3-pyridyl]-2-oxo-acetamide (42.43 mg, 38.57% yield; RT=16.671 min).

Compound 697: RT (OJ-H, Hexane-IPA-MeOH, 70-15-15, 0.6 mL/min)=15.362 min.

¹H NMR (DMSO-d₆, 600 MHz): δ (ppm) 0.99 (m, 3H), 1.30 (m, 1H), 1.70 (m, 1H), 1.87 (m, 1H), 2.02 (m, 1H), 2.16 (m, 1H), 2.43 (m, 2H), 2.56 (m, 3H), 2.86 (m, 3H), 3.78 (m, 1H), 5.29 (m, 1H), 6.83 (m, 1H), 7.08 (t, 2H), 8.39 (m, 1H), 8.87 (m, 1H), 10.02 (m, 1H), 11.29 (m, 1H).

LCMS(ESI): [M+H]⁺ m/z: calcd 474.2; found 475.4; Rt=1.311 min.

Compound 698: RT (OJ-H, Hexane-IPA-MeOH, 70-15-15, 0.6 mL/min)=51.594 min.

¹H NMR (DMSO-d₆, 600 MHz): δ (ppm) 1.00 (m, 3H), 1.32 (m, 1H), 1.69 (m, 1H), 1.88 (m, 1H), 2.04 (m, 1H), 2.16 (m, 1H), 2.37 (m, 1H), 2.43 (m, 2H), 2.56 (m, 3H), 2.99 (m, 2H), 3.79 (m, 1H), 5.30 (m, 1H), 6.83 (m, 1H), 7.08 (m, 2H), 8.39 (m, 1H), 8.88 (m, 1H), 10.02 (m, 1H), 11.28 (m, 1H)

LCMS(ESI): [M+H]⁺ m/z: calcd 474.2; found 475.2; Rt=1.311 min.

Example 77. The Synthesis of 2-[(2R,5S)-5-methyl-2-(2-oxo-3,4-dihydro-1H-Quinolin-6-yl)-1-piperidyl]-N-[5-methyl-6-(trifluoromethyl)-3-pyridyl]-2-oxo-acetamide (Compound 650)

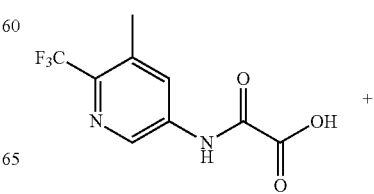

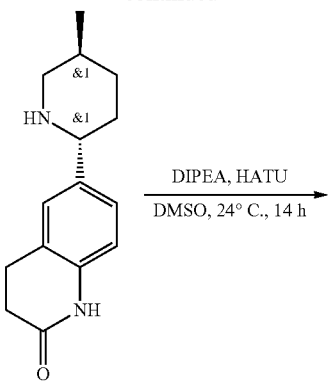

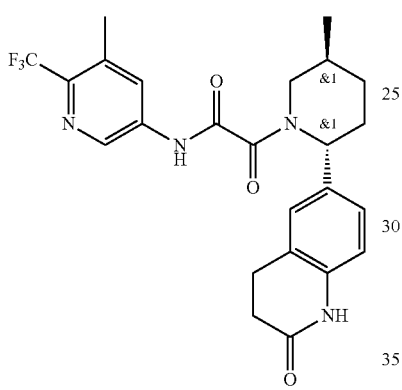

Compound 650

2-[[5-methyl-6-(trifluoromethyl)-3-pyridyl]amino]-2-oxo-acetic acid (0.25 g, 980.01 μmol, Li+), 6-[(2R,5S)-5-methyl-2-piperidyl]-3,4-dihydro-1H-quinolin-2-one (239.45 mg, 980.01 μmol) and DIPEA (151.99 mg, 1.18 mmol, 204.84 μL) were dissolved in DMSO (6 mL) under gentle heating. HATU (558.94 mg, 1.47 mmol) was added in small portions under vigorous stirring and occasional heating. LCMS of the reaction mixture shows formation of the product; crude reaction mixture was subjected for HPLC (37% 0.5-6.5 min water-acetonitrile; flow 30 ml/min (loading pump 4 ml/min acetonitrile); target mass 474; column SunFire C18 100×19 mm 5 um (R)) and repurification (62% 0.5-5 min water-MeOH; flow: 30 ml/min; (loading pump 4 ml/min MeOH); target mass 474; column SunFire 100×19 mm 5 um (L)) to give 2-[(2R,5S)-5-methyl-2-(2-oxo-3,4-dihydro-1H-quinolin-6-yl)-1-piperidyl]-N-[5-methyl-6-(trifluoromethyl)-3-pyridyl]-2-oxo-acetamide (18 mg, 37.94 μmol, 3.87% yield) with 2% impurity of N',N'-dimethyl-N-[5-methyl-6-(trifluoromethyl)-3-pyridyl]oxamide.

$^1$H NMR (DMSO-$d_6$, 600 MHz): δ (ppm) 1.00 (dd, 3H), 1.31 (m, 1H), 1.71 (m, 1H), 1.88 (m, 1H), 2.02 (m, 1H), 2.16 (m, 1H), 2.37 (m, 3H), 2.44 (m, 3H), 2.85 (m, 2H), 3.68 (m, 1H), 5.26 (m, 1H), 6.83 (m, 1H), 7.09 (m, 2H), 8.16 (m, 1H), 8.70 (m, 1H), 10.03 (m, 1H), 11.37 (m, 1H).

LCMS(ESI): [M+H]$^+$ m/z: calcd 474.2; found 475.0; Rt=3.166 min.

Example 78. The Synthesis of rac-N-[5-(difluoromethyl)-6-methyl-3-pyridyl]-2-[(2S,5R)-5-methyl-2-(2-oxo-3,4-dihydro-1H-Quinolin-6-yl)-1-piperidyl]-2-oxo-acetamide (Compound 803) and N-[5-(difluoromethyl)-6-methyl-3-pyridyl]-2-[(2S,5R)-5-methyl-2-(2-oxo-3,4-dihydro-1H-Quinolin-6-yl)-1-piperidyl]-2-oxo-acetamide (Compound 874) and N-[5-(difluoromethyl)-6-methyl-3-pyridyl]-2-[(2R,5S)-5-methyl-2-(2-oxo-3,4-dihydro-1H-Quinolin-6-yl)-1-piperidyl]-2-oxo-acetamide (Compound 903

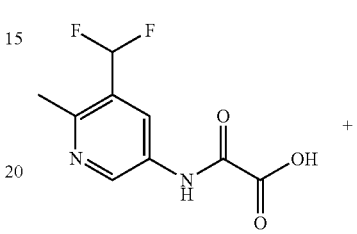

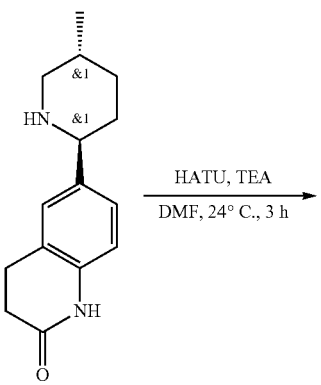

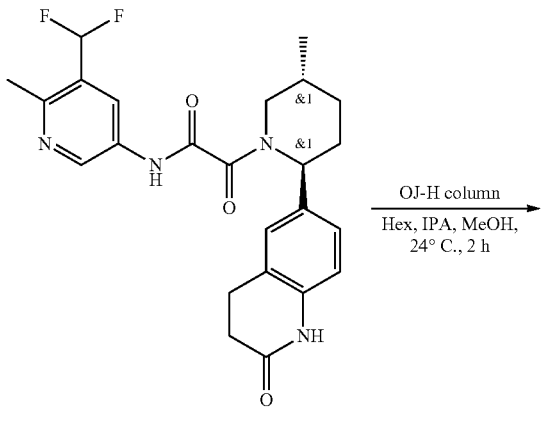

Compound 803

-continued

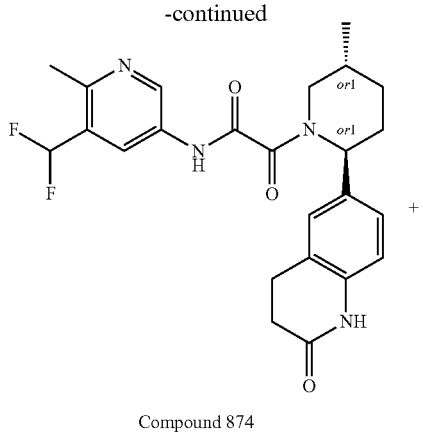

Compound 874

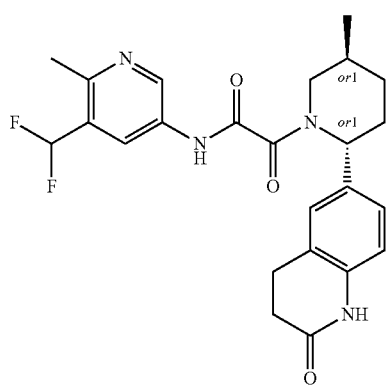

Compound 903

Step 1: The Synthesis of N-[5-(difluoromethyl)-6-methyl-3-pyridyl]-2-[(2S,5R)-5-methyl-2-(2-oxo-3,4-dihydro-1H-Quinolin-6-yl)-1-piperidyl]-2-oxo-acetamide (Compound 803

6-[(2S,5R)-5-methyl-2-piperidyl]-3,4-dihydro-1H-quinolin-2-one (309.14 mg, 1.27 mmol) and TEA (1.28 g, 12.65 mmol, 1.76 mL) were dissolved in DMF (10 mL) and cooled to 0° C., HATU (721.62 mg, 1.90 mmol) was added and the mixture was stirred for 15 min at 0° C. 2-[[5-(difluoromethyl)-6-methyl-3-pyridyl]amino]-2-oxo-acetic acid (0.3 g, 1.27 mmol, Li) was added and the mixture was warmed to r.t. and stirred for 3 hr. 10 ml of Ethyl acetate was added and organic phase was washed with brine three times. Organic phase was dried over Na₂SO₄, filtered and concentrated in vacuo at 45° C. to give crude product which was purified by HPLC (2-10 min 20-30% MeCN/H₂O 30 ml/min (loading pump 4 ml MeCN); column: SunFire C18, 5 micro) to give N-[5-(difluoromethyl)-6-methyl-3-pyridyl]-2-[(2S,5R)-5-methyl-2-(2-oxo-3,4-dihydro-1H-quinolin-6-yl)-1-piperidyl]-2-oxo-acetamide (0.053 g, 116.10 μmol, 9.18% yield).

$^1$H NMR (600 MHz, DMSO-d$_6$) δ 0.99 (d, 3H), 1.29 (m, 1H), 1.89 (m, 4H), 2.16 (m, 2H), 2.43 (s, 3H), 2.84 (m, 3H), 3.96 (m, 1H), 5.06 (m, 1H), 5.25 (d, 1H), 6.85 (m, 1H), 7.09 (m, 2H), 8.27 (s, 1H), 8.78 (s, 1H), 10.04 (m, 1H), 11.22 (m, 1H).

Step 2: The Synthesis of N-[5-(difluoromethyl)-6-methyl-3-pyridyl]-2-[(2S,5R)-5-methyl-2-(2-oxo-3,4-dihydro-1H-quinolin-6-yl)-1-piperidyl]-2-oxo-acetamide (Compound 874) and N-[5-(difluoromethyl)-6-methyl-3-pyridyl]-2-[(2R,5S)-5-methyl-2-(2-oxo-3,4-dihydro-1H-quinolin-6-yl)-1-piperidyl]-2-oxo-acetamide (Compound 903

Chiral separation was performed using Column: Chiralcel OJ-H 250*20, 5-I Hexane-IPA-MeOH, 50-25-25, 12 ml/min, RT=12.43 min, 0.361/injection, 16 mg/injection, 0.6 hours per two runs to give Compound 874—N-[5-(difluoromethyl)-6-methyl-3-pyridyl]-2-[(2S,5R)-5-methyl-2-(2-oxo-3,4-dihydro-1H-quinolin-6-yl)-1-piperidyl]-2-oxo-acetamide (0.02 g, 43.81 μmol, 37.74% yield) and Compound 903—N-[5-(difluoromethyl)-6-methyl-3-pyridyl]-2-[(2R,5S)-5-methyl-2-(2-oxo-3,4-dihydro-1H-quinolin-6-yl)-1-piperidyl]-2-oxo-acetamide (0.017 g, 37.24 μmol, 32.08% yield).

Compound 874: RT (Chiracel OJ-3, Hexane-IPA-MeOH, 50-25-25, 0.15 mL/min)=6.864 min.

$^1$H NMR (600 MHz, DMSO-d$_6$) δ 0.99 (d, 3H), 1.29 (m, 1H), 2.06 (m, 4H), 2.16 (m, 3H), 2.58 (s, 3H), 2.83 (m, 3H), 3.96 (m, 1H), 5.30 (m, 1H), 6.84 (m, 1H), 7.08 (m, 2H), 8.25 (s, 1H), 8.74 (s, 1H), 10.04 (m, 1H), 11.22 (m, 1H).

LCMS(ESI): [M+H]⁺ m/z: calcd 456.2; found 457.2; Rt=2.794 min.

Compound 903: RT (Chiracel OJ-3, Hexane-IPA-MeOH, 50-25-25, 0.15 mL/min)=12.683 min.

$^1$H NMR (600 MHz, DMSO-d$_6$) δ 0.99 (m, 3H), 1.27 (m, 1H), 2.08 (m, 4H), 2.23 (m, 3H), 2.88 (s, 3H), 2.61 (m, 3H), 3.98 (m, 1H), 5.32 (m, 1H), 7.10 (m, 1H), 7.63 (m, 2H), 8.26 (s, 1H), 8.76 (s, 1H), 10.03 (m, 1H), 11.25 (m, 1H).

LCMS(ESI): [M+H]⁺ m/z: calcd 456.2; found 457.2; Rt=2.794 min.

Example 79. The Synthesis of N-[6-(difluoromethyl)-5-methyl-3-pyridyl]-2-[(2S,5R)-5-methyl-2-(2-oxo-3,4-dihydro-1H-Quinolin-6-yl)-1-piperidyl]-2-oxo-acetamide (Compound 641

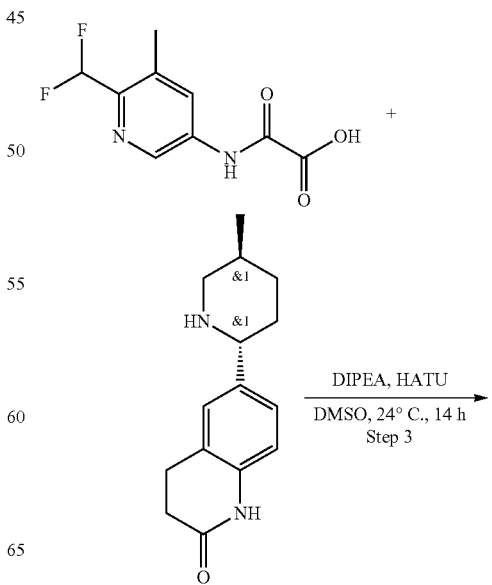

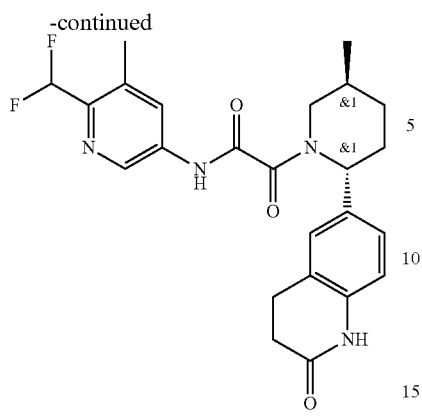

Compound 641

2-[[6-(difluoromethyl)-5-methyl-3-pyridyl]amino]-2-oxo-acetic acid (0.25 g, 1.05 mmol, Li+), 6-[(2R,5S)-5-methyl-2-piperidyl]-3,4-dihydro-1H-quinolin-2-one (257.62 mg, 1.05 mmol) and DIPEA (163.52 mg, 1.27 mmol, 220.38 μL) were dissolved in DMSO (3 mL) under gentle heating. HATU (601.35 mg, 1.58 mmol) was added in small portions under vigorous stirring and occasional heating. LCMS of the reaction mixture shows formation of the product; the reaction mixture was subjected to HPLC (28% 0.5-6.5 min water-acetonitrile; flow 30 ml/min (loading pump 4 ml/min acetonitrile); target mass 440; column SunFire C18 100×19 mm 5 um (R)) and re-purified (56% 0.5-6.5 min water-MeOH; flow: 30 ml/min; (loading pump 4 ml/min MeOH); target mass 456; column SunFire 100×19 mm 5 um (L)) to give N-[6-(difluoromethyl)-5-methyl-3-pyridyl]-2-[(2S,5R)-5-methyl-2-(2-oxo-3,4-dihydro-1H-quinolin-6-yl)-1-piperidyl]-2-oxo-acetamide (18 mg, 39.43 μmol, 3.74% yield) with 3% impurity of N-[6-(difluoromethyl)-5-methyl-3-pyridyl]-N',N'-dimethyl-oxamide.

$^1$H NMR (DMSO-d$_6$, 600 MHz): δ (ppm) 1.00 (m, 3H), 1.32 (m, 1H), 1.69 (m, 1H), 1.88 (m, 1H), 2.03 (m, 1H), 2.16 (m, 1H), 2.36 (m, 3H), 2.42 (m, 2H), 2.87 (m, 2H), 3.23 (m, 1H), 3.68 (m, 1H), 5.27 (m, 1H), 6.83 (m, 1H), 7.03 (m, 3H), 8.04 (m, 1H), 8.65 (m, 1H), 10.03 (m, 1H), 11.23 (m, 1H)

LCMS(ESI): [M+H]$^+$ m/z: calcd 456.2; found 457.4; Rt=2.799 min.

Example 80. The Synthesis of 2-methoxy-5-(2-(5-methyl-2-phenylpiperidin-1-yl)-2-oxoacetamido) Nicotinamide (Compound 308, Compound 291, Compound 333

Compound 322) and rac-2-hydroxy-5-(2-((2R,5S)-5-methyl-2-phenylpiperidin-1-yl)-2-oxoacetamido)Nicotinamide (Compound 494

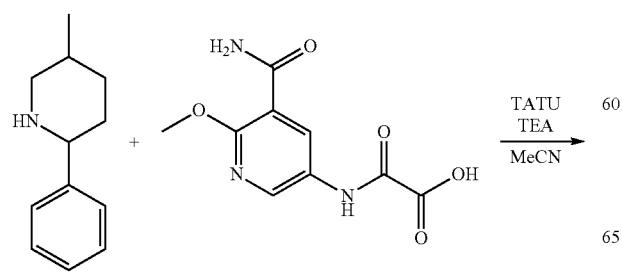

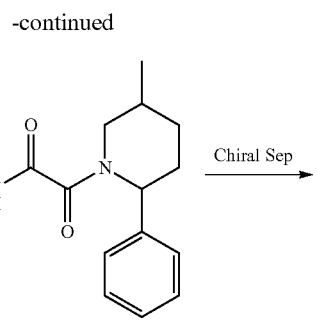

-continued

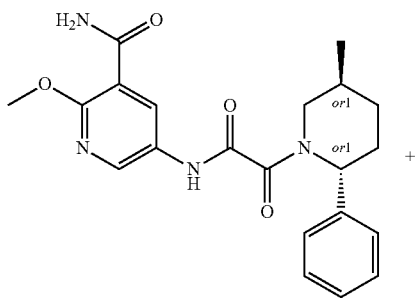

Compound 291

Compound 333

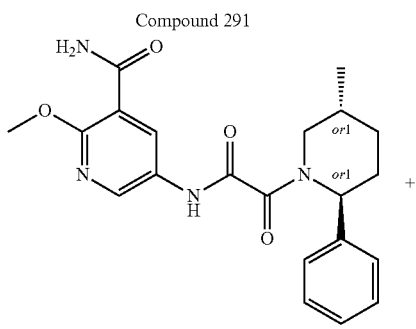

Compound 308

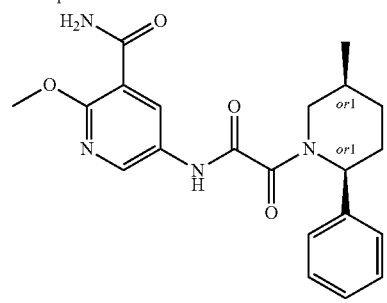

Compound 322

-continued

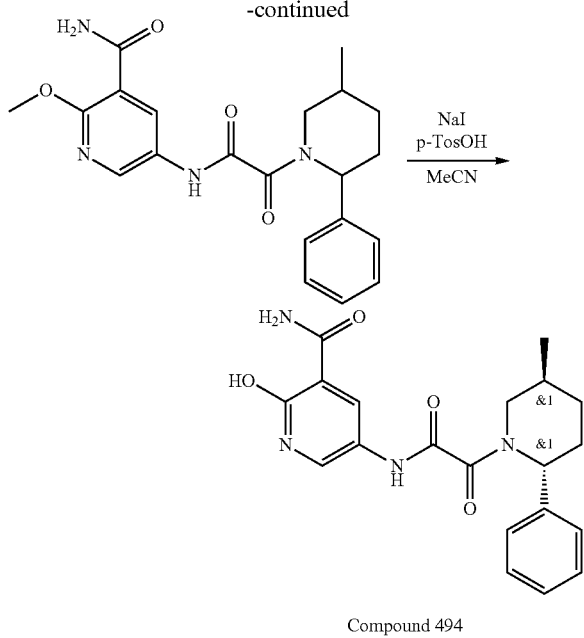

Compound 494

Step 1: Synthesis of 2-methoxy-5-(2-(5-methyl-2-phenylpiperidin-1-yl)-2-oxoacetamido)Nicotinamide 2-[(5-carbamoyl-6-methoxy-3-pyridyl)amino]-2-oxo-acetic acid (0.5 g, 1.47 mmol, Et$_3$N), TATU (567.73 mg, 1.76 mmol), 5-methyl-2-phenyl-piperidine (257.47 mg, 1.47 mmol) and triethylamine (148.64 mg, 1.47 mmol, 204.74 µL) were mixed in dry DMF (25 mL) at 21° C. and the resulting mixture was stirred overnight. The resulting mixture was poured into water, extracted 3 times with EtOAc, combined organics were washed with water, brine and evaporated. The residue was subjected to HPLC (0-5 min 30-80% water-methanol (NH$_3$ 0.1%), flow 30 ml/min (loading pump 4 ml/min Methanol (NH$_3$ 0.1%)), column: YMC-Actus Triart C18 100*20 mm.D. S-5 um). 2-methoxy-5-[[2-(5-methyl-2-phenyl-1-piperidyl)-2-oxo-acetyl]amino]pyridine-3-carboxamide (0.211 g, 532.24 µmol, 36.23% yield) was obtained as a white solid.

$^1$H NMR (500 MHz, CDCl$_3$) δ (ppm) 0.86 (d, 3H), 1.11 (m, 1H), 1.40 (m, 2H), 1.96 (m, 2H), 2.24 (m, 2H), 3.72 (m, 1H), 4.12 (s, 3H), 5.83 (m, 1H), 6.03 (m, 1H), 7.40 (m, 4H), 7.76 (m, 1H), 8.80 (m, 2H), 9.62 (m, 1H).

LCMS(ESI): [M+1]$^+$ m/z: calcd 396.4; found 397.2; Rt=3.545 min.

Step 3: Chiral Separation (Compound 308, Compound 291, Compound 333 and Compound 322

2-methoxy-5-[[2-(5-methyl-2-phenyl-1-piperidyl)-2-oxo-acetyl]amino]pyridine-3-carboxamide (211 mg, 532.24 µmol) was separated using Chiralpak OJ-H 250*20, 5 mkm column; CO$_2$-MeOH, 60-40 as a mobile phase; Flow rate 2 mL/min; affording Compound 308-2-methoxy-5-[[2-[(2R,5R)-5-methyl-2-phenyl-1-piperidyl]-2-oxo-acetyl]amino]pyridine-3-carboxamide (15.38 mg, 38.80 µmol, 7.29% yield) (RT=15.74 min) as a white solid, Compound 291—2-methoxy-5-[[2-[(2R,5S)-5-methyl-2-phenyl-1-piperidyl]-2-oxo-acetyl]amino]pyridine-3-carboxamide (63.97 mg, 161.36 µmol, 30.32% yield) (RT=19.53 min) as a white solid, Compound 333—2-methoxy-5-[[2-[(2S,5R)-5-methyl-2-phenyl-1-piperidyl]-2-oxo-acetyl]amino]pyridine-3-carboxamide (70.77 mg, 178.51 µmol, 33.54% yield) (RT=22.71 min) as a white solid and Compound 322—2-methoxy-5-[[2-[(2S,5S)-5-methyl-2-phenyl-1-piperidyl]-2-oxo-acetyl]amino]pyridine-3-carboxamide (10.02 mg, 25.28 µmol, 4.75% yield) (RT=20.29 min) as a white solid.

Compound 308: $^1$H NMR (500 MHz, DMSO-d$_6$) δ (ppm) 0.70-0.84 (m, 3H), 1.02-1.09 (m, 2H), 1.56-1.82 (m, 2H), 1.82-2.02 (m, 1H), 2.59-2.66 (m, 1H), 3.59-4.35 (m, 4H), 5.17-5.72 (m, 1H), 7.28-7.39 (m, 3H), 7.39-7.46 (m, 2H), 7.70-7.85 (m, 2H), 8.41-8.52 (m, 1H), 8.52-8.63 (m, 1H), 11.03-11.17 (m, 1H).

LCMS(ESI): [M+1]$^+$ m/z: calcd 396.4; found 397.2; Rt=5.305 min.

Compound 291: $^1$H NMR (500 MHz, DMSO-d$_6$) δ (ppm) 1.01-1.07 (m, 3H), 1.30-1.40 (m, 1H), 1.62-1.75 (m, 1H), 1.83-1.99 (m, 1H), 2.04-2.19 (m, 1H), 2.20-2.31 (m, 1H), 2.76-3.24 (m, 1H), 3.48-4.07 (m, 4H), 5.15-5.67 (m, 1H), 7.25-7.33 (m, 2H), 7.34-7.45 (m, 3H), 7.67-7.81 (m, 2H), 8.42-8.50 (m, 1H), 8.50-8.61 (m, 1H), 10.98-11.13 (m, 1H).

LCMS(ESI): [M+1]$^+$ m/z: calcd 396.4; found 397.2; Rt=3.338 min.

Compound 333: $^1$H NMR (500 MHz, DMSO-d$_6$) δ (ppm) 1.04 (m, 3H), 1.35 (m, 1H), 1.67 (m, 1H), 1.89 (m, 1H), 2.06 (m, 1H), 2.23 (m, 1H), 3.47 (m, 1H), 3.96 (m, 3H), 4.22 (m, 1H), 5.40 (m, 1H), 7.32 (m, 2H), 7.40 (m, 3H), 7.75 (m, 2H), 8.47 (m, 1H), 8.55 (m, 1H), 11.04 (m, 1H).

LCMS(ESI): [M+1]$^+$ m/z: calcd 396.4; found 397.2; Rt=3.361 min.

Compound 322: $^1$H NMR (500 MHz, DMSO-d$_6$) δ (ppm) 0.77 (m, 3H), 1.06 (m, 2H), 1.66 (m, 2H), 1.99 (m, 1H), 3.57 (m, 1H), 3.96 (m, 3H), 4.28 (m, 1H), 5.55 (m, 1H), 7.31 (m, 2H), 7.37 (m, 1H), 7.41 (m, 2H), 7.75 (m, 2H), 8.52 (m, 2H), 11.09 (m, 1H).

LCMS(ESI): [M+1]$^+$ m/z: calcd 396.4; found 397.2; Rt=3.405 min.

Step 4: The Synthesis of rac-2-hydroxy-5-(2-((2R,5S)-5-methyl-2-phenylpiperidin-1-yl)-2-oxoacetamido)Nicotinamide (Compound 494

To the stirred solution of the 2-methoxy-5-[[2-[(2R,5S)-5-methyl-2-phenyl-1-piperidyl]-2-oxo-acetyl]amino]pyridine-3-carboxamide (350 mg, 882.86 µmol) in MeCN (15 mL) sodium iodide (423.47 mg, 2.83 mmol, 115.39 µL) was added followed by addition of p-toluenesulfonic acid monohydrate (503.81 mg, 2.65 mmol, 406.29 µL). The resulting mixture was stirred at 80° C. for 2 hr. Acetonitrile was evaporated. The residue was purified by reverse phase HPLC (15-70% 0-1-6 min 0.1% NH$_3$-methanol 30 ml/min (loading pump 4 ml/min 0.1% NH$_3$-methanol); column: YMC-Triart C18 100×20 mm 5 um) to give 2-hydroxy-5-[[2-[(2R,5S)-5-methyl-2-phenyl-1-piperidyl]-2-oxo-acetyl]amino]pyridine-3-carboxamide (53 mg, 138.59 µmol, 15.70% yield).

$^1$H NMR (500 MHz, DMSO-d$_6$) δ (ppm) 0.90-1.11 (m, 3H), 1.26-1.43 (m, 1H), 1.60-1.75 (m, 1H), 1.78-1.95 (m, 1H), 1.95-2.19 (m, 1H), 2.19-2.37 (m, 1H), 2.70-3.26 (m, 1H), 3.47-4.11 (m, 1H), 5.07-5.72 (m, 1H), 7.25-7.46 (m, 5H), 7.59-7.77 (m, 1H), 8.03-8.26 (m, 1H), 8.40-8.60 (m, 1H), 9.01-9.21 (m, 1H), 10.78-10.94 (m, 1H), 12.28-12.57 (m, 1H).

LCMS(ESI): [M+1]$^+$ m/z: calcd 382.4; found 383.2; Rt=2.950 min.

Example 81. The Synthesis of N-(6-amino-5-ethylpyridin-3-yl)-2-(5-methyl-2-phenylpiperidin-1-yl)-2-oxoacetamide (Compound 736 and Compound 709

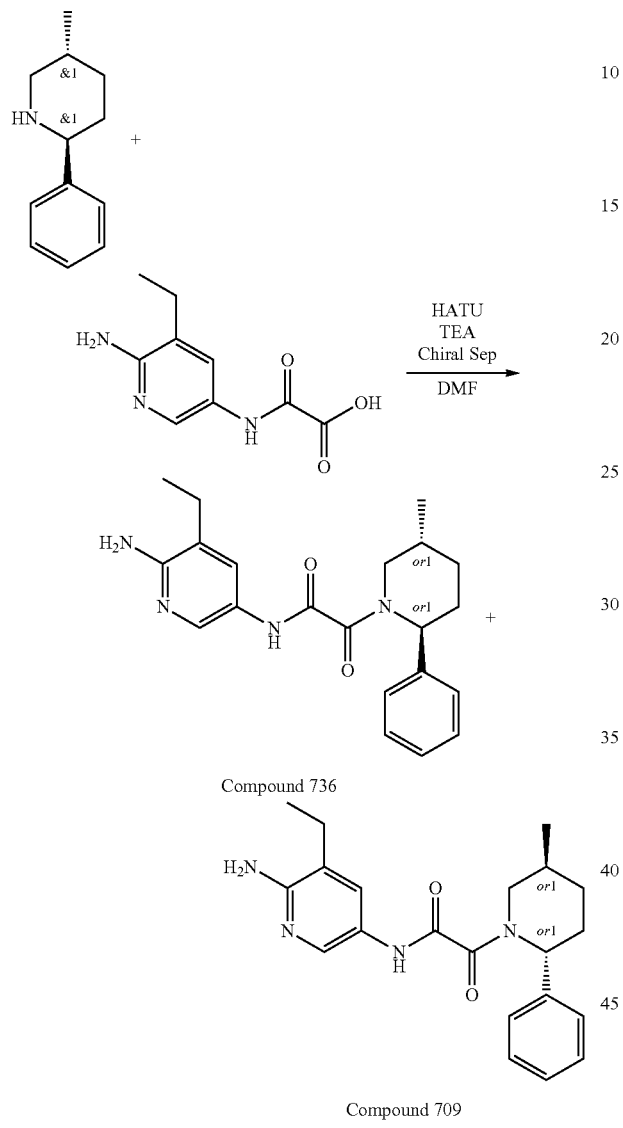

Compound 736

Compound 709

2-[(6-amino-5-ethyl-3-pyridyl)amino]-2-oxo-acetic acid (0.5 g, 2.39 mmol), (2R,5S)-5-methyl-2-phenyl-piperidine (418.90 mg, 2.39 mmol) and DIPEA (926.67 mg, 7.17 mmol, 1.25 mL) were dissolved in DMF (6 mL) under gentle heating. HATU (1.09 g, 2.87 mmol) was added in small portions under vigorous stirring and occasional heating. After the reaction was complete, the mixture was purified by HPLC (35% 0.5-6.5 min water-MeCN; flow 30 ml/min; (loading pump 4 ml/min MeCN); target mass 366; column SunFire C18 100×19 mm 5 um (L)) and re-purified (58% 0.5-6.5 min water-MeOH+NH₃; flow 30 ml/min; (loading pump 4 ml/min MeOH); target mass 366; column SunFire C18 100×19 mm 5 um (L)) to give racemic product, which was subjected to chiral HPLC (OJ-H—I (250*20, 0,5 mkm), Hexane-IPA-MeOH, 60-20-20, 12 ml/min) to give N-(6-amino-5-ethyl-3-pyridyl)-2-[(2R,5S)-5-methyl-2-phenyl-1-piperidyl]-2-oxo-acetamide (0.02 g, 54.58 μmol, 2.28% yield) (with 10% impurity of cis-isomeric piperidine) and N-(6-amino-5-ethyl-3-pyridyl)-2-[(2S,5R)-5-methyl-2-phenyl-1-piperidyl]-2-oxo-acetamide (0.022 g, 60.03 μmol, 2.51% yield).

Ret time for Compound 736 in analytical conditions (column: OJ-H, Hexane-IPA-MeOH, 50-25-25, 0.6 ml/min as mobile phase) 11.91 min and for Compound 709 24.37 min.

Compound 736: Retention time: 11.91 min
¹H NMR (600 MHz, DMSO-d₆) δ (ppm) 0.99 (d, 3H), 1.08 (m, 3H), 1.31 (m, 1H), 1.63 (m, 1H), 1.83 (m, 1H), 2.01 (m, 1H), 2.22 (m, 1H), 2.39 (m, 2H), 3.19 (m, 1H), 4.00 (m, 1H), 5.15 (m, 1H), 5.58 (m, 2H), 7.28 (m, 2H), 7.38 (m, 3H), 7.49 (m, 1H), 8.05 (m, 1H), 10.48 (m, 1H).
LCMS(ESI): [M]⁺ m/z: calcd 366.2; found 367.2; Rt=1.645 min.

Compound 709: Retention time: 24.37 min
¹H NMR (600 MHz, DMSO-d₆) δ (ppm) 0.99 (d, 3H), 1.06 (m, 3H), 1.31 (m, 1H), 1.65 (m, 1H), 1.83 (m, 1H), 2.01 (m, 1H), 2.20 (m, 1H), 2.39 (m, 2H), 3.19 (m, 1H), 4.00 (m, 1H), 5.15 (m, 1H), 5.58 (m, 2H), 7.28 (m, 2H), 7.38 (m, 3H), 7.49 (m, 1H), 8.05 (m, 1H), 10.48 (m, 1H).
LCMS(ESI): [M]⁺ m/z: calcd 366.2; found 367.2; Rt=1.638 min.

Example 82. The Synthesis of Rel-5-[[2-[(2R,5S)-2-(6-amino-3-pyridyl)-5-methyl-1-piperidyl]-2-oxo-acetyl]amino]pyridine-3-carboxamide (Compound 493) and Rel-5-[[2-[(2S,5R)-2-(6-amino-3-pyridyl)-5-methyl-1-piperidyl]-2-oxo-acetyl]amino]pyridine-3-carboxamide (Compound 492

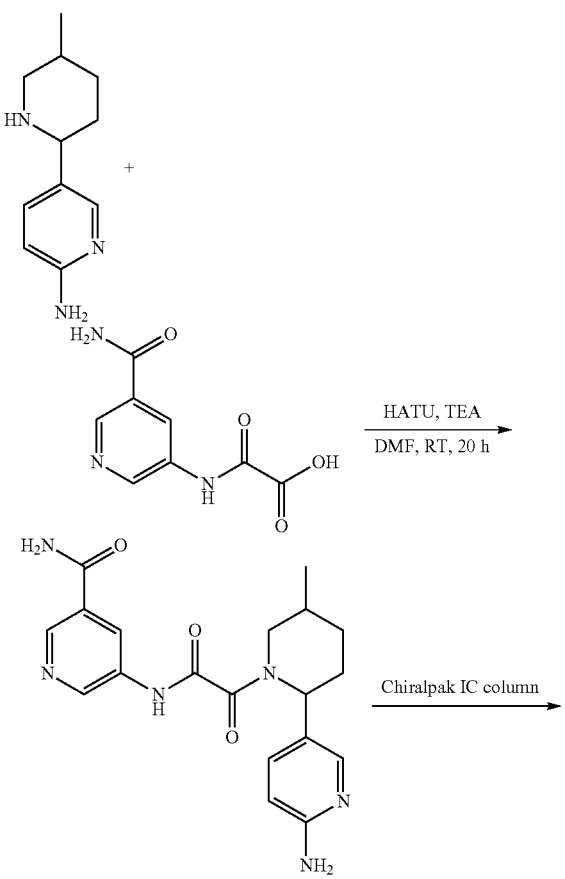

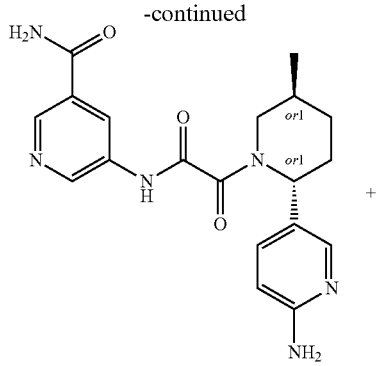

Compound 493

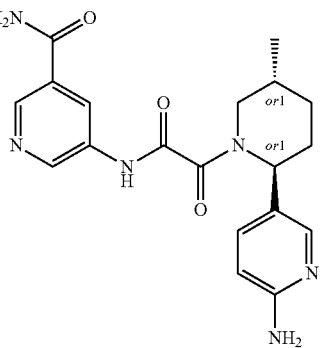

Compound 492

Step 1: The Synthesis of 5-[[2-[2-(6-amino-3-pyridyl)-5-methyl-1-piperidyl]-2-oxo-acetyl]amino]pyridine-3-carboxamide 5-(5-methyl-2-piperidyl)pyridin-2-amine (0.3 g, 1.57 mmol), 2-[(5-carbamoyl-3-pyridyl)amino]-2-oxo-acetic acid (385.24 mg, 1.57 mmol, HCl) and triethylamine (1.59 g, 15.68 mmol, 2.19 mL) were mixed together in DMF (6 mL) and HATU (894.56 mg, 2.35 mmol) was added. The reaction mixture was stirred for 20 hr. The reaction mixture was concentrated in vacuo and the residue was purified by HPLC (2-10 min 35-100% MeCN/H₂O 30 mL/min (loading pump 4 mL MeCN column: SunFire 100*19 mm, 5 microM) to obtain 5-[[2-[2-(6-amino-3-pyridyl)-5-methyl-1-piperidyl]-2-oxo-acetyl]amino]pyridine-3-carboxamide (0.2533 g, 662.37 μmol, 42.23% yield)

LCMS(ESI): [M+H]⁺ m/z: calcd 382.2; found 383.2; Rt=0.778 min.

Step 2: The Synthesis of Rel-5-[[2-[(2R,5S)-2-(6-amino-3-pyridyl)-5-methyl-1-piperidyl]-2-oxo-acetyl]amino]pyridine-3-carboxamide (Compound 493) and Rel-5-[[2-[(2S,5R)-2-(6-amino-3-pyridyl)-5-methyl-1-piperidyl]-2-oxo-acetyl]amino]pyridine-3-carboxamide (Compound 492

5-[[2-[2-(6-amino-3-pyridyl)-5-methyl-1-piperidyl]-2-oxo-acetyl]amino]pyridine-3-carboxamide (0.2533 g, 662.37 μmol) was chirally separated (Column: Chiralpak IC (250*20 mm, 5 mkm); Mobile phase: Hexane-IPA-MeOH-DEA, 40-30-30-0.1. Flow Rate: 12 mL/min; Column Temperature: 40° C.; Wavelength: 205 nm. RetTime (isomer A)=36.22 min and RetTime (isomer B)=53.07 min) to obtain Compound 493—5-[[2-[(2R,5S)-2-(6-amino-3-pyridyl)-5-methyl-1-piperidyl]-2-oxo-acetyl]amino]pyridine-3-carboxamide (27.46 mg, 71.81 μmol, 10.84% yield; Rt=53.07) and Compound 492—5-[[2-[(2S,5R)-2-(6-amino-3-pyridyl)-5-methyl-1-piperidyl]-2-oxo-acetyl]amino]pyridine-3-carboxamide (0.02459 g, 64.30 μmol, 9.71% yield; Rt=36.22)

Compound 493: RT (IC, Hexane-IPA-MeOH, 40-30-30, 0.6 mL/min)=55.490 min.

¹H NMR (600 MHz, DMSO-d₆) δ 0.96-1.05 (m, 3H), 1.27-1.39 (m, 1H), 1.65-1.78 (m, 1H), 1.82-1.92 (m, 1H), 1.94-2.05 (m, 1H), 2.06-2.16 (m, 1H), 2.75-3.25 (m, 1H), 3.38-3.99 (m, 1H), 4.96-5.54 (m, 1H), 5.86 (s, 2H), 6.38-6.51 (m, 1H), 7.24-7.38 (m, 1H), 7.55-7.66 (m, 1H), 7.85 (s, 1H), 8.05-8.22 (m, 1H), 8.43-8.53 (m, 1H), 8.70-8.81 (m, 1H), 8.82-8.91 (m, 1H), 11.05-11.33 (m, 1H).

LCMS(ESI): [M+H]⁺ m/z: calcd 382.2; found 383.2; Rt=2.940 min.

Compound 492: RT (IC, Hexane-IPA-MeOH, 40-30-30, 0.6 mL/min)=33.637 min.

¹H NMR (600 MHz, DMSO-d₆) δ 0.97-1.04 (m, 3H), 1.28-1.39 (m, 1H), 1.66-1.77 (m, 1H), 1.78-1.92 (m, 1H), 1.93-2.05 (m, 1H), 2.05-2.15 (m, 1H), 2.73-3.23 (m, 1H), 3.38-3.98 (m, 1H), 4.95-5.50 (m, 1H), 5.87 (s, 2H), 6.39-6.49 (m, 1H), 7.21-7.38 (m, 1H), 7.56-7.63 (m, 1H), 7.85 (s, 1H), 8.11-8.21 (m, 1H), 8.41-8.50 (m, 1H), 8.73-8.80 (m, 1H), 8.83-8.91 (m, 1H), 11.15-11.37 (m, 1H).

LCMS(ESI): [M+H]⁺ m/z: calcd 382.2; found 383.0; Rt=2.948 min.

Example 83. The Synthesis of Rel-5-[[2-[(2S,5R)-2-[6-(methanesulfonamido)-3-pyridyl]-5-methyl-1-piperidyl]-2-oxo-acetyl]amino]pyridine-3-carboxamide (Compound 1003) and Rel-5-[[2-[(2R,5S)-2-[6-(methanesulfonamido)-3-pyridyl]-5-methyl-1-piperidyl]-2-oxo-acetyl]amino]pyridine-3-carboxamide (Compound 985

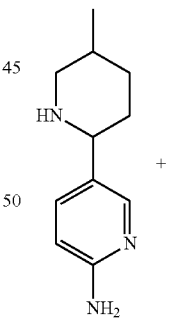

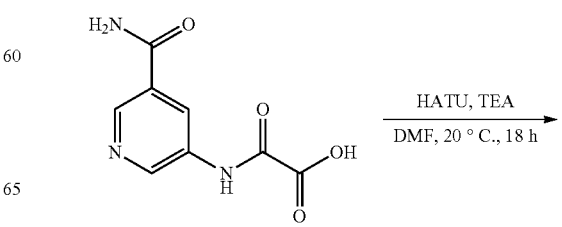

1399

-continued

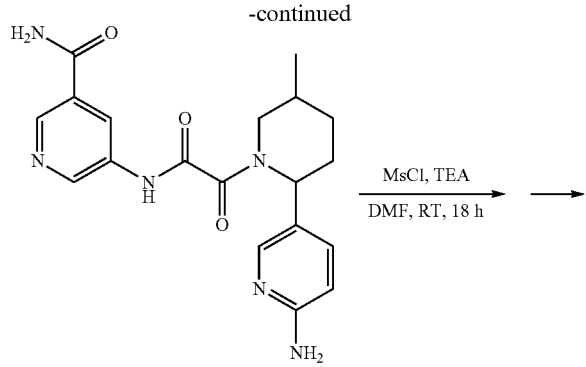

MsCl, TEA
DMF, RT, 18 h

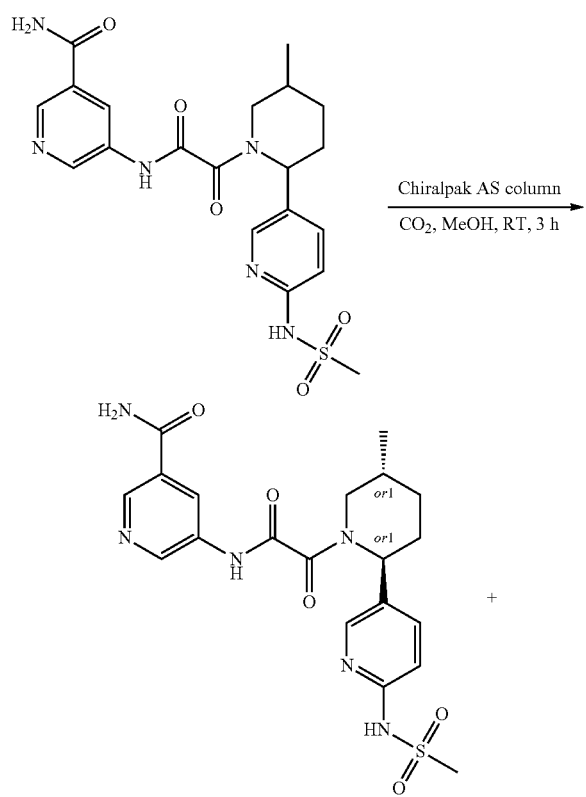

Chiralpak AS column
CO₂, MeOH, RT, 3 h

Compound 1003
+
Compound 985

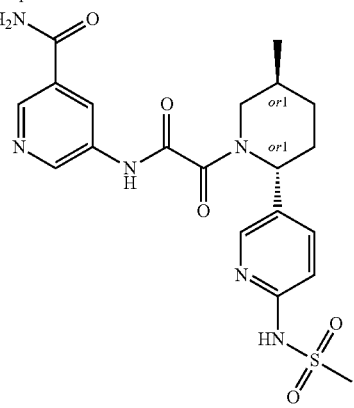

1400

Step 1: The Synthesis of 5-[[2-[2-(6-amino-3-pyridyl)-5-methyl-1-piperidyl]-2-oxo-acetyl]amino]pyridine-3-carboxamide HATU (496.98 mg, 1.31 mmol) was added portionwise at room temperature to a suspension of 2-[(5-carbamoyl-3-pyridyl)amino]-2-oxo-acetic acid (369.19 mg, 1.50 mmol, HCl), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give 5-[[2-[2-(6-amino-3-pyridyl)-5-methyl-1-piperidyl]-2-oxo-acetyl]amino]pyridine-3-carboxamide (1 g, crude).

LCMS(ESI): [M+H]⁺ m/z: calcd 382.2; found 383.2; Rt=0.723 min.

Step 2: The Synthesis of 5-[[2-[2-[6-(methanesulfonamido)-3-pyridyl]-5-methyl-1-piperidyl]-2-oxo-acetyl]amino]pyridine-3-carboxamide Methanesulfonyl chloride (165.07 mg, 1.44 mmol, 111.53 µL) was added dropwise at room temperature to a suspension of 5-[[2-[2-(6-amino-3-pyridyl)-5-methyl-1-piperidyl]-2-oxo-acetyl]amino]pyridine-3-carboxamide (982.28 mg, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: Chromatorex 18 SMB100-5T 100*19 mm 5 um; 0-20% 0-5 min H₂O/MeCN/0.1% TFA, flow: 30 mL/min as mobile phase) to give 5-[[2-[2-[6-(methanesulfonamido)-3-pyridyl]-5-methyl-1-piperidyl]-2-oxo-acetyl]amino]pyridine-3-carboxamide (103 mg, 223.67 µmol, 17.07% yield).

LCMS(ESI): [M+H]⁺ m/z: calcd 460.0; found 461.0; Rt=1.568 min.

Step 3: The Synthesis of rel-5-[[2-[(2S,5R)-2-[6-(methanesulfonamido)-3-pyridyl]-5-methyl-1-piperidyl]-2-oxo-acetyl]amino]pyridine-3-carboxamide (Compound 1003) and rel-5-[[2-[(2R,5S)-2-[6-(methanesulfonamido)-3-pyridyl]-5-methyl-1-piperidyl]-2-oxo-acetyl]amino]pyridine-3-carboxamide (Compound 985

The enantiomers were separated by chiral HPLC (column: AS (250*20, 5 mkm), CO₂-MeOH, 65-35, 50 mL/min make up flow rate—15 mL/min as mobile phase) to give the two individual enantiomers Compound 1003—rel-5-[[2-[(2S,5R)-2-[6-(methanesulfonamido)-3-pyridyl]-5-methyl-1-piperidyl]-2-oxo-acetyl]amino]pyridine-3-carboxamide (30.2 mg, 65.58 µmol, 54.91% yield) RetTime=6.20 min and Compound 985—rel-5-[[2-[(2R,5S)-2-[6-(methanesulfonamido)-3-pyridyl]-5-methyl-1-piperidyl]-2-oxo-acetyl]amino]pyridine-3-carboxamide (25.4 mg, 55.16 µmol, 46.18% yield) RetTime=9.28 min.

Compound 1003: RT (AS-H (250*4.6, 5 mkm), CO₂-MeOH, 65-35, 3.0 mL/min)=3.413 min.

LCMS(ESI): [M+H]⁺ m/z: calcd 460.0; found 461.0; Rt=0.772 min.

Compound 985: RT (AS-H (250*4.6, 5 mkm), CO₂-MeOH, 65-35, 3.0 mL/min)=4.856 min.

LCMS(ESI): [M+H]⁺ m/z: calcd 460.0; found 461.0; Rt=0.772 min.

Example 84. The Synthesis of Rel-5-[[2-[(2S,5R)-2-(6-acetamido-3-pyridyl)-5-methyl-1-piperidyl]-2-oxo-acetyl]amino]pyridine-3-carboxamide (Compound 934) and Rel-5-[[2-[(2R,5S)-2-(6-acetamido-3-pyridyl)-5-methyl-1-piperidyl]-2-oxo-acetyl]amino]pyridine-3-carboxamide (Compound 905

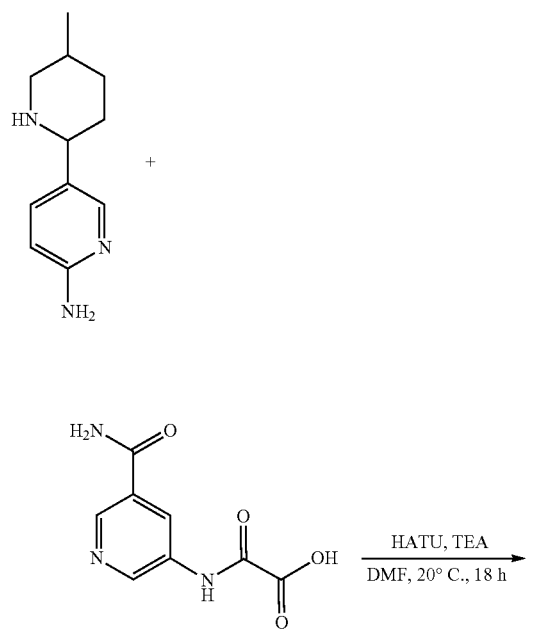

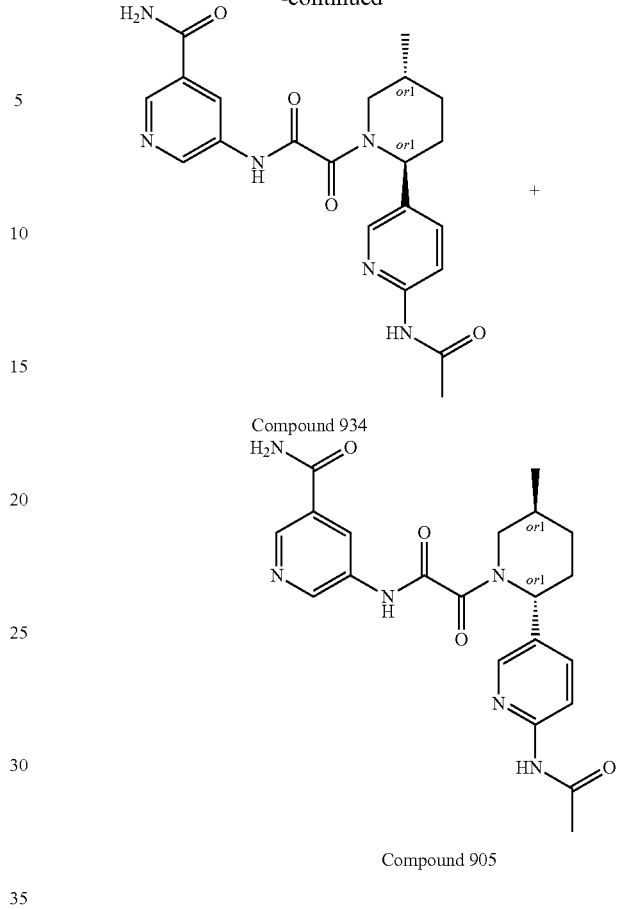

Compound 934

Compound 905

Step 1: The Synthesis of 5-[[2-[2-(6-amino-3-pyridyl)-5-methyl-1-piperidyl]-2-oxo-acetyl]amino]pyridine-3-carboxamide HATU (496.98 mg, 1.31 mmol) was added portionwise at room temperature to a suspension of 2-[(5-carbamoyl-3-pyridyl)amino]-2-oxo-acetic acid (353.14 mg, 1.44 mmol, HCl), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give 5-[[2-[2-(6-amino-3-pyridyl)-5-methyl-1-piperidyl]-2-oxo-acetyl]amino]pyridine-3-carboxamide (1 g, crude).

LCMS(ESI): [M+H]⁺ m/z: calcd 382.2; found 383.2; Rt=0.706 min.

Step 2: The Synthesis of 5-[[2-[2-(6-acetamido-3-pyridyl)-5-methyl-1-piperidyl]-2-oxo-acetyl]amino]pyridine-3-carboxamide Acetyl chloride (113.11 mg, 1.44 mmol, 87.69 μL) was added dropwise at room temperature to a suspension of 5-[[2-[2-(6-amino-3-pyridyl)-5-methyl-1-piperidyl]-2-oxo-acetyl]amino]pyridine-3-carboxamide (705.58 mg, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: YMC Triart C18 100*20 mm.I.D. S-5 um; 0-1-6 min 15-15-50% water-methanol-NH₄OH 0.1%, flow 30 mL/min as mobile phase) to give 5-[[2-[2-(6-

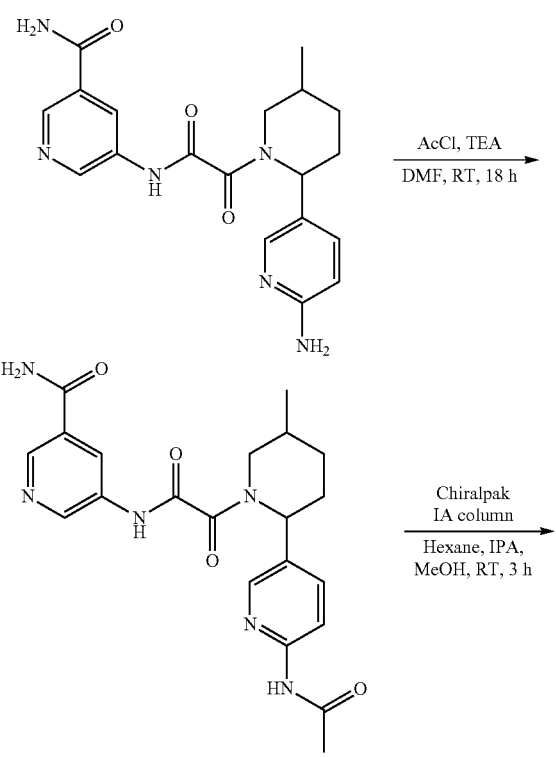

acetamido-3-pyridyl)-5-methyl-1-piperidyl]-2-oxo-acetyl] amino]pyridine-3-carboxamide (113 mg, 266.23 μmol, 20.32% yield).

LCMS(ESI): [M+2H]⁺ m/z: calcd 424.2; found 426.2; Rt=1.735 min.

Step 3: The Synthesis of Rel-5-[[2-[(2S,5R)-2-(6-acetamido-3-pyridyl)-5-methyl-1-piperidyl]-2-oxo-acetyl]amino]pyridine-3-carboxamide (Compound 934) and Re-5-[[2-[(2R,5S)-2-(6-acetamido-3-pyridyl)-5-methyl-1-piperidyl]-2-oxo-acetyl]amino] pyridine-3-carboxamide (Compound 905

The enantiomers were separated by chiral HPLC (column: Chiralpak IA (250*20, 5 mkm), Hexane-IPA-MeOH, 50-25-25, 12 mL/min as mobile phase) to give the two individual enantiomers Compound 934—rel-5-[[2-[(2S,5R)-2-(6-acetamido-3-pyridyl)-5-methyl-1-piperidyl]-2-oxo-acetyl] amino]pyridine-3-carboxamide (41.8 mg, 98.48 μmol, 73.98% yield) RetTime=150.7 min and Compound 905—rel-5-[[2-[(2R,5S)-2-(6-acetamido-3-pyridyl)-5-methyl-1-piperidyl]-2-oxo-acetyl]amino]pyridine-3-carboxamide (35 mg, 82.46 μmol, 61.95% yield) RetTime=256.3 min.

Compound 934: RT (IA (250*4.6, 5 mkm), Hexane-IPA-MeOH, 50-25-25, 0.155 mL/min)=63.750 min.

¹H NMR (DMSO-d₆, 600 MHz): δ (ppm) 1.01 (m, 3H), 1.32 (m, 1H), 1.68 (m, 1H), 1.89 (m, 1H), 2.06 (m, 4H), 2.20 (m, 1H), 3.01 (m, 1H), 3.73 (dd, 1H), 5.37 (m, 1H), 7.59 (m, 1H), 7.71 (m, 1H), 8.10 (m, 2H), 8.24 (m, 1H), 8.46 (m, 1H), 8.75 (m, 1H), 8.86 (m, 1H), 10.49 (s, 1H), 11.22 (m, 1H)

LCMS(ESI): [M+H]⁺ m/z: calcd 424.2; found 425.2; Rt=0.784 min.

Compound 905: RT (IA (250*4.6, 5 mkm), Hexane-IPA-MeOH, 50-25-25, 0.155 mL/min)=98.302 min.

¹H NMR (DMSO-d₆, 600 MHz): δ (ppm) 1.01 (m, 3H), 1.33 (m, 1H), 1.69 (m, 1H), 1.88 (m, 1H), 2.06 (m, 4H), 2.18 (m, 1H), 3.02 (m, 1H), 3.82 (m, 1H), 5.37 (m, 1H), 7.59 (m, 1H), 7.71 (m, 1H), 8.15 (m, 3H), 8.46 (d, 1H), 8.75 (m, 1H), 8.86 (m, 1H), 10.49 (s, 1H), 11.22 (m, 1H).

LCMS(ESI): [M+H]⁺ m/z: calcd 424.2; found 425.0; Rt=0.784 min.

Example 85. The Synthesis of Rel-5-[[2-[(2S,5R)-2-(6-amino-3-pyridyl)-5-methyl-1-piperidyl]-2-oxo-acetyl]amino]-2-methoxy-pyridine-3-carboxamide (Compound 471) and Rel-5-[[2-[(2R,5S)-2-(6-amino-3-pyridyl)-5-methyl-1-piperidyl]-2-oxo-acetyl]amino]-2-methoxy-pyridine-3-carboxamide (Compound 460

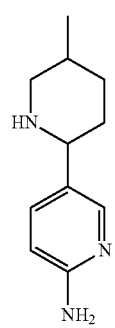

+

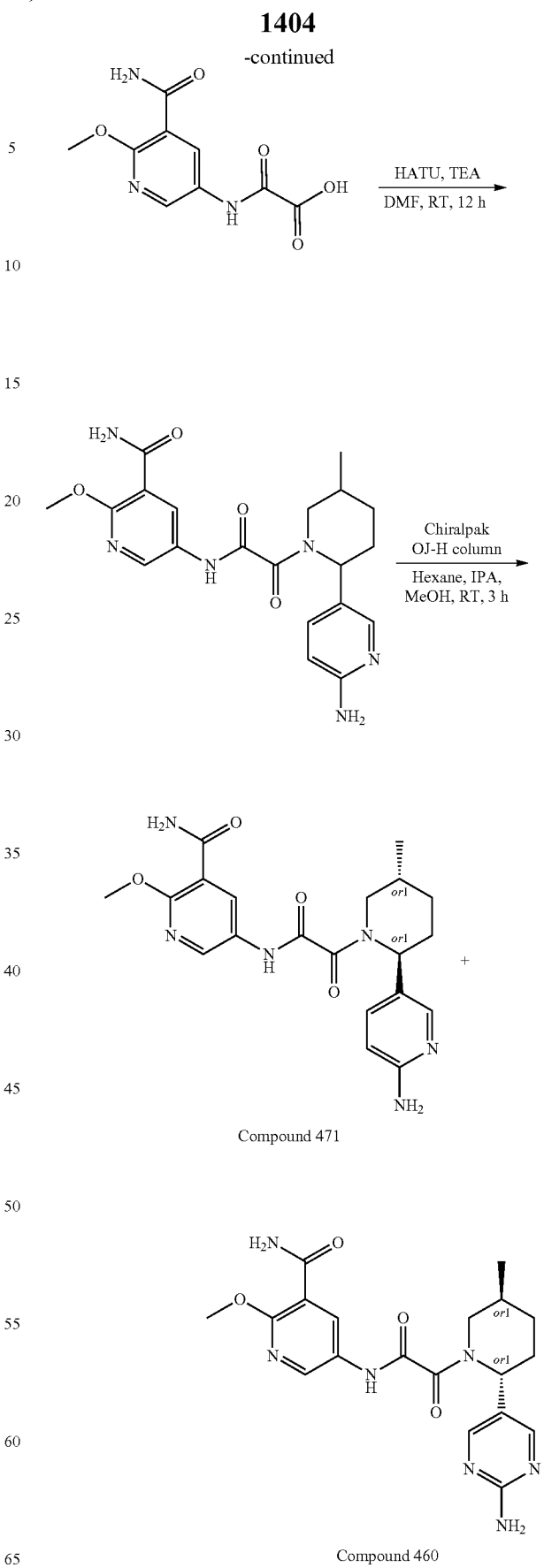

Step 1: The Synthesis of 5-[[2-[(2S,5R)-2-(6-amino-3-pyridyl)-5-methyl-1-piperidyl]-2-oxo-acetyl]amino]-2-methoxy-pyridine-3-carboxamide 5-[(2R,5S)-5-methyl-2-piperidyl]pyridin-2-amine (168.58 mg, 881.38 μmol), 2-[(5-carbamoyl-6-methoxy-3-pyridyl)amino]-2-oxo-acetic acid (300 mg, 881.38 μmol, Et₃N), triethylamine (445.94 mg, 4.41 mmol, 614.24 μL) were mixed in DMF (5 mL) and then HATU (502.69 mg, 1.32 mmol) were added. The resulting mixture was stirred at 25° C. for 12 hr. The mixture was evaporated under reduce pressure and purified with HPLC (2-10 min 35-100% MeCN/H₂O 30 mL/min) to obtain 5-[[2-[(2S,5R)-2-(6-amino-3-pyridyl)-5-methyl-1-piperidyl]-2-oxo-acetyl]amino]-2-methoxy-pyridine-3-carboxamide (61.6 mg, 149.35 μmol, 16.95% yield).

LCMS(ESI): [M+H]⁺ m/z: calcd 412.2; found 413.2; Rt=0.869 min.

Step 2: The Synthesis of Rel-5-[[2-[(2S,5R)-2-(6-amino-3-pyridyl)-5-methyl-1-piperidyl]-2-oxo-acetyl]amino]-2-methoxy-pyridine-3-carboxamide (Compound 471) and Rel-5-[[2-[(2R,5S)-2-(6-amino-3-pyridyl)-5-methyl-1-piperidyl]-2-oxo-acetyl]amino]-2-methoxy-pyridine-3-carboxamide (Compound 460

The mixture of diastereomers was separated by chiral chromatography (Column: Chiralcel OD-H (250*30 mm, 5 m); Mobile phase: Hexane-IPA-MeOH, 70-15-15 Flow Rate: 25 mL/min; Column Temperature: 24° C.; Wavelength: 205 nm, 245 nm, 300 nm; RetTime (isomer A)=20.78 min; RetTime (isomers B)=29.49 min) to obtain Compound 471—rel-5-[[2-[(2S,5R)-2-(6-amino-3-pyridyl)-5-methyl-1-piperidyl]-2-oxo-acetyl]amino]-2-methoxy-pyridine-3-carboxamide (10.95 mg, 26.55 μmol, 17.78% yield) (RT=20.78) and Compound 460—rel-5-[[2-[(2R,5S)-2-(6-amino-3-pyridyl)-5-methyl-1-piperidyl]-2-oxo-acetyl]amino]-2-methoxy-pyridine-3-carboxamide (10.13 mg, 24.56 μmol, 16.44% yield) (RT=29.49).

Compound 460: RT (OD-3, Hexane-IPA-MeOH, 70-15-15, 0.6 mL/min)=12.283 min.

¹H NMR (600 MHz, DMSO-d₆) δ 0.96-1.04 (m, 3H), 1.26-1.38 (m, 1H), 1.64-1.74 (m, 1H), 1.74-1.90 (m, 1H), 1.90-2.05 (m, 1H), 2.05-2.16 (m, 1H), 2.70-3.26 (m, 1H), 3.39-3.98 (m, 4H), 4.95-5.50 (m, 1H), 5.86 (s, 2H), 6.39-6.47 (m, 1H), 7.24-7.37 (m, 1H), 7.69-7.76 (m, 2H), 7.84 (s, 1H), 8.40-8.47 (m, 1H), 8.50-8.58 (m, 1H), 10.87-11.11 (m, 1H).

LCMS(ESI): [M+H]⁺ m/z: calcd 412.2; found 413.2; Rt=3.290 min.

Compound 471: RT (OD-3, Hexane-IPA-MeOH, 70-15-15, 0.6 mL/min)=8.759 min.

¹H NMR (600 MHz, DMSO-d₆) δ 0.96-1.03 (m, 3H), 1.23-1.37 (m, 1H), 1.66-1.76 (m, 1H), 1.78-2.06 (m, 2H), 2.06-2.15 (m, 1H), 2.74-3.21 (m, 1H), 3.36-3.91 (m, 1H), 3.92-3.97 (m, 3H), 4.93-5.49 (m, 1H), 5.86 (s, 2H), 6.41-6.48 (m, 1H), 7.25-7.37 (m, 1H), 7.68-7.78 (m, 2H), 7.84 (s, 1H), 8.40-8.47 (m, 1H), 8.49-8.58 (m, 1H), 10.94-11.03 (m, 1H).

LCMS(ESI): [M+H]⁺ m/z: calcd 412.2; found 413.2; Rt=3.288 min.

Example 86. The Synthesis of Rel-5-[[2-[(2S,5R)-2-[6-(methanesulfonamido)-3-pyridyl]-5-methyl-1-piperidyl]-2-oxo-acetyl]amino]-2-methoxy-pyridine-3-carboxamide (Compound 986) and Rel-5-[[2-[(2R,5S)-2-[6-(methanesulfonamido)-3-pyridyl]-5-methyl-1-piperidyl]-2-oxo-acetyl]amino]-2-methoxy-pyridine-3-carboxamide (Compound 999

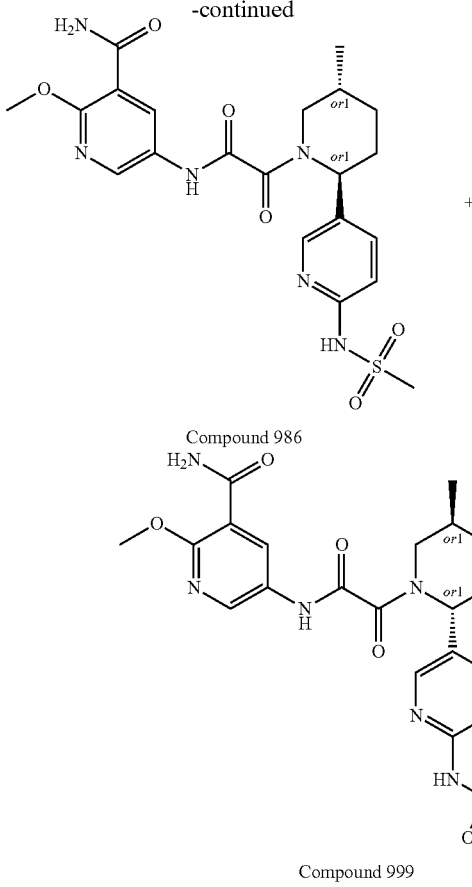

Compound 986

Compound 999

Step 1: The Synthesis of 5-[[2-[2-(6-amino-3-pyridyl)-5-methyl-1-piperidyl]-2-oxo-acetyl]amino]-2-methoxy-pyridine-3-carboxamide HATU (496.98 mg, 1.31 mmol) was added portionwise at room temperature to a suspension of 2-[(5-carbamoyl-6-methoxy-3-pyridyl)amino]-2-oxo-acetic acid (359.52 mg, 1.50 mmol), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give 5-[[2-[2-(6-amino-3-pyridyl)-5-methyl-1-piperidyl]-2-oxo-acetyl]amino]-2-methoxy-pyridine-3-carboxamide (1 g, crude).

LCMS(ESI): [M+H]$^+$ m/z: calcd 412.2; found 413.2; Rt=0.819 min.

Step 2: The Synthesis of 5-[[2-[2-[6-(methanesulfonamido)-3-pyridyl]-5-methyl-1-piperidyl]-2-oxo-acetyl]amino]-2-methoxy-pyridine-3-carboxamide Methanesulfonyl chloride (165.07 mg, 1.44 mmol, 111.53 μL) was added dropwise at room temperature to a suspension of 5-[[2-[2-(6-amino-3-pyridyl)-5-methyl-1-piperidyl]-2-oxo-acetyl]amino]-2-methoxy-pyridine-3-carboxamide (1.10 g, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: Chromatorex 18 SMB100-5T 100*19 mm 5 um; 0-40% 0-5 min H$_2$O/MeCN/ 0.1% TFA, flow: 30 mL/min as mobile phase) to give 5-[[2-[2-[6-(methanesulfonamido)-3-pyridyl]-5-methyl-1-piperidyl]-2-oxo-acetyl]amino]-2-methoxy-pyridine-3-carboxamide (158 mg, 322.10 μmol, 24.59% yield).

LCMS(ESI): [M+H]$^+$ m/z: calcd 490.2; found 491.2; Rt=1.857 min.

Step 3: The Synthesis of Rel-5-[[2-[(2S,5R)-2-[6-(methanesulfonamido)-3-pyridyl]-5-methyl-1-piperidyl]-2-oxo-acetyl]amino]-2-methoxy-pyridine-3-carboxamide (Compound 986) and Rel-5-[[2-[(2R,5S)-2-[6-(methanesulfonamido)-3-pyridyl]-5-methyl-1-piperidyl]-2-oxo-acetyl]amino]-2-methoxy-pyridine-3-carboxamide (Compound 999

The enantiomers were separated by chiral HPLC (column: AS (250*20, 5 mkm), CO$_2$-MeOH, 60-40, 50 mL/min make up flow rate—15 mL/min as mobile phase) to give the two individual enantiomers Compound 986—rel-5-[[2-[(2S,5R)-2-[6-(methanesulfonamido)-3-pyridyl]-5-methyl-1-piperidyl]-2-oxo-acetyl]amino]-2-methoxy-pyridine-3-carboxamide (29.4 mg, 59.93 μmol, 37.22% yield) RetTime=6.52 min and Compound 999—rel-5-[[2-[(2R,5S)-2-[6-(methanesulfonamido)-3-pyridyl]-5-methyl-1-piperidyl]-2-oxo-acetyl]amino]-2-methoxy-pyridine-3-carboxamide (30.7 mg, 62.59 μmol, 38.86% yield) RetTime=8.26 min.

Compound 986: RT (AS (250*20, 5 mkm), CO$_2$-MeOH, 60-40, 2.0 mL/min)=4.972 min.

LCMS(ESI): [M+H]$^+$ m/z: calcd 490.2; found 491.2; Rt=0.827 min.

Compound 999: RT (AS (250*20, 5 mkm), CO$_2$-MeOH, 60-40, 2.0 mL/min)=6.367 min.

LCMS(ESI): [M+H]$^+$ m/z: calcd 490.2; found 491.2; Rt=0.828 min.

Example 87. The Synthesis of Rel-5-[[2-[(2S,5R)-2-(6-acetamido-3-pyridyl)-5-methyl-1-piperidyl]-2-oxo-acetyl]amino]-2-methoxy-pyridine-3-carboxamide (Compound 930) and Rel-5-[[2-[(2R,5S)-2-(6-acetamido-3-pyridyl)-5-methyl-1-piperidyl]-2-oxo-acetyl]amino]-2-methoxy-pyridine-3-carboxamide (Compound 910

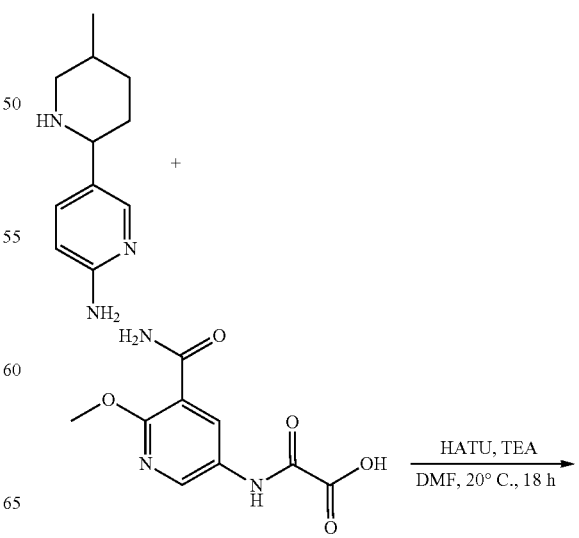

1409

-continued

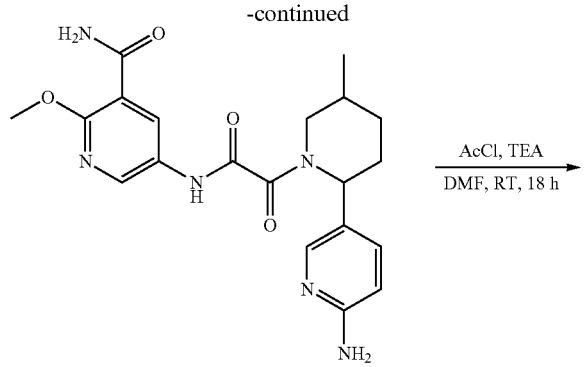

AcCl, TEA
DMF, RT, 18 h
→

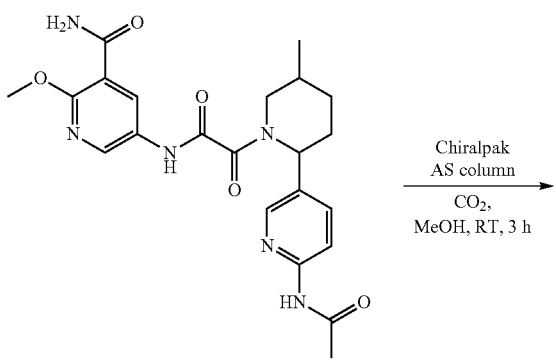

Chiralpak
AS column
CO₂,
MeOH, RT, 3 h
→

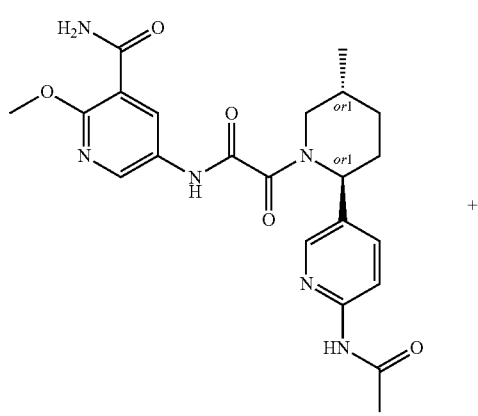

Compound 930
+

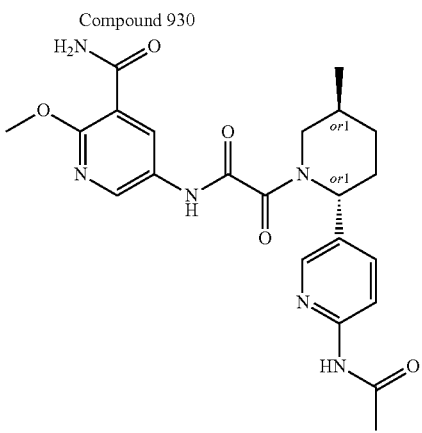

Compound 910

1410

Step 1: The Synthesis of 5-[[2-[2-(6-amino-3-pyridyl)-5-methyl-1-piperidyl]-2-oxo-acetyl]amino]-2-methoxy-pyridine-3-carboxamide HATU (496.98 mg, 1.31 mmol) was added portionwise at room temperature to a suspension of 2-[(5-carbamoyl-6-methoxy-3-pyridyl)amino]-2-oxo-acetic acid (359.52 mg, 1.50 mmol), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give 5-[[2-[2-(6-amino-3-pyridyl)-5-methyl-1-piperidyl]-2-oxo-acetyl]amino]-2-methoxy-pyridine-3-carboxamide (1 g, crude).

LCMS(ESI): [M+H]⁺ m/z: calcd 412.2; found 413.2; Rt=0.788 min.

Step 2: The Synthesis of 5-[[2-[2-(6-acetamido-3-pyridyl)-5-methyl-1-piperidyl]-2-oxo-acetyl]amino]-2-methoxy-pyridine-3-carboxamide Acetyl chloride (113.11 mg, 1.44 mmol, 87.69 µL) was added dropwise at room temperature to a suspension of 5-[[2-[2-(6-amino-3-pyridyl)-5-methyl-1-piperidyl]-2-oxo-acetyl]amino]-2-methoxy-pyridine-3-carboxamide (1.17 g, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: Chromatorex 18 SMB100-5T 100*19 mm 5 um; 5-22% 0-5 min H₂O/MeCN/0.1% TFA, flow: 30 mL/min as mobile phase) to give 5-[[2-[2-(6-acetamido-3-pyridyl)-5-methyl-1-piperidyl]-2-oxo-acetyl]amino]-2-methoxy-pyridine-3-carboxamide (77 mg, 169.43 µmol, 12.93% yield).

LCMS(ESI): [M+H]⁺ m/z: calcd 454.2; found 455.4; Rt=2.009 min.

Step 3: The Synthesis of Rel-5-[[2-[(2S,5R)-2-(6-acetamido-3-pyridyl)-5-methyl-1-piperidyl]-2-oxo-acetyl]amino]-2-methoxy-pyridine-3-carboxamide (Compound 930) and Re-5-[[2-[(2R,5S)-2-(6-acetamido-3-pyridyl)-5-methyl-1-piperidyl]-2-oxo-acetyl]amino]-2-methoxy-pyridine-3-carboxamide (Compound 910

The enantiomers were separated by chiral HPLC (column: AS (250*20, 10 mkm), CO₂-MeOH, 65-35, 50 mL/min make up flow rate—20 mL/min as mobile phase) to give the two individual enantiomers Compound 930—rel-5-[[2-[(2S,5R)-2-(6-acetamido-3-pyridyl)-5-methyl-1-piperidyl]-2-oxo-acetyl]amino]-2-methoxy-pyridine-3-carboxamide (19 mg, 41.81 µmol, 49.35% yield) RetTime=7.33 min and Compound 910—rel-5-[[2-[(2R,5S)-2-(6-acetamido-3-pyridyl)-5-methyl-1-piperidyl]-2-oxo-acetyl]amino]-2-methoxy-pyridine-3-carboxamide (16 mg, 35.21 µmol, 41.56% yield) RetTime=9.85 min.

Compound 930: RT (IC (250*4.6, 5 mkm), IPA-MeOH, 50-50, 0.6 mL/min)=25.671 min.

¹H NMR (DMSO-d₆, 600 MHz): δ (ppm) 1.01 (m, 3H), 1.34 (m, 1H), 1.68 (m, 1H), 1.89 (m, 1H), 2.06 (m, 4H), 2.18 (m, 1H), 3.09 (m, 1H), 3.93 (m, 4H), 5.36 (m, 1H), 7.72 (m, 3H), 8.05 (m, 1H), 8.23 (m, 1H), 8.47 (m, 2H), 10.48 (s, 1H), 11.01 (m, 1H).

LCMS(ESI): [M+H]⁺ m/z: calcd 454.2; found 455.2; Rt=1.032 min.

Compound 910: RT (IC (250*4.6, 5 mkm), IPA-MeOH, 50-50, 0.6 mL/min)=18.813 min.

1411

$^1$H NMR (DMSO-$d_6$, 600 MHz): δ (ppm) 1.01 (m, 3H), 1.35 (m, 1H), 1.68 (m, 1H), 1.89 (m, 1H), 2.06 (m, 4H), 2.18 (m, 1H), 3.09 (m, 1H), 3.77 (m, 4H), 5.36 (m, 1H), 7.71 (m, 3H), 8.04 (m, 1H), 8.23 (m, 1H), 8.47 (m, 2H), 10.48 (s, 1H), 11.01 (m, 1H).

LCMS(ESI): [M+H]$^+$ m/z: calcd 454.2; found 455.2; Rt=1.030 min.

Example 88. The Synthesis of Rel-5-[[2-[(2R,5S)-5-methyl-2-[6-(methylamino)-3-pyridyl]-1-piperidyl]-2-oxo-acetyl]amino]pyridine-3-carboxamide (Compound 444) and Rel-5-[[2-[(2S,5R)-5-methyl-2-[6-(methylamino)-3-pyridyl]-1-piperidyl]-2-oxo-acetyl]amino]pyridine-3-carboxamide (Compound 443

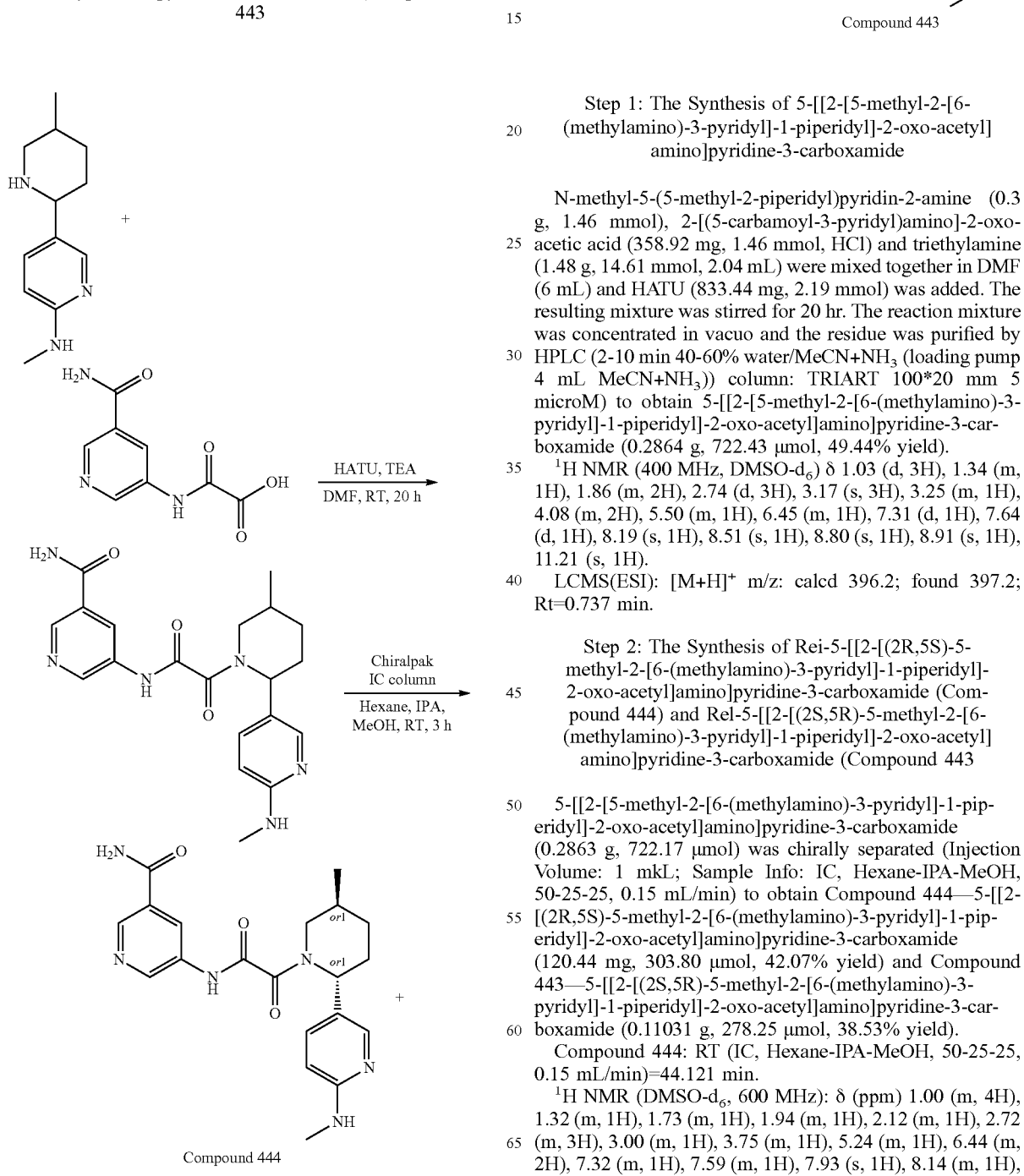

Compound 443

Step 1: The Synthesis of 5-[[2-[5-methyl-2-[6-(methylamino)-3-pyridyl]-1-piperidyl]-2-oxo-acetyl]amino]pyridine-3-carboxamide N-methyl-5-(5-methyl-2-piperidyl)pyridin-2-amine (0.3 g, 1.46 mmol), 2-[(5-carbamoyl-3-pyridyl)amino]-2-oxo-acetic acid (358.92 mg, 1.46 mmol, HCl) and triethylamine (1.48 g, 14.61 mmol, 2.04 mL) were mixed together in DMF (6 mL) and HATU (833.44 mg, 2.19 mmol) was added. The resulting mixture was stirred for 20 hr. The reaction mixture was concentrated in vacuo and the residue was purified by HPLC (2-10 min 40-60% water/MeCN+NH$_3$ (loading pump 4 mL MeCN+NH$_3$)) column: TRIART 100*20 mm 5 microM) to obtain 5-[[2-[5-methyl-2-[6-(methylamino)-3-pyridyl]-1-piperidyl]-2-oxo-acetyl]amino]pyridine-3-carboxamide (0.2864 g, 722.43 μmol, 49.44% yield).

$^1$H NMR (400 MHz, DMSO-$d_6$) δ 1.03 (d, 3H), 1.34 (m, 1H), 1.86 (m, 2H), 2.74 (d, 3H), 3.17 (s, 3H), 3.25 (m, 1H), 4.08 (m, 2H), 5.50 (m, 1H), 6.45 (m, 1H), 7.31 (d, 1H), 7.64 (d, 1H), 8.19 (s, 1H), 8.51 (s, 1H), 8.80 (s, 1H), 8.91 (s, 1H), 11.21 (s, 1H).

LCMS(ESI): [M+H]$^+$ m/z: calcd 396.2; found 397.2; Rt=0.737 min.

Step 2: The Synthesis of Rel-5-[[2-[(2R,5S)-5-methyl-2-[6-(methylamino)-3-pyridyl]-1-piperidyl]-2-oxo-acetyl]amino]pyridine-3-carboxamide (Compound 444) and Rel-5-[[2-[(2S,5R)-5-methyl-2-[6-(methylamino)-3-pyridyl]-1-piperidyl]-2-oxo-acetyl]amino]pyridine-3-carboxamide (Compound 443

5-[[2-[5-methyl-2-[6-(methylamino)-3-pyridyl]-1-piperidyl]-2-oxo-acetyl]amino]pyridine-3-carboxamide (0.2863 g, 722.17 μmol) was chirally separated (Injection Volume: 1 mkL; Sample Info: IC, Hexane-IPA-MeOH, 50-25-25, 0.15 mL/min) to obtain Compound 444—5-[[2-[(2R,5S)-5-methyl-2-[6-(methylamino)-3-pyridyl]-1-piperidyl]-2-oxo-acetyl]amino]pyridine-3-carboxamide (120.44 mg, 303.80 μmol, 42.07% yield) and Compound 443—5-[[2-[(2S,5R)-5-methyl-2-[6-(methylamino)-3-pyridyl]-1-piperidyl]-2-oxo-acetyl]amino]pyridine-3-carboxamide (0.11031 g, 278.25 μmol, 38.53% yield).

Compound 444: RT (IC, Hexane-IPA-MeOH, 50-25-25, 0.15 mL/min)=44.121 min.

$^1$H NMR (DMSO-$d_6$, 600 MHz): δ (ppm) 1.00 (m, 4H), 1.32 (m, 1H), 1.73 (m, 1H), 1.94 (m, 1H), 2.12 (m, 1H), 2.72 (m, 3H), 3.00 (m, 1H), 3.75 (m, 1H), 5.24 (m, 1H), 6.44 (m, 2H), 7.32 (m, 1H), 7.59 (m, 1H), 7.93 (s, 1H), 8.14 (m, 1H), 8.46 (m, 1H), 8.75 (m, 1H), 8.86 (m, 1H), 11.17 (m, 1H).

1413

LCMS(ESI): [M+H]+ m/z: calcd 396.2; found 397.2; Rt=1.638 min.

Compound 443: RT (IC, Hexane-IPA-MeOH, 50-25-25, 0.15 mL/min)=32.216 min.

$^1$H NMR (DMSO-d$_6$, 600 MHz): δ (ppm) 1.00 (m, 4H), 1.32 (m, 1H), 1.75 (m, 2H), 1.95 (m, 1H), 2.72 (m, 3H), 3.08 (m, 1H), 4.04 (m, 1H), 5.24 (m, 1H), 6.43 (m, 2H), 7.33 (m, 1H), 7.59 (m, 1H), 7.93 (s, 1H), 8.14 (m, 1H), 8.46 (m, 1H), 8.75 (m, 1H), 8.86 (m, 1H), 11.17 (m, 1H).

LCMS(ESI): [M+H]+ m/z: calcd 396.2; found 397.2; Rt=1.633 min.

Example 89. The Synthesis of Rel-2-methoxy-5-[[2-[(2R,5R)-5-methyl-2-[6-(methylamino)-3-pyridyl]-1-piperidyl]-2-oxo-acetyl]amino]pyridine-3-carboxamide (Compound 467), Rel-2-methoxy-5-[[2-[(2R,5S)-5-methyl-2-[6-(methylamino)-3-pyridyl]-1-piperidyl]-2-oxo-acetyl]amino]pyridine-3-carboxamide (Compound 447), Rel-2-methoxy-5-[[2-[(2S,5R)-5-methyl-2-[6-(methylamino)-3-pyridyl]-1-piperidyl]-2-oxo-acetyl]amino]pyridine-3-carboxamide (Compound 448) and Rel-2-methoxy-5-[[2-[(2S,5S)-5-methyl-2-[6-(methylamino)-3-pyridyl]-1-piperidyl]-2-oxo-acetyl]amino]pyridine-3-carboxamide (Compound 468

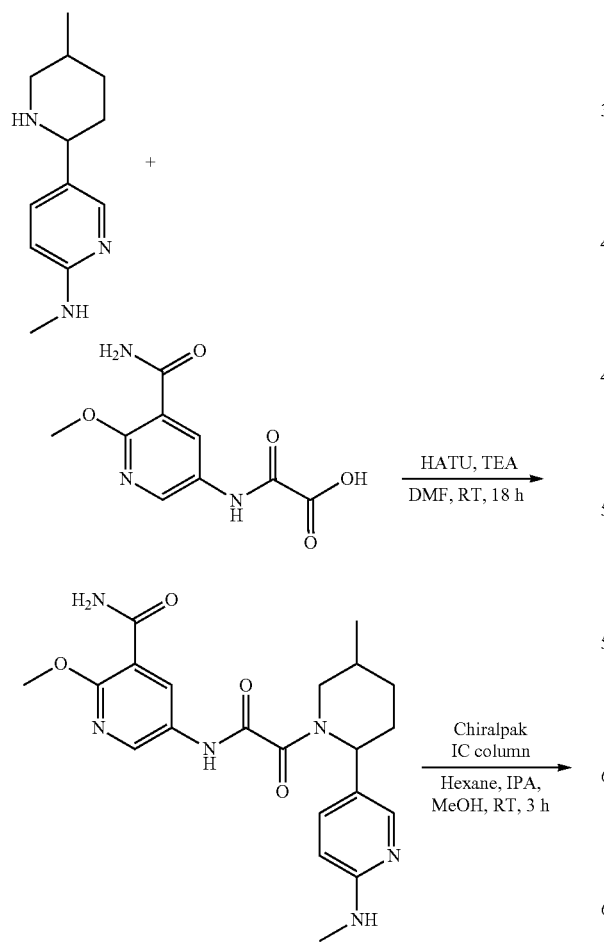

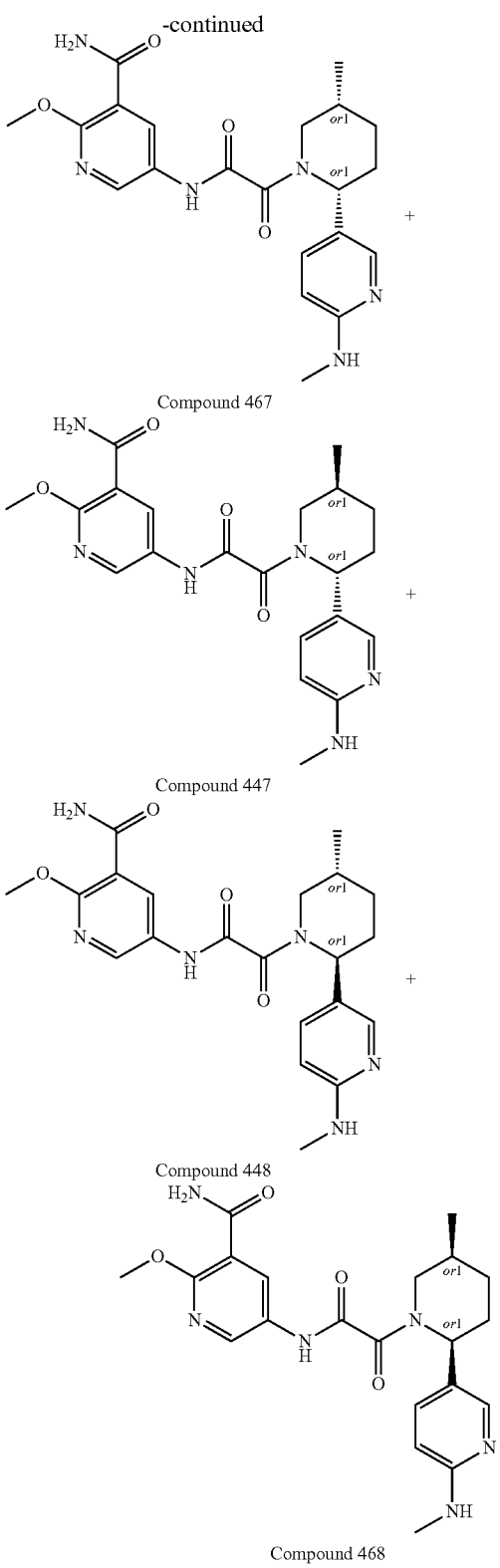

Step 1: The Synthesis of 2-methoxy-5-[[2-[(2S,5R)-5-methyl-2-[6-(methylamino)-3-pyridyl]-1-piperidyl]-2-oxo-acetyl]amino]pyridine-3-carboxamide N-methyl-5-[(2R,5S)-5-methyl-2-piperidyl]pyridin-2-amine (180.95 mg, 881.38 μmol), 2-[(5-carbamoyl-6- methoxy-3-pyridyl)amino]-2-oxo-acetic acid (300 mg, 881.38 μmol, Et₃N), triethylamine (445.94 mg, 4.41 mmol, 614.24 μL) were mixed in DMF (5 mL) and then HATU (502.69 mg, 1.32 mmol) were added. The resulting mixture was stirred at 25° C. for 12 hr. The mixture was evaporated under reduce pressure and purified with HPLC (2-10 min 40-60% water/MeCN+NH₃) to obtain 2-methoxy-5-[[2-[(2S,5R)-5-methyl-2-[6-(methylamino)-3-pyridyl]-1-piperidyl]-2-oxo-acetyl]amino]pyridine-3-carboxamide (86.2 mg, 202.13 μmol, 22.93% yield).

¹H NMR (400 MHz, DMSO-d₆) δ 1.02 (d, 3H), 1.03 (m, 1H), 1.95 (m, 4H), 2.75 (d, 3H), 3.17 (m, 1H), 3.24 (m, 1H), 3.34 (m, 2H), 3.97 (s, 3H), 5.27 (m, 1H), 6.45 (m, 2H), 7.80 (s, 1H), 7.82 (s, 1H), 8.52 (m, 1H), 11.05 (m, 1H).

LCMS(ESI): [M+H]⁺ m/z: calcd 426.2; found 427.2; Rt=0.824 min.

Step 2: The Synthesis of Rel-2-methoxy-5-[[2-[(2R, 5R)-5-methyl-2-[6-(methylamino)-3-pyridyl]-1-piperidyl]-2-oxo-acetyl]amino]pyridine-3-carboxamide (Compound 467), Rel-2-methoxy-5-[[2-[(2R,5S)-5-methyl-2-[6-(methylamino)-3-pyridyl]-1-piperidyl]-2-oxo-acetyl]amino]pyridine-3-carboxamide (Compound 447), Rel-2-methoxy-5-[[2-[(2S,5R)-5-methyl-2-[6-(methylamino)-3-pyridyl]-1-piperidyl]-2-oxo-acetyl]amino]pyridine-3-carboxamide (Compound 448) and Rel-2-methoxy-5-[[2-[(2S, 5S)-5-methyl-2-[6-(methylamino)-3-pyridyl]-1-piperidyl]-2-oxo-acetyl]amino]pyridine-3-carboxamide (Compound 468

The mixture of diastereomers was separated by chiral chromatography (Column: Chiralpak IC (250, 20 mm, 5 mkm); Mobile phase: Hexane-IPA-MeOH, 50-25-25 Flow Rate: 12 mL/min; Column Temperature: 24° C.; Wavelength: 205 nm, 252 nm, 306 nm; RetTime (isomer A)=23.52 min; RetTime (isomers B)=29.28 min; RetTime (isomers C)=36.86 min; RetTime (isomer D)=51.27 min) to obtain Compound 467—2-methoxy-5-[[2-[(2R,5R)-5-methyl-2-[6-(methylamino)-3-pyridyl]-1-piperidyl]-2-oxo-acetyl]amino]pyridine-3-carboxamide (8.01 mg, 18.78 μmol; RT=29.28), Compound 447—2-methoxy-5-[[2-[(2R, 5S)-5-methyl-2-[6-(methylamino)-3-pyridyl]-1-piperidyl]-2-oxo-acetyl]amino]pyridine-3-carboxamide (23.01 mg, 53.95 μmol, 26.69% yield; RT=51.27), Compound 448—2-methoxy-5-[[2-[(2S,5R)-5-methyl-2-[6-(methylamino)-3-pyridyl]-1-piperidyl]-2-oxo-acetyl]amino]pyridine-3-carboxamide (24.25 mg, 56.86 μmol, 28.13% yield; RT=36.86), Compound 468—2-methoxy-5-[[2-[(2S,5S)-5-methyl-2-[6-(methylamino)-3-pyridyl]-1-piperidyl]-2-oxo-acetyl]amino] pyridine-3-carboxamide (6.87 mg, 16.11 μmol, 7.97% yield; RT=23.53).

Compound 467:

RT (IC-3, Hexane-IPA-MeOH, 40-30-30, 0.15 mL/min)=15.419 min.

¹H NMR (DMSO-d₆, 600 MHz) δ 0.92-1.06 (m, 3H), 1.26-1.38 (m, 1H), 1.65-1.77 (m, 1H), 1.79-2.06 (m, 2H), 2.06-2.17 (m, 1H), 2.70-2.75 (m, 3H), 3.15-3.42 (m, 1H), 3.91-3.95 (m, 3H), 4.95-5.51 (m, 1H), 6.37-6.46 (m, 2H), 7.23-7.40 (m, 1H), 7.65-7.77 (m, 2H), 7.93 (s, 1H), 8.38-8.47 (m, 1H), 8.47-8.57 (m, 1H), 10.89-11.03 (m, 1H).

LCMS(ESI): [M+H]⁺ m/z: calcd 426.2; found 427.2; Rt=3.452 min.

Compound 447: RT (IC-3, Hexane-IPA-MeOH, 40-30-30, 0.15 mL/min)=26.173 min.

¹H NMR (DMSO-d₆, 500 MHz): δ (ppm) 1.03 (m, 3H), 1.36 (m, 1H), 1.75 (m, 1H), 2.00 (m, 3H), 2.75 (m, 3H), 3.24 (m, 1H), 3.41 (m, 1H), 3.96 (m, 3H), 5.25 (m, 1H), 6.46 (m, 2H), 7.34 (m, 1H), 7.75 (m, 2H), 7.95 (s, 1H), 8.46 (m, 1H), 8.54 (m, 1H), 10.98 (m, 1H).

LCMS(ESI): [M+H]⁺ m/z: calcd 426.2; found 427.2; Rt=3.339 min.

Compound 448: RT (IC-3, Hexane-IPA-MeOH, 40-30-30, 0.15 mL/min)=18.859 min.

¹H NMR (DMSO-d₆, 600 MHz): δ (ppm) 1.00 (m, 3H), 1.31 (m, 1H), 1.71 (m, 1H), 1.87 (m, 1H), 1.95 (m, 1H), 2.10 (m, 1H), 2.72 (m, 3H), 3.20 (m, 1H), 3.93 (m, 4H), 5.23 (m, 1H), 6.43 (m, 2H), 7.31 (m, 1H), 7.72 (m, 2H), 7.93 (s, 1H), 8.43 (m, 1H), 8.52 (m, 1H), 10.96 (m, 1H).

LCMS(ESI): [M+H]⁺ m/z: calcd 426.2; found 427.2; Rt=3.342 min.

Compound 468: RT (IC-3, Hexane-IPA-MeOH, 40-30-30, 0.15 mL/min)=12.322 min.

¹H NMR (DMSO-d₆, 600 MHz) δ 0.92-1.06 (m, 3H), 1.26-1.38 (m, 1H), 1.65-1.77 (m, 1H), 1.79-2.06 (m, 2H), 2.06-2.17 (m, 1H), 2.70-2.75 (m, 3H), 3.15-3.42 (m, 1H), 3.91-3.95 (m, 3H), 4.95-5.51 (m, 1H), 6.37-6.46 (m, 2H), 7.23-7.40 (m, 1H), 7.65-7.77 (m, 2H), 7.93 (s, 1H), 8.38-8.47 (m, 1H), 8.47-8.57 (m, 1H), 10.89-11.03 (m, 1H).

LCMS(ESI): [M+H]⁺ m/z: calcd 426.2; found 427.2; Rt=3.428 min.

Example 90. The Synthesis of rac-5-[[2-[(2S,5R)-2-(Benzothiophen-5-yl)-5-methyl-1-piperidyl]-2-oxo-acetyl]amino]pyridine-3-carboxamide (Compound 409), 5-[[2-[(2S,5R)-2-(Benzothiophen-5-yl)-5-methyl-1-piperidyl]-2-oxo-acetyl]amino]pyridine-3-carboxamide (Compound 586) and 5-[[2-[(2R,5S)-2-(Benzothiophen-5-yl)-5-methyl-1-piperidyl]-2-oxo-acetyl]amino]pyridine-3-carboxamide (Compound 585

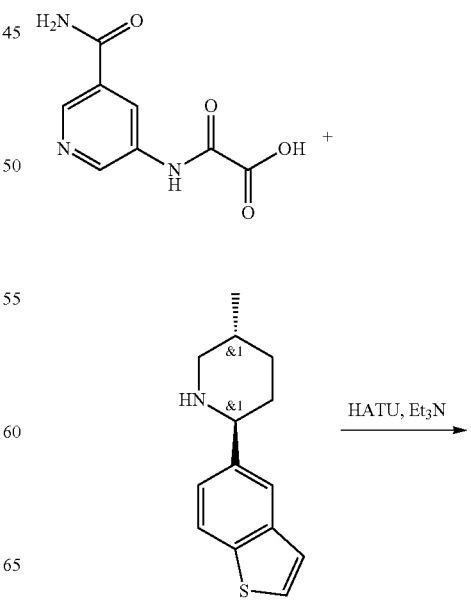

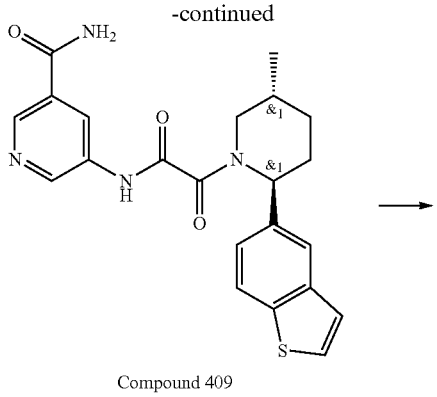

Compound 409

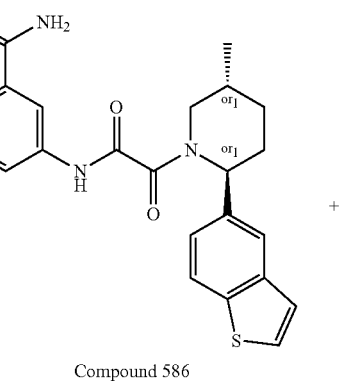

Compound 586

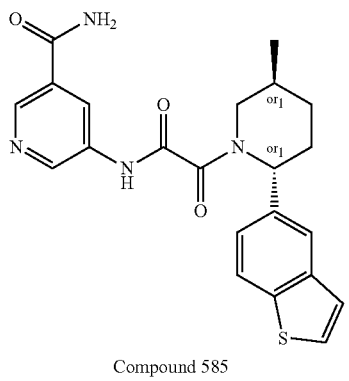

Compound 585

Step 1: Synthesis of rac-5-[[2-[(2S,5R)-2-(Benzothiophen-5-yl)-5-methyl-1-piperidyl]-2-oxo-acetyl]amino]pyridine-3-carboxamide (Compound 409

To a solution of (2S,5R)-2-(benzothiophen-5-yl)-5-methyl-piperidine (0.3 g, 1.30 mmol), 2-[(5-carbamoyl-3-pyridyl)amino]-2-oxo-acetic acid (318.50 mg, 1.30 mmol, HCl) and Triethylamine (656.07 mg, 6.48 mmol, 903.67 µL), HATU (542.35 mg, 1.43 mmol) was added. The resulting mixture was stirred at 25° C. for 3 hr and subjected to HPLC: 50-50-90% 0-1-6 min 0.1% NH$_3$-methanol, flow: 30 ml/min (loading pump 4 ml/min methanol) target mass 414 column: YMC Triart C18 100×20 mm, 5 um) to give 5-[[2-[(2S,5R)-2-(benzothiophen-5-yl)-5-methyl-1-piperidyl]-2-oxo-acetyl]amino]pyridine-3-carboxamide (278 mg, 657.99 µmol, 50.74% yield).

$^1$H NMR (500 MHz, DMSO) δ 1.03-1.07 (m, 3H), 1.32-1.49 (m, 1H), 1.72-1.84 (m, 1H), 1.86-1.99 (m, 1H), 2.09-2.27 (m, 1H), 2.29-2.36 (m, 1H), 2.83-3.27 (m, 1H), 3.54-4.11 (m, 1H), 5.26-5.81 (m, 1H), 7.32-7.43 (m, 1H), 7.43-7.51 (m, 1H), 7.56-7.68 (m, 1H), 7.73-7.84 (m, 1H), 7.84-7.93 (m, 1H), 7.95-8.08 (m, 1H), 8.09-8.25 (m, 1H), 8.44-8.58 (m, 1H), 8.71-8.83 (m, 1H), 8.83-8.98 (m, 1H), 11.18-11.43 (m, 1H).

LCMS(ESI): [M+1]$^+$ m/z: calcd 422.2; found 423.0; Rt=3.485 min.

Step 2: The Synthesis of 5-[[2-[(2S,5R)-2-(Benzothiophen-5-yl)-5-methyl-1-piperidyl]-2-oxo-acetyl]amino]pyridine-3-carboxamide (Compound 586) and 5-[[2-[(2R,5S)-2-(Benzothiophen-5-yl)-5-methyl-1-piperidyl]-2-oxo-acetyl]amino]pyridine-3-carboxamide (Compound 585

5-[[2-[(2S,5R)-2-(benzothiophen-5-yl)-5-methyl-1-piperidyl]-2-oxo-acetyl]amino]pyridine-3-carboxamide (169.5 mg, 401.18 µmol) was separated using Chiralpak IA 250*20, 5 mkm column; Hexane-IPA-MeOH, 50-25-25 as a mobile phase; Flow rate 25 mL/min; Injection Volume: 900 mkl; 3 pins; 56 mg/1 pin; affording Compound 586—5-[[2-[(2S,5R)-2-(benzothiophen-5-yl)-5-methyl-1-piperidyl]-2-oxo-acetyl]amino]pyridine-3-carboxamide (59.73 mg, 141.37 µmol, 35.24% yield) (RT (IA-3, Hexane-IPA-MeOH, 50-25-25, 0.155 ml/min)=10.599 min) as a yellow solid and Compound 585—5-[[2-[(2R,5S)-2-(benzothiophen-5-yl)-5-methyl-1-piperidyl]-2-oxo-acetyl]amino]pyridine-3-carboxamide (60.8 mg, 143.91 µmol, 35.87% yield) (RT (IA-3, Hexane-IPA-MeOH, 50-25-25, 0.155 ml/min)=14.975 min) as a beige solid.

Compound 586: $^1$H NMR (500 MHz, DMSO) δ 1.03-1.07 (m, 3H), 1.32-1.49 (m, 1H), 1.72-1.84 (m, 1H), 1.86-1.99 (m, 1H), 2.09-2.27 (m, 1H), 2.29-2.36 (m, 1H), 2.83-3.27 (m, 1H), 3.54-4.11 (m, 1H), 5.26-5.81 (m, 1H), 7.32-7.43 (m, 1H), 7.43-7.51 (m, 1H), 7.56-7.68 (m, 1H), 7.73-7.84 (m, 1H), 7.84-7.93 (m, 1H), 7.95-8.08 (m, 1H), 8.09-8.25 (m, 1H), 8.44-8.58 (m, 1H), 8.71-8.83 (m, 1H), 8.83-8.98 (m, 1H), 11.18-11.43 (m, 1H).

LCMS(ESI): [M+1]$^+$ m/z: calcd 422.2; found 423.0; Rt=2.884 min.

RT(IA-3, Hexane-IPA-MeOH, 50-25-25, 0.155 ml/min)=10.599 min

Compound 585: $^1$H NMR (500 MHz, DMSO) δ 1.03-1.07 (m, 3H), 1.32-1.49 (m, 1H), 1.72-1.84 (m, 1H), 1.86-1.99 (m, 1H), 2.09-2.27 (m, 1H), 2.29-2.36 (m, 1H), 2.83-3.27 (m, 1H), 3.54-4.11 (m, 1H), 5.26-5.81 (m, 1H), 7.32-7.43 (m, 1H), 7.43-7.51 (m, 1H), 7.56-7.68 (m, 1H), 7.73-7.84 (m, 1H), 7.84-7.93 (m, 1H), 7.95-8.08 (m, 1H), 8.09-8.25 (m, 1H), 8.44-8.58 (m, 1H), 8.71-8.83 (m, 1H), 8.83-8.98 (m, 1H), 11.18-11.43 (m, 1H).

LCMS(ESI): [M+1]$^+$ m/z: calcd 422.2; found 423.0; Rt=2.884 min.

RT(IA-3, Hexane-IPA-MeOH, 50-25-25, 0.155 ml/min)=14.975 min.

Example 91. The Synthesis of 5-[[2-[(2R,5S)-2-(Benzothiophen-5-yl)-5-methyl-1-piperidyl]-2-oxo-acetyl]amino]-2-methoxy-pyridine-3-carboxamide (Compound 618) and 5-[[2-[(2R,5S)-2-(Benzothiophen-5-yl)-5-methyl-1-piperidyl]-2-oxo-acetyl]amino]pyridine-3-carboxamide (Compound 633

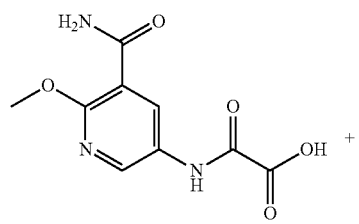

+

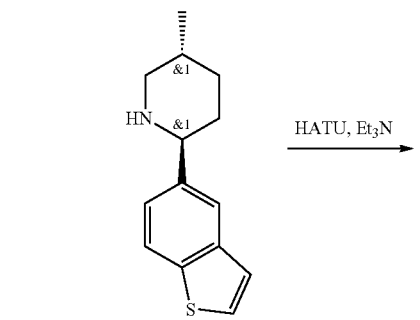

HATU, Et₃N →

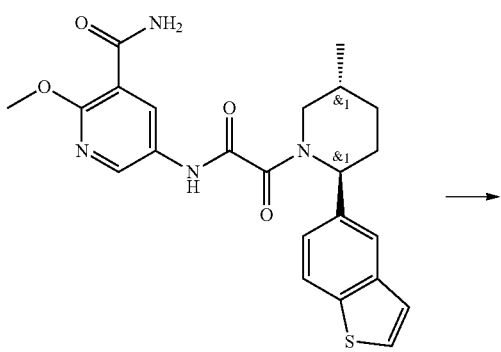

→

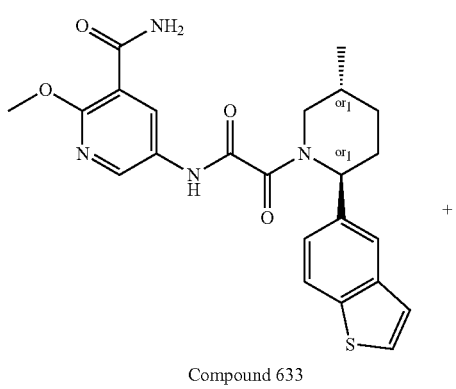

Compound 633

+

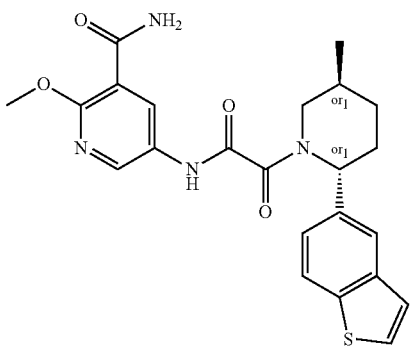

Compound 618

Step 1: Synthesis of 5-[[2-[(2S,5R)-2-(Benzothiophen-5-yl)-5-methyl-1-piperidyl]-2-oxo-acetyl]amino]-2-methoxy-pyridine-3-carboxamide To a solution of (2S,5R)-2-(benzothiophen-5-yl)-5-methyl-piperidine (0.3 g, 1.30 mmol), 2-[(5-carbamoyl-6-methoxy-3-pyridyl)amino]-2-oxo-acetic acid (441.36 mg, 1.30 mmol, Et₃N) and Triethylamine (656.07 mg, 6.48 mmol, 903.67 µL), HATU (542.35 mg, 1.43 mmol) was added portionwise. The resulting mixture was stirred at 25° C. for 3 hr and purified by HPLC (50-100% 1-6 min water-methanol (NH₃ 0.1%), flow 30 ml/min (loading pump 4 ml/min methanol (NH₃ 0.1%)) target mass 453 column: SunFire C18 100*19 mm Sum) to obtain 5-[[2-[(2S,5R)-2-(benzothiophen-5-yl)-5-methyl-1-piperidyl]-2-oxo-acetyl]amino]-2-methoxy-pyridine-3-carboxamide (190 mg, 419.87 µmol, 32.38% yield).

LCMS(ESI): [M+1]⁺ m/z: calcd 452.2; found 453.2; Rt=1.381 min.

Step 2: Synthesis of 5-[[2-[(2R,5S)-2-(Benzothiophen-5-yl)-5-methyl-1-piperidyl]-2-oxo-acetyl]amino]-2-methoxy-pyridine-3-carboxamide (Compound 618) and 5-[[2-[(2S,5R)-2-(Benzothiophen-5-yl)-5-methyl-1-piperidyl]-2-oxo-acetyl]amino]-2-methoxy-pyridine-3-carboxamide (Compound 633

5-[[2-[(2S,5R)-2-(benzothiophen-5-yl)-5-methyl-1-piperidyl]-2-oxo-acetyl]amino]-2-methoxy-pyridine-3-carboxamide (190 mg, 419.87 µmol) was chirally separated (Injection Volume: 900 mkl; Sample Info: IC II, Hexane-IPA-MeOH, 50-25-25, 12 ml/min) to obtain 5-[[2-[(2R,5S)-2-(benzothiophen-5-yl)-5-methyl-1-piperidyl]-2-oxo-acetyl]amino]-2-methoxy-pyridine-3-carboxamide (57 mg, 125.96 µmol, 60.00% yield) and 5-[[2-[(2S,5R)-2-(benzothiophen-5-yl)-5-methyl-1-piperidyl]-2-oxo-acetyl]amino]-2-methoxy-pyridine-3-carboxamide (44 mg, 97.23 µmol, 46.32% yield).

Compound 618: ¹H NMR (600 MHz, DMSO-d₆) δ 0.99-1.08 (m, 3H), 1.30-1.42 (m, 1H), 1.67-1.80 (m, 1H), 1.81-1.95 (m, 1H), 2.05-2.21 (m, 1H), 2.22-2.33 (m, 1H), 2.77-3.25 (m, 1H), 3.47-4.07 (m, 4H), 5.16-5.88 (m, 1H), 7.27-7.38 (m, 1H), 7.41-7.47 (m, 1H), 7.66-7.73 (m, 1H), 7.73-7.78 (m, 2H), 7.81-7.88 (m, 1H), 7.96-8.03 (m, 1H), 8.39-8.60 (m, 2H), 10.91-11.23 (m, 1H).

LCMS(ESI): [M+1]⁺ m/z: calcd 452.2; found 453.0; Rt=3.159 min.

RT(IC, Hexane-IPA-MeOH, 50-25-25, 0.6 ml/min)=30.076 min

Compound 633: $^1$H NMR (600 MHz, DMSO-d$_6$) δ 0.98-1.13 (m, 3H), 1.29-1.43 (m, 1H), 1.71-1.80 (m, 1H), 1.82-1.95 (m, 1H), 2.05-2.23 (m, 1H), 2.26-2.36 (m, 1H), 2.78-3.27 (m, 1H), 3.49-4.09 (m, 4H), 5.23-5.81 (m, 1H), 7.28-7.38 (m, 1H), 7.41-7.47 (m, 1H), 7.66-7.73 (m, 1H), 7.73-7.78 (m, 2H), 7.80-7.88 (m, 1H), 7.96-8.04 (m, 1H), 8.40-8.60 (m, 2H), 10.98-11.13 (m, 1H).

LCMS(ESI): [M+1]$^+$ m/z: calcd 452.2; found 453.2; Rt=3.159 min. with a cis-impurity less than 5%.

RT(IC, Hexane-IPA-MeOH, 50-25-25, 0.6 ml/min)=25.019 min with a cis-impurity less than 5%

Example 92. The Synthesis of 5-(2-(5-methyl-2-(2-methylbenzo[d]thiazol-5-yl)piperidin-1-yl)-2-oxoacetamido)Nicotinamide (Compound 702 and Compound 693

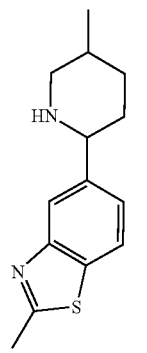

+

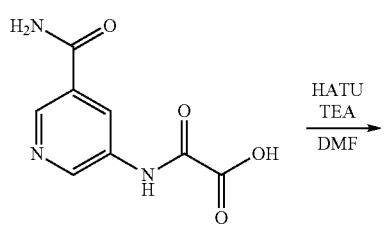

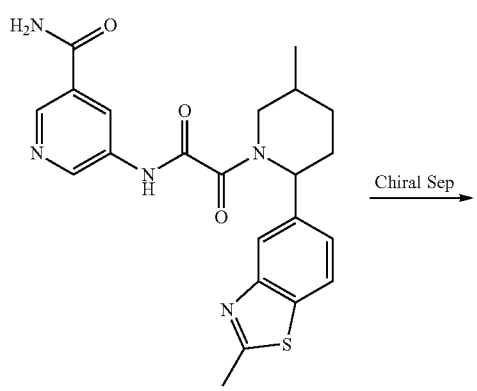

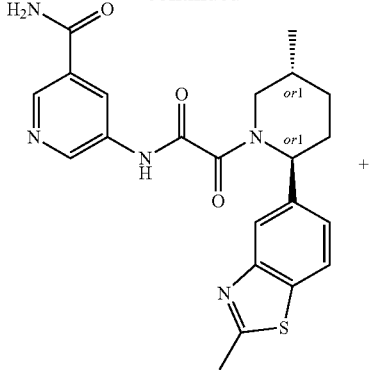

Compound 693

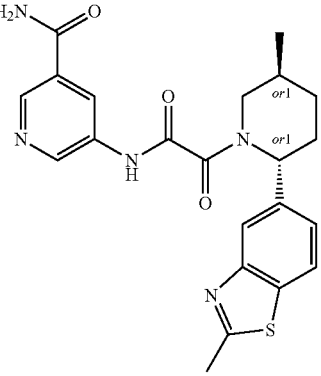

Compound 702

Step 1: Synthesis of 5-(2-(5-methyl-2-(2-methylbenzo[d]thiazol-5-yl)piperidin-1-yl)-2-oxoacetamido)Nicotinamide HATU (463.00 mg, 1.22 mmol) was added portionwise at rt to a suspension of 2-[(5-carbamoyl-3-pyridyl)amino]-2-oxo-acetic acid (299.09 mg, 1.22 mmol, HCl), 2-methyl-5-(5-methyl-2-piperidyl)-1,3-benzothiazole (300 mg, 1.22 mmol) and TEA (739.30 mg, 7.31 mmol, 1.02 mL) in DMF (10 mL). The clear solution was stirred at 20° C. for 18 hr and the solvents were evaporated in vacuo to give 1 g of crude material. It was subjected to RP-HPLC (column: YMC-Actus Triart C18 100*20 mml.D. S-5 um; 1-6 min 45-60% water-MeOH (NH$_3$ 0.1%), flow: 30 ml/min as mobile phase) to give 5-[[2-[5-methyl-2-(2-methyl-1,3-benzothiazol-5-yl)-1-piperidyl]-2-oxo-acetyl]amino]pyridine-3-carboxamide (249 mg, 569.12 μmol, 46.74% yield).

LCMS(ESI): [M]$^+$ m/z: calcd 437.2; found 438.2; Rt=2.680 min.

Step 2: Chiral Separation (Compound 702 and Compound 693

The enantiomers were separated by chiral HPLC (column: OJ (250*30, 20 mkm), C02-MeOH, 70-30, 80 ml/min make up flow rate—30 ml/min as mobile phase) to give the two individual enantiomers Compound 693 5-[[2-[(2S,5R)-5-methyl-2-(2-methyl-1,3-benzothiazol-5-yl)-1-piperidyl]-2-oxo-acetyl]amino]pyridine-3-carboxamide (74 mg, 169.14 μmol, 76.68% yield) RetTime=6.46 min and Compound 702 5-[[2-[(2R,5S)-5-methyl-2-(2-methyl-1,3-benzothiazol-5-yl)-1-piperidyl]-2-oxo-acetyl]amino]pyridine-3-carboxamide (72.3 mg, 165.25 μmol, 74.92% yield) RetTime=9.11 min.

Ret time for Compound 693 in analytical conditions (column: OJ-H, CO$_2$-MeOH, 70-30, 3 ml/min as mobile phase) 3.18 min and for Compound 702 5.82 min.

Compound 693: Retention time: 3.18 min $^1$H NMR (600 MHz, DMSO-d$_6$) δ (ppm) 1.03 (m, 3H), 1.37 (m, 1H), 1.71 (m, 1H), 1.89 (m, 1H), 2.19 (m, 2H), 2.77 (m, 3H), 3.04 (m, 1H), 3.76 (m, 1H), 5.49 (m, 1H), 7.37 (m, 1H), 7.59 (m, 1H), 7.86 (m, 1H), 8.01 (m, 1H), 8.14 (m, 1H), 8.46 (m, 1H), 8.75 (m, 1H), 8.87 (m, 1H), 11.26 (m, 1H).

LCMS(ESI): [M]$^+$ m/z: calcd 437.2; found 438.2; Rt=1.143 min.

Compound 702: Retention time: 5.82 min $^1$H NMR (600 MHz, DMSO-d$_6$) δ (ppm) 1.03 (m, 3H), 1.37 (m, 1H), 1.71 (m, 1H), 1.88 (m, 1H), 2.13 (m, 1H), 2.29 (m, 1H), 2.77 (m, 3H), 2.85 (m, 1H), 3.67 (m, 1H), 5.49 (m, 1H), 7.37 (m, 1H), 7.58 (m, 1H), 7.86 (m, 1H), 8.02 (m, 1H), 8.14 (m, 1H), 8.46 (m, 1H), 8.75 (m, 1H), 8.87 (m, 1H), 11.26 (m, 1H).

LCMS(ESI): [M]$^+$ m/z: calcd 437.2; found 438.2; Rt=1.143 min.

Example 93. The Synthesis of 2-methoxy-5-(2-(5-methyl-2-(2-methylbenzo[d]thiazol-5-yl)piperidin-1-yl)-2-oxoacetamido)Nicotinamide (Compound 797 and Compound 808

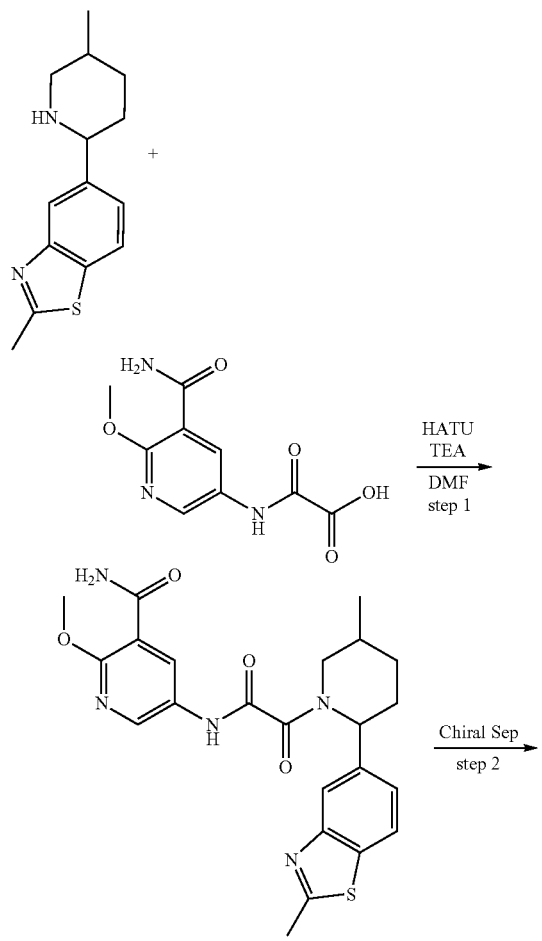

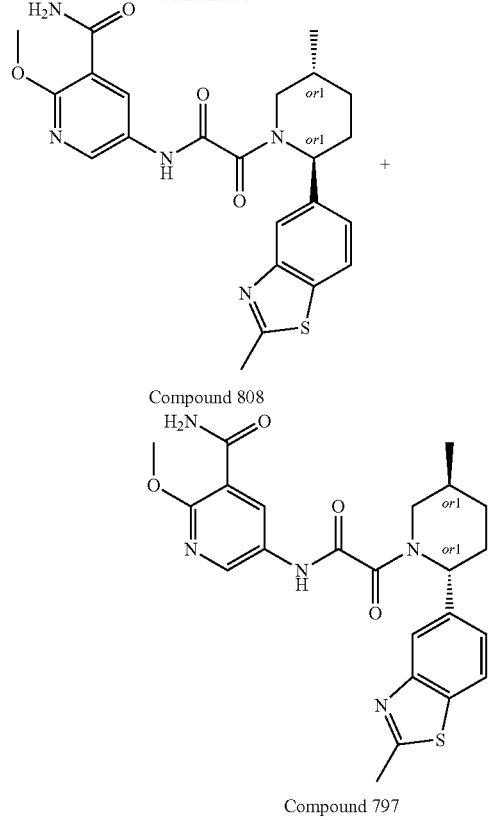

Compound 808

Compound 797

Step 1: Synthesis of 2-methoxy-5-(2-(5-methyl-2-(2-methylbenzo[d]thiazol-5-yl)piperidin-1-yl)-2-oxoacetamido)Nicotinamide HATU (390.98 mg, 1.03 mmol) was added portionwise at rt to a suspension of 2-[(5-carbamoyl-6-methoxy-3-pyridyl)amino]-2-oxo-acetic acid (350 mg, 1.03 mmol), 2-methyl-5-(5-methyl-2-piperidyl)-1,3-benzothiazole (253.34 mg, 1.03 mmol) and TEA (624.31 mg, 6.17 mmol, 859.93 μL) in DMF (10 mL). The clear solution was stirred at 20° C. for 18 hr and the solvents were evaporated in vacuo to give 1 g of crude material. It was subjected to RP-HPLC (column: YMC-Actus Triart C18 100*20 mm I.D. S-5 um; 1-6 min 60-70% water-MeOH (NH$_3$0.1%), flow: 30 ml/min as mobile phase) to give 2-methoxy-5-[[2-[5-methyl-2-(2-methyl-1,3-benzothiazol-5-yl)-1-piperidyl]-2-oxo-acetyl]amino]pyridine-3-carboxamide (260 mg, 556.10 μmol, 54.08% yield).

LCMS(ESI): [M]$^+$ m/z: calcd 467.2; found 468.2; Rt=3.043 min.

Step 2: Chiral Separation (Compound 808 and Compound 797

The enantiomers were separated by chiral HPLC (column: IA-I, Hexane-IPA-MeOH, 40-30-30, 12 ml/min as mobile phase) to give the two individual enantiomers Compound 808 2-methoxy-5-[[2-[(2S,5R)-5-methyl-2-(2-methyl-1,3-benzothiazol-5-yl)-1-piperidyl]-2-oxo-acetyl]amino]pyridine-3-carboxamide (45.7 mg, 97.75 μmol, 91.40% yield) RetTime=52.2 min and Compound 797 2-methoxy-5-[[2-[(2R,5S)-5-methyl-2-(2-methyl-1,3-benzothiazol-5-yl)-1- piperidyl]-2-oxo-acetyl]amino]pyridine-3-carboxamide (48.1 mg, 102.88 µmol, 96.20% yield) RetTime=96.7 min.

Ret time for Compound 808 in analytical conditions (column: IA, IPA-MeOH, 50-50, 0.6 ml/min as mobile phase) 39.25 min and for Compound 797 51.68 min.

Compound 808: Retention time: 39.25 min $^1$H NMR (600 MHz, DMSO-d$_6$) δ (ppm) 0.97-1.06 (m, 3H), 1.30-1.40 (m, 1H), 1.64-1.76 (m, 1H), 1.81-1.94 (m, 1H), 2.07-2.21 (m, 1H), 2.25-2.34 (m, 1H), 2.73-2.80 (m, 3H), 2.80-3.27 (m, 1H), 3.37-3.54 (m, 0.6H), 3.86-3.98 (m, 3H), 3.99-4.06 (m, 0.4H), 5.26-5.75 (m, 1H), 7.31-7.42 (m, 1H), 7.63-7.78 (m, 2H), 7.80-7.88 (m, 1H), 7.97-8.10 (m, 1H), 8.37-8.60 (m, 2H), 10.93-11.23 (m, 1H).

LCMS(ESI): [M]$^+$ m/z: calcd 467.2; found 468.2; Rt=3.030 min.

Compound 797: Retention time: 51.68 min $^1$H NMR (600 MHz, DMSO-d$_6$) δ (ppm) 0.97-1.06 (m, 3H), 1.29-1.41 (m, 1H), 1.60-1.78 (m, 1H), 1.79-1.93 (m, 1H), 2.05-2.21 (m, 1H), 2.25-2.34 (m, 1H), 2.73-2.79 (m, 3H), 2.79-3.27 (m, 1H), 3.42-3.52 (m, 0.6H), 3.85-3.98 (m, 3H), 3.99-4.07 (m, 0.4H), 5.22-5.77 (m, 1H), 7.30-7.44 (m, 1H), 7.65-7.78 (m, 2H), 7.81-7.89 (m, 1H), 7.96-8.11 (m, 1H), 8.37-8.61 (m, 2H), 10.98-11.18 (m, 1H).

LCMS(ESI): [M]$^+$ m/z: calcd 467.2; found 468.2; Rt=3.032 min.

Example 94. The Synthesis of N-(6-amino-5-ethylpyridin-3-yl)-2-(5-methyl-2-(2-methylbenzo[d]thiazol-5-yl)piperidin-1-yl)-2-oxoacetamide (Compound 801 and Compound 800

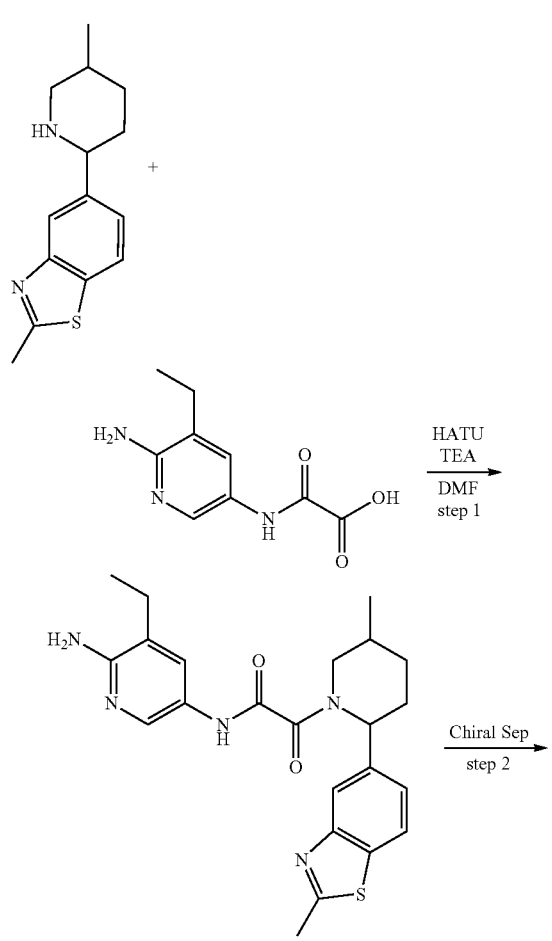

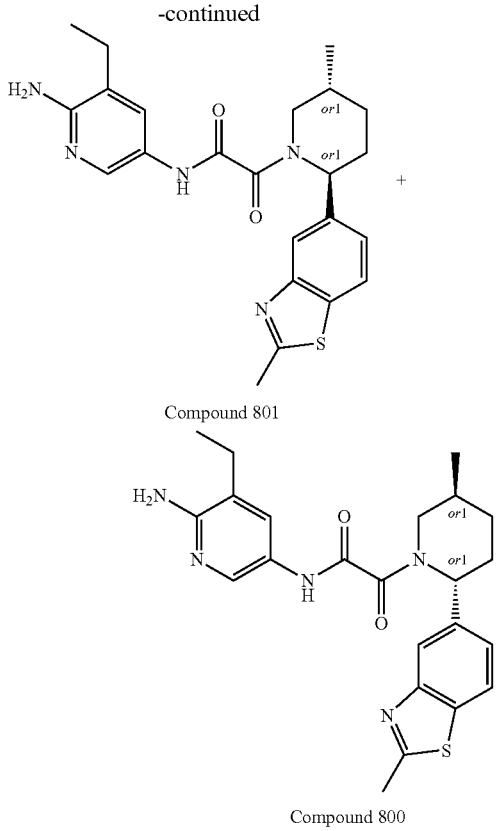

Compound 801

Compound 800

Step 1: Synthesis of N-(6-amino-5-ethylpyridin-3-yl)-2-(5-methyl-2-(2-methylbenzo[d]thiazol-5-yl)piperidin-1-yl)-2-oxoacetamide HATU (363.51 mg, 956.01 µmol) was added portionwise at rt to a suspension of 2-[(6-amino-5-ethyl-3-pyridyl)amino]-2-oxo-acetic acid (200 mg, 956.02 µmol), 2-methyl-5-(5-methyl-2-piperidyl)-1,3-benzothiazole (235.53 mg, 956.01 µmol) and TEA (580.43 mg, 5.74 mmol, 799.50 µL) in DMF (10 mL). The clear solution was stirred at 20° C. for 18 hr and the solvents were evaporated in vacuo to give 1 g of crude material. It was subjected to RP-HPLC (column: YMC-Actus Triart C18 100*20 mml.D. S-5 um; 1-6 min 60-70% water-MeOH (NH$_3$0.1%), flow: 30 ml/min as mobile phase) to give N-(6-amino-5-ethyl-3-pyridyl)-2-[5-methyl-2-(2-methyl-1,3-benzothiazol-5-yl)-1-piperidyl]-2-oxo-acetamide (249 mg, 569.07 µmol, 59.53% yield).

LCMS(ESI): [M]$^+$ m/z: calcd 437.2; found 438.2; Rt=2.393 min.

Step 2: Chiral Separation (Compound 800 and Compound 808

The enantiomers were separated by chiral HPLC (column: IC, Hexane-IPA-MeOH, 50-25-25, 12 ml/min as mobile phase) to give the two individual enantiomers Compound 801 N-(6-amino-5-ethyl-3-pyridyl)-2-[(2S,5R)-5-methyl-2-(2-methyl-1,3-benzothiazol-5-yl)-1-piperidyl]-2-oxo-acetamide (75 mg, 171.41 µmol, 62.50% yield) RetTime=29.5 min and Compound 800 N-(6-amino-5-ethyl-3-pyridyl)-2-[(2R,5S)-5-methyl-2-(2-methyl-1,3-benzothiazol-5-yl)-1-piperidyl]-2-oxo-acetamide (99 mg, 226.26 µmol, 82.50% yield) RetTime=49.4 min.

Ret Time for Compound 800 in analytical conditions (column: IC, Hexane-IPA-MeOH, 50-25-25, 0.6 ml/min as mobile phase) 47.90 min and for Compound 801 29.65 min.

Compound 800: Retention time: 47.90 min $^1$H NMR (600 MHz, DMSO-d$_6$) δ (ppm) 0.98-1.04 (m, 3H), 1.04-1.15 (m, 3H), 1.30-1.41 (m, 1H), 1.65-1.73 (m, 1H), 1.80-1.91 (m, 1H), 2.02-2.21 (m, 1H), 2.25-2.33 (m, 1H), 2.35-2.41 (m, 2H), 2.75-2.78 (m, 3H), 2.80-3.27 (m, 1H), 3.41-4.09 (m, 1H), 5.24-5.59 (m, 1H), 5.60-5.72 (m, 2H), 7.30-7.41 (m, 1H), 7.42-7.55 (m, 1H), 7.79-7.88 (m, 1H), 7.97-8.07 (m, 2H), 10.48-10.63 (m, 1H).

LCMS(ESI): [M]$^+$ m/z: calcd 437.2; found 438.2; Rt=2.313 min.

Compound 801: Retention time: 29.65 min $^1$H NMR (600 MHz, DMSO-d$_6$) δ (ppm) 0.99-1.04 (m, 3H), 1.04-1.15 (m, 3H), 1.30-1.42 (m, 1H), 1.63-1.75 (m, 1H), 1.81-1.93 (m, 1H), 2.01-2.21 (m, 1H), 2.24-2.32 (m, 1H), 2.36-2.43 (m, 2H), 2.77 (s, 3H), 2.79-3.26 (m, 1H), 3.42-4.08 (m, 1H), 5.23-5.60 (m, 1H), 5.60-5.75 (m, 2H), 7.30-7.41 (m, 1H), 7.41-7.59 (m, 1H), 7.79-7.89 (m, 1H), 7.95-8.09 (m, 2H), 10.44-10.61 (m, 1H).

LCMS(ESI): [M]$^+$ m/z: calcd 437.2; found 438.2; Rt=2.313 min.

Example 95. The Synthesis of 5-(2-(2-(3,4-difluorophenyl)-5-methylpiperidin-1-yl)-2-oxoacetamido) Nicotinamide (Compound 475, Compound 474

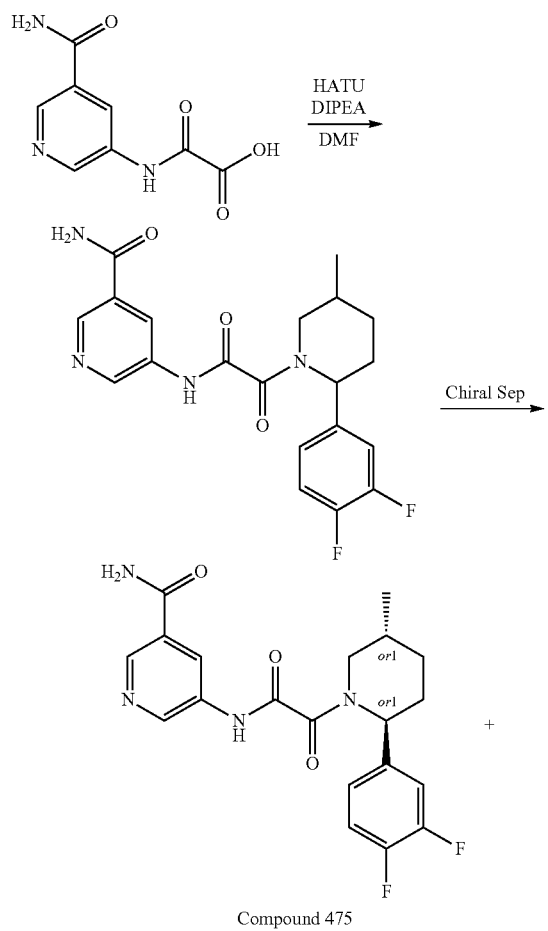

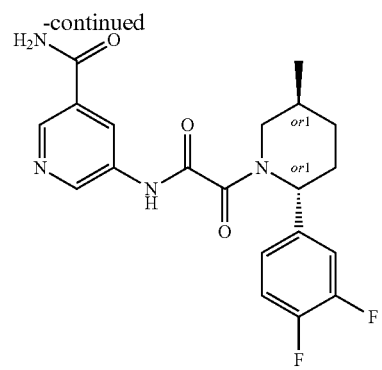

Compound 474

Step 1: Synthesis of 5-(2-(2-(3,4-difluorophenyl)-5-methylpiperidin-1-yl)-2-oxoacetamido)Nicotinamide DIPEA (385.43 mg, 2.98 mmol, 519.45 µL) was added to the solution of respective 2-(3,4-difluorophenyl)-5-methylpiperidine (0.18 g, 852.07 µmol) and 2-[(5-carbamoyl-3-pyridyl)amino]-2-oxo-acetic acid (178.22 mg, 725.59 µmol, HCl) in DMF (10 mL). The resulting mixture was stirred for 5 min followed by the addition of the solution of HATU (356.38 mg, 937.28 µmol). Then, the reaction mixture was stirred overnight at room temperature. After the completion of the reaction, monitored by LCMS, the resulting suspension was concentrated under reduced pressure. The obtained solid was subjected to HPLC (column: Triart 100*20, 5 mkl; MeOH+NH$_3$ as an eluent mixture) to afford pure 5-[[2-[(2R,5S)-2-(3,4-difluorophenyl)-5-methyl-1-piperidyl]-2-oxo-acetyl]amino]pyridine-3-carboxamide (0.19 g, 472.17 µmol, 55.41% yield).

$^1$H NMR (400 MHz, CDCl$_3$) δ (ppm)

LCMS(ESI): [M]$^+$ m/z: calcd 402.2; found 403.2; Rt=3.380 min.

Step 2: Chiral Separation (Compound 475 and Compound 474

5-[[2-[(2R,5S)-2-(3,4-difluorophenyl)-5-methyl-1-piperidyl]-2-oxo-acetyl]amino]pyridine-3-carboxamide (108 mg, 268.39 µmol) was separated using Chiralpak IC-II 250*20, 5 mkm column; Hexane-IPA-MeOH, 50-25-25 as a mobile phase; Flow rate 12 mL/min; Injection Volume: 900 mkl; affording Compound 475—5-[[2-[(2S,5R)-2-(3,4-difluorophenyl)-5-methyl-1-piperidyl]-2-oxo-acetyl]amino] pyridine-3-carboxamide (56.59 mg, 140.63 µmol, 52.40% yield) (RT (IC, Hexane-IPA-MeOH, 50-25-25, 0.6 ml/min)=24.70 min) as a yellow solid and Compound 474—5-[[2-[(2R,5S)-2-(3,4-difluorophenyl)-5-methyl-1-piperidyl]-2-oxo-acetyl]amino]pyridine-3-carboxamide (50.99 mg, 126.72 µmol, 47.21% yield) (RT (IC, Hexane-IPA-MeOH, 50-25-25, 0.6 ml/min)=15.21 min) as a yellow solid.

Compound 475: Retention time: 24.70 min $^1$H NMR (600 MHz, DMSO-d$_6$) δ (ppm) 0.99-1.03 (m, 3H), 1.26-1.37 (m, 1H), 1.58-1.71 (m, 1H), 1.82-1.97 (m, 1H), 2.00-2.13 (m, 1H), 2.14-2.25 (m, 1H), 2.74-3.24 (m, 1H), 3.42-4.02 (m, 1H), 5.11-5.58 (m, 1H), 7.11-7.22 (m, 1H), 7.32-7.50 (m, 2H), 7.55-7.64 (m, 1H), 8.08-8.21 (m, 1H), 8.42-8.52 (m, 1H), 8.71-8.80 (m, 1H), 8.81-8.92 (m, 1H), 11.15-11.40 (m, 1H).

LCMS(ESI): [M]$^+$ m/z: calcd 402.2; found 403.2; Rt=1.225 min.

Compound 474: Retention time: 15.21 min

¹H NMR (600 MHz, DMSO-d₆) δ (ppm) 0.99-1.08 (m, 3H), 1.21-1.43 (m, 1H), 1.59-1.74 (m, 1H), 1.83-1.98 (m, 1H), 1.99-2.16 (m, 1H), 2.17-2.30 (m, 1H), 2.74-3.31 (m, 1H), 3.43-4.11 (m, 1H), 5.12-5.63 (m, 1H), 7.14-7.27 (m, 1H), 7.33-7.53 (m, 2H), 7.58-7.69 (m, 1H), 8.12-8.24 (m, 1H), 8.44-8.56 (m, 1H), 8.73-8.85 (m, 1H), 8.85-8.98 (m, 1H), 11.18-11.36 (m, 1H).

LCMS(ESI): [M]⁺ m/z: calcd 402.2; found 403.2; Rt=1.226 min.

Example 96. The Synthesis of 5-(2-(5-methyl-2-(3,4,5-trifluorophenyl)piperidin-1-yl)-2-oxoacetamido) Nicotinamide (Compound 476, Compound 477

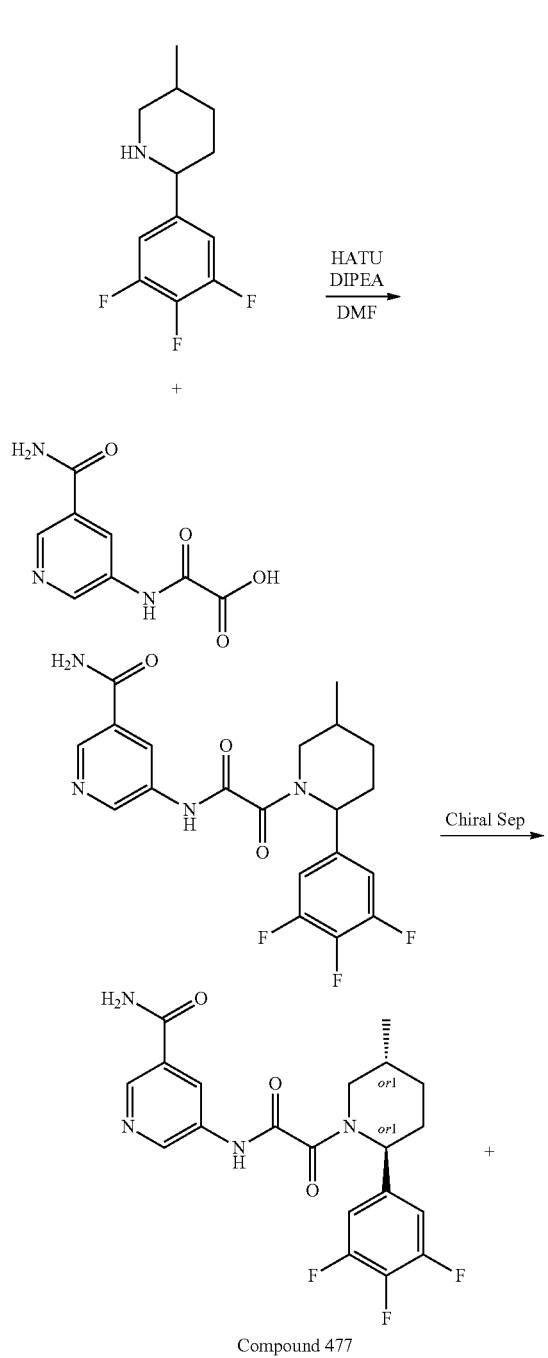

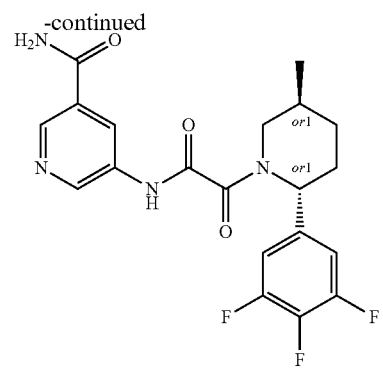

Compound 476

Step 1: Synthesis of 5-(2-(5-methyl-2-(3,4,5-trifluorophenyl)piperidin-1-yl)-2-oxoacetamido)Nicotinamide DIPEA (394.65 mg, 3.05 mmol, 531.87 µL) was added to the solution of respective 5-methyl-2-(3,4,5-trifluorophenyl)piperidine (0.2 g, 872.44 µmol) and 2-[(5-carbamoyl-3-pyridyl)amino]-2-oxo-acetic acid (182.48 mg, 742.94 µmol, HCl) in DMF (10 mL). The resulting mixture was stirred for 5 min followed by the addition of the solution of HATU (364.90 mg, 959.69 µmol). Then, the reaction mixture was stirred overnight at rt. After the completion of the reaction, monitored by LCMS, the resulting suspension was concentrated under reduced pressure. The obtained solid was subjected to HPLC to afford pure 5-[[2-[(2R,5S)-5-methyl-2-(3,4,5-trifluorophenyl)-1-piperidyl]-2-oxo-acetyl]amino]pyridine-3-carboxamide (209 mg, 497.16 µmol, 56.99% yield).

¹H NMR (400 MHz, CDCl₃) δ (ppm)

LCMS(ESI): [M]⁺ m/z: calcd 420.2; found 421.2; Rt=3.479 min.

Step 2: Chiral Separation (Compound 476 and Compound 477

5-[[2-[(2R,5S)-5-methyl-2-(3,4,5-trifluorophenyl)-1-piperidyl]-2-oxo-acetyl]amino]pyridine-3-carboxamide (209 mg, 497.16 µmol) was separated using Chiralpak IC-II 250*20, 5 mkm column; Hexane-IPA-MeOH, 70-15-15 as a mobile phase; Flow rate 14 mL/min; Injection Volume: 900 mkl; affording Compound 476—5-[[2-[(2R,5S)-5-methyl-2-(3,4,5-trifluorophenyl)-1-piperidyl]-2-oxo-acetyl]amino]pyridine-3-carboxamide (104.08 mg, 247.58 µmol, 49.80% yield) (RT (IC, Hexane-IPA-MeOH, 50-25-25, 0.6 ml/min)=143.22 min) as a yellow solid and Compound 477—5-[[2-[(2S,5R)-5-methyl-2-(3,4,5-trifluorophenyl)-1-piperidyl]-2-oxo-acetyl]amino]pyridine-3-carboxamide (104.85 mg, 249.41 µmol, 50.17% yield) (RT (IC, Hexane-IPA-MeOH, 50-25-25, 0.6 ml/min)=19.38 min) as a yellow solid.

Compound 476: Retention time: 13.22 min

¹H NMR (600 MHz, DMSO-d₆) δ (ppm) 0.99-1.01 (m, 3H), 1.24-1.38 (m, 1H), 1.58-1.68 (m, 1H), 1.82-1.94 (m, 1H), 1.98-2.12 (m, 1H), 2.13-2.24 (m, 1H), 2.76-3.28 (m, 1H), 3.45-4.05 (m, 1H), 5.10-5.53 (m, 1H), 7.22-7.31 (m, 2H), 7.55-7.63 (m, 1H), 8.11-8.22 (m, 1H), 8.42-8.52 (m, 1H), 8.73-8.81 (m, 1H), 8.81-8.93 (m, 1H), 11.20-11.32 (m, 1H).

LCMS(ESI): [M]⁺ m/z: calcd 420.2; found 421.2; Rt=3.351 min.

Compound 477: Retention time: 19.38 min

¹H NMR (600 MHz, DMSO-d₆) δ (ppm) 0.99-1.01 (m, 3H), 1.24-1.38 (m, 1H), 1.57-1.69 (m, 1H), 1.79-1.94 (m, 1H), 1.94-2.11 (m, 1H), 2.11-2.23 (m, 1H), 2.77-3.28 (m, 1H), 3.44-4.04 (m, 1H), 5.11-5.53 (m, 1H), 7.20-7.33 (m, 2H), 7.54-7.65 (m, 1H), 8.10-8.21 (m, 1H), 8.42-8.51 (m, 1H), 8.72-8.81 (m, 1H), 8.81-8.92 (m, 1H), 11.11-11.39 (m, 1H).

LCMS(ESI): [M]⁺ m/z: calcd 420.2; found 421.2; Rt=3.348 min.

Example 97. The Synthesis of 2-methoxy-5-(2-(5-methyl-2-(3,4,5-trifluorophenyl)piperidin-1-yl)-2-oxoacetamido)Nicotinamide (Compound 739, Compound 742

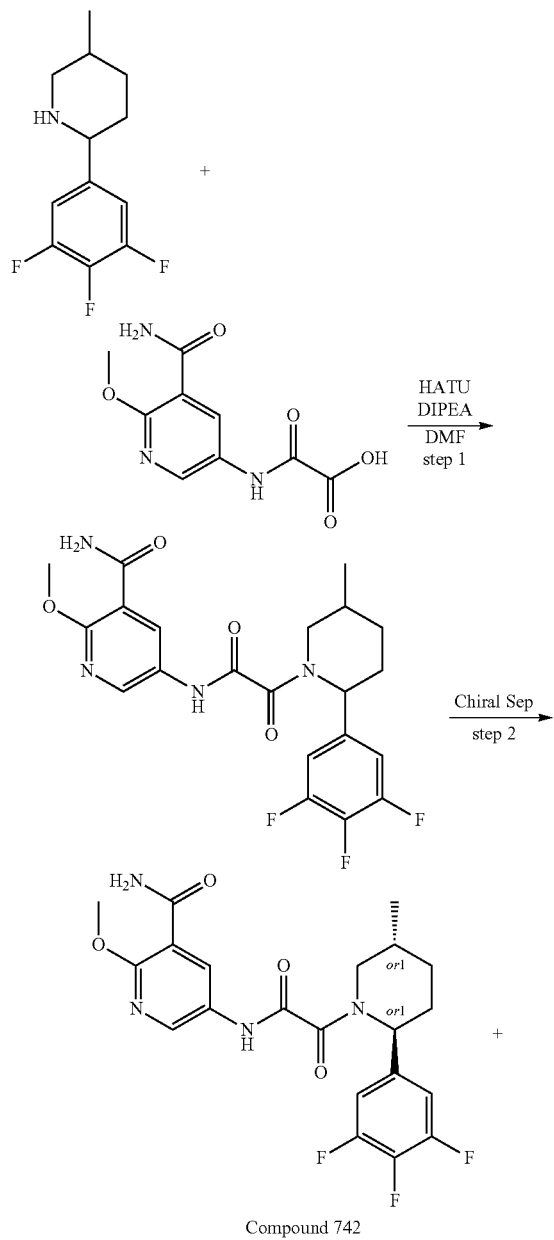

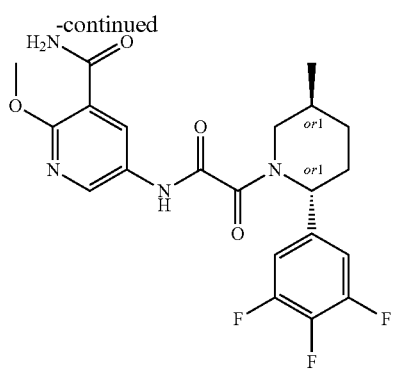

Compound 739

Step 1: Synthesis of 2-methoxy-5-(2-(5-methyl-2-(3,4,5-trifluorophenyl)piperidin-1-yl)-2-oxoacetamido)Nicotinamide DIPEA (398.69 mg, 3.08 mmol, 537.32 μL) was added to the solution of respective 5-methyl-2-(3,4,5-trifluorophenyl)piperidine (202.05 mg, 760.44 μmol, HCl) and 2-[(5-carbamoyl-6-methoxy-3-pyridyl)amino]-2-oxo-acetic acid (0.3 g, 881.38 μmol, Et₃N) in DMF (5 mL). The resulting mixture was stirred for 5 min followed by the addition of HATU (368.64 mg, 969.52 μmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and H₂O-MeOH+NH₃ as an eluent mixture) to afford 2-methoxy-5-[[2-[5-methyl-2-(3,4,5-trifluorophenyl)-1-piperidyl]-2-oxo-acetyl]amino]pyridine-3-carboxamide (166 mg, 368.55 μmol, 41.82% yield).

¹H NMR (400 MHz, DMSO-d₆) δ (ppm) 1.02 (d, 3H), 1.24 (m, 1H), 1.58 (m, 1H), 1.98 (m, 1H), 2.24 (m, 2H), 3.36 (m, 1H), 3.96 (s, 3H), 4.02 (m, 1H), 5.48 (m, 1H), 7.28 (m, 2H), 7.86 (m, 2H), 8.52 (m, 1H), 8.62 (m, 1H), 11.12 (m, 1H).

LCMS(ESI): [M]⁺ m/z: calcd 450.2; found 451.2; Rt=3.229 min.

Step 2: Chiral Separation (Compound 739 and Compound 742

2-methoxy-5-[[2-[5-methyl-2-(3,4,5-trifluorophenyl)-1-piperidyl]-2-oxo-acetyl]amino]pyridine-3-carboxamide (100 mg, 222.02 μmol) was separated using Chiralpak IA 250*20, 5 mkm column; Hexane-IPA-MeOH, 60-20-20 as a mobile phase; Flow rate 12 mL/min; Injection Volume: 900 mkl; affording Compound 739—2-methoxy-5-[[2-[(2R,5S)-5-methyl-2-(3,4,5-trifluorophenyl)-1-piperidyl]-2-oxo-acetyl]amino]pyridine-3-carboxamide (49.57 mg, 110.06 μmol, 49.57% yield) (RT (IC, CO₂-MeOH, 60-40, 2 ml/min) =6.03 min) as a yellow solid and Compound 742—2-methoxy-5-[[2-[(2S,5R)-5-methyl-2-(3,4,5-trifluorophenyl)-1-piperidyl]-2-oxo-acetyl]amino]pyridine-3-carboxamide (45.74 mg, 101.55 μmol, 45.74% yield) (RT (IC, CO₂-MeOH, 60-40, 2 ml/min)=8.50 min) as a yellow solid.

Compound 739: Retention time: 6.03 min

¹H NMR (600 MHz, DMSO-d₆) δ (ppm) 0.99 (m, 3H), 1.27 (m, 1H), 1.63 (m, 1H), 1.87 (m, 1H), 2.01 (m, 1H), 2.16

(m, 1H), 3.01 (m, 1H), 3.78 (m, 4H), 5.30 (m, 1H), 7.25 (m, 2H), 7.72 (m, 2H), 8.48 (m, 2H), 11.04 (m, 1H).
LCMS(ESI): [M]+ m/z: calcd 450.2; found 451.2; Rt=1.158 min.
Compound 742: Retention time: 8.50 min
$^1$H NMR (600 MHz, DMSO-$d_6$) δ (ppm) 0.99 (m, 3H), 1.28 (m, 1H), 1.62 (m, 1H), 1.87 (m, 1H), 2.02 (m, 1H), 2.18 (m, 1H), 2.92 (m, 1H), 3.93 (m, 4H), 5.30 (m, 1H), 7.26 (m, 2H), 7.72 (m, 2H), 8.48 (m, 2H), 11.04 (m, 1H).
LCMS(ESI): [M]+ m/z: calcd 450.2; found 451.2; Rt=1.159 min.

Example 98. The Synthesis of 5-(2-(2-(4-hydroxy-cyclohexyl)-5-methylpiperidin-1-yl)-2-oxoacetamido)Nicotinamide (Compound 393, Compound 382 and Compound 394, Compound 395

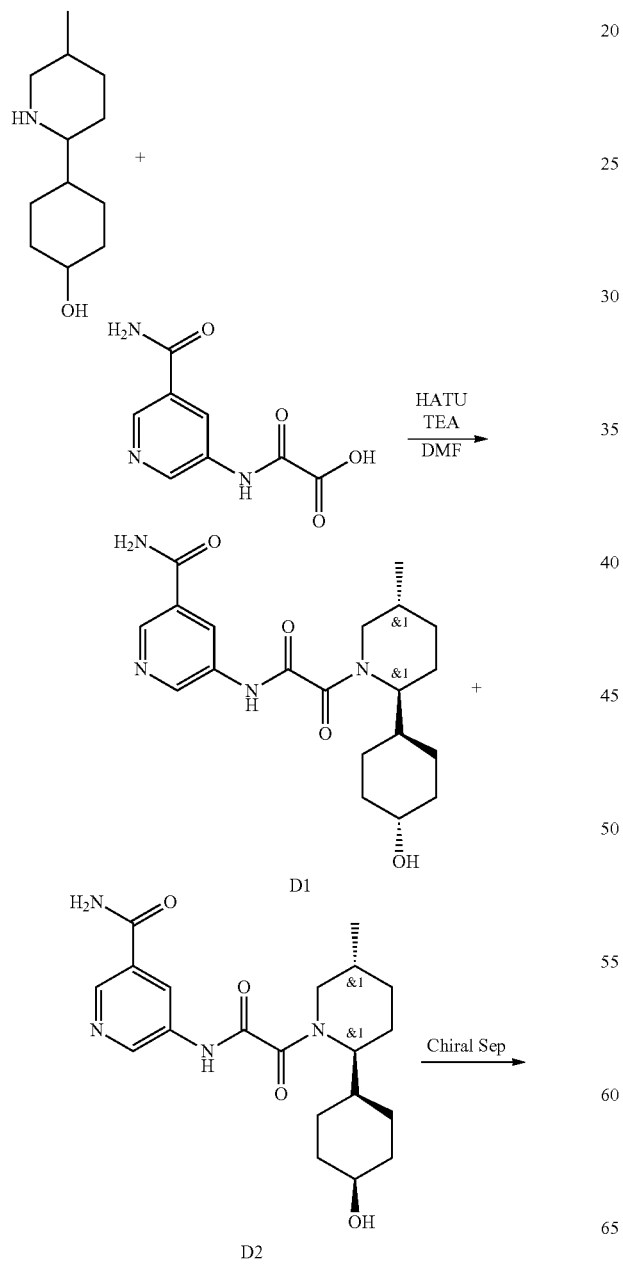

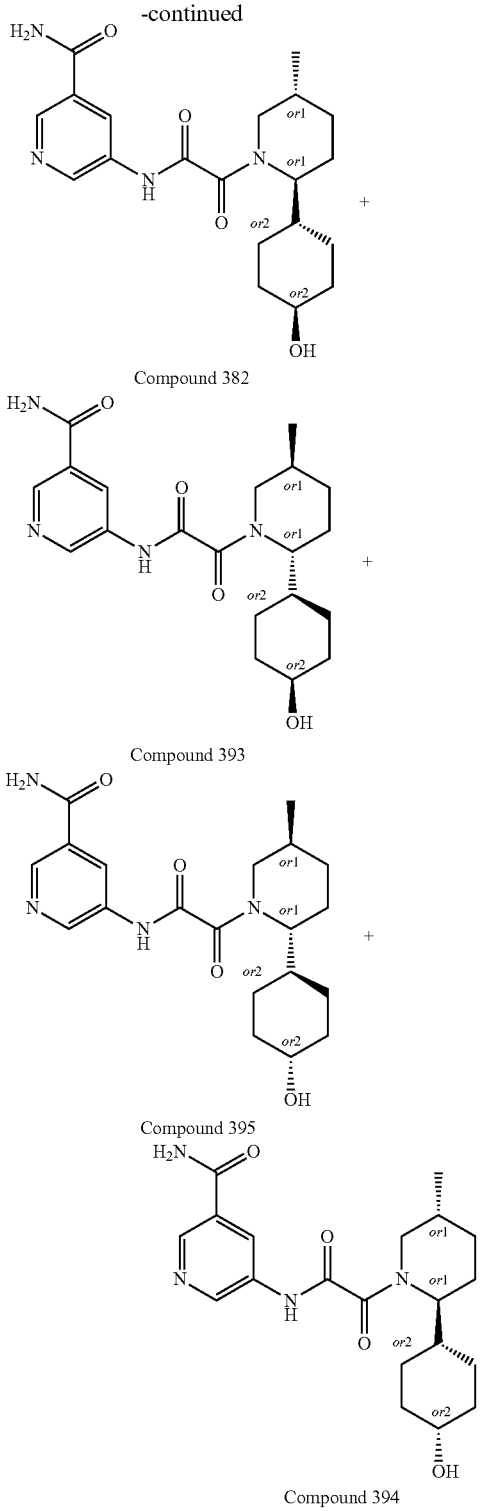

Step 1: Synthesis of 5-(2-(2-(4-hydroxycyclohexyl)-5-methylpiperidin-1-yl)-2-oxoacetamido)Nicotinamide A mixture of 4-(5-methyl-2-piperidyl)cyclohexanol (0.4 g, 2.03 mmol), 2-[(5-carbamoyl-3-pyridyl)amino]-2-oxoacetic acid (566.22 mg, 1.82 mmol) and TEA (2.05 g, 20.27 mmol, 2.83 mL) in DMF (20 mL) was stirred at 25° C. for 0.25 hr, then HATU (693.72 mg, 1.82 mmol) was added in small portions over 0.5 hr. The reaction mixture was stirred at 25° C. for 2 hr, then concentrated in vacuo to 5 ml and submitted to reverse phase HPLC (column: SunFire C18 100×19 mm 5 um, mobile phase 20-65% 0-5 min water-MeOH+FA, flow: 30 ml/min), which afforded 5-[[2-[(2S,5R)-2-(4-hydroxycyclohexyl)-5-methyl-1-piperidyl]-2-oxo-acetyl]amino]pyridine-3-carboxamide (148 mg, 380.99 μmol, 18.79% yield) and 5-[[2-[(2S,5R)-2-(4-hydroxycyclohexyl)-5-methyl-1-piperidyl]-2-oxo-acetyl]amino]pyridine-3-carboxamide (212 mg, 545.75 μmol, 26.92% yield) as light-yellow gums.

D1: $^1$H NMR (400 MHz, DMSO-d$_6$) δ (ppm) 0.96 (d, 3H), 1.28 (m, 8H), 1.62 (m, 4H), 1.84 (m, 4H), 3.71 (m, 1H), 4.23 (m, 2H), 7.57 (s, 1H), 8.10 (m, 1H), 8.47 (m, 1H), 8.73 (s, 1H), 8.87 (m, 1H), 11.06 (m, 1H).

LCMS(ESI): [M]$^+$ m/z: calcd 388.2; found 389.2; Rt=2.388 min.

D2: $^1$H NMR (400 MHz, DMSO-d$_6$) δ (ppm) 0.96 (d, 3H), 1.28 (m, 8H), 1.62 (m, 4H), 1.84 (m, 4H), 3.71 (m, 1H), 4.23 (m, 2H), 7.57 (s, 1H), 8.10 (m, 1H), 8.47 (m, 1H), 8.73 (s, 1H), 8.87 (m, 1H), 11.06 (m, 1H).

LCMS(ESI): [M]$^+$ m/z: calcd 388.2; found 389.2; Rt=2.595 min.

Step 2: Chiral Separation (Compound 393, Compound 382 and Compound 394, Compound 395

Racemic 5-[[2-[(2S,5R)-2-(4-hydroxycyclohexyl)-5-methyl-1-piperidyl]-2-oxo-acetyl]amino]pyridine-3-carboxamide (212.00 mg, 545.75 μmol) was submitted to preparative chiral HPLC (Column: Chiralcel IA (250*20, 5 mkm), Mobile phase: Hexane-IPA-MeOH, 60-20-20; Flow rate: 12 ml/min. 24° C., Wavelength: 205 nm, 225 nm) to afford Compound 382 5-[[2-[(2S,5R)-2-(4-hydroxycyclohexyl)-5-methyl-1-piperidyl]-2-oxo-acetyl]amino]pyridine-3-carboxamide (63.1 mg, 162.44 μmol, 29.76% yield) (Ret.time=13.45 min.) and Compound 393 5-[[2-[(2R,5S)-2-(4-hydroxycyclohexyl)-5-methyl-1-piperidyl]-2-oxo-acetyl]amino]pyridine-3-carboxamide (63.3 mg, 162.95 μmol, 29.86% yield) (Ret.time=31.52 min.).

Racemic 5-[[2-[(2S,5R)-2-(4-hydroxycyclohexyl)-5-methyl-1-piperidyl]-2-oxo-acetyl]amino]pyridine-3-carboxamide (148 mg, 380.99 μmol) was submitted to preparative chiral HPLC (column:Chiralpak IB (250*20, 5 mkm); mobile phase: Hexane-IPA-MeOH, 80-10-10, flow rate: 15 ml/min) to afford Compound 395 5-[[2-[(2R,5S)-2-(4-hydroxycyclohexyl)-5-methyl-1-piperidyl]-2-oxo-acetyl]amino]pyridine-3-carboxamide (47.9 mg, 123.31 μmol, 32.36% yield) (Ret. time=17.290 min.) and Compound 394 5-[[2-[(2S,5R)-2-(4-hydroxycyclohexyl)-5-methyl-1-piperidyl]-2-oxo-acetyl]amino]pyridine-3-carboxamide (43.6 mg, 112.24 μmol, 29.46% yield) (Ret.time=24.069 min.).

Compound 393: Retention time: 31.52 min $^1$H NMR (600 MHz, DMSO-d$_6$) δ (ppm) 0.92-1.02 (m, 3H), 1.09-1.21 (m, 1H), 1.21-1.32 (m, 3H), 1.33-1.45 (m, 3H), 1.45-1.57 (m, 1H), 1.58-1.67 (m, 3H), 1.81-2.00 (m, 3H), 2.84-3.25 (m, 1H), 3.33-3.57 (m, 1H), 3.69-3.80 (m, 1H), 3.95-4.37 (m, 2H), 7.59 (s, 1H), 8.15 (s, 1H), 8.42-8.53 (m, 1H), 8.71-8.80 (m, 1H), 8.84-8.92 (m, 1H), 10.98-11.16 (m, 1H).

LCMS(ESI): [M]$^+$ m/z: calcd 388.2; found 389.2; Rt=2.415 min.

Compound 382: Retention time: 13.45 min $^1$H NMR (600 MHz, DMSO-d$_6$) δ (ppm) 0.89-1.04 (m, 3H), 1.07-1.29 (m, 3H), 1.29-1.45 (m, 4H), 1.45-1.57 (m, 1H), 1.57-1.66 (m, 3H), 1.80-1.99 (m, 3H), 2.84-3.22 (m, 1H), 3.34-3.58 (m, 1H), 3.67-3.81 (m, 1H), 3.98-4.33 (m, 2H), 7.59 (s, 1H), 8.15 (s, 1H), 8.43-8.51 (m, 1H), 8.65-8.80 (m, 1H), 8.84-8.93 (m, 1H), 10.95-11.13 (m, 1H).

LCMS(ESI): [M]$^+$ m/z: calcd 388.2; found 389.2; Rt=2.417 min.

Compound 394: Retention time: 24.07 min $^1$H NMR (600 MHz, DMSO-d$_6$) δ (ppm) 0.77-0.87 (m, 1H), 0.89-1.02 (m, 5H), 1.07-1.16 (m, 2H), 1.21-1.30 (m, 1H), 1.50-1.68 (m, 3H), 1.72-2.00 (m, 6H), 2.86-3.19 (m, 1H), 3.35-3.78 (m, 1H), 3.95-4.11 (m, 1H), 4.31-4.50 (m, 1H), 7.59 (s, 1H), 8.09-8.23 (m, 1H), 8.37-8.52 (m, 1H), 8.70-8.79 (m, 1H), 8.82-8.92 (m, 1H), 10.94-11.13 (m, 1H).

LCMS(ESI): [M]$^+$ m/z: calcd 388.2; found 389.2; Rt=2.225 min.

Compound 395: Retention time: 17.29 min $^1$H NMR (600 MHz, DMSO-d$_6$) δ (ppm) 0.71-0.91 (m, 2H), 0.91-1.01 (m, 4H), 1.04-1.18 (m, 2H), 1.22-1.34 (m, 1H), 1.50-1.68 (m, 3H), 1.72-1.98 (m, 6H), 2.85-3.24 (m, 1H), 3.40-3.76 (m, 1H), 3.96-4.11 (m, 1H), 4.31-4.51 (m, 1H), 7.59 (s, 1H), 8.07-8.22 (m, 1H), 8.42-8.50 (m, 1H), 8.72-8.79 (m, 1H), 8.81-8.95 (m, 1H), 10.97-11.09 (m, 1H).

LCMS(ESI): [M]$^+$ m/z: calcd 388.2; found 389.2; Rt=2.222 min.

Example 99. The Synthesis of 5-[[2-[(2R,5S)-5-methyl-2-(1H-pyrazolo[3,4-b]pyridin-5-yl)-1-piperidyl]-2-oxo-acetyl]amino]pyridine-3-carboxamide (Compound 550 and 5-[[2-[(2S,5R)-5-methyl-2-(1H-pyrazolo[3,4-b]pyridin-5-yl)-1-piperidyl]-2-oxo-acetyl]amino]pyridine-3-carboxamide (Compound 574

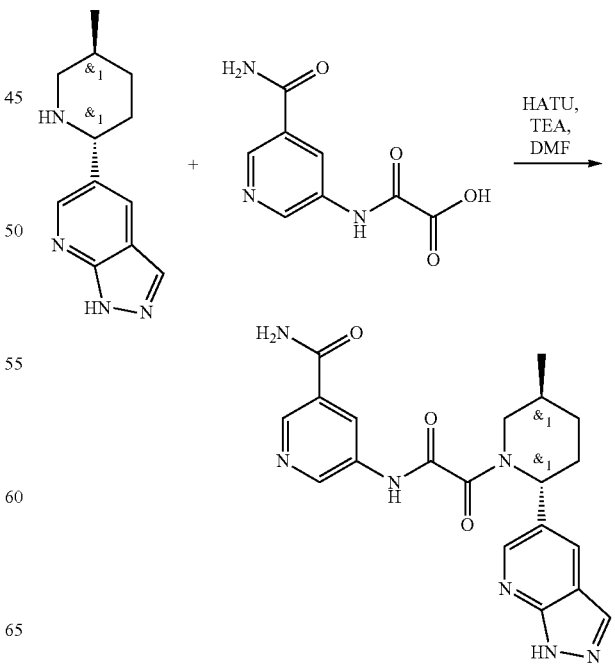

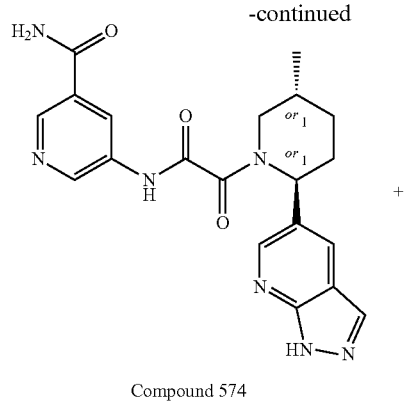

Compound 574

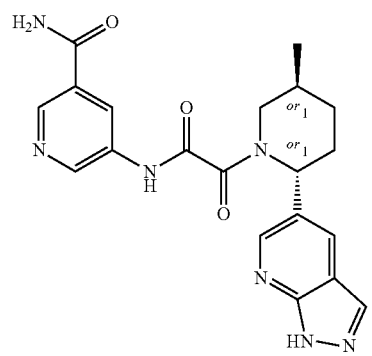

Compound 550

Step 1: Synthesis of 5-[[2-[5-methyl-2-(1H-pyrazolo[3,4-b]pyridin-5-yl)-1-piperidyl]-2-oxo-acetyl]amino]pyridine-3-carboxamide 2-[(5-carbamoyl-3-pyridyl)amino]-2-oxo-acetic acid (340.69 mg, 1.39 mmol, HCl) (190.00 mg, 1.01 mmol) and 5-(5-methyl-2-piperidyl)-1H-pyrazolo[3,4-b]pyridine (0.3 g, 1.39 mmol) were mixed in DMF (10 mL). The reaction suspension was cooled to 20° C. and HATU (527.41 mg, 1.39 mmol) followed by TEA (421.08 mg, 4.16 mmol, 579.99 μL) were added and stirred at ambient temperature for 14 hr. The reaction mixture was evaporated in vacuo and obtained crude product 0.41 g was purified by preparative 20-70% 0-9.5 min water-methanol (NH$_3$ 0.1%), flow 30 ml/min to afford product 5-[[2-[5-methyl-2-(1H-pyrazolo[3,4-b]pyridin-5-yl)-1-piperidyl]-2-oxo-acetyl]amino]pyridine-3-carboxamide (0.045 g, 110.45 μmol, 7.96% yield).

LCMS(ESI): [M+H]$^+$ m/z: calcd 407.2; found 408.2; Rt=1.945 min.

Step 2: Synthesis of 5-[[2-[(2R,5S)-5-methyl-2-(1H-pyrazolo[3,4-b]pyridin-5-yl)-1-piperidyl]-2-oxo-acetyl]amino]pyridine-3-carboxamide (Compound 550) and 5-[[2-[(2S,5R)-5-methyl-2-(1H-pyrazolo[3,4-b]pyridin-5-yl)-1-piperidyl]-2-oxo-acetyl]amino]pyridine-3-carboxamide (Compound 574

The enantiomers were separated by chiral HPLC (column: OJ-H (250*20, 5 mkm)), Hexane-IPA-MeOH, 60-20-20, 14 ml/min as mobile phase) to give the two individual enantiomers Compound 574 5-[[2-[(2R,5S)-5-methyl-2-(1H-pyrazolo[3,4-b]pyridin-5-yl)-1-piperidyl]-2-oxo-acetyl]amino]pyridine-3-carboxamide (11.97 mg, 29.38 μmol, 26.60% yield) and Compound 550 5-[[2-[(2S,5R)-5-methyl-2-(1H-pyrazolo[3,4-b]pyridin-5-yl)-1-piperidyl]-2-oxo-acetyl]amino]pyridine-3-carboxamide (0.01063 g, 26.09 μmol, 23.62% yield)

Compound 550: $^1$H NMR (600 MHz, DMSO-d$_6$) δ 1.00-1.06 (m, 3H), 1.32-1.43 (m, 1H), 1.73-1.81 (m, 1H), 1.86-1.93 (m, 1H), 2.08-2.23 (m, 1H), 2.26-2.33 (m, 1H), 2.84-3.05 (m, 1H), 3.47-4.02 (m, 1H), 5.33-5.75 (m, 1H), 7.51-7.65 (m, 1H), 8.09-8.22 (m, 3H), 8.40-8.56 (m, 2H), 8.69-8.79 (m, 1H), 8.79-8.95 (m, 1H), 11.11-11.46 (m, 1H), 13.56-13.81 (m, 1H).

LCMS(ESI): [M+H]$^+$ m/z: calcd 407.4; found 408.2; Rt=3.677 min.

RT (Hexane-IPA-MeOH, 60-20-20, 14 ml/min)=16.901 min.

Compound 574: $^1$H NMR (600 MHz, DMSO-d$_6$) δ 1.02-1.07 (m, 3H), 1.30-1.44 (m, 1H), 1.71-1.84 (m, 1H), 1.84-1.96 (m, 1H), 2.06-2.28 (m, 1H), 2.28-2.36 (m, 1H), 2.80-3.22 (m, 1H), 3.49-4.07 (m, 1H), 5.27-5.73 (m, 1H), 7.50-7.65 (m, 1H), 8.06-8.21 (m, 3H), 8.41-8.57 (m, 2H), 8.70-8.79 (m, 1H), 8.79-8.96 (m, 1H), 11.07-11.56 (m, 1H), 13.42-13.84 (m, 1H).

LCMS(ESI): [M+H]$^+$ m/z: calcd 407.4; found 408.2; Rt=3.676 min.

RT (Hexane-IPA-MeOH, 60-20-20, 14 ml/min)=22.91 min.

Example 100. The Synthesis of 2-methoxy-5-[[2-[(2S,5R)-5-methyl-2-(1H-pyrazolo[3,4-b]pyridin-5-yl)-1-piperidyl]-2-oxo-acetyl]amino]pyridine-3-carboxamide (Compound 537) and 2-methoxy-5-[[2-[(2R,5S)-5-methyl-2-(1H-pyrazolo[3,4-b]pyridin-5-yl)-1-piperidyl]-2-oxo-acetyl]amino]pyridine-3-carboxamide (Compound 546

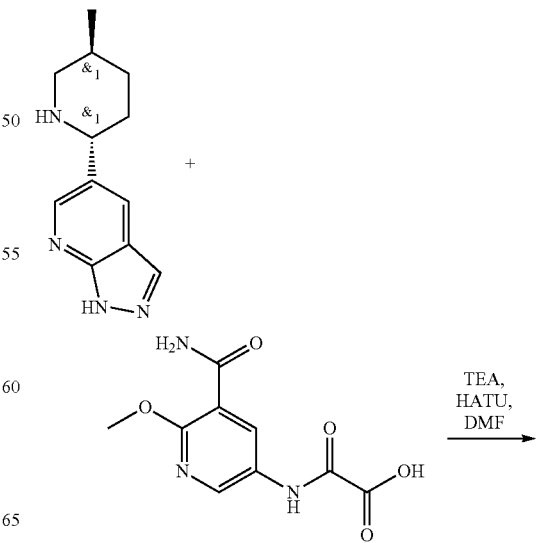

-continued

Compound 537

Compound 546

Step 1: Synthesis of 2-methoxy-5-[[2-[5-methyl-2-(1H-pyrazolo[3,4-b]pyridin-5-yl)-1-piperidyl]-2-oxo-acetyl]amino]pyridine-3-carboxamide 2-[(5-carbamoyl-6-methoxy-3-pyridyl)amino]-2-oxo-acetic acid (472.13 mg, 1.39 mmol, C6H15N) and 5-(5-methyl-2-piperidyl)-1H-pyrazolo[3,4-b]pyridine (0.3 g, 1.39 mmol) were mixed in DMF. The reaction suspension was cooled to 0° C. and HATU (527.41 mg, 1.39 mmol) followed by TEA (421.08 mg, 4.16 mmol, 579.99 µL) were added and stirred at ambient temperature for 12 hr. The reaction mixture was evaporated in vacuo and obtained crude product 0.4 g was purified by preparative HPLC (C18 column, 30-80% 0-9.5 min water-methanol (NH₃0.1%), flow 30 mL/min) to afford product 2-methoxy-5-[[2-[5-methyl-2-(1H-pyrazolo[3,4-b]pyridin-5-yl)-1-piperidyl]-2-oxo-acetyl]amino]pyridine-3-carboxamide (0.11 g, 251.46 µmol, 18.13% yield).

LCMS(ESI): [M+H]⁺ m/z: calcd 437.2; found 438.2; Rt=1.037 min.

Step 2: The Synthesis of 2-methoxy-5-[[2-[(2S,5R)-5-methyl-2-(1H-pyrazolo[3,4-b]pyridin-5-yl)-1-piperidyl]-2-oxo-acetyl]amino]pyridine-3-carboxamide (Compound 537) and 2-methoxy-5-[[2-[(2R,5S)-5-methyl-2-(1H-pyrazolo[3,4-b]pyridin-5-yl)-1-piperidyl]-2-oxo-acetyl]amino]pyridine-3-carboxamide (Compound 546

The enantiomers were separated by HPLC (30-80% 0-9.5 min water-methanol (NH₃0.1%), flow 30 mL/min; (loading pump 4 mL/min methanol (NH₃ 0.1%)) target mass 438 column: YMC-Actus Triart C18 100*20 mmI.D. S-5 um) as mobile phase) to give the two individual enantiomers Compound 537—rel-2-methoxy-5-[[2-[(2S,5R)-5-methyl-2-(1H-pyrazolo[3,4-b]pyridin-5-yl)-1-piperidyl]-2-oxo-acetyl]amino]-pyridine-3-carboxamide (0.03614 g, 82.61 µmol, 32.85% yield) and Compound 546—rel-2-methoxy-5-[[2-[(2R,5S)-5-methyl-2-(1H-pyrazolo[3,4-b]pyridin-5-yl)-1-piperidyl]-2-oxo-acetyl]amino]pyridine-3-carboxamide (0.04262 g, 97.43 µmol, 38.75% yield)

Compound 537: ¹H NMR (600 MHz, DMSO-d₆) δ 0.97-1.09 (m, 3H), 1.28-1.43 (m, 1H), 1.69-1.81 (m, 1H), 1.84-1.96 (m, 1H), 2.05-2.23 (m, 1H), 2.23-2.35 (m, 1H), 2.64-3.27 (m, 1H), 3.45-4.04 (m, 4H), 5.27-5.77 (m, 1H), 7.63-7.82 (m, 2H), 8.06-8.22 (m, 2H), 8.39-8.59 (m, 3H), 10.99-11.11 (m, 1H), 13.57-13.67 (m, 1H).

LCMS(ESI): [M+H]⁺ m/z: calcd 437.5; found 438.0; Rt=4.053 min.

RT (IB, CO₂-MeOH, 70-30, 2.0 mL/min)=8.8722 min.

Compound 546: ¹H NMR (600 MHz, DMSO-d₆) δ 0.99-1.07 (m, 3H), 1.28-1.43 (m, 1H), 1.71-1.81 (m, 1H), 1.84-1.95 (m, 1H), 2.07-2.23 (m, 1H), 2.24-2.34 (m, 1H), 2.63-3.26 (m, 1H), 3.47-4.04 (m, 4H), 5.25-5.80 (m, 1H), 7.62-7.81 (m, 2H), 8.03-8.26 (m, 2H), 8.37-8.62 (m, 3H), 10.97-11.12 (m, 1H), 13.57-13.68 (m, 1H).

LCMS(ESI): [M+H]⁺ m/z: calcd 437.5; found 438.0; Rt=4.051 min.

RT (IB, CO₂-MeOH, 70-30, 2.0 mL/min)=12.1912 min.

Example 101. The Synthesis of 5-[[2-[(2S,5R)-2-(3-chloro-4-fluoro-phenyl)-5-methyl-1-piperidyl]-2-oxo-acetyl]amino]pyridine-3-carboxamide (Compound 513) and 5-[[2-[(2R,5S)-2-(3-chloro-4-fluoro-phenyl)-5-methyl-1-piperidyl]-2-oxo-acetyl]amino]pyridine-3-carboxamide (Compound 512

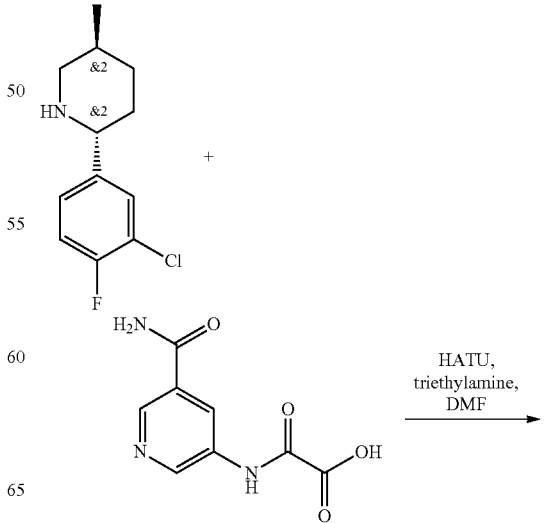

-continued

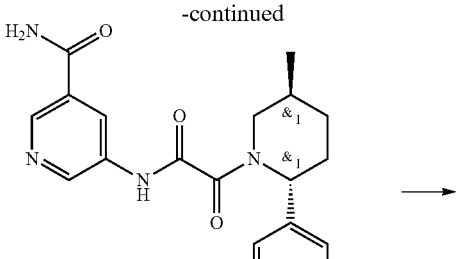

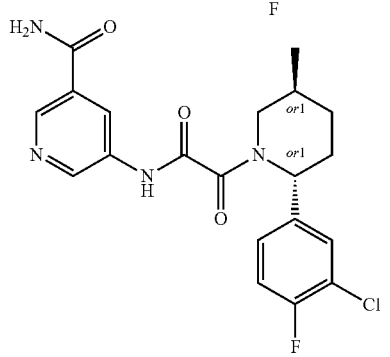

Compound 513

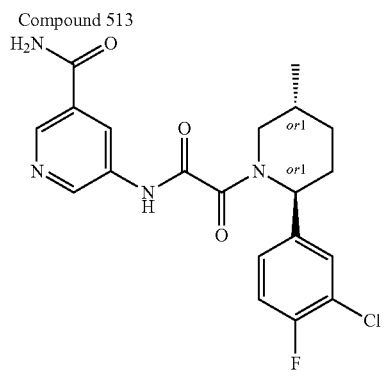

Compound 512

Step 1: Synthesis of 5-[[2-[2-(3-chloro-4-fluoro-phenyl)-5-methyl-1-piperidyl]-2-oxo-acetyl]amino] pyridine-3-carboxamide 2-[(5-carbamoyl-3-pyridyl)amino]-2-oxo-acetic acid (545.17 mg, 1.76 mmol, Et₃N), HATU (667.93 mg, 1.76 mmol) and triethylamine (177.76 mg, 1.76 mmol, 244.84 µL) were mixed in dry DMF (5 mL) at 21° C. and the resulting mixture was stirred for 1 hr. 2-(3-chloro-4-fluoro-phenyl)-5-methyl-piperidine (0.4 g, 1.76 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (50-80% 2-7 min; water—r1+nh3; 30 ml/min; loading pump 4 ml/min r1+nh3; column SunFire 19*100 mm). Two fractions of 5-[[2-[2-(3-chloro-4-fluoro-phenyl)-5-methyl-1-piperidyl]-2-oxo-acetyl]amino]pyridine-3-carboxamide (404.2 mg, 965.03 µmol, 54.94% yield) were obtained: 1st—95.9 mg (92.55% trans) and 2nd—308.3 mg (88.21% trans).

LCMS(ESI): [M+H]⁺ m/z: calcd 418.1; found 419.2; Rt=3.248 min.

Step 2: Synthesis of 5-[[2-[(2S,5R)-2-(3-chloro-4-fluoro-phenyl)-5-methyl-1-piperidyl]-2-oxo-acetyl] amino]pyridine-3-carboxamide (Compound 513) and 5-[[2-[(2R,5S)-2-(3-chloro-4-fluoro-phenyl)-5-methyl-1-piperidyl]-2-oxo-acetyl]amino]pyridine-3-carboxamide (Compound 512)

Chiral separation: IA (100*20, 5 mkm), Hexane-IPA-MeOH, 50-25-25, 15 ml/min, V (solvent)=0.225 L/injection; V injection=10 mL/injection; Time is 0.5 hours/injection; Rt (Compound 513)=11.9 min; Rt (Compound 512)=15.07 min; RT for 5-[[2-[(2S,5R)-2-(3-chloro-4-fluoro-phenyl)-5-methyl-1-piperidyl]-2-oxo-acetyl]amino]pyridine-3-carboxamide (36.54 mg, 87.24 µmol, 38.10% yield)=7.7912 min (IA-3, Hexane-IPA-MeOH, 50-25-25, 0.155 ml/min)

RT for 5-[[2-[(2R,5S)-2-(3-chloro-4-fluoro-phenyl)-5-methyl-1-piperidyl]-2-oxo-acetyl]amino]pyridine-3-carboxamide (31.56 mg, 75.35 µmol, 32.91% yield)=10.0042 min (IA-3, Hexane-IPA-MeOH, 50-25-25, 0.155 ml/min)

Compound 512: ¹H NMR (600 MHz, DMSO-$d_6$) δ 0.98-1.05 (m, 3H), 1.25-1.41 (m, 1H), 1.59-1.69 (m, 1H), 1.81-1.95 (m, 1H), 1.99-2.14 (m, 1H), 2.14-2.28 (m, 1H), 2.77-3.24 (m, 1H), 3.46-4.06 (m, 1H), 5.11-5.59 (m, 1H), 7.29-7.38 (m, 1H), 7.38-7.46 (m, 1H), 7.46-7.53 (m, 1H), 7.56-7.66 (m, 1H), 8.08-8.23 (m, 1H), 8.43-8.53 (m, 1H), 8.71-8.81 (m, 1H), 8.81-8.92 (m, 1H), 11.09-11.39 (m, 1H).

LCMS(ESI): [M+H]⁺ m/z: calcd 418.1; found 419.2; Rt=2.789 min.

RT (IA-3, Hexane-IPA-MeOH, 50-25-25, 0.155 ml/min)=10.0042 min

Compound 513: ¹H NMR (600 MHz, DMSO-$d_6$) δ 0.98-1.05 (m, 3H), 1.26-1.39 (m, 1H), 1.61-1.71 (m, 1H), 1.81-1.96 (m, 1H), 2.00-2.14 (m, 1H), 2.14-2.25 (m, 1H), 2.77-3.23 (m, 1H), 3.46-4.04 (m, 1H), 5.08-5.58 (m, 1H), 7.28-7.38 (m, 1H), 7.38-7.46 (m, 1H), 7.46-7.54 (m, 1H), 7.55-7.64 (m, 1H), 8.02-8.22 (m, 1H), 8.37-8.54 (m, 1H), 8.71-8.80 (m, 1H), 8.81-8.95 (m, 1H), 11.01-11.49 (m, 1H).

LCMS(ESI): [M+H]⁺ m/z: calcd 418.1; found 419.2; Rt=2.787 min.

RT (IA-3, Hexane-IPA-MeOH, 50-25-25, 0.155 ml/min)=7.7912 min.

Example 102. The Synthesis of 5-[[2-[(2S,5R)-2-(3,4-Dichlorophenyl)-5-methyl-1-piperidyl]-2-oxo-acetyl]amino]pyridine-3-carboxamide (Compound 488) and 5-[[2-[(2R,5S)-2-(3,4-Dichlorophenyl)-5-methyl-1-piperidyl]-2-oxo-acetyl]amino]pyridine-3-carboxamide (Compound 489

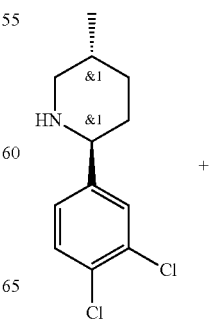

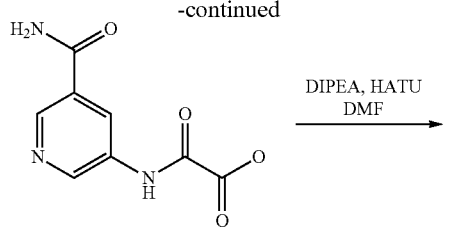

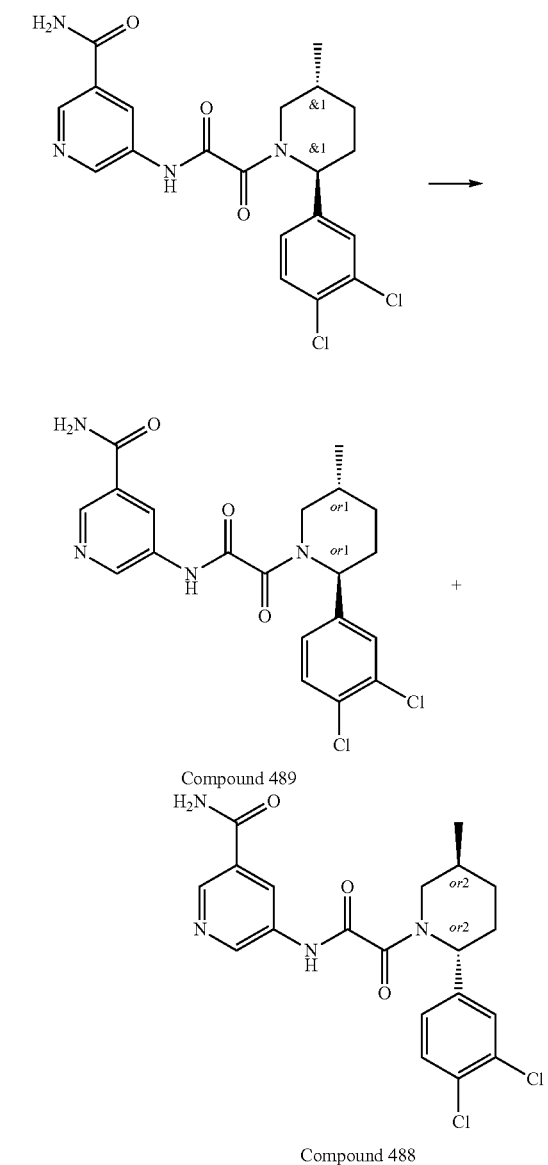

Compound 489

Compound 488

Step 1: Synthesis of 5-[[2-[2-(3,4-Dichlorophenyl)-5-methyl-1-piperidyl]-2-oxo-acetyl]amino]pyridine-3-carboxamide(-[[2-[2-(3,4-Dichlorophenyl)-5-methyl-1-piperidyl]-2-oxo-acetyl]amino]pyridine-3-carboxamide DIPEA (762.25 mg, 5.90 mmol, 1.03 mL) was added to the solution of respective 2-(3,4-dichlorophenyl)-5-methyl-piperidine (0.36 g, 1.47 mmol) and 2-[(5-carbamoyl-3-pyridyl)amino]-2-oxo-acetic acid (308.39 mg, 1.26 mmol, HCl) in DMF (10 mL). The resulting mixture was stirred for 5 min followed by the addition of the solution of HATU (616.69 mg, 1.62 mmol). Then, the reaction mixture was stirred overnight at room temperature. After the completion of the reaction, monitored by LCMS, the resulting suspension was concentrated under reduced pressure. The obtained solid was subjected to HPLC (2-10 min 40-60% water/acn+ $NH_3$ (loading pump 4 ml) column: TRIART 100*20 5 MicroM) to afford pure 5-[[2-[2-(3,4-dichlorophenyl)-5-methyl-1-piperidyl]-2-oxo-acetyl]amino]pyridine-3-carboxamide (0.43 g, 987.82 μmol, 67.00% yield).

$^1$H NMR (400 MHz, DMSO) 1.03 (d, 3H), 1.23 (m, 1H), 1.62 (m, 1H), 2.10 (m, 3H), 2.39 (s, 3H), 4.10 (m, 1H), 2.35 (m, 1H), 7.38 (s, 1H), 7.61 (d, 1H), 8.10 (d, 1H), 8.28 (s, 1H), 8.52 (s, 1H), 8.92 (s, 1H), 11.30 (s, 1H).

LCMS(ESI): [M+H]$^+$ m/z: calcd 434.1; found 435.2; Rt=3.547 min.

Step 2: The Synthesis of 5-[[2-[(2S,5R)-2-(3,4-Dichlorophenyl)-5-methyl-1-piperidyl]-2-oxo-acetyl]amino]pyridine-3-carboxamide (Compound 488) and 5-[[2-[(2R,5S)-2-(3,4-Dichlorophenyl)-5-methyl-1-piperidyl]-2-oxo-acetyl]amino]pyridine-3-carboxamide (Compound 489

5-[[2-[2-(3,4-Dichlorophenyl)-5-methyl-1-piperidyl]-2-oxo-acetyl]amino]pyridine-3-carboxamide (0.43 g, 987.82 μmol) was chirally separated affording Compound 489—rel-5-[[2-[(2R,5S)-2-(3,4-dichlorophenyl)-5-methyl-1-piperidyl]-2-oxo-acetyl]amino]pyridine-3-carboxamide (125.57 mg, 29.20% yield) and Compound 488—rel-5-[[2-[(2S,5R)-2-(3,4-dichlorophenyl)-5-methyl-1-piperidyl]-2-oxo-acetyl]amino]pyridine-3-carboxamide (132.39 mg, 30.79% yield).

Chiral Separation Conditions: Chiralpak IA (250*30 mm, 5 mkm); Hexane-IPA-MeOH, 50-25-25. Flow Rate: 28 mL/min; Column Temperature: 21° C.; Wavelength: 205 nm. RetTime (isomer A)=12.85 min; RetTime (isomer B)=13.87 min, RetTime (isomer C)=16.97 min, RetTime (isomer D)=24.58 min Compound 488: $^1$H NMR (600 MHz, DMSO-d$_6$) δ 0.98-1.04 (m, 3H), 1.26-1.38 (m, 1H), 1.59-1.68 (m, 1H), 1.82-1.95 (m, 1H), 1.99-2.12 (m, 1H), 2.13-2.25 (m, 1H), 2.75-3.27 (m, 1H), 3.42-4.05 (m, 1H), 5.12-5.56 (m, 1H), 7.26-7.36 (m, 1H), 7.51-7.56 (m, 1H), 7.56-7.62 (m, 1H), 7.62-7.68 (m, 1H), 8.09-8.19 (m, 1H), 8.42-8.52 (m, 1H), 8.71-8.80 (m, 1H), 8.81-8.91 (m, 1H), 11.21-11.39 (m, 1H).

LCMS(ESI): [M+H]$^+$ m/z: calcd 434.1; found 435.0; Rt=1.324 min.

RT(Hexane-IPA-MeOH, 50-25-25, 0.155 ml/min)=14.85 min

Compound 489: $^1$H NMR (600 MHz, DMSO-d$_6$) δ 0.94-1.04 (m, 3H), 1.24-1.40 (m, 1H), 1.56-1.71 (m, 1H), 1.83-1.96 (m, 1H), 2.00-2.13 (m, 1H), 2.14-2.25 (m, 1H), 2.75-3.27 (m, 1H), 3.45-4.08 (m, 1H), 5.13-5.59 (m, 1H), 7.27-7.36 (m, 1H), 7.51-7.57 (m, 1H), 7.57-7.62 (m, 1H), 7.62-7.68 (m, 1H), 8.09-8.19 (m, 1H), 8.42-8.52 (m, 1H), 8.70-8.80 (m, 1H), 8.80-8.92 (m, 1H), 11.13-11.37 (m, 1H).

LCMS(ESI): [M+1]$^+$ m/z: calcd 434.1; found 435.2; Rt=1.325 min.

RT(Hexane-IPA-MeOH, 50-25-25, 0.155 ml/min)=9.49 min.

1445

Example 103. The Synthesis of 5-[[2-[(2S,5R)-2-(3-chloro-4-methyl-phenyl)-5-methyl-1-piperidyl]-2-oxo-acetyl]amino]pyridine-3-carboxamide (Compound 484) and 5-[[2-[(2R,5S)-2-(3-chloro-4-methyl-phenyl)-5-methyl-1-piperidyl]-2-oxo-acetyl]amino]pyridine-3-carboxamide (Compound 485

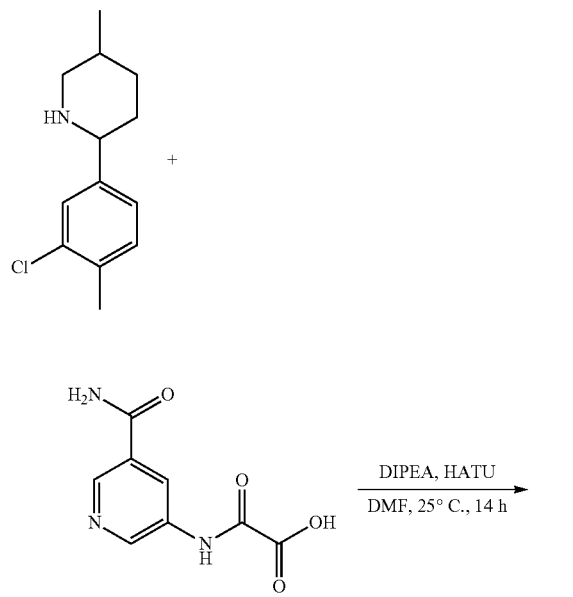

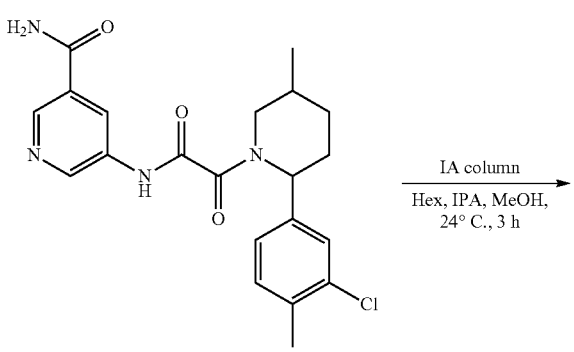

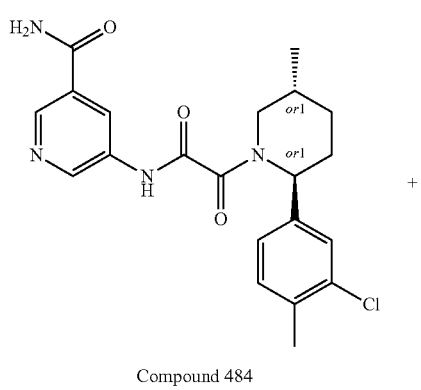

Compound 484

1446

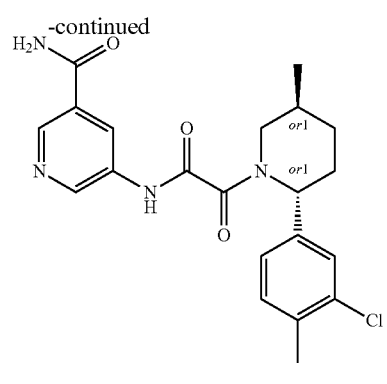

Compound 485

Step 1: The Synthesis of 5-[[2-[2-(3-chloro-4-methyl-phenyl)-5-methyl-1-piperidyl]-2-oxo-acetyl]amino]pyridine-3-carboxamide DIPEA (554.54 mg, 4.29 mmol, 747.36 μL) was added to the solution of respective 2-(3-chloro-4-methyl-phenyl)-5-methyl-piperidine (0.24 g, 1.07 mmol) and 2-[(5-carbamoyl-3-pyridyl)amino]-2-oxo-acetic acid (263.47 mg, 1.07 mmol, HCl) in DMF (10 mL). The resulting mixture was stirred for 5 min followed by the addition of the solution of HATU (448.65 mg, 1.18 mmol). Then, the reaction mixture was stirred overnight at room temperature. After the completion of the reaction, monitored by LCMS, the resulting suspension was concentrated under reduced pressure. The obtained solid was subjected to HPLC (Waters SunFire C18 19*100 mm 5 mkm column, Hexane-MeOH 50-50 as an mobile phase, Flow 12 mL/min) to afford 5-[[2-[2-(3-chloro-4-methyl-phenyl)-5-methyl-1-piperidyl]-2-oxo- acetyl]amino]pyridine-3-carboxamide (0.349 g, 841.20 μmol, 78.42% yield).

LCMS(ESI): [M+H]+ m/z: calcd 414.1; found 415.2; Rt=3.513 min.

Step 2: The Synthesis of 5-[[2-[(2S,5R)-2-(3-chloro-4-methyl-phenyl)-5-methyl-1-piperidyl]-2-oxo-acetyl]amino]pyridine-3-carboxamide (Compound 484) and 5-[[2-[(2R,5S)-2-(3-chloro-4-methyl-phenyl)-5-methyl-1-piperidyl]-2-oxo-acetyl]amino]pyridine-3-carboxamide (Compound 485)

Column: IA (100*20 mm, 5 mkm) Chiralpak column; Reverse Phase & Gradient: Hexane-IPA-MeOH, 50-25-25, 15.0 mL/min 5-[[2-[(2R,5S)-2-(3-chloro-4-methyl-phenyl)-5-methyl-1-piperidyl]-2-oxo-acetyl]amino]pyridine-3-carboxamide (64.53 mg, 18.49% yield) Rel.Time for Compound 485 in analytical conditions 46.81 min 5-[[2-[(2S,5R)-2-(3-chloro-4-methyl-phenyl)-5-methyl-1-piperidyl]-2-oxo-acetyl]amino]pyridine-3-carboxamide (62.68 mg, 17.96% yield) Rel.Time for Compound 484 in analytical conditions 15.45 min Compound 485: RT (IA, Hexane-IPa-MeOH, 50-25-25, 0.6 mL/min)=46.840 min.

1H NMR (600 MHz, DMSO-d6) δ 0.98-1.04 (m, 3H), 1.26-1.39 (m, 1H), 1.60-1.69 (m, 1H), 1.81-1.93 (m, 1H), 1.97-2.13 (m, 1H), 2.14-2.23 (m, 1H), 2.25-2.32 (m, 3H), 2.75-3.25 (m, 1H), 3.43-4.05 (m, 1H), 5.08-5.58 (m, 1H), 7.16-7.24 (m, 1H), 7.28-7.40 (m, 2H), 7.54-7.66 (m, 1H), 8.10-8.20 (m, 1H), 8.42-8.52 (m, 1H), 8.72-8.79 (m, 1H), 8.80-8.93 (m, 1H), 11.11-11.46 (m, 1H).

LCMS(ESI): [M+H]⁺ m/z: calcd 414.2; found 415.2; Rt=1.324 min.

Compound 484: RT (IA, Hexane-IPa-MeOH, 50-25-25, 0.6 mL/min)=15.499 min.

¹H NMR (600 MHz, DMSO-d₆) δ 0.98-1.05 (m, 3H), 1.24-1.36 (m, 1H), 1.58-1.69 (m, 1H), 1.80-1.94 (m, 1H), 1.96-2.14 (m, 1H), 2.14-2.22 (m, 1H), 2.26-2.32 (m, 3H), 2.74-3.25 (m, 1H), 3.43-4.05 (m, 1H), 5.10-5.58 (m, 1H), 7.15-7.24 (m, 1H), 7.28-7.40 (m, 2H), 7.51-7.64 (m, 1H), 8.08-8.21 (m, 1H), 8.40-8.52 (m, 1H), 8.69-8.80 (m, 1H), 8.80-8.92 (m, 1H), 11.05-11.44 (m, 1H).

LCMS(ESI): [M+H]⁺ m/z: calcd 414.2; found 415.2; Rt=1.325 min.

Example 104. The Synthesis of 5-[[2-[(2R,5S)-5-methyl-2-(2-methyl-4-pyridyl)-1-piperidyl]-2-oxo-acetyl]amino]pyridine-3-carboxamide and 5-[[2-[(2S,5R)-5-methyl-2-(2-methyl-4-pyridyl)-1-piperidyl]-2-oxo-acetyl]amino]pyridine-3-carboxamide (Compound 534 and Compound 519

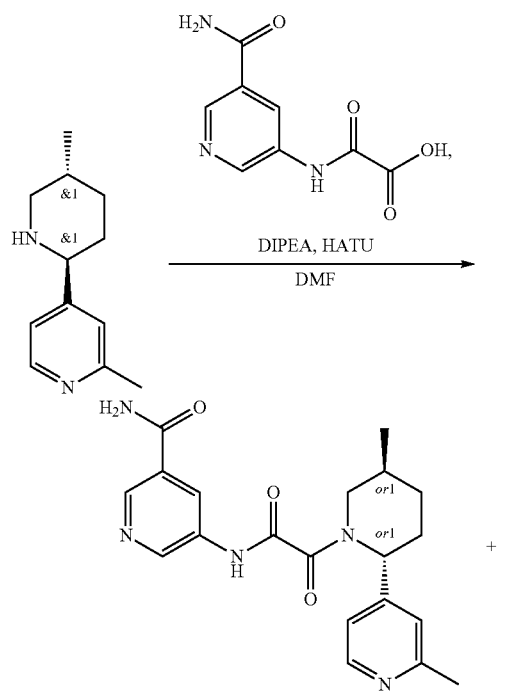

Compound 534

Compound 519

2-methyl-4-(5-methyl-2-piperidyl)pyridine (0.3 g, 1.58 mmol), 2-[(5-carbamoyl-3-pyridyl)amino]-2-oxo-acetic acid (Et₃N salt, 362.73 mg, 1.73 mmol) and DIPEA (611.28 mg, 4.73 mmol, 823.82 µL) were dissolved in DMF (6 mL) under gentle heating. HATU (719.36 mg, 1.89 mmol) was added in small portions under vigorous stirring and occasional heating. The reaction mixture was stirred at 50° C. for 3 hours. Upon completion, the reaction mixture was purified by reverse phase HPLC (Eluent: water-acetonitrile, 10% 0.5-6.5 min; flow rate: 30 mL/min; loading pump: 4 mL/min, acetonitrile; column SunFire 19*100 mm, 5 um) and chiral HPLC (Column: Chiralpak AD-H (250×20 mm×5 um); Mobile phase: Hexane-IPA-MeOH, 60-20-20; Flow Rate: 12 mL/min) to obtain 5-[[2-[(2R,5S)-5-methyl-2-(2-methyl-4-pyridyl)-1-piperidyl]-2-oxo-acetyl]amino]pyridine-3-carboxamide (Compound 534, 80 mg, 209.74 µmol, 13.30% yield) and 5-[[2-[(2S,5R)-5-methyl-2-(2-methyl-4-pyridyl)-1-piperidyl]-2-oxo-acetyl]amino]pyridine-3-carboxamide (Compound 519, 90 mg, 235.96 µmol, 14.97% yield) as white solid.

Compound 534: ¹H NMR (DMSO-d₆, 600 MHz): δ (ppm) 1.01 (m, 3H), 1.33 (m, 1H), 1.56 (m, 1H), 2.06 (m, 3H), 2.44 (s, 2H), 2.77 (m, 0.4H), 3.23 (m, 0.6H), 3.51 (m, 0.6H), 4.06 (d, 0.4H), 5.17 (s, 0.4H), 5.52 (s, 0.6H), 7.14 (m, 2H), 7.59 (m, 1H), 8.14 (m, 1H), 8.44 (m, 2H), 8.82 (m, 2H), 11.25 (m, 1H).

LCMS(ESI): [M+H]⁺ m/z: calcd 381.2; found 382.2; Rt=2.926 min.

Chiral HPLC: Rt=33.14 min (Column: AD-H; Eluent: Hexane-IPA-MeOH, 60-20-20; flow rate: 0.6 mL/min).

Compound 519: ¹H NMR (DMSO-d₆, 600 MHz): δ (ppm) 1.01 (m, 3H), 1.33 (m, 1H), 1.56 (m, 1H), 2.06 (m, 3H), 2.44 (s, 2H), 2.77 (m, 0.4H), 3.23 (m, 0.6H), 3.51 (m, 0.6H), 4.06 (d, 0.4H), 5.17 (s, 0.4H), 5.52 (s, 0.6H), 7.14 (m, 2H), 7.59 (m, 1H), 8.14 (m, 1H), 8.44 (m, 2H), 8.82 (m, 2H), 11.25 (m, 1H).

LCMS(ESI): [M+H]⁺ m/z: calcd 381.2; found 382.2; Rt=2.922 min.

Chiral HPLC: Rt=19.89 min (Column: AD-H; Eluent: Hexane-IPA-MeOH, 60-20-20; flow rate: 0.6 mL/min).

Example 105. The Synthesis of Rac 5-[[2-[(2S,5R)-5-methyl-2-[4-(1H-pyrazol-5-yl)phenyl]-1-piperidyl]-2-oxo-acetyl]amino]pyridine-3-carboxamide (Compound 524), 5-[[2-[(2S,5R)-5-methyl-2-[4-(1H-pyrazol-3-yl)phenyl]-1-piperidyl]-2-oxo-acetyl]amino]pyridine-3-carboxamide (Compound 626) and 5-[[2-[(2R,5S)-5-methyl-2-[4-(1H-pyrazol-3-yl)phenyl]-1-piperidyl]-2-oxo-acetyl]amino]pyridine-3-carboxamide (Compound 627

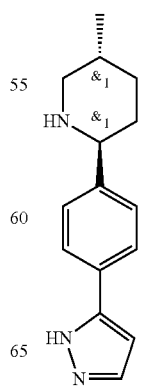

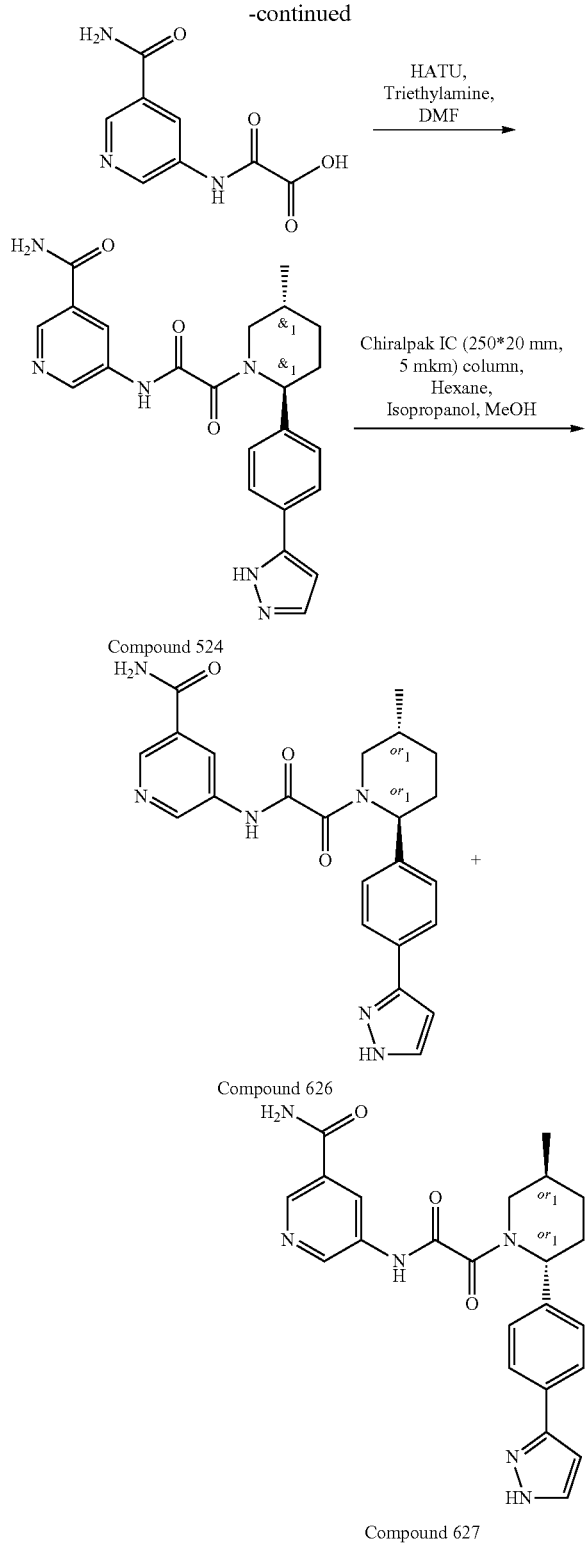

Step 1: Synthesis of rac-5-[[2-[(2S,5R)-5-methyl-2-[4-(1H-pyrazol-5-yl)phenyl]-1-piperidyl]-2-oxo-acetyl]amino]pyridine-3-carboxamide (Compound 524

To a solution of (2S,5R)-5-methyl-2-[4-(1H-pyrazol-5-yl)phenyl]piperidine (125 mg, 397.77 μmol, 2HCl), 2-[(5-carbamoyl-3-pyridyl)amino]-2-oxo-acetic acid (97.70 mg, 397.77 μmol, HCl) and Triethylamine (241.50 mg, 2.39 mmol, 332.65 μL), HATU (166.37 mg, 437.55 μmol) was added portionwise. The resulting mixture was stirred at 25° C. for 3 hr and subjected to HPLC: 30-30-70% 0-1-6 min water-methanol (NH$_3$ 0.1%), flow 30 ml/min (loading pump 4 ml/min methanol (NH$_3$ 0.1%)) column: YMC-Actus Triart C18 100*20 mm1.D. S-5 um) to give 5-[[2-[(2S,5R)-5-methyl-2-[4-(1H-pyrazol-5-yl)phenyl]-1-piperidyl]-2-oxo-acetyl]amino]pyridine-3-carboxamide (92 mg, 212.73 μmol, 53.48% yield).

$^1$H NMR (600 MHz, DMSO-d$_6$) δ 1.00-1.06 (m, 3H), 1.29-1.43 (m, 1H), 1.65-1.76 (m, 1H), 1.79-1.97 (m, 1H), 2.02-2.16 (m, 1H), 2.16-2.30 (m, 1H), 2.75-3.27 (m, 1H), 3.47-4.07 (m, 1H), 5.13-5.65 (m, 1H), 6.66-6.73 (m, 1H), 7.32-7.39 (m, 2H), 7.39-7.98 (m, 5H), 8.07-8.23 (m, 1H), 8.44-8.53 (m, 1H), 8.65-8.80 (m, 1H), 8.82-8.96 (m, 1H).

LCMS(ESI): [M+H]$^+$ m/z: calcd 432.2; found 433.2; Rt=2.020 min.

Step 2: Synthesis of 5-[[2-[(2S,5R)-5-methyl-2-[4-(1H-pyrazol-3-yl)phenyl]-1-piperidyl]-2-oxo-acetyl]amino]pyridine-3-carboxamide (Compound 626) and 5-[[2-[(2R,5S)-5-methyl-2-[4-(1H-pyrazol-3-yl)phenyl]-1-piperidyl]-2-oxo-acetyl]amino]pyridine-3-carboxamide Compound 627

Chiral separation of 5-[[2-[(2S,5R)-5-methyl-2-[4-(1H-pyrazol-3-yl)phenyl]-1-piperidyl]-2-oxo-acetyl]amino]pyridine-3-carboxamide (82.7 mg, 191.23 μmol) (Compound 524) was performed using Chiralpak IC (250*20 mm, 5 mkm) column (191.23 μmol) Hexane-IPA-MeOH, 50-25-25 as a mobile phase; Flow Rate: 12 mL/min; Column Temperature: 21° C.; Wavelength: 205 nm affording Compound 626—rel-5-[[2-[(2S,5R)-5-methyl-2-[4-(1H-pyrazol-3-yl)phenyl]-1-piperidyl]-2-oxo-acetyl]amino]pyridine-3-carboxamide (19.1 mg, 44.16 μmol, 23.10% yield) (RetTime=138.94 min) and Compound 627—rel-5-[[2-[(2R,5S)-5-methyl-2-[4-(1H-pyrazol-3-yl)phenyl]-1-piperidyl]-2-oxo-acetyl]amino]pyridine-3-carboxamide (22.03 mg, 50.94 μmol, 26.64% yield)RetTime (isomer B)=158.77 min).

Compound 626: $^1$H NMR (600 MHz, DMSO-d$_6$) δ 0.99-1.06 (m, 3H), 1.29-1.43 (m, 1H), 1.64-1.76 (m, 1H), 1.83-1.96 (m, 1H), 2.00-2.19 (m, 1H), 2.20-2.31 (m, 1H), 2.77-3.28 (m, 1H), 3.45-4.08 (m, 1H), 5.15-5.67 (m, 1H), 6.62-6.74 (m, 1H), 7.29-7.41 (m, 2H), 7.41-7.61 (m, 1H), 7.61-7.79 (m, 2H), 7.80-7.85 (m, 1H), 8.08-8.21 (m, 1H), 8.43-8.53 (m, 1H), 8.72-8.79 (m, 1H), 8.83-8.94 (m, 1H), 11.20-11.39 (m, 1H), 12.75-13.38 (m, 1H).

LCMS(ESI): [M+H]$^+$ m/z: calcd 432.2; found 433.2; Rt=2.311 min.

RT (Hexane-IPA-MeOH, 50-25-25, 12 ml/min)=10.3252 min

Compound 627: $^1$H NMR (600 MHz, DMSO-d$_6$) δ 1.01-1.06 (m, 3H), 1.31-1.41 (m, 1H), 1.65-1.75 (m, 1H), 1.83-1.95 (m, 1H), 2.01-2.19 (m, 1H), 2.20-2.30 (m, 1H), 2.76-3.28 (m, 1H), 3.44-4.07 (m, 1H), 5.14-5.65 (m, 1H), 6.65-6.73 (m, 1H), 7.32-7.43 (m, 2H), 7.48-7.62 (m, 1H), 7.62-7.76 (m, 1H), 7.75-7.86 (m, 2H), 8.08-8.22 (m, 1H), 8.41-8.54 (m, 1H), 8.66-8.81 (m, 1H), 8.84-8.98 (m, 1H), 11.15-11.40 (m, 1H), 12.79-13.30 (m, 1H).

LCMS(ESI): [M+H]$^+$ m/z: calcd 432.2; found 433.2; Rt=2.316 min.

RT (Hexane-IPA-MeOH, 50-25-25, 12 ml/min)=6.410 min

Example 106. The Synthesis of 5-(2-(2-(3-hydroxy-4-methylphenyl)-5-methylpiperidin-1-yl)-2-oxoacetamido)Nicotinamide (Compound 554

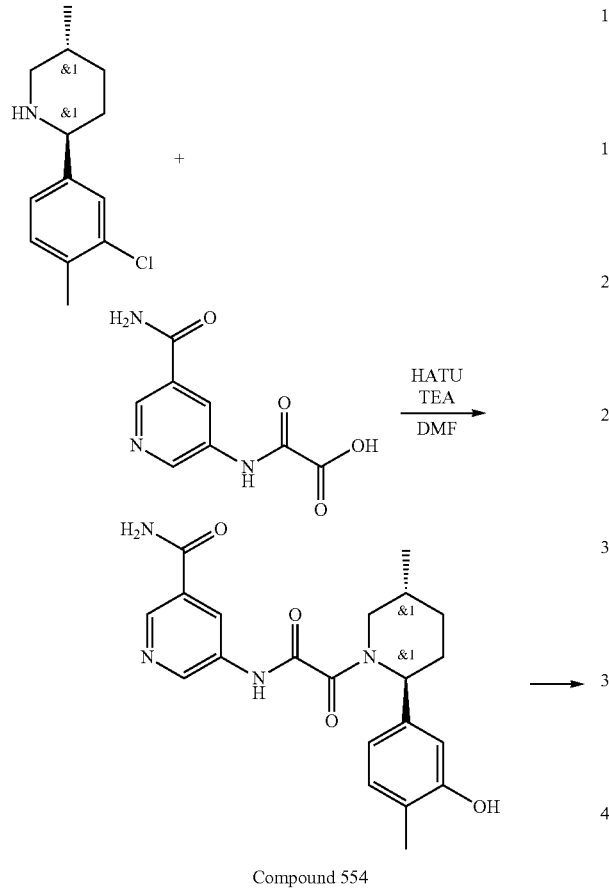

Compound 554

To the solution of 2-methyl-5-[(2S,5R)-5-methyl-2-piperidyl]phenol (299.37 mg, 1.46 mmol, HCl), 2-[(5-carbamoyl-3-pyridyl)amino]-2-oxo-acetic acid (358.18 mg, 1.15 mmol, Et₃N) and TEA (1.03 g, 10.21 mmol, 1.42 mL) in DMF (5 mL) HATU (609.92 mg, 1.60 mmol) was added portionwise. Mixture was stirred at 25° C. for 2 hr. The reaction mixture was submitted for HPLC (20-20-70% 0-1-6 min 0.1% NH₃-MeOH, flow: 30 ml/min (loading pump 4 ml/minMeOH) target mass 396 column: YMC Triart C18 100×20 mm, 5 um) to give 5-[[2-[(2S,5R)-2-(3-hydroxy-4-methyl-phenyl)-5-methyl-1-piperidyl]-2-oxo-acetyl]amino] pyridine-3-carboxamide (48 mg, 121.08 μmol, 8.30% yield). Product contains 6% of cis-isomer.

$^1$H NMR (600 MHz, DMSO-d$_6$) δ (ppm) 0.94-1.07 (m, 3H), 1.25-1.35 (m, 1H), 1.66-1.73 (m, 1H), 1.79-1.91 (m, 1H), 1.92-2.04 (m, 1H), 2.04-2.09 (m, 4H), 2.78-3.24 (m, 1H), 3.48-4.06 (m, 1H), 5.04-5.56 (m, 1H), 6.61-6.69 (m, 1H), 6.70-6.82 (m, 1H), 7.00-7.08 (m, 1H), 7.52-7.65 (m, 1H), 8.07-8.23 (m, 1H), 8.38-8.54 (m, 1H), 8.67-8.80 (m, 1H), 8.82-8.96 (m, 1H), 9.16-9.30 (m, 1H), 11.01-11.37 (m, 1H).

LCMS(ESI): [M]⁺ m/z: calcd 396.4; found 397.2; Rt=2.351 min.

Example 107. The Synthesis of 5-[[2-[(2S,5R)-2-(1H-indazol-4-yl)-5-methyl-1-piperidyl]-2-oxo-acetyl]amino]pyridine-3-carboxamide (Compound 883) and 5-[[2-[(2R,5S)-2-(1H-indazol-4-yl)-5-methyl-1-piperidyl]-2-oxo-acetyl]amino]pyridine-3-carboxamide (Compound 897

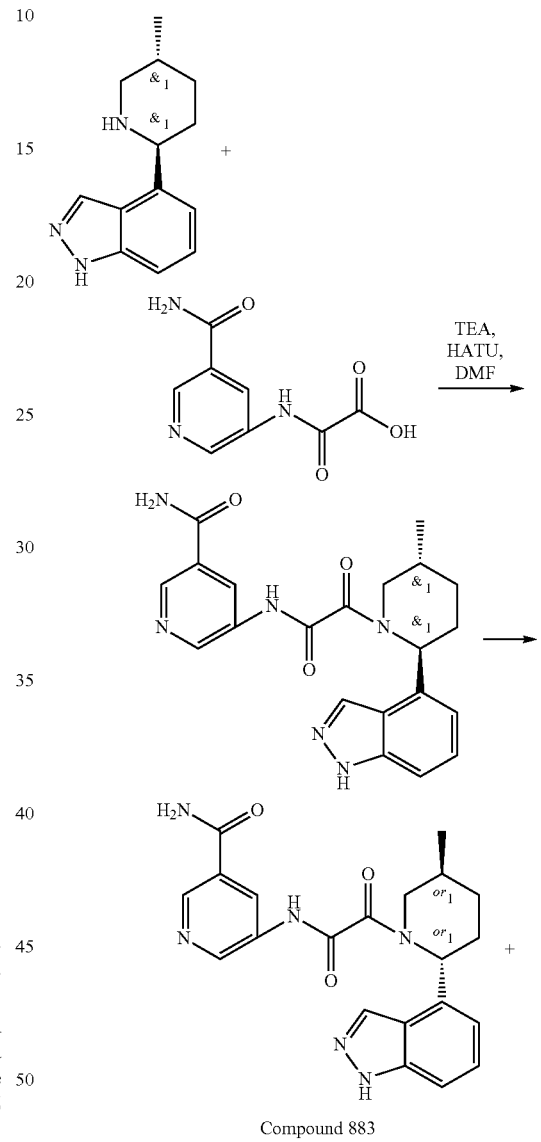

Compound 883

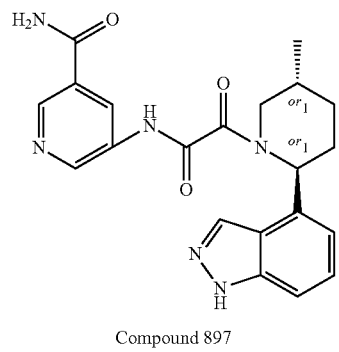

Compound 897

1453

Step 1: Synthesis of 5-[[2-[(2S,5R)-2-(1H-indazol-4-yl)-5-methyl-1-piperidyl]-2-oxo-acetyl]amino]pyridine-3-carboxamide To a stirred mixture of 4-[(2S,5R)-5-methyl-2-piperidyl]-1H-indazole (475 mg, 1.32 mmol, 2HCl), 2-[(5-carbamoyl-3-pyridyl)amino]-2-oxo-acetic acid (275.77 mg, 1.12 mmol, HCl) and Triethylamine (667.07 mg, 6.59 mmol, 918.83 μL) in Dimethylformamide (4 mL) was added HATU (551.45 mg, 1.45 mmol). The resulting reaction mixture was stirred at 20° C. for 4 hr. Then, it was subjected to HPLC (30-30-60% 0-1-6 min H₂O/MeOH/0.1% NH₄OH, flow: 30 ml/min; column: YMC Triart C18 100×20 mm, 5 um), affording 5-[[2-[(2S,5R)-2-(1H-indazol-4-yl)-5-methyl-1-piperidyl]-2-oxo-acetyl]amino]pyridine-3-carboxamide (100 mg, 246.04 μmol, 18.66% yield).

LCMS(ESI): [M+H]⁺ m/z: calcd 406.2; found 407.2; Rt=2.098 min.

Step 2: The Synthesis of 5-[[2-[(2S,5R)-2-(1H-indazol-4-yl)-5-methyl-1-piperidyl]-2-oxo-acetyl]amino]pyridine-3-carboxamide (Compound 883) and 5-[[2-[(2R,5S)-2-(1H-indazol-4-yl)-5-methyl-1-piperidyl]-2-oxo-acetyl]amino]pyridine-3-carboxamide (Compound 897

5-[[2-[(2S,5R)-2-(1H-indazol-4-yl)-5-methyl-1-piperidyl]-2-oxo-acetyl]amino]pyridine-3-carboxamide (10 mg, 24.60 μmol) was divided into enantiomers by Chiral HPLC (Column: Chiralpak IA-I(250*20 mm, 5 mkm); Mobile phase: Hexane-IPA-MeOH 50-25-25, Flow Rate: 12 mL/min; 5 inj., 2 mg/inj. V=3.5 L,time 5.5 h.), affording: Compound 883—5-[[2-[(2S,5R)-2-(1H-indazol-4-yl)-5-methyl-1-piperidyl]-2-oxo-acetyl]amino]pyridine-3-carboxamide (3.5 mg, 8.61 μmol, 70.00% yield) with ret.time=35.174 min and Compound 897—5-[[2-[(2R,5S)-2-(1H-indazol-4-yl)-5-methyl-1-piperidyl]-2-oxo-acetyl]amino]pyridine-3-carboxamide (3 mg, 7.38 μmol, 60.00% yield) with ret.time=42.954 min.

Compound 883: LCMS(ESI): [M+H]⁺ m/z: calcd 406.4; found 407.4; Rt=3.303 min.

RT (Hexane-IPA-MeOH, 50-25-25, 12 ml/min)=25.1832 min.

Compound 897: LCMS(ESI): [M+H]⁺ m/z: calcd 406.4; found 407.4; Rt=3.287 min.

RT (Hexane-IPA-MeOH, 50-25-25, 12 ml/min)=35.4262 min.

Example 108. The Synthesis of 5-[[2-[(2R,5S)-2-(1H-indazol-4-yl)-5-methyl-1-piperidyl]-2-oxo-acetyl]amino]-2-methoxy-pyridine-3-carboxamide (Compound 918) and 5-[[2-[(2S,5R)-2-(1H-indazol-4-yl)-5-methyl-1-piperidyl]-2-oxo-acetyl]amino]-2-methoxy-pyridine-3-carboxamide (Compound 926

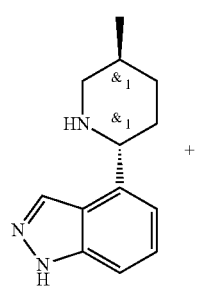

1454

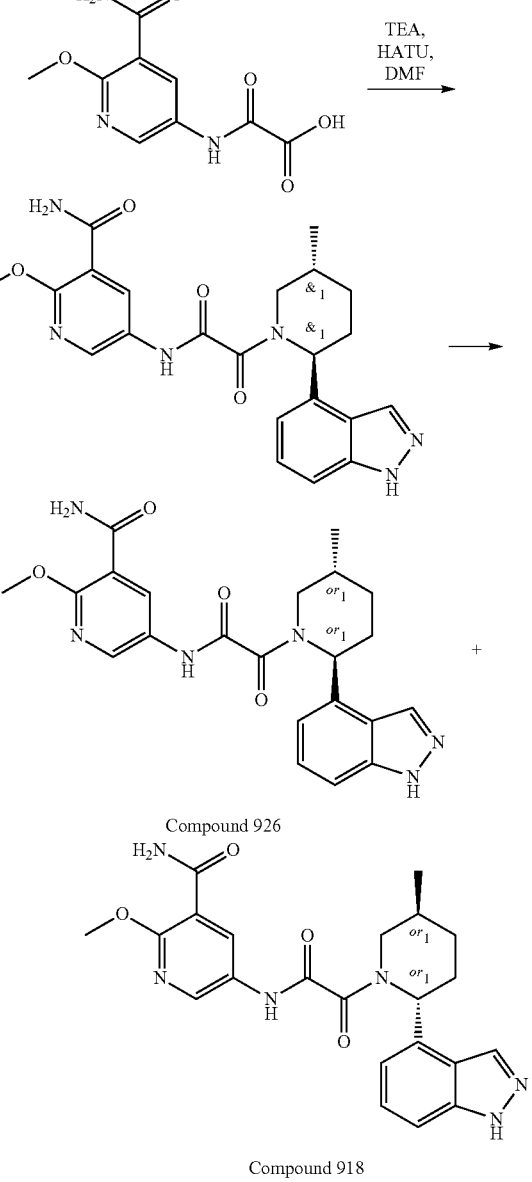

Compound 926

Compound 918

Step 1: Synthesis of 5-[[2-[(2S,5R)-2-(1H-indazol-4-yl)-5-methyl-1-piperidyl]-2-oxo-acetyl]amino]-2-methoxy-pyridine-3-carboxamide To a stirred mixture of 4-[(2S,5R)-5-methyl-2-piperidyl]-1H-indazole (475 mg, 1.32 mmol, 2HCl), 2-[(5-carbamoyl-6-methoxy-3-pyridyl)amino]-2-oxo-acetic acid (315.35 mg, 1.32 mmol) and Triethylamine (667.07 mg, 6.59 mmol, 918.83 μL) in Dimethylformamide (4 mL) was added HATU (551.45 mg, 1.45 mmol). The resulting reaction mixture was stirred at 20° C. for 4 hr. Then, it was subjected to HPLC (20-20-50% 0-1-6 min H₂O/MeCN/0.1% NH₄OH, flow: 30 ml/min; column: YMC Triart C18 100×20 mm, 5 um), affording 5-[[2-[(2S,5R)-2-(1H-indazol-4-yl)-5-methyl-1-piperidyl]-2-oxo-acetyl]amino]-2-methoxy-pyridine-3-carboxamide (135 mg, 309.30 μmol, 23.46% yield).

LCMS(ESI): [M+H]⁺ m/z: calcd 436.2; found 437.0; Rt=2.420 min.

1455

Step 2: Synthesis of 5-[[2-[(2R,5S)-2-(1H-indazol-4-yl)-5-methyl-1-piperidyl]-2-oxo-acetyl]amino]-2-methoxy-pyridine-3-carboxamide (Compound 918 and 5-[[2-[(2S,5R)-2-(1H-indazol-4-yl)-5-methyl-1-piperidyl]-2-oxo-acetyl]amino]-2-methoxy-pyridine-3-carboxamide (Compound 926

5-[[2-[(2S,5R)-2-(1H-indazol-4-yl)-5-methyl-1-piperidyl]-2-oxo-acetyl]amino]-2-methoxy-pyridine-3-carboxamide (135 mg, 309.30 μmol) was divided into enantiomers by Chiral HPLC (Column: Chiralpak IB (250*30 mm, 5 mkm); Mobile phase: CO$_2$-MeOH, 60-40. Flow Rate: 80 mL/min; Column Temperature: 40° C.; Wavelength: 215 nm.), affording:

Compound 926—5-[[2-[(2S,5R)-2-(1H-indazol-4-yl)-5-methyl-1-piperidyl]-2-oxo-acetyl]amino]-2-methoxy-pyridine-3-carboxamide (25 mg, 57.28 μmol, 37.04% yield) with ret.time=7.46 min and Compound 918—5-[[2-[(2R,5S)-2-(1H-indazol-4-yl)-5-methyl-1-piperidyl]-2-oxo-acetyl]amino]-2-methoxy-pyridine-3-carboxamide (24 mg, 54.99 μmol, 35.56% yield) with ret.time=9.87 min.

Compound 918: $^1$H NMR (DMSO-d$_6$, 600 MHz): δ (ppm) 1.03 (m, 3H), 1.34 (m, 1H), 1.87 (m, 2H), 2.18 (m, 2H), 3.46 (m, 2H), 3.92 (m, 3H), 5.74 (m, 1H), 7.07 (m, 1H), 7.32 (m, 1H), 7.45 (d, 1H), 7.71 (m, 2H), 8.07 (m, 1H), 8.46 (m, 2H), 10.98 (m, 1H), 13.12 (s, 1H)

LCMS(ESI): [M+H]$^+$ m/z: calcd 436.2; found 437.2; Rt=2.431 min.

RT (CO$_2$-MeOH, 60-40, 80 ml/min)=5.8212 min.

Compound 926: $^1$H NMR (DMSO-d$_6$, 600 MHz): δ (ppm) 1.02 (m, 3H), 1.34 (m, 1H), 1.86 (m, 2H), 2.22 (m, 2H), 3.38 (m, 1H), 3.92 (m, 4H), 5.75 (m, 1H), 7.04 (m, 1H), 7.32 (t, 1H), 7.45 (d, 1H), 7.71 (m, 2H), 8.07 (m, 1H), 8.45 (m, 2H), 10.99 (m, 1H), 13.12 (s, 1H)

LCMS(ESI): [M+H]$^+$ m/z: calcd 436.2; found 437.2; Rt=2.455 min.

RT (CO$_2$-MeOH, 60-40, 80 ml/min)=6.9102 min.

Example 109. The Synthesis of 5-(2-(5-methyl-2-(3-oxoisoindolin-5-yl)piperidin-1-yl)-2-oxoacetamido)Nicotinamide (Compound 746 and Compound 751

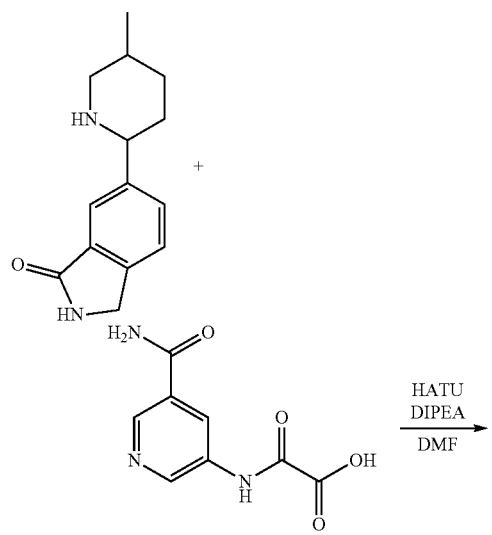

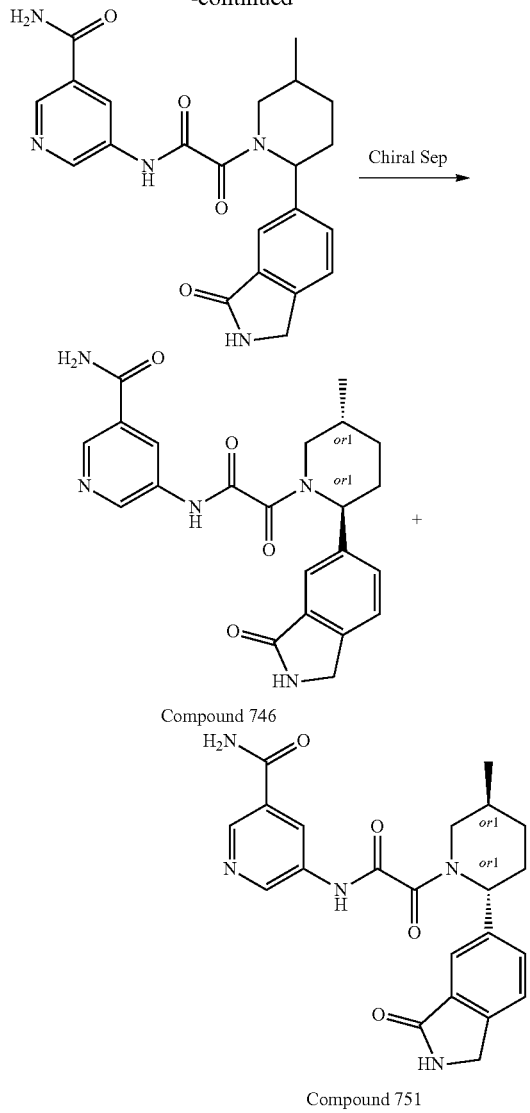

Compound 746

Compound 751

Step 1: Synthesis of 5-(2-(5-methyl-2-(3-oxoisoindolin-5-yl)piperidin-1-yl)-2-oxoacetamido)Nicotinamide DIPEA (412.47 mg, 3.19 mmol, 555.89 μL) was added to the solution of respective 2-[(5-carbamoyl-3-pyridyl)amino]-2-oxo-acetic acid (190.72 mg, 776.48 μmol, HCl) and 6-(5-methyl-2-piperidyl)isoindolin-1-one (0.21 g, 911.84 μmol) in DMF (5 mL). The resulting mixture was stirred for 5 min followed by the addition of HATU (381.38 mg, 1.00 mmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and H$_2$O-MeOH as an eluent mixture) to afford 5-[[2-[5-methyl-2-(3-oxoisoindolin-5-yl)-1-piperidyl]-2-oxo-acetyl]amino]pyridine-3-carboxamide (0.14 g, 332.19 μmol, 36.43% yield).

$^1$H NMR (500 MHz, DMSO-d$_6$) δ (ppm) 1.02 (d, 3H), 1.36 (m, 1H), 1.68 (m, 1H), 1.89 (m, 1H), 2.08 (m, 1H), 2.28

(m, 1H), 2.72 (m, 1H), 3.56 (m, 1H), 3.96 (m, 1H), 4.34 (s, 2H), 5.56 (m, 1H), 7.62 (m, 3H), 8.21 (m, 1H), 8.49 (m, 1H), 8.62 (m, 1H), 8.78 (m, 1H), 8.96 (m, 1H), 11.32 (m, 1H).

LCMS(ESI): [M]$^+$ m/z: calcd 421.2; found 422.2; Rt=1.882 min.

Step 2: Chiral Separation (Compound 751 and Compound 746

The enantiomers were separated by chiral HPLC (column: AS (250*20, 10 mkm), CO$_2$-MeOH, 60-40, 50 ml/min make up flow rate—15 ml/min as mobile phase) to give the two individual enantiomers Compound 751 5-[[2-[(2R,5S)-5-methyl-2-(3-oxoisoindolin-5-yl)-1-piperidyl]-2-oxo-acetyl]amino]pyridine-3-carboxamide (68.43 mg, 162.37 μmol, 48.88% yield) and Compound 746 5-[[2-[(2S,5R)-5-methyl-2-(3-oxoisoindolin-5-yl)-1-piperidyl]-2-oxo-acetyl]amino]pyridine-3-carboxamide (65.37 mg, 155.11 μmol, 46.69% yield).

Ret time for Compound 751 in analytical conditions (column: AS-H, CO$_2$-MeOH, 60-40, 2 ml/min as mobile phase) 5.80 min and for Compound 746 3.93 min.

Compound 751: Retention time: 5.80 min $^1$H NMR (600 MHz, DMSO-d$_6$) δ (ppm) 1.01-1.06 (m, 3H), 1.27-1.40 (m, 1H), 1.60-1.70 (m, 1H), 1.83-1.95 (m, 1H), 2.07-2.21 (m, 1H), 2.21-2.33 (m, 1H), 2.77-3.26 (m, 1H), 3.45-4.11 (m, 1H), 4.28-4.38 (m, 2H), 5.22-5.71 (m, 1H), 7.52-7.64 (m, 4H), 8.07-8.19 (m, 1H), 8.39-8.51 (m, 1H), 8.52-8.57 (m, 1H), 8.71-8.80 (m, 1H), 8.81-8.93 (m, 1H), 11.21-11.39 (m, 1H).

LCMS(ESI): [M]$^+$ m/z: calcd 421.2; found 422.2; Rt=0.812 min.

Compound 746:Retention time: 3.93 min $^1$H NMR (600 MHz, DMSO-d$_6$) δ (ppm) 1.00-1.05 (m, 3H), 1.29-1.41 (m, 1H), 1.63-1.70 (m, 1H), 1.83-1.93 (m, 1H), 2.08-2.21 (m, 1H), 2.22-2.29 (m, 1H), 2.78-3.26 (m, 1H), 3.48-4.09 (m, 1H), 4.31-4.41 (m, 2H), 5.22-5.72 (m, 1H), 7.52-7.64 (m, 4H), 8.08-8.20 (m, 1H), 8.38-8.52 (m, 1H), 8.51-8.60 (m, 1H), 8.69-8.80 (m, 1H), 8.81-8.93 (m, 1H), 11.19-11.39 (m, 1H).

LCMS(ESI): [M]$^+$ m/z: calcd 421.2; found 422.2; Rt=0.812 min.

Example 110. The Synthesis of 2-methoxy-5-(2-(5-methyl-2-(3-oxoisoindolin-5-yl)piperidin-1-yl)-2-oxoacetamido)Nicotinamide (Compound 759

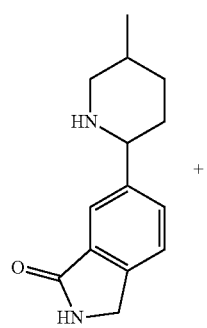

+

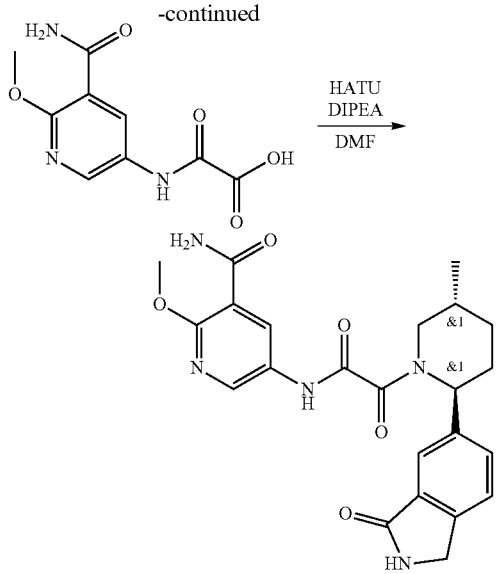

Compound 759

DIPEA (284.78 mg, 2.20 mmol, 383.80 μL) was added to the solution of respective 2-[(5-carbamoyl-6-methoxy-3-pyridyl)amino]-2-oxo-acetic acid (0.3 g, 881.38 μmol, Et$_3$N) and 6-(5-methyl-2-piperidyl)isoindolin-1-one (202.99 mg, 881.38 μmol) in DMF (10 mL). The resulting mixture was stirred for 5 min followed by the addition of HATU (368.64 mg, 969.52 μmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and H$_2$O-MeOH as an eluent mixture) to afford 2-methoxy-5-[[2-[(2S,5R)-5-methyl-2-(3-oxoisoindolin-5-yl)-1-piperidyl]-2-oxo-acetyl]amino]pyridine-3-carboxamide (164.5 mg, 364.36 μmol, 41.34% yield).

$^1$H NMR (600 MHz, DMSO-d$_6$) δ (ppm) 1.01-1.03 (m, 3H), 1.28-1.41 (m, 1H), 1.60-1.71 (m, 1H), 1.81-1.93 (m, 1H), 2.05-2.20 (m, 1H), 2.20-2.32 (m, 1H), 2.74-3.27 (m, 1H), 3.48-4.04 (m, 4H), 4.32-4.35 (m, 2H), 5.20-5.69 (m, 1H), 7.51-7.60 (m, 3H), 7.64-7.78 (m, 2H), 8.37-8.47 (m, 1H), 8.48-8.58 (m, 2H), 10.99-11.10 (m, 1H).

LCMS(ESI): [M]$^+$ m/z: calcd 451.2; found 452.2; Rt=2.197 min.

Example 111. The Synthesis of N-(6-amino-5-ethylpyridin-3-yl)-2-(5-methyl-2-(3-oxoisoindolin-5-yl)piperidin-1-yl)-2-oxoacetamide (Compound 700 and Compound 695

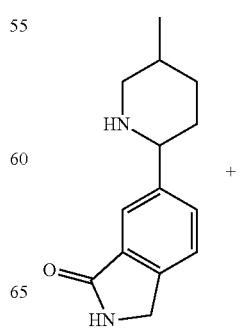

+

-continued

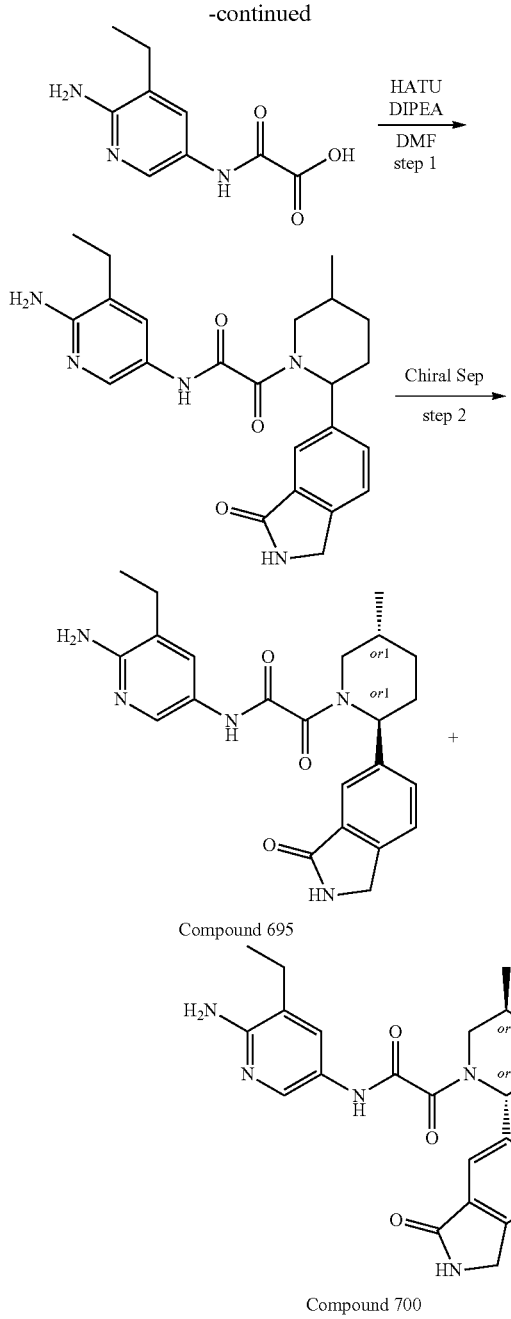

Compound 695

Compound 700

Step 1: Synthesis of N-(6-amino-5-ethylpyridin-3-yl)-2-(5-methyl-2-(3-oxoisoindolin-5-yl)piperidin-1-yl)-2-oxoacetamide DIPEA (617.79 mg, 4.78 mmol, 832.60 µL) was added to the solution of respective 2-[(6-amino-5-ethyl-3-pyridyl) amino]-2-oxo-acetic acid (0.25 g, 1.20 mmol) and 6-(5-methyl-2-piperidyl)isoindolin-1-one (275.22 mg, 1.20 mmol) in DMF (10 mL). The resulting mixture was stirred for 5 min followed by the addition of HATU (499.82 mg, 1.31 mmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and H$_2$O-MeOH+NH$_3$ as an eluent mixture) to afford N-(6-amino-5-ethyl-3-pyridyl)-2-[5-methyl-2-(3-oxoisoindolin-5-yl)-1-piperidyl]-2-oxo-acetamide (0.37 g, 877.84 µmol, 73.46% yield).

LCMS(ESI): [M]$^+$ m/z: calcd 421.2; found 422.2; Rt=1.852 min.

Step 2: Chiral Separation (Compound 700 and Compound 695

The enantiomers were separated by chiral HPLC (column: IC-II, Hexane-IPA-MeOH, 60-20-20, 12 ml/min as mobile phase) to give the two individual enantiomers Compound 700 N-(6-amino-5-ethyl-3-pyridyl)-2-[(2R,5S)-5-methyl-2-(3-oxoisoindolin-5-yl)-1-piperidyl]-2-oxo-acetamide (118.61 mg, 281.41 µmol, 32.06% yield) and Compound 695 N-(6-amino-5-ethyl-3-pyridyl)-2-[(2S,5R)-5-methyl-2-(3-oxoisoindolin-5-yl)-1-piperidyl]-2-oxo-acetamide (113.03 mg, 268.17 µmol, 30.55% yield).

Ret time for Compound 700 in analytical conditions (column: IC, Hexane-IPA-MeOH, 50-25-25, 0.6 ml/min as mobile phase) 50.38 min and for Compound 695 37.16 min.

Compound 700: Retention time: 50.38 min $^1$H NMR (600 MHz, DMSO-d$_6$) δ (ppm) 1.07 (m, 6H), 1.36 (m, 1H), 1.65 (m, 1H), 1.87 (m, 1H), 2.08 (m, 1H), 2.33 (m, 3H), 2.97 (m, 1H), 3.76 (m, 1H), 4.33 (m, 2H), 5.61 (m, 3H), 7.56 (m, 4H), 8.01 (m, 1H), 8.54 (s, 1H), 10.54 (m, 1H).

LCMS(ESI): [M]$^+$ m/z: calcd 421.2; found 422.2; Rt=1.789 min.

Compound 695: Retention time: 37.16 min $^1$H NMR (600 MHz, DMSO-d$_6$) δ (ppm) 1.07 (m, 6H), 1.36 (m, 1H), 1.65 (m, 1H), 1.87 (m, 1H), 2.08 (m, 1H), 2.33 (m, 3H), 2.97 (m, 1H), 3.76 (m, 1H), 4.33 (m, 2H), 5.61 (m, 3H), 7.56 (m, 4H), 8.01 (m, 1H), 8.54 (m, 1H), 10.54 (m, 1H).

LCMS(ESI): [M]$^+$ m/z: calcd 421.2; found 422.2; Rt=1.793 min.

Example 112. The Synthesis of 5-(2-(2-(3-chloro-4,5-difluorophenyl)-5-methylpiperidin-1-yl)-2-oxoacetamido)Nicotinamide (Compound 834 and Compound 846

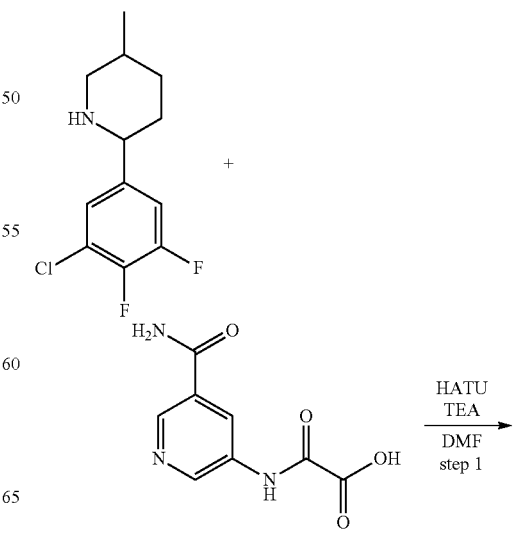

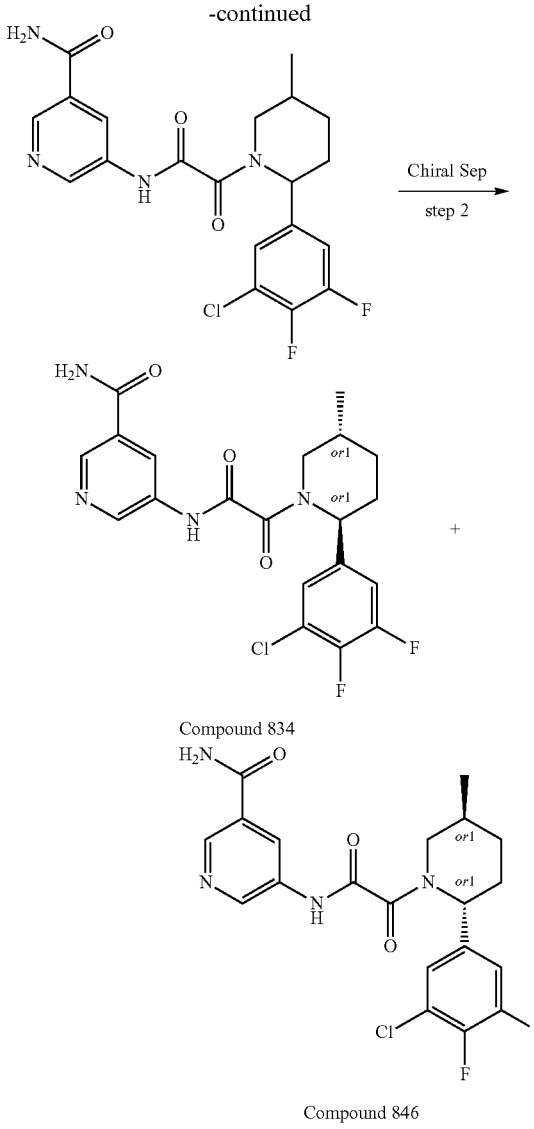

Compound 834

Compound 846

Step 1: Synthesis of 5-(2-(2-(3-chloro-4,5-difluoro-phenyl)-5-methylpiperidin-1-yl)-2-oxoacetamido) Nicotinamide To a stirred mixture of (2R,5S)-2-(3-chloro-4,5-difluoro-phenyl)-5-methyl-piperidine (200 mg, 814.02 μmol), 2-[(5-carbamoyl-3-pyridyl)amino]-2-oxo-acetic acid (199.94 mg, 814.02 μmol, HCl) and TEA (247.11 mg, 2.44 mmol, 340.37 μL) in DMF (3 mL) was added HATU (340.46 mg, 895.42 μmol). The resulting reaction mixture was stirred at 20° C. for 5 hr. Then, it was subjected to HPLC (40-90%0-5 min $H_2O$/MeOH/0.1% $NH_4OH$, flow: 30 ml/min; column: YMC Triart C18 100×20 mm, 5 um), affording 5-[[2-[(2R,5S)-2-(3-chloro-4,5-difluoro-phenyl)-5-methyl-1-piperidyl]-2-oxo-acetyl]amino]pyridine-3-carboxamide (192 mg, 439.52 μmol, 53.99% yield).

LCMS(ESI): $[M]^+$ m/z: calcd 436.2; found 437.2; Rt=2.972 min.

Step 2: Chiral Separation (Compound 834 and Compound 846

5-[[2-[(2R,5S)-2-(3-chloro-4,5-difluoro-phenyl)-5-methyl-1-piperidyl]-2-oxo-acetyl]amino]pyridine-3-carbox-amide (192 mg, 439.52 μmol) was divided into enantiomers by Chiral HPLC(Column: Chiralpak AD-H—I (250*20 mm, 5 mkm); Mobile phase: $CO_2$-MeOH 50-50; Flow Rate: 40 mL/min), affording: 5-[[2-[(2R,5S)-2-(3-chloro-4,5-difluoro-phenyl)-5-methyl-1-piperidyl]-2-oxo-acetyl]amino]pyridine-3-carboxamide (55 mg, 125.90 μmol, 57.29% yield) with ret.time=6.3 min (Compound 846) and 5-[[2-[(2S,5R)-2-(3-chloro-4,5-difluoro-phenyl)-5-methyl-1-piperidyl]-2-oxo-acetyl]amino]pyridine-3-carboxamide (68 mg, 155.66 μmol, 70.83% yield) with ret.time=8.98 min (Compound 834).

Ret time for Compound 834 in analytical conditions (column: AD-H, $CO_2$-MeOH, 50-50, 2 ml/min as mobile phase) 8.34 min and for Compound 846 5.93 min.

Compound 834: Retention time: 8.34 min $^1$H NMR (600 MHz, DMSO-$d_6$) δ (ppm) 0.93-1.06 (m, 3H), 1.24-1.40 (m, 1H), 1.58-1.68 (m, 1H), 1.78-1.96 (m, 1H), 1.96-2.12 (m, 1H), 2.12-2.25 (m, 1H), 2.77-3.28 (m, 1H), 3.44-4.03 (m, 1H), 5.12-5.52 (m, 1H), 7.31-7.48 (m, 2H), 7.55-7.65 (m, 1H), 8.09-8.21 (m, 1H), 8.41-8.51 (m, 1H), 8.71-8.80 (m, 1H), 8.80-8.93 (m, 1H), 11.20-11.34 (m, 1H).

LCMS(ESI): $[M]^+$ m/z: calcd 436.2; found 437.2; Rt=1.277 min.

Compound 846: Retention time: 5.93 min $^1$H NMR (600 MHz, DMSO-$d_6$) δ (ppm) 0.95-1.05 (m, 3H), 1.23-1.37 (m, 1H), 1.58-1.68 (m, 1H), 1.81-1.93 (m, 1H), 1.97-2.11 (m, 1H), 2.11-2.25 (m, 1H), 2.77-3.29 (m, 1H), 3.44-4.04 (m, 1H), 5.10-5.52 (m, 1H), 7.30-7.46 (m, 2H), 7.55-7.65 (m, 1H), 8.10-8.20 (m, 1H), 8.42-8.51 (m, 1H), 8.71-8.79 (m, 1H), 8.80-8.91 (m, 1H), 11.16-11.33 (m, 1H).

LCMS(ESI): $[M]^+$ m/z: calcd 436.2; found 437.2; Rt=1.284 min.

Example 113. The Synthesis of 5-(2-(2-(3-chloro-5-(trifluoromethyl)phenyl)-5-methylpiperidin-1-yl)-2-oxoacetamido)Nicotinamide (Compound 646 and Compound 653

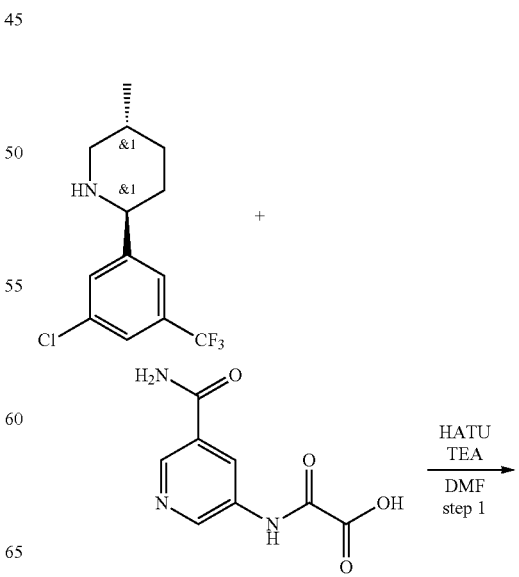

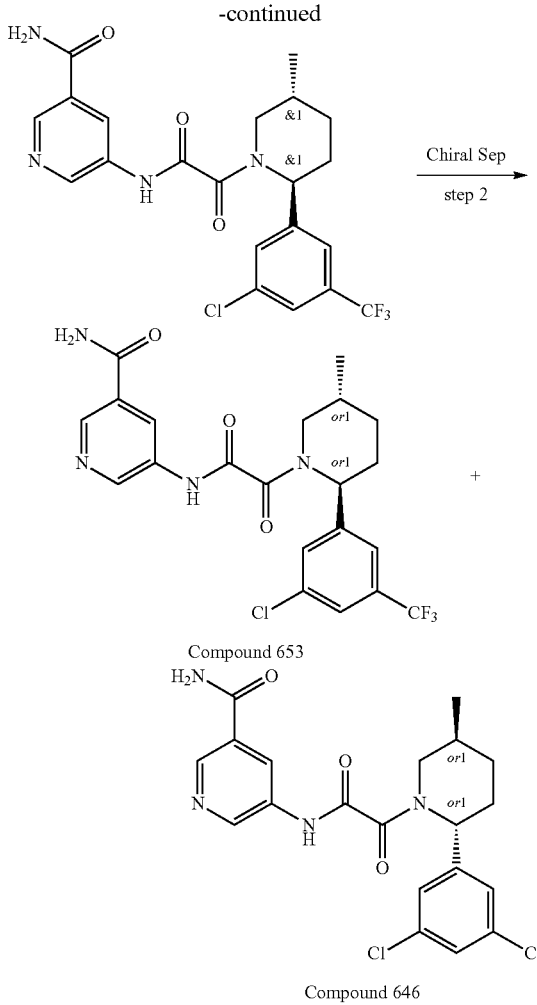

Compound 653

Compound 646

Step 1: Synthesis of 5-(2-(2-(3-chloro-5-(trifluoromethyl)phenyl)-5-methylpiperidin-1-yl)-2-oxoacetamido)Nicotinamide 2-[(5-carbamoyl-3-pyridyl)amino]-2-oxo-acetic acid (279.38 mg, 900.21 μmol, (2R,5S)-2-[3-chloro-5-(trifluoromethyl)phenyl]-5-methyl-piperidine (250 mg, 900.21 μmol), HATU (342.29 mg, 900.21 μmol) and TEA (91.09 mg, 900.21 μmol, 125.47 μL) were mixed in DMSO (2 mL) and stirred for 3 hr at 20° C. Reaction mixture was subjected to HPLC 2-10 min 45-60% water/ACN(loading pump 4 ml ACN) column: TRIART 100*20, 5 microM. 5-[[2-[(2R,5S)-2-[3-chloro-5-(trifluoromethyl)phenyl]-5-methyl-1-piperidyl]-2-oxo-acetyl]amino]pyridine-3-carboxamide (240 mg, 511.88 μmol, 56.86% yield) was obtained.

LCMS(ESI): [M]+ m/z: calcd 468.2; found 469.2; Rt=3.311 min.

Step 2: Chiral Separation (Compound 653 and Compound 646

Racemic 5-[[2-[(2R,5S)-2-[3-chloro-5-(trifluoromethyl)phenyl]-5-methyl-1-piperidyl]-2-oxo-acetyl]amino]pyridine-3-carboxamide (240 mg, 511.88 μmol) was separated using Chiralpak IA-II 250*20, 5 mkm column; Hexane-IPA-MeOH, 80-10-10 as a mobile phase; Flow rate 12 mL/min; Injection Volume: 900 mkl; affording 5-[[2-[(2S,5R)-2-[3-chloro-5-(trifluoromethyl)phenyl]-5-methyl-1-piperidyl]-2-oxo-acetyl]amino]pyridine-3-carboxamide (82 mg, 174.89 μmol, 68.33% yield) and 5-[[2-[(2R,5S)-2-[3-chloro-5-(trifluoromethyl)phenyl]-5-methyl-1-piperidyl]-2-oxo-acetyl]amino]pyridine-3-carboxamide (86 mg, 183.43 μmol, 71.67% yield). Ret time for Compound 653 in analytical conditions (column: IA, Hexane-IPA-MeOH, 70-15-15, 0.6 ml/min as mobile phase) 13.53 min and for Compound 646 20.36 min.

Compound 653: Retention time: 13.53 min $^1$H NMR (600 MHz, DMSO-$d_6$) δ (ppm) 1.01 (m, 3H), 1.32 (m, 1H), 1.62 (m, 1H), 1.91 (m, 1H), 2.18 (m, 3H), 3.78 (m, 1H), 5.41 (m, 1H), 7.59 (m, 2H), 7.68 (m, 1H), 7.77 (m, 1H), 8.14 (m, 1H), 8.46 (m, 1H), 8.80 (m, 2H), 11.30 (m, 1H).

LCMS(ESI): [M]+ m/z: calcd 468.2; found 469.2; Rt=3.312 min.

Compound 646: Retention time: 20.36 min $^1$H NMR (600 MHz, DMSO-$d_6$) δ (ppm) 1.01 (m, 3H), 1.33 (m, 1H), 1.61 (m, 1H), 1.91 (m, 1H), 2.19 (m, 3H), 3.78 (m, 1H), 5.41 (m, 1H), 7.63 (m, 3H), 7.77 (m, 1H), 8.14 (m, 1H), 8.46 (m, 1H), 8.80 (m, 2H), 11.29 (m, 1H).

LCMS(ESI): [M]+ m/z: calcd 468.2; found 469.2; Rt=3.313 min.

Example 114. The Synthesis of 5-(2-(2-(3-chloro-5-fluorophenyl)-5-methylpiperidin-1-yl)-2-oxoacetamido)Nicotinamide (Compound 1084, Compound 615, Compound 625 and Compound 624

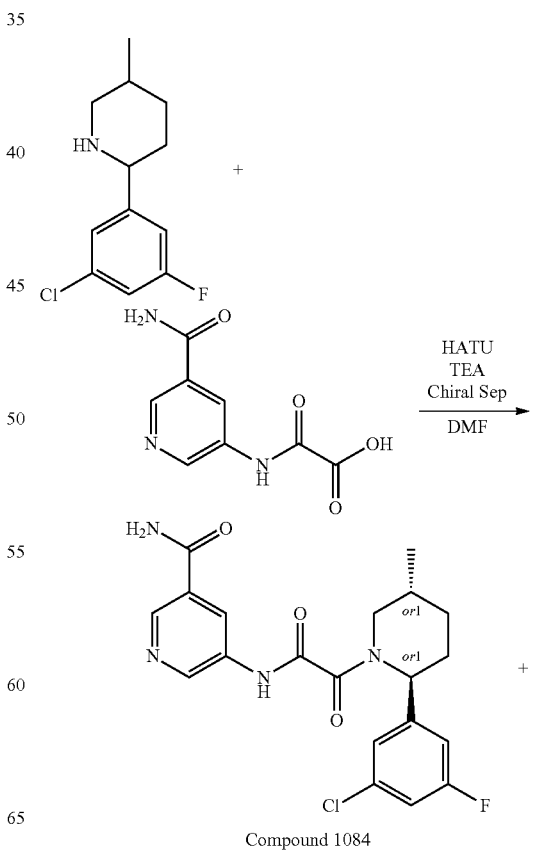

Compound 1084

-continued

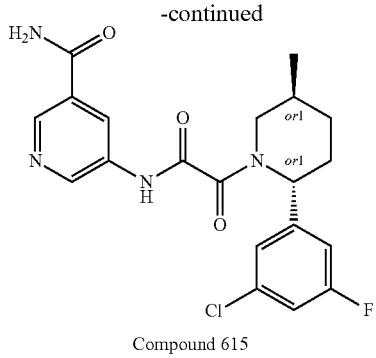

Compound 615

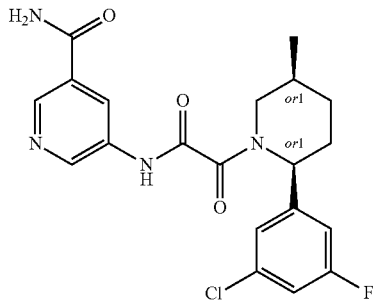

Compound 624

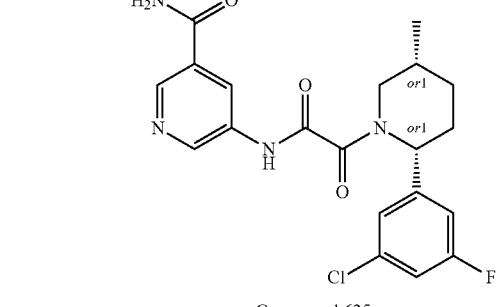

Compound 625

(2R,5S)-2-(3-chloro-5-fluoro-phenyl)-5-methyl-piperidine (0.3 g, 1.32 mmol), 2-[(5-carbamoyl-3-pyridyl)amino]-2-oxo-acetic acid (323.60 mg, 1.32 mmol, HCl) and DIPEA (340.55 mg, 2.63 mmol, 458.97 μL) were dissolved in DMF (8 mL) under gentle heating. HATU (500.95 mg, 1.32 mmol) was added in small portions under vigorous stirring and occasional heating. After the reaction was complete, the mixture was purified by HPLC (23% 0.5-6.5 min water-MeCN; flow: 30 ml/min; (loading pump 4 ml/minMeCN); target mass 380; column: SunFire C18 100×19 mm 5 um (L)) and enantiomers were separated by chiral chromatography (IA (250*30, 5 mkm), Hexane-IPA-MeOH, 70-15-15, 20 ml/min) to give 5-[[2-[(2R,5S)-2-(3-chloro-5-fluoro-phenyl)-5-methyl-1-piperidyl]-2-oxo-acetyl]amino]pyridine-3-carboxamide (83 mg, 198.16 μmol, 15.04% yield), 5-[[2-[(2S,5R)-2-(3-chloro-5-fluoro-phenyl)-5-methyl-1-piperidyl]-2-oxo-acetyl]amino]pyridine-3-carboxamide (87 mg, 207.71 μmol, 15.77% yield), 5-[[2-[(2R,5R)-2-(3-chloro-5-fluoro-phenyl)-5-methyl-1-piperidyl]-2-oxo-acetyl]amino]pyridine-3-carboxamide (10 mg, 23.88 μmol, 1.81% yield) and 5-[[2-[(2S,5S)-2-(3-chloro-5-fluoro-phenyl)-5-methyl-1-piperidyl]-2-oxo-acetyl]amino]pyridine-3-carboxamide (10 mg, 23.88 μmol, 1.81% yield).

Ret time for Compound 1084 in analytical conditions (column: IC, $CO_2$-MeOH, 70-30, 3 ml/min as mobile phase) 9.30 min, Compound 615 10.08 min, for Compound 625 7.53 min and for Compound 624 6.97 min.

Compound 1084: Retention time: 9.30 min
$^1$H NMR (600 MHz, DMSO-$d_6$) δ (ppm) 0.99-1.01 (m, 3H), 1.26-1.39 (m, 1H), 1.53-1.67 (m, 1H), 1.78-1.95 (m, 1H), 2.01-2.13 (m, 1H), 2.15-2.26 (m, 1H), 2.74-3.28 (m, 1H), 3.47-4.04 (m, 1H), 5.11-5.65 (m, 1H), 7.12-7.20 (m, 1H), 7.20-7.26 (m, 1H), 7.30-7.39 (m, 1H), 7.56-7.65 (m, 1H), 8.11-8.20 (m, 1H), 8.41-8.52 (m, 1H), 8.69-8.81 (m, 1H), 8.81-8.96 (m, 1H), 11.11-11.46 (m, 1H).

LCMS(ESI): [M]$^+$ m/z: calcd 418.2; found 419.2; Rt=2.922 min.

Compound 615: Retention time: 10.08 min
$^1$H NMR (600 MHz, DMSO-$d_6$) δ (ppm) 0.98-1.03 (m, 3H), 1.25-1.39 (m, 1H), 1.58-1.66 (m, 1H), 1.83-1.94 (m, 1H), 2.02-2.13 (m, 1H), 2.15-2.29 (m, 1H), 2.78-3.28 (m, 1H), 3.47-4.09 (m, 1H), 5.14-5.58 (m, 1H), 7.09-7.20 (m, 1H), 7.20-7.26 (m, 1H), 7.30-7.40 (m, 1H), 7.55-7.67 (m, 1H), 8.10-8.22 (m, 1H), 8.39-8.54 (m, 1H), 8.69-8.80 (m, 1H), 8.80-8.96 (m, 1H), 11.19-11.43 (m, 1H).

LCMS(ESI): [M]$^+$ m/z: calcd 418.2; found 419.2; Rt=2.921 min.

Compound 625: Retention time: 7.53 min
$^1$H NMR (600 MHz, DMSO-$d_6$) δ (ppm) 0.73-0.82 (m, 3H), 0.98-1.05 (m, 1H), 1.60-1.76 (m, 2H), 1.79-1.96 (m, 1H), 2.11-2.18 (m, 0.4H), 2.57-2.60 (m, 1.6H), 3.63-4.28 (m, 1H), 5.15-5.67 (m, 1H), 7.13-7.19 (m, 1H), 7.19-7.24 (m, 1H), 7.32-7.41 (m, 1H), 7.58-7.65 (m, 1H), 8.10-8.22 (m, 1H), 8.41-8.56 (m, 1H), 8.70-8.80 (m, 1H), 8.80-8.96 (m, 1H), 11.27-11.36 (m, 1H).

LCMS(ESI): [M]$^+$ m/z: calcd 418.2; found 419.2; Rt=2.981 min.

Compound 624: Retention time: 6.97 min
$^1$H NMR (600 MHz, DMSO-$d_6$) δ (ppm) 0.66-0.86 (m, 3H), 0.94-1.09 (m, 1H), 1.55-1.77 (m, 2H), 1.80-1.98 (m, 1H), 2.11-2.19 (m, 0.4H), 2.53-2.61 (m, 1.6H), 3.62-4.29 (m, 1H), 5.14-5.68 (m, 1H), 7.13-7.19 (m, 1H), 7.19-7.26 (m, 1H), 7.32-7.40 (m, 1H), 7.54-7.66 (m, 1H), 8.09-8.20 (m, 1H), 8.43-8.55 (m, 1H), 8.72-8.80 (m, 1H), 8.80-8.94 (m, 1H), 11.28-11.44 (m, 1H).

LCMS(ESI): [M]$^+$ m/z: calcd 418.2; found 419.2; Rt=2.979 min.

Example 115. The Synthesis of 5-(2-(2-(3,4-difluorophenyl)-4,4-difluoro-5-methylpiperidin-1-yl)-2-oxoacetamido)Nicotinamide (Compound 683 and Compound 706

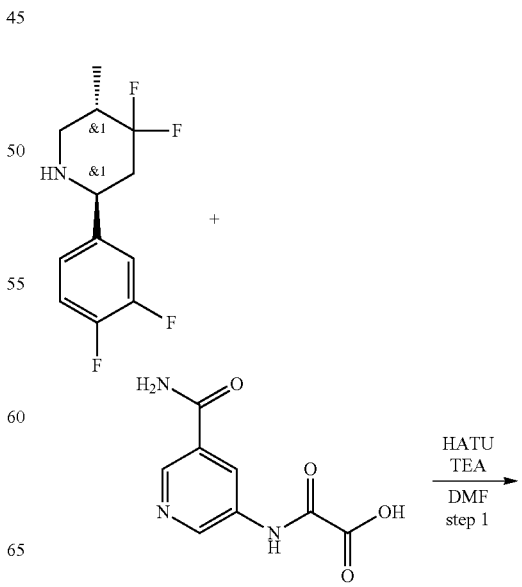

1467
-continued

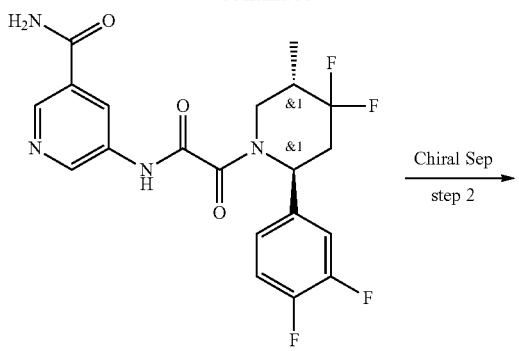

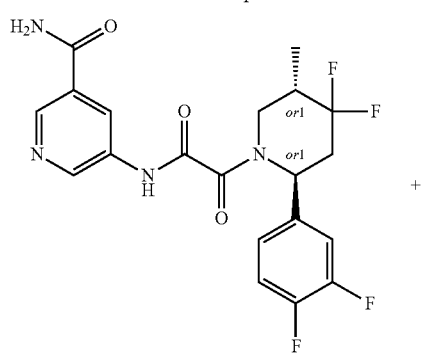

Compound 683

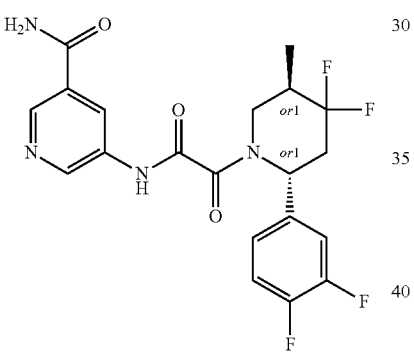

Compound 706

Step 1: Synthesis of 5-(2-(2-(3,4-difluorophenyl)-4,4-difluoro-5-methylpiperidin-1-yl)-2-oxoacetamido) Nicotinamide To a solution of (2S,5S)-2-(3,4-difluorophenyl)-4,4-difluoro-5-methyl-piperidine (0.3 g, 1.21 mmol), 2-[(5-carbamoyl-3-pyridyl)amino]-2-oxo-acetic acid (298.04 mg, 1.21 mmol, HCl) and TEA (613.94 mg, 6.07 mmol, 845.65 µL), HATU (507.52 mg, 1.33 mmol) was added portion wise. The resulting mixture was stirred at 25° C. for 3 hr and purified by HPLC: 30-70% 0-5 min water-MeOH, flow 30 ml/min (loading pump 4 ml/min MeOH) column: SunFire C18 100*19 mm Sum) to obtain 5-[[2-[(2S,5S)-2-(3,4-difluorophenyl)-4,4-difluoro-5-methyl-1-piperidyl]-2-oxo-acetyl]amino]pyridine-3-carboxamide (160 mg, 364.98 µmol, 30.08% yield). This compound was used for chiral resolution without H-NMR.

LCMS(ESI): [M]+ m/z: calcd 438.2; found 439.2; Rt=2.684 min.

1468

Step 2: Chiral Separation (Compound 683 and Compound 706

5-[[2-[(2S,5S)-2-(3,4-difluorophenyl)-4,4-difluoro-5-methyl-1-piperidyl]-2-oxo-acetyl]amino]pyridine-3-carboxamide (160 mg, 364.98 µmol) was chirally separated (Sample Info: IA-I (250*.0, 5 mkm), Hexane-IPA-MeOH, 50-25-25, 14 ml/min) to obtain 5-[[2-[(2S,5S)-2-(3,4-difluorophenyl)-4,4-difluoro-5-methyl-1-piperidyl]-2-oxo-acetyl]amino]pyridine-3-carboxamide (73 mg, 166.52 µmol, 91.25% yield) and 5-[[2-[(2R,5R)-2-(3,4-difluorophenyl)-4,4-difluoro-5-methyl-1-piperidyl]-2-oxo-acetyl]amino]pyridine-3-carboxamide (75 mg, 171.09 µmol, 93.75% yield).

Ret time for Compound 683 in analytical conditions (column: AD-H, Hexane-IPA-MeOH, 50-25-25, 0.6 ml/min as mobile phase) 28.60 min and for Compound 706 16.55 min.

Compound 683: Retention time: 28.60 min $^1$H NMR (600 MHz, DMSO-d$_6$) δ (ppm) 1.08 (m, 3H), 2.20 (m, 2H), 2.86 (m, 1H), 3.45 (m, 1H), 4.07 (m, 1H), 5.69 (m, 1H), 7.17 (m, 1H), 7.43 (m, 2H), 7.60 (m, 1H), 8.18 (m, 1H), 8.48 (m, 1H), 8.82 (m, 2H), 11.36 (m, 1H).

LCMS(ESI): [M]+ m/z: calcd 438.2; found 439.2; Rt=2.800 min.

Compound 706: Retention time: 16.55 min $^1$H NMR (600 MHz, DMSO-d$_6$) δ (ppm) 1.08 (m, 3H), 2.27 (m, 2H), 2.93 (m, 1H), 3.45 (m, 1H), 4.08 (m, 1H), 5.69 (m, 1H), 7.17 (m, 1H), 7.44 (m, 2H), 7.60 (m, 1H), 8.15 (m, 1H), 8.48 (m, 1H), 8.82 (m, 2H), 11.28 (m, 1H).

LCMS(ESI): [M]+ m/z: calcd 438.2; found 439.2; Rt=2.796 min.

Example 116. The Synthesis of N-(6-amino-5-ethylpyridin-3-yl)-2-(2-(3,4-difluorophenyl)-4,4-difluoro-5-methylpiperidin-1-yl)-2-oxoacetamide (Compound 721 and Compound 728

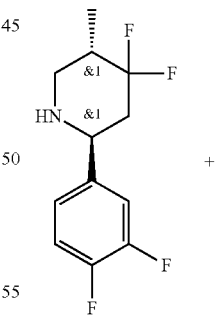

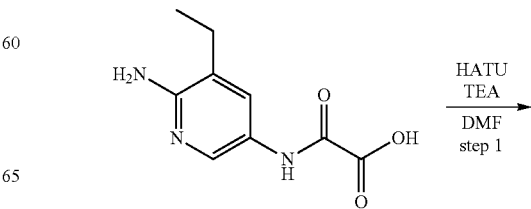

1469
-continued

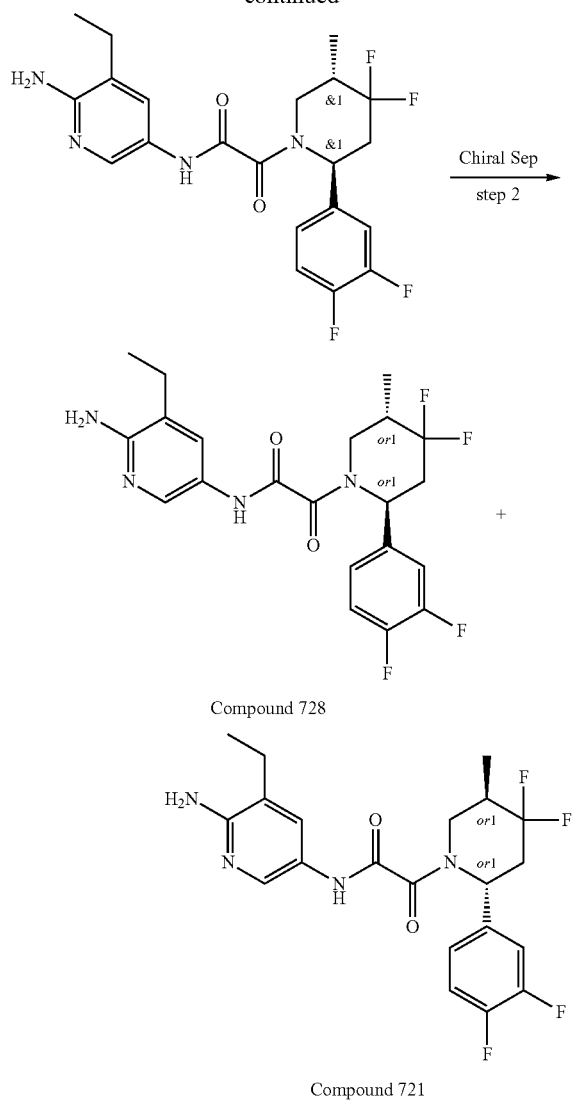

Compound 728

Compound 721

Step 1: Synthesis of N-(6-amino-5-ethylpyridin-3-yl)-2-(2-(3,4-difluorophenyl)-4,4-difluoro-5-methylpiperidin-1-yl)-2-oxoacetamide To a solution of (2S,5S)-2-(3,4-difluorophenyl)-4,4-difluoro-5-methyl-piperidine (0.25 g, 1.01 mmol), 2-[(6-amino-5-ethyl-3-pyridyl)amino]-2-oxo-acetic acid (296.16 mg, 1.42 mmol) and TEA (511.62 mg, 5.06 mmol, 704.71 μL), HATU (499.83 mg, 1.31 mmol) was added portion wise. The resulting mixture was stirred at 40° C. for 3 hr and purified by HPLC: 0-5 min 40-80% water-MeOH (NH₃ 0.1%), flow 30 ml/min (loading pump 4 ml/min MeOH (NH₃ 0.1%)) column: YMC-Actus Triart C18 100*20 mm I.D. S-5 um) to obtain N-(6-amino-5-ethyl-3-pyridyl)-2-[(2S,5S)-2-(3,4-difluorophenyl)-4,4-difluoro-5-methyl-1-piperidyl]-2-oxo-acetamide (190 mg, 433.38 μmol, 42.86% yield). This compound was used for chiral resolution without H-NMR.

LCMS(ESI): [M]⁺ m/z: calcd 438.2; found 439.2; Rt=2.475 min.

1470
Step 2: Chiral Separation (Compound 721 and Compound 728

N-(6-amino-5-ethyl-3-pyridyl)-2-[(2S,5S)-2-(3,4-difluorophenyl)-4,4-difluoro-5-methyl-1-piperidyl]-2-oxo-acetamide (190 mg, 433.38 μmol) was chirally separated (Injection Volume: 900 mkl Sample Info: AD-H I (250*20, 5 mkm), Hexane-IPA-MeOH, 50-25-25, 13 ml/min) to obtain N-(6-amino-5-ethyl-3-pyridyl)-2-[(2S,5S)-2-(3,4-difluorophenyl)-4,4-difluoro-5-methyl-1-piperidyl]-2-oxo-acetamide (73 mg, 166.51 μmol, 76.84% yield) and N-(6-amino-5-ethyl-3-pyridyl)-2-[(2R,5R)-2-(3,4-difluorophenyl)-4,4-difluoro-5-methyl-1-piperidyl]-2-oxo-acetamide (74 mg, 168.79 μmol, 77.89% yield).

Ret time for Compound 721 in analytical conditions (column: AD-H, Hexane-IPA-MeOH, 50-25-25, 0.6 ml/min as mobile phase) 31.65 min and for Compound 728 18.67 min.

Compound 721: Retention time: 31.65 min

¹H NMR (600 MHz, DMSO-d₆) δ (ppm) 1.08 (m, 6H), 2.18 (m, 1H), 2.39 (m, 2H), 2.93 (m, 2H), 3.41 (m, 1H), 3.96 (m, 1H), 5.69 (m, 3H), 7.15 (m, 1H), 7.43 (m, 3H), 8.03 (m, 1H), 10.58 (m, 1H).

LCMS(ESI): [M]⁺ m/z: calcd 438.2; found 439.2; Rt=1.208 min.

Compound 728: Retention time: 18.67 min

¹H NMR (600 MHz, DMSO-d₆) δ (ppm) 1.09 (m, 6H), 2.18 (m, 1H), 2.40 (m, 2H), 2.92 (m, 2H), 3.41 (m, 1H), 3.97 (m, 1H), 5.69 (m, 3H), 7.15 (m, 1H), 7.43 (m, 3H), 8.03 (m, 1H), 10.58 (m, 1H).

LCMS(ESI): [M]⁺ m/z: calcd 438.2; found 439.2; Rt=1.205 min.

Example 117. The Synthesis of 5-(2-(2-(3-chloro-4-(trifluoromethyl)phenyl)-5-methylpiperidin-1-yl)-2-oxoacetamido)Nicotinamide (Compound 655, Compound 647

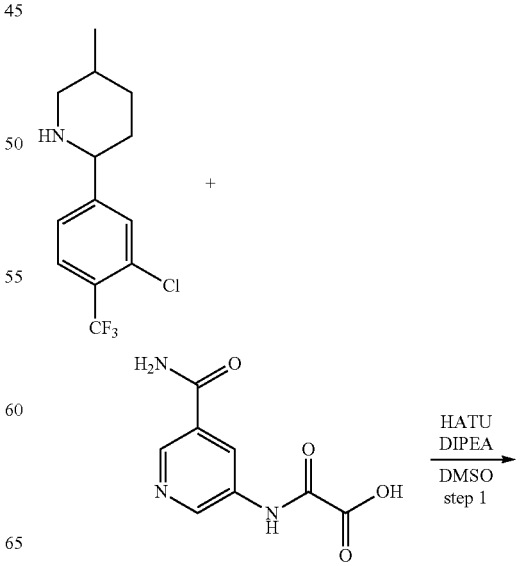

-continued

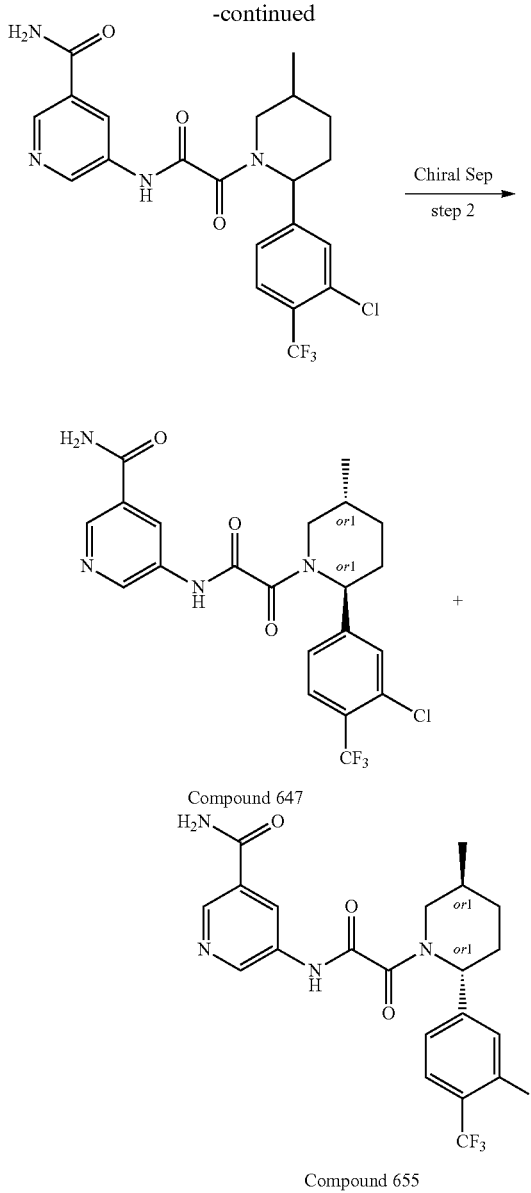

Compound 647

Compound 655

Step 1: Synthesis of 5-(2-(2-(3-chloro-4-(trifluoromethyl)phenyl)-5-methylpiperidin-1-yl)-2-oxoacetamido)Nicotinamide To a stirred solution of (2R,5S)-2-[3-chloro-4-(trifluoromethyl)phenyl]-5-methyl-piperidine (0.9 g, 3.24 mmol), 2-[(5-carbamoyl-3-pyridyl)amino]-2-oxo-acetic acid (955.19 mg, 3.89 mmol, HCl) and DIPEA (1.05 g, 8.10 mmol, 1.41 mL) in DMSO (5 mL) was added HATU (1.48 g, 3.89 mmol). The resulting reaction mixture was stirred at 20° C. for 13 hr. Upon completion, the reaction mixture was submitted to reverse phase HPLC (column: SunFire 19*100 mm, 5 mkl; MeOH as an eluent mixture) to afford 5-[[2-[(2R,5S)-2-[3-chloro-4-(trifluoromethyl)phenyl]-5-methyl-1-piperidyl]-2-oxo-acetyl]amino]pyridine-3-carboxamide (0.1 g, 213.29 μmol, 6.58% yield) as light-yellow solid.

LCMS(ESI): [M]+ m/z: calcd 468.2; found 469.2; Rt=1.202 min.

Step 2: Chiral Separation (Compound 655 and Compound 647

5-[[2-[(2R,5S)-2-[3-chloro-4-(trifluoromethyl)phenyl]-5-methyl-1-piperidyl]-2-oxo-acetyl]amino]pyridine-3-carboxamide (0.1 g, 213.29 μmol) was submitted to chiral separation (IA-II (250*20, 5 mkm), Hexane-IPA-MeOH, 60-20-20, 12 ml/min) to afford 5-[[2-[(2R,5S)-2-[3-chloro-4-(trifluoromethyl)phenyl]-5-methyl-1-piperidyl]-2-oxo-acetyl]amino]pyridine-3-carboxamide (0.038 g, 81.05 μmol, 38.00% yield) and 5-[[2-[(2S,5R)-2-[3-chloro-4-(trifluoromethyl)phenyl]-5-methyl-1-piperidyl]-2-oxo-acetyl]amino]pyridine-3-carboxamide (0.039 g, 83.18 μmol, 39.00% yield). Ret time for Compound 655 in analytical conditions (column: IC, $CO_2$-MeOH, 60-40, 2.5 ml/min as mobile phase) 5.15 min and for Compound 647 4.04 min.

Compound 655: Retention time: 5.15 min $^1$H NMR (600 MHz, DMSO-$d_6$) δ (ppm) 1.01 (m, 3H), 1.31 (m, 1H), 1.63 (m, 1H), 1.90 (m, 1H), 2.15 (m, 2H), 2.82 (m, 1H), 3.78 (m, 1H), 5.42 (m, 1H), 7.49 (m, 1H), 7.63 (m, 2H), 7.86 (m, 1H), 8.14 (m, 1H), 8.46 (m, 1H), 8.76 (m, 1H), 8.86 (m, 1H), 11.27 (m, 1H).

LCMS(ESI): [M]+ m/z: calcd 468.2; found 469.2; Rt=3.227 min.

Compound 647: Retention time: 4.04 min $^1$H NMR (600 MHz, DMSO-$d_6$) δ (ppm) 1.01 (m, 3H), 1.31 (m, 1H), 1.63 (m, 1H), 1.90 (m, 1H), 2.17 (m, 2H), 2.83 (m, 1H), 3.70 (m, 1H), 5.42 (d, 1H), 7.50 (m, 1H), 7.63 (m, 2H), 7.86 (m, 1H), 8.13 (d, 1H), 8.46 (m, 1H), 8.76 (m, 1H), 8.86 (m, 1H), 11.27 (m, 1H).

LCMS(ESI): [M]+ m/z: calcd 468.2; found 469.2; Rt=3.226 min.

Example 118. The Synthesis of N-(5,6-dimethylpyridin-3-yl)-2-(5-methyl-2-(3-(methylsulfonyl)phenyl)piperidin-1-yl)-2-oxoacetamide (Compound 648

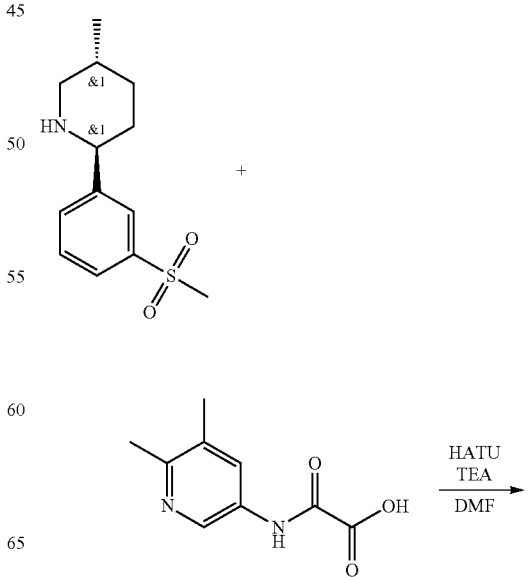

1473

-continued

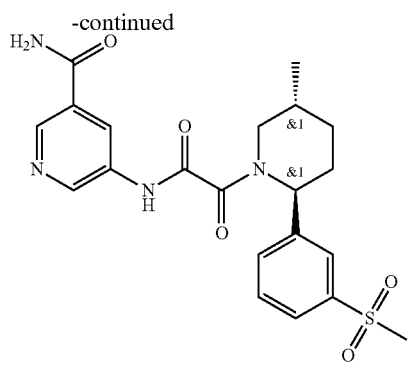

Compound 648

To a stirring solution of (2R,5S)-5-methyl-2-(3-methylsulfonylphenyl)piperidine (250.00 mg, 986.74 μmol), 2-[(5,6-dimethyl-3-pyridyl)amino]-2-oxo-acetic acid (291.46 mg, 986.74 μmol) and TEA (998.48 mg, 9.87 mmol, 1.38 mL) in DMF (5 mL) was added HATU (412.71 mg, 1.09 mmol) at 25° C. in small portions over 0.5 hr. The resulting reaction mixture was stirred at 25° C. for 18 hr. The crude reaction mixture was purified by reverse phase HPLC (column: YMC Triart C18 100×20 mm, 5 um, Mobile Phase: 40-54% 0-5 min 0.10% NH$_3$-MeOH, flow: 30 ml/min (loading pump 4 ml/min MeOH)) to afford Compound 648 N-(5,6-dimethyl-3-pyridyl)-2-[(2R,5S)-5-methyl-2-(3-methylsulfonylphenyl)-1-piperidyl]-2-oxo-acetamide (180 mg, 419.06 μmol, 42.47% yield).

$^1$H NMR (600 MHz, DMSO-d$_6$) δ (ppm) 1.01 (dd, 3H), 1.34 (m, 1H), 1.64 (m, 1H), 1.89 (d, 1H), 2.07 (m, 1H), 2.20 (m, 4H), 2.34 (m, 4H), 3.21 (m, 3H), 3.77 (m, 1H), 5.43 (m, 1H), 7.66 (m, 2H), 7.82 (m, 3H), 8.43 (m, 1H), 10.96 (m, 1H).

LCMS(ESI): [M]$^+$ m/z: calcd 429.4; found 430.2; Rt=1.980 min.

Example 119. The Synthesis of 5-(2-(5-methyl-2-(3-(N-methylsulfamoyl)phenyl)piperidin-1-yl)-2-oxoacetamido)Nicotinamide (Compound 666

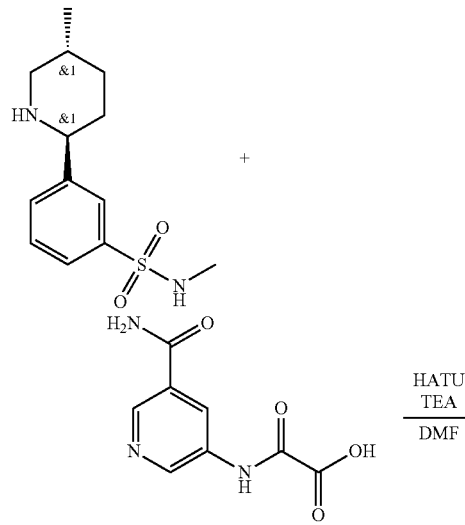

1474

-continued

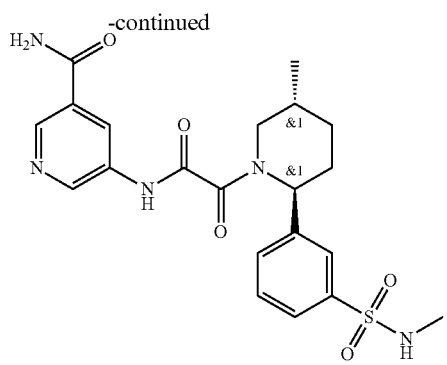

Compound 666

To a stirred mixture of N-methyl-3-[(2S,5R)-5-methyl-2-piperidyl]benzenesulfonamide (535 mg, 1.99 mmol), 2-[(5-carbamoyl-3-pyridyl)amino]-2-oxo-acetic acid (489.64 mg, 1.99 mmol, HCl) and TEA (605.16 mg, 5.98 mmol, 833.56 μL) in DMF (4 mL) was added HATU (833.78 mg, 2.19 mmol). The resulting reaction mixture was stirred at 20° C. for 4 hr. Then, it was subjected to HPLC (Column: YMC-Actus Triart C18 100*20 mm, 5 um; 0-5 min 10-60% water-MeOH (NH$_3$ 0.1%), flow 30 ml/min), affording 5-[[2-[(2S,5R)-5-methyl-2-[3-(methylsulfamoyl)phenyl]-1-piperidyl]-2-oxo-acetyl]amino]pyridine-3-carboxamide (237 mg, 515.76 μmol, 25.87% yield).

$^1$H NMR (600 MHz, DMSO-d$_6$) δ (ppm) 1.02 (m, 3H), 1.36 (m, 1H), 1.65 (m, 1H), 1.90 (m, 1H), 2.16 (m, 2H), 2.38 (m, 3H), 2.99 (m, 1H), 3.80 (m, 1H), 5.46 (m, 1H), 7.46 (m, 1H), 7.56 (m, 1H), 7.63 (m, 2H), 7.69 (m, 2H), 8.16 (m, 1H), 8.47 (m, 1H), 8.75 (m, 1H), 8.86 (m, 1H), 11.26 (m, 1H).

LCMS(ESI): [M]$^+$ m/z: calcd 459.4; found 460.2; Rt=2.036 min.

Example 120. The Synthesis of 5-(2-(5-methyl-2-(2-(methylamino)benzo[D]thiazol-5-yl)piperidin-1-yl)-2-oxoacetamido)Nicotinamide (Compound 862 and Compound 877

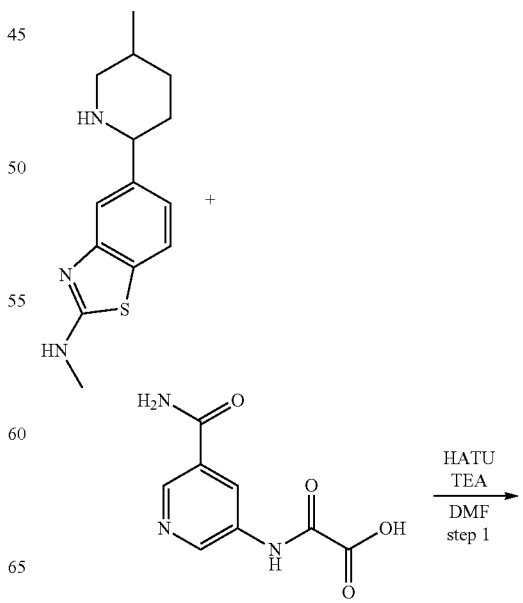

-continued

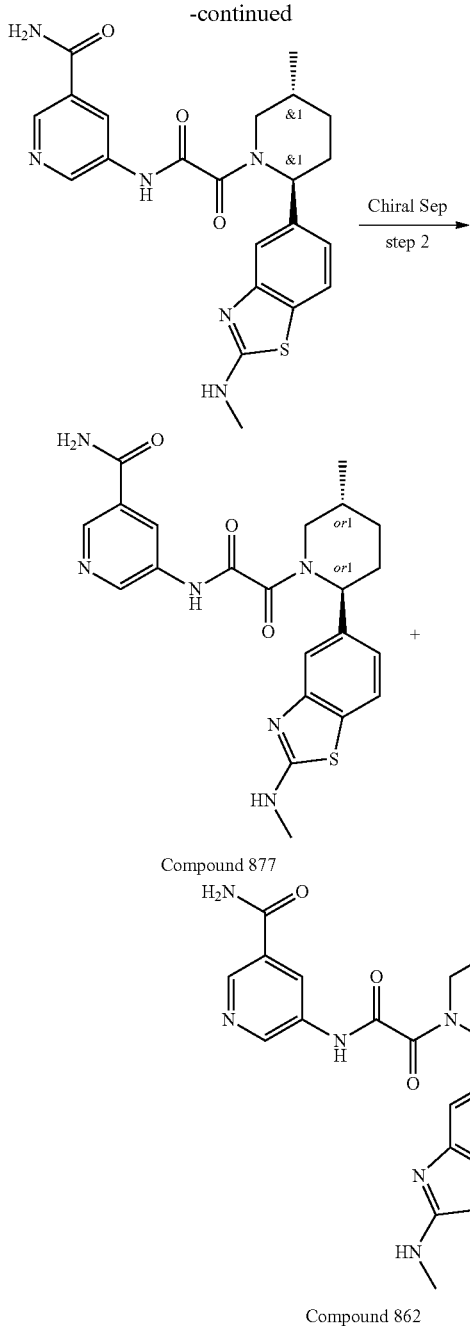

Compound 877

Compound 862

Step 1: Synthesis of 5-(2-(5-methyl-2-(2-(methyl-amino)benzo[d]thiazol-5-yl)piperidin-1-yl)-2-oxoac-etamido)Nicotinamide 2-[(5-carbamoyl-3-pyridyl)amino]-2-oxo-acetic acid (281.91 mg, 1.15 mmol, HCl) and N-methyl-5-(5-methyl-2-piperidyl)-1,3-benzothiazol-2-amine (0.3 g, 1.15 mmol) were mixed in DMF (20 mL). The reaction suspension was cooled to 0° C. and HATU (523.68 mg, 1.38 mmol) followed by TEA (348.42 mg, 3.44 mmol, 479.91 μL) were added and stirred at ambient temperature for 12 hr. The reaction mixture was evaporated in vacuum and obtained crude product 0.36 g was purified by preparative 50-50-55% 0-1-6 min H$_2$O/MeOH/0.1% NH$_4$OH, flow: 30 ml to afford product 5-[[2-[(2R,5S)-5-methyl-2-[2-(methylamino)-1,3-ben-zothiazol-5-yl]-1-piperidyl]-2-oxo-acetyl]amino]pyridine-3-carboxamide (0.15 g, 331.47 μmol, 28.88% yield).

LCMS(ESI): [M]$^+$ m/z: calcd 452.2; found 453.2; Rt=1.875 min.

Step 2: Chiral Separation (Compound 862 and Compound 877

The 5-[[2-[(2R,5S)-5-methyl-2-[2-(methylamino)-1,3-benzothiazol-5-yl]-1-piperidyl]-2-oxo-acetyl]amino]pyridine-3-carboxamide (0.15 g, 331.47 μmol) was subjected to chiral HPLC purification (Column: IA-II (250*20.5 mkm), Eluent: Hexane-IPA-MeOH, 70-15-15, flow rate: 15 mL/min) to give the two individual enantiomers Compound 877 5-[[2-[(2S,5R)-5-methyl-2-[2-(methylamino)-1,3-benzothiazol-5-yl]-1-piperidyl]-2-oxo-acetyl]amino]pyridine-3-carboxamide (0.02767 g, 61.15 μmol, 18.45% yield) and Compound 862 5-[[2-[(2R,5S)-5-methyl-2-[2-(methylamino)-1,3-benzothiazol-5-yl]-1-piperidyl]-2-oxo-acetyl]amino]pyridine-3-carboxamide (0.03257 g, 71.97 μmol, 21.71% yield).

Ret time for Compound 862 in analytical conditions (column: IA-3, Hexane-IPA-MeOH, 50-25-25, 0.15 ml/min as mobile phase) 7.95 min and for Compound 877 12.36 min.

Compound 862: Retention time: 7.95 min
$^1$H NMR (600 MHz, DMSO-d$_6$) δ (ppm) 0.98-1.06 (m, 3H), 1.26-1.40 (m, 1H), 1.63-1.77 (m, 1H), 1.81-1.94 (m, 1H), 1.98-2.19 (m, 1H), 2.20-2.31 (m, 1H), 2.78-2.84 (m, 0.4H), 2.89-2.96 (m, 3H), 3.22-3.28 (m, 0.6H), 3.44-4.04 (m, 1H), 5.15-5.66 (m, 1H), 6.91-7.05 (m, 1H), 7.28-7.40 (m, 1H), 7.53-7.62 (m, 1H), 7.62-7.71 (m, 1H), 7.81-7.98 (m, 1H), 8.03-8.25 (m, 1H), 8.41-8.55 (m, 1H), 8.69-8.79 (m, 1H), 8.83-8.94 (m, 1H), 11.11-11.39 (m, 1H).

LCMS(ESI): [M]$^+$ m/z: calcd 452.2; found 453.2; Rt=1.960 min.

Compound 877: Retention time: 12.36 min
$^1$H NMR (600 MHz, DMSO-d$_6$) δ (ppm) 0.99-1.06 (m, 3H), 1.30-1.40 (m, 1H), 1.65-1.77 (m, 1H), 1.81-1.93 (m, 1H), 1.98-2.18 (m, 1H), 2.19-2.31 (m, 1H), 2.79-2.82 (m, 0.3H), 2.88-2.93 (m, 3H), 3.25-3.28 (m, 0.7H), 3.44-4.03 (m, 1H), 5.15-5.67 (m, 1H), 6.94-7.03 (m, 1H), 7.29-7.40 (m, 1H), 7.54-7.62 (m, 1H), 7.62-7.70 (m, 1H), 7.89-7.94 (m, 1H), 8.09-8.22 (m, 1H), 8.42-8.51 (m, 1H), 8.69-8.80 (m, 1H), 8.82-8.94 (m, 1H), 10.97-11.54 (m, 1H).

LCMS(ESI): [M]$^+$ m/z: calcd 452.2; found 453.2; Rt=1.961 min.

Example 121. The Synthesis of 2-methoxy-5-(2-(5-methyl-2-(2-(methylamino)benzo[d]thiazol-5-yl)piperidin-1-yl)-2-oxoacetamido)Nicotinamide

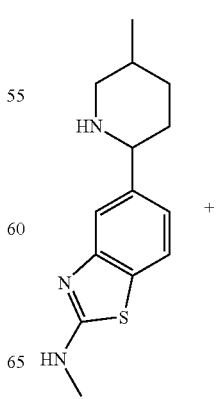

+

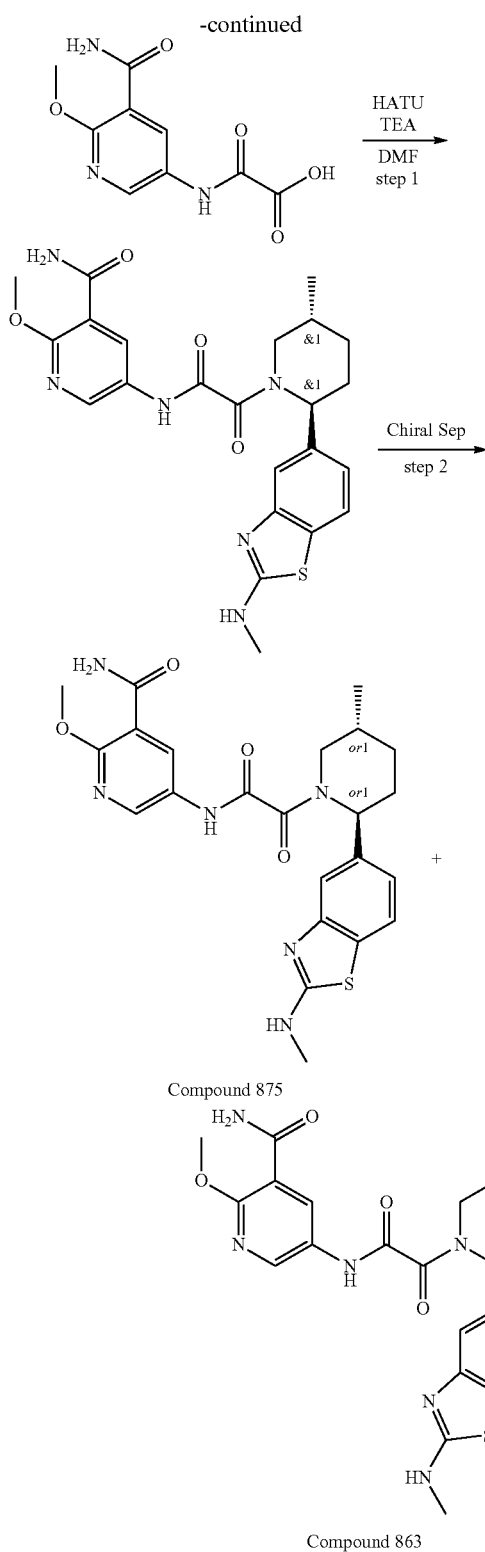

Compound 875

Compound 863

Step 1: Synthesis of 2-methoxy-5-(2-(5-methyl-2-(2-(methylamino)benzo[d]thiazol-5-yl)piperidin-1-yl)-2-oxoacetamido)Nicotinamide 2-[(5-carbamoyl-6-methoxy-3-pyridyl)amino]-2-oxo-acetic acid (201.31 mg, 841.67 μmol) and N-methyl-5-(5-methyl-2-piperidyl)-1,3-benzothiazol-2-amine (0.22 g, 841.67 μmol) were mixed in DMF (20 mL). The reaction suspension was cooled to 0° C. and HATU (384.03 mg, 1.01 mmol) followed by TEA (170.34 mg, 1.68 mmol, 234.62 μL) were added and stirred at ambient temperature for 12 hr. The reaction mixture was evaporated in vacuum and obtained crude product 0.5 g was purified by preparative 55-75% 0-1-6 min H$_2$O/MeOH/0.1% NH$_4$OH, flow: 30 ml/min to afford product 2-methoxy-5-[[2-[(2R,5S)-5-methyl-2-[2-(methylamino)-1,3-benzothiazol-5-yl]-1-piperidyl]-2-oxo-acetyl]amino]pyridine-3-carboxamide (0.155 g, 321.21 μmol, 38.16% yield).

$^1$H NMR (400 MHz, DMSO-d$_6$) δ (ppm) 1.11 (d, 3H), 1.42 (m, 1H), 2.12 (m, 4H), 2.98 (m, 3H), 3.32 (m, 1H), 3.52 (m, 1H), 3.98 (m, 3H), 5.55 (m, 1H), 7.02 (m, 1H), 7.46 (m, 1H), 7.82 (m, 3H), 7.96 (m, 1H), 8.56 (m, 2H), 11.12 (m, 1H).

LCMS(ESI): [M]$^+$ m/z: calcd 482.2; found 483.2; Rt=2.409 min.

Step 2: Chiral Separation (Compound 863 and Compound 875

The 2-methoxy-5-[[2-[(2R,5S)-5-methyl-2-[2-(methylamino)-1,3-benzothiazol-5-yl]-1-piperidyl]-2-oxo-acetyl]amino]pyridine-3-carboxamide (0.155 g, 321.21 μmol) was subjected to chiral HPLC purification (Column: IA-II (250*20.5 mkm), Eluent: Hexane-IPA-MeOH, 50-25-25, flow rate: 12 mL/min) to give the two individual enantiomers Compound 863 2-methoxy-5-[[2-[(2R,5S)-5-methyl-2-[2-(methylamino)-1,3-benzothiazol-5-yl]-1-piperidyl]-2-oxo-acetyl]amino]pyridine-3-carboxamide (0.05441 g, 112.75 μmol, 35.10% yield) and Compound 875 2-methoxy-5-[[2-[(2S,5R)-5-methyl-2-[2-(methylamino)-1,3-benzothiazol-5-yl]-1-piperidyl]-2-oxo-acetyl]amino]pyridine-3-carboxamide (0.0451 g, 93.46 μmol, 29.10% yield).

Ret time for Compound 863 in analytical conditions (column: IA, Hexane-IPA-MeOH, 50-25-25, 0.6 ml/min as mobile phase) 63.81 min and for Compound 875 38.60 min.

Compound 863: Retention time: 63.81 min $^1$H NMR (600 MHz, DMSO-d$_6$) δ (ppm) 0.99-1.03 (m, 3H), 1.27-1.37 (m, 1H), 1.65-1.74 (m, 1H), 1.79-1.92 (m, 1H), 1.99-2.17 (m, 1H), 2.20-2.30 (m, 1H), 2.77-2.81 (m, 0.3H), 2.89-2.92 (m, 3H), 3.24-3.28 (m, 0.7H), 3.42-3.49 (m, 0.7H), 3.89-3.96 (m, 3H), 3.99-4.04 (m, 0.3H), 5.13-5.74 (m, 1H), 6.90-7.04 (m, 1H), 7.29-7.38 (m, 1H), 7.58-7.68 (m, 1H), 7.68-7.78 (m, 2H), 7.87-7.95 (m, 1H), 8.33-8.48 (m, 1H), 8.49-8.59 (m, 1H), 10.93-11.21 (m, 1H).

LCMS(ESI): [M]$^+$ m/z: calcd 482.2; found 483.2; Rt=1.749 min.

Compound 875: Retention time: 38.60 min $^1$H NMR (600 MHz, DMSO-d$_6$) δ (ppm) 0.97-1.10 (m, 3H), 1.27-1.42 (m, 1H), 1.64-1.76 (m, 1H), 1.81-1.93 (m, 1H), 2.01-2.20 (m, 1H), 2.20-2.33 (m, 1H), 2.76-2.83 (m, 0.3H), 2.88-2.97 (m, 3H), 3.24-3.28 (m, 0.7H), 3.43-3.47 (m, 0.7H), 3.88-3.98 (m, 3H), 3.98-4.03 (m, 0.3H), 5.11-5.65 (m, 1H), 6.91-7.04 (m, 1H), 7.27-7.38 (m, 1H), 7.59-7.67 (m, 1H), 7.66-7.77 (m, 2H), 7.84-7.96 (m, 1H), 8.37-8.49 (m, 1H), 8.49-8.60 (m, 1H), 10.89-11.25 (m, 1H).

LCMS(ESI): [M]$^+$ m/z: calcd 482.2; found 483.2; Rt=1.743 min.

Example 122. The Synthesis of N-(6-amino-5-eth-ylpyridin-3-yl)-2-(5-methyl-2-(2-(methylamino)benzo[d]thiazol-5-yl)piperidin-1-yl)-2-oxoacetamide (Compound 896 and Compound 884

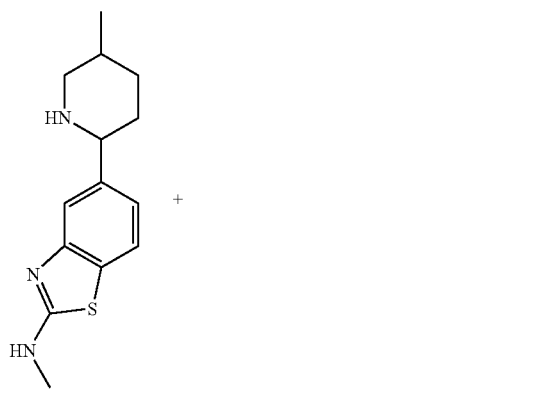

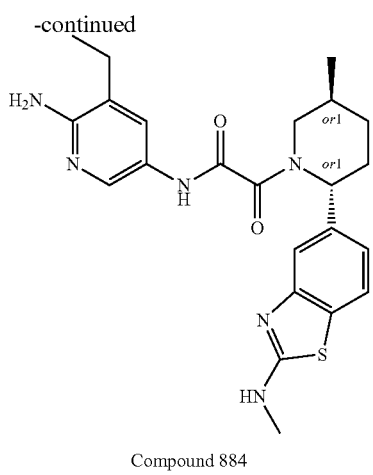

Compound 884

Step 1: Synthesis of N-(6-amino-5-ethylpyridin-3-yl)-2-(5-methyl-2-(2-(methylamino)benzo[d]thiazol-5-yl)piperidin-1-yl)-2-oxoacetamide 2-[(6-amino-5-ethyl-3-pyridyl)amino]-2-oxo-acetic acid (230.50 mg, 1.10 mmol) and N-methyl-5-(5-methyl-2-piperidyl)-1,3-benzothiazol-2-amine (0.32 g, 1.22 mmol) were mixed in DMF (20 mL). The reaction suspension was cooled to 0° C. and HATU (465.50 mg, 1.22 mmol) followed by TEA (247.76 mg, 2.45 mmol, 341.27 μL) were added and stirred at ambient temperature for 12 hr. The reaction mixture was evaporated in vacuum and obtained crude product 0.61 g was purified by preparative 60-60-70% 0-1-6 min H₂O/MeOH/0.1% NH₄OH, flow: 30 ml/min to afford product N-(6-amino-5-ethyl-3-pyridyl)-2-[(2R,5S)-5-methyl-2-[2-(methylamino)-1,3-benzothiazol-5-yl]-1-piperidyl]-2-oxo-acetamide (0.18 g, 397.73 μmol, 32.49% yield).

¹H NMR (400 MHz, DMSO-d₆) δ (ppm) 1.18 (m, 6H), 1.36 (m, 1H), 2.12 (m, 3H), 2.48 (m, 2H), 2.98 (m, 2H), 3.12 (m, 2H), 3.36 (m, 2H), 4.12 (m, 1H), 5.62 (m, 2H), 7.02 (m, 1H), 7.51 (m, 2H), 7.68 (m, 1H), 8.06 (m, 2H), 10.58 (m, 1H).

LCMS(ESI): [M]⁺ m/z: calcd 452.2; found 453.2; Rt=1.983 min.

Step 2: Chiral Separation (Compound 896 and Compound 884

The N-(6-amino-5-ethyl-3-pyridyl)-2-[(2R,5S)-5-methyl-2-[2-(methylamino)-1,3-benzothiazol-5-yl]-1-piperidyl]-2-oxo-acetamide (0.18 g, 397.73 μmol) was subjected to chiral HPLC purification (Column: IA-II (250*20.5 mkm), Eluent: Hexane-IPA-MeOH, 60-20-20, flow rate: 12 mL/min) to give the two individual enantiomers Compound 884 N-(6-amino-5-ethyl-3-pyridyl)-2-[(2R,5S)-5-methyl-2-[2-(methylamino)-1,3-benzothiazol-5-yl]-1-piperidyl]-2-oxo-acetamide (0.026 g, 57.45 μmol, 14.44% yield) and Compound 896 N-(6-amino-5-ethyl-3-pyridyl)-2-[(2R,5S)-5-methyl-2-[2-(methylamino)-1,3-benzothiazol-5-yl]-1-piperidyl]-2-oxo-acetamide (30.20 mg, 66.73 μmol, 16.78% yield).

Ret time for Compound 896 in analytical conditions (column: IA, Hexane-IPA-MeOH, 50-25-25, 0.6 ml/min as mobile phase) 24.85 min and for Compound 884 43.94 min.

Compound 896: Retention time: 24.85 min

¹H NMR (500 MHz, DMSO-d₆) δ (ppm) 1.03 (m, 6H), 1.34 (m, 1H), 1.70 (m, 1H), 1.86 (m, 1H), 2.01 (m, 1H), 2.14

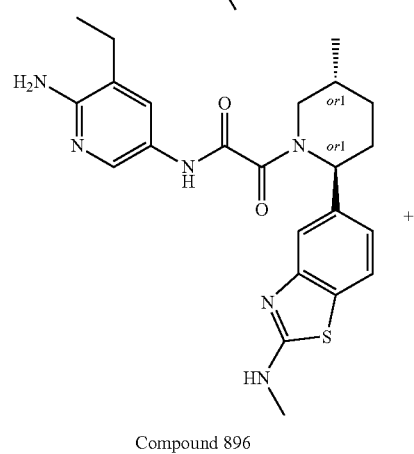

Compound 896

(m, 1H), 2.24 (m, 1H), 2.38 (m, 2H), 2.92 (m, 3H), 3.43 (m, 1H), 5.63 (m, 3H), 6.98 (m, 1H), 7.34 (d, 1H), 7.48 (d, 1H), 7.64 (m, 1H), 7.92 (m, 1H), 8.03 (d, 1H), 10.54 (m, 1H).

LCMS(ESI): [M]+ m/z: calcd 452.2; found 453.2; Rt=2.047 min.

Compound 884: Retention time: 43.94 min $^1$H NMR (500 MHz, DMSO-d$_6$) δ (ppm) 1.03 (m, 6H), 1.32 (m, 1H), 1.71 (m, 1H), 1.87 (m, 1H), 2.01 (d, 1H), 2.18 (m, 1H), 2.38 (m, 3H), 2.92 (s, 3H), 3.43 (m, 1H), 5.62 (m, 3H), 6.98 (dd, 1H), 7.34 (d, 1H), 7.48 (d, 1H), 7.64 (m, 1H), 7.92 (m, 1H), 8.03 (d, 1H), 10.53 (m, 1H).

LCMS(ESI): [M]+ m/z: calcd 452.2; found 453.2; Rt=2.051 min.

Example 123. The Synthesis of N-(5,6-dimethylpyridin-3-yl)-2-(5-methyl-2-(2-(methylamino)benzo[d]thiazol-5-yl)piperidin-1-yl)-2-oxoacetamide (Compound 828

2-oxo-acetic acid (339.01 mg, 1.15 mmol), N-methyl-5-[(2R,5S)-5-methyl-2-piperidyl]-1,3-benzothiazol-2-amine (300 mg, 1.15 mmol) and TEA (696.83 mg, 6.89 mmol, 959.83 µL) in DMF (13 mL). The clear solution was stirred at ambient temperature for 18 hr and the solvents were evaporated in vacuum to give 1 g of crude material. It was subjected to RP-HPLC (column: YMC Triart C18 100×20 mm, 5 um; 40-55% 0-5 min H$_2$O/MeCN/0.1% NH$_4$OH, flow: 30 ml/min as mobile phase) to give Compound 828 N-(5,6-dimethyl-3-pyridyl)-2-[(2R,5S)-5-methyl-2-[2-(methylamino)-1,3-benzothiazol-5-yl]-1-piperidyl]-2-oxo-acetamide (293 mg, 669.63 µmol, 58.34% yield).

$^1$H NMR (600 MHz, DMSO-d$_6$) δ (ppm) 0.70-1.03 (m, 3H), 1.11-1.36 (m, 1H), 1.64-1.73 (m, 1H), 1.79-1.92 (m, 1H), 2.12-2.19 (m, 2H), 2.20-2.27 (m, 3H), 2.31-2.37 (m, 3H), 2.78-3.26 (m, 4H), 3.38-4.24 (m, 1H), 5.07-6.70 (m, 1H), 6.92-7.02 (m, 1H), 7.28-7.39 (m, 1H), 7.58-7.66 (m, 1H), 7.72-7.86 (m, 1H), 7.86-7.97 (m, 1H), 8.36-8.53 (m, 1H), 10.85-11.03 (m, 1H).

LCMS(ESI): [M]+ m/z: calcd 437.2; found 438.2; Rt=1.992 min.

Example 124. The Synthesis of 5-[[2-[(2S,5R)-2-(5-acetamido-2-thienyl)-5-methyl-1-piperidyl]-2-oxo-acetyl]amino]pyridine-3-carboxamide (Compound 704) and 5-[[2-[(2R,5S)-2-(5-acetamido-2-thienyl)-5-methyl-1-piperidyl]-2-oxo-acetyl]amino]pyridine-3-carboxamide (Compound 686

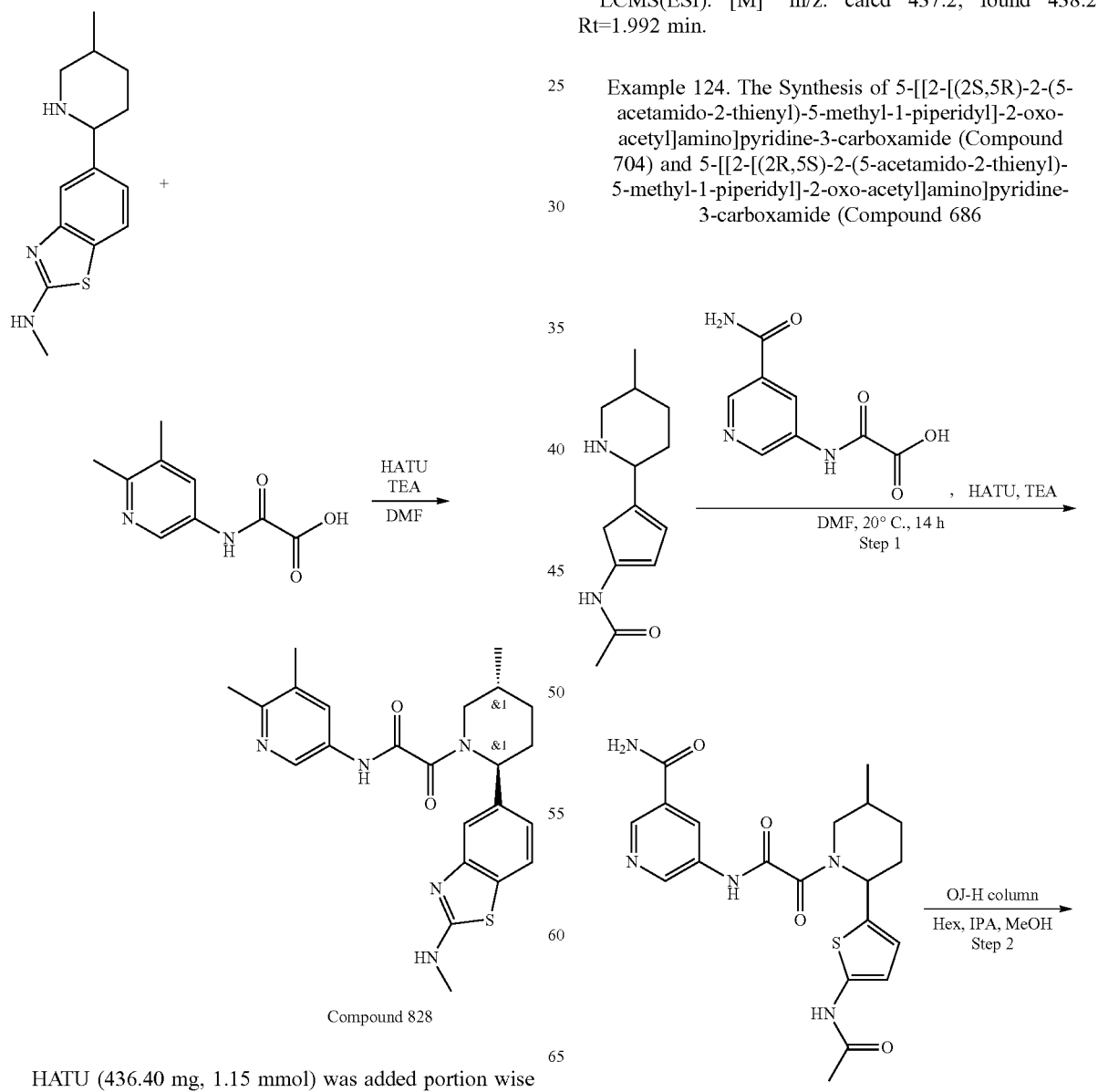

Compound 828

HATU (436.40 mg, 1.15 mmol) was added portion wise at rt to a suspension of 2-[(5,6-dimethyl-3-pyridyl)amino]-

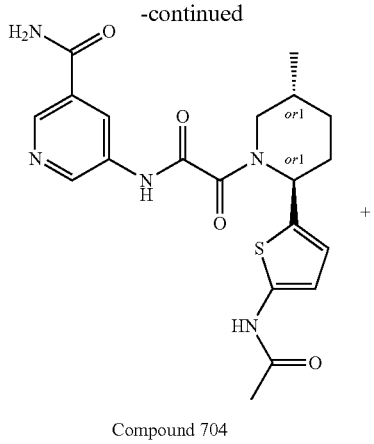

Compound 704

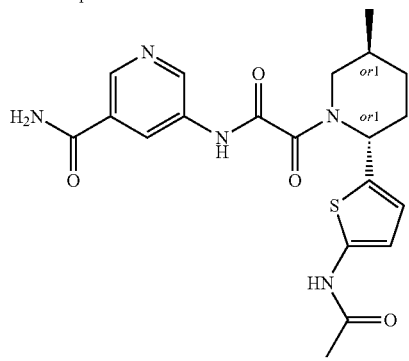

Compound 686

Step 1: The Synthesis of 5-[[2-[2-(5-acetamido-2-thienyl)-5-methyl-1-piperidyl]-2-oxo-acetyl]amino]pyridine-3-carboxamide 2-[(5-carbamoyl-3-pyridyl)amino]-2-oxo-acetic acid (627.34 mg, 2.55 mmol, HCl) and N-[5-(5-methyl-2-piperidyl)-2-thienyl]acetamide (0.9 g, 2.55 mmol, CF₃COOH) were mixed in DMF (15 mL). The reaction suspension was cooled to 20° C. and HATU (971.15 mg, 2.55 mmol) followed by TEA (1.29 g, 12.77 mmol, 1.78 mL) were added and stirred at ambient temperature for 14 hr. The reaction mixture was evaporated in vacuo and poured into water (100 ml) and extracted with EtOAc (2*30 ml). The combined organic extracts were washed with water (2*30 ml), dried over sodium sulphate and evaporated in vacuo and obtained crude product 0.45 g was purified by preparative 25-75% 0-5 min water-methanol, flow 30 ml/min to afford product 5-[[2-[2-(5-acetamido-2-thienyl)-5-methyl-1-piperidyl]-2-oxo-acetyl]amino]pyridine-3-carboxamide (0.100 g, 232.83 µmol, 9.12% yield).

LCMS(ESI): [M+H]⁺ m/z: calcd 429.1; found 430.0; Rt=1.948 min.

Step 2: The Synthesis of 5-[[2-[(2S,5R)-2-(5-acetamido-2-thienyl)-5-methyl-1-piperidyl]-2-oxo-acetyl]amino]pyridine-3-carboxamide (Compound 704) and 5-[[2-[(2R,5S)-2-(5-acetamido-2-thienyl)-5-methyl-1-piperidyl]-2-oxo-acetyl]amino]pyridine-3-carboxamide (Compound 686

The enantiomers were separated by chiral HPLC (column: OJ-H (250*20, 5 mkm)), Hexane-IPA-MeOH, 70-15-15, 14 ml/min as mobile phase) to give the two individual enantiomers Compound 704 5-[[2-[(2S,5R)-2-(5-acetamido-2-thienyl)-5-methyl-1-piperidyl]-2-oxo-acetyl]amino]pyridine-3-carboxamide (37.20 mg, 86.61 µmol, 37.20% yield) and Compound 686 5-[[2-[(2R,5S)-2-(5-acetamido-2-thienyl)-5-methyl-1-piperidyl]-2-oxo-acetyl]amino]pyridine-3-carboxamide (0.0461 g, 107.34 µmol, 46.10% yield).

Compound 686: RT (IA, Hexane-IPA-MeOH, 70-15-15, 0.6 mL/min)=30.346 min.

¹H NMR (DMSO-d₆, 600 MHz): δ (ppm) 0.78 (m, 3H), 1.30 (m, 2H), 1.68 (m, 2H), 1.88 (m, 1H), 2.02 (m, 3H), 2.21 (m, 1H), 3.90 (m, 1H), 5.53 (m, 1H), 6.47 (m, 1H), 6.69 (m, 1H), 7.58 (m, 1H), 8.15 (m, 1H), 8.49 (m, 1H), 8.81 (m, 2H), 11.05 (s, 1H), 11.23 (s, 1H).

LCMS(ESI): [M+H]⁺ m/z: calcd 429.2; found 430.2; Rt=1.042 min.

Compound 704: RT (IA, Hexane-IPA-MeOH, 70-15-15, 0.6 mL/min)=26.867 min.

¹H NMR (DMSO-d₆, 600 MHz): δ (ppm) 0.79 (dd, 3H), 1.31 (m, 1H), 1.68 (m, 2H), 1.89 (m, 1H), 2.01 (m, 3H), 2.20 (m, 1H), 2.72 (m, 1H), 3.89 (m, 1H), 5.53 (m, 1H), 6.47 (m, 1H), 6.69 (m, 1H), 7.59 (d, 1H), 8.15 (d, 1H), 8.49 (m, 1H), 8.75 (m, 1H), 8.87 (m, 1H), 11.05 (s, 1H), 11.23 (s, 1H).

LCMS(ESI): [M+H]⁺ m/z: calcd 429.2; found 430.2; Rt=1.041 min.

Example 125. The Synthesis of 5-(2-(2-(5-carbamoylthiophen-2-yl)-5-methylpiperidin-1-yl)-2-oxoacetamido)Nicotinamide (Compound 796 and Compound 792

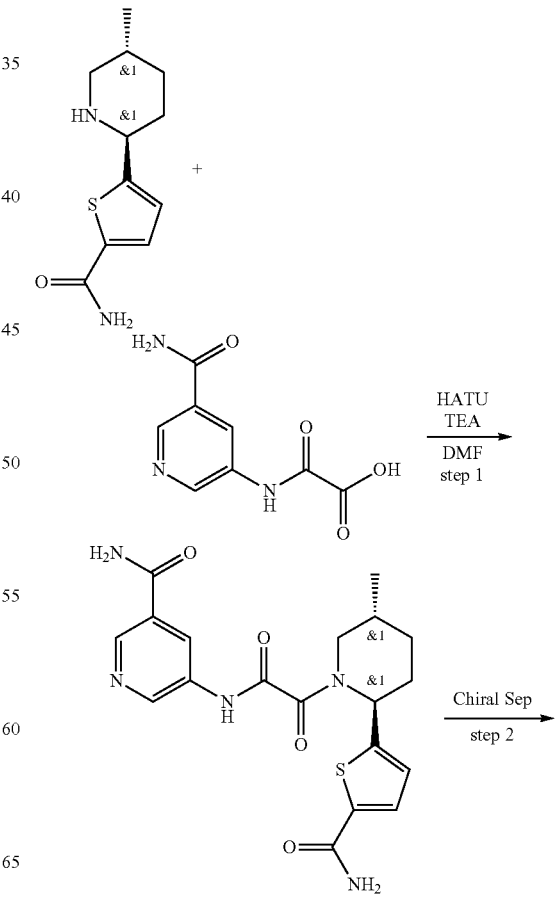

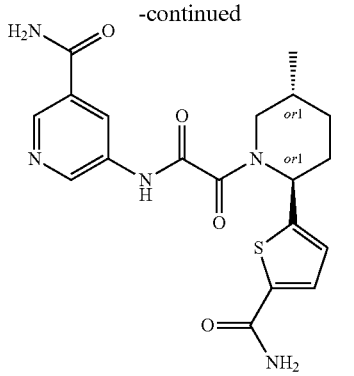

Compound 792

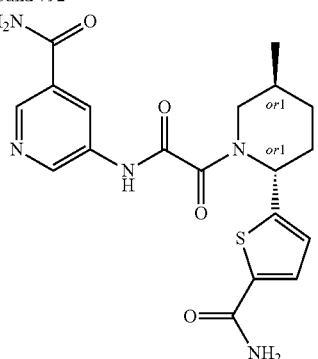

Compound 796

Step 1: Synthesis of 5-(2-(2-(5-carbamoylthiophen-2-yl)-5-methylpiperidin-1-yl)-2-oxoacetamido)Nicotinamide To a stirred mixture of 5-[(2S,5R)-5-methyl-2-piperidyl]thiophene-2-carboxamide (185 mg, 824.71 μmol), 2-[(5-carbamoyl-3-pyridyl)amino]-2-oxo-acetic acid (202.56 mg, 824.71 μmol, HCl) and TEA (250.36 mg, 2.47 mmol, 344.84 μL) in DMF (3 mL) was added HATU (344.94 mg, 907.18 μmol). The resulting reaction mixture was stirred at 20° C. for 4 hr. Then, it was subjected to HPLC (column: YMC-Actus Triart C18 100*20 mml.D. S-5 um; 20-40% 1-6 min water-MeOH (NH₃ 0.1%), flow 30 ml/min), affording 5-[[2-[(2S,5R)-2-(5-carbamoyl-2-thienyl)-5-methyl-1-piperidyl]-2-oxo-acetyl]amino]pyridine-3-carboxamide (127 mg, 305.68 μmol, 37.07% yield).

LCMS(ESI): [M]⁺ m/z: calcd 415.2; found 416.2; Rt=1.784 min.

Step 2: Chiral Separation (Compound 796 and Compound 792

5-[[2-[(2S,5R)-2-(5-carbamoyl-2-thienyl)-5-methyl-1-piperidyl]-2-oxo-acetyl]amino]pyridine-3-carboxamide (59 mg, 142.01 μmol) was divided into enantiomers by Chiral HPLC (CHIRALPAC IB 250*20 mm, 5 mkm; Hexane-IPA-MeOH, 70-15-15, flow rate: 15 ml/min, 10 mg/inj., 6 injections), affording: 5-[[2-[(2S,5R)-2-(5-carbamoyl-2-thienyl)-5-methyl-1-piperidyl]-2-oxo-acetyl]amino]pyridine-3-carboxamide (24 mg, 57.77 μmol, 81.36% yield) with ret.time=27.71 min (Compound 792) and 5-[[2-[(2R,5S)-2-(5-carbamoyl-2-thienyl)-5-methyl-1-piperidyl]-2-oxo-acetyl]amino]pyridine-3-carboxamide (26 mg, 62.58 μmol, 88.14% yield) with ret.time=46.89 min (Compound 796).

Ret time for Compound 796 in analytical conditions (column: IB, Hexane-IPA-MeOH, 70-15-15, 0.6 ml/min as mobile phase) 55.18 min and for Compound 792 30.99 min.

Compound 796: Retention time: 55.18 min
¹H NMR (600 MHz, DMSO-d₆) δ (ppm) 0.99-1.03 (m, 3H), 1.37-1.47 (m, 1H), 1.76-1.86 (m, 1H), 1.86-1.97 (m, 1H), 1.99-2.04 (m, 1H), 2.06-2.22 (m, 1H), 2.88-2.93 (m, 0.4H), 3.32-3.36 (m, 0.6H), 3.44-4.09 (m, 1H), 5.43-5.85 (m, 1H), 7.01 (s, 1H), 7.25-7.40 (m, 1H), 7.55-7.67 (m, 2H), 7.84-7.97 (m, 1H), 8.10-8.20 (m, 1H), 8.45-8.51 (m, 1H), 8.71-8.91 (m, 2H), 11.09-11.46 (m, 1H).

LCMS(ESI): [M]⁺ m/z: calcd 415.2; found 416.2; Rt=1.699 min.

Compound 792: Retention time: 30.99 min
¹H NMR (600 MHz, DMSO-d₆) δ (ppm) 0.98-1.01 (m, 3H), 1.37-1.45 (m, 1H), 1.77-1.85 (m, 1H), 1.87-1.98 (m, 1H), 1.99-2.04 (m, 1H), 2.06-2.21 (m, 1H), 2.88-2.93 (m, 0.4H), 3.32-3.35 (m, 0.6H), 3.46-4.07 (m, 1H), 5.43-5.87 (m, 1H), 7.01 (s, 1H), 7.27-7.40 (m, 1H), 7.55-7.66 (m, 2H), 7.86-7.97 (m, 1H), 8.11-8.21 (m, 1H), 8.44-8.52 (m, 1H), 8.72-8.83 (m, 1H), 8.83-8.91 (m, 1H), 11.09-11.37 (m, 1H).

LCMS(ESI): [M]⁺ m/z: calcd 415.2; found 416.2; Rt=1.699 min.

Example 126. The Synthesis of 5-(2-(2-(5-carbamoylthiophen-2-yl)-5-methylpiperidin-1-yl)-2-oxoacetamido)-2-methoxynicotinamide (Compound 844 and Compound 837

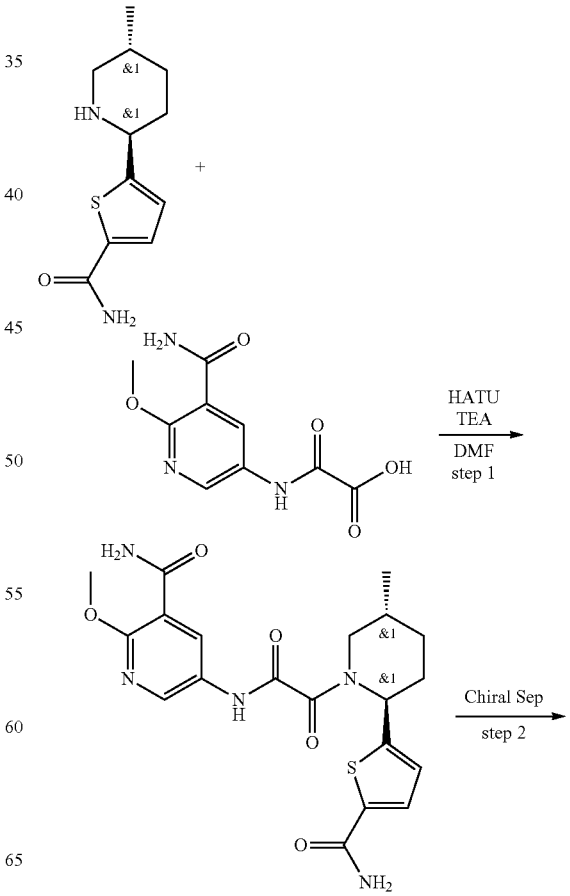

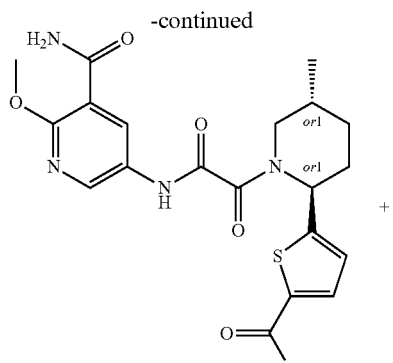

Compound 844

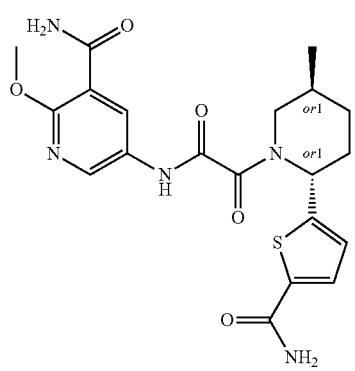

Compound 837

Step 1: Synthesis of 5-(2-(2-(5-carbamoylthiophen-2-yl)-5-methylpiperidin-1-yl)-2-oxoacetamido)-2-methoxynicotinamide To a stirred mixture of 5-[(2S,5R)-5-methyl-2-piperidyl]thiophene-2-carboxamide (190 mg, 847.00 μmol), 2-[(5-carbamoyl-6-methoxy-3-pyridyl)amino]-2-oxo-acetic acid (202.59 mg, 847.00 μmol) and TEA (171.42 mg, 1.69 mmol, 236.11 μL) in DMF (3 mL) was added HATU (354.26 mg, 931.70 μmol). The resulting reaction mixture was stirred at 20° C. for 4 hr. Then, it was subjected to HPLC (20-60%0-5 min H₂O/MeOH/0.1% NH₄OH, flow: 30 ml/min; column: YMC Triart C18 100×20 mm, 5 um), affording 5-[[2-[(2S,5R)-2-(5-carbamoyl-2-thienyl)-5-methyl-1-piperidyl]-2-oxo-acetyl]amino]-2-methoxy-pyridine-3-carboxamide (164 mg, 368.13 μmol, 43.46% yield).

$^1$H NMR (500 MHz, CDCl₃) δ (ppm)
LCMS(ESI): [M]⁺ m/z: calcd 445.2; found 446.2; Rt=2.187 min.

Step 2: Chiral Separation (Compound 844 and Compound 837

5-[[2-[(2S,5R)-2-(5-carbamoyl-2-thienyl)-5-methyl-1-piperidyl]-2-oxo-acetyl]amino]-2-methoxy-pyridine-3-carboxamide (164 mg, 368.13 μmol) was divided into enantiomers by Chiral HPLC (Column: Chiralpak IA (250×20 mm, 5 mkm); Mobile phase: Hexane-IPA-MeOH, 50-25-25, Flow Rate: 12 mL/min; Column Temperature: 24° C.), affording: 5-[[2-[(2S,5R)-2-(5-carbamoyl-2-thienyl)-5-methyl-1-piperidyl]-2-oxo-acetyl]amino]-2-methoxy-pyridine-3-carboxamide (40 mg, 89.79 μmol, 48.78% yield) with ret.time=45.11 min (Compound 844) and 5-[[2-[(2R,5S)-2-(5-carbamoyl-2-thienyl)-5-methyl-1-piperidyl]-2-oxo-acetyl]amino]-2-methoxy-pyridine-3-carboxamide (40 mg, 89.79 μmol, 48.78% yield) with ret.time=77.66 min (Compound 837).

Ret time for Compound 844 in analytical conditions (column: IA, Hexane-IPA-MeOH, 40-30-30, 0.6 ml/min as mobile phase) 30.58 min and for Compound 837 49.18 min.

Compound 844: Retention time: 30.58 min $^1$H NMR (600 MHz, DMSO-d₆) δ (ppm) 0.97-1.00 (m, 3H), 1.37-1.45 (m, 1H), 1.75-1.84 (m, 1H), 1.85-1.96 (m, 1H), 1.98-2.04 (m, 1H), 2.07-2.21 (m, 1H), 2.88 (d, 1H), 3.44-4.06 (m, 4H), 5.43-5.81 (m, 1H), 6.98-7.02 (m, 1H), 7.29-7.35 (m, 1H), 7.59-7.64 (m, 1H), 7.68-7.76 (m, 2H), 7.86-7.94 (m, 1H), 8.42-8.49 (m, 1H), 8.51-8.55 (m, 1H), 10.99-11.04 (m, 1H).

LCMS(ESI): [M]⁺ m/z: calcd 445.2; found 446.2; Rt=1.016 min.

Compound 837: Retention time: 49.18 min $^1$H NMR (600 MHz, DMSO-d₆) δ (ppm) 0.96-1.00 (m, 3H), 1.36-1.45 (m, 1H), 1.76-1.94 (m, 2H), 1.95-2.03 (m, 1H), 2.05-2.19 (m, 1H), 2.85-3.27 (m, 1H), 3.44-4.07 (m, 4H), 5.40-5.82 (m, 1H), 6.93-7.06 (m, 1H), 7.24-7.40 (m, 1H), 7.55-7.67 (m, 1H), 7.67-7.78 (m, 2H), 7.83-7.97 (m, 1H), 8.42-8.49 (m, 1H), 8.51-8.56 (m, 1H), 10.97-11.06 (m, 1H).

LCMS(ESI): [M]⁺ m/z: calcd 445.2; found 446.2; Rt=1.017 min.

Example 127. The Synthesis of 5-(1-(2-((6-amino-5-ethylpyridin-3-yl)amino)-2-oxoacetyl)-5-methylpiperidin-2-yl)thiophene-2-carboxamide (Compound 845 and Compound 838

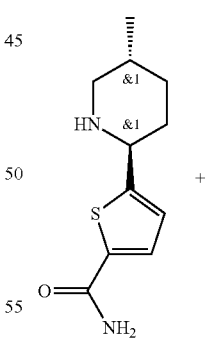

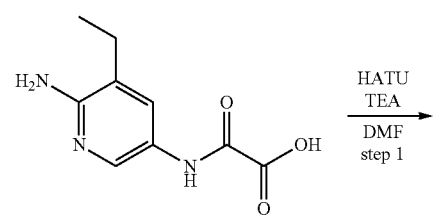

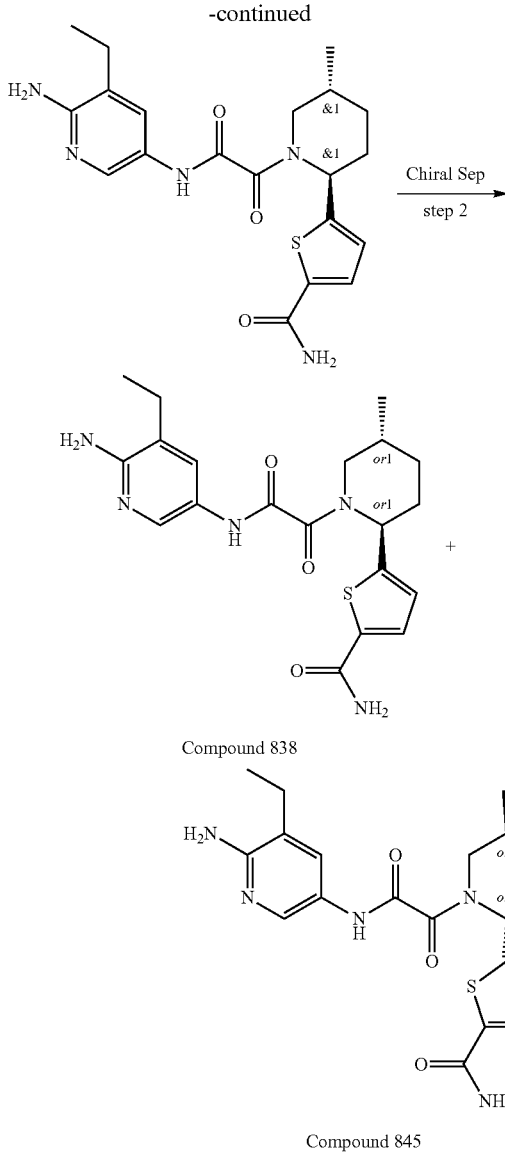

Compound 838

Compound 845

Step 1: Synthesis of 5-(1-(2-((6-amino-5-ethylpyridin-3-yl)amino)-2-oxoacetyl)-5-methylpiperidin-2-yl)thiophene-2-carboxamide To a stirred mixture of 5-[(2S,5R)-5-methyl-2-piperidyl]thiophene-2-carboxamide (190 mg, 847.00 μmol), 2-[(6-amino-5-ethyl-3-pyridyl)amino]-2-oxo-acetic acid (177.19 mg, 847.00 μmol) and TEA (171.42 mg, 1.69 mmol, 236.11 μL) in DMF (3 mL) was added HATU (354.26 mg, 931.70 μmol). The resulting reaction mixture was stirred at 20° C. for 4 hr. Then, it was subjected to HPLC (25-50% 0-5 min H$_2$O/ACN/0.1% NH$_4$OH, flow: 30 ml/min; column: YMC Triart C18 100×20 mm, 5 um), affording 5-[(2S,5R)-1-[2-[(6-amino-5-ethyl-3-pyridyl)amino]-2-oxo-acetyl]-5-methyl-2-piperidyl]thiophene-2-carboxamide (147 mg, 353.78 μmol, 41.77% yield).

$^1$H NMR (500 MHz, CDCl$_3$) δ (ppm)

LCMS(ESI): [M]$^+$ m/z: calcd 415.2; found 416.2; Rt=1.753 min.

Step 2: Chiral Separation (Compound 845 and Compound 838

5-[(2S,5R)-1-[2-[(6-amino-5-ethyl-3-pyridyl)amino]-2-oxo-acetyl]-5-methyl-2-piperidyl]thiophene-2-carboxamide (147 mg, 353.78 μmol) was divided into enantiomers by Chiral HPLC (Column: Chiralpak IA(250*20, 5 mkm), Mobile phase: Hexane-IPA-MeOH, 60-20-20; Flow rate: 12 ml/min. 24° C.), affording: 5-[(2R,5S)-1-[2-[(6-amino-5-ethyl-3-pyridyl)amino]-2-oxo-acetyl]-5-methyl-2-piperidyl]thiophene-2-carboxamide (60 mg, 144.40 μmol, 81.63% yield) with ret.time=32.2 min (Compound 845) and 5-[(2S,5R)-1-[2-[(6-amino-5-ethyl-3-pyridyl)amino]-2-oxo-acetyl]-5-methyl-2-piperidyl]thiophene-2-carboxamide (68 mg, 163.66 μmol, 92.52% yield) with ret.time=43.5 min (Compound 838).

Ret time for Compound 845 in analytical conditions (column: IA, Hexane-IPA-MeOH, 50-25-25, 0.6 ml/min as mobile phase) 35.87 min and for Compound 838 54.27 min.

Compound 845: Retention time: 35.87 min $^1$H NMR (600 MHz, DMSO-d$_6$) δ (ppm) 0.97-1.11 (m, 6H), 1.34-1.44 (m, 1H), 1.73-1.96 (m, 2H), 1.96-2.17 (m, 2H), 2.36-2.42 (m, 2H), 2.82-3.28 (m, 1H), 3.38-4.04 (m, 1H), 5.38-5.83 (m, 3H), 6.94-7.03 (m, 1H), 7.23-7.39 (m, 1H), 7.42-7.52 (m, 1H), 7.58-7.65 (m, 1H), 7.80-7.95 (m, 1H), 7.95-8.06 (m, 1H), 10.42-10.54 (m, 1H).

LCMS(ESI): [M]$^+$ m/z: calcd 415.2; found 416.2; Rt=0.915 min.

Compound 838: Retention time: 54.27 min $^1$H NMR (600 MHz, DMSO-d$_6$) δ (ppm) 0.97-1.01 (m, 3H), 1.06-1.12 (m, 3H), 1.34-1.44 (m, 1H), 1.74-1.85 (m, 1H), 1.85-1.96 (m, 1H), 2.00-2.19 (m, 2H), 2.33-2.36 (m, 1H), 2.38-2.40 (m, 1H), 3.29 (s, 1H), 3.42-4.06 (m, 1H), 5.39-5.80 (m, 3H), 6.94-7.02 (m, 1H), 7.32 (s, 1H), 7.45-7.51 (m, 1H), 7.59-7.65 (m, 1H), 7.90 (s, 1H), 7.97-8.06 (m, 1H), 10.45-10.53 (m, 1H).

LCMS(ESI): [M]$^+$ m/z: calcd 415.2; found 416.2; Rt=0.916 min.

Example 128. The Synthesis of 2-methoxy-5-(2-(5-methyl-2-(5-(methylcarbamoyl)thiophen-2-yl)piperidin-1-yl)-2-oxoacetamido)Nicotinamide (Compound 833 and Compound 843

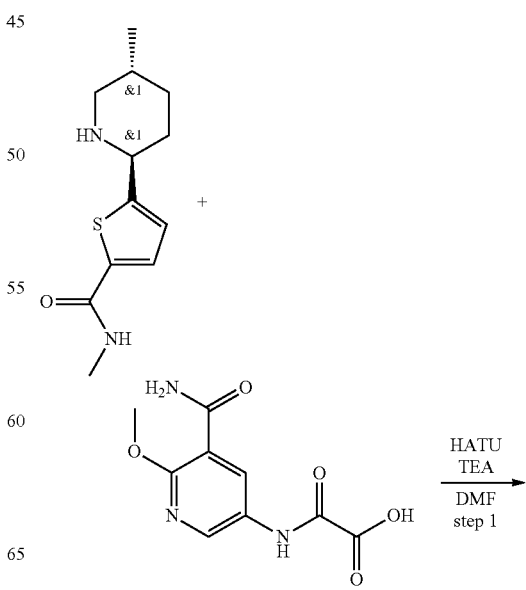

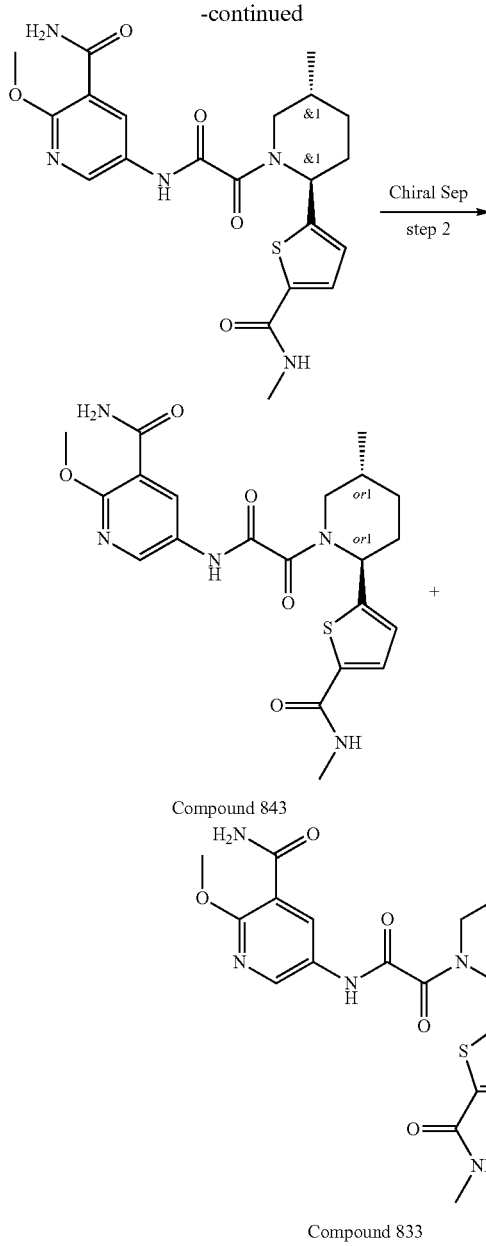

Compound 843

Compound 833

Step 1: Synthesis of 2-methoxy-5-(2-(5-methyl-2-(5-(methylcarbamoyl)thiophen-2-yl)piperidin-1-yl)-2-oxoacetamido)Nicotinamide To a stirred mixture of N-methyl-5-[(2S,5R)-5-methyl-2-piperidyl]thiophene-2-carboxamide (186 mg, 780.37 μmol), 2-[(5-carbamoyl-6-methoxy-3-pyridyl)amino]-2-oxo-acetic acid (186.65 mg, 780.37 μmol) and TEA (157.93 mg, 1.56 mmol, 217.54 μL) in DMF (3 mL) was added HATU (326.39 mg, 858.41 μmol). The resulting reaction mixture was stirred at 20° C. for 4 hr. Then, it was subjected to HPLC (30-50% 0-5 min H$_2$O/MeOH/0.1% NH$_4$OH, flow: 30 ml/min; column: YMC Triart C18 100×20 mm, 5 um), affording 2-methoxy-5-[[2-[(2S,5R)-5-methyl-2-[5-(methylcarbamoyl)-2-thienyl]-1-piperidyl]-2-oxo-acetyl]amino]pyridine-3-carboxamide (185 mg, 402.60 μmol, 51.59% yield).

LCMS(ESI): [M]$^+$ m/z: calcd 459.2; found 460.2; Rt=2.264 min.

Step 2: Chiral Separation (Compound 833 and Compound 843

2-methoxy-5-[[2-[(2S,5R)-5-methyl-2-[5-(methylcarbamoyl)-2-thienyl]-1-piperidyl]-2-oxo-acetyl]amino]pyridine-3-carboxamide (185 mg, 402.60 μmol) was divided into enantiomers by Chiral HPLC (Column: Chiralpak IA (250×20 mm, 5 mkm); Mobile phase: Hexane-IPA-MeOH, 60-20-20, Flow Rate: 12 mL/min; Column Temperature: 24° C.), affording: 2-methoxy-5-[[2-[(2S,5R)-5-methyl-2-[5-(methylcarbamoyl)-2-thienyl]-1-piperidyl]-2-oxo-acetyl]amino]pyridine-3-carboxamide (81 mg, 176.27 μmol, 87.57% yield) with ret.time=55.00 min (Compound 843) and 2-methoxy-5-[[2-[(2R,5S)-5-methyl-2-[5-(methylcarbamoyl)-2-thienyl]-1-piperidyl]-2-oxo-acetyl]amino]pyridine-3-carboxamide (83 mg, 180.62 μmol, 89.73% yield) with ret.time=74.84 min (Compound 833).

Ret time for Compound 833 in analytical conditions (column: IA, Hexane-IPA-MeOH, 50-25-25, 0.6 ml/min as mobile phase) 46.47 min and for Compound 843 34.75 min.

Compound 833: Retention time: 46.47 min $^1$H NMR (600 MHz, DMSO-d$_6$) δ (ppm) 0.96-1.02 (m, 3H), 1.36-1.44 (m, 1H), 1.72-1.85 (m, 1H), 1.86-1.97 (m, 1H), 1.98-2.04 (m, 1H), 2.06-2.19 (m, 1H), 2.69-2.74 (m, 3H), 2.84-3.29 (m, 1H), 3.44-4.07 (m, 4H), 5.43-5.80 (m, 1H), 6.97-7.04 (m, 1H), 7.54-7.61 (m, 1H), 7.68-7.77 (m, 2H), 8.34-8.42 (m, 1H), 8.44-8.49 (m, 1H), 8.52-8.56 (m, 1H), 10.95-11.08 (m, 1H).

LCMS(ESI): [M]$^+$ m/z: calcd 459.2; found 460.2; Rt=0.958 min.

Compound 843: Retention time: 34.75 min $^1$H NMR (600 MHz, DMSO-d$_6$) δ (ppm) 0.97-1.01 (m, 3H), 1.37-1.44 (m, 1H), 1.72-1.95 (m, 2H), 1.96-2.04 (m, 1H), 2.08-2.22 (m, 1H), 2.67-2.76 (m, 3H), 2.84-3.29 (m, 1H), 3.45-4.05 (m, 4H), 5.41-5.81 (m, 1H), 6.96-7.03 (m, 1H), 7.53-7.60 (m, 1H), 7.67-7.77 (m, 2H), 8.32-8.43 (m, 1H), 8.43-8.49 (m, 1H), 8.51-8.55 (m, 1H), 11.00-11.05 (m, 1H).

LCMS(ESI): [M]$^+$ m/z: calcd 459.2; found 460.2; Rt=0.958 min.

Example 129. The synthesis of 5-(1-(2-((6-amino-5-ethylpyridin-3-yl)amino)-2-oxoacetyl)-5-methylpiperidin-2-yl)-N-methylthiophene-2-carboxamide (Compound 840 and Compound 835

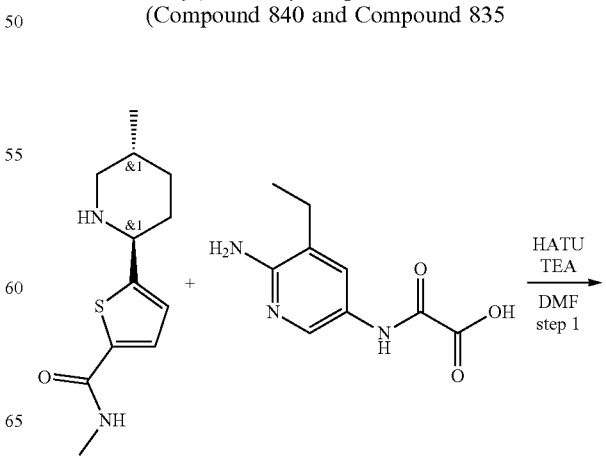

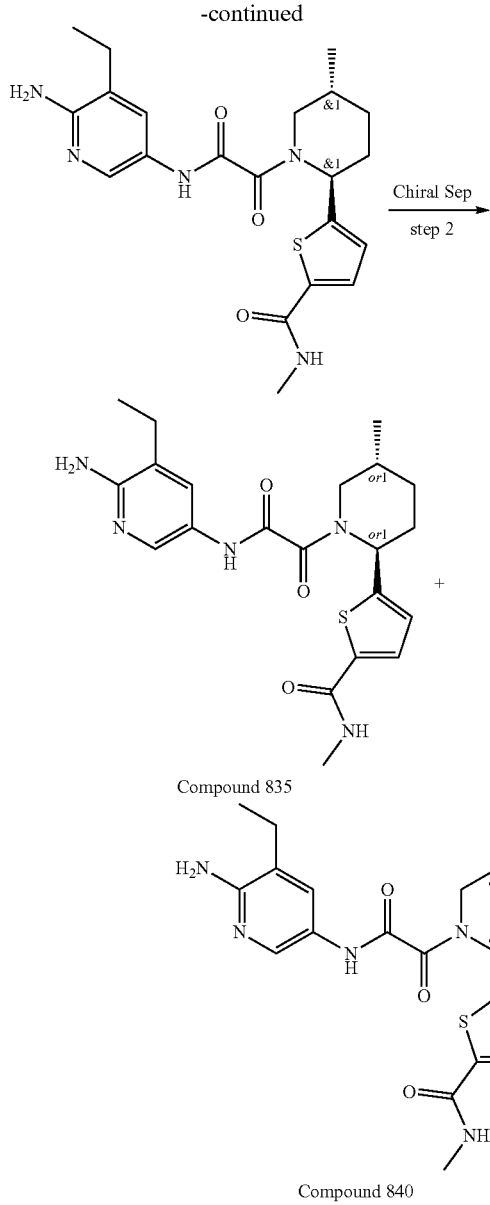

Compound 835

Compound 840

Step 1: Synthesis of 5-(1-(2-((6-amino-5-ethylpyridin-3-yl)amino)-2-oxoacetyl)-5-methylpiperidin-2-yl)-N-methylthiophene-2-carboxamide To a stirred mixture of N-methyl-5-[(2S,5R)-5-methyl-2-piperidyl]thiophene-2-carboxamide (186 mg, 780.37 μmol), 2-[(6-amino-5-ethyl-3-pyridyl)amino]-2-oxo-acetic acid (163.26 mg, 780.37 μmol) and TEA (157.93 mg, 1.56 mmol, 217.54 μL) in DMF (3 mL) was added HATU (326.39 mg, 858.41 μmol). The resulting reaction mixture was stirred at 20° C. for 4 hr. Then, it was subjected to HPLC (20-45% 0-5 min H$_2$O/ACN/0.1% NH$_4$OH, flow: 30 ml/min; column: YMC Triart C18 100×20 mm, 5 um), affording 5-[(2S,5R)-1-[2-[(6-amino-5-ethyl-3-pyridyl)amino]-2-oxo-acetyl]-5-methyl-2-piperidyl]-N-methyl-thiophene-2-carboxamide (145 mg, 337.57 μmol, 43.26% yield).

LCMS(ESI): [M]$^+$ m/z: calcd 429.2; found 430.2; Rt=1.942 min.

Step 2: Chiral Separation (Compound 840 and Compound 835

5-[(2S,5R)-1-[2-[(6-amino-5-ethyl-3-pyridyl)amino]-2-oxo-acetyl]-5-methyl-2-piperidyl]-N-methyl-thiophene-2-carboxamide (145 mg, 337.57 μmol) was divided into enantiomers by Chiral HPLC (Column: Chiralpak AD-H (250*20 mm, 5 mkm); Mobile phase: Hexane-IPA-MeOH, 50-25-25. Flow Rate: 11 mL/min; Column Temperature: 20° C.), affording: 5-[(2S,5R)-1-[2-[(6-amino-5-ethyl-3-pyridyl)amino]-2-oxo-acetyl]-5-methyl-2-piperidyl]-N-methyl-thiophene-2-carboxamide (76 mg, 176.94 μmol, 52.41% yield) with ret.time=30.25 min (Compound 835) and 5-[(2R,5S)-1-[2-[(6-amino-5-ethyl-3-pyridyl)amino]-2-oxo-acetyl]-5-methyl-2-piperidyl]-N-methyl-thiophene-2-carboxamide (88 mg, 204.87 μmol, 60.69% yield) with ret.time=64.89 min (Compound 840).

Ret time for Compound 840 in analytical conditions (column: AD-H, Hexane-IPA-MeOH, 40-30-30, 0.6 ml/min as mobile phase) 50.87 min and for Compound 835 25.71 min.

Compound 840: Retention time: 50.87 min $^1$H NMR (600 MHz, DMSO-d$_6$) δ (ppm) 0.96-1.01 (m, 3H), 1.07-1.12 (m, 3H), 1.35-1.44 (m, 1H), 1.73-1.84 (m, 1H), 1.86-2.04 (m, 2H), 2.05-2.18 (m, 1H), 2.36-2.41 (m, 2H), 2.69-2.74 (m, 3H), 2.82-3.28 (m, 1H), 3.41-4.06 (m, 1H), 5.41-5.78 (m, 3H), 6.95-7.03 (m, 1H), 7.44-7.50 (m, 1H), 7.53-7.59 (m, 1H), 7.99-8.05 (m, 1H), 8.34-8.40 (m, 1H), 10.46-10.53 (m, 1H).

LCMS(ESI): [M]$^+$ m/z: calcd 429.2; found 430.2; Rt=1.753 min.

Compound 835: Retention time: 25.71 min $^1$H NMR (600 MHz, DMSO-d$_6$) δ (ppm) 0.97-1.01 (m, 3H), 1.06-1.12 (m, 3H), 1.34-1.44 (m, 1H), 1.74-1.84 (m, 1H), 1.86-2.03 (m, 2H), 2.04-2.17 (m, 1H), 2.36-2.41 (m, 2H), 2.69-2.75 (m, 3H), 2.82-3.28 (m, 1H), 3.33-4.06 (m, 1H), 5.39-5.81 (m, 3H), 6.95-7.03 (m, 1H), 7.45-7.52 (m, 1H), 7.53-7.60 (m, 1H), 8.01-8.05 (m, 1H), 8.34-8.39 (m, 1H), 10.47-10.52 (m, 1H).

LCMS(ESI): [M]$^+$ m/z: calcd 429.2; found 430.2; Rt=0.975 min.

Example 130. The Synthesis of 5-(2-(5-methyl-2-(5-(methylcarbamoyl)thiophen-2-yl)piperidin-1-yl)-2-oxoacetamido)Nicotinamide (Compound 839 and Compound 829

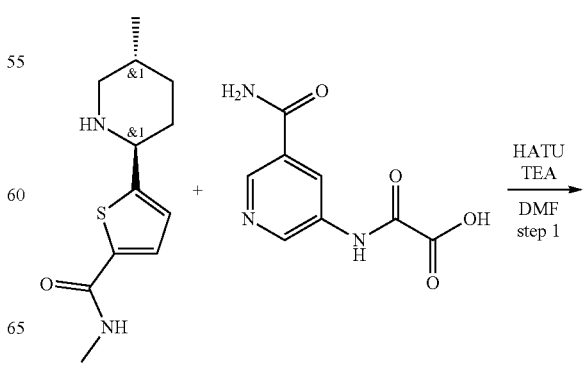

1495
-continued

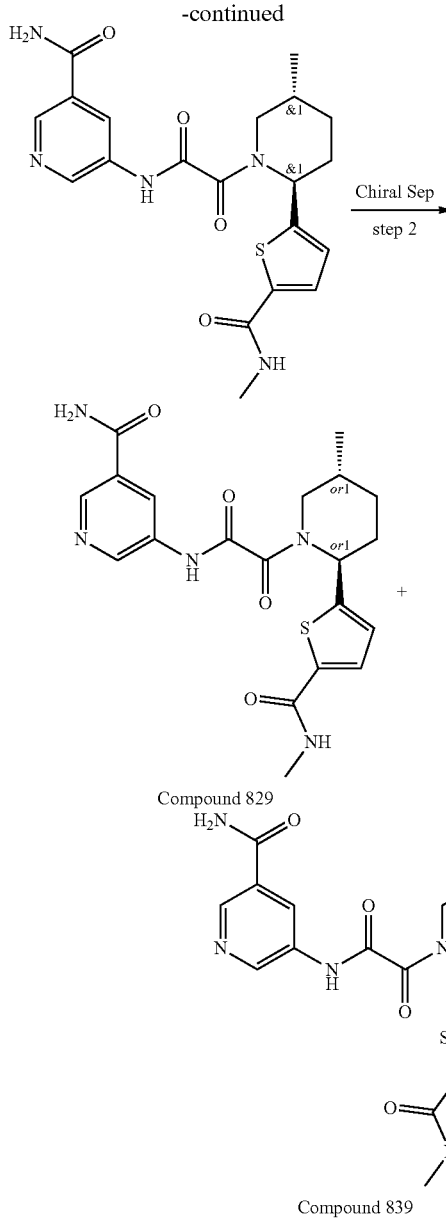

Compound 829

Compound 839

Step 1: Synthesis of 5-(2-(5-methyl-2-(5-(methyl-carbamoyl)thiophen-2-yl)piperidin-1-yl)-2-oxoacet-amido)Nicotinamide To a stirred mixture of N-methyl-5-[(2S,5R)-5-methyl-2-piperidyl]thiophene-2-carboxamide (186 mg, 780.37 µmol), 2-[(5-carbamoyl-3-pyridyl)amino]-2-oxo-acetic acid (191.67 mg, 780.37 µmol, HCl) and TEA (236.90 mg, 2.34 mmol, 326.30 µL) in DMF (3 mL) was added HATU (326.39 mg, 858.41 µmol). The resulting reaction mixture was stirred at 20° C. for 4 hr. Then, it was subjected to HPLC (20-45%0-5 min H₂O/MeOH/0.10% NH₄OH, flow: 30 ml/min; column: YMC Triart C18 100×20 mm, 5 um), affording 5-[[2-[(2S,5R)-5-methyl-2-[5-(methylcarbamoyl)-2-thienyl]-1-piperidyl]-2-oxo-acetyl]amino]pyridine-3-carboxamide (195 mg, 454.02 µmol, 58.18% yield).

LCMS(ESI): [M]⁺ m/z: calcd 429.2; found 430.2; Rt=1.898 min.

1496

Step 2: Chiral Separation (Compound 839 and Compound 829

5-[[2-[(2S,5R)-5-methyl-2-[5-(methylcarbamoyl)-2-thie-nyl]-1-piperidyl]-2-oxo-acetyl]amino]pyridine-3-carbox-amide (195 mg, 454.02 µmol) was divided into enantiomers by Chiral HPLC (Column: Chiralpak IA(250*20, 5 mkm), Mobile phase: Hexane-IPA-MeOH, 60-20-20; Flow rate: 12 ml/min. column temperature 24° C.), affording: 5-[[2-[(2R, 5S)-5-methyl-2-[5-(methylcarbamoyl)-2-thienyl]-1-pip-eridyl]-2-oxo-acetyl]amino]pyridine-3-carboxamide (45 mg, 104.77 µmol, 46.15% yield) with ret.time=27.9 min (Compound 839) and 5-[[2-[(2S,5R)-5-methyl-2-[5-(meth-ylcarbamoyl)-2-thienyl]-1-piperidyl]-2-oxo-acetyl]amino] pyridine-3-carboxamide (48 mg, 111.76 µmol, 49.23% yield) with ret.time=35.6 min (Compound 829).

Ret time for Compound 839 in analytical conditions (column: IA, Hexane-IPA-MeOH, 50-25-25, 0.6 ml/min as mobile phase) 20.57 min and for Compound 829 25.04 min.

Compound 839: Retention time: 20.57 min

¹H NMR (600 MHz, DMSO-d₆) δ (ppm) 0.92-1.06 (m, 3H), 1.36-1.46 (m, 1H), 1.74-1.97 (m, 2H), 2.00-2.21 (m, 2H), 2.69-2.76 (m, 3H), 2.85-3.28 (m, 1H), 3.45-4.08 (m, 1H), 5.42-5.82 (m, 1H), 6.95-7.05 (m, 1H), 7.53-7.64 (m, 2H), 8.10-8.19 (m, 1H), 8.35-8.43 (m, 1H), 8.45-8.52 (m, 1H), 8.73-8.79 (m, 1H), 8.87-8.91 (m, 1H), 11.20-11.30 (m, 1H).

LCMS(ESI): [M]⁺ m/z: calcd 429.2; found 430.2; Rt=1.000 min.

Compound 829: Retention time: 25.04 min

¹H NMR (600 MHz, DMSO-d₆) δ (ppm) 0.98-1.01 (m, 3H), 1.37-1.45 (m, 1H), 1.74-1.91 (m, 2H), 1.91-2.02 (m, 1H), 2.07-2.18 (m, 1H), 2.66-2.77 (m, 3H), 2.87-3.29 (m, 1H), 3.33-4.08 (m, 1H), 5.42-5.83 (m, 1H), 6.98-7.08 (m, 1H), 7.50-7.66 (m, 2H), 8.07-8.21 (m, 1H), 8.32-8.44 (m, 1H), 8.44-8.51 (m, 1H), 8.68-8.81 (m, 1H), 8.83-8.93 (m, 1H), 11.18-11.30 (m, 1H).

LCMS(ESI): [M]⁺ m/z: calcd 429.2; found 430.2; Rt=0.999 min.

Example 131. The Synthesis of Rel-N-(6-amino-5-ethyl-3-pyridyl)-2-[(2S,5R)-2-(1H-indazol-5-yl)-5-methyl-1-piperidyl]-2-oxo-acetamide (Compound 579) and Rel-N-(6-amino-5-ethyl-3-pyridyl)-2-[(2R, 5S)-2-(1H-indazol-5-yl)-5-methyl-1-piperidyl]-2-oxo-acetamide (Compound 589

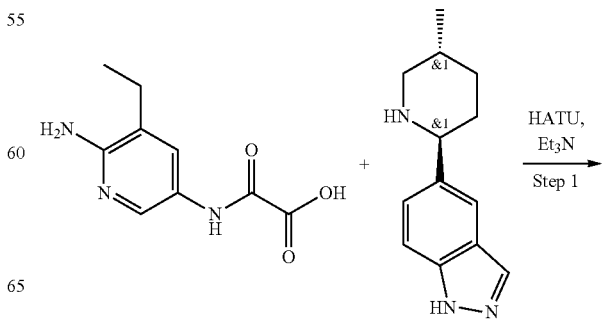

-continued

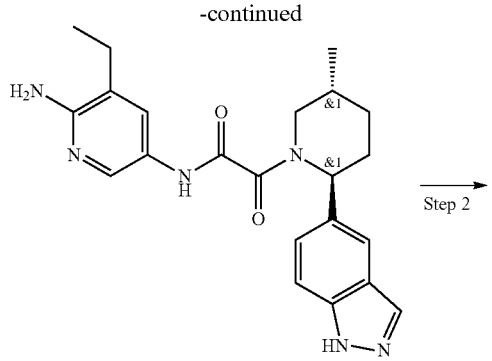

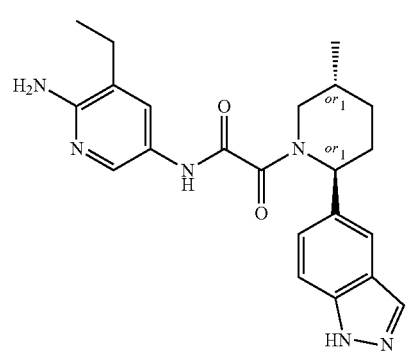

Compound 579

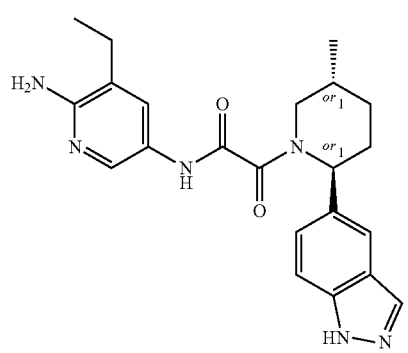

Compound 589

Step 1: Synthesis of N-(6-amino-5-ethyl-3-pyridyl)-2-[(2R,5S)-2-(1H-indazol-5-yl)-5-methyl-1-piperidyl]-2-oxo-acetamide To a solution of 2-[(6-amino-5-ethyl-3-pyridyl)amino]-2-oxo-acetic acid (0.5 g, 2.39 mmol), 5-[(2R,5S)-5-methyl-2-piperidyl]-1H-indazole (321.60 mg, 1.49 mmol) and triethylamine (906.93 mg, 8.96 mmol, 1.25 mL) in DMF (5.0 mL), HATU (681.57 mg, 1.79 mmol) was added portionwise. The resulting mixture was stirred at 50° C. for 3 hr and subjected to HPLC (40-40-80% 0-1-5 min 0.1% NH$_3$-methanol, flow: 30 ml/min (loading pump 4 ml/min methanol) target mass 406 column: YMC Triart C18 100*20 mm, 5 um) to give N-(6-amino-5-ethyl-3-pyridyl)-2-[(2R,5S)-2-(1H-indazol-5-yl)-5-methyl-1-piperidyl]-2-oxo-acetamide (0.2 g, 492.03 μmol, 32.94% yield). This compound was used for chiral resolution without HNMR.

Step 2: Chiral Separation of N-(6-amino-5-ethyl-3-pyridyl)-2-[(2R,5S)-2-(1H-indazol-5-yl)-5-methyl-1-piperidyl]-2-oxo-acetamide N-(6-amino-5-ethyl-3-pyridyl)-2-[(2R,5S)-2-(1H-indazol-5-yl)-5-methyl-1-piperidyl]-2-oxo-acetamide (0.2 g, 492.03 μmol) was chirally separated (Sample Info: IC—I (250*20, 5 mkm), Hexane-IPA-MeOH, 50-25-25, Flow 12 ml/min) to obtain Compound 579—rel-2-((2R,5S)-2-(1H-indazol-5-yl)-5-methylpiperidin-1-yl)-N-(6-amino-5-ethylpyridin-3-yl)-2-oxoacetamide (92 mg, 226.33 μmol, 92.00% yield) and Compound 589—rel-2-((2R,5S)-2-(1H-indazol-5-yl)-5-methylpiperidin-1-yl)-N-(6-amino-5-ethylpyridin-3-yl)-2-oxoacetamide (88 mg, 216.49 μmol, 88.00% yield).

Compound 579: RT (IB, Hexane-IPA-MeOH, 50-25-25, 0.6 ml/min)=9.16 min.

$^1$H NMR (600 MHz, DMSO-d$_6$) δ 1.00-1.04 (m, 4H), 1.05-1.14 (m, 3H), 1.29-1.38 (m, 1H), 1.71-1.80 (m, 1H), 1.80-1.89 (m, 1H), 2.03-2.16 (m, 1H), 2.22-2.30 (m, 1H), 2.38-2.41 (m, 1H), 2.72-3.24 (m, 1H), 3.43-4.03 (m, 1H), 5.20-5.60 (m, 1H), 5.61-5.71 (m, 2H), 7.25-7.38 (m, 1H), 7.41-7.50 (m, 1H), 7.51-7.56 (m, 1H), 7.66-7.73 (m, 1H), 7.95-8.03 (m, 1H), 8.03-8.09 (m, 1H), 10.43-10.58 (m, 1H), 13.01 (s, 1H).

LCMS(ESI): [M+H]$^+$ m/z: calcd 406.2; found 407.2; Rt=3.684 min.

Compound 589: RT (IB, Hexane-IPA-MeOH, 50-25-25, 0.6 ml/min)=12.20 min.

$^1$H NMR (600 MHz, DMSO-d$_6$) δ 0.97-1.14 (m, 6H), 1.28-1.42 (m, 1H), 1.68-1.80 (m, 1H), 1.80-1.92 (m, 1H), 2.00-2.21 (m, 1H), 2.23-2.30 (m, 1H), 2.31-2.35 (m, 1H), 2.37-2.41 (m, 1H), 2.71-3.26 (m, 1H), 3.40-4.04 (m, 1H), 5.18-5.60 (m, 1H), 5.61-5.74 (m, 2H), 7.23-7.38 (m, 1H), 7.38-7.57 (m, 2H), 7.65-7.73 (m, 1H), 7.95-8.09 (m, 2H), 10.44-10.57 (m, 1H), 13.01 (s, 1H).

LCMS(ESI): [M+H]$^+$ m/z: calcd 406.2; found 407.2; Rt=1.957 min.

Example 132. Synthesis of 5-[[2-[(2S,5R)-2-(1,3-benzothiazol-5-yl)-5-methyl-1-piperidyl]-2-oxo-acetyl]amino]pyridine-3-carboxamide (Compound 495), 5-[[2-[(2S,5R)-2-(1,3-benzothiazol-5-yl)-5-methyl-1-piperidyl]-2-oxo-acetyl]amino]pyridine-3-carboxamide (Compound 587) and 5-[[2-[(2R,5S)-2-(1,3-benzothiazol-5-yl)-5-methyl-1-piperidyl]-2-oxo-acetyl]amino]pyridine-3-carboxamide (Compound 588

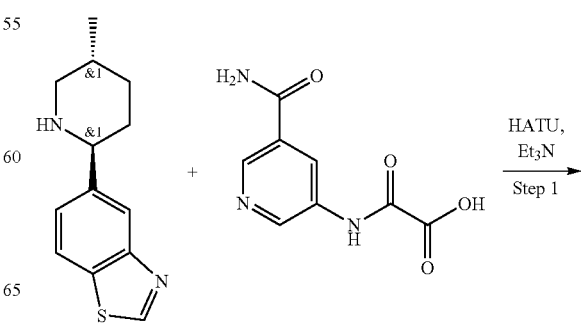

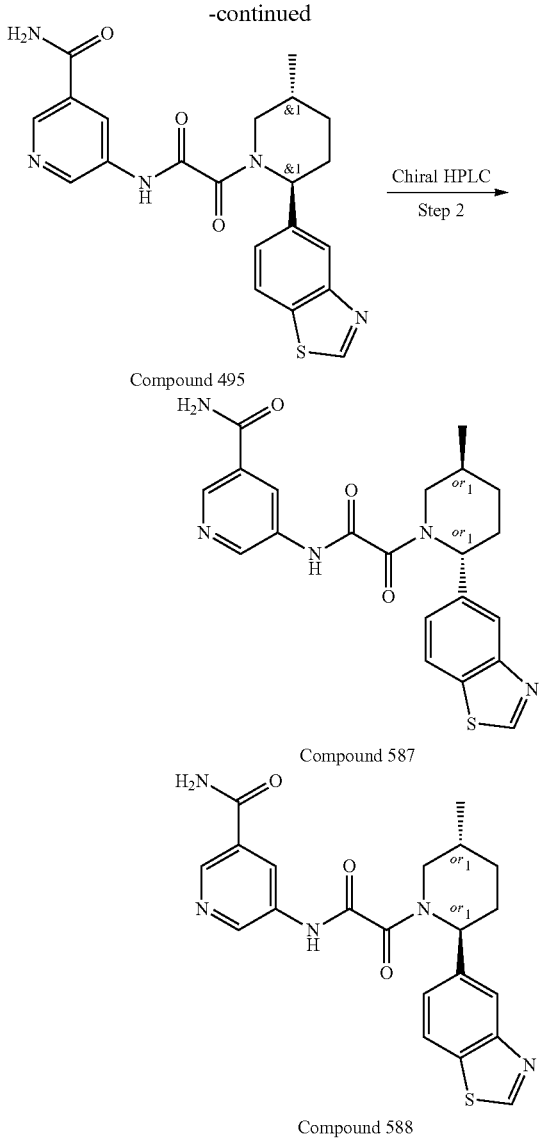

Compound 495

Compound 587

Compound 588

Step 1. Synthesis of 5-[[2-[(2S,5R)-2-(1,3-benzothiazol-5-yl)-5-methyl-1-piperidyl]-2-oxo-acetyl]amino]pyridine-3-carboxamide (Compound 495

HATU (654.60 mg, 1.72 mmol) was added portionwise at r.t. to a suspension of 2-[(5-carbamoyl-3-pyridyl)amino]-2-oxo-acetic acid (422.86 mg, 1.72 mmol, HCl), 5-(5-methyl-2-piperidyl)-1,3-benzothiazole (400 mg, 1.72 mmol) and TEA (1.05 g, 10.33 mmol, 1.44 mL) in DMF (10 mL). The clear solution was stirred at 25° C. for 32 hr and the solvents were evaporated in vacuo to give 1 g of crude material. It was subjected to RP-HPLC (column: YMC Triart C18 100×20 mm, 5 um; 30-60% 0-5 min 0.10% $NH_3$-methanol, flow: 30 ml/min as mobile phase) to give Compound 495 5-[[2-[(2S,5R)-2-(1,3-benzothiazol-5-yl)-5-methyl-1-piperidyl]-2-oxo-acetyl]amino]pyridine-3-carboxamide (290 mg, 684.79 μmol, 39.78% yield).

$^1$H NMR (600 MHz, DMSO-$d_6$) δ 0.98-1.09 (m, 3H), 1.31-1.44 (m, 1H), 1.67-1.77 (m, 1H), 1.81-1.97 (m, 1H), 2.07-2.24 (m, 1H), 2.29-2.36 (m, 1H), 2.81-3.29 (m, 1H), 3.46-4.12 (m, 1H), 5.28-5.79 (m, 1H), 7.42-7.52 (m, 1H), 7.52-7.65 (m, 1H), 8.01-8.06 (m, 1H), 8.09-8.24 (m, 2H), 8.35-8.54 (m, 1H), 8.69-8.79 (m, 1H), 8.81-8.93 (m, 1H), 9.35-9.43 (m, 1H), 11.05-11.46 (m, 1H).

LCMS(ESI): [M+1]$^+$ m/z: calcd 423.2; found 242.0; Rt=2.322 min.

Step 2. Synthesis of 5-[[2-[(2S,5R)-2-(1,3-benzothiazol-5-yl)-5-methyl-1-piperidyl]-2-oxo-acetyl]amino]pyridine-3-carboxamide (Compound 587) and 5-[[2-[(2R,5S)-2-(1,3-benzothiazol-5-yl)-5-methyl-1-piperidyl]-2-oxo-acetyl]amino]pyridine-3-carboxamide (Compound 588

5-[[2-[(2S,5R)-2-(1,3-benzothiazol-5-yl)-5-methyl-1-piperidyl]-2-oxo-acetyl]amino]pyridine-3-carboxamide (125.6 mg, 296.59 μmol) was chirally separated using Chiralpak IA-I(250*20 mm, 5 mkm) column; Hexane-IPA-MeOH 40-30-30 as a mobile phase; Flow Rate: 12 mL/min; 2 pins, 60 mg/1 pin affording Compound 587—5-[[2-[(2S,5R)-2-(1,3-benzothiazol-5-yl)-5-methyl-1-piperidyl]-2-oxo-acetyl]amino]pyridine-3-carboxamide (52.93 mg, 124.99 μmol, 42.14% yield) (RT (IA, Hexane-IPA-MeOH, 40-30-30, 0.6 ml/min)=44.85 min) as a yellow solid and Compound 588—5-[[2-[(2R,5S)-2-(1,3-benzothiazol-5-yl)-5-methyl-1-piperidyl]-2-oxo-acetyl]amino]pyridine-3-carboxamide (50.51 mg, 119.27 μmol, 40.21% yield) (RT (IA, Hexane-IPA-MeOH, 40-30-30, 0.6 ml/min=72.39 min) as a beige solid.

Compound 587: 1H NMR (600 MHz, DMSO-$d_6$) δ 1.00-1.09 (m, 3H), 1.32-1.45 (m, 1H), 1.68-1.76 (m, 1H), 1.83-1.98 (m, 1H), 2.05-2.32 (m, 1H), 2.32-2.37 (m, 1H), 2.80-3.27 (m, 1H), 3.48-4.08 (m, 1H), 5.30-5.76 (m, 1H), 7.42-7.53 (m, 1H), 7.53-7.66 (m, 1H), 8.00-8.05 (m, 1H), 8.08-8.23 (m, 2H), 8.39-8.52 (m, 1H), 8.69-8.79 (m, 1H), 8.80-8.93 (m, 1H), 9.36-9.41 (m, 1H), 11.15-11.40 (m, 1H).

LCMS(ESI): [M+1]$^+$ m/z: calcd 423.2; found 242.2; Rt=2.381 min.

Compound 588: 1H NMR (600 MHz, DMSO-$d_6$) δ 1.00-1.09 (m, 3H), 1.32-1.45 (m, 1H), 1.68-1.76 (m, 1H), 1.83-1.98 (m, 1H), 2.05-2.32 (m, 1H), 2.32-2.37 (m, 1H), 2.80-3.27 (m, 1H), 3.48-4.08 (m, 1H), 5.30-5.76 (m, 1H), 7.42-7.53 (m, 1H), 7.53-7.66 (m, 1H), 8.00-8.05 (m, 1H), 8.08-8.23 (m, 2H), 8.39-8.52 (m, 1H), 8.69-8.79 (m, 1H), 8.80-8.93 (m, 1H), 9.36-9.41 (m, 1H), 11.15-11.40 (m, 1H).

LCMS(ESI): [M+1]$^+$ m/z: calcd 423.2; found 242.2; Rt=2.380 min.

Example 133. The Synthesis of Rel-5-[[2-[(2S,5R)-2-(1,3-benzothiazol-5-yl)-5-methyl-1-piperidyl]-2-oxo-acetyl]amino]-2-methoxy-pyridine-3-carboxamide (Compound 603) and Rel-5-[[2-[(2R,5S)-2-(1,3-benzothiazol-5-yl)-5-methyl-1-piperidyl]-2-oxo-acetyl]amino]-2-methoxy-pyridine-3-carboxamide (Compound 602

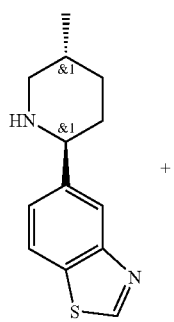

+

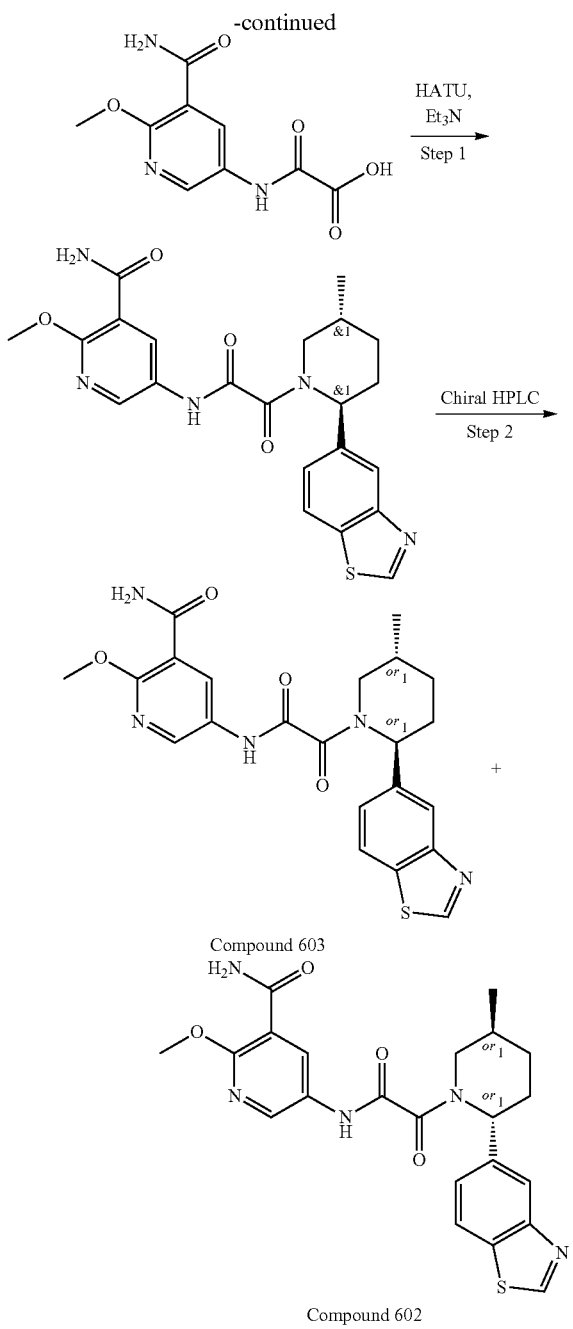

Compound 603

Compound 602

Step 1: Synthesis of 5-[[2-[2-(1,3-benzothiazol-5-yl)-5-methyl-1-piperidyl]-2-oxo-acetyl]amino]-2-methoxy-pyridine-3-carboxamide HATU (490.95 mg, 1.29 mmol) was added portionwise at r.t. to suspension of 2-[(5-carbamoyl-6-methoxy-3-pyridyl)amino]-2-oxo-acetic acid (439.49 mg, 1.29 mmol, C6H15N), 5-(5-methyl-2-piperidyl)-1,3-benzothiazole (300 mg, 1.29 mmol) and TEA (783.93 mg, 7.75 mmol, 1.08 mL) in DMF (10 mL). The clear solution was stirred at 20° C. for 18 hr and the solvents were evaporated in vacuo to give 1 g of crude material. It was subjected to RP-HPLC (column: YMC-Actus Triart C18 100*20 mml.D. S-5 um; 0-5 min 20-70% water-methanol (NH3 0.1%), flow: 30 ml/min as mobile phase) to give 5-[[2-[2-(1,3-benzothiazol-5-yl)-5-methyl-1-piperidyl]-2-oxo-acetyl]amino]-2-methoxy-pyridine-3-carboxamide (214 mg, 471.87 µmol, 36.55% yield).

LCMS(ESI): [M+H]+ m/z: calcd 453.2; found 454.2; Rt=2.724 min.

Step 2: Synthesis of Rel-5-[[2-[(2S,5R)-2-(1,3-benzothiazol-5-yl)-5-methyl-1-piperidyl]-2-oxo-acetyl]amino]-2-methoxy-pyridine-3-carboxamide (Compound 603) and Rel-5-[[2-[(2R,5S)-2-(1,3-benzothiazol-5-yl)-5-methyl-1-piperidyl]-2-oxo-acetyl]amino]-2-methoxy-pyridine-3-carboxamide (Compound 602

The enantiomers were separated by chiral HPLC (column: IC—I (250*20, 5 mkm), Hexane-IPA-MeOH, 50-25-25, 12 ml/min as mobile phase) to give the two individual enantiomers Compound 603 5-[[2-[(2S,5R)-2-(1,3-benzothiazol-5-yl)-5-methyl-1-piperidyl]-2-oxo-acetyl]amino]-2-methoxy-pyridine-3-carboxamide (44 mg, 97.02 µmol, 41.12% yield) RetTime=69.1 min and Compound 602 5-[[2-[(2R,5S)-2-(1,3-benzothiazol-5-yl)-5-methyl-1-piperidyl]-2-oxo-acetyl]amino]-2-methoxy-pyridine-3-carboxamide (62 mg, 136.71 µmol, 57.94% yield) RetTime=96.6 min.

Compound 603: RT (IC, Hexane-IPA-MeOH, 50-25-25, 0.6 ml/min)=49.073 min.

$^1$H NMR (600 MHz, DMSO-$d_6$) δ 1.01-1.05 (m, 3H), 1.32-1.42 (m, 1H), 1.68-1.76 (m, 1H), 1.83-1.94 (m, 1H), 2.07-2.22 (m, 1H), 2.28-2.35 (m, 1H), 2.80-3.26 (m, 1H), 3.51-4.10 (m, 4H), 5.28-5.77 (m, 1H), 7.39-7.53 (m, 1H), 7.66-7.80 (m, 2H), 7.97-8.07 (m, 1H), 8.12-8.20 (m, 1H), 8.39-8.59 (m, 2H), 9.36-9.41 (m, 1H), 11.01-11.17 (m, 1H).

LCMS(ESI): [M+H]+ m/z: calcd 453.1; found 454.2; Rt=4.695 min.

Compound 602: RT (IC, Hexane-IPA-MeOH, 50-25-25, 0.6 ml/min)=67.435 min.

$^1$H NMR (600 MHz, DMSO-$d_6$) δ 1.01-1.06 (m, 3H), 1.32-1.40 (m, 1H), 1.69-1.75 (m, 1H), 1.83-1.93 (m, 1H), 2.08-2.23 (m, 1H), 2.29-2.35 (m, 1H), 2.77-3.28 (m, 1H), 3.50-4.09 (m, 4H), 5.26-5.75 (m, 1H), 7.41-7.51 (m, 1H), 7.65-7.78 (m, 2H), 8.00-8.04 (m, 1H), 8.14-8.20 (m, 1H), 8.38-8.57 (m, 2H), 9.35-9.44 (m, 1H), 10.98-11.21 (m, 1H).

LCMS(ESI): [M+H]+ m/z: calcd 453.1; found 454.0; Rt=4.695 min.

Example 134. The Synthesis of 2-methoxy-5-[[2-[5-methyl-2-(6-oxo-5H-1,5-naphthyridin-2-yl)-1-piperidyl]-2-oxo-acetyl]amino]pyridine-3-carboxamide (Compound 1077

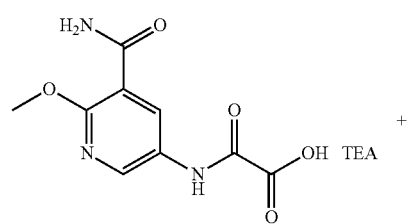

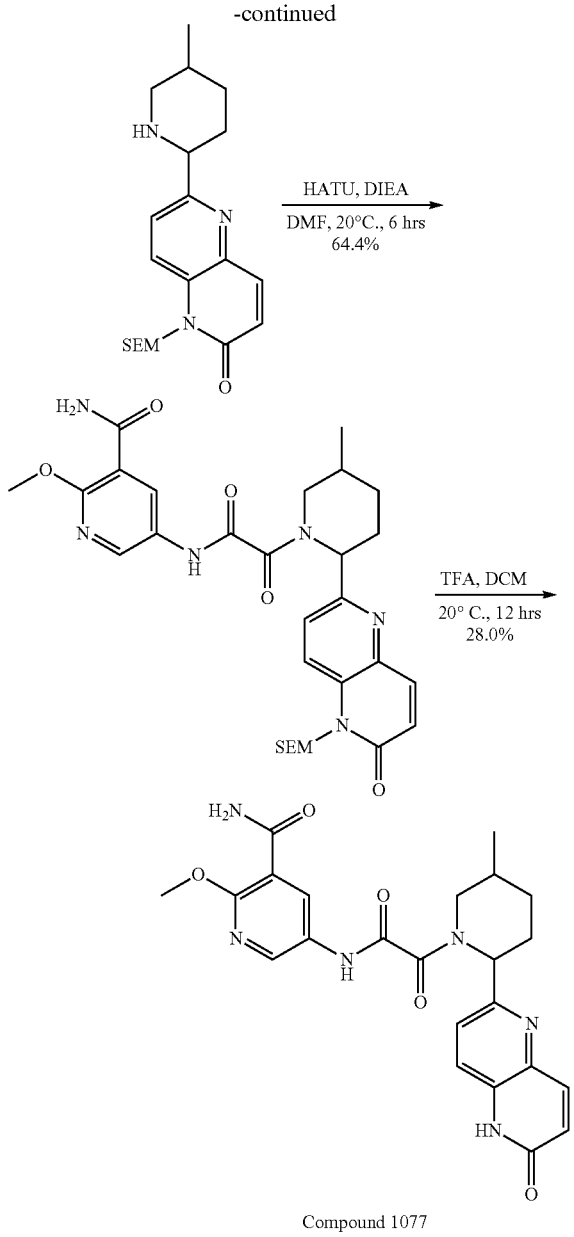

Compound 1077

Step 1: Synthesis of 2-methoxy-5-[[2-[5-methyl-2-[6-oxo-5-(2-trimethylsilylethoxymethyl)-1,5-naphthyridin-2-yl]-1-piperidyl]-2-oxo-acetyl]amino]pyridine-3-carboxamide To a solution of 2-[(5-carbamoyl-6-methoxy-3-pyridyl)amino]-2-oxo-acetic acid (100 mg, 0.418 mmol, TEA), 6-(5-methyl-2-piperidyl)-1-(2-trimethylsilylethoxymethyl)-1,5-naphthyridin-2-one (300 mg, 0.803 mmol), HATU (250 mg, 0.658 mmol) in DMF (8 mL) was added DIEA (300 µL, 1.72 mmol). The mixture was stirred at 20° C. for 6 hours. The resulting mixture was concentrated under reduced pressure. The residue was purified by flash chromatography (ISCO®; 12 g AgelaFlash® Silica Flash Column, petroleum ether/EtOAc with EtOAc from 0~100%, then EtOAc/MeOH with MeOH from 0~5%, flow rate=30 mL/min, 254 nm) to afford 2-methoxy-5-[[2-[5-methyl-2-[6-oxo-5-(2-trimethylsilylethoxymethyl)-1,5-naphthyridin-2-yl]-1-piperidyl]-2-oxo-acetyl]amino]pyridine-3-carboxamide (160 mg, 64.4% yield) as yellow oil.

Step 2: Synthesis of 2-methoxy-5-[[2-[5-methyl-2-(6-oxo-5H-1,5-naphthyridin-2-yl)-1-piperidyl]-2-oxo-acetyl]amino]pyridine-3-carboxamide (Compound 1077

To a solution of 2-methoxy-5-[[2-[5-methyl-2-[6-oxo-5-(2-trimethylsilylethoxymethyl)-1,5-naphthyridin-2-yl]-1-piperidyl]-2-oxo-acetyl]amino]pyridine-3-carboxamide (160 mg, 0.269 mmol) in DCM (2 mL) was added TFA (800 µL, 0.010 mol). The mixture was stirred at 20° C. for 12 hours. The resulting mixture was concentrated under reduced pressure. The residue was purified by preparative HPLC (Instrument: Gilson GX-281 Liquid Handler, Gilson 322 Pump, Gilson 156 UV Detector; Column: Welch Xtimate C18 150×25 mm×5 m; Mobile phase A: $H_2O$ with 0.225% FA (v %); Mobile phase B: MeCN; Gradient: B from 16% to 46% in 9.5 min, hold 100% B for 2 min; Flow Rate: 25 mL/min; Column Temperature: 30° C.; Wavelength: 220 nm, 254 nm) to afford 2-methoxy-5-[[2-[5-methyl-2-(6-oxo-5H-1,5-naphthyridin-2-yl)-1-piperidyl]-2-oxo-acetyl]amino]pyridine-3-carboxamide (35 mg, 28.0%) as white solid. $^1$H NMR (400 MHz, DMSO-$d_6$) δ ppm 11.58 (br s, 1H), 10.72 (br s, 1H), 8.42-8.69 (m, 2H), 7.90 (d, J 9.8 Hz, 1H), 7.72 (br d, J 8.5 Hz, 1H), 7.50 (br s, 3H), 6.72 (d, J 9.8 Hz, 1H), 5.29-5.81 (m, 1H), 3.88-4.16 (m, 4H), 2.43 (br d, J=10.8 Hz, 1H), 1.73-2.23 (m, 4H), 1.37 (br d, J 9.8 Hz, 1H), 1.07 (br d, J 7.0 Hz, 3H); LCMS (ESI) [M+H]$^+$ m/z: calcd 465.2, found 465.1; HPLC: 98.73% @254 nm.

Example 135. The Synthesis of 5-[[2-oxo-2-[(1S,4S,5R)-4-(2-thienyl)-3-azabicyclo[3.2.1]octan-3-yl]acetyl]amino]pyridine-3-carboxamide (Compound 79

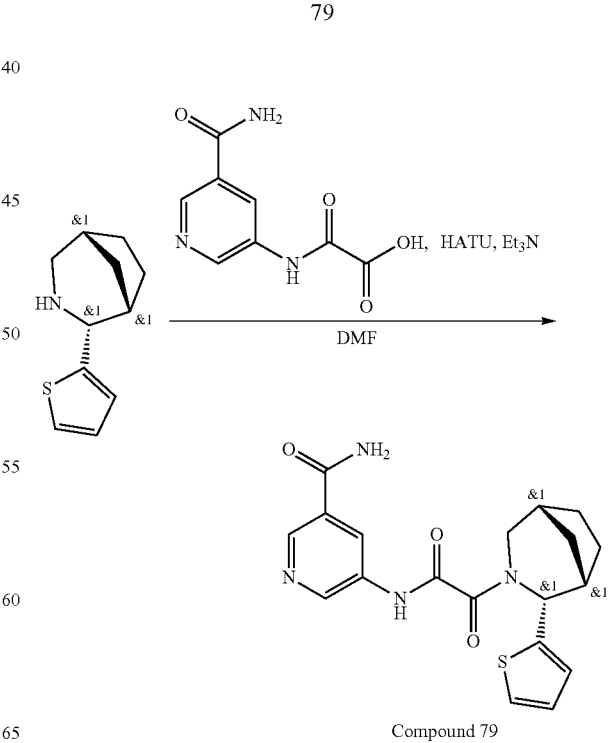

Compound 79

A suspension of (1S,4S,5R)-4-(2-thienyl)-3-azabicyclo[3.2.1]octane (300.00 mg, 1.55 mmol), 2-[(5-carbamoyl-3-pyridyl)amino]-2-oxo-acetic acid (Et₃N salt, 324.60 mg, 1.05 mmol), HATU (619.59 mg, 1.63 mmol) and Triethylamine (785.20 mg, 7.76 mmol, 1.08 mL) in DMF (3 mL) was stirred at 40° C. for 12 hours. After 12 hours, the reaction mixture was concentrated in vacuo and the crude product was subjected to reverse phase HPLC purification (Eluent: 40-40-60%, 0-1-6 min 0.1% NH₃-methanol, flow rate: 30 mL/min; loading pump: 4 mL/min, methanol; column: YMC Actus Triart C18 100×20 mm, 5 um) to obtain product 5-[[2-oxo-2-[(1S,4S,5R)-4-(2-thienyl)-3-azabicyclo[3.2.1]octan-3-yl]acetyl]amino]pyridine-3-carboxamide (Compound 79, 56 mg, 145.66 μmol, 9.39% yield) as a white solid.

Note: The title compound was obtained as a single diastereomer. The structure was proved as trans- by 2D NMR.

LCMS(ESI): [M+H]⁺ m/z: calcd 384.1; found 385.0; Rt=1.121 min.

Example 136. The Synthesis of 5-[[2-[2-(4,4-difluorocyclohexyl)-1-piperidyl]-2-oxo-acetyl]amino]pyridine-3-carboxamide (Compound 170

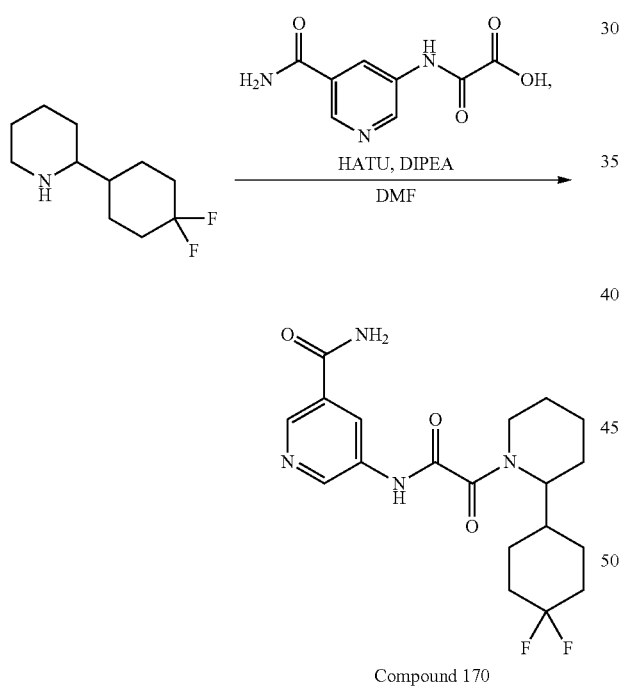

Compound 170

A mixture of 2-(4,4-difluorocyclohexyl)piperidine (0.2 g, 983.91 μmol), 2-[(5-carbamoyl-3-pyridyl)amino]-2-oxo-acetic acid (305.35 mg, 983.91 μmol, Et₃N salt) and triethylamine (995.62 mg, 9.84 mmol, 1.37 mL) in DMF (3 mL) was stirred at 25° C. for 20 minutes. After 20 minutes, HATU (561.17 mg, 1.48 mmol) was added. The resulting reaction mixture was stirred at 25° C. for overnight. Upon completion, water (20 mL) was added to the reaction mixture and extracted with Ethyl acetate (2×25 mL). The combined organic phase was washed with water (3×20 mL), brine, dried over Na₂SO₄, filtered and dried under reduced pressure. The crude product was subjected to reverse phase HPLC purification (Eluent: 20-60%, 1.3-11 min, 0.1% NH₃-methanol; flow rate: 30 mL/min; column: XBridge C18 100×20 mm, 5 um) to obtain 5-[[2-[2-(4,4-difluorocyclohexyl)-1-piperidyl]-2-oxo-acetyl]amino]pyridine-3-carboxamide (Compound 170, 50.3 mg, 127.53 μmol, 12.96% yield) as a light-yellow solid.

Compound 170: ¹H NMR (CDCl₃ 400 MHz): δ (ppm) 1.34 (m, 3H), 1.83 (m, 14H), 2.95 (m, 1H), 4.55 (m, 2H), 7.24 (s, 1H), 8.56 (m, 1H), 8.78 (m, 1H), 8.97 (m, 1H).

LCMS(ESI): [M+H]⁺ m/z: calcd 394.2; found 395.2; Rt=2.927 min.

Example 137. The Synthesis of 5-[[2-[(2S,5R)-2-Isopropyl-5-methyl-1-piperidyl]-2-oxo-acetyl]amino]pyridine-3-carboxamide (Compound 176

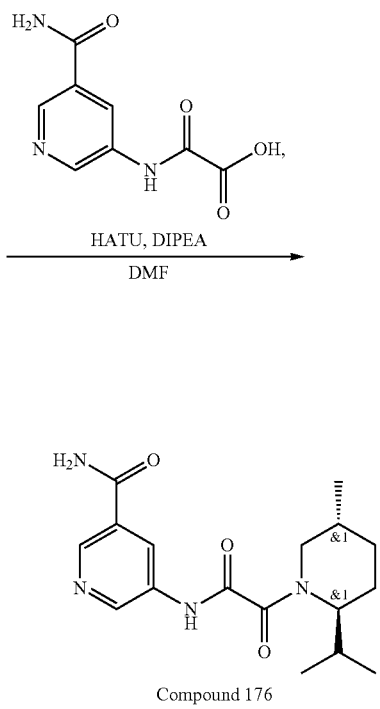

Compound 176

To a stirred solution of 2-[(5-carbamoyl-3-pyridyl)amino]-2-oxo-acetic acid (0.23 g, 1.10 mmol) and 2-isopropyl-5-methyl-piperidine (195.42 mg, 1.10 mmol, HCl) in DMF (10 mL) was added DIPEA (497.42 mg, 3.85 mmol, 670.38 μL). The resulting mixture was stirred for 5 minutes. After 5 minutes, a solution of HATU (439.02 mg, 1.15 mmol) in DMF (2 mL) was added. The resulting reaction mixture was stirred for overnight at room temperature. Upon completion, the resulting suspension was concentrated under reduced pressure and the crude product was purified by HPLC and freeze dried to afford 5-[[2-[(2S,5R)-2-isopropyl-5-methyl-1-piperidyl]-2-oxo-acetyl]amino]pyridine-3-carboxamide (Compound 176, 50.9 mg, 153.13 μmol, 13.93% yield) as a white solid.

¹H NMR (DMSO-d₆, 500 MHz): δ (ppm) 0.89 (m, 9H), 1.30 (m, 1H), 1.64 (m, 1H), 1.89 (m, 3H), 2.21 (m, 1H), 2.90

(m, 1H), 3.42 (m, 1H), 4.04 (m, 1H), 7.61 (s, 1H), 8.17 (s, 1H), 8.49 (m, 1H), 8.77 (s, 1H), 8.89 (m, 1H), 11.08 (m, 1H).

LCMS(ESI): [M+H]⁺ m/z: calcd 332.2; found 333.4; Rt=2.739 min.

Example 138. The Synthesis of 5-[[2-(2-Isopropyl-1-piperidyl)-2-oxo-acetyl]amino]pyridine-3-carboxamide (Compound 100

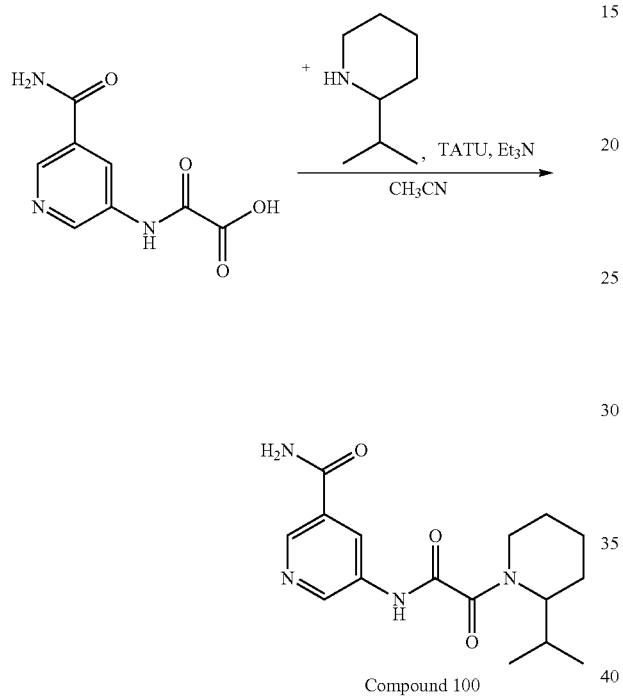

Compound 100

2-[(5-carbamoyl-3-pyridyl)amino]-2-oxo-acetic acid (0.3 g, 966.66 µmol, Et₃N salt), TATU (342.46 mg, 1.06 mmol) and triethylamine (195.63 mg, 1.93 mmol, 269.47 µL) were mixed together in dry CH₃CN (25 mL) at 21° C. and the resulting mixture was stirred for 15 minutes. After 15 minutes, 2-isopropylpiperidine (135.28 mg, 826.47 µmol, HCl salt) was added and the resulting mixture was stirred at 21° C. for overnight. The resulting mixture was evaporated to dryness and subjected to HPLC purification (Eluent: 2-7 min, 15-30% CH₃CN, flow rate: 30 mL/min; column: SunFire C18 100*19 mm, 5 um) to get 5-[[2-(2-isopropyl-1-piperidyl)-2-oxo-acetyl]amino]pyridine-3-carboxamide (Compound 100, 52.9 mg, 166.16 µmol, 17.19% yield) as an off-white solid.

1H NMR (DMSO-d₆, 400 MHz): δ (ppm) 0.89 (m, 6H), 1.58 (m, 5H), 1.85 (m, 1H), 2.20 (m, 1H), 2.99 (m, 1H), 3.49 (m, 1H), 4.14 (m, 1H), 7.63 (s, 1H), 8.18 (s, 1H), 8.50 (s, 1H), 8.78 (s, 1H), 8.89 (d, 1H), 11.10 (m, 1H).

LCMS(ESI): [M+Boc]⁺ m/z: calcd 318.2; found 319.2; Rt=0.983 min.

Example 139. The Synthesis of 5-[[2-[(2R,53)-2-cyclobutyl-5-methyl-1-piperidyl]-2-oxo-acetyl] amino]pyridine-3-carboxamide (Compound 155), 5-[[2-[(2S,5R)-2-cyclobutyl-5-methyl-1-piperidyl]-2-oxo-acetyl]amino]pyridine-3-carboxamide and 5-[[2-[(2R,5S)-2-cyclobutyl-5-methyl-1-piperidyl]-2-oxo-acetyl]amino]pyridine-3-carboxamide (Compound 216 and Compound 211

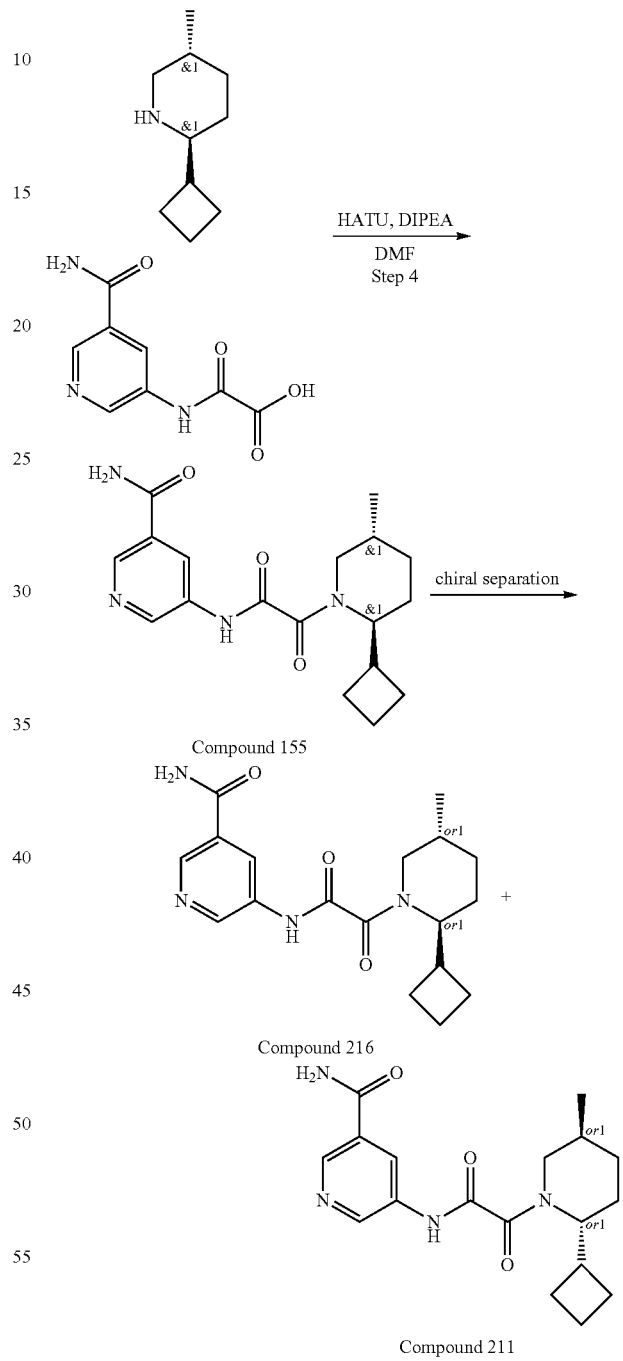

Compound 155

Compound 216

Compound 211

Step 1: Synthesis of 5-[[2-[(2R,5S)-2-cyclobutyl-5-methyl-1-piperidyl]-2-oxo-acetyl]amino]pyridine-3-carboxamide (Compound 155

To a stirred solution of 2-[(5-carbamoyl-3-pyridyl) amino]-2-oxo-acetic acid (0.23 g, 1.10 mmol) and 2-cyclobutyl-5-methyl-piperidine (168.54 mg, 1.10 mmol) in DMF (10 mL) was added DIPEA (355.30 mg, 2.75 mmol, 478.84 µL). The resulting mixture was stirred for 5 minutes. After 5 minutes, a solution of HATU (439.02 mg, 1.15 mmol) in DMF (2 mL) was added. The resulting reaction mixture was stirred for overnight at room temperature. Upon completion, the resulting suspension was concentrated under reduced pressure and the crude product was purified by HPLC and freeze dried to afford rac-5-[[2-[(2R,5S)-2-cyclobutyl-5-methyl-1-piperidyl]-2-oxo-acetyl]amino]pyridine-3-carboxamide (Compound 155, 20.4 mg, 59.23 µmol, 5.39% yield) as a white solid.

$^1$H NMR (DMSO-$d_6$, 500 MHz): δ (ppm) 0.95 (dd, 3H), 1.32 (m, 2H), 1.80 (m, 9H), 2.93 (m, 2H), 3.81 (m, 1H), 4.24 (m, 1H), 7.62 (m, 1H), 8.18 (m, 1H), 8.50 (m, 1H), 8.78 (m, 1H), 8.90 (m, 1H), 11.09 (m, 1H).

LCMS(ESI): [M+H]$^+$ m/z: calcd 344.2; found 345.4; Rt=2.876 min.

Step 2: Chiral Separation of 5-[[2-[(2S,5R)-2-cyclobutyl-5-methyl-1-piperidyl]-2-oxo-acetyl]amino]pyridine-3-carboxamide and 5-[[2-[(2R,5S)-2-cyclobutyl-5-methyl-1-piperidyl]-2-oxo-acetyl]amino]pyridine-3-carboxamide (Compound 216 and Compound 211 rac-5-[[2-[(2R,5S)-2-cyclobutyl-5-methyl-1-piperidyl]-2-oxo-acetyl]amino]pyridine-3-carboxamide (Compound 155) was subjected to chiral chromatography (Column: IA-II 250*20 mm, 5 um, Eluent: Hexane-IPA-MeOH, 70-15-15, flow rate: 12 mL/min) to give 5-[[2-[(2R,5S)-2-cyclobutyl-5-methyl-1-piperidyl]-2-oxo-acetyl]amino]pyridine-3-carboxamide (Compound 211) and 5-[[2-[(2S,5R)-2-cyclobutyl-5-methyl-1-piperidyl]-2-oxo-acetyl]amino]pyridine-3-carboxamide (Compound 216) as white solid.

Compound 216: LCMS(ESI): [M+H]$^+$ m/z: calcd 344.2; found 345.2; Rt=4.427 min.

Chiral HPLC: Rt=31.56 min (Column: IA; Eluent: Hexane-MeOH-IPA, 70-15-15; Flow Rate: 0.6 mL/min).

1H NMR (Chloroform-d, 400 MHz): δ (ppm) 0.99 (m, 3H), 1.38 (m, 2H), 1.83 (m, 10H), 3.04 (m, 2H), 4.29 (m, 1H), 4.75 (m, 1H), 6.35 (s, 1H), 6.70 (s, 1H), 8.70 (m, 1H), 8.91 (m, 1H), 9.10 (m, 1H), 10.05 (m, 1H)

Compound 211: LCMS(ESI): [M+H]$^+$ m/z: calcd 344.2; found 345.2; Rt=4.425 min.

Chiral HPLC: Rt=22.02 min (Column: IA; Eluent: Hexane-MeOH-IPA, 70-15-15; Flow Rate: 0.6 mL/min).

1H NMR (Chloroform-d, 400 MHz): δ (ppm) 0.99 (m, 3H), 1.38 (m, 2H), 1.83 (m, 10H), 3.04 (m, 2H), 4.29 (m, 1H), 4.75 (m, 1H), 6.35 (s, 1H), 6.70 (s, 1H), 8.70 (m, 1H), 8.91 (m, 1H), 9.10 (m, 1H), 10.05 (m, 1H)

Example 140. The Synthesis of 5-[[2-(2-cyclobutyl-1-piperidyl)-2-oxo-acetyl]amino]pyridine-3-carboxamide (Compound 103

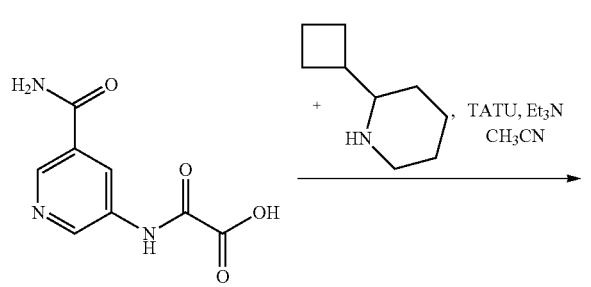

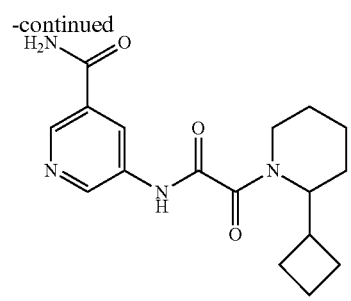

Compound 103

2-[(5-carbamoyl-3-pyridyl)amino]-2-oxo-acetic acid (0.3 g, 966.66 µmol, Et$_3$N salt), TATU (311.33 mg, 966.66 µmol) and triethylamine (97.82 mg, 966.66 µmol, 134.73 µL) were mixed in dry CH$_3$CN (25 mL) at 21° C. and the resulting mixture was stirred for 15 minutes. After 15 minutes, 2-cyclobutylpiperidine (148.05 mg, 1.06 mmol) was added and the resulting mixture was stirred at 21° C. for overnight. The resulting mixture was evaporated to dryness and subjected to HPLC purification (Eluent: 2-7 min, 15-30% CH$_3$CN; flow rate: 30 mL/min; column: SunFire C18 100*19 mm, 5 µM) to get 5-[[2-(2-cyclobutyl-1-piperidyl)-2-oxo-acetyl]amino]pyridine-3-carboxamide (Compound 103, 91.3 mg, 276.35 µmol, 28.59% yield) as an off-white solid.

1H NMR (CDCl$_3$, 400 MHz): δ (ppm) 1.92 (m, 13H), 3.00 (m, 2H), 4.89 (m, 1H), 6.27 (m, 2H), 8.73 (d, 1H), 8.98 (m, 2H), 9.72 (s, 1H).

LCMS(ESI): [M+H]$^+$ m/z: calcd 330.2; found 331.2; Rt=2.637 min.

Example 141. The Synthesis of 5-[[2-[(2S,5R)-2-(4,4-difluorocyclohexyl)-5-methyl-1-piperidyl]-2-oxo-acetyl]amino]pyridine-3-carboxamide and 5-[[2-[(2R,5S)-2-(4,4-difluorocyclohexyl)-5-methyl-1-piperidyl]-2-oxo-acetyl]amino]pyridine-3-carboxamide (Compound 486 and Compound 320

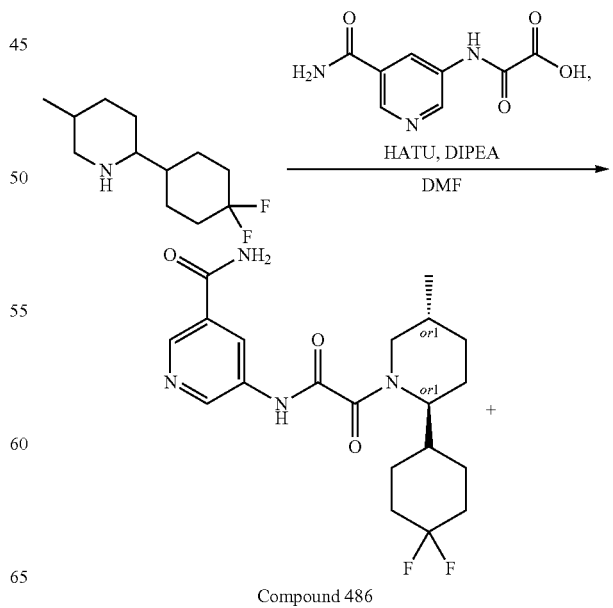

Compound 486

Example 142. The Synthesis of 5-(2-(2-cyclopentyl-5-methylpiperidin-1-yl)-2-oxoacetamido)Nicotinamide (Compound 172

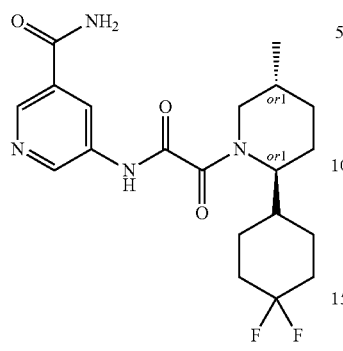

Compound 320

A mixture of 2-(4,4-difluorocyclohexyl)-5-methyl-piperidine (370 mg, 1.70 mmol), 2-[(5-carbamoyl-3-pyridyl)amino]-2-oxo-acetic acid (418.22 mg, 1.70 mmol, HCl salt) and triethyl amine (1.72 g, 17.03 mmol, 2.37 mL) in DMF (5 mL) was stirred at 25° C. for 20 minutes. After 20 minutes, HATU (712.17 mg, 1.87 mmol) was added in small portions over 30 minutes. The resulting reaction mixture was stirred at 25° C. for 12 hours. Upon completion, the crude reaction mixture was subjected to reverse phase HPLC purification (Eluent: 35-40%, 0-5 min, 0.1% $NH_3$-methanol; flow rate: 30 mL/min; column: YMC Triart C18 100×20 mm, 5 um) to afford 120 mg of racemic product (100% purity by LCMS), which was further purified by chiral HPLC (Eluent: Hexane-IPA-MeOH, 60-20-20; flow rate: 12 mL/min; column: AD-H—III (250×20 mm, 5 um) to afford 5-[[2-[(2S,5R)-2-(4,4-difluorocyclohexyl)-5-methyl-1-piperidyl]-2-oxo-acetyl]amino]pyridine-3-carboxamide (Compound 486, 62.1 mg, 152.04 μmol, 8.93% yield) and 5-[[2-[(2R,5S)-2-(4,4-difluorocyclohexyl)-5-methyl-1-piperidyl]-2-oxo-acetyl]amino]pyridine-3-carboxamide (Compound 320, 62 mg, 151.80 μmol, 8.91% yield) as white solids.

Compound 486:

$^1$H NMR (DMSO-$d_6$, 600 MHz): δ (ppm) 0.91-0.99 (m, 3H), 1.10-1.23 (m, 2H), 1.25-1.34 (m, 1H), 1.53-1.73 (m, 3H), 1.73-1.90 (m, 5H), 1.90-2.11 (m, 4H), 2.90-3.27 (m, 1H), 3.53-4.18 (m, 1H), 7.59 (s, 1H), 8.15 (s, 1H), 8.42-8.51 (m, 1H), 8.70-8.80 (m, 1H), 8.84-8.89 (m, 1H), 11.01-11.10 (m, 1H).

LCMS(ESI): [M+H]$^+$ m/z: calcd 408.2; found 409.2; Rt=3.077 min.

Chiral HPLC: Rt=10.737 min (Eluent: Hexane-IPA-MeOH, 50-25-25; flow rate: 0.6 mL/min; column: AD-H).

Compound 320:

$^1$H NMR (DMSO-$d_6$, 600 MHz): δ (ppm) 0.93-0.99 (m, 3H), 1.08-1.23 (m, 2H), 1.24-1.34 (m, 1H), 1.56-1.73 (m, 3H), 1.73-1.89 (m, 5H), 1.91-2.13 (m, 4H), 2.89-3.28 (m, 1H), 3.52-4.17 (m, 1H), 7.59 (s, 1H), 8.15 (s, 1H), 8.42-8.49 (m, 1H), 8.70-8.79 (m, 1H), 8.84-8.91 (m, 1H), 11.00-11.11 (m, 1H).

LCMS(ESI): [M+H]$^+$ m/z: calcd 408.2; found 409.2; Rt=3.090 min.

Chiral HPLC: Rt=28.151 min (Eluent: Hexane-IPA-MeOH, 50-25-25; flow rate: 0.6 mL/min; column: AD-H).

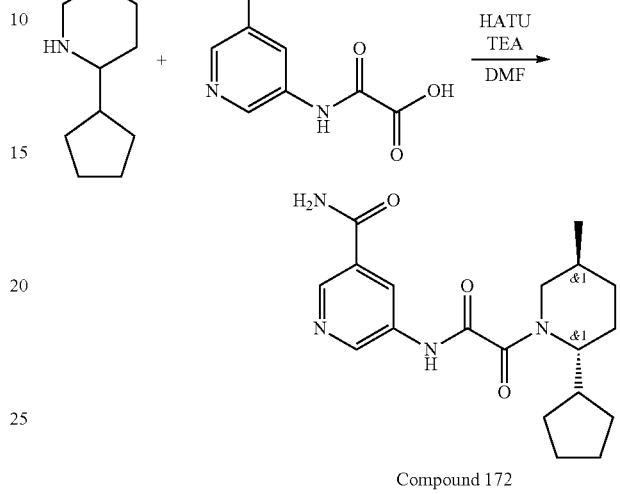

Compound 172

2-cyclopentyl-5-methyl-piperidine (200.00 mg, 1.20 mmol), 2-[(5-carbamoyl-3-pyridyl)amino]-2-oxo-acetic acid (371.03 mg, 1.20 mmol), triethylamine (1.21 g, 11.96 mmol, 1.67 mL) were mixed in DMF (5 mL) and then HATU (681.86 mg, 1.79 mmol) was added. Resulting mixture was stirred at 25° C. for 12 hr. The mixture was evaporated under reduce pressure and purified with HPLC (30-40% water-MeCN, 10 min, flow 30 ml/min) to obtain 5-[[2-[(2R,5S)-2-cyclopentyl-5-methyl-1-piperidyl]-2-oxo-acetyl]amino]pyridine-3-carboxamide (45.1 mg, 125.83 μmol, 10.52% yield), E/Z=1/9.

$^1$H NMR (400 MHz, DMSO-$d_6$) δ (ppm) 0.97 (m, 3H), 1.24 (m, 3H), 1.64 (m, 9H), 1.94 (m, 3H), 3.53 (m, 1H), 4.14 (m, 1H), 7.63 (s, 1H), 8.18 (s, 1H), 8.50 (m, 1H), 8.78 (s, 1H), 8.90 (s, 1H), 11.09 (s, 1H).

LCMS(ESI): [M]$^+$ m/z: calcd 358.4; found 359.2; Rt=1.249 min.

Example 143. The Synthesis of 5-(2-(2-cyclopentyl-5-methylpiperidin-1-yl)-2-oxoacetamido)-2-methoxynicotinamide (Compound 306, Compound 298, Compound 295, Compound 312

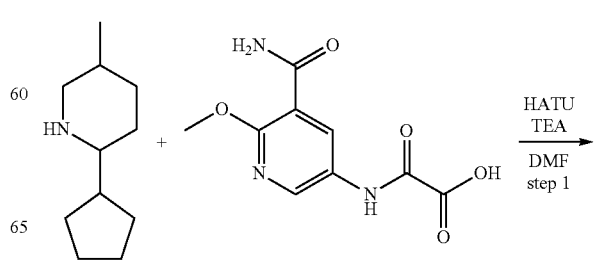

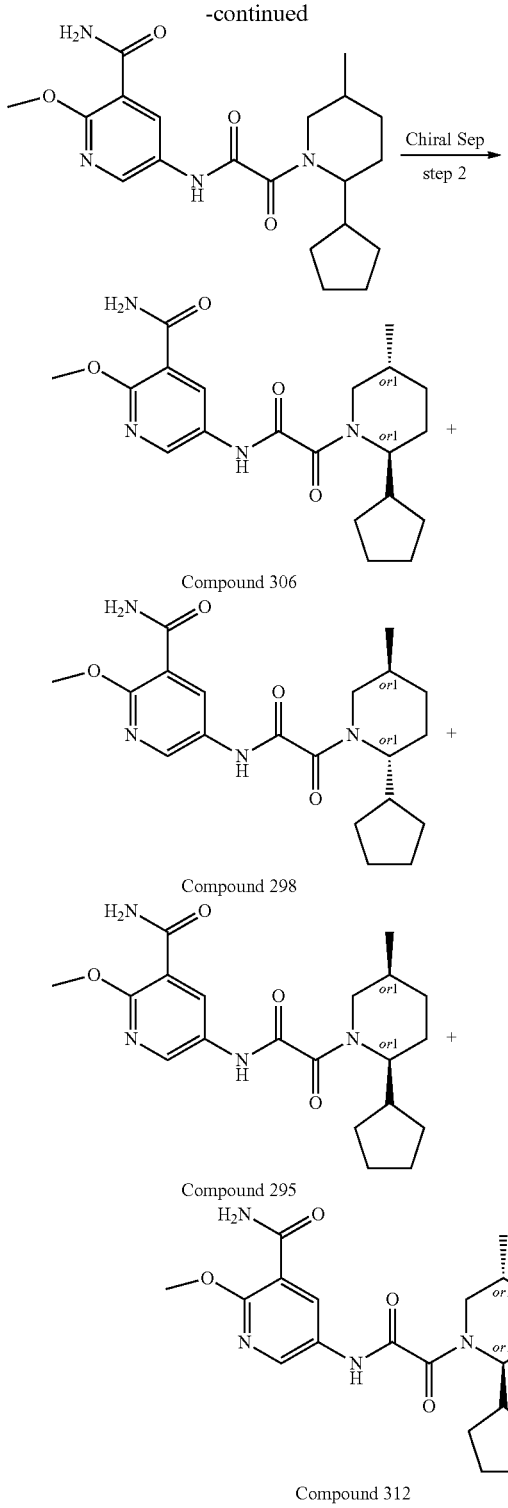

Compound 306

Compound 298

Compound 295

Compound 312

Step 1: Synthesis of 5-(2-(2-cyclopentyl-5-methylpiperidin-1-yl)-2-oxoacetamido)-2-methoxynicotinamide 2-[(5-carbamoyl-6-methoxy-3-pyridyl)amino]-2-oxo-acetic acid (0.5 g, 1.47 mmol, Et₃N), TATU (567.73 mg, 1.76 mmol) and TEA (148.65 mg, 1.47 mmol, 204.75 μL) were mixed in dry DMF (15 mL) at 21° C. and the resulting mixture was stirred for 15 min. 2-cyclopentyl-5-methyl-piperidine (245.75 mg, 1.47 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (50-100%2-7 min; water-MeOH+NH₃; 30 ml/min; loading pump 4 ml/min water; column XBridge 19*100 mm). 5-[[2-(2-cyclopentyl-5-methyl-1-piperidyl)-2-oxo-acetyl]amino]-2-methoxy-pyridine-3-carboxamide (189 mg, 486.54 μmol, 33.12% yield) was obtained as a white solid.

¹H NMR (400 MHz, CDCl₃) δ (ppm) 0.97 (d, 3H), 1.57 (m, 11H), 2.05 (m, 2H), 2.44 (m, 1H), 3.40 (m, 1H), 4.22 (s, 3H), 4.56 (m, 2H), 6.24 (m, 1H), 7.75 (m, 1H), 8.71 (m, 1H), 8.86 (s, 1H), 9.70 (m, 1H).

LCMS(ESI): [M]⁺ m/z: calcd 388.4; found 389.2; Rt=3.704 min.

Step 2: Chiral Separation (Compound 306, Compound 298, Compound 295 and Compound 312

5-[[2-(2-cyclopentyl-5-methyl-1-piperidyl)-2-oxo-acetyl]amino]-2-methoxy-pyridine-3-carboxamide (180 mg, 463.37 μmol) was separated using Chiralpak IC 250*20, 5 mkm column; Hexane-IPA-MeOH, 70-15-15 as a mobile phase; Flow rate 12 mL/min; Injection Volume: 900 mkl and Chiralpak IA 250*30, 5 mkm column; Hexane-IPA-MeOH, 70-15-15 as a mobile phase; Flow rate 27 mL/min; Injection Volume: 900 mkl; affording Compound 306-5-[[2-[(2S,5R)-2-cyclopentyl-5-methyl-1-piperidyl]-2-oxo-acetyl]amino]-2-methoxy-pyridine-3-carboxamide (60.96 mg, 156.93 μmol, 33.87% yield) (RT (IB, Hexane-IPA-MeOH, 90-5-5, 0.6 ml/min)=43.14 min) as a white solid, Compound 298—5-[[2-[(2R,5S)-2-cyclopentyl-5-methyl-1-piperidyl]-2-oxo-acetyl]amino]-2-methoxy-pyridine-3-carboxamide (75.83 mg, 195.21 μmol, 42.13% yield) (RT (IB, Hexane-IPA-MeOH, 90-5-5, 0.6 ml/min)=29.19 min) as a white solid, Compound 295—5-[[2-[(2S,5S)-2-cyclopentyl-5-methyl-1-piperidyl]-2-oxo-acetyl]amino]-2-methoxy-pyridine-3-carboxamide (12.95 mg, 33.34 μmol, 7.19% yield) (RT (IB, Hexane-IPA-MeOH, 90-5-5, 0.6 ml/min)=27.47 min) as a white solid and Compound 312—5-[[2-[(2R,5R)-2-cyclopentyl-5-methyl-1-piperidyl]-2-oxo-acetyl]amino]-2-methoxy-pyridine-3-carboxamide (10.81 mg, 27.83 μmol, 6.01% yield) (RT (IB, Hexane-IPA-MeOH, 90-5-5, 0.6 ml/min)=39.37 min) as a white solid.

Compound 306: Retention time: 43.14 min
¹H NMR (500 MHz, DMSO-d₆) δ (ppm) 0.91-1.00 (m, 3H), 1.02-1.23 (m, 2H), 1.27-1.35 (m, 1H), 1.42-1.78 (m, 8H), 1.87-2.00 (m, 2H), 2.93-3.26 (m, 1H), 3.36-3.60 (m, 2H), 3.95 (s, 3H), 4.00-4.27 (m, 1H), 7.74 (s, 2H), 8.41-8.48 (m, 1H), 8.52-8.58 (m, 1H), 10.81-10.90 (m, 1H).

LCMS(ESI): [M]⁺ m/z: calcd 388.2; found 389.2; Rt=3.520 min.

Compound 298: Retention time: 29.19 min
¹H NMR (500 MHz, DMSO-d₆) δ (ppm) 0.92-0.98 (m, 3H), 1.00-1.08 (m, 1H), 1.12-1.28 (m, 2H), 1.28-1.36 (m, 1H), 1.45-1.77 (m, 8H), 1.87-1.98 (m, 2H), 2.96-3.19 (m, 1H), 3.42-3.59 (m, 1H), 3.95 (s, 3H), 4.00-4.25 (m, 1H), 7.74 (s, 2H), 8.41-8.48 (m, 1H), 8.53-8.57 (m, 1H), 10.82-10.89 (m, 1H).

LCMS(ESI): [M]⁺ m/z: calcd 388.2; found 389.2; Rt=3.513 min.

Compound 295: Retention time: 27.47 min
¹H NMR (500 MHz, DMSO-d₆) δ (ppm) 0.78-0.93 (m, 3H), 1.01-1.23 (m, 2H), 1.29-1.40 (m, 1H), 1.48-1.75 (m, 10H), 2.41-2.44 (m, 1H), 2.78-3.19 (m, 1H), 3.49-3.56 (m, 1H), 3.92-3.98 (m, 3H), 4.15-4.29 (m, 1H), 7.70-7.80 (m, 2H), 8.43-8.49 (m, 1H), 8.51-8.57 (m, 1H), 10.79-10.96 (m, 1H).

LCMS(ESI): [M]+ m/z: calcd 388.2; found 389.2; Rt=3.556 min.

Compound 312: Retention time: 39.37 min
$^1$H NMR (500 MHz, DMSO-d$_6$) δ (ppm) 0.81-0.92 (m, 3H), 1.00-1.26 (m, 3H), 1.32-1.41 (m, 1H), 1.49-1.61 (m, 7H), 1.64-1.79 (m, 3H), 2.41-2.44 (m, 1H), 2.79-2.86 (m, 0.5H), 3.50-3.53 (m, 0.5H), 3.95-3.98 (m, 3H), 4.12-4.25 (m, 1H), 7.72-7.79 (m, 2H), 8.43-8.49 (m, 1H), 8.49-8.57 (m, 1H), 10.81-10.93 (m, 1H).

LCMS(ESI): [M]+ m/z: calcd 388.2; found 389.2; Rt=3.556 min.

Example 144. The Synthesis of 5-(2-(4-hydroxy-2-phenylpiperidin-1-yl)-2-oxoacetamido)Nicotinamide (Compound 185

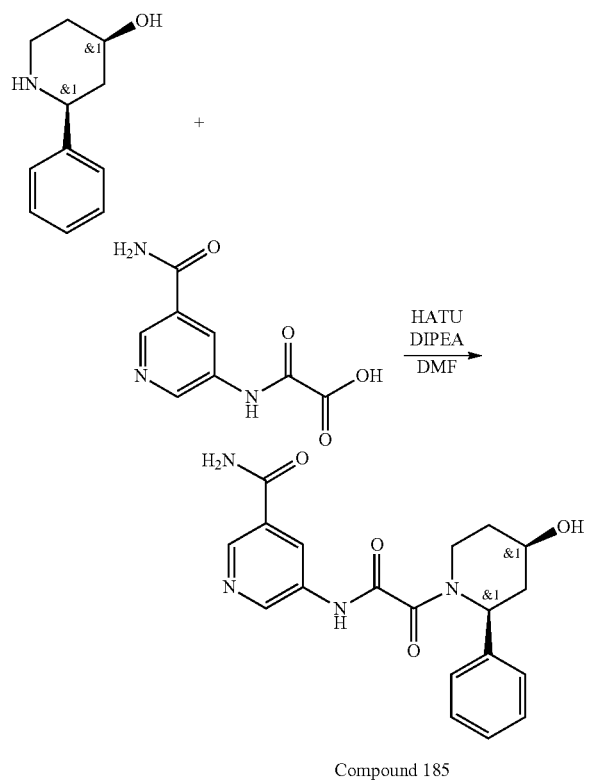

Compound 185

DIPEA (145.76 mg, 1.13 mmol, 196.44 μL) was added to the solution of respective 2-[(5-carbamoyl-3-pyridyl)amino]-2-oxo-acetic acid (0.1 g, 322.22 μmol, Et$_3$N) and (2S,4R)-2-phenylpiperidin-4-ol (57.11 mg, 267.24 μmol, HCl) in DMF (10 mL). The resulting mixture was stirred for 5 min followed by the addition of the solution of HATU (134.77 mg, 354.44 μmol) in DMF (2 mL). Then, the reaction mixture was stirred overnight at rt. After the completion of the reaction, monitored by LCMS, the resulting suspension was concentrated under reduced pressure. The obtained solid was subjected to HPLC to afford pure 5-[[2-[(2R,4S)-4-hydroxy-2-phenyl-1-piperidyl]-2-oxo-acetyl]amino]pyridine-3-carboxamide (61.2 mg, 166.13 μmol, 51.56% yield).

$^1$H NMR (600 MHz, DMSO-d$_6$) δ (ppm) 1.54 (m, 1H), 1.89 (m, 1H), 2.07 (m, 1H), 2.37 (m, 1H), 3.49 (m, 1H), 3.83 (m, 2H), 4.46 (m, 1H), 5.29 (m, 1H), 7.29 (m, 5H), 7.57 (m, 1H), 8.13 (m, 1H), 8.44 (m, 1H), 8.80 (m, 2H), 11.14 (m, 1H).

LCMS(ESI): [M]+ m/z: calcd 368.4; found 369.2; Rt=1.828 min.

Example 145. The Synthesis of rac-5-[[2-[(2R,4R,5R)-4-hydroxy-5-methyl-2-phenyl-1-piperidyl]-2-oxo-acetyl]amino]pyridine-3-carboxamide (Compound 459), rac-5-[[2-[(2R,4S,5R)-4-hydroxy-5-methyl-2-phenyl-1-piperidyl]-2-oxo-acetyl]amino]pyridine-3-carboxamide (Compound 470

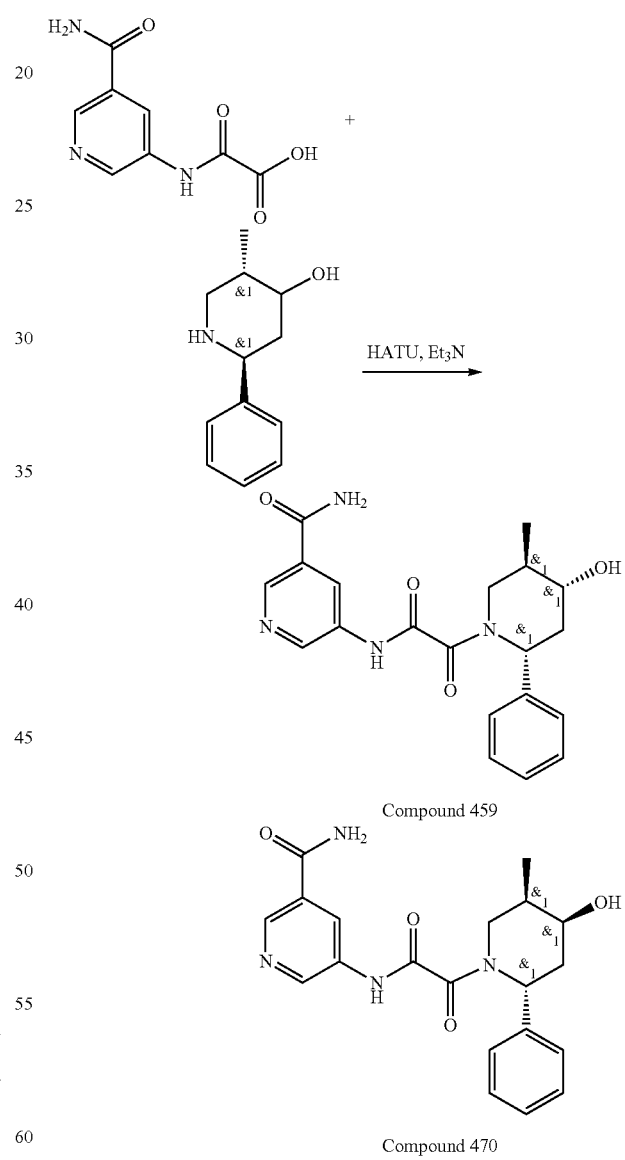

Compound 459

Compound 470

(2R,5R)-5-methyl-2-phenyl-piperidin-4-ol (0.1 g, 522.82 μmol), 2-[(5-carbamoyl-3-pyridyl)amino]-2-oxo-acetic acid (162.26 mg, 522.82 μmol, NEt$_3$), TEA (529.05 mg, 5.23 mmol, 728.71 μL) and HATU (298.19 mg, 784.24 μmol) was dissolved in DMF (5 mL) and stirred at 20° C. for 3 hr.

Reaction mixture was diluted with water and extracted three times with ethyl acetate, and then organic layer was washed three times with brine. Organic phase was dried over $Na_2SO_4$, filtered and evaporated at 40° C. to give crude product which was purified by HPLC (0-80% MeCN/water, 2-10 min, flow 30 ml/min (loading pump 4 ml/min MeCN) column: SunFire 100*19 5 mM) to give 5-[[2-[(2R,4R,5R)-4-hydroxy-5-methyl-2-phenyl-1-piperidyl]-2-oxo-acetyl]amino]pyridine-3-carboxamide (0.034 g, 88.91 µmol, 17.01% yield) Compound 459 and 5-[[2-[(2R,4S,5R)-4-hydroxy-5-methyl-2-phenyl-1-piperidyl]-2-oxo-acetyl]amino]pyridine-3-carboxamide (0.017 g, 44.45 µmol, 8.50% yield) Compound 470.

Compound 470:
$^1$H NMR (600 MHz, DMSO) δ 0.88-0.95 (m, 3H), 1.78-1.99 (m, 2H), 2.32-2.38 (m, 1H), 2.67-3.21 (m, 1H), 3.56-4.22 (m, 2H), 4.75-4.82 (m, 1H), 5.25-5.81 (m, 1H), 7.23-7.31 (m, 2H), 7.31-7.42 (m, 3H), 7.54-7.66 (m, 1H), 8.08-8.22 (m, 1H), 8.43-8.53 (m, 1H), 8.71-8.80 (m, 1H), 8.82-8.95 (m, 1H), 11.19-11.33 (m, 1H).
LCMS(ESI): [M+1]$^+$ m/z: calcd 382.2; found 383.2; Rt=2.221 min.

Compound 459:
$^1$H NMR (600 MHz, DMSO) δ 0.99 (d, 3H), 1.67-1.73 (m, 1H), 2.10-2.19 (m, 2H), 3.48-3.52 (m, 1H), 3.71-3.91 (m, 1H), 4.61-4.69 (m, 1H), 5.13-5.38 (m, 1H), 7.09-7.28 (m, 2H), 7.29-7.36 (m, 4H), 7.51-7.64 (m, 1H), 8.07-8.19 (m, 1H), 8.26-8.52 (m, 1H), 8.68-8.77 (m, 1H), 8.77-8.94 (m, 1H), 10.87-11.24 (m, 1H).
LCMS(ESI): [M+1]$^+$ m/z: calcd 382.2; found 383.2; Rt=2.221 min.

Example 146. The Synthesis of 5-[[2-[(4aR,8aS)-5,5-dimethyl-1,3,4,4a,6,7,8,8a-Octahydroisoquinolin-2-yl]-2-oxo-acetyl]amino]pyridine-3-carboxamide (Compound 193) and 5-[[2-[(4aS,8aR)-5,5-dimethyl-1,3,4,4a,6,7,8,8a-Octahydroisoquinolin-2-yl]-2-oxo-acetyl]amino]pyridine-3-carboxamide (Compound 197

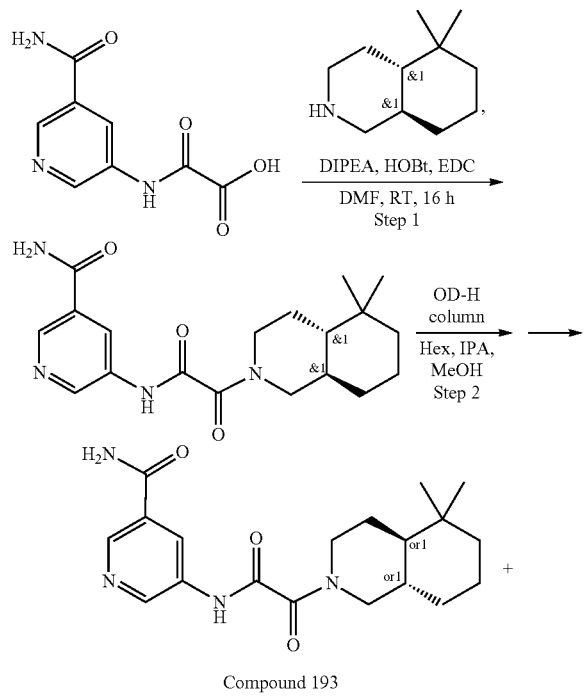

Compound 193

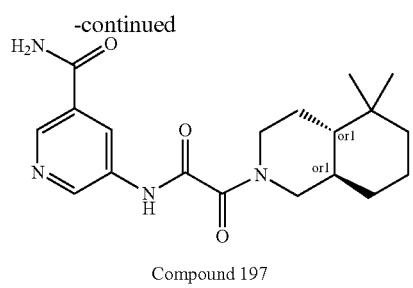

Compound 197

Step 1: The Synthesis of 5-[[2-[(4aS,8aR)-5,5-dimethyl-1,3,4,4a,6,7,8,8a-Octahydroisoquinolin-2-yl]-2-oxo-acetyl]amino]pyridine-3-carboxamide To a solution of (4aS,8aR)-5,5-dimethyl-2,3,4,4a,6,7,8,8a-octahydro-1H-isoquinoline (239.95 mg, 1.43 mmol), 2-[(5-carbamoyl-3-pyridyl)amino]-2-oxo-acetic acid (300 mg, 1.43 mmol, Triethylamine), DIPEA (556.11 mg, 4.30 mmol, 749.48 µL) in DMF (5 mL), EDC (329.95 mg, 1.72 mmol) was added portionwise. The resulting solution was stirred for 16 hr at 25° C. Then, the solvent was evaporated and residue was subjected to HPLC (35-70% 0-5 min 0.1% $NH_3$-methanol, flow: 30 ml/min) to give 5-[[2-[(4aS,8aR)-5,5-dimethyl-1,3,4,4a,6,7,8,8a-octahydroisoquinolin-2-yl]-2-oxo-acetyl]amino]pyridine-3-carboxamide (87 mg, 242.72 µmol, 16.92% yield).
LCMS(ESI): [M+H]$^+$ m/z: calcd 358.2; found 359.2; Rt=3.392 min.

Step 2: The Synthesis of 5-[[2-[(4aR,8aS)-5,5-dimethyl-1,3,4,4a,6,7,8,8a-Octahydroisoquinolin-2-yl]-2-oxo-acetyl]amino]pyridine-3-carboxamide (Compound 193) and 5-[[2-[(4aS,8aR)-5,5-dimethyl-1,3,4,4a,6,7,8,8a-Octahydroisoquinolin-2-yl]-2-oxo-acetyl]amino]pyridine-3-carboxamide (Compound 197

5-[[2-[(4aS,8aR)-5,5-dimethyl-1,3,4,4a,6,7,8,8a-octahydroisoquinolin-2-yl]-2-oxo-acetyl]amino]pyridine-3-carboxamide (87 mg, 242.72 µmol) was separated by chiral chromatography (OD-H (250*30, 5 mkm), Hexane-IPA-MeOH, 70-15-15, 30 ml/min) to give 5-[[2-[(4aR,8aS)-5,5-dimethyl-1,3,4,4a,6,7,8,8a-octahydroisoquinolin-2-yl]-2-oxo-acetyl]amino]pyridine-3-carboxamide (37 mg, 103.23 µmol, 42.53% yield) (RT=12.56 min) and 5-[[2-[(4aS,8aR)-5,5-dimethyl-1,3,4,4a,6,7,8,8a-octahydroisoquinolin-2-yl]-2-oxo-acetyl]amino]pyridine-3-carboxamide (36 mg, 100.44 µmol, 41.38% yield) (RT=19.56 min).

Compound 193:
RT (OD-H, Hexane-IPA-MeOH, 60-20-20, 0.6 mL/min)=12.56 min.
$^1$H NMR (dmso, 600 MHz): δ (ppm) 0.82 (m, 6H), 0.91 (d, 1H), 1.04 (m, 2H), 1.18 (m, 2H), 1.36 (m, 3H), 1.57 (m, 1H), 1.70 (m, 1H), 2.30 (m, 1H), 2.65 (m, 1H), 2.88 (m, 1H), 3.74 (m, 1H), 4.31 (m, 1H), 7.60 (s, 1H), 8.15 (s, 1H), 8.47 (m, 1H), 8.75 (s, 1H), 8.85 (s, 1H), 11.09 (s, 1H).
LCMS(ESI): [M+H]$^+$ m/z: calcd 358.2; found 359.2; Rt=3.175 min.

Compound 197:
RT (OD-H, Hexane-IPA-MeOH, 60-20-20, 0.6 mL/min)=19.56 min.
$^1$H NMR (dmso, 600 MHz): δ (ppm) 0.80 (m, 6H), 1.03 (m, 2H), 1.18 (m, 2H), 1.38 (m, 4H), 1.70 (m, 1H), 2.30 (m, 1H), 2.64 (m, 1H), 2.88 (m, 1H), 3.74 (m, 1H), 4.31 (m, 1H), 7.59 (s, 1H), 8.14 (s, 1H), 8.47 (m, 1H), 8.75 (s, 1H), 8.84 (s, 1H), 11.09 (s, 1H).

LCMS(ESI): [M+H]$^+$ m/z: calcd 358.2; found 359.2; Rt=3.175 min.

Example 147. The Synthesis of 5-[[2-[(2R,4S)-4-Cyano-2-phenyl-1-piperidyl]-2-oxo-acetyl]amino]pyridine-3-carboxamide and 5-[[2-[(2S,4R)-4-Cyano-2-phenyl-1-piperidyl]-2-oxo-acetyl]amino]pyridine-3-carboxamide (Compound 353 and Compound 352

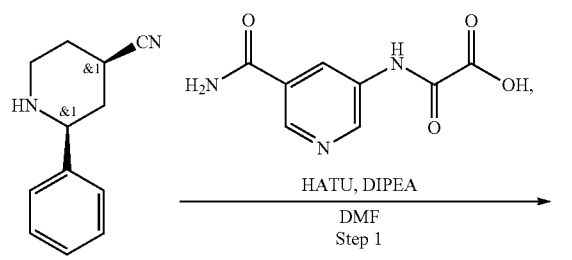

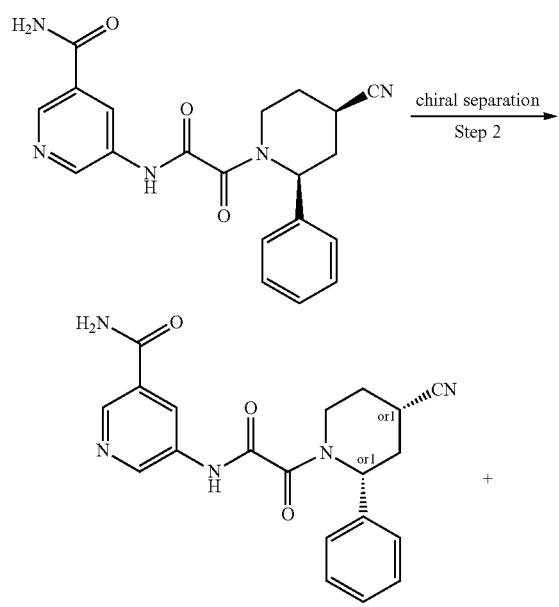

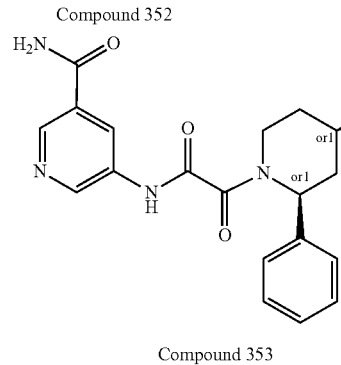

Compound 353

Step 1: Synthesis of 5-[[2-[(2S,4R)-4-Cyano-2-phenyl-1-piperidyl]-2-oxo-acetyl]amino]pyridine-3-carboxamide To a stirred solution of 2-[(5-carbamoyl-3-pyridyl)amino]-2-oxo-acetic acid (0.2 g, 814.27 µmol, HCl salt) and (2S,4R)-2-phenylpiperidine-4-carbonitrile (151.66 mg, 680.96 µmol, HCl salt) in DMF (10 mL) was added DIPEA (578.81 mg, 4.48 mmol, 780.07 µL). The resulting reaction mixture was stirred for 5 minutes. After 5 minutes, HATU (340.57 mg, 895.69 µmol) was added. The resulting reaction mixture was stirred for overnight at room temperature. Upon completion, the resulting suspension was concentrated under reduced pressure. The obtained crude product was purified by HPLC to afford pure 5-[[2-[(2S,4R)-4-cyano-2-phenyl-1-piperidyl]-2-oxo-acetyl]amino]pyridine-3-carboxamide (0.15 g, 397.46 µmol, 48.81% yield) as a light-yellow solid.

LCMS(ESI): [M+Boc]$^+$ m/z: calcd 377.2; found 378.4; Rt=2.314 min.

Step 2: Chiral Separation of 5-[[2-[(2R,4S)-4-Cyano-2-phenyl-1-piperidyl]-2-oxo-acetyl]amino]pyridine-3-carboxamide and 5-[[2-[(2S,4R)-4-Cyano-2-phenyl-1-piperidyl]-2-oxo-acetyl]amino]pyridine-3-carboxamide (Compound 353 and Compound 352

5-[[2-[(2S,4R)-4-cyano-2-phenyl-1-piperidyl]-2-oxo-acetyl]amino]pyridine-3-carboxamide (0.15 g) was subjected to chiral HPLC (column: IB (250*20, 5 um); Eluent: Hexane-IPA-MeOH, 50-25-25; flow rate: 13 mL/min) to get 5-[[2-[(2R,4S)-4-cyano-2-phenyl-1-piperidyl]-2-oxo-acetyl]amino]pyridine-3-carboxamide (Compound 353, 48.8 mg) and 5-[[2-[(2S,4R)-4-cyano-2-phenyl-1-piperidyl]-2-oxo-acetyl]amino]pyridine-3-carboxamide (Compound 352, 57.1 mg) as light-yellow solids.

Compound 353: $^1$H NMR (DMSO-d$_6$, 600 MHz): δ (ppm) 1.84-1.90 (m, 1H), 1.98-2.06 (m, 1H), 2.20-2.29 (m, 1H), 2.59-2.71 (m, 1H), 3.05-3.23 (m, 1H), 3.34-3.50 (m, 1H), 3.88-4.44 (m, 1H), 5.30-5.62 (m, 1H), 7.22-7.29 (m, 1H), 7.31-7.40 (m, 4H), 7.51-7.65 (m, 1H), 8.09-8.21 (m, 1H), 8.34-8.56 (m, 1H), 8.71-8.95 (m, 2H), 11.06-11.32 (m, 1H).

LCMS(ESI): [M+H]$^+$ m/z: calcd 377.2; found 378.2; Rt=3.903 min.

Chiral HPLC: Rt=14.44 min (column: IB; Eluent: Hexane-IPA-MeOH, 50-25-25; flow rate: 0.15 mL/min).

Compound 352: $^1$H NMR (DMSO-d$_6$, 600 MHz): δ (ppm) 1.83-2.04 (m, 2H), 2.20-2.25 (m, 1H), 2.59-2.72 (m, 1H), 3.04-3.24 (m, 1H), 3.32-3.52 (m, 1H), 3.87-4.46 (m, 1H), 5.31-5.58 (m, 1H), 7.21-7.28 (m, 1H), 7.31-7.38 (m, 4H), 7.51-7.65 (m, 1H), 8.06-8.21 (m, 1H), 8.36-8.55 (m, 1H), 8.71-8.93 (m, 2H), 11.07-11.31 (m, 1H).

LCMS(ESI): [M+H]$^+$ m/z: calcd 377.2; found 378.2; Rt=3.897 min.

Chiral HPLC: Rt=8.97 min (column: IB; Eluent: Hexane-IPA-MeOH, 50-25-25; flow rate: 0.15 mL/min).

Example 148. The Synthesis of 5-[[2-[(2S,4aR,8aR)-2-methyl-3,4,4a,5,6,7,8,8a-Octahydro-2H-Quinolin-1-yl]-2-oxo-acetyl]amino]pyridine-3-carboxamide and 5-[[2-[(2R,4aS,8aS)-2-methyl-3,4,4a,5,6,7,8,8a-Octahydro-2H-Quinolin-1-yl]-2-oxo-acetyl]amino]pyridine-3-carboxamide (Compound 245 and Compound 236)

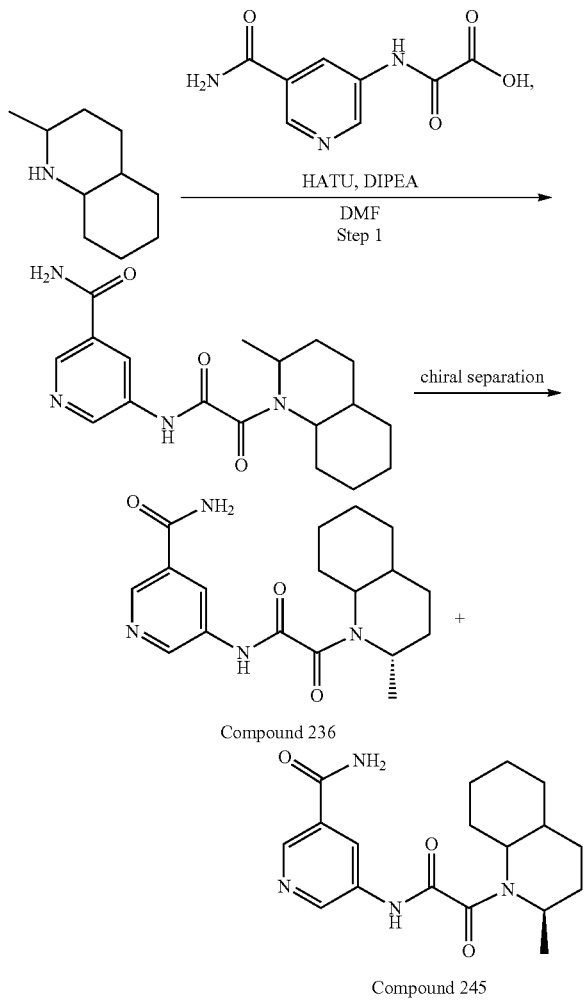

Step 1: Synthesis of 5-[[2-(2-methyl-3,4,4a,5,6,7,8,8a-Octahydro-2H-Quinolin-1-yl)-2-oxo-acetyl]amino]pyridine-3-carboxamide To a stirred solution of 2-[(5-carbamoyl-3-pyridyl)amino]-2-oxo-acetic acid (0.5 g, 1.61 mmol, Et$_3$N salt) and 2-methyl-1,2,3,4,4a,5,6,7,8,8a-decahydroquinoline (305.67 mg, 1.61 mmol, HCl salt) in DMF (10 mL) was added DIPEA (728.78 mg, 5.64 mmol, 982.18 μL). The resulting reaction mixture was stirred for 5 minutes. After 5 minutes, HATU (673.85 mg, 1.77 mmol) was added. The reaction mixture was stirred for overnight at room temperature. Upon completion, the resulting suspension was concentrated under reduced pressure. The obtained crude product was purified by column chromatography to obtain 5-[[2-(2-methyl-3,4,4a,5,6,7,8,8a-octahydro-2H-quinolin-1-yl)-2-oxo-acetyl]amino]pyridine-3-carboxamide (0.18 g, 522.64 μmol, 32.44% yield) as a light-yellow solid.

LCMS(ESI): [M+H]$^+$ m/z: calcd 344.2; found 345.2; Rt=1.180 min.

Chiral separation of 5-[[2-[(2S,4aR,8aR)-2-methyl-3,4,4a,5,6,7,8,8a-octahydro-2H-quinolin-1-yl]-2-oxo-acetyl]amino]pyridine-3-carboxamide and 5-[[2-[(2R,4aS,8aS)-2-methyl-3,4,4a,5,6,7,8,8a-octahydro-2H-quinolin-1-yl]-2-oxo-acetyl]amino]pyridine-3-carboxamide (Compound 245 and Compound 236)

5-[[2-(2-methyl-3,4,4a,5,6,7,8,8a-octahydro-2H-quinolin-1-yl)-2-oxo-acetyl]amino]pyridine-3-carboxamide (0.18 g) was subjected to chiral HPLC (Column: Chiralpak IA (250*20 mm, 5 um); Eluent: Hexane-IPA-MeOH, 80-10-10; Flow Rate: 12 mL/min) to get 5-[[2-[(2S,4aR,8aR)-2-methyl-3,4,4a,5,6,7,8,8a-octahydro-2H-quinolin-1-yl]-2-oxo-acetyl]amino]pyridine-3-carboxamide (Compound 245, 10 mg) and 5-[[2-[(2R,4aS,8aS)-2-methyl-3,4,4a,5,6,7,8,8a-octahydro-2H-quinolin-1-yl]-2-oxo-acetyl]amino]pyridine-3-carboxamide (Compound 236, 9.6 mg) as white solids.

Compound 236: $^1$H NMR (DMSO-d$_6$, 600 MHz): δ (ppm) 0.96-1.18 (m, 1H), 1.20-1.30 (m, 5H), 1.30-1.40 (m, 1H), 1.40-1.55 (m, 1H), 1.55-1.66 (m, 4H), 1.68-1.77 (m, 2H), 1.78-1.87 (m, 1H), 1.90-2.03 (m, 1H), 3.61-4.00 (m, 1H), 4.28-4.58 (m, 1H), 7.58-7.65 (m, 1H), 8.09-8.19 (m, 1H), 8.43-8.50 (m, 1H), 8.72-8.78 (m, 1H), 8.80-8.86 (m, 1H), 11.00-11.11 (m, 1H).

LCMS(ESI): [M+H]$^+$ m/z: calcd 344.2; found 345.2; Rt=3.080 min.

Chiral HPLC: Rt=21.02 min (column: IA; Eluent: Hexane-IPA-MeOH, 70-15-15; flow rate: 0.6 mL/min).

Compound 245: $^1$H NMR (DMSO-d$_6$, 600 MHz): δ (ppm) 0.95-1.18 (m, 1H), 1.20-1.30 (m, 5H), 1.31-1.43 (m, 1H), 1.44-1.56 (m, 1H), 1.56-1.66 (m, 4H), 1.68-1.77 (m, 2H), 1.78-1.89 (m, 1H), 1.93-2.05 (m, 1H), 3.59-4.03 (m, 1H), 4.24-4.58 (m, 1H), 7.54-7.66 (m, 1H), 8.11-8.20 (m, 1H), 8.41-8.49 (m, 1H), 8.71-8.79 (m, 1H), 8.81-8.87 (m, 1H), 10.99-11.12 (m, 1H).

LCMS(ESI): [M+H]$^+$ m/z: calcd 344.2; found 345.2; Rt=2.560 min.

Chiral HPLC: Rt=17.37 min (column: IA; Eluent: Hexane-IPA-MeOH, 70-15-15; flow rate: 0.6 mL/min).

Example 149. The Synthesis of 5-[[2-[2-(Benzothiophen-3-yl)-5-methyl-1-piperidyl]-2-oxo-acetyl]amino]-2-methoxy-pyridine-3-carboxamide (Compound 501

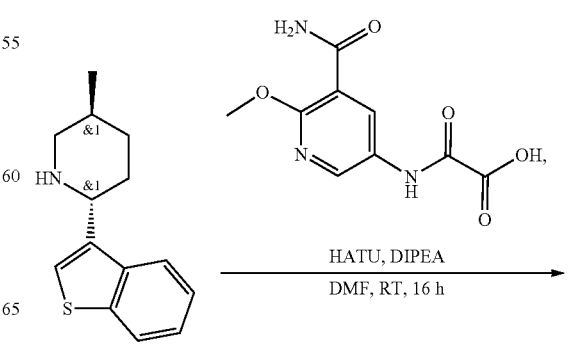

1523

-continued

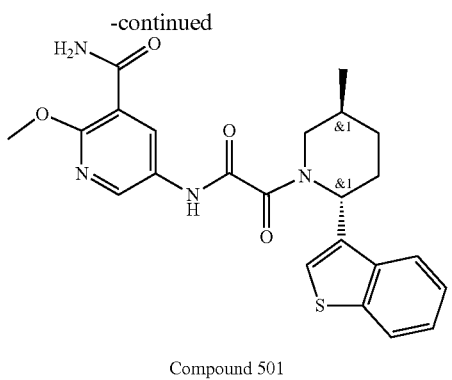

Compound 501

To a stirred solution of 2-(benzothiophen-3-yl)-5-methyl-piperidine (0.3 g, 1.30 mmol), 2-[(5-carbamoyl-6-methoxy-3-pyridyl)amino]-2-oxo-acetic acid (441.36 mg, 1.30 mmol, Et₃N) and N,N-diisopropylethylamine (837.95 mg, 6.48 mmol, 1.13 mL) in DMF (6 mL) was added HATU (591.65 mg, 1.56 mmol) at 25° C. The resulting reaction mixture was stirred at the same temperature for 16 hr. LCMS analysis of the crude reaction mixture indicated 31.88% of desired product mass under the curve area at RT=1.353 min. The crude reaction mixture was purified by Prep-HPLC (column: SunFire C18 100*19 mm 5 um, Mobile phase: 30-30-70% 0-1-5 min water-acetonitrile, flow: 30 mL/min, loading pump 4 mL/min acetonitrile) to afford product Compound 501—5-[[2-[2-(benzothiophen-3-yl)-5-methyl-1-piperidyl]-2-oxo-acetyl]amino]-2-methoxy-pyridine-3-carboxamide (200 mg, 441.96 μmol, 34.08% yield) as an off-white solid.

$^1$H NMR (600 MHz, DMSO-d$_6$) δ 0.94-1.08 (m, 3H), 1.33-1.57 (m, 1H), 1.91-1.99 (m, 1H), 2.00-2.13 (m, 2H), 2.13-2.30 (m, 1H), 3.35-3.48 (m, 1H), 3.48-3.65 (m, 1H), 3.91-4.05 (m, 3H), 5.51-6.00 (m, 1H), 7.28-7.41 (m, 2H), 7.67-7.74 (m, 2H), 7.75-7.81 (m, 1H), 7.81-7.90 (m, 1H), 7.92-8.02 (m, 1H), 8.34-8.46 (m, 1H), 8.45-8.58 (m, 1H), 10.86-11.12 (m, 1H).

LCMS(ESI): [M+H]⁺ m/z: calcd 452.1; found 453.4; Rt=3.392 min.

Example 150. The Synthesis of 5-[[2-[(2R,5S)-2-(Benzothiophen-3-yl)-5-methyl-1-piperidyl]-2-oxo-acetyl]amino]pyridine-3-carboxamide (Compound 466) and 5-[[2-[(2S,5R)-2-(Benzothiophen-3-yl)-5-methyl-1-piperidyl]-2-oxo-acetyl]amino]pyridine-3-carboxamide (Compound 463

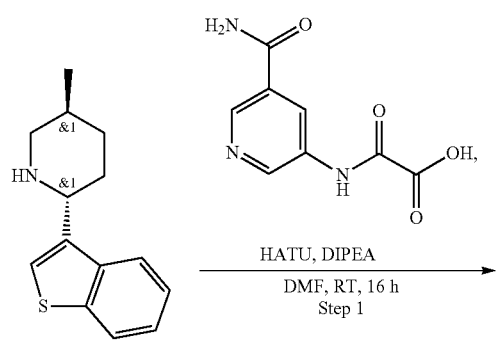

HATU, DIPEA
DMF, RT, 16 h
Step 1

1524

-continued

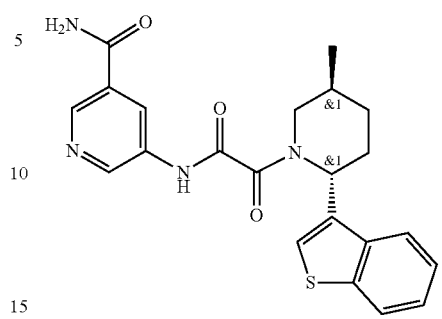

IB-I
Chiralpak column
Hex-IPA-MeOH
Step 2

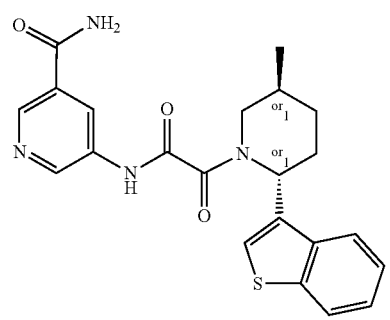

Compound 466

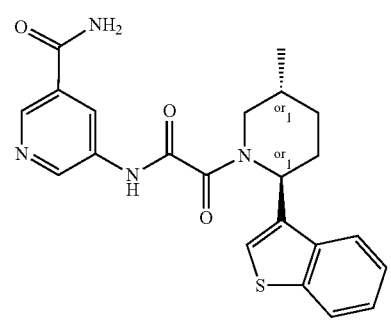

Compound 463

Step 1: The Synthesis of 5-[[2-[2-(Benzothiophen-3-yl)-5-methyl-1-piperidyl]-2-oxo-acetyl]amino]pyridine-3-carboxamide To a stirred solution of 2-(benzothiophen-3-yl)-5-methyl-piperidine (0.3 g, 1.30 mmol), 2-[(5-carbamoyl-3-pyridyl)amino]-2-oxo-acetic acid (318.50 mg, 1.30 mmol, HCl) and N,N-diisopropylethylamine (837.95 mg, 6.48 mmol, 1.13 mL) in DMF (6 mL), HATU (591.65 mg, 1.56 mmol) was added at 25° C. The resulting reaction mixture was stirred at 25° C. for 16 hr.

LCMS of the crude reaction mixture indicated 55.77% of desired product mass under the curve area at RT=1.25 min. The crude reaction mixture was purified by prep-HPLC (column: SunFire C18 100*19 mm 5um, Mobile Phase: 30-30-65% 0-1-5 min water-acetonitrile, flow: 30 mL/min, loading pump 4 mL/min acetonitrile) to afford 5-[[2-[2-(benzothiophen-3-yl)-5-methyl-1-piperidyl]-2-oxo-acetyl]amino]pyridine-3-carboxamide (400 mg, 946.75 μmol, 73.01% yield) as an off-white solid.

$^1$H NMR (400 MHz, DMSO-d$_6$) δ 1.04 (m, 3H), 1.42 (m, 1H), 2.12 (m, 4H), 3.40 (m, 1H), 3.56 (m, 2H), 6.00 (m, 1H), 7.33 (m, 1H), 7.40 (s, 1H), 7.83 (m, 1H), 7.94 (m, 1H), 8.01 (m, 1H), 8.18 (m, 1H), 8.51 (m, 1H), 8.79 (s, 1H), 8.91 (m, 1H), 11.28 (m, 1H).

LCMS(ESI): [M+H]$^+$ m/z: calcd 422.1; found 423.2; Rt=3.45 min.

Step 2: The Synthesis of 5-[[2-[(2R,5S)-2-(Benzothiophen-3-yl)-5-methyl-1-piperidyl]-2-oxo-acetyl]amino]pyridine-3-carboxamide (Compound 466) and 5-[[2-[(2S,5R)-2-(Benzothiophen-3-yl)-5-methyl-1-piperidyl]-2-oxo-acetyl]amino]pyridine-3-carboxamide (Compound 463

A racemic 5-[[2-[(2S,5R)-2-(benzothiophen-3-yl)-5-methyl-1-piperidyl]-2-oxo-acetyl]amino]pyridine-3-carboxamide (130 mg, 307.69 μmol) was submitted to preparative chiral HPLC (column: IB—I (250*20, 5 mkm), mobile phase: Hexane-IPA-MeOH, 70-15-15, flow rate: 12 mL/min) to afford pure product (Compound 466) 5-[[2-[(2R, 5S)-2-(benzothiophen-3-yl)-5-methyl-1-piperidyl]-2-oxo-acetyl]amino]pyridine-3-carboxamide (68.5 mg, 162.13 μmol, 52.69% yield) (RT=28.469 min) as a white solid and impure fraction (RT=18.587 min) which was further purified by preparative chiral HPLC (column: IA-II (250*20, 5 mkm), mobile phase: Hexane-IPA-MeOH, 50-25-25, flow rate: 10 mL/min) to obtain pure product (Compound 463) 5-[[2-[(2S,5R)-2-(benzothiophen-3-yl)-5-methyl-1-piperidyl]-2-oxo-acetyl]amino]pyridine-3-carboxamide (49.8 mg, 117.87 μmol, 38.31% yield) (RT=26.354 min) as a white solid.

Compound 466: RT (IA, Hex-IPA-MeOH, 50-25-25, 0.6 mL/min)=19.058 min.

$^1$H NMR (600 MHz, DMSO-d$_6$) δ 0.97-1.04 (m, 3H), 1.36-1.47 (m, 1H), 1.91-2.01 (m, 1H), 2.05-2.15 (m, 2H), 2.15-2.32 (m, 1H), 3.33-3.45 (m, 1H), 3.50-4.06 (m, 1H), 5.50-5.97 (m, 1H), 7.24-7.41 (m, 2H), 7.52-7.63 (m, 1H), 7.70-7.87 (m, 2H), 7.90-8.02 (m, 1H), 8.06-8.19 (m, 1H), 8.34-8.50 (m, 1H), 8.69-8.91 (m, 2H), 11.01-11.39 (m, 1H).

LCMS(ESI): [M+H]$^+$ m/z: calcd 422.1; found 423.0; Rt=3.309 min.

Compound 463: RT (IA, Hex-IPA-MeOH, 50-25-25, 0.6 mL/min)=23.854 min.

$^1$H NMR (600 MHz, DMSO-d$_6$) δ 0.98-1.06 (m, 3H), 1.37-1.46 (m, 1H), 1.93-2.01 (m, 1H), 2.05-2.14 (m, 2H), 2.14-2.31 (m, 1H), 3.33-3.43 (m, 1H), 3.52-4.04 (m, 1H), 5.52-5.94 (m, 1H), 7.28-7.41 (m, 2H), 7.53-7.62 (m, 1H), 7.69-7.88 (m, 2H), 7.90-8.01 (m, 1H), 8.07-8.19 (m, 1H), 8.34-8.52 (m, 1H), 8.68-8.91 (m, 2H), 11.01-11.34 (m, 1H).

LCMS(ESI): [M+H]$^+$ m/z: calcd 422.1; found 423.0; Rt=3.310 min.

Example 151. The Synthesis of 5-(2-(Octahydroisoquinolin-2(1-H)-yl)-2-oxoacetamido)Nicotinamide (Compound 429

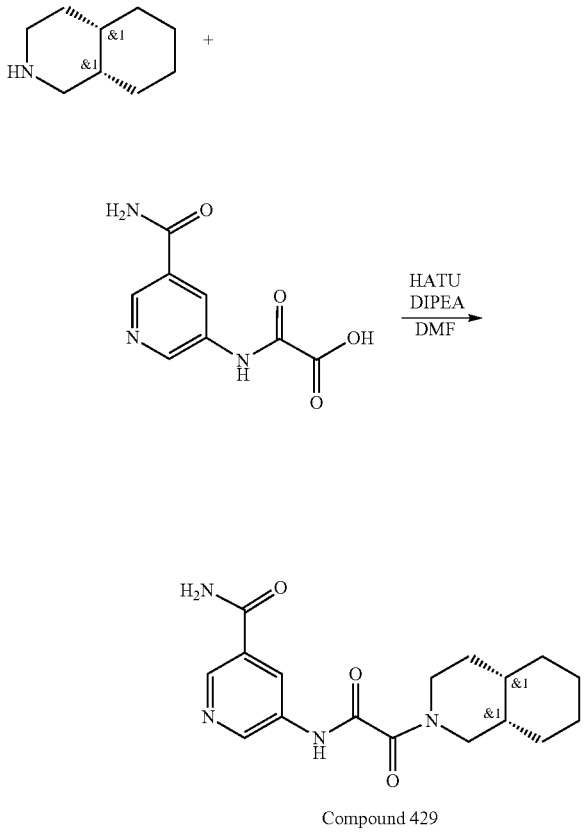

Compound 429

DIPEA (123.14 mg, 952.77 μmol, 165.96 μL) was added to the solution of respective (4aS,8aS)-1,2,3,4,4a,5,6,7,8,8a-decahydroisoquinoline (37.2 mg, 211.73 μmol, HCl) and 2-[(5-carbamoyl-3-pyridyl)amino]-2-oxo-acetic acid (57.20 mg, 232.90 μmol, HCl) in DMF (5 mL). The resulting mixture was stirred for 5 min followed by the addition of HATU (96.61 mg, 254.07 μmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and MeOH+NH$_3$ as an eluent mixture) to afford 5-[[2-[(4aS,8aS)-3,4,4a,5,6,7,8,8a-octahydro-1H-isoquinolin-2-yl]-2-oxo-acetyl]amino]pyridine-3-carboxamide (51.4 mg, 155.58 μmol, 73.48% yield).

$^1$H NMR (500 MHz, DMSO-d$_6$) δ (ppm) 1.17-1.33 (m, 2H), 1.33-1.42 (m, 3H), 1.43-1.52 (m, 2H), 1.52-1.62 (m, 2H), 1.63-1.81 (m, 2H), 1.84-1.95 (m, 1H), 2.92-3.25 (m, 2H), 3.52-3.73 (m, 1H), 3.77-4.11 (m, 1H), 7.47-7.76 (s, 1H), 8.08-8.24 (s, 1H), 8.38-8.58 (m, 1H), 8.69-8.81 (m, 1H), 8.82-8.94 (m, 1H), 10.57-11.17 (br s, 1H).

LCMS(ESI): [M]$^+$ m/z: calcd 330.4; found 331.2; Rt=2.719 min.

Example 152. The Synthesis of 5-[[2-[(2S,5R)-2-[(1S,3S)-3-hydroxycyclohexyl]-5-methyl-1-piperidyl]-2-oxo-acetyl]amino]pyridine-3-carboxamide (Compound 530), 5-[[2-[(2R,5S)-2-[(1R,3R)-3-hydroxycyclohexyl]-5-methyl-1-piperidyl]-2-oxo-acetyl]amino]pyridine-3-carboxamide (Compound 520), 5-[[2-[(2R,5S)-2-[(1R,3S)-3-hydroxycyclohexyl]-5-methyl-1-piperidyl]-2-oxo-acetyl]amino]pyridine-3-carboxamide (Compound 529) and 5-[[2-[(2S,5R)-2-[(1S,3R)-3-hydroxycyclohexyl]-5-methyl-1-piperidyl]-2-oxo-acetyl]amino]pyridine-3-carboxamide (Compound 531

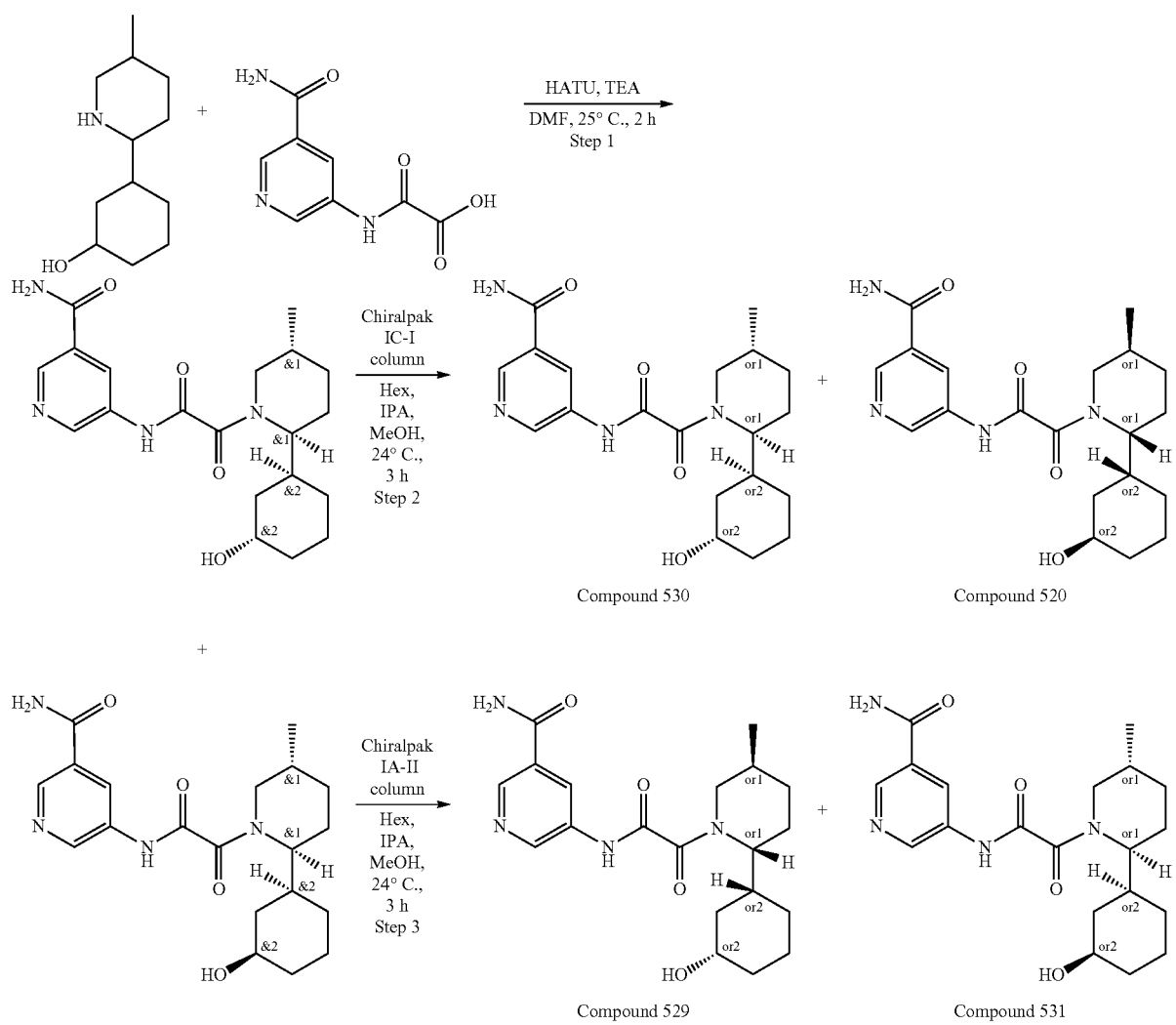

Step 1: The Synthesis of 5-[[2-[(2S,5R)-2-[(1S,3S)-3-hydroxycyclohexyl]-5-methyl-1-piperidyl]-2-oxo-acetyl]amino]pyridine-3-carboxamide and 5-[[2-[(2S,5R)-2-[(1S,3R)-3-hydroxycyclohexyl]-5-methyl-1-piperidyl]-2-oxo-acetyl]amino]pyridine-3-carboxamide A mixture of 3-(5-methyl-2-piperidyl)cyclohexanol (400.00 mg, 2.03 mmol), 2-[(5-carbamoyl-3-pyridyl)amino]-2-oxo-acetic acid (497.92 mg, 2.03 mmol, HCl) and triethyl amine (2.05 g, 20.27 mmol, 2.83 mL) in DMF (6 mL) was stirred at 25° C. for 0.25 hr, then HATU (847.88 mg, 2.23 mmol) was added in small portions over 0.5 hr. The reaction mixture was stirred at 25° C. for 12 hr, submitted to reverse phase HPLC (column: YMC-Triart C18 100*20 mm 5 um, mobile phase: 20-55% 0-5 min 0.1% $NH_3$-methanol, flow: 30 ml/min), which afforded 5-[[2-[(2S,5R)-2-[(1S,3S)-3-hydroxycyclohexyl]-5-methyl-1-piperidyl]-2-oxo-acetyl]amino]pyridine-3-carboxamide (161 mg, 414.46 μmol, 20.44% yield) and 5-[[2-[(2S,5R)-2-[(1S,3R)-3-hydroxycyclohexyl]-5-methyl-1-piperidyl]-2-oxo-acetyl]amino]pyridine-3-carboxamide (257 mg, 661.59 μmol, 32.64% yield) as light-yellow gums.

1st Fraction:

¹H NMR (400 MHz, DMSO-d₆) δ 0.9 (m, 2H), 1.01 (m, 3H), 1.31 (m, 2H), 1.65 (m, 4H), 1.98 (m, 5H), 2.87 (m, 1H), 3.61 (m, 1H), 4.12 (m, 3H), 4.56 (m, 1H), 7.62 (s, 1H), 8.18 (s, 1H), 8.51 (m, 1H), 8.78 (s, 1H), 8.90 (m, 1H), 11.05 (s, 1H).

LCMS(ESI): [M+H]⁺ m/z: calcd 388.2; found 389.2; Rt=2.317 min.

2nd Fraction:

¹H NMR (400 MHz, DMSO-d₆) δ 0.9 (m, 2H), 1.00 (m, 3H), 1.31 (m, 2H), 1.82 (m, 10H), 3.61 (m, 1H), 4.09 (m, 3H), 4.52 (m, 1H), 7.62 (s, 1H), 8.18 (s, 1H), 8.51 (m, 1H), 8.78 (s, 1H), 8.90 (m, 1H), 11.05 (s, 1H).

LCMS(ESI): [M+H]⁺ m/z: calcd 388.2; found 389.2; Rt=2.636 min.

Step 2: The Synthesis of 5-[[2-[(2S,5R)-2-[(1S,3S)-3-hydroxycyclohexyl]-5-methyl-1-piperidyl]-2-oxo-acetyl]amino]pyridine-3-carboxamide (Compound 530) and 5-[[2-[(2R,5S)-2-[(R,3R)-3-hydroxycyclohexyl]-5-methyl-1-piperidyl]-2-oxo-acetyl]amino]pyridine-3-carboxamide (Compound 520

Racemic 5-[[2-[(2S,5R)-2-[(1S,3S)-3-hydroxycyclohexyl]-5-methyl-1-piperidyl]-2-oxo-acetyl]amino]pyridine-3-carboxamide (161 mg, 414.46 μmol) was submitted to preparative chiral HPLC (Column: Chiralpak IC—I (250*20 mm, 5 mkm); Mobile phase: Hexane-IPA-MeOH, 50-25-25. Flow Rate: 12 mL/min; Column Temperature: 23° C.; Wavelength: 205 nm.) to afford Compound 530 5-[[2-[(2S,5R)-2-[(1S,3S)-3-hydroxycyclohexyl]-5-methyl-1-piperidyl]-2-oxo-acetyl]amino]pyridine-3-carboxamide (62.7 mg, 161.41 μmol, 38.94% yield) (R.T.=25.85 min) and Compound 520 5-[[2-[(2R,5S)-2-[(1R,3R)-3-hydroxycyclohexyl]-5-methyl-1-piperidyl]-2-oxo-acetyl]amino]pyridine-3-carboxamide (62.7 mg, 161.41 μmol, 38.94% yield) (R.T.=49.50 min) as white solids.

Compound 530: RT (IC-3, Hexane-IPA-MeOH, 50-25-25, 0.15 mL/min)=11.276 min.

¹H NMR (600 MHz, DMSO-d₆) δ 0.58-0.81 (m, 2H), 0.92-0.98 (m, 3H), 1.13-1.31 (m, 2H), 1.41-1.53 (m, 1H), 1.53-1.69 (m, 3H), 1.69-2.04 (m, 6H), 2.83-3.26 (m, 1H), 3.32-3.53 (m, 2H), 3.92-4.19 (m, 1H), 4.43-4.56 (m, 1H), 7.59 (s, 1H), 8.14 (s, 1H), 8.42-8.51 (m, 1H), 8.71-8.79 (m, 1H), 8.82-8.90 (m, 1H), 10.95-11.15 (m, 1H).

LCMS(ESI): [M+H]⁺ m/z: calcd 388.2; found 389.2; Rt=3.610 min.

Compound 520: RT (IC-3, Hexane-IPA-MeOH, 50-25-25, 0.15 mL/min)=21.019 min.

¹H NMR (600 MHz, DMSO-d₆) δ 0.59-0.79 (m, 2H), 0.93-1.02 (m, 3H), 1.13-1.30 (m, 2H), 1.40-1.53 (m, 1H), 1.52-1.68 (m, 3H), 1.68-2.01 (m, 6H), 2.85-3.26 (m, 1H), 3.32-3.53 (m, 2H), 3.95-4.17 (m, 1H), 4.43-4.57 (m, 1H), 7.53-7.62 (m, 1H), 8.09-8.19 (m, 1H), 8.43-8.50 (m, 1H), 8.70-8.78 (m, 1H), 8.83-8.91 (m, 1H), 10.92-11.13 (m, 1H).

LCMS(ESI): [M+H]⁺ m/z: calcd 388.2; found 389.2; Rt=3.615 min.

Step 3: The Synthesis of 5-[[2-[(2R,5S)-2-[(1R,3S)-3-hydroxycyclohexyl]-5-methyl-1-piperidyl]-2-oxo-acetyl]amino]pyridine-3-carboxamide (Compound 529) and 5-[[2-[(2S,5R)-2-[(1S,3R)-3-hydroxycyclohexyl]-5-methyl-1-piperidyl]-2-oxo-acetyl]amino]pyridine-3-carboxamide (Compound 531)

Racemic 5-[[2-[(2S,5R)-2-[(1S,3R)-3-hydroxycyclohexyl]-5-methyl-1-piperidyl]-2-oxo-acetyl]amino]pyridine-3-carboxamide (257 mg, 661.59 μmol) was first purified from other impurities using preparative chiral HPLC (Column: Chiralpak IA-II (250*20 mm, 5 mkm); Mobile phase: Hexane-IPA-MeOH, 50-25-25; Flow Rate: 12 mL/min) and then separated to enantiomers using preparative chiral HPLC (Column: Chiralpak IC—I (250*20 mm, 5 mkm); Mobile phase: Hexane-IPA-MeOH, 50-25-25; Flow Rate: 12 mL/min) to afford Compound 529 5-[[2-[(2R,5S)-2-[(1R,3S)-3-hydroxycyclohexyl]-5-methyl-1-piperidyl]-2-oxo-acetyl]amino]pyridine-3-carboxamide (78 mg, 200.79 μmol, 30.35% yield) (R.T.=35.628 min.) and Compound 531 5-[[2-[(2S,5R)-2-[(1S,3R)-3-hydroxycyclohexyl]-5-methyl-1-piperidyl]-2-oxo-acetyl]amino]pyridine-3-carboxamide (76 mg, 195.64 μmol, 29.57% yield) (R.T.=53.630 min.) as white solids.

Compound 529: RT (IC-3, Hexane-IPA-MeOH, 50-25-25, 0.15 mL/min)=14.944 min.

¹H NMR (600 MHz, DMSO-d₆) δ 0.58-0.78 (m, 2H), 0.92-0.98 (m, 3H), 1.17-1.30 (m, 2H), 1.54-1.75 (m, 5H), 1.75-2.00 (m, 5H), 2.84-3.27 (m, 1H), 3.34-3.57 (m, 2H), 3.99-4.15 (m, 1H), 4.43-4.54 (m, 1H), 7.59 (s, 1H), 8.15 (s, 1H), 8.41-8.55 (m, 1H), 8.69-8.79 (m, 1H), 8.84-8.92 (m, 1H), 10.92-11.20 (m, 1H).

LCMS(ESI): [M+H]⁺ m/z: calcd 388.2; found 389.2; Rt=4.009 min.

Compound 531: RT (IC-3, Hexane-IPA-MeOH, 50-25-25, 0.15 mL/min)=23.569 min.

¹H NMR (600 MHz, DMSO-d₆) δ 0.57-0.78 (m, 2H), 0.92-0.98 (m, 3H), 1.17-1.30 (m, 2H), 1.52-1.75 (m, 5H), 1.75-2.01 (m, 5H), 2.84-3.24 (m, 1H), 3.33-3.57 (m, 2H), 3.98-4.15 (m, 1H), 4.42-4.52 (m, 1H), 7.59 (s, 1H), 8.15 (s, 1H), 8.42-8.52 (m, 1H), 8.73-8.78 (m, 1H), 8.86-8.91 (m, 1H), 10.92-11.19 (m, 1H).

LCMS(ESI): [M+H]⁺ m/z: calcd 388.2; found 389.2; Rt=4.013 min.

Example 153. The Synthesis of 5-(2-(2-(3-bromophenyl)-5-methylpiperidin-1-yl)-2-oxoacetamido) Nicotinamide (Compound 601

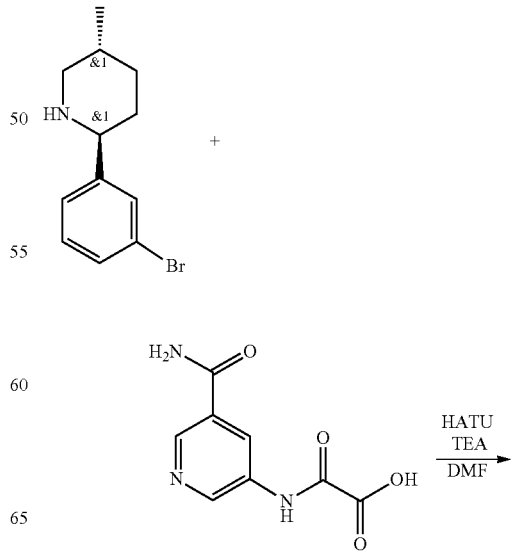

1531

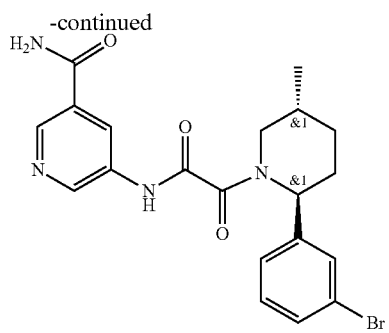

Compound 601

To the solution of (2S,5R)-2-(3-bromophenyl)-5-methyl-piperidine (374.58 mg, 1.29 mmol, HCl), 2-[(5-carbamoyl-3-pyridyl)amino]-2-oxo-acetic acid (400 mg, 1.29 mmol, Et₃N) and TEA (1.30 g, 12.89 mmol, 1.80 mL) in DMF (3 mL) HATU (539.08 mg, 1.42 mmol) was added portion wise. Mixture was stirred at 25° C. for 1.5 hr. The reaction mixture was then purified by reverse phase HPLC (50-50-90% 0-1-5 min 0.2% FA-MeOH, flow: 30 ml/min (loading pump 4 ml/min MeCN) target mass 445 column: YMC Triart C18 100×20 mm, 5 um) to give 5-[[2-[(2S,5R)-2-(3-bromophenyl)-5-methyl-1-piperidyl]-2-oxo-acetyl]amino]pyridine-3-carboxamide (153 mg, 343.58 μmol, 26.66% yield) as 2 fractions: 1st: 55 mg (100% LCMS); 2nd: 98 mg (97% LCMS).

¹H NMR (600 MHz, DMSO-d₆) δ (ppm) 0.99-1.03 (m, 3H), 1.27-1.36 (m, 1H), 1.59-1.68 (m, 1H), 1.82-1.94 (m, 1H), 1.99-2.14 (m, 1H), 2.15-2.25 (m, 1H), 2.75-3.26 (m, 1H), 3.47-4.06 (m, 1H), 5.10-5.60 (m, 1H), 7.31-7.37 (m, 2H), 7.43-7.50 (m, 2H), 7.55-7.67 (m, 1H), 8.09-8.21 (m, 1H), 8.44-8.52 (m, 1H), 8.70-8.80 (m, 1H), 8.80-8.95 (m, 1H), 11.11-11.42 (m, 1H).

LCMS(ESI): [M]⁺ m/z: calcd 445.4; found 446.2; Rt=3.051 min.

Example 154. The Synthesis of 5-(2-(2-(5-chloro-pyridin-3-yl)-5-methylpiperidin-1-yl)-2-oxoacetamido)Nicotinamide (Compound 791

1532

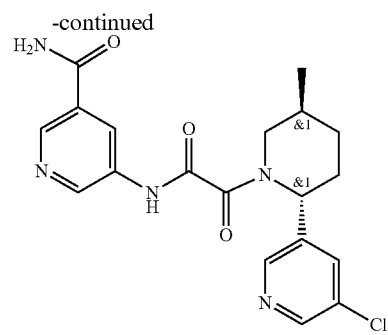

Compound 791

3-chloro-5-[(2R,5S)-5-methyl-2-piperidyl]pyridine (0.17 g, 806.82 μmol) and 2-[(5-carbamoyl-3-pyridyl)amino]-2-oxo-acetic acid (168.75 mg, 687.06 μmol, HCl) were dissolved in DMSO (6 mL) under gentle heating. HATU (368.13 mg, 968.19 μmol) was added in small portions under vigorous stirring and occasional heating. After the reaction was complete (concluded by LCMS of the reaction mixture), the mixture was purified by HPLC (14% 0.5-6.5 min water-MeCN; flow 30 ml/min; (loading pump 4 ml/min MecN); target mass 575; column SunFire C18 100×19 mm 5 um (L)) to give 5-[[2-[(2R,5S)-2-(5-chloro-3-pyridyl)-5-methyl-1-piperidyl]-2-oxo-acetyl]amino]pyridine-3-carboxamide (0.3 g, 746.55 μmol, 92.53% yield) in 2 fractions with different ratio of cis/trans isomers: 1 fraction 3:97 (200 mg); 2 fraction 20:80 (100 mg) (concluded by HNMR and LCMS).

Compound 791: ¹H NMR (600 MHz, DMSO-d₆) δ (ppm) 0.95-1.10 (m, 3H), 1.26-1.41 (m, 1H), 1.61-1.71 (m, 1H), 1.84-1.95 (m, 1H), 2.04-2.14 (m, 1H), 2.19-2.31 (m, 1H), 2.80-3.29 (m, 1H), 3.36-4.08 (m, 1H), 5.24-5.62 (m, 1H), 7.56-7.67 (m, 1H), 7.80-7.88 (m, 1H), 8.09-8.22 (m, 1H), 8.40-8.50 (m, 1H), 8.50-8.60 (m, 2H), 8.71-8.80 (m, 1H), 8.80-8.92 (m, 1H), 11.15-11.34 (m, 1H).

LCMS(ESI): [M]⁺ m/z: calcd 401.2; found 402.2; Rt=2.211 min.

Example 155. The Synthesis of 5-[[2-[(2R,5S)-5-methyl-2-[5-(methylamino)-2-pyridyl]-1-piperidyl]-2-oxo-acetyl]amino]pyridine-3-carboxamide (Compound 907

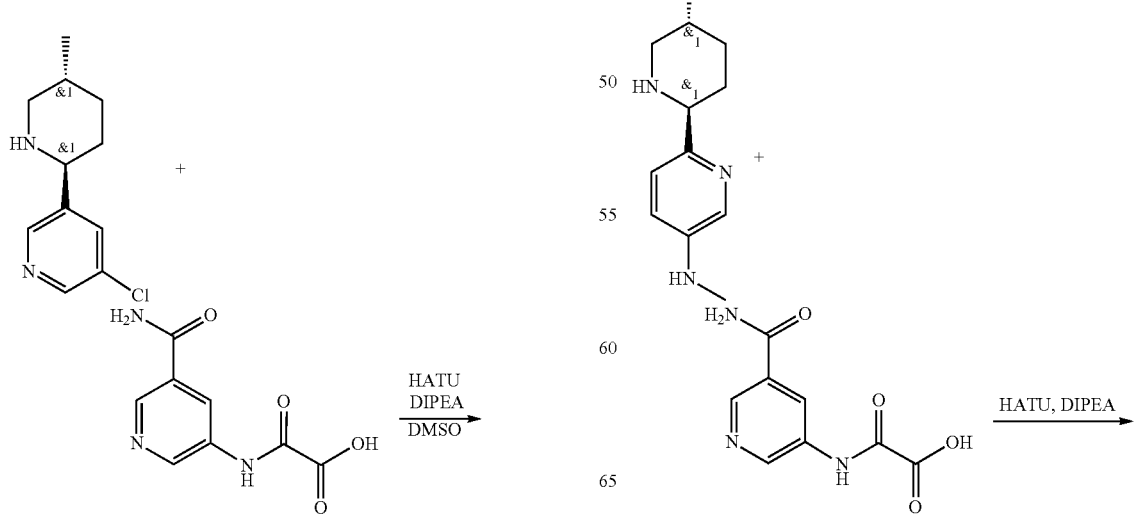

1533

-continued

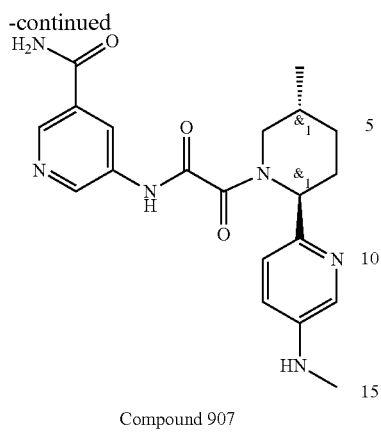

Compound 907

2-[(5-carbamoyl-3-pyridyl)amino]-2-oxo-acetic acid (10.77 mg, 43.84 µmol, HCl) and N-methyl-6-(5-methyl-2-piperidyl)pyridin-3-amine (0.009 g, 43.84 µmol) were mixed in DMF (2 mL). The reaction suspension was cooled to 20° C. and HATU (18.34 mg, 48.22 µmol) followed by TEA (13.31 mg, 131.52 µmol, 18.33 µL) were added and stirred at ambient temperature for 5 hr. The reaction mixture was evaporated in vacuo and obtained crude product 0.06 g was purified by preparative 25-60% 0-5 min H₂O/MeOH/ 0.1% NH₄OH, flow: 30 ml/min to afford product 5-[[2-[(2R, 5S)-5-methyl-2-[5-(methylamino)-2-pyridyl]-1-piperidyl]-2-oxo-acetyl]amino]pyridine-3-carboxamide (0.0035 g, 8.83 µmol, 20.14% yield).

$^1$H NMR (DMSO-d$_6$, 600 MHz): δ (ppm) 1.00 (m, 3H), 1.30 (m, 1H), 1.72 (m, 1H), 1.86 (m, 2H), 2.36 (m, 2H), 2.68 (m, 3H), 2.77 (m, 1H), 3.81 (m, 1H), 5.26 (m, 1H), 5.83 (m, 1H), 6.88 (m, 1H), 7.08 (m, 1H), 7.56 (m, 1H), 7.90 (m, 1H), 8.12 (m, 1H), 8.45 (m, 1H), 8.72 (m, 1H), 8.84 (m, 1H)

LCMS(ESI): [M+1]⁺ m/z: calcd 396.2; found 397.2; Rt=1.457 min.

Example 156. The Synthesis of 5-[[2-[(2R,5S)-2-(2-methoxy-4-pyridyl)-5-methyl-1-piperidyl]-2-oxo-acetyl]amino]pyridine-3-carboxamide (Compound 533) and 5-[[2-[(2S,5R)-2-(2-methoxy-4-pyridyl)-5-methyl-1-piperidyl]-2-oxo-acetyl]amino]pyridine-3-carboxamide (Compound 532

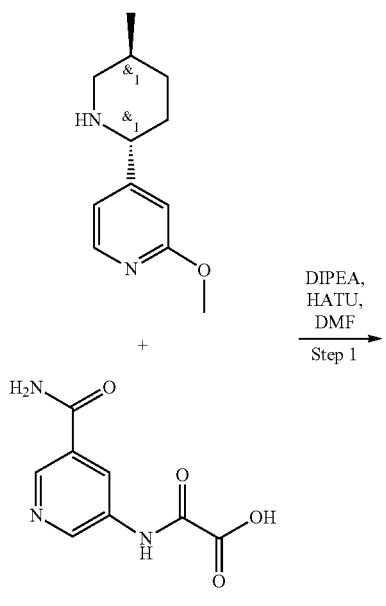

1534

-continued

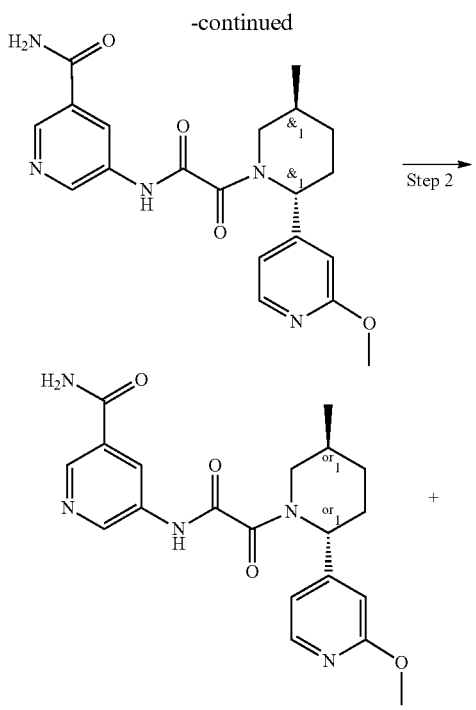

Step 1: Synthesis of 5-[[2-[2-(2-methoxy-4-pyridyl)-5-methyl-1-piperidyl]-2-oxo-acetyl]amino] pyridine-3-carboxamide DIPEA (701.72 mg, 5.43 mmol, 945.71 µL) was added to the solution of respective 2-methoxy-4-(5-methyl-2-piperidyl)pyridine (0.28 g, 1.36 mmol) and 2-[(5-carbamoyl-3-pyridyl)amino]-2-oxo-acetic acid (333.39 mg, 1.36 mmol, HCl) in DMF (10 mL). The resulting mixture was stirred for 5 min followed by the addition of the solution of HATU (448.65 mg, 1.18 mmol). Then, the reaction mixture was stirred overnight at room temperature. After the completion of the reaction, monitored by LCMS, the resulting suspension was concentrated under reduced pressure. The obtained solid was subjected to HPLC to afford pure 5-[[2-[2-(2-methoxy-4-pyridyl)-5-methyl-1-piperidyl]-2-oxo-acetyl] amino]pyridine-3-carboxamide (0.33 g, 830.34 µmol, 61.17% yield).

LCMS(ESI): [M+H]⁺ m/z: calcd 397.2; found 398.2; Rt=2.593 min.

Step 2: The Synthesis of 5-[[2-[(2R,5S)-2-(2-methoxy-4-pyridyl)-5-methyl-1-piperidyl]-2-oxo-acetyl]amino]pyridine-3-carboxamide (Compound 533) and 5-[[2-[(2S,5R)-2-(2-methoxy-4-pyridyl)-5-methyl-1-piperidyl]-2-oxo-acetyl]amino]pyridine-3-carboxamide (Compound 532

5-[[2-[2-(2-methoxy-4-pyridyl)-5-methyl-1-piperidyl]-2-oxo-acetyl]amino]pyridine-3-carboxamide (330.0 mg, 830.34 µmol) was chirally separated using Chiralpak IC 250*20 mm 5 mkm column, IPA-MeOH, 50-50 as a mobile phase, Flow 12 mL/min affording Compound 532—5-[[2-[(2S,5R)-2-(2-methoxy-4-pyridyl)-5-methyl-1-piperidyl]-2-oxo-acetyl]amino]pyridine-3-carboxamide (162.88 mg, 49.36% yield) and Compound 533—5-[[2-[(2R,5S)-2-(2-methoxy-4-pyridyl)-5-methyl-1-piperidyl]-2-oxo-acetyl] amino]pyridine-3-carboxamide (141.67 mg, 42.93% yield).

Rel.Time for Compound 532 (IC, MeOH-IPA, 50-50, 0.6 mL/min)=18.87 min

Rel.Time for Compound 533 (IC, MeOH-IPA, 50-50, 0.6 mL/min)=35.96 min

Compound 533: $^1$H NMR (600 MHz, DMSO-$d_6$) δ 0.99-1.01 (m, 3H), 1.29-1.42 (m, 1H), 1.51-1.61 (m, 1H), 1.80-1.94 (m, 1H), 1.97-2.14 (m, 1H), 2.13-2.24 (m, 1H), 2.74-3.25 (m, 1H), 3.45-3.54 (m, 0.7H), 3.80-3.88 (m, 3H), 4.00-4.09 (m, 0.3H), 5.06-5.69 (m, 1H), 6.70-6.78 (m, 1H), 6.91-6.97 (m, 1H), 7.50-7.67 (m, 1H), 8.05-8.21 (m, 2H), 8.40-8.54 (m, 1H), 8.69-8.80 (m, 1H), 8.81-8.96 (m, 1H), 11.18-11.35 (m, 1H).

LCMS(ESI): [M+H]$^+$ m/z: calcd 397.2; found 398.2; Rt=0.895 min.

RT (IC, IPA-MeOH, 50-50, 12 ml/min)=35.9532 min

Compound 532: $^1$H NMR (600 MHz, DMSO-$d_6$) δ 1.00-1.01 (m, 3H), 1.29-1.36 (m, 1H), 1.54-1.60 (m, 1H), 1.75-1.97 (m, 1H), 1.97-2.13 (m, 1H), 2.13-2.23 (m, 1H), 2.75-3.23 (m, 1H), 3.47-3.50 (m, 0.7H), 3.82-3.85 (m, 3H), 4.02-4.06 (m, 0.3H), 5.12-5.50 (m, 1H), 6.71-6.73 (m, 1H), 6.92-6.95 (m, 1H), 7.56-7.63 (m, 1H), 8.11-8.17 (m, 2H), 8.43-8.50 (m, 1H), 8.71-8.78 (m, 1H), 8.83-8.90 (m, 1H), 11.20-11.30 (m, 1H).

LCMS(ESI): [M+H]$^+$ m/z: calcd 397.2; found 398.2; Rt=4.140 min.

RT (IC, IPA-MeOH, 50-50, 12 ml/min)=18.8732 min.

Example 157. The Synthesis of 5-[[2-[(2R,5S)-5-methyl-2-(7-methyl-1H-indazol-5-yl)-1-piperidyl]-2-oxo-acetyl]amino]pyridine-3-carboxamide (Compound 638) and 5-[[2-[(2R,5S)-5-methyl-2-(7-methyl-1H-indazol-5-yl)-1-piperidyl]-2-oxo-acetyl] amino]pyridine-3-carboxamide (Compound 611

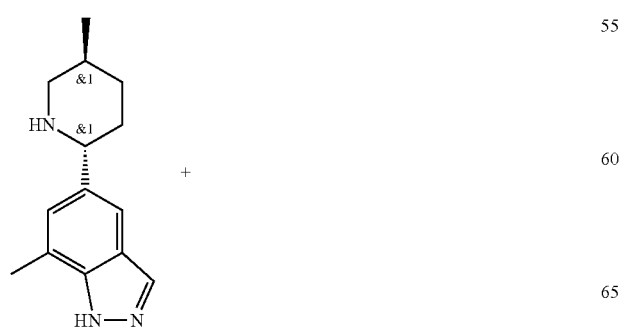

+

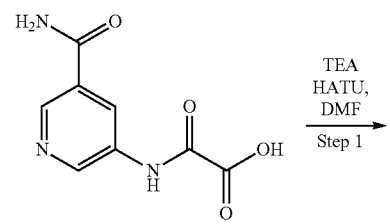

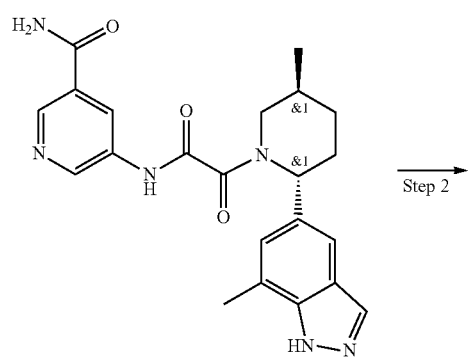

Compound 638

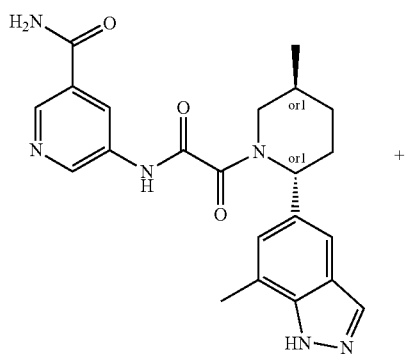

+

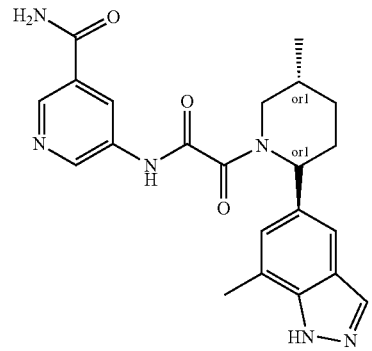

Compound 611

Step 1: Synthesis of 5-[[2-[5-methyl-2-(7-methyl-1H-indazol-5-yl)-1-piperidyl]-2-oxo-acetyl]amino]pyridine-3-carboxamide 2-[(5-carbamoyl-3-pyridyl)amino]-2-oxo-acetic acid (638.46 mg, 3.05 mmol) and 7-methyl-5-(5-methyl-2-piperidyl)-1H-indazole (0.7 g, 3.05 mmol) were mixed in DMF (25 mL). The reaction suspension was cooled to 0° C. and HATU (1.16 g, 3.05 mmol) followed by TEA (926.65 mg, 9.16 mmol, 1.28 mL) were added and stirred at ambient temperature for 14 hr. The reaction mixture was evaporated in vacuo and poured into water (100 ml) and extracted with EtOAc (2×30 ml). The combined organic extracts were washed with water (2*30 ml), dried over sodium sulphate and evaporated in vacuo and obtained crude product 0.82 g was purified by preparative 30-80% 1-6 min water-methanol (NH$_3$ 0.1%), flow 30 ml/min to afford product 5-[[2-[5-methyl-2-(7-methyl-1H-indazol-5-yl)-1-piperidyl]-2-oxo-acetyl]amino]pyridine-3-carboxamide (0.042 g, 99.89 μmol, 3.27% yield).

LCMS(ESI): [M+H]$^+$ m/z: calcd 420.2; found 421.2; Rt=1.124 min.

Step 2: The Synthesis of 5-[[2-[(2R,5S)-5-methyl-2-(7-methyl-1H-indazol-5-yl)-1-piperidyl]-2-oxo-acetyl]amino]pyridine-3-carboxamide (Compound 638) and 5-[[2-[(2R,5S)-5-methyl-2-(7-methyl-1H-indazol-5-yl)-1-piperidyl]-2-oxo-acetyl]amino]pyridine-3-carboxamide (Compound 611)

The 5-[[2-[5-methyl-2-(7-methyl-1H-indazol-5-yl)-1-piperidyl]-2-oxo-acetyl]amino]pyridine-3-carboxamide (0.03 g, 71.35 μmol) was subjected to chiral HPLC purification (Column: IC-II (250*20, 5 um), Eluent: Hexane-IPA-MeOH, 60-20-20 as a mobile phase, flow rate: 12 mL/min) to give the two individual enantiomers Compound 611—5-[[2-[(2R,5S)-5-methyl-2-(7-methyl-1H-indazol-5-yl)-1-piperidyl]-2-oxo-acetyl]amino]pyridine-3-carboxamide (0.007 g, 16.65 μmol, 23.33% yield) and Compound 638—5-[[2-[(2R,5S)-5-methyl-2-(7-methyl-1H-indazol-5-yl)-1-piperidyl]-2-oxo-acetyl]amino]pyridine-3-carboxamide (0.007 g, 16.65 μmol, 23.33% yield).

Compound 638: $^1$H NMR (500 MHz, DMSO-d$_6$) δ 1.00-1.06 (m, 3H), 1.33-1.42 (m, 1H), 1.75-1.91 (m, 2H), 1.98-2.11 (m, 1H), 2.11-2.25 (m, 1H), 2.41-2.45 (m, 3H), 2.79-3.24 (m, 1H), 3.46-4.05 (m, 1H), 5.19-5.70 (m, 1H), 7.05-7.16 (m, 1H), 7.48-7.68 (m, 2H), 7.99-8.08 (m, 1H), 8.09-8.22 (m, 1H), 8.41-8.56 (m, 1H), 8.70-8.79 (m, 1H), 8.79-8.99 (m, 1H), 11.16-11.38 (m, 1H), 13.06-13.17 (m, 1H).

LCMS(ESI): [M+H]$^+$ m/z: calcd 420.5; found 421.4; Rt=3.923 min.

RT (Hexane-IPA-MeOH, 60-20-20, 12 ml/min)=52.9202 min.

Compound 611: $^1$H NMR (500 MHz, DMSO-d$_6$) δ 0.97-1.10 (m, 3H), 1.30-1.44 (m, 1H), 1.72-1.92 (m, 2H), 2.04-2.19 (m, 1H), 2.23-2.30 (m, 1H), 2.40-2.47 (m, 3H), 2.81-3.28 (m, 1H), 3.46-4.08 (m, 1H), 5.10-5.73 (m, 1H), 7.04-7.17 (m, 1H), 7.49-7.55 (m, 1H), 7.55-7.69 (m, 1H), 7.99-8.08 (m, 1H), 8.09-8.21 (m, 1H), 8.41-8.57 (m, 1H), 8.70-8.80 (m, 1H), 8.80-8.96 (m, 1H), 11.10-11.46 (m, 1H), 13.01-13.27 (m, 1H).

LCMS(ESI): [M+H]$^+$ m/z: calcd 420.5; found 421.4; Rt=3.926 min.

RT (Hexane-IPA-MeOH, 60-20-20, 12 ml/min)=34.8442 min.

Example 158. The Synthesis of 5-[[2-[(2R,5S)-2-(4-fluoro-1H-indazol-5-yl)-5-methyl-1-piperidyl]-2-oxo-acetyl]amino]pyridine-3-carboxamide (Compound 637) and 5-[[2-[(2S,5R)-2-(4-fluoro-1H-indazol-5-yl)-5-methyl-1-piperidyl]-2-oxo-acetyl]amino]pyridine-3-carboxamide (Compound 612

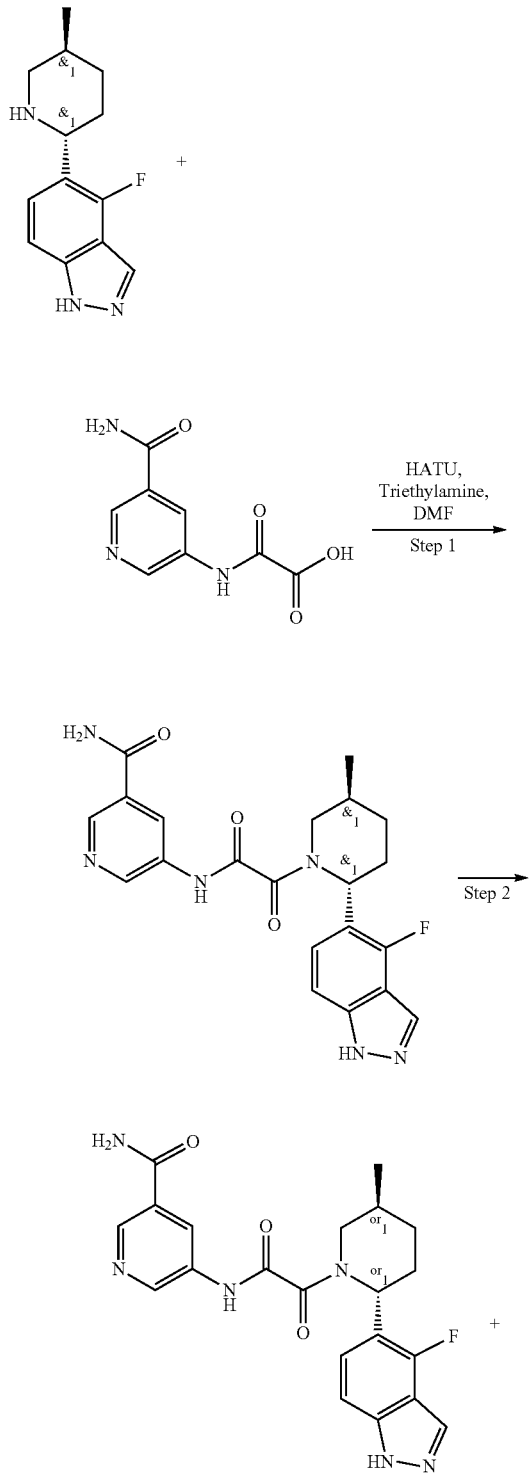

Compound 637

-continued

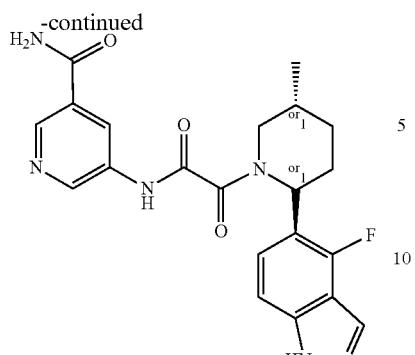

Compound 612

Step 1: Synthesis of 5-[[2-[2-(4-fluoro-1H-indazol-5-yl)-5-methyl-1-piperidyl]-2-oxo-acetyl]amino]pyridine-3-carboxamide 4-fluoro-5-(5-methyl-2-piperidyl)-1H-indazole (0.3 g, 1.29 mmol), 2-[(5-carbamoyl-3-pyridyl)amino]-2-oxo-acetic acid (315.86 mg, 1.29 mmol, HCl) and Triethylamine (1.30 g, 12.86 mmol, 1.79 mL) were mixed together in DMF (5 mL). HATU (733.46 mg, 1.93 mmol) was added to the previous mixture and the resulting mixture was stirred overnight. The reaction mixture was concentrated in vacuo and the residue was purified by HPLC (2-10 min 50-60% MeOH/H$_2$O, 30 ml/min (loading pump 4 ml MeOH, column: SunFire 100*19 mm, 5 micro) to obtain 5-[[2-[2-(4-fluoro-1H-indazol-5-yl)-5-methyl-1-piperidyl]-2-oxo-acetyl]amino]pyridine-3-carboxamide (0.0866 g, 204.04 µmol, 15.87% yield).

LCMS(ESI): [M+H]$^+$ m/z: calcd 424.2; found 425.2; Rt=1.066 min.

Step 2: The Synthesis of 5-[[2-[(2R,5S)-2-(4-fluoro-1H-indazol-5-yl)-5-methyl-1-piperidyl]-2-oxo-acetyl]amino]pyridine-3-carboxamide (Compound 637) and 5-[[2-[(2S,5R)-2-(4-fluoro-1H-indazol-5-yl)-5-methyl-1-piperidyl]-2-oxo-acetyl]amino]pyridine-3-carboxamide (Compound 612)

5-[[2-[2-(4-fluoro-1H-indazol-5-yl)-5-methyl-1-piperidyl]-2-oxo-acetyl]amino]pyridine-3-carboxamide (0.0886 g, 208.75 µmol) was chirally separated (Column: Chiralpak IC (250*20 mm, 5 mkm); Mobile phase: Hexane-IPA-MeOH, 50-25-25. Flow Rate: 12 mL/min; Column Temperature: 24° C.; Wavelength: 205 nm. to obtain: RetTime=54.05 min: 5-[[2-[(2R,5S)-2-(4-fluoro-1H-indazol-5-yl)-5-methyl-1-piperidyl]-2-oxo-acetyl]amino]pyridine-3-carboxamide (0.04274 g, 100.70 µmol, 48.24% yield)

$^1$H NMR (600 MHz, DMSO-d$_6$) δ 1.00-1.03 (m, 3H), 1.16-1.36 (m, 1H), 1.83-1.94 (m, 1H), 1.98-2.20 (m, 3H), 3.53-3.98 (m, 2H), 5.45-5.58 (m, 1H), 7.23-7.39 (m, 2H), 7.51-7.65 (m, 1H), 7.98-8.20 (m, 2H), 8.27-8.54 (m, 1H), 8.58-8.91 (m, 2H), 10.70-11.39 (m, 1H), 13.11-13.52 (m, 1H).

LCMS(ESI): [M+H]$^+$ m/z: calcd 424.4; found 425.2; Rt=4.117 min.

RetTime=26.80 min: 5-[[2-[(2S,5R)-2-(4-fluoro-1H-indazol-5-yl)-5-methyl-1-piperidyl]-2-oxo-acetyl]amino]pyridine-3-carboxamide (43.61 mg, 102.75 µmol, 49.22% yield)

$^1$H NMR (600 MHz, DMSO-d$_6$) δ 1.00-1.01 (m, 3H), 1.18-1.41 (m, 1H), 1.82-2.02 (m, 3H), 2.04-2.13 (m, 1H), 3.56-3.91 (m, 2H), 5.45-5.56 (m, 1H), 7.22-7.38 (m, 2H), 7.48-7.64 (m, 1H), 8.00-8.17 (m, 2H), 8.26-8.48 (m, 1H), 8.61-8.92 (m, 2H), 10.75-11.33 (m, 1H), 13.12-13.46 (m, 1H).

LCMS(ESI): [M+H]$^+$ m/z: calcd 424.4; found 425.2; Rt=4.115 min.

Example 159. The Synthesis of 5-[[2-[(2R,5S)-2-(4-fluoro-3-hydroxy-phenyl)-5-methyl-1-piperidyl]-2-oxo-acetyl]amino]pyridine-3-carboxamide (Compound 540

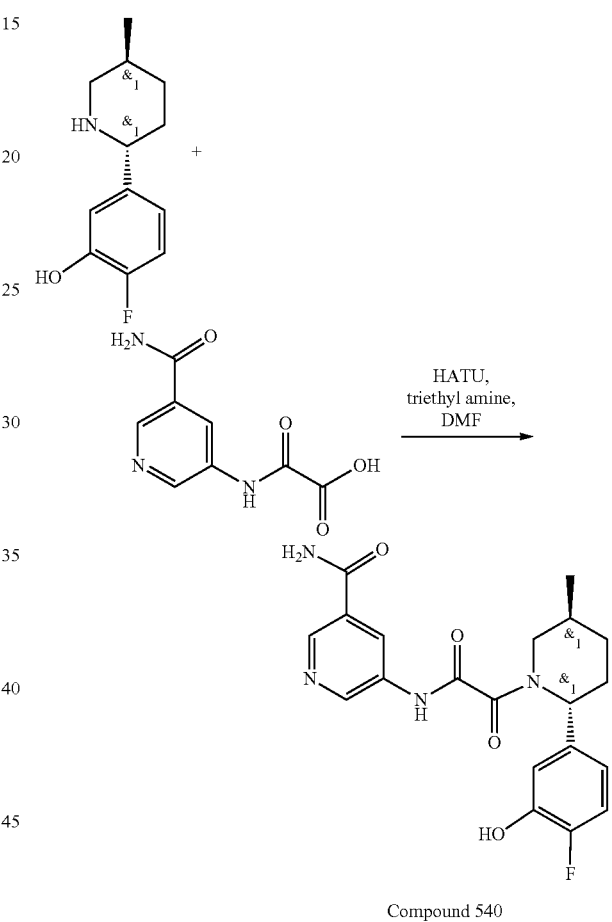

Compound 540

To a stirred solution of 2-fluoro-5-[(2R,5S)-5-methyl-2-piperidyl]phenol (500 mg, 1.72 mmol, HBr), 2-[(5-carbamoyl-3-pyridyl)amino]-2-oxo-acetic acid (423.23 mg, 1.72 mmol, HCl) and triethyl amine (1.74 g, 17.23 mmol, 2.40 mL) in DMF (20 mL) was added HATU (1.31 g, 3.45 mmol) in small portions at 25° C. The resulting reaction mixture was stirred at 25° C. for 16 hr, then concentrated in vacuo to approximately 5 ml and submitted to reverse phase HPLC (column: YMC Triart C18 100×20 mm, 5um, mobile phase 30-30-60% 0-1-6 min 0.2% formic acid-methanol, flow rate: 30 ml/min) to afford Compound 540 5-[[2-[(2R,5S)-2-(4-fluoro-3-hydroxy-phenyl)-5-methyl-1-piperidyl]-2-oxo-acetyl]amino]pyridine-3-carboxamide (128 mg, 319.68 µmol, 18.55% yield) as white solid.

$^1$H NMR (600 MHz, DMSO-d$_6$) δ 0.93-1.07 (m, 3H), 1.25-1.38 (m, 1H), 1.62-1.73 (m, 1H), 1.81-2.14 (m, 3H), 2.74-3.24 (m, 1H), 3.44-4.04 (m, 1H), 5.06-5.52 (m, 1H), 6.67-6.78 (m, 1H), 6.84-6.97 (m, 1H), 7.04-7.16 (m, 1H), 7.54-7.63 (m, 1H), 8.08-8.20 (m, 1H), 8.42-8.50 (m, 1H), 8.71-8.79 (m, 1H), 8.83-8.92 (m, 1H), 9.75-9.92 (m, 1H), 11.13-11.31 (m, 1H).

LCMS(ESI): [M+H]+ m/z: calcd 400.4; found 401.2; Rt=2.299 min.

Example 160. The Synthesis of 2-[(2R,5S)-2-(3-amino-1H-indazol-5-yl)-5-methyl-1-piperidyl]-N-(5,6-dimethyl-3-pyridyl)-2-oxo-acetamide (Compound 958) and 2-[(2S,5R)-2-(3-amino-1H-indazol-5-yl)-5-methyl-1-piperidyl]-N-(5,6-dimethyl-3-pyridyl)-2-oxo-acetamide (Compound 948

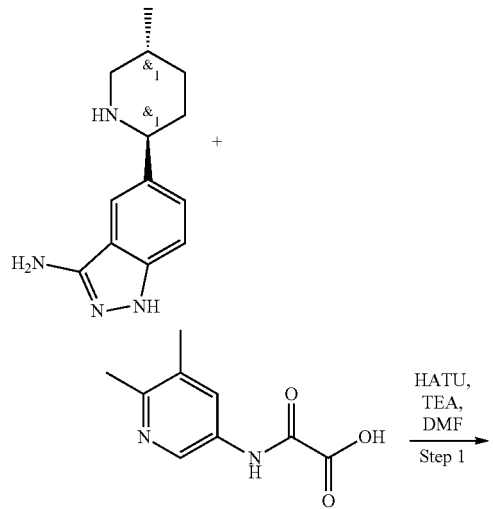

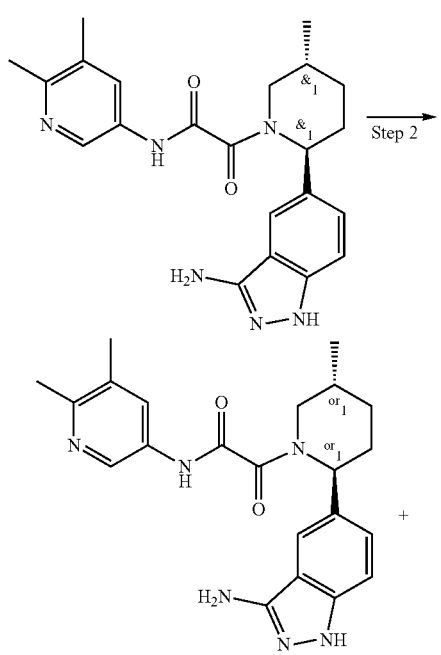

Compound 958

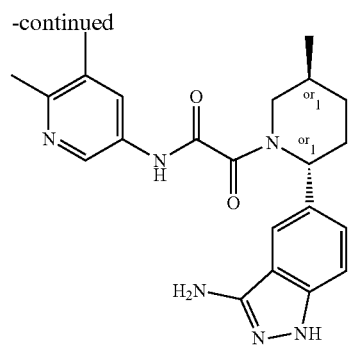

Compound 948

Step 1: Synthesis of 2-[(2R,5S)-2-(3-amino-1H-indazol-5-yl)-5-methyl-1-piperidyl]-N-(5,6-dimethyl-3-pyridyl)-2-oxo-acetamide 2-[(5,6-dimethyl-3-pyridyl)amino]-2-oxo-acetic acid (177.07 mg, 599.47 μmol, C6H15N) and 5-(5-methyl-2-piperidyl)-1H-indazol-3-amine (0.21 g, 911.82 μmol) were mixed in DMF (15 mL). The reaction suspension was cooled to 0° C. and HATU (381.37 mg, 1.00 mmol) followed by TEA (276.80 mg, 2.74 mmol, 381.27 μL) were added and stirred at ambient temperature for 14 hr. The reaction mixture was evaporated in vacuo and obtained crude product 0.31 g was purified by preparative 40-70% 0-5 min H2O/MeOH/0.1% NH4OH, flow: 30 ml/min to afford product 2-[(2R,5S)-2-(3-amino-1H-indazol-5-yl)-5-methyl-1-piperidyl]-N-(5,6-dimethyl-3-pyridyl)-2-oxo-acetamide (22.60 mg, 55.60 μmol, 6.10% yield).

LCMS(ESI): [M+H]+ m/z: calcd 406.2; found 407.0; Rt=1.599 min.

Step 2: The Synthesis of 2-[(2R,5S)-2-(3-amino-1H-indazol-5-yl)-5-methyl-1-piperidyl]-N-(5,6-dimethyl-3-pyridyl)-2-oxo-acetamide (Compound 958) and 2-[(2S,5R)-2-(3-amino-1H-indazol-5-yl)-5-methyl-1-piperidyl]-N-(5,6-dimethyl-3-pyridyl)-2-oxo-acetamide (Compound 948

The 2-[(2R,5S)-2-(3-amino-1H-indazol-5-yl)-5-methyl-1-piperidyl]-N-(5,6-dimethyl-3-pyridyl)-2-oxo-acetamide (0.0456 g, 112.18 μmol) was subjected to chiral HPLC purification (Column: IA-II (250*20.5 mkm), Eluent: Hexane-IPA-MeOH, 60-20-20, flow rate: 12 mL/min) to give the two individual enantiomers Compound 958 2-[(2R,5S)-2-(3-amino-1H-indazol-5-yl)-5-methyl-1-piperidyl]-N-(5,6-dimethyl-3-pyridyl)-2-oxo-acetamide (0.01055 g, 25.95 μmol, 23.14% yield) and Compound 948 2-[(2S,5R)-2-(3-amino-1H-indazol-5-yl)-5-methyl-1-piperidyl]-N-(5,6-dimethyl-3-pyridyl)-2-oxo-acetamide (0.01676 g, 41.23 μmol, 36.75% yield) Compound 958: 1H NMR (600 MHz, DMSO-d6) δ 0.97-1.06 (m, 3H), 1.30-1.40 (m, 1H), 1.79-1.93 (m, 2H), 2.01-2.28 (m, 5H), 2.31-2.37 (m, 3H), 2.75-3.24 (m, 1H), 3.41-4.02 (m, 1H), 5.13-5.69 (m, 3H), 7.09-7.20 (m, 1H), 7.20-7.26 (m, 1H), 7.68 (s, 1H), 7.73-7.85 (m, 1H), 8.37-8.55 (m, 1H), 10.82-10.92 (m, 1H), 11.28-11.36 (m, 1H).

LCMS(ESI): [M+H]+ m/z: calcd 406.2; found 407.2; Rt=0.762 min.

RT (Hexane-IPA-MeOH, 80-10-10, 0.6 ml/min)=31.4212 min.

Compound 948: $^1$H NMR (600 MHz, DMSO-$d_6$) δ 1.00-1.05 (m, 3H), 1.30-1.38 (m, 1H), 1.82-1.93 (m, 2H), 2.00-2.12 (m, 1H), 2.13-2.27 (m, 5H), 2.30-2.36 (m, 3H), 2.78-3.19 (m, 1H), 3.41-4.02 (m, 1H), 5.14-5.30 (m, 2H), 7.10-7.20 (m, 1H), 7.20-7.26 (m, 1H), 7.68 (s, 1H), 7.73-7.85 (m, 1H), 8.38-8.52 (m, 1H), 10.82-10.91 (m, 1H), 11.29-11.35 (m, 1H).

LCMS(ESI): [M+H]$^+$ m/z: calcd 406.2; found 407.2; Rt=0.692 min.

RT (Hexane-IPA-MeOH, 80-10-10, 0.6 ml/min)=36.6272 min.

Example 161. The Synthesis of N-(5,6-dimethyl-3-pyridyl)-2-[(2R,5S)-5-methyl-2-(4-methylsulfonylphenyl)-1-piperidyl]-2-oxo-acetamide (Compound 649

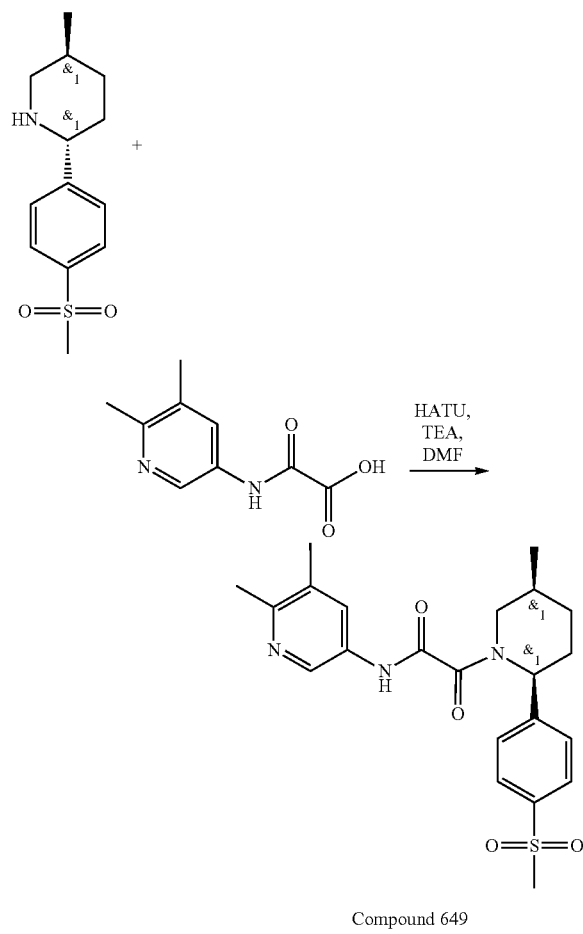

Compound 649

To a stirring solution of (2R,5S)-5-methyl-2-(4-methylsulfonylphenyl)piperidine (250 mg, 986.74 μmol), 2-[(5,6-dimethyl-3-pyridyl)amino]-2-oxo-acetic acid (291.46 mg, 986.74 μmol, N(C2H5)3) and triethyl amine (998.48 mg, 9.87 mmol, 1.38 mL) in DMF (5 mL) was added HATU (412.71 mg, 1.09 mmol) at 25° C. in small portions over 0.5 hr. The resulting reaction mixture was stirred at 25° C. for 18 hr. The crude reaction mixture was purified by reverse phase HPLC (column: SunFire C18 100×19 mm Sum, Mobile Phase: 15-40% 0-5 min water-methanol+FA, flow: 30 ml/min (loading pump 4 ml/min methanol)) to afford Compound 649 N-(5,6-dimethyl-3-pyridyl)-2-[(2R,5S)-5-methyl-2-(4-methylsulfonylphenyl)-1-piperidyl]-2-oxo-acetamide (87 mg, 202.55 μmol, 20.53% yield).

$^1$H NMR (DMSO-$d_6$, 600 MHz): δ (ppm) 1.01 (dd, 3H), 1.33 (m, 1H), 1.63 (m, 1H), 1.88 (m, 1H), 2.06 (m, 1H), 2.21 (m, 4H), 2.36 (m, 4H), 3.20 (m, 3H), 3.76 (m, 1H), 5.41 (m, 1H), 7.60 (m, 2H), 7.81 (m, 1H), 7.92 (m, 2H), 8.48 (m, 1H), 10.97 (m, 1H).

LCMS(ESI): [M+H]$^+$ m/z: calcd 429.2; found 430.2; Rt=1.962 min.

Example 162. The Synthesis of Rac 5-[[2-[(2S,5R)-5-methyl-2-(4-Sulfamoylphenyl)-1-piperidyl]-2-oxo-acetyl]amino]pyridine-3-carboxamide (Compound 651), 5-[[2-[(2S,5R)-5-methyl-2-(4-Sulfamoylphenyl)-1-piperidyl]-2-oxo-acetyl]amino]pyridine-3-carboxamide (Compound 725) and 5-[[2-[(2R,5S)-5-methyl-2-(4-Sulfamoylphenyl)-1-piperidyl]-2-oxo-acetyl]amino]pyridine-3-carboxamide (Compound 724

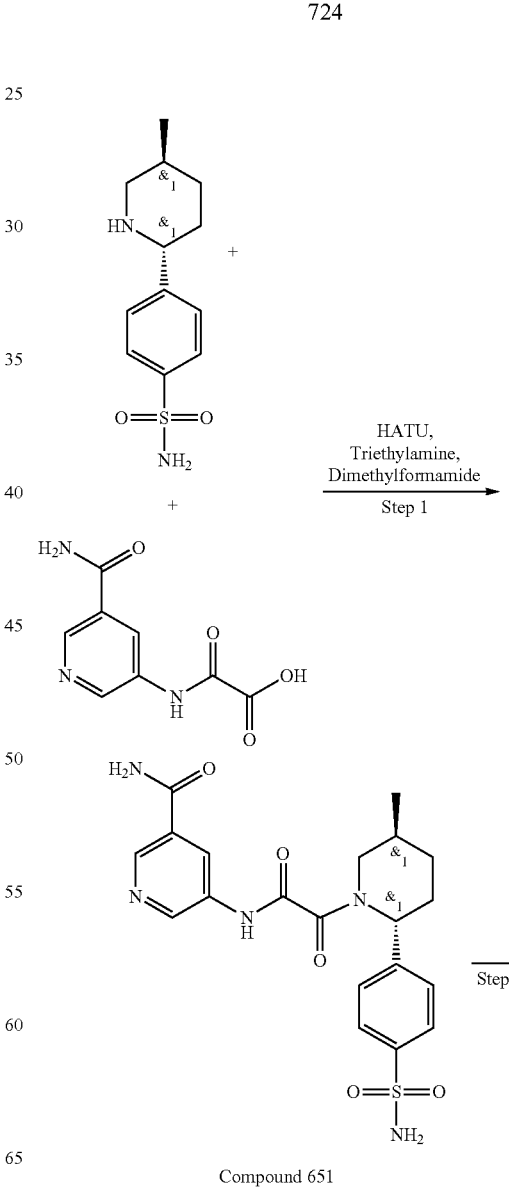

Compound 651

1545

-continued

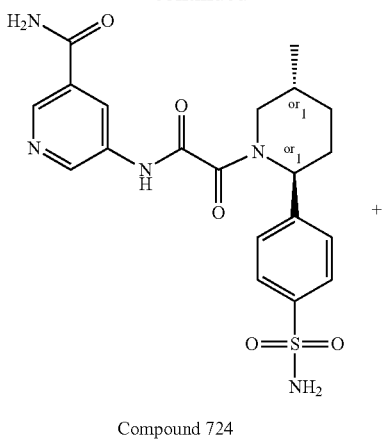

Compound 724

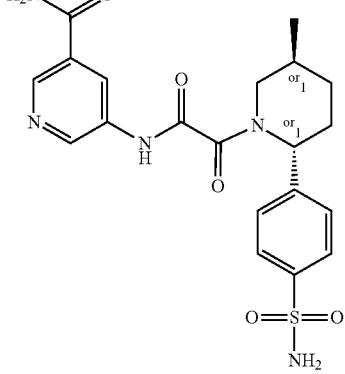

Compound 725

Step 1: The Synthesis of 5-[[2-[(2S,5R)-5-methyl-2-(4-Sulfamoylphenyl)-1-piperidyl]-2-oxo-acetyl]amino]pyridine-3-carboxamide (Compound 651

To a stirred mixture of 4-(5-methyl-2-piperidyl)benzenesulfonamide (350 mg, 1.20 mmol, HCl), 2-[(5-carbamoyl-3-pyridyl)amino]-2-oxo-acetic acid (295.61 mg, 1.20 mmol, HCl) and Triethylamine (608.93 mg, 6.02 mmol, 838.75 μL) in Dimethylformamide (4 mL) was added HATU (503.38 mg, 1.32 mmol). The resulting reaction mixture was stirred at 20° C. for 5 hr. Then, it was subjected to HPLC (Column: YMC Triart C18 100×20 mm, 5 um; 10-10-40% 0-2-6 min 0.1% NH$_3$-methanol, flow: 30 ml/min—1st run, and 30-30-65% 0-1-5 min 0.2% FA-methanol, flow: 30 ml/min; 2-nd run), affording 5-[[2-[(2S,5R)-5-methyl-2-(4-sulfamoylphenyl)-1-piperidyl]-2-oxo-acetyl]amino]pyridine-3-carboxamide (57 mg, 127.95 μmol, 10.63% yield).

$^1$H NMR (DMSO-d$_6$, 600 MHz): δ (ppm) 1.01 (dd, 3H), 1.35 (m, 1H), 1.62 (m, 1H), 1.93 (m, 1H), 2.19 (m, 3H), 3.79 (m, 1H), 5.42 (m, 1H), 7.32 (m, 2H), 7.52 (m, 2H), 7.59 (m, 1H), 7.82 (m, 2H), 8.14 (m, 1H), 8.47 (m, 1H), 8.76 (m, 1H), 8.90 (m, 1H), 11.23 (m, 1H)

LCMS(ESI): [M+H]$^+$ m/z: calcd 445.2; found 446.2; Rt=1.855 min.

1546

Step 2: The Synthesis of 5-[[2-[(2S,5R)-5-methyl-2-(4-Sulfamoylphenyl)-1-piperidyl]-2-oxo-acetyl]amino]pyridine-3-carboxamide (Compound 725) and 5-[[2-[(2R,5S)-5-methyl-2-(4-Sulfamoylphenyl)-1-piperidyl]-2-oxo-acetyl]amino]pyridine-3-carboxamide (Compound 724

5-[[2-[(2R,5S)-5-methyl-2-(4-sulfamoylphenyl)-1-piperidyl]-2-oxo-acetyl]amino]pyridine-3-carboxamide (47.0 mg, 105.50 μmol) was chirally separated using IB (250*20, 5 mkm) Chiralpak column, Hexane-IPA-MeOH, 70-15-15 as a mobile phase, Flow rate 12 ml/min affording Compound 724—5-[[2-[(2R,5S)-5-methyl-2-(4-sulfamoylphenyl)-1-piperidyl]-2-oxo-acetyl]amino]pyridine-3-carboxamide (22.43 mg, 50.35 μmol, 47.72% yield) (RT=58.148 min) as beige solid and Compound 725—5-[[2-[(2S,5R)-5-methyl-2-(4-sulfamoylphenyl)-1-piperidyl]-2-oxo-acetyl]amino]pyridine-3-carboxamide (20.4 mg, 45.79 μmol, 43.40% yield) (RT=39.671 min) as beige solid.

Compound 724: (IB, Hexane-IPA-MeOH, 70-15-15, 0.6 ml/min)=72.148 min

Compound 725: (IB, Hexane-IPA-MeOH, 70-15-15, 0.6 ml/min)=51.595 min

Compound 725: $^1$H NMR (DMSO-d$_6$, 600 MHz): δ (ppm) 1.02 (m, 3H), 1.34 (m, 1H), 1.64 (m, 1H), 1.89 (m, 1H), 2.17 (m, 2H), 2.77 (m, 1H), 3.79 (m, 1H), 5.42 (m, 1H), 7.32 (m, 2H), 7.55 (m, 3H), 7.82 (m, 2H), 8.14 (m, 1H), 8.47 (m, 1H), 8.75 (m, 1H), 8.87 (m, 1H), 11.24 (m, 1H)

LCMS(ESI): [M+H]$^+$ m/z: calcd 445.2; found 446.2; Rt=0.785 min.

RT (Hexane-IPA-MeOH, 70-15-15, 0.6 ml/min)=51.622 min.

Compound 724: $^1$H NMR (DMSO-d$_6$, 600 MHz): δ (ppm) 1.00 (m, 3H), 1.34 (m, 1H), 1.61 (m, 1H), 1.89 (m, 1H), 2.17 (m, 2H), 2.79 (m, 1H), 3.79 (m, 1H), 5.42 (m, 1H), 7.32 (m, 2H), 7.54 (m, 3H), 7.82 (m, 2H), 8.14 (m, 1H), 8.47 (m, 1H), 8.77 (m, 1H), 8.87 (m, 1H), 11.22 (m, 1H)

LCMS(ESI): [M+H]$^+$ m/z: calcd 445.2; found 446.2; Rt=0.785 min.

RT (Hexane-IPA-MeOH, 70-15-15, 0.6 ml/min)=72.1842 min.

Example 163. The Synthesis of Rac 5-[[2-[(2S,5R)-5-methyl-2-[4-(methylsulfamoyl)phenyl]-1-piperidyl]-2-oxo-acetyl]amino]pyridine-3-carboxamide (Compound 652), 5-[[2-[(2R,5S)-5-methyl-2-[4-(methylsulfamoyl)phenyl]-1-piperidyl]-2-oxo-acetyl]amino]pyridine-3-carboxamide (Compound 722) and 5-[[2-[(2S,5R)-5-methyl-2-[4-(methylsulfamoyl)phenyl]-1-piperidyl]-2-oxo-acetyl]amino]pyridine-3-carboxamide (Compound 723

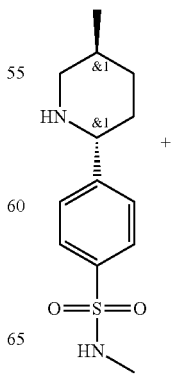

-continued

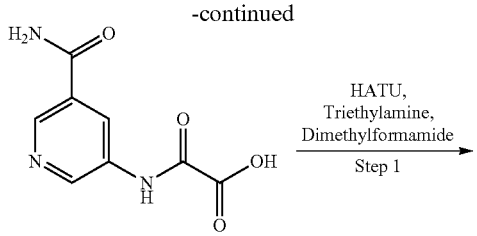

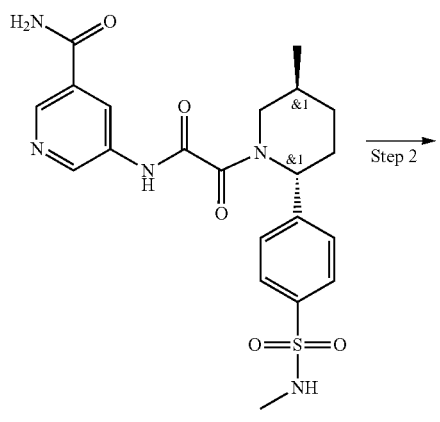

Compound 652

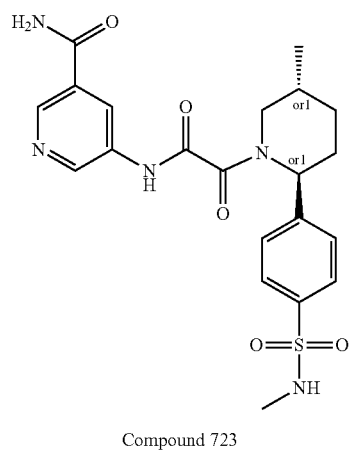

Compound 723

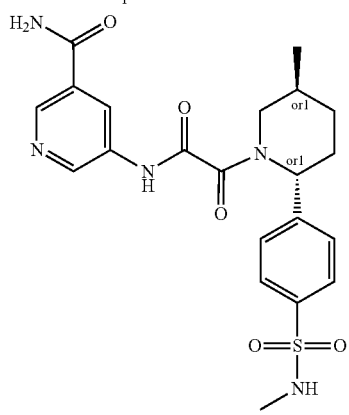

Compound 722

Step 1: Synthesis of Rac 5-[[2-[(2S,5R)-5-methyl-2-[4-(methylsulfamoyl)phenyl]-1-piperidyl]-2-oxo-acetyl]amino]pyridine-3-carboxamide (Compound 652

To a stirred mixture of N-methyl-4-(5-methyl-2-piperidyl)benzenesulfonamide (370 mg, 1.38 mmol, HCl), 2-[(5-carbamoyl-3-pyridyl)amino]-2-oxo-acetic acid (338.63 mg, 1.38 mmol, HCl) and Triethylamine (697.54 mg, 6.89 mmol, 960.80 µL) in Dimethylformamide (4 mL) was added HATU (576.63 mg, 1.52 mmol). The resulting reaction mixture was stirred at 20° C. for 5 hr. Then, it was subjected to HPLC (Column: YMC Triart C18 100×20 mm, 5 um; 10-10-60% 0-1-6 min 0.1% $NH_3$-methanol, flow: 30 ml/min), affording 5-[[2-[(2S,5R)-5-methyl-2-[4-(methylsulfamoyl)phenyl]-1-piperidyl]-2-oxo-acetyl]amino]pyridine-3-carboxamide (130 mg, 282.91 µmol, 20.52% yield).

$^1$H NMR (DMSO-$d_6$, 600 MHz): δ (ppm) 1.02 (m, 3H), 1.34 (m, 1H), 1.64 (m, 1H), 1.89 (m, 1H), 2.20 (m, 3H), 2.37 (m, 3H), 3.78 (m, 1H), 5.60 (m, 1H), 7.42 (m, 1H), 7.56 (m, 3H), 7.77 (m, 2H), 8.13 (m, 1H), 8.45 (m, 1H), 8.74 (m, 1H), 8.86 (m, 1H), 11.22 (s, 1H)

LCMS(ESI): [M+H]$^+$ m/z: calcd 459.2; found 460.2; Rt=2.096 min.

Step 2: The Synthesis of 5-[[2-[(2R,5S)-5-methyl-2-[4-(methylsulfamoyl)phenyl]-1-piperidyl]-2-oxo-acetyl]amino]pyridine-3-carboxamide (Compound 722) and 5-[[2-[(2S,5R)-5-methyl-2-[4-(methylsulfamoyl)phenyl]-1-piperidyl]-2-oxo-acetyl]amino]pyridine-3-carboxamide (Compound 723)

5-[[2-[(2S,5R)-5-methyl-2-[4-(methylsulfamoyl)phenyl]-1-piperidyl]-2-oxo-acetyl]amino]pyridine-3-carboxamide (120.00 mg, 261.14 µmol) was divided into enantiomers by Chiral HPLC (Column: Chiralpak IA II(250*20 mm, 5 mkm); Mobile phase: Hexane-IPA-MeOH 40-30-30 Flow Rate: 12 mL/min; m=0.12 g, 2 injections, 60 mg/ing., V=2.5 L, time=3 h.), affording: 5-[[2-[(2S,5R)-5-methyl-2-[4-(methylsulfamoyl)phenyl]-1-piperidyl]-2-oxo-acetyl]amino]pyridine-3-carboxamide (33 mg, 71.81 µmol, 55.00% yield), with ret.time=19.304 min(Compound 723) and 5-[[2-[(2R,5S)-5-methyl-2-[4-(methylsulfamoyl)phenyl]-1-piperidyl]-2-oxo-acetyl]amino]pyridine-3-carboxamide (30 mg, 65.29 µmol, 50.00% yield), with ret.time=42.724 min (Compound 722

Compound 722: $^1$H NMR (DMSO-$d_6$, 600 MHz): δ (ppm) 1.02 (m, 3H), 1.34 (m, 1H), 1.64 (m, 1H), 1.89 (m, 1H), 2.10 (m, 1H), 2.23 (m, 1H), 2.38 (m, 3H), 2.77 (m, 1H), 3.69 (m, 1H), 5.43 (m, 1H), 7.42 (m, 1H), 7.56 (m, 3H), 7.77 (m, 2H), 8.14 (m, 1H), 8.46 (m, 1H), 8.75 (m, 1H), 8.86 (m, 1H), 11.25 (m, 1H)

LCMS(ESI): [M+H]$^+$ m/z: calcd 459.2; found 460.2; Rt=2.059 min.

RT (IPA-MeOH, 50-50, 0.6 ml/min)=18.2272 min.

Compound 723: $^1$H NMR (DMSO-$d_6$, 600 MHz): δ (ppm) 1.02 (m, 3H), 1.34 (m, 1H), 1.64 (m, 1H), 1.89 (m, 1H), 2.15 (m, 2H), 2.38 (m, 3H), 2.91 (m, 1H), 3.78 (m, 1H), 5.43 (m, 1H), 7.42 (m, 1H), 7.56 (m, 3H), 7.77 (m, 2H), 8.14 (m, 1H), 8.46 (d, 1H), 8.75 (m, 1H), 8.87 (m, 1H), 11.23 (m, 1H)

LCMS(ESI): [M+H]$^+$ m/z: calcd 459.2; found 460.2; Rt=2.059 min.

RT (IPA-MeOH, 50-50, 0.6 ml/min)=11.0232 min.

Example 164. The Synthesis of 5-[[2-[(2S,5S)-3,3-difluoro-2-(4-fluorophenyl)-5-methyl-1-piperidyl]-2-oxo-acetyl]amino]pyridine-3-carboxamide (Compound 836

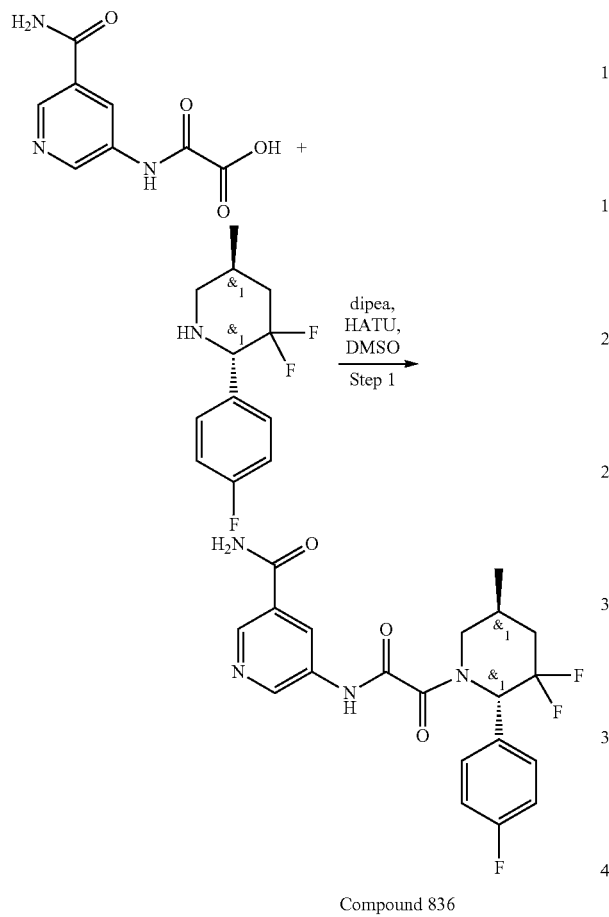

Compound 836

2-[(5-carbamoyl-3-pyridyl)amino]-2-oxo-acetic acid (203.76 mg, 974.21 µmol), (2S,5S)-3,3-difluoro-2-(4-fluorophenyl)-5-methyl-piperidine (223.33 mg, 974.21 µmol) and dipea (377.73 mg, 2.92 mmol, 509.07 µL) were dissolved in DMSO (6 mL) under gentle heating. HATU (444.51 mg, 1.17 mmol) was added in small portions under vigorous stirring and occasional heating. After the reaction was complete, the mixture was purified by HPLC to give 5-[[2-[(2S,5S)-3,3-difluoro-2-(4-fluorophenyl)-5-methyl-1-piperidyl]-2-oxo-acetyl]amino]pyridine-3-carboxamide (35 mg, 83.26 µmol, 8.55% yield)

HPLC conditions: (23% 0.5-6.5 min water-acetonitrile; flow 30 ml/min; (loading pump 4 ml/min acetonitrile); target mass 420; column SunFire C18 100×19 mm 5 um (L))

$^1$H NMR (600 MHz, DMSO-$d_6$) δ 1.04-1.09 (m, 3H), 1.90-2.01 (m, 1H), 2.20-2.27 (m, 1H), 2.37-2.46 (m, 1H), 3.38-3.54 (m, 1H), 3.58-4.05 (m, 1H), 5.58-5.78 (m, 1H), 7.15-7.29 (m, 2H), 7.44-7.53 (m, 2H), 7.60 (s, 1H), 8.15 (s, 1H), 8.47 (s, 1H), 8.77 (s, 1H), 8.80-8.91 (m, 1H), 11.11-11.34 (m, 1H).

LCMS(ESI): [M+H]$^+$ m/z: calcd 420.2; found 421.2; Rt=2.607 min.

Example 0.165. The Synthesis of 5-[[2-[(2R,3R,5R)-3-fluoro-2-(4-fluorophenyl)-5-methyl-1-piperidyl]-2-oxo-acetyl]amino]pyridine-3-carboxamide (Compound 898) and 5-[[2-[(2R,3S,5R)-3-fluoro-2-(4-fluorophenyl)-5-methyl-1-piperidyl]-2-oxo-acetyl]amino]pyridine-3-carboxamide (Compound 879

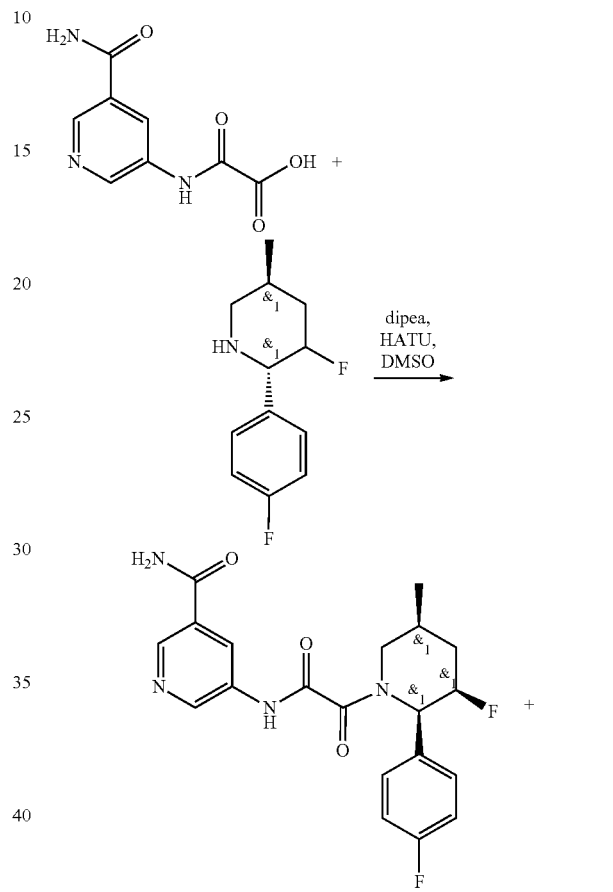

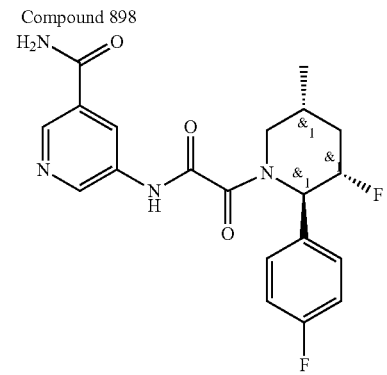

Compound 879

2-[(5-carbamoyl-3-pyridyl)amino]-2-oxo-acetic acid (203.76 mg, 974.21 µmol), (2S,5S)-3-fluoro-2-(4-fluorophenyl)-5-methyl-piperidine (205.80 mg, 974.21 µmol) and dipea (377.73 mg, 2.92 mmol, 509.07 µL) were dissolved in DMSO (6 mL) under gentle heating. HATU (444.51 mg, 1.17 mmol) was added in small portions under vigorous stirring and occasional heating. After the reaction was complete, the mixture was purified by HPLC to give 5-[[2-[(2R,3R,5R)-3-fluoro-2-(4-fluorophenyl)-5-methyl-1-piperidyl]-2-oxo-acetyl]amino]pyridine-3-carboxamide (130 mg, 323.07 μmol, 33.16% yield) and second isomer, which was repurificated (16-18% 0.5-7 min water-acetonitrile+NH₃; flow 30 ml/min (loading pump 4 ml/min acetonitrile); target mass 200; column XBridge 100×19 mm Sum) to give 5-[[2-[(2R,3S,5R)-3-fluoro-2-(4-fluorophenyl)-5-methyl-1-piperidyl]-2-oxo-acetyl]amino]pyridine-3-carboxamide (15 mg, 37.28 μmol, 3.83% yield)

HPLC conditions: 19-23% 0.5-6 min water-acetonitrile; flow 30 ml/min; (loading pump 4 ml/min acetonitrile); target mass 402; column SunFire C18 100×19 mm 5 um (L))

Compound 879: $^1$H NMR (DMSO-$d_6$, 600 MHz): δ (ppm) 1.07 (m, 3H), 1.73 (m, 1H), 1.89 (m, 2H), 3.36 (m, 1H), 3.71 (m, 1H), 5.59 (m, 2H), 7.23 (m, 2H), 7.42 (m, 2H), 7.58 (m, 1H), 8.14 (m, 1H), 8.49 (m, 1H), 8.75 (m, 1H), 8.87 (m, 1H), 11.28 (m, 1H)

LCMS(ESI): [M+H]$^+$ m/z: calcd 402.2; found 403.2; Rt=2.565 min.

Compound 898: $^1$H NMR (DMSO-$d_6$, 600 MHz): δ (ppm) 1.03 (d, 3H), 1.36 (m, 1H), 2.20 (m, 2H), 3.63 (m, 2H), 5.34 (m, 2H), 7.20 (m, 2H), 7.36 (m, 2H), 7.59 (m, 1H), 8.13 (m, 1H), 8.40 (m, 1H), 8.79 (m, 2H), 11.09 (m, 1H).

LCMS(ESI): [M+H]$^+$ m/z: calcd 402.2; found 403.0; Rt=2.

Example 166. The Synthesis of 5-[[2-[(2S,5R)-5-methyl-2-(1H-pyrazol-4-yl)-1-piperidyl]-2-oxo-acetyl]amino]pyridine-3-carboxamide (Compound 970) and 5-[[2-[(2R,5S)-5-methyl-2-(1H-pyrazol-4-yl)-1-piperidyl]-2-oxo-acetyl]amino]pyridine-3-carboxamide (Compound 942

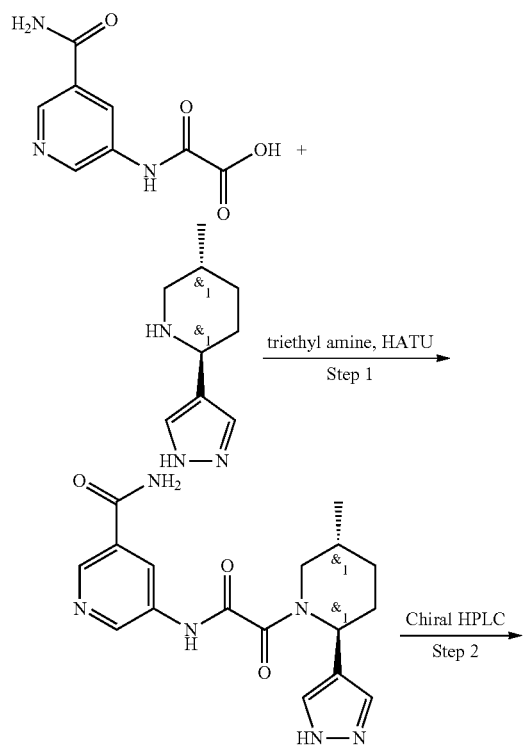

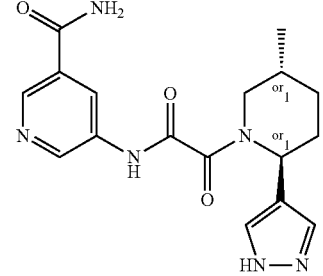

Compound 970

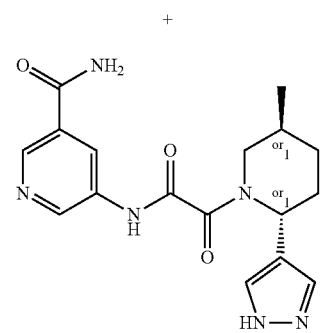

Compound 942

Step 1. 5-[[2-[(2R,5S)-5-methyl-2-(1H-pyrazol-4-yl)-1-piperidyl]-2-oxo-acetyl]amino]pyridine-3-carboxamide HATU (702.48 mg, 1.85 mmol) was added in small portions over 1.5 hr period to a stirred mixture of (2R,5S)-5-methyl-2-(1H-pyrazol-4-yl)piperidine (400 mg, 1.68 mmol, 2HCl), 2-[(5-carbamoyl-3-pyridyl)amino]-2-oxo-acetic acid (474.41 mg, 1.93 mmol, HCl) and triethyl amine (1.36 g, 13.44 mmol, 1.87 mL) in DMF (6 mL) at 25° C. The resulting mixture was stirred at 25° C. for 18 hr, and then submitted to reverse phase HPLC (column: YMC Triart C18 100×20 mm, 5 um; mobile phase: 10-50% 0-5 min H₂O/MeOH/0.1% NH₄OH, flow rate: 30 ml/min (loading pump 4 ml/min methanol) to afford 5-[[2-[(2R,5S)-5-methyl-2-(1H-pyrazol-4-yl)-1-piperidyl]-2-oxo-acetyl]amino]pyridine-3-carboxamide (173 mg, 485.44 μmol, 28.90% yield) as light-yellow gum, which was directly submitted to preparative chiral HPLC.

LCMS(ESI): [M+1]$^+$ m/z: calcd 356.2; found 357.2; Rt=1.525 min.

Step 2. The Synthesis of 5-[[2-[(2S,5R)-5-methyl-2-(1H-pyrazol-4-yl)-1-piperidyl]-2-oxo-acetyl]amino]pyridine-3-carboxamide (Compound 970) and 5-[[2-[(2R,5S)-5-methyl-2-(1H-pyrazol-4-yl)-1-piperidyl]-2-oxo-acetyl]amino]pyridine-3-carboxamide (Compound 942

Racemic 5-[[2-[(2R,5S)-5-methyl-2-(1H-pyrazol-4-yl)-1-piperidyl]-2-oxo-acetyl]amino]pyridine-3-carboxamide (173 mg, 485.44 μmol) was submitted to preparative chiral HPLC (Column: Chiralpak AD-H—III(250*20 mm, 5 mkm); Mobile phase:Hexane-IPA-MeOH 60-20-20; Flow Rate: 12 mL/min) to afford Compound 970 5-[[2-[(2S,5R)-5-methyl-2-(1H-pyrazol-4-yl)-1-piperidyl]-2-oxo-acetyl]amino]pyridine-3-carboxamide (73 mg, 204.84 μmol, 42.20% yield) (R.T.=23.439 min.), and Compound 942 5-[[2-[(2R,5S)-5-methyl-2-(1H-pyrazol-4-yl)-1-piperidyl]-2-oxo-acetyl]amino]pyridine-3-carboxamide (72 mg, 202.03 μmol, 41.62% yield) (R.T.=32.685 min.).

Compound 970 1H NMR (600 MHz, DMSO-$d_6$) δ 0.96-1.01 (m, 3H), 1.30-1.43 (m, 1H), 1.74-1.89 (m, 2H), 1.90-2.02 (m, 2H), 2.79-3.27 (m, 1H), 3.34-3.97 (m, 1H), 5.02-5.63 (m, 1H), 7.35-7.77 (m, 3H), 8.10-8.21 (m, 1H), 8.43-8.52 (m, 1H), 8.72-8.79 (m, 1H), 8.84-8.91 (m, 1H), 11.08-11.21 (m, 1H), 12.77 (s, 1H).

LCMS(ESI): [M+1]$^+$ m/z: calcd 356.2; found 357.4; Rt=1.589 min.

Compound 942 1H NMR (600 MHz, DMSO-$d_6$) δ 0.96-1.01 (m, 3H), 1.30-1.43 (m, 1H), 1.74-1.89 (m, 2H), 1.90-2.02 (m, 2H), 2.79-3.27 (m, 1H), 3.34-3.97 (m, 1H), 5.02-5.63 (m, 1H), 7.35-7.77 (m, 3H), 8.10-8.21 (m, 1H), 8.43-8.52 (m, 1H), 8.72-8.79 (m, 1H), 8.84-8.91 (m, 1H), 11.08-11.21 (m, 1H), 12.77 (s, 1H).

LCMS(ESI): [M+1]$^+$ m/z: calcd 356.2; found 357.2; Rt=1.584 min.

Example 167. The Synthesis of 5-[[2-[(2S,5R)-2-(5-amino-2-pyridyl)-5-methyl-1-piperidyl]-2-oxo-acetyl]amino]pyridine-3-carboxamide (Compound 607) and 5-[[2-[(2R,5S)-2-(5-amino-2-pyridyl)-5-methyl-1-piperidyl]-2-oxo-acetyl]amino]pyridine-3-carboxamide (Compound 594

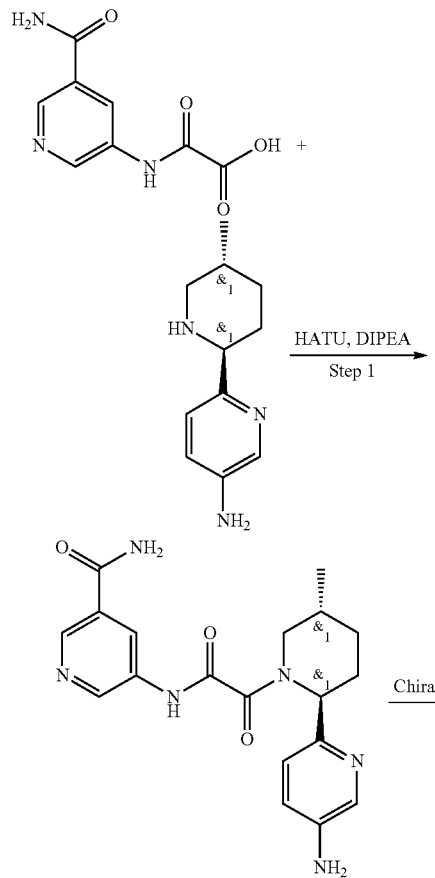

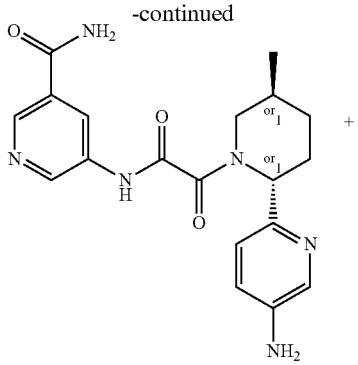

Compound 594

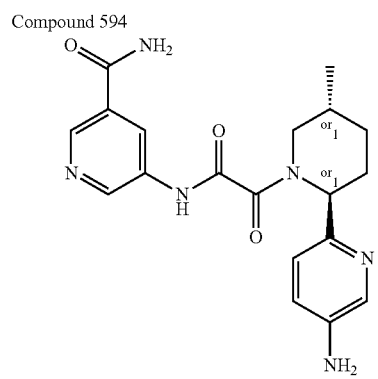

Compound 607

Step 1. Tert-butyl (2R,5S)-5-methyl-2-[1-(1H-pyrazol-3-yl)pyrazol-4-yl]piperidine DIPEA (260.15 mg, 2.01 mmol, 350.60 μL) was added to the solution of respective 2-[(5-carbamoyl-3-pyridyl)amino]-2-oxo-acetic acid (120.29 mg, 489.73 μmol, HCl) and 6-(5-methyl-2-piperidyl)pyridin-3-amine (0.11 g, 575.10 μmol) in DMF (5 mL). The resulting mixture was stirred for 5 min followed by the addition of HATU (240.54 mg, 632.61 μmol). Then, the reaction mixture was stirred overnight at room temperature. After the completion of the reaction, monitored by LCMS, the resulting suspension was concentrated under reduced pressure. The obtained solid was subjected to HPLC to afford pure 5-[[2-[2-(5-amino-2-pyridyl)-5-methyl-1-piperidyl]-2-oxo-acetyl]amino]pyridine-3-carboxamide (69.4 mg, 181.48 μmol, 31.56% yield) with cis-impurity.

LCMS(ESI): [M+1]$^+$ m/z: calcd 382.2; found 383.2; Rt=1.322 min.

Step 2. The Synthesis of 5-[[2-[(2S,5R)-2-(5-amino-2-pyridyl)-5-methyl-1-piperidyl]-2-oxo-acetyl]amino]pyridine-3-carboxamide (Compound 607) and 5-[[2-[(2R,5S)-2-(5-amino-2-pyridyl)-5-methyl-1-piperidyl]-2-oxo-acetyl]amino]pyridine-3-carboxamide (Compound 594)

The racemate was separated in the following conditions OJ-H (250*30, 5 mkm), Hexane-IPA-MeOH, 50-25-25, 13 ml/min, RT(Compound 607)=10.557 min, RT(Compound 594)=20.873 min. From 69 mg of racemate, 17.8 mg (Compound 607) and 4.96 mg (Compound 594) of enantiomers were obtained.

Analytical data are recorded in the following conditions—Instrument:Reverse Phase & Gradient:

Hexane-IPA-MeOH, 60-20-20, 0.6 ml/min, Column: OD-H

Rel.Time for Compound 594 in analytical conditions 20.10 min

Rel.Time for Compound 607 in analytical conditions 35.91 min

Compound 594: $^1$H NMR (600 MHz, DMSO-$d_6$) δ 0.68-0.83 (m, 3H), 1.02-1.18 (m, 1H), 1.37-1.67 (m, 2H), 1.67-1.85 (m, 1H), 2.11-2.36 (m, 1H), 2.66-3.28 (m, 1H), 3.57-4.22 (m, 1H), 5.00-5.57 (m, 3H), 6.88-7.10 (m, 2H), 7.53-7.63 (m, 1H), 7.87-7.95 (m, 1H), 8.08-8.19 (m, 1H), 8.44-8.54 (m, 1H), 8.70-8.79 (m, 1H), 8.79-8.91 (m, 1H), 11.09-11.37 (m, 1H).

LCMS(ESI): [M+1]$^+$ m/z: calcd 382.4; found 383.2; Rt=3,825 min.

Compound 607: $^1$H NMR (600 MHz, DMSO-$d_6$) δ 0.69-0.84 (m, 3H), 1.07-1.15 (m, 1H), 1.52-1.68 (m, 2H), 1.68-1.84 (m, 1H), 2.15-2.21 (m, 0.5H), 2.58-2.73 (m, 1.5H), 3.57-4.22 (m, 1H), 5.01-5.55 (m, 3H), 6.88-7.08 (m, 2H), 7.51-7.66 (m, 1H), 7.86-7.93 (m, 1H), 8.09-8.19 (m, 1H), 8.43-8.55 (m, 1H), 8.67-8.79 (m, 1H), 8.79-8.94 (m, 1H), 11.05-11.28 (m, 1H).

LCMS(ESI): [M+1]$^+$ m/z: calcd 382.4; found 383.2; Rt=3,742 min.

Example 168. The Synthesis of 5-[[2-[5-methyl-2-(2-pyridyl)-1-piperidyl]-2-oxo-acetyl]amino]pyridine-3-carboxamide and 5-[[2-[(2R,5R)-5-methyl-2-(2-pyridyl)-1-piperidyl]-2-oxo-acetyl]amino]pyridine-3-carboxamide (Compound 584), 5-[[2-[(2R,5S)-5-methyl-2-(2-pyridyl)-1-piperidyl]-2-oxo-acetyl]amino]pyridine-3-carboxamide (Compound 590) and 5-[[2-[(2S,5R)-5-methyl-2-(2-pyridyl)-1-piperidyl]-2-oxo-acetyl]amino]pyridine-3-carboxamide (Compound 578

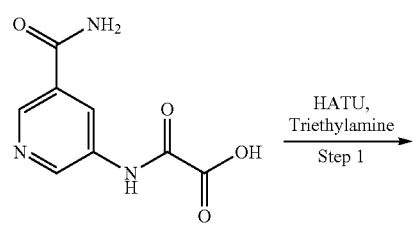

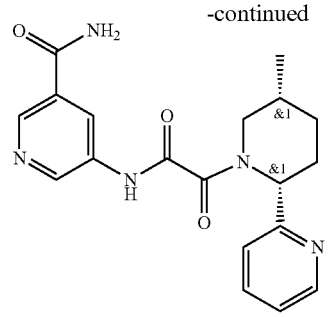

Compound 584

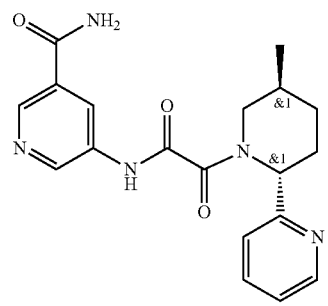

Compound 590

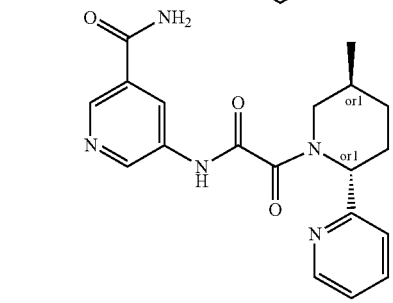

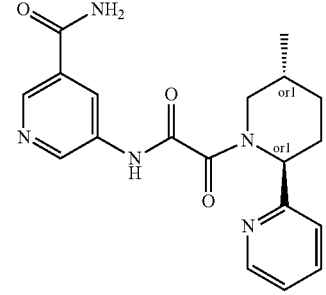

Compound 578

Step 1. Synthesis of 5-[[2-[5-methyl-2-(2-pyridyl)-1-piperidyl]-2-oxo-acetyl]amino]pyridine-3-carboxamide and 5-[[2-[(2R,5R)-5-methyl-2-(2-pyridyl)-1-piperidyl]-2-oxo-acetyl]amino]pyridine-3-carboxamide (Compound 584

2-(5-methyl-2-piperidyl)pyridine (0.5 g, 2.35 mmol, HCl) was dissolved in DMF (8 mL) and Triethylamine (2.38 g, 23.51 mmol, 3.28 mL) was added, followed by 2-[(5-carbamoyl-3-pyridyl)amino]-2-oxo-acetic acid (491.63 mg, 2.00 mmol, HCl). Then the HATU (1.34 g, 3.53 mmol) was added dropwise and the reaction mixture was stirred overnight. The next day it was evaporated in vacuo and purified by HPLC to obtain 5-[[2-[5-methyl-2-(2-pyridyl)-1-piperidyl]-2-oxo-acetyl]amino]pyridine-3-carboxamide (0.1135 g, 308.93 µmol, 13.14% yield) and 5-[[2-[(2R,5R)-5-methyl-2-(2-pyridyl)-1-piperidyl]-2-oxo-acetyl]amino]pyridine-3-carboxamide (86.47 mg, 235.36 µmol, 53.05% yield)

LCMS(ESI): [M+1]+ m/z: calcd 367.2; found 368.2; Rt=1.758 min. (trans-)

Compound 584

¹H NMR (600 MHz, DMSO-d₆) δ 0.72-0.83 (m, 3H), 0.98-1.08 (m, 1H), 1.59-1.73 (m, 2H), 1.78-1.95 (m, 1H), 2.25-2.30 (m, OH), 2.63-2.80 (m, 2H), 3.66-4.28 (m, 1H), 5.45 (dd, 1H), 7.25-7.31 (m, 1H), 7.31-7.43 (m, 1H), 7.54-7.65 (m, 1H), 7.77-7.89 (m, 1H), 8.09-8.21 (m, 1H), 8.42-8.54 (m, 1H), 8.54-8.62 (m, 1H), 8.69-8.80 (m, 1H), 8.80-8.94 (m, 1H), 11.11-11.39 (m, 1H).

LCMS(ESI): [M+1]+ m/z: calcd 367.2; found 368.2; Rt=1.876 min. (cis-)

Step 2. Synthesis of 5-[[2-[(2R,5S)-5-methyl-2-(2-pyridyl)-1-piperidyl]-2-oxo-acetyl]amino]pyridine-3-carboxamide (Compound 590) and 5-[[2-[(2S,5R)-5-methyl-2-(2-pyridyl)-1-piperidyl]-2-oxo-acetyl]amino]pyridine-3-carboxamide (Compound 578

5-[[2-[5-methyl-2-(2-pyridyl)-1-piperidyl]-2-oxo-acetyl]amino]pyridine-3-carboxamide (0.1135 g, 308.93 µmol) was chiral separated (Column: YMC CHIRAL ART Cellulose-SC 250*20, 5 Hexane-IPA-MeOH, 50-25-25, 13 ml/min RetTime (Compound 578)=19.244 min and RetTime (Compound 578)=29.63 min) to obtain 5-[[2-[(2S,5R)-5-methyl-2-(2-pyridyl)-1-piperidyl]-2-oxo-acetyl]amino]pyridine-3-carboxamide (0.047 g, 127.93 µmol, 41.41% yield) and 5-[[2-[(2R,5S)-5-methyl-2-(2-pyridyl)-1-piperidyl]-2-oxo-acetyl]amino]pyridine-3-carboxamide (0.046 g, 125.20 µmol, 40.53% yield)

Compound 590:

¹H NMR (600 MHz, DMSO-d₆) δ 1.01-1.04 (m, 3H), 1.29-1.37 (m, 1H), 1.58-1.65 (m, 1H), 1.83-1.94 (m, 1H), 1.94-2.04 (m, 1H), 2.04-2.14 (m, 1H), 2.85-3.40 (m, 1H), 3.51-4.08 (m, 1H), 5.21-5.61 (m, 1H), 7.23-7.44 (m, 2H), 7.49-7.64 (m, 1H), 7.74-7.87 (m, 1H), 8.05-8.22 (m, 1H), 8.39-8.52 (m, 1H), 8.53-8.61 (m, 1H), 8.68-8.79 (m, 1H), 8.79-8.93 (m, 1H), 11.05-11.34 (m, 1H).

LCMS(ESI): [M+1]+ m/z: calcd 367.2; found 368.2; Rt=1.758 min.

Compound 578:

¹H NMR (600 MHz, DMSO-d₆) δ 1.02-1.05 (m, 3H), 1.26-1.38 (m, 1H), 1.56-1.69 (m, 1H), 1.81-1.95 (m, 1H), 1.95-2.13 (m, 1H), 2.41-2.44 (m, 1H), 2.85-3.39 (m, 1H), 3.44-4.14 (m, 1H), 5.21-5.61 (m, 1H), 7.22-7.31 (m, 1H), 7.31-7.46 (m, 1H), 7.51-7.65 (m, 1H), 7.75-7.87 (m, 1H), 8.05-8.20 (m, 1H), 8.42-8.50 (m, 1H), 8.53-8.61 (m, 1H), 8.69-8.80 (m, 1H), 8.81-8.92 (m, 1H), 11.07-11.28 (m, 1H).

LCMS(ESI): [M+1]+ m/z: calcd 367.2; found 368.2; Rt=1.758 min.

Example 169. The Synthesis of 5-[[2-[(2R,5R)-4,4-difluoro-2-(4-fluorophenyl)-5-methyl-1-piperidyl]-2-oxo-acetyl]amino]pyridine-3-carboxamide (Compound 718) and 5-[[2-[(2S,5S)-4,4-difluoro-2-(4-fluorophenyl)-5-methyl-1-piperidyl]-2-oxo-acetyl]amino]pyridine-3-carboxamide (Compound 731

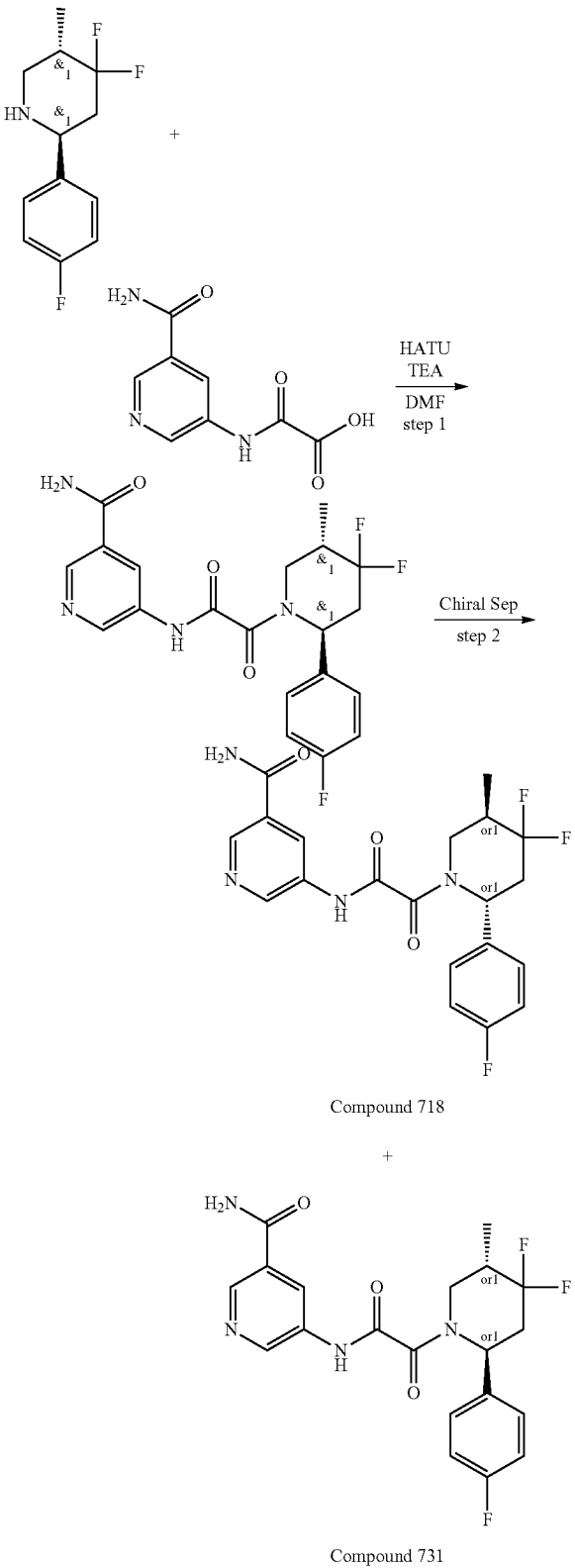

Compound 718

Compound 731

Step 1: Synthesis of rac-5-[[2-[(2R,5R)-4,4-difluoro-2-(4-fluorophenyl)-5-methyl-1-piperidyl]-2-oxo-acetyl]amino]pyridine-3-carboxamide (2R,5R)-4,4-difluoro-2-(4-fluorophenyl)-5-methyl-piperidine (0.6 g, 2.62 mmol), TEA (2.65 g, 26.17 mmol, 3.65 mL) and 2-[(5-carbamoyl-3-pyridyl)amino]-2-oxo-acetic acid (642.87 mg, 2.62 mmol, HCl) was dissolved in (26 mL) and HATU (1.49 g, 3.93 mmol) was added in one portion, the resulting mixture was stirred for 3 hr at 20° C. The reaction mixture was poured into water and the aqueous phase was extracted with EA (3 times), then the combined organic phase was washed with brine (3 times), dried over $Na_2SO_4$ and concentrated on vacuo. The crude product was purified by reverse phase HPLC (2-10 min 50-60% ACN/$H_2O$ 30 ml/min (loading pump 4 ml ACN) column: SunFire 100*19 mm, 5 micro). The reaction was successful. The desired product (5-[[2-[(2R,5R)-4,4-difluoro-2-(4-fluorophenyl)-5-methyl-1-piperidyl]-2-oxo-acetyl]amino]pyridine-3-carboxamide (0.205 g, 487.65 µmol, 18.63% yield)) was isolated as a brown solid.

LCMS(ESI): [M+1]$^+$ m/z: calcd 420.2; found 421.2; Rt=1.146 min.

Step 2: Chiral Separation for 5-[[2-[(2R,5R)-4,4-difluoro-2-(4-fluorophenyl)-5-methyl-1-piperidyl]-2-oxo-acetyl]amino]pyridine-3-carboxamide (Compound 718) and 5-[[2-[(2S,5S)-4,4-difluoro-2-(4-fluorophenyl)-5-methyl-1-piperidyl]-2-oxo-acetyl]amino]pyridine-3-carboxamide (Compound 731

Chiral separation was performed using (Column: Chiralcel OJ-H (250*20, 5 mkm), Hexane-IPA-MeOH, 50-25-25, 12 ml/min) to give 5-[[2-[(2R,5R)-4,4-difluoro-2-(4-fluorophenyl)-5-methyl-1-piperidyl]-2-oxo-acetyl]amino]pyridine-3-carboxamide (0.083 g, 197.44 µmol, 40.49% yield)—Compound 731 ret. time is 16.022 min (Chiralcel OJ-3 (150*2.1, 3 mkm), Hexane-IPA-MeOH, 50-25-25, 0.15 ml/min), and 5-[[2-[(2S,5S)-4,4-difluoro-2-(4-fluorophenyl)-5-methyl-1-piperidyl]-2-oxo-acetyl]amino]pyridine-3-carboxamide (0.085 g, 202.20 µmol, 41.46% yield)—Compound 718 ret. time is 10.577 min (Chiralcel OJ-3 (150*2.1, 3 mkm), Hexane-IPA-MeOH, 50-25-25, 0.15 ml/min).

Compound 718 $^1$H NMR (600 MHz, DMSO-$d_6$) δ (ppm) 1.08 (m, 3H), 2.20 (m, 1H), 2.84 (m, 1H), 3.05 (d, 1H), 3.44 (m, 1H), 3.99 (m, 1H), 5.69 (m, 1H), 7.19 (m, 2H), 7.36 (m, 2H), 7.59 (m, 1H), 8.14 (m, 1H), 8.47 (m, 1H), 8.76 (m, 1H), 8.87 (m, 1H), 11.27 (m, 1H)

LCMS(ESI): [M+1]$^+$ m/z: calcd 420.2; found 421.2; Rt=2.034 min.

Compound 731 $^1$H NMR (600 MHz, DMSO-$d_6$) δ (ppm) 1.08 (m, 3H), 2.20 (m, 1H), 2.84 (m, 1H), 3.05 (d, 1H), 3.44 (m, 1H), 3.99 (m, 1H), 5.69 (m, 1H), 7.19 (m, 2H), 7.36 (m, 2H), 7.59 (m, 1H), 8.14 (m, 1H), 8.47 (m, 1H), 8.76 (m, 1H), 8.87 (m, 1H), 11.27 (m, 1H)

LCMS(ESI): [M+1]$^+$ m/z: calcd 420.2; found 421.2; Rt=2.034 min.

Example 170. The Synthesis of 5-[[2-[(2S,5S)-4,4-difluoro-2-(4-fluorophenyl)-5-methyl-1-piperidyl]-2-oxo-acetyl]amino]-2-methoxy-pyridine-3-carboxamide (Compound 1047) and 5-[[2-[(2R,5R)-4,4-difluoro-2-(4-fluorophenyl)-5-methyl-1-piperidyl]-2-oxo-acetyl]amino]-2-methoxy-pyridine-3-carboxamide (Compound 1068

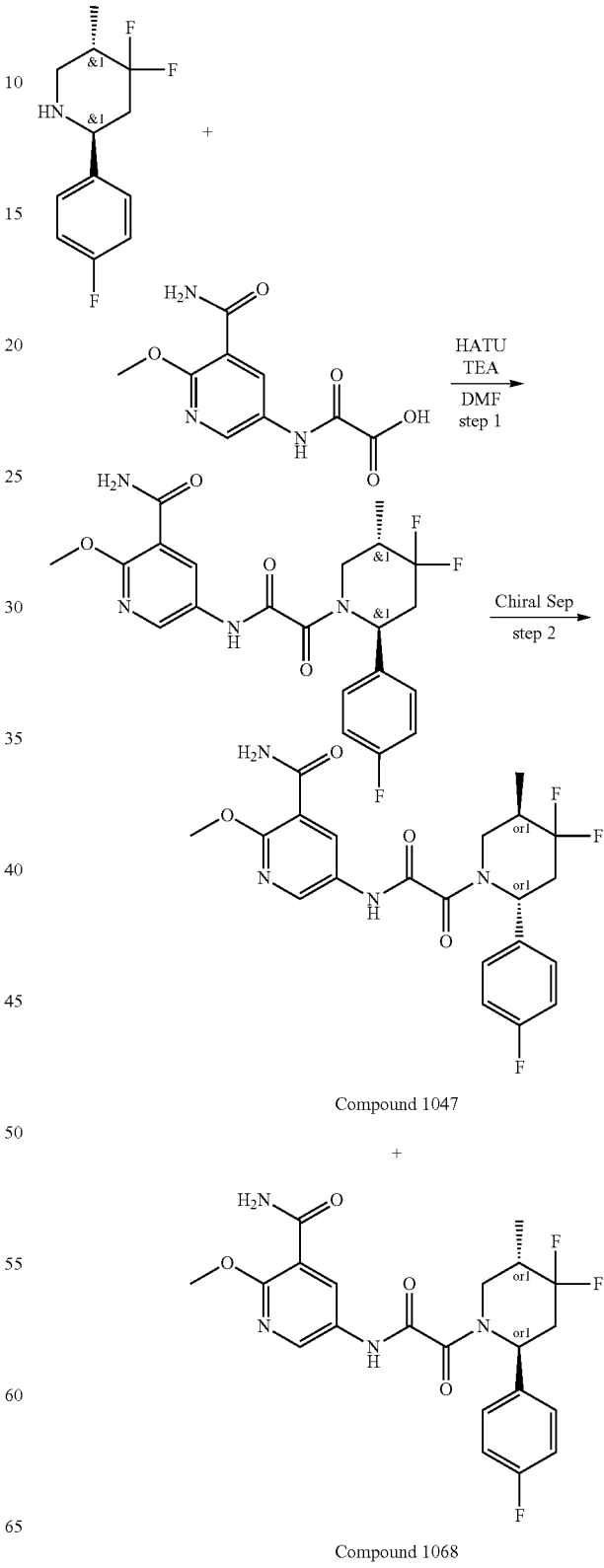

Compound 1047

Compound 1068

Step 1: Synthesis of 5-[[2-[(2R,5R)-4,4-difluoro-2-(4-fluorophenyl)-5-methyl-1-piperidyl]-2-oxo-acetyl]amino]-2-methoxy-pyridine-3-carboxamide (2R,5R)-4,4-difluoro-2-(4-fluorophenyl)-5-methyl-piperidine (0.4 g, 1.74 mmol), TEA (1.77 g, 17.45 mmol, 2.43 mL) and 2-[(5-carbamoyl-6-methoxy-3-pyridyl)amino]-2-oxo-acetic acid (417.35 mg, 1.74 mmol) was dissolved in DMF (18 mL) and HATU (995.19 mg, 2.62 mmol) was added in one portion, the resulting mixture was stirred for 3 hr at 20° C. The reaction mixture was poured into water and the aqueous phase was extracted with EA (3 times), then the combined organic phase was washed with brine (3 times), dried over $Na_2SO_4$ and concentrated on vacuo. The crude product was purified by reverse phase HPLC (2-10 min 10-50% methanol, 30 ml/min (loading pump 4 ml methanol) column: SunFire 100*19 mm, 5 microM). The reaction was successful. The desired product 5-[[2-[(2R,5R)-4,4-difluoro-2-(4-fluorophenyl)-5-methyl-1-piperidyl]-2-oxo-acetyl]amino]-2-methoxy-pyridine-3-carboxamide (0.151 g, 335.25 µmol, 19.21% yield) was isolated as a light-yellow solid.

LCMS(ESI): [M+1]$^+$ m/z: calcd 450.2; found 451.2; Rt=1.340 min.

Step 2. Separation for 5-[[2-[(2S,5S)-4,4-difluoro-2-(4-fluorophenyl)-5-methyl-1-piperidyl]-2-oxo-acetyl]amino]-2-methoxy-pyridine-3-carboxamide (Compound 1047) and 5-[[2-[(2R,5R)-4,4-difluoro-2-(4-fluorophenyl)-5-methyl-1-piperidyl]-2-oxo-acetyl]amino]-2-methoxy-pyridine-3-carboxamide (Compound 1068

Chiral separation was performed using (Column: Chiralcel OJ-H (250*20, 5 mkm), IPA-MeOH, 50-50, 12 ml/min) to give 5-[[2-[(2S,5S)-4,4-difluoro-2-(4-fluorophenyl)-5-methyl-1-piperidyl]-2-oxo-acetyl]amino]-2-methoxy-pyridine-3-carboxamide (0.068 g, 150.97 µmol, 45.03% yield)—ret. time is 32.799 min and 5-[[2-[(2R,5R)-4,4-difluoro-2-(4-fluorophenyl)-5-methyl-1-piperidyl]-2-oxo-acetyl]amino]-2-methoxy-pyridine-3-carboxamide (0.063 g, 139.87 µmol, 41.72% yield)—ret. time is 10.884 min.

Compound 1068 1H NMR (600 MHz, DMSO-d$_6$) δ 1.08 (d, 3H), 2.12-2.28 (m, 1H), 2.40-2.46 (m, 1H), 2.79-2.89 (m, 1H), 2.99-3.07 (m, 0.3H), 3.41-3.50 (m, 0.7H), 3.79-3.91 (m, 0.7H), 3.90-3.99 (m, 3H), 4.23-4.34 (m, 0.3H), 5.52-6.01 (m, 1H), 7.13-7.27 (m, 2H), 7.33-7.41 (m, 2H), 7.66-7.81 (m, 2H), 8.41-8.62 (m, 2H), 10.76-11.27 (m, 1H).

LCMS(ESI): [M+1]$^+$ m/z: calcd 450.2; found 451.2; Rt=3.147 min.

Compound 1047 1H NMR (600 MHz, DMSO-d$_6$) δ 1.08 (d, 3H), 2.12-2.28 (m, 1H), 2.40-2.46 (m, 1H), 2.79-2.89 (m, 1H), 2.99-3.07 (m, 0.3H), 3.41-3.50 (m, 0.7H), 3.79-3.91 (m, 0.7H), 3.90-3.99 (m, 3H), 4.23-4.34 (m, 0.3H), 5.52-6.01 (m, 1H), 7.13-7.27 (m, 2H), 7.33-7.41 (m, 2H), 7.66-7.81 (m, 2H), 8.41-8.62 (m, 2H), 10.76-11.27 (m, 1H).

LCMS(ESI): [M+1]$^+$ m/z: calcd 450.2; found 451.2; Rt=3.147 min.

Example 171. The Synthesis of 5-[[2-[(2S,5R)-5-methyl-2-(1H-pyrazolo[4,3-b]pyridin-5-yl)-1-piperidyl]-2-oxo-acetyl]amino]pyridine-3-carboxamide (Compound 787) and 5-[[2-[(2R,5S)-5-methyl-2-(1H-pyrazolo[4,3-b]pyridin-5-yl)-1-piperidyl]-2-oxo-cetyl]amino]pyridine-3-carboxamide (Compound 778

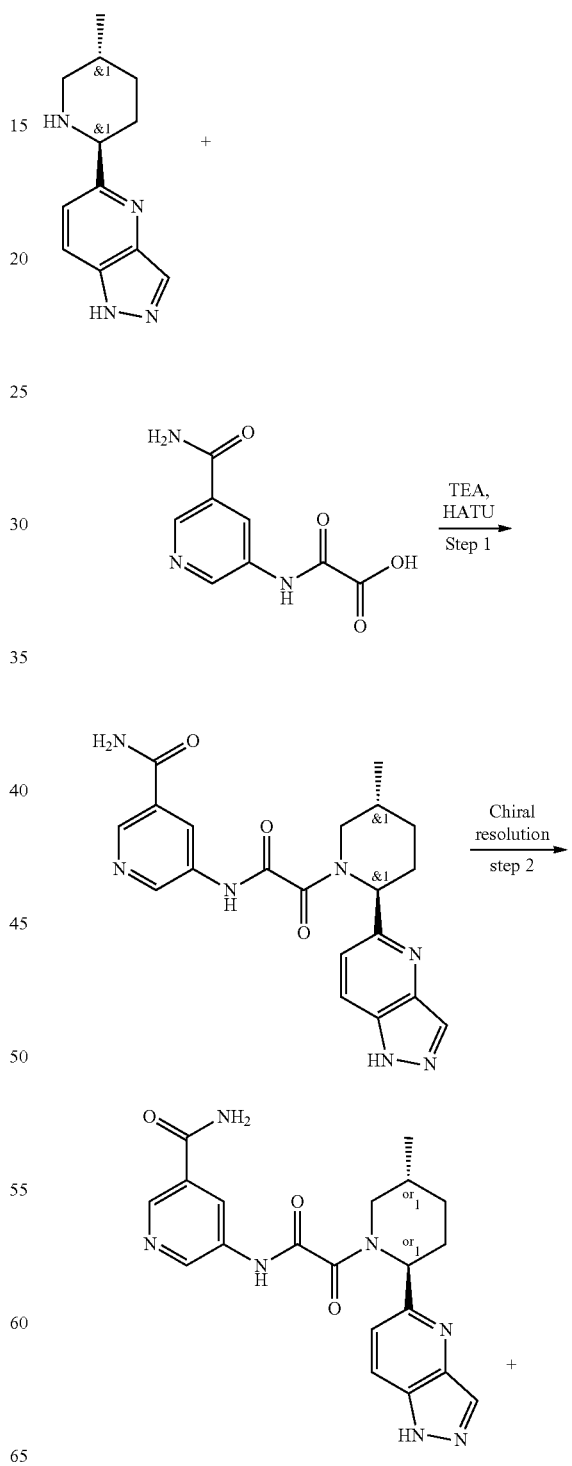

Compound 787

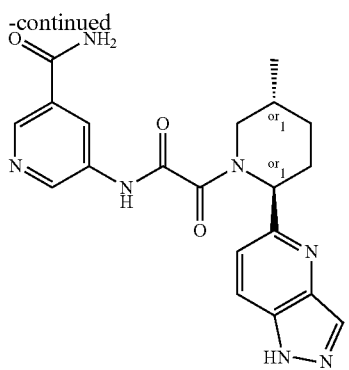

Compound 778

Step 1. Synthesis of rac-5-[[2-[(2R,5S)-5-methyl-2-(1H-pyrazolo[4,3-b]pyridin-5-yl)-1-piperidyl]-2-oxo-acetyl]amino]pyridine-3-carboxamide 2-[(5-carbamoyl-3-pyridyl)amino]-2-oxo-acetic acid (241.77 mg, 1.16 mmol) and 5-(5-methyl-2-piperidyl)-1H-pyrazolo[4,3-b]pyridine (0.25 g, 1.16 mmol) were mixed in DMF (20 mL). The reaction suspension was cooled to 0° C. and HATU (439.51 mg, 1.16 mmol) followed by TEA (116.97 mg, 1.16 mmol, 161.11 μL) were added and stirred at ambient temperature for 12 hr. The reaction mixture was evaporated in vacuo and obtained crude product 0.48 g was purified by preparative 25-45% 1-6 min water-methanol (NH$_3$ 0.1%), flow 30 ml/min to afford product 5-[[2-[(2R,5S)-5-methyl-2-(1H-pyrazolo[4,3-b]pyridin-5-yl)-1-piperidyl]-2-oxo-acetyl]amino]pyridine-3-carboxamide (0.14 g, 343.62 μmol, 29.73% yield).

LCMS(ESI): [M+1]$^+$ m/z: calcd 407.2; found 408.2; Rt=1.756 min.

Step 2. Separation for 5-[[2-[(2S,5R)-5-methyl-2-(1H-pyrazolo[4,3-b]pyridin-5-yl)-1-piperidyl]-2-oxo-acetyl]amino]pyridine-3-carboxamide (Compound 787) and 5-[[2-[(2R,5S)-5-methyl-2-(1H-pyrazolo[4,3-b]pyridin-5-yl)-1-piperidyl]-2-oxo-acetyl]amino]pyridine-3-carboxamide (Compound 778

The 5-[[2-[(2R,5S)-5-methyl-2-(1H-pyrazolo[4,3-b]pyridin-5-yl)-1-piperidyl]-2-oxo-acetyl]amino]pyridine-3-carboxamide (187.70 mg, 460.70 μmol) was subjected to chiral HPLC separation (Column: IC-II (250*20, 5 um), Eluent: Hexane-IPA-MeOH, 60-20-20, flow rate: 12 mL/min) to give the two individual enantiomers Compound 778 5-[[2-[(2R,5S)-5-methyl-2-(1H-pyrazolo[4,3-b]pyridin-5-yl)-1-piperidyl]-2-oxo-acetyl]amino]pyridine-3-carboxamide (0.056 g, 137.45 μmol, 29.83% yield) and Compound 787 5-[[2-[(2S,5R)-5-methyl-2-(1H-pyrazolo[4,3-b]pyridin-5-yl)-1-piperidyl]-2-oxo-acetyl]amino]pyridine-3-carboxamide (61.63 mg, 151.27 μmol, 32.83% yield)

Compound 778 RT (AD-H, CO$_2$-MeOH, 60-40, 2.0 ml/min)=11.035 min $^1$H NMR (600 MHz, DMSO-d$_6$) δ 1.01-1.10 (m, 3H), 1.33-1.41 (m, 1H), 1.73-1.85 (m, 1H), 1.85-1.98 (m, 1H), 1.99-2.15 (m, 1H), 2.50-2.55 (m, 1H), 2.88-2.95 (m, 0.4H), 3.34-3.42 (m, 0.6H), 3.50-4.13 (m, 1H), 5.28-5.82 (m, 1H), 7.28-7.50 (m, 1H), 7.53-7.65 (m, 1H), 8.00-8.07 (m, 1H), 8.08-8.19 (m, 1H), 8.22-8.31 (m, 1H), 8.42-8.53 (m, 1H), 8.69-8.79 (m, 1H), 8.81-8.93 (m, 1H), 11.07-11.37 (m, 1H), 13.30 (br s, 1H).

LCMS(ESI): [M+H]$^+$ m/z: calcd 408.2; found 415.2; Rt=1.558 min.

Compound 787 RT (AD-H, CO$_2$-MeOH, 60-40, 2.0 ml/min)=7.7 min $^1$H NMR (600 MHz, DMSO-d$_6$) δ 1.01-1.10 (m, 3H), 1.33-1.41 (m, 1H), 1.73-1.85 (m, 1H), 1.85-1.98 (m, 1H), 1.99-2.15 (m, 1H), 2.50-2.55 (m, 1H), 2.88-2.95 (m, 0.4H), 3.34-3.42 (m, 0.6H), 3.50-4.13 (m, 1H), 5.28-5.82 (m, 1H), 7.28-7.50 (m, 1H), 7.53-7.65 (m, 1H), 8.00-8.07 (m, 1H), 8.08-8.19 (m, 1H), 8.22-8.31 (m, 1H), 8.42-8.53 (m, 1H), 8.69-8.79 (m, 1H), 8.81-8.93 (m, 1H), 11.07-11.37 (m, 1H), 13.30 (br s, 1H).

LCMS(ESI): [M+H]$^+$ m/z: calcd 408.2; found 415.2; Rt=1.558 min.

Example 172. The Synthesis of 5-[[2-[(2S,5R)-2-(3,5-Dichlorophenyl)-5-methyl-1-piperidyl]-2-oxo-acetyl]amino]pyridine-3-carboxamide (Compound 490) and 5-[[2-[(2R,5S)-2-(3,5-Dichlorophenyl)-5-methyl-1-piperidyl]-2-oxo-acetyl]amino]pyridine-3-carboxamide (Compound 491

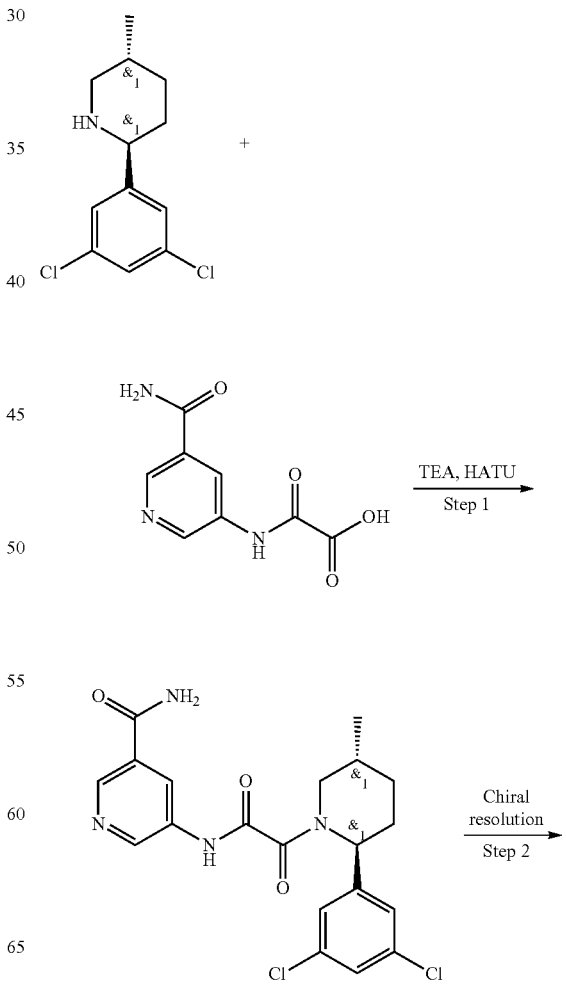

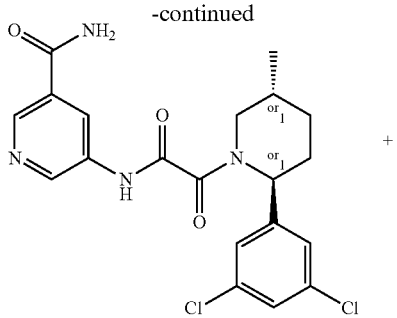

Compound 490

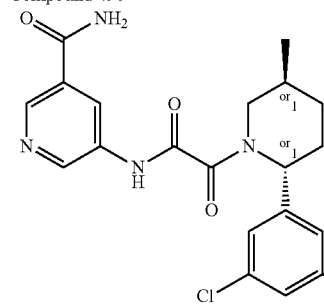

Compound 491

Step 1. Synthesis of 5-[[2-[2-(3,5-Dichlorophenyl)-5-methyl-1-piperidyl]-2-oxo-acetyl]amino]pyridine-3-carboxamide 2-[(5-carbamoyl-3-pyridyl)amino]-2-oxo-acetic acid (508.43 mg, 1.64 mmol, Et₃N), HATU (622.92 mg, 1.64 mmol) and Triethylamine (165.78 mg, 1.64 mmol, 228.34 µL) were mixed in dry DMF (5 mL) at 21° C. and the resulting mixture was stirred for 5 hr. 2-(3,5-dichlorophenyl)-5-methyl-piperidine (0.4 g, 1.64 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (50-100% 2-7 min; water-r1+nh3 30 ml/min; loading pump r1+h3 4 ml/min; column YMC-Actus triat 19*100 mm). Two fractions of 5-[[2-[2-(3,5-dichlorophenyl)-5-methyl-1-piperidyl]-2-oxo-acetyl]amino]pyridine-3-carboxamide (347.9 mg, 799.21 µmol, 48.78% yield) were obtained: 233.7 mg (90.57% of trans) and 114.2 mg (80.33% of trans).

LCMS(ESI): [M+1]⁺ m/z: calcd 435.1; found 436.0; Rt=1.222 min.

Step 2. Separation for 5-[[2-[(2S,5R)-2-(3,5-Dichlorophenyl)-5-methyl-1-piperidyl]-2-oxo-acetyl]amino]pyridine-3-carboxamide (Compound 490 and 5-[[2-[(2R,5S)-2-(3,5-Dichlorophenyl)-5-methyl-1-piperidyl]-2-oxo-acetyl]amino]pyridine-3-carboxamide (Compound 491)

Chiral separation was done in the following conditions: IA-II (250*20, 5 mkm), Hexane-IPA-MeOH, 70-15-15, 12 ml/min, RT (Compound 491)=29.063 min, RT (Compound 490)=19.574 min RT of 5-[[2-[(2S,5R)-2-(3,5-dichlorophenyl)-5-methyl-1-piperidyl]-2-oxo-acetyl]amino]pyridine-3-carboxamide Compound 490 (85.97 mg, 197.49 µmol, 36.79% yield) =20.8502 min (IA, Hexane-IPA-MeOH, 70-15-15, 0.6 ml/min)

RT of 5-[[2-[(2R,5S)-2-(3,5-dichlorophenyl)-5-methyl-1-piperidyl]-2-oxo-acetyl]amino]pyridine-3-carboxamide Compound 491 (92.28 mg, 211.99 µmol, 39.49% yield)=31.7442 min (IA, Hexane-IPA-MeOH, 70-15-15, 0.6 ml/min)

Compound 490: ¹H NMR (600 MHz, DMSO-d₆) δ 0.96-1.04 (m, 3H), 1.23-1.38 (m, 1H), 1.56-1.68 (m, 1H), 1.84-1.95 (m, 1H), 1.98-2.14 (m, 1H), 2.14-2.29 (m, 1H), 2.76-3.27 (m, 1H), 3.47-4.07 (m, 1H), 5.12-5.56 (m, 1H), 7.30-7.38 (m, 2H), 7.49-7.55 (m, 1H), 7.56-7.65 (m, 1H), 8.04-8.20 (m, 1H), 8.41-8.54 (m, 1H), 8.72-8.80 (m, 1H), 8.80-8.91 (m, 1H), 11.23-11.44 (m, 1H).

LCMS(ESI): [M+H]⁺ m/z: calcd 434.2; found 345.2; Rt=3.594 min.

Compound 491: ¹H NMR (600 MHz, DMSO-d₆) δ 0.96-1.04 (m, 3H), 1.23-1.38 (m, 1H), 1.56-1.68 (m, 1H), 1.84-1.95 (m, 1H), 1.98-2.14 (m, 1H), 2.14-2.29 (m, 1H), 2.76-3.27 (m, 1H), 3.47-4.07 (m, 1H), 5.12-5.56 (m, 1H), 7.30-7.38 (m, 2H), 7.49-7.55 (m, 1H), 7.56-7.65 (m, 1H), 8.04-8.20 (m, 1H), 8.41-8.54 (m, 1H), 8.72-8.80 (m, 1H), 8.80-8.91 (m, 1H), 11.23-11.44 (m, 1H).

LCMS(ESI): [M+H]⁺ m/z: calcd 434.2; found 345.2; Rt=3.594 min.

Example 0.173. The Synthesis of N-(6-amino-5-ethyl-3-pyridyl)-2-[(2S,5R)-2-(3,5-Dichlorophenyl)-5-methyl-1-piperidyl]-2-oxo-acetamide (Compound 966) and N-(6-amino-5-ethyl-3-pyridyl)-2-[(2R,5S)-2-(3,5-Dichlorophenyl)-5-methyl-1-piperidyl]-2-oxo-acetamide (Compound 951

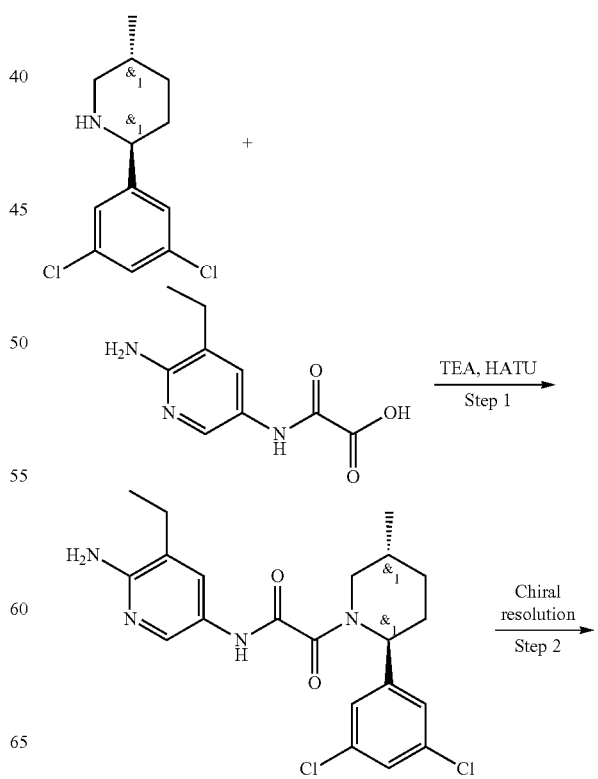

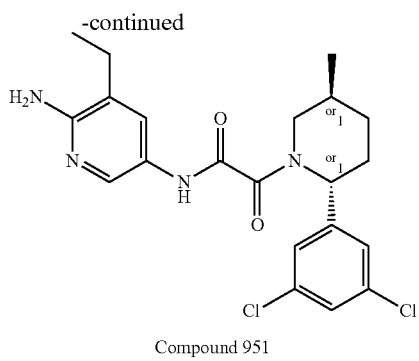

Compound 951

+

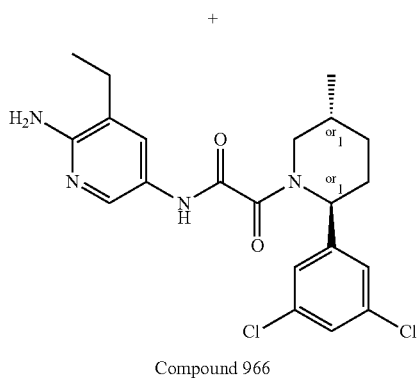

Compound 966

Step 1. Synthesis of N-(6-amino-5-ethyl-3-pyridyl)-2-[(2S,5R)-2-(3,5-Dichlorophenyl)-5-methyl 1-piperidyl]-2-oxo-acetamide 2-[(6-amino-5-ethyl-3-pyridyl)amino]-2-oxo-acetic acid (0.2 g, 956.01 μmol), HATU (363.51 mg, 956.01 μmol) and triethylamine (106.41 mg, 1.05 mmol, 146.57 μL) were mixed in dry DMF (5 mL) at 21° C. and the resulting mixture was stirred for 15 min. (2S,5R)-2-(3,5-dichlorophenyl)-5-methyl-piperidine (233.42 mg, 956.01 μmol) was added thereto and the resulting mixture was stirred at 21° C. overnight. The resulting mixture was poured into water, extracted 3 times with EtOAc, combined organics were washed with water, brine, and evaporated. The residue was subjected to HPLC (50-75% 0.5-6 min water-acetonitrile; flow 30 ml/min (loading pump 4 ml/min; acetonitrile); column SunFire 100×19 mm 5 um (R)). Three fractions of N-(6-amino-5-ethyl-3-pyridyl)-2-[(2S,5R)-2-(3,5-dichlorophenyl)-5-methyl-1-piperidyl]-2-oxo-acetamide (258.3 mg, 593.32 μmol, 62.06% yield) were obtained: 1st—41.1 mg (100% by LCMS); 2nd—109.3 mg (93.46% trans, 6.54% cis); 3rd—107.9 mg (84.79% trans, 13.83% cis) as beige solids.

LCMS(ESI): [M]$^+$ m/z: calcd 434.2; found 435.2; Rt=2.909 min.

Step 2. Synthesis of N-(6-amino-5-ethyl-3-pyridyl)-2-[(2S,5R)-2-(3,5-Dichlorophenyl)-5-methyl-1-piperidyl]-2-oxo-acetamide (Compound 966) and N-(6-amino-5-ethyl-3-pyridyl)-2-[(2R,5S)-2-(3,5-Dichlorophenyl)-5-methyl-1-piperidyl]-2-oxo-acetamide (Compound 951

Enantiomers were separated in the following conditions: CHIRALPAC AD-H 250*20, 5 Hexane-IPA-MeOH, 50-25-25, 12 ml/min. RT (Compound 966)=13.308 min, RT (Compound 951)=25.111 min RT of N-(6-amino-5-ethyl-3-pyridyl)-2-[(2S,5R)-2-(3,5-dichlorophenyl)-5-methyl-1-piperidyl]-2-oxo-acetamide (39.37 mg, 90.43 μmol, 26.18% yield)=7.7182 min (Chiralpak AD-3 (150*2.1, 3 mkm), Hexane-IPA-MeOH, 50-25-25, 0.15 ml/min)

RT of N-(6-amino-5-ethyl-3-pyridyl)-2-[(2R,5S)-2-(3,5-dichlorophenyl)-5-methyl-1-piperidyl]-2-oxo-acetamide (53.66 mg, 123.26 μmol, 35.68% yield)=15.6142 min (Chiralpak AD-3 (150*2.1, 3 mkm), Hexane-IPA-MeOH, 50-25-25, 0.15 ml/min)

Compound 951: $^1$H NMR (600 MHz, DMSO-d$_6$) δ 0.96-1.02 (m, 3H), 1.06-1.13 (m, 3H), 1.23-1.36 (m, 1H), 1.56-1.65 (m, 1H), 1.82-1.93 (m, 1H), 1.96-2.10 (m, 1H), 2.11-2.24 (m, 1H), 2.39 (q, 2H), 2.70-3.28 (m, 1H), 3.44-4.04 (m, 1H), 5.09-5.54 (m, 1H), 5.56-5.68 (m, 2H), 7.26-7.39 (m, 2H), 7.39-7.55 (m, 2H), 7.90-8.10 (m, 1H), 10.48-10.64 (m, 1H).

LCMS(ESI): [M+1]$^+$ m/z: calcd 434.2; found 435.2; Rt=2.936 min.

Compound 966: $^1$H NMR (600 MHz, DMSO-d$_6$) δ 0.96-1.02 (m, 3H), 1.06-1.13 (m, 3H), 1.23-1.36 (m, 1H), 1.56-1.65 (m, 1H), 1.82-1.93 (m, 1H), 1.96-2.10 (m, 1H), 2.11-2.24 (m, 1H), 2.39 (q, 2H), 2.70-3.28 (m, 1H), 3.44-4.04 (m, 1H), 5.09-5.54 (m, 1H), 5.56-5.68 (m, 2H), 7.26-7.39 (m, 2H), 7.39-7.55 (m, 2H), 7.90-8.10 (m, 1H), 10.48-10.64 (m, 1H).

LCMS(ESI): [M+1]$^+$ m/z: calcd 434.2; found 435.2; Rt=2.936 min.

Example 174. The Synthesis of 5-[[2-[(2R,5S)-2-(3,5-Dichlorophenyl)-5-methyl-1-piperidyl]-2-oxo-acetyl]amino]-2-methoxy-pyridine-3-carboxamide (Compound 945) and 5-[[2-[(2S,5R)-2-(3,5-Dichlorophenyl)-5-methyl-1-piperidyl]-2-oxo-acetyl]amino]-2-methoxy-pyridine-3-carboxamide (Compound 965

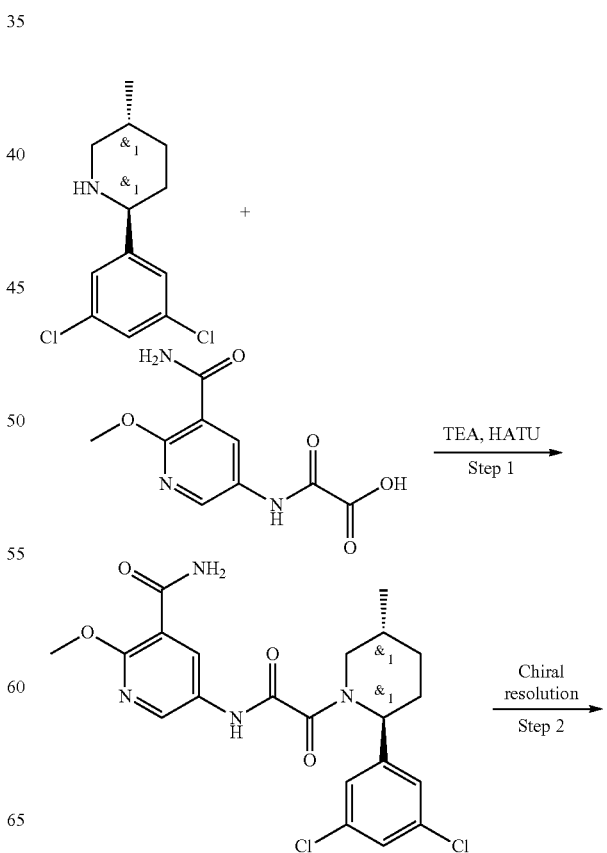

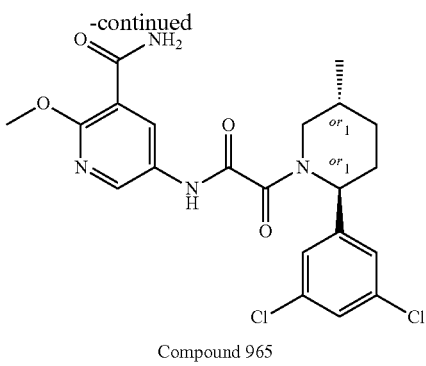

Compound 965

+

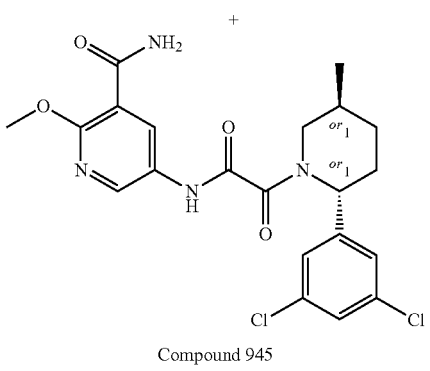

Compound 945

Step 1. Synthesis of 5-[[2-[(2S,5R)-2-(3,5-Dichlorophenyl)-5-methyl-1-piperidyl]-2-oxo-acetyl]amino]-2-methoxy-pyridine-3-carboxamide 2-[(5-carbamoyl-6-methoxy-3-pyridyl)amino]-2-oxoacetic acid (0.2 g, 836.17 μmol), HATU (317.94 mg, 836.17 μmol) and triethylamine (93.07 mg, 919.79 μmol, 128.20 μL) were mixed in dry DMF (5 mL) at 21° C. and the resulting mixture was stirred for 15 min. (2S,5R)-2-(3,5-dichlorophenyl)-5-methyl-piperidine (204.16 mg, 836.17 μmol) was added thereto and the resulting mixture was stirred at 21° C. overnight. The resulting mixture was poured into water, extracted 3 times with EtOAc, combined organics were washed with water, brine, and evaporated. The residue was subjected to HPLC (45-70% 0.5-6 min water-acetonitrile; flow 30 ml/min (loading pump 4 ml/min; acetonitrile); column SunFire 100×19 mm 5 um (R)). Three fractions were obtained: 1st—76.5 mg (100%); 2nd—89.8 mg (89.71% trans, 10.29% cis); 3rd—95.8 mg (82.39% trans, 17.61% cis) as a white solids.

LCMS(ESI): [M+1]$^+$ m/z: calcd 464.2; found 465.2; Rt=3.489 min.

Step 2. Separation for 5-[[2-[(2R,5S)-2-(3,5-Dichlorophenyl)-5-methyl-1-piperidyl]-2-oxo-acetyl]amino]-2-methoxy-pyridine-3-carboxamide (Compound 945) and 5-[[2-[(2S,5R)-2-(3,5-Dichlorophenyl)-5-methyl-1-piperidyl]-2-oxo-acetyl]amino]-2-methoxy-pyridine-3-carboxamide (Compound 965

Enantiomers were separated in the following conditions: Chiralpak IC 250*20, 5-II Hexane-IPA-MeOH, 60-20-20, 15 ml/min Preparative: CHIRALPAK-IC (250*20 mm, 5 mkm) Hexane-IPAMeOH, 60-20-20, 15 ml/min RT of 5-[[2-[(2S,5R)-2-(3,5-dichlorophenyl)-5-methyl-1-piperidyl]-2-oxo-acetyl]amino]-2-methoxy-pyridine-3-carboxamide Compound 965 (74.22 mg, 159.50 μmol, 44.63% yield)=17.005 min RT of 5-[[2-[(2R,5S)-2-(3,5-dichlorophenyl)-5-methyl-1-piperidyl]-2-oxo-acetyl]amino]-2-methoxy-pyridine-3-carboxamide Compound 945 (77.71 mg, 167.00 μmol, 46.73% yield)=23.346 min RT of 5-[[2-[(2R,5S)-2-(3,5-dichlorophenyl)-5-methyl-1-piperidyl]-2-oxo-acetyl]amino]-2-methoxy-pyridine-3-carboxamide Compound 945 (74.22 mg, 159.50 μmol, 44.63% yield)=21.185 min (Chiralpak IC-3 (150*2.1, 3 mkm), Hexane-IPA-MeOH, 70-15-15, 0.15 ml/min)

RT of 5-[[2-[(2S,5R)-2-(3,5-dichlorophenyl)-5-methyl-1-piperidyl]-2-oxo-acetyl]amino]-2-methoxy-pyridine-3-carboxamide Compound 965 (77.71 mg, 167.00 μmol, 46.73% yield)=15,456 min (Chiralpak IC-3 (150*2.1, 3 mkm), Hexane-IPA-MeOH, 70-15-15, 0.15 ml/min)

Compound 945: 1H NMR (600 MHz, DMSO-d$_6$) δ 0.97-1.02 (m, 3H), 1.23-1.37 (m, 1H), 1.56-1.67 (m, 1H), 1.82-1.94 (m, 1H), 1.95-2.24 (m, 2H), 2.59-3.11 (m, 1H), 3.48-4.04 (m, 4H), 5.14-5.52 (m, 1H), 7.29-7.38 (m, 2H), 7.48-7.55 (m, 1H), 7.66-7.78 (m, 2H), 8.40-8.58 (m, 2H), 10.99-11.18 (m, 1H).

LCMS(ESI): [M+1]$^+$ m/z: calcd 464.2; found 465.2; Rt=3.591 min.

Compound 965: 1H NMR (600 MHz, DMSO-d$_6$) δ 0.97-1.02 (m, 3H), 1.23-1.37 (m, 1H), 1.56-1.67 (m, 1H), 1.82-1.94 (m, 1H), 1.95-2.24 (m, 2H), 2.59-3.11 (m, 1H), 3.48-4.04 (m, 4H), 5.14-5.52 (m, 1H), 7.29-7.38 (m, 2H), 7.48-7.55 (m, 1H), 7.66-7.78 (m, 2H), 8.40-8.58 (m, 2H), 10.99-11.18 (m, 1H).

LCMS(ESI): [M+1]$^+$ m/z: calcd 464.2; found 465.2; Rt=3.591 min.

Example 175. The Synthesis of rac-5-(2-((2R,5S)-5-methyl-2-(2-oxo-1,2-dihydroquinolin-6-yl)piperidin-1-yl)-2-oxoacetamido)Nicotinamide (Compound 670), Rel-5-[[2-[(2S,5R)-5-methyl-2-(2-oxo-1H-Quinolin-6-yl)-1-piperidyl]-2-oxo-acetyl]amino]pyridine-3-carboxamide (Compound 804) and Rel-5-[[2-[(2R,5S)-5-methyl-2-(2-oxo-1H-Quinolin-6-yl)-1-piperidyl]-2-oxo-acetyl]amino]pyridine-3-carboxamide (Compound 809

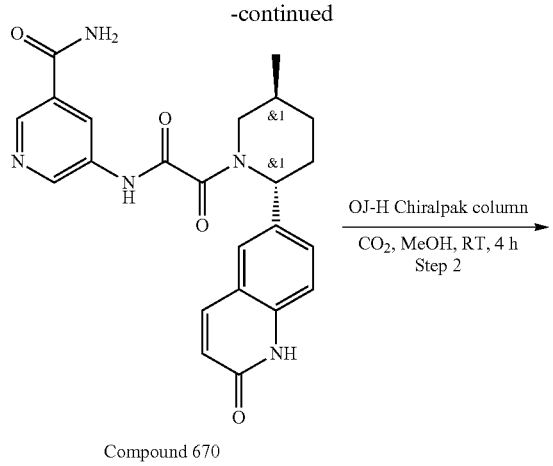

Compound 670

Compound 804

+

Compound 809

Step 1: The Synthesis of rac-5-(2-((2R,5S)-5-methyl-2-(2-oxo-1,2-dihydroquinolin-6-yl)piperidin-1-yl)-2-oxoacetamido)Nicotinamide (Compound 670

6-(5-methyl-2-piperidyl)-1H-quinolin-2-one (0.25 g, 1.03 mmol), 2-[(5-carbamoyl-3-pyridyl)amino]-2-oxo-acetic acid (253.41 mg, 1.03 mmol, HCl) and triethylamine (1.04 g, 10.32 mmol, 1.44 mL) were mixed together in DMF (5 mL). HATU (588.43 mg, 1.55 mmol) was added thereto and the resulting mixture was stirred for 18 hr. The reaction mixture was concentrated in vacuo and the residue was purified by HPLC 2-10 min 50-60% MeOH/H$_2$O, 30 mL/min (loading pump 4 mL MeOH), column: SunFire 100*19 mm, 5 microm) to obtain 5-[[2-[(2S,5R)-5-methyl-2-(2-oxo-1H-quinolin-6-yl)-1-piperidyl]-2-oxo-acetyl] amino]pyridine-3-carboxamide (0.2025 g, 467.17 μmol, 45.28% yield).

$^1$H NMR (DMSO-d$_6$, 600 MHz): δ (ppm) 1.03 (m, 3H), 1.35 (m, 1H), 1.73 (m, 1H), 1.88 (m, 1H), 2.19 (m, 2H), 2.82 (m, 1H), 3.74 (m, 1H), 5.40 (m, 1H), 6.47 (m, 1H), 7.30 (m, 1H), 7.45 (m, 1H), 7.61 (m, 2H), 7.87 (m, 1H), 8.14 (m, 1H), 8.47 (m, 1H), 8.80 (m, 2H), 11.21 (m, 1H), 11.70 (m, 1H).

LCMS(ESI): [M+H]$^+$ m/z: calcd 433.2; found 434.0; Rt=1.879 min.

Step 2: The Synthesis of Rel-5-[[2-[(2S,5R)-5-methyl-2-(2-oxo-1H-Quinolin-6-yl)-1-piperidyl]-2-oxo-acetyl]amino]pyridine-3-carboxamide (Compound 804) and Rel-5-[[2-[(2R,5S)-5-methyl-2-(2-oxo-1H-Quinolin-6-yl)-1-piperidyl]-2-oxo-acetyl] amino]pyridine-3-carboxamide (Compound 809)

The mixture of diastereomers was separated by chiral chromatography (OJ-H, C02-MeOH, 70-30, 3.0 ml/min) to obtain Compound 804—rel-5-[[2-[(2S,5R)-5-methyl-2-(2-oxo-1H-quinolin-6-yl)-1-piperidyl]-2-oxo-acetyl]amino] pyridine-3-carboxamide (36.05 mg, 83.17 μmol, 23.02% yield) and Compound 809—rel-5-[[2-[(2R,5S)-5-methyl-2-(2-oxo-1H-quinolin-6-yl)-1-piperidyl]-2-oxo-acetyl]amino] pyridine-3-carboxamide (37.44 mg, 86.37 μmol, 23.91% yield).

Compound 804: RT (OJ-H, CO$_2$-MeOH, 70-30, 3.0 mL/min)=2.726 min.

$^1$H NMR (dmso, 600 MHz): δ (ppm) 0.99-1.07 (m, 3H), 1.28-1.44 (m, 1H), 1.66-1.77 (m, 1H), 1.81-1.95 (m, 1H), 2.01-2.16 (m, 1H), 2.20-2.31 (m, 1H), 2.78-3.23 (m, 1H), 3.45-4.05 (m, 1H), 5.15-5.67 (m, 1H), 6.42-6.50 (m, 1H), 7.26-7.36 (m, 1H), 7.40-7.52 (m, 1H), 7.54-7.68 (m, 2H), 7.82-7.96 (m, 1H), 8.05-8.24 (m, 1H), 8.40-8.56 (m, 1H), 8.68-8.79 (m, 1H), 8.79-8.96 (m, 1H), 10.92-11.49 (m, 1H), 11.51-11.89 (m, 1H).

LCMS(ESI): [M+H]$^+$ m/z: calcd 433.2; found 434.2; Rt=1.005 min.

Compound 809: RT (OJ-H, CO$_2$-MeOH, 70-30, 3.0 mL/min)=4.383 min.

$^1$H NMR (dmso, 600 MHz): δ (ppm) 1.00-1.09 (m, 3H), 1.30-1.42 (m, 1H), 1.67-1.79 (m, 1H), 1.82-1.95 (m, 1H), 2.01-2.19 (m, 1H), 2.20-2.29 (m, 1H), 2.78-3.23 (m, 1H), 3.44-4.02 (m, 1H), 5.11-5.70 (m, 1H), 6.41-6.56 (m, 1H), 7.25-7.37 (m, 1H), 7.39-7.52 (m, 1H), 7.53-7.67 (m, 2H), 7.84-7.93 (m, 1H), 8.08-8.23 (m, 1H), 8.39-8.54 (m, 1H), 8.69-8.79 (m, 1H), 8.79-8.98 (m, 1H), 11.11-11.52 (m, 1H), 11.52-11.92 (m, 1H).

LCMS(ESI): [M+H]$^+$ m/z: calcd 433.2; found 434.2; Rt=1.917 min.

1573

Example 176. The Synthesis of Rel-2-methoxy-5-[[2-[(2S,5R)-5-methyl-2-(2-oxo-1H-Quinolin-6-yl)-1-piperidyl]-2-oxo-acetyl]amino]pyridine-3-carboxamide (Compound 810) and Rel-2-methoxy-5-[[2-[(2R,5S)-5-methyl-2-(2-oxo-1H-Quinolin-6-yl)-1-piperidyl]-2-oxo-acetyl]amino]pyridine-3-carboxamide (Compound 807

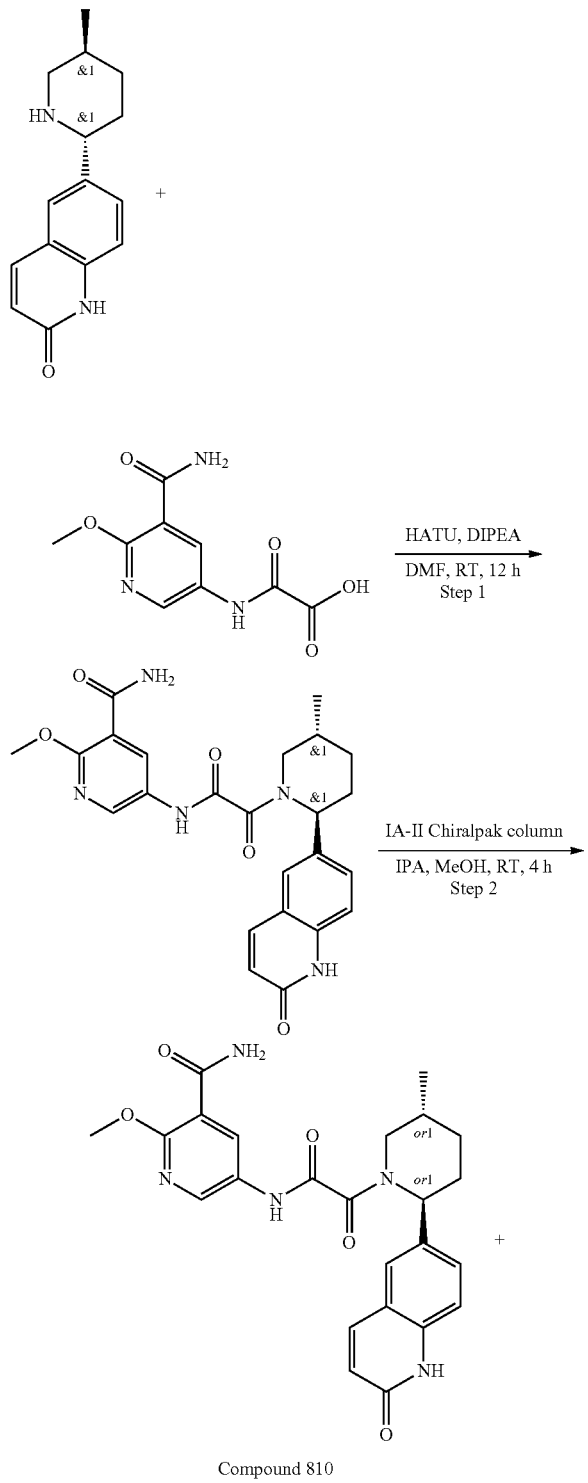

1574

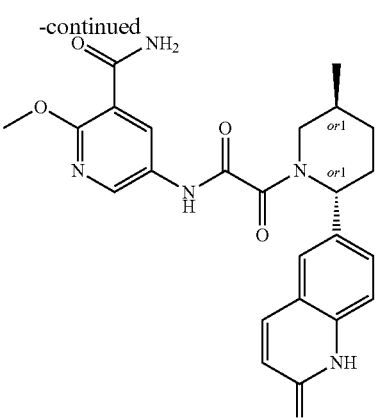

Compound 807

Step 1: The Synthesis of rac-2-methoxy-5-[[2-[(2S,5R)-5-methyl-2-(2-oxo-1H-Quinolin-6-yl)-1-piperidyl]-2-oxo-acetyl]amino]pyridine-3-carboxamide 6-(5-methyl-2-piperidyl)-1H-quinolin-2-one (0.3 g, 1.24 mmol), 2-[(5-carbamoyl-6-methoxy-3-pyridyl)amino]-2-oxo-acetic acid (296.12 mg, 1.24 mmol), triethylamine (626.39 mg, 6.19 mmol, 862.80 µL) were mixed in DMF (10 mL) and then HATU (706.12 mg, 1.86 mmol) were added. Resulting mixture were stirred at 25° C. for 12 hr. The solvent was evaporated and resulting mixture was stirred with SiliaMetS® DMT (50 mg) in methanol (10 ml). The mixture was filtered and evaporated under reduce pressure. Resulting crude material was purified by HPLC (2-10 min 40-45% Methanol/$H_2O$, 30 mL/min) to obtain rac-2-methoxy-5-[[2-[(2S,5R)-5-methyl-2-(2-oxo-1H-quinolin-6-yl)-1-piperidyl]-2-oxo-acetyl]amino]pyridine-3-carboxamide (138.6 mg, 299.04 µmol, 24.15% yield).

LCMS(ESI): $[M+H]^+$ m/z: calcd 463.2; found 464.1; Rt=1.087 min.

Step 2: The Synthesis of Rel-2-methoxy-5-[[2-[(2S,5R)-5-methyl-2-(2-oxo-1H-Quinolin-6-yl)-1-piperidyl]-2-oxo-acetyl]amino]pyridine-3-carboxamide (Compound 810) and Rel-2-methoxy-5-[[2-[(2R,5S)-5-methyl-2-(2-oxo-1H-Quinolin-6-yl)-1-piperidyl]-2-oxo-acetyl]amino]pyridine-3-carboxamide (Compound 807

The mixture of diastereomers was separated by chiral chromatography (IA-II(250*20.5 mkm), IPA-MeOH, 50-50, 12 mL/min) to obtain (Compound 807)—rel-2-methoxy-5-[[2-[(2R,5S)-5-methyl-2-(2-oxo-1H-quinolin-6-yl)-1-piperidyl]-2-oxo-acetyl]amino]pyridine-3-carboxamide (38.31 mg, 82.66 µmol, 27.64% yield) and (Compound 810)—rel-2-methoxy-5-[[2-[(2S,5R)-5-methyl-2-(2-oxo-1H-quinolin-6-yl)-1-piperidyl]-2-oxo-acetyl]amino]pyridine-3-carboxamide (37.06 mg, 79.96 µmol, 26.74% yield)
Preparative:

RT for Compound 807 (IA-II(250*20, 5 mkm), IPA-MeOH, 50-50, 12 ml/min)=41.297 min.

RT for Compound 810 (IA-II(250*20, 5 mkm), IPA-MeOH, 50-50, 12 ml/min)=31.249 min.

Compound 810: RT (IC, IPA-MeOH, 50-50, 0.6 mL/min)=24.885 min.

$^1$H NMR (dmso, 600 MHz): δ (ppm) 0.98-1.09 (m, 3H), 1.30-1.44 (m, 1H), 1.63-1.76 (m, 1H), 1.81-1.93 (m, 1H), 2.02-2.18 (m, 1H), 2.19-2.28 (m, 1H), 2.77-3.24 (m, 1H), 3.45-3.50 (m, 0.6H), 3.88-3.96 (m, 3H), 3.97-4.02 (m, 0.4H), 5.11-5.72 (m, 1H), 6.40-6.54 (m, 1H), 7.21-7.36 (m, 1H), 7.37-7.50 (m, 1H), 7.57-7.64 (m, 1H), 7.65-7.77 (m, 2H), 7.82-7.93 (m, 1H), 8.37-8.59 (m, 2H), 10.91-11.11 (m, 1H), 11.66-11.76 (m, 1H).

LCMS(ESI): [M+H]+ m/z: calcd 463.2; found 464.2; Rt=2.401 min.

Compound 807: RT (IC, IPA-MeOH, 50-50, 0.6 mL/min)=32.686 min.

¹H NMR (dmso, 600 MHz): δ (ppm) 0.97-1.04 (m, 3H), 1.27-1.38 (m, 1H), 1.66-1.75 (m, 1H), 1.81-1.94 (m, 1H), 2.01-2.17 (m, 1H), 2.20-2.31 (m, 1H), 2.80-3.23 (m, 1H), 3.46-3.53 (m, 1H), 3.89-3.96 (m, 3H), 5.15-5.67 (m, 1H), 6.40-6.52 (m, 1H), 7.23-7.36 (m, 1H), 7.39-7.50 (m, 1H), 7.57-7.62 (m, 1H), 7.66-7.77 (m, 2H), 7.83-7.91 (m, 1H), 8.40-8.59 (m, 2H), 10.92-11.14 (m, 1H), 11.60-11.77 (m, 1H).

LCMS(ESI): [M+H]+ m/z: calcd 463.2; found 464.0; Rt=2.401 min.

Example 177. The Synthesis of Rel-5-[[2-[(2S,5R)-2-(6-isoquinolyl)-5-methyl-1-piperidyl]-2-oxo-acetyl]amino]pyridine-3-carboxamide (Compound 892) and Rel-5-[[2-[(2R,5S)-2-(6-isoquinolyl)-5-methyl-1-piperidyl]-2-oxo-acetyl]amino]pyridine-3-carboxamide (Compound 885

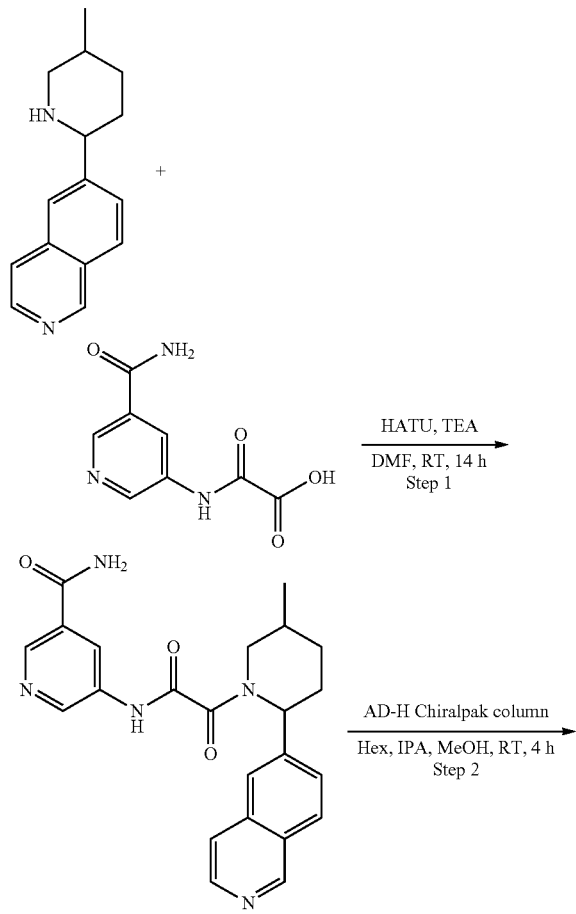

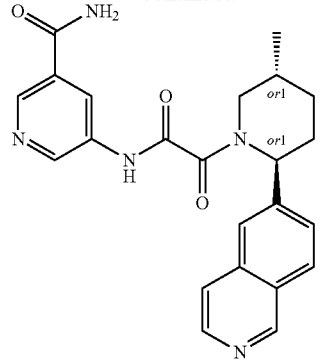

Compound 892

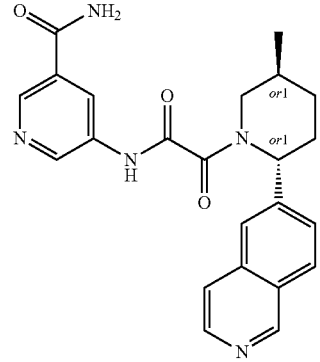

Compound 885

Step 1: The Synthesis of 5-[[2-[2-(6-isoquinolyl)-5-methyl-1-piperidyl]-2-oxo-acetyl]amino]pyridine-3-carboxamide 6-(5-methyl-2-piperidyl)isoquinoline (0.3 g, 1.33 mmol) was dissolved in DMF and Triethylamine (1.34 g, 13.26 mmol, 1.85 mL) was added, followed by 2-[(5-carbamoyl-3-pyridyl)amino]-2-oxo-acetic acid (325.59 mg, 1.33 mmol, HCl). Then the HATU (756.04 mg, 1.99 mmol) was added dropwise and the reaction mixture was stirred overnight. The next day it was evaporated in vacuo and purified by HPLC to obtain 5-[[2-[2-(6-isoquinolyl)-5-methyl-1-piperidyl]-2-oxo-acetyl]amino]pyridine-3-carboxamide (0.11 g, 263.50 µmol, 19.88% yield).

LCMS(ESI): [M+H]+ m/z: calcd 417.2; found 418.2; Rt=0.681 min.

Step 2: The Synthesis of Rel-5-[[2-[(2S,5R)-2-(6-isoquinolyl)-5-methyl-1-piperidyl]-2-oxo-acetyl]amino]pyridine-3-carboxamide (Compound 892) and Re-5-[[2-[(2R,5S)-2-(6-isoquinolyl)-5-methyl-1-piperidyl]-2-oxo-acetyl]amino]pyridine-3-carboxamide (Compound 885)

rac-5-[[2-[2-(6-isoquinolyl)-5-methyl-1-piperidyl]-2-oxo-acetyl]amino]pyridine-3-carboxamide (0.11 g, 263.50 µmol) was chiral separated (Column: Chiralpak AD-H (250*20 mm, 5 m); Mobile phase: Hexane-IPA-MeOH, 70-15-15 Flow Rate: 12 mL/min; Column Temperature: 24° C.; Wavelength: 205 nm, 210 nm, 254 nm RetTime (isomer A)=41.75 min) to obtain Compound 892—5-[[2-[(2S,5R)-2-(6-isoquinolyl)-5-methyl-1-piperidyl]-2-oxo-acetyl]amino]pyridine-3-carboxamide (0.05085 g, 121.81 µmol, 46.23% yield) and Compound 885—5-[[2-[(2R,5S)-2-(6-isoquinolyl)-5-methyl-1-piperidyl]-2-oxo-acetyl]amino]pyridine-3-carboxamide (0.04934 g, 118.19 μmol, 44.85% yield).

Compound 892: RT (AD-H, Hex-IPA-MeOH, 50-25-25, 0.6 mL/min)=23.254 min.

$^1$H NMR (DMSO-$d_6$, 500 MHz): δ (ppm) 1.06 (t, 3H), 1.39 (m, 1H), 1.73 (m, 1H), 1.89 (m, 1H), 2.18 (m, 1H), 2.39 (m, 2H), 3.83 (dd, 1H), 5.58 (m, 1H), 7.66 (m, 2H), 7.83 (m, 1H), 7.92 (m, 1H), 8.15 (m, 2H), 8.49 (m, 2H), 8.75 (m, 1H), 8.87 (m, 1H), 9.28 (m, 1H), 11.29 (m, 1H).

LCMS(ESI): [M+H]$^+$ m/z: calcd 417.2; found 418.2; Rt=0.854 min.

Compound 885: RT (AD-H, Hex-IPA-MeOH, 50-25-25, 0.6 mL/min)=34.603 min.

$^1$H NMR (DMSO-$d_6$, 500 MHz): δ (ppm) 1.06 (m, 3H), 1.39 (m, 1H), 1.79 (m, 2H), 2.25 (m, 3H), 3.83 (dd, 1H), 5.58 (m, 1H), 7.66 (m, 2H), 7.82 (t, 1H), 7.92 (d, 1H), 8.15 (m, 2H), 8.49 (m, 2H), 8.76 (m, 1H), 8.87 (m, 1H), 9.28 (m, 1H), 11.29 (m, 1H).

LCMS(ESI): [M+H]$^+$ m/z: calcd 417.2; found 418.2; Rt=0.855 min.

Example 178. The Synthesis of Rel-5-[[2-[(2R,5S)-2-(6-isoquinolyl)-5-methyl-1-piperidyl]-2-oxo-acetyl]amino]-2-methoxy-pyridine-3-carboxamide (Compound 914) and Rel-5-[[2-[(2S,5R)-2-(6-isoquinolyl)-5-methyl-1-piperidyl]-2-oxo-acetyl]amino]-2-methoxy-pyridine-3-carboxamide (Compound 933

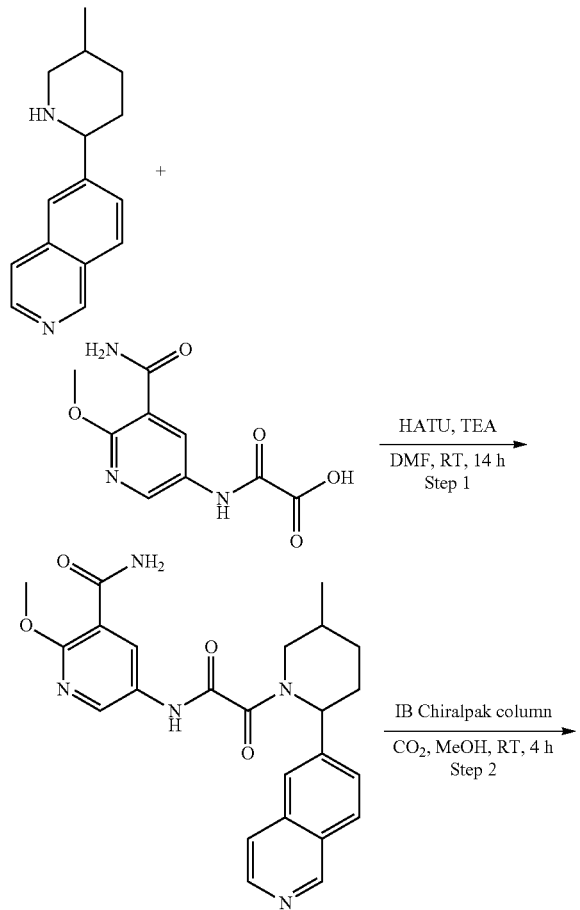

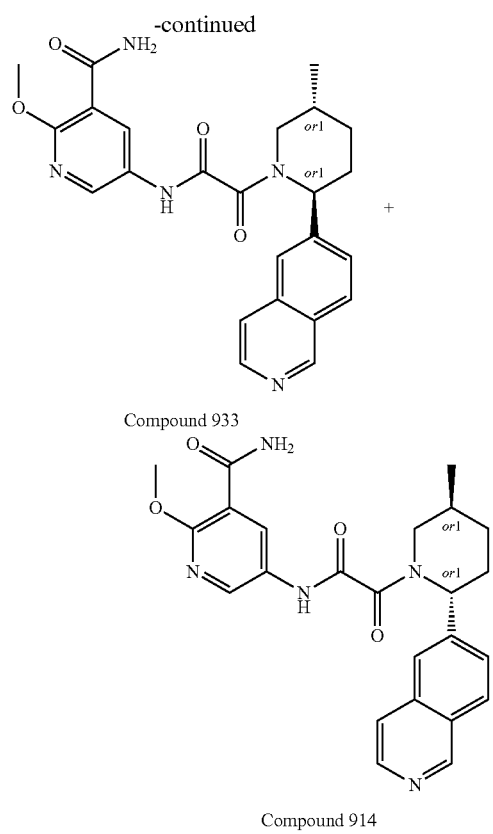

Compound 933

Compound 914

Step 1: The Synthesis of 5-[[2-[2-(6-isoquinolyl)-5-methyl-1-piperidyl]-2-oxo-acetyl]amino]-2-methoxy-pyridine-3-carboxamide 6-(5-methyl-2-piperidyl)isoquinoline (0.44 g, 1.94 mmol) was dissolved in DMF (10 mL) and triethylamine (1.97 g, 19.44 mmol, 2.71 mL) was added, followed by 2-[(5-carbamoyl-6-methoxy-3-pyridyl)amino]-2-oxo-acetic acid (465.02 mg, 1.94 mmol). Then the HATU (1.11 g, 2.92 mmol) was added dropwise and the reaction mixture was stirred overnight. The next day it was evaporated in vacuo and purified by HPLC to obtain 5-[[2-[2-(6-isoquinolyl)-5-methyl-1-piperidyl]-2-oxo-acetyl]amino]-2-methoxy-pyridine-3-carboxamide (0.12 g, 268.17 μmol, 13.79% yield).

LCMS(ESI): [M+H]$^+$ m/z: calcd 447.2; found 448.0; Rt=0.954 min.

Step 2: The Synthesis of Rei-5-[[2-[(2R,5S)-2-(6-isoquinolyl)-5-methyl-1-piperidyl]-2-oxo-acetyl]amino]-2-methoxy-pyridine-3-carboxamide (Compound 914) and Re-5-[[2-[(2S,5R)-2-(6-isoquinolyl)-5-methyl-1-piperidyl]-2-oxo-acetyl]amino]-2-methoxy-pyridine-3-carboxamide (Compound 933

5-[[2-[2-(6-isoquinolyl)-5-methyl-1-piperidyl]-2-oxo-acetyl]amino]-2-methoxy-pyridine-3-carboxamide (0.12 g, 268.17 μmol) was chiral separated (Column: Chiralpak IB (250*30 mm, 5 mkm); CO$_2$-MeOH, 65-35 as a mobile phase, 90 mL/min; Column Temperature: 40° C.; Wavelength: 215 nm. RetTime (isomer A)=8.55 min; RetTime (isomer B)=9.23 min) to obtain Compound 933—rel-5-[[2-[(2S,5R)-2-(6-isoquinolyl)-5-methyl-1-piperidyl]-2-oxoacetyl]amino]-2-methoxy-pyridine-3-carboxamide (0.04984 g, 111.38 μmol, 41.53% yield) and Compound 914—5-[[2-[(2R,5S)-2-(6-isoquinolyl)-5-methyl-1-piperidyl]-2-oxo-acetyl]amino]-2-methoxy-pyridine-3-carboxamide (56.12 mg, 125.41 μmol, 46.77% yield).

Compound 933: RT (IB, CO$_2$-MeOH, 60-40, 2.0 mL/min)=6.159 min.

$^1$H NMR (DMSO-d$_6$, 600 MHz): δ (ppm) 1.04 (m, 3H), 1.37 (m, 1H), 1.72 (m, 1H), 1.90 (m, 1H), 2.19 (m, 1H), 2.37 (m, 1H), 2.84 (m, 1H), 3.92 (m, 4H), 5.56 (d, 1H), 7.66 (m, 3H), 7.81 (m, 1H), 7.90 (m, 1H), 8.13 (m, 1H), 8.51 (m, 3H), 9.27 (m, 1H), 11.07 (m, 1H).

LCMS(ESI): [M+H]$^+$ m/z: calcd 447.2; found 448.2; Rt=0.964 min.

Compound 914: RT (IB, CO$_2$-MeOH, 60-40, 2.0 mL/min)=6.890 min.

$^1$H NMR (DMSO-d$_6$, 600 MHz): δ (ppm) 1.02 (m, 3H), 1.38 (m, 1H), 1.72 (m, 1H), 1.90 (m, 1H), 2.20 (m, 1H), 2.37 (m, 1H), 2.84 (m, 1H), 3.92 (m, 4H), 5.56 (d, 1H), 7.61 (d, 1H), 7.68 (m, 1H), 7.74 (m, 1H), 7.81 (m, 1H), 7.90 (m, 1H), 8.13 (dd, 1H), 8.50 (m, 3H), 9.27 (m, 1H), 11.07 (m, 1H).

LCMS(ESI): [M+H]$^+$ m/z: calcd 447.2; found 448.2; Rt=0.962 min.

Example 179. The Synthesis of Rel-5-[[2-[(2R,5S)-5-methyl-2-(6-methyl-3-pyridyl)-1-piperidyl]-2-oxo-acetyl]amino]pyridine-3-carboxamide (Compound 645) and Rel-5-[[2-[(2S,5R)-5-methyl-2-(6-methyl-3-pyridyl)-1-piperidyl]-2-oxo-acetyl]amino]pyridine-3-carboxamide (Compound 654

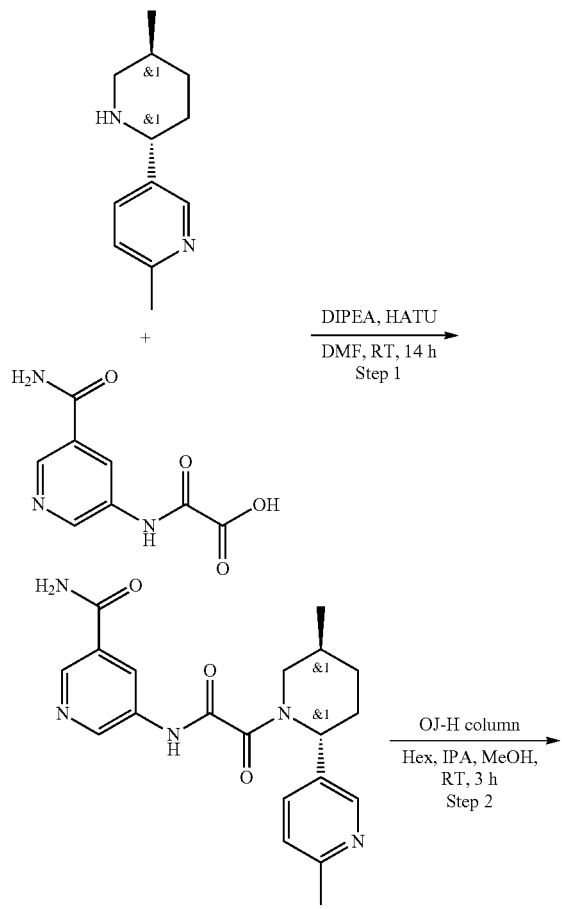

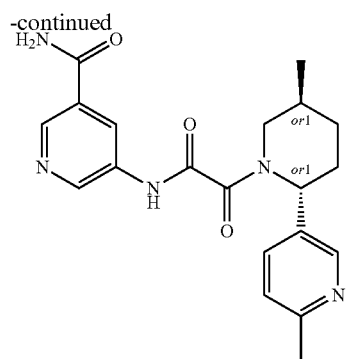

Compound 645

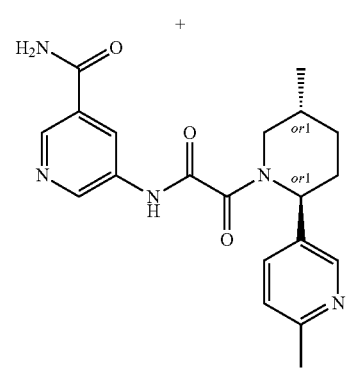

Compound 654

Step 1: The Synthesis of 5-[[2-[5-methyl-2-(6-methyl-3-pyridyl)-1-piperidyl]-2-oxo-acetyl]amino]pyridine-3-carboxamide DIPEA (631.43 mg, 4.89 mmol, 850.98 μL) was added to the solution of respective 2-[(5-carbamoyl-3-pyridyl)amino]-2-oxo-acetic acid (0.3 g, 1.22 mmol, HCl) and 2-methyl-5-(5-methyl-2-piperidyl)pyridine (232.41 mg, 1.22 mmol) in DMF (10 mL). The resulting mixture was stirred for 5 min followed by the addition of HATU (510.85 mg, 1.34 mmol). Then, the reaction mixture was stirred overnight at room temperature. After the completion of the reaction, monitored by LCMS, the resulting suspension was concentrated under reduced pressure. The obtained solid was subjected to HPLC (Waters SunFire 100*19 mm, 5 mkm column and H$_2$O-MeOH as an eluent mixture) to afford 5-[[2-[5-methyl-2-(6-methyl-3-pyridyl)-1-piperidyl]-2-oxo-acetyl]amino]pyridine-3-carboxamide (0.23 g, 603.00 μmol, 49.37% yield).

LCMS(ESI): [M+H]$^+$ m/z: calcd 381.4; found 382.4; Rt=1.202 min.

Step 2: The Synthesis of Rel-5-[[2-[(2R,5S)-5-methyl-2-(6-methyl-3-pyridyl)-1-piperidyl]-2-oxo-acetyl]amino]pyridine-3-carboxamide (Compound 645) and Rel-5-[[2-[(2S,5R)-5-methyl-2-(6-methyl-3-pyridyl)-1-piperidyl]-2-oxo-acetyl]amino]pyridine-3-carboxamide (Compound 654

5-[[2-[5-methyl-2-(6-methyl-3-pyridyl)-1-piperidyl]-2-oxo-acetyl]amino]pyridine-3-carboxamide (180.0 mg, 471.91 μmol) was chirally separated using OJ-H I (250*20 mm, 5 mkm) Chiralpak column and Hexane-IPA-MeOH, 70-15-15 as a mobile phase, Flow 15 mL/min affording Compound 645—rel-5-[[2-[(2R,5S)-5-methyl-2-(6-methyl-3-pyridyl)-1-piperidyl]-2-oxo-acetyl]amino]pyridine-3-carboxamide (79.97 mg, 43.89% yield) and Compound 654—rel-5-[[2-[(2S,5R)-5-methyl-2-(6-methyl-3-pyridyl)-1-piperidyl]-2-oxo-acetyl]amino]pyridine-3-carboxamide (94.9 mg, 52.72% yield).

Compound 645: RT (OJ-H, Hexane-IPA-MeOH, 70-15-15, 0.6 mL/min)=23.503 min.

$^1$H NMR (DMSO-d$_6$, 600 MHz): δ (ppm) 1.02 (m, 3H), 1.34 (m, 1H), 1.65 (m, 1H), 1.88 (m, 1H), 2.07 (m, 1H), 2.21 (m, 1H), 2.38 (m, 3H), 3.00 (m, 1H), 3.73 (m, 1H), 5.38 (m, 1H), 7.25 (m, 1H), 7.61 (m, 2H), 8.17 (m, 1H), 8.44 (m, 2H), 8.75 (m, 1H), 8.86 (m, 1H), 11.21 (m, 1H).

LCMS(ESI): [M+H]$^+$ m/z: calcd 381.2; found 382.2; Rt=0.787 min.

Compound 654: RT (OJ-H, Hexane-IPA-MeOH, 70-15-15, 0.6 mL/min)=14.127 min.

$^1$H NMR (DMSO-d$_6$, 600 MHz): δ (ppm) 1.01 (m, 3H), 1.33 (m, 1H), 1.65 (m, 1H), 1.89 (m, 1H), 2.05 (m, 1H), 2.20 (m, 1H), 2.38 (m, 3H), 2.99 (m, 1H), 3.69 (m, 1H), 5.38 (m, 1H), 7.25 (m, 1H), 7.60 (m, 2H), 8.14 (m, 1H), 8.44 (m, 2H), 8.75 (m, 1H), 8.86 (m, 1H), 11.21 (m, 1H).

LCMS(ESI): [M+H]$^+$ m/z: calcd 381.2; found 382.2; Rt=0.789 min.

Example 180. The Synthesis of Rel-2-methoxy-5-[[2-[(2S,5R)-5-methyl-2-(6-methyl-3-pyridyl)-1-piperidyl]-2-oxo-acetyl]amino]pyridine-3-carboxamide (Compound 754) and Rel-2-methoxy-5-[[2-[(2R,5S)-5-methyl-2-(6-methyl-3-pyridyl)-1-piperidyl]-2-oxo-acetyl]amino]pyridine-3-carboxamide (Compound 770

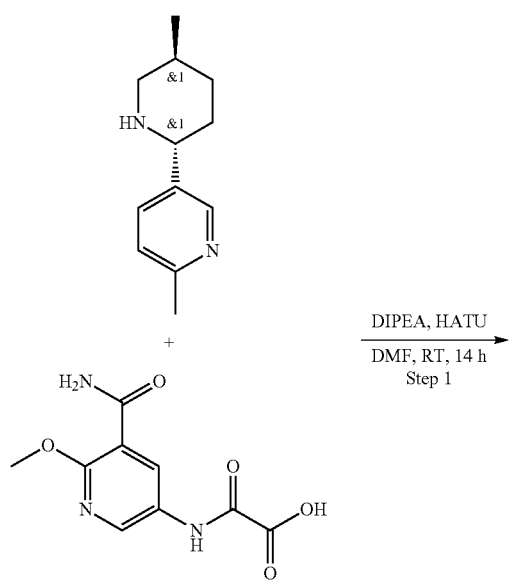

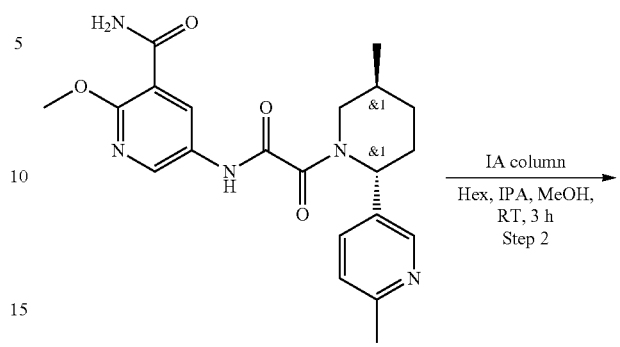

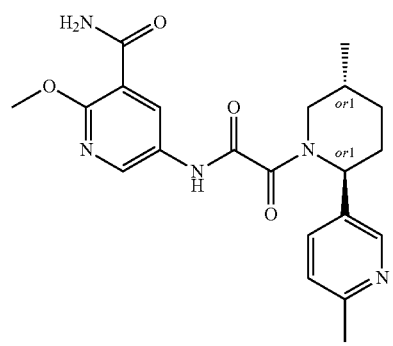

Compound 754

+

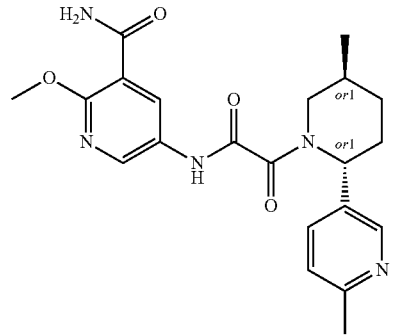

Compound 770

Step 1: The Synthesis of 2-methoxy-5-[[2-[5-methyl-2-(6-methyl-3-pyridyl)-1-piperidyl]-2-oxo-acetyl]amino]pyridine-3-carboxamide DIPEA (398.69 mg, 3.08 mmol, 537.32 μL) was added to the solution of respective 2-[(5-carbamoyl-6-methoxy-3-pyridyl)amino]-2-oxo-acetic acid (0.3 g, 881.38 μmol, Et$_3$N) and 2-methyl-5-(5-methyl-2-piperidyl)pyridine (167.71 mg, 881.38 μmol) in DMF (5 mL). The resulting mixture was stirred for 5 min followed by the addition of HATU (368.64 mg, 969.52 μmol). Then, the reaction mixture was stirred overnight at room temperature. After the completion of the reaction, monitored by LCMS, the resulting suspension was concentrated under reduced pressure. The obtained solid was subjected to HPLC (Waters SunFire C18 20*100 5 mkm column and H$_2$O-MeCN as an eluent mixture) to afford 2-methoxy-5-[[2-[5-methyl-2-(6-methyl-3-pyridyl)-1-piperidyl]-2-oxo-acetyl]amino]pyridine-3-carboxamide (0.13 g, 315.95 μmol, 35.85% yield).

$^1$H NMR (500 MHz, DMSO-d$_6$) δ 0.94 (s, 3H), 1.07 (m, 1H), 1.44 (m, 1H), 1.62 (m, 1H), 2.01 (m, 2H), 2.41 (m, 2H), 3.09 (s, 3H), 3.42 (m, 1H), 4.01 (s, 3H), 5.19 (m, 1H), 7.22 (m, 1H), 7.59 (m, 1H), 7.72 (m, 2H), 8.49 (m, 2H), 8.56 (s, 1H).

LCMS(ESI): [M+H]$^+$ m/z: calcd 411.2; found 412.0; Rt=1.467 min.

Step 5: The Synthesis of Rel-2-methoxy-5-[[2-[(2S,5R)-5-methyl-2-(6-methyl-3-pyridyl)-1-piperidyl]-2-oxo-acetyl]amino]pyridine-3-carboxamide (Compound 754) and Rel-2-methoxy-5-[[2-[(2R,5S)-5-methyl-2-(6-methyl-3-pyridyl)-1-piperidyl]-2-oxo-acetyl]amino]pyridine-3-carboxamide (Compound 770

2-methoxy-5-[[2-[5-methyl-2-(6-methyl-3-pyridyl)-1-piperidyl]-2-oxo-acetyl]amino]pyridine-3-carboxamide (130.0 mg, 315.95 μmol) was chirally separated using Chiralpak IA (250*20 mm, 5 mkm) and Hexane-IPA-MeOH, 40-30-30 as a mobile phase, Flow Rate: 12 mL/min; Column Temperature: 24° C.; Wavelength: 205 nm, 266 nm, 308 nm), RetTime (isomer A)=35.04 min; RetTime (isomers B)=46.12 min affording Compound 754-rel-2-methoxy-5-[[2-[(2S,5R)-5-methyl-2-(6-methyl-3-pyridyl)-1-piperidyl]-2-oxo-acetyl]amino]pyridine-3-carboxamide (22.66 mg, 17.43% yield) and Compound 770—2-methoxy-5-[[2-[(2R,5S)-5-methyl-2-(6-methyl-3-pyridyl)-1-piperidyl]-2-oxo-acetyl]amino]pyridine-3-carboxamide (40.84 mg, 31.42% yield).

Compound 754: RT (IA, Hexane-IPA-MeOH, 40-30-30, 0.6 mL/min)=10.508 min.

$^1$H NMR (600 MHz, DMSO-d$_6$) δ 0.93-1.08 (m, 3H), 1.26-1.40 (m, 1H), 1.56-1.74 (m, 1H), 1.83-1.93 (m, 1H), 1.98-2.15 (m, 1H), 2.15-2.25 (m, 1H), 2.41-2.45 (m, 3H), 2.71-3.24 (m, 1H), 3.44-4.02 (m, 4H), 5.12-5.62 (m, 1H), 7.19-7.32 (m, 1H), 7.51-7.65 (m, 1H), 7.65-7.77 (m, 2H), 8.34-8.47 (m, 2H), 8.47-8.58 (m, 1H), 10.88-11.10 (m, 1H).

LCMS(ESI): [M+H]$^+$ m/z: calcd 411.2; found 412.2; Rt=0.862 min.

Compound 770: RT (IA, Hexane-IPA-MeOH, 40-30-30, 0.6 mL/min)=72.637 min.

$^1$H NMR (600 MHz, DMSO-d$_6$) δ 1.02-1.04 (m, 3H), 1.27-1.38 (m, 1H), 1.59-1.70 (m, 1H), 1.80-1.93 (m, 1H), 1.99-2.15 (m, 1H), 2.15-2.25 (m, 1H), 2.41-2.44 (m, 3H), 2.72-3.24 (m, 1H), 3.44-4.02 (m, 4H), 5.13-5.60 (m, 1H), 7.19-7.30 (m, 1H), 7.54-7.65 (m, 1H), 7.66-7.78 (m, 2H), 8.37-8.47 (m, 2H), 8.47-8.56 (m, 1H), 10.94-11.08 (m, 1H).

LCMS(ESI): [M+H]$^+$ m/z: calcd 411.2; found 412.2; Rt=0.862 min.

Example 181. The Synthesis of 5-[[2-[(2S,5R)-2-(5-acetamido-2-thienyl)-5-methyl-1-piperidyl]-2-oxo-acetyl]amino]pyridine-3-carboxamide (Compound 704) and 5-[[2-[(2R,5S)-2-(5-acetamido-2-thienyl)-5-methyl-1-piperidyl]-2-oxo-acetyl]amino]pyridine-3-carboxamide (Compound 686

Compound 704

1585

-continued

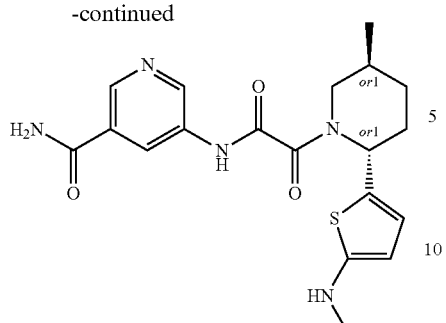

Compound 686

Step 1: The Synthesis of 5-[[2-[2-(5-acetamido-2-thienyl)-5-methyl-1-piperidyl]-2-oxo-acetyl]amino]pyridine-3-carboxamide 2-[(5-carbamoyl-3-pyridyl)amino]-2-oxo-acetic acid (627.34 mg, 2.55 mmol, HCl) and N-[5-(5-methyl-2-piperidyl)-2-thienyl]acetamide (0.9 g, 2.55 mmol, CF₃COOH) were mixed in DMF (15 mL). The reaction suspension was cooled to 20° C. and HATU (971.15 mg, 2.55 mmol) followed by TEA (1.29 g, 12.77 mmol, 1.78 mL) were added and stirred at ambient temperature for 14 hr. The reaction mixture was evaporated in vacuo and poured into water (100 ml) and extracted with EtOAc (2*30 ml). The combined organic extracts were washed with water (2*30 ml), dried over sodium sulphate and evaporated in vacuo and obtained crude product 0.45 g was purified by preparative 25-75% 0-5 min water-methanol, flow 30 ml/min to afford product 5-[[2-[2-(5-acetamido-2-thienyl)-5-methyl-1-piperidyl]-2-oxo-acetyl]amino]pyridine-3-carboxamide (0.100 g, 232.83 µmol, 9.12% yield).

LCMS(ESI): [M+H]⁺ m/z: calcd 429.1; found 430.0; Rt=1.948 min.

Step 2: The Synthesis of 5-[[2-[(2S,5R)-2-(5-acetamido-2-thienyl)-5-methyl-1-piperidyl]-2-oxo-acetyl]amino]pyridine-3-carboxamide (Compound 704) and 5-[[2-[(2R,5S)-2-(5-acetamido-2-thienyl)-5-methyl-1-piperidyl]-2-oxo-acetyl]amino]pyridine-3-carboxamide (Compound 686

The enantiomers were separated by chiral HPLC (column: OJ-H (250*20, 5 mkm)), Hexane-IPA-MeOH, 70-15-15, 14 ml/min as mobile phase) to give the two individual enantiomers Compound 704 5-[[2-[(2S,5R)-2-(5-acetamido-2-thienyl)-5-methyl-1-piperidyl]-2-oxo-acetyl]amino]pyridine-3-carboxamide (37.20 mg, 86.61 µmol, 37.20% yield) and Compound 686 5-[[2-[(2R,5S)-2-(5-acetamido-2-thienyl)-5-methyl-1-piperidyl]-2-oxo-acetyl]amino]pyridine-3-carboxamide (0.0461 g, 107.34 µmol, 46.10% yield).

Compound 686: RT (IA, Hexane-IPA-MeOH, 70-15-15, 0.6 mL/min)=30.346 min.

¹H NMR (DMSO-d₆, 600 MHz): δ (ppm) 0.78 (m, 3H), 1.30 (m, 2H), 1.68 (m, 2H), 1.88 (m, 1H), 2.02 (m, 3H), 2.21 (m, 1H), 3.90 (m, 1H), 5.53 (m, 1H), 6.47 (m, 1H), 6.69 (m, 1H), 7.58 (m, 1H), 8.15 (m, 1H), 8.49 (m, 1H), 8.81 (m, 2H), 11.05 (s, 1H), 11.23 (s, 1H).

LCMS(ESI): [M+H]⁺ m/z: calcd 429.2; found 430.2; Rt=1.042 min.

1586

Compound 704: RT (IA, Hexane-IPA-MeOH, 70-15-15, 0.6 mL/min)=26.867 min.

¹H NMR (DMSO-d₆, 600 MHz): δ (ppm) 0.79 (dd, 3H), 1.31 (m, 1H), 1.68 (m, 2H), 1.89 (m, 1H), 2.01 (m, 3H), 2.20 (m, 1H), 2.72 (m, 1H), 3.89 (m, 1H), 5.53 (m, 1H), 6.47 (m, 1H), 6.69 (m, 1H), 7.59 (d, 1H), 8.15 (d, 1H), 8.49 (m, 1H), 8.75 (m, 1H), 8.87 (m, 1H), 11.05 (s, 1H), 11.23 (s, 1H).

LCMS(ESI): [M+H]⁺ m/z: calcd 429.2; found 430.2; Rt=1.041 min.

Example 182. The Synthesis of 5-(2-(2-(3,4-di-hydro-2H-benzo[b][1,4]Oxazin-7-yl)-5-methylpiperidin-1-yl)-2-oxoacetamido)Nicotinamide (Compound 598 and Compound 605

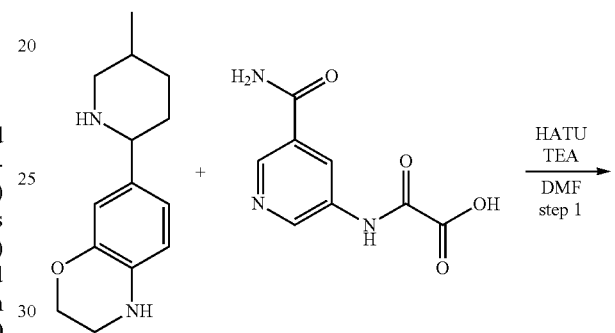

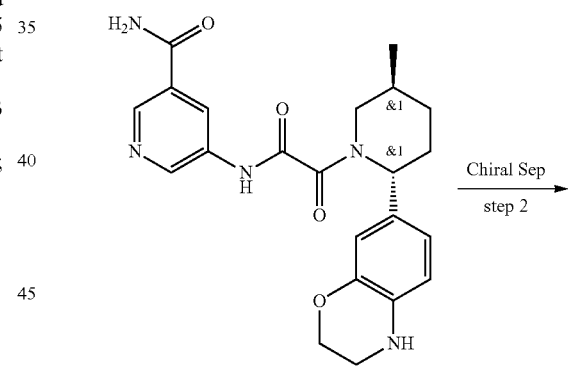

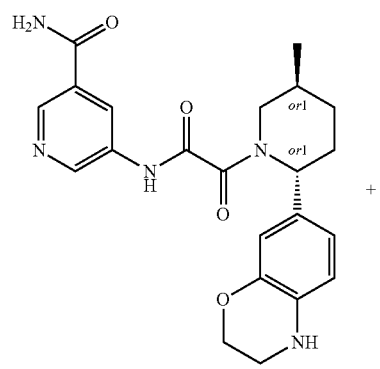

Compound 598

-continued

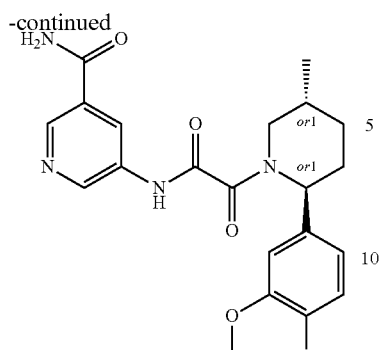

Compound 605

Step 1: Synthesis of 5-(2-(2-(3,4-dihydro-2H-benzo[b][1,4]Oxazin-7-yl)-5-methylpiperidin-1-yl)-2-oxoacetamido)Nicotinamide 7-(5-methyl-2-piperidyl)-3,4-dihydro-2H-1,4-benzoxazine (0.68 g, 1.46 mmol), 2-[(5-carbamoyl-3-pyridyl)amino]-2-oxo-acetic acid (359.46 mg, 1.46 mmol, HCl), TEA (740.46 mg, 7.32 mmol, 1.02 mL) were mixed in DMF (10 mL) and then HATU (834.70 mg, 2.20 mmol) were added. Resulting mixture were stirred at 25° C. for 13 hr. The mixture was evaporated under reduce pressure and purified with HPLC (2-10 min 50-60% MeOH/H₂O+NH₃, 30 ml/min) to obtain 5-[[2-[(2S,5R)-2-(3,4-dihydro-2H-1,4-benzoxazin-7-yl)-5-methyl-1-piperidyl]-2-oxo-acetyl]amino]pyridine-3-carboxamide (166.9 mg, 394.13 µmol, 26.93% yield).

LCMS(ESI): [M]⁺ m/z: calcd 423.2; found 424.2; Rt=1.029 min.

Step 2: Chiral Separation (Compound 598 and Compound 605

The mixture of diastereomers was separated by chiral chromatography (IA-II (250*20, 5 mkm), Hexane-IPA-MeOH, 40-30-30, 10 ml/min) to obtain 5-[[2-[(2R,5S)-2-(3,4-dihydro-2H-1,4-benzoxazin-7-yl)-5-methyl-1-piperidyl]-2-oxo-acetyl]amino]pyridine-3-carboxamide (58.99 mg, 139.30 µmol, 35.34% yield) (RT=57.029) and 5-[[2-[(2S,5R)-2-(3,4-dihydro-2H-1,4-benzoxazin-7-yl)-5-methyl-1-piperidyl]-2-oxo-acetyl]amino]pyridine-3-carboxamide (48.14 mg, 113.68 µmol, 28.84% yield) (RT=32.475).

Ret time for Compound 598 in analytical conditions (column: IA, IPA-MeOH, 50-50, 0.6 ml/min as mobile phase) 48.55 min and for Compound 605 15.51 min.

Compound 598: Retention time: 48.55 min

¹H NMR (600 MHz, DMSO-d₆) δ (ppm) 0.96-1.03 (m, 3H), 1.24-1.35 (m, 1H), 1.65-1.78 (m, 1H), 1.78-1.90 (m, 1H), 1.91-2.06 (m, 1H), 2.06-2.14 (m, 1H), 2.77-3.26 (m, 3H), 3.36-3.97 (m, 1H), 4.05-4.17 (m, 2H), 4.92-5.74 (m, 2H), 6.49-6.60 (m, 2H), 6.60-6.65 (m, 1H), 7.47-7.63 (m, 1H), 8.08-8.21 (m, 1H), 8.42-8.51 (m, 1H), 8.70-8.80 (m, 1H), 8.81-8.95 (m, 1H), 10.84-11.39 (m, 1H).

LCMS(ESI): [M]⁺ m/z: calcd 423.2; found 424.2; Rt=2.289 min.

Compound 605: Retention time: 15.51 min

¹H NMR (600 MHz, DMSO-d₆) δ (ppm) 0.95-1.03 (m, 3H), 1.24-1.37 (m, 1H), 1.65-1.76 (m, 1H), 1.79-1.90 (m, 1H), 1.93-2.06 (m, 1H), 2.06-2.15 (m, 1H), 2.75-3.24 (m, 3H), 3.37-3.98 (m, 1H), 4.05-4.12 (m, 2H), 4.86-5.77 (m, 2H), 6.49-6.60 (m, 2H), 6.60-6.64 (m, 1H), 7.45-7.65 (m, 1H), 8.07-8.21 (m, 1H), 8.38-8.51 (m, 1H), 8.68-8.79 (m, 1H), 8.83-8.93 (m, 1H), 10.94-11.31 (m, 1H).

LCMS(ESI): [M]⁺ m/z: calcd 423.2; found 424.2; Rt=2.290 min.

Example 183. The Synthesis of 5-(2-(2-(3,4-dihydro-2H-benzo[b][1,4]Oxazin-7-yl)-5-methylpiperidin-1-yl)-2-oxoacetamido)-2-methoxynicotinamide (Compound 869

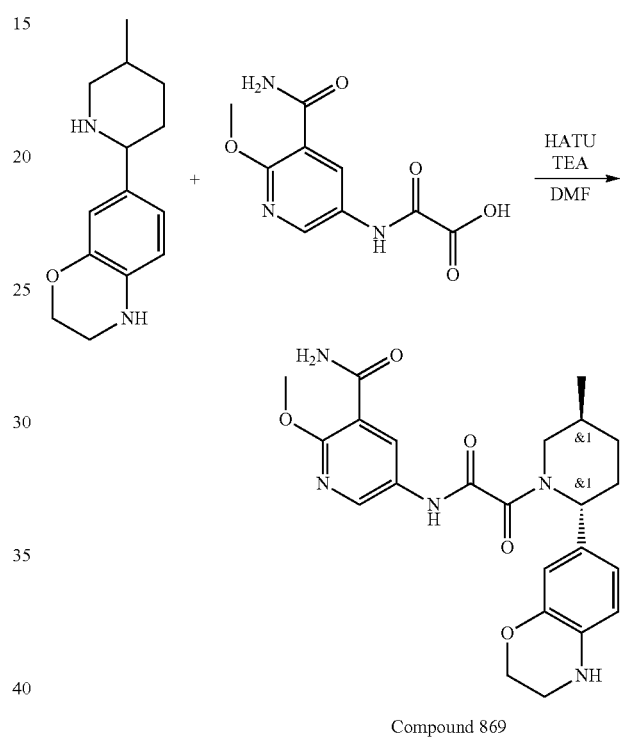

Compound 869

7-[(2R,5S)-5-methyl-2-piperidyl]-3,4-dihydro-2H-1,4-benzoxazine (0.2 g, 860.88 µmol), TEA (871.12 mg, 8.61 mmol, 1.20 mL) and 2-[(5-carbamoyl-6-methoxy-3-pyridyl)amino]-2-oxo-acetic acid (205.91 mg, 860.88 µmol) was dissolved in DMF (8.5 mL) and HATU (491.00 mg, 1.29 mmol) was added in one portion, the resulting mixture was stirred for 3 hr at 20° C. Reaction mixture was poured into water and the aqueous phase was extracted with EtOAc (3 times), then the combined organic phase was washed with brine (3 times), dried over Na₂SO₄ and concentrated on vacuum. The crude product was purified by reverse phase HPLC (2-10 min 10-25% MeCN/H₂O 30 ml/min (loading pump 4 ml MeCN); column: SunFire 100*19 mm, 5 microM) to give 5-[[2-[(2R,5S)-2-(3,4-dihydro-2H-1,4-benzoxazin-7-yl)-5-methyl-1-piperidyl]-2-oxo-acetyl]amino]-2-methoxy-pyridine-3-carboxamide (0.052 g, 114.67 µmol, 13.32% yield) as a white solid. The reaction was successful. The desired product 5-[[2-[(2R,5S)-2-(3,4-dihydro-2H-1,4-benzoxazin-7-yl)-5-methyl-1-piperidyl]-2-oxo-acetyl]amino]-2-methoxy-pyridine-3-carboxamide (0.052 g, 114.67 µmol, 13.32% yield) was isolated as white solid.

Compound 869: ¹H NMR (600 MHz, DMSO-d₆) δ (ppm) 0.94-1.03 (m, 3H), 1.25-1.34 (m, 1H), 1.62-1.75 (m, 1H), 1.77-1.88 (m, 1H), 1.90-2.04 (m, 1H), 2.06-2.13 (m, 1H), 2.74-3.20 (m, 1H), 3.21-3.25 (m, 2H), 3.36-3.40 (m, 1H), 3.90-3.95 (m, 3H), 4.05-4.13 (m, 2H), 4.91-5.50 (m, 1H), 5.69 (s, 1H), 6.48-6.68 (m, 3H), 7.66-7.79 (m, 2H), 8.39-8.47 (m, 1H), 8.48-8.60 (m, 1H), 10.75-11.21 (m, 1H).

LCMS(ESI): [M]+ m/z: calcd 453.2; found 454.2; Rt=1.129 min.

Example 184. The Synthesis of 5-(2-(5-methyl-2-(1-oxoisoindolin-5-yl)piperidin-1-yl)-2-oxoacetamido)Nicotinamide (Compound 741 and Compound 740

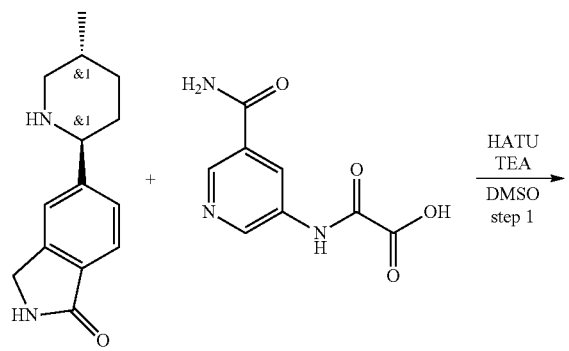

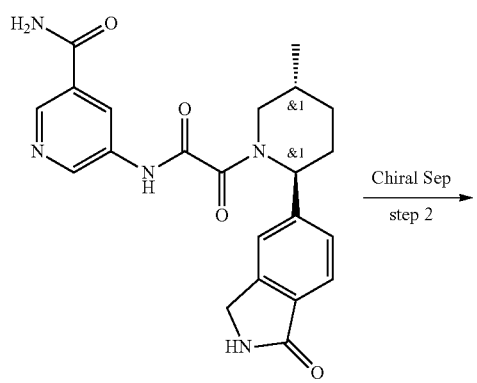

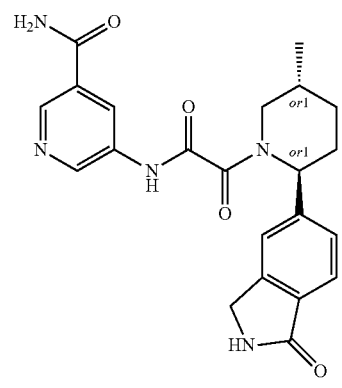

Compound 740

+

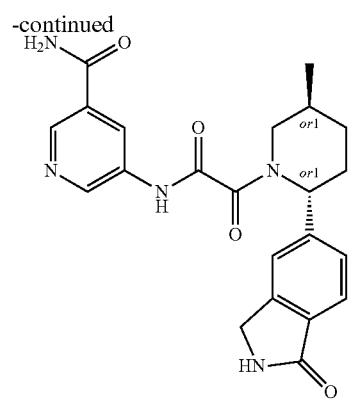

Compound 741

Step 1: Synthesis of 5-(2-(5-methyl-2-(1-oxoisoindolin-5-yl)piperidin-1-yl)-2-oxoacetamido)Nicotinamide 5-[(2R,5S)-5-methyl-2-piperidyl]isoindolin-1-one (200.00 mg, 868.41 μmol), 2-[(5-carbamoyl-3-pyridyl) amino]-2-oxo-acetic acid (269.51 mg, 868.41 μmol), HATU (363.22 mg, 955.26 μmol) and TEA (87.87 mg, 868.41 μmol, 121.04 μL) were mixed in DMSO (4 mL) and stirred for 3 hr at 20° C. Reaction mixture was subjected to HPLC (2-10 min 0-65% MeCN/water 30 ml/min (loading pump 4 ml MeCN) column: YMC-ACTUS TRIART C18 100*20 5 microM) to afford to 5-[[2-[(2R,5S)-5-methyl-2-(1-oxoisoindolin-5-yl)-1-piperidyl]-2-oxo-acetyl]amino]pyridine-3-carboxamide (190 mg, 450.83 μmol, 51.91% yield).

LCMS(ESI): [M]+ m/z: calcd 421.2; found 422.2; Rt=1.884 min.

Step 2: Chiral Separation (Compound 741 and Compound 740 rac-5-(2-((2R,5S)-5-methyl-2-(1-oxoisoindolin-5-yl)piperidin-1-yl)-2-oxoacetamido)nicotinamide (190 mg, 450.83 mmol) was divided into enantiomers by Chiral HPLC (AD (250*30, 20 mkm), CO2-MeOH, 55-45, 90 ml/min make up flow rate—30 ml/min).

Ret time for Compound 741 in analytical conditions (column: AD-H, CO2-MeOH, 50-50, 2 ml/min as mobile phase) 14.43 min and for Compound 740 10.20 min.

Compound 741: Retention time: 14.43 min H NMR (600 MHz, DMSO-d6) δ (ppm) 1.03 (m, 3H), 1.35 (m, 1H), 1.68 (m, 1H), 1.89 (m, 1H), 2.07 (m, 1H), 2.20 (m, 1H), 2.97 (m, 1H), 3.69 (m, 1H), 4.35 (m, 2H), 5.46 (m, 1H), 7.44 (m, 1H), 7.53 (m, 1H), 7.59 (m, 1H), 7.67 (m, 1H), 8.15 (m, 1H), 8.48 (m, 2H), 8.75 (m, 1H), 8.87 (m, 1H), 11.23 (m, 1H).

LCMS(ESI): [M]+ m/z: calcd 421.2; found 422.2; Rt=1.981 min.

Compound 740: Retention time: 10.20 min

1H NMR (600 MHz, DMSO-d6) δ (ppm) 1.03 (m, 3H), 1.35 (m, 1H), 1.68 (m, 1H), 1.96 (m, 2H), 2.23 (m, 1H), 2.83 (m, 1H), 3.78 (m, 1H), 4.35 (m, 2H), 5.46 (m, 1H), 7.57 (m, 4H), 8.14 (m, 1H), 8.48 (m, 2H), 8.80 (m, 2H), 11.23 (m, 1H).

LCMS(ESI): [M]+ m/z: calcd 421.2; found 422.2; Rt=1.982 min.

Example 185. The Synthesis of 2-methoxy-5-(2-(5-methyl-2-(1-oxoisoindolin-5-yl)piperidin-1-yl)-2-oxoacetamido)Nicotinamide (Compound 749 and Compound 750

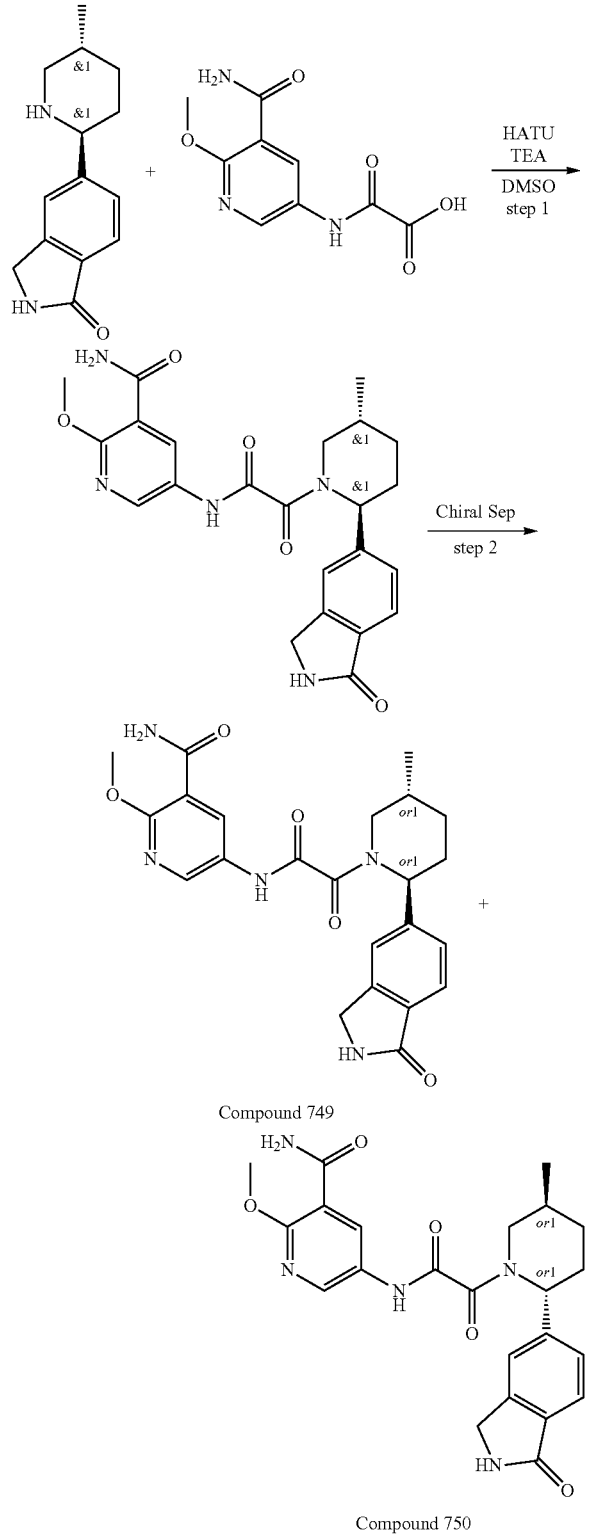

Compound 749

Compound 750

Step 1: Synthesis of 2-methoxy-5-(2-(5-methyl-2-(1-oxoisoindolin-5-yl)piperidin-1-yl)-2-oxoacetamido)Nicotinamide 5-[(2R,5S)-5-methyl-2-piperidyl]isoindolin-1-one (200.00 mg, 868.41 μmol), 2-[(5-carbamoyl-6-methoxy-3-pyridyl)amino]-2-oxo-acetic acid (295.59 mg, 868.41 μmol), HATU (363.22 mg, 955.26 μmol) and TEA (87.87 mg, 868.41 μmol, 121.04 μL) were mixed in DMSO (4 mL) and stirred for 3 hr at 20° C. Reaction mixture was subjected to HPLC (2-10 min 45-60% water/MeOH+NH₃ (loading pump 4 ml MeOH+NH₃) column: TRIART 100*20 5 microM). 2-methoxy-5-[[2-[(2R,5S)-5-methyl-2-(1-oxoisoindolin-5-yl)-1-piperidyl]-2-oxo-acetyl]amino]pyridine-3-carboxamide (170 mg, 376.54 μmol, 43.36% yield) was obtained.

LCMS(ESI): [M]⁺ m/z: calcd 451.2; found 452.2; Rt=2.251 min.

Step 2: Chiral Separation (Compound 749 and Compound 750 rac-2-methoxy-5-(2-((2R,5S)-5-methyl-2-(1-oxoisoindolin-5-yl)piperidin-1-yl)-2-oxoacetamido) nicotinamide (170 mg, 376.54 mmol) was divided into enantiomers by Chiral HPLC (IA, IPA-MeOH, 50-50, 12 ml/min).

Ret time for Compound 749 in analytical conditions (column: IA, IPA-MeOH, 50-50, 0.6 ml/min as mobile phase) 20.24 min and for Compound 750 37.82 min.

Compound 749: Retention time: 20.24 min

¹H NMR (600 MHz, DMSO-d₆) δ (ppm) 1.00-1.04 (m, 3H), 1.26-1.41 (m, 1H), 1.59-1.74 (m, 1H), 1.81-1.94 (m, 1H), 2.04-2.19 (m, 1H), 2.19-2.32 (m, 1H), 2.79-3.27 (m, 1H), 3.47-3.56 (m, 0.6H), 3.89-3.98 (m, 3H), 4.00-4.06 (m, 0.4H), 4.31-4.41 (m, 2H), 5.24-5.70 (m, 1H), 7.39-7.47 (m, 1H), 7.49-7.56 (m, 1H), 7.62-7.68 (m, 1H), 7.68-7.78 (m, 2H), 8.41-8.58 (m, 3H), 10.87-11.15 (m, 1H).

LCMS(ESI): [M]⁺ m/z: calcd 451.2; found 452.2; Rt=2.124 min.

Compound 750: Retention time: 37.82 min

¹H NMR (600 MHz, DMSO-d₆) δ (ppm) 1.00-1.07 (m, 3H), 1.30-1.42 (m, 1H), 1.61-1.71 (m, 1H), 1.82-1.95 (m, 1H), 2.02-2.18 (m, 1H), 2.20-2.31 (m, 1H), 2.78-3.26 (m, 1H), 3.46-3.56 (m, 0.7H), 3.87-3.98 (m, 3H), 4.01-4.05 (m, 0.3H), 4.28-4.42 (m, 2H), 5.25-5.71 (m, 1H), 7.39-7.47 (m, 1H), 7.49-7.55 (m, 1H), 7.62-7.67 (m, 1H), 7.68-7.79 (m, 2H), 8.40-8.60 (m, 3H), 11.01 (br s, 1H).

LCMS(ESI): [M]⁺ m/z: calcd 451.2; found 452.2; Rt=2.134 min.

Example 186. The Synthesis of N-(6-amino-5-ethylpyridin-3-yl)-2-(5-methyl-2-(1-oxoisoindolin-5-yl)piperidin-1-yl)-2-oxoacetamide (Compound 696 and Compound 699

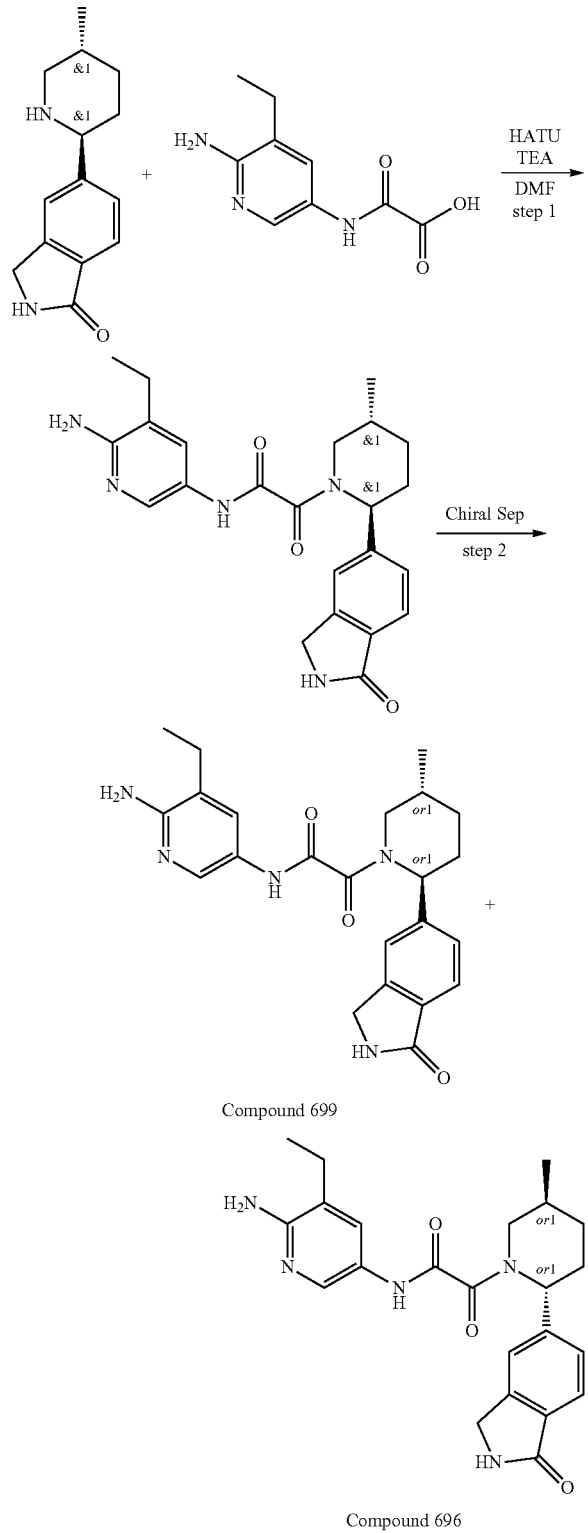

Step 1: Synthesis of N-(6-amino-5-ethylpyridin-3-yl)-2-(5-methyl-2-(1-oxoisoindolin-5-yl)piperidin-1-yl)-2-oxoacetamide 2-[(6-amino-5-ethyl-3-pyridyl)amino]-2-oxo-acetic acid (472.35 mg, 2.26 mmol) and TEA (1.76 g, 17.37 mmol, 2.42 mL) were dissolved in DMF (12 mL) and cooled to 0° C., HATU (990.59 mg, 2.61 mmol) was added and the mixture was stirred for 15 min at 0° C. 5-[(2S,5R)-5-methyl-2-piperidyl]isoindolin-1-one (0.4 g, 1.74 mmol) was added and the mixture was warmed to rt and stirred for 3 hr. Ethyl acetate was added and organic phase was washed with brine three times. Organic phase was dried over $Na_2SO_4$, filtered and concentrated in vacuum at 45° C. to give crude product which was purified by HPLC (2-10 min 60-80% MeOH/$H_2O$ 30 ml/min (loading pump 4 ml MeOH) column: SunFire 100*19 mm, 5 micro) to give N-(6-amino-5-ethyl-3-pyridyl)-2-[(2S,5R)-5-methyl-2-(1-oxoisoindolin-5-yl)-1-piperidyl]-2-oxo-acetamide (0.049 g, 116.25 μmol, 6.69% yield).

LCMS(ESI): $[M]^+$ m/z: calcd 421.2; found 422.2; Rt=0.967 min.

Step 2: Chiral Separation (Compound 696 and Compound 699

Chiral separation was performed using Column: Chiralpak IB (250*30 mm, 5 mkm); Mobile phase: $CO_2$-MeOH 70-30 Flow Rate: 80 mL/min to give N-(6-amino-5-ethyl-3-pyridyl)-2-[(2S,5R)-5-methyl-2-(1-oxoisoindolin-5-yl)-1-piperidyl]-2-oxo-acetamide (0.016 g, 37.96 μmol, 32.65% yield) and N-(6-amino-5-ethyl-3-pyridyl)-2-[(2R,5S)-5-methyl-2-(1-oxoisoindolin-5-yl)-1-piperidyl]-2-oxo-acetamide (15.7 mg, 37.25 μmol, 32.04% yield).

Ret time for Compound 699 in analytical conditions (column: IB, $CO_2$-MeOH, 70-30, 2 ml/min as mobile phase) 28.36 min and for Compound 696 14.52 min.

Compound 699: Retention time: 28.36 min $^1$H NMR (600 MHz, DMSO-$d_6$) δ (ppm) 1.06 (m, 6H), 1.33 (m, 1H), 1.65 (m, 1H), 1.87 (m, 1H), 2.06 (m, 1H), 2.23 (m, 1H), 2.36 (m, 1H), 2.40 (m, 1H), 2.77 (m, 1H), 3.76 (m, 1H), 4.35 (m, 2H), 5.52 (m, 3H), 7.46 (m, 3H), 7.66 (m, 1H), 8.01 (m, 1H), 8.50 (s, 1H), 10.50 (m, 1H).

LCMS(ESI): $[M]^+$ m/z: calcd 421.2; found 422.2; Rt=0.859 min.

Compound 696: Retention time: 14.52 min $^1$H NMR (600 MHz, DMSO-$d_6$) δ (ppm) 1.05 (m, 6H), 1.34 (m, 1H), 1.65 (m, 1H), 1.87 (m, 1H), 2.06 (m, 1H), 2.24 (m, 1H), 2.36 (m, 2H), 2.78 (m, 1H), 3.76 (m, 1H), 4.35 (m, 2H), 5.52 (m, 3H), 7.46 (m, 3H), 7.65 (m, 1H), 8.02 (m, 1H), 8.51 (s, 1H), 10.51 (m, 1H).

LCMS(ESI): $[M]^+$ m/z: calcd 421.2; found 422.2; Rt=0.864 min.

1595

Example 187. The Synthesis of 5-(2-(5-methyl-2-(4-(Thiazol-5-yl)phenyl)piperidin-1-yl)-2-oxoacetamido)Nicotinamide (Compound 821 and Compound 817

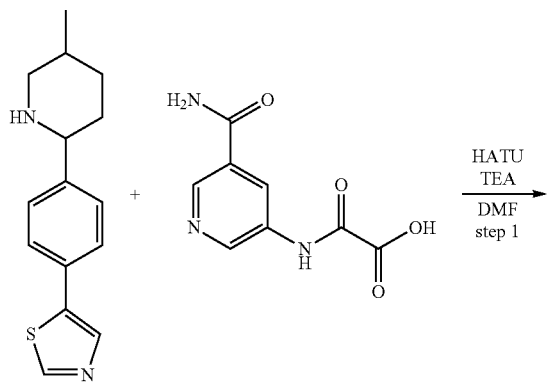

HATU
TEA
DMF
step 1

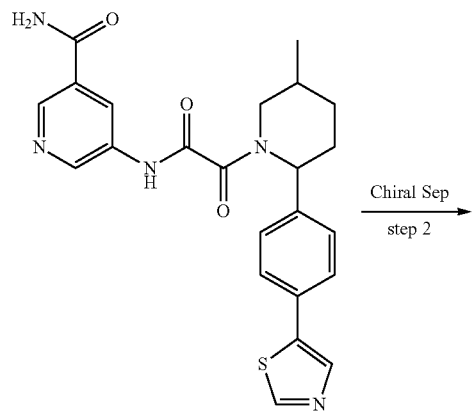

Chiral Sep
step 2

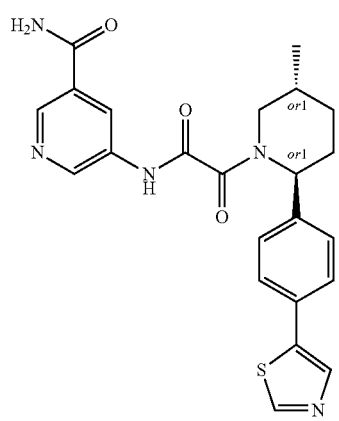

Compound 821
+

1596

-continued

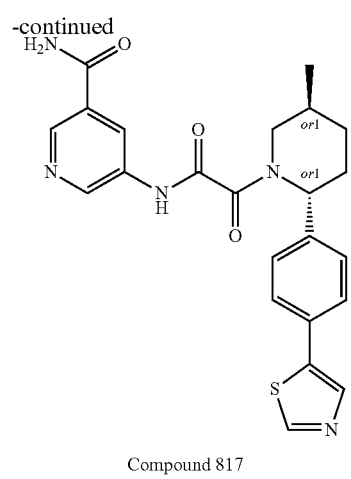

Compound 817

Step 1: Synthesis of 5-(2-(5-methyl-2-(4-(Thiazol-5-yl)phenyl)piperidin-1-yl)-2-oxoacetamido)Nicotinamide DIPEA (331.50 mg, 2.56 mmol, 446.77 µL) was added to the solution of respective 2-[(5-carbamoyl-3-pyridyl)amino]-2-oxo-acetic acid (0.18 g, 732.84 µmol, HCl) and 5-[4-(5-methyl-2-piperidyl)phenyl]thiazole (189.35 mg, 732.84 µmol) in DMF (10 mL). The resulting mixture was stirred for 5 min followed by the addition of HATU (306.51 mg, 806.12 µmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and MeCN as an eluent mixture) to afford 5-[[2-[5-methyl-2-(4-thiazol-5-ylphenyl)-1-piperidyl]-2-oxo-acetyl]amino]pyridine-3-carboxamide (0.18 g, 400.42 µmol, 54.64% yield).

LCMS(ESI): $[M]^+$ m/z: calcd 449.2; found 450.2; Rt=2.576 min.

Step 6: Chiral Separation (Compound 817 and Compound 821

5-(2-(5-methyl-2-(4-(thiazol-5-yl)phenyl)piperidin-1-yl)-2-oxoacetamido)nicotinamide (185 mg, 411.55 mmol) was divided into enantiomers by Chiral HPLC (IC-II (250*20, 5 mkm), IPA-MeOH, 50-50, 10 ml/min).

Ret time for Compound 817 in analytical conditions (column: IC, $CO_2$-MeOH, 50-50, 2 ml/min as mobile phase) 25.94 min and for Compound 821 56.45 min.

Compound 817: Retention time: 25.94 min $^1$H NMR (600 MHz, DMSO-$d_6$) δ (ppm) 1.00-1.05 (m, 3H), 1.32-1.41 (m, 1H), 1.63-1.73 (m, 1H), 1.85-1.96 (m, 1H), 2.04-2.17 (m, 1H), 2.20-2.30 (m, 1H), 2.77-3.26 (m, 1H), 3.47-4.08 (m, 1H), 5.15-5.69 (m, 1H), 7.36-7.44 (m, 2H), 7.55-7.63 (m, 1H), 7.66-7.73 (m, 2H), 8.10-8.20 (m, 1H), 8.28-8.33 (m, 1H), 8.45-8.52 (m, 1H), 8.71-8.81 (m, 1H), 8.82-8.93 (m, 1H), 9.04-9.09 (m, 1H), 11.21-11.34 (m, 1H).

LCMS(ESI): $[M]^+$ m/z: calcd 449.2; found 450.2; Rt=2.573 min.

Compound 821: Retention time: 56.45 min $^1$H NMR (600 MHz, DMSO-$d_6$) δ (ppm) 1.00-1.05 (m, 3H), 1.33-1.40 (m, 1H), 1.64-1.72 (m, 1H), 1.84-1.94 (m, 1H), 2.03-2.15 (m, 1H), 2.22-2.32 (m, 1H), 2.79-3.27 (m, 1H), 3.47-4.08 (m, 1H), 5.14-5.64 (m, 1H), 7.35-7.45 (m, 2H), 7.56-7.66 (m, 1H), 7.66-7.77 (m, 2H), 8.10-8.22 (m, 1H), 8.25-8.35 (m, 1H), 8.41-8.55 (m, 1H), 8.71-8.81 (m, 1H), 8.82-8.93 (m, 1H), 9.02-9.11 (m, 1H), 11.18-11.33 (m, 1H).

LCMS(ESI): [M]⁺ m/z: calcd 449.2; found 450.2; Rt=2.573 min.

Example 188. The Synthesis of 2-methoxy-5-(2-(5-methyl-2-(4-(Thiazol-5-yl)phenyl)piperidin-1-yl)-2-oxoacetamido)Nicotinamide (Compound 830 and Compound 842

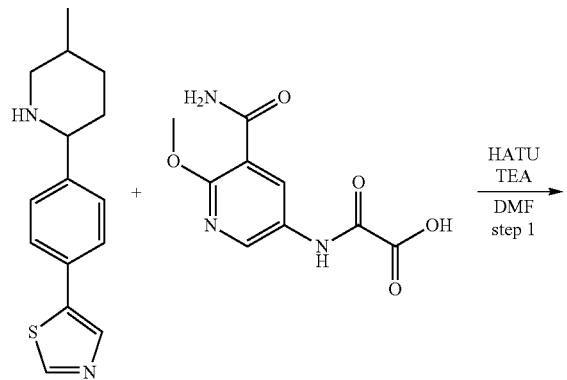

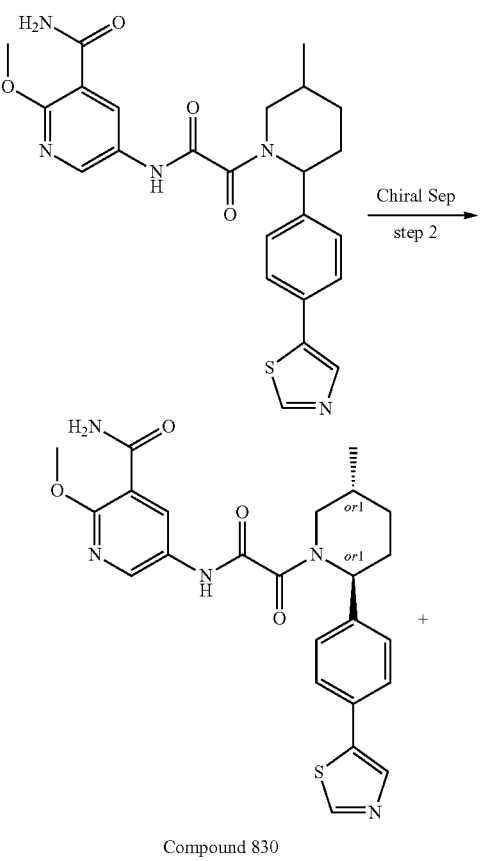

Compound 830

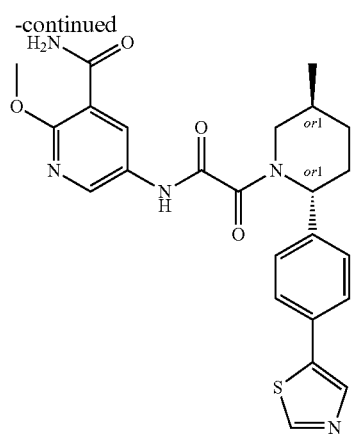

Compound 842

Step 1: Synthesis of 2-methoxy-5-(2-(5-methyl-2-(4-(Thiazol-5-yl)phenyl)piperidin-1-yl)-2-oxoacetamido)Nicotinamide DIPEA (187.58 mg, 1.45 mmol, 252.80 μL) was added to the solution of respective 5-[4-(5-methyl-2-piperidyl)phenyl]thiazole (0.15 g, 580.54 μmol) and 2-[(5-carbamoyl-6-methoxy-3-pyridyl)amino]-2-oxo-acetic acid (138.86 mg, 580.54 μmol) in DMF (10 mL). The resulting mixture was stirred for 5 min followed by the addition of HATU (242.81 mg, 638.59 μmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and MeCN as an eluent mixture) to afford 2-methoxy-5-[[2-[5-methyl-2-(4-thiazol-5-ylphenyl)-1-piperidyl]-2-oxo-acetyl]amino]pyridine-3-carboxamide (187.1 mg, 390.16 μmol, 67.21% yield).

LCMS(ESI): [M]⁺ m/z: calcd 479.2; found 480.2; Rt=2.929 min.

Step 2: Chiral Separation (Compound 830 and Compound 842

2-methoxy-5-[[2-[5-methyl-2-(4-thiazol-5-ylphenyl)-1-piperidyl]-2-oxo-acetyl]amino]pyridine-3-carboxamide (187.1 mg, 390.16 mmol) was divided into enantiomers by Chiral HPLC (AS (250*20 mm, 5 mkm), CO₂-MeOH, 55-45, 50 mL/min;).

Ret time for Compound 830 in analytical conditions (column: AS-H, CO₂-MeOH, 55-45, 2 ml/min as mobile phase) 5.64 min and for Compound 842 7.27 min.

Compound 830: Retention time: 5.64 min
¹H NMR (600 MHz, DMSO-d₆) δ (ppm) 1.00-1.05 (m, 3H), 1.30-1.40 (m, 1H), 1.63-1.71 (m, 1H), 1.83-1.92 (m, 1H), 2.03-2.15 (m, 1H), 2.20-2.28 (m, 1H), 2.77-3.27 (m, 1H), 3.45-4.05 (m, 4H), 5.15-5.62 (m, 1H), 7.35-7.43 (m, 2H), 7.65-7.72 (m, 3H), 7.72-7.75 (m, 1H), 8.26-8.33 (m, 1H), 8.41-8.48 (m, 1H), 8.48-8.58 (m, 1H), 9.03-9.10 (m, 1H), 10.98-11.08 (m, 1H).

LCMS(ESI): [M]⁺ m/z: calcd 479.2; found 480.2; Rt=1.299 min.

Compound 842: Retention time: 7.27 min
¹H NMR (600 MHz, DMSO-d₆) δ (ppm) 0.99-1.04 (m, 3H), 1.28-1.38 (m, 1H), 1.59-1.72 (m, 1H), 1.82-1.95 (m, 1H), 2.00-2.15 (m, 1H), 2.19-2.28 (m, 1H), 2.76-3.26 (m, 1H), 3.45-4.05 (m, 4H), 5.15-5.63 (m, 1H), 7.36-7.43 (m, 2H), 7.65-7.76 (m, 4H), 8.28-8.32 (m, 1H), 8.40-8.48 (m, 1H), 8.48-8.58 (m, 1H), 9.03-9.08 (m, 1H), 10.99-11.08 (m, 1H).

LCMS(ESI): [M]⁺ m/z: calcd 479.2; found 480.2; Rt=1.297 min.

Example 189. The Synthesis of N-(6-amino-5-ethylpyridin-3-yl)-2-(5-methyl-2-(4-(Thiazol-5-yl)phenyl)piperidin-1-yl)-2-oxoacetamide (Compound 827 and Compound 841

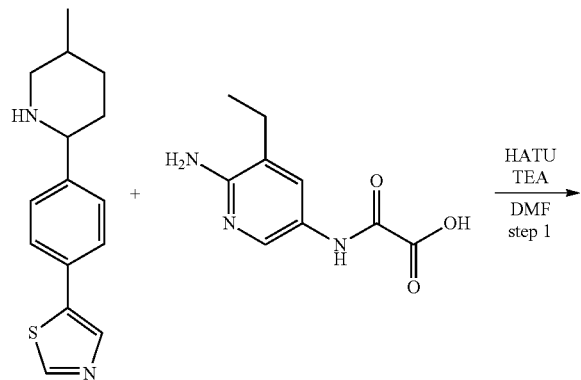

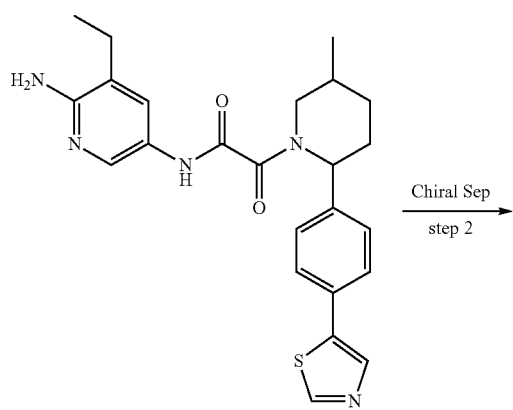

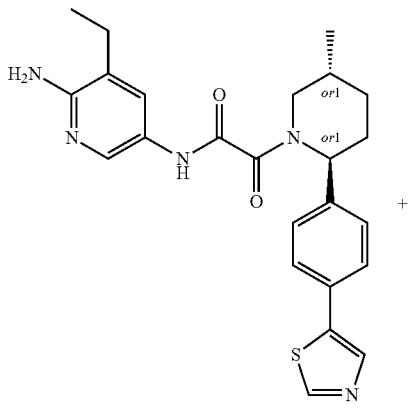

Compound 841

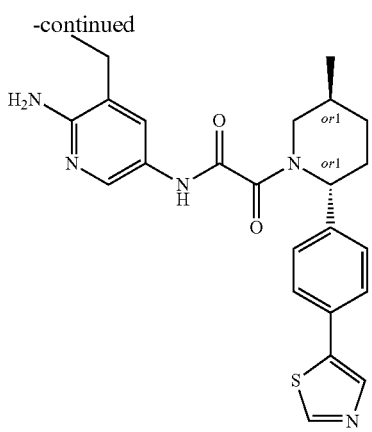

Compound 827

Step 1: Synthesis of N-(6-amino-5-ethylpyridin-3-yl)-2-(5-methyl-2-(4-(Thiazol-5-yl)phenyl)piperidin-1-yl)-2-oxoacetamide DIPEA (231.67 mg, 1.79 mmol, 312.23 μL) was added to the solution of respective 2-[(6-amino-5-ethyl-3-pyridyl)amino]-2-oxo-acetic acid (0.15 g, 717.01 μmol) and 5-[4-(5-methyl-2-piperidyl)phenyl]thiazole (185.26 mg, 717.01 μmol) in DMF (10 mL). The resulting mixture was stirred for 5 min followed by the addition of HATU (299.89 mg, 788.71 μmol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and MeCN as an eluent mixture) to afford N-(6-amino-5-ethyl-3-pyridyl)-2-[5-methyl-2-(4-thiazol-5-ylphenyl)-1-piperidyl]-2-oxoacetamide (140 mg, 311.41 μmol, 43.43% yield).

LCMS(ESI): [M]⁺ m/z: calcd 449.2; found 450.2; Rt=0.948 min.

Step 2: Chiral Separation (Compound 841 and Compound 827

N-(6-amino-5-ethyl-3-pyridyl)-2-[5-methyl-2-(4-thiazol-5-ylphenyl)-1-piperidyl]-2-oxo-acetamide (140 mg, 311.46 mmol) was divided into enantiomers by Chiral HPLC (OD-H (250*30 mm, 5 mkm), Hexane-IPA-MeOH, 75-15-15, 28 mL/min;).

Ret time for Compound 841 in analytical conditions (column: IB, CO₂-MeOH, 70-30, 2 ml/min as mobile phase) 17.44 min and for Compound 827 13.86 min.

Compound 841: Retention time: 17.44 min
¹H NMR (600 MHz, DMSO-d₆) δ (ppm) 0.99-1.02 (m, 3H), 1.04-1.13 (m, 3H), 1.29-1.38 (m, 1H), 1.59-1.71 (m, 1H), 1.80-1.94 (m, 1H), 1.97-2.14 (m, 1H), 2.16-2.27 (m, 1H), 2.31-2.35 (m, 1H), 2.38-2.41 (m, 1H), 2.71-3.25 (m, 1H), 3.42-4.06 (m, 1H), 5.13-5.69 (m, 3H), 7.32-7.51 (m, 3H), 7.64-7.73 (m, 2H), 7.97-8.09 (m, 1H), 8.24-8.33 (m, 1H), 9.04-9.79 (m, 1H), 10.47-10.57 (m, 1H).

LCMS(ESI): [M]⁺ m/z: calcd 449.2; found 450.2; Rt=1.082 min.

Compound 827: Retention time: 13.86 min
¹H NMR (600 MHz, DMSO-d₆) δ (ppm) 0.99-1.02 (m, 3H), 1.04-1.12 (m, 3H), 1.26-1.40 (m, 1H), 1.59-1.69 (m, 1H), 1.81-1.92 (m, 1H), 1.98-2.14 (m, 1H), 2.16-2.29 (m, 1H), 2.29-2.35 (m, 1H), 2.38-2.41 (m, 1H), 2.69-3.26 (m, 1H), 3.42-4.04 (m, 1H), 5.10-5.68 (m, 3H), 7.31-7.52 (m, 3H), 7.61-7.73 (m, 2H), 7.95-8.07 (m, 1H), 8.24-8.34 (m, 1H), 9.06 (s, 1H), 10.45-10.55 (m, 1H).

LCMS(ESI): [M]+ m/z: calcd 449.2; found 450.2; Rt=1.088 min.

Example 190. The Synthesis of 4-(1-(2-((5-carbamoylpyridin-3-yl)amino)-2-oxoacetyl)-5-methylpiperidin-2-yl)phenyl Acetate (Compound 599 and Compound 604

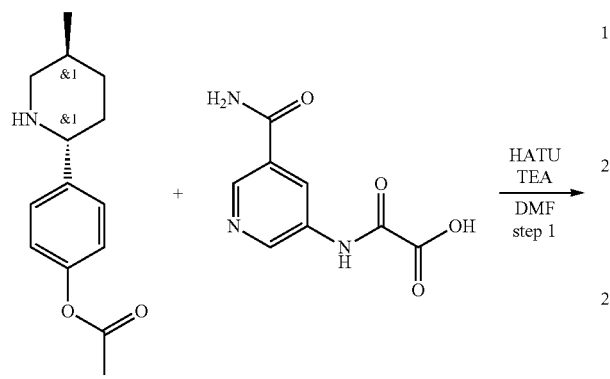

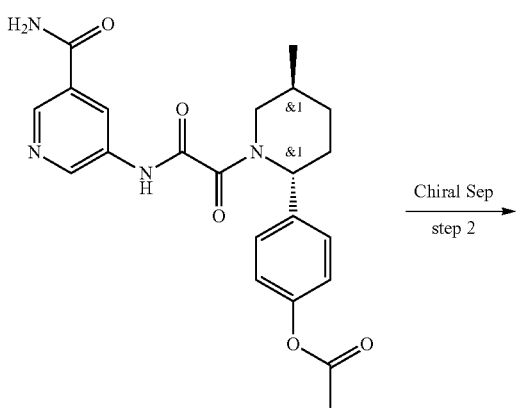

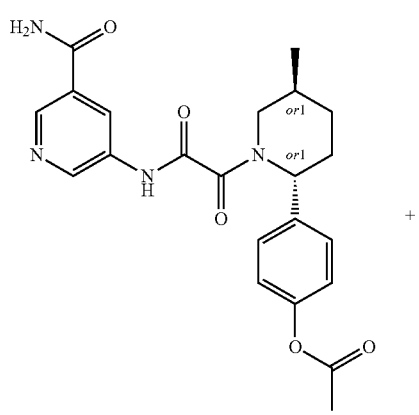

Compound 599

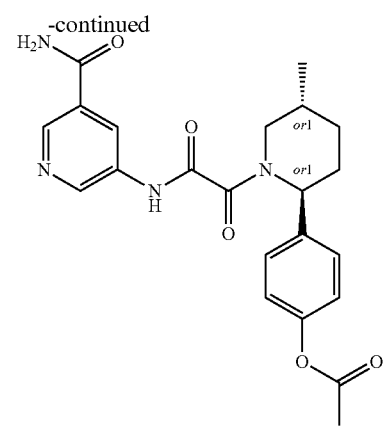

Compound 604

Step 1: Synthesis of 4-(1-(2-((5-carbamoylpyridin-3-yl)amino)-2-oxoacetyl)-5-methylpiperidin-2-yl) phenyl Acetate 2-[(5-carbamoyl-3-pyridyl)amino]-2-oxo-acetic acid (291.36 mg, 1.19 mmol, HCl) and TEA (1.20 g, 11.86 mmol, 1.65 mL) were dissolved in DMF (12 mL) and cooled to 0° C., HATU (676.55 mg, 1.78 mmol) was added and the mixture was stirred for 15 min at 0° C. [4-[(2S,5R)-5-methyl-2-piperidyl]phenyl]acetate (0.32 g, 1.19 mmol, HCl) was added and the mixture was warmed to rt and stirred for 3 hr. 10 ml of Ethyl acetate was added and organic phase was washed with brine three times. Organic phase was dried over $Na_2SO_4$, filtered and concentrated in vacuum at 45° C. to give crude product which was purified by HPLC (2-10 min 35-60% MeOH, 30 ml/min (loading pump 4 ml of MeOH) column: SunFire 100*19 mm, 5 microM) to give [4-[(2S,5R)-1-[2-[(5-carbamoyl-3-pyridyl)amino]-2-oxo-acetyl]-5-methyl-2-piperidyl]phenyl]acetate (0.101 g, 237.96 μmol, 20.06% yield).

LCMS(ESI): [M]+ m/z: calcd 424.2; found 425.2; Rt=1.181 min.

Step 2: Chiral Separation (Compound 604 and Compound 599

Chiral separation was performed using Column: Chiralpak IB (250*20 mm, 5 mkm); Mobile phase: Hexane-IPA-MeOH 60-20-20 Flow Rate: 13 mL/min to give [4-[(2S, 5R)-1-[2-[(5-carbamoyl-3-pyridyl)amino]-2-oxo-acetyl]-5-methyl-2-piperidyl]phenyl]acetate (0.051 g, 120.16 μmol, 51.00% yield) and [4-[(2R,5S)-1-[2-[(5-carbamoyl-3-pyridyl)amino]-2-oxo-acetyl]-5-methyl-2-piperidyl]phenyl]acetate (0.048 g, 113.09 μmol, 48.00% yield).

Ret time for Compound 604 in analytical conditions (column: IB, Hexane-IPA-MeOH, 50-25-25, 0.6 ml/min as mobile phase) 11.42 min and for Compound 599 15.56 min.

Compound 604: Retention time: 11.42 min $^1$H NMR (600 MHz, DMSO-$d_6$) δ (ppm) 0.99-1.05 (m, 3H), 1.29-1.39 (m, 1H), 1.63-1.71 (m, 1H), 1.83-1.94 (m, 1H), 1.99-2.13 (m, 1H), 2.13-2.23 (m, 1H), 2.23-2.26 (m, 3H), 2.72-3.23 (m, 1H), 3.46-4.05 (m, 1H), 5.13-5.60 (m, 1H), 7.08-7.16 (m, 2H), 7.30-7.41 (m, 2H), 7.53-7.65 (m, 1H), 8.09-8.20 (m, 1H), 8.40-8.51 (m, 1H), 8.67-8.80 (m, 1H), 8.81-8.92 (m, 1H), 11.17-11.30 (m, 1H).

LCMS(ESI): [M]+ m/z: calcd 424.2; found 425.2; Rt=2.373 min.

Compound 599: Retention time: 15.56 min $^1$H NMR (600 MHz, DMSO-$d_6$) δ (ppm) 0.99-1.04 (m, 3H), 1.25-1.41 (m, 1H), 1.60-1.75 (m, 1H), 1.79-1.97 (m, 1H), 2.00-2.15 (m, 1H), 2.15-2.23 (m, 1H), 2.23-2.25 (m, 3H), 2.73-3.27 (m, 1H), 3.45-4.06 (m, 1H), 5.15-5.58 (m, 1H), 7.10-7.16 (m, 2H), 7.33-7.41 (m, 2H), 7.53-7.65 (m, 1H), 8.10-8.20 (m, 1H), 8.39-8.50 (m, 1H), 8.72-8.79 (m, 1H), 8.83-8.91 (m, 1H), 11.13-11.29 (m, 1H).

LCMS(ESI): [M]$^+$ m/z: calcd 424.2; found 425.2; Rt=2.372 min.

Example 191. The Synthesis of Rel-5-[[2-[(2S,5R)-2-(7-fluoro-1H-indazol-5-yl)-5-methyl-1-piperidyl]-2-oxo-acetyl]amino]pyridine-3-carboxamide (Compound 663) and Rel-5-[[2-[(2R,5S)-2-(7-fluoro-1H-indazol-5-yl)-5-methyl-1-piperidyl]-2-oxo-acetyl]amino]pyridine-3-carboxamide (Compound 680

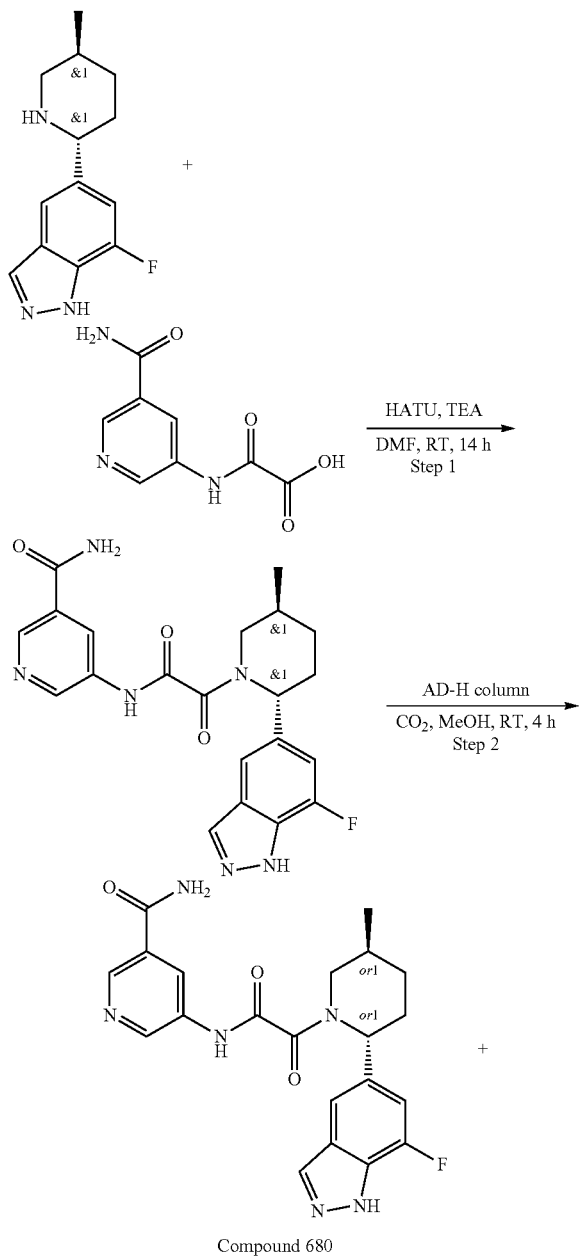

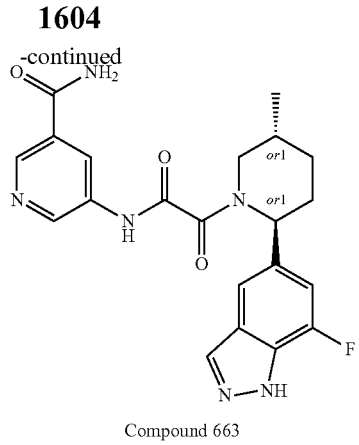

Compound 663

Step 1: The Synthesis of rac-5-[[2-[2-(7-fluoro-1H-indazol-5-yl)-5-methyl-1-piperidyl]-2-oxo-acetyl]amino]pyridine-3-carboxamide 7-fluoro-5-(5-methyl-2-piperidyl)-1H-indazole (0.180 g, 771.59 μmol) was dissolved in DMF (6 mL) and triethylamine (780.77 mg, 7.72 mmol, 1.08 mL) was added, followed by 2-[(5-carbamoyl-3-pyridyl)amino]-2-oxo-acetic acid (159.42 mg, 649.07 μmol, HCl). Then the HATU (440.07 mg, 1.16 mmol) was added dropwise and the reaction mixture was stirred overnight. The reaction mixture was concentrated in vacuo and the residue was purified by HPLC (2-10 min 50-60% Methanol/H$_2$O 30 mL/min (loading pump 4 mL Methanol) column: SunFire 100*19 mm, 5 micro) to obtain 62.9 mg.

LCMS(ESI): [M+H]$^+$ m/z: calcd 424.1; found 425.2; Rt=1.034 min.

Step 2: The Synthesis of Rel-5-[[2-[(2S,5R)-2-(7-fluoro-1H-indazol-5-yl)-5-methyl-1-piperidyl]-2-oxo-acetyl]amino]pyridine-3-carboxamide (Compound 663) and Re-5-[[2-[(2R,5S)-2-(7-fluoro-1H-indazol-5-yl)-5-methyl-1-piperidyl]-2-oxo-acetyl]amino]pyridine-3-carboxamide (Compound 680 rac-5-[[2-[2-(7-fluoro-1H-indazol-5-yl)-5-methyl-1-piperidyl]-2-oxo-acetyl]amino]pyridine-3-carboxamide (0.0629 g, 148.20 μmol) was chiral separated (Column: Chiralpak AD-H (250*20 mm, 5 mkm); Mobile phase: CO$_2$-MeOH, 50-50. Flow Rate: 45 mL/min; Column Temperature: 40° C.; Wavelength: 215 nm. RetTime (isomer B)=6.48 min) to obtain Compound 680—rel-5-[[2-[(2R,5S)-2-(7-fluoro-1H-indazol-5-yl)-5-methyl-1-piperidyl]-2-oxo-acetyl]amino]pyridine-3-carboxamide (0.022 g, 51.83 μmol, 34.98% yield) and Compound 680: $^1$H NMR (DMSO-$d_6$, 600 MHz): δ (ppm) 1.03 (m, 3H), 1.35 (m, 1H), 1.74 (m, 1H), 1.88 (m, 1H), 2.11 (m, 1H), 2.27 (m, 1H), 2.96 (m, 1H), 3.75 (m, 1H), 5.44 (m, 1H), 7.17 (m, 1H), 7.57 (m, 2H), 8.14 (m, 2H), 8.47 (m, 1H), 8.75 (m, 1H), 8.86 (m, 1H), 11.26 (m, 1H), 13.59 (m, 1H).

LCMS(ESI): [M+H]$^+$ m/z: calcd 424.2; found 425.0; Rt=1.055 min.

Compound 663: $^1$H NMR (DMSO-$d_6$, 600 MHz): δ (ppm) 1.03 (m, 3H), 1.35 (m, 1H), 1.77 (m, 1H), 1.89 (m, 1H), 2.11 (m, 1H), 2.27 (m, 1H), 2.82 (m, 1H), 3.75 (m, 1H), 5.44 (m, 1H), 7.17 (m, 1H), 7.57 (m, 2H), 8.12 (m, 1H), 8.17 (m, 1H), 8.47 (m, 1H), 8.75 (m, 1H), 8.86 (m, 1H), 11.26 (m, 1H), 13.59 (m, 1H).

LCMS(ESI): [M+H]⁺ m/z: calcd 424.2; found 425.2; Rt=1.055 min.

Example 192. The Synthesis of rac-5-[[2-[(2R,5S)-5-methyl-2-(2-oxo-1,3-dihydrobenzimidazol-5-yl)-1-piperidyl]-2-oxo-acetyl]amino]pyridine-3-carboxamide (Compound 623)

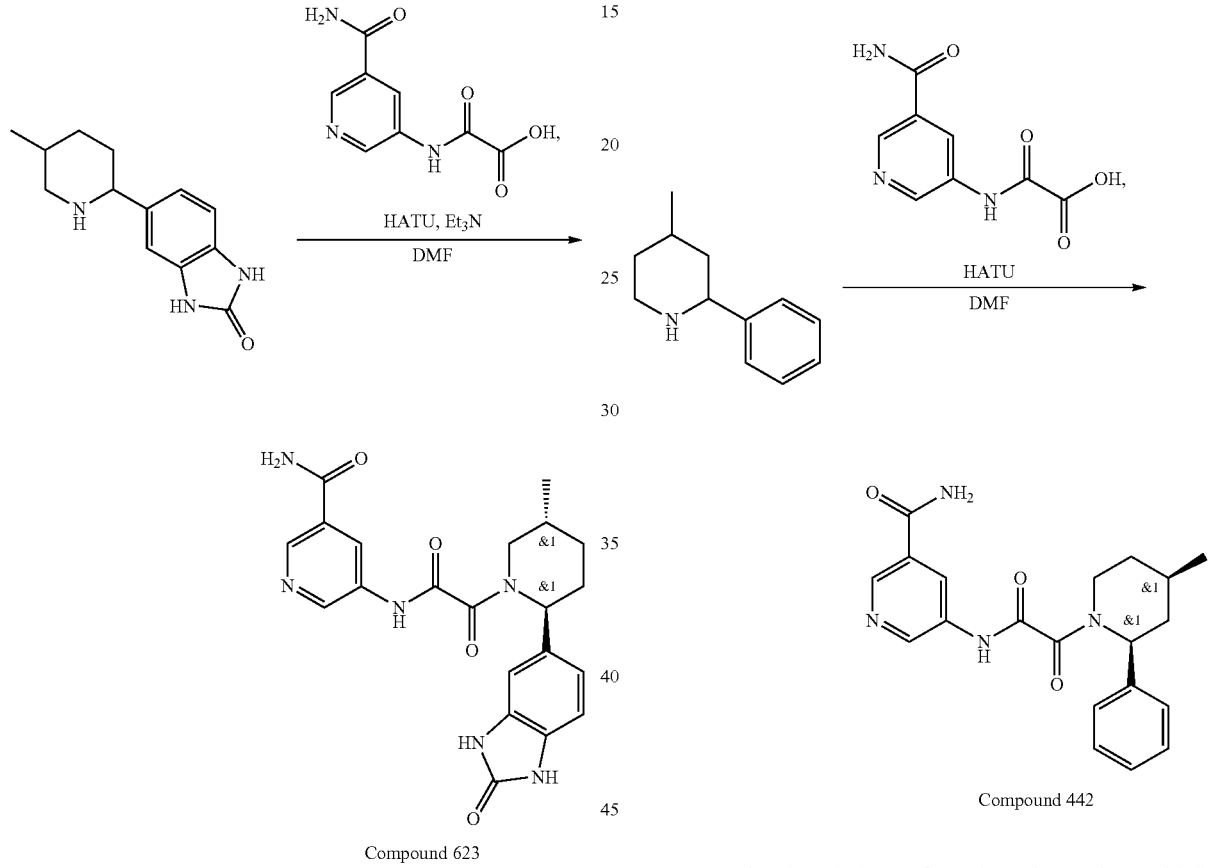

Compound 623

To a stirred solution of rac-5-[(2R,5S)-5-methyl-2-piperidyl]-1,3-dihydrobenzimidazol-2-one (50.4 mg, 217.91 μmol), 2-[(5-carbamoyl-3-pyridyl)amino]-2-oxo-acetic acid (46.02 mg, 217.91 μmol) and Triethylamine (110.25 mg, 1.09 mmol, 151.86 μL) in DMF (1 mL) was added HATU (124.28 mg, 326.86 μmol) at the room temperature. The resulting reaction mixture was stirred for 12 hours at the same temperature. After 12 hours, the reaction mixture was concentrated under reduced pressure. The obtained residue was purified by HPLC to get rac-5-[[2-[(2R,5S)-5-methyl-2-(2-oxo-1,3-dihydrobenzimidazol-5-yl)-1-piperidyl]-2-oxo-acetyl]amino]pyridine-3-carboxamide (Compound 623, 23 mg, 54.45 μmol, 24.99% yield) as a white solid.

¹H NMR (DMSO-d₆, 600 MHz): δ (ppm) 0.98-1.05 (m, 3H), 1.28-1.38 (m, 1H), 1.68-1.77 (m, 1H), 1.81-1.94 (m, 1H), 1.96-2.12 (m, 1H), 2.13-2.24 (m, 1H), 2.78-3.25 (m, 1H), 3.43-4.04 (m, 1H), 5.08-5.64 (m, 1H), 6.83-6.96 (m, 3H), 7.47-7.65 (m, 1H), 8.04-8.19 (m, 1H), 8.43-8.52 (m, 1H), 8.69-8.81 (m, 1H), 8.81-8.94 (m, 1H), 10.53-10.62 (m, 2H), 11.13-11.37 (m, 1H).

LCMS(ESI): [M+H]⁺ m/z: calcd 422.2; found 423.2; Rt=1.916 min.

Example 193. The Synthesis of 5-(2-(4-methyl-2-phenylpiperidin-1-yl)-2-oxoacetamido)Nicotinamide (Compound 442)

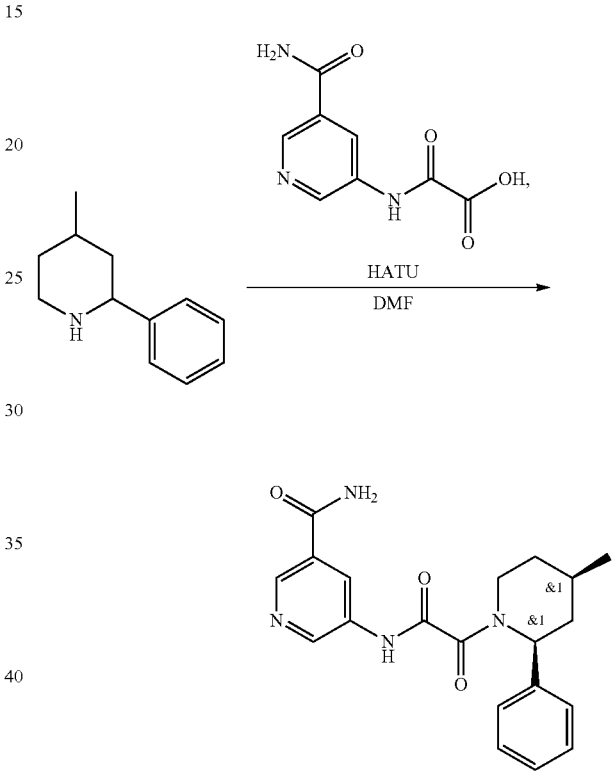

Compound 442

To a stirred solution of 2-[(5-carbamoyl-3-pyridyl)amino]-2-oxo-acetic acid (177.07 mg, 570.55 μmol, Et₃N salt) in DMF (2 mL) was added HATU (216.94 mg, 570.55 μmol). The resulting mixture was stirred at 20° C. for 10 minutes. After 10 minutes, 4-methyl-2-phenyl-piperidine (0.1 g, 570.55 μmol) was added. The resulting reaction mixture was stirred at 20° C. for 12 hours. After 12 hours, the crude reaction mixture was purified by HPLC (Eluent: 0.5-6.5 min, 15-30%, water—acetonitrile; flow rate: 30 mL/min; loading pump: 4 mL/min; acetonitrile; column: SunFire 19×100 mm, 5 um) to obtain 5-(2-(4-methyl-2-phenylpiperidin-1-yl)-2-oxoacetamido)nicotinamide (Compound 442, 0.0114 g, 31.11 μmol, 5.45% yield) as an off-white solid.

¹H NMR (DMSO-d₆, 600 MHz): δ (ppm) 0.86 (m, 4H), 1.27 (m, 1H), 1.86 (m, 1H), 2.07 (m, 2H), 3.48 (m, 1H), 5.18 (m, 1H), 7.29 (m, 6H), 7.62 (m, 1H), 8.16 (m, 1H), 8.52 (m, 1H), 8.78 (m, 1H), 8.92 (m, 1H), 11.20 (m, 1H)

Example 194. LCMS(ESI): [M+H]+ m/z: Calcd 366.2; Found 367.0; Rt=2.951 Min. The Synthesis of rac-5-[[2-[(2S,4R)-4-ethyl-2-phenyl-1-piperidyl]-2-oxo-acetyl]amino]pyridine-3-carboxamide (Compound 497

Example 195. The Synthesis of rac-5-[[2-[(2R,5S)-2-(3,5-difluoro-4-hydroxy-phenyl)-5-methyl-1-piperidyl]-2-oxo-acetyl]amino]pyridine-3-carboxamide (Compound 560

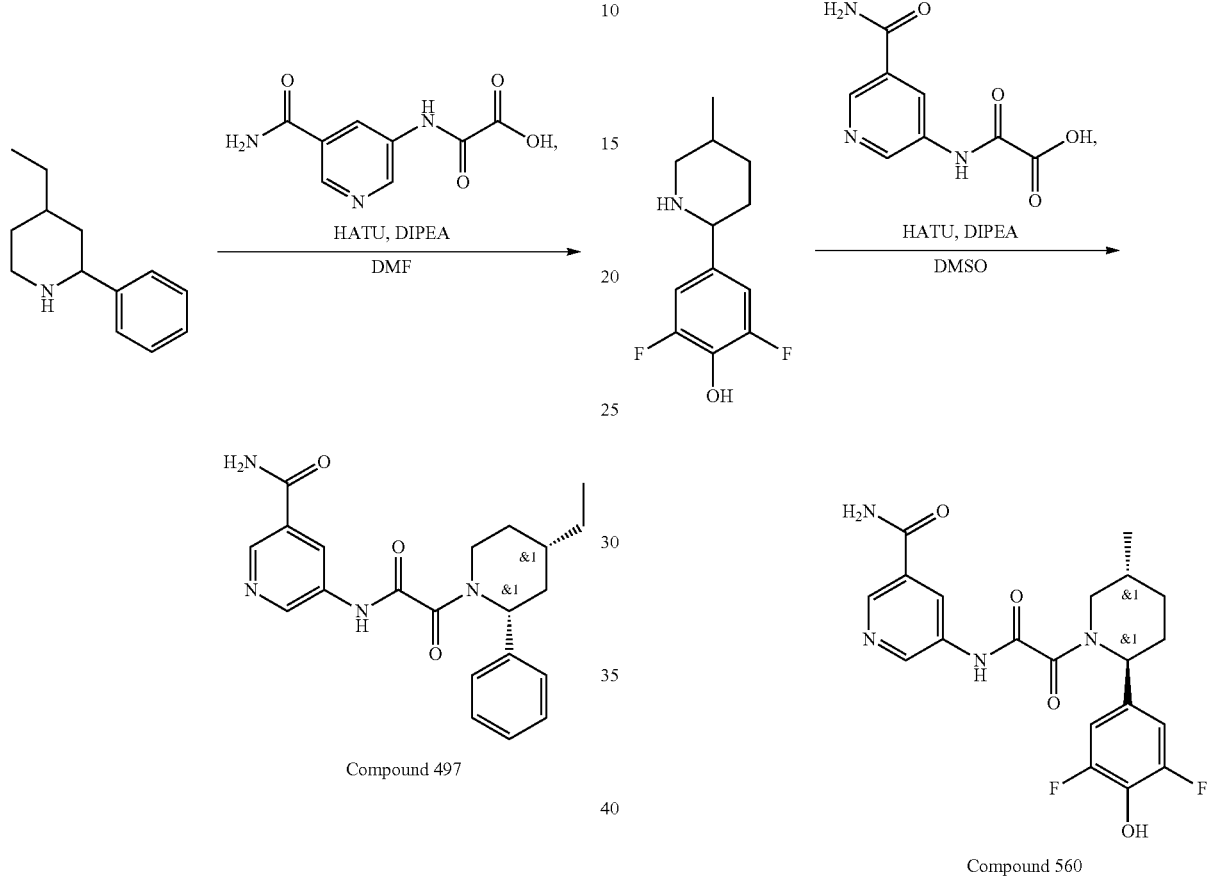

Compound 497

Compound 560

To a stirring solution of 2-[(5-carbamoyl-3-pyridyl)amino]-2-oxo-acetic acid (331.48 mg, 1.58 mmol, Et$_3$N salt), rac-(2S,4R)-4-ethyl-2-phenyl-piperidine (0.3 g, 1.58 mmol) and DIPEA (614.47 mg, 4.75 mmol, 828.12 µL) in DMF (6 mL) was added HATU (723.12 mg, 1.90 mmol) under gentle heating in small portions under vigorous stirring. Upon completion, the crude reaction mixture was purified by reverse phase HPLC (Eluent: 0.5-6.5 min, 21%, water-acetonitrile; flow rate: 30 mL/min; loading pump: 4 mL/min; column: SunFire 19×100 mm, 5 um) to give rac-5-[[2-[(2S,4R)-4-ethyl-2-phenyl-1-piperidyl]-2-oxo-acetyl]amino]pyridine-3-carboxamide (Compound 497, 0.35 g, 919.99 µmol, 58.05% yield).

$^1$H NMR (DMSO-d$_6$, 400 MHz): δ (ppm) 0.76-0.91 (m, 3H), 1.14-1.42 (m, 3H), 1.54-1.91 (m, 2H), 1.97-2.19 (m, 2H), 3.17-3.31 (0.25H), 3.42-3.56 (m, 0.75H), 3.77-4.28 (m, 1H), 5.11-5.18 (m, 1H), 7.08-7.30 (m, 2H), 7.30-7.39 (m, 3H), 7.56-7.70 (m, 1H), 8.08-8.24 (m, 1H), 8.27-8.58 (m, 1H), 8.63-8.99 (m, 2H), 10.73-11.31 (m, 1H).

LCMS(ESI): [M+H]+ m/z: calcd 380.2; found 381.2; Rt=3.236 min.

To a stirred solution of rac-2,6-difluoro-4-[(2R,5S)-5-methyl-2-piperidyl]phenol (0.05 g, 220.02 µmol), 2-[(5-carbamoyl-3-pyridyl)amino]-2-oxo-acetic acid (55.22 mg, 264.03 µmol, Et$_3$N salt) and HATU (117.12 mg, 308.03 µmol) in DMSO (1 mL) was added DIPEA (56.87 mg, 440.04 µmol, 76.65 µL). The reaction mixture was stirred at 25° C. for 16 hours. After 16 hours, the reaction mixture was purified by reverse phase HPLC (Eluent: 2-10 min, 90%, MeOH/H$_2$O; flow rate: 30 mL/min; loading pump: 4 mL, MeOH; column: SunFire C18 100×19 mm, 5 um) to obtain rac-5-[[2-[(2R,5S)-2-(3,5-difluoro-4-hydroxy-phenyl)-5-methyl-1-piperidyl]-2-oxo-acetyl]amino]pyridine-3-carboxamide (Compound 560, 0.012 g, 28.68 µmol, 13.04% yield) as a beige solid.

$^1$H NMR (DMSO-d$_6$, 600 MHz): δ (ppm) 0.97-1.02 (m, 3H), 1.23-1.35 (m, 1H), 1.58-1.74 (m, 1H), 1.80-1.93 (m, 1H), 1.94-2.10 (m, 1H), 2.10-2.19 (m, 1H), 2.75-3.24 (m, 1H), 3.40-4.04 (m, 1H), 4.98-5.53 (m, 1H), 6.85-7.02 (m, 2H), 7.51-7.65 (m, 1H), 8.12-8.19 (m, 1H), 8.40-8.52 (m, 1H), 8.68-8.80 (m, 1H), 8.80-8.91 (m, 1H), 11.07-11.49 (m, 1H).

LCMS(ESI): [M+H]+ m/z: calcd 418.2; found 419.2; Rt=2.057 min.

1609

Example 0.196. The Synthesis of rac-5-[[2-[(2S,5R)-5-methyl-2-(3-methyl-1H-indazol-5-yl)-1-piperidyl]-2-oxo-acetyl]amino]pyridine-3-carboxamide (Compound 500

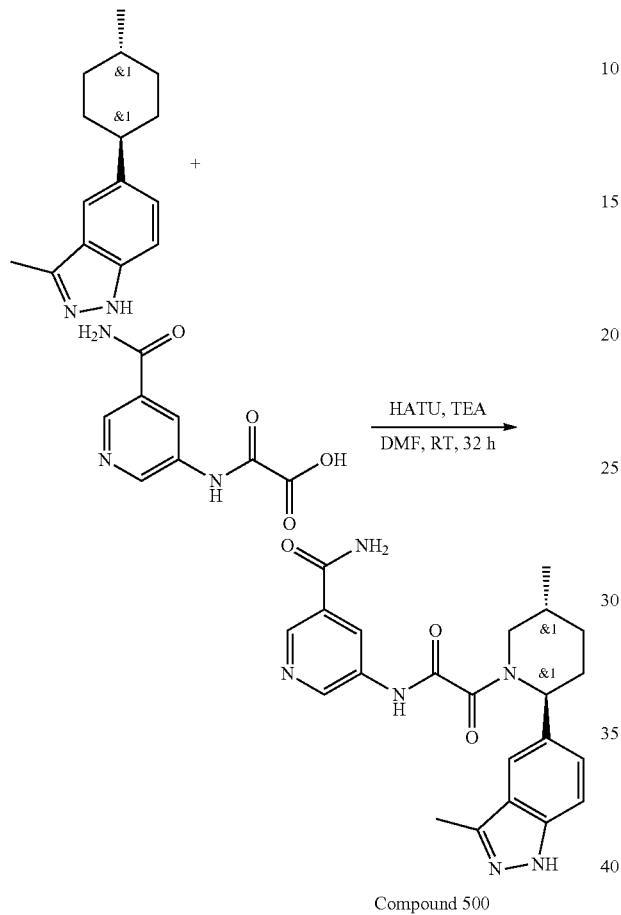

Compound 500

HATU (411.20 mg, 1.08 mmol) was added portionwise at r.t. to a suspension of 2-[(5-carbamoyl-3-pyridyl)amino]-2-oxo-acetic acid (265.63 mg, 1.08 mmol, HCl), 3-methyl-5-(5-methyl-2-piperidyl)-1H-indazole (310 mg, 1.08 mmol) and TEA (656.60 mg, 6.49 mmol, 904.40 µL) in DMF (10 mL). The clear solution was stirred at 25° C. for 32 hr and the solvents were evaporated in vacuo to give 1 g of crude material. It was subjected to RP-HPLC (column: SunFire C18 100×19 mm 5 um; 40-50% 0-6 min water-methanol+FA, flow: 30 ml/min as mobile phase) to give Compound 500 rac-5-[[2-[(2S,5R)-5-methyl-2-(3-methyl-1H-indazol-5-yl)-1-piperidyl]-2-oxo-acetyl]amino]pyridine-3-carboxamide (150 mg, 356.75 µmol, 32.99% yield).

$^1$H NMR (600 MHz, DMSO-d$_6$) δ 1.01-1.07 (m, 3H), 1.30-1.42 (m, 1H), 1.71-1.94 (m, 2H), 1.95-2.25 (m, 1H), 2.28-2.37 (m, 1H), 2.42-2.46 (m, 3H), 2.82-3.27 (m, 1H), 3.36-4.08 (m, 1H), 5.17-5.73 (m, 1H), 7.24-7.36 (m, 1H), 7.39-7.47 (m, 1H), 7.53-7.67 (m, 2H), 8.07-8.21 (m, 1H), 8.42-8.54 (m, 1H), 8.71-8.79 (m, 1H), 8.79-8.95 (m, 1H), 11.14-11.32 (m, 1H), 12.54-12.63 (m, 1H).

LCMS(ESI): [M+H]$^+$ m/z: calcd 420.2; found 421.2; Rt=2.640 min.

1610

Example 197. The Synthesis of Rel-5-[[2-[(2R,5S)-5-methyl-2-(4-thiazol-2-ylphenyl)-1-piperidyl]-2-oxo-acetyl]amino]pyridine-3-carboxamide (Compound 772) and Rel-5-[[2-[(2S,5R)-5-methyl-2-(4-thiazol-2-ylphenyl)-1-piperidyl]-2-oxo-acetyl]amino]pyridine-3-carboxamide (Compound 783

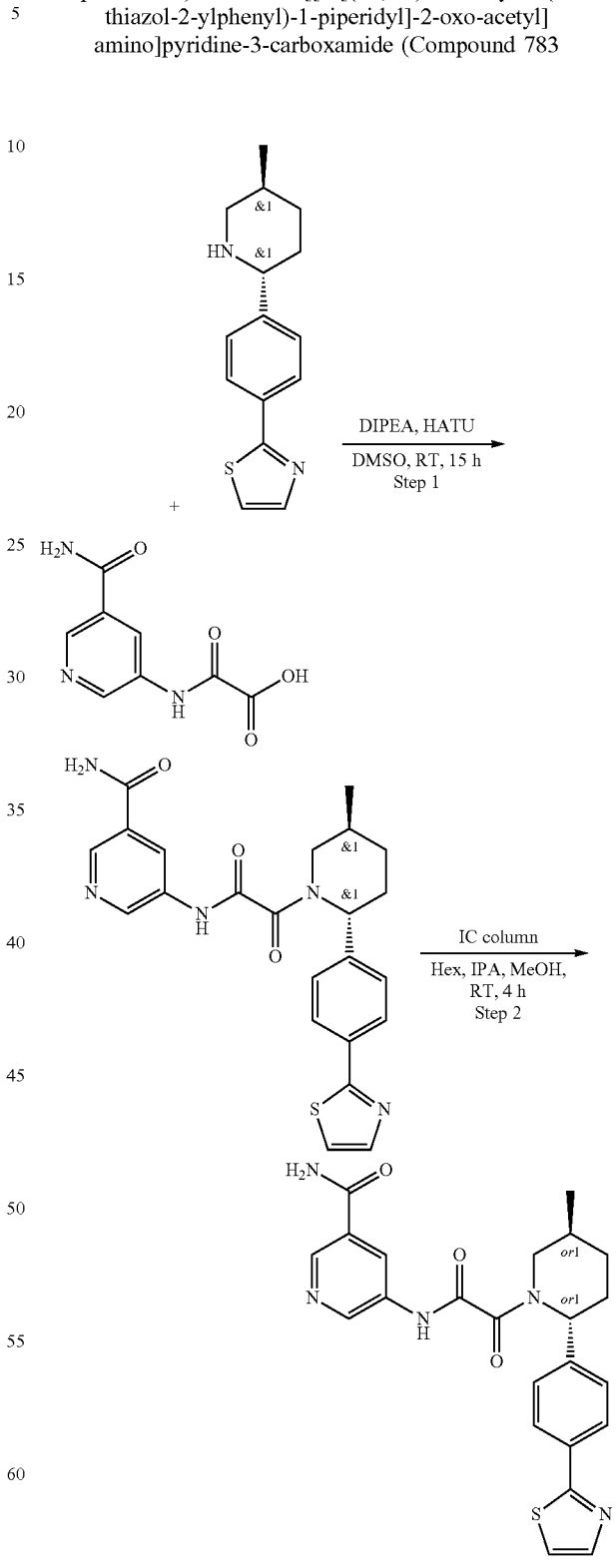

Compound 772

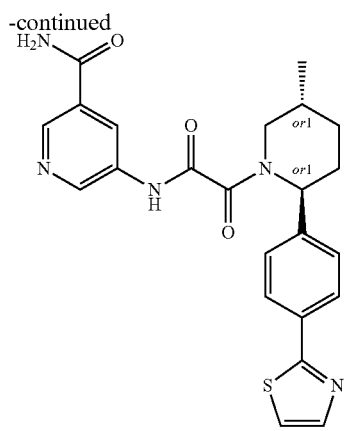

Compound 783

Step 1: The Synthesis of rac-5-[[2-[(2R,5S)-5-methyl-2-(4-thiazol-2-ylphenyl)-1-piperidyl]-2-oxo-acetyl]amino]pyridine-3-carboxamide To a stirred solution of 2-[4-[(2R,5S)-5-methyl-2-piperidyl]phenyl]thiazole (315.59 mg, 1.22 mmol), DIPEA (473.56 mg, 3.66 mmol, 638.22 μL) and DIPEA (473.56 mg, 3.66 mmol, 638.22 μL) in DMSO (4 mL) was added HATU (557.30 mg, 1.47 mmol). The resulting reaction mixture was stirred at 25° C. for 15 h. Upon completion, the reaction mixture was submitted to reverse phase HPLC to afford rac-5-[[2-[(2R,5S)-5-methyl-2-(4-thiazol-2-ylphenyl)-1-piperidyl]-2-oxo-acetyl]amino]pyridine-3-carboxamide (0.12 g, 266.95 μmol, 21.86% yield).

HPLC data: 2-10 min 50-60% R1/H$_2$O, 30 ml/min (loading pump 4 ml ACN), column: HILIC, 5 micro LCMS(ESI): [M+H]$^+$ m/z: calcd 449.2; found 450.2; Rt=1.171 min.

Step 2: The Synthesis of Rel-5-[[2-[(2R,5S)-5-methyl-2-(4-thiazol-2-ylphenyl)-1-piperidyl]-2-oxo-acetyl]amino]pyridine-3-carboxamide (Compound 772) and Re-5-[[2-[(2S,5R)-5-methyl-2-(4-thiazol-2-ylphenyl)-1-piperidyl]-2-oxo-acetyl]amino]pyridine-3-carboxamide (Compound 783 rac-5-[[2-[(2R,5S)-5-methyl-2-(4-thiazol-2-ylphenyl)-1-piperidyl]-2-oxo-acetyl]amino]pyridine-3-carboxamide (0.12 g, 266.95 μmol) was submitted to chiral separation to afford Compound 772—rel-5-[[2-[(2R,5S)-5-methyl-2-(4-thiazol-2-ylphenyl)-1-piperidyl]-2-oxo-acetyl]amino]pyridine-3-carboxamide (0.056 g, 124.58 μmol, 46.67% yield) and Compound 783—rel-5-[[2-[(2S,5R)-5-methyl-2-(4-thiazol-2-ylphenyl)-1-piperidyl]-2-oxo-acetyl]amino]pyridine-3-carboxamide (0.051 g, 113.45 μmol, 42.50% yield) as white solids. Chromatography data: Column: Chiralpak IC (250*20, 5 mkm), Mobile phase: Hexane-IPA-MeOH, 50-25-25; Flow rate: 12 mL/min. 24° C., Wavelength: 205 nm, 225 nm Retention time (isomer 1(SR)) Compound 783=35.4; Retention time (isomer 2(RS)) Compound 772)=109.9

Compound 772: RT (IB, Hexane-IPA-MeOH, 60-20-20, 0.6 mL/min)=24.123 min.

$^1$H NMR (600 MHz, DMSO-d$_6$) δ 0.99-1.05 (m, 3H), 1.33-1.44 (m, 1H), 1.65-1.73 (m, 1H), 1.84-1.97 (m, 1H), 2.07-2.18 (m, 1H), 2.22-2.31 (m, 1H), 2.81-3.27 (m, 1H), 3.48-4.08 (m, 1H), 5.20-5.66 (m, 1H), 7.43-7.51 (m, 2H), 7.55-7.64 (m, 1H), 7.75-7.78 (m, 1H), 7.87-7.93 (m, 1H), 7.93-8.00 (m, 2H), 8.11-8.22 (m, 1H), 8.42-8.54 (m, 1H), 8.70-8.81 (m, 1H), 8.84-8.96 (m, 1H), 11.09-11.34 (m, 1H).

LCMS(ESI): [M+H]$^+$ m/z: calcd 449.2; found 450.2; Rt=2.715 min.

Compound 783: RT (IB, Hexane-IPA-MeOH, 60-20-20, 0.6 mL/min)=20.994 min.

$^1$H NMR (600 MHz, DMSO-d$_6$) δ 0.99-1.06 (m, 3H), 1.29-1.43 (m, 1H), 1.59-1.76 (m, 1H), 1.84-1.96 (m, 1H), 2.04-2.19 (m, 1H), 2.19-2.32 (m, 1H), 2.78-3.27 (m, 1H), 3.48-4.09 (m, 1H), 5.20-5.69 (m, 1H), 7.43-7.53 (m, 2H), 7.54-7.64 (m, 1H), 7.75-7.78 (m, 1H), 7.89-7.92 (m, 1H), 7.92-7.99 (m, 2H), 8.08-8.21 (m, 1H), 8.43-8.53 (m, 1H), 8.69-8.81 (m, 1H), 8.82-8.95 (m, 1H), 11.15-11.43 (m, 1H).

LCMS(ESI): [M+H]$^+$ m/z: calcd 449.2; found 450.2; Rt=2.734 min.

Example 198. The Synthesis of Rel-2-methoxy-5-[[2-[(2R,5S)-5-methyl-2-(4-thiazol-2-ylphenyl)-1-piperidyl]-2-oxo-acetyl]amino]pyridine-3-carboxamide (Compound 811) and Rel-2-methoxy-5-[[2-[(2S,5R)-5-methyl-2-(4-thiazol-2-ylphenyl)-1-piperidyl]-2-oxo-acetyl]amino]pyridine-3-carboxamide (Compound 799

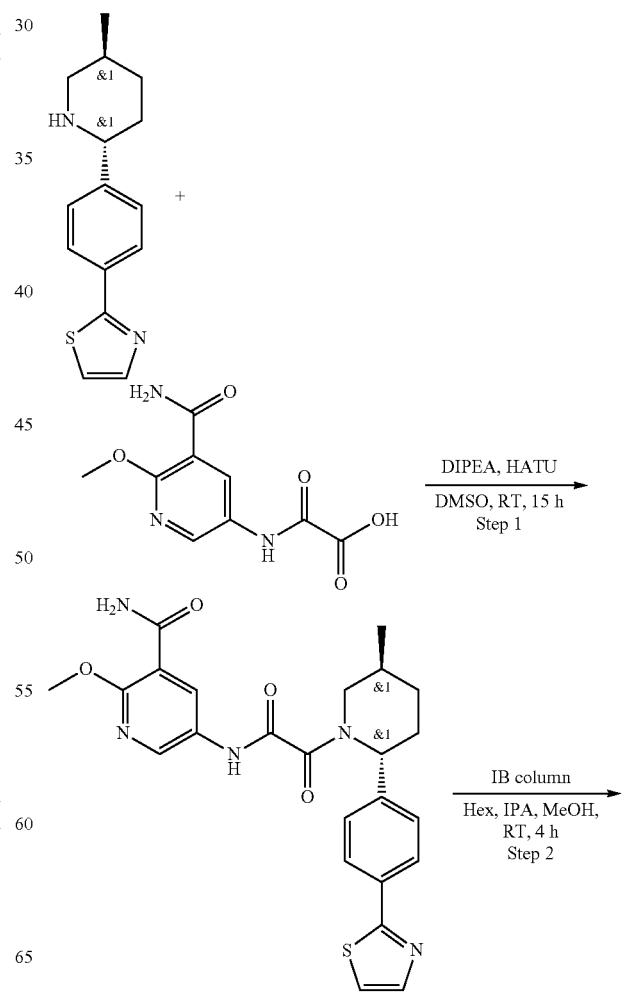

-continued

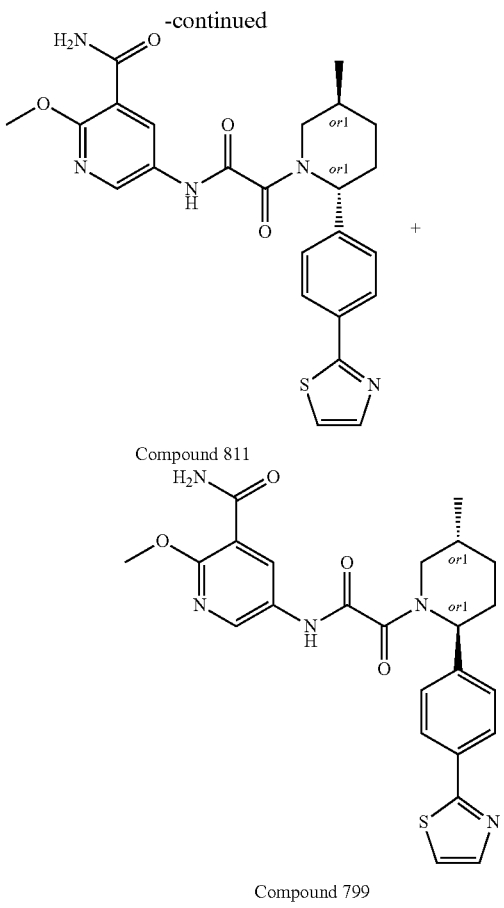

Compound 811

Compound 799

Step 1: The Synthesis of rac-2-methoxy-5-[[2-[(2R,5S)-5-methyl-2-(4-thiazol-2-ylphenyl)-1-piperidyl]-2-oxo-acetyl]amino]pyridine-3-carboxamide To a stirred solution of rac-2-[4-[(2R,5S)-5-methyl-2-piperidyl]phenyl]thiazole (0.15 g, 580.54 µmol), 2-[(5-carbamoyl-6-methoxy-3-pyridyl)amino]-2-oxo-acetic acid (138.86 mg, 580.54 µmol, triethylamine) and DIPEA (150.06 mg, 1.16 mmol, 202.23 µL) in DMSO (3 mL) was added HATU (264.89 mg, 696.65 µmol). The resulting reaction mixture was stirred at 25° C. for 14 hr. Upon completion, the reaction mixture was submitted to reverse phase HPLC to afford rac-2-methoxy-5-[[2-[(2R,5S)-5-methyl-2-(4-thiazol-2-ylphenyl)-1-piperidyl]-2-oxo-acetyl]amino]pyridine-3-carboxamide (0.085 g, 177.25 µmol, 30.53% yield).

HPLC: 2-10 min 50-60% MeOH/H$_2$O; 30 mL/min (loading pump 4 mL MeOH), column: SunFire C18, 5 micro LCMS(ESI): [M+H]$^+$ m/z: calcd 479.2; found 480.2; Rt=1.316 min.

Step 2: The Synthesis of Rel-2-methoxy-5-[[2-[(2R,5S)-5-methyl-2-(4-thiazol-2-ylphenyl)-1-piperidyl]-2-oxo-acetyl]amino]pyridine-3-carboxamide (Compound 811) and Rel-2-methoxy-5-[[2-[(2S,5R)-5-methyl-2-(4-thiazol-2-ylphenyl)-1-piperidyl]-2-oxo-acetyl]amino]pyridine-3-carboxamide (Compound 799 rac-2-methoxy-5-[[2-[(2R,5S)-5-methyl-2-(4-thiazol-2-ylphenyl)-1-piperidyl]-2-oxo-acetyl]amino]pyridine-3-carboxamide (0.085 g, 177.25 µmol) was submitted to chiral separation to afford Compound 811—rel-2-methoxy-5-[[2-[(2R,5S)-5-methyl-2-(4-thiazol-2-ylphenyl)-1-piperidyl]-2-oxo-acetyl]amino]pyridine-3-carboxamide (0.034 g, 70.90 µmol, 40.00% yield) and Compound 799—rel-2-methoxy-5-[[2-[(2S,5R)-5-methyl-2-(4-thiazol-2-ylphenyl)-1-piperidyl]-2-oxo-acetyl]amino]pyridine-3-carboxamide (0.034 g, 70.90 µmol, 40.00% yield). Separation data: Chiralpak IB 250*20, 5-II Hexane-IPA-MeOH, 70-15-15, 15 mL/min; Rt1=23.43 min; Rt2=30.94 min Compound 811: RT (IB, Hexane-IPA-MeOH, 50-25-25, 0.6 mL/min)=17.214 min.

$^1$H NMR (dmso, 600 MHz): δ (ppm) 0.97-1.05 (m, 3H), 1.31-1.41 (m, 1H), 1.64-1.72 (m, 1H), 1.83-1.94 (m, 1H), 2.04-2.17 (m, 1H), 2.19-2.29 (m, 1H), 2.80-3.26 (m, 1H), 3.46-3.54 (m, 0.6H), 3.89-3.99 (m, 3H), 4.01-4.07 (m, 0.4H), 5.20-5.69 (m, 1H), 7.40-7.51 (m, 2H), 7.66-7.76 (m, 2H), 7.76-7.78 (m, 1H), 7.88-7.92 (m, 1H), 7.92-8.00 (m, 2H), 8.36-8.68 (m, 2H), 10.87-11.31 (m, 1H).

LCMS(ESI): [M+H]$^+$ m/z: calcd 479.2; found 480.2; Rt=2.983 min.

Compound 799: RT (IB, Hexane-IPA-MeOH, 50-25-25, 0.6 mL/min)=13.684 min.

$^1$H NMR (dmso, 600 MHz): δ (ppm) 1.00-1.08 (m, 3H), 1.31-1.43 (m, 1H), 1.63-1.74 (m, 1H), 1.81-1.94 (m, 1H), 2.02-2.17 (m, 1H), 2.20-2.29 (m, 1H), 2.79-3.26 (m, 1H), 3.47-3.54 (m, 0.6H), 3.87-3.97 (m, 3H), 4.01-4.06 (m, 0.4H), 5.19-5.71 (m, 1H), 7.41-7.50 (m, 2H), 7.67-7.75 (m, 2H), 7.76-7.79 (m, 1H), 7.88-7.92 (m, 1H), 7.92-8.00 (m, 2H), 8.41-8.60 (m, 2H), 10.87-11.23 (m, 1H).

LCMS(ESI): [M+H]$^+$ m/z: calcd 479.2; found 480.2; Rt=2.983 min.

Example 199. The Synthesis of 5-[[2-[(2R,5R)-5-methyl-2-(5-methyl-2-pyridyl)-1-piperidyl]-2-oxo-acetyl]amino]pyridine-3-carboxamide (Compound 880) and 5-[[2-[(2R,5S)-5-methyl-2-(5-methyl-2-pyridyl)-1-piperidyl]-2-oxo-acetyl]amino]pyridine-3-carboxamide (Compound 937

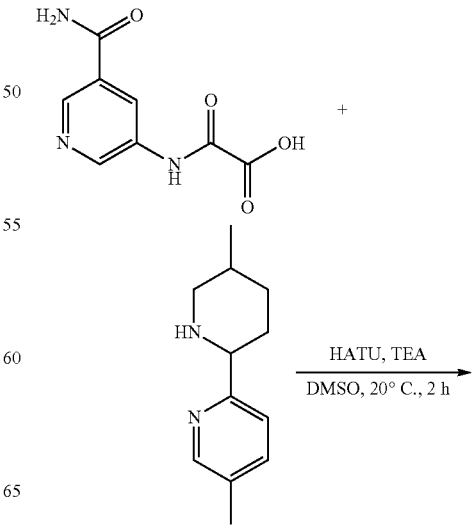

HATU, TEA
DMSO, 20° C., 2 h

-continued

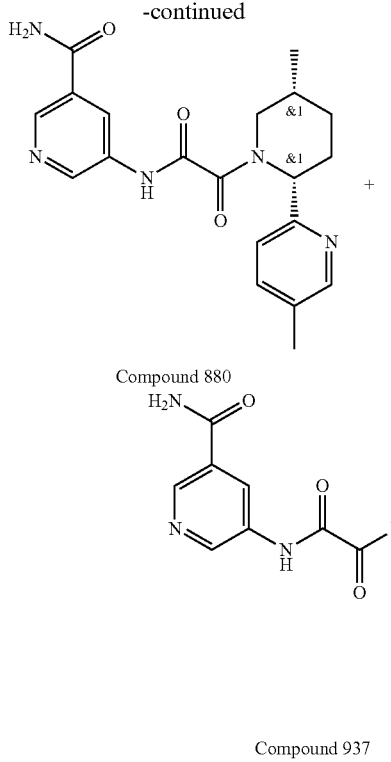

Compound 880

Compound 937

2-[(5-carbamoyl-3-pyridyl)amino]-2-oxo-acetic acid (195.72 mg, 630.64 µmol, N(C2H5)3), 5-methyl-2-(5-methyl-2-piperidyl)pyridine (120 mg, 630.64 µmol), HATU (263.77 mg, 693.70 µmol) and TEA (70.20 mg, 693.70 µmol, 96.69 µL) were mixed in DMSO (2 mL) and stirred for 2 hr at 20° C. Reaction mixture was subjected to HPLC.

HPLC data: 2-10 min 20-45% MeCN/H₂O+TFA 30 mL/min (loading pump 4 mL MeCN) column: SunFire 100*19 mm, 5 microM 5-[[2-[(2R,5R)-5-methyl-2-(5-methyl-2-pyridyl)-1-piperidyl]-2-oxo-acetyl]amino]pyridine-3-carboxamide (96.7 mg, 253.52 µmol, 40.20% yield) was obtained (cis, light-brown, solid) Cis-configuration was confirmed by 2D HNMR (Compound 880, H₂₃₅₉₆₂₀)

5-[[2-[(2R,5S)-5-methyl-2-(5-methyl-2-pyridyl)-1-piperidyl]-2-oxo-acetyl]amino]pyridine-3-carboxamide (44.7 mg, 117.19 µmol, 18.58% yield) was obtained (trans). Trans-configuration was confirmed by 2D HNMR (Compound 937, H₂₃₅₉₆₁₉)

Compound 880: ¹H NMR (DMSO-d₆, 600 MHz): δ (ppm) 0.76 (dd, 3H), 1.03 (m, 1H), 1.70 (m, 3H), 2.27 (m, 3H), 2.68 (m, 2H), 3.96 (dd, 1H), 5.40 (m, 1H), 7.27 (dd, 1H), 7.61 (m, 2H), 8.14 (d, 1H), 8.46 (m, 2H), 8.75 (dd, 1H), 8.86 (dd, 1H), 11.21 (m, 1H).

LCMS(ESI): [M+H]⁺ m/z: calcd 381.2; found 382.2; Rt=1.971 min.

Compound 937: ¹H NMR (DMSO-d₆, 600 MHz): δ (ppm) 1.02 (t, 3H), 1.32 (m, 1H), 1.61 (m, 1H), 1.91 (m, 2H), 2.27 (m, 3H), 2.41 (m, 2H), 2.86 (m, 1H), 3.77 (dd, 1H), 5.38 (m, 1H), 7.29 (dd, 1H), 7.59 (m, 1H), 7.66 (m, 1H), 8.14 (m, 1H), 8.41 (m, 1H), 8.47 (m, 1H), 8.75 (m, 1H), 8.87 (m, 1H), 11.19 (m, 1H).

LCMS(ESI): [M+H]⁺ m/z: calcd 381.2; found 382.0; Rt=1.831 min.

Example 200. The Synthesis of 2-methoxy-5-[[2-[(2R,5R)-5-methyl-2-(5-methyl-2-pyridyl)-1-piperidyl]-2-oxo-acetyl]amino]pyridine-3-carboxamide (Compound 886) and 2-methoxy-5-[[2-[(2R,5S)-5-methyl-2-(5-methyl-2-pyridyl)-1-piperidyl]-2-oxo-acetyl]amino]pyridine-3-carboxamide (Compound 932

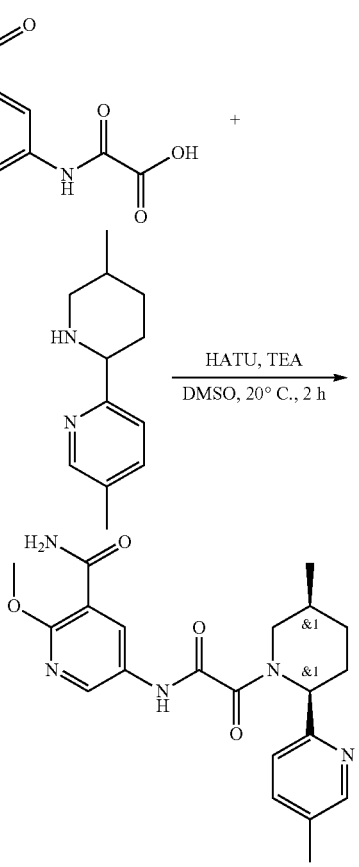

Compound 886

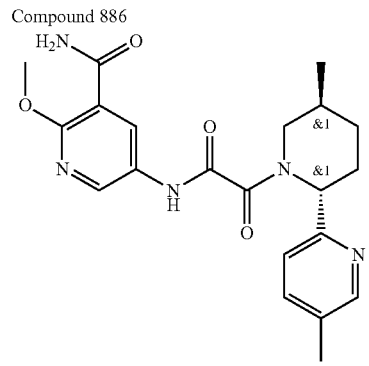

Compound 932

2-[(5-carbamoyl-6-methoxy-3-pyridyl)amino]-2-oxo-acetic acid (214.65 mg, 630.64 µmol, N(C2H5)3), 5-methyl-2-(5-methyl-2-piperidyl)pyridine (120 mg, 630.64 µmol), HATU (263.77 mg, 693.70 µmol) and TEA (70.20 mg, 693.70 µmol, 96.69 µL) were mixed in DMSO (2 mL) and stirred for 2 hr at 20° C. Reaction mixture was subjected to HPLC.

HPLC data: 2-10 min 20-45% MeCN/H₂O+TFA 30 mL/min (loading pump 4 mL MeCN) column: SunFire 100*19 mm, 5 microM 2-methoxy-5-[[2-[(2R,5R)-5-methyl-2-(5-methyl-2-pyridyl)-1-piperidyl]-2-oxo-acetyl]amino]pyridine-3-carboxamide (101.7 mg, 247.17 μmol, 39.19% yield) was obtained.

Cis-configuration was confirmed by 2D HNMR (Compound 886, H$_{2359596}$) 2-methoxy-5-[[2-[(2R,5S)-5-methyl-2-(5-methyl-2-pyridyl)-1-piperidyl]-2-oxo-acetyl]amino]pyridine-3-carboxamide (36.2 mg, 87.98 μmol, 13.95% yield) was obtained. Trans-configuration was confirmed by 2D HNMR (Compound 932, H$_{2359618}$)

Compound 886: ¹H NMR (DMSO-d₆, 600 MHz): δ (ppm) 0.75 (dd, 3H), 1.02 (m, 1H), 1.62 (m, 2H), 1.79 (m, 1H), 2.27 (m, 3H), 2.69 (m, 2H), 3.93 (m, 4H), 5.40 (m, 1H), 7.25 (dd, 1H), 7.62 (m, 1H), 7.71 (m, 2H), 8.44 (m, 2H), 8.53 (dd, 1H), 11.01 (m, 1H).

LCMS(ESI): [M+H]⁺ m/z: calcd 411.2; found 412.2; Rt=2.337 min.

Compound 932: ¹H NMR (DMSO-d₆, 600 MHz): δ (ppm) 1.01 (m, 3H), 1.31 (m, 1H), 1.62 (m, 1H), 1.95 (m, 2H), 2.27 (m, 3H), 2.41 (m, 1H), 2.72 (m, 1H), 3.78 (m, 4H), 5.37 (m, 1H), 7.27 (m, 1H), 7.69 (m, 3H), 8.48 (m, 3H), 10.98 (m, 1H).

LCMS(ESI): [M+H]⁺ m/z: calcd 411.2; found 412.0; Rt=2.194 min.

Example 201. The Synthesis of Rel-5-[[2-[(2S,5R)-5-methyl-2-[2-(trifluoromethyl)-1,3-benzothiazol-5-yl]-1-piperidyl]-2-oxo-acetyl]amino]pyridine-3-carboxamide (Compound 1029) and Rel-5-[[2-[(2R,5S)-5-methyl-2-[2-(trifluoromethyl)-1,3-benzothiazol-5-yl]-1-piperidyl]-2-oxo-acetyl]amino]pyridine-3-carboxamide (Compound 1023

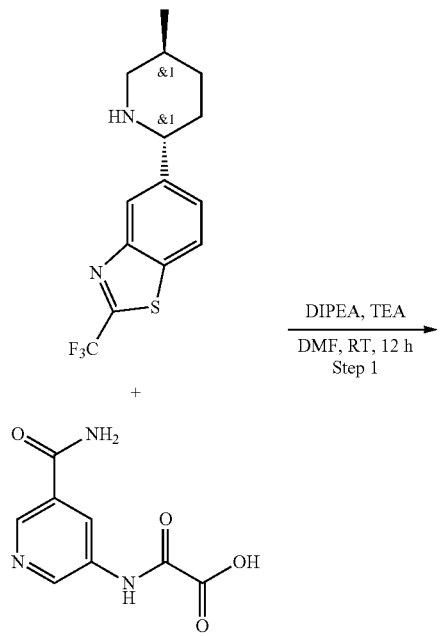 [SMILES: C[C@H]1CC[C@H](c2ccc3sc(C(F)(F)F)nc3c2)NC1 ; "DIPEA, TEA" ; "DMF, RT, 12 hStep 1" ; NC(=O)c1cncc(NC(=O)C(=O)O)c1]

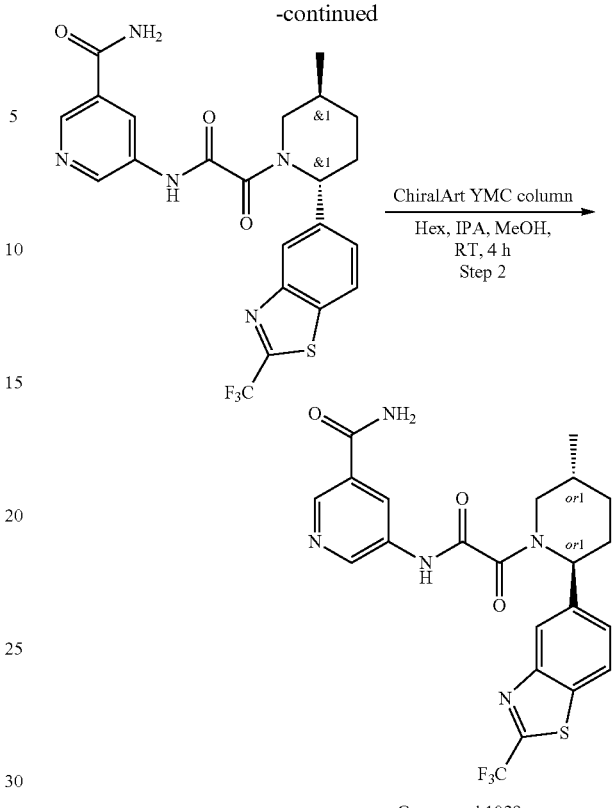

Compound 1029

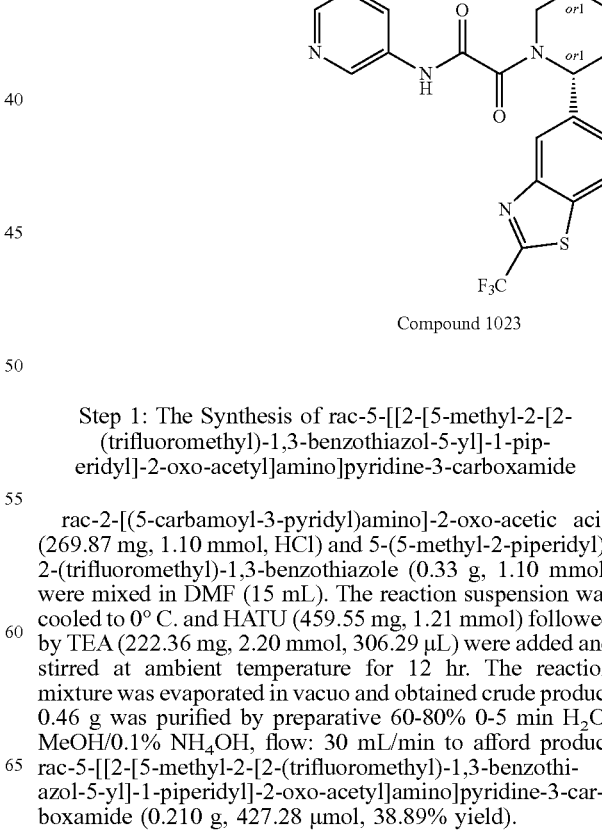

Compound 1023

Step 1: The Synthesis of rac-5-[[2-[5-methyl-2-[2-(trifluoromethyl)-1,3-benzothiazol-5-yl]-1-piperidyl]-2-oxo-acetyl]amino]pyridine-3-carboxamide rac-2-[(5-carbamoyl-3-pyridyl)amino]-2-oxo-acetic acid (269.87 mg, 1.10 mmol, HCl) and 5-(5-methyl-2-piperidyl)-2-(trifluoromethyl)-1,3-benzothiazole (0.33 g, 1.10 mmol) were mixed in DMF (15 mL). The reaction suspension was cooled to 0° C. and HATU (459.55 mg, 1.21 mmol) followed by TEA (222.36 mg, 2.20 mmol, 306.29 μL) were added and stirred at ambient temperature for 12 hr. The reaction mixture was evaporated in vacuo and obtained crude product 0.46 g was purified by preparative 60-80% 0-5 min H₂O/MeOH/0.1% NH₄OH, flow: 30 mL/min to afford product rac-5-[[2-[5-methyl-2-[2-(trifluoromethyl)-1,3-benzothiazol-5-yl]-1-piperidyl]-2-oxo-acetyl]amino]pyridine-3-carboxamide (0.210 g, 427.28 μmol, 38.89% yield).

LCMS(ESI): [M+H]+ m/z: calcd 491.2; found 492.2; Rt=3.092 min.

Step 2: The Synthesis of Rei-5-[[2-[(2S,5R)-5-methyl-2-[2-(trifluoromethyl)-], 3-benzothiazol-5-yl]-1-piperidyl]-2-oxo-acetyl]amino]pyridine-3-carboxamide (Compound 1029) and Rel-5-[[2-[(2R,5S)-5-methyl-2-[2-(trifluoromethyl)-1,3-benzothiazol-5-yl]-1-piperidyl]-2-oxo-acetyl]amino] pyridine-3-carboxamide (Compound 1023

The rac-5-[[2-[5-methyl-2-[2-(trifluoromethyl)-1,3-benzothiazol-5-yl]-1-piperidyl]-2-oxo-acetyl]amino]pyridine-3-carboxamide (0.210 g, 427.28 μmol) was subjected to chiral HPLC purification (Column: ChiralArt YMC (250*20, 5 um), Eluent: Hexane-IPA-MeOH, 50-25-25, flow rate: 14 mL/min) to give the two individual enantiomers Compound 1029—rel-5-[[2-[(2S,5R)-5-methyl-2-[2-(trifluoromethyl)-1,3-benzothiazol-5-yl]-1-piperidyl]-2-oxo-acetyl]amino]pyridine-3-carboxamide (0.0696 g, 141.61 μmol, 33.14% yield) and Compound 1023—rel-5-[[2-[(2R,5S)-5-methyl-2-[2-(trifluoromethyl)-1,3-benzothiazol-5-yl]-1-piperidyl]-2-oxo-acetyl]amino]pyridine-3-carboxamide (0.0876 g, 178.24 μmol, 41.71% yield).

Compound 1029: RT (IC, Hexane-IPA-MeOH, 50-25-25, 0.6 mL/min)=18.399 min.

LCMS(ESI): [M+H]+ m/z: calcd 491.2; found 492.0; Rt=1.224 min.

Compound 1023: RT (IC, Hexane-IPA-MeOH, 50-25-25, 0.6 mL/min)=34.083 min.

LCMS(ESI): [M+H]+ m/z: calcd 491.2; found 492.0; Rt=1.224 min.

Example 202. The Synthesis of Rel-2-methoxy-5-[[2-[(2S,5R)-5-methyl-2-[2-(trifluoromethyl)-1,3-benzothiazol-5-yl]-1-piperidyl]-2-oxo-acetyl]amino] pyridine-3-carboxamide (Compound 1030) and Rel-2-methoxy-5-[[2-[(2R,5S)-5-methyl-2-[2-(trifluoromethyl)-1,3-benzothiazol-5-yl]-1-piperidyl]-2-oxo-acetyl]amino]pyridine-3-carboxamide (Compound 1024

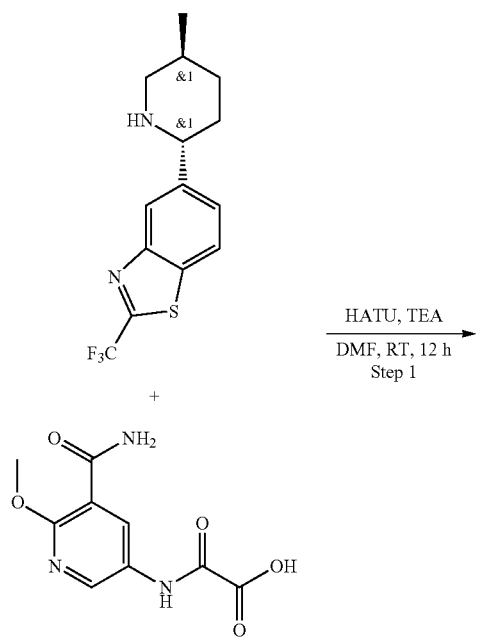 [SMILES: C[C@H]1CC[C@H](c2ccc3sc(C(F)(F)F)nc3c2)NC1 ; "HATU, TEA" ; "DMF, RT, 12 hStep 1" ; COc1ncc(NC(=O)C(=O)O)cc1C(N)=O]

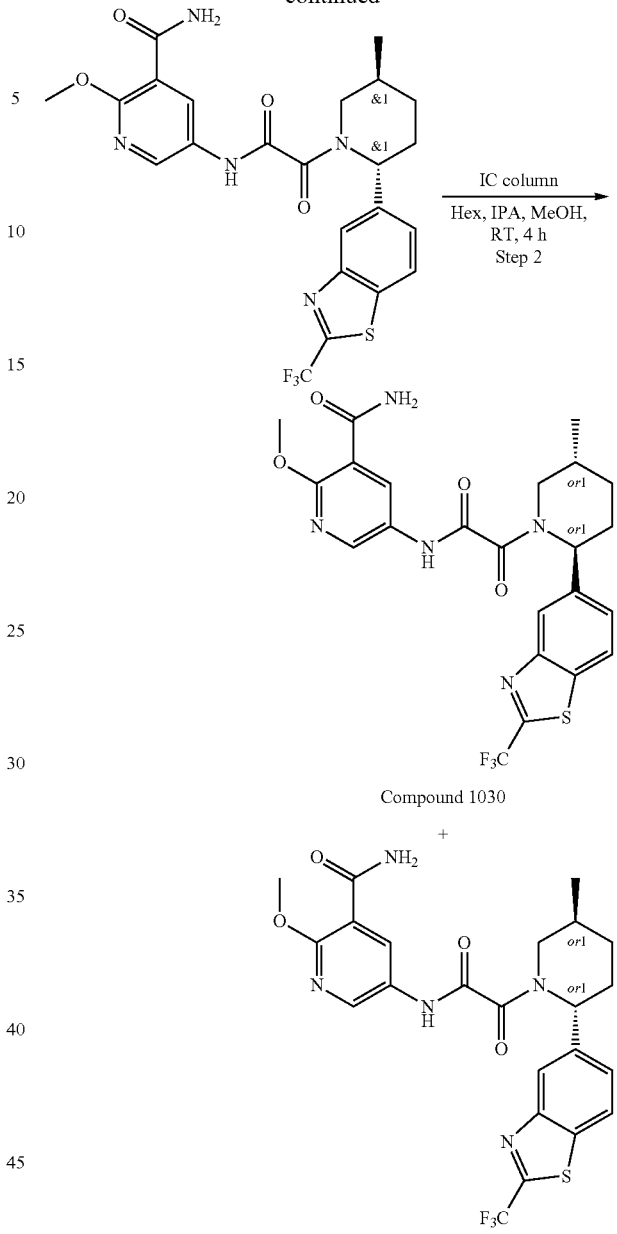

Step 1: The Synthesis of rac-2-methoxy-5-[[2-[5-methyl-2-[2-(trifluoromethyl)-1,3-benzothiazol-5-yl]-1-piperidyl]-2-oxo-acetyl]amino]pyridine-3-carboxamide 2-[(5-carbamoyl-6-methoxy-3-pyridyl)amino]-2-oxo-acetic acid (238.91 mg, 998.86 μmol) and rac-5-(5-methyl-2-piperidyl)-2-(trifluoromethyl)-1,3-benzothiazole (0.30 g, 998.86 μmol) were mixed in DMF (15 mL). The reaction suspension was cooled to 0° C. and HATU (417.78 mg, 1.10 mmol) followed by TEA (202.15 mg, 2.00 mmol, 278.44 μL) were added and stirred at ambient temperature for 12 hr. The reaction mixture was evaporated in vacuo and obtained crude product 0.39 g was purified by preparative 55-90% 0-5 min H2O/MeOH/0.1% NH4OH, flow: 30 mL/min to afford product rac-2-methoxy-5-[[2-[5-methyl-2-[2-(trifluoromethyl)-1,3-benzothiazol-5-yl]-1-piperidyl]-2-oxo-acetyl] amino]pyridine-3-carboxamide (0.1596 g, 306.03 µmol, 30.64% yield).

LCMS(ESI): [M+H]+ m/z: calcd 521.2; found 522.2; Rt=3.608 min.

Step 2: The Synthesis of Rel-2-methoxy-5-[[2-[(2S, 5R)-5-methyl-2-[2-(trifluoromethyl)-1,3-benzothiazol-5-yl]-1-piperidyl]-2-oxo-acetyl]amino]pyridine-3-carboxamide (Compound 1030) and Rel-2-methoxy-5-[[2-[(2R,5S)-5-methyl-2-[2-(trifluoromethyl)-], 3-benzothiazol-5-yl]-1-piperidyl]-2-oxo-acetyl]amino]pyridine-3-carboxamide (Compound 1024

The rac-2-methoxy-5-[[2-[5-methyl-2-[2-(trifluoromethyl)-1,3-benzothiazol-5-yl]-1-piperidyl]-2-oxo-acetyl] amino]pyridine-3-carboxamide (0.1596 g, 306.03 µmol) was subjected to chiral HPLC purification (Column: ChiralPac IC (250*20, 5 um), Eluent: Hexane-IPA-MeOH, 60-20-20, flow rate: 15 mL/min) to give the two individual enantiomers Compound 1030—rel-2-methoxy-5-[[2-[(2S, 5R)-5-methyl-2-[2-(trifluoromethyl)-1,3-benzothiazol-5-yl]-1-piperidyl]-2-oxo-acetyl]amino]pyridine-3-carboxamide (0.0521 g, 99.90 µmol, 32.64% yield) and Compound 1024—rel-2-methoxy-5-[[2-[(2R,5S)-5-methyl-2-[2-(trifluoromethyl)-1,3-benzothiazol-5-yl]-1-piperidyl]-2-oxo-acetyl]amino]pyridine-3-carboxamide (0.0575 g, 110.26 µmol, 36.03% yield).

Compound 1030: RT (IC, Hexane-IPA-MeOH, 50-25-25, 0.6 mL/min)=19.034 min.

LCMS(ESI): [M+H]+ m/z: calcd 521.0; found 522.0; Rt=3.459 min.

Compound 1024: RT (IC, Hexane-IPA-MeOH, 50-25-25, 0.6 mL/min)=29.406 min.

LCMS(ESI): [M+H]+ m/z: calcd 521.0; found 522.0; Rt=3.459 min.

Example 203. The Synthesis of Rel-N-(6-amino-5-ethyl-3-pyridyl)-2-[(2S,5R)-5-methyl-2-[2-(trifluoromethyl)-1,3-benzothiazol-5-yl]-1-piperidyl]-2-oxo-acetamide (Compound 1027) and Rel-N-(6-amino-5-ethyl-3-pyridyl)-2-[(2R,5S)-5-methyl-2-[2-(trifluoromethyl)-1,3-benzothiazol-5-yl]-1-piperidyl]-2-oxo-acetamide (Compound 1022)

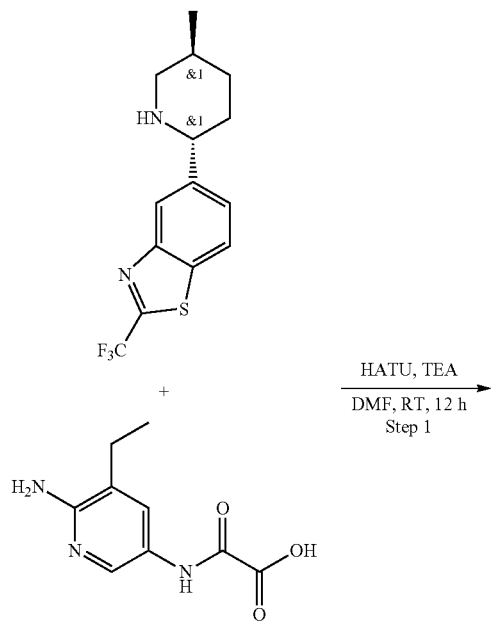 [SMILES: C[C@H]1CC[C@H](c2ccc3sc(C(F)(F)F)nc3c2)NC1 ; "HATU, TEA" ; "DMF, RT, 12 hStep 1" ; CCc1cc(NC(=O)C(=O)O)cnc1N]

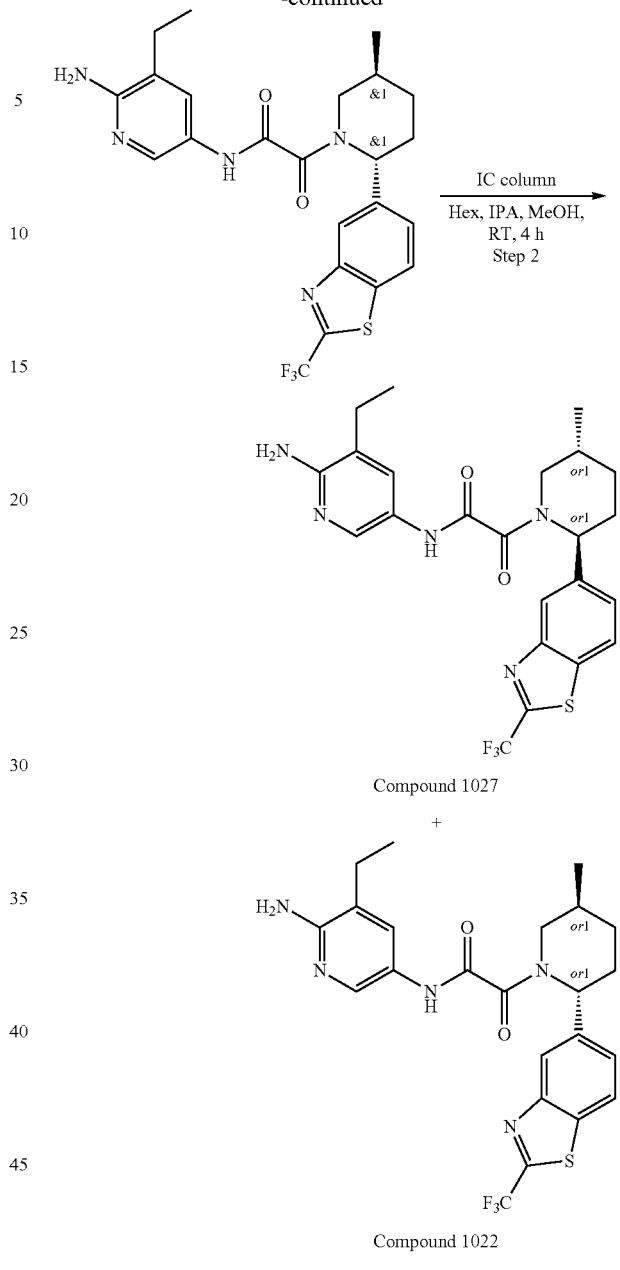

Compound 1027

Compound 1022

Step 1: The Synthesis of rac-N-(6-amino-5-ethyl-3-pyridyl)-2-[5-methyl-2-[2-(trifluoromethyl)-1,3-benzothiazol-5-yl]-1-piperidyl]-2-oxo-acetamide 2-[(6-amino-5-ethyl-3-pyridyl)amino]-2-oxo-acetic acid (208.96 mg, 998.86 µmol) and rac-5-(5-methyl-2-piperidyl)-2-(trifluoromethyl)-1,3-benzothiazole (0.3 g, 998.86 µmol) were mixed in DMF (15 mL). The reaction suspension was cooled to 0° C. and HATU (417.78 mg, 1.10 mmol) followed by TEA (202.15 mg, 2.00 mmol, 278.44 µL) were added and stirred at ambient temperature for 12 hr. The reaction mixture was evaporated in vacuo and obtained crude product 0.39 g was purified by preparative 65-85% 0-5 min H₂O/MeOH/0.1% NH₄OH, flow: 30 mL/min to afford product rac-N-(6-amino-5-ethyl-3-pyridyl)-2-[5-methyl-2-[2-(trifluoromethyl)-1,3-benzothiazol-5-yl]-1-piperidyl]-2-oxo-acetamide (227.20 mg, 462.23 µmol, 46.28% yield).

LCMS(ESI): [M+H]⁺ m/z: calcd 491.2; found 492.2; Rt=2.992 min.

Step 2: The Synthesis of Rel-N-(6-amino-5-ethyl-3-pyridyl)-2-[(2S,5R)-5-methyl-2-[2-(trifluoromethyl)-], 3-benzothiazol-5-yl]-1-piperidyl]-2-oxo-acetamide (Compound 1027) and Rel-N-(6-amino-5-ethyl-3-pyridyl)-2-[(2R,5S)-5-methyl-2-[2-(trifluoromethyl)-1,3-benzothiazol-5-yl]-1-piperidyl]-2-oxo-acetamide (Compound 1022

The rac-N-(6-amino-5-ethyl-3-pyridyl)-2-[5-methyl-2-[2-(trifluoromethyl)-1,3-benzothiazol-5-yl]-1-piperidyl]-2-oxo-acetamide (227.20 mg, 462.23 μmol) was subjected to chiral HPLC purification (Column: ChiralArt YMC (250*20, 5 um), Eluent: Hexane-IPA-MeOH, 50-25-25, flow rate: 14 mL/min) to give the two individual enantiomers Compound 1027—rel-N-(6-amino-5-ethyl-3-pyridyl)-2-[(2S,5R)-5-methyl-2-[2-(trifluoromethyl)-1,3-benzothiazol-5-yl]-1-piperidyl]-2-oxo-acetamide (0.0675 g, 137.33 μmol, 29.71% yield) and Compound 1022—rel-N-(6-amino-5-ethyl-3-pyridyl)-2-[(2R,5S)-5-methyl-2-[2-(trifluoromethyl)-1,3-benzothiazol-5-yl]-1-piperidyl]-2-oxo-acetamide (0.0795 g, 161.74 μmol, 34.99% yield).

Compound 1027: RT (IC, Hexane-IPA-MeOH, 50-25-25, 0.6 mL/min)=12.813 min.

LCMS(ESI): [M+H]⁺ m/z: calcd 491.0; found 492.0; Rt=1.146 min.

Compound 1022: RT (IC, Hexane-IPA-MeOH, 50-25-25, 0.6 mL/min)=20.716 min.

LCMS(ESI): [M+H]⁺ m/z: calcd 491.0; found 492.2; Rt=3.364 min.

Example 204. Synthesis of 5-(2-(5-methyl-2-(1H-thieno[3,2-c]pyrazol-5-yl)piperidin-1-yl)-2-oxoacetamido)Nicotinamide (Compound 868 and Compound 873

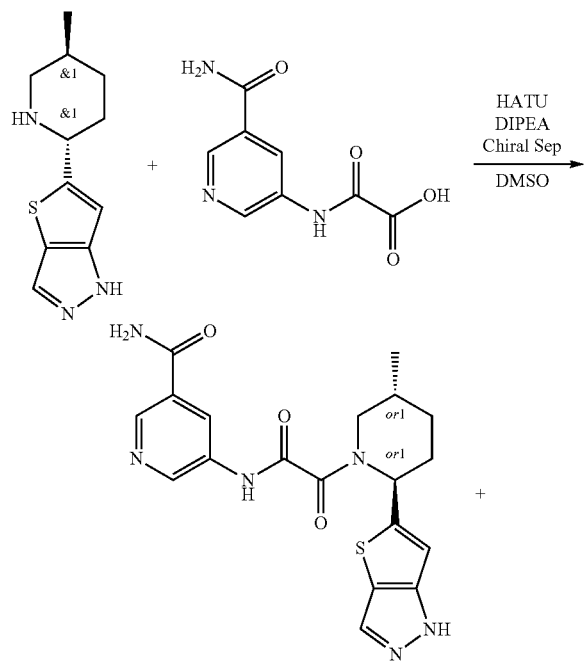

Compound 868

-continued

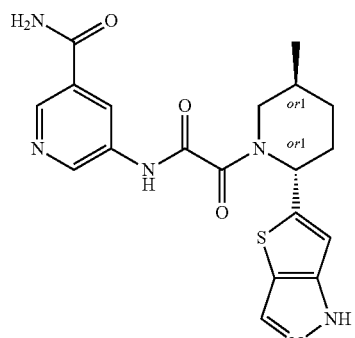

Compound 873

2-[(5-carbamoyl-3-pyridyl)amino]-2-oxo-acetic acid (236.26 mg, 1.13 mmol), 5-[(2R,5S)-5-methyl-2-piperidyl]-1H-thieno[3,2-c]pyrazole (0.25 g, 1.13 mmol) and DIPEA (437.96 mg, 3.39 mmol, 590.24 μL) were dissolved in DMSO (6 mL) under gentle heating. HATU (515.40 mg, 1.36 mmol) was added in small portions under vigorous stirring and occasional heating. After the reaction was complete, the mixture was purified by HPLC (39% 0.5-6.5 min water-MeOH; flow 30 ml/min (loading pump 4 ml/min MeOH); target mass 412; column SunFire C18 100×19 mm 5 um (R)) to give racemic product. After chiral HPLC (IA-I (250*20, 5 mkm), Hexane-IPA-MeOH, 50-25-25, 12 ml/min) 5-[[2-[(2S,5R)-5-methyl-2-(1H-thieno[3,2-c]pyrazol-5-yl)-1-piperidyl]-2-oxo-acetyl]amino]pyridine-3-carboxamide (29 mg, 70.31 μmol, 6.22% yield) and 5-[[2-[(2R,5S)-5-methyl-2-(1H-thieno[3,2-c]pyrazol-5-yl)-1-piperidyl]-2-oxo-acetyl]amino]pyridine-3-carboxamide (29 mg, 70.31 μmol, 6.22% yield) were obtained.

Ret time for Compound 868 in analytical conditions (column: IA, Hexane-IPA-MeOH, 50-25-25, 0.6 ml/min as mobile phase) 37.50 min and for Compound 873 54.49 min.

Compound 868: Retention time: 37.50 min

¹H NMR (600 MHz, DMSO-d₆) δ (ppm) 0.97-1.03 (m, 3H), 1.35-1.49 (m, 1H), 1.82-2.01 (m, 2H), 2.04-2.20 (m, 2H), 2.96-3.02 (m, 0.4H), 3.39-3.43 (m, 0.6H), 3.45-4.14 (m, 1H), 5.46-5.89 (m, 1H), 6.98-7.20 (m, 1H), 7.55-7.66 (m, 1H), 7.68-8.02 (m, 1H), 8.10-8.23 (m, 1H), 8.44-8.52 (m, 1H), 8.71-8.94 (m, 2H), 11.19-11.32 (m, 1H), 12.93-13.36 (m, 1H).

LCMS(ESI): [M]⁺ m/z: calcd 412.2; found 413.2; Rt=1.676 min.

Compound 873: Retention time: 54.49 min

¹H NMR (600 MHz, DMSO-d₆) δ (ppm) 0.95-1.02 (m, 3H), 1.39-1.48 (m, 1H), 1.81-1.98 (m, 2H), 2.05-2.24 (m, 2H), 2.96-3.02 (m, 0.4H), 3.37-3.43 (m, 0.6H), 3.43-4.14 (m, 1H), 5.43-5.91 (m, 1H), 7.00-7.15 (m, 1H), 7.54-7.65 (m, 1H), 7.66-8.01 (m, 1H), 8.11-8.21 (m, 1H), 8.49 (s, 1H), 8.70-8.94 (m, 2H), 11.11-11.39 (m, 1H), 12.79-13.38 (m, 1H).

LCMS(ESI): [M]⁺ m/z: calcd 412.2; found 413.2; Rt=1.700 min.

Example 205. The Synthesis of 2-methoxy-5-(2-(5-methyl-2-(JH-thieno[3,2-c]pyrazol-5-yl)piperidin-1-yl)-2-oxoacetamido)Nicotinamide (Compound 1006 and Compound 952

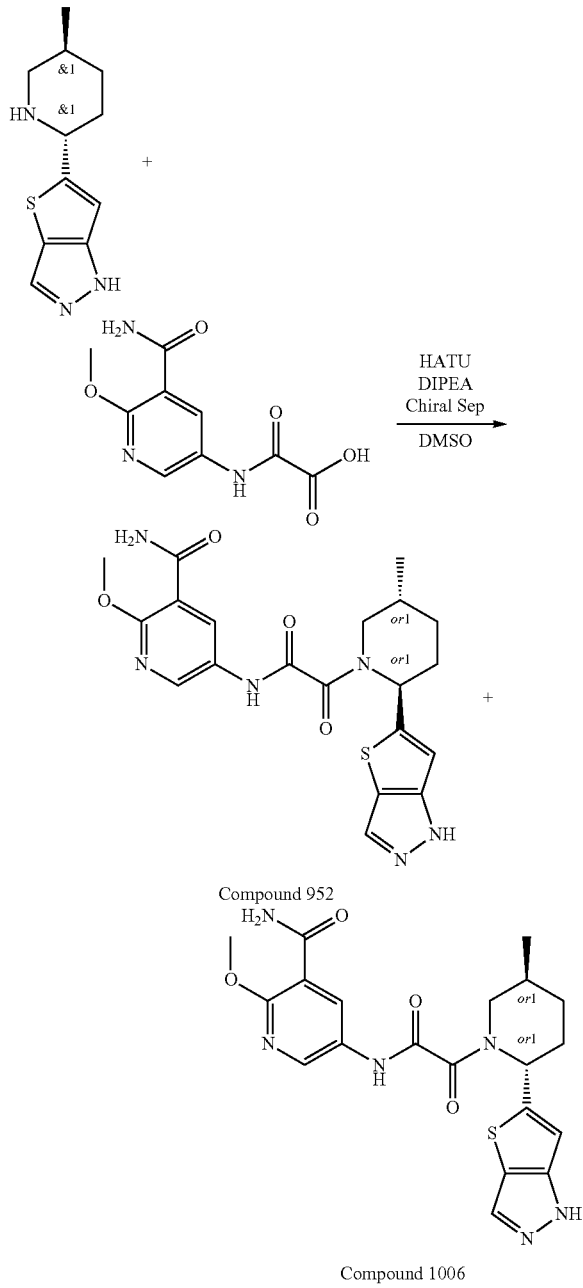

Compound 1006

5-[(2R,5S)-5-methyl-2-piperidyl]-1H-thieno[3,2-c]pyrazole (300.79 mg, 1.36 mmol), 2-[(5-carbamoyl-6-methoxy-3-pyridyl)amino]-2-oxo-acetic acid (325.07 mg, 1.36 mmol) and DIPEA (526.94 mg, 4.08 mmol, 710.16 µL) were dissolved in DMSO (6 mL) under gentle heating. HATU (620.11 mg, 1.63 mmol) was added in small portions under vigorous stirring and occasional heating. After the reaction was complete, the mixture was purified by HPLC (46% 0.5-6.5 min water-MeOH; flow 30 ml/min (loading pump 4 ml/min MeOH); target mass 442; column SunFire C18 100×19 mm 5 um (R)) to give racemic product. After chiral HPLC (Chiral ART Cellulose-SC (250*20, 5 mkm), Hexane-IPA-MeOH, 50-25-25, 12 ml/min) isomer 2-methoxy-5-[[2-[(2R,5S)-5-methyl-2-(1H-thieno[3,2-c]pyrazol-5-yl)-1-piperidyl]-2-oxo-acetyl]amino]pyridine-3-carboxamide (40 mg, 90.40 µmol, 6.65% yield) was isolated in optically pure form, but with unknown impurity; purified with HPLC(18% 0.5-6.5 min water-MeCN; flow 30 ml/min (loading pump 4 ml/min MeCN); target mass 442; column SunFire C18 100×19 mm Sum (R)) to give pure product. Isomer 2-methoxy-5-[[2-[(2S,5R)-5-methyl-2-(1H-thieno[3,2-c]pyrazol-5-yl)-1-piperidyl]-2-oxo-acetyl]amino]pyridine-3-carboxamide (53 mg, 119.78 µmol, 8.81% yield) was isolated with corresponding cis-impurity and purified with chiral HPLC (Chiralcel OJ-H (250*20 mm, 5 mkm); Mobile phase: IPA-MeOH, 50-50, Flow Rate: 10 mL/min; Column Temperature: 24° C.; Wavelength: 205 nm, 254 nm, 306 nm), RetTime (isomer A)=21.24 min; RetTime (isomer B)=29.74 min) to give pure product 2-methoxy-5-[[2-[(2S,5R)-5-methyl-2-(1H-thieno[3,2-c]pyrazol-5-yl)-1-piperidyl]-2-oxo-acetyl]amino]pyridine-3-carboxamide (53 mg, 119.78 µmol, 8.81% yield).

Ret time for Compound 1006 in analytical conditions (column: IC, Hexane-IPA-MeOH, 50-25-25, 0.6 ml/min as mobile phase) 74.26 min and for Compound 952 31.77 min.

Compound 1006: Retention time: 74.26 min $^1$H NMR (600 MHz, DMSO-$d_6$) δ (ppm) 0.95-1.06 (m, 3H), 1.37-1.48 (m, 1H), 1.84-1.99 (m, 2H), 2.03-2.22 (m, 2H), 2.94-3.01 (m, 0.4H), 3.39-3.44 (m, 0.6H), 3.47-3.52 (m, 0.6H), 3.91-3.97 (m, 3H), 4.03-4.08 (m, 0.4H), 5.42-5.88 (m, 1H), 7.00-7.10 (m, 1H), 7.68-7.75 (m, 2H), 7.80 (br s, 1H), 8.44-8.50 (m, 1H), 8.52-8.57 (m, 1H), 11.01 (br s, 1H), 13.06 (br s, 1H).

LCMS(ESI): [M]$^+$ m/z: calcd 442.2; found 443.2; Rt=2.428 min.

Compound 952: Retention time: 31.77 min $^1$H NMR (600 MHz, DMSO-$d_6$) δ (ppm) 0.98-1.02 (m, 3H), 1.37-1.46 (m, 1H), 1.82-1.98 (m, 2H), 2.05-2.20 (m, 2H), 2.92-3.42 (m, 1H), 3.47-4.06 (m, 4H), 5.45-5.86 (m, 1H), 6.97-7.15 (m, 1H), 7.63-8.04 (m, 3H), 8.41-8.51 (m, 1H), 8.51-8.57 (m, 1H), 11.05 (s, 1H), 12.93-13.34 (m, 1H).

LCMS(ESI): [M]$^+$ m/z: calcd 442.2; found 443.2; Rt=2.430 min.

Example 206. Synthesis of 5-(2-(5-methyl-2-(1H-thieno[2,3-c]pyrazol-5-yl)piperidin-1-yl)-2-oxoacetamido)Nicotinamide (Compound 971 and Compound 943

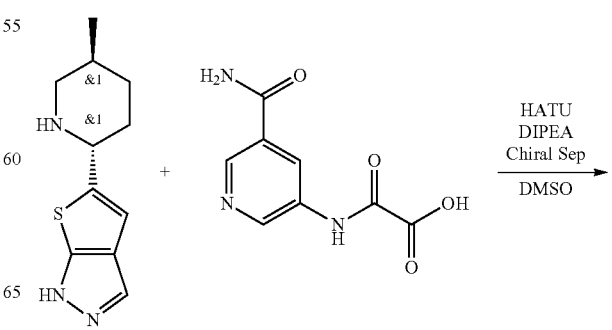

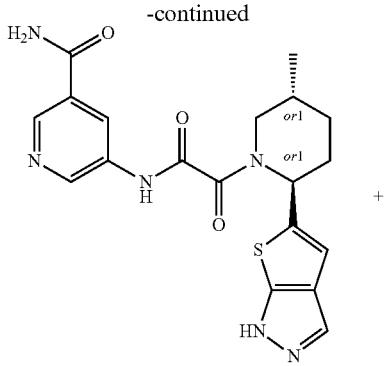

Compound 943

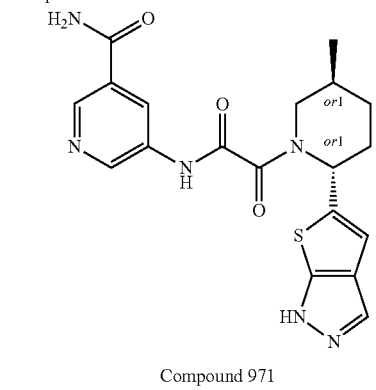

Compound 971

2-[(5-carbamoyl-3-pyridyl)amino]-2-oxo-acetic acid (284.26 mg, 1.36 mmol), 5-[(2S,5R)-5-methyl-2-piperidyl]-2H-thieno[2,3-c]pyrazole (300.79 mg, 1.36 mmol) and DIPEA (526.94 mg, 4.08 mmol, 710.16 μL) were dissolved in DMSO (6 mL) under gentle heating. HATU (620.11 mg, 1.63 mmol) was added in small portions under vigorous stirring and occasional heating. After the reaction was complete, the mixture was purified by HPLC (40-90% 0.5-6.5 min water-MeOH; flow 30 ml/min; (loading pump 4 ml/min MeOH); target mass 498; column SunFire C18 100×19 mm 5 um (L)) and chiral HPLC (Chiralpak IA-II (250*30, 5 mkm), Hexane-IPA-MeOH, 50-25-25, 12 ml/min) to give 5-[[2-[(2S,5R)-5-methyl-2-(1H-thieno[2,3-c]pyrazol-5-yl)-1-piperidyl]-2-oxo-acetyl]amino]pyridine-3-carboxamide (55 mg, 133.34 μmol, 9.81% yield) and 5-[[2-[(2R,5S)-5-methyl-2-(1H-thieno[2,3-c]pyrazol-5-yl)-1-piperidyl]-2-oxo-acetyl]amino]pyridine-3-carboxamide (90 mg, 218.20 μmol, 16.06% yield) and 5-[[2-[(2S,5R)-5-methyl-2-(1H-thieno[2,3-c]pyrazol-5-yl)-1-piperidyl]-2-oxo-acetyl]amino]pyridine-3-carboxamide (55 mg, 133.34 μmol, 9.81% yield).

Ret time for Compound 971 in analytical conditions (column: IA, Hexane-IPA-MeOH, 50-25-25, 0.6 ml/min as mobile phase) 81.55 min and for Compound 943 41.81 min.

Compound 971: Retention time: 81.55 min $^{1}$H NMR (600 MHz, DMSO-$d_6$) δ (ppm) 1.01 (d, 3H), 1.41 (m, 1H), 1.89 (m, 2H), 2.17 (m, 2H), 3.12 (m, 1H), 4.02 (m, 1H), 5.65 (m, 1H), 6.95 (s, 1H), 7.58 (d, 1H), 7.94 (bds, 1H), 8.13 (d, 1H), 8.49 (s, 1H), 8.77 (s, 1H), 8.89 (s, 1H), 11.23 (bds, 1H), 13.29 (bds, 1H).

LCMS(ESI): [M]$^+$ m/z: calcd 412.2; found 413.2; Rt=2.028 min.

Compound 943: Retention time: 41.81 min $^{1}$H NMR (600 MHz, DMSO-$d_6$) δ (ppm) 1.02 (d, 3H), 1.42 (m, 1H), 1.95 (m, 2H), 2.07 (m, 2H), 3.12 (m, 1H), 4.05 (m, 1H), 5.65 (m, 1H), 6.95 (s, 1H), 7.60 (d, 1H), 7.94 (bds, 1H), 8.13 (d, 1H), 8.49 (s, 1H), 8.77 (s, 1H), 8.89 (s, 1H), 11.23 (bds, 1H), 13.29 (bds, 1H).

LCMS(ESI): [M]$^+$ m/z: calcd 412.2; found 413.2; Rt=2.020 min.

Example 207. The Synthesis of 2-methoxy-5-(2-(5-methyl-2-(JH-thieno[2,3-c]pyrazol-5-yl)piperidin-1-yl)-2-oxoacetamido)Nicotinamide (Compound 950 and Compound 968

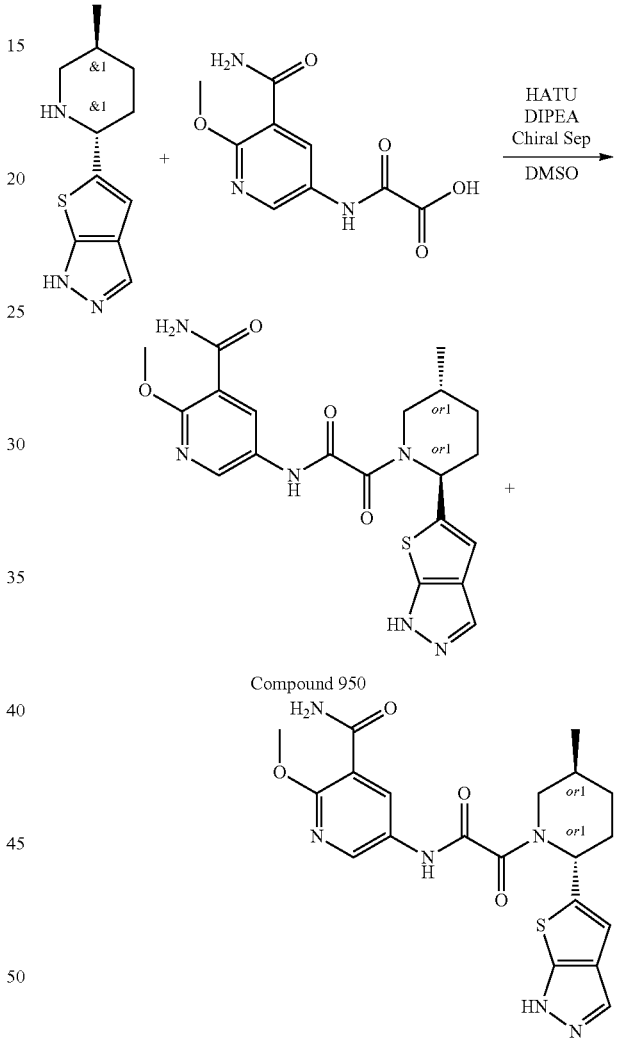

Compound 950

Compound 968

2-[(5-carbamoyl-6-methoxy-3-pyridyl)amino]-2-oxo-acetic acid (325.07 mg, 1.36 mmol), 5-[(2S,5R)-5-methyl-2-piperidyl]-2H-thieno[2,3-c]pyrazole (300.79 mg, 1.36 mmol) and DIPEA (526.94 mg, 4.08 mmol, 710.16 μL) were dissolved in DMSO (6 mL) under gentle heating. HATU (620.11 mg, 1.63 mmol) was added in small portions under vigorous stirring and occasional heating. After the reaction was complete, the mixture was purified by HPLC (45-50% 0.5-6 min water-MeOH; flow 30 ml/min (loading pump 4 ml/min R1); target mass 442; column SunFire C18 100×19 mm 5 um (R)) and purificated racemic mixture was subjected for chiral HPLC (Chiralcel OD-H (250*30, 5 mkm), Hexane-IPA-MeOH, 70-15-15, 30 ml/min) to give 2-methoxy-5-[[2-[(2S,5R)-5-methyl-2-(1H-thieno[2,3-c]pyrazol-5-yl)-1-piperidyl]-2-oxo-acetyl]amino]pyridine-3-carboxamide (210 mg, 474.59 µmol, 34.92% yield) and 2-methoxy-5-[[2-[(2R,5S)-5-methyl-2-(1H-thieno[2,3-c]pyrazol-5-yl)-1-piperidyl]-2-oxo-acetyl]amino]pyridine-3-carboxamide (140 mg, 316.39 µmol, 23.28% yield) and 2-methoxy-5-[[2-[(2S,5R)-5-methyl-2-(1H-thieno[2,3-c]pyrazol-5-yl)-1-piperidyl]-2-oxo-acetyl]amino]pyridine-3-carboxamide (210 mg, 474.59 µmol, 34.92% yield).

Ret time for Compound 950 in analytical conditions (column: OD-H, Hexane-IPA-MeOH, 50-25-25, 0.6 ml/min as mobile phase) 11.75 min and for Compound 968 14.25 min.

Compound 950: Retention time: 11.75 min $^1$H NMR (600 MHz, DMSO-$d_6$) δ (ppm) 1.01 (d, 3H), 1.40 (m, 1H), 1.89 (m, 2H), 2.04 (m, 2H), 3.12 (m, 1H), 3.92 (m, 1H), 3.94 (s, 3H), 5.65 (m, 1H), 6.95 (s, 1H), 7.73 (m, 2H), 7.93 (m, 1H), 8.46 (m, 1H), 8.55 (s, 1H), 11.02 (s, 1H), 13.30 (m, 1H).

LCMS(ESI): [M]$^+$ m/z: calcd 452.2; found 453.2; Rt=2.390 min.

Compound 968: Retention time: 14.25 min $^1$H NMR (600 MHz, DMSO-$d_6$) δ (ppm) 1.01 (d, 3H), 1.42 (m, 1H), 1.89 (m, 2H), 2.05 (m, 2H), 3.12 (m, 1H), 3.86 (m, 1H), 3.94 (s, 3H), 5.65 (m, 1H), 6.95 (s, 1H), 7.73 (m, 2H), 7.93 (m, 1H), 8.46 (m, 1H), 8.55 (s, 1H), 11.02 (s, 1H), 13.30 (m, 1H).

LCMS(ESI): [M]$^+$ m/z: calcd 452.2; found 453.2; Rt=2.394 min.

Example 208. The Synthesis of 5-(2-(5-methyl-2-(JH-pyrazol-3-yl)piperidin-1-yl)-2-oxoacetamido) Nicotinamide (Compound 978 and Compound 1007

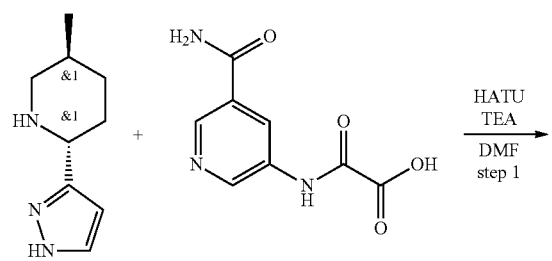

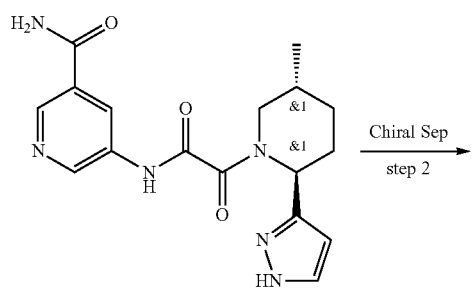

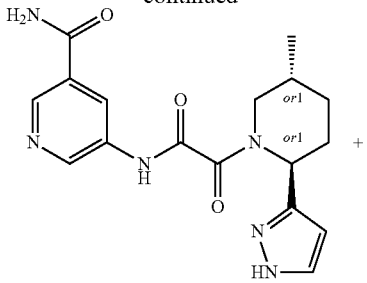

Compound 1007

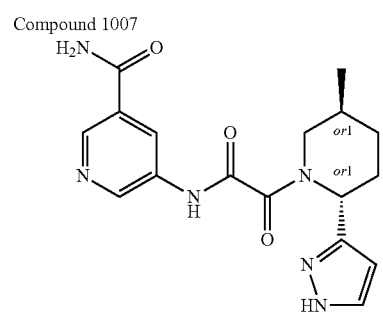

Compound 978

Step 1: Synthesis of 5-(2-(5-methyl-2-(1H-pyrazol-3-yl)piperidin-1-yl)-2-oxoacetamido)Nicotinamide HATU (702.48 mg, 1.85 mmol) was added in small portions over 1 hr period to a stirred mixture of (2R,5S)-5-methyl-2-(1H-pyrazol-3-yl)piperidine (400 mg, 1.68 mmol, 2HCl), 2-[(5-carbamoyl-3-pyridyl)amino]-2-oxo-acetic acid (474.41 mg, 1.93 mmol, HCl) and TEA (1.36 g, 13.44 mmol, 1.87 mL) in DMF (6 mL) at 25° C. The resulting mixture was stirred at 25° C. for 18 hr, and then submitted to reverse phase HPLC (column: YMC Triart C18 100×20 mm, 5 um; mobile phase: 5-55% 0-5 min H$_2$O/MeOH; flow rate: 30 ml/min (loading pump 4 ml/min MeOH) to afford 5-[[2-[(2R,5S)-5-methyl-2-(1H-pyrazol-3-yl)-1-piperidyl]-2-oxo-acetyl]amino]pyridine-3-carboxamide (125 mg, 350.75 µmol, 20.88% yield) as light-yellow gum, which was directly submitted to preparative chiral HPLC.

LCMS(ESI): [M]$^+$ m/z: calcd 356.2; found 357.2; Rt=1.694 min.

Step 2: Chiral Separation (Compound 978 and Compound 1007

Racemic 5-[[2-[(2R,5S)-5-methyl-2-(1H-pyrazol-3-yl)-1-piperidyl]-2-oxo-acetyl]amino]pyridine-3-carboxamide (125 mg, 350.75 µmol) was submitted to preparative chiral HPLC (Column: Chiralpak IC (250*20, 5 mkm); Mobile phase: Hexane-IPA-MeOH, 60-20-20; Flow rate: 12 ml/min, column temperature: 20° C.; Wavelength: 205 nm, 215 nm) to afford Compound 1007 5-[[2-[(2S,5R)-5-methyl-2-(1H-pyrazol-3-yl)-1-piperidyl]-2-oxo-acetyl]amino]pyridine-3-carboxamide (28 mg, 78.57 µmol, 22.40% yield) (RT=36.540 min.), and Compound 978 5-[[2-[(2R,5S)-5-methyl-2-(1H-pyrazol-3-yl)-1-piperidyl]-2-oxo-acetyl]amino]pyridine-3-carboxamide (32 mg, 89.79 µmol, 25.60% yield) (RT=58.232 min.).

Ret time for Compound 978 in analytical conditions (column: IC, Hexane-IPA-MeOH, 50-25-25, 0.6 ml/min as mobile phase) 31.91 min and for Compound 1007 22.90 min.

Compound 978: Retention time: 31.91 min

¹H NMR (600 MHz, DMSO-d₆) δ (ppm) 0.69-0.95 (m, 3H), 1.16-1.40 (m, 2H), 1.54-1.69 (m, 1H), 1.76-2.00 (m, 3H), 2.03-2.12 (m, 1H), 2.73-2.96 (m, 1H), 3.42-3.62 (m, 1H), 6.01-6.34 (m, 1H), 7.24-7.62 (m, 2H), 7.64-7.89 (m, 1H), 8.13-8.20 (m, 1H), 8.46-8.52 (m, 1H), 8.71-8.79 (m, 1H), 11.09-11.19 (m, 1H).

LCMS(ESI): [M]⁺ m/z: calcd 356.2; found 357.2; Rt=1.637 min.

Compound 1007: Retention time: 22.90 min

¹H NMR (600 MHz, DMSO-d₆) δ (ppm) 0.69-0.95 (m, 3H), 1.16-1.40 (m, 2H), 1.54-1.69 (m, 1H), 1.76-2.00 (m, 3H), 2.03-2.12 (m, 1H), 2.73-2.96 (m, 1H), 3.42-3.62 (m, 1H), 6.01-6.34 (m, 1H), 7.24-7.62 (m, 2H), 7.64-7.89 (m, 1H), 8.13-8.20 (m, 1H), 8.46-8.52 (m, 1H), 8.71-8.79 (m, 1H), 11.09-11.19 (m, 1H).

LCMS(ESI): [M]⁺ m/z: calcd 356.2; found 357.2; Rt=1.638 min.

Example 209. The Synthesis of 2-(2-(1'H-[1,3'-Bipyrazol]-3-yl)-5-methylpiperidin-1-yl)-N-(6-amino-5-ethylpyridin-3-yl)-2-oxoacetamide (Compound 931 and Compound 913

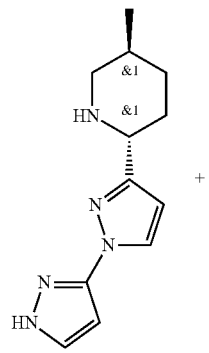

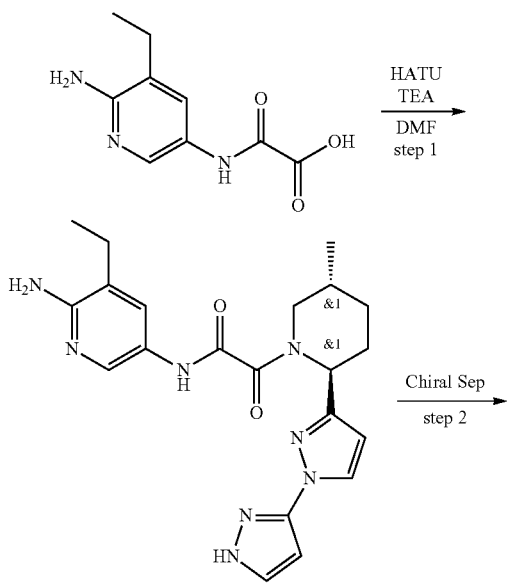

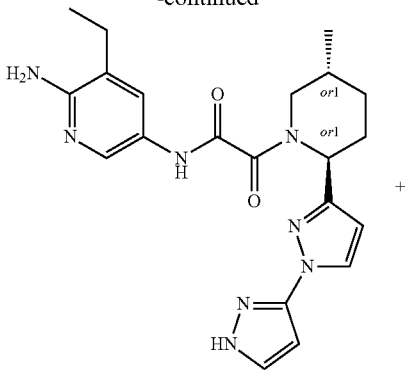

Compound 931

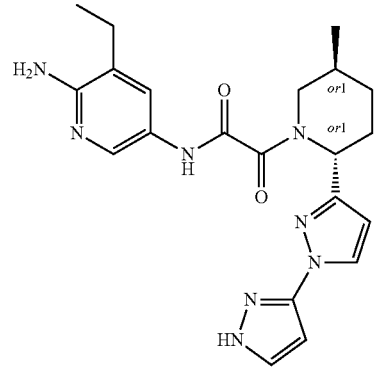

Compound 913

Step 1: Synthesis of 2-(2-(1'H-[1,3'-Bipyrazol]-3-yl)-5-methylpiperidin-1-yl)-N-(6-amino-5-ethylpyridin-3-yl)-2-oxoacetamide HATU (798.01 mg, 2.10 mmol) was added in small portions over 1.5 hr period to a stirred mixture of (2R,5S)-5-methyl-2-[1-(1H-pyrazol-3-yl)pyrazol-3-yl]piperidine (650 mg, 1.91 mmol, 3HCl), 2-[(6-amino-5-ethyl-3-pyridyl)amino]-2-oxo-acetic acid (399.15 mg, 1.91 mmol) and TEA (1.5 g, 14.82 mmol, 2.07 mL) in DMF (4.5 mL) at 25° C. The resulting mixture was stirred at 25° C. for 18 hr, and then submitted to reverse phase HPLC (column: YMC Triart C18 100×20 mm, 5 um) mobile phase: 45-55% 0-5 min H₂O/MeOH/0.1% NH₄OH, flow rate: 30 ml/min (loading pump 4 ml/min MeOH) to afford 230 mg of crude product, which was purified by reverse phase HPLC (column: Chromatorex 18 SMB100-5T 100×19 mm 5 um; mobile phase: 20-70% 0-5 min H₂O/MeOH; flow rate: 30 ml/min (loading pump 4 ml/min MeOH)) to afford N-(6-amino-5-ethyl-3-pyridyl)-2-[(2R,5S)-5-methyl-2-[1-(1H-pyrazol-3-yl)pyrazol-3-yl]-1-piperidyl]-2-oxo-acetamide (64 mg, 151.49 μmol, 7.94% yield) as pink gum, which was used directly in the next step.

LCMS(ESI): [M]⁺ m/z: calcd 422.2; found 423.2; Rt=1.017 min.

Step 2: Chiral Separation (Compound 931 and Compound 913

Racemic N-(6-amino-5-ethyl-3-pyridyl)-2-[(2R,5S)-5-methyl-2-[1-(1H-pyrazol-3-yl)pyrazol-3-yl]-1-piperidyl]-2-oxo-acetamide (64 mg, 151.49 μmol) was submitted to preparative chiral HPLC (Column Chiralpak AD-H-II (250*20, 5 mkm); Mobile phase: Hexane-IPA-MeOH, 60-20-20; Flow rate: 12 ml/min.; column temperature 20° C.; Wavelength: 230 nm, 225 nm) to afford Compound 913 N-(6-amino-5-ethyl-3-pyridyl)-2-[(2R,5S)-5-methyl-2-[1-(1H-pyrazol-3-yl)pyrazol-3-yl]-1-piperidyl]-2-oxo-acetamide (21 mg, 49.71 μmol, 32.81% yield) (RT=26.645 min.), and Compound 931 N-(6-amino-5-ethyl-3-pyridyl)-2-[(2S,5R)-5-methyl-2-[1-(1H-pyrazol-3-yl)pyrazol-3-yl]-1-piperidyl]-2-oxo-acetamide (22.6 mg, 53.49 μmol, 35.31% yield) (RT=36.187 min.).

Ret time for Compound 931 in analytical conditions (column: IC, Hexane-IPA-MeOH, 70-15-15, 0.6 ml/min as mobile phase) 46.80 min and for Compound 913 37.45 min.

Compound 931: Retention time: 46.80 min $^1$H NMR (600 MHz, DMSO-$d_6$) δ (ppm) 1.06 (m, 6H), 1.38 (m, 1H), 1.89 (m, 3H), 2.16 (m, 1H), 2.38 (m, 2H), 2.87 (m, 1H), 3.65 (m, 1H), 5.63 (m, 3H), 6.40 (m, 2H), 7.48 (m, 1H), 7.78 (d, 1H), 8.03 (m, 1H), 8.17 (m, 1H), 10.45 (s, 1H), 12.78 (s, 1H).

LCMS(ESI): [M]$^+$ m/z: calcd 422.2; found 423.2; Rt=1.947 min.

Compound 913: Retention time: 37.45 min $^1$H NMR (600 MHz, DMSO-$d_6$) δ (ppm) 1.07 (m, 6H), 1.37 (m, 1H), 1.85 (m, 1H), 1.97 (m, 2H), 2.17 (m, 1H), 2.37 (m, 2H), 2.86 (m, 1H), 3.74 (dd, 1H), 5.63 (m, 3H), 6.40 (m, 2H), 7.48 (m, 1H), 7.78 (d, 1H), 8.03 (m, 1H), 8.17 (dd, 1H), 10.45 (s, 1H), 12.78 (s, 1H).

LCMS(ESI): [M]$^+$ m/z: calcd 422.2; found 423.2; Rt=1.931 min.

Example 210. The Synthesis of 5-(2-(2-(1'H-[1,3'-Bipyrazol]-3-yl)-5-methylpiperidin-1-yl)-2-oxoacetamido)-2-methoxynicotinamide (Compound 894 and Compound 881

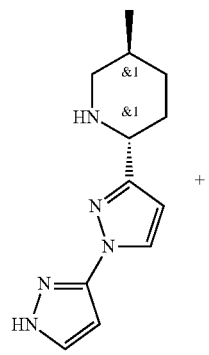

+

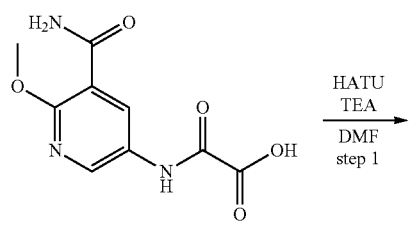

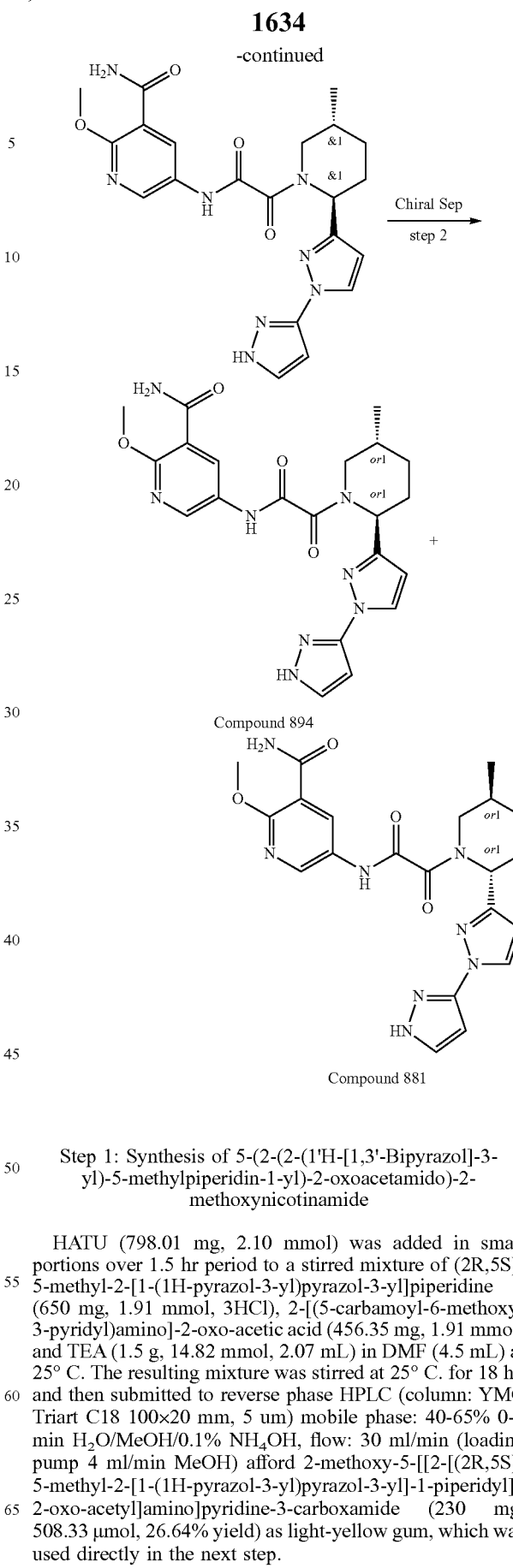

Compound 894

Compound 881

Step 1: Synthesis of 5-(2-(2-(1'H-[1,3'-Bipyrazol]-3-yl)-5-methylpiperidin-1-yl)-2-oxoacetamido)-2-methoxynicotinamide HATU (798.01 mg, 2.10 mmol) was added in small portions over 1.5 hr period to a stirred mixture of (2R,5S)-5-methyl-2-[1-(1H-pyrazol-3-yl)pyrazol-3-yl]piperidine (650 mg, 1.91 mmol, 3HCl), 2-[(5-carbamoyl-6-methoxy-3-pyridyl)amino]-2-oxo-acetic acid (456.35 mg, 1.91 mmol) and TEA (1.5 g, 14.82 mmol, 2.07 mL) in DMF (4.5 mL) at 25° C. The resulting mixture was stirred at 25° C. for 18 hr, and then submitted to reverse phase HPLC (column: YMC Triart C18 100×20 mm, 5 um) mobile phase: 40-65% 0-5 min H$_2$O/MeOH/0.1% NH$_4$OH, flow: 30 ml/min (loading pump 4 ml/min MeOH) afford 2-methoxy-5-[[2-[(2R,5S)-5-methyl-2-[1-(1H-pyrazol-3-yl)pyrazol-3-yl]-1-piperidyl]-2-oxo-acetyl]amino]pyridine-3-carboxamide (230 mg, 508.33 μmol, 26.64% yield) as light-yellow gum, which was used directly in the next step.

LCMS(ESI): [M]+ m/z: calcd 452.2; found 453.2; Rt=2.399 min.

Step 2: Chiral Separation (Compound 894 and Compound 881

Racemic 2-methoxy-5-[[2-[(2R,5S)-5-methyl-2-[1-(1H-pyrazol-3-yl)pyrazol-3-yl]-1-piperidyl]-2-oxo-acetyl]amino]pyridine-3-carboxamide (230 mg, 508.33 µmol) was submitted to preparative chiral HPLC (column:Chiralpak AD-H III (250*30 mm,5 mkm); mobile phase: Hexane-IPA-MeOH, 50-25-25; flow rate: 12 ml/min) to afford Compound 894 2-methoxy-5-[[2-[(2S,5R)-5-methyl-2-[1-(1H-pyrazol-3-yl)pyrazol-3-yl]-1-piperidyl]-2-oxo-acetyl]amino]pyridine-3-carboxamide (47.8 mg, 105.64 µmol, 20.78% yield) (RT=21.268 min.), and Compound 881 2-methoxy-5-[[2-[(2R,5S)-5-methyl-2-[1-(1H-pyrazol-3-yl)pyrazol-3-yl]-1-piperidyl]-2-oxo-acetyl]amino]pyridine-3-carboxamide (59.5 mg, 131.50 µmol, 25.87% yield) (RT=29.096 min.).

Ret time for Compound 894 in analytical conditions (column: AD-H, Hexane-IPA-MeOH, 50-25-25, 0.6 ml/min as mobile phase) 22.91 min and for Compound 881 33.22 min.

Compound 894: Retention time: 22.91 min
$^1$H NMR (500 MHz, DMSO-$d_6$) δ (ppm) 1.02 (d, 3H), 1.39 (m, 1H), 2.00 (m, 5H), 3.78 (m, 4H), 5.47 (dd, 1H), 6.41 (m, 2H), 7.76 (m, 3H), 8.18 (dd, 1H), 8.53 (m, 2H), 11.01 (s, 1H), 12.79 (s, 1H).
LCMS(ESI): [M]+ m/z: calcd 452.2; found 453.2; Rt=1.118 min.

Compound 881: Retention time: 33.22 min
$^1$H NMR (500 MHz, DMSO-$d_6$) δ (ppm) 1.02 (d, 3H), 1.38 (m, 1H), 1.86 (m, 1H), 2.10 (m, 3H), 3.78 (m, 5H), 5.48 (dd, 1H), 6.41 (m, 2H), 7.76 (m, 3H), 8.18 (dd, 1H), 8.47 (s, 1H), 8.54 (m, 1H), 10.99 (s, 1H), 12.80 (s, 1H).
LCMS(ESI): [M]+ m/z: calcd 452.2; found 453.2; Rt=1.120 min.

Example 211. The Synthesis of 5-(2-(2-(1'H-[1,3'-Bipyrazol]-3-yl)-5-methylpiperidin-1-yl)-2-oxoacetamido)Nicotinamide (Compound 899 and Compound 882

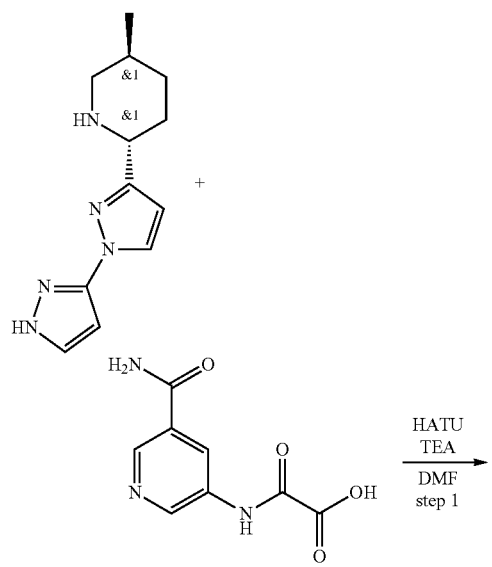

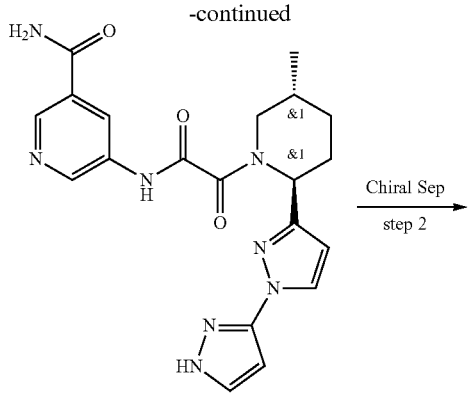

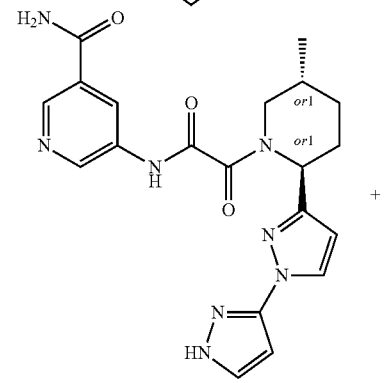

Compound 899

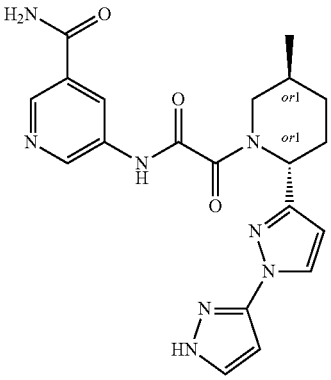

Compound 882

Step 1: Synthesis of 5-(2-(2-(1'H-[1,3'-Bipyrazol]-3-yl)-5-methylpiperidin-1-yl)-2-oxoacetamido)Nicotinamide HATU (798.01 mg, 2.10 mmol) was added in small portions over 1.5 hr period to a stirred mixture of (2R,5S)-5-methyl-2-[1-(1H-pyrazol-3-yl)pyrazol-3-yl]piperidine (650 mg, 1.91 mmol, 3HCl), 2-[(5-carbamoyl-3-pyridyl)amino]-2-oxo-acetic acid (468.63 mg, 1.91 mmol, HCl) and TEA (1.5 g, 14.82 mmol, 2.07 mL) in DMF (4.5 mL) at 25° C. The resulting mixture was stirred at 25° C. for 18 hr, and then submitted to reverse phase HPLC (column: YMC Triart C18 100×20 mm, 5 um; mobile phase: 25-50% 0-5 min H$_2$O/MeOH/0.1% NH$_4$OH, flow rate: 30 ml/min (loading pump 4 ml/min MeOH) to afford 5-[[2-[(2R,5S)-5-methyl-2-[1-(1H-pyrazol-3-yl)pyrazol-3-yl]-1-piperidyl]-2-oxo-acetyl]amino]pyridine-3-carboxamide (56 mg, 132.56 µmol, 6.95% yield) as light-yellow gum, which was used directly in the next step (all 3 fractions were submitted to preparative chiral HPLC).

LCMS(ESI): [M]⁺ m/z: calcd 422.2; found 423.2; Rt=2.060 min.

Step 2: Chiral Separation (Compound 899 and Compound 882

Racemic 5-[[2-[(2R,5S)-5-methyl-2-[1-(1H-pyrazol-3-yl)pyrazol-3-yl]-1-piperidyl]-2-oxo-acetyl]amino]pyridine-3-carboxamide (56 mg, 132.56 μmol) was submitted to preparative chiral HPLC (Chiralcel OJ-H—I (250*20, 5 mkm); Mobile phase: Hexane-IPA-MeOH, 50-25-25 Flow Rate: 12 mL/min; Column Temperature: 24° C.; Wavelength: 205 nm, 215 nm) to afford Compound 899 5-[[2-[(2S,5R)-5-methyl-2-[1-(1H-pyrazol-3-yl)pyrazol-3-yl]-1-piperidyl]-2-oxo-acetyl]amino]pyridine-3-carboxamide (13.7 mg, 32.43 μmol, 24.46% yield) (RT=14.700 min.), and Compound 882 5-[[2-[(2R,5S)-5-methyl-2-[1-(1H-pyrazol-3-yl)pyrazol-3-yl]-1-piperidyl]-2-oxo-acetyl]amino]pyridine-3-carboxamide (15.2 mg, 35.98 μmol, 27.14% yield) (RT=33.865 min.).

Ret time for Compound 899 in analytical conditions (column: OJ-H, Hexane-IPA-MeOH, 50-25-25, 0.6 ml/min as mobile phase) 11.87 min and for Compound 882 33.79 min.

Compound 899: Retention time: 11.87 min
¹H NMR (500 MHz, DMSO-d₆) δ (ppm) 1.03 (d, 3H), 1.40 (m, 1H), 2.02 (m, 5H), 3.68 (m, 1H), 5.48 (m, 1H), 6.40 (m, 1H), 6.45 (m, 1H), 7.60 (d, 1H), 7.79 (d, 1H), 8.17 (m, 2H), 8.50 (s, 1H), 8.76 (m, 1H), 8.88 (m, 1H), 11.22 (s, 1H), 12.79 (s, 1H).
LCMS(ESI): [M]⁺ m/z: calcd 422.2; found 423.2; Rt=1.016 min.

Compound 882: Retention time: 33.79 min
¹H NMR (500 MHz, DMSO-d₆) δ (ppm) 1.03 (d, 3H), 1.38 (m, 1H), 1.94 (m, 3H), 2.18 (m, 2H), 3.70 (m, 1H), 5.48 (dd, 1H), 6.40 (m, 1H), 6.45 (m, 1H), 7.59 (dd, 1H), 7.79 (m, 1H), 8.18 (m, 2H), 8.50 (s, 1H), 8.75 (d, 1H), 8.88 (d, 1H), 11.19 (s, 1H), 12.80 (s, 1H).
LCMS(ESI): [M]⁺ m/z: calcd 422.2; found 423.2; Rt=1.016 min.

Example 212. The Synthesis of Rel-5-[[2-[(2S,5S)-4,4-difluoro-5-methyl-2-(6-methyl-3-pyridyl)-1-piperidyl]-2-oxo-acetyl]amino]pyridine-3-carboxamide (Compound 946) and Rel-5-[[2-[(2R,5R)-4,4-difluoro-5-methyl-2-(6-methyl-3-pyridyl)-1-piperidyl]-2-oxo-acetyl]amino]pyridine-3-carboxamide (Compound 974

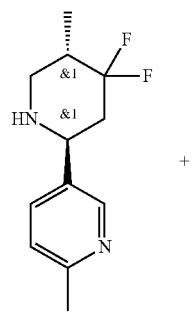

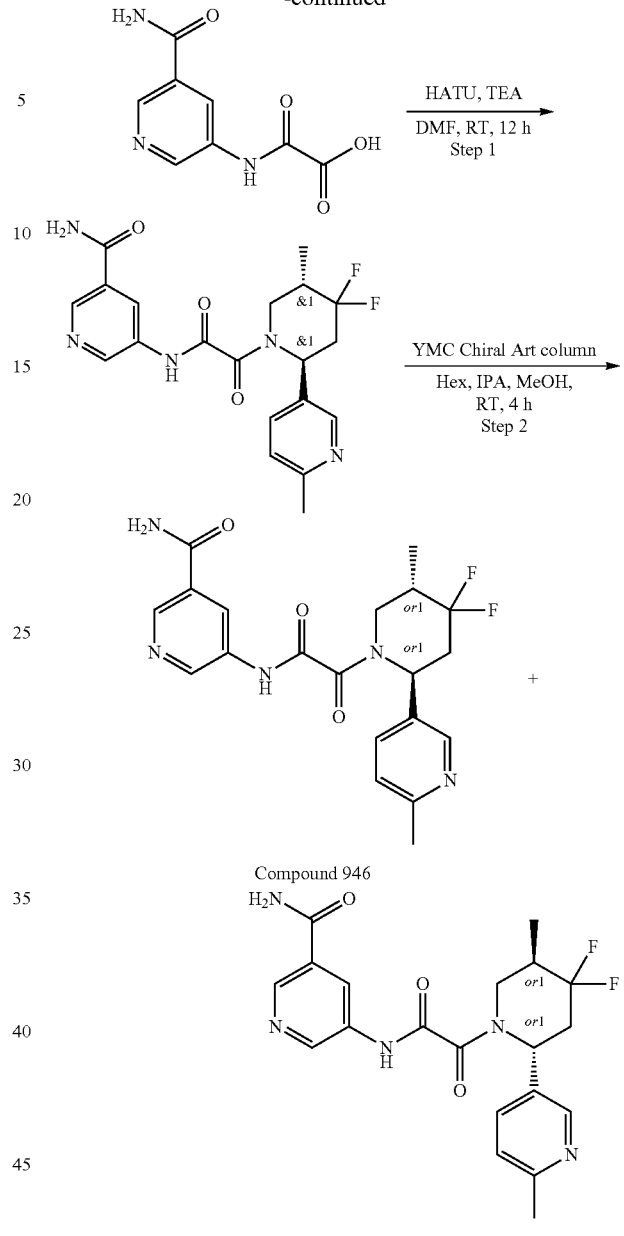

Compound 946

Compound 974

Step 1: The Synthesis of rac-5-[[2-[(2S,5S)-4,4-difluoro-5-methyl-2-(6-methyl-3-pyridyl)-1-piperidyl]-2-oxo-acetyl]amino]pyridine-3-carboxamide To a solution of 5-[(2S,5S)-4,4-difluoro-5-methyl-2-piperidyl]-2-methyl-pyridine (0.35 g, 1.55 mmol), 2-[(5-carbamoyl-3-pyridyl)amino]-2-oxo-acetic acid (417.93 mg, 1.70 mmol, HCl) and triethylamine (782.63 mg, 7.73 mmol, 1.08 mL), HATU (705.79 mg, 1.86 mmol) was added portionwise. The resulting mixture was stirred at 25° C. for 12 hr and purified by HPLC (5-5-50% 0-1-5 min H₂O/MeOH/0.1% NH₄OH, flow: 30 mL/min (loading pump 4 mL/min methanol) target mass 417.42 column: YMC Triart C18 100×20 mm, 5 um) to obtain 5-[[2-[(2S,5S)-4,4-difluoro-5-methyl-2-(6-methyl-3-pyridyl)-1-piperidyl]-2-oxo-acetyl]amino]pyridine-3-carboxamide (170 mg, 407.27 μmol, 26.33% yield).

This compound was used for chiral resolution without HNMR.

LCMS(ESI): [M+H]+ m/z: calcd 417.2; found 418.2; Rt=1.295 min.

Step 2: The Synthesis of Rel-5-[[2-[(2S,5S)-4,4-difluoro-5-methyl-2-(6-methyl-3-pyridyl)-1-piperidyl]-2-oxo-acetyl]amino]pyridine-3-carboxamide (Compound 946) and Rel-5-[[2-[(2R,5R)-4,4-difluoro-5-methyl-2-(6-methyl-3-pyridyl)-1-piperidyl]-2-oxo-acetyl]amino]pyridine-3-carboxamide (Compound 974 rac-5-[[2-[(2S,5S)-4,4-difluoro-5-methyl-2-(6-methyl-3-pyridyl)-1-piperidyl]-2-oxo-acetyl]amino]pyridine-3-carboxamide (0.17 g, 407.27 μmol) was chirally separated (Sample Info: YMC Chiral Art (250*20 mm, 5 mkm), Hexane-IPA-MeOH, 40-30-30, 12 mL/min) to obtain Compound 946—rel-5-[[2-[(2S,5S)-4,4-difluoro-5-methyl-2-(6-methyl-3-pyridyl)-1-piperidyl]-2-oxo-acetyl]amino]pyridine-3-carboxamide (81 mg, 194.05 μmol, 95.29% yield) and Compound 974—rel-5-[[2-[(2R,5R)-4,4-difluoro-5-methyl-2-(6-methyl-3-pyridyl)-1-piperidyl]-2-oxo-acetyl]amino]pyridine-3-carboxamide (84 mg, 201.24 μmol, 98.82% yield).

Compound 946: RT (IC, CO₂-MeOH, 60-40, 0.6 mL/min)=6.533 min.

¹H NMR (600 MHz, DMSO-d₆) δ 1.05-1.15 (m, 3H), 2.12-2.28 (m, 1H), 2.37-2.45 (m, 4H), 2.80-2.91 (m, 1H), 3.01-3.47 (m, 1H), 3.81-4.29 (m, 1H), 5.57-5.88 (m, 1H), 7.15-7.29 (m, 1H), 7.54-7.66 (m, 2H), 8.07-8.21 (m, 1H), 8.37-8.52 (m, 2H), 8.72-8.80 (m, 1H), 8.80-8.95 (m, 1H), 11.16-11.39 (m, 1H).

LCMS(ESI): [M+H]+ m/z: calcd 417.2; found 418.4; Rt=1.332 min.

Compound 974: RT (IC, CO₂-MeOH, 60-40, 0.6 mL/min)=7.087 min.

¹H NMR (600 MHz, DMSO-d₆) δ 1.05-1.13 (m, 3H), 2.11-2.26 (m, 1H), 2.37-2.45 (m, 4H), 2.79-2.90 (m, 1H), 3.00-3.46 (m, 1H), 3.79-4.29 (m, 1H), 5.57-5.87 (m, 1H), 7.16-7.28 (m, 1H), 7.53-7.66 (m, 2H), 8.08-8.21 (m, 1H), 8.34-8.53 (m, 2H), 8.70-8.80 (m, 1H), 8.80-8.94 (m, 1H), 11.15-11.38 (m, 1H).

LCMS(ESI): [M+H]+ m/z: calcd 417.2; found 418.4; Rt=1.338 min.

Example 213. The Synthesis of Rel-5-[[2-[(2S,5S)-4,4-difluoro-5-methyl-2-(6-methyl-3-pyridyl)-1-piperidyl]-2-oxo-acetyl]amino]-2-methoxy-pyridine-3-carboxamide (Compound 936) and Rel-5-[[2-[(2R,5R)-4,4-difluoro-5-methyl-2-(6-methyl-3-pyridyl)-1-piperidyl]-2-oxo-acetyl]amino]-2-methoxy-pyridine-3-carboxamide (Compound 908

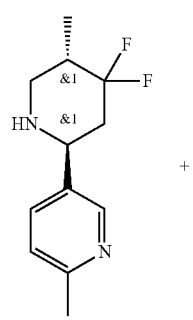

+

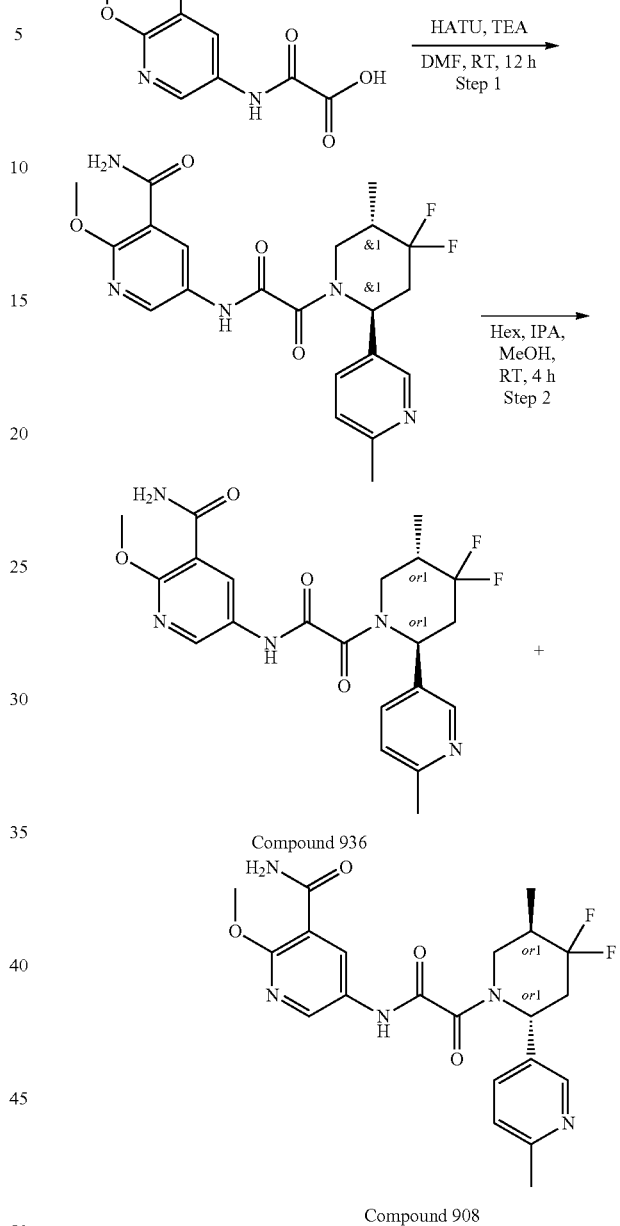

Step 1: The Synthesis of rac-5-[[2-[(2S,5S)-4,4-difluoro-5-methyl-2-(6-methyl-3-pyridyl)-1-piperidyl]-2-oxo-acetyl]amino]-2-methoxy-pyridine-3-carboxamide To a solution of 5-[(2S,5S)-4,4-difluoro-5-methyl-2-piperidyl]-2-methyl-pyridine (0.35 g, 1.55 mmol), 2-[(5-carbamoyl-6-methoxy-3-pyridyl)amino]-2-oxo-acetic acid (406.98 mg, 1.70 mmol) and triethylamine (782.63 mg, 7.73 mmol, 1.08 mL), HATU (705.79 mg, 1.86 mmol) was added portionwise. The resulting mixture was stirred at 25° C. for 12 hr and purified by HPLC: 15-65% 0-5 min H₂O/MeOH, flow: 30 mL/min (loading pump 4 mL/min methanol) target mass 447.45 column: YMC Triart C18 100×20 mm, 5 um) to obtain 5-[[2-[(2S,5S)-4,4-difluoro-5-methyl-2-(6-methyl- 3-pyridyl)-1-piperidyl]-2-oxo-acetyl]amino]-2-methoxy-pyridine-3-carboxamide (0.27 g, 603.44 μmol, 39.01% yield).

This compound was used for chiral resolution without HNMR.

LCMS(ESI): [M+H]⁺ m/z: calcd 447.2; found 448.2; Rt=1.747 min.

Step 2: The Synthesis of Rel-5-[[2-[(2S,5S)-4,4-difluoro-5-methyl-2-(6-methyl-3-pyridyl)-1-piperidyl]-2-oxo-acetyl]amino]-2-methoxy-pyridine-3-carboxamide (Compound 936) and Rel-5-[[2-[(2R,5R)-4,4-difluoro-5-methyl-2-(6-methyl-3-pyridyl)-1-piperidyl]-2-oxo-acetyl]amino]-2-methoxy-pyridine-3-carboxamide (Compound 908 rac-5-[[2-[(2S,5S)-4,4-difluoro-5-methyl-2-(6-methyl-3-pyridyl)-1-piperidyl]-2-oxo-acetyl]amino]-2-methoxy-pyridine-3-carboxamide (0.27 g, 603.44 μmol) was chirally separated (Chiralpak IC-II (250*20, 5 mkm), Hexane-IPA-MeOH, 50-25-25, 12 mL/min) to obtain 5-[[2-[(2S,5S)-4,4-difluoro-5-methyl-2-(6-methyl-3-pyridyl)-1-piperidyl]-2-oxo-acetyl]amino]-2-methoxy-pyridine-3-carboxamide (106 mg, 236.91 μmol, 78.52% yield) and 5-[[2-[(2R,5R)-4,4-difluoro-5-methyl-2-(6-methyl-3-pyridyl)-1-piperidyl]-2-oxo-acetyl]amino]-2-methoxy-pyridine-3-carboxamide (98 mg, 219.03 μmol, 72.59% yield).

Compound 936: RT (IC, Hexane-IPA-MeOH, 50-25-25, 0.6 mL/min)=23.904 min.

¹H NMR (DMSO-d₆, 600 MHz): δ (ppm) 1.06 (d, 3H), 2.19 (m, 1H), 2.42 (m, 4H), 2.87 (m, 2H), 3.62 (dd, 1H), 3.91 (m, 3H), 5.72 (dd, 1H), 7.23 (dd, 1H), 7.61 (d, 1H), 7.72 (m, 2H), 8.42 (m, 1H), 8.49 (m, 2H), 11.09 (m, 1H)

LCMS(ESI): [M+H]⁺ m/z: calcd 447.2; found 448.4; Rt=1.648 min.

Compound 908: RT (IC, Hexane-IPA-MeOH, 50-25-25, 0.6 mL/min)=39.401 min.

¹H NMR (DMSO-d₆, 600 MHz): δ (ppm) 1.08 (d, 3H), 2.19 (m, 1H), 2.42 (m, 4H), 2.88 (m, 2H), 3.62 (dd, 1H), 3.93 (m, 3H), 5.72 (dd, 1H), 7.23 (dd, 1H), 7.61 (d, 1H), 7.72 (m, 2H), 8.40 (m, 1H), 8.49 (m, 2H), 11.08 (m, 1H).

LCMS(ESI): [M+H]⁺ m/z: calcd 447.2; found 448.4; Rt=1.650 min.

Example 214. The Synthesis of Rel-N-(6-amino-5-ethyl-3-pyridyl)-2-[(2S,5S)-4,4-difluoro-5-methyl-2-(6-methyl-3-pyridyl)-1-piperidyl]-2-oxo-acetamide (Compound 935) and Rel-N-(6-amino-5-ethyl-3-pyridyl)-2-[(2R,5R)-4,4-difluoro-5-methyl-2-(6-methyl-3-pyridyl)-1-piperidyl]-2-oxo-acetamide (Compound 909

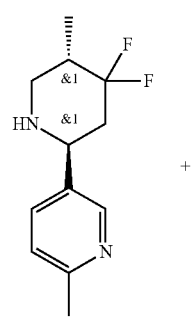

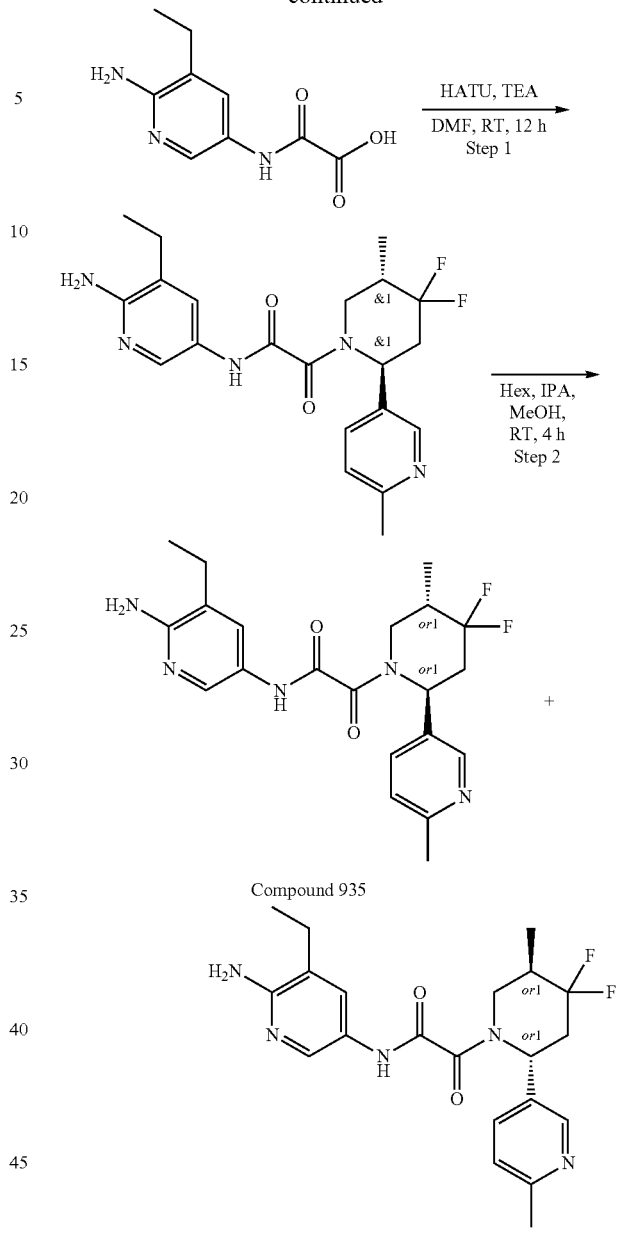

Step 1: The Synthesis of rac-N-(6-amino-5-ethyl-3-pyridyl)-2-[(2S,5S)-4,4-difluoro-5-methyl-2-(6-methyl-3-pyridyl)-1-piperidyl]-2-oxo-acetamide To a solution of 5-[(2S,5S)-4,4-difluoro-5-methyl-2-piperidyl]-2-methyl-pyridine (0.35 g, 1.55 mmol), 2-[(6-amino-5-ethyl-3-pyridyl)amino]-2-oxo-acetic acid (355.97 mg, 1.70 mmol) and triethylamine (782.63 mg, 7.73 mmol, 1.08 mL), HATU (705.79 mg, 1.86 mmol) was added portionwise. The resulting mixture was stirred at 25° C. for 12 hr and purified by HPLC: 15-65% 0-5 min H₂O/MeOH/0.1% NH₄OH, flow: 30 mL/min (loading pump 4 mL/min methanol) target mass 417.46 column: YMC Triart C18 100×20 mm, 5 um) to obtain N-(6-amino-5-ethyl-3-pyridyl)-2-[(2S,5S)-4,4-difluoro-5-methyl-2-(6-methyl-3-pyridyl)-1-piperidyl]-2-oxo-acetamide (0.2 g, 479.10 μmol, 30.97% yield).

This compound was used for chiral resolution without HNMR.

LCMS(ESI): [M+H]⁺ m/z: calcd 417.0; found 418.0; Rt=1.282 min.

Step 2 the Synthesis of Rel-N-(6-amino-5-ethyl-3-pyridyl)-2-[(2S,5S)-4,4-difluoro-5-methyl-2-(6-methyl-3-pyridyl)-1-piperidyl]-2-oxo-acetamide (Compound 935) and Rel-N-(6-amino-5-ethyl-3-pyridyl)-2-[(2R,5R)-4,4-difluoro-5-methyl-2-(6-methyl-3-pyridyl)-1-piperidyl]-2-oxo-acetamide (Compound 909 rac-N-(6-amino-5-ethyl-3-pyridyl)-2-[(2S,5S)-4,4-difluoro-5-methyl-2-(6-methyl-3-pyridyl)-1-piperidyl]-2-oxo-acetamide (0.2 g, 479.10 μmol) was chirally separated (YMC Chiral Art (250*20, 5 mkm), Hexane-IPA-MeOH, 60-20-20, 12 mL/min) to obtain rel-N-(6-amino-5-ethyl-3-pyridyl)-2-[(2S,5S)-4,4-difluoro-5-methyl-2-(6-methyl-3-pyridyl)-1-piperidyl]-2-oxo-acetamide (86 mg, 206.01 μmol, 86.00% yield) and rel-N-(6-amino-5-ethyl-3-pyridyl)-2-[(2R,5R)-4,4-difluoro-5-methyl-2-(6-methyl-3-pyridyl)-1-piperidyl]-2-oxo-acetamide (86 mg, 206.01 μmol, 86.00% yield).

Compound 935:
RT (IC, Hexane-IPA-MeOH, 50-25-25, 0.6 mL/min)=15.626 min.

¹H NMR (DMSO-d₆, 600 MHz): δ (ppm) 1.08 (m, 6H), 2.18 (m, 1H), 2.40 (m, 5H), 2.57 (m, 2H), 2.89 (m, 1H), 3.59 (m, 1H), 5.70 (m, 3H), 7.24 (m, 1H), 7.47 (m, 1H), 7.60 (m, 1H), 8.03 (m, 1H), 8.39 (s, 1H), 10.58 (m, 1H).

LCMS(ESI): [M+H]⁺ m/z: calcd 417.2; found 418.2; Rt=1.298 min.

Compound 909:
RT (IC, Hexane-IPA-MeOH, 50-25-25, 0.6 mL/min)=19.9458 min.

¹H NMR (DMSO-d₆, 600 MHz): δ (ppm) 1.08 (m, 7H), 2.19 (m, 1H), 2.40 (m, 6H), 2.91 (m, 1H), 3.67 (m, 1H), 5.71 (m, 3H), 7.23 (m, 1H), 7.51 (m, 2H), 8.03 (m, 1H), 8.39 (s, 1H), 10.58 (m, 1H).

LCMS(ESI): [M+H]⁺ m/z: calcd 417.2; found 418.2; Rt=1.335 min.

Example 215. The Synthesis of rac-2-methoxy-5-[[2-[(2S,5R)-5-methyl-2-(7-oxo-6,8-dihydro-5H-1,8-naphthyridin-3-yl)-1-piperidyl]-2-oxo-acetyl]amino]pyridine-3-carboxamide (Compound 891

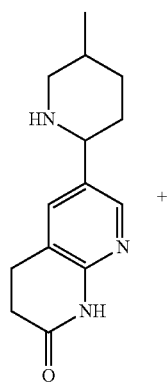

+

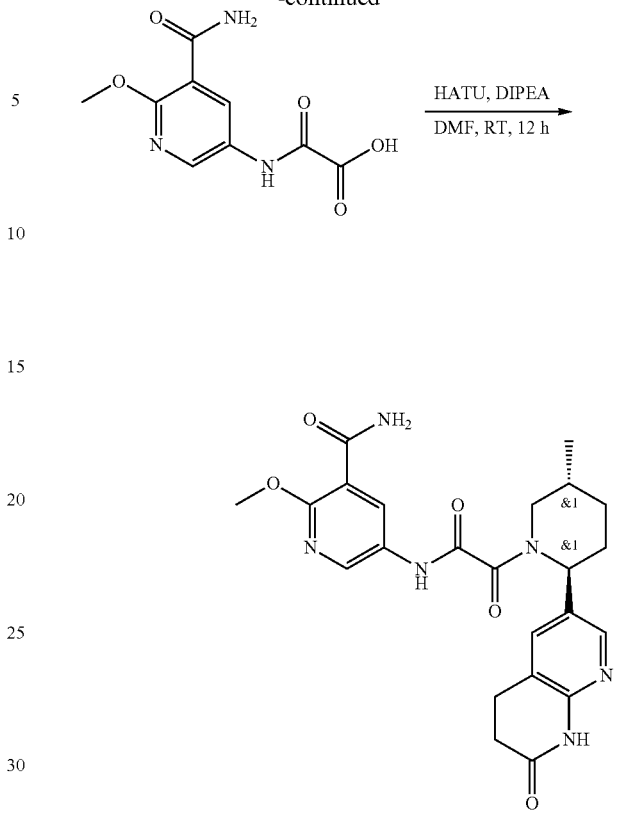

Compound 891 rac-6-[(2S,5R)-5-methyl-2-piperidyl]-3,4-dihydro-1H-1,8-naphthyridin-2-one (200 mg, 815.26 μmol), 2-[(5-carbamoyl-6-methoxy-3-pyridyl)amino]-2-oxo-acetic acid (195.00 mg, 815.26 μmol), triethylamine (412.48 mg, 4.08 mmol, 568.16 μL) were mixed in DMF (5 mL) and then HATU (464.98 mg, 1.22 mmol) were added. Resulting mixture were stirred at 24° C. for 12 hr. The solvent was evaporated and resulting mixture was stirred with SiliaMetS® DMT (50 mg) in methanol (10 mL). The mixture was filtered and evaporated under reduce pressure. Resulting crude material was purified by HPLC (2-10 min 50-100% Methanol/H₂O) to obtain 2-methoxy-5-[[2-[(2S,5R)-5-methyl-2-(7-oxo-6,8-dihydro-5H-1,8-naphthyridin-3-yl)-1-piperidyl]-2-oxo-acetyl]amino]pyridine-3-carboxamide (51 mg, 109.33 μmol, 13.41% yield).

¹H NMR (DMSO-d₆, 600 MHz): δ (ppm) 1.01 (m, 3H), 1.33 (m, 1H), 1.71 (m, 1H), 1.89 (m, 1H), 2.04 (m, 1H), 2.18 (m, 1H), 2.98 (m, 4H), 3.45 (m, 1H), 3.93 (m, 4H), 5.32 (m, 1H), 7.53 (m, 1H), 7.72 (m, 2H), 8.03 (s, 1H), 8.49 (m, 2H), 10.44 (m, 1H), 11.01 (m, 1H).

LCMS(ESI): [M+H]⁺ m/z: calcd 466.2; found 467.2; Rt=1.028 min.

1645

Example 216. The Synthesis of rac-5-[[2-[(2S,5R)-5-methyl-2-(7-oxo-6,8-dihydro-5H-1,8-naphthyridin-3-yl)-1-piperidyl]-2-oxo-acetyl]amino]pyridine-3-carboxamide (Compound 888

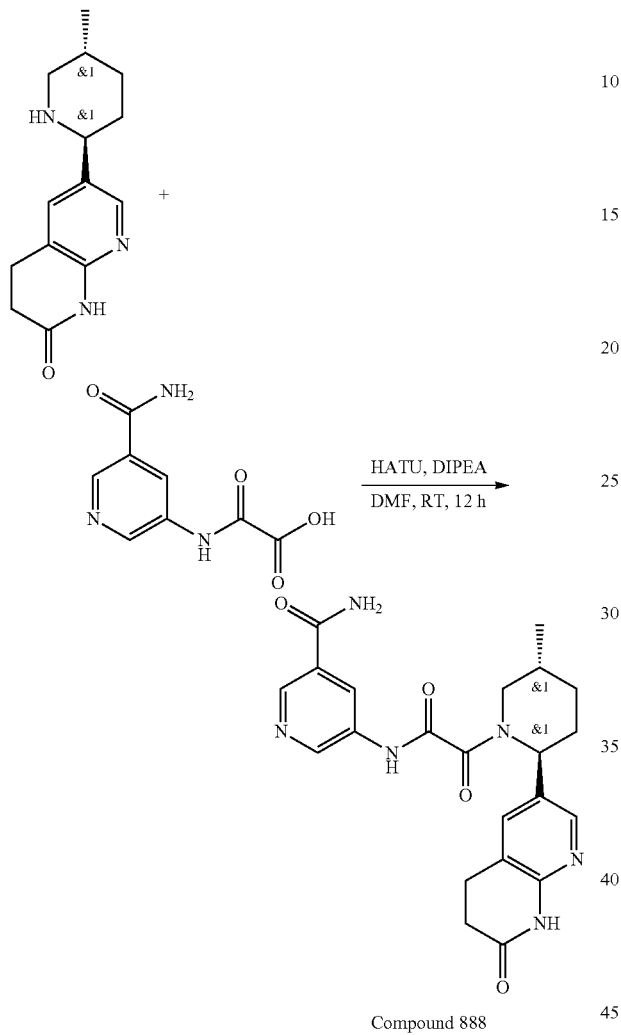

Compound 888 rac-6-[(2S,5R)-5-methyl-2-piperidyl]-3,4-dihydro-1H-1,8-naphthyridin-2-one (200 mg, 815.26 μmol), 2-[(5-carbamoyl-3-pyridyl)amino]-2-oxo-acetic acid (200.24 mg, 815.26 μmol, HCl), triethylamine (412.48 mg, 4.08 mmol, 568.16 μL) were mixed in DMF (5 mL) and then HATU (464.98 mg, 1.22 mmol) were added. Resulting mixture were stirred at 25° C. for 12 hr. The solvent was evaporated and resulting mixture was stirred with SiliaMetS® DMT (50 mg) in methanol (10 ml). The mixture was filtered and evaporated under reduce pressure. Resulting crude material was purified by HPLC (2-10 min 50-100% Methanol/H$_2$O) to obtain 5-[[2-[(2S,5R)-5-methyl-2-(7-oxo-6,8-dihydro-5H-1,8-naphthyridin-3-yl)-1-piperidyl]-2-oxo-acetyl]amino]pyridine-3-carboxamide (126.9 mg, 290.75 μmol, 35.66% yield).

$^1$H NMR (DMSO-d$_6$, 600 MHz): δ (ppm) 1.01 (m, 3H), 1.33 (m, 1H), 1.70 (m, 1H), 1.89 (m, 1H), 2.05 (m, 1H), 2.17 (m, 1H), 2.87 (m, 4H), 3.81 (m, 1H), 5.32 (m, 1H), 7.54 (m, 1H), 7.59 (m, 1H), 8.04 (s, 1H), 8.15 (m, 1H), 8.47 (m, 1H), 8.75 (m, 1H), 8.85 (m, 1H), 10.44 (m, 1H), 11.22 (m, 1H).

1646

LCMS(ESI): [M+H]$^+$ m/z: calcd 436.2; found 437.0; Rt=0.930 min.

Example 217. The Synthesis of 5-(2-(2-(2-aminobenzo[d]thiazol-5-yl)-5-methylpiperidin-1-yl)-2-oxoacetamido)Nicotinamide (Compound 987 and Compound 1001

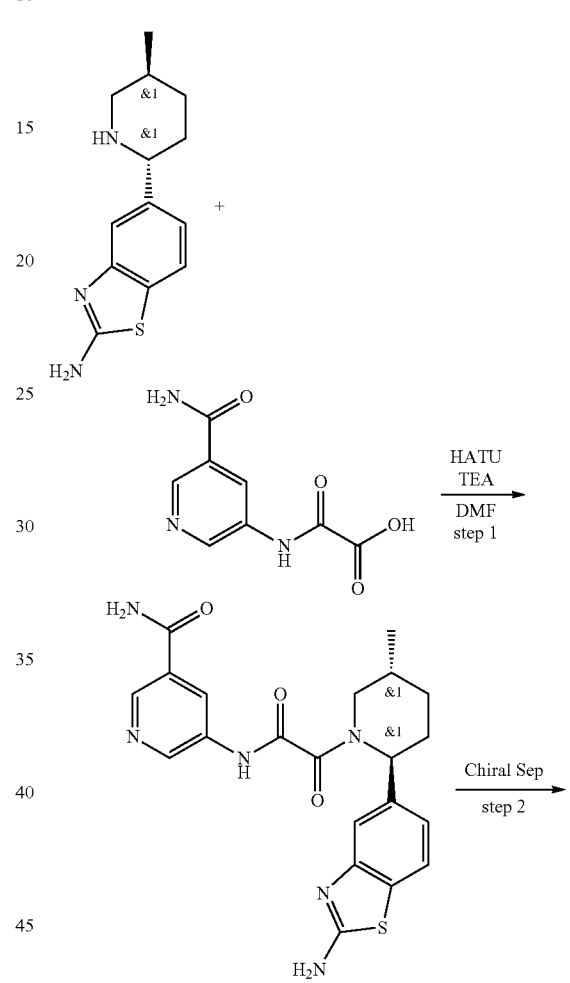

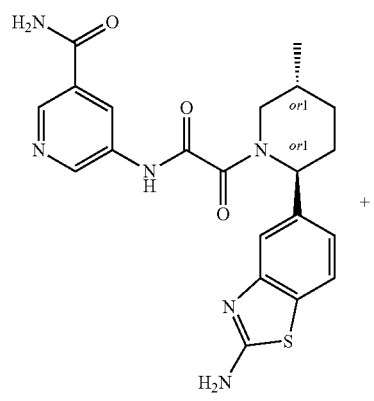

Compound 1001

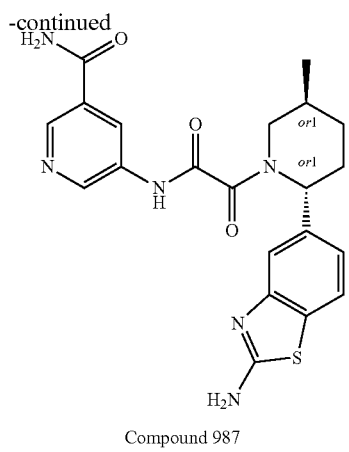

Compound 987

Step 1: Synthesis of 5-(2-(2-(2-aminobenzo[d]thiazol-5-yl)-5-methylpiperidin-1-yl)-2-oxoacetamido) Nicotinamide HATU (169.09 mg, 444.70 μmol) was added in small portions over 0.5 hr period to a stirred mixture of 5-[(2R,5S)-5-methyl-2-piperidyl]-1,3-benzothiazol-2-amine (100 mg, 404.27 μmol), 2-[(5-carbamoyl-3-pyridyl)amino]-2-oxo-acetic acid (114.19 mg, 464.91 μmol, HCl) and TEA (204.54 mg, 2.02 mmol, 281.74 μL) in DMF (4 mL) at 25° C. The resulting mixture was stirred at 25° C. for 18 hr, and then submitted to reverse phase HPLC (column: YMC Triart C18 100×20 mm, 5 um; mobile phase: 10-60% 0-5 min H$_2$O/MeOH/0.1% NH$_4$OH, flow rate: 30 ml/min (loading pump 4 ml/min MeOH) to afford 5-[[2-[(2R,5S)-2-(2-amino-1,3-benzothiazol-5-yl)-5-methyl-1-piperidyl]-2-oxo-acetyl]amino]pyridine-3-carboxamide (106 mg, 241.73 μmol, 59.79% yield) as white solid, which was directly submitted to preparative chiral HPLC.

LCMS(ESI): [M]$^+$ m/z: calcd 438.2; found 439.2; Rt=1.810 min.

Step 2: Chiral Separation (Compound 987 and Compound 1001

Racemic 5-[[2-[(2R,5S)-2-(2-amino-1,3-benzothiazol-5-yl)-5-methyl-1-piperidyl]-2-oxo-acetyl]amino]pyridine-3-carboxamide (106 mg, 241.73 μmol) was submitted to preparative chiral HPLC (column: Chiralpak IA-I (250*20, 5 mkm); mobile phase: Hexane-IPA-MeOH, 50-25-25; flow rate: 12 ml/min; Column Temperature: 24° C.; Wavelength: 205 nm, 215 nm, 254 nm) to afford Compound 1001 5-[[2-[(2S,5R)-2-(2-amino-1,3-benzothiazol-5-yl)-5-methyl-1-piperidyl]-2-oxo-acetyl]amino]pyridine-3-carboxamide (45 mg, 102.62 μmol, 42.45% yield) (RT=22.501 min) and Compound 987 5-[[2-[(2R,5S)-2-(2-amino-1,3-benzothiazol-5-yl)-5-methyl-1-piperidyl]-2-oxo-acetyl]amino]pyridine-3-carboxamide (116 mg, crude) (RT=39.531 min).

Ret time for Compound 987 in analytical conditions (column: IA, Hexane-IPA-MeOH, 50-25-25, 0.6 ml/min as mobile phase) 43.57 min and for Compound 1001 23.68 min.

Compound 987: Retention time: 43.57 min $^1$H NMR (600 MHz, DMSO-d$_6$) δ (ppm) 0.98-1.06 (m, 3H), 1.26-1.41 (m, 1H), 1.67-1.77 (m, 1H), 1.82-1.94 (m, 1H), 2.02-2.19 (m, 1H), 2.19-2.28 (m, 1H), 2.80-3.20 (m, 1H), 3.44-4.04 (m, 1H), 5.16-5.66 (m, 1H), 6.92-7.03 (m, 1H), 7.25-7.32 (m, 1H), 7.42-7.47 (m, 2H), 7.53-7.61 (m, 1H), 7.61-7.66 (m, 1H), 8.09-8.20 (m, 1H), 8.42-8.53 (m, 1H), 8.69-8.79 (m, 1H), 8.82-8.94 (m, 1H), 11.06-11.43 (m, 1H).

LCMS(ESI): [M]$^+$ m/z: calcd 438.2; found 439.2; Rt=1.705 min.

Compound 1001: Retention time: 23.68 min $^1$H NMR (600 MHz, DMSO-d$_6$) δ (ppm) 0.98-1.06 (m, 3H), 1.26-1.41 (m, 1H), 1.67-1.77 (m, 1H), 1.82-1.94 (m, 1H), 2.02-2.19 (m, 1H), 2.19-2.28 (m, 1H), 2.80-3.20 (m, 1H), 3.44-4.04 (m, 1H), 5.16-5.66 (m, 1H), 6.92-7.03 (m, 1H), 7.25-7.32 (m, 1H), 7.42-7.47 (m, 2H), 7.53-7.61 (m, 1H), 7.61-7.66 (m, 1H), 8.09-8.20 (m, 1H), 8.42-8.53 (m, 1H), 8.69-8.79 (m, 1H), 8.82-8.94 (m, 1H), 11.06-11.43 (m, 1H).

LCMS(ESI): [M]$^+$ m/z: calcd 438.2; found 439.2; Rt=1.703 min.

Example 218. The Synthesis of 2-methoxy-5-(2-(5-methyl-2-(JH-thieno[3,2-c]pyrazol-5-yl)piperidin-1-yl)-2-oxoacetamido)Nicotinamide (Compound 954

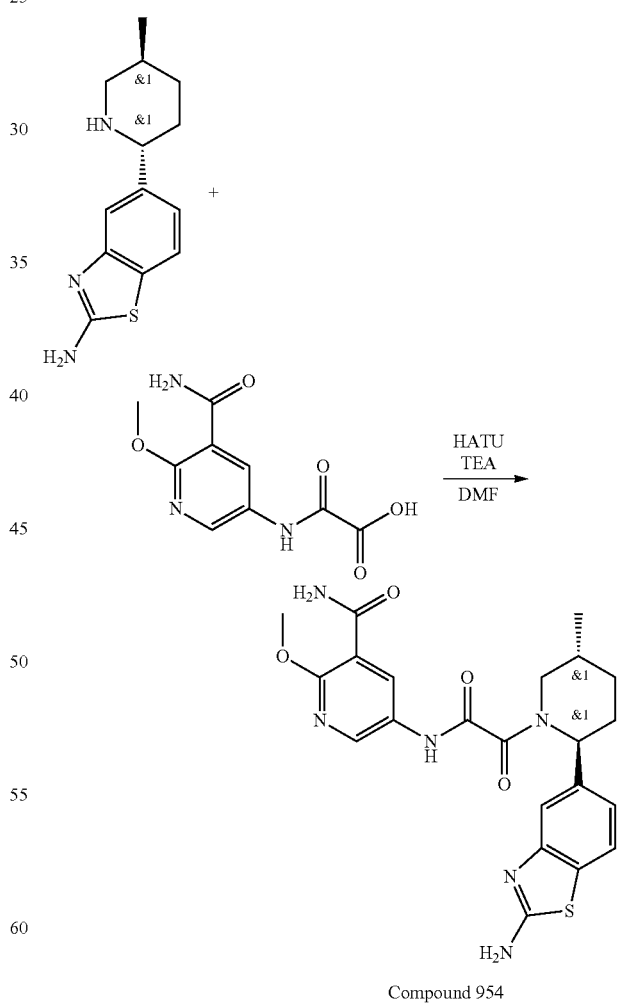

Compound 954

HATU (169.09 mg, 444.70 μmol) was added in small portions over 0.5 hr period to a stirred mixture of 5-[(2R,5S)-5-methyl-2-piperidyl]-1,3-benzothiazol-2-amine (100 mg, 404.27 µmol), 2-[(5-carbamoyl-6-methoxy-3-pyridyl)amino]-2-oxo-acetic acid (111.20 mg, 464.91 µmol) and TEA (163.63 mg, 1.62 mmol, 225.39 µL) in DMF (4 mL) at 25° C. The resulting mixture was stirred at 25° C. for 18 hr, and then submitted to reverse phase HPLC (column: YMC Triart C18 100×20 mm, 5 um; mobile phase: 15-65% 0-5 min H₂O/MeOH/0.1% NH₄OH, flow rate: 30 ml/min (loading pump 4 ml/min MeOH) to afford Compound 954 5-[[2-[(2R,5S)-2-(2-amino-1,3-benzothiazol-5-yl)-5-methyl-1-piperidyl]-2-oxo-acetyl]amino]-2-methoxy-pyridine-3-carboxamide (123 mg, 262.52 µmol, 64.94% yield) as white solid.

Compound 954: $^1$H NMR (600 MHz, DMSO-$d_6$) δ (ppm) 0.94-1.08 (m, 3H), 1.27-1.39 (m, 1H), 1.65-1.73 (m, 1H), 1.81-1.91 (m, 1H), 2.08-2.29 (m, 2H), 2.75-3.02 (m, 1H), 3.43-4.03 (m, 4H), 5.14-5.64 (m, 1H), 6.92-7.01 (m, 1H), 7.24-7.32 (m, 1H), 7.37-7.48 (m, 2H), 7.58-7.65 (m, 1H), 7.65-7.77 (m, 2H), 8.38-8.47 (m, 1H), 8.49-8.59 (m, 1H), 11.06 (s, 1H).

LCMS(ESI): [M]$^+$ m/z: calcd 468.2; found 469.2; Rt=2.106 min.

Example 219. The Synthesis of 2-(2-(2-aminobenzo[d]thiazol-5-yl)-5-methylpiperidin-1-yl)-N-(5,6-dimethylpyridin-3-yl)-2-oxoacetamide (Compound 920

5S)-5-methyl-2-piperidyl]-1,3-benzothiazol-2-amine (100 mg, 404.27 µmol), 2-[(5,6-dimethyl-3-pyridyl)amino]-2-oxo-acetic acid (137.32 mg, 464.91 µmol) and TEA (163.63 mg, 1.62 mmol, 225.39 µL) in DMF (4 mL) at 25° C. The resulting mixture was stirred at 25° C. for 18 hr, and then submitted to reverse phase HPLC (column: YMC Triart C18 100×20 mm, 5 um; mobile phase: 50-80% 0-5 min H₂O/MeOH/0.1% NH₄OH, flow rate: 30 ml/min (loading pump 4 ml/min MeOH) to afford Compound 920 2-[(2R,5S)-2-(2-amino-1,3-benzothiazol-5-yl)-5-methyl-1-piperidyl]-N-(5,6-dimethyl-3-pyridyl)-2-oxo-acetamide (70 mg, 165.28 µmol, 40.88% yield) as white solid.

Compound 920: $^1$H NMR (600 MHz, DMSO-$d_6$) δ (ppm) 1.01 (dd, 3H), 1.33 (m, 1H), 1.70 (m, 1H), 1.86 (m, 1H), 2.02 (m, 1H), 2.20 (m, 4H), 2.34 (m, 3H), 2.95 (m, 1H), 3.71 (dd, 1H), 5.37 (m, 1H), 6.96 (dd, 1H), 7.27 (m, 1H), 7.44 (m, 2H), 7.62 (m, 1H), 7.78 (m, 1H), 8.46 (m, 1H), 10.92 (m, 1H).

LCMS(ESI): [M]$^+$ m/z: calcd 423.2; found 424.2; Rt=1.861 min.

Example 220. The Synthesis of N-(6-amino-5-ethylpyridin-3-yl)-2-(2-(2-aminobenzo[d]thiazol-5-yl)-5-methylpiperidin-1-yl)-2-oxoacetamide (Compound 984 and Compound 996

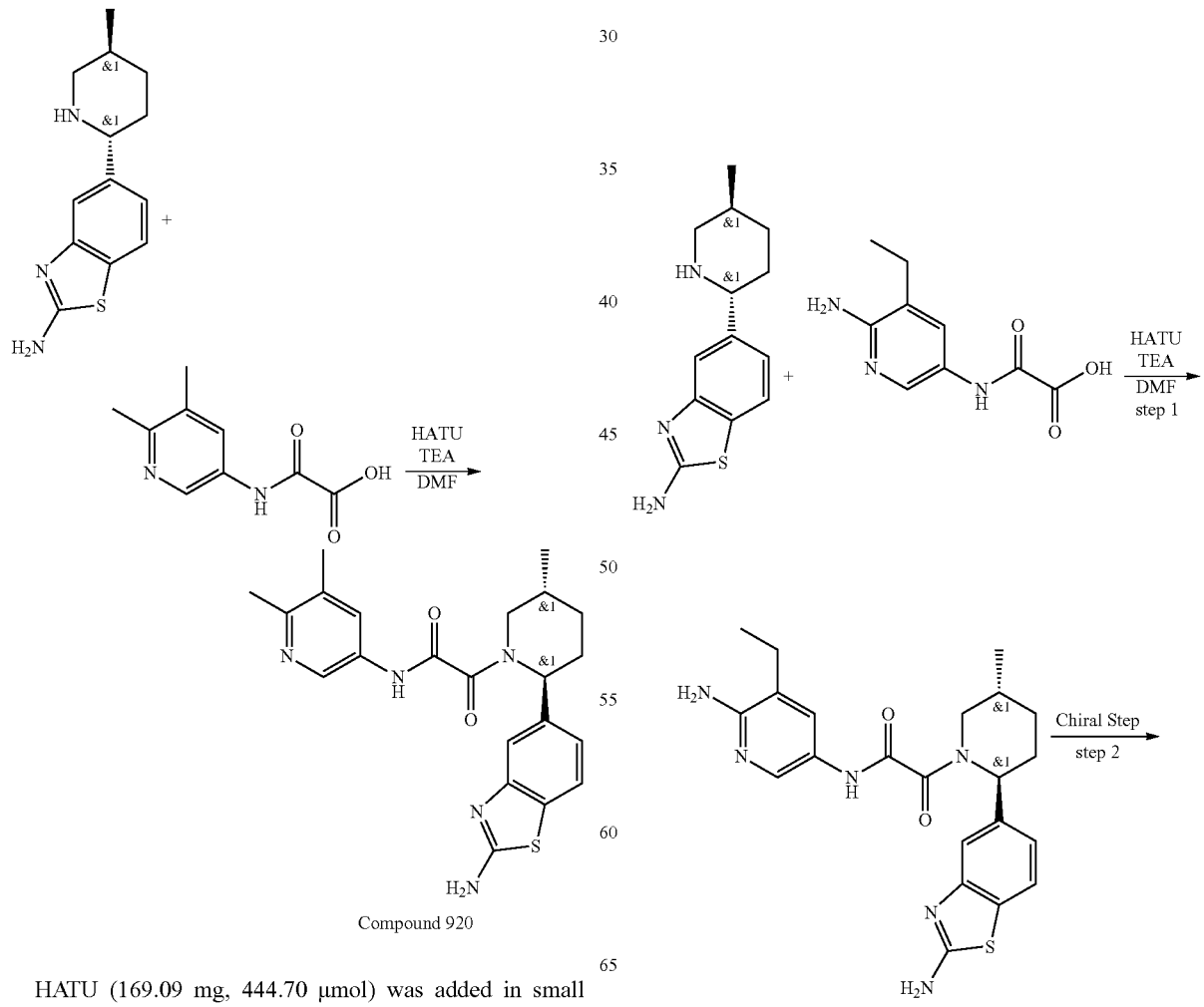

Compound 920

HATU (169.09 mg, 444.70 µmol) was added in small portions over 0.5 hr period to a stirred mixture of 5-[(2R,

1651

-continued

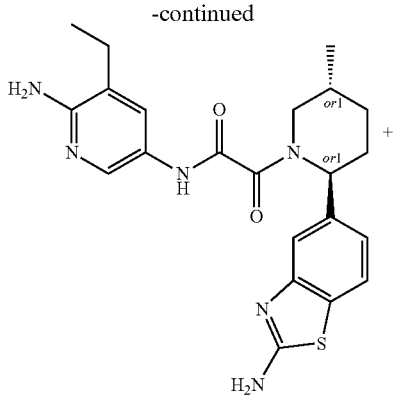

Compound 984

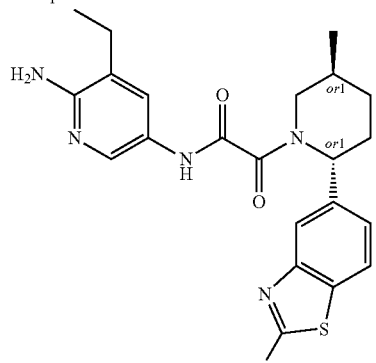

Compound 996

Step 1: Synthesis of N-(6-amino-5-ethylpyridin-3-yl)-2-(2-(2-aminobenzo[d]thiazol-5-yl)-5-methylpiperidin-1-yl)-2-oxoacetamide HATU (169.09 mg, 444.70 μmol) was added in small portions over 0.5 hr period to a stirred mixture of 5-[(2R,5S)-5-methyl-2-piperidyl]-1,3-benzothiazol-2-amine (100 mg, 404.27 μmol), 2-[(6-amino-5-ethyl-3-pyridyl)amino]-2-oxo-acetic acid (97.26 mg, 464.91 μmol) and TEA (163.63 mg, 1.62 mmol, 225.39 μL) in DMF (4 mL) at 25° C. The resulting mixture was stirred at 25° C. for 18 hr, and then submitted to reverse phase HPLC (column: YMC Triart C18 100×20 mm, 5 um; mobile phase: 20-70% 0-5 min H₂O/MeOH/0.1% NH₄OH, flow rate: 30 ml/min (loading pump 4 ml/min MeOH) to afford 2-[(2R,5S)-2-(2-amino-1,3-benzothiazol-5-yl)-5-methyl-1-piperidyl]-N-(6-amino-5-ethyl-3-pyridyl)-2-oxo-acetamide (110 mg, 250.83 μmol, 62.04% yield) as pink gum, which was directly submitted to preparative chiral HPLC.

LCMS(ESI): [M]⁺ m/z: calcd 438.2; found 439.2; Rt=1.781 min.

Step 2: Chiral Separation (Compound 984 and Compound 996

Racemic 2-[(2R,5S)-2-(2-amino-1,3-benzothiazol-5-yl)-5-methyl-1-piperidyl]-N-(6-amino-5-ethyl-3-pyridyl)-2-oxo-acetamide (110 mg, 250.83 μmol) was submitted to preparative chiral HPLC (column: Chiralpak IA-I (250*20, 5 mkm); mobile phase: Hexane-IPA-MeOH, 50-25-25; flow rate: 12 ml/min; column temperature: 24° C.; Wavelength: 205 nm, 215 nm, 254 nm) to afford 1st crude fraction (RT=30.983 min), and Compound 996 2-[(2R,5S)-2-(2-amino-1,3-benzothiazol-5-yl)-5-methyl-1-piperidyl]-N-(6-amino-5-ethyl-3-pyridyl)-2-oxo-acetamide (46.8 mg, 106.72 μmol, 42.55% yield) (RT=48.378 min). Crude 1st fraction was purified by preparative chiral HPLC (column: Chiralpak IC-II(250*20, 5 mkm); mobile phase: Hexane-IPA-MeOH, 60-20-20; flow rate: 12 ml/min; column temperature: 24° C.; Wavelength: 205 nm, 215 nm) to afford Compound 984 2-[(2S,5R)-2-(2-amino-1,3-benzothiazol-5-yl)-5-methyl-1-piperidyl]-N-(6-amino-5-ethyl-3-pyridyl)-2-oxo-acetamide (53 mg, 120.85 μmol, 48.18% yield) (RT=44.479 min).

Ret time for Compound 996 in analytical conditions (column: IA, Hexane-IPA-MeOH, 50-25-25, 0.6 ml/min as mobile phase) 64.84 min and for Compound 984 34.41 min.

Compound 996: Retention time: 64.84 min

¹H NMR (600 MHz, DMSO-d₆) δ (ppm) 0.98-1.02 (m, 3H), 1.05-1.14 (m, 3H), 1.28-1.41 (m, 1H), 1.65-1.76 (m, 1H), 1.80-1.90 (m, 1H), 1.98-2.15 (m, 1H), 2.17-2.27 (m, 1H), 2.35-2.42 (m, 2H), 2.75-3.26 (m, 1H), 3.45-4.03 (m, 1H), 5.14-5.66 (m, 3H), 6.91-7.00 (m, 1H), 7.23-7.32 (m, 1H), 7.41-7.54 (m, 3H), 7.59-7.66 (m, 1H), 7.96-8.07 (m, 1H), 10.37-10.62 (m, 1H).

LCMS(ESI): [M]⁺ m/z: calcd 438.2; found 439.2; Rt=1.700 min.

Compound 984: Retention time: 34.41 min

¹H NMR (600 MHz, DMSO-d₆) δ (ppm) 0.99-1.03 (m, 3H), 1.05-1.15 (m, 3H), 1.26-1.39 (m, 1H), 1.65-1.75 (m, 1H), 1.80-1.92 (m, 1H), 1.95-2.17 (m, 1H), 2.17-2.28 (m, 1H), 2.35-2.42 (m, 2H), 2.73-3.24 (m, 1H), 3.43-4.04 (m, 1H), 5.15-5.67 (m, 3H), 6.91-7.02 (m, 1H), 7.24-7.31 (m, 1H), 7.41-7.51 (m, 3H), 7.59-7.64 (m, 1H), 7.95-8.08 (m, 1H), 10.43-10.62 (m, 1H).

LCMS(ESI): [M]⁺ m/z: calcd 438.2; found 439.2; Rt=1.690 min.

Example 221. The Synthesis of 2-methoxy-5-[[2-[(2R,5S)-5-methyl-2-thiazol-5-yl-1-piperidyl]-2-oxo-acetyl]amino]pyridine-3-carboxamide (Compound 514) and 2-methoxy-5-[[2-[(2S,5R)-5-methyl-2-thiazol-5-yl-1-piperidyl]-2-oxo-acetyl]amino]pyridine-3-carboxamide (Compound 516

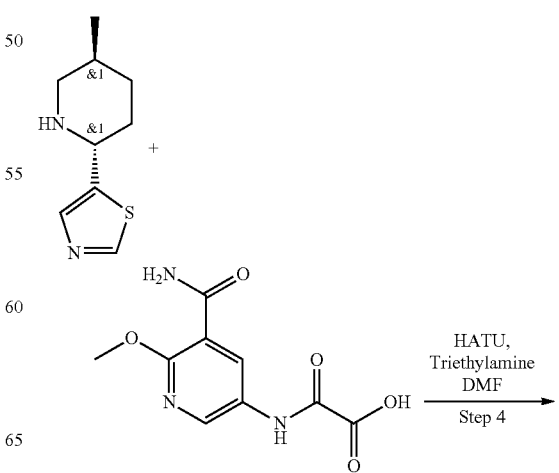

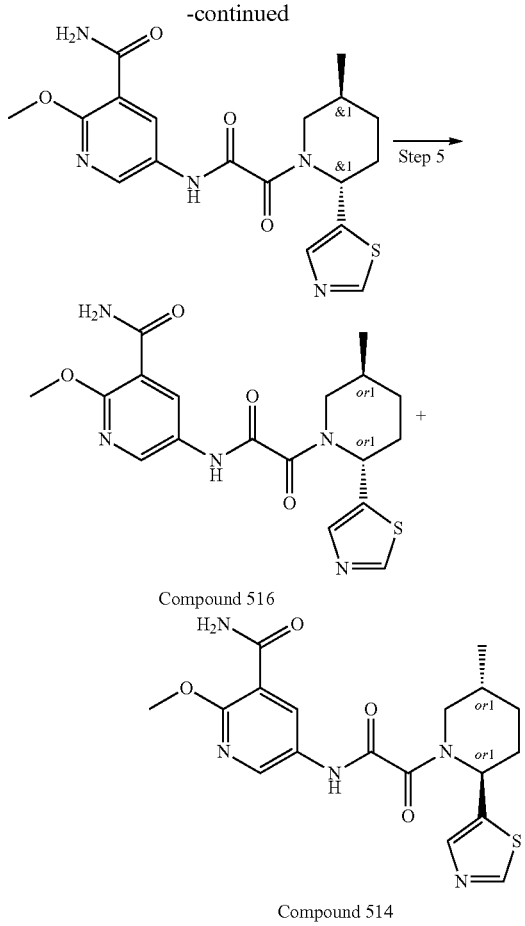

Compound 516

Compound 514

Step 1: Synthesis of 2-methoxy-5-[[2-[(2S,5R)-5-methyl-2-thiazol-5-yl-1-piperidyl]-2-oxo-acetyl]amino]pyridine-3-carboxamide (no)pyridine-3-carboxamide To a solution of 5-[(2S,5R)-5-methyl-2-piperidyl]thiazole (0.25 g, 1.37 mmol), 2-[(5-carbamoyl-6-methoxy-3-pyridyl)amino]-2-oxo-acetic acid (466.81 mg, 1.37 mmol, Et₃N) and Triethylamine (693.90 mg, 6.86 mmol, 955.78 μL), HATU (547.55 mg, 1.44 mmol) was added portionwise. The resulting mixture was stirred at 25° C. for 3 hr and subjected to HPLC: 40-40-75% 0-1-5 min water-methanol, flow: 30 ml/min (loading pump 4 ml/min methanol) target mass 403 column: YMC Triart C18 100×20 mm, 5 um) to give 2-methoxy-5-[[2-[(2S,5R)-5-methyl-2-thiazol-5-yl-1-piperidyl]-2-oxo-acetyl]amino]pyridine-3-carboxamide (150 mg, 371.79 μmol, 27.11% yield).

This substance was used for the chiral resolution without NMR-spectra.

LCMS(ESI): [M+H]⁺ m/z: calcd 403.1; found 404.2; Rt=2.305 min.

Step 2: The Synthesis of 2-methoxy-5-[[2-[(2R,5S)-5-methyl-2-thiazol-5-yl-1-piperidyl]-2-oxo-acetyl]amino]pyridine-3-carboxamide (Compound 514) and 2-methoxy-5-[[2-[(2S,5R)-5-methyl-2-thiazol-5-yl-1-piperidyl]-2-oxo-acetyl]amino]pyridine-3-carboxamide (Compound 516)

Enantiomers were separated in the following conditions—Column: Chiral ART Cellulose-SC (250*20, 5 mkm); Mobile phase: IPA-MeOH, 50-50, Flow Rate: 10 mL/min; Column Temperature: 24° C.; Wavelength: 218 nm, 246 nm, 302 nm), RetTime (Compound 514)=17.49 min; RetTime (Compound 516)=34.43 min Separated enantiomers were additionally purified in the following conditions:

Column: Chiralcel OJ-H (250*20 mm/5 m); Mobile phase: Hexane-IPA-MeOH, 60-20-20 Flow Rate: 12 mL/min; Column Temperature: 24° C.; Wavelength: 218 nm, 246 nm, 302 nm), RetTime (Compound 514)=41.12 min RetTime (Compound 516)=30.488 min Compound 514: ¹H NMR (600 MHz, DMSO-d₆) δ 0.96-1.02 (m, 3H), 1.38-1.48 (m, 1H), 1.79-1.88 (m, 1H), 1.88-1.98 (m, 1H), 1.98-2.04 (m, 1H), 2.04-2.29 (m, 1H), 2.78-3.27 (m, 1H), 3.43-3.50 (m, 0.7H), 3.92-3.96 (m, 3H), 4.02-4.05 (m, 0.3H), 5.53-5.92 (m, 1H), 7.69-7.78 (m, 2H), 7.79-7.88 (m, 1H), 8.43-8.50 (m, 1H), 8.51-8.56 (m, 1H), 9.02-9.09 (m, 1H), 10.93-11.19 (m, 1H).

LCMS(ESI): [M+H]⁺ m/z: calcd 403.5; found 404.0; Rt=4.221 min.

RT(IPA-MeOH, 50-50, 10 ml/min)=33.40 min

Compound 516: ¹H NMR (600 MHz, DMSO-d₆) δ 0.97-1.01 (m, 3H), 1.37-1.47 (m, 1H), 1.79-1.87 (m, 1H), 1.88-1.97 (m, 1H), 1.99-2.06 (m, 1H), 2.09-2.24 (m, 1H), 2.80-3.27 (m, 1H), 3.44-3.50 (m, 0.7H), 3.93-3.96 (m, 3H), 4.02-4.06 (m, 0.3H), 5.46-5.95 (m, 1H), 7.69-7.77 (m, 2H), 7.78-7.88 (m, 1H), 8.41-8.51 (m, 1H), 8.51-8.56 (m, 1H), 9.03-9.08 (m, 1H), 11.00-11.04 (m, 1H).

LCMS(ESI): [M+H]⁺ m/z: calcd 403.5; found 404.0; Rt=4.222 min.

RT(IPA-MeOH, 50-50, 10 ml/min)=27.93 min

Example 222. The Synthesis of 5-[[2-[(2R,5S)-5-methyl-2-(6-oxo-5H-1,5-naphthyridin-2-yl)-1-piperidyl]-2-oxo-acetyl]amino]pyridine-3-carboxamide (Compound 1076) and 5-[[2-[(2S,5R)-5-methyl-2-(6-oxo-5H-1,5-naphthyridin-2-yl)-1-piperidyl]-2-oxo-acetyl]amino]pyridine-3-carboxamide (Compound 1079

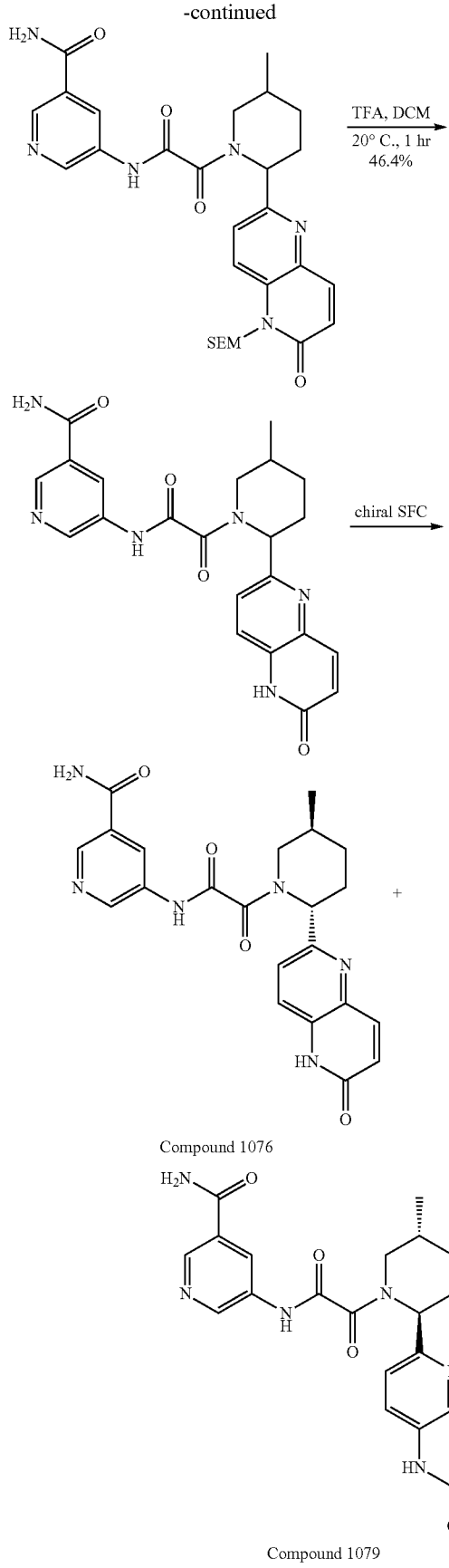

Step 1: Synthesis of 5-[[2-[5-methyl-2-[6-oxo-5-(2-trimethylsilylethoxymethyl)-1,5-naphthyridin-2-yl]-1-piperidyl]-2-oxo-acetyl]amino]pyridine-3-carboxamide A mixture of 6-(5-methyl-2-piperidyl)-1-(2-trimethylsilylethoxymethyl)-1,5-naphthyridin-2-one (300 mg, 0.803 mmol), 2-[(5-carbamoyl-3-pyridyl)amino]-2-oxo-acetic acid (100 mg, 0.322 mmol, Et₃N), HATU (147 mg, 0.387 mmol) and TEA (0.130 mL, 0.933 mmol) in DMF (6 mL) was stirred at 25° C. for 2 hours. The resulting mixture was quenched by addition of water (20 mL) and extracted with DCM (100 mL*3). The combined organic layer was washed with brine (50 mL), dried over anhydrous Na₂SO₄, filtered and concentrated under reduced pressure. The residue was purified by flash chromatography (ISCO®; 25 g AgelaFlash® Silica Flash Column, petroleum ether/EtOAc with EtOAc from 0~50%, then EtOAc/MeOH with MeOH from 0~5%, flow rate=30 mL/min, 254 nm) to afford 5-[[2-[5-methyl-2-[6-oxo-5-(2-trimethylsilylethoxymethyl)-1,5-naphthyridin-2-yl]-1-piperidyl]-2-oxo-acetyl]amino]pyridine-3-carboxamide (150 mg, 82.4% yield) as white solid. LCMS (ESI) [M+H]⁺ m/z: calcd 565.3, found 565.3.

Step 2: Synthesis of 5-[[2-[5-methyl-2-(6-oxo-5H-1,5-naphthyridin-2-yl)-1-piperidyl]-2-oxo-acetyl]amino]pyridine-3-carboxamide To a mixture of 5-[[2-[5-methyl-2-[6-oxo-5-(2-trimethylsilylethoxymethyl)-1,5-naphthyridin-2-yl]-1-piperidyl]-2-oxo-acetyl]amino]pyridine-3-carboxamide (140 mg, 0.248 mmol) in DCM (5 mL) was added TFA (1 mL, 13.0 mmol). The resulting mixture was stirred at 20° C. for 1 hour. The resulting mixture was adjusted to pH=8 with saturated NaHCO₃ solution, and then the mixture was concentrated in vacuo to give crude product, which was purified by flash chromatography (ISCO®; 12 g AgelaFlash® Silica Flash Column, DCM/MeOH with MeOH from 0~20%, flow rate=30 mL/min, 254 nm) to afford 5-[[2-[5-methyl-2-(6-oxo-5H-1,5-naphthyridin-2-yl)-1-piperidyl]-2-oxo-acetyl]amino]pyridine-3-carboxamide (50 mg, 46.4% yield) as white solid. LCMS (ESI) [M+H]⁺ m/z: calcd 435.2, found 435.2; HPLC: 90.34% @254 nm.

Step 3: Synthesis of 5-[[2-[(2R,5S)-5-methyl-2-(6-oxo-5H-1,5-naphthyridin-2-yl)-1-piperidyl]-2-oxo-acetyl]amino]pyridine-3-carboxamide (Compound 1076) and 5-[[2-[(2S,5R)-5-methyl-2-(6-oxo-5H-1,5-naphthyridin-2-yl)-1-piperidyl]-2-oxo-acetyl]amino]pyridine-3-carboxamide (Compound 1079

5-[[2-[5-methyl-2-(6-oxo-5H-1,5-naphthyridin-2-yl)-1-piperidyl]-2-oxo-acetyl]amino]pyridine-3-carboxamide (50 mg, 0.115 mmol) was separated by SFC (Instrument: Berger, Multigr AM-II; Column: Daicel Chiralcel OJ-H 250 mm×30 mm×5 m; Mobile phase: supercritical CO₂/MeOH (0.1% NH₃—H₂O, v %)=70/30; Flow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1076 (peak 3, retention time=4.899 min) and Compound 1079 (peak 4, retention time=6.996 min).

Compound 1076: 5-[[2-[(2R,5S)-5-methyl-2-(6-oxo-5H-1,5-naphthyridin-2-yl)-1-piperidyl]-2-oxo-acetyl]amino]pyridine-3-carboxamide (10.5 mg, single unknown enantiomer with trans relative chemistry, peak 3, retention time=4.899 min, white solid). ¹H NMR (400 MHz, DMSO-d₆) δ ppm 8.64-8.95 (m, 2H), 8.40 (br s, 1H), 7.88 (d, J=9.8 Hz, 1H), 7.71 (br d, J=8.5 Hz, 2H), 7.49 (br s, 2H), 6.71 (d, J=9.8 Hz, 1H), 5.32-5.71 (m, 1H), 2.44 (br dd, J=13.8, 3.3 Hz, 1H), 2.10 (br s, 1H), 1.92 (br s, 1H), 1.81 (br t, J=12.7 Hz, 2H), 1.36 (br d, J=10.8 Hz, 2H), 1.07 (d, J=6.8 Hz, 4H); LCMS (ESI) [M+H]⁺ m/z: calcd 435.2, found 435.1; HPLC: 1000% @254 nm; 97.5% ee.

Compound 1079: 5-[[2-[(2S,5R)-5-methyl-2-(6-oxo-5H-1,5-naphthyridin-2-yl)-1-piperidyl]-2-oxo-acetyl]amino]pyridine-3-carboxamide (10 mg, single unknown enantiomer with trans relative chemistry, peak 4, retention time=6.996 min, white solid). ¹H NMR (400 MHz, DMSO-d₆) δ ppm 8.61-8.94 (m, 2H), 8.40 (br s, 1H), 7.88 (d, J=9.5 Hz, 1H), 7.70 (br d, J=8.5 Hz, 2H), 7.49 (br s, 2H), 6.70 (d, J=9.8 Hz, 1H), 5.34-5.68 (m, 1H), 2.41 (br d, J=3.0 Hz, 1H), 1.99-2.20 (m, 1H), 1.92 (br s, 1H), 1.70-1.87 (m, 2H), 1.36 (br d, J=9.0 Hz, 2H), 1.06 (d, J=6.8 Hz, 3H); LCMS (ESI) [M+H]⁺ m/z: calcd 435.2, found 435.1; HPLC: 100% @254 nm; 100% ee.

Example 223. Synthesis of 5-(2-(6-(4-fluorophenyl)-5-azaspiro[2.5]octan-5-yl)-2-oxoacetamido)Nicotinamide (Compound 776

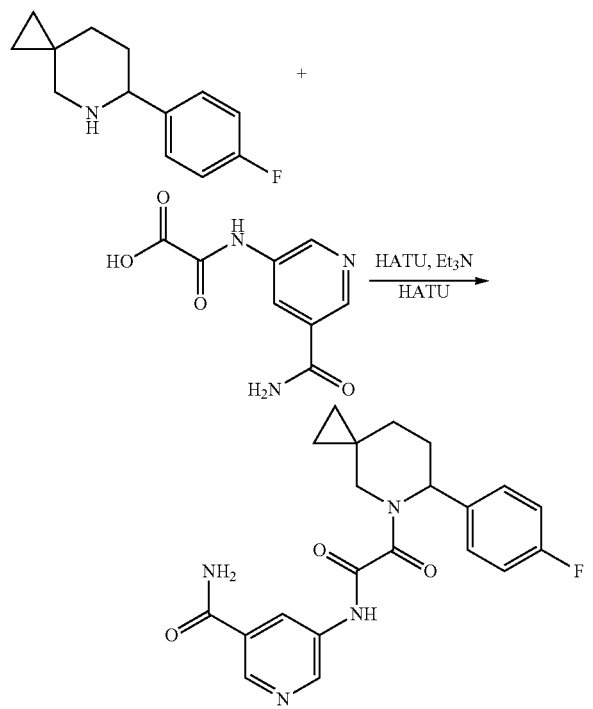

To a stirred solution of acid 2-((5-carbamoylpyridin-3-yl)amino)-2-oxoacetic acid (36 mg, 0.17 mmol) and 6-(4-fluorophenyl)-5-azaspiro[2.5]octane (35 mg, 0.17 mmol) in DMF (1.00 mL) was added HATU (65 mg, 0.17 mmol) and triethylamine (52 mg, 71 μL, 0.51 mmol) at 0° C. The resulting reaction mixture was stirred at ambient temperature for 18 hours. After 18 hours, the reaction mixture was concentrated under reduced pressure and water was added. The aqueous layer was extracted with EtOAc (2×). The combined organic phase was washed with water (2×), dried (Na₂SO₄) and concentrated under reduced pressure to obtain crude product. The residue was purified by silica gel column chromatography (5/5 Cyclohexane/Ethylacetate to 0/1) to give benzyl 5-(2-(6-(4-fluorophenyl)-5-azaspiro[2.5]octan-5-yl)-2-oxoacetamido)nicotinamide (Compound 776) as white solid (14 mg, 25%)

¹H NMR (CD₃OD, 400 MHz) δ 8.96 (d, J=2.4 Hz, 0.7H), 8.90 (d, J=2.4 Hz, 0.3H), 8.79 (d, J=1.9 Hz, 0.7H), 8.76 (d, J=1.9 Hz, 0.3H), 8.62 (t, J=2.2 Hz, 0.7H), 8.58 (t, J=2.2 Hz, 0.3H), 7.48-7.36 (m, 2H), 7.19-7.10 (m, 2H), 5.90 (app s, 0.7H), 5.52 (app s, 0.3H), 3.63 (d, J=13.7 Hz, 0.3H), 3.52 (d, J=13.7 Hz, 0.7H), 3.17-3.08 (m, 1H), 2.52-2.61 (m, 1H), 2.32-2.01 (m, 2H), 1.02-0.93 (m, 1H), 0.70-0.59 (m, 1H), 0.48-0.32 (m, 3H). 19F NMR (CD₃OD, 376 MHz) δ −118.3, 118.1.

Example 224. The Synthesis of 5-(2-(2-(4-fluorophenyl)-5-methylpiperidin-1-yl-2-d)-2-oxoacetamido)Nicotinamide (Compound 1008

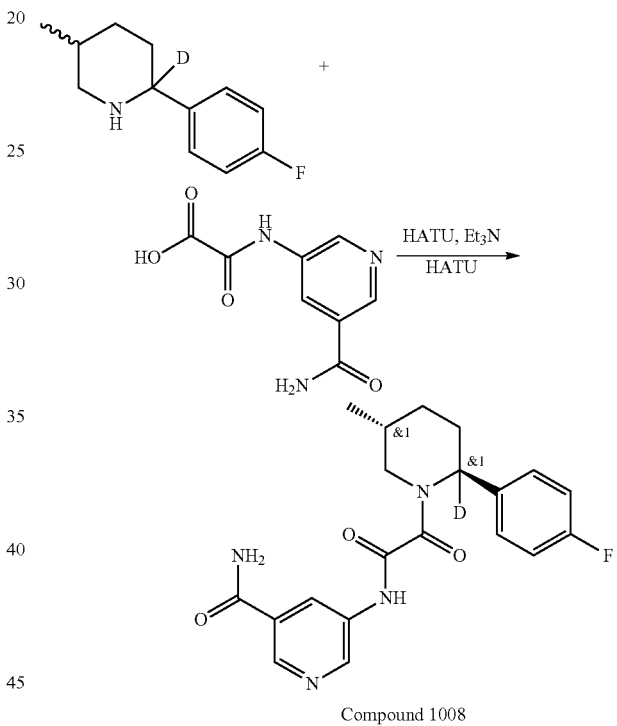

Compound 1008

To a stirred solution of acid 2-((5-carbamoylpyridin-3-yl)amino)-2-oxoacetic acid hydrochloride (108 mg, 0.51 mmol) and 2-(4-fluorophenyl)-5-methylpiperidine-2-d (100 mg, 0.51 mmol) in DMF (0.2 mL) was added HATU (196 mg, 0.51 mmol) and triethylamine (215 μL, 1.54 mmol) at 0° C. The resulting reaction mixture was stirred at ambient temperature for 18 hours. After 18 hours, the reaction mixture was concentrated under reduced pressure and water was added. The aqueous layer was extracted with EtOAc (2×). The combined organic phase was washed with water (2×), dried (Na₂SO₄) and concentrated under reduced pressure to obtain crude product. The residue was purified by silica gel column chromatography (CH₂Cl₂/MeOH 10/0 to 9/1) to give 5-(2-(2-(4-fluorophenyl)-5-methylpiperidin-1-yl-2-d)-2-oxoacetamido)nicotinamide (Compound 1008) as white solid (60 mg, 30%)

¹H NMR (CDCl₃, 400 MHz) 9.93 (s, 1H), 9.06-8.91 (m, 1H), 8.75 (s, 1H), 8.56 (s, 1H), 7.24-7.11 (m, 2H), 7.04-6.90 (m, 2H), 6.56 (s, 1H), 6.22 (s, 1H), 4.41 (d, J=13.2 Hz, 0.7H), 4.12 (d, J=13.2 Hz, 0.3H) 3.28 (d, J=12.5 Hz, 1H), 2.19-2.02 (m, 1H), 1.98-1.84 (m, 1H), 1.84-1.70 (m, 1H), 1.05-0.95 (m, 3H)

$^{19}$F NMR (CDCl$_3$, 376 MHz) δ −115.9, −115.8.

Example 225. Synthesis of 5-(2-(2-(4-Fluorophenyl-2,3,5,6-d4)-5-methylpiperidin-1-yl)-2-oxoacetamido)Nicotinamide (Compound 1004

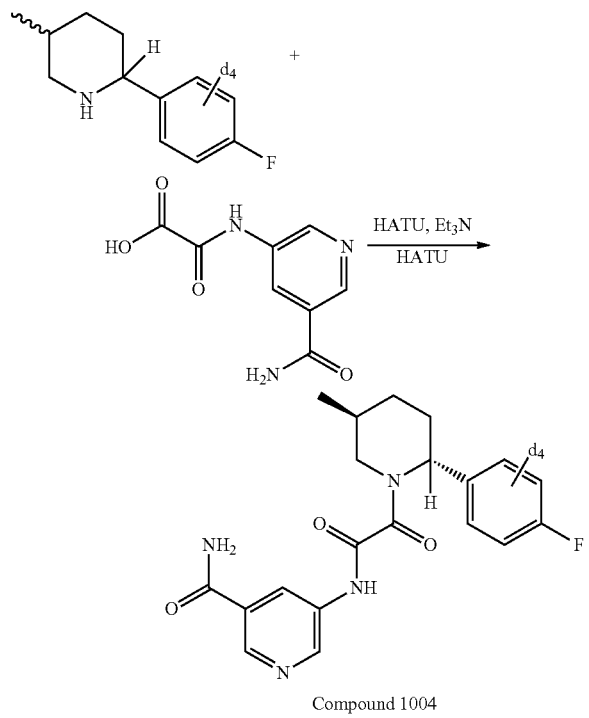

Compound 1004

To a stirred solution of acid 2-((5-carbamoylpyridin-3-yl)amino)-2-oxoacetic acid hydrochloride (62 mg, 0.25 mmol) and 2-(4-fluorophenyl-2,3,5,6-d4)-5-methylpiperidine (50 mg, 0.25 mmol) in DMF (4 mL) was added HATU (96 mg, 0.25 mmol) and triethylamine (140 µL, 1.0 mmol) at 0° C. The resulting reaction mixture was stirred at ambient temperature for 18 hours. After 18 hours, the reaction mixture was concentrated under reduced pressure and water was added. The aqueous layer was extracted with EtOAc (2×). The combined organic phase was washed with water (2×), dried (Na$_2$SO$_4$) and concentrated under reduced pressure to obtain crude product. The residue was purified by silica gel column chromatography (Cyclohexane/Ethyl Acetate 10/0 to 0/10) to give 5-(2-(2-(4-fluorophenyl-2,3,5,6-d4)-5-methylpiperidin-1-yl)-2-oxoacetamido)nicotinamide (Compound 1004) as white solid (60 mg, 30%)

$^1$H NMR (DMSO-d$_6$, 400 MHz) 11.3 (s, 0.6H), 11.2 (m, 0.4H), 8.93 (app d, 0.6H), 8.86 (s, 0.4H), 8.81 (s, 0.6H), 8.77 (s, 0.4H), 8.52 (s, 0.6H), 8.48 (s, 0.4H), 8.20 (s, 0.6H), 8.16 (s, 0.4H), 7.65 (s, 0.6H), 7.60 (s, 0.4H), 5.59 (s, 0.6H), 5.16 (s, 0.4H), 3.48 (d, J=13.6 Hz), 3.25 (dd, J=3.2, 13.7 Hz, 1H), 2.82-2.75 (m, 1H) 2.24-1.80 (m, 3.4H), 1.75-1.62 (m, 1H), 1.42-1.35 (m, 1H), 1.10-1.01 (m, 3H)

$^{19}$F NMR (DMSO-d$_6$, 376 MHz) δ −116.9, −117.0.

LRMS (APCI$^-$) m/z (C$_{20}$H$_{16}$D$_4$FN$_4$O$_3$): theor. 387.2, exp. 387.3.

Example 226. Synthesis of 5-(2-(2-(4-Fluorophenyl-2,3,5,6-d4)-5-methylpiperidin-1-yl-2-d)-2-oxoacetamido)Nicotinamide (Compound 1010

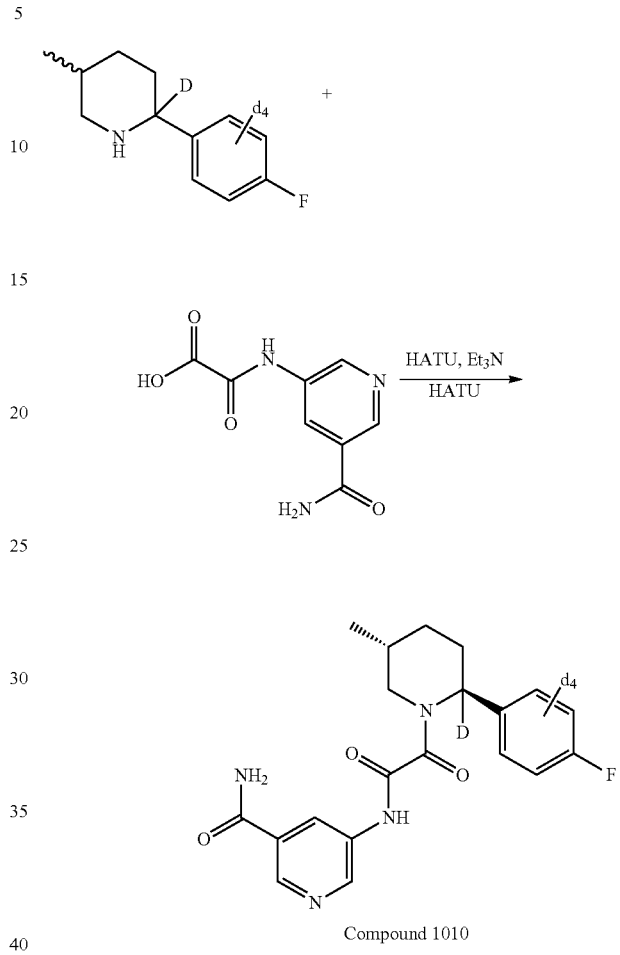

Compound 1010

To a stirred solution of acid 2-((5-carbamoylpyridin-3-yl)amino)-2-oxoacetic acid hydrochloride (108 mg, 0.51 mmol) and 2-(4-fluorophenyl-2,3,5,6-d4)-5-methylpiperidine-2-d (100 mg, 0.51 mmol) in DMF (0.2 mL) was added HATU (196 mg, 0.51 mmol) and triethylamine (215 µL, 1.54 mmol) at 0° C. The resulting reaction mixture was stirred at ambient temperature for 18 hours. After 18 hours, the reaction mixture was concentrated under reduced pressure and water was added. The aqueous layer was extracted with EtOAc (2×). The combined organic phase was washed with water (2×), dried (Na$_2$SO$_4$) and concentrated under reduced pressure to obtain crude product. The residue was purified by silica gel column chromatography (CH$_2$Cl$_2$/MeOH 10/0 to 9/1) to 5-(2-(2-(4-fluorophenyl-2,3,5,6-d4)-5-methylpiperidin-1-yl-2-d)-2-oxoacetamido)nicotinamide (Compound 1010) as white solid (60 mg, 30%)

$^1$H NMR (DMSO-d$_6$, 400 MHz) 11.3 (s, 0.6H), 11.2 (m, 0.4H), 8.93 (app d, 0.6H), 8.87 (s, 0.4H), 8.81 (app d, 0.6H), 8.77 (app d, 0.4H), 8.52 (s, 0.6H), 8.48 (s, 0.4H), 8.20 (s, 0.6H), 8.16 (s, 0.4H), 7.64 (s, 0.6H), 7.60 (s, 0.4H), 4.04 (d, J=13.2 Hz, 0.7H), 4.12 (d, J=13.0 Hz, 0.3H), 3.25 (d, J=3.4, 14.3 Hz, 1H), 2.81-2.75 (m, 1H) 2.27-1.85 (m, 3.4H), 1.75-1.62 (m, 1H), 1.42-1.29 (m, 1H), 1.10-1.01 (m, 3H)

$^{19}$F NMR (DMSO-d$_6$, 376 MHz) δ −116.9, −117.0.

LRMS (APCI$^+$) m/z (C$_{20}$H$_{16}$D5FN$_4$O$_3$H): theor. 390.1, exp. 390.4.

Example 227. The Synthesis of 5-(2-(5-methyl-2-(pyridin-4-yl)piperidin-1-yl)-2-oxoacetamido)Nicotinamide (Compound 539 and Compound 544

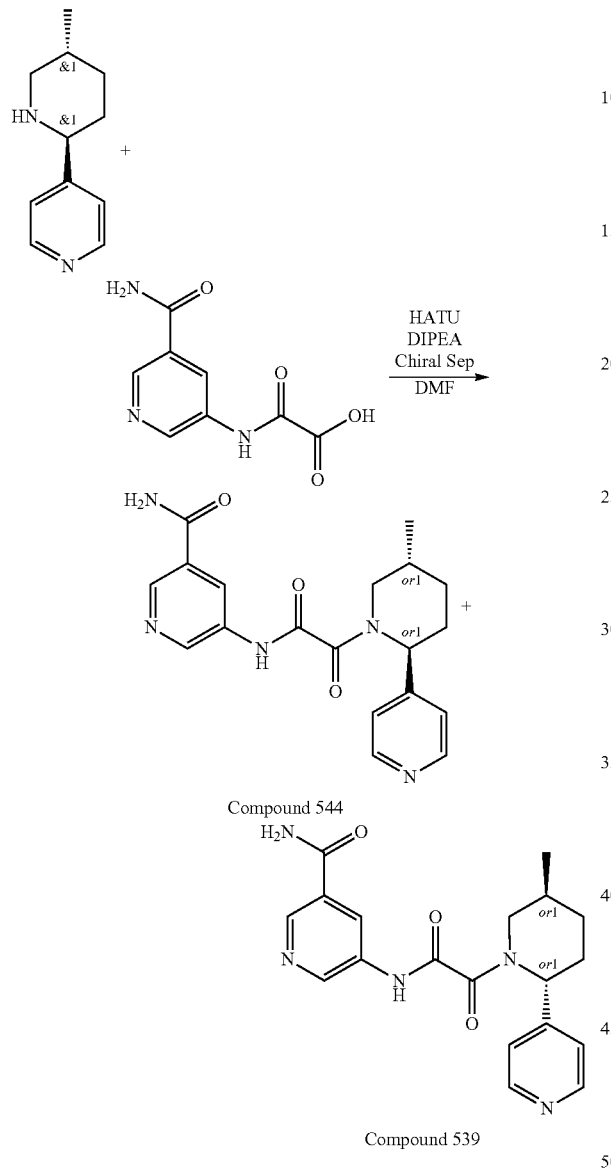

Compound 544

Compound 539

4-[(2R,5S)-5-methyl-2-piperidyl]pyridine (0.3 g, 1.70 mmol), 2-[(5-carbamoyl-3-pyridyl)amino]-2-oxo-acetic acid (356.00 mg, 1.70 mmol, TEA) and DIPEA (659.92 mg, 5.11 mmol, 889.38 µL) were dissolved in DMF (6 mL) under gentle heating. HATU (776.60 mg, 2.04 mmol) was added in small portions under vigorous stirring and occasional heating. After the reaction was complete, the mixture was purified by HPLC (0-25%, 0.5-6.5 min; 30 ml/min; water-MeCN (loading pump 4 ml/min MeCN); target mass 368; column SunFire 100*19 mm 5 um) and the obtained racemic mixture was separated by chiral HPLC (System 2. Column: Chiralpak IA (250*20 mm*5 mm); Mobile phase: Hexane-IPA-MeOH, 50-25-25 Flow Rate: 12 mL/min; Column Temperature: 24° C.; Wavelength: 210 nm, 215 nm, 254 nm) to give 5-[[2-[(2R,5S)-5-methyl-2-(4-pyridyl)-1-piperidyl]-2-oxo-acetyl]amino]pyridine-3-carboxamide (44 mg, 119.76 µmol, 7.04% yield) and 5-[[2-[(2S,5R)-5-methyl-2-(4-pyridyl)-1-piperidyl]-2-oxo-acetyl]amino]pyridine-3-carboxamide (43 mg, 117.04 µmol, 6.88% yield).

Ret time for Compound 539 in analytical conditions (column: IA, Hexane-IPA-MeOH, 50-25-25, 0.6 ml/min as mobile phase) 38.74 min and for Compound 544 31.88 min.

Compound 539: Retention time: 38.74 min
$^1$H NMR (600 MHz, DMSO-$d_6$) δ (ppm) 0.96-1.05 (m, 3H), 1.28-1.40 (m, 1H), 1.51-1.61 (m, 1H), 1.80-1.94 (m, 1H), 1.99-2.15 (m, 1H), 2.15-2.25 (m, 1H), 2.73-3.25 (m, 1H), 3.46-4.12 (m, 1H), 5.18-5.63 (m, 1H), 7.27-7.39 (m, 2H), 7.52-7.66 (m, 1H), 8.09-8.21 (m, 1H), 8.39-8.53 (m, 1H), 8.53-8.63 (m, 2H), 8.70-8.81 (m, 1H), 8.81-8.93 (m, 1H), 11.14-11.38 (m, 1H).
LCMS(ESI): [M]$^+$ m/z: calcd 367.2; found 368.2; Rt=1.211 min.

Compound 544: Retention time: 31.88 min
$^1$H NMR (600 MHz, DMSO-$d_6$) δ (ppm) 0.99-1.04 (m, 3H), 1.29-1.39 (m, 1H), 1.51-1.60 (m, 1H), 1.82-1.93 (m, 1H), 2.01-2.15 (m, 1H), 2.17-2.24 (m, 1H), 2.74-3.25 (m, 1H), 3.46-4.10 (m, 1H), 5.17-5.63 (m, 1H), 7.28-7.37 (m, 2H), 7.53-7.67 (m, 1H), 8.09-8.21 (m, 1H), 8.41-8.52 (m, 1H), 8.53-8.61 (m, 2H), 8.71-8.81 (m, 1H), 8.82-8.93 (m, 1H), 11.19-11.31 (m, 1H).
LCMS(ESI): [M]$^+$ m/z: calcd 367.2; found 368.2; Rt=1.209 min.

Example 228. The Synthesis of 5-(2-(5-methyl-2-(3-Sulfamoylphenyl)piperidin-1-yl)-2-oxoacetamido)Nicotinamide (Compound 661

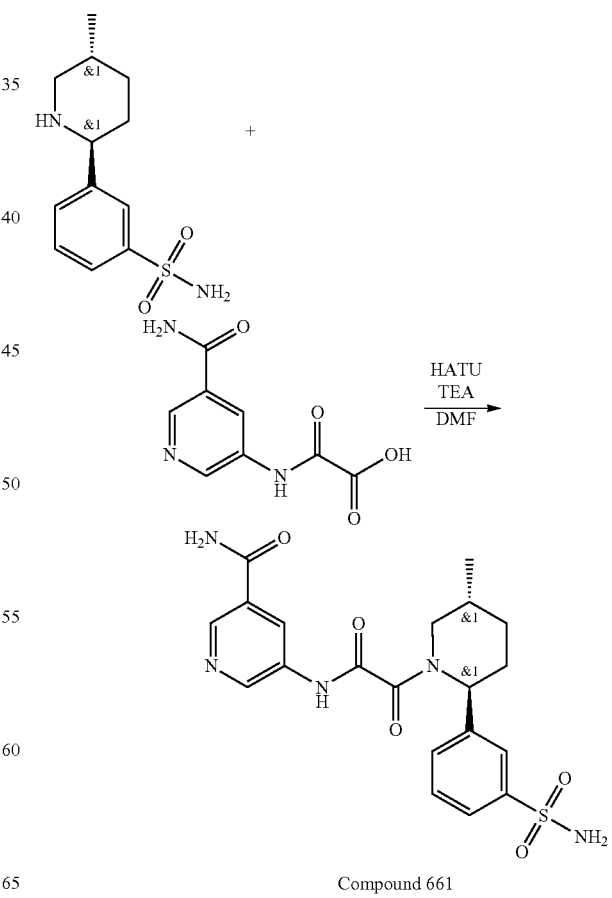

Compound 661

1663

To a stirred mixture of 3-[(2S,5R)-5-methyl-2-piperidyl]benzenesulfonamide (490 mg, 1.93 mmol), 2-[(5-carbamoyl-3-pyridyl)amino]-2-oxo-acetic acid (473.19 mg, 1.93 mmol, HCl) and TEA (584.83 mg, 5.78 mmol, 805.55 uL) in DMF (4 mL) was added HATU (805.76 mg, 2.12 mmol). The resulting reaction mixture was stirred at 20° C. for 4 hr. Then, it was subjected to HPLC (Column: YMC-Actus Triart C18 100*20 mm, 5 um; 0-1-6 min 5-5-50% water-CAN (NH$_3$0.1%), flow 30 ml/min), affording 5-[[2-[(2S,5R)-5-methyl-2-(3-sulfamoylphenyl)-1-piperidyl]-2-oxo-acetyl]amino]pyridine-3-carboxamide (190 mg, 426.50 umol, 22.14% yield).

$^1$H NMR (600 MHz, DMSO-d$_6$) δ (ppm) 1.03 (m, 3H), 1.36 (m, 1H), 1.66 (m, 1H), 1.91 (m, 1H), 2.18 (m, 2H), 3.01 (m, 1H), 3.81 (m, 1H), 5.46 (m, 1H), 7.36 (m, 2H), 7.55 (m, 3H), 7.75 (m, 2H), 8.14 (m, 1H), 8.48 (m, 1H), 8.75 (m, 1H), 8.86 (m, 1H), 11.24 (m, 1H).

LCMS(ESI): [M]$^+$ m/z: calcd 445.4; found 446.2; Rt=1.855 min.

Example 229. The Synthesis of 5-[[2-[(2R,5R)-5-methyl-2-phenyl-1-piperidyl]-2-oxo-acetyl]amino]pyridine-3-carboxamide (Compound 75), 5-[[2-[(2R,5S)-5-methyl-2-phenyl-1-piperidyl]-2-oxo-acetyl]amino]pyridine-3-carboxamide (Compound 88), 5-[[2-[(2S,5R)-5-methyl-2-phenyl-1-piperidyl]-2-oxo-acetyl]amino]pyridine-3-carboxamide (Compound 71), and 5-[[2-[(2S,5S)-5-methyl-2-phenyl-1-piperidyl]-2-oxo-acetyl]amino]pyridine-3-carboxamide (Compound 82

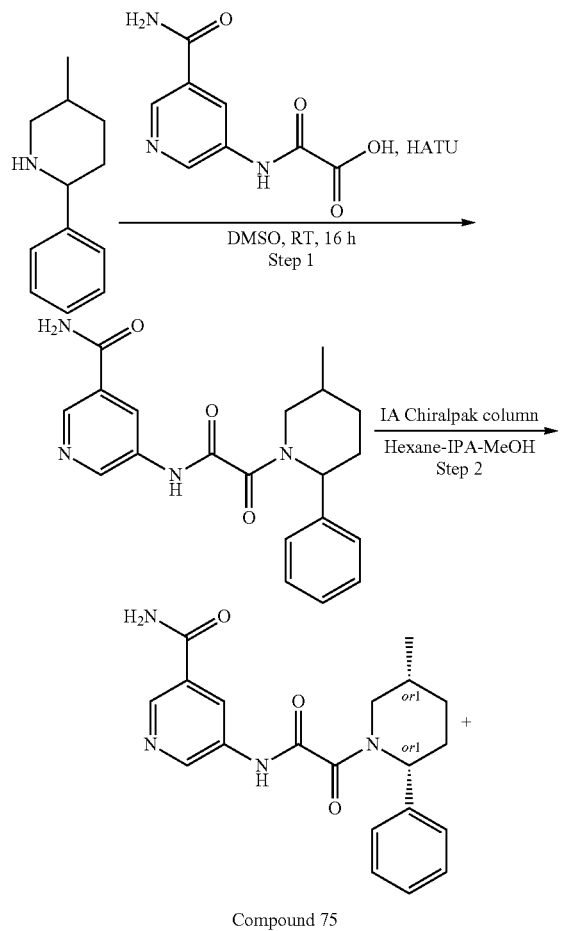

Compound 75

1664

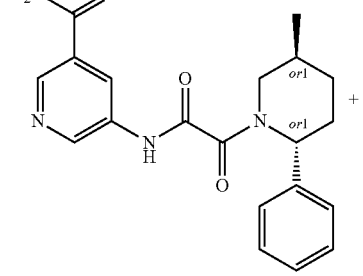

Compound 88

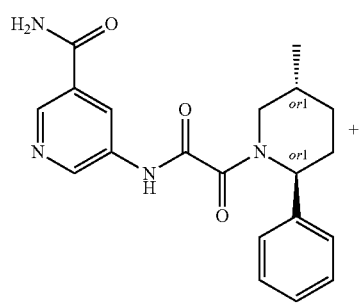

Compound 71

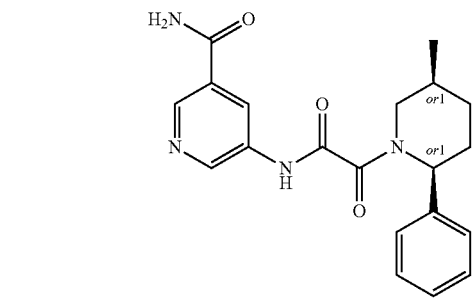

Compound 82

Step 1: The Synthesis of 5-[[2-(5-methyl-2-phenyl-1-piperidyl)-2-oxo-acetyl]amino]pyridine-3-carboxamide 5-methyl-2-phenyl-piperidine (200 mg, 1.14 mmol), 2-[(5-carbamoyl-3-pyridyl)amino]-2-oxo-acetic acid (354.14 mg, 1.14 mmol, N(Et)$_3$) and HATU (477.27 mg, 1.26 mmol) were mixed in DMSO (4 mL) and stirred at 25° C. for 16 h. Final solution was subjected to HPLC (03_MeCN 2-9 min 20-45% MeCN, 30 ml/min column: SunFire C18 100*19 5 microM) to afford 5-[[2-(5-methyl-2-phenyl-1-piperidyl)-2-oxo-acetyl]amino]pyridine-3-carboxamide (229 mg, 624.98 μmol, 54.77% yield).

$^1$H NMR (400 MHz, DMSO-d$_6$) δ 1.02 (d, 3H), 1.65 (m, 2H), 2.10 (m, 2H), 2.60 (m, 1H), 3.11 (m, 3H), 3.26 (m, 1H), 4.12 (m, 1H), 5.36 (m, 1H), 7.31 (m, 5H), 7.54 (d, 1H), 8.36 (d, 1H), 8.50 (m, 1H), 8.82 (m, 2H).

LCMS(ESI): [M+H]$^+$ m/z: calcd 366.1; found 367.2; Rt=1.199 min.

Step 2: The Synthesis of 5-[[2-[(2R,5R)-5-methyl-2-phenyl-1-piperidyl]-2-oxo-acetyl]amino]pyridine-3-carboxamide (Compound 75), 5-[[2-[(2R,5S)-5-methyl-2-phenyl-1-piperidyl]-2-oxo-acetyl]amino]pyridine-3-carboxamide (Compound 88), 5-[[2-[(2S,5R)-5-methyl-2-phenyl-1-piperidyl]-2-oxo-acetyl]amino]pyridine-3-carboxamide (Compound 71), and 5-[[2-[(2S,5S)-5-methyl-2-phenyl-1-piperidyl]-2-oxo-acetyl]amino]pyridine-3-carboxamide (Compound 82

5-[[2-(5-methyl-2-phenyl-1-piperidyl)-2-oxo-acetyl]amino]pyridine-3-carboxamide was chirally separated using IA (250*25, 5 mkm) column, Hexane-IPA-MeOH, 70-15-15 as a mobile phase; Flow 12 ml/min affording Compound 75—of 5-[[2-[(2R,5R)-5-methyl-2-phenyl-1-piperidyl]-2-oxo-acetyl]amino]pyridine-3-carboxamide (19.9 mg, 12.54%; RT=29.173 min), Compound 88—5-[[2-[(2R,5S)-5-methyl-2-phenyl-1-piperidyl]-2-oxo-acetyl]amino]pyridine-3-carboxamide (56.2 mg, 35.41%; RT=78.286 min), Compound 71—5-[[2-[(2S,5R)-5-methyl-2-phenyl-1-piperidyl]-2-oxo-acetyl]amino]pyridine-3-carboxamide (49.2 mg, 31.0%; RT=40.746 min), and Compound 82—5-[[2-[(2S,5S)-5-methyl-2-phenyl-1-piperidyl]-2-oxo-acetyl]amino]pyridine-3-carboxamide (14.2 mg, 8.95%; RT=34.172 min).

Compound 71: RT (IA (250*25, 5 mkm), Hexane-IPA-MeOH, 60-20-20, 0.6 ml/min)=19.56 min.

$^1$H NMR (500 MHz, DMSO-$d_6$) δ 1.05 (m, 3H), 1.35 (m, 1H), 1.69 (m, 1H), 1.90 (m, 1H), 2.23 (m, 1H), 3.23 (m, 2H), 3.77 (m, 1H), 5.41 (m, 1H), 7.35 (m, 5H), 7.60 (m, 1H), 8.16 (m, 1H), 8.49 (m, 1H), 8.78 (m, 1H), 8.90 (m, 1H), 11.24 (m, 1H).

LCMS(ESI): [M+H]$^+$ m/z: calcd 366.2; found 367.2; Rt=4.361 min.

Compound 82: RT (IA (250*25, 5 mkm), Hexane-IPA-MeOH, 60-20-20, 0.6 ml/min)=16.02 min.

$^1$H NMR (500 MHz, DMSO-$d_6$) δ 0.77 (m, 3H), 1.07 (m, 1H), 1.66 (m, 2H), 1.92 (m, 1H), 2.21 (m, 1H), 2.59 (m, 1H), 3.94 (m, 1H), 5.44 (m, 1H), 7.37 (m, 5H), 7.61 (m, 1H), 8.17 (m, 1H), 8.50 (m, 1H), 8.78 (m, 1H), 8.89 (m, 1H), 11.28 (m, 1H).

LCMS(ESI): [M+H]$^+$ m/z: calcd 366.2; found 367.2; Rt=4.421 min.

Compound 88: RT (IA (250*25, 5 mkm), Hexane-IPA-MeOH, 60-20-20, 0.6 ml/min)=38.93 min.

$^1$H NMR (600 MHz, DMSO-$d_6$) δ 1.03 (m, 3H), 1.34 (m, 1H), 1.66 (m, 1H), 1.85 (m, 1H), 2.05 (m, 1H), 2.21 (m, 1H), 3.26 (m, 1H), 3.75 (m, 1H), 5.61 (m, 1H), 7.27 (m, 1H), 7.37 (m, 4H), 7.59 (m, 1H), 8.15 (m, 1H), 8.48 (m, 1H), 8.77 (m, 1H), 8.89 (m, 1H), 11.23 (m, 1H).

LCMS(ESI): [M+H]$^+$ m/z: calcd 366.2; found 367.2; Rt=4.363 min.

Compound 75: RT (IA (250*25, 5 mkm), Hexane-IPA-MeOH, 60-20-20, 0.6 ml/min)=14.26 min.

$^1$H NMR (500 MHz, DMSO-$d_6$) δ 0.77 (m, 3H), 1.07 (m, 1H), 1.69 (m, 2H), 1.92 (m, 1H), 2.23 (m, 1H), 2.60 (m, 1H), 3.94 (m, 1H), 5.44 (m, 1H), 7.36 (m, 5H), 7.61 (m, 1H), 8.17 (m, 1H), 8.50 (m, 1H), 8.78 (m, 1H), 8.89 (m, 1H), 11.28 (m, 1H).

LCMS(ESI): [M+H]$^+$ m/z: calcd 366.2; found 367.2; Rt=4.421 min.

Example 230. The Synthesis of rac-2-((2R,5S)-5-methyl-2-(Naphthalen-2-yl)piperidin-1-yl)-N-(5-methylpyridin-3-yl)-2-oxoacetamide (Compound 83

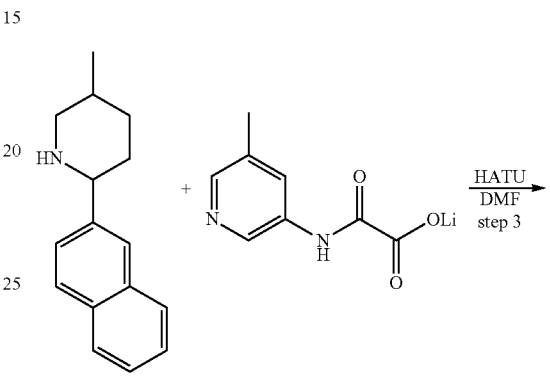

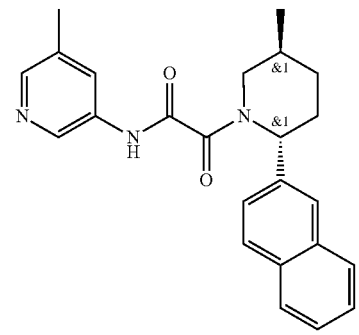

Compound 83

[2-[(5-methyl-3-pyridyl)amino]-2-oxo-acetyl]oxylithium (412.94 mg, 2.22 mmol) and HATU (843.73 mg, 2.22 mmol) were mixed in DMF (3 mL) and the resulting mixture was stirred at 20° C. for 20 min followed by addition of 5-methyl-2-(2-naphthyl)piperidine (0.5 g, 2.22 mmol) and the resulting mixture was stirred at 20° C. for 12 hr. The resulting mixture was subjected to HPLC to obtain 2-[(2S,5R)-5-methyl-2-(2-naphthyl)-1-piperidyl]-N-(m-tolyl)-2-oxo-acetamide (0.029 g, 75.04 μmol, 3.38% yield).

$^1$H NMR (400 MHz, CDCl$_3$) δ (ppm) 1.11 (d, 3H), 1.43 (m, 1H), 1.96 (m, 2H), 2.31 (m, 5H), 3.23 (m, 1H), 4.55 (m, 1H), 6.27 (m, 1H), 7.42 (m, 3H), 7.79 (m, 4H), 8.00 (m, 1H), 8.21 (m, 1H), 8.48 (m, 1H), 9.40 (m, 1H).

LCMS(ESI): [M]$^+$ m/z: calcd 386.5; found 387.2; Rt=3.213 min.

1667

Example 231. The Synthesis of N-(6-amino-5-methyl-3-pyridyl)-2-[(2R,5S)-5-methyl-2-(2-methyl-1,3-benzoxazol-5-yl)-1-piperidyl]-2-oxo-acetamide (Ent-Compound 1170)) and N-(6-amino-5-methyl-3-pyridyl)-2-[(2S,5S)-5-methyl-2-(2-methyl-1,3-benzoxazol-5-yl)-1-piperidyl]-2-oxo-acetamide (Compound 1170

1668

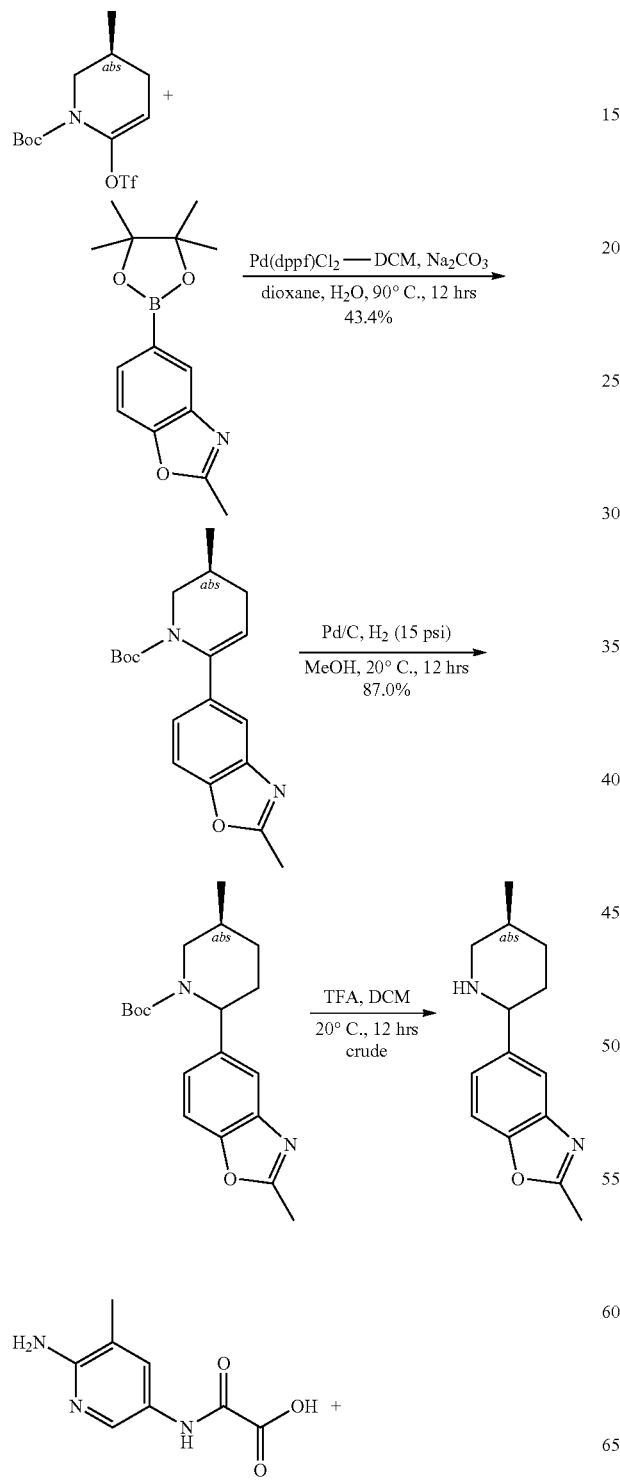

Step 1: Synthesis of tert-butyl (3S)-3-methyl-6-(2-methyl-1,3-benzoxazol-5-yl)-3,4-dihydro-2H-pyridine-1-carboxylate To a round bottom flask were added 2-methyl-5-(4,4,5,5-tetramethyl-1,3,2-dioxaborolan-2-yl)-1,3-benzoxazole (100 mg, 0.386 mmol), tert-butyl (3S)-3-methyl-6-(trifluoromethylsulfonyloxy)-3,4-dihydro-2H-pyridine-1-carboxylate (135 mg, 0.391 mmol), Pd(dppf)Cl$_2$-DCM (65 mg, 0.0796 mmol), Na$_2$CO$_3$ (125 mg, 1.18 mmol), H$_2$O (0.5 mL) and dioxane (2 mL). The mixture was degassed and backfilled with nitrogen for three times and then stirred for 12 hours at 90° C. under nitrogen. The resulting mixture was quenched by addition of water (10 mL) and extracted with EtOAc (20 mL*3). The combined organic layer was washed with saturated NH$_4$Cl aqueous solution (20 mL*2), brine (20 mL), dried over anhydrous Na$_2$SO$_4$, filtered and concentrated under reduced pressure. The residue was purified by flash chromatography (ISCO®; 8 g Agela Flash® Silica Flash Column, petroleum ether/EtOAc with EtOAc from 0~30%, Flow rate: 30 mL/min) to afford tert-butyl (3S)-3-methyl-6-(2-methyl-1,3-benzoxazol-5-yl)-3,4-dihydro-2H-pyridine-1-carboxylate (100 mg, 78.9% yield) as white gum. LCMS (ESI) [M+H]$^+$ m/z: calcd 329.2, found 329.1.

Step 2: Synthesis of tert-butyl (5S)-5-methyl-2-(2-methyl-1,3-benzoxazol-5-yl)piperidine-1-carboxylate To a solution of tert-butyl (3S)-3-methyl-6-(2-methyl-1,3-benzoxazol-5-yl)-3,4-dihydro-2H-pyridine-1-carboxylate (80 mg, 0.244 mmol) in MeOH (5 mL) was added Pd/C (10 mg, 10 wt % of Pd with 50 wt % of water). The mixture was degassed and backfilled with hydrogen for 3 times. The mixture was stirred at 20° C. for 12 hours under hydrogen atmosphere (in balloon, ~15 psi). The resulting mixture was filtered and concentrated under reduced pressure to afford tert-butyl (5S)-5-methyl-2-(2-methyl-1,3-benzoxazol-5-yl)piperidine-1-carboxylate (70 mg 87.0% yield) as yellow oil. LCMS (ESI) [M+H]$^+$ m/z: calcd 331.1, found 331.1.

Step 3: Synthesis of 2-methyl-5-[(5S)-5-methyl-2-piperidyl]-1,3-benzoxazole

To a solution of tert-butyl (5S)-5-methyl-2-(2-methyl-1,3-benzoxazol-5-yl)piperidine-1-carboxylate (70 mg, 0.212 mmol) in DCM (3 mL) was added TFA (0.5 mL, 6.49 mmol). The mixture was stirred at 20° C. for 12 hours. The resulting mixture was quenched by addition of saturated NaHCO$_3$ aqueous solution (20 mL) and extracted with DCM (50 mL*3). The combined organic layer was dried over anhydrous Na$_2$SO$_4$, filtered and concentrated under reduced pressure to afford 2-methyl-5-[(5S)-5-methyl-2-piperidyl]-1,3-benzoxazole (50 mg, crude) as yellow oil. LCMS (ESI) [M+H]$^+$ m/z: calcd 231.1, found 231.1.

Step 4: Synthesis of N-(6-amino-5-methyl-3-pyridyl)-2-[(5S)-5-methyl-2-(2-methyl-1,3-benzoxazol-5-yl)-1-piperidyl]-2-oxo-acetamide To a solution of 2-methyl-5-[(5S)-5-methyl-2-piperidyl]-1,3-benzoxazole (45 mg, 0.195 mmol) in DMF (5 mL) were added 2-[(6-amino-5-methyl-3-pyridyl)amino]-2-oxo-acetic acid (45 mg, 0.231 mmol) and HATU (80 mg, 0.210 mmol). Then DIPEA (90 mg, 0.696 mmol) was added and the mixture was stirred at 20° C. for 12 hours. The resulting mixture was quenched by addition of water (10 mL) and extracted with EtOAc (20 mL*3). The combined organic layer was washed with saturated NH$_4$Cl aqueous solution (10 mL*2), brine (10 mL*3), dried over anhydrous Na$_2$SO$_4$, filtered and concentrated under reduced pressure. The residue was purified by preparative TLC (silica, DCM/MeOH=10:1, 254 nm) to afford N-(6-amino-5-methyl-3-pyridyl)-2-[(5S)-5-methyl-2-(2-methyl-1,3-benzoxazol-5-yl)-1-piperidyl]-2-oxo-acetamide (35 mg, 44.0% yield) as yellow oil. LCMS (ESI) [M+H]$^+$ m/z: calcd 408.2, found 408.1.

Step 5: Synthesis of N-(6-amino-5-methyl-3-pyridyl)-2-[(2R,5S)-5-methyl-2-(2-methyl-1,3-benzoxazol-5-yl)-1-piperidyl]-2-oxo-acetamide (Ent-Compound 1170) and N-(6-amino-5-methyl-3-pyridyl)-2-[(2S,5S)-5-methyl-2-(2-methyl-1,3-benzoxazol-5-yl)-1-piperidyl]-2-oxo-acetamide (Compound 1170

N-(6-amino-5-methyl-3-pyridyl)-2-[(5S)-5-methyl-2-(2-methyl-1,3-benzoxazol-5-yl)-1-piperidyl]-2-oxo-acetamide (30 mg, 73.6 μmol) was separated by chiral SFC (Instrument: Thar80; Column: Daicel Chiralcel OJ (250 mm*30 mm, 10 μm); Mobile phase: supercritical CO$_2$/EtOH (0.1% NH$_3$—H$_2$O, v %)=65/35; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford ent-Compound 1170 (peak 1, retention time=1.520 min) and Compound 1170 (peak 2, retention time=1.641 min).

Ent-Compound 1170: N-(6-amino-5-methyl-3-pyridyl)-2-[(2R,5S)-5-methyl-2-(2-methyl-1,3-benzoxazol-5-yl)-1-piperidyl]-2-oxo-acetamide (5 mg, single unknown enantiomer with one known chiral center, peak 1, retention time=1.520 min, 16.7% yield, yellow solid). 1H NMR (400 MHz, methanol-d4) δ ppm 7.87-8.02 (1H, m), 7.43-7.58 (3H, m), 7.23-7.36 (1H, m), 5.39-5.82 (1H, m), 3.71 (1H, dd, J=13.30, 3.76 Hz), 2.46-2.64 (4H, m), 2.02-2.27 (3H, m), 1.86-1.99 (1H, m), 1.62-1.82 (2H, m), 0.69-0.82 (5H, m); LCMS (ESI) [M+H]$^+$ m/z: calcd 408.2, found 408.1; HPLC: 98.32% @220 nm, 99.30%0@254 nm; >95% ee, 99.8% de.

Compound 1170: N-(6-amino-5-methyl-3-pyridyl)-2-[(2S,5S)-5-methyl-2-(2-methyl-1,3-benzoxazol-5-yl)-1-piperidyl]-2-oxo-acetamide (3 mg, 16.7% yield), yellow solid. 1H NMR (400 MHz, methanol-d4) δ ppm 7.88-8.12 (1H, m), 7.53-7.67 (3H, m), 7.39 (1H, br s), 5.79 (1H, br s), 4.07-3.72 (1H, m), 2.61-2.65 (3H, m), 2.30 (2H, br s), 2.09-2.18 (3H, m), 1.93 (2H, br d, J=12.30 Hz), 1.45 (1H, br d, J=12.30 Hz), 1.14 (3H, d, J=6.78 Hz), 0.89 (1H, br d, J=7.53 Hz); LCMS (ESI) [M+H]$^+$ m/z: calcd 408.2, found 408.1; HPLC: 92.860% @220 nm, 94.72% @254 nm; >95% ee, 93.0% de.

Example 232. The Synthesis of N-(6-amino-5-methyl-3-pyridyl)-2-[(2R,5S)-5-methyl-2-(3-methyl-1,2-benzothiazol-5-yl)-1-piperidyl]-2-oxo-Acetamid (Compound 1166) and N-(6-amino-5-methyl-3-pyridyl)-2-[(2S,5R)-5-methyl-2-(3-methyl-1,2-benzothiazol-5-yl)-1-piperidyl]-2-oxo-Acetamid (Ent-Compound 1166

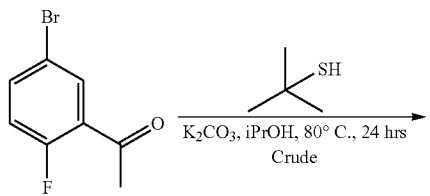

-continued
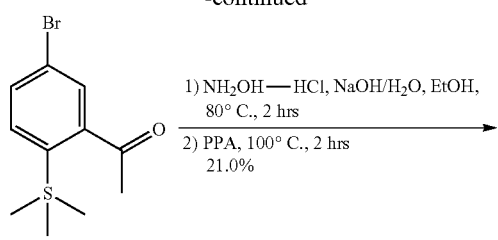
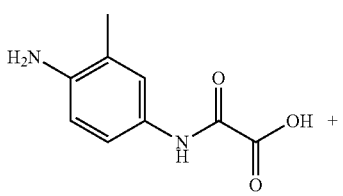
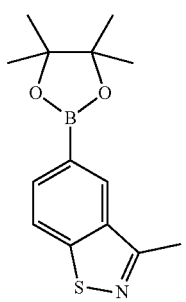
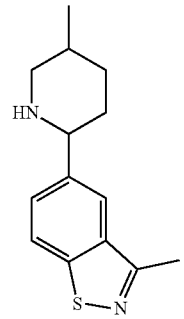
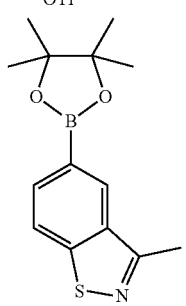
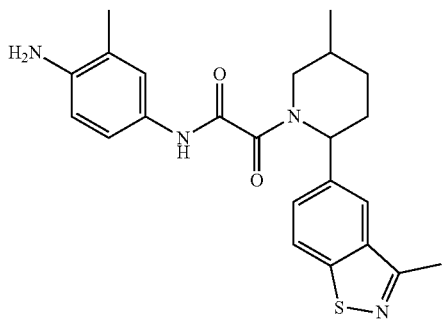
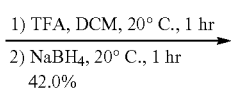
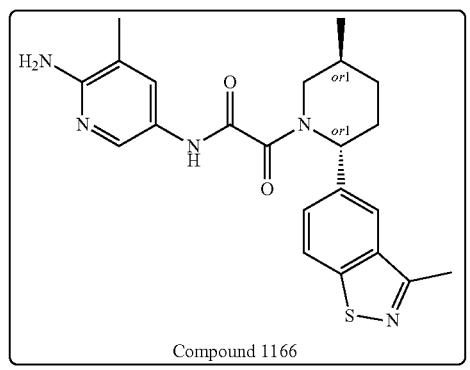
Compound 1166

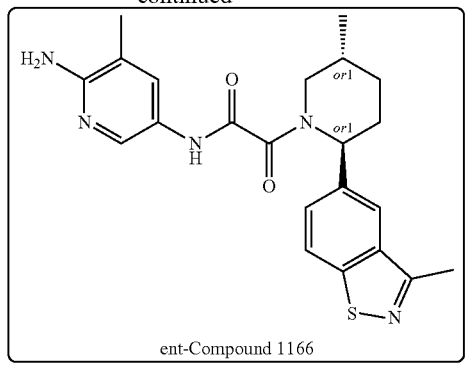

ent-Compound 1166

Step 6: Synthesis of N-(6-amino-5-methyl-3-pyridyl)-2-[5-methyl-2-(3-methyl-1,2-benzothiazol-5-yl)-1-piperidyl]-2-oxo-acetamide A mixture of 2-[(6-amino-5-methyl-3-pyridyl)amino]-2-oxo-acetic acid (59 mg, 0.302 mmol), 3-methyl-5-(5-methyl-2-piperidyl)-1,2-benzothiazole (75.0 mg, 0.304 mmol) and DMF (2 mL) were added HATU (118 mg, 0.310 mmol) and DIPEA (117 mg, 0.903 mmol), then the mixture was stirred at 20° C. for 12 hours. The resulting mixture was quenched by addition of water (10 mL) and extracted with EtOAc (10 mL*3). The combined organic layer was washed with saturated NH₄Cl aqueous solution (10 mL*2), brine (10 mL), dried over anhydrous Na₂SO₄, filtered and concentrated under reduced pressure to give a crude product which was purified by flash chromatography (ISCO®; 12 g AgelaFlash® Silica Flash Column, EtOAc/MeOH with MeOH from 0-5%, Flow Rate: 30 mL/min, 254 nm) to afford N-(6-amino-5-methyl-3-pyridyl)-2-[5-methyl-2-(3-methyl-1,2-benzothiazol-5-yl)-1-piperidyl]-2-oxo-acetamide (52 mg, 40.6% yield) as yellow oil. LCMS (ESI) [M+H]⁺ m/z: calcd 424.1, found 424.1.

Step 7: Synthesis of N-(6-amino-5-methyl-3-pyridyl)-2-[(2R,5S)-5-methyl-2-(3-methyl-1,2-benzothiazol-5-yl)-1-piperidyl]-2-oxo-Acetamid (Compound 1166) and N-(6-amino-5-methyl-3-pyridyl)-2-[(2S,5R)-5-methyl-2-(3-methyl-1,2-benzothiazol-5-yl)-1-piperidyl]-2-oxo-Acetamid (Ent-Compound 1166

N-(6-amino-5-methyl-3-pyridyl)-2-[5-methyl-2-(3-methyl-1,2-benzothiazol-5-yl)-1-piperidyl]-2-oxo-acetamide (50 mg, 0.118 mmol) was purified by chiral SFC (Instrument: Thar800Q; Daicel Chiralpak IG (250 mm*30 mm, 10 m); Mobile phase: supercritical CO₂/EtOH (0.1% NH₃—H₂O, v %)=60/40; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give Compound 1166 and ent-Compound 1166.

Compound 1166: N-(6-amino-5-methyl-3-pyridyl)-2-[(2R,5S)-5-methyl-2-(3-methyl-1,2-benzothiazol-5-yl)-1-piperidyl]-2-oxo-acetamide (16 mg, single unknown enantiomer with trans relative chemistry, peak 3, retention time=4.341 min, white solid), ¹H NMR (400 MHz, DMSO-d₆) δ ppm 10.26 (br s, 1H), 8.12 (d, J=8.5 Hz, 1H), 8.02 (br s, 1H), 7.97 (s, 1H), 7.59 (br d, J=8.5 Hz, 1H), 7.47 (br s, 1H), 5.62 (br s, 1H), 5.34 (br s, 2H), 3.55-3.87 (m, 1H), 3.05-3.09 (m, 1H), 2.66-2.75 (m, 3H), 2.16-2.35 (m, 2H), 2.01-2.08 (m, 3H), 1.96 (br d, J=11.3 Hz, 1H), 1.75-1.87 (m, 1H), 1.34-1.43 (m, 1H), 1.08 (d, J=7.0 Hz, 3H); LCMS (ESI) [M+H]⁺ m/z: calcd 424.1, found 424.1; HPLC: 1000% @220 nm, 1000% @254 nm; 100% ee. ent-Compound 1166: N-(6-amino-5-methyl-3-pyridyl)-2-[(2S,5R)-5-methyl-2-(3-methyl-1,2-benzothiazol-5-yl)-1-piperidyl]-2-oxo-acetamide (16 mg, single unknown enantiomer with trans relative chemistry, peak 4, retention time=5.604 min, white solid), ¹H NMR (400 MHz, DMSO-d₆) δ ppm 10.26 (br s, 1H), 8.12 (d, J=8.5 Hz, 1H), 8.02 (br s, 1H), 7.97 (s, 1H), 7.59 (br d, J=8.5 Hz, 1H), 7.47 (br s, 1H), 5.62 (br s, 1H), 5.34 (br s, 2H), 3.55-3.87 (m, 1H), 3.05-3.09 (m, 1H), 2.66-2.75 (m, 3H), 2.16-2.35 (m, 2H), 2.01-2.08 (m, 3H), 1.96 (br d, J=11.3 Hz, 1H), 1.75-1.87 (m, 1H), 1.34-1.43 (m, 1H), 1.08 (d, J=7.0 Hz, 3H); LCMS(ESI) [M+H]+m/z: calcd 424.1, found 424.1; HPLC: 1000% @220 nm, 1000% @254 nm; 100% ee.

Example 233. The Synthesis of N-(6-amino-5-cyclopropyl-3-pyridyl)-2-[(2R,5S)-2-(1,3-benzothiazol-5-yl)-5-methyl-1-piperidyl]-2-oxo-acetamide (Compound 1319)

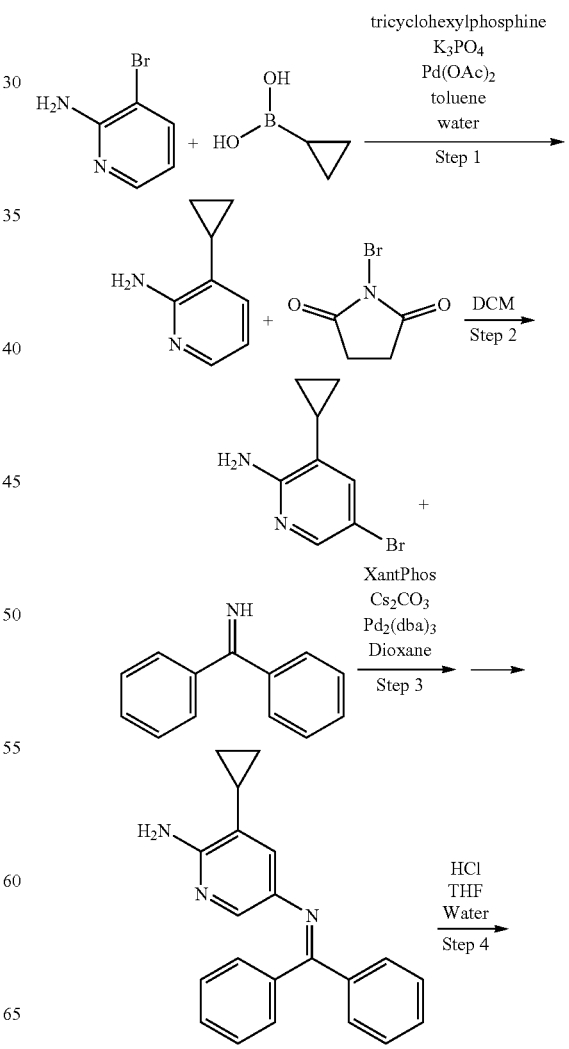

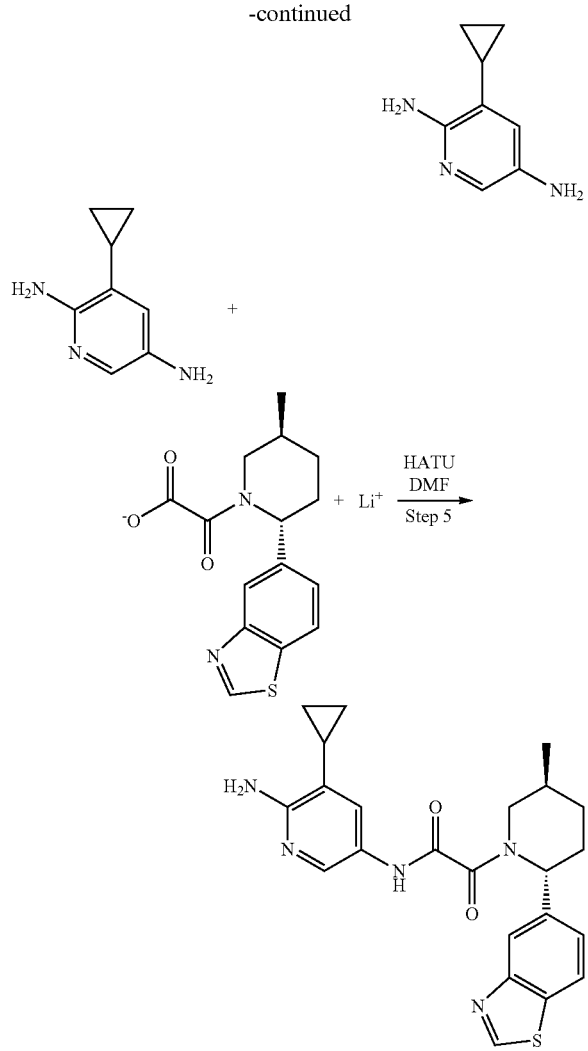

Step 1: The Synthesis of 3-cyclopropylpyridin-2-amine

To a solution of 3-bromopyridin-2-amine (50.0 g, 289 mmol) in toluene (500 mL) and water (100 mL) Cyclopropyl boronic acid (32.3 g, 376 mmol), tricyclohexylphosphine (8.10 g, 28.9 mmol), Potassium phosphate tribasic anhydrous (184 g, 867 mmol) and Palladium (II) acetate (3.24 g, 14.5 mmol) were added. The reaction mixture was evacuated and then backfilled with Ar. The reaction mixture was stirred at 90° C. for 16 hr. The obtained mixture was concentrated in vacuo. The resulting mass was diluted with water and extracted with MTBE (3×500 mL). The combined organic layers were dried over sodium sulfate and concentrated to dryness in vacuo to afford 3-cyclopropylpyridin-2-amine (59.0 g, crude) as brown oil.

LCMS(ESI): [M+H]$^+$ m/z: calcd 135.1; found 135.2; Rt=0.609.

Step 2: The Synthesis of 5-bromo-3-cyclopropyl-pyridin-2-amine

NBS (50.9 g, 286 mmol, 24.2 mL) was added portionwise to a solution of 3-cyclopropylpyridin-2-amine (59.0 g, 286 mmol) in dry DCM. The reaction mixture was stirred at r.t. for 3 hr. The obtained mixture was washed with water. The aqueous layer was extracted with dichloromethane. The combined organic extracts were washed with brine and dried over Na$_2$SO$_4$. The solvent was removed under reduced pressure. The residue was purified by CC (Interchim; 800 g SiO$_2$, chloroform/acetonitrile with acetonitrile from 0-40%, flow rate=150 mL/min, Rv=5-6 CV) to afford 5-bromo-3-cyclopropyl-pyridin-2-amine (30.4 g, 143 mmol, 49.9% yield) as a brown solid.

LCMS(ESI): [M+H]$^+$ m/z: calcd 213.01 and 215.01; found 215.0; Rt=0.834.

Step 3: The Synthesis of 5-(Benzhydrylideneamino)-3-cyclopropyl-pyridin-2-amine A mixture of 5-bromo-3-cyclopropyl-pyridin-2-amine (15.0 g, 70.4 mmol), diphenylmethanimine (14.0 g, 77.4 mmol, 12.9 mL), Cesium carbonate (68.8 g, 211 mmol), XantPhos (2.04 g, 3.52 mmol) and Pd$_2$(dba)$_3$ (1.61 g, 1.76 mmol) in dioxane (250 mL) was evacuated and then backfilled with Ar. The reaction mixture was stirred at 90° C. for 12 hr under Ar atmosphere. The reaction mixture was cooled to room temperature, diluted with MTBE (250 mL), and filtered. The filtrate was concentrated in vacuo to afford 5-(benzhydrylideneamino)-3-cyclopropyl-pyridin-2-amine (27.3 g, crude) as brown gum.

1H NMR (400 MHz, CDCl$_3$) δ 0.26-0.27 (m, 2H), 0.75-0.76 (m, 2H), 1.46-1.47 (m, 1H), 4.52 (br, 2H), 6.62 (m, 1H), 7.08 (m, 2H), 7.29-7.41 (m, 6H), 7.53 (m, 1H), 7.69 (m, 2H).

Step 4: The Synthesis of 3-cyclopropylpyridine-2,5-Diamine

Hydrochloric acid, 36% w/w aq. soln. (4.50 g, 123 mmol, 5.63 mL) was added to a solution of 5-(benzhydrylideneamino)-3-cyclopropyl-pyridin-2-amine (15.0 g, 35.9 mmol) in THF (150 mL) and water (100 mL). The resulting mixture was stirred at 21° C. for 18 hr. The obtained mixture was diluted with water (20.0 mL) and extracted with MTBE (2×25.0 mL). The organic layers were collected and discarded. The aqueous layer was basified to pH≈10-11 with solid K$_2$CO$_3$ and extracted with DCM (4×25.0 mL). The combined organic layers were dried over K$_2$CO$_3$ and concentrated under reduced pressure to afford 3-cyclopropylpyridine-2,5-diamine (5.30 g, crude) as a red oil.

LCMS(ESI): [M+H]$^+$ m/z: calcd 150.11; found 150.2; Rt=0.323.

Step 5: The Synthesis of N-(6-amino-5-cyclopropyl-3-pyridyl)-2-[(2R,5S)-2-(1,3-benzothiazol-5-yl)-5-methyl-1-piperidyl]-2-oxo-acetamide (Compound 1319

3-cyclopropylpyridine-2,5-diamine (1.15 g, 2.31 mmol) and HATU (923 mg, 2.43 mmol) were mixed in dry DMF (10.0 mL) at rt. The resulting mixture was stirred for 15 min. lithium; 2-[(2R,5S)-2-(1,3-benzothiazol-5-yl)-5-methyl-1-piperidyl]-2-oxo-acetate (718 mg, 2.31 mmol) was added thereto and stirring was continued at rt overnight. The obtained mixture was poured into water and extracted 3 times with EtOAc. The combined organic layers were washed with water, brine and concentrated in vacuo. The residue was subjected to HPLC (0.5-6.5 min 30-65% water—ACN; flow: 30 mL/min, column: Waters SunFire C18, 100×19 mm, 5 μm). The obtained mass (236.5 mg) was purified by chiral column (Chiral ART (250*20, 5 mkm), Hexane-IPA-MeOH, 50-25-25, 12 ml/min, RT=34.231 min)

to afford N-(6-amino-5-cyclopropyl-3-pyridyl)-2-[(2R,5S)-2-(1,3-benzothiazol-5-yl)-5-methyl-1-piperidyl]-2-oxo-acetamide (168 mg, 385 μmol, 16.7% yield) as a brown solid.

RT=58.171 min (Chiralpak IC (250*4.6, 5 mkm), Hexane-IPA-MeOH, 50-25-25, 0.6 mL/min)

1H NMR (600 MHz, DMSO-$d_6$) δ 0.40-0.47 (m, 2H), 0.83-0.89 (m, 2H), 1.00-1.04 (m, 3H), 1.32-1.40 (m, 2H), 1.60-1.90 (m, 2H), 2.05-2.37 (m, 2H), 3.50 (d, 1H), 4.05 (d, 1H), 5.30-5.77 (m, 3H), 7.28-7.50 (m, 2H), 7.99-8.06 (m, 2H), 8.15-8.18 (m, 1H), 9.39 (m, 1H), 10.55 (m, 1H)

LCMS(ESI): [M+H]$^+$ m/z: calcd 436.2; found 436.2; Rt=2.536.

Example 234. The Synthesis of Rel-N-(6-amino-5-cyclopropyl-3-pyridyl)-2-[(2S,5R)-5-methyl-2-(2-methyl-1,3-benzothiazol-5-yl)-1-piperidyl]-2-oxo-acetamide (Ent-Compound 1313) and Rel-N-(6-amino-5-cyclopropyl-3-pyridyl)-2-[(2R,5S)-5-methyl-2-(2-methyl-1,3-benzothiazol-5-yl)-1-piperidyl]-2-oxo-acetamide (Compound 1313

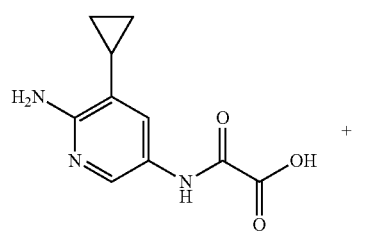

+

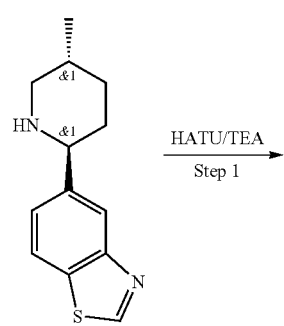

HATU/TEA
Step 1

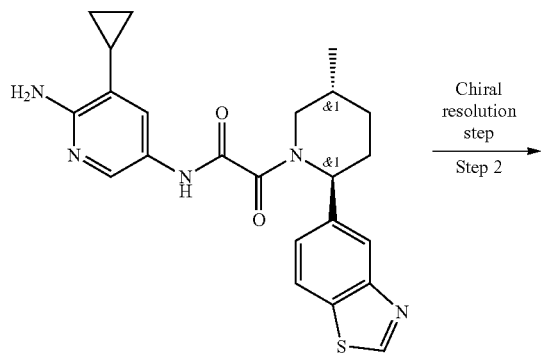

Chiral resolution step
Step 2

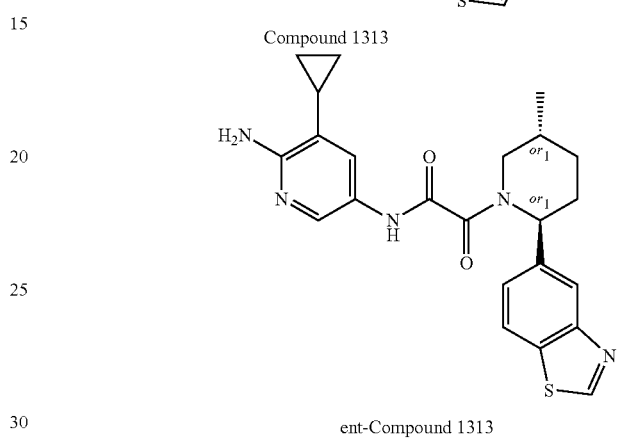

Compound 1313 ent-Compound 1313

Step 1: N-(6-amino-5-cyclopropyl-3-pyridyl)-2-[5-methyl-2-(2-methyl-1,3-benzothiazol-5-yl)-1-piperidyl]-2-oxo-acetamide Lithium salt of 2-[(6-amino-5-cyclopropyl-3-pyridyl)amino]-2-oxo-acetate (2.10 g, 3.25 mmol) and HATU (1.36 g, 3.57 mmol) were mixed in dry DMF (25 mL) at rt and the resulting mixture was stirred for 15 min. 2-methyl-5-(5-methyl-2-piperidyl)-1,3-benzothiazole (0.8 g, 3.25 mmol) was added thereto and the resulting mixture was stirred at rt for 2 hr. The resulting mixture was subjected to HPLC (40-65 0.5-6.5 min water-acn; flow 30 ml/min (loading pump 4 ml/min acn); column SunFire 100×19 mm 5 um (R)). N-(6-amino-5-cyclopropyl-3-pyridyl)-2-[5-methyl-2-(2-methyl-1,3-benzothiazol-5-yl)-1-piperidyl]-2-oxo-acetamide (0.3398 g, 755.84 umol, 23.28% yield) was obtained as a beige solid with 13% of cis-impurity.

LCMS(ESI): [M+1]$^+$ m/z: calcd 449.2; found 450.2; Rt=2.663 min.

Step 2: The Synthesis of Rel-N-(6-amino-5-cyclopropyl-3-pyridyl)-2-[(2S,5R)-5-methyl-2-(2-methyl-1,3-benzothiazol-5-yl)-1-piperidyl]-2-oxo-acetamide (Ent-Compound 1313) and Rel-N-(6-amino-5-cyclopropyl-3-pyridyl)-2-[(2R,5S)-5-methyl-2-(2-methyl-, 3-benzothiazol-5-yl)-1-piperidyl]-2-oxo-acetamide (Compound 1313

The mixture of diastereomers was separated by chiral chromatography (irs run: Chiralpak IC—III (250*20, 5 mkm), IPA-MeOH, 50-50, 10 ml/min and then 2nd run: Chiralcel OD-H (250*20, 5 mkm), Hexane-IPA-MeOH, 60-20-20, 12 ml/min) to obtain N-(6-amino-5-cyclopropyl-3-pyridyl)-2-[(2R,5S)-5-methyl-2-(2-methyl-1,3-benzothiazol-5-yl)-1-piperidyl]-2-oxo-acetamide (117.08 mg, 260.43 umol, 34.46% yield) and N-(6-amino-5-cyclopropyl-3-pyridyl)-2-[(2S,5R)-5-methyl-2-(2-methyl-1,3-benzothiazol-5-yl)-1-piperidyl]-2-oxo-acetamide (110.18 mg, 245.08 umol, 32.42% yield)

Analytical:
 RT for Compound 1313 (Chiralpak IC (250*4.6, 5 mkm), IPA-MeOH, 50-50, 0.6 ml/min)—26.667 min;
 RT for ent-Compound 1313 (Chiralpak IC (250*4.6, 5 mkm), IPA-MeOH, 50-50, 0.5 ml/min)—16.52 min.

Preparative:
 Install run (separation of P1 from the mixture of P2 and its cis-impurity):
 RT for Compound 1313 (Chiralpak IC—III(250*20, 5 mkm), IPA-MeOH, 50-50, 10 ml/min)–34.014 min;
 RT for ent-Compound 1313 (with cis-impurity) (Chiralpak IC—III(250*20, 5 mkm), IPA-MeOH, 50-50, 10 ml/min)–19.557 min.

Preparative, second run (separation of P2 from cis-impurity)
 RT for ent-Compound 1313 (Chiralcel OD-H (250*20, 5 mkm), Hexane-IPA-MeOH, 60-20-20, 12 ml/min) =17.823 min.

Compound 1313:
 $^1$H NMR (600 MHz, dmso) δ 0.40-0.47 (m, 2H), 0.83-0.89 (m, 2H), 1.00-1.04 (m, 3H), 1.22-1.39 (m, 2H), 1.61-1.89 (m, 2H), 2.05-2.36 (m, 2H), 2.78 (s, 3H), 3.48 (d, 1H), 4.03 (d, 1H), 5.28-5.76 (m, 3H), 7.28-7.40 (m, 2H), 7.83-7.86 (m, 1H), 7.99-8.06 (m, 2H), 10.54 (m, 1H). LCMS (ESI): [M+1]$^+$ m/z: calcd 263.1; found 264.2; Rt=2.800 min.
 LCMS(ESI): [M+1]$^+$ m/z: calcd 449.2; found 450.2; Rt=2.551 min.

Ent-Compound 1313:
 $^1$H NMR (600 MHz, dmso) δ 0.40-0.47 (m, 2H), 0.83-0.89 (m, 2H), 1.00-1.04 (m, 3H), 1.22-1.38 (m, 2H), 1.60-1.89 (m, 2H), 2.05-2.36 (m, 2H), 2.78 (s, 3H), 3.48 (d, 1H), 4.03 (d, 1H), 5.28-5.76 (m, 3H), 7.28-7.39 (m, 2H), 7.83-7.86 (m, 1H), 7.99-8.06 (m, 2H), 10.54 (m, 1H).
 LCMS(ESI): [M+1]$^+$ m/z: calcd 449.2; found 450.2; Rt=2.527 min.

Example 235. The Synthesis of N-(6-amino-5-cyclopropyl-3-pyridyl)-2-[(2S,5R)-2-(1H-indazol-5-yl)-5-methyl-1-piperidyl]-2-oxo-acetamide (Compound 1361) and N-(6-amino-5-cyclopropyl-3-pyridyl)-2-[(2R,5S)-2-(1H-indazol-5-yl)-5-methyl-1-piperidyl]-2-oxo-acetamide (Compound 1251

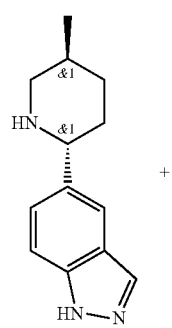

+

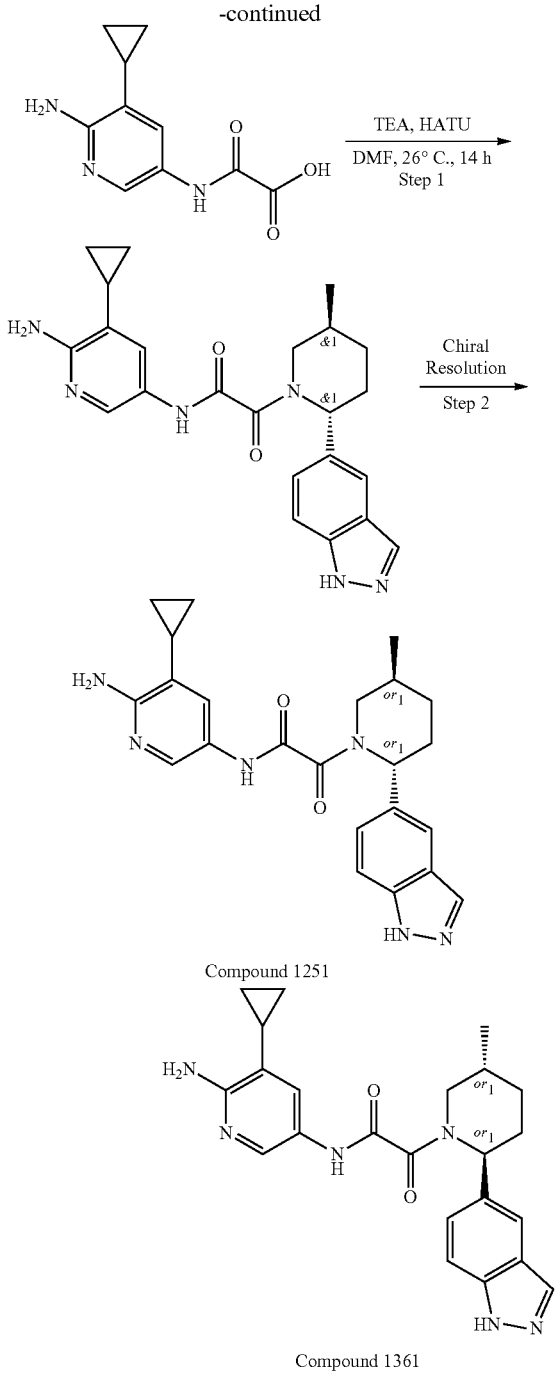

Compound 1251

Compound 1361

Step 1: The Synthesis of N-(6-amino-5-cyclopropyl-3-pyridyl)-2-[2-(1H-indazol-5-yl)-5-methyl-1-piperidyl]-2-oxo-acetamide 5-(5-methyl-2-piperidyl)-1H-indazole (0.1 g, 464.48 umol), HATU (229.59 mg, 603.83 umol) were mixed in dry DMF (5 mL) at 21° C. and the resulting mixture was stirred for 15 min. sodium; 2-[(6-amino-5-cyclopropyl-3-pyridyl)amino]-2-oxo-acetate (225.92 mg, 464.48 umol) was added thereto and the resulting mixture was stirred at 21° C. overnight. The resulting mixture was subjected to HPLC (30-55 0.5-6.5 min water-acn; flow 30 ml/min (loading pump 5 ml/min acn); column SunFire 100×19 mm 5 um (R)). N-(6-amino-5-cyclopropyl-3-pyridyl)-2-[2-(1H-indazol-5-yl)-5-methyl-1-piperidyl]-2-oxo-acetamide (57.1 mg, 136.44 umol, 29.38% yield) was obtained as a yellowish solid.

LCMS(ESI): [M+H]+ m/z: calcd 418.2; found 419.4; Rt=2.211 min.

Step 2: Example 236. The Synthesis of N-(6-amino-5-cyclopropyl-3-pyridyl)-2-[(2S,5R)-2-(1H-indazol-5-yl)-5-methyl-1-piperidyl]-2-oxo-acetamide (Compound 1361) and N-(6-amino-5-cyclopropyl-3-pyridyl)-2-[(2R,5S)-2-(1H-indazol-5-yl)-5-methyl-1-piperidyl]-2-oxo-acetamide (Compound 1251

The mixture of diastereomers was separated by chiral chromatography (Column: Chiralpak IC—III(250*20 mm, 5 mkm); Mobile phase: IPA-MeOH 50-50 Flow Rate: 10 mL/min) to obtain N-(6-amino-5-cyclopropyl-3-pyridyl)-2-[(2S,5R)-2-(1H-indazol-5-yl)-5-methyl-1-piperidyl]-2-oxo-acetamide Compound 1361 (21.4 mg, 51.14 umol, 37.48% yield, has 5.4% of cis impurity) and N-(6-amino-5-cyclopropyl-3-pyridyl)-2-[(2R,5S)-2-(1H-indazol-5-yl)-5-methyl-1-piperidyl]-2-oxo-acetamide Compound 1251 (20.41 mg, 48.77 umol, 35.74% yield)
Analytical:
RT for Compound 1361 (Chiralpak IC (250*4.6, 5 mkm), IPA-MeOH, 50-50, 0.5 ml/min)–11.4912 min;
RT for Compound 1251 (Chiralpak IC (250*4.6, 5 mkm), IPA-MeOH, 50-50, 0.5 ml/min)–24.8342 min.
Preparative:
RT for Compound 1361 (Chiralpak IC—III(250*20, 5 mkm), IPA-MeOH, 50-50, 10 ml/min)–12.466 min;
RT for Compound 1251 (Chiralpak IC—III(250*20, 5 mkm), IPA-MeOH, 50-50, 10 ml/min)–25.178 min.
Compound 1361:
$^1$H NMR (DMSO-$d_6$, 600 MHz): δ (ppm) 0.44 (m, 2H), 0.87 (m, 2H), 1.02 (m, 3H), 1.33 (m, 1H), 1.76 (m, 3H), 2.19 (m, 2H), 2.76 (m, 1H), 3.74 (m, 1H), 5.72 (m, 3H), 7.27 (d, 1H), 7.36 (m, 1H), 7.53 (m, 1H), 7.69 (m, 1H), 8.03 (m, 2H), 10.50 (s, 1H), 13.00 (s, 1H).
LCMS(ESI): [M+H]+ m/z: calcd 418.2; found 419.2; Rt=1.843 min.
Compound 1251:
$^1$H NMR (DMSO-$d_6$, 600 MHz): δ (ppm) 0.44 (m, 2H), 0.87 (m, 2H), 1.01 (m, 3H), 1.35 (m, 1H), 1.76 (m, 3H), 2.19 (m, 2H), 2.76 (m, 1H), 3.74 (dd, 1H), 5.72 (m, 3H), 7.27 (m, 1H), 7.37 (m, 1H), 7.53 (m, 1H), 7.69 (m, 1H), 8.03 (m, 2H), 10.49 (s, 1H).
LCMS(ESI): [M+H]+ m/z: calcd 418.2; found 419.2; Rt=1.838 min.

Example 236. Library Synthesis of Bicyclic Piperidine Compounds

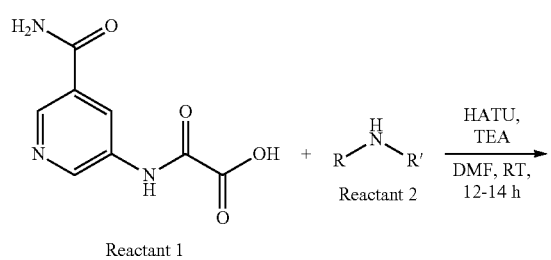

Reactant 1

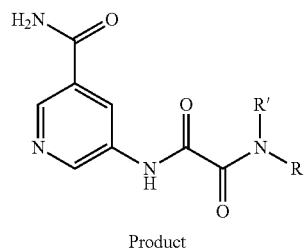

Product

DIPEA (3.5 equiv) was added to the solution of 2-((5-carbamoylpyridin-3-yl)amino)-2-oxoacetic acid (1.1 equiv; Reactant 1) and corresponding amine (1.0 equiv; Reactant 2) in DMF (2.0 mL). The resulting mixture was stirred for 5 min followed by the addition of the solution of HATU (1.2 equiv) in DMF (1.0 mL). The reaction mixture was stirred at room temperature overnight. After all starting material was consumed, as was shown by LCMS, the resulting mixture was concentrated under reduced pressure. The residue was subjected to HPLC (C18 column and MeOH-H$_2$O+ 0.1% NH$_3$ as a mobile phase, RunTime 5 min) to afford pure product.

The Synthesis of 5-[2-(1-benzyl-Decahydro-1,6-naphthyridin-6-yl)-2-oxoacetamido]pyridine-3-carboxamide (Compound 412

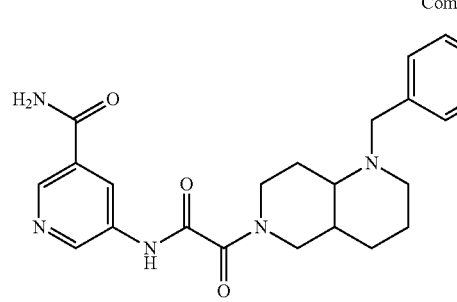

Compound 412

Yield: 31.0 mg, 43.44%
$^1$H NMR (500 MHz, DMSO) δ 1.34-1.49 (m, 2H), 1.50-1.65 (m, 3H), 1.88-2.09 (m, 2H), 2.16-2.34 (m, 1H), 2.44-2.47 (m, 1H), 2.68-2.99 (m, 2H), 3.04-3.16 (m, 1H), 3.48-3.57 (m, 1H), 3.59-3.83 (m, 2H), 3.98-4.15 (m, 1H), 7.20-7.27 (m, 1H), 7.27-7.35 (m, 4H), 7.62 (s, 1H), 8.18 (s, 1H), 8.47-8.55 (m, 1H), 8.75-8.80 (m, 1H), 8.85-8.92 (m, 1H), 11.11 (s, 1H).
LCMS(ESI): [M+H]+ m/z: calcd 421.2; found 422.2; Rt=0.759 min.

The Synthesis of 5-[2-(4a-hydroxy-Decahydroisoquinolin-2-yl)-2-oxoacetamido]pyridine-3-carboxamide (Compound 421

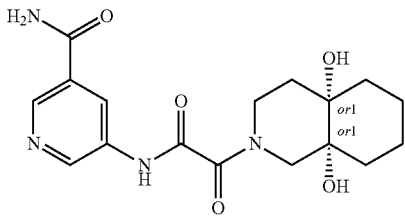

Compound 421

Yield: 21.8 mg, 30.16%
¹H NMR (500 MHz, DMSO) δ 1.16-1.29 (m, 3H), 1.30-1.51 (m, 4H), 1.53-1.64 (m, 4H), 1.83-1.99 (m, 1H), 3.12-3.27 (m, 1H), 3.55-3.69 (m, 1H), 3.77-4.11 (m, 1H), 4.48-4.55 (m, 1H), 7.62 (s, 1H), 8.17 (s, 1H), 8.47-8.54 (m, 1H), 8.74-8.80 (m, 1H), 8.87 (dd, 1H), 11.08 (s, 1H).
LCMS(ESI): [M+H]⁺ m/z: calcd 346.2; found 347.2; Rt=2.126 min.

The Synthesis of 5-[2-(6-hydroxy-Decahydroisoquinolin-2-yl)-2-oxoacetamido]pyridine-3-carboxamide (Compound 418

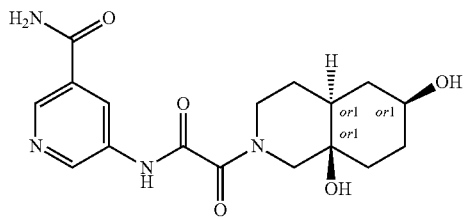

Compound 418

Yield: 5.4 mg, 8.35%
LCMS(ESI): [M+H]⁺ m/z: calcd 346.2; found 347.2; Rt=1.765 min.

The Synthesis of 5-{2-[6-(Carbamoylmethyl)-Decahydroisoquinolin-2-yl]-2-oxoacetamido}pyridine-3-carboxamide (Compound 420

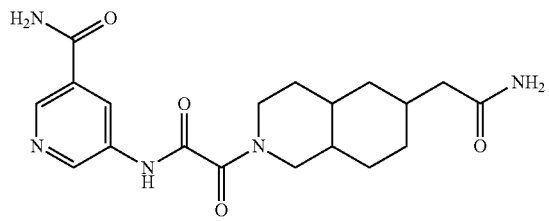

Compound 420

Yield: 19.9 mg, 28.46%
¹H NMR (500 MHz, DMSO) δ 0.87-1.02 (m, 1H), 1.17-1.31 (m, 1H), 1.33-1.56 (m, 4H), 1.60-1.84 (m, 3H), 1.86-1.95 (m, 1H), 1.96-2.02 (m, 1H), 2.07-2.26 (m, 1H), 2.68-2.97 (m, 2H), 3.09-3.26 (m, 1H), 3.59-4.00 (m, 1H), 4.11-4.48 (m, 1H), 6.70 (s, 1H), 7.11-7.30 (m, 1H), 7.62 (s, 1H), 8.17 (s, 1H), 8.44-8.57 (m, 1H), 8.73-8.81 (m, 1H), 8.84-9.14 (m, 1H), 11.10 (br s, 1H).
LCMS(ESI): [M+H]⁺ m/z: calcd 387.2; found 388.2; Rt=2.023 min.

The Synthesis of rac-5-{2-[(R,5S)-3-oxaspiro[bicyclo[3.1.0]hexane-2,3'-piperidine]-]1'-yl]-2-oxoacetamido}pyridine-3-carboxamide (Compound 124

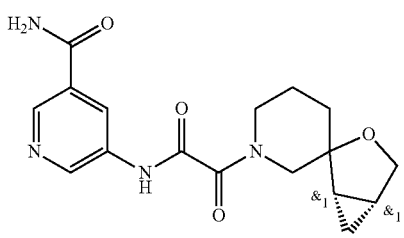

Compound 124

Prepared by general procedure. Yield: 16.0 mg, 32.0%
¹H NMR (500 MHz, CDCl₃) δ0.52 (m, 2H), 1.42 (m, 1H), 1.80 (m, 4H), 3.05 (m, 1H), 3.40 (m, 1H), 3.75 (m, 3H), 4.10 (m, 1H), 4.43 (m, 1H), 5.96 (m, 2H), 8.62 (m, 1H), 8.86 (m, 2H), 9.41 (m, 1H).
LCMS(ESI): [M+H]⁺ m/z: calcd 344.2; found 345.4; Rt=2.275 min.

The Synthesis of 5-(2-{Decahydro-1H-cyclohepta[c]pyridin-2-yl}-2-oxoacetamido)pyridine-3-carboxamide (Compound 133

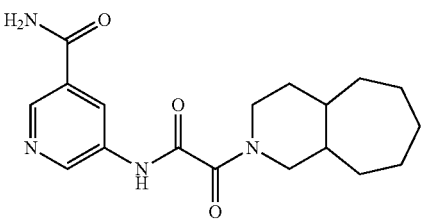

Compound 133

Prepared by general procedure. Yield: 18.1 mg, 51.71%
¹H NMR (500 MHz, DMSO-d₆) δ 1.27 (m, 5H), 1.52 (m, 3H), 1.64 (m, 4H), 1.76 (m, 1H), 1.83 (m, 1H), 1.92 (m, 1H), 3.18 (m, 1H), 3.49 (m, 1H), 3.64 (m, 1H), 7.61 (s, 1H), 8.16 (s, 1H), 8.50 (m, 1H), 8.77 (m, 1H), 8.86 (m, 1H), 10.77 (m, 1H).
LCMS(ESI): [M+H]⁺ m/z: calcd 344.2; found 345.1; Rt=1.161 min.

The Synthesis of 5-[2-(5-cyclopentyl-2-methylpiperidin-1-yl)-2-oxoacetamido]pyridine-3-carboxamide (Compound 143

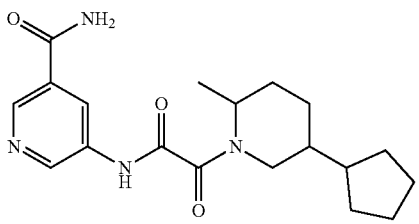

Compound 143

Prepared by general procedure. Yield: 18.0 mg, 51.43%
$^1$H NMR (500 MHz, DMSO-d$_6$) δ 0.97 (m, 2H), 1.23 (m, 3H), 1.35 (m, 2H), 1.44 (m, 2H), 1.56 (m, 3H), 1.71 (m, 2H), 1.88 (m, 3H), 3.01 (m, 0.5H), 3.45 (m, 1H), 4.23 (m, 1.5H), 7.61 (s, 1H), 8.17 (s, 1H), 8.49 (s, 1H), 8.77 (m, 1H), 8.87 (m, 1H), 10.80 (m, 1H).
LCMS(ESI): [M+H]$^+$ m/z: calcd 358.2; found 359.1; Rt=1.214 min.

The Synthesis of 5-(2-{3-oxaspiro[bicyclo[3.1.0] hexane-2,4'-piperidine]-1'-yl}-2-oxoacetamido)pyridine-3-carboxamide (Compound 149

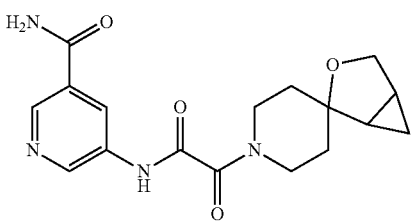

Compound 149

Prepared by general procedure. Yield: 16.0 mg, 45.71%
$^1$H NMR (DMSO-d$_6$, 600 MHz): δ (ppm) 0.27 (m, 1H), 0.45 (m, 1H), 1.54 (m, 3H), 1.63 (m, 3H), 3.20 (m, 1H), 3.35 (m, 1H), 3.59 (m, 1H), 3.68 (m, 2H), 3.90 (m, 1H), 7.59 (s, 1H), 8.15 (s, 1H), 8.47 (s, 1H), 8.75 (m, 1H), 8.85 (m, 1H).
LCMS(ESI): [M+H]$^+$ m/z: calcd 344.2; found 345.1; Rt=0.916 min.

The Synthesis of 5-[2-(2-methyl-Decahydroquinolin-1-yl)-2-oxoacetamido]pyridine-3-carboxamide (Compound 144

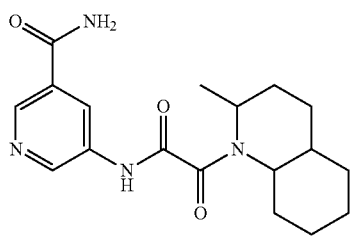

Compound 144

Prepared by general procedure. Yield: 3.4 mg, 9.71%
$^1$H NMR (Chloroform-d, 600 MHz): δ (ppm) 1.33 (m, 6H), 1.48 (m, 1H), 1.66 (m, 2H), 1.73 (m, 2H), 1.89 (m, 3H), 2.01 (m, 3H), 4.53 (m, 1H), 4.75 (m, 1H), 6.25 (s, 1H), 6.86 (s, 1H), 8.78 (s, 1H), 8.98 (s, 1H), 9.11 (s, 1H), 10.02 (s, 1H).
LCMS(ESI): [M+H]$^+$ m/z: calcd 344.2; found 345.1; Rt=1.141 min.

The Synthesis of 5-{2-[2-(2-hydroxycyclopentyl) piperidin-1-yl]-2-oxoacetamido}pyridine-3-carboxamide (Compound 169

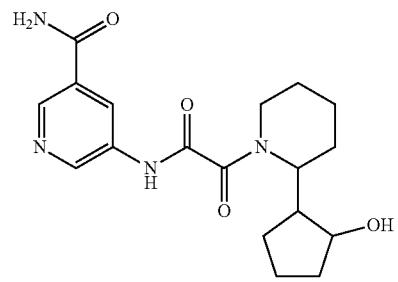

Compound 169

Prepared by general procedure. Yield: 6.1 mg, 17.43%
$^1$H NMR (Chloroform-d, 500 MHz): δ (ppm) 1.31 (m, 1H), 1.73 (m, 8H), 2.05 (m, 2H), 2.42 (m, 1H), 3.01 (m, 1H), 4.03 (m, 1H), 4.52 (m, 1H), 5.06 (m, 1H), 8.63 (s, 1H), 8.83 (m, 1H), 8.89 (m, 1H), 9.47 (m, 1H).
LCMS(ESI): [M+H]$^+$ m/z: calcd 360.2; found 361.2; Rt=0.830 min.

The Synthesis of 5-(2-oxo-2-{9-thia-2-azaspiro[5.5] undecan-2-yl}acetamido)pyridine-3-carboxamide (Compound 166

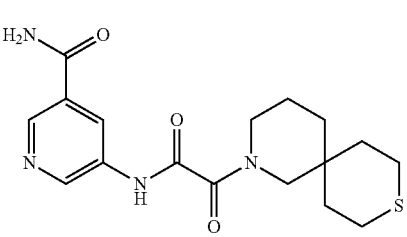

Compound 166

Prepared by general procedure. Yield: 10.2 mg, 29.14%
$^1$H NMR (DMSO-d$_6$, 500 MHz): δ (ppm) 1.53 (m, 6H), 2.43 (m, 2H), 2.66 (m, 2H), 3.28 (m, 2H), 3.43 (m, 4H), 7.62 (m, 1H), 8.17 (m, 1H), 8.49 (s, 1H), 8.77 (s, 1H), 8.88 (m, 1H), 10.47 (s, 1H)
LCMS(ESI): [M+H]$^+$ m/z: calcd 362.2; found 363.1; Rt=1.002 min.

The Synthesis of 5-[2-(5,5-dimethyl-decahydroiso-quinolin-2-yl)-2-oxoacetamido]pyridine-3-carboxamide (Compound 141

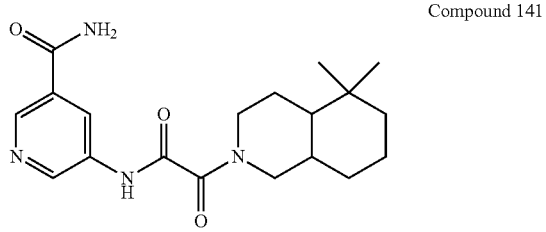 [SMILES: CC1(C)CCCC2CN(C(=O)C(=O)Nc3cncc(C(N)=O)c3)CCC21]

Compound 141

Prepared by general procedure. Yield: 14.5 mg, 41.43%

$^1$H NMR (500 MHz, DMSO-$d_6$) δ 0.84 (m, 6H), 1.01 (m, 2H), 1.21 (m, 2H), 1.37 (m, 1H), 1.46 (m, 3H), 1.69 (m, 1H), 2.31 (m, 1H), 2.87 (m, 2H), 3.77 (m, 1H), 4.34 (m, 1H), 7.61 (s, 1H), 8.16 (s, 1H), 8.49 (m, 1H), 8.77 (s, 1H), 8.86 (s, 1H), 10.70 (m, 1H).

LCMS(ESI): [M+H]$^+$ m/z: calcd 358.2; found 359.2; Rt=1.289 min.

Example 237. Library Synthesis of Spiro Piperidine Compounds

General Procedure:

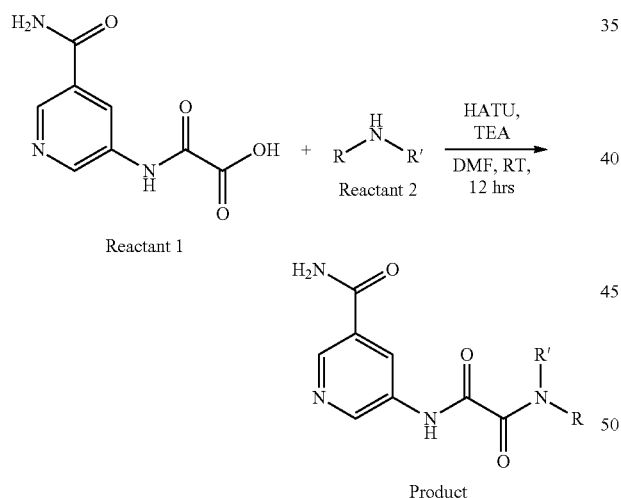

TEA (10.0 equiv) was added to a solution of 2-((5-carbamoylpyridin-3-yl)amino)-2-oxoacetic acid (1.1 equiv; Reactant 1), corresponding amine (1.0 equiv; Reactant 2), and HATU (1.1 equiv) in DMF (3 mL). The reaction mixture was stirred at 25° C. for 12 hr, then submitted to reverse phase HPLC (column: YMC-Triart C18 100×20 mm 5 um, mobile phase: 0-20% 0-5 min 0.1% NH$_3$-methanol) to afford crude product. The obtained solid was re-purified by reverse phase HPLC (column: SunFire C18 100×19 mm 5 um, mobile phase: 0-25% 0-5 min water+methanol+formic acid) to afford the target product.

The Synthesis of 5-[[2-(3-oxa-9-azaspiro[5.5]undecan-9-yl)-2-oxo-acetyl]amino]pyridine-3-carboxamide (Compound 191

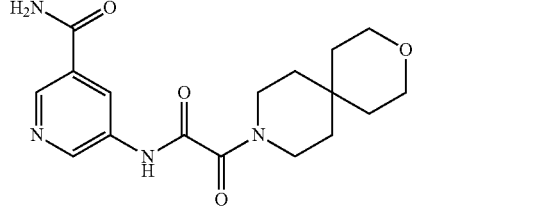

Compound 191

Prepared by General Procedure. Yield: 28.0 mg (12.55%)

$^1$H NMR (CD$_3$OD, 400 MHz): δ (ppm) 1.58 (m, 4H), 1.65 (m, 4H), 3.67 (m, 8H), 8.07 (s, 1H), 8.58 (m, 1H), 8.77 (d, 1H), 8.93 (d, 1H)

LCMS(ESI): [M+H]$^+$ m/z: calcd 346.2; found 347.2; Rt=2.062 min.

The Synthesis of 5-(2-(3,3-Dioxido-3-thia-9-azaspiro[5.5]undecan-9-yl)-2-oxoacetamido)Nicotinamide (Compound 195

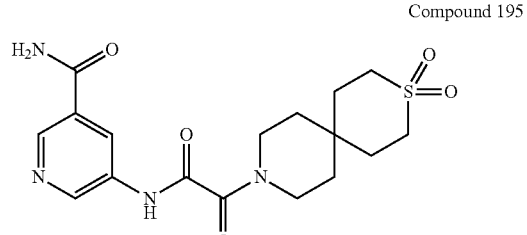

Compound 195

Prepared by General Procedure. Yield: 44.0 mg (26.75%)

$^1$H NMR (dmso, 600 MHz): δ (ppm) 1.53 (m, 4H), 1.89 (m, 4H), 3.02 (m, 4H), 3.43 (m, 2H), 3.50 (m, 2H), 7.59 (s, 1H), 8.15 (s, 1H), 8.47 (s, 1H), 8.75 (s, 1H), 8.85 (s, 1H), 11.11 (s, 1H).

LCMS(ESI): [M+H]$^+$ m/z: calcd 394.2; found 395.2; Rt=1.565 min.

The Synthesis of 5-[[2-(3-azaspiro[5.5]undecan-3-yl)-2-oxo-acetyl]amino]pyridine-3-carboxamide (Compound 203

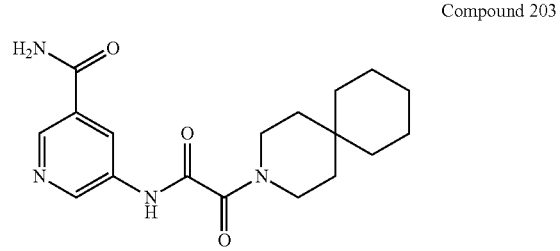 [SMILES: NC(=O)c1cncc(NC(=O)C(=O)N2CCC3(CCCCC3)CC2)c1]

Compound 203

1689
Prepared by General Procedure. Yield: 53.0 mg (29.20%)
$^1$H NMR (400 MHz, DMSO-$d_6$) δ 1.39 (m, 15H), 3.43 (m, 4H), 7.64 (s, 1H), 8.49 (s, 1H), 8.78 (s, 1H), 8.86 (s, 1H), 11.12 (s, 1H).
LCMS(ESI): [M+H]$^+$ m/z: calcd 344.2; found 345.2; Rt=3.186 min.
Example 238. The Synthesis of N-(6-amino-5-methyl-3-pyridyl)-2-[(2R,5S)-5-methyl-2-[2-(1-methyl-4-piperidyl)-1,3-benzothiazol-5-yl]-1-piperidyl]-2-oxo-acetamide (Compound 1314) and N-(6-amino-5-methyl-3-pyridyl)-2-[(2R,5S)-5-methyl-2-[2-(1-methyl-4-piperidyl)-1,3-benzothiazol-5-yl]-1-piperidyl]-2-oxo-acetamide (Compound 1293
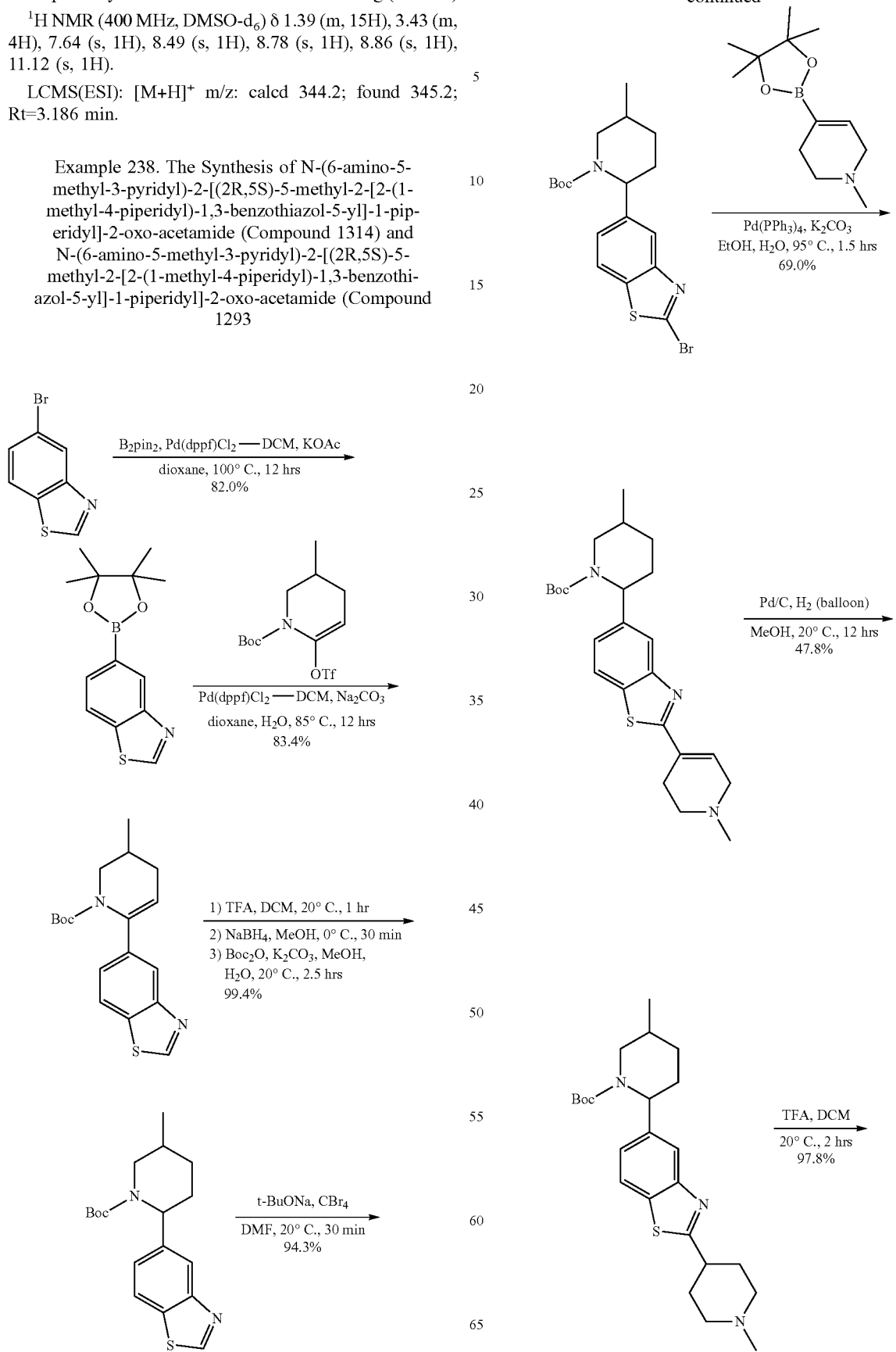

1691

-continued

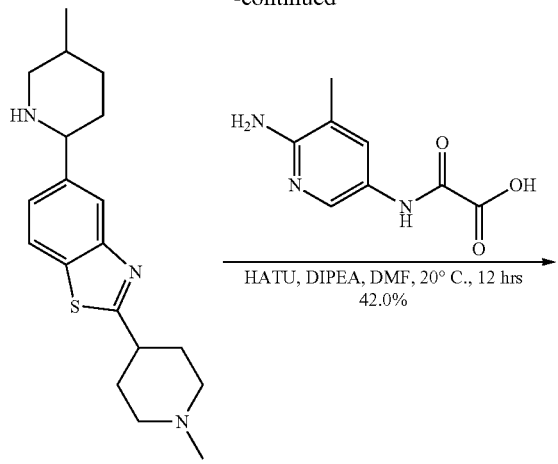

1692

-continued

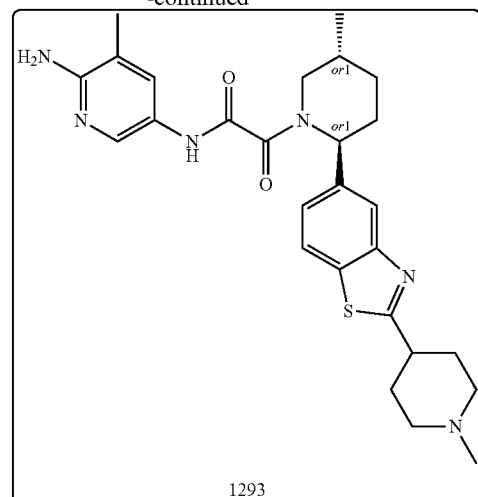

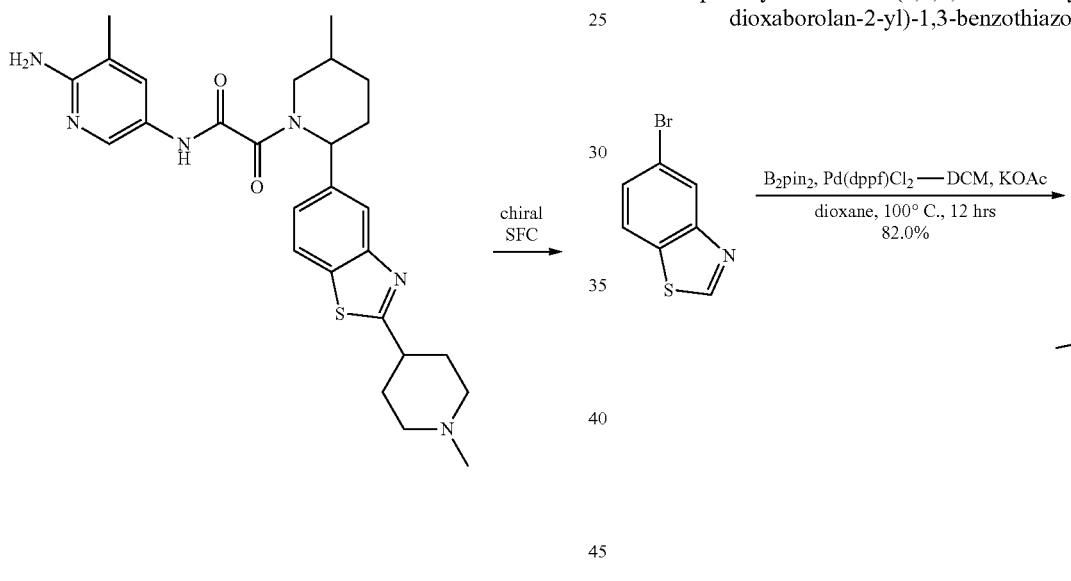

Step 1: Synthesis of 5-(4,4,5,5-tetramethyl-1,3,2-dioxaborolan-2-yl)-1,3-benzothiazole

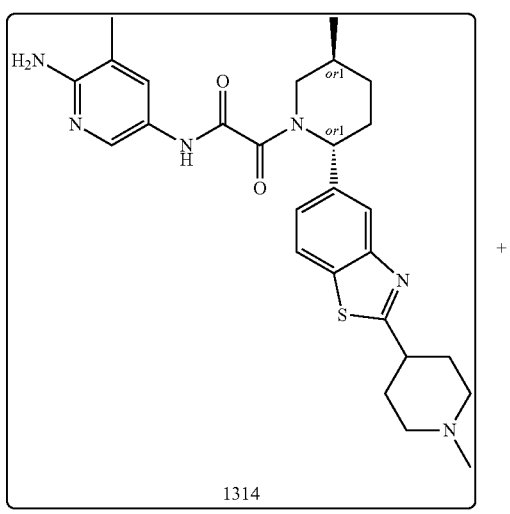

A mixture of 5-bromo-1,3-benzothiazole (500 mg, 2.34 mmol), KOAc (1.32 g, 4.67 mmol), 4,4,5,5-tetramethyl-2-(4,4,5,5-tetramethyl-1,3,2-dioxaborolan-2-yl)-1,3,2-dioxaborolane (900 mg, 3.54 mmol), cyclopentyl(diphenyl)phosphane; dichloropalladium; iron (171 mg, 0.234 mmol) and dioxane (10 mL) was stirred at 100° C. for 12 hours. The resulting mixture was quenched by addition of water (100 mL) and extracted with EtOAc (100 mL*3). The combined organic layer was washed with saturated $NH_4Cl$ aqueous solution (100 mL*2), brine (100 mL), dried over anhydrous $Na_2SO_4$, filtered and concentrated under reduced pressure to give a residue which was purified by flash chromatography (ISCO®; 24 g AgelaFlash® Silica Flash Column, petroleum ether/EtOAc with EtOAc from 0~40%, Flow Rate: 30 mL/min, 254 nm) to afford 5-(4,4,5,5-tetramethyl-1,3,2-dioxaborolan-2-yl)-1,3-benzothiazole (500 mg, 82.0% yield) as yellow solid.

Step 2: Synthesis of tert-butyl 6-(1,3-benzothiazol-5-yl)-3-methyl-3,4-dihydro-2H-pyridine-1-carboxylate

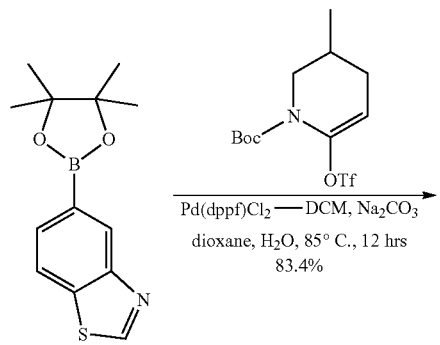

A mixture of 5-(4,4,5,5-tetramethyl-1,3,2-dioxaborolan-2-yl)-1,3-benzothiazole (500 mg, 1.91 mmol), tert-butyl 3-methyl-6-(trifluoromethylsulfonyloxy)-3,4-dihydro-2H-pyridine-1-carboxylate (800 mg, 2.32 mmol), $Na_2CO_3$ (660 mg, 6.23 mmol), Pd(dppf)$Cl_2$-DCM (160 mg, 0.196 mmol), dioxane (10 mL) and $H_2O$ (3 mL) was stirred at 85° C. for 12 hours. The resulting mixture was quenched by addition of water (100 mL) and extracted with EtOAc (100 mL*3). The combined organic layer was washed with saturated $NH_4Cl$ aqueous solution (100 mL*2), brine (100 mL), dried over anhydrous $Na_2SO_4$, filtered and concentrated under reduced pressure to give a residue which was purified by flash chromatography (ISCO®; 24 g AgelaFlash® Silica Flash Column, petroleum ether/EtOAc with EtOAc from 0~20%, Flow Rate: 30 mL/min, 254 nm) to afford tert-butyl 6-(1,3-benzothiazol-5-yl)-3-methyl-3,4-dihydro-2H-pyridine-1-carboxylate (528 mg, 83.4% yield) as yellow oil.

Step 3: Synthesis of tert-butyl 2-(1,3-benzothiazol-5-yl)-5-methyl-piperidine-1-carboxylate

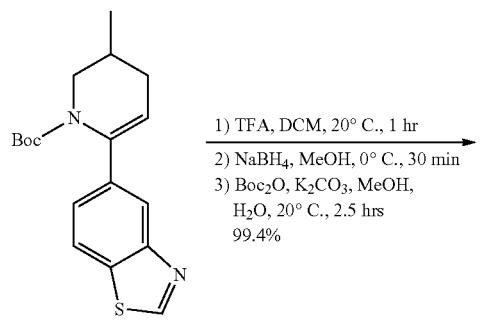

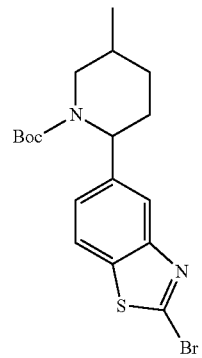

A mixture of tert-butyl 6-(1,3-benzothiazol-5-yl)-3-methyl-3,4-dihydro-2H-pyridine-1-carboxylate (300 mg, 0.908 mmol), TFA (2.5 mL, 32.4 mmol) and DCM (2 mL) was stirred at 20° C. for 1 hour. Then the mixture was concentrated under reduced pressure and the residue was dissolved in MeOH (5 mL), followed by addition of $NaBH_4$ (120 mg, 3.17 mmol). The mixture was stirred at 0° C. for 30 minutes. $Boc_2O$ (500 mg, 2.29 mmol), $K_2CO_3$ (400 mg, 2.89 mmol) and $H_2O$ (2 mL) were added and the mixture was stirred at 20° C. for 2.5 hours. The resulting mixture was quenched by addition of water (50 mL) and extracted with EtOAc (50 mL*3). The combined organic layer was washed with saturated $NH_4Cl$ aqueous solution (10 mL*2), brine (10 mL), dried over anhydrous $Na_2SO_4$, filtered and concentrated under reduced pressure. The residue was purified by flash chromatography (ISCO®; 24 g AgelaFlash® Silica Flash Column, petroleum ether/EtOAc with EtOAc from 0~20%, Flow Rate: 30 mL/min, 254 nm) to afford tert-butyl 2-(1,3-benzothiazol-5-yl)-5-methyl-piperidine-1-carboxylate (300 mg, 99.4% yield) as yellow oil.

Step 4: Synthesis of tert-butyl 2-(2-bromo-1,3-benzothiazol-5-yl)-5-methyl-piperidine-1-carboxylate

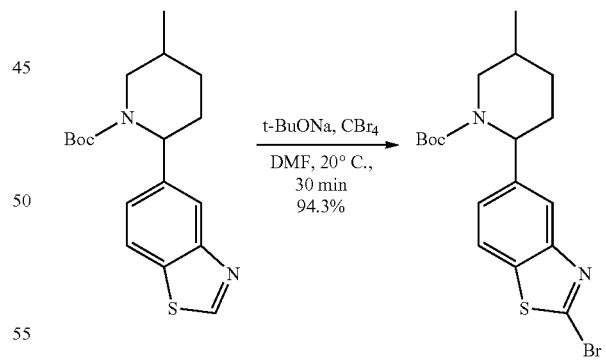

To a mixture of tert-butyl 2-(1,3-benzothiazol-5-yl)-5-methyl-piperidine-1-carboxylate (300 mg, 0.902 mol), sodium; 2-methylpropan-2-olate (350 mg, 3.64 mmol) and DMF (1 mL) was added $CBr_4$ (333 mg, 1.00 mmol) and the mixture was stirred at 20° C. for 30 minutes. The resulting mixture was quenched by addition of water (10 mL) and extracted with EtOAc (30 mL*3). The combined organic layer was washed with saturated $NH_4Cl$ aqueous solution (10 mL*2), brine (10 mL), dried over anhydrous $Na_2SO_4$, filtered and concentrated under reduced pressure to give tert-butyl 2-(2-bromo-1,3-benzothiazol-5-yl)-5-methyl-piperidine-1-carboxylate (350 mg, 94.3% yield) as yellow oil.

Step 5: Synthesis of tert-butyl 3-methyl-6-[2-(1-methyl-3,6-dihydro-2H-pyridin-4-yl)-1,3-benzothiazol-5-yl]-3,4-dihydro-2H-pyridine-1-carboxylate anhydrous Na$_2$SO$_4$, filtered and concentrated under reduced pressure to give a residue which was purified by flash chromatography (ISCO®; 12 g A gelaFlash® Silica Flash Column, DCM/MeOH with MeOH from 0~20%, Flow Rate: 30 mL/min, 254 nm) to afford tert-butyl 3-methyl-6-[2-(1-methyl-3,6-dihydro-2H-pyridin-4-yl)-1,3-benzothiazol-5-yl]-3,4-dihydro-2H-pyridine-1-carboxylate (250 mg, 69.0% yield) as yellow solid.

Step 6: Synthesis of tert-butyl 5-methyl-2-[2-(1-methyl-4-piperidyl)-1,3-benzothiazol-5-yl]piperidine-1-carboxylate

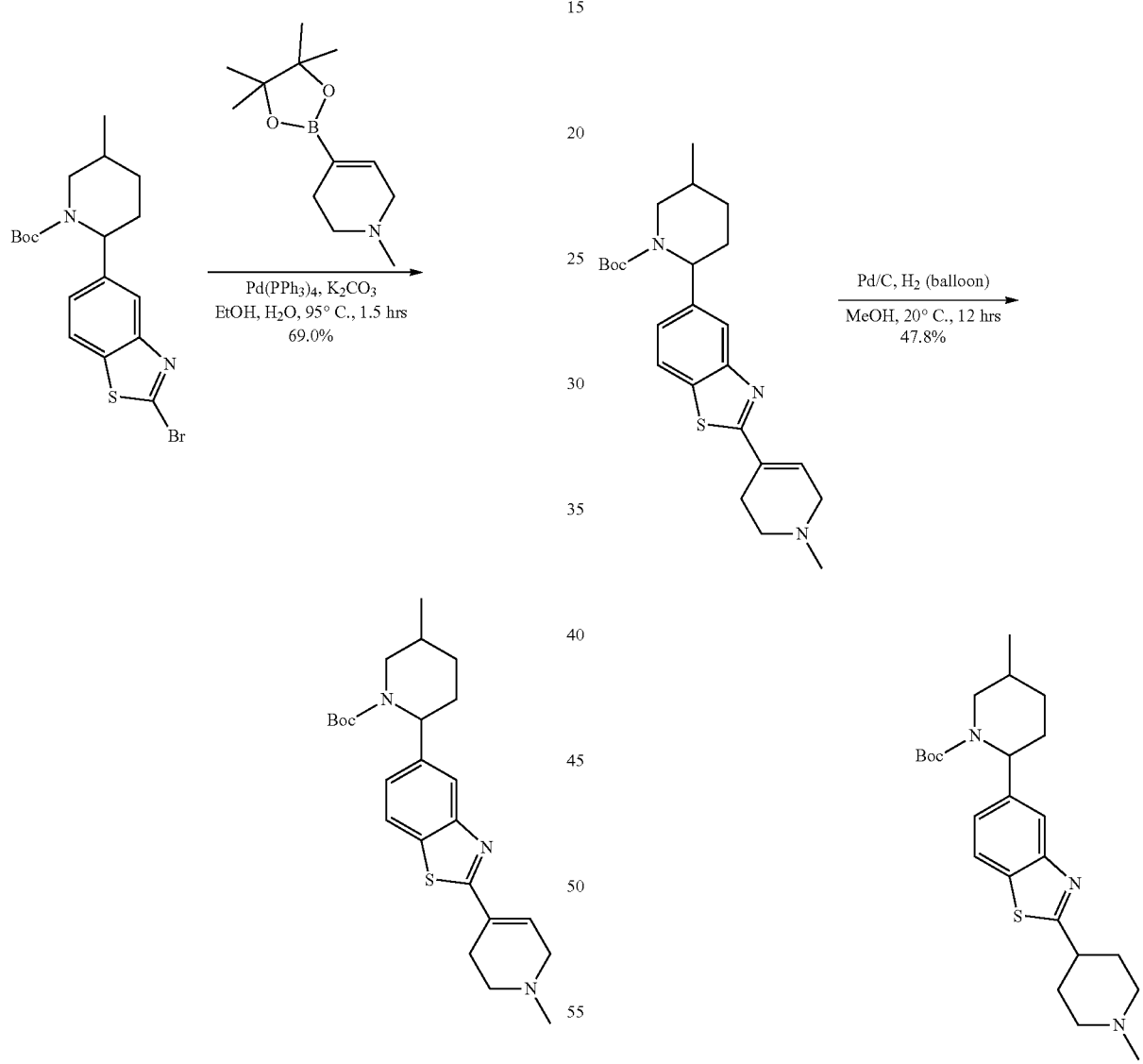

A mixture of tert-butyl 2-(2-bromo-1,3-benzothiazol-5-yl)-5-methyl-piperidine-1-carboxylate (350 mg, 0.851 mmol), 1-methyl-1,2,3,6-tetrahydropyridine-4-boronicacidpinacolester (280 mg, 1.25 mmol), Pd(PPh$_3$)$_4$ (105 mg, 90.9 umol), K$_2$CO$_3$ (364.00 mg, 2.63 mmol), H$_2$O (3 mL) and EtOH (10 mL) was stirred at 95° C. for 1.5 hours under microwave. The resulting mixture was quenched by addition of water (10 mL) and extracted with EtOAc (50 mL*3). The combined organic layer was washed with saturated NH$_4$Cl aqueous solution (10 mL*2), brine (10 mL), dried over A mixture of tert-butyl 5-methyl-2-[2-(1-methyl-3,6-dihydro-2H-pyridin-4-yl)-1,3-benzothiazol-5-yl]piperidine-1-carboxylate (250 mg, 0.585 mmol), Pd/C (170 mg, 10 wt % of Pd with 50 wt % of water) in MeOH (5 mL) was stirred at 20° C. for 12 hours under hydrogen (in balloon, 15 psi). The mixture was filtered and concentrated under reduced pressure to give tert-butyl 5-methyl-2-[2-(1-methyl-4-piperidyl)-1,3-benzothiazol-5-yl]piperidine-1-carboxylate (120 mg, 47.8% yield) as yellow oil

Step 7: Synthesis of 2-(1-methyl-4-piperidyl)-5-(5-methyl-2-piperidyl)-1,3-benzothiazole

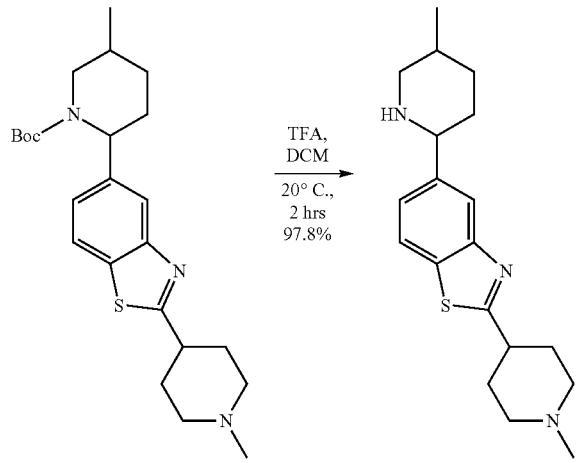 [SMILES: CC1CCC(c2ccc3sc(C4CCN(C)CC4)nc3c2)N(C(=O)OC(C)(C)C)C1 ; CC1CCC(c2ccc3sc(C4CCN(C)CC4)nc3c2)NC1]

A mixture of tert-butyl 5-methyl-2-[2-(1-methyl-4-piperidyl)-1,3-benzothiazol-5-yl]piperidine-1-carboxylate (120 mg, 0.279 mmol), TFA (1 mL, 13.0 mmol) and DCM (2 mL) was stirred 20° C. for 2 hours. The mixture was concentrated under reduced pressure to give a residue which was dissolved in MeOH (~5 mL) and neutralized by $Na_2CO_3$ solid to pH=7. The mixture was concentrated under reduced pressure to give a residue which was triturated with DCM (50 mL). The mixture was filtered and the filtrate was concentrated under reduced pressure to give 2-(1-methyl-4-piperidyl)-5-(5-methyl-2-piperidyl)-1,3-benzothiazole (90 mg, 97.8% yield) as yellow oil

Step 8: Synthesis of N-(6-amino-5-methyl-3-pyridyl)-2-[5-methyl-2-[2-(1-methyl-4-piperidyl)-1,3-benzothiazol-5-yl]-1-piperidyl]-2-oxo-acetamide

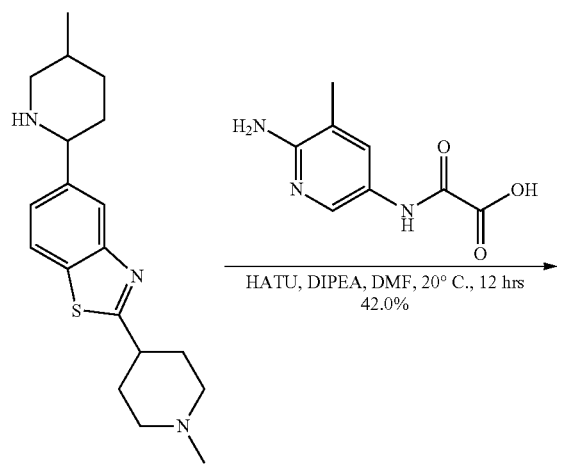

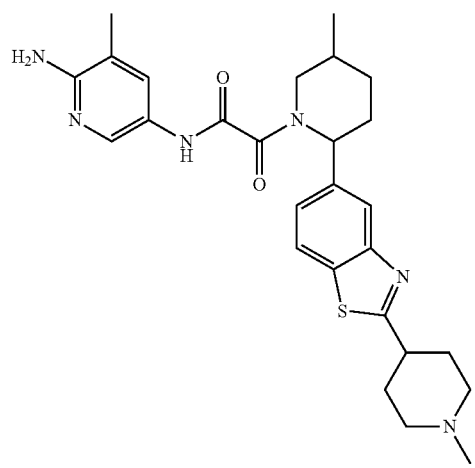

A mixture of 2-[(6-amino-5-methyl-3-pyridyl)amino]-2-oxo-acetic acid (55 mg, 0.22 mmol), 2-(1-methyl-4-piperidyl)-5-(5-methyl-2-piperidyl)-1,3-benzothiazole (90 mg, 0.273 mmol), HATU (104 mg, 0.274 mmol) and DMF (5 mL) was added DIPEA (0.3 mL, 1.72 mmol) and the mixture was stirred at 20° C. for 12 hours. The mixture was purified by flash chromatography (Column: SepaFlash® Spherical C18, 25 g, 40-60 m, 120 Å; MeCN/water (0.5 v % $NH_3$—$H_2O$) with MeCN from 0-45%, 25 mL/min, 254 nm) to give N-(6-amino-5-methyl-3-pyridyl)-2-[5-methyl-2-[2-(1-methyl-4-piperidyl)-1,3-benzothiazol-5-yl]-1-piperidyl]-2-oxo-acetamide (60 mg, 42.0% yield) as yellow oil.

Step 9: Synthesis of N-(6-amino-5-methyl-3-pyridyl)-2-[(2R,5S)-5-methyl-2-[2-(1-methyl-4-piperidyl)-1,3-benzothiazol-5-yl]-1-piperidyl]-2-oxo-acetamide (Compound 1314) and N-(6-amino-5-methyl-3-pyridyl)-2-[(2R,5S)-5-methyl-2-[2-(1-methyl-4-piperidyl)-1,3-benzothiazol-5-yl]-1-piperidyl]-2-oxo-acetamide (Compound 1293

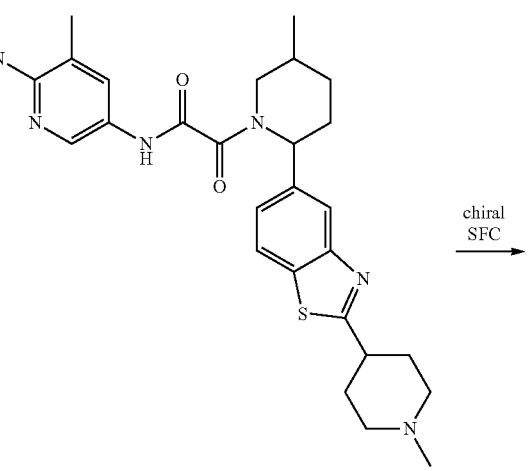

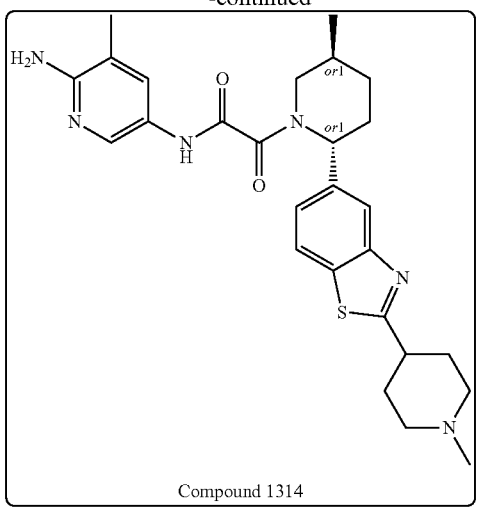

Compound 1314

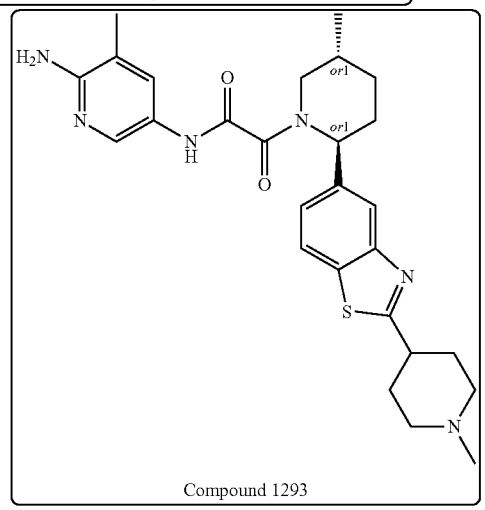

Compound 1293

N-(6-amino-5-methyl-3-pyridyl)-2-[5-methyl-2-[2-(1-methyl-4-piperidyl)-1,3-benzothiazol-5-yl]-1-piperidyl]-2-oxo-acetamide (45 mg, 88.8 μmol) was separated by chiral SFC separation (Instrument: Thar800Q; Column: Daicel Chiralpak IG (250 mm*30 mm, 10 m); Mobile phase: supercritical $CO_2$/EtOH (0.1% $NH_3$—$H_2O$, v %)=50/50; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give Compound 1314 (peak 2, retention time=1.610 min) and Compound 1293 (peak 3, retention time=2.469 min).

Compound 1314: N-(6-amino-5-methyl-3-pyridyl)-2-[(2R,5S)-5-methyl-2-[2-(1-methyl-4-piperidyl)-1,3-benzothiazol-5-yl]-1-piperidyl]-2-oxo-acetamide (15 mg, single unknown enantiomer with trans relative chemistry, peak 2, retention time=1.610 min, white solid). $^1$H NMR (400 MHz, DMSO-$d_6$) δ ppm 10.30 (br s, 1H), 8.03 (br d, J=8.3 Hz, 2H), 7.90 (s, 1H), 7.50 (br s, 1H), 7.40 (br d, J=8.0 Hz, 1H), 5.60 (br s, 1H), 5.37 (br s, 2H), 3.71 (br s, 1H), 2.89 (br d, J=11.8 Hz, 2H), 2.23-2.34 (m, 5H), 2.08-2.20 (m, 6H), 2.06 (s, 3H), 1.84-1.96 (m, 3H), 1.71-1.83 (m, 1H), 1.38 (br d, J=7.5 Hz, 1H), 1.07 (d, J=7.0 Hz, 3H); LCMS (ESI) [M+H]$^+$ m/z: calcd 507.2, found 507.2; HPLC: 1000% @220 nm, 1000% @254 nm; 100% ee Compound 1293: N-(6-amino-5-methyl-3-pyridyl)-2-[(2R,5S)-5-methyl-2-[2-(1-methyl-4-piperidyl)-1,3-benzothiazol-5-yl]-1-piperidyl]-2-oxo-acetamide (15 mg, single unknown enantiomer with trans relative chemistry, peak 3, retention time=2.469 min, white solid). $^1$H NMR (400 MHz, DMSO-$d_6$) δ ppm 10.31 (br s, 1H), 8.04 (br d, J=8.3 Hz, 2H), 7.90 (s, 1H), 7.50 (br s, 1H), 7.41 (br d, J=8.3 Hz, 1H), 5.60 (br s, 1H), 5.37 (br s, 2H), 3.70-3.90 (m, 1H), 2.60 (br t, J=11.0 Hz, 4H), 2.09-2.35 (m, 8H), 2.06 (br s, 3H), 1.90-2.02 (m, 4H), 1.71-1.83 (m, 1H), 1.37 (br d, J=11.3 Hz, 1H), 1.07 (d, J=7.0 Hz, 3H); LCMS (ESI) [M+H]$^+$ m/z: calcd 507.2, found 507.2; HPLC: 100% @220 nm, 100% @254 nm; 100% ee.

Example 239. The Synthesis of 5-(2-(2-(2-(2-(dimethylamino)ethyl)benzo[d]thiazol-5-yl)-5-methylpiperidin-1-yl)-2-oxoacetamido)-2-methoxynicotinamide (Compound 1281, Compound 1281 and Compound 1197

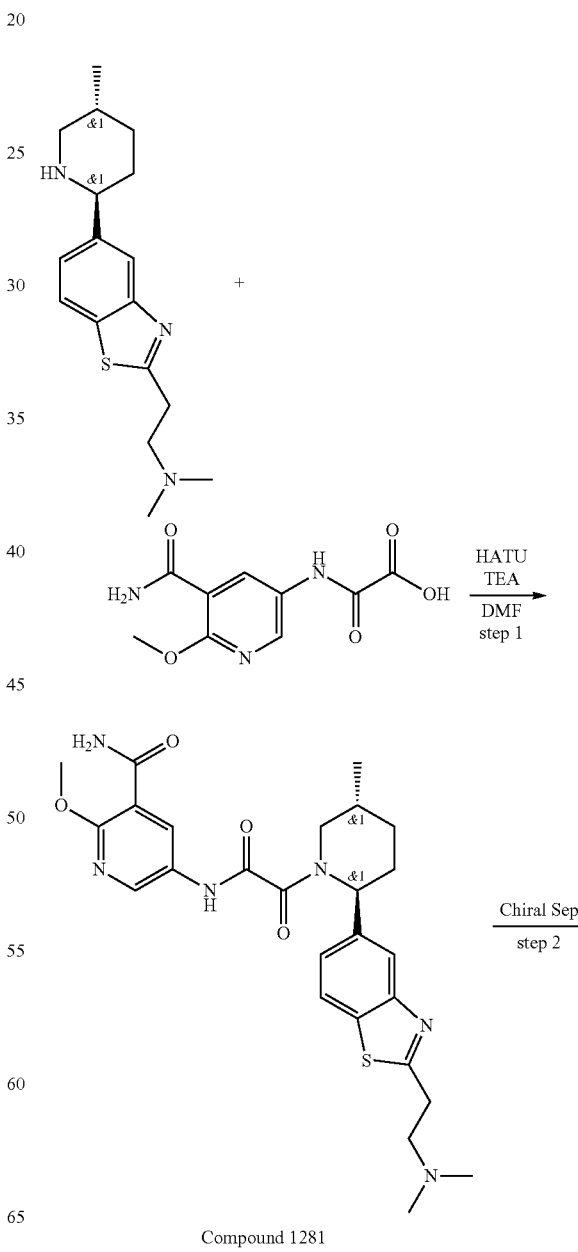

Compound 1281

1701

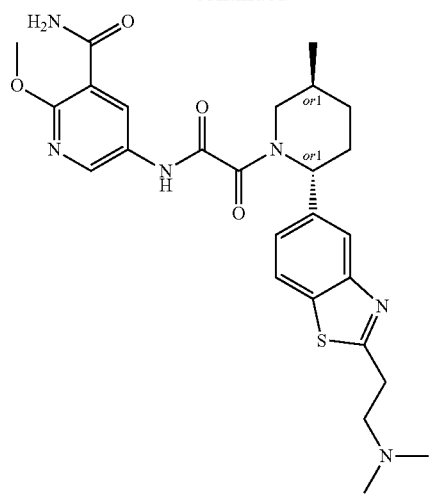

Compound 1197

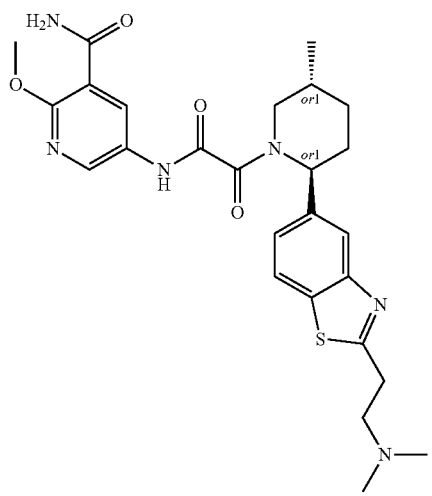

Compound 1197

Step 1: Synthesis of 5-(2-(2-(2-(2-(dimethylamino)ethyl)benzo[d]thiazol-d Yl)-5-methylpiperidin-1-yl)-2-oxoacetamido)-2-methoxynicotinamide (Compound 128

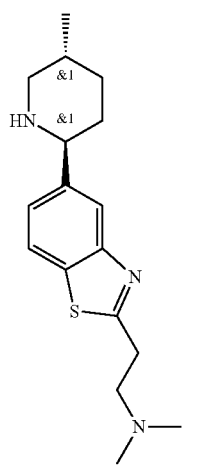

+

1702

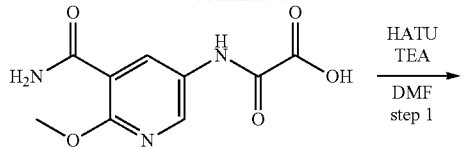

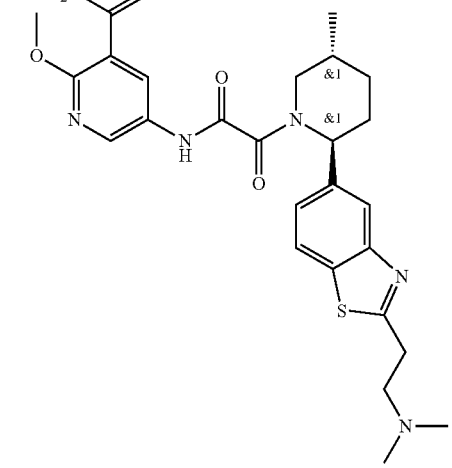

Prepared by general procedure 2. Yield: 19.8 mg (5.730%).

HPLC conditions: Column: YMC Triart C18 100*20 mm, 5 microM; 0-5 min 40-90% water-MeOH+0.100 NH$_4$OH, flow: 30 ml/min; (loading pump 4 ml/min MeOH).

$^1$H NMR (600 MHz, DMSO-d$_6$) δ (ppm) 1.02-1.06 (m, 3H), 1.35 (m, 1H), 1.70 (m, 1H), 1.90 (m, 1H), 2.09 (m, 2H), 2.20 (s, 6H), 2.29 (m, 2H), 2.69 (m, 2H), 3.22 (m, 2H), 3.91-3.96 (m, 3H), 5.71 (m, 1H), 7.35 (m, 1H), 7.65-7.74 (m, 2H), 7.85 (m, 1H), 7.98-8.05 (m, 1H), 8.40-8.57 (m, 2H), 11.10 (m, 1H).

LCMS(ESI): [M]$^+$ m/z: calcd 524.2; found 525.2; Rt=2.151 min.

Step 2: Chiral Separation (Compound 1281 and Compound 1197

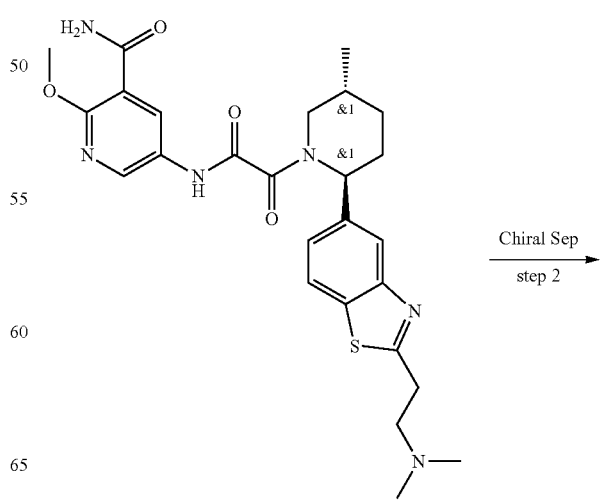

-continued

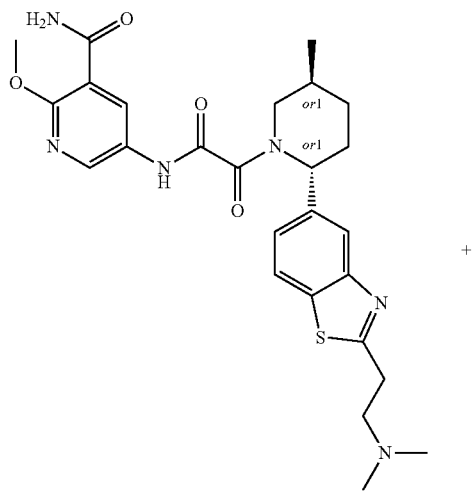

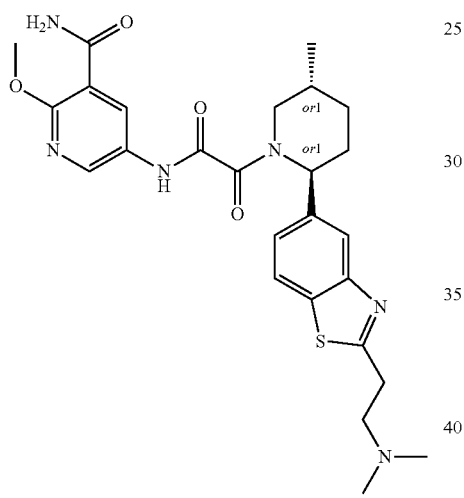

Racemic 5-(2-(2-(2-(2-(dimethylamino)ethyl)benzo[d]thiazol-5-yl)-5-methylpiperidin-1-yl)-2-oxoacetamido)-2-methoxynicotinamide (290 mg, 552.77 umol) was chiral separated (Column: Chirapak IC—III (250*20 mm, 5 mkm), IPA-MeOH, 50-50, 12 ml/min) to obtain 5-[[2-[(2R,5S)-2-[2-[2-(dimethylamino)ethyl]-1,3-benzothiazol-5-yl]-5-methyl-1-piperidyl]-2-oxo-acetyl]amino]-2-methoxy-pyridine-3-carboxamide (140 mg, 266.85 umol, 96.5500 yield) (RT=53.79 min) and 5-[[2-[(2S,5R)-2-[2-[2-(dimethylamino)ethyl]-1,3-benzothiazol-5-yl]-5-methyl-1-piperidyl]-2-oxo-acetyl]amino]-2-methoxy-pyridine-3-carboxamide (140 mg, 266.85 umol, 96.55% yield) (RT=27.78 min).
Rel Time for Compound 1197 in analytical conditions (column: IC, IPA-MeOH, 50-50, 0.6 ml/min as mobile phase) 57.47 min and for Compound 1197 29.97 min.
Compound 1281:
  Retention time: 57.47 min
  $^1$HNMR (600 MHz, DMSO-d$_6$) δ (ppm) 1.04 (m, 3H), 1.35 (m, 1H), 1.72 (m, 1H), 1.88 (m, 1H), 2.11 (m, 1H), 2.20 (d, 6H), 2.31 (m, 1H), 2.69 (m, 3H), 3.21 (m, 2H), 3.50 (m, 1H), 3.94 (m, 3H), 5.50 (m, 1H), 7.37 (dd, 1H), 7.72 (m, 2H), 7.86 (d, 1H), 8.02 (dd, 1H), 8.50 (m, 2H), 11.07 (in, 1H).

LCMS(ESI): [M]$^+$ m/z: calcd 524.2; found 525.2; Rt=2.635 min.
Compound 1197:
  Retention time: 29.97 min
  $^1$H NMR (600 MHz, DMSO-d$_6$) δ (ppm) 1.04 (m, 3H), 1.37 (m, 1H), 1.72 (m, 1H), 1.88 (m, 1H), 2.11 (m, 1H), 2.20 (m, 6H), 2.31 (m, 1H), 2.69 (m, 3H), 3.21 (m, 2H), 3.95 (m, 4H), 5.50 (m, 1H), 7.37 (dd, 1H), 7.73 (m, 2H), 7.86 (m, 1H), 8.02 (dd, 1H), 8.52 (m, 2H), 11.07 (m, 1H).

LCMS(ESI): [M]$^+$ m/z: calcd 524.2; found 525.2; Rt=2.632 min.

Example 240. The Synthesis of N-(6-amino-5-ethyl-3-pyridyl)-2-[(2R,5S)-2-[6-[(2S)-2,4-dimethylpiperazin-1-yl]-3-pyridyl]-5-methyl-1-piperidyl]-2-oxo-acetamide (Compound 1099) and N-(6-amino-5-ethyl-3-pyridyl)-2-[(2R,5S)-2-[6-[(2R)-2,4-dimethylpiperazin-1-yl]-3-pyridyl]-5-methyl-1-piperidyl]-2-oxo-acetamide (Compound 1294

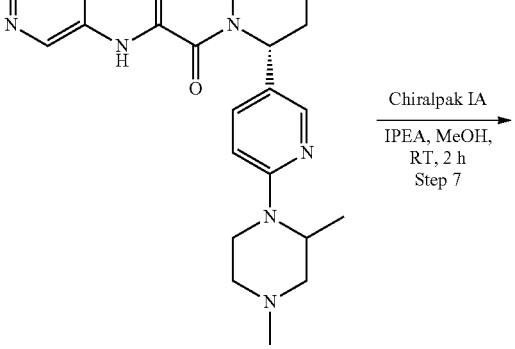

Chiralpak IA
IPEA, MeOH,
RT, 2 h
Step 7

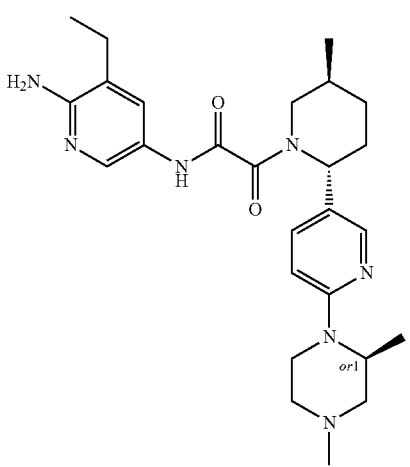

Compound 1099

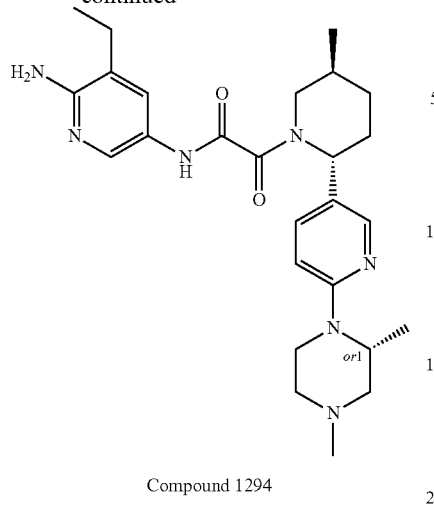

Compound 1294

Chiral separation conditions: Chiralpak IA, 250*20 mm, 5 mkm, IPA-MeOH, 50-50, 10 mL/min, Inj Volume: 200.000 μl; Column Temperature: 24° C.; Wavelength: 205 nm, 264 nm), RetTime (isomer A)=34.968 min; RetTime (isomer B)=51.008 min N-(6-amino-5-ethyl-3-pyridyl)-2-[(2R,5S)-2-[6-(2,4-dimethylpiperazin-1-yl)-3-pyridyl]-5-methyl-1-piperidyl]-2-oxo-acetamide (100 mg, 208.50 umol) was divided into enantiomers by Chiral HPLC affording: Compound 1099— N-(6-amino-5-ethyl-3-pyridyl)-2-[(2R,5S)-2-[6-[(2S)-2,4-dimethylpiperazin-1-yl]-3-pyridyl]-5-methyl-1-piperidyl]-2-oxo-acetamide (41 mg, 85.49 umol, 42.00% yield) with ret.time=28.721 min(analytical), 34.968 min(preparative) and Compound 1294—N-(6-amino-5-ethyl-3-pyridyl)-2-[(2R,5S)-2-[6-[(2R)-2,4-dimethylpiperazin-1-yl]-3-pyridyl]-5-methyl-1-piperidyl]-2-oxo-acetamide (38 mg, 79.23 umol, 38.00% yield) with ret.time=40.733 min(analytical), 51.008 min(preparative).

Compound 1294:

Yield: 41.0 mg (42.00%)

RT (Chiralpak IA (250*20 mm, 5 mkm), IPA-MeOH, 50-50, 0.6 mL/min)=38.669 min.

$^1$H NMR (500 MHz, dmso) δ 0.96-1.03 (m, 3H), 1.07-1.14 (m, 6H), 1.26-1.38 (m, 1H), 1.66-1.77 (m, 1H), 1.81-2.00 (m, 3H), 2.04-2.14 (m, 2H), 2.17 (s, 3H), 2.36-2.41 (m, 2H), 2.65-2.72 (m, 1H), 2.79-3.19 (m, 3H), 3.36-3.99 (m, 2H), 4.43 (s, 1H), 5.00-5.53 (m, 1H), 5.58-5.67 (m, 2H), 6.71-6.80 (m, 1H), 7.38-7.54 (m, 2H), 7.98-8.09 (m, 2H), 10.42-10.52 (m, 1H).

LCMS(ESI): [M+2H]$^+$ m/z: calcd 481.2; found 481.2; Rt=0.736 min.

Compound 1099:

Yield: 38.0 mg (38.00%)

RT (Chiralpak IA (250*20 mm, 5 mkm), IPA-MeOH, 50-50, 0.6 mL/min)=28.704 min.

$^1$H NMR (500 MHz, dmso) δ 0.97-1.03 (m, 3H), 1.07-1.13 (m, 6H), 1.27-1.37 (m, 1H), 1.63-1.76 (m, 1H), 1.78-2.02 (m, 3H), 2.03-2.12 (m, 2H), 2.17 (s, 3H), 2.36-2.41 (m, 2H), 2.65-3.23 (m, 4H), 3.38-3.97 (m, 2H), 4.43 (s, 1H), 5.00-5.52 (m, 1H), 5.56-5.67 (m, 2H), 6.71-6.80 (m, 1H), 7.38-7.54 (m, 2H), 8.00-8.10 (m, 2H), 10.44-10.54 (m, 1H). 6 LCMS(ESI): [M+H]$^+$ m/z: calcd 481.2; found 481.4; Rt=0.734 min.

Example 241. Synthesis of N-(6-amino-5-methyl-3-pyridyl)-2-[(2R,5S)-5-methyl-2-[2-(3-pyridyl)-1,3-benzothiazol-5-yl]-1-piperidyl]-2-oxo-acetamide (Compound 1310

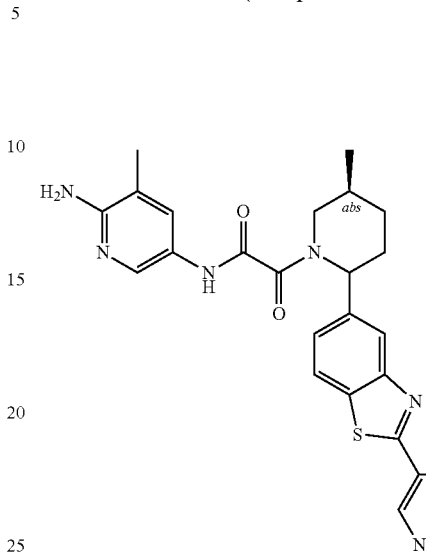

chiral SFC

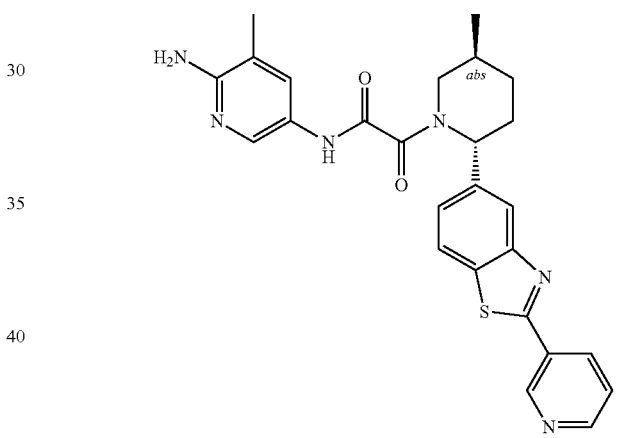

Compound 1310

N-(6-amino-5-methyl-3-pyridyl)-2-[(5S)-5-methyl-2-[2-(3-pyridyl)-1,3-benzothiazol-5-yl]-1-piperidyl]-2-oxo-acetamide (50 mg, 0.103 mmol) was purified by SFC (Instrument: Berger, Multigr AM-II; Column: Daicel Chiralcel OD-H 250 mm×30 mm×5 m; Mobile phase: supercritical CO$_2$/EtOH (0.1% NH$_3$—H$_2$O, v %)=55/45; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford N-(6-amino-5-methyl-3-pyridyl)-2-[(2R,5S)-5-methyl-2-[2-(3-pyridyl)-1,3-benzothiazol-5-yl]-1-piperidyl]-2-oxo-acetamide (44.4 mg, single known enantiomer with trans relative chemistry, peak 2, retention time: 8.370 min, white solid). $^1$H NMR (400 MHz, methanol-d4) δ ppm 9.27 (br s, 1H), 8.70 (br s, 1H), 8.26-8.57 (m, 2H), 7.99-8.23 (m, 2H), 7.39-7.88 (m, 3H), 5.49-5.89 (m, 1H), 3.77-4.13 (m, 1H), 3.50 (br s, 1H), 2.37 (br s, 2H), 2.25 (br s, 2H), 2.13 (br s, 1H), 1.85-2.09 (m, 2H), 1.50 (br s, 1H), 1.15 (br d, J=6.5 Hz, 3H); LCMS (ESI) [M+H]$^+$ m/z: calcd 487.2, found 487.3; HPLC: 100% @254 nm; 100% ee, 99.5% de.

Example 242. The Synthesis of Rel-5-[[2-[(2S,4R, 5S)-2-(1,3-benzothiazol-5-yl)-4-methoxy-5-methyl-1-piperidyl]-2-oxo-acetyl]amino]-2-methoxy-pyridine-3-carboxamide (Compound 1364) and Rel-5-[[2-[(2R,4S,5R)-2-(1,3-benzothiazol-5-yl)-4-methoxy-5-methyl-1-piperidyl]-2-oxo-acetyl]amino]-2-methoxy-pyridine-3-carboxamide (Compound 1344
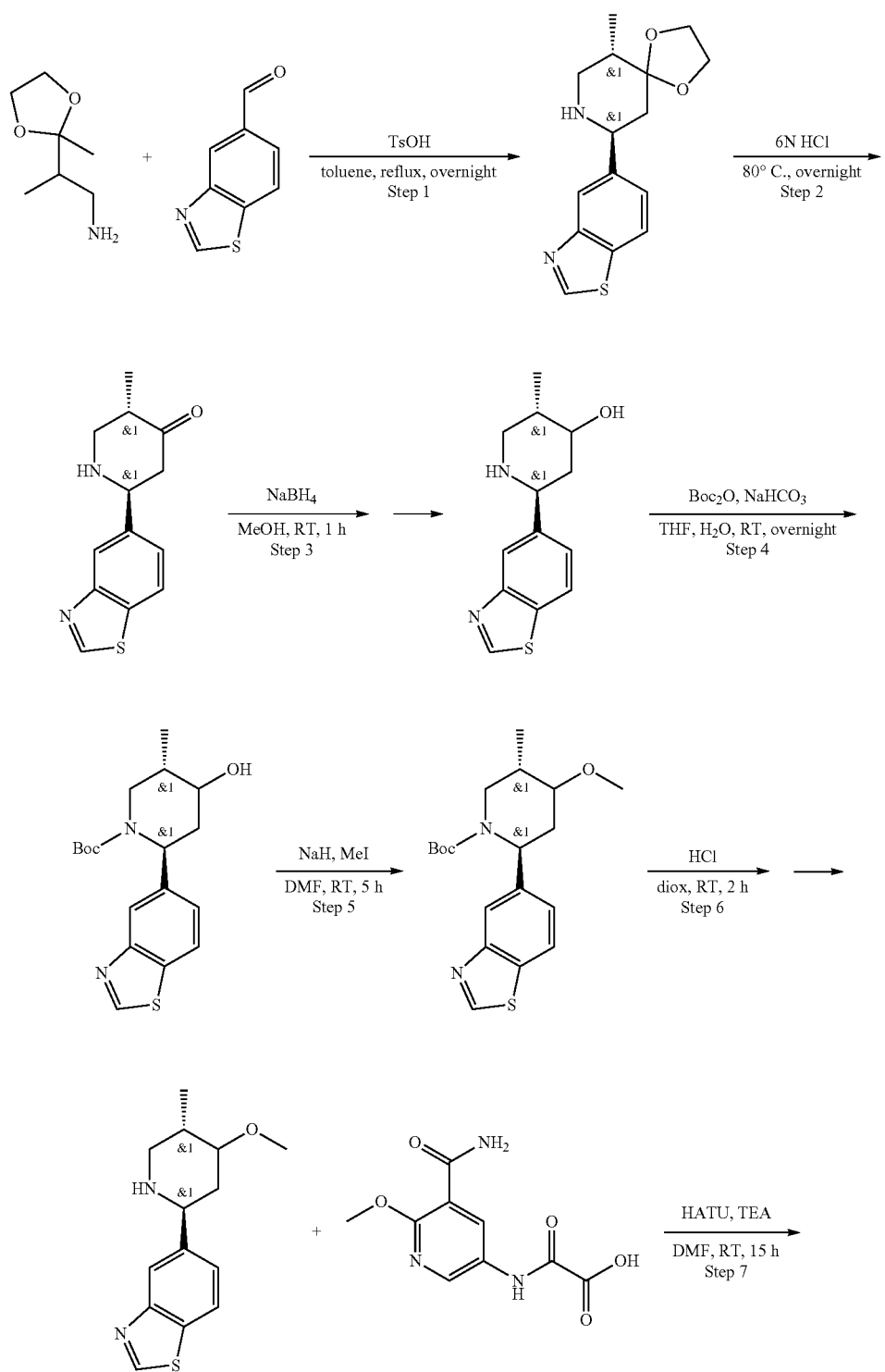

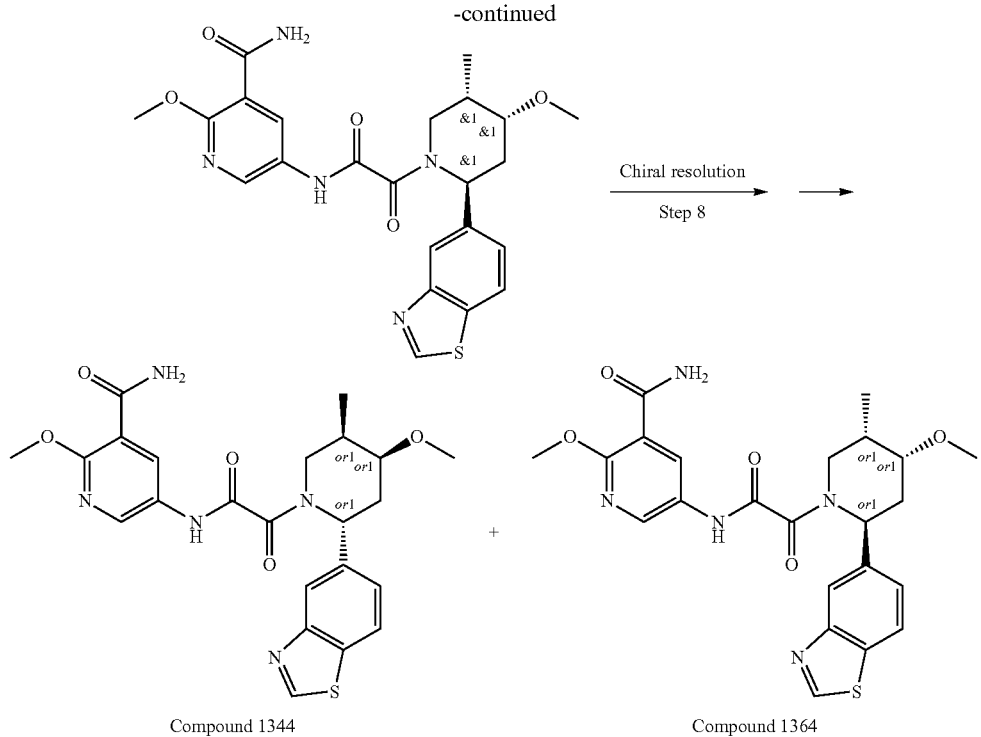

Compound 1344 + Compound 1364

Step 1: The Synthesis of rac-(6S,9S)-9-(1,3-benzothiazol-5-yl)-6-methyl-1,4-dioxa-8-azaspiro[4.5]decane

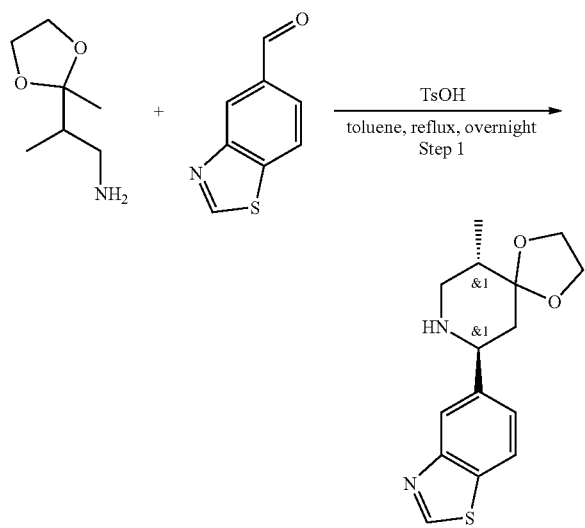

2-(2-methyl-1,3-dioxolan-2-yl)propan-1-amine (6.67 g, 45.96 mmol) was dissolved in Toluene (60 mL) and 1,3-benzothiazole-5-carbaldehyde (7.5 g, 45.96 mmol) was added thereto followed by addition of p-Toluenesulfonic acid monohydrate (26.23 g, 137.87 mmol, 21.15 mL). The resulting mixture was heated to reflux and refluxed under Dean-Stark trap overnight. The reaction mixture was cooled and aq. $K_2CO_3$ solution (50 mL) was added. The resulting mixture was transferred to a separation funnel and an organic layer was separated. The aqueous layer was extracted with EtOAc (2×100 mL) and combined organic layers were dried over $Na_2SO_4$, filtered and evaporated. The residue was dissolved in $CHCl_3$ (200 mL) and the resulting mixture was extracted with aq. $NaHSO_4$ (1 g in 10 mL of water, 2*50 mL). Combined aqueous layers were washed with $CHCl_3$ (2*100 mL) and then basified with $K_2CO_3$ (20 g). The resulting mixture was extracted with $CHCl_3$ (2*100 mL) and combined organic layers were dried over $Na_2SO_4$, filtered and evaporated to obtain (6S,9S)-9-(1,3-benzothiazol-5-yl)-6-methyl-1,4-dioxa-8-azaspiro[4.5]decane (4.63 g, crude).

$^1$H NMR (600 MHz, DMSO-$d_6$) δ (ppm) 0093 (d, 3H), 1.70 (m, 4H), 1.99 (m, 2H), 2.84 (m, 1H), 3.14 (m, 1H), 4.01 (m, 3H), 7.54 (d, 1H), 7.91 (d, 1H), 8.13 (s, 1H), 9.00 (s, 1H).

LCMS(ESI): [M+H]$^+$ m/z: calcd 291.2; found 291.2; Rt=0.752 min.

Step 2: The Synthesis of rac-(2S,5S)-2-(1,3-benzothiazol-5-yl)-5-methyl-piperidin-4-one

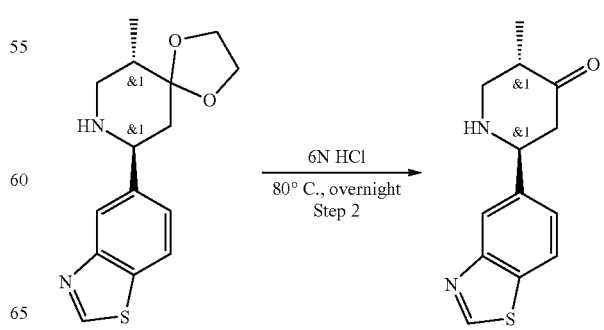

(6S,9S)-9-(1,3-benzothiazol-5-yl)-6-methyl-1,4-dioxa-8-azaspiro[4.5]decane (7.53 g, 25.93 mmol) was dissolved in 6N HCl (300 mL) and the resulting mixture was heated at 80° C. (in an oil bath) overnight. The reaction mixture was cooled and basified with $K_2CO_3$ to pH=10.

The resulting mixture was extracted with DCM (2*200 mL) and combined organic layers were dried over $Na_2SO_4$, filtered and evaporated to obtain (2S,5S)-2-(1,3-benzothiazol-5-yl)-5-methyl-piperidin-4-one (6.3 g, crude).

$^1$H NMR (500 MHz, $CDCl_3$) δ (ppm) 1.08 (d, 3H), 2.89 (m, 4H), 3.53 (m, 1H), 4.12 (m, 1H), 7.50 (d, 1H), 7.95 (d, 1H), 8.16 (s, 1H), 9.01 (s, 1H).

LCMS(ESI): [M+H]$^+$ m/z: calcd 247.0; found 247.0; Rt=0.551 min.

Step 3: The Synthesis of rac-(2S,5S)-2-(1,3-benzothiazol-5-yl)-5-methyl-piperidin-4-ol

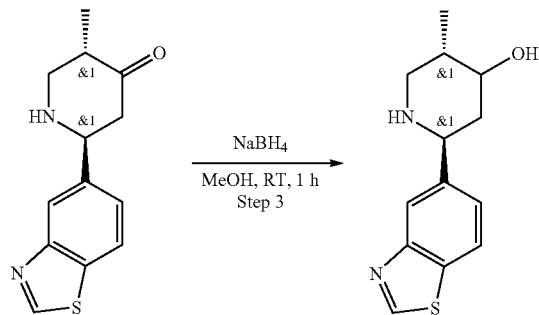 [SMILES: C[C@H]1CN[C@H](c2ccc3scnc3c2)CC1=O ; "MeOH, RT, 1 hStep 3" ; "NaBH4" ; C[C@H]1CN[C@H](c2ccc3scnc3c2)CC1O]

Sodium Borohydride (635.80 mg, 16.81 mmol, 594.21 uL) was added portionwise to a solution of (2S,5S)-2-(1,3-benzothiazol-5-yl)-5-methyl-piperidin-4-one (6.9 g, 28.01 mmol) in Methanol. Resulting suspension was stirred at room temperature for 1 hr. Water (10 mL) was added and the mixture was extracted with MTBE (2×10 mL). Organic phase was dried over $Na_2SO_4$, filtered and evaporated to obtain (2S,5S)-2-(1,3-benzothiazol-5-yl)-5-methyl-piperidin-4-ol (5.06 g, crude).

$^1$H NMR (500 MHz, $CDCl_3$) δ (ppm) 1.02 (d, 3H), 1.69 (m, 4H), 2.17 (m, 1H), 2.49 (m, 1H), 3.28 (m, 2H), 3.85 (m, 1H), 7.47 (d, 1H), 7.89 (d, 1H), 8.09 (s, 1H), 8.95 (s, 1H).

LCMS(ESI): [M+H]$^+$ m/z: calcd 249.0; found 249.0; Rt=0.463 min.

Step 4: The Synthesis of rac-tert-butyl (2S,5S)-2-(1,3-benzothiazol-5-yl)-4-hydroxy-5-methyl-piperidine-1-carboxylate

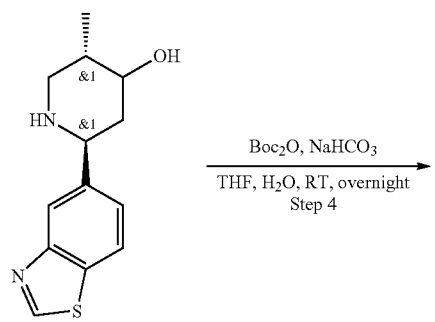

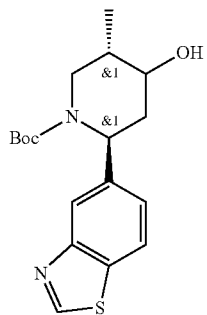

Sodium hydrogen carbonate, 99% (3.04 g, 36.24 mmol, 1.41 mL) was dissolved in THF (15 mL) and Water (15 mL), then (2S,5S)-2-(1,3-benzothiazol-5-yl)-5-methyl-piperidin-4-ol (3 g, 12.08 mmol) was added. The reaction mixture was stirred for 5 min at room temperature following by the addition of di-tert-butyl dicarbonate (2.90 g, 13.29 mmol, 3.05 mL). The reaction mixture was stirred overnight at room temperature. The reaction mixture was diluted with EtOAc/water, organic phase was separated and aqueous layer was washed with EtOAc (2 times), combined organic phase was washed with brine, dried over $Na_2SO_4$, filtered and concentrated in vacuo to give tert-butyl (2S,5S)-2-(1,3-benzothiazol-5-yl)-4-hydroxy-5-methyl-piperidine-1-carboxylate (4.4 g, crude).

LCMS(ESI): [M+H]$^+$ m/z: calcd 349.2; found 349.2; Rt=1.107 min.

Step 5: The Synthesis of rac-tert-butyl (2S,5S)-2-(1,3-benzothiazol-5-yl)-4-methoxy-5-methyl-piperidine-1-carboxylate

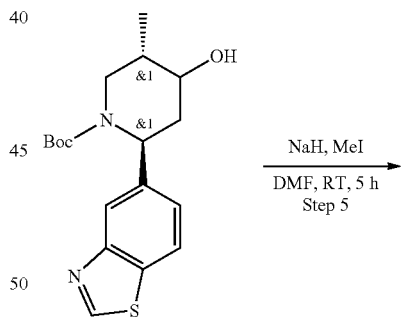

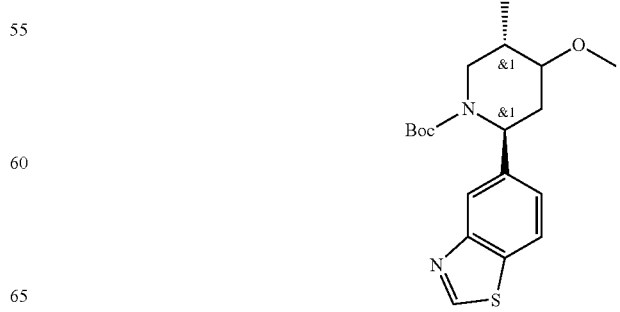

Sodium hydride (909.15 mg, 37.88 mmol) was added to a solution of tert-butyl (2S,5S)-2-(1,3-benzothiazol-5-yl)-4-hydroxy-5-methyl-piperidine-1-carboxylate (4.4 g, 12.63 mmol) in DMF (44 mL) and the mixture was stirred for 30 minutes. Methyl iodide (5.38 g, 37.88 mmol, 2.36 mL) was added and the mixture was stirred for 5 h. Water (10 mL) was added and the mixture was extracted with diethyl ether (2×10 mL). The combined organic fractions were washed with water (4×10 mL) and brine, dried (MgSO₄) and the solvent was evaporated under reduced pressure to give the title compound tert-butyl (2S,5S)-2-(1,3-benzothiazol-5-yl)-4-methoxy-5-methyl-piperidine-1-carboxylate (4.23 g, crude) that was used in the next step without further purification.

LCMS(ESI): [M+H]⁺ m/z: calcd 363.2; found 363.2; Rt=1.342 min.

Step 6: The Synthesis of rac-5-[(2S,5S)-4-methoxy-5-methyl-2-piperidyl]-1,3-benzothiazole

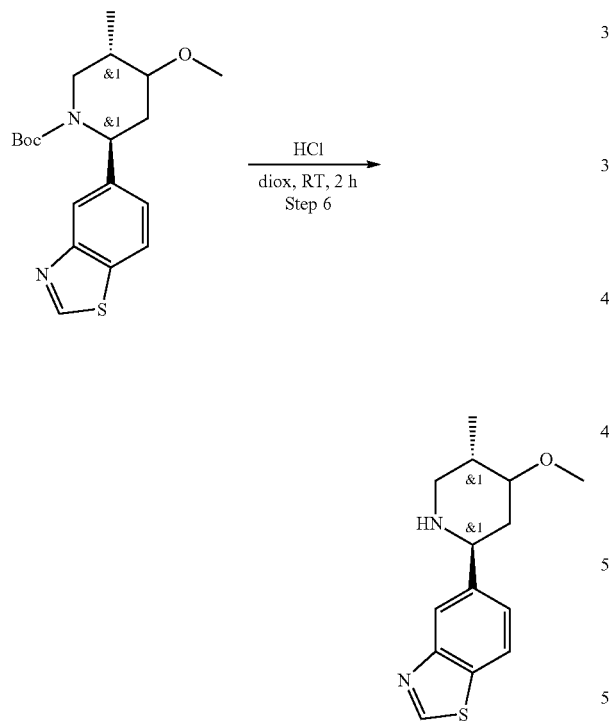

A solution of tert-butyl (2S,5S)-2-(1,3-benzothiazol-5-yl)-4-methoxy-5-methyl-piperidine-1-carboxylate (4.23 g, 11.67 mmol) in Dioxane/HCl (5 mL) was stirred at rt for 2 hr. Precipitate that was formed was filtered, washed with MTBE (2×10 mL) and dried under reduced pressure to obtain 5-[(2S,5S)-4-methoxy-5-methyl-2-piperidyl]-1,3-benzothiazole (2.98 g, crude, HCl).

LCMS(ESI): [M+H]⁺ m/z: calcd 263.0; found 263.0; Rt=0.802 min.

Step 7: The Synthesis of rac-5-[[2-[(2S,4R,5S)-2-(1,3-benzothiazol-5-yl)-4-methoxy-5-methyl-1-piperidyl]-2-oxo-acetyl]amino]-2-methoxy-pyridine-3-carboxamide

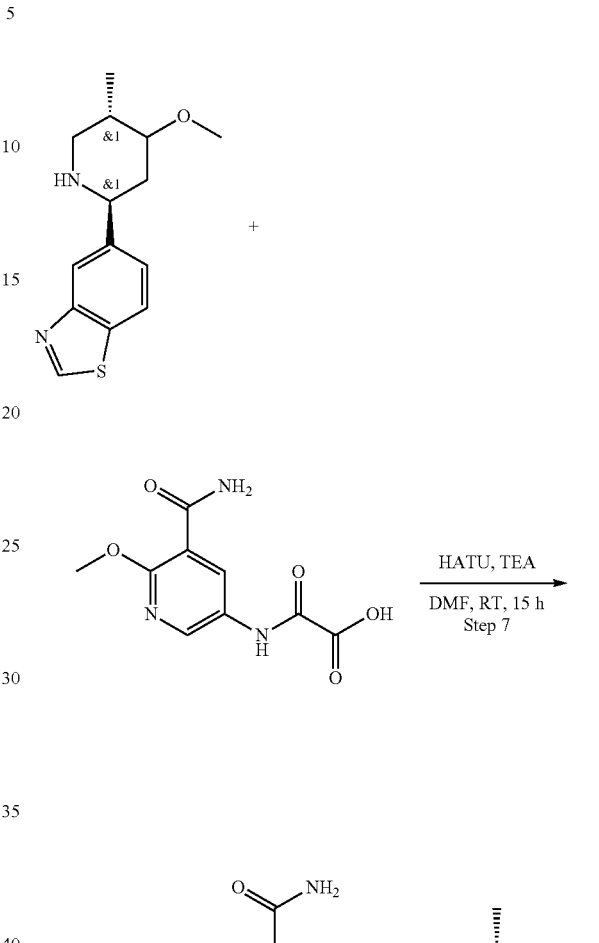

5-[(2S,5S)-4-methoxy-5-methyl-2-piperidyl]-1,3-benzothiazole (0.2 g, 762.28 umol), 2-[(5-carbamoyl-2-methoxy-3-pyridyl)amino]-2-oxo-acetic acid (182.33 mg, 762.28 umol), triethylamine (385.68 mg, 3.81 mmol, 531.24 uL) were mixed in DMF (2 mL) and then HATU (434.76 mg, 1.14 mmol) was added. Resulting mixture was stirred at 25° C. for 12 hr. The solvent was evaporated. Resulting crude product was purified by HPLC (2-10 min 0-45% MeCN 30 mL/min (loading pump 4 mL MeCN; column: SunFire 100*19 mm, 5 microM) to obtain rac-5-[[2-[(2S,4R,5S)-2-(1,3-benzothiazol-5-yl)-4-methoxy-5-methyl-1-piperidyl]-2-oxo-acetyl]amino]-2-methoxy-pyridine-3-carboxamide (44.2 mg, 91.41 umol, 11.99% yield)

LCMS(ESI): [M+H]⁺ m/z: calcd 484.2; found 484.2; Rt=1.013 min.

Step 8: The Synthesis of Rel-5-[[2-[(2S,4R,5S)-2-(1,3-benzothiazol-5-yl)-4-methoxy-5-methyl-1-piperidyl]-2-oxo-acetyl]amino]-2-methoxy-pyridine-3-carboxamide (Compound 1364) and Rel-5-[[2-[(2R,4S,5R)-2-(1,3-benzothiazol-5-yl)-4-methoxy-5-methyl-1-piperidyl]-2-oxo-acetyl]amino]-2-methoxy-pyridine-3-carboxamide (Compound 1344

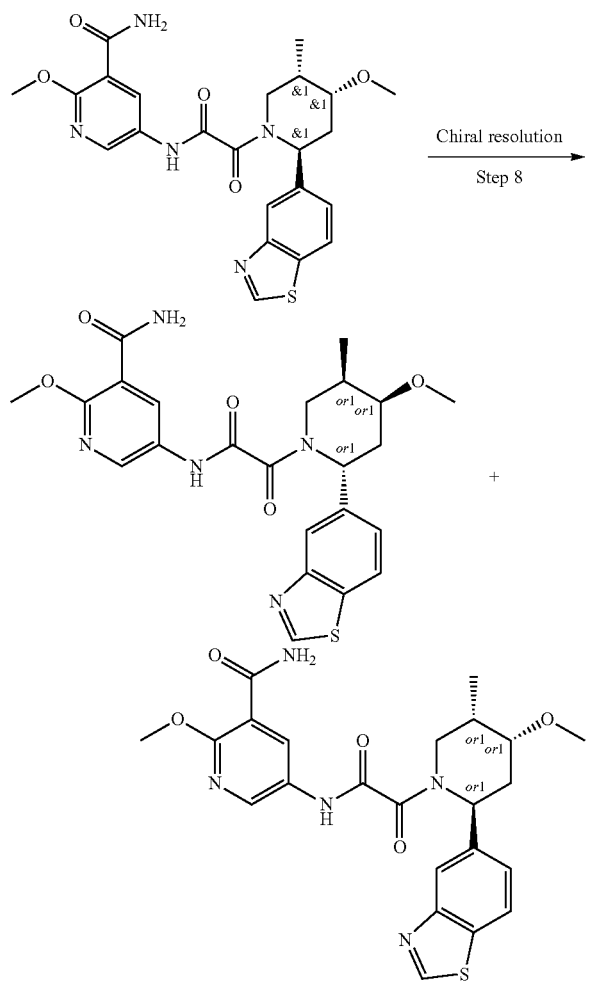

rac-5-[[2-[(2S,4R,5S)-2-(1,3-benzothiazol-5-yl)-4-methoxy-5-methyl-1-piperidyl]-2-oxo-acetyl]amino]-2-methoxy-pyridine-3-carboxamide (44.20 mg, 91.41 umol) was chiral separated (Chiralpak AD-HIII (250*20, 5 mkm), IPA-MeOH, 50-50, 11 mL/min) to obtain Compound 1344—rel-5-[[2-[(2R,4S,5R)-2-(1,3-benzothiazol-5-yl)-4-methoxy-5-methyl-1-piperidyl]-2-oxo-acetyl]amino]-2-methoxy-pyridine-3-carboxamide (12.84 mg, 26.55 umol, 29.05% yield) and Compound 1364—rel-5-[[2-[(2S,4R,5S)-2-(1,3-benzothiazol-5-yl)-4-methoxy-5-methyl-1-piperidyl]-2-oxo-acetyl]amino]-2-methoxy-pyridine-3-carboxamide (14.14 mg, 29.24 umol, 31.99% yield).

Preparative:

RT for Compound 1344 (Chiralpak AD-HIII(250*20, 5 mkm), IPA-MeOH, 50-50, 11 ml/min)=89.951

RT for Compound 1364 (Chiralpak AD-HIII(250*20, 5 mkm), IPA-MeOH, 50-50, 11 ml/min)=67.124

Compound 1344:

Yield: 12.84 mg (29.05%)

RT (Chiralcel OD-H (250*4.6, 5 mkm), Hexane-IPA-MeOH, 50-25-25, 0.6 mL/min)=15.273 min.

$^1$H NMR (DMSO-d$_6$, 600 MHz): δ (ppm) 1.04 (d, 3H), 1.88 (m, 1H), 2.28 (m, 1H), 2.38 (m, 1H), 3.06 (m, 3H), 3.18 (m, 1H), 3.59 (m, 1H), 3.93 (m, 4H), 5.44 (m, 1H), 7.48 (m, 1H), 7.71 (m, 2H), 8.05 (m, 2H), 8.42 (m, 2H), 9.35 (m, 1H), 10.95 (m, 1H).

LCMS(ESI): [M+H]$^+$ m/z: calcd 484.2; found 484.2; Rt=2.873 min.

Compound 1364:

Yield: 14.14 mg (31.99%)

RT (Chiralcel OD-H (250*4.6, 5 mkm), Hexane-IPA-MeOH, 50-25-25, 0.6 mL/min)=19.962 min.

$^1$H NMR (DMSO-d$_6$, 600 MHz): δ (ppm) 1.04 (d, 3H), 1.88 (m, 1H), 2.28 (m, 1H), 2.38 (m, 1H), 3.06 (m, 3H), 3.18 (m, 1H), 3.58 (m, 1H), 3.92 (m, 4H), 5.44 (m, 1H), 7.48 (m, 1H), 7.71 (m, 2H), 8.04 (m, 2H), 8.42 (m, 2H), 9.35 (m, 1H), 10.95 (m, 1H).

LCMS(ESI): [M+H]$^+$ m/z: calcd 484.2; found 484.2; Rt=2.873 min.

Example 243. The Synthesis of Rel-5-[[2-[(2R,4S,5R)-2-(1,3-benzothiazol-5-yl)-4-methoxy-5-methyl-1-piperidyl]-2-oxo-acetyl]amino]pyridine-3-carboxamide (Compound 1161) and Rel-5-[[2-[(2S,4R,5S)-2-(1,3-benzothiazol-5-yl)-4-methoxy-5-methyl-1-piperidyl]-2-oxo-acetyl]amino]pyridine-3-carboxamide (Compound 1221

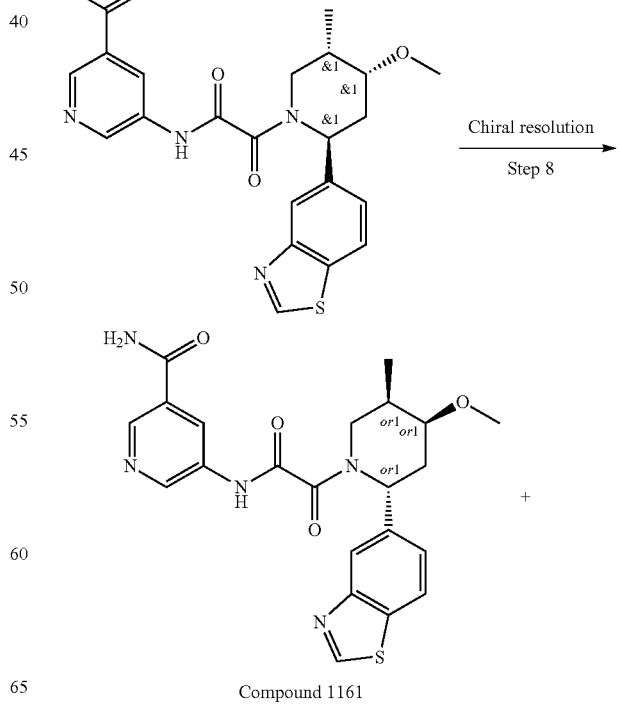

Compound 1161

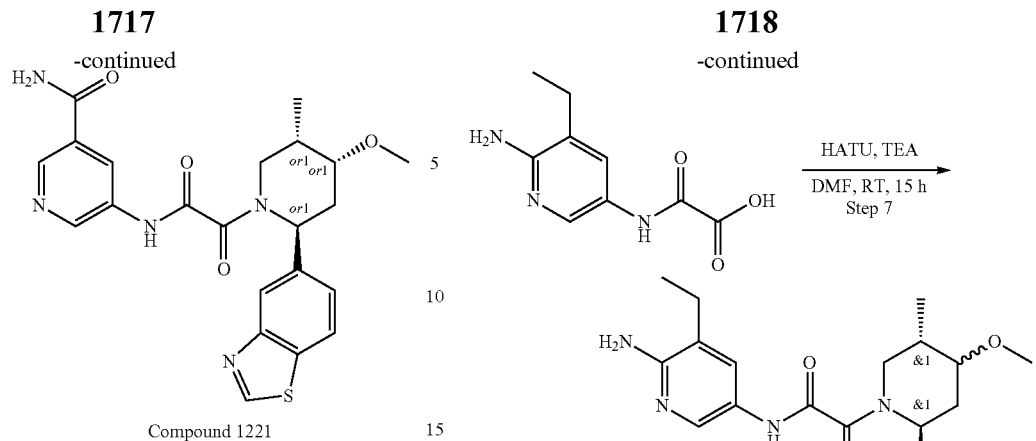

Compound 1221

Prepared according to general methods.
Preparative:
  RT for Compound 1221 (ChirapakAS-H (250*20 mm, 5 mkm), Hexane-IPA-MeOH, 70-15-15, 15 mL/min) =28.857 min.
  RT for Compound 1161 (ChirapakAS-H (250*20 mm, 5 mkm), Hexane-IPA-MeOH, 70-15-15, 15 mL/min) =17.976 min.
Compound 1221:
  Yield: 7.87 mg (32.66%)
  RT (Chiralpak AS-H (250*4.6, 5 mkm), Hexane-IPA-MeOH, 70-15-15, 0.6 mL/min)=29.012 min.
  $^1$H NMR (DMSO-$d_6$, 600 MHz): δ (ppm) 1.05 (d, 3H), 1.91 (m, 1H), 2.28 (m, 2H), 3.06 (m, 3H), 3.19 (m, 1H), 3.76 (m, 2H), 5.44 (m, 1H), 7.52 (m, 2H), 8.07 (m, 3H), 8.41 (m, 1H), 8.79 (m, 2H), 9.34 (m, 1H), 11.15 (m, 1H).
  LCMS(ESI): [M+H]$^+$ m/z: calcd 454.2; found 454.2; Rt=2.517 min.
Compound 1161:
  Yield: 8.35 mg (34.65%)
  RT (Chiralpak AS-H (250*4.6, 5 mkm), Hexane-IPA-MeOH, 70-15-15, 0.6 mL/min)=19.651 min.
  $^1$H NMR (DMSO-$d_6$, 600 MHz): δ (ppm) 1.05 (d, 3H), 1.93 (m, 1H), 2.28 (m, 2H), 3.06 (m, 3H), 3.19 (m, 1H), 3.76 (m, 2H), 5.44 (m, 1H), 7.52 (m, 2H), 8.08 (m, 3H), 8.41 (m, 1H), 8.79 (m, 2H), 9.35 (m, 1H), 11.15 (m, 1H).
  LCMS(ESI): [M+H]$^+$ m/z: calcd 454.2; found 454.2; Rt=2.520 min.

Example 244. Synthesis of Rel-N-(6-amino-5-ethyl-3-pyridyl)-2-[(2S,4R,5S)-2-(1,3-benzothiazol-5-yl)-4-methoxy-5-methyl-1-piperidyl]-2-oxo-acetamide (Compound 1138) and Rel-N-(6-amino-5-ethyl-3-pyridyl)-2-[(2R,4S,5R)-2-(1,3-benzothiazol-5-yl)-4-methoxy-5-methyl-1-piperidyl]-2-oxo-acetamide (Compound 1286

Step 1: The Synthesis of rac-N-(6-amino-5-ethyl-3-pyridyl)-2-[(2S,5S)-2-(1,3-benzothiazol-5-yl)-4-methoxy-5-methyl-1-piperidyl]-2-oxo-acetamide

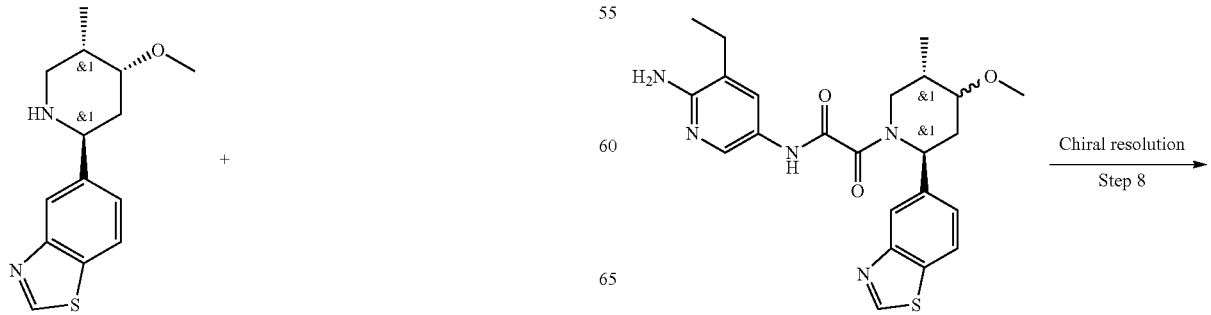

5-[(2S,5S)-4-methoxy-5-methyl-2-piperidyl]-1,3-benzothiazole (246.00 mg, 937.61 mol), 2-[(6-amino-5-ethyl-3-pyridyl)amino]-2-oxo-acetic acid (196.15 mg, 937.61 μmol) and triethylamine (474.38 mg, 4.69 mmol, 653.42 μL) were mixed together in DMF (3 mL) and HATU (427.81 mg, 1.13 mmol) was added thereto. The resulting mixture was stirred overnight. The reaction mixture was submitted to HPLC and purified (2-10 min 45-55% methanol+NH$_3$Flow 30 mL/min (loading pump 4 mL methanol), column: SunFire 100*19 mm, 5 microM) to obtain N-(6-amino-5-ethyl-3-pyridyl)-2-[(2S,5S)-2-(1,3-benzothiazol-5-yl)-4-methoxy-5-methyl-1-piperidyl]-2-oxo-acetamide (44.1 mg, 97.23 μmol, 10.37% yield), N-(6-amino-5-ethyl-3-pyridyl)-2-[(2S,5S)-2-(1,3-benzothiazol-5-yl)-4-methoxy-5-methyl-1-piperidyl]-2-oxo-acetamide (33 mg, 72.76 μmol, 7.76% yield) and N-(6-amino-5-ethyl-3-pyridyl)-2-[(2S,5S)-2-(1,3-benzothiazol-5-yl)-4-methoxy-5-methyl-1-piperidyl]-2-oxo-acetamide (31.7 mg, 69.89 mol, 7.45% yield)
  LCMS(ESI): [M+H]$^+$ m/z: calcd 454.0; found 454.0; Rt=0.964 min.

Step 2: The Synthesis of Rel-N-(6-amino-5-ethyl-3-pyridyl)-2-[(2S,4R,5S)-2-(1,3-benzothiazol-5-yl)-4-methoxy-5-methyl-1-piperidyl]-2-oxo-acetamide (Compound 1138) and Rel-N-(6-amino-5-ethyl-3-pyridyl)-2-[(2R,4S,5R)-2-(1,3-benzothiazol-5-yl)-4-methoxy-5-methyl-1-piperidyl]-2-oxo-acetamide (Compound 1286

-continued

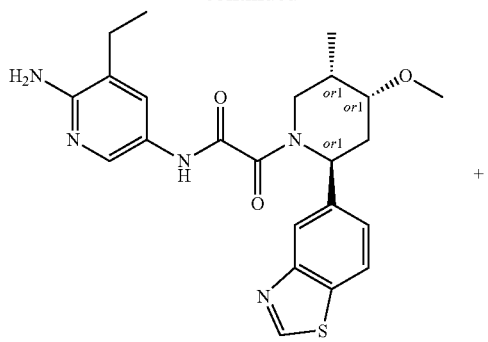

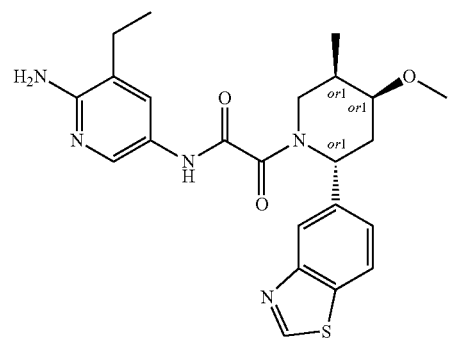

rac-N-(6-amino-5-ethyl-3-pyridyl)-2-[(2S,5S)-2-(1,3-benzothiazol-5-yl)-4-methoxy-5-methyl-1-piperidyl]-2-oxo-acetamide (108.8 mg, 239.88 μmol) (combined fractions) was chirally separated (Chiralcel OD-H (250*20 mm, 5 mkm), Hexane-IPA-MeOH, 50-25-25, 12 mL/min, Retention time (Compound 1138)=12.331 min, Retention time (Compound 1286)=14.940 min) to obtain rel-N-(6-amino-5-ethyl-3-pyridyl)-2-[(2S,4R,5S)-2-(1,3-benzothiazol-5-yl)-4-methoxy-5-methyl-1-piperidyl]-2-oxo-acetamide (34.1 mg, 75.18 μmol, 31.34% yield) (Compound 1138) and rel-N-(6-amino-5-ethyl-3-pyridyl)-2-[(2R,4S,5R)-2-(1,3-benzothiazol-5-yl)-4-methoxy-5-methyl-1-piperidyl]-2-oxo-acetamide (30.98 mg, 68.30 μmol, 28.47% yield) (Compound 1286)

Compound 1138:

Yield: 34.1 mg (31.34%)

RT (Chiracel OD-H (250*4.6, 5 mkm), Hexane-IPA-MeOH, 50-25-25, 0.6 mL/min)=11.014 min.

$^1$H NMR (DMSO-$d_6$, 600 MHz): δ (ppm) 1.05 (m, 6H), 1.89 (m, 1H), 2.26 (m, 2H), 2.41 (m, 2H), 3.05 (m, 3H), 3.18 (m, 1H), 3.64 (m, 2H), 5.58 (m, 3H), 7.49 (m, 2H), 8.07 (m, 3H), 9.37 (s, 1H), 10.43 (m, 1H).

LCMS(ESI): [M+H]$^+$ m/z: calcd 454.0; found 454.0; Rt=0.967 min.

Compound 1286:

Yield: 30.98 mg (28.47%)

RT (Chiracel OD-H (250*4.6, 5 mkm), Hexane-IPA-MeOH, 50-25-25, 0.6 mL/min)=13.123 min.

$^1$H NMR (DMSO-$d_6$, 600 MHz): δ (ppm) 1.05 (m, 6H), 1.89 (m, 1H), 2.26 (m, 2H), 2.41 (m, 2H), 3.05 (m, 3H), 3.18 (m, 1H), 3.65 (m, 2H), 5.58 (m, 3H), 7.49 (m, 2H), 8.07 (m, 3H), 9.37 (s, 1H), 10.43 (m, 1H).

LCMS(ESI): [M+H]$^+$ m/z: calcd 454.0; found 454.0; Rt=0.967 min.

Example 245. The Synthesis of Rel-N-(6-amino-5-methyl-3-pyridyl)-2-[(2S,4R,5S)-2-(1,3-benzothiazol-5-yl)-4-methoxy-5-methyl-1-piperidyl]-2-oxo-acetamide (Compound 1130) and Rel-N-(6-amino-5-methyl-3-pyridyl)-2-[(2R,4S,5R)-2-(1,3-benzothiazol-5-yl)-4-methoxy-5-methyl-1-piperidyl]-2-oxo-acetamide (Compound 1216

Step 1: The Synthesis of rac-N-(6-amino-5-methyl-3-pyridyl)-2-[(2S,5S)-2-(1,3-benzothiazol-5-yl)-4-methoxy-5-methyl-1-piperidyl]-2-oxo-acetamide

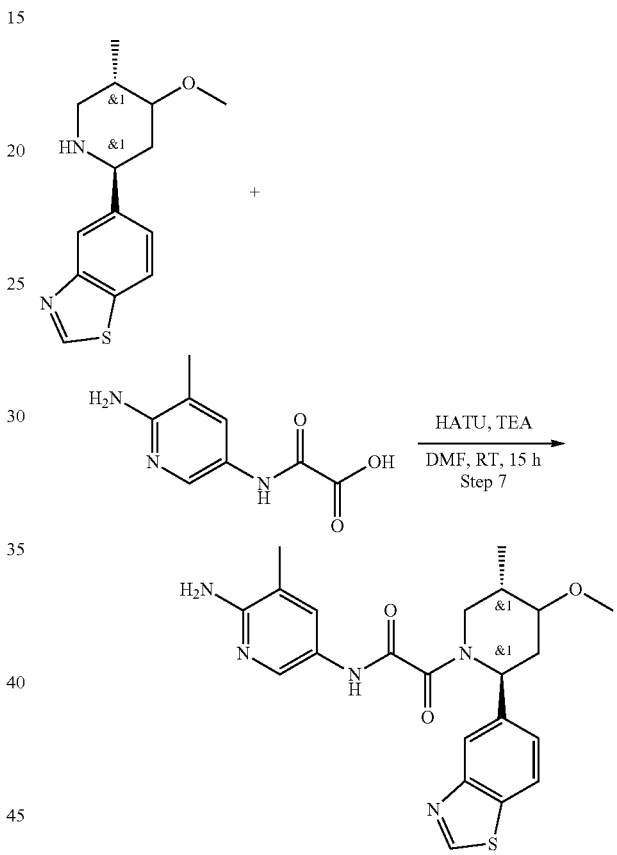

5-[(2S,5S)-4-methoxy-5-methyl-2-piperidyl]-1,3-benzothiazole (200 mg, 762.28 μmol), 2-[(6-amino-5-methyl-3-pyridyl)amino]-2-oxo-acetic acid (148.78 mg, 762.28 μmol) and triethylamine (385.68 mg, 3.81 mmol, 531.24 μL) were mixed together in DMF (3 mL) and HATU (347.81 mg, 914.74 μmol) was added thereto. The resulting mixture was stirred at room temperature overnight. The reaction mixture was submitted to HPLC and purified (2-10 min 30-45% MeOH 30 mL/min (loading pump 4 mL MeOH column: SunFire 100*19 mm, 5 microM) to obtain N-(6-amino-5-methyl-3-pyridyl)-2-[(2S,5S)-2-(1,3-benzothiazol-5-yl)-4-methoxy-5-methyl-1-piperidyl]-2-oxo-acetamide (34.4 mg, 78.27 μmol, 10.27% yield) and N-(6-amino-5-methyl-3-pyridyl)-2-[(2S,5S)-2-(1,3-benzothiazol-5-yl)-4-methoxy-5-methyl-1-piperidyl]-2-oxo-acetamide (20.7 mg, 47.10 μmol, 6.18% yield)

LCMS(ESI): [M+H]$^+$ m/z: calcd 440.1; found 440.1; Rt=0.912 min.

Step 2: The Synthesis of Rel-N-(6-amino-5-methyl-3-pyridyl)-2-[(2S,4R,5S)-2-(1,3-benzothiazol-5-yl)-4-methoxy-5-methyl-1-piperidyl]-2-oxo-acetamide (Compound 1130) and Rel-N-(6-amino-5-methyl-3-pyridyl)-2-[(2R,4S,5R)-2-(1,3-benzothiazol-5-yl)-4-methoxy-5-methyl-1-piperidyl]-2-oxo-acetamide (Compound 1216

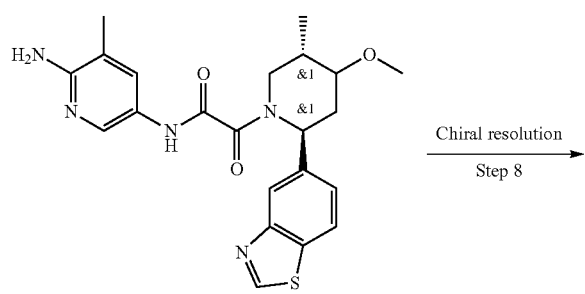

Chiral resolution
Step 8

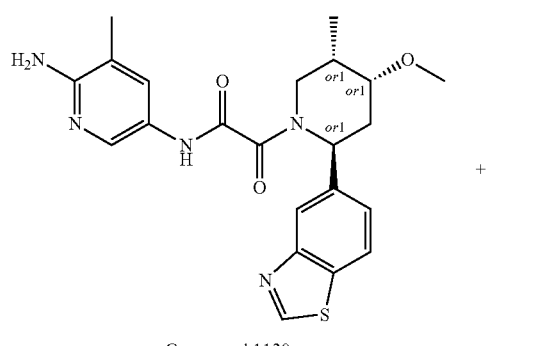

Compound 1130

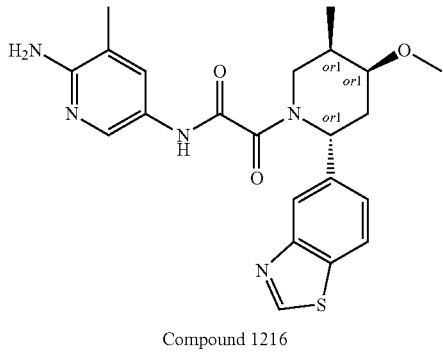

Compound 1216 rac-N-(6-amino-5-methyl-3-pyridyl)-2-[(2S,5S)-2-(1,3-benzothiazol-5-yl)-4-methoxy-5-methyl-1-piperidyl]-2-oxo-acetamide (55.1 mg, 125.36 μmol) was chirally separated (Chiralpak IA (250*30 mm, 5 mkm), IPA-MeOH, 50-50, 20 mL/min, Rt (Compound 1130)=40.066 min, Rt (Compound 1216)=56.059 min) to obtain rel-N-(6-amino-5-methyl-3-pyridyl)-2-[(2S,4R,5S)-2-(1,3-benzothiazol-5-yl)-4-methoxy-5-methyl-1-piperidyl]-2-oxo-acetamide (14.26 mg, 32.44 μmol, 25.88% yield) and rel-N-(6-amino-5-methyl-3-pyridyl)-2-[(2R,4S,5R)-2-(1,3-benzothiazol-5-yl)-4-methoxy-5-methyl-1-piperidyl]-2-oxo-acetamide (14.09 mg, 32.06 μmol, 25.57% yield).

Compound 1130:

Yield: 14.26 mg (25.88%)

RT (Chiralpak IA (250*4.6, 5 mkm), IPA-MeOH, 50-50, 0.6 mL/min)=31.408 min.

$^1$H NMR (600 MHz, dmso) δ 1.00-1.10 (m, 3H), 1.83-2.21 (m, 5H), 2.22-2.35 (m, 1H), 3.03-3.29 (m, 4H), 3.34-4.10 (m, 2H), 5.30-5.67 (m, 3H), 7.21-7.54 (m, 2H), 7.79-8.15 (m, 3H), 9.32-9.39 (m, 1H), 10.28-10.58 (m, 1H).

LCMS(ESI): [M+H]$^+$ m/z: calcd 440.2; found 440.2; Rt=2.399 min.

Compound 1216:

Yield: 14.09 mg (25.57%)

RT (Chiralpak IA (250*4.6, 5 mkm), IPA-MeOH, 50-50, 0.6 mL/min)=51.749 min.

$^1$H NMR (600 MHz, dmso) δ 0.99-1.09 (m, 3H), 1.84-2.18 (m, 5H), 2.24-2.35 (m, 1H), 3.01-3.28 (m, 4H), 3.34-4.08 (m, 2H), 5.29-5.73 (m, 3H), 7.20-7.54 (m, 2H), 7.80-8.16 (m, 3H), 9.33-9.41 (m, 1H), 10.28-10.64 (m, 1H).

LCMS(ESI): [M+H]$^+$ m/z: calcd 440.2; found 440.2; Rt=2.395 min.

Example 246. The Synthesis of N-(6-amino-5-methylpyridin-3-yl)-2-(5-methyl-2-(3-(4-methylpiperazin-1-yl)phenyl)piperidin-1-yl)-2-oxoacetamide (Compound 1223, Compound 1121 and Compound 1229

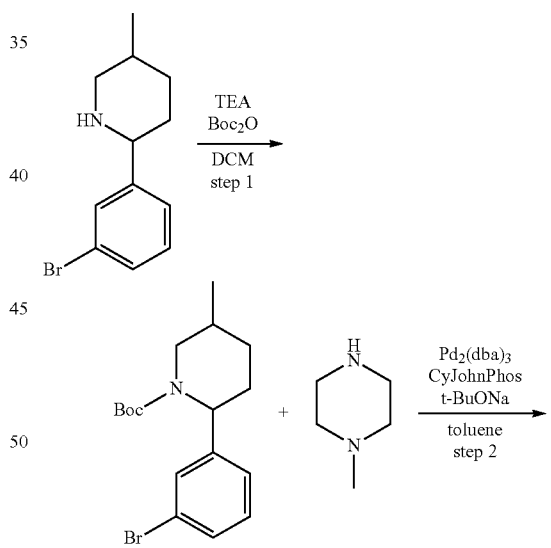

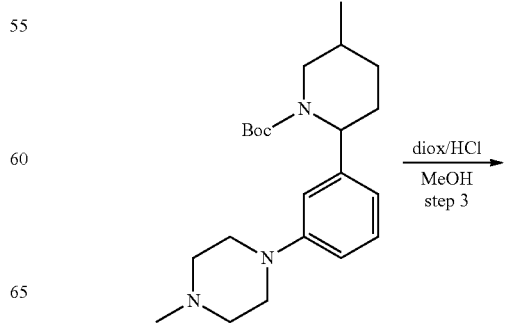

1723
-continued

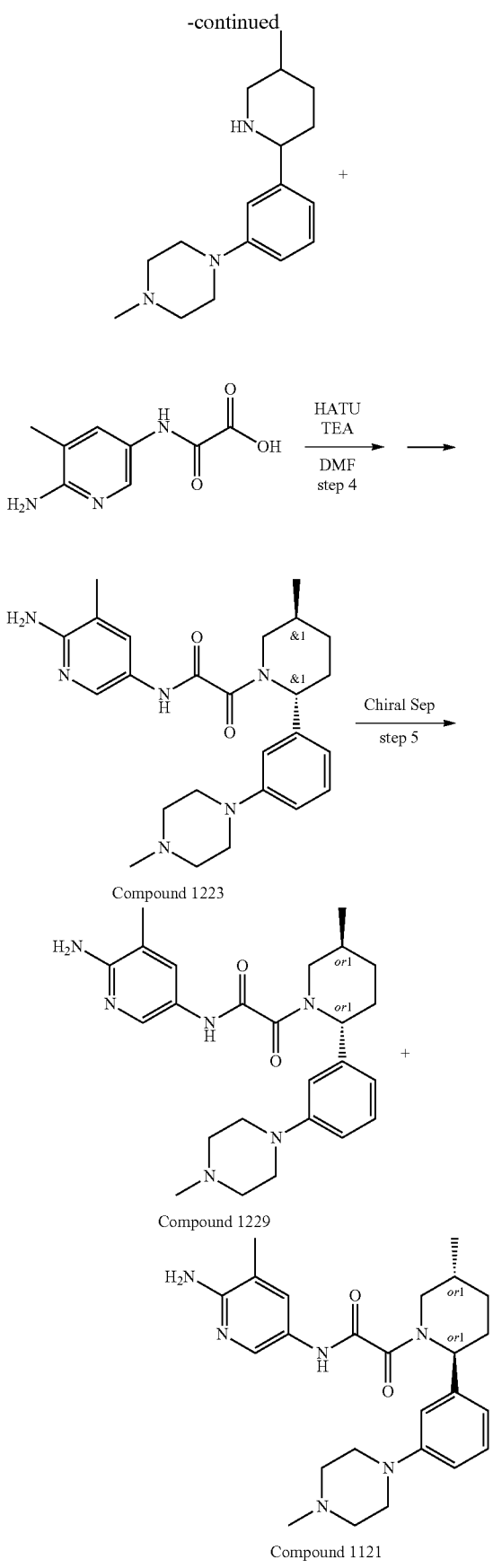

Compound 1223

Compound 1229

Compound 1121

1724

Step 4: Synthesis of N-(6-amino-5-methylpyridin-3-yl)-2-(5-methyl-2-(3-(4-methylpiperazin-1-yl)phenyl)piperidin-1-yl)-2-oxoacetamide (Compound 1223

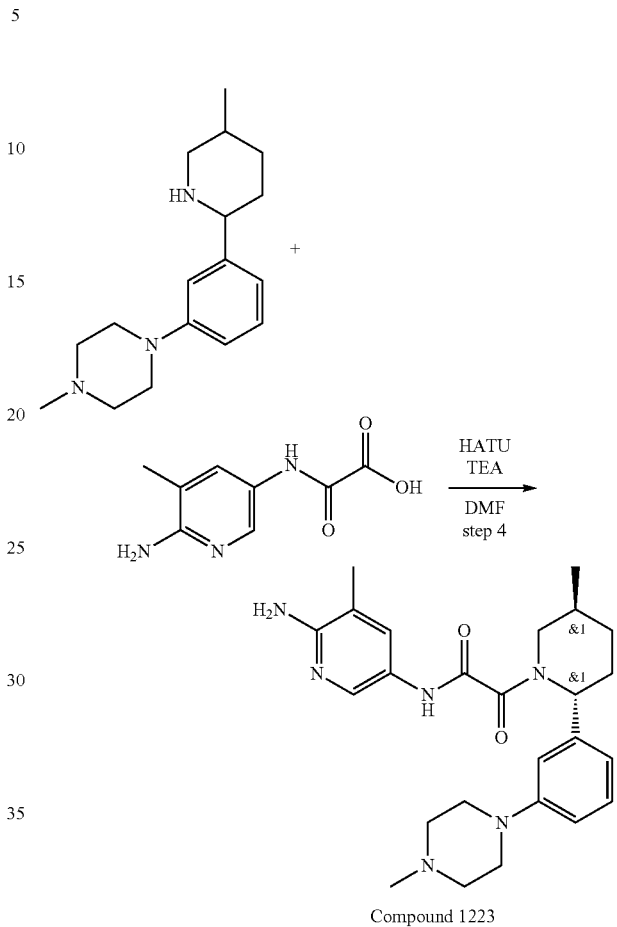

Compound 1223

DIPEA (87.45 mg, 676.63 umol, 117.86 uL) was added to the solution of respective 2-[(6-amino-5-methyl-3-pyridyl)amino]-2-oxo-acetic acid (52.82 mg, 270.65 umol) and 1-methyl-4-[3-(5-methyl-2-piperidyl)phenyl]piperazine (74 mg, 270.65 umol) in DMF (5 mL). The resulting mixture was stirred for 5 min followed by the addition of HATU (113.20 mg, 297.72 umol). Then the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and MeOH+NH$_3$ as an eluent mixture) to afford N-(6-amino-5-methyl-3-pyridyl)-2-[(2R,5S)-5-methyl-2-[3-(4-methylpiperazin-1-yl)phenyl]-1-piperidyl]-2-oxo-acetamide (30.7 mg, 68.14 umol, 25.17% yield).

Compound 1223:

$^1$H NMR (500 MHz, DMSO-d$_6$) δ (ppm) 0.96-1.03 (m, 3H), 1.25-1.38 (m, 1H), 1.61-1.76 (m, 1H), 1.80-1.93 (m, 1H), 1.96-2.03 (m, 3H), 2.04-2.17 (m, 1H), 2.17-2.23 (m, 4H), 2.40-2.44 (m, 4H), 2.72-2.76 (m, 0.4H), 3.07-3.13 (m, 4H), 3.22-3.26 (m, 0.6H), 3.39-4.04 (m, 1H), 5.07-5.55 (m, 1H), 5.58-5.67 (m, 2H), 6.68-6.79 (m, 1H), 6.78-6.84 (m, 2H), 7.15-7.24 (m, 1H), 7.40-7.50 (m, 1H), 7.94-8.06 (m, 1H), 10.45-10.58 (m, 1H).

LCMS(ESI): [M]$^+$ m/z: calcd 450.2; found 451.2; Rt=1.880 min.

Step 5: Chiral Separation (Compound 1121 and Compound 1229

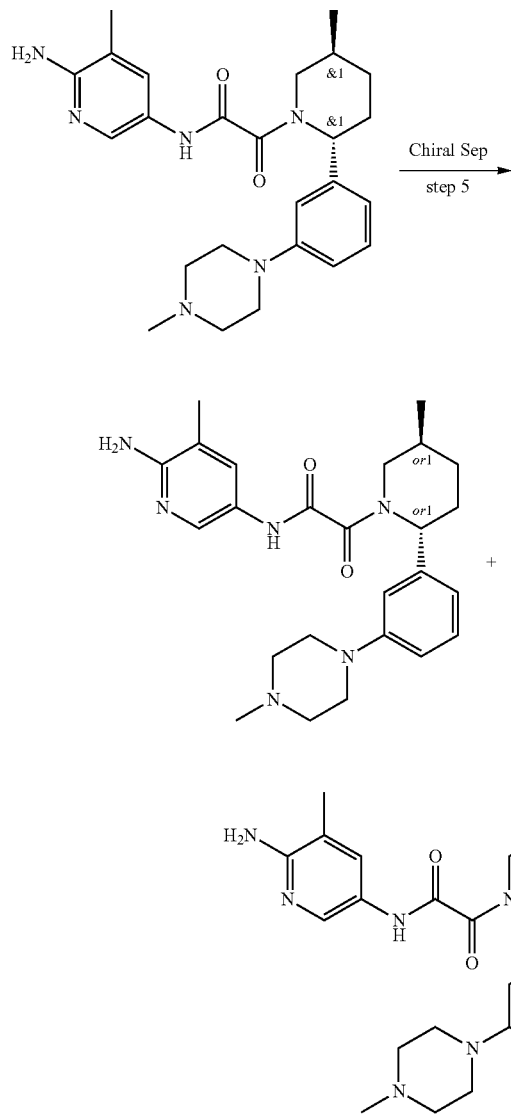

Racemic N-(6-amino-5-methyl-3-pyridyl)-2-[(2R,5S)-5-methyl-2-[3-(4-methylpiperazin-1-yl)phenyl]-1-piperidyl]-2-oxo-acetamide (18.5 mg, 41.06 μmol) was chiral separated (Column: Chiralpak AD-H (250-20 mm-5 m); Mobile phase: Hexane-IPA-MeOH, 40-30-30 Flow Rate: 12 mL/min) to obtain N-(6-amino-5-methyl-3-pyridyl)-2-[(2S,5R)-5-methyl-2-[3-(4-methylpiperazin-1-yl)phenyl]-1-piperidyl]-2-oxo-acetamide (8.66 mg, 19.22 mol, 46.81% yield) (RT=25.5 min) and N-(6-amino-5-methyl-3-pyridyl)-2-[(2R,5S)-5-methyl-2-[3-(4-methylpiperazin-1-yl)phenyl]-1-piperidyl]-2-oxo-acetamide (8.29 mg, 18.40 μmol, 44.81% yield) (RT=47.1 min).

Compound 1121:

$^1$H NMR (600 MHz, DMSO-d$_6$) δ (ppm) 0.99-1.00 (m, 3H), 1.33-1.36 (m, 2H), 1.64-1.90 (m, 3H), 1.99-2.20 (m, 6H), 2.42-2.43 (m, 2H), 3.08-3.26 (m, 4H), 3.41-4.01 (m, 3H), 5.10-5.62 (m, 4H), 6.70-6.82 (m, 3H), 7.19-7.22 (m, 1H), 7.44-7.49 (m, 1H), 7.96-8.01 (m, 1H), 10.48-10.51 (m, 1H).

LCMS(ESI): [M]$^+$ m/z: calcd 450.2; found 451.2; Rt=1.934 min.

Compound 1229:

$^1$H NMR (600 MHz, DMSO-d$_6$) δ (ppm) 0.99-1.00 (m, 3H), 1.22-1.36 (m, 2H), 1.62-1.90 (m, 3H), 1.99-2.20 (m, 6H), 2.42-2.43 (m, 2H), 3.08-3.24 (m, 4H), 3.41-4.01 (m, 3H), 5.10-5.62 (m, 4H), 6.70-6.82 (m, 3H), 7.19-7.22 (m, 1H), 7.44-7.49 (d, 1H), 7.96-8.01 (d, 1H), 10.48-10.51 (d, 1H).

LCMS(ESI): [M]$^+$ m/z: calcd 450.2; found 451.2; Rt=1.603 min.

Example 247. The Synthesis of Rel-N-(6-amino-5-methyl-3-pyridyl)-2-[(2R,4R,5R)-4-Isopropoxy-5-methyl-2-phenyl-1-piperidyl]-2-oxo-acetamide (Compound 1327), Rel-N-(6-amino-5-methyl-3-pyridyl)-2-[(2S,4S,5S)-4-Isopropoxy-5-methyl-2-phenyl-1-piperidyl]-2-oxo-acetamide (Compound 1088), Rel-N-(6-amino-5-methyl-3-pyridyl)-2-[(2R,4S,5R)-4-Isopropoxy-5-methyl-2-phenyl-1-piperidyl]-2-oxo-acetamide (Compound 1302) and Rel-N-(6-amino-5-methyl-3-pyridyl)-2-[(2S,4R,5S)-4-Isopropoxy-5-methyl-2-phenyl-1-piperidyl]-2-oxo-acetamide (Compound 1351

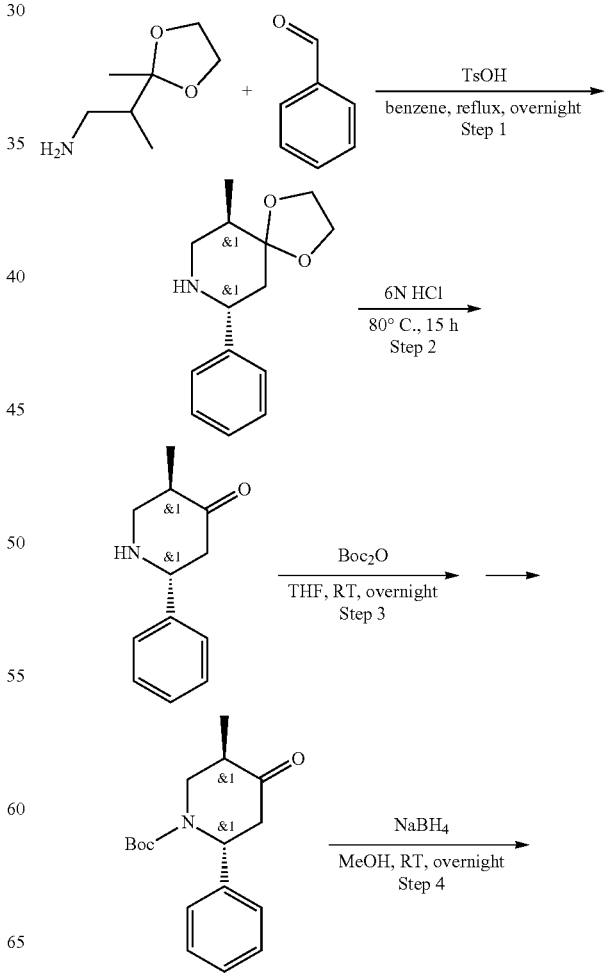

1727
-continued
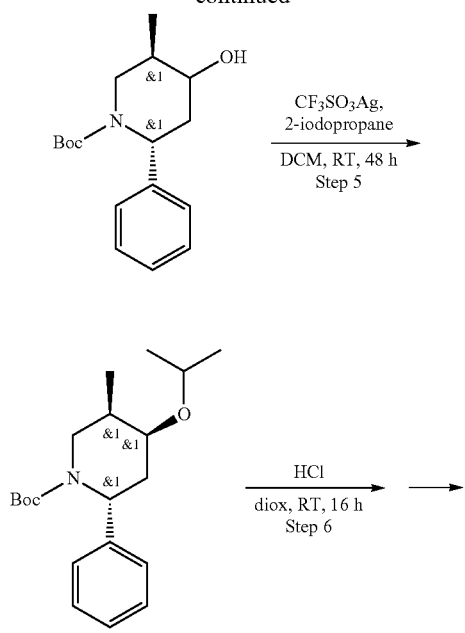
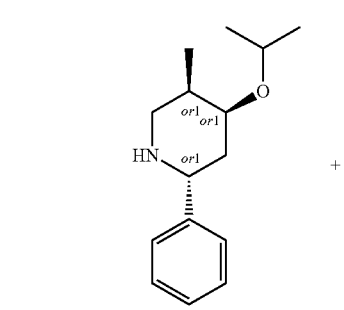
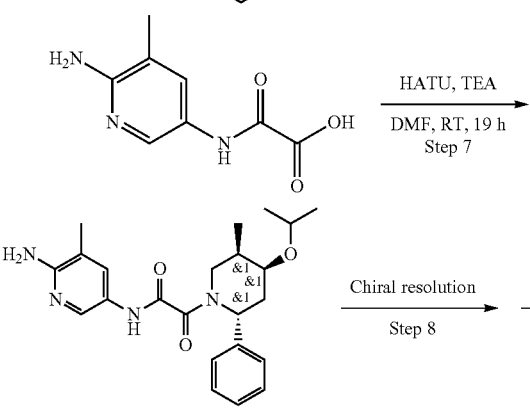
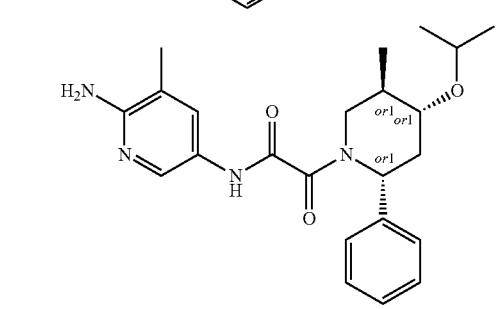
Compound 1327
1728
-continued
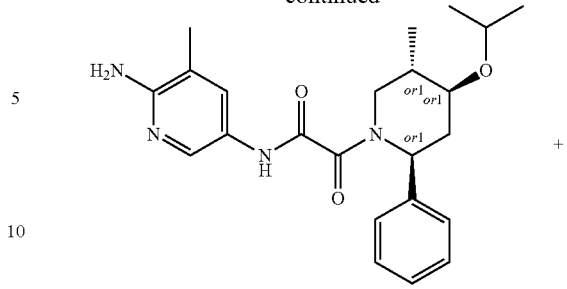
Compound 1088
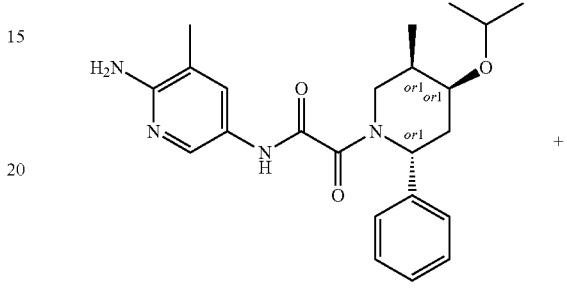
Compound 1302
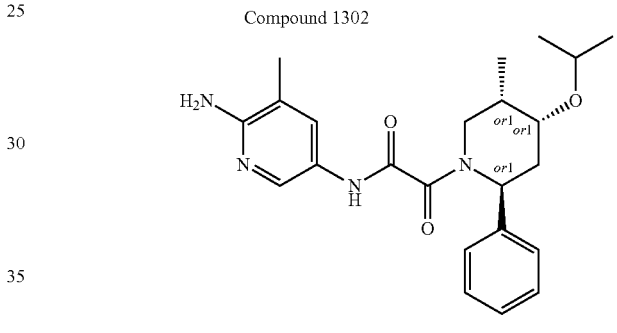
Compound 1351
Step 1: The Synthesis of (6R,9R)-6-methyl-9-phenyl-1,4-dioxa-8-azaspiro[4.5]decane
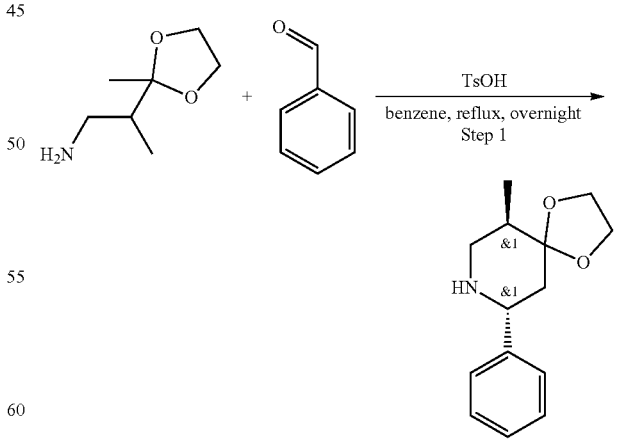
2-(2-methyl-1,3-dioxolan-2-yl)propan-1-amine (2 g, 13.77 mmol) was dissolved in Benzene (40 mL) and benzaldehyde (1.46 g, 13.77 mmol, 1.41 mL) was added thereto followed by addition of p-Toluenesulfonic acid monohydrate (7.86 g, 41.32 mmol, 6.34 mL). The resulting mixture was heated to reflux and refluxed under Dean-Stark trap overnight. Upon completion of the reaction benzene was evaporated. Residue was dissolved in 20 mL of water, $K_2CO_3$ was added to alkaline pH, aqueous phase were extracted with $CHCl_3$ (3*15 mL). The combined organic layers were extracted with aqueous $NaHSO_4$ (2 g in 20 mL of water, 2*20 mL). The combined aqueous layers were basified with $K_2CO_3$. The resulting mixture was extracted with $CHCl_3$ (3*20 mL). Combined organic layers were dried over $Na_2SO_4$, filtered and evaporated to obtain (6R,9R)-6-methyl-9-phenyl-1,4-dioxa-8-azaspiro[4.5]decane (1.1 g, 4.71 mmol, 34.23% yield).

$^1$H NMR (500 MHz, $CDCl_3$) δ (ppm) 0.88 (d, 3H), 1.64 (m, 2H), 1.88 (m, 1H), 1.89 (m, 1H), 2.73 (m, 1H), 3.03 (m, 1H), 3.82 (m, 1H), 3.98 (m, 4H), 7.29-7.33 (m, 5H).

LCMS(ESI): [M+H]$^+$ m/z: calcd 234.2; found 234.2; Rt=0.803 min.

Step 2: The Synthesis of (2R,5R)-5-methyl-2-phenyl-piperidin-4-one

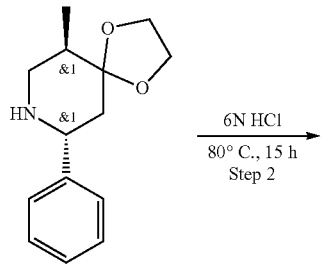

The mixture of (6R,9R)-6-methyl-9-phenyl-1,4-dioxa-8-azaspiro[4.5]decane (1 g, 4.29 mmol) in 6N HCl (10 mL) was allowed to stir at 80° C. for 15 hr. Upon completion of the reaction, 10 mL of water was added to mixture and solution was basified with $K_2CO_3$ to alkaline pH. Aqueous layer was extracted with $CHCl_3$ (3*10 mL), combined organic phase was dried over $Na_2SO_4$, filtered and concentrated under reduced pressure to obtain (2R,5R)-5-methyl-2-phenyl-piperidin-4-one (0.76 g, 4.02 mmol, 93.69% yield).

$^1$H NMR (500 MHz, $CDCl_3$) δ (ppm) 1.08 (d, 3H), 2.57 (m, 2H), 2.70 (m, 2H), 3.47 (m, 1H), 3.95 (m, 1H), 7.37 (m, 5H).

LCMS(ESI): [M+H]$^+$ m/z: calcd 190.2; found 190.2; Rt=0.626 min.

Step 3. The Synthesis of tert-butyl 2R,5R)-5-methyl-oxo-2-phenyl-piperidine-1-carboxylate

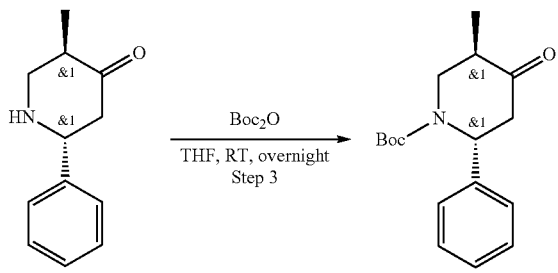 [SMILES: "Boc2O" ; C[C@@H]1CN[C@@H](c2ccccc2)CC1=O ; "THF, RT, overnightStep 3" ; C[C@@H]1CN(C(=O)OC(C)(C)C)[C@@H](c2ccccc2)CC1=O]

To the mixture of (2R,5R)-5-methyl-2-phenyl-piperidin-4-one (0.76 g, 4.02 mmol) in THF (15 mL), tert-butoxycarbonyl tert-butyl carbonate (876.43 mg, 4.02 mmol, 921.59 uL) was added in one portion. The resulting mixture was allowed to stir overnight at room temperature.

Upon the completion of the reaction, THF was evaporated under reduced pressure to afford tert-butyl (2R,5R)-5-methyl-4-oxo-2-phenyl-piperidine-1-carboxylate (1.1 g, 3.80 mmol, 94.66% yield).

$^1$H NMR (500 MHz, $CDCl_3$) δ (ppm) 1.17 (m, 3H), 1.43 (s, 9H), 2.48 (m, 1H), 2.94 (m, 2H), 3.58 (m, 1H), 3.81 (m, 1H), 5.60 (m, 1H), 7.22-7.32 (m, 5H).

LCMS(ESI): [M-Boc]$^+$ m/z: calcd 190.2; found 190.2; Rt=1.414 min.

Step 4: The Synthesis of tert-butyl (2R,4S,5R)-4-hydroxy-5-methyl-2-phenyl-piperidine-1-carboxylate

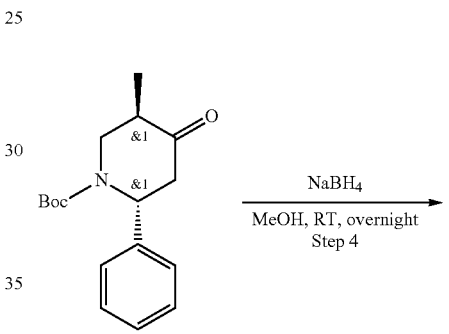

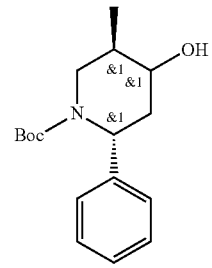

Sodium Borohydride (143.81 mg, 3.80 mmol, 134.40 uL) was added in one portion to an ice cooled solution of tert-butyl (2R,5R)-5-methyl-4-oxo-2-phenyl-piperidine-1-carboxylate (1.1 g, 3.80 mmol) in MeOH (20 mL). The resulting mixture was allowed to stir overnight at 25° C. Upon completion of the reaction, MeOH was evaporated to dryness. 20 mL of water was added to residue and mixture was basified with $K_2CO_3$ to alkaline pH, aqueous phase was extracted with $CHCl_3$ (3*15 mL), combined organic layers were dried over $Na_2SO_4$, filtered and evaporated under reduced pressure to afford tert-butyl (2R,4S,5R)-4-hydroxy-5-methyl-2-phenyl-piperidine-1-carboxylate (0.9 g, 3.09 mmol, 81.25% yield).

LCMS(ESI): [M-Boc]$^+$ m/z: calcd 192.2; found 192.2; Rt=1.362 min.

Step 5: The Synthesis of tert-butyl (2R,4S,5R)-4-methoxy-5-methyl-2-phenyl-piperidine-1-carboxylate

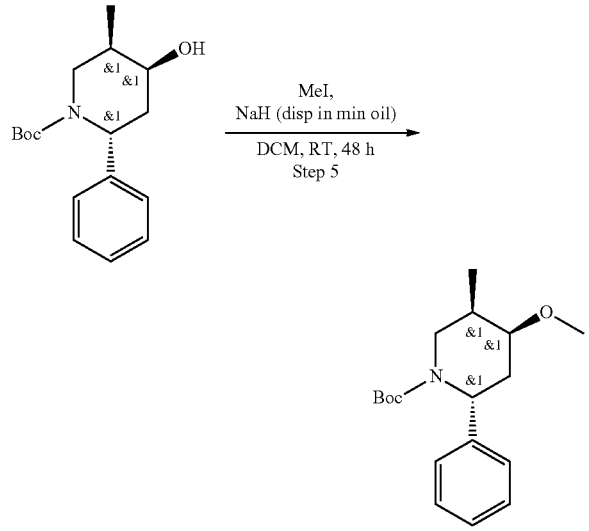

To a mixture of tert-butyl (2R,4S,5R)-4-hydroxy-5-methyl-2-phenyl-piperidine-1-carboxylate (0.4 g, 1.37 mmol) in DMF (10 mL), sodium hydride (in oil dispersion) 60% dispersion in mineral oil (47.34 mg, 2.06 mmol) was added portionwise, the resulting mixture was stirred at room temperature for 20 min and cooled with ice to 0° C. Iodomethane (292.27 mg, 2.06 mmol, 128.19 uL) was added in one portion and the reaction was allowed to stir at room temperature for 48 hr. Upon completion of the reaction, 25 mL of water was added to the mixture. The aqueous phase was extracted with EtOAc (3*15 mL), combined organic layers was washed with brine (3*10 mL), dried over $Na_2SO_4$, filtered and concentrated under reduced pressure to obtain tert-butyl (2R,4S,5R)-4-methoxy-5-methyl-2-phenyl-piperidine-1-carboxylate (0.4 g, 1.31 mmol, 95.41% yield).

LCMS(ESI): $[M+H]^+$ m/z: calcd 306.2; found 306.2; Rt=1.428 min.

Step 6: The Synthesis of (2R,4S,5R)-4-methoxy-5-methyl-2-phenyl-piperidine

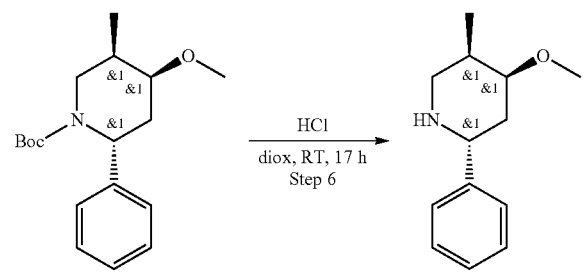

tert-butyl (2R,4S,5R)-4-methoxy-5-methyl-2-phenyl-piperidine-1-carboxylate (0.41 g, 1.34 mmol) was dissolved in Diox/HCl (10 mL). The resulting mixture was allowed to stir at 25° C. for 17 hr. Upon the completion of the reaction, solvent was evaporated to dryness to obtain (2R,4S,5R)-4-methoxy-5-methyl-2-phenyl-piperidine (0.23 g, 951.37 umol, 70.87% yield, HCl).

LCMS(ESI): $[M+H]^+$ m/z: calcd 206.2; found 206.2; Rt=0.842 min.

Step 7: The Synthesis of rac-N-(6-amino-5-methyl-3-pyridyl)-2-[(2R,4S,5R)-4-Isopropoxy-5-methyl-2-phenyl-1-piperidyl]-2-oxo-acetamide

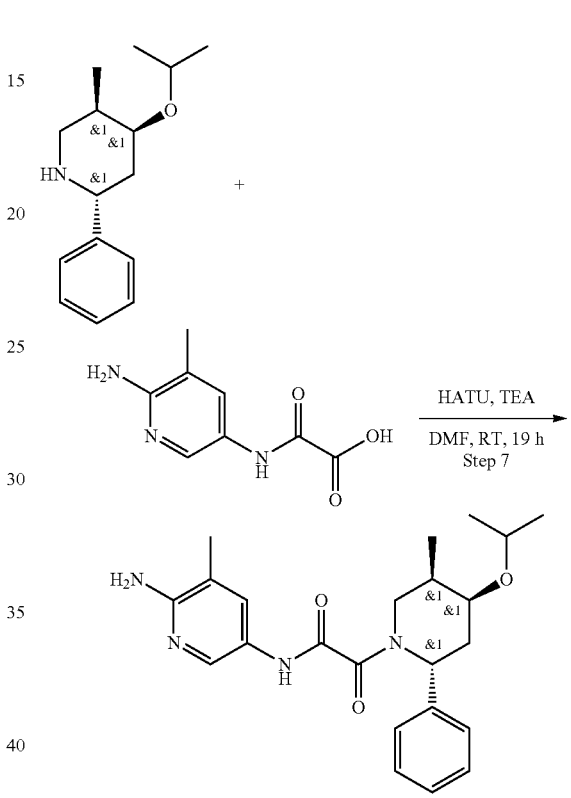

To a mixture of (2R,4S,5R)-4-isopropoxy-5-methyl-2-phenyl-piperidine (0.2 g, 741.26 umol, HCl), 2-[(6-amino-5-methyl-3-pyridyl)amino]-2-oxo-acetic acid (144.68 mg, 741.26 umol) and triethylamine (525.06 mg, 5.19 mmol, 723.22 uL) in DMF (4 mL), HATU (338.22 mg, 889.52 umol) was added in one portion. The resulting mixture was left to stir at room temperature for 19 hr. Upon the completion of the reaction, DMF was evaporated, residue was subjected to HPLC (0-5 min 30-80% Water/MeOH/0.1% $NH_4OH$ flow: 30 mL/min (loading pump 4 mL/min MeOH), column: YMC Triart C18 100*20 mm, 5 um) to afford N-(6-amino-5-methyl-3-pyridyl)-2-[(2R,4S,5R)-4-isopropoxy-5-methyl-2-phenyl-1-piperidyl]-2-oxo-acetamide (0.052 g, 126.67 umol, 17.09% yield).

$^1$H NMR (500 MHz, dmso) δ 0.62-1.05 (m, 9H), 1.67-1.92 (m, 1H), 1.94-2.05 (m, 3H), 2.15 (s, 1H), 2.67-3.14 (m, 1H), 3.37-3.68 (m, 3H), 3.69-4.20 (m, 1H), 5.14-5.57 (m, 1H), 5.58-5.80 (m, 2H), 7.02-7.23 (m, 1H), 7.24-7.32 (m, 3H), 7.34-7.42 (m, 1H), 7.43-7.53 (m, 1H), 7.80-8.06 (m, 1H), 10.18-10.60 (m, 1H).

LCMS(ESI): $[M+H]^+$ m/z: calcd 411.2; found 411.2; Rt=2.297 min.

Step 8: The Synthesis of Rel-N-(6-amino-5-methyl-3-pyridyl)-2-[(2R,4R,5R)-4-Isopropoxy-5-methyl-2-phenyl-1-piperidyl]-2-oxo-acetamide (Compound 1327), Rel-N-(6-amino-5-methyl-3-pyridyl)-2-[(2S, 4S,5S)-4-Isopropoxy-5-methyl-2-phenyl-1-piperidyl]-2-oxo-acetamide (Compound 1088), Rel-N-(6-amino-5-methyl-3-pyridyl)-2-[(2R,4S,5R)-4-Isopropoxy-5-methyl-2-phenyl-1-piperidyl]-2-oxo-acetamide (Compound 1302) and Rel-N-(6-amino-5-methyl-3-pyridyl)-2-[(2S,4R,5S)-4-Isopropoxy-5-methyl-2-phenyl-1-piperidyl]-2-oxo-acetamide (Compound 1351

The mixture of diastereomers was separated by chiral chromatography (Chiralcel OD-H (250*20, 5 mkm), Hexane-IPA-MeOH, 90-5-5, 12 mL/min) to obtain Compound 1327 rel-N-(6-amino-5-methyl-3-pyridyl)-2-[(2R,4R,5R)-4-isopropoxy-5-methyl-2-phenyl-1-piperidyl]-2-oxo-acetamide (0.00422 g, 10.28 µmol, 8.12% yield), Compound 1088 rel-N-(6-amino-5-methyl-3-pyridyl)-2-[(2S,4S,5S)-4-isopropoxy-5-methyl-2-phenyl-1-piperidyl]-2-oxo-acetamide (3.39 mg, 8.26 µmol, 6.52% yield), Compound 1302 rel-N-(6-amino-5-methyl-3-pyridyl)-2-[(2R,4S,5R)-4-isopropoxy-5-methyl-2-phenyl-1-piperidyl]-2-oxo-acetamide (0.01669 g, 40.66 µmol, 32.10% yield), Compound 1351 rel-N-(6-amino-5-methyl-3-pyridyl)-2-[(2S,4R,5S)-4-isopropoxy-5-methyl-2-phenyl-1-piperidyl]-2-oxo-acetamide (0.01743 g, 42.46 mol, 33.52% yield).

Preparative:

RT for Compound 1088 (Chiralcel OD-H (250*20, 5 mkm), Hexane-IPA-MeOH, 90-5-5, 12 mL/min)=33.950 min.

RT for Compound 1351 (Chiralcel OD-H (250*20, 5 mkm), Hexane-IPA-MeOH, 90-5-5, 12 mL/min)=45.434 min.

RT to Compound 1302 (Chiralcel OD-H (250* 20, 5 mkm), Hexane-IPA-MeOH, 90-5-5, 12 mL/min)=57.493 min.

RT to Compound 1327 (Chiralcel OD-H (250*20, 5 mkm), Hexane-IPA-MeOH, 90-5-5, 12 mL/min)=79.390 min.

Compound 1327:

Yield: 4.22 mg (8.12%)

RT (Chiralcel OD-H (250*4.6, 5 mkm), Hexane-IPA-MeOH, 80-10-10, 0.6 mL/min)=26.456 min.

$^1$H NMR (dmso, 600 MHz): δ (ppm) 0.87-0.91 (m, 3H), 1.00-1.04 (m, 6H), 1.78-1.85 (m, 1H), 1.92-1.99 (m, 1H), 1.99-2.05 (m, 3H), 2.05-2.11 (m, 1H), 2.65-3.14 (m, 1H), 3.45-3.61 (m, 2H), 3.61-4.21 (m, 1H), 5.23-5.89 (m, 3H), 7.27-7.31 (m, 2H), 7.35-7.37 (m, 1H), 7.38-7.44 (m, 2H), 7.47-7.55 (m, 1H), 7.95-8.09 (m, 1H), 10.50-10.67 (m, 1H).

LCMS(ESI): [M+H]$^+$ m/z: calcd 411.2; found 411.2; Rt=2.149 min.

Compound 1088:

Yield: 3.39 mg (6.52%)

RT (Chiralcel OD-H (250*4.6, 5 mkm), Hexane-IPA-MeOH, 80-10-10, 0.6 mL/min)=14.072 min.

$^1$H NMR (dmso, 600 MHz): δ (ppm) 0.87-0.91 (m, 3H), 1.00-1.04 (m, 6H), 1.78-1.85 (m, 1H), 1.92-1.99 (m, 1H), 1.99-2.05 (m, 3H), 2.05-2.10 (m, 1H), 2.65-3.14 (m, 1H), 3.45-3.61 (m, 2H), 3.61-4.21 (m, 1H), 5.23-5.88 (m, 3H), 7.27-7.31 (m, 2H), 7.35-7.38 (m, 1H), 7.38-7.42 (m, 2H), 7.47-7.55 (m, 1H), 7.95-8.09 (m, 1H), 10.50-10.67 (m, 1H).

LCMS(ESI): [M+H]$^+$ m/z: calcd 411.2; found 411.2; Rt=2.147 min.

Compound 1302:

Yield: 16.69 mg (32.10%)

RT (Chiralcel OD-H (250*4.6, 5 mkm), Hexane-IPA-MeOH, 80-10-10, 0.6 mL/min)=20.214 min.

$^1$H NMR (dmso, 600 MHz): δ (ppm) 0.43-0.72 (m, 3H), 0.88-0.97 (m, 3H), 0.97-1.07 (m, 3H), 1.64-1.81 (m, 1H), 1.94-2.05 (m, 3H), 2.09-2.27 (m, 2H), 2.89-3.29 (m, 1H), 3.36-3.57 (m, 2H), 3.66-4.07 (m, 1H), 5.15-5.43 (m, 1H), 5.54-6.02 (m, 2H), 7.11-7.22 (m, 1H), 7.23-7.33 (m, 4H), 7.33-7.54 (m, 1H), 7.69-8.11 (m, 1H), 9.67-10.69 (m, 1H).

LCMS(ESI): [M+H]$^+$ m/z: calcd 411.2; found 411.2; Rt=2.105 min.

Compound 1351:

Yield: 17.43 mg (33.52%)

RT (Chiralcel OD-H (250*4.6, 5 mkm), Hexane-IPA-MeOH, 80-10-10, 0.6 mL/min)=17.795 min.

$^1$H NMR (dmso, 600 MHz): δ (ppm) 0.42-0.72 (m, 3H), 0.87-0.98 (m, 3H), 0.97-1.07 (m, 3H), 1.64-1.81 (m, 1H), 1.94-2.05 (m, 3H), 2.09-2.26 (m, 2H), 2.89-3.28 (m, 1H), 3.36-3.57 (m, 2H), 3.66-4.07 (m, 1H), 5.16-5.43 (m, 1H), 5.55-6.02 (m, 2H), 7.11-7.22 (m, 1H), 7.21-7.33 (m, 4H), 7.33-7.54 (m, 1H), 7.69-8.11 (m, 1H), 9.67-10.69 (m, 1H).

LCMS(ESI): [M+H]$^+$ m/z: calcd 411.2; found 411.2; Rt=2.103 min.

Example 248. The Synthesis of N-(6-amino-5-ethylpyridin-3-yl)-2-((2R,5S)-2-(4-(2-(dimethylamino)ethyl)phenyl)-5-methylpiperidin-1-yl)-2-oxoacetamide (Compound 1228)

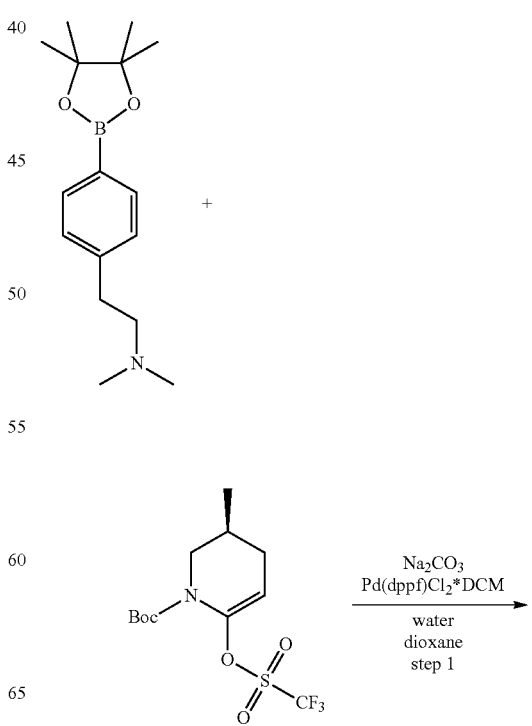

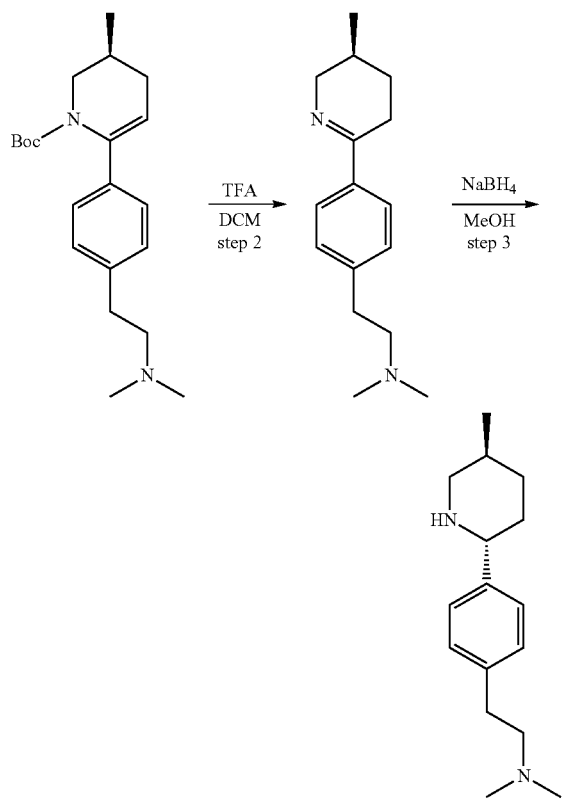

Step 1: Synthesis of (S)-tert-butyl 6-(4-(2-(dimethylamino)ethyl)phenyl)-3-methyl-3,4-dihydropyridine-1(2H)-carboxylate

[4-[2-(dimethylamino)ethyl]phenyl]boronic acid (8 g, 41.44 mmol) and tert-butyl (3S)-3-methyl-6-(trifluoromethylsulfonyloxy)-3,4-dihydro-2H-pyridine-1-carboxylate (21.47 g, 62.16 mmol) were mixed together in dioxane (91.71 mL). The resulting mixture was evacuated and then backfilled with argon, this operation was repeated three times, then sodium carbonate (8.78 g, 82.88 mmol, 3.47 mL) in water (4.83 mL) and [1,1'-bis(diphenylphosphino)ferrocene]dichloropalladium(II), complex with DCM (1.52 g, 2.07 mmol) were added under argon. The reaction mixture was stirred under argon at 90° C. for 15 hr, then cooled and evaporated in vacuum poured into water (180 ml) and extracted with EtOAc (2×150 ml). The combined organic extracts were washed with water (2*40 ml), dried over sodium sulphate and evaporated in vacuum to leave 14 g of crude product, 14 g of which was purification by column chromatography on silica gel using hexane/MTBE gradient (10-100% MTBE) to afford tert-butyl (3S)-6-[4-[2-(dimethylamino)ethyl]phenyl]-3-methyl-3,4-dihydro-2H-pyridine-1-carboxylate (3.5 g, 10.16 mmol, 24.52% yield).

LCMS(ESI): [M]$^+$ m/z: calcd 344.2; found 345.2; Rt=1.163 min.

Step 2: Synthesis of (S)—N,N-dimethyl-2-(4-(5-methyl-3,4,5,6-tetrahydropyridin-2-yl)phenyl)ethanamine

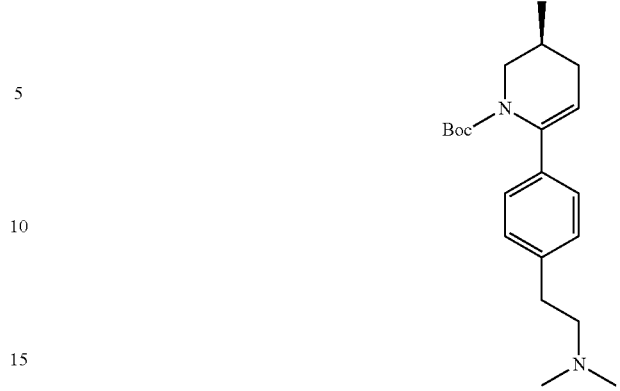

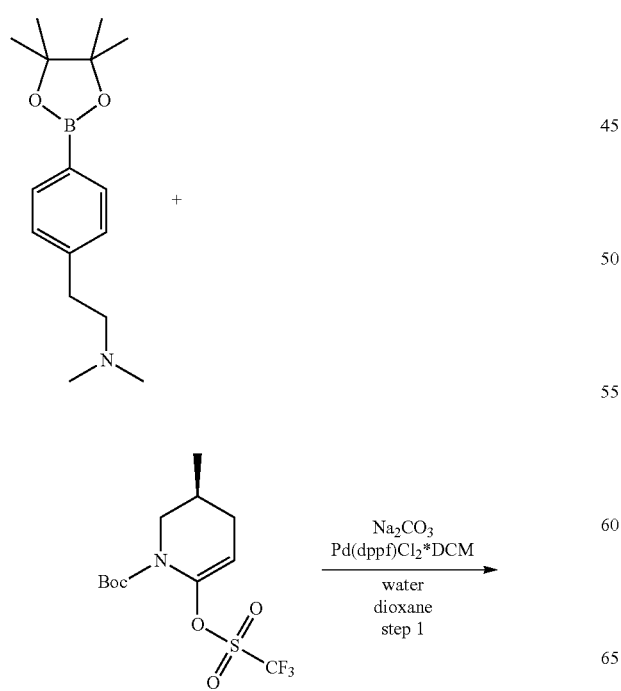

The solution of tert-butyl (3S)-6-[4-[2-(dimethylamino)ethyl]phenyl]-3-methyl-3,4-dihydro-2H-pyridine-1-carboxylate (3.50 g, 10.16 mmol) in DCM (20 mL) and TFA, 99% (20 g, 175.40 mmol, 13.51 mL) was stirred at 0° C. for 5 hr, and then evaporated in vacuum. Crushed ice (50 g) was added to the residue and pH was adjusted to 8 with a 10% aqueous solution of sodium hydro carbonate. The resulting mixture was extracted with MTBE (2*40 mL). The combined organic extracts were dried over sodium sulphate and evaporated in vacuum to afford N,N-dimethyl-2-[4-[(3S)-3-methyl-1,2,3,4-tetrahydropyridin-6-yl]phenyl]ethanamine (2 g, 8.18 mmol, 80.55% yield).

LCMS(ESI): [M]+ m/z: calcd 244.2; found 245.2; Rt=0.584 min.

Step 3: Synthesis of N,N-dimethyl-2-(4-((2R,5S)-5-methylpiperidin-2-yl)phenyl)ethanamine

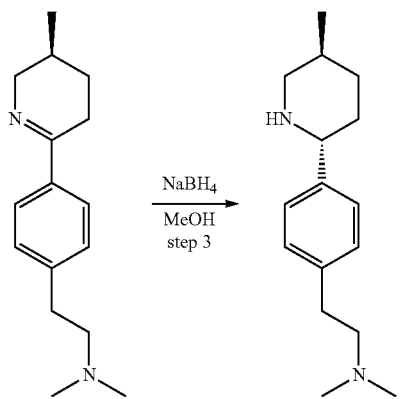 [SMILES: C[C@H]1CCC(c2ccc(CCN(C)C)cc2)=NC1 ; "MeOHstep 3" ; "NaBH4" ; C[C@H]1CC[C@H](c2ccc(CCN(C)C)cc2)NC1]

Sodium borohydride (619.26 mg, 16.37 mmol, 576.59 µL) was added in one portion to a stirred solution of N,N-dimethyl-2-[4-[(3S)-3-methyl-1,2,3,4-tetrahydropyridin-6-yl]phenyl]ethanamine (2.00 g, 8.18 mmol) in MeOH (20 mL) at 0° C. The resulting mixture was stirred at 0° C. for 6 hr, and then evaporated in vacuum. The residue was diluted with water (40 mL) and extracted with DCM (2*50 mL). The combined organic extracts were dried over sodium sulphate and evaporated in vacuum to afford N,N-dimethyl-2-[4-[(2R,5S)-5-methyl-2-piperidyl]phenyl]ethanamine (1.7 g, 6.90 mmol, 84.30% yield).

LCMS(ESI): [M]+ m/z: calcd 246.2; found 247.2; Rt=0.556 min.

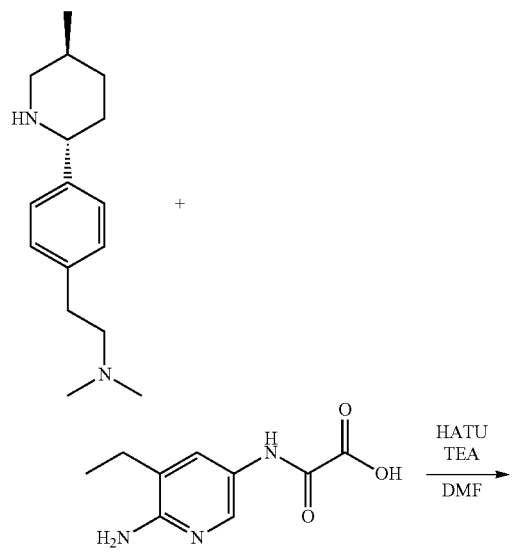

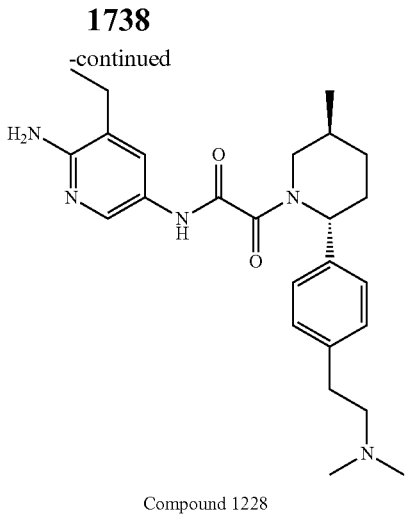

Compound 1228

2-[(6-amino-5-ethyl-3-pyridyl)amino]-2-oxo-acetic acid (339.63 mg, 1.62 mmol) and N,N-dimethyl-2-[4-[(2R,5S)-5-methyl-2-piperidyl]phenyl]ethanamine (0.32 g, 1.30 mmol) were mixed in DMF (20 mL). The reaction suspension was cooled to 0° C. and HATU (617.28 mg, 1.62 mmol) followed by TEA (131.42 mg, 1.30 mmol, 181.02 µL) were added and stirred at ambient temperature for 14 hr. The reaction mixture was evaporated in vacuum and obtained crude product 0.7 g was purified by preparative 50-50-75% 0-1-6 min H$_2$O/MeOH/0.1% NH$_4$OH, flow: 30 ml/min to afford product N-(6-amino-5-ethyl-3-pyridyl)-2-[(2R,5S)-2-[4-[2-(dimethylamino)ethyl]phenyl]-5-methyl-1-piperidyl]-2-oxo-acetamide (0.268 g, 612.46 µmol, 47.16% yield).

Compound 1228:

$^1$H NMR (600 MHz, DMSO-d$_6$) δ (ppm) 0.71-1.36 (m, 6H), 1.29-1.36 (m, 2H), 1.65-1.89 (m, 2H), 1.99-2.21 (m, 8H), 2.35-2.39 (m, 2H), 2.65-2.72 (m, 2H), 3.19-3.21 (m, 1H), 3.42-4.01 (m, 2H), 5.11-5.64 (m, 3H), 7.18-7.23 (m, 4H), 7.45-7.50 (d, 1H), 8.00-8.08 (d, 1H), 10.46-10.54 (d, 1H).

LCMS(ESI): [M]+ m/z: calcd 437.2; found 438.2; Rt=1.969 min.

Example 249. The Synthesis of N-(6-amino-5-ethylpyridin-3-yl)-2-(5-methyl-2-(4-(pyridin-4-yl)phenyl)piperidin-1-yl)-2-oxoacetamide (Compound 1233, Compound 1322, and Compound 1358

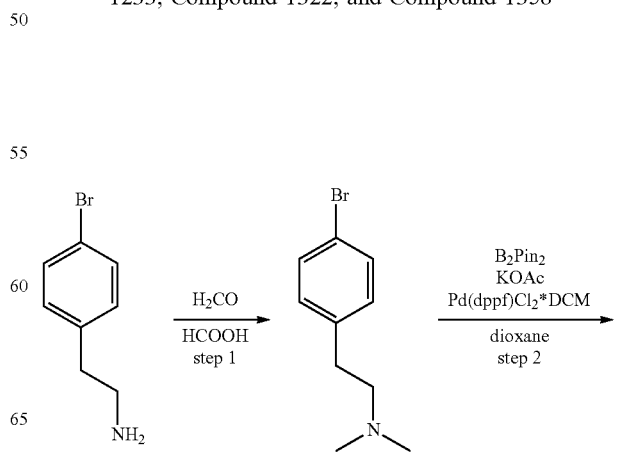

-continued
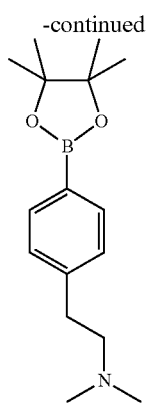
+
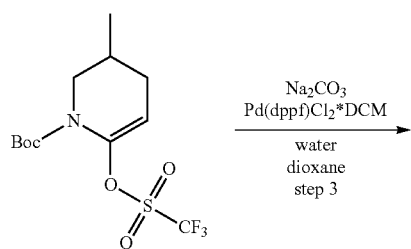
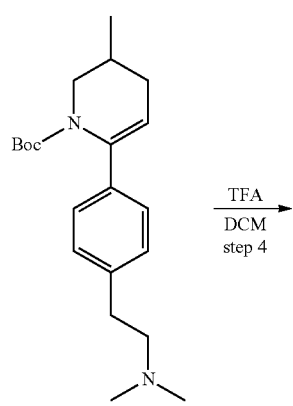
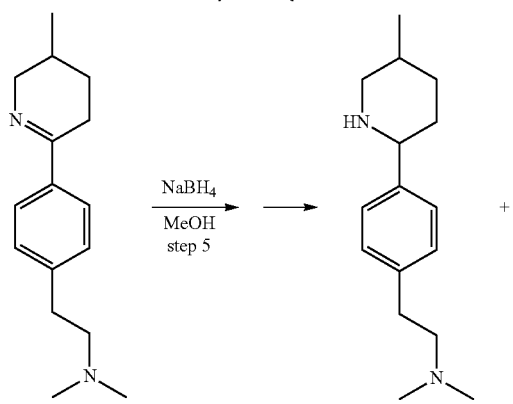
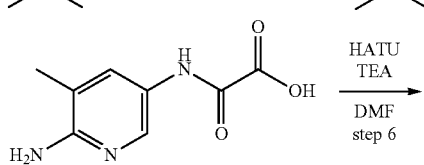
-continued
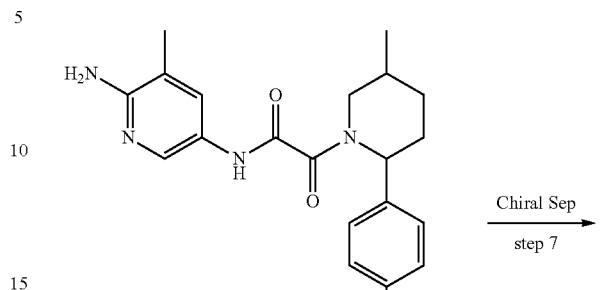
Compound 1233
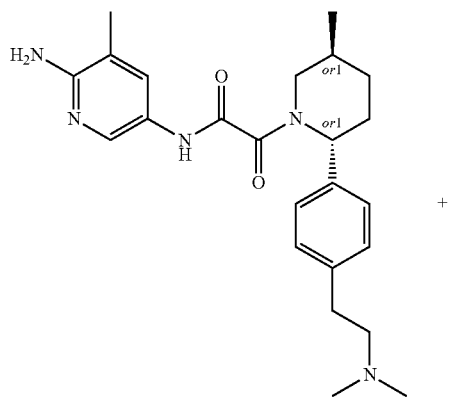
Compound 1322
+
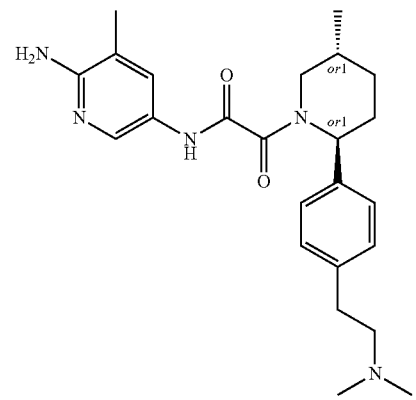
Compound 1358

Step 1: Synthesis of 2-(4-bromophenyl)-N,N-dimethylethanamine

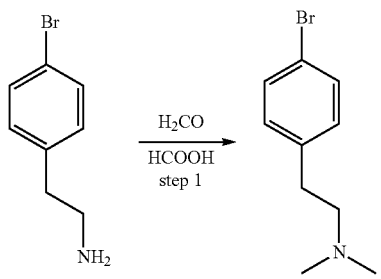

To a solution of 2-(4-bromophenyl)ethanamine (5 g, 24.99 mmol, 3.88 mL) in formic acid (30 mL) was added formaldehyde, 37% w/w aq. soln., stab. with 7-8% MeOH (4.50 g, 149.94 mmol, 4.17 mL). After stirring at 100° C. for 48 hr the reaction mixture was evaporated and poured in H₂O (200 ml) and pH was adjusted to 9 with a 10% aqueous solution of sodium hydro carbonate, extracted with MTBE (50 ml*2) and the combined organic layer was washed with H₂O (40 ml*2), dried and concentrated to afford product 2-(4-bromophenyl)-N,N-dimethyl-ethanamine (5.1 g, 22.36 mmol, 89.46% yield).

LCMS(ESI): [M]⁺ m/z: calcd 228.2; found 229.2; Rt=0.622 min.

Step 2: Synthesis of N,N-dimethyl-2-(4-(4,4,5,5-tetramethyl-1,3,2-dioxaborolan-2-yl)phenyl)ethanamine

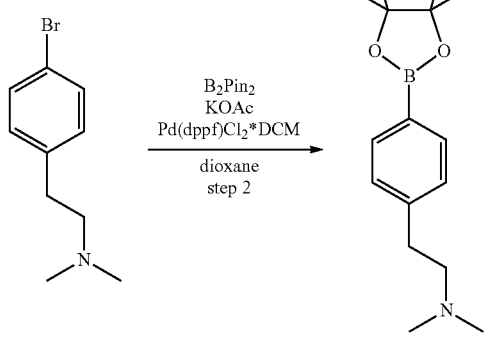

Potassium acetate (4.39 g, 44.71 mmol, 2.79 mL) was added to a solution of 2-(4-bromophenyl)-N,N-dimethyl-ethanamine (5.1 g, 22.36 mmol) and 4,4,5,5-tetramethyl-2-(4,4,5,5-tetramethyl-1,3,2-dioxaborolan-2-yl)-1,3,2-dioxaborolane (7.38 g, 29.06 mmol) in dioxane (150 mL). Reaction flask was evacuated and refilled with argon 3 times. Then Pd(dppf)Cl₂*DCM (817.89 mg, 1.12 mmol) was added under stream of argon. Resulting mixture was stirred at 100° C. for 12 hr under inert atmosphere, then cooled and evaporated in vacuum poured into water (200 ml) and extracted with DCM (2×100 ml). The combined organic extracts were washed with water (150 ml), dried over sodium sulphate and evaporated in vacuum to afford product N,N-dimethyl-2-[4-(4,4,5,5-tetramethyl-1,3,2-dioxaborolan-2-yl)phenyl]ethanamine (5.5 g, 19.99 mmol, 89.40% yield).

LCMS(ESI): [M]⁺ m/z: calcd 275.2; found 276.2; Rt=0.974 min.

Step 3: Synthesis of tert-butyl 6-(4-(2-(dimethylamino)ethyl)phenyl)-3-methyl-3,4-dihydropyridine-1(2H)-carboxylate

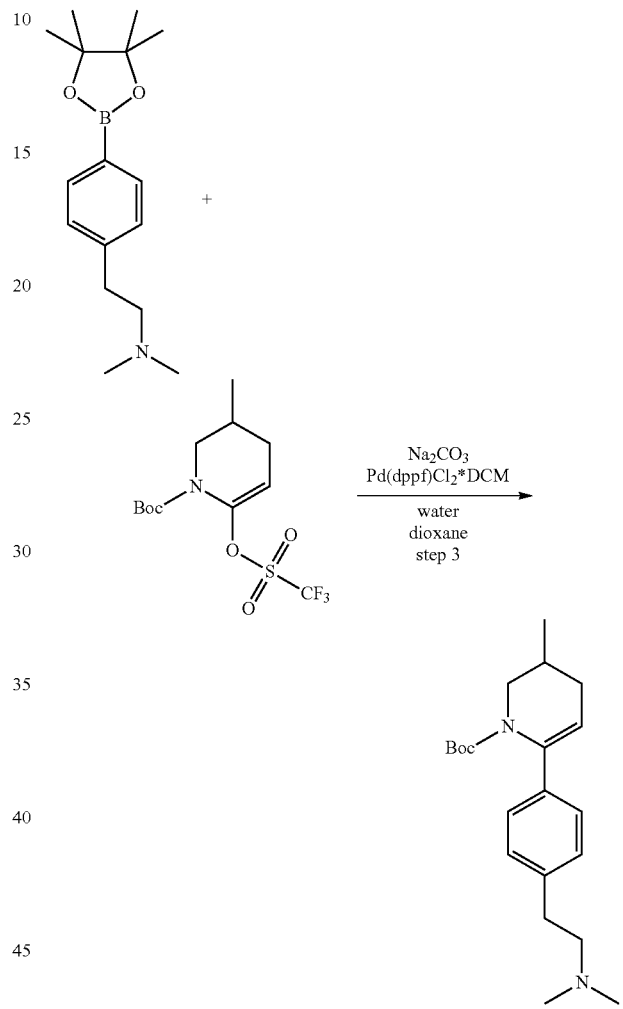

N,N-dimethyl-2-[4-(4,4,5,5-tetramethyl-1,3,2-dioxaborolan-2-yl)phenyl]ethanamine (3 g, 10.90 mmol) and tert-butyl 3-methyl-6-(trifluoromethylsulfonyloxy)-3,4-dihydro-2H-pyridine-1-carboxylate (8.28 g, 23.98 mmol) were mixed together in dioxane (95 mL). The resulting mixture was evacuated and then backfilled with argon, this operation was repeated three times, then sodium carbonate (2.31 g, 21.80 mmol, 913.39 uL) in water (5 mL) and [1,1'-bis(diphenylphosphino)ferrocene]dichloropalladium(II), complex with DCM (398.83 mg, 545.07 umol) were added under argon. The reaction mixture was stirred under argon at 90° C. for 48 hr, then cooled and evaporated in vacuum poured into water (180 ml) and extracted with EtOAc (2×150 ml). The combined organic extracts were washed with water (2*40 ml), dried over sodium sulphate and evaporated in vacuum to leave 4 g of crude product, 4 g of which was purification by column chromatography on silica gel using hexane/MTBE gradient (10-100% MTBE) to afford tertbutyl 6-[4-[2-(dimethylamino)ethyl]phenyl]-3-methyl-3,4-dihydro-2H-pyridine-1-carboxylate (0.35 g, 1.02 mmol, 9.32% yield).

LCMS(ESI): [M]+ m/z: calcd 344.2; found 345.2; Rt=1.139 min.

Step 4: Synthesis of N,N-dimethyl-2-(4-(5-methyl-3,4,5,6-tetrahydropyridin-2-yl)phenyl)ethanamine

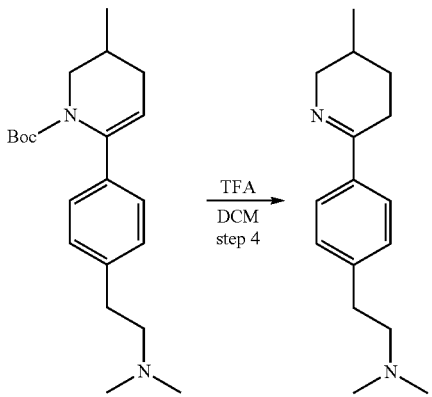 [SMILES: "TFA" ; CC1CC=C(c2ccc(CCN(C)C)cc2)N(C(=O)OC(C)(C)C)C1 ; "DCMstep 4" ; CC1CCC(c2ccc(CCN(C)C)cc2)=NC1]

The solution of tert-butyl 6-[4-[2-(dimethylamino)ethyl] phenyl]-3-methyl-3,4-dihydro-2H-pyridine-1-carboxylate (0.35 g, 1.02 mmol) in DCM (20 mL) and TFA (20 g, 175.41 mmol, 13.51 mL) was stirred at 0° C. for 5 hr, and then evaporated in vacuum. Crushed ice (50 g) was added to the residue and pH was adjusted to 8 with a 10% aqueous solution of sodium hydro carbonate. The resulting mixture was extracted with MTBE (2*40 mL). The combined organic extracts were dried over sodium sulphate and evaporated in vacuum to afford N,N-dimethyl-2-[4-(3-methyl-2,3,4,5-tetrahydropyridin-6-yl)phenyl]ethanamine (0.248 g, 1.01 mmol, 99.89% yield).

$^1$H NMR (500 MHz, CDCl$_3$) δ (ppm) 1.01 (d, 3H), 1.22 (m, 1H), 1.38 (m, 1H), 1.95 (m, 1H), 2.29 (s, 6H), 2.53 (m, 3H), 2.82 (m, 3H), 3.28 (m, 1H), 3.93 (m, 1H), 7.21 (m, 2H), 7.70 (m, 2H).

Step 5: Synthesis of N,N-dimethyl-2-(4-(5-methylpiperidin-2-yl)phenyl)ethanamine

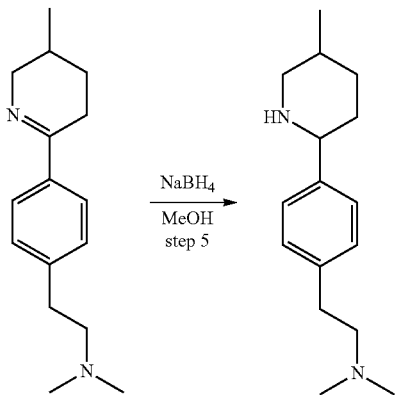 [SMILES: CC1CCC(c2ccc(CCN(C)C)cc2)=NC1 ; "MeOHstep 5" ; "NaBH4" ; CC1CCC(c2ccc(CCN(C)C)cc2)NC1]

Sodium borohydride (84.46 mg, 2.23 mmol, 78.94 uL) was added in one portion to a stirred solution of N,N-dimethyl-2-[4-(3-methyl-2,3,4,5-tetrahydropyridin-6-yl) phenyl]ethanamine (0.248 g, 1.01 mmol) in MeOH (20 mL) at 0° C. The resulting mixture was stirred at 0° C. for 5 hr, and then evaporated in vacuum. The residue was diluted with water (40 mL) and extracted with DCM (2*50 mL). The combined organic extracts were dried over sodium sulphate and evaporated in vacuum to afford N,N-dimethyl-2-[4-(5-methyl-2-piperidyl)phenyl]ethanamine (0.2 g, 811.72 umol, 79.99% yield).

LCMS(ESI): [M]+ m/z: calcd 246.2; found 247.2; Rt=0.344 min.

Step 6: Synthesis of N-(6-amino-5-ethylpyridin-3-yl)-2-(5-methyl-2-(4-(pyridin-4-yl)phenyl)piperidin-1-yl)-2-oxoacetamide (Compound 1233

2-[(6-amino-5-methyl-3-pyridyl)amino]-2-oxo-acetic acid (158.43 mg, 811.72 umol) and N,N-dimethyl-2-[4-(5-methyl-2-piperidyl)phenyl]ethanamine (0.2 g, 811.72 umol) were mixed in DMF (15 mL). The reaction suspension was cooled to 20° C. and HATU (339.50 mg, 892.89 umol) followed by TEA (328.55 mg, 3.25 mmol, 452.55 uL) were added and stirred at ambient temperature for 7 hr. The reaction mixture was evaporated in vacuum and obtained crude product 0.5 g was purified by preparative 30-30-80% 0-1-6 min H$_2$O/MeOH, flow: 30 ml/mi to afford product N-(6-amino-5-methyl-3-pyridyl)-2-[2-[4-[2-(dimethylamino)ethyl]phenyl]-5-methyl-1-piperidyl]-2-oxo-acetamide (0.1175 g, 277.42 umol, 34.18% yield).

Compound 1233:

$^1$H NMR (500 MHz, DMSO-d$_6$) δ (ppm) 0.96-1.05 (m, 3H), 1.25-1.39 (m, 1H), 1.58-1.69 (m, 1H), 1.80-1.91 (m, 1H), 1.97-2.03 (m, 3H), 2.05-2.13 (m, 1H), 2.14-2.16 (m, 6H), 2.17-2.28 (m, 1H), 2.41-2.44 (m, 2H), 2.65-2.70 (m, 2H), 2.72-3.21 (m, 1H), 3.39-4.04 (m, 1H), 5.06-5.57 (m, 1H), 5.58-5.72 (m, 2H), 7.17-7.25 (m, 4H), 7.42-7.54 (m, 1H), 7.92-8.07 (m, 1H), 10.42-10.55 (m, 1H).

LCMS(ESI): [M]f m/z: calcd 423.2; found 424.2; Rt=1.704 min.

Step 7: Chiral Separation (Compound 1322 and Compound 1358

Racemic N-(6-amino-5-methyl-3-pyridyl)-2-[(2R,5S)-2-[4-[2-(dimethylamino)ethyl]phenyl]-5-methyl-1-piperidyl]-2-oxo-acetamide (0.0979 g, 231.14 μmol) was chiral separated (Column: Chiralpak AD-H (250-20 mm-5 m); Mobile phase: IPA-MeOH, 50-50 Flow Rate: 12 mL/min) to obtain N-(6-amino-5-methyl-3-pyridyl)-2-[(2R,5S)-2-[4-[2-(dimethylamino)ethyl]phenyl]-5-methyl-1-piperidyl]-2-oxo-acetamide (0.04862 g, 114.79 mol, 49.66% yield) and N-(6-amino-3-pyridyl)-2-[(2S,5R)-5-methyl-2-[2-(trifluoromethyl)-1,3-benzothiazol-5-yl]-1-piperidyl]-2-oxo-acetamide (0.05775 g, 124.60 umol, 50.22% yield).

Rel Time for Compound 1322 in analytical conditions (column: AD-H, IPA-MeOH, 50-50, 0.6 ml/min as mobile phase) 52.72 min and for Compound 1358 36.60 min.

Compound 1322:

Retention time: 52.72 min $^1$H NMR (600 MHz, DMSO-d$_6$) δ (ppm) 0.99-1.2 (m, 3H), 1.22-1.36 (m, 2H), 1.63-1.88 (m, 2H), 1.98-2.26 (m, 10H), 2.37-2.44 (m, 2H), 2.65-2.72 (m, 2H), 3.18-3.21 (m, 1H), 3.42-4.01 (m, 1H), 5.10-5.62 (m, 3H), 7.18-7.25 (m, 4H), 7.44-7.49 (d, 1H), 7.96-8.02 (d, 1H), 10.46-10.49 (d, 1H).

LCMS(ESI): [M]+ m/z: calcd 423.2; found 424.2; Rt=2.040 min.

Compound 1358:
Retention time: 36.60 min
$^1$H NMR (600 MHz, DMSO-$d_6$) δ (ppm) 0.99-1.02 (m, 3H), 1.22-1.36 (m, 2H), 1.63-1.88 (m, 2H), 1.98-2.26 (m, 10H), 2.41-2.44 (m, 2H), 2.65-2.71 (m, 2H) 3.18-3.21 (m, 1H), 3.42-4.01 (m, 1H), 5.10-5.62 (m, 3H), 7.18-7.25 (m, 4H), 7.44-7.49 (d, 1H), 7.96-8.02 (d, 1H), 10.45-10.49 (d, 1H).
LCMS(ESI): [M]$^+$ m/z: calcd 423.2; found 424.2; Rt=2.051 min.

Example 250. The Synthesis of N-(6-amino-5-methylpyridin-3-yl)-2-(5-methyl-2-(3-(1-methylpiperidin-4-yl)phenyl)piperidin-1-yl)-2-oxoacetamide (Compound 1149, Compound 1253 and Compound 1291

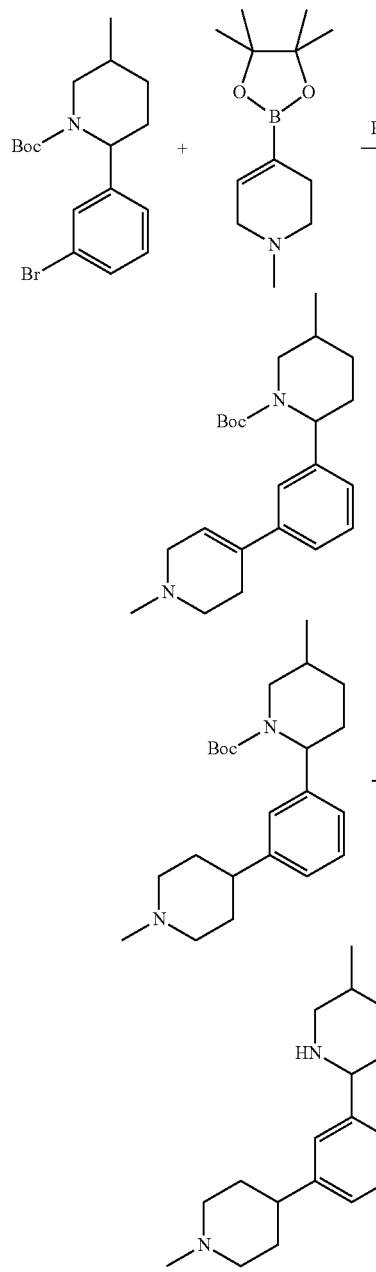

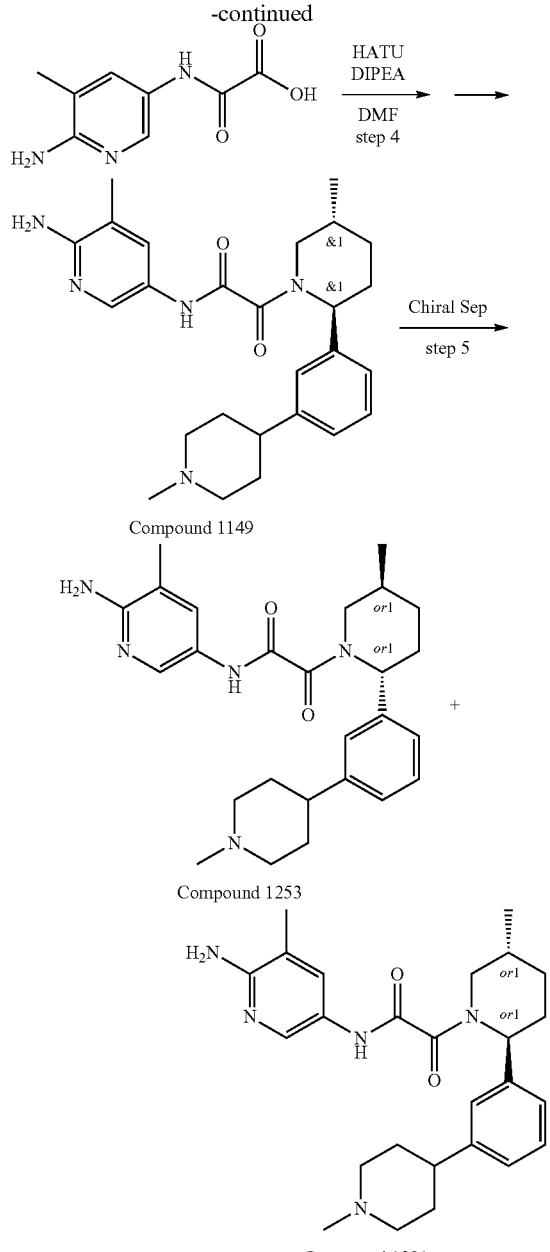

Step 1: Synthesis of tert-butyl 5-methyl-2-(3-(1-methyl-1,2,3,6-tetrahydropyridin-4-yl)phenyl)piperidine-1-carboxylate 1-methyl-4-(4,4,5,5-tetramethyl-1,3,2-dioxaborolan-2-yl)-3,6-dihydro-2H-pyridine (314.89 mg, 1.41 mmol), tert-butyl 2-(3-bromophenyl)-5-methyl-piperidine-1-carboxylate (0.5 g, 1.41 mmol) and sodium carbonate (448.75 mg, 4.23 mmol, 177.37 uL) were added to a mixture of water (5 mL) and dioxane (15 mL). The resulting mixture was evacuated and then backfilled with argon, this operation was repeated three times, then Pd(dppf)Cl$_2$ DCM (57.63 mg, 70.57 umol) was added under argon. The reaction mixture was stirred under argon at 70° C. for 16 hr, then cooled and filtered. The filter cake was washed with dioxane (2*20 ml) and discarded. The filtrate was evaporated in vacuum to afford tert-butyl 5-methyl-2-[3-(1-methyl-3,6-dihydro-2H-pyridin-4-yl)phenyl]piperidine-1-carboxylate (0.45 g, 1.21 mmol, 86.05% yield) as yellow oil, which was used in next step without purification.

LCMS(ESI): [M]$^+$ m/z: calcd 370.2; found 371.2; Rt=1.094 min.

Step 2: Synthesis of tert-butyl 5-methyl-2-(3-(1-methylpiperidin-4-yl)phenyl)piperidine-1-carboxylate tert-butyl 5-methyl-2-[3-(1-methyl-3,6-dihydro-2H-pyridin-4-yl)phenyl]piperidine-1-carboxylate (0.45 g, 1.21 mmol) was dissolved in MeOH (30 mL) and palladium on carbon, 10% (129.25 mg, 1.21 mmol) was added. The resulting mixture was evacuated and then backfilled with H$_2$ and it was stirred 48 hr at rt. Then it was evaporated to afford tert-butyl 5-methyl-2-[3-(1-methyl-4-piperidyl)phenyl]piperidine-1-carboxylate (0.4 g, 1.07 mmol, 88.41% yield).

LCMS(ESI): [M]$^+$ m/z: calcd 372.2; found 373.2; Rt=1.134 min.

Step 3: Synthesis of 1-methyl-4-(3-(5-methylpiperidin-2-yl)phenyl)piperidine tert-butyl 5-methyl-2-[3-(1-methyl-4-piperidyl)phenyl]piperidine-1-carboxylate (0.4 g, 1.07 mmol) was dissolved in MeOH (20 mL) and diox/HCl (1.07 mmol, 5 mL) was added. Then it was evaporated and subjected to HPLC (Waters SunFire C18 19*100 5 mkm column and water-MeOH+NH$_3$ as an eluent mixture) to afford 1-methyl-4-[3-(5-methyl-2-piperidyl)phenyl]piperidine (107.4 mg, 394.23 umol, 36.72% yield)1-methyl-4-[3-(5-methyl-2-piperidyl)phenyl]piperidine (107.4 mg, 394.23 umol, 36.72% yield).

LCMS(ESI): [M]$^+$ m/z: calcd 272.2; found 273.2; Rt=1.334 min.

Step 4: Synthesis of N-(6-amino-5-methylpyridin-3-yl)-2-(5-methyl-2-(3-(1-methylpiperidin-4-yl)phenyl)piperidin-1-yl)-2-oxoacetamide (Compound 1149

DIPEA (127.38 mg, 985.58 umol, 171.67 uL) was added to the solution of respective 2-[(6-amino-5-methyl-3-pyridyl)amino]-2-oxo-acetic acid (76.94 mg, 394.23 umol) and 1-methyl-4-[3-(5-methyl-2-piperidyl)phenyl]piperidine (107.4 mg, 394.23 umol) in DMF (5 mL). The resulting mixture was stirred for 5 min followed by the addition of HATU (164.89 mg, 433.66 umol). Then, the reaction mixture was stirred overnight at rt. After the completion of the reaction, monitored by LCMS, the resulting suspension was concentrated under reduced pressure. The obtained solid was subjected to HPLC (Waters SunFire C18 20*100 5 mkm column and MeOH+NH$_3$ as an eluent mixture) to afford N-(6-amino-5-methyl-3-pyridyl)-2-[(2S,5R)-5-methyl-2-[3-(1-methyl-4-piperidyl)phenyl]-1-piperidyl]-2-oxo-acetamide (40.4 mg, 89.86 umol, 22.79% yield).

Compound 1149:
$^1$H NMR (500 MHz, DMSO-d$_6$) δ (ppm) 0.82-1.02 (m, 3H), 1.29-1.40 (m, 1H), 1.61-1.71 (m, 4H), 1.83-2.03 (m, 6H), 2.17-2.26 (m, 4H), 2.44 (m, 1H), 2.70-3.22 (m, 4H), 3.43-4.02 (m, 2H), 5.12-5.62 (m, 3H), 7.00-7.31 (m, 4H), 7.44-7.50 (m, 1H), 7.95-8.02 (m, 1H), 10.50-10.55 (m, 1H).

LCMS(ESI): [M]$^+$ m/z: calcd 449.2; found 450.2; Rt=2.102 min.

Step 5: Chiral Separation (Compound 1253 and Compound 1291

Racemic N-(6-amino-5-methyl-3-pyridyl)-2-[(2S,5R)-5-methyl-2-[3-(1-methyl-4-piperidyl)phenyl]-1-piperidyl]-2-oxo-acetamide (34.6 mg, 76.96 μmol) was chiral separated (Column: Chiralpak AD-H—V (250*20 mm, 5 mkm); Mobile phase: Hexane-IPA-MeOH 50-25-25 Flow Rate: 12 mL/min) to obtain N-(6-amino-5-methyl-3-pyridyl)-2-[(2S,5R)-5-methyl-2-[3-(1-methyl-4-piperidyl)phenyl]-1-piperidyl]-2-oxo-acetamide (13.99 mg, 31.12 μmol, 40.43% yield) (RT=17.07 min) and N-(6-amino-5-methyl-3-pyridyl)-2-[(2R,5S)-5-methyl-2-[3-(1-methyl-4-piperidyl)phenyl]-1-piperidyl]-2-oxo-acetamide (12.8 mg, 28.47 μmol, 36.99% yield) (RT=22.83 min).

Rel Time for Compound 1253 in analytical conditions (column: AD-H, Hexane-IPA-MeOH, 50-25-25, 0.6 ml/min as mobile phase) 22.91 min and for Compound 1291 16.11 min.

Compound 1253:
Retention time: 22.91 min
$^1$H NMR (600 MHz, DMSO-d$_6$) δ (ppm) 0.97-1.04 (m, 3H), 1.22-1.40 (m, 1H), 1.60-1.73 (m, 5H), 1.79-1.90 (m, 1H), 1.90-2.06 (m, 6H), 2.06-2.18 (m, 1H), 2.20 (s, 3H), 2.21-2.29 (m, 1H), 2.69-2.74 (m, 0.4H), 2.84-2.90 (m, 2H), 3.19-3.23 (m, 0.6H), 3.41-4.03 (m, 1H), 5.08-5.57 (m, 1H), 5.57-5.67 (m, 2H), 7.08-7.19 (m, 3H), 7.26-7.33 (m, 1H), 7.41-7.54 (m, 1H), 7.92-8.06 (m, 1H), 10.46-10.54 (m, 1H).

LCMS(ESI): [M]$^+$ m/z: calcd 449.2; found 450.2; Rt=2.009 min.

Compound 1291:
Retention time: 16.11 min
$^1$H NMR (600 MHz, DMSO-d$_6$) δ (ppm) 0.98-1.05 (m, 3H), 1.26-1.40 (m, 1H), 1.60-1.73 (m, 5H), 1.81-1.92 (m, 1H), 1.94-2.04 (m, 5H), 2.04-2.17 (m, 1H), 2.20 (s, 3H), 2.21-2.29 (m, 1H), 2.42-2.45 (m, 1H), 2.70-2.74 (m, 0.4H), 2.83-2.90 (m, 2H), 3.19-3.23 (m, 0.6H), 3.41-4.06 (m, 1H), 5.10-5.57 (m, 1H), 5.57-5.65 (m, 2H), 7.07-7.14 (m, 2H), 7.14-7.21 (m, 1H), 7.24-7.35 (m, 1H), 7.42-7.52 (m, 1H), 7.94-8.05 (m, 1H), 10.41-10.57 (m, 1H).

LCMS(ESI): [M]$^+$ m/z: calcd 449.2; found 450.2; Rt=2.007 min.

Example 251. The Synthesis of N-(6-amino-5-ethylpyridin-3-yl)-2-((2R,5S)-5-methyl-2-(3-(4-methylpiperazin-1-yl)phenyl)piperidin-1-yl)-2-oxoacetamide (Compound 1230

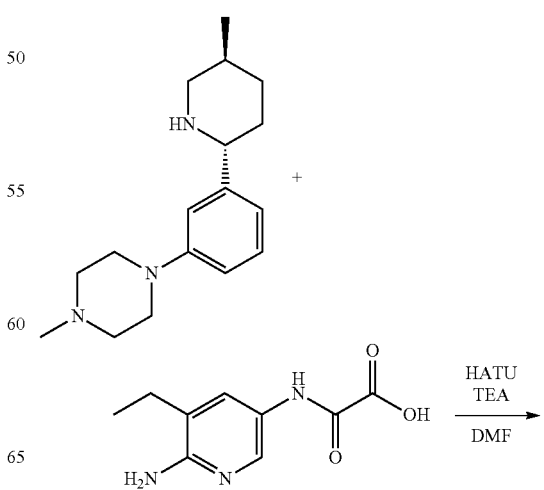

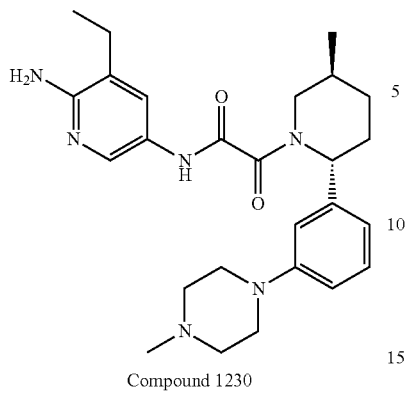

Compound 1230

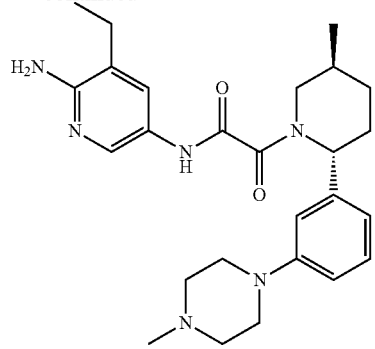

Compound 1367

1-methyl-4-[3-[(2R,5S)-5-methyl-2-piperidyl]phenyl] piperazine (130 mg, 475.47 μmol) was dissolved in DMF (5 mL) and TEA (481.13 mg, 4.75 mmol, 662.71 μL) was added, followed by 2-[(6-amino-5-ethyl-3-pyridyl)amino]-2-oxo-acetic acid (99.47 mg, 475.47 μmol). Then the HATU (271.18 mg, 713.20 μmol) was added dropwise and the reaction mixture was stirred overnight. The next day it was evaporated in vacuum and purified by HPLC (2-10 min 34-45% water/MeOH+NH$_3$; 30 ml/min; loading pump MeOH 4 ml/min; column SunFire 19*100 mm) to obtain N-(6-amino-5-ethyl-3-pyridyl)-2-[(2R,5S)-5-methyl-2-[3-(4-methylpiperazin-1-yl)phenyl]-1-piperidyl]-2-oxo-acetamide (30.9 mg, 66.51 μmol, 13.99% yield).

Compound 1230:

$^1$H NMR (600 MHz, DMSO-d$_6$) δ (ppm) 0.97-1.04 (m, 3H), 1.07-1.13 (m, 3H), 1.26-1.38 (m, 1H), 1.62-1.75 (m, 1H), 1.80-1.92 (m, 1H), 1.95-2.12 (m, 1H), 2.15-2.22 (m, 4H), 2.34-2.40 (m, 2H), 2.40-2.44 (m, 4H), 2.72-3.27 (m, 5H), 3.41-4.05 (m, 1H), 5.08-5.53 (m, 1H), 5.57-5.67 (m, 2H), 6.69-6.79 (m, 1H), 6.79-6.85 (m, 2H), 7.17-7.23 (m, 1H), 7.43-7.53 (m, 1H), 7.99-8.08 (m, 1H), 10.49-10.57 (m, 1H).

LCMS(ESI): [M]$^+$ m/z: calcd 464.2; found 465.2; Rt=0.806 min.

Example 252. The Synthesis of N-(6-amino-5-ethylpyridin-3-yl)-2-((2R,5S)-5-methyl-2-(3-(4-methylpiperazin-1-yl)phenyl)piperidin-1-yl)-2-oxoacetamide (Compound 1367

N-(6-amino-5-ethyl-3-pyridyl)-2-oxo-2-[(2R,5S)-5-methyl-2-[3-(4-methylpiperazin-1-yl)phenyl]-1-piperidyl] acetamide (75 mg, 161.43 μmol) was chirally separated Chiralcel OJ-H—I (250*20 mm, 5 mkm), Hexane-IPA-MeOH, 70-15-15, 12 ml/min to obtain N-(6-amino-5-ethyl-3-pyridyl)-2-oxo-2-[(2R,5S)-5-methyl-2-[3-(4-methylpiperazin-1-yl)phenyl]-1-piperidyl]acetamide (54 mg, 116.23 μmol, 72.00% yield).

Rel Time for Compound 1367 in analytical conditions (column: OJ-H, Hexane-IPA-MeOH, 50-25-25, 0.6 ml/min as mobile phase) 8.51 min Compound 1367:

Retention time: 8.51 min $^1$H NMR (600 MHz, DMSO-d$_6$) δ (ppm) 0.98-1.03 (m, 3H), 1.07-1.16 (m, 3H), 1.25-1.38 (m, 1H), 1.59-1.76 (m, 1H), 1.79-1.92 (m, 1H), 1.95-2.15 (m, 1H), 2.15-2.19 (m, 1H), 2.20 (s, 3H), 2.34-2.38 (m, 1H), 2.40-2.45 (m, 5H), 2.73-2.77 (m, 0.3H), 3.03-3.14 (m, 4H), 3.23-3.27 (m, 0.7H), 3.43-4.04 (m, 1H), 5.08-5.55 (m, 1H), 5.58-5.66 (m, 2H), 6.68-6.78 (m, 1H), 6.79-6.84 (m, 2H), 7.14-7.25 (m, 1H), 7.41-7.54 (m, 1H), 7.94-8.10 (m, 1H), 10.44-10.58 (m, 1H).

LCMS(ESI): [M]$^+$ m/z: calcd 464.2; found 465.2; Rt=1.766 min.

Example 253. Synthesis of N-(6-amino-5-ethylpyridin-3-yl)-2-((2R,5S)-2-(3-chloro-4-(2-(dimethylamino)ethyl)phenyl)-5-methylpiperidin-1-yl)-2-oxoacetamide (Compound 1402)

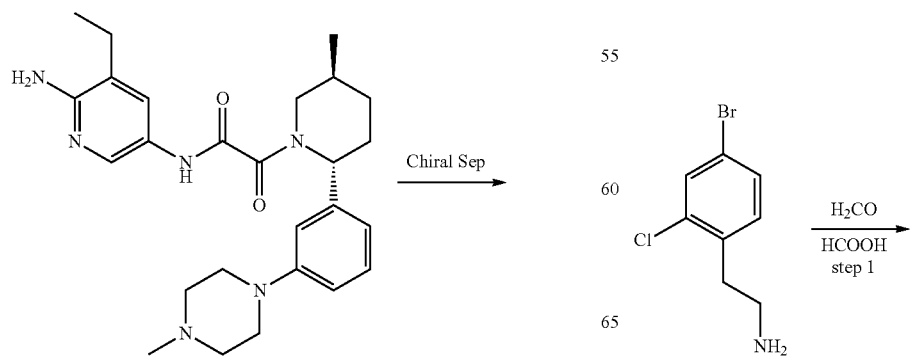

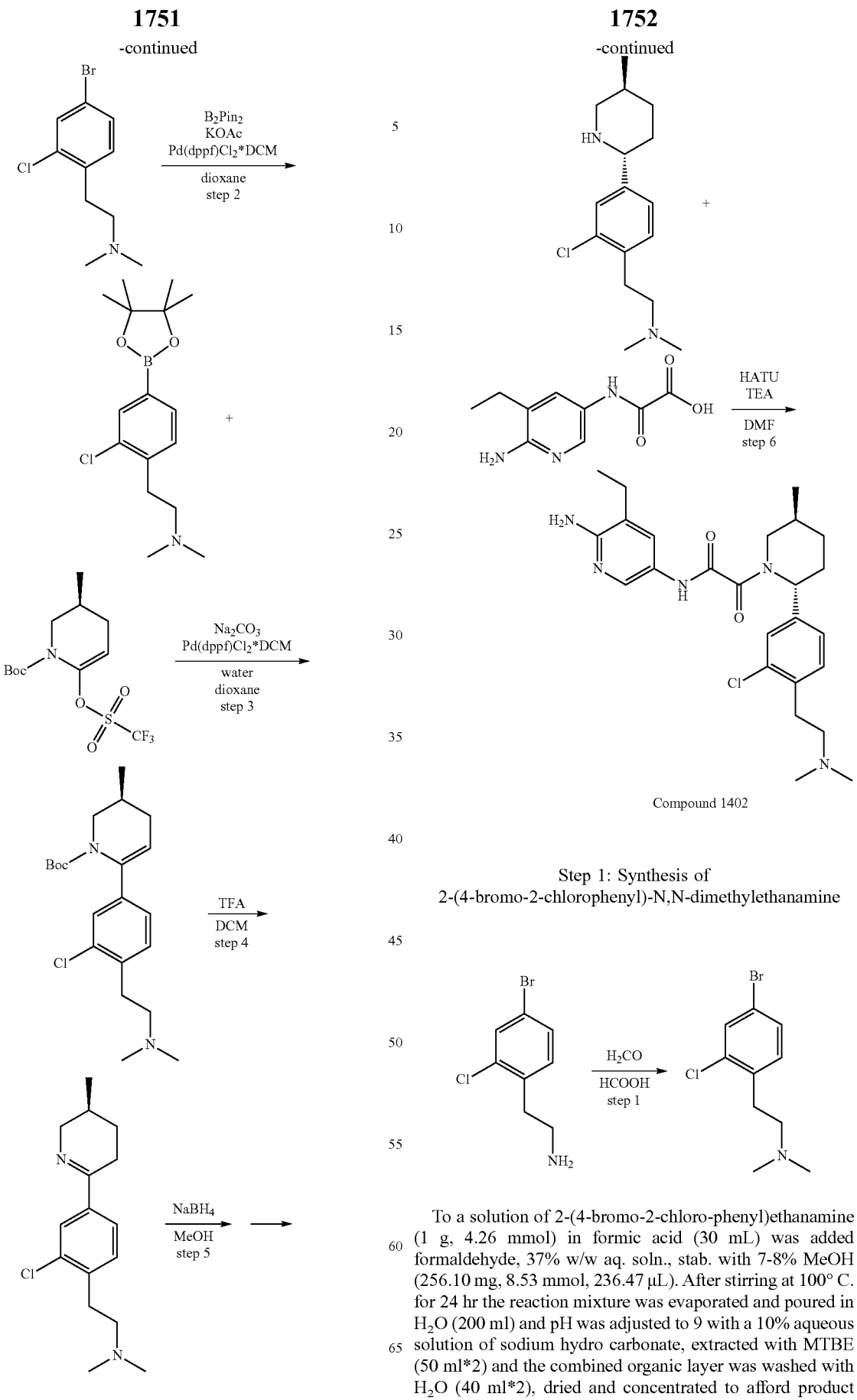

Step 1: Synthesis of
2-(4-bromo-2-chlorophenyl)-N,N-dimethylethanamine

To a solution of 2-(4-bromo-2-chloro-phenyl)ethanamine (1 g, 4.26 mmol) in formic acid (30 mL) was added formaldehyde, 37% w/w aq. soln., stab. with 7-8% MeOH (256.10 mg, 8.53 mmol, 236.47 μL). After stirring at 100° C. for 24 hr the reaction mixture was evaporated and poured in H₂O (200 ml) and pH was adjusted to 9 with a 10% aqueous solution of sodium hydro carbonate, extracted with MTBE (50 ml*2) and the combined organic layer was washed with H₂O (40 ml*2), dried and concentrated to afford product 2-(4-bromo-2-chloro-phenyl)-N,N-dimethyl-ethanamine (0.6 g, 2.29 mmol, 53.59% yield).

LCMS(ESI): [M]+ m/z: calcd 262.2; found 263.2; Rt=2.009 min.

Step 2: Synthesis of 2-(2-chloro-4-(4,4,5,5-tetramethyl-1,3,2-dioxaborolan-2-yl)phenyl)-N,N-dimethylethanamine

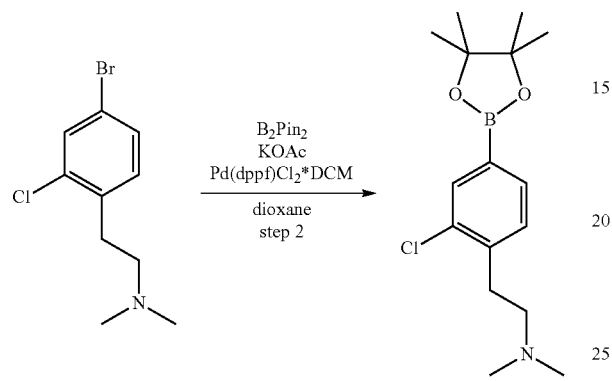

Potassium acetate (3.59 g, 36.56 mmol, 2.29 mL) was added to a solution of 2-(4-bromo-2-chloro-phenyl)-N,N-dimethyl-ethanamine (4.8 g, 18.28 mmol) and 4,4,5,5-tetramethyl-2-(4,4,5,5-tetramethyl-1,3,2-dioxaborolan-2-yl)-1,3,2-dioxaborolane (5.57 g, 21.94 mmol) in dioxane (200 mL). Reaction flask was evacuated and refilled with argon 3 times. Then Pd(dppf)Cl$_2$*DCM (1.34 g, 1.83 mmol) was added under stream of argon. Resulting mixture was stirred at 100° C. for 12 hr under inert atmosphere, then cooled and evaporated in vacuum poured into water (300 ml) and extracted with DCM (2×80 ml). The combined organic extracts were washed with water (80 ml), dried over sodium sulphate and evaporated in vacuum to afford product 2-[2-chloro-4-(4,4,5,5-tetramethyl-1,3,2-dioxaborolan-2-yl)phenyl]-N,N-dimethyl-ethanamine (7.2 g, crude).

LCMS(ESI): [M]+ m/z: calcd 309.2; found 310.2; Rt=1.074 min.

Step 3: Synthesis of (S)-tert-butyl 6-(3-chloro-4-(2-(dimethylamino)ethyl)phenyl)-3-methyl-3,4-dihydropyridine-1(2H)-carboxylate

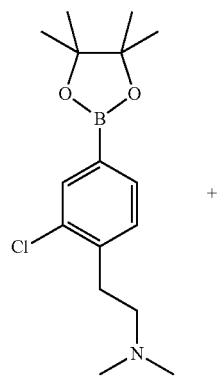

+

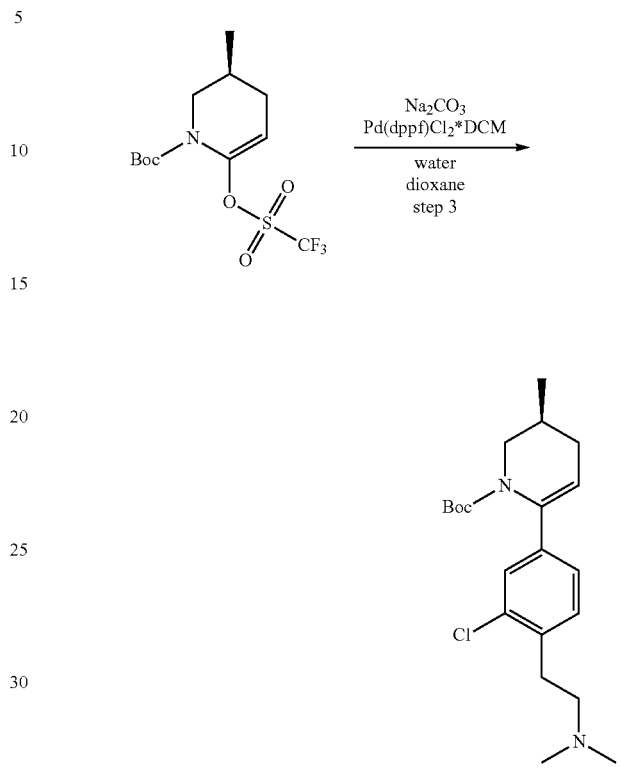

2-[2-chloro-4-(4,4,5,5-tetramethyl-1,3,2-dioxaborolan-2-yl)phenyl]-N,N-dimethyl-ethanamine (3 g, 9.69 mmol) and tert-butyl (3S)-3-methyl-6-(trifluoromethylsulfonyloxy)-3,4-dihydro-2H-pyridine-1-carboxylate (3.35 g, 9.69 mmol) were mixed together in dioxane (90 mL) The resulting mixture was evacuated and then backfilled with argon, this operation was repeated three times, then Sodium carbonate (2.05 g, 19.38 mmol, 811.14 µL) in water (10 mL) and [1,1'-bis(diphenylphosphino)ferrocene]dichloropalladium (II), complex with DCM (354.46 mg, 484.44 µmol) were added under argon. The reaction mixture was stirred under argon at 90° C. for 18 hr, then cooled and evaporated in vacuum poured into water (180 ml) and extracted with EtOAc (2×150 ml). The combined organic extracts were washed with water (2*40 ml), dried over sodium sulphate and evaporated in vacuum to leave 4.2 g of crude product, 4.2 g of which was purification by column chromatography on silica gel using MTBE/MeOH gradient (10-100% MeOH) to afford tert-butyl (3S)-6-[3-chloro-4-[2-(dimethylamino)ethyl]phenyl]-3-methyl-3,4-dihydro-2H-pyridine-1-carboxylate (1.1 g, 2.90 mmol, 29.96% yield).

LCMS(ESI): [M]+ m/z: calcd 378.2; found 379.2; Rt=1.110 min.

Step 4: Synthesis of (S)-2-(2-chloro-4-(5-methyl-3,4,5,6-tetrahydropyridin-2-yl)phenyl)-N,N-dimethylethanamine

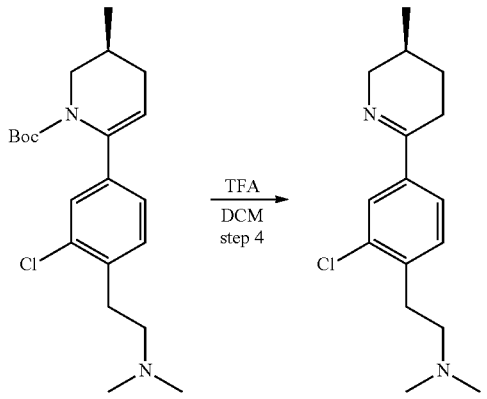 [SMILES: "TFA" ; C[C@H]1CC=C(c2ccc(CCN(C)C)c(Cl)c2)N(C(=O)OC(C)(C)C)C1 ; "DCMstep 4" ; C[C@H]1CCC(c2ccc(CCN(C)C)c(Cl)c2)=NC1]

The solution of tert-butyl (3S)-6-[3-chloro-4-[2-(dimethylamino)ethyl]phenyl]-3-methyl-3,4-dihydro-2H-pyridine-1-carboxylate (1.1 g, 2.90 mmol) in DCM (10 mL) and TFA (10 g, 87.70 mmol, 6.76 mL) was stirred at 0° C. for 8 hr, and then evaporated in vacuum. Crushed ice (50 g) was added to the residue and pH was adjusted to 8 with a 10% aqueous solution of sodium hydro carbonate. The resulting mixture was extracted with MTBE (2*40 mL). The combined organic extracts were dried over sodium sulphate and evaporated in vacuum to afford 2-[2-chloro-4-[(3S)-3-methyl-2,3,4,5-tetrahydropyridin-6-yl]phenyl]-N,N-dimethyl-ethanamine (0.3 g, 1.08 mmol, 37.07% yield).

LCMS(ESI): [M]f m/z: calcd 278.2; found 279.2; Rt=0.669 min.

Step 5: Synthesis of 2-(2-chloro-4-((2R,5S)-5-methylpiperidin-2-yl)phenyl)-N,N-dimethylethanamine

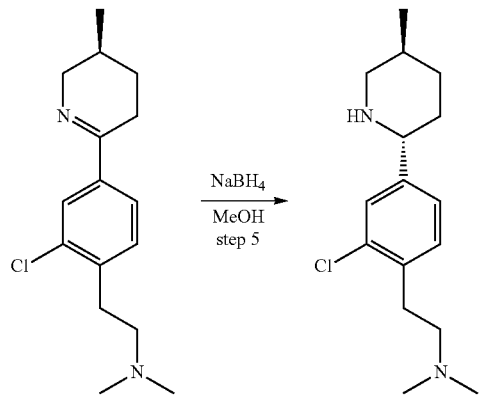 [SMILES: C[C@H]1CCC(c2ccc(CCN(C)C)c(Cl)c2)=NC1 ; "MeOHstep 5" ; "NaBH4" ; C[C@H]1CC[C@H](c2ccc(CCN(C)C)c(Cl)c2)NC1]

Sodium borohydride (81.41 mg, 2.15 mmol, 75.80 µL) was added in one portion to a stirred solution of 2-[2-chloro-4-[(3S)-3-methyl-2,3,4,5-tetrahydropyridin-6-yl]phenyl]-N,N-dimethyl-ethanamine (0.3 g, 1.08 mmol) in MeOH (10 mL) at 0° C. The resulting mixture was stirred at 0° C. for 5 hr, and then evaporated in vacuum. The residue was diluted with water (20 mL) and extracted with DCM (2*20 mL). The combined organic extracts were dried over sodium sulphate and evaporated in vacuum to afford 2-[2-chloro-4-[(2R,5S)-5-methyl-2-piperidyl]phenyl]-N,N-dimethyl-ethanamine (0.15 g, 534.12 µmol, 49.64% yield).

LCMS(ESI): [M]⁺ m/z: calcd 280.2; found 281.2; Rt=1.250 min.

2-[(6-amino-5-ethyl-3-pyridyl)amino]-2-oxo-acetic acid (139.67 mg, 667.65 µmol) and 2-[2-chloro-4-[(2R,5S)-5-methyl-2-piperidyl]phenyl]-N,N-dimethyl-ethanamine (0.15 g, 534.12 µmol) were mixed in DMF (10 mL). The reaction suspension was cooled to 20° C. and HATU (253.86 mg, 667.65 µmol) followed by TEA (162.14 mg, 1.60 mmol, 223.34 µL) were added and stirred at ambient temperature for 14 hr. The reaction mixture was evaporated in vacuum and obtained crude product 0.5 g was purified by preparative 45-90% 0-5 min H₂O/MeOH/0.1% NH₄OH, flow: 30 ml/min to afford product N-(6-amino-5-ethyl-3-pyridyl)-2-[(2R,5S)-2-[3-chloro-4-[2-(dimethylamino)ethyl]phenyl]-5-methyl-1-piperidyl]-2-oxo-acetamide (0.0702 g, 148.72 µmol, 27.84% yield).

Compound 1402:

¹H NMR (600 MHz, DMSO-d₆) δ (ppm) 0.97-1.03 (m, 3H), 1.07-1.13 (m, 3H), 1.25-1.37 (m, 1H), 1.57-1.66 (m, 1H), 1.80-1.93 (m, 1H), 1.97-2.09 (m, 1H), 2.12-2.21 (m, 8H), 2.35-2.40 (m, 2H), 2.42-2.45 (m, 1H), 2.70-3.25 (m, 3H), 3.41-4.04 (m, 1H), 5.09-5.53 (m, 1H), 5.59-5.70 (m, 2H), 7.18-7.25 (m, 1H), 7.27-7.39 (m, 2H), 7.42-7.53 (m, 1H), 7.94-8.09 (m, 1H), 10.48-10.60 (m, 1H).

LCMS(ESI): [M]⁺ m/z: calcd 472.2; found 473.2; Rt=1.885 min.

Example 254. Synthesis of N-(6-amino-5-ethyl-3-pyridyl)-2-oxo-2-[(2R,5S)-5-methyl-2-[3-(1-methyl-4-piperidyl)phenyl]-1-piperidyl]acetamide (Compound 1363

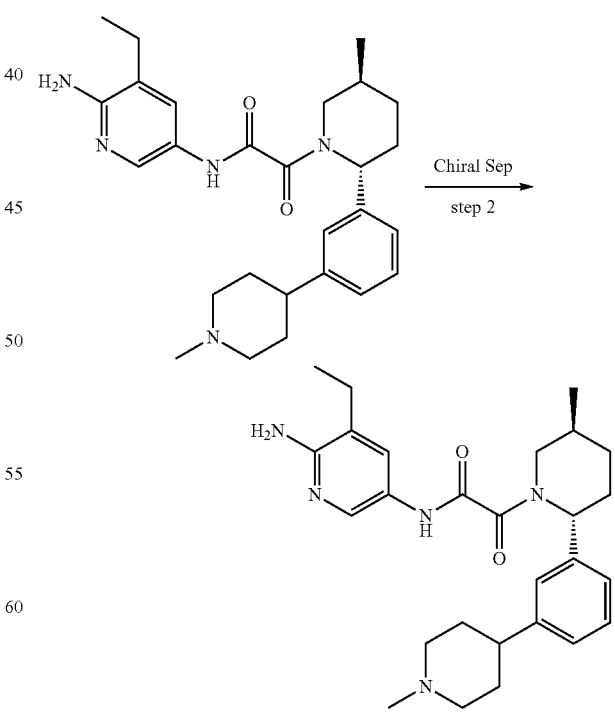

Compound 1363

N-(6-amino-5-ethyl-3-pyridyl)-2-oxo-2-[(2R,5S)-5-methyl-2-[3-(1-methyl-4-piperidyl)phenyl]-1-piperidyl]acetamide (54 mg, 116.48 μmol) was chirally separated Chiralpak IA-III (250*20 mm, 5 mkm), Hexane-IPA-MeOH, 70-15-15, 12 ml/min to obtain N-(6-amino-5-ethyl-3-pyridyl)-2-oxo-2-[(2R,5S)-5-methyl-2-[3-(1-methyl-4-piperidyl)phenyl]-1-piperidyl]acetamide (44 mg, 94.91 μmol, 81.48% yield) (RT=31.06 min). Rel Time for Compound 1363 in analytical conditions (column: IA, Hexane-IPA-MeOH, 70-15-15, 0.6 ml/min as mobile phase) 33.82 min Compound 1363:

Retention time: 33.82 min $^1$H NMR (600 MHz, DMSO-$d_6$) δ (ppm) 0.98-1.03 (m, 3H), 1.06-1.13 (m, 3H), 1.27-1.37 (m, 1H), 1.60-1.71 (m, 5H), 1.80-2.04 (m, 4H), 2.07-2.27 (m, 5H), 2.39-2.44 (m, 2H), 2.70-3.21 (m, 3H), 3.40-4.03 (m, 1H), 5.11-5.58 (m, 1H), 5.58-5.66 (m, 2H), 7.09-7.19 (m, 3H), 7.26-7.32 (m, 1H), 7.42-7.52 (m, 1H), 7.97-8.07 (m, 1H), 10.49-10.55 (m, 1H).

LCMS(ESI): [M]$^+$ m/z: calcd 463.2; found 464.2; Rt=2.081 min.

Example 255. The Synthesis of N-(6-amino-5-ethylpyridin-3-yl)-2-((2R,5S)-5-methyl-2-(3-((1-methylpyrrolidin-2-yl)Methoxy)phenyl)piperidin-1-yl)-2-oxoacetamide (Compound 1362)

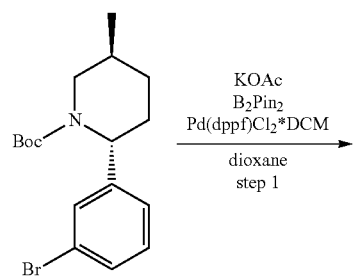

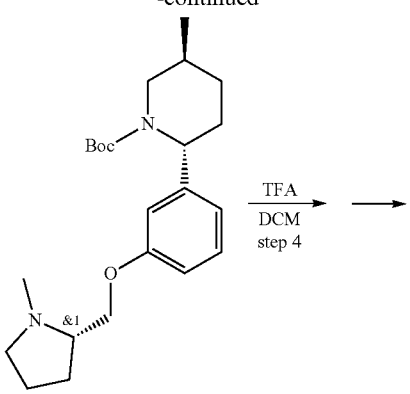

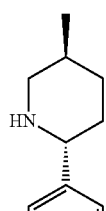

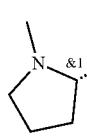

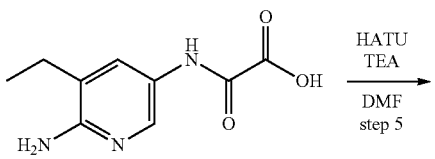

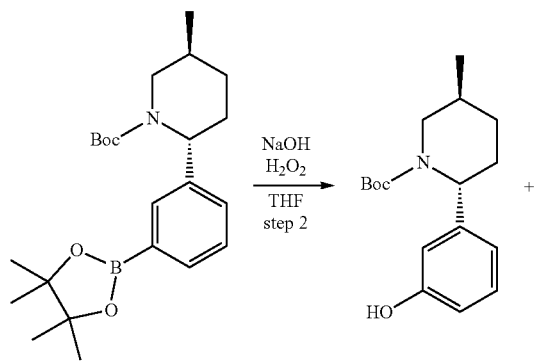

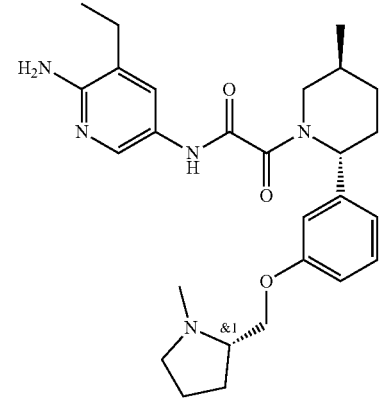

Compound 1362

Step 1: Synthesis of (2R,5S)-tert-butyl 5-methyl-2-(3-(4,4,5,5-tetramethyl-1,3,2-dioxaborolan-2-yl)phenyl)piperidine-1-carboxylate

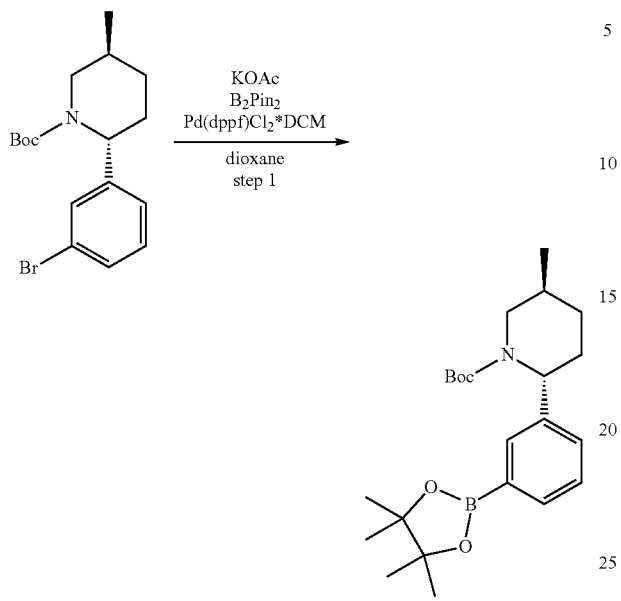

tert-butyl (2R,5S)-2-(3-bromophenyl)-5-methyl-piperidine-1-carboxylate (3.4 g, 9.60 mmol), 4,4,5,5-tetramethyl-2-(4,4,5,5-tetramethyl-1,3,2-dioxaborolan-2-yl)-1,3,2-dioxaborolane (2.68 g, 10.56 mmol) and potassium acetate (2.35 g, 23.99 mmol, 1.50 mL) were mixed together in dioxane (40.00 mL) and the resulting mixture was evacuated and backfilled three times with argon. Pd(dppf)Cl$_2$*DCM (391.86 mg, 479.85 µmol) was added to the previous mixture and the resulting mixture was heated at 100° C. overnight. The reaction mixture was concentrated in vacuum and water (25 mL) was added to the residue. The resulting mixture was extracted with MTBE (2*40 mL) and combined organic layers were washed with water (25 mL), brine (25 mL), dried over Na$_2$SO$_4$, filtered and concentrated in vacuum to obtain tert-butyl (2R,5S)-5-methyl-2-[3-(4,4,5,5-tetramethyl-1,3,2-dioxaborolan-2-yl)phenyl]piperidine-1-carboxylate (3.5 g, 8.72 mmol, 90.87% yield).

LCMS(ESI): [M-Boc]$^+$ m/z: calcd 301.2; found 302.2; Rt=1.745 min.

Step 2: Synthesis of (2R,5S)-tert-butyl 2-(3-hydroxyphenyl)-5-methylpiperidine-1-carboxylate

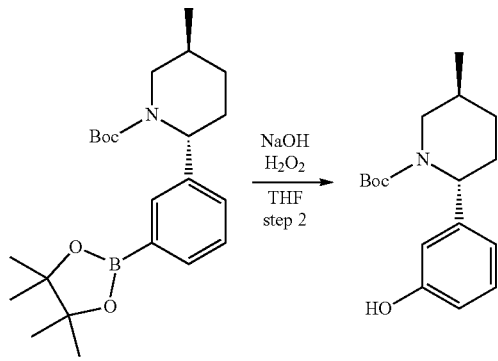

tert-butyl (2R,5S)-5-methyl-2-[3-(4,4,5,5-tetramethyl-1,3,2-dioxaborolan-2-yl)phenyl]piperidine-1-carboxylate (3.7 g, 9.22 mmol) was dissolved in THF (50.73 mL) and hydrogen peroxide 35% (1.34 g, 13.83 mmol, 1.22 mL, 35% purity) was carefully added dropwise at rt. After addition completed, the reaction mixture was stirred for 1 hr and aq. solution of Sodium hydroxide, pearl (590.01 mg, 14.75 mmol, 277.00 µL) was added dropwise at room temperature. After addition completed, the reaction mixture was stirred for 1 hr. The reaction mixture was acidified with citric acid and the resulting mixture was transferred to a separation funnel. An organic layer was separated and the aqueous layer was extracted with MTBE (2*40 mL). Combined organic layers were washed with aq. sodium sulfite, dried over Na$_2$SO$_4$, filtered and concentrated in vacuum to obtain tert-butyl (2R,5S)-2-(3-hydroxyphenyl)-5-methyl-piperidine-1-carboxylate (3 g, crude).

LCMS(ESI): [M-Boc]$^+$ m/z: calcd 191.2; found 192.2; Rt=1.482 min.

Step 3: Synthesis of (2R,5S)-tert-butyl 5-methyl-2-(3-(((rac-S)-1-methylpyrrolidin-2-yl)Methoxy)phenyl)piperidine-1-carboxylate

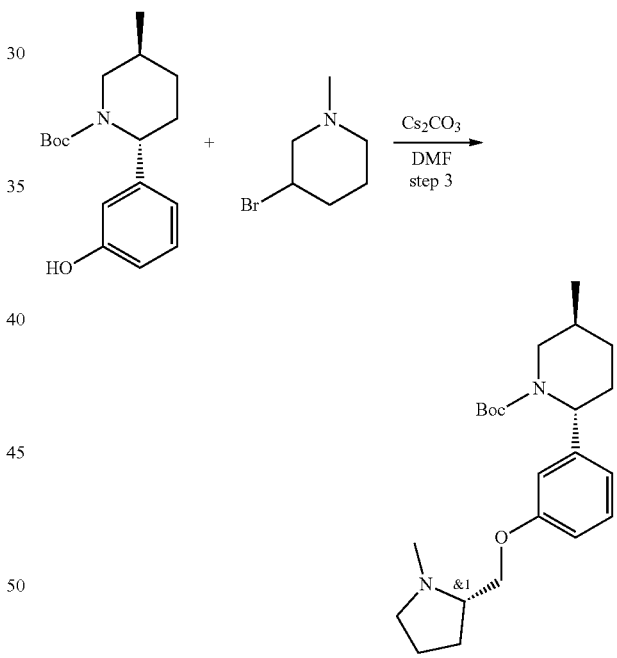

tert-butyl (2R,5S)-2-(3-hydroxyphenyl)-5-methyl-piperidine-1-carboxylate (0.75 g, 2.57 mmol) was dissolved in DMF (10 mL) and 3-bromo-1-methyl-piperidine (1.33 g, 5.15 mmol, HBr) was added thereto followed by addition of cesium carbonate (3.35 g, 10.30 mmol). The resulting mixture was heated at 50° C. overnight. The reaction mixture was poured into water (5 mL) and the resulting mixture was extracted with EtOAc (3*20 mL). Combined organic layers were washed with water (3*10 mL), brine (10 mL), dried over Na$_2$SO$_4$, filtered, and concentrated in vacuum.

LCMS(ESI): [M]$^+$ m/z: calcd 388.2; found 389.2; Rt=1.063 min.

Step 4: Synthesis of (2R,5S)-5-methyl-2-(3-(((rac-S)-1-methylpyrrolidin-2-yl)Methoxy)phenyl)piperidine

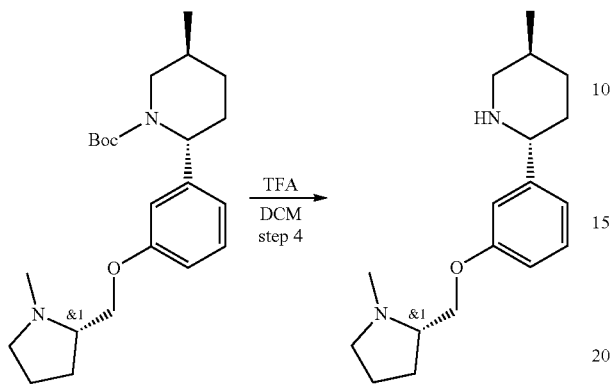

tert-butyl (2R,5S)-5-methyl-2-[3-[[rac-(2S)-1-methylpyrrolidin-2-yl]methoxy]phenyl]piperidine-1-carboxylate (550.00 mg, 1.42 mmol) was dissolved in DCM (5 mL) and TFA (3 mL) was added thereto. The resulting mixture was stirred for 1 hr. The reaction mixture was carefully poured into aq.NaHCO₃ solution (3 g in 10 mL of water) and the resulting mixture was extracted with DCM (2*15 mL). Combined organic layers were dried over sodium sulfate, filtered, and concentrated in vacuum to obtain (2R,5S)-5-methyl-2-[3-[[rac-(2S)-1-methylpyrrolidin-2-yl]methoxy]phenyl]piperidine (350 mg, 1.21 mmol, 85.73% yield).

LCMS(ESI): [M]⁺ m/z: calcd 288.2; found 289.2; Rt=0.685 min.

Step 5: Synthesis of N-(6-amino-5-ethylpyridin-3-yl)-2-((2R,5S)-5-methyl-2-(3-((1-methylpyrrolidin-2-yl)Methoxy)phenyl)piperidin-1-yl)-2-oxoacetamide (Compound 1362

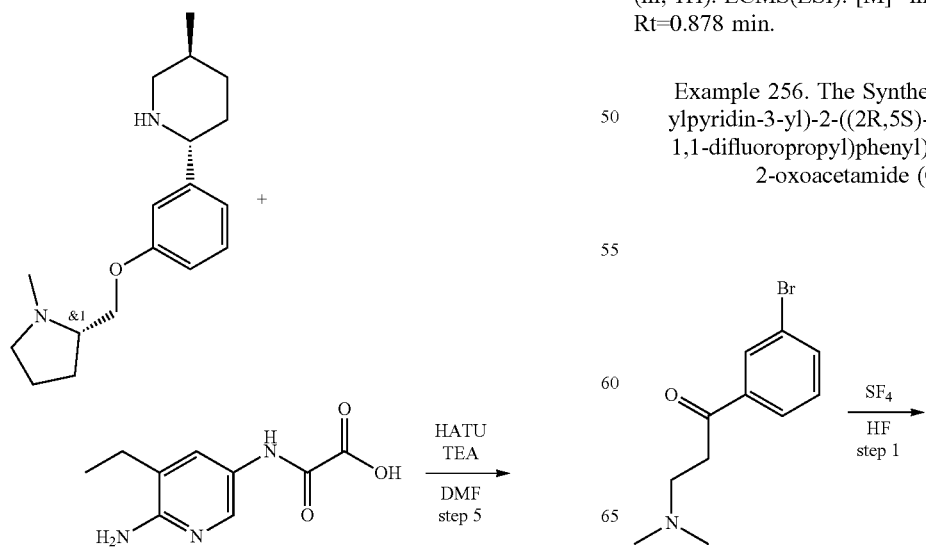

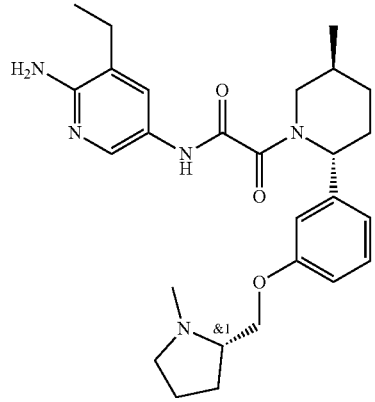

(2R,5S)-5-methyl-2-[3-[[rac-(2S)-1-methylpyrrolidin-2-yl]methoxy]phenyl]piperidine (0.35 g, 1.21 mmol) was dissolved in DMF (5 mL) and TEA (1.23 g, 12.13 mmol, 1.69 mL) was added, followed by 2-[(6-amino-5-ethyl-3-pyridyl)amino]-2-oxo-acetic acid (253.86 mg, 1.21 mmol). Then the HATU (692.10 mg, 1.82 mmol) was added dropwise and the reaction mixture was stirred overnight. The next day it was evaporated in vacuum and purified by HPLC (2-10 min 35-60% MeOH+NH₃30 mL/min (loading pump 4 mL MeOH+NH₃) column: SunFire 100*19 mm, 5 microM) to obtain N-(6-amino-5-ethyl-3-pyridyl)-2-oxo-2-[(2R,5S)-5-methyl-2-[3-[[rac-(2S)-1-methylpyrrolidin-2-yl]methoxy]phenyl]-1-piperidyl]acetamide (56.4 mg, 117.59 mol, 9.69% yield) and N-(6-amino-5-ethyl-3-pyridyl)-2-oxo-2-[(2R,5S)-5-methyl-2-[3-[[rac-(2S)-1-methylpyrrolidin-2-yl]methoxy]phenyl]-1-piperidyl]acetamide (84.6 mg, 176.39 µmol, 14.54% yield).

Compound 1362: ¹H NMR (600 MHz, dmso) δ 0.97-1.03 (m, 3H), 1.06-1.13 (m, 3H), 1.27-1.36 (m, 1H), 1.53-1.69 (m, 4H), 1.77-2.24 (m, 6H), 2.31-2.35 (m, 3H), 2.38-2.42 (m, 2H), 2.72-3.27 (m, 3H), 3.78-4.03 (m, 2H), 5.07-5.57 (m, 1H), 5.57-5.68 (m, 2H), 6.77-6.95 (m, 3H), 7.24-7.32 (m, 1H), 7.43-7.53 (m, 1H), 7.98-8.09 (m, 1H), 10.46-10.63 (m, 1H). LCMS(ESI): [M]⁺ m/z: calcd 479.2; found 480.2; Rt=0.878 min.

Example 256. The Synthesis of N-(6-amino-5-ethylpyridin-3-yl)-2-((2R,5S)-2-(3-(3-(dimethylamino)-1,1-difluoropropyl)phenyl)-5-methylpiperidin-1-yl)-2-oxoacetamide (Compound 1381

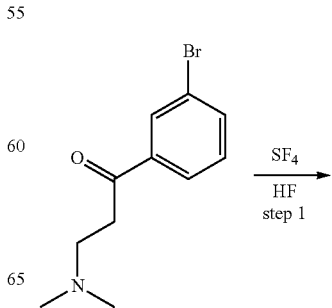

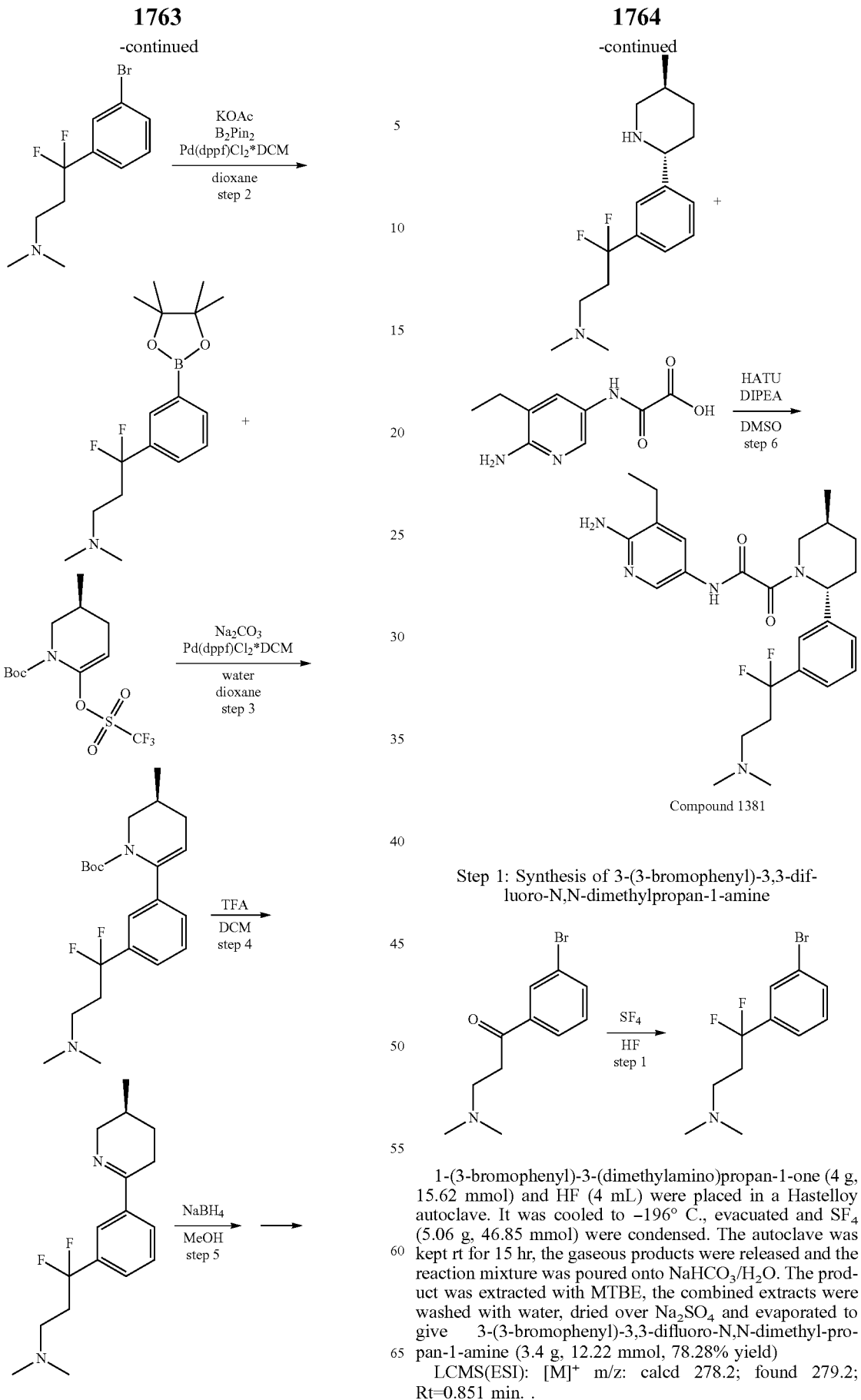

Step 1: Synthesis of 3-(3-bromophenyl)-3,3-difluoro-N,N-dimethylpropan-1-amine 1-(3-bromophenyl)-3-(dimethylamino)propan-1-one (4 g, 15.62 mmol) and HF (4 mL) were placed in a Hastelloy autoclave. It was cooled to −196° C., evacuated and SF$_4$ (5.06 g, 46.85 mmol) were condensed. The autoclave was kept rt for 15 hr, the gaseous products were released and the reaction mixture was poured onto NaHCO$_3$/H$_2$O. The product was extracted with MTBE, the combined extracts were washed with water, dried over Na$_2$SO$_4$ and evaporated to give 3-(3-bromophenyl)-3,3-difluoro-N,N-dimethyl-propan-1-amine (3.4 g, 12.22 mmol, 78.28% yield)

LCMS(ESI): [M]$^+$ m/z: calcd 278.2; found 279.2; Rt=0.851 min. .

Step 2: Synthesis of 3,3-difluoro-N,N-dimethyl-3-(3-(4,4,5,5-tetramethyl-1,3,2-dioxaborolan-2-yl)phenyl)Propan-1-amine

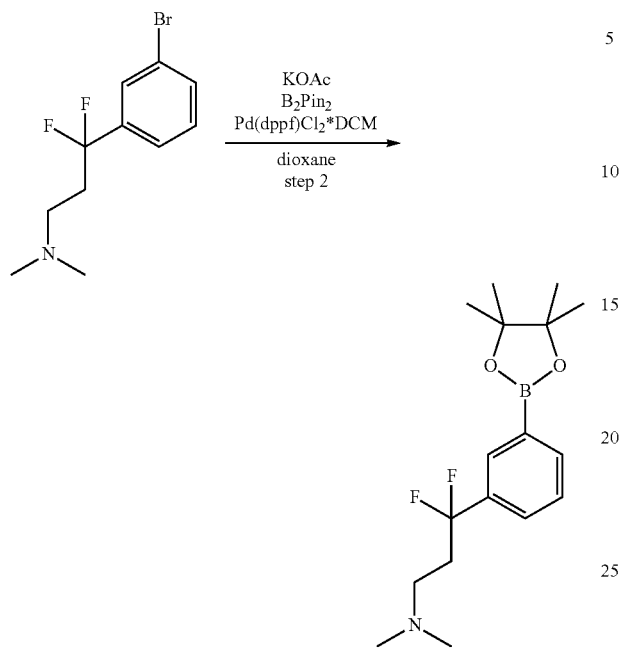

A mixture of 3-(3-bromophenyl)-3,3-difluoro-N,N-dimethyl-propan-1-amine (3.4 g, 12.22 mmol), bis(pinacolato)diboron (3.73 g, 14.67 mmol) and potassium acetate (3.60 g, 36.67 mmol, 2.29 mL) in dioxane (50 mL) was degassed with argon for 10 min. Pd(dppf)Cl$_2$*DCM (499.14 mg, 611.21 µmol) was next added and the reaction mixture was heated at 90° C. for 12 hr. The reaction mixture was cooled to rt, diluted with DCM and water. Organic phase was separated and concentrated under reduced pressure. Crude product was treated with HCl/diox solution and concentrated again. The residue was treated with MTBE and precipitate was collected by filtration to give 3,3-difluoro-N,N-dimethyl-3-[3-(4,4,5,5-tetramethyl-1,3,2-dioxaborolan-2-yl)phenyl]propan-1-amine (1.55 g, crude, HCl).

LCMS(ESI): [M]$^+$ m/z: calcd 325.2; found 326.2; Rt=1.123 min.

Step 3: Synthesis of (S)-tert-butyl 6-(3-(3-(dimethylamino)-1,1-difluoropropyl)phenyl)-3-methyl-3,4-dihydropyridine-1(2H)-carboxylate

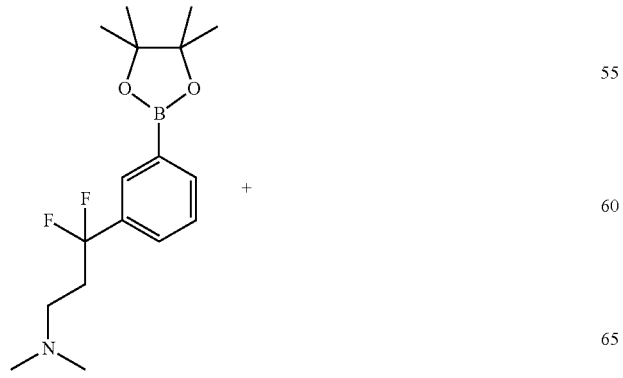

+

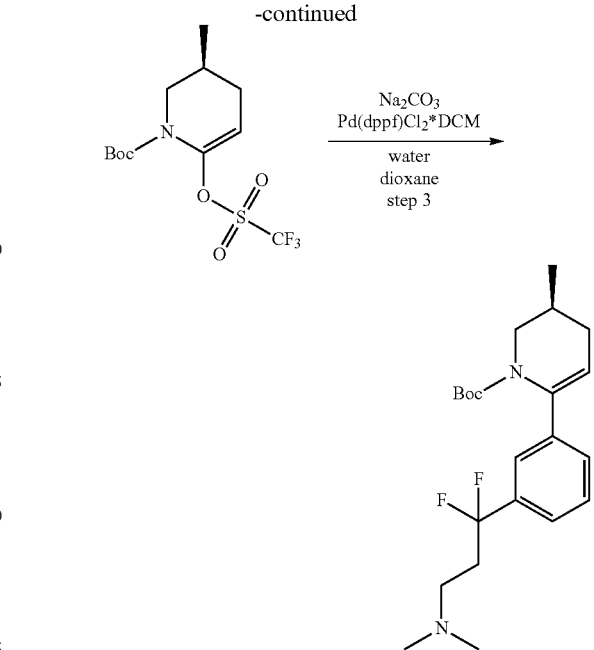

3,3-difluoro-N,N-dimethyl-3-[3-(4,4,5,5-tetramethyl-1,3,2-dioxaborolan-2-yl)phenyl]propan-1-amine (1.55 g, 3.21 mmol, HCl) and sodium carbonate (1.36 g, 12.86 mmol, 538.21 µL) were mixed in H$_2$O (10 mL) and dioxane (30 mL) and stirred for 20 min, then tert-butyl (3S)-3-methyl-6-(trifluoromethylsulfonyloxy)-3,4-dihydro-2H-pyridine-1-carboxylate (1.33 g, 3.86 mmol) and Pd(dppf)Cl$_2$*DCM (262.29 mg, 321.43 µmol) were added under argon and stirred at 75° C. for 12 hr. Reaction mixture was diluted with water and needed product was extracted with DCM, dried over Na$_2$SO$_4$ and concentrated in vacuum. tert-butyl (3S)-6-[3-[3-(dimethylamino)-1,1-difluoro-propyl]phenyl]-3-methyl-3,4-dihydro-2H-pyridine-1-carboxylate (1.95 g, crude) was obtained.

LCMS(ESI): [M]$^+$ m/z: calcd 394.2; found 395.2; Rt=1.236 min.

Step 4: Synthesis of (S)-3,3-difluoro-N,N-dimethyl-3-(3-(5-methyl-3,4,5,6-tetrahydropyridin-2-yl)phenyl)Propan-1-amine

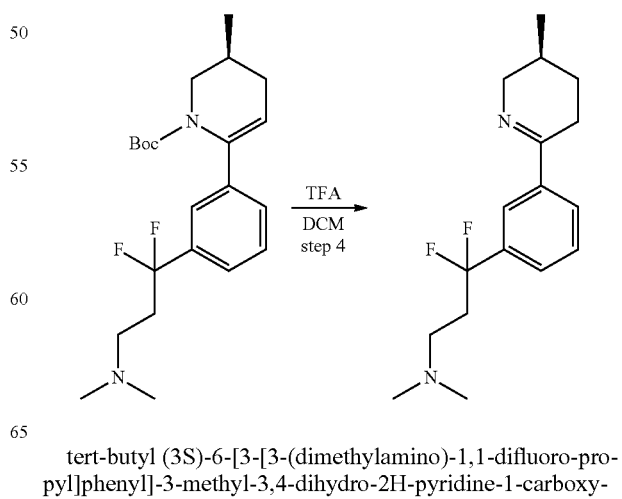

tert-butyl (3S)-6-[3-[3-(dimethylamino)-1,1-difluoro-propyl]phenyl]-3-methyl-3,4-dihydro-2H-pyridine-1-carboxylate (1.95 g, 2.17 mmol) was dissolved in mixture of TFA (6.64 g, 58.23 mmol, 4.49 mL) and DCM (20.93 mL) and stirred for 1 hr. The reaction mixture was concentrated in vacuum and the residue was treated with NaHCO$_3$ solution followed by extraction with DCM (2*50 mL). Then the aqueous layer was treated again with EtOAc, organic phase was dried over Na$_2$SO$_4$ and concentrated under reduced pressure to afford 3,3-difluoro-N,N-dimethyl-3-[3-[(3S)-3-methyl-2,3,4,5-tetrahydropyridin-6-yl]phenyl]propan-1-amine (210 g, crude) which was used in the next step without purification.

LCMS(ESI): [M]$^+$ m/z: calcd 294.2; found 295.2; Rt=0.645 min.

Step 5: Synthesis of 3,3-difluoro-N,N-dimethyl-3-(3-((2R,5S)-5-methylpiperidin-2-yl)phenyl)Propan-1-amine

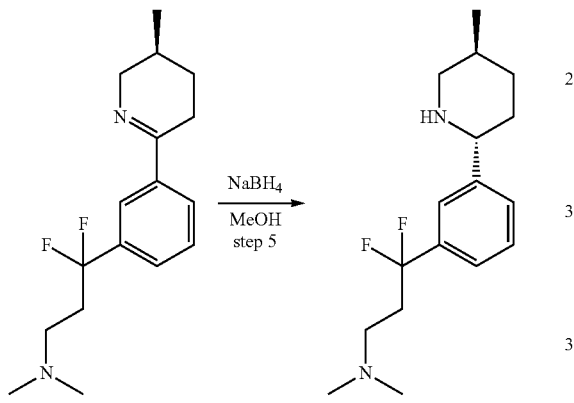

3,3-difluoro-N,N-dimethyl-3-[3-[(3S)-3-methyl-2,3,4,5-tetrahydropyridin-6-yl]phenyl]propan-1-amine (210 mg, 292.48 µmol) was dissolved in MeOH (20 mL) and sodium borohydride (22.13 mg, 584.95 µmol, 20.60 µL) was added. After stirring for 12 hr reaction mixture was concentrated and used in the next step without any purification. 3,3-difluoro-N,N-dimethyl-3-[3-[(2R,5S)-5-methyl-2-piperidyl]phenyl]propan-1-amine (250 mg, crude).

LCMS(ESI): [M]$^+$ m/z: calcd 296.2; found 297.2; Rt=0.244 min.

Step 6: Synthesis of N-(6-amino-5-ethylpyridin-3-yl)-2-((2R,5S)-2-(3-(3-(dimethylamino)-1,1-difluoropropyl)phenyl)-5-methylpiperidin-1-yl)-2-oxoacetamide (Compound 1381

Crude product 3,3-difluoro-N,N-dimethyl-3-[3-[(2R,5S)-5-methyl-2-piperidyl]phenyl]propan-1-amine (250 mg, 337.38 µmol) from previous stage was mixed with TEA (400 mg, 3.95 mmol, 550.96 µL) in DMSO (3.92 mL), next 2-[(6-amino-5-ethyl-3-pyridyl)amino]-2-oxo-acetic acid (70.58 mg, 337.38 µmol) and HATU (179.60 mg, 472.34 µmol) was added and stirred overnight. RM was filtered and subjected to HPLC (2-10 min 0-55% water/MeOH+NH$_3$30 mL/min; loading pump 4 mL/min MeOH; column SunFire 19*100 mm) to afford N-(6-amino-5-ethyl-3-pyridyl)-2-oxo-2-[(2R,5S)-2-[3-[3-(dimethylamino)-1,1-difluoro-propyl]phenyl]-5-methyl-1-piperidyl]acetamide (29.8 mg, 61.12 µmol, 18.12% yield).

$^1$H NMR (600 MHz, DMSO-d$_6$) δ (ppm) 0.73-1.04 (m, 3H), 1.05-1.16 (m, 3H), 1.25-1.41 (m, 1H), 1.58-1.72 (m, 1H), 1.80-1.96 (m, 1H), 2.04-2.08 (m, 6H), 2.08-2.20 (m, 1H), 2.20-2.32 (m, 3H), 2.34-2.43 (m, 4H), 2.70-3.23 (m, 1H), 3.46-4.05 (m, 1H), 5.14-5.75 (m, 3H), 7.36-7.47 (m, 3H), 7.47-7.58 (m, 2H), 7.97-8.12 (m, 1H), 10.49-10.62 (m, 1H).

LCMS(ESI): [M]$^+$ m/z: calcd 487.2; found 488.2; Rt=1.923 min.

Example 257. The Synthesis of N-(6-amino-5-ethylpyridin-3-yl)-2-((2R,5S)-2-(3-((2,6-dimethylpyridin-4-yl)oxy)phenyl)-5-methylpiperidin-1-yl)-2-oxoacetamide (Compound 1297)

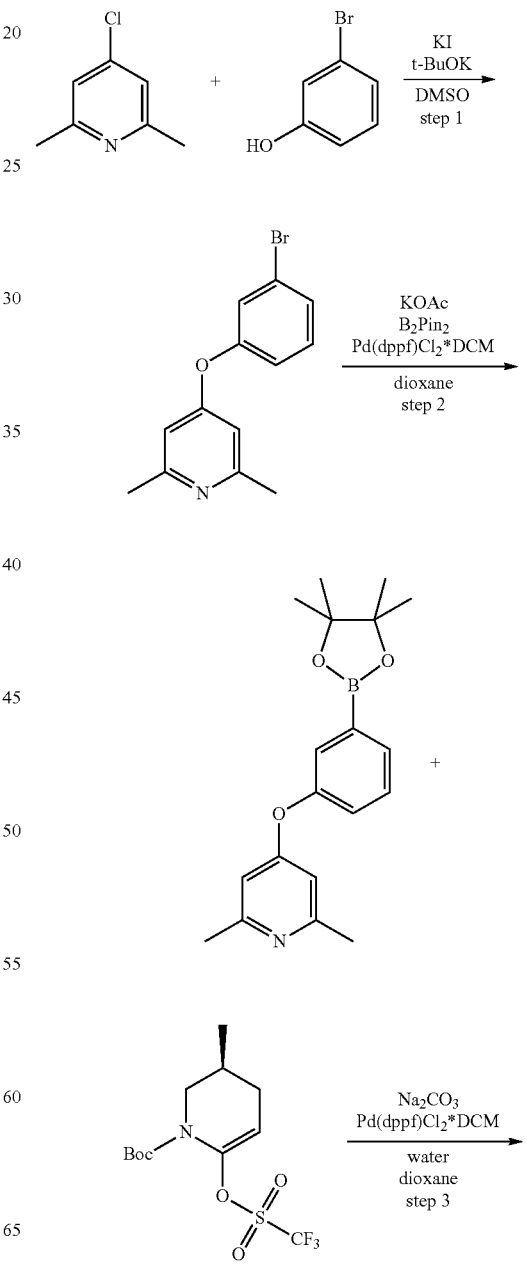

-continued

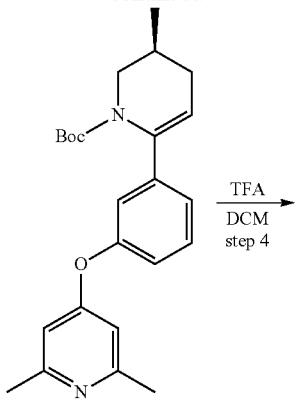

TFA
DCM
step 4

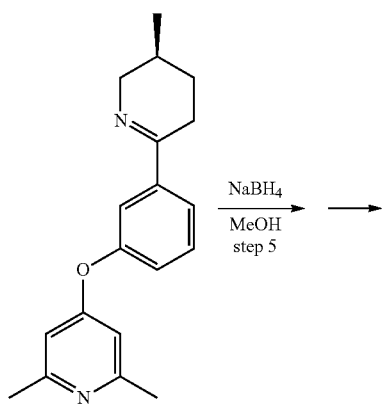

NaBH₄
MeOH
step 5

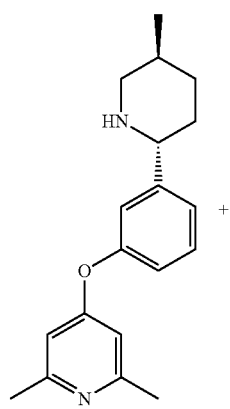

+

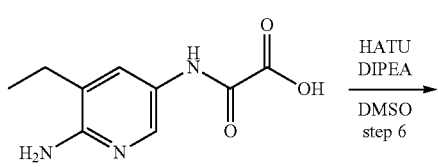

HATU
DIPEA
DMSO
step 6

-continued

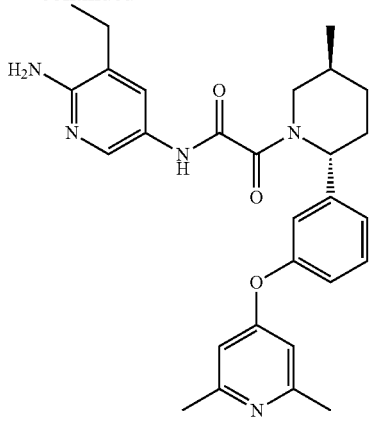

Cmpd 1297

Step 1: Synthesis of
4-(3-bromophenoxy)-2,6-dimethylpyridine

3-bromophenol (30 g, 173.40 mmol) was dissolved in DMSO (400 mL) followed by addition of potassium tert-butoxide (29.19 g, 260.10 mmol). The reaction mixture was stirred at rt for 1 hr and then 4-chloro-2,6-dimethyl-pyridine (36.83 g, 260.10 mmol) was added. The reaction mixture was stirred at 160° C. for 16 hr. Upon completion, the reaction mixture was diluted with water (3 L) and extracted with ethyl acetate. The organic phase was dried, concentrated under reduced pressure and the residue was submitted to flash column chromatography (Interchim; 330 g SiO₂, CHCl₃-MeCN from 0-100%, flow rate=100 mL/min, cv=7.6) to afford 4-(3-bromophenoxy)-2,6-dimethyl-pyridine (12 g, 43.14 mmol, 24.88% yield).

LCMS(ESI): [M]⁺ m/z: calcd 278.2; found 279.2; Rt=0.870 min.

Step 2: Synthesis of 2,6-dimethyl-4-(3-(4,4,5,5-tetramethyl-1,3,2-dioxaborolan-2-yl)phenoxy)pyridine

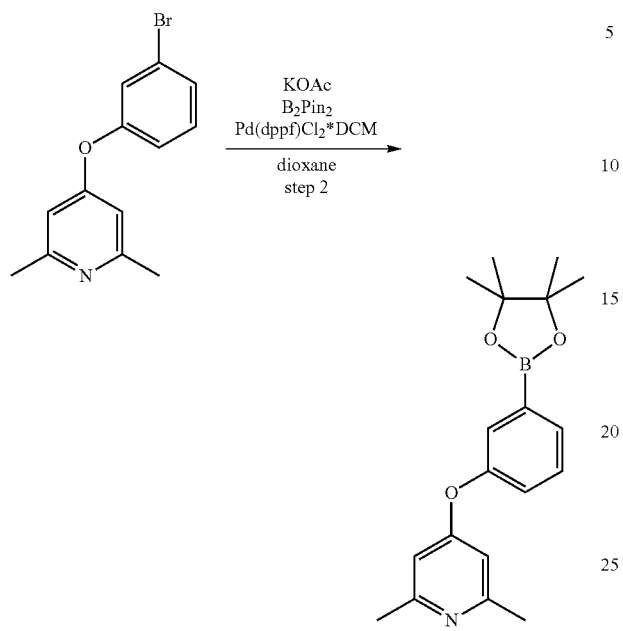

4-(3-bromophenoxy)-2,6-dimethyl-pyridine (12 g, 43.14 mmol), 4,4,5,5-tetramethyl-2-(4,4,5,5-tetramethyl-1,3,2-dioxaborolan-2-yl)-1,3,2-dioxaborolane (13.2 g, 51.98 mmol), potassium acetate (12.7 g, 129.40 mmol, 8.09 mL) and Pd(dppf)Cl₂*DCM (1.76 g, 2.16 mmol) were mixed in dioxane (250 mL) and the reaction mixture was stirred under inert atmosphere at 85° C. for 17 hr. Upon completion, the reaction mixture was filtered through thin pad of SiO₂. The filtrate was diluted with DCM, washed with water and concentrated. The residue was treated with hexane, filtered and concentrated under reduced pressure to afford 2,6-dimethyl-4-[3-(4,4,5,5-tetramethyl-1,3,2-dioxaborolan-2-yl)phenoxy]pyridine (12 g, crude) which was used in the next step without purification.

LCMS(ESI): [M]⁺ m/z: calcd 325.2; found 326.2; Rt=1.186 min.

Step 3: Synthesis of (S)-tert-butyl 6-(3-((2,6-dimethylpyridin-4-yl)oxy)phenyl)-3-methyl-3,4-dihydropyridine-1(2H)-carboxylate

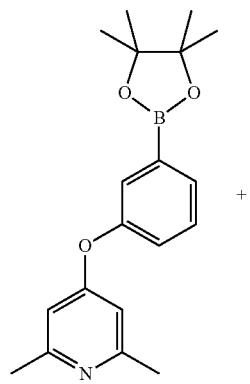
+

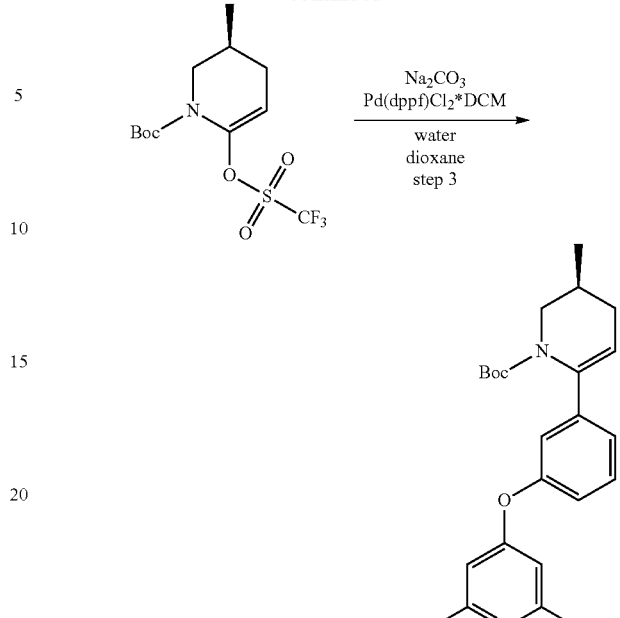

2,6-dimethyl-4-[3-(4,4,5,5-tetramethyl-1,3,2-dioxaborolan-2-yl)phenoxy]pyridine (4 g, 12.30 mmol), tert-butyl (3S)-3-methyl-6-(trifluoromethylsulfonyloxy)-3,4-dihydro-2H-pyridine-1-carboxylate (4.3 g, 12.45 mmol), sodium carbonate (3.9 g, 36.80 mmol, 1.54 mL) and Pd(dppf)Cl₂*DCM (0.5 g, 612.27 μmol) were stirred in a mixture of dioxane (60 mL) and water (20 mL) under inert atmosphere at 85° C. for 15 hr. Upon completion, the reaction mixture was cooled down, diluted with water and extracted with DCM. The organic layer was separated, dried over Na₂SO₄ and the residue was submitted to flash column chromatography (Interchim; 120 g SiO₂, Hexane-EtOAc from 0-100%, flow rate=70 mL/min, cv=13.3) to afford tert-butyl (3S)-6-[3-[(2,6-dimethyl-4-pyridyl)oxy]phenyl]-3-methyl-3,4-dihydro-2H-pyridine-1-carboxylate (3 g, 7.60 mmol, 61.83% yield).

LCMS(ESI): [M]⁺ m/z: calcd 394.2; found 395.2; Rt=1.262 min.

Step 4: Synthesis of (S)-2,6-dimethyl-4-(3-(5-methyl-3,4,5,6-tetrahydropyridin-2-yl)phenoxy)pyridine

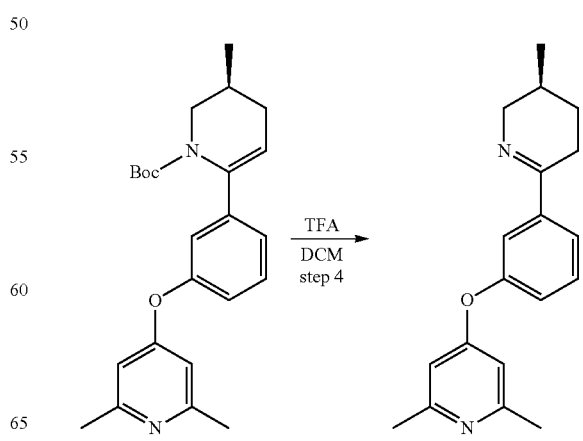

tert-butyl (3S)-6-[3-[(2,6-dimethyl-4-pyridyl)oxy]phenyl]-3-methyl-3,4-dihydro-2H-pyridine-1-carboxylate (0.7 g, 1.77 mmol) was dissolved in a mixture of TFA (1.48 g, 12.98 mmol, 1 mL) and DCM (1 mL). The reaction mixture was stirred at rt for 0.5 hr and concentrated in vacuum to afford 2,6-dimethyl-4-[3-[(3S)-3-methyl-2,3,4,5-tetrahydropyridin-6-yl]phenoxy]pyridine (0.5 g, crude) which was used directly in the next step without purification and analytical data collection.

Step 5: Synthesis of 2,6-dimethyl-4-(3-((2R,5S)-5-methylpiperidin-2-yl)phenoxy)pyridine

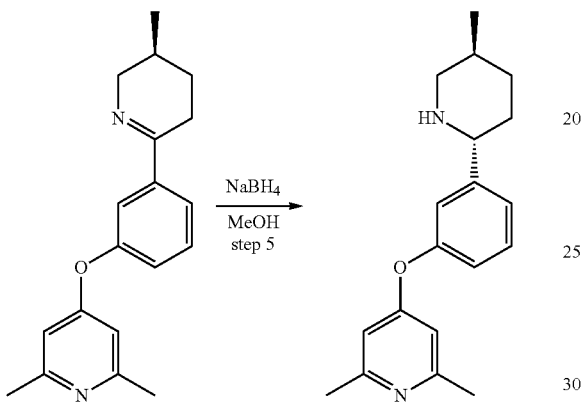

2,6-dimethyl-4-[3-[(3S)-3-methyl-2,3,4,5-tetrahydropyridin-6-yl]phenoxy]pyridine (0.5 g, 1.70 mmol) was dissolved in MeOH (6 mL) followed by portion wise addition of sodium borohydride (192.77 mg, 5.10 mmol, 179.49 μL). The reaction mixture was stirred at rt for 15 hr and concentrated in vacuum. The residue was dissolved in DCM, washed with water. The organic layer was dried over Na$_2$SO$_4$ and concentrated under reduced pressure to afford 2,6-dimethyl-4-[3-[(2R,5S)-5-methyl-2-piperidyl]phenoxy]pyridine (0.2 g, crude) which was used in the next step without purification.

LCMS(ESI): [M]$^+$ m/z: calcd 296.2; found 297.2; Rt=0.710 min.

Step 6: Synthesis of N-(6-amino-5-ethylpyridin-3-yl)-2-((2R,5S)-2-(3-((2,6-dimethylpyridin-4-yl)oxy)phenyl)-5-methylpiperidin-1-yl)-2-oxoacetamide (Compound 1297

To a stirred solution of 2,6-dimethyl-4-[3-[(2R,5S)-5-methyl-2-piperidyl]phenoxy]pyridine (0.2 g, 674.75 μmol), 2-[(6-amino-5-ethyl-3-pyridyl)amino]-2-oxo-acetic acid (155.27 mg, 742.23 μmol) and DIPEA (348.83 mg, 2.70 mmol, 470.12 μL) in DMSO (2 mL) was added HATU (359.18 mg, 944.65 μmol). The resulting reaction mixture was stirred at 25° C. for 4 hr. Upon completion, the reaction mixture was submitted to reverse phase HPLC (2-10 min 55-75% MeOH+NH$_3$ flow 30 mL/min (loading pump 4 mL/min MeOH), Column Sun Fire C18 100*19 mm) to afford N-(6-amino-5-ethyl-3-pyridyl)-2-oxo-2-[(2R,5S)-2-[3-[(2,6-dimethyl-4-pyridyl)oxy]phenyl]-5-methyl-1-piperidyl]acetamide (0.1 μg, 205.09 μmol, 30.39% yield).

$^1$H NMR (600 MHz, DMSO-d$_6$) δ (ppm) 0.98-1.04 (m, 3H), 1.07-1.13 (m, 3H), 1.29-1.38 (m, 1H), 1.61-1.71 (m, 1H), 1.83-1.94 (m, 1H), 1.98-2.11 (m, 1H), 2.16-2.26 (m, 1H), 2.30-2.34 (m, 6H), 2.36-2.41 (m, 2H), 2.74-3.23 (m, 1H), 3.44-4.05 (m, 1H), 5.16-5.66 (m, 3H), 6.55-6.60 (m, 2H), 7.02 (dd, 1H), 7.05-7.16 (m, 1H), 7.18-7.29 (m, 1H), 7.41-7.52 (m, 2H), 7.97-8.06 (m, 1H), 10.43-10.58 (m, 1H).

LCMS(ESI): [M]$^+$ m/z: calcd 487.2; found 488.2; Rt=2.203 min.

Example 258. The Synthesis of N-(6-amino-5-ethylpyridin-3-yl)-2-((2R,5S)-5-methyl-2-(3-(pyridin-3-yloxy)phenyl)piperidin-1-yl)-2-oxoacetamide (Compound 1297

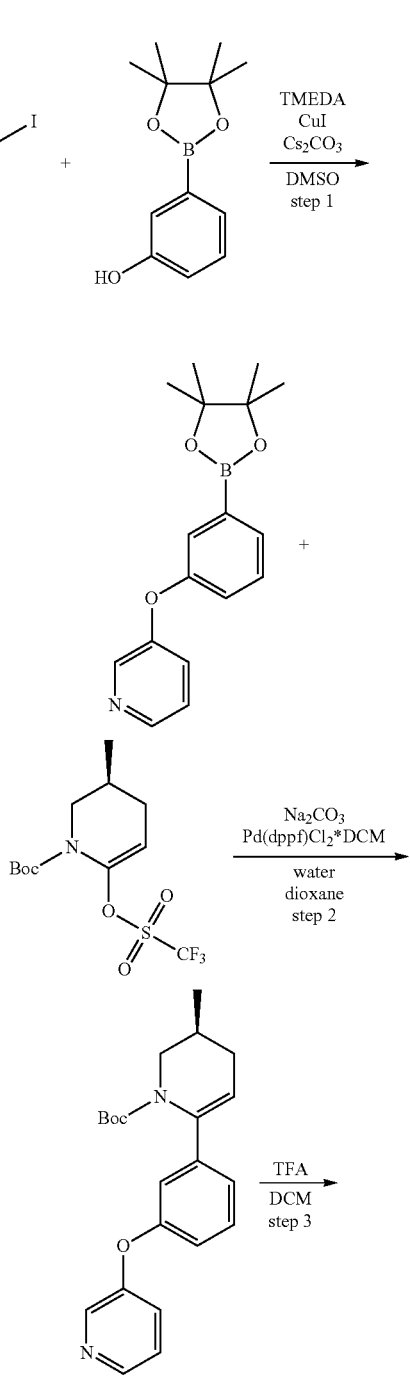

1775
-continued

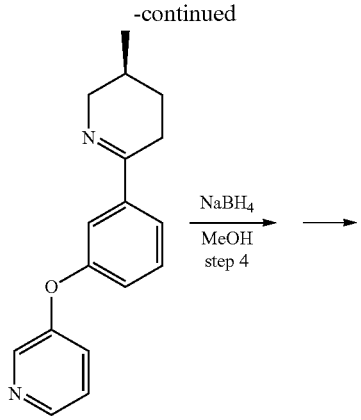
NaBH₄
MeOH
step 4
→

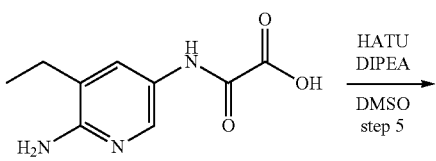
+

HATU
DIPEA
DMSO
step 5
→

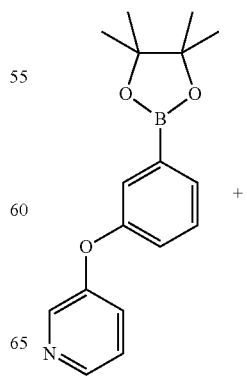
Compound 1180

1776

Step 1: Synthesis of 3-(3-(4,4,5,5-tetramethyl-1,3,2-dioxaborolan-2-yl)phenoxy)pyridine

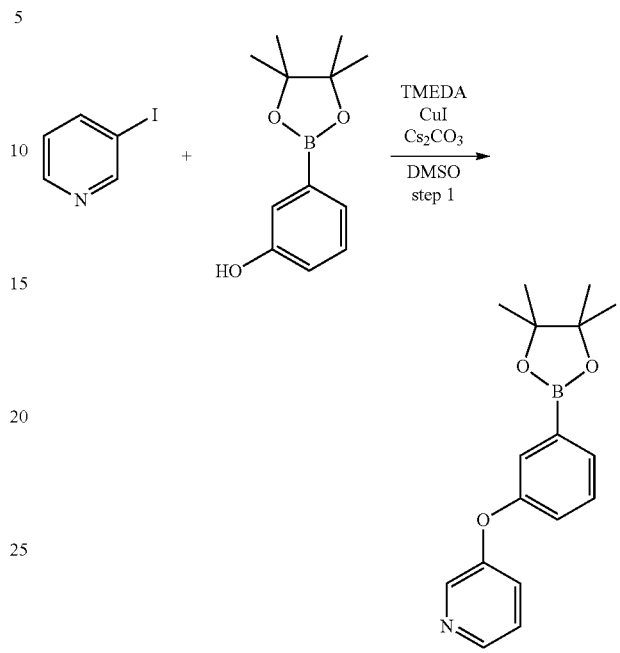

3-iodopyridine (30 g, 146.34 mmol), 3-(4,4,5,5-tetramethyl-1,3,2-dioxaborolan-2-yl)phenol (32.21 g, 146.34 mmol), TMEDA (1.70 g, 14.63 mmol, 2.19 mL), copper (I) iodide (2.79 g, 14.63 mmol, 495.93 µL), and cesium carbonate (95.36 g, 292.69 mmol) were mixed in DMSO (500 mL). The reaction mixture was charged with Ar and stirred at 130° C. for 24 hr. Upon completion, the reaction mixture was diluted with water (3 L) and extracted with ethyl acetate. The organic layer was washed with water several times, separated, dried over Na₂SO₄ and concentrated under reduced pressure. The residue was submitted to flash column chromatography (Interchim; 120 g SiO₂, CHCl₃-MeCN from 0-100%, flow rate=70 mL/min, cv=16) to afford 3-[3-(4,4,5,5-tetramethyl-1,3,2-dioxaborolan-2-yl)phenoxy]pyridine (7 g, crude).

LCMS(ESI): [M]⁺ m/z: calcd 297.2; found 298.2; Rt=1.437 min.

Step 2: Synthesis of (S)-tert-butyl 3-methyl-6-(3-(pyridin-3-yloxy)phenyl)-3,4-dihydropyridine-1(2H)-carboxylate -continued

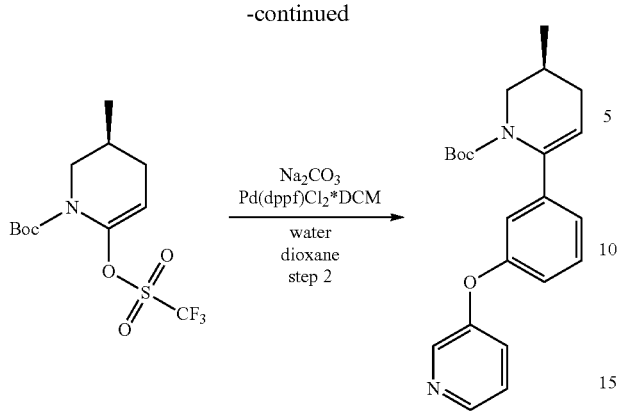

3-[3-(4,4,5,5-tetramethyl-1,3,2-dioxaborolan-2-yl)phenoxy]pyridine (4 g, 13.46 mmol), tert-butyl (3S)-3-methyl-6-(trifluoromethylsulfonyloxy)-3,4-dihydro-2H-pyridine-1-carboxylate (4.71 g, 13.63 mmol), sodium carbonate (4.27 g, 40.27 mmol, 1.69 mL) and Pd(dppf)Cl$_2$*DCM (547.20 mg, 670.07 µmol) were stirred in a mixture of dioxane (60 mL) and water (20 mL) under inert atmosphere at 85° C. for 16 hr. Upon completion, the reaction mixture was cooled down, diluted with water and extracted with DCM. The organic layer was separated, dried over Na$_2$SO$_4$ and concentrated under reduced pressure to afford tert-butyl (3S)-3-methyl-6-[3-(3-pyridyloxy)phenyl]-3,4-dihydro-2H-pyridine-1-carboxylate (5 g, crude) which was used in the next step without purification.

LCMS(ESI): [M]$^+$ m/z: calcd 366.2; found 367.2; Rt=1.578 min.

Step 3: Synthesis of (S)-3-(3-(5-methyl-3,4,5,6-tetrahydropyridin-2-yl)phenoxy)pyridine

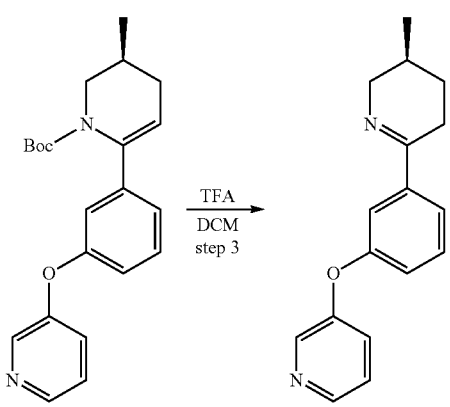

tert-butyl (3S)-3-methyl-6-[3-(3-pyridyloxy)phenyl]-3,4-dihydro-2H-pyridine-1-carboxylate (1 g, 2.73 mmol) was dissolved in a mixture of TFA (2.22 g, 19.47 mmol, 1.5 mL) and DCM (1.5 mL). The reaction mixture was stirred at rt for 0.5 hr and concentrated in vacuum to afford 3-[3-[(3S)-3-methyl-2,3,4,5-tetrahydropyridin-6-yl]phenoxy]pyridine (0.5 g, crude) which was used directly in the next step without purification and analytical data collection.

LCMS(ESI): [M]$^+$ m/z: calcd 266.2; found 267.2; Rt=min.

Step 4: Synthesis of 3-(3-((2R,5S)-5-methylpiperidin-2-yl)phenoxy)pyridine

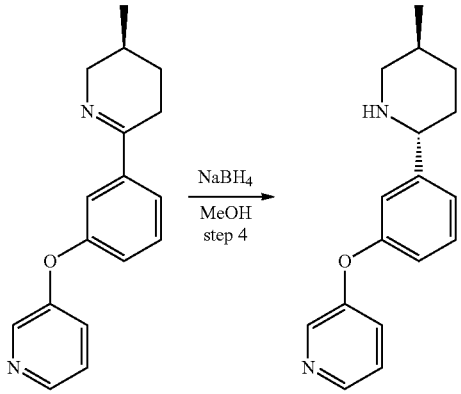 [SMILES: C[C@H]1CCC(c2cccc(Oc3cccnc3)c2)=NC1 ; "MeOHstep 4" ; "NaBH4" ; C[C@H]1CC[C@H](c2cccc(Oc3cccnc3)c2)NC1]

3-[3-[(3S)-3-methyl-2,3,4,5-tetrahydropyridin-6-yl]phenoxy]pyridine (0.5 g, 1.88 mmol) was dissolved in MeOH (5 mL) followed by portion wise addition of sodium borohydride (142.04 mg, 3.75 mmol, 132.25 µL). The reaction mixture was stirred at rt for 15 hr and concentrated in vacuum. The residue was dissolved in DCM, washed with water. The organic layer was dried over Na$_2$SO$_4$ and concentrated under reduced pressure to afford 3-[3-[(2R,5S)-5-methyl-2-piperidyl]phenoxy]pyridine (0.5 g, crude) which was used in the next step without purification.

LCMS(ESI): [M]$^+$ m/z: calcd 268.2; found 269.2; Rt=0.713 min.

Step 5: Synthesis of N-(6-amino-5-ethylpyridin-3-yl)-2-((2R,5S)-5-methyl-2-(3-(pyridin-3-yloxy)phenyl)piperidin-1-yl)-2-oxoacetamide (Compound 1297

To a stirred solution of 3-[3-[(2R,5S)-5-methyl-2-piperidyl]phenoxy]pyridine (0.5 g, 1.86 mmol), 2-[(6-amino-5-ethyl-3-pyridyl)amino]-2-oxo-acetic acid (428.77 mg, 2.05 mmol) and DIPEA (722.41 mg, 5.59 mmol, 973.59 µL) in DMSO (8.32 mL) was added HATU (991.83 mg, 2.61 mmol). The resulting reaction mixture was stirred at 25° C. for 4 hr. Upon completion, the reaction mixture was submitted to reverse phase HPLC (2-10 min 55-75% MeOH+ NH$_3$ flow 30 mL/min (loading pump 4 mL/min MeOH), Column Sun Fire C18 100*19 mm) to afford N-(6-amino-5-ethyl-3-pyridyl)-2-oxo-2-[(2R,5S)-5-methyl-2-[3-(3-pyridyloxy)phenyl]-1-piperidyl]acetamide (0.023 g, 50.05 µmol, 2.69% yield).

$^1$H NMR (600 MHz, DMSO-d$_6$) δ (ppm) 0.98-1.05 (m, 3H), 1.06-1.12 (m, 3H), 1.25-1.37 (m, 1H), 1.60-1.73 (m, 1H), 1.82-1.91 (m, 1H), 1.96-2.12 (m, 1H), 2.14-2.24 (m, 1H), 2.37-2.43 (m, 2H), 2.76-3.21 (m, 1H), 3.46-4.08 (m, 1H), 5.14-5.59 (m, 1H), 5.60-5.69 (m, 2H), 6.89-6.96 (m, 1H), 7.03-7.11 (m, 1H), 7.12-7.22 (m, 1H), 7.36-7.52 (m, 4H), 7.95-8.09 (m, 1H), 8.29-8.41 (m, 2H), 10.25 (s, 1H).

LCMS(ESI): [M]$^+$ m/z: calcd 459.2; found 460.2; Rt=0.855 min.

Example 259. The Synthesis of N-(6-amino-5-ethylpyridin-3-yl)-2-((2R,5S)-2-(3-(3-(dimethylamino)Propyl)phenyl)-5-methylpiperidin-1-yl)-2-oxoacetamide (Compound 1393

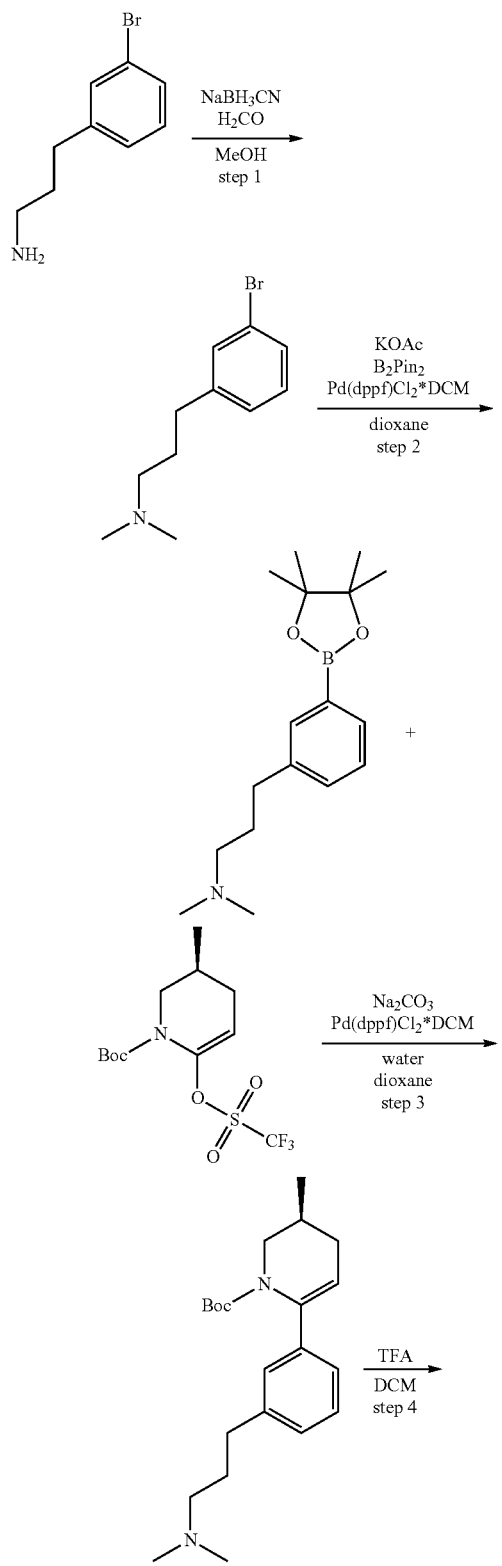

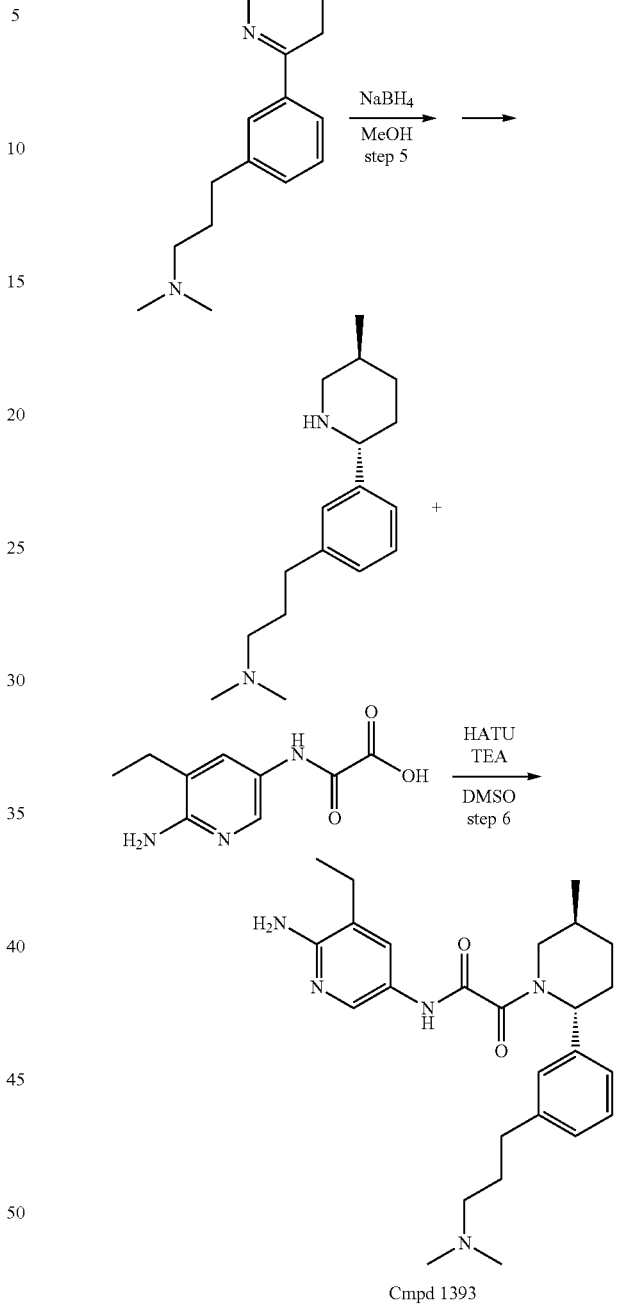

Step 1: Synthesis of 3-(3-bromophenyl)-N,N-dimethylpropan-1-amine

Sodium cyan borohydride (13.22 g, 210.33 mmol) was added in 4 portions to a mixture of 3-(3-bromophenyl)propan-1-amine (5.27 g, 21.03 mmol, HCl) and formalin (12.34 g, 152.04 mmol, 11.39 mL, 37% purity) in MeOH (100.00 mL) and stirred overnight. The reaction mixture was treated with aq. solution of $NaHCO_3$ and desired product was extracted with 300 mL of DCM, dried over $Na_2SO_4$ and concentrated in vacuum to give 3-(3-bromophenyl)-N,N-dimethyl-propan-1-amine (3.4 g, crude).

LCMS(ESI): [M]⁺ m/z: calcd 242.2; found 243.2; Rt=0.631 min.

Step 2: Synthesis of N,N-dimethyl-3-(3-(4,4,5,5-tetramethyl-1,3,2-dioxaborolan-2-yl)phenyl)Propan-1-amine A mixture of 3-(3-bromophenyl)-N,N-dimethyl-propan-1-amine (3.4 g, 14.04 mmol), Bis(pinacolato)diboron (4.64 g, 18.25 mmol) and potassium acetate (4.13 g, 42.12 mmol, 2.63 mL) in dioxane (49.66 mL) was degassed with argon for 10 min. Pd(dppf)Cl$_2$*DCM (573.30 mg, 702.03 µmol) was next added and the reaction mixture was heated at 90° C. for 12 hr. The reaction mixture was cooled to rt, diluted with DCM. Organic phase was separated and concentrated under reduced pressure. Crude product was treated with HCl/diox solution (10% HCl) and concentrated again. The residue was treated with MTBE and precipitate was collected by filtration to give N,N-dimethyl-3-[3-(4,4,5,5-tetramethyl-1,3,2-dioxaborolan-2-yl)phenyl]propan-1-amine (2.67 g, crude, HCl).

LCMS(ESI): [M]⁺ m/z: calcd 289.2; found 290.2; Rt=1.085 min.

Step 3: Synthesis of (S)-tert-butyl 6-(3-(3-(dimethylamino)Propyl)phenyl)-3-methyl-3,4-dihydropyridine-1(2H)-carboxylate N,N-dimethyl-3-[3-(4,4,5,5-tetramethyl-1,3,2-dioxaborolan-2-yl)phenyl]propan-1-amine (2.67 g, 6.15 mmol, HCl) and sodium carbonate (2.61 g, 24.59 mmol, 1.03 mL) were mixed in H$_2$O (10 mL) and dioxane (30 mL) and stirred for 20 min, then tert-butyl (3S)-3-methyl-6-(trifluoromethylsulfonyloxy)-3,4-dihydro-2H-pyridine-1-carboxylate (2.55 g, 7.38 mmol) and Pd(dppf)Cl$_2$*DCM (501.73 mg, 614.87 µmol) were added under argon and stirred at 75° C. for 12 hr. Reaction mixture was diluted with water and desired product was extracted with 100 mL of DCM, dried over Na$_2$SO$_4$ and concentrated in vacuum. tert-butyl (3S)-6-[3-[3-(dimethylamino)propyl]phenyl]-3-methyl-3,4-dihydro-2H-pyridine-1-carboxylate (3.2 g, crude) was obtained.

LCMS(ESI): [M]f m/z: calcd 358.2; found 359.2; Rt=1.226 min.

Step 4: Synthesis of (S)—N,N-dimethyl-3-(3-(5-methyl-3,4,5,6-tetrahydropyridin-2-yl)phenyl)Propan-1-amine tert-butyl (3S)-6-[3-[3-(dimethylamino)propyl]phenyl]-3-methyl-3,4-dihydro-2H-pyridine-1-carboxylate (3.2 g, 3.79 mmol) was dissolved in mixture of TFA (8 g, 70.16 mmol, 5.41 mL) and DCM (20 mL) and stirred for 1 hr. The reaction mixture was concentrated in vacuum and the residue was treated with NaHCO$_3$ solution followed by extraction with DCM (2*50 mL). Then the aqueous layer was treated again with EtOAc, organic phase was dried over Na$_2$SO$_4$ and concentrated under reduced pressure to afford N,N-dimethyl-3-[3-[(3S)-3-methyl-2,3,4,5-tetrahydropyridin-6-yl]phenyl]propan-1-amine (320 mg, crude) which was used in the next step without purification.

LCMS(ESI): [M]f m/z: calcd 258.2; found 259.2; Rt=0.613 min.

Step 5: Synthesis of N,N-dimethyl-3-(3-((2R,5S)-5-methylpiperidin-2-yl)phenyl)Propan-1-amine N,N-dimethyl-3-[3-[(3S)-3-methyl-2,3,4,5-tetrahydropyridin-6-yl]phenyl]propan-1-amine (320 mg, 850.52 µmol) was dissolved in MeOH (20 mL) and sodium borohydride (64.35 mg, 1.70 mmol, 59.92 µL) was added. After stirring for 12 hr RM was concentrated and used in the next step without purification. N,N-dimethyl-3-[3-[(2R,5S)-5-methyl-2-piperidyl]phenyl]propan-1-amine (250 mg, crude) was obtained.

LCMS(ESI): [M]⁺ m/z: calcd 260.2; found 261.2; Rt=0.203 min.

Step 6: Synthesis of N-(6-amino-5-ethylpyridin-3-yl)-2-((2R,5S)-2-(3-(3-(dimethylamino)Propyl)phenyl)-5-methylpiperidin-1-yl)-2-oxoacetamide (Compound 1393)

Crude product N,N-dimethyl-3-[3-[(2R,5S)-5-methyl-2-piperidyl]phenyl]propan-1-amine (320 mg, 847.87 µmol) from previous stage was mixed with TEA (400 mg, 3.95 mmol, 550.96 µL) in DMSO (4 mL), next 2-[(6-amino-5-ethyl-3-pyridyl)amino]-2-oxo-acetic acid (177.38 mg, 847.87 µmol) and HATU (451.34 mg, 1.19 mmol) was added and stirred overnight. RM was filtered and subjected to HPLC (2-10 min 0-55% water/MeOH+NH$_3$30 mL/min; loading pump 4 mL/min MeOH; column SunFire 19*100 mm) to afford N-(6-amino-5-ethyl-3-pyridyl)-2-oxo-2-((2R,5S)-2-[3-[3-(dimethylamino)propyl]phenyl]-5-methyl-1-piperidyl]acetamide (34.2 mg, 75.73 µmol, 8.93% yield).

¹H NMR (500 MHz, DMSO-d$_6$) δ (ppm) 0.75-1.03 (m, 3H), 1.06-1.15 (m, 3H), 1.28-1.39 (m, 1H), 1.61-1.69 (m, 3H), 1.79-1.93 (m, 1H), 1.96-2.07 (m, 1H), 2.07-2.11 (m, 6H), 2.14-2.25 (m, 3H), 2.35-2.42 (m, 2H), 2.56-2.62 (m, 2H), 2.72-3.23 (m, 1H), 3.44-4.05 (m, 1H), 5.11-5.58 (m, 1H), 5.59-5.67 (m, 2H), 7.06-7.12 (m, 2H), 7.12-7.18 (m, 1H), 7.25-7.32 (m, 1H), 7.43-7.54 (m, 1H), 7.95-8.09 (m, 1H), 10.47-10.58 (m, 1H).

LCMS(ESI): [M]⁺ m/z: calcd 451.2; found 452.2; Rt=1.832 min.

Example 260. The Synthesis of N-(6-amino-5-ethylpyridin-3-yl)-2-((2R,5S)-2-(3-(3-(dimethylamino)Propoxy)phenyl)-5-methylpiperidin-1-yl)-2-oxoacetamide (Compound 1384)

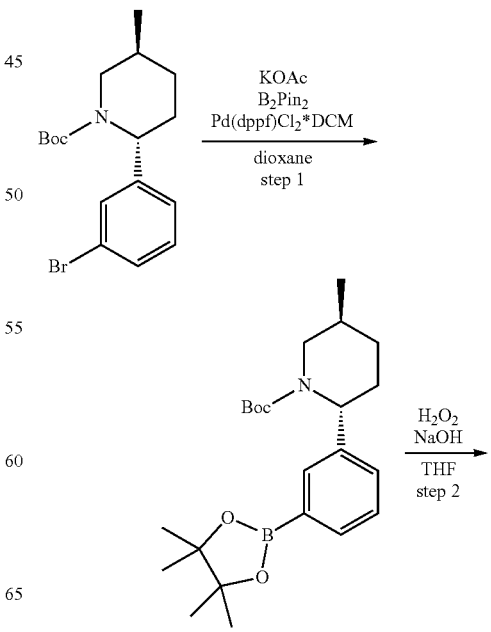

1783

-continued

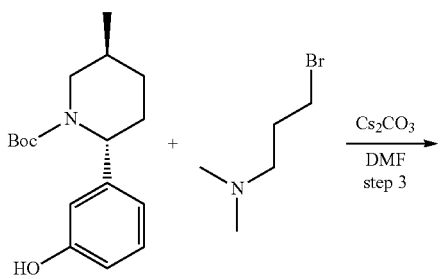

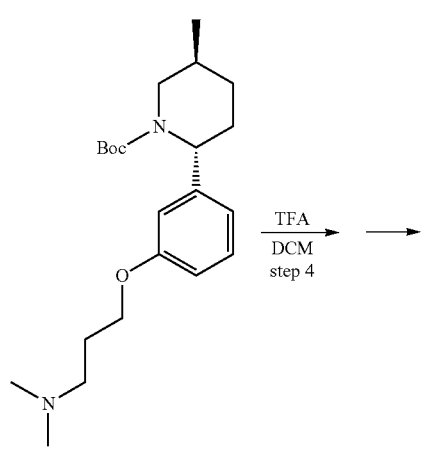

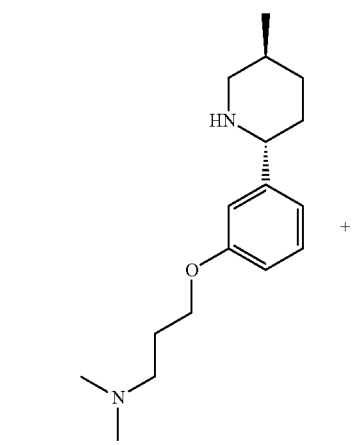

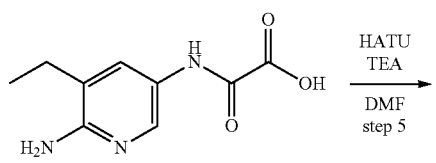

1784

-continued

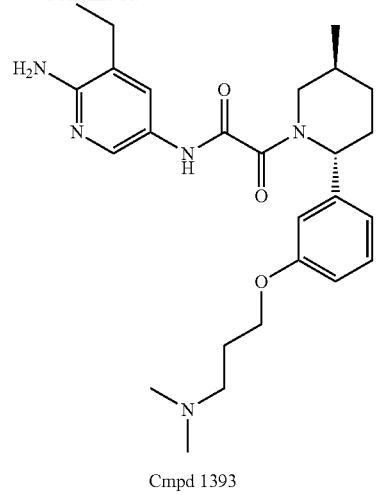

Cmpd 1393

Step 1: Synthesis of (2R,5S)-tert-butyl 5-methyl-2-(3-(4,4,5,5-tetramethyl-1,3,2-dioxaborolan-2-yl)phenyl)piperidine-1-carboxylate tert-butyl (2R,5S)-2-(3-bromophenyl)-5-methyl-piperidine-1-carboxylate (3.4 g, 9.60 mmol), 4,4,5,5-tetramethyl-2-(4,4,5,5-tetramethyl-1,3,2-dioxaborolan-2-yl)-1,3,2-dioxaborolane (2.68 g, 10.56 mmol) and potassium acetate (2.35 g, 23.99 mmol, 1.50 mL) were mixed together in dioxane (40.00 mL) and the resulting mixture was evacuated and backfilled three times with argon. Pd(dppf)Cl$_2$*DCM (391.86 mg, 479.85 μmol) was added to the previous mixture and the resulting mixture was heated at 100° C. overnight. The reaction mixture was concentrated in vacuum and water (25 mL) was added to the residue. The resulting mixture was extracted with MTBE (2*40 mL) and combined organic layers were washed with water (25 mL), brine (25 mL), dried over Na$_2$SO$_4$, filtered and concentrated in vacuum to obtain tert-butyl (2R,5S)-5-methyl-2-[3-(4,4,5,5-tetramethyl-1,3,2-dioxaborolan-2-yl)phenyl]piperidine-1-carboxylate (3.5 g, 8.72 mmol, 90.87% yield).

LCMS(ESI): [M-Boc]$^+$ m/z: calcd 301.2; found 302.2; Rt=1.745 min.

Step 2: Synthesis of (2R,5S)-tert-butyl 2-(3-hydroxyphenyl)-S-methylpiperidine-1-carboxylate tert-butyl (2R,5S)-5-methyl-2-[3-(4,4,5,5-tetramethyl-1,3,2-dioxaborolan-2-yl)phenyl]piperidine-1-carboxylate (3.7 g, 9.22 mmol) was dissolved in THF (50.73 mL) and hydrogen peroxide 35% (1.34 g, 13.83 mmol, 1.22 mL, 35% purity) was carefully added dropwise at room temperature. After addition completed, the reaction mixture was stirred for 1 hr and aq. solution of sodium hydroxide, pearl (590.01 mg, 14.75 mmol, 277.00 μL) was added dropwise at room temperature. After addition completed, the reaction mixture was stirred for 1 hr. The reaction mixture was acidified with citric acid and the resulting mixture was transferred to a separation funnel. An organic layer was separated and the aqueous layer was extracted with MTBE (2*40 mL). Combined organic layers were washed with aq. sodium sulfite, dried over Na$_2$SO$_4$, filtered and concentrated in vacuum to obtain tert-butyl (2R,5S)-2-(3-hydroxyphenyl)-5-methyl-piperidine-1-carboxylate (3 g, crude).

LCMS(ESI): [M-Boc]⁺ m/z: calcd 191.2; found 192.2; Rt=1.428 min.

Step 3: Synthesis of (2R,5S)-tert-butyl 2-(3-(3-(dimethylamino)Propoxy)phenyl)-5-methylpiperidine-1-carboxylate tert-butyl (2R,5S)-2-(3-hydroxyphenyl)-5-methyl-piperidine-1-carboxylate (0.75 g, 2.57 mmol) was dissolved in DMF (10 mL) and 3-bromo-N,N-dimethyl-propan-1-amine (1.27 g, 5.15 mmol, HBr) was added thereto followed by addition of cesium carbonate (3.35 g, 10.30 mmol). The resulting mixture was heated at 50° C. overnight. The reaction mixture was poured into water (5 mL) and the resulting mixture was extracted with EtOAc (3*20 mL). Combined organic layers were washed with water (3*10 mL), brine (10 mL), dried over Na₂SO₄, filtered, and concentrated in vacuum to afford product.

LCMS(ESI): [M]⁺ m/z: calcd 376.2; found 377.2; Rt=1.109 min.

Step 4: Synthesis of N,N-dimethyl-3-(3-((2R,5S)-5-methylpiperidin-2-yl)phenoxy)Propan-1-amine tert-butyl (2R,5S)-2-[3-[3-(dimethylamino)propoxy]phenyl]-5-methyl-piperidine-1-carboxylate (350 mg, 929.54 μmol) was dissolved in DCM (1.5 mL) and TFA (1.5 mL) was added thereto. The resulting mixture was stirred for 1 hr. The reaction mixture was carefully poured into aq.NaHCO₃ solution (3 g in 10 mL of water) and the resulting mixture was extracted with DCM (2*15 mL). Combined organic layers were dried over sodium sulfate, filtered, and concentrated in vacuum to obtain N,N-dimethyl-3-[3-[(2R,5S)-5-methyl-2-piperidyl]phenoxy]propan-1-amine (250 mg, crude).

LCMS(ESI): [M]f m/z: calcd 276.2; found 277.2; Rt=0.581 min.

Step 5: Synthesis of N-(6-amino-5-ethylpyridin-3-yl)-2-((2R,5S)-2-(3-(3-(dimethylamino)Propoxy)phenyl)-5-methylpiperidin-1-yl)-2-oxoacetamide (Compound 1384

N,N-dimethyl-3-[3-[(2R,5S)-5-methyl-2-piperidyl]phenoxy]propan-1-amine (250 mg, 904.43 μmol) was dissolved in DMF (5 mL) and TEA (915.20 mg, 9.04 mmol, 1.26 mL) was added, followed by 2-[(6-amino-5-ethyl-3-pyridyl)amino]-2-oxo-acetic acid (189.21 mg, 904.43 mol). Then the HATU (515.84 mg, 1.36 mmol) was added dropwise and the reaction mixture was stirred overnight. The next day it was evaporated in vacuum and purified by HPLC (2-10 min 0-55% water/MeOH+NH₃30 mL/min; loading pump 4 mL/min MeOH+NH₃; column SunFire 19*100 mm) to obtain N-(6-amino-5-ethyl-3-pyridyl)-2-oxo-2-[(2R,5S)-2-[3-[3-(dimethylamino)propoxy]phenyl]-5-methyl-1-piperidyl]acetamide (33.4 mg, 71.43 μmol, 7.90% yield).

¹H NMR (500 MHz, DMSO-d₆) δ (ppm) 0.99-1.05 (m, 3H), 1.07-1.13 (m, 3H), 1.26-1.37 (m, 1H), 1.60-1.72 (m, 1H), 1.80-1.91 (m, 3H), 1.97-2.09 (m, 1H), 2.11-2.14 (m, 6H), 2.15-2.25 (m, 1H), 2.34-2.43 (m, 4H), 2.72-3.23 (m, 1H), 3.44-4.02 (m, 3H), 5.11-5.55 (m, 1H), 5.59-5.67 (m, 2H), 6.78-6.95 (m, 3H), 7.25-7.31 (m, 1H), 7.43-7.53 (m, 1H), 7.99-8.09 (m, 1H), 10.41-10.62 (m, 1H).

LCMS(ESI): [M]⁺ m/z: calcd 467.2; found 468.2; Rt=0.779 min.

Example 261. The Synthesis of N-(6-amino-5-ethylpyridin-3-yl)-2-((2R,5)-5-methyl-2-(3-(2-(pyrrolidin-1-yl)ethoxy)phenyl)piperidin-1-yl)-2-oxoacetamide (Compound 1391

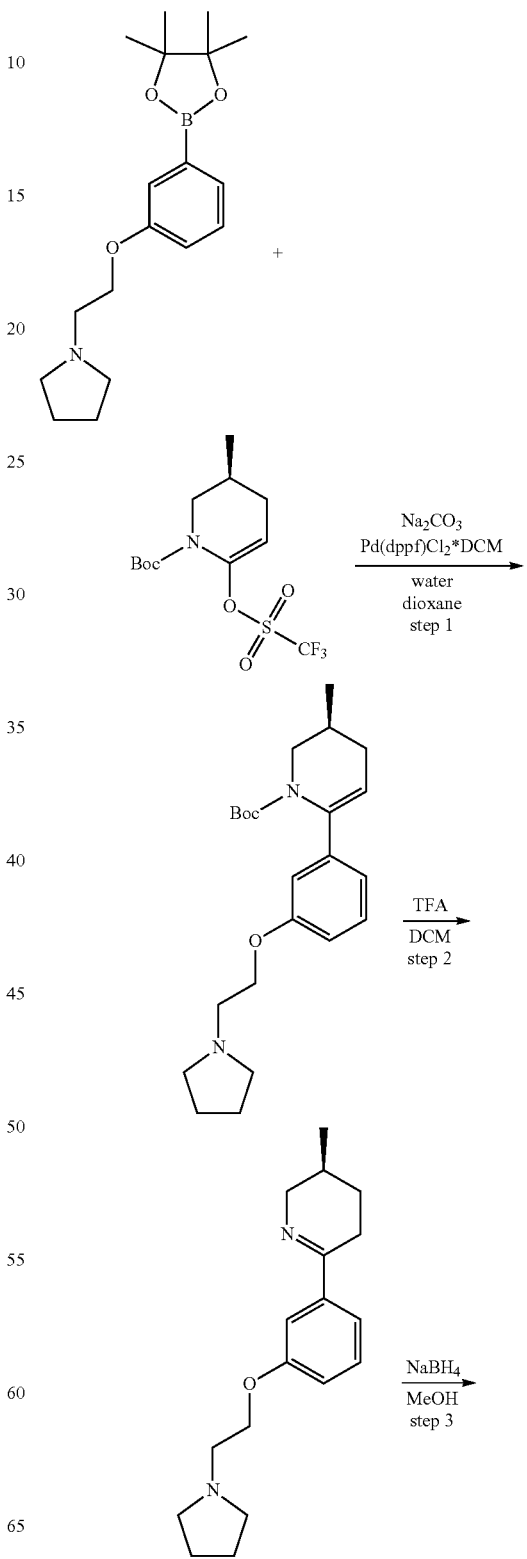

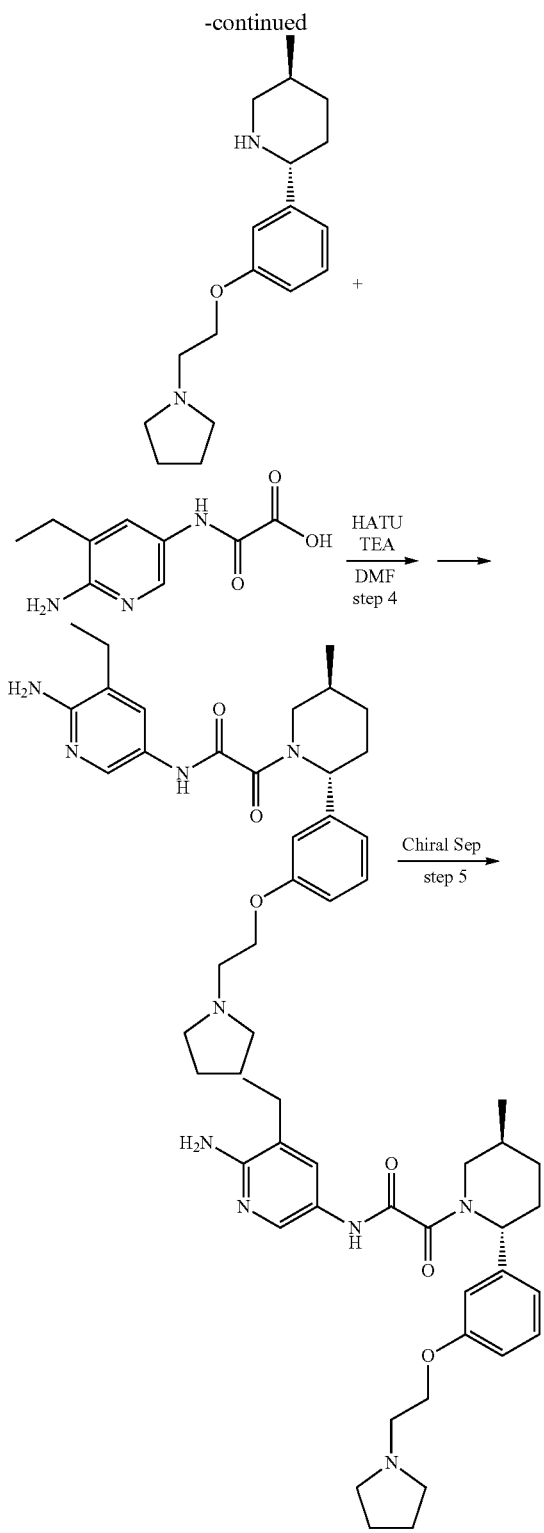

Step 1: Synthesis of (S)-tert-butyl 3-methyl-6-(3-(2-(pyrrolidin-1-yl)ethoxy)phenyl)-3,4-dihydropyridine-1(2H)-carboxylate tert-butyl (3S)-3-methyl-6-(trifluoromethylsulfonyloxy)-3,4-dihydro-2H-pyridine-1-carboxylate (1 g, 2.90 mmol), 1-[2-[3-(4,4,5,5-tetramethyl-1,3,2-dioxaborolan-2-yl)phenoxy]ethyl]pyrrolidine (853.50 mg, 2.41 mmol, HCl) and sodium carbonate (767.30 mg, 7.24 mmol, 303.04 µL) were mixed together in a mixture of dioxane (12 mL) and Water (4 mL). The resulting mixture was evacuated and backfilled three times with argon and Pd(dppf)Cl$_2$*DCM (98.53 mg, 120.66 µmol) was added thereto. The resulting mixture was heated at 90° C. overnight. The resulting mixture was cooled and diluted with water (40 mL). The resulting mixture was extracted with EtOAc (2*45 mL) and combined organic layers were washed with brine (40 mL), dried over Na$_2$SO$_4$, filtered, and concentrated in vacuum. The residue (1.12 g of crude product) was purified by column chromatography (gradient MeOH in chloroform, from 0% to 9%) to obtain tert-butyl (3S)-3-methyl-6-[3-(2-pyrrolidin-1-ylethoxy)phenyl]-3,4-dihydro-2H-pyridine-1-carboxylate (0.534 g, 1.38 mmol, 57.25% yield).

LCMS(ESI): [M]$^+$ m/z: calcd 386.2; found 387.2; Rt=1.210 min.

Step 2: Synthesis of (S)-3-methyl-6-(3-(2-(pyrrolidin-1-yl)ethoxy)phenyl)-2,3,4,5-tetrahydropyridine tert-butyl(3S)-3-methyl-6-[3-(2-pyrrolidin-1-ylethoxy)phenyl]-3,4-dihydro-2H-pyridine-1-carboxylate (0.534 g, 1.38 mmol) was dissolved in DCM (2 mL) and TFA (2 mL) was added thereto. The resulting mixture was stirred for 1 hr. The reaction mixture was carefully poured into aq.NaHCO$_3$ solution (3 g in 25 mL of water) and the resulting mixture was extracted with DCM (2*30 mL). Combined organic layers were dried over sodium sulfate, filtered, and concentrated in vacuum to obtain (3S)-3-methyl-6-[3-(2-pyrrolidin-1-ylethoxy)phenyl]-2,3,4,5-tetrahydropyridine (333 mg, 1.16 mmol, 84.16% yield).

LCMS(ESI): [M]$^+$ m/z: calcd 286.2; found 287.2; Rt=0.386 min.

Step 3: Synthesis of (2R,5S)-5-methyl-2-(3-(2-(pyrrolidin-1-yl)ethoxy)phenyl)piperidine (3S)-3-methyl-6-[3-(2-pyrrolidin-1-ylethoxy)phenyl]-2,3,4,5-tetrahydropyridine (333 mg, 1.16 mmol) was dissolved in MeOH (5 mL) and sodium borohydride (87.97 mg, 2.33 mmol, 81.91 µL) was added portion wise. The resulting mixture was stirred overnight. Water (10 mL) was added to the reaction mixture and the resulting mixture was concentrated in vacuum. The residue was diluted with water (15 mL) and the resulting mixture was extracted with DCM (2*35 mL). Combined organic layers were dried over Na$_2$SO$_4$, filtered, and concentrated in vacuum to obtain (2R,5S)-5-methyl-2-[3-(2-pyrrolidin-1-ylethoxy)phenyl]piperidine (235 mg, 814.77 µmol, 70.08% yield).

LCMS(ESI): [M]$^+$ m/z: calcd 288.2; found 289.2; Rt=0.548 min.

Step 4: Synthesis of N-(6-amino-5-ethylpyridin-3-yl)-2-((2R,5S)-5-methyl-2-(3-(2-(pyrrolidin-1-yl)ethoxy)phenyl)piperidin-1-yl)-2-oxoacetamide (2R,5S)-5-methyl-2-[3-(2-pyrrolidin-1-ylethoxy)phenyl]piperidine (235.00 mg, 814.77 mol), 2-[(6-amino-5-ethyl-3-pyridyl)amino]-2-oxo-acetic acid (170.45 mg, 814.77 µmol) and TEA (412.23 mg, 4.07 mmol, 567.81 µL) were mixed together in DMF (2 mL) and HATU (371.76 mg, 977.72 µmol) was added thereto. The resulting mixture was stirred overnight. The reaction mixture was submitted to HPLC and purified (2-10 min 40-65% MeOH+NH$_3$, 30 mL/min (loading pump 4 mL MeOH+NH$_3$) column: SunFire 100*19 mm, 5 microM) to obtain N-(6-amino-5-ethyl-3-pyridyl)-2-oxo-2-[(2R,5S)-5-methyl-2-[3-(2-pyrrolidin-1-ylethoxy)phenyl]-1-piperidyl]acetamide (87.7 mg, 182.86 μmol, 22.44% yield) and N-(6-amino-5-ethyl-3-pyridyl)-2-oxo-2-[(2R,5S)-5-methyl-2-[3-(2-pyrrolidin-1-ylethoxy)phenyl]-1-piperidyl]acetamide (49.4 mg, 103.00 μmol, 12.64% yield).

LCMS(ESI): [M]+ m/z: calcd 479.2; found 480.2; Rt=0.909 min.

Step 5: Synthesis of Chiral Separation (Compound 1391

N-(6-amino-5-ethyl-3-pyridyl)-2-oxo-2-[(2R,5S)-5-methyl-2-[3-(2-pyrrolidin-1-ylethoxy)phenyl]-1-piperidyl]acetamide (49.4 mg, 103.00 μmol) was chiral separated Chiralpak AS-H (250*20 mm, 5 mkm); Mobile phase: Hexane-IPA-MeOH, 50-25-25. Flow Rate: 10 mL/min to obtain N-(6-amino-5-ethyl-3-pyridyl)-2-oxo-2-[(2R,5S)-5-methyl-2-[3-(2-pyrrolidin-1-ylethoxy)phenyl]-1-piperidyl]acetamide (34.53 mg, 72.00 μmol, 69.90% yield) (RT=8 min).

Rel Time for Compound 1391 in analytical conditions (column: AS-H, Hexane-IPA-MeOH, 50-25-25, 0.6 mL/min as mobile phase) 6.92 min Compound 1391: Retention time: 6.92 min $^1$H NMR (500 MHz, DMSO-d$_6$) δ (ppm) 0.99-1.04 (m, 3H), 1.05-1.13 (m, 3H), 1.25-1.39 (m, 1H), 1.62-1.71 (m, 5H), 1.81-1.95 (m, 1H), 1.96-2.13 (m, 1H), 2.14-2.25 (m, 1H), 2.35-2.45 (m, 3H), 2.68-2.84 (m, 3H), 3.20-3.27 (m, 1H), 3.34-3.50 (m, 2H), 3.96-4.36 (m, 3H), 5.09-5.57 (m, 1H), 5.57-5.69 (m, 2H), 6.78-6.94 (m, 3H), 7.23-7.33 (m, 1H), 7.42-7.53 (m, 1H), 7.97-8.09 (m, 1H), 10.43-10.64 (m, 1H).

LCMS(ESI): [M]+ m/z: calcd 479.2; found 480.2; Rt=2.115 min.

Example 262. The Synthesis of Rel-N-(6-amino-5-methyl-3-pyridyl)-2-oxo-2-[rac-(2R,4S,5S)-2-(1,3-benzothiazol-5-yl)-4-Isobutyl-5-methyl-1-piperidyl]acetamide (Compound 1157), Rel-N-(6-amino-5-methyl-3-pyridyl)-2-oxo-2-[rac-(2R,4R,5S)-2-(1,3-benzothiazol-5-yl)-4-Isobutyl-5-methyl-1-piperidyl]acetamide (Compound 1284), Rel-N-(6-amino-5-methyl-3-pyridyl)-2-oxo-2-[rac-(2S,4S,5R)-2-(1,3-benzothiazol-5-yl)-4-Isobutyl-5-methyl-1-piperidyl]acetamide (Compound 1210) and Rel-N-(6-amino-5-methyl-3-pyridyl)-2-oxo-2-[rac-(2S,4R,5R)-2-(1,3-benzothiazol-5-yl)-4-Isobutyl-5-methyl-1-piperidyl]acetamide (Compound 1190

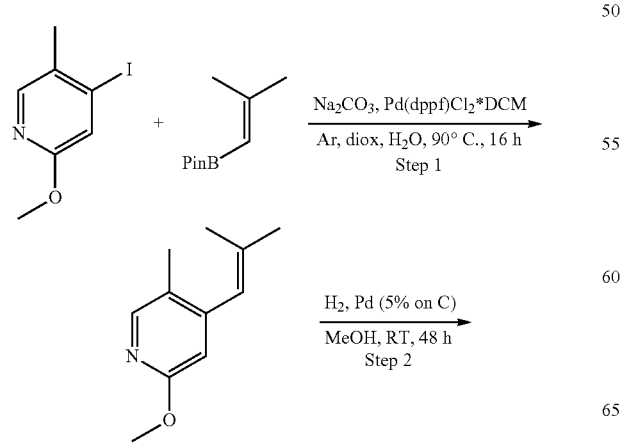

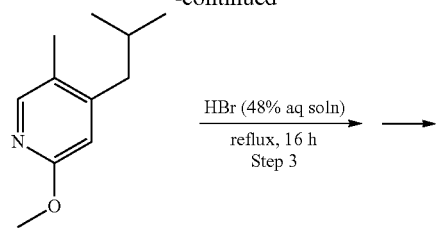

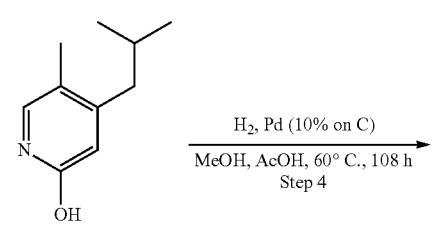

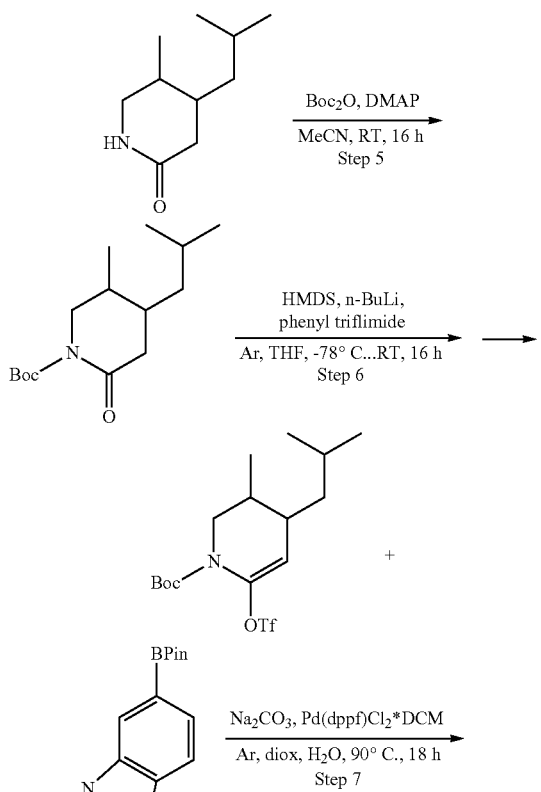

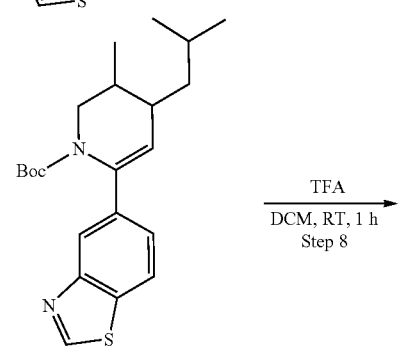

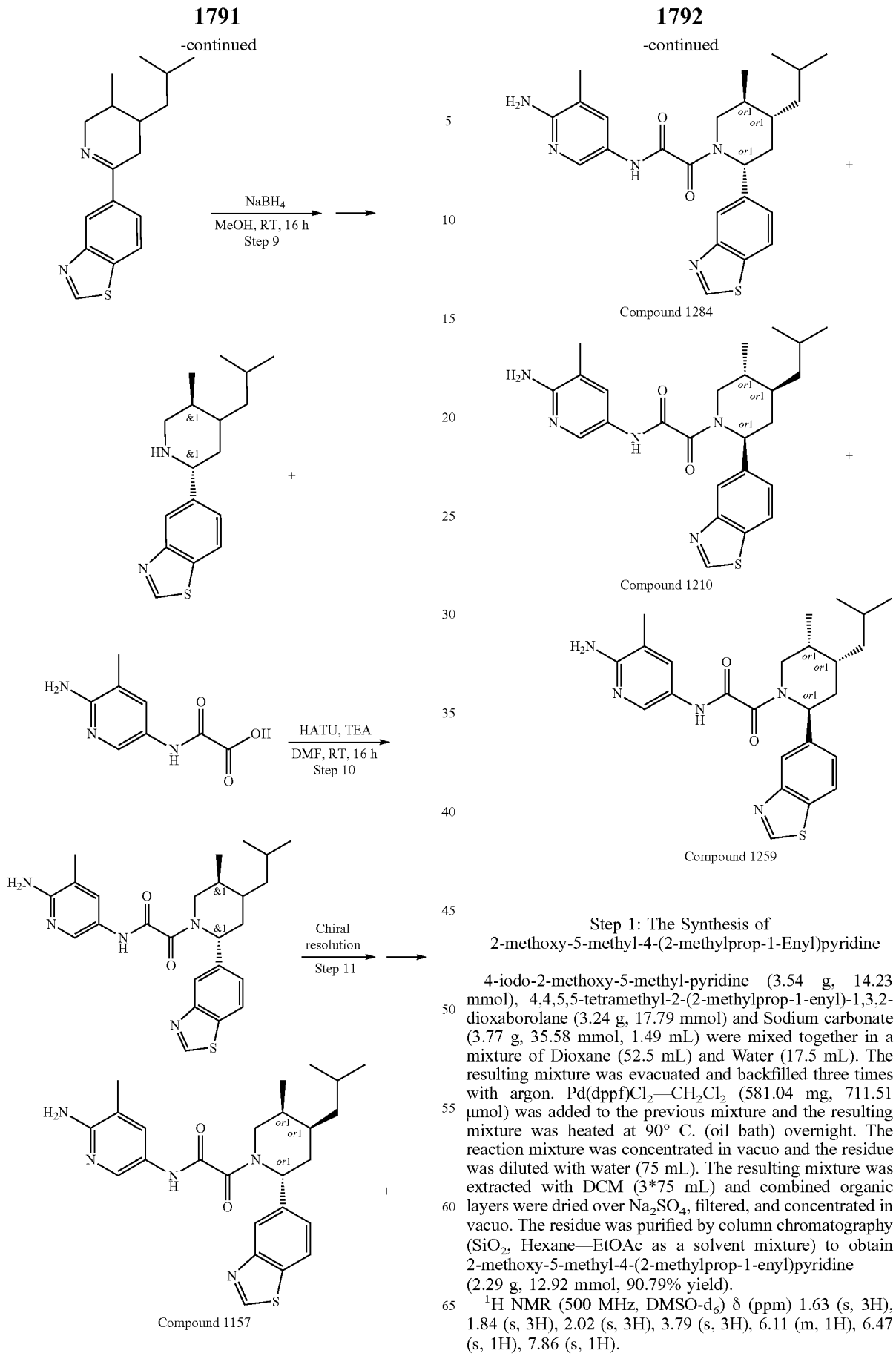

Step 1: The Synthesis of 2-methoxy-5-methyl-4-(2-methylprop-1-Enyl)pyridine 4-iodo-2-methoxy-5-methyl-pyridine (3.54 g, 14.23 mmol), 4,4,5,5-tetramethyl-2-(2-methylprop-1-enyl)-1,3,2-dioxaborolane (3.24 g, 17.79 mmol) and Sodium carbonate (3.77 g, 35.58 mmol, 1.49 mL) were mixed together in a mixture of Dioxane (52.5 mL) and Water (17.5 mL). The resulting mixture was evacuated and backfilled three times with argon. Pd(dppf)Cl$_2$—CH$_2$Cl$_2$ (581.04 mg, 711.51 µmol) was added to the previous mixture and the resulting mixture was heated at 90° C. (oil bath) overnight. The reaction mixture was concentrated in vacuo and the residue was diluted with water (75 mL). The resulting mixture was extracted with DCM (3*75 mL) and combined organic layers were dried over Na$_2$SO$_4$, filtered, and concentrated in vacuo. The residue was purified by column chromatography (SiO$_2$, Hexane—EtOAc as a solvent mixture) to obtain 2-methoxy-5-methyl-4-(2-methylprop-1-enyl)pyridine (2.29 g, 12.92 mmol, 90.79% yield).

$^1$H NMR (500 MHz, DMSO-d$_6$) δ (ppm) 1.63 (s, 3H), 1.84 (s, 3H), 2.02 (s, 3H), 3.79 (s, 3H), 6.11 (m, 1H), 6.47 (s, 1H), 7.86 (s, 1H).

LCMS(ESI): [M+H]⁺ m/z: calcd 178.2; found 178.2; Rt=1.122 min.

Step 2: The Synthesis of 4-Isobutyl-2-methoxy-5-methyl-pyridine 2-methoxy-5-methyl-4-(2-methylprop-1-enyl)pyridine (2.29 g, 12.92 mmol) was dissolved in MeOH (30 mL) and Palladium, 5% on carbon, Noblyst P1093 (549.99 mg, 5.17 mmol) was added. The resulting mixture was evacuated and backfilled three times with hydrogen and the resulting mixture was hydrogenated at 1 atm (balloon) over the weekend. The catalyst was filtered off and the filtrate was concentrated in vacuo to obtain 4-isobutyl-2-methoxy-5-methyl-pyridine (2.13 g, 11.91 mmol, 92.18% yield).

LCMS(ESI): [M+H]⁺ m/z: calcd 180.2; found 180.2; Rt=1.327 min.

Step 3: The Synthesis of 4-Isobutyl-5-methyl-pyridin-2-ol

4-Isobutyl-2-methoxy-5-methyl-pyridine (1.88 g, 10.49 mmol) was dissolved in 48% HBr solution (53 mL) and the resulting mixture was refluxed overnight. The reaction mixture was cooled and neutralized with $Na_2CO_3$. The resulting mixture was extracted with chloroform (2*50 mL) and combined organic layers were dried over $Na_2SO_4$, filtered, and concentrated in vacuo to obtain 4-isobutyl-5-methyl-pyridin-2-ol (1.69 g, 10.20 mmol, 97.29% yield).

¹H NMR (500 MHz, DMSO-d₆) δ (ppm) 0.89 (m, 6H), 1.79 (m, 1H), 1.94 (s, 3H), 2.26 (m, 2H), 6.05 (s, 1H), 7.08 (s, 1H), 11.18 (s, 1H).

LCMS(ESI): [M+H]⁺ m/z: calcd 166.2; found 166.2; Rt=1.104 min.

Step 4: The Synthesis of 4-Isobutyl-5-methyl-piperidin-2-one

4-Isobutyl-5-methyl-pyridin-2-ol (1.91 g, 11.57 mmol) was dissolved in MeOH (20 mL) and AcOH (7 mL) was added thereto. Pd/C JM A402028-10 (369.24 mg, 3.47 mmol) was added to the previous mixture and the resulting mixture was hydrogenated at 50 atm at 60° C. overnight. 10% of the product by NMR of aliquot. Palladium, 10% on carbon, Type 487, dry (738.49 mg, 6.94 mmol) was added to the reaction mixture and the resulting mixture was hydrogenated at 50 atm at 60° C. overnight. 80% of the product by NMR of aliquot. Palladium, 10% on carbon, Type 487, dry (246.16 mg, 2.31 mmol) was added to the reaction mixture and the resulting mixture was hydrogenated at 50 atm at 60° C. over the weekend. The reaction mixture was cooled and filtered. The filtrate was concentrated in vacuo and the residue was dissolved in $CHCl_3$. The resulting solution was washed with aq. $NaHCO_3$ solution and the organic layer was concentrated in vacuo to obtain 4-isobutyl-5-methyl-piperidin-2-one (1.80 g, 10.61 mmol, 91.74% yield).

¹H NMR (500 MHz, DMSO-d₆) δ (ppm) 0.79-0.99 (m, 9H), 0.99-1.10 (m, 2H), 1.27-1.86 (m, 4H), 2.12-2.21 (m, 1H), 2.76-2.85 (m, 1H), 3.09-3.19 (m, 1H), 7.26-7.36 (m, 1H).

LCMS(ESI): [M+H]⁺ m/z: calcd 170.2; found 170.2; Rt=1.179 min.

Step 5: The Synthesis of tert-butyl 4-Isobutyl-5-methyl-2-oxo-piperidine-1-carboxylate 4-Isobutyl-5-methyl-piperidin-2-one (1.80 g, 10.61 mmol) and DMAP (129.63 mg, 1.06 mmol) were dissolved in MeCN (35 mL) and Di-tert-butyl dicarbonate (2.66 g, 12.20 mmol, 2.80 mL) was added. The resulting mixture was stirred overnight. The reaction mixture was concentrated in vacuo and the residue was dissolved in chloroform (75 mL). The resulting solution was washed with $NaHSO_4$ solution (2*40 mL), dried over $Na_2SO_4$, filtered, and concentrated in vacuo to obtain tert-butyl 4-isobutyl-5-methyl-2-oxo-piperidine-1-carboxylate (2.77 g, 10.28 mmol, 96.91% yield).

LCMS(ESI): [M-tBu]⁺ m/z: calcd 214.2; found 214.2; Rt=1.575 min.

Step 6: The Synthesis of tert-butyl 4-Isobutyl-3-methyl-6-(trifluoromethylsulfonyloxy)-3,4-dihydro-2H-pyridine-1-carboxylate Hexamethyldisilazane (2.07 g, 12.85 mmol, 2.68 mL) was dissolved THE (30 mL) and the resulting solution was cooled to -78° C. under argon atmosphere. n-butyllithium (803.64 mg, 12.55 mmol) was added dropwise at -78° C. and the resulting mixture was stirred for 30 min. A solution of tert-butyl 4-isobutyl-5-methyl-2-oxo-piperidine-1-carboxylate (2.77 g, 10.28 mmol) in THE (10 mL) was added dropwise at -78° C. and after addition completed, the resulting mixture was stirred at -78° C. for 1.5 hr. 1,1,1-trifluoro-N-phenyl-N-(trifluoromethylsulfonyl)methane-sulfonamide (3.86 g, 10.80 mmol) was added in one portion to the reaction mixture and the resulting mixture was stirred at -78° C. for 30 min. Then the reaction mixture was allowed to warm to room temperature and stirred overnight. The reaction mixture was diluted with water (15 mL) and MTBE (50 mL) and the organic layer was separated. The aqueous layer was additionally extracted with MTBE (35 mL) and combined organic layers were washed with 10% aqueous sodium hydroxide solution (3*15 mL), dried over potassium carbonate and concentrated in vacuo. The residue was diluted with hexane/MTBE mixture (3:1, 40 mL, repeated 5 times) and stirred for 30 min. The resulting cloudy solution was decanted from the oily residue, filtered through a short pad of silica gel (20 g of dry silica gel), and evaporated to obtain crude tert-butyl 4-isobutyl-3-methyl-6-(trifluoromethylsulfonyloxy)-3,4-dihydro-2H-pyridine-1-carboxylate (3.92 g, 9.76 mmol, 94.91% yield) which was used in further steps without purification.

LCMS(ESI): [M-Tf-tBu]⁺ m/z: calcd 214.2; found 214.2; Rt=1.291 min.

Step 7: The Synthesis of tert-butyl 6-(1,3-benzothiazol-5-yl)-4-Isobutyl-3-methyl-3,4-dihydro-2H-pyridine-1-carboxylate tert-butyl 4-isobutyl-3-methyl-6-(trifluoromethylsulfonyloxy)-3,4-dihydro-2H-pyridine-1-carboxylate (1.2 g, 2.99 mmol), 5-(4,4,5,5-tetramethyl-1,3,2-dioxaborolan-2-yl)-1,3-benzothiazole (936.76 mg, 3.59 mmol) and Sodium carbonate (633.66 mg, 5.98 mmol, 250.26 L) were mixed in a mixture of Dioxane (9 mL) and Water (3 mL). The resulting mixture was evacuated and backfilled three times with argon and Pd(dppf)Cl₂—CH₂Cl₂ (122.06 mg, 149.46 mol) was added. The resulting mixture was evacuated and backfilled with argon and the resulting mixture was heated at 90° C. overnight. The resulting mixture was cooled and diluted with water (45 mL). The resulting mixture was extracted with EtOAc (2*75 mL) and combined organic layers were washed with brine (10 mL), dried over $Na_2SO_4$, filtered, and concentrated in vacuo. The residue (1.3 g of crude product) was combined with the residue (240 mg of crude product) and purified by column chromatography (gradient EtOAc in hexane from 0% to 9%) to obtain tert-butyl 6-(1,3-benzothiazol-5-yl)-4-isobutyl-3-methyl-3,4-dihydro-2H-pyridine-1-carboxylate (0.922 g, 2.39 mmol, 79.79% yield).

LCMS(ESI): [M+H]$^+$ m/z: calcd 387.2; found 387.5; Rt=1.756 min.

Step 8: The Synthesis of 5-(4-Isobutyl-3-methyl-2,3,4,5-tetrahydropyridin-6-yl)-1,3-benzothiazole tert-butyl 6-(1,3-benzothiazol-5-yl)-4-isobutyl-3-methyl-3,4-dihydro-2H-pyridine-1-carboxylate (0.922 g, 2.39 mmol) was dissolved in DCM (4 mL) and TFA (4 mL) was added. The resulting mixture was stirred for 1 hr. The reaction mixture was poured into aq. NaHCO$_3$ (7 g in 40 mL of water) and the resulting mixture was extracted with DCM (2*45 mL). Combined organic layers were washed with water (20 mL), dried over sodium sulfate, filtered, and concentrated in vacuo to obtain 5-(4-isobutyl-3-methyl-2,3,4,5-tetrahydropyridin-6-yl)-1,3-benzothiazole (642 mg, 2.24 mmol, 93.97% yield).

$^1$H NMR (500 MHz, DMSO-d$_6$) δ (ppm) 0.88-1.01 (m, 9H), 1.50-2.01 (m, 4H), 2.25 (m, 1H), 2.48-2.96 (m, 2H), 3.86-4.02 (m, 2H), 7.96 (d, 1H), 8.01 (d, 1H), 8.46 (s, 1H), 9.01 (s, 1H).

LCMS(ESI): [M+H]$^+$ m/z: calcd 287.2; found 287.2; Rt=0.904 min.

Step 9: The Synthesis of rac-5-[(2R,5S)-4-Isobutyl-5-methyl-2-piperidyl]-1,3-benzothiazole 5-(4-Isobutyl-3-methyl-2,3,4,5-tetrahydropyridin-6-yl)-1,3-benzothiazole (642 mg, 2.24 mmol) was dissolved and Sodium Borohydride (169.59 mg, 4.48 mmol, 157.91 μL) was added. The resulting mixture was stirred overnight. Water (10 mL) was added to the reaction mixture and the resulting mixture was concentrated in vacuo. The residue was diluted with water (20 mL) and the resulting mixture was extracted with DCM (2*45 mL). Combined organic layers were dried over sodium sulfate, filtered, and concentrated in vacuo to obtain 5-[(2R,5S)-4-isobutyl-5-methyl-2-piperidyl]-1,3-benzothiazole (644 mg, 2.23 mmol, 99.61% yield).

LCMS(ESI): [M+H]$^+$ m/z: calcd 289.0; found 289.0; Rt=0.963 min.

Step 10: The Synthesis of rac-N-(6-amino-5-methyl-3-pyridyl)-2-[(2R,5S)-2-(1,3-benzothiazol-5-yl)-4-Isobutyl-5-methyl-1-piperidyl]-2-oxo-acetamide 5-[(2R,5S)-4-isobutyl-5-methyl-2-piperidyl]-1,3-benzothiazole (235 mg, 814.70 μmol), 2-[(6-amino-5-methyl-3-pyridyl)amino]-2-oxo-acetic acid (159.01 mg, 814.70 μmol) and Triethylamine (412.20 mg, 4.07 mmol, 567.76 μL) were mixed together in DMF (2 mL) and HATU (371.73 mg, 977.64 μmol) was added. The resulting mixture was stirred overnight. The reaction mixture was submitted to HPLC and purified (2-10 min; 55-70% methanol+NH$_3$; flow 30 mL/min (loading pump 4 mL/min methanol), Column Sun Fire C18 100*19 mm, 5 um) to obtain N-(6-amino-5-methyl-3-pyridyl)-2-[(2R,5S)-2-(1,3-benzothiazol-5-yl)-4-isobutyl-5-methyl-1-piperidyl]-2-oxo-acetamide (158.4 mg, 340.20 μmol, 41.76% yield) and N-(6-amino-5-methyl-3-pyridyl)-2-[(2R,5S)-2-(1,3-benzothiazol-5-yl)-4-isobutyl-5-methyl-1-piperidyl]-2-oxo-acetamide (42.6 mg, 91.49 μmol, 11.23% yield).

LCMS(ESI): [M+H]$^+$ m/z: calcd 466.2; found 466.2; Rt=1.107 min.

Step 11: The Synthesis of Rel-N-(6-amino-5-methyl-3-pyridyl)-2-oxo-2-[rac-(2R,4S,5S)-2-(1,3-benzothiazol-5-yl)-4-Isobutyl-5-methyl-1-piperidyl]acetamide (Compound 1157), Rel-N-(6-amino-5-methyl-3-pyridyl)-2-oxo-2-[rac-(2R,4R,5S)-2-(1,3-benzothiazol-5-yl)-4-Isobutyl-5-methyl-1-piperidyl]acetamide (Compound 1284), Rel-N-(6-amino-5-methyl-3-pyridyl)-2-oxo-2-[rac-(2S,4S,5R)-2-(1,3-benzothiazol-5-yl)-4-Isobutyl-5-methyl-1-piperidyl]acetamide (Compound 1210) and Rel-N-(6-amino-5-methyl-3-pyridyl)-2-oxo-2-[rac-(2S,4R,5R)-2-(1,3-benzothiazol-5-yl)-4-Isobutyl-5-methyl-1-piperidyl]acetamide (Compound 1190 rac-N-(6-amino-5-methyl-3-pyridyl)-2-oxo-2-[rac-(2R,5S)-2-(1,3-benzothiazol-5-yl)-4-isobutyl-5-methyl-1-piperidyl]acetamide (158.4 mg, 340.20 μmol) was chirally separated (Column: Chiralcel OD-H (250×20 mm, 5 mkm); Mobile phase: Hexane-IPA-MeOH, 80-10-10; Flow Rate: 12 mL/min; Column Temperature: 24° C.; Wavelength: 205 nm, 215 nm, RetTime (Compound 1157)=29.35 min; RetTime (Compound 1284)=35.45 min; RetTime (Compound 1210)=41.11 min; RetTime (Compound 1190)=44.65 min) to obtain N-(6-amino-5-methyl-3-pyridyl)-2-oxo-2-[rac-(2R,4S,5S)-2-(1,3-benzothiazol-5-yl)-4-isobutyl-5-methyl-1-piperidyl]acetamide (44.91 mg, 96.45 μmol, 28.35% yield), N-(6-amino-5-methyl-3-pyridyl)-2-oxo-2-[rac-(2R,4R,5S)-2-(1,3-benzothiazol-5-yl)-4-isobutyl-5-methyl-1-piperidyl]acetamide (24.39 mg, 52.38 μmol, 15.40% yield), N-(6-amino-5-methyl-3-pyridyl)-2-oxo-2-[rac-(2S,4S,5R)-2-(1,3-benzothiazol-5-yl)-4-isobutyl-5-methyl-1-piperidyl]acetamide (23.15 mg, 49.72 μmol, 14.61% yield) and N-(6-amino-5-methyl-3-pyridyl)-2-oxo-2-[rac-(2S,4R,5R)-2-(1,3-benzothiazol-5-yl)-4-isobutyl-5-methyl-1-piperidyl]acetamide (47.5 mg, 102.02 μmol, 29.99% yield).

Compound 1157: Yield: 44.91 mg (28.35%)
RT (Chiralpak OD-H (250*4.6, 5 mkm), Hexane-IPA-MeOH, 80-10-10, 0.6 mL/min)=26.450 min.
$^1$H NMR (600 MHz, dmso) δ 0.80-0.86 (m, 6H), 0.98-1.02 (m, 3H), 1.07-1.20 (m, 3H), 1.48-1.55 (m, 1H), 1.58-1.71 (m, 2H), 1.86-2.04 (m, 3H), 2.11-2.22 (m, 1H), 3.41-3.68 (m, 1H), 3.74-4.12 (m, 1H), 5.14-5.38 (m, 1H), 5.47-5.68 (m, 2H), 7.35-7.63 (m, 2H), 7.89-8.03 (m, 2H), 8.03-8.15 (m, 1H), 9.27-9.40 (m, 1H), 9.85-10.53 (m, 1H).
LCMS(ESI): [M+H]$^+$ m/z: calcd 466.2; found 466.2; Rt=1.104 min.

Compound 1284: Yield: 24.39 mg (15.40%)
RT (Chiralpak OD-H (250*4.6, 5 mkm), Hexane-IPA-MeOH, 80-10-10, 0.6 mL/min)=31.136 min.
$^1$H NMR (600 MHz, dmso) δ 0.42-0.64 (m, 3H), 0.71-0.81 (m, 6H), 0.83-0.98 (m, 2H), 1.42-1.57 (m, 1H), 1.74-1.83 (m, 1H), 1.87-2.10 (m, 5H), 2.12-2.20 (m, 1H), 2.71-3.05 (m, 1H), 3.80-4.34 (m, 1H), 5.23-5.70 (m, 3H), 7.21-7.56 (m, 2H), 7.77-8.07 (m, 2H), 8.07-8.16 (m, 1H), 9.34-9.41 (m, 1H), 10.30-10.59 (m, 1H).
LCMS(ESI): [M+H]$^+$ m/z: calcd 466.2; found 466.2; Rt=1.118 min.

Compound 1210: Yield: 23.15 mg (14.61%)
RT (Chiralpak OD-H (250*4.6, 5 mkm), Hexane-IPA-MeOH, 80-10-10, 0.6 mL/min)=35.461 min.
$^1$H NMR (600 MHz, dmso) δ 0.41-0.63 (m, 3H), 0.70-0.81 (m, 6H), 0.82-0.98 (m, 2H), 1.43-1.56 (m, 1H), 1.71-1.84 (m, 1H), 1.91-2.09 (m, 5H), 2.12-2.21 (m, 1H), 2.72-3.06 (m, 1H), 3.78-4.36 (m, 1H), 5.28-5.68 (m, 3H), 7.22-

7.56 (m, 2H), 7.75-8.07 (m, 2H), 8.07-8.16 (m, 1H), 9.35-9.40 (m, 1H), 10.27-10.57 (m, 1H).

LCMS(ESI): [M+H]⁺ m/z: calcd 466.2; found 466.2; Rt=1.121 min.

Compound 1190: Yield: 47.5 mg (29.99%) RT (Chiralpak OD-H (250*4.6, 5 mkm), Hexane-IPA-MeOH, 80-10-10, 0.6 mL/min)=38.015 min.

¹H NMR (600 MHz, dmso) δ 0.80-0.87 (m, 6H), 0.98-1.02 (m, 3H), 1.08-1.25 (m, 3H), 1.48-1.55 (m, 1H), 1.57-1.69 (m, 2H), 1.87-2.05 (m, 3H), 2.11-2.21 (m, 1H), 3.39-3.67 (m, 1H), 3.75-4.09 (m, 1H), 5.11-5.37 (m, 1H), 5.46-5.67 (m, 2H), 7.31-7.52 (m, 2H), 7.87-8.18 (m, 3H), 9.33-9.41 (m, 1H), 9.93-10.51 (m, 1H).

LCMS(ESI): [M+H]⁺ m/z: calcd 466.2; found 466.2; Rt=1.119 min.

Example 263. The Synthesis of N-(6-amino-5-ethylpyridin-3-yl)-2-((2R,5S)-2-(3-(2-(dimethylamino)ethoxy)phenyl)-5-methylpiperidin-1-yl)-2-oxoacetamide (Compound 1175

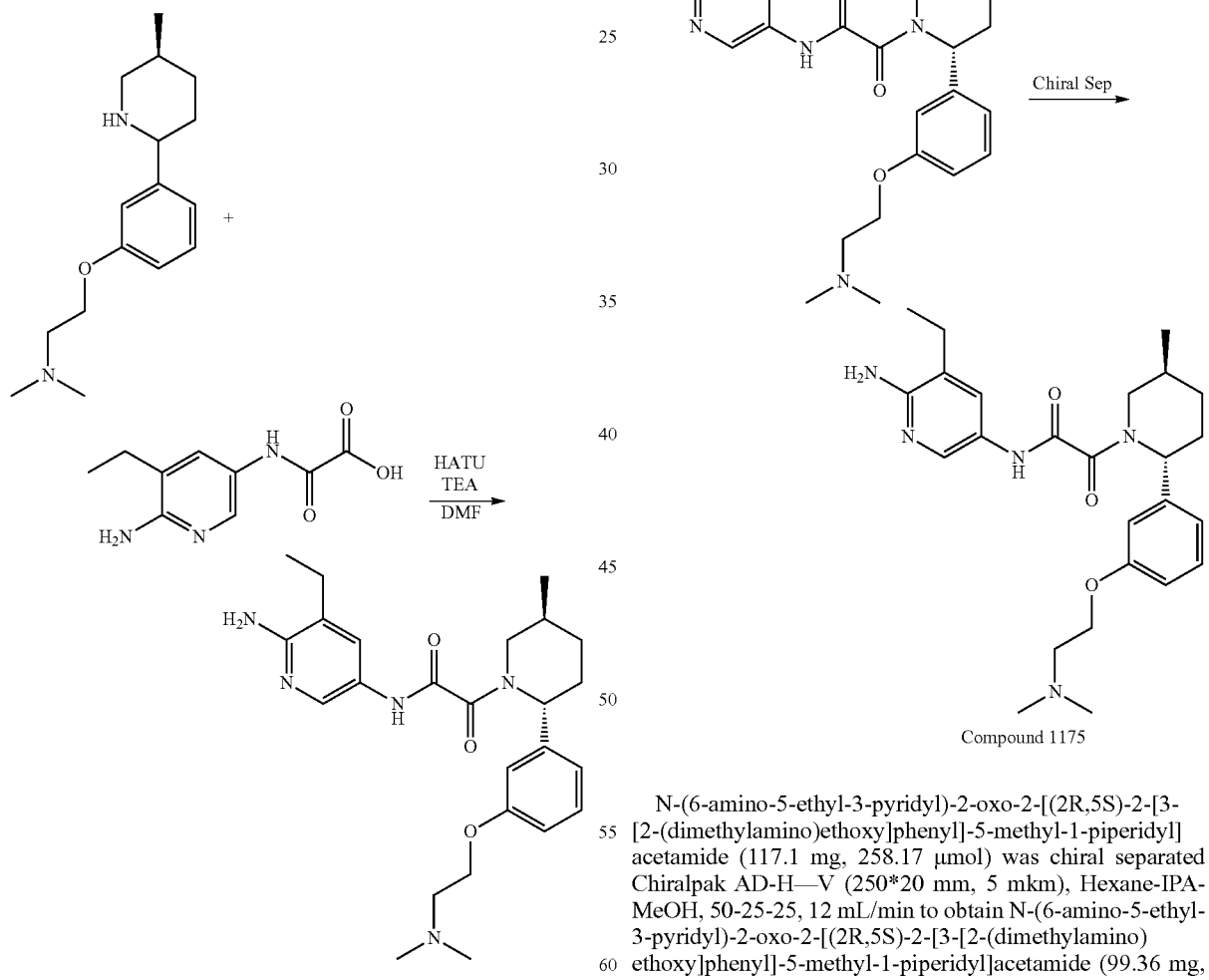

N,N-dimethyl-2-[3-[(2R,5S)-5-methyl-2-piperidyl]phenoxy]ethanamine (293 mg, 1.12 mmol), 2-[(6-amino-5-ethyl-3-pyridyl)amino]-2-oxo-acetic acid (233.61 mg, 1.12 mmol) and TEA (564.97 mg, 5.58 mmol, 778.20 µL) were mixed together in DMF (3 mL) and HATU (509.51 mg, 1.34 mmol) was added thereto. The resulting mixture was stirred overnight. The reaction mixture was submitted to HPLC and purified (2-10 min 10-50% MeCN+FA, 30 mL/min (loading pump 4 mL MeCN+FA) column: SunFire 100*19 mm, 5 microM) to obtain N-(6-amino-5-ethyl-3-pyridyl)-2-[(2R,5S)-2-[3-[2-(dimethylamino)ethoxy]phenyl]-5-methyl-1-piperidyl]-2-oxo-acetamide (18.7 mg, 37.43 µmol, 3.35% yield, HCOOH).

¹H NMR (600 MHz, DMSO-d₆) δ (ppm) 0.96-1.06 (m, 3H), 1.06-1.17 (m, 3H), 1.27-1.38 (m, 1H), 1.58-1.76 (m, 1H), 1.82-1.92 (m, 1H), 1.97-2.15 (m, 1H), 2.19-2.21 (m, 6H), 2.36-2.43 (m, 2H), 2.59-2.76 (m, 3H), 3.22-3.24 (m, 1H), 3.42-3.48 (m, 1H), 4.01-4.07 (m, 2H), 5.09-5.57 (m, 1H), 5.57-5.66 (m, 2H), 6.77-6.94 (m, 3H), 7.25-7.32 (m, 1H), 7.43-7.52 (m, 1H), 7.97-8.07 (m, 1H), 10.49-10.56 (m, 1H).

LCMS(ESI): [M]⁺ m/z: calcd 453.2; found 454.2; Rt=1.946 min.

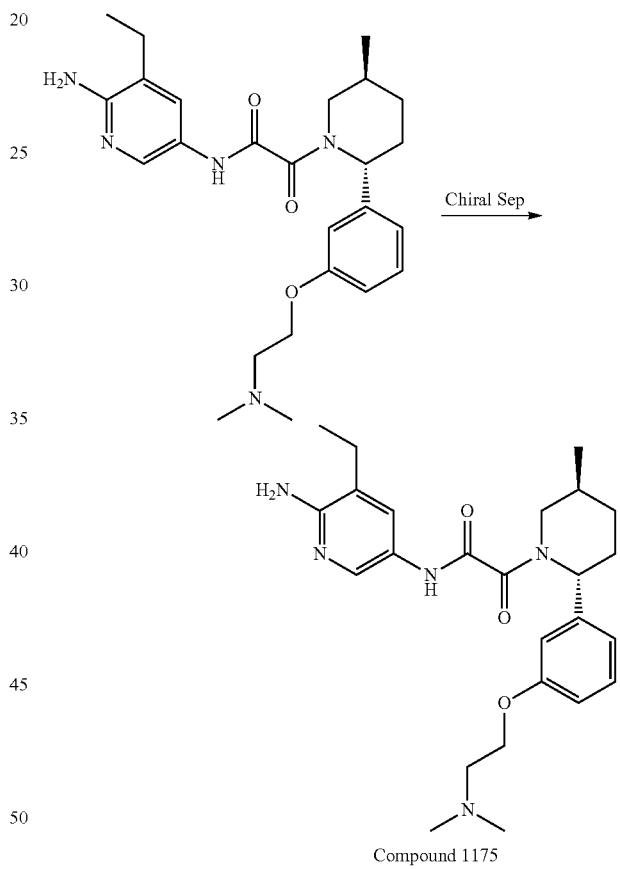

Compound 1175

N-(6-amino-5-ethyl-3-pyridyl)-2-oxo-2-[(2R,5S)-2-[3-[2-(dimethylamino)ethoxy]phenyl]-5-methyl-1-piperidyl]acetamide (117.1 mg, 258.17 µmol) was chiral separated Chiralpak AD-H—V (250*20 mm, 5 mkm), Hexane-IPA-MeOH, 50-25-25, 12 mL/min to obtain N-(6-amino-5-ethyl-3-pyridyl)-2-oxo-2-[(2R,5S)-2-[3-[2-(dimethylamino)ethoxy]phenyl]-5-methyl-1-piperidyl]acetamide (99.36 mg, 219.06 µmol, 84.85% yield) (RT=41.69 min).

Rel Time for Compound 1175 in analytical conditions (column: AD-H, IPA-MeOH, 50-50, 0.6 mL/min as mobile phase) 35.98 min Compound 1175: Retention time: 35.98 min ¹H NMR (600 MHz, DMSO-d₆) δ (ppm) 0.96-1.03 (m, 3H), 1.06-1.14 (m, 3H), 1.26-1.39 (m, 1H), 1.60-1.72 (m, 1H), 1.82-1.92 (m, 1H), 1.96-2.13 (m, 1H), 2.13-2.18 (m, 1H), 2.18-2.23 (m, 6H), 2.34-2.41 (m, 2H), 2.58-2.61 (m, 2H), 2.72-3.24 (m, 1H), 3.42-4.00 (m, 1H), 4.00-4.06 (m, 2H), 5.06-5.57 (m, 1H), 5.57-5.66 (m, 2H), 6.77-6.84 (m, 1H), 6.84-6.93 (m, 2H), 7.20-7.34 (m, 1H), 7.41-7.56 (m, 1H), 7.96-8.11 (m, 1H), 10.46-10.57 (m, 1H).
LCMS(ESI): [M]+ m/z: calcd 453.2; found 454.2; Rt=0.895 min.
Example 264. The Synthesis of N-(6-amino-5-ethylpyridin-3-yl)-2-((2R,5)-5-methyl-2-(3-(1-methylpiperidin-3-yl)phenyl)piperidin-1-yl)-2-oxoacetamide (Compound 1353, Compound 1285 and Compound 1090
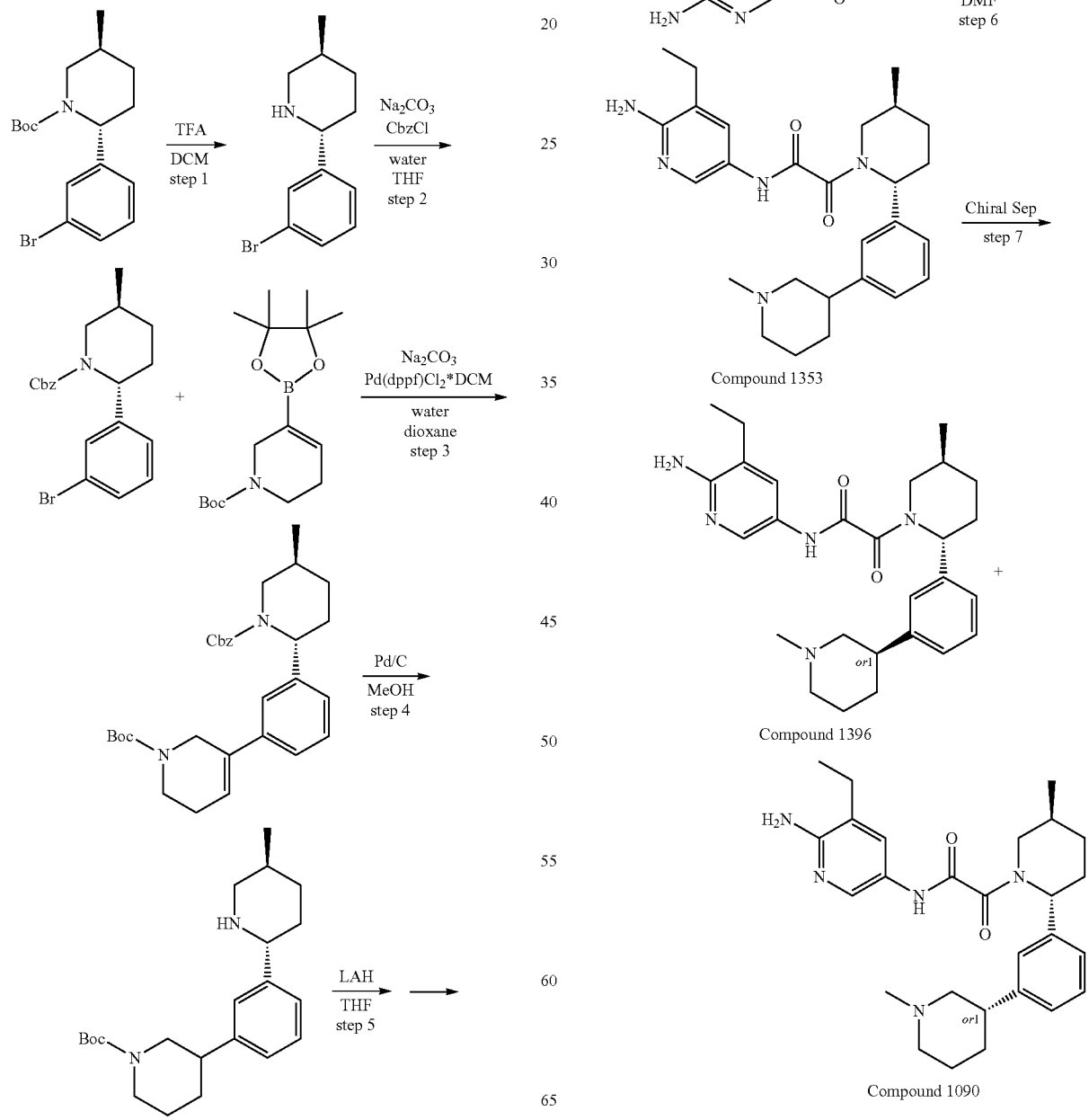

Step 1: Synthesis of (2R,5S)-2-(3-bromophenyl)-5-methylpiperidine tert-butyl (2R,5S)-2-(3-bromophenyl)-5-methyl-piperidine-1-carboxylate (4.3 g, 12.14 mmol) was dissolved in DCM (16 mL) and TFA (16 mL) was added thereto. The resulting mixture was stirred for 1 hr. The reaction mixture was concentrated in vacuum and aq.$K_2CO_3$ solution (25 g in 70 mL of water) was carefully added to the residue. The resulting mixture was extracted with DCM (2*40 mL) and combined organic layers were dried over $Na_2SO_4$, filtered, and concentrated in vacuum to obtain (2R,5S)-2-(3-bromophenyl)-5-methyl-piperidine (2.70 g, 10.60 mmol, 87.36% yield).

LCMS(ESI): $[M]^+$ m/z: calcd 254.2; found 255.2; Rt=0.619 min.

Step 2: Synthesis of (2R,5S)-benzyl 2-(3-bromophenyl)-5-methylpiperidine-1-carboxylate (2R,5S)-2-(3-bromophenyl)-5-methyl-piperidine (2.7 g, 10.62 mmol) was dissolved in THF (25 mL) and sodium carbonate (2.25 g, 21.25 mmol, 889.35 µL) was added thereto followed by the addition of water (30 mL). The resulting mixture was cooled to 0° C. in an ice bath and a solution of benzyl carbonochloridate (1.90 g, 11.15 mmol, 1.59 mL) in THF (5 mL) was added dropwise at 0° C. After addition completed, the reaction mixture was allowed to warm to rt and stirred overnight. The reaction mixture was concentrated in vacuum and the residue was diluted with water (50 mL). The resulting mixture was extracted with MTBE (2*50 mL) and combined organic layers were dried over $Na_2SO_4$, filtered, and concentrated in vacuum to obtain benzyl (2R,5S)-2-(3-bromophenyl)-5-methyl-piperidine-1-carboxylate (4.27 g, crude).

LCMS(ESI): $[M]^+$ m/z: calcd 388.2; found 389.2; Rt=1.636 min.

Step 3: Synthesis of tert-butyl 3-(3-((2R,5S)-1-((Benzyloxy)Carbonyl)-5-methylpiperidin-2-yl)phenyl)-5,6-dihydropyridine-1(2H)-carboxylate Benzyl(2R,5S)-2-(3-bromophenyl)-5-methyl-piperidine-1-carboxylate (1 g, 2.58 mmol), tert-butyl 5-(4,4,5,5-tetramethyl-1,3,2-dioxaborolan-2-yl)-3,6-dihydro-2H-pyridine-1-carboxylate (915.76 mg, 2.96 mmol) and sodium carbonate (545.92 mg, 5.15 mmol, 215.61 µL) were dissolved in a mixture of dioxane (7.5 mL) and water (2.5 mL). The resulting mixture was evacuated and backfilled three times with argon and $Pd(dppf)Cl_2$*DCM (105.16 mg, 128.77 µmol) was added thereto. The resulting mixture was heated at 90° C. overnight. The reaction mixture was concentrated in vacuum and the residue was diluted with water (20 mL). The resulting mixture was extracted with EtOAc (2*30 mL) and combined organic layers were dried over $Na_2SO_4$, filtered, and concentrated in vacuum. The residue was purified by column chromatography to obtain tert-butyl 5-[3-[(2R,5S)-1-benzyloxycarbonyl-5-methyl-2-piperidyl]phenyl]-3,6-dihydro-2H-pyridine-1-carboxylate (800 mg, 1.63 mmol, 63.31% yield).

LCMS(ESI): $[M-Boc]^+$ m/z: calcd 390.2; found 391.2; Rt=1.885 min.

Step 4: Synthesis of tert-butyl 3-(3-((2R,5S)-5-methylpiperidin-2-yl)phenyl)piperidine-1-carboxylate tert-butyl 5-[3-[(2R,5S)-1-benzyloxycarbonyl-5-methyl-2-piperidyl]phenyl]-3,6-dihydro-2H-pyridine-1-carboxylate (800.00 mg, 1.63 mmol) was dissolved in MeOH (30 mL) and palladium, 10% on carbon (433.81 mg, 407.64 µmol, 10% purity) was added thereto. The resulting mixture was hydrogenated at 50 atm overnight. The catalyst was filtered off and the filtrate was concentrated in vacuum to obtain tert-butyl 3-[3-[(2R,5S)-5-methyl-2-piperidyl]phenyl]piperidine-1-carboxylate (661 mg, crude).

LCMS(ESI): [M]f m/z: calcd 358.2; found 359.2; Rt=1.201 min.

Step 5: Synthesis of 1-methyl-3-(3-((2R,5S)-5-methylpiperidin-2-yl)phenyl)piperidine LAH (349.88 mg, 9.22 mmol) was dissolved in THF (8 mL) and a solution of tert-butyl 3-[3-[(2R,5S)-5-methyl-2-piperidyl]phenyl]piperidine-1-carboxylate (661.00 mg, 1.84 mmol) in THF (2 mL) was added dropwise to the previous mixture. The resulting mixture was heated to reflux and refluxed for 3 hr. The reaction mixture was allowed to cool to room temperature and stirred overnight. Water (350 mkl) was added to the reaction mixture followed by the addition of aq.KOH solution (350 mkl) and water (700 mkl). The reaction mixture was stirred for 30 min and filtered. The filter cake was washed with THF (15 mL) and the filtrate was concentrated to obtain 1-methyl-3-[3-[(2R,5S)-5-methyl-2-piperidyl]phenyl]piperidine (450 mg, 1.65 mmol, 89.59% yield).

LCMS(ESI): $[M]^+$ m/z: calcd 272.2; found 273.2; Rt=0.684 min.

Step 6: Synthesis of N-(6-amino-5-ethylpyridin-3-yl)-2-((2R,5S)-5-methyl-2-(3-(1-methylpiperidin-3-yl)phenyl)piperidin-1-yl)-2-oxoacetamide (Compound 1353

1-methyl-3-[3-[(2R,5S)-5-methyl-2-piperidyl]phenyl]piperidine (250 mg, 917.68 µmol), 2-[(6-amino-5-ethyl-3-pyridyl)amino]-2-oxo-acetic acid (191.98 mg, 917.68 µmol) and TEA (464.30 mg, 4.59 mmol, 639.53 µL) were mixed in DMF (2.5 mL) and HATU (418.71 mg, 1.10 mmol) was added thereto. The resulting mixture was stirred overnight. The reaction mixture was submitted to HPLC and purified (2-10 min 60-80% MeOH+$NH_3$30 min (loading pump 4 mL MeOH), column: SunFire 100*19 mm, 5 microM) to obtain N-(6-amino-5-ethyl-3-pyridyl)-2-[(2R,5S)-5-methyl-2-[3-(1-methyl-3-piperidyl)phenyl]-1-piperidyl]-2-oxo-acetamide (165.3 mg, 356.55 µmol, 38.85% yield).

$^1$H NMR (600 MHz, DMSO-$d_6$) δ (ppm) 0.98-1.03 (m, 3H), 1.06-1.13 (m, 3H), 1.29-1.41 (m, 2H), 1.55-1.69 (m, 3H), 1.72-1.79 (m, 1H), 1.82-1.90 (m, 3H), 1.95-2.11 (m, 1H), 2.14-2.16 (m, 3H), 2.18-2.28 (m, 1H), 2.39-2.42 (m, 1H), 2.69-3.24 (m, 5H), 3.42-4.04 (m, 1H), 5.10-5.58 (m, 1H), 5.58-5.68 (m, 2H), 7.11-7.19 (m, 3H), 7.24-7.33 (m, 1H), 7.42-7.53 (m, 1H), 7.98-8.07 (m, 1H), 10.49-10.56 (m, 1H).

LCMS(ESI): $[M]^+$ m/z: calcd 463.2; found 464.2; Rt=2.113 min.

Step 7: Chiral Separation (Compound 1396 and Compound 1090

Racemic N-(6-amino-5-ethyl-3-pyridyl)-2-oxo-2-[(2R,5S)-5-methyl-2-[3-(1-methyl-3-piperidyl)phenyl]-1-piperidyl]acetamide (50.7 mg, 109.36 µmol) was chiral separated (Column: Chiralpak IA (250*20 mm, 5 mkm); Mobile phase: IPA-MeOH, 50-50. Flow Rate: 10 mL/min) to obtain N-(6-amino-5-ethyl-3-pyridyl)-2-oxo-2-[(2R,5S)-5-methyl- 2-[3-[(3S)-1-methyl-3-piperidyl]phenyl]-1-piperidyl]acetamide (19.97 mg, 43.07 μmol, 39.39% yield) (RT=15.04 min) and N-(6-amino-5-ethyl-3-pyridyl)-2-oxo-2-[(2R,5S)-5-methyl-2-[3-[(3R)-1-methyl-3-piperidyl]phenyl]-1-piperidyl]acetamide (25.54 mg, 55.09 μmol, 50.37% yield) (RT=23.16 min).

Rel Time for Compound 1396 in analytical conditions (column: IA, MeOH, 50-50, 0.6 mL/min as mobile phase) 21.21 min and for Compound 1090 12.00 min.

Compound 1396: Retention time: 21.21 min
$^1$H NMR (600 MHz, DMSO-$d_6$) δ (ppm) 0.98-1.04 (m, 3H), 1.06-1.15 (m, 3H), 1.28-1.41 (m, 2H), 1.51-1.70 (m, 3H), 1.72-1.79 (m, 1H), 1.80-1.92 (m, 3H), 1.96-2.36 (m, 6H), 2.38-2.42 (m, 1H), 2.72-3.22 (m, 4H), 3.41-4.04 (m, 1H), 5.11-5.57 (m, 1H), 5.58-5.67 (m, 2H), 7.11-7.20 (m, 3H), 7.27-7.32 (m, 1H), 7.41-7.53 (m, 1H), 7.98-8.09 (m, 1H), 10.49-10.55 (m, 1H).
LCMS(ESI): [M]$^+$ m/z: calcd 463.2; found 464.2; Rt=2.107 min.

Compound 1090: Retention time: 12.00 min
$^1$H NMR (600 MHz, DMSO-$d_6$) δ (ppm) 0.98-1.03 (m, 3H), 1.06-1.13 (m, 3H), 1.28-1.41 (m, 2H), 1.54-1.70 (m, 3H), 1.72-1.80 (m, 1H), 1.81-1.90 (m, 3H), 1.97-2.12 (m, 1H), 2.13-2.16 (m, 3H), 2.18-2.27 (m, 1H), 2.32-2.36 (m, 1H), 2.38-2.42 (m, 1H), 2.72-3.22 (m, 4H), 3.42-4.06 (m, 1H), 5.11-5.58 (m, 1H), 5.59-5.67 (m, 2H), 7.09-7.21 (m, 3H), 7.26-7.32 (m, 1H), 7.43-7.52 (m, 1H), 7.99-8.08 (m, 1H), 10.48-10.55 (m, 1H).
LCMS(ESI): [M]$^+$ m/z: calcd 463.2; found 464.2; Rt=2.104 min.

Example 265. The Synthesis of N-(6-amino-5-ethyl-3-pyridyl)-2-oxo-2-[rac-(2R,5S)-2-[3-chloro-4-[2-(dimethylamino)Ethoxy]phenyl]-5-methyl-1-piperidyl]acetamide (Compound 1305)

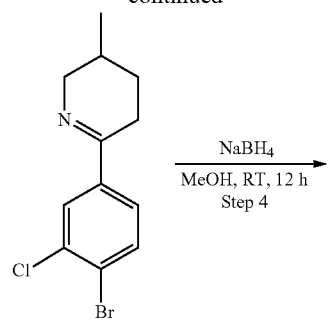

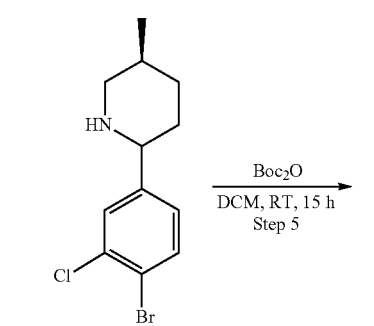

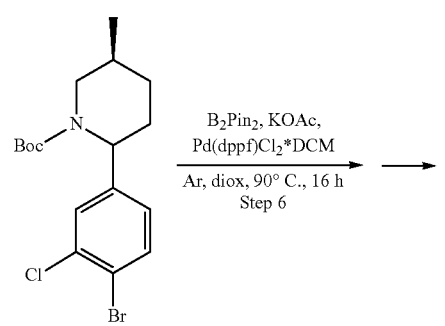

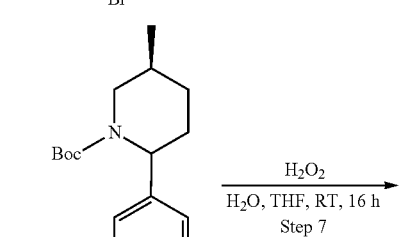

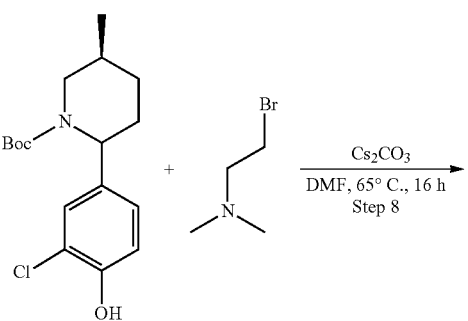

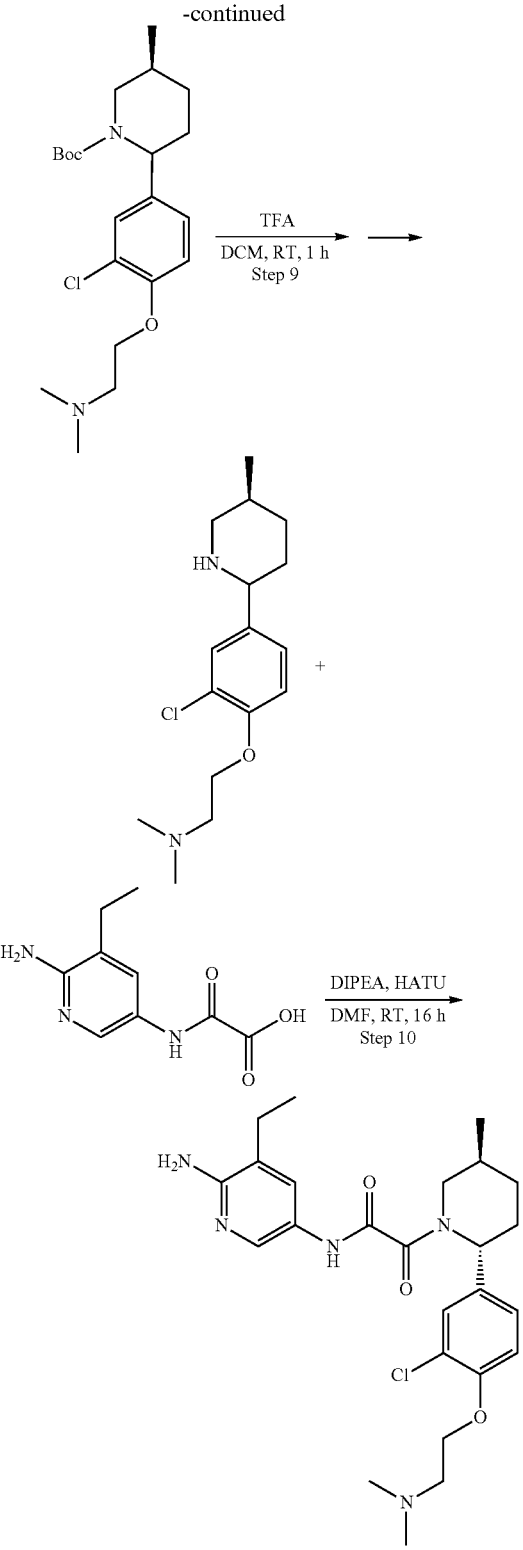

Step 1: The Synthesis of 4-bromo-3-chloro-benzoyl Chloride 4-bromo-3-chloro-benzoic acid (22 g, 93.43 mmol) were suspended in DCM (250 mL). Dimethylformamide (204.88 mg, 2.80 mmol, 217.04 uL) was added. The resulting mixture was stirred at 25° C. for 15 hr. When gas evolution ceased, resulting clear solution was concentrated under reduced pressure. Residue was redissolved in hexane (30 mL), filtered and evaporated in vacuo, affording 4-bromo-3-chloro-benzoyl chloride (21.8 g, 85.86 mmol, 91.89% yield).

$^1$H NMR (500 MHz, DMSO-$d_6$) δ (ppm) 7.71 (d, 1H), 7.81 (d, 1H), 7.98 (s, 1H).

Step 2: The Synthesis of tert-butyl 3-(4-bromo-3-chloro-benzoyl)-5-methyl-2-oxo-piperidine-1-carboxylate Sodium bis(trimethylsilyl)amide (15.17 g, 82.71 mmol) was added dropwise to a precooled solution of tert-butyl 5-methyl-2-oxo-piperidine-1-carboxylate (8.40 g, 39.38 mmol) in THF (50 mL) at −78° C. After addition was complete, it was stirred at the same temperature for 1 hr. After that, 4-bromo-3-chloro-benzoyl chloride (10 g, 39.38 mmol) solution in THF was added dropwise. After addition was complete cooling bath was removed. Resulting mixture was slowly warmed up to 20° C. and stirred at this temperature for 1 hr. Then, it was quenched with 15% aq. NH$_4$Cl(150 mL) and extracted with ethyl acetate (2*200 mL). Organic layer was washed with 20% aq. NaCl (2×100 mL), dried over Na$_2$SO$_4$ and evaporated under reduced pressure, affording tert-butyl 3-(4-bromo-3-chloro-benzoyl)-5-methyl-2-oxo-piperidine-1-carboxylate (16 g, 37.15 mmol, 94.32% yield).

LCMS(ESI): [M+H]$^+$ m/z: calcd 430.2; found 430.0; Rt=1.598 min.

Step 3: The Synthesis of 6-(4-bromo-3-chloro-phenyl)-3-methyl-2,3,4,5-tetrahydropyridine tert-butyl 3-(4-bromo-3-chloro-benzoyl)-5-methyl-2-oxo-piperidine-1-carboxylate (16 g, 37.15 mmol) was dissolved in AcOH (100 mL) and Hydrochloric acid, 36% w/w aq. soln. (19.23 g, 527.49 mmol, 24.04 mL) was added portionwise. After addition was complete, resulting mixture was stirred at 100° C. for 15 hr. Then, solvents were removed under reduced pressure and residue was partitioned between 1 N HCl (100 mL) and DCM (200 mL). Organic layer was separated and discarded. Aqueous layer was basified to pH≈10 with 10% NaOH and extracted with DCM (2×200 mL). DCM layers were combined, dried over Na$_2$SO$_4$ and evaporated under reduced pressure, affording 6-(4-bromo-3-chloro-phenyl)-3-methyl-2,3,4,5-tetrahydropyridine (1.6 g, 5.58 mmol, 15.03% yield).

LCMS(ESI): [M+H]$^+$ m/z: calcd 286.0; found 286.0; Rt=0.775 min.

Step 4: The Synthesis of (5S)-2-(4-bromo-3-chloro-phenyl)-5-methyl-piperidine To a stirred solution of (3S)-6-(4-bromo-3-chloro-phenyl)-3-methyl-2,3,4,5-tetrahydropyridine (3.3 g, 11.51 mmol) in MeOH (34.19 mL) was added Sodium Borohydride (871.25 mg, 23.03 mmol, 811.22 μL) at 0° C. The resulting reaction mixture was stirred at 25° C. for 12 hr. Upon completion, the reaction mixture was concentrated under reduced pressure, and then quenched with water 20 mL and 50 mL EtOAc. The combined organic phase was washed with Brine 20 mL, dried over Na$_2$SO$_4$ and concentrated under reduced pressure to obtain (5S)-2-(4-bromo-3-chloro-phenyl)-5-methyl-piperidine (3.2 g, 11.09 mmol, 96.29% yield).

LCMS(ESI): [M+H]⁺ m/z: calcd 288.0; found 288.0; Rt=0.851 min.

Step 5: The Synthesis of tert-butyl (5S)-2-(4-bromo-3-chloro-phenyl)-5-methyl-piperidine-1-carboxylate To a stirred solution of (5S)-2-(4-bromo-3-chloro-phenyl)-5-methyl-piperidine (3.2 g, 11.09 mmol) in DCM (47.46 mL) was added di-tert-butyl dicarbonate 2.0 M in THF (2.42 g, 11.09 mmol, 2.54 mL) at 25° C. The resulting reaction mixture was stirred at 25° C. for 15 hr. Upon completion, the reaction mixture was concentrated under reduced pressure to obtain tert-butyl (5S)-2-(4-bromo-3-chloro-phenyl)-5-methyl-piperidine-1-carboxylate (4 g, 10.29 mmol, 92.81% yield).
LCMS(ESI): [M-tBu]⁺ m/z: calcd 332.0; found 332.0; Rt=1.793 min.

Step 6: The Synthesis of tert-butyl (5S)-2-[3-chloro-4-(4,4,5,5-tetramethyl-1,3,2-dioxaborolan-2-yl)phenyl]-5-methyl-piperidine-1-carboxylate To a solution of tert-butyl (5S)-2-(4-bromo-3-chloro-phenyl)-5-methyl-piperidine-1-carboxylate (4 g, 10.29 mmol) was added Potassium Acetate (2.02 g, 20.58 mmol, 1.29 mL) and Bis(pinacolato)diboron (2.61 g, 10.29 mmol). The reaction mixture was degassed and Pd(dppf)Cl₂*DCM (420.16 mg, 514.50 µmol) added in one portion. The mixture was further degassed with Ar and heated at 90° C. for 16 hr. After this time the reaction mixture was allowed to cool to rt, filtered and the solvent removed in vacuo to obtain tert-butyl (5S)-2-[3-chloro-4-(4,4,5,5-tetramethyl-1,3,2-dioxaborolan-2-yl)phenyl]-5-methyl-piperidine-1-carboxylate (4 g, 9.18 mmol, 89.20% yield).
LCMS(ESI): [M-tBu]⁺ m/z: calcd 380.2; found 380.2; Rt=1.886 min.

Step 7: The Synthesis of tert-butyl (5S)-2-(3-chloro-4-hydroxy-phenyl)-5-methyl-piperidine-1-carboxylate To a solution of tert-butyl (5S)-2-[3-chloro-4-(4,4,5,5-tetramethyl-1,3,2-dioxaborolan-2-yl)phenyl]-5-methyl-piperidine-1-carboxylate (4 g, 9.18 mmol) in mixture of water (18.94 mL) and THF (18.94 mL) Hydrogen peroxide 35% (2.34 g, 68.84 mmol, 2.13 mL) was added and stirred overnight. Reaction mixture was diluted with water (40 mL) and MTBE (40 mL), and treated with sodium thiosulfate, then organic phase was washed with water, dried over Na₂SO₄ and concentrated in vacuo. The crude was subjected to CC (CHCl₃/MTBE was used as an eluent mixture) to give tert-butyl (5S)-2-(3-chloro-4-hydroxy-phenyl)-5-methyl-piperidine-1-carboxylate (2 g, 6.14 mmol, 66.87% yield).
LCMS(ESI): [M-tBu]⁺ m/z: calcd 270.0; found 270.0; Rt=1.461 min.

Step 8: The Synthesis of tert-butyl (5S)-2-[3-chloro-4-[2-(dimethylamino)Ethoxy]phenyl]-5-methyl-piperidine-1-carboxylate tert-butyl (5S)-2-(3-chloro-4-hydroxy-phenyl)-5-methyl-piperidine-1-carboxylate (2 g, 6.14 mmol) was dissolved in DMF (50 mL) and Cesium carbonate (18.00 g, 55.24 mmol) was added. Then 2-bromo-N,N-dimethyl-ethanamine (6.43 g, 27.62 mmol, HBr) was added. The reaction mixture was stirred overnight at 65° C. After that it was evaporated and extracted between water and EtOAc, then it was washed with brine and dried over Na₂SO₄. It was evaporated to afford tert-butyl (5S)-2-3-chloro-4-[2-(dimethylamino)ethoxy]phenyl]-5-methyl-piperidine-1-carboxylate (1.3 g, 3.27 mmol, 53.35% yield).
LCMS(ESI): [M+H]⁺ m/z: calcd 397.2; found 397.2; Rt=0.998 min.

Step 9: The Synthesis of 2-[2-chloro-4-[(5S)-5-methyl-2-piperidyl]Phenoxy]-N,N-dimethyl-Ethanamine tert-butyl (5S)-2-[3-chloro-4-[2-(dimethylamino)ethoxy]phenyl]-5-methyl-piperidine-1-carboxylate (0.65 g, 1.64 mmol) was dissolved in DCM (5.74 mL) and TFA (1.87 g, 16.37 mmol, 1.26 mL) was added. Then reaction was stirred for 1 hr at rt. It was evaporated to afford 2-[2-chloro-4-[(5S)-5-methyl-2-piperidyl]phenoxy]-N,N-dimethyl-ethanamine (0.7 g, 1.34 mmol, 81.76% yield, 2TFA).
LCMS(ESI): [M+H]⁺ m/z: calcd 297.2; found 297.2; Rt=0.354 min.

Step 10: The Synthesis of N-(6-amino-5-ethyl-3-pyridyl)-2-oxo-2-[rac-(2R,5S)-2-[3-chloro-4-[2-(dimethylamino)Ethoxy]phenyl]-5-methyl-1-piperidyl]acetamide (Compound 1305

DIPEA (1.73 g, 13.39 mmol, 2.33 mL) was added to the solution of respective 2-[(6-amino-5-ethyl-3-pyridyl)amino]-2-oxo-acetic acid (280.07 mg, 1.34 mmol) and 2-[2-chloro-4-[(5S)-5-methyl-2-piperidyl]phenoxy]-N,N-dimethyl-ethanamine (0.7 g, 1.34 mmol, 2TFA) in DMF (7.67 mL). The resulting mixture was stirred for 5 min followed by the addition of HATU (559.95 mg, 1.47 mmol). Then, the reaction mixture was stirred overnight at rt. After the completion of the reaction, monitored by LCMS, the resulting suspension was concentrated under reduced pressure, dissolved in EtOAc and washed with water and brine, dried over Na₂SO₄. The obtained solid was subjected to HPLC (Waters SunFire C18 20*100 5 mkm column and MeCN+FA as an eluent mixture) to afford N-(6-amino-5-ethyl-3-pyridyl)-2-oxo-2-[rac-(2R,5S)-2-[3-chloro-4-[2-(dimethylamino)ethoxy]phenyl]-5-methyl-1-piperidyl]acetamide (51.8 mg, 97.00 µmol, 7.25% yield, HCOOH).
¹H NMR (600 MHz, dmso) δ 0.96-1.06 (m, 3H), 1.05-1.14 (m, 3H), 1.26-1.37 (m, 1H), 1.62-1.70 (m, 1H), 1.80-1.91 (m, 1H), 1.96-2.10 (m, 1H), 2.11-2.20 (m, 1H), 2.23 (s, 6H), 2.37-2.42 (m, 2H), 2.64-2.68 (m, 2H), 2.69-3.23 (m, 1H), 3.43-4.02 (m, 1H), 4.09-4.16 (m, 2H), 5.05-5.55 (m, 1H), 5.57-5.70 (m, 2H), 7.09-7.26 (m, 2H), 7.28-7.39 (m, 1H), 7.43-7.53 (m, 1H), 7.97-8.08 (m, 1H), 10.30-10.68 (m, 1H).
LCMS(ESI): [M+H]⁺ m/z: calcd 488.2; found 488.2; Rt=2.126 min.

Example 266. The Synthesis of N-(6-amino-5-ethyl-3-pyridyl)-2-oxo-2-[rac-(2R,5S)-2-[3-chloro-4-(4-methylpiperazin-1-yl)phenyl]-5-methyl-1-piperidyl]acetamide (Compound 1265)

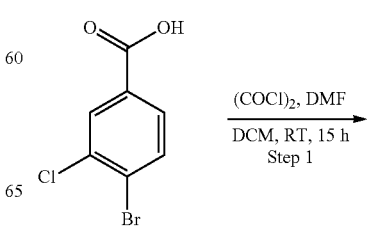

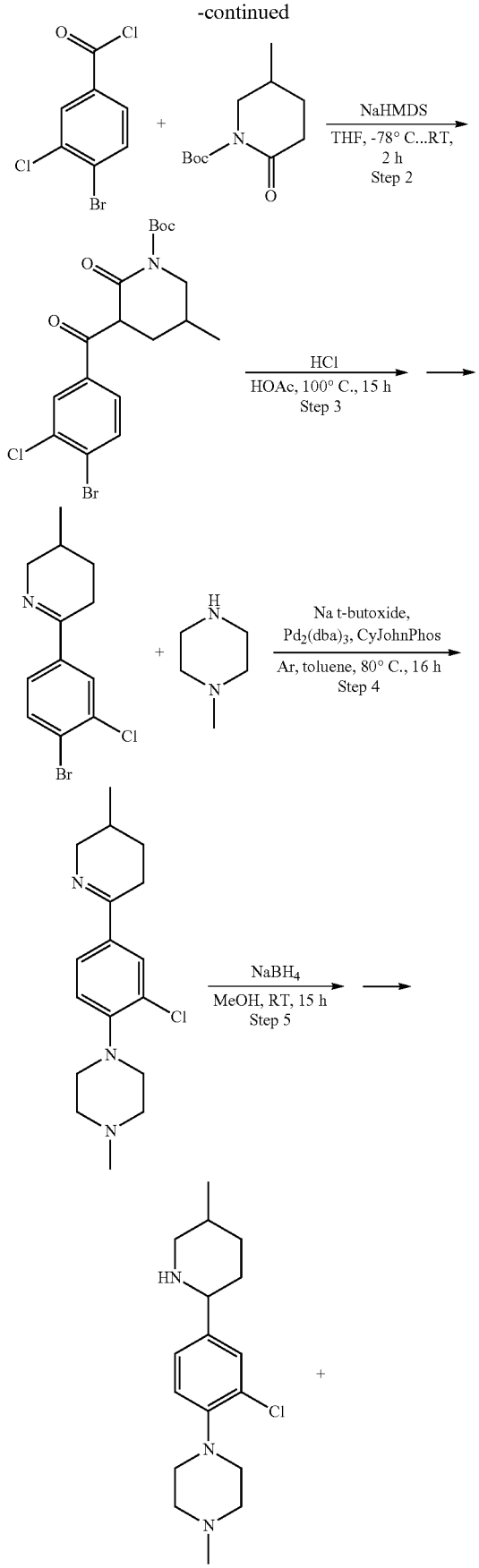

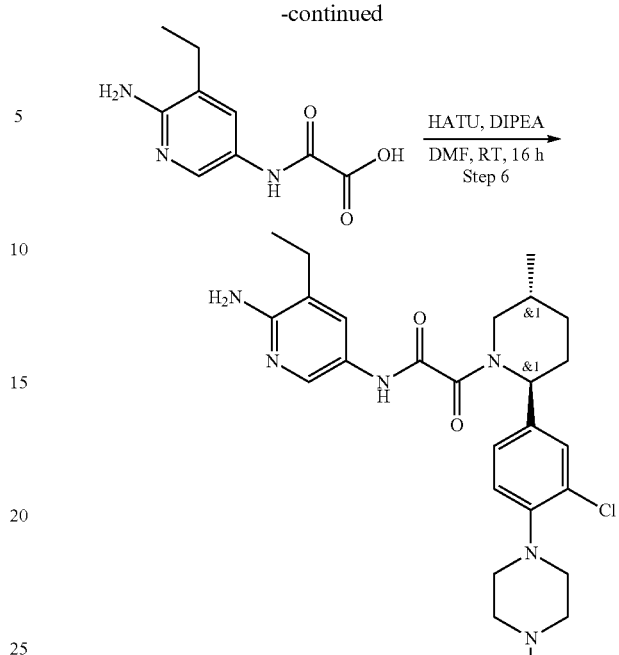

Step 4: The Synthesis of 1-[2-chloro-4-(3-methyl-2,3,4,5-tetrahydropyridin-6-yl)phenyl]-4-methyl-Piperazine To a suspension of 1-methylpiperazine (524.23 mg, 5.23 mmol, 580.55 uL), 6-(4-bromo-3-chloro-phenyl)-3-methyl-2,3,4,5-tetrahydropyridine (1.5 g, 5.23 mmol) and [1,1'-biphenyl]-2-yldicyclohexylphosphine (366.87 mg, 1.05 mmol) in toluene (10 mL), sodium tert-butoxide (754.49 mg, 7.85 mmol) and Tris(Dibenzylideneacetone)dipalladium (0) (143.78 mg, 157.02 umol) were added under Ar atmosphere. The resulting mixture was stirred at 80° C. for 16 hr. The reaction mixture was cooled, precipitate was filtered, the solvent was evaporated to obtain 1-[2-chloro-4-(3-methyl-2,3,4,5-tetrahydropyridin-6-yl)phenyl]-4-methyl-piperazine (1 g, 3.27 mmol, 62.47% yield).

LCMS(ESI): [M+H]$^+$ m/z: calcd 306.2; found 306.2; Rt=0.650 min.

Step 5: The Synthesis of 1-[2-chloro-4-(5-methyl-2-piperidyl)phenyl]-4-methyl-Piperazine Sodium Borohydride (247.40 mg, 6.54 mmol, 230.35 μL) was added in one portion to a stirred solution of 1-[2-chloro-4-(3-methyl-2,3,4,5-tetrahydropyridin-6-yl)phenyl]-4-methyl-piperazine (1 g, 3.27 mmol) in MeOH (49.77 mL) at 0° C. The resulting mixture was stirred at 25° C. for 15 hr, and then evaporated in vacuo. The residue was diluted with water (20 mL) and extracted with EtOAc (2*40 mL). The combined organic extracts were dried over sodium sulphate and evaporated in vacuo. The obtained oil was subjected to HPLC (Waters SunFire C18 19*100 5 mkm column and MeCN+NH$_3$ as an eluent mixture) to afford 1-[2-chloro-4-(5-methyl-2-piperidyl)phenyl]-4-methyl-piperazine (0.13 g, 422.27 μmol, 12.91% yield).

LCMS(ESI): [M+H]$^+$ m/z: calcd 308.2; found 308.2; Rt=1.500 min.

Step 6: The Synthesis of N-(6-amino-5-ethyl-3-pyridyl)-2-oxo-2-[rac-(2R,5S)-2-[3-chloro-4-(4-methylpiperazin-1-yl)phenyl]-5-methyl-1-piperidyl]acetamide (Compound 1265

DIPEA (136.44 mg, 1.06 mmol, 183.88 µL) was added to the solution of respective 2-[(6-amino-5-ethyl-3-pyridyl)amino]-2-oxo-acetic acid (88.34 mg, 422.27 µmol) and 1-[2-chloro-4-(5-methyl-2-piperidyl)phenyl]-4-methyl-piperazine (0.13 g, 422.27 µmol) in DMF (4.82 mL). The resulting mixture was stirred for 5 min followed by the addition of HATU (176.62 mg, 464.50 µmol). Then, the reaction mixture was stirred overnight at rt. After the completion of the reaction, monitored by LCMS, the resulting suspension was concentrated under reduced pressure, dissolved in EtOAc and washed with water and brine, dried over Na₂SO₄. The obtained solid was subjected to HPLC (Waters SunFire C18 20*100 5 mkm column and water-MeCN+FA as an eluent mixture) to afford N-(6-amino-5-ethyl-3-pyridyl)-2-oxo-2-[rac-(2R,5S)-2-[3-chloro-4-(4-methylpiperazin-1-yl)phenyl]-5-methyl-1-piperidyl]acetamide (17 mg, 28.76 µmol, 6.81% yield, 2HCOOH).

$^1$H NMR (600 MHz, dmso) δ 0.97-1.05 (m, 3H), 1.12-1.18 (m, 3H), 1.26-1.38 (m, 1H), 1.60-1.70 (m, 1H), 1.82-1.93 (m, 1H), 1.99-2.09 (m, 1H), 2.14-2.25 (m, 1H), 2.62-2.85 (m, 1H), 2.88 (s, 3H), 2.96-3.02 (m, 2H), 3.17-3.26 (m, 4H), 3.50-3.55 (m, 4H), 3.70-4.05 (m, 1H), 5.09-5.58 (m, 1H), 7.22-7.30 (m, 2H), 7.31-7.40 (m, 1H), 7.42-7.80 (m, 2H), 7.80-7.87 (m, 1H), 8.24-8.35 (m, 1H), 9.68-9.84 (m, 1H), 11.01-11.16 (m, 1H).

LCMS(ESI): [M+H]⁺ m/z: calcd 500.2; found 500.2; Rt=1.580 min.

Example 267. The Synthesis of Rel-N-(6-amino-5-methylpyridin-3-yl)-2-((2R,4S,5R)-2-(4-fluorophenyl)-5-methyl-4-(trifluoromethoxy)piperidin-1-yl)-2-oxoacetamide (Compound 1323) and Rel-N-(6-amino-5-methylpyridin-3-yl)-2-((2R,4S,5R)-2-(4-fluorophenyl)-5-methyl-4-(trifluoromethoxy)piperidin-1-yl)-2-oxoacetamide (Compound 1213

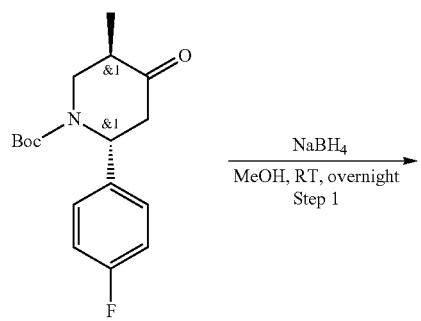

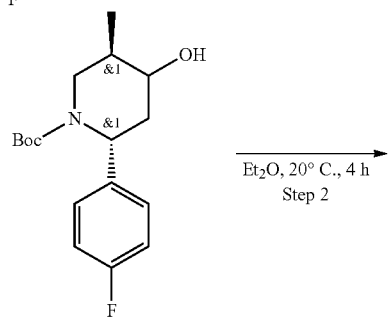

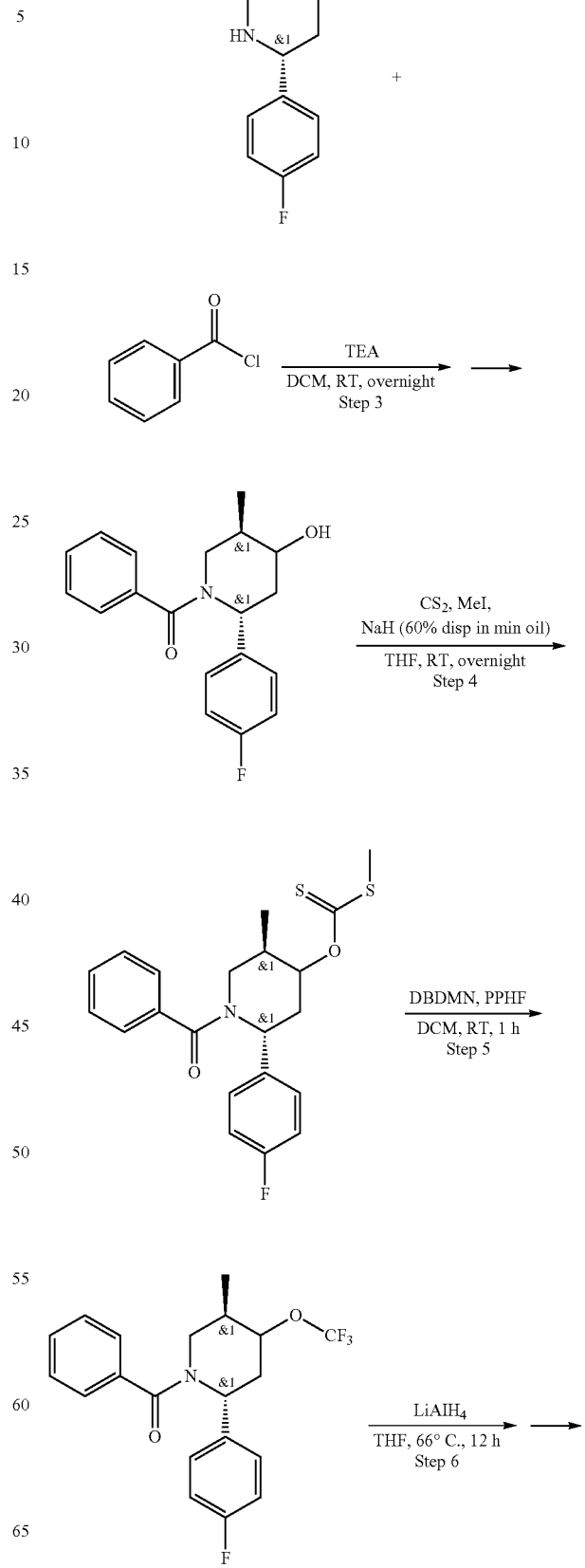

1813
-continued

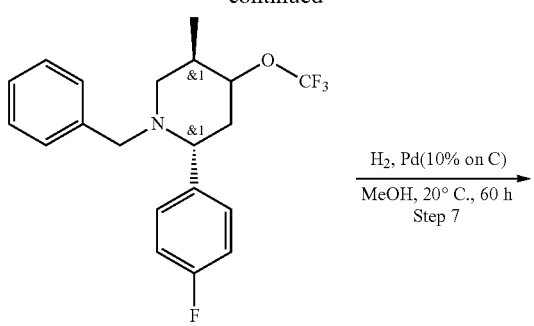

H₂, Pd(10% on C)
MeOH, 20° C., 60 h
Step 7

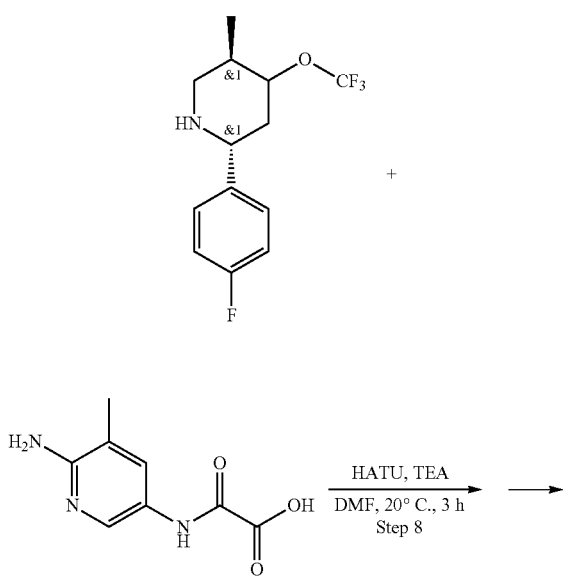

Compound 1323

1814
-continued

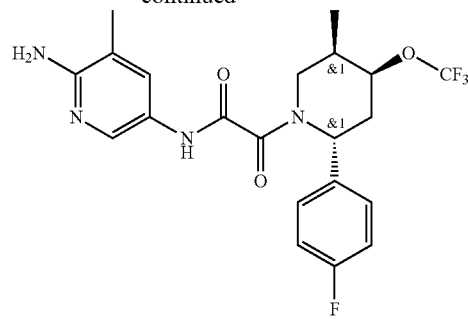

Compound 1213

Step 3: The Synthesis of [(2R,5R)-2-(4-fluorophenyl)-4-hydroxy-5-methyl-1-piperidyl]-phenyl-methanone (2R,5R)-2-(4-fluorophenyl)-5-methyl-piperidin-4-ol (1.7 g, 6.92 mmol, HCl) and TEA (3.50 g, 34.59 mmol, 4.82 mL) were mixed together in DCM (20 mL) and the resulting solution was cooled to 0° C. in an ice/methanol bath. Benzoyl chloride (1.07 g, 7.61 mmol) was added dropwise to the previous solution and the resulting mixture was allowed to warm to room temperature and stirred overnight. The reaction mixture was diluted with DCM and the resulting solution was washed with water, dried over Na₂SO₄, filtered and evaporated to obtain [(2R,5R)-2-(4-fluorophenyl)-4-hydroxy-5-methyl-1-piperidyl]-phenyl-methanone (2.15 g, 6.86 mmol, 99.17% yield) which was used in the next step without further purification.
LCMS(ESI): [M+H]⁺ m/z: calcd 314.2; found 314.2; Rt=1.276 min.

Step 4: The Synthesis of O-[(2R,5R)-1-benzoyl-2-(4-fluorophenyl)-5-methyl-4-piperidyl]methylsulfanylmethanethioate (2R,5R)-2-(4-fluorophenyl)-4-hydroxy-5-methyl-1-piperidyl]-phenyl-methanone (2.15 g, 6.86 mmol) was dissolved in THF (20 mL) and to the resulting mixture Sodium hydride (in oil dispersion) 60% dispersion in mineral oil (473.20 mg, 20.58 mmol) was added under cooling with ice/water, the reaction mixture left stirred for 1 h then carbon disulfide (1.57 g, 20.58 mmol) was added under cooling with ice/water, the reaction mixture was heated to RT and stirred for 30 min, then the reaction mixture was cooled again with ice/water and methyl iodide (2.92 g, 20.58 mmol, 1.28 mL) was added, the resulting mixture was heated to RT and stirred overnight. The reaction mixture was diluted with EA and washed twice with brine. 0-[(2R,5R)-1-benzoyl-2-(4-fluorophenyl)-5-methyl-4-piperidyl]methylsulfanylmethanethioate (2.5 g, 6.20 mmol, 90.30% yield) was obtained as a brown gum. The obtained product was used in the next step without further purification
LCMS(ESI): [M+H]⁺ m/z: calcd 404.2; found 404.2; Rt=1.483 min.

Step 5: The Synthesis of [(2R,5R)-2-(4-fluorophenyl)-5-methyl-4-(trifluoromethoxy)-1-piperidyl]-phenyl-methanone 1,3-Dibromo-5,5-dimethylhydantoin (7.09 g, 24.78 mmol) was dissolved in DCM (60 mL) and the obtained solution was cooled to −70° C. and at this temperature Hydrogen fluoride-pyridine (70% HF) (8.60 g, 86.73 mmol, 7.54 mL) was added, the reaction mixture was left stirred at −70° C. for 30 min. Then the solution of O-[(2R,5R)-1-benzoyl-2-(4-fluorophenyl)-5-methyl-4-piperidyl]methyl-sulfanylmethanethioate (2.5 g, 6.20 mmol) in DCM (5 mL) was added at −70° C. and the obtained mixture was stirred for 1 h then heated to RT at stirred overnight. The reaction mixture was poured into sat. aq. s-n of $Na_2CO_3$, DCM layer was separated and the aqueous layer was extracted with additional DCM, the combined organic phases was dried over $Na_2SO_4$, filtered and concentrated in vacuo. The obtained crude product was purified by FCC (EtOAc in hexanes from 0% to 100%). [(2R,5R)-2-(4-fluorophenyl)-5-methyl-4-(trifluoromethoxy)-1-piperidyl]-phenyl-methanone (0.3 g, 786.65 μmol, 12.70% yield) was obtained as an yellow gum.

LCMS(ESI): [M+H]⁺ m/z: calcd 382.0; found 382.0; Rt=1.538 min.

Step 6: The Synthesis of (2R,5R)-1-benzyl-2-(4-fluorophenyl)-5-methyl-4-(trifluoromethoxy)piperidine Lithium aluminium hydride (40.91 mg, 1.21 mmol) was suspended in THF (10 mL) and heated under reflux, then the solution of [(2R,5R)-2-(4-fluorophenyl)-5-methyl-4-(trifluoromethoxy)-1-piperidyl]-phenyl-methanone (0.115 g, 301.55 μmol) in THE (2 mL) was added dropwise and the reaction mixture was stirred at 66° C. for 12 hr. The reaction mixture was cooled with ice/methanol and water (1 mL/g of $LiAlH_4$) was added dropwise, then 40% aq. s-n of KOH (1 mL/g of $LiAlH_4$) was added dropwise, then water (2 mL/g of $LiAlH_4$) was added dropwise. The solid which formed was filtered off and washed three times with EA, the filtrate was concentrated in vacuo. (2R,5R)-1-benzyl-2-(4-fluorophenyl)-5-methyl-4-(trifluoromethoxy)piperidine (0.1 g, 272.20 μmol, 90.27% yield) was obtained as an yellow gum.

LCMS(ESI): [M+H]⁺ m/z: calcd 368.2; found 368.2; Rt=1.196 min.

Step 7: The Synthesis of (2R,5R)-2-(4-fluorophenyl)-5-methyl-4-(trifluoromethoxy)piperidine (2R,5R)-1-benzyl-2-(4-fluorophenyl)-5-methyl-4-(trifluoromethoxy)piperidine (0.1 g, 272.20 μmol) was dissolved in MeOH and Pd/C (10%) (0.01 g, 272.20 μmol) was added thereto. The resulting reaction mixture was degassed and filled with hydrogen and stirred at 20° C. for 60 hr. The reaction mixture was filtered, the filter cake was washed with additional MeOH and the filtrate was concentrated in vacuo. (2R,5R)-2-(4-fluorophenyl)-5-methyl-4-(trifluoromethoxy)piperidine (0.07 g, 252.47 μmol, 92.75% yield) was obtained as a yellow gum.

LCMS(ESI): [M+H]⁺ m/z: calcd 278.0; found 278.0; Rt=0.967 min.

Step 8: The Synthesis of N-(6-amino-5-methyl-3-pyridyl)-2-[(2R,5R)-2-(4-fluorophenyl)-5-methyl-4-(trifluoromethoxy)-1-piperidyl]-2-oxo-acetamide (2R,5R)-2-(4-fluorophenyl)-5-methyl-4-(trifluoromethoxy)piperidine (0.07 g, 252.47 mol), TEA (76.64 mg, 757.42 μmol, 105.57 μL) and 2-[(6-amino-5-methyl-3-pyridyl)amino]-2-oxo-acetic acid (49.28 mg, 252.47 μmol) were dissolved in DMF (4 mL) and HATU (105.60 mg, 277.72 μmol) was added in one portion, the resulting mixture was stirred for 3 hr at 20° C. The reaction mixture was purified by reverse phase HPLC (2-10 min; 65-75% MeCN Flow rate 30 mL/min (loading pump 4 mL MeCN) column: SunFire 100*19 mm, 5 microM). The desired product N-(6-amino-5-methyl-3-pyridyl)-2-[(2R,5R)-2-(4-fluorophenyl)-5-methyl-4-(trifluoromethoxy)-1-piperidyl]-2-oxo-acetamide (0.028 g, 61.62 μmol, 24.41% yield) was isolated as a light-yellow solid.

LCMS(ESI): [M+H]⁺ m/z: calcd 455.2; found 455.2; Rt=1.225 min.

Step 9: Example 1. The Synthesis of Rel-N-(6-amino-5-methylpyridin-3-yl)-2-((2R,4S,5R)-2-(4-fluorophenyl)-5-methyl-4-(trifluoromethoxy)piperidin-1-yl)-2-oxoacetamide (Compound 1323) and Rel-N-(6-amino-5-methylpyridin-3-yl)-2-((2R,4S,5R)-2-(4-fluorophenyl)-5-methyl-4-(trifluoromethoxy)piperidin-1-yl)-2-oxoacetamide (Compound 1213

Chiral resolution was performing using:
Column: ChiralART YMC (250*20 mm, 5 mkm), Hexane-IPA-MeOH, 90-5-5, Flow 12 mL:/min; Column Temperature: 24° C.; Wavelength: 205 nm, 215 nm, to give: Compound 1323-rel-N-(6-amino-5-methylpyridin-3-yl)-2-((2R,4S,5R)-2-(4-fluorophenyl)-5-methyl-4-(trifluoromethoxy)piperidin-1-yl)-2-oxoacetamide (0.008 g, 17.60 μmol, 28.57% yield), with ret.time=12.706 min(analytical), 43.854 min(preparative) and Compound 1213—rel-N-(6-amino-5-methylpyridin-3-yl)-2-((2R,4S,5R)-2-(4-fluorophenyl)-5-methyl-4-(trifluoromethoxy)piperidin-1-yl)-2-oxoacetamide (0.009 g, 19.81 μmol, 32.14% yield), with ret.time=17.66 min(analytical), 66.502 min(preparative).

Compound 1323: RT (Chiralpak IC (250*4.6, 5 mkm), Hexane-IPA-MeOH, 70-15-15, 0.6 mL/min)=12.607 min.

¹H NMR (600 MHz, dmso) δ 0.98-1.03 (m, 3H), 2.00-2.07 (m, 3H), 2.14-2.30 (m, 2H), 2.60-2.66 (m, 1H), 2.80-3.26 (m, 1H), 3.63-4.27 (m, 1H), 4.43-4.57 (m, 1H), 5.34-6.14 (m, 3H), 7.23-7.30 (m, 2H), 7.31-7.41 (m, 2H), 7.48-7.57 (m, 1H), 8.00-8.09 (m, 1H), 10.59-10.69 (m, 1H).

LCMS(ESI): [M+H]⁺ m/z: calcd 455.2; found 455.2; Rt=2.941 min.

Compound 1213: RT (Chiralpak IC (250*4.6, 5 mkm), Hexane-IPA-MeOH, 70-15-15, 0.6 mL/min)=17.532 min.

¹H NMR (600 MHz, dmso) δ 0.99-1.04 (m, 3H), 1.99-2.07 (m, 3H), 2.13-2.30 (m, 2H), 2.60-2.65 (m, 1H), 2.78-3.25 (m, 1H), 3.61-4.30 (m, 1H), 4.47-4.54 (m, 1H), 5.34-6.00 (m, 3H), 7.24-7.30 (m, 2H), 7.31-7.42 (m, 2H), 7.49-7.56 (m, 1H), 7.98-8.10 (m, 1H), 10.58-10.67 (m, 1H).

LCMS(ESI): [M+H]⁺ m/z: calcd 455.2; found 455.2; Rt=2.938 min.

Example 268. The Synthesis of N-(6-amino-5-ethylpyridin-3-yl)-2-((2R,5S)-2-(3-(2-(dimethylamino)ethyl)phenyl)-5-methylpiperidin-1-yl)-2-oxoacetamide (Compound 1226

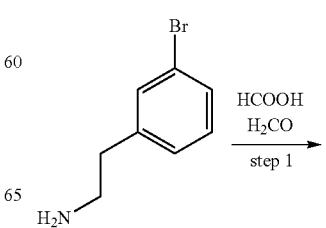

-continued

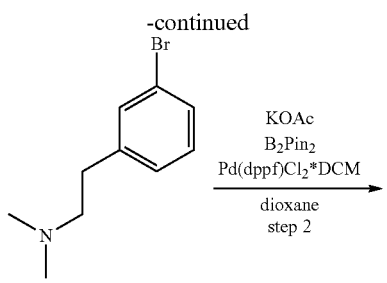

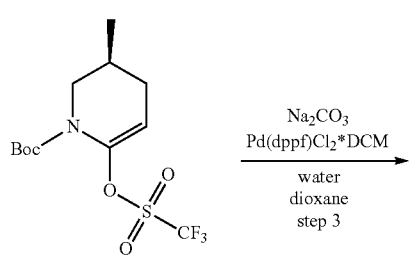

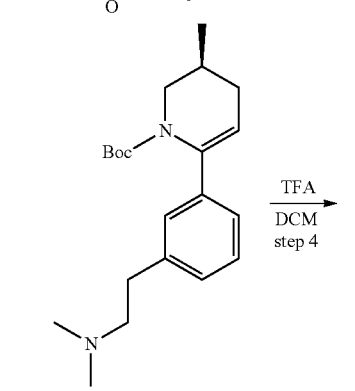

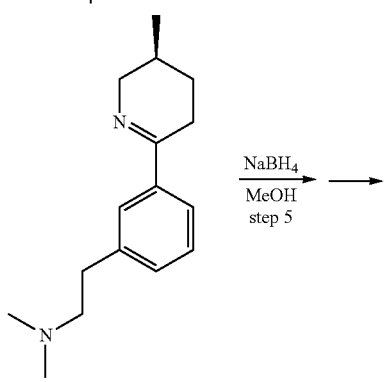

-continued

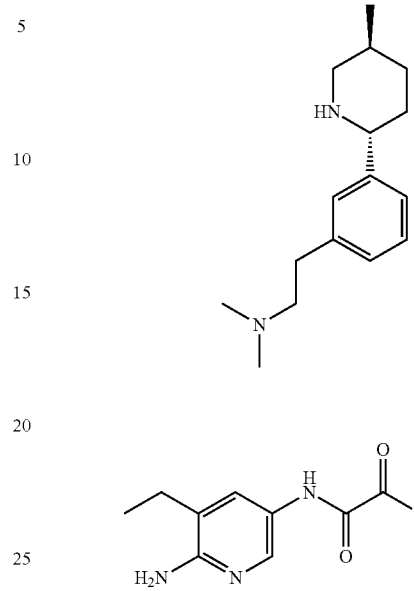

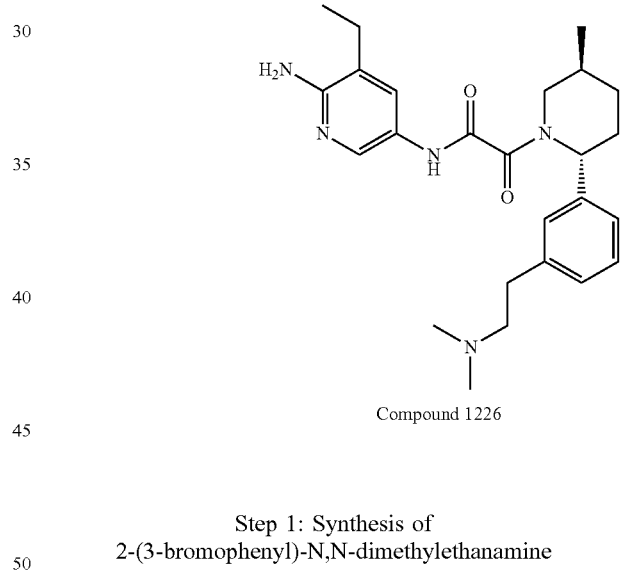

Compound 1226

Step 1: Synthesis of 2-(3-bromophenyl)-N,N-dimethylethanamine

Formic acid (6.61 g, 143.50 mmol, 5.41 mL) was added to 2-(3-bromophenyl)ethanamine (9.57 g, 47.83 mmol) cautiously. After that formaldehyde, 37% w/w aq. soln., stab. with 7-8% MeOH (4.31 g, 143.50 mmol, 3.98 mL) was added (careful: gas evolution!) and the reaction mixture was stirred for 16 hr at 80° C. The mixture was cooled and 20 mL of 6N HCl was added. It was washed with 30 mL MTBE. Then the aqueous layer was basified with $K_2CO_3$ and extracted with DCM (3×15 mL). DCM layers were combined, dried over $Na_2SO_4$ and evaporated under reduced. Crude product was purified by column chromatography to afford 2-(3-bromophenyl)-N,N-dimethyl-ethanamine (2 g, 8.77 mmol, 18.33% yield).

LCMS(ESI): $[M]^+$ m/z: calcd 228.2; found 229.2; Rt=0.840 min.

Step 2: Synthesis of N,N-dimethyl-2-(3-(4,4,5,5-tetramethyl-1,3,2-dioxaborolan-2-yl)phenyl)ethanamine A mixture of 2-(3-bromophenyl)-N,N-dimethylethanamine (1 g, 4.38 mmol), 4,4,5,5-tetramethyl-2-(4,4,5,5-tetramethyl-1,3,2-dioxaborolan-2-yl)-1,3,2-dioxaborolane (1.11 g, 4.38 mmol) and potassium acetate (860.39 mg, 8.77 mmol, 548.02 µL) in dioxane (24.45 mL) was evacuated and then backfilled with argon. This operation was repeated two times, then Pd(dppf)Cl$_2$*DCM (178.99 mg, 219.17 µmol) was added and the reaction mixture was stirred under argon at 100° C. for 15 hr. Upon completion, the mixture was evaporated under reduced pressure; crude product was purified by pass through SiO$_2$, MeOH as eluent. Combined layers were concentrated in vacuum, 30 mL CHCl$_3$ was added, mixture was stirred for 30 min and precipitate was filtered off. Mother liquid was evaporated under reduced pressure to afford N,N-dimethyl-2-[3-(4,4,5,5-tetramethyl-1,3,2-dioxaborolan-2-yl)phenyl]ethanamine (1.2 g, 4.36 mmol, 99.48% yield).

LCMS(ESI): [M]$^+$ m/z: calcd 275.2; found 276.2; Rt=0.870 min.

Step 3: Synthesis of (S)-tert-butyl 6-(3-(2-(dimethylamino)ethyl)phenyl)-3-methyl-3,4-dihydropyridine-1(2H)-carboxylate Sodium carbonate (924.35 mg, 8.72 mmol, 365.07 µL) was added to a solution of N,N-dimethyl-2-[3-(4,4,5,5-tetramethyl-1,3,2-dioxaborolan-2-yl)phenyl]ethanamine (1.2 g, 4.36 mmol) and tert-butyl (3S)-3-methyl-6-(trifluoromethylsulfonyloxy)-3,4-dihydro-2H-pyridine-1-carboxylate (1.81 g, 5.23 mmol) in water (7.95 mL) and dioxane (23.86 mL). Reaction flask was evacuated and refilled with argon 3 times. Then, Pd(dppf)Cl$_2$*DCM (178.05 mg, 218.03 µmol) was added under stream of argon. Resulting mixture was stirred at 90° C. for 15 hr under inert atmosphere. Upon completion, solvent was evaporated, 40 mL CHCl$_3$ was added to the residue, precipitate was filtered off. Mother liquid was concentrated to dryness to afford tert-butyl (3S)-6-[3-[2-(dimethylamino)ethyl]phenyl]-3-methyl-3,4-dihydro-2H-pyridine-1-carboxylate (2 g, crude).

LCMS(ESI): [M]$^+$ m/z: calcd 344.2; found 345.2; Rt=1.214 min.

Step 4: Synthesis of (S)—N,N-dimethyl-2-(3-(5-methyl-3,4,5,6-tetrahydropyridin-2-yl)phenyl)ethanamine To a mixture of tert-butyl (3S)-6-[3-[2-(dimethylamino)ethyl]phenyl]-3-methyl-3,4-dihydro-2H-pyridine-1-carboxylate (2 g, 5.81 mmol) in DCM (40 mL), TFA (9.93 g, 87.09 mmol, 6.71 mL) was added in one portion and the resulting mixture was left to stir at 25° C. for 48 hr. Upon completion of the reaction, solvent was concentrated, 40 mL of water was added to the residue. The resulting mixture was basified with K$_2$CO$_3$ to alkaline pH, extracted with DCM (3*20 mL), combined organic layers were dried over Na$_2$SO$_4$, filtered and concentrated to obtain N,N-dimethyl-2-[3-[(3S)-3-methyl-1,2,3,4-tetrahydropyridin-6-yl]phenyl]ethanamine (0.7 g, crude).

LCMS(ESI): [M]$^+$ m/z: calcd 244.2; found 245.2; Rt=0.224 min.

Step 5: Synthesis of N,N-dimethyl-2-(3-((2R,5S)-5-methylpiperidin-2-yl)phenyl)ethanamine To a mixture of N,N-dimethyl-2-[3-[(3S)-3-methyl-1,2,3,4-tetrahydropyridin-6-yl]phenyl]ethanamine (0.7 g, 2.86 mmol) in MeOH (30 mL), sodium borohydride (130.04 mg, 3.44 mmol, 121.08 µL) was added in one portion. The resulting mixture was allowed to stir overnight at 25° C. Upon completion, solvent was evaporated to dryness. The residue was subjected by HPLC (column: YMC Triart C18 100×20 mm, 5 um; mobile phase: 50-50-75% 0-1-6 min H$_2$O/MeOH/0.1% NH$_4$OH, flow rate: 30 mL/min (loading pump 4 mL/min MeOH)) to afford N,N-dimethyl-2-[3-[(2R,5S)-5-methyl-2-piperidyl]phenyl]ethanamine (0.0587 g, 238.24 mol, 8.32% yield).

LCMS(ESI): [M]$^+$ m/z: calcd 246.2; found 247.2; Rt=0.603 min.

Step 6: Synthesis of N-(6-amino-5-ethylpyridin-3-yl)-2-((2R,5S)-2-(3-(2-(dimethylamino)ethyl)phenyl)-5-methylpiperidin-1-yl)-2-oxoacetamide (Compound 1226)

To a mixture of N,N-dimethyl-2-[3-[(2R,5S)-5-methyl-2-piperidyl]phenyl]ethanamine (0.0587 g, 238.24 µmol), 2-[(6-amino-5-ethyl-3-pyridyl)amino]-2-oxo-acetic acid (49.84 mg, 238.24 µmol) and TEA (120.54 mg, 1.19 mmol, 166.03 µL) in DMF (3 mL), HATU (108.70 mg, 285.89 µmol) was added in one portion. The resulting mixture was allowed to stir at 25° C. for 15 hr. Upon completion, DMF was evaporated, the residue was subjected by HPLC (column: XBridge BEH C18 5 um 130A; mobile phase: 30-80% 0-5 min H$_2$O/MeOH/0.1% NH$_4$OH, flow rate: 30 mL/min (loading pump 4 mL/min MeOH)) to afford N-(6-amino-5-ethyl-3-pyridyl)-2-oxo-2-[(2R,5S)-2-[3-[2-(dimethylamino)ethyl]phenyl]-5-methyl-1-piperidyl]acetamide (67.2 mg, 153.57 µmol, 64.46% yield).

$^1$H NMR (500 MHz, DMSO-d$_6$) δ (ppm) 0.75-1.03 (m, 3H), 1.06-1.15 (m, 3H), 1.22-1.41 (m, 1H), 1.59-1.71 (m, 1H), 1.79-1.92 (m, 1H), 1.97-2.10 (m, 1H), 2.12-2.16 (m, 6H), 2.18-2.29 (m, 1H), 2.37-2.44 (m, 4H), 2.68-2.73 (m, 2H), 3.18-3.26 (m, 1H), 3.48-4.04 (m, 1H), 5.13-5.59 (m, 1H), 5.59-5.72 (m, 2H), 7.07-7.19 (m, 3H), 7.24-7.32 (m, 1H), 7.41-7.53 (m, 1H), 7.97-8.11 (m, 1H), 10.45-10.62 (m, 1H).

LCMS(ESI): [M]$^+$ m/z: calcd 437.2; found 438.2; Rt=1.759 min.

Example 269. The Synthesis of 2-[(2R,5S)-2-[4-[(3aR,7aS)-2-methyl-3,3a,4,6,7,7a-Hexahydro-1H-pyrrolo[3,4-c]pyridin-5-yl]phenyl]-5-methyl-1-piperidyl]-N-(6-amino-5-ethyl-3-pyridyl)-2-oxo-acetamide (Compound 1349
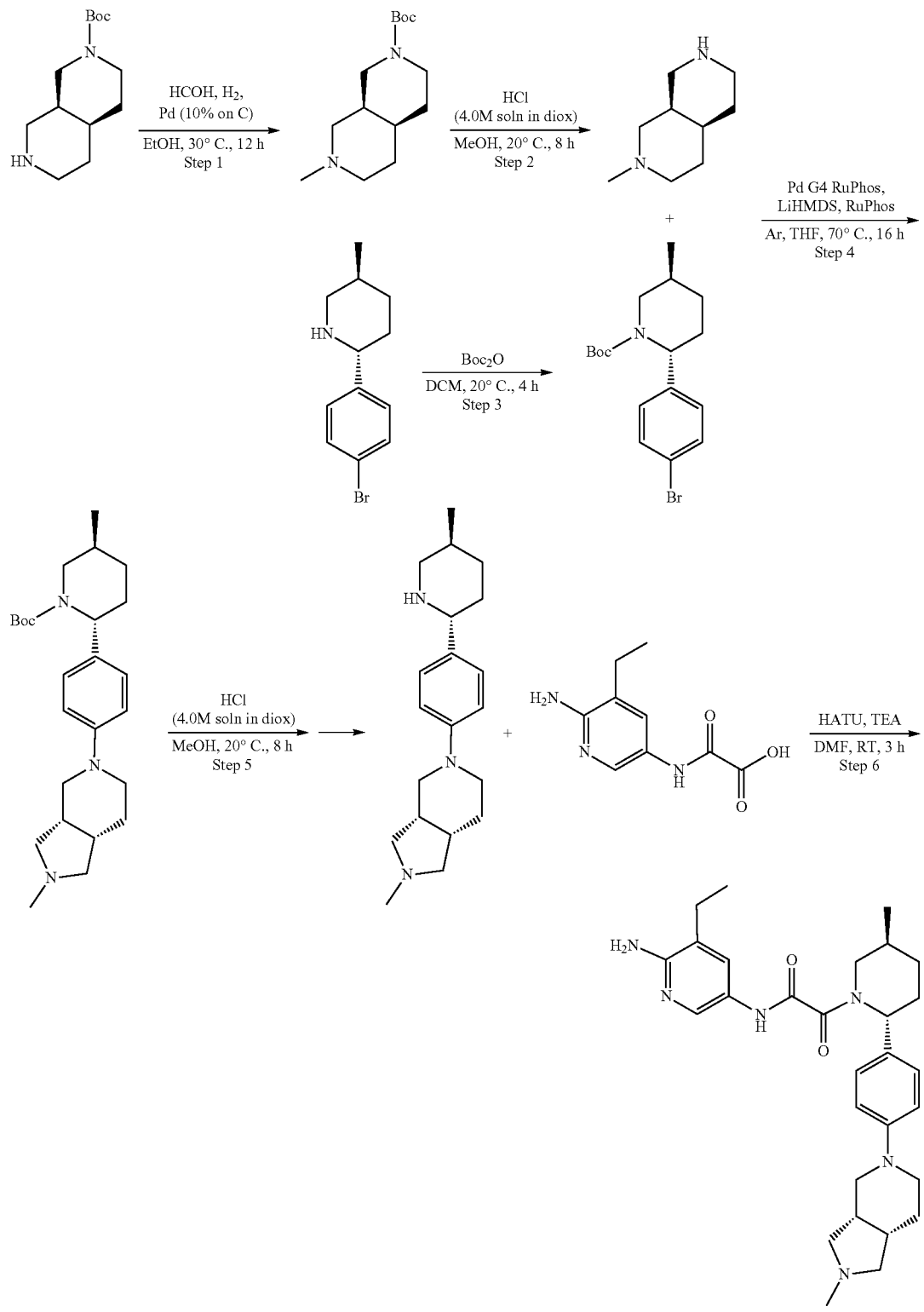

Step 1: The Synthesis of tert-butyl (3aS,7aR)-2-methyl-3,3a,4,6,7,7a-Hexahydro-1H-pyrrolo[3,4-c]pyridine-5-carboxylate To a solution of tert-butyl (3aS,7aR)-1,2,3,3a,4,6,7,7a-octahydropyrrolo[3,4-c]pyridine-5-carboxylate (2 g, 8.84 mmol) and Formaldehyde, 37% in aq. soln., ACS, 36.5-38.0%, stab. with 10-15% methanol (610.38 mg, 20.33 mmol, 563.60 µL) in EtOH (30 mL), Palladium, 10% on carbon, Type 487, dry (188.09 mg, 1.77 mmol) was added. The resulting mixture was stirred under Hydrogen atmosphere at 30° C. for 12 hr. The catalyst was filtered off and the solvent was removed in vacuo to give tert-butyl (3aS,7aR)-2-methyl-3,3a,4,6,7,7a-hexahydro-1H-pyrrolo[3,4-c]pyridine-5-carboxylate (1.9 g, 7.91 mmol, 89.46% yield). Yield: 1.9 g (89.46%)

$^1$H NMR (500 MHz, CDCl$_3$) δ (ppm) 1.20 (m, 2H), 1.45 (s, 9H), 1.62 (m, 2H), 2.18-2.30 (m, 5H), 2.72-2.78 (m, 2H), 3.15-3.16 (m, 2H), 3.64-3.68 (m, 3H), 4.78-4.91 (m, 1H).

Step 2: The Synthesis of (3aR,7aR)-2-methyl-1,3,3a,4,5,6,7,7a-Octahydropyrrolo[3,4-c]pyridine A solution of tert-butyl (3aS,7aR)-2-methyl-3,3a,4,6,7,7a-hexahydro-1H-pyrrolo[3,4-c]pyridine-5-carboxylate (1.9 g, 7.91 mmol) and Hydrogen chloride, 4 M in 1,4-dioxane, 99% (4.00 g, 109.71 mmol, 5 mL) in MeOH (30 mL) was stirred at 20° C. for 8 hr. The resulting mixture was evaporated in vacuo and residue was triturated with MTBE, filtered and dried to give (3aR,7aR)-2-methyl-1,3,3a,4,5,6,7,7a-octahydropyrrolo[3,4-c]pyridine (1.5 g, 7.04 mmol, 89.02% yield, 2HCl).

Yield: 1.5 g (89.02%)

LCMS(ESI): [M-Boc]$^+$ m/z: calcd 141.2; found 141.2; Rt=0.133 min.

Step 3: The Synthesis of tert-butyl (5S)-2-(4-bromophenyl)-5-methyl-piperidine-1-carboxylate Prepared by general procedure 2.

Yield: 14 g (87.34%)

LCMS(ESI): [M-Boc]$^+$ m/z: calcd 254.0; found 254.0; Rt=1.539 min.

Step 4: The Synthesis of tert-butyl (2R,5S)-2-[4-[(3aS,7aR)-2-methyl-3,3a,4,6,7,7a-Hexahydro-1H-pyrrolo[3,4-c]pyridin-5-yl]phenyl]-5-methyl-piperidine-1-carboxylate Prepared by general procedure 2 (Method B) Yield: 0.7 g (crude).

LCMS(ESI): [M+H]$^+$ m/z: calcd 414.2; found 414.4; Rt=2.565 min.

Step 5: The Synthesis of (3aS,7aR)-2-methyl-5-[4-[(2R,5S)-5-methyl-2-piperidyl]phenyl]-3,3a,4,6,7,7a-Hexahydro-1H-pyrrolo[3,4-c]pyridine Prepared by general procedure 2 (Method A) Yield: 0.55 g (76.85%, 3HCl).

LCMS(ESI): [M+2H]$^+$ m/z: calcd 315.2; found 315.2; Rt=0.542 min.

Step 6: The Synthesis of 2-[(2R,5S)-2-[4-[(3aR,7aS)-2-methyl-3,3a,4,6,7,7a-Hexahydro-1H-pyrrolo[3,4-c]pyridin-5-yl]phenyl]-5-methyl-1-piperidyl]-N-(6-amino-5-ethyl-3-pyridyl)-2-oxo-acetamide (Compound 1349)

Prepared by general procedure 2. Yield: 82.30 mg (20.45%).

HPLC conditions: Column: SunFire 100*19 mm, 5 microM; 2-10 min 50-50-80% MeOH+NH$_3$30 mL/min (loading pump 4 mL MeOH).

$^1$H NMR (500 MHz, dmso) δ 0.70-1.01 (m, 3H), 1.06-1.14 (m, 3H), 1.23-1.40 (m, 1H), 1.62-1.73 (m, 2H), 1.79-1.90 (m, 2H), 1.92-2.07 (m, 1H), 2.09-2.17 (m, 1H), 2.21 (s, 3H), 2.24-2.30 (m, 2H), 2.36-2.44 (m, 4H), 2.59-2.71 (m, 2H), 3.05-3.12 (m, 2H), 3.16-3.26 (m, 2H), 3.38-4.00 (m, 2H), 4.96-5.55 (m, 1H), 5.58-5.68 (m, 2H), 6.63-6.75 (m, 2H), 7.03-7.15 (m, 2H), 7.42-7.55 (m, 1H), 7.93-8.12 (m, 1H), 10.42-10.54 (m, 1H).

LCMS(ESI): [M]$^+$ m/z: calcd 506.2; found 506.2; Rt=1.916 min.

Example 270. The Synthesis of N-(6-amino-5-ethylpyridin-3-yl)-2-((2R,5S)-5-methyl-2-(4-((1-methylpiperidin-4-yl)Methoxy)phenyl)piperidin-1-yl)-2-oxoacetamide (Compound 1216)

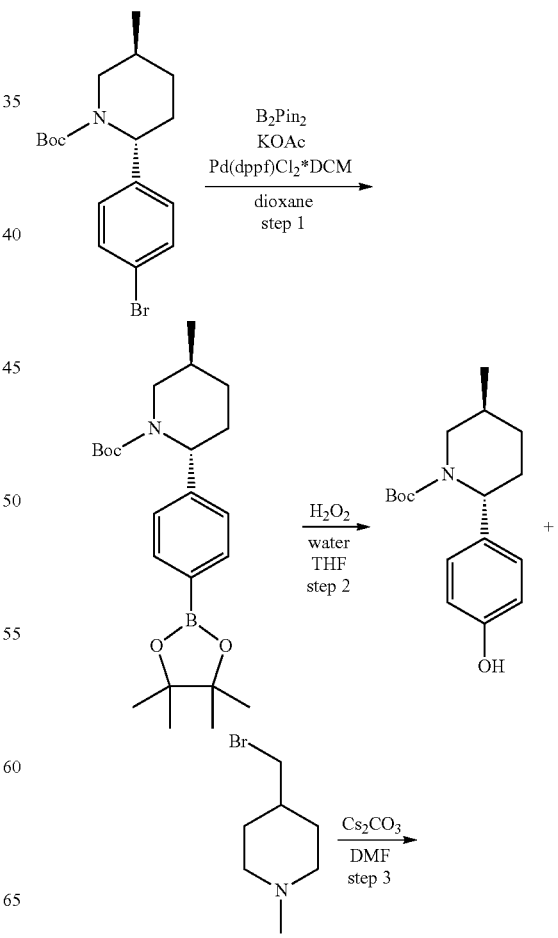

1825
-continued

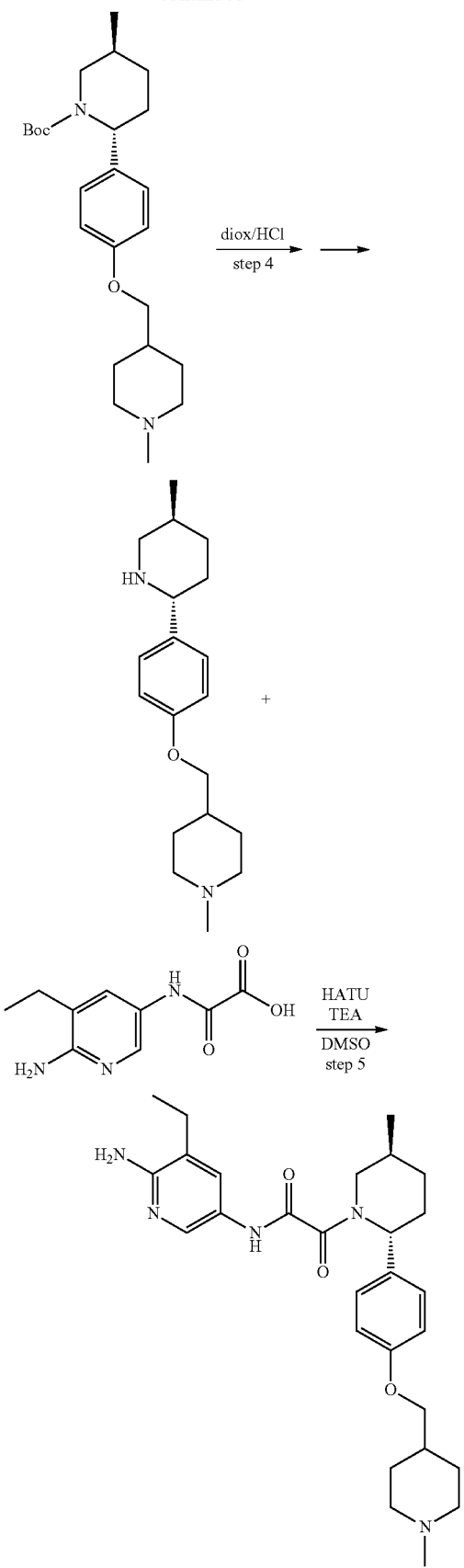

1826

Step 1: Synthesis of (2R,5S)-tert-butyl 5-methyl-2-(4-(4,4,5,5-tetramethyl-1,3,2-dioxaborolan-2-yl)phenyl)piperidine-1-carboxylate To a solution of tert-butyl (2R,5S)-2-(4-bromophenyl)-5-methyl-piperidine-1-carboxylate (1 g, 2.82 mmol), potassium acetate (637.13 mg, 6.49 mmol, 405.81 μL) and 4,4,5,5-tetramethyl-2-(4,4,5,5-tetramethyl-1,3,2-dioxaborolan-2-yl)-1,3,2-dioxaborolane (788.45 mg, 3.10 mmol) in dioxane (15 mL) was added Pd(dppf)Cl$_2$*DCM (138.30 mg, 169.36 μmol) under argon. Reaction mixture was stirred at 90° C. for 14 hr. Then the reaction mixture was concentrated, dissolved in 10 mL of ethyl acetate and washed with water. The organic layer was dried with sodium sulfate and evaporated under reduced pressure. The residue was purified by FCC to give tert-butyl (2R,5S)-5-methyl-2-[4-(4,4,5,5-tetramethyl-1,3,2-dioxaborolan-2-yl)phenyl]piperidine-1-carboxylate (0.6 g, 1.49 mmol, 52.96% yield).

LCMS(ESI): [M-Boc]$^+$ m/z: calcd 301.2; found 302.2; Rt=1.769 min.

Step 2: Synthesis of (2R,5S)-tert-butyl 2-(4-hydroxyphenyl)-5-methylpiperidine-1-carboxylate To a solution of tert-butyl (2R,5S)-5-methyl-2-[4-(4,4,5,5-tetramethyl-1,3,2-dioxaborolan-2-yl)phenyl]piperidine-1-carboxylate (700 mg, 1.57 mmol) in mixture of H$_2$O (6 mL) and THF (6 mL) hydrogen peroxide 35% (400 mg, 11.76 mmol, 363.64 μL) was added and stirred overnight. Reaction mixture was diluted with water (40 mL) and MTBE (40 mL), and treated with sodium thiosulfate, then organic phase was washed with water, dried over Na$_2$SO$_4$ and concentrated in vacuum to give tert-butyl (2R,5S)-2-(4-hydroxyphenyl)-5-methyl-piperidine-1-carboxylate (0.5 g, crude).

LCMS(ESI): [M-Boc]$^+$ m/z: calcd 191.2; found 192.2; Rt=1.456 min.

Step 3: Synthesis of (2R,5S)-tert-butyl 5-methyl-2-(4-((1-methylpiperidin-4-yl)Methoxy)phenyl)piperidine-1-carboxylate tert-butyl (2R,5S)-2-(4-hydroxyphenyl)-5-methyl-piperidine-1-carboxylate (250 mg, 857.97 μmol), 4-(bromomethyl)-1-methyl-piperidine (257.66 mg, 943.77 μmol, HBr) and cesium carbonate (838.63 mg, 2.57 mmol) were mixed in DMFA (5 mL) and heated with stirring at 90° C. for 24 hr. Reaction mixture was diluted with water and extracted with 30 mL of EtOAc, dried over Na$_2$SO$_4$ and concentrated in vacuum. DMSO-solution was subjected to HPLC (2-10 min 30-45% water/MeOH+NH$_3$; 30 mL/min; loading pump MeOH; 4 mL/min; column SunFire 19*100 mm). tert-butyl (2R,5S)-5-methyl-2-[4-[(1-methyl-4-piperidyl)methoxy]phenyl]piperidine-1-carboxylate (72.2 mg, 179.35 μmol, 20.90% yield) was obtained.

LCMS(ESI): [M]$^+$ m/z: calcd 402.2; found 403.2; Rt=3.477 min.

Step 4: Synthesis of 1-methyl-4-((4-((2R,5S)-5-methylpiperidin-2-yl)phenoxy)methyl)piperidine tert-butyl (2R,5S)-5-methyl-2-[4-[(1-methyl-4-piperidyl)methoxy]phenyl]piperidine-1-carboxylate (72.2 mg, 179.35 μmol) was dissolved in 5 mL of HCl/dioxane (10%) (6.54 mg, 179.35 μmol) and then 1 mL of MeOH was added for better solubility of product. After stirring for 1 hr RM was

1827 concentrated in vacuum. 1-methyl-4-[[4-[(2R,5S)-5-methyl-2-piperidyl]phenoxy]methyl]piperidine (80 mg, crude, 2HCl) was obtained.

LCMS(ESI): [M]+ m/z: calcd 302.2; found 303.2; Rt=0.602 min.

Step 5: Synthesis of N-(6-amino-5-ethylpyridin-3-yl)-2-((2R,5S)-5-methyl-2-(4-((1-methylpiperidin-4-yl)Methoxy)phenyl)piperidin-1-yl)-2-oxoacetamide (Compound 1250

1-methyl-4-[[4-[(2R,5S)-5-methyl-2-piperidyl]phenoxy]methyl]piperidine (80 mg, 213.12 μmol, 2HCl) and TEA (107.83 mg, 1.07 mmol, 148.52 μL) were mixed in DMSO (2 mL) and stirred for 5 min. Then 2-[(6-amino-5-ethyl-3-pyridyl)amino]-2-oxo-acetic acid (44.59 mg, 213.12 μmol) was added and stirred for next 10 min. Finally HATU (105.35 mg, 277.06 μmol) was added and stirred for 2 hr. Reaction mixture was subjected to HPLC. First loading HPLC data: Device (Mobile Phase, Column): SYSTEM 2-10 min 10-50% MeOH+FA 30 mL/min (loading pump 4 mL MeOH) column: SunFire 100*19 mm, 5 microM. Second loading HPLC data: Device (Mobile Phase, Column): SYSTEM 2-10 min 10-50% MeOH+NH₃, 30 mL/min (loading pump 4 mL MeOH) column: SunFire 100*19 mm, 5 microM. N-(6-amino-5-ethyl-3-pyridyl)-2-[(2R,5S)-5-methyl-2-[4-[(1-methyl-4-piperidyl)methoxy]phenyl]-1-piperidyl]-2-oxo-acetamide (36.2 mg, 73.33 μmol, 34.41% yield) was obtained as mixture of isomers.

¹H NMR (600 MHz, DMSO-d₆) δ (ppm) 0.76-1.02 (m, 3H), 1.06-1.14 (m, 3H), 1.17-1.43 (m, 3H), 1.64-1.76 (m, 3H), 1.81-1.85 (m, 1H), 1.86-2.04 (m, 2H), 2.05-2.10 (m, 1H), 2.13-2.20 (m, 3H), 2.20-2.28 (m, 1H), 2.32-2.41 (m, 3H), 2.60-2.65 (m, 1H), 2.68-2.78 (m, 1H), 3.13-3.28 (m, 1H), 3.38-3.45 (m, 1H), 3.77-3.95 (m, 2H), 4.93-5.58 (m, 1H), 5.58-5.74 (m, 2H), 6.85-7.01 (m, 2H), 7.16-7.31 (m, 2H), 7.38-7.57 (m, 1H), 7.96-8.16 (m, 1H), 10.42 (s, 1H).

LCMS(ESI): [M]+ m/z: calcd 493.2; found 494.2; Rt=1.753 min.

Example 271. The Synthesis of N-(6-amino-5-ethylpyridin-3-yl)-2-((2R,5S)-5-methyl-2-(3-((1-methylpiperidin-2-yl)methyl)phenyl)piperidin-1-yl)-2-oxoacetamide (Compound 1273

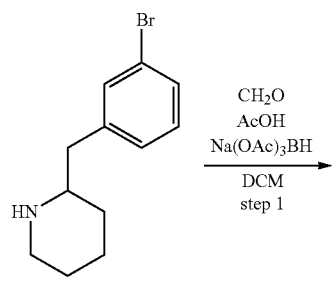

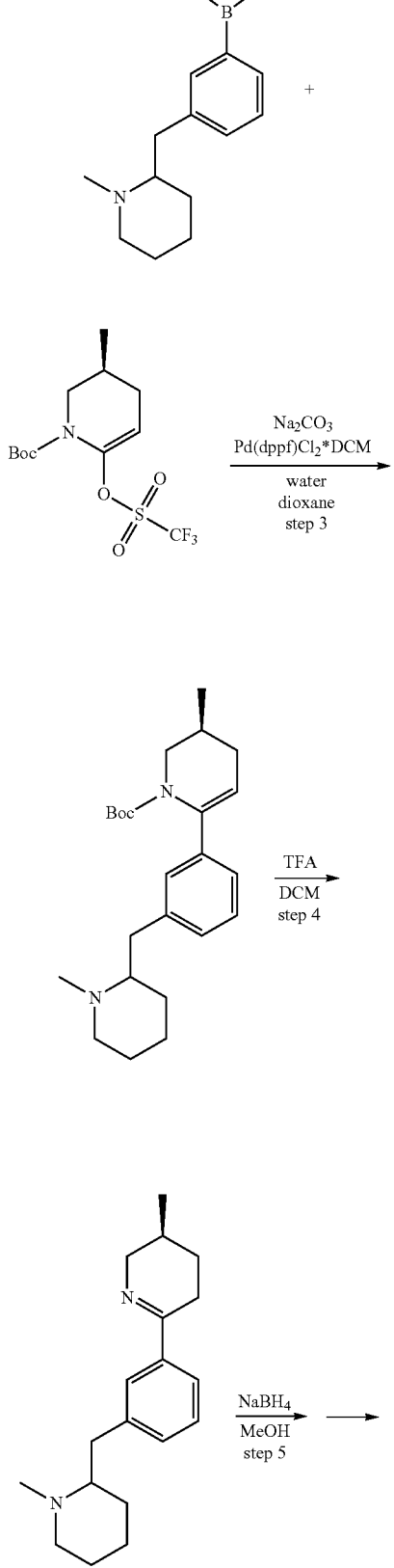

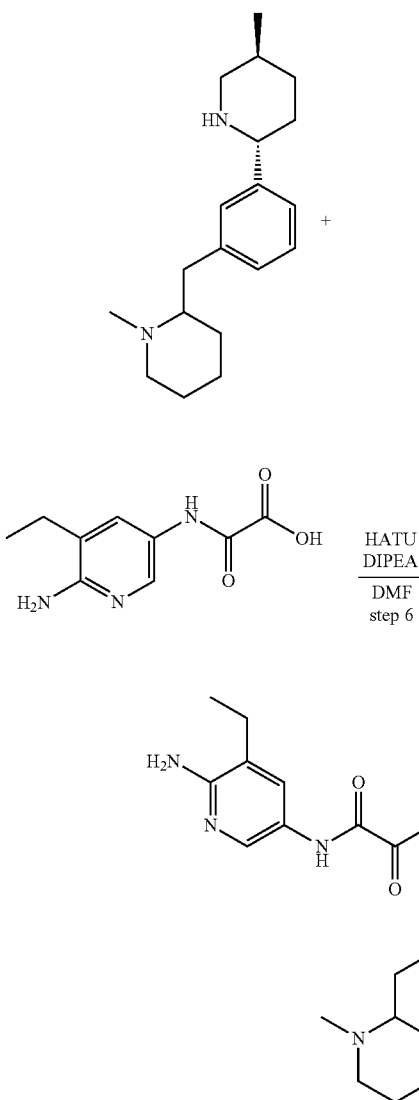

Step 1: Synthesis of 2-(3-bromobenzyl)-1-methylpiperidine

To a stirred solution of 2-[(3-bromophenyl)methyl]piperidine (1 g, 3.93 mmol) in DCM were added formaldehyde, 37% w/w aq. soln. (7.87 mmol) and acetic acid (708.79 mg, 11.80 mmol, 675.68 µL) respectively at 25° C. The resulting reaction mixture was stirred at 25° C. for 1 hr. Then sodium cyan borohydride (494.48 mg, 7.87 mmol) was added. Mixture was continued stirring for 12 hr. Upon completion, the reaction mixture was quenched with NaHCO₃ solution 20 mL. Then organic phase was washed with water 20 mL, dried over Na₂SO₄ and concentrated under reduced pressure to obtain crude product as yellow color state. The obtained crude product was purified by reverse phase HPLC (Device (Mobile Phase, Column): SYSTEM 20-20-65% 0-1-5 min H₂O/MeOH/0.01% HCl, flow: 30 mL/min (loading pump 4 mL/min MeOH); column: Chromatorex 18 SMB100-5T 100×19 mm 5 um) to afford HCl salt of product as a yellow color state. And another Device ((Mobile Phase, Column): SYSTEM 40-40-90% 0-1-6 min H₂O/MeOH/0.1% NH₄OH, flow: 30 mL/min (loading pump 4 mL/min MeOH) to obtain product as a base. The desired product 2-[(3-bromophenyl) methyl]-1-methyl-piperidine (0.25 g, 932.17 mol, 23.69% yield) was isolated as white color state.

LCMS(ESI): [M]⁺ m/z: calcd 268.2; found 269.2; Rt=2.094 min.

Step 2: Synthesis of 1-methyl-2-(3-(4,4,5,5-tetramethyl-1,3,2-dioxaborolan-2-yl)benzyl)piperidine To a stirred solution of 2-[(3-bromophenyl)methyl]-1-methyl-piperidine (1.2 g, 4.47 mmol) in dioxane (6.45 mL) was added 4,4,5,5-tetramethyl-2-(tetramethyl-1,3,2-dioxaborolan-2-yl)-1,3,2-dioxaborolane (1.25 g, 4.92 mmol) and potassium acetate (1.10 g, 11.19 mmol, 699.23 L). The resulting suspension was degassed with argon. Pd(dppf)Cl₂*DCM (327.08 mg, 447.44 mol) was added. The reaction mixture was stirred at 90° C. for 16 hr. Upon completion, the reaction mixture was filtered and the filtrate was evaporated in vacuum to get an oily residue. Then product was extracted with MTBE/water (50 mL/50 mL). Organic layer was dried over Na₂SO₄ and evaporated. Then diox/HCl (15 mL) was added and evaporated again. Then compound was washed with MTBE (20 mL) and filtered. Precipitation was dried under reduced pressure. The desired product 1-methyl-2-[[3-(4,4,5,5-tetramethyl-1,3,2-dioxaborolan-2-yl)phenyl]methyl]piperidine (0.9 g, 2.56 mmol, 57.19% yield, HCl) was isolated.

LCMS(ESI): [M]⁺ m/z: calcd 315.2; found 316.2; Rt=2.758 min.

Step 3: Synthesis of (3S)-tert-butyl 3-methyl-6-(3-((1-methylpiperidin-2-yl)methyl)phenyl)-3,4-dihydropyridine-1(2H)-carboxylate To a stirred solution of 1-methyl-2-[[3-(4,4,5,5-tetramethyl-1,3,2-dioxaborolan-2-yl)phenyl]methyl]piperidine (0.7 g, 1.99 mmol, HCl) and tert-butyl (3R)-3-methyl-6-(trifluoromethylsulfonyloxy)-3,4-dihydro-2H-pyridine-1-carboxylate (687.30 mg, 1.99 mmol) in dioxane (5 mL) was added sodium carbonate (210.94 mg, 1.99 mmol, 83.31 µL). The resulting suspension was degassed with argon. Pd(dppf)Cl₂*DCM (1.63 g, 1.99 mmol) was added. The reaction mixture was stirred at 90° C. for 16 hr. Upon completion, the reaction mixture was filtered and the filtrate was evaporated in vacuum to get an oily residue. The desired product tert-butyl (3S)-3-methyl-6-[3-[(1-methyl-2-piperidyl)methyl]phenyl]-3,4-dihydro-2H-pyridine-1-carboxylate (0.9 g, 2.34 mmol, 117.59% yield) was isolated.

LCMS(ESI): [M]⁺ m/z: calcd 384.2; found 385.2; Rt=3.113 min.

Step 4: Synthesis of (3S)-3-methyl-6-(3-((1-methylpiperidin-2-yl)methyl)phenyl)-2,3,4,5-tetrahydropyridine To a stirred solution of tert-butyl (3S)-3-methyl-6-[3-[(1-methyl-2-piperidyl)methyl]phenyl]-3,4-dihydro-2H-pyridine-1-carboxylate (0.9 g, 2.34 mmol) in DCM were added TFA (13.34 g, 117.02 mmol, 9.02 mL) respectively at 25° C. The resulting reaction mixture was stirred at 25° C. for 12 hr. Upon completion, the reaction mixture was concentrated under reduced pressure. Then crude product trifluoroacetic salt was dissolved in water 100 mL, water was washed with MTBE (30 mL). Then water layer was basified with Na₂CO₃ and extracted with DCM twice (100 mL). Organic layer was washed with water (50 mL), dried over Na₂SO₄ and evaporated. The desired product (3S)-3-methyl-6-[3-[(1-methyl-2-piperidyl)methyl]phenyl]-2,3,4,5-tetrahydropyridine (0.5 g, crude) was isolated as a brown color state.

LCMS(ESI): [M]⁺ m/z: calcd 284.2; found 285.2; Rt=0.650 min.

Step 5: Synthesis of 1-methyl-2-(3-((2R,5S)-5-methylpiperidin-2-yl)benzyl)piperidine To a stirred solution of (3S)-3-methyl-6-[3-[(1-methyl-2-piperidyl)methyl]phenyl]-2,3,4,5-tetrahydropyridine (0.5 g, 1.76 mmol) in MeOH (9.94 mL) were added sodium borohydride (66.50 mg, 1.76 mmol, 61.92 µL) respectively at 25° C. The resulting reaction mixture was stirred at 25° C. for 12 hr. Upon completion, the reaction mixture was concentrated under reduced pressure. Then compound was extracted with DCM/H₂O (100 mL/20 mL). Organic layer was washed with water, dried over Na₂SO₄ and evaporated. The obtained crude product was purified by reverse phase HPLC (Device (Mobile Phase, Column): SYSTEM 40-80% 0-6 min H₂O/MeCN/0.1% NH₄OH, flow: 30 mL/min (loading pump 4 mL/min MeOH); column: XBridge BEH C18 5 um) to afford product 1-methyl-2-[[3-[(2R,5S)-5-methyl-2-piperidyl]phenyl]methyl]piperidine (37 mg, 129.17 µmol, 7.35% yield) as brown color state.

LCMS(ESI): [M]⁺ m/z: calcd 286.2; found 287.2; Rt=1.011 min.

Step 6: Synthesis of N-(6-amino-5-ethylpyridin-3-yl)-2-((2R,5S)-5-methyl-2-(3-((1-methylpiperidin-2-yl)methyl)phenyl)piperidin-1-yl)-2-oxoacetamide (Compound 1273

To a stirred solution of 1-methyl-2-[[3-[(2R,5S)-5-methyl-2-piperidyl]phenyl]methyl]piperidine (37 mg, 129.17 µmol) in DMF (1.98 mL) were added DIPEA (33.39 mg, 258.33 µmol, 45.00 µL), 2-[(6-amino-5-ethyl-3-pyridyl)amino]-2-oxo-acetic acid (27.02 mg, 129.17 µmol) and HATU (49.11 mg, 129.17 µmol) respectively at 25° C. The resulting reaction mixture was allowed to stir at 25° C. for 12 hr. Upon completion, the reaction mixture was concentrated under reduced pressure to obtain crude product as brown color state. The obtained crude product was purified by reverse phase HPLC (Device (Mobile Phase, Column): SYSTEM 40-40-70% 0-1-6 min H₂O/MeCN/0.1% NH₄OH, flow: 30 mL/min (loading pump 4 mL/min MeOH); column: YMC Triart C18 100×20 mm, 5 um) to afford product N-(6-amino-5-ethyl-3-pyridyl)-2-[(2R,5S)-5-methyl-2-[3-[(1-methyl-2-piperidyl)methyl]phenyl]-1-piperidyl]-2-oxo-acetamide (23 mg, 48.15 µmol, 37.28% yield) as a brown color state.

¹H NMR (600 MHz, DMSO-d₆) δ (ppm) 0.98-1.14 (m, 8H), 1.19-1.37 (m, 2H), 1.37-1.47 (m, 2H), 1.49-1.58 (m, 1H), 1.59-1.73 (m, 1H), 1.79-1.94 (m, 1H), 1.95-2.07 (m, 2H), 2.09-2.21 (m, 1H), 2.24-2.29 (m, 3H), 2.33-2.43 (m, 3H), 2.60-2.76 (m, 2H), 2.93-3.23 (m, 2H), 3.45-4.04 (m, 1H), 5.12-5.59 (m, 1H), 5.58-5.68 (m, 2H), 7.03-7.17 (m, 3H), 7.24-7.32 (m, 1H), 7.42-7.54 (m, 1H), 7.97-8.10 (m, 1H), 10.52 (s, 1H).

LCMS(ESI): [M]⁺ m/z: calcd 477.2; found 478.2; Rt=1.698 min.

Example 272. The Synthesis of N-(6-amino-5-ethylpyridin-3-yl)-2-((2R,5S)-2-(4-(2-(dimethylamino)ethoxy)phenyl)-5-methylpiperidin-1-yl)-2-oxoacetamide (Compound 1292

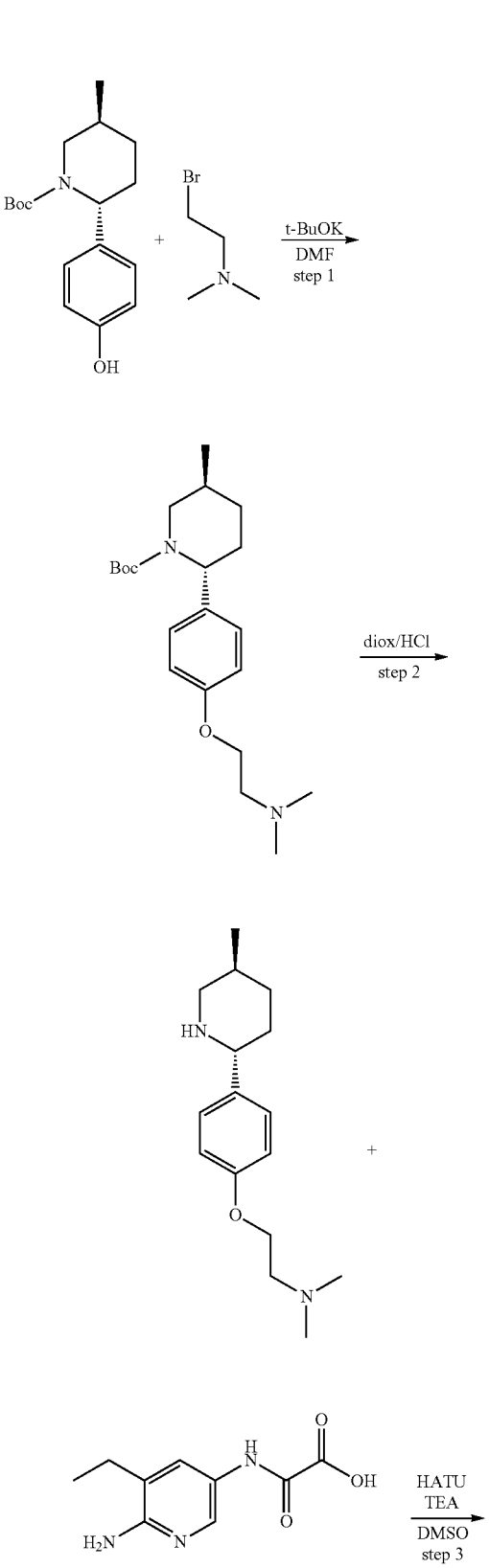

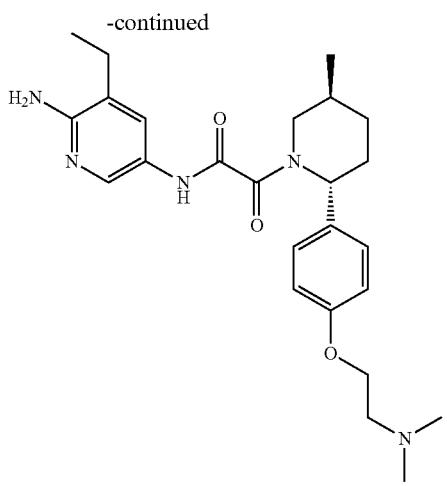

Step 1: Synthesis of (2R,5S)-tert-butyl 2-(4-(2-(dimethylamino)ethoxy)phenyl)-5-methylpiperidine-1-carboxylate tert-butyl (2R,5S)-2-(4-hydroxyphenyl)-5-methyl-piperidine-1-carboxylate (50 mg, 171.59 μmol), 2-bromo-N,N-dimethyl-ethanamine (43.97 mg, 188.75 μmol, HBr) and potassium tert-butoxide (48.14 mg, 428.99 μmol) were mixed in DMF (5 mL) and heated with stirring at 90° C. for 12 hr. Conversion after 12 hr-55%. Additionally 20 mg of 2-bromo-N,N-dimethyl-ethanamine and 25 mg of potassium tert-butoxide were added. Conversion after +24 hr-71%. Additionally 20 mg of 2-bromo-N,N-dimethyl-ethanamine and 25 mg of potassium tert-butoxide were added. Conversion after +24 hr-100%. Reaction mixture was diluted with water and extracted with 30 mL of EtOAc, dried over $Na_2SO_4$ and concentrated in vacuum to give tert-butyl (2R,5S)-2-[4-[2-(dimethylamino)ethoxy]phenyl]-5-methyl-piperidine-1-carboxylate (120 mg, crude).

LCMS(ESI): $[M]^+$ m/z: calcd 362.2; found 363.2; Rt=1.169 min.

Step 2: Synthesis of N,N-dimethyl-2-(4-((2R,5S)-5-methylpiperidin-2-yl)phenoxy)ethanamine tert-butyl (2R,5S)-2-[4-[2-(dimethylamino)ethoxy]phenyl]-5-methyl-piperidine-1-carboxylate (120 mg, 182.07 μmol) was dissolved in 5 mL of HCl/dioxane (10%) (6.64 mg, 182.07 μmol) and then 1 mL of MeOH was added for better solubility of product. After stirring for 2 hr RM was concentrated in vacuum. N,N-dimethyl-2-[4-[(2R,5S)-5-methyl-2-piperidyl]phenoxy]ethanamine (70 mg, crude, 2HCl) was obtained.

LCMS(ESI): $[M]^+$ m/z: calcd 262.2; found 263.2; Rt=0.243 min.

Step 3: Synthesis of N-(6-amino-5-ethylpyridin-3-yl)-2-((2R,5S)-2-(4-(2-(dimethylamino)ethoxy)phenyl)-5-methylpiperidin-1-yl)-2-oxoacetamide (Compound 1292

N,N-dimethyl-2-[4-[(2R,5S)-5-methyl-2-piperidyl]phenoxy]ethanamine (70 mg, 177.45 mol, 2HCl) and HATU (87.71 mg, 230.68 μmol) were mixed in DMSO (1.91 mL) and stirred for 5 min. Then 2-[(6-amino-5-ethyl-3-pyridyl)amino]-2-oxo-acetic acid (44.55 mg, 212.94 mol) was added and stirred for next 10 min. Finally TEA (89.78 mg, 887.24 μmol, 123.66 μL) was added and stirred for 2 hr. Reaction mixture was subjected to HPLC. First loading HPLC data: Device (Mobile Phase, Column): SYSTEM 2-10 min 10-50% MeOH+FA 30 mL/min (loading pump 4 mL MeOH) column: SunFire 100*19 mm, 5 microM. Second loading HPLC data: 2-10 min 10-50% water/MeOH+$NH_3$ 30 mL/min; loading pump 4 mL/min MeOH+$NH_3$; column SunFire 19*100 mm. N-(6-amino-5-ethyl-3-pyridyl)-2-[(2R,5S)-2-[4-[2-(dimethylamino)ethoxy]phenyl]-5-methyl-1-piperidyl]-2-oxo-acetamide (19.3 mg, 42.55 μmol, 23.98% yield) was obtained.

$^1$H NMR (600 MHz, DMSO-$d_6$) δ (ppm) 0.71-1.02 (m, 3H), 1.07-1.15 (m, 3H), 1.26-1.39 (m, 1H), 1.59-1.73 (m, 1H), 1.79-1.92 (m, 1H), 1.96-2.12 (m, 1H), 2.12-2.18 (m, 1H), 2.19 (s, 6H), 2.35-2.41 (m, 2H), 2.58-2.61 (m, 2H), 2.67-3.21 (m, 1H), 3.37-3.99 (m, 1H), 3.99-4.06 (m, 2H), 5.02-5.58 (m, 1H), 5.58-5.69 (m, 2H), 6.90-6.98 (m, 2H), 7.15-7.28 (m, 2H), 7.43-7.54 (m, 1H), 7.98-8.11 (m, 1H), 10.52 (s, 1H).

LCMS(ESI): $[M]^+$ m/z: calcd 453.2; found 454.2; Rt=1.532 min.

Example 273. The Synthesis of Rel-N-(6-amino-5-ethyl-3-pyridyl)-2-[(2S,4S,5S)-4-methoxy-5-methyl-2-[4-(4-methylpiperazin-1-yl)phenyl]-1-piperidyl]-2-oxo-acetamide (Compound 1159), rac-N-(6-amino-5-ethyl-3-pyridyl)-2-[(2R,4S,5R)-4-methoxy-5-methyl-2-[4-(4-methylpiperazin-1-yl)phenyl]-1-piperidyl]-2-oxo-acetamide (Compound 1349), Rel-N-(6-amino-5-ethylpyridin-3-yl)-2-((2S,4R,5S)-4-methoxy-5-methyl-2-(4-(4-methylpiperazin-1-yl)phenyl)piperidin-1-yl)-2-oxoacetamide (Compound 1089

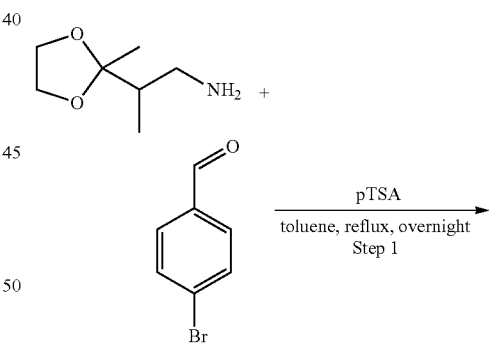

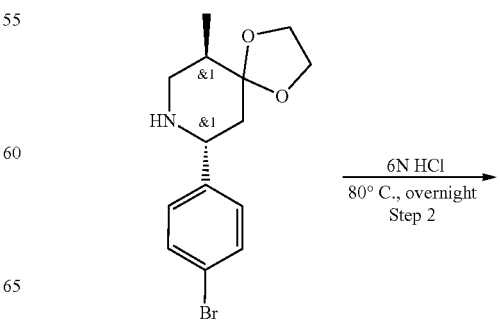

1835
-continued
1836
-continued
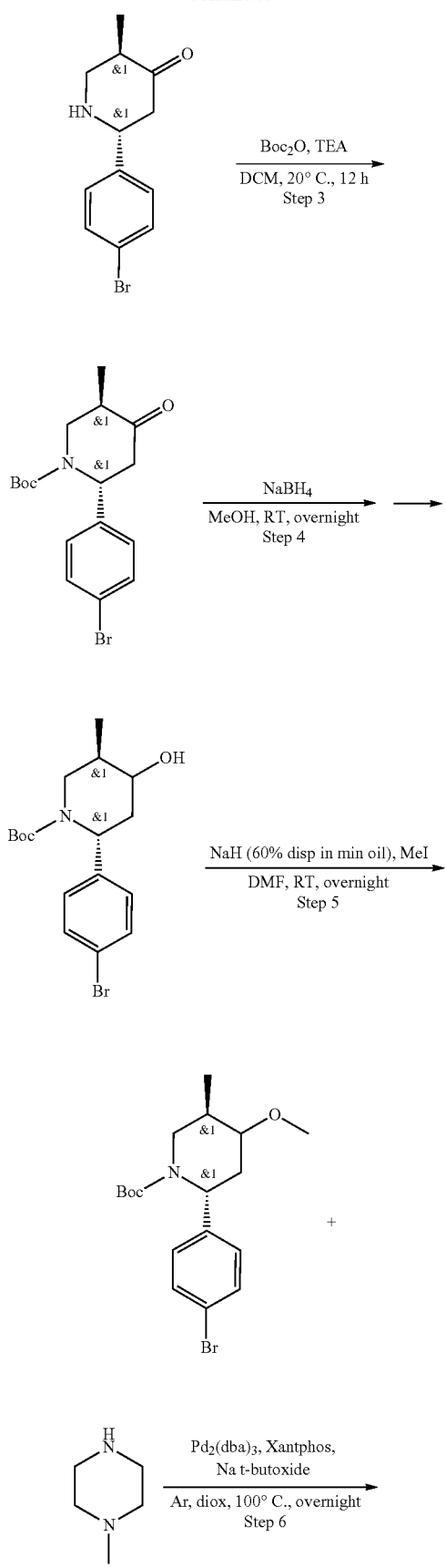
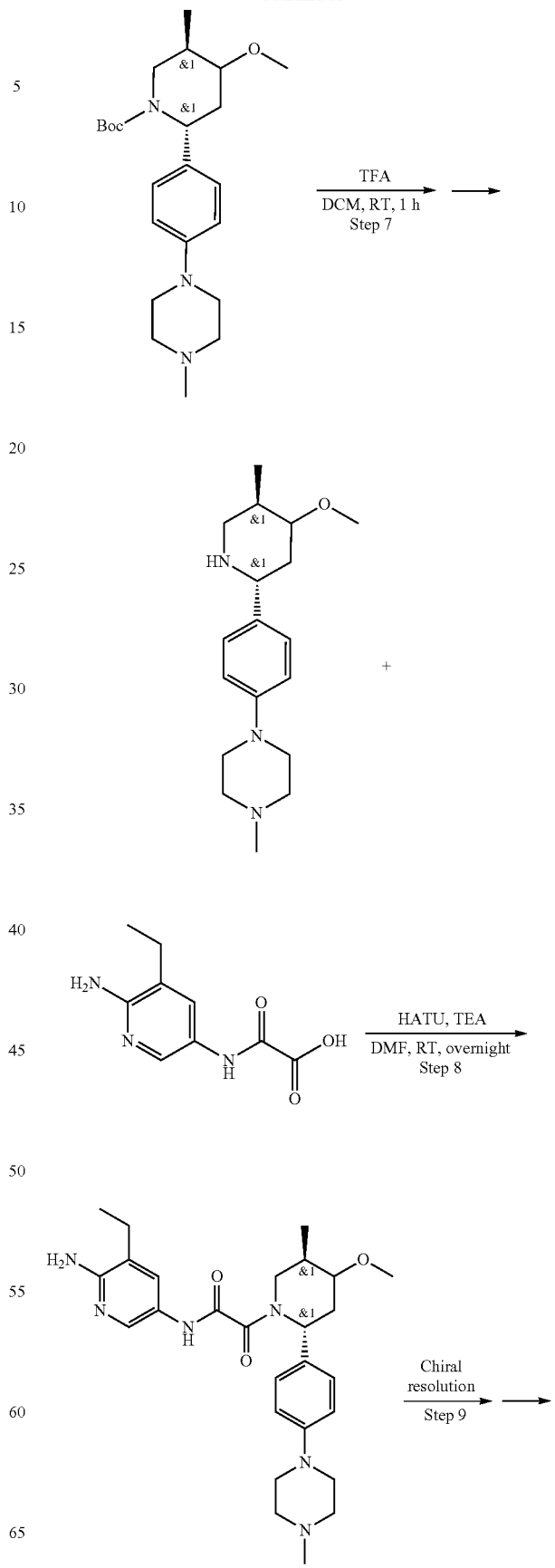

-continued

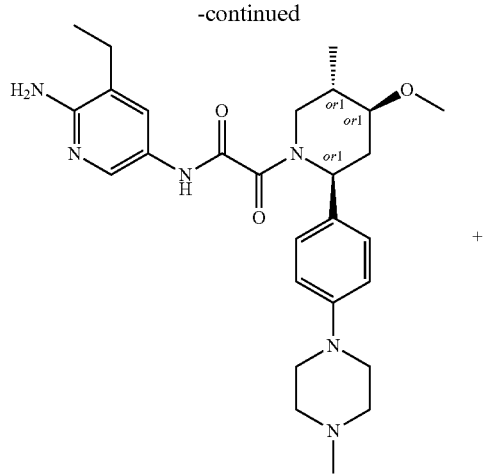

Compound 1159

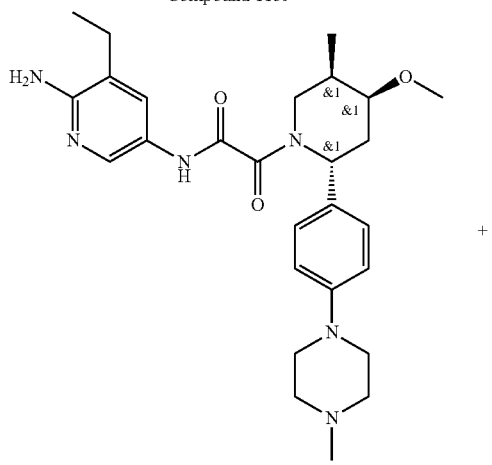

Compound 1349

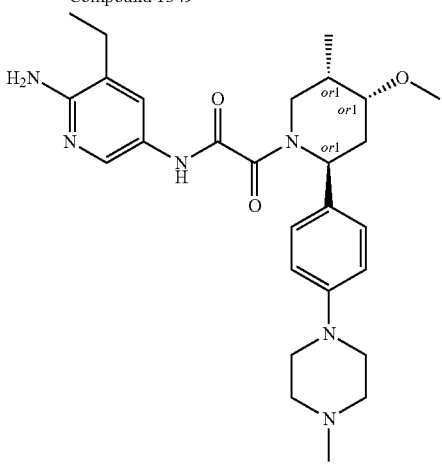

Compound 1089

Step 1: The Synthesis of rac-(6R,9R)-9-(4-bromophenyl)-6-methyl-1,4-dioxa-8-azaspiro[4.5]decane 2-(2-methyl-1,3-dioxolan-2-yl)propan-1-amine (6.9 g, 47.52 mmol) was dissolved in Toluene (150 mL) and 4-bromobenzaldehyde (8.79 g, 47.52 mmol) was added thereto followed by addition of p-TSA (24.55 g, 142.56 mmol). The resulting mixture was heated to reflux and refluxed under Dean-Stark trap overnight.

The reaction mixture was cooled and aq. $K_2CO_3$ solution (50 mL) was added. The resulting mixture was transferred to a separation funnel and an organic layer was separated. The aqueous layer was extracted with EtOAc (50 mL) and combined organic layers were dried over $Na_2SO_4$, filtered and evaporated. The residue was dissolved in $CHCl_3$ (100 mL) and the resulting mixture was extracted with aq. $NaHSO_4$ (5 g in 50 mL of water, 2*50 mL). Combined aqueous layers were washed with $CHCl_3$ (2*50 mL) and then basified with $K_2CO_3$ (10 g). The resulting mixture was extracted with $CHCl_3$ (2*50 mL) and combined organic layers were dried over $Na_2SO_4$, filtered and evaporated to obtain (6R,9R)-9-(4-bromophenyl)-6-methyl-1,4-dioxa-8-azaspiro[4.5]decane (2.7 g, 8.65 mmol, 18.20% yield).

LCMS(ESI): $[M+H]^+$ m/z: calcd 312.0; found 312.0; Rt=0.712 min.

Step 2: The Synthesis of (2R,5R)-2-(4-bromophenyl)-5-methyl-piperidin-4-one (6R,9R)-9-(4-bromophenyl)-6-methyl-1,4-dioxa-8-azaspiro[4.5]decane (2.7 g, 8.65 mmol) was dissolved in 6N HCl (80 mL) and the resulting mixture was heated at 80° C. (in an oil bath) overnight. The reaction mixture was cooled, extracted with MTBE (twice) then the aqueous layer was basified with $K_2CO_3$. The resulting mixture was extracted with $CHCl_3$ (twice) and combined organic layers were dried over $Na_2SO_4$, filtered and evaporated to obtain (2R,5R)-2-(4-bromophenyl)-5-methyl-piperidin-4-one (1 g, 3.73 mmol, 43.12% yield).

LCMS(ESI): $[M+H]^+$ m/z: calcd 270.2; found 270.2; Rt=0.812 min.

Step 3: The Synthesis of tert-butyl (2R,5R)-2-(4-bromophenyl)-5-methyl-4-oxo-piperidine-1-carboxylate (2R,5R)-2-(4-bromophenyl)-5-methyl-piperidin-4-one (2.1 g, 7.83 mmol) and triethylamine (1.19 g, 11.75 mmol, 1.64 mL) were dissolved in DCM (20 mL), then di-tert-butyl dicarbonate (1.97 g, 9.01 mmol, 2.07 mL) was added dropwise under ice/water cooling, after that the reaction mixture was stirred at 20° C. for 12 hr. After the reaction mixture was washed with $NaHSO_4$ (aq) three times, the DCM layer was dried over $Na_2SO_4$, filtered and concentrated in vacuo. The crude product was purified by FCC to obtain tert-butyl (2R,5R)-2-(4-bromophenyl)-5-methyl-4-oxo-piperidine-1-carboxylate (3 g, crude).

LCMS(ESI): $[M+H]^+$ m/z: calcd 368.2; found 368.2; Rt=1.545 min.

Step 4: The Synthesis of tert-butyl (2R,5R)-2-(4-bromophenyl)-4-hydroxy-5-methyl-piperidine-1-carboxylate Sodium Borohydride (148.95 mg, 3.94 mmol, 138.69 μL) was added portionwise to tert-butyl (2R,5R)-2-(4-bromophenyl)-5-methyl-4-oxo-piperidine-1-carboxylate (2.9 g, 7.87 mmol) in dry Methanol (30 mL) and then stirred overnight. The reaction was quenched by the addition of a saturated aqueous solution of ammonium chloride. Extract with ethyl acetate (15 mL×3) and combined organic layers were washed with saturated brine and dry over anhydrous sodium sulfate. Filtration and concentration of the filtrate under reduced pressure afforded tert-butyl (2R,5R)-2-(4-bromophenyl)-4-hydroxy-5-methyl-piperidine-1-carboxylate (2.5 g, 6.75 mmol, 85.74% yield)

Step 5: The Synthesis of tert-butyl (2R,5R)-2-(4-bromophenyl)-4-methoxy-5-methyl-piperidine-1-carboxylate tert-butyl (2R,5R)-2-(4-bromophenyl)-4-hydroxy-5-methyl-piperidine-1-carboxylate (1 g, 2.70 mmol) was dissolved in DMF (10.00 mL) and Sodium hydride (in oil dispersion) 60% dispersion in mineral oil (186.26 mg, 8.10 mmol, 310.44 µL) was added thereto. The resulting mixture was stirred for 1 hr and Methyl iodide (1.15 g, 8.10 mmol, 504.38 µL) was added to the previous mixture and the resulting mixture was stirred overnight. The reaction mixture was poured into water (30 mL) and the resulting mixture was extracted with MTBE (3*20 mL). Combined organic layers were washed with water (3*20 mL), dried over Na$_2$SO$_4$, filtered, and concentrated in vacuo. Due to the poor conversion the procedure was repeated with the residue to obtain tert-butyl (2R,5R)-2-(4-bromophenyl)-4-methoxy-5-methyl-piperidine-1-carboxylate (1.0 g, crude)

Step 6: The Synthesis of tert-butyl (2R,5R)-4-methoxy-5-methyl-2-[4-(4-methylpiperazin-1-yl)phenyl]piperidine-1-carboxylate tert-butyl (2R,5R)-2-(4-bromophenyl)-4-methoxy-5-methyl-piperidine-1-carboxylate (700.00 mg, 1.82 mmol), 1-methylpiperazine (182.44 mg, 1.82 mmol, 202.04 µL), 4,5-Bis(diphenylphosphino)-9,9-dimethylxanthene (105.39 mg, 182.15 µmol) and Sodium tert-butoxide (262.56 mg, 2.73 mmol) were mixed together in Dioxane (15 mL) and the resulting mixture was evacuated and backfilled three times with argon.

Tris(Dibenzylideneacetone)dipalladium (0) chloroform adduct (94.27 mg, 91.07 µmol) was added to the previous mixture and the resulting mixture was heated at 100° C. (oil bath) overnight. The reaction mixture was cooled and diluted with water (5 mL). The resulting mixture was extracted with EtOAc (2*5 mL). Combined organic layers were washed with brine (2 mL), dried over Na$_2$SO$_4$, filtered and evaporated. The residue was purified by column chromatography to obtain tert-butyl (2R,5R)-4-methoxy-5-methyl-2-[4-(4-methylpiperazin-1-yl)phenyl]piperidine-1-carboxylate (0.6 g, crude).

LCMS(ESI): [M+H]$^+$ m/z: calcd 402.2; found 402.2; Rt=1.082 min.

Step 7: The Synthesis of 1-[4-[(2R,5R)-4-methoxy-5-methyl-2-piperidyl]phenyl]-4-methyl-Piperazine tert-butyl (2R,5R)-4-methoxy-5-methyl-2-[4-(4-methylpiperazin-1-yl)phenyl]piperidine-1-carboxylate (400.00 mg, 991.19 µmol) was dissolved in DCM (1.5 mL) and TFA (1.5 mL) was added. The resulting mixture was stirred for 1 hr. The reaction mixture was poured into aq. K$_2$CO$_3$ solution and the resulting mixture was extracted with DCM. Combined organic layers were dried over Na$_2$SO$_4$, filtered and evaporated to obtain 1-[4-[(2R,5R)-4-methoxy-5-methyl-2-piperidyl]phenyl]-4-methyl-piperazine which was used in the next step without further purification.

LCMS(ESI): [M+H]$^+$ m/z: calcd 304.2; found 304.2; Rt=0.227 min.

Step 8: The Synthesis of N-(6-amino-5-ethyl-3-pyridyl)-2-[(2R,5R)-4-methoxy-5-methyl-2-[4-(4-methylpiperazin-1-yl)phenyl]-1-piperidyl]-2-oxo-acetamide 1-[4-[(2R,5R)-4-methoxy-5-methyl-2-piperidyl]phenyl]-4-methyl-piperazine (300.00 mg, 988.66 µmol) was dissolved in DMF (5 mL) and Triethylamine (1.00 g, 9.89 mmol, 1.38 mL) was added, followed by 2-[(6-amino-5-ethyl-3-pyridyl)amino]-2-oxo-acetic acid (206.83 mg, 988.66 µmol). Then the HATU (563.88 mg, 1.48 mmol) was added dropwise and the reaction mixture was stirred overnight. The next day it was evaporated in vacuo and purified by HPLC (1.2-10 min 40-60% methanol+nh3 30 min (loading pump 4 mL methanol), column: SunFire 100*19 mm, 5 microM; 2.2-10 min 0-25% acetonitrile+fa 30 min (loading pump 4 mL acetonitrile), column: SunFire 100*19 mm, 5 microM) to obtain N-(6-amino-5-ethyl-3-pyridyl)-2-[(2R,5R)-4-methoxy-5-methyl-2-[4-(4-methylpiperazin-1-yl)phenyl]-1-piperidyl]-2-oxo-acetamide (400.0 mg, crude).

LCMS(ESI): [M+2H]$^+$ m/z: calcd 496.2; found 496.2; Rt=0.802 min.

Step 9: The Synthesis of Rel-N-(6-amino-5-ethyl-3-pyridyl)-2-[(2S,4S,5S)-4-methoxy-5-methyl-2-[4-(4-methylpiperazin-1-yl)phenyl]-1-piperidyl]-2-oxo-acetamide (Compound 1159), rac-N-(6-amino-5-ethyl-3-pyridyl)-2-[(2R,4S,5R)-4-methoxy-5-methyl-2-[4-(4-methylpiperazin-1-yl)phenyl]-1-piperidyl]-2-oxo-acetamide (Compound 1349), Rel-N-(6-amino-5-ethylpyridin-3-yl)-2-((2S,4R,5S)-4-methoxy-5-methyl-2-(4-(4-methylpiperazin-1-yl)phenyl)piperidin-1-yl)-2-oxoacetamide N-(6-amino-5-ethyl-3-pyridyl)-2-[(2R,5R)-4-methoxy-5-methyl-2-[4-(4-methylpiperazin-1-yl)phenyl]-1-piperidyl]-2-oxo-acetamide (17.60 mg, 35.58 µmol) was chiral separated (Column: Chiralpak IB (250*20 mm, 5 mkm); Mobile phase: Hexane-IPA-MeOH, 60-20-20. Flow Rate: 10 mL/min; Column Temperature: 24° C.; Wavelength: 205 nm. RetTime (isomer A)=22.31 min; RetTime (isomer B)=25.87 min Column: Chiralcel OD-H (250*20 mm, 5 mkm); Mobile phase: Hexane-IPA-MeOH, 80-10-10. Flow Rate: 12 mL/min; Column Temperature: 24° C.; Wavelength: 205 nm. RetTime (isomer A)=74.42 min; RetTime (isomer B)=90.87 min) to obtain N-(6-amino-5-ethyl-3-pyridyl)-2-[(2S,4S,5S)-4-methoxy-5-methyl-2-[4-(4-methylpiperazin-1-yl)phenyl]-1-piperidyl]-2-oxo-acetamide (6.17 mg, 12.47 µmol, 35.06% yield) and Compound 1159: LCMS(ESI): [M+H]$^+$ m/z: calcd 495.2; found 495.2; Rt=1.419 min.

Compound 1349: LCMS(ESI): [M+H]$^+$ m/z: calcd 495.2; found 495.2; Rt=1.440 min.

Example 274. The Synthesis of N-(6-amino-5-eth-ylpyridin-3-yl)-2-((2R,5S)-5-methyl-2-(3-(1-methylpyrrolidin-3-yl)phenyl)piperidin-1-yl)-2-oxoacetamide (Compound 1342

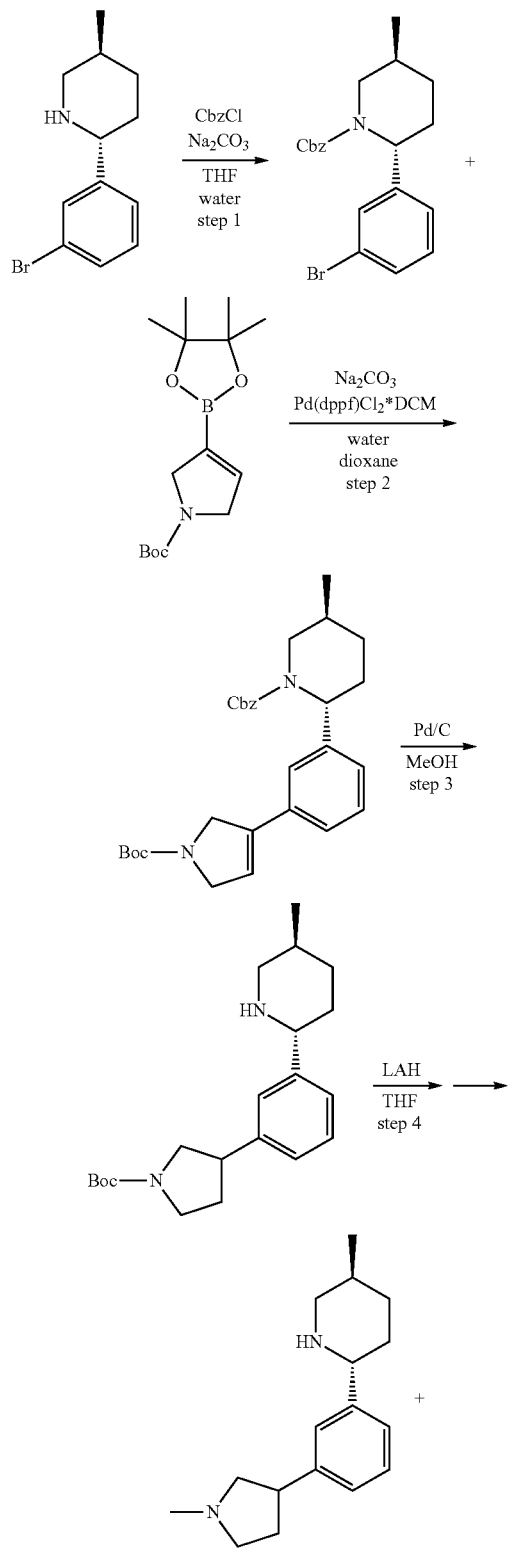

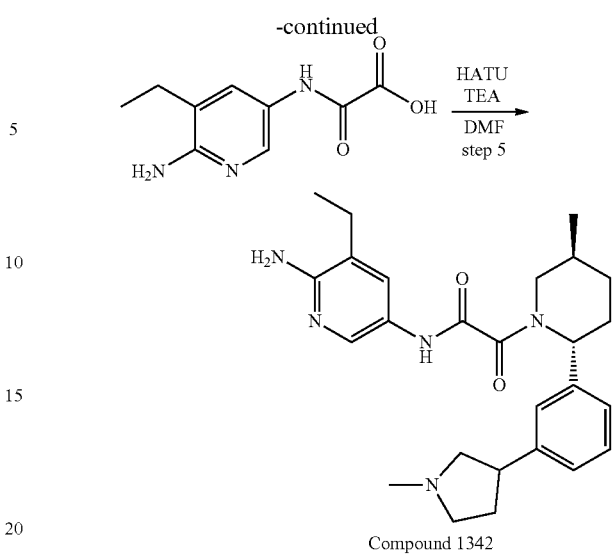

Compound 1342

Step 1: Synthesis of (2R,5S)-benzyl 2-(3-bromophenyl)-5-methylpiperidine-1-carboxylate (2R,5S)-2-(3-bromophenyl)-5-methyl-piperidine (2.7 g, 10.62 mmol) was dissolved in THF (25 mL) and sodium carbonate (2.25 g, 21.25 mmol, 889.35 µL) was added thereto followed by the addition of water (30 mL). The resulting mixture was cooled to 0° C. in an ice bath and a solution of CbzCl (1.90 g, 11.15 mmol, 1.59 mL) in THF (5 mL) was added dropwise at 0° C. After addition completed, the reaction mixture was allowed to warm to rt and stirred overnight. The reaction mixture was concentrated in vacuum and the residue was diluted with water (50 ml). The resulting mixture was extracted with MTBE (2*50 ml) and combined organic layers were dried over $Na_2SO_4$, filtered, and concentrated in vacuum to obtain benzyl (2R,5S)-2-(3-bromophenyl)-5-methyl-piperidine-1-carboxylate (4.27 g, crude).

LCMS(ESI): $[M]^+$ m/z: calcd 388.2; found 389.2; Rt=1.636 min.

Step 2: Synthesis of (2R,5S)-benzyl 2-(3-(1-(tert-butoxycarbonyl)-2,5-dihydro-1H-pyrrol-3-yl)phenyl)-5-methylpiperidine-1-carboxylate Benzyl(2R,5S)-2-(3-bromophenyl)-5-methyl-piperidine-1-carboxylate (1 g, 2.58 mmol), tert-butyl 3-(4,4,5,5-tetramethyl-1,3,2-dioxaborolan-2-yl)-2,5-dihydropyrrole-1-carboxylate (874.22 mg, 2.96 mmol) and sodium carbonate (545.92 mg, 5.15 mmol, 215.61 µL) were mixed together in a mixture of dioxane (7.5 mL) and water (2.5 mL). A flask containing the previous mixture was evacuated and back-filled three times with argon. Pd(dppf)Cl$_2$*DCM (105.16 mg, 128.77 µmol) was added to the previous mixture and the resulting mixture was heated at 90° C. overnight. The reaction mixture was concentrated in vacuum and the residue was diluted with water (20 ml). The resulting mixture was extracted with EtOAc (2*30 ml) and combined organic layers were dried over $Na_2SO_4$, filtered, and concentrated in vacuum. The residue was purified by column chromatography to obtain benzyl (2R,5S)-2-[3-(1-tert-butoxycarbonyl-2,5-dihydropyrrol-3-yl)phenyl]-5-methyl-piperidine-1-carboxylate (750 mg, 1.57 mmol, 61.10% yield).

LCMS(ESI): [M-Boc]$^+$ m/z: calcd 376.2; found 377.2; Rt=1.594 min.

Step 3: Synthesis of tert-butyl 3-(3-((2R,5S)-5-methylpiperidin-2-yl)phenyl)Pyrrolidine-1-carboxylate Benzyl(2R,5S)-2-[3-(1-tert-butoxycarbonyl-2,5-dihydropyrrol-3-yl)phenyl]-5-methyl-piperidine-1-carboxylate (750 mg, 1.57 mmol) was dissolved in MeOH (10 mL) and palladium, 10% on carbon, type 487, dry (251.20 mg, 2.36 mmol) was added thereto. The resulting mixture was hydrogenated at 50 atm over weekend. The catalyst was filtered off and the filtrate was concentrated in vacuum. The residue was re-dissolved in MeOH (10 mL) and palladium, 10% on carbon, type 487, dry (251.20 mg, 2.36 mmol) was added thereto. The resulting mixture was hydrogenated at 50 atm overnight. The catalyst was filtered off and the filtrate was concentrated in vacuum to obtain tert-butyl 3-[3-[(2R,5S)-5-methyl-2-piperidyl]phenyl]pyrrolidine-1-carboxylate (416 mg, 1.21 mmol, 76.74% yield).

LCMS(ESI): [M]f m/z: calcd 344.2; found 345.2; Rt=1.160 min.

Step 4: Synthesis of (2R,5S)-5-methyl-2-(3-(1-methylpyrrolidin-3-yl)phenyl)piperidine LAH (152.04 mg, 4.01 mmol) was dissolved in THF (5 mL) and a solution of tert-butyl 3-[3-[(2R,5S)-5-methyl-2-piperidyl]phenyl]pyrrolidine-1-carboxylate (276 mg, 801.19 μmol) in THE (2 mL) was added dropwise. The resulting mixture was heated to reflux and refluxed for 3 hr. The reaction mixture was allowed to cool to rt and stirred overnight. Water (150 mkl) was added to the reaction mixture followed by the addition of aq. KOH solution (150 mkl) and water (300 mkl). The reaction mixture was stirred for 30 min and filtered. The filter cake was washed with THE (10 ml) and the filtrate was concentrated in vacuum to obtain (2R,5S)-5-methyl-2-[3-(1-methylpyrrolidin-3-yl)phenyl]piperidine (227 mg, crude).

LCMS(ESI): [M]$^+$ m/z: calcd 258.2; found 259.2; Rt=0.644 min.

Step 5: Synthesis of N-(6-amino-5-ethylpyridin-3-yl)-2-((2R,5S)-5-methyl-2-(3-(1-methylpyrrolidin-3-yl)phenyl)piperidin-1-yl)-2-oxoacetamide (Compound 1342

(2R,5S)-5-methyl-2-[3-(1-methylpyrrolidin-3-yl)phenyl]piperidine (292 mg, 1.13 mmol), 2-[(6-amino-5-ethyl-3-pyridyl)amino]-2-oxo-acetic acid (236.40 mg, 1.13 mmol) and TEA (571.74 mg, 5.65 mmol, 787.52 μL) were mixed together in DMF (3 mL) and HATU (515.60 mg, 1.36 mmol) was added thereto. The resulting mixture was stirred overnight. The reaction mixture was submitted to HPLC and purified (2-10 min 60-80% MeOH+NH$_3$30 min (loading pump 4 ml MeOH), column: SunFire 100*19 mm, 5 microM) to obtain N-(6-amino-5-ethyl-3-pyridyl)-2-[(2R,5S)-5-methyl-2-[3-(1-methylpyrrolidin-3-yl)phenyl]-1-piperidyl]-2-oxo-acetamide (87.9 mg, 195.51 μmol, 17.30% yield) and N-(6-amino-5-ethyl-3-pyridyl)-2-[(2R,5S)-5-methyl-2-[3-(1-methylpyrrolidin-3-yl)phenyl]-1-piperidyl]-2-oxo-acetamide (54.3 mg, 120.78 mol, 10.69% yield).

$^1$H NMR (600 MHz, DMSO-d$_6$) δ (ppm) 0.99-1.03 (m, 3H), 1.06-1.13 (m, 3H), 1.28-1.38 (m, 1H), 1.62-1.75 (m, 2H), 1.82-1.92 (m, 1H), 1.96-2.25 (m, 4H), 2.25-2.27 (m, 3H), 2.31-2.36 (m, 1H), 2.38-2.43 (m, 2H), 2.51-2.58 (m, 2H), 2.72-3.24 (m, 2H), 3.43-4.03 (m, 1H), 5.12-5.57 (m, 1H), 5.58-5.67 (m, 2H), 7.09-7.20 (m, 3H), 7.26-7.32 (m, 1H), 7.42-7.52 (m, 1H), 7.98-8.07 (m, 1H), 10.45-10.54 (m, 1H).

LCMS(ESI): [M]$^+$ m/z: calcd 449.2; found 450.2; Rt=2.033 min.

Example 275. The Synthesis of N-(6-amino-5-ethyl-3-pyridyl)-2-[(2S,4S,5S)-2-(1,3-benzothiazol-5-yl)-4-Isopropoxy-5-methyl-1-piperidyl]-2-oxo-acetamide (Compound 1343) and N-(6-amino-5-ethyl-3-pyridyl)-2-[(2S,4R,5S)-2-(1,3-benzothiazol-5-yl)-4-Isopropoxy-5-methyl-1-piperidyl]-2-oxo-acetamide (Compound 1094

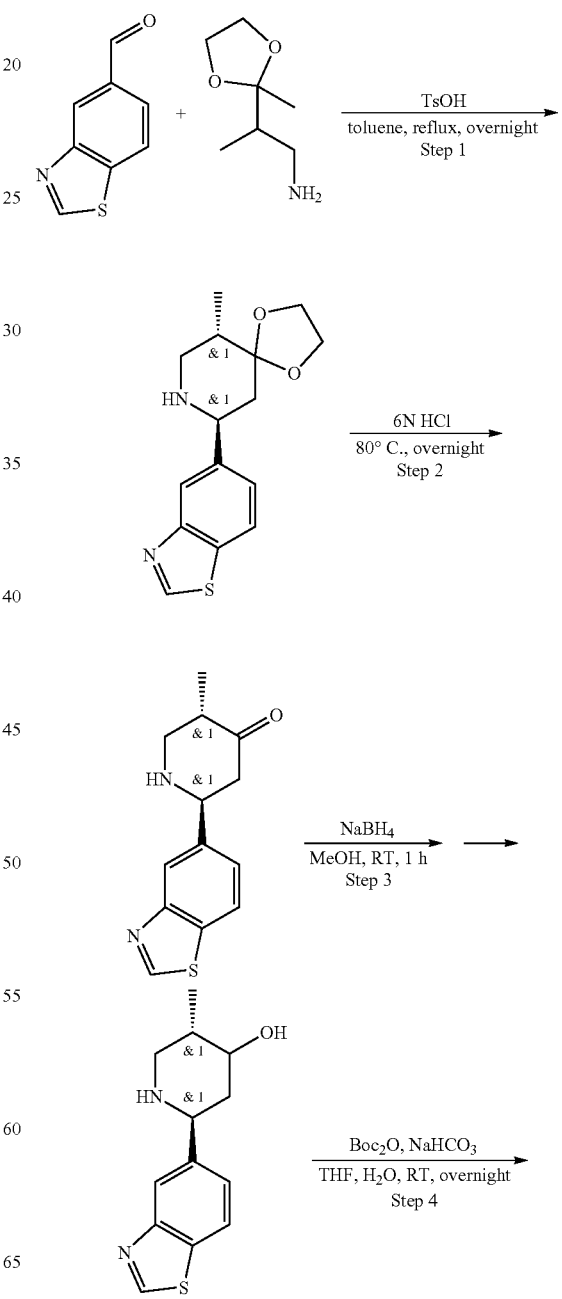

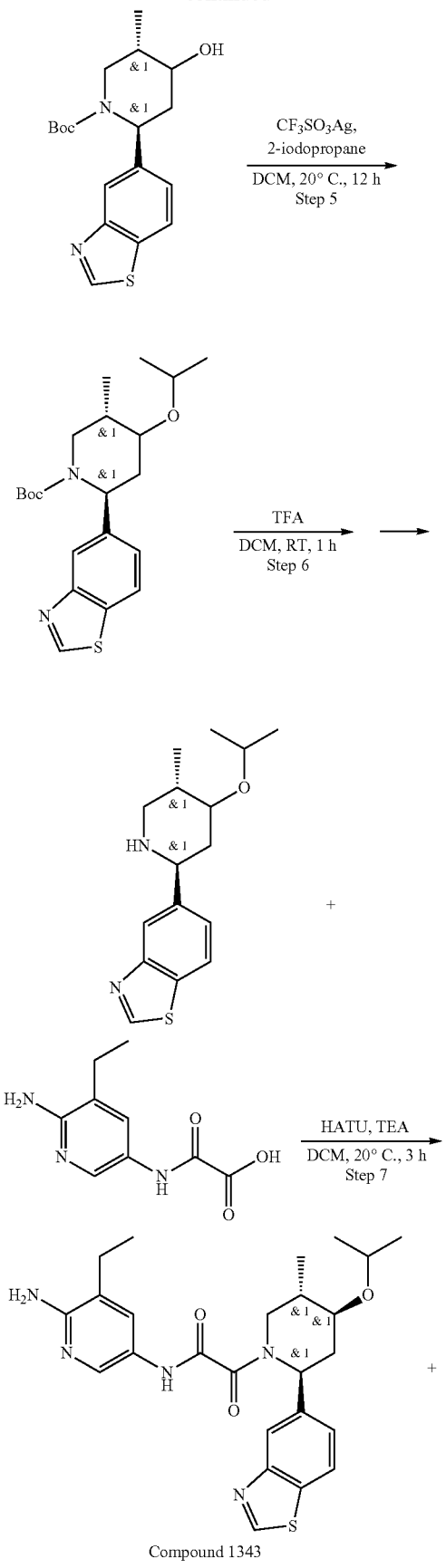

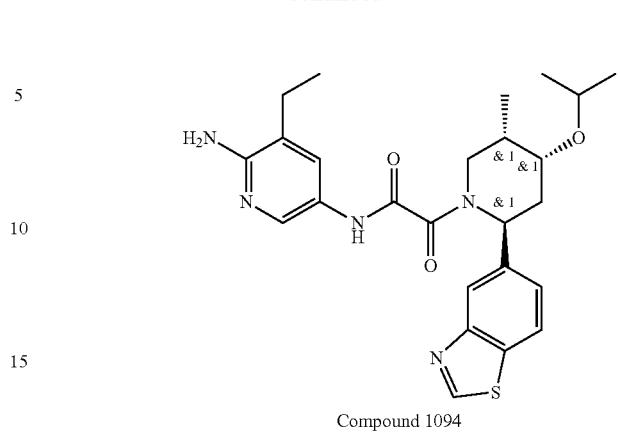

Compound 1094

Step 7: The Synthesis of N-(6-amino-5-ethyl-3-pyridyl)-2-[(2S,4S,5S)-2-(1,3-benzothiazol-5-yl)-4-Isopropoxy-5-methyl-1-piperidyl]-2-oxo-acetamide (Compound 1343) and N-(6-amino-5-ethyl-3-pyridyl)-2-[(2S,4R,5S)-2-(1,3-benzothiazol-5-yl)-4-Isopropoxy-5-methyl-1-piperidyl]-2-oxo-acetamide (Compound 1094

5-[(2S,5S)-4-Isopropoxy-5-methyl-2-piperidyl]-1,3-benzothiazole (0.085 g, 292.68 mol), TEA (88.85 mg, 878.03 µmol, 122.38 µL) and 2-[(6-amino-5-ethyl-3-pyridyl)amino]-2-oxo-acetic acid (61.23 mg, 292.68 µmol) were dissolved in DMF (4 mL) and HATU (122.41 mg, 321.94 µmol) was added in one portion. The resulting mixture was stirred for 3 hr at 20° C. The crude reaction mixture was purified by reverse phase HPLC (2-10 min 50-65% methanol+NH$_3$Flow 30 mL/min (loading pump 4 mL methanol), column: SunFire 100*19 mm, 5 microM). The desired products N-(6-amino-5-ethyl-3-pyridyl)-2-[(2S,4S,5S)-2-(1,3-benzothiazol-5-yl)-4-isopropoxy-5-methyl-1-piperidyl]-2-oxo-acetamide (4.10 mg, 8.51 µmol, 2.91% yield) and N-(6-amino-5-ethyl-3-pyridyl)-2-[(2S,4R,5S)-2-(1,3-benzothiazol-5-yl)-4-isopropoxy-5-methyl-1-piperidyl]-2-oxo-acetamide (0.0029 g, 6.02 µmol, 2.06% yield) were isolated as a light-yellow solids.

Compound 1343: $^1$H NMR (600 MHz, dmso) δ 0.92 (d, 3H), 1.02-1.05 (m, 6H), 1.13 (t, 3H), 1.84-2.01 (m, 1H), 2.03-2.13 (m, 1H), 2.32-2.36 (m, 1H), 2.39-2.43 (m, 2H), 2.77-3.24 (m, 1H), 3.52-4.27 (m, 3H), 5.44-5.63 (m, 1H), 5.64-5.98 (m, 2H), 7.42-7.48 (m, 1H), 7.48-7.56 (m, 1H), 7.96-8.02 (m, 1H), 8.02-8.11 (m, 1H), 8.17-8.25 (m, 1H), 9.34-9.45 (m, 1H).

LCMS(ESI): [M+H]$^+$ m/z: calcd 482.2; found 482.2; Rt=0.934 min.

Compound 1094: $^1$H NMR (600 MHz, dmso) δ 0.59-0.69 (m, 3H), 0.87-0.93 (m, 3H), 1.02-1.14 (m, 6H), 1.74-1.84 (m, 1H), 2.22-2.30 (m, 2H), 2.37-2.43 (m, 2H), 3.39-3.60 (m, 3H), 3.72-4.11 (m, 1H), 5.35-5.53 (m, 1H), 5.55-5.67 (m, 2H), 7.24-7.46 (m, 1H), 7.47-7.71 (m, 1H), 7.84-8.06 (m, 2H), 8.06-8.28 (m, 1H), 9.28-9.39 (m, 1H), 10.35 (br s, 1H).

LCMS(ESI): [M+H]$^+$ m/z: calcd 482.2; found 482.2; Rt=2.647 min.

Example 276. The Synthesis of N-(6-amino-5-ethylpyridin-3-yl)-2-((2R,5S)-5-methyl-2-(2-morpholinobenzo[d]thiazol-5-yl)piperidin-1-yl)-2-oxoacetamide (Compound 1267)

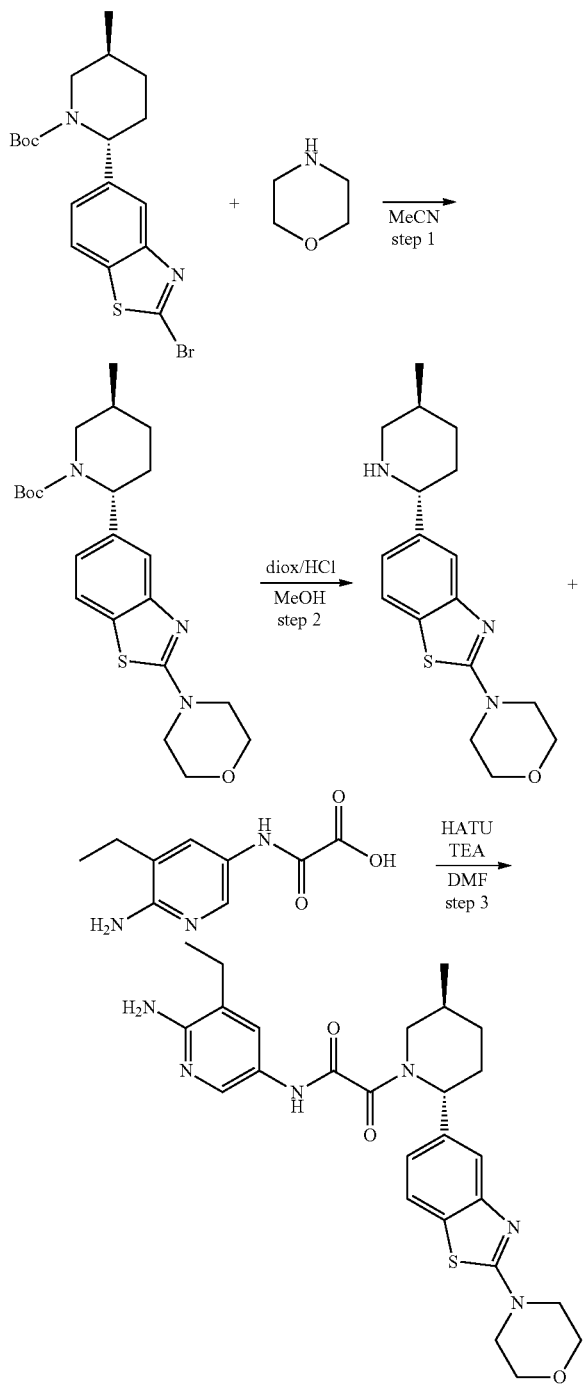

Step 1: Synthesis of (2R,5S)-tert-butyl 5-methyl-2-(2-morpholinobenzo[d]thiazol-5-yl)piperidine-1-carboxylate Morpholine (847.15 mg, 9.72 mmol, 850.55 µL) was added in one portion at 25° C. to a solution of tert-butyl (2R,5S)-2-(2-bromo-1,3-benzothiazol-5-yl)-5-methyl-piperidine-1-carboxylate (0.8 g, 1.94 mmol) in MeCN (15 mL). The resulting mixture was stirred at 70° C. for 12 hr, then cooled down and concentrated in vacuum. The residue was basified to pH 11 with 10% aqueous sodium hydroxide solution and extracted with DCM (2*25 ml). The combined organic extracts were dried over sodium sulphate and concentrated in vacuum to afford tert-butyl (2R,5S)-5-methyl-2-(2-morpholino-1,3-benzothiazol-5-yl)piperidine-1-carboxylate (0.7 g, 1.68 mmol, 86.20% yield) as brown solid, which was used directly in the next step.

LCMS(ESI): [M]+ m/z: calcd 417.2; found 418.2; Rt=1.593 min.

Step 2: Synthesis of 4-(5-((2R,5S)-5-methylpiperidin-2-yl)benzo[d]thiazol-2-yl)morpholine Hydrogen chloride solution 4.0 M in dioxane (21.00 g, 80.06 mmol, 20 mL, 13.9% purity) was added in one portion to a stirred solution of tert-butyl (2R,5S)-5-methyl-2-(2-morpholino-1,3-benzothiazol-5-yl)piperidine-1-carboxylate (0.7 g, 1.68 mmol) in MeOH (15 mL). The resulting mixture was stirred at 25° C. for 12 hr, and then evaporated to dryness in vacuum to afford crude 4-[5-[(2R,5S)-5-methyl-2-piperidyl]-1,3-benzothiazol-2-yl]morpholine (0.65 g, 1.67 mmol, 99.33% yield, 2HCl) as brown solid, which was used directly in the next step.

LCMS(ESI): [M]+ m/z: calcd 317.2; found 318.2; Rt=0.934 min.

Step 3: Synthesis of N-(6-amino-5-ethylpyridin-3-yl)-2-((2R,5S)-5-methyl-2-(2-morpholinobenzo[d]thiazol-5-yl)piperidin-1-yl)-2-oxoacetamide (Compound 1267

HATU (219.16 mg, 576.38 µmol) was added in small portions over 0.5 hr period to a stirred mixture of 4-[5-[(2R,5S)-5-methyl-2-piperidyl]-1,3-benzothiazol-2-yl]morpholine (150 mg, 384.25 µmol, 2HCl), 2-[(6-amino-5-ethyl-3-pyridyl)amino]-2-oxo-acetic acid (160.77 mg, 768.50 µmol) and triethyl amine (466.59 mg, 4.61 mmol, 642.68 µL) in DMF (3 mL) at 25° C. The resulting mixture was stirred at 25° C. for 12 hr and then submitted to reverse phase HPLC (column: YMC Triart C18 100×20 mm, 5 um; mobile phase: 40-40-80% 0-1-6 min H2O/MeOH/0.1% NH4OH, flow rate: 30 ml/min (loading pump 4 ml/min methanol) afford Compound 1267 N-(6-amino-5-ethyl-3-pyridyl)-2-[(2R,5S)-5-methyl-2-(2-morpholino-1,3-benzothiazol-5-yl)-1-piperidyl]-2-oxo-acetamide (62 mg, 121.90 µmol, 31.72% yield). 2 mg of this product was shipped, the rest of the amount was repurified by preparative chiral HPLC (Column: Chiralpak IC—III (250*20 mm, 5 mkm); Mobile phase: IPA-MeOH 50-50; Flow Rate: 10 mL/min) to afford 2nd lot of the product Compound 1267 N-(6-amino-5-ethyl-3-pyridyl)-2-oxo-2-[rac-(2R,5S)-5-methyl-2-(2-morpholino-1,3-benzothiazol-5-yl)-1-piperidyl]acetamide (44.6 mg, 87.69 µmol, 22.82% yield) (Ret. Time=45.951 min.).

Compound 1267: $^1$H NMR (600 MHz, DMSO-$d_6$) δ (ppm) 0.97-1.05 (m, 3H), 1.06-1.15 (m, 3H), 1.26-1.39 (m, 1H), 1.62-1.76 (m, 1H), 1.79-1.94 (m, 1H), 2.01-2.19 (m, 1H), 2.21-2.32 (m, 1H), 2.33-2.37 (m, 1H), 2.39-2.42 (m, 1H), 2.74-3.25 (m, 1H), 3.41-3.49 (m, 0.7H), 3.51-3.56 (m, 4H), 3.68-3.73 (m, 4H), 3.98-4.06 (m, 0.3H), 5.15-5.67 (m, 3H), 7.02-7.12 (m, 1H), 7.35-7.53 (m, 2H), 7.71-7.82 (m, 1H), 7.98-8.10 (m, 1H), 10.46-10.64 (m, 1H).

LCMS(ESI): [M]+ m/z: calcd 508.2; found 509.2; Rt=2.757 min.
Example 277. The Synthesis of N-[6-amino-5-[(3S)-tetrahydrofuran-3-yl]-3-pyridyl]-2-[(2R,5S)-5-methyl-2-[2-(1-methyl-4-piperidyl)-1,3-benzothiazol-5-yl]-1-piperidyl]-2-oxo-acetamide (Compound 1154) and N-[6-amino-5-[(3R)-tetrahydrofuran-3-yl]-3-pyridyl]-2-[(2R,5S)-5-methyl-2-[2-(1-methyl-4-piperidyl)-1,3-benzothiazol-5-yl]-1-piperidyl]-2-oxo-acetamide (Compound 1312
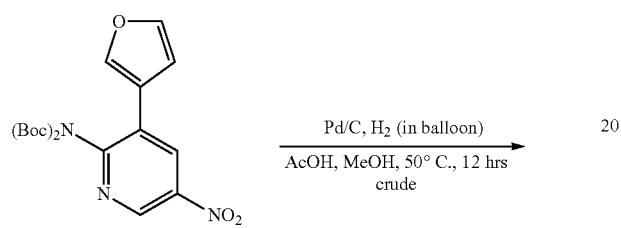
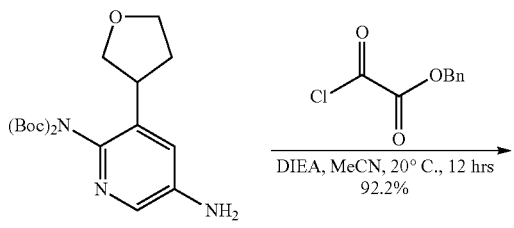
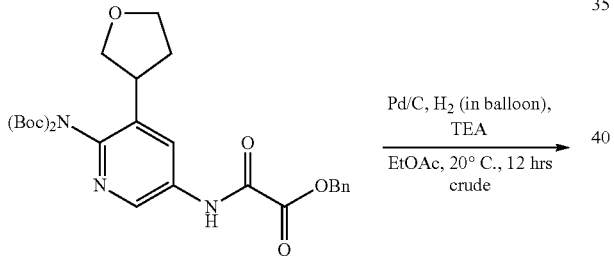
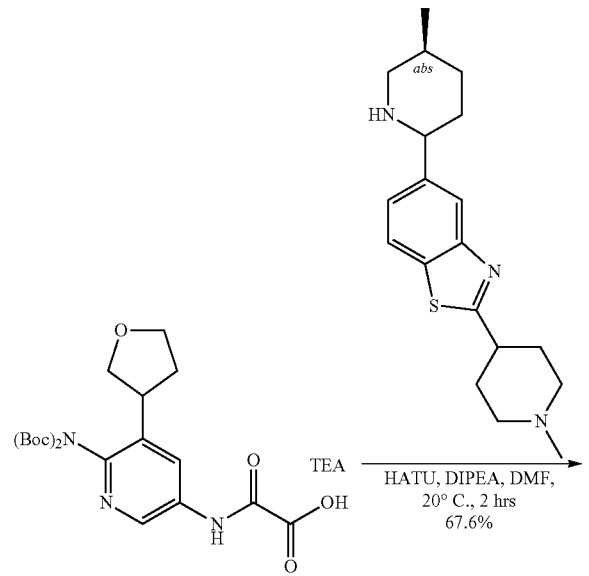
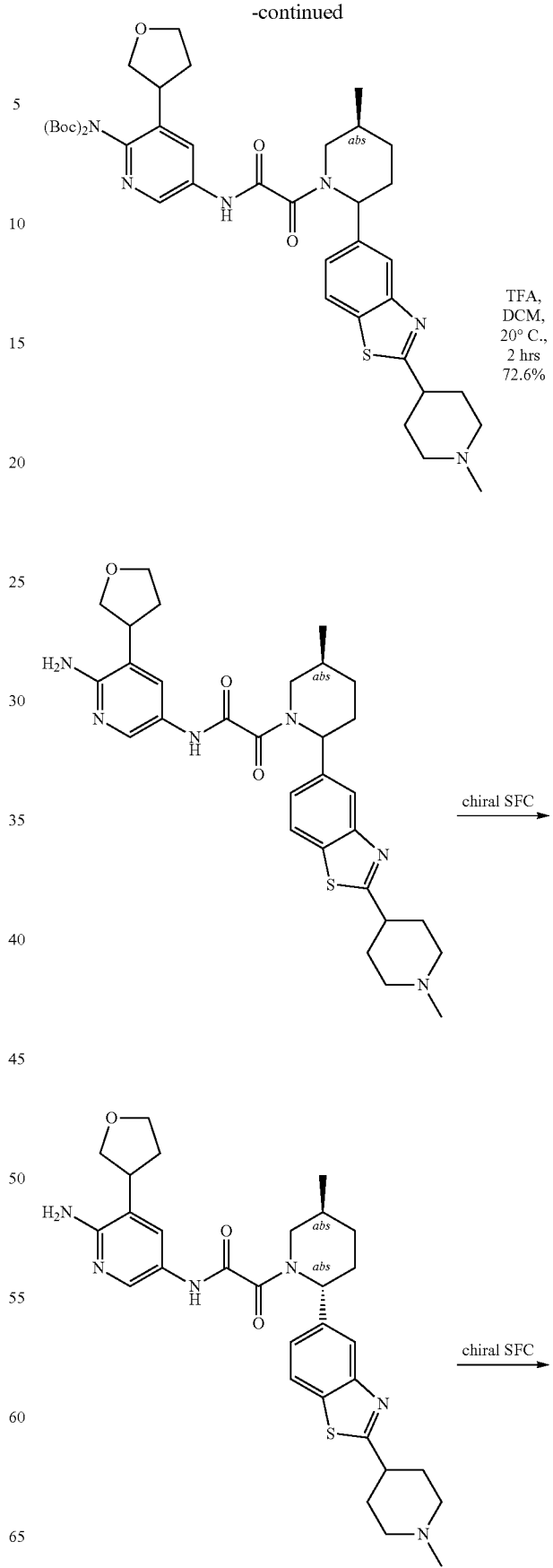

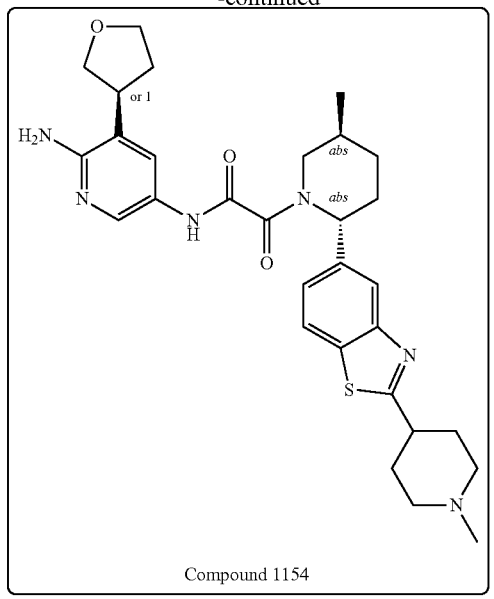

Compound 1154

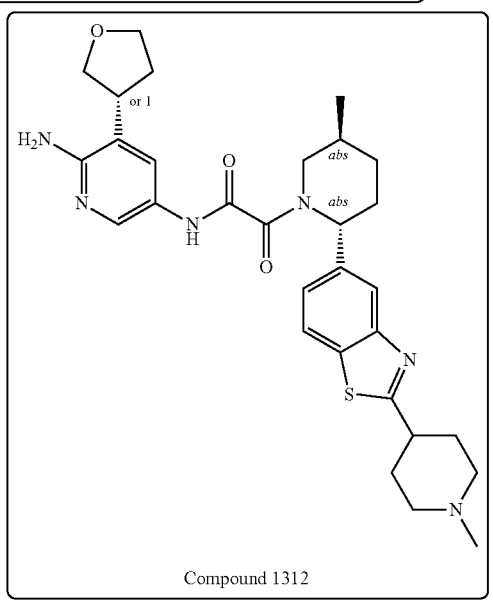

Compound 1312

Step 1: Synthesis of tert-butyl N-(5-amino-3-tetrahydrofuran-3-yl-2-pyridyl)-N-tert-butoxycarbonyl-carbamate A mixture of tert-butyl N-tert-butoxycarbonyl-N-[3-(3-furyl)-5-nitro-2-pyridyl]carbamate (1 g, 2.47 mmol), MeOH (6 mL), AcOH (5 mL, 2.47 mmol) and Pd/C (400 mg, 10% Pd/C with 50% water, wt %) was stirred at 50° C. for 12 hours under hydrogen (in balloon). The resulting mixture was filtered and concentrated under reduced pressure to give tert-butyl N-(5-amino-3-tetrahydrofuran-3-yl-2-pyridyl)-N-tert-butoxycarbonyl-carbamate (1.2 g, crude, 2CH₃COOH) as white solid.

Step 2: Synthesis of benzyl 2-[[6-[bis(tert-butoxycarbonyl)amino]-5-tetrahydrofuran-3-yl-3-pyridyl]amino]-2-oxo-acetate A mixture of tert-butyl N-(5-amino-3-tetrahydrofuran-3-yl-2-pyridyl)-N-tert-butoxycarbonyl-carbamate (1.2 g, 2.40 mmol, 2CH₃COOH), benzyl 2-chloro-2-oxo-acetate (1 g, 5.04 mmol), DIPEA (2 mL, 11.5 mmol) in MeCN (15 mL) was stirred at 20° C. for 12 hours. The resulting mixture was quenched by addition of water (50 mL) and extracted with EtOAc (100 mL*3). The combined organic layer was washed with saturated NH₄Cl aqueous solution (100 mL), brine (100 mL), dried over anhydrous Na₂SO₄, filtered and concentrated under reduced pressure. The residue was purified by flash chromatography (ISCO®; 25 g AgelaFlash Silica Flash Column, petroleum ether/EtOAc with EtOAc from 0~50%, flow rate=30 mL/min, 254 nm) to afford benzyl 2-[[6-[bis(tert-butoxycarbonyl)amino]-5-tetrahydrofuran-3-yl-3-pyridyl]amino]-2-oxo-acetate (1.2 g, 92.2% yield) as white solid. $^1$H NMR (400 MHz, methanol-d4) δ ppm 8.73 (d, J=2.3 Hz, 1H), 8.34 (d, J=2.3 Hz, 1H), 7.19-7.41 (m, 5H), 4.60 (s, 2H), 4.11-4.15 (m, 2H), 4.03 (t, J=7.9 Hz, 1H), 3.73 (dd, J=8.5, 5.5 Hz, 1H), 3.37-3.50 (m, 1H), 2.33-2.48 (m, 1H), 1.94-2.00 (m, 1H), 1.40 (s, 18H); LCMS (ESI) [M+H]⁺ m/z: calcd 542.2, found 542.3.

Step 3: Synthesis of 2-[[6-[bis(tert-butoxycarbonyl)amino]-5-tetrahydrofuran-3-yl-3-pyridyl]amino]-2-oxo-acetic acid To a mixture of benzyl 2-[[6-[bis(tert-butoxycarbonyl)amino]-5-tetrahydrofuran-3-yl-3-pyridyl]amino]-2-oxo-acetate (1.2 g, 2.22 mmol) in EtOAc (15 mL) were added TEA (0.93 mL, 6.67 mmol) and Pd/C (130 mg, 10% Pd/C with 50% water, wt %). The resulting mixture was sealed and degassed under vacuum and purged with hydrogen for three times, and then stirred at 20° C. for 12 hours under hydrogen (in balloon). The resulting mixture was filtered and concentrated under reduced pressure to give 2-[[6-[bis(tert-butoxycarbonyl)amino]-5-tetrahydrofuran-3-yl-3-pyridyl]amino]-2-oxo-acetic acid (850 mg, crude, Et₃N) as white solid.

$^1$H NMR (400 MHz, methanol-d4) δ ppm 8.74 (d, J=2.3 Hz, 1H), 8.35 (d, J=2.3 Hz, 1H), 4.09-4.17 (m, 1H), 4.04 (t, J=8.0 Hz, 1H), 3.90 (q, J=7.9 Hz, 1H), 3.72 (dd, J=8.4, 6.1 Hz, 1H), 3.35-3.48 (m, 1H), 2.32-2.48 (m, 1H), 2.00-2.06 (m, 1H), 1.39 (s, 18H).

Step 4: Synthesis of tert-butyl N-tert-butoxycarbonyl-N-[5-[[2-[(5S)-5-methyl-2-[2-(1-methyl-4-piperidyl)-1,3-benzothiazol-5-yl]-1-piperidyl]-2-oxo-acetyl]amino]-3-tetrahydrofuran-3-yl-2-pyridyl]carbamate To a mixture of 2-[[6-[bis(tert-butoxycarbonyl)amino]-5-tetrahydrofuran-3-yl-3-pyridyl]amino]-2-oxo-acetic acid (300 mg, 0.543 mmol, Et₃N) and 2-(1-methyl-4-piperidyl)-5-[(5S)-5-methyl-2-piperidyl]-1,3-benzothiazole (195 mg, 0.592 mmol) in DMF (6 mL) were added HATU (250 mg, 0.658 mmol) and DIPEA (0.3 mL, 1.72 mmol). The resulting mixture was stirred at 20° C. for 2 hours. The resulting mixture was quenched by addition of water (50 mL) and extracted with EtOAc (100 mL*3). The combined organic layer was washed with saturated NH₄Cl aqueous solution (100 mL), brine (100 mL), dried over anhydrous Na₂SO₄, filtered and concentrated under reduced pressure. The residue was purified by flash chromatography (ISCO®; 12 g AgelaFlash® Silica Flash Column, EtOAc/MeOH with MeOH from 0~20%, flow rate=30 mL/min, 254 nm) to afford tert-butyl N-tert-butoxycarbonyl-N-[5-[[2-[(5S)-5-methyl-2-[2-(1-methyl-4-piperidyl)-1,3-benzothiazol-5-yl]-1-piperidyl]-2-oxo-acetyl]amino]-3-tetrahydrofuran-3-yl-2- pyridyl]carbamate (280 mg, 67.6% yield) as yellow solid. LCMS (ESI) [M+H]+ m/z: calcd 763.4, found 763.4.

Step 5: Synthesis of N-(6-amino-5-tetrahydrofuran-3-yl-3-pyridyl)-2-[(5S)-5-methyl-2-[2-(1-methyl-4-piperidyl)-1,3-benzothiazol-5-yl]-1-piperidyl]-2-oxo-acetamide A mixture of tert-butyl N-tert-butoxycarbonyl-N-[5-[[2-[(5S)-5-methyl-2-[2-(1-methyl-4-piperidyl)-1,3-benzothiazol-5-yl]-1-piperidyl]-2-oxo-acetyl]amino]-3-tetrahydrofuran-3-yl-2-pyridyl]carbamate (280 mg, 0.367 mmol), DCM (4 mL) and TFA (4 mL, 51.9 mmol) was stirred at 20° C. for 2 hours. The mixture was concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80*40 mm*3 m; Mobile phase A: H$_2$O with 10 mmol NH$_4$HCO$_3$ (v %); Mobile phase B: MeCN; Gradient: B from 20% to 50% in 9.5 min, hold 100% B for 1 min; Flow Rate: 25 mL/min; Column Temperature: 30° C.; Wavelength: 220 nm, 254 nm) to afford N-(6-amino-5-tetrahydrofuran-3-yl-3-pyridyl)-2-[(5S)-5-methyl-2-[2-(1-methyl-4-piperidyl)-1,3-benzothiazol-5-yl]-1-piperidyl]-2-oxo-acetamide (150 mg, 72.6% yield) as white solid. LCMS (ESI) [M+H]+ m/z: calcd 563.3, found 563.3; HPLC: 1000% @220 nm, 1000% @254 nm.

Step 6: Synthesis of N-(6-amino-5-tetrahydrofuran-3-yl-3-pyridyl)-2-[(2R,5S)-5-methyl-2-[2-(]-methyl-4-piperidyl)-1,3-benzothiazol-5-yl]-1-piperidyl]-2-oxo-acetamide N-(6-amino-5-tetrahydrofuran-3-yl-3-pyridyl)-2-[(5S)-5-methyl-2-[2-(1-methyl-4-piperidyl)-1,3-benzothiazol-5-yl]-1-piperidyl]-2-oxo-acetamide (150 mg, 0.267 mmol) was purified by SFC (Instrument: Berger, Multigr AM-II; Column: Daicel chiralpak IG (250 mm*30 mm*10 μm); Mobile phase: supercritical CO$_2$/MeOH (0.1% NH$_3$—H$_2$O, IPA v %)=60/40; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm). The fraction was concentrated under reduced pressure and then lyophilized for overnight to afford N-(6-amino-5-tetrahydrofuran-3-yl-3-pyridyl)-2-[(2R,5S)-5-methyl-2-[2-(1-methyl-4-piperidyl)-1,3-benzothiazol-5-yl]-1-piperidyl]-2-oxo-acetamide (100 mg, Peak 2, Retention time: 5.588 min) as white dry powder. HPLC: 100% @220 nm, 100% @254 nm.

Step 7: Synthesis of N-[6-amino-5-[(3S)-tetrahydrofuran-3-yl]-3-pyridyl]-2-[(2R,5S)-5-methyl-2-[2-(1-methyl-4-piperidyl)-1,3-benzothiazol-5-yl]-1-piperidyl]-2-oxo-acetamide (Compound 1154) and N-[6-amino-5-[(3R)-tetrahydrofuran-3-yl]-3-pyridyl]-2-[(2R,5S)-5-methy-2-[2-(1-methyl-4-piperidyl)-1,3-benzothiazol-5-yl]-1-piperidyl]-2-oxo-acetamide (Compound 1312

N-(6-amino-5-tetrahydrofuran-3-yl-3-pyridyl)-2-[(2R,5S)-5-methyl-2-[2-(1-methyl-4-piperidyl)-1,3-benzothiazol-5-yl]-1-piperidyl]-2-oxo-acetamide (50 mg, 0.0889 mmol) was purified by SFC (Instrument: Berger, Multigr AM-II; Column: Daicel chiralpak IC (250 mm*30 mm*5 μm); Mobile phase: supercritical Hexane-IPA (0.1% NH$_3$, IPA v %)=60/40; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm). The fraction was concentrated under reduced pressure and then lyophilized for overnight to give Compound 1154 and Compound 1312.

Compound 1154: N-[6-amino-5-[(3S)-tetrahydrofuran-3-yl]-3-pyridyl]-2-[(2R,5S)-5-methyl-2-[2-(1-methyl-4-piperidyl)-1,3-benzothiazol-5-yl]-1-piperidyl]-2-oxo-acetamide (20 mg, single unknown enantiomer, Peak 1, Retention time: 5.181 min, white solid). $^1$H NMR (400 MHz, methanol-d4) δ ppm 8.16 (br s, 1H), 7.91-8.03 (m, 1H), 7.91-8.03 (m, 1H), 7.55-7.77 (m, 1H), 7.34-7.49 (m, 1H), 5.48-5.85 (m, 1H), 4.05 (br d, J=7.5 Hz, 2H), 3.71-3.92 (m, 2H), 3.43 (br d, J=9.8 Hz, 2H), 3.15 (br d, J=13.1 Hz, 1H), 3.03 (br d, J=11.0 Hz, 2H), 2.16-2.46 (m, 10H), 1.89-2.07 (m, 5H), 1.36-1.53 (m, 2H), 1.14 (d, J=7.0 Hz, 3H); LCMS (ESI) [M+H]+ m/z: calcd 563.3, found 563.3; HPLC: 1000% @220 nm, 1000% @254 nm; 99.9% ee.

Compound 1312: N-[6-amino-5-[(3R)-tetrahydrofuran-3-yl]-3-pyridyl]-2-[(2R,5S)-5-methyl-2-[2-(1-methyl-4-piperidyl)-1,3-benzothiazol-5-yl]-1-piperidyl]-2-oxo-acetamide (20.1 mg, single unknown enantiomer, Peak 2, Retention time: 6.562 min, white solid). $^1$H NMR (400 MHz, methanol-d4) δ ppm 8.16 (br s, 1H), 7.91-8.04 (m, 2H), 7.54-7.80 (m, 1H), 7.43 (br d, J=8.8 Hz, 1H), 5.47-5.88 (m, 1H), 4.05 (br d, J=6.9 Hz, 2H), 3.70-3.92 (m, 2H), 3.43 (br d, J=9.6 Hz, 2H), 3.17 (br s, 1H), 3.04 (br d, J=11.5 Hz, 2H), 2.15-2.44 (m, 10H), 1.89-2.09 (m, 5H), 1.41-1.54 (m, 2H), 1.14 (d, J=6.9 Hz, 3H); LCMS (ESI) [M+H]+ m/z: calcd 563.3, found 563.3; HPLC: 1000% @220 nm, 1000% @254 nm; 99.2% ee.

Example 278. The Synthesis of N-(6-amino-5-ethyl-3-pyridyl)-2-oxo-2-[rac-(2S,5R)-2-[1-[2-(dimethylamino)ethyl]indazol-5-yl]-5-methyl-1-piperidyl]acetamide (Compound 1374) and N-(6-amino-5-ethyl-3-pyridyl)-2-oxo-2-[rac-(2R,5S)-2-[1-[2-(dimethylamino)ethyl]indazol-5-yl]-5-methyl-1-piperidyl]acetamide (Ent-Compound 1374

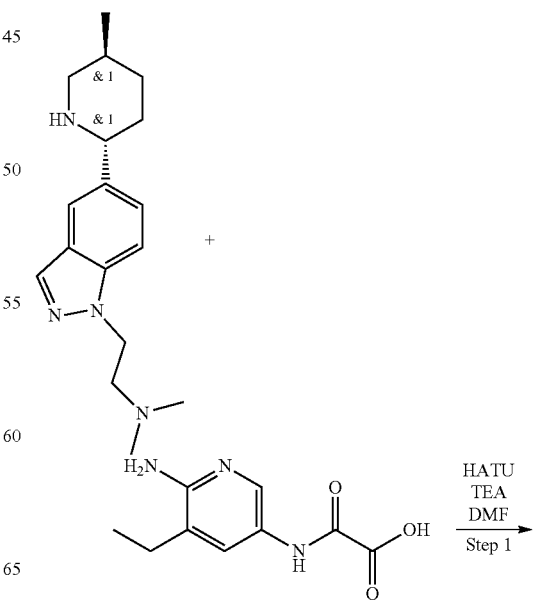

-continued

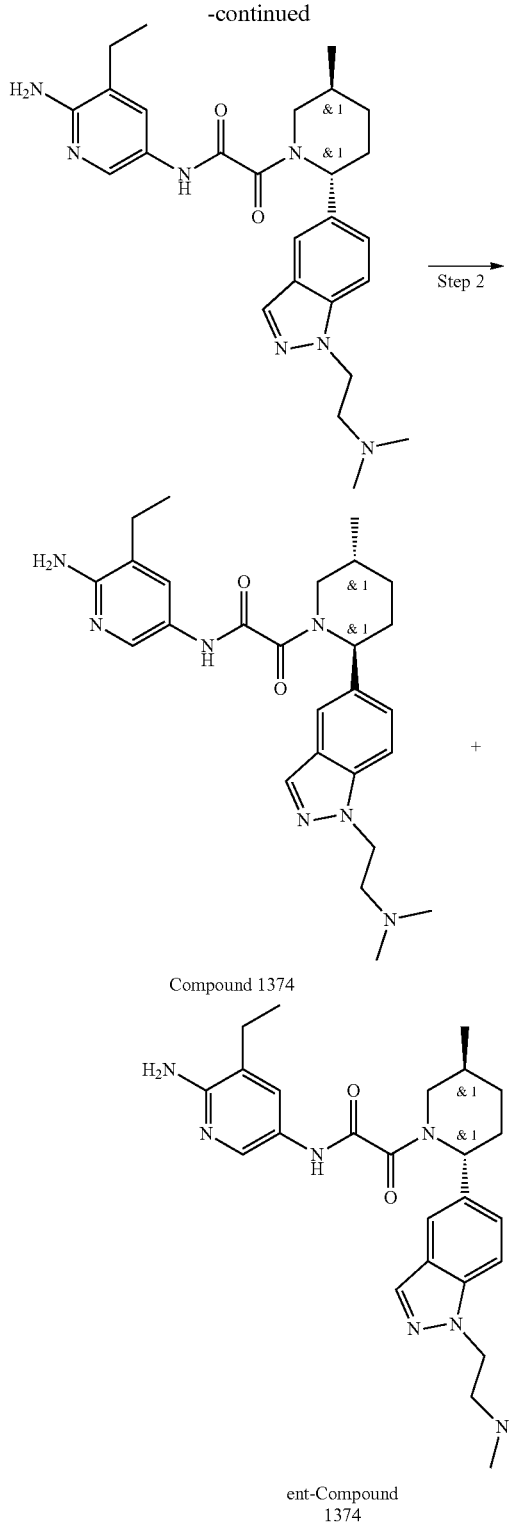

Compound 1374 ent-Compound 1374

Step 1: The Synthesis of N-(6-amino-5-ethyl-3-pyridyl)-2-oxo-2-[rac-(2R,5S)-2-[1-[2-(dimethylamino)ethyl]indazol-5-yl]-5-methyl-1-piperidyl]acetamide To a stirred mixture of N,N-dimethyl-2-[5-[(2R,5S)-5-methyl-2-piperidyl]indazol-1-yl]ethanamine (220 mg, 556 µmol, 3HCl salt), 2-[(6-amino-5-ethyl-3-pyridyl)amino]-2-oxo-acetic acid (128 mg, 611 µmol) and Triethylamine (337 mg, 3.34 mmol, 465 µL) in Dimethylformamide (4.00 mL) HATU (243 mg, 639 µmol) was added. The reaction mixture was stirred at 20° C. for 4 hr. The obtained mixture was subjected to HPLC (0-1-6 min 30-30-80% water—methanol, +0.1% vol. of 25% aq. NH₃, 30 mL/min, column: XBridge BEH C18, 100×20 mm, 5 µm), to afford N-(6-amino-5-ethyl-3-pyridyl)-2-oxo-2-[rac-(2R,5S)-2-[1-[2-(dimethylamino)ethyl]indazol-5-yl]-5-methyl-1-piperidyl]acetamide (160 mg, 335 µmol, 60.3% yield) as a yellow solid.

LCMS(ESI): [M+H]⁺ m/z: calcd 478.33; found 479.2; Rt=2.044.

Step 2: The Synthesis of N-(6-amino-5-ethyl-3-pyridyl)-2-oxo-2-[rac-(2S,5R)-2-[1-[2-(dimethylamino)ethyl]indazol-5-yl]-5-methyl-1-piperidyl]acetamide and N-(6-amino-5-ethyl-3-pyridyl)-2-oxo-2-[rac-(2R,5S)-2-[1-[2-(dimethylamino)ethyl]indazol-5-yl]-5-methyl-1-piperidyl]acetamide N-(6-amino-5-ethyl-3-pyridyl)-2-oxo-2-[rac-(2R,5S)-2-[1-[2-(dimethylamino)ethyl]indazol-5-yl]-5-methyl-1-piperidyl]acetamide (160 mg, 335 µmol) was subjected to Chiral HPLC (Column: Chiralpak IA-II (250*20 mm, 5 mkm), Mobile phase: IPA-MeOH, 50-50, Flow rate: 10 mL/min, 5 injections, 32 mg/inj., V=4 L) to afford: N-(6-amino-5-ethyl-3-pyridyl)-2-oxo-2-[rac-(2S,5R)-2-[1-[2-(dimethylamino)ethyl]indazol-5-yl]-5-methyl-1-piperidyl]acetamide (60.0 mg, 126 µmol, 75.0% yield) Compound 1374, with ret.time=11.570 min(analytical), 29.630 min(preparative) and N-(6-amino-5-ethyl-3-pyridyl)-2-oxo-2-[rac-(2R,5S)-2-[1-[2-(dimethylamino)ethyl]indazol-5-yl]-5-methyl-1-piperidyl]acetamide (53.0 mg, 111 µmol, 66.3% yield) Ent-Compound 1374, with ret.time=16.312 min(analytical), 49.692 min(preparative) as light-yellow solids.

Compound 1374: N-(6-amino-5-ethyl-3-pyridyl)-2-oxo-2-[rac-(2S,5R)-2-[1-[2-(dimethylamino)ethyl]indazol-5-yl]-5-methyl-1-piperidyl]acetamide 1H NMR (600 MHz, DMSO-d₆): δ (ppm) 1.03 (m, 3H), 1.11 (m, 3H), 1.36 (m, 1H), 1.76 (m, 1H), 1.88 (m, 1H), 2.06 (m, 1H), 2.14 (s, 6H), 2.30 (m, 4H), 2.68 (m, 2H), 2.76 (m, 1H), 3.74 (dd, 1H), 4.46 (m, 2H), 5.63 (t, 2H), 7.34 (m, 1H), 7.48 (m, 1H), 7.67 (m, 2H), 8.03 (m, 2H), 10.52 (m, 1H).

LCMS(ESI): [M+H]⁺ m/z: calcd 478.33; found 479.4; Rt=1.656.

Ent-Compound 1374: N-(6-amino-5-ethyl-3-pyridyl)-2-oxo-2-[rac-(2R,5S)-2-[1-[2-(dimethylamino)ethyl]indazol-5-yl]-5-methyl-1-piperidyl]acetamide 1H NMR (600 MHz, DMSO-d₆): δ (ppm) 1.02 (m, 3H), 1.12 (m, 3H), 1.36 (m, 1H), 1.76 (m, 1H), 1.88 (m, 1H), 2.07 (m, 1H), 2.14 (s, 6H), 2.26 (m, 1H), 2.37 (m, 3H), 2.68 (m, 2H), 3.01 (m, 1H), 3.84 (m, 1H), 4.46 (m, 2H), 5.63 (m, 3H), 7.34 (dd, 1H), 7.48 (d, 1H), 7.67 (m, 2H), 8.03 (m, 2H), 10.52 (m, 1H).

LCMS(ESI): [M+H]⁺ m/z: calcd 478.33; found 479.4; Rt=1.651.

Example 279. The Synthesis of N-(6-amino-5-eth-ylpyridin-3-yl)-2-((2R,5S)-2-(3-chloro-5-(2-(dimeth-ylamino)ethoxy)phenyl)-5-methylpiperidin-1-yl)-2-oxoacetamide (Compound 1247)

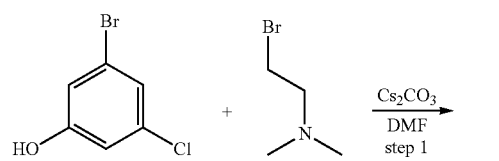

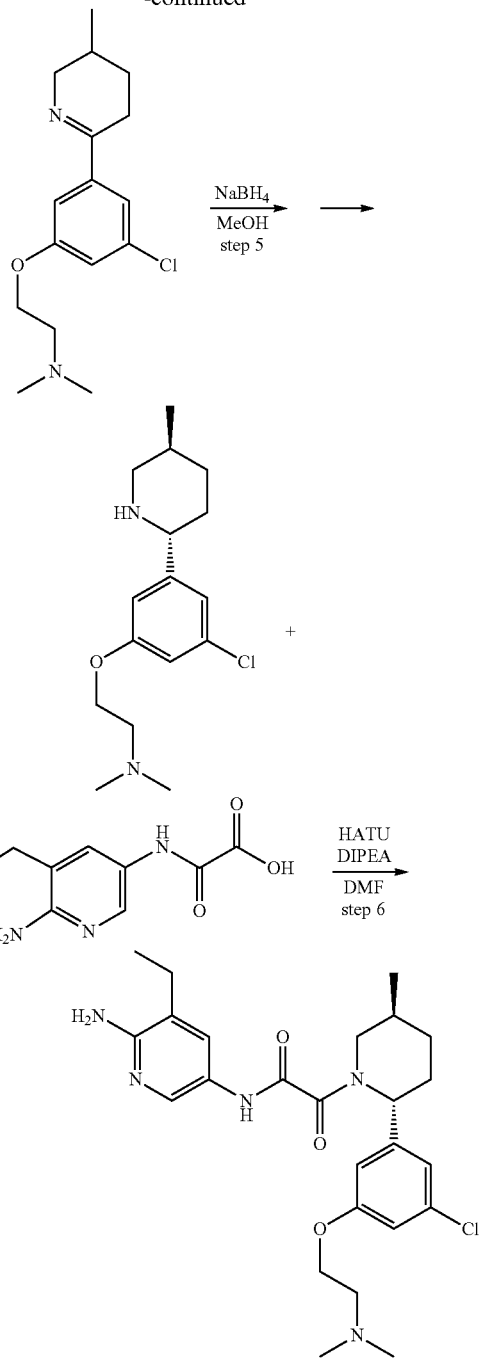

Step 1: Synthesis of
2-(3-bromo-5-chlorophenoxy)-N,N-dimethylethanamine

To a stirred solution of 3-bromo-5-chlorophenol (4 g, 19.28 mmol) in DMF (200 mL) were added (2-bromoethyl)dimethylamine hydrobromide (5.39 g, 23.14 mmol) and cesium carbonate (21.99 g, 67.49 mmol) respectively at 50° C. After aliquot, product wasn't detected. Then (2-bromoethyl)dimethylamine hydrobromide (5.39 g, 23.14 mmol) and cesium carbonate (43.98 g, 134.97 mmol) were added and temperature was raised to 70° C. Next day (2-bromoethyl)dimethylamine hydrobromide (16.17 g, 69.41 mmol) and cesium carbonate (21.99 g, 67.49 mmol) were added and temperature raised to 80° C. The reaction mixture was cooled and poured into water (800 ml) and the resulting mixture was extracted with MTBE (2*100 ml). Combined organic layers were washed with water (3*100 ml), brine (100 ml), dried over Na$_2$SO$_4$, filtered, and concentrated in vacuum. Then crude product was purified with flash chromatography. It was filtered with SiO$_2$ pad. In EtOAc/Hexane eluent only s.m. was obtained. Then SiO$_2$ pad was washed with mixture of MeOH and 5% of Et$_3$N (1000 ml). The desired product 2-(3-bromo-5-chloro-phenoxy)-N,N-dimethyl-ethanamine (0.5 g, 1.79 mmol, 9.31% yield) was isolated as yellow color state.

$^1$H NMR (500 MHz, CDCl$_3$) δ (ppm) 2.33 (s, 6H), 2.71 (t, 2H), 4.03 (t, 2H), 6.86 (s, 1H), 6.96 (s, 1H), 7.09 (s, 1H).

Step 2: Synthesis of 2-(3-chloro-5-(4,4,5,5-tetramethyl-1,3,2-dioxaborolan-2-yl)phenoxy)-N,N-dimethylethanamine To a stirred solution of 2-(3-bromo-5-chloro-phenoxy)-N,N-dimethyl-ethanamine (200 mg, 717.95 µmol) and 4,4,5,5-tetramethyl-2-(4,4,5,5-tetramethyl-1,3,2-dioxaborolan-2-yl)-1,3,2-dioxaborolane (200.54 mg, 789.74 µmol) in dioxane (20 mL) was added potassium acetate (176.15 mg, 1.79 mmol, 112.20 µL). The resulting suspension was degassed with argon. Pd(dppf)Cl$_2$*DCM (58.58 mg, 71.79 µmol) was added. The reaction mixture was stirred at 85° C. for 16 hr. Upon completion, the reaction mixture was filtered and the filtrate was evaporated in vacuum to get an oily residue. Then compound was extracted with DCM/water (50 ml/10 ml), organic layer was dried over Na$_2$SO$_4$ and evaporated. Then 10 ml of diox/HCl was added and evaporated again. Then crude product was washed with 20 ml MTBE and filtered. The desired product 2-[3-chloro-5-(4,4,5,5-tetramethyl-1,3,2-dioxaborolan-2-yl)phenoxy]-N,N-dimethyl-ethanamine (240 mg, crude, HCl) was isolated.

LCMS(ESI): [M]$^+$ m/z: calcd 325.2; found 326.2; Rt=1.154 min.

Step 3: Synthesis of (S)-tert-butyl 6-(3-chloro-5-(2-(dimethylamino)ethoxy)phenyl)-3-methyl-3,4-dihydropyridine-1(2H)-carboxylate To a stirred solution of 2-[3-chloro-5-(4,4,5,5-tetramethyl-1,3,2-dioxaborolan-2-yl)phenoxy]-N,N-dimethyl-ethanamine (240 mg, 662.80 µmol, HCl) and tert-butyl (3S)-3-methyl-6-(trifluoromethylsulfonyloxy)-3,4-dihydro-2H-pyridine-1-carboxylate (251.78 mg, 729.08 µmol) in dioxane (6 mL) was added cesium carbonate (431.91 mg, 1.33 mmol). The resulting suspension was degassed with argon. Pd(dppf)Cl$_2$*DCM (27.04 mg, 33.14 µmol) was added. The reaction mixture was stirred at 85° C. for 16 hr. Upon completion, the reaction mixture was filtered and the filtrate was evaporated in vacuum to get an oily residue. Then compound was extracted with DCM/water (30 ml/10 ml), organic layer was dried over Na$_2$SO$_4$ and evaporated. The desired product tert-butyl (3S)-6-[3-chloro-5-[2-(dimethylamino)ethoxy]phenyl]-3-methyl-3,4-dihydro-2H-pyridine-1-carboxylate (240 mg, crude) was isolated.

LCMS(ESI): [M]$^+$ m/z: calcd 394.2; found 395.2; Rt=1.232 min.

Step 4: Synthesis of (S)-2-(3-chloro-5-(5-methyl-3,4,5,6-tetrahydropyridin-2-yl)phenoxy)-N,N-dimethylethanamine To a stirred solution of tert-butyl (3S)-6-[3-chloro-5-[2-(dimethylamino)ethoxy]phenyl]-3-methyl-3,4-dihydro-2H-pyridine-1-carboxylate (240 mg, 607.70 µmol) in DCM (3 mL) were added TFA (2.77 g, 24.31 mmol, 1.87 mL) respectively at 25° C. The resulting reaction mixture was stirred at 25° C. for 12 hr. Upon completion, the reaction mixture was concentrated under reduced pressure. Then water layer was basified with 10% KOH and extracted with DCM twice (10 ml). Organic layer was washed with water (10 ml), dried over Na$_2$SO$_4$ and evaporated. The desired product 2-[3-chloro-5-[(3S)-3-methyl-2,3,4,5-tetrahydropyridin-6-yl]phenoxy]-N,N-dimethyl-ethanamine (115 mg, 390.07 µmol, 64.19% yield) was isolated as a brown color state.

LCMS(ESI): [M]$^+$ m/z: calcd 294.2; found 295.2; Rt=0.639 min.

Step 5: Synthesis of 2-(3-chloro-5-((2R,5S)-5-methylpiperidin-2-yl)phenoxy)-N,N-dimethylethanamine To a stirred solution of 2-[3-chloro-5-[(3S)-3-methyl-2,3,4,5-tetrahydropyridin-6-yl]phenoxy]-N,N-dimethyl-ethanamine (115 mg, 390.07 µmol) in MeOH (4.97 mL) was added sodium borohydride (29.51 mg, 780.14 µmol, 27.48 µL) respectively at 25° C. The resulting reaction mixture was stirred at 25° C. for 12 hr. Upon completion, the reaction mixture was evaporated. Then compound was extracted with DCM/water (40 ml/10 ml), organic layer was dried over Na$_2$SO$_4$ and concentrated under reduced pressure to obtain crude product as brown color state. The desired product 2-[3-chloro-5-[(2R,5S)-5-methyl-2-piperidyl]phenoxy]-N,N-dimethyl-ethanamine (52 mg, 175.18 µmol, 44.91% yield) was isolated as brown color state.

LCMS(ESI): [M]$^+$ m/z: calcd 296.2; found 297.2; Rt=0.714 min.

Step 6: Synthesis of N-(6-amino-5-ethylpyridin-3-yl)-2-((2R,5S)-2-(3-chloro-5-(2-(dimethylamino)ethoxy)phenyl)-5-methylpiperidin-1-yl)-2-oxoacetamide (Compound 1247

To a stirred solution of 2-[3-chloro-5-[(2R,5S)-5-methyl-2-piperidyl]phenoxy]-N,N-dimethyl-ethanamine (52 mg, 175.18 µmol) in DMF (2 mL) were added 2-[(6-amino-5-ethyl-3-pyridyl)amino]-2-oxo-acetic acid (36.65 mg, 175.18 µmol), DIPEA (22.64 mg, 175.18 µmol, 30.51 µL) and HATU (66.61 mg, 175.18 µmol) respectively at 25° C. The resulting reaction mixture was allowed to stirred at 25° C. for 12 hr. Upon completion, the reaction mixture was concentrated under reduced pressure to obtain crude product as brown color state. The obtained crude product was purified by reverse phase HPLC (Device (Mobile Phase, Column): SYSTEM 5-5-45% 0-1-6 min H$_2$O/MeCN/0.1% FA, flow: 30 ml/min (loading pump 4 ml/min MeCN); column: XBridge BEH C18 5 um). The desired product N-(6-amino-5-ethyl-3-pyridyl)-2-oxo-2-[(2R,5S)-2-[3-chloro-5-[2-(dimethylamino)ethoxy]phenyl]-5-methyl-1-piperidyl]acetamide (14.9 mg, 30.53 µmol, 17.43% yield) was isolated as a brown color state.

$^1$H NMR (600 MHz, dmso) δ 0.96-1.03 (m, 3H), 1.07-1.14 (m, 3H), 1.24-1.38 (m, 1H), 1.55-1.70 (m, 1H), 1.78-1.94 (m, 1H), 1.94-2.07 (m, 1H), 2.10-2.17 (m, 1H), 2.20 (s, 6H), 2.37-2.42 (m, 2H), 2.71-2.83 (m, 1H), 3.98-4.10 (m, 3H), 5.07-5.53 (m, 1H), 5.57-5.71 (m, 2H), 6.73-6.86 (m, 1H), 6.86-6.97 (m, 2H), 7.41-7.54 (m, 1H), 7.96-8.09 (m, 1H), 8.12-9.05 (m, 2H), 10.47-10.73 (m, 1H). LCMS(ESI): [M]$^+$ m/z: calcd 488.2; found 489.2; Rt=1.959 min.

Example 280. The Synthesis of N-(6-amino-5-methyl-3-pyridyl)-2-[(2S,5R)-2-[1-[2-(dimethylamino)ethyl]indazol-5-yl]-5-methyl-1-piperidyl]-2-oxo-acetamide (Ent-Compound 1182) and N-(6-amino-5-methyl-3-pyridyl)-2-[(2R,5S)-2-[1-[2-(dimethylamino)ethyl]indazol-5-yl]-5-methyl-1-piperidyl]-2-oxo-acetamide (Compound 1182)
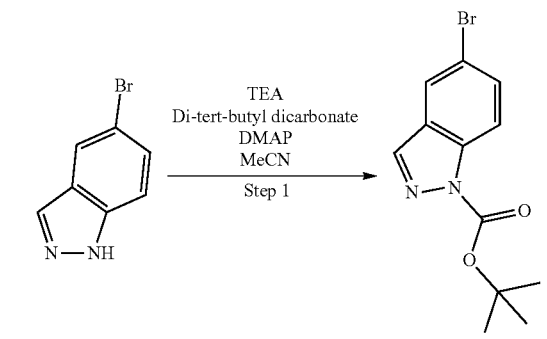
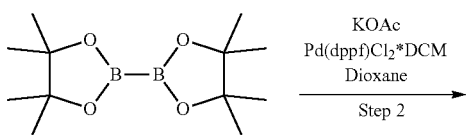
-continued
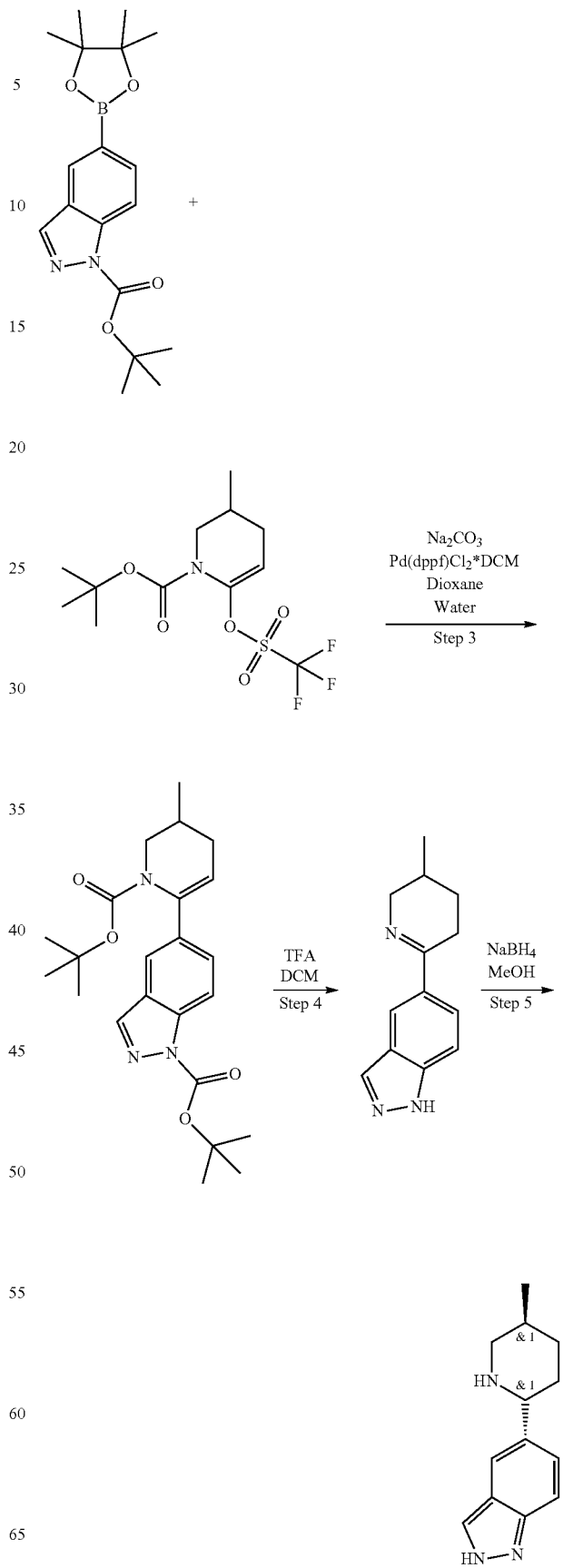
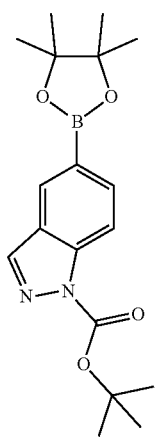

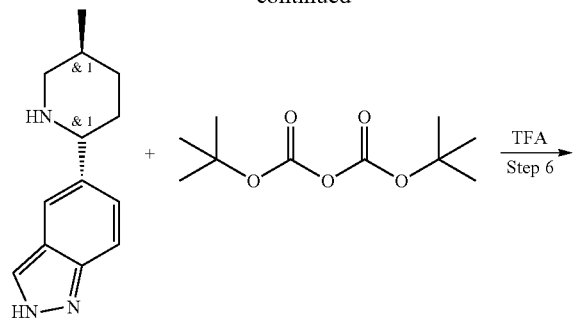
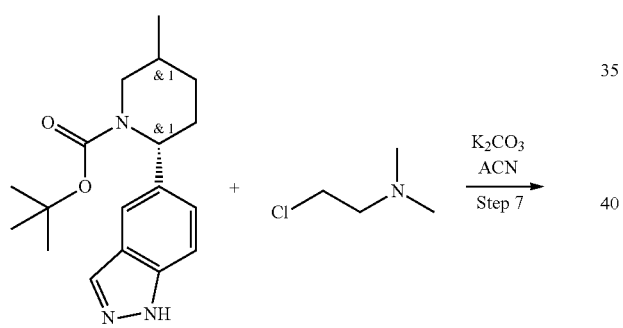
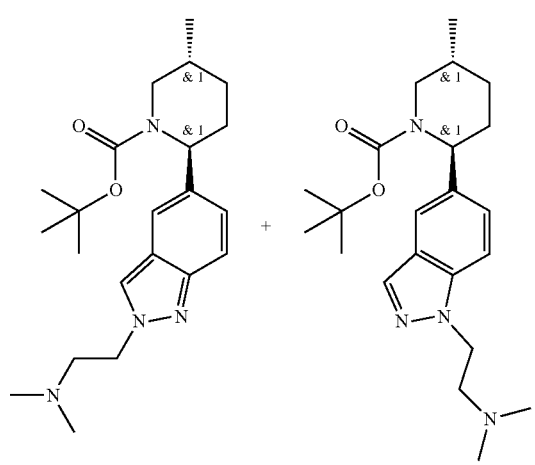
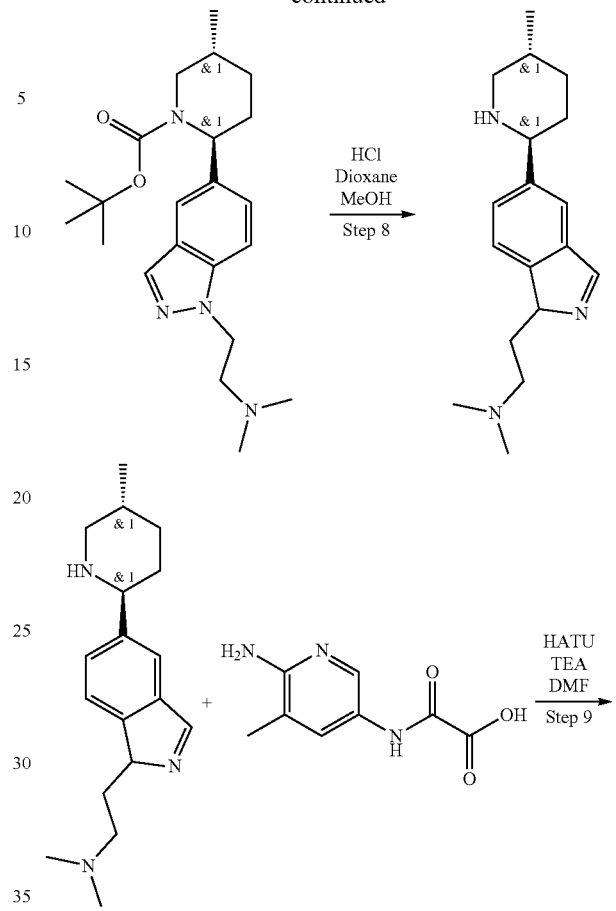
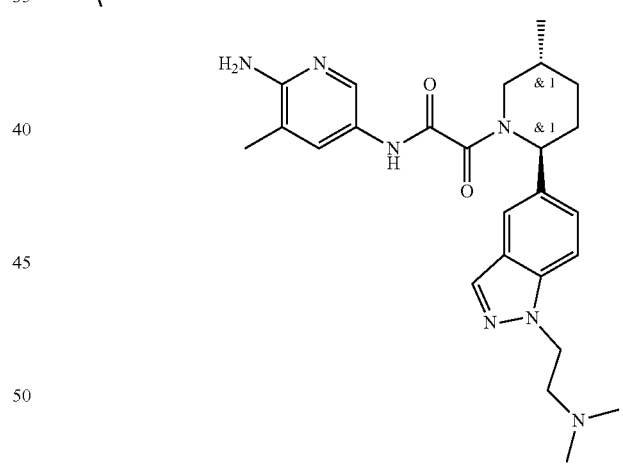

Step 1: The Synthesis of tert-butyl 5-bromoindazole-1-carboxylate

To a stirring solution of 5-bromo-1H-indazole (50.0 g, 254 mmol) in acetonitrile (500 mL) triethyl amine (25.7 g, 254 mmol, 35.4 mL), Di-tert-butyl dicarbonate (66.5 g, 305 mmol, 69.9 mL) and DMAP (3.10 g, 25.4 mmol) were added at 25° C. The reaction mixture was stirred at the same temperature for 3 hr. The obtained mixture was concentrated under reduced pressure. The crude product (80.0 g) was subjected to column chromatography (SiO$_2$; hexane/MTBE gradient (0-100% MTBE in Hexane)) to afford tert-butyl 5-bromoindazole-1-carboxylate (49.0 g, 165 mmol, 64.9% yield) as a yellow gum.

1H NMR (500 MHz, CDCl$_3$) δ 1.72 (s, 9H). 7.26-7.28 (m, 1H), 7.62 (s, 1H), 8.10-8.11 (m, 2H).

Step 2: The Synthesis of tert-butyl 5-(4,4,5,5-tetramethyl-1,3,2-dioxaborolan-2-yl)indazole-1-carboxylate To a stirred solution of tert-butyl 5-bromoindazole-1-carboxylate (49.0 g, 165 mmol) in Dioxane (1000 mL) 4,4,5,5-tetramethyl-2-(4,4,5,5-tetramethyl-1,3,2-dioxaborolan-2-yl)-1,3,2-dioxaborolane (46.1 g, 181 mmol), Potassium Acetate (32.4 g, 330 mmol, 20.6 mL) and Pd(dppf)Cl$_2$CH$_2$Cl$_2$ (13.5 g, 16.5 mmol) were added at room temperature. The reaction mixture was stirred at 90° C. for 20 hr in an inert atmosphere. The obtained mixture was cooled to room temperature and filtered through a pad of silica. The filter cake was washed ethyl acetate (200 mL). The filtrate was concentrated under reduced pressure. The crude product was purified by column chromatography (SiO$_2$; hexane/ethyl acetate gradient (0-100% ethyl acetate)) to afford tert-butyl 5-(4,4,5,5-tetramethyl-1,3,2-dioxaborolan-2-yl)indazole-1-carboxylate (45.0 g, 131 mmol, 79.3% yield) as a light-yellow solid.

1H NMR (500 MHz, CDCl$_3$) δ 1.37 (s, 12H), 1.73 (s, 9H), 7.94 (m, 1H), 8.16-8.23 (m, 3H).

Step 3: The Synthesis of tert-butyl 5-(1-tert-butoxycarbonyl-3-methyl-3,4-dihydro-2H-pyridin-6-yl)indazole-1-carboxylate A suspension of tert-butyl 5-(4,4,5,5-tetramethyl-1,3,2-dioxaborolan-2-yl)indazole-1-carboxylate (15.7 g, 45.6 mmol), tert-butyl 3-methyl-6-(trifluoromethylsulfonyloxy)-3,4-dihydro-2H-pyridine-1-carboxylate (18.9 g, 54.7 mmol) and Sodium carbonate (14.50 g, 136.8 mmol) in Dioxane (200 mL) and Water (70.0 mL) was evacuated and then backfilled with Ar.

[1,1'-Bis(diphenylphosphino)ferrocene]dichloropalladium(II), complex with dichloromethane (1.86 g, 2.28 mmol) was added. The resulting mixture was stirred at 90° C. for 24 hr. The obtained mixture was cooled to 25° C., filtered and concentrated in vacuo. The residue was subjected to gradient chromatography (SiO$_2$; Hexane-EA) to afford tert-butyl 5-(1-tert-butoxycarbonyl-3-methyl-3,4-dihydro-2H-pyridin-6-yl)indazole-1-carboxylate (7.30 g, 17.7 mmol, 38.7% yield) as light-yellow gum.

LCMS(ESI): [M-boc+H]$^+$ m/z: calcd 314.27; found 314.0; Rt=1.445.

Step 4: The Synthesis of 5-(3-methyl-2,3,4,5-tetrahydropyridin-6-yl)-1H-indazole Trifluoroacetic acid (29.6 g, 260 mmol, 20.0 mL) was added to a solution of tert-butyl 5-(1-tert-butoxycarbonyl-3-methyl-3,4-dihydro-2H-pyridin-6-yl)indazole-1-carboxylate (7.30 g, 17.6 mmol) in Dichloromethane (25.0 mL). The resulting mixture was stirred at 25° C. for 14 hr. The obtained mixture was concentrated under reduced pressure. The residue was dissolved in water (60.0 mL) and filtered through a cotton wool plug. The filtrate was basified to pH≈10 with solid K$_2$CO$_3$. The white solid formed was filtered and dried to afford 5-(3-methyl-2,3,4,5-tetrahydropyridin-6-yl)-1H-indazole (3.40 g, 15.9 mmol, 90.3% yield) as a white solid.

LCMS(ESI): [M+H]$^+$ m/z: calcd 214.15; found 214.2; Rt=0.700.

Step 5: The Synthesis of 5-[(2R,5S)-5-methyl-2-piperidyl]-1H-indazole

To a stirring suspension of 5-(3-methyl-2,3,4,5-tetrahydropyridin-6-yl)-1H-indazole (3.40 g, 15.9 mmol) in Methanol (60.0 mL) Sodium Borohydride (905 mg, 23.9 mmol, 845 µL) was added portion-wise. The resulting mixture was stirred at 25° C. for 2 hr. The obtained mixture was concentrated under reduced pressure. The residue was partitioned between water (50.0 mL) and ethyl acetate (80.0 mL). The organic layer was separated, dried over Na$_2$SO$_4$ and concentrated in vacuo to afford 5-[(2R,5S)-5-methyl-2-piperidyl]-1H-indazole (3.50 g, crude) as a grey solid.

LCMS(ESI): [M+H]$^+$ m/z: calcd 216.17; found 216.3; Rt=0.792.

Step 6: The Synthesis of tert-butyl (2R,5S)-2-(2H-indazol-5-yl)-5-methyl-piperidine-1-carboxylate Tert-butoxycarbonyl tert-butyl carbonate (2.66 g, 12.2 mmol, 2.80 mL) was added to a solution of 5-[(2R,5S)-5-methyl-2-piperidyl]-2H-indazole (2.60 g, 12.1 mmol) in THF (50.0 mL). The resulting mixture was stirred at 25° C. for 15 hr and concentrated under reduced pressure to afford tert-butyl (2R,5S)-2-(2H-indazol-5-yl)-5-methyl-piperidine-1-carboxylate (3.20 g, crude) as a light-yellow gum.

LCMS(ESI): [M+H]$^+$ m/z: calcd 316.23; found 316.0; Rt=1.458.

Step 7: The Synthesis of tert-butyl (2S,5R)-2-[2-[2-(dimethylamino)ethyl]indazol-5-yl]-5-methyl-piperidine-1-carboxylate and Tert-butyl (2S,5R)-2-[1-[2-(dimethylamino)ethyl]indazol-5-yl]-5-methyl-piperidine-1-carboxylate To a stirred solution of tert-butyl (2S,5R)-2-(1H-indazol-5-yl)-5-methyl-piperidine-1-carboxylate (500 mg, 1.59 mmol) in ACN (50.0 mL) Potassium carbonate, anhydrous, 99% (548 mg, 3.96 mmol) was added, followed by addition of 2-chloro-N,N-dimethyl-ethanamine (274 mg, 1.90 mmol, 205 µL, HCl salt). The resulting mixture was stirred at 70° C. for 90 hr. The reaction mixture was subjected to HPLC (0-5 min 55-65% water—methanol, +0.1% vol. of 25% aq. NH$_3$, 30 mL/min, column: XBridge C18, 100×19 mm, 5 µm) to afford tert-butyl (2S,5R)-2-[2-[2-(dimethylamino)ethyl]indazol-5-yl]-5-methyl-piperidine-1-carboxylate (60.0 mg, 155 µmol, 19.6% yield) and tert-butyl (2S,5R)-2-[1-[2-(dimethylamino)ethyl]indazol-5-yl]-5-methyl-piperidine-1-carboxylate (70.0 mg, 181 µmol, 22.8% yield) as colorless oil. tert-butyl (2S,5R)-2-[2-[2-(dimethylamino)ethyl]indazol-5-yl]-5-methyl-piperidine-1-carboxylate LCMS(ESI): [M+H]$^+$ m/z: calcd 387.32; found 387.4; Rt=2.687. tert-butyl (2S,5R)-2-[1-[2-(dimethylamino)ethyl]indazol-5-yl]-5-methyl-piperidine-1-carboxylate LCMS(ESI): [M–H]$^+$ m/z: calcd 385.32; found 386.2; Rt=1.431.

Step 8: The Synthesis of N,N-dimethyl-2-[5-[(2S,5R)-5-methyl-2-piperidyl]indazol-1-yl]ethanamine To a solution of tert-butyl (2S,5R)-2-[1-[2-(dimethylamino)ethyl]indazol-5-yl]-5-methyl-piperidine-1-carboxylate (71.0 mg, 184 µmol) in MeOH (2.00 mL), Hydrogen chloride solution 40 M in dioxane (837 mg, 1.84 mmol, 1.05 mL, 8% purity) was added. The reaction mixture was stirred at 25° C. for 12 hr and the solvent was evaporated in vacuo to afford N,N-dimethyl-2-[5-[(2S,5R)-5-methyl-2-piperidyl] indazol-1-yl]ethanamine (65.0 mg, 181 μmol, 98.5% yield, 2HCl salt) as a light-yellow solid.

LCMS(ESI): [M+H]+ m/z: calcd 387.26; found 387.0; Rt=0.442.

Step 9: The Synthesis of N-(6-amino-5-methyl-3-pyridyl)-2-[(2S,5R)-2-[1-[2-(dimethylamino)ethyl] indazol-5-yl]-5-methyl-1-piperidyl]-2-oxo-acetamide To a solution of N,N-dimethyl-2-[5-[(2S,5R)-5-methyl-2-piperidyl]indazol-1-yl]ethanamine (65.0 mg, 181 μmol, 2HCl salt), 2-[(6-amino-5-methyl-3-pyridyl)amino]-2-oxo-acetic acid (45.9 mg, 235 μmol) and Triethylamine (91.5 mg, 904 μmol, 126 μL) in DMF (3.00 mL) HATU (82.5 mg, 217 μmol) was added. The resulting mixture was stirred at 25° C. for 2 hr. The reaction mixture was subjected to HPLC (0-6 min 25-50% water—ACN, +0.1% vol. of 25% aq. NH₃, 30 mL/min, column: YMC-Actus Triart C18, 100×20 mm, 5 μm) to afford N-(6-amino-5-methyl-3-pyridyl)-2-[(2S,5R)-2-[1-[2-(dimethylamino)ethyl]indazol-5-yl]-5-methyl-1-piperidyl]-2-oxo-acetamide (57.0 mg, 123 μmol, 67.9% yield) as a white solid.

1H NMR (600 MHz, DMSO-d₆) δ 0.98-1.07 (m, 3H), 1.30-1.42 (m, 1H), 1.71-1.82 (m, 1H), 1.82-1.92 (m, 1H), 1.97-2.05 (m, 3H), 2.06-2.13 (m, 1H), 2.15 (s, 6H), 2.24-2.36 (m, 1H), 2.65-2.71 (m, 2H), 2.74-3.23 (m, 1H), 3.44-4.04 (m, 1H), 4.42-4.51 (m, 2H), 5.18-5.60 (m, 1H), 5.60-5.74 (m, 2H), 7.27-7.41 (m, 1H), 7.41-7.52 (m, 1H), 7.64-7.71 (m, 2H), 7.94-8.07 (m, 2H), 10.47-10.56 (m, 1H).

LCMS(ESI): [M+H]+ m/z: calcd 464.31; found 464.4; Rt=1.507.

Step 10: The Synthesis of N-(6-amino-5-methyl-3-pyridyl)-2-[(2S,5R)-2-[1-[2-(dimethylamino)ethyl] indazol-5-yl]-5-methyl-1-piperidyl]-2-oxo-acetamide (Ent-Compound 1182) and N-(6-amino-5-methyl-3-pyridyl)-2-[(2R,5S)-2-[1-[2-(dimethylamino)ethyl] indazol-5-yl]-5-methyl-1-piperidyl]-2-oxo-acetamide (Compound 1182

N-(6-amino-5-methyl-3-pyridyl)-2-[(2S,5R)-2-[1-[2-(dimethylamino)ethyl]indazol-5-yl]-5-methyl-1-piperidyl]-2-oxo-acetamide (50.0 mg, 108 μmol) was subjected to chiral separation (Column: Chiralcel OJ-H (250/20 mm/5 m); Mobile phase: Hexane-IPA-MeOH, 50-25-25, Flow Rate: 12 mL/min; Column Temperature: 24° C.; Wavelength: 205 nm, 220 nm, 265 nm, 298 nm) to afford N-(6-amino-5-methyl-3-pyridyl)-2-[(2S,5R)-2-[1-[2-(dimethylamino) ethyl]indazol-5-yl]-5-methyl-1-piperidyl]-2-oxo-acetamide (19.0 mg, 40.9 μmol, 76.0% yield) RetTime (ent-Compound 1182)=23.94 min and N-(6-amino-5-methyl-3-pyridyl)-2-[(2R,5S)-2-[1-[2-(dimethylamino)ethyl]indazol-5-yl]-5-methyl-1-piperidyl]-2-oxo-acetamide (18.0 mg, 38.8 μmol, 72.0% yield) RetTime (Compound 1182)=17.00 min. (ent-Compound 1182): N-(6-amino-5-methyl-3-pyridyl)-2-[(2S,5R)-2-[1-[2-(dimethylamino)ethyl]indazol-5-yl]-5-methyl-1-piperidyl]-2-oxo-acetamide 1H NMR (600 MHz, DMSO-d₆) δ 1.01-1.04 (m, 3H), 1.32-1.40 (m, 2H), 1.72-1.88 (m, 2H), 1.97-2.16 (m, 9H), 2.25-2.37 (m, 1H), 2.64-2.77 (m, 2H), 3.46 (d, 1H), 4.01 (d, 1H), 4.45-4.47 (m, 2H), 5.57-5.67 (m, 3H), 7.29-7.50 (m, 2H), 7.66-7.75 (m, 2H), 7.96-8.04 (m, 2H), 10.52 (m, 1H).

LCMS(ESI): [M+H]+ m/z: calcd 464.31; found 464.4; Rt=1.640.

(Compound 1182): N-(6-amino-5-methyl-3-pyridyl)-2-[(2R,5S)-2-[1-[2-(dimethylamino)ethyl]indazol-5-yl]-5-methyl-1-piperidyl]-2-oxo-acetamide 1H NMR (600 MHz, DMSO-d₆) δ 1.01-1.04 (m, 3H), 1.32-1.39 (m, 2H), 1.68-1.89 (m, 3H), 1.97-2.37 (m, 8H), 2.67-2.98 (m, 4H), 3.45 (m, 1H), 4.01 (m, 1H), 4.46 (m, 2H), 5.57-5.67 (m, 2H), 7.29-7.50 (m, 2H), 7.66-7.73 (m, 2H), 7.96-8.04 (m, 2H), 10.53 (m, 1H).

LCMS(ESI): [M+H]+ m/z: calcd 464.31; found 464.4; Rt=1.910.

Example 281. The Synthesis of N-(6-amino-5-ethyl-3-pyridyl)-2-[(5S)-5-methyl-2-(2-methylindazol-6-yl)-1-piperidyl]-2-oxo-acetamide (Compound 1199

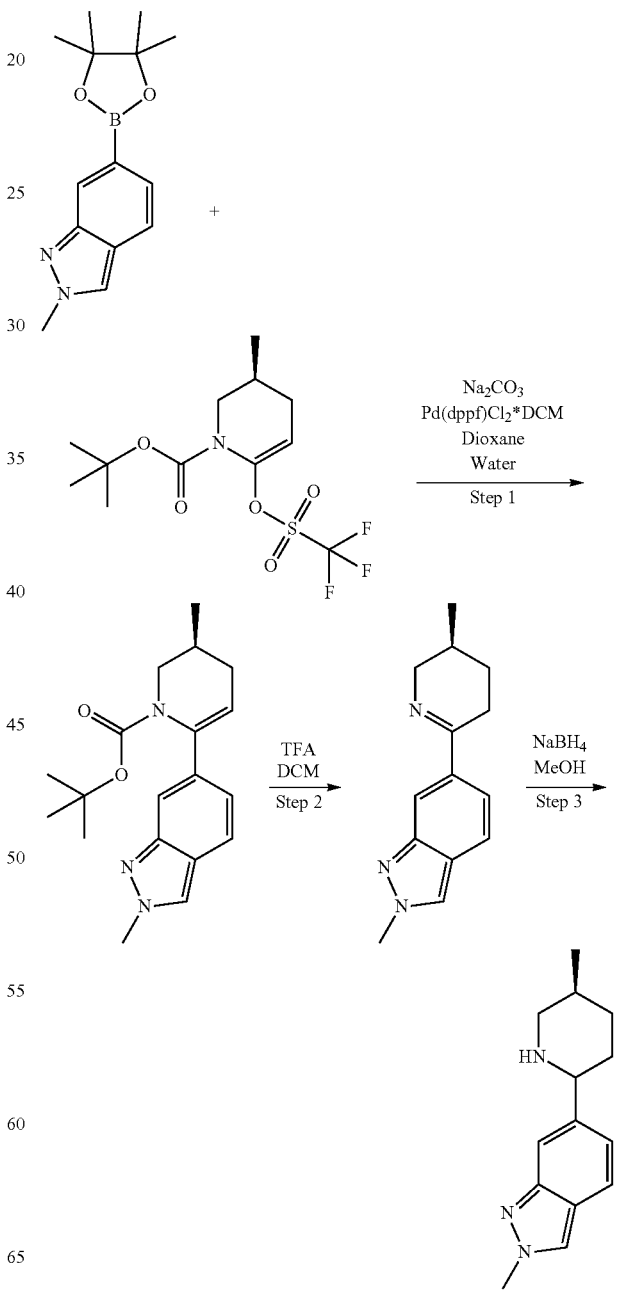

-continued

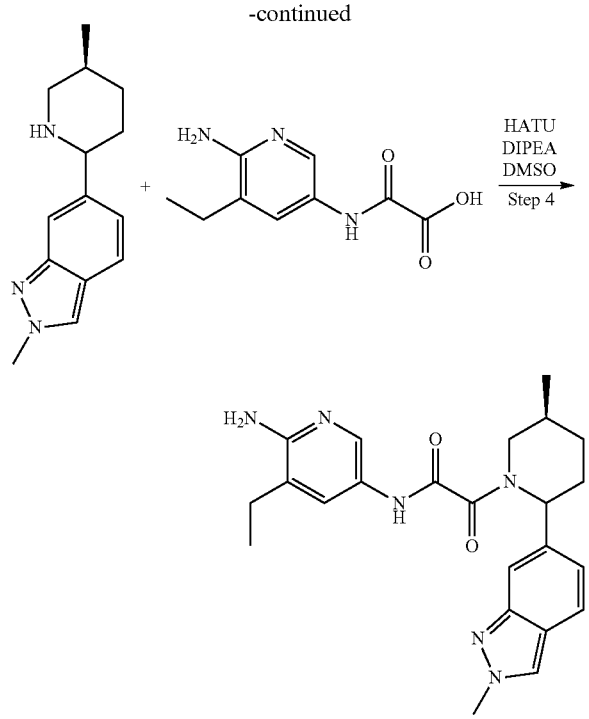

Step 1: The Synthesis of tert-butyl (3S)-3-methyl-6-(2-methylindazol-6-yl)-3,4-dihydro-2H-pyridine-1-carboxylate 2-methyl-6-(4,4,5,5-tetramethyl-1,3,2-dioxaborolan-2-yl)indazole (1.00 g, 3.87 mmol), tert-butyl (3S)-3-methyl-6-(trifluoromethylsulfonyloxy)-3,4-dihydro-2H-pyridine-1-carboxylate (1.47 g, 4.26 mmol), Sodium carbonate (1.23 g, 11.6 mmol, 487 μL) and Pd(dppf)Cl$_2$*DCM (158 mg, 194 μmol) were added to a mixture of water (5.00 mL) and 1,4-dioxane (15.0 mL). The reaction mixture was stirred in an inert atmosphere at 80° C. for 16 hr. The resulting mixture was cooled, diluted with water and extracted with DCM. The organic layer was separated, dried over Na$_2$SO$_4$, and concentrated under reduced pressure. The residue was suspended in MTBE, stirred for 2 hr, and filtered. The filtrate was concentrated under reduced pressure to afford tert-butyl (3S)-3-methyl-6-(2-methylindazol-6-yl)-3,4-dihydro-2H-pyridine-1-carboxylate (1.00 g, crude).

LCMS(ESI): [M+H]$^+$ m/z: calcd 328.23; found 328.2; Rt=1.367.

Step 2: The Synthesis of 2-methyl-6-[(3S)-3-methyl-2,3,4,5-tetrahydropyridin-6-yl]indazole Tert-butyl (3 S)-3-methyl-6-(2-methylindazol-6-yl)-3,4-dihydro-2H-pyridine-1-carboxylate (1.00 g, 3.05 mmol) was dissolved in a mixture of TFA (4.00 mL) and DCM (6.00 mL). The reaction mixture was stirred at 25° C. for 0.5 hr. The obtained mixture was concentrated under reduced pressure to afford 2-methyl-6-[(3S)-3-methyl-2,3,4,5-tetrahydropyridin-6-yl]indazole (0.76 g, crude).

LCMS(ESI): [M+H]$^+$ m/z: calcd 228.17; found 228.2; Rt=0.781.

Step 3: The Synthesis of 2-methyl-6-[(5S)-5-methyl-2-piperidyl]indazole

To a solution of 2-methyl-6-[(3S)-3-methyl-2,3,4,5-tetrahydropyridin-6-yl]indazole (0.76 g, 3.34 mmol) in methanol (8.00 mL) Sodium Borohydride (164 mg, 4.35 mmol, 154 μL) was added portion-wise. The reaction mixture was stirred overnight. A mixture of HCl-methanol was added. The obtained mixture was concentrated under reduced pressure to afford 2-methyl-6-[(5S)-5-methyl-2-piperidyl]indazole (1.00 g, crude, HCl salt).

LCMS(ESI): [M+H]$^+$ m/z: calcd 230.19; found 230.2; Rt=0.821.

Step 4: The Synthesis of N-(6-amino-5-ethyl-3-pyridyl)-2-[(5S)-5-methyl-2-(2-methylindazol-6-yl)-1-piperidyl]-2-oxo-acetamide (Compound 1199

To a stirred solution of 2-methyl-6-[(5S)-5-methyl-2-piperidyl]indazole (0.14 g, 527 μmol, HCl salt), 2-[(6-amino-5-ethyl-3-pyridyl)amino]-2-oxo-acetic acid (121 mg, 579 μmol) and DIPEA (306 mg, 2.37 mmol, 413 μL) in DMSO (2.00 mL) HATU (240 mg, 632 μmol) was added. The reaction mixture was stirred at 25° C. for 16 hr. The resulting mixture was submitted to reverse phase HPLC (the 1-st run: 2-10 min 10-35% water+FA (0.1% vol.)—MeOH+FA (0.1% vol.); flow: 30 mL/min, column: Waters SunFire C18, 100×19 mm, 5 μm; the 2-nd run: 2-10 min 10-35% water-methanol, +0.1% vol. of 25% aq. NH$_3$, 30 mL/min, column: Waters SunFire C18, 100×19 mm, 5 μm) to afford N-(6-amino-5-ethyl-3-pyridyl)-2-[(5S)-5-methyl-2-(2-methylindazol-6-yl)-1-piperidyl]-2-oxo-acetamide (0.02 g, 40.4 μmol, 7.67% yield) as beige solid.

$^1$H NMR (600 MHz, DMSO-d$_6$): δ (ppm) 0.98-1.05 (m, 3H), 1.05-1.16 (m, 3H), 1.30-1.45 (m, 1H), 1.68-1.81 (m, 1H), 1.82-1.92 (m, 1H), 2.04-2.20 (m, 1H), 2.23-2.32 (m, 1H), 2.37-2.44 (m, 2H), 2.74-3.24 (m, 1H), 3.42-4.06 (m, 1H), 4.14 (s, 3H), 5.18-5.61 (m, 1H), 5.61-5.69 (m, 2H), 6.89-7.08 (m, 1H), 7.40-7.53 (m, 2H), 7.62-7.71 (m, 1H), 7.97-8.09 (m, 1H), 8.11-8.36 (m, 1H), 10.45-10.60 (m, 1H)

LCMS(ESI): [M+H]$^+$ m/z: calcd 421.26; found 421.2; Rt=2.443.

Example 282. The Synthesis of N-(6-amino-5-methyl-3-pyridyl)-2-[(2R,5S)-5-methyl-2-[2-(1-methyl-4-piperidyl)benzothiophen-5-yl]-1-piperidyl]-2-oxo-acetamide (Compound 1220

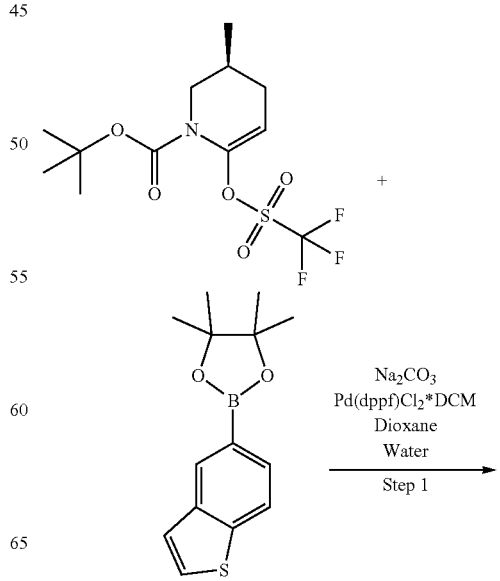

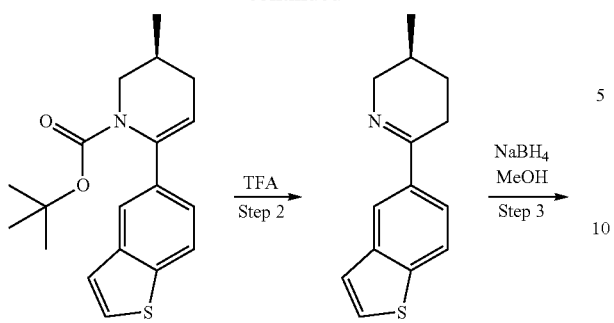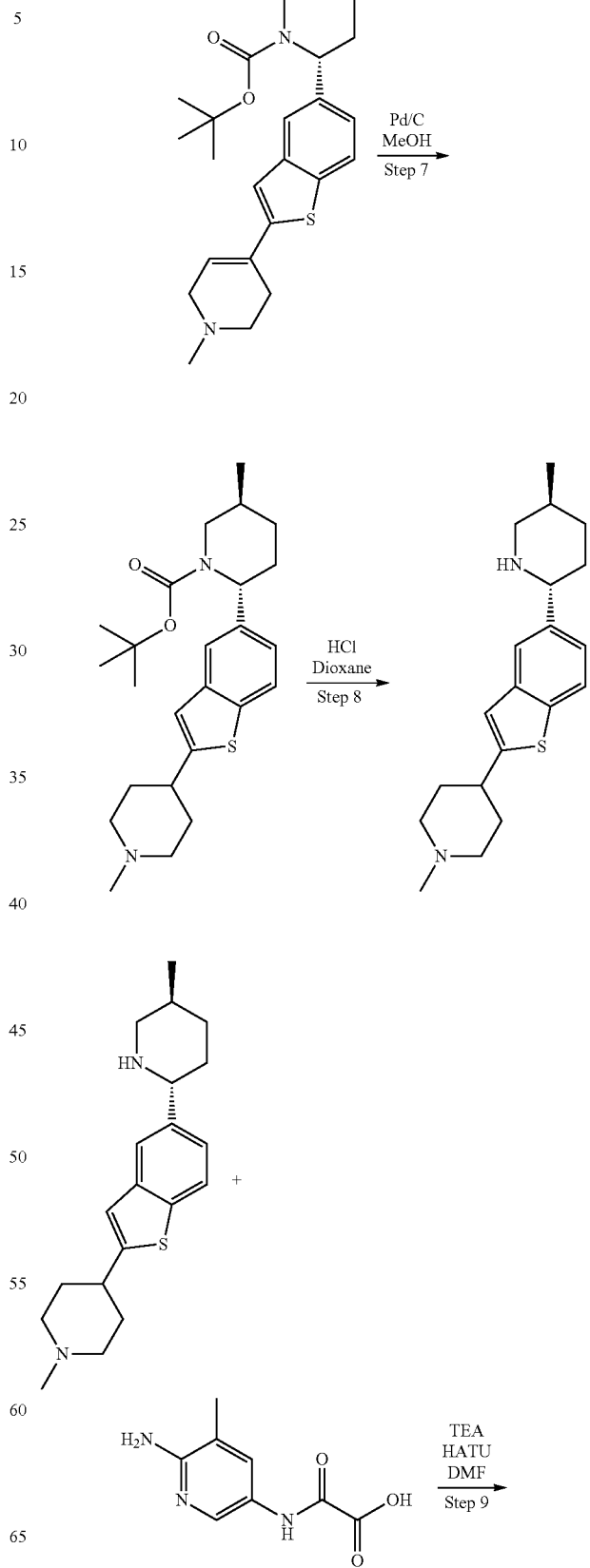

-continued

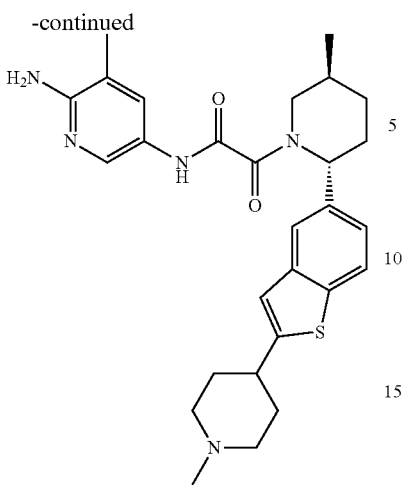

Step 1: The Synthesis of tert-butyl (3S)-6-(benzothiophen-5-yl)-3-methyl-3,4-dihydro-2H-pyridine-1-carboxylate Sodium carbonate (4.24 g, 39.9 mmol, 1.67 mL) was added to a solution of tert-butyl (3S)-3-methyl-6-(trifluoromethylsulfonyloxy)-3,4-dihydro-2H-pyridine-1-carboxylate (8.28 g, 23.9 mmol) and 2-(benzothiophen-5-yl)-4,4,5,5-tetramethyl-1,3,2-dioxaborolane (5.20 g, 19.9 mmol) in Dioxane (15.0 mL) and Water (55.0 mL). The reaction mixture was evacuated and then backfilled with Ar. Pd(dppf)Cl$_2$*DCM (1.63 g, 2.00 mmol) was added. The resulting mixture was stirred at 90° C. for 14 hr. The obtained mixture was concentrated under reduced pressure. The residue was subjected to gradient column chromatography (SiO$_2$; Hexanes-MTBE) to afford tert-butyl (3S)-6-(benzothiophen-5-yl)-3-methyl-3,4-dihydro-2H-pyridine-1-carboxylate (3.00 g, 9.11 mmol, 45.6% yield) as a brown solid.

$^1$H NMR (500 MHz, CDCl$_3$) δ 1.01 (m, 12H), 1.84-1.90 (m, 1H), 1.91-1.98 (m, 1H), 2.39-2.45 (m, 1H), 3.01-3.05 (m, 1H), 4.09-4.13 (m, 1H), 5.35-5.37 (m, 1H), 7.25-7.31 (m, 2H), 7.40-7.42 (d, 1H), 7.72 (s, 1H), 7.80-7.82 (d, 1H).

Step 2: The Synthesis of (3S)-6-(benzothiophen-5-yl)-3-methyl-2,3,4,5-tetrahydropyridine Tert-butyl (3S)-6-(benzothiophen-5-yl)-3-methyl-3,4-dihydro-2H-pyridine-1-carboxylate (3.00 g, 9.11 mmol) was mixed in Trifluoroacetic acid (10.4 g, 91.1 mmol, 7.02 mL). The resulting mixture was stirred at 25° C. for 1 hr. The obtained mixture was concentrated in vacuo. The residue was diluted with DCM (25.0 mL) and washed with NaHCO$_3$ solution (3*15.0 mL). The organic phase was dried over Na$_2$SO$_4$ and concentrated in vacuo to afford (3S)-6-(benzothiophen-5-yl)-3-methyl-2,3,4,5-tetrahydropyridine (2.00 g, 8.72 mmol, 95.8% yield) as a yellow solid.

LCMS(ESI): [M+H]$^+$ m/z: calcd 230.12; found 230.0; Rt=0.765.

Step 3: The Synthesis of (2R,5S)-2-(benzothiophen-5-yl)-5-methyl-piperidine

To a stirred solution of (3S)-6-(benzothiophen-5-yl)-3-methyl-2,3,4,5-tetrahydropyridine (2.00 g, 8.72 mmol) in Methanol (20.0 mL) Sodium Borohydride (330 mg, 8.72 mmol, 308 μL) was added portion-wise. The reaction mixture was stirred at 25° C. for 1.5 hr. The obtained mixture was concentrated in vacuo. The residue was diluted with water (50.0 mL) and extracted with DCM (2*25.0 mL). The combined organic layers were washed with brine, dried over Na$_2$SO$_4$ and concentrated in vacuo to afford (2R,5S)-2-(benzothiophen-5-yl)-5-methyl-piperidine (2.00 g, 8.64 mmol, 99.1% yield) as a brown solid.

LCMS(ESI): [M+H]$^+$ m/z: calcd 232.14; found 232.2; Rt=0.784.

Step 4: The Synthesis of tert-butyl (2R,5S)-2-(benzothiophen-5-yl)-5-methyl-piperidine-1-carboxylate To a stirred solution of (2R,5S)-2-(benzothiophen-5-yl)-5-methyl-piperidine (2.00 g, 8.64 mmol) in DCM (50.0 mL) Di-tert-butyl dicarbonate (1.98 g, 9.08 mmol, 2.08 mL) was added dropwise. The reaction mixture was stirred at 25° C. for 14 hr. The obtained mixture was washed with water (3*25.0 mL). The organic layer was dried over Na$_2$SO$_4$ and concentrated in vacuo to afford tert-butyl (2R,5S)-2-(benzothiophen-5-yl)-5-methyl-piperidine-1-carboxylate (2.50 g, 7.54 mmol, 87.3% yield) as a light-yellow solid.

LCMS(ESI): [M-boc]$^+$ m/z: calcd 230.2; found 232.0; Rt=1.603.

Step 5: The Synthesis of tert-butyl (2R,5S)-2-(2-bromobenzothiophen-5-yl)-5-methyl-piperidine-1-carboxylate To a stirred solution of tert-butyl (2R,5S)-2-(benzothiophen-5-yl)-5-methyl-piperidine-1-carboxylate (2.94 g, 7.54 mmol) in ACN (29.8 mL) N-bromosuccinimide (1.34 g, 7.54 mmol, 640 μL) was added portion-wise. The reaction mixture was stirred at 25° C. for 14 hr. The obtained mixture was concentrated in vacuo. The residue was diluted with DCM (40.0 mL), washed with water and NaHSO$_4$ solution. The organic layer was dried over Na$_2$SO$_4$ and concentrated in vacuo to afford tert-butyl (2R,5S)-2-(2-bromobenzothiophen-5-yl)-5-methyl-piperidine-1-carboxylate (2.80 g, 6.82 mmol, 90.5% yield) as a red solid.

LCMS(ESI): [M-boc]$^+$ m/z: calcd 310.01; found 310.2; Rt=1.831.

Step 6: The Synthesis of tert-butyl (2R,5S)-5-methyl-2-[2-(1-methyl-3,6-dihydro-2H-pyridin-4-yl)benzothiophen-5-yl]piperidine-1-carboxylate Sodium carbonate (1.45 g, 13.7 mmol) was added to a solution of tert-butyl (2R,5S)-2-(2-bromobenzothiophen-5-yl)-5-methyl-piperidine-1-carboxylate (2.80 g, 6.82 mmol) and 1-methyl-4-(4,4,5,5-tetramethyl-1,3,2-dioxaborolan-2-yl)-3,6-dihydro-2H-pyridine (1.52 g, 6.82 mmol) in Dioxane (20.0 mL) and Water (5.00 mL). The reaction mixture was evacuated and then backfilled with Ar. Pd(dppf)Cl$_2$*DCM (279 mg, 341 μmol) was added. The resulting mixture was stirred at 90° C. for 14 hr. The reaction mixture was concentrated under reduced pressure. The residue was subjected to gradient column chromatography (SiO$_2$; MTBE—MeOH) to afford tert-butyl (2R,5S)-5-methyl-2-[2-(1-methyl-3,6-dihydro-2H-pyridin-4-yl)benzothiophen-5-yl]piperidine-1-carboxylate (2.90 g, 6.80 mmol, 99.6% yield) as a brown solid.

LCMS(ESI): [M+H]$^+$ m/z: calcd 427.29; found 427.2; Rt=1.315.

Step 7: The Synthesis of tert-butyl (2R,5S)-5-methyl-2-[2-(1-methyl-4-piperidyl)benzothiophen-5-yl]piperidine-1-carboxylate Palladium, 5% on activated carbon, 5R452 (0.50 g, 4.70 mmol) was added to a solution of tert-butyl (2R,5S)-5-methyl-2-[2-(1-methyl-3,6-dihydro-2H-pyridin-4-yl)benzothiophen-5-yl]piperidine-1-carboxylate (2.30 g, 5.39 mmol) in Methanol (30.0 mL). The reaction mixture was evacuated and then backfilled with hydrogen. The resulting mixture was stirred at 50° C. for 6 days. The reaction mixture was filtered and concentrated in vacuo to afford tert-butyl (2R,5S)-5-methyl-2-[2-(1-methyl-4-piperidyl)benzothiophen-5-yl]piperidine-1-carboxylate (1.80 g, 4.20 mmol, 77.9% yield) as yellow oil.

LCMS(ESI): [M+H]$^+$ m/z: calcd 429.31; found 429.2; Rt=3.591.

Step 8: The Synthesis of 1-methyl-4-[5-[(2R,5S)-5-methyl-2-piperidyl]benzothiophen-2-yl]piperidine Tert-butyl (2R,5S)-5-methyl-2-[2-(1-methyl-4-piperidyl)benzothiophen-5-yl]piperidine-1-carboxylate (1.80 g, 4.20 mmol) was mixed in Hydrogen chloride solution 4.0 M in dioxane (40.0 g, 1.10 mol, 50.0 mL). The resulting mixture was stirred at 25° C. for 14 hr. The obtained mixture was diluted with MTBE (15.0 mL) and filtered. The filter cake was washed with MTBE and dried in vacuo to afford 1-methyl-4-[5-[(2R,5S)-5-methyl-2-piperidyl]benzothiophen-2-yl]piperidine (1.50 g, 3.74 mmol, 88.9% yield, 2HCl salt) as a brown solid.

LCMS(ESI): [M+H]$^+$ m/z: calcd 329.25; found 329.2; Rt=0.502.

Step 9: The Synthesis of N-(6-amino-5-methyl-3-pyridyl)-2-[(2R,5S)-5-methyl-2-[2-(1-methyl-4-piperidyl)benzothiophen-5-yl]-1-piperidyl]-2-oxo-acetamide (Compound 1220

To a solution of 1-methyl-4-[5-[(2R,5S)-5-methyl-2-piperidyl]benzothiophen-2-yl]piperidine (0.50 g, 1.37 mmol, HCl salt), 2-[(6-amino-5-methyl-3-pyridyl)amino]-2-oxo-acetic acid (267 mg, 1.37 mmol) and Triethylamine (693 mg, 6.85 mmol, 955 μL) in DMF (4.00 mL) HATU (573 mg, 1.51 mmol) was added portion-wise. The reaction mixture was stirred at 25° C. for 1.5 hr. The obtained mixture was subjected to reverse phase HPLC (0-1-5 min 30-30-60% water-ACN, +0.1% vol. of 25% aq. NH$_3$, 30 mL/min, column: YMC-Actus Triart C18, 100×20 mm, 5 μm) to afford N-(6-amino-5-methyl-3-pyridyl)-2-[(2R,5S)-5-methyl-2-[2-(1-methyl-4-piperidyl)benzothiophen-5-yl]-1-piperidyl]-2-oxo-acetamide (23.0 mg, 45.5 μmol, 3.32% yield) as a yellow solid.

$^1$H NMR (600 MHz, DMSO-d$_6$) δ 1.00-1.06 (m, 3H), 1.30-1.40 (m, 1H), 1.59-1.95 (m, 7H), 1.95-2.05 (m, 4H), 2.06-2.12 (m, 2H), 2.19 (s, 3H), 2.30 (d, 1H), 2.82-2.87 (m, 2H), 2.89-3.29 (m, 1H), 3.46-4.06 (m, 1H), 5.23-5.73 (m, 3H), 7.30-7.39 (m, 1H), 7.40-7.52 (m, 2H), 7.67-7.71 (m, 1H), 7.93-8.09 (m, 2H), 10.46-10.60 (m, 1H).

LCMS(ESI): [M+H]$^+$ m/z: calcd 506.3; found 506.2; Rt=1.794.

Example 283. The Synthesis of 2-methoxy-5-[[2-oxo-2-[rac-(2R,5S)-5-methyl-2-[2-[rac-(3R,4S)-1,3-dimethyl-4-piperidyl]-1,3-benzothiazol-5-yl]-1-piperidyl]acetyl]amino]pyridine-3-carboxamide (Compound 1168

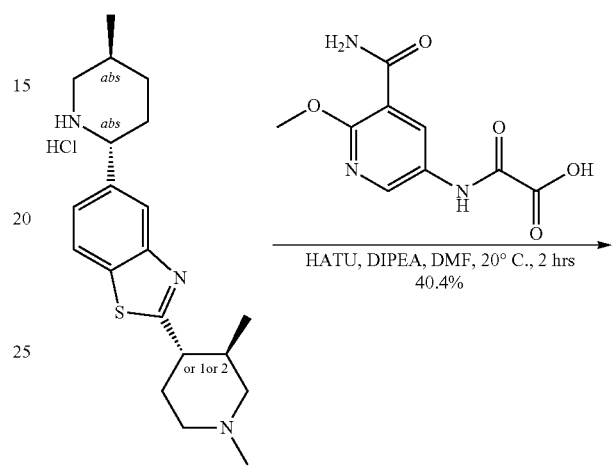

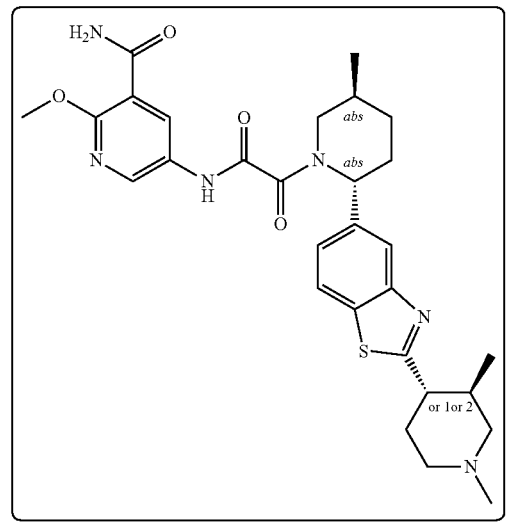

To a mixture of 2-[rac-(3R,4S)-1,3-dimethyl-4-piperidyl]-5-[rac-(2R,5S)-5-methyl-2-piperidyl]-1,3-benzothiazole (80 mg, 0.211 mmol, HCl), 2-[(5-carbamoyl-6-methoxy-3-pyridyl)amino]-2-oxo-acetic acid (76 mg, 0.318 mmol) and HATU (136 mg, 0.358 mmol) in DMF (2 mL) was added DIPEA (0.18 mL, 1.03 mmol). The mixture was stirred at 20° C. for 2 hours. The mixture was purified by preparative HPLC (Instrument: Gilson GX-281 Liquid Handler, Gilson 322 Pump, Gilson 156 UV Detector; Column: Phenomenex C18 80×40 mm×3 μm; Mobile phase A: H$_2$O with 10 mmol NH$_4$HCO$_3$ (v %); Mobile phase B: MeCN; Gradient: B from 36% to 66% in 9.5 min, hold 100% B for 2 min; Flow Rate:

25 mL/min; Column Temperature: 30° C.; Wavelength: 220 nm, 254 nm) to give 2-methoxy-5-[[2-oxo-2-[rac-(2R,5S)-5-methyl-2-[2-[rac-(3R,4S)-1,3-dimethyl-4-piperidyl]-1,3-benzothiazol-5-yl]-1-piperidyl]acetyl]amino]pyridine-3-carboxamide (48 mg, 40.4% yield) as white dry powder. $^1$H NMR (400 MHz, methanol-$d_4$) δ ppm 8.35-8.76 (m, 2H), 7.89-8.03 (m, 2H), 7.37-7.56 (m, 1H), 5.39-5.93 (m, 1H), 4.01-4.16 (m, 3H), 3.76 (d, J=13.9 Hz, 1H), 3.44 (d, J=12.1 Hz, 1H), 2.99-3.22 (m, 2H), 2.71-2.88 (m, 1H), 1.84-2.50 (m, 12H), 1.47 (d, J=11.1 Hz, 1H), 1.14 (d, J=6.9 Hz, 3H), 0.86 (d, J=6.3 Hz, 3H); LCMS (ESI) [M+H]$^+$ m/z: calcd 565.3; found 565.2; HPLC: 99.71%@220 nm, 99.69%@254 nm; 98.1% ee.

Example 284. The Synthesis of 2-methoxy-5-[[2-oxo-2-[rac-(2R,5S)-5-methyl-2-[2-[rac-(3R,4S)-1,3-dimethyl-4-piperidyl]-1,3-benzothiazol-5-yl]-1-piperidyl]acetyl]amino]pyridine-3-carboxamide (WX-TGX-1498A_002) and 2-methoxy-5-[[2-oxo-2-[rac-(2R,5S)-5-methyl-2-[2-[rac-(3R,4R)-1,3-dimethyl-4-piperidyl]-1,3-benzothiazol-5-yl]-1-piperidyl]acetyl]amino]pyridine-3-carboxamide (WX-TGX-1498B_001

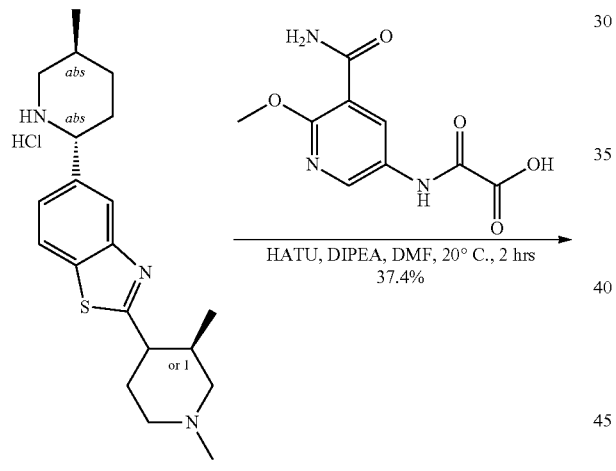

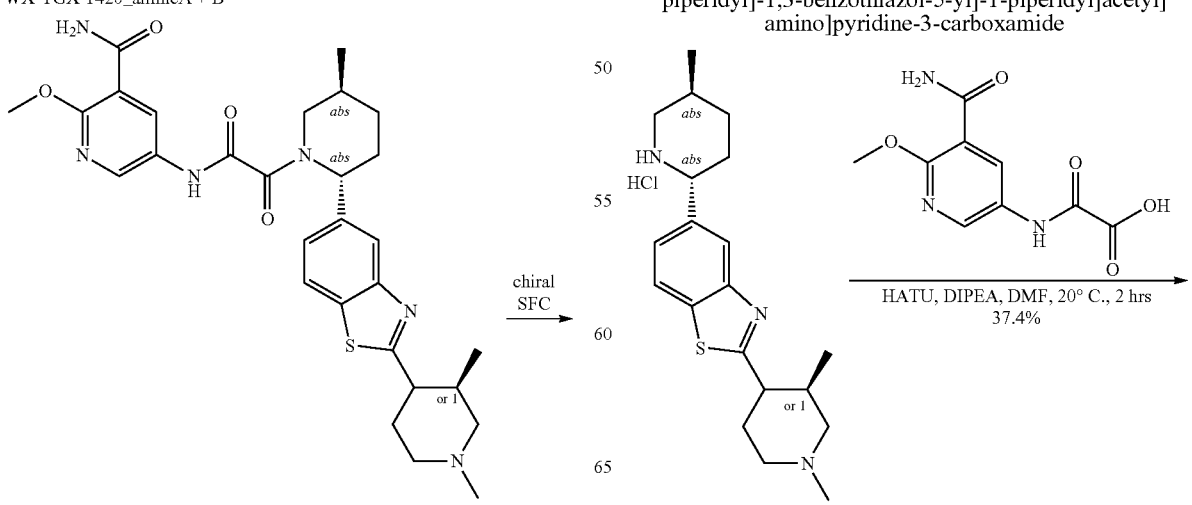

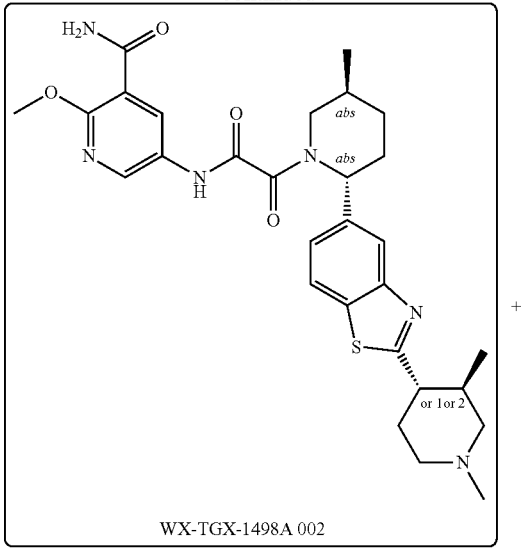

WX-TGX-1498A_002

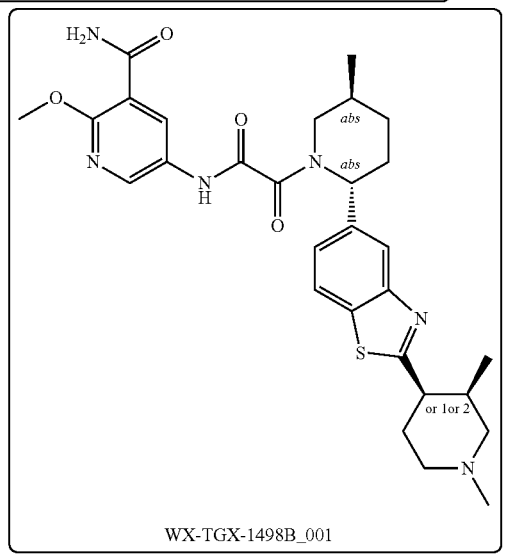

WX-TGX-1498B_001

Step 1: Synthesis of 2-methoxy-5-[[2-oxo-2-[rac-(2R,5S)-5-methyl-2-[2-[rac-(3R)-1,3-dimethyl-4-piperidyl]-1,3-benzothiazol-5-yl]-1-piperidyl]acetyl]amino]pyridine-3-carboxamide

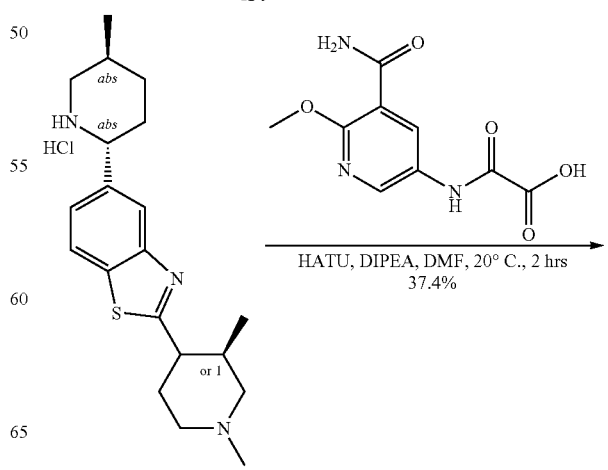

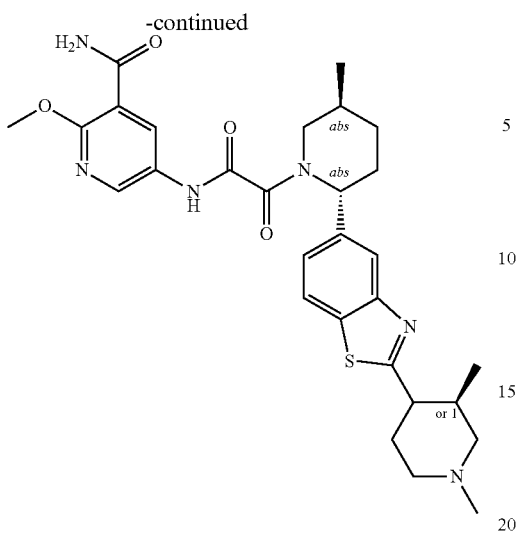

A mixture of 2-[(5-carbamoyl-6-methoxy-3-pyridyl)amino]-2-oxo-acetic acid (85 mg, 355.37 mol), 2-[rac-(3R)-1,3-dimethyl-4-piperidyl]-5-[rac-(2R,5S)-5-methyl-2-piperidyl]-1,3-benzothiazole (80 mg, 0.233 mmol), HATU (130 mg, 0.342 mmol), DIPEA (130 µL, 0.746 mmol) in DMF (4 mL) was stirred at 20° C. for 2 hours. The residue was purified by preparative HPLC (Instrument: Gilson GX-281 Liquid Handler, Gilson 322 Pump, Gilson 156 UV Detector; Column: Phenomenex C18 80×40 mm×3 m; Mobile phase A: H$_2$O with 0.05% NH$_3$—H$_2$O (v %); Mobile phase B: MeCN; Gradient: B from 40% to 70% in 9.5 min, hold 100% B for 0 min; Flow Rate: 30 mL/min; Column Temperature: 30° C.; Wavelength: 220 nm, 254 nm) to afford 2-methoxy-5-[[2-oxo-2-[rac-(2R,5S)-5-methyl-2-[2-[rac-(3R)-1,3-dimethyl-4-piperidyl]-1,3-benzothiazol-5-yl]-1-piperidyl]acetyl]amino]pyridine-3-carboxamide (50 mg, 37.4% yield) as a white solid. LCMS (ESI) [M+H]$^+$ m/z: calcd 565.3, found 565.3

Step 2: Synthesis of 2-methoxy-5-[[2-oxo-2-[rac-(2R,5S)-5-methyl-2-[2-[rac-(3R,4S)-1,3-dimethyl-4-piperidyl]-1,3-benzothiazol-5-yl]-1-piperidyl]acetyl]amino]pyridine-3-carboxamide (WX-TGX-1498A_002) and 2-methoxy-5-[[2-oxo-2-[rac-(2R,5S)-5-methyl-2-[2-[rac-(3R,4R)-1,3-dimethyl-4-piperidyl]-1,3-benzothiazol-5-yl]-1-piperidyl]acetyl]amino]pyridine-3-carboxamide (WX-TGX-1498B_001

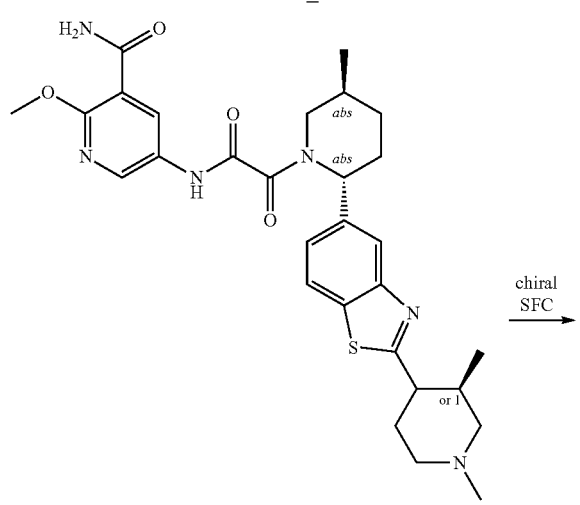

chiral SFC

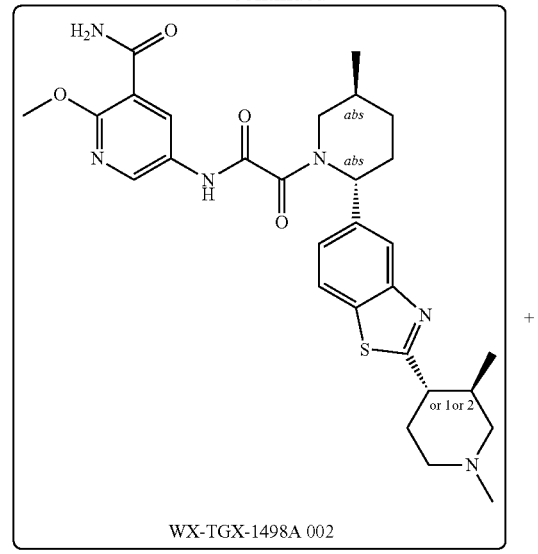

WX-TGX-1498A_002

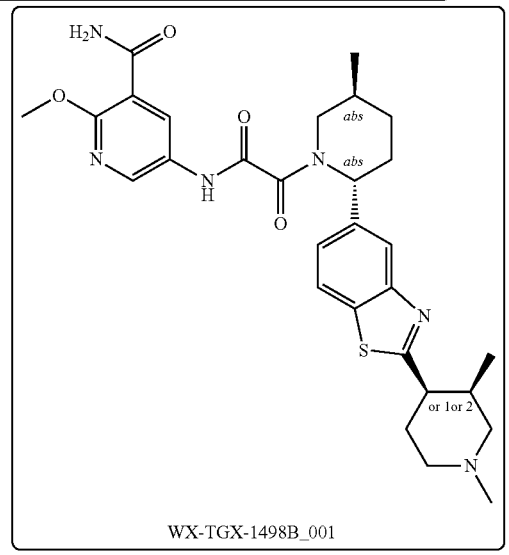

WX-TGX-1498B_001

2-methoxy-5-[[2-oxo-2-[rac-(2R,5S)-5-methyl-2-[2-[rac-(3R)-1,3-dimethyl-4-piperidyl]-1,3-benzothiazol-5-yl]-1-piperidyl]acetyl]amino]pyridine-3-carboxamide (50 mg, 0.089 mmol) was purified by chiral SFC (Instrument: Berger, MULTIGR AM-II; Column: Chiralpak OD 250×30 mm I.D. 10 m; Mobile phase: supercritical CO$_2$/EtOH (0.1% NH$_3$·H$_2$O, v %)=40/40; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford WX-TGX-1498A_002 and TGX-1498B_001.
WX-TGX-1498A_002
2-methoxy-5-[[2-oxo-2-[rac-(2R,5S)-5-methyl-2-[2-[rac-(3R,4S)-1,3-dimethyl-4-piperidyl]-1,3-benzothiazol-5-yl]-1-piperidyl]acetyl]amino]pyridine-3-carboxamide (40 mg, peak 1, Retention time=3.651 min, single unknown enantiomer with trans relative chemistry, white solid).
$^1$H NMR (400 MHz, methanol-d$_4$) δ ppm 8.38-8.90 (m, 2H), 7.84-8.11 (m, 2H), 7.46 (br d, J 8.5 Hz, 1H), 5.43-5.96 (m, 1H), 4.02-4.22 (m, 3H), 3.40-3.86 (m, 1H), 3.13 (br t, J=13.3 Hz, 2H), 2.85 (br d, J 9.3 Hz, 1H), 2.47 (s, 3H), 1.78-2.42 (m, 9H), 1.48 (br d, J 13.1 Hz, 1H), 1.15 (d, J 6.8

Hz, 3H), 0.88 (br d, J 5.5 Hz, 3H); LCMS (ESI) [M+H]+ m/z: calcd 565.3, found 565.3; HPLC: 99.9%/@254 nm; 98.86% ee.

WX-TGX-1498B_001

2-methoxy-5-[[2-oxo-2-[rac-(2R,5S)-5-methyl-2-[2-[rac-(3R,4R)-1,3-dimethyl-4-piperidyl]-1,3-benzothiazol-5-yl]-1-piperidyl]acetyl]amino]pyridine-3-carboxamide (11 mg, peak 2, Retention time=4.177 min, single unknown enantiomer with trans relative chemistry, white solid).

$^1$H NMR (400 MHz, methanol-d$_4$) δ ppm 8.38-8.72 (m, 1H), 7.84-8.06 (m, 2H), 7.26-7.71 (m, 2H), 5.36-6.04 (m, 1H), 3.98-4.27 (m, 3H), 3.35-3.88 (m, 2H), 2.77-3.27 (m, 2H), 1.81-2.58 (m, 9H), 1.48 (br d, J 12.8 Hz, 1H), 1.28 (s, 1H), 1.15 (d, J 7.0 Hz, 3H), 0.93 (br d, J 7.0 Hz, 3H); LCMS (ESI) [M+H]+ m/z: calcd 565.3, found 565.4; HPLC: 100.0%@254 nm; 99.4% ee.

Example 285. The Synthesis of 2-methoxy-5-[[2-oxo-2-[rac-(2R,5S)-5-methyl-2-[2-[rac-(3R,4R)-1,3-dimethyl-4-piperidyl]-1,3-benzothiazol-5-yl]-1-piperidyl]acetyl]amino]pyridine-3-carboxamide (Compound 1127

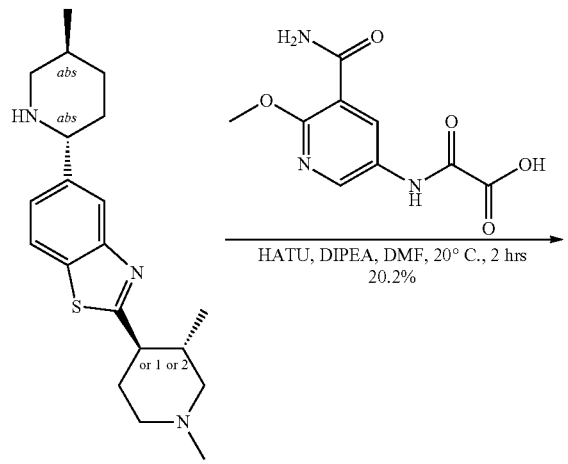

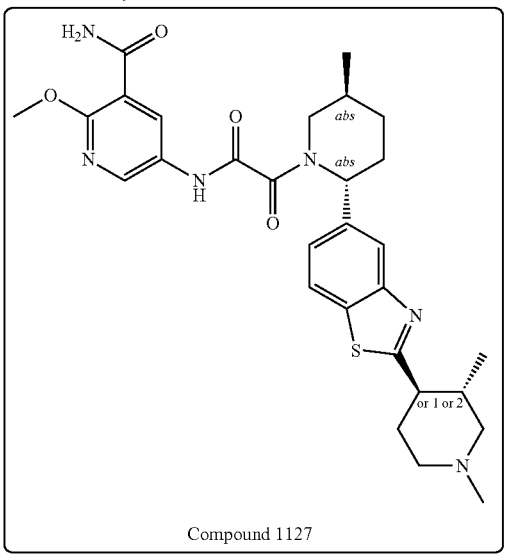

Compound 1127

A mixture of 2-[(5-carbamoyl-6-methoxy-3-pyridyl)amino]-2-oxo-acetic acid (85 mg, 0.355 mmol), 2-[rac-(3S,4R)-1,3-dimethyl-4-piperidyl]-5-[rac-(2R,5S)-5-methyl-2-piperidyl]-1,3-benzothiazole (80 mg, 0.233 mmol), HATU (135 mg, 0.355 mmol), DIPEA (0.13 mL, 0.746 mmol) in DMF (4 mL) was stirred at 20° C. for 2 hours. The mixture was concentrated under reduced pressure. The residue was purified by preparative HPLC (Instrument: Gilson GX-281 Liquid Handler, Gilson 322 Pump, Gilson 156 UV Detector; Column: Phenomenex C18 80*40 mm*3 μm; Mobile phase A: H$_2$O with NH$_4$HCO$_3$ (v %); Mobile phase B: MeCN; Gradient: B from 43% to 73% in 9.5 min, hold 100% B for 1 min; Flow Rate: 25 mL/min; Column Temperature: 30° C.; Wavelength: 220 nm, 254 nm) to afford 2-methoxy-5-[[2-oxo-2-[rac-(2R,5S)-5-methyl-2-[2-[rac-(3S,4R)-1,3-dimethyl-4-piperidyl]-1,3-benzothiazol-5-yl]-1-piperidyl]acetyl]amino]pyridine-3-carboxamide (27 mg, 20.2% yield, single unknown enantiomer) as white solid. $^1$H NMR (400 MHz, methanol-d$_4$) δ ppm 8.59-8.74 (m, 1H), 8.36-8.56 (m, 1H), 7.91-8.04 (m, 2H), 7.45 (br s, 1H), 5.84 (br s, 1H), 4.05-4.13 (m, 3H), 3.76 (br d, J=14.0 Hz, 2H), 2.86 (br s, 2H), 2.02-2.45 (m, 13H), 1.49 (br s, 1H), 1.15 (br s, 3H), 0.86 (br d, J=6.0 Hz, 3H); LCMS (ESI) [M+H]+ m/z: calcd 565.3, found 565.3; HPLC: 98.220%@254 nm, 99.120%@254 nm; 100% ee.

Example 286. The Synthesis of 2-methoxy-5-[[2-oxo-2-[rac-(2R,5S)-5-methyl-2-[2-[rac-(3S,4S)-1,3-dimethyl-4-piperidyl]-1,3-benzothiazol-5-yl]-1-piperidyl]acetyl]amino]pyridine-3-carboxamide (Compound 1185

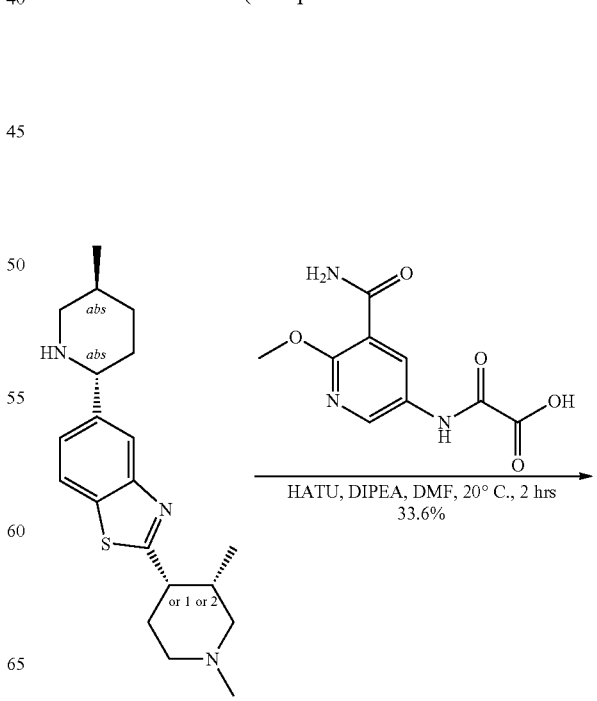

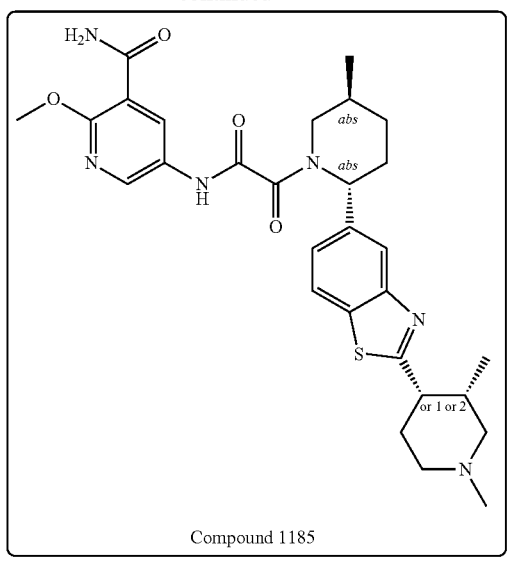

Compound 1185

A mixture of 2-[(5-carbamoyl-6-methoxy-3-pyridyl)amino]-2-oxo-acetic acid (85 mg, 0.355 mmol), 2-[rac-(3S,4S)-1,3-dimethyl-4-piperidyl]-5-[rac-(2R,5S)-5-methyl-2-piperidyl]-1,3-benzothiazole (80 mg, 0.233 mmol), HATU (130 mg, 0.342 mmol), DIPEA (130 μL, 0.746 mmol) in DMF (4 mL) was stirred at 20° C. for 2 hours. The residue was purified by preparative HPLC (Instrument: Gilson GX-281 Liquid Handler, Gilson 322 Pump, Gilson 156 UV Detector; Column: Phenomenex C18 80×40 mm×3 m; Mobile phase A: $H_2O$ with 0.05% $NH_3$—$H_2O$ (v %); Mobile phase B: MeCN; Gradient: B from 42% to 72% in 7.8 min, hold 100% B for 1 min; Flow Rate: 30 mL/min; Column Temperature: 30° C.; Wavelength: 220 nm, 254 nm) to afford 2-methoxy-5-[[2-oxo-2-[rac-(2R,5S)-5-methyl-2-[2-[rac-(3S,4S)-1,3-dimethyl-4-piperidyl]-1,3-benzothiazol-5-yl]-1-piperidyl]acetyl]amino]pyridine-3-carboxamide (45 mg, 33.6% yield) as a white solid.

$^1$H NMR (400 MHz, methanol-$d_4$) δ ppm 8.36-8.75 (m, 2H), 7.91-8.02 (m, 2H), 7.37-7.48 (m, 1H), 5.41-5.93 (m, 1H), 4.02-4.12 (m, 3H), 3.35-3.86 (m, 2H), 3.03-3.26 (m, 1H), 2.88 (br s, 1H), 2.14-2.62 (m, 10H), 1.85-2.13 (m, 3H), 1.47 (br d, J 11.8 Hz, 1H), 1.14 (d, J=7.0 Hz, 3H), 0.93 (br d, J=6.5 Hz, 3H); LCMS (ESI) [M+H]$^+$ m/z: calcd 565.3, found 565.1; HPLC: 98.46%@254 nm; 99.7% ee.

Example 287. The Synthesis of N-(6-amino-5-ethyl-3-pyridyl)-2-oxo-2-[(2R,5S)-5-methyl-2-[2-(1-methyl-4-piperidyl)-7-quinolyl]-1-piperidyl]acetamide (Compound 1365

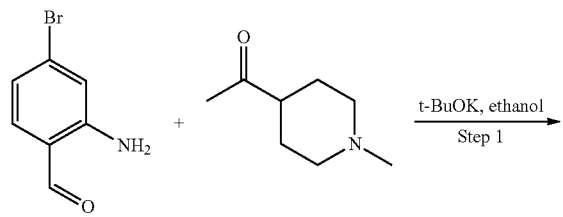

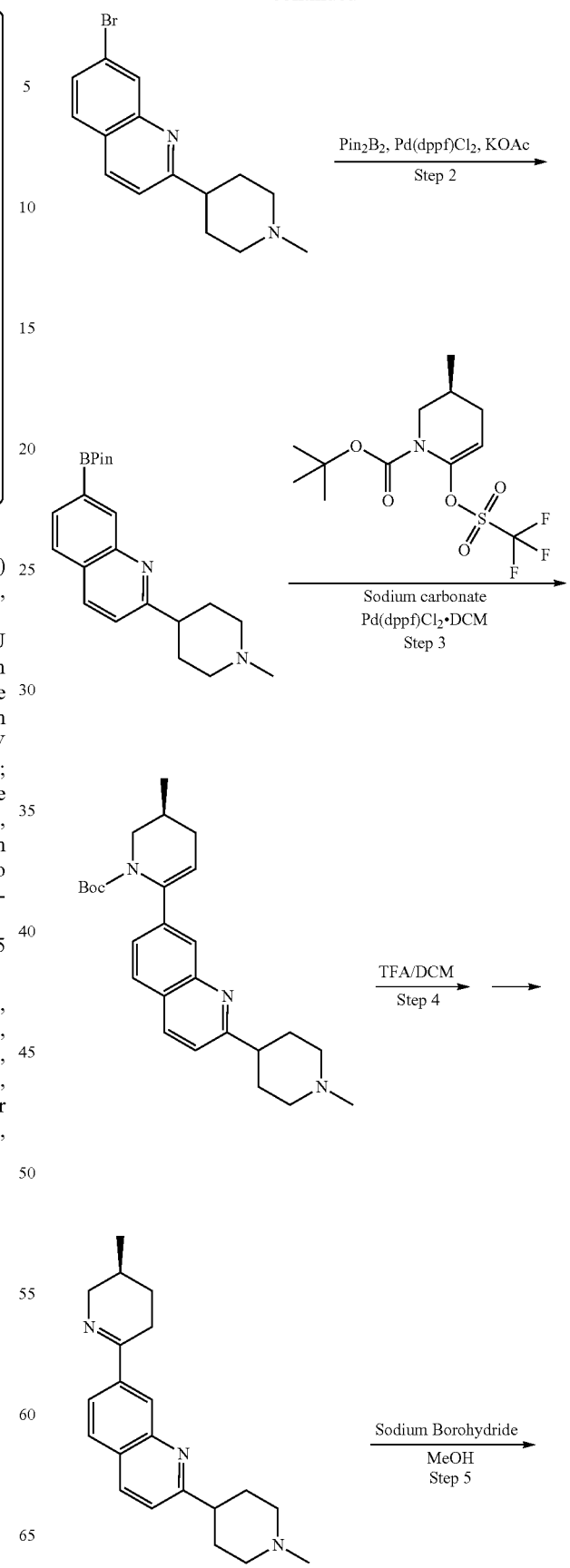

-continued

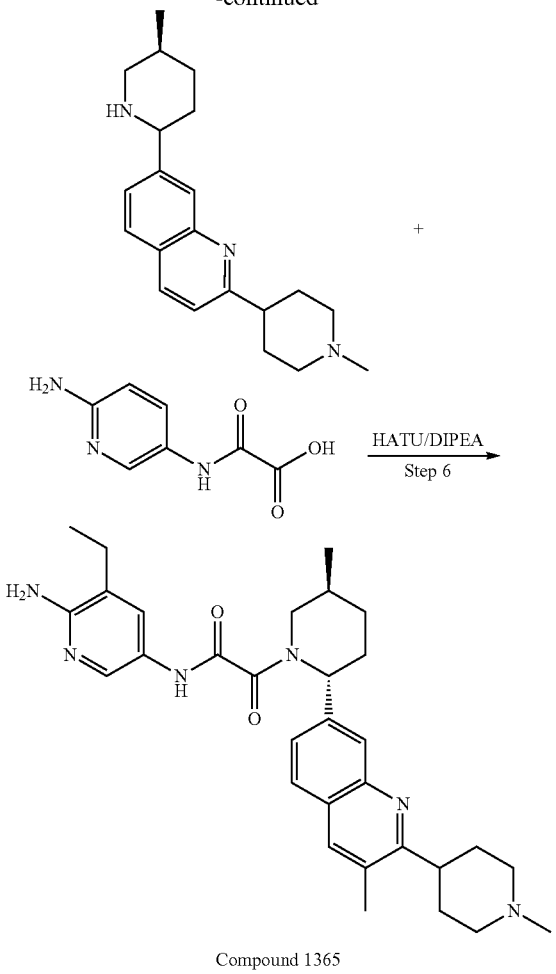

Compound 1365

Step 1: 7-bromo-2-(1-methyl-4-piperidyl)quinoline 2-amino-4-bromo-benzaldehyde (1.3 g, 6.50 mmol), 1-(1-methyl-4-piperidyl)ethanone (917.72 mg, 6.50 mmol) and Sodium tert-butoxide (1.25 g, 13.00 mmol) were mixed in ethanol (20 mL) and stirred for 12 hr at 80° C. The RM was concentrated in vacuo, then treated with DCM, washed with water. Organic phase was dried over $Na_2SO_4$ and evaporated to give 7-bromo-2-(1-methyl-4-piperidyl)quinoline (1.65 g, crude)

LCMS(ESI): $[M+1]^+$ m/z: calcd 304.1; found 305; Rt=0.934 min.

Step 2: 2-(1-methyl-4-piperidyl)-7-(4,4,5,5-tetramethyl-1,3,2-dioxaborolan-2-yl)quinoline A mixture of 7-bromo-2-(1-methyl-4-piperidyl)quinoline (1.95 g, 6.39 mmol) (300 mg), Bis(pinacolato)diboron (2.11 g, 8.31 mmol) and Potassium Acetate (1.88 g, 19.17 mmol, 1.20 mL) in Dioxane (30.03 mL) was degassed with argon for 10 min. Pd(dppf)Cl₂*DCM (521.75 mg, 638.90 µmol) was next added and the reaction mixture was heated at 80° C. for 12 hr. The reaction mixture was filtered, then concentrated in vacuo. The residue was treated with mixture of MTBE-Hex (1:1), filtered and then concentrated under reduced pressure to give 2-(1-methyl-4-piperidyl)-7-(4,4,5,5-tetramethyl-1,3,2-dioxaborolan-2-yl)quinoline (3 g, crude).

LCMS(ESI): $[M+1]^+$ m/z: calcd 352.3; found 353.2; Rt=1.119 min.

Step 3: Tert-butyl (3S)-3-methyl-6-[2-(1-methyl-4-piperidyl)-7-quinolyl]-3,4-dihydro-2H-pyridine-1-carboxylate 2-(1-methyl-4-piperidyl)-7-(4,4,5,5-tetramethyl-1,3,2-dioxaborolan-2-yl)quinoline (2.8 g, 7.95 mmol), Sodium carbonate (2.53 g, 23.84 mmol, 998.15 µL), tert-butyl (3S)-3-methyl-6-(trifluoromethylsulfonyloxy)-3,4-dihydro-2H-pyridine-1-carboxylate (2.74 g, 7.95 mmol) and Pd(dppf)Cl₂*DCM (0.5 g, 612.75 µmol) were mixed in $H_2O$ (15 mL) and dioxane (50 mL) under argon and stirred at 75° C. for 12 hr. Reaction mixture was diluted with water and desired product extracted with DCM, dried over $Na_2SO_4$ and concentrated in vacuo. tert-butyl (3S)-3-methyl-6-[2-(1-methyl-4-piperidyl)-7-quinolyl]-3,4-dihydro-2H-pyridine-1-carboxylate (4 g, crude) was obtained.

LCMS(ESI): $[M+1]^+$ m/z: calcd 421.3; found 422.2; Rt=1.174 min.

Step 4: 2-(1-methyl-4-piperidyl)-7-[(3S)-3-methyl-2,3,4,5-tetrahydropyridin-6-yl]quinoline tert-butyl (3S)-3-methyl-6-[2-(1-methyl-4-piperidyl)-7-quinolyl]-3,4-dihydro-2H-pyridine-1-carboxylate (4 g, 9.49 mmol) was dissolved in DCM (40 mL) and $CF_3COOH$ (15 g, 9.49 mmol) was added. The RM was stirred for 2 hr, then concentrated. The residue was treated with MTBE two times. Black gum was treated with aq. solution of $NaHCO_3$ and then extracted with DCM. Organic phase was dried over $Na_2SO_4$ and then concentrated in vacuo to give 2-(1-methyl-4-piperidyl)-7-[(3S)-3-methyl-2,3,4,5-tetrahydropyridin-6-yl]quinoline (1 g, crude)

LCMS(ESI): $[M+1]^+$ m/z: calcd 321.2; found 322.2; Rt=0.682 min.

Step 5: 2-(1-methyl-4-piperidyl)-7-[(2R,5S)-5-methyl-2-piperidyl]quinoline

To a solution of 2-(1-methyl-4-piperidyl)-7-[(3S)-3-methyl-2,3,4,5-tetrahydropyridin-6-yl]quinoline (1 g, 2.49 mmol) in methanol (30 mL) Sodium Borohydride (188.30 mg, 4.98 mmol, 175.33 µL) was added, then stirred overnight. The RM was concentrated in vacuo, then treated with DCM, filtered and evaporated to give 2-(1-methyl-4-piperidyl)-7-[(2R,5S)-5-methyl-2-piperidyl]quinoline (0.75 g, crude)

LCMS(ESI): $[M+1]^+$ m/z: calcd 323.2; found 324.2; Rt=0.705 min.

Step 6: The Synthesis of N-(6-amino-5-ethyl-3-pyridyl)-2-oxo-2-[(2R,5S)-5-methyl-2-[2-(1-methyl-4-piperidyl)-7-quinolyl]-1-piperidyl]acetamide (Compound 1365

Crude product 2-(1-methyl-4-piperidyl)-7-[(2R,5S)-5-methyl-2-piperidyl]quinoline (100.00 mg, 216.40 µmol) from previous stage was mixed with TEA (109.49 mg, 1.08 mmol, 150.81 µL) in DMSO (2 mL), next 2-[(6-amino-5-ethyl-3-pyridyl)amino]-2-oxo-acetic acid (54.33 mg, 259.68 µmol) and HATU (98.74 mg, 259.68 µmol) were added and stirred overnight. RM was treated with water and desired product was filtered, washed with water and dissolved in DMSO, then subjected to HPLC. HPLC data: SYSTEM 2-10 min 30-60% ACN+FA 30 ml/min (loading pump 4 ml ACN) column: SunFire 100*19 mm, 5 microM N-(6-amino-5-ethyl-3-pyridyl)-2-oxo-2-[(2R,5S)-5-methyl-2-[2-(1-methyl-4-piperidyl)-7-quinolyl]-1-piperidyl]acetamide (42.3 mg, 82.19 μmol, 37.98% yield) was obtained.

¹H NMR (600 MHz, dmso) δ 1.03-1.15 (m, 6H), 1.33-1.44 (m, 1H), 1.70-1.76 (m, 1H), 1.86-1.94 (m, 5H), 2.10-2.20 (m, 3H), 2.27-2.31 (m, 3H), 2.32-2.35 (m, 1H), 2.37-2.43 (m, 2H), 2.80-2.88 (m, 2H), 2.97-3.00 (m, 2H), 4.08-4.24 (m, 1H), 5.35-5.78 (m, 3H), 7.42-7.49 (m, 2H), 7.51-7.57 (m, 1H), 7.80-7.86 (m, 1H), 7.92-7.98 (m, 1H), 7.99-8.10 (m, 1H), 8.23-8.31 (m, 1H), 10.54-10.66 (m, 1H).

LCMS(ESI): [M+1]⁺ m/z: calcd 514.3; found 515.2; Rt=2.125 min.

Example 288. Synthesis of N-(6-amino-5-methyl-3-pyridyl)-2-[(2R,5S)-2-(2-deuterio-1,3-benzothiazol-5-yl)-5-methyl-1-piperidyl]-2-oxo-acetamide (WX-TANT_17

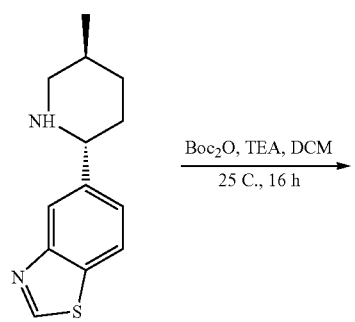

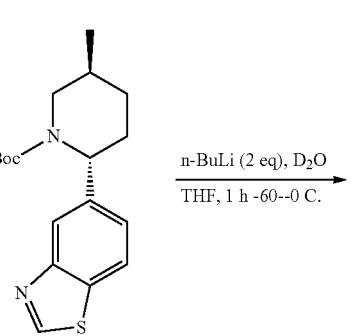

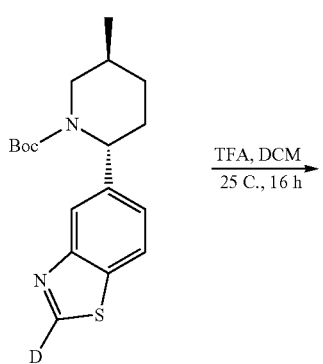

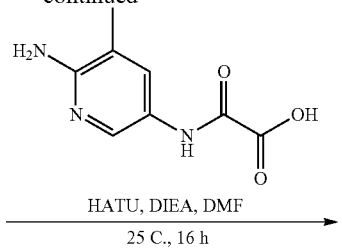

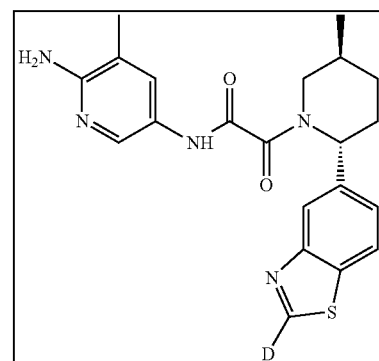

Step 1: Synthesis of tert-butyl (2R,5S)-2-(1,3-benzothiazol-5-yl)-5-methyl-piperidine-1-carboxylate (ES18795-7

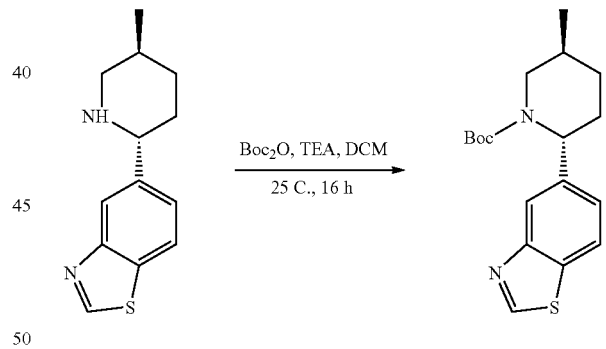

A mixture of 5-[(2R,5S)-5-methyl-2-piperidyl]-1,3-benzothiazole (2 g, 8.61 mmol, 1 eq), TEA (1.74 g, 17.22 mmol, 2.40 mL, 2 eq), Boc2O (2.82 g, 12.91 mmol, 2.97 mL, 1.5 eq) in DCM (10 mL) was degassed and purged with N₂ for 3 times, and then the mixture was stirred at 25° C. for 16 hr under N₂ atmosphere. LC-MS showed Reactant 1 was consumed completely, DCM was evaporated. The residue was purified by column chromatography (SiO₂, Petroleum ether/Ethyl acetate=0/1 to 3/1), Compound tert-butyl (2R,5S)-2-(1,3-benzothiazol-5-yl)-5-methyl-piperidine-1-carboxylate (2.4 g, 7.22 mmol, 83.86% yield) was obtained as a white solid.

¹H NMR (400 MHz, DMSO-d₆) δ ppm 9.19-9.52 (m, 1H) 8.15 (d, J=8.38 Hz, 1H) 7.82-7.94 (m, 1H) 7.36 (dd, J=8.50, 1.25 Hz, 1H) 5.33 (t, J=4.57 Hz, 1H) 3.67 (br d, J=13.38 Hz, 1H) 3.00 (dd, J=13.45, 3.81 Hz, 1H) 2.01-2.22 (m, 2H) 1.82

(br s, 1H) 1.56-1.72 (m, 1H) 1.18-1.33 (m, 1H) 0.99 (d, J=6.88 Hz, 3H). LCMS (ESI) [M+H]+ m/z calcd 333.1, found 333.2.

Step 2: Synthesis of tert-butyl (2R,5S)-2-(2-deuterio-1,3-benzothiazol-5-yl)-5-methylpiperidine-1-carboxylate (ES18795-8

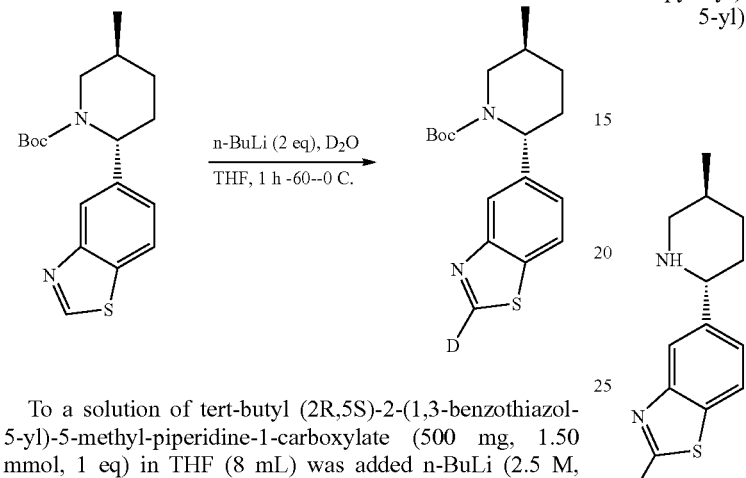

To a solution of tert-butyl (2R,5S)-2-(1,3-benzothiazol-5-yl)-5-methyl-piperidine-1-carboxylate (500 mg, 1.50 mmol, 1 eq) in THF (8 mL) was added n-BuLi (2.5 M, 902.37 uL, 1.5 eq) dropwise at −60° C. Then D2O (602.4 mg, 30.1 mmol, 20 eq) was added at 0° C. The resulting mixture was stirred at 0° C. for 30 min. LCMS showed the reaction was completed. The reaction mixture was concentrated to give a residue. The residue was purified by prep-HPLC (basic condition). Compound tertbutyl(2R,5S)-2-(2-deuterio-1,3-benzothiazol-5-yl)-5-methyl-piperidine-1-carboxylate (250 mg, 749.70 umol, 49.85% yield) was obtained as a white solid. 1H NMR (400 MHz, DMSO-$d_6$) δ ppm 9.40 (s, 1H) 8.15 (d, J=8.38 Hz, 1H) 7.84-7.94 (m, 1H) 7.36 (dd, J=8.38, 1.25 Hz, 1H) 5.33 (t, J=4.57 Hz, 1H) 3.67 (br d, J=13.51 Hz, 1H) 3.01 (dd, J=13.51, 3.75 Hz, 1H) 2.04-2.22 (m, 2H) 1.82 (br s, 1H) 1.53-1.71 (m, 1H) 1.22-1.33 (m, 1H) 1.00 (d, J=7.00 Hz, 3H). LCMS (ESI) [M+H]+ m/z calcd 334.1, found 334.1.

Step 3: Synthesis of 2-deuterio-5-[(2R,5S)-5-methyl-2-piperidyl]-1,3-benzothiazole (ES18795

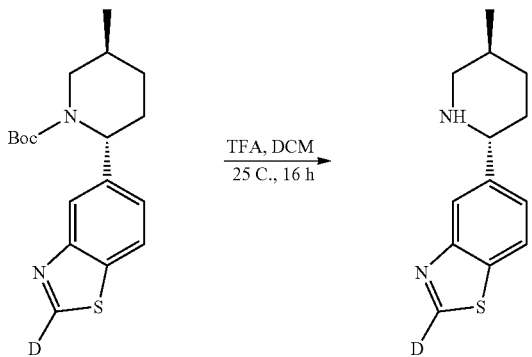 [SMILES: [2H]c1nc2cc([C@H]3CC[C@H](C)CN3C(=O)OC(C)(C)C)ccc2s1 ; [2H]c1nc2cc([C@H]3CC[C@H](C)CN3)ccc2s1]

A mixture of tert-butyl (2R,5S)-2-(2-deuterio-1,3-benzothiazol-5-yl)-5-methyl-piperidine-1-carboxylate (250 mg, 749.70 umol, 1 eq) in TFA/DCM (5 mL) was degassed and purged with N2 for 3 times, and then the mixture was stirred at 25° C. for 2 h under N2 atmosphere. LCMS showed the reaction was completed. TFA/DCM was evaporated. The crude product 2-deuterio-5-[(2R,5S)-5-methyl-2-piperidyl]-1,3-benzothiazole (175 mg, crude) as white solid was used into the next step without further purification. LCMS (ESI) [M+H]+ m/z calcd 234.1, found 234.1.

Step 4: Synthesis of N-(6-amino-5-methyl-3-pyridyl)-2-[(2R,5S)-2-(2-deuterio-1,3-benzothiazol-5-yl)-5-methyl-1-piperidyl]-2-oxo-acetamide (ES18795-12

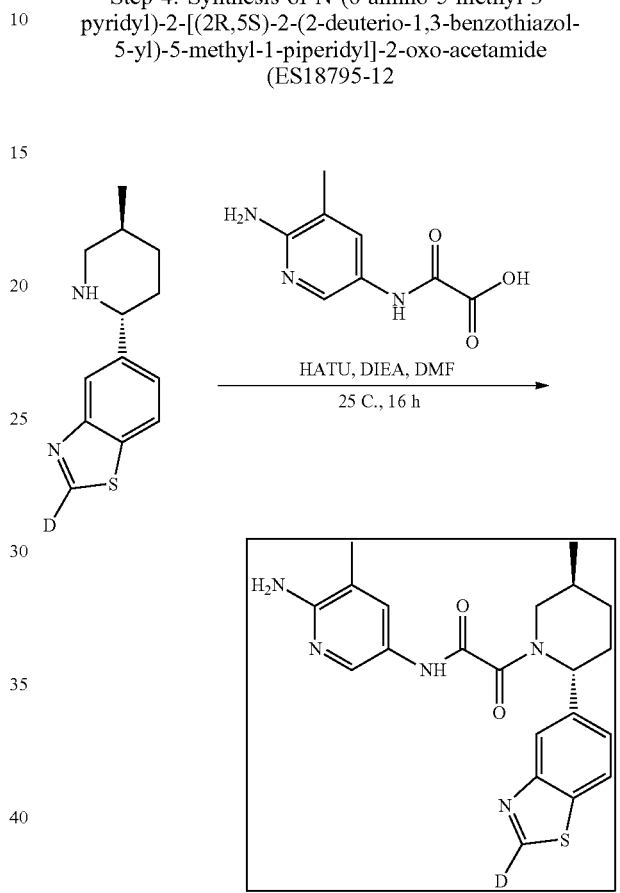

A mixture of 2-deuterio-5-[(2R,5S)-5-methyl-2-piperidyl]-1,3-benzothiazole (175 mg, 749.95 umol, 1 eq), 2-[(6-amino-5-methyl-3-pyridyl)amino]-2-oxo-acetic acid (220 mg, 1.13 mmol, 1.50 eq), HATU (570.30 mg, 1.50 mmol, 2 eq), DIEA (484.63 mg, 3.75 mmol, 653.14 uL, 5 eq) and in DMF (10 mL) was degassed and purged with N2 for 3 times, and then the mixture was stirred at 25° C. for 16 h under N2 atmosphere. LC-MS showed ~80% desired compound was detected. The reaction mixture was extracted with EtOAc 30 mL (10 mL*3). The combined organic layers were washed with saturated aq. NaCl (20 mL), dried over Na2SO4, filtered and concentrated under reduced pressure to give a residue. The residue was purified by prep-HPLC (basic condition). Compound N-(6-amino-5-methyl-3-pyridyl)-2-[(2R,5S)-2-(2-deuterio-1,3-benzothiazol-5-yl)-5-methyl-1-piperidyl]-2-oxo-acetamide (52 mg, 126.67 umol, 16.89% yield) was obtained as a white solid. 1H NMR (400 MHz, DMSO-$d_6$) δ ppm 10.33 (br s, 1H)8.15 (d, J=8.44 Hz, 1H)8.05 (s, 2H) 7.49 (br d, J=8.56 Hz, 2H)5.17-5.88 (m, 3H)2.12-2.38 (m, 2H) 2.00-2.11 (m, 3H) 1.93 (br s, 1H) 1.72-1.85 (m, 1H) 1.38 (br d, J=9.90 Hz, 1H) 1.07 (d, J=6.97 Hz, 3H). LCMS (ESI) [M+H]+ m/z calcd 411.1, found 411.1.

1891
Example 289. The Synthesis of N-(6-amino-5-ethyl-3-pyridyl)-2-oxo-2-[(2R,5S)-5-methyl-2-[3-methyl-2-(1-methyl-4-piperidyl)-7-quinolyl]-1-piperidyl]acetamide (Compound 1368
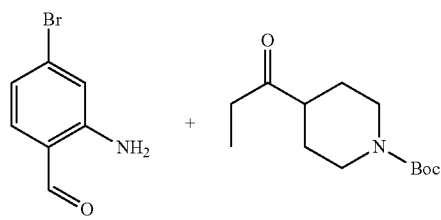
t-BuOK, ethanol
Step 1
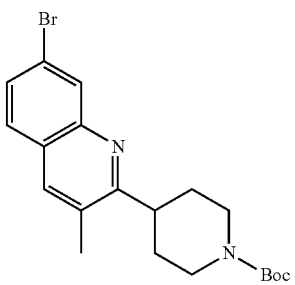
TFA/DCM
Step 2
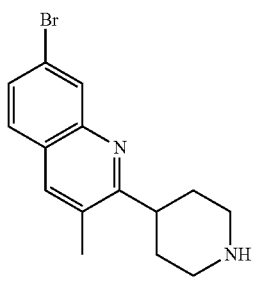
Formalin,
Sodium cyanoborohydride
Step 3
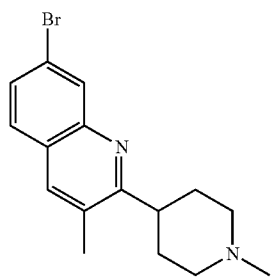
Pin₂B₂, Pd(dppf)Cl₂, KOAc
Step 4
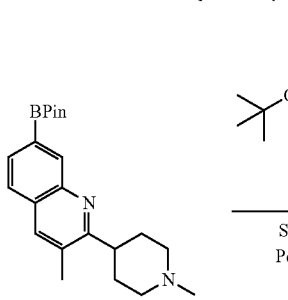
Sodium carbonate
Pd(dppf)Cl₂·DCM
Step 5
1892
-continued
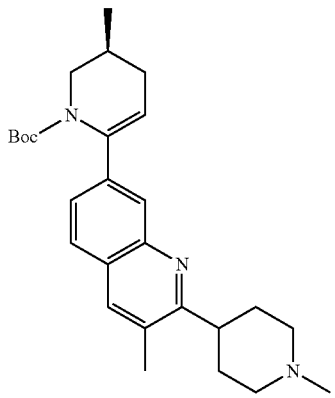
TFA/DCM
Step 6
Sodium Borohydride
MeOH
Step 7
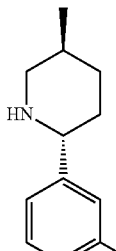
+
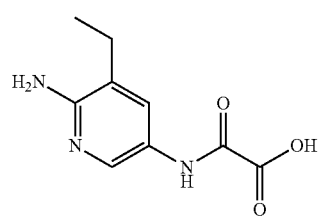
HATU/DIPEA
Step 8

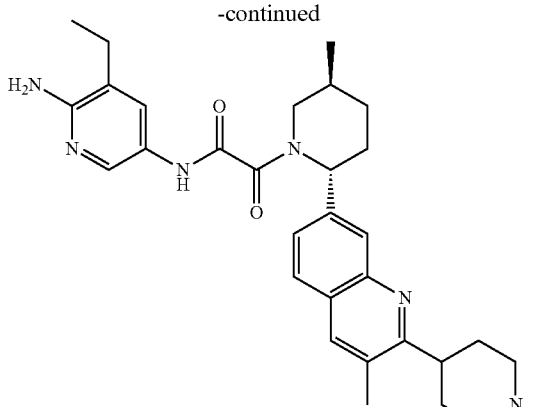

Compound 1368

Step 1: Tert-butyl 4-(7-bromo-3-methyl-2-quinolyl)piperidine-1-carboxylate 2-amino-4-bromo-benzaldehyde (1.5 g, 7.50 mmol), tert-butyl 4-propanoylpiperidine-1-carboxylate (1.81 g, 7.50 mmol) and Sodium tert-butoxide (1.44 g, 15.00 mmol) were mixed in ethanol (20 mL) and stirred for 12 hr at 80° C. The RM was concentrated in vacuo, then treated with DCM, washed with water. Organic phase was dried over $Na_2SO_4$ and evaporated to give tert-butyl 4-(7-bromo-3-methyl-2-quinolyl)piperidine-1-carboxylate (2.2 g, crude)

LCMS(ESI): $[M+1]^+$ m/z: calcd 405.3; found 406.0; Rt=1.771 min.

Step 2: 7-bromo-3-methyl-2-(4-piperidyl)quinoline tert-butyl 4-(7-bromo-3-methyl-2-quinolyl)piperidine-1-carboxylate (2.5 g, 6.17 mmol) was dissolved in DCM (19.87 mL) and Trifluoroacetic acid (15 g, 131.55 mmol, 10.14 mL) was added dropwise, then stirred for 0.5 hr. The RM was concentrated, treated with aq. solution of $NaHCO_3$ and desired product was extracted with DCM. Organic phase was dried over $Na_2SO_4$ and then evaporated to give 7-bromo-3-methyl-2-(4-piperidyl)quinoline (1.6 g, crude)

LCMS(ESI): $[M+1]^+$ m/z: calcd 305.2; found 306.2; Rt=0.781 min.

Step 3: 7-bromo-3-methyl-2-(1-methyl-4-piperidyl)quinoline

Sodium cyanoborohydride (1.77 g, 28.10 mmol) was added in 4 portions to a mixture of 7-bromo-3-methyl-2-(4-piperidyl)quinoline (1.6 g, 4.68 mmol, HCl) and Formalin (1.90 g, 23.41 mmol, 1.75 mL, 37% purity) in methanol (20.08 mL) and stirred overnight. The reaction mixture was treated with aq. solution of $NaHCO_3$ and desired product was extracted with 100 ml of DCM, dried over $Na_2SO_4$ and concentrated in vacuo to give 7-bromo-3-methyl-2-(1-methyl-4-piperidyl)quinoline (1.1 g, crude)

LCMS(ESI): $[M+1]^+$ m/z: calcd 318.1; found 321.2; Rt=0.958 min.

Step 4: 3-methyl-2-(1-methyl-4-piperidyl)-7-(4,4,5,5-tetramethyl-1,3,2-dioxaborolan-2-yl)quinoline A mixture of 7-bromo-3-methyl-2-(1-methyl-4-piperidyl)quinoline (1.1 g, 3.45 mmol), Bis(pinacolato)diboron (1.14 g, 4.48 mmol) and Potassium Acetate (1.01 g, 10.34 mmol, 646.17 μL) in Dioxane (20 mL) was degassed with argon for 10 min. Pd(dppf)$Cl_2$*DCM (281.39 mg, 344.57 μmol) was next added and the reaction mixture was heated at 80° C. for 12 hr. The reaction mixture was filtered, then concentrated in vacuo. The residue was treated with mixture of MTBE-Hex (1:1), filtered and then concentrated under reduced pressure to give 3-methyl-2-(1-methyl-4-piperidyl)-7-(4,4,5,5-tetramethyl-1,3,2-dioxaborolan-2-yl)quinoline (2.2 g, crude).

LCMS(ESI): $[M+1]^+$ m/z: calcd 366.2; found 367.2; Rt=1.193 min.

Step 5: Tert-butyl (3S)-3-methyl-6-[3-methyl-2-(1-methyl-4-piperidyl)-7-quinolyl]-3,4-dihydro-2H-pyridine-1-carboxylate 3-methyl-2-(1-methyl-4-piperidyl)-7-(4,4,5,5-tetramethyl-1,3,2-dioxaborolan-2-yl)quinoline (2 g, 5.46 mmol), Sodium carbonate (1.74 g, 16.38 mmol, 685.66 μL), tert-butyl (3S)-3-methyl-6-(trifluoromethylsulfonyloxy)-3,4-dihydro-2H-pyridine-1-carboxylate (1.89 g, 5.46 mmol) and Pd(dppf)$Cl_2$*DCM (343.47 mg, 420.92 μmol) were mixed in $H_2O$ (15 mL) and dioxane (50 mL) under argon and stirred at 75° C. for 12 hr. Reaction mixture was diluted with water and desired product was extracted with DCM, dried over $Na_2SO_4$ and concentrated in vacuo. tert-butyl rac-(3S)-3-methyl-6-[3-methyl-2-(1-methyl-4-piperidyl)-7-quinolyl]-3,4-dihydro-2H-pyridine-1-carboxylate (2.8 g, crude) was obtained.

LCMS(ESI): $[M+1]^+$ m/z: calcd 435.3; found 436.3; Rt=1.161 min.

Step 6: The Synthesis of 3-methyl-2-(1-methyl-4-piperidyl)-7-[(3S)-3-methyl-2,3,4,5-tetrahydropyridin-6-yl]quinoline tert-butyl rac-(3S)-3-methyl-6-[3-methyl-2-(1-methyl-4-piperidyl)-7-quinolyl]-3,4-dihydro-2H-pyridine-1-carboxylate (2.8 g, 2.89 mmol) was dissolved in DCM (40 mL) and $CF_3COOH$ (15 g, 2.89 mmol) was added. The RM was stirred for 3 hr, then concentrated. The residue was treated with MTBE two times. Black gum was treated with aq. solution of $NaHCO_3$ and then extracted with DCM. Organic phase was dried over $Na_2SO_4$ and then concentrated in vacuo to give 3-methyl-2-(1-methyl-4-piperidyl)-7-[rac-(3S)-3-methyl-2,3,4,5-tetrahydropyridin-6-yl]quinoline (600 mg, crude)

LCMS(ESI): $[M+1]^+$ m/z: calcd 335.2; found 336.2; Rt=0.737 min.

Step 7: The Synthesis of 3-methyl-2-(1-methyl-4-piperidyl)-7-[(2R,5S)-5-methyl-2-piperidyl]quinoline To a solution of 3-methyl-2-(1-methyl-4-piperidyl)-7-[rac-(3S)-3-methyl-2,3,4,5-tetrahydropyridin-6-yl]quinoline (600 mg, 1.25 mmol) in methanol (15 mL) Sodium Borohydride (94.73 mg, 2.50 mmol, 88.20 μL) was added, then stirred overnight. The RM was concentrated in vacuo, then treated with DCM and water, organic phase was washed with water, dried over $Na_2SO_4$ and evaporated to give 3-methyl-2-(1-methyl-4-piperidyl)-7-[rac-(2R,5S)-5-methyl-2-piperidyl]quinoline (0.5 g, crude).

LCMS(ESI): $[M+1]^+$ m/z: calcd 337.2; found 338.2; Rt=0.765 min.

Step 8: The Synthesis of N-(6-amino-5-ethyl-3-pyridyl)-2-oxo-2-[(2R,5S)-5-methyl-2-[3-methyl-2-(1-methyl-4-piperidyl)-7-quinolyl]-1-piperidyl]acetamide (Compound 1868

Crude product 3-methyl-2-(1-methyl-4-piperidyl)-7-[rac-(2R,5S)-5-methyl-2-piperidyl]quinoline (100.00 mg, 192.59 µmol) from previous stage was mixed with TEA (97.44 mg, 962.96 µmol, 134.22 µL) in DMSO (1.95 mL), next 2-[(6-amino-5-ethyl-3-pyridyl)amino]-2-oxo-acetic acid (48.35 mg, 231.11 µmol) and HATU (87.88 mg, 231.11 µmol) were added and stirred overnight. RM was treated with water and desired product was filtered, washed with water and dissolved in DMSO, then subjected to HPLC. HPLC data: SYSTEM 2-10 min 30-60% ACN+FA 30 ml/min (loading pump 4 ml ACN) column: SunFire 100*19 mm, 5 microM N-(6-amino-5-ethyl-3-pyridyl)-2-oxo-2-[rac-(2R,5S)-5-methyl-2-[3-methyl-2-(1-methyl-4-piperidyl)-7-quinolyl]-1-piperidyl]acetamide (14.2 mg, 26.86 µmol, 13.95% yield) was obtained.

$^1$H NMR (600 MHz, dmso) δ 1.02-1.14 (m, 6H), 1.33-1.42 (m, 1H), 1.69-2.02 (m, 7H), 2.09-2.35 (m, 9H), 2.40-2.43 (m, 2H), 2.94-3.02 (m, 4H), 3.50-4.09 (m, 1H), 5.29-5.77 (m, 3H), 7.41-7.54 (m, 2H), 7.76-7.87 (m, 2H), 7.99-8.09 (m, 2H), 10.53-10.61 (m, 1H).

LCMS(ESI): [M+1]$^+$ m/z: calcd 530.2; found 528.4; Rt=2.396 min.

Example 290. The Synthesis of N-(6-amino-5-ethyl-3-pyridyl)-2-oxo-2-[rac-(2R,5S)-2-[4-(4-isopropylpiperazin-1-yl)-3-methyl-phenyl]-5-methyl-1-piperidyl]acetamide (Compound 1163

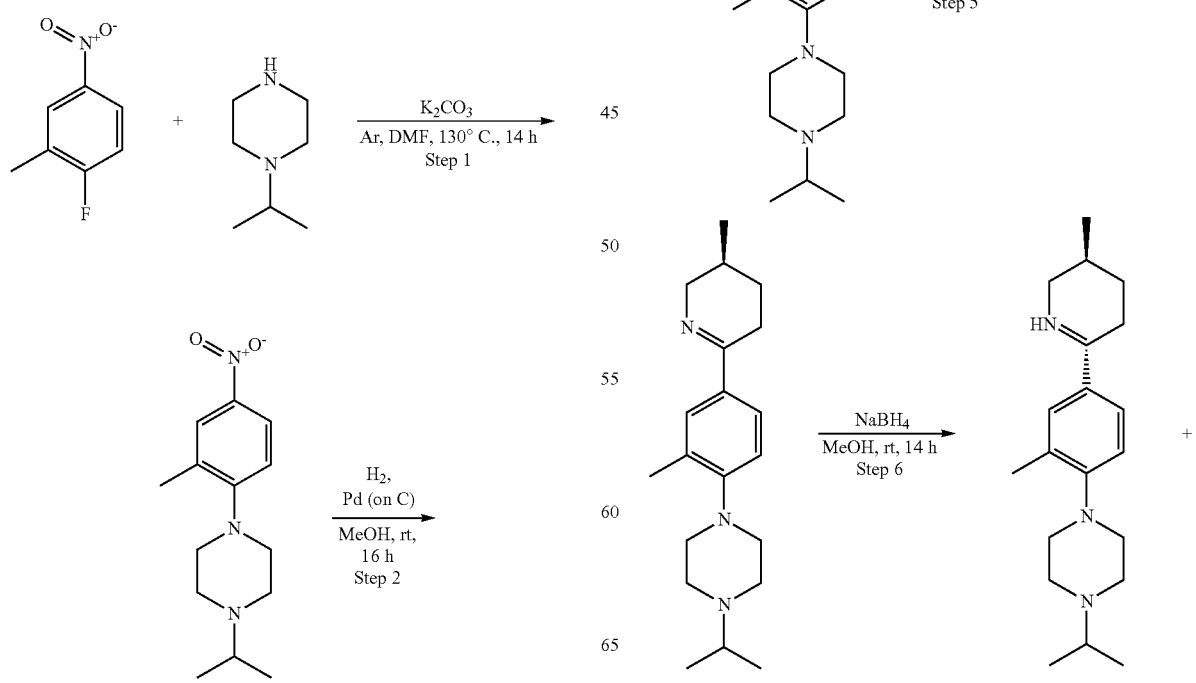

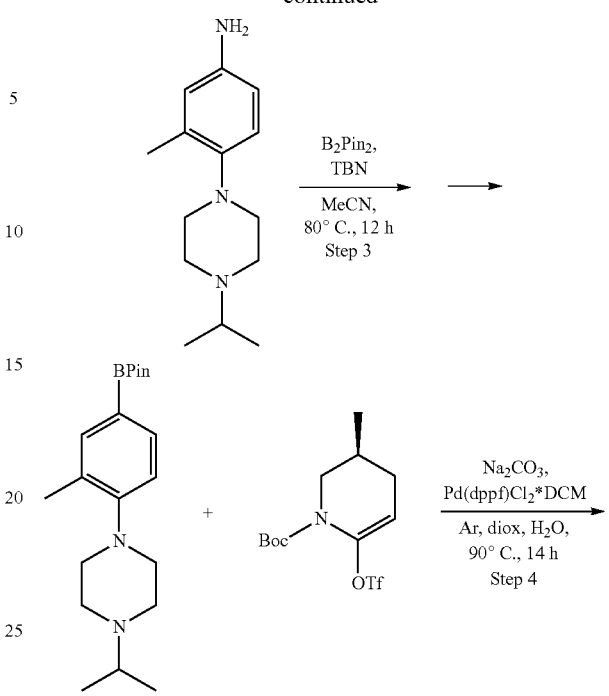

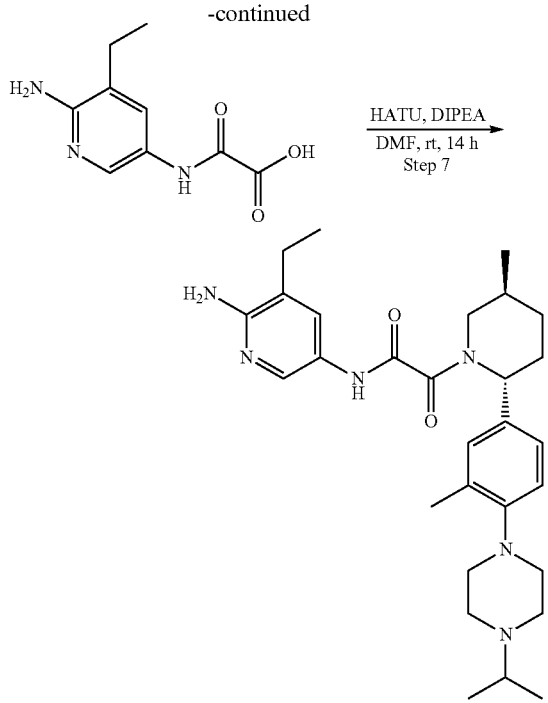

Step 1: The Synthesis of
1-isopropyl-4-(2-methyl-4-nitro-phenyl)piperazine

1-Isopropylpiperazine (2.5 g, 19.50 mmol, 2.79 mL), 1-fluoro-2-methyl-4-nitro-benzene (4.23 g, 27.30 mmol), potassium carbonate (6.74 g, 48.75 mmol, 2.94 mL) were mixed in DMF (20 mL) under Ar. Reaction mixture was stirred overnight at 130° C. After cooling to room temperature, the reaction mixture was diluted with water, extracted with EtOAc. Organic phase was evaporated in vacuo giving 1-isopropyl-4-(2-methyl-4-nitro-phenyl)piperazine (4.8 g, crude)

LCMS(ESI): [M+H]⁺ m/z: calcd 264.2; found 264.2; Rt=0.880 min.

Step 2: The Synthesis of
4-(4-isopropylpiperazin-1-yl)-3-methyl-aniline

The mixture of 1-isopropyl-4-(2-methyl-4-nitro-phenyl)piperazine (4.8 g, 18.23 mmol) and Pd/C (1.94 g, 18.23 mmol) in Methanol was stirred at 25° C. for 16 hr under H₂ atmosphere. The mixture was filtrated and filtrate was evaporated. The residue was crystalized in hexane to give 4-(4-isopropylpiperazin-1-yl)-3-methyl-aniline (2.7 g, 11.57 mmol, 63.48% yield).

LCMS(ESI): [M+H]⁺ m/z: calcd 234.2; found 234.4; Rt=0.539 min.

Step 3: The Synthesis of 1-isopropyl-4-[2-methyl-4-(4,4,5,5-tetramethyl-1,3,2-dioxaborolan-2-yl)phenyl]piperazine 4-(4-isopropylpiperazin-1-yl)-3-methyl-aniline (2.65 g, 11.36 mmol) and Bis(pinacolato)diboron (3.46 g, 13.63 mmol) were weighed in a round-bottom flask. MeCN (25 mL) and tert-butyl nitrite (1.76 g, 17.03 mmol, 2.03 mL) were then added in succession. The resulting reaction solution was stirred for 12 hr at 80° C. (N₂ evolution completed within 5 to 15 min). The solution was then concentrated under reduced pressure, and the crude residue was purified by flash chromatography to obtain 1-isopropyl-4-[2-methyl-4-(4,4,5,5-tetramethyl-1,3,2-dioxaborolan-2-yl)phenyl]piperazine (6 g, crude).

LCMS(ESI): [M+H]⁺ m/z: calcd 345.2; found 345.2; Rt=1.027 min.

Step 4: The Synthesis of tert-butyl rac-(3S)-6-[4-(4-isopropylpiperazin-1-yl)-3-methyl-phenyl]-3-methyl-3,4-dihydro-2H-pyridine-1-carboxylate 1-isopropyl-4-[2-methyl-4-(4,4,5,5-tetramethyl-1,3,2-dioxaborolan-2-yl)phenyl]piperazine (5.8 g, 16.85 mmol), tert-butyl rac-(3S)-3-methyl-6-(trifluoromethylsulfonyloxy)-3,4-dihydro-2H-pyridine-1-carboxylate (5.82 g, 16.85 mmol) and Sodium carbonate (3.57 g, 33.69 mmol, 1.41 mL) were mixed together in a mixture of Dioxane (60 mL) and Water (20 mL). The resulting mixture was purged with argon for 10 min and Pd(dppf)Cl₂ DCM (687.85 mg, 842.29 μmol) was added. The resulting mixture was heated at 90° C. overnight. The resulting mixture was cooled and diluted with water (5 mL). The resulting mixture was extracted with EtOAc (2*15 mL) and combined organic layers were washed with brine (10 mL), dried over Na₂SO₄, filtered, and concentrated in vacuo.

LCMS(ESI): [M+H]⁺ m/z: calcd 414.2; found 414.2; Rt=1.287 min.

Step 5: The Synthesis of 1-isopropyl-4-[2-methyl-4-[rac-(3S)-3-methyl-2,3,4,5-tetrahydropyridin-6-yl]phenyl]piperazine Trifluoroacetic acid (23.16 g, 203.10 mmol, 15.65 mL) was added in one portion to a stirred solution of tert-butyl rac-(3S)-6-[4-(4-isopropylpiperazin-1-yl)-3-methyl-phenyl]-3-methyl-3,4-dihydro-2H-pyridine-1-carboxylate (7 g, 16.92 mmol) in DCM (20 mL). The resulting solution was stirred at 25° C. for 1 hr, and then concentrated in vacuo. The residue was diluted with water (100 mL). The resulting solution of TFA salt of the product was decanted from dark-brown oily residue, which was additionally rinsed with water (2*25 mL). The combined aqueous solution was filtered through a cotton pad to remove traces of oily impurities, then basified to pH 11-12 with 10% aqueous sodium hydroxide solution and extracted with dichloromethane (2*50 mL). The combined organic extracts were dried over sodium sulfate and concentrated in vacuo to afford 1-isopropyl-4-[2-methyl-4-[rac-(3S)-3-methyl-2,3,4,5-tetrahydropyridin-6-yl]phenyl]piperazine (1.5 g, 4.79 mmol, 28.27% yield) as light-yellow gum, which was directly used in the next step LCMS(ESI): [M+H]⁺ m/z: calcd 314.2; found 314.2; Rt=0.643 min.

Step 6: The Synthesis of 1-isopropyl-4-[2-methyl-4-[rac-(2R,5S)-5-methyl-2-piperidyl]phenyl]piperazine 1-isopropyl-4-[2-methyl-4-[rac-(3S)-3-methyl-2,3,4,5-tetrahydropyridin-6-yl]phenyl]piperazine (1.5 g, 4.79 mmol) was dissolved in Methanol (15 mL) and Sodium Borohydride (362.06 mg, 9.57 mmol, 337.11 μL) was added portionwise. The resulting mixture was stirred overnight. Water (20 mL) was added to the reaction mixture and the resulting mixture was concentrated in vacuo. The residue was diluted with water (30 mL) and the resulting mixture was extracted with DCM (2*50 mL). Combined organic layers were dried over Na$_2$SO$_4$, filtered, and concentrated in vacuo to obtain 1-isopropyl-4-[2-methyl-4-[rac-(2R,5S)-5-methyl-2-piperidyl]phenyl]piperazine (0.5 g, 1.58 mmol, 33.12% yield)

LCMS(ESI): [M+H]$^+$ m/z: calcd 316.2; found 316.2; Rt=0.670 min.

Step 7: The Synthesis of N-(6-amino-5-ethyl-3-pyridyl)-2-oxo-2-[rac-(2R,5S)-2-[4-(4-isopropylpiperazin-1-yl)-3-methyl-phenyl]-5-methyl-1-piperidyl]acetamide (Compound 7234

1-isopropyl-4-[2-methyl-4-[rac-(2R,5S)-5-methyl-2-piperidyl]phenyl]piperazine (150 mg, 475.44 µmol) was dissolved in DMF (2 mL) and triethylamine (481.10 mg, 4.75 mmol, 662.67 µL) was added, followed by 2-[(6-amino-5-ethyl-3-pyridyl)amino]-2-oxo-acetic acid (99.46 mg, 475.44 µmol). Then the HATU (271.17 mg, 713.17 µmol) was added dropwise and the reaction mixture was stirred overnight. The next day it was evaporated in vacuo and purified by HPLC (2-10 min 0-65% water/MeOH+NH$_3$30 mL/min; loading pump 4 mL/min MeOH; column SunFire 19*100 mm) to obtain N-(6-amino-5-ethyl-3-pyridyl)-2-oxo-2-[rac-(2R,5S)-2-[4-(4-isopropylpiperazin-1-yl)-3-methyl-phenyl]-5-methyl-1-piperidyl]acetamide (22.3 mg, 44.01 µmol, 9.26% yield).

$^1$H NMR (600 MHz, dmso) δ 0.98-1.01 (m, 9H), 1.07-1.14 (m, 3H), 1.26-1.37 (m, 1H), 1.62-1.73 (m, 1H), 1.80-1.93 (m, 1H), 1.96-2.11 (m, 1H), 2.12-2.20 (m, 1H), 2.21-2.25 (m, 3H), 2.37-2.43 (m, 2H), 2.53-2.58 (m, 4H), 2.65-2.70 (m, 1H), 2.72-2.77 (m, 0.3H), 2.78-2.85 (m, 4H), 3.18-3.23 (m, 0.7H), 3.43-4.01 (m, 1H), 5.03-5.54 (m, 1H), 5.55-5.67 (m, 2H), 6.95-7.02 (m, 1H), 7.05-7.16 (m, 2H), 7.44-7.53 (m, 1H), 7.98-8.10 (m, 1H), 10.39-10.64 (m, 1H).

LCMS(ESI): [M+H]$^+$ m/z: calcd 507.2; found 507.4; Rt=0.838 min.

Example 291. The Synthesis of N-(6-amino-5-ethyl-3-pyridyl)-2-oxo-2-[rac-(2R,5S)-2-[4-(4-ethylpiperazin-1-yl)-3-methyl-phenyl]-5-methyl-1-piperidyl]acetamide (Compound 1376)

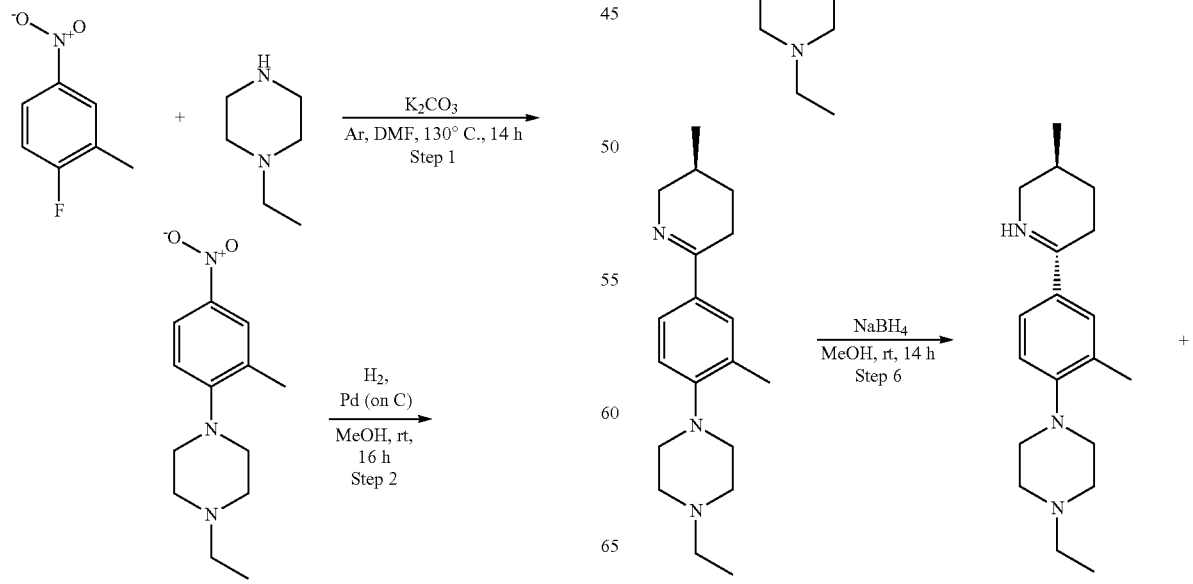

-continued

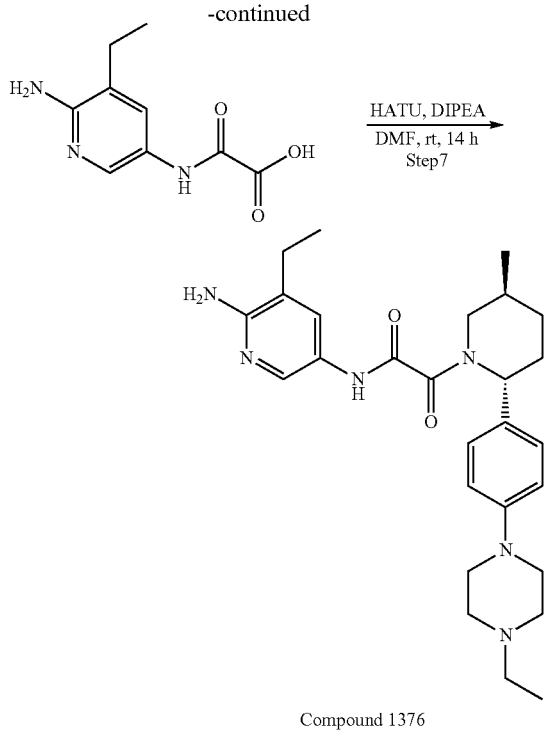

Compound 1376

Step 1: The Synthesis of 1-ethyl-4-(2-methyl-4-nitro-phenyl)piperazine 1-ethylpiperazine (2.5 g, 21.89 mmol, 2.78 mL), 1-fluoro-2-methyl-4-nitro-benzene (4.75 g, 30.65 mmol), Potassium carbonate (9.08 g, 65.68 mmol, 3.96 mL) were mixed in DMF (25 mL) under Ar. Reaction mixture was stirred overnight at 130° C. After cooling to room temp., the reaction mixture was diluted with water, extracted with EA. Organic phase was evaporated in vacuo giving 1-ethyl-4-(2-methyl-4-nitro-phenyl)piperazine (5 g, crude).

LCMS(ESI): [M+H]$^+$ m/z: calcd 250.2; found 250.2; Rt=0.761 min.

Step 2: The Synthesis of 4-(4-ethylpiperazin-1-yl)-3-methyl-aniline

The mixture of 1-ethyl-4-(2-methyl-4-nitro-phenyl)piperazine (5 g, 20.06 mmol) and Pd/C (2.13 g, 20.06 mmol) in Methanol was stirred at 25° C. for 16 hr under H$_2$ atmosphere. The mixture was filtrated and filtrate was evaporated. The residue was crystalized in hexane to give 4-(4-ethylpiperazin-1-yl)-3-methyl-aniline (2.9 g, 13.22 mmol, 65.93% yield).

LCMS(ESI): [M+H]$^+$ m/z: calcd 220.2; found 220.4; Rt=0.511 min.

Step 3: The Synthesis of 1-ethyl-4-[2-methyl-4-(4,4,5,5-tetramethyl-1,3,2-dioxaborolan-2-yl)phenyl]piperazine 4-(4-ethylpiperazin-1-yl)-3-methyl-aniline (2.8 g, 12.77 mmol) and Bis(pinacolato)diboron (3.89 g, 15.32 mmol) were weighed in a round-bottom flask. MeCN (28 mL) and tert-butyl nitrite (1.97 g, 19.15 mmol, 2.28 mL) were then added in succession. The resulting reaction solution was stirred for 12 hr at 80° C. (N$_2$ evolution completed within 5 to 15 min). The solution was then concentrated under reduced pressure, and the crude residue was purified by flash chromatography to obtain 1-ethyl-4-[2-methyl-4-(4,4,5,5-tetramethyl-1,3,2-dioxaborolan-2-yl)phenyl]piperazine (7 g, crude).

LCMS(ESI): [M+H]$^+$ m/z: calcd 331.2; found 331.2; Rt=1.005 min.

Step 4: The Synthesis of tert-butyl rac-(3S)-6-[4-(4-ethylpiperazin-1-yl)-3-methyl-phenyl]-3-methyl-3,4-dihydro-2H-pyridine-1-carboxylate 1-ethyl-4-[2-methyl-4-(4,4,5,5-tetramethyl-1,3,2-dioxaborolan-2-yl)phenyl]piperazine (6.8 g, 20.59 mmol), tert-butyl rac-(3S)-3-methyl-6-(trifluoromethylsulfonyloxy)-3,4-dihydro-2H-pyridine-1-carboxylate (7.11 g, 20.59 mmol) and sodium carbonate (4.36 g, 41.18 mmol, 1.72 mL) were mixed together in a mixture of Dioxane (60 mL) and Water (20 mL). The resulting mixture was purged with argon for 10 min and Pd(dppf)Cl$_2$ DCM (840.69 mg, 1.03 mmol) was added thereto. The resulting mixture was heated at 90° C. overnight. The resulting mixture was cooled and diluted with water (5 mL). The resulting mixture was extracted with EtOAc (2*15 mL) and combined organic layers were washed with brine (10 mL), dried over Na$_2$SO$_4$, filtered, and concentrated in vacuo.

LCMS(ESI): [M+H]$^+$ m/z: calcd 400.2; found 400.2; Rt=1.270 min.

Step 5: The Synthesis of 1-ethyl-4-[2-methyl-4-[rac-(3S)-3-methyl-2,3,4,5-tetrahydropyridin-6-yl]phenyl]piperazine Trifluoroacetic acid (23.97 g, 210.23 mmol, 16.20 mL) was added in one portion to a stirred solution of tert-butyl rac-(3S)-6-[4-(4-ethylpiperazin-1-yl)-3-methyl-phenyl]-3-methyl-3,4-dihydro-2H-pyridine-1-carboxylate (7 g, 17.52 mmol) in DCM (20 mL). The resulting solution was stirred at 25° C. for 1 hr, and then concentrated in vacuo. The residue was diluted with water (100 mL). The resulting solution of TFA salt of the product was decanted from dark-brown oily residue, which was additionally rinsed with water (2*25 mL). The combined aqueous solution was filtered through a cotton pad to remove traces of oily impurities, then basified to pH 11-12 with 10% aqueous sodium hydroxide solution and extracted with dichloromethane (2*50 mL). The combined organic extracts were dried over sodium sulfate and concentrated in vacuo to afford 1-ethyl-4-[2-methyl-4-[rac-(3S)-3-methyl-2,3,4,5-tetrahydropyridin-6-yl]phenyl]piperazine (1.2 g, 4.01 mmol, 22.87% yield) as light-yellow gum, which was directly used in the next step LCMS(ESI): [M+H]$^+$ m/z: calcd 300.2; found 300.4; Rt=0.682 min.

Step 6: The Synthesis of 1-ethyl-4-[2-methyl-4-[rac-(2R,5S)-5-methyl-2-piperidyl]phenyl]piperazine 1-ethyl-4-[2-methyl-4-[rac-(3S)-3-methyl-2,3,4,5-tetrahydropyridin-6-yl]phenyl]piperazine (1.2 g, 4.01 mmol) was dissolved in Methanol (12 mL) and Sodium Borohydride (303.19 mg, 8.01 mmol, 282.30 µL) was added portionwise. The resulting mixture was stirred overnight. Water (20 mL) was added to the reaction mixture and the resulting mixture was concentrated in vacuo. The residue was diluted with water (30 mL) and the resulting mixture was extracted with DCM (2*50 mL). Combined organic layers were dried over Na$_2$SO$_4$, filtered, and concentrated in vacuo to obtain 1-ethyl-4-[2-methyl-4-[rac-(2R,5S)-5-methyl-2-piperidyl]phenyl]piperazine (0.5 g, 1.66 mmol, 41.39% yield).

LCMS(ESI): [M+H]$^+$ m/z: calcd 302.2; found 302.2; Rt=0.643 min.

Step 7: The Synthesis of N-(6-amino-5-ethyl-3-pyridyl)-2-oxo-2-[rac-(2R,5S)-2-[4-(4-ethylpiperazin-1-yl)-3-methyl-phenyl]-5-methyl-1-piperidyl]acetamide (Compound 1376

1-ethyl-4-[2-methyl-4-[rac-(2R,5S)-5-methyl-2-piperidyl]phenyl]piperazine (150 mg, 497.56 μmol) was dissolved in DMF (1.38 mL) and triethylamine (503.49 mg, 4.98 mmol, 693.51 μL) was added, followed by 2-[(6-amino-5-ethyl-3-pyridyl)amino]-2-oxo-acetic acid (104.09 mg, 497.56 μmol). Then the HATU (283.78 mg, 746.35 μmol) was added dropwise and the reaction mixture was stirred overnight. The next day it was evaporated in vacuo and purified by HPLC (2-10 min 0-55% water/ACN+fa 30 ml/min; loading pump 4 ml/minACN; column SunFire 19*100 mm) to obtain N-(6-amino-5-ethyl-3-pyridyl)-2-oxo-2-[rac-(2R,5S)-2-[4-(4-ethylpiperazin-1-yl)-3-methyl-phenyl]-5-methyl-1-piperidyl]acetamide (7.9 mg, 16.04 μmol, 3.22% yield).

$^1$H NMR (600 MHz, dmso) δ 0.97-1.04 (m, 6H), 1.07-1.14 (m, 3H), 1.25-1.36 (m, 1H), 1.63-1.75 (m, 1H), 1.79-1.91 (m, 1H), 1.93-2.07 (m, 1H), 2.12-2.18 (m, 1H), 2.21-2.27 (m, 3H), 2.35-2.41 (m, 5H), 2.73-3.06 (m, 8H), 3.95-4.21 (m, 1H), 5.01-5.55 (m, 1H), 5.55-5.68 (m, 2H), 6.95-7.16 (m, 3H), 7.43-7.57 (m, 1H), 7.98-8.09 (m, 1H), 10.43-10.55 (m, 1H).

LCMS(ESI): [M+2H]+m/z: calcd 494.2; found 494.4; Rt=0.881 min.

Example 292. The Synthesis of N-(6-amino-5-ethyl-3-pyridyl)-2-[(2R,5S)-5-methyl-2-[3-methyl-4-(4-methylpiperazin-1-yl)phenyl]-1-piperidyl]-2-oxo-acetamide (Compound 1390)

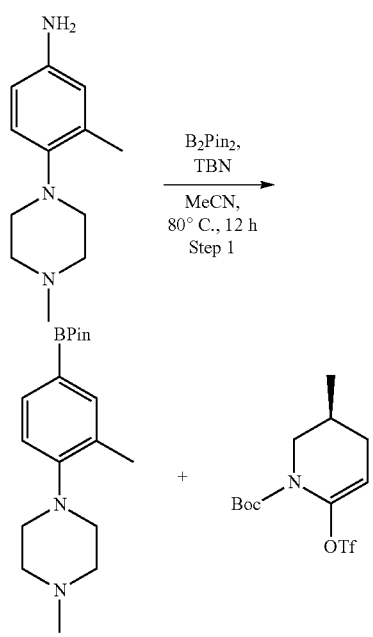

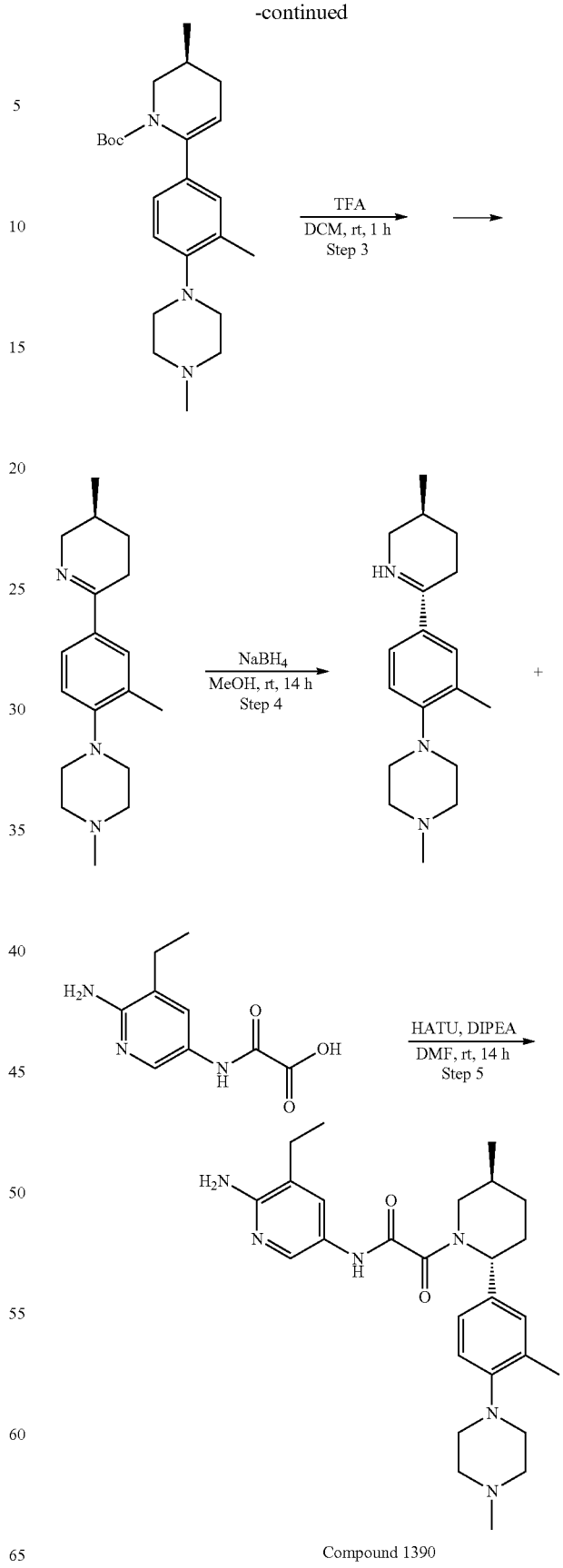

Compound 1390

Step 1: The Synthesis of 1-methyl-4-[2-methyl-4-(4,4,5,5-tetramethyl-1,3,2-dioxaborolan-2-yl)phenyl] piperazine 3-methyl-4-(4-methylpiperazin-1-yl) aniline (4.5 g, 21.92 mmol) and Bis(pinacolato)diboron (6.12 g, 24.11 mmol) were weighed in a round-bottom flask. MeCN (120 mL) and tert-butyl nitrite (3.39 g, 32.88 mmol, 3.91 mL) were then added in succession. The resulting reaction solution was stirred for 12 hr at 80° C. ($N_2$ evolution completed within 5 to 15 min). The solution was then concentrated under reduced pressure, and the crude residue was purified by flash chromatography to obtain 1-methyl-4-[2-methyl-4-(4,4,5,5-tetramethyl-1,3,2-dioxaborolan-2-yl)phenyl]piperazine (1.5 g, 4.74 mmol, 21.64% yield)

LCMS(ESI): $[M+H]^+$ m/z: calcd 317.2; found 317.2; Rt=0.893 min.

Step 2: The Synthesis of tert-butyl (3S)-3-methyl-6-[3-methyl-4-(4-methylpiperazin-1-yl)phenyl]-3,4-dihydro-2H-pyridine-1-carboxylate 1-methyl-4-[2-methyl-4-(4,4,5,5-tetramethyl-1,3,2-dioxaborolan-2-yl)phenyl]piperazine (1.35 g, 4.27 mmol), tert-butyl (3S)-3-methyl-6-(trifluoromethylsulfonyl)-3,4-dihydro-2H-pyridine-1-carboxylate (1.41 g, 4.27 mmol) and Sodium carbonate (678.68 mg, 6.40 mmol, 268.04 µL) were mixed together in Dioxane (15 mL) and $H_2O$ (5 mL) was added. The resulting mixture was evacuated and backfield three times with argon. Pd(dppf)$Cl_2$ DCM (174.30 mg, 213.44 µmol) was added to the previous mixture and the resulting mixture was heated at 90° C. for 12 hr. The reaction mixture was cooled and diluted with water (15 mL). The resulting mixture was filtered and rinsed with water (10 mL) and EtOAc (20 mL). The filtrated was transferred to a separating funnel and an organic layer was separated. An aqueous layer was extracted with EtOAc (2*20 mL). Combined organic layers were washed with brine, dried over $Na_2SO_4$ and evaporated to obtain crude tert-butyl (3S)-3-methyl-6-[3-methyl-4-(4-methylpiperazin-1-yl)phenyl]-3,4-dihydro-2H-pyridine-1-carboxylate (0.75 g, crude).

LCMS(ESI): $[M+H]^+$ m/z: calcd 386.2; found 386.2; Rt=1.055 min.

Step 3: The Synthesis of 1-methyl-4-[2-methyl-4-[(3S)-3-methyl-2,3,4,5-tetrahydropyridin-6-yl]phenyl]piperazine tert-butyl (3S)-3-methyl-6-[3-methyl-4-(4-methylpiperazin-1-yl)phenyl]-3,4-dihydro-2H-pyridine-1-carboxylate (0.75 g, 1.95 mmol) was dissolved in DCM (3 mL) and TFA (3 mL) was added thereto. The resulting mixture was stirred for 1 hr. The reaction mixture was poured into aq. $K_2CO_3$ solution and the resulting mixture was extracted with DCM. Combined organic layers were dried over $Na_2SO_4$, filtered and evaporated to obtain 1-methyl-4-[2-methyl-4-[(3S)-3-methyl-2,3,4,5-tetrahydropyridin-6-yl]phenyl]piperazine (0.6 g, crude) which was used in the next step without further purification. LCMS(ESI): $[M+H]^+$ m/z: calcd 286.2; found 286.2; Rt=0.787 min.

Step 4: The Synthesis of 1-methyl-4-[2-methyl-4-[(2R,5S)-5-methyl-2-piperidyl]phenyl]piperazine 1-methyl-4-[2-methyl-4-[(3S)-3-methyl-2,3,4,5-tetrahydropyridin-6-yl]phenyl]piperazine (0.6 g, 2.10 mmol) was dissolved in Methanol (10 mL) and Sodium Borohydride (159.05 mg, 4.20 mmol, 148.09 µL) was added dropwise. The reaction mixture was stirred overnight at room temperature. The reaction mixture was evaporated to dryness. The residue was dissolved in DCM (10 mL) and the resulting mixture was extracted with citric acid solution (2*10 mL). Combined aqueous layers were washed with DCM (3*10 mL) and then basified with $K_2CO_3$. The resulting mixture was extracted with DCM (2*15 mL) and combined organic layers were dried over $Na_2SO_4$, filtered and evaporated to obtain 1-methyl-4-[2-methyl-4-[(2R,5S)-5-methyl-2-piperidyl]phenyl]piperazine (0.2 g, 695.79 µmol, 33.10% yield).

LCMS(ESI): $[M+H]^+$ m/z: calcd 288.2; found 288.2; Rt=0.713 min.

Step 5: The Synthesis of N-(6-amino-5-ethyl-3-pyridyl)-2-[(2R,5S)-5-methyl-2-[3-methyl-4-(4-methylpiperazin-1-yl)phenyl]-1-piperidyl]-2-oxo-acetamide (Compound 1390

1-methyl-4-[2-methyl-4-[(2R,5S)-5-methyl-2-piperidyl]phenyl]piperazine (270 mg, 939.32 µmol) was dissolved in DMF (5 mL) and triethylamine (950.50 mg, 9.39 mmol, 1.31 mL) was added, followed by 2-[(6-amino-5-ethyl-3-pyridyl)amino]-2-oxo-acetic acid (196.51 mg, 939.32 µmol). Then the HATU (535.74 mg, 1.41 mmol) was added dropwise and the reaction mixture was stirred overnight. The next day it was evaporated in vacuo and purified by HPLC (2-10 min 0-30% acetonitrile+fa 30 min (loading pump 4 mL/min acetonitrile), column: SunFire 100*19 mm, 5 microM) to obtain N-(6-amino-5-ethyl-3-pyridyl)-2-[(2R,5S)-5-methyl-2-[3-methyl-4-(4-methylpiperazin-1-yl)phenyl]-1-piperidyl]-2-oxo-acetamide (12.6 mg, 26.33 µmol, 2.80% yield) and N-(6-amino-5-ethyl-3-pyridyl)-2-[(2R,5S)-5-methyl-2-[3-methyl-4-(4-methylpiperazin-1-yl)phenyl]-1-piperidyl]-2-oxo-acetamide (10 mg, 20.89 µmol, 2.22% yield)

$^1$H NMR (600 MHz, dmso) δ 1.00 (t, 3H), 1.06-1.13 (m, 3H), 1.26-1.36 (m, 1H), 1.63-1.73 (m, 1H), 1.79-1.92 (m, 1H), 1.93-2.09 (m, 1H), 2.11-2.19 (m, 1H), 2.20-2.25 (m, 7H), 2.31-2.36 (m, 1H), 2.38-2.42 (m, 2H), 2.72-3.22 (m, 7H), 3.40-4.00 (m, 1H), 5.03-5.53 (m, 1H), 5.58-5.68 (m, 2H), 6.97-7.02 (m, 1H), 7.03-7.07 (m, 1H), 7.08-7.14 (m, 1H), 7.42-7.53 (m, 1H), 7.96-8.09 (m, 1H), 10.41-10.55 (m, 1H).

LCMS(ESI): $[M+2H]^+$ m/z: calcd 480.2; found 480.2; Rt=0.741 min.

Scheme C. Synthesis of Compounds of Formula 3

Compounds of Formula 3, 3a, 3b, 3c and 3d are compounds of Formula (I), (Ia), (Ib), (Ic) and (Id) wherein $R^1$ is $NH_2$ and $R^2$, $R^3$, $R^4$, $R^6$, $R^7$, and $R^8$ are as described herein General Procedure 3

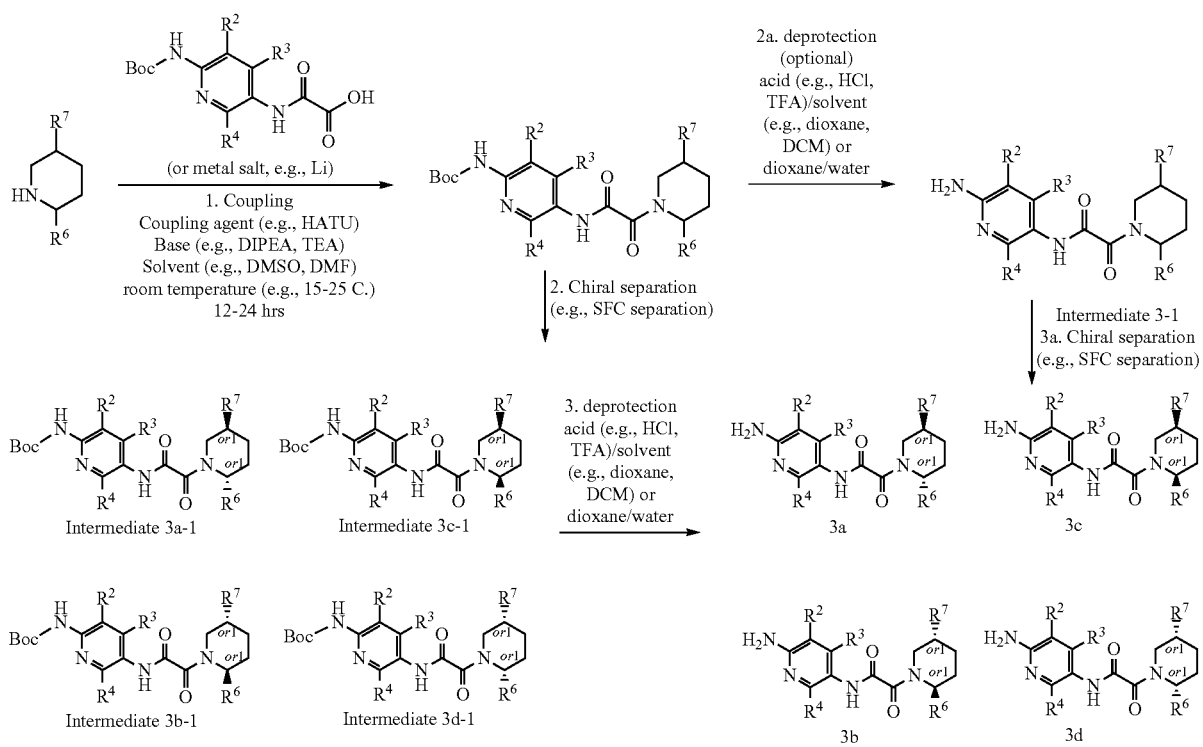

Intermediate 3a-1
Intermediate 3b-1
Intermediate 3c-1
Intermediate 3d-1

3a
3b
3c
3d

Note that the separation step is optional and is used in certain cases to separate the cis/trans diastereomers, and in certain cases to separate distinct enantiomers, as described in the detailed procedures. In certain instances, the starting piperidine is in a defined cis or trans configuration—in those instances, the chiral separation step results only in two of the four enantiomers depicted.

As shown in Scheme C, compounds of Formula (3a), (3b), (3c), and (3d) can be separated from a mixture of compounds of Formula (3-1), wherein $R^1$, $R^2$, $R^3$, $R^4$, $R^6$, $R^7$, $R^8$, and n are as described herein. Methods of chiral separation are known to persons of ordinary skill in the art. For example, in some embodiments, chiral separation can be accomplished through the use of chiral HPLC purification (Column: AD-H III (250*20 mm, 5 m). Exemplary eluents include, but are not limited to, hexane, IPA, MeOH, MeCN, and H₂O, and mixtures thereof.

Alternatively, compounds of Formula (3a), (3b), (3c), and (3d) can be prepared from Intermediates (3a-1), (3b-1), (3c-1), and (3d-1). In some embodiments, deprotection can take place before or after chiral separation. Conditions for removing a protecting group-PG (e.g., —Boc) can employ, for example, acidic conditions, (e.g., water/dioxane, hydrochoric acid in a protic solvent (e.g., methanol), hydrochloric acid in an aprotic solvent (e.g., dioxane), TFA in an an aprotic solvent (e.g., dichloromethane, chloroform, etc)). In some embodiments, a deprotection step employs HCl (4.0 M) in dioxane. In some embodiments, a deprotection step employs HCl (4.0 M) in DCM.

In some embodiments, compounds of the present disclosure can be prepared through a method that comprises an amide bond coupling. In some embodiments, an amide bond coupling employs a piperadine and a carboxylic acid. Examples of conditions known to facilitate an amide bond coupling include but are not limited to adding a coupling agent such as CDI, HATU, HOBT, HBTU or PyBOP, a base such as a hydride base e.g., NaH, or KH, an amine base such as DBU, NEt₃, and NEt(ⁱPr)₂ or a carbonate base e.g., Na₂CO₃, K₂CO₃, or Cs₂CO₃, and in one embodiment stirring a reaction at 0° C. to room temperature or another embodiment at a temperature of 70° C. or higher, for example at a temperature in a range of 70° C. to 110° C., or in a range of 70° C. to 80° C., or at 80° C. A reaction may be carried out in solvents such as but not limited to DMF, and MTBE. In some embodiments, a reaction comprises comprises of HATU, Et₃N, and DMF. In some embodiments, a reaction comprises employment of HATU, Et₃N, and MeCN. In some embodiments, a reaction comprises comprises of TATU, Et₃N, and DMF. In some embodiments, a reaction comprises comprises of HATU, DIPEA, and DMSO. In some embodiments, a reaction comprises comprises of HATU, DIPEA, and DMF. In some embodiments, a reaction comprises comprises of HATU, TEA, and DMSO.

Example 293. Synthesis of rac-N-(6-amino-5-methylpyridin-3-yl)-2-((2R,5)-5-methyl-2-(1-methyl-1H-pyrazol-5-yl)piperidin-1-yl)-2-oxoacetamide (Compound 235

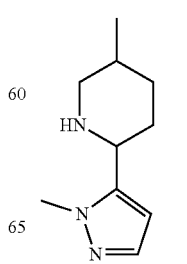

+

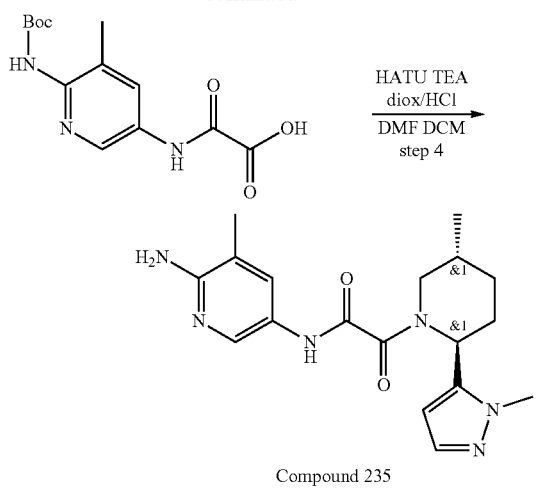

Compound 235

Triethylamine (1.41 g, 13.95 mmol, 1.94 mL) was added to a stirred mixture of 5-methyl-2-(2-methylpyrazol-3-yl)piperidine (250 mg, 1.39 mmol) from intermediate synthesis 2A, 2-[[6-(tert-butoxycarbonylamino)-5-methyl-3-pyridyl]amino]-2-oxo-acetic acid (411.82 mg, 1.39 mmol) and HATU (583.30 mg, 1.53 mmol) in DMF (5 mL). The resulting mixture was stirred at 25° C. for 2 hr, and then evaporated in vacuo. The residue was dissolved in DCM (4 mL) and hydrogen chloride solution 4.0 M in dioxane (4.20 g, 16.01 mmol, 5.25 mL, 13.9% purity) was added. The resulting suspension was stirred at 25° C. for 18 hr, then evaporated in vacuo and the residue was purified by reverse phase HPLC (column:XBridge C18 100×20 mm, 5 um) using 20-40% 0-5 min 0.1% NH$_3$-methanol to afford Compound 235 N-(6-amino-5-methyl-3-pyridyl)-2-[(2R,5S)-5-methyl-2-(2-methylpyrazol-3-yl)-1-piperidyl]-2-oxo-acetamide (201 mg, 563.94 µmol, 40.44% yield) as white solid.

$^1$H NMR (500 MHz, DMSO-d$_6$) δ (ppm) 0.96-1.05 (m, 3H), 1.35-1.46 (m, 1H), 1.82-1.91 (m, 1H), 1.93-2.00 (m, 1H), 2.01-2.14 (m, 5H), 3.16-3.29 (m, 1H), 3.43-3.54 (m, 1H), 3.70-3.80 (m, 3H), 5.40-5.66 (m, 2H), 5.66-5.79 (m, 1H), 6.38-6.54 (m, 1H), 7.30-7.40 (m, 1H), 7.47 (s, 1H), 7.91-8.23 (m, 1H), 10.34-10.54 (m, 1H).

LCMS(ESI): [M+1] m/z: calcd 356.4; found 357.2; Rt=1.889 min.

Example 294. The Synthesis of N-(6-amino-5-methylpyridin-3-yl)-2-(5-methyl-2-(thiophen-2-yl)piperidin-1-yl)-2-oxoacetamide (Compound 122, Compound 115

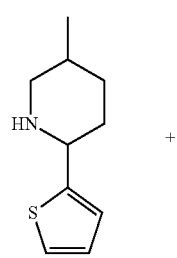

+

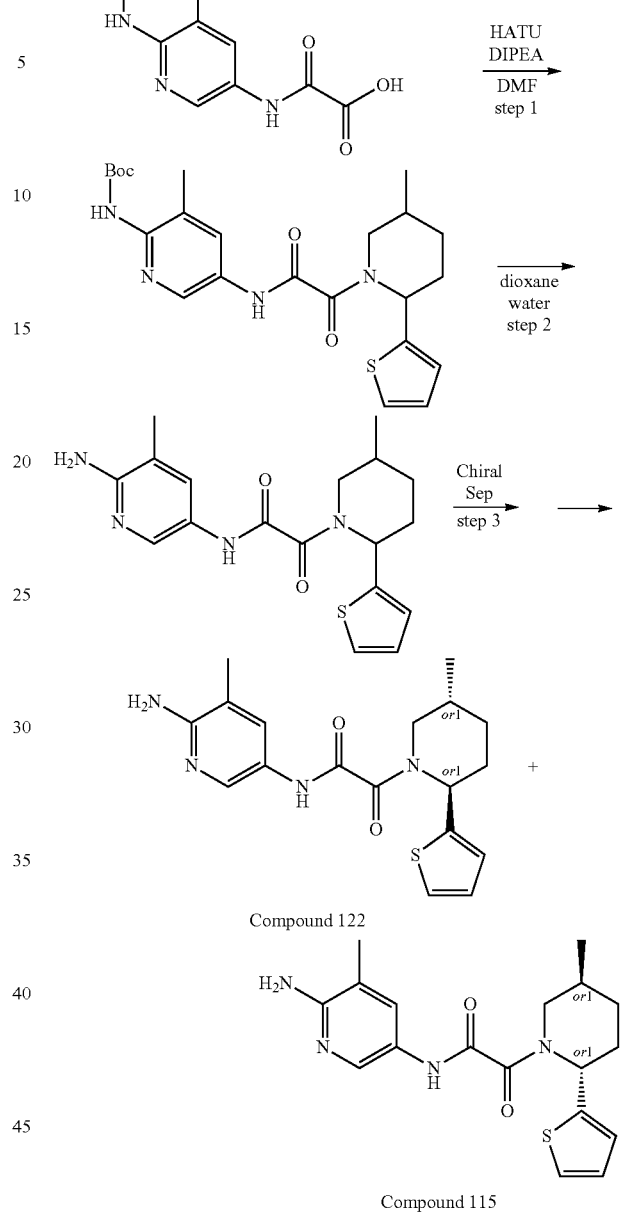

Step 1: Synthesis of tert-butyl (3-methyl-5-(2-(5-methyl-2-(thiophen-2-yl)piperidin-1-yl)-2-oxoacetamido)pyridin-2-yl)carbamate DIPEA (461.13 mg, 3.57 mmol, 621.47 µL) was added to the solution of 2-[[6-(tert-butoxycarbonylamino)-5-methyl-3-pyridyl]amino]-2-oxo-acetic acid (421.43 mg, 1.43 mmol) and 5-methyl-2-(2-thienyl)piperidine (258.74 mg, 1.43 mmol) in DMF (10 mL). The resulting mixture was stirred for 5 min followed by the addition of the solution of HATU (569.78 mg, 1.50 mmol) in DMF. Then, the reaction mixture was stirred overnight at room temperature. The resulting suspension was concentrated under reduced pressure and it was subjected to HPLC (column SunFire 100*20 mm 5 um, MeCN+NH$_3$ as eluent mixture) to afford pure tert-butyl N-[3-methyl-5-[[2-[5-methyl-2-(2-thienyl)-1-piperidyl]-2-oxo-acetyl]amino]-2-pyridyl]carbamate (0.27 g, 588.78 μmol, 41.26% yield).

$^1$H NMR (400 MHz, CDCl$_3$) δ (ppm) 1.08 (d, 3H), 1.48 (s, 9H), 2.04 (m, 3H), 2.28 (s, 3H), 2.62 (m, 1H), 3.48 (m, 2H), 4.72 (m, 2H), 6.65 (m, 1H), 6.96 (m, 2H), 7.22 (m, 1H), 8.02 (m, 1H), 8.32 (m, 1H), 9.31 (m, 1H).

LCMS(ESI): [M]$^+$ m/z: calcd 458.4; found 459.2; Rt=3.715 min.

Step 2: Synthesis of N-(6-amino-5-methylpyridin-3-yl)-2-(5-methyl-2-(thiophen-2-yl)piperidin-1-yl)-2-oxoacetamide tert-butyl N-[3-methyl-5-[[2-[5-methyl-2-(2-thienyl)-1-piperidyl]-2-oxo-acetyl]amino]-2-pyridyl]carbamate (279.14 mg, 608.71 μmol) was dissolved in dioxane (2 mL) and water (5 mL). Then resulting mixture was stirred at 100° C. overnight. After solution was evaporated in vacuo to afford to N-(6-amino-5-methyl-3-pyridyl)-2-[5-methyl-2-(2-thienyl)-1-piperidyl]-2-oxo-acetamide (87 mg, 242.71 μmol, 39.87% yield).

$^1$H NMR (400 MHz, CDCl$_3$) δ (ppm) 1.11 (d, 3H), 1.46 (m, 1H), 2.18 (m, 3H), 2.32 (m, 2H), 3.48 (s, 3H), 3.88 (m, 1H), 4.51 (m, 2H), 5.55 (m, 1H), 6.99 (m, 2H), 7.22 (m, 1H), 7.72 (m, 1H), 8.09 (m, 1H), 9.07 (m, 1H).

LCMS(ESI): [M]$^+$ m/z: calcd 358.4; found 359.2; Rt=2.688 min.

Step 3: Chiral Separation (Compound 122 and Compound 115

Purification on the chiral column was taken in the system Hex-IPA-MeOH, 75-15-15, 12 mL/min. Number of injections: 1, injection volume: 900 mkl. From 87 mg of racemate, 17.8 mg and 22.7 mg of the individual enantiomers were obtained.

rel-N-(6-amino-5-methylpyridin-3-yl)-2-((2S,5R)-5-methyl-2-(thiophen-2-yl)piperidin-1-yl)-2-oxoacetamide Compound 122:

Retention time: 23.37 min $^1$H NMR (600 MHz, DMSO-d$_6$) δ (ppm) 0.98 (m, 3H), 1.40 (m, 1H), 1.83 (m, 2H), 1.95 (m, 1H), 2.01 (m, 3H), 2.09 (m, 1H), 2.86 (m, 1H), 3.82 (m, 1H), 5.67 (m, 3H), 7.01 (m, 2H), 7.48 (m, 2H), 8.00 (s, 1H), 10.48 (m, 1H).

LCMS(ESI): [M]$^+$ m/z: calcd 358.4; found 359.2; Rt=2.275 min.

rel-N-(6-amino-5-methylpyridin-3-yl)-2-((2R,5S)-5-methyl-2-(thiophen-2-yl)piperidin-1-yl)-2-oxoacetamide Compound 115

Retention time: 18.58 min $^1$H NMR (600 MHz, DMSO-d$_6$) δ (ppm) 0.98 (m, 3H), 1.40 (t, 1H), 1.91 (m, 3H), 2.01 (m, 3H), 2.11 (m, 1H), 2.85 (m, 1H), 3.72 (m, 1H), 5.51 (m, 1H), 5.71 (m, 2H), 7.01 (m, 2H), 7.48 (m, 2H), 8.00 (m, 1H), 10.48 (m, 1H).

LCMS(ESI): [M]$^+$ m/z: calcd 358.4; found 359.2; Rt=2.278 min.

Example 295. The Synthesis of 2-(2-(3-(1-acetylpiperidin-4-yl)phenyl)piperidin-1-yl)-N-(6-amino-5-methylpyridin-3-yl)-2-oxoacetamide (Compound 95, Compound 94, Compound 96

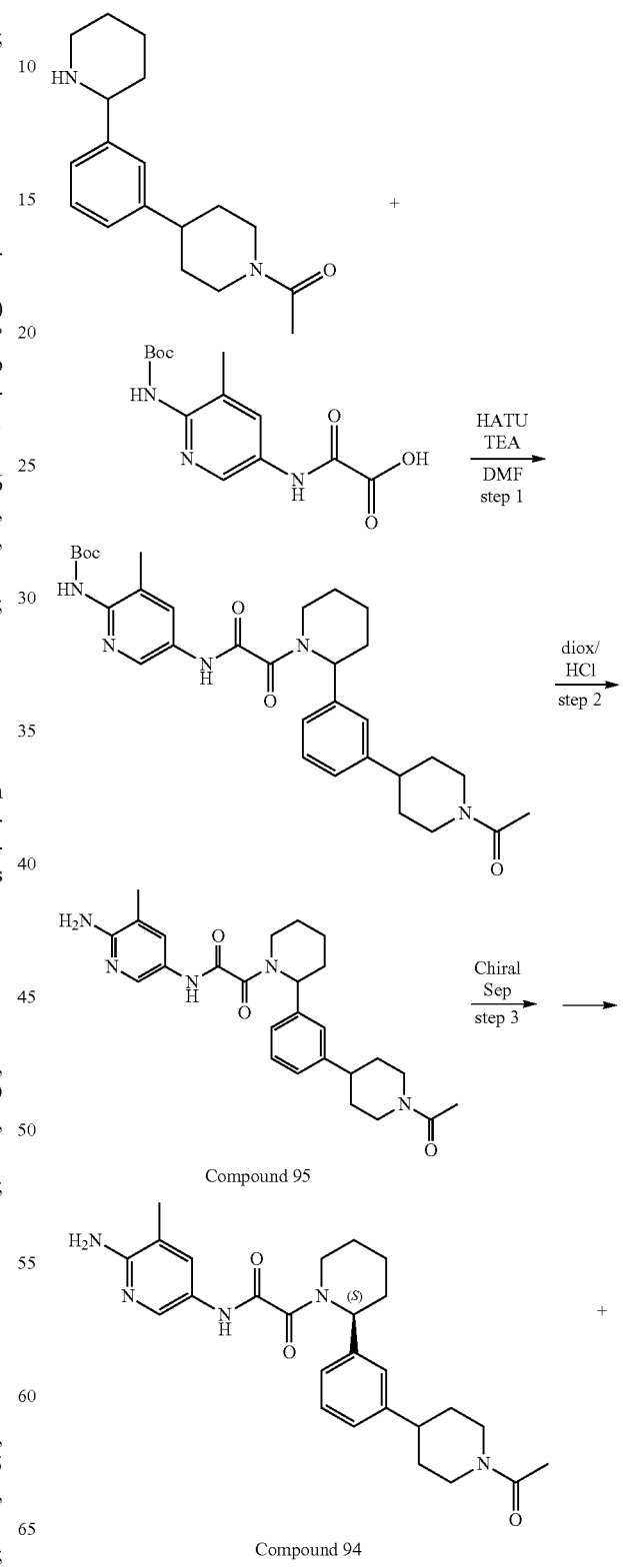

Compound 95

Compound 94

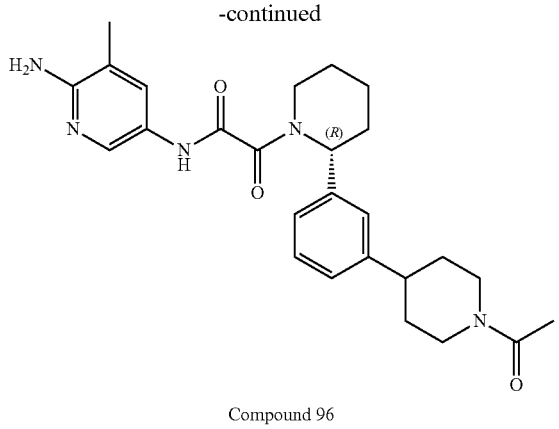

Compound 96

Step 1: Synthesis of tert-butyl (5-(2-(2-(3-(1-acetylpiperidin-4-yl)phenyl)piperidin-1-yl)-2-oxoacetamido)-3-methylpyridin-2-yl)carbamate To a suspension of 1-[4-[3-(2-piperidyl)phenyl]-1-piperidyl]ethanone (161.65 mg, 564.42 µmol), 2-[[6-(tert-butoxycarbonylamino)-5-methyl-3-pyridyl]amino]-2-oxo-acetic acid (0.2 g, 677.30 µmol) and HATU (257.53 mg, 677.30 µmol) in DMF (3 mL), triethylamine (171.34 mg, 1.69 mmol, 236.01 µL) was added. The resulting mixture was stirred at 25° C. for 3 hr. The resulting mixture was evaporated to dryness to obtain tert-butyl N-[5-[[2-[2-[3-(1-acetyl-4-piperidyl)phenyl]-1-piperidyl]-2-oxo-acetyl]amino]-3-methyl-2-pyridyl]carbamate (0.7 g, crude). It was used for the next step without purification.

LCMS(ESI): [M]$^+$ m/z: calcd 563.6; found 564.2; Rt=1.371 min.

Step 2: Synthesis of 2-(2-(3-(1-acetylpiperidin-4-yl)phenyl)piperidin-1-yl)-N-(6-amino-5-methylpyridin-3-yl)-2-oxoacetamide (Compound 95 tert-butyl N-[5-[[2-[2-[3-(1-acetyl-4-piperidyl)phenyl]-1-piperidyl]-2-oxo-acetyl]amino]-3-methyl-2-pyridyl]carbamate (0.3 g, 532.21 µmol) was dissolved in hydrogen chloride solution 4.0 M in dioxane (3.20 g, 87.77 mmol, 4 mL) and stirred at 25° C. for 12 hr. The solvent was evaporated and residue was dried in vacuo to obtain crude product (0.7 g). This compound was purified by HPLC (LC 09 40-40-60% 0-1-6 min 0.10% NH$_3$-methanol, flow: 30 ml/min (loading pump 4 ml/min methanol) target mass 463 column: YMC Triart C18 100×20 mm, 5 um), second HPLC (LC 11 50-50-60% 0-1-5 min water-acetonitrile, flow: 30 ml/min (loading pump 4 ml/min acetonitrile), target mass 463 column: SunFire C18 100×19 mm, 5 um) to obtain 2-[2-[3-(1-acetyl-4-piperidyl)phenyl]-1-piperidyl]-N-(6-amino-5-methyl-3-pyridyl)-2-oxo-acetamide (61 mg, 131.59 µmol, 24.72% yield).

$^1$H NMR (400 MHz, CDCl$_3$) δ (ppm) 1.67 (m, 6H), 1.84 (m, 2H), 1.97 (m, 1H), 2.11 (m, 6H), 2.52 (m, 2H), 2.93 (m, 3H), 4.14 (m, 3H), 4.84 (m, 2H), 6.15 (m, 1H), 7.08 (m, 3H), 7.31 (m, 1H), 7.74 (m, 1H), 8.06 (m, 1H), 9.08 (m, 1H).

LCMS(ESI): [M]$^+$ m/z: calcd 463.6; found 464.2; Rt=2.592 min.

Step 3: Chiral Separation (Compound 94 and Compound 96

Purification on the chiral column was taken in the system Hex-IPA-MeOH, 60-20-20, 0.6 mL/min. Number of injections: 1, injection volume: 1 mkl. From 53 mg of racemate, 16 mg and 18 mg of the individual enantiomers were obtained.

rel-(R)-2-(2-(3-(1-acetylpiperidin-4-yl)phenyl)piperidin-1-yl)-N-(6-amino-5-methylpyridin-3-yl)-2-oxoacetamide Peak 1 Compound 94

Retention time: 18.09 min $^1$H NMR (600 MHz, DMSO-d$_6$) δ (ppm) 1.42 (m, 2H), 1.59 (m, 4H), 1.79 (m, 3H), 2.01 (m, 6H), 2.62 (m, 2H), 3.03 (m, 2H), 3.65 (m, 2H), 4.30 (m, 2H), 5.61 (m, 3H), 7.16 (m, 3H), 7.31 (m, 1H), 7.48 (m, 1H), 8.00 (m, 1H), 10.53 (m, 1H).

LCMS(ESI): [M]$^+$ m/z: calcd 463.6; found 464.2; Rt=3.543 min.

rel-(R)-2-(2-(3-(1-acetylpiperidin-4-yl)phenyl)piperidin-1-yl)-N-(6-amino-5-methylpyridin-3-yl)-2-oxoacetamide Peak 2 Compound 96

Retention time: 23.84 min $^1$H NMR (600 MHz, DMSO-d$_6$) δ (ppm) 1.42 (m, 2H), 1.59 (m, 4H), 1.79 (m, 3H), 2.01 (m, 6H), 2.66 (m, 2H), 3.03 (m, 2H), 3.73 (m, 2H), 4.31 (m, 2H), 5.60 (m, 3H), 7.13 (m, 2H), 7.17 (m, 1H), 7.31 (m, 1H), 7.52 (m, 1H), 8.04 (m, 1H), 10.53 (m, 1H).

LCMS(ESI): [M]$^+$ m/z: calcd 463.6; found 464.2; Rt=3.544 min.

Example 296. The Synthesis of 2-(2-(3-(1-acetylpiperidin-4-yl)phenyl)-5-methylpiperidin-1-yl)-N-(6-amino-5-methylpyridin-3-yl)-2-oxoacetamide (Compound 324, Compound 331

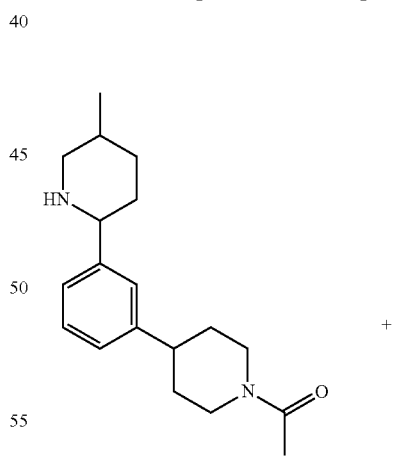

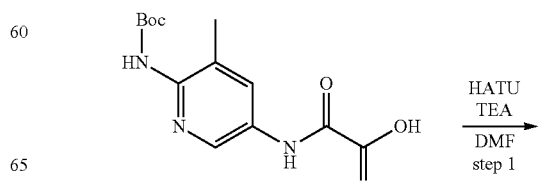

-continued

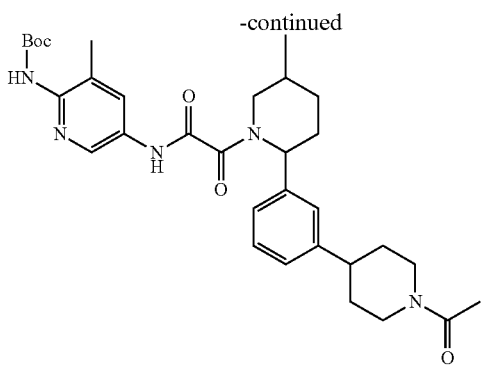

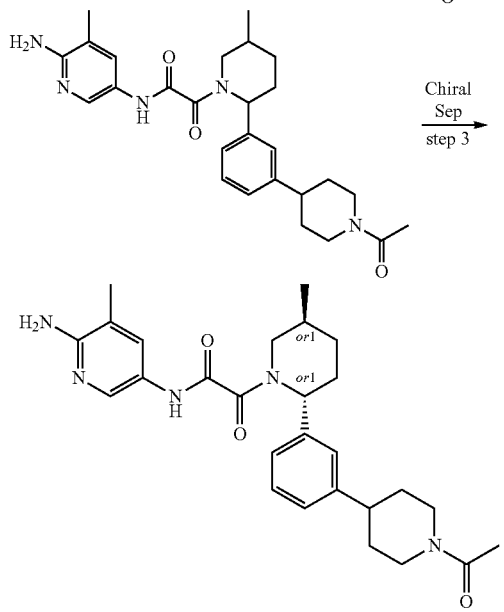

Compound 324

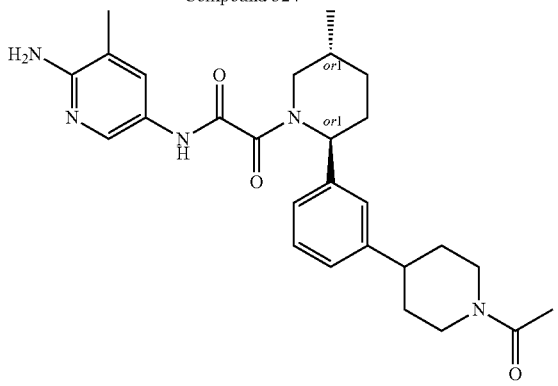

Compound 331

Step 1: Synthesis of tert-butyl (5-(2-(2-(3-(1-acetylpiperidin-4-yl)phenyl)-5-methylpiperidin-1-yl)-2-oxoacetamido)-3-methylpyridin-2-yl)carbamate To a suspension of 1-[4-[3-(5-methyl-2-piperidyl)phenyl]-1-piperidyl]ethanone (0.4 g, 1.33 mmol), 2-[[6-(tert-butoxycarbonylamino)-5-methyl-3-pyridyl]amino]-2-oxoacetic acid (393.15 mg, 1.33 mmol) and HATU (556.86 mg, 1.46 mmol) in DMF (5 mL), triethylamine (673.62 mg, 6.66 mmol, 927.85 μL) was added. The resulting mixture was stirred at 25° C. for 24 hr, taken up with water (50 ml) and extracted with EtOAc (3*20 ml). The combined organic layer was washed with brine (3*20 ml), dried over $Na_2SO_4$ and evaporated to obtain tert-butyl N-[5-[[2-[2-[3-(1-acetyl-4-piperidyl)phenyl]-5-methyl-1-piperidyl]-2-oxo-acetyl]amino]-3-methyl-2-pyridyl]carbamate (0.7 g, crude). This compound was used for the next step without purification.

$^1$H NMR (400 MHz, DMSO-$d_6$) δ (ppm) 0.99 (m, 3H), 1.40 (s, 9H), 1.73 (m, 3H), 1.98 (m, 5H), 2.16 (m, 3H), 2.65 (m, 5H), 3.07 (m, 1H), 3.86 (m, 1H), 4.50 (m, 1H), 5.35 (m, 1H), 7.14 (m, 3H), 7.23 (m, 2H), 7.91 (m, 3H), 8.39 (m, 1H), 9.04 (m, 1H), 11.03 (m, 1H).

LCMS(ESI): [M]$^+$ m/z: calcd 577.6; found 578.2; Rt=1.396 min.

Step 2: Synthesis of 2-(2-(3-(1-acetylpiperidin-4-yl)phenyl)-5-methylpiperidin-1-yl)-N-(6-amino-5-methylpyridin-3-yl)-2-oxoacetamide To a solution of tert-butyl N-[5-[[2-[2-[3-(1-acetyl-4-piperidyl)phenyl]-5-methyl-1-piperidyl]-2-oxo-acetyl]amino]-3-methyl-2-pyridyl]carbamate (0.7 g, 1.21 mmol) in DCM (10 mL), hydrogen chloride solution 4.0 M in dioxane (8.00 g, 219.41 mmol, 10 mL) was added. The resulting mixture was stirred at 25° C. for 12 hr and evaporated in vacuo and subjected to HPLC: 50-55% 0-5 min 0.1% $NH_3$-methanol, flow: 30 ml/min (loading pump 4 ml/min methanol) target mass 478 column: YMC Triart C18 100×20 mm, 5 um) to give 2-[2-[3-(1-acetyl-4-piperidyl)phenyl]-5-methyl-1-piperidyl]-N-(6-amino-5-methyl-3-pyridyl)-2-oxo-acetamide (200 mg, 418.76 μmol, 34.56% yield).

$^1$H NMR (500 MHz, DMSO-$d_6$) δ (ppm) 1.02 (m, 3H), 1.32 (m, 3H), 1.78 (m, 7H), 2.02 (m, 4H), 2.12 (m, 1H), 2.55 (m, 1H), 2.74 (m, 1H), 3.16 (m, 2H), 3.43 (m, 1H), 3.89 (m, 1H), 4.51 (m, 1H), 5.63 (m, 3H), 7.16 (m, 3H), 7.32 (m, 1H), 7.51 (m, 1H), 8.02 (m, 1H), 10.54 (m, 1H).

LCMS(ESI): [M]$^+$ m/z: calcd 477.6; found 478.2; Rt=2.475 min.

Step 3: Chiral Separation (Compound 324 and Compound 331

Purification on the chiral column was taken in the system Hex-IPA-MeOH, 50-25-25, 10 mL/min. Number of injections: 1, injection volume: 500 mkl. From 200 mg of racemate, 63 mg and 60 mg of the individual enantiomers were obtained.

Rel-2-((2R,5S)-2-(3-(1-acetylpiperidin-4-yl)phenyl)-5-methylpiperidin-1-yl)-N-(6-amino-5-methylpyridin-3-yl)-2-oxoacetamide Peak 2 Compound 324

Retention time: 36.18 min $^1$H NMR (600 MHz, DMSO-$d_6$) δ (ppm) 1.00 (m, 3H), 1.31 (m, 1H), 1.42 (m, 1H), 1.58 (m, 2H), 1.74 (m, 2H), 1.86 (m, 1H), 2.00 (m, 6H), 2.05 (m, 1H), 2.19 (m, 1H), 2.54 (m, 1H), 2.81 (m, 2H), 3.17 (m, 1H), 3.83 (m, 2H), 4.50 (m, 1H), 5.33 (m, 1H), 5.60 (m, 2H), 7.13 (m, 3H), 7.30 (m, 1H), 7.46 (m, 1H), 7.98 (m, 1H), 10.50 (m, 1H).

LCMS(ESI): [M]$^+$ m/z: calcd 477.6; found 478.2; Rt=2.441 min.

Rel-2-((2R,5S)-2-(3-(1-acetylpiperidin-4-yl)phenyl)-5-methylpiperidin-1-yl)-N-(6-amino-5-methylpyridin-3-yl)-2-oxoacetamide Peak 1 Compound 331

Retention time: 22.94 min $^1$H NMR (600 MHz, DMSO-$d_6$) δ (ppm) 1.00 (m, 3H), 1.31 (m, 1H), 1.42 (m, 1H), 1.58 (m, 2H), 1.75 (m, 2H), 1.85

(m, 1H), 2.00 (m, 6H), 2.07 (m, 1H), 2.20 (m, 1H), 2.54 (m, 1H), 2.85 (m, 2H), 3.17 (m, 1H), 3.83 (m, 2H), 4.50 (m, 1H), 5.33 (m, 1H), 5.60 (m, 2H), 7.12 (m, 2H), 7.17 (m, 1H), 7.30 (m, 1H), 7.46 (m, 1H), 7.98 (m, 1H), 10.50 (m, 1H).

LCMS(ESI): [M]⁺ m/z: calcd 477.6; found 478.2; Rt=2.445 min.

Example 297. The Synthesis of N-(6-amino-5-methyl-3-pyridyl)-2-oxo-2-(2-phenyl-1-piperidyl)acetamide (Compound 53, N-(6-amino-5-methyl-3-pyridyl)-2-oxo-2-[(2R)-2-phenyl-1-piperidyl]acetamide (Compound 55) and N-(6-amino-5-methyl-3-pyridyl)-2-oxo-2-[(2S)-2-phenyl-1-piperidyl]acetamide (Compound 51

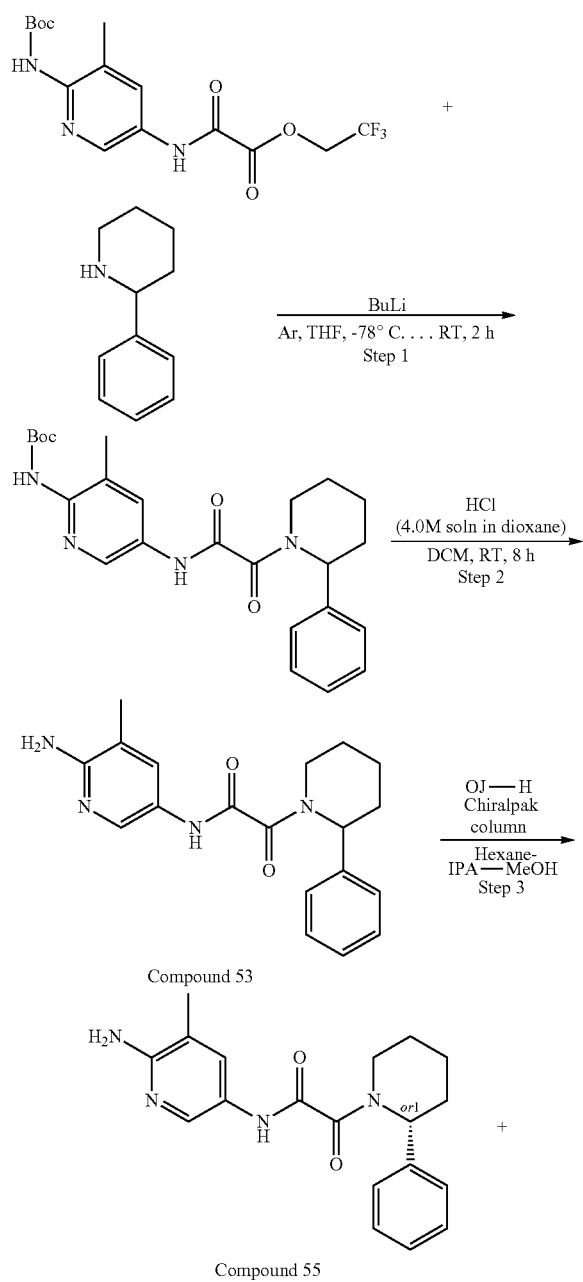

Compound 53

Compound 55

-continued

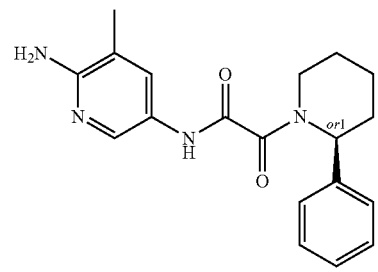

Compound 51

Step 1: The Synthesis of N-[3-methyl-5-[[2-oxo-2-(2-phenyl-1-piperidyl)acetyl]amino]-2-pyridyl]carbamate To a solution of 2-phenylpiperidine (345.82 mg, 1.75 mmol, HCl) in THF (15 mL) was added butyllithium (481.83 mg, 7.52 mmol, 3 mL) dropwise at −78° C. under Ar. The reaction mixture was stirred at −78° C. for 20 min, then 2,2,2-trifluoroethyl 2-[[6-(tert-butoxycarbonylamino)-5-methyl-3-pyridyl]amino]-2-oxo-acetate (0.66 g, 1.75 mmol) was added portionwise. The resulting solution was stirred at −78° C. for 30 min. and at room temperature for 1 hr. The resulting solution was cooled to −50° C. and quenched with sat. NH₄Cl (aq) (40 ml). The organic layer was separated and the aqueous layer was extracted with EtOAc (20 mL×2). The combined organic layers were washed with brine, dried over Na₂SO₄ and concentrated to dryness to give tert-butyl N-[3-methyl-5-[[2-oxo-2-(2-phenyl-1-piperidyl)acetyl]amino]-2-pyridyl]carbamate (0.67 g, crude).

LCMS(ESI): [M+H]⁺ m/z: calcd 438.2; found 439.2; Rt=1.352 min.

Step 2: The Synthesis of N-(6-amino-5-methyl-3-pyridyl)-2-oxo-2-(2-phenyl-1-piperidyl)acetamide (Compound 53

Hydrogen chloride solution 4.0 M in dioxane (800.00 mg, 21.94 mmol, 1 mL) was added to a solution of tert-butyl N-[3-methyl-5-[[2-oxo-2-(2-phenyl-1-piperidyl)acetyl]amino]-2-pyridyl]carbamate (0.67 g, 1.53 mmol) in DCM (10 mL). The reaction mixture was stirred at 25° C. for 8 hr, then evaporated in vacuo and obtained crude product 0.5 g was purified by preparative 45-70% 0-9.5 min water-methanol, flow 30 ml/min to afford product N-(6-amino-5-methyl-3-pyridyl)-2-oxo-2-(2-phenyl-1-piperidyl)acetamide (16.30 mg, 43.48 µmol, 2.85% yield, HCl). ¹H NMR (400 MHz, CDCl₃) δ 1.58 (m, 3H), 1.99 (m, 3H), 2.11 (m, 3H), 2.47 (m, 1H), 2.98 (m, 1H), 4.64 (m, 3H), 6.19 (m, 1H), 7.26 (m, 3H), 7.35 (m, 2H), 7.74 (m, 1H), 8.05 (m, 1H), 9.12 (m, 1H). LCMS(ESI): [M+H]⁺ m/z: calcd 338.2; found 339.2; Rt=0.922 min.

Step 3: The Synthesis of N-(6-amino-5-methyl-3-pyridyl)-2-oxo-2-[(2R)-2-phenyl-1-piperidyl]acetamide (Compound 55) and N-(6-amino-5-methyl-3-pyridyl)-2-oxo-2-[(2S)-2-phenyl-1-piperidyl]acetamide (Compound 51

The enantiomers were separated by chiral HPLC (column: OJ-H (250*20, 5 mkm), Hexane-IPA-MeOH, 50-25-25%, 15 ml/min as mobile phase) to give the two individual enantiomers Compound 55—N-(6-amino-5-methyl-3-pyridyl)-2-oxo-2-[(2R)-2-phenyl-1-piperidyl]acetamide (0.0027 g, 7.20 μmol, 16.56% yield, HCl; RT=34.348 min) and Compound 51—N-(6-amino-5-methyl-3-pyridyl)-2-oxo-2-[(2S)-2-phenyl-1-piperidyl]acetamide (0.0026 g, 6.94 μmol, 15.95% yield, HCl; RT=15.833 min).

Compound 51: RT (OJ-H, Hexane-IPA-MeOH, 50-25-25, 0.6 ml/min)=15.411 min.

LCMS(ESI): [M+H]$^+$ m/z: calcd 338.2; found 339.2; Rt=1.048 min.

Compound 55: RT (OJ-H, Hexane-IPA-MeOH, 50-25-25, 0.6 ml/min)=41.216 min.

LCMS(ESI): [M+H]$^+$ m/z: calcd 338.2; found 339.2; Rt=1.043 min.

Example 298. The Synthesis of N-(6-amino-5-methyl-3-pyridyl)-2-(5-methyl-2-phenyl-1-piperidyl)-2-oxo-acetamide (Compound 27), N-(6-amino-5-methylpyridin-3-yl)-2-((2R,5S)-5-methyl-2-phenylpiperidin-1-yl)-2-oxoacetamide (Compound 33), N-(6-amino-5-methyl-3-pyridyl)-2-[(2S,5S)-5-methyl-2-phenyl-1-piperidyl]-2-oxo-acetamide (Compound 37), N-(6-amino-5-methyl-3-pyridyl)-2-[(2R,5R)-5-methyl-2-phenyl-1-piperidyl]-2-oxo-acetamide (Compound 43), and N-(6-amino-5-methyl-3-pyridyl)-2-[(2R,5S)-5-methyl-2-phenyl-1-piperidyl]-2-oxo-acetamide (Compound 40

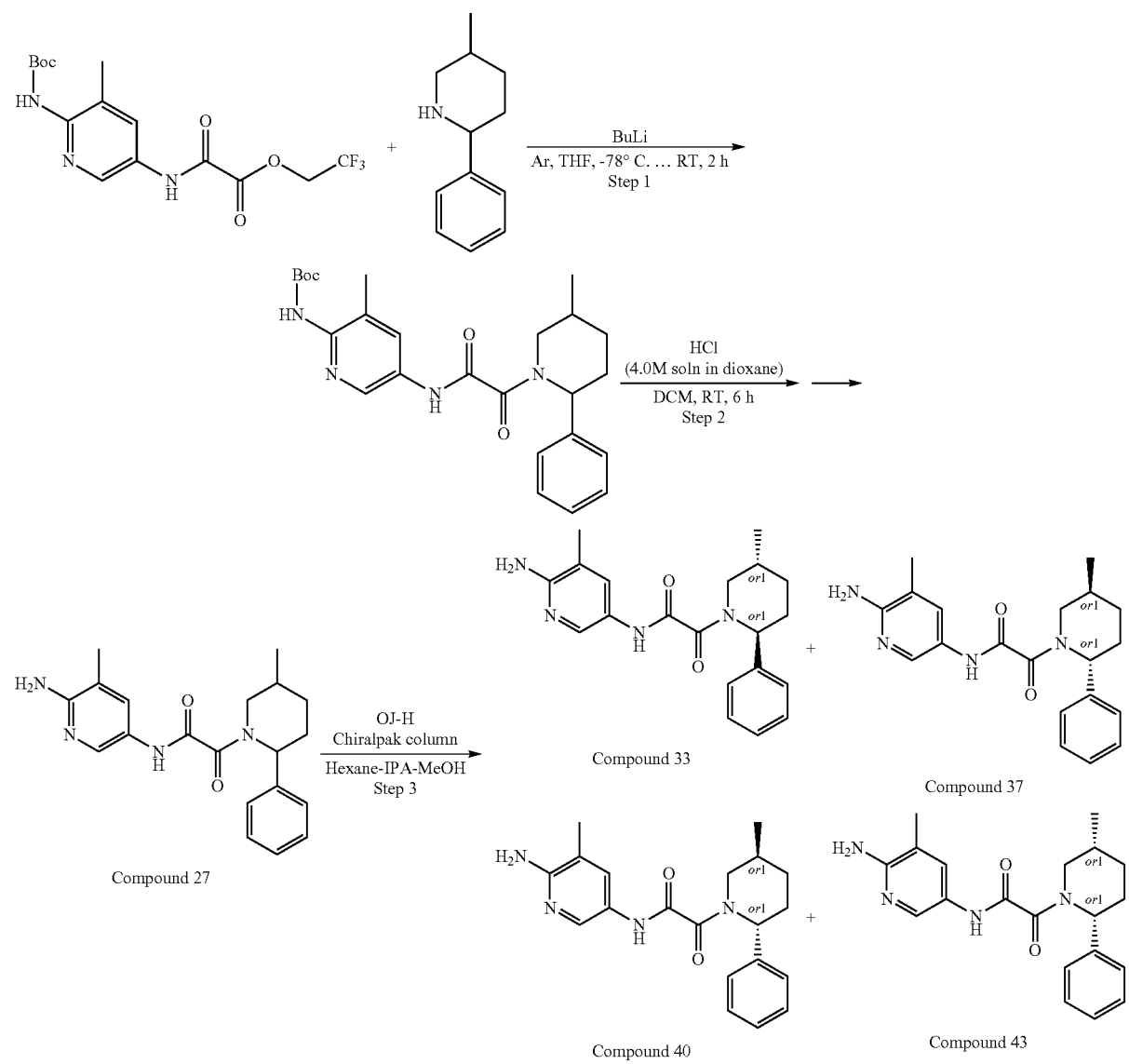

Step 1: The Synthesis of tert-butyl N-[3-methyl-5-[[2-(5-methyl-2-phenyl-1-piperidyl)-2-oxo-acetyl]amino]-2-pyridyl]carbamate To a solution of 5-methyl-2-phenyl-piperidine (222.97 mg, 1.27 mmol) in THF (15 mL) was added butyllithium (268.91 mg, 4.20 mmol, 2.4 mL) dropwise at −78° C. under Ar. The reaction mixture was stirred at −78° C. for 20 min, then 2,2,2-trifluoroethyl 2-[[6-(tert-butoxycarbonylamino)-5-methyl-3-pyridyl]amino]-2-oxo-acetate (0.48 g, 1.27 mmol) was added portionwise. The resulting solution was stirred at −78° C. for 30 min. and at room temperature for 1 hr. The resulting solution was cooled to −50° C. and quenched with sat. NH$_4$Cl (aq) (30 ml). The organic layer was separated and the aqueous layer was extracted with EtOAc (20 mL×2). The combined organic layers were washed with brine, dried over Na$_2$SO$_4$ and concentrated to dryness to give tert-butyl N-[3-methyl-5-[[2-(5-methyl-2-phenyl-1-piperidyl)-2-oxo-acetyl]amino]-2-pyridyl]carbamate (0.54 g, crude). $^1$H NMR (400 MHz, CDCl$_3$) δ 0.87 (d, 3H), 1.16 (m, 4H), 1.48 (s, 9H), 1.62 (m, 2H), 1.82 (m, 2H), 2.27 (m, 2H), 3.72 (m, 2H), 6.68 (m, 1H), 7.19 (m, 5H), 8.04 (m, 1H). LCMS(ESI): [M+H]$^+$ m/z: calcd 452.2; found 453.2; Rt=1.419 min.

Step 2: The Synthesis of N-(6-amino-5-methyl-3-pyridyl)-2-(5-methyl-2-phenyl-1-piperidyl)-2-oxo-acetamide (Compound 27

Hydrogen chloride solution 4.0 M in dioxane (800.00 mg, 21.94 mmol, 1 mL) was added to a solution of tert-butyl N-[3-methyl-5-[[2-(5-methyl-2-phenyl-1-piperidyl)-2-oxo-acetyl]amino]-2-pyridyl]carbamate (0.54 g, 1.19 mmol) in DCM (10 mL). The reaction mixture was stirred at 25° C. for 6 hr, then evaporated in vacuo and obtained crude product 0.4 g was purified by preparative 50-75% 0-10.5 min water-methanol, flow 30 ml/min to afford product N-(6-amino-5-methyl-3-pyridyl)-2-(5-methyl-2-phenyl-1-piperidyl)-2-oxo-acetamide (0.0167 g, 42.94 µmol, 3.60% yield, HCl)$^1$H NMR (400 MHz, CD$_3$OD) δ 0.85 (m, 2H), 1.13 (m, 3H), 1.35 (m, 1H), 1.64 (m, 1H), 1.87 (m, 2H), 2.13 (m, 3H), 2.26 (m, 1H), 3.60 (m, 1H), 5.62 (m, 1H), 7.26 (m, 1H), 7.37 (m, 4H), 7.57 (m, 1H), 8.02 (m, 1H). LCMS(ESI): [M+H]$^+$ m/z: calcd 352.2; found 353.4; Rt=2.499 min.

Step 3: The Synthesis of N-(6-amino-5-methylpyridin-3-yl)-2-((2R,5S)-5-methyl-2-phenylpiperidin-1-yl)-2-oxoacetamide (Compound 33), N-(6-amino-5-methyl-3-pyridyl)-2-[(2S,5S)-5-methyl-2-phenyl-1-piperidyl]-2-oxo-acetamide Compound 37), N-(6-amino-5-methyl-3-pyridyl)-2-[(2R,5R)-5-methyl-2-phenyl-1-piperidyl]-2-oxo-acetamide (Compound 43), and N-(6-amino-5-methyl-3-pyridyl)-2-[(2R,5S)-5-methyl-2-phenyl-1-piperidyl]-2-oxo-acetamide (Compound 40

Chiral separation of N-(6-amino-5-methylpyridin-3-yl)-2-(5-methyl-2-phenylpiperidin-1-yl)-2-oxoacetamide (22.0 mg, 62.42 µmol) was performed using OJ-H Chiralpak column, Hexane-IPA-MeOH as a solvent mixture, 70-15-15, Flow 15 ml/min affording Compound 33-N-(6-amino-5-methylpyridin-3-yl)-2-((2R,5S)-5-methyl-2-phenylpiperidin-1-yl)-2-oxoacetamide (7.8 mg, 22.13 µmol, 35.45% yield; RT=22.466 min), Compound 37—N-(6-amino-5-methyl-3-pyridyl)-2-[(2S,5S)-5-methyl-2-phenyl-1-piperidyl]-2-oxo-acetamide (3.4 mg, 9.65 µmol, 15.45% yield; RT=17.308 min), Compound 43—N-(6-amino-5-methyl-3-pyridyl)-2-[(2R,5R)-5-methyl-2-phenyl-1-piperidyl]-2-oxo-acetamide (2.7 mg, 7.66 µmol, 12.27% yield; RT=42.900 min), and Compound 40—N-(6-amino-5-methyl-3-pyridyl)-2-[(2R,5S)-5-methyl-2-phenyl-1-piperidyl]-2-oxo-acetamide (7.8 mg, 22.13 µmol, 35.45% yield; RT=49.446 min) as a yellow solids.

Compound 33: RT (OJ-H, Hexane-IPA-MeOH, 70-15-15, 0.6 ml/min)=23.187 min. $^1$H NMR (500 MHz, CDCl$_3$) δ 1.11 (d, 3H), 1.41 (m, 1H), 1.90 (m, 2H), 2.15 (m, 3H), 2.23 (m, 2H), 3.26 (m, 1H), 4.62 (m, 3H), 5.82 (m, 1H), 7.30 (m, 3H), 7.38 (m, 2H), 7.76 (s, 1H), 8.04 (m, 1H), 9.08 (s, 1H). LCMS(ESI): [M+H]$^+$ m/z: calcd 352.2; found 353.0; Rt=3.821 min.

Compound 37: RT (OJ-H, Hexane-IPA-MeOH, 70-15-15, 0.6 ml/min)=16.722 min. $^1$H NMR (500 MHz, CDCl$_3$) δ 0.86 (m, 3H), 1.32 (m, 1H), 1.44 (m, 1H), 1.72 (m, 2H), 1.86 (m, 1H), 2.03 (m, 1H), 2.15 (m, 3H), 2.56 (m, 2H), 4.65 (m, 2H), 6.25 (m, 1H), 7.30 (m, 2H), 7.39 (m, 2H), 7.78 (m, 1H), 8.07 (m, 1H), 9.03 (m, 1H). LCMS(ESI): [M+H]$^+$ m/z: calcd 352.2; found 353.0; Rt=3.789 min.

Compound 43: RT (OJ-H, Hexane-IPA-MeOH, 70-15-15, 0.6 ml/min)=47.178 min. $^1$H NMR (500 MHz, CDCl$_3$) δ 0.86 (m, 3H), 1.31 (m, 1H), 1.46 (m, 1H), 1.73 (m, 2H), 1.87 (m, 1H), 2.03 (m, 1H), 2.15 (m, 3H), 2.53 (m, 2H), 4.66 (m, 2H), 6.24 (m, 1H), 7.30 (m, 2H), 7.39 (m, 2H), 7.78 (m, 1H), 8.07 (m, 1H), 9.04 (m, 1H). LCMS(ESI): [M+H]$^+$ m/z: calcd 352.2; found 353.0; Rt=3.792 min.

Compound 40: RT (OJ-H, Hexane-IPA-MeOH, 70-15-15, 0.6 ml/min)=57.061 min. $^1$H NMR (500 MHz, CDCl$_3$)) δ 1.11 (d, 3H), 1.41 (m, 1H), 1.92 (m, 2H), 2.15 (m, 3H), 2.26 (m, 2H), 3.32 (m, 1H), 4.73 (m, 3H), 6.17 (m, 1H), 7.30 (m, 3H), 7.38 (m, 2H), 7.76 (s, 1H), 8.07 (m, 1H), 9.08 (s, 1H). LCMS(ESI): [M+H]$^+$ m/z: calcd 352.2; found 353.0; Rt=3.710 min.

Example 299. The Synthesis of N-(6-amino-5-methyl-3-pyridyl)-2-oxo-2-[2-(4-pyridyl)-1-piperidyl]acetamide (Compound 36), N-(6-amino-5-methyl-3-pyridyl)-2-oxo-2-[(2R)-2-(4-pyridyl)-1-piperidyl]acetamide (Compound 50) and N-(6-amino-5-methyl-3-pyridyl)-2-oxo-2-[(2S)-2-(4-pyridyl)-1-piperidyl]acetamide (Compound 47

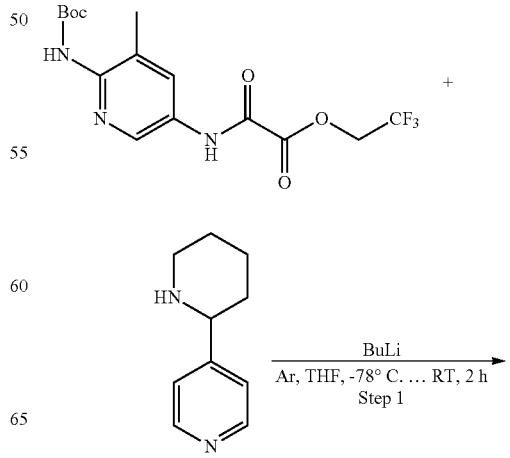

-continued

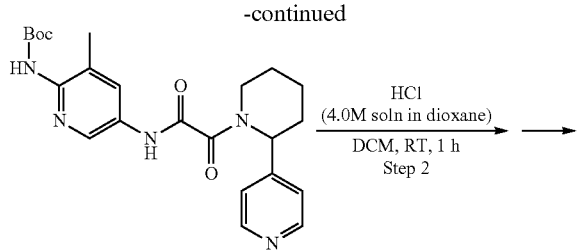

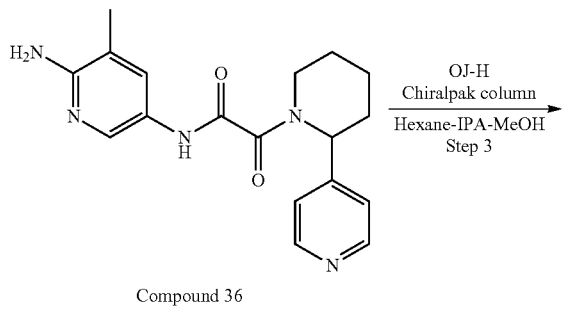

Compound 36

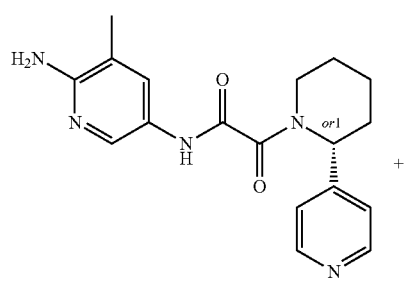

Compound 50

+

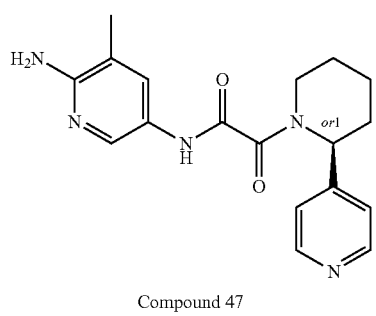

Compound 47

Step 1: The Synthesis of tert-butyl N-[3-methyl-5-[[2-oxo-2-[2-(4-pyridyl)-1-piperidyl]acetyl]amino]-2-pyridyl]carbamate To a solution of 4-(2-piperidyl)pyridine (300.97 mg, 1.86 mmol) in THF (19 mL) was added butyllithium (392.19 mg, 6.12 mmol, 2.45 mL) dropwise at −78° C. under Ar. The reaction mixture was stirred at −78° C. for 20 min, then 2,2,2-trifluoroethyl 2-[[6-(tert-butoxycarbonylamino)-5-methyl-3-pyridyl]amino]-2-oxo-acetate (0.7 g, 1.86 mmol) was added portionwise. The resulting solution was stirred at −78° C. for 30 min and at room temperature for 1 hr. The resulting solution was cooled to −50° C. and quenched with sat. NH₄Cl (aq) (30 ml). The organic layer was separated and the aqueous layer was extracted with EtOAc (20 mL×2). The combined organic layers were washed with brine, dried over Na₂SO₄ and concentrated to dryness to give tert-butyl N-[3-methyl-5-[[2-oxo-2-[2-(4-pyridyl)-1-piperidyl]acetyl]amino]-2-pyridyl]carbamate (0.48 g, 1.09 mmol, 58.87% yield). ¹H NMR (500 MHz, DCMSO-d₆) δ 0.87 (m, 3H), 1.44 (s, 9H), 2.08 (m, 2H), 2.31 (m, 4H), 2.60 (m, 2H), 3.71 (m, 2H), 6.75 (d, 1H), 7.22 (d, 1H), 7.99 (d, 1H), 8.05 (s, 1H), 8.33 (d, 1H), 8.62 (s, 1H), 9.45 (m, 1H). LCMS(ESI): [M−Boc]⁺ m/z: calcd 339.2; found 340.2; Rt=1.033 min.

Step 2: The Synthesis of N-(6-amino-5-methyl-3-pyridyl)-2-oxo-2-[2-(4-pyridyl)-1-piperidyl]acetamide (Compound 36

Hydrogen chloride solution 4.0 M in dioxane (640.00 mg, 17.55 mmol, 0.8 mL) was added to a solution of tert-butyl N-[3-methyl-5-[[2-oxo-2-[2-(4-pyridyl)-1-piperidyl]acetyl]amino]-2-pyridyl]carbamate (0.48 g, 1.09 mmol) in DCM (5 mL). The reaction mixture was stirred at 25° C. for 1 hr, then evaporated in vacuo and obtained crude product 0.32 g was purified by preparative 20-70% methanol-NH₃, flow 30 ml/min to afford product N-(6-amino-5-methyl-3-pyridyl)-2-oxo-2-[2-(4-pyridyl)-1-piperidyl]acetamide (0.037 g, 109.02 μmol, 9.98% yield). ¹H NMR (500 MHz, DMSO-d₆) δ 1.45 (m, 2H), 1.65 (m, 2H), 1.73 (m, 1H), 1.96 (m, 1H), 2.07 (m, 3H), 2.45 (m, 1H), 4.12 (m, 1H), 5.24 (m, 2H), 5.55 (m, 1H), 7.30 (m, 2H), 7.55 (m, 1H), 8.03 (m, 1H), 8.53 (m, 2H), 10.41 (m, 1H). LCMS(ESI): [M+H]⁺ m/z: calcd 339.2; found 340.2; Rt=0.522 min.

Step 3: The Synthesis of N-(6-amino-5-methyl-3-pyridyl)-2-oxo-2-[(2R)-2-(4-pyridyl)-1-piperidyl]acetamide (Compound 50) and N-(6-amino-5-methyl-3-pyridyl)-2-oxo-2-[(2S)-2-(4-pyridyl)-1-piperidyl]acetamide (Compound 47

The enantiomers were separated by chiral HPLC (column: OJ-H (250*20, 5 mkm), Hexane-IPA-MeOH, 50-25-25%, 15 ml/min as mobile phase) to give the two individual enantiomers Compound 50—N-(6-amino-5-methyl-3-pyridyl)-2-oxo-2-[(2R)-2-(4-pyridyl)-1-piperidyl]acetamide (0.0125 g, 36.83 μmol, 31.25% yield; RT=27.483 min) and Compound 47—N-(6-amino-5-methyl-3-pyridyl)-2-oxo-2-[(2S)-2-(4-pyridyl)-1-piperidyl]acetamide (0.0108 g, 31.82 μmol, 27.00% yield; RT=14.224 min).

Compound 47: RT (OJ-H, Hexane-IPA-MeOH, 50-25-25, 0.6 ml/min)=15.367 min. ¹H NMR (500 MHz, CDCl₃) δ 1.53 (m, 1H), 1.86 (m, 1H), 2.04 (m, 2H), 2.17 (m, 3H), 2.46 (m, 1H), 2.71 (m, 1H), 3.05 (m, 1H), 4.79 (m, 3H), 6.26 (m, 1H), 7.22 (m, 2H), 7.77 (m, 1H), 8.14 (m, 1H), 8.62 (m, 2H), 9.14 (m, 1H). LCMS(ESI): [M+2H]⁺ m/z: calcd 339.2; found 341.2; Rt=2.309 min.

Compound 50: RT (OJ-H, Hexane-IPA-MeOH, 50-25-25, 0.6 ml/min)=39.557 min. ¹H NMR (500 MHz, CDCl₃) δ 1.54 (m, 2H), 2.04 (m, 2H), 2.20 (m, 3H), 2.48 (m, 1H), 2.71 (m, 1H), 3.05 (m, 1H), 4.81 (m, 3H), 6.26 (m, 1H), 7.22 (m, 2H), 7.76 (m, 1H), 8.13 (m, 1H), 8.62 (m, 2H), 9.13 (m, 1H). LCMS(ESI): [M+2H]⁺ m/z: calcd 339.2; found 341.2; Rt=2.352 min.

Example 300. Synthesis of N-(6-amino-5-methyl-3-pyridyl)-2-[2-(m-tolyl)-1-piperidyl]-2-oxo-acetamide (Compound 31), N-(6-amino-5-methyl-3-pyridyl)-2-[(2R)-2-(m-tolyl)-1-piperidyl]-2-oxo-acetamide (Compound 57) and N-(6-amino-5-methyl-3-pyridyl)-2-[(2S)-2-(m-tolyl)-1-piperidyl]-2-oxo-acetamide (Compound 54

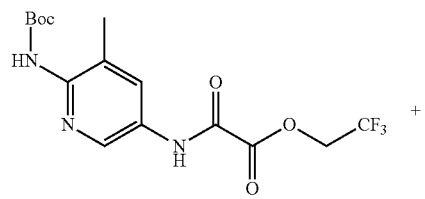

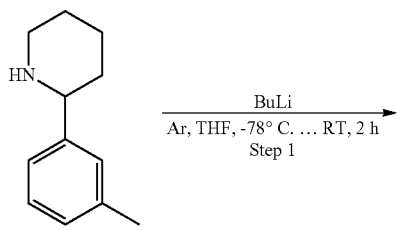

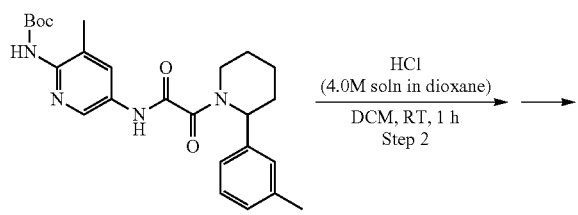

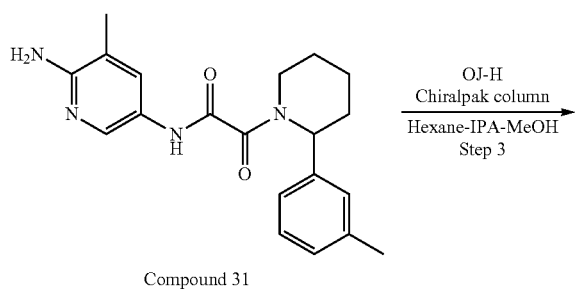

Compound 31

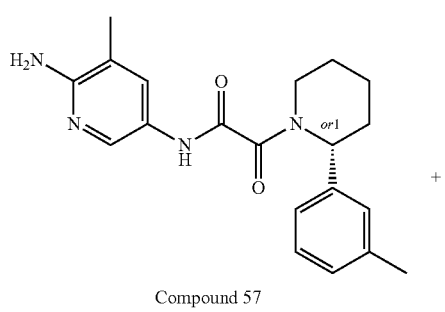

Compound 57

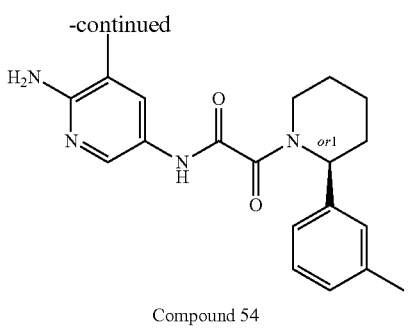

Compound 54

Step 1: The Synthesis of tert-butyl N-[3-methyl-5-[[2-[2-(m-tolyl)-1-piperidyl]-2-oxo-acetyl]amino]-2-pyridyl]carbamate To a solution of 2-(m-tolyl)piperidine (315.87 mg, 1.80 mmol) in THF (15 mL) was added butyllithium (380.98 mg, 5.95 mmol, 2.4 mL) dropwise at −78° C. under Ar. The reaction mixture was stirred at −78° C. for 20 min., then 2,2,2-trifluoroethyl 2-[[6-(tert-butoxycarbonylamino)-5-methyl-3-pyridyl]amino]-2-oxo-acetate (0.68 g, 1.80 mmol) was added portionwise. The resulting solution was stirred at −78° C. for 30 min. and at room temperature for 1 hr. The resulting solution was cooled to −50° C. and quenched with sat. NH$_4$Cl (aq) (30 ml). The organic layer was separated and the aqueous layer was extracted with EtOAc (20 mL×2). The combined organic layers were washed with brine, dried over Na$_2$SO$_4$ and concentrated to dryness to give tert-butyl N-[3-methyl-5-[[2-[2-(m-tolyl)-1-piperidyl]-2-oxo-acetyl]amino]-2-pyridyl]carbamate (0.64 g, 1.41 mmol, 78.47% yield). LCMS(ESI): [M+H]$^+$ m/z: calcd 452.2; found 453.2; Rt=1.449 min.

Step 2: The Synthesis of N-(6-amino-5-methyl-3-pyridyl)-2-[2-(m-tolyl)-1-piperidyl]-2-oxo-acetamide (Compound 31

Hydrogen chloride solution 4.0 M in dioxane (800.00 mg, 21.94 mmol, 1 mL) was added to a solution of tert-butyl N-[3-methyl-5-[[2-[2-(m-tolyl)-1-piperidyl]-2-oxo-acetyl]amino]-2-pyridyl]carbamate (0.64 g, 1.41 mmol) in DCM (5 mL). The reaction mixture was stirred at 25° C. for 1 hr, then evaporated in vacuo and obtained crude product 0.51 g was purified by preparative 50-100% 0-9.5 min water-methanol, flow 30 ml/min to afford product N-(6-amino-5-methyl-3-pyridyl)-2-[2-(m-tolyl)-1-piperidyl]-2-oxo-acetamide (54.70 mg, 140.66 μmol, 9.95% yield, HCl). $^1$H NMR (400 MHz, CDCl$_3$) δ 1.59 (m, 3H), 1.95 (m, 2H), 2.10 (m, 3H), 2.33 (s, 3H), 2.45 (m, 1H), 3.00 (m, 1H), 4.73 (m, 3H), 6.13 (m, 1H), 7.05 (m, 3H), 7.23 (m, 1H), 7.73 (m, 1H), 8.04 (m, 1H), 9.18 (m, 1H). LCMS(ESI): [M+H]$^+$ m/z: calcd 352.2; found 353.2; Rt=1.013 min.

Step 3: Synthesis of N-(6-amino-5-methyl-3-pyridyl)-2-[(2R)-2-(m-tolyl)-1-piperidyl]-2-oxo-acetamide (Compound 57) and N-(6-amino-5-methyl-3-pyridyl)-2-[(2S)-2-(m-tolyl)-1-piperidyl]-2-oxo-acetamide (Compound 54

The enantiomers were separated by chiral HPLC (column: OJ-H (250*20, 5 mkm), Hexane-IPA-MeOH, 50-25-25, 15 ml/min as mobile phase) to give the two individual enantiomers Compound 57—N-(6-amino-5-methyl-3-pyridyl)-

2-[(2R)-2-(m-tolyl)-1-piperidyl]-2-oxo-acetamide (0.0145 g, 41.14 μmol, 94.62% yield; RT=24.885 min) and Compound 54—N-(6-amino-5-methyl-3-pyridyl)-2-[(2S)-2-(m-tolyl)-1-piperidyl]-2-oxo-acetamide (13.70 mg, 38.87 μmol, 89.40% yield; RT=11.660 min).

Compound 54: RT (OJ-H, Hexane-IPA-MeOH, 50-25-25, 0.6 ml/min)=11.352 min. $^1$H NMR (Chloroform-d, 400 MHz): δ (ppm) 1.62 (m, 4H), 1.96 (m, 1H), 2.11 (m, 3H), 2.34 (s, 3H), 2.45 (m, 1H), 2.94 (m, 1H), 4.60 (m, 3H), 6.17 (m, 1H), 7.05 (m, 4H), 7.75 (m, 1H), 8.05 (m, 1H), 9.08 (s, 1H). LCMS(ESI): [M+H]$^+$ m/z: calcd 352.2; found 353.0; Rt=3.847 min.

Compound 57: RT (OJ-H, Hexane-IPA-MeOH, 50-25-25, 0.6 ml/min)=31.245 min. $^1$H NMR (Chloroform-d, 400 MHz): δ (ppm) 1.19 (d, 3H), 1.60 (m, 2H), 1.96 (m, 1H), 2.13 (m, 1H), 2.33 (s, 3H), 2.45 (m, 1H), 2.94 (m, 1H), 4.15 (m, 3H), 4.69 (m, 1H), 6.16 (m, 1H), 7.05 (m, 4H), 7.74 (m, 1H), 8.04 (m, 1H), 9.08 (s, 1H). LCMS(ESI): [M+H]$^+$ m/z: calcd 352.2; found 353.0; Rt=3.854 min.

Example 301. Synthesis of N-(6-amino-5-methyl-3-pyridyl)-2-[2-(4-methylthiazol-2-yl)-1-piperidyl]-2-oxo-acetamide (Compound 49

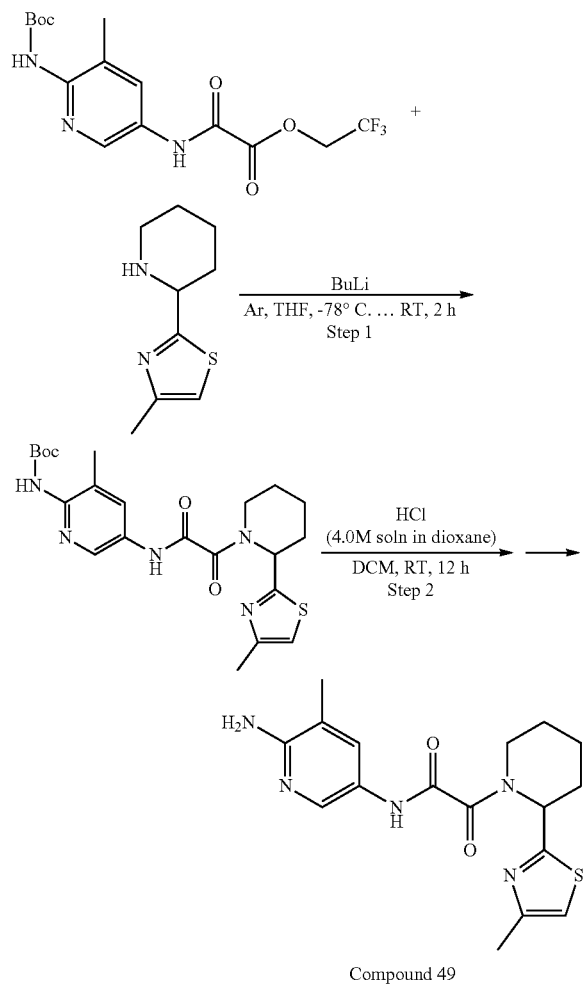

Step 1: Synthesis of tert-butyl N-[3-methyl-5-[[2-[2-(4-methylthiazol-2-yl)-1-piperidyl]-2-oxo-acetyl]amino]-2-pyridyl]carbamate To a solution of 4-methyl-2-(2-piperidyl)thiazole (217.40 mg, 1.19 mmol) and 2,2,2-trifluoroethyl 2-[[6-(tert-butoxycarbonylamino)-5-methyl-3-pyridyl]amino]-2-oxo-acetate (600.00 mg, 1.19 mmol) in THF (15 mL) was added n-butyllithium solution 2.5 M in hexanes (252.12 mg, 3.94 mmol, 1.6 mL) dropwise at −70° C. under Ar. The reaction mixture was stirred at −70° C. for for 30 min. and at room temperature for 1 hr. The resulting solution was cooled to −50° C. and quenched with sat. NH$_4$Cl (aq) (40 ml). The organic layer was separated and the aqueous layer was extracted with EtOAc (20 mL×2). The combined organic layers were washed with brine, dried over Na$_2$SO$_4$ and concentrated to dryness to give tert-butyl N-[3-methyl-5-[[2-[2-(4-methylthiazol-2-yl)-1-piperidyl]-2-oxo-acetyl]amino]-2-pyridyl]carbamate (0.5 g, crude).

LCMS(ESI): [M+H]$^+$ m/z: calcd 459.2; found 460.2; Rt=1.318 min.

Step 2: Synthesis of N-(6-amino-5-methyl-3-pyridyl)-2-[2-(4-methylthiazol-2-yl)-1-piperidyl]-2-oxo-acetamide (Compound 49

Hydrogen chloride solution 4.0 M in dioxane (141.67 mg, 544.00 μmol, 177.09 μL, 14% purity) was carefully added at r.t. to a solution of tert-butyl N-[3-methyl-5-[[2-[2-(4-methylthiazol-2-yl)-1-piperidyl]-2-oxo-acetyl]amino]-2-pyridyl]carbamate (0.5 g, 54.40 μmol) in DCM (20 mL). The reaction mixture was then stirred for 12 hr at r.t. and the solvents were evaporated in vacuo to give 0.5 g of crude material. It was subjected to RP-HPLC (column: YMC Triart C18 100*20 mm, 5 um; 40-40-65%, 0-1-6 min 0.1% NH$_3$-methanol as mobile phase) to give Compound 49—N-(6-amino-5-methyl-3-pyridyl)-2-[2-(4-methylthiazol-2-yl)-1-piperidyl]-2-oxo-acetamide (8 mg, 22.26 μmol, 40.91% yield). $^1$H NMR (400 MHz, CDCl$_3$) δ 1.74 (m, 2H), 1.96 (m, 3H), 2.11 (m, 3H), 2.41 (m, 3H), 2.53 (m, 1H), 3.02 (m, 1H), 4.41 (m, 2H), 4.63 (m, 1H), 6.25 (m, 1H), 6.83 (m, 1H), 7.73 (m, 1H), 8.01 (m, 1H), 9.19 (m, 1H).

LCMS(ESI): [M+H]$^+$ m/z: calcd 359.2; found 360.2; Rt=2.128 min.

Example 302. The Synthesis of N-(6-amino-5-methyl-3-pyridyl)-2-oxo-2-[(1S,4S,5R)-4-(2-thienyl)-3-azabicyclo[3.2.1]octan-3-yl]acetamide (Compound 134 and Compound 137

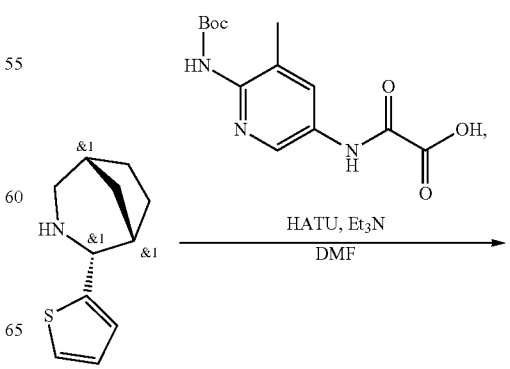

-continued

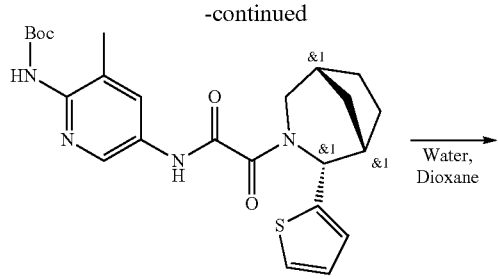

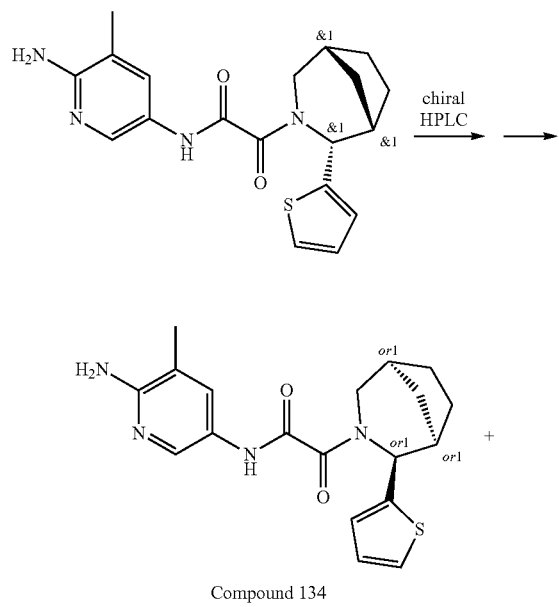

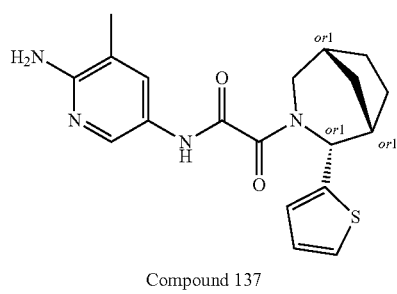

Compound 137

Step 1: Synthesis of tert-butyl N-[3-methyl-5-[[2-oxo-2-[(1S,4S,5R)-4-(2-thienyl)-3-azabicyclo[3.2.1]octan-3-yl]acetyl]amino]-2-pyridyl]carbamate A suspension of (1S,4S,5R)-4-(2-thienyl)-3-azabicyclo[3.2.1]octane (400.00 mg, 2.07 mmol), 2-[[6-(tert-butoxycarbonylamino)-5-methyl-3-pyridyl]amino]-2-oxo-acetic acid (611.03 mg, 2.07 mmol), HATU (826.13 mg, 2.17 mmol) and Triethylamine (1.05 g, 10.35 mmol, 1.44 mL) in DMF (3 mL) was stirred at 30° C. for 3 hours. After 3 hours, the crude product was concentrated in vacuo and the crude product was subjected to reverse phase HPLC purification (Eluent: 1-6 min, 45% water-acetonitrile; flow rate: 30 mL/min; loading pump: 4 mL/min, acetonitrile) to obtain product tert-butyl N-[3-methyl-5-[[2-oxo-2-[(1S,4S,5R)-4-(2-thienyl)-3-azabicyclo[3.2.1]octan-3-yl]acetyl]amino]-2-pyridyl]carbamate (170 mg, 361.25 μmol, 17.46% yield) as a white solid.

LCMS(ESI): $[M+H]^+$ m/z: calcd 470.2; found 471.2; Rt=3.682 min.

Step 2: Synthesis of N-(6-amino-5-methyl-3-pyridyl)-2-oxo-2-[(1S,4S,5R)-4-(2-thienyl)-3-azabicyclo[3.2.1]octan-3-yl]acetamide A suspension of tert-butyl N-[3-methyl-5-[[2-oxo-2-[(1S,4S,5R)-4-(2-thienyl)-3-azabicyclo[3.2.1]octan-3-yl]acetyl]amino]-2-pyridyl]carbamate (170.00 mg, 361.25 μmol) in Water (3 mL) and dioxane (1 mL) was heated at 100° C. for 24 hours. The crude reaction mixture was subjected to reverse phase HPLC purification (Eluent: 40-40-90%, 0-1-5 min 0.1% $NH_3$-methanol, flow rate: 30 mL/min; loading pump: 4 mL/min, methanol; column: YMC Triart C18 100×20 mm, 5 um) to obtain product N-(6-amino-5-methyl-3-pyridyl)-2-oxo-2-[(1S,4S,5R)-4-(2-thienyl)-3-azabicyclo[3.2.1]octan-3-yl]acetamide (78 mg, 210.54 μmol, 58.28% yield) as a white solid.

LCMS(ESI): $[M+H]^+$ m/z: calcd 370.2; found 371.2; Rt=2.184 min.

Step 3: Chiral Separation of N-(6-amino-5-methyl-3-pyridyl)-2-oxo-2-[(1S,4S,5R)-4-(2-thienyl)-3-azabicyclo[3.2.1]octan-3-yl]acetamide and N-(6-amino-5-methyl-3-pyridyl)-2-oxo-2-[(1R,4R,5S)-4-(2-thienyl)-3-azabicyclo[3.2.1]octan-3-yl]acetamide (Compound 134 and Compound 137

N-(6-amino-5-methyl-3-pyridyl)-2-oxo-2-[(1S,4S,5R)-4-(2-thienyl)-3-azabicyclo[3.2.1]octan-3-yl]acetamide (40.00 mg, 107.97 μmol) was subjected to chiral HPLC purification (Column: Chiralpak OJ (250×30 mm, 20 um; Mobile phase: Hexane-IPA-MeOH, 50-25-25. Flow Rate: 28 mL/min; Column Temperature: 24° C.; Wavelength: 205 nm) to get product N-(6-amino-5-methyl-3-pyridyl)-2-oxo-2-[(1S,4S,5R)-4-(2-thienyl)-3-azabicyclo[3.2.1]octan-3-yl]acetamide (Compound 134, 17 mg, 45.89 μmol) and N-(6-amino-5-methyl-3-pyridyl)-2-oxo-2-[(1R,4R,5S)-4-(2-thienyl)-3-azabicyclo[3.2.1]octan-3-yl]acetamide (Compound 137.16 mg, 43.19 μmol) as white solids.

Compound 134 $^1H$ NMR (DMSO-$d_6$, 500 MHz): δ (ppm) 1.41 (m, 5H), 1.63 (m, 2H), 2.00 (m, 4H), 3.92 (m, 1H), 5.56 (m, 3H), 6.88 (m, 3H), 7.42 (m, 2H), 8.03 (m, 1H), 10.34 (m, 1H).

LCMS(ESI): $[M+H]^+$ m/z: calcd 370.2; found 371.0; Rt=3.685 min Chiral HPLC: Rt=14.19 min (OJ-H, Mobile phase: Hexane-IPA-MeOH, 50-25-25. Flow Rate: 0.6 mL/min).

Compound 137 $^1H$ NMR (DMSO-$d_6$, 500 MHz): δ (ppm) 1.41 (m, 5H), 1.63 (m, 2H), 2.01 (m, 4H), 3.92 (m, 1H), 5.56 (m, 3H), 6.88 (m, 3H), 7.42 (m, 2H), 8.02 (m, 1H), 10.34 (m, 1H).

LCMS(ESI): $[M+H]^+$ m/z: calcd 370.2; found 371.0; Rt=3.689 min Chiral HPLC: Rt=28.84 min (OJ-H, Mobile phase: Hexane-IPA-MeOH, 50-25-25. Flow Rate: 0.6 mL/min).

Example 303. The Synthesis of N-(6-amino-5-methylpyridin-3-yl)-2-(5,5-dimethyl-2-phenylpiperidin-1-yl)-2-oxoacetamide Compound 56, Compound 52 and Compound 58

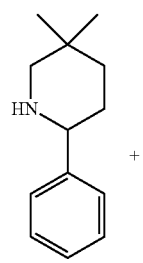

+

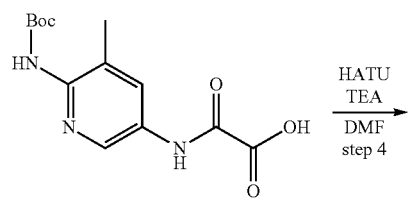

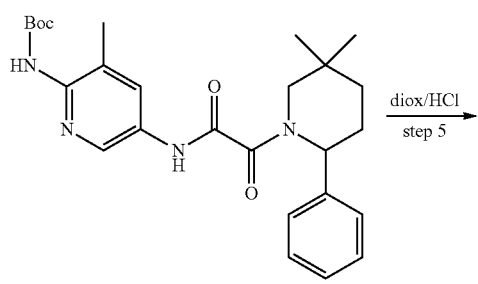

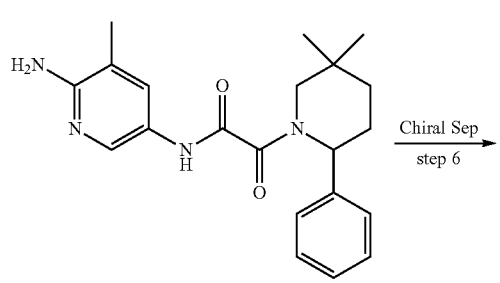

Compound 56

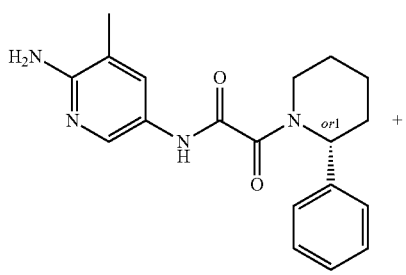

Compound 52

+

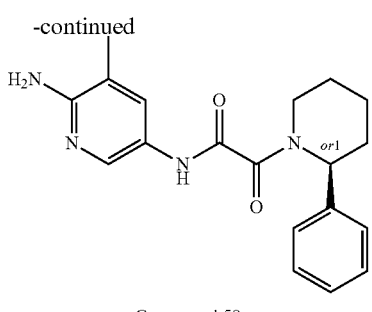

Compound 58

Step 1: Synthesis of tert-butyl (5-(2-(5,5-dimethyl-2-phenylpiperidin-1-yl)-2-oxoacetamido)-3-methylpyridin-2-yl)carbamate To a suspension of 5,5-dimethyl-2-phenyl-piperidine (0.3 g, 1.58 mmol), 2-[[6-(tert-butoxycarbonylamino)-5-methyl-3-pyridyl]amino]-2-oxo-acetic acid (561.58 mg, 1.90 mmol) and HATU (723.12 mg, 1.90 mmol) in DMF (3 mL), triethylamine (481.10 mg, 4.75 mmol, 662.68 μL) was added. The resulting mixture was stirred at 25° C. for 3 hr and subjected to HPLC (column: SunFire C18 100*19 5 um and water-MeCN as a mobile phase) to obtain tert-butyl N-[5-[[2-(5,5-dimethyl-2-phenyl-1-piperidyl)-2-oxo-acetyl]amino]-3-methyl-2-pyridyl]carbamate (0.3 g, 642.99 μmol, 40.57% yield).
$^1$H NMR (500 MHz, CDCl$_3$) δ (ppm) 0.87 (m, 3H), 1.05 (m, 3H), 1.36 (m, 2H), 1.51 (s, 9H), 1.59 (m, 2H), 2.45 (s, 3H), 2.75 (m, 1H), 4.55 (m, 1H), 5.89 (m, 1H), 6.51 (d, 1H), 7.26 (m, 3H), 7.38 (m, 2H), 8.06 (s, 1H), 8.38 (d, 1H), 9.33 (s, 1H). LCMS(ESI): [M]$^+$ m/z: calcd 466.6; found 467.2; Rt=4.129 min.

Step 2: Synthesis of N-(6-amino-5-methylpyridin-3-yl)-2-(5,5-dimethyl-2-phenylpiperidin-1-yl)-2-oxoacetamide (Compound 56 tert-butyl N-[5-[[2-(5,5-dimethyl-2-phenyl-1-piperidyl)-2-oxo-acetyl]amino]-3-methyl-2-pyridyl]carbamate (0.3 g, 642.99 μmol) was dissolved in hydrogen chloride solution 4.0 M in dioxane (2.00 g, 54.85 mmol, 2.5 mL) and stirred at 25° C. for 3 hr. The solvent was evaporated and residue was dried in vacuo and subjected to HPLC (column: YMC Actus Triart C18 100×20 mm, 5 um and MeOH as a mobile phase) to obtain N-(6-amino-5-methyl-3-pyridyl)-2-(5,5-dimethyl-2-phenyl-1-piperidyl)-2-oxo-acetamide (0.220 g, 546.02 μmol, 84.92% yield, HCl).
$^1$H NMR (400 MHz, DMSO-d$_6$) δ (ppm) 0.78 (m, 3H), 0.97 (m, 3H), 1.33 (m, 2H), 2.03 (m, 1H), 2.18 (m, 3H), 2.30 (m, 2H), 2.77 (m, 0.5H), 3.93 (m, 0.5H), 5.42 (m, 1H), 7.29 (m, 2H), 7.38 (m, 3H), 7.90 (m, 3H), 8.29 (m, 1H), 11.20 (m, 1H), 13.94 (m, 1H). LCMS(ESI): [M]$^+$ m/z: calcd 366.2; found 367.2; Rt=2.915 min.

Step 3: Chiral Separation (Compound 52 and Compound 58

Purification on the chiral column was taken in the system Hex-IPA-MeOH, 50-25-25, 0.15 mL/min. Number of injections: 1, injection volume: 1 mkl. From 50 mg of racemate, 18 mg and 15 mg of the individual enantiomers were obtained.

Compound 52: Retention time: 5.22 min. $^1$H NMR (500 MHz, DMSO-$d_6$) δ (ppm) 0.84 (m, 3H), 1.02 (m, 3H), 1.40 (m, 2H), 2.08 (m, 1H), 2.22 (m, 3H), 2.33 (m, 1H), 2.79 (m, 1H), 3.75 (m, 1H), 5.53 (m, 1H), 7.26 (m, 2H), 7.34 (m, 3H), 7.75 (m, 2H), 7.92 (m, 1H), 8.32 (m, 1H), 11.04 (m, 1H). LCMS(ESI): [M]$^+$ m/z: calcd 366.2; found 367.2; Rt=4.009 min.

Compound 58: Retention time: 8.92 min $^1$H NMR (500 MHz, DMSO-$d_6$) δ (ppm) 0.83 (m, 3H), 1.03 (m, 3H), 1.40 (m, 2H), 2.08 (m, 3H), 2.28 (m, 2H), 2.78 (m, 1H), 3.81 (m, 1H), 5.30 (m, 2H), 5.72 (m, 1H), 7.26 (m, 2H), 7.35 (m, 3H), 7.55 (m, 1H), 8.09 (m, 1H), 10.40 (m, 1H).

LCMS(ESI): [M]$^+$ m/z: calcd 366.2; found 367.2; Rt=4.033 min.

Example 304. The Synthesis of N-(6-amino-5-methyl-3-pyridyl)-2-(3,5-dimethyl-2-phenyl-1-piperidyl)-2-oxo-acetamide (Compound 314, Compound 339, Compound 343

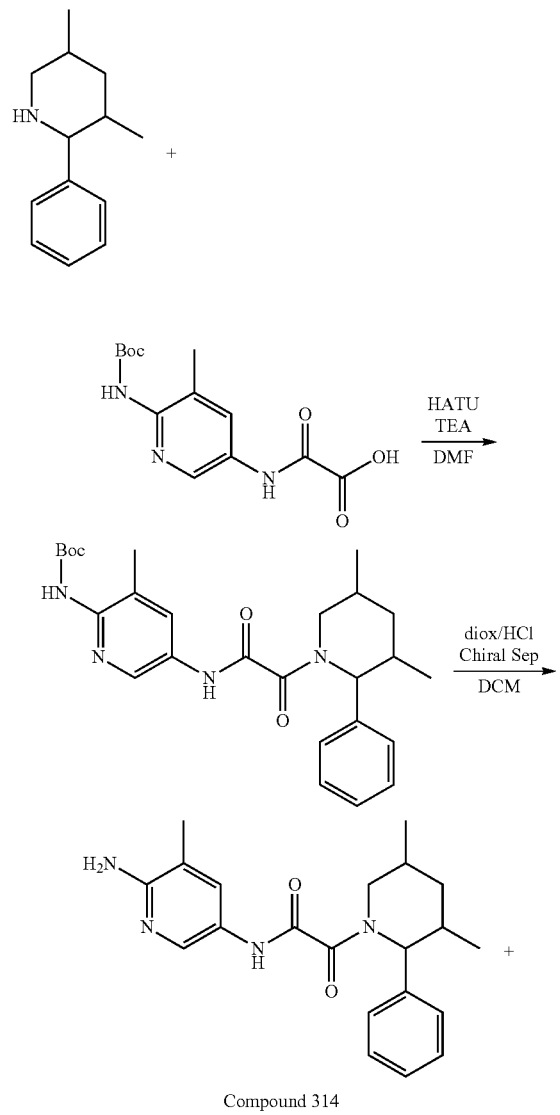

Compound 314

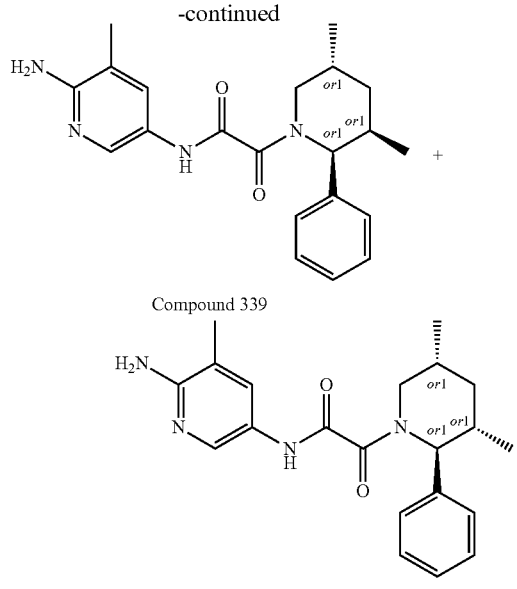

Compound 339

Compound 343

Step 1: Synthesis of tert-butyl (5-(2-(3,5-dimethyl-2-phenylpiperidin-1-yl)-2-oxoacetamido)-3-methylpyridin-2-yl)carbamate 2-[[6-(tert-butoxycarbonylamino)-5-methyl-3-pyridyl]amino]-2-oxo-acetic acid (779.97 mg, 2.64 mmol), HATU (1.10 g, 2.91 mmol) and TEA (534.56 mg, 5.28 mmol, 736.31 μL) were mixed together in DMF (8 mL) and 3,5-dimethyl-2-phenyl-piperidine (500 mg, 2.64 mmol) was added thereto. Resulting mixture was stirred at 25° C. for 4 hr. Then, it was diluted with water (30 ml) and extracted with ethyl acetate (2×30 ml). Organic layer was successively washed with water (3×20 ml) and brine (30 ml), dried over Na$_2$SO$_4$ and concentrated in vacuo, affording tert-butyl N-[5-[[2-(3,5-dimethyl-2-phenyl-1-piperidyl)-2-oxo-acetyl]amino]-3-methyl-2-pyridyl]carbamate (930 mg, 1.99 mmol, 75.46% yield).

$^1$H NMR (500 MHz, DMSO-$d_6$) δ (ppm) 0.95 (d, 3H), 1.04 (d, 3H), 1.17 (m, 1H), 1.43 (s, 9H), 1.98 (m, 1H), 2.16 (s, 3H), 2.91 (m, 2H), 3.83 (m, 1H), 4.03 (m, 1H), 4.46 (m, 1H), 7.88 (m, 7H), 8.39 (m, 1H), 9.04 (m, 1H). LCMS(ESI): [M]$^+$ m/z: calcd 466.5; found 467.2; Rt=1.490 min.

Step 2: Chiral Separation (Compound 314, Compound 339 and Compound 343

Hydrogen chloride solution 4.0 M in dioxane (6.25 g, 17.15 mmol, 7.82 mL, 10% purity) was added to a solution of tert-butyl N-[5-[[2-(3,5-dimethyl-2-phenyl-1-piperidyl)-2-oxo-acetyl]amino]-3-methyl-2-pyridyl]carbamate (800.07 mg, 1.71 mmol) in DCM (5 mL). Resulting mixture was stirred at 25° C. for 15 hr. Then, it was concentrated under reduced pressure and residue was subjected to HPLC (Column: YMC Triart C18 100×20 mm, 5 um; 40-40-90% 0-1-6 min 0.1% NH$_3$-methanol, flow: 30 ml/min), affording 167 mg mixture of isomers. Obtained racemate was subjected to chiral HPLC(Column: OD-H (250*30, 5 mkm), Hexane-IPA-MeOH, 90-5-5, 30 ml/min), affording: N-(6-amino-5-methyl-3-pyridyl)-2-[(2S,3S,5R)-3,5-dimethyl-2-phenyl-1-piperidyl]-2-oxo-acetamide (20 mg, 54.58 μmol, 3.18% yield), N-(6-amino-5-methyl-3-pyridyl)-2-(3,5-dimethyl-2- phenyl-1-piperidyl)-2-oxo-acetamide (59 mg, 161.00 µmol, 9.39% yield), N-(6-amino-5-methyl-3-pyridyl)-2-[(2S,3R,5R)-3,5-dimethyl-2-phenyl-1-piperidyl]-2-oxo-acetamide (29 mg, 79.14 µmol, 4.61% yield).

Compound 314: Retention time: 34.68+37.54 min LCMS (ESI): [M]+ m/z: calcd 366.2; found 367.2; Rt=2.434 min.
Compound 339: Retention time: 41.95 min $^1$H NMR (600 MHz, DMSO-$d_6$) δ (ppm) 0.78 (m, 1H), 0.84 (m, 3H), 0.94 (m, 3H), 1.85 (m, 1H), 1.99 (m, 4H), 2.12 (m, 1H), 3.53 (m, 1H), 3.77 (m, 1H), 4.48 (m, 1H), 5.59 (m, 2H), 7.33 (m, 6H), 7.94 (m, 1H), 10.37 (m, 1H). LCMS(ESI): [M]+ m/z: calcd 366.2; found 367.2; Rt=4.059 min.
Compound 343: Retention time: 31.46 min $^1$H NMR (600 MHz, DMSO-$d_6$) δ (ppm) 0.70 (m, 3H), 1.02 (m, 3H), 1.38 (m, 1H), 1.90 (td, 1H), 1.99 (m, 3H), 2.15 (m, 1H), 2.26 (m, 1H), 3.40 (m, 1H), 3.69 (m, 1H), 5.18 (m, 1H), 5.61 (m, 2H), 7.31 (m, 4H), 7.44 (m, 2H), 7.95 (m, 1H), 10.29 (m, 1H). LCMS(ESI): [M]+ m/z: calcd 366.2; found 367.2; Rt=4.101 min.

Example 305. The Synthesis of N-(6-amino-5-methyl-3-pyridyl)-2-[2-(Benzothiophen-3-yl)-1-piperidyl]-2-oxo-acetamide (Compound 123

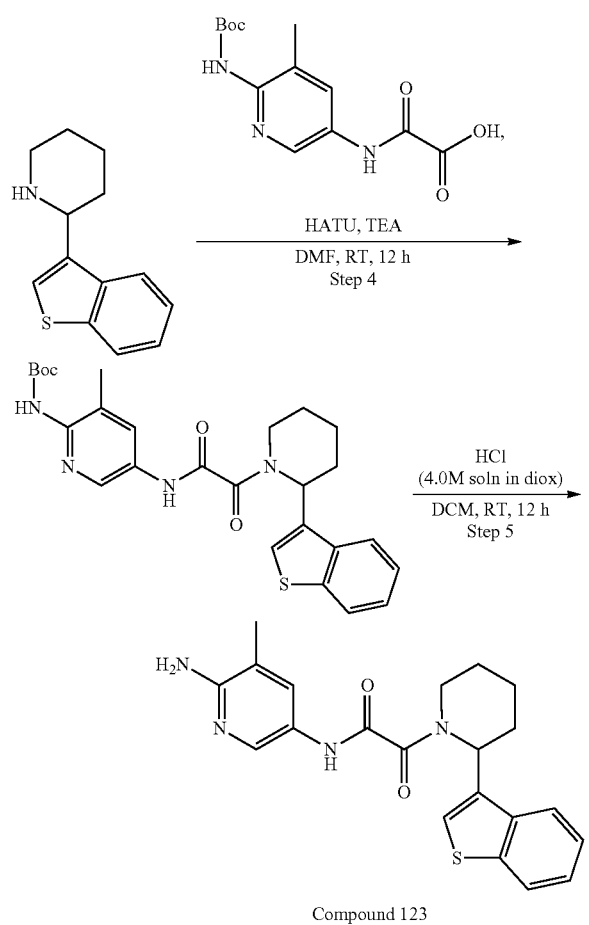

Compound 123

Step 1: The Synthesis of tert-butyl N-[5-[[2-[2-(Benzothiophen-3-yl)-1-piperidyl]-2-oxo-acetyl]amino]-3-methyl-2-pyridyl]carbamate To a suspension of 2-(benzothiophen-3-yl)piperidine (0.4 g, 1.84 mmol), 2-[[6-(tert-butoxycarbonylamino)-5-methyl-3-pyridyl]amino]-2-oxo-acetic acid (543.49 mg, 1.84 mmol) and HATU (699.82 mg, 1.84 mmol) in DMF (3 mL), triethylamine (931.21 mg, 9.20 mmol, 1.28 mL) was added. The resulting mixture was stirred at ambient temperature for 12 hr. Then, the mixture was taken up with water (40 ml) and extracted with EtOAc (3*20 ml). The combined organic layer was washed with brine (3*20 ml), dried over $Na_2SO_4$ and evaporated to obtain tert-butyl N-[5-[[2-[2-(benzothiophen-3-yl)-1-piperidyl]-2-oxo-acetyl]amino]-3-methyl-2-pyridyl]carbamate (0.9 g, crude). This compound was used for the next step without purification.

$^1$H NMR (400 MHz, DMSO-$d_6$) δ 1.43 (s, 9H), 1.69 (m, 2H), 1.98 (m, 2H), 2.18 (s, 3H), 2.32 (m, 2H), 3.09 (m, 2H), 3.67 (m, 1H), 5.99 (m, 1H), 7.39 (m, 2H), 7.93 (m, 3H), 8.45 (s, 1H), 9.06 (s, 1H), 11.02 (m, 1H).

LCMS(ESI): [M+H]+ m/z: calcd 494.2; found 495.2; Rt=1.417 min.

Step 2: The Synthesis of N-(6-amino-5-methyl-3-pyridyl)-2-[2-(Benzothiophen-3-yl)-1-piperidyl]-2-oxo-acetamide (Compound 123

To a solution of tert-butyl N-[5-[[2-[2-(benzothiophen-3-yl)-1-piperidyl]-2-oxo-acetyl]amino]-3-methyl-2-pyridyl]carbamate (0.9 g, 1.82 mmol) in DCM (20 mL), Hydrogen chloride solution 4.0 M in dioxane (8.00 g, 219.41 mmol, 10 mL) was added. The resulting mixture was stirred at 25° C. for 12 hr and evaporated in vacuo to obtain crude product (0 g). The crude product was purified by HPLC (40/60% 0-5 min 0.1% $NH_3$-methanol, flow: 30 ml/min (loading pump 4 ml/min methanol) target mass 394 column: YMC Triart C18 100*20 mm, 5 um) to give N-(6-amino-5-methyl-3-pyridyl)-2-[2-(benzothiophen-3-yl)-1-piperidyl]-2-oxo-acetamide (57 mg, 144.49 µmol, 7.94% yield).

$^1$H NMR (500 MHz, DMSO+CCL4) δ 1.72 (m, 3H), 1.89 (m, 1H), 2.01 (m, 4H), 2.32 (m, 1H), 3.08 (m, 1H), 3.68 (m, 1H), 5.87 (m, 3H), 7.41 (m, 3H), 7.82 (m, 1H), 7.90 (m, 1H), 8.02 (m, 2H), 10.50 (m, 1H).

LCMS(ESI): [M+H]+ m/z: calcd 394.2; found 395.2; Rt=2.609 min.

Example 306. The Synthesis of rac-N-(6-amino-5-methylpyridin-3-yl)-2-((2R,5S)-2-(3-hydroxyphenyl)-5-methylpiperidin-1-yl)-2-oxoacetamide (Compound 187

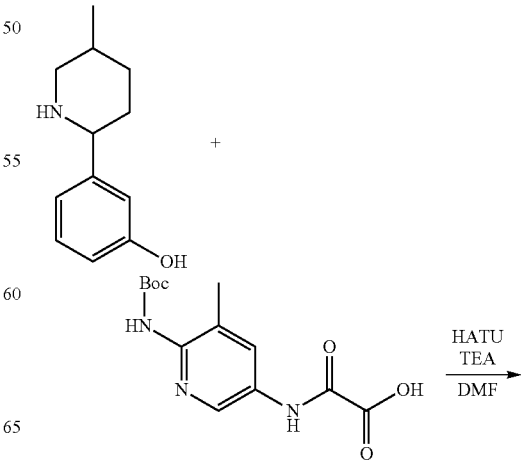

-continued

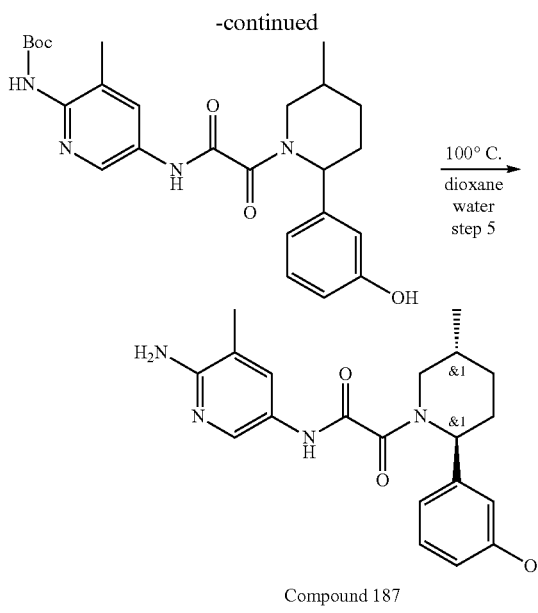

Compound 187

Step 1: Synthesis of tert-butyl (5-(2-(2-(3-hydroxyphenyl)-5-methylpiperidin-1-yl)-2-oxoacetamido)-3-methylpyridin-2-yl)carbamate TEA (2.49 g, 24.57 mmol, 3.42 mL) was added to a mixture of 3-(5-methyl-2-piperidyl)phenol (0.47 g, 2.46 mmol), 2-[[6-(tert-butoxycarbonylamino)-5-methyl-3-pyridyl]amino]-2-oxo-acetic acid (725.61 mg, 2.46 mmol) and HATU (1.03 g, 2.70 mmol) in DMF (5 mL). The reaction mixture was stirred at 25° C. for 1 hr and then submitted to reverse phase HPLC (column: SunFire C18 100×19 mm 5um, mobile phase 35-40% 0-5 min water-MeCN) to afford tert-butyl N-[5-[[2-[2-(3-hydroxyphenyl)-5-methyl-1-piperidyl]-2-oxo-acetyl]amino]-3-methyl-2-pyridyl]carbamate (130 mg, 277.46 μmol, 11.29% yield) as white solid.

$^1$H NMR (400 MHz, CDCl$_3$) δ (ppm) 1.11 (d, 3H), 1.32 (m, 1H), 1.48 (s, 9H), 1.99 (m, 2H), 2.12 (m, 2H), 2.28 (s, 3H), 2.98 (m, 1H), 3.42 (d, 1H), 4.38 (m, 1H), 5.98 (m, 1H), 6.76 (m, 4H), 7.18 (m, 1H), 7.97 (m, 1H), 8.34 (m, 1H).

LCMS(ESI): [M]$^+$ m/z: calcd 468.5; found 469.2; Rt=3.448 min.

Step 2: Synthesis of rac-N-(6-amino-5-methylpyridin-3-yl)-2-((2R,5S)-2-(3-hydroxyphenyl)-5-methylpiperidin-1-yl)-2-oxoacetamide (Compound 187 tert-butyl N-[5-[[2-[2-(3-hydroxyphenyl)-5-methyl-1-piperidyl]-2-oxo-acetyl]amino]-3-methyl-2-pyridyl]carbamate (130 mg, 277.46 μmol) was dissolved in a mixture of 1,4-dioxane (1.5 mL) and water (2.5 mL). The resulting mixture was stirred at 90° C. for 48 hr, then cooled down and submitted to reverse phase HPLC (column: YMC Triart C18 100×20 mm, 5um, mobile phase: 40-60% 0-5 min 0.1% NH$_3$-MeOH) to afford 51 mg of crude product, which was again repurified using reverse phase HPLC (column: YMC Triart C18 100×20 mm, 5um, mobile phase: 15-40% 0-5 min 0.1% NH$_3$-MeOH) to afford two fractions of Compound 187: 11 mg (1st fraction) and 20 mg (2nd fraction)N-(6-amino-5-methyl-3-pyridyl)-2-[(2S,5R)-2-(3-hydroxyphenyl)-5-methyl-1-piperidyl]-2-oxo-acetamide (31 mg, 84.14 μmol, 30.33% yield) as white solid.

$^1$H NMR (500 MHz, DMSO-d$_6$) δ (ppm) 1.01 (m, 3H), 1.32 (m, 1H), 1.69 (m, 1H), 1.88 (m, 1H), 2.02 (m, 4H), 2.12 (m, 1H), 3.08 (m, 1H), 3.74 (m, 1H), 5.62 (m, 3H), 6.71 (m, 3H), 7.17 (m, 1H), 7.48 (m, 1H), 8.01 (m, 1H), 9.40 (m, 1H), 10.48 (m, 1H).

LCMS(ESI): [M]$^+$ m/z: calcd 368.4; found 369.2; Rt=2.020 min.

Example 307. The Synthesis of rac-N-(6-amino-5-methylpyridin-3-yl)-2-((2R,5S)-2-(4-hydroxyphenyl)-5-methylpiperidin-1-yl)-2-oxoacetamide (Compound 164

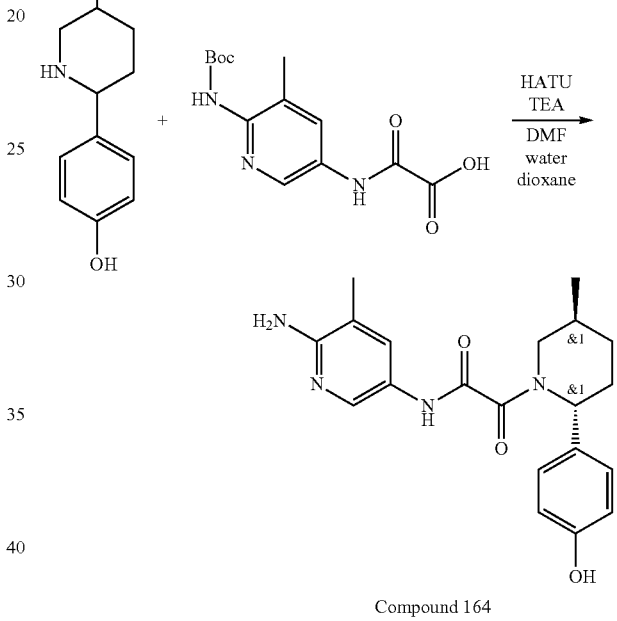

Compound 164

TEA (1.75 g, 17.25 mmol, 2.40 mL) was added to a mixture of 4-(5-methyl-2-piperidyl)phenol (2.2 g, 1.73 mmol) (crude from previous step), 2-[[6-(tert-butoxycarbonylamino)-5-methyl-3-pyridyl]amino]-2-oxo-acetic acid (509.47 mg, 1.73 mmol) and HATU (1.31 g, 3.45 mmol) in DMF (15 mL). The reaction mixture was stirred at 25° C. for 12 hr, and then evaporated in vacuo. The residue diluted with water (30 ml) and extracted with ethyl acetate (2*20 ml). The combined organic extracts were washed with brine (10 ml), dried over sodium sulphate and evaporated in vacuo to leave 800 mg of the residue, which was purified by reverse phase HPLC (column: SunFire C18 100×8 mm 5 um) using 25-50% 0-5 min water-MeCN as mobile phase to afford two fractions of boc-protected amide: 20 mg (40% by LCMS, 1st fraction) and 40 mg (73% by LCMS, 2nd fraction). Two fractions were combined, dissolved in a mixture of 1,4-dioxane (1.5 mL) and water (2 mL), and stirred at 95° C. for 48 hr.

LCMS of the aliquot showed complete boc-deprotection, the reaction mixture was cooled down and submitted to reverse phase HPLC (column: YMC Triart C18 100×20 mm, 5 um) using 35-60% 0-5 min 0.1% NH$_3$-MeOH as mobile phase to afford Compound 164 N-(6-amino-5-methyl-3- pyridyl)-2-[(2S,5R)-2-(4-hydroxyphenyl)-5-methyl-1-piperidyl]-2-oxo-acetamide (16 mg, 43.43 μmol, 2.52% yield) as white solid.

$^1$H NMR (500 MHz, DMSO-d$_6$) δ (ppm) 1.00 (m, 3H), 1.30 (m, 1H), 1.68 (m, 1H), 1.86 (m, 1H), 2.02 (m, 4H), 2.14 (m, 1H), 2.96 (m, 2H), 3.97 (m, 1H), 5.58 (m, 3H), 6.76 (m, 2H), 7.12 (m, 2H), 7.48 (m, 1H), 8.00 (m, 1H), 10.46 (s, 1H).

LCMS(ESI): [M]$^+$ m/z: calcd 368.4; found 369.2; Rt=2.266 min.

Example 308. The Synthesis of rac-N-(6-amino-5-methylpyridin-3-yl)-2-((2R,5R)-5-methyl-2-(1-methyl-1H-pyrazol-5-yl)piperidin-1-yl)-2-oxoacetamide (Compound 66

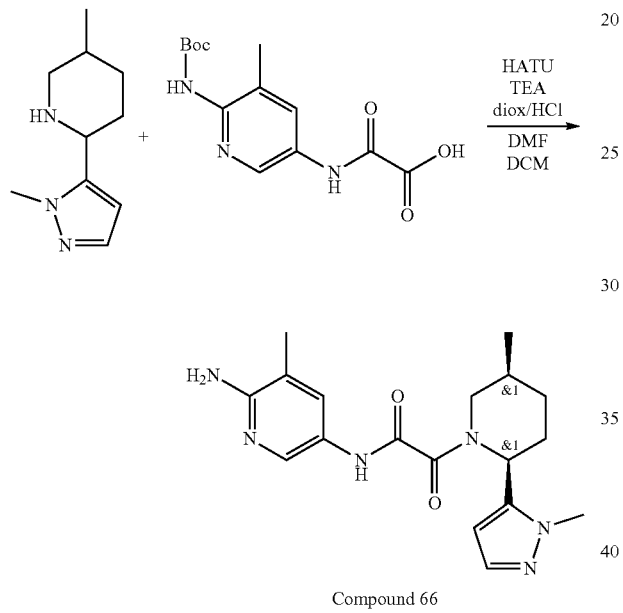

Compound 66

TEA (1.20 g, 11.90 mmol, 1.66 mL) was added to a mixture of 5-methyl-2-(2-methylpyrazol-3-yl)piperidine (300 mg, 1.19 mmol, 2HCl), 2-[[6-(tert-butoxycarbonylamino)-5-methyl-3-pyridyl]amino]-2-oxo-acetic acid (351.28 mg, 1.19 mmol) and HATU (497.56 mg, 1.31 mmol) in DMF (15 mL). The reaction mixture was stirred at 25° C. for 1 hr, then evaporated in vacuo. the residue was dissolved in dichloromethane (10 mL) and hydrogen chloride solution 4.0 M in dioxane (21.00 g, 80.06 mmol, 26.25 mL, 13.9% purity) was added. The resulting mixture was stirred at 25° C. for 2 hr, then evaporated in vacuo and the residue was purified by reverse phase HPLC (column: YMC Triart C18 100×20 mm, 5 um) using 30-50%, 50-60% 0-5 min 0.1% NH$_3$-methanol as mobile phase to afford Compound 66 N-(6-amino-5-methyl-3-pyridyl)-2-[(2S,5S)-5-methyl-2-(2-methylpyrazol-3-yl)-1-piperidyl]-2-oxo-acetamide (98 mg, 274.96 μmol, 23.11% yield).

$^1$H NMR (400 MHz, DMSO-d$_6$) δ (ppm) 0.82 (m, 3H), 1.56 (m, 2H), 1.74 (m, 2H), 1.92 (m, 1H), 2.03 (m, 5H), 2.62 (m, 1H), 3.54 (m, 1H), 5.71 (m, 4H), 6.44 (m, 1H), 7.37 (m, 1H), 7.50 (m, 1H), 8.02 (m, 1H), 10.47 (m, 1H). LCMS (ESI): [M+1] m/z: calcd 356.4; found 357.2; Rt=2.214 min.

Example 309. The Synthesis of N-(6-amino-5-methyl-3-pyridyl)-2-[(2S,5R)-5-methyl-2-[4-(methylamino)phenyl]-1-piperidyl]-2-oxo-acetamide (Compound 498

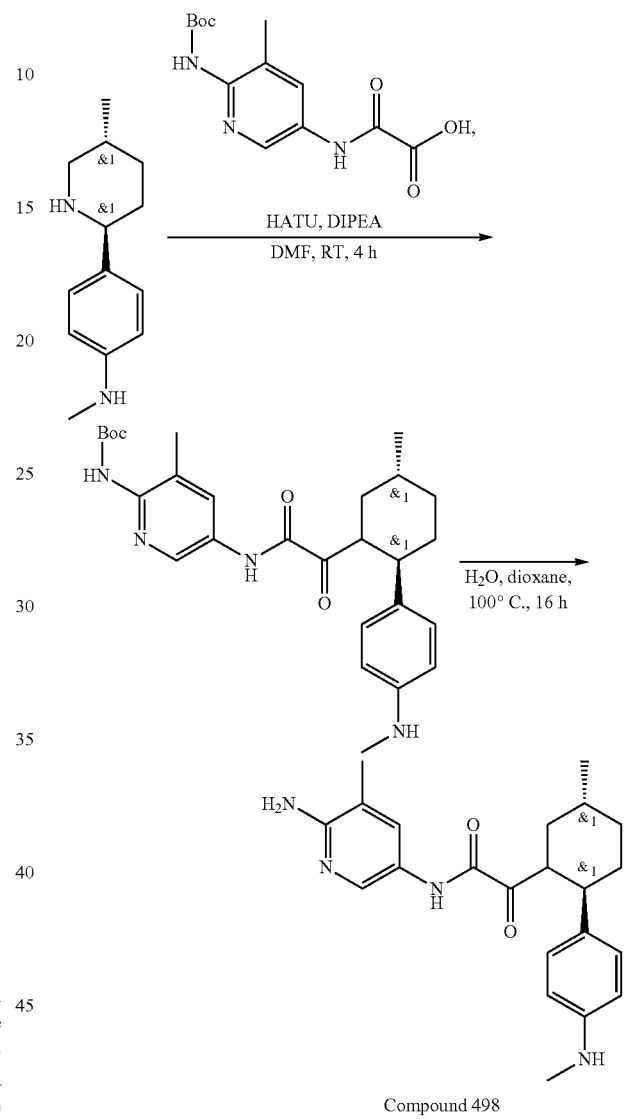

Compound 498

Step 1: The Synthesis of tert-butyl (3-methyl-5-(2-((2S,5R)-5-methyl-2-(4-(methylamino)phenyl)piperidin-1-yl)-2-oxoacetamido)pyridin-2-yl)carbamate 2-[[6-(tert-butoxycarbonylamino)-5-methyl-3-pyridyl]amino]-2-oxo-acetic acid (213.03 mg, 721.42 μmol), N-methyl-4-[(2S,5R)-5-methyl-2-piperidyl]aniline (0.2 g, 721.42 μmol, 2HCl), HATU (301.73 mg, 793.56 μmol) and DIPEA (279.71 mg, 2.16 mmol, 376.96 μL) were mixed together in DMSO (4 mL) and stirred for 4 h. The obtained solution in DMSO was subjected to HPLC (purification was repeated twice in order to obtain 95+% purity product: 1$^{st}$ loading: 2-10 min 35-100% MeOH/H$_2$O as a mobile phase; flow rate 30 mL/min; loading pump 4 ml MeOH; SunFire 100*19 mm, 5 microM column; 2$^{nd}$ loading: 2-10 min 40-60% water/MeCN+NH₃ as a mobile phase; loading pump 4 mL MeCN+NH₃; TRIART 100*20 5 microM column) to obtain tert-butyl N-[3-methyl-5-[[2-[(2S,5R)-5-methyl-2-[4-(methylamino)phenyl]-1-piperidyl]-2-oxo-acetyl]amino]-2-pyridyl]carbamate (16 mg, 33.22 μmol, 4.61% yield).

LCMS(ESI): [M+2H]⁺ m/z: calcd 481.2; found 483.2; Rt=1.074 min.

Step 2: The Synthesis of N-(6-amino-5-methyl-3-pyridyl)-2-[(2S,5R)-5-methyl-2-[4-(methylamino)phenyl]-1-piperidyl]-2-oxo-acetamide (Compound 498 tert-butyl N-[3-methyl-5-[[2-[(2S,5R)-5-methyl-2-[4-(methylamino)phenyl]-1-piperidyl]-2-oxo-acetyl]amino]-2-pyridyl]carbamate (16 mg, 33.22 μmol) was dissolved in the mixture of water (0.5 mL) and dioxane (0.5 mL). The reaction mixture was stirred at 100° C. for 16 hr. Then, the crude product in current solution was subjected to HPLC (2-10 min 40-60% water/MeCN+NH₃ as a mobile phase; loading pump 4 mL MeCN+NH₃; TRIART 100*20 5 microM column) to afford N-(6-amino-5-methyl-3-pyridyl)-2-[(2S,5R)-5-methyl-2-[4-(methylamino)phenyl]-1-piperidyl]-2-oxo-acetamide (8.7 mg, 22.81 μmol, 68.65% yield).

¹H NMR (600 MHz, DMSO-d₆) δ 1.04-1.22 (m, 3H), 1.27-1.41 (m, 1H), 1.63-1.94 (m, 2H), 1.95-2.11 (m, 4H), 2.10-2.18 (m, 1H), 2.69 (s, 3H), 2.74-2.79 (m, 0.4H), 3.19-3.26 (m, 0.6H), 3.50-4.04 (m, 1H), 5.06-5.13 (m, 0.4H), 5.16-5.35 (m, 3H), 5.53-5.62 (m, 0.6H), 6.44-6.53 (m, 2H), 6.92-6.98 (m, 1H), 6.99-7.08 (m, 1H), 7.48-7.59 (m, 1H), 7.97-8.05 (m, 1H), 10.24-10.35 (m, 1H).

LCMS(ESI): [M+H]⁺ m/z: calcd 381.2; found 382.2; Rt=2.042 min.

Example 310. The Synthesis of 2-(2-(1H-Indol-5-yl)-5-methylpiperidin-1-yl)-N-(6-amino-5-methylpyridin-3-yl)-2-oxoacetamide (Compound 385, Compound 388

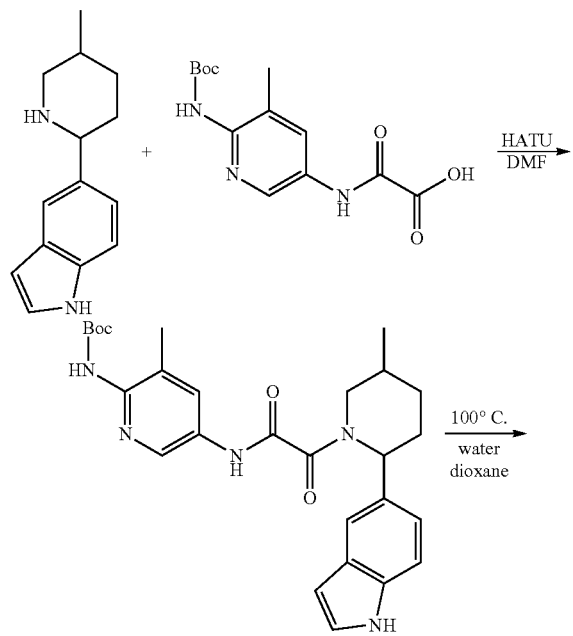

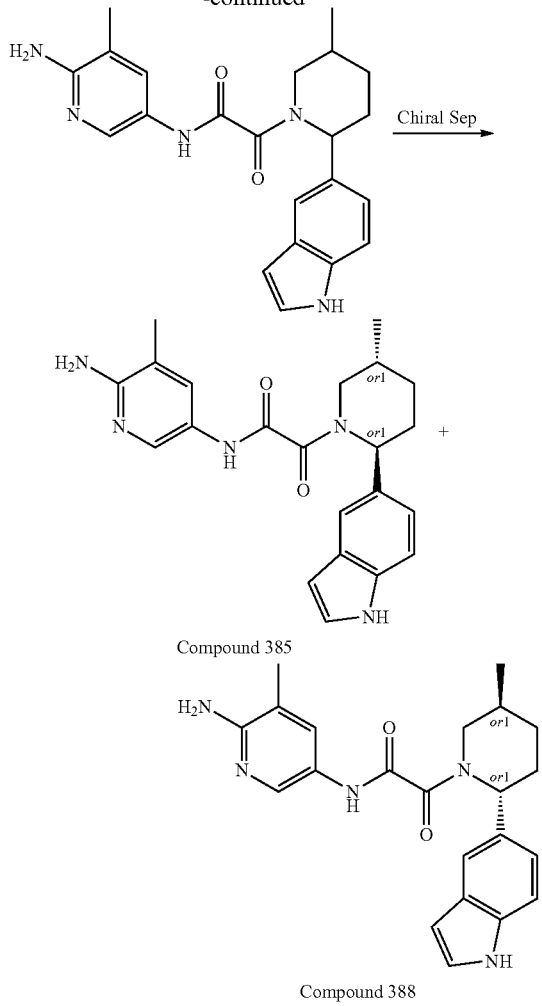

Compound 385

Compound 388

Step 1: Synthesis of tert-butyl (5-(2-(2-(1H-Indol-5-yl)-5-methylpiperidin-1-yl)-2-oxoacetamido)-3-methylpyridin-2-yl)carbamate HATU (603.24 mg, 1.59 mmol) was added portionwise at rt to a suspension of 2-[[6-(tert-butoxycarbonylamino)-5-methyl-3-pyridyl]amino]-2-oxo-acetic acid (468.48 mg, 1.59 mmol), 5-(5-methyl-2-piperidyl)-1H-indole (400 mg, 1.59 mmol) and TEA (963.24 mg, 9.52 mmol, 1.33 mL) in DMF (9 mL). The clear solution was stirred at 30° C. for 32 hr and the solvents were evaporated in vacuo to give 1 g of crude material. It was subjected to RP-HPLC (column: SunFire C18 100×19 mm 5 um; 65-56-90% 0-1-5 min water-MeOH as mobile phase) to give tert-butyl N-[5-[[2-[2-(1H-indol-5-yl)-5-methyl-1-piperidyl]-2-oxo-acetyl]amino]-3-methyl-2-pyridyl]carbamate (192.8 mg, 392.20 μmol, 24.72% yield).

¹H NMR (400 MHz, DMSO-d₆) δ (ppm)
LCMS(ESI): [M]⁺ m/z: calcd 491.2; found 492.2; Rt=3.712 min.

Step 2: Synthesis of 2-(2-(1H-Indol-5-yl)-5-methylpiperidin-1-yl)-N-(6-amino-5-methylpyridin-3-yl)-2-oxoacetamide The solution of tert-butyl N-[5-[[2-[2-(1H-indol-5-yl)-5-methyl-1-piperidyl]-2-oxo-acetyl]amino]-3-methyl-2- pyridyl]carbamate (170 mg, 345.82 μmol) in dioxane (2 mL) and water (1 mL) was stirred for 12 hr at 95° C. and the solvents were evaporated in vacuo to give N-(6-amino-5-methyl-3-pyridyl)-2-[2-(1H-indol-5-yl)-5-methyl-1-piperidyl]-2-oxo-acetamide (120 mg, 306.54 μmol, 88.64% yield).

$^1$H NMR (400 MHz, DMSO-d$_6$) δ (ppm)

LCMS(ESI): [M]$^+$ m/z: calcd 391.2; found 392.2; Rt=1.051 min.

Step 3: Chiral Separation (Compound 385 and Compound 388

The enantiomers were separated by chiral HPLC to give the two individual enantiomers Compound 385 N-(6-amino-5-methyl-3-pyridyl)-2-[(2S,5R)-2-(1H-indol-5-yl)-5-methyl-1-piperidyl]-2-oxo-acetamide (50 mg, 127.73 μmol, 83.33% yield) RetTime=56.6 min and Compound 388 N-(6-amino-5-methyl-3-pyridyl)-2-[(2R,5S)-2-(1H-indol-5-yl)-5-methyl-1-piperidyl]-2-oxo-acetamide (50 mg, 127.73 μmol, 83.33% yield) RetTime=68.8 min.

System 1. Column: Chiralpak IA (250*20, 5 mkm); Mobile phase: Hexane-IPA-MeOH, 70-15-15 Flow Rate: 12 mL/min; Column Temperature: 24° C.; Wavelength: 205 nm, 225 nm, 372 nm);

System 2. Column: Chiralpak IC (250*20, 5 mkm); Mobile phase: Hexane-IPA-MeOH, 80-10-10 Flow Rate: 12 mL/min; Column Temperature: 24° C.; Wavelength: 205 nm, 225 nm, 372 nm).

Ret time for Compound 385 in analytical conditions (column: IC, Hexane-IPA-MeOH, 60-20-20, 0.6 ml/min as mobile phase) 19.53 min and for Compound 388 27.05 min.

Compound 385: Retention time: 19.53 min $^1$H NMR (600 MHz, DMSO-d$_6$) δ (ppm) 1.00-1.03 (m, 3H), 1.26-1.39 (m, 1H), 1.74-1.90 (m, 2H), 1.96-2.03 (m, 3H), 2.04-2.21 (m, 1H), 2.23-2.32 (m, 1H), 2.75-3.24 (m, 1H), 3.37-4.01 (m, 1H), 5.14-5.58 (m, 1H), 5.58-5.72 (m, 2H), 6.34-6.42 (m, 1H), 6.96-7.12 (m, 1H), 7.29-7.32 (m, 1H), 7.33-7.39 (m, 1H), 7.41-7.47 (m, 1H), 7.48-7.52 (m, 1H), 7.91-8.09 (m, 1H), 10.41-10.58 (m, 1H), 11.03 (s, 1H).

LCMS(ESI): [M]$^+$ m/z: calcd 391.2; found 392.2; Rt=2.214 min.

Compound 388: Retention time: 27.05 min $^1$H NMR (600 MHz, DMSO-d$_6$) δ (ppm) 0.98-1.05 (m, 3H), 1.28-1.39 (m, 1H), 1.72-1.91 (m, 2H), 1.95-2.03 (m, 3H), 2.04-2.21 (m, 1H), 2.22-2.33 (m, 1H), 2.77-3.24 (m, 1H), 3.39-4.03 (m, 1H), 5.19-5.57 (m, 1H), 5.57-5.74 (m, 2H), 6.38 (s, 1H), 6.96-7.12 (m, 1H), 7.27-7.33 (m, 1H), 7.33-7.40 (m, 1H), 7.40-7.48 (m, 1H), 7.48-7.54 (m, 1H), 7.92-8.09 (m, 1H), 10.38-10.62 (m, 1H), 11.03 (s, 1H).

LCMS(ESI): [M]$^+$ m/z: calcd 391.2; found 392.2; Rt=2.228 min.

Example 311. The Synthesis of N-(6-amino-5-methyl-3-pyridyl)-2-[(2S)-2-(1H-indazol-5-yl)-1-piperidyl]-2-oxo-acetamide (Compound 518) and N-(6-amino-5-methyl-3-pyridyl)-2-[(2R)-2-(1H-indazol-5-yl)-1-piperidyl]-2-oxo-acetamide (Compound 535

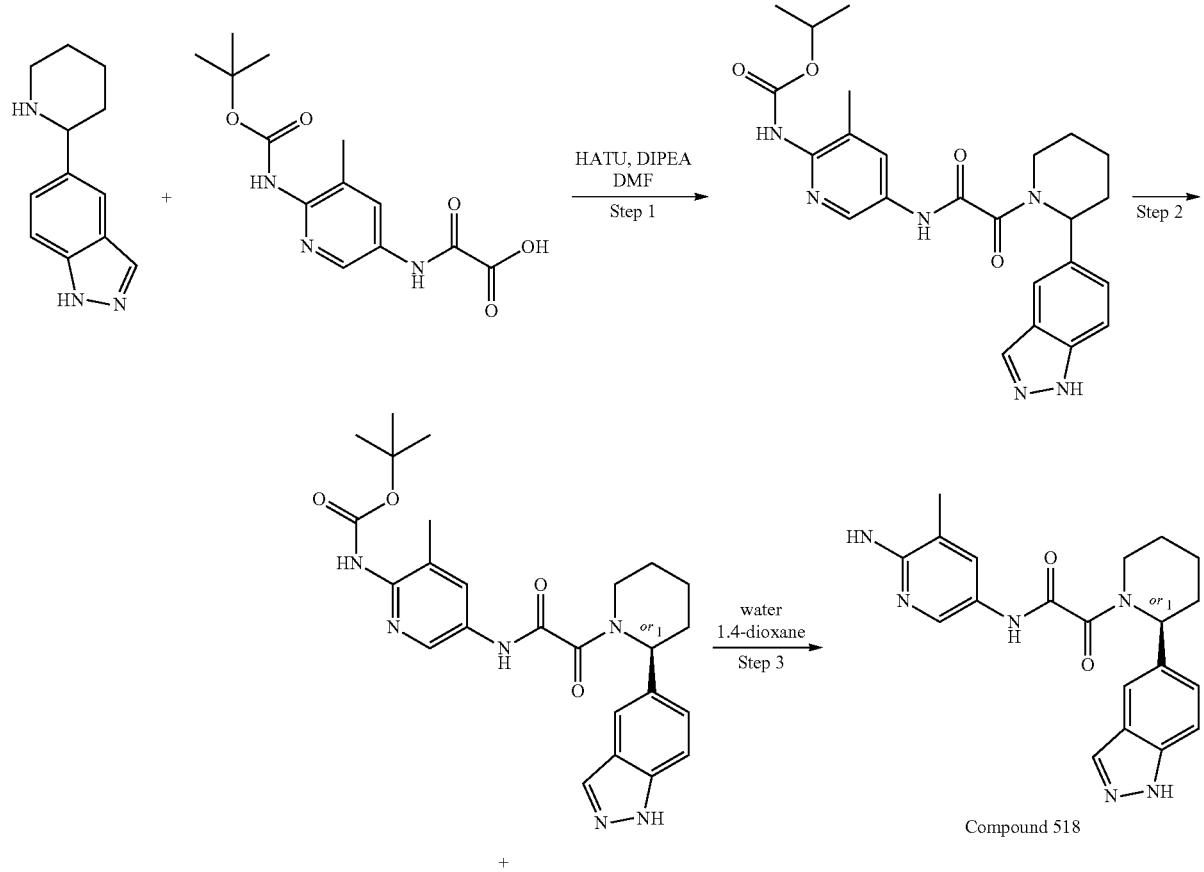

Compound 518

-continued

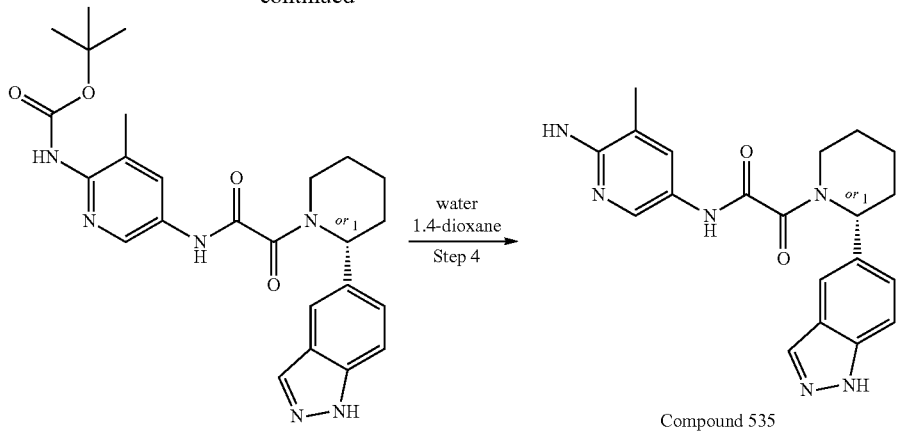

water
1.4-dioxane
Step 4

Compound 535

Step 1: Synthesis of tert-butyl N-[5-[[2-[2-(H-indazol-5-yl)-1-piperidyl]-2-oxo-acetyl]amino]-3-methyl-2-pyridyl]carbamate To a stirring solution of 5-(2-piperidyl)-1H-indazole (200 mg, 993.70 μmol), 2-[[6-(tert-butoxycarbonylamino)-5-methyl-3-pyridyl]amino]-2-oxo-acetic acid (293.43 mg, 993.70 μmol) and DIPEA (642.15 mg, 4.97 mmol, 865.43 μL) in DMF (5 mL) was added HATU (566.75 mg, 1.49 mmol) at 25° C. The resulting reaction mixture was stirred at 25° C. for 16 hr. A reaction mixture sample was submitted for LCMS analysis. LCMS indicated 34.89% of desired product mass under the curve area at RT=1.169 min. The crude reaction mixture was purified by reverse phase HPLC (column: YMC Triart C18 100×20 mm, 5 um, Mobile Phase: 40-40-80% 0-1-6 min 0.1% $NH_3$-methanol, flow: 30 ml/min, loading pump 4 ml/min methanol) to afford tert-butyl N-[5-[[2-[2-(1H-indazol-5-yl)-1-piperidyl]-2-oxo-acetyl]amino]-3-methyl-2-pyridyl]carbamate (267 mg, 557.94 μmol, 56.15% yield) as a light-yellow solid.

$^1$H NMR (500 MHz, DMSO) δ 1.20-1.30 (m, 9H), 1.45-1.70 (m, 4H), 1.95 (m, 1H), 2.13 (m, 3H), 2.59 and 3.02 (m, 2H for both rotamers), 3.70 and 4.29 (d, 1H for both rotamers), 5.25 and 5.78 (s, 1H for both rotamers), 7.29 and 7.37 (d, 1H for both rotamers), 7.55 (m, 1H), 7.73 (d, 1H), 7.88 and 7.97 (s, 1H for both rotamers), 8.07 (s, 1H), 8.37 and 8.48 (s, 1H for both rotamers), 9.02 and 9.07 (s, 1H for both rotamers), 11.07 (s, 1H), 13.05 (s, 1H).

LCMS(ESI): [M+H]$^+$ m/z: calcd 478.3; found 479.2; Rt=2.787 min.

Step 2: The Synthesis of tert-butyl N-[5-[[2-[(2S)-2-(1H-indazol-5-yl)-1-piperidyl]-2-oxo-acetyl]amino]-3-methyl-2-pyridyl]carbamate (P1) and Tert-butyl N-[5-[[2-[(2R)-2-(1H-indazol-5-yl)-1-piperidyl]-2-oxo-acetyl]amino]-3-methyl-2-pyridyl]carbamate (P2)

A racemic tert-butyl N-[5-[[2-[2-(1H-indazol-5-yl)-1-piperidyl]-2-oxo-acetyl]amino]-3-methyl-2-pyridyl]carbamate (267 mg, 557.94 μmol) was submitted to preparative chiral HPLC (Column: Chiralpak IA-II (250*20 mm, 5 mkm); Mobile phase: Hexane-IPA-MeOH 60-20-20 Flow Rate: 12 mL/min;) to afford tert-butyl N-[5-[[2-[(2S)-2-(1H-indazol-5-yl)-1-piperidyl]-2-oxo-acetyl]amino]-3-methyl-2-pyridyl]carbamate (P1) (88 mg, 183.89 μmol, 32.96% yield) (R.T.=23.157 min.) and tert-butyl N-[5-[[2-[(2R)-2-(1H-indazol-5-yl)-1-piperidyl]-2-oxo-acetyl]amino]-3-methyl-2-pyridyl]carbamate (P2) (83 mg, 173.44 μmol, 31.09% yield) (R.T.=32.819) as light-yellow solids.

P1: $^1$H NMR (500 MHz, DMSO) δ 1.20-1.30 (m, 9H), 1.45-1.70 (m, 4H), 1.95 (m, 1H), 2.13 (m, 3H), 2.59 and 3.02 (m, 2H for both rotamers), 3.70 and 4.29 (d, 1H for both rotamers), 5.25 and 5.78 (s, 1H for both rotamers), 7.29 and 7.37 (d, 1H for both rotamers), 7.55 (m, 1H), 7.73 (d, 1H), 7.88 and 7.97 (s, 1H for both rotamers), 8.07 (s, 1H), 8.37 and 8.48 (s, 1H for both rotamers), 9.02 and 9.07 (s, 1H for both rotamers), 11.07 (s, 1H), 13.05 (s, 1H).

LCMS(ESI): [M+H]$^+$ m/z: calcd 478.3; found 479.2; Rt=3.158 min.
RT (IA-3, Hexane-IPA-MeOH, 60-20-20, 12 ml/min)=24.48 min P2: $^1$H NMR (500 MHz, DMSO) δ 1.20-1.30 (m, 9H), 1.45-1.70 (m, 4H), 1.95 (m, 1H), 2.13 (m, 3H), 2.59 and 3.02 (m, 2H for both rotamers), 3.70 and 4.29 (d, 1H for both rotamers), 5.25 and 5.78 (s, 1H for both rotamers), 7.29 and 7.37 (d, 1H for both rotamers), 7.55 (m, 1H), 7.73 (d, 1H), 7.88 and 7.97 (s, 1H for both rotamers), 8.07 (s, 1H), 8.37 and 8.48 (s, 1H for both rotamers), 9.02 and 9.07 (s, 1H for both rotamers), 11.07 (s, 1H), 13.05 (s, 1H).

LCMS(ESI): [M+H]$^+$ m/z: calcd 478.3; found 479.2; Rt=3.159 min.
RT (IA-3, Hexane-IPA-MeOH, 60-20-20, 12 ml/min)=34.42 min.

Step 3: The Synthesis of N-(6-amino-5-methyl-3-pyridyl)-2-[(2S)-2-(1H-indazol-5-yl)-1-piperidyl]-2-oxo-acetamide (Compound 518

A solution of tert-butyl N-[5-[[2-[(2S)-2-(1H-indazol-5-yl)-1-piperidyl]-2-oxo-acetyl]amino]-3-methyl-2-pyridyl]carbamate (P1) (88 mg, 183.89 μmol) in a mixture of water (2 mL) and 1,4-dioxane (2 mL) was stirred at 95° C. for 24 hr, then cooled down and submitted to reverse phase HPLC (column: YMC Triart C18 100×20 mm, 5 um; mobile phase 30-30-80% 0-1-5 min 0.1% $NH_3$-methanol, flow: 30 ml/min) to afford Compound 518 N-(6-amino-5-methyl-3-pyridyl)-2-[(2S)-2-(1H-indazol-5-yl)-1-piperidyl]-2-oxo-acetamide (48.4 mg, 127.90 μmol, 69.55% yield) as white solid.

$^1$H NMR (600 MHz, DMSO-d$_6$) δ 1.43-1.61 (m, 3H), 1.61-1.70 (m, 1H), 1.77-1.96 (m, 1H), 1.96-2.07 (m, 3H), 2.51-2.57 (m, 2H), 2.93-3.27 (m, 1H), 3.61-4.29 (m, 1H), 5.17-5.57 (m, 1H), 5.57-5.79 (m, 2H), 7.24-7.38 (m, 1H), 7.41-7.58 (m, 2H), 7.65-7.73 (m, 1H), 7.93-8.06 (m, 2H), 10.45-13.05 (m, 1H).

LCMS(ESI): [M+H]⁺ m/z: calcd 378.2; found 379.2; Rt=1.420 min.

Step 4: The Synthesis of N-(6-amino-5-methyl-3-pyridyl)-2-[(2R)-2-(1H-indazol-5-yl)-1-piperidyl]-2-oxo-acetamide (Compound 535

A solution of tert-butyl N-[5-[[2-[(2R)-2-(1H-indazol-5-yl)-1-piperidyl]-2-oxo-acetyl]amino]-3-methyl-2-pyridyl]carbamate (P2) (83 mg, 173.44 µmol) in a mixture of water (2 mL) and 1,4-dioxane (2 mL) was stirred at 95° C. for 24 hr, then cooled down and submitted to reverse phase HPLC (column: YMC Triart C18 100×20 mm, 5 um; mobile phase 30-30-80% 0-1-5 min 0.1% NH₃-methanol, flow: 30 ml/min) to afford Compound 535 N-(6-amino-5-methyl-3-pyridyl)-2-[(2R)-2-(1H-indazol-5-yl)-1-piperidyl]-2-oxo-acetamide (49.2 mg, 130.01 µmol, 74.96% yield) as white solid.

¹H NMR (600 MHz, DMSO-d₆) δ 1.42-1.61 (m, 3H), 1.62-1.68 (m, 1H), 1.81-1.95 (m, 1H), 1.95-2.06 (m, 3H), 2.50-2.56 (m, 2H), 2.94-3.27 (m, 1H), 3.59-4.32 (m, 1H), 5.20-5.59 (m, 1H), 5.59-6.00 (m, 2H), 7.24-7.39 (m, 1H), 7.40-7.59 (m, 2H), 7.65-7.73 (m, 1H), 7.92-8.07 (m, 2H), 10.30-13.30 (m, 1H).

LCMS(ESI): [M+H]⁺ m/z: calcd 378.2; found 379.2; Rt=1.413 min.

Example 312. The Synthesis of N-(6-amino-5-methyl-3-pyridyl)-2-[(2R,5S)-2-(1H-indazol-5-yl)-5-methyl-1-piperidyl]-2-oxo-acetamide (Compound 364), N-(6-amino-5-methyl-3-pyridyl)-2-[(2S,5R)-2-(1H-indazol-5-yl)-5-methyl-1-piperidyl]-2-oxo-acetamide (Compound 363), N-(6-amino-5-methyl-3-pyridyl)-2-[(2R,5R)-2-(1H-indazol-5-yl)-5-methyl-1-piperidyl]-2-oxo-acetamide (Compound 1083), and N-(6-amino-5-methyl-3-pyridyl)-2-[(2S,5S)-2-(1H-indazol-5-yl)-5-methyl-1-piperidyl]-2-oxo-acetamide (Compound 392

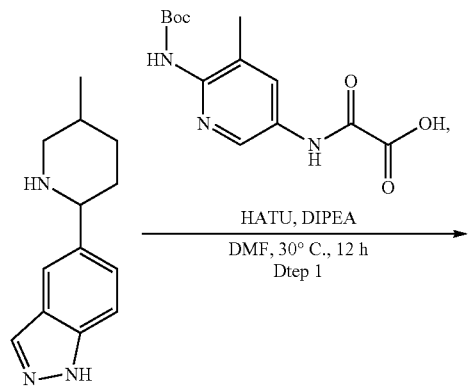

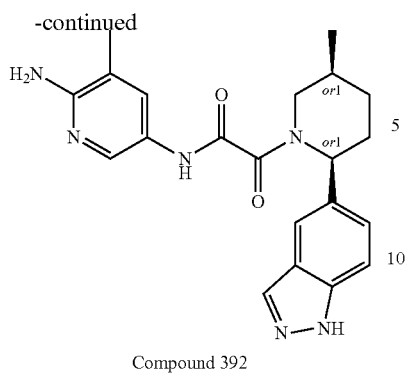

Compound 392

Step 1: The Synthesis of tert-butyl N-[5-[[2-[2-(H-indazol-5-yl)-5-methyl-1-piperidyl]-2-oxo-acetyl]amino]-3-methyl-2-pyridyl]carbamate To a suspension of 5-(5-methyl-2-piperidyl)-1H-indazole (0.23 g, 1.07 mmol), 2-[[6-(tert-butoxycarbonylamino)-5-methyl-3-pyridyl]amino]-2-oxo-acetic acid (315.46 mg, 1.07 mmol) and HATU (446.82 mg, 1.18 mmol) in DMF (6 mL), triethylamine (540.51 mg, 5.34 mmol, 744.51 µL) was added. The resulting mixture was stirred at 30° C. for 12 hr, quenched with water (50 ml) and extracted with EtOAc (3*30 ml). The combined organic layer was washed with brine (3*20 ml), dried over $Na_2SO_4$ and evaporated to obtain tert-butyl N-[5-[[2-[2-(1H-indazol-5-yl)-5-methyl-1-piperidyl]-2-oxo-acetyl]amino]-3-methyl-2-pyridyl]carbamate (0.6 g, crude).

This compound was used for the next step without purification.

$^1$H NMR (400 MHz, DMSO-$d_6$) δ 1.00 (d, 3H), 1.40 (s, 9H), 1.74 (m, 4H), 2.16 (s, 3H), 3.98 (m, 2H), 5.21 (m, 2H), 5.67 (m, 2H), 7.27 (d, 1H), 7.49 (d, 1H), 7.67 (s, 1H), 8.02 (s, 1H), 8.44 (s, 1H), 9.04 (s, 1H), 11.03 (s, 1H).

LCMS(ESI): [M+H]$^+$ m/z: calcd 492.2; found 493.2; Rt=1.158 min.

Step 2: The Synthesis of N-(6-amino-5-methyl-3-pyridyl)-2-[2-(1H-indazol-5-yl)-5-methyl-1-piperidyl]-2-oxo-acetamide To a solution of tert-butyl N-[5-[[2-[2-(1H-indazol-5-yl)-5-methyl-1-piperidyl]-2-oxo-acetyl]amino]-3-methyl-2-pyridyl]carbamate (0.6 g, 1.22 mmol) in DCM (10 mL), hydrogen chloride solution 4.0 M in dioxane (8.00 g, 219.41 mmol, 10 mL) was added. The resulting mixture was stirred at 25° C. for 18 hr, evaporated in vacuo and subjected to HPLC (40-40-80% 0-1-5 min 0.1% $NH_3$-methanol, flow: 30 ml/min (loading pump 4 ml/min methanol) target mass 392 column: YMC Triart C18 100×20 mm, 5 um) to give N-(6-amino-5-methyl-3-pyridyl)-2-[2-(1H-indazol-5-yl)-5-methyl-1-piperidyl]-2-oxo-acetamide (152 mg, 387.31 µmol, 31.80% yield).

NMR spectrum of this compound was not obtained and it was directly used for chiral resolution.

LCMS(ESI): [M+H]$^+$ m/z: calcd 392.2; found 393.2; Rt=2.085 min.

Step 3: The Synthesis of N-(6-amino-5-methyl-3-pyridyl)-2-[(2R,5S)-2-(1H-indazol-5-yl)-5-methyl-1-piperidyl]-2-oxo-acetamide (Compound 364), N-(6-amino-5-methyl-3-pyridyl)-2-[(2S,5R)-2-(1H-indazol-5-yl)-5-methyl-1-piperidyl]-2-oxo-acetamide (Compound 363), N-(6-amino-5-methyl-3-pyridyl)-2-[(2R,5R)-2-(1H-indazol-5-yl)-5-methyl-1-piperidyl]-2-oxo-acetamide (Compound 1083), and N-(6-amino-5-methyl-3-pyridyl)-2-[(2S,5S)-2-(1H-indazol-5-yl)-5-methyl-1-piperidyl]-2-oxo-acetamide (Compound 392

N-(6-amino-5-methyl-3-pyridyl)-2-[2-(1H-indazol-5-yl)-5-methyl-1-piperidyl]-2-oxo-acetamide (152.0 mg) was subjected to HPLC (IA_II column, Hexane-IPA-MeOH, 50-25-25 as a mobile phase; Flow 10 ml/min) to afford Compound 364—N-(6-amino-5-methyl-3-pyridyl)-2-[(2R,5S)-2-(1H-indazol-5-yl)-5-methyl-1-piperidyl]-2-oxo-acetamide (43.0 mg, 62.87% yield; RT=41.665 min), Compound 363—N-(6-amino-5-methyl-3-pyridyl)-2-[(2S,5R)-2-(1H-indazol-5-yl)-5-methyl-1-piperidyl]-2-oxo-acetamide (42.0 mg, 61.4% yield; RT=26.796 min), Compound 1083—N-(6-amino-5-methyl-3-pyridyl)-2-[(2R,5R)-2-(1H-indazol-5-yl)-5-methyl-1-piperidyl]-2-oxo-acetamide (2.0 mg, 26.32% yield; RT=36.456 min), and Compound 392—N-(6-amino-5-methyl-3-pyridyl)-2-[(2S,5S)-2-(1H-indazol-5-yl)-5-methyl-1-piperidyl]-2-oxo-acetamide (4.0 mg, 52.63% yield; RT=23.296 min).

Compound 364: RT (IA-3, Hexane-IPA-MeOH, 60-20-20, 0.15 ml/min)=28.600 min.

$^1$H NMR (600 MHz, DMSO-$d_6$) δ 1.00-1.04 (m, 3H), 1.29-1.40 (m, 1H), 1.71-1.80 (m, 1H), 1.81-1.91 (m, 1H), 1.95-2.03 (m, 3H), 2.05-2.20 (m, 1H), 2.25-2.34 (m, 1H), 2.75-3.23 (m, 1H), 3.35-4.05 (m, 1H), 5.19-5.57 (m, 1H), 5.57-5.70 (m, 2H), 7.31 (dd, 1H), 7.40-7.55 (m, 2H), 7.66-7.72 (m, 1H), 7.93-8.07 (m, 2H), 10.40-10.56 (m, 1H), 12.96-13.07 (m, 1H).

LCMS(ESI): [M+H]$^+$ m/z: calcd 392.2; found 393.2; Rt=3.563 min.

Compound 363: RT (IA-3, Hexane-IPA-MeOH, 60-20-20, 0.15 ml/min)=16.782 min.

$^1$H NMR (600 MHz, DMSO-$d_6$) δ 0.98-1.03 (m, 3H), 1.29-1.40 (m, 1H), 1.71-1.79 (m, 1H), 1.82-1.94 (m, 1H), 1.96-2.04 (m, 3H), 2.05-2.20 (m, 1H), 2.22-2.30 (m, 1H), 2.74-3.23 (m, 1H), 3.41-4.03 (m, 1H), 5.20-5.58 (m, 1H), 5.59-5.70 (m, 2H), 7.24-7.38 (m, 1H), 7.40-7.57 (m, 2H), 7.67-7.73 (m, 1H), 7.93-8.07 (m, 2H), 10.43-10.55 (m, 1H), 12.94 13.08 (m, 1H).

LCMS(ESI): [M+H]$^+$ m/z: calcd 392.2; found 393.2; Rt=3.551 min.

Compound 1083: RT (IA-3, Hexane-IPA-MeOH, 60-20-20, 0.15 ml/min)=24.432 min.

LCMS(ESI): [M+H]$^+$ m/z: calcd 392.2; found 393.2; Rt=3.599 min.

Compound 392: RT (IA-3, Hexane-IPA-MeOH, 60-20-20, 0.15 ml/min)=15.413 min.

$^1$H NMR (600 MHz, DMSO-$d_6$) δ 0.68-0.79 (m, 3H), 1.10-1.21 (m, 1H), 1.57-1.78 (m, 2H), 1.81-1.96 (m, 1H), 1.96-2.07 (m, 3H), 2.54-2.57 (m, 1H), 3.52-3.60 (m, 1.7H), 4.16-4.22 (m, 0.3H), 5.17-6.02 (m, 3H), 7.24-7.39 (m, 1H), 7.41-7.52 (m, 1H), 7.52-7.56 (m, 1H), 7.64-7.75 (m, 1H), 7.92-8.03 (m, 1H), 8.04-8.20 (m, 1H), 10.49-10.61 (m, 1H), 13.02 (s, 1H).

LCMS(ESI): [M+H]⁺ m/z: calcd 392.2; found 393.2; Rt=3.600 min.

Example 313. The Synthesis of N-(6-amino-5-methyl-3-pyridyl)-2-[(2R,5S)-2-(4-hydroxy-3-methyl-phenyl)-5-methyl-1-piperidyl]-2-oxo-acetamide and N-(6-amino-5-methyl-3-pyridyl)-2-[(2S,5R)-2-(4-hydroxy-3-methyl-phenyl)-5-methyl-1-piperidyl]-2-oxo-acetamide (Compound 551 and Compound 572

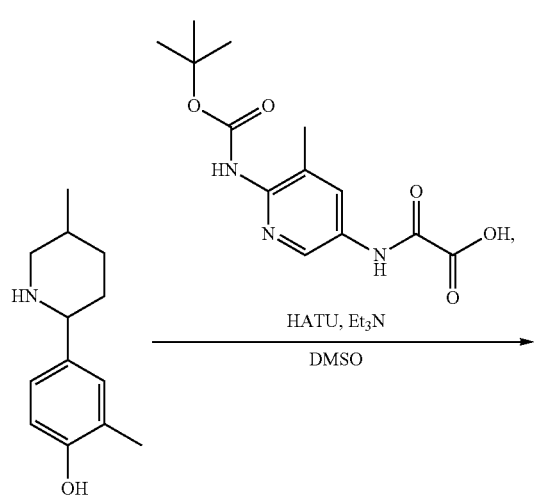

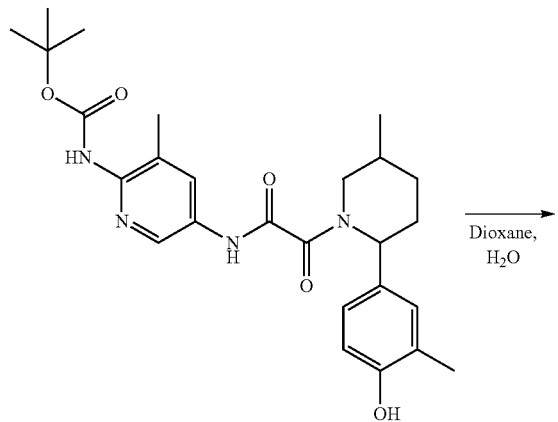

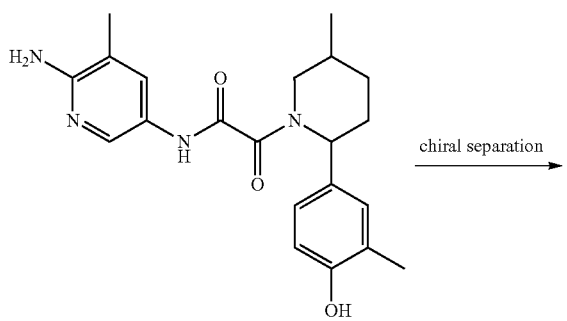

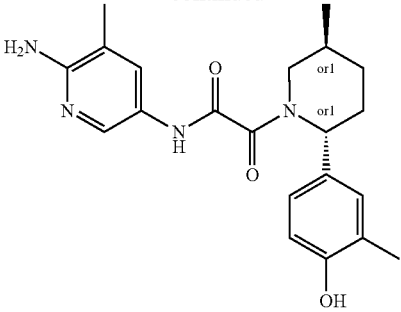

Compound 551

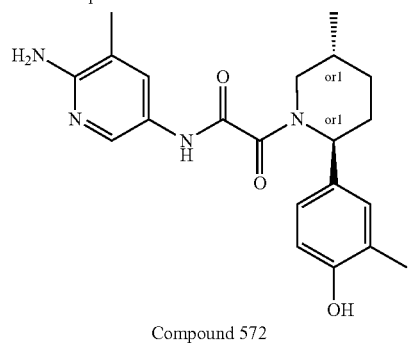

Compound 572

Step 1: Synthesis of tert-butyl N-[5-[[2-[2-(4-hydroxy-3-methyl-phenyl)-5-methyl-1-piperidyl]-2-oxo-acetyl]amino]-3-methyl-2-pyridyl]carbamate To a stirred solution of 2-methyl-4-(5-methyl-2-piperidyl)phenol (250 mg, 1.22 mmol), 2-[[6-(tert-butoxycarbonylamino)-5-methyl-3-pyridyl]amino]-2-oxo-acetic acid (359.59 mg, 1.22 mmol) and HATU (509.33 mg, 1.34 mmol) in DMSO (4 mL) was added Et₃N (246.45 mg, 2.44 mmol, 339.46 µL). The reaction mixture was stirred at 20° C. for 16 hours. After 16 hours, LCMS indicated not complete consumption of starting materials. HATU (120 mg) was further added to the reaction mixture and the reaction mixture was stirred for 40 hours. After 40 hours, the reaction mixture was purified by reverse phase HPLC (Eluent: 2-10 min, 40-60%, H₂O-MeOH; flow rate: 30 mL/min; loading pump: 4 mL, MeOH; column: TRIART 100×20 mm, 5 µM) to obtain tert-butyl N-[5-[[2-[2-(4-hydroxy-3-methyl-phenyl)-5-methyl-1-piperidyl]-2-oxo-acetyl]amino]-3-methyl-2-pyridyl]carbamate (0.12 g, 248.67 µmol, 20.42% yield) as a brown solid.

LCMS(ESI): [M+H]⁺ m/z: calcd 482.3; found 483.2; Rt=3.257 min.

Step 2: Synthesis of N-(6-amino-5-methyl-3-pyridyl)-2-[2-(4-hydroxy-3-methyl-phenyl)-5-methyl-1-piperidyl]-2-oxo-acetamide tert-butyl N-[5-[[2-[2-(4-hydroxy-3-methyl-phenyl)-5-methyl-1-piperidyl]-2-oxo-acetyl]amino]-3-methyl-2-pyridyl]carbamate (0.12 g, 248.67 µmol) was dissolved in 1,4-dioxane (1 mL) and water (1 mL). The resulting reaction mixture was stirred at 100° C. for overnight. The reaction mixture was then purified by reverse phase HPLC (Eluent: 2-10 min, 40-60%, water+NH₃/MeOH+NH₃; loading pump: 4 mL, MeOH+NH₃; column: TRIART 100×20 mm, 5 µM) to get N-(6-amino-5-methyl-3-pyridyl)-2-[2-(4-hydroxy-3- methyl-phenyl)-5-methyl-1-piperidyl]-2-oxo-acetamide (69 mg, 180.41 μmol, 72.55% yield) as a light brown solid.

LCMS(ESI): [M+H]⁺ m/z: calcd 382.3; found 383.4; Rt=1.960 min.

Step 3: Chiral Separation of N-(6-amino-5-methyl-3-pyridyl)-2-[(2R,5S)-2-(4-hydroxy-3-methyl-phenyl)-5-methyl-1-piperidyl]-2-oxo-acetamide and N-(6-amino-5-methyl-3-pyridyl)-2-[(2S,5R)-2-(4-hydroxy-3-methyl-phenyl)-5-methyl-1-piperidyl]-2-oxo-acetamide (Compound 551 and Compound 572

N-(6-amino-5-methyl-3-pyridyl)-2-[2-(4-hydroxy-3-methyl-phenyl)-5-methyl-1-piperidyl]-2-oxo-acetamide (69 mg, 180.41 μmol) was subjected to chiral HPLC purification (Column: OJ-H-I (250×20 mm, 5 um), Eluent: Hexane-MeOH-IPA, 60-20-20, flow rate: 12 mL/min) to get N-(6-amino-5-methyl-3-pyridyl)-2-[(2R,5S)-2-(4-hydroxy-3-methyl-phenyl)-5-methyl-1-piperidyl]-2-oxo-acetamide (Compound 551, 24.61 mg) and N-(6-amino-5-methyl-3-pyridyl)-2-[(2S,5R)-2-(4-hydroxy-3-methyl-phenyl)-5-methyl-1-piperidyl]-2-oxo-acetamide (Compound 572, 24.03 mg) as light-yellow solids.

Compound 551:
¹H NMR (DMSO-d₆, 600 MHz): δ (ppm) 0.94-1.03 (m, 3H), 1.23-1.35 (m, 1H), 1.63-1.76 (m, 1H), 1.77-1.88 (m, 1H), 1.90-1.97 (m, 1H), 1.96-2.02 (m, 3H), 2.07-2.16 (m, 4H), 2.68-3.23 (m, 1H), 3.37-3.99 (m, 1H), 4.94-5.52 (m, 1H), 5.52-5.63 (m, 2H), 6.70-6.77 (m, 1H), 6.84-6.94 (m, 1H), 6.95-7.04 (m, 1H), 7.39-7.51 (m, 1H), 7.91-8.05 (m, 1H), 9.20 (s, 1H), 10.34-10.53 (m, 1H).

LCMS(ESI): [M+H]⁺ m/z: calcd 382.3; found 383.2; Rt=1.265 min.

Chiral HPLC: Rt=21.77 min (Column: AD-H; Mobile phase: Hexane-IPA-MeOH, 50-25-25;

Flow Rate: 0.6 mL/min).

Compound 572:
¹H NMR (DMSO-d₆, 600 MHz): δ (ppm) 0.95-1.01 (m, 3H), 1.24-1.33 (m, 1H), 1.63-1.75 (m, 1H), 1.78-1.89 (m, 1H), 1.90-1.97 (m, 1H), 1.98-2.03 (m, 3H), 2.08-2.17 (m, 4H), 2.68-3.21 (m, 1H), 3.37-3.97 (m, 1H), 4.95-5.53 (m, 1H), 5.55-5.63 (m, 2H), 6.70-6.80 (m, 1H), 6.86-6.95 (m, 1H), 6.95-7.03 (m, 1H), 7.39-7.55 (m, 1H), 7.93-8.09 (m, 1H), 9.03-9.43 (m, 1H), 10.32-10.60 (m, 1H).

LCMS(ESI): [M+H]⁺ m/z: calcd 382.3; found 383.2; Rt=1.265 min.

Chiral HPLC: Rt=19.12 min (Column: AD-H; Mobile phase: Hexane-IPA-MeOH, 50-25-25;

Flow Rate: 0.6 mL/min).

Example 314. The Synthesis of N-(6-amino-5-methyl-3-pyridyl)-2-[5-methyl-2-(2-oxoindolin-5-yl)-1-piperidyl]-2-oxo-acetamide (Compound 373

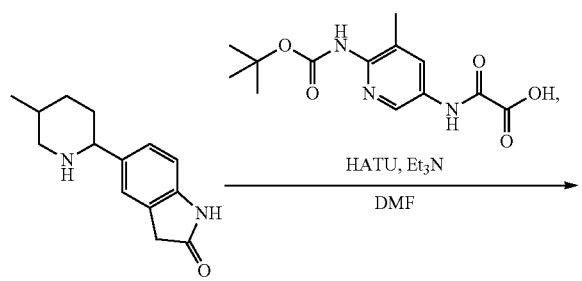

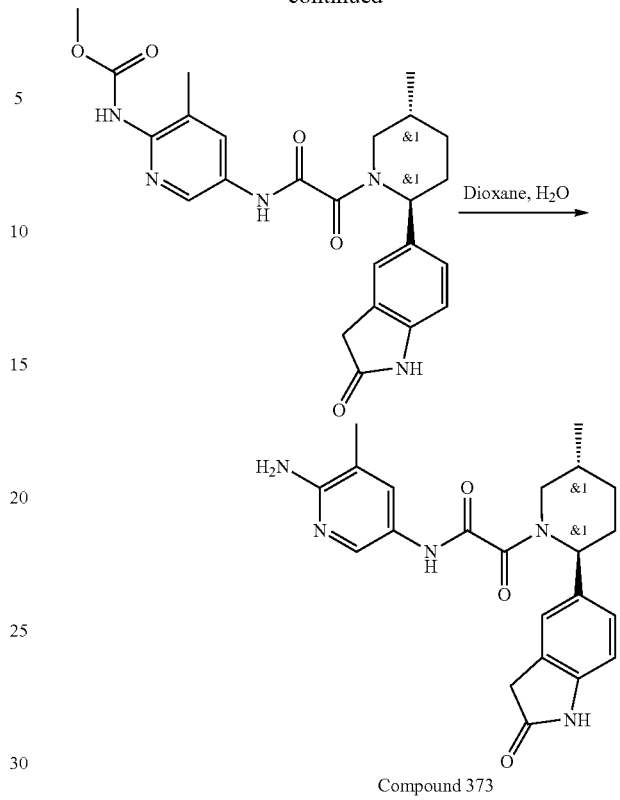

Compound 373

Step 1: Synthesis of tert-butyl N-[3-methyl-5-[[2-[5-methyl-2-(2-oxoindolin-5-yl)-1-piperidyl]-2-oxo-acetyl]amino]-2-pyridyl]carbamate To a stirred solution of 5-(5-methyl-2-piperidyl)indolin-2-one (0.4 g, 1.74 mmol), 2-[[6-(tert-butoxycarbonylamino)-5-methyl-3-pyridyl]amino]-2-oxo-acetic acid (512.87 mg, 1.74 mmol) and Triethylamine (1.76 g, 17.37 mmol, 2.42 mL) in DMF (5 mL) was added HATU (990.59 mg, 2.61 mmol) at the room temperature. The resulting reaction mixture was stirred for 18 hours at the same temperature. After 18 hours, the reaction mixture was concentrated under reduced pressure. The obtained residue was purified by HPLC (Eluent: 2-10 min, 60-85%, MeOH/H₂O; flow rate: 30 mL/min; loading pump: 4 mL, MeOH; column: SunFire 100×19 mm, 5 μM) to get tert-butyl N-[3-methyl-5-[[2-[5-methyl-2-(2-oxoindolin-5-yl)-1-piperidyl]-2-oxo-acetyl]amino]-2-pyridyl]carbamate (0.1017 g, 200.36 μmol, 11.54% yield) as a red solid.

LCMS(ESI): [M+H]⁺ m/z: calcd 507.3; found 508.2; Rt=1.298 min.

Step 2: Synthesis of N-(6-amino-5-methyl-3-pyridyl)-2-[5-methyl-2-(2-oxoindolin-5-yl)-1-piperidyl]-2-oxo-acetamide (Compound 373 tert-butyl N-[3-methyl-5-[[2-[5-methyl-2-(2-oxoindolin-5-yl)-1-piperidyl]-2-oxo-acetyl]amino]-2-pyridyl]carbamate (0.1017 g, 200.36 μmol) was dissolved in Dioxane (2 mL) and Water (2 mL). The resulting reaction mixture was heated at 100° C. for 18 hours. Upon completion, the reaction mixture was evaporated to dryness to obtain N-(6-amino-5-methyl-3-pyridyl)-2-[5-methyl-2-(2-oxoindolin-5- yl)-1-piperidyl]-2-oxo-acetamide (Compound 373, 0.056 g, 137.44 µmol, 68.59% yield) as red solid.

$^1$H NMR (DMSO-d$_6$, 500 MHz): δ (ppm) 0.99-1.03 (m, 3H), 1.22-1.37 (m, 1H), 1.67-1.77 (m, 1H), 1.82-1.93 (m, 1H), 2.00-2.07 (m, 3H), 2.09-2.24 (m, 1H), 2.72-2.81 (m, 0.3H), 3.21-3.25 (m, 0.7H), 3.40-3.53 (m, 3H), 3.64-4.02 (m, 1H), 5.03-5.58 (m, 1H), 5.58-5.70 (m, 2H), 6.78-6.89 (m, 1H), 7.07-7.27 (m, 2H), 7.40-7.54 (m, 1H), 7.93-8.08 (m, 1H), 10.36 (s, 1H), 10.43-10.57 (m, 1H).

LCMS(ESI): [M+H]$^+$ m/z: calcd 407.2; found 408.2; Rt=0.856 min.

Example 315. The Synthesis of N-(6-amino-5-methyl-3-pyridyl)-2-[(2R,4R,5R)-4,5-dimethyl-2-phenyl-1-piperidyl]-2-oxo-acetamide (Compound 304), N-(6-amino-5-methyl-3-pyridyl)-2-[(2S,4S,5S)-4,5-dimethyl-2-phenyl-1-piperidyl]-2-oxo-acetamide (Compound 299), N-(6-amino-5-methyl-3-pyridyl)-2-[(2R,4R,5S)-4,5-dimethyl-2-phenyl-1-piperidyl]-2-oxo-acetamide (Compound 313), and N-(6-amino-5-methyl-3-pyridyl)-2-[(2S,4S,5R)-4,5-dimethyl-2-phenyl-1-piperidyl]-2-oxo-acetamide (Compound 305)

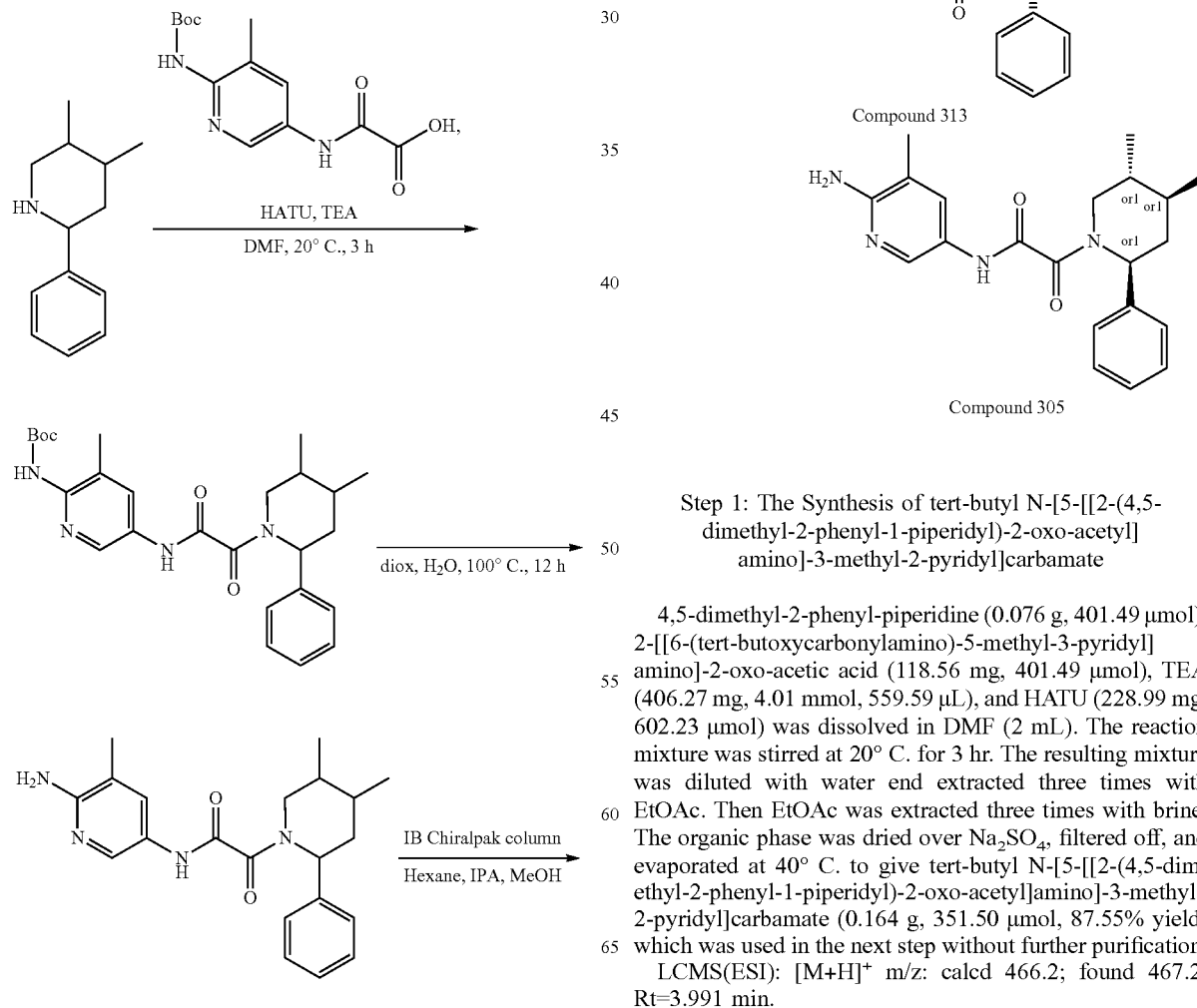

Step 1: The Synthesis of tert-butyl N-[5-[[2-(4,5-dimethyl-2-phenyl-1-piperidyl)-2-oxo-acetyl]amino]-3-methyl-2-pyridyl]carbamate 4,5-dimethyl-2-phenyl-piperidine (0.076 g, 401.49 µmol), 2-[[6-(tert-butoxycarbonylamino)-5-methyl-3-pyridyl]amino]-2-oxo-acetic acid (118.56 mg, 401.49 µmol), TEA (406.27 mg, 4.01 mmol, 559.59 µL), and HATU (228.99 mg, 602.23 µmol) was dissolved in DMF (2 mL). The reaction mixture was stirred at 20° C. for 3 hr. The resulting mixture was diluted with water end extracted three times with EtOAc. Then EtOAc was extracted three times with brine. The organic phase was dried over Na$_2$SO$_4$, filtered off, and evaporated at 40° C. to give tert-butyl N-[5-[[2-(4,5-dimethyl-2-phenyl-1-piperidyl)-2-oxo-acetyl]amino]-3-methyl-2-pyridyl]carbamate (0.164 g, 351.50 µmol, 87.55% yield) which was used in the next step without further purification.

LCMS(ESI): [M+H]$^+$ m/z: calcd 466.2; found 467.2; Rt=3.991 min.

Step 2: The Synthesis of N-(6-amino-5-methyl-3-pyridyl)-2-(4,5-dimethyl-2-phenyl-1-piperidyl)-2-oxo-acetamide tert-butyl N-[5-[[2-(4,5-dimethyl-2-phenyl-1-piperidyl)-2-oxo-acetyl]amino]-3-methyl-2-pyridyl]carbamate (0.164 g, 351.50 µmol) was dissolved in mixture of diaxane (2 mL) and water (2 mL). Then, stirred at 100° C. for 12 hr. The reaction mixture was concentrated on vacuo at 55° C. to give crude product which was purified by HPLC (35-60% water-methanol+NH$_3$, 2-10 min, flow 30 ml/min (loading pump 4 ml/min methanol+NH$_3$), column: SUNFIRE C18 100*20 mm) to give N-(6-amino-5-methyl-3-pyridyl)-2-(4,5-dimethyl-2-phenyl-1-piperidyl)-2-oxo-acetamide (0.047 g, 128.26 µmol, 36.49% yield).

$^1$H NMR (400 MHz, DMSO-d$_6$) δ 0.72 (m, 2H), 0.93 (m, 3H), 1.45 (m, 1H), 2.03 (m, 3H), 3.66 (m, 1H), 5.64 (m, 2H), 7.31 (m, 4H), 7.48 (m, 1H), 8.02 (d, 1H), 10.46 (s, 1H).

LCMS(ESI): [M+H]$^+$ m/z: calcd 366.2; found 367.2; Rt=1.110 min.

Step 3: The Synthesis of N-(6-amino-5-methyl-3-pyridyl)-2-[(2R,4R,5R)-4,5-dimethyl-2-phenyl-1-piperidyl]-2-oxo-acetamide (Compound 304), N-(6-amino-5-methyl-3-pyridyl)-2-[(2S,4S,5S)-4,5-dimethyl-2-phenyl-1-piperidyl]-2-oxo-acetamide (Compound 299), N-(6-amino-5-methyl-3-pyridyl)-2-[(2R,4R,5S)-4,5-dimethyl-2-phenyl-1-piperidyl]-2-oxo-acetamide (Compound 313), and N-(6-amino-5-methyl-3-pyridyl)-2-[(2S,4S,5R)-4,5-dimethyl-2-phenyl-1-piperidyl]-2-oxo-acetamide (Compound 305

N-(6-amino-5-methyl-3-pyridyl)-2-(4,5-dimethyl-2-phenyl-1-piperidyl)-2-oxo-acetamide (0.047 g, 128.26 µmol) was chirally separated using Column: Chiralpak IB (250*20 mm, 5 mkm); Mobile phase: Hexane-IPA-MeOH, 80-10-10 Flow Rate: 12 mL/min; Column Temperature: 24° C.; Wavelength: 205 nm, 266 nm, 308 nm) affording Compound 304—N-(6-amino-5-methyl-3-pyridyl)-2-[(2R,4R,5R)-4,5-dimethyl-2-phenyl-1-piperidyl]-2-oxo-acetamide (6.5 mg, 17.74 µmol, 13.83% yield; RT=20.645 min), Compound 299—N-(6-amino-5-methyl-3-pyridyl)-2-[(2S,4S,5S)-4,5-dimethyl-2-phenyl-1-piperidyl]-2-oxo-acetamide (6.90 mg, 18.83 µmol, 14.68% yield; RT=28.632 min), Compound 313—N-(6-amino-5-methyl-3-pyridyl)-2-[(2R,4R,5S)-4,5-dimethyl-2-phenyl-1-piperidyl]-2-oxo-acetamide (14.8 mg, 40.39 µmol, 31.49% yield; RT=22.209 min), and Compound 305—N-(6-amino-5-methyl-3-pyridyl)-2-[(2S,4S,5R)-4,5-dimethyl-2-phenyl-1-piperidyl]-2-oxo-acetamide (14.1 mg, 38.48 µmol, 30.0% yield; RT=25.742 min).

Compound 304: RT (IB, Hexane-IPA-MeOH, 80-10-10, 0.6 ml/min)=20.891 min.

$^1$H NMR (500 MHz, DMSO-d$_6$) δ 0.44-0.63 (m, 3H), 0.70-0.83 (m, 3H), 1.87-1.92 (m, 1H), 1.94-2.15 (m, 6H), 2.91-3.01 (m, 1H), 3.43-4.27 (m, 1H), 5.12-5.47 (m, 1H), 5.91 (br s, 2H), 7.18-7.29 (m, 2H), 7.29-7.39 (m, 3H), 7.40-7.63 (m, 1H), 7.87-8.14 (m, 1H), 10.39-10.67 (m, 1H).

LCMS(ESI): [M+H]$^+$ m/z: calcd 366.2; found 367.2; Rt=4.101 min.

Compound 299: RT (IB, Hexane-IPA-MeOH, 80-10-10, 0.6 ml/min)=28.641 min.

$^1$H NMR (500 MHz, DMSO-d$_6$) δ 0.45-0.60 (m, 3H), 0.70-0.80 (m, 3H), 1.89-1.94 (m, 1H), 1.97-2.09 (m, 5H), 2.09-2.18 (m, 1H), 2.84-3.09 (m, 1H), 3.40-4.35 (m, 1H), 5.13-5.45 (m, 1H), 5.56-5.97 (m, 2H), 7.21-7.36 (m, 5H), 7.38-7.58 (m, 1H), 7.68-8.14 (m, 1H), 9.82-10.60 (m, 1H).

LCMS(ESI): [M+H]$^+$ m/z: calcd 366.2; found 367.2; Rt=4.069 min.

Compound 313: RT (IB, Hexane-IPA-MeOH, 80-10-10, 0.6 ml/min)=22.277 min.

$^1$H NMR (500 MHz, DMSO-d$_6$) δ 0.91-1.04 (m, 6H), 1.14-1.27 (m, 1H), 1.45-1.55 (m, 1H), 1.55-1.68 (m, 1H), 1.96-2.10 (m, 4H), 3.42-4.03 (m, 2H), 5.03-5.26 (m, 1H), 5.51-5.71 (m, 2H), 7.19-7.35 (m, 5H), 7.36-7.54 (m, 1H), 7.70-8.08 (m, 1H), 9.98-10.53 (m, 1H).

LCMS(ESI): [M+H]$^+$ m/z: calcd 366.2; found 367.2; Rt=4.036 min.

Compound 305: RT (IB, Hexane-IPA-MeOH, 80-10-10, 0.6 ml/min)=25.609 min.

$^1$H NMR (500 MHz, DMSO-d$_6$) δ 0.89-1.00 (m, 6H), 1.15-1.25 (m, 1H), 1.44-1.53 (m, 1H), 1.55-1.68 (m, 1H), 1.97-2.10 (m, 4H), 3.55-4.02 (m, 2H), 5.03-5.27 (m, 1H), 5.53-5.67 (m, 2H), 7.18-7.34 (m, 5H), 7.36-7.54 (m, 1H), 7.68-8.10 (m, 1H), 9.98-10.51 (m, 1H).

LCMS(ESI): [M+H]$^+$ m/z: calcd 366.2; found 367.2; Rt=4.009 min.

Example 316. The Synthesis of N-(6-amino-5-methyl-3-pyridyl)-2-[(2S,5R)-5-methyl-2-[4-(2,2,2-trifluoroethylamino)phenyl]-1-piperidyl]-2-oxo-acetamide (Compound 522) and N-(6-amino-5-methyl-3-pyridyl)-2-[(2R,5S)-5-methyl-2-[4-(2,2,2-trifluoroethylamino)phenyl]-1-piperidyl]-2-oxo-acetamide (Compound 528

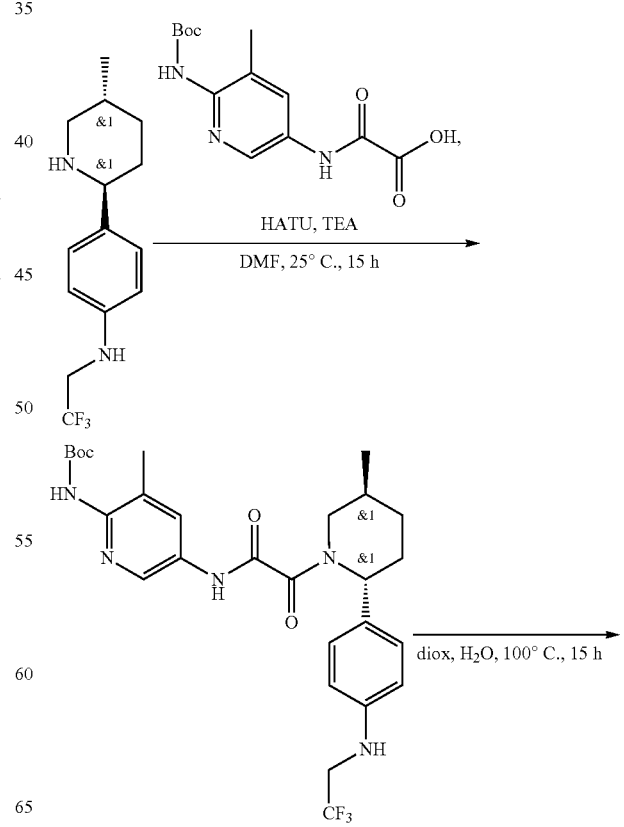

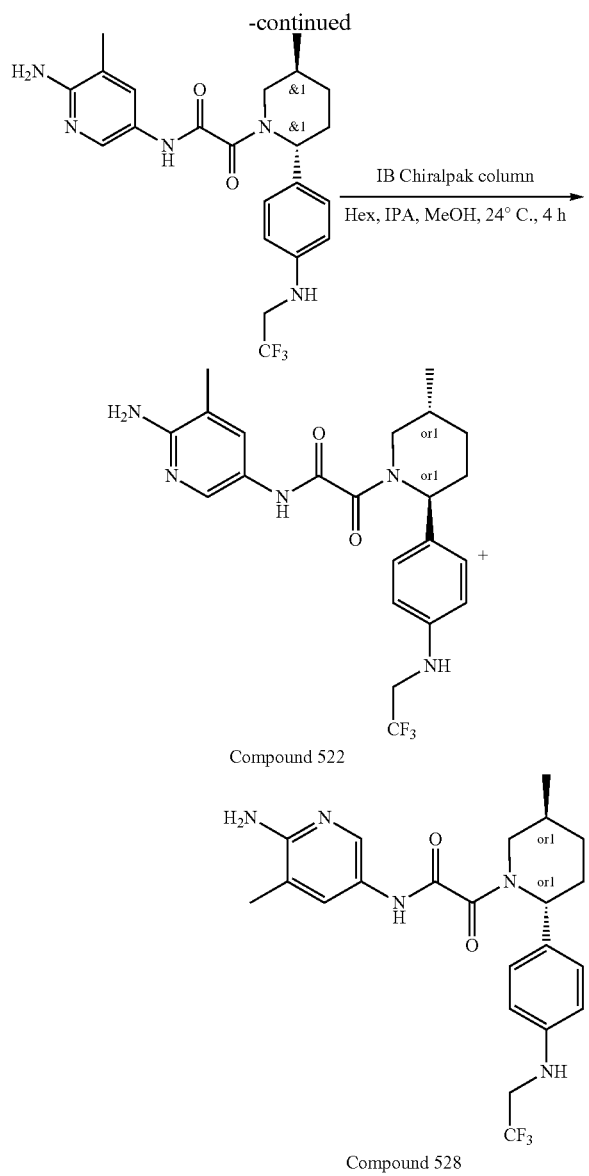

Compound 522

Compound 528

Step 1: The Synthesis of tert-butyl N-[3-methy-5-[[2-[(2R,5S)-5-methyl-2-[4-(2,2,2-trifluoroethyl-amino)phenyl]-1-piperidyl]-2-oxo-acetyl]amino]-2-pyridyl]carbamate 4-[(2R,5S)-5-methyl-2-piperidyl]-N-(2,2,2-trifluoro-ethyl) aniline (300 mg, 1.10 mmol, 2HCl), 2-[[6-(tert-butoxycarbonylamino)-5-methyl-3-pyridyl]amino]-2-oxo-acetic acid (325.32 mg, 1.10 mmol, HCl) and triethylamine (557.40 mg, 5.51 mmol, 767.77 μL) were mixed together in dimethylformamide (5 mL). Obtained mixture was briefly heated to 60-70° C. until clear solution was formed. After cooling to 5-10° C., HATU (460.78 mg, 1.21 mmol) was added portionwise during 5 min. Resulting solution was stirred at 25° C. for 15 hr. Then it was subjected to HPLC (Column: SunFire C18 100*19 mm, 5 um; 60-60-90% 0-1-6 min water-methanol, flow: 30 ml/min), affording tert-butyl N-[3-methyl-5-[[2-[(2R,5S)-5-methyl-2-[4-(2,2,2-trifluoro-ethylamino)phenyl]-1-piperidyl]-2-oxo-acetyl]amino]-2-pyridyl]carbamate (99 mg, 180.14 μmol, 16.35% yield).

$^1$H NMR (500 MHz, DMSO-$d_6$) δ 0.73 (m, 2H), 1.01 (m, 2H), 1.43 (m, 9H), 1.64 (m, 2H), 2.19 (d, 3H), 3.54 (m, 2H), 3.90 (m, 2H), 4.15 (m, 2H), 5.00 (m, 1H), 5.57 (m, 1H), 6.22 (s, 1H), 6.76 (m, 2H), 7.06 (m, 2H), 7.96 (m, 1H), 8.45 (m, 1H), 9.05 (m, 1H).

LCMS(ESI): [M+H]$^+$ m/z: calcd 549.2; found 550.2; Rt=3.496 min.

Step 2: The Synthesis of N-(6-amino-5-methyl-3-pyridyl)-2-[(2R,5S)-5-methyl-2-[4-(2,2,2-trifluoro-ethylamino)phenyl]-1-piperidyl]-2-oxo-acetamide tert-butyl N-[3-methyl-5-[[2-[(2R,5S)-5-methyl-2-[4-(2,2,2-trifluoroethylamino)phenyl]-1-piperidyl]-2-oxo-acetyl]amino]-2-pyridyl]carbamate (99 mg, 180.14 μmol) was dissolved in dioxane (1 mL) and water (0.5 mL). Resulting solution was stirred at 100° C. for 15 hr. Then, it was subjected to HPLC (column: YMC Triart C18 100*20 mm, 5 um; 50-90% 0-5 min 0.1% NH$_3$-methanol, flow: 30 ml/min), affording N-(6-amino-5-methyl-3-pyridyl)-2-[(2R,5S)-5-methyl-2-[4-(2,2,2-trifluoroethylamino)phenyl]-1-piperidyl]-2-oxo-acetamide (55 mg, 122.37 μmol, 67.93% yield).

LCMS(ESI): [M+H]$^+$ m/z: calcd 449.2; found 450.2; Rt=2.468 min.

Step 3: The Synthesis of N-(6-amino-5-methyl-3-pyridyl)-2-[(2S,5R)-5-methyl-2-[4-(2,2,2-trifluoro-ethylamino)phenyl]-1-piperidyl]-2-oxo-acetamide (Compound 522) and N-(6-amino-5-methyl-3-pyridyl)-2-[(2R,5S)-5-methyl-2-[4-(2,2,2-trifluoro-ethylamino)phenyl]-1-piperidyl]-2-oxo-acetamide (Compound 528

N-(6-amino-5-methyl-3-pyridyl)-2-[(2R,5S)-5-methyl-2-[4-(2,2,2-trifluoroethylamino)phenyl]-1-piperidyl]-2-oxo-acetamide (55 mg, 122.37 μmol) was divided into enantiomers by Chiral HPLC (Column: Chiralpak IB (250*20 mm, 5 mkm; mobile phase: Hexane-IPA-MeOH, 60-20-20; flow rate: 12 mL/min; Temperature=24° C.), affording:

Compound 522—N-(6-amino-5-methyl-3-pyridyl)-2-[(2S,5R)-5-methyl-2-[4-(2,2,2-trifluoroethylamino)phenyl]-1-piperidyl]-2-oxo-acetamide (19 mg, 42.27 μmol, 69.09% yield) with ret.time=16.417 min (Compound 522) and Compound 528—N-(6-amino-5-methyl-3-pyridyl)-2-[(2R,5S)-5-methyl-2-[4-(2,2,2-trifluoroethylamino)phenyl]-1-piperidyl]-2-oxo-acetamide (33.9 mg, crude) with ret.time=36.985-38.961 min (Compound 528)

Compound 522: RT (IB, Hexane-IPA-MeOH, 60-20-20, 0.15 mL/min)=7.556 min.

$^1$H NMR (600 MHz, DMSO-$d_6$) δ 0.70-0.78 (m, 3H), 1.08-1.15 (m, 1H), 1.56-1.65 (m, 2H), 1.72-1.86 (m, 1H), 1.86-2.18 (m, 5H), 3.46-3.54 (m, 0.5H), 3.85-3.89 (m, 2H), 4.09-4.17 (m, 0.5H), 4.94-5.53 (m, 1H), 5.57-5.63 (m, 2H), 6.18-6.21 (m, 1H), 6.70-6.73 (m, 2H), 7.01-7.08 (m, 2H), 7.43-7.52 (m, 1H), 7.95-8.05 (m, 1H), 10.46-10.51 (m, 1H).

LCMS(ESI): [M+H]$^+$ m/z: calcd 449.2; found 450.2; Rt=2.543 min.

Compound 528: RT (IB, Hexane-IPA-MeOH, 60-20-20, 0.15 mL/min)=4.220 min.

$^1$H NMR (600 MHz, DMSO-$d_6$) δ 0.69-0.99 (m, 3H), 1.03-1.18 (m, 1H), 1.45-1.72 (m, 2H), 1.74-1.90 (m, 1H), 1.97-2.03 (m, 3H), 2.04-2.20 (m, 1H), 2.65-3.28 (m, 1H), 3.36-3.54 (m, 0.7H), 3.84-3.92 (m, 2H), 4.10-4.16 (m, 0.3H), 4.92-5.55 (m, 1H), 5.54-5.66 (m, 2H), 6.14-6.25 (m, 1H), 6.65-6.78 (m, 2H), 7.00-7.12 (m, 2H), 7.39-7.55 (m, 1H), 7.89-8.07 (m, 1H), 10.38-10.58 (m, 1H).

LCMS(ESI): [M+H]⁺ m/z: calcd 449.2; found 450.2; Rt=19.009 min.

Example 317. The Synthesis of N-(6-amino-5-ethyl-3-pyridyl)-2-[(2S,5R)-5-methyl-2-(2-oxo-3,4-dihydro-1H-quinolin-6-yl)-1-piperidyl]-2-oxo-acetamide (Compound 720) and N-(6-amino-5-ethyl-3-pyridyl)-2-[(2R,5S)-5-methyl-2-(2-oxo-3,4-dihydro-1H-quinolin-6-yl)-1-piperidyl]-2-oxo-acetamide (Compound 729)

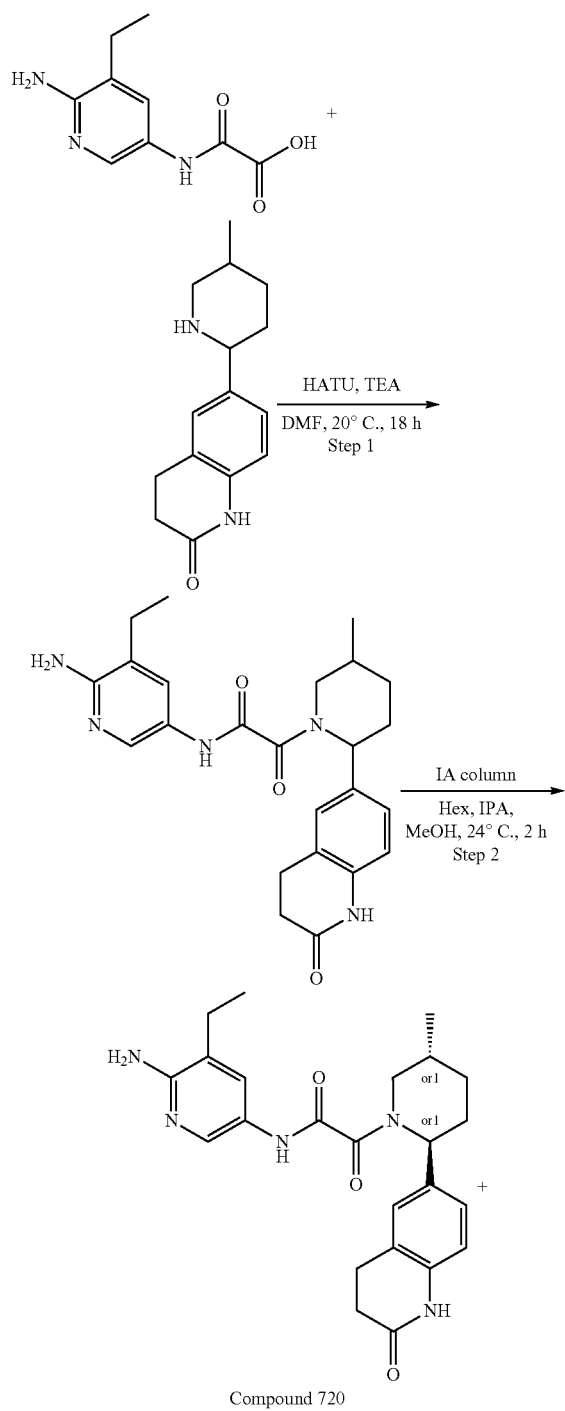

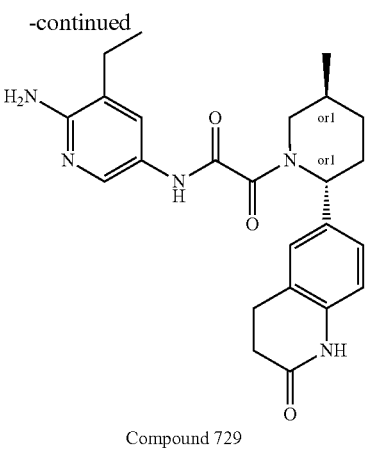

Compound 729

Step 1: The Synthesis of N-(6-amino-5-ethyl-3-pyridyl)-2-[5-methyl-2-(2-oxo-3,4-dihydro-1H-Quinolin-6-yl)-1-piperidyl]-2-oxo-acetamide HATU (176.04 mg, 462.98 µmol) was added portionwise at r.t. to a suspension of 2-[(6-amino-5-ethyl-3-pyridyl)amino]-2-oxo-acetic acid (96.86 mg, 462.98 µmol), 6-(5-methyl-2-piperidyl)-3,4-dihydro-1H-quinolin-2-one (130 mg, 462.98 µmol, HCl) and TEA (281.09 mg, 2.78 mmol, 387.18 µL) in DMF (10 mL). The clear solution was stirred at 20° C. for 18 hr and the solvents were evaporated in vacuo to give 1 g of crude material. It was subjected to RP-HPLC (column: YMC-Actus Triart C18 100*20 mm I.D. S-5 um; 1-6 min 45-55% water-methanol (NH₃ 0.1%), flow: 30 ml/min as mobile phase) to give N-(6-amino-5-ethyl-3-pyridyl)-2-[5-methyl-2-(2-oxo-3,4-dihydro-1H-quinolin-6-yl)-1-piperidyl]-2-oxo-acetamide (75 mg, 172.21 µmol, 37.20% yield).

LCMS(ESI): [M+H]⁺ m/z: calcd 435.2; found 436.2; Rt=2.017 min.

Step 2: The Synthesis of N-(6-amino-5-ethyl-3-pyridyl)-2-[(2S,5R)-5-methyl-2-(2-oxo-3,4-dihydro-1H-Quinolin-6-yl)-1-piperidyl]-2-oxo-acetamide (Compound 720) and N-(6-amino-5-ethyl-3-pyridyl)-2-[(2R,5S)-5-methyl-2-(2-oxo-3,4-dihydro-1H-Quinolin-6-yl)-1-piperidyl]-2-oxo-acetamide (Compound 729

The enantiomers were separated by chiral HPLC (column: IA (250*20, 5 mkm), Hexane-IPA-MeOH, 60-20-20, 12 ml/min as mobile phase) to give the two individual enantiomers Compound 720—N-(6-amino-5-ethyl-3-pyridyl)-2-[(2S,5R)-5-methyl-2-(2-oxo-3,4-dihydro-1H-quinolin-6-yl)-1-piperidyl]-2-oxo-acetamide (28.7 mg, 65.90 µmol, 76.53% yield) RetTime=59.6 min and Compound 729—N-(6-amino-5-ethyl-3-pyridyl)-2-[(2R,5S)-5-methyl-2-(2-oxo-3,4-dihydro-1H-quinolin-6-yl)-1-piperidyl]-2-oxo-acetamide (28.6 mg, 65.67 µmol, 76.27% yield) RetTime=79.4 min.

Compound 720: RT (IA, Hexane-IPA-MeOH, 60-20-20, 0.6 mL/min)=43.376 min.

¹H NMR (DMSO-d₆, 600 MHz): δ (ppm) 1.06 (m, 6H), 1.29 (m, 1H), 1.69 (m, 1H), 1.92 (m, 2H), 2.11 (m, 2H), 2.42 (m, 2H), 2.99 (m, 4H), 3.79 (m, 1H), 5.57 (m, 3H), 6.84 (m, 1H), 7.08 (m, 2H), 7.46 (m, 1H), 8.03 (m, 1H), 10.02 (m, 1H), 10.45 (m, 1H).

LCMS(ESI): [M+H]+ m/z: calcd 435.2; found 436.4; Rt=1.014 min.

Compound 729: RT (IA, Hexane-IPA-MeOH, 60-20-20, 0.6 mL/min)=60.621 min.

$^1$H NMR (DMSO-$d_6$, 600 MHz): δ (ppm) 1.03 (m, 6H), 1.33 (m, 1H), 1.67 (m, 1H), 1.85 (m, 1H), 1.97 (m, 1H), 2.14 (m, 1H), 2.39 (m, 2H), 2.86 (m, 4H), 3.45 (m, 1H), 4.09 (m, 1H), 5.57 (m, 3H), 6.84 (m, 1H), 7.08 (m, 2H), 7.46 (m, 1H), 8.03 (m, 1H), 10.02 (m, 1H), 10.45 (m, 1H). LCMS(ESI): [M+H]+ m/z: calcd 435.2; found 436.2; Rt=0.778 min.

Example 318. The Synthesis of rel-N-(6-amino-5-methyl-3-pyridyl)-2-[(2R,5S)-2-(6-amino-3-pyridyl)-5-methyl-1-piperidyl]-2-oxo-acetamide (Compound 860) and rel-N-(6-amino-5-methyl-3-pyridyl)-2-[(2S,5R)-2-(6-amino-3-pyridyl)-5-methyl-1-piperidyl]-2-oxo-acetamide (Compound 848

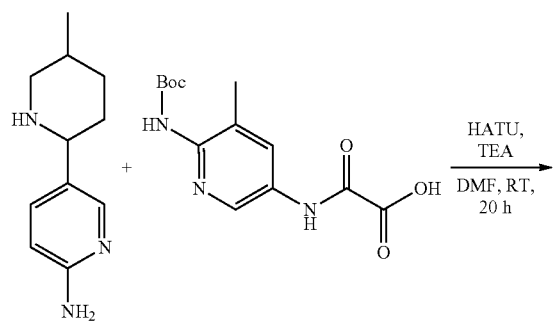

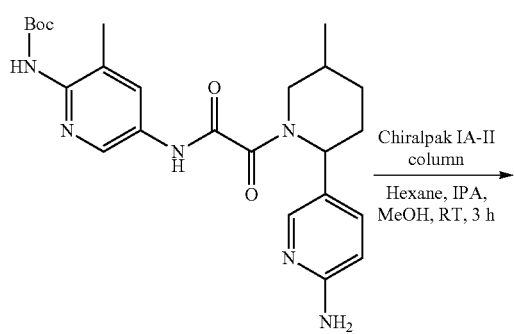

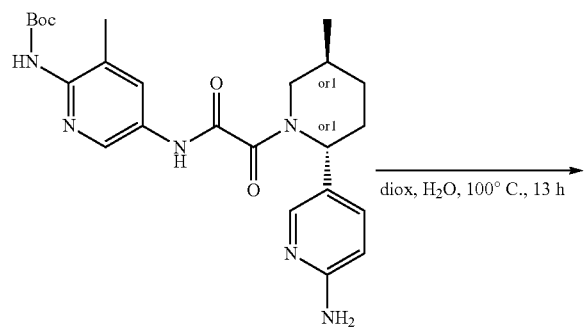

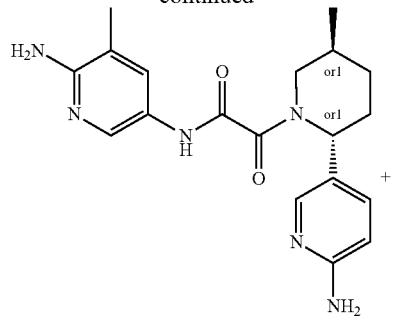

Compound 860

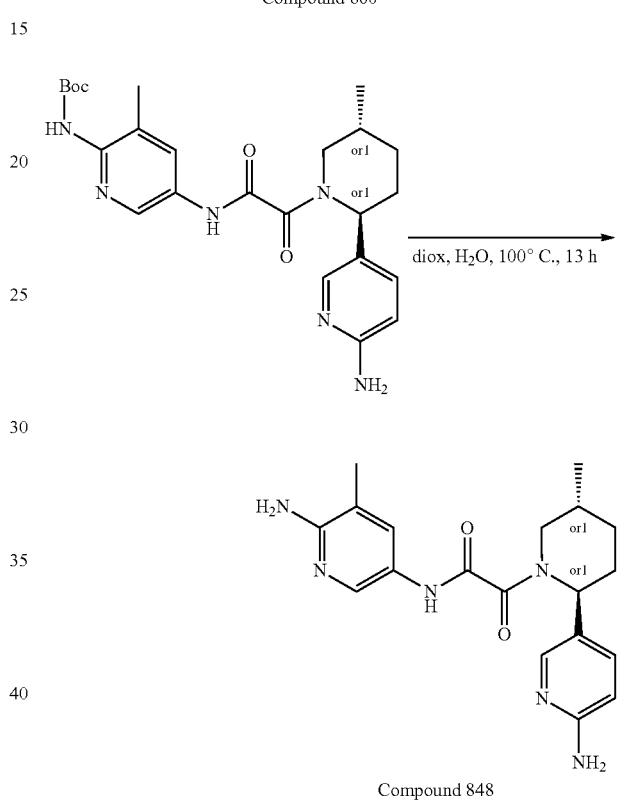

Compound 848

Step 1: The Synthesis of tert-butyl N-[5-[[2-[(2R, 5S)-2-(6-amino-3-pyridyl)-5-methyl-1-piperidyl]-2-oxo-acetyl]amino]-3-methyl-2-pyridyl]carbamate 5-(5-methyl-2-piperidyl)pyridin-2-amine (300 mg, 1.57 mmol), 2-[[6-(tert-butoxycarbonylamino)-5-methyl-3-pyridyl]amino]-2-oxo-acetic acid (463.15 mg, 1.57 mmol), triethylamine (793.56 mg, 7.84 mmol, 1.09 mL) were mixed in DMF (5 mL) and then HATU (894.56 mg, 2.35 mmol) were added. The resulting mixture were stirred at 25° C. for 12 hr. The solvent was evaporated and resulting mixture was stirred with SiliaMetS® DMT (50 mg) in methanol (10 mL). The mixture was filtered off and evaporated under reduce pressure. The obtained crude material was purified by HPLC (2-10 min 50-75% Methanol/H$_2$O, 30 mL/min) to obtain tert-butyl N-[5-[[2-[(2R,5S)-2-(6-amino-3-pyridyl)-5-methyl-1-piperidyl]-2-oxo-acetyl]amino]-3-methyl-2-pyridyl]carbamate (48.5 mg, 103.51 μmol, 6.60% yield).

LCMS(ESI): [M+H]+ m/z: calcd 468.2; found 469.2; Rt=0.943 min.

Step 2: The Synthesis of rel-tert-butyl N-[5-[[2-[(2R,5S)-2-(6-amino-3-pyridyl)-5-methyl-1-piperidyl]-2-oxo-acetyl]amino]-3-methyl-2-pyridyl]carbamate and Rel-tert-butyl N-[5-[[2-[(2S,5R)-2-(6-amino-3-pyridyl)-5-methyl-1-piperidyl]-2-oxo-acetyl]amino]-3-methyl-2-pyridyl]carbamate The mixture of diastereomers was separated by chiral chromatography (IA-II (250*20 mm,5 mkm), IPA-MeOH, 50-50, 12 mL/min) to obtain tert-butyl N-[5-[[2-[(2R,5S)-2-(6-amino-3-pyridyl)-5-methyl-1-piperidyl]-2-oxo-acetyl]amino]-3-methyl-2-pyridyl]carbamate (14.71 mg, 31.39 µmol, 30.33% yield; P1) and tert-butyl N-[5-[[2-[(2S,5R)-2-(6-amino-3-pyridyl)-5-methyl-1-piperidyl]-2-oxo-acetyl]amino]-3-methyl-2-pyridyl]carbamate (11.26 mg, 24.03 µmol, 23.22% yield; P2).

Preparative: RT for P2 (IC-II (250*20, 5 mkm), Hexane-IPA-MeOH, 50-25-25, 12 mL/min)=35.062 min.

Analytical: RT for P2 (IC, Hexane-IPA-MeOH, 50-25-25, 0.6 mL/min)=29.410 min.

LCMS(ESI): [M+2H]$^+$ m/z: calcd 468.2; found 470.2; Rt=2.001 min.

Preparative: RT for P1 (IC-II (250*20, 5 mkm), Hexane-IPA-MeOH, 50-25-25, 12 mL/min)=76.389 min.

Analytical: RT for P1 (IC, Hexane-IPA-MeOH, 50-25-25, 0.6 mL/min)=64.482 min.

LCMS(ESI): [M+H]$^+$ m/z: calcd 468.2; found 469.2; Rt=2.005 min.

Step 3: The Synthesis of rel-N-(6-amino-5-methyl-3-pyridyl)-2-[(2R,5S)-2-(6-amino-3-pyridyl)-5-methyl-1-piperidyl]-2-oxo-acetamide (Compound 860

A solution of tert-butyl N-[5-[[2-[(2R,5S)-2-(6-amino-3-pyridyl)-5-methyl-1-piperidyl]-2-oxo-acetyl]amino]-3-methyl-2-pyridyl]carbamate (14.71 mg, 31.39 µmol) in Dioxane (1 mL) and Water (1 mL) was heated at 100° C. for 13 hr. Solvents were evaporated and resulting precipitate was purified by HPLC (2-10 min 20-65% methanol/H$_2$O+NH$_3$30 mL/min (loading pump 4 mL methanol+NH$_3$)) to obtain N-(6-amino-5-methyl-3-pyridyl)-2-[(2R,5S)-2-(6-amino-3-pyridyl)-5-methyl-1-piperidyl]-2-oxo-acetamide (6.9 mg, 18.73 µmol, 59.65% yield).

$^1$H NMR (DMSO-d$_6$, 600 MHz): δ (ppm) 0.94-1.01 (m, 3H), 1.26-1.36 (m, 1H), 1.66-1.73 (m, 1H), 1.75-1.88 (m, 1H), 1.88-1.96 (m, 1H), 1.98-2.02 (m, 3H), 2.04-2.12 (m, 1H), 2.67-3.19 (m, 1H), 3.34-3.96 (m, 1H), 4.93-5.49 (m, 1H), 5.56-5.63 (m, 2H), 5.84 (s, 2H), 6.40-6.45 (m, 1H), 7.23-7.38 (m, 1H), 7.43-7.49 (m, 1H), 7.82-7.88 (m, 1H), 7.94-8.02 (m, 1H), 10.26-10.48 (m, 1H).

LCMS(ESI): [M+2H]$^+$ m/z: calcd 368.2; found 370.2; Rt=0.514 min.

Step 4: The Synthesis of rel-N-(6-amino-5-methyl-3-pyridyl)-2-[(2S,5R)-2-(6-amino-3-pyridyl)-5-methyl-1-piperidyl]-2-oxo-acetamide (Compound 848

A solution of tert-butyl N-[5-[[2-[(2S,5R)-2-(6-amino-3-pyridyl)-5-methyl-1-piperidyl]-2-oxo-acetyl]amino]-3-methyl-2-pyridyl]carbamate (11.26 mg, 24.03 µmol) in Dioxane (1 mL) and Water (1 mL) was heated at 100° C. for 12 hr. Solvents were evaporated and resulting precipitate was purified by HPLC (2-10 min 20-65% methanol/H$_2$O+ NH$_3$30 mL/min (loading pump 4 mL methanol+NH$_3$)) to obtain N-(6-amino-5-methyl-3-pyridyl)-2-[(2S,5R)-2-(6-amino-3-pyridyl)-5-methyl-1-piperidyl]-2-oxo-acetamide (5.2 mg, 14.11 µmol, 58.73% yield).

$^1$H NMR (DMSO-d$_6$, 600 MHz): δ (ppm) 0.94-1.01 (m, 3H), 1.26-1.36 (m, 1H), 1.66-1.73 (m, 1H), 1.75-1.88 (m, 1H), 1.88-1.96 (m, 1H), 1.98-2.02 (m, 3H), 2.04-2.12 (m, 1H), 2.67-3.19 (m, 1H), 3.34-3.96 (m, 1H), 4.93-5.49 (m, 1H), 5.56-5.63 (m, 2H), 5.84 (s, 2H), 6.40-6.45 (m, 1H), 7.23-7.38 (m, 1H), 7.43-7.49 (m, 1H), 7.82-7.88 (m, 1H), 7.94-8.02 (m, 1H), 10.26-10.48 (m, 1H).

LCMS(ESI): [M+H]$^+$ m/z: calcd 368.2; found 370.2; Rt=0.516 min.

Example 319. The Synthesis of rel-N-(6-amino-5-methyl-3-pyridyl)-2-[(2S,5R)-2-[6-(methanesulfonamido)-3-pyridyl]-5-methyl-1-piperidyl]-2-oxo-acetamide (Compound 980) and rel-N-(6-amino-5-methyl-3-pyridyl)-2-[(2R,5S)-2-[6-(methanesulfonamido)-3-pyridyl]-5-methyl-1-piperidyl]-2-oxo-acetamide (Compound 998

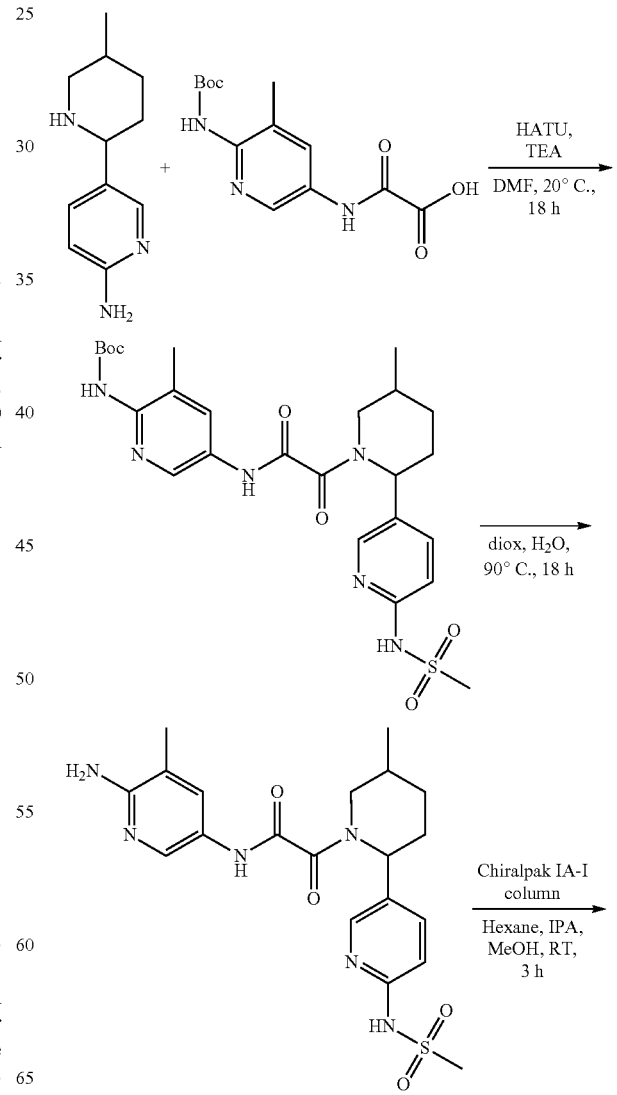

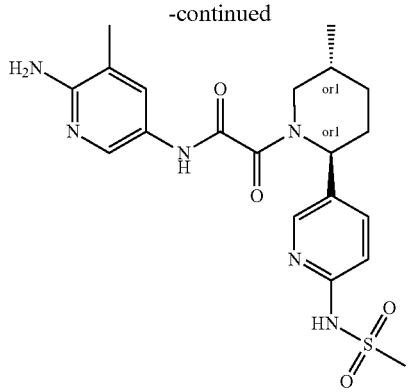

Compound 980

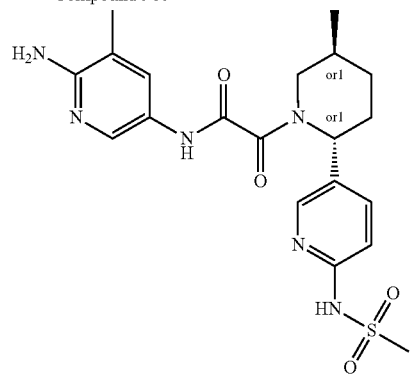

Compound 998

Step 1: The Synthesis of tert-butyl N-[5-[[2-[2-(6-amino-3-pyridyl)-5-methyl-1-piperidyl]-2-oxo-acetyl]amino]-3-methyl-2-pyridyl]carbamate HATU (496.98 mg, 1.31 mmol) was added portionwise at room temperature to a suspension of 2-[[6-(tert-butoxycarbonylamino)-5-methyl-3-pyridyl]amino]-2-oxo-acetic acid (424.55 mg, 1.44 mmol), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give tert-butyl N-[5-[[2-[2-(6-amino-3-pyridyl)-5-methyl-1-piperidyl]-2-oxo-acetyl]amino]-3-methyl-2-pyridyl]carbamate (1 g, crude).

LCMS(ESI): [M+H]$^+$ m/z: calcd 468.2; found 469.2; Rt=0.974 min.

Step 2: The Synthesis of tert-butyl N-[5-[[2-[2-[6-(methanesulfonamido)-3-pyridyl]-5-methyl-1-piperidyl]-2-oxo-acetyl]amino]-3-methyl-2-pyridyl]carbamate Methanesulfonyl chloride (165.07 mg, 1.44 mmol, 111.53 µL) was added dropwise at room temperature to a suspension of tert-butyl N-[5-[[2-[2-(6-amino-3-pyridyl)-5-methyl-1-piperidyl]-2-oxo-acetyl]amino]-3-methyl-2-pyridyl]carbamate (1.33 g, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: YMC Triart C18 100*20 mm, 5 um; 30-75% 0-1-6 min H$_2$O/MeOH, flow: 30 mL/min as mobile phase) to give tert-butyl N-[5-[[2-[2-[6-(methanesulfonamido)-3-pyridyl]-5-methyl-1-piperidyl]-2-oxo-acetyl]amino]-3-methyl-2-pyridyl]carbamate (165 mg, 301.85 µmol, 23.04% yield).

LCMS(ESI): [M+H]$^+$ m/z: calcd 546.2; found 547.2; Rt=1.876 min.

Step 3: The Synthesis of N-(6-amino-5-methyl-3-pyridyl)-2-[2-[6-(methanesulfonamido)-3-pyridyl]-5-methyl-1-piperidyl]-2-oxo-acetamide The solution of tert-butyl N-[5-[[2-[2-[6-(methanesulfonamido)-3-pyridyl]-5-methyl-1-piperidyl]-2-oxo-acetyl]amino]-3-methyl-2-pyridyl]carbamate (165 mg, 301.85 µmol) in dioxane (2 mL) and water (1 mL) was stirred for 18 hr at 90° C. and the solvents were evaporated in vacuo to give N-(6-amino-5-methyl-3-pyridyl)-2-[2-[6-(methanesulfonamido)-3-pyridyl]-5-methyl-1-piperidyl]-2-oxo-acetamide (130 mg, 291.14 µmol, 96.45% yield).

LCMS(ESI): [M+H]$^+$ m/z: calcd 446.2; found 447.0; Rt=0.827 min.

Step 4: The Synthesis of rel-N-(6-amino-5-methyl-3-pyridyl)-2-[(2S,5R)-2-[6-(methanesulfonamido)-3-pyridyl]-5-methyl-1-piperidyl]-2-oxo-acetamide (Compound 980) and Rel-N-(6-amino-5-methyl-3-pyridyl)-2-[(2R,5S)-2-[6-(methanesulfonamido)-3-pyridyl]-5-methyl-1-piperidyl]-2-oxo-acetamide (Compound 998

The enantiomers were separated by chiral HPLC (column: Chiralpak IA-I (250*20 mm, 5 mkm), IPA-MeOH, 50-50, 12 mL/min as mobile phase) to give the two individual enantiomers Compound 980—rel-N-(6-amino-5-methyl-3-pyridyl)-2-[(2S,5R)-2-[6-(methanesulfonamido)-3-pyridyl]-5-methyl-1-piperidyl]-2-oxo-acetamide (31.2 mg, 69.87 µmol, 48.00% yield) RetTime=31.1 min and Compound 998-rel-N-(6-amino-5-methyl-3-pyridyl)-2-[(2R,5S)-2-[6-(methanesulfonamido)-3-pyridyl]-5-methyl-1-piperidyl]-2-oxo-acetamide (31.4 mg, 70.32 µmol, 48.31% yield) RetTime=45.6 min.

Compound 980: RT (IA (250*4.6, 5 mkm), IPA-MeOH, 50-50, 0.6 mL/min)=30.873 min.

LCMS(ESI): [M+H]$^+$ m/z: calcd 446.2; found 447.2; Rt=1.493 min.

Compound 998: RT (IA (250*4.6, 5 mkm), IPA-MeOH, 50-50, 0.6 mL/min)=48.374 min.

LCMS(ESI): [M+H]$^+$ m/z: calcd 446.2; found 447.2; Rt=1.495 min.

Example 320. The Synthesis of rel-2-[(2S,5R)-2-(6-acetamido-3-pyridyl)-5-methyl-1-piperidyl]-N-(6-amino-5-methyl-3-pyridyl)-2-oxo-acetamide (Compound 927) and Rel-2-[(2R,5S)-2-(6-acetamido-3-pyridyl)-5-methyl-1-piperidyl]-N-(6-amino-5-methyl-3-pyridyl)-2-oxo-acetamide (Compound 915

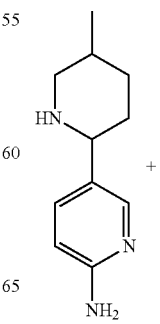

1975

-continued

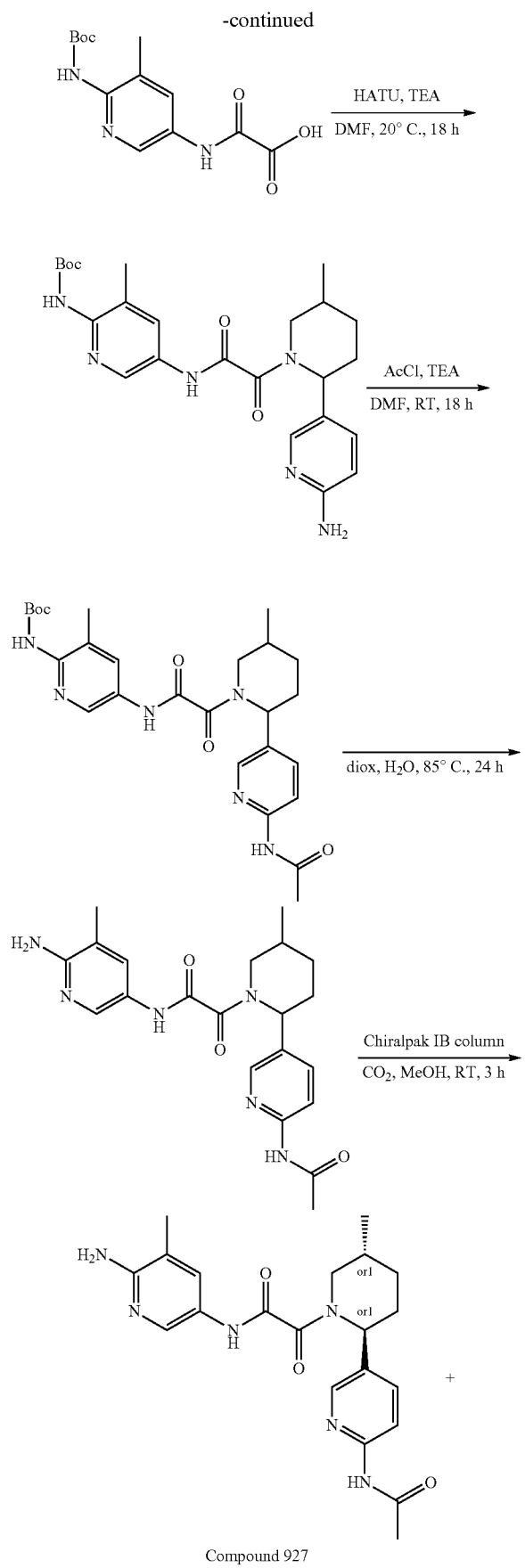

Compound 927

1976

-continued

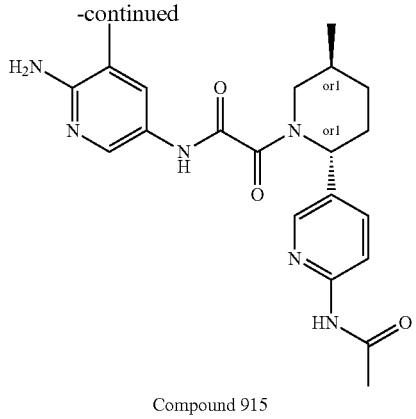

Compound 915

Step 1: The Synthesis of tert-butyl N-[5-[[2-[2-(6-amino-3-pyridyl)-5-methyl-1-piperidyl]-2-oxo-acetyl]amino]-3-methyl-2-pyridyl]carbamate HATU (496.98 mg, 1.31 mmol) was added portionwise at room temperature to a suspension of 2-[[6-(tert-butoxycarbonylamino)-5-methyl-3-pyridyl]amino]-2-oxo-acetic acid (424.55 mg, 1.44 mmol), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give tert-butyl N-[5-[[2-[2-(6-amino-3-pyridyl)-5-methyl-1-piperidyl]-2-oxo-acetyl]amino]-3-methyl-2-pyridyl]carbamate (1 g, crude).

LCMS(ESI): [M+H]$^+$ m/z: calcd 468.2; found 469.2; Rt=0.901 min.

Step 2: The Synthesis of tert-butyl N-[5-[[2-[2-(6-acetamido-3-pyridyl)-5-methyl-1-piperidyl]-2-oxo-acetyl]amino]-3-methyl-2-pyridyl]carbamate Acetyl chloride (113.11 mg, 1.44 mmol, 87.69 µL) was added dropwise at room temperature to a suspension of tert-butyl N-[5-[[2-[2-(6-amino-3-pyridyl)-5-methyl-1-piperidyl]-2-oxo-acetyl]amino]-3-methyl-2-pyridyl]carbamate (1.33 g, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: Chromatorex 18 SMB100-5T 100*19 mm 5 um; 0-1-6 min 30-40% water-MeCN, flow 30 mL/min as mobile phase) to give tert-butyl N-[5-[[2-[2-(6-acetamido-3-pyridyl)-5-methyl-1-piperidyl]-2-oxo-acetyl]amino]-3-methyl-2-pyridyl]carbamate (209 mg, 409.34 µmol, 31.25% yield).

LCMS(ESI): [M+H]$^+$ m/z: calcd 510.2; found 511.2; Rt=2.557 min.

Step 3: The Synthesis of 2-[2-(6-acetamido-3-pyridyl)-5-methyl-1-piperidyl]-N-(6-amino-5-methyl-3-pyridyl)-2-oxo-acetamide The solution of tert-butyl N-[5-[[2-[2-(6-acetamido-3-pyridyl)-5-methyl-1-piperidyl]-2-oxo-acetyl]amino]-3-methyl-2-pyridyl]carbamate (203.41 mg, 398.39 µmol) in dioxane (2 mL) and water (1 mL) was stirred for 24 hr at 85° C. and the solvents were evaporated in vacuo to give 2-[2-(6-acetamido-3-pyridyl)-5-methyl-1-piperidyl]-N-(6-amino-5-methyl-3-pyridyl)-2-oxo-acetamide (160 mg, 389.80 µmol, 97.84% yield).

LCMS(ESI): [M+H]⁺ m/z: calcd 410.2; found 411.2; Rt=0.725 min.

Step 4: The Synthesis of rel-2-[(2S,5R)-2-(6-acetamido-3-pyridyl)-5-methyl-1-piperidyl]-N-(6-amino-5-methyl-3-pyridyl)-2-oxo-acetamide (Compound 927) and Rel-2-[(2R,5S)-2-(6-acetamido-3-pyridyl)-5-methyl-1-piperidyl]-N-(6-amino-5-methyl-3-pyridyl)-2-oxo-acetamide (Compound 915

The enantiomers were separated by chiral HPLC (column: IB (250*30, 5 mkm), $CO_2$-MeOH, 60-40, 80 mL/min make up flow rate—30 mL/min as mobile phase) to give the two individual enantiomers Compound 927-rel-2-[(2S,5R)-2-(6-acetamido-3-pyridyl)-5-methyl-1-piperidyl]-N-(6-amino-5-methyl-3-pyridyl)-2-oxo-acetamide (31.2 mg, 76.01 μmol, 39.00% yield) RetTime=5.99 min and Compound 915—rel-2-[(2R,5S)-2-(6-acetamido-3-pyridyl)-5-methyl-1-piperidyl]-N-(6-amino-5-methyl-3-pyridyl)-2-oxo-acetamide (31.8 mg, 77.47 μmol, 39.75% yield) RetTime=6.76 min.

Compound 927: RT (OJ-H (250*4.6, 5 mkm), Hexane-IPA-MeOH, 50-25-25, 0.6 mL/min)=15.921 min.

¹H NMR (DMSO-$d_6$, 600 MHz): δ (ppm) 0.99 (m, 3H), 1.32 (m, 1H), 1.66 (m, 1H), 1.84 (m, 1H), 2.03 (m, 7H), 2.18 (m, 1H), 2.89 (m, 1H), 3.71 (dd, 1H), 5.58 (m, 3H), 7.45 (m, 1H), 7.69 (m, 1H), 8.00 (m, 2H), 8.22 (m, 1H), 10.48 (s, 2H)

LCMS(ESI): [M+2H]⁺ m/z: calcd 410.2; found 412.2; Rt=0.894 min.

Compound 915: RT (OJ-H (250*4.6, 5 mkm), Hexane-IPA-MeOH, 50-25-25, 0.6 mL/min)=24.255 min.

¹H NMR (DMSO-$d_6$, 600 MHz): δ (ppm) 1.00 (m, 3H), 1.32 (m, 1H), 1.66 (m, 1H), 1.86 (m, 1H), 2.02 (m, 7H), 2.19 (m, 1H), 2.97 (dd, 1H), 3.71 (dd, 1H), 5.58 (m, 3H), 7.45 (m, 1H), 7.70 (m, 1H), 8.00 (m, 2H), 8.22 (m, 1H), 10.48 (s, 2H)

LCMS(ESI): [M+H]⁺ m/z: calcd 410.2; found 412.2; Rt=0.894 min.

Example 321. The Synthesis of rel-N-(6-amino-5-ethyl-3-pyridyl)-2-[(2S,5R)-2-(6-amino-3-pyridyl)-5-methyl-1-piperidyl]-2-oxo-acetamide (Compound 856) and rel-N-(6-amino-5-ethyl-3-pyridyl)-2-[(2R,5S)-2-(6-amino-3-pyridyl)-5-methyl-1-piperidyl]-2-oxo-acetamide (Compound 851

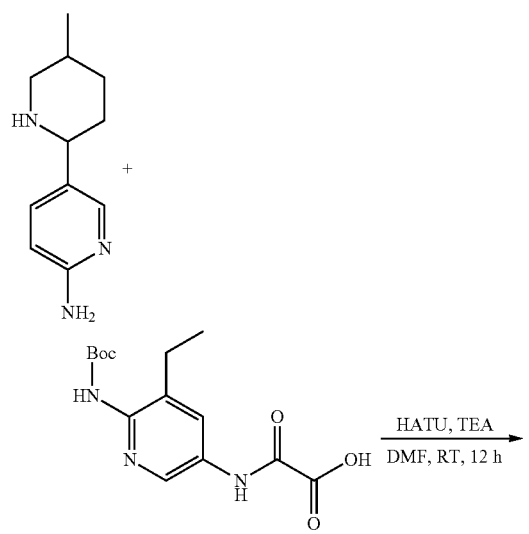

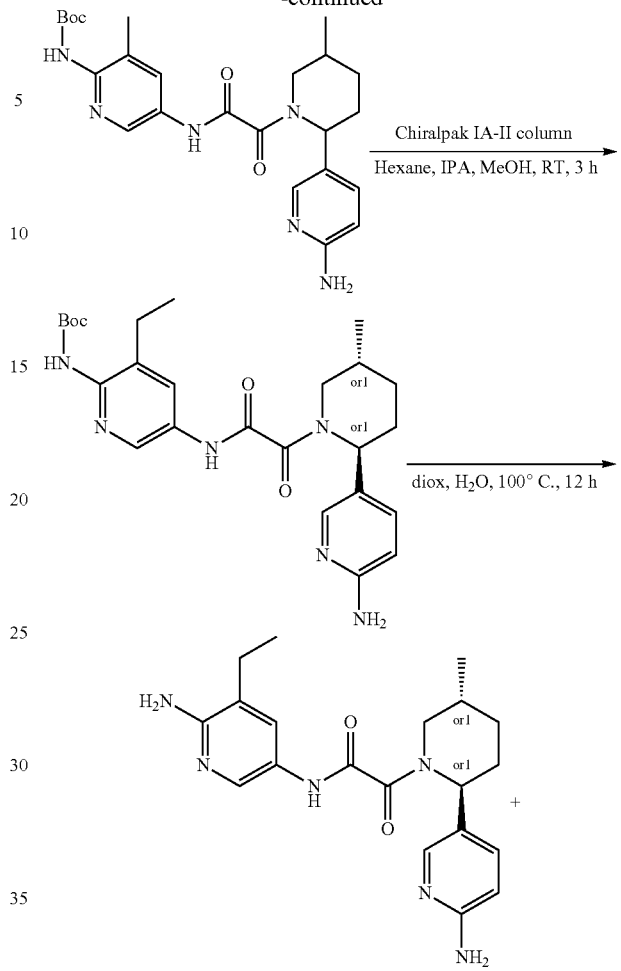

Compound 856

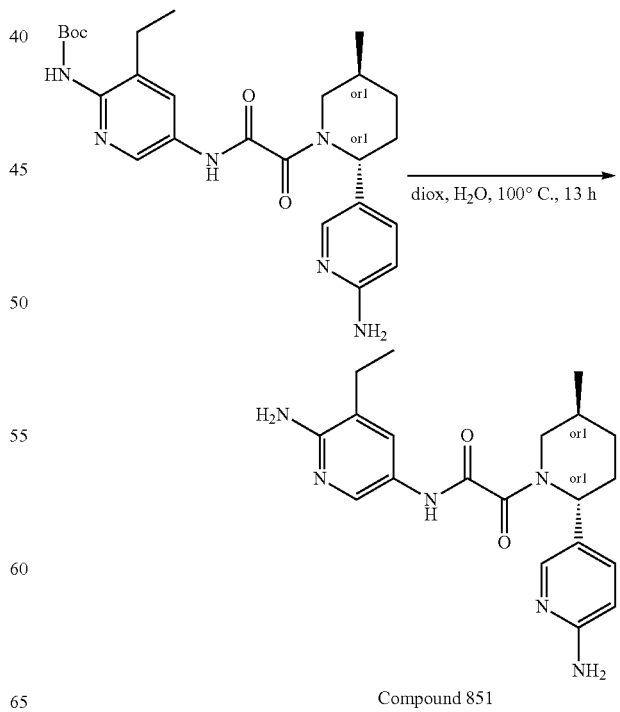

Compound 851

Step 1: The Synthesis of tert-butyl N-[5-[[2-[(2R,5S)-2-(6-amino-3-pyridyl)-5-methyl-1-piperidyl]-2-oxo-acetyl]amino]-3-ethyl-2-pyridyl]carbamate 5-(5-methyl-2-piperidyl)pyridin-2-amine (250 mg, 1.31 mmol), 2-[[6-(tert-butoxycarbonylamino)-5-ethyl-3-pyridyl]amino]-2-oxo-acetic acid (404.29 mg, 1.31 mmol), triethylamine (661.30 mg, 6.54 mmol, 910.88 µL) were mixed in DMF (5 mL) and then HATU (745.46 mg, 1.96 mmol) was added. The resulting mixture was stirred at 25° C. for 12 hr. The solvent was evaporated and resulting mixture was stirred with SiliaMetS® DMT (50 mg) in methanol (10 mL). The mixture was filtered off and evaporated under reduce pressure. The obtained crude material was purified by HPLC (2-10 min 50-65% Methanol/H$_2$O, 30 mL/min) to obtain tert-butyl N-[5-[[2-[(2R,5S)-2-(6-amino-3-pyridyl)-5-methyl-1-piperidyl]-2-oxo-acetyl]amino]-3-ethyl-2-pyridyl]carbamate (61.6 mg, 127.65 µmol, 9.77% yield).

LCMS(ESI): [M+H]$^+$ m/z: calcd 482.2; found 483.2; Rt=0.984 min.

Step 2: The Synthesis of rel-tert-butyl N-[5-[[2-[(2S,5R)-2-(6-amino-3-pyridyl)-5-methyl-1-piperidyl]-2-oxo-acetyl]amino]-3-ethyl-2-pyridyl]carbamate and Rel-tert-butyl N-[5-[[2-[(2R,5S)-2-(6-amino-3-pyridyl)-5-methyl-1-piperidyl]-2-oxo-acetyl]amino]-3-ethyl-2-pyridyl]carbamate The mixture of diastereomers was separated by chiral chromatography (IA-II (250*20.5 mkm), IPA-MeOH, 50-50, 12 mL/min) to obtain tert-butyl N-[5-[[2-[(2S,5R)-2-(6-amino-3-pyridyl)-5-methyl-1-piperidyl]-2-oxo-acetyl]amino]-3-ethyl-2-pyridyl]carbamate (21.02 mg, 43.56 µmol, 34.12% yield; P1) and tert-butyl N-[5-[[2-[(2R,5S)-2-(6-amino-3-pyridyl)-5-methyl-1-piperidyl]-2-oxo-acetyl]amino]-3-ethyl-2-pyridyl]carbamate (22.05 mg, 45.69 µmol, 35.80% yield; P2).

Preparative: RT for P1 (IA (250*30, 5 mkm), IPA-MeOH, 50-50, 20 mL/min)=19.231 min.

Analytical: RT for P1 (IA, IPA-MeOH, 50-50, 0.6 mL/min)=16.786 min. LCMS(ESI): [M+2H]$^+$ m/z: calcd 482.2; found 484.2; Rt=2.159 min.

Preparative: RT for P2 (IA (250*30, 5 mkm), IPA-MeOH, 50-50, 20 mL/min)=42.391 min.

Analytical: RT for P2 (IA, IPA-MeOH, 50-50, 0.6 mL/min)=38.638 min. LCMS(ESI): [M+2H]$^+$ m/z: calcd 482.2; found 484.2; Rt=2.174 min.

Step 3: The Synthesis of rel-N-(6-amino-5-ethyl-3-pyridyl)-2-[(2S,5R)-2-(6-amino-3-pyridyl)-5-methyl-1-piperidyl]-2-oxo-acetamide (Compound 856

A solution of tert-butyl N-[5-[[2-[(2S,5R)-2-(6-amino-3-pyridyl)-5-methyl-1-piperidyl]-2-oxo-acetyl]amino]-3-ethyl-2-pyridyl]carbamate (21.02 mg, 43.56 µmol) in Dioxane (1 mL) and Water (1 mL) was heated at 100° C. for 12 hr. Solvents were evaporated and resulting precipitate was purified by HPLC (2-10 min 20-65% methanol/H$_2$O+NH$_3$ 30 mL/min (loading pump 4 mL methanol+NH$_3$)) to obtain N-(6-amino-5-ethyl-3-pyridyl)-2-[(2S,5R)-2-(6-amino-3-pyridyl)-5-methyl-1-piperidyl]-2-oxo-acetamide (10.8 mg, 28.24 µmol, 64.83% yield).

$^1$H NMR (DMSO-d$_6$, 600 MHz): δ (ppm) 0.95-1.02 (m, 3H), 1.06-1.14 (m, 3H), 1.23-1.37 (m, 1H), 1.64-1.75 (m, 1H), 1.80-2.06 (m, 2H), 2.06-2.15 (m, 1H), 2.36-2.41 (m, 2H), 2.65-3.20 (m, 1H), 3.35-3.99 (m, 1H), 4.95-5.50 (m, 1H), 5.58-5.65 (m, 2H), 5.84 (s, 2H), 6.39-6.47 (m, 1H), 7.19-7.35 (m, 1H), 7.43-7.52 (m, 1H), 7.78-7.88 (m, 1H), 7.98-8.06 (m, 1H), 10.36-10.54 (m, 1H).

LCMS(ESI): [M+H]$^+$ m/z: calcd 382.4; found 383.4; Rt=0.557 min.

Step 4: The Synthesis of rel-N-(6-amino-5-ethyl-3-pyridyl)-2-[(2R,5S)-2-(6-amino-3-pyridyl)-5-methyl-1-piperidyl]-2-oxo-acetamide (Compound 851

A solution of tert-butyl N-[5-[[2-[(2R,5S)-2-(6-amino-3-pyridyl)-5-methyl-1-piperidyl]-2-oxo-acetyl]amino]-3-ethyl-2-pyridyl]carbamate (22.05 mg, 45.69 µmol) in Dioxane (1 mL) and Water (1 mL) was heated at 100° C. for 12 hr. Solvents were evaporated and resulting precipitate was purified by HPLC (2-10 min 20-65% methanol/H$_2$O+NH$_3$ 30 mL/min (loading pump 4 mL methanol+NH$_3$)) to obtain N-(6-amino-5-ethyl-3-pyridyl)-2-[(2R,5S)-2-(6-amino-3-pyridyl)-5-methyl-1-piperidyl]-2-oxo-acetamide (8.2 mg, 21.44 µmol, 46.92% yield).

$^1$H NMR (DMSO-d$_6$, 600 MHz): δ (ppm) 0.97-1.02 (m, 3H), 1.07-1.11 (m, 3H), 1.26-1.34 (m, 1H), 1.61-1.77 (m, 1H), 1.78-1.90 (m, 1H), 1.90-2.05 (m, 1H), 2.06-2.17 (m, 1H), 2.36-2.41 (m, 2H), 2.64-3.21 (m, 1H), 3.35-3.98 (m, 1H), 4.93-5.49 (m, 1H), 5.59-5.65 (m, 2H), 5.85 (s, 2H), 6.40-6.48 (m, 1H), 7.25-7.36 (m, 1H), 7.43-7.51 (m, 1H), 7.81-7.87 (m, 1H), 7.94-8.05 (m, 1H), 10.43-10.51 (m, 1H).

LCMS(ESI): [M+H]$^+$ m/z: calcd 382.4; found 383.4; Rt=0.554 min.

Example 322. The Synthesis of rel-N-(6-amino-5-ethyl-3-pyridyl)-2-[(2S,5R)-2-[6-(methanesulfonamido)-3-pyridyl]-5-methyl-1-piperidyl]-2-oxo-acetamide (Compound 995) and rel-N-(6-amino-5-ethyl-3-pyridyl)-2-[(2R,5S)-2-[6-(methanesulfonamido)-3-pyridyl]-5-methyl-1-piperidyl]-2-oxo-acetamide (Compound 983

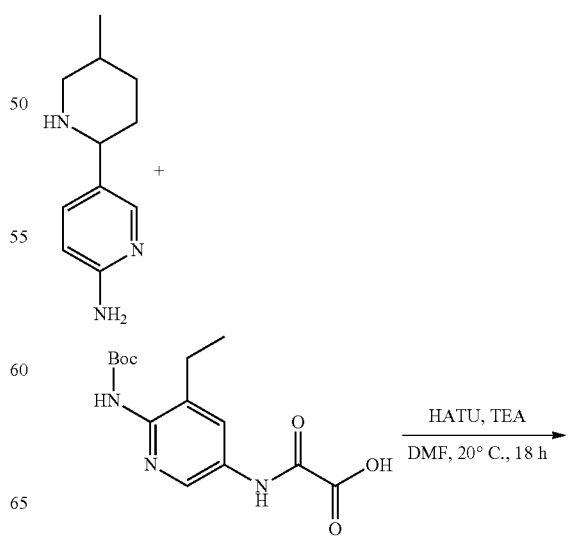

1981

-continued

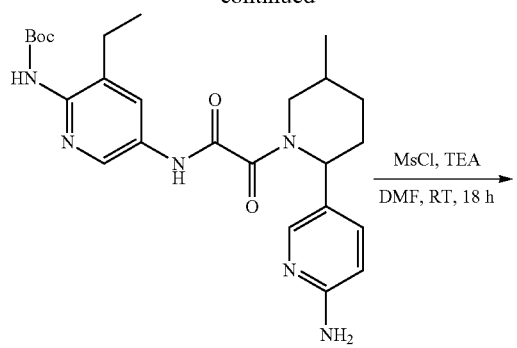

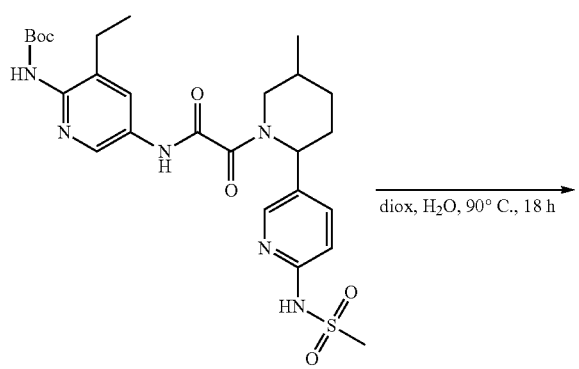

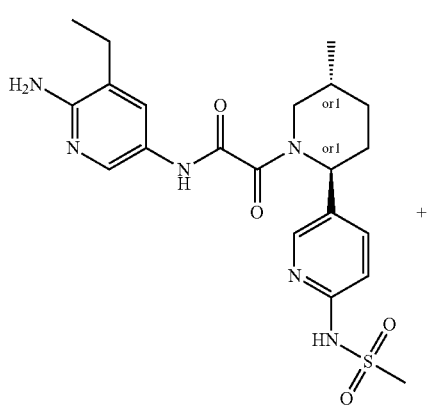

Compound 995

1982

-continued

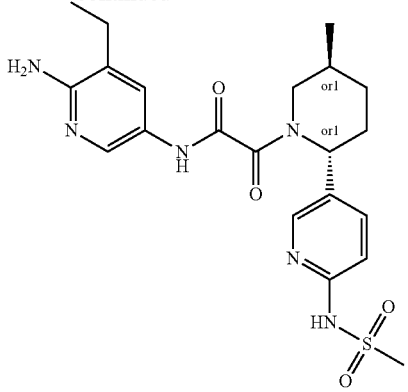

Compound 983

Step 1: The Synthesis of 5-[[2-[2-(6-amino-3-pyridyl)-5-methyl-1-piperidyl]-2-oxo-acetyl]amino]-2-methoxy-pyridine-3-carboxamide HATU (496.98 mg, 1.31 mmol) was added portionwise at room temperature to a suspension of 2-[(5-carbamoyl-6-methoxy-3-pyridyl)amino]-2-oxo-acetic acid (359.52 mg, 1.50 mmol), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give 5-[[2-[2-(6-amino-3-pyridyl)-5-methyl-1-piperidyl]-2-oxo-acetyl]amino]-2-methoxy-pyridine-3-carboxamide (1 g, crude).

LCMS(ESI): [M+H]$^+$ m/z: calcd 482.2; found 483.4; Rt=1.021 min.

Step 2: The Synthesis of tert-butyl N-[3-ethyl-5-[[2-[2-[6-(methanesulfonamido)-3-pyridyl]-5-methyl-1-piperidyl]-2-oxo-acetyl]amino]-2-pyridyl] carbamate Methanesulfonyl chloride (165.07 mg, 1.44 mmol, 111.53 μL) was added dropwise at room temperature to a suspension of tert-butyl N-[5-[[2-[2-(6-amino-3-pyridyl)-5-methyl-1-piperidyl]-2-oxo-acetyl]amino]-3-ethyl-2-pyridyl] carbamate (1.92 g, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: YMC Triart C18 100*20 mm, 5 um; 40-70% 0-1-6 min H$_2$O/MeOH, flow: 30 mL/min as mobile phase) to give tert-butyl N-[3-ethyl-5-[[2-[2-[6-(methanesulfonamido)-3-pyridyl]-5-methyl-1-piperidyl]-2-oxo-acetyl]amino]-2-pyridyl]carbamate (135 mg, 240.79 μmol, 18.38% yield).

LCMS(ESI): [M+H]$^+$ m/z: calcd 560.2; found 561.2; Rt=2.029 min.

Step 3: The Synthesis of N-(6-amino-5-ethyl-3-pyridyl)-2-[2-[6-(methanesulfonamido)-3-pyridyl]-5-methyl-1-piperidyl]-2-oxo-acetamide The solution of tert-butyl N-[3-ethyl-5-[[2-[2-[6-(methanesulfonamido)-3-pyridyl]-5-methyl-1-piperidyl]-2-oxo-acetyl]amino]-2-pyridyl]carbamate (135 mg, 240.79 μmol) in dioxane (2 mL) and water (1 mL) was stirred for 18 hr at 90° C. and the solvents were evaporated in vacuo to give N-(6-amino-5-ethyl-3-pyridyl)-2-[2-[6-(methanesulfonamido)-3-pyridyl]-5-methyl-1-piperidyl]-2-oxo-acetamide (110 mg, 238.85 μmol, 99.19% yield).

LCMS(ESI): [M+H]+ m/z: calcd 460.2; found 461.2; Rt=0.854 min.

Step 4: The Synthesis of rel-N-(6-amino-5-ethyl-3-pyridyl)-2-[(2S,5R)-2-[6-(methanesulfonamido)-3-pyridyl]-5-methyl-1-piperidyl]-2-oxo-acetamide (Compound 995) and Rel-N-(6-amino-5-ethyl-3-pyridyl)-2-[(2R,5S)-2-[6-(methanesulfonamido)-3-pyridyl]-5-methyl-1-piperidyl]-2-oxo-acetamide (Compound 983

The enantiomers were separated by chiral HPLC (column: Chiralpak IA-I (250*20, 5 mkm), IPA-MeOH, 50-50, 12 mL/min as mobile phase) to give the two individual enantiomers Compound 995—rel-N-(6-amino-5-ethyl-3-pyridyl)-2-[(2S,5R)-2-[6-(methanesulfonamido)-3-pyridyl]-5-methyl-1-piperidyl]-2-oxo-acetamide (29.3 mg, 63.62 μmol, 53.27% yield) RetTime=23.87 min and Compound 983—rel-N-(6-amino-5-ethyl-3-pyridyl)-2-[(2R,5S)-2-[6-(methanesulfonamido)-3-pyridyl]-5-methyl-1-piperidyl]-2-oxo-acetamide (33.8 mg, 73.39 μmol, 61.45% yield) RetTime=41.22 min.

Compound 995: RT (IA (250*4.6, 5 mkm), IPA-MeOH, 50-50, 0.6 mL/min)=23.505 min.

LCMS(ESI): [M+H]+ m/z: calcd 460.2; found 461.2; Rt=1.647 min.

Compound 983: RT (IA (250*4.6, 5 mkm), IPA-MeOH, 50-50, 0.6 mL/min)=41.482 min.

LCMS(ESI): [M+H]+ m/z: calcd 460.2; found 461.2; Rt=1.640 min.

Example 323. The Synthesis of rel-2-[(2S,5R)-2-(6-acetamido-3-pyridyl)-5-methyl-1-piperidyl]-N-(6-amino-5-ethyl-3-pyridyl)-2-oxo-acetamide (Compound 921) and Rel-2-[(2R,5S)-2-(6-acetamido-3-pyridyl)-5-methyl-1-piperidyl]-N-(6-amino-5-ethyl-3-pyridyl)-2-oxo-acetamide (Compound 925

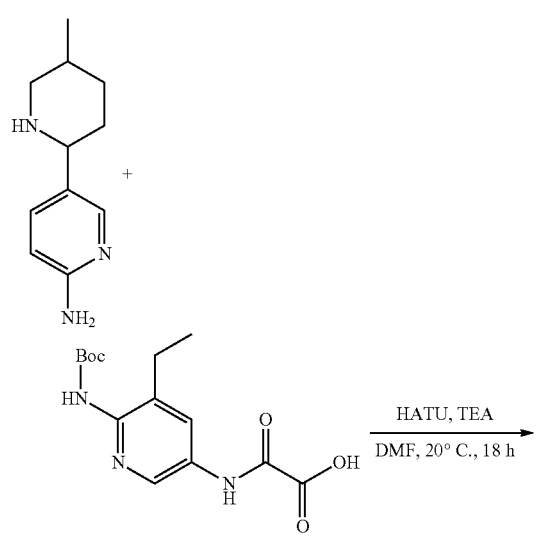

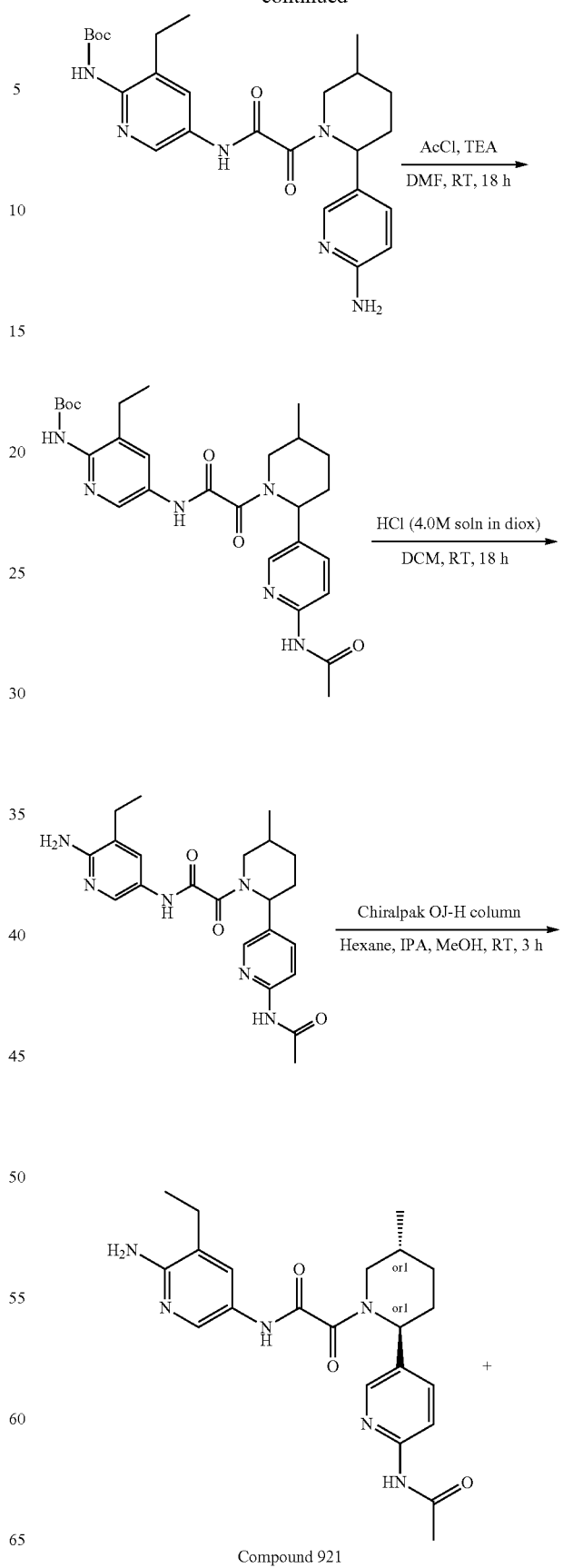

Compound 921

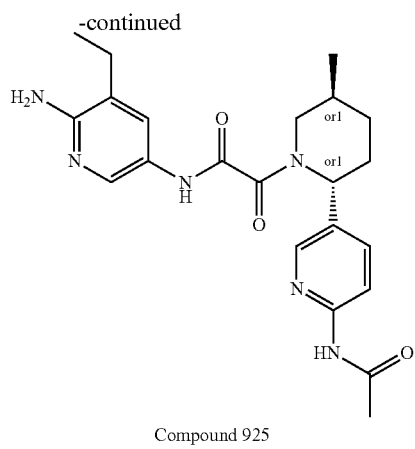

Compound 925

Step 1: The Synthesis of tert-butyl N-[5-[[2-[2-(6-amino-3-pyridyl)-5-methyl-1-piperidyl]-2-oxo-acetyl]amino]-3-ethyl-2-pyridyl]carbamate HATU (496.98 mg, 1.31 mmol) was added portionwise at room temperature to a suspension of 2-[[6-(tert-butoxycarbonylamino)-5-ethyl-3-pyridyl]amino]-2-oxo-acetic acid (444.72 mg, 1.44 mmol), 5-(5-methyl-2-piperidyl)pyridin-2-amine (250 mg, 1.31 mmol) and TEA (793.56 mg, 7.84 mmol, 1.09 mL) in DMF (10 mL). The clear solution was stirred at 20° C. for 18 hr and the solvents were evaporated in vacuo to give tert-butyl N-[5-[[2-[2-(6-amino-3-pyridyl)-5-methyl-1-piperidyl]-2-oxo-acetyl]amino]-3-ethyl-2-pyridyl]carbamate (1 g, crude).

LCMS(ESI): [M+H]+ m/z: calcd 482.2; found 483.2; Rt=0.944 min.

Step 2: The Synthesis of tert-butyl N-[5-[[2-[2-(6-acetamido-3-pyridyl)-5-methyl-1-piperidyl]-2-oxo-acetyl]amino]-3-ethyl-2-pyridyl]carbamate Acetyl chloride (113.11 mg, 1.44 mmol, 87.69 μL) was added dropwise at room temperature to a suspension of tert-butyl N-[5-[[2-[2-(6-amino-3-pyridyl)-5-methyl-1-piperidyl]-2-oxo-acetyl]amino]-3-ethyl-2-pyridyl]carbamate (632.17 mg, 1.31 mmol), TEA (795.35 mg, 7.86 mmol, 1.10 mL) in DMF (10 mL). The solution was stirred at 25° C. for 18 hr and the solvents were evaporated in vacuo. The residue was purified by RP-HPLC (column: YMC Triart C18 100*20 mml.D. S-5 um; 0-5 min 48-65% water-methanol (NH$_3$ 0.1%), flow 30 mL/min as mobile phase) to give tert-butyl N-[5-[[2-[2-(6-acetamido-3-pyridyl)-5-methyl-1-piperidyl]-2-oxo-acetyl]amino]-3-ethyl-2-pyridyl]carbamate (169 mg, 322.14 μmol, 24.59% yield).

LCMS(ESI): [M+H]+ m/z: calcd 524.2; found 525.2; Rt=2.093 min.

Step 3: The Synthesis of 2-[2-(6-acetamido-3-pyridyl)-5-methyl-1-piperidyl]-N-(6-amino-5-ethyl-3-pyridyl)-2-oxo-acetamide Hydrogen chloride solution 4.0 M in dioxane (838.98 mg, 3.22 mmol, 791.49 μL, 14% purity) was carefully added at room temperature to a solution of tert-butyl N-[5-[[2-[2-(6-acetamido-3-pyridyl)-5-methyl-1-piperidyl]-2-oxo-acetyl]amino]-3-ethyl-2-pyridyl]carbamate (169 mg, 322.14 μmol) in DCM (2 mL). The reaction mixture was then stirred for 18 hr at room temperature and the solvents were evaporated in vacuo. The residue was subjected to RP-HPLC (column: YMC Triart C18 100*20 mm, 5 um; 35-60% 0-5 min H$_2$O/MeOH/0.1% NH$_4$OH, flow: 30 mL/min as mobile phase) to give 2-[2-(6-acetamido-3-pyridyl)-5-methyl-1-piperidyl]-N-(6-amino-5-ethyl-3-pyridyl)-2-oxo-acetamide (70.6 mg, 166.32 μmol, 51.63% yield).

LCMS(ESI): [M+H]+ m/z: calcd 424.2; found 425.4; Rt=1.712 min.

Step 4: The Synthesis of rel-2-[(2S,5R)-2-(6-acetamido-3-pyridyl)-5-methyl-1-piperidyl]-N-(6-amino-5-ethyl-3-pyridyl)-2-oxo-acetamide (EN-TG1-4950) and Rel-2-[(2R,5S)-2-(6-acetamido-3-pyridyl)-5-methyl-1-piperidyl]-N-(6-amino-5-ethyl-3-pyridyl)-2-oxo-acetamide (Compound 925)

The enantiomers were separated by chiral HPLC (Column: Chiralcel OJ-H (250*20 mm, 5 mkm); Mobile phase: Hexane-IPA-MeOH, 60-20-20. Flow Rate: 12 mL/min; then another conditions for Compound 921: Column OJ-H (250*20, 5 mkm), Hexane-IPA-MeOH, 70-15-15, 14 mL/min as mobile phase) to give the two individual enantiomers Compound 921—rel-2-[(2S,5R)-2-(6-acetamido-3-pyridyl)-5-methyl-1-piperidyl]-N-(6-amino-5-ethyl-3-pyridyl)-2-oxo-acetamide (24.2 mg, 57.01 μmol, 29.25% yield) RetTime=13.8 min and Compound 925—rel-2-[(2R,5S)-2-(6-acetamido-3-pyridyl)-5-methyl-1-piperidyl]-N-(6-amino-5-ethyl-3-pyridyl)-2-oxo-acetamide (28.5 mg, 67.14 μmol, 34.45% yield) RetTime=22.7 min.

Compound 921: RT (OJ-H (250*4.6, 5 mkm), Hexane-IPA-MeOH, 50-25-25, 0.6 mL/min)=13.066 min.

$^1$H NMR (DMSO-d$_6$, 600 MHz): δ (ppm) 1.04 (m, 6H), 1.34 (m, 1H), 1.68 (m, 1H), 1.88 (m, 1H), 2.06 (m, 4H), 2.19 (m, 1H), 2.39 (m, 2H), 3.05 (m, 1H), 3.62 (m, 1H), 5.60 (m, 3H), 7.45 (m, 1H), 7.69 (dd, 1H), 8.01 (m, 2H), 8.22 (m, 1H), 10.49 (m, 2H).

LCMS(ESI): [M+H]+ m/z: calcd 424.2; found 425.2; Rt=0.909 min.

Compound 925: RT (OJ-H (250*4.6, 5 mkm), Hexane-IPA-MeOH, 50-25-25, 0.6 mL/min)=19.819 min.

$^1$H NMR (DMSO-d$_6$, 600 MHz): δ (ppm) 1.00 (m, 3H), 1.08 (m, 3H), 1.32 (m, 1H), 1.66 (m, 1H), 1.87 (m, 1H), 2.06 (m, 4H), 2.18 (m, 1H), 2.38 (m, 2H), 2.88 (m, 1H), 3.81 (m, 1H), 5.60 (m, 3H), 7.48 (m, 1H), 7.70 (m, 1H), 8.01 (m, 2H), 8.22 (m, 1H), 10.49 (m, 2H).

LCMS(ESI): [M+H]+ m/z: calcd 424.2; found 425.2; Rt=0.906 min.

Example 324. The Synthesis of N-(6-amino-5-methyl-3-pyridyl)-2-[(2S,5R)-2-(Benzothiophen-5-yl)-5-methyl-1-piperidyl]-2-oxo-acetamide (Compound 617) and N-(6-amino-5-methyl-3-pyridyl)-2-[(2R,5S)-2-(Benzothiophen-5-yl)-5-methyl-1-piperidyl]-2-oxo-acetamide (Compound 634

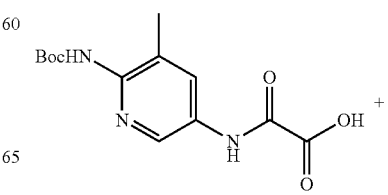

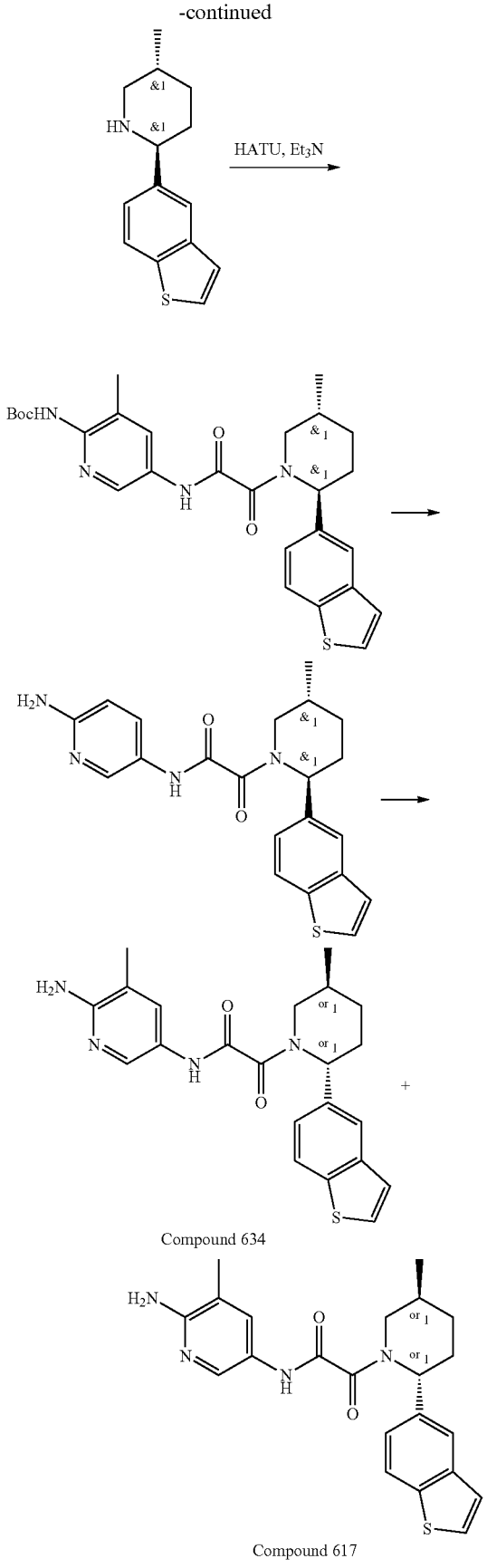

Step 1: Synthesis of tert-butyl N-[5-[[2-[(2S,5R)-2-(benzothiophen-5-yl)-5-methyl-1-piperidyl]-2-oxo-acetyl]amino]-3-methyl-2-pyridyl]carbamate To a solution of (2S,5R)-2-(benzothiophen-5-yl)-5-methyl-piperidine (0.3 g, 1.30 mmol), 2-[[6-(tert-butoxycarbonylamino)-5-methyl-3-pyridyl]amino]-2-oxo-acetic acid (382.91 mg, 1.30 mmol) and Triethylamine (656.07 mg, 6.48 mmol, 903.67 µL), HATU (542.35 mg, 1.43 mmol) was added portionwise. The resulting mixture was stirred at 25° C. for 3 hr, taken up with water (50 ml) and extracted with EtOAc (3*20 ml). The combined organic layer was washed with brine (2*15 ml), dried over $Na_2SO_4$ and the solvent was removed to give tert-butyl N-[5-[[2-[(2S,5R)-2-(benzothiophen-5-yl)-5-methyl-1-piperidyl]-2-oxo-acetyl]amino]-3-methyl-2-pyridyl]carbamate (0.6 g, 1.18 mmol, 90.97% yield). This compound was used for the next step without further purification.

LCMS(ESI): $[M+1]^+$ m/z: calcd 508.2; found 509.2; Rt=1.306 min.

Step 2: Synthesis of N-(6-amino-5-methyl-3-pyridyl)-2-[(2S,5R)-2-(benzothiophen-5-yl)-5-methyl-1-piperidyl]-2-oxo-acetamide A solution of tert-butyl N-[5-[[2-[(2S,5R)-2-(benzothiophen-5-yl)-5-methyl-1-piperidyl]-2-oxo-acetyl]amino]-3-methyl-2-pyridyl]carbamate (0.6 g, 1.18 mmol) in DCM (20 mL) and Hydrogen chloride solution 4.0 M in dioxane (4.00 g, 109.71 mmol, 5 mL) was stirred at 25° C. for 12 hr. The solvent was removed and residue was purified by HPLC: 60-65% 0-5 min 0.10% $NH_3$-methanol, flow: 30 ml/min (loading pump 4 ml/min methanol) target mass 409 column: YMC Triart C18 100×20 mm, 5 um) to obtain N-(6-amino-5-methyl-3-pyridyl)-2-[(2S,5R)-2-(benzothiophen-5-yl)-5-methyl-1-piperidyl]-2-oxo-acetamide (190 mg, 465.10 µmol, 39.43% yield).

LCMS(ESI): $[M+1]^+$ m/z: calcd 408.2; found 409.2; Rt=2.556 min.

Step 3 Synthesis of N-(6-amino-5-methyl-3-pyridyl)-2-[(2S,5R)-2-(benzothiophen-5-yl)-5-methyl-1-piperidyl]-2-oxo-acetamide A solution of tert-butyl N-[5-[[2-[(2S,5R)-2-(benzothiophen-5-yl)-5-methyl-1-piperidyl]-2-oxo-acetyl]amino]-3-methyl-2-pyridyl]carbamate (0.6 g, 1.18 mmol) in DCM (20 mL) and Hydrogen chloride solution 4.0 M in dioxane (4.00 g, 109.71 mmol, 5 mL) was stirred at 25° C. for 12 hr. The solvent was removed and residue was purified by HPLC: 60-65% 0-5 min 0.1% $NH_3$-methanol, flow: 30 ml/min (loading pump 4 ml/min methanol) target mass 409 column: YMC Triart C18 100×20 mm, 5 um) to obtain N-(6-amino-5-methyl-3-pyridyl)-2-[(2S,5R)-2-(benzothiophen-5-yl)-5-methyl-1-piperidyl]-2-oxo-acetamide (190 mg, 465.10 µmol, 39.43% yield).

LCMS(ESI): $[M+1]^+$ m/z: calcd 408.2; found 409.2; Rt=2.556 min.

Step 4: Synthesis of N-(6-amino-5-methyl-3-pyridyl)-2-[(2S,5R)-2-(benzothiophen-5-yl)-5-methyl-1-piperidyl]-2-oxo-acetamide (Compound 617) and N-(6-amino-5-methyl-3-pyridyl)-2-[(2R,5S)-2-(benzothiophen-5-yl)-5-methyl-1-piperidyl]-2-oxo-acetamide (Compound 634

N-(6-amino-5-methyl-3-pyridyl)-2-[(2S,5R)-2-(benzothiophen-5-yl)-5-methyl-1-piperidyl]-2-oxo-acetamide (190 mg, 465.10 µmol) was chirally separated (Injection Volume: 100 mkl; Sample Info: IB (250*20, 5 mkm), Hexane-IPA-MeOH, 70-15-15, 12 ml/min) to obtain N-(6-amino-5-methyl-3-pyridyl)-2-[(2S,5R)-2-(benzothiophen-5-yl)-5-methyl-1-piperidyl]-2-oxo-acetamide (56 mg, 137.08 µmol, 58.95% yield) and N-(6-amino-5-methyl-3-pyridyl)-2-[(2R,5S)-2-(benzothiophen-5-yl)-5-methyl-1-piperidyl]-2-oxo-acetamide (55 mg, 134.63 µmol, 57.89% yield). RetTime (Compound 617)=20.82 min; RetTime (Compound 634)=22.48 min with a cis-impurity less than 5%

Compound 617: $^1$H NMR (600 MHz, DMSO-$d_6$) δ 0.99-1.04 (m, 3H), 1.30-1.40 (m, 1H), 1.69-1.77 (m, 1H), 1.81-1.92 (m, 1H), 1.93-2.03 (m, 3H), 2.04-2.22 (m, 1H), 2.24-2.35 (m, 1H), 2.76-3.27 (m, 1H), 3.37-4.08 (m, 1H), 5.22-5.73 (m, 3H), 7.26-7.38 (m, 1H), 7.39-7.51 (m, 2H), 7.72-7.77 (m, 1H), 7.79-7.87 (m, 1H), 7.92-7.99 (m, 1H), 7.99-8.05 (m, 1H), 10.46-10.56 (m, 1H).

LCMS(ESI): [M+1]$^+$ m/z: calcd 408.2; found 409.2; Rt=2.677 min.

RT(IA, Hexane-IPA-MeOH, 50-25-25, 0.6 ml/min)=33.903 min

Compound 634: $^1$H NMR (600 MHz, DMSO-$d_6$) δ 0.99-1.03 (m, 3H), 1.28-1.41 (m, 1H), 1.66-1.78 (m, 1H), 1.80-1.93 (m, 1H), 1.94-2.04 (m, 3H), 2.05-2.22 (m, 1H), 2.24-2.36 (m, 1H), 2.77-3.28 (m, 1H), 3.31-4.11 (m, 1H), 5.21-5.57 (m, 1H), 5.65 (d, 2H), 7.27-7.38 (m, 1H), 7.39-7.52 (m, 2H), 7.72-7.77 (m, 1H), 7.80-7.88 (m, 1H), 7.93-8.06 (m, 2H), 10.40-10.61 (m, 1H).

LCMS(ESI): [M+1]$^+$ m/z: calcd 408.2; found 409.2; Rt=2.676 min.

RT(IA, Hexane-IPA-MeOH, 50-25-25, 0.6 ml/min)=45.004 min

Example 325. Synthesis of N-(6-amino-5-ethyl-3-pyridyl)-2-[(2S,5R)-2-(1,3-benzothiazol-5-yl)-5-methyl-1-piperidyl]-2-oxo-acetamide (Compound 694) and N-(6-amino-5-ethyl-3-pyridyl)-2-[(2R,5S)-2-(1,3-benzothiazol-5-yl)-5-methyl-1-piperidyl]-2-oxo-acetamide (Compound 701

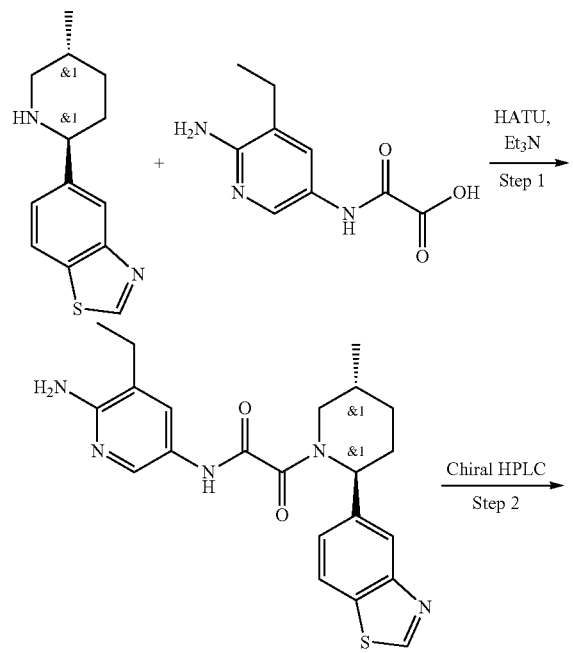

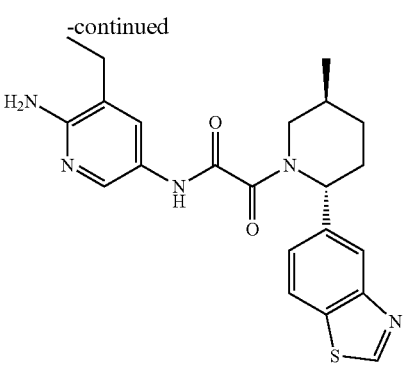

Compound 694

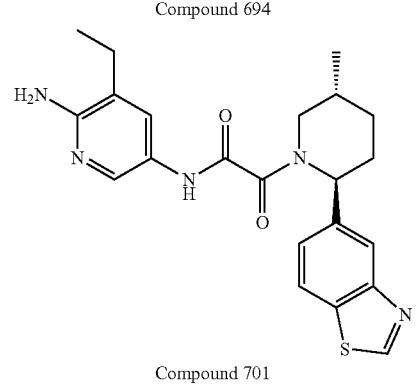

Compound 701

Step 1. Synthesis of N-(6-amino-5-ethyl-3-pyridyl)-2-[2-(1,3-benzothiazol-5-yl)-5-methyl-1-piperidyl]-2-oxo-acetamide (Compound 495)

HATU (392.76 mg, 1.03 mmol) was added portionwise at r.t. to a suspension of 2-[(6-amino-5-ethyl-3-pyridyl)amino]-2-oxo-acetic acid (216.10 mg, 1.03 mmol), 5-(5-methyl-2-piperidyl)-1,3-benzothiazole (240 mg, 1.03 mmol) and TEA (627.15 mg, 6.20 mmol, 863.84 µL) in DMF (10 mL). The clear solution was stirred at 20° C. for 18 hr and the solvents were evaporated in vacuo to give 1 g of crude material. It was subjected to RP-HPLC (column: YMC-Actus Triart C18 100*20 mml.D. S-5 um; 1-6 min 55-60% water-methanol (NH$_3$ 0.1%), flow: 30 ml/min as mobile phase) to give N-(6-amino-5-ethyl-3-pyridyl)-2-[2-(1,3-benzothiazol-5-yl)-5-methyl-1-piperidyl]-2-oxo-acetamide (265 mg, 625.69 µmol, 60.57% yield).

LCMS(ESI): [M+1]$^+$ m/z: calcd 423.2; found 424.2; Rt=2.048 min.

Step 2. Synthesis of N-(6-amino-5-ethyl-3-pyridyl)-2-[(2S,5R)-2-(1,3-benzothiazol-5-yl)-5-methyl-1-piperidyl]-2-oxo-acetamide (Compound 694) and N-(6-amino-5-ethyl-3-pyridyl)-2-[(2R,5S)-2-(1,3-benzothiazol-5-yl)-5-methyl-1-piperidyl]-2-oxo-acetamide (Compound 701

The enantiomers were separated by chiral HPLC (column: OJ-H (250*0.0, 5 mkm), Hexane-IPA-MeOH, 80-10-10, 14 ml/min as mobile phase) to give the two individual enantiomers Compound 701 N-(6-amino-5-ethyl-3-pyridyl)-2-[(2S,5R)-2-(1,3-benzothiazol-5-yl)-5-methyl-1-piperidyl]-2-oxo-acetamide (49 mg, 115.69 µmol, 52.45% yield) RetTime=39.0 min and Compound 694 N-(6-amino-5-ethyl-3-pyridyl)-2-[(2R,5S)-2-(1,3-benzothiazol-5-yl)-5-methyl- 1-piperidyl]-2-oxo-acetamide (40.9 mg, 96.57 μmol, 43.78% yield) RetTime=46.3 min.

Compound 694

$^1$H NMR (DMSO-d$_6$, 600 MHz): δ (ppm) 1.09 (m, 6H), 1.36 (m, 2H), 1.70 (m, 1H), 1.87 (m, 1H), 2.14 (m, 1H), 2.34 (m, 2H), 2.39 (m, 1H), 2.78 (m, 1H), 3.77 (m, 1H), 5.65 (m, 3H), 7.42 (s, 1H), 7.50 (m, 1H), 7.99 (m, 1H), 8.05 (m, 1H), 8.17 (m, 1H), 9.39 (s, 1H), 10.55 (m, 1H)

LCMS(ESI): [M+1]$^+$ m/z: calcd 423.2; found 424.2; Rt=2.048 min.

Compound 701

$^1$H NMR (DMSO-d$_6$, 600 MHz): δ (ppm) 1.09 (m, 6H), 1.36 (m, 2H), 1.70 (m, 1H), 1.87 (m, 1H), 2.14 (m, 1H), 2.34 (m, 2H), 2.39 (m, 1H), 2.78 (m, 1H), 3.77 (m, 1H), 5.65 (m, 3H), 7.42 (s, 1H), 7.50 (m, 1H), 7.99 (m, 1H), 8.05 (m, 1H), 8.17 (m, 1H), 9.39 (s, 1H), 10.55 (m, 1H)

LCMS(ESI): [M+1]$^+$ m/z: calcd 423.2; found 424.2; Rt=2.048 min.

Example 326. The Synthesis of N-(6-amino-5-methylpyridin-3-yl)-2-(5-methyl-2-(2-methylbenzo[d]thiazol-5-yl)piperidin-1-yl)-2-oxoacetamide (Compound 730 and Compound 719

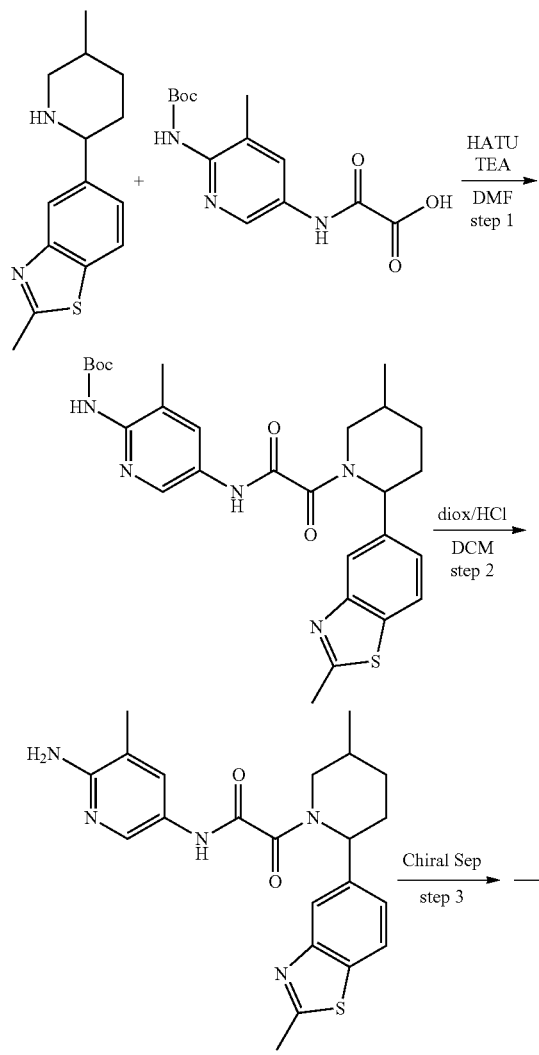

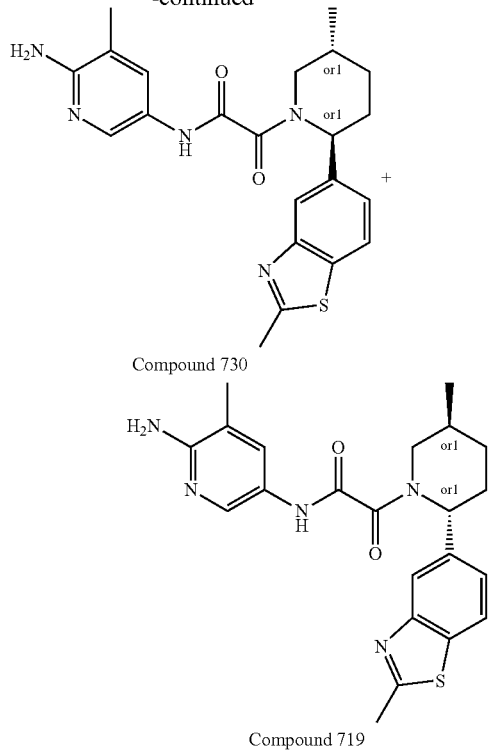

Compound 730

Compound 719

Step 1: Synthesis of tert-butyl (3-methyl-5-(2-(5-methyl-2-(2-methylbenzo[d]thiazol-5-yl)piperidin-1-yl)-2-oxoacetamido)pyridin-2-yl)carbamate HATU (463.00 mg, 1.22 mmol) was added portionwise at rt to a suspension of 2-[[6-(tert-butoxycarbonylamino)-5-methyl-3-pyridyl]amino]-2-oxo-acetic acid (359.57 mg, 1.22 mmol), 2-methyl-5-(5-methyl-2-piperidyl)-1,3-benzothiazole (300 mg, 1.22 mmol) and TEA (739.30 mg, 7.31 mmol, 1.02 mL) in DMF (10 mL). The clear solution was stirred at 25° C. for 18 hr and the solvents were evaporated in vacuo. The residue was dissolved in EtOAc (50 mL), washed with water (3×10 mL) and evaporated in vacuo to give tert-butyl N-[3-methyl-5-[[2-[5-methyl-2-(2-methyl-1,3-benzothiazol-5-yl)-1-piperidyl]-2-oxo-acetyl]amino]-2-pyridyl]carbamate (700 mg, crude).

$^1$H NMR (500 MHz, CDCl$_3$) δ (ppm) 0.96 (m, 1H), 1.09 (d, 3H), 1.22 (m, 1H), 1.48 (s, 9H), 2.02 (m, 2H), 2.27 (m, 4H), 2.78 (s, 3H), 2.84 (m, 1H), 3.86 (m, 1H), 4.12 (m, 1H), 6.25 (m, 1H), 7.80 (m, 4H), 8.09 (m, 1H), 9.61 (m, 1H).

LCMS(ESI): [M]$^+$ m/z: calcd 523.2; found 524.2; Rt=1.396 min.

Step 2: Synthesis of N-(6-amino-5-methylpyridin-3-yl)-2-(5-methyl-2-(2-methylbenzo[d]thiazol-5-yl)piperidin-1-yl)-2-oxoacetamide Hydrogen chloride solution 4.0 M in dioxane (3.48 g, 13.37 mmol, 3.32 mL, 14% purity) was carefully added at rt to a solution of tert-butyl N-[3-methyl-5-[[2-[5-methyl-2-(2-methyl-1,3-benzothiazol-5-yl)-1-piperidyl]-2-oxo-acetyl]amino]-2-pyridyl]carbamate (700 mg, 1.34 mmol) in DCM (10 mL). The reaction mixture was then stirred for 12 hr at rt and the solvents were evaporated in vacuo. The residue was subjected to RP-HPLC (column: YMC Triart C18 100×20 mm, 5 um; 50-50-80% 0-1-6 min 0.1% water—MeOH—0.1% NH₃ as mobile phase) to give N-(6-amino-5-methyl-3-pyridyl)-2-[5-methyl-2-(2-methyl-1,3-benzothiazol-5-yl)-1-piperidyl]-2-oxo-acetamide (178 mg, 420.28 µmol, 31.44% yield).

LCMS(ESI): [M]⁺ m/z: calcd 423.2; found 424.2; Rt=2.323 min.

Step 3: Chiral Separation (Compound 730 and Compound 719

The enantiomers were separated by chiral HPLC (column: IC-II (250*20, 5 mkm), Hexane-MeOH-IPA, 50-25-25, 12 ml/min as mobile phase) to give the two individual enantiomers Compound 730 N-(6-amino-5-methyl-3-pyridyl)-2-[(2S,5R)-5-methyl-2-(2-methyl-1,3-benzothiazol-5-yl)-1-piperidyl]-2-oxo-acetamide (42.5 mg, 100.35 µmol, 47.75% yield) RetTime=32.9 min and Compound 719 N-(6-amino-5-methyl-3-pyridyl)-2-[(2R,5S)-5-methyl-2-(2-methyl-1,3-benzothiazol-5-yl)-1-piperidyl]-2-oxo-acetamide (43.3 mg, 102.24 µmol, 48.65% yield) RetTime=51.1 min.

Ret time for Compound 719 in analytical conditions (column: IC, IPA-MeOH, 50-50, 0.6 ml/min as mobile phase) 22.22 min and for Compound 730 15.44 min.

Compound 719: Retention time: 22.22 min

¹H NMR (600 MHz, DMSO-d₆) δ (ppm) 1.01 (m, 3H), 1.34 (m, 1H), 1.69 (m, 1H), 1.86 (m, 1H), 1.99 (m, 3H), 2.19 (m, 1H), 2.29 (m, 1H), 2.77 (m, 3H), 3.25 (m, 1H), 3.65 (m, 1H), 5.62 (m, 3H), 7.35 (m, 1H), 7.45 (m, 1H), 7.84 (m, 1H), 7.99 (m, 2H), 10.52 (m, 1H).

LCMS(ESI): [M]⁺ m/z: calcd 423.2; found 424.2; Rt=2.399 min.

Compound 730: Retention time: 15.44 min

¹H NMR (600 MHz, DMSO-d₆) δ (ppm) 1.01 (d, 3H), 1.35 (m, 1H), 1.69 (m, 1H), 1.86 (m, 1H), 1.99 (m, 3H), 2.12 (m, 1H), 2.28 (m, 1H), 2.77 (s, 3H), 3.25 (m, 1H), 3.74 (m, 1H), 5.62 (m, 3H), 7.32 (m, 1H), 7.49 (m, 1H), 7.84 (m, 1H), 7.99 (m, 2H), 10.52 (m, 1H).

LCMS(ESI): [M]⁺ m/z: calcd 423.2; found 424.2; Rt=2.422 min.

Example 327. The Synthesis of N-(6-amino-5-methyl-3-pyridyl)-2-[(2S,5R)-5-methyl-2-(1H-pyrazolo[3,4-b]pyridin-5-yl)-1-piperidyl]-2-oxo-acetamide (Compound 549) and N-(6-amino-5-methyl-3-pyridyl)-2-[(2R,5S)-5-methyl-2-(1H-pyrazolo[3,4-b]pyridin-5-yl)-1-piperidyl]-2-oxo-acetamide (Compound 573

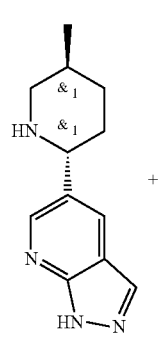

+

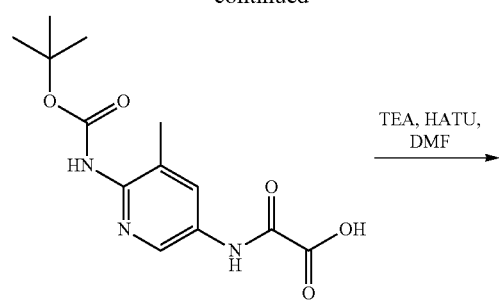

TEA, HATU, DMF →

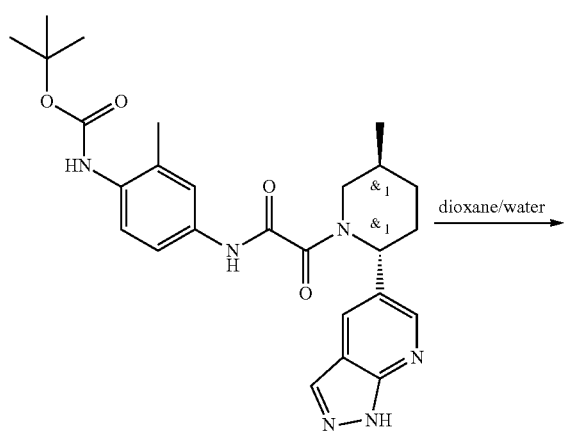

dioxane/water →

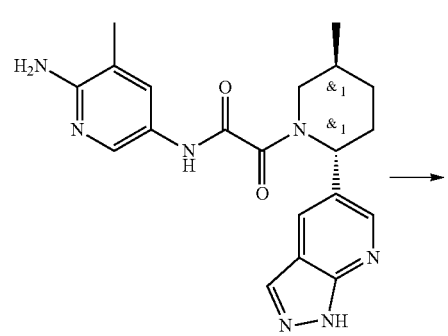

→

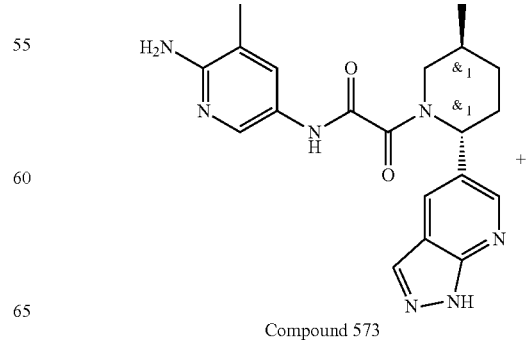

Compound 573

1995

-continued

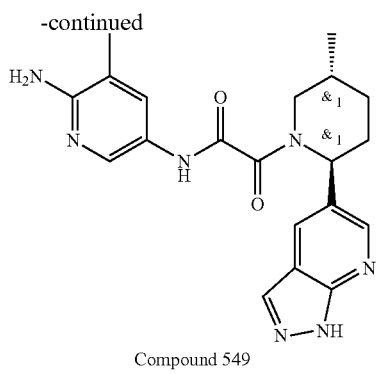

Compound 549

Step 1: Synthesis of tert-butyl N-[3-methyl-5-[[2-[5-methyl-2-(1H-pyrazolo[3,4-b]pyridin-5-yl)-1-piperidyl]-2-oxo-acetyl]amino]-2-pyridyl]carbamate 2-[[6-(tert-butoxycarbonylamino)-5-methyl-3-pyridyl]amino]-2-oxo-acetic acid (1.10 g, 2.77 mmol, C6H15N) and 5-(5-methyl-2-piperidyl)-1H-pyrazolo[3,4-b]pyridine (0.6 g, 2.77 mmol) were mixed in DMF (20 mL). The reaction suspension was cooled to 0° C. and HATU (1.05 g, 2.77 mmol) followed by TEA (842.15 mg, 8.32 mmol, 1.16 mL) were added and stirred at ambient temperature for 15 hr. The reaction mixture was evaporated in vacuo and poured into water (150 ml) and extracted with EtOAc (2×50 ml). The combined organic extracts were washed with water (2*30 ml), dried over sodium sulphate and evaporated in vacuo to afford product tert-butyl N-[3-methyl-5-[[2-[5-methyl-2-(1H-pyrazolo[3,4-b]pyridin-5-yl)-1-piperidyl]-2-oxo-acetyl]amino]-2-pyridyl]carbamate (0.8 g, 1.62 mmol, 58.43% yield)

LCMS(ESI): [M+H]+ m/z: calcd 493.6; found 494.2; Rt=1.194 min.

Step 2: Synthesis of N-(6-amino-5-methyl-3-pyridyl)-2-[5-methyl-2-(1H-pyrazolo[3,4-b]pyridin-5-yl)-1-piperidyl]-2-oxo-acetamide water (20 mL) was added in one portion to a stirred solution of tert-butyl N-[3-methyl-5-[[2-[5-methyl-2-(1H-pyrazolo[3,4-b]pyridin-5-yl)-1-piperidyl]-2-oxo-acetyl]amino]-2-pyridyl]carbamate (0.8 g, 1.62 mmol) in dioxane (10 mL) at room temperature. The resulting mixture was stirred at 90° C. for 48 hr, and then evaporated in vacuo. The residue was diluted with water (20 mL) and extracted with dichloromethane (2*30 mL). The combined organic extracts were dried over sodium sulphate and evaporated in vacuo and obtained crude product 0.5 g was purified by preparative HPLC (10-30% 2-7 min water-acetonitrile+nh3; flow: 30 ml/min) to afford product N-(6-amino-5-methyl-3-pyridyl)-2-[5-methyl-2-(1H-pyrazolo[3,4-b]pyridin-5-yl)-1-piperidyl]-2-oxo-acetamide (0.106 g, 269.42 µmol, 16.62% yield)

$^1$H NMR (600 MHz, DMSO-d$_6$) 0.98-1.06 (m, 3H), 1.30-1.41 (m, 1H), 1.65-1.79 (m, 1H), 1.79-1.93 (m, 1H), 1.95-2.06 (m, 3H), 2.07-2.21 (m, 1H), 2.22-2.34 (m, 1H), 2.79-3.16 (m, 1H), 3.43-4.04 (m, 1H), 5.25-5.77 (m, 3H), 7.38-7.52 (m, 1H), 7.90-8.03 (m, 1H), 8.08-8.20 (m, 2H), 8.44-8.55 (m, 1H), 10.48-10.60 (m, 1H), 13.54-13.68 (m, 1H).

LCMS(ESI): [M+H]+ m/z: calcd 393.2; found 394.2; Rt=1.715 min.

1996

Step 3: The Synthesis of N-(6-amino-5-methyl-3-pyridyl)-2-[(2S,5R)-5-methyl-2-(1H-pyrazolo[3,4-b]pyridin-5-yl)-1-piperidyl]-2-oxo-acetamide (Compound 549) and N-(6-amino-5-methyl-3-pyridyl)-2-[(2R,5S)-5-methyl-2-(1H-pyrazolo[3,4-b]pyridin-5-yl)-1-piperidyl]-2-oxo-acetamide (Compound 573

The enantiomers were separated by chiral HPLC OD-H (250*30, 5 mkm), Hexane-IPA-MeOH, 50-25-2, 25 ml/min as mobile phase) to give the two individual enantiomers Compound 549 N-(6-amino-5-methyl-3-pyridyl)-2-[(2S,5R)-5-methyl-2-(1H-pyrazolo[3,4-b]pyridin-5-yl)-1-piperidyl]-2-oxo-acetamide (33.96 mg, 86.32 µmol, 32.04% yield) and Compound 573 N-(6-amino-5-methyl-3-pyridyl)-2-[(2R,5S)-5-methyl-2-(1H-pyrazolo[3,4-b]pyridin-5-yl)-1-piperidyl]-2-oxo-acetamide (0.03314 g, 84.23 µmol, 31.26% yield)

Compound 549:
$^1$H NMR (600 MHz, DMSO-d$_6$) δ 0.98-1.06 (m, 3H), 1.30-1.41 (m, 1H), 1.65-1.79 (m, 1H), 1.79-1.93 (m, 1H), 1.95-2.06 (m, 3H), 2.07-2.21 (m, 1H), 2.22-2.34 (m, 1H), 2.79-3.16 (m, 1H), 3.43-4.04 (m, 1H), 5.25-5.77 (m, 3H), 7.38-7.52 (m, 1H), 7.90-8.03 (m, 1H), 8.08-8.20 (m, 2H), 8.44-8.55 (m, 1H), 10.48-10.60 (m, 1H), 13.54-13.68 (m, 1H).

LCMS(ESI): [M+H]+ m/z: calcd 393.4; found 416.0; Rt=3.349 min.

RT (Hexane-IPA-MeOH, 50-25-25, 25 ml/min)=30.1052 min.

Compound 573:
$^1$H NMR (600 MHz, DMSO-d$_6$) δ 0.99-1.05 (m, 3H), 1.29-1.42 (m, 1H), 1.71-1.79 (m, 1H), 1.85-1.93 (m, 1H), 1.96-2.06 (m, 3H), 2.08-2.20 (m, 1H), 2.23-2.34 (m, 1H), 2.75-3.27 (m, 1H), 3.44-4.05 (m, 1H), 5.19-5.74 (m, 3H), 7.36-7.53 (m, 1H), 7.89-8.05 (m, 1H), 8.07-8.21 (m, 2H), 8.42-8.55 (m, 1H), 10.47-10.57 (m, 1H), 13.42-13.68 (m, 1H).

LCMS(ESI): [M+H]+ m/z: calcd 393.4; found 394.0; Rt=3.330 min.

RT (Hexane-IPA-MeOH, 50-25-25, 25 ml/min)=13.1472 min.

Example 328. The Synthesis of Rac N-(6-amino-5-methyl-3-pyridyl)-2-[(2S,5R)-5-methyl-2-[4-(1H-pyrazol-5-yl)phenyl]-1-piperidyl]-2-oxo-acetamide (Compound 526), N-(6-amino-5-methyl-3-pyridyl)-2-[(2S,5R)-5-methyl-2-[4-(1H-pyrazol-5-yl)phenyl]-1-piperidyl]-2-oxo-acetamide (Compound 675) and N-(6-amino-5-methyl-3-pyridyl)-2-[(2R,5S)-5-methyl-2-[4-(1H-pyrazol-5-yl)phenyl]-1-piperidyl]-2-oxo-acetamide (Compound 676

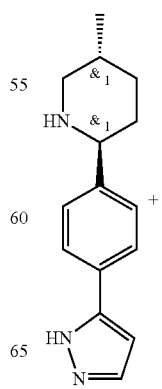

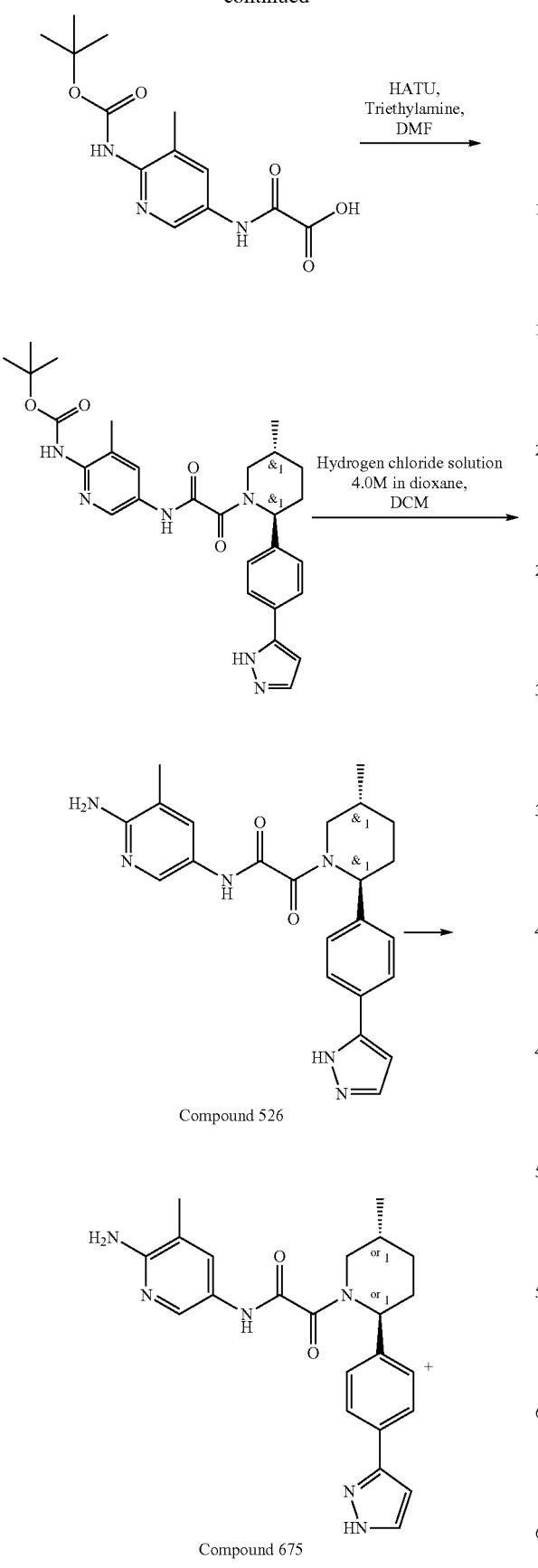

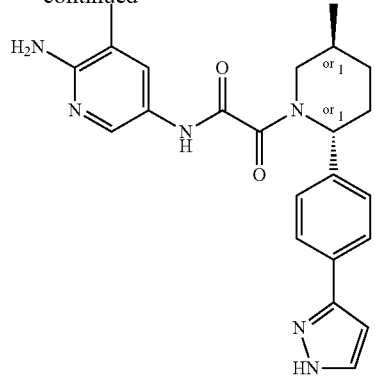

Compound 676

Step 1: Synthesis of tert-butyl N-[3-methyl-5-[[2-[(2S,5R)-5-methyl-2-[4-(1H-pyrazol-5-yl)phenyl]-1-piperidyl]-2-oxo-acetyl]amino]-2-pyridyl]carbamate To a solution of (2S,5R)-5-methyl-2-[4-(1H-pyrazol-5-yl)phenyl]piperidine (125 mg, 397.77 μmol, 2HCl), 2-[[6-(tert-butoxycarbonylamino)-5-methyl-3-pyridyl]amino]-2-oxo-acetic acid (117.46 mg, 397.77 μmol) and Triethylamine (241.50 mg, 2.39 mmol, 332.65 μL), HATU (166.37 mg, 437.55 μmol) was added portionwise. The resulting mixture was stirred at 25° C. for 3 hr, quenched with water (30 ml) and extracted with EtOAc (3*20 ml). The combined organic layer was washed with brine (2*20 ml), dried over Na$_2$SO$_4$ and evaporated in vacuo to obtain tert-butyl N-[3-methyl-5-[[2-[(2S,5R)-5-methyl-2-[4-(1H-pyrazol-5-yl)phenyl]-1-piperidyl]-2-oxo-acetyl]amino]-2-pyridyl]carbamate (0.2 g, 385.65 μmol, 96.95% yield).

This compound was used for the next step without purification.

LCMS(ESI): [M+H]$^+$ m/z: calcd 518.3; found 519.2; Rt=1.190 min.

Step 2: Synthesis of Rac N-(6-amino-5-methyl-3-pyridyl)-2-[(2S,5R)-5-methyl-2-[4-(1H-pyrazol-5-yl)phenyl]-1-piperidyl]-2-oxo-acetamide (Compound 526

To a solution of tert-butyl N-[3-methyl-5-[[2-[(2S,5R)-5-methyl-2-[4-(1H-pyrazol-5-yl)phenyl]-1-piperidyl]-2-oxo-acetyl]amino]-2-pyridyl]carbamate (0.2 g, 385.65 μmol) in DCM (5 mL), Hydrogen chloride solution 4.0 M in dioxane (4.00 g, 109.71 mmol, 5 mL) was added. The resulting mixture was stirred at 25° C. for 12 hr, the solvent was removed and the residue was purified by HPLC: 40-60% 0-5 min 0.1% NH$_3$-methanol, flow: 30 ml/min (loading pump 4 ml/min methanol) target mass 419 column: YMC Triart C18 100×20 mm, 5 um) to give N-(6-amino-5-methyl-3-pyridyl)-2-[(2S,5R)-5-methyl-2-[4-(1H-pyrazol-5-yl)phenyl]-1-piperidyl]-2-oxo-acetamide (40 mg, 95.58 μmol, 24.78% yield).

$^1$H NMR (600 MHz, DMSO-d$_6$) δ 0.98-1.08 (m, 3H), 1.29-1.39 (m, 1H), 1.63-1.74 (m, 1H), 1.80-1.92 (m, 1H), 1.95-2.04 (m, 4H), 2.12-2.29 (m, 1H), 2.72-3.24 (m, 1H), 3.35-4.06 (m, 1H), 5.14-5.58 (m, 1H), 5.58-5.65 (m, 2H), 6.68 (s, 1H), 7.30-7.39 (m, 2H), 7.42-7.51 (m, 1H), 7.66-7.74 (m, 1H), 7.74-7.81 (m, 2H), 7.95-8.05 (m, 1H).

LCMS(ESI): [M+H]$^+$ m/z: calcd 418.2; found 419.2; Rt=1.805 min.

Step 3: Synthesis of N-(6-amino-5-methyl-3-pyridyl)-2-[(2S,5R)-5-methyl-2-[4-(1H-pyrazol-5-yl)phenyl]-1-piperidyl]-2-oxo-acetamide (Compound 675) and N-(6-amino-5-methyl-3-pyridyl)-2-[(2R,5S)-5-methyl-2-[4-(1H-pyrazol-5-yl)phenyl]-1-piperidyl]-2-oxo-acetamide (Compound 676

N-(6-amino-5-methyl-3-pyridyl)-2-[(2S,5R)-5-methyl-2-[4-(1H-pyrazol-5-yl)phenyl]-1-piperidyl]-2-oxo-acetamide (200 mg, 477.91 µmol) was chirally separated (Sample Info: IC-II (250*20, 5 mkm), Hexane-IPA-MeOH, 60-20-20, 12 ml/min) to obtain N-(6-amino-5-methyl-3-pyridyl)-2-[(2S,5R)-5-methyl-2-[4-(1H-pyrazol-5-yl)phenyl]-1-piperidyl]-2-oxo-acetamide (88 mg, 210.28 µmol, 88.00% yield) and N-(6-amino-5-methyl-3-pyridyl)-2-[(2R,5S)-5-methyl-2-[4-(1H-pyrazol-5-yl)phenyl]-1-piperidyl]-2-oxo-acetamide (91 mg, 217.45 µmol, 91.00% yield).

Compound 675:
$^1$H NMR (DMSO-d$_6$, 600 MHz): δ (ppm) 1.02 (m, 3H), 1.35 (m, 1H), 1.69 (m, 1H), 1.88 (m, 1H), 1.99 (m, 4H), 2.21 (m, 1H), 2.98 (m, 1H), 3.75 (m, 1H), 5.59 (m, 3H), 6.68 (m, 1H), 7.43 (m, 3H), 7.78 (m, 3H), 7.99 (m, 1H), 10.50 (m, 1H), 12.84 (m, 1H)

LCMS(ESI): [M+H]$^+$ m/z: calcd 418.2; found 419.2; Rt=1.016 min.

RT (Hexane-IPA-MeOH, 60-20-20, 12 ml/min)=41.6162 min

Compound 676:
$^1$H NMR (DMSO-d$_6$, 600 MHz): δ (ppm) 1.00 (m, 3H), 1.34 (m, 1H), 1.68 (m, 1H), 1.86 (m, 1H), 1.99 (m, 4H), 2.18 (m, 2H), 3.23 (m, 1H), 3.59 (m, 1H), 5.59 (m, 3H), 6.68 (s, 1H), 7.35 (m, 2H), 7.49 (m, 1H), 7.77 (m, 3H), 7.99 (m, 1H), 10.49 (m, 1H)

LCMS(ESI): [M+H]$^+$ m/z: calcd 418.2; found 419.2; Rt=1.011 min.

RT (Hexane-IPA-MeOH, 60-20-20, 12 ml/min)=59.3602 min

Example 329. The Synthesis of Rac N-(6-amino-5-methyl-3-pyridyl)-2-[(2S,5R)-5-methyl-2-[4-(1H-pyrazol-4-yl)phenyl]-1-piperidyl]-2-oxo-acetamide (Compound 525), Rel-2-((2R,5S)-2-(4-(1H-pyrazol-4-yl)phenyl)-5-methylpiperidin-1-yl)-N-(6-amino-5-methylpyridin-3-yl)-2-oxoacetamide (Compound 628) and Rel-2-((2R,5S)-2-(4-(1H-pyrazol-4-yl)phenyl)-5-methylpiperidin-1-yl)-N-(6-amino-5-methylpyridin-3-yl)-2-oxoacetamide (Compound 629

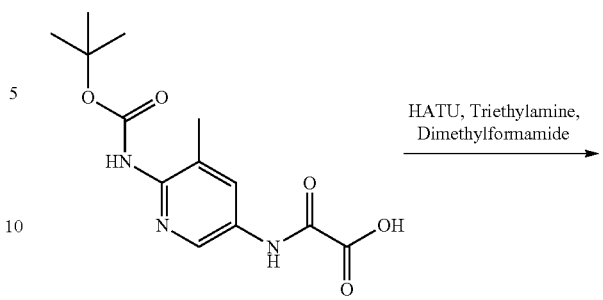

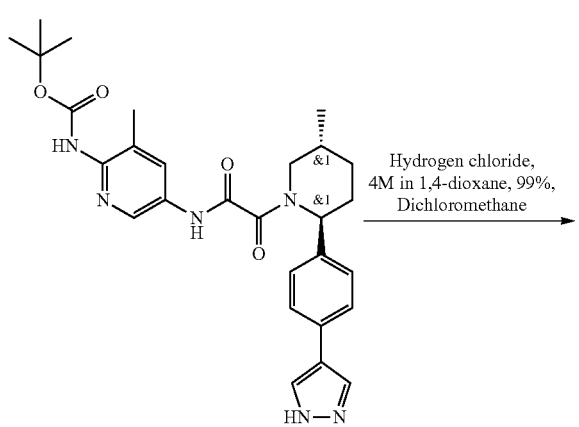

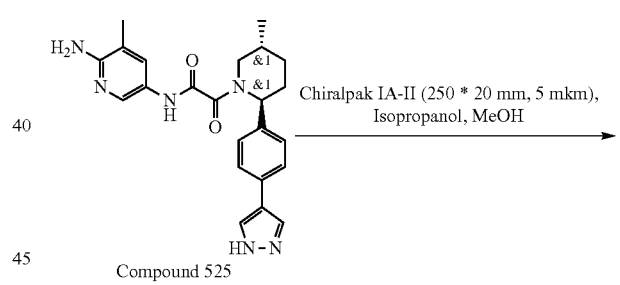

Compound 525

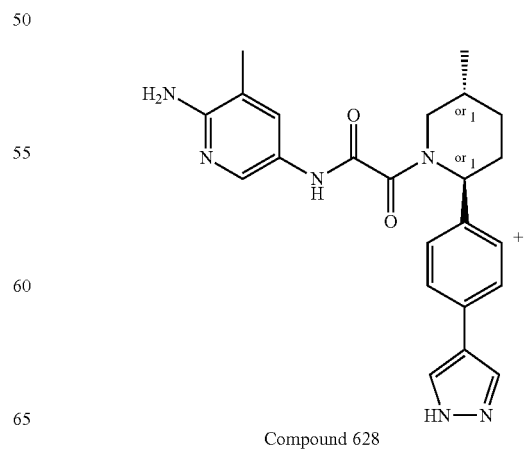

Compound 628

Compound 629

Step 1: Synthesis of tert-butyl N-[3-methyl-5-[[2-[(2S,5R)-5-methyl-2-[4-(1H-pyrazol-4-yl)phenyl]-1-piperidyl]-2-oxo-acetyl]amino]-2-pyridyl]carbamate (2S,5R)-5-methyl-2-[4-(1H-pyrazol-4-yl)phenyl]piperidine (250 mg, 795.54 μmol, 2HCl), 2-[[6-(tert-butoxycarbonylamino)-5-methyl-3-pyridyl]amino]-2-oxo-acetic acid (234.92 mg, 795.54 μmol) and Triethylamine (402.50 mg, 3.98 mmol, 554.41 μL) were mixed together in Dimethylformamide (3 mL). Obtained mixture was briefly heated to 60-70° C. until clear solution was formed. After cooling to 5-10° C., HATU (332.74 mg, 875.09 μmol) was added portionwise during 5 min. Resulting solution was stirred at 20° C. for 4 hr. Then, it was diluted with with water (15 ml) and extracted with ethyl acetate (30 ml). Organic layer was washed with water (2×15 ml) and brine (15 ml), dried over $Na_2SO_4$ and evaporated under reduced pressure, affording tert-butyl N-[3-methyl-5-[[2-[(2S,5R)-5-methyl-2-[4-(1H-pyrazol-4-yl)phenyl]-1-piperidyl]-2-oxo-acetyl]amino]-2-pyridyl]carbamate (330 mg, 636.32 μmol, 79.99% yield).

$^1$H NMR (DMSO-$d_6$, 600 MHz) δ 0.83 (m, 3H), 1.13 (m, 1H), 1.41 (s, 9H), 1.67 (m, 1H), 1.94 (m, 1H), 2.00 (d, 4H), 2.16 (m, 1H), 2.28 (m, 1H), 3.00 (m, 1H), 5.10-5.57 (m, 2H), 7.22-7.33 (m, 2H), 7.26 (m, 1H), 7.48 (m, 2H), 7.60-7.85 (m, 3H), 11.03 (s, 1H).

LCMS(ESI): [M+H]$^+$ m/z: calcd 518.3; found 519.4; Rt=1.171 min.

Step 2: Synthesis of N-(6-amino-5-methyl-3-pyridyl)-2-[(2S,5R)-5-methyl-2-[4-(1H-pyrazol-4-yl)phenyl]-1-piperidyl]-2-oxo-acetamide (Compound 525

Hydrogen chloride, 4M in 1,4-dioxane, 99% (2.32 g, 6.36 mmol, 2.30 mL, 10% purity) was added to a solution of tert-butyl N-[3-methyl-5-[[2-[(2S,5R)-5-methyl-2-[4-(1H-pyrazol-4-yl)phenyl]-1-piperidyl]-2-oxo-acetyl]amino]-2-pyridyl]carbamate (330 mg, 636.32 μmol) in Dichloromethane (10 mL). Resulting mixture was stirred at 20° C. for 18 hr. Then, it was concentrated under reduced pressure and residue was subjected to HPLC(Column: YMC Triart C18 100×20 mm, 5 um; 40-40-80% 0-1-5 min 0.10% $NH_3$-methanol, flow: 30 ml/min), affording N-(6-amino-5-methyl-3-pyridyl)-2-[(2S,5R)-5-methyl-2-[4-(1H-pyrazol-4-yl)phenyl]-1-piperidyl]-2-oxo-acetamide (100 mg, 238.95 μmol, 37.55% yield).

$^1$H NMR (600 MHz, DMSO-$d_6$) δ 0.93-1.05 (m, 3H), 1.27-1.39 (m, 1H), 1.61-1.74 (m, 1H), 1.80-1.93 (m, 1H), 2.00 (d, 4H), 2.11-2.28 (m, 1H), 2.71-3.22 (m, 1H), 3.41-4.04 (m, 1H), 5.05-5.73 (m, 3H), 7.22-7.33 (m, 2H), 7.41-7.54 (m, 1H), 7.54-7.61 (m, 2H), 7.87-8.17 (m, 3H), 10.42-10.64 (m, 1H), 12.89 (s, 1H).

LCMS(ESI): [M+H]$^+$ m/z: calcd 418.2; found 419.2; Rt=1.761 min.

Step 3: The Synthesis of rel-2-((2R,5S)-2-(4-(1H-pyrazol-4-yl)phenyl)-5-methylpiperidin-1-yl)-N-(6-amino-5-methylpyridin-3-yl)-2-oxoacetamide (Compound 628) and Rel-2-((2R,5S)-2-(4-(1H-pyrazol-4-yl)phenyl)-5-methylpiperidin-1-yl)-N-(6-amino-5-methylpyridin-3-yl)-2-oxoacetamide (Compound 629

Chiral separation of Compound 525—rac-2-((2R,5S)-2-(4-(1H-pyrazol-4-yl)phenyl)-5-methylpiperidin-1-yl)-N-(6-amino-5-methylpyridin-3-yl)-2-oxoacetamide (103 mg, 246.12 μmol) was performed using Chiralpak IA-II (250*20 mm, 5 mkm) column; IPA-MeOH, 50-50 as a mobile phase; Flow Rate: 10 mL/min; Column Temperature: 22'C; Wavelength: 254 nm affording Compound 628—rel-2-((2R,5S)-2-(4-(1H-pyrazol-4-yl)phenyl)-5-methylpiperidin-1-yl)-N-(6-amino-5-methylpyridin-3-yl)-2-oxoacetamide (41.65 mg, 99.52 μmol, 40.44% yield)RetTime (enantiomer A)=22.41 min) and Compound 629—rel-2-((2R,5S)-2-(4-(1H-pyrazol-4-yl)phenyl)-5-methylpiperidin-1-yl)-N-(6-amino-5-methylpyridin-3-yl)-2-oxoacetamide (38.47 mg, 91.93 μmol, 37.35% yield)RetTime (enantiomer B)=35.83 min).

Compound 628: $^1$H NMR (600 MHz, DMSO-$d_6$) δ 0.96-1.03 (m, 3H), 1.28-1.37 (m, 1H), 1.63-1.73 (m, 1H), 1.80-1.92 (m, 1H), 1.97-2.03 (m, 3H), 2.03-2.16 (m, 1H), 2.18-2.28 (m, 1H), 2.70-3.22 (m, 1H), 3.40-4.04 (m, 1H), 5.09-5.66 (m, 3H), 7.22-7.33 (m, 2H), 7.42-7.51 (m, 1H), 7.56-7.63 (m, 2H), 7.86-7.94 (m, 1H), 7.95-8.20 (m, 2H), 10.40-10.61 (m, 1H), 12.90 (s, 1H).

LCMS(ESI): [M+H]$^+$ m/z: calcd 418.2; found 419.2; Rt=1.998 min.

RT (IPA-MeOH, 50-50, 10 ml/min)=21.379 min

Compound 629: $^1$H NMR (600 MHz, DMSO-$d_6$) δ 0.98-1.03 (m, 3H), 1.28-1.40 (m, 1H), 1.62-1.74 (m, 1H), 1.80-1.91 (m, 1H), 1.97-2.03 (m, 3H), 2.02-2.16 (m, 1H), 2.17-2.28 (m, 1H), 2.73-3.21 (m, 1H), 3.40-4.04 (m, 1H), 5.08-5.66 (m, 3H), 7.23-7.33 (m, 2H), 7.42-7.50 (m, 1H), 7.56-7.65 (m, 2H), 7.82-7.97 (m, 1H), 7.97-8.05 (m, 1H), 8.05-8.22 (m, 1H), 10.45-10.61 (m, 1H), 12.90 (s, 1H).

LCMS(ESI): [M+H]$^+$ m/z: calcd 418.2; found 419.2; Rt=1.990 min.

RT (IPA-MeOH, 50-50, 10 ml/min)=33.245 min.

Example 330. The Synthesis of N-(6-amino-5-methylpyridin-3-yl)-2-(2-(3-hydroxy-4-methylphenyl)-5-methylpiperidin-1-yl)-2-oxoacetamide (Compound 580

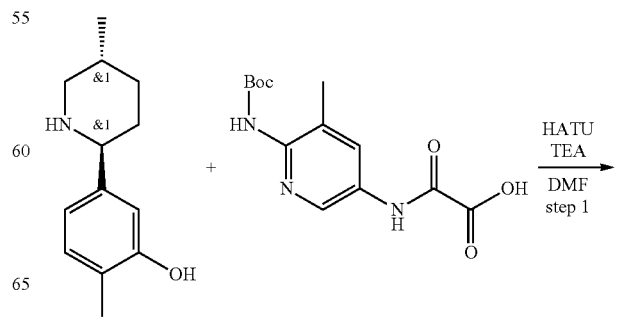

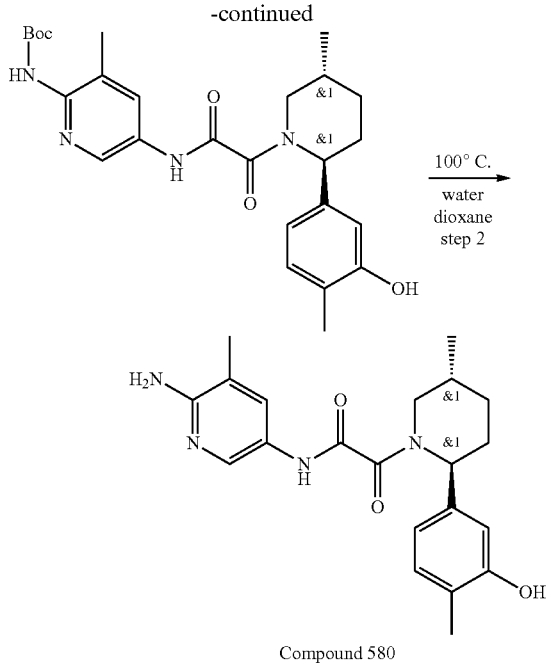

Compound 580

Step 1: Synthesis of rac-tert-butyl (5-(2-((2R,5S)-2-(3-hydroxy-4-methylphenyl)-5-methylpiperidin-1-yl)-2-oxoacetamido)-3-methylpyridin-2-yl)carbamate To the solution of 2-methyl-5-[(2S,5R)-5-methyl-2-piperidyl]phenol (0.25 g, 1.03 mmol, HCl), 2-[[6-(tert-butoxycarbonylamino)-5-methyl-3-pyridyl]amino]-2-oxo-acetic acid (241.67 mg, 818.42 μmol) and TEA (732.48 mg, 7.24 mmol, 1.01 mL) in DMF (5 mL) HATU (432.52 mg, 1.14 mmol) was added portion wise. Mixture was stirred at 25° C. for 2 hr. The reaction mixture was submitted for HPLC (0-1-6 min 45-45-90% water-MeOH (NH$_3$ 0.1%), flow 30 ml/min; column: YMC-Actus Triart C18 100*20 mml) to give tert-butyl N-[5-[[2-[(2S,5R)-2-(3-hydroxy-4-methylphenyl)-5-methyl-1-piperidyl]-2-oxo-acetyl]amino]-3-methyl-2-pyridyl]carbamate (69 mg, 142.98 μmol, 13.83% yield).

$^1$H NMR (500 MHz, DMSO-d$_6$) δ (ppm) 1.03 (d, 3H), 1.40 (m, 1H), 1.42 (s, 9H), 1.92 (m, 3H), 2.08 (m, 4H), 2.17 (s, 3H), 5.25 (m, 1H), 6.62 (m, 1H), 6.67 (m, 1H), 7.05 (m, 1H), 7.91 (m, 1H), 8.44 (m, 1H), 9.05 (m, 1H), 9.27 (m, 1H), 11.01 (m, 1H).

LCMS(ESI): [M]$^+$ m/z: calcd 482.4; found 483.2; Rt=3.265 min.

Step 2: Synthesis of N-(6-amino-5-methylpyridin-3-yl)-2-(2-(3-hydroxy-4-methylphenyl)-5-methylpiperidin-1-yl)-2-oxoacetamide (Compound 580 tert-butyl N-[5-[[2-[(2S,5R)-2-(3-hydroxy-4-methyl-phenyl)-5-methyl-1-piperidyl]-2-oxo-acetyl]amino]-3-methyl-2-pyridyl]carbamate (69 mg, 142.98 μmol) was dissolved in dioxane (1 mL) and water (1.5 mL) and stirred at 95° C. for 14 hr. Solvent were evaporated. The residue was purified by reverse phase HPLC (40-90% 0-9.5 min water-MeOH (NH$_3$ 0.1%)) to give N-(6-amino-5-methyl-3-pyridyl)-2-[(2S,5R)-2-(3-hydroxy-4-methyl-phenyl)-5-methyl-1-piperidyl]-2-oxo-acetamide (29 mg, 75.83 μmol, 53.03% yield). Product contains 6% of cis-isomer.

$^1$H NMR (600 MHz, DMSO-d$_6$) δ (ppm) 0.95-1.02 (m, 3H), 1.25-1.35 (m, 1H), 1.64-1.73 (m, 1H), 1.79-1.88 (m, 1H), 1.97-2.02 (m, 3H), 2.03-2.10 (m, 5H), 2.74-3.22 (m, 1H), 3.39-4.02 (m, 1H), 5.00-5.53 (m, 1H), 5.55-5.62 (m, 2H), 6.59-6.67 (m, 1H), 6.69-6.77 (m, 1H), 7.00-7.05 (m, 1H), 7.41-7.49 (m, 1H), 7.95-8.02 (m, 1H), 9.21 (br. s, 1H), 10.44 (br. s, 1H).

LCMS(ESI): [M]$^+$ m/z: calcd 382.4; found 383.2; Rt=2.173 min.

Example 331. The Synthesis of rac-N-(6-amino-5-methyl-3-pyridyl)-2-[(2S,5R)-2-(1H-indazol-4-yl)-5-methyl-1-piperidyl]-2-oxo-acetamide (Compound 690), N-(6-amino-5-methyl-3-pyridyl)-2-[(2S,5R)-2-(2H-indazol-4-yl)-5-methyl-1-piperidyl]-2-oxo-acetamide (Compound 785) and N-(6-amino-5-methyl-3-pyridyl)-2-[(2R,5S)-2-(2H-indazol-4-yl)-5-methyl-1-piperidyl]-2-oxo-acetamide (Compound 790

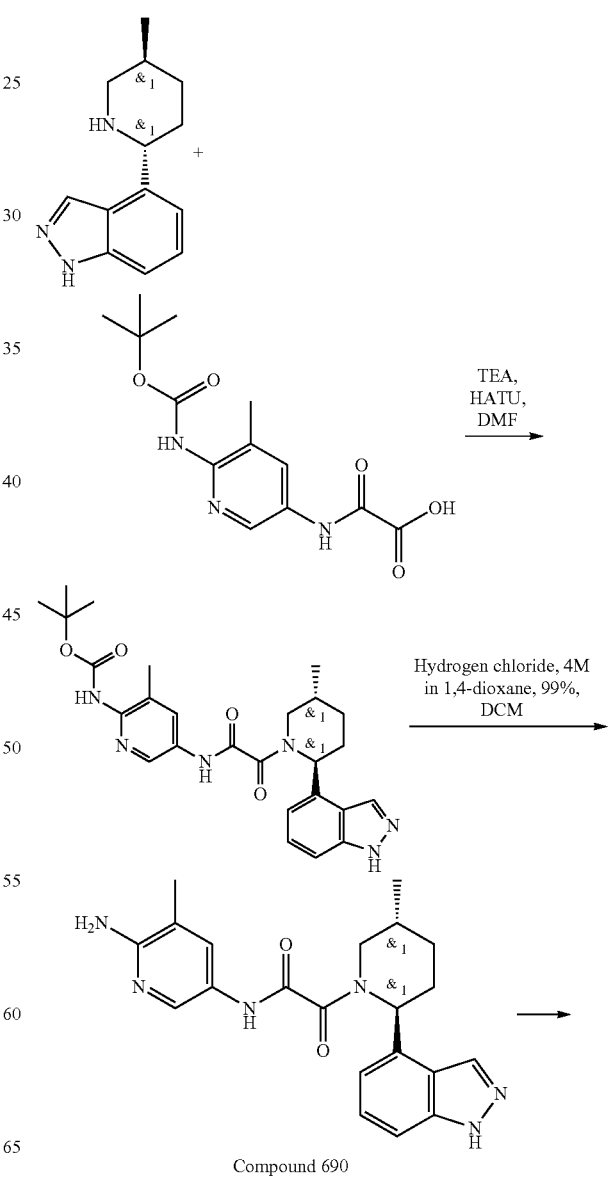

Compound 690

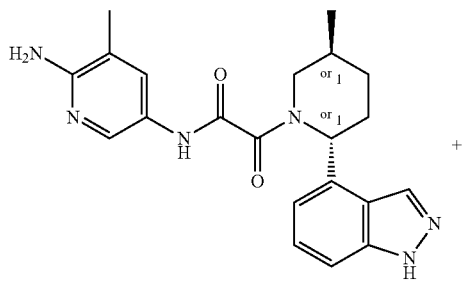

Compound 785

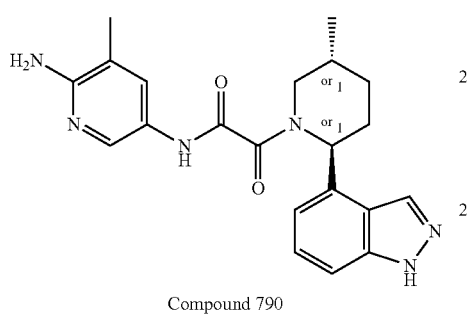

Compound 790

Step 1: Synthesis of tert-butyl N-[5-[[2-[(2S,5R)-2-(H-indazol-4-yl)-5-methyl-1-piperidyl]-2-oxo-acetyl]amino]-3-methyl-2-pyridyl]carbamate To the solution of 4-[(2S,5R)-5-methyl-2-piperidyl]-1H-indazole (360 mg, 1.43 mmol, HCl), 2-[[6-(tert-butoxycarbonylamino)-5-methyl-3-pyridyl]amino]-2-oxo-acetic acid (422.25 mg, 1.43 mmol) and Triethylamine (1.01 g, 10.01 mmol, 1.40 mL) in DMF (3 mL) HATU (598.09 mg, 1.57 mmol) was added portionwise. Mixture was stirred at 25° C. for 2 hr. The reaction mixture was diluted with water (50 ml) and product was extracted with EtOAc (3*25 ml). Combined organic layer were washed with water, brine and dried over Na$_2$SO$_4$. Solvent was evaporated to give tert-butyl N-[5-[[2-[(2S,5R)-2-(1H-indazol-4-yl)-5-methyl-1-piperidyl]-2-oxo-acetyl]amino]-3-methyl-2-pyridyl]carbamate (320 mg, 649.66 μmol, 45.43% yield).

$^1$H NMR (DMSO-d$_6$, 400 MHz): δ (ppm) 1.11 (m, 3H), 1.40 (s, 9H), 1.95 (m, 4H), 2.16 (s, 3H), 2.21 (m, 2H), 2.65 (m, 2H), 2.85 (m, 2H), 7.05 (m, 1H), 7.44 (d, 2H), 7.91 (s, 1H), 8.12 (s, 1H), 8.43 (s, 1H), 11.07 (m, 1H).

LCMS(ESI): [M-Boc+H]$^+$ m/z: calcd 492.3; found 392.2; Rt=1.278 min.

Step 2: Synthesis of N-(6-amino-5-methyl-3-pyridyl)-2-[(2S,5R)-2-(1H-indazol-4-yl)-5-methyl-1-piperidyl]-2-oxo-acetamide (Compound 690

To the stirred solution of tert-butyl N-[5-[[2-[(2S,5R)-2-(1H-indazol-4-yl)-5-methyl-1-piperidyl]-2-oxo-acetyl]amino]-3-methyl-2-pyridyl]carbamate (320 mg, 649.66 μmol) in DCM (10 mL) Hydrogen chloride, 4M in 1,4-dioxane, 99% (236.87 mg, 6.50 mmol, 296.09 μL) was added. The reaction mixture was stirred at 25° C. for 2 hr. Solvents were evaporated in vacuo to give crude product (220 mg) which was purified by reverse phase HPLC (0-5 min 20-70% water-methanol (NH$_3$ 0.1%), flow 30 ml/min (loading pump 4 ml/min methanol (NH$_3$ 0.1%)), target mass 392.46 column: YMC-Actus Triart C18 100*20 mml.D. S-5 um) to give N-(6-amino-5-methyl-3-pyridyl)-2-[(2S,5R)-2-(1H-indazol-4-yl)-5-methyl-1-piperidyl]-2-oxo-acetamide (42 mg, 107.02 μmol, 16.47% yield) in 2 fractions:

1st: 42 mg (100% LCMS)

2nd: 78 mg (89% of trans-isomer; 9.5% of cis-isomer)

$^1$H NMR (DMSO-d$_6$, 600 MHz): δ (ppm) 1.01 (m, 3H), 1.32 (m, 1H), 1.90 (m, 3H), 2.02 (s, 3H), 2.21 (m, 2H), 3.54 (m, 1H), 5.74 (m, 3H), 7.05 (m, 1H), 7.31 (t, 1H), 7.44 (d, 1H), 7.49 (s, 1H), 8.03 (s, 1H), 8.13 (s, 1H), 10.45 (m, 1H), 13.10 (s, 1H)

LCMS(ESI): [M+H]$^+$ m/z: calcd 392.2; found 393.2; Rt=1.626 min.

Step 3: Synthesis of N-(6-amino-5-methyl-3-pyridyl)-2-[(2S,5R)-2-(2H-indazol-4-yl)-5-methyl-1-piperidyl]-2-oxo-acetamide (Compound 785) and N-(6-amino-5-methyl-3-pyridyl)-2-[(2R,5S)-2-(2H-indazol-4-yl)-5-methyl-1-piperidyl]-2-oxo-acetamide (Compound 790

N-(6-amino-5-methyl-3-pyridyl)-2-[(2S,5R)-2-(2H-indazol-4-yl)-5-methyl-1-piperidyl]-2-oxo-acetamide (82.0 mg, 208.94 μmol) was chirally separated using IA-II (250*20.5 mkm) column, Hexane-IPA-MeOH, 40-30-30 as a mobile phase; Flow 12 ml/min; 24° C., Wavelength: 205 nm, 210 nm affording Compound 785—N-(6-amino-5-methyl-3-pyridyl)-2-[(2S,5R)-2-(2H-indazol-4-yl)-5-methyl-1-piperidyl]-2-oxo-acetamide (49.32 mg, 125.67 μmol, 60.15% yield) (RT=65.675 min) as an yellow solid and Compound 790—N-(6-amino-5-methyl-3-pyridyl)-2-[(2R,5S)-2-(2H-indazol-4-yl)-5-methyl-1-piperidyl]-2-oxo-acetamide (31.2 mg, 79.50 μmol, 38.05% yield) (RT=46.697 min) as an yellow solid.

Compound 785: $^1$H NMR (600 MHz, DMSO-d$_6$) δ 0.99-1.03 (m, 3H), 1.28-1.34 (m, 1H), 1.74-1.86 (m, 1H), 1.86-1.92 (m, 1H), 1.93-2.04 (m, 3H), 2.13-2.33 (m, 2H), 3.31-3.37 (m, 1H), 3.54-4.09 (m, 1H), 5.54-5.93 (m, 3H), 7.00-7.08 (m, 1H), 7.29-7.33 (m, 1H), 7.39-7.45 (m, 1H), 7.50 (s, 1H), 7.82-8.03 (m, 1H), 8.03-8.17 (m, 1H), 10.33-10.58 (m, 1H), 13.11 (s, 1H).

LCMS(ESI): [M+H]$^+$ m/z: calcd 392.2; found 393.2; Rt=1.777 min.

RT (Hexane-IPA-MeOH, 40-30-30, 12 ml/min)=34.8612 min.

Compound 790: $^1$H NMR (600 MHz, DMSO-d$_6$) δ 0.99-1.03 (m, 3H), 1.27-1.37 (m, 1H), 1.73-1.86 (m, 1H), 1.86-1.92 (m, 1H), 1.93-2.05 (m, 3H), 2.12-2.32 (m, 2H), 2.94-3.01 (m, 0.2H), 3.32-3.36 (m, 0.8H), 3.51-4.12 (m, 1H), 5.53-5.91 (m, 3H), 6.98-7.08 (m, 1H), 7.26-7.32 (m, 1H), 7.32-7.44 (m, 1H), 7.44-7.52 (m, 1H), 7.84-8.03 (m, 1H), 8.03-8.15 (m, 1H), 10.36-10.59 (m, 1H), 13.10 (s, 1H).

LCMS(ESI): [M+H]$^+$ m/z: calcd 392.3; found 393.2; Rt=1.771 min.

RT (Hexane-IPA-MeOH, 40-30-30, 12 ml/min)=25.8692 min.

Example 332. The Synthesis of N-(6-amino-5-ethyl-3-pyridyl)-2-[(2S,5R)-2-(1H-indazol-4-yl)-5-methyl-1-piperidyl]-2-oxo-acetamide (Compound 911) and N-(6-amino-5-ethyl-3-pyridyl)-2-[(2R,5S)-2-(1H-indazol-4-yl)-5-methyl-1-piperidyl]-2-oxo-acetamide (Compound 928

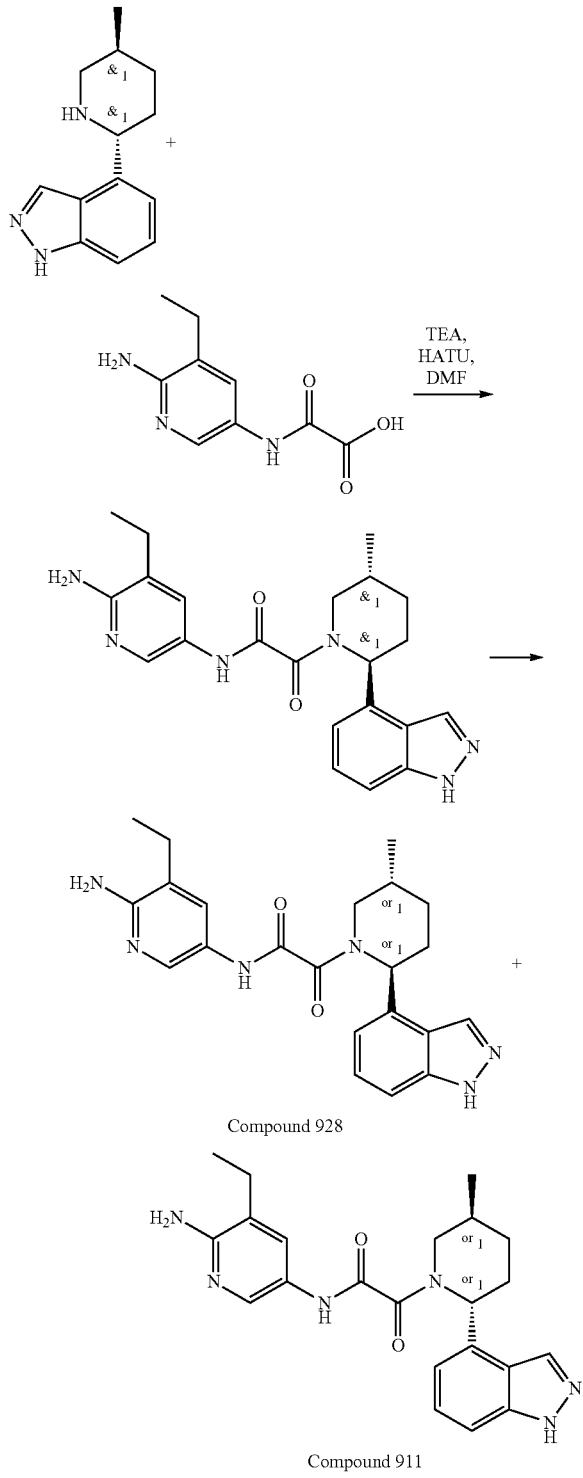

Step 1: Synthesis of N-(6-amino-5-ethyl-3-pyridyl)-2-[(2S,5R)-2-(1H-indazol-4-yl)-5-methyl-1-piperidyl]-2-oxo-acetamide To a stirred mixture of 4-[(2S,5R)-5-methyl-2-piperidyl]-1H-indazole (475 mg, 1.32 mmol, 2HCl), 2-[(6-amino-5-ethyl-3-pyridyl)amino]-2-oxo-acetic acid (275.82 mg, 1.32 mmol) and Triethylamine (667.07 mg, 6.59 mmol, 918.83 µL) in Dimethylformamide (4 mL) was added HATU (551.45 mg, 1.45 mmol). The resulting reaction mixture was stirred at 20° C. for 4 hr. Then, it was subjected to HPLC (30-30-55% 0-1-6 min H$_2$O/ACN/0.1% NH$_4$OH, flow: 30 ml/min; column: YMC Triart C18 100×20 mm, 5 um), affording N-(6-amino-5-ethyl-3-pyridyl)-2-[(2S,5R)-2-(1H-indazol-4-yl)-5-methyl-1-piperidyl]-2-oxo-acetamide (88 mg, 216.49 µmol, 16.42% yield).

LCMS(ESI): [M+H]$^+$ m/z: calcd 406.2; found 407.2; Rt=2.041 min.

Step 2: Synthesis of N-(6-amino-5-ethyl-3-pyridyl)-2-[(2S,5R)-2-(1H-indazol-4-yl)-5-methyl-1-piperidyl]-2-oxo-acetamide (Compound 911) and N-(6-amino-5-ethyl-3-pyridyl)-2-[(2R,5S)-2-(1H-indazol-4-yl)-5-methyl-1-piperidyl]-2-oxo-acetamide (Compound 928

N-(6-amino-5-ethyl-3-pyridyl)-2-[(2S,5R)-2-(1H-indazol-4-yl)-5-methyl-1-piperidyl]-2-oxo-acetamide (88 mg, 216.49 µmol) was divided into enantiomers by Chiral HPLC (Column: Chiralpak IA-I (250*20 mm, 5 mkm); Mobile phase: Hexane-IPA-MeOH 50-25-25 Flow Rate: 12 mL/min; 5 inj., 17 mg/inj., V=6 L, time=9.3 h.), affording: Compound 911-N-(6-amino-5-ethyl-3-pyridyl)-2-[(2S,5R)-2-(1H-indazol-4-yl)-5-methyl-1-piperidyl]-2-oxo-acetamide (31.7 mg, 77.99 µmol, 72.05% yield) with ret.time=62.752 min and Compound 928—N-(6-amino-5-ethyl-3-pyridyl)-2-[(2R,5S)-2-(1H-indazol-4-yl)-5-methyl-1-piperidyl]-2-oxo-acetamide (27.9 mg, 68.64 µmol, 63.41% yield) with ret.time=75.464 min.

Compound 911:

$^1$H NMR (DMSO-d$_6$, 600 MHz): δ (ppm) 1.06 (m, 6H), 1.32 (m, 1H), 1.85 (m, 2H), 2.19 (m, 2H), 2.29 (m, 1H), 2.39 (m, 1H), 2.97 (m, 1H), 3.54 (m, 1H), 5.76 (m, 3H), 7.06 (d, 1H), 7.31 (t, 1H), 7.44 (d, 1H), 7.51 (s, 1H), 8.07 (m, 2H), 10.46 (m, 1H), 13.11 (s, 1H).

LCMS(ESI): [M+H]$^+$ m/z: calcd 406.2; found 407.4; Rt=2.015 min.

RT (Hexane-IPA-MeOH, 50-25-25, 12 ml/min)=55.1092 min.

Compound 928:

$^1$H NMR (DMSO-d$_6$, 600 MHz): δ (ppm) 1.05 (m, 6H), 1.32 (m, 1H), 1.85 (m, 2H), 2.18 (m, 2H), 2.30 (m, 1H), 2.39 (m, 2H), 3.72 (m, 1H), 5.76 (m, 3H), 7.06 (d, 1H), 7.31 (t, 1H), 7.44 (d, 1H), 7.51 (s, 1H), 8.09 (m, 2H), 10.47 (m, 1H), 13.11 (s, 1H).

LCMS(ESI): [M+H]$^+$ m/z: calcd 406.2; found 407.4; Rt=2.008 min.

RT (Hexane-IPA-MeOH, 50-25-25, 12 ml/min)=72.1832 min.

Example 333. The Synthesis of N-(6-amino-5-methylpyridin-3-yl)-2-(5-methyl-2-(3-oxoisoindolin-5-yl)piperidin-1-yl)-2-oxoacetamide (Compound 582, Compound 657 and Compound 656

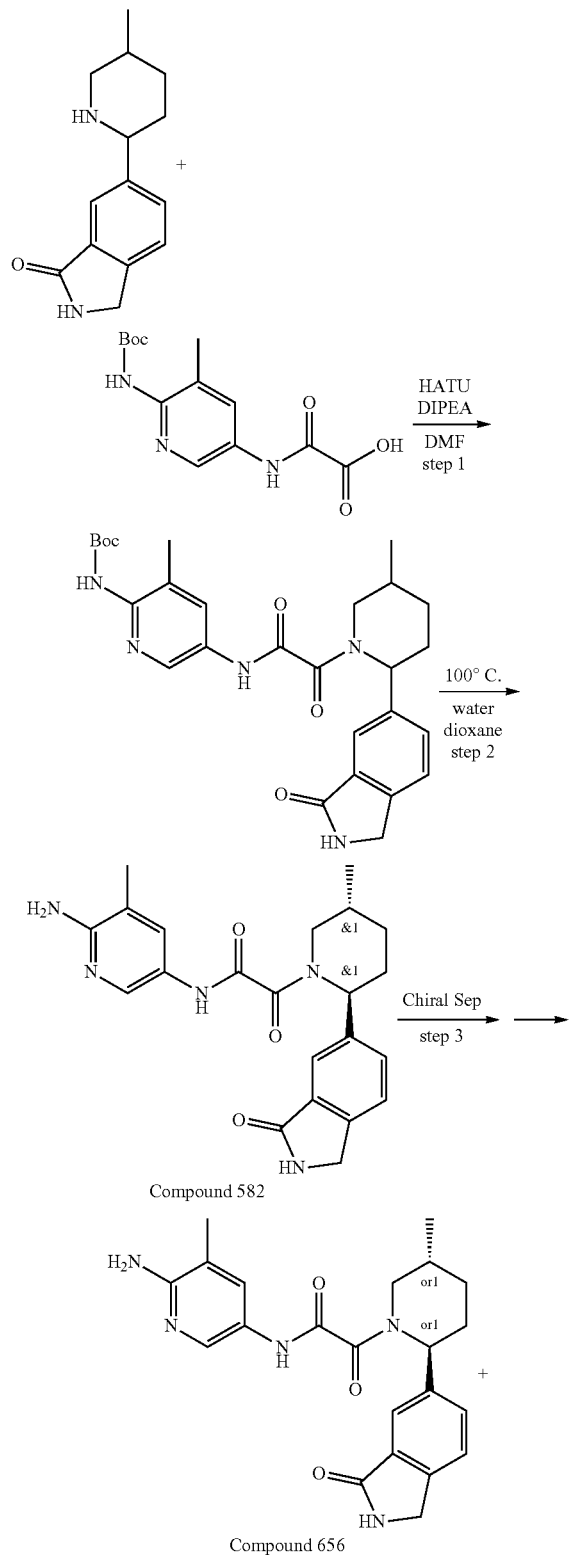

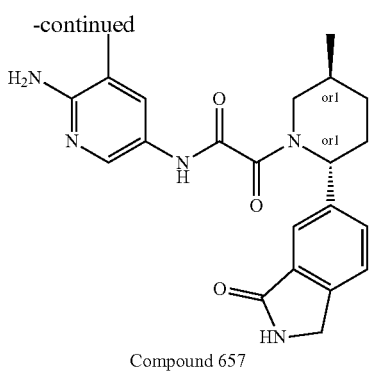

Compound 657

Step 1: Synthesis of tert-butyl (3-methyl-5-(2-(5-methyl-2-(3-oxoisoindolin-5-yl)piperidin-1-yl)-2-oxoacetamido)pyridin-2-yl)carbamate DIPEA (322.68 mg, 2.50 mmol, 434.88 μL) was added to the solution of respective 2-[[6-(tert-butoxycarbonylamino)-5-methyl-3-pyridyl]amino]-2-oxo-acetic acid (294.90 mg, 998.68 μmol) and 6-(5-methyl-2-piperidyl)isoindolin-1-one (0.23 g, 998.68 μmol) in DMF (5 mL). The resulting mixture was stirred for 5 min followed by the addition of HATU (417.70 mg, 1.10 mmol). Then, the reaction mixture was stirred overnight at rt. After the completion of the reaction, monitored by LCMS, the resulting suspension was concentrated under reduced pressure. The obtained solid was subjected to HPLC to afford pure tert-butyl N-[3-methyl-5-[[2-[5-methyl-2-(3-oxoisoindolin-5-yl)-1-piperidyl]-2-oxo-acetyl]amino]-2-pyridyl]carbamate (291.6 mg, 574.49 μmol, 57.53% yield).

$^1$H NMR (500 MHz, DMSO-$d_6$) δ (ppm) 1.03 (d, 3H), 1.48 (s, 9H), 1.68 (m, 1H), 1.92 (m, 1H), 2.18 (m, 3H), 2.22 (s, 3H), 2.78 (m, 1H), 3.86 (m, 1H), 4.36 (s, 2H), 5.55 (m, 1H), 7.68 (m, 3H), 7.96 (m, 1H), 8.49 (m, 2H), 8.98 (m, 1H), 11.08 (m, 1H).

LCMS(ESI): [M]$^+$ m/z: calcd 507.2; found 508.2; Rt=2.791 min.

Step 2: Synthesis of N-(6-amino-5-methylpyridin-3-yl)-2-(5-methyl-2-(3-oxoisoindolin-5-yl)piperidin-1-yl)-2-oxoacetamide tert-butyl N-[3-methyl-5-[[2-[5-methyl-2-(3-oxoisoindolin-5-yl)-1-piperidyl]-2-oxo-acetyl]amino]-2-pyridyl]carbamate (0.29 g, 571.34 μmol) was dissolved in dioxane (2 mL) and water (5 mL) mixture. Then reaction mixture was stirred for 14 hr at 100° C. After the completion of the reaction, monitored by LCMS, the resulting suspension was concentrated under reduced pressure. The obtained solid was subjected to HPLC to afford pure N-(6-amino-5-methyl-3-pyridyl)-2-[(2R,5S)-5-methyl-2-(3-oxoisoindolin-5-yl)-1-piperidyl]-2-oxo-acetamide (112.2 mg, 275.36 μmol, 48.20% yield). Sample contain 95% trans- and 5% cis-isomer.

Compound 582: $^1$H NMR (500 MHz, DMSO-$d_6$) δ (ppm) 1.01 (d, 3H), 1.33 (m, 1H), 1.66 (m, 1H), 1.84 (m, 1H), 1.97 (s, 3H), 2.02 (m, 1H), 2.28 (m, 1H), 3.02 (m, 1H), 3.78 (m, 1H), 4.34 (s, 2H), 5.57 (m, 3H), 7.48 (m, 2H), 7.59 (m, 2H), 8.02 (m, 1H), 8.55 (s, 1H), 10.54 (m, 1H).

LCMS(ESI): [M]$^+$ m/z: calcd 407.2; found 408.2; Rt=1.300 min.

2011

Step 3: Chiral Separation (Compound 657 and Compound 656

Chiral separation of N-(6-amino-5-methyl-3-pyridyl)-2-[(2S,5R)-5-methyl-2-(3-oxoisoindolin-5-yl)-1-piperidyl]-2-oxo-acetamide (60 mg, 147.25 μmol) was performed using Chiralpak AS (250*20 mm, 10 mkm) column; Hexane-IPA-MeOH 60-20-20 as a mobile phase;

Flow Rate: 12 mL/min; 4 pins affording Compound 656—N-(6-amino-5-methyl-3-pyridyl)-2-[(2S,5R)-5-methyl-2-(3-oxoisoindolin-5-yl)-1-piperidyl]-2-oxo-acetamide (27.22 mg, 66.80 μmol, 45.37% yield) (RT (IC, Hexane-IPA-MeOH, 50-25-25, 0.6 ml/min)=40.546 min) as a beige solid and Compound 657—N-(6-amino-5-methyl-3-pyridyl)-2-[(2R,5S)-5-methyl-2-(3-oxoisoindolin-5-yl)-1-piperidyl]-2-oxo-acetamide (26.87 mg, 65.94 μmol, 44.78% yield) (IC, Hexane-IPA-MeOH, 50-25-25, 0.6 ml/min)=50.183 min) as a beige solid.

Compound 656: Retention time: 40.54 min $^1$H NMR (600 MHz, DMSO-$d_6$) δ (ppm) 1.01 (m, 3H), 1.34 (m, 1H), 1.65 (m, 1H), 1.85 (m, 1H), 1.99 (m, 3H), 2.14 (m, 1H), 2.26 (m, 1H), 3.21 (m, 1H), 3.76 (m, 1H), 4.33 (m, 2H), 5.61 (m, 3H), 7.47 (m, 2H), 7.58 (m, 2H), 7.98 (m, 1H), 8.54 (s, 1H), 10.53 (m, 1H).

LCMS(ESI): [M]$^+$ m/z: calcd 407.2; found 408.2; Rt=1.687 min.

Compound 657: Retention time: 50.18 min $^1$H NMR (600 MHz, DMSO-$d_6$) δ (ppm) 1.01 (m, 3H), 1.34 (m, 1H), 1.66 (m, 1H), 1.84 (m, 1H), 1.99 (m, 3H), 2.14 (m, 1H), 2.24 (m, 1H), 3.05 (m, 1H), 3.66 (m, 1H), 4.33 (m, 2H), 5.61 (m, 3H), 7.55 (m, 4H), 7.98 (m, 1H), 8.54 (m, 1H), 10.53 (m, 1H).

LCMS(ESI): [M]$^+$ m/z: calcd 407.2; found 408.2; Rt=1.696 min.

Example 334. The Synthesis of N-(6-amino-5-methylpyridin-3-yl)-2-(2-(3-chloro-4,5-difluorophenyl)-5-methylpiperidin-1-yl)-2-oxoacetamide (Compound 857 and Compound 847

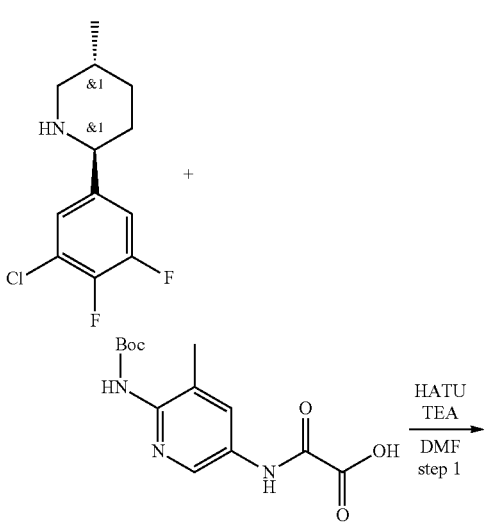

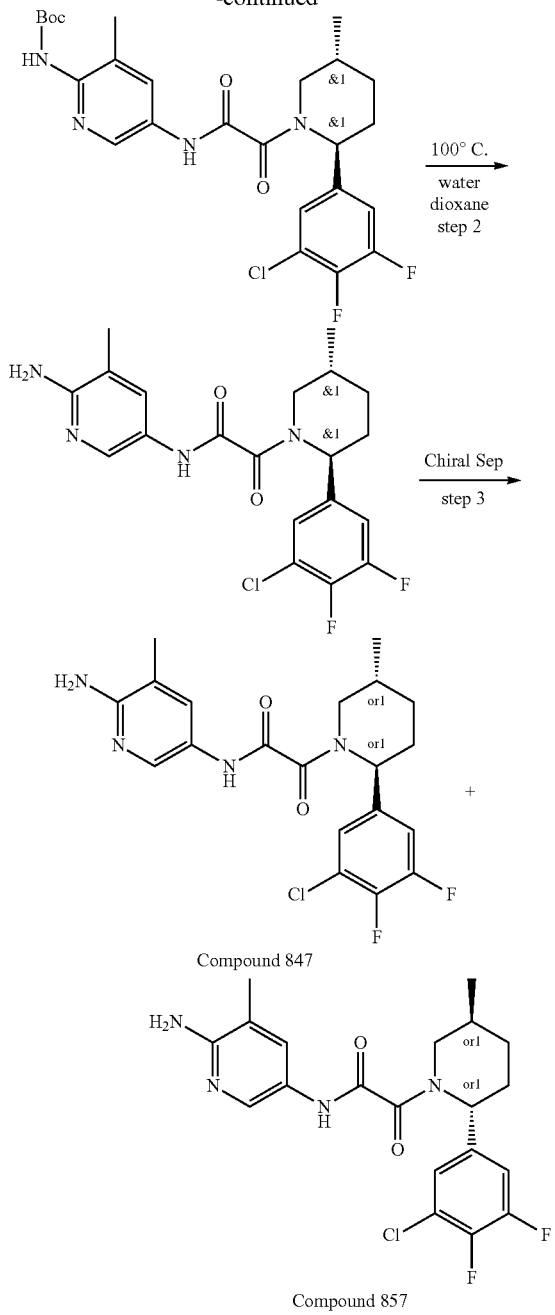

Compound 847

Compound 857

Step 1: Synthesis of rac-tert-butyl (5-(2-((2R,5S)-2-(3-chloro-4,5-difluorophenyl)-5-methylpiperidin-1-yl)-2-oxoacetamido)-3-methylpyridin-2-yl)carbamate To a stirred mixture of (2R,5S)-2-(3-chloro-4,5-difluorophenyl)-5-methyl-piperidine (200 mg, 814.02 μmol), 2-[[6-(tert-butoxycarbonylamino)-5-methyl-3-pyridyl]amino]-2-oxo-acetic acid (240.37 mg, 814.02 μmol) and TEA (164.74 mg, 1.63 mmol, 226.92 μL) in DCM (3 mL) was added HATU (340.46 mg, 895.42 μmol). The resulting reaction mixture was stirred at 20° C. for 5 hr. Then, it was subjected to HPLC (55-90% 0-5 min H$_2$O/MeOH/0.1% NH$_4$OH, flow: 30 ml/min; column: YMC Triart C18 100×20 mm, 5 um), affording tert-butyl N-[5-[[2-[(2R,5S)-2-(3-chloro-4,5-difluoro-phenyl)-5-methyl-1-piperidyl]-2-oxo-acetyl]amino]-3-methyl-2-pyridyl]carbamate (220 mg, 420.67 μmol, 51.68% yield).

LCMS(ESI): [M]+ m/z: calcd 522.2; found 523.2; Rt=3.873 min.

Step 2: Synthesis of N-(6-amino-5-methylpyridin-3-yl)-2-(2-(3-chloro-4,5-difluorophenyl)-5-methylpiperidin-1-yl)-2-oxoacetamide Water (1.00 g, 55.51 mmol, 1 mL) was added to a solution of tert-butyl N-[5-[[2-[(2R,5S)-2-(3-chloro-4,5-difluoro-phenyl)-5-methyl-1-piperidyl]-2-oxo-acetyl]amino]-3-methyl-2-pyridyl]carbamate (220 mg, 420.67 μmol) in dioxane (2 mL). Resulting mixture was stirred at 100° C. for 15 hr. Then, it was subjected to HPLC (60-60-90% 0-1-6 min H₂O/MeOH/0.1% NH₄OH, flow: 30 ml/min; column: YMC Triart C18 100×20 mm, 5 um), affording N-(6-amino-5-methyl-3-pyridyl)-2-[(2R,5S)-2-(3-chloro-4,5-difluoro-phenyl)-5-methyl-1-piperidyl]-2-oxo-acetamide (145 mg, 342.91 μmol, 81.51% yield).

LCMS(ESI): [M]+ m/z: calcd 422.2; found 423.2; Rt=2.565 min.

Step 3: Chiral Separation (Compound 847 and Compound 857

N-(6-amino-5-methyl-3-pyridyl)-2-[(2R,5S)-2-(3-chloro-4,5-difluoro-phenyl)-5-methyl-1-piperidyl]-2-oxo-acetamide (145 mg, 342.91 μmol) was divided into enantiomers by Chiral HPLC (Chiralpak AD-H (250*20 mm, 5 mkm); Hexane-IPA-MeOH, 50-25-25, 10 mL/min; Column Temperature: 20° C.), affording: N-(6-amino-5-methyl-3-pyridyl)-2-[(2S,5R)-2-(3-chloro-4,5-difluoro-phenyl)-5-methyl-1-piperidyl]-2-oxo-acetamide (59 mg, 139.53 μmol, 81.38% yield) with ret.time=18.50 min (Compound 847) and N-(6-amino-5-methyl-3-pyridyl)-2-[(2R,5S)-2-(3-chloro-4,5-difluoro-phenyl)-5-methyl-1-piperidyl]-2-oxo-acetamide (62 mg, 146.62 μmol, 85.52% yield) with ret.time=25.84 min (Compound 857).

Ret time for Compound 847 in analytical conditions (column: AD-H, Hexane-IPA-MeOH, 50-25-25, 0.6 ml/min as mobile phase) 18.96 min and for Compound 857 32.05 min.

Compound 847: Retention time: 18.96 min

¹H NMR (600 MHz, DMSO-d₆) δ (ppm) 0.96-1.00 (m, 3H), 1.21-1.36 (m, 1H), 1.58-1.68 (m, 1H), 1.80-1.91 (m, 1H), 1.96-2.04 (m, 4H), 2.12-2.24 (m, 1H), 2.71-3.25 (m, 1H), 3.41-4.05 (m, 1H), 5.04-5.50 (m, 1H), 5.56-5.69 (m, 2H), 7.28-7.42 (m, 2H), 7.42-7.50 (m, 1H), 7.91-8.05 (m, 1H), 10.34-10.64 (m, 1H).

LCMS(ESI): [M]+ m/z: calcd 422.2; found 423.2; Rt=2.680 min.

Compound 857: Retention time: 32.05 min

¹H NMR (600 MHz, DMSO-d₆) δ (ppm) 0.97-1.01 (m, 3H), 1.23-1.35 (m, 1H), 1.57-1.66 (m, 1H), 1.82-1.91 (m, 1H), 1.95-2.04 (m, 4H), 2.12-2.25 (m, 1H), 2.71-3.24 (m, 1H), 3.42-4.05 (m, 1H), 5.02-5.50 (m, 1H), 5.56-5.68 (m, 2H), 7.28-7.42 (m, 2H), 7.42-7.51 (m, 1H), 7.85-8.05 (m, 1H), 10.38-10.71 (m, 1H).

LCMS(ESI): [M]+ m/z: calcd 422.2; found 423.2; Rt=2.684 min.

Example 335. The Synthesis of N-(6-amino-5-methylpyridin-3-yl)-2-(2-(3-chloro-5-(trifluoromethyl)phenyl)-5-methylpiperidin-1-yl)-2-oxoacetamide (Compound 665 and Compound 679

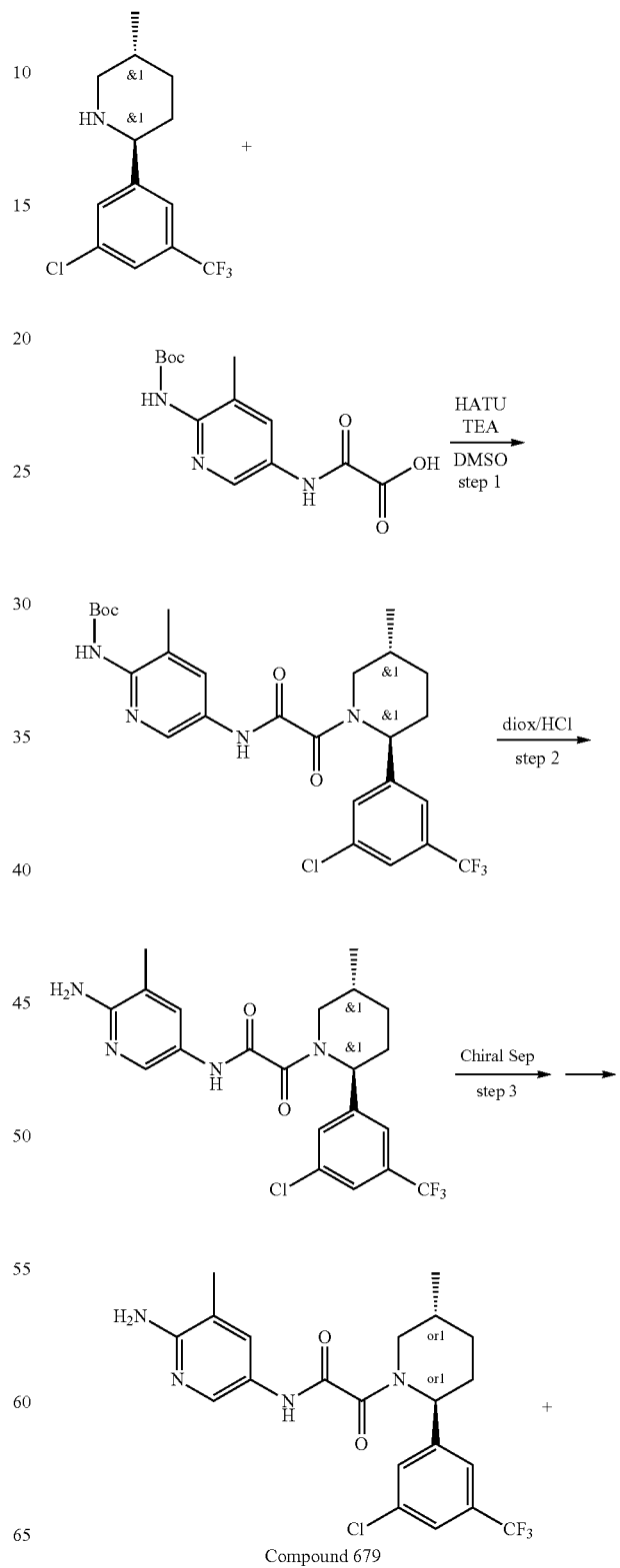

Compound 679

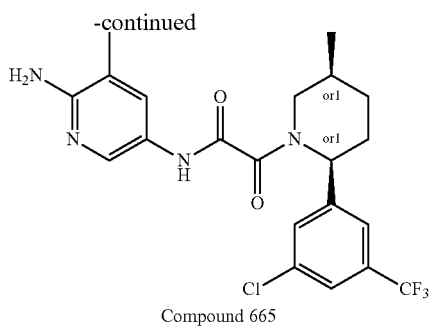

Compound 665

Step 1: Synthesis of rac-tert-butyl (5-(2-((2R,5S)-2-(3-chloro-5-(trifluoromethyl)phenyl)-5-methylpiperidin-1-yl)-2-oxoacetamido)-3-methylpyridin-2-yl) carbamate 2-[[6-(tert-butoxycarbonylamino)-5-methyl-3-pyridyl]amino]-2-oxo-acetic acid (265.82 mg, 900.21 μmol), (2R,5S)-2-[3-chloro-5-(trifluoromethyl)phenyl]-5-methyl-piperidine (250 mg, 900.21 μmol), HATU (342.29 mg, 900.21 μmol) and TEA (91.09 mg, 900.21 μmol, 125.47 μL) were mixed in DMSO (2 mL) and stirred for 3 hr at 20° C. Reaction mixture was subjected to HPLC 2-10 min 45-60% water/ACN (loading pump 4 ml ACN) column: TRIART 100*20 5 microM. tert-butyl N-[5-[[2-[(2R,5S)-2-[3-chloro-5-(trifluoromethyl)phenyl]-5-methyl-1-piperidyl]-2-oxo-acetyl]amino]-3-methyl-2-pyridyl]carbamate (306 mg, 551.36 μmol, 61.25% yield) was obtained.

LCMS(ESI): [M]$^+$ m/z: calcd 554.2; found 555.2; Rt=4.179 min.

Step 2: Synthesis of N-(6-amino-5-methylpyridin-3-yl)-2-(2-(3-chloro-5-(trifluoromethyl)phenyl)-5-methylpiperidin-1-yl)-2-oxoacetamide tert-butyl N-[5-[[2-[(2R,5S)-2-[3-chloro-5-(trifluoromethyl)phenyl]-5-methyl-1-piperidyl]-2-oxo-acetyl]amino]-3-methyl-2-pyridyl]carbamate (306 mg, 551.36 μmol) was dissolved in dioxane (4 mL) saturated with HCl. After 1 hr of vigorous stirring reaction mixture was concentrated in vacuo. N-(6-amino-5-methyl-3-pyridyl)-2-[(2R,5S)-2-[3-chloro-5-(trifluoromethyl)phenyl]-5-methyl-1-piperidyl]-2-oxo-acetamide (270 mg, crude) was obtained.

Crude product was subjected to chiral separation.

LCMS(ESI): [M]$^+$ m/z: calcd 454.2; found 455.2; Rt=1.223 min.

Step 3: Chiral Separation (Compound 665 and Compound 679

Racemic N-(6-amino-5-methyl-3-pyridyl)-2-[(2R,5S)-2-[3-chloro-5-(trifluoromethyl)phenyl]-5-methyl-1-piperidyl]-2-oxo-acetamide (150 mg, 329.76 μmol) was separated using Chiralpak AD-H-III 250*20, 5 mkm column; Hexane-IPA-MeOH, 60-20-20 as a mobile phase; Flow rate 12 mL/min; Injection Volume: 900 mkl; affording N-(6-amino-5-methyl-3-pyridyl)-2-[(2S,5R)-2-[3-chloro-5-(trifluoromethyl)phenyl]-5-methyl-1-piperidyl]-2-oxo-acetamide (20 mg, 43.97 μmol, 26.67% yield) and N-(6-amino-5-methyl-3-pyridyl)-2-[(2R,5S)-2-[3-chloro-5-(trifluoromethyl)phenyl]-5-methyl-1-piperidyl]-2-oxo-acetamide (53 mg, 116.52 μmol, 70.67% yield). Ret time for Compound 665 in analytical conditions (column: AD-H, Hexane-IPA-MeOH, 60-20-20, 0.6 ml/min as mobile phase) 31.13 min and for Compound 679 13.31 min.

Compound 665: Retention time: 31.13 min $^1$H NMR (600 MHz, DMSO-d$_6$) δ (ppm) 0.99 (m, 3H), 1.61 (m, 1H), 1.88 (m, 1H), 2.01 (m, 4H), 2.26 (m, 3H), 3.76 (m, 1H), 5.37 (m, 1H), 5.76 (s, 2H), 7.48 (m, 1H), 7.57 (m, 1H), 7.66 (m, 1H), 7.77 (m, 1H), 7.99 (m, 1H), 10.61 (m, 1H).

LCMS(ESI): [M]$^+$ m/z: calcd 454.2; found 455.2; Rt=2.869 min.

Compound 679: Retention time: 13.31 min $^1$H NMR (600 MHz, DMSO-d$_6$) δ (ppm) 0.98 (m, 3H), 1.30 (m, 1H), 1.58 (m, 1H), 1.86 (m, 1H), 2.02 (m, 4H), 2.20 (m, 2H), 3.82 (m, 1H), 5.37 (m, 1H), 5.61 (m, 2H), 7.45 (m, 1H), 7.57 (m, 1H), 7.66 (m, 1H), 7.77 (m, 1H), 7.96 (m, 1H), 10.57 (m, 1H).

LCMS(ESI): [M]$^+$ m/z: calcd 454.2; found 455.2; Rt=2.874 min.

Example 336. The Synthesis of N-(6-amino-5-methylpyridin-3-yl)-2-(2-(3,4-difluorophenyl)-4,4-difluoro-5-methylpiperidin-1-yl)-2-oxoacetamide (Compound 684 and Compound 705

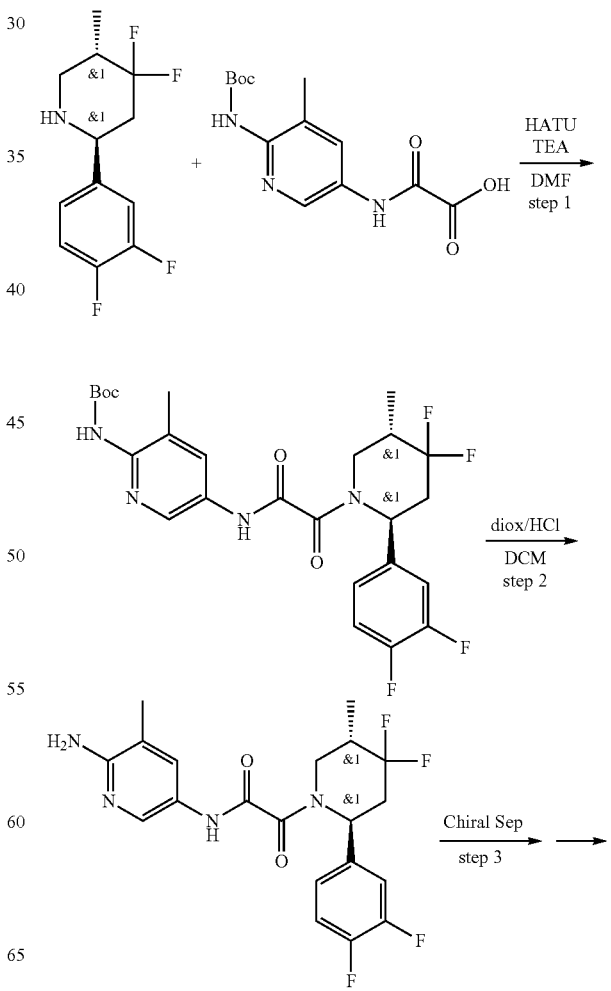

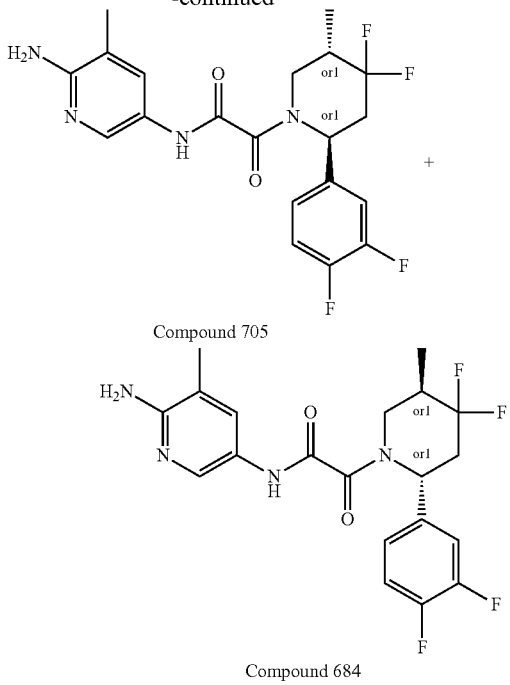

Compound 705

Compound 684

Step 1: Synthesis of rac-tert-butyl (5-(2-((2R,5R)-2-(3,4-difluorophenyl)-4,4-difluoro-5-methylpiperidin-1-yl)-2-oxoacetamido)-3-methylpyridin-2-yl)carbamate To a solution of (2S,5S)-2-(3,4-difluorophenyl)-4,4-difluoro-5-methyl-piperidine (0.3 g, 1.21 mmol), 2-[[6-(tert-butoxycarbonylamino)-5-methyl-3-pyridyl]amino]-2-oxo-acetic acid (358.32 mg, 1.21 mmol) and TEA (613.94 mg, 6.07 mmol, 845.65 µL), HATU (507.52 mg, 1.33 mmol) was added portion wise. The resulting mixture was stirred at 25° C. for 3 hr, taken up with water (50 ml) and extracted with EtOAc (3*20 ml). The combined organic layer was washed with brine (2*25 ml), dried over Na$_2$SO$_4$ and the solvent was removed to give tert-butyl N-[5-[[2-[(2S,5S)-2-(3,4-difluorophenyl)-4,4-difluoro-5-methyl-1-piperidyl]-2-oxo-acetyl]amino]-3-methyl-2-pyridyl]carbamate (0.6 g, 1.14 mmol, 94.27% yield). This compound was used for the next step without further purification.

$^1$H NMR (500 MHz, DMSO-d$_6$) δ (ppm) 1.07 (d, 3H), 1.42 (s, 9H), 2.18 (s, 3H), 2.87 (m, 1H), 2.97 (m, 1H), 3.73 (m, 1H), 4.02 (m, 1H), 5.75 (m, 1H), 7.23 (m, 1H), 7.43 (m, 3H), 7.95 (m, 1H), 8.46 (m, 1H), 9.08 (m, 1H), 11.15 (m, 1H).

LCMS(ESI): [M]$^+$ m/z: calcd 524.2; found 525.2; Rt=1.475 min.

Step 2: Synthesis of rac-N-(6-amino-5-methylpyridin-3-yl)-2-((2R,5R)-2-(3,4-difluorophenyl)-4,4-difluoro-5-methylpiperidin-1-yl)-2-oxoacetamide A solution of tert-butyl N-[5-[[2-[(2S,5S)-2-(3,4-difluorophenyl)-4,4-difluoro-5-methyl-1-piperidyl]-2-oxo-acetyl]amino]-3-methyl-2-pyridyl]carbamate (0.6 g, 1.14 mmol) in DCM (20 mL) and hydrogen chloride solution 4.0 M in dioxane (5 g, 137.13 mmol, 6.25 mL) was stirred at 25° C. for 12 hr. The solvent was removed and residue (0.5 g) was purified by HPLC: 50-65% 0-5 min Water/MeOH/0.1% NH$_3$, flow: 30 ml/min (loading pump 4 ml/min MeOH) target mass 425 column: YMC Triart C18 100×20 mm, 5 um) to obtain N-(6-amino-5-methyl-3-pyridyl)-2-[(2S,5S)-2-(3,4-difluorophenyl)-4,4-difluoro-5-methyl-1-piperidyl]-2-oxo-acetamide (127 mg, 299.25 µmol, 26.16% yield). This compound was used for chiral resolution without H-NMR.

LCMS(ESI): [M]$^+$ m/z: calcd 424.2; found 425.2; Rt=2.412 min.

Step 3: Chiral Separation (Compound 684 and Compound 705

N-(6-amino-5-methyl-3-pyridyl)-2-[(2S,5S)-2-(3,4-difluorophenyl)-4,4-difluoro-5-methyl-1-piperidyl]-2-oxo-acetamide (127 mg, 299.25 µmol) was chirally separated (Sample Info: OJ-H-I (250*0.0, 5 mkm), Hexane-IPA-MeOH, 60-20-20, 12 ml/min) to obtain N-(6-amino-5-methyl-3-pyridyl)-2-[(2R,5R)-2-(3,4-difluorophenyl)-4,4-difluoro-5-methyl-1-piperidyl]-2-oxo-acetamide (49 mg, 115.46 µmol, 77.17% yield) and N-(6-amino-5-methyl-3-pyridyl)-2-[(2S,5S)-2-(3,4-difluorophenyl)-4,4-difluoro-5-methyl-1-piperidyl]-2-oxo-acetamide (49 mg, 115.46 µmol, 77.17% yield).

Ret time for Compound 684 in analytical conditions (column: AD-H, Hexane-IPA-MeOH, 50-25-25, 0.6 ml/min as mobile phase) 38.68 min and for Compound 705 27.92 min.

Compound 684: Retention time: 38.68 min
$^1$H NMR (600 MHz, DMSO-d$_6$) δ (ppm) 1.05 (m, 3H), 2.00 (m, 3H), 2.19 (m, 2H), 2.86 (m, 1H), 3.41 (m, 1H), 4.03 (m, 1H), 5.56 (m, 1H), 5.71 (m, 2H), 7.14 (m, 1H), 7.44 (m, 3H), 7.99 (m, 1H), 10.57 (m, 1H).

LCMS(ESI): [M]$^+$ m/z: calcd 424.2; found 425.2; Rt=2.424 min.

Compound 705: Retention time: 27.92 min
$^1$H NMR (600 MHz, DMSO-d$_6$) δ (ppm) 1.05 (m, 3H), 2.00 (m, 3H), 2.19 (m, 2H), 2.86 (m, 1H), 3.41 (m, 1H), 3.95 (m, 1H), 5.68 (m, 3H), 7.44 (m, 4H), 7.99 (m, 1H), 10.58 (m, 1H).

LCMS(ESI): [M]$^+$ m/z: calcd 424.2; found 425.2; Rt=2.426 min.

Example 337. The Synthesis of N-(6-amino-5-methylpyridin-3-yl)-2-(5-methyl-2-(3-Sulfamoylphenyl)piperidin-1-yl)-2-oxoacetamide (Compound 688

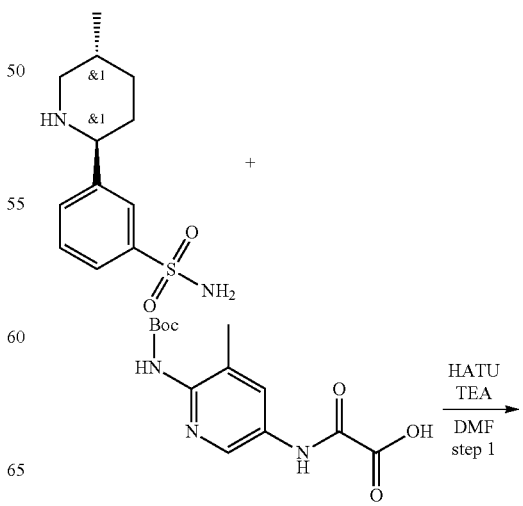

2019

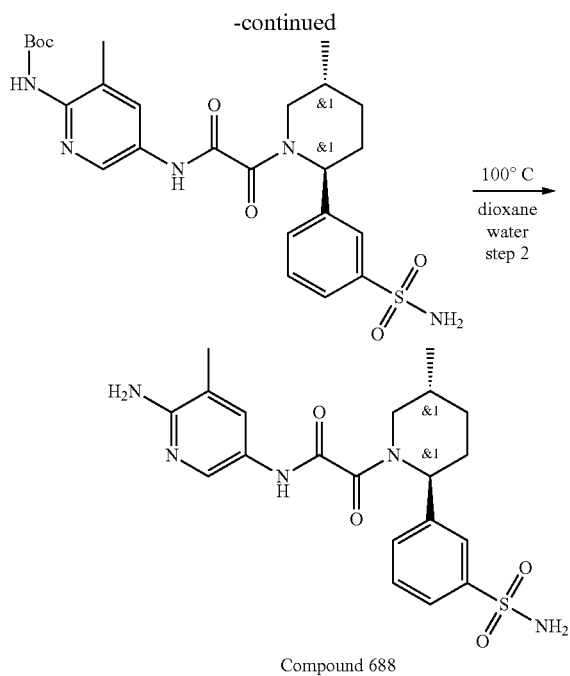

Compound 688

Step 1: Synthesis of rac-tert-butyl (3-methyl-5-(2-((2R,5S)-5-methyl-2-(3-Sulfamoylphenyl)piperidin-1-yl)-2-oxoacetamido)pyridin-2-yl)carbamate To a stirred mixture of 3-[(2S,5R)-5-methyl-2-piperidyl]benzenesulfonamide (490 mg, 1.93 mmol), 2-[[6-(tert-butoxycarbonylamino)-5-methyl-3-pyridyl]amino]-2-oxo-acetic acid (568.88 mg, 1.93 mmol) and TEA (584.83 mg, 5.78 mmol, 805.55 μL) in DMF (4 mL) was added HATU (805.76 mg, 2.12 mmol). The resulting reaction mixture was stirred at 20° C. for 4 hr. Then, it was subjected to HPLC (Column: YMC-Actus Triart C18 100*20 mm, 5 um; 40-90% 1-6 min water-MeOH (NH$_3$ 0.1%), flow 30 ml/min), affording tert-butyl N-[3-methyl-5-[[2-[(2S,5R)-5-methyl-2-(3-sulfamoylphenyl)-1-piperidyl]-2-oxo-acetyl]amino]-2-pyridyl]carbamate (200 mg, 376.21 μmol, 19.53% yield).

LCMS(ESI): [M]$^+$ m/z: calcd 531.4; found 532.2; Rt=2.752 min.

Step 2: Synthesis of N-(6-amino-5-methylpyridin-3-yl)-2-(5-methyl-2-(3-Sulfamoylphenyl)piperidin-1-yl)-2-oxoacetamide (Compound 688 tert-butyl N-[3-methyl-5-[[2-[(2S,5R)-5-methyl-2-(3-sulfamoylphenyl)-1-piperidyl]-2-oxo-acetyl]amino]-2-pyridyl]carbamate (200 mg, 376.21 μmol) was dissolved in the mixture of water (1.00 g, 55.49 mmol, 1 mL) and dioxane (2 mL). Resulting solution was stirred at 100° C. for 18 hr. Then, it was subjected to HPLC (Column: YMC-Actus Triart C18 100*20 mm, 5 um; 0-5 min 20-70% water-MeOH (NH$_3$ 0.1%)), affording N-(6-amino-5-methyl-3-pyridyl)-2-[(2S,5R)-5-methyl-2-(3-sulfamoylphenyl)-1-piperidyl]-2-oxo-acetamide (45 mg, 104.29 μmol, 27.72% yield).

$^1$H NMR (600 MHz, DMSO-d$_6$) δ (ppm) 1.01 (m, 3H), 1.35 (m, 1H), 1.64 (m, 1H), 1.87 (m, 1H), 1.99 (m, 5H), 2.18 (m, 2H), 2.96 (m, 1H), 3.79 (m, 1H), 5.60 (m, 3H), 7.46 (m, 2H), 7.58 (m, 2H), 7.72 (d, 1H), 7.77 (d, 1H), 8.00 (m, 1H). LCMS(ESI): [M]$^+$ m/z: calcd 431.4; found 432.2; Rt=1.582 min.

2020

Example 338. The Synthesis of N-(6-amino-5-methylpyridin-3-yl)-2-(5-methyl-2-(3-(methylsulfonyl)phenyl)piperidin-1-yl)-2-oxoacetamide (Compound 667, Compound 901, Compound 895

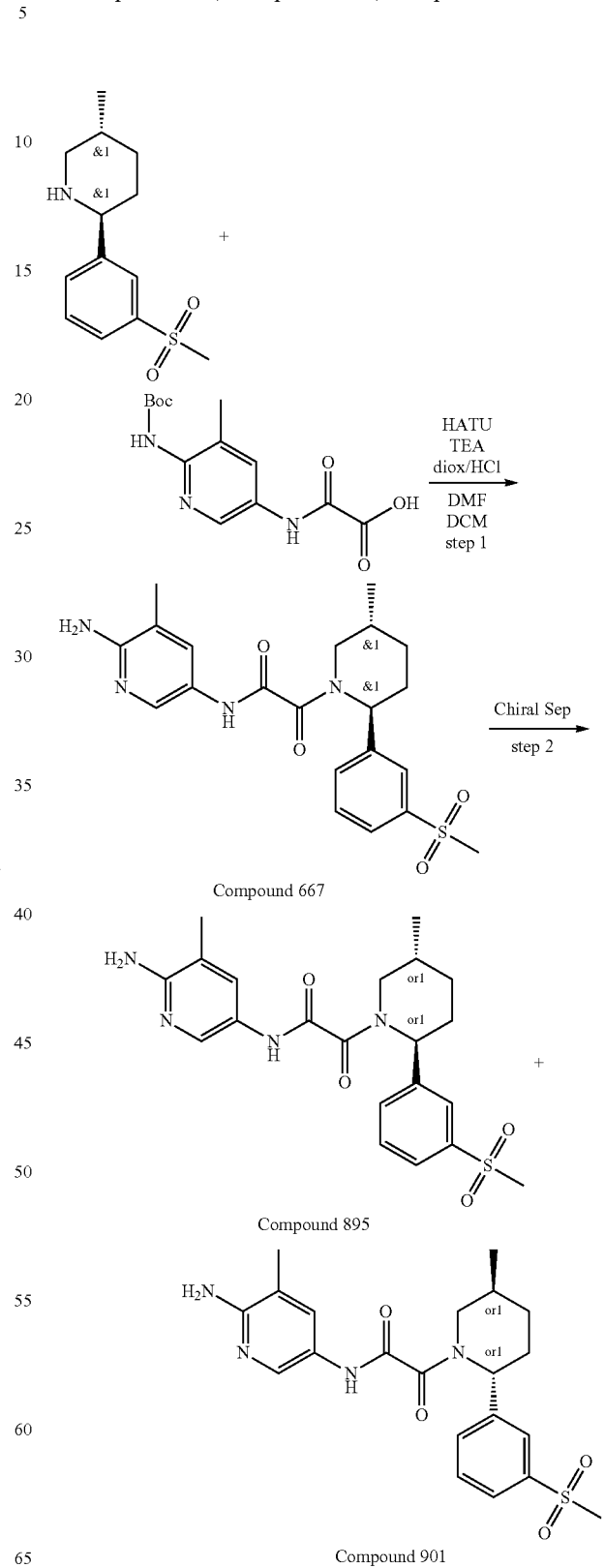

Step 1: Synthesis of N-(6-amino-5-methylpyridin-3-yl)-2-(5-methyl-2-(3-(methylsulfonyl)phenyl)piperidin-1-yl)-2-oxoacetamide To a stirring solution of (2R,5S)-5-methyl-2-(3-methylsulfonylphenyl)piperidine (250.00 mg, 986.74 µmol), 2-[[6-(tert-butoxycarbonylamino)-5-methyl-3-pyridyl]amino]-2-oxo-acetic acid (291.37 mg, 986.74 µmol) and TEA (998.48 mg, 9.87 mmol, 1.38 mL) in DMF (5 mL) was added HATU (412.71 mg, 1.09 mmol) at 25° C. in small portions over 0.5 hr. The resulting reaction mixture was stirred at 25° C. for 18 hr. The reaction mixture was concentrated in vacuo, the residue was dissolved in dichloromethane (10 mL), and hydrogen chloride solution 4.0 M in dioxane (15.75 g, 60.04 mmol, 15.00 mL, 13.9% purity) was added in one portion. The resulting mixture was stirred at 25° C. for 3 hr, and then concentrated in vacuo. The residue was purified by reverse phase HPLC (column:YMC Triart C18 100×20 mm, 5 um; mobile phase: 35-45% 0-5 min Water/MeOH/0.1% NH$_3$, flow rate: 30 ml/min (loading pump 4 ml/min MeOH)) to afford Compound 667 N-(6-amino-5-methyl-3-pyridyl)-2-[(2R,5S)-5-methyl-2-(3-methylsulfonylphenyl)-1-piperidyl]-2-oxo-acetamide (111 mg, 257.83 µmol, 26.13% yield) as white solid.

$^1$H NMR (600 MHz, DMSO-d$_6$) δ (ppm) 1.01 (m, 3H), 1.35 (m, 1H), 1.62 (m, 1H), 1.87 (m, 1H), 1.99 (m, 3H), 2.19 (m, 2H), 3.21 (m, 4H), 3.77 (m, 1H), 5.41 (m, 1H), 5.62 (m, 2H), 7.45 (m, 1H), 7.65 (m, 2H), 7.83 (m, 2H), 7.97 (m, 1H), 10.54 (s, 1H).

LCMS(ESI): [M]$^+$ m/z: calcd 430.2; found 431.2; Rt=1.744 min.

Step 2: Chiral Separation (Compound 901 and Compound 895

Column: Chiralpak IA-II (250*20 mm, 5 mkm); Mobile phase: Hexane-IPA-MeOH 40-30-30 Flow Rate: 12 mL/min; m=0.09$_\Gamma$, 2 injections, 45 mL per injection, V=2 L, 2.5 hr, RT (Compound 895)=20.805 min, RT (Compound 901)=37.044 min. Enantiomers were additionally purified in the following conditions: Compound 895—N-(6-amino-5-methyl-3-pyridyl)-2-[(2S,5R)-5-methyl-2-(3-methylsulfonylphenyl)-1-piperidyl]-2-oxo-acetamide (30.78 mg, 71.50 µmol, 32.68% yield). Column: Chiralcel OJ-H-I (250*20 mm, 5 mkm); Mobile phase: Hexane-IPA-MeOH 50-25-25 Flow Rate: 12 mL/min; m=0.04$_\Gamma$, 2 injections, 20 mL per injection V=2 L, 2 hours (RT=28.825 min). Compound 901—N-(6-amino-5-methyl-3-pyridyl)-2-[(2R,5S)-5-methyl-2-(3-methylsulfonylphenyl)-1-piperidyl]-2-oxo-acetamide (30.81 mg, 71.56 µmol, 32.71% yield). Column: Chiralpak IC-II (250*20 mm, 5 mkm); Mobile phase: Hexane-IPA-MeOH 50-25-25 Flow Rate: 12 mL/min; m=0.04$_\Gamma$, 2 injections, 20 mL per injection V=1.5 L, 2.5 hours (RT=31.957 min). Ret time for Compound 901 in analytical conditions (column: OJ-H, Hexane-IPA-MeOH 50-25-25, 0.6 ml/min as mobile phase) 31.97 min and for Compound 895 28.82 min.

Compound 901: Retention time: 31.97 min
$^1$H NMR (500 MHz, DMSO-d$_6$) δ (ppm) 1.04 (m, 3H), 1.32 (m, 1H), 1.64 (m, 1H), 1.88 (m, 1H), 2.00 (m, 3H), 2.21 (m, 1H), 3.22 (m, 3H), 3.42 (m, 2H), 3.78 (m, 1H), 5.61 (m, 3H), 7.46 (d, 1H), 7.67 (m, 2H), 7.83 (m, 2H), 7.98 (d, 1H), 10.55 (s, 1H).
LCMS(ESI): [M]$^+$ m/z: calcd 430.2; found 431.2; Rt=1.703 min.

Compound 895: Retention time: 28.82 min
$^1$H NMR (500 MHz, DMSO-d$_6$) δ (ppm) 1.02 (m, 3H), 1.34 (m, 1H), 1.61 (m, 1H), 1.89 (m, 1H), 2.00 (m, 3H), 2.18 (m, 2H), 3.22 (m, 4H), 3.78 (dd, 1H), 5.61 (m, 3H), 7.46 (d, 1H), 7.66 (m, 2H), 7.84 (m, 2H), 7.98 (d, 1H), 10.55 (s, 1H).
LCMS(ESI): [M]$^+$ m/z: calcd 430.2; found 431.2; Rt=1.768 min.

Example 339. The Synthesis of N-(6-amino-5-methylpyridin-3-yl)-2-(5-methyl-2-(3-(N-methylsulfamoyl)phenyl)piperidin-1-yl)-2-oxoacetamide (Compound 691

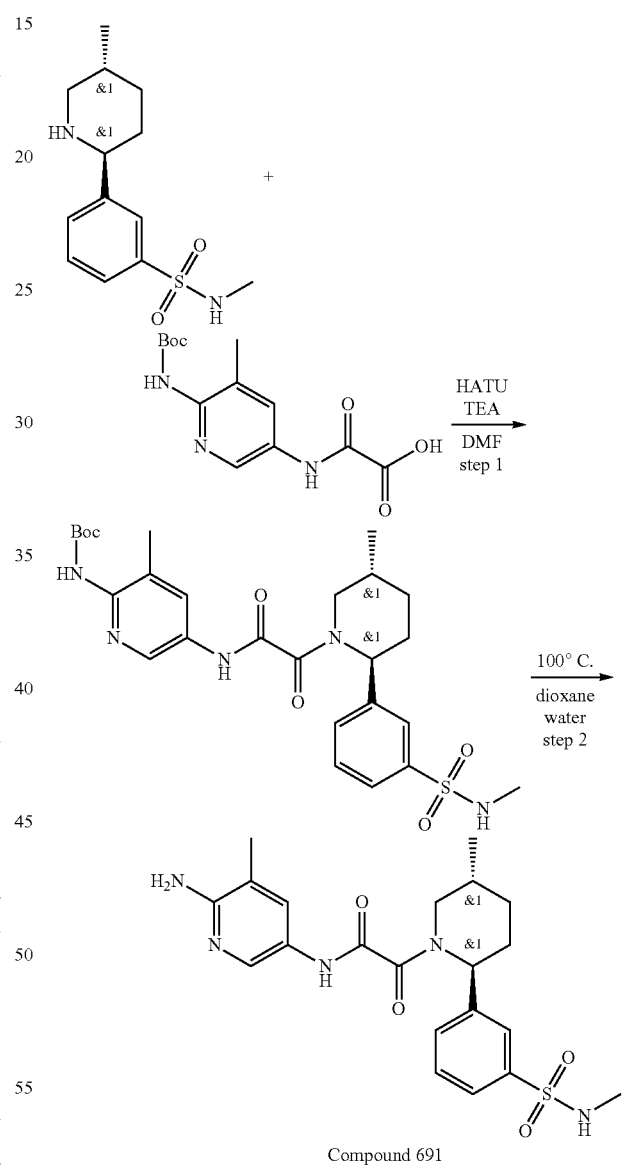

Compound 691

Step 1: Synthesis of rac-tert-butyl (3-methyl-5-(2-((2R,5S)-5-methyl-2-(3-(N-methylsulfamoyl)phenyl)piperidin-1-yl)-2-oxoacetamido)pyridin-2-yl)carbamate To a stirred mixture of N-methyl-3-[(2S,5R)-5-methyl-2-piperidyl]benzenesulfonamide (535 mg, 1.99 mmol), 2-[[6-

(tert-butoxycarbonylamino)-5-methyl-3-pyridyl]amino]-2-oxo-acetic acid (588.66 mg, 1.99 mmol) and TEA (605.16 mg, 5.98 mmol, 833.56 μL) in DMF (4 mL) was added HATU (833.78 mg, 2.19 mmol). The resulting reaction mixture was stirred at 20° C. for 4 hr. Then, it was subjected to HPLC (Column: YMC-Actus Triart C18 100*20 mm, 5 um; 40-90% 1-6 min water-MeOH (NH₃ 0.1%), flow 30 ml/min), affording tert-butyl N-[3-methyl-5-[[2-[(2S,5R)-5-methyl-2-[3-(methylsulfamoyl)phenyl]-1-piperidyl]-2-oxo-acetyl]amino]-2-pyridyl]carbamate (242 mg, 443.51 μmol, 22.25% yield).

LCMS(ESI): [M]⁺ m/z: calcd 545.4; found 546.2; Rt=2.969 min.

Step 2: Synthesis of N-(6-amino-5-methylpyridin-3-yl)-2-(5-methyl-2-(3-(N-methylsulfamoyl)phenyl)piperidin-1-yl)-2-oxoacetamide (Compound 691 tert-butyl N-[3-methyl-5-[[2-[(2S,5R)-5-methyl-2-[3-(methylsulfamoyl)phenyl]-1-piperidyl]-2-oxo-acetyl]amino]-2-pyridyl]carbamate (242 mg, 443.51 μmol) was dissolved in the mixture of water (1.00 g, 55.51 mmol, 1 mL) and dioxane (2 mL). Resulting solution was stirred at 100° C. for 18 hr. Then, it was subjected to HPLC (Column: YMC-Actus Triart C18 100*20 mm, 5 um; 0-5 min 30-70% water-MeOH (NH₃ 0.1%), flow 30 ml/min), affording N-(6-amino-5-methyl-3-pyridyl)-2-[(2S,5R)-5-methyl-2-[3-(methylsulfamoyl)phenyl]-1-piperidyl]-2-oxo-acetamide (107 mg, 240.16 μmol, 54.15% yield).

$^1$H NMR (600 MHz, DMSO-$d_6$) δ (ppm) 1.01 (m, 3H), 1.34 (m, 1H), 1.62 (m, 1H), 1.89 (m, 1H), 1.99 (m, 3H), 2.12 (m, 2H), 2.36 (m, 1H), 2.40 (m, 3H), 2.87 (m, 1H), 3.77 (m, 1H), 5.60 (m, 3H), 7.45 (m, 1H), 7.58 (m, 3H), 7.68 (m, 2H), 7.97 (m, 1H). LCMS(ESI): [M]⁺ m/z: calcd 445.4; found 446.2; Rt=1.824 min.

Example 340. The Synthesis of N-(6-amino-5-methylpyridin-3-yl)-2-(5-methyl-2-(2-(methylamino)benzo[d]thiazol-5-yl)piperidin-1-yl)-2-oxoacetamide (Compound 852 and Compound 855

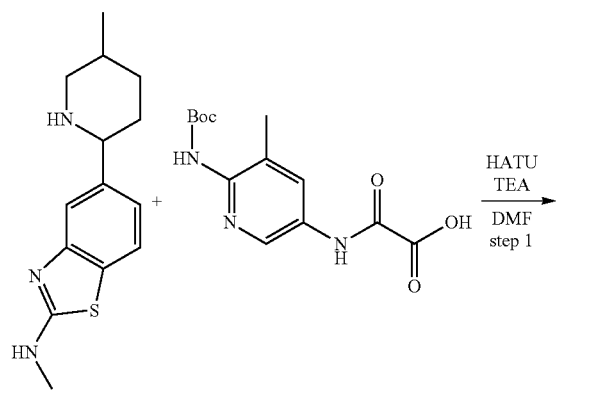

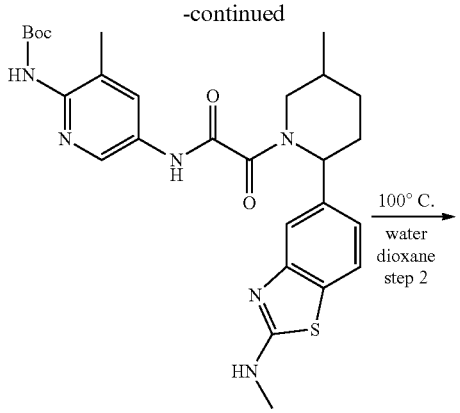

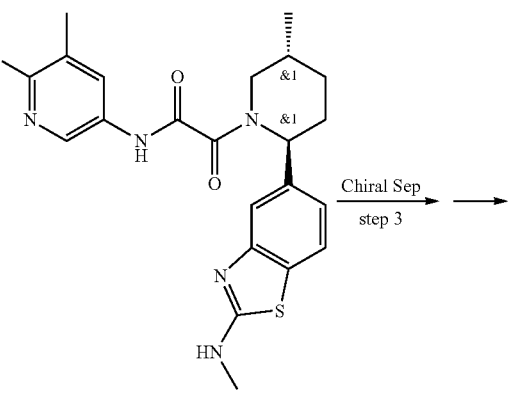

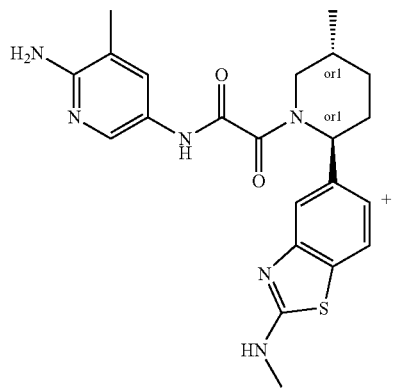

Compound 852

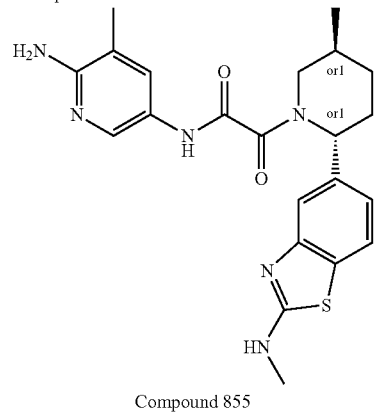

Compound 855

Step 1: Synthesis of tert-butyl (3-methyl-5-(2-(5-methyl-2-(2-(methylamino)benzo[d]thiazol-5-yl)piperidin-1-yl)-2-oxoacetamido)pyridin-2-yl)carbamate 2-[[6-(tert-butoxycarbonylamino)-5-methyl-3-pyridyl]amino]-2-oxo-acetic acid (338.91 mg, 1.15 mmol) and N-methyl-5-(5-methyl-2-piperidyl)-1,3-benzothiazol-2-amine (0.3 g, 1.15 mmol) were mixed in DMF (20 mL). The reaction suspension was cooled to 0° C. and HATU (523.68 mg, 1.38 mmol) followed by TEA (348.42 mg, 3.44 mmol, 479.91 µL) were added and stirred at ambient temperature for 14 hr. The reaction mixture was evaporated in vacuum and poured into water (100 ml) and extracted with EtOAc (2×40 ml). The combined organic extracts were washed with water (2*30 ml), dried over sodium sulphate and evaporated in vacuum to afford product tert-butyl N-[3-methyl-5-[[2-[5-methyl-2-[2-(methylamino)-1,3-benzothiazol-5-yl]-1-piperidyl]-2-oxo-acetyl]amino]-2-pyridyl]carbamate (0.35 g, 649.76 µmol, 56.61% yield).

$^1$H NMR (600 MHz, CDCl$_3$) δ (ppm) 1.11 (d, 3H), 1.22 (d, 3H), 1.44 (m, 1H), 1.53 (s, 9H), 1.98 (m, 1H), 2.24 (s, 3H), 2.30 (m, 3H), 3.11 (m, 1H), 4.56 (m, 1H), 5.48 (m, 1H), 6.68 (m, 1H), 7.02 (m, 1H), 7.55 (m, 3H), 8.04 (m, 1H), 8.35 (m, 1H), 9.40 (m, 1H).

LCMS(ESI): [M]$^+$ m/z: calcd 538.2; found 539.2; Rt=1.356 min.

Step 2: Synthesis of N-(6-amino-5-methylpyridin-3-yl)-2-(5-methyl-2-(2-(methylamino)benzo[d]thiazol-5-yl)piperidin-1-yl)-2-oxoacetamide Dioxane (20 mL) was added to a stirred solution of tert-butyl N-[3-methyl-5-[[2-[5-methyl-2-[2-(methylamino)-1,3-benzothiazol-5-yl]-1-piperidyl]-2-oxo-acetyl]amino]-2-pyridyl]carbamate (0.35 g, 649.76 µmol) in water (10 mL) at rt. The resulting mixture was stirred at 100° C. for 12 hr, and then evaporated in vacuum and obtained crude product 0.25 g was purified by preparative 55-55-75% 0-1-6 min H$_2$O/MeOH/0.1% NH$_4$OH, flow: 30 ml/min (loading pump 4 ml/min MeOH) target mass to afford product N-(6-amino-5-methyl-3-pyridyl)-2-[(2R,5S)-5-methyl-2-[2-(methylamino)-1,3-benzothiazol-5-yl]-1-piperidyl]-2-oxo-acetamide (0.12 g, 273.63 µmol, 42.11% yield).

LCMS(ESI): [M]$^+$ m/z: calcd 438.2; found 439.2; Rt=1.828 min.

Step 3: Chiral Separation (Compound 852 and Compound 855

The N-(6-amino-5-methyl-3-pyridyl)-2-[(2R,5S)-5-methyl-2-[2-(methylamino)-1,3-benzothiazol-5-yl]-1-piperidyl]-2-oxo-acetamide (120.00 mg, 273.63 µmol) was subjected to chiral HPLC purification (Column: IA-II (250*20.5 mkm), Eluent: Hexane-IPA-MeOH, 50-25-25, flow rate: 12 mL/min) to give the two individual enantiomers Compound 855 N-(6-amino-5-methyl-3-pyridyl)-2-[(2R,5S)-5-methyl-2-[2-(methylamino)-1,3-benzothiazol-5-yl]-1-piperidyl]-2-oxo-acetamide (0.05076 g, 115.75 µmol, 42.30% yield) and Compound 852 N-(6-amino-5-methyl-3-pyridyl)-2-[(2S,5R)-5-methyl-2-[2-(methylamino)-1,3-benzothiazol-5-yl]-1-piperidyl]-2-oxo-acetamide (58.16 mg, 132.62 µmol, 48.47% yield).

Ret time for Compound 852 in analytical conditions (column: IC, Hexane-IPA-MeOH, 50-25-25, 0.6 ml/min as mobile phase) 38.91 min and for Compound 855 29.63 min.

Compound 852: Retention time: 38.91 min $^1$H NMR (600 MHz, DMSO-d$_6$) δ (ppm) 0.98-1.02 (m, 3H), 1.26-1.39 (m, 1H), 1.63-1.74 (m, 1H), 1.77-1.90 (m, 1H), 1.97-2.03 (m, 3H), 2.03-2.17 (m, 1H), 2.19-2.29 (m, 1H), 2.72-2.78 (m, 0.4H), 2.88-2.95 (m, 3H), 3.20-3.26 (m, 0.6H), 3.41-4.04 (m, 1H), 5.11-5.59 (m, 1H), 5.59-5.67 (m, 2H), 6.90-7.02 (m, 1H), 7.28-7.38 (m, 1H), 7.39-7.51 (m, 1H), 7.59-7.66 (m, 1H), 7.88-7.94 (m, 1H), 7.94-8.05 (m, 1H), 10.34-10.77 (m, 1H).

LCMS(ESI): [M]$^+$ m/z: calcd 438.2; found 439.2; Rt=0.821 min.

Compound 855: Retention time: 29.63 min $^1$H NMR (600 MHz, DMSO-d$_6$) δ (ppm) 0.98-1.02 (m, 3H), 1.28-1.37 (m, 1H), 1.63-1.78 (m, 1H), 1.80-1.91 (m, 1H), 1.96-2.02 (m, 3H), 2.03-2.17 (m, 1H), 2.18-2.28 (m, 1H), 2.73-2.78 (m, 0.4H), 2.88-2.93 (m, 3H), 3.21-3.26 (m, 0.6H), 3.41-4.03 (m, 1H), 5.12-5.58 (m, 1H), 5.58-5.64 (m, 2H), 6.93-7.01 (m, 1H), 7.27-7.38 (m, 1H), 7.41-7.50 (m, 1H), 7.60-7.66 (m, 1H), 7.85-7.93 (m, 1H), 7.95-8.05 (m, 1H), 10.44-10.65 (m, 1H).

LCMS(ESI): [M]$^+$ m/z: calcd 438.2; found 439.2; Rt=0.821 min.

Example 341. The Synthesis of 2-[(2S,5R)-2-(5-acetamido-2-thienyl)-5-methyl-1-piperidyl]-N-(6-amino-5-methyl-3-pyridyl)-2-oxo-acetamide (Compound 732) and 2-[(2R,5S)-2-(5-acetamido-2-thienyl)-5-methyl-1-piperidyl]-N-(6-amino-5-methyl-3-pyridyl)-2-oxo-acetamide (Compound 717

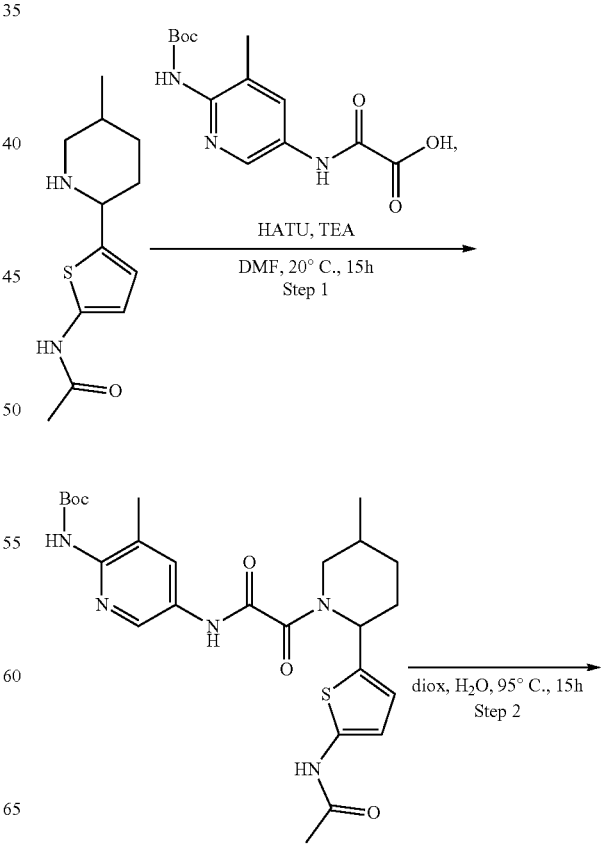

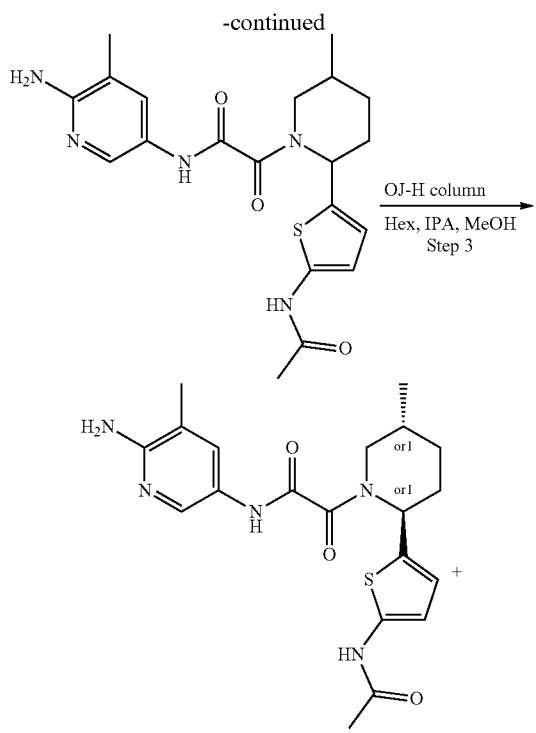

Compound 732

Compound 717

Step 1: The Synthesis of tert-butyl N-[5-[[2-[2-(5-acetamido-2-thienyl)-5-methyl-1-piperidyl]-2-oxo-acetyl]amino]-3-methyl-2-pyridyl]carbamate 2-[[6-(tert-butoxycarbonylamino)-5-methyl-3-pyridyl]amino]-2-oxo-acetic acid (1.01 g, 3.41 mmol) and N-[5-(5-methyl-2-piperidyl)-2-thienyl]acetamide (1.2 g, 3.41 mmol, CF$_3$COOH) were mixed in DMF. The reaction suspension was cooled to 20° C. and HATU (1.29 g, 3.41 mmol) followed by TEA (1.38 g, 13.62 mmol, 1.90 mL) were added and stirred at ambient temperature for 15 hr. The reaction mixture was evaporated in vacuo and poured into water (100 ml) and extracted with EtOAc (2*30 ml). The combined organic extracts were washed with water (2*30 ml), dried over sodium sulphate and evaporated in vacuo to afford product tert-butyl N-[5-[[2-[2-(5-acetamido-2-thienyl)-5-methyl-1-piperidyl]-2-oxo-acetyl]amino]-3-methyl-2-pyridyl]carbamate (0.8 g, 1.55 mmol, 45.56% yield).

$^1$H NMR (400 MHz, CDCl$_3$) δ 0.88 (m, 3H), 1.21 (m, 1H), 1.47 (s, 9H), 2.02 (m, 3H), 2.24 (s, 3H), 2.26 (m, 4H), 4.10 (m, 2H), 6.43 (d, 1H), 6.56 (d, 1H), 6.80 (s, 1H), 8.02 (s, 1H), 8.58 (m, 1H), 9.32 (m, 1H), 9.58 (s, 1H).

LCMS(ESI): [M+H]$^+$ m/z: calcd 515.2; found 516.4; Rt=1.227 min.

Step 2: The Synthesis of 2-[2-(5-acetamido-2-thienyl)-5-methyl-1-piperidyl]-N-(6-amino-5-methyl-3-pyridyl)-2-oxo-acetamide Water (10 mL) was added to a stirred solution of tert-butyl N-[5-[[2-[2-(5-acetamido-2-thienyl)-5-methyl-1-piperidyl]-2-oxo-acetyl]amino]-3-methyl-2-pyridyl]carbamate (0.8 g, 1.55 mmol) in dioxane (20 mL) at room temperature. The resulting mixture was stirred at 95° C. for 15 hr, and then evaporated in vacuo. The residue was diluted with water (20 mL) and extracted with EtOAc (2*30 mL). The combined organic extracts were dried over sodium sulphate and evaporated in vacuo and obtained crude product 0.55 g was purified by preparative 40-55% 1-6 min water-methanol (NH$_3$ 0.1%), flow 30 ml/min to afford product 2-[2-(5-acetamido-2-thienyl)-5-methyl-1-piperidyl]-N-(6-amino-5-methyl-3-pyridyl)-2-oxo-acetamide (0.16 g, 385.07 μmol, 24.82% yield).

LCMS(ESI): [M+H]$^+$ m/z: calcd 415.2; found 416.4; Rt=1.777 min.

Step 3: The Synthesis of 2-[(2S,5R)-2-(5-acetamido-2-thienyl)-5-methyl-1-piperidyl]-N-(6-amino-5-methyl-3-pyridyl)-2-oxo-acetamide (Compound 732) and 2-[(2R,5S)-2-(5-acetamido-2-thienyl)-5-methyl-1-piperidyl]-N-(6-amino-5-methyl-3-pyridyl)-2-oxo-acetamide (Compound 717)

The enantiomers were separated by chiral HPLC (column: OJ-H (250*20, 5 mkm)), Hexane-MeOH-IPA, 80-10-10, 13 ml/min as mobile phase) to give the two individual enantiomers Compound 732 2-[(2S,5R)-2-(5-acetamido-2-thienyl)-5-methyl-1-piperidyl]-N-(6-amino-5-methyl-3-pyridyl)-2-oxo-acetamide (0.126 g, 303.24 μmol, 78.75% yield) and Compound 717 2-[(2R,5S)-2-(5-acetamido-2-thienyl)-5-methyl-1-piperidyl]-N-(6-amino-5-methyl-3-pyridyl)-2-oxo-acetamide (0.0426 g, 102.53 μmol, 26.63% yield).

Compound 717: RT (OD-H, Hexane-IPA-MeOH, 50-25-25, 0.6 mL/min)=20.402 min.

$^1$H NMR (DMSO-d$_6$, 600 MHz): δ (ppm) 0.78 (m, 3H), 1.29 (m, 1H), 1.67 (m, 2H), 1.88 (m, 1H), 2.00 (m, 6H), 2.22 (m, 1H), 2.69 (m, 1H), 3.86 (m, 1H), 5.64 (m, 3H), 6.46 (m, 1H), 6.66 (m, 1H), 7.48 (d, 1H), 8.00 (d, 1H), 10.49 (m, 1H), 11.03 (s, 1H).

LCMS(ESI): [M+H]$^+$ m/z: calcd 415.2; found 416.2; Rt=1.837 min.

Compound 732: RT (OD-H, Hexane-IPA-MeOH, 50-25-25, 0.6 mL/min)=7.887 min.

$^1$H NMR (DMSO-d$_6$, 600 MHz): δ (ppm) 0.79 (m, 3H), 1.29 (m, 1H), 1.67 (m, 2H), 1.88 (m, 1H), 2.01 (d, 6H), 2.24 (m, 1H), 2.68 (m, 1H), 3.86 (m, 1H), 5.61 (m, 3H), 6.47 (m, 1H), 6.66 (m, 1H), 7.50 (d, 1H), 8.01 (d, 1H), 10.51 (m, 1H), 11.04 (s, 1H).

LCMS(ESI): [M+H]$^+$ m/z: calcd 415.2; found 416.2; Rt=1.831 min.

Example 342. The Synthesis of 5-(1-(2-((6-amino-5-methylpyridin-3-yl)amino)-2-oxoacetyl)-5-methylpiperidin-2-yl)thiophene-2-carboxamide (Compound 644, Compound 823, Compound 733 and Compound 733

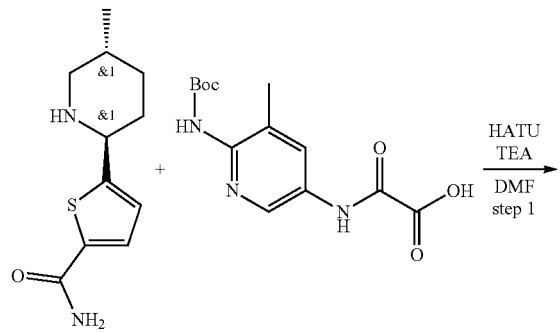

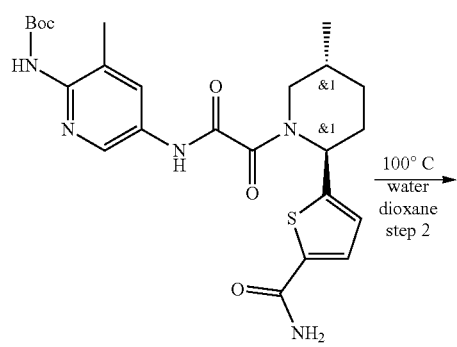

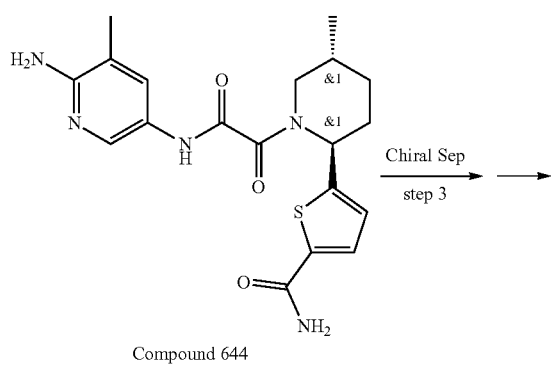

Compound 644

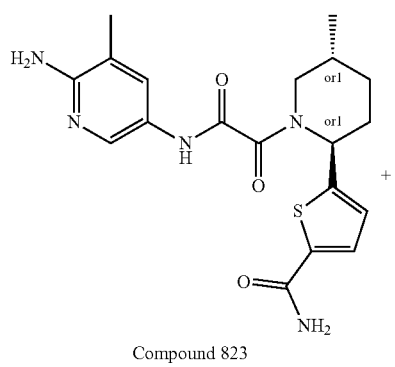

Compound 823

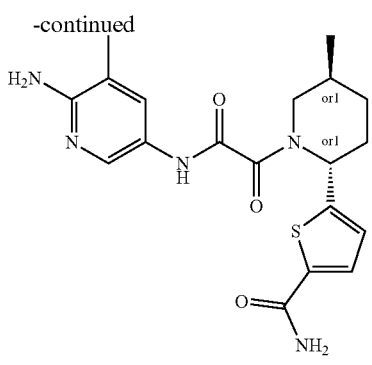

Compound 733

Step 1: Synthesis of rac-tert-butyl (5-(2-((2R,5S)-2-(5-carbamoylthiophen-2-yl)-5-methylpiperidin-1-yl)-2-oxoacetamido)-3-methylpyridin-2-yl)carbamate To a stirred mixture of 5-[(2S,5R)-5-methyl-2-piperidyl]thiophene-2-carboxamide (185 mg, 824.71 μmol), 2-[[6-(tert-butoxycarbonylamino)-5-methyl-3-pyridyl]amino]-2-oxo-acetic acid (243.53 mg, 824.71 μmol) and TEA (250.36 mg, 2.47 mmol, 344.84 μL) in DMF (3 mL) was added HATU (344.94 mg, 907.18 μmol). The resulting reaction mixture was stirred at 20° C. for 4 hr. Then, it was subjected to HPLC (column: YMC-Actus Triart C18 100*20 mml, 5 um; 50-75% 1-6 min water-MeOH (NH$_3$ 0.1%), flow 30 ml/min), affording tert-butyl N-[5-[[2-[(2S,5R)-2-(5-carbamoyl-2-thienyl)-5-methyl-1-piperidyl]-2-oxo-acetyl]amino]-3-methyl-2-pyridyl]carbamate (165 mg, 328.95 μmol, 39.89% yield).

$^1$H NMR (500 MHz, DMSO-d$_6$) δ (ppm)

LCMS(ESI): [M]$^+$ m/z: calcd 501.2; found 502.2; Rt=2.438 min.

Step 2: Synthesis of 5-(1-(2-((6-amino-5-methylpyridin-3-yl)amino)-2-oxoacetyl)-5-methylpiperidin-2-yl)thiophene-2-carboxamide (Compound 644

Water (1.00 g, 55.51 mmol, 1 mL) was added to a solution of tert-butyl N-[5-[[2-[(2S,5R)-2-(5-carbamoyl-2-thienyl)-5-methyl-1-piperidyl]-2-oxo-acetyl]amino]-3-methyl-2-pyridyl]carbamate (165 mg, 328.95 μmol) in dioxane (2 mL). Resulting solution was stirred at 100° C. for 16 hr. Then, it was subjected to HPLC (column: YMC Triart C18 100×20 mm, 5 um; 10-60% 0-5 min H$_2$O/MeOH/0.1% NH$_4$OH, flow: 30 ml/min), affording 5-[(2S,5R)-1-[2-[(6-amino-5-methyl-3-pyridyl)amino]-2-oxo-acetyl]-5-methyl-2-piperidyl]thiophene-2-carboxamide (130 mg, 323.80 μmol, 98.43% yield).

$^1$H NMR (600 MHz, DMSO-d$_6$) δ (ppm) 0.98 (d, 3H), 1.40 (m, 1H), 1.79 (m, 1H), 1.90 (m, 1H), 2.00 (m, 4H), 2.07 (m, 1H), 2.16 (m, 1H), 3.73 (m, 1H), 5.66 (m, 3H), 6.99 (m, 1H), 7.31 (s, 1H), 7.48 (d, 1H), 7.61 (m, 1H), 7.91 (s, 1H), 8.00 (s, 1H), 10.48 (m, 1H).

LCMS(ESI): [M]$^+$ m/z: calcd 401.2; found 402.2; Rt=1.607 min.

Step 3: Chiral Separation (Compound 823, Compound 733 and Compound 733

5-[(2S,5R)-1-[2-[(6-amino-5-methyl-3-pyridyl)amino]-2-oxo-acetyl]-5-methyl-2-piperidyl]thiophene-2-carboxamide (130 mg, 323.80 μmol) was divided into enantiomers by Chiral HPLC: System 1: Column: Chiralcel OJ-H (250×20 mm, 5 mkm); Mobile phase: Hexane-IPA-MeOH, 70-15-15, Flow Rate: 12 mL/min; Column Temperature: 24° C.; Wavelength: 205 nm, 272 nm); System 2: System 2. Column: Chiralpak IC (250×20 mm, 5 mkm); Mobile phase: Hexane-IPA-MeOH, 50-25-25, Flow Rate: 12 mL/min; Column Temperature: 24° C.; Wavelength: 205 nm, 272 nm), affording: 5-[(2S,5R)-1-[2-[(6-amino-5-methyl-3-pyridyl)amino]-2-oxo-acetyl]-5-methyl-2-piperidyl]thiophene-2-carboxamide (50 mg, 124.54 μmol, 76.92% yield) with ret.time=34.629 min (Compound 823) and 5-[(2R,5S)-1-[2-[(6-amino-5-methyl-3-pyridyl)amino]-2-oxo-acetyl]-5-methyl-2-piperidyl]thiophene-2-carboxamide (52 mg, 129.52 μmol, 80.00% yield) with ret.time=50.495 min (Compound 733). Ret time for Compound 823 in analytical conditions (column: IB, $CO_2$-MeOH, 80-20, 3 ml/min as mobile phase) 17.78 min and for Compound 733, Compound 733 19.47 min.

Compound 823: Retention time: 17.78 min
$^1$H NMR (600 MHz, DMSO-$d_6$) δ (ppm) 0.96-1.01 (m, 3H), 1.36-1.44 (m, 1H), 1.74-1.85 (m, 1H), 1.85-1.96 (m, 1H), 1.97-2.04 (m, 4H), 2.04-2.19 (m, 1H), 2.83-3.28 (m, 1H), 3.42-4.05 (m, 1H), 5.37-5.85 (m, 3H), 6.94-7.02 (m, 1H), 7.32 (br s, 1H), 7.45-7.51 (m, 1H), 7.58-7.67 (m, 1H), 7.90 (br s, 1H), 7.98-8.03 (m, 1H), 10.36-10.61 (m, 1H).
LCMS(ESI): [M]$^+$ m/z: calcd 401.2; found 402.2; Rt=0.915 min.

Compound 733: Retention time: 19.47 min
$^1$H NMR (600 MHz, DMSO-$d_6$) δ (ppm) 0.96-1.01 (m, 3H), 1.36-1.44 (m, 1H), 1.74-1.85 (m, 1H), 1.85-1.96 (m, 1H), 1.97-2.04 (m, 4H), 2.04-2.19 (m, 1H), 2.83-3.28 (m, 1H), 3.42-4.05 (m, 1H), 5.37-5.85 (m, 3H), 6.94-7.02 (m, 1H), 7.32 (br s, 1H), 7.45-7.51 (m, 1H), 7.58-7.67 (m, 1H), 7.90 (br s, 1H), 7.98-8.03 (m, 1H), 10.36-10.61 (m, 1H).
LCMS(ESI): [M]$^+$ m/z: calcd 401.2; found 402.2; Rt=0.917 min.

Example 343. The Synthesis of 5-(1-(2-((6-amino-5-methylpyridin-3-yl)amino)-2-oxoacetyl)-5-methylpiperidin-2-yl)-N-methylthiophene-2-carboxamide (Compound 859 and Compound 849

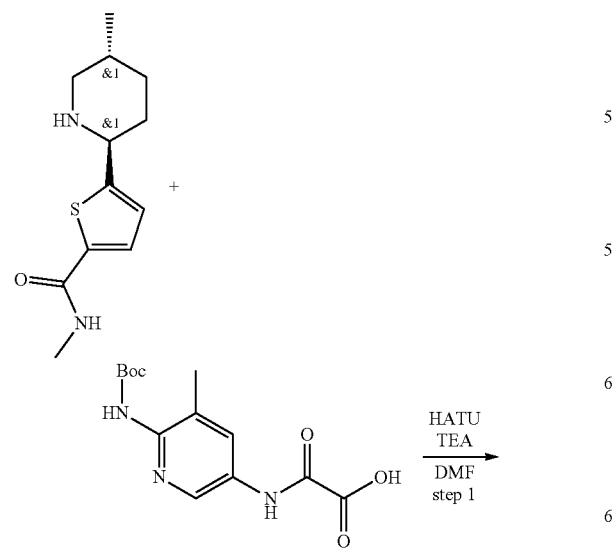

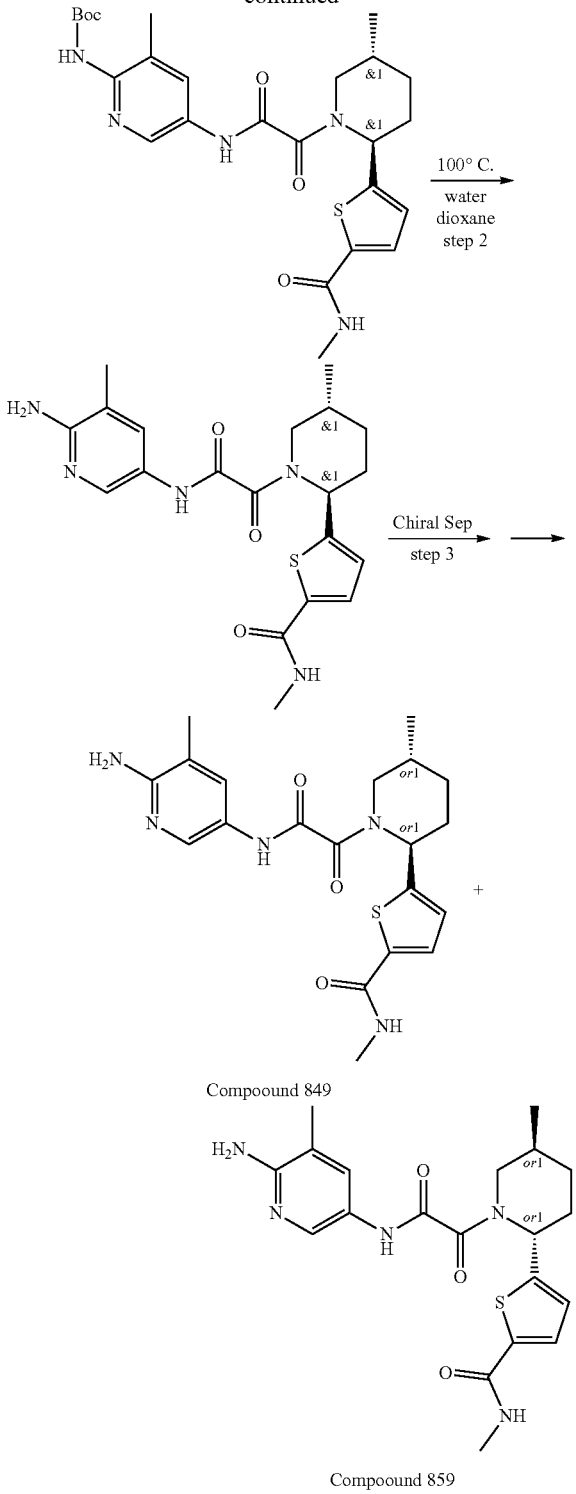

Step 1: Synthesis of rac-tert-butyl (3-methyl-5-(2-((2R,5S)-5-methyl-2-(5-(methylcarbamoyl)thiophen-2-yl)piperidin-1-yl)-2-oxoacetamido)pyridin-2-yl) carbamate To a stirred mixture of N-methyl-5-[(2S,5R)-5-methyl-2-piperidyl]thiophene-2-carboxamide (186 mg, 780.37 μmol), 2-[[6-(tert-butoxycarbonylamino)-5-methyl-3-pyridyl]amino]-2-oxo-acetic acid (230.44 mg, 780.37 μmol) and TEA (157.93 mg, 1.56 mmol, 217.54 μL) in DMF (3 mL) was added HATU (326.39 mg, 858.41 μmol). The resulting reaction mixture was stirred at 20° C. for 4 hr. Then, it was subjected to HPLC (20-50% 0-5 min H$_2$O/ACN, flow: 30 ml/min; column: YMC Triart C18 100×20 mm, 5 um), affording tert-butyl N-[3-methyl-5-[[2-[(2S,5R)-5-methyl-2-[5-(methylcarbamoyl)-2-thienyl]-1-piperidyl]-2-oxo-acetyl]amino]-2-pyridyl]carbamate (167 mg, 323.88 μmol, 41.50% yield).

LCMS(ESI): [M]$^+$ m/z: calcd 515.2; found 516.2; Rt=2.621 min.

Step 2: Synthesis of 5-(1-(2-((6-amino-5-methylpyridin-3-yl)amino)-2-oxoacetyl)-5-methylpiperidin-2-yl)-N-methylthiophene-2-carboxamide Water (5.83 mg, 323.88 μmol, 5.83 μL) was added to a solution of tert-butyl N-[3-methyl-5-[[2-[(2S,5R)-5-methyl-2-[5-(methylcarbamoyl)-2-thienyl]-1-piperidyl]-2-oxo-acetyl]amino]-2-pyridyl]carbamate (167 mg, 323.88 μmol) in dioxane (2 mL). Resulting mixture was stirred at 100° C. for 15 hr. Then, it was subjected to HPLC (30-30-80% 0-1-6 min H$_2$O/MeOH/0.1% NH$_4$OH, flow: 30 ml/min; column: YMC Triart C18 100×20 mm, 5 um), affording 5-[(2S,5R)-1-[2-[(6-amino-5-methyl-3-pyridyl)amino]-2-oxo-acetyl]-5-methyl-2-piperidyl]-N-methyl-thiophene-2-carboxamide (89 mg, 214.20 μmol, 66.13% yield).

LCMS(ESI): [M]$^+$ m/z: calcd 415.2; found 416.2; Rt=1.708 min.

Step 3: Chiral Separation (Compound 859 and Compound 849

5-[(2S,5R)-1-[2-[(6-amino-5-methyl-3-pyridyl)amino]-2-oxo-acetyl]-5-methyl-2-piperidyl]-N-methyl-thiophene-2-carboxamide (89 mg, 214.20 μmol) was divided into enantiomers by Chiral HPLC (Chiralpak IA 250*20 mm, 5 mkm; Hexane-IPA-MeOH, 50-25-25, 12 ml/min), affording: 5-[(2S,5R)-1-[2-[(6-amino-5-methyl-3-pyridyl)amino]-2-oxo-acetyl]-5-methyl-2-piperidyl]-N-methyl-thiophene-2-carboxamide (28.9 mg, 69.55 μmol, 64.94% yield) with ret.time=24.6 min (Compound 849) and 5-[(2R,5S)-1-[2-[(6-amino-5-methyl-3-pyridyl)amino]-2-oxo-acetyl]-5-methyl-2-piperidyl]-N-methyl-thiophene-2-carboxamide (33.3 mg, 80.14 μmol, 74.83% yield) with ret.time=56.64 min (Compound 859).

Ret time for Compound 859 in analytical conditions (column: IA, Hexane-IPA-MeOH, 50-25-25, 0.6 ml/min as mobile phase) 49.85 min and for Compound 849 29.12 min.

Compound 859: Retention time: 49.85 min $^1$H NMR (600 MHz, DMSO-d$_6$) δ (ppm) 0.97-1.01 (m, 3H), 1.34-1.49 (m, 2H), 1.75-1.84 (m, 1H), 1.86-1.96 (m, 1H), 2.03-2.06 (m, 3H), 2.06-2.19 (m, 1H), 2.70-2.74 (m, 3H), 2.84-3.24 (m, 1H), 3.45-4.06 (m, 1H), 5.34-5.85 (m, 1H), 6.21 (br s, 2H), 6.97-7.02 (m, 1H), 7.54-7.62 (m, 2H), 8.08 (s, 1H), 8.33-8.41 (m, 1H), 10.55-10.79 (m, 1H).

LCMS(ESI): [M]$^+$ m/z: calcd 415.2; found 416.2; Rt=1.755 min.

Compound 849: Retention time: 29.12 min $^1$H NMR (600 MHz, DMSO-d$_6$) δ (ppm) 0.95-1.00 (m, 3H), 1.37-1.44 (m, 1H), 1.76-1.84 (m, 1H), 1.86-1.96 (m, 1H), 2.00-2.04 (m, 3H), 2.12-2.19 (m, 3H), 2.69-2.74 (m, 3H), 2.84-3.21 (m, 1H), 3.46-4.09 (m, 1H), 5.38-5.88 (m, 1H), 6.98-7.03 (m, 1H), 7.25 (br s, 2H), 7.53-7.60 (m, 1H), 7.71-7.84 (m, 1H), 8.22 (s, 1H), 8.35-8.41 (m, 1H), 10.95 (s, 1H), 13.14 (brs, 1H).

LCMS(ESI): [M]$^+$ m/z: calcd 415.2; found 416.2; Rt=1.756 min.

Example 344. The Synthesis of rel-N-(6-amino-5-methyl-3-pyridyl)-2-[(2S,5R)-2-(1,3-benzothiazol-5-yl)-5-methyl-1-piperidyl]-2-oxo-acetamide (Compound 616) and rel-N-(6-amino-5-methyl-3-pyridyl)-2-[(2R,5S)-2-(1,3-benzothiazol-5-yl)-5-methyl-1-piperidyl]-2-oxo-acetamide (Compound 635

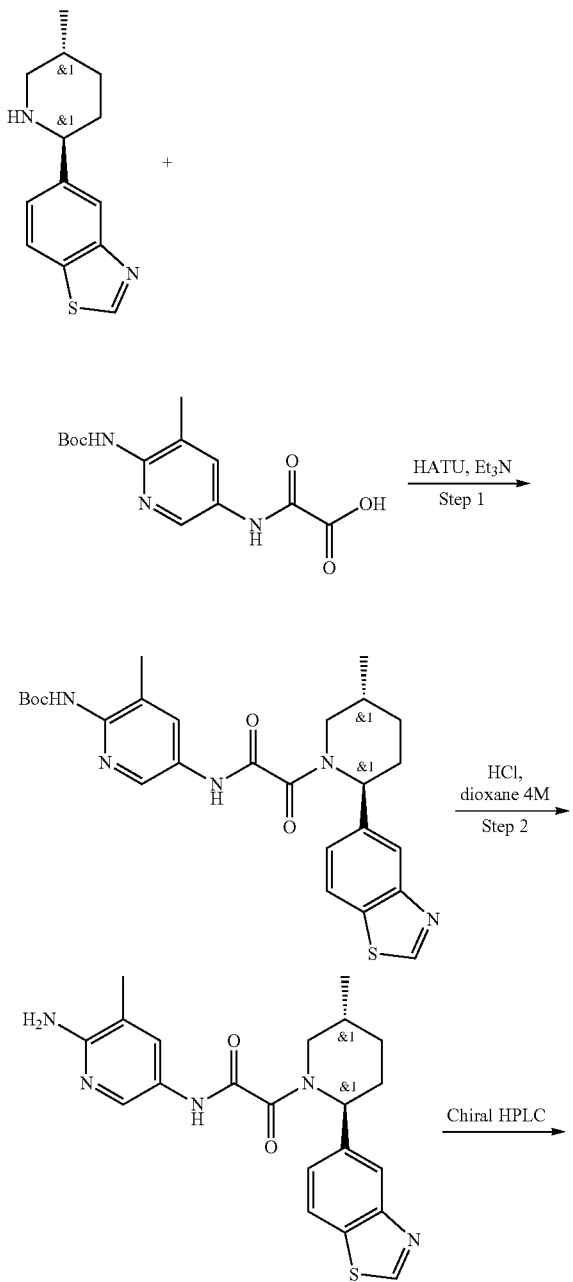

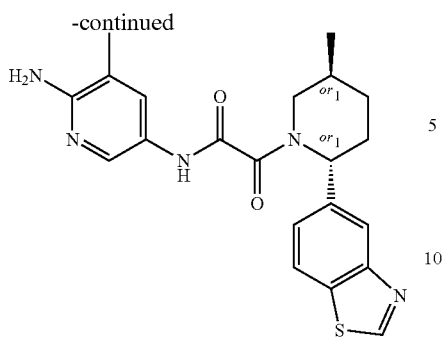

Compoound 616

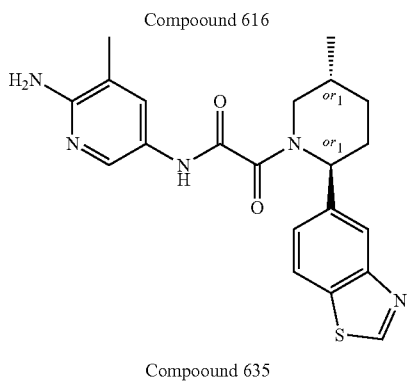

Compoound 635

Step 1: Synthesis of tert-butyl N-[5-[[2-[2-(1,3-benzothiazol-5-yl)-5-methyl-1-piperidyl]-2-oxo-acetyl]amino]-3-methyl-2-pyridyl]carbamate HATU (490.95 mg, 1.29 mmol) was added portionwise at r.t. to a suspension of 2-[[6-(tert-butoxycarbonylamino)-5-methyl-3-pyridyl]amino]-2-oxo-acetic acid (381.28 mg, 1.29 mmol), 5-(5-methyl-2-piperidyl)-1,3-benzothiazole (300 mg, 1.29 mmol) and TEA (783.93 mg, 7.75 mmol, 1.08 mL) in DMF (10 mL). The clear solution was stirred at 25° C. for 18 hr and the solvents were evaporated in vacuo. The residue was dissolved in EtOAc (100 mL), washed with water (3×50 mL) and evaporated in vacuo to give tert-butyl N-[5-[[2-[2-(1,3-benzothiazol-5-yl)-5-methyl-1-piperidyl]-2-oxo-acetyl]amino]-3-methyl-2-pyridyl]carbamate (700 mg, crude).

$^1$H NMR (DMSO-$d_6$, 400 MHz): δ 1.01 (d, 3H), 1.39 (m, 13H), 2.09 (m, 8H), 5.71 (m, 1H), 7.43 (m, 2H), 8.12 (m, 1H), 8.43 (s, 1H), 9.03 (s, 1H), 9.38 (m, 1H), 11.00 (s, 1H).

LCMS(ESI): [M+H]$^+$ m/z: calcd 509.2; found 510.2; Rt=1.319 min.

Step 2: Synthesis of N-(6-amino-5-methyl-3-pyridyl)-2-[2-(1,3-benzothiazol-5-yl)-5-methyl-1-piperidyl]-2-oxo-acetamide Hydrogen chloride solution 4.0 M in dioxane (3.58 g, 13.74 mmol, 3.41 mL, 14% purity) was carefully added at r.t. to a solution of tert-butyl N-[5-[[2-[2-(1,3-benzothiazol-5-yl)-5-methyl-1-piperidyl]-2-oxo-acetyl]amino]-3-methyl-2-pyridyl]carbamate (700 mg, 1.37 mmol) in DCM (10 mL). The reaction mixture was then stirred for 12 hr at r.t. and the solvents were evaporated in vacuo. The residue was subjected to RP-HPLC (column: YMC Triart C18 100×20 mm, 5 um; 40-40-90% 0-1-5 min 0.10% NH$_3$-methanol as mobile phase) to give N-(6-amino-5-methyl-3-pyridyl)-2-[2-(1,3-benzothiazol-5-yl)-5-methyl-1-piperidyl]-2-oxo-acetamide (331 mg, 808.30 μmol, 58.85% yield).

LCMS(ESI): [M+H]$^+$ m/z: calcd 409.2; found 410.2; Rt=2.176 min.

Step 3: Synthesis of rel-N-(6-amino-5-methyl-3-pyridyl)-2-[(2S,5R)-2-(1,3-benzothiazol-5-yl)-5-methyl-1-piperidyl]-2-oxo-acetamide (Compound 616) and rel-N-(6-amino-5-methyl-3-pyridyl)-2-[(2R,5S)-2-(1,3-benzothiazol-5-yl)-5-methyl-1-piperidyl]-2-oxo-acetamide (Compound 635

The enantiomers were separated by chiral HPLC (column: IC II, Hexane-IPA-MeOH, 50-25-25, 12 ml/min as mobile phase) to give the two individual enantiomers Compound 635 N-(6-amino-5-methyl-3-pyridyl)-2-[(2S,5R)-2-(1,3-benzothiazol-5-yl)-5-methyl-1-piperidyl]-2-oxo-acetamide (161 mg, 393.16 μmol, 97.28% yield) RetTime=32.4 min, [α]21D=−176.7° (c=0.1 g/100 mL, EtOH) and Compound 616 N-(6-amino-5-methyl-3-pyridyl)-2-[(2R,5S)-2-(1,3-benzothiazol-5-yl)-5-methyl-1-piperidyl]-2-oxo-acetamide (160 mg, 390.72 μmol, 96.68% yield) RetTime=45.8 min, [α]21D=+191.5° (c=0.1 g/100 mL, EtOH).

Compound 616: RT (IC, Hexane-IPA-MeOH, 50-25-25, 0.6 ml/min)=47.098 min.

$^1$H NMR (600 MHz, DMSO-$d_6$) δ 0.98-1.06 (m, 3H), 1.30-1.42 (m, 1H), 1.66-1.75 (m, 1H), 1.82-1.91 (m, 1H), 1.95-2.04 (m, 3H), 2.06-2.23 (m, 1H), 2.26-2.35 (m, 1H), 2.76-3.27 (m, 1H), 3.38-4.06 (m, 1H), 5.26-5.60 (m, 1H), 5.60-5.76 (m, 2H), 7.39-7.46 (m, 1H), 7.50 (s, 1H), 7.92-8.01 (m, 1H), 8.01-8.06 (m, 1H), 8.13-8.20 (m, 1H), 9.37-9.43 (m, 1H), 10.50-10.70 (m, 1H).

LCMS(ESI): [M+H]$^+$ m/z: calcd 409.2; found 410.0; Rt=1.992 min.

Compound 635 RT (IC, Hexane-IPA-MeOH, 50-25-25, 0.6 ml/min)=35.176 min.

$^1$H NMR (600 MHz, DMSO-$d_6$) δ 1.00-1.05 (m, 3H), 1.27-1.40 (m, 1H), 1.64-1.75 (m, 1H), 1.82-1.93 (m, 1H), 1.95-2.04 (m, 3H), 2.07-2.25 (m, 1H), 2.27-2.35 (m, 1H), 2.75-3.27 (m, 1H), 3.42-4.11 (m, 1H), 5.28-5.59 (m, 1H), 5.60-5.74 (m, 2H), 7.40-7.45 (m, 1H), 7.49 (s, 1H), 7.94-8.01 (m, 1H), 8.01-8.06 (m, 1H), 8.13-8.19 (m, 1H), 9.36-9.42 (m, 1H), 10.52-10.58 (m, 1H).

LCMS(ESI): [M+H]$^+$ m/z: calcd 409.2; found 410.2; Rt=2.001 min.

Example 345. The Synthesis of N-(6-amino-5-methyl-3-pyridyl)-2-[2-(4,4-difluorocyclohexyl)-1-piperidyl]-2-oxo-acetamide (Compound 186

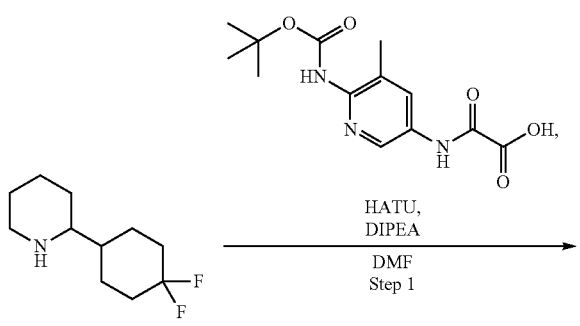

2037

-continued

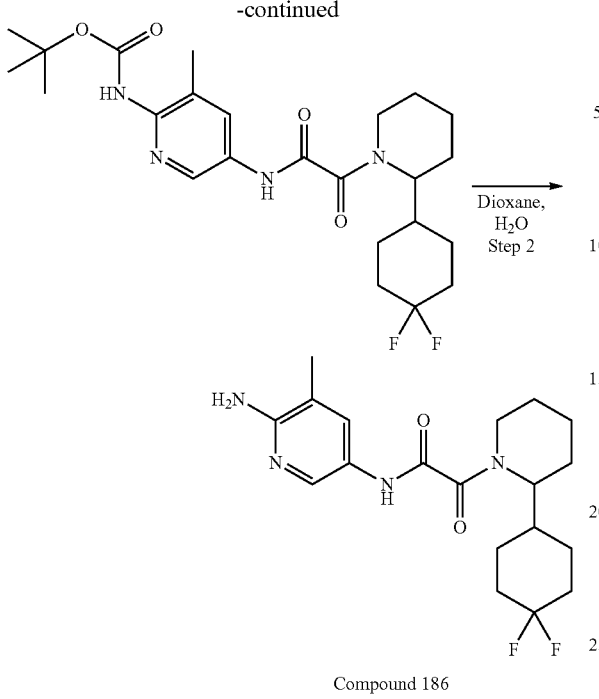

Compound 186

Step 1: Synthesis of tert-butyl N-[5-[[2-[2-(4,4-difluorocyclohexyl)-1-piperidyl]-2-oxo-acetyl]amino]-3-methyl-2-pyridyl]carbamate A mixture of 2-(4,4-difluorocyclohexyl)piperidine (0.2 g, 983.91 µmol), 2-[[6-(tert-butoxycarbonylamino)-5-methyl-3-pyridyl]amino]-2-oxo-acetic acid (330.77 mg, 1.12 mmol) and triethylamine (844.19 mg, 8.34 mmol, 1.16 mL) in DMF (3 mL) was stirred at 25° C. for 20 minutes. After 20 minutes, HATU (475.82 mg, 1.25 mmol) was added. The resulting reaction mixture was stirred at 25° C. for overnight. Upon completion, water (20 mL) was added to the reaction mixture and extracted with Ethyl acetate (2×25 mL). The combined organic phase was washed with water (3×25 mL), brine, dried over Na$_2$SO$_4$, filtered and dried under reduced pressure. The crude reaction mixture was subjected to reverse phase HPLC purification (Eluent: 10-50%, 2-10 min, methanol; flow rate: 30 mL/min; loading pump: 4 mL MeOH; column: SunFire 100*19 mm, 5 µM) to get tert-butyl N-[5-[[2-[2-(4,4-difluorocyclohexyl)-1-piperidyl]-2-oxo-acetyl]amino]-3-methyl-2-pyridyl]carbamate (81.10 mg, 168.77 µmol, 20.23% yield) as a light-yellow solid.

LCMS(ESI): [M+Boc]$^+$ m/z: calcd 480.3; found 481.2; Rt=1.386 min.

Step 2: Synthesis of N-(6-amino-5-methyl-3-pyridyl)-2-[2-(4,4-difluorocyclohexyl)-1-piperidyl]-2-oxo-acetamide (Compound 186

A stirring solution of tert-butyl N-[5-[[2-[2-(4,4-difluorocyclohexyl)-1-piperidyl]-2-oxo-acetyl]amino]-3-methyl-2-pyridyl]carbamate (81.10 mg, 168.77 µmol) in Dioxane (2 mL) and Water (2 mL) was heated at 100° C. for 18 hours. Then, the reaction mixture was evaporated to dryness and the crude product was purified by HPLC (Eluent: 2-10 min, 35-60%, water-MeOH+NH$_3$; loading pump: 4 mL/min, MeOH+NH$_3$; column: Sunfire 100*20 mm, 5 µM) to obtain

2038

N-(6-amino-5-methyl-3-pyridyl)-2-[2-(4,4-difluorocyclohexyl)-1-piperidyl]-2-oxo-acetamide (Compound 186, 22.60 mg, 59.41 µmol, 35.20% yield) as a light-yellow solid.

Compound 186: $^1$H NMR (DMSO-d$_6$, 400 MHz): δ (ppm) 1.18 (m, 2H), 1.44 (m, 2H), 1.63 (m, 4H), 1.81 (m, 4H), 2.01 (d, 6H), 2.91 (m, 1H), 3.53 (m, 1H), 4.21 (m, 1H), 5.63 (m, 2H), 7.47 (m, 1H), 7.99 (m, 1H), 10.34 (m, 1H).

LCMS(ESI): [M+H]$^+$ m/z: calcd 380.2; found 381.1; Rt=1.014 min.

Example 346. The Synthesis of N-(6-amino-5-methyl-3-pyridyl)-2-[(2S,5R)-2-isopropyl-5-methyl-1-piperidyl]-2-oxo-acetamide (Compound 165

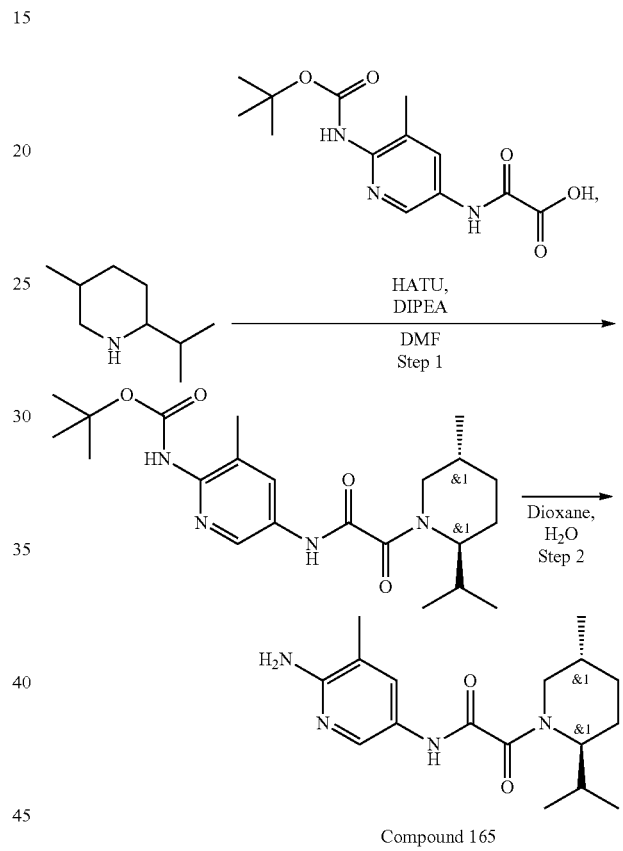

Compound 165

Step 1: Synthesis of tert-butyl N-[5-[[2-(2-isopropyl-5-methyl-1-piperidyl)-2-oxo-acetyl]amino]-3-methyl-2-pyridyl]carbamate To a stirred solution of 2-[[6-(tert-butoxycarbonylamino)-5-methyl-3-pyridyl]amino]-2-oxo-acetic acid (0.33 g, 1.12 mmol) and 2-isopropyl-5-methyl-piperidine (198.60 mg, 1.12 mmol, HCl) in DMF (10 mL) was added DIPEA (505.52 mg, 3.91 mmol, 681.29 µL). The resulting mixture was stirred for 5 minutes. After 5 minutes, a solution of HATU (446.17 mg, 1.17 mmol) in DMF (2 mL) was added. The resulting reaction mixture was stirred for overnight at room temperature. Upon completion, the resulting suspension was concentrated under reduced pressure and the crude product was purified by HPLC to afford tert-butyl N-[5-[[2-(2-isopropyl-5-methyl-1-piperidyl)-2-oxo-acetyl]amino]-3-methyl-2-pyridyl]carbamate (131.5 mg, 314.20 µmol, 28.11% yield) as a light-yellow solid.

LCMS(ESI): [M+Boc]⁺ m/z: calcd 418.2; found 419.4; Rt=3.635 min.

Step 2: Synthesis of N-(6-amino-5-methyl-3-pyridyl)-2-[(2S,5R)-2-isopropyl-5-methyl-1-piperidyl]-2-oxo-acetamide (Compound 165

A stirring solution of tert-butyl N-[5-[[2-[(2S,5R)-2-isopropyl-5-methyl-1-piperidyl]-2-oxo-acetyl]amino]-3-methyl-2-pyridyl]carbamate (131.50 mg, 314.20 μmol) in Dioxane (2 mL) and Water (5 mL) was heated at 100° C. for 17 hours. Then, the reaction mixture was evaporated to dryness and the crude product was purified by HPLC (Eluent: 2-10 min, 10-50% CH₃CN+NH₃; flow rate: 30 mL/min; loading pump: 4 mL/min, CH₃CN; column: Triart C18 100*20 mm, 5 um) to obtain N-(6-amino-5-methyl-3-pyridyl)-2-[(2S,5R)-2-isopropyl-5-methyl-1-piperidyl]-2-oxo-acetamide (Compound 165, 50 mg, 157.03 μmol, 49.98% yield) as a light-yellow solid.

Compound 165: ¹H NMR (CDCl₃, 400 MHz): δ (ppm) 0.94 (m, 8H), 1.29 (m, 1H), 1.82 (m, 5H), 2.11 (s, 4H), 3.11 (m, 1H), 4.21 (m, 1H), 4.43 (s, 2H), 4.65 (m, 1H), 7.70 (d, 1H), 8.02 (s, 1H), 9.14 (s, 1H).

LCMS(ESI): [M+H]⁺ m/z: calcd 318.2; found 319.4 Rt=2.464 min.

Example 347. The Synthesis of N-(6-amino-5-methyl-3-pyridyl)-2-(2-isopropyl-1-piperidyl)-2-oxo-acetamide (Compound 135), N-(6-amino-5-methyl-3-pyridyl)-2-[(2R)-2-isopropyl-1-piperidyl)-2-oxo-acetamide and N-(6-amino-5-methyl-3-pyridyl)-2-[(2S)-2-isopropyl-1-piperidyl)-2-oxo-acetamide (Compound 204 and Compound 192

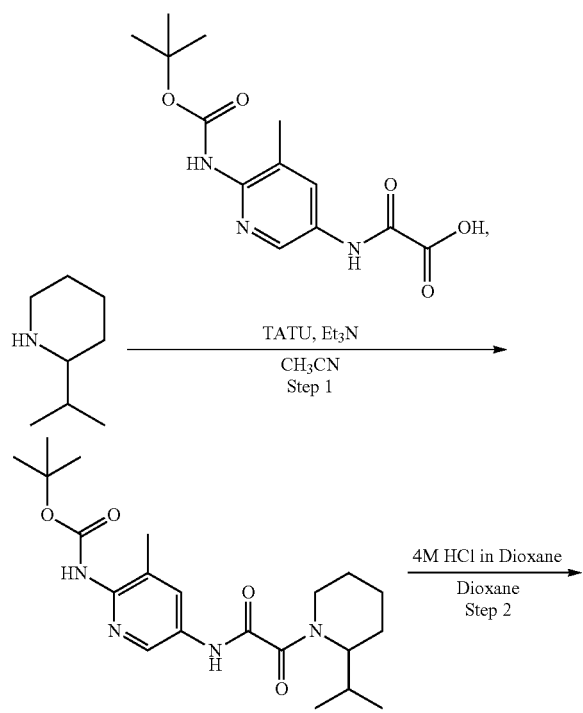

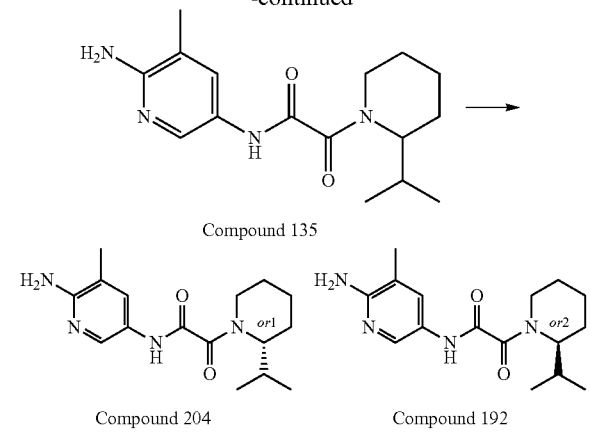

Step 1: Synthesis of tert-butyl N-[5-[[2-(2-isopropyl-1-piperidyl)-2-oxo-acetyl]amino]-3-methyl-2-pyridyl]carbamate 2-[[6-(tert-butoxycarbonylamino)-5-methyl-3-pyridyl]amino]-2-oxo-acetic acid (0.3 g, 1.02 mmol), TATU (392.65 mg, 1.22 mmol) and triethylamine (308.41 mg, 3.05 mmol, 424.81 μL) were mixed together in dry CH₃CN (25 mL) at 21° C. and the resulting mixture was stirred for 6 hours. After 6 hours, 2-isopropylpiperidine (182.93 mg, 1.12 mmol, HCl salt) was added and the resulting mixture was stirred at 21° C. for overnight. The resulting mixture was then evaporated to dryness and subjected to HPLC purification (Eluent: 0.1% formic acid/CH₃CN, 5-95% CH₃CN, 6 min; column: Zorbax Eclipse-plus C18, 4.6*100 mm, 3.5 um) to get tert-butyl N-[5-[[2-(2-isopropyl-1-piperidyl)-2-oxo-acetyl]amino]-3-methyl-2-pyridyl]carbamate (45.7 mg, 112.98 μmol, 11.12% yield) as a white solid.

LCMS(ESI): [M+Boc]⁺ m/z: calcd 404.3; found 405.4; Rt=3.291 min.

Step 2: Synthesis of N-(6-amino-5-methyl-3-pyridyl)-2-(2-isopropyl-1-piperidyl)-2-oxo-acetamide (Compound 135

To a stirred solution of tert-butyl N-[5-[[2-(2-isopropyl-1-piperidyl)-2-oxo-acetyl]amino]-3-methyl-2-pyridyl]carbamate (45.7 mg, 112.98 μmol) in dioxane (5 mL) was added 4.0 M HCl in dioxane (800.00 mg, 21.94 mmol, 1 mL) at 21° C. The resulting reaction mixture was stirred for 12 hours. Upon completion, the precipitated solid was filtered off, washed with MTBE and dried under high vacuum (0.3 mbar). The obtained crude product was purified by reverse phase HPLC (Eluent: 2-7 min, 15-30% CH₃CN, flow rate: 30 mL/min; column: SunFire C18 100*19 mm, 5 μM) to give N-(6-amino-5-methyl-3-pyridyl)-2-(2-isopropyl-1-piperidyl)-2-oxo-acetamide (Compound 135, 15.9 mg, 52.24 μmol, 46.24% yield) as a light-yellow solid.

¹H NMR (DMSO-d₆, 500 MHz): δ (ppm) 0.85 (m, 6H), 1.33 (m, 2H), 1.59 (m, 4H), 1.82 (m, 1H), 2.16 (m, 1H), 2.97 (m, 2H), 3.47 (m, 2H), 4.13 (m, 1H), 5.60 (m, 2H), 7.48 (m, 1H), 8.00 (m, 1H), 10.32 (m, 1H).

LCMS(ESI): [M+H]⁺ m/z: calcd 304.2; found 305.2; Rt=0.973 min.

Chiral Separation of N-(6-amino-5-methyl-3-pyridyl)-2-[(2R)-2-isopropyl-1-piperidyl]-2-oxo-acetamide and N-(6-amino-5-methyl-3-pyridyl)-2-[(2S)-2-isopropyl-1-piperidyl]-2-oxo-acetamide (Compound 204 and Compound 192 rac-N-(6-amino-5-methyl-3-pyridyl)-2-(2-isopropyl-1-piperidyl)-2-oxo-acetamide (Compound 135) was subjected to chiral chromatography to give N-(6-amino-5-methyl-3-pyridyl)-2-[(2R)-2-isopropyl-1-piperidyl]-2-oxo-acetamide (Compound 204) and N-(6-amino-5-methyl-3-pyridyl)-2-[(2S)-2-isopropyl-1-piperidyl]-2-oxo-acetamide (Compound 192) as white solids.

Compound 204: LCMS(ESI): [M+H]$^+$ m/z: calcd 304.2; found 305.0; Rt=3.318 min.

Chiral HPLC: Rt=11.54 min (Column: OJ-H; Eluent: Hexane-MeOH-IPA, 80-10-10; Flow Rate: 0.6 mL/min).

Compound 192: LCMS(ESI): [M+H]$^+$ m/z: calcd 304.2; found 305.0; Rt=3.363 min.

Chiral HPLC: Rt=13.54 min (Column: OJ-H; Eluent: Hexane-MeOH-IPA, 80-10-10; Flow Rate: 0.6

Example 348. The Synthesis of 5-[[2-[(2R,5S)-2-cyclobutyl-5-methyl-1-piperidyl]-2-oxo-acetyl]amino]pyridine-3-carboxamide (Compound 161

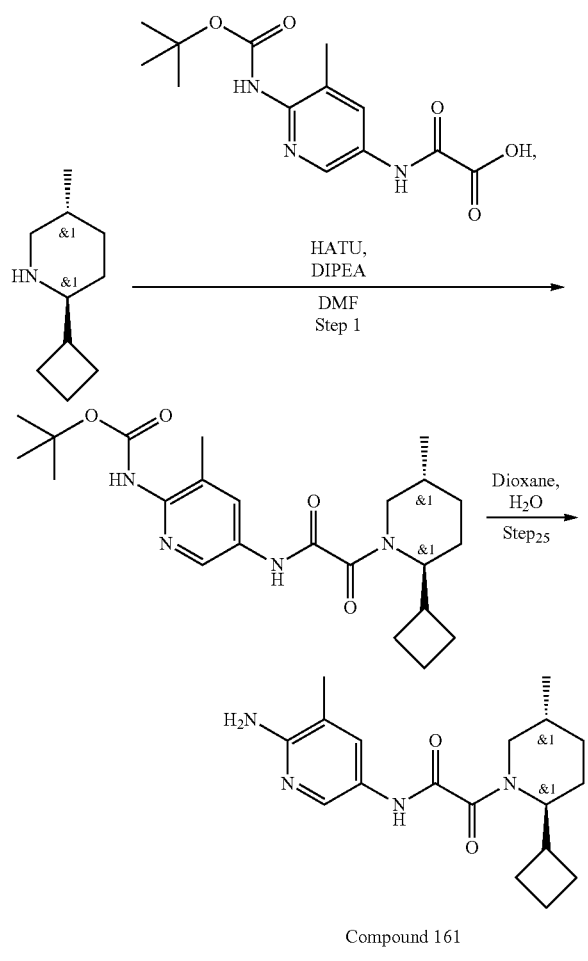

Step 1: Synthesis of 5-[[2-[(2R,5S)-2-cyclobutyl-5-methyl-1-piperidyl]-2-oxo-acetyl]amino]pyridine-3-carboxamide (Compound 155

To a stirred solution of 2-[(5-carbamoyl-3-pyridyl)amino]-2-oxo-acetic acid (0.23 g, 1.10 mmol) and 2-cyclobutyl-5-methyl-piperidine (168.54 mg, 1.10 mmol) in DMF (10 mL) was added DIPEA (355.30 mg, 2.75 mmol, 478.84 μL). The resulting mixture was stirred for 5 minutes. After 5 minutes, a solution of HATU (439.02 mg, 1.15 mmol) in DMF (2 mL) was added. The resulting reaction mixture was stirred for overnight at room temperature. Upon completion, the resulting suspension was concentrated under reduced pressure and the crude product was purified by HPLC and freeze dried to afford rac-5-[[2-[(2R,5S)-2-cyclobutyl-5-methyl-1-piperidyl]-2-oxo-acetyl]amino]pyridine-3-carboxamide (Compound 155, 20.4 mg, 59.23 μmol, 5.39% yield) as a white solid.

$^1$H NMR (DMSO-$d_6$, 500 MHz): δ (ppm) 0.95 (dd, 3H), 1.32 (m, 2H), 1.80 (m, 9H), 2.93 (m, 2H), 3.81 (m, 1H), 4.24 (m, 1H), 7.62 (m, 1H), 8.18 (m, 1H), 8.50 (m, 1H), 8.78 (m, 1H), 8.90 (m, 1H), 11.09 (m, 1H).

LCMS(ESI): [M+H]$^+$ m/z: calcd 344.2; found 345.4; Rt=2.876 min.

Step 2: Synthesis of 5-[[2-[(2R,5S)-2-cyclobutyl-5-methyl-1-piperidyl]-2-oxo-acetyl]amino]pyridine-3-carboxamide (Compound 155

To a stirred solution of 2-[(5-carbamoyl-3-pyridyl)amino]-2-oxo-acetic acid (0.23 g, 1.10 mmol) and 2-cyclobutyl-5-methyl-piperidine (168.54 mg, 1.10 mmol) in DMF (10 mL) was added DIPEA (355.30 mg, 2.75 mmol, 478.84 μL). The resulting mixture was stirred for 5 minutes. After 5 minutes, a solution of HATU (439.02 mg, 1.15 mmol) in DMF (2 mL) was added. The resulting reaction mixture was stirred for overnight at room temperature. Upon completion, the resulting suspension was concentrated under reduced pressure and the crude product was purified by HPLC and freeze dried to afford rac-5-[[2-[(2R,5S)-2-cyclobutyl-5-methyl-1-piperidyl]-2-oxo-acetyl]amino]pyridine-3-carboxamide (Compound 155, 20.4 mg, 59.23 μmol, 5.39% yield) as a white solid.

$^1$H NMR (DMSO-$d_6$, 500 MHz): δ (ppm) 0.95 (dd, 3H), 1.32 (m, 2H), 1.80 (m, 9H), 2.93 (m, 2H), 3.81 (m, 1H), 4.24 (m, 1H), 7.62 (m, 1H), 8.18 (m, 1H), 8.50 (m, 1H), 8.78 (m, 1H), 8.90 (m, 1H), 11.09 (m, 1H).

LCMS(ESI): [M+H]$^+$ m/z: calcd 344.2; found 345.4; Rt=2.876 min.

Example 349. The Synthesis of N-(6-amino-5-methyl-3-pyridyl)-2-(2-cyclobutyl-1-piperidyl)-2-oxo-acetamide (Compound 182

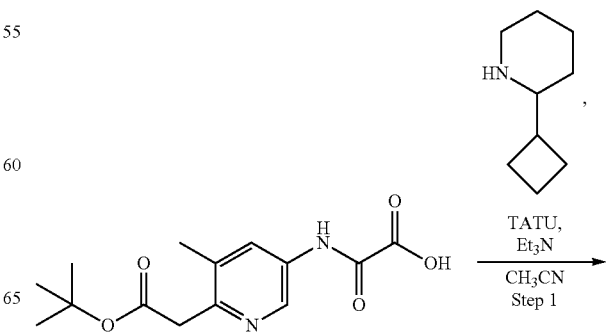

2044

Example 350. The Synthesis of N-(6-amino-5-methylpyridin-3-yl)-2-(2-cyclopentyl-5-methylpiperidin-1-yl)-2-oxoacetamide (Compound 190

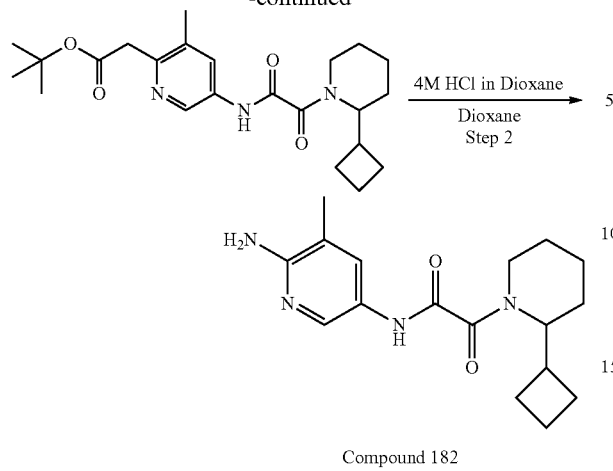

Compound 182

Step 1: Synthesis of tert-butyl N-[5-[[2-(2-cyclobutyl-1-piperidyl)-2-oxo-acetyl]amino]-3-methyl-2-pyridyl]carbamate 2-[[6-(tert-butoxycarbonylamino)-5-methyl-3-pyridyl]amino]-2-oxo-acetic acid (0.3 g, 1.02 mmol), TATU (392.65 mg, 1.22 mmol) and triethylamine (205.61 mg, 2.03 mmol, 283.21 µL) were mixed in dry CH₃CN (25 mL) at 21° C. and the resulting mixture was stirred for 15 minutes. After 15 minutes, 2-cyclobutylpiperidine (155.60 mg, 1.12 mmol) was added and the resulting mixture was stirred at 21° C. for overnight. The resulting mixture was evaporated to dryness and subjected to HPLC (Eluent: 50-90%, 0-9.5 min, H₂O-MeOH (0.1% NH₃); flow rate: 30 mL/min; loading pump: 4 mL/min, MeOH (0.1% NH₃); column: YMC-Actus Triart C18 100*20 mm, 5 um) to get tert-butyl N-[5-[[2-(2-cyclobutyl-1-piperidyl)-2-oxo-acetyl]amino]-3-methyl-2-pyridyl]carbamate (7.3 mg, 17.53 µmol, 1.73% yield) as a white solid.

LCMS(ESI): [M+Boc]⁺ m/z: calcd 416.3; found 417.2; Rt=3.640 min.

Step 2: Synthesis of N-(6-amino-5-methyl-3-pyridyl)-2-(2-cyclobutyl-1-piperidyl)-2-oxo-acetamide (Compound 182

To a stirring solution of tert-butyl N-[5-[[2-(2-cyclobutyl-1-piperidyl)-2-oxo-acetyl]amino]-3-methyl-2-pyridyl]carbamate (7.3 mg, 17.53 µmol) in Dioxane (1 mL) was added Hydrogen chloride solution 4.0 M in dioxane (3.20 mg, 87.63 µmol, 3.99 µL) at 21° C. The resulting mixture was stirred for 2 hours. After 2 hours, the resulting mixture was evaporated to dryness and purified by HPLC (Eluent: 2-7 min, 15-30% CH₃CN; flow rate: 30 mL/min; column: SunFire C18 100*19 mm, 5 µM) and freeze dried to get N-(6-amino-5-methyl-3-pyridyl)-2-(2-cyclobutyl-1-piperidyl)-2-oxo-acetamide (Compound 182, 3.3 mg, 10.43 µmol, 59.51% yield) as a yellow solid.

¹H NMR (CDCl₃, 400 MHz): δ (ppm) 1.54 (m, 4H), 1.85 (m, 8H), 2.12 (m, 3H), 2.86 (m, 2H), 4.69 (m, 3H), 4.99 (m, 1H), 7.72 (d, 1H), 8.03 (s, 1H), 9.00 (s, 1H).

LCMS(ESI): [M+H]⁺ m/z: calcd 316.2; found 317.2; Rt=0.953 min.

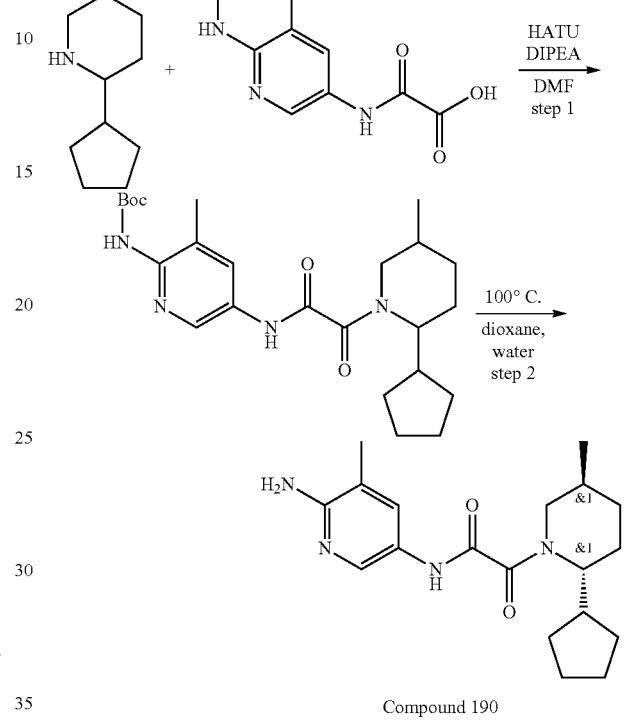

Compound 190

Step 1: Synthesis of tert-butyl (5-(2-(2-cyclopentyl-5-methylpiperidin-1-yl)-2-oxoacetamido)-3-methylpyridin-2-yl)carbamate 2-cyclopentyl-5-methyl-piperidine (200 mg, 1.20 mmol), 2-[[6-(tert-butoxycarbonylamino)-5-methyl-3-pyridyl]amino]-2-oxo-acetic acid (353.03 mg, 1.20 mmol), TEA (604.88 mg, 5.98 mmol, 833.16 µL) were mixed in DMF (5 mL) and then HATU (681.86 mg, 1.79 mmol) were added. Resulting mixture were stirred at 25° C. for 12 hr. The mixture was evaporated under reduce pressure and purified with HPLC (2-10 min 10-50% MeOH, 30 ml/min) to obtain tert-butyl N-[5-[[2-(2-cyclopentyl-5-methyl-1-piperidyl)-2-oxo-acetyl]amino]-3-methyl-2-pyridyl]carbamate (176.1 mg, 396.12 µmol, 33.13% yield).

¹H NMR (400 MHz, CDCl₃) δ (ppm) 0.97 (d, 3H), 1.26 (m, 3H), 1.44 (s, 9H), 1.65 (m, 7H), 1.88 (m, 2H), 2.17 (s, 3H), 3.16 (m, 1H), 3.45 (m, 1H), 4.17 (m, 3H), 7.91 (d, 1H), 8.42 (s, 1H), 9.06 (s, 1H), 10.86 (m, 1H).

LCMS(ESI): [M]⁺ m/z: calcd 113.2; found 114.2; Rt=1.524 min.

Step 2: Synthesis of N-(6-amino-5-methylpyridin-3-yl)-2-(2-cyclopentyl-5-methylpiperidin-1-yl)-2-oxoacetamide (Compound 190

The solution of tert-butyl N-[5-[[2-[(2S,5R)-2-cyclopentyl-5-methyl-1-piperidyl]-2-oxo-acetyl]amino]-3-methyl-2-pyridyl]carbamate (171.60 mg, 385.99 µmol) in dioxane (2 mL) and water (2 mL) was heated at 100° C. for 12 hr. The mixture was evaporated under reduce pressure and purified with HPLC (2-10 min 10-50% MeCN+NH₃) to obtain N-(6-amino-5-methyl-3-pyridyl)-2-[(2S,5R)-2-cyclopentyl-5-methyl-1-piperidyl]-2-oxo-acetamide (16.7 mg, 48.48 μmol, 12.56% yield).

¹H NMR (600 MHz, DMSO-d₆) δ (ppm) 0.92 (m, 3H), 1.22 (m, 3H), 1.57 (m, 8H), 1.89 (m, 2H), 2.00 (s, 3H), 3.48 (m, 3H), 4.08 (dd, 1H), 5.59 (m, 2H), 7.44 (m, 1H), 7.98 (s, 1H), 10.28 (m, 1H).

LCMS(ESI): [M]⁺ m/z: calcd 344.4; found 345.2; Rt=1.070 min.

Example 351. The Synthesis of N-(6-amino-5-methylpyridin-3-yl)-2-(2-(3-bromophenyl)-5-methylpiperidin-1-yl)-2-oxoacetamide (Compound 600

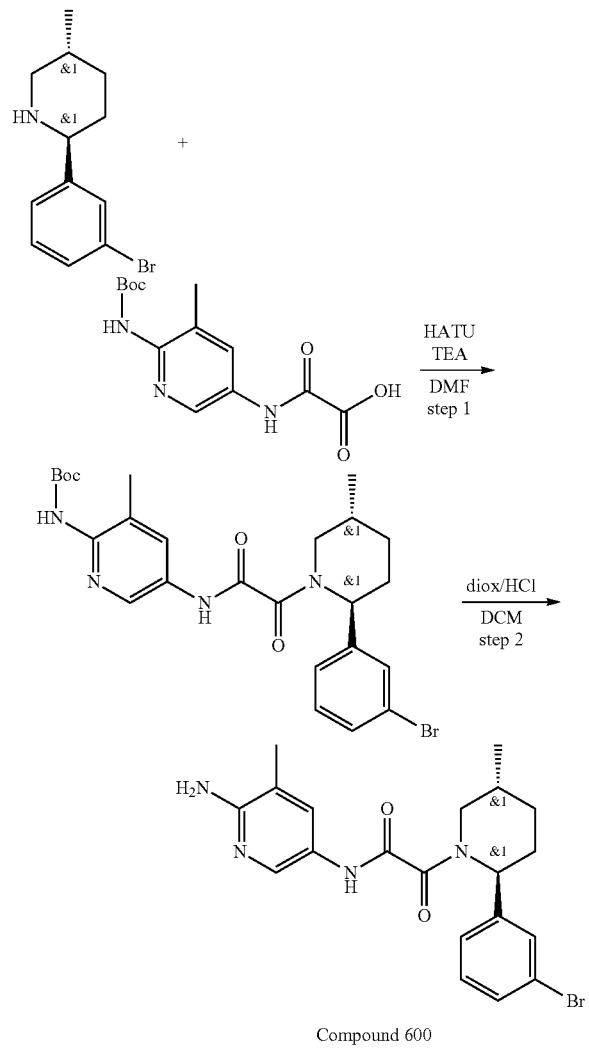

Compound 600

Step 1: Synthesis of rac-tert-butyl (5-(2-((2R,5S)-2-(3-bromophenyl)-5-methylpiperidin-1-yl)-2-oxoacetamido)-3-methylpyridin-2-yl)carbamate To the solution of (2S,5R)-2-(3-bromophenyl)-5-methyl-piperidine (262.83 mg, 1.03 mmol, HCl), 2-[[6-(tert-butoxy-carbonylamino)-5-methyl-3-pyridyl]amino]-2-oxo-acetic acid (400 mg, 1.35 mmol) and TEA (1.05 g, 10.34 mmol, 1.44 mL) in DMF (3 mL) HATU (432.52 mg, 1.14 mmol) was added portion wise. Mixture was stirred at 25° C. for 1.5 hr. The reaction mixture was diluted with water (20 ml) and product was extracted with EtOAc (3*25 ml).

Combined organic layer were washed with water, brine and dried over Na₂SO₄. Solvent was evaporated to give tert-butyl N-[5-[[2-[(2S,5R)-2-(3-bromophenyl)-5-methyl-1-piperidyl]-2-oxo-acetyl]amino]-3-methyl-2-pyridyl]carbamate (800 mg, crude). Crude product was used in the next step without further purification.

¹H NMR (400 MHz, CDCl₃) δ (ppm) 1.05 (d, 3H), 1.23 (m, 1H), 1.48 (s, 9H), 1.98 (m, 2H), 2.21 (s, 3H), 2.28 (m, 2H), 2.93 (m, 1H), 3.35 (m, 1H), 4.08 (m, 1H), 5.72 (m, 1H), 6.71 (m, 1H), 7.24 (m, 2H), 7.37 (m, 1H), 8.01 (m, 1H), 8.35 (m, 1H), 9.39 (m, 1H).

LCMS(ESI): [M]⁺ m/z: calcd 531.4; found 532.2; Rt=1.527 min.

Step 2: Synthesis of N-(6-amino-5-methylpyridin-3-yl)-2-(2-(3-bromophenyl)-5-methylpiperidin-1-yl)-2-oxoacetamide (Compound 600

To the stirred solution of tert-butyl N-[5-[[2-[(2S,5R)-2-(3-bromophenyl)-5-methyl-1-piperidyl]-2-oxo-acetyl]amino]-3-methyl-2-pyridyl]carbamate (800 mg, 1.51 mmol) in DCM (15 mL). Hydrogen chloride solution 4.0 M in dioxane (548.86 mg, 15.05 mmol, 686.08 μL) was added and the reaction mixture was stirred for 2 hr at 25° C. Solvents were evaporated to give crude product (700 mg) which was purified by reverse phase HPLC (60-60-90% 0-1-5 min 0.1% NH₃-MeOH, flow: 30 ml/min (loading pump 4 ml/min MeOH) target mass 431 column: YMC Triart C18 100×20 mm, 5 um) to give N-(6-amino-5-methyl-3-pyridyl)-2-[(2S,5R)-2-(3-bromophenyl)-5-methyl-1-piperidyl]-2-oxo-acetamide (270 mg, 625.98 μmol, 41.58% yield).

¹H NMR (600 MHz, DMSO-d₆) δ (ppm) 0.96-1.03 (m, 3H), 1.25-1.37 (m, 1H), 1.58-1.66 (m, 1H), 1.80-1.93 (m, 1H), 1.97-2.07 (m, 4H), 2.13-2.25 (m, 1H), 2.68-3.25 (m, 1H), 3.33-4.07 (m, 1H), 5.12-5.57 (m, 1H), 5.57-5.68 (m, 2H), 7.29-7.38 (m, 2H), 7.42-7.55 (m, 3H), 7.93-8.04 (m, 1H), 10.42-10.64 (m, 1H).

LCMS(ESI): [M]⁺ m/z: calcd 431.4; found 432.2; Rt=2.503 min.

Example 352. The Synthesis of N-(6-amino-5-methylpyridin-3-yl)-2-(2-(6-hydroxyspiro[3.3]heptan-2-yl)-5-methylpiperidin-1-yl)-2-oxoacetamide (Compound 711, Compound 768, Compound 769, Compound 766 and Compound 767

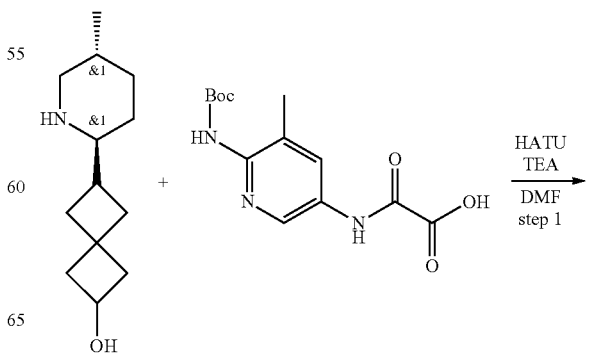

2047 -continued

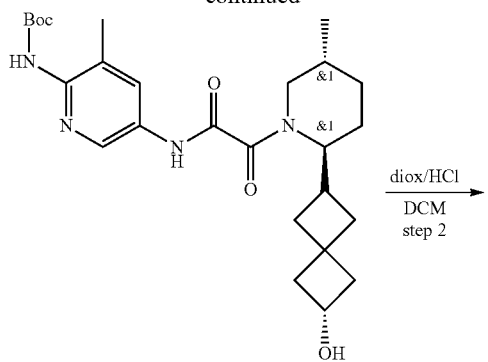

Compound 711

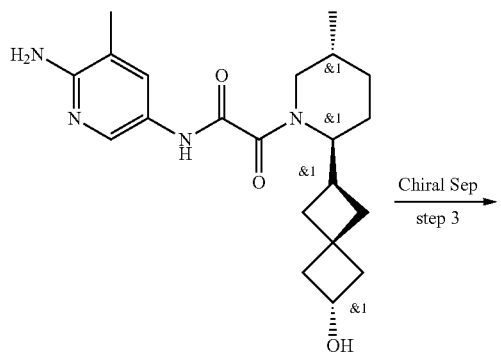

Compound 767

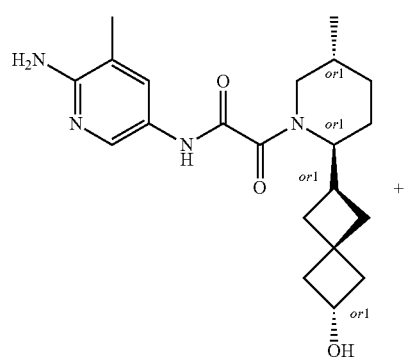

Compound 766

2048 -continued

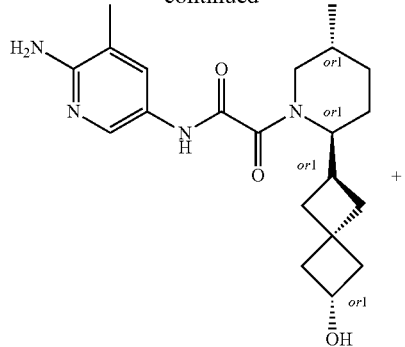

Compound 769

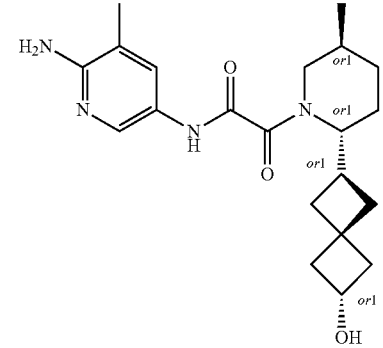

Compound 768

Step 1: Synthesis of rac-tert-butyl (5-(2-((2R,5S)-2-(6-hydroxyspiro[3.3]heptan-2-yl)-5-methylpiperidin-1-yl)-2-oxoacetamido)-3-methylpyridin-2-yl)carbamate To the solution of 6-[(2S,5R)-5-methyl-2-piperidyl]spiro[3.3]heptan-2-ol (250 mg, 1.19 mmol, HCl), 2-[[6-(tert-butoxycarbonylamino)-5-methyl-3-pyridyl]amino]-2-oxo-acetic acid (352.67 mg, 1.19 mmol) and TEA (845.96 mg, 8.36 mmol, 1.17 mL) in DMF (4 mL) HATU (499.52 mg, 1.31 mmol) was added portion wise. Mixture was stirred at 25° C. for 2 hr. The reaction mixture was diluted with water (50 ml) and product was extracted with EtOAc (3*25 ml). Combined organic layer were washed with water, brine and dried over Na$_2$SO$_4$. Solvent was evaporated to give tert-butyl N-[5-[[2-[(2S,5R)-2-(2-hydroxyspiro[3.3]heptan-6-yl)-5-methyl-1-piperidyl]-2-oxo-acetyl]amino]-3-methyl-2-pyridyl]carbamate (500 mg, 1.03 mmol, 86.04% yield).

$^1$H NMR (500 MHz, DMSO-d$_6$) δ (ppm) 0.89 (d, 3H), 1.22 (m, 3H), 1.42 (s, 9H), 1.88 (m, 6H), 2.08 (m, 6H), 2.15 (m, 1H), 2.87 (s, 3H), 3.98 (m, 2H), 4.98 (m, 1H), 7.88 (m, 1H), 8.39 (m, 1H), 9.05 (s, 1H), 10.87 (m, 1H).

LCMS(ESI): [M]$^+$ m/z: calcd 486.2; found 487.2; Rt=1.252 min.

Step 2: Synthesis of N-(6-amino-5-methyl-3-pyridyl)-2-[(2R,5S)-2-(2-hydroxyspiro[3.3]heptan-6-yl)-5-methyl-1-piperidyl]-2-oxo-acetamide (Compound 711

To the stirred solution of tert-butyl N-[5-[[2-[(2S,5R)-2-(2-hydroxyspiro[3.3]heptan-6-yl)-5-methyl-1-piperidyl]-2-oxo-acetyl]amino]-3-methyl-2-pyridyl]carbamate (500 mg, 1.03 mmol) in DCM (15 mL) hydrogen chloride solution 4.0

M in dioxane (374.64 mg, 10.28 mmol, 468.30 µL) was added and the reaction mixture was stirred for 2 hr at 25° C. Solvents were evaporated to give crude product (550 mg) which was purified by reverse phase HPLC (30-30-65% 0-1-6 min H$_2$O/MeOH/0.1% NH$_3$, flow: 30 ml/min (loading pump 4 ml/min methanol) target mass 386 column: YMC Triart C18 100×20 mm, 5 um) to give N-(6-amino-5-methyl-3-pyridyl)-2-[(2R,5S)-2-(2-hydroxyspiro[3.3]heptan-6-yl)-5-methyl-1-piperidyl]-2-oxo-acetamide (25 mg, 64.69 µmol, 6.30% yield) as single diastereomer and N-(6-amino-5-methyl-3-pyridyl)-2-[(2R,5S)-2-(2-hydroxyspiro[3.3]heptan-6-yl)-5-methyl-1-piperidyl]-2-oxo-acetamide (60 mg, 155.24 µmol, 15.11% yield) as mixture of diastereomers. All amount of product (85 mg) was submitted for chiral resolution.

$^1$H NMR (600 MHz, DMSO-d$_6$) δ (ppm) 0.89 (m, 3H), 1.26 (m, 2H), 1.73 (m, 7H), 1.92 (m, 3H), 2.01 (m, 3H), 2.22 (m, 1H), 2.76 (m, 2H), 3.95 (m, 3H), 4.79 (m, 1H), 5.58 (m, 2H), 7.44 (m, 1H), 7.98 (m, 1H), 10.28 (m, 1H).

LCMS(ESI): [M]$^+$ m/z: calcd 386.2; found 387.2; Rt=1.788 min.

Step 3: Chiral Separation (Compound 768, Compound 769, Compound 766 and Compound 767

Racemic N-(6-amino-5-methyl-3-pyridyl)-2-[(2S,5R)-2-(2-hydroxyspiro[3.3]heptan-6-yl)-5-methyl-1-piperidyl]-2-oxo-acetamide (85 mg, 219.93 µmol) was submitted for chiral resolution to give N-(6-amino-5-methyl-3-pyridyl)-2-[(2S,5R)-2-(2-hydroxyspiro[3.3]heptan-6-yl)-5-methyl-1-piperidyl]-2-oxo-acetamide (6.4 mg, 16.56 µmol, 7.53% yield) (RetTime=47.305 min); N-(6-amino-5-methyl-3-pyridyl)-2-[(2S,5R)-2-(2-hydroxyspiro[3.3]heptan-6-yl)-5-methyl-1-piperidyl]-2-oxo-acetamide (13.6 mg, 35.19 µmol, 16.00% yield) (RetTime=21.24); N-(6-amino-5-methyl-3-pyridyl)-2-[(2R,5S)-2-(2-hydroxyspiro[3.3]heptan-6-yl)-5-methyl-1-piperidyl]-2-oxo-acetamide (4.6 mg, 11.90 µmol, 5.41% yield) (RetTime=20.477); N-(6-amino-5-methyl-3-pyridyl)-2-[(2R,5S)-2-(2-hydroxyspiro[3.3]heptan-6-yl)-5-methyl-1-piperidyl]-2-oxo-acetamide (15.7 mg, 40.62 µmol, 18.47% yield) (RetTime=34.600). Ret time for Compound 767 in analytical conditions (column: IC, Hexane-IPA-MeOH, 60-20-20, 0.6 ml/min as mobile phase) 47.30 min, for Compound 766 20.48 min, for Compound 769 21.24 min and for Compound 768 34.60 min.

Compound 767: Retention time: 47.30 min $^1$H NMR (600 MHz, DMSO-d$_6$) δ (ppm) 0.84-0.94 (m, 3H), 1.20-1.49 (m, 3H), 1.53-1.64 (m, 1H), 1.65-1.78 (m, 4H), 1.79-1.83 (m, 1H), 1.84-1.93 (m, 2H), 1.93-1.98 (m, 1.5H), 1.99-2.04 (m, 3H), 2.15-2.19 (m, 0.5H), 2.25-2.30 (m, 1H), 2.69-2.76 (m, 1H), 2.79-3.25 (m, 1H), 3.61-3.75 (m, 0.5H), 3.80-3.90 (m, 1H), 4.27-4.42 (m, 0.5H), 4.71-4.85 (m, 1H), 5.50-5.64 (m, 2H), 7.36-7.50 (m, 1H), 7.90-8.05 (m, 1H), 10.18-10.37 (m, 1H).

LCMS(ESI): [M]$^+$ m/z: calcd 386.2; found 387.2; Rt=1.835 min.

Compound 766: Retention time: 20.48 min $^1$H NMR (600 MHz, DMSO-d$_6$) δ (ppm) 0.86-0.92 (m, 3H), 1.20-1.30 (m, 2H), 1.45-1.62 (m, 2H), 1.64-1.78 (m, 4H), 1.78-1.92 (m, 3H), 1.93-1.98 (m, 1.5H), 1.99-2.03 (m, 3H), 2.11-2.21 (m, 0.5H), 2.23-2.31 (m, 1H), 2.66-2.79 (m, 1H), 2.79-3.24 (m, 1H), 3.65-3.71 (m, 0.5H), 3.79-3.89 (m, 1H), 4.32-4.38 (m, 1H), 4.75-4.82 (m, 0.5H), 5.53-5.64 (m, 2H), 7.38-7.48 (m, 1H), 7.92-8.01 (m, 1H), 10.19-10.37 (m, 1H).

LCMS(ESI): [M]$^+$ m/z: calcd 386.2; found 387.2; Rt=1.837 min.

Compound 769: Retention time: 21.24 min $^1$H NMR (600 MHz, DMSO-d$_6$) δ (ppm) 0.83-0.94 (m, 3H), 1.20-1.30 (m, 2H), 1.44-1.62 (m, 2H), 1.63-1.76 (m, 4H), 1.78-1.93 (m, 3H), 1.93-1.98 (m, 1H), 2.00-2.02 (m, 3H), 2.02-2.15 (m, 1H), 2.24-2.34 (m, 1H), 2.68-2.76 (m, 1H), 2.77-3.25 (m, 1H), 3.66-3.73 (m, 0.5H), 3.87-3.94 (m, 1H), 4.31-4.38 (m, 0.5H), 4.74-4.83 (m, 1H), 5.50-5.62 (m, 2H), 7.39-7.47 (m, 1H), 7.93-8.02 (m, 1H), 10.20-10.35 (m, 1H).

LCMS(ESI): [M]$^+$ m/z: calcd 386.2; found 387.2; Rt=2.066 min.

Compound 768: Retention time: 34.60 min $^1$H NMR (600 MHz, DMSO-d$_6$) δ (ppm) 0.86-0.93 (m, 3H), 1.19-1.31 (m, 2H), 1.45-1.62 (m, 2H), 1.64-1.76 (m, 4H), 1.78-1.92 (m, 3H), 1.93-1.99 (m, 1H), 2.00-2.02 (m, 3H), 2.03-2.14 (m, 1H), 2.25-2.33 (m, 1H), 2.66-2.77 (m, 1H), 2.77-3.24 (m, 1H), 3.67-3.73 (m, 0.5H), 3.86-3.94 (m, 1H), 4.31-4.42 (m, 0.5H), 4.74-4.84 (m, 1H), 5.52-5.63 (m, 2H), 7.39-7.49 (m, 1H), 7.93-8.03 (m, 1H), 10.19-10.39 (m, 1H).

LCMS(ESI): [M]$^+$ m/z: calcd 386.2; found 387.2; Rt=2.078 min.

The Synthesis of N-(6-amino-5-methylpyridin-3-yl)-2-(2-(5-chloropyridin-3-yl)-5-methylpiperidin-1-yl)-2-oxoacetamide (Compound 1025

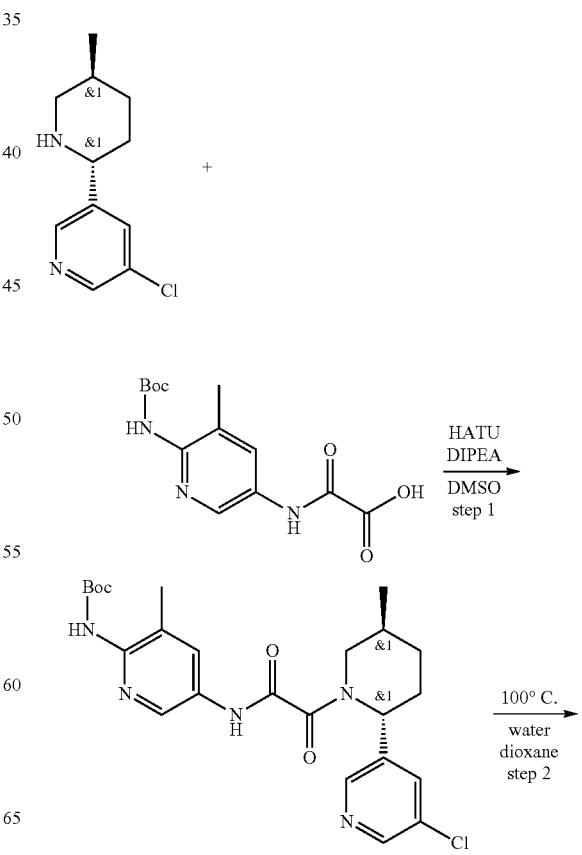

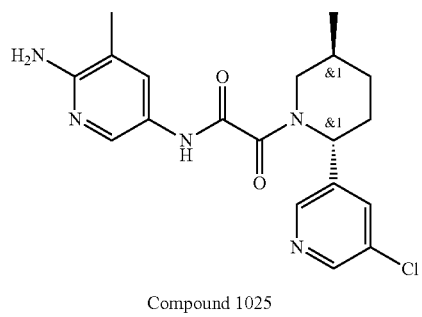

Compound 1025

Step 1: Synthesis of rac-tert-butyl (5-(2-((2R,5S)-2-(5-chloropyridin-3-yl)-5-methylpiperidin-1-yl)-2-oxoacetamido)-3-methylpyridin-2-yl)carbamate 3-chloro-5-[(2R,5S)-5-methyl-2-piperidyl]pyridine (0.3 g, 1.42 mmol) and 2-[[6-(tert-butoxycarbonylamino)-5-methyl-3-pyridyl]amino]-2-oxo-acetic acid (358.03 mg, 1.21 mmol, HCl) were dissolved in DMSO (6 mL) under gentle heating. HATU (649.65 mg, 1.71 mmol) was added in small portions under vigorous stirring and occasional heating. After the reaction was complete (concluded by LCMS of the reaction mixture), the mixture was purified by HPLC (42% 0.5-6.5 min water-MeCN; flow 30 ml/min (42% 0.5-6.5 min water-MeCN; flow 30 ml/min (loading pump 4 ml/min MeCN); target mass 487; column SunFire C18 100×19 mm 5 um (R)) to give tert-butyl N-[5-[[2-[(2R,5S)-2-(5-chloro-3-pyridyl)-5-methyl-1-piperidyl]-2-oxo-acetyl]amino]-3-methyl-2-pyridyl]carbamate (290 mg, 594.29 μmol, 41.74% yield) in 2 fractions with different purity.

LCMS(ESI): [M]⁺ m/z: calcd 487.2; found 488.2; Rt=3.236 min.

Step 2: Synthesis of N-(6-amino-5-methylpyridin-3-yl)-2-(2-(5-chloropyridin-3-yl)-5-methylpiperidin-1-yl)-2-oxoacetamide (Compound 1025 tert-butyl N-[5-[[2-[(2R,5S)-2-(5-chloro-3-pyridyl)-5-methyl-1-piperidyl]-2-oxo-acetyl]amino]-3-methyl-2-pyridyl]carbamate (99 mg, 202.88 μmol) was dissolved in dioxane (4 mL) and H₂O (0.5 mL). Obtained solution was stirred at 100° C. for 48 hr; after the reaction was complete, the mixture was subjected to HPLC (20-30% 0.5-6.5 min water-MeCN; flow 30 ml/min (loading pump 4 ml/min MeCN); target mass 387; column SunFire 100×19 mm 5 um (R)) to give N-(6-amino-5-methyl-3-pyridyl)-2-[(2R,5S)-2-(5-chloro-3-pyridyl)-5-methyl-1-piperidyl]-2-oxo-acetamide (21 mg, 54.14 μmol, 26.69% yield) with 3% impurity of the corresponding cis-isomer.

Compound 1025: LCMS(ESI): [M]⁺ m/z: calcd 387.2; found 388.2; Rt=1.898 min.

Example 353. The Synthesis of N-(6-amino-5-methyl-3-pyridyl)-2-[(2R,5S)-2-(4-fluoro-3-hydroxy-phenyl)-5-methyl-1-piperidyl]-2-oxo-acetamide (Compound 555

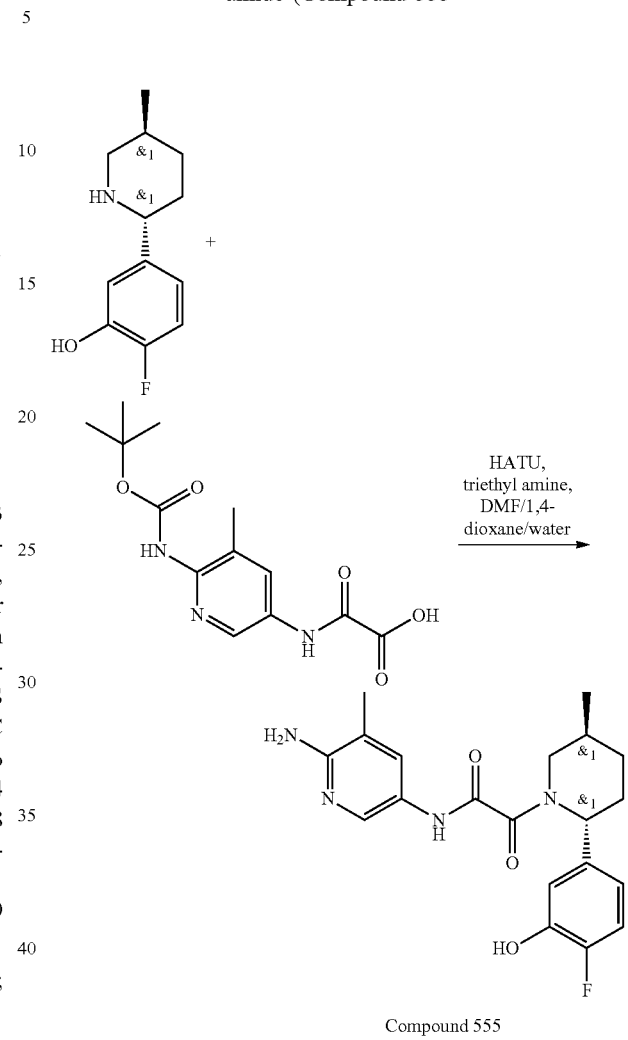

Compound 555

To a stirred solution of 2-fluoro-5-[(2R,5S)-5-methyl-2-piperidyl]phenol (550 mg, 1.90 mmol, HBr), 2-[[6-(tert-butoxycarbonylamino)-5-methyl-3-pyridyl]amino]-2-oxo-acetic acid (559.70 mg, 1.90 mmol) and triethyl amine (1.92 g, 18.95 mmol, 2.64 mL) in DMF (20 mL) was added HATU (1.44 g, 3.79 mmol) in small portions at 25° C. The resulting reaction mixture was stirred at 25° C. for 16 hr, then concentrated in vacuo to approximately 5 ml and submitted to reverse phase HPLC (column: YMC-Actus Triart C18 100*20 mml.D. S-5 um, mobile phase: 0-5 min 25-80% water-methanol (NH₃ 0.1%), flow rate: 30 ml/min) to afford 3 fractions of Boc-protected amide 75 mg 91% purity by LCMS (1st fraction), 68 mg 95.66% purity by LCMS (2nd fraction), and 70 mg 93.86% purity by LCMS (3rd fraction). Second fraction of Boc-protected amide (68 mg) was dissolved in a mixture of 1,4-dioxane (2 mL) and water (2.5 mL). The resulting mixture was stirred at 95° C. for 12 hr, then cooled down and submitted to reverse phase HPLC (column: YMC-Actus Triart C18 100*20 mml.D. S-5 um, mobile phase: 20-40% 1-6 min water-methanol (NH₃ 0.1%), flow rate: 30 ml/min) to afford 25 mg of the product 93.69% purity by LCMS, which was again repurified by reverse phase HPLC (column: SunFire C18 100*19 mm 5um, mobile phase: 15-45% 1-6 min water-acetonitrile, flow rate: 30 ml/min) to afford Compound 555 N-(6-amino-5-methyl-3-pyridyl)-2-[(2R,5S)-2-(4-fluoro-3-hydroxy-phenyl)-5-methyl-1-piperidyl]-2-oxo-acetamide (18 mg, 46.58 μmol, 2.46% yield) as white solid.

¹H NMR (600 MHz, DMSO-d₆) δ 0.95-1.05 (m, 3H), 1.24-1.35 (m, 1H), 1.62-1.71 (m, 1H), 1.80-1.91 (m, 1H), 1.92-2.05 (m, 4H), 2.05-2.13 (m, 1H), 2.69-3.23 (m, 1H), 3.43-4.06 (m, 1H), 5.01-5.51 (m, 1H), 5.55-5.69 (m, 2H), 6.62-6.78 (m, 1H), 6.80-6.96 (m, 1H), 7.03-7.15 (m, 1H), 7.40-7.50 (m, 1H), 7.93-8.03 (m, 1H), 9.57-10.06 (m, 1H), 10.24-10.70 (m, 1H).

LCMS(ESI): [M+H]⁺ m/z: calcd 386.4; found 387.2; Rt=1.948 min.

Example 354. The Synthesis of Rac N-(6-amino-5-methyl-3-pyridyl)-2-[(2R,5S)-5-methyl-2-(4-methylsulfonylphenyl)-1-piperidyl]-2-oxo-acetamide (Compound 643)

rel-N-(6-amino-5-methylpyridin-3-yl)-2-((2R,5S)-5-methyl-2-(4-(methylsulfonyl)phenyl)piperidin-1-yl)-2-oxoacetamide (Compound 976) and rel-N-(6-amino-5-methylpyridin-3-yl)-2-((2S,5R)-5-methyl-2-(4-(methylsulfonyl)phenyl)piperidin-1-yl)-2-oxoacetamide (Compound 938)

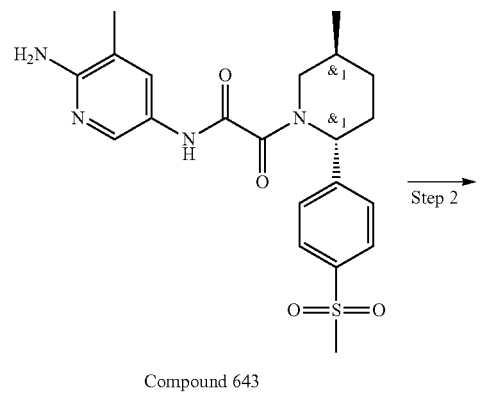

Compound 643

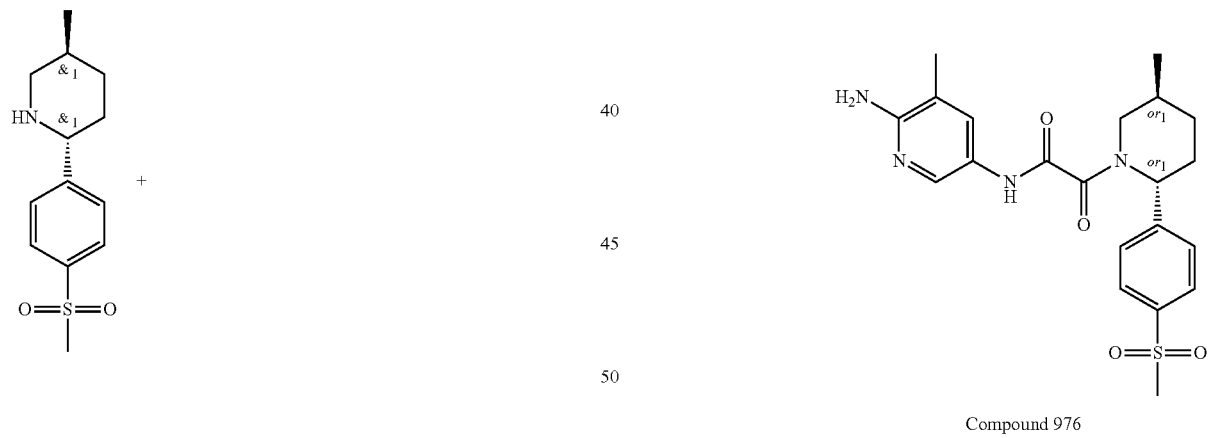

Compound 938

Compound 976

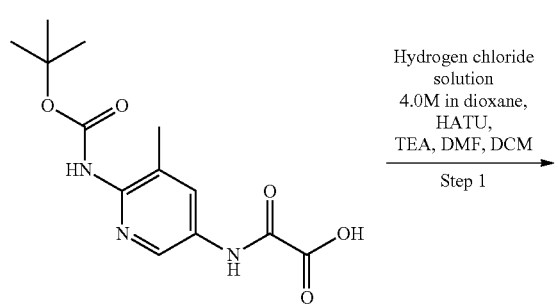

Step 1: Synthesis of Rac N-(6-amino-5-methyl-3-pyridyl)-2-[(2R,5S)-5-methyl-2-(4-methylsulfonylphenyl)-1-piperidyl]-2-oxo-acetamide (Compound 643

To a stirring solution of (2R,5S)-5-methyl-2-(4-methylsulfonylphenyl)piperidine (250 mg, 986.74 μmol), 2-[[6-(tert-butoxycarbonylamino)-5-methyl-3-pyridyl]amino]-2-oxo-acetic acid (291.37 mg, 986.74 μmol) and triethyl amine (998.48 mg, 9.87 mmol, 1.38 mL) in DMF (5 mL) was added HATU (412.71 mg, 1.09 mmol) at 25° C. in small portions over 0.5 hr. The resulting reaction mixture was stirred at 25° C. for 18 hr. The reaction mixture was concentrated in vacuo, the residue was dissolved in dichloromethane (10 mL), and Hydrogen chloride solution 4.0 M in dioxane (15.75 g, 60.04 mmol, 15 mL, 13.9% purity) was added in one portion. The resulting mixture was stirred at 25° C. for 3 hr, and then concentrated in vacuo. The residue was purified by reverse phase HPLC (column: YMC-Actus Triart C18 100*20 mm I.D. S-5 um, mobile phase: 0-5 min 20-70% water-methanol ($NH_3$ 0.1%), flow 30 ml/min (loading pump 4 ml/min methanol ($NH_3$ 0.1%)) to afford Compound 643 N-(6-amino-5-methyl-3-pyridyl)-2-[(2R,5S)-5-methyl-2-(4-methylsulfonylphenyl)-1-piperidyl]-2-oxo-acetamide (143 mg, 332.16 μmol, 33.66% yield) as white solid.

$^1$H NMR (DMSO-$d_6$, 600 MHz): δ (ppm) 1.00 (m, 3H), 1.34 (m, 1H), 1.60 (m, 1H), 1.89 (m, 1H), 2.01 (m, 4H), 2.23 (m, 2H), 3.20 (m, 3H), 3.68 (m, 1H), 5.62 (m, 3H), 7.46 (m, 1H), 7.59 (m, 2H), 7.95 (m, 3H), 10.51 (m, 1H)

LCMS(ESI): [M+H]$^+$ m/z: calcd 430.2; found 431.2; Rt=1.827 min.

Step 2: The Synthesis of rel-N-(6-amino-5-methylpyridin-3-yl)-2-((2R,5S)-5-methyl-2-(4-(methylsulfonyl)phenyl)piperidin-1-yl)-2-oxoacetamide (Compound 976) and rel-N-(6-amino-5-methylpyridin-3-yl)-2-((2S,5R)-5-methyl-2-(4-(methylsulfonyl)phenyl)piperidin-1-yl)-2-oxoacetamide (Compound 938

Enantiomers were separated in the following conditions: Column: Chiralpak IB (250*30 mm, 5 mkm); Mobile phase: $CO_2$-MeOH, 60-40. Flow Rate: 90 mL/min; Column Temperature: 40'C; Wavelength: 215 nm. RetTime (Compound 938)=6.53 min; RetTime (Compound 643)=10.14 min Compound 643 was additionally purified from an cis-impurity in the flowing conditions: Column: Chiralcel OJ-H (250*20 mm, 5 mkm); Mobile phase: Hexane-IPA-MeOH, 50-25-25. Flow Rate: 10 mL/min; Column Temperature: 20'C; Wavelength: 205 nm. RetTime (isomer A)=36.22 min; RetTime (isomer B)=38.61 min, to give Compound 976 (47.78 mg, 110.98 μmol, 41.99% yield) (RT (Chiralpak IB (250*4.6, 5 mkm), Hexane-IPA-MeOH, 40-30-30, 0.6 ml/min)=21.522 min) as an orange solid and Compound 938 (47.82 mg, 111.08 μmol, 42.02% yield) (RT (Chiralpak IB (250*4.6, 5 mkm), Hexane-IPA-MeOH, 40-30-30, 0.6 ml/min)=13.780 min) as an yellow solid.

Compound 976: $^1$H NMR (DMSO-$d_6$, 600 MHz): δ (ppm) 1.00 (m, 3H), 1.33 (m, 1H), 1.62 (m, 1H), 1.88 (m, 1H), 1.99 (m, 3H), 2.15 (m, 2H), 3.19 (m, 4H), 3.76 (dd, 1H), 5.60 (m, 3H), 7.45 (m, 1H), 7.61 (m, 2H), 7.91 (m, 2H), 7.98 (m, 1H), 10.51 (s, 1H).

LCMS(ESI): [M+H]$^+$ m/z: calcd 430.2; found 431.4; Rt=1.765 min.

RT (Hexane-IPA-MeOH, 40-30-30, 0.6 ml/min)=21.5222 min.

Compound 938: $^1$H NMR (DMSO-$d_6$, 600 MHz): δ (ppm) 1.00 (m, 3H), 1.33 (m, 1H), 1.61 (m, 1H), 1.87 (m, 1H), 1.99 (m, 3H), 2.15 (m, 2H), 3.19 (m, 4H), 3.76 (dd, 1H), 5.60 (m, 3H), 7.45 (m, 1H), 7.58 (dd, 2H), 7.91 (m, 2H), 7.98 (m, 1H), 10.51 (m, 1H).

LCMS(ESI): [M+H]$^+$ m/z: calcd 430.2; found 431.4; Rt=1.750 min.

RT (Hexane-IPA-MeOH, 40-30-30, 0.6 ml/min)=13.7802 min.

Example 355. The Synthesis of of N-(6-amino-5-methyl-3-pyridyl)-2-[(2S,5R)-5-methyl-2-(4-sulfamoylphenyl)-1-piperidyl]-2-oxo-acetamide (Compound 662

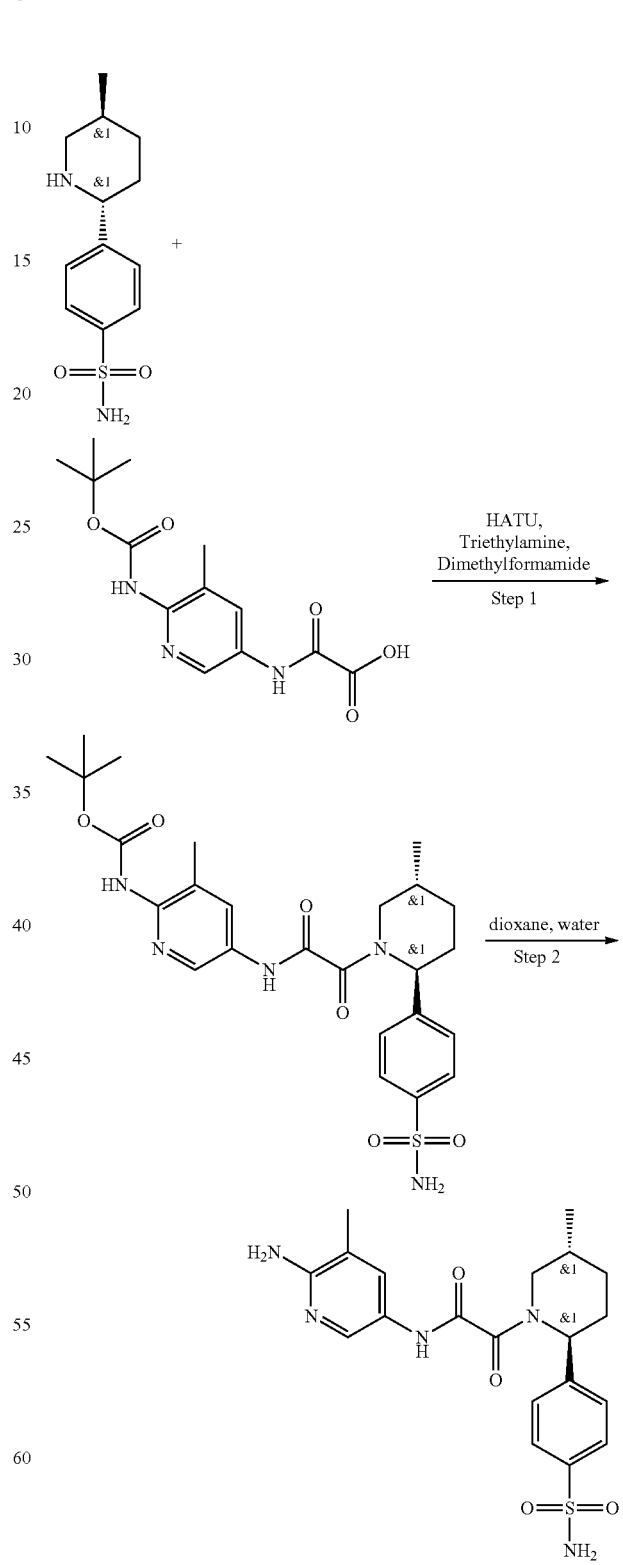

Compound 662

Step 1: Synthesis of tert-butyl N-[3-methyl-5-[[2-[(2S,5R)-5-methyl-2-(4-Sulfamoylphenyl)-1-piperidyl]-2-oxo-acetyl]amino]-2-pyridyl]carbamate To a stirred mixture of 4-(5-methyl-2-piperidyl)benzenesulfonamide (350 mg, 1.20 mmol, HCl), 2-[[6-(tert-butoxycarbonylamino)-5-methyl-3-pyridyl]amino]-2-oxo-acetic acid (355.39 mg, 1.20 mmol) and Triethylamine (365.36 mg, 3.61 mmol, 503.25 µL) in Dimethylformamide (4 mL) was added HATU (503.38 mg, 1.32 mmol). The resulting reaction mixture was stirred at 20° C. for 5 hr. Then, it was subjected to HPLC (Column: YMC Triart C18 100×20 mm, 5 um; 40-55% 0-5 min 0.1% NH$_3$-methanol, flow: 30 ml/min), affording tert-butyl N-[3-methyl-5-[[2-[(2S,5R)-5-methyl-2-(4-sulfamoylphenyl)-1-piperidyl]-2-oxo-acetyl]amino]-2-pyridyl]carbamate (97 mg, 182.46 µmol, 15.16% yield).

Two fractions were combined before next step.

LCMS(ESI): [M+H]$^+$ m/z: calcd 531.2; found 532.2; Rt=2.860 min.

Step 2: Synthesis of N-(6-amino-5-methyl-3-pyridyl)-2-[(2S,5R)-5-methyl-2-(4-Sulfamoylphenyl)-1-piperidyl]-2-oxo-acetamide (Compound 662

Water (1.00 g, 55.51 mmol, 1 mL) was added to a solution of tert-butyl N-[3-methyl-5-[[2-[(2S,5R)-5-methyl-2-(4-sulfamoylphenyl)-1-piperidyl]-2-oxo-acetyl]amino]-2-pyridyl]carbamate (97 mg, 182.46 µmol) in dioxane (2 mL). Resulting mixture was stirred at 95° C. for 36 hr. Then, it was subjected to HPLC(Column: YMC-Actus Triart C18 100*20 mm, 5um; 0-5 min 5-55% water-MeOH(NH$_3$ 0.1%), flow 30 ml/min), affording N-(6-amino-5-methyl-3-pyridyl)-2-[(2S,5R)-5-methyl-2-(4-sulfamoylphenyl)-1-piperidyl]-2-oxo-acetamide (27 mg, 62.57 µmol, 34.29% yield).

$^1$H NMR (DMSO-d$_6$, 600 MHz): δ (ppm) 1.00 (m, 3H), 1.32 (m, 1H), 1.62 (m, 1H), 1.86 (m, 1H), 1.99 (m, 4H), 2.22 (m, 1H), 2.96 (m, 1H), 3.67 (m, 1H), 5.47 (m, 3H), 7.32 (m, 2H), 7.50 (m, 3H), 7.80 (m, 2H), 7.98 (m, 1H), 10.50 (m, 1H)

LCMS(ESI): [M+H]$^+$ m/z: calcd 431.2; found 432.2; Rt=1.645 min.

Example 356. The Synthesis of N-(6-amino-5-methyl-3-pyridyl)-2-[(2S,5R)-5-methyl-2-[4-(methylsulfamoyl)phenyl]-1-piperidyl]-2-oxo-acetamide (Compound 668

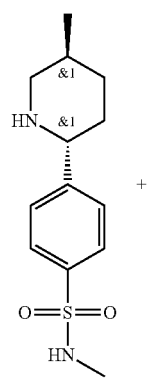

+

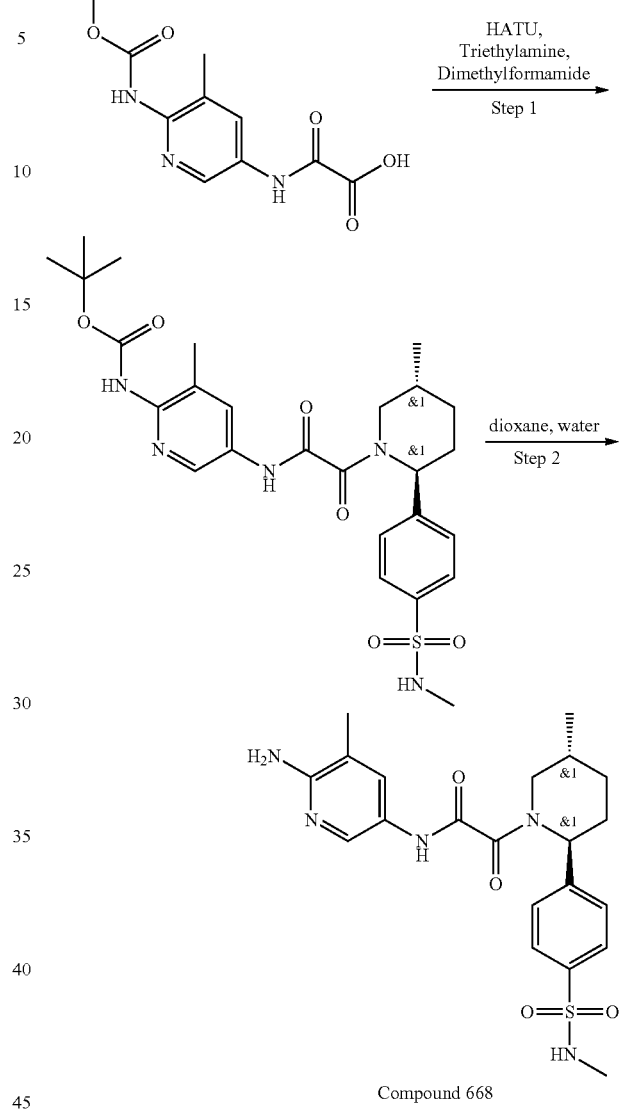

Compound 668

Step 1: Synthesis of tert-butyl N-[3-methyl-5-[[2-[(2S,5R)-5-methyl-2-[4-(methylsulfamoyl)phenyl]-1-piperidyl]-2-oxo-acetyl]amino]-2-pyridyl]carbamate To a stirred mixture of N-methyl-4-(5-methyl-2-piperidyl)benzenesulfonamide (370 mg, 1.38 mmol, HCl), 2-[[6-(tert-butoxycarbonylamino)-5-methyl-3-pyridyl]amino]-2-oxo-acetic acid (407.11 mg, 1.38 mmol) and Triethylamine (418.52 mg, 4.14 mmol, 576.48 µL) in Dimethylformamide (4 mL) was added HATU (576.63 mg, 1.52 mmol). The resulting reaction mixture was stirred at 20° C. for 5 hr. Then, it was subjected to HPLC (Column: YMC Triart C18 100×20 mm, 5 um; 40-70% 0-5 min 0.1% NH$_3$-methanol, flow: 30 ml/min), affording tert-butyl N-[3-methyl-5-[[2-[(2S,5R)-5-methyl-2-[4-(methylsulfamoyl)phenyl]-1-piperidyl]-2-oxo-acetyl]amino]-2-pyridyl]carbamate (140 mg, 256.57 µmol, 18.61% yield).

LCMS(ESI): [M+H]$^+$ m/z: calcd 545.3; found 546.2; Rt=3.010 min.

Step 2: Synthesis of N-(6-amino-5-methyl-3-pyridyl)-2-[(2S,5R)-5-methyl-2-[4-(methylsulfamoyl)phenyl]-1-piperidyl]-2-oxo-acetamide (Compound 668 water (1.00 g, 55.49 mmol, 1 mL) was added to a solution of tert-butyl N-[3-methyl-5-[[2-[(2S,5R)-5-methyl-2-[4-(methylsulfamoyl)phenyl]-1-piperidyl]-2-oxo-acetyl]amino]-2-pyridyl]carbamate (140 mg, 256.57 μmol) in dioxane (2 mL). Resulting mixture was stirred at 95° C. for 18 hr. Then, it was subjected to HPLC (Column: YMC-Actus Triart C18 100*20 mm, 5 um; 0-5 min 10-60% water-MeOH (NH₃ 0.1%), flow 30 ml/min), affording N-(6-amino-5-methyl-3-pyridyl)-2-[(2S,5R)-5-methyl-2-[4-(methylsulfamoyl)phenyl]-1-piperidyl]-2-oxo-acetamide (85 mg, 190.78 μmol, 74.36% yield).

$^1$H NMR (DMSO-d$_6$, 600 MHz): δ (ppm) 1.00 (m, 3H), 1.33 (m, 1H), 1.62 (m, 1H), 1.87 (m, 1H), 1.99 (m, 3H), 2.14 (m, 2H), 2.39 (m, 3H), 2.97 (m, 1H), 3.76 (m, 1H), 5.60 (m, 3H), 7.43 (m, 1H), 7.50 (m, 2H), 7.56 (m, 1H), 7.76 (m, 2H), 7.98 (m, 1H), 10.49 (m, 1H)

LCMS(ESI): [M+H]$^+$ m/z: calcd 445.2; found 446.2; Rt=1.267 min.

Example 357. The Synthesis of N-(6-amino-5-methyl-3-pyridyl)-2-[(2S,5R)-5-methyl-2-Thiazolo[5,4-b]pyridin-6-yl-1-piperidyl]-2-oxo-acetamide (Compound 685

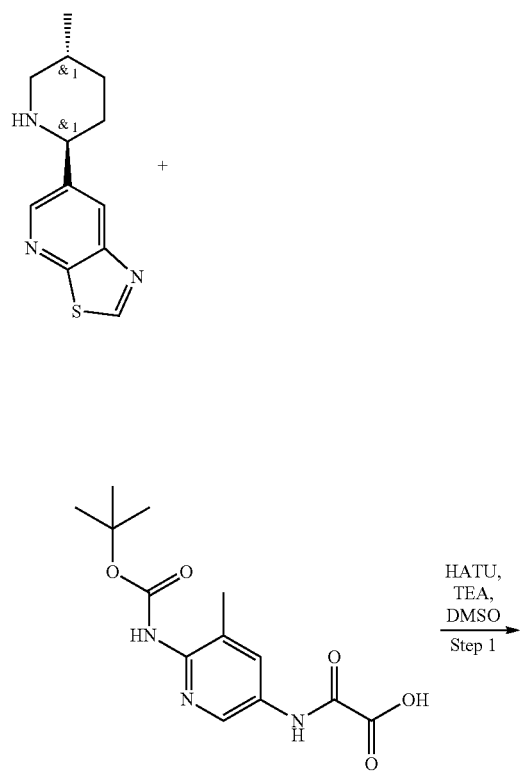

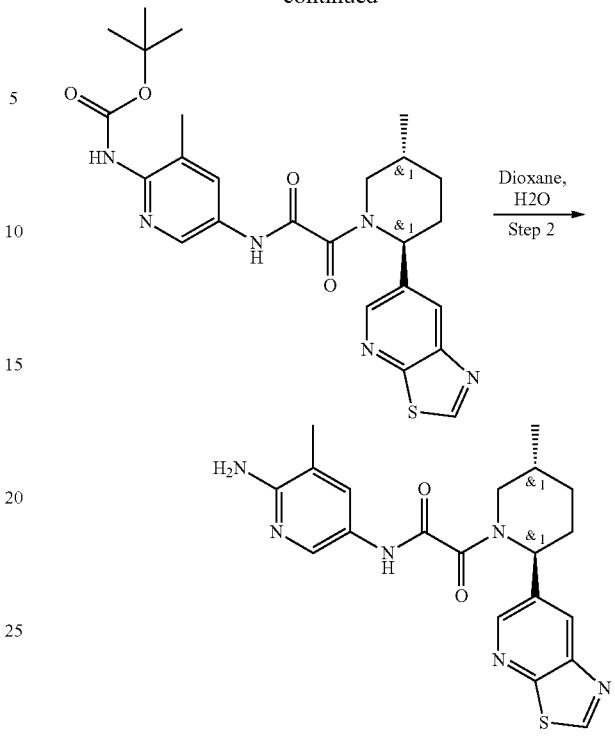

Compound 685

Step 1: Synthesis of tert-butyl N-[3-methyl-5-[[2-[(2S,5R)-5-methyl-2-Thiazolo[5,4-b]pyridin-6-yl-1-piperidyl]-2-oxo-acetyl]amino]-2-pyridyl]carbamate 2-[[6-(tert-butoxycarbonylamino)-5-methyl-3-pyridyl]amino]-2-oxo-acetic acid (316.38 mg, 1.07 mmol), 6-[(2S,5R)-5-methyl-2-piperidyl]thiazolo[5,4-b]pyridine (250.00 mg, 1.07 mmol), HATU (448.13 mg, 1.18 mmol) and TEA (119.26 mg, 1.18 mmol, 164.27 μL) were mixed in DMSO (2 mL) with vigorous stirring. Reaction mixture was treated with water and needed product was extracted with 50 ml of EA, dried over Na$_2$SO$_4$ and concentrated in vacuo to give tert-butyl N-[3-methyl-5-[[2-[(2S,5R)-5-methyl-2-thiazolo[5,4-b]pyridin-6-yl-1-piperidyl]-2-oxo-acetyl]amino]-2-pyridyl]carbamate (0.45 g, crude).

LCMS(ESI): [M+H]$^+$ m/z: calcd 510.2; found 511.0; Rt=1.340 min.

Step 2: The Synthesis of N-(6-amino-5-methyl-3-pyridyl)-2-[(2S,5R)-5-methyl-2-Thiazolo[5,4-b]pyridin-6-yl-1-piperidyl]-2-oxo-acetamide (Compound 685 tert-butyl N-[3-methyl-5-[[2-[(2S,5R)-5-methyl-2-thiazolo[5,4-b]pyridin-6-yl-1-piperidyl]-2-oxo-acetyl]amino]-2-pyridyl]carbamate (200.00 mg, 391.69 μmol) was dissolved in Dioxane (3 mL) and H$_2$O (3 mL) was added. Reaction mixture was stirred with vigorous stirring for 64 hr at 90° C. The solution was concentrated in vacuo, redissolved in 4 ml of methanol and subjected to HPLC.

HPLC data: 2-10 min 10-60% water/R1(loading pump 4 ml R1) column: TRIART 100*20 5 microM N-(6-amino-5-methyl-3-pyridyl)-2-[(2S,5R)-5-methyl-2-thiazolo[5,4-b]pyridin-6-yl-1-piperidyl]-2-oxo-acetamide (0.051 g, 124.24 μmol, 31.72% yield) was obtained.

¹H NMR (DMSO-d₆, 600 MHz): δ (ppm) 1.02 (m, 3H), 1.37 (m, 1H), 1.72 (m, 1H), 1.87 (m, 1H), 1.99 (m, 3H), 2.15 (m, 1H), 2.31 (m, 1H), 3.33 (m, 1H), 3.75 (m, 1H), 5.64 (m, 3H), 7.44 (m, 1H), 8.01 (m, 1H), 8.39 (m, 1H), 8.66 (m, 1H), 9.56 (m, 1H), 10.54 (m, 1H)

LCMS(ESI): [M+H]⁺ m/z: calcd 410.2; found 411.2; Rt=1.543 min.

Example 358. The Synthesis of N-(6-amino-5-methyl-3-pyridyl)-2-[(2S,5S)-3,3-difluoro-2-(4-fluorophenyl)-5-methyl-1-piperidyl]-2-oxo-acetamide (Compound 871

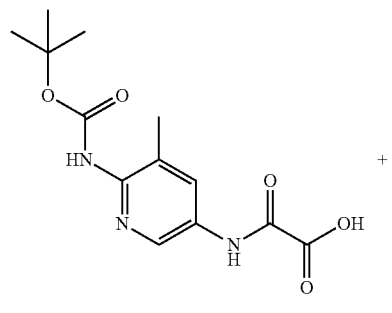

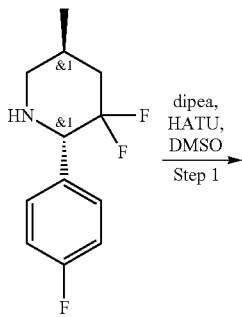

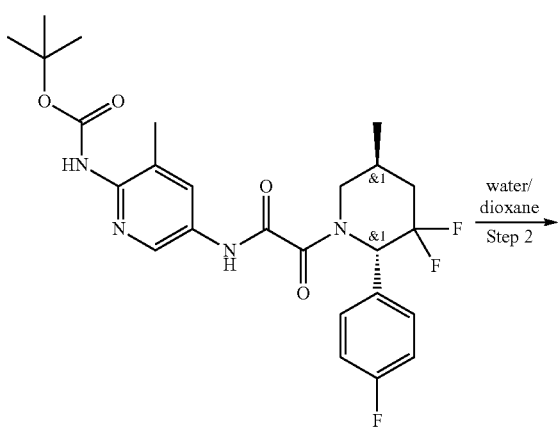

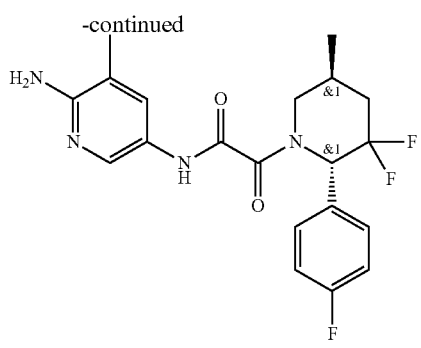

Compound 871

Step 1: Synthesis of tert-butyl N-[5-[[2-[(2S,5S)-3,3-difluoro-2-(4-fluorophenyl)-5-methyl-1-piperidyl]-2-oxo-acetyl]amino]-3-methyl-2-pyridyl]carbamate 2-[[6-(tert-butoxycarbonylamino)-5-methyl-3-pyridyl]amino]-2-oxo-acetic acid (287.67 mg, 974.21 μmol), (2S,5S)-3,3-difluoro-2-(4-fluorophenyl)-5-methyl-piperidine (223.33 mg, 974.21 μmol) and dipea (377.73 mg, 2.92 mmol, 509.07 μL) were dissolved in DMSO (6 mL) under gentle heating. HATU (444.51 mg, 1.17 mmol) was added in small portions under vigorous stirring and occasional heating. After the reaction was complete, the mixture was purified by HPLC to give tert-butyl N-[5-[[2-[(2S,5S)-3,3-difluoro-2-(4-fluorophenyl)-5-methyl-1-piperidyl]-2-oxo-acetyl]amino]-3-methyl-2-pyridyl]carbamate (80 mg, 157.94 μmol, 16.21% yield)

HPLC conditions: (48% 0.5-6.5 min water-acetonitrile; flow 30 ml/min; (loading pump 4 ml/min acetonitrile); target mass 506; column SunFire C18 100×19 mm 5 um (L)).

LCMS(ESI): [M+H]⁺ m/z: calcd 506.3; found 507.2; Rt=3.521 min.

Step 2: The Synthesis of N-(6-amino-5-methyl-3-pyridyl)-2-[(2S,5S)-3,3-difluoro-2-(4-fluorophenyl)-5-methyl-1-piperidyl]-2-oxo-acetamide (Compound 871 tert-butyl N-[5-[[2-[(2S,5S)-3,3-difluoro-2-(4-fluorophenyl)-5-methyl-1-piperidyl]-2-oxo-acetyl]amino]-3-methyl-2-pyridyl]carbamate (80 mg, 157.94 μmol) was dissolved in water (1 mL)/dioxane (1 mL) mixture and stirred at reflux overnight. Aliquot shows the full consumption of the starting material; evaporation of the solvents under reduced pressure and purification with HPLC (5-40% 0.5-6.5 min water-acetonitrile; flow 30 ml/min (loading pump 4 ml/min acetonitrile); target mass 382; column SunFire C18 100×19 mm 5 um (R)) results in N-(6-amino-5-methyl-3-pyridyl)-2-[(2S,5S)-3,3-difluoro-2-(4-fluorophenyl)-5-methyl-1-piperidyl]-2-oxo-acetamide (31 mg, 76.28 μmol, 48.30% yield)

¹H NMR (600 MHz, DMSO-d₆) δ 0.98-1.08 (m, 3H), 1.28-1.42 (m, 1H), 1.57-1.70 (m, 1H), 1.82-1.96 (m, 1H), 2.03-2.19 (m, 1H), 2.19-2.32 (m, 1H), 2.70-3.24 (m, 1H), 3.50-4.07 (m, 1H), 5.22-5.76 (m, 1H), 7.57-7.72 (m, 5H), 8.08-8.19 (m, 1H), 8.38-8.53 (m, 1H), 8.67-8.78 (m, 1H), 8.78-8.93 (m, 1H), 11.29 (br s, 1H).

LCMS(ESI): [M+H]⁺ m/z: calcd 406.2; found 407.2; Rt=2.294 min.

Example 359. The Synthesis of N-(6-amino-5-methyl-3-pyridyl)-2-[(2R,3R,5R)-3-fluoro-2-(4-fluorophenyl)-5-methyl-1-piperidyl]-2-oxo-acetamide (Compound 939), N-(6-amino-5-methyl-3-pyridyl)-2-[(2R,3R,5S)-3-fluoro-2-(4-fluorophenyl)-5-methyl-1-piperidyl]-2-oxo-acetamide (Compound 940) and N-(6-amino-5-methyl-3-pyridyl)-2-[(2R,3S,5S)-3-fluoro-2-(4-fluorophenyl)-5-methyl-1-piperidyl]-2-oxo-acetamide (Compound 904
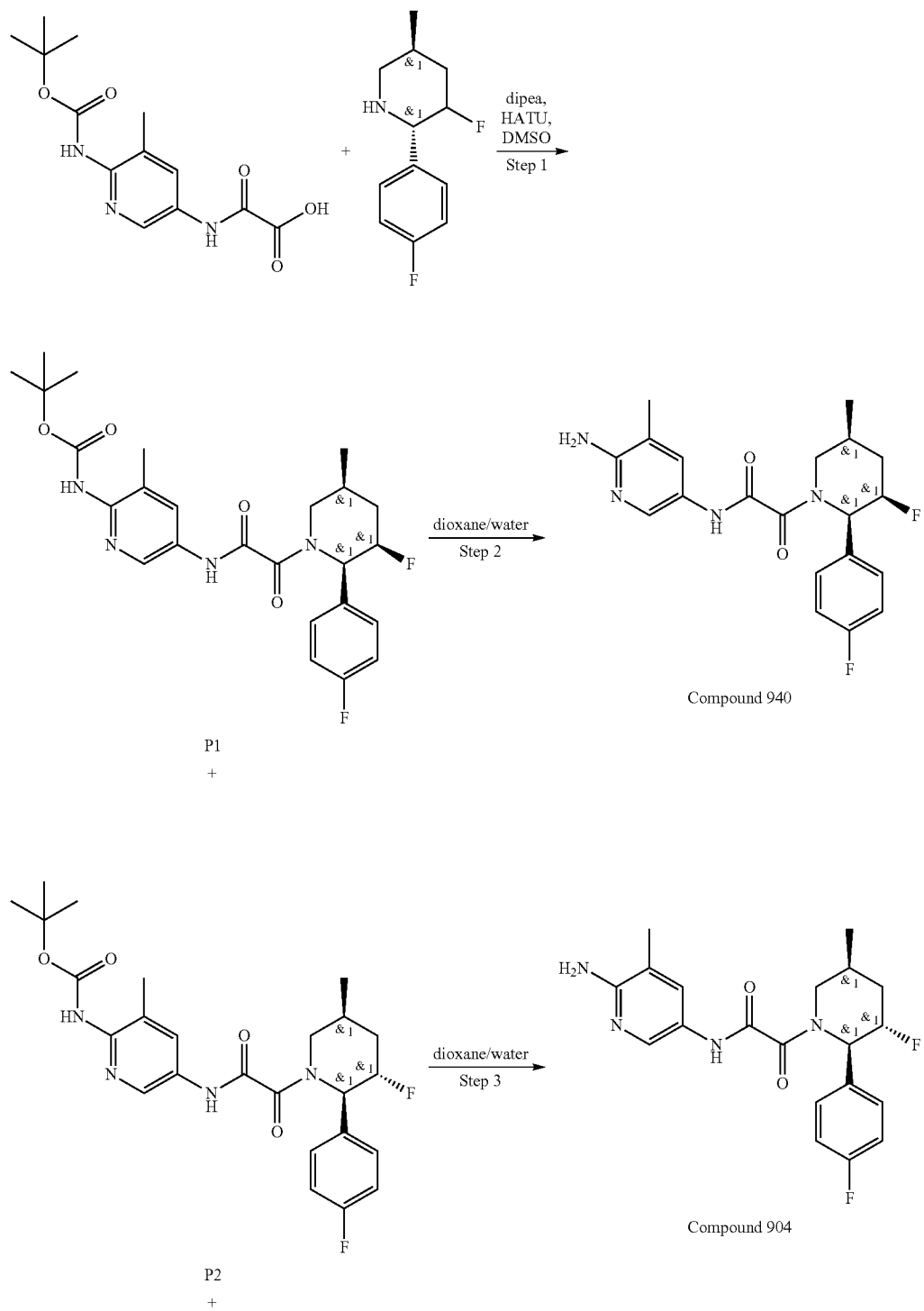

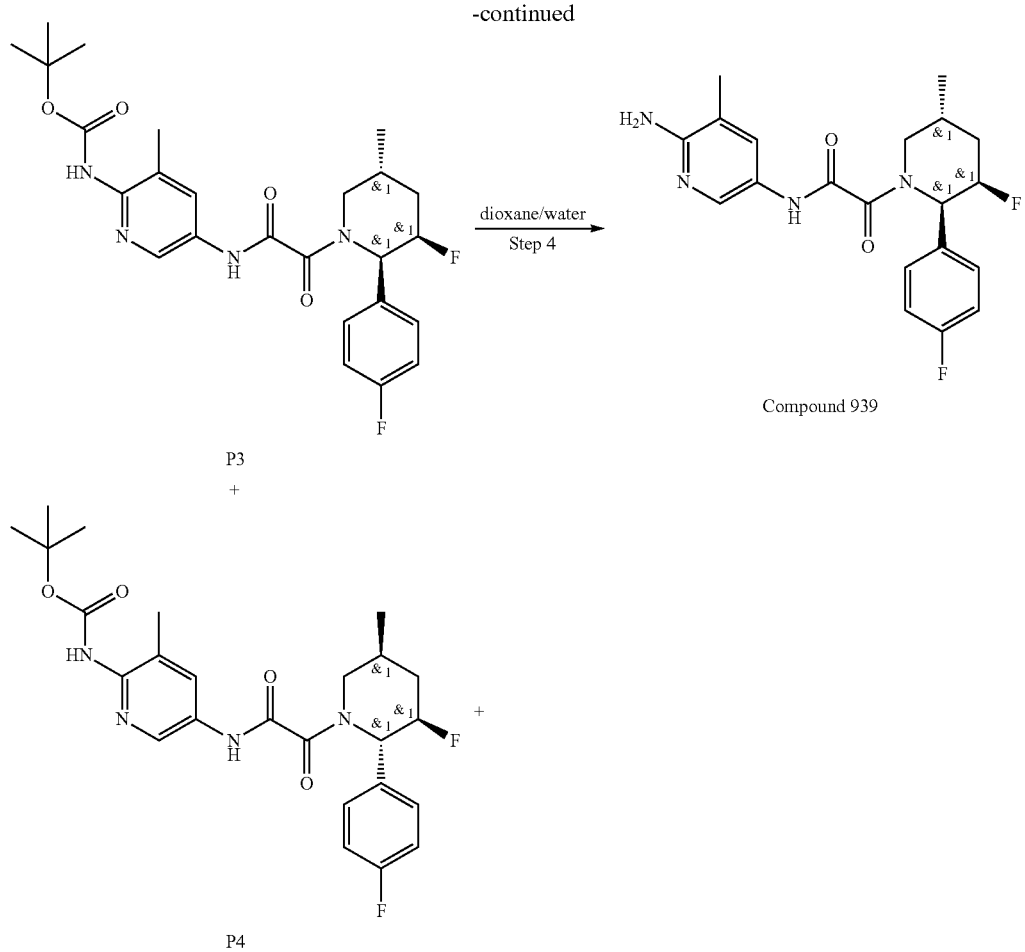

Compound 939

P3

+

P4

Step 1: Synthesis of tert-butyl N-[5-[[2-[(2R,3R,5S)-3-fluoro-2-(4-fluorophenyl)-5-methyl-1-piperidyl]-2-oxo-acetyl]amino]-3-methyl-2-pyridyl]carbamate (P1), Tert-butyl N-[5-[[2-[(2R,3S,5S)-3-fluoro-2-(4-fluorophenyl)-5-methyl-1-piperidyl]-2-oxo-acetyl]amino]-3-methyl-2-pyridyl]carbamate (P2), Tert-butyl N-[5-[[2-[(2R,3R,5R)-3-fluoro-2-(4-fluorophenyl)-5-methyl-1-piperidyl]-2-oxo-acetyl]amino]-3-methyl-2-pyridyl]carbamate (P4) and Tert-butyl N-[5-[[2-[(2R,3R,5R)-3-fluoro-2-(4-fluorophenyl)-5-methyl-1-piperidyl]-2-oxo-acetyl]amino]-3-methyl-2-pyridyl]carbamate (P3

2-[[6-(tert-butoxycarbonylamino)-5-methyl-3-pyridyl]amino]-2-oxo-acetic acid (287.67 mg, 974.21 μmol), (2S,5S)-3-fluoro-2-(4-fluorophenyl)-5-methyl-piperidine (205.80 mg, 974.21 μmol) and dipea (377.73 mg, 2.92 mmol, 509.07 μL) were dissolved in DMSO (6 mL) under gentle heating. HATU (444.51 mg, 1.17 mmol) was added in small portions under vigorous stirring and occasional heating. After the reaction was complete, the mixture was purified by HPLC to give tert-butyl N-[5-[[2-[(2R,3R,5S)-3-fluoro-2-(4-fluorophenyl)-5-methyl-1-piperidyl]-2-oxo-acetyl]amino]-3-methyl-2-pyridyl]carbamate P1 (10 mg, 20.47 μmol, 2.10% yield) tert-butyl N-[5-[[2-[(2R,3S,5S)-3-fluoro-2-(4-fluorophenyl)-5-methyl-1-piperidyl]-2-oxo-acetyl]amino]-3-methyl-2-pyridyl]carbamate (30 mg, 61.41 μmol, 6.30% yield) tert-butyl N-[5-[[2-[(2R,3R,5R)-3-fluoro-2-(4-fluorophenyl)-5-methyl-1-piperidyl]-2-oxo-acetyl]amino]-3-methyl-2-pyridyl]carbamate P3 (100 mg, 204.70 μmol, 21.01% yield) and tert-butyl N-[5-[[2-[(2R,3R,5R)-3-fluoro-2-(4-fluorophenyl)-5-methyl-1-piperidyl]-2-oxo-acetyl]amino]-3-methyl-2-pyridyl]carbamate P4 (40 mg, 81.88 μmol, 8.40% yield)

HPLC conditions: (48% 0.5-6.5 min water-acetonitrile; flow 30 ml/min; (loading pump 4 ml/minacetonitrile); target mass 506; column SunFire C18 100×19 mm 5 um (L))

P1: LCMS(ESI): [M+H]$^+$ m/z: calcd 488.3; found 489.4; Rt=3.580 min.

P2: LCMS(ESI): [M+H]$^+$ m/z: calcd 488.3; found 489.0; Rt=3.350 min.

P3: LCMS(ESI): [M+H]$^+$ m/z: calcd 488.3; found 489.2; Rt=2.906 min.

P4: LCMS(ESI): [M+H]$^+$ m/z: calcd 488.3; found 489.4; Rt=3.379 min.

Step 2: Synthesis of N-(6-amino-5-methyl-3-pyridyl)-2-[(2R,3R,5S)-3-fluoro-2-(4-fluorophenyl)-5-methyl-1-piperidyl]-2-oxo-acetamide (Compound 940 tert-butyl N-[5-[[2-[(2R,3R,5S)-3-fluoro-2-(4-fluorophenyl)-5-methyl-1-piperidyl]-2-oxo-acetyl]amino]-3-methyl-2-pyridyl]carbamate P1 (10 mg, 20.47 μmol) was dissolved in dioxane (2 mL)/H$_2$O (0.5 mL) mixture and stirred at reflux overnight. Aliquot shows the full consumption of the starting material; evaporation of the solvents under reduced pressure and purification with HPLC (32-36% 0.5-6.5 min water-acetonitrile; flow 30 ml/min (loading pump 4 ml/min acetonitrile); target mass 388; column SunFire C18 100×19 mm 5 um (R)) results in N-(6-amino-5-methyl-3-pyridyl)-2-[(2R,3R,5S)-3-fluoro-2-(4-fluorophenyl)-5-methyl-1-piperidyl]-2-oxo-acetamide (5 mg, 12.87 μmol, 62.89% yield).

¹H NMR (DMSO-d₆, 600 MHz): δ (ppm) 0.87 (dd, 3H), 1.63 (m, 2H), 2.00 (m, 4H), 2.08 (m, 1H), 2.72 (m, 1H), 3.68 (m, 1H), 5.03 (m, 1H), 5.65 (m, 3H), 7.20 (m, 2H), 7.46 (m, 2H), 7.97 (m, 1H), 10.51 (m, 1H)

LCMS(ESI): [M+H]⁺ m/z: calcd 388.2; found 389.0; Rt=2.128 min.

Step 3: Synthesis of N-(6-amino-5-methyl-3-pyridyl)-2-[(2R,3S,5S)-3-fluoro-2-(4-fluorophenyl)-5-methyl-1-piperidyl]-2-oxo-acetamide (Compound 904 tert-butyl N-[5-[[2-[(2R,3S,5S)-3-fluoro-2-(4-fluorophenyl)-5-methyl-1-piperidyl]-2-oxo-acetyl]amino]-3-methyl-2-pyridyl]carbamate P2 (30 mg, 61.41 μmol) was dissolved in dioxane (4 mL)/H₂O (0.5 mL) mixture and stirred at reflux overnight. Aliquot shows the full consumption of the starting material; evaporation of the solvents under reduced pressure and purification with HPLC 32-36% 0.5-6.5 min water-acetonitrile; flow 30 ml/min (loading pump 4 ml/min acetonitrile); target mass 388; column SunFire C18 100×19 mm 5 um (R)) results in tert-butyl N-[5-[[2-[(2R,3S,5S)-3-fluoro-2-(4-fluorophenyl)-5-methyl-1-piperidyl]-2-oxo-acetyl]amino]-3-methyl-2-pyridyl]carbamate (11 mg, 22.52 μmol, 36.67% yield).

¹H NMR (DMSO-d₆, 600 MHz): δ (ppm) 1.05 (m, 3H), 1.72 (m, 1H), 1.87 (m, 2H), 2.00 (m, 3H), 3.01 (m, 1H), 3.70 (m, 1H), 5.60 (m, 4H), 7.22 (m, 2H), 7.43 (m, 3H), 8.00 (m, 1H), 10.51 (m, 1H).

LCMS(ESI): [M+H]⁺ m/z: calcd 388.2; found 389.2; Rt=2.419 min.

Step 4: The Synthesis of N-(6-amino-5-methyl-3-pyridyl)-2-[(2R,3R,5R)-3-fluoro-2-(4-fluorophenyl)-5-methyl-1-piperidyl]-2-oxo-acetamide (Compound 939 tert-butyl N-[5-[[2-[(2R,3R,5R)-3-fluoro-2-(4-fluorophenyl)-5-methyl-1-piperidyl]-2-oxo-acetyl]amino]-3-methyl-2-pyridyl]carbamate (P3) (100 mg, 204.70 μmol) was dissolved in dioxane (2 mL)/water (0.5 mL) mixture and stirred at reflux overnight. Aliquot shows the full consumption of the starting material; evaporation of the solvents under reduced pressure and purification with HPLC (32-36% 0.5-6.5 min water-acetonitrile; flow 30 ml/min (loading pump 4 ml/min acetonitrile); target mass 388; column SunFire C18 100×19 mm 5 um (R)) results in N-(6-amino-5-methyl-3-pyridyl)-2-[(2R,3R,5R)-3-fluoro-2-(4-fluorophenyl)-5-methyl-1-piperidyl]-2-oxo-acetamide (54 mg, 139.03 μmol, 67.92% yield).

¹H NMR (DMSO-d₆, 600 MHz): δ (ppm) 1.02 (d, 3H), 1.36 (m, 1H), 2.03 (m, 4H), 2.26 (m, 1H), 3.53 (m, 1H), 3.61 (m, 1H), 5.26 (m, 2H), 5.61 (m, 2H), 7.18 (m, 2H), 7.34 (m, 2H), 7.45 (s, 1H), 7.99 (m, 1H), 10.37 (m, 1H).

LCMS(ESI): [M+H]⁺ m/z: calcd 388.2; found 389.2; Rt=2.090 min.

Example 360. The Synthesis of N-(6-amino-5-methyl-3-pyridyl)-2-[(2R,5S)-5-methyl-2-[1-(1H-pyrazol-3-yl)pyrazol-4-yl]-1-piperidyl]-2-oxo-acetamide (Compound 793

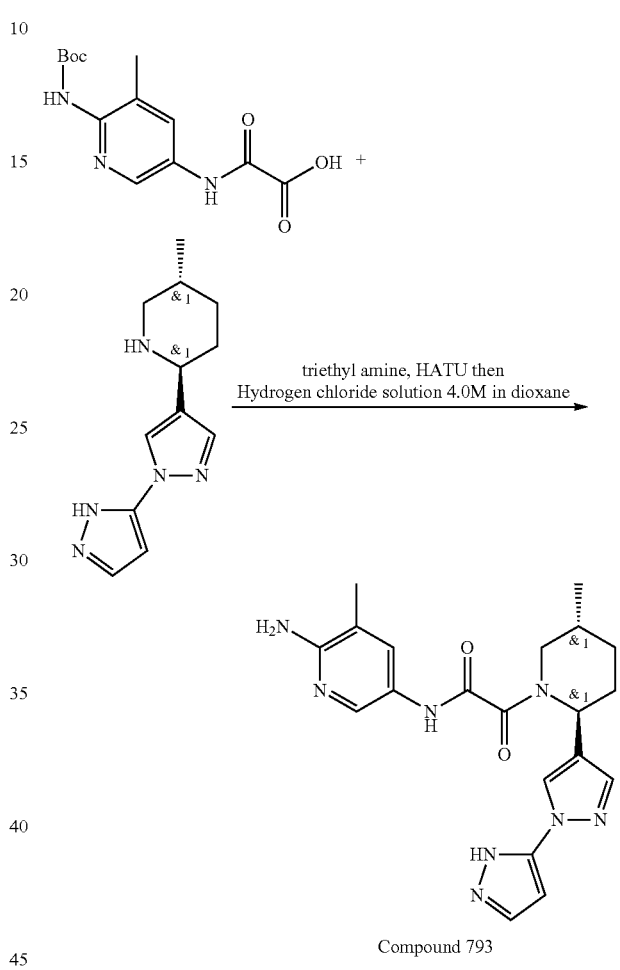

Compound 793

HATU (877.81 mg, 2.31 mmol) was added in small portions over 0.5 hr period to a stirred mixture of (2R,5S)-5-methyl-2-[1-(1H-pyrazol-3-yl)pyrazol-4-yl]piperidine (1.1 g, 2.10 mmol, 3HCl), 2-[[6-(tert-butoxycarbonylamino)-5-methyl-3-pyridyl]amino]-2-oxo-acetic acid (619.74 mg, 2.10 mmol) and triethyl amine (2.12 g, 20.99 mmol, 2.93 mL) in DMF (10 mL) at 25° C. The resulting mixture was stirred at 25° C. for 18 hr, and then concentrated in vacuo. The residue was dissolved in dichloromethane (10 mL) and Hydrogen chloride solution 4.0 M in dioxane (19.25 g, 73.39 mmol, 24.06 mL, 13.9% purity) was added in one portion. The resulting mixture was stirred at 25° C. for 3 hr, and then concentrated in vacuo. The residue was twice purified by reverse phase HPLC (column: YMC Triart C18 100×20 mm, 5 um) mobile phase: 35-60% 0-5 min H₂O/MeOH/0.1% NH₄OH, flow: 30 ml/min (loading pump 4 ml/min methanol) for 1st HPLC and 35-50% 0-5 min H₂O/MeOH/0.1% NH₄OH, flow: 30 ml/min (loading pump 4 ml/min methanol) for 2nd HPLC to afford Compound 793 N-(6-amino-5-methyl-3-pyridyl)-2-[(2R,5S)-5-methyl-2-[1-

(1H-pyrazol-3-yl)pyrazol-4-yl]-1-piperidyl]-2-oxo-acetamide (61 mg, 149.34 μmol, 7.12% yield) as white solid.

$^1$H NMR (dmso, 600 MHz): δ (ppm) 0.75-1.01 (m, 3H), 1.18-1.39 (m, 1H), 1.53-1.88 (m, 2H), 1.89-1.98 (m, 1H), 1.98-2.02 (m, 3H), 2.02-2.10 (m, 1H), 2.79-3.25 (m, 1H), 3.36-4.00 (m, 1H), 5.07-5.59 (m, 1H), 5.59-5.64 (m, 2H), 6.41-6.49 (m, 1H), 7.42-7.53 (m, 1H), 7.56-7.68 (m, 1H), 7.73-7.84 (m, 1H), 7.94-8.05 (m, 1H), 8.09-8.20 (m, 1H), 10.44-10.55 (m, 1H), 12.71-12.85 (m, 1H)

LCMS(ESI): [M+1]$^+$ m/z: calcd 408.2; found 409.2; Rt=1.719 min.

Example 361. The Synthesis of N-(6-amino-5-methyl-3-pyridyl)-2-[(2S,5R)-5-methyl-2-(1H-pyrazol-4-yl)-1-piperidyl]-2-oxo-acetamide (Compound 969) and N-(6-amino-5-methyl-3-pyridyl)-2-[(2R,5S)-5-methyl-2-(1H-pyrazol-4-yl)-1-piperidyl]-2-oxo-acetamide (Compound 941

DMF (10 mL) at 25° C. The resulting mixture was stirred at 25° C. for 18 hr, and then concentrated in vacuo. The residue was dissolved in dichloromethane (10 mL) and Hydrogen chloride solution 4.0 M in dioxane (10.50 g, 40.03 mmol, 10 mL, 13.9% purity) was added in one portion. The resulting mixture was stirred at 25° C. for 12 hr, and then concentrated in vacuo. The residue was purified by reverse phase HPLC (column: YMC Triart C18 100×20 mm, 5 um; mobile phase: 25-55% 0-5 min H$_2$O/MeOH/0.1% NH$_4$OH, flow: 30 ml/min (loading pump 4 ml/min methanol) to afford N-(6-amino-5-methyl-3-pyridyl)-2-[(2R,5S)-5-methyl-2-(1H-pyrazol-4-yl)-1-piperidyl]-2-oxo-acetamide (227 mg, 662.98 μmol, 60.73% yield) as light-yellow gum, which was directly submitted to preparative chiral HPLC.

LCMS(ESI): [M+1]$^+$ m/z: calcd 342.4; found 343.2; Rt=1.329 min.

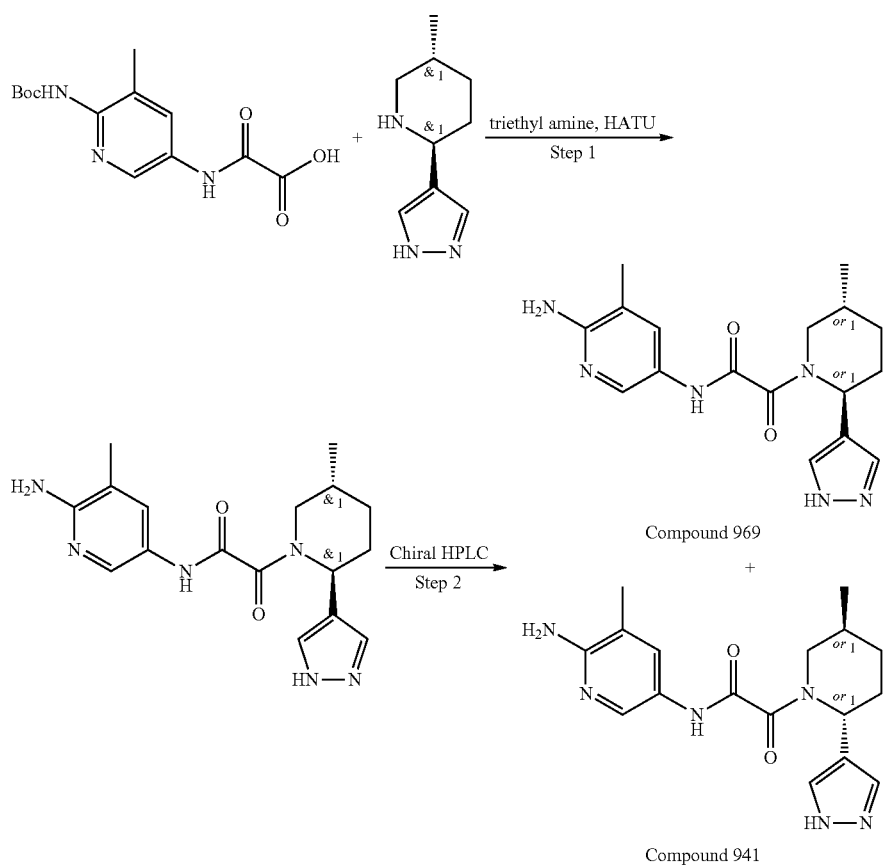

Step 1. N-(6-amino-5-methyl-3-pyridyl)-2-[(2R,5S)-5-methyl-2-(1H-pyrazol-4-yl)-1-piperidyl]-2-oxo-acetamide HATU (456.61 mg, 1.20 mmol) was added in small portions over 0.5 hr period to a stirred mixture of (2R,5S)-5-methyl-2-(1H-pyrazol-4-yl)piperidine (400 mg, 1.09 mmol, 2HCl), 2-[[6-(tert-butoxycarbonylamino)-5-methyl-3-pyridyl]amino]-2-oxo-acetic acid (370.73 mg, 1.26 mmol) and triethyl amine (883.77 mg, 8.73 mmol, 1.22 mL) in Step 2. The Synthesis of N-(6-amino-5-methyl-3-pyridyl)-2-[(2S,5R)-5-methyl-2-(1H-pyrazol-4-yl)-1-piperidyl]-2-oxo-acetamide (Compound 969) and N-(6-amino-5-methyl-3-pyridyl)-2-[(2R,5S)-5-methyl-2-(1H-pyrazol-4-yl)-1-piperidyl]-2-oxo-acetamide (Compound 941

Racemic N-(6-amino-5-methyl-3-pyridyl)-2-[(2R,5S)-5-methyl-2-(1H-pyrazol-4-yl)-1-piperidyl]-2-oxo-acetamide (227 mg, 662.98 μmol) was submitted to preparative chiral HPLC (Column: Chiralpak IC-II (250*20 mm, 5 mkm); Mobile phase:Hexane-IPA-MeOH 60-20-20;

Flow Rate: 12 mL/min) to afford crude 1st fraction (R.T.=27.732 min., 60 mg), and Compound 941 (2nd fraction)N-(6-amino-5-methyl-3-pyridyl)-2-[(2R,5S)-5-methyl-2-(1H-pyrazol-4-yl)-1-piperidyl]-2-oxo-acetamide (54.8 mg, 160.05 μmol, 24.14% yield) (R.T.=39.160 min.). Crude 1st fraction (60 mg) was repurified by preparative chiral HPLC (Column: Chiralcel OJ-H (250*20 mm, 5 mkm); Mobile phase:Hexane-IPA-MeOH 80-10-10; Flow Rate: 12 mL/min) to afford Compound 969 N-(6-amino-5-methyl-3-pyridyl)-2-[(2S,5R)-5-methyl-2-(1H-pyrazol-4-yl)-1-piperidyl]-2-oxo-acetamide (42.7 mg, 124.71 μmol, 18.81% yield) (R.T.=25.846 min.).

Compound 941: $^1$H NMR (600 MHz, DMSO-d$_6$) δ 0.94-1.00 (m, 3H), 1.29-1.39 (m, 1H), 1.76-1.83 (m, 1H), 1.84-1.94 (m, 2H), 1.94-2.07 (m, 4H), 2.72-3.24 (m, 1H), 3.38-3.95 (m, 1H), 4.98-5.57 (m, 1H), 5.57-5.65 (m, 2H), 7.22-7.80 (m, 3H), 7.91-8.05 (m, 1H), 10.28-10.53 (m, 1H), 12.75 (s, 1H).

LCMS(ESI): [M+1]$^+$ m/z: calcd 342.4; found 343.4; Rt=1.388 min.

Compound 969: $^1$H NMR (600 MHz, DMSO-d$_6$) δ 0.94-0.99 (m, 3H), 1.29-1.40 (m, 1H), 1.70-1.89 (m, 2H), 1.89-1.99 (m, 2H), 1.99-2.03 (m, 3H), 2.74-3.22 (m, 1H), 3.35-3.95 (m, 1H), 4.96-5.57 (m, 1H), 5.57-5.65 (m, 2H), 7.31-7.71 (m, 3H), 7.98 (d, 1H), 10.30-10.51 (m, 1H), 12.75 (s, 1H).

LCMS(ESI): [M+1]$^+$ m/z: calcd 342.4; found 343.4; Rt=1.379 min.

Example 362. The Synthesis of N-(6-amino-5-methyl-3-pyridyl)-2-[2-(5-amino-2-pyridyl)-5-methyl-1-piperidyl]-2-oxo-acetamide (Compound 658

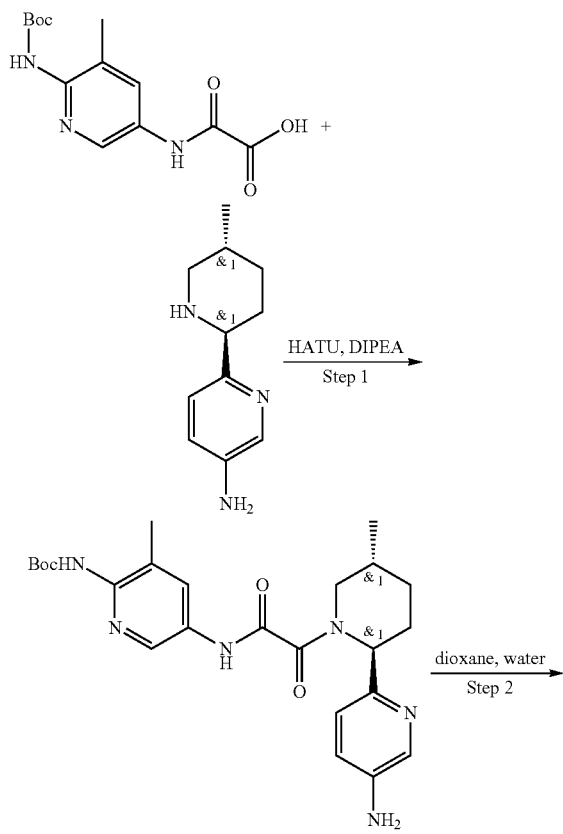

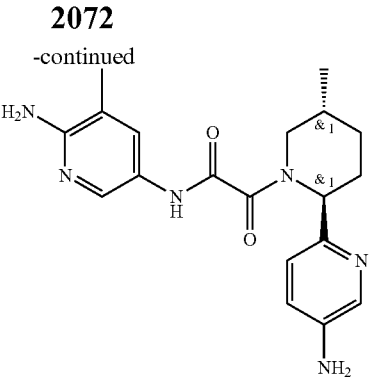

Compound 658

Step 1. Synthesis of tert-butyl N-[5-[[2-[2-(5-amino-2-pyridyl)-5-methyl-1-piperidyl]-2-oxo-acetyl]amino]-3-methyl-2-pyridyl]carbamate DIPEA (787.83 mg, 6.10 mmol, 1.06 mL) was added to the solution of respective 2-[[6-(tert-butoxycarbonylamino)-5-methyl-3-pyridyl]amino]-2-oxo-acetic acid (0.3 g, 1.02 mmol) and 6-(5-methyl-2-piperidyl)pyridin-3-amine (194.32 mg, 735.53 μmol, 2HCl) in DMF (10 mL). The resulting mixture was stirred for 5 min followed by the addition of HATU (424.92 mg, 1.12 mmol). Then, the reaction mixture was stirred overnight at room temperature. After the completion of the reaction, monitored by LCMS, the resulting suspension was concentrated under reduced pressure. The obtained solid was subjected to HPLC (Waters Sunfire C18 2*100 5 mkm column and H$_2$O-MeCN as an eluent mixture) to afford tert-butyl N-[5-[[2-[2-(5-amino-2-pyridyl)-5-methyl-1-piperidyl]-2-oxo-acetyl]amino]-3-methyl-2-pyridyl]carbamate (0.11 g, 234.77 μmol, 23.11% yield)

LCMS(ESI): [M+1]$^+$ m/z: calcd 468.2; found 369.2; Rt=2.265 min.

Step 2. N-(6-amino-5-methyl-3-pyridyl)-2-[2-(5-amino-2-pyridyl)-5-methyl-1-piperidyl]-2-oxo-acetamide (Compound 658 tert-butyl N-[5-[[2-[2-(5-amino-2-pyridyl)-5-methyl-1-piperidyl]-2-oxo-acetyl]amino]-3-methyl-2-pyridyl]carbamate (0.11 g, 234.77 μmol) was dissolved in water (5 mL) and dioxane (2 mL) mixture. Then reaction mixture was stirred for 17 hr at 100° C. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford pure N-(6-amino-5-methyl-3-pyridyl)-2-[2-(5-amino-2-pyridyl)-5-methyl-1-piperidyl]-2-oxo-acetamide (3.9 mg, 10.59 μmol, 4.51% yield).

$^1$H NMR (DMSO-d$_6$, 600 MHz): δ (ppm) 0.75 (m, 3H), 1.12 (m, 1H), 1.64 (m, 3H), 2.01 (m, 3H), 2.63 (m, 1H), 3.44 (m, 1H), 4.27 (m, 1H), 5.36 (m, 5H), 6.98 (m, 2H), 7.47 (m, 1H), 7.89 (m, 1H), 7.98 (m, 1H), 10.43 (m, 1H)

LCMS(ESI): [M+1]$^+$ m/z: calcd 368.2; found 370.4; Rt=1.148 min.

Example 363. The Synthesis of N-(6-amino-5-ethyl-3-pyridyl)-2-[(2R,5S)-2-(1,3-benzothiazol-5-yl)-5-methyl-1-piperidyl]-2-oxo-acetamide (Compound 701)

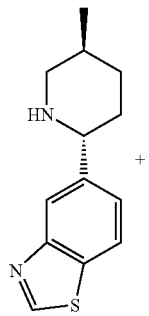

+

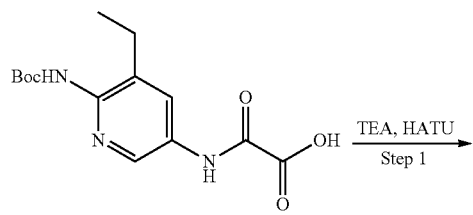

TEA, HATU
Step 1

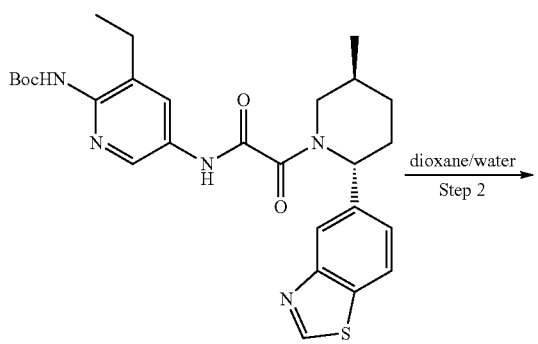

dioxane/water
Step 2

Compound 701

Step 1. Synthesis of tert-butyl N-[5-[[2-[(2R,5S)-2-(1,3-benzothiazol-5-yl)-5-methyl-1-piperidyl]-2-oxo-acetyl]amino]-3-ethyl-2-pyridyl]carbamate HATU (4.50 g, 11.84 mmol) was added portionwise at r.t. to a suspension of 2-[[6-(tert-butoxycarbonylamino)-5-ethyl-3-pyridyl]amino]-2-oxo-acetic acid (3.66 g, 11.84 mmol), 5-[(2R,5S)-5-methyl-2-piperidyl]-1,3-benzothiazole (2.5 g, 10.76 mmol) (intermediate 6LL) and TEA (6.53 g, 64.56 mmol, 9.00 mL) in DMF (35 mL). The clear solution was stirred at 20° C. for 32 hr and the solvents were evaporated in vacuo. The residue was dissolved in EtOAc (300 mL), washed with water (5×100 mL), evaporated in vacuo and purified by silica gel flash chromatography eluting with a 0 to 100 percent ACN-chloroform gradient to give 2.5 g of product with cis impurity. The individual trans-isomer was separated by chiral HPLC (column: Chiralcel OJ (250*30, 20 mkm), $CO_2$-MeOH, 75-25, 80 ml/min make up flow rate—30 ml/min as mobile phase) to give tert-butyl N-[5-[[2-[(2R,5S)-2-(1,3-benzothiazol-5-yl)-5-methyl-1-piperidyl]-2-oxo-acetyl]amino]-3-ethyl-2-pyridyl]carbamate (1.94 g, 3.70 mmol, 34.43% yield). Boc-deprotected product was purified by RP-HPLC (column: YMC-Actus Triart C18 100*20 mml.D. S-5 um; 35-55% 0-5 min $H_2O$/ACN/0.1% $NH_4OH$, flow: 30 ml/min as mobile phase) to give N-(6-amino-5-ethyl-3-pyridyl)-2-[(2R,5S)-2-(1,3-benzothiazol-5-yl)-5-methyl-1-piperidyl]-2-oxo-acetamide (0.9 g, 2.12 mmol, 19.75% yield).

LCMS(ESI): $[M+1]^+$ m/z: calcd 523.2; found 524.2; Rt=1.288 min.

LCMS(ESI): $[M+1]^+$ m/z: calcd 423.2; found 424.2; Rt=2.199 min.

RT (OJ-H, $CO_2$-MeOH, 80-20, 3.0 mL/min)=2.859 min for Boc-intermediate (99+ee)

Step 2. Synthesis of N-(6-amino-5-ethyl-3-pyridyl)-2-[(2R,5S)-2-(1,3-benzothiazol-5-yl)-5-methyl-1-piperidyl]-2-oxo-acetamide (Compound 701

The solution of tert-butyl N-[5-[[2-[(2R,5S)-2-(1,3-benzothiazol-5-yl)-5-methyl-1-piperidyl]-2-oxo-acetyl]amino]-3-ethyl-2-pyridyl]carbamate (1.94 g, 3.70 mmol) in dioxane (20 mL) and water (10 mL) was stirred for 12 hr at 85° C. and the solvents were evaporated in vacuo. The residue was purified by RP-HPLC (column: YMC-Actus Triart C18 100*20 mml.D. S-5 um; 35-60% 0-5 min $H_2O$/ACN/0.1% $NH_4OH$, flow: 30 ml/min as mobile phase then another column: Chromatorex 18 SMB 100-5T 100×19 mm 5 um; 30-60% 0-5 min $H_2O$/MeOH/0.1% FA, flow: 30 ml/min as mobile phase) to give 0.8 g of product with solvents. It was dissolved in 15 mL of dry ethanol, evaporated in vacuo and dried in vacuo for 24 hr at 45° C. to give Compound 701 N-(6-amino-5-ethyl-3-pyridyl)-2-[(2R,5S)-2-(1,3-benzothiazol-5-yl)-5-methyl-1-piperidyl]-2-oxo-acetamide (0.5 g, 1.18 mmol, 31.87% yield). $[\alpha]21D=+135.0°$ (c=0.1 g/100 mL EtOH).

$^1H$ NMR (DMSO-$d_6$, 500 MHz): δ (ppm) 1.04 (t, 6H), 1.36 (m, 1H), 1.72 (m, 1H), 1.87 (m, 1H), 2.13 (m, 1H), 2.35 (m, 2H), 3.78 (m, 3H), 4.33 (s, 1H), 5.66 (m, 3H), 7.43 (d, 1H), 7.51 (d, 1H), 8.00 (d, 1H), 8.06 (d, 1H), 8.17 (m, 1H), 9.40 (s, 1H), 10.56 (m, 1H)

LCMS(ESI): $[M+1]^+$ m/z: calcd 423.2; found 424.2; Rt=2.082 min.

Example 364. The Synthesis of N-(6-amino-5-methyl-3-pyridyl)-2-[(2R,5S)-5-methyl-2-(1H-pyrazolo[4,3-b]pyridin-5-yl)-1-piperidyl]-2-oxo-acetamide (Compound 788) and N-(6-amino-5-methyl-3-pyridyl)-2-[(2S,5R)-5-methyl-2-(1H-pyrazolo[4,3-b]pyridin-5-yl)-1-piperidyl]-2-oxo-acetamide (Compound 780

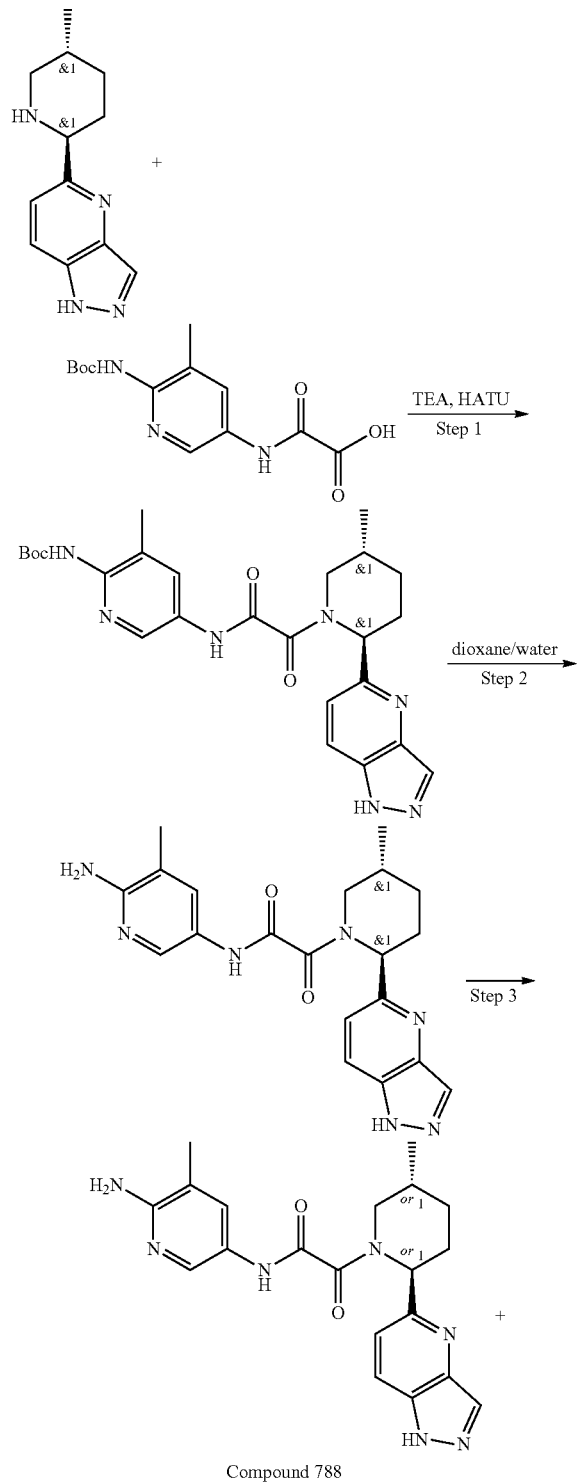

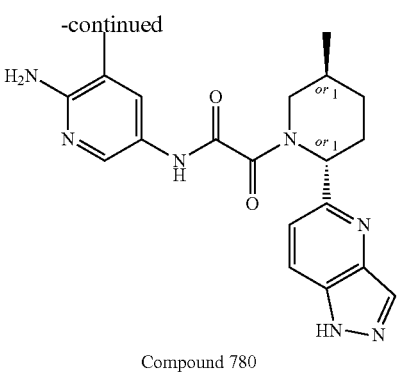

Compound 780

Step 1. The Synthesis of tert-butyl N-[3-methyl-5-[[2-[5-methyl-2-(1H-pyrazolo[4,3-b]pyridin-5-yl)-1-piperidyl]-2-oxo-acetyl]amino]-2-pyridyl]carbamate 2-[[6-(tert-butoxycarbonylamino)-5-methyl-3-pyridyl]amino]-2-oxo-acetic acid (327.67 mg, 1.11 mmol) and 5-(5-methyl-2-piperidyl)-1H-pyrazolo[4,3-b]pyridine (0.24 g, 1.11 mmol) were mixed in DMF (20 mL). The reaction suspension was cooled to 0° C. and HATU (506.31 mg, 1.33 mmol) followed by TEA (336.86 mg, 3.33 mmol, 464.00 µL) were added and stirred at ambient temperature for 14 hr. The reaction mixture was evaporated in vacuo to afford product tert-butyl N-[3-methyl-5-[[2-[5-methyl-2-(1H-pyrazolo[4,3-b]pyridin-5-yl)-1-piperidyl]-2-oxo-acetyl]amino]-2-pyridyl]carbamate (0.7 g, crude)

LCMS(ESI): [M+H]$^+$ m/z: calcd 493.5; found 494.2; Rt=1.214 min.

Step 2. Synthesis of N-(6-amino-5-methyl-3-pyridyl)-2-[5-methyl-2-(1H-pyrazolo[4,3-b]pyridin-5-yl)-1-piperidyl]-2-oxo-acetamide Water (10 mL) was added in one portion to a stirred solution of tert-butyl N-[3-methyl-5-[[2-[5-methyl-2-(1H-pyrazolo[4,3-b]pyridin-5-yl)-1-piperidyl]-2-oxo-acetyl]amino]-2-pyridyl]carbamate (0.7 g, 1.42 mmol) in dioxane (50 mL) at room temperature. The resulting mixture was stirred at 100° C. for 14 hr, and then evaporated in vacuo. The residue was diluted with water (20 mL) and extracted with dichloromethane (2*30 mL). The combined organic extracts were dried over sodium sulphate and evaporated in vacuo and obtained crude product 0.45 g was purified by preparative 30-65% 0-5 min H$_2$O/MeOH/0.1% NH$_4$OH, flow 30 ml/min to afford product N-(6-amino-5-methyl-3-pyridyl)-2-[5-methyl-2-(1H-pyrazolo[4,3-b]pyridin-5-yl)-1-piperidyl]-2-oxo-acetamide (0.082 g, 208.42 µmol, 14.70% yield)

LCMS(ESI): [M+1]$^+$ m/z: calcd 393.2; found 394.2; Rt=2.082 min.

Step 3. Separation for N-(6-amino-5-methyl-3-pyridyl)-2-[(2R,5S)-5-methyl-2-(1H-pyrazolo[4,3-b]pyridin-5-yl)-1-piperidyl]-2-oxo-acetamide (Compound 788) and N-(6-amino-5-methyl-3-pyridyl)-2-[(2S,5R)-5-methyl-2-(1H-pyrazolo[4,3-b]pyridin-5-yl)-1-piperidyl]-2-oxo-acetamide (Compound 780

The N-(6-amino-5-methyl-3-pyridyl)-2-[(2R,5S)-5-methyl-2-(1H-pyrazolo[4,3-b]pyridin-5-yl)-1-piperidyl]-2-oxo-acetamide (0.082 g, 208.42 µmol) was subjected to chiral HPLC purification (Column: OJ-H (250*20, 5 mkm), Eluent: Hexane-IPA-MeOH, 70-15-15, flow rate: 12 mL/min) to give the two individual enantiomers Compound 788 N-(6-amino-5-methyl-3-pyridyl)-2-[(2R,5S)-5-methyl-2-(1H-pyrazolo[4,3-b]pyridin-5-yl)-1-piperidyl]-2-oxo-acetamide (0.0159 g, 40.41 µmol, 19.39% yield) and Compound 780 N-(6-amino-5-methyl-3-pyridyl)-2-[(2S,5R)-5-methyl-2-(1H-pyrazolo[4,3-b]pyridin-5-yl)-1-piperidyl]-2-oxo-acetamide (0.0189 g, 48.04 µmol, 23.05% yield)

Compound 788: $^1$H NMR (600 MHz, DMSO-$d_6$) δ 1.00-1.07 (m, 3H), 1.32-1.41 (m, 1H), 1.74-1.82 (m, 1H), 1.81-1.92 (m, 1H), 1.96-2.11 (m, 4H), 2.53-2.56 (m, 1H), 2.80-3.25 (m, 1H), 3.44-4.10 (m, 1H), 5.30-5.59 (m, 1H), 5.59-5.75 (m, 2H), 7.25-7.45 (m, 1H), 7.45-7.51 (m, 1H), 7.95-8.06 (m, 2H), 8.24-8.32 (m, 1H), 10.41-10.57 (m, 1H), 13.30 (s, 1H).

LCMS(ESI): [M+1]$^+$ m/z: calcd 393.2; found 394.0; Rt=1.898 min.

Compound 780: $^1$H NMR (600 MHz, DMSO-$d_6$) δ 1.00-1.07 (m, 3H), 1.32-1.41 (m, 1H), 1.74-1.82 (m, 1H), 1.81-1.92 (m, 1H), 1.96-2.11 (m, 4H), 2.53-2.56 (m, 1H), 2.80-3.25 (m, 1H), 3.44-4.10 (m, 1H), 5.30-5.59 (m, 1H), 5.59-5.75 (m, 2H), 7.25-7.45 (m, 1H), 7.45-7.51 (m, 1H), 7.95-8.06 (m, 2H), 8.24-8.32 (m, 1H), 10.41-10.57 (m, 1H), 13.30 (s, 1H).

LCMS(ESI): [M+1]$^+$ m/z: calcd 393.2; found 394.0; Rt=1.898 min.

Example 365. The Synthesis of rac-N-(6-amino-5-methyl-3-pyridyl)-2-[5-methyl-2-(2-oxo-1H-Quinolin-6-yl)-1-piperidyl]-2-oxo-acetamide (Compound 671), rel-N-(6-amino-5-methyl-3-pyridyl)-2-[(2R,5S)-5-methyl-2-(2-oxo-1H-Quinolin-6-yl)-1-piperidyl]-2-oxo-acetamide (Compound 762, Compound 762) and rel-N-(6-amino-5-methyl-3-pyridyl)-2-[(2S,5R)-5-methyl-2-(2-oxo-1H-Quinolin-6-yl)-1-piperidyl]-2-oxo-acetamide (EN-TG-4743, Compound 763

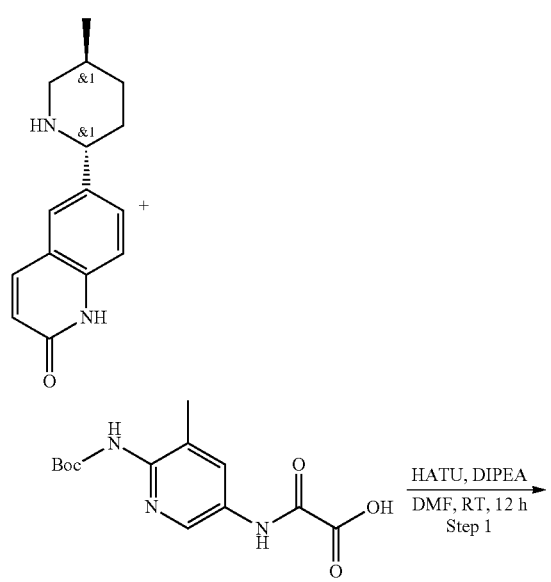

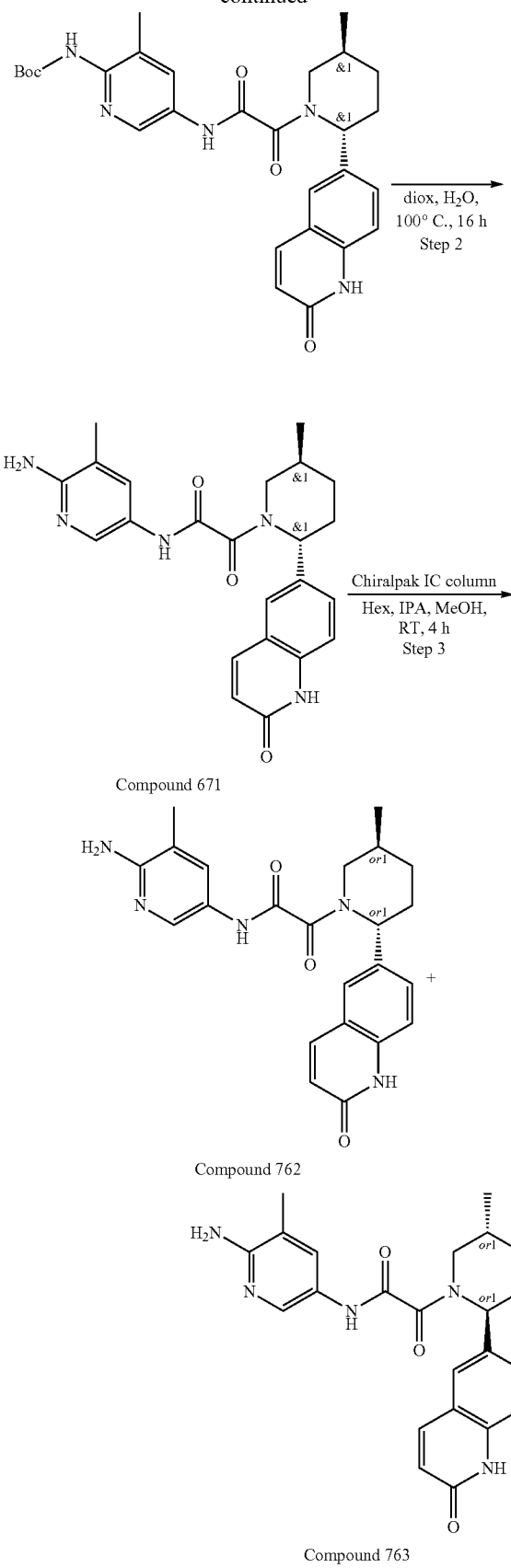

Step 1: The Synthesis of rac-tert-butyl N-[3-methyl-5-[[2-[5-methyl-2-(2-oxo-1H-quinolin-6-yl)-1-piperidyl]-2-oxo-acetyl]amino]-2-pyridyl]carbamate DIPEA (266.68 mg, 2.06 mmol, 359.41 μL) was added to the solution of respective 6-(5-methyl-2-piperidyl)-1H-quinolin-2-one (0.2 g, 825.37 μmol) and 2-[[6-(tert-butoxycarbonylamino)-5-methyl-3-pyridyl]amino]-2-oxo-acetic acid (243.72 mg, 825.37 μmol) in DMF (10 mL). The resulting mixture was stirred for 5 min followed by the addition of HATU (345.21 mg, 907.91 μmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford tert-butyl N-[3-methyl-5-[[2-[5-methyl-2-(2-oxo-1H-quinolin-6-yl)-1-piperidyl]-2-oxo-acetyl]amino]-2-pyridyl]carbamate (0.21 g, 404.16 μmol, 48.97% yield).

LCMS(ESI): [M+H]$^+$ m/z: calcd 519.2; found 520.4; Rt=2.748 min.

Step 2: The Synthesis of rac-N-(6-amino-5-methyl-3-pyridyl)-2-[5-methyl-2-(2-oxo-1H-quinolin-6-yl)-1-piperidyl]-2-oxo-acetamide (Compound 671 tert-butyl N-[3-methyl-5-[[2-[5-methyl-2-(2-oxo-1H-quinolin-6-yl)-1-piperidyl]-2-oxo-acetyl]-amino]-2-pyridyl] carbamate (0.21 g, 404.16 μmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford N-(6-amino-5-methyl-3-pyridyl)-2-[5-methyl-2-(2-oxo-1H-quinolin-6-yl)-1-piperidyl]-2-oxo-acetamide (121.9 mg, 290.60 μmol, 71.90% yield).

$^1$H NMR (DMSO-d$_6$, 600 MHz): δ (ppm) 1.01 (m, 3H), 1.34 (m, 1H), 1.69 (m, 1H), 1.86 (m, 1H), 2.01 (m, 4H), 2.20 (m, 1H), 2.90 (m, 1H), 3.63 (m, 1H), 5.59 (m, 3H), 6.47 (m, 1H), 7.29 (m, 1H), 7.40 (m, 1H), 7.48 (m, 1H), 7.59 (m, 1H), 7.87 (m, 1H), 7.97 (m, 1H), 10.46 (m, 1H), 11.70 (m, 1H).

LCMS(ESI): [M+H]$^+$ m/z: calcd 419.2; found 420.2; Rt=1.670 min.

Step 3: The Synthesis of rel-N-(6-amino-5-methyl-3-pyridyl)-2-[(2R,5S)-5-methyl-2-(2-oxo-1H-quinolin-6-yl)-1-piperidyl]-2-oxo-acetamide (Compound 762, Compound 762) and rel-N-(6-amino-5-methyl-3-pyridyl)-2-[(2S,5R)-5-methyl-2-(2-oxo-1H-quinolin-6-yl)-1-piperidyl]-2-oxo-acetamide (EN-TG-4743, Compound 763 rac-N-(6-amino-5-methyl-3-pyridyl)-2-[5-methyl-2-(2-oxo-1H-quinolin-6-yl)-1-piperidyl]-2-oxo-acetamide (121.9 mg, 290.60 μmol) was chirally separated using Chiralpak IC (250*20 mm, 5 mm) column and Hexane-IPA-MeOH, 50-25-25 as a mobile phase, Flow Rate: 12 mL/min; Column Temperature: 24° C.; Wavelength: 205 nm, 215 nm, 254 nm affording Compound 762 (Compound 762)—rel-N-(6-amino-5-methyl-3-pyridyl)-2-[(2R,5S)-5-methyl-2-(2-oxo-1H-quinolin-6-yl)-1-piperidyl]-2-oxo-acetamide (42.1 mg, 34.54% yield) and Compound 763 (Compound 763)—rel-N-(6-amino-5-methyl-3-pyridyl)-2-[(2S,5R)-5-methyl-2-(2-oxo-1H-quinolin-6-yl)-1-piperidyl]-2-oxo-acetamide (52.29 mg, 42.90% yield). etTime (is A)=60.01 min; RetTime (is B)=66.66 min RetTime (is C)=89.81

Compound 762 (Compound 762): RT (IC (250*4.6, 5 mkm, IPA-MeOH, 50-50, 0.5 mL/min)=28.057 min.

$^1$H NMR (600 MHz, DMSO-d$_6$) δ 0.99-1.02 (m, 3H), 1.28-1.37 (m, 1H), 1.66-1.73 (m, 1H), 1.82-1.90 (m, 1H), 1.96-2.03 (m, 3H), 2.04-2.16 (m, 1H), 2.18-2.26 (m, 1H), 2.72-3.22 (m, 1H), 3.42-4.02 (m, 1H), 5.13-5.58 (m, 1H), 5.58-5.65 (m, 2H), 6.42-6.50 (m, 1H), 7.24-7.32 (m, 1H), 7.36-7.44 (m, 1H), 7.44-7.51 (m, 1H), 7.54-7.65 (m, 1H), 7.82-7.90 (m, 1H), 7.90-8.04 (m, 1H), 10.35-10.57 (m, 1H), 11.58-11.82 (m, 1H).

LCMS(ESI): [M+H]$^+$ m/z: calcd 419.2; found 420.2; Rt=0.991 min.

Compound 763 (Compound 763): RT (IC (250*4.6, 5 mkm, IPA-MeOH, 50-50, 0.5 mL/min)=20.804 min.

$^1$H NMR (600 MHz, DMSO-d$_6$) δ 0.98-1.02 (m, 3H), 1.28-1.37 (m, 1H), 1.65-1.74 (m, 1H), 1.81-1.90 (m, 1H), 1.96-2.03 (m, 3H), 2.04-2.16 (m, 1H), 2.19-2.27 (m, 1H), 2.70-3.23 (m, 1H), 3.40-4.03 (m, 1H), 5.10-5.58 (m, 1H), 5.58-5.65 (m, 2H), 6.42-6.51 (m, 1H), 7.22-7.33 (m, 1H), 7.35-7.42 (m, 1H), 7.45-7.52 (m, 1H), 7.54-7.65 (m, 1H), 7.83-7.90 (m, 1H), 7.90-8.05 (m, 1H), 10.36-10.57 (m, 1H), 11.70 (s, 1H).

LCMS(ESI): [M+H]$^+$ m/z: calcd 419.2; found 420.2; Rt=0.988 min.

Example 366. The Synthesis of rel-N-(6-amino-5-ethyl-3-pyridyl)-2-[(2R,5S)-5-methyl-2-(2-oxo-1H-Quinolin-6-yl)-1-piperidyl]-2-oxo-acetamide (Compound 825, Compound 825) and rel-N-(6-amino-5-ethyl-3-pyridsyl)-2-[(2S,5R)-5-methyl-2-(2-oxo-1H-Quinolin-6-yl)-1-piperidyl]-2-oxo-acetamide (Compound 819, Compound 819

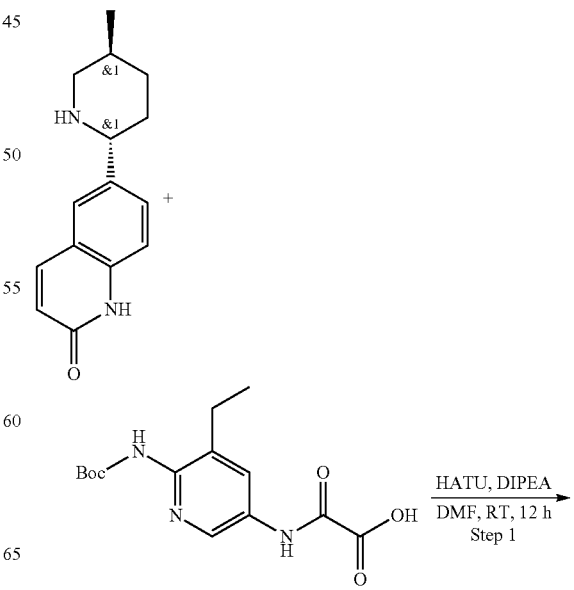

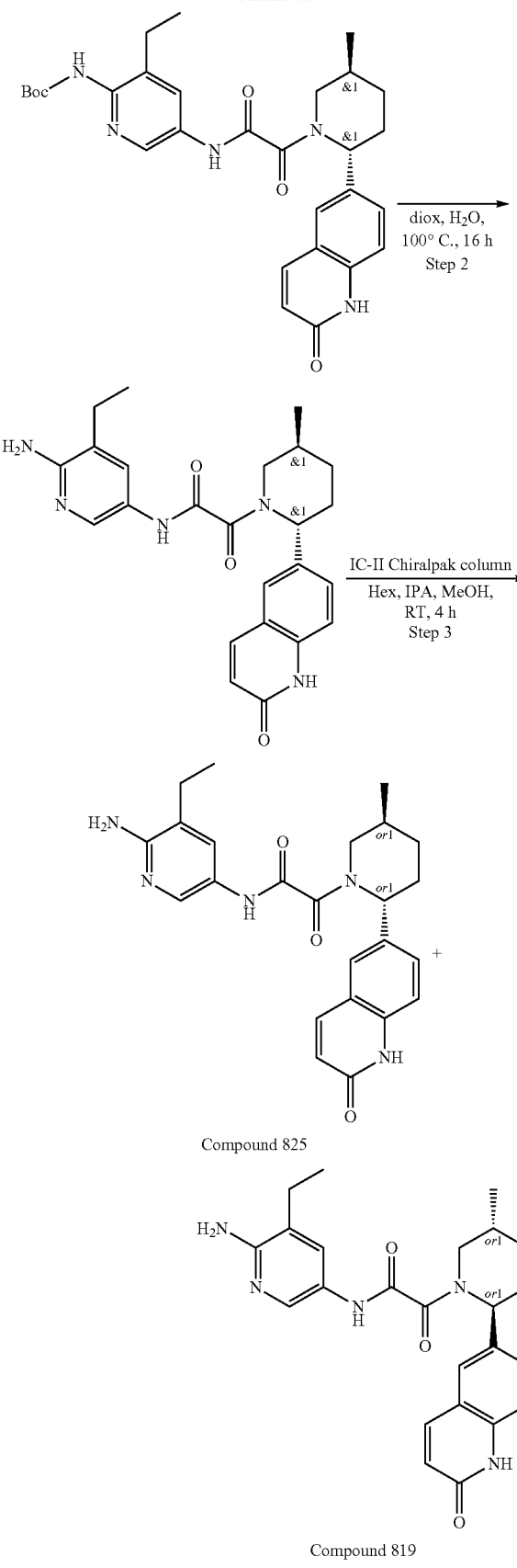

Compound 825

Compound 819

Step 1: The Synthesis of rac-tert-butyl N-[3-ethyl-5-[[2-[5-methyl-2-(2-oxo-1H-quinolin-6-yl)-1-piperidyl]-2-oxo-acetyl]amino]-2-pyridyl]carbamate DIPEA (266.68 mg, 2.06 mmol, 359.41 µL) was added to the solution of respective 6-(5-methyl-2-piperidyl)-1H-quinolin-2-one (0.2 g, 825.37 µmol) and 2-[[6-(tert-butoxycarbonylamino)-5-ethyl-3-pyridyl]amino]-2-oxo-acetic acid (255.30 mg, 825.37 µmol) in DMF (10 mL). The resulting mixture was stirred for 5 min followed by the addition of HATU (345.21 mg, 907.91 µmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford tert-butyl N-[3-ethyl-5-[[2-[5-methyl-2-(2-oxo-1H-quinolin-6-yl)-1-piperidyl]-2-oxo-acetyl]amino]-2-pyridyl]carbamate (0.2 g, 374.80 µmol, 45.41% yield).

LCMS(ESI): [M+H]$^+$ m/z: calcd 533.2; found 534.4; Rt=2.921 min.

Step 2: The Synthesis of rac-N-(6-amino-5-ethyl-3-pyridyl)-2-[5-methyl-2-(2-oxo-1H-Quinolin-6-yl)-1-piperidyl]-2-oxo-acetamide tert-butyl N-[3-ethyl-5-[[2-[5-methyl-2-(2-oxo-1H-quinolin-6-yl)-1-piperidyl]-2-oxo-acetyl]amino]-2-pyridyl]carbamate (0.2 g, 374.80 µmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and MeOH+NH$_3$ as an eluent mixture) to afford N-(6-amino-5-ethyl-3-pyridyl)-2-[5-methyl-2-(2-oxo-1H-quinolin-6-yl)-1-piperidyl]-2-oxo-acetamide (97.2 mg, 224.22 µmol, 59.82% yield).

LCMS(ESI): [M+H]$^+$ m/z: calcd 433.2; found 434.2; Rt=1.882 min.

Step 3: The Synthesis of rel-N-(6-amino-5-ethyl-3-pyridyl)-2-[(2R,5S)-5-methyl-2-(2-oxo-1H-Quinolin-6-yl)-1-piperidyl]-2-oxo-acetamide (Compound 825, Compound 825) and rel-N-(6-amino-5-ethyl-3-pyridyl)-2-[(2S,5R)-5-methyl-2-(2-oxo-1H-Quinolin-6-yl)-1-piperidyl]-2-oxo-acetamide (Compound 819, Compound 819 rac-N-(6-amino-5-ethyl-3-pyridyl)-2-[5-methyl-2-(2-oxo-1H-quinolin-6-yl)-1-piperidyl]-2-oxo-acetamide (97.2 mg, 224.22 µmol) was chirally separated using Chiralpak IC-II (250*20 mm, 5 mkm) column and Hexane-IPA-MeOH 50-25-25 as a mobile phase, Flow Rate: 12 mL/min affording Compound 825 (Compound 825)—rel-N-(6-amino-5-ethyl-3-pyridyl)-2-[(2R,5S)-5-methyl-2-(2-oxo-1H-quinolin-6-yl)-1-piperidyl]-2-oxo-acetamide (32.76 mg, 33.70% yield) and Compound 819 (Compound 819)—rel-N-(6-amino-5-ethyl-3-pyridyl)-2-[(2S,5R)-5-methyl-2-(2-oxo-1H-quinolin-6-yl)-1-piperidyl]-2-oxo-acetamide (28.39 mg, 29.21% yield).

Compound 825 (Compound 825): RT (OJ-H (250*4.6, 5 mkm), Hex-IPA-MeOH, 50-25-25, 0.6 mL/min)=30.120 min.

$^1$H NMR (dmso, 600 MHz): δ (ppm) 0.97-1.03 (m, 3H), 1.04-1.13 (m, 3H), 1.28-1.40 (m, 1H), 1.66-1.74 (m, 1H), 1.80-1.93 (m, 1H), 2.01-2.16 (m, 1H), 2.18-2.28 (m, 1H), 2.35-2.42 (m, 2H), 2.72-3.21 (m, 1H), 3.39-4.05 (m, 1H), 5.09-5.59 (m, 1H), 5.59-5.71 (m, 2H), 6.45-6.51 (m, 1H), 7.25-7.34 (m, 1H), 7.38-7.43 (m, 1H), 7.45-7.51 (m, 1H), 7.56-7.64 (m, 1H), 7.84-7.90 (m, 1H), 7.94-8.09 (m, 1H), 10.24-10.70 (m, 1H), 11.70 (br s, 1H).

LCMS(ESI): [M+H]+ m/z: calcd 433.2; found 434.2; Rt=1.910 min.

Compound 819 (Compound 819): RT (OJ-H (250*4.6, 5 mkm), Hex-IPA-MeOH, 50-25-25, 0.6 mL/min)=12.280 min.

¹H NMR (dmso, 600 MHz): δ (ppm) 0.99-1.03 (m, 3H), 1.04-1.15 (m, 3H), 1.29-1.38 (m, 1H), 1.64-1.77 (m, 1H), 1.81-1.91 (m, 1H), 2.00-2.16 (m, 1H), 2.18-2.30 (m, 1H), 2.33-2.41 (m, 2H), 2.76-3.21 (m, 1H), 3.46-4.03 (m, 1H), 5.11-5.59 (m, 1H), 5.59-5.69 (m, 2H), 6.43-6.50 (m, 1H), 7.26-7.33 (m, 1H), 7.39-7.43 (m, 1H), 7.46-7.52 (m, 1H), 7.55-7.64 (m, 1H), 7.84-7.91 (m, 1H), 7.95-8.08 (m, 1H), 10.46 (br s, 1H), 11.66 (br s, 1H).

LCMS(ESI): [M+H]+ m/z: calcd 433.2; found 434.2; Rt=1.905 min.

Example 367. The Synthesis of rel-N-(6-amino-5-ethyl-3-pyridyl)-2-[(2S,5R)-5-methyl-2-(6-methyl-3-pyridyl)-1-piperidyl]-2-oxo-acetamide (Compound 756) and rel-N-(6-amino-5-ethyl-3-pyridyl)-2-[(2R,5S)-5-methyl-2-(6-methyl-3-pyridyl)-1-piperidyl]-2-oxo-acetamide (Compound 784

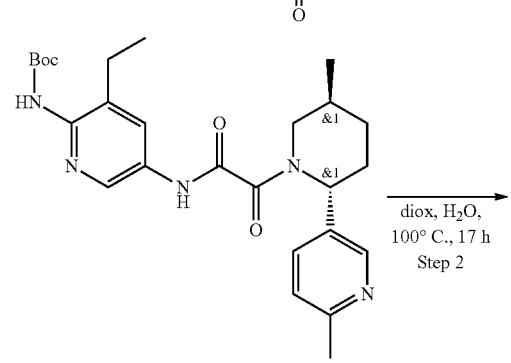

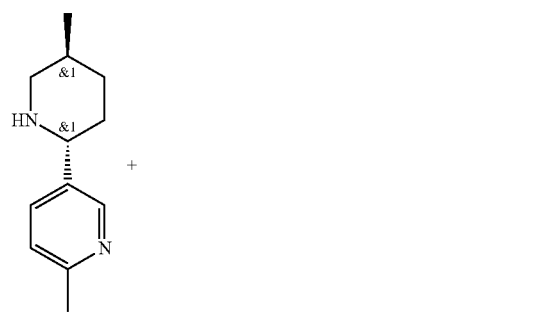

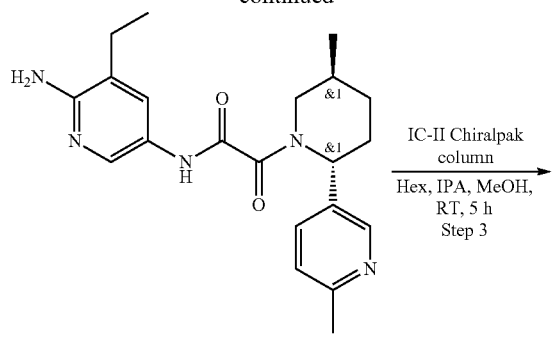

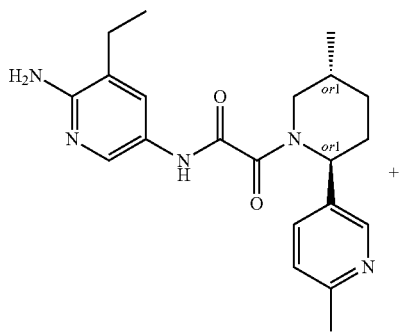

Compound 756

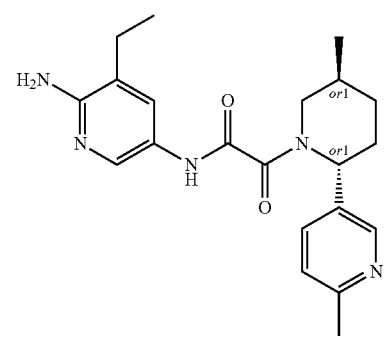

Compound 784

Step 1: The Synthesis of rel-tert-butyl N-[3-ethyl-5-[[2-[5-methyl-2-(6-methyl-3-pyridyl)-1-piperidyl]-2-oxo-acetyl]amino]-2-pyridyl]carbamate DIPEA (522.29 mg, 4.04 mmol, 703.90 μL) was added to the solution of respective 2-[[6-(tert-butoxycarbonylamino)-5-ethyl-3-pyridyl]amino]-2-oxo-acetic acid (0.5 g, 1.62 mmol) and 2-methyl-5-(5-methyl-2-piperidyl)pyridine (307.59 mg, 1.62 mmol) in DMF (15 mL). The resulting mixture was stirred for 5 min followed by the addition of HATU (676.09 mg, 1.78 mmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford rel-tert-butyl N-[3-ethyl-5-[[2-[5-methyl-2-(6-methyl-3-pyridyl)-1-piperidyl]-2-oxo-acetyl]amino]-2-pyridyl]carbamate (430.2 mg, 893.30 μmol, 55.26% yield).

LCMS(ESI): [M+2H]+ m/z: calcd 481.2; found 483.2; Rt=2.306 min.

Step 2: The Synthesis of rel-N-(6-amino-5-ethyl-3-pyridyl)-2-[5-methyl-2-(6-methyl-3-pyridyl)-1-piperidyl]-2-oxo-acetamide Rel-tert-butyl N-[3-ethyl-5-[[2-[5-methyl-2-(6-methyl-3-pyridyl)-1-piperidyl]-2-oxo-acetyl]amino]-2-pyridyl]carbamate (430.2 mg, 893.30 μmol) was dissolved in dioxane (2 mL) and water (5 mL) mixture. Then reaction mixture was stirred for 17 hr at 100° C. After the completion of the reaction, monitored by LCMS, the resulting suspension was concentrated under reduced pressure. The obtained solid was subjected to HPLC (Waters Sunfire C18 20*100 5 mkm column and MeCN as an eluent mixture) to afford rel-N-(6-amino-5-ethyl-3-pyridyl)-2-[5-methyl-2-(6-methyl-3-pyridyl)-1-piperidyl]-2-oxo-acetamide (184.6 mg, 483.92 μmol, 54.17% yield).

LCMS(ESI): [M+2H]+ m/z: calcd 381.2; found 383.2; Rt=1.209 min.

Step 3: The Synthesis of rel-N-(6-amino-5-ethyl-3-pyridyl)-2-[(2S,5R)-5-methyl-2-(6-methyl-3-pyridyl)-1-piperidyl]-2-oxo-acetamide (Compound 756) and rel-N-(6-amino-5-ethyl-3-pyridyl)-2-[(2R,5S)-5-methyl-2-(6-methyl-3-pyridyl)-1-piperidyl]-2-oxo-acetamide (Compound 784 rel-N-(6-amino-5-ethyl-3-pyridyl)-2-[5-methyl-2-(6-methyl-3-pyridyl)-1-piperidyl]-2-oxo-acetamide (184.6 mg, 483.92 μmol) was chirally separated using Chiralpak IC-II (250*20 mm, 5 mkm) column and Hexane-IPA-MeOH 60-20-20 as a mobile phase, Flow Rate: 12 mL/min affording Compound 756—rel-N-(6-amino-5-ethyl-3-pyridyl)-2-[(2S,5R)-5-methyl-2-(6-methyl-3-pyridyl)-1-piperidyl]-2-oxo-acetamide (72.55 mg, 39.30% yield) and Compound 784—rel-N-(6-amino-5-ethyl-3-pyridyl)-2-[(2R,5S)-5-methyl-2-(6-methyl-3-pyridyl)-1-piperidyl]-2-oxo-acetamide (71.94 mg, 38.97% yield).

Compound 756: RT (Chiralpak IC (250*4.6, 5 mkm), Hexane-IPA-MeOH, 50-25-25, 0.6 mL/min)=24.564 min.

$^1$H NMR (600 MHz, DMSO-$d_6$) δ 0.98-1.01 (m, 3H), 1.05-1.12 (m, 3H), 1.25-1.40 (m, 1H), 1.57-1.67 (m, 1H), 1.78-1.93 (m, 1H), 1.94-2.14 (m, 1H), 2.14-2.26 (m, 1H), 2.37-2.45 (m, 5H), 2.66-3.22 (m, 1H), 3.40-4.03 (m, 1H), 5.11-5.58 (m, 1H), 5.58-5.66 (m, 2H), 7.17-7.28 (m, 1H), 7.41-7.51 (m, 1H), 7.53-7.64 (m, 1H), 7.95-8.07 (m, 1H), 8.34-8.43 (m, 1H), 10.43-10.53 (m, 1H).

LCMS(ESI): [M+2H]+ m/z: calcd 381.2; found 383.4; Rt=1.211 min.

Compound 784: RT (Chiralpak IC (250*4.6, 5 mkm), Hexane-IPA-MeOH, 50-25-25, 0.6 mL/min)=34.051 min.

$^1$H NMR (600 MHz, DMSO-$d_6$) δ 0.98-1.02 (m, 3H), 1.05-1.12 (m, 3H), 1.28-1.38 (m, 1H), 1.60-1.67 (m, 1H), 1.82-1.91 (m, 1H), 1.99-2.13 (m, 1H), 2.16-2.26 (m, 1H), 2.39-2.45 (m, 5H), 2.69-3.19 (m, 1H), 3.40-4.03 (m, 1H), 5.14-5.59 (m, 1H), 5.59-5.66 (m, 2H), 7.23-7.27 (m, 1H), 7.43-7.50 (m, 1H), 7.54-7.64 (m, 1H), 7.98-8.07 (m, 1H), 8.35-8.41 (m, 1H), 10.44-10.60 (m, 1H).

LCMS(ESI): [M+2H]+ m/z: calcd 381.2; found 383.4; Rt=1.217 min.

Example 368. The Synthesis of N-(6-amino-5-methylpyridin-3-yl)-2-(1',5-dimethyl-[2,4'-bipiperidin]-1-yl)-2-oxoacetamide (Compound 614

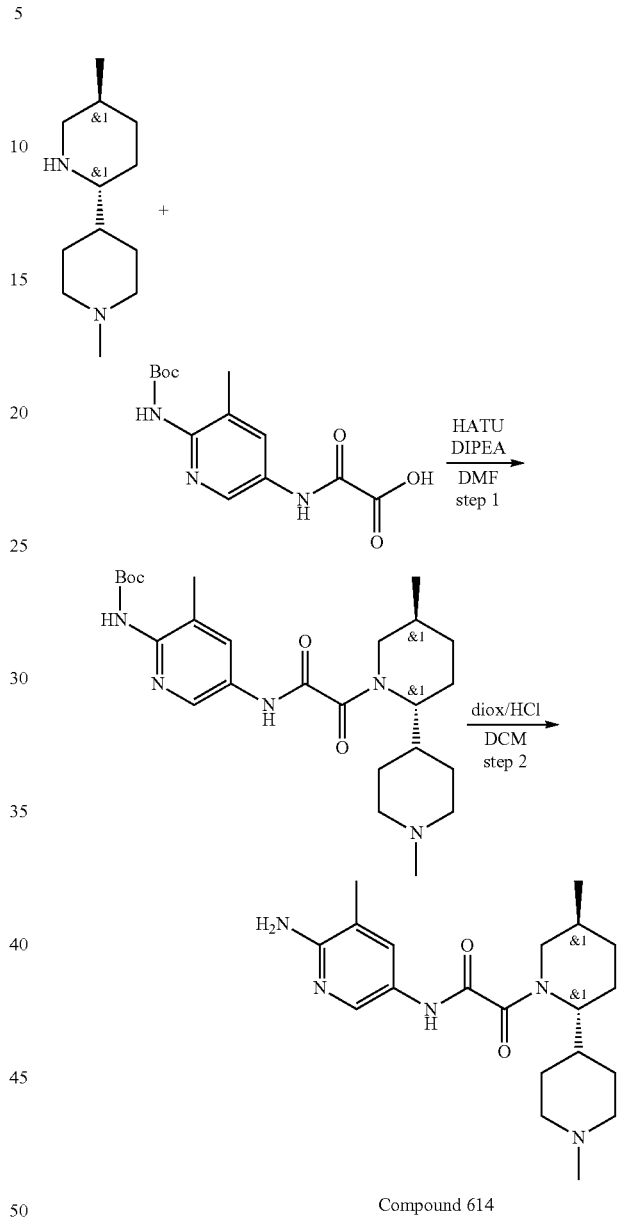

Compound 614

Step 1: Synthesis of rac-tert-butyl (5-(2-((2R,5S)-1', 5-dimethyl-[2,4'-bipiperidin]-1-yl)-2-oxoacetamido)-3-methylpyridin-2-yl)carbamate HATU (490.95 mg, 1.29 mmol) was added portion wise at rt to a suspension of 2-[[6-(tert-butoxycarbonylamino)-5-methyl-3-pyridyl]amino]-2-oxo-acetic acid (381.28 mg, 1.29 mmol), 1-methyl-4-[(2R,5S)-5-methyl-2-piperidyl]piperidine (298.24 mg, 1.29 mmol) and DIPEA (1.00 g, 7.75 mmol, 1.35 mL) in DMF (10 mL). The clear solution was stirred at 25° C. for 18 hr and the solvents were evaporated in vacuum. The residue was subjected to RP-HPLC (column: YMC Triart C18 100×20 mm, 5 um; 50-80% 0-5 min water-MeOH (NH$_3$ 0.1%), flow 30 ml/min as mobile phase)

to give tert-butyl N-[3-methyl-5-[[2-[(2R,5S)-5-methyl-2-(1-methyl-4-piperidyl)-1-piperidyl]-2-oxo-acetyl]amino]-2-pyridyl]carbamate (206 mg, 434.96 μmol, 33.69% yield).

$^1$H NMR (400 MHz, CDCl$_3$) δ (ppm) 0.85 (d, 3H), 1.12 (m, 2H), 1.36 (m, 5H), 1.48 (s, 9H), 1.76 (m, 4H), 2.12 (m, 2H), 2.27 (m, 6H), 2.96 (m, 1H), 3.04 (m, 2H), 4.12 (m, 1H), 6.62 (m, 1H), 8.03 (m, 1H), 8.33 (m, 1H), 9.36 (m, 1H).

LCMS(ESI): [M]$^+$ m/z: calcd 473.2; found 474.2; Rt=2.046 min.

Step 2: Synthesis of N-(6-amino-5-methylpyridin-3-yl)-2-(1',5-dimethyl-[2,4'-bipiperidin]-1-yl)-2-oxoacetamide (Compound 614

Hydrogen chloride solution 4.0 M in dioxane (1.13 g, 4.35 mmol, 1.08 mL, 14% purity) was carefully added at rt to a solution of tert-butyl N-[3-methyl-5-[[2-[(2R,5S)-5-methyl-2-(1-methyl-4-piperidyl)-1-piperidyl]-2-oxo-acetyl]amino]-2-pyridyl]carbamate (206.00 mg, 434.96 μmol) in DCM (2 mL). The reaction mixture was then stirred for 12 hr at rt and the solvents were evaporated in vacuum. The residue was subjected to RP-HPLC (column: YMC Triart C18 100×20 mm, 5 um; 30-80% 1-6 min water-MeOH (NH$_3$ 0.1%), flow 30 ml/min as mobile phase) to give Compound 614 N-(6-amino-5-methyl-3-pyridyl)-2-[(2R,5S)-5-methyl-2-(1-methyl-4-piperidyl)-1-piperidyl]-2-oxo-acetamide (114 mg, 305.23 μmol, 70.17% yield).

Compound 614: $^1$H NMR (600 MHz, DMSO-d$_6$) δ (ppm) 0.91-0.96 (m, 3H), 1.00-1.17 (m, 2H), 1.21-1.32 (m, 1H), 1.39-1.48 (m, 1H), 1.51-1.66 (m, 3H), 1.72-1.81 (m, 4H), 1.81-1.96 (m, 2H), 1.98-2.03 (m, 3H), 2.07-2.14 (m, 3H), 2.64-2.86 (m, 3H), 3.47-4.11 (m, 1H), 5.54-5.65 (m, 2H), 7.41-7.48 (m, 1H), 7.94-8.00 (m, 1H), 10.16-10.38 (m, 1H).

LCMS(ESI): [M]$^+$ m/z: calcd 373.2; found 374.2; Rt=1.064 min.

Example 369. The Synthesis of N-(6-amino-5-ethylpyridin-3-yl)-2-(2-(3,4-dihydro-2H-benzo[b][1,4]oxazin-7-yl)-5-methylpiperidin-1-yl)-2-oxoacetamide (Compound 870

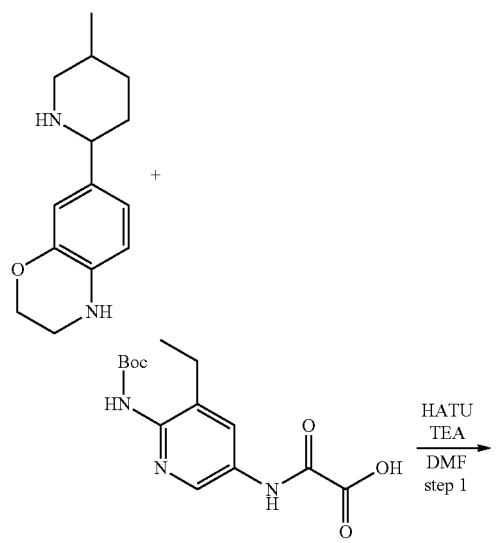

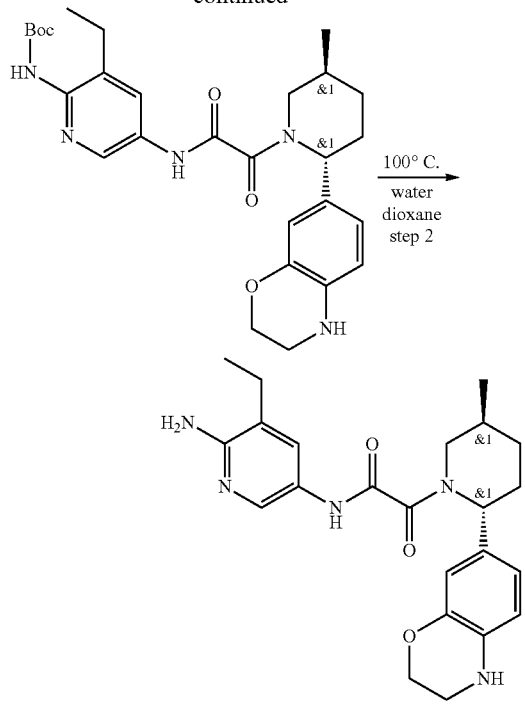

Compound 870

Step 1: Synthesis of rac-tert-butyl (5-(2-((2R,5S)-2-(3,4-dihydro-2H-benzo[b][1,4]oxazin-7-yl)-5-methylpiperidin-1-yl)-2-oxoacetamido)-3-ethylpyridin-2-yl)carbamate 7-[(2R,5S)-5-methyl-2-piperidyl]-3,4-dihydro-2H-1,4-benzoxazine (0.2 g, 860.88 μmol), TEA (871.12 mg, 8.61 mmol, 1.20 mL) and 2-[[6-(tert-butoxycarbonylamino)-5-ethyl-3-pyridyl]amino]-2-oxo-acetic acid (266.28 mg, 860.88 μmol) was dissolved in DMF (8.5 mL) and HATU (491.00 mg, 1.29 mmol) was added in one portion, the resulting mixture was stirred for 3 hr at 20° C. The reaction mixture was poured into water and the aqueous phase was extracted with EtOAc (3 times), then the combined organic phase was washed with brine (3 times), dried over Na$_2$SO$_4$ and concentrated on vacuum. The crude product was purified by reverse phase HPLC (55-65% 2-10 min; water-MeOH; flow 30 ml/min (loading pump 4 ml/min MeOH); column SunFire C18 100*19 mm 5 um) to give tert-butyl N-[5-[[2-[(2R,5S)-2-(3,4-dihydro-2H-1,4-benzoxazin-7-yl)-5-methyl-1-piperidyl]-2-oxo-acetyl]amino]-3-ethyl-2-pyridyl]carbamate (0.096 g, 183.34 μmol, 21.30% yield) as a pink solid. The reaction was successful. The desired tert-butyl N-[5-[[2-[(2R,5S)-2-(3,4-dihydro-2H-1,4-benzoxazin-7-yl)-5-methyl-1-piperidyl]-2-oxo-acetyl]amino]-3-ethyl-2-pyridyl]carbamate (0.096 g, 183.34 μmol, 21.30% yield) was isolated as a pink solid.

LCMS(ESI): [M]$^+$ m/z: calcd 523.2; found 524.2; Rt=1.377 min.

Step 2: Synthesis of N-(6-amino-5-ethylpyridin-3-yl)-2-(2-(3,4-dihydro-2H-benzo[b][1,4]oxazin-7-yl)-5-methylpiperidin-1-yl)-2-oxoacetamide (Compound 870 tert-butyl N-[5-[[2-[(2R,5S)-2-(3,4-dihydro-2H-1,4-benzoxazin-7-yl)-5-methyl-1-piperidyl]-2-oxo-acetyl]amino]-

3-ethyl-2-pyridyl]carbamate (0.096 g, 183.34 µmol) was dissolved in mixture of dioxane (2 mL) and water (2 mL) then stirred at 100° C. for 12 hr. The reaction mixture was concentrated on vacuum. The crude product which was purified by HPLC (35-55% MeCN/H₂O—2-10 min Flow rate: 30 ml/min; loading pump 4 ml/min MeCN; Column Sun Fire C18 100×19 mm, 5 mk) to give N-(6-amino-5-ethyl-3-pyridyl)-2-[(2R,5S)-2-(3,4-dihydro-2H-1,4-benzoxazin-7-yl)-5-methyl-1-piperidyl]-2-oxo-acetamide (0.02 g, 47.22 µmol, 25.76% yield) as a white solid.

Compound 870: $^1$H NMR (600 MHz, DMSO-d$_6$) δ (ppm) 0.94-1.04 (m, 3H), 1.06-1.14 (m, 3H), 1.23-1.34 (m, 1H), 1.63-1.76 (m, 1H), 1.77-1.87 (m, 1H), 1.88-2.04 (m, 1H), 2.04-2.13 (m, 1H), 2.36-2.42 (m, 2H), 2.70-3.16 (m, 1H), 3.21-3.25 (m, 2H), 3.35-3.96 (m, 1H), 4.05-4.12 (m, 2H), 4.89-5.58 (m, 1H), 5.58-5.65 (m, 2H), 5.66-5.71 (m, 1H), 6.48-6.65 (m, 3H), 7.43-7.53 (m, 1H), 7.96-8.07 (m, 1H), 10.38-10.55 (m, 1H).

LCMS(ESI): [M]⁺ m/z: calcd 423.2; found 424.2; Rt=1.004 min.

Example 370. The Synthesis of 1-(2-((6-amino-5-methylpyridin-3-yl)amino)-2-oxoacetyl)-N,5-dimethyl-[2,3'-bipiperidine]-1'-carboxamide (Compound 814

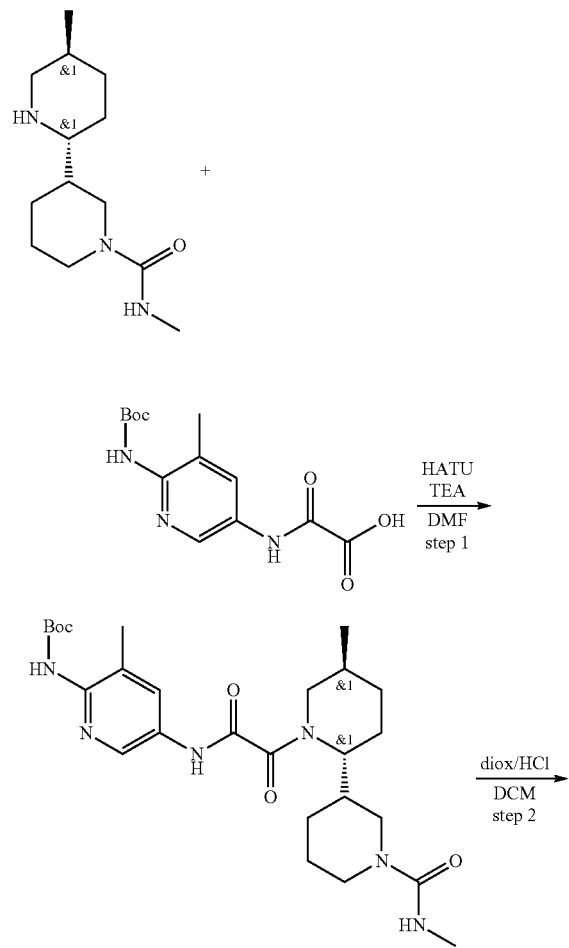

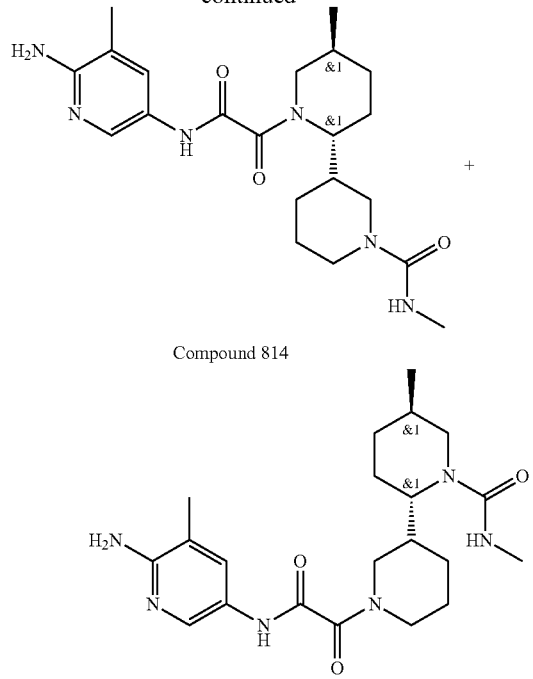

Compound 814

Step 1: Synthesis of tert-butyl N-[3-methyl-5-[[2-[(2R,5S)-5-methyl-2-[1-(methylcarbamoyl)-3-piperidyl]-1-piperidyl]-2-oxo-acetyl]amino]-2-pyridyl]carbamate To a solution of N-methyl-3-[(2R,5S)-5-methyl-2-piperidyl]piperidine-1-carboxamide (0.75 g, 2.72 mmol, HCl), 2-[[6-(tert-butoxycarbonylamino)-5-methyl-3-pyridyl]amino]-2-oxo-acetic acid (802.95 mg, 2.72 mmol) and TEA (1.38 g, 13.60 mmol, 1.90 mL), HATU (1.14 g, 2.99 mmol) was added portion wise. The resulting mixture was stirred at 25° C. for 3 hr, taken up with water (50 ml) and extracted with EtOAc (3*20 ml). The combined organic layer was washed with brine (2*25 ml), dried over Na₂SO₄ and the solvent was removed to give tert-butyl N-[3-methyl-5-[[2-[(2R,5S)-5-methyl-2-[1-(methylcarbamoyl)-3-piperidyl]-1-piperidyl]-2-oxo-acetyl]amino]-2-pyridyl]carbamate (1.1 g, 2.13 mmol, 78.30% yield). This compound was used for the next step without further purification.

LCMS(ESI): [M]⁺ m/z: calcd 516.2; found 517.2; Rt=1.147 min.

Step 2: Synthesis of 1-(2-((6-amino-5-methylpyridin-3-yl)amino)-2-oxoacetyl)-N,5-dimethyl-[2,3'-bipiperidine]-1'-carboxamide (Compound 814

A solution of tert-butyl N-[3-methyl-5-[[2-[(2R,5S)-5-methyl-2-[1-(methylcarbamoyl)-3-piperidyl]-1-piperidyl]-2-oxo-acetyl]amino]-2-pyridyl]carbamate (1.1 g, 2.13 mmol) and hydrogen chloride solution 4.0 M in dioxane (8 g, 219.41 mmol, 10.00 mL) in DCM (30 mL) was stirred at 25° C. for 3 hr. The solvent was removed and residue was purified by HPLC: 20-20-65% 0-1-6 min H₂O/MeOH/0.1% NH₄OH, flow: 30 ml/min (loading pump 4 ml/min MeOH) target mass 320 column: YMC Triart C18 100×20 mm, 5 um) to obtain 3-[(2R,5S)-1-[2-[(6-amino-5-methyl-3-pyridyl)amino]-2-oxo-acetyl]-5-methyl-2-piperidyl]-N-methyl-piperidine-1-carboxamide (172 mg, 412.95 µmol, 19.39% yield) and (2S,5R)-2-[1-[2-[(6-amino-5-methyl-3-pyridyl)amino]-2-oxo-acetyl]-3-piperidyl]-N,5-dimethyl-piperidine-1-carboxamide (111 mg, 266.50 µmol, 12.52% yield).

Compound 814: $^1$H NMR (600 MHz, DMSO-$d_6$) δ (ppm) 0.78-0.94 (m, 3H), 0.97-1.04 (m, 1H), 1.23-1.33 (m, 2H), 1.51-1.65 (m, 4H), 1.78-1.88 (m, 2H), 1.91-1.96 (m, 1H), 1.99-2.04 (m, 3H), 2.25-2.46 (m, 1H), 2.51-2.54 (m, 3H), 2.58-2.70 (m, 1H), 2.81-3.26 (m, 1H), 3.31-3.63 (m, 1H), 3.67-3.74 (m, 1H), 3.79-3.90 (m, 1H), 3.94-4.22 (m, 1H), 5.24-5.63 (m, 2H), 6.32-6.42 (m, 1H), 7.23-7.49 (m, 1H), 7.87-8.01 (m, 1H), 9.47-10.54 (m, 1H).

LCMS(ESI): [M]$^+$ m/z: calcd 416.2; found 417.2; Rt=1.427 min.

Example 371. The Synthesis of rac-2-[(2R,5S)-2-(1-acetyl-3-piperidyl)-5-methyl-1-piperidyl]-N-(6-amino-5-methyl-3-pyridyl)-2-oxo-acetamide (Compound 757

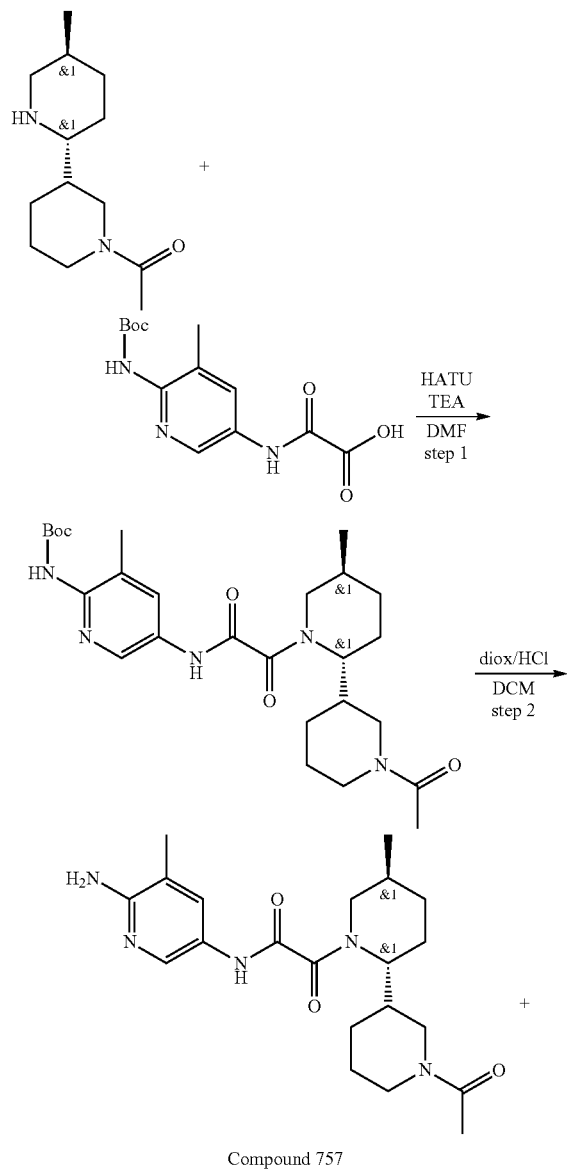

Compound 757

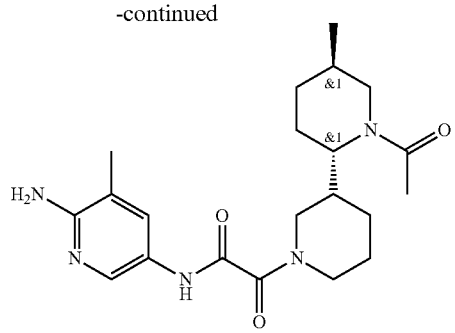

Step 1: Synthesis of rac-tert-butyl N-[5-[[2-[(2R,5S)-2-(1-acetyl-3-piperidyl)-5-methyl-1-piperidyl]-2-oxo-acetyl]amino]-3-methyl-2-pyridyl]carbamate To a solution of 1-[3-[(2R,5S)-5-methyl-2-piperidyl]-1-piperidyl]ethanone (0.7 g, 2.68 mmol, HCl), 2-[[6-(tert-butoxycarbonylamino)-5-methyl-3-pyridyl]amino]-2-oxo-acetic acid (792.57 mg, 2.68 mmol) and TEA (1.36 g, 13.42 mmol, 1.87 mL), HATU (1.12 g, 2.95 mmol) was added portion wise. The resulting mixture was stirred at 25° C. for 3 hr, taken up with water (50 ml) and extracted with EtOAc (3*20 ml). The combined organic layer was washed with brine (2*25 ml), dried over Na$_2$SO$_4$ and the solvent was removed to give tert-butyl N-[5-[[2-[(2R,5S)-2-(1-acetyl-3-piperidyl)-5-methyl-1-piperidyl]-2-oxo-acetyl]amino]-3-methyl-2-pyridyl]carbamate (1.2 g, 2.39 mmol, 89.13% yield). This compound was used for the next step without further purification.

$^1$H NMR (500 MHz, DMSO-$d_6$) δ (ppm) 0.93 (d, 3H), 1.12 (m, 3H), 1.42 (s, 9H), 1.62 (m, 4H), 1.85 (m, 2H), 1.97 (s, 3H), 2.16 (s, 3H), 2.66 (m, 5H), 3.78 (m, 2H), 4.21 (m, 1H), 7.93 (m, 1H), 8.41 (m, 1H), 9.04 (m, 1H), 10.86 (m, 1H).

LCMS(ESI): [M]$^+$ m/z: calcd 501.2; found 502.2; Rt=1.286 min.

Step 2: Synthesis of rac-2-[(2R,5S)-2-(1-acetyl-3-piperidyl)-5-methyl-1-piperidyl]-N-(6-amino-5-methyl-3-pyridyl)-2-oxo-acetamide (Compound 757

A solution of tert-butyl N-[5-[[2-[(2R,5S)-2-(1-acetyl-3-piperidyl)-5-methyl-1-piperidyl]-2-oxo-acetyl]amino]-3-methyl-2-pyridyl]carbamate (1.2 g, 2.39 mmol) and hydrogen chloride solution 4.0 M in dioxane (4 g, 109.71 mmol, 5.00 mL) in DCM (25 mL) was stirred at 25° C. for 12 hr. The solvent was removed and residue was purified by HPLC: 25-50% 0.5-7.5 min water-MeOH (NH$_3$ 0.1%), flow 30 ml/min (loading pump 4 ml/min MeOH) target mass 402) to obtain two 2-[(2R,5S)-2-(1-acetyl-3-piperidyl)-5-methyl-1-piperidyl]-N-(6-amino-5-methyl-3-pyridyl)-2-oxo-acetamide (146 mg, 363.64 µmol, 15.20% yield) and 2-[3-[(2R,5S)-1-acetyl-5-methyl-2-piperidyl]-1-piperidyl]-N-(6-amino-5-methyl-3-pyridyl)-2-oxo-acetamide (106 mg, 264.01 µmol, 11.04% yield). The structure of hydrogenated product was proved by 2D-NMR as trans-. The structures of final compounds were also proved by 2D-NMR.

Compound 757: $^1$H NMR (600 MHz, DMSO-$d_6$) δ (ppm) 0.89-0.96 (m, 3H), 1.05-1.16 (m, 1H), 1.18-1.40 (m, 2H), 1.51-1.70 (m, 4H), 1.74-1.88 (m, 2H), 1.89-1.95 (m, 2H), 1.95-1.99 (m, 3H), 1.99-2.02 (m, 3H), 2.78-2.96 (m, 1H), 2.97-3.27 (m, 1H), 3.55-3.67 (m, 1H), 3.68-4.00 (m, 1H), 4.09-4.24 (m, 2H), 5.53-5.63 (m, 2H), 7.40-7.49 (m, 1H), 7.94-8.02 (m, 1H), 10.26-10.35 (m, 1H).

Example 372

LCMS(ESI): [M]⁺ m/z: calcd 401.2; found 402.2; rt=1.517 min.

The Synthesis of N-(6-amino-5-methylpyridin-3-yl)-2-(1',5-dimethyl-[2,3'-bipiperidin]-1-yl)-2-oxoacetamide (Compound 832

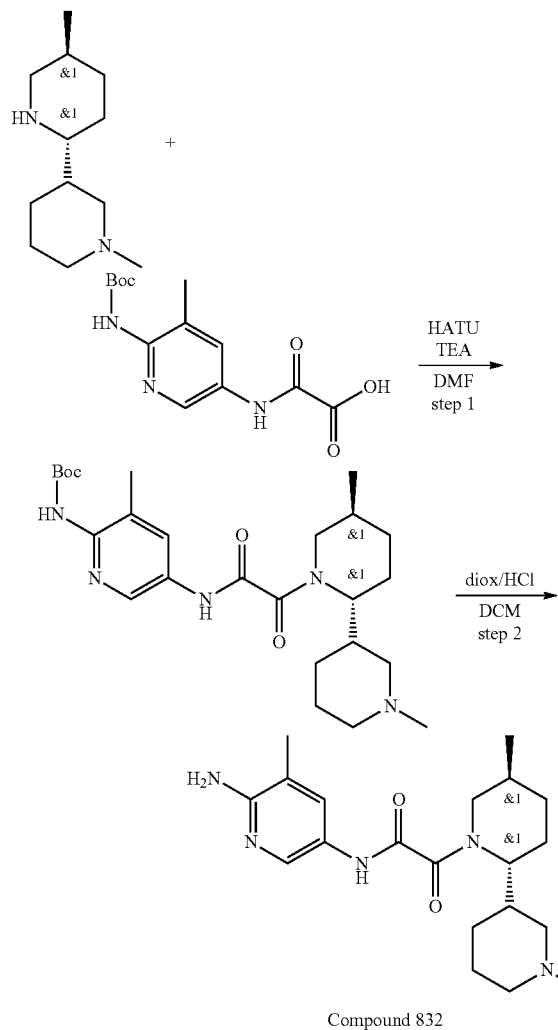

Compound 832

Step 1: Synthesis of rac-tert-butyl N-[3-methyl-5-[[2-[(2R,5S)-5-methyl-2-(1-methyl-3-piperidyl)-1-piperidyl]-2-oxo-acetyl]amino]-2-pyridyl]carbamate To a solution of 1-methyl-3-[(2R,5S)-5-methyl-2-piperidyl]piperidine (0.7 g, 2.60 mmol, 2HCl), 2-[[6-(tert-butoxycarbonylamino)-5-methyl-3-pyridyl]amino]-2-oxo-acetic acid (767.69 mg, 2.60 mmol) and TEA (1.58 g, 15.60 mmol, 2.17 mL), HATU (1.09 g, 2.86 mmol) was added portion wise. The resulting mixture was stirred at 25° C. for 3 hr, taken up with water (50 ml) and extracted with EtOAc (3*20 ml). The combined organic layer was washed with brine (2*25 ml), dried over Na₂SO₄ and the solvent was removed to give tert-butyl N-[3-methyl-5-[[2-[(2R,5S)-5-methyl-2-(1-methyl-3-piperidyl)-1-piperidyl]-2-oxo-acetyl]amino]-2-pyridyl]carbamate (0.95 g, 2.01 mmol, 77.16% yield). This compound was used for the next step without further purification.

¹H NMR (500 MHz, DMSO-d₆) δ (ppm) 0.78 (m, 2H), 0.93 (d, 3H), 1.12 (m, 2H), 1.42 (s, 9H), 1.62 (m, 6H), 2.56 (m, 2H), 2.65 (s, 3H), 2.86 (m, 6H), 3.31 (m, 2H), 7.46 (m, 1H), 8.41 (m, 1H), 9.04 (m, 1H), 10.87 (m, 1H).

LCMS(ESI): [M–Boc]⁺ m/z: calcd 373.2; found 374.2; Rt=1.080 min.

Step 2: Synthesis of N-(6-amino-5-methylpyridin-3-yl)-2-(1',5-dimethyl-[2,3'-bipiperidin]-1-yl)-2-oxoacetamide (Compound 832

A solution of tert-butyl N-[3-methyl-5-[[2-[(2R,5S)-5-methyl-2-(1-methyl-3-piperidyl)-1-piperidyl]-2-oxo-acetyl]amino]-2-pyridyl]carbamate (0.95 g, 2.01 mmol) and hydrogen chloride solution 4.0 M in dioxane (5 g, 137.13 mmol, 6.25 mL) in DCM (15 mL) was stirred at 25° C. for 5 hr. The solvent was removed and residue was purified by HPLC: 45-45-65% 0-1-6 min H₂O/MeOH/0.1% NH₄OH, flow: 30 ml/min (loading pump 4 ml/min MeOH) column: YMC Triart C18 100×20 mm, 5 um) and second time: 20-20-30% 0-1-6 min H₂O/ACN/0.1% NH₄OH, flow: 30 ml/min (loading pump 4 ml/min MeOH) target mass 373.49 column: YMC Triart C18 100×20 mm, 5 um) to obtain N-(6-amino-5-methyl-3-pyridyl)-2-[(2R,5S)-5-methyl-2-(1-methyl-3-piperidyl)-1-piperidyl]-2-oxo-acetamide (24 mg, 64.26 μmol, 3.20% yield).

Compound 832:

¹H NMR (600 MHz, DMSO-d₆) δ (ppm) 0.73-0.89 (m, 1H), 0.89-0.97 (m, 3H), 1.22-1.31 (m, 1H), 1.34-1.41 (m, 1H), 1.42-1.56 (m, 3H), 1.56-1.68 (m, 2H), 1.70-1.79 (m, 1H), 1.79-1.85 (m, 2H), 1.86-1.98 (m, 1H), 1.99-2.03 (m, 3H), 2.05-2.09 (m, 2H), 2.10-2.16 (m, 2H), 2.61-2.70 (m, 1H), 2.80-3.28 (m, 1H), 3.32-4.29 (m, 2H), 5.53-5.65 (m, 2H), 7.39-7.48 (m, 1H), 7.90-8.03 (m, 1H), 10.23-10.35 (m, 1H).

LCMS(ESI): [M]⁺ m/z: calcd 373.2; found 374.2; Rt=0.703 min.

Example 373. The Synthesis of N-(6-amino-5-methylpyridin-3-yl)-2-(5-methyl-[2,3'-bipiperidin]-1-yl)-2-oxoacetamide (Compound 744

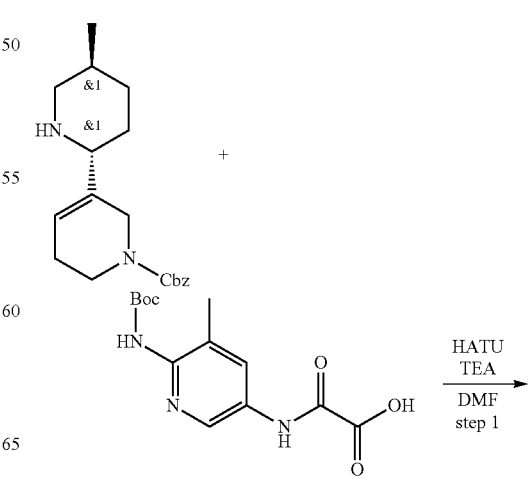

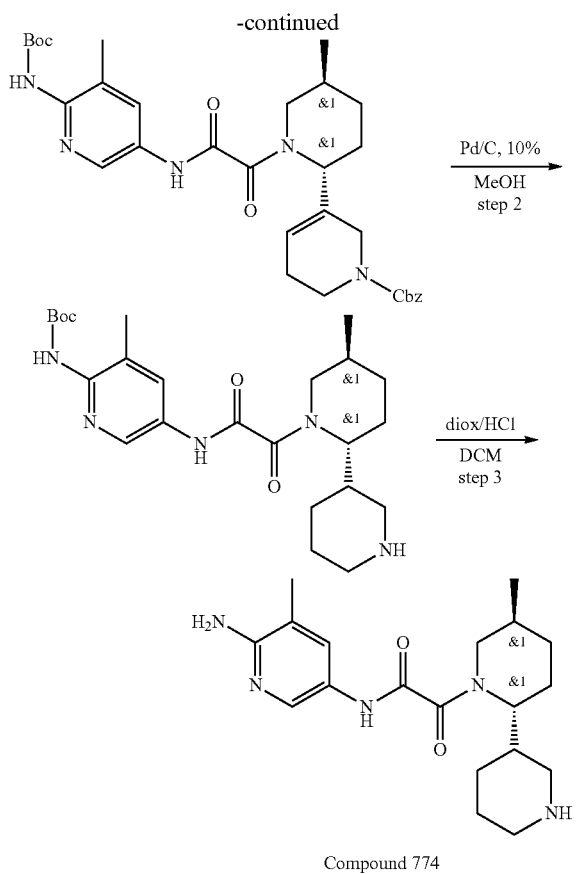

Compound 774

Step 1: Synthesis of rac-benzyl 3-((2R,5S)-1-(2-((6-((Tert-butoxycarbonyl)amino)-5-methylpyridin-3-yl)amino)-2-oxoacetyl)-5-methylpiperidin-2-yl)-5,6-dihydropyridine-1(2H)-carboxylate To solution of benzyl 5-[(2R,5S)-5-methyl-2-piperidyl]-3,6-dihydro-2H-pyridine-1-carboxylate (10 g, 3.18 mmol), 2-[[6-(tert-butoxycarbonylamino)-5-methyl-3-pyridyl]amino]-2-oxo-acetic acid (939.16 mg, 3.18 mmol) and TEA (1.61 g, 15.90 mmol, 2.22 mL) in DMF (50 mL), HATU (1.33 g, 3.50 mmol) was added portion wise. The resulting mixture was stirred at 25° C. for 3 hr, taken up with water (300 ml) and extracted with EtOAc (3*100 ml). The combined organic layer was washed with brine (3*100 ml), dried over $Na_2SO_4$ and evaporated to obtain crude product (11 g). The crude product was purified by gradient chromatography ($CHCl_3$-MTBE) to obtain benzyl 5-[(2R,5S)-1-[2-[[6-(tert-butoxycarbonylamino)-5-methyl-3-pyridyl]amino]-2-oxo-acetyl]-5-methyl-2-piperidyl]-3,6-dihydro-2H-pyridine-1-carboxylate (1 g, 1.69 mmol, 53.14% yield).

$^1$H NMR (400 MHz, DMSO-$d_6$) δ (ppm) 0.90 (d, 3H), 1.12 (m, 1H), 1.42 (s, 9H), 1.98 (m, 4H), 2.22 (m, 2H), 2.24 (s, 3H), 2.78 (m, 4H), 3.12 (m, 2H), 3.78 (m, 4H), 4.12 (m, 1H), 4.56 (m, 1H), 5.06 (s, 2H), 7.32 (m, 5H).

LCMS(ESI): [M]$^+$ m/z: calcd 591.2; found 592.2; Rt=1.606 min.

Step 2: Synthesis of rac-tert-butyl N-[3-methy-5-[[2-[(2R,5S)-5-methyl-2-(3-piperidyl)-1-piperidyl]-2-oxo-acetyl]amino]-2-pyridyl]carbamate To a solution of benzyl 5-[(2R,5S)-1-[2-[[6-(tert-butoxycarbonylamino)-5-methyl-3-pyridyl]amino]-2-oxo-acetyl]-5-methyl-2-piperidyl]-3,6-dihydro-2H-pyridine-1-carboxylate (1 g, 1.69 mmol) in MeOH (40 mL), palladium, 10% on carbon, Type 487, dry (0.5 g, 469.84 µmol, 10% purity) was added and the resulting mixture was stirred under hydrogen atmosphere at 40° C. for 72 hr. Conversion was controlled by LCMS. The catalyst was filtered off and solvent was removed to obtain crude product—mixture cis- and trans-isomers (during hydrogenation migration of double bond was observed). The crude product was purified by HPLC: 50-50-80% 0-1-6 min $H_2O$/MeOH/0.1% $NH_3$, flow: 30 ml/min (loading pump 4 ml/min MeOH) target mass 459 column: YMC Triart C18 100×20 mm, 5 um) to obtain three fraction. Each fraction was purified to obtain two products: tert-butyl N-[3-methyl-5-[[2-[(2R,5S)-5-methyl-2-(3-piperidyl)-1-piperidyl]-2-oxo-acetyl]amino]-2-pyridyl]carbamate (170 mg, 369.90 µmol, 21.89% yield) and tert-butyl N-[3-methyl-5-[[2-[(2S,5S)-5-methyl-2-(3-piperidyl)-1-piperidyl]-2-oxo-acetyl]amino]-2-pyridyl]carbamate (80 mg, 174.07 µmol, 10.30% yield). The structure of major fraction was proved by 2D-NMR as trans-. This fraction was used for the next step.

LCMS(ESI): [M]$^+$ m/z: calcd 459.2; found 460.2; Rt=1.620 min.

Step 3: Synthesis of N-(6-amino-5-methylpyridin-3-yl)-2-(5-methyl-[2,3'-bipiperidin]-1-yl)-2-oxoacetamide (Compound 744

A solution of tert-butyl N-[3-methyl-5-[[2-[(2R,5S)-5-methyl-2-(3-piperidyl)-1-piperidyl]-2-oxo-acetyl]amino]-2-pyridyl]carbamate (80 mg, 174.07 µmol) in DCM (5 mL) was stirred at 25° C. for 12 hr. The solvent was removed and residue was purified by HPLC: 0-5 min 30-80% water-MeOH ($NH_3$ 0.1%), flow 30 ml/min (loading pump 4 ml/min MeCN ($NH_3$ 0.1%)) column: YMC-Actus Triart C18 100*20 mml.D. S-5 um) to give N-(6-amino-5-methyl-3-pyridyl)-2-[(2R,5S)-5-methyl-2-(3-piperidyl)-1-piperidyl]-2-oxo-acetamide (11 mg, 30.60 µmol, 17.58% yield) and other fraction with impurities of cis-isomer 29 mg.

Compound 744: $^1$H NMR (600 MHz, DMSO-$d_6$) δ (ppm) 0.91-0.94 (m, 3H), 1.19-1.33 (m, 2H), 1.47-1.64 (m, 4H), 1.73-2.00 (m, 6H), 2.00-2.03 (m, 3H), 2.15-2.28 (m, 2H), 2.77-2.82 (m, 1H), 2.87-2.99 (m, 1H), 3.38-3.57 (m, 1H), 3.98-4.34 (m, 1H), 5.52-5.64 (m, 2H), 7.40-7.50 (m, 1H), 7.93-8.04 (m, 1H), 10.18-10.42 (m, 1H).

LCMS(ESI): [M]$^+$ m/z: calcd 359.2; found 360.2; Rt=0.887 min.

Example 374. The Synthesis of N-(6-amino-5-methylpyridin-3-yl)-2-(5-methyl-2-(4-(Thiazol-5-yl)phenyl)piperidin-1-yl)-2-oxoacetamide (Compound 887 and Compound 900

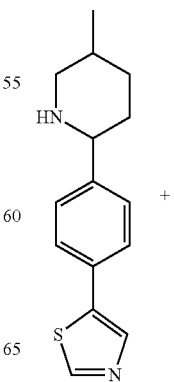

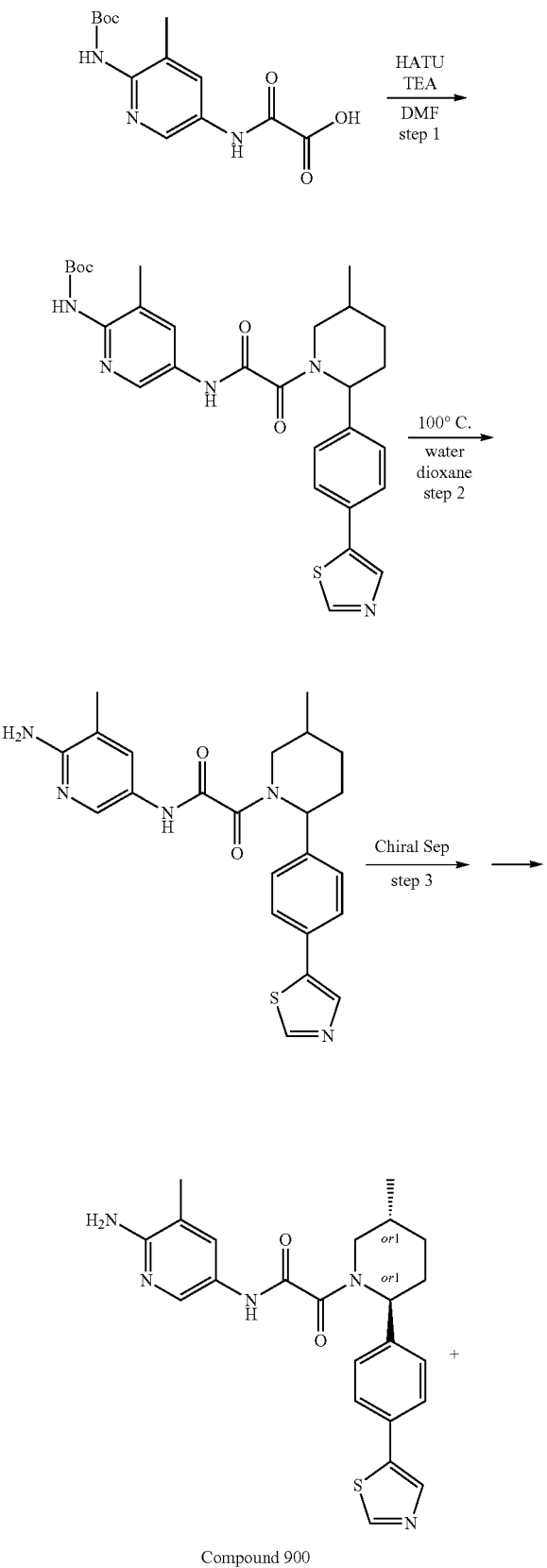

Compound 900

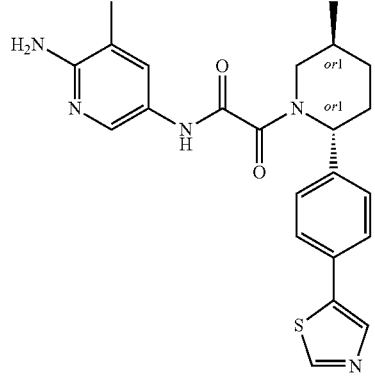

Compound 887

Step 1: Synthesis of tert-butyl (3-methyl-5-(2-(5-methyl-2-(4-(thiazol-5-yl)phenyl)piperidin-1-yl)-2-oxoacetamido)pyridin-2-yl)carbamate DIPEA (656.52 mg, 5.08 mmol, 884.80 μL) was added to the solution of respective 2-((6-((tert-butoxycarbonyl)amino)-5-methylpyridin-3-yl)amino)-2-oxoacetic acid (0.6 g, 2.03 mmol) and 5-(4-(5-methylpiperidin-2-yl)phenyl)thiazole (525.00 mg, 2.03 mmol) in DMF (10 mL). The resulting mixture was stirred for 5 min followed by the addition of HATU (849.85 mg, 2.24 mmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and MeOH-water as an eluent mixture) to afford tert-butyl (3-methyl-5-(2-(5-methyl-2-(4-(thiazol-5-yl)phenyl)piperidin-1-yl)-2-oxoacetamido)pyridin-2-yl)carbamate (119.4 mg, 222.90 μmol, 10.97% yield).

LCMS(ESI): [M]⁺ m/z: calcd 535.2; found 536.2; Rt=3.532 min.

Step 2: Synthesis of N-(6-amino-5-methylpyridin-3-yl)-2-(5-methyl-2-(4-(thiazol-5-yl)phenyl)piperidin-1-yl)-2-oxoacetamide tert-butyl (3-methyl-5-(2-(5-methyl-2-(4-(thiazol-5-yl)phenyl)piperidin-1-yl)-2-oxoacetamido)pyridin-2-yl)carbamate (119.4 mg, 222.90 μmol) was dissolved in water (5 mL) and dioxane (2 mL) mixture. Then reaction mixture was stirred for 17 hr at 100° C. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford N-(6-amino-5-methylpyridin-3-yl)-2-(5-methyl-2-(4-(thiazol-5-yl)phenyl)piperidin-1-yl)-2-oxoacetamide (46.5 mg, 106.76 μmol, 47.90% yield).

LCMS(ESI): [M]⁺ m/z: calcd 435.2; found 436.2; Rt=2.221 min.

Step 3: Chiral Separation (Compound 887 and Compound 900

N-(6-amino-5-methylpyridin-3-yl)-2-(5-methyl-2-(4-(thiazol-5-yl)phenyl)piperidin-1-yl)-2-oxoacetamide (46.5 mg, 106.76 mmol) was divided into enantiomers by Chiral HPLC (Column: YMC Chiral Art Cellulose-SC (250*20 mm, 5 mkm), IPA-MeOH, 50-50, 10 mL/min; 215 nm. Column Temperature: 20° C.; RetTime (isomer A)=17.69 min; RetTime (isomer B)=18.70 min; RetTime (isomer C)=23.65 min; RetTime (isomer D)=33.10 min). Ret time for Compound 887 in analytical conditions (column: IC, IPA-MeOH, 50-50, 0.5 ml/min as mobile phase) 48.43 min and for Compound 900 25.41 min.

Compound 887: Retention time: 48.43 min $^1$H NMR (600 MHz, DMSO-d$_6$) δ (ppm) 1.01 (m, 3H), 1.34 (m, 1H), 1.65 (m, 1H), 1.87 (m, 1H), 1.99 (m, 3H), 2.19 (m, 2H), 2.98 (dd, 1H), 3.73 (dd, 1H), 5.60 (m, 3H), 7.36 (d, 1H), 7.41 (m, 1H), 7.48 (s, 1H), 7.68 (m, 2H), 7.99 (m, 1H), 8.30 (s, 1H), 9.06 (s, 1H), 10.50 (m, 1H).

LCMS(ESI): [M]$^+$ m/z: calcd 435.2; found 436.2; Rt=0.858 min.

Compound 900: Retention time: 25.41 min $^1$H NMR (600 MHz, DMSO-d$_6$) δ (ppm) 1.01 (m, 3H), 1.34 (m, 1H), 1.66 (m, 1H), 1.86 (m, 1H), 1.99 (m, 4H), 2.18 (m, 1H), 2.99 (m, 1H), 3.83 (m, 1H), 5.60 (m, 3H), 7.41 (m, 3H), 7.68 (m, 2H), 7.99 (m, 1H), 8.30 (s, 1H), 9.06 (s, 1H), 10.50 (m, 1H).

LCMS(ESI): [M]$^+$ m/z: calcd 435.2; found 436.2; Rt=0.867 min.

Example 375. The Synthesis of N-(6-amino-5-methyl-3-pyridyl)-2-[(2S,5S)-2-(1,3-benzothiazol-5-yl)-4,4-difluoro-5-methyl-1-piperidyl]-2-oxo-acetamide (Compound 1069) and N-(6-amino-5-methyl-3-pyridyl)-2-[(2R,5R)-2-(1,3-benzothiazol-5-yl)-4,4-difluoro-5-methyl-1-piperidyl]-2-oxo-acetamide (Compound 1049)

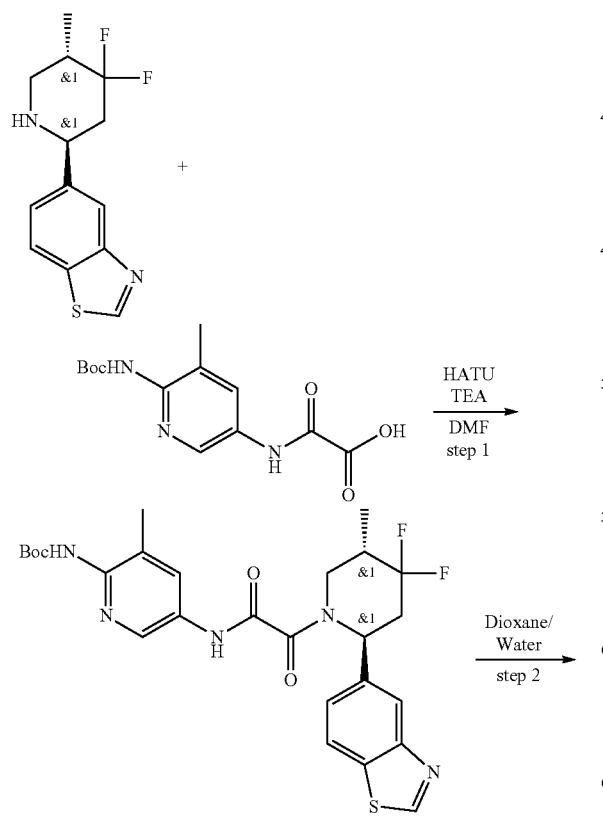

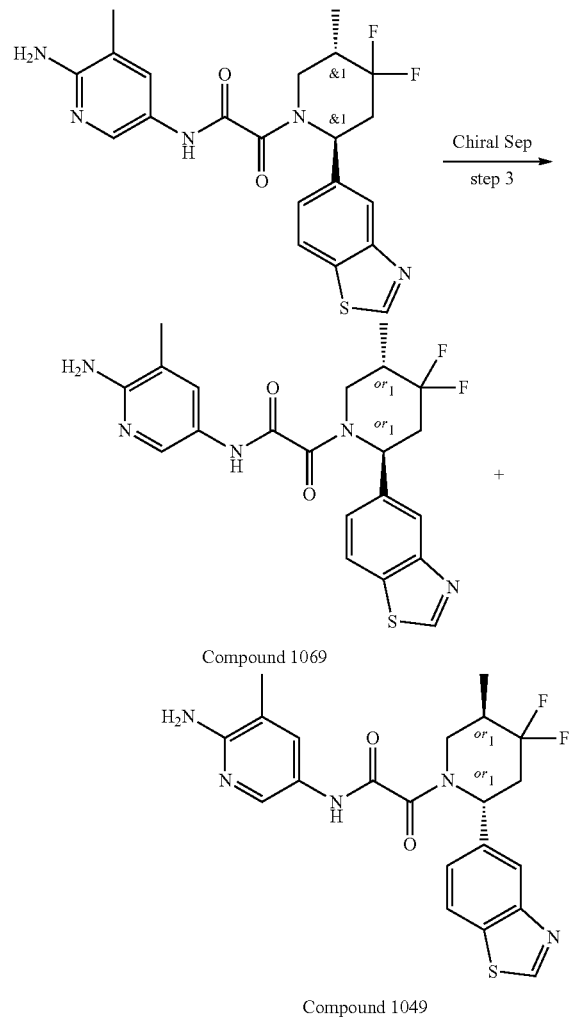

Step 1. Synthesis of tert-butyl N-[5-[[2-[(2R,5R)-2-(1,3-benzothiazol-5-yl)-4,4-difluoro-5-methyl-1-piperidyl]-2-oxo-acetyl]amino]-3-methyl-2-pyridyl] carbamate 5-[(2R,5R)-4,4-difluoro-5-methyl-2-piperidyl]-1,3-benzothiazole (480 mg, 1.79 mmol), 2-[[6-(tert-butoxycarbonylamino)-5-methyl-3-pyridyl]amino]-2-oxo-acetic acid (528.24 mg, 1.79 mmol), Triethylamine (905.08 mg, 8.94 mmol, 1.25 mL) were mixed in DMF (10 mL) and then HATU (1.02 g, 2.68 mmol) were added. Resulting mixture was stirred at 25° C. for 12 hr. The solvent was evaporated and the crude precipate was purified by HPLC (2-10 min 60-65% methanol 30 ml/min, loading pump 4 ml/min methanol, target mass 545, column: SunFire 100*19 mm, 5 microM) to obtain tert-butyl N-[5-[[2-[(2R,5R)-2-(1,3-benzothiazol-5-yl)-4,4-difluoro-5-methyl-1-piperidyl]-2-oxo-acetyl]amino]-3-methyl-2-pyridyl]carbamate (69.2 mg, 126.83 μmol, 7.09% yield)

LCMS(ESI): [M+1]$^+$ m/z: calcd 545.2; found 546.2; Rt=1.403 min.

Step 2. Synthesis of N-(6-amino-5-methyl-3-pyridyl)-2-[(2R,5R)-2-(1,3-benzothiazol-5-yl)-4,4-difluoro-5-methyl-1-piperidyl]-2-oxo-acetamide A solution of tert-butyl N-[5-[[2-[(2R,5R)-2-(1,3-benzothiazol-5-yl)-4,4-difluoro-5-methyl-1-piperidyl]-2-oxo-acetyl]amino]-3-methyl-2-pyridyl]carbamate (56.8 mg, 104.11 μmol) in Dioxane (2 mL) and Water (2 mL) was heated at 100° C. for 12 hr. Solvents were evaporated to obtain N-(6-amino-5-methyl-3-pyridyl)-2-[(2R,5R)-2-(1,3-benzothiazol-5-yl)-4,4-difluoro-5-methyl-1-piperidyl]-2-oxo-acetamide (44 mg, crude).

LCMS(ESI): [M+1]$^+$ m/z: calcd 445.2; found 446.0; Rt=2.330 min.

Step 3. Resolution for N-(6-amino-5-methyl-3-pyridyl)-2-[(2S,5S)-2-(1,3-benzothiazol-5-yl)-4,4-difluoro-5-methyl-1-piperidyl]-2-oxo-acetamide (Compound 1069) and N-(6-amino-5-methyl-3-pyridyl)-2-[(2R,5R)-2-(1,3-benzothiazol-5-yl)-4,4-difluoro-5-methyl-1-piperidyl]-2-oxo-acetamide (Compound 1049

The mixture of diastereomers was separated by chiral chromatography (Chiralpak IC-II (250*30 mm,5 mkm), Hexane-IPA-MeOH, 60-20-20, 12 ml/min) to obtain N-(6-amino-5-methyl-3-pyridyl)-2-[(2R,5R)-2-(1,3-benzothiazol-5-yl)-4,4-difluoro-5-methyl-1-piperidyl]-2-oxo-acetamide (15.7 mg, 35.24 μmol, 35.68% yield) and N-(6-amino-5-methyl-3-pyridyl)-2-[(2S,5S)-2-(1,3-benzothiazol-5-yl)-4,4-difluoro-5-methyl-1-piperidyl]-2-oxo-acetamide (12.73 mg, 28.58 μmol, 28.93% yield)

Preparative: RT for Compound 1069 (Chiralpak IC-II (250*30 mm,5 mkm), Hexane-IPA-MeOH, 60-20-20, 12 ml/min)=31.414; RT for Compound 1049 (Chiralpak IC-II (250*30 mm,5 mkm), Hexane-IPA-MeOH, 60-20-20, 12 ml/min)=37.133

Analytical: RT for Compound 1049 (Chiralpak IC (250*4.6, 5 mkm), Hexane-IPA-MeOH, 50-25-25, 0.6 ml/min)=24.265; Analytical: RT for Compound 1069 (Chiralpak IC (250*4.6, 5 mkm), Hexane-IPA-MeOH, 50-25-25, 0.6 ml/min)=20.813

Compound 1049 1H NMR (600 MHz, DMSO-d$_6$) δ 1.09-1.14 (m, 3H), 1.95-2.08 (m, 3H), 2.15-2.30 (m, 1H), 2.95-3.16 (m, 2H), 3.38-3.56 (m, 1H), 3.80-4.41 (m, 1H), 5.54-5.69 (m, 2H), 5.69-6.06 (m, 1H), 7.38-7.56 (m, 2H), 7.91-8.09 (m, 2H), 8.11-8.21 (m, 1H), 9.40 (s, 1H), 10.51-10.75 (m, 1H).

LCMS(ESI): [M+1]$^+$ m/z: calcd 445.2; found 446.0; Rt=2.330 min.

Compound 1069 1H NMR (600 MHz, DMSO-d$_6$) δ 1.09-1.14 (m, 3H), 1.95-2.08 (m, 3H), 2.15-2.30 (m, 1H), 2.95-3.16 (m, 2H), 3.38-3.56 (m, 1H), 3.80-4.41 (m, 1H), 5.54-5.69 (m, 2H), 5.69-6.06 (m, 1H), 7.38-7.56 (m, 2H), 7.91-8.09 (m, 2H), 8.11-8.21 (m, 1H), 9.40 (s, 1H), 10.51-10.75 (m, 1H).

LCMS(ESI): [M+1]$^+$ m/z: calcd 445.2; found 446.0; Rt=2.330 min.

Example 376. The Synthesis of N-(6-amino-5-methyl-3-pyridyl)-2-[(2R,5S)-5-ethyl-2-(1H-pyrazol-4-yl)-1-piperidyl]-2-oxo-acetamide (Compound 1032

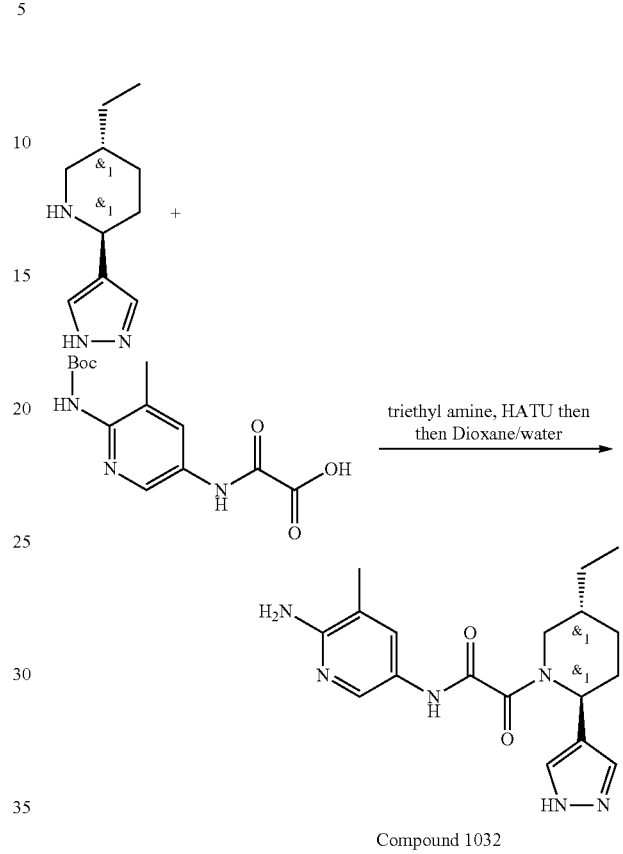

Compound 1032

To a stirred mixture of (2R,5S)-5-ethyl-2-(1H-pyrazol-4-yl)piperidine (200 mg, 793.07 μmol, 2HCl), 2-[[6-(tert-butoxycarbonylamino)-5-methyl-3-pyridyl]amino]-2-oxo-acetic acid (245.90 mg, 832.73 μmol) and Triethylamine (401.26 mg, 3.97 mmol, 552.69 μL) in Dimethylformamide (3 mL) was added TATU (280.97 mg, 872.38 μmol). The resulting reaction mixture was stirred at 25° C. for 4 hr. Then, it was subjected to HPLC (40-40-75% 0-1-6 min H$_2$O/MeOH, flow: 30 ml/min; column: Chromatorex 18 SMB 100-5T 100×19 mm, 5 um), affording tert-butyl N-[5-[[2-[(2R,5S)-5-ethyl-2-(1H-pyrazol-4-yl)-1-piperidyl]-2-oxo-acetyl]amino]-3-methyl-2-pyridyl]carbamate (133 mg, 291.32 μmol, 36.73% yield).

LCMS(ESI): [M+1]$^+$ m/z: calcd 456.2; found 457.2; Rt=2.741 min.

Water (500.00 mg, 27.75 mmol, 0.5 mL) was added to a solution of tert-butyl N-[5-[[2-[(2R,5S)-5-ethyl-2-(1H-pyrazol-4-yl)-1-piperidyl]-2-oxo-acetyl]amino]-3-methyl-2-pyridyl]carbamate (133 mg, 291.32 μmol) in Dioxane (1.5 mL). Resulting mixture was stirred at 100° C. for 16 hr. Then, it was subjected to HPLC (30-75% 0-5 min H$_2$O/MeOH/0.1% NH$_4$OH, flow: 30 ml/min; Column: YMC Triart C18 100×20 mm, 5 um), affording N-(6-amino-5-methyl-3-pyridyl)-2-[(2R,5S)-5-ethyl-2-(1H-pyrazol-4-yl)-1-piperidyl]-2-oxo-acetamide (69 mg, 193.59 μmol, 66.45% yield).

LCMS(ESI): [M+1]$^+$ m/z: calcd 356.2; found 357.2; Rt=2.161 min.

Example 377. Synthesis of N-(6-amino-5-methyl-3-pyridyl)-2-[(2S,5R)-2-(1,3-benzothiazol-6-yl)-5-methyl-1-piperidyl]-2-oxo-acetamide (Compound 716)

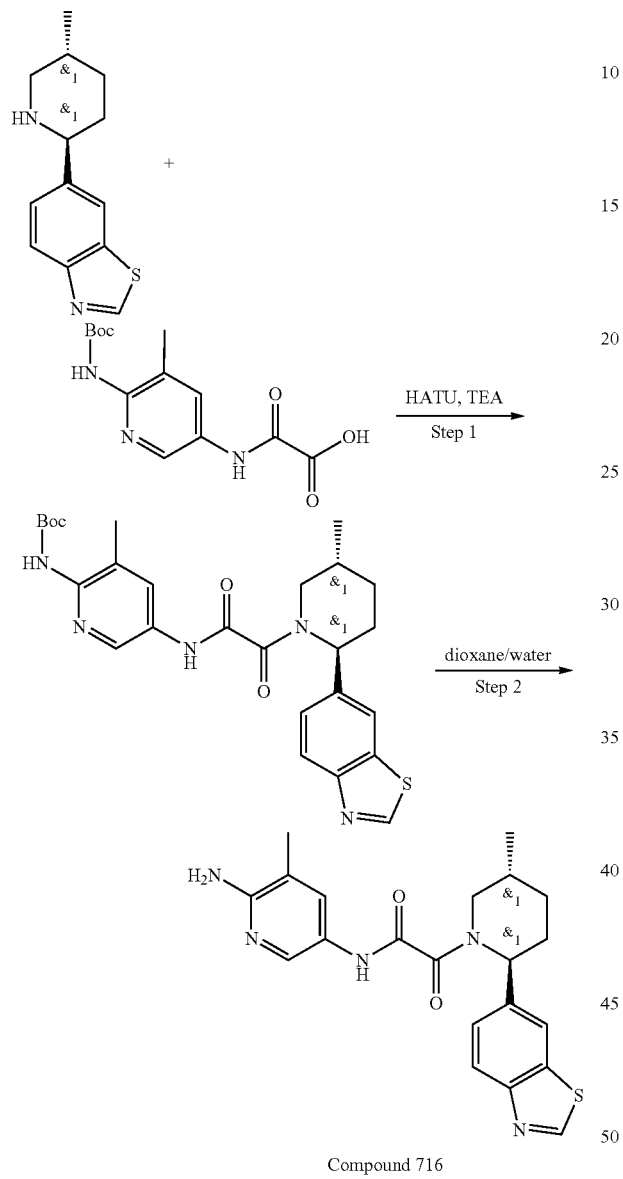

Compound 716

Step 1. Synthesis of tert-butyl N-[5-[[2-[(2S,5R)-2-(1,3-benzothiazol-6-yl)-5-methyl-1-piperidyl]-2-oxo-acetyl]amino]-3-methyl-2-pyridyl]carbamate 2-[[6-(tert-butoxycarbonylamino)-5-methyl-3-pyridyl]amino]-2-oxo-acetic acid (508.37 mg, 1.72 mmol) and TEA (1.74 g, 17.22 mmol, 2.40 mL) were dissolved in DMF (12 mL) and cooled to 0° C., HATU (981.90 mg, 2.58 mmol) was added and the mixture was stirred for 15 min at 0° C. 6-[(2S,5R)-5-methyl-2-piperidyl]-1,3-benzothiazole (0.4 g, 1.72 mmol) was added and the mixture was warmed to r.t. and stirred for 3 hr. 10 ml of ethyl acetate was added and organic phase was washed with brine three times. Organic phase was dried over Na₂SO₄, filtered and concentrated in vacuo at 45° C. to give crude product which was purified by HPLC (2-10 min 10-60% water/methanol (loading pump 4 ml methanol) column: TRIART 100*20 5 microM) to give tert-butyl N-[5-[[2-[(2S,5R)-2-(1,3-benzothiazol-6-yl)-5-methyl-1-piperidyl]-2-oxo-acetyl]amino]-3-methyl-2-pyridyl]carbamate (0.147 g, 288.45 μmol, 16.75% yield)

LCMS(ESI): [M+1]⁺ m/z: calcd 509.2; found 510.2; Rt=1.35 min.

Step 2. Synthesis of N-(6-amino-5-methyl-3-pyridyl)-2-[(2S,5R)-2-(1,3-benzothiazol-6-yl)-5-methyl-1-piperidyl]-2-oxo-acetamide (Compound 716)

tert-butyl N-[5-[[2-[(2S,5R)-2-(1,3-benzothiazol-6-yl)-5-methyl-1-piperidyl]-2-oxo-acetyl]amino]-3-methyl-2-pyridyl]carbamate (0.147 g, 288.45 μmol) was dissolved in mixture of dioxane (2 mL) and water (2 mL) then stirred at 100° C. for 12 hr. The reaction mixture was concentrated on vacuo at 55° C. to give crude product which was purified by HPLC (2-10 min 50-60% methanol/H₂O 30 ml/min (loading pump 4 ml methanol) column: SunFire 100*19 mm, 5 microM) to give N-(6-amino-5-methyl-3-pyridyl)-2-[(2S,5R)-2-(1,3-benzothiazol-6-yl)-5-methyl-1-piperidyl]-2-oxo-acetamide (0.04 g, 97.68 μmol, 33.86% yield).

¹H NMR (DMSO-d₆, 600 MHz): δ (ppm) 1.01 (m, 3H), 1.35 (m, 1H), 1.71 (m, 1H), 1.87 (m, 1H), 1.99 (m, 3H), 2.13 (m, 1H), 2.29 (m, 1H), 2.78 (m, 1H), 3.76 (m, 1H), 5.63 (m, 3H), 7.45 (m, 2H), 8.08 (m, 3H), 9.36 (s, 1H), 10.49 (m, 1H)

LCMS(ESI): [M+1]⁺ m/z: calcd 409.2; found 410.2; Rt=1.745 min.

Example 378. The Synthesis of 2-[(2S,5R)-2-(4-acetamidocyclohexyl)-5-methyl-1-piperidyl]-N-(6-amino-5-methyl-3-pyridyl)-2-oxo-acetamide and 2-[(2R,5S)-2-(4-acetamidocyclohexyl)-5-methyl-1-piperidyl]-N-(6-amino-5-methyl-3-pyridyl)-2-oxo-acetamide (Compound 281 and Compound 296

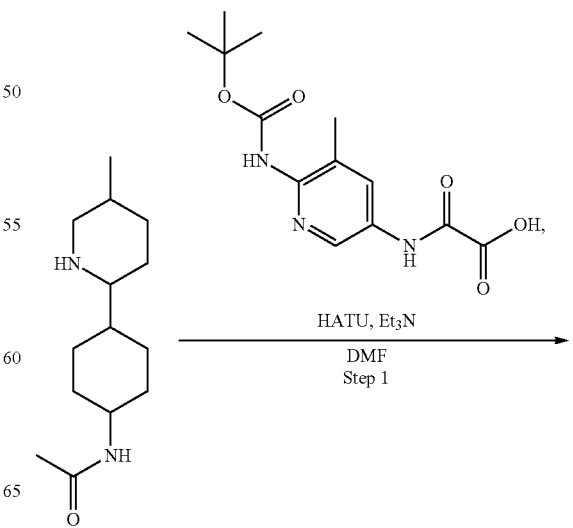

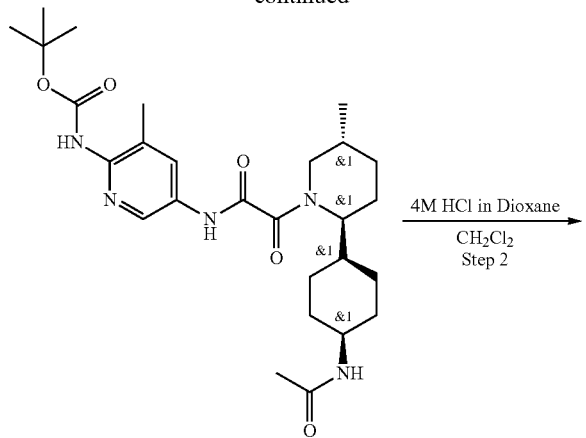

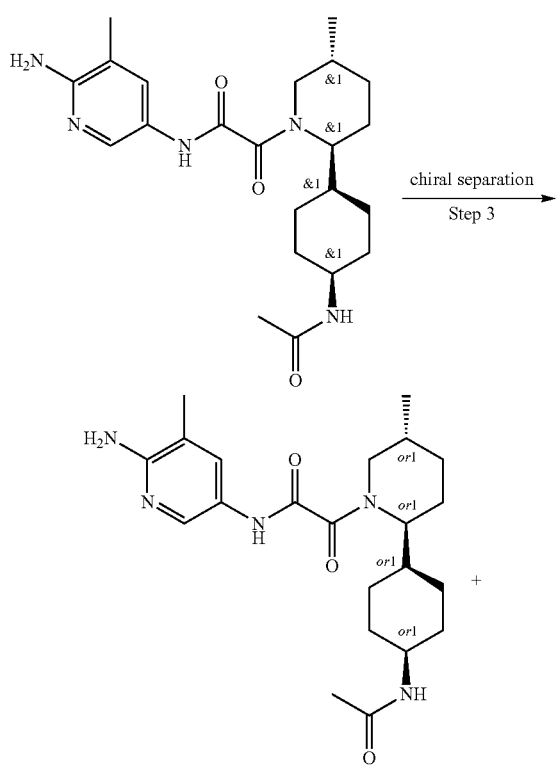

Compound 281

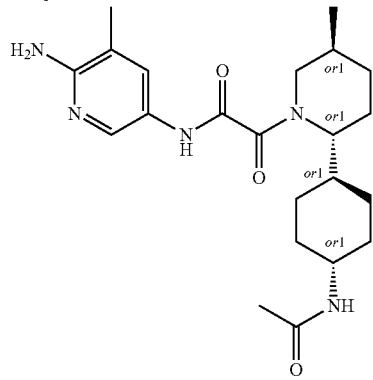

Compound 296

Step 1: Synthesis of rac-tert-butyl N-[5-[[2-[(2S, 5R)-2-(4-acetamidocyclohexyl)-5-methyl-1-piperidyl]-2-oxo-acetyl]amino]-3-methyl-2-pyridyl] carbamate To a stirred solution of N-[4-(5-methyl-2-piperidyl)cyclohexyl]acetamide (0.5 g, 2.10 mmol), 2-[[6-(tert-butoxycarbonylamino)-5-methyl-3-pyridyl]amino]-2-oxo-acetic acid (619.40 mg, 2.10 mmol) and HATU (797.57 mg, 2.10 mmol) in DMF (4 mL) was added Triethylamine (1.06 g, 10.49 mmol, 1.46 mL). The resulting reaction mixture was stirred at room temperature for 12 hours. After 12 hours, water (40 mL) was added and extracted with EtOAc (3×20 mL). The combined organic layer was washed with brine (3×20 mL), dried over $Na_2SO_4$ and evaporated under reduced pressure to obtain crude product, which was purified by HPLC (Eluent: 30-30-65%, 0-1-5 min, water-acetonitrile; flow rate: 30 mL/min; loading pump: 4 mL/min, acetonitrile; column: SunFire C18 100×19 mm, 5 um) to obtain rac-tert-butyl N-[5-[[2-[(2S,5R)-2-(4-acetamidocyclohexyl)-5-methyl-1-piperidyl]-2-oxo-acetyl]amino]-3-methyl-2-pyridyl]carbamate (220 mg, 426.65 μmol, 20.34% yield) as a light-yellow solid.

LCMS(ESI): [M+H]$^+$ m/z: calcd 515.4; found 516.4; Rt=3.229 min.

Step 2: Synthesis of rac-(2-[(2S,5R)-2-(4-acetamidocyclohexyl)-5-methyl-1-piperidyl]-N-(6-amino-5-methyl-3-pyridyl)-2-oxo-acetamide To a stirred solution of rac-tert-butyl N-[5-[[2-[(2S,5R)-2-(4-acetamidocyclohexyl)-5-methyl-1-piperidyl]-2-oxo-acetyl]amino]-3-methyl-2-pyridyl]carbamate (220.00 mg, 426.65 μmol) in DCM (10 mL), was added 4M Hydrogen chloride solution in dioxane (4.00 g, 109.71 mmol, 5 mL). The resulting reaction mixture was stirred at 25° C. for 12 hours. After 12 hours, the reaction mixture was evaporated in vacuo and the crude product was subjected to HPLC purification (Eluent: 0-5 min, 30-40%, water-methanol (0.1% $NH_3$); flow rate: 30 mL/min; loading pump: 5 mL/min, methanol (0.1% $NH_3$); column: YMC-Actus Triart C18 100×20 mm, 5 um) to give rac-(2-[(2S,5R)-2-(4-acetamidocyclohexyl)-5-methyl-1-piperidyl]-N-(6-amino-5-methyl-3-pyridyl)-2-oxo-acetamide (73 mg, 175.68 μmol, 41.18% yield) as a white solid.

LCMS(ESI): [M+H]$^+$ m/z: calcd 415.3; found 416.4; Rt=2.120 min.

Step 3: Chiral Separation of 2-[(2S,5R)-2-(4-acetamidocyclohexyl)-5-methyl-1-piperidyl]-N-(6-amino-5-methyl-3-pyridyl)-2-oxo-acetamide and 2-[(2R,5S)-2-(4-acetamidocyclohexyl)-5-methyl-1-piperidyl]-N-(6-amino-5-methyl-3-pyridyl)-2-oxo-acetamide (Compound 281 and Compound 296 rac-(2-[(2S,5R)-2-(4-acetamidocyclohexyl)-5-methyl-1-piperidyl]-N-(6-amino-5-methyl-3-pyridyl)-2-oxo-acetamide (73 mg, 175.68 μmol) was subjected to chiral HPLC purification (Column: Chiralpak OJ-H (250×20 mm, 5 um); Mobile phase: Hexane-IPA-MeOH, 80-10-10; Flow Rate: 12 mL/min) to get 2-[(2S,5R)-2-(4-acetamidocyclohexyl)-5-methyl-1-piperidyl]-N-(6-amino-5-methyl-3-pyridyl)-2-oxo-acetamide (Compound 281, 21 mg) and 2-[(2R,5S)-2-(4-acetamidocyclohexyl)-5-methyl-1-piperidyl]-N-(6-amino-5-methyl-3-pyridyl)-2-oxo-acetamide (Compound 296, 39 mg) as white solids.

Compound 281: $^1$H NMR (DMSO-$d_6$, 500 MHz): δ (ppm) 0.81-0.98 (m, 5H), 1.02-1.24 (m, 3H), 1.27-1.46 (m, 1H), 1.54-1.68 (m, 3H), 1.73-1.92 (m, 9H), 2.00-2.08 (m, 3H), 2.65-2.97 (m, 1H), 3.40-3.47 (m, 1H), 3.95-4.21 (m, 1H), 5.61 (s, 2H), 7.41-7.53 (m, 1H), 7.63-7.73 (m, 1H), 7.96-8.04 (m, 1H), 10.25-10.37 (m, 1H).

LCMS(ESI): [M+H]$^+$ m/z: calcd 415.3; found 416.2; Rt=3.326 min.

Chiral HPLC: Rt=23.08 min (Column: OJ-H; Mobile phase: Hexane-IPA-MeOH, 80-10-10;

Flow Rate: 0.6 mL/min).

Compound 296: $^1$H NMR (DMSO-$d_6$, 500 MHz): δ (ppm) 0.81-0.98 (m, 5H), 1.02-1.24 (m, 3H), 1.27-1.46 (m, 1H), 1.54-1.68 (m, 3H), 1.73-1.92 (m, 9H), 2.00-2.08 (m, 3H), 2.65-2.97 (m, 1H), 3.40-3.47 (m, 1H), 3.95-4.21 (m, 1H), 5.61 (s, 2H), 7.41-7.53 (m, 1H), 7.63-7.73 (m, 1H), 7.96-8.04 (m, 1H), 10.25-10.37 (m, 1H).

LCMS(ESI): [M+H]$^+$ m/z: calcd 415.3; found 416.2; Rt=3.375 min.

Chiral HPLC: Rt=11.89 min (Column: OJ-H; Mobile phase: Hexane-IPA-MeOH, 80-10-10;

Flow Rate: 0.6 mL/min).

Example 379. The Synthesis of rac-N-(6-amino-5-methyl-3-pyridyl)-2-[(2R,5S)-5-methyl-2-[2-(trifluoromethyl)-1,3-benzothiazol-5-yl]-1-piperidyl]-2-oxo-acetamide (Compound 861), rel-N-(6-amino-5-methyl-3-pyridyl)-2-[(2S,5R)-5-methyl-2-[2-(trifluoromethyl)-1,3-benzothiazol-5-yl]-1-piperidyl]-2-oxo-acetamide (Compound 959) and rel-N-(6-amino-5-methyl-3-pyridyl)-2-[(2R,5S)-5-methyl-2-[2-(trifluoromethyl)-1,3-benzothiazol-5-yl]-1-piperidyl]-2-oxo-acetamide (Compound 972

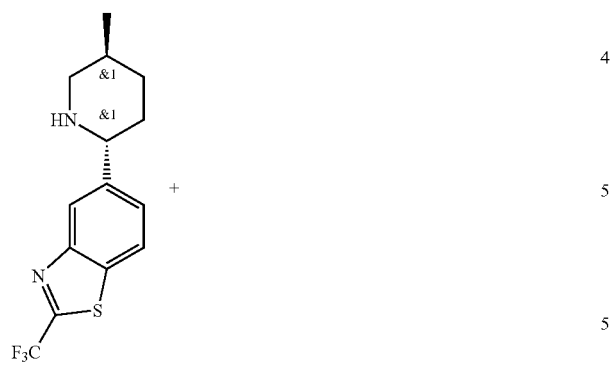

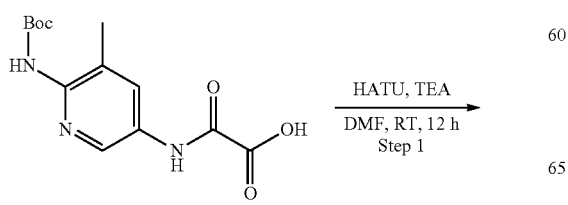

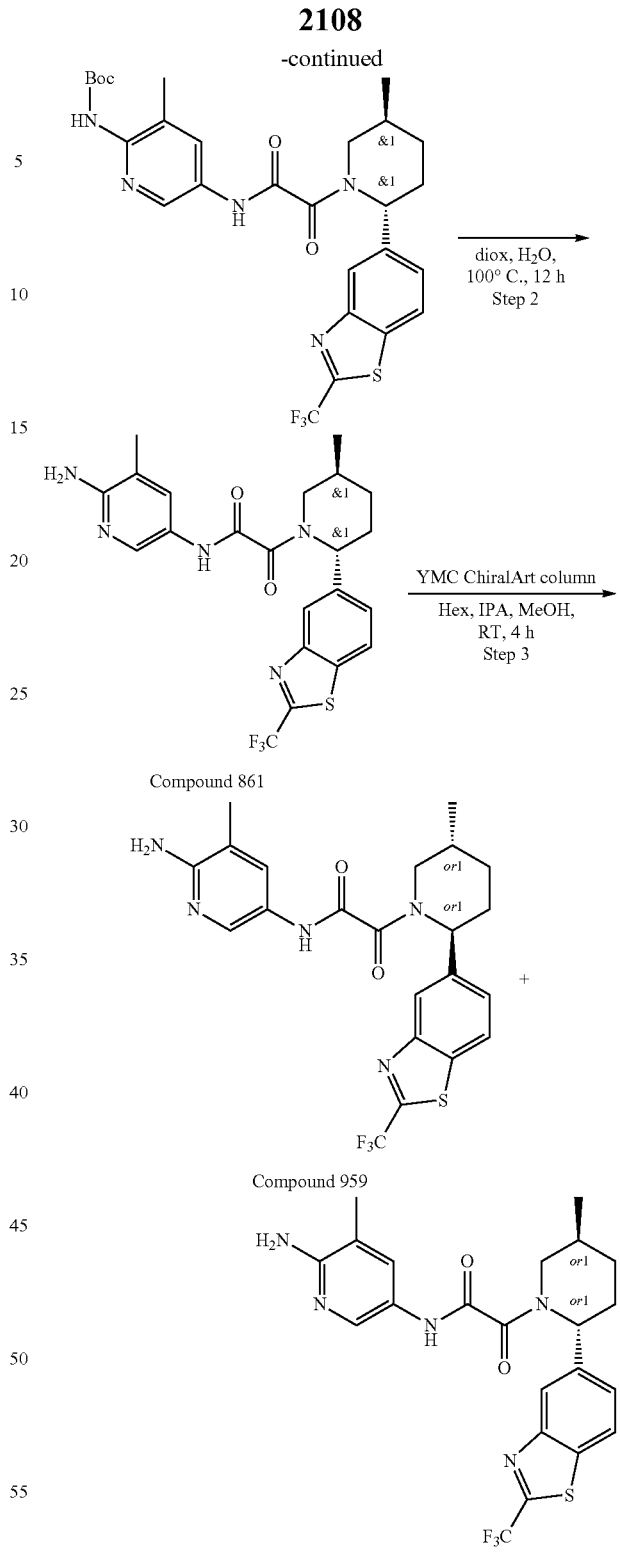

Step 1: The Synthesis of rac-tert-butyl N-[3-methyl-5-[[2-[5-methyl-2-[2-(trifluoromethyl)-1,3-benzothiazol-5-yl]-1-piperidyl]-2-oxo-acetyl]amino]-2-pyridyl]carbamate 2-[[6-(tert-butoxycarbonylamino)-5-methyl-3-pyridyl]amino]-2-oxo-acetic acid (294.95 mg, 998.86 μmol) and rac-5-(5-methyl-2-piperidyl)-2-(trifluoromethyl)-1,3-benzothiazole (0.3 g, 998.86 μmol) were mixed in DMF (15 mL). The reaction suspension was cooled to 0° C. and HATU (417.78 mg, 1.10 mmol) followed by TEA (202.15 mg, 2.00 mmol, 278.44 μL) were added and stirred at ambient temperature for 12 hr. The reaction mixture was evaporated in vacuo and poured into water (100 ml) and extracted with EtOAc (2×40 ml). The combined organic extracts were washed with water (2*30 ml), dried over sodium sulphate and evaporated in vacuo to afford product rac-tert-butyl N-[3-methyl-5-[[2-[5-methyl-2-[2-(trifluoromethyl)-1,3-benzothiazol-5-yl]-1-piperidyl]-2-oxo-acetyl]amino]-2-pyridyl]carbamate (0.42 g, 727.13 μmol, 72.80% yield).

LCMS(ESI): [M+H]$^+$ m/z: calcd 577.2; found 578.2; Rt=1.469 min.

Step 2: The Synthesis of rac-N-(6-amino-5-methyl-3-pyridyl)-2-[(2R,5S)-5-methyl-2-[2-(trifluoromethyl)-1,3-benzothiazol-5-yl]-1-piperidyl]-2-oxo-acetamide (Compound 861

Dioxane (20 mL) was added to a stirred solution of rac-tert-butyl N-[3-methyl-5-[[2-[5-methyl-2-[2-(trifluoromethyl)-1,3-benzothiazol-5-yl]-1-piperidyl]-2-oxo-acetyl]amino]-2-pyridyl]carbamate (0.42 g, 727.13 μmol) in water (10 mL) at room temperature. The resulting mixture was stirred at 100° C. for 12 hr, and then evaporated in vacuo and obtained crude product 0.3 g was purified by preparative 70-70-90% 0-1-6 min H$_2$O/MeOH/0.1% NH$_4$OH, flow: 30 mL/min target mass to afford product rac-N-(6-amino-5-methyl-3-pyridyl)-2-[(2R,5S)-5-methyl-2-[2-(trifluoromethyl)-1,3-benzothiazol-5-yl]-1-piperidyl]-2-oxo-acetamide (0.148 g, 309.95 μmol, 42.63% yield).

$^1$H NMR (dmso, 600 MHz): δ (ppm) 0.89-1.12 (m, 3H), 1.29-1.43 (m, 1H), 1.63-1.75 (m, 1H), 1.79-1.93 (m, 1H), 1.94-2.05 (m, 3H), 2.07-2.23 (m, 1H), 2.27-2.35 (m, 1H), 2.81-3.22 (m, 1H), 3.48-4.06 (m, 1H), 5.28-5.59 (m, 1H), 5.59-5.82 (m, 2H), 7.36-7.54 (m, 1H), 7.60-7.73 (m, 1H), 7.90-8.08 (m, 1H), 8.14-8.24 (m, 1H), 8.29-8.42 (m, 1H), 10.42-10.77 (m, 1H).

LCMS(ESI): [M+H]$^+$ m/z: calcd 477.2; found 478.4; Rt=2.825 min.

Step 3: The Synthesis of rel-N-(6-amino-5-methyl-3-pyridyl)-2-[(2S,5R)-5-methyl-2-[2-(trifluoromethyl)-1,3-benzothiazol-5-yl]-1-piperidyl]-2-oxo-acetamide (Compound 959) and rel-N-(6-amino-5-methyl-3-pyridyl)-2-[(2R,5S)-5-methyl-2-[2-(trifluoromethyl)-]1,3-benzothiazol-5-yl]-1-piperidyl]-2-oxo-acetamide (Compound 972

The rac-N-(6-amino-5-methyl-3-pyridyl)-2-[(2R,5S)-5-methyl-2-[2-(trifluoromethyl)-1,3-benzothiazol-5-yl]-1-piperidyl]-2-oxo-acetamide (0.1155 g, 241.88 μmol) was subjected to chiral HPLC purification (Column: YMC ChiralArt (250*20 mm, 5 mkm); Eluent: Hexane-IPA-MeOH, 50-25-25, flow rate: 12 mL/min) to give the two individual enantiomers Compound 959—rel-N-(6-amino-5-methyl-3-pyridyl)-2-[(2S,5R)-5-methyl-2-[2-(trifluoromethyl)-1,3-benzothiazol-5-yl]-1-piperidyl]-2-oxo-acetamide (0.05461 g, 114.37 μmol, 47.28% yield) and Compound 972—rel-N-(6-amino-5-methyl-3-pyridyl)-2-[(2R,5S)-5-methyl-2-[2-(trifluoromethyl)-1,3-benzothiazol-5-yl]-1-piperidyl]-2-oxo-acetamide (43.86 mg, 91.85 μmol, 37.97% yield).

Compound 959: RT (IC, Hexane-IPA-MeOH, 50-25-25, 0.6 mL/min)=13.762 min.

$^1$H NMR (600 MHz, DMSO-d$_6$) δ 0.98-1.06 (m, 3H), 1.29-1.44 (m, 1H), 1.63-1.73 (m, 1H), 1.80-1.92 (m, 1H), 1.94-2.03 (m, 3H), 2.08-2.21 (m, 1H), 2.26-2.33 (m, 1H), 2.76-3.20 (m, 1H), 3.45-4.06 (m, 1H), 5.27-5.59 (m, 1H), 5.61-5.74 (m, 2H), 7.37-7.51 (m, 1H), 7.60-7.72 (m, 1H), 7.91-8.04 (m, 1H), 8.15-8.22 (m, 1H), 8.30-8.37 (m, 1H), 10.48-10.59 (m, 1H).

LCMS(ESI): [M+H]$^+$ m/z: calcd 477.2; found 478.2; Rt=2.884 min.

Compound 972: RT (IC, Hexane-IPA-MeOH, 50-25-25, 0.6 mL/min)=21.265 min.

$^1$H NMR (600 MHz, DMSO-d$_6$) δ 1.00-1.05 (m, 3H), 1.30-1.39 (m, 1H), 1.63-1.72 (m, 1H), 1.83-1.91 (m, 1H), 1.94-2.03 (m, 3H), 2.09-2.21 (m, 1H), 2.22-2.34 (m, 1H), 2.75-3.08 (m, 1H), 3.45-4.07 (m, 1H), 5.28-5.59 (m, 1H), 5.60-5.75 (m, 2H), 7.36-7.54 (m, 1H), 7.59-7.72 (m, 1H), 7.90-8.04 (m, 1H), 8.15-8.23 (m, 1H), 8.30-8.39 (m, 1H), 10.49-10.60 (m, 1H).

LCMS(ESI): [M+H]$^+$ m/z: calcd 477.2; found 478.2; Rt=2.833 min.

Example 380. The Synthesis of N-(6-amino-5-methylpyridin-3-yl)-2-(5-methyl-2-(1H-thieno[3,2-c]pyrazol-5-yl)piperidin-1-yl)-2-oxoacetamide (Compound 743, Compound 824 and Compound 826

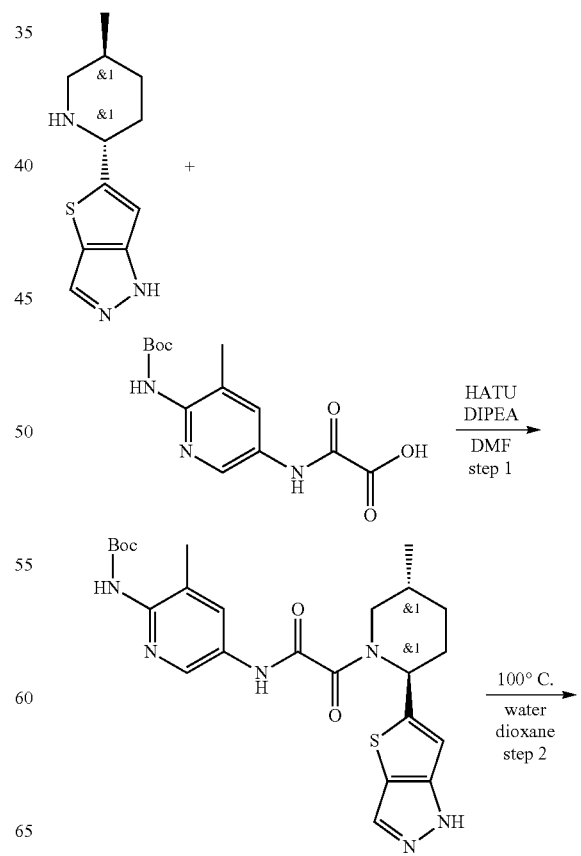

-continued

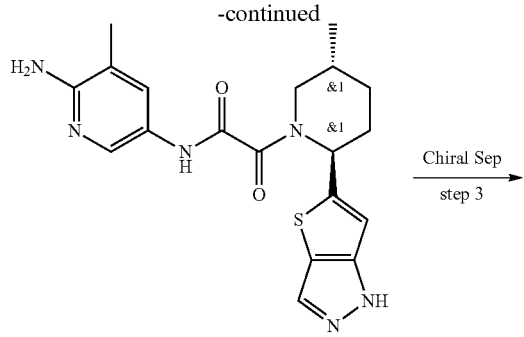

Compound 743

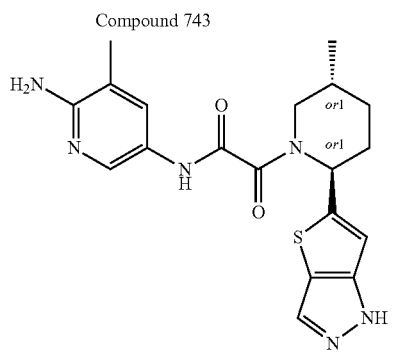

Compound 826

+

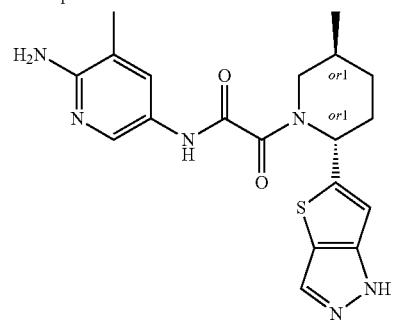

Compound 824

Step 1: Synthesis of rac-tert-butyl (3-methyl-5-(2-((2R,5S)-5-methyl-2-(1H-thieno[3,2-c]pyrazol-5-yl)piperidin-1-yl)-2-oxoacetamido)pyridin-2-yl)carbamate DIPEA (765.94 mg, 5.93 mmol, 1.03 mL) was added to the solution of respective 2-[[6-(tert-butoxycarbonylamino)-5-methyl-3-pyridyl]amino]-2-oxo-acetic acid (0.5 g, 1.69 mmol) and 5-(5-methyl-2-piperidyl)-1H-thieno[3,2-c]pyrazole (374.75 mg, 1.69 mmol) in DMF (10 mL). The resulting mixture was stirred for 5 min followed by the addition of HATU (708.20 mg, 1.86 mmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and $H_2O$-MeOH as an eluent mixture) to afford tert-butyl N-[3-methyl-5-[[2-[5-methyl-2-(1H-thieno[3,2-c]pyrazol-5-yl)-1-piperidyl]-2-oxo-acetyl]amino]-2-pyridyl]carbamate (275.4 mg, 552.35 μmol, 32.62% yield).

LCMS(ESI): $[M]^+$ m/z: calcd 498.2; found 499.2; Rt=2.933 min.

Step 2: Synthesis of N-(6-amino-5-methylpyridin-3-yl)-2-(5-methyl-2-(1H-thieno[3,2-c]pyrazol-5-yl)piperidin-1-yl)-2-oxoacetamide (Compound 743 tert-butyl N-[3-methyl-5-[[2-[5-methyl-2-(1H-thieno[3,2-c]pyrazol-5-yl)-1-piperidyl]-2-oxo-acetyl]amino]-2-pyridyl]carbamate (275.40 mg, 552.35 μmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and $H_2O$-MeOH (45-60%)+$NH_3$ as an eluent mixture) to afford N-(6-amino-5-methyl-3-pyridyl)-2-[(2R,5S)-5-methyl-2-(1H-thieno[3,2-c]pyrazol-5-yl)-1-piperidyl]-2-oxo-acetamide (148.6 mg, 372.92 μmol, 67.51% yield).

Compound 743: $^1$H NMR (600 MHz, DMSO-$d_6$) δ (ppm) 0.97-1.00 (m, 3H), 1.37-1.45 (m, 1H), 1.80-1.98 (m, 3H), 1.98-2.02 (m, 3H), 2.07-2.21 (m, 1H), 2.93-2.97 (m, 0.4H), 3.36-3.40 (m, 0.6H), 3.45-4.08 (m, 1H), 5.47-5.60 (m, 1H), 5.61-5.82 (m, 2H), 7.02-7.06 (m, 1H), 7.48 (s, 1H), 7.69-7.90 (m, 1H), 8.01 (d, 1H), 10.50 (bs s, 1H), 13.05 (br s, 1H).

LCMS(ESI): $[M]^+$ m/z: calcd 398.2; found 399.2; Rt=1.779 min.

Step 3: Chiral Separation (Compound 824 and Compound 826

N-(6-amino-5-methyl-3-pyridyl)-2-[(2R,5S)-5-methyl-2-(1H-thieno[3,2-c]pyrazol-5-yl)-1-piperidyl]-2-oxo-acetamide (148.60 g, 372.92 mmol) was separated by Chiral Chromatography in conditions: Column: Chiralpak IB (250*20 mm, 5 mkm); Mobile phase: Hexane-IPA-MeOH 70-15-15 Flow Rate: 12 mL/min; m (compound)=0.12 g, 5 injections were made, 20 mg/1 injection V(fractions)=3 L, 4.5 hours. Rt(Compound 826)=24.57 min and Rt(Compound 824)=33.68 min to afford N-(6-amino-5-methyl-3-pyridyl)-2-[(2R,5S)-5-methyl-2-(1H-thieno[3,2-c]pyrazol-5-yl)-1-piperidyl]-2-oxo-acetamide (37.74 mg, 94.71 μmol, 2.54e-2% yield) and N-(6-amino-5-methyl-3-pyridyl)-2-[(2S,5R)-5-methyl-2-(1H-thieno[3,2-c]pyrazol-5-yl)-1-piperidyl]-2-oxo-acetamide (38.75 mg, 97.24 μmol, 2.61e-2% yield).

Ret time for Compound 824 in analytical conditions (column: IB, Hexane-IPA-MeOH, 70-15-15, 0.6 ml/min as mobile phase) 29.27 min and for Compound 826 21.00 min.

Compound 824: Retention time: 29.27 min $^1$H NMR (600 MHz, DMSO-$d_6$) δ (ppm) 0.98-1.01 (m, 3H), 1.37-1.45 (m, 1H), 1.83-1.97 (m, 2H), 1.97-2.03 (m, 3H), 2.04-2.19 (m, 2H), 2.92-2.97 (m, 0.4H), 3.35-3.39 (m, 0.6H), 3.43-4.08 (m, 1H), 5.43-5.85 (m, 3H), 6.95-7.13 (m, 1H), 7.48 (s, 1H), 7.69-7.97 (m, 1H), 8.01 (d, 1H), 10.38-10.61 (m, 1H), 12.91-13.34 (m, 1H).

LCMS(ESI): $[M]^+$ m/z: calcd 398.2; found 399.2; Rt=1.762 min.

Compound 826: Retention time: 21.00 min $^1$H NMR (600 MHz, DMSO-$d_6$) δ (ppm) 0.95-1.03 (m, 3H), 1.37-1.47 (m, 1H), 1.81-1.97 (m, 2H), 1.98-2.03 (m, 3H), 2.03-2.20 (m, 2H), 2.92-2.97 (m, 0.4H), 3.35-3.41 (m, 0.6H), 3.43-4.08 (m, 1H), 5.44-5.84 (m, 3H), 6.97-7.12 (m, 1H), 7.46-7.52 (m, 1H), 7.67-7.99 (m, 1H), 7.99-8.03 (m, 1H), 10.47-10.55 (m, 1H), 12.91-13.32 (m, 1H).

LCMS(ESI): $[M]^+$ m/z: calcd 398.2; found 399.2; Rt=1.752 min.

Example 381. The Synthesis of N-(6-amino-5-ethylpyridin-3-yl)-2-(5-methyl-2-(1H-thieno[3,2-c]pyrazol-5-yl)piperidin-1-yl)-2-oxoacetamide (Compound 955 and Compound 967

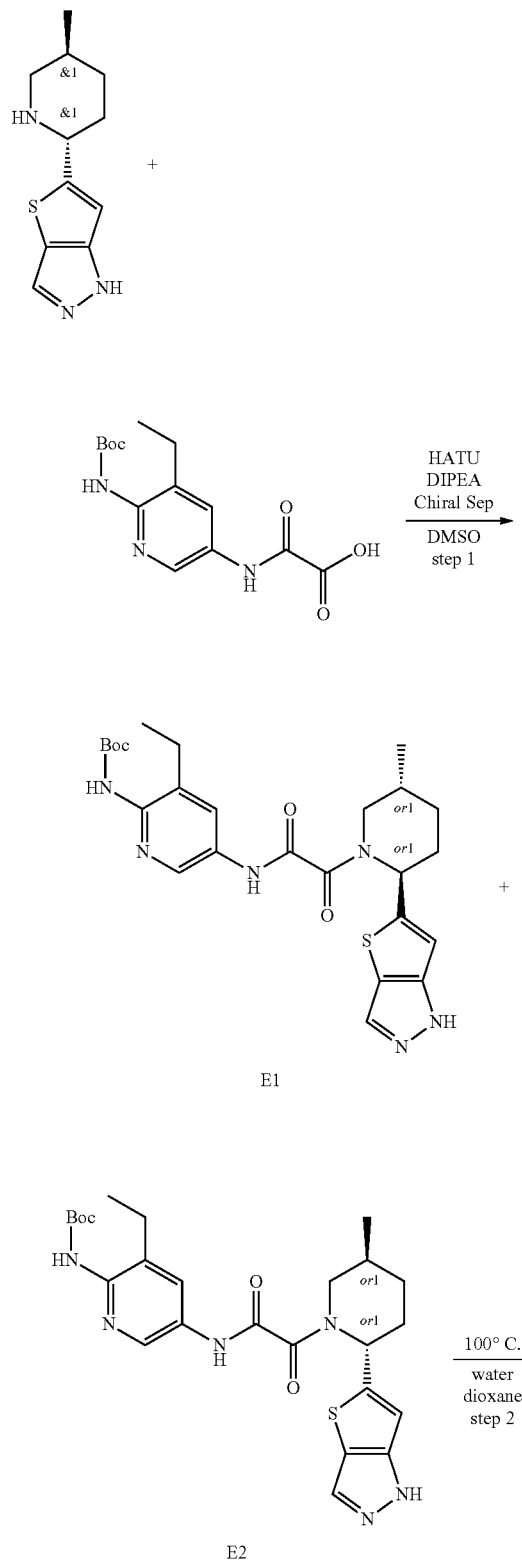

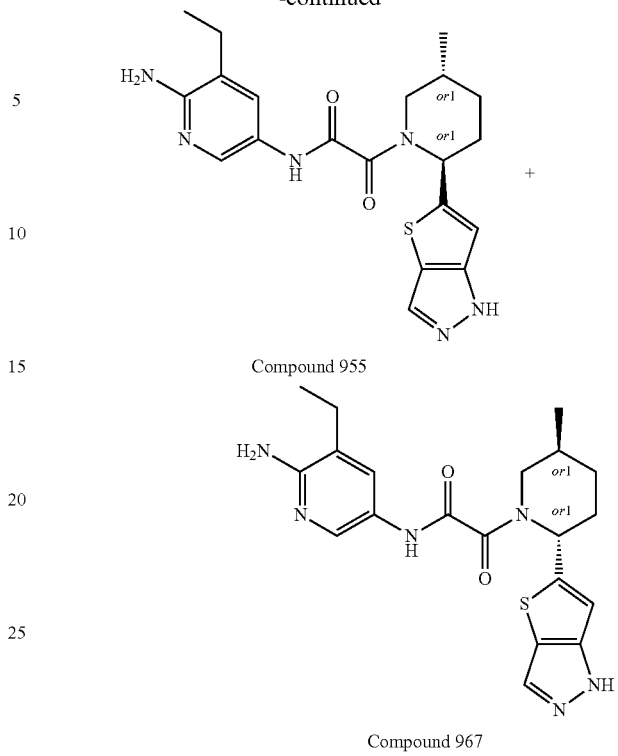

Compound 955

Compound 967

Step 1: Synthesis of tert-butyl (3-ethyl-5-(2-(5-methyl-2-(1H-thieno[3,2-c]pyrazol-5-yl)piperidin-1-yl)-2-oxoacetamido)pyridin-2-yl)carbamate 2-[[6-(tert-butoxycarbonylamino)-5-ethyl-3-pyridyl]amino]-2-oxo-acetic acid (349.40 mg, 1.13 mmol), 5-[(2R,5S)-5-methyl-2-piperidyl]-1H-thieno[3,2-c]pyrazole (0.25, 1.13 mmol) and DIPEA (437.96 mg, 3.39 mmol, 590.24 µL) were dissolved in DMSO (6 mL) under gentle heating. HATU (515.40 mg, 1.36 mmol) was added in small portions under vigorous stirring and occasional heating. After the reaction was complete, the mixture was purified by HPLC (60% 0.5-6.5 min water-MeOH; flow 30 ml/min (loading pump 4 ml/min MeOH); target mass 512; column SunFire C18 100×19 mm 5 um (R)) to give racemic product. After chiral HPLC (Chiral ART Cellulose-SC (250*20, 5 mkm), Hexane-IPA-MeOH, 50-25-25, 12 ml/min) tert-butyl N-[3-ethyl-5-[[2-[(2S,5R)-5-methyl-2-(1H-thieno[3,2-c]pyrazol-5-yl)-1-piperidyl]-2-oxo-acetyl]amino]-2-pyridyl]carbamate (32 mg, 62.42 µmol, 5.53% yield) and tert-butyl N-[3-ethyl-5-[[2-[(2R,5S)-5-methyl-2-(1H-thieno[3,2-c]pyrazol-5-yl)-1-piperidyl]-2-oxo-acetyl]amino]-2-pyridyl]carbamate (34 mg, 66.33 µmol, 5.87% yield) were obtained.

Ret time for E1 in analytical conditions (column: IB, Hexane-IPA-MeOH, 80-10-10, 0.6 ml/min as mobile phase) 27.65 min and for E2 24.09 min.

E1: Retention time: 27.65 min

LCMS(ESI): [M]+ m/z: calcd 512.2; found 513.2; Rt=3.142 min.

E2: Retention time: 24.09 min

LCMS(ESI): [M]+ m/z: calcd 512.2; found 513.2; Rt=3.202 min.

Step 2: Synthesis of N-(6-amino-5-ethylpyridin-3-yl)-2-(5-methyl-2-(1H-thieno[3,2-c]pyrazol-5-yl)piperidin-1-yl)-2-oxoacetamide (Compound 955 and Compound 967 tert-butyl N-[3-ethyl-5-[[2-[(2S,5R)-5-methyl-2-(1H-thieno[3,2-c]pyrazol-5-yl)-1-piperidyl]-2-oxo-acetyl]amino]-2-pyridyl]carbamate (32 mg, 62.42 µmol) and tert-butyl N-[3-ethyl-5-[[2-[(2R,5S)-5-methyl-2-(1H-thieno[3,2-c]pyrazol-5-yl)-1-piperidyl]-2-oxo-acetyl]amino]-2-pyridyl]carbamate (32 mg, 62.42 µmol) were dissolved in dioxane (2 mL) and H₂O (0.5 mL). Obtained solution was stirred at 100° C. for 3 hr; after the reaction was complete, the mixture was subjected to HPLC (22% 0.5-6.5 min water-MeCN; flow 30 ml/min (loading pump 4 ml/min MeCN); target mass 412; column SunFire 100×19 mm 5 um (R)) to give N-(6-amino-5-ethyl-3-pyridyl)-2-[(2S,5R)-5-methyl-2-(1H-thieno[3,2-c]pyrazol-5-yl)-1-piperidyl]-2-oxo-acetamide (15 mg, 36.36 µmol, 58.25% yield) and N-(6-amino-5-ethyl-3-pyridyl)-2-[(2R,5S)-5-methyl-2-(1H-thieno[3,2-c]pyrazol-5-yl)-1-piperidyl]-2-oxo-acetamide (15 mg, 36.36 µmol, 58.25% yield).

Compound 955: ¹H NMR (600 MHz, DMSO-d₆) δ (ppm) 0.95-1.02 (m, 3H), 1.04-1.14 (m, 3H), 1.36-1.47 (m, 1H), 1.80-1.97 (m, 2H), 2.01-2.20 (m, 2H), 2.39 (q, 2H), 2.92-3.40 (m, 1H), 3.44-4.08 (m, 1H), 5.43-5.87 (m, 3H), 6.99-7.12 (m, 1H), 7.42-7.53 (m, 1H), 7.59-7.93 (m, 1H), 8.02-8.09 (m, 1H), 10.52 (s, 1H), 13.03 (s, 1H).

LCMS(ESI): [M]⁺ m/z: calcd 412.2; found 413.2; Rt=1.018 min.

Compound 967: ¹H NMR (600 MHz, DMSO-d₆) δ (ppm) 0.80-1.01 (m, 3H), 1.06-1.12 (m, 3H), 1.37-1.45 (m, 1H), 1.82-1.97 (m, 2H), 2.02-2.20 (m, 2H), 2.39 (q, 2H), 2.91-3.40 (m, 1H), 3.76 (dd, 1H), 5.46-5.83 (m, 3H), 6.95-7.09 (m, 1H), 7.42-7.53 (m, 1H), 7.59-7.98 (m, 1H), 7.98-8.09 (m, 1H), 10.52 (s, 1H), 12.88-13.41 (m, 1H).

LCMS(ESI): [M]⁺ m/z: calcd 412.2; found 413.2; Rt=1.442 min.

Example 382. The Synthesis of N-(6-amino-5-methylpyridin-3-yl)-2-(5-methyl-2-(1H-thieno[2,3-c]pyrazol-5-yl)piperidin-1-yl)-2-oxoacetamide (Compound 815, Compound 1085 and Compound 1086

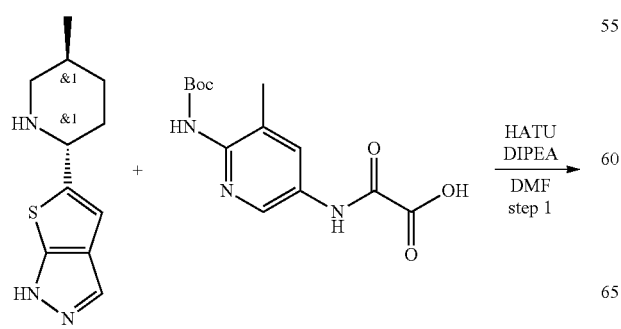

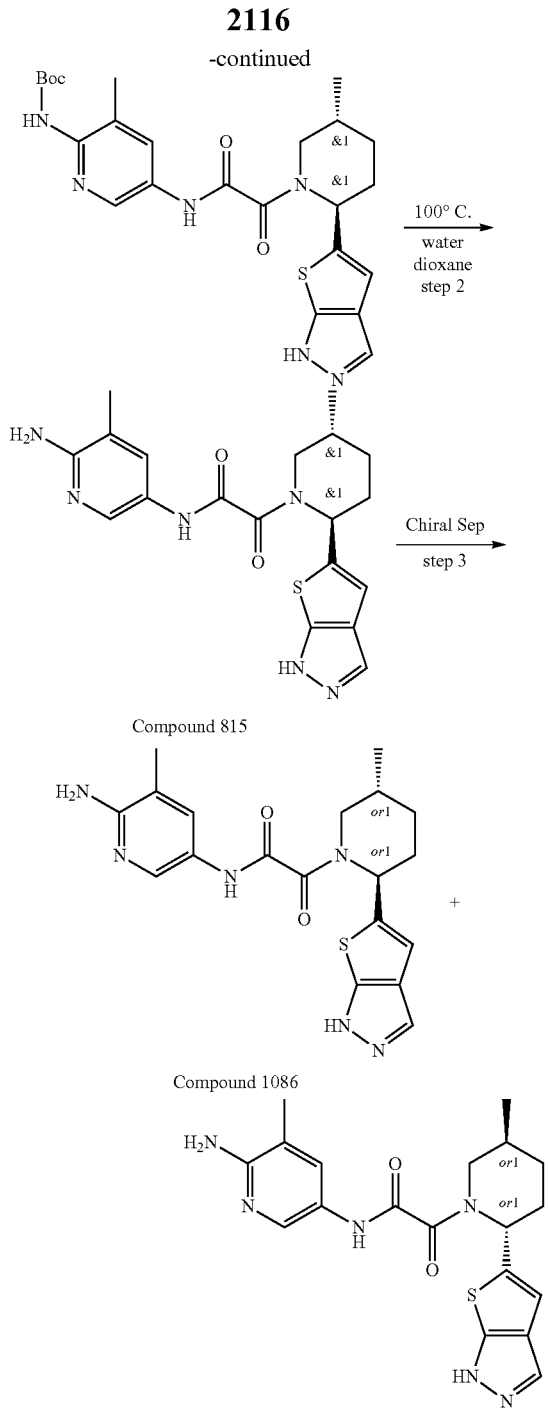

Step 1: Synthesis of rac-tert-butyl (3-methyl-5-(2-((2R,5S)-5-methyl-2-(1H-thieno[2,3-c]pyrazol-5-yl)piperidin-1-yl)-2-oxoacetamido)pyridin-2-yl)carbamate 2-[[6-(tert-butoxycarbonylamino)-5-methyl-3-pyridyl]amino]-2-oxo-acetic acid (401.32 mg, 1.36 mmol), 5-[(2S,5R)-5-methyl-2-piperidyl]-2H-thieno[2,3-c]pyrazole (300.79 mg, 1.36 mmol) and DIPEA (526.94 mg, 4.08 mmol, 710.16 µL) were dissolved in DMSO (6 mL) under gentle heating. HATU (620.11 mg, 1.63 mmol) was added in small portions under vigorous stirring and occasional heating. After the reaction was complete, the mixture was purified by HPLC (40-90% 0.5-6.5 min water-MeOH; flow 30 ml/min; (loading pump 4 ml/min MeOH); target mass 498; column SunFire C18 100×19 mm 5 um (L)) to give tert-butyl N-[3-methyl-5-[[2-[(2S,5R)-5-methyl-2-(1H-thieno[2,3-c]pyrazol-5-yl)-1-piperidyl]-2-oxo-acetyl]amino]-2-pyridyl]carbamate (80 mg, 160.45 μmol, 11.81% yield).

LCMS(ESI): [M]+ m/z: calcd 498.2; found 499.2; Rt=2.857 min.

Step 2: Synthesis of N-(6-amino-5-methylpyridin-3-yl)-2-(5-methyl-2-(1H-thieno[2,3-c]pyrazol-5-yl)piperidin-1-yl)-2-oxoacetamide (Compound 815 tert-butyl N-[3-methyl-5-[[2-[(2S,5R)-5-methyl-2-(1H-thieno[2,3-c]pyrazol-5-yl)-1-piperidyl]-2-oxo-acetyl]amino]-2-pyridyl]carbamate (80 mg, 160.45 μmol) was dissolved in dioxane (2 mL) and water (0.5 mL). Obtained solution was stirred at 100° C. for 2 hr; after the reaction was complete, the mixture was subjected to HPLC (18% 0.5-6.5 min water-MeCN; flow 30 ml/min (loading pump 4 ml/min MeCN); target mass 398; column SunFire C18 100×19 mm 5 um (R)) to give N-(6-amino-5-methyl-3-pyridyl)-2-[(2S,5R)-5-methyl-2-(1H-thieno[2,3-c]pyrazol-5-yl)-1-piperidyl]-2-oxo-acetamide (40 mg, 100.38 μmol, 62.56% yield).

Compound 815: $^1$H NMR (600 MHz, DMSO-$d_6$) δ (ppm) 0.98 (d, 3H), 1.37-1.48 (m, 1H), 1.83-1.96 (m, 2H), 1.98-2.02 (m, 3H), 2.02-2.17 (m, 2H), 2.91-2.96 (m, 0.4H), 3.34-3.39 (m, 0.6H), 3.44-4.08 (m, 1H), 5.40-5.81 (m, 3H), 6.88-6.98 (m, 1H), 7.46-7.51 (m, 1H), 7.87-8.00 (m, 1H), 8.01 (s, 1H), 10.42-10.64 (m, 1H), 13.29 (s, 1H).

LCMS(ESI): [M]+ m/z: calcd 398.2; found 399.2; Rt=1.722 min.

Step 3: Chiral Separation (Compound 1085 and Compound 1086

Racemate was purification with chiral HPLC (Chiralpak IA (250*20, 5 mkm), Hexane-IPA-MeOH, 50-25-25, 12 ml/min) results in N-(6-amino-5-methyl-3-pyridyl)-2-[(2R,5S)-5-methyl-2-(1H-thieno[2,3-c]pyrazol-5-yl)-1-piperidyl]-2-oxo-acetamide (8 mg, 20.08 μmol, 25.02% yield) and N-(6-amino-5-methyl-3-pyridyl)-2-[(2S,5R)-5-methyl-2-(1H-thieno[2,3-c]pyrazol-5-yl)-1-piperidyl]-2-oxo-acetamide (8 mg, 20.08 μmol, 25.02% yield).

Ret time for Compound 1085 in analytical conditions (column: IA, Hexane-IPA-MeOH, 50-25-25, 0.6 ml/min as mobile phase) 65.80 min and for Compound 1086 43.62 min.

Compound 1085: Retention time: 65.80 min
$^1$H NMR (600 MHz, DMSO-$d_6$) δ (ppm) 0.96-1.03 (m, 3H), 1.39-1.44 (m, 1H), 1.86-1.96 (m, 2H), 1.99-2.03 (m, 3H), 2.04-2.19 (m, 2H), 2.90-3.40 (m, 1H), 3.45-4.09 (m, 1H), 5.39-5.81 (m, 3H), 6.89-7.00 (m, 1H), 7.49 (s, 1H), 7.95 (s, 1H), 7.99-8.05 (m, 1H), 10.43-10.53 (m, 1H), 13.29 (s, 1H).

LCMS(ESI): [M]+ m/z: calcd 398.2; found 399.2; Rt=0.803 min.

Compound 1086: Retention time: 43.62 min
$^1$H NMR (600 MHz, DMSO-$d_6$) δ (ppm) 0.97-1.03 (m, 3H), 1.38-1.45 (m, 1H), 1.84-1.97 (m, 2H), 1.99-2.18 (m, 5H), 2.91-3.40 (m, 1H), 3.44-4.07 (m, 1H), 5.41-5.60 (m, 1H), 5.61-5.79 (m, 2H), 6.87-6.97 (m, 1H), 7.45-7.52 (m, 1H), 7.89-7.97 (m, 1H), 8.02 (d, 1H), 10.43-10.52 (m, 1H), 13.29 (s, 1H).

LCMS(ESI): [M]+ m/z: calcd 398.2; found 399.2; Rt=0.803 min.

Example 383. The Synthesis of N-(6-amino-5-ethylpyridin-3-yl)-2-(5-methyl-2-(1H-thieno[2,3-c]pyrazol-5-yl)piperidin-1-yl)-2-oxoacetamide (Compound 1055 and Compound 1075

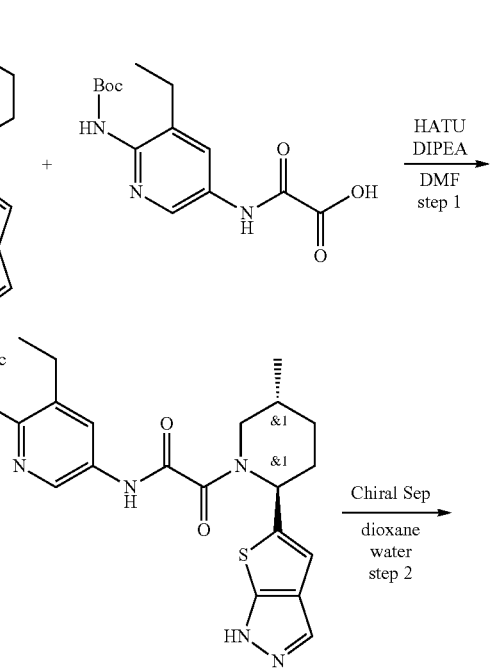

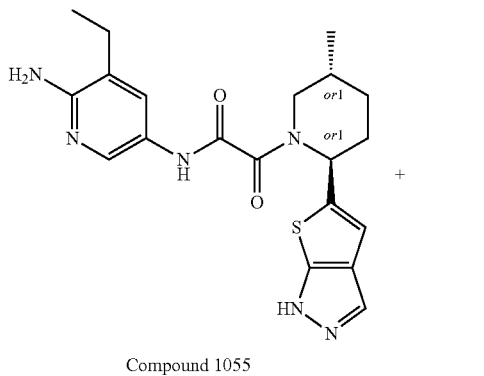

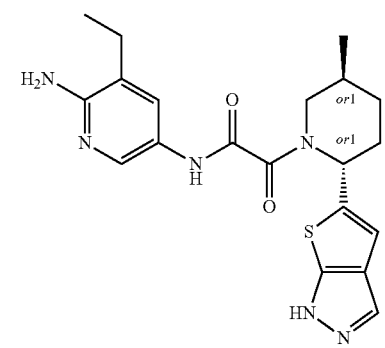

Compound 1055

Compound 1075

Step 1: Synthesis of rac-tert-butyl (3-ethyl-5-(2-((2R,5S)-5-methyl-2-(1H-thieno[2,3-c]pyrazol-5-yl)piperidin-1-yl)-2-oxoacetamido)pyridin-2-yl)carbamate 2-[[6-(tert-butoxycarbonylamino)-5-ethyl-3-pyridyl]amino]-2-oxo-acetic acid (419.28 mg, 1.36 mmol), 5-[(2R,5S)-5-methyl-2-piperidyl]-1H-thieno[3,2-c]pyrazole (0.3 g, 1.36 mmol) and HATU (566.94 mg, 1.49 mmol) were dissolved in DMSO (10 mL) under gentle heating. DIPEA (613.14 mg, 4.74 mmol, 826.34 μL) was added in small portions under vigorous stirring and occasional heating. After the reaction was complete, the mixture was purified by HPLC (37-39-56-70% 0.5-4.5-4.6-8 min water-MeCN; flow 30 ml/min (loading pump 4 ml/min MeCN); target mass 512; column SunFire C18 100×19 mm 5 um (R)) to give tert-butyl N-[3-ethyl-5-[[2-[(2R,5S)-5-methyl-2-(1H-thieno[2,3-c]pyrazol-5-yl)-1-piperidyl]-2-oxo-acetyl]amino]-2-pyridyl]carbamate (33 mg, 64.37 μmol, 4.75% yield) and tert-butyl N-[5-[[2-[(2R,5S)-2-(2-tert-butylthieno[2,3-c]pyrazol-5-yl)-5-methyl-1-piperidyl]-2-oxo-acetyl]amino]-3-ethyl-2-pyridyl]carbamate (190 mg, 334.08 μmol, 24.65% yield). Structure of the second product was approved by 2D-NMR spectroscopy. tert-butyl N-[3-ethyl-5-[[2-[(2R,5S)-5-methyl-2-(1H-thieno[2,3-c]pyrazol-5-yl)-1-piperidyl]-2-oxo-acetyl]amino]-2-pyridyl]carbamate (33 mg, 64.37 μmol, 4.75% yield).

LCMS(ESI): [M]$^+$ m/z: calcd 512.2; found 513.2; Rt=3.221 min.

Step 2: Synthesis of N-(6-amino-5-ethylpyridin-3-yl)-2-(5-methyl-2-(1H-thieno[2,3-c]pyrazol-5-yl)piperidin-1-yl)-2-oxoacetamide (Compound 1055 and Compound 1075 tert-butyl N-[3-ethyl-5-[[2-[(2R,5S)-5-methyl-2-(1H-thieno[2,3-c]pyrazol-5-yl)-1-piperidyl]-2-oxo-acetyl]amino]-2-pyridyl]carbamate (41.13 mg, 80.23 μmol) was dissolved in dioxane (3 mL)/water (0.5 mL) mixture and stirred at reflux overnight. Aliquot shows the full consumption of the starting material; evaporation of the solvents under reduced pressure and purification with chiral HPLC (Chiralpak IA (250*20, 5 mkm), Hexane-IPA-MeOH, 50-25-25, 14 ml/min) results in N-(6-amino-5-ethyl-3-pyridyl)-2-[(2R,5S)-5-methyl-2-(1H-thieno[2,3-c]pyrazol-5-yl)-1-piperidyl]-2-oxo-acetamide (9 mg, 21.82 μmol, 27.20% yield) and N-(6-amino-5-ethyl-3-pyridyl)-2-[(2S,5R)-5-methyl-2-(1H-thieno[2,3-c]pyrazol-5-yl)-1-piperidyl]-2-oxo-acetamide (7 mg, 16.97 μmol, 21.15% yield).

Ret time for Compound 1055 in analytical conditions (column: IA, Hexane-IPA-MeOH, 50-25-25, 0.6 ml/min as mobile phase) 33.52 min and for Compound 1075 50.94 min.

Compound 1055: Retention time: 33.52 min
$^1$H NMR (600 MHz, DMSO-d$_6$) δ (ppm) 1.00 (d, 3H), 1.07-1.13 (m, 3H), 1.38-1.48 (m, 1H), 1.88-1.99 (m, 2H), 2.02-2.06 (m, 1H), 2.06-2.19 (m, 1H), 2.38-2.43 (m, 2H), 2.93-2.98 (m, 0.3H), 3.35-3.39 (m, 0.7H), 3.44-4.10 (m, 1H), 5.43-5.63 (m, 1H), 5.63-5.79 (m, 2H), 6.91-6.96 (m, 1H), 7.47-7.53 (m, 1H), 7.91-7.98 (m, 1H), 8.05 (s, 1H), 10.47-10.54 (m, 1H), 13.29 (s, 1H).

LCMS(ESI): [M]$^+$ m/z: calcd 412.2; found 413.2; Rt=0.838 min.

Compound 1075: Retention time: 50.94 min
$^1$H NMR (600 MHz, DMSO-d$_6$) δ (ppm) 0.96-1.02 (m, 3H), 1.08-1.15 (m, 3H), 1.39-1.46 (m, 1H), 1.85-1.97 (m, 2H), 2.02-2.17 (m, 2H), 2.37-2.43 (m, 2H), 2.93-2.98 (m, 0.3H), 3.36-3.39 (m, 0.7H), 3.48-4.11 (m, 1H), 5.41-5.63 (m, 1H), 5.63-5.81 (m, 2H), 6.90-7.00 (m, 1H), 7.46-7.58 (m, 1H), 7.88-8.13 (m, 2H), 10.44-10.57 (m, 1H), 13.30 (s, 1H).

LCMS(ESI): [M]$^+$ m/z: calcd 412.2; found 413.2; Rt=0.837 min.

Example 384. The Synthesis of N-(6-amino-5-methylpyridin-3-yl)-2-(5-methyl-2-(1H-pyrazol-3-yl)piperidin-1-yl)-2-oxoacetamide (Compound 1071 and Compound 1050

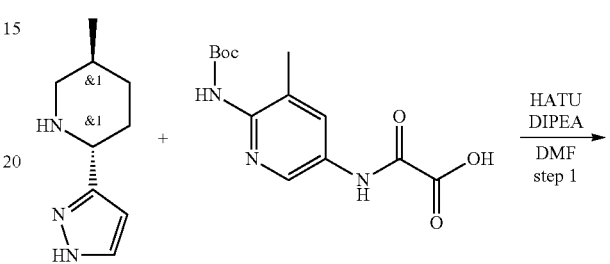

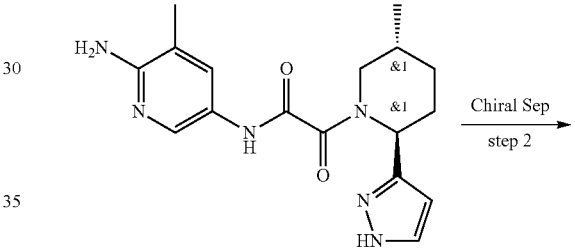

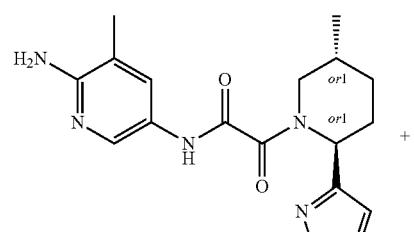

Compound 1050

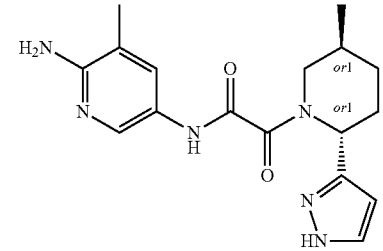

Compound 1071

Step 1: Synthesis of N-(6-amino-5-methylpyridin-3-yl)-2-(5-methyl-2-(1H-pyrazol-3-yl)piperidin-1-yl)-2-oxoacetamide HATU (1.10 g, 2.89 mmol) was added in small portions over 0.5 hr period to a stirred mixture of (2R,5S)-5-methyl-2-(1H-pyrazol-3-yl)piperidine (530 mg, 2.63 mmol, HCl), 2-[(6-amino-5-methyl-3-pyridyl)amino]-2-oxo-acetic acid (589.79 mg, 3.02 mmol) and TEA (1.60 g, 15.77 mmol, 2.20 mL) in DMF (5 mL) at 25° C. The resulting mixture was stirred at 25° C. for 18 hr and then submitted to reverse phase HPLC (column: YMC Triart C18 100×20 mm, 5 um; mobile phase: 35-50% 0-5 min H₂O/MeOH/0.1% NH₄OH, flow: 30 ml/min (loading pump 4 ml/min MeOH) to afford 430 mg of crude product, which was purified by reverse phase HPLC (column: YMC Triart C18 100×20 mm, 5 um; mobile phase: 35-40% 0-5 min H₂O/MeOH/0.1% NH₄OH, flow: 30 ml/min (loading pump 4 ml/min MeOH) to afford N-(6-amino-5-methyl-3-pyridyl)-2-[(2R,5S)-5-methyl-2-(1H-pyrazol-3-yl)-1-piperidyl]-2-oxo-acetamide (200 mg, 584.12 µmol, 22.23% yield) as light-yellow gum, which was directly submitted to preparative chiral HPLC.

LCMS(ESI): [M]⁺ m/z: calcd 342.2; found 343.2; Rt=1.020 min.

Step 2: Chiral Separation (Compound 1071 and Compound 1050

Racemic N-(6-amino-5-methyl-3-pyridyl)-2-[(2R,5S)-5-methyl-2-(1H-pyrazol-3-yl)-1-piperidyl]-2-oxo-acetamide (200 mg, 584.12 µmol) was submitted to preparative chiral HPLC (column: Chiralpak IC-II (250*20, 5 mkm); mobile phase: Hexane-IPA-MeOH; flow rate: 70-15-15, 12 ml/min; Column Temperature: 24° C.; Wavelength: 205 nm, 215 nm, 254 nm) to afford Compound 1050 N-(6-amino-5-methyl-3-pyridyl)-2-[(2S,5R)-5-methyl-2-(1H-pyrazol-3-yl)-1-piperidyl]-2-oxo-acetamide (38 mg, 110.98 µmol, 19.00% yield) (RT=37.07 min); and Compound 1071 N-(6-amino-5-methyl-3-pyridyl)-2-[(2R,5S)-5-methyl-2-(1H-pyrazol-3-yl)-1-piperidyl]-2-oxo-acetamide (13.8 mg, 40.30 µmol, 6.90% yield) (RT=48.1 min).

Ret time for Compound 1071 in analytical conditions (column: IC, Hexane-IPA-MeOH, 70-15-15, 0.6 ml/min as mobile phase) 46.80 min and for Compound 1050 37.45 min.

Compound 1071: Retention time: 46.80 min
¹H NMR (600 MHz, DMSO-d₆) δ (ppm) 0.75-1.02 (m, 3H), 1.25-1.40 (m, 1H), 1.51-1.68 (m, 1H), 1.78-1.87 (m, 1H), 1.88-1.97 (m, 1H), 1.99-2.04 (m, 3H), 2.11-2.32 (m, 1H), 2.69-3.22 (m, 1H), 3.42-4.21 (m, 1H), 5.14-5.66 (m, 3H), 6.10-6.25 (m, 1H), 7.21-7.49 (m, 1H), 7.68 (s, 1H), 7.96-8.03 (m, 1H), 10.36-10.49 (m, 1H), 12.60-12.72 (m, 1H).

LCMS(ESI): [M]⁺ m/z: calcd 342.2; found 343.2; Rt=1.854 min.

Compound 1050: Retention time: 37.45 min
¹H NMR (600 MHz, DMSO-d₆) δ (ppm) 0.72-0.96 (m, 3H), 1.33 (d, 1H), 1.52-1.62 (m, 1H), 1.67-1.94 (m, 2H), 1.99-2.04 (m, 3H), 2.07-2.27 (m, 1H), 2.73-3.20 (m, 1H), 3.42-4.20 (m, 1H), 5.14-5.64 (m, 3H), 6.10-6.23 (m, 1H), 7.46-7.51 (m, 1H), 7.68 (br s, 1H), 7.97-8.03 (m, 1H), 10.36-10.46 (m, 1H), 12.66 (br s, 1H).

LCMS(ESI): [M]⁺ m/z: calcd 342.2; found 343.2; Rt=1.859 min.

Example 385. The Synthesis of 2-(2-(1'H-[1,3'-bipyrazol]-3-yl)-5-methylpiperidin-1-yl)-N-(6-amino-5-methylpyridin-3-yl)-2-oxoacetamide (Compound 715, Compound 789 and Compound 782

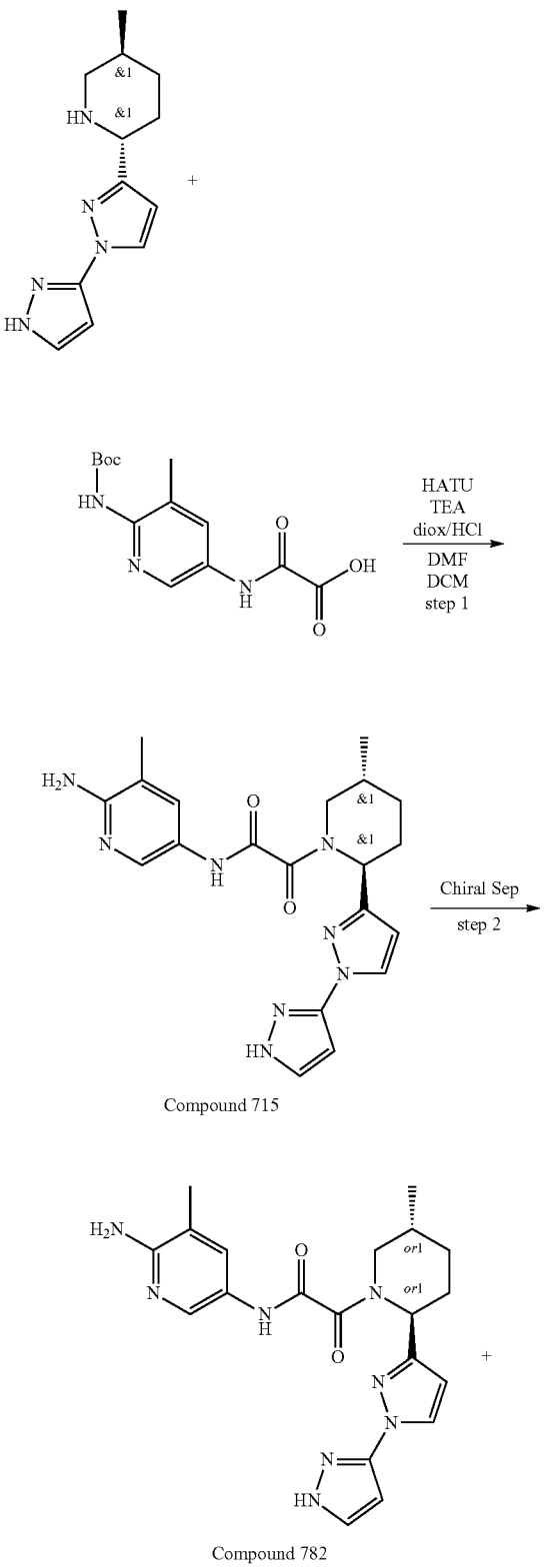

Compound 715

Compound 782

2123

-continued

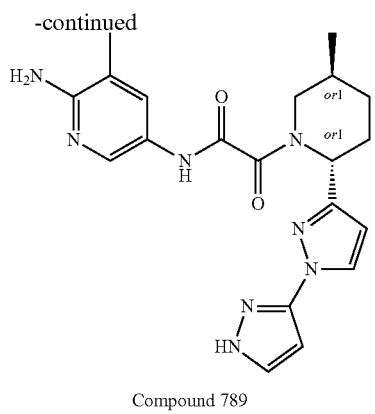

Compound 789

Step 1: Synthesis of 2-(2-(1'H-[1,3'-bipyrazol]-3-yl)-5-methylpiperidin-1-yl)-N-(6-amino-5-methylpyridin-3-yl)-2-oxoacetamide (Compound 715

HATU (718.21 mg, 1.89 mmol) was added in small portions over 0.5 hr period to a stirred mixture of (2R,5S)-5-methyl-2-[1-(1H-pyrazol-3-yl)pyrazol-3-yl]piperidine (900 mg, 1.72 mmol, 3HCl), 2-[[6-(tert-butoxycarbonylamino)-5-methyl-3-pyridyl]amino]-2-oxo-acetic acid (507.06 mg, 1.72 mmol) and TEA (1.74 g, 17.17 mmol, 2.39 mL) in DMF (10 mL) at 25° C. The resulting mixture was stirred at 25° C. for 18 hr, and then concentrated in vacuum. The residue was dissolved in DCM (10 mL) and hydrogen chloride solution 4.0 M in dioxane (15.75 g, 60.04 mmol, 15 mL, 13.9% purity) was added in one portion. The resulting mixture was stirred at 25° C. for 3 hr, and then concentrated in vacuum. The residue was twice purified by reverse phase HPLC (column: YMC Triart C18 100×20 mm, 5 um) mobile phase: 30-30-80% 0-1-6 min $H_2O$/MeOH/0.1% $NH_3$, flow: 30 ml/min (loading pump 4 ml/min MeOH) for 1st HPLC and 30-30-60% 0-1-6 min $H_2O$/MeOH/0.1% $NH_3$, flow: 30 ml/min (loading pump 4 ml/min MeOH) for 2nd HPLC to afford Compound 715 N-(6-amino-5-methyl-3-pyridyl)-2-[(2R,5S)-5-methyl-2-[1-(1H-pyrazol-3-yl)pyrazol-3-yl]-1-piperidyl]-2-oxo-acetamide (112 mg, 274.20 μmol, 15.97% yield) as white solid.

Compound 715: $^1$H NMR (600 MHz, DMSO-$d_6$) δ (ppm) 1.00 (d, 3H), 1.37 (m, 1H), 1.85 (m, 1H), 1.93 (m, 1H), 2.00 (m, 4H), 2.16 (m, 1H), 2.87 (m, 1H), 3.74 (m, 1H), 5.61 (m, 3H), 6.38 (m, 2H), 7.48 (s, 1H), 7.78 (m, 1H), 8.00 (m, 1H), 8.16 (d, 1H), 10.43 (s, 1H), 12.77 (s, 1H).

LCMS(ESI): [M]$^+$ m/z: calcd 408.2; found 409.2; Rt=1.753 min.

Step 2: Chiral Separation (Compound 789 and Compound 782

N-(6-amino-5-methyl-3-pyridyl)-2-[(2S,5R)-5-methyl-2-[1-(1H-pyrazol-5-yl)pyrazol-3-yl]-1-piperidyl]-2-oxo-acetamide (89.8 mg, 219.85 μmol) was chirally separated using Chiralcel OJ-H (250*20, 5 mkm) column, Hexane-IPA-MeOH, 60-20-20 as a mobile phase; Flow rate: 12 ml/min. 24° C., Wavelength: 205 nm, 210 nm affording Compound 782—N-(6-amino-5-methyl-3-pyridyl)-2-[(2S,5R)-5-methyl-2-[1-(1H-pyrazol-5-yl)pyrazol-3-yl]-1-piperidyl]-2-oxo-acetamide (26.64 mg, 65.22 μmol, 29.67% yield) (RT=14.5 min) as an yellow gum and Compound 789—N-(6-amino-5-methyl-3-pyridyl)-2-[(2R,5S)-5-methyl-2-[1-(1H-pyrazol-5-yl)pyrazol-3-yl]-1-piperidyl]-2-oxo-acetamide (RT=22.2 min) as a beige solid.

Ret time for Compound 789 in analytical conditions (column: OJ-H, Hexane-IPA-MeOH, 60-20-20, 0.6 ml/min as mobile phase) 28.28 min and for Compound 782 16.98 min.

Compound 789: Retention time: 28.28 min $^1$H NMR (600 MHz, DMSO-$d_6$) δ (ppm) 0.99-1.01 (m, 3H), 1.34-1.42 (m, 1H), 1.81-1.87 (m, 1H), 1.90-1.95 (m, 1H), 1.96-2.10 (m, 4H), 2.13-2.19 (m, 1H), 2.85-2.89 (m, 0.4H), 3.33-3.38 (m, 0.6H), 3.43-4.06 (m, 1H), 5.21-5.24 (m, 0.4H), 5.57-5.62 (m, 2H), 5.64-5.68 (m, 0.6H), 6.33-6.45 (m, 2H), 7.47-7.49 (m, 1H), 7.76-7.81 (m, 1H), 7.99-8.02 (m, 1H), 8.14-8.20 (m, 1H), 10.44 (s, 1H), 12.77 (s, 1H).

LCMS(ESI): [M]$^+$ m/z: calcd 408.2; found 409.2; Rt=1.722 min.

Compound 782: Retention time: 16.98 min $^1$H NMR (600 MHz, DMSO-$d_6$) δ (ppm) 0.98-1.01 (m, 3H), 1.34-1.41 (m, 1H), 1.80-1.87 (m, 1H), 1.87-1.95 (m, 1H), 1.95-2.10 (m, 4H), 2.14-2.19 (m, 1H), 2.85-2.89 (m, 0.4H), 3.33-3.38 (m, 0.6H), 3.42-4.05 (m, 1H), 5.57-5.62 (m, 2H), 5.63-5.67 (m, 1H), 6.33-6.44 (m, 2H), 7.48 (d, 1H), 7.78 (d, 1H), 7.96-8.02 (m, 1H), 8.14-8.19 (m, 1H), 10.44 (s, 1H), 12.77 (s, 1H).

LCMS(ESI): [M]$^+$ m/z: calcd 408.2; found 409.2; Rt=1.723 min.

Example 386. The Synthesis of N-(6-amino-5-methyl-3-pyridyl)-2-[(2R,4S)-4-methyl-2-phenyl-1-piperidyl]-2-oxo-acetamide (Compound 640

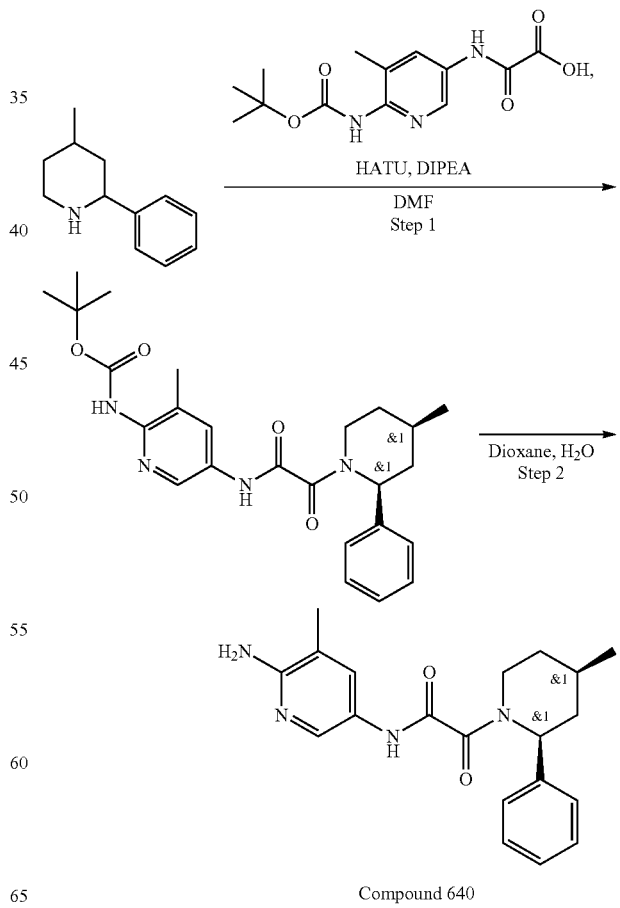

Compound 640

Step 1: Synthesis of tert-butyl N-[3-methyl-5-[[2-(4-methyl-2-phenyl-1-piperidyl)-2-oxo-acetyl]amino]-2-pyridyl]carbamate To a stirred solution of 2-[[6-(tert-butoxycarbonylamino)-5-methyl-3-pyridyl]amino]-2-oxo-acetic acid (0.4 g, 1.35 mmol) and 4-methyl-2-phenyl-piperidine (237.42 mg, 1.35 mmol) in DMF (10 mL) was added DIPEA (525.22 mg, 4.06 mmol, 707.84 µL). The resulting mixture was stirred at 20° C. for 5 minutes. After 5 minutes, HATU (566.56 mg, 1.49 mmol) was added. The resulting reaction mixture was stirred at 20° C. Upon completion, the reaction mixture was concentrated under reduced pressure and the crude product was purified by HPLC to obtain tert-butyl N-[3-methyl-5-[[2-(4-methyl-2-phenyl-1-piperidyl)-2-oxo-acetyl]amino]-2-pyridyl]carbamate (80.5 mg, 177.88 µmol, 13.13% yield) as a yellow solid.

LCMS(ESI): [M+H]$^+$ m/z: calcd 452.3; found 453.4; Rt=3.209 min.

Step 2: Synthesis of N-(6-amino-5-methyl-3-pyridyl)-2-[(2R,4S)-4-methyl-2-phenyl-1-piperidyl]-2-oxo-acetamide (Compound 640 tert-butyl N-[3-methyl-5-[[2-(4-methyl-2-phenyl-1-piperidyl)-2-oxo-acetyl]amino]-2-pyridyl]carbamate (38.9 mg, 85.96 µmol) was dissolved in dioxane (2 mL) and water (5 mL). The reaction mixture was then stirred at 100° C. for 17 hours. Upon completion, the resulting suspension was concentrated under reduced pressure. The obtained solid residue was subjected to HPLC purification (Eluent: 60-85% H$_2$O—CH$_3$CN; column: Sunfire C18 20×100 mm, 5 um) to get N-(6-amino-5-methyl-3-pyridyl)-2-[(2R,4S)-4-methyl-2-phenyl-1-piperidyl]-2-oxo-acetamide (Compound 640, 13.7 mg, 38.87 µmol, 45.22% yield) as a light-yellow solid.

$^1$H NMR (DMSO-d$_6$, 600 MHz): δ (ppm) 0.84 (m, 3H), 1.22 (m, 1H), 1.78 (m, 2H), 2.04 (m, 5H), 3.40 (m, 1H), 3.76 (m, 1H), 5.15 (m, 1H), 5.60 (m, 2H), 7.33 (m, 6H), 8.02 (m, 1H), 10.43 (m, 1H).

LCMS(ESI): [M+H]$^+$ m/z: calcd 352.2; found 353.4; Rt=2.251 min.

Example 387. The Synthesis of rac-N-(6-amino-5-methyl-3-pyridyl)-2-[(2S,5R)-5-methyl-2-(7-oxo-6,8-dihydro-5H-1,8-naphthyridin-3-yl)-1-piperidyl]-2-oxo-acetamide (Compound 923

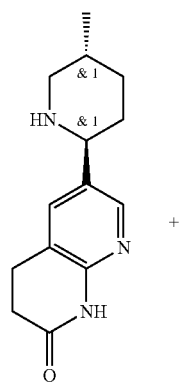
+

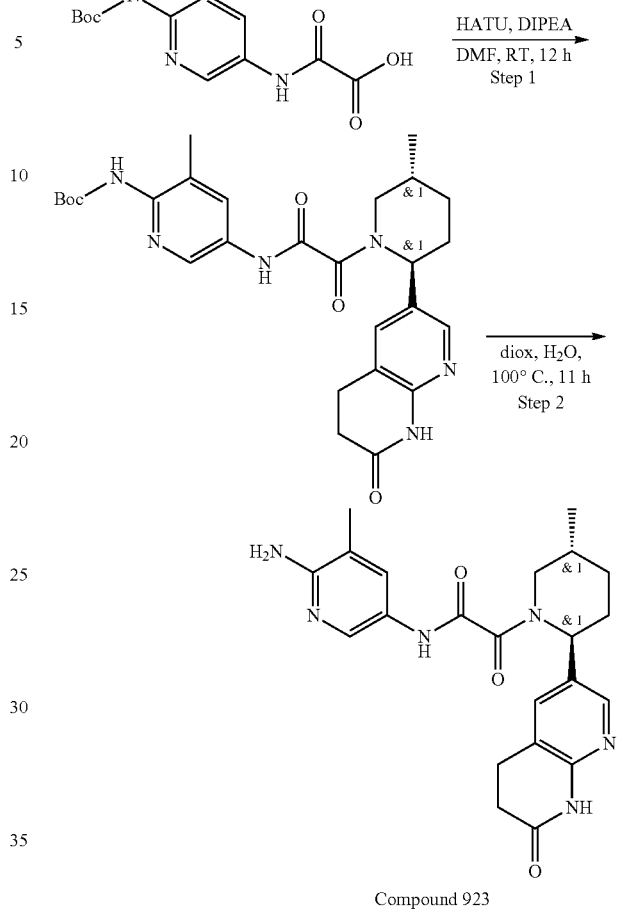

Compound 923

Step 1: The Synthesis of rac-tert-butyl N-[3-methy-5-[[2-[(2S,5R)-5-methy-2-(7-oxo-6,8-dihydro-5H-1,8-naphthyridin-3-yl)-1-piperidyl]-2-oxo-acetyl]amino]-2-pyridyl]carbamate rac-6-[(2S,5R)-5-methyl-2-piperidyl]-3,4-dihydro-1H-1,8-naphthyridin-2-one (300 mg, 1.22 mmol), 2-[[6-(tert-butoxycarbonylamino)-5-methyl-3-pyridyl]amino]-2-oxo-acetic acid (361.11 mg, 1.22 mmol), triethylamine (618.72 mg, 6.11 mmol, 852.24 µL) were mixed in DMF (5 mL) and then HATU (697.47 mg, 1.83 mmol) were added. Resulting mixture were stirred at 25° C. for 12 hr. The solvent was evaporated and the crude precipate was purified by HPLC (2-10 min 20-45% MeCN/H$_2$O 30 mL/min (loading pump 4 mL MeCN) column: SunFire 100*19 mm, 5 microM) to obtain tert-butyl N-[3-methyl-5-[[2-[(2S,5R)-5-methyl-2-(7-oxo-6,8-dihydro-5H-1,8-naphthyridin-3-yl)-1-piperidyl]-2-oxo-acetyl]amino]-2-pyridyl]carbamate (80.8 mg, 154.61 µmol, 12.64% yield).

LCMS(ESI): [M+H]$^+$ m/z: calcd 522.2; found 523.2; Rt=1.178 min.

Step 2: The Synthesis of rac-N-(6-amino-5-methyl-3-pyridyl)-2-[(2S,5R)-5-methyl-2-(7-oxo-6,8-dihydro-5H-1,8-naphthyridin-3-yl)-1-piperidyl]-2-oxo-acetamide (Compound 923

A solution of rac-tert-butyl N-[3-methyl-5-[[2-[(2S,5R)-5-methyl-2-(7-oxo-6,8-dihydro-5H-1,8-naphthyridin-3-yl)-

1-piperidyl]-2-oxo-acetyl]amino]-2-pyridyl]carbamate (80.8 mg, 154.61 µmol) in Dioxane (2 mL) and Water (2 mL) was heated at 100° C. for 11 hr. Solvents were evaporated and resulting precipitate was purified by HPLC (35-55% MeCN/H₂O—2-10 min Flow rate: 30 mL/min; loading pump 4 mL/min MeCN) to obtain rac-N-(6-amino-5-methyl-3-pyridyl)-2-[(2S,5R)-5-methyl-2-(7-oxo-6,8-dihydro-5H-1,8-naphthyridin-3-yl)-1-piperidyl]-2-oxo-acetamide (44.1 mg, 104.38 µmol, 67.51% yield).

¹H NMR (DMSO-d₆, 600 MHz): δ (ppm) 0.99 (m, 3H), 1.33 (m, 1H), 1.68 (m, 1H), 1.87 (m, 1H), 2.00 (m, 4H), 2.18 (m, 1H), 2.41 (m, 2H), 3.04 (m, 3H), 3.70 (dd, 1H), 5.57 (m, 3H), 7.48 (m, 2H), 8.00 (m, 2H), 10.47 (m, 2H).

LCMS(ESI): [M+H]⁺ m/z: calcd 422.2; found 423.2; Rt=0.870 min.

Example 388. The Synthesis of rac-N-(6-amino-5-ethyl-3-pyridyl)-2-[(2S,5R)-5-methyl-2-(7-oxo-6,8-dihydro-5H-1,8-naphthyridin-3-yl)-1-piperidyl]-2-oxo-acetamide (Compound 916

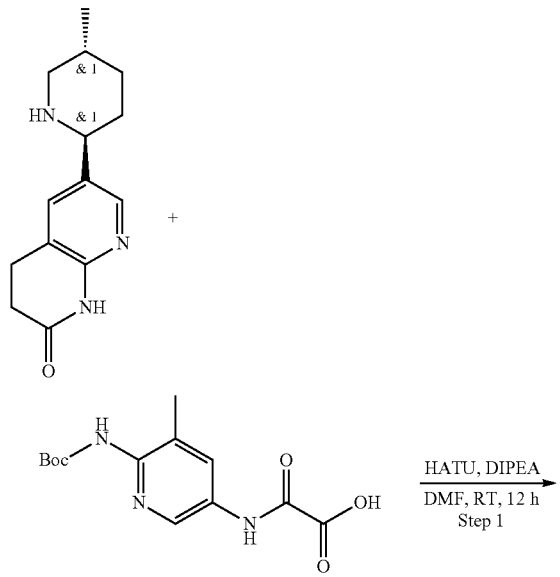

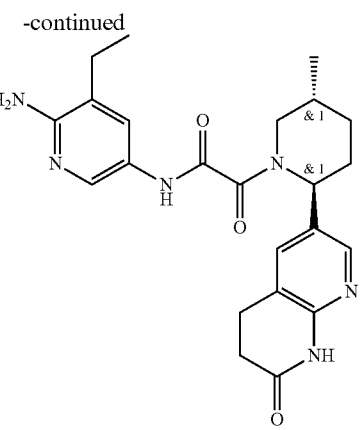

Compound 916

Step 1: The Synthesis of rac-tert-butyl N-[3-ethyl-5-[[2-[(2S,5R)-5-methyl-2-(7-oxo-6,8-dihydro-5H-1,8-naphthyridin-3-yl)-1-piperidyl]-2-oxo-acetyl]amino]-2-pyridyl]carbamate rac-6-[(2S,5R)-5-methyl-2-piperidyl]-3,4-dihydro-1H-1,8-naphthyridin-2-one (300 mg, 1.22 mmol), 2-[[6-(tert-butoxycarbonylamino)-5-ethyl-3-pyridyl]amino]-2-oxo-acetic acid (378.26 mg, 1.22 mmol), triethylamine (618.72 mg, 6.11 mmol, 852.24 µL) were mixed in DMF (5 mL) and then HATU (697.47 mg, 1.83 mmol) were added. Resulting mixture were stirred at 25° C. for 12 hr. The solvent was evaporated and the crude precipitate was purified by HPLC (40-100% 2-10 min; water-acetonitrile 30 mL/min; loading pump acetonitrile 4 mL/min, target mass 536, column SunFire 19*100 mm 5 um) to obtain rac-rert-butyl N-[3-ethyl-5-[[2-[(2S,5R)-5-methyl-2-(7-oxo-6,8-dihydro-5H-1,8-naphthyridin-3-yl)-1-piperidyl]-2-oxo-acetyl]amino]-2-pyridyl]carbamate (62.9 mg, 117.21 µmol, 9.59% yield).

LCMS(ESI): [M+H]⁺ m/z: calcd 536.2; found 537.2; Rt=0.993 min.

Step 2: The Synthesis of rac-N-(6-amino-5-ethyl-3-pyridyl)-2-[(2S,5R)-5-methyl-2-(7-oxo-6,8-dihydro-5H-1,8-naphthyridin-3-yl)-1-piperidyl]-2-oxo-acetamide (Compound 916

A solution of tert-butyl N-[3-ethyl-5-[[2-[(2S,5R)-5-methyl-2-(7-oxo-6,8-dihydro-5H-1,8-naphthyridin-3-yl)-1-piperidyl]-2-oxo-acetyl]amino]-2-pyridyl]carbamate (62.9 mg, 117.21 µmol) in dioxane (2 mL) and water (2 mL) was heated at 100° C. for 12 hr. Solvents were evaporated and resulting precipitate was purified by HPLC (35-55% MeCN-Water 2-10 min Flow rate: 30 mL/min; loading pump 4 mL/min MeCN) to obtain N-(6-amino-5-ethyl-3-pyridyl)-2-[(2S,5R)-5-methyl-2-(7-oxo-6,8-dihydro-5H-1,8-naphthyridin-3-yl)-1-piperidyl]-2-oxo-acetamide (24 mg, 54.98 µmol, 46.91% yield).

¹H NMR (DMSO-d₆, 600 MHz): δ (ppm) 1.05 (m, 6H), 1.33 (m, 1H), 1.69 (m, 1H), 1.87 (m, 1H), 2.00 (m, 1H), 2.16 (m, 1H), 2.38 (m, 3H), 3.01 (m, 4H), 3.70 (m, 1H), 5.59 (m, 3H), 7.49 (m, 2H), 8.01 (m, 2H), 10.48 (m, 2H).

LCMS(ESI): [M+H]⁺ m/z: calcd 436.2; found 437.2; Rt=0.908 min.

Example 389. The Synthesis of N-(6-amino-5-methylpyridin-3-yl)-2-(2-(2-aminobenzo[d]thiazol-5-yl)-5-methylpiperidin-1-yl)-2-oxoacetamide (Compound 997 and Compound 981

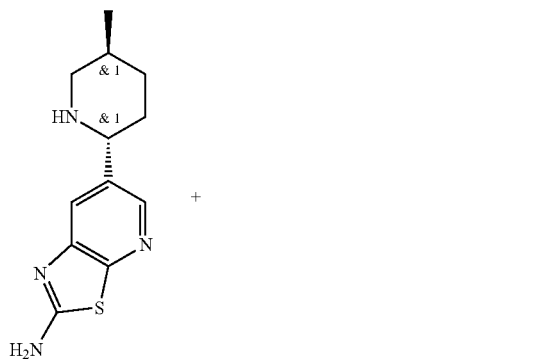

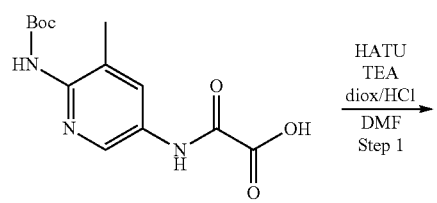

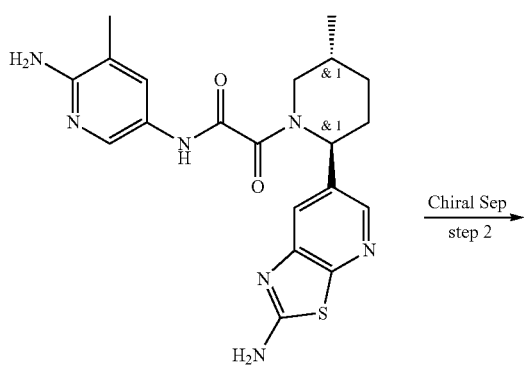

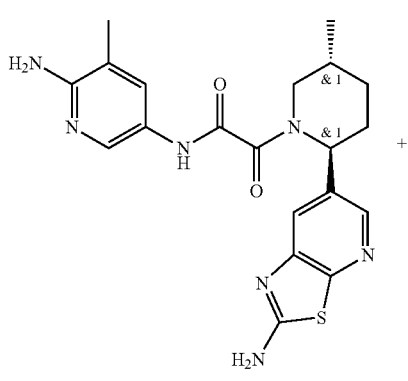

Compound 981

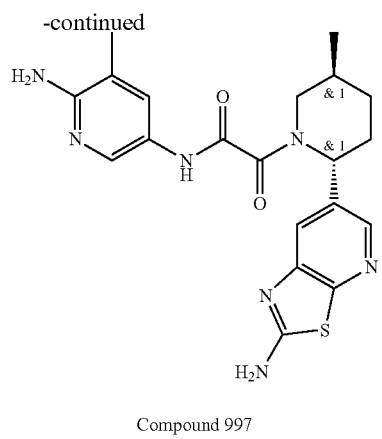

Compound 997

Step 1: Synthesis of N-(6-amino-5-methylpyridin-3-yl)-2-(2-(2-aminobenzo[d]thiazol-5-yl)-5-methylpiperidin-1-yl)-2-oxoacetamide HATU (253.63 mg, 667.05 μmol) was added in small portions over 0.5 hr period to a stirred mixture of 5-[(2R,5S)-5-methyl-2-piperidyl]-1,3-benzothiazol-2-amine (150 mg, 606.41 μmol), 2-[[6-(tert-butoxycarbonylamino)-5-methyl-3-pyridyl]amino]-2-oxo-acetic acid (205.93 mg, 697.37 μmol) and TEA (245.45 mg, 2.43 mmol, 338.08 μL) in DMF (5 mL) at 25° C. The resulting mixture was stirred at 25° C. for 18 hr, and then concentrated in vacuum. The residue was dissolved in DCM (10 mL) and hydrogen chloride solution 4.0 M in dioxane (10.50 g, 40.03 mmol, 10.00 mL, 13.9% purity) was added in one portion. The resulting mixture was stirred at 25° C. for 12 hr, and then concentrated in vacuum. The residue was purified by reverse phase HPLC (column: YMC Triart C18 100×20 mm, 5 um; mobile phase: 40-70% 0-5 min H$_2$O/MeOH/0.1% NH$_4$OH, flow: 30 ml/min (loading pump 4 ml/min MeOH) to afford 2-[(2R,5S)-2-(2-amino-1,3-benzothiazol-5-yl)-5-methyl-1-piperidyl]-N-(6-amino-5-methyl-3-pyridyl)-2-oxo-acetamide (131 mg, 308.59 μmol, 50.89% yield) as light-yellow gum, which was directly submitted to preparative chiral HPLC.

LCMS(ESI): [M]$^+$ m/z: calcd 424.2; found 425.2; Rt=1.719 min.

Step 2: Chiral Separation (Compound 997 and Compound 981

Racemic 2-[(2R,5S)-2-(2-amino-1,3-benzothiazol-5-yl)-5-methyl-1-piperidyl]-N-(6-amino-5-methyl-3-pyridyl)-2-oxo-acetamide (131 mg, 308.59 μmol) was submitted to preparative chiral HPLC (column:Chiralpak IA-II(250*20, 5 mkm); mobile phase: IPA-MeOH, 50-50; flow rate: 9 ml/min; Column Temperature: 24° C.; Wavelength: 205 nm, 215 nm, 254 nm) to afford Compound 981 2-[(2S,5R)-2-(2-amino-1,3-benzothiazol-5-yl)-5-methyl-1-piperidyl]-N-(6-amino-5-methyl-3-pyridyl)-2-oxo-acetamide (57 mg, 134.27 μmol, 43.51% yield) (RT=22.601 min), and crude 2nd fraction (RT=35.267 min), which was repurified by preparative chiral HPLC (column: Chiralpak IC-II(250*20, 5 mkm); mobile phase: Hexane-IPA-MeOH, 60-20-20; flow rate: 12 ml/min; Column Temperature: 24° C.; Wavelength: 205 nm, 215 nm) to afford Compound 997 2-[(2R,5S)-2-(2-amino-1,3-benzothiazol-5-yl)-5-methyl-1-piperidyl]-N-(6-amino-5-methyl-3-pyridyl)-2-oxo-acetamide (51 mg, 120.14 μmol, 38.93% yield) (RT=45.230 min).

Ret time for Compound 997 in analytical conditions (column: IA, IPA-MeOH, 50-50, 0.6 ml/min as mobile phase) 30.40 min and for Compound 981 18.36 min.

Compound 997: Retention time: 30.40 min $^1$H NMR (600 MHz, DMSO-d$_6$) δ (ppm) 0.99-1.02 (m, 3H), 1.27-1.38 (m, 1H), 1.65-1.73 (m, 1H), 1.80-1.91 (m, 1H), 1.95-2.02 (m, 3H), 2.02-2.16 (m, 1H), 2.17-2.27 (m, 1H), 2.74-3.24 (m, 1H), 3.41-4.03 (m, 1H), 5.13-5.58 (m, 1H), 5.58-5.64 (m, 2H), 6.91-7.01 (m, 1H), 7.22-7.30 (m, 1H), 7.39-7.50 (m, 3H), 7.58-7.64 (m, 1H), 7.93-8.03 (m, 1H), 10.39-10.56 (m, 1H).

LCMS(ESI): [M]$^+$ m/z: calcd 424.2; found 425.2; Rt=1.550 min.

Compound 981: Retention time: 18.36 min $^1$H NMR (600 MHz, DMSO-d$_6$) δ (ppm) 0.99-1.03 (m, 3H), 1.27-1.37 (m, 1H), 1.66-1.75 (m, 1H), 1.80-1.91 (m, 1H), 1.96-2.02 (m, 3H), 2.03-2.17 (m, 1H), 2.18-2.28 (m, 1H), 2.73-3.23 (m, 1H), 3.43-4.03 (m, 1H), 5.13-5.57 (m, 1H), 5.58-5.65 (m, 2H), 6.88-7.01 (m, 1H), 7.21-7.31 (m, 1H), 7.40-7.50 (m, 3H), 7.58-7.64 (m, 1H), 7.94-8.03 (m, 1H), 10.39-10.68 (m, 1H).

LCMS(ESI): [M]$^+$ m/z: calcd 424.2; found 425.2; Rt=1.552 min.

Example 390. The Synthesis of rel-N-(6-amino-5-methyl-3-pyridyl)-2-[(2S,5R)-2-(1-hydroxy-6-isoquinolyl)-5-methyl-1-piperidyl]-2-oxo-acetamide (Compound 953) and Rel-N-(6-amino-5-methyl-3-pyridyl)-2-[(2R,5S)-2-(1-hydroxy-6-isoquinolyl)-5-methyl-1-piperidyl]-2-oxo-acetamide (Compound 961

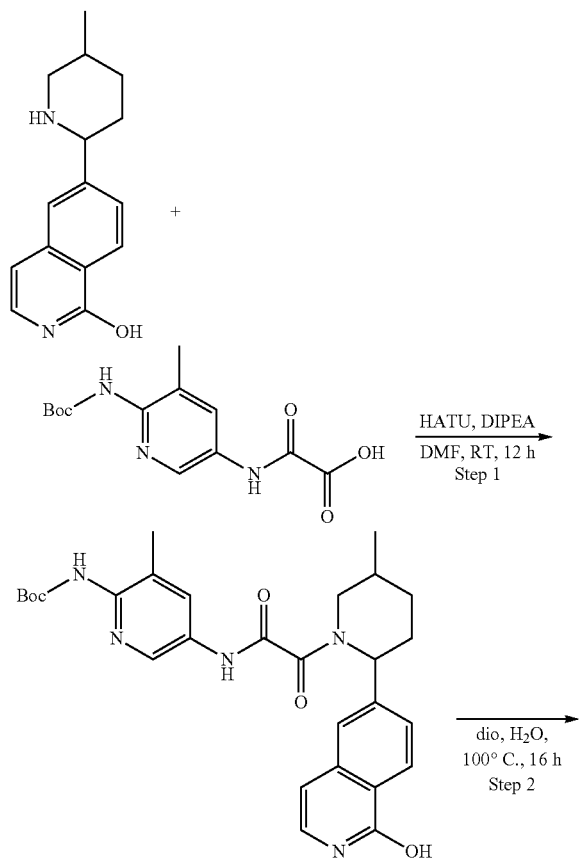

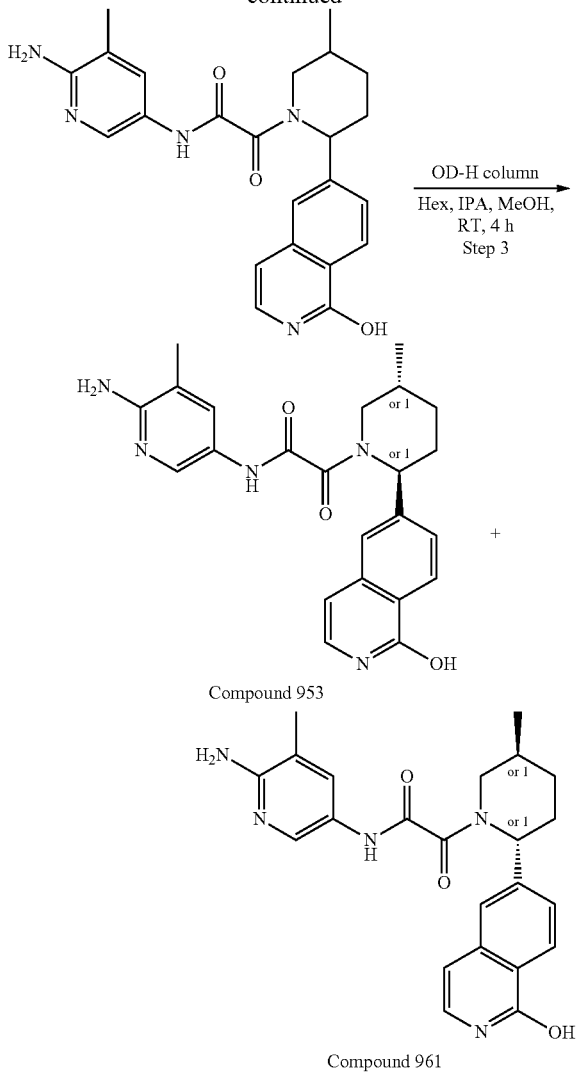

Step 1: The Synthesis of tert-butyl N-[5-[[2-[2-(1-hydroxy-6-isoquinolyl)-5-methyl-1-piperidyl]-2-oxo-acetyl]amino]-3-methyl-2-pyridyl]carbamate DIPEA (133.34 mg, 1.03 mmol, 179.71 µL) was added to the solution of respective 2-[[6-(tert-butoxycarbonylamino)-5-methyl-3-pyridyl]amino]-2-oxo-acetic acid (121.86 mg, 412.69 µmol) and 6-(5-methyl-2-piperidyl)isoquinolin-1-ol (0.1 g, 412.69 µmol) in DMF (5 mL). The resulting mixture was stirred for 5 min followed by the addition of HATU (172.61 mg, 453.95 µmol). Then, the reaction mixture was stirred overnight at room temperature. After the completion of the reaction, monitored by LCMS, the resulting suspension was concentrated under reduced pressure. The obtained solid was subjected to HPLC (Waters Sunfire C18 20*100 5 mkm column and MeCN as an eluent mixture) to afford tert-butyl N-[5-[[2-[2-(1-hydroxy-6-isoquinolyl)-5-methyl-1-piperidyl]-2-oxo-acetyl]amino]-3-methyl-2-pyridyl]carbamate (83.7 mg, 161.09 µmol, 39.03% yield).

LCMS(ESI): [M+H]$^+$ m/z: calcd 519.2; found 520.4; Rt=1.062 min.

Step 2: The Synthesis of N-(6-amino-5-methyl-3-pyridyl)-2-[2-(1-hydroxy-6-Isoquinolyl)-5-methyl-1-piperidyl]-2-oxo-acetamide tert-butyl N-[5-[[2-[2-(1-hydroxy-6-isoquinolyl)-5-methyl-1-piperidyl]-2-oxo-acetyl]amino]-3-methyl-2-pyridyl]carbamate (83.7 mg, 161.09 µmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford N-(6-amino-5-methyl-3-pyridyl)-2-[2-(1-hydroxy-6-isoquinolyl)-5-methyl-1-piperidyl]-2-oxo-acetamide (60.8 mg, 144.94 µmol, 89.98% yield).

LCMS(ESI): [M+H]$^+$ m/z: calcd 419.2; found 420.2; Rt=0.747 min.

Step 3: The Synthesis of rel-N-(6-amino-5-methyl-3-pyridyl)-2-[(2S,5R)-2-(1-hydroxy-6-Isoquinolyl)-5-methyl-1-piperidyl]-2-oxo-acetamide (Compound 953) and rel-N-(6-amino-5-methyl-3-pyridyl)-2-[(2R,5S)-2-(1-hydroxy-6-isoquinolyl)-5-methyl-1-piperidyl]-2-oxo-acetamide (Compound 961

N-(6-amino-5-methyl-3-pyridyl)-2-[2-(1-hydroxy-6-isoquinolyl)-5-methyl-1-piperidyl]-2-oxo-acetamide (60.8 mg, 144.94 µmol) was chirally separated using Chiralcel OD-H 250*20 mm column, Hexane-IPA-MeOH, 50-25-25 as a mobile phase, Floe rate 30 mL/min (Rt1=99.95 min and Rt2=104.3 min) affording Compound 953—rel-N-(6-amino-5-methyl-3-pyridyl)-2-[(2S,5R)-2-(1-hydroxy-6-isoquinolyl)-5-methyl-1-piperidyl]-2-oxo-acetamide (10.55 mg, 17.35% yield) and Compound 961—rel-N-(6-amino-5-methyl-3-pyridyl)-2-[(2R,5S)-2-(1-hydroxy-6-isoquinolyl)-5-methyl-1-piperidyl]-2-oxo-acetamide (18.02 mg, 29.64% yield).

Compound 953: RT (OD-H, Hexane-IPA-MeOH, 50-25-25, 0.6 mL/min)=18.325 min.

$^1$H NMR (600 MHz, DMSO-d$_6$) δ 0.98-1.03 (m, 3H), 1.29-1.39 (m, 1H), 1.61-1.70 (m, 1H), 1.80-1.91 (m, 1H), 1.95-2.03 (m, 3H), 2.06-2.19 (m, 1H), 2.23-2.32 (m, 1H), 2.74-3.14 (m, 1H), 3.47-4.07 (m, 1H), 5.23-5.61 (m, 1H), 5.61-5.69 (m, 2H), 6.49-6.57 (m, 1H), 7.08-7.20 (m, 1H), 7.37-7.50 (m, 2H), 7.52-7.61 (m, 1H), 7.90-8.05 (m, 1H), 8.11-8.18 (m, 1H), 10.47-10.55 (m, 1H), 11.15-11.24 (m, 1H).

LCMS(ESI): [M+H]$^+$ m/z: calcd 419.2; found 420.2; Rt=0.729 min.

Compound 961: RT (OD-H, Hexane-IPA-MeOH, 50-25-25, 0.6 mL/min)=22.983 min.

$^1$H NMR (600 MHz, DMSO-d$_6$) δ 0.98-1.04 (m, 3H), 1.29-1.41 (m, 1H), 1.61-1.70 (m, 1H), 1.82-1.92 (m, 1H), 1.95-2.04 (m, 3H), 2.07-2.21 (m, 1H), 2.23-2.34 (m, 1H), 2.76-3.25 (m, 1H), 3.47-4.07 (m, 1H), 5.19-5.62 (m, 1H), 5.65 (s, 2H), 6.50-6.55 (m, 1H), 7.10-7.18 (m, 1H), 7.36-7.52 (m, 2H), 7.52-7.63 (m, 1H), 7.91-8.07 (m, 1H), 8.10-8.18 (m, 1H), 10.46-10.57 (m, 1H), 11.15-11.22 (m, 1H).

LCMS(ESI): [M+H]$^+$ m/z: calcd 419.2; found 420.2; Rt=0.730 min.

Example 391. Synthesis of N-(6-amino-5-methylpyridin-3-yl)-2-(2-(4-fluorophenyl)-5-methylpiperidin-1-yl-2-d)-2-oxoacetamide Hydrochloride (Compound 1009

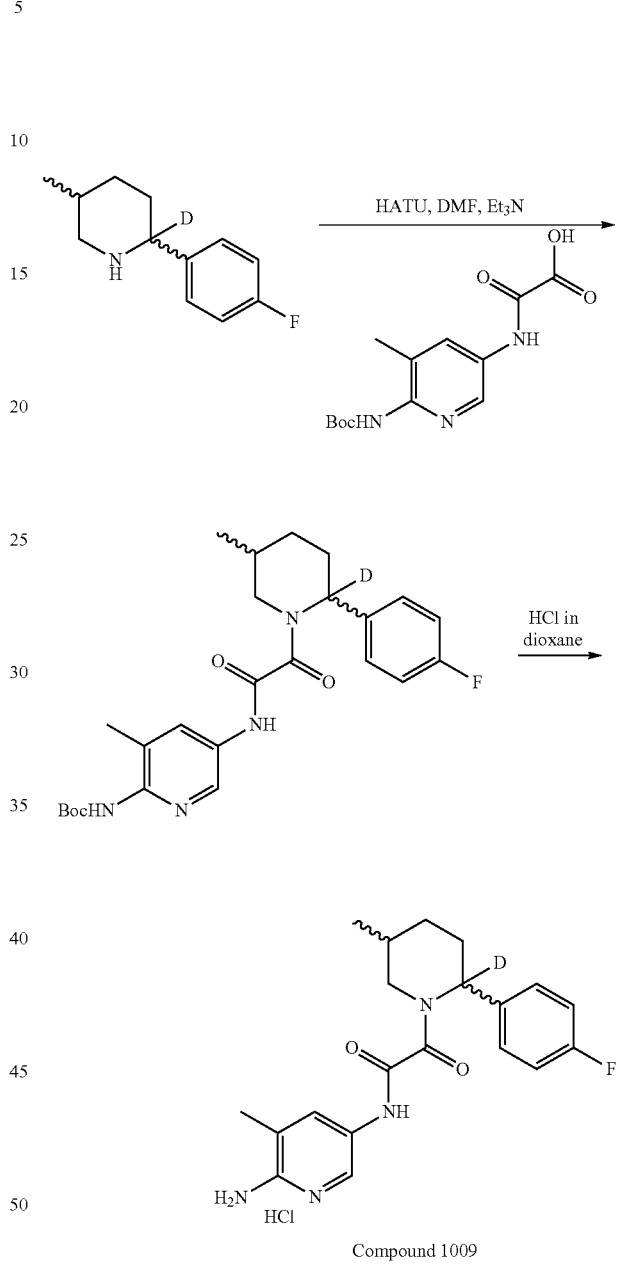

Compound 1009

Step 1: Synthesis of tert-butyl (5-(2-(2-(4-fluorophenyl)-5-methylpiperidin-1-yl-2-d)-2-oxoacetamido)-3-methylpyridin-2-yl)carbamate To a stirred solution of 2-((6-((tert-butoxycarbonyl)amino)-5-methylpyridin-3-yl)amino)-2-oxoacetic acid (167 mg, 0.57 mmol) and 2-(4-fluorophenyl)-5-methylpiperidine-2-d (110 mg, 0.57 mmol) in DMF (0.2 mL) was added HATU (215 mg, 0.57 mmol) and triethylamine (237 µL, 1.70 mmol) at 0° C. The resulting reaction mixture was stirred at ambient temperature for 18 hours. After 18 hours, the reaction mixture was concentrated under reduced pressure and water was added. The aqueous layer was extracted with EtOAc (2×). The combined organic phase was washed with water (2×), dried ($Na_2SO_4$) and concentrated under reduced pressure to obtain crude product. The residue was purified by silica gel column chromatography (Hexane/Ethyl acetate 10/0 to 0/10) to tert-butyl (5-(2-(2-(4-fluorophenyl)-5-methylpiperidin-1-yl-2-d)-2-oxoacetamido)-3-methylpyridin-2-yl)carbamate) as white solid (170 mg, 64%)

$^1$H NMR (DMSO-$d_6$, 400 MHz) 11.05 (s, 0.6H), 10.98 (s, 0.4H), 9.07 (s, 0.6H), 9.03 (s, 0.4H), 8.45 (s, 0.6H), 8.38 (s, 0.4H), 7.93 (app d, 0.6H), 7.89 (s, 0.4H), 7.44-7.32 (m, 2H), 7.28-7.17 (m, 2H), 3.46 (d, J=13.7 Hz, 0.6H), 3.24 (dd, J=3.7, 13.8 Hz, 0.6H), 2.76 (dd, J=3.7, 13.4 Hz, 0.4H), 2.26-1.99 (m, 4H), 1.96-1.80 (m, 1H) 1.74-1.61 (m, 1H), 1.47-1.41 (m, 9H), 1.07-0.99 (m, 3H).

$^{19}$F NMR (DMSO-$d_6$, 376 MHz) δ −116.4, −116.5.

LRMS (APCI$^+$) m/z ($C_{25}H_{30}DFN_4O_4H$): theor. 472.2, exp. 472.5.

Step 2: Synthesis of N-(6-amino-5-methylpyridin-3-yl)-2-(2-(4-fluorophenyl)-5-methylpiperidin-1-yl-2-d)-2-oxoacetamide Hydrochloride (Compound 1009

To a stirred solution of -(4-fluorophenyl)-5-methylpiperidin-1-yl-2-d)-2-oxoacetamido)-3-methylpyridin-2-yl)carbamate (20 mg, 42 μmol) was added HCl 4M in dioxane (11 mL, 4.0 molar, 0.42 mmol). The resulting reaction mixture was stirred at ambient temperature until all starting material was consumed (3 h). The volatiles were concentrated under vacuum and the solid residue was triturated in ether. The solid was filtered and rinsed with ether (the operation was repeated 1 time). After filtration, N-(6-amino-5-methylpyridin-3-yl)-2-(2-(4-fluorophenyl)-5-methylpiperidin-1-yl-2-d)-2-oxoacetamide hydrochloride (Compound 1009) was obtained as a white solid (15 mg, 87%)

$^1$H NMR (CD$_3$OD, 400 MHz) 11.10 (s, 0.6H), 11.04 (s, 0.4H), 8.30 (s, 0.6H), 8.24 (s, 0.4H), 7.84 (s, 0.6H), 7.82 (s, 0.4H), 7.75-7.50 (br s, 2H), 7.42-7.31 (m, 2H), 7.28-7.18 (m, 2H), 4.01 (d, J=13.4 Hz, 0.4H), 3.48 (d, J=12.9 Hz, 0.6H), 3.26-3.20 (app d, 0.6H), 2.780-2.73 (app d, 0.4H), 2.24-2.12 (m, 4H), 2.12-1.82 (m, 2H) 1.74-1.60 (m, 1H), 1.40-1.27 (m, 1H), 1.06-0.98 (app t, 3H).

LRMS (APCI$^+$) m/z ($C_{20}H_{22}DFN_4O_2H$): theor. 372.2, exp. 372.4.

Example 392. The Synthesis of N-(6-amino-5-methyl-3-pyridyl)-2-[(2R)-2-[3-(methylamino)phenyl]-1-piperidyl]-2-oxo-acetamide (Compound 356) and N-(6-amino-5-methyl-3-pyridyl)-2-[(2S)-2-[3-(methylamino)phenyl]-1-piperidyl]-2-oxo-acetamide (Compound 357

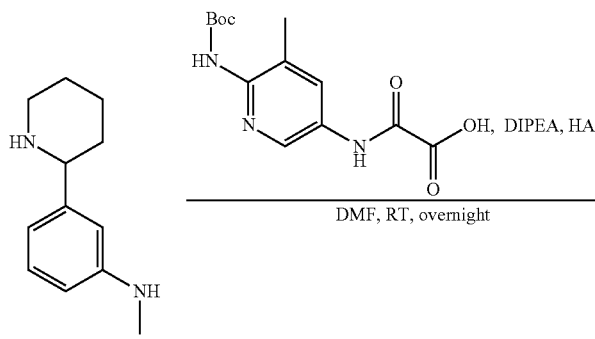

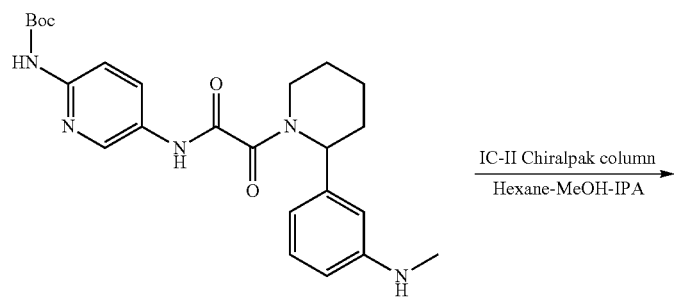

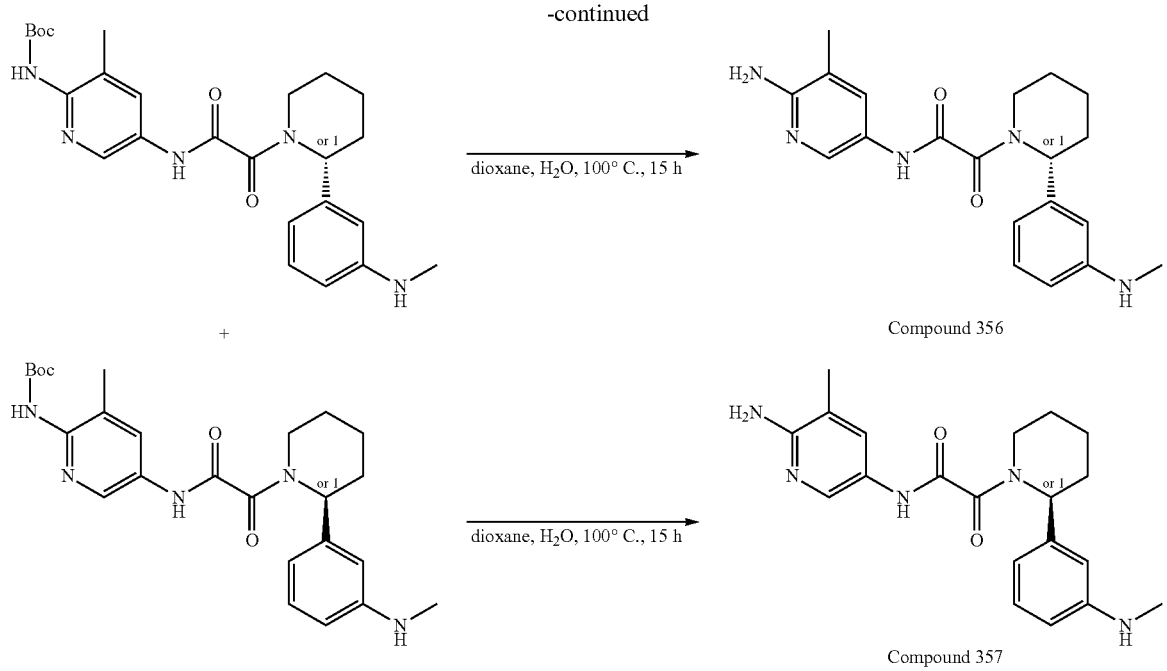

Compound 356

Compound 357

Step 1: The Synthesis of tert-butyl N-[3-methyl-5-[[2-[2-[3-(methylamino)phenyl]-1-piperidyl]-2-oxo-acetyl]amino]-2-pyridyl]carbamate DIPEA (273.55 mg, 2.12 mmol, 368.67 µL) was added to the solution of respective 2-[[6-(tert-butoxycarbonylamino)-5-methyl-3-pyridyl]amino]-2-oxo-acetic acid (0.25 g, 846.62 µmol) and N-methyl-3-(2-piperidyl) aniline (161.10 mg, 846.62 µmol) in DMF (10 mL). The resulting mixture was stirred for 5 min followed by the addition of the solution of HATU (354.10 mg, 931.28 µmol). Then, the reaction mixture was stirred overnight at room temperature. After the completion of the reaction, monitored by LCMS, the resulting suspension was concentrated under reduced pressure. The obtained solid was subjected to HPLC (2-10, in 85-100% H₂O-MeOH+NH₃; loading pump 4.0 mL MeOH+NH₃); Triart C18 100*20 5 mkm column) to afford pure tert-butyl N-[3-methyl-5-[[2-[2-[3-(methylamino)phenyl]-1-piperidyl]-2-oxo-acetyl]amino]-2-pyridyl]carbamate (0.15 g, 320.82 µmol, 37.89% yield).

$^1$H NMR (400 MHz, CDCl₃) δ 1.43 (m, 11H), 1.82 (m, 1H), 2.25 (m, 4H), 2.41 (m, 1H), 2.84 (s, 3H), 3.20 (m, 1H), 3.47 (m, 1H), 4.72 (m, 1H), 6.01 (m, 1H), 6.41 (m, 2H), 6.54 (m, 2H), 7.20 (m, 1H), 8.01 (m, 1H), 8.30 (m, 1H), 9.37 (m, 1H).

LCMS(ESI): [M+2H]⁺ m/z: calcd 467.2; found 469.2; Rt=2.998 min.

Step 2: Chiral Separation of Tert-butyl N-[3-methyl-5-[[2-[2-[3-(methylamino)phenyl]-1-piperidyl]-2-oxo-acetyl]amino]-2-pyridyl]carbamate Chiral separation of tert-butyl N-[3-methyl-5-[[2-[2-[3-(methylamino)phenyl]-1-piperidyl]-2-oxo-acetyl]amino]-2-pyridyl]carbamate was performed using IC-II (250*20, 5 mkm) column; Hexane-MeOH-IPA, 50-25-25 as a mobile phase; flow rate 12 mL/min affording Isomer 2—tert-butyl N-[3-methyl-5-[[2-[(2R)-2-[3-(methylamino)phenyl]-1-piperidyl]-2-oxo-acetyl]amino]-2-pyridyl]carbamate (46.5 mg; 31.0% yield; RT=) and Isomer 1—tert-butyl N-[3-methyl-5-[[2-[(2S)-2-[3-(methylamino)phenyl]-1-piperidyl]-2-oxo-acetyl]amino]-2-pyridyl]carbamate (52.0 mg, 34.67% yield).

Isomer 1:
RT (IC, CO₂-MeOH, 50-50, 2.0 mL/min)=7.218 min.
LCMS(ESI): [M+H]⁺ m/z: calcd 467.2; found 469.2; Rt=4.512 min.

Isomer 2:
RT (IC, CO₂-MeOH, 50-50, 2.0 mL/min)=4.665 min.
LCMS(ESI): [M+H]⁺ m/z: calcd 467.2; found 468.2; Rt=4.512 min.

Step 3: The Synthesis of N-(6-amino-5-methyl-3-pyridyl)-2-[(2R)-2-[3-(methylamino)phenyl]-1-piperidyl]-2-oxo-acetamide (Compound 356 tert-butyl N-[3-methyl-5-[[2-[(2R)-2-[3-(methylamino)phenyl]-1-piperidyl]-2-oxo-acetyl]amino]-2-pyridyl]carbamate Isomer 2 (46.5 mg, 99.45 µmol) was dissolved in water (5 mL) and dioxane (2 mL). Then, the reaction mixture was stirred for 15 hr at 100° C. After the completion of the reaction, monitored by LCMS, the resulting suspension was concentrated under reduced pressure. The obtained solid was subjected to HPLC (2-10 min 0-70% MeOH—H₂O; flow rate 30 mL/min; loading pump 4 mL MeOH; SunFire C18 100*19 mm, 5 mkm column) to afford pure N-(6-amino-5-methyl-3-pyridyl)-2-[(2R)-2-[3-(methylamino)phenyl]-1-piperidyl]-2-oxo-acetamide (14 mg, 38.10 µmol, 38.31% yield).

$^1$H NMR (600 MHz, DMSO-d₆) δ 1.40-1.52 (m, 2H), 1.54-1.64 (m, 2H), 1.71-1.88 (m, 1H), 1.97-2.03 (m, 3H), 2.32-2.36 (m, 1H), 2.54-2.57 (m, 0.4H), 2.61-2.67 (m, 3H), 2.96-3.04 (m, 0.6H), 3.56-4.33 (m, 1H), 5.03-5.54 (m, 1H), 5.54-5.63 (m, 3H), 6.37-6.42 (m, 1H), 6.43-6.46 (m, 1H), 6.46-6.52 (m, 1H), 7.04-7.11 (m, 1H), 7.40-7.53 (m, 1H), 7.94-8.05 (m, 1H), 10.40-10.53 (m, 1H).

LCMS(ESI): [M+H]⁺ m/z: calcd 367.2; found 368.4; Rt=1.968 min.

Step 4: The Synthesis of N-(6-amino-5-methyl-3-pyridyl)-2-[(2S)-2-[3-(methylamino)phenyl]-1-piperidyl]-2-oxo-acetamide (Compound 357 tert-butyl N-[3-methyl-5-[[2-[(2S)-2-[3-(methylamino)phenyl]-1-piperidyl]-2-oxo-acetyl]amino]-2-pyridyl]carbamate Isomer 1 (52 mg, 111.22 μmol) was dissolved in dioxane (2 mL) and water (5 mL). Then, the reaction mixture was stirred for 15 hr at 100° C. After the completion of the reaction, monitored by LCMS, the resulting suspension was concentrated under reduced pressure. The obtained solid was subjected to HPLC (2-10 min 0-70% MeOH—H$_2$O; flow rate 30 mL/min; loading pump 4 mL MeOH; SunFire C18 100*19 mm, 5 mkm column) to afford pure N-(6-amino-5-methyl-3-pyridyl)-2-[(2S)-2-[3-(methyl-amino)phenyl]-1-piperidyl]-2-oxo-acetamide (22.2 mg, 60.42 μmol, 54.32% yield).

$^1$H NMR (600 MHz, DMSO-d$_6$) δ 1.50 (m, 4H), 1.79 (m, 1H), 2.00 (m, 3H), 2.32 (m, 1H), 2.55 (m, 1H), 2.63 (m, 3H), 3.00 (m, 0.6H), 3.41 (m, 0.4H), 3.93 (m, 1H), 5.37 (m, 1H), 5.59 (m, 2H), 6.39 (m, 1H), 6.44 (m, 1H), 6.48 (m, 1H), 7.07 (m, 1H), 7.47 (m, 1H), 7.99 (m, 1H), 10.46 (m, 1H).

LCMS(ESI): [M+H]$^+$ m/z: calcd 367.2; found 368.4; Rt=1.967 min.

Example 393. The Synthesis of N-(6-amino-5-methylpyridin-3-yl)-2-(2-cyclopentylpiperidin-1-yl)-2-oxoacetamide (Compound 61, Compound 336, Compound 340

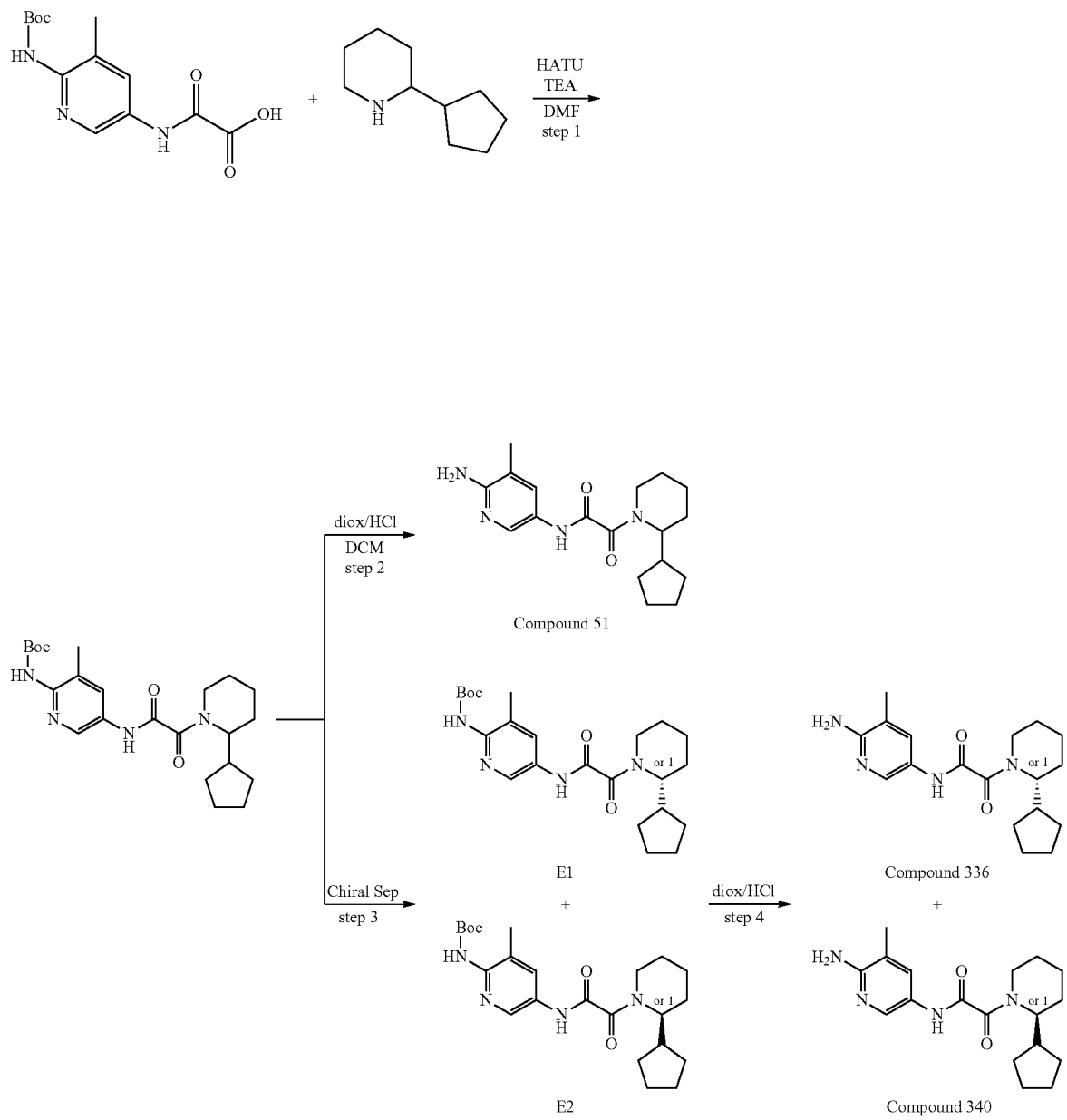

Step 1: Synthesis of tert-butyl (5-(2-(2-cyclopentylpiperidin-1-yl)-2-oxoacetamido)-3-methylpyridin-2-yl)carbamate 2-[[6-(tert-butoxycarbonylamino)-5-methyl-3-pyridyl]amino]-2-oxo-acetic acid (352.94 mg, 1.02 mmol) and 2-cyclopentylpiperidine (155.71 mg, 1.02 mmol) were mixed in DMF (15 mL). The reaction suspension was cooled to 0° C. and HATU (386.29 mg, 1.02 mmol) followed by TEA (308.41 mg, 3.05 mmol, 424.81 µL) were added. The clear solution was stirred at ambient temperature for 5 hr then volatiles were evaporated under reduced pressure and residue (1 g) was subjected to RP-HPLC (column: SunFire C18 100×19 mm, 5 um; 60-60-90% 0-1-5 min water-methanol as mobile phase) to give tert-butyl N-[5-[[2-(2-cyclopentyl-1-piperidyl)-2-oxo-acetyl]amino]-3-methyl-2-pyridyl]carbamate (264 mg, 613.18 µmol, 60.36% yield).

$^1$H NMR (400 MHz, DMSO-$d_6$) δ (ppm) 1.03 (m, 3H), 1.43 (s, 9H), 1.65 (m, 12H), 2.17 (s, 3H), 3.16 (m, 1H), 3.53 (m, 1H), 4.23 (m, 1H), 7.91 (m, 1H), 8.41 (m, 1H), 9.05 (m, 1H), 10.88 (m, 1H). LCMS(ESI): [M+1]$^+$ m/z: calcd 430.5; found 431.2; Rt=3.533 min.

Step 2: Synthesis of N-(6-amino-5-methylpyridin-3-yl)-2-(2-cyclopentylpiperidin-1-yl)-2-oxoacetamide (Compound 61

Hydrogen chloride solution 4.0 M in dioxane (1.51 g, 5.81 mmol, 1.44 mL, 14% purity) was carefully added at rt to a solution of tert-butyl N-[5-[[2-(2-cyclopentyl-1-piperidyl)-2-oxo-acetyl]amino]-3-methyl-2-pyridyl]carbamate (250 mg, 580.67 µmol) in DCM (4 mL). The reaction mixture was then stirred for 12 hr at rt and the solvents were evaporated in vacuo to give 0.25 g of crude material. It was subjected to RP-HPLC (column: YMC Triart C18 100×20 mm, Sum; 50-60% 0-5 min 0.1% NH$_3$-methanol as mobile phase) to give Compound 61 N-(6-amino-5-methyl-3-pyridyl)-2-(2-cyclopentyl-1-piperidyl)-2-oxo-acetamide (98 mg, 296.59 µmol, 51.08% yield).

$^1$H NMR (400 MHz, DMSO-$d_6$) δ (ppm) 1.12 (m, 2H), 1.40 (m, 1H), 1.55 (m, 6H), 1.66 (m, 5H), 2.03 (s, 3H), 2.74 (m, 1H), 3.14 (m, 1H), 3.54 (m, 1H), 4.21 (m, 1H), 5.62 (m, 2H), 7.48 (m, 1H), 8.01 (m, 1H), 10.26 (m, 1H). LCMS(ESI): [M+1] m/z: calcd 330.5; found 331.2; Rt=2.706 min.

Step 3: Chiral Separation

Purification on the chiral column was taken in the system CO$_2$-MeOH, 90-10, 2 mL/min. Number of injections: 1, injection volume: 1 mkl. From 183.1 mg of racemate, 71.84 mg and 60 mg of the individual enantiomers were obtained.

E1:Retention time: 3.58 min $^1$H NMR (400 MHz, CDCl$_3$) δ (ppm) 1.23 (m, 3H), 1.47 (s, 9H), 1.61 (m, 12H), 2.14 (s, 3H), 3.02 (m, 1H), 4.43 (m, 1H), 4.78 (m, 1H), 7.08 (m, 1H), 8.08 (s, 1H), 8.46 (s, 1H), 9.51 (m, 1H). LCMS(ESI): [M+1] m/z: calcd 430.2; found 431.2; Rt=5.746 min.

Retention time: 4.22 min $^1$H NMR (400 MHz, CDCl$_3$) δ (ppm) 1.21 (m, 3H), 1.48 (s, 9H), 1.62 (m, 12H), 2.14 (s, 3H), 3.03 (m, 1H), 4.42 (m, 1H), 4.82 (m, 1H), 6.98 (m, 1H), 8.08 (s, 1H), 8.42 (s, 1H), 9.41 (m, 1H). LCMS(ESI): [M+1] m/z: calcd 430.2; found 431.2; Rt=5.757 min.

Step 4: Synthesis of N-(6-amino-5-methylpyridin-3-yl)-2-(2-cyclopentylpiperidin-1-yl)-2-oxoacetamide (Compound 336, Compound 340

The solution of tert-butyl N-[5-[[2-[(2S)-2-cyclopentyl-1-piperidyl]-2-oxo-acetyl]amino]-3-methyl-2-pyridyl]carbamate (0.07184 g, 166.86 µmol) and tert-butyl N-[5-[[2-[(2R)-2-cyclopentyl-1-piperidyl]-2-oxo-acetyl]amino]-3-methyl-2-pyridyl]carbamate (0.06 g, 139.36 µmol) in dioxane/HCl (5 mL) were stirred at 20° C. for 12 hr. The resulting mixtures were subjected to HPLC (column SunFire 19*100 mm, water-MeCN+HCl as mobile phase) to obtain N-(6-amino-5-methyl-3-pyridyl)-2-[(2S)-2-cyclopentyl-1-piperidyl]-2-oxo-acetamide (0.0329 g, 89.67 µmol, 53.74% yield, HCl) and N-(6-amino-5-methyl-3-pyridyl)-2-[(2R)-2-cyclopentyl-1-piperidyl]-2-oxo-acetamide (0.0329, 89.67 µmol, 64.35% yield, HCl).

Compound 336: $^1$H NMR (600 MHz, DMSO-$d_6$) δ (ppm) 1.08 (m, 2H), 1.37 (m, 1H), 1.56 (m, 11H), 2.16 (s, 3H), 2.42 (m, 1H), 3.05 (m, 1H), 3.53 (m, 1H), 4.19 (m, 1H), 7.72 (m, 2H), 7.82 (m, 1H), 8.26 (m, 1H), 10.93 (m, 1H), 13.49 (br s, 1H). LCMS(ESI): [M+1] m/z: calcd 330.2; found 331.2; Rt=2.281 min.

Compound 340: $^1$H NMR (600 MHz, DMSO-$d_6$) δ (ppm) 1.11 (m, 2H), 1.36 (m, 1H), 1.55 (m, 11H), 2.16 (s, 3H), 2.43 (m, 1H), 2.94 (m, 1H), 3.53 (m, 1H), 4.19 (m, 1H), 7.69 (m, 2H), 7.81 (m, 1H), 8.26 (m, 1H), 10.92 (m, 1H), 13.44 (br s, 1H). LCMS(ESI): [M+1] m/z: calcd 330.2; found 331.2; Rt=2.424 min.

Example 394. The Synthesis of N-(6-amino-5-methyl-3-pyridyl)-2-[(2R)-2-[3-(dimethylamino)phenyl]-1-piperidyl]-2-oxo-acetamide (Compound 390) and N-(6-amino-5-methyl-3-pyridyl)-2-[(2S)-2-[3-(dimethylamino)phenyl]-1-piperidyl]-2-oxo-acetamide (Compound 384

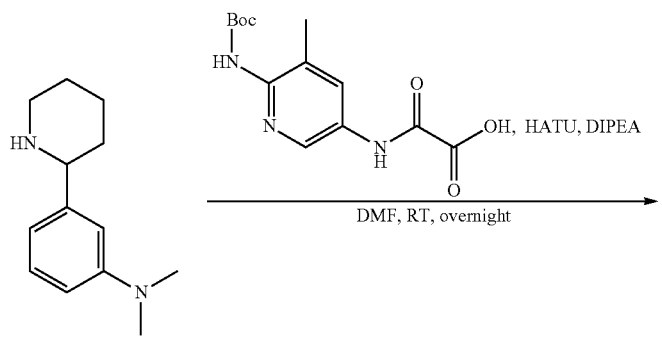

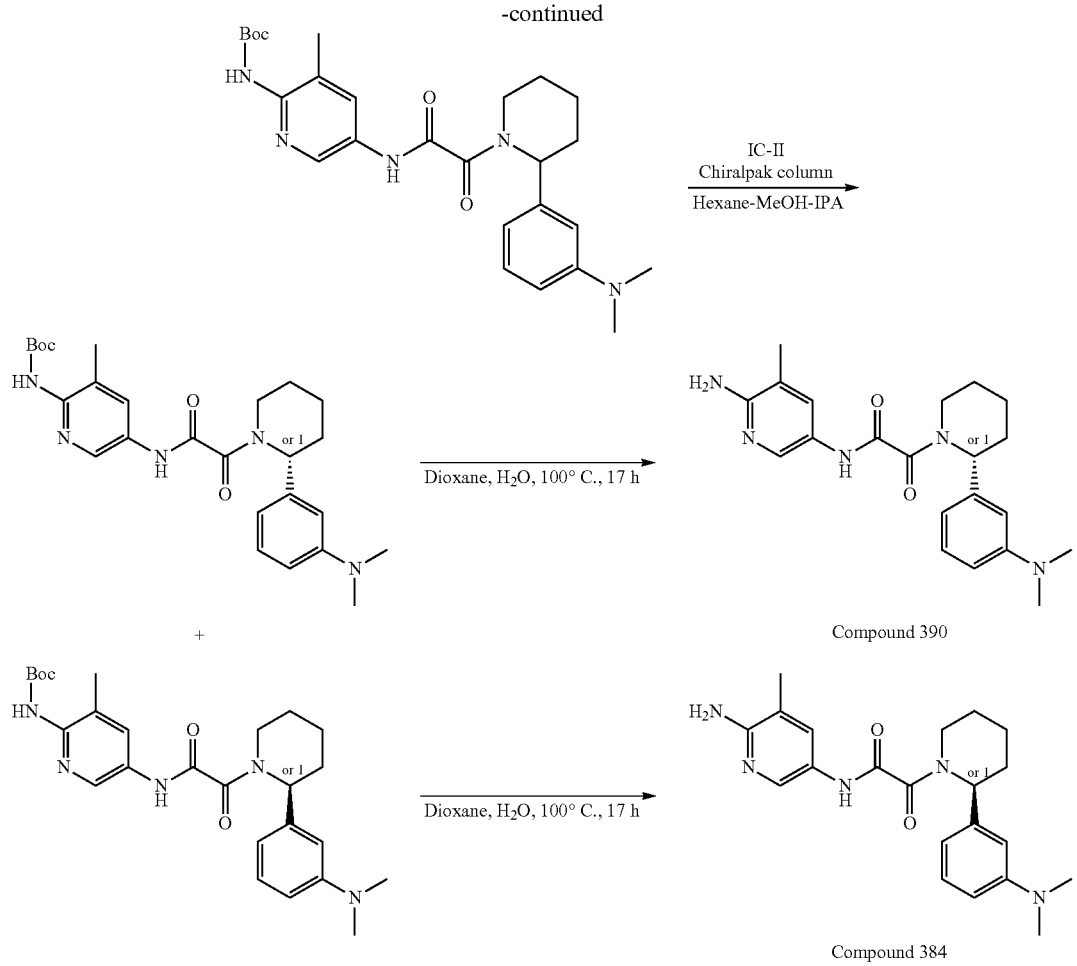

Compound 390

Compound 384

Step 1: The Synthesis of tert-butyl N-[5-[[2-[2-[3-(dimethylamino)phenyl]-1-piperidyl]-2-oxo-acetyl]amino]-3-methyl-2-pyridyl]carbamate DIPEA (262.61 mg, 2.03 mmol, 353.92 μL) was added to the solution of respective 2-[[6-(tert-butoxycarbonylamino)-5-methyl-3-pyridyl]amino]-2-oxo-acetic acid (0.2 g, 677.30 μmol) and N,N-dimethyl-3-(2-piperidyl) aniline (138.38 mg, 677.30 μmol) in DMF (10 mL) DMF (10 mL) The resulting mixture was stirred for 5 min followed by the addition of the solution of HATU (283.28 mg, 745.03 μmol). Then, the reaction mixture was stirred overnight at room temperature. After the completion of the reaction, monitored by LCMS, the resulting suspension was concentrated under reduced pressure. The obtained solid was subjected to HPLC (2-10 min 35-60% $H_2O$-MeOH; loading pump 4 mL MeOH; SunFire C18 100*19 mm 5 mkm column) to afford pure tert-butyl N-[5-[[2-[2-[3-(dimethylamino)phenyl]-1-piperidyl]-2-oxo-acetyl]amino]-3-methyl-2-pyridyl]carbamate (0.1 g, 207.65 μmol, 30.66% yield)

$^1$H NMR (400 MHz, DMSO-$d_6$) δ 1.42 (m, 9H), 1.63 (m, 4H), 2.18 (m, 2H), 2.36 (m, 2H), 2.93 (m, 6H), 3.22 (m, 3H), 4.01 (m, 2H), 6.64 (m, 3H), 7.20 (m, 1H), 7.94 (m, 1H), 8.43 (m, 1H).

LCMS(ESI): [M+H]$^+$ m/z: calcd 481.2; found 482.2; Rt=3.235 min.

Step 2: Chiral Separation of Tert-butyl N-[5-[[2-[2-[3-(dimethylamino)phenyl]-1-piperidyl]-2-oxo-acetyl]amino]-3-methyl-2-pyridyl]carbamate Chiral separation of tert-butyl N-[5-[[2-[2-[3-(dimethylamino)phenyl]-1-piperidyl]-2-oxo-acetyl]amino]-3-methyl-2-pyridyl]carbamate was performed using IC-II (250*20, 5 mkm) column; Hexane-MeOH-IPA, 50-25-25 as a mobile phase; flow rate 12 mL/min affording Isomer 1—tert-butyl N-[5-[[2-[(2R)-2-[3-(dimethylamino)phenyl]-1-piperidyl]-2-oxo-acetyl]amino]-3-methyl-2-pyridyl]carbamate (29.4 mg, 29.40% yield; RT=39.731 min) and Isomer 2—tert-butyl N-[5-[[2-[(2S)-2-[3-(dimethylamino)phenyl]-1-piperidyl]-2-oxo-acetyl]amino]-3-methyl-2-pyridyl]carbamate (29.5 mg, 29.50% yield; RT=30.341 min).

Isomer 1: RT (IC, Hexane-IPA-MeOH, 50-25-25, 0.6 mL/min)=33.49 min.

LCMS(ESI): [M+H]$^+$ m/z: calcd 481.2; found 482.2; Rt=4.733 min.

Isomer 2: RT (IC, Hexane-IPA-MeOH, 50-25-25, 0.6 mL/min)=25.16 min.

LCMS(ESI): [M+2H]$^+$ m/z: calcd 481.2; found 483.2; Rt=4.742 min.

Step 3: The Synthesis of N-(6-amino-5-methyl-3-pyridyl)-2-[(2R)-2-[3-(dimethylamino)phenyl]-1-piperidyl]-2-oxo-acetamide (Compound 390 tert-butyl N-[5-[[2-[(2R)-2-[3-(dimethylamino)phenyl]-1-piperidyl]-2-oxo-acetyl]amino]-3-methyl-2-pyridyl]carbamate Isomer 1 (29.4 mg, 61.05 μmol) was dissolved in dioxane (2 mL) and water (5 mL) mixture. Then reaction mixture was stirred for 17 hr at 100° C. After the completion of the reaction, monitored by LCMS, the resulting suspension was concentrated under reduced pressure. The obtained solid was subjected to HPLC (2-10 min 0-60% H$_2$O-MeOH+NH$_3$; loading pupm 4 mL MeOH+NH$_3$; Triart 100*20 5 mkm column) to afford pure N-(6-amino-5-methyl-3-pyridyl)-2-[(2R)-2-[3-(dimethylamino)phenyl]-1-piperidyl]-2-oxo-acetamide (16.1 mg, 42.21 μmol, 69.13% yield)

$^1$H NMR (600 MHz, DMSO-d$_6$) δ 1.37-1.53 (m, 2H), 1.53-1.64 (m, 2H), 1.72-1.87 (m, 1H), 1.96-2.04 (m, 3H), 2.39-2.42 (m, 1H), 2.54-2.56 (m, 0.3H), 2.83-2.90 (m, 6H), 2.99-3.06 (m, 0.7H), 3.61-4.32 (m, 1H), 5.03-5.58 (m, 1H), 5.58-5.66 (m, 2H), 6.55-6.63 (m, 3H), 7.13-7.21 (m, 1H), 7.42-7.53 (m, 1H), 7.92-8.04 (m, 1H), 10.45-10.56 (m, 1H).

LCMS(ESI): [M+H]$^+$ m/z: calcd 381.2; found 382.2; Rt=1.900 min.

Step 4: The Synthesis of N-(6-amino-5-methyl-3-pyridyl)-2-[(2S)-2-[3-(dimethylamino)phenyl]-1-piperidyl]-2-oxo-acetamide (Compound 384 tert-butyl N-[5-[[2-[(2S)-2-[3-(dimethylamino)phenyl]-1-piperidyl]-2-oxo-acetyl]amino]-3-methyl-2-pyridyl]carbamate Isomer 2 (29.5 mg, 61.26 μmol) was dissolved in dioxane (2 mL) and water (5 mL) mixture. Then reaction mixture was stirred for 17 hr at 100° C. After the completion of the reaction, monitored by LCMS, the resulting suspension was concentrated under reduced pressure. The obtained solid was subjected to HPLC (2-10 min 0-60% H$_2$O-MeOH+NH$_3$; loading pupm 4 mL MeOH+NH$_3$; Triart 100*20 5 mkm column) to afford pure N-(6-amino-5-methyl-3-pyridyl)-2-[(2S)-2-[3-(dimethylamino)phenyl]-1-piperidyl]-2-oxo-acetamide (16.2 mg, 42.47 μmol, 69.33% yield).

$^1$H NMR (600 MHz, DMSO-d$_6$) δ 1.35-1.53 (m, 2H), 1.53-1.65 (m, 2H), 1.72-1.90 (m, 1H), 1.96-2.03 (m, 3H), 2.38-2.43 (m, 1H), 2.84-2.88 (m, 6H), 2.98-3.27 (m, 1H), 3.62-4.27 (m, 1H), 5.06-5.64 (m, 3H), 6.55-6.65 (m, 3H), 7.13-7.22 (m, 1H), 7.40-7.55 (m, 1H), 7.90-8.08 (m, 1H), 10.47-10.55 (m, 1H).

LCMS(ESI): [M+H]$^+$ m/z: calcd 381.2; found 382.2; Rt=2.225 min.

Example 395. The Synthesis of N-(6-amino-5-methyl-3-pyridyl)-2-[(2R,5S)-5-methyl-2-[3-(methylamino)phenyl]-1-piperidyl]-2-oxo-acetamide (Compound 449) and N-(6-amino-5-methyl-3-pyridyl)-2-[(2S,5R)-5-methyl-2-[3-(methylamino)phenyl]-1-piperidyl]-2-oxo-acetamide (Compound 450

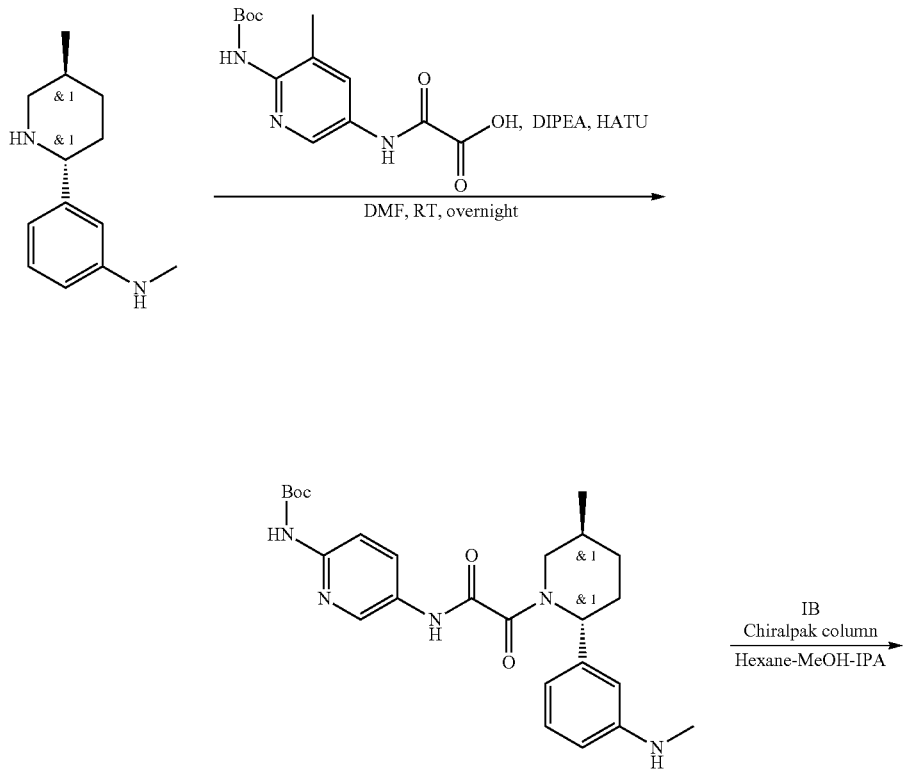

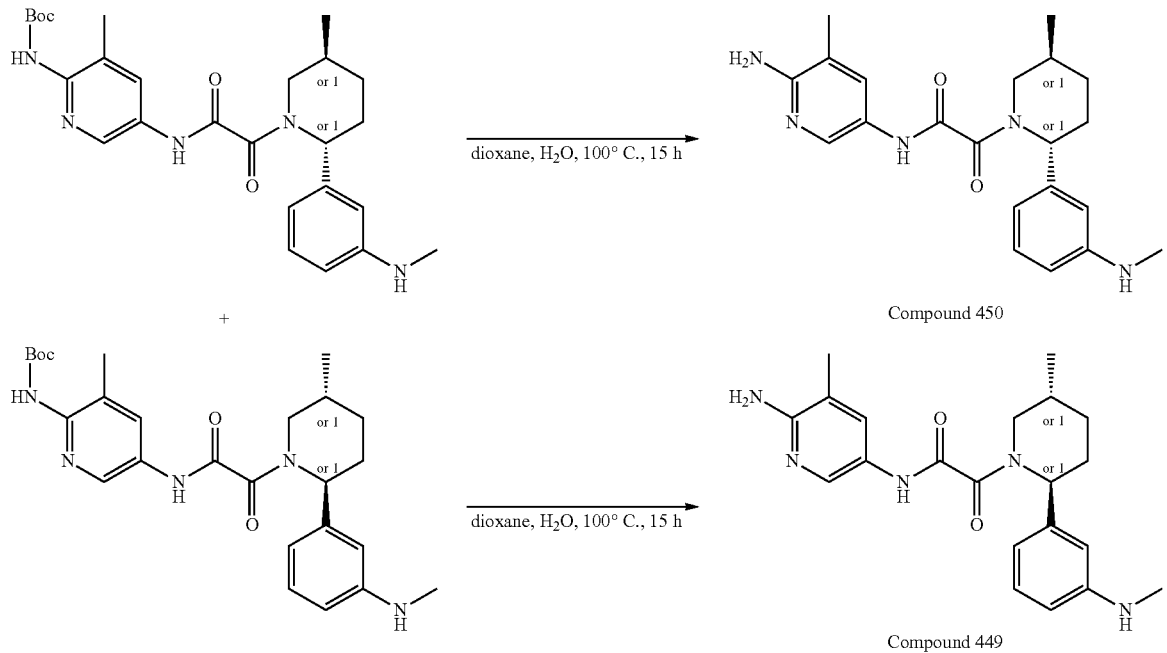

Compound 450

Compound 449

Step 1: The Synthesis of tert-butyl N-[3-methy-5-[[2-[(2R,5S)-5-methyl-2-[3-(methylamino)phenyl]-1-piperidyl]-2-oxo-acetyl]amino]-2-pyridyl]carbamate DIPEA (765.94 mg, 5.93 mmol, 1.03 mL) was added to the solution of respective 2-[[6-(tert-butoxycarbonylamino)-5-methyl-3-pyridyl]amino]-2-oxo-acetic acid (0.5 g, 1.69 mmol) and N-methyl-3-[(2S,5R)-5-methyl-2-piperidyl]aniline (345.95 mg, 1.69 mmol) in DMF (15 mL). The resulting mixture was stirred for 5 min followed by the addition of the solution of HATU (708.20 mg, 1.86 mmol). Then, the reaction mixture was stirred overnight at room temperature. After the completion of the reaction, monitored by LCMS, the resulting suspension was concentrated under reduced pressure. The obtained solid was subjected to HPLC (2-10 min 35-100% MeCN—H$_2$O as a mobile phase; flow rate 30 mL/min; loading pump 4 mL MeCN; Sunfire C18 19*100 mm 5 mkm column) to afford pure tert-butyl N-[3-methyl-5-[[2-[(2R,5S)-5-methyl-2-[3-(methylamino)phenyl]-1-piperidyl]-2-oxo-acetyl]amino]-2-pyridyl]carbamate (0.29 g, 602.18 μmol, 35.56% yield).

$^1$H NMR (400 MHz, CDCl$_3$) δ 1.04 (m, 3H), 1.32 (m, 2H), 1.47 (s, 9H), 2.12 (m, 6H), 2.91 (m, 3H), 3.41 (m, 3H), 4.61 (m, 1H), 6.67 (m, 3H), 7.21 (m, 1H), 8.05 (m, 1H), 8.38 (m, 1H), 9.41 (m, 1H).

LCMS(ESI): [M+H]$^+$ m/z: calcd 481.2; found 482.2; Rt=1.297 min.

Step 2: Chiral Separation of Tert-butyl N-[3-methy-5-[[2-[(2R,5S)-5-methyl-2-[3-(methylamino)phenyl]-1-piperidyl]-2-oxo-acetyl]amino]-2-pyridyl]carbamate Chiral separation of tert-butyl N-[3-methyl-5-[[2-[(2R,5S)-5-methyl-2-[3-(methylamino)phenyl]-1-piperidyl]-2-oxo-acetyl]amino]-2-pyridyl]carbamate was performed using IB (250*20, 5 mkm) column, Hexane-MeOH-IPA, 50-25-25 as a mobile phase; flow rate 12 mL/min affording Isomer 1—tert-butyl N-[3-methyl-5-[[2-[(2R,5S)-5-methyl-2-[3-(methylamino)phenyl]-1-piperidyl]-2-oxo-acetyl]amino]-2-pyridyl]carbamate)101.59 mg, 35.03% yield; RT=15.696 min) and Isomer 2—tert-butyl N-[3-methyl-5-[[2-[(2S,5R)-5-methyl-2-[3-(methylamino)phenyl]-1-piperidyl]-2-oxo-acetyl]amino]-2-pyridyl]carbamate (111.87 mg, 38.58% yield; RT=33.861 min).

Isomer 1: RT (IC, Hexane-IPA-MeOH, 50-25-25, 0.6 mL/min)=17.22 min.

LCMS(ESI): [M+H]$^+$ m/z: calcd 481.2; found 482.2; Rt=2.964 min.

Isomer 2: RT (IC, Hexane-IPA-MeOH, 50-25-25, 0.6 mL/min)=42.79 min.

LCMS(ESI): [M+2H]$^+$ m/z: calcd 481.2; found 483.2; Rt=2.961 min.

Step 3: The Synthesis of N-(6-amino-5-methyl-3-pyridyl)-2-[(2S,5R)-5-methyl-2-[3-(methylamino)phenyl]-1-piperidyl]-2-oxo-acetamide (Compound 450 tert-butyl N-[3-methyl-5-[[2-[(2S,5R)-5-methyl-2-[3-(methylamino)phenyl]-1-piperidyl]-2-oxo-acetyl]amino]-2-pyridyl]carbamate Isomer 2 (111.87 mg, 232.30 μmol) was dissolved in water (5 mL) and dioxane (2 mL) mixture. Then reaction mixture was stirred for 15 hr at 100° C. After the completion of the reaction, monitored by LCMS, the resulting suspension was concentrated under reduced pressure. The obtained solid was subjected to HPLC (2-10 min 35-100% MeCN—H$_2$O; flow rate 30 mL/min; loading pumn 4 mL MeCN; Sunfire C18 19*100 mm 5 mkm column) to afford pure N-(6-amino-5-methyl-3-pyridyl)-2-[(2S,5R)-5- methyl-2-[3-(methylamino)phenyl]-1-piperidyl]-2-oxo-acetamide (61.6 mg, 161.48 μmol, 69.52% yield).

$^1$H NMR (DMSO-d$_6$, 500 MHz): δ (ppm) 1.02 (m, 3H), 1.33 (m, 1H), 1.68 (m, 1H), 1.86 (m, 1H), 2.03 (m, 3H), 2.14 (m, 1H), 2.66 (m, 3H), 2.95 (m, 1H), 3.65 (m, 1H), 5.30 (m, 1H), 5.61 (m, 3H), 6.46 (m, 3H), 6.52 (d, 1H), 7.09 (m, 1H), 7.48 (m, 1H), 8.01 (m, 1H), 10.45 (m, 1H).

LCMS(ESI): [M+H]$^+$ m/z: calcd 381.2; found 382.2; Rt=1.866 min.

Step 4: The Synthesis of N-(6-amino-5-methyl-3-pyridyl)-2-[(2R,5S)-5-methyl-2-[3-(methylamino)phenyl]-1-piperidyl]-2-oxo-acetamide (Compound 449 tert-butyl N-[3-methyl-5-[[2-[(2R,5S)-5-methyl-2-[3-(methylamino)phenyl]-1-piperidyl]-2-oxo-acetyl]amino]-2-pyridyl]carbamate Isomer 1 (101.59 mg, 210.95 μmol) was dissolved in water (5 mL) and dioxane (2 mL) mixture. Then reaction mixture was stirred for 15 hr at 100° C. After the completion of the reaction, monitored by LCMS, the resulting suspension was concentrated under reduced pressure.

The obtained solid was subjected to HPLC (2-10 min 35-100% MeCN—H$_2$O; flow rate 30 mL/min; loading pumn 4 mL MeCN; Sunfire C18 19*100 mm 5 mkm column) to afford pure N-(6-amino-5-methyl-3-pyridyl)-2-[(2R,5S)-5-methyl-2-[3-(methylamino)phenyl]-1-piperidyl]-2-oxo-acetamide (55.3 mg, 144.97 μmol, 68.72% yield).

$^1$H NMR (DMSO-d$_6$, 500 MHz): δ (ppm) 1.02 (m, 3H), 1.34 (m, 1H), 1.76 (m, 1H), 2.03 (m, 3H), 2.13 (m, 1H), 2.66 (m, 5H), 3.03 (m, 1H), 3.74 (m, 1H), 5.30 (m, 1H), 5.61 (m, 3H), 6.43 (d, 1H), 6.50 (m, 2H), 7.09 (t, 1H), 7.49 (m, 1H), 8.02 (m, 1H), 10.45 (m, 1H).

LCMS(ESI): [M+H]$^+$ m/z: calcd 381.2; found 382.2; Rt=1.831 min.

Example 396. The Synthesis of N-(6-amino-5-methyl-3-pyridyl)-2-[(2S,5R)-2-[3-(dimethylamino)phenyl]-5-methyl-1-piperidyl]-2-oxo-acetamide (Compound 387) and N-(6-amino-5-methyl-3-pyridyl)-2-[(2R,5S)-2-[3-(dimethylamino)phenyl]-5-methyl-1-piperidyl]-2-oxo-acetamide (Compound 386

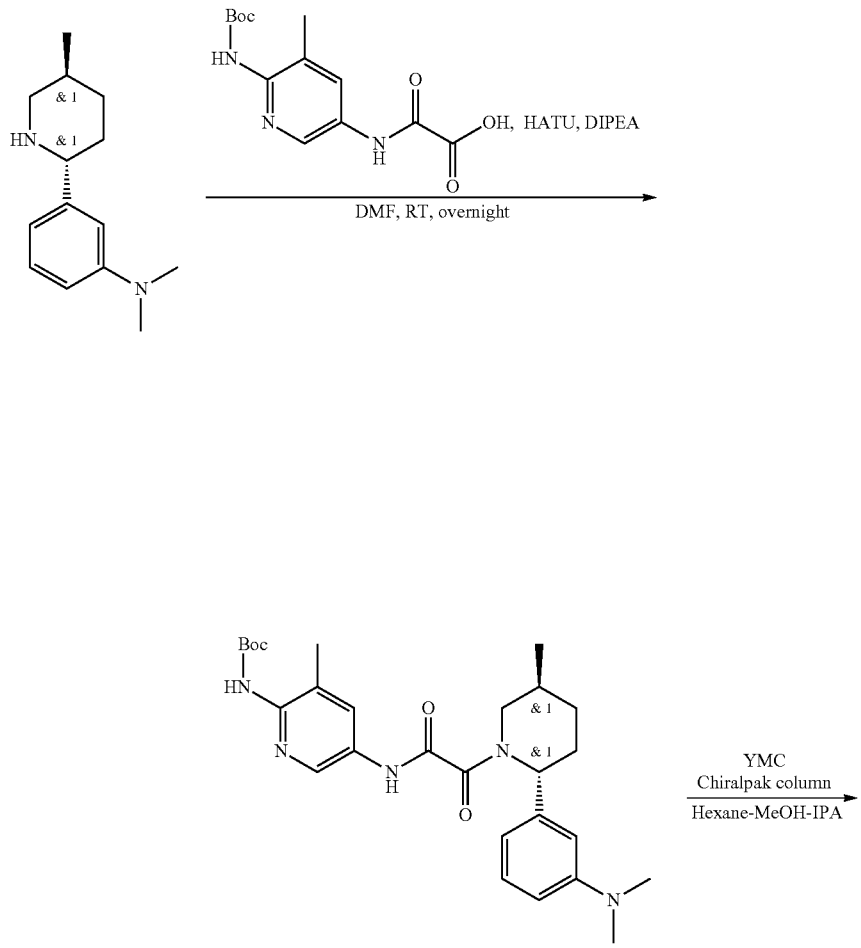

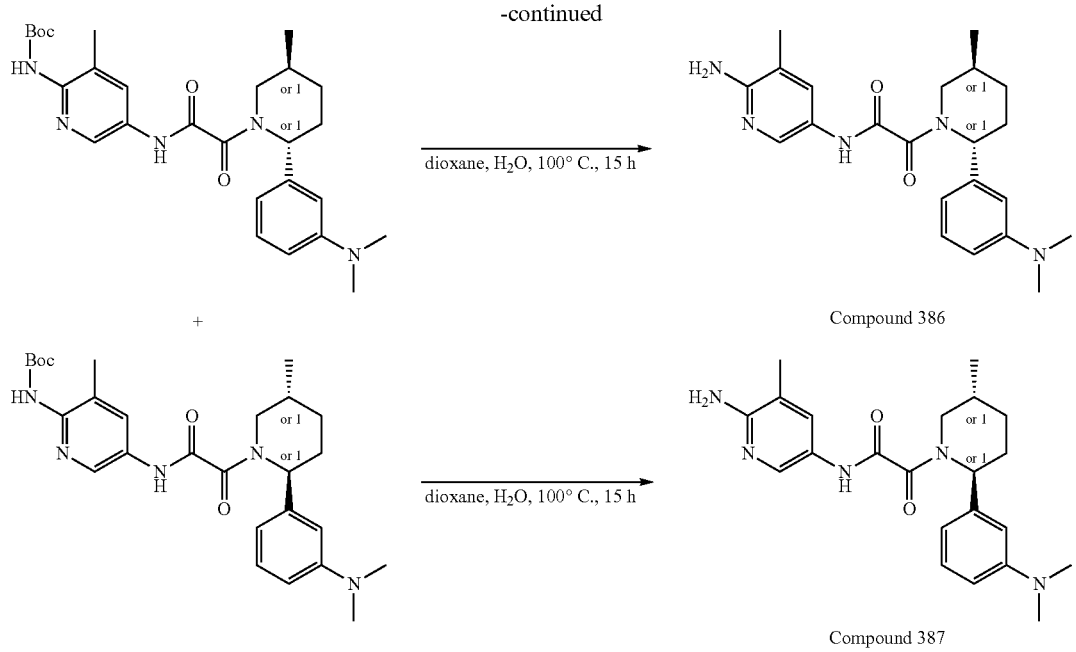

Compound 386

Compound 387

Step 1: The Synthesis of tert-butyl N-[5-[[2-[(2R,5S)-2-[3-(dimethylamino)phenyl]-5-methyl-1-piperidyl]-2-oxo-acetyl]amino]-3-methyl-2-pyridyl]carbamate DIPEA (207.90 mg, 1.61 mmol, 280.19 μL) was added to the solution of respective 2-[[6-(tert-butoxycarbonylamino)-5-methyl-3-pyridyl]amino]-2-oxo-acetic acid (0.19 g, 643.43 μmol) and N,N-dimethyl-3-[(2S,5R)-5-methyl-2-piperidyl]aniline (140.49 mg, 643.43 μmol) in DMF (10 mL)DMF (10 mL) The resulting mixture was stirred for 5 min followed by the addition of the solution of HATU (269.12 mg, 707.78 μmol). Then, the reaction mixture was stirred overnight at room temperature. After the completion of the reaction, monitored by LCMS, the resulting suspension was concentrated under reduced pressure. The obtained solid was subjected to HPLC (2-10 min 35-60% H$_2$O-MeCN as a mobile phase; loading pump 4 mL MeCN; Triart C18 100*20 mm 5 mkm column) to afford pure tert-butyl N-[5-[[2-[(2R,5S)-2-[3-(dimethylamino)phenyl]-5-methyl-1-piperidyl]-2-oxo-acetyl]amino]-3-methyl-2-pyridyl]carbamate (67 mg, 135.19 μmol, 21.01% yield).

$^1$H NMR (400 MHz, CDCl$_3$) δ 1.05 (m, 3H), 1.37 (m, 2H), 1.51 (s, 9H), 2.12 (m, 6H), 2.91 (m, 6H), 3.48 (s, 3H), 4.22 (m, 1H), 5.78 (m, 1H), 6.51 (m, 2H), 7.20 (m, 1H), 7.94 (m, 1H), 8.31 (m, 1H), 9.43 (m, 1H).

LCMS(ESI): [M+H]$^+$ m/z: calcd 495.2; found 496.2; Rt=1.398 min.

Step 2: Chiral Separation of Tert-butyl N-[5-[[2-[(2R,5S)-2-[3-(dimethylamino)phenyl]-5-methyl-1-piperidyl]-2-oxo-acetyl]amino]-3-methyl-2-pyridyl]carbamate Chiral separation of tert-butyl N-[5-[[2-[(2R,5S)-2-[3-(dimethylamino)phenyl]-5-methyl-1-piperidyl]-2-oxo-acetyl]amino]-3-methyl-2-pyridyl]carbamate was performed using YMC (250*20, 5 mkm) column, Hexane-MeOH-IPA, 50-25-25 as a mobile phase; flow rate 12 mL/min affording Isomer 1—tert-butyl N-[5-[[2-[(2R,5S)-2-[3-(dimethylamino)phenyl]-5-methyl-1-piperidyl]-2-oxo-acetyl]amino]-3-methyl-2-pyridyl]carbamate (67.0 g, 29.55%; RT=14.517 min) and Isomer 2—tert-butyl N-[5-[[2-[(2S,5R)-2-[3-(dimethylamino)phenyl]-5-methyl-1-piperidyl]-2-oxo-acetyl]amino]-3-methyl-2-pyridyl]carbamate (20.1 mg, 30.0% yield; RT=19.991 min).

Isomer 1: RT (IC, Hexane-IPA-MeOH, 40-30-30, 0.6 mL/min)=15.76 min.

LCMS(ESI): [M+H]$^+$ m/z: calcd 495.2; found 496.4; Rt=1.315 min.

Isomer 2: RT (IC, Hexane-IPA-MeOH, 40-30-30, 0.6 mL/min)=25.50 min.

LCMS(ESI): [M+H]$^+$ m/z: calcd 495.2; found 496.4; Rt=1.316 min.

Step 3: The Synthesis of N-(6-amino-5-methyl-3-pyridyl)-2-[(2R,5S)-2-[3-(dimethylamino)phenyl]-5-methyl-1-piperidyl]-2-oxo-acetamide (Compound 386 tert-butyl N-[5-[[2-[(2R,5S)-2-[3-(dimethylamino)phenyl]-5-methyl-1-piperidyl]-2-oxo-acetyl]amino]-3-methyl-2-pyridyl]carbamate Isomer 1 (19.8 mg, 39.95 μmol) was dissolved in dioxane (2 mL) and water (5 mL) mixture. Then reaction mixture was stirred for 15 hr at 100° C. After the completion of the reaction, monitored by LCMS, the resulting suspension was concentrated under reduced pressure. The obtained solid was subjected to HPLC (2-10 min 45-60% H$_2$O-MeCN—NH$_3$ as a mobile phase; loading pump 4 mL MeCN; Triart 100*20 mm 5 mkm column) to afford pure N-(6-amino-5-methyl-3-pyridyl)-2-[(2R,5S)-2-[3-(dimethylamino)phenyl]-5-methyl-1-piperidyl]-2-oxo-acetamide (7.5 mg, 18.96 μmol, 47.47% yield).

$^1$H NMR (600 MHz, DMSO-d$_6$) δ 0.96-1.02 (m, 3H), 1.24-1.37 (m, 1H), 1.59-1.75 (m, 1H), 1.80-1.91 (m, 1H), 1.95-2.02 (m, 3H), 2.02-2.23 (m, 2H), 2.75-2.79 (m, 0.4H), 2.83-2.88 (m, 6H), 3.24-3.27 (m, 0.6H), 3.40-4.03 (m, 1H), 5.03-5.53 (m, 1H), 5.53-5.67 (m, 2H), 6.55-6.67 (m, 3H), 7.10-7.21 (m, 1H), 7.41-7.55 (m, 1H), 7.90-8.05 (m, 1H), 10.43-10.60 (m, 1H).

LCMS(ESI): [M+H]+ m/z: calcd 395.2; found 396.2; Rt=1.838 min.

Step 4: The Synthesis of N-(6-amino-5-methyl-3-pyridyl)-2-[(2S,5R)-2-[3-(dimethylamino)phenyl]-5-methyl-1-piperidyl]-2-oxo-acetamide (Compound 387 tert-butyl N-[5-[[2-[(2S,5R)-2-[3-(dimethylamino)phenyl]-5-methyl-1-piperidyl]-2-oxo-acetyl]amino]-3-methyl-2-pyridyl]carbamate Isomer 2 (20.1 mg, 40.56 µmol) was dissolved in dioxane (2 mL) and water (5 mL) mixture. Then reaction mixture was stirred for 15 hr at 100° C. After the completion of the reaction, monitored by LCMS, the resulting suspension was concentrated under reduced pressure. The obtained solid was subjected to HPLC (2-10 min 45-60% H$_2$O-MeCN—NH$_3$ as a mobile phase; loading pump 4 mL MeCN; Triart 100*20 mm 5 mkm column) to afford pure N-(6-amino-5-methyl-3-pyridyl)-2-[(2S,5R)-2-[3-(dimethylamino)phenyl]-5-methyl-1-piperidyl]-2-oxo-acetamide (7 mg, 17.70 µmol, 43.64% yield).

$^1$H NMR (600 MHz, DMSO-d$_6$) δ 0.96-1.02 (m, 3H), 1.25-1.38 (m, 1H), 1.63-1.75 (m, 1H), 1.80-1.91 (m, 1H), 1.97-2.02 (m, 3H), 2.02-2.23 (m, 2H), 2.75-2.79 (m, 0.4H), 2.83-2.90 (m, 6H), 3.24-3.27 (m, 0.6H), 3.40-4.03 (m, 1H), 5.04-5.54 (m, 1H), 5.56-5.66 (m, 2H), 6.55-6.64 (m, 3H), 7.09-7.20 (m, 1H), 7.41-7.52 (m, 1H), 7.92-8.03 (m, 1H), 10.40-10.55 (m, 1H).

LCMS(ESI): [M+H]+ m/z: calcd 395.2; found 396.2; Rt=1.837 min.

Example 397. The Synthesis of Compound 148, Compound 152, Compound 175

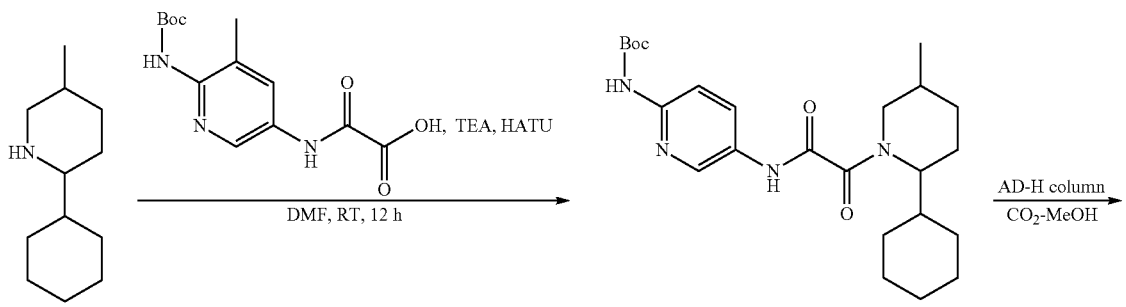

Compound 148

+

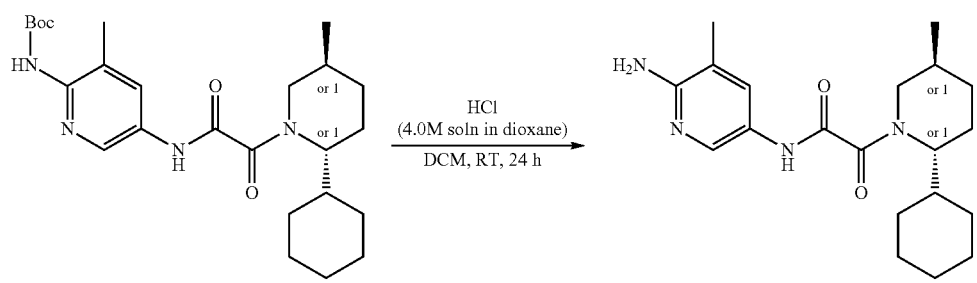

Compound 152

+

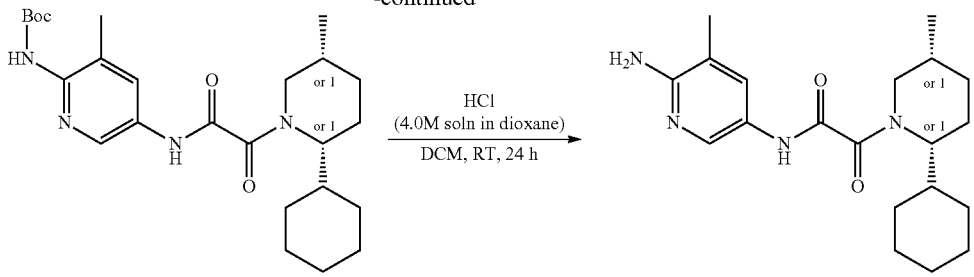

Compound 175

Step 1: The Synthesis of tert-butyl N-[5-[[2-(2-cyclohexyl-5-methyl-1-piperidyl)-2-oxo-acetyl]amino]-3-methyl-2-pyridyl]carbamate 2-[[6-(tert-butoxycarbonylamino)-5-methyl-3-pyridyl]amino]-2-oxo-acetic acid (200 mg, 609.57 μmol) and 2-cyclohexyl-5-methyl-piperidine (165.94 mg, 609.57 μmol, HCl) were mixed in DMF (10 mL). The reaction suspension was cooled to 0° C. and HATU (231.78 mg, 609.57 μmol) followed by TEA (370.09 mg, 3.66 mmol, 509.77 μL) were added. The clear solution was stirred at ambient temperature for 12 h. Then volatiles were evaporated under reduced pressure and residue (1 g) was subjected to RP-HPLC (column: SunFire C18 100*19 mm, 5 um; 60-60-100% 0-1-6 min water-methanol as mobile phase) to give tert-butyl N-[5-[[2-(2-cyclohexyl-5-methyl-1-piperidyl)-2-oxo-acetyl]amino]-3-methyl-2-pyridyl]carbamate (88 mg, 191.89 μmol, 31.48% yield) and 30 mg of Boc-deprotected product (as diastereomeric mixture).

$^1$H NMR (400 MHz, CDCl$_3$) δ 0.93 (m, 6H), 1.15 (m, 6H), 1.56 (m, 16H), 1.91 (m, 2H), 2.28 (s, 3H), 3.47 (m, 1H), 6.60 (s, 1H), 8.03 (m, 1H), 8.32 (s, 1H), 9.17 (s, 1H).

LCMS(ESI): [M+H]$^+$ m/z: calcd 458.2; found 459.4; Rt=4.306 min.

Step 2: The Synthesis Tert-butyl N-[5-[[2-[(2R,5R)-2-cyclohexyl-5-methyl-1-piperidyl]-2-oxo-acetyl]amino]-3-methyl-2-pyridyl]carbamate, Tert-butyl N-[5-[[2-[(2R,5S)-2-cyclohexyl-5-methyl-1-piperidyl]-2-oxo-acetyl]amino]-3-methyl-2-pyridyl]carbamate and Tert-butyl N-[5-[[2-[(2S,5R)-2-cyclohexyl-5-methyl-1-piperidyl]-2-oxo-acetyl]amino]-3-methyl-2-pyridyl]carbamate The diastereomers were separated by chiral HPLC (column: AD-H (I, 250*20, 5 mkm), CO$_2$-MeOH, 80-20, 50 mL/min as mobile phase) to give the mixture of cis-enantiomers tert-butyl N-[5-[[2-[(2R,5R)-2-cyclohexyl-5-methyl-1-piperidyl]-2-oxo-acetyl]amino]-3-methyl-2-pyridyl]carbamate (Isomer 3) (13.3 mg, 29.00 μmol, 30.23% yield), and two individual trans-enantiomers tert-butyl N-[5-[[2-[(2R,5S)-2-cyclohexyl-5-methyl-1-piperidyl]-2-oxo-acetyl]amino]-3-methyl-2-pyridyl]carbamate (Isomer 2) (15.1 mg, 32.93 μmol, 68.64% yield) and tert-butyl N-[5-[[2-[(2S,5R)-2-cyclohexyl-5-methyl-1-piperidyl]-2-oxo-acetyl]amino]-3-methyl-2-pyridyl]carbamate (Isomer 1) (19.4 mg, 42.30 μmol, 88.18% yield).

Compound 1:
$^1$H NMR (500 MHz, CDCl$_3$) δ 0.92 (m, 3H), 1.17 (m, 4H), 1.62 (m, 22H), 2.28 (s, 3H), 4.30 (m, 1H), 4.81 (m, 1H), 6.63 (s, 1H), 8.02 (m, 1H), 8.33 (s, 1H), 9.22 (s, 1H).

LCMS(ESI): [M+2H]$^+$ m/z: calcd 458.2; found 460.2; Rt=6.157 min.

RT (AD-H, CO$_2$-MeOH, 70-30, 3.0 mL/min)=7.018 min.

Compound 2:
$^1$H NMR (400 MHz, CDCl$_3$) δ 0.92 (m, 3H), 1.17 (m, 4H), 1.62 (m, 22H), 2.28 (s, 3H), 4.29 (m, 1H), 4.76 (m, 1H), 6.69 (s, 1H), 8.02 (m, 1H), 8.33 (s, 1H), 9.28 (m, 1H).

LCMS(ESI): [M+2H]$^+$ m/z: calcd 458.2; found 460.2; Rt=6.157 min.

RT (AD-H, CO$_2$-MeOH, 70-30, 3.0 mL/min)=9.507 min.

Compound 3:
$^1$H NMR (500 MHz, CDCl$_3$) δ 0.92 (m, 3H), 1.17 (m, 4H), 1.62 (m, 22H), 2.28 (s, 3H), 4.32 (m, 1H), 4.81 (m, 1H), 6.61 (s, 1H), 8.01 (s, 1H), 8.32 (s, 1H), 9.14 (s, 1H).

LCMS(ESI): [M+2H]$^+$ m/z: calcd 458.2; found 460.2; Rt=6.191 min.

RT (AD-H, CO$_2$-MeOH, 70-30, 3.0 mL/min)=5.690 min and 6.463 min (mixture).

Step 3: The Synthesis N-(6-amino-5-methyl-3-pyridyl)-2-[(2S,5R)-2-cyclohexyl-5-methyl-1-piperidyl]-2-oxo-acetamide (Compound 148

Hydrogen chloride solution 4.0 M in dioxane (110.17 mg, 423.03 μmol, 104.92 μL, 14% purity) was carefully added at r.t. to a solution of tert-butyl N-[5-[[2-[(2S,5R)-2-cyclohexyl-5-methyl-1-piperidyl]-2-oxo-acetyl]amino]-3-methyl-2-pyridyl]carbamate Isomer 1 (19.40 mg, 42.30 μmol) in DCM (2 mL). The reaction mixture was then stirred for 24 hr at r.t. and the solvents were evaporated in vacuo to give 15 mg of crude material. It was subjected to RP-HPLC (column: YMC Triart C18 100*20 mm, 5 um; 50-75%, 0-5 min, 0.1% NH$_3$-methanol as mobile phase) to give Compound 148 N-(6-amino-5-methyl-3-pyridyl)-2-[(2S,5R)-2-cyclohexyl-5-methyl-1-piperidyl]-2-oxo-acetamide (9 mg, 25.11 μmol, 59.35% yield).

$^1$H NMR (Chloroform-d, 400 MHz): δ (ppm) 0.91 (m, 2H), 1.01 (m, 3H), 1.20 (m, 4H), 1.49 (m, 1H), 1.71 (m, 8H), 1.97 (m, 2H), 2.12 (s, 3H), 3.09 (m, 1H), 4.27 (m, 3H), 4.73 (m, 1H), 7.71 (m, 1H), 8.03 (s, 1H), 9.07 (m, 1H).

LCMS(ESI): [M+H]$^+$ m/z: calcd 358.2; found 359.2; Rt=1.166 min.

Step 4: The Synthesis N-(6-amino-5-methyl-3-pyridyl)-2-[(2R,5S)-2-cyclohexyl-5-methyl-1-piperidyl]-2-oxo-acetamide (Compound 152

Hydrogen chloride solution 4.0 M in dioxane (85.75 mg, 329.27 μmol, 81.67 μL, 14% purity) was carefully added at r.t. to a solution of tert-butyl N-[5-[[2-[(2R,5S)-2-cyclohexyl-5-methyl-1-piperidyl]-2-oxo-acetyl]amino]-3-methyl-2-pyridyl]carbamate Isomer 2 (15.10 mg, 32.93

μmol) in DCM (2 mL). The reaction mixture was then stirred for 24 hr at r.t. and the solvents were evaporated in vacuo to give 15 mg of crude material. It was subjected to RP-HPLC (column: YMC Triart C18 100*20 mm, 5 um; 50-75%, 0-5 min, 0.1% $NH_3$-methanol as mobile phase) to give Compound 152 N-(6-amino-5-methyl-3-pyridyl)-2-[(2R,5S)-2-cyclohexyl-5-methyl-1-piperidyl]-2-oxo-acetamide (8 mg, 22.32 μmol, 67.78% yield).

$^1$H NMR (Chloroform-d, 400 MHz): δ (ppm) 0.91 (m, 2H), 1.02 (m, 3H), 1.18 (m, 4H), 1.74 (m, 9H), 1.96 (m, 2H), 2.12 (s, 3H), 3.09 (m, 1H), 4.29 (m, 3H), 4.76 (m, 1H), 7.72 (m, 1H), 8.02 (s, 1H), 9.02 (m, 1H).

LCMS(ESI): [M+H]$^+$ m/z: calcd 358.2; found 359.2; Rt=1.154 min.

Step 5: The Synthesis N-(6-amino-5-methyl-3-pyridyl)-2-[(2R,5R)-2-cyclohexyl-5-methyl-1-piperidyl]-2-oxo-acetamide (Compound 175

Hydrogen chloride solution 4.0 M in dioxane (75.53 mg, 290.02 μmol, 71.93 μL, 14% purity) was carefully added at r.t. to a solution of tert-butyl N-[5-[[2-[(2R,5R)-2-cyclohexyl-5-methyl-1-piperidyl]-2-oxo-acetyl]amino]-3-methyl-2-pyridyl]carbamate Isomer 3 (13.3 mg, 29.00 μmol) in DCM (2 mL). The reaction mixture was then stirred for 24 hr at r.t. and the solvents were evaporated in vacuo to give 15 mg of crude material. It was subjected to RP-HPLC (column: YMC Triart C18 100*20 mm, 5 um; 50-75%, 0-5 min, 0.1% $NH_3$-methanol as mobile phase) to give Compound 175 N-(6-amino-5-methyl-3-pyridyl)-2-[(2R,5R)-2-cyclohexyl-5-methyl-1-piperidyl]-2-oxo-acetamide (6.5 mg, 18.13 μmol, 62.52% yield).

$^1$H NMR (Chloroform-d, 400 MHz): δ (ppm) 0.91 (m, 5H), 1.20 (m, 3H), 1.67 (m, 9H), 1.91 (m, 2H), 2.13 (s, 3H), 2.48 (m, 1H), 4.32 (m, 1H), 4.45 (s, 2H), 4.77 (m, 1H), 7.72 (s, 1H), 8.03 (s, 1H), 8.98 (m, 1H).

LCMS(ESI): [M+H]$^+$ m/z: calcd 358.2; found 359.2; Rt=3.090 min.

Example 398. The Synthesis of N-(6-amino-5-methyl-3-pyridyl)-2-[(2S,5R)-2-(4-aminophenyl)-5-methyl-1-piperidyl]-2-oxo-acetamide (Compound 1081) and N-(6-amino-5-methyl-3-pyridyl)-2-[(2R,5S)-2-(4-aminophenyl)-5-methyl-1-piperidyl]-2-oxo-acetamide (Compound 461

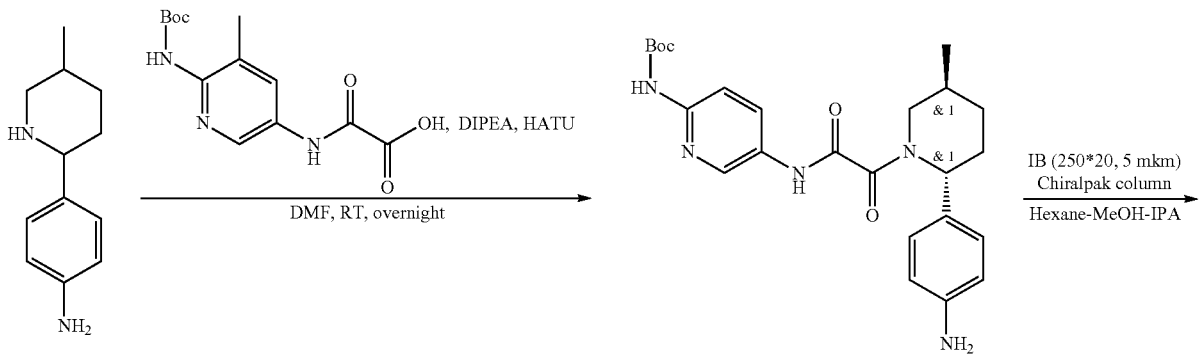

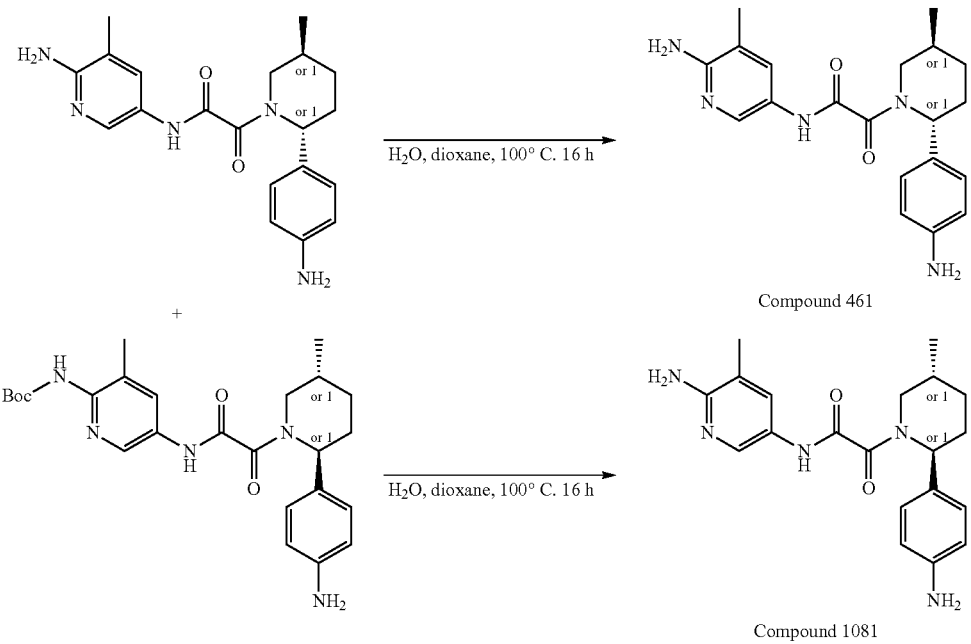

Compound 461

Compound 1081

Step 1: The Synthesis of tert-butyl N-[5-[[2-[(2R,5S)-2-(4-aminophenyl)-5-methyl-1-piperidyl]-2-oxo-acetyl]amino]-3-methyl-2-pyridyl]carbamate DIPEA (765.94 mg, 5.93 mmol, 1.03 mL) was added to the solution of 2-[[6-(tert-butoxycarbonylamino)-5-methyl-3-pyridyl]amino]-2-oxo-acetic acid (0.5 g, 1.69 mmol) and 4-[(2S,5R)-5-methyl-2-piperidyl]aniline (322.20 mg, 1.69 mmol) in DMF (10 mL). The resulting mixture was stirred for 5 min followed by the addition of HATU (708.20 mg, 1.86 mmol). Then, the reaction mixture was stirred overnight at room temperature. After the completion of the reaction, monitored by LCMS, the resulting suspension was concentrated under reduced pressure. The obtained solid was subjected to HPLC (2-10 min 40-60% water/MeCN+NH$_3$ as a mobile phase; loading pump 4 mL MeCN+NH$_3$; column: TRIART 100*20 5 mkm) to afford pure tert-butyl N-[5-[[2-[(2R,5S)-2-(4-aminophenyl)-5-methyl-1-piperidyl]-2-oxo-acetyl]amino]-3-methyl-2-pyridyl]carbamate (174 mg, 372.15 µmol, 21.98% yield).

$^1$H NMR (400 MHz, CDCl$_3$) δ 1.12 (m, 3H), 1.43 (m, 2H), 1.52 (d, 9H), 1.96 (m, 2H), 2.18 (m, 5H), 2.87 (m, 1H), 3.32 (m, 1H), 4.22 (m, 1H), 4.62 (m, 1H), 5.74 (m, 1H), 6.62 (m, 2H), 7.29 (m, 2H), 8.11 (s, 1H), 8.42 (m, 1H), 9.41 (m, 1H).

LCMS(ESI): [M+H]$^+$ m/z: calcd 467.2; found 468.2; Rt=1.018 min.

Step 2: Chiral Resolution of Tert-butyl N-[5-[[2-[(2R,5S)-2-(4-aminophenyl)-5-methyl-1-piperidyl]-2-oxo-acetyl]amino]-3-methyl-2-pyridyl]carbamate Chiral separation was performed using IB (250*20, 5 mkm) Chiralpak column; Hexane-MeOH-IPA, 80-10-10 as a mobile phase; Flow rate 15 mL/min; Injection volume: 900 mkL affording two isomers: tert-butyl (5-(2-((2R,5S)-2-(4-aminophenyl)-5-methylpiperidin-1-yl)-2-oxoacetamido)-3-methylpyridin-2-yl)carbamate Isomer 1(174.0 mg, 32.06% yield; RT (IB-3, Hexane-IPA-MeOH, 70-15-15, 0.15 mL/min)=8.93 min)) and tert-butyl (5-(2-((2S,5R)-2-(4-aminophenyl)-5-methylpiperidin-1-yl)-2-oxoacetamido)-3-methylpyridin-2-yl)carbamate Isomer 2 (174.0 mg, 35.00% yield; RT (IB-3, Hexane-IPA-MeOH, 70-15-15, 0.15 mL/min)=14.96 min).

Isomer 1: RT (IB-3, Hexane-IPA-MeOH, 70-15-15, 0.15 mL/min)=8.93 min

LCMS(ESI): [M+2H]$^+$ m/z: calcd 467.2; found 469.2; Rt=4.211 min.

Isomer 2: RT (IB-3, Hexane-IPA-MeOH, 70-15-15, 0.15 mL/min)=14.96 min

LCMS(ESI): [M+2H]$^+$ m/z: calcd 467.2; found 469.2; Rt=4.196 min.

Step 3: The Synthesis of N-(6-amino-5-methyl-3-pyridyl)-2-[(2R,5S)-2-(4-aminophenyl)-5-methyl-1-piperidyl]-2-oxo-acetamide (Compound 461 tert-butyl N-[5-[[2-[(2R,5S)-2-(4-aminophenyl)-5-methyl-1-piperidyl]-2-oxo-acetyl]amino]-3-methyl-2-pyridyl]carbamate Isomer 1 (55.78 mg, 119.30 µmol) was dissolved in the mixture of dioxane (2 mL) and water (5 mL). Then, the reaction mixture was stirred for 16 hr at 100° C. After the completion of the reaction, monitored by LCMS, the resulting suspension was concentrated under reduced pressure. The obtained solid was subjected to HPLC (2-10 min 40-60% water/MeCN+NH$_3$ as a mobile phase; loading pump 4 mL; TRIART 100*20 5 microM column) to afford pure N-(6-amino-5-methyl-3-pyridyl)-2-[(2R,5S)-2-(4-aminophenyl)-5-methyl-1-piperidyl]-2-oxo-acetamide (9.8 mg, 26.67 µmol, 22.36% yield).

$^1$H NMR (600 MHz, DMSO-d$_6$) δ 0.94-1.04 (m, 3H), 1.23-1.36 (m, 1H), 1.65-1.75 (m, 1H), 1.75-1.87 (m, 1H), 1.87-1.98 (m, 1H), 1.98-2.05 (m, 3H), 2.06-2.15 (m, 1H), 2.65-3.25 (m, 1H), 3.35-3.97 (m, 1H), 4.89-5.49 (m, 3H), 5.54-5.64 (m, 2H), 6.50-6.59 (m, 2H), 6.88-7.00 (m, 2H), 7.41-7.51 (m, 1H), 7.92-8.08 (m, 1H), 10.36-10.54 (m, 1H).

LCMS(ESI): [M+H]$^+$ m/z: calcd 367.2; found 368.2; Rt=1.524 min.

Step 4: The Synthesis of N-(6-amino-5-methyl-3-pyridyl)-2-[(2S,5R)-2-(4-aminophenyl)-5-methyl-1-piperidyl]-2-oxo-acetamide (Compound 1081 tert-butyl N-[5-[[2-[(2S,5R)-2-(4-aminophenyl)-5-methyl-1-piperidyl]-2-oxo-acetyl]amino]-3-methyl-2-pyridyl]carbamate Isomer 2 (60.9 mg, 130.25 µmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (2-10 min 40-60% water/MeCN+NH$_3$ as a mobile phase; loading pump 4 mL; TRIART 100*20 5 microM column) to afford pure N-(6-amino-5-methyl-3-pyridyl)-2-[(2S,5R)-2-(4-aminophenyl)-5-methyl-1-piperidyl]-2-oxo-acetamide (14.8 mg, 40.28 µmol, 30.92% yield).

$^1$H NMR (600 MHz, DMSO-d$_6$) δ 0.91-1.04 (m, 3H), 1.20-1.37 (m, 1H), 1.60-1.97 (m, 3H), 1.97-2.04 (m, 3H), 2.05-2.16 (m, 1H), 2.63-3.24 (m, 1H), 3.34-3.96 (m, 1H), 4.94-5.48 (m, 3H), 5.54-5.63 (m, 2H), 6.48-6.56 (m, 2H), 6.88-7.00 (m, 2H), 7.41-7.52 (m, 1H), 7.93-8.04 (m, 1H), 10.36-10.54 (m, 1H).

LCMS(ESI): [M+H]$^+$ m/z: calcd 367.2; found 368.2; Rt=1.928 min.

Example 399. The Synthesis of N-(6-amino-5-methyl-3-pyridyl)-2-[(2R,5S)-2-[4-(methanesulfonamido)phenyl]-5-methyl-1-piperidyl]-2-oxo-acetamide (Compound 499) and N-(6-amino-5-methyl-3-pyridyl)-2-[(2S,5R)-2-[4-(methanesulfonamido)phenyl]-5-methyl-1-piperidyl]-2-oxo-acetamide (Compound 506)
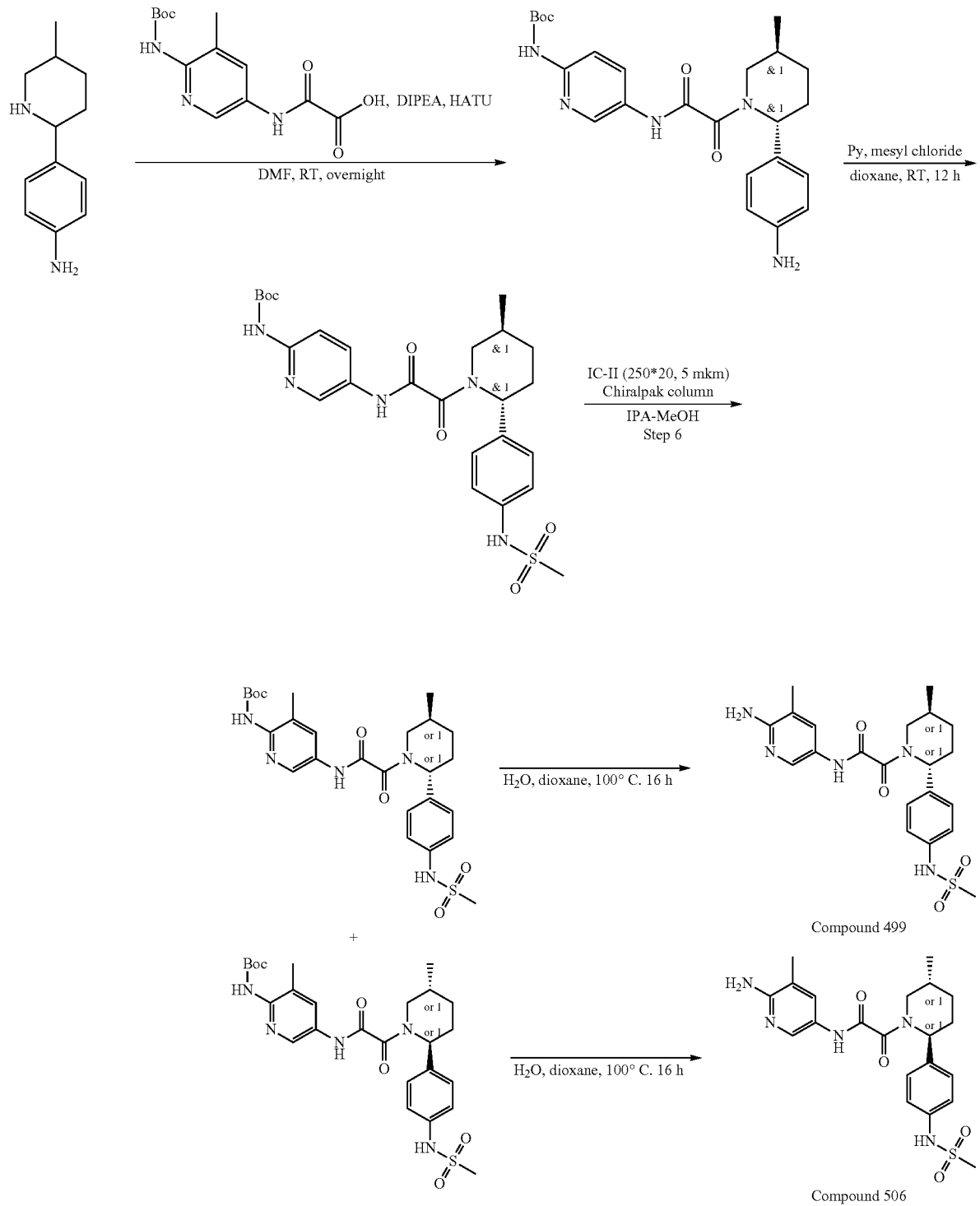

Step 1: The Synthesis of tert-butyl N-[5-[[2-[(2R,5S)-2-[4-(methanesulfonamido)phenyl]-5-methyl-1-piperidyl]-2-oxo-acetyl]amino]-3-methyl-2-pyridyl]carbamate To a pre-cooled solution of tert-butyl N-[5-[[2-[(2R,5S)-2-(4-aminophenyl)-5-methyl-1-piperidyl]-2-oxo-acetyl]amino]-3-methyl-2-pyridyl]carbamate (156.8 mg, 335.36 µmol) in dioxane (10 mL), pyridine (66.32 mg, 838.40 µmol, 67.81 µL) was added. After that, methanesulfonyl chloride (42.26 mg, 368.89 µmol, 28.55 µL) was added dropwise at 0° C. Then, the reaction mixture was stirred for 12 hr at room temperature. After the completion of the reaction, monitored by LCMS, the resulting suspension was concentrated under reduced pressure. The obtained solid was subjected to HPLC (2-10 min 40-60% water/MeCN+$NH_3$ as a mobile phase; loading pump 4 mL; TRIART 100*20 5 microM column) to afford pure tert-butyl N-[5-[[2-[(2R,5S)-2-[4-(methanesulfonamido)phenyl]-5-methyl-1-piperidyl]-2-oxo-acetyl]amino]-3-methyl-2-pyridyl]carbamate (74.6 mg, 136.72 µmol, 40.77% yield).

$^1$H NMR (400 MHz, $CDCl_3$) δ 1.2 (m, 3H), 1.34 (m, 2H), 1.49 (s, 9H), 2.1 (m, 9H), 3.12 (s, 3H), 3.62 (m, 1H), 4.32 (m, 1H), 6.02 (m, 1H), 7.21 (m, 3H), 8.12 (m, 1H), 8.36 (m, 1H), 9.52 (m, 1H).

LCMS(ESI): [M+H]$^+$ m/z: calcd 545.2; found 546.2; Rt=3.362 min.

Step 2: Chiral Separation of Tert-butyl N-[5-[[2-[(2R,5S)-2-[4-(methanesulfonamido)phenyl]-5-methyl-1-piperidyl]-2-oxo-acetyl]amino]-3-methyl-2-pyridyl]carbamate Chiral separation of tert-butyl N-[5-[[2-[(2R,5S)-2-[4-(methanesulfonamido)phenyl]-5-methyl-1-piperidyl]-2-oxo-acetyl]amino]-3-methyl-2-pyridyl]carbamate was performed using IC-II (250*20, 5 mkm) column; IPA-MeOH, 50-50 as a mobile phase; flow rate 12 mL/min; affording two isomers: tert-butyl N-[5-[[2-[(2R,5S)-2-[4-(methanesulfonamido)phenyl]-5-methyl-1-piperidyl]-2-oxo-acetyl]amino]-3-methyl-2-pyridyl]carbamate (isomer 1: RT (IC column; MeOH-IPA, 50-50, 0.6 mL/min)=19.14 min; 14.78 mg, 33.22% yield) and tert-butyl N-[5-[[2-[(2S,5R)-2-[4-(methanesulfonamido)phenyl]-5-methyl-1-piperidyl]-2-oxo-acetyl]amino]-3-methyl-2-pyridyl]carbamate (isomer 1: RT (IC column; MeOH-IPA, 50-50, 0.6 mL/min)=11.48 min; 23.98 mg, 32.14% yield).

Isomer 1: RT (IC column; MeOH-IPA, 50-50, 0.6 mL/min)=19.14 min

LCMS(ESI): [M+H]$^+$ m/z: calcd 545.2; found 546.2; Rt=1.270 min.

Isomer 2: RT (IC column; MeOH-IPA, 50-50, 0.6 mL/min)=11.48 min

LCMS(ESI): [M+H]$^+$ m/z: calcd 545.2; found 546.2; Rt=1.270 min.

Step 3: The Synthesis of N-(6-amino-5-methyl-3-pyridyl)-2-[(2R,5S)-2-[4-(methanesulfonamido)phenyl]-5-methyl-1-piperidyl]-2-oxo-acetamide (Compound 499 tert-butyl N-[5-[[2-[(2R,5S)-2-[4-(methanesulfonamido)phenyl]-5-methyl-1-piperidyl]-2-oxo-acetyl]amino]-3-methyl-2-pyridyl]carbamate isomer 1(14.78 mg, 45.41 µmol) was dissolved in dioxane (2 mL) and water (5 mL) mixture. Then, the reaction mixture was stirred for 16 hr at 100° C. After the completion of the reaction, monitored by LCMS, the resulting suspension was concentrated under reduced pressure. The obtained solid was subjected to HPLC (2-10 min, 25-70% MeCN—$H_2O$ as a mobile phase; flow rate: 30 mL/min; loading pump 4 mL, MeCN; SunFire 100*19 mm, 5 mkm column) to afford pure N-(6-amino-5-methyl-3-pyridyl)-2-[(2R,5S)-2-[4-(methanesulfonamido)phenyl]-5-methyl-1-piperidyl]-2-oxo-acetamide (13.6 mg, 30.53 µmol, 67.22% yield).

$^1$H NMR (600 MHz, DMSO-$d_6$) δ 0.95-1.04 (m, 3H), 1.25-1.37 (m, 1H), 1.60-1.72 (m, 1H), 1.80-1.91 (m, 1H), 1.96-2.07 (m, 4H), 2.12-2.21 (m, 1H), 2.68-2.74 (m, OH), 2.93-2.97 (m, 3H), 3.16-3.21 (m, 1H), 3.41-4.01 (m, 1H), 5.04-5.55 (m, 1H), 5.55-5.65 (m, 2H), 7.15-7.21 (m, 2H), 7.22-7.31 (m, 2H), 7.40-7.51 (m, 1H), 7.91-8.03 (m, 1H), 9.66-9.76 (m, 1H), 10.38-10.50 (m, 1H).

LCMS(ESI): [M+H]$^+$ m/z: calcd 445.3; found 446.2; Rt=2.479 min.

Step 4: The Synthesis of N-(6-amino-5-methyl-3-pyridyl)-2-[(2S,5R)-2-[4-(methanesulfonamido)phenyl]-5-methyl-1-piperidyl]-2-oxo-acetamide (Compound 506 tert-butyl N-[5-[[2-[(2S,5R)-2-[4-(methanesulfonamido)phenyl]-5-methyl-1-piperidyl]-2-oxo-acetyl]amino]-3-methyl-2-pyridyl]carbamate isomer 2 (23.98 mg, 43.95 µmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (2-10 min, 25-70% MeCN—$H_2O$ as a mobile phase; flow rate: 30 mL/min; loading pump 4 mL, MeCN; SunFire 100*19 mm, 5 mkm column) to afford pure N-(6-amino-5-methyl-3-pyridyl)-2-[(2S,5R)-2-[4-(methanesulfonamido)phenyl]-5-methyl-1-piperidyl]-2-oxo-acetamide (12 mg, 26.93 µmol, 61.29% yield).

$^1$H NMR (600 MHz, DMSO-$d_6$) δ 0.97-1.03 (m, 3H), 1.26-1.36 (m, 1H), 1.60-1.72 (m, 1H), 1.80-1.93 (m, 1H), 1.96-2.09 (m, 4H), 2.11-2.23 (m, 1H), 2.68-2.73 (m, 0.4H), 2.93-2.97 (m, 3H), 3.17-3.20 (m, 0.6H), 3.47-4.00 (m, 1H), 5.05-5.55 (m, 1H), 5.56-5.66 (m, 2H), 7.16-7.22 (m, 2H), 7.23-7.32 (m, 2H), 7.40-7.52 (m, 1H), 7.94-8.05 (m, 1H), 9.61-9.79 (m, 1H), 10.40-10.50 (m, 1H).

LCMS(ESI): [M+H]$^+$ m/z: calcd 445.3; found 446.2; Rt=2.467 min.

Example 400. The Synthesis of 2-[(2R,5S)-2-(4-acetamidophenyl)-5-methyl-1-piperidyl]-N-(6-amino-5-methyl-3-pyridyl)-2-oxo-acetamide (Compound 527) and 2-[(2S,5R)-2-(4-acetamidophenyl)-5-methyl-1-piperidyl]-N-(6-amino-5-methyl-3-pyridyl)-2-oxo-acetamide (Compound 523

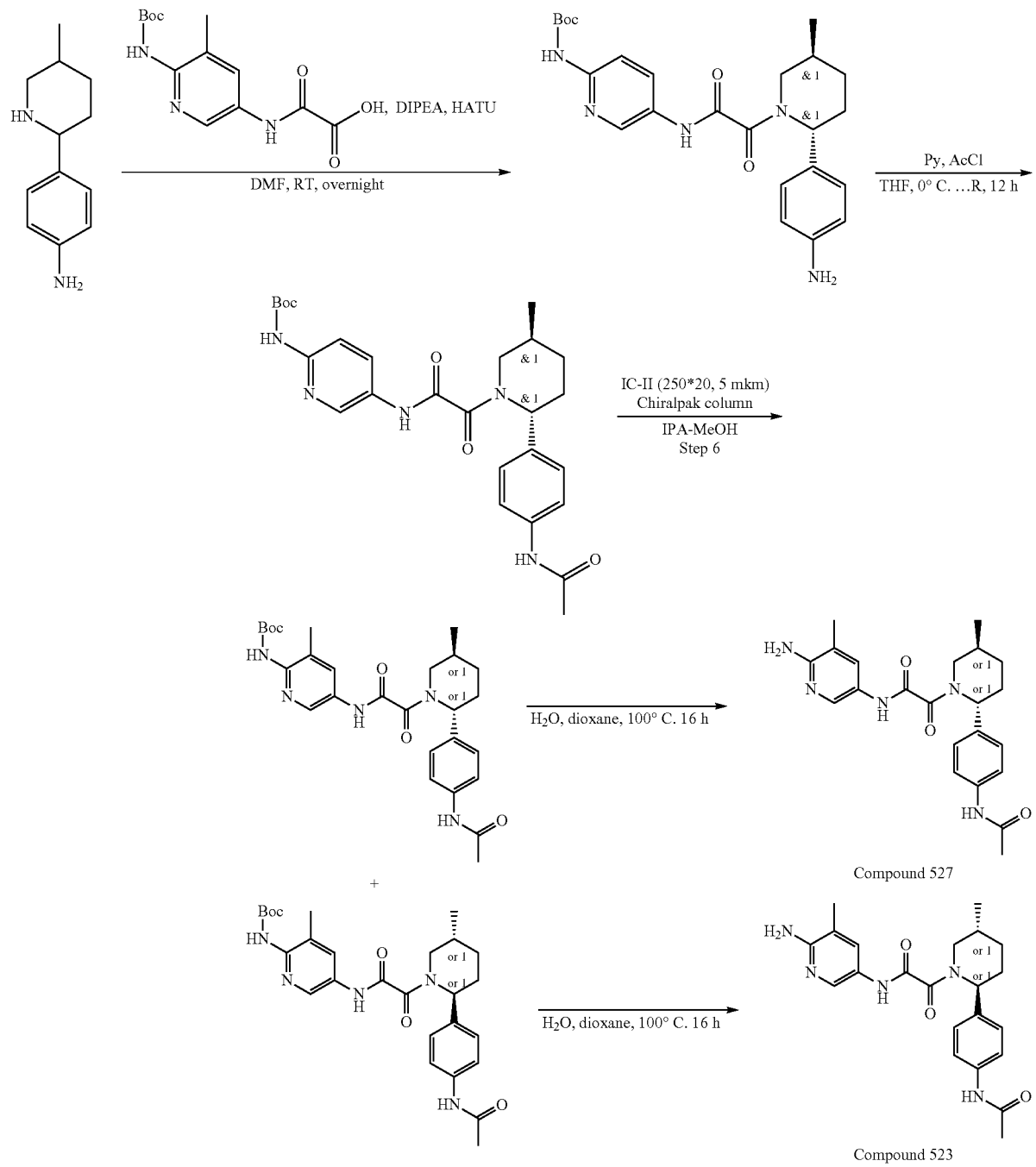

Step 1: The Synthesis of tert-butyl N-[5-[[2-[(2R,5S)-2-(4-acetamidophenyl)-5-methyl-1-piperidyl]-2-oxo-acetyl]amino]-3-methyl-2-pyridyl]carbamate To a pre-cooled solution of tert-butyl N-[5-[[2-[(2R,5S)-2-(4-aminophenyl)-5-methyl-1-piperidyl]-2-oxo-acetyl]amino]-3-methyl-2-pyridyl]carbamate (155 mg, 331.51 µmol) in THF (15 mL), pyridine (65.56 mg, 828.77 µmol, 67.03 µL) was added. After that Acetyl chloride (28.62 mg, 364.66 µmol, 22.19 µL) was added dropwise at 0° C. Then, the reaction mixture was stirred for 12 hr at room temperature. After the completion of the reaction, monitored by LCMS, the resulting suspension was concentrated under reduced pressure. The obtained solid was subjected to HPLC (2-10 min 50-70% MeOH/H$_2$O as a mobile phase; flow rate 30 mL/min; loading pump 4 mL MeOH; SunFire 100*19 mm, 5 mkm column) to afford pure tert-butyl N-[5-[[2-[(2R,5S)-2-(4-acetamidophenyl)-5-methyl-1-piperidyl]-2-oxo-acetyl]amino]-3-methyl-2-pyridyl]carbamate (76 mg, 149.14 µmol, 44.99% yield).

LCMS(ESI): [M+H]$^+$ m/z: calcd 509.2; found 510.2; Rt=2.784 min.

Step 2: Chiral Separation of Tert-butyl N-[5-[[2-[(2R,5S)-2-(4-acetamidophenyl)-5-methyl-1-piperidyl]-2-oxo-acetyl]amino]-3-methyl-2-pyridyl]carbamate Chiral separation of tert-butyl N-[5-[[2-[(2R,5S)-2-(4-acetamidophenyl)-5-methyl-1-piperidyl]-2-oxo-acetyl]amino]-3-methyl-2-pyridyl]carbamate was performed using IC-I (250*20, 5 mkm) column; IPA-MeOH, 50-50 as a mobile phase; flow rate 11 mL/min affording two isomers: tert-butyl N-[5-[[2-[(2R,5S)-2-(4-acetamidophenyl)-5-methyl-1-piperidyl]-2-oxo-acetyl]amino]-3-methyl-2-pyridyl]carbamate Isomer 1 (RT (IC column, MeOH-IPA, 50-50, 0.6 mL/min)=10.07 min; 22.33 mg, 35.67% yield) and tert-butyl N-[5-[[2-[(2S,5R)-2-(4-acetamidophenyl)-5-methyl-1-piperidyl]-2-oxo-acetyl]amino]-3-methyl-2-pyridyl]carbamate Isomer 2 (RT (IC column, MeOH-IPA, 50-50, 0.6 mL/min)=38.88 min; 53.20 mg, 29.38% yield).

Isomer 1: RT (IC column, MeOH-IPA, 50-50, 0.6 mL/min)=10.07 min

LCMS(ESI): [M+H]$^+$ m/z: calcd 509.2; found 510.2; Rt=2.843 min.

Isomer 2: RT (IC column, MeOH-IPA, 50-50, 0.6 mL/min)=38.88 min

LCMS(ESI): [M+H]$^+$ m/z: calcd 509.2; found 510.2; Rt=2.839 min.

Step 3: The Synthesis of 2-[(2R,5S)-2-(4-acetamidophenyl)-5-methyl-1-piperidyl]-N-(6-amino-5-methyl-3-pyridyl)-2-oxo-acetamide (Compound 527 tert-butyl N-[5-[[2-[(2R,5S)-2-(4-acetamidophenyl)-5-methyl-1-piperidyl]-2-oxo-acetyl]amino]-3-methyl-2-pyridyl]carbamate Isomer 1 (22.33 mg, 43.82 µmol) was dissolved in water (5 mL) and dioxane (2 mL) mixture. Then reaction mixture was stirred for 17 hr at 100° C. After the completion of the reaction, monitored by LCMS, the resulting suspension was concentrated under reduced pressure. The obtained solid was subjected to HPLC (2-10 min 40-60% water/MeOH as a solvent mixture; loading pump 4 mL MeOH; TRIART 100*20 5 microM as a column) to afford pure 2-[(2R,5S)-2-(4-acetamidophenyl)-5-methyl-1-piperidyl]-N-(6-amino-5-methyl-3-pyridyl)-2-oxo-acetamide (14.2 mg, 34.68 µmol, 79.14% yield).

$^1$H NMR (600 MHz, DMSO-d$_6$) δ 0.94-1.02 (m, 3H), 1.24-1.38 (m, 1H), 1.60-1.74 (m, 1H), 1.76-1.91 (m, 1H), 1.92-2.04 (m, 7H), 2.10-2.23 (m, 1H), 2.66-3.25 (m, 1H), 3.38-3.99 (m, 1H), 5.06-5.56 (m, 1H), 5.56-5.69 (m, 2H), 7.16-7.30 (m, 2H), 7.40-7.49 (m, 1H), 7.52-7.59 (m, 2H), 7.92-8.05 (m, 1H), 9.88-9.96 (m, 1H), 10.36-10.53 (m, 1H).

LCMS(ESI): [M+H]$^+$ m/z: calcd 409.2; found 410.4; Rt=1.894 min.

Step 4: The Synthesis of 2-[(2S,5R)-2-(4-acetamidophenyl)-5-methyl-1-piperidyl]-N-(6-amino-5-methyl-3-pyridyl)-2-oxo-acetamide (Compound 523 tert-butyl N-[5-[[2-[(2S,5R)-2-(4-acetamidophenyl)-5-methyl-1-piperidyl]-2-oxo-acetyl]amino]-3-methyl-2-pyridyl]carbamate Isomer 2 (27.11 mg, 53.20 µmol) was dissolved in water (5 mL) and dioxane (2 mL) mixture. Then reaction mixture was stirred for 17 hr at 100° C. After the completion of the reaction, monitored by LCMS, the resulting suspension was concentrated under reduced pressure. The obtained solid was subjected to HPLC (2-10 min 40-60% water/MeOH as a solvent mixture; loading pump 4 mL MeOH; TRIART 100*20 5 microM as a column) to afford pure 2-[(2S,5R)-2-(4-acetamidophenyl)-5-methyl-1-piperidyl]-N-(6-amino-5-methyl-3-pyridyl)-2-oxo-acetamide (17.5 mg, 42.74 µmol, 80.33% yield).

$^1$H NMR (600 MHz, DMSO-d$_6$) δ 0.92-1.03 (m, 3H), 1.23-1.39 (m, 1H), 1.58-1.73 (m, 1H), 1.76-1.92 (m, 1H), 1.94-2.06 (m, 7H), 2.08-2.22 (m, 1H), 2.66-3.21 (m, 1H), 3.36-4.02 (m, 1H), 5.06-5.56 (m, 1H), 5.56-5.66 (m, 2H), 7.16-7.29 (m, 2H), 7.38-7.49 (m, 1H), 7.51-7.60 (m, 2H), 7.93-8.05 (m, 1H), 9.88-9.98 (m, 1H), 10.39-10.50 (m, 1H).

LCMS(ESI): [M+H]$^+$ m/z: calcd 409.2; found 410.2; Rt=1.90 min.

Example 401. The Synthesis of N-(6-amino-5-methylpyridin-3-yl)-2-(2-(4-hydroxyphenyl)-5-methylpiperidin-1-yl)-2-oxoacetamide (Compound 397, Compound 396

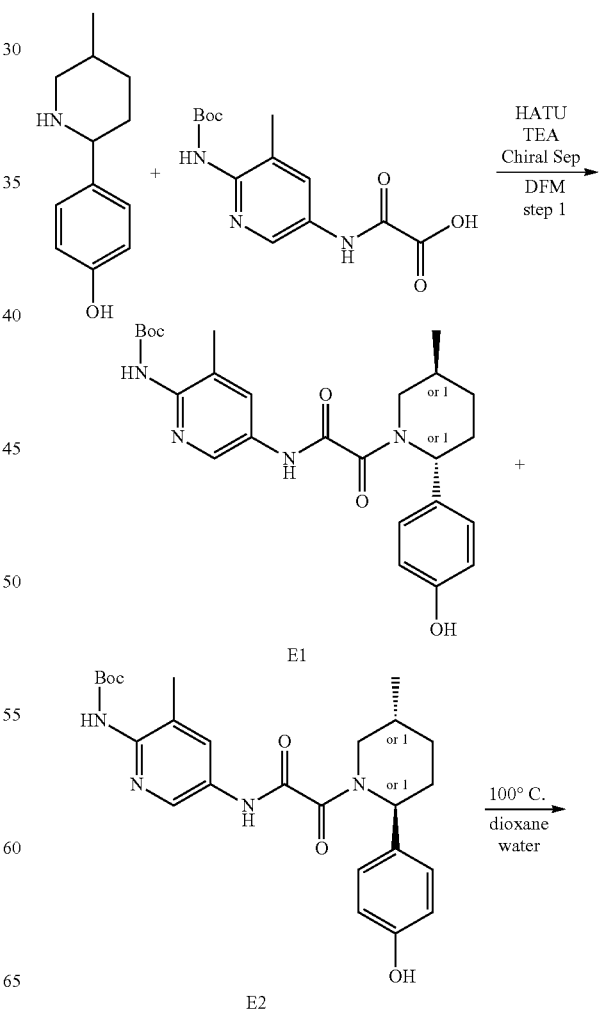

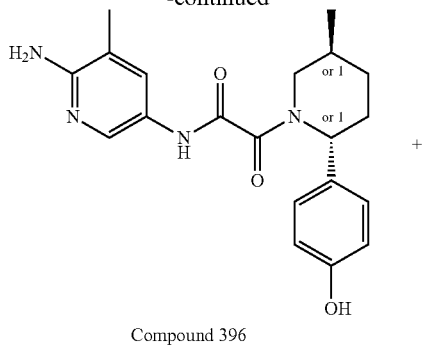

Compound 396

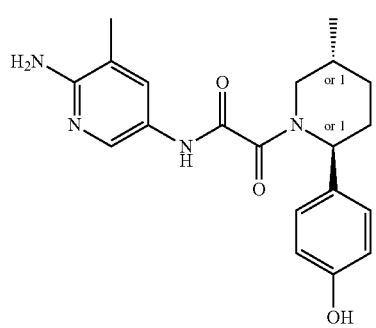

Compound 397

Step 1: Synthesis of tert-butyl (5-(2-(2-(4-hydroxyphenyl)-5-methylpiperidin-1-yl)-2-oxoacetamido)-3-methylpyridin-2-yl)carbamate A mixture of 4-(5-methyl-2-piperidyl)phenol (300 mg, 895.80 µmol, HCl), 2-[[6-(tert-butoxycarbonylamino)-5-methyl-3-pyridyl]amino]-2-oxo-acetic acid (264.52 mg, 895.80 µmol) and TEA (906.46 mg, 8.96 mmol, 1.25 mL) in DMF (10 mL) was stirred at 25° C. for 0.25 hr, then HATU (340.61 mg, 895.80 µmol) was added in small portions over 0.5 hr. The reaction mixture was stirred at 25° C. for 2 hr, then concentrated in vacuo to 5 ml and submitted to reverse phase HPLC (column: XBridge C18 100×20 mm, 5 um; mobile phase 40-80% 0-5 min 0.1% NH$_3$-MeOH, flow: 30 ml/min), which afforded 190 mg of the racemic amide, which was then submitted to preparative chiral HPLC (Column: Chiralpak IC (250*20 mm, 5 mkm); CO$_2$-MeOH, 55-45. Flow Rate: 35 mL/min; Column Temperature: 40'C; Wavelength: 215 nm.) to afford tert-butyl N-[5-[[2-[(2S,5R)-2-(4-hydroxyphenyl)-5-methyl-1-piperidyl]-2-oxo-acetyl]amino]-3-methyl-2-pyridyl]carbamate E1 (49 mg, 104.58 µmol, 11.67% yield) (RT=5.47 min) and tert-butyl N-[5-[[2-[(2R,5S)-2-(4-hydroxyphenyl)-5-methyl-1-piperidyl]-2-oxo-acetyl]amino]-3-methyl-2-pyridyl]carbamate E2 (67 mg, 143.00 µmol, 15.96% yield) (RT=23.21 min) as light-yellow gums, which were used directly in the next step. Ret time for E1 in analytical conditions (column: IC, CO$_2$-MeOH, 50-50, 2 ml/min as mobile phase) 8.40 min and for E2 3.72 min.

E1: Retention time: 8.40 min $^1$H NMR (500 MHz, DMSO-d$_6$) δ (ppm)

LCMS(ESI): [M]$^+$ m/z: calcd 468.5; found 469.2; Rt=4.932 min.

E2: Retention time: 3.72 min $^1$H NMR (500 MHz, DMSO-d$_6$) δ (ppm)

LCMS(ESI): [M]$^+$ m/z: calcd 468.5; found 469.2; Rt=4.924 min.

Step 2: N-(6-amino-5-methylpyridin-3-yl)-2-(2-(4-hydroxyphenyl)-5-methylpiperidin-1-yl)-2-oxoacetamide (Compound 397 and Compound 396

A solution of tert-butyl N-[5-[[2-[(2S,5R)-2-(4-hydroxyphenyl)-5-methyl-1-piperidyl]-2-oxo-acetyl]amino]-3-methyl-2-pyridyl]carbamate E1 (49 mg, 104.58 µmol) and tert-butyl N-[5-[[2-[(2R,5S)-2-(4-hydroxyphenyl)-5-methyl-1-piperidyl]-2-oxo-acetyl]amino]-3-methyl-2-pyridyl]carbamate E2 (67 mg, 143.00 µmol) in a mixture of water (2 mL) and 1,4-dioxan (1.5 mL) was stirred at 95° C. for 18 hr, then cooled down and submitted to reverse phase HPLC (column: YMC Triart C18 100×20 mm, 5 um; mobile phase 30-30-80% 0-1-6 min 0.1% NH$_3$-MeOH, flow: 30 ml/min) to afford Compound 397 N-(6-amino-5-methyl-3-pyridyl)-2-[(2S,5R)-2-(4-hydroxyphenyl)-5-methyl-1-piperidyl]-2-oxo-acetamide (25.7 mg, 69.76 µmol, 66.70% yield) and Compound 396 N-(6-amino-5-methyl-3-pyridyl)-2-[(2R,5S)-2-(4-hydroxyphenyl)-5-methyl-1-piperidyl]-2-oxo-acetamide (33.5 mg, 90.93 µmol, 63.59% yield) as white solid.

Compound 397:

$^1$H NMR (600 MHz, DMSO-d$_6$) δ (ppm) 0.96-1.01 (m, 3H), 1.26-1.36 (m, 1H), 1.63-1.75 (m, 1H), 1.78-1.89 (m, 1H), 1.93-2.04 (m, 4H), 2.11-2.19 (m, 1H), 2.68-3.18 (m, 1H), 3.37-3.96 (m, 1H), 4.96-5.52 (m, 1H), 5.53-5.66 (m, 2H), 6.69-6.79 (m, 2H), 7.04-7.15 (m, 2H), 7.39-7.53 (m, 1H), 7.91-8.06 (m, 1H), 9.26-9.38 (m, 1H), 10.40-10.51 (m, 1H).

LCMS(ESI): [M]$^+$ m/z: calcd 368.4; found 369.2; Rt=2.013 min.

Compound 396:

$^1$H NMR (600 MHz, DMSO-d$_6$) δ (ppm) 0.95-1.01 (m, 3H), 1.25-1.35 (m, 1H), 1.61-1.75 (m, 1H), 1.78-1.90 (m, 1H), 1.91-2.03 (m, 4H), 2.09-2.19 (m, 1H), 2.65-3.22 (m, 1H), 3.40-3.98 (m, 1H), 4.98-5.52 (m, 1H), 5.54-5.67 (m, 2H), 6.71-6.77 (m, 2H), 7.05-7.16 (m, 2H), 7.42-7.50 (m, 1H), 7.93-8.04 (m, 1H), 9.08-9.49 (m, 1H), 10.32-10.67 (m, 1H).

LCMS(ESI): [M]$^+$ m/z: calcd 368.4; found 369.2; Rt=1.932 min.

Example 402. The Synthesis of N-(6-amino-5-methyl-3-pyridyl)-2-[(2S,5S)-4,4-difluoro-5-methyl-2-phenyl-1-piperidyl]-2-oxo-acetamide (Compound 713), N-(6-amino-5-methyl-3-pyridyl)-2-[(2R,5R)-4,4-difluoro-5-methyl-2-phenyl-1-piperidyl]-2-oxo-acetamide (Compound 735 was added and the mixture was stirred for 15 min at 0° C. (2R,5R)-4,4-difluoro-5-methyl-2-phenyl-piperidine (0.36 g, 1.70 mmol) was added and the mixture was warmed to r.t. and stirred for 3 hr. Ethyl acetate was added and organic phase was washed with brine three times. Organic phase was dried over Na₂SO₄, filtered and concentrated in vacuo at 45° C. to give crude product which was purified by HPLC (2-10

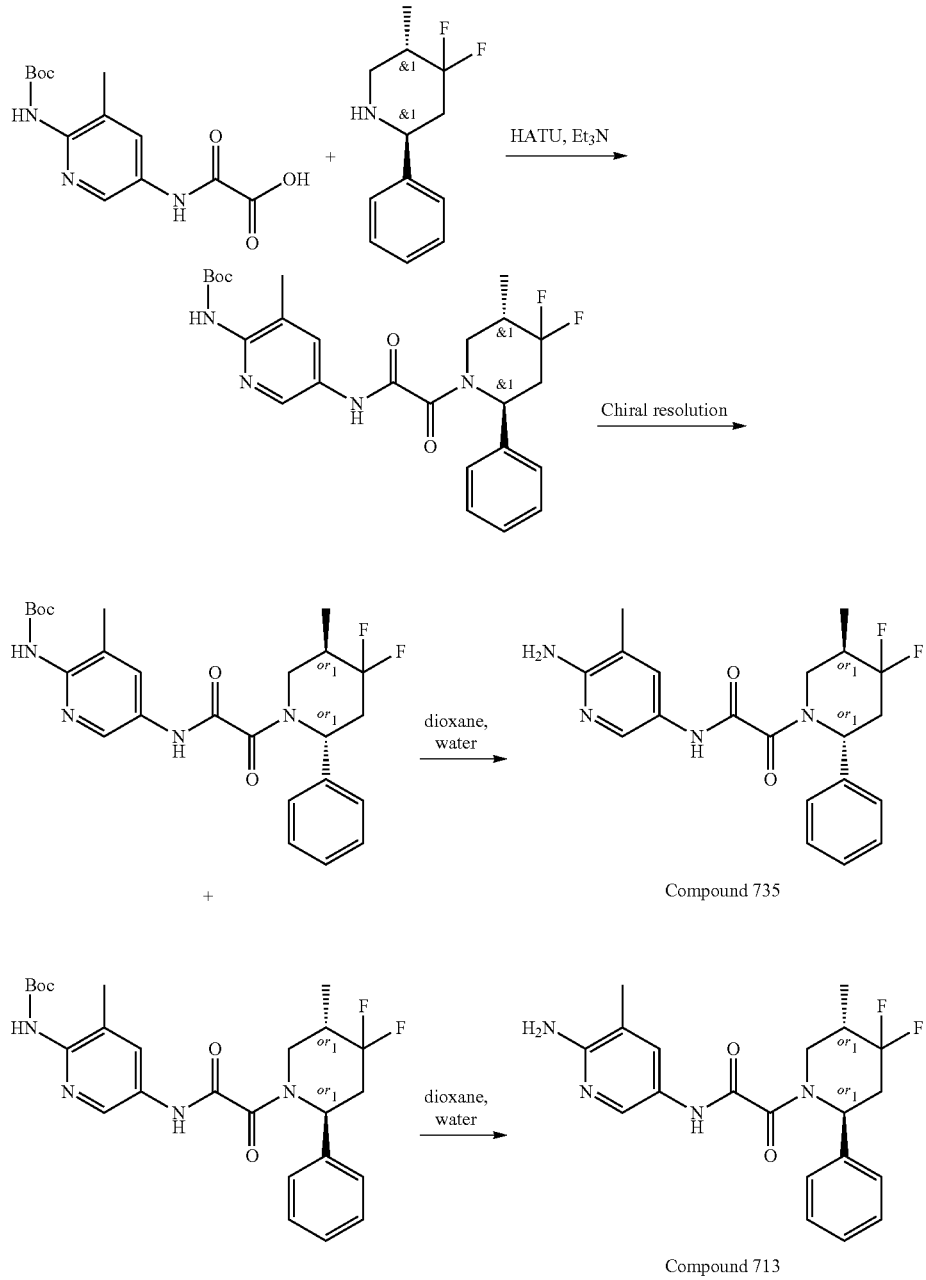

Compound 735

Compound 713

Step 1: Synthesis of rac-tert-butyl N-[5-[[2-[(2R,5R)-4,4-difluoro-5-methyl-2-phenyl-1-piperidyl]-2-oxo-acetyl]amino]-3-methyl-2-pyridyl]carbamate 2-[[6-(tert-butoxycarbonyl amino)-5-methyl-3-pyridyl]amino]-2-oxo-acetic acid (503.22 mg, 1.70 mmol) and TEA (1.72 g, 17.04 mmol, 2.38 mL) were dissolved in DMF (8 mL) and cooled to 0° C., HATU (971.95 mg, 2.56 mmol)

min 60-80% methanol/H₂O 30 ml/min (loading pump 4 ml methanol) column: SunFire 100*19 mm, 5 micro) to give tert-butyl N-[5-[[2-[(2R,5R)-4,4-difluoro-5-methyl-2-phenyl-1-piperidyl]-2-oxo-acetyl]amino]-3-methyl-2-pyridyl]carbamate (0.095 g, 194.46 μmol, 11.41% yield).

LCMS(ESI): [M+1]⁺ m/z: calcd 488.2; found 489.2; Rt=3.194 min.

Step 2: Synthesis of tert-butyl N-[5-[[2-[(2R,5R)-4,4-difluoro-5-methyl-2-phenyl-1-piperidyl]-2-oxo-acetyl]amino]-3-methyl-2-pyridyl]carbamate and Tert-butyl N-[5-[[2-[(2S,5S)-4,4-difluoro-5-methyl-2-phenyl-1-piperidyl]-2-oxo-acetyl]amino]-3-methyl-2-pyridyl]carbamate Chiral separation was performed using Column: Chiralpak IA-II (250*20 mm, 5 mkm); Mobile phase: Hexane-IPA-MeOH 50-25-25 Flow Rate: 12 mL/min to give tert-butyl N-[5-[[2-[(2R,5R)-4,4-difluoro-5-methyl-2-phenyl-1-piperidyl]-2-oxo-acetyl]amino]-3-methyl-2-pyridyl]carbamate (0.037 g, 75.74 μmol, 38.95% yield) and tert-butyl N-[5-[[2-[(2S,5S)-4,4-difluoro-5-methyl-2-phenyl-1-piperidyl]-2-oxo-acetyl]amino]-3-methyl-2-pyridyl]carbamate (0.033 g, 67.55 μmol, 34.74% yield). LCMS (ESI): [M+1]+ m/z: calcd 488.2; found 489.2; Rt=3.194 min.

Step 3: Synthesis of N-(6-amino-5-methyl-3-pyridyl)-2-[(2R,5R)-4,4-difluoro-5-methyl-2-phenyl-1-piperidyl]-2-oxo-acetamide (Compound 735 tert-butyl N-[5-[[2-[(2R,5R)-4,4-difluoro-5-methyl-2-phenyl-1-piperidyl]-2-oxo-acetyl]amino]-3-methyl-2-pyridyl]carbamate (0.036 g, 73.69 μmol) was dissolved in mixture of dioxane (2 mL) and water (2 mL) then stirred at 100° C. for 12 hr. The reaction mixture was concentrated on vacuo at 55° C. to give crude product which was purified by HPLC (6 min 5-95% H₂O/MeCN 30 ml/min (loading pump 4 ml MeCN) column: SunFire 100*19 mm, 5 microM) to give N-(6-amino-5-methyl-3-pyridyl)-2-[(2R,5R)-4,4-difluoro-5-methyl-2-phenyl-1-piperidyl]-2-oxo-acetamide (0.023 g, 59.22 μmol, 80.36% yield).

$^1$H NMR (DMSO-d$_6$, 600 MHz): δ (ppm) 1.06 (m, 3H), 2.00 (m, 3H), 2.17 (m, 1H), 2.91 (m, 2H), 3.43 (m, 1H), 3.97 (m, 1H), 5.61 (m, 3H), 7.31 (m, 5H), 7.47 (m, 1H), 7.99 (m, 1H), 10.56 (m, 1H)

LCMS(ESI): [M+1]+ m/z: calcd 388.2; found 389.2; Rt=1.820 min.

Step 4: Synthesis of N-(6-amino-5-methyl-3-pyridyl)-2-[(2S,5S)-4,4-difluoro-5-methyl-2-phenyl-1-piperidyl]-2-oxo-acetamide (Compound 713 tert-butyl N-[5-[[2-[(2S,5S)-4,4-difluoro-5-methyl-2-phenyl-1-piperidyl]-2-oxo-acetyl]amino]-3-methyl-2-pyridyl]carbamate (0.033 g, 67.55 μmol) was dissolved in mixture of dioxane (2 mL) and water (2 mL) then stirred at 100° C. for 12 hr. The reaction mixture was concentrated on vacuo at 55° C. to give crude product which was purified by HPLC (6 min 5-95% H₂O/MeCN 30 ml/min (loading pump 4 ml MeCN) column: SunFire 100*19 mm, 5 microM) to give N-(6-amino-5-methyl-3-pyridyl)-2-[(2S,5S)-4,4-difluoro-5-methyl-2-phenyl-1-piperidyl]-2-oxo-acetamide (0.022 g, 56.64 μmol, 83.85% yield).

$^1$H NMR (DMSO-d$_6$, 600 MHz): δ (ppm) 1.06 (m, 3H), 2.00 (m, 3H), 2.17 (m, 1H), 2.91 (m, 2H), 3.43 (m, 1H), 3.97 (m, 1H), 5.61 (m, 3H), 7.31 (m, 5H), 7.47 (m, 1H), 7.99 (m, 1H), 10.56 (m, 1H)

LCMS(ESI): [M+1]+ m/z: calcd 388.2; found 389.2; Rt=1.820 min.

Example 403. The Synthesis of 2-(2-(1H-benzo[d]imidazol-5-yl)-5-methylpiperidin-1-yl)-N-(6-amino-5-methylpyridin-3-yl)-2-oxoacetamide (Compound 408, Compound 404)

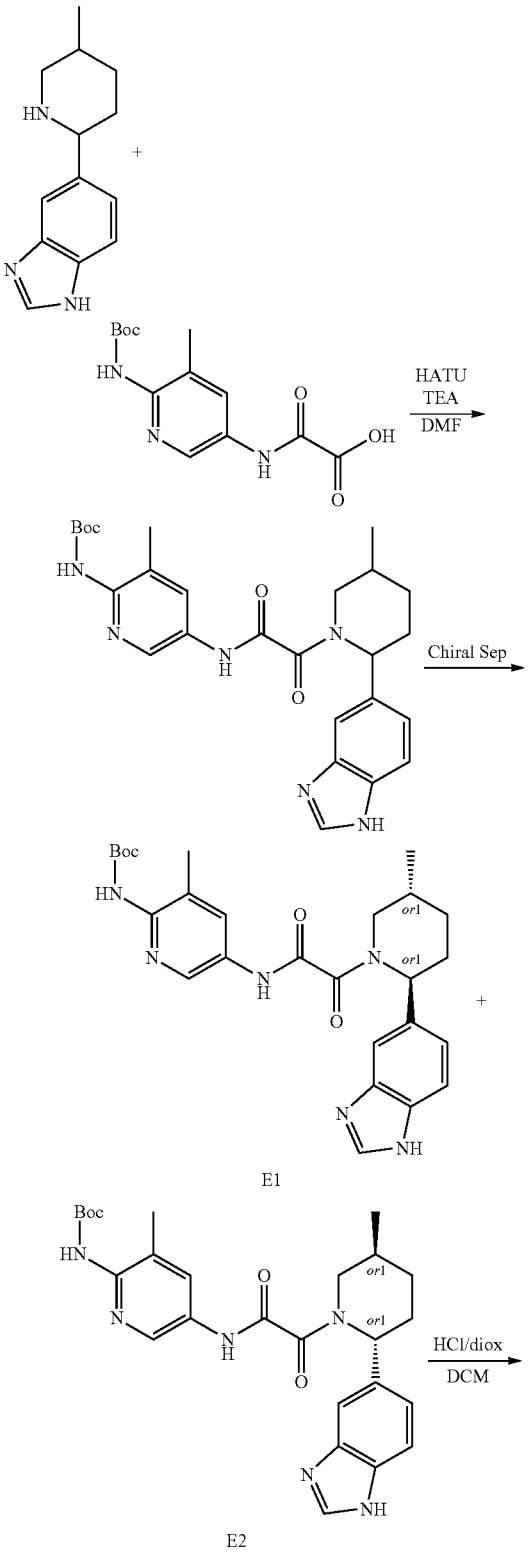

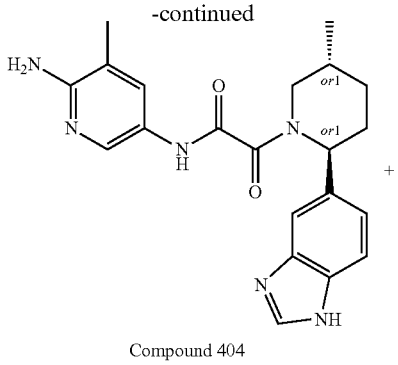

Compound 404

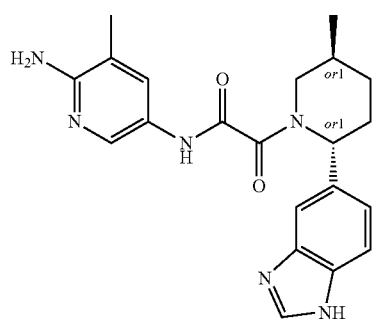

Compound 408

Step 1: Synthesis of tert-butyl (5-(2-(2-(1H-benzo[d]imidazol-5-yl)-5-methylpiperidin-1-yl)-2-oxoacetamido)-3-methylpyridin-2-yl)carbamate HATU (353.22 mg, 928.96 µmol) was added portionwise at rt to a suspension of 2-[[6-(tert-butoxycarbonylamino)-5-methyl-3-pyridyl]amino]-2-oxo-acetic acid (274.31 mg, 928.96 µmol), 5-(5-methyl-2-piperidyl)-1H-benzimidazole (250 mg, 928.96 µmol) and TEA (564.01 mg, 5.57 mmol, 776.88 µL) in DMF (9 mL). The clear solution was stirred at ambient temperature for 108 hr and the solvents were evaporated in vacuo to give 1 g of crude material. It was subjected to RP-HPLC (column: YMC Triart C18 100×20 mm, 5 um; 40-72% 0-5 min 0.1% NH₃-MeOH as mobile phase) to give tert-butyl N-[5-[[2-[2-(1H-benzimidazol-5-yl)-5-methyl-1-piperidyl]-2-oxo-acetyl]amino]-3-methyl-2-pyridyl]carbamate (65 mg, 131.96 µmol, 14.21% yield).

$^1$H NMR (400 MHz, DMSO-d$_6$) δ (ppm)

LCMS(ESI): [M]$^+$ m/z: calcd 492.2; found 493.2; Rt=2.724 min.

Step 2: Chiral Separation

The enantiomers were separated by chiral HPLC (column: IA (250*20, 5 mkm), Hexane-IPA-MeOH, 50-25-25, 12 ml/min as mobile phase) to give the two individual enantiomers tert-butyl N-[5-[[2-[(2S,5R)-2-(1H-benzimidazol-5-yl)-5-methyl-1-piperidyl]-2-oxo-acetyl]amino]-3-methyl-2-pyridyl]carbamate (E1) (39 mg, 79.18 µmol, 70.91% yield) RetTime=12.95 min and tert-butyl N-[5-[[2-[(2R,5S)-2-(1H-benzimidazol-5-yl)-5-methyl-1-piperidyl]-2-oxo-acetyl]amino]-3-methyl-2-pyridyl]carbamate (E2) (35 mg, 71.06 µmol, 63.64% yield) RetTime=16.57 min.

E1: Retention time: 12.95 min $^1$H NMR (500 MHz, DMSO-d$_6$) δ (ppm)

LCMS(ESI): [M]$^+$ m/z: calcd 492.5; found 493.2; Rt=3.851 min.

E2: Retention time: 16.57 min $^1$H NMR (500 MHz, DMSO-d$_6$) δ (ppm)

LCMS(ESI): [M]$^+$ m/z: calcd 492.5; found 493.2; Rt=3.850 min.

Step 3: Synthesis of 2-(2-(1H-benzo[d]imidazol-5-yl)-5-methylpiperidin-1-yl)-N-(6-amino-5-methylpyridin-3-yl)-2-oxoacetamide (Compound 404 and Compound 408

Hydrogen chloride solution 4.0 M in dioxane (206.20 mg, 791.77 µmol, 196.38 µL, 14% purity) was carefully added at rt to a solution of tert-butyl N-[5-[[2-[(2S,5R)-2-(1H-benzimidazol-5-yl)-5-methyl-1-piperidyl]-2-oxo-acetyl]amino]-3-methyl-2-pyridyl]carbamate E1 (39 mg, 79.18 µmol) and tert-butyl N-[5-[[2-[(2R,5S)-2-(1H-benzimidazol-5-yl)-5-methyl-1-piperidyl]-2-oxo-acetyl]amino]-3-methyl-2-pyridyl]carbamate E2 (35 mg, 71.06 µmol) in DCM (0.5 mL). The reaction mixture was then stirred for 12 hr at rt and the solvents were evaporated in vacuo. The residue was subjected to RP-HPLC (column: YMC Triart C18 100×20 mm, 5 um; 30-70% 0-5 min 0.10% NH₃-MeOH as mobile phase) to give N-(6-amino-5-methyl-3-pyridyl)-2-[(2S,5R)-2-(1H-benzimidazol-5-yl)-5-methyl-1-piperidyl]-2-oxo-acetamide Compound 404 (17 mg, 43.32 µmol, 54.71% yield) as solid material and N-(6-amino-5-methyl-3-pyridyl)-2-[(2R,5S)-2-(1H-benzimidazol-5-yl)-5-methyl-1-piperidyl]-2-oxo-acetamide Compound 408 (15 mg, 38.22 µmol, 53.79% yield).

Compound 404:

$^1$H NMR (600 MHz, DMSO-d$_6$) δ (ppm) 0.98-1.05 (m, 3H), 1.27-1.41 (m, 1H), 1.69-1.81 (m, 1H), 1.79-1.91 (m, 1H), 1.96-2.03 (m, 3H), 2.03-2.20 (m, 1H), 2.22-2.34 (m, 1H), 2.72-3.21 (m, 1H), 3.43-4.05 (m, 1H), 5.20-5.59 (m, 1H), 5.59-5.74 (m, 2H), 7.11-7.24 (m, 1H), 7.38-7.52 (m, 2H), 7.55-7.67 (m, 1H), 7.92-8.07 (m, 1H), 8.18 (s, 1H), 10.40-10.59 (m, 1H), 12.28-12.44 (m, 1H).

LCMS(ESI): [M]$^+$ m/z: calcd 392.4; found 393.2; Rt=1.523 min.

Compound 408:

$^1$H NMR (500 MHz, DMSO-d$_6$) δ (ppm) 1.03-1.06 (m, 3H), 1.29-1.45 (m, 1H), 1.71-1.83 (m, 1H), 1.82-1.94 (m, 1H), 1.94-2.19 (m, 4H), 2.20-2.35 (m, 1H), 2.77-3.28 (m, 1H), 3.47-4.08 (m, 1H), 5.23-5.62 (m, 1H), 5.61-5.78 (m, 2H), 7.12-7.27 (m, 1H), 7.40-7.56 (m, 2H), 7.59-7.68 (m, 1H), 7.94-8.10 (m, 1H), 8.18-8.24 (m, 1H), 10.48-10.59 (m, 1H), 12.33-12.47 (m, 1H).

LCMS(ESI): [M]$^+$ m/z: calcd 392.4; found 393.2; Rt=1.857 min.

Example 404. The Synthesis of N-(6-amino-5-methyl-3-pyridyl)-2-[(2S,5R)-5-methyl-2-(2-oxoindolin-5-yl)-1-piperidyl]-2-oxo-acetamide (Compound 677) and N-(6-amino-5-methyl-3-pyridyl)-2-[(2R,5S)-5-methyl-2-(2-oxoindolin-5-yl)-1-piperidyl]-2-oxo-acetamide (Compound 678
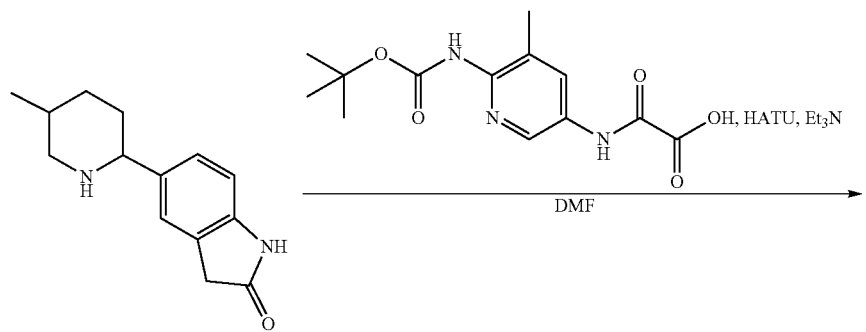
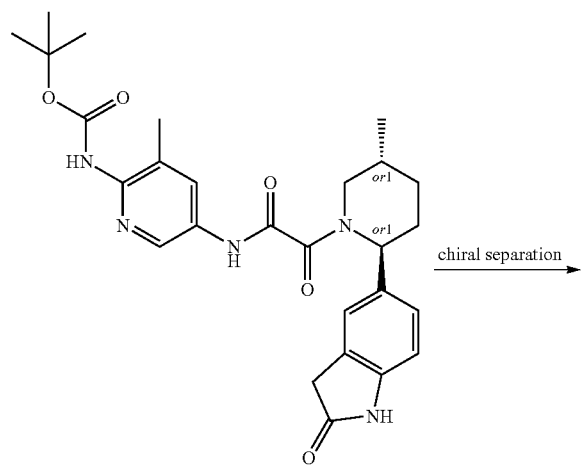
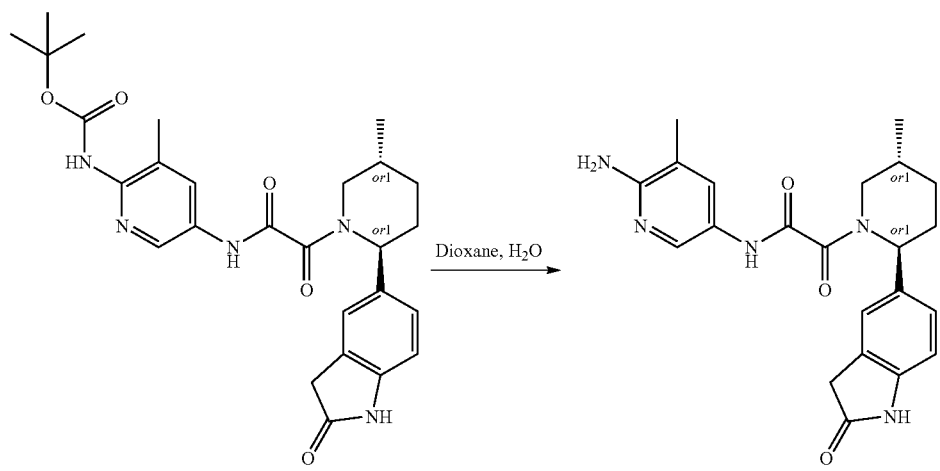

-continued

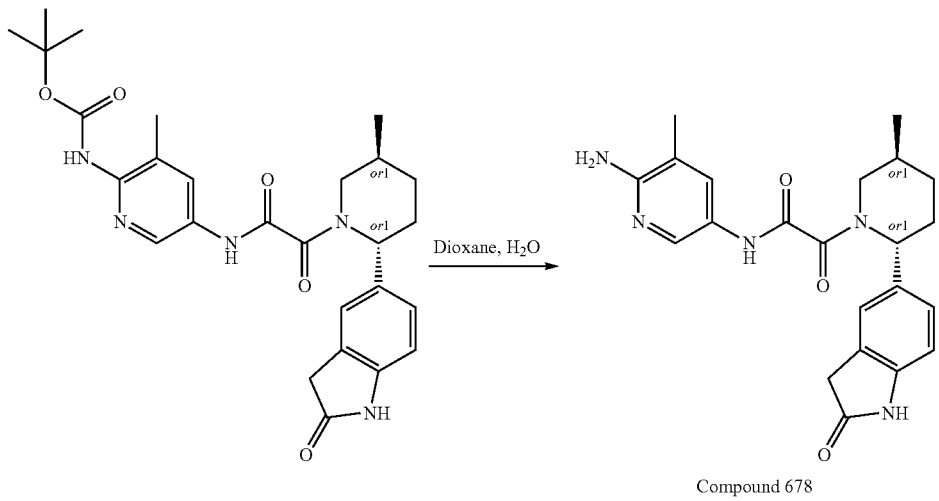

Compound 678

The first step was performed as described for the synthesis of compound Compound 373

Step 2: Chiral Separation of Tert-butyl N-[3-methy-5-[[2-[(2S,5R)-5-methyl-2-(2-oxoindolin-5-yl)-1-piperidyl]-2-oxo-acetyl]amino]-2-pyridyl]carbamate and Tert-butyl N-[3-methyl-5-[[2-[(2R,5S)-5-methyl-2-(2-oxoindolin-5-yl)-1-piperidyl]-2-oxo-acetyl]amino]-2-pyridyl]carbamate tert-butyl N-[3-methyl-5-[[2-[5-methyl-2-(2-oxoindolin-5-yl)-1-piperidyl]-2-oxo-acetyl]amino]-2-pyridyl]carbamate (0.2028 g, 399.54 μmol) was subjected to chiral HPLC purification (Column: Chiralpak IB (250×20 mm, 5 um); Mobile phase: CO₂-MeOH, 80-20;
Flow Rate: 50 mL/min) to obtain tert-butyl N-[3-methyl-5-[[2-[(2S,5R)-5-methyl-2-(2-oxoindolin-5-yl)-1-piperidyl]-2-oxo-acetyl]amino]-2-pyridyl]carbamate (0.07683 g, 151.37 μmol, 37.88% yield) and tert-butyl N-[3-methyl-5-[[2-[(2R,5S)-5-methyl-2-(2-oxoindolin-5-yl)-1-piperidyl]-2-oxo-acetyl]amino]-2-pyridyl]carbamate (74.80 mg, 147.37 μmol, 36.88% yield) as light-yellow solids.

tert-butyl N-[3-methyl-5-[[2-[(2S,5R)-5-methyl-2-(2-oxoindolin-5-yl)-1-piperidyl]-2-oxo-acetyl]amino]-2-pyridyl]carbamate:
LCMS(ESI): [M+H]⁺ m/z: calcd 507.3; found 508.4; Rt=3.951 min.
tert-butyl N-[3-methyl-5-[[2-[(2R,5S)-5-methyl-2-(2-oxoindolin-5-yl)-1-piperidyl]-2-oxo-acetyl]amino]-2-pyridyl]carbamate
LCMS(ESI): [M+H]⁺ m/z: calcd 507.3; found 508.6; Rt=3.951 min.

Step 3: Synthesis of N-(6-amino-5-methyl-3-pyridyl)-2-[(2S,5R)-5-methyl-2-(2-oxoindolin-5-yl)-1-piperidyl]-2-oxo-acetamide (Compound 677 tert-butyl N-[3-methyl-5-[[2-[(2S,5R)-5-methyl-2-(2-oxoindolin-5-yl)-1-piperidyl]-2-oxo-acetyl]amino]-2-pyridyl]carbamate (0.07683 g, 151.37 μmol) was dissolved in Dioxane (2.5 mL) and Water (2.5 mL). The resulting reaction mixture was heated at 100° C. for overnight. Then, the reaction mixture was concentrated in vacuo and the residue was purified by HPLC (Eluent: 2-10 min, 30-55%, MeOH/H₂O; flow rate: 30 ml/min (loading pump 4 ml MeOH), column: SunFire 100×19 mm, 5 um) to obtain N-(6-amino-5-methyl-3-pyridyl)-2-[(2S,5R)-5-methyl-2-(2-oxoindolin-5-yl)-1-piperidyl]-2-oxo-acetamide (Compound 677, 0.031 g, 76.08 μmol, 50.26% yield) as a white solid.

¹H NMR (DMSO-d₆, 600 MHz): δ (ppm) 1.00 (m, 3H), 1.30 (m, 1H), 1.70 (m, 1H), 1.84 (m, 1H), 1.99 (m, 4H), 2.14 (m, 1H), 3.05 (m, 1H), 3.43 (m, 3H), 5.52 (m, 1H), 5.59 (m, 2H), 6.79 (m, 1H), 7.13 (m, 2H), 7.44 (m, 1H), 7.98 (m, 1H), 10.40 (m, 2H).
LCMS(ESI): [M+H]⁺ m/z: calcd 407.2; found 408.0; Rt=1.634 min.

Step 4: Synthesis of N-(6-amino-5-methyl-3-pyridyl)-2-[(2R,5S)-5-methyl-2-(2-oxoindolin-5-yl)-1-piperidyl]-2-oxo-acetamide (Compound 678 tert-butyl N-[3-methyl-5-[[2-[(2R,5S)-5-methyl-2-(2-oxoindolin-5-yl)-1-piperidyl]-2-oxo-acetyl]amino]-2-pyridyl]carbamate (74.80 mg, 147.37 μmol) was dissolved in Dioxane (2.5 mL) and Water (2.5 mL). The resulting reaction mixture was heated at 100° C. for overnight. Then, the reaction mixture was concentrated in vacuo and the residue was purified by HPLC (Eluent: 2-10 min, 30-55%, MeOH/H₂O; flow rate: 30 ml/min (loading pump 4 ml MeOH), column: SunFire 100×19 mm, 5 um) to obtain N-(6-amino-5-methyl-3-pyridyl)-2-[(2R,5S)-5-methyl-2-(2-oxoindolin-5-yl)-1-piperidyl]-2-oxo-acetamide (Compound 678, 0.042 g, 103.08 μmol, 69.95% yield) as a white solid.

¹H NMR (DMSO-d₆, 600 MHz): δ (ppm) 1.00 (m, 3H), 1.30 (m, 1H), 1.70 (m, 1H), 1.85 (m, 1H), 1.99 (m, 4H), 2.15 (m, 1H), 3.04 (m, 1H), 3.43 (m, 3H), 5.56 (m, 3H), 6.80 (m, 1H), 7.10 (m, 2H), 7.44 (m, 1H), 7.98 (m, 1H), 10.40 (m, 2H).
LCMS(ESI): [M+H]⁺ m/z: calcd 407.2; found 408.0; Rt=1.634 min.

Example 405. The Synthesis of N-(6-amino-5-methyl-3-pyridyl)-2-[(2S,5R)-5-methyl-2-(1,2,3,4-tetrahydroquinolin-6-yl)-1-piperidyl]-2-oxo-acetamide (Compound 504) and N-[3-methyl-5-[[2-[(2R,5S)-5-methyl-2-(1,2,3,4-tetrahydroquinolin-6-yl)-1-piperidyl]-2-oxo-acetyl]amino]-2-pyridyl] carbamate (Compound 503
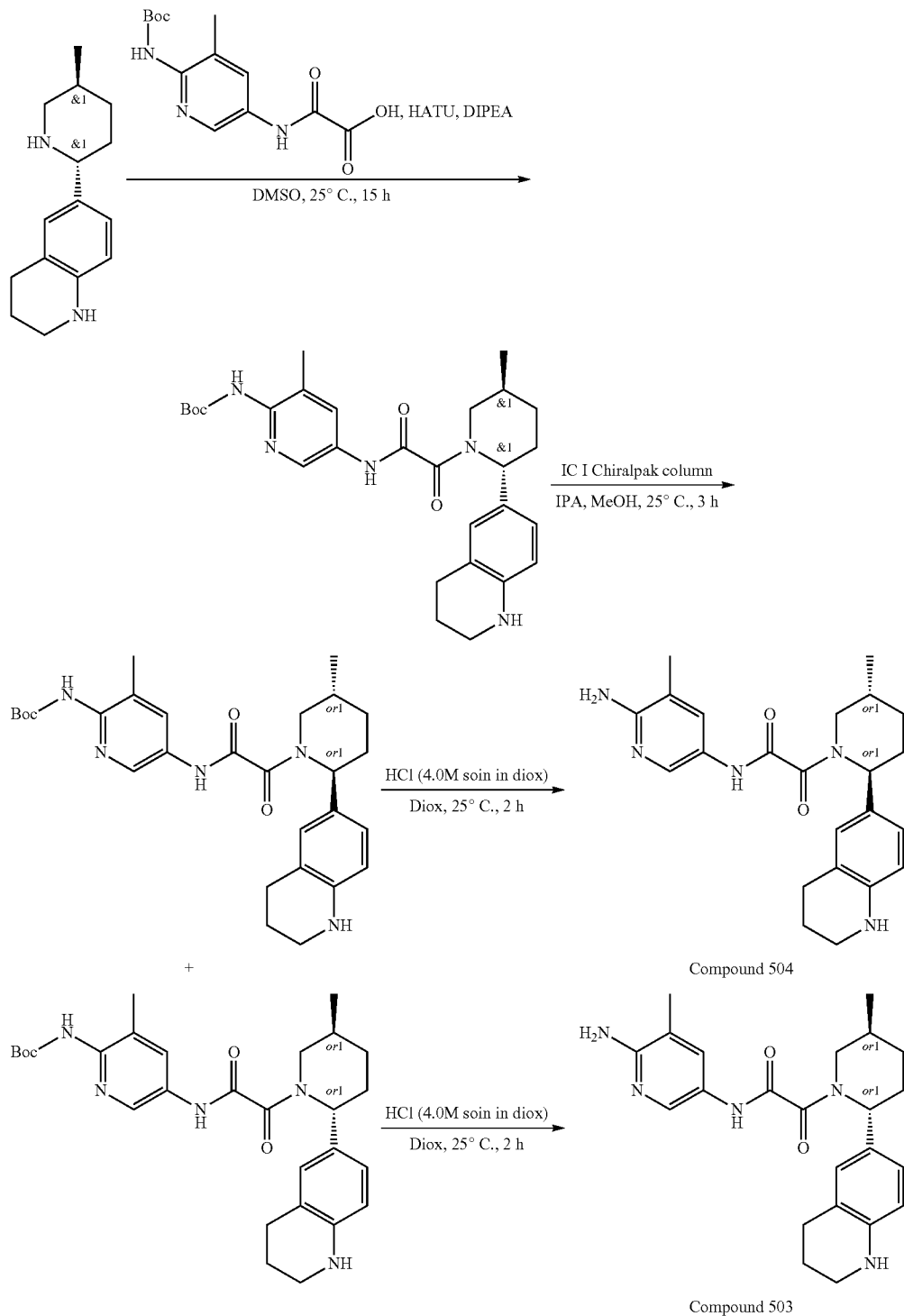

Step 1: The Synthesis of tert-butyl N-[3-methyl-5-[[2-[(2R,5S)-5-methyl-2-(1,2,3,4-tetrahydroquinolin-6-yl)-1-piperidyl]-2-oxo-acetyl]amino]-2-pyridyl]carbamate 6-[(2R,5S)-5-methyl-2-piperidyl]-1,2,3,4-tetrahydroquinoline (0.3 g, 1.30 mmol), 2-[[6-(tert-butoxycarbonylamino)-5-methyl-3-pyridyl]amino]-2-oxo-acetic acid (461.50 mg, 1.56 mmol), HATU (693.28 mg, 1.82 mmol) and DIPEA (336.65 mg, 2.60 mmol, 453.70 µL) were stirred in DMSO (4 mL) at 25° C. for 15 hr. HPLC of the reaction mixture shows 13% of desired product. The reaction mixture was submitted to LCMS to afford tert-butyl N-[3-methyl-5-[[2-[(2R,5S)-5-methyl-2-(1,2,3,4-tetrahydroquinolin-6-yl)-1-piperidyl]-2-oxo-acetyl]amino]-2-pyridyl]carbamate (0.077 g, 151.69 µmol, 11.65% yield).

HPLC data: 2-10 min 0-70% MeCN/H$_2$O 30 ml/min (loading pump 4 mL MeCN; column: SunFire 100*19 mm, 5 microM.

LCMS(ESI): [M+2H]$^+$ m/z: calcd 507.2; found 509.2; Rt=1.107 min.

Step 2: The Synthesis of tert-butyl N-[3-methyl-5-[[2-[(2S,5R)-5-methyl-2-(1,2,3,4-tetrahydroquinolin-6-yl)-1-piperidyl]-2-oxo-acetyl]amino]-2-pyridyl]carbamate and tert-butyl N-[3-methyl-5-[[2-[(2R,5S)-5-methyl-2-(1,2,3,4-tetrahydroquinolin-6-yl)-1-piperidyl]-2-oxo-acetyl]amino]-2-pyridyl]carbamate tert-butyl N-[3-methyl-5-[[2-[(2R,5S)-5-methyl-2-(1,2,3,4-tetrahydroquinolin-6-yl)-1-piperidyl]-2-oxo-acetyl]amino]-2-pyridyl]carbamate (0.077 g, 147.14 µmol) was submitted to chiral separation (Sample Info: IC I (250*20 mm,5 mkm) IPA-MeOH, 50-50, 10 ml/min; Inj Volume: 900.000 l) to afford tert-butyl N-[3-methyl-5-[[2-[(2S,5R)-5-methyl-2-(1,2,3,4-tetrahydroquinolin-6-yl)-1-piperidyl]-2-oxo-acetyl]amino]-2-pyridyl]carbamate (0.022 g, 43.34 µmol, 29.46% yield) and tert-butyl N-[3-methyl-5-[[2-[(2R,5S)-5-methyl-2-(1,2,3,4-tetrahydroquinolin-6-yl)-1-piperidyl]-2-oxo-acetyl]amino]-2-pyridyl]carbamate (0.021 g, 41.37 µmol, 28.12% yield).

tert-butyl N-[3-methyl-5-[[2-[(2S,5R)-5-methyl-2-(1,2,3,4-tetrahydroquinolin-6-yl)-1-piperidyl]-2-oxo-acetyl]amino]-2-pyridyl]carbamate:

RT (IC, MeOH-IPA, 50-50, 0.5 mL/min)=11.391 min.

LCMS(ESI): [M+H]$^+$ m/z: calcd 507.2; found 508.2; Rt=4.556 min.

tert-butyl N-[3-methyl-5-[[2-[(2R,5S)-5-methyl-2-(1,2,3,4-tetrahydroquinolin-6-yl)-1-piperidyl]-2-oxo-acetyl]amino]-2-pyridyl]carbamate:

RT (IC, MeOH-IPA, 50-50, 0.5 mL/min)=36.735 min.

LCMS(ESI): [M+H]$^+$ m/z: calcd 507.2; found 508.2; Rt=4.561 min.

Step 3: The Synthesis of N-(6-amino-5-methyl-3-pyridyl)-2-[(2S,5R)-5-methyl-2-(1,2,3,4-tetrahydroquinolin-6-yl)-1-piperidyl]-2-oxo-acetamide (Compound 504 tert-butyl N-[3-methyl-5-[[2-[(2S,5R)-5-methyl-2-(1,2,3,4-tetrahydroquinolin-6-yl)-1-piperidyl]-2-oxo-acetyl]amino]-2-pyridyl]carbamate (0.022 g, 43.34 µmol) was dissolved in a solution of HCl in 1,4-dioxane (10%) and stirred at 25° C. for 2 hr. The reaction mixture was concentrated in vacuo and a crude material was submitted to HPLC (HPLC data: 2-10 min 40-60% water/MeOH+NH$_3$(loading pump 4 ml MeOH) column: TRIART 100*20 mm 5 microM; Inj. volume 4000.000) to afford N-(6-amino-5-methyl-3-pyridyl)-2-[(2S,5R)-5-methyl-2-(1,2,3,4-tetrahydroquinolin-6-yl)-1-piperidyl]-2-oxo-acetamide (0.003 g, 7.36 µmol, 16.99% yield).

$^1$H NMR (400 MHz, CDCl$_3$) δ 1.06-1.17 (m, 3H), 1.27-1.40 (m, 1H), 1.88-2.05 (m, 5H), 2.10-2.23 (m, 5H), 2.69-2.81 (m, 2H), 2.96-3.33 (m, 2H), 3.33-3.86 (m, 1H), 4.11-4.28 (m, 0.3H), 4.40-4.61 (m, 2H), 4.68-4.97 (m, 0.7H), 5.63-6.35 (m, 1H), 6.42-6.52 (m, 1H), 6.80-6.97 (m, 2H), 7.78 (s, 1H), 8.00-8.18 (m, 1H), 9.02-9.26 (m, 1H).

LCMS(ESI): [M+H]$^+$ m/z: calcd 407.2; found 408.2; Rt=1.74 min.

Step 4: The Synthesis of N-(6-amino-5-methyl-3-pyridyl)-2-[(2R,5S)-5-methyl-2-(1,2,3,4-tetrahydroquinolin-6-yl)-1-piperidyl]-2-oxo-acetamide (Compound 503 tert-butyl N-[3-methyl-5-[[2-[(2R,5S)-5-methyl-2-(1,2,3,4-tetrahydroquinolin-6-yl)-1-piperidyl]-2-oxo-acetyl]amino]-2-pyridyl]carbamate (0.021 g, 41.37 µmol) was dissolved in a solution of HCl in 1,4-dioxane (10%) and stirred at 25° C. for 2 hr. The reaction mixture was concentrated in vacuo and the residue was submitted to HPLC (HPLC data: 2-10 min 40-60% water/MeOH+NH$_3$(loading pump 4 ml MeOH) column: TRIART 100*20 5 microM) to afford N-(6-amino-5-methyl-3-pyridyl)-2-[(2R,5S)-5-methyl-2-(1,2,3,4-tetrahydroquinolin-6-yl)-1-piperidyl]-2-oxo-acetamide (0.002 g, 4.91 µmol, 11.86% yield).

$^1$H NMR (400 MHz, CDCl$_3$) δ 1.10 (s, 3H), 1.35-1.40 (m, 1H), 1.94-2.03 (m, 4H), 2.14-2.22 (m, 5H), 2.75-2.81 (m, 2H), 3.29-3.35 (m, 2H), 3.37-3.46 (m, 1H), 4.21-4.87 (m, 3H), 5.66-6.35 (m, 1H), 6.45-6.51 (m, 1H), 6.85-6.93 (m, 2H), 7.28-7.30 (m, 1H), 7.76-7.80 (m, 1H), 8.03-8.14 (m, 1H), 9.02-9.21 (m, 1H).

LCMS(ESI): [M+H]$^+$ m/z: calcd 407.2; found 408.2; Rt=1.738 min.

Example 406. The Synthesis of N-(6-amino-5-methyl-3-pyridyl)-2-[(2S,5R)-5-methyl-2-(2-oxo-3,4-dihydro-1H-Quinolin-6-yl)-1-piperidyl]-2-oxo-acetamide (Compound 505), N-(6-amino-5-methyl-3-pyridyl)-2-[(2R,5S)-5-methyl-2-(2-oxo-3,4-dihydro-1H-Quinolin-6-yl)-1-piperidyl]-2-oxo-acetamide (Compound 502), and N-(6-amino-5-methyl-3-pyridyl)-2-[(2R,5R)-5-methyl-2-(2-oxo-3,4-dihydro-1H-Quinolin-6-yl)-1-piperidyl]-2-oxo-acetamide (Compound 583
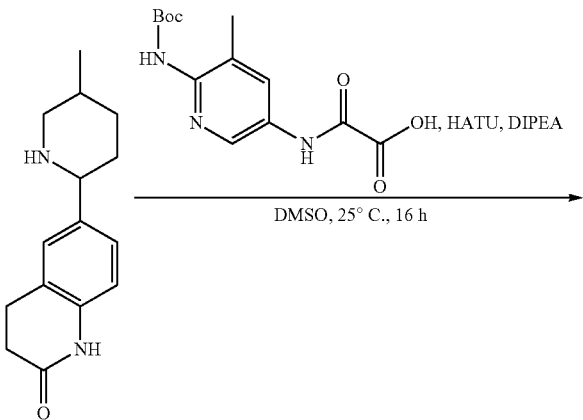
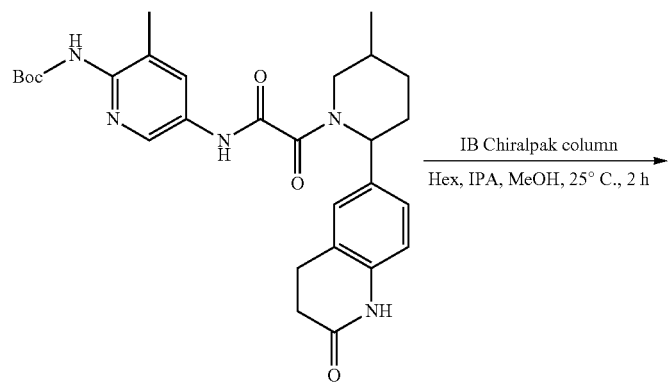
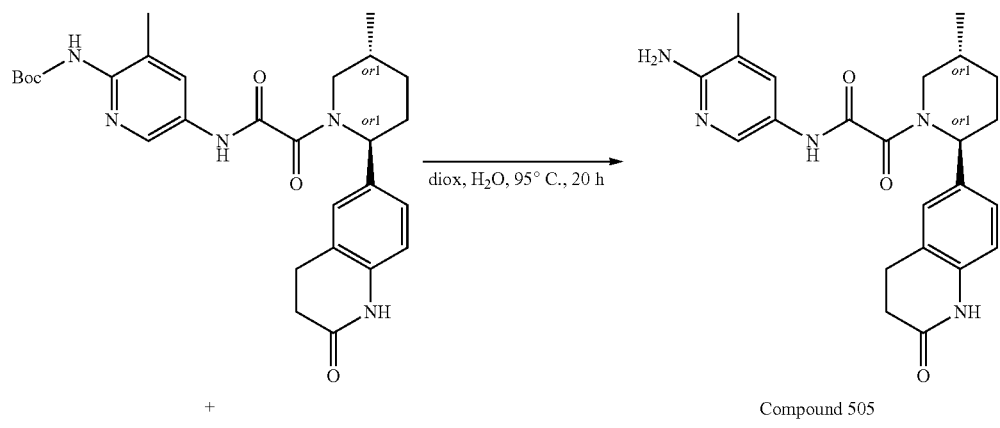
Compound 505

-continued

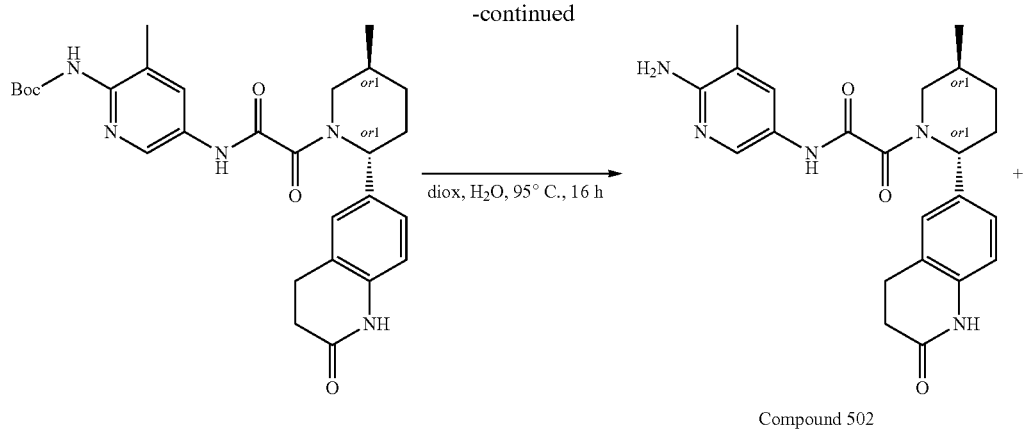

Compound 502

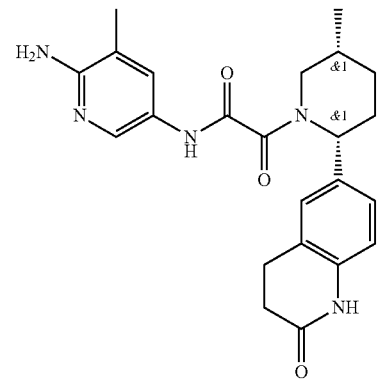

Compound 583

Step 1: The Synthesis of tert-butyl N-[3-methyl-5-[[2-[5-methyl-2-(2-oxo-3,4-dihydro-1H-Quinolin-6-yl)-1-piperidyl]-2-oxo-acetyl]amino]-2-pyridyl]carbamate A mixture of 6-(5-methyl-2-piperidyl)-3,4-dihydro-1H-quinolin-2-one (0.5 g, 1.44 mmol, HC), 2-[[6-(tert-butoxycarbonylamino)-5-methyl-3-pyridyl]amino]-2-oxo-acetic acid (425.91 mg, 1.44 mmol), HATU (712.95 mg, 1.88 mmol) and DIPEA (932.07 mg, 7.21 mmol, 1.26 mL) was stirred at 25° C. in DMSO (5 mL) for 16 hr. After completion of the reaction, the reaction mixture was poured into water (10 mL) and extracted with DCM. The organic layer was separated, dried over $Na_2SO_4$ and concentrated in vacuo. The crude material was submitted to HPLC (2-10 min 40-60% water/MeCN+$NH_3$(loading pump 4 ml MeCN+$NH_3$) column: TRIART 100*20 5 microM) to afford tert-butyl N-[3-methyl-5-[[2-[5-methyl-2-(2-oxo-3,4-dihydro-1H-quinolin-6-yl)-1-piperidyl]-2-oxo-acetyl]amino]-2-pyridyl]carbamate (0.137 g, 262.65 μmol, 18.21% yield) in two fractions: 91 mg 93% by LCMS and 48 mg 90% by LCMS.

LCMS(ESI): [M−Boc]$^+$ m/z: calcd 421.2; found 422.2; Rt=3.057 min.

Step 2: The Synthesis of tert-butyl N-[3-methy-5-[[2-[(2S,5R)-5-methyl-2-(2-oxo-3,4-dihydro-1H-Quinolin-6-yl)-1-piperidyl]-2-oxo-acetyl]amino]-2-pyridyl]carbamate and Tert-butyl N-[3-methyl-5-[[2-[(2R,5S)-5-methyl-2-(2-oxo-3,4-dihydro-1H-Quinolin-6-yl)-1-piperidyl]-2-oxo-acetyl]amino]-2-pyridyl]carbamate tert-butyl N-[3-methyl-5-[[2-[5-methyl-2-(2-oxo-3,4-dihydro-1H-quinolin-6-yl)-1-piperidyl]-2-oxo-acetyl]amino]-2-pyridyl]carbamate (0.137 g, 262.65 μmol) was submitted to chiral separation (IB (250*20, 5 mkm), Hexane-IPA-MeOH, 70-15-15, 12 ml/min) to afford tert-butyl N-[3-methyl-5-[[2-[(2S,5R)-5-methyl-2-(2-oxo-3,4-dihydro-1H-quinolin-6-yl)-1-piperidyl]-2-oxo-acetyl]amino]-2-pyridyl]carbamate (0.05 g, 95.86 μmol, 36.50% yield) and tert-butyl N-[3-methyl-5-[[2-[(2R,5S)-5-methyl-2-(2-oxo-3,4-dihydro-1H-quinolin-6-yl)-1-piperidyl]-2-oxo-acetyl]amino]-2-pyridyl]carbamate (0.047 g, 90.11 μmol, 34.31% yield).

tert-butyl N-[3-methyl-5-[[2-[(2S,5R)-5-methyl-2-(2-oxo-3,4-dihydro-1H-quinolin-6-yl)-1-piperidyl]-2-oxo-acetyl]amino]-2-pyridyl]carbamate:

RT (IB, Hexane-IPA-MeOH, 70-15-15, 0.6 ml/min)=17.300 min.

LCMS(ESI): [M+H]$^+$ m/z: calcd 521.2; found 522.2; Rt=4.990 min.

tert-butyl N-[3-methyl-5-[[2-[(2R,5S)-5-methyl-2-(2-oxo-3,4-dihydro-1H-quinolin-6-yl)-1-piperidyl]-2-oxo-acetyl]amino]-2-pyridyl]carbamate:

RT (IB, Hexane-IPA-MeOH, 70-15-15, 0.6 ml/min)=15.437 min.
LCMS(ESI): [M+H]$^+$ m/z: calcd 521.2; found; Rt=4.989 min.

Step 3: The Synthesis of N-(6-amino-5-methyl-3-pyridyl)-2-[(2S,5R)-5-methyl-2-(2-oxo-3,4-dihydro-1H-Quinolin-6-yl)-1-piperidyl]-2-oxo-acetamide (Compound 505 tert-butyl N-[3-methyl-5-[[2-[(2S,5R)-5-methyl-2-(2-oxo-3,4-dihydro-1H-quinolin-6-yl)-1-piperidyl]-2-oxo-acetyl]amino]-2-pyridyl]carbamate (0.05 g, 92.98 μmol) was dissolved in a mixture of water (1.5 mL) and 1,4-dioxane (0.5 mL) and stirred at 95° C. for 20 h. The reaction mixture was concentrated in vacuo to afford N-(6-amino-5-methyl-3-pyridyl)-2-[(2S,5R)-5-methyl-2-(2-oxo-3,4-dihydro-1H-quinolin-6-yl)-1-piperidyl]-2-oxo-acetamide (0.036 g, 85.41 μmol, 91.86% yield).
$^1$H NMR (600 MHz, DMSO-d$_6$) δ 0.95-1.12 (m, 3H), 1.24-1.36 (m, 1H), 1.61-1.74 (m, 1H), 1.78-1.90 (m, 1H), 1.93-2.07 (m, 4H), 2.09-2.22 (m, 1H), 2.39-2.44 (m, 2H), 2.72-2.76 (m, 0.4H), 2.82-2.90 (m, 2H), 3.17-3.24 (m, 0.6H), 3.41-4.00 (m, 1H), 4.99-5.53 (m, 1H), 5.57-5.72 (m, 2H), 6.79-6.86 (m, 1H), 7.03-7.13 (m, 2H), 7.37-7.57 (m, 1H), 7.92-8.10 (m, 1H), 10.03 (s, 1H), 10.40-10.56 (m, 1H).
LCMS(ESI): [M+H]$^+$ m/z: calcd 421.2; found 422.4; Rt=1.872 min.

Step 4: The Synthesis of N-(6-amino-5-methyl-3-pyridyl)-2-[(2R,5S)-5-methyl-2-(2-oxo-3,4-dihydro-1H-Quinolin-6-yl)-1-piperidyl]-2-oxo-acetamide (Compound 502, Compound 502, Compound 502_3), and N-(6-amino-5-methyl-3-pyridyl)-2-[(2R,5R)-5-methyl-2-(2-oxo-3,4-dihydro-1H-Quinolin-6-yl)-1-piperidyl]-2-oxo-acetamide (Compound 583 tert-butyl N-[3-methyl-5-[[2-[(2R,5S)-5-methyl-2-(2-oxo-3,4-dihydro-1H-quinolin-6-yl)-1-piperidyl]-2-oxo-acetyl]amino]-2-pyridyl]carbamate (0.047 g, 89.21 μmol) was dissolved in a mixture of water (1.5 mL) and 1,4-dioxane (0.5 mL) and the reaction mixture was stirred at 95° C. for 16 hr. After cooling down, the reaction mixture was concentrated in vacuo to afford N-(6-amino-5-methyl-3-pyridyl)-2-[(2R,5S)-5-methyl-2-(2-oxo-3,4-dihydro-1H-quinolin-6-yl)-1-piperidyl]-2-oxo-acetamide (0.032 g, 75.92 μmol, 85.11% yield) with cis-impurity, which was purified in the following conditions: Column: Chiralpak IA (250/20 mm/5 m); Mobile phase: Hexane-IPA-MeOH, 60-20-20 Flow Rate: 12 mL/min; Column Temperature: 24° C.; Wavelength: 205 nm, 210 nm, 308 nm), RetTime (isomer A)=70.02 min; RetTime (isomers B)=77.91 min To give 20 mg of N-(6-amino-5-methyl-3-pyridyl)-2-[(2R,5S)-5-methyl-2-(2-oxo-3,4-dihydro-1H-quinolin-6-yl)-1-piperidyl]-2-oxo-acetamide (0.032 g, 75.92 μmol, 85.11% yield) (Compound 502) and N-(6-amino-5-methyl-3-pyridyl)-2-[(2R,5R)-5-methyl-2-(2-oxo-3,4-dihydro-1H-quinolin-6-yl)-1-piperidyl]-2-oxo-acetamide (0.0015 g, 3.56 μmol, 3.99% yield) Compound 583.

Compound 502:
$^1$H NMR (600 MHz, DMSO-d$_6$) δ 0.98-1.20 (m, 3H), 1.26-1.37 (m, 1H), 1.63-1.75 (m, 1H), 1.80-1.92 (m, 1H), 1.95-2.07 (m, 4H), 2.11-2.21 (m, 1H), 2.40-2.43 (m, 2H), 2.72-2.75 (m, 0.4H), 2.83-2.89 (m, 2H), 3.17-3.22 (m, 0.6H), 3.42-3.99 (m, 1H), 5.01-5.53 (m, 1H), 5.57-5.66 (m, 2H), 6.79-6.86 (m, 1H), 7.04-7.13 (m, 2H), 7.39-7.52 (m, 1H), 7.91-8.07 (m, 1H), 10.02 (s, 1H), 10.41-10.52 (m, 1H).
LCMS(ESI): [M+H]$^+$ m/z: calcd 421.2; found 422.4; Rt=1.868 min.
LCMS(ESI): [M+H]$^+$ m/z: calcd 421.2; found 422.2; Rt=1.782 min.

Compound 583:
$^1$H NMR (600 MHz, DMSO-d$_6$) δ 0.70-0.98 (m, 3H), 1.24-1.38 (m, 1H), 1.60-1.67 (m, 1H), 1.78-1.89 (m, 1H), 1.95-2.07 (m, 4H), 2.09-2.18 (m, 1H), 2.42-2.44 (m, 2H), 2.74-3.20 (m, 3H), 3.34-4.20 (m, 1H), 4.98-5.63 (m, 1H), 5.87 (br. s, 2H), 6.77-6.88 (m, 1H), 7.03-7.13 (m, 2H), 7.42-7.60 (m, 1H), 7.95-8.10 (m, 1H), 10.03 (s, 1H), 10.48-10.64 (m, 1H).
LCMS(ESI): [M+H]$^+$ m/z: calcd 421.2; found 422.2; Rt=1.23 min.

Example 407. The Synthesis of N-(6-amino-5-methyl-3-pyridyl)-2-[(2S,5R)-5-methyl-2-[6-(methylamino)-3-pyridyl]-1-piperidyl]-2-oxo-acetamide (Compound 864) and N-(6-amino-5-methyl-3-pyridyl)-2-[(2R,5S)-5-methyl-2-[6-(methylamino)-3-pyridyl]-1-piperidyl]-2-oxo-acetamide (Compound 876

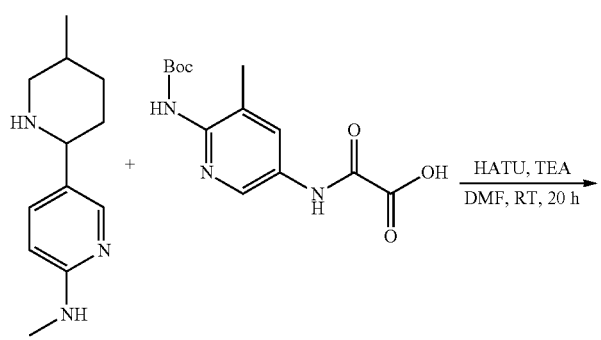

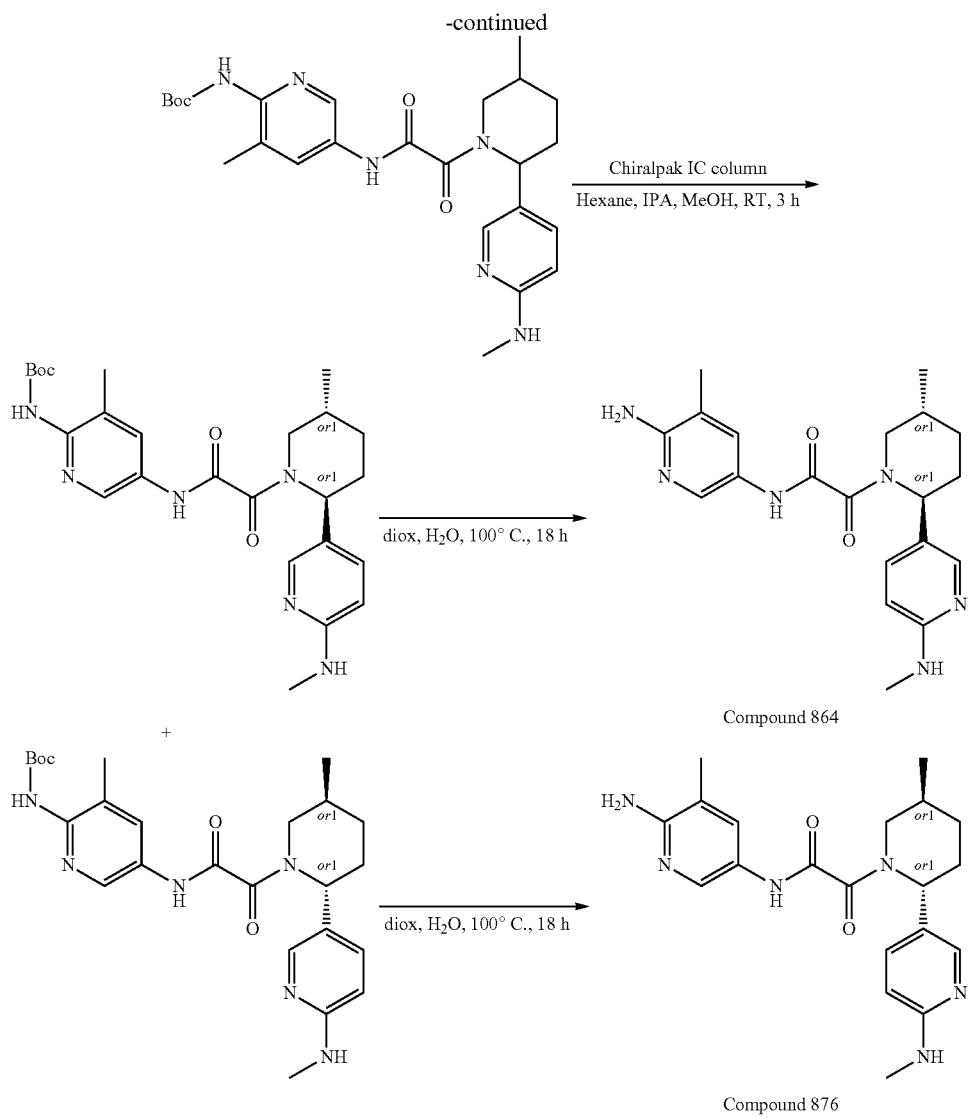

Compound 864

Compound 876

Step 1: The Synthesis of tert-butyl N-[3-methyl-5-[[2-[5-methyl-2-[6-(methylamino)-3-pyridyl]-1-piperidyl]-2-oxo-acetyl]amino]-2-pyridyl]carbamate N-methyl-5-(5-methyl-2-piperidyl)pyridin-2-amine (0.5 g, 2.44 mmol), 2-[[6-(tert-butoxycarbonylamino)-5-methyl-3-pyridyl]amino]-2-oxo-acetic acid (719.17 mg, 2.44 mmol) and triethylamine (2.46 g, 24.35 mmol, 3.39 mL) were mixed together in DMF (10 mL). HATU (1.39 g, 3.65 mmol) was added and the resulting mixture was stirred for 18 hr. The reaction mixture was concentrated in vacuo and the residue was purified by HPLC (50-75% MeOH—2-10 min Flow rate: 30 mL/min; loading pump 4 mL/min MeOH; Column Sun Fire 100*19 mm, 5 mkm) to obtain tert-butyl N-[3-methyl-5-[[2-[5-methyl-2-[6-(methylamino)-3-pyridyl]-1-piperidyl]-2-oxo-acetyl]amino]-2-pyridyl]carbamate (0.184 g, 381.29 μmol, 15.66% yield).

LCMS(ESI): [M+H]+ m/z: calcd 482.2; found 483.2; Rt=0.991 min.

Step 2: The Synthesis of tert-butyl N-[3-methyl-5-[[2-[(2S,5R)-5-methyl-2-[6-(methylamino)-3-pyridyl]-1-piperidyl]-2-oxo-acetyl]amino]-2-pyridyl]carbamate and Tert-butyl N-[3-methyl-5-[[2-[(2R,5S)-5-methyl-2-[6-(methylamino)-3-pyridyl]-1-piperidyl]-2-oxo-acetyl]amino]-2-pyridyl]carbamate tert-butyl N-[3-methyl-5-[[2-[5-methyl-2-[6-(methylamino)-3-pyridyl]-1-piperidyl]-2-oxo-acetyl]amino]-2-pyridyl]carbamate (0.184 g, 381.29 μmol) was chirally separated (Column: Chiralpak ICII (250*20 mm, 5 mkm); Mobile phase: Hexane-IPA-MeOH 50-25-25 Flow Rate: 12 mL/min; 9 inj., 20 mg/inj, 11 hr) to obtain tert-butyl N-[3-methyl-5-[[2-[(2S,5R)-5-methyl-2-[6-(methylamino)-3-pyridyl]-1-piperidyl]-2-oxo-acetyl]amino]-2-pyridyl]carbamate Isomer 1 (0.05273 g, 109.27 μmol, 28.66% yield; RetTime=28.35) and tert-butyl N-[3-methyl-5-[[2-[(2R,5S)-5-methyl-2-[6-(methylamino)-3-pyridyl]-1-piperidyl]-2-oxo-acetyl]amino]-2-pyridyl]carbamate Isomer 2 (0.06791 g, 140.72 μmol, 36.91% yield; RetTime=54.813).

1st Isomer: RT (IC, Hexane-IPA-MeOH, 50-25-25, 0.6 mL/min)=28.386 min.

LCMS(ESI): [M+2H]$^+$ m/z: calcd 482.2; found 484.2; Rt=2.009 min.

2$^{nd}$ Isomer: RT (IC, Hexane-IPA-MeOH, 50-25-25, 0.6 mL/min)=56.615 min.

LCMS(ESI): [M+2H]$^+$ m/z: calcd 482.2; found 484.2; Rt=2.002 min.

Step 3: The Synthesis of N-(6-amino-5-methyl-3-pyridyl)-2-[(2S,5R)-5-methyl-2-[6-(methylamino)-3-pyridyl]-1-piperidyl]-2-oxo-acetamide (Compound 864 tert-butyl N-[3-methyl-5-[[2-[(2S,5R)-5-methyl-2-[6-(methylamino)-3-pyridyl]-1-piperidyl]-2-oxo-acetyl]amino]-2-pyridyl]carbamate Isomer 1 (0.05273 g, 109.27 µmol) was dissolved in a mixture of Dioxane (1 mL) and Water (1 mL) and the resulting mixture was heated at 100° C. for 18 hr. The reaction mixture was concentrated in vacuo and the residue was purified by HPLC (35-55% MeOH/H$_2$O+NH$_3$-2-10 min, Flow rate: 30 ml/min; loading pump 4 ml/min MeOH+NH$_3$; target mass 382) to obtain N-(6-amino-5-methyl-3-pyridyl)-2-[(2S,5R)-5-methyl-2-[6-(methylamino)-3-pyridyl]-1-piperidyl]-2-oxo-acetamide (0.0281 g, 73.47 µmol, 67.24% yield).

$^1$H NMR (DMSO-d$_6$, 600 MHz): δ (ppm) 0.95-1.03 (m, 3H), 1.24-1.40 (m, 1H), 1.65-1.77 (m, 1H), 1.77-1.89 (m, 1H), 1.89-1.98 (m, 1H), 1.98-2.03 (m, 3H), 2.06-2.15 (m, 1H), 2.71-2.74 (m, 3H), 2.77-3.18 (m, 1H), 3.39-3.95 (m, 1H), 4.95-5.50 (m, 1H), 5.54-5.66 (m, 2H), 6.38-6.46 (m, 2H), 7.24-7.38 (m, 1H), 7.42-7.50 (m, 1H), 7.89-7.94 (m, 1H), 7.95-8.03 (m, 1H), 10.32-10.65 (m, 1H).

LCMS(ESI): [M+2H]$^+$ m/z: calcd 382.2; found 384.2; Rt=0.684 min.

Step 4: The Synthesis of N-(6-amino-5-methyl-3-pyridyl)-2-[(2R,5S)-5-methyl-2-[6-(methylamino)-3-pyridyl]-1-piperidyl]-2-oxo-acetamide Compound 876 tert-butyl N-[3-methyl-5-[[2-[(2R,5S)-5-methyl-2-[6-(methylamino)-3-pyridyl]-1-piperidyl]-2-oxo-acetyl]amino]-2-pyridyl]carbamate Isomer 2 (0.06791 g, 140.72 µmol) was dissolved in a mixture of Dioxane (1 mL) and Water (1 mL) and the resulting mixture was heated at 100° C. for 18 hr. The reaction mixture was concentrated in vacuo and the residue was purified by HPLC (35-55% MeOH/H$_2$O+NH$_3$-2-10 min, Flow rate: 30 mL/min; loading pump 4 mL/min MeOH+NH$_3$; target mass 382) to obtain N-(6-amino-5-methyl-3-pyridyl)-2-[(2R,5S)-5-methyl-2-[6-(methylamino)-3-pyridyl]-1-piperidyl]-2-oxo-acetamide (0.0368 g, 96.22 µmol, 68.37% yield).

$^1$H NMR (DMSO-d$_6$, 600 MHz): δ (ppm) 0.94-1.01 (m, 3H), 1.26-1.36 (m, 1H), 1.65-1.78 (m, 1H), 1.78-1.97 (m, 2H), 1.97-2.03 (m, 3H), 2.06-2.15 (m, 1H), 2.72 (s, 3H), 2.75-3.20 (m, 1H), 3.38-3.95 (m, 1H), 4.92-5.50 (m, 1H), 5.56-5.66 (m, 2H), 6.37-6.47 (m, 2H), 7.23-7.40 (m, 1H), 7.42-7.50 (m, 1H), 7.92 (s, 1H), 7.95-8.02 (m, 1H), 10.44 (s, 1H).

LCMS(ESI): [M+2H]$^+$ m/z: calcd 382.2; found 384.2; Rt=0.681 min.

Example 408. The Synthesis of N-(6-amino-5-ethyl-3-pyridyl)-2-[(2S,5R)-5-methyl-2-[6-(methylamino)-3-pyridyl]-1-piperidyl]-2-oxo-acetamide (Compound 865) and N-(6-amino-5-ethyl-3-pyridyl)-2-[(2R,5S)-5-methyl-2-[6-(methylamino)-3-pyridyl]-1-piperidyl]-2-oxo-acetamide (Compound 878

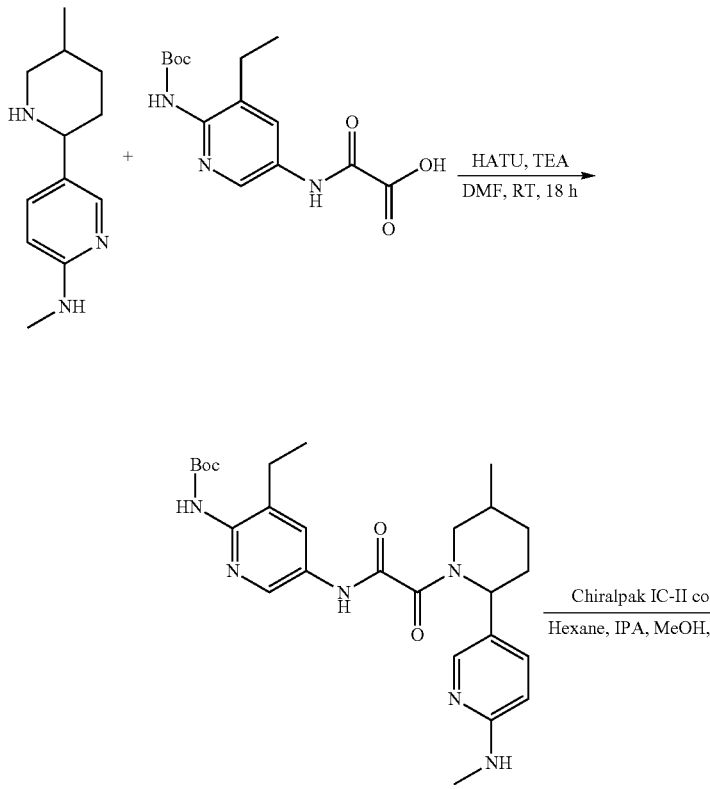

-continued

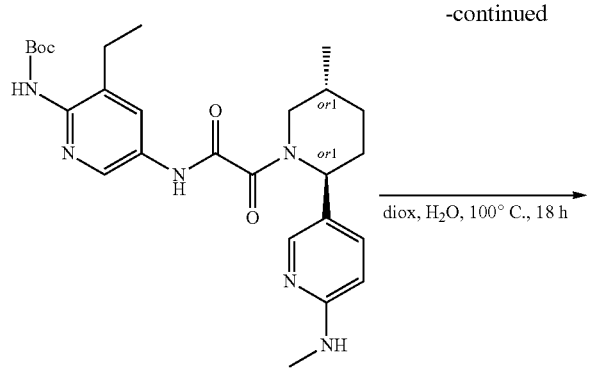

Compound 865

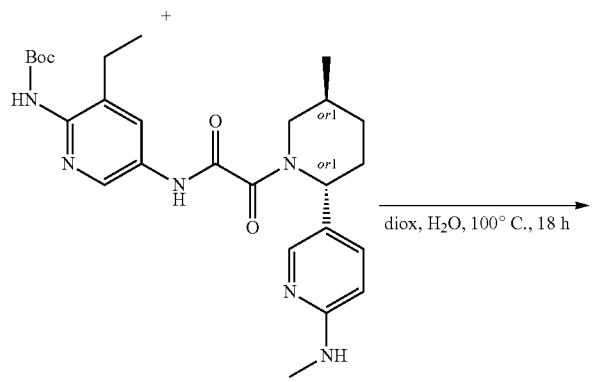

Compound 878

Step 1: The Synthesis of tert-butyl N-[3-ethyl-5-[[2-[5-methyl-2-[6-(methylamino)-3-pyridyl]-1-piperidyl]-2-oxo-acetyl]amino]-2-pyridyl]carbamate N-methyl-5-(5-methyl-2-piperidyl)pyridin-2-amine (0.4 g, 1.95 mmol), 2-[[6-(tert-butoxycarbonylamino)-5-ethyl-3-pyridyl]amino]-2-oxo-acetic acid (602.67 mg, 1.95 mmol) and triethylamine (1.97 g, 19.48 mmol, 2.72 mL) were mixed together in DMF (10 mL). HATU (1.11 g, 2.92 mmol) was added thereto and the resulting mixture was stirred for 18 hr. The reaction mixture was concentrated in vacuo and the residue was purified by HPLC (50-75% MeOH 2-10 min Flow rate: 30 mL/min; loading pump 4 mL/min MeOH; Column Sun Fire 100*19 mm, 5 mkm) to obtain tert-butyl N-[3-ethyl-5-[[2-[5-methyl-2-[6-(methylamino)-3-pyridyl]-1-piperidyl]-2-oxo-acetyl]amino]-2-pyridyl]carbamate (0.1351 g, 272.05 μmol, 13.96% yield)

LCMS(ESI): [M+H]$^+$ m/z: calcd 496.2; found 497.2; Rt=1.023 min.

Step 2: The Synthesis of tert-butyl N-[3-ethyl-5-[[2-[(2S,5R)-5-methyl-2-[6-(methylamino)-3-pyridyl]-1-piperidyl]-2-oxo-acetyl]amino]-2-pyridyl]carbamate and Tert-butyl N-[3-ethyl-5-[[2-[(2R,5S)-5-methyl-2-[6-(methylamino)-3-pyridyl]-1-piperidyl]-2-oxo-acetyl]amino]-2-pyridyl]carbamate tert-butyl N-[3-ethyl-5-[[2-[5-methyl-2-[6-(methylamino)-3-pyridyl]-1-piperidyl]-2-oxo-acetyl]amino]-2-pyridyl]carbamate (0.1351 g, 272.05 μmol) was chirally separated (Column: Chiralpak ICII(250*20 mm, 5 mkm); Mobile phase: Hexane-IPA-MeOH 50-25-25 Flow Rate: 12 mL/min; 7 inj., 20 mg/inj, 7.5 hr) to obtain tert-butyl N-[3-ethyl-5-[[2-[(2S,5R)-5-methyl-2-[6-(methylamino)-3-pyridyl]-1-piperidyl]-2-oxo-acetyl]amino]-2-pyridyl]carbamate Isomer 1 (0.04623 g, 93.09 μmol, 34.22% yield; RetTime=28.48) and tert-butyl N-[3-ethyl-5-[[2-[(2R,5S)-5-methyl-2-[6-(methylamino)-3-pyridyl]-1-piperidyl]-2-oxo-acetyl]amino]-2-pyridyl]carbamate Isomer 2 (0.0479 g, 96.46 μmol, 35.46% yield; RetTime=51.36)

1$^{st}$ Isomer: RT (IC, Hexane-IPA-MeOH, 50-25-25, 0.6 mL/min)=27.861 min.

LCMS(ESI): [M+2H]$^+$ m/z: calcd 496.2; found 497.2; Rt=2.178 min.

2$^{nd}$ Isomer: RT (IC, Hexane-IPA-MeOH, 50-25-25, 0.6 mL/min)=52.672 min.

LCMS(ESI): [M+2H]$^+$ m/z: calcd 496.2; found 497.2; Rt=2.173 min.

Step 3: The Synthesis of N-(6-amino-5-ethyl-3-pyridyl)-2-[(2S,5R)-5-methyl-2-[6-(methylamino)-3-pyridyl]-1-piperidyl]-2-oxo-acetamide (Compound 865 tert-butyl N-[3-ethyl-5-[[2-[(2S,5R)-5-methyl-2-[6-(methylamino)-3-pyridyl]-1-piperidyl]-2-oxo-acetyl]amino]-2-pyridyl]carbamate Isomer 1 (0.04623 g, 93.09 μmol) was dissolved in a mixture of Dioxane (1 mL) and Water (1 mL) and the resulting mixture was heated at 100° C. for 18 hr. The reaction mixture was concentrated in vacuo and the residue was purified by HPLC (35-55% MeOH/H$_2$O+NH$_3$ 2-10 min, Flow rate: 30 mL/min; loading pump 4 mL/min MeOH+NH$_3$) to obtain N-(6-amino-5-ethyl-3-pyridyl)-2-[(2S,5R)-5-methyl-2-[6-(methylamino)-3-pyridyl]-1-piperidyl]-2-oxo-acetamide (0.0251 g, 63.31 μmol, 68.00% yield).

2197

$^1$H NMR (DMSO-d$_6$, 600 MHz): δ (ppm) 0.96-1.02 (m, 3H), 1.06-1.13 (m, 3H), 1.25-1.36 (m, 1H), 1.67-1.77 (m, 1H), 1.79-1.91 (m, 1H), 1.92-2.05 (m, 1H), 2.06-2.18 (m, 1H), 2.36-2.42 (m, 2H), 2.73 (s, 3H), 2.77-3.17 (m, 1H), 3.40-3.96 (m, 1H), 4.96-5.50 (m, 1H), 5.55-5.65 (m, 2H), 6.37-6.46 (m, 2H), 7.24-7.38 (m, 1H), 7.43-7.49 (m, 1H), 7.92 (s, 1H), 7.97-8.06 (m, 1H), 10.44 (s, 1H).

LCMS(ESI): [M+2H]$^+$ m/z: calcd 396.2; found 398.2; Rt=0.719 min.

Step 4: The Synthesis of N-(6-amino-5-ethyl-3-pyridyl)-2-[(2R,5S)-5-methyl-2-[6-(methylamino)-3-pyridyl]-1-piperidyl]-2-oxo-acetamide (Compound 878 tert-butyl N-[3-ethyl-5-[[2-[(2R,5S)-5-methyl-2-[6-(methylamino)-3-pyridyl]-1-piperidyl]-2-oxo-acetyl]amino]-2-pyridyl]carbamate Isomer 2 (0.0479 g, 96.46 µmol) was dissolved in a mixture of Dioxane (1 mL) and Water (1 mL) and the resulting mixture was heated at 100° C. for 18 hr. The reaction mixture was concentrated in vacuo and the residue was purified by HPLC (35-55% MeOH/H$_2$O+NH$_3$ 2-10 min, Flow rate: 30 mL/min; loading pump 4 mL/min MeOH+NH$_3$) to obtain N-(6-amino-5-ethyl-3-pyridyl)-2-[(2R,5S)-5-methyl-2-[6-(methylamino)-3-pyridyl]-1-piperidyl]-2-oxo-acetamide (0.0248 g, 62.55 µmol, 64.85% yield).

$^1$H NMR (DMSO-d$_6$, 600 MHz): δ (ppm) 0.95-1.02 (m, 3H), 1.07-1.12 (m, 3H), 1.25-1.36 (m, 1H), 1.65-1.77 (m, 1H), 1.79-1.91 (m, 1H), 1.92-2.05 (m, 1H), 2.06-2.14 (m, 1H), 2.36-2.41 (m, 2H), 2.73 (s, 3H), 2.82-3.19 (m, 1H), 3.42-3.97 (m, 1H), 4.94-5.51 (m, 1H), 5.56-5.65 (m, 2H), 6.37-6.46 (m, 2H), 7.23-7.39 (m, 1H), 7.41-7.52 (m, 1H), 7.92 (s, 1H), 7.98-8.06 (m, 1H), 10.45 (s, 1H).

LCMS(ESI): [M+2H]$^+$ m/z: calcd 396.2; found 398.2; Rt=0.723 min.

Example 409. The Synthesis of N-(6-amino-5-methylpyridin-3-yl)-2-(2-(3,4-difluorophenyl)-5-methylpiperidin-1-yl)-2-oxoacetamide (Compound 472, Compound 458

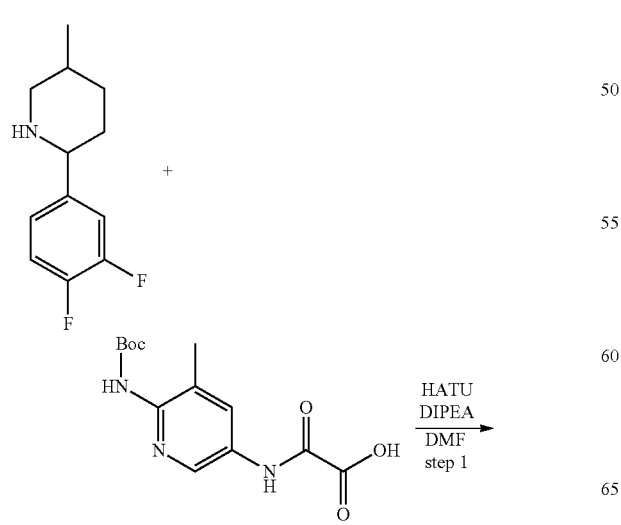

2198

-continued

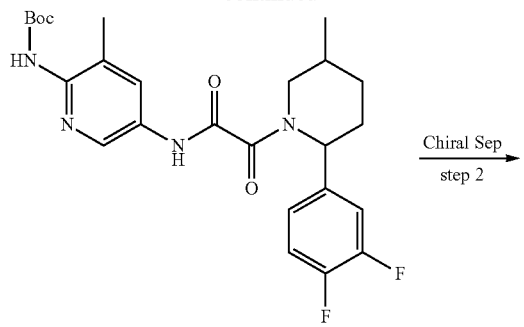

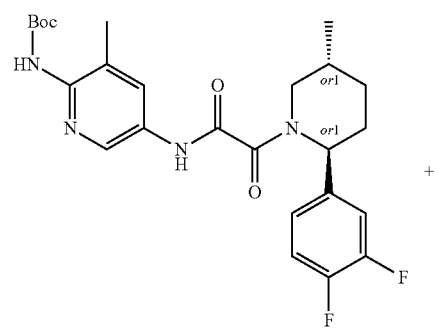

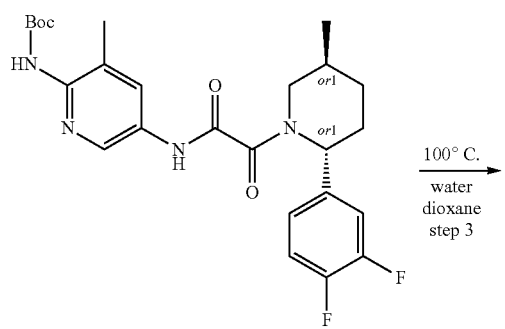

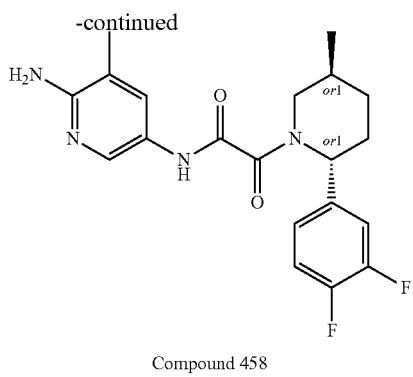

Compound 458

Step 1: Synthesis of tert-butyl (5-(2-(2-(3,4-difluorophenyl)-5-methylpiperidin-1-yl)-2-oxoacetamido)-3-methylpyridin-2-yl)carbamate DIPEA (525.22 mg, 4.06 mmol, 707.84 μL) was added to the solution of respective 2-[[6-(tert-butoxycarbonylamino)-5-methyl-3-pyridyl]amino]-2-oxo-acetic acid (0.4 g, 1.35 mmol) and (2S,5R)-2-(3,4-difluorophenyl)-5-methyl-piperidine (286.16 mg, 1.35 mmol) in DMF (10 mL). The resulting mixture was stirred for 5 min followed by the addition of the solution of HATU (566.56 mg, 1.49 mmol). Then, the reaction mixture was stirred overnight at rt. After the completion of the reaction, monitored by LCMS, the resulting suspension was concentrated under reduced pressure. The obtained solid was subjected to HPLC (column: Triart 100*20, 5 mkl; MeOH+NH₃ as an eluent mixture) to afford pure tert-butyl N-[5-[[2-[(2R,5S)-2-(3,4-difluorophenyl)-5-methyl-1-piperidyl]-2-oxo-acetyl]amino]-3-methyl-2-pyridyl]carbamate (370 mg, 757.38 μmol, 55.91% yield).

$^1$H NMR (400 MHz, CDCl$_3$) δ (ppm)

LCMS(ESI): [M]$^+$ m/z: calcd 488.2; found 489.2; Rt=4.078 min.

Step 2: Chiral Separation tert-butyl N-[5-[[2-[(2R,5S)-2-(3,4-difluorophenyl)-5-methyl-1-piperidyl]-2-oxo-acetyl]amino]-3-methyl-2-pyridyl]carbamate (370 mg, 757.38 μmol) was separated using Chiralpak IC 250*20, 5 mkm column; CO₂-MeOH, 70-30 as a mobile phase; Flow rate 50 mL/min; Injection Volume: 900 mkl; affording E1—tert-butyl N-[5-[[2-[(2S,5R)-2-(3,4-difluorophenyl)-5-methyl-1-piperidyl]-2-oxo-acetyl]amino]-3-methyl-2-pyridyl]carbamate (142.29 mg, 291.26 μmol, 38.46% yield) (RT (IC, CO₂-MeOH, 60-40, 2 ml/min)=5.93 min) as a beige solid and E2—tert-butyl N-[5-[[2-[(2R,5S)-2-(3,4-difluorophenyl)-5-methyl-1-piperidyl]-2-oxo-acetyl]amino]-3-methyl-2-pyridyl]carbamate (111.93 mg, 229.12 μmol, 30.25% yield) (RT (IC, CO₂-MeOH, 60-40, 2 ml/min)=4.83 min) as a beige solid.

E1: Retention time: 5.93 min $^1$H NMR (600 MHz, DMSO-d$_6$) δ (ppm)

LCMS(ESI): [M]$^+$ m/z: calcd 488.2; found 489.2; Rt=5.938 min.

E2: Retention time: 4.83 min $^1$H NMR (600 MHz, DMSO-d$_6$) δ (ppm)

LCMS(ESI): [M]$^+$ m/z: calcd 488.2; found 489.2; Rt=5.939 min.

Step 3: Synthesis of N-(6-amino-5-methylpyridin-3-yl)-2-(2-(3,4-difluorophenyl)-5-methylpiperidin-1-yl)-2-oxoacetamide (Compound 472 and Compound 458 tert-butyl N-[5-[[2-[(2R,5S)-2-(3,4-difluorophenyl)-5-methyl-1-piperidyl]-2-oxo-acetyl]amino]-3-methyl-2-pyridyl]carbamate E2 (111.93 mg, 229.12 μmol) and tert-butyl N-[5-[[2-[(2S,5R)-2-(3,4-difluorophenyl)-5-methyl-1-piperidyl]-2-oxo-acetyl]amino]-3-methyl-2-pyridyl] carbamate E1 (142.29 mg, 291.26 μmol) were dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (column: Triart 100*20, 5 mkl; MeCN+NH₃ as an eluent mixture) to afford pure N-(6-amino-5-methyl-3-pyridyl)-2-[(2R,5S)-2-(3,4-difluorophenyl)-5-methyl-1-piperidyl]-2-oxo-acetamide Compound 458 (67.1 mg, 172.76 μmol, 75.40% yield) and N-(6-amino-5-methyl-3-pyridyl)-2-[(2S,5R)-2-(3,4-difluorophenyl)-5-methyl-1-piperidyl]-2-oxo-acetamide Compound 472 (87.2 mg, 224.51 μmol, 77.08% yield).

Compound 472: $^1$H NMR (600 MHz, DMSO-d$_6$) δ (ppm) 0.94-1.02 (m, 3H), 1.25-1.38 (m, 1H), 1.57-1.68 (m, 1H), 1.80-1.92 (m, 1H), 1.95-2.07 (m, 4H), 2.12-2.23 (m, 1H), 2.67-3.23 (m, 1H), 3.38-4.05 (m, 1H), 5.07-5.54 (m, 1H), 5.56-5.65 (m, 2H), 7.10-7.21 (m, 1H), 7.31-7.40 (m, 1H), 7.40-7.49 (m, 2H), 7.93-8.04 (m, 1H), 10.45-10.64 (m, 1H).

LCMS(ESI): [M]$^+$ m/z: calcd 388.2; found 389.2; Rt=2.875 min.

Compound 458: $^1$H NMR (600 MHz, DMSO-d$_6$) δ (ppm) 0.97-1.00 (m, 3H), 1.25-1.36 (m, 1H), 1.57-1.67 (m, 1H), 1.80-1.92 (m, 1H), 1.96-2.03 (m, 4H), 2.12-2.24 (m, 1H), 2.68-3.22 (m, 1H), 3.41-4.03 (m, 1H), 5.08-5.52 (m, 1H), 5.58-5.63 (m, 2H), 7.09-7.20 (m, 1H), 7.30-7.40 (m, 1H), 7.41-7.49 (m, 2H), 7.93-8.03 (m, 1H), 10.47-10.53 (m, 1H).

LCMS(ESI): [M]$^+$ m/z: calcd 388.2; found 389.2; Rt=2.882 min.

Example 410. The Synthesis of N-(6-amino-5-methylpyridin-3-yl)-2-(5-methyl-2-(3,4,5-trifluorophenyl)piperidin-1-yl)-2-oxoacetamide (Compound 478, Compound 487

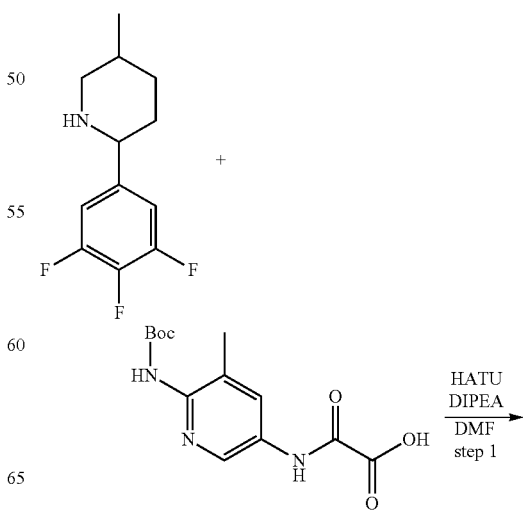

2201
-continued

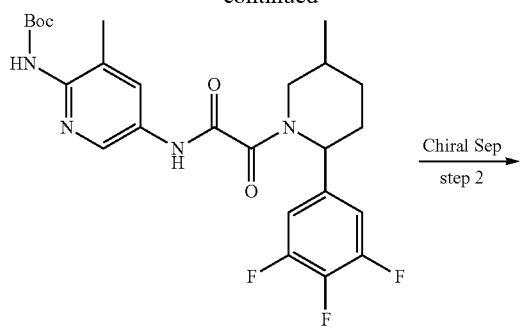

Chiral Sep
step 2

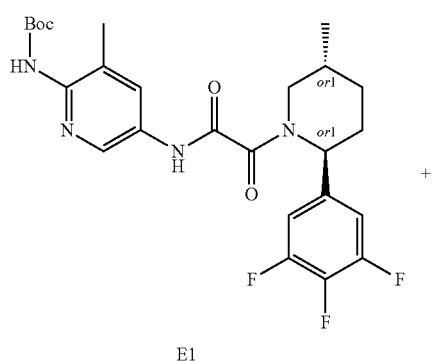

E1

+

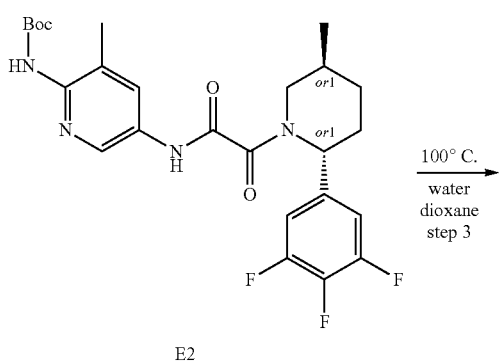

100° C.
water
dioxane
step 3

E2

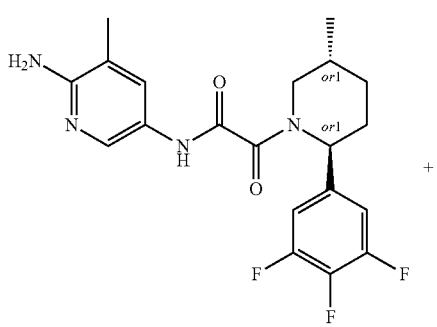

+

Compound 487

2202
-continued

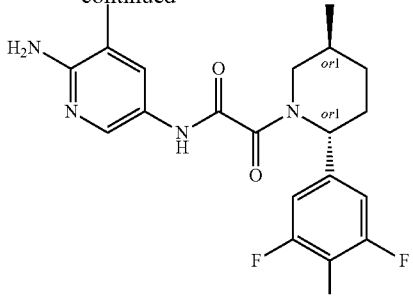

Compound 478

Step 1: Synthesis of tert-butyl (3-methyl-5-(2-(5-methyl-2-(3,4,5-trifluorophenyl)piperidin-1-yl)-2-oxoacetamido)pyridin-2-yl)carbamate DIPEA (459.56 mg, 3.56 mmol, 619.36 µL) was added to the solution of respective 2-[[6-(tert-butoxycarbonylamino)-5-methyl-3-pyridyl]amino]-2-oxo-acetic acid (0.3 g, 1.02 mmol) and 5-methyl-2-(3,4,5-trifluorophenyl)piperidine (232.90 mg, 1.02 mmol) in DMF (10 mL). The resulting mixture was stirred for 5 min followed by the addition of the solution of HATU (424.92 mg, 1.12 mmol). Then, the reaction mixture was stirred overnight at room temperature. After the completion of the reaction, monitored by LCMS, the resulting suspension was concentrated under reduced pressure. The obtained solid was subjected to HPLC (column: Triart 100*20, 5 mkl; MeOH+$NH_3$ as an eluent mixture) to afford pure tert-butyl N-[3-methyl-5-[[2-[5-methyl-2-(3,4,5-trifluorophenyl)-1-piperidyl]-2-oxo-acetyl]amino]-2-pyridyl]carbamate (0.21 g, 414.60 µmol, 40.81% yield).

LCMS(ESI): $[M]^+$ m/z: calcd 506.2; found 507.2; Rt=4.196 min.

Step 2: Chiral Separation tert-butyl N-[3-methyl-5-[[2-[5-methyl-2-(3,4,5-trifluorophenyl)-1-piperidyl]-2-oxo-acetyl]amino]-2-pyridyl]carbamate (57 mg, 149.04 µmol) was separated using Chiralpak AD 250*30, 5 mkm column; $CO_2$-MeOH, 60-40 as a mobile phase; Flow rate 30 mL/min; Injection Volume: 900 mkl; affording E1—tert-butyl N-[3-methyl-5-[[2-[(2S,5R)-5-methyl-2-(3,4,5-trifluorophenyl)-1-piperidyl]-2-oxo-acetyl]amino]-2-pyridyl]carbamate (66.11 mg, 130.52 µmol, 31.48% yield) (RT (AD-H, $CO_2$-MeOH, 60-40, 2 ml/min)=9.02 min) as a yellow solid and E2-tert-butyl N-[3-methyl-5-[[2-[(2R,5S)-5-methyl-2-(3,4,5-trifluorophenyl)-1-piperidyl]-2-oxo-acetyl]amino]-2-pyridyl]carbamate (70.13 mg, 138.46 µmol, 33.40% yield) (RT (AD-H, $CO_2$-MeOH, 60-40, 2 ml/min)=5.75 min) as a yellow solid.

E1: Retention time: 9.02 min
LCMS(ESI): $[M]^+$ m/z: calcd 506.2; found 507.2; Rt=6.118 min.
E2: Retention time: 5.75 min
LCMS(ESI): $[M]^+$ m/z: calcd 506.2; found 507.2; Rt=6.118 min.

Step 3: Synthesis of N-(6-amino-5-methylpyridin-3-yl)-2-(5-methyl-2-(3,4,5-trifluorophenyl)piperidin-1-yl)-2-oxoacetamide (Compound 487 and Compound 478 tert-butyl N-[3-methyl-5-[[2-[(2S,5R)-5-methyl-2-(3,4,5-trifluorophenyl)-1-piperidyl]-2-oxo-acetyl]amino]-2- pyridyl]carbamate E1 (66.11 mg, 130.52 μmol) and tert-butyl N-[3-methyl-5-[[2-[(2R,5S)-5-methyl-2-(3,4,5-trifluorophenyl)-1-piperidyl]-2-oxo-acetyl]amino]-2-pyridyl]carbamate E2 (70.13 mg, 138.46 μmol) were dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (column: Triart 100*20, 5 mkl; MeOH+NH$_3$ as an eluent mixture) to afford pure N-(6-amino-5-methyl-3-pyridyl)-2-[(2S,5R)-5-methyl-2-(3,4,5-trifluorophenyl)-1-piperidyl]-2-oxo-acetamide Compound 487 (34.9 mg, 85.88 μmol, 65.80% yield) and N-(6-amino-5-methyl-3-pyridyl)-2-[(2R,5S)-5-methyl-2-(3, 4,5-trifluorophenyl)-1-piperidyl]-2-oxo-acetamide Compound 478 (44.3 mg, 109.01 μmol, 78.73% yield).

Compound 487: $^1$H NMR (600 MHz, DMSO-d$_6$) δ (ppm) 0.95-1.02 (m, 3H), 1.24-1.36 (m, 1H), 1.57-1.67 (m, 1H), 1.79-1.91 (m, 1H), 1.97-2.06 (m, 4H), 2.12-2.24 (m, 1H), 2.70-3.25 (m, 1H), 3.39-4.03 (m, 1H), 5.05-5.50 (m, 1H), 5.56-5.68 (m, 2H), 7.17-7.33 (m, 2H), 7.41-7.52 (m, 1H), 7.91-8.06 (m, 1H), 10.40-10.67 (m, 1H).

LCMS(ESI): [M]$^+$ m/z: calcd 406.2; found 407.2; Rt=2.170 min.

Compound 478: $^1$H NMR (600 MHz, DMSO-d$_6$) δ (ppm) 0.96-1.01 (m, 3H), 1.23-1.36 (m, 1H), 1.55-1.68 (m, 1H), 1.80-1.92 (m, 1H), 1.95-2.04 (m, 4H), 2.13-2.24 (m, 1H), 2.70-3.24 (m, 1H), 3.40-4.05 (m, 1H), 5.06-5.48 (m, 1H), 5.58-5.65 (m, 2H), 7.19-7.32 (m, 2H), 7.40-7.51 (m, 1H), 7.91-8.06 (m, 1H), 10.45-10.64 (m, 1H).

LCMS(ESI): [M]$^+$ m/z: calcd 406.2; found 407.2; Rt=2.169 min.

Example 411. The Synthesis of N-(6-amino-5-methylpyridin-3-yl)-2-(2-(4-hydroxycyclohexyl)-5-methylpiperidin-1-yl)-2-oxoacetamide (Compound 423, Compound 436, Compound 431 and Compound 434

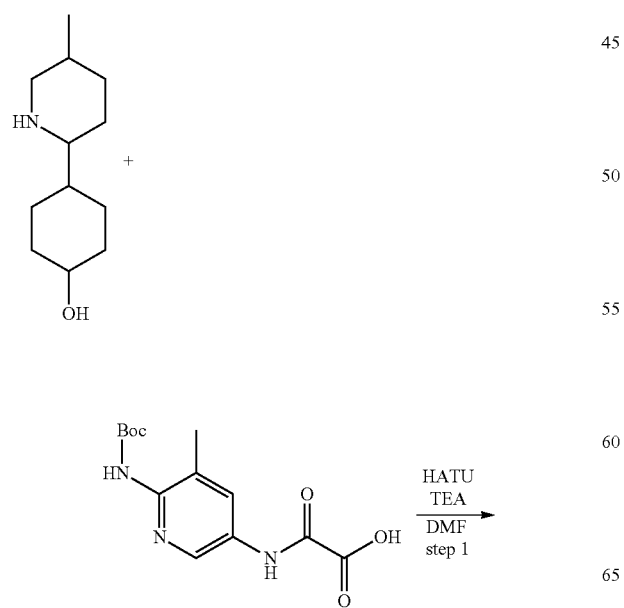

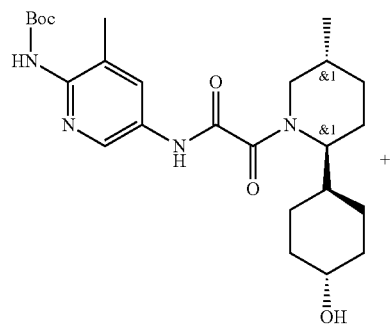

D1

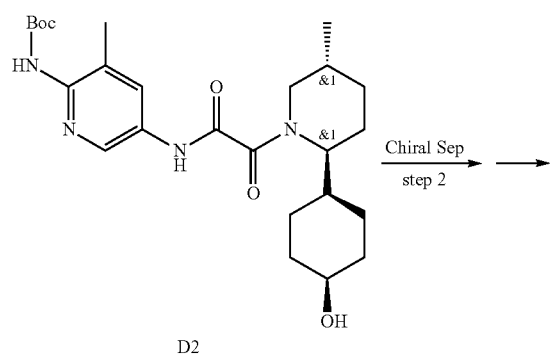

D2

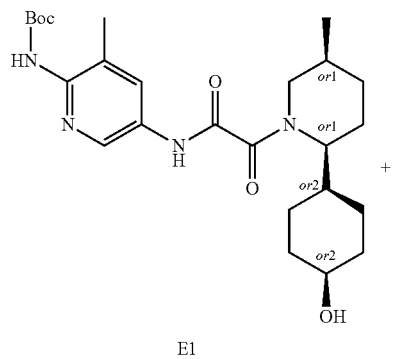

E1

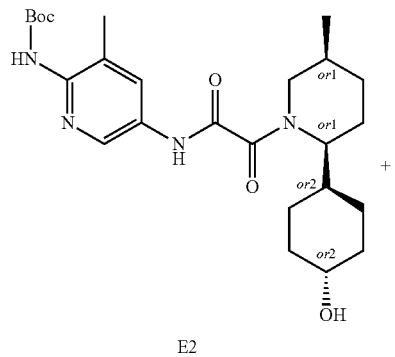

E2

2205

-continued

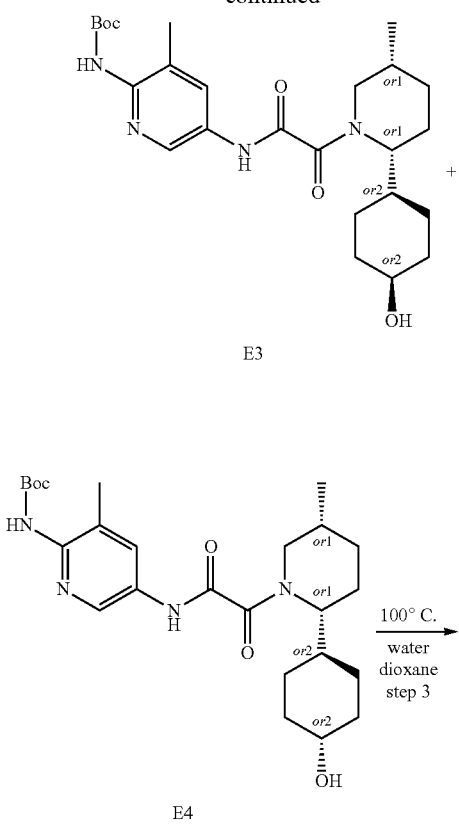

E3

E4

Compound 423

Compound 436

2206

-continued

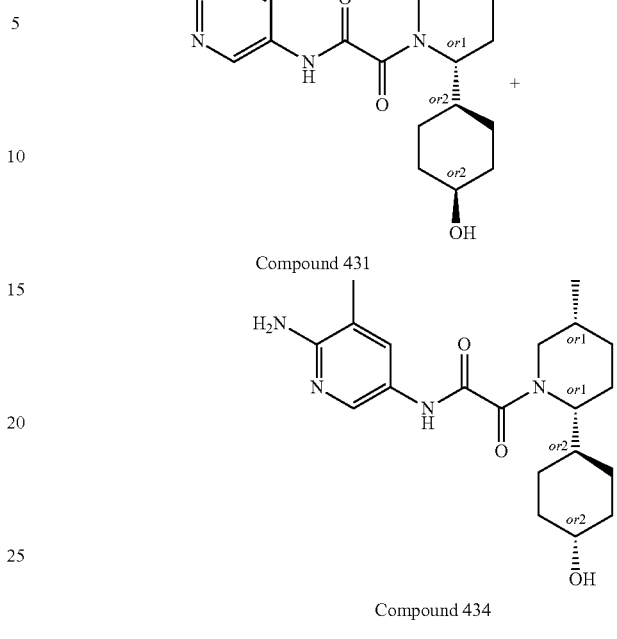

Compound 431

Compound 434

Step 1: Synthesis of tert-butyl (5-(2-(2-(4-hydroxy-cyclohexyl)-5-methylpiperidin-1-yl)-2-oxoacet-amido)-3-methylpyridin-2-yl)carbamate A mixture of 4-(5-methyl-2-piperidyl)cyclohexanol (500 mg, 2.53 mmol), 2-[[6-(tert-butoxycarbonylamino)-5-methyl-3-pyridyl]amino]-2-oxo-acetic acid (748.27 mg, 2.53 mmol) and TEA (2.56 g, 25.34 mmol, 3.53 mL) in DMF (20 mL) was stirred at 25° C. for 0.25 hr, then HATU (963.50 mg, 2.53 mmol) was added in small portions over 0.5 hr. The reaction mixture was stirred at 25° C. for 2 hr, then concentrated in vacuo to 5 ml and submitted to reverse phase HPLC (column: SunFire C18 100×19 mm 5um, mobile phase 20-65% 0-5 min water-MeOH+FA, flow: 30 ml/min), which afforded tert-butyl N-[5-[[2-[(2S,5R)-2-(4-hydroxycyclohexyl)-5-methyl-1-piperidyl]-2-oxo-acetyl] amino]-3-methyl-2-pyridyl]carbamate (260 mg, 547.84 μmol, 21.62% yield) and tert-butyl N-[5-[[2-[(2S,5R)-2-(4-hydroxycyclohexyl)-5-methyl-1-piperidyl]-2-oxo-acetyl] amino]-3-methyl-2-pyridyl]carbamate (240 mg, 505.70 μmol, 19.96% yield) as light-yellow gums, which were directly submitted to preparative chiral HPLC.

D1: LCMS(ESI): [M]⁺ m/z: calcd 474.2; found 475.2; Rt=2.953 min.

D2: CMS(ESI): [M]⁺ m/z: calcd 474.2; found 475.2; Rt=3.100 min.

Step 2: Chiral Separation

Racemic tert-butyl N-[5-[[2-[(2S,5R)-2-(4-hydroxycyclo-hexyl)-5-methyl-1-piperidyl]-2-oxo-acetyl]amino]-3-methyl-2-pyridyl]carbamate (240 mg, 505.70 μmol) was submitted to preparative chiral HPLC (Column: Chiralpak IC (250*20 mm, 5 mkm); Mobile phase: Hexane-IPA-MeOH, 40-30-30. Flow Rate: 11 mL/min; Column Temperature: 21° C.; Wavelength: 205 nm) to afford crude, containing traces of solvents tert-butyl N-[5-[[2-[(2S,5R)-2-

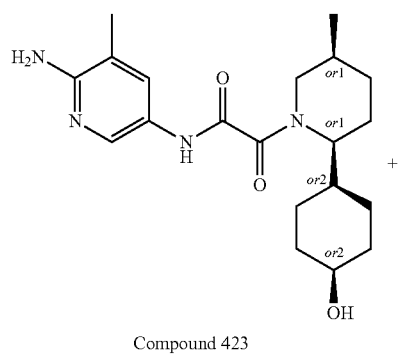


(4-hydroxycyclohexyl)-5-methyl-1-piperidyl]-2-oxo-acetyl]amino]-3-methyl-2-pyridyl]carbamate (121 mg, 254.96 µmol, 50.42% yield) E2 (R.T.=14.766 min.) and tert-butyl N-[5-[[2-[(2R,5S)-2-(4-hydroxycyclohexyl)-5-methyl-1-piperidyl]-2-oxo-acetyl]amino]-3-methyl-2-pyridyl]carbamate (119 mg, 250.74 µmol, 49.58% yield) E1 (R.T.=24.933 min.), which were used directly in the next step.

Racemic tert-butyl N-[5-[[2-[(2S,5R)-2-(4-hydroxycyclohexyl)-5-methyl-1-piperidyl]-2-oxo-acetyl]amino]-3-methyl-2-pyridyl]carbamate (260 mg, 547.84 µmol) was submitted to preparative chiral HPLC (Column: IB (250*30, 5 mkm), mobile phase:Hexane-IPA-MeOH, 80-10-10, flow rate 12 ml/min) to afford crude, containing traces of solvents tert-butyl N-[5-[[2-[(2R,5S)-2-(4-hydroxycyclohexyl)-5-methyl-1-piperidyl]-2-oxo-acetyl]amino]-3-methyl-2-pyridyl]carbamate (117 mg, 246.53 µmol, 45.00% yield) E4 (R.T.=14.531 min.) and tert-butyl N-[5-[[2-[(2S,5R)-2-(4-hydroxycyclohexyl)-5-methyl-1-piperidyl]-2-oxo-acetyl]amino]-3-methyl-2-pyridyl]carbamate E3 (114 mg, 240.21 µmol, 43.85% yield) (R.T.=29.070 min.), which were used directly in the next step.

E1: Retention time: 24.93 min
LCMS(ESI): [M]+ m/z: calcd 474.5; found 475.2; Rt=4.856 min.

E2: Retention time: 14.76 min
LCMS(ESI): [M]+ m/z: calcd 474.5; found 475.2; Rt=4.854 min.

E3: Retention time: 29.07 min
LCMS(ESI): [M]+ m/z: calcd 474.5; found 475.2; Rt=4.621 min.

E4: Retention time: 14.53 min
LCMS(ESI): [M]+ m/z: calcd 474.5; found 475.2; Rt=4.622 min.

Step 3: Synthesis of N-(6-amino-5-methylpyridin-3-yl)-2-(2-(4-hydroxycyclohexyl)-5-methylpiperidin-1-yl)-2-oxoacetamide (Compound 423, Compound 436 and Compound 431, Compound 434

A solution of tert-butyl N-[5-[[2-[(2S,5R)-2-(4-hydroxycyclohexyl)-5-methyl-1-piperidyl]-2-oxo-acetyl]amino]-3-methyl-2-pyridyl]carbamate E2 (121 mg, 254.96 µmol), tert-butyl N-[5-[[2-[(2R,5S)-2-(4-hydroxycyclohexyl)-5-methyl-1-piperidyl]-2-oxo-acetyl]amino]-3-methyl-2-pyridyl]carbamate E1 (119 mg, 250.74 µmol), tert-butyl N-[5-[[2-[(2R,5S)-2-(4-hydroxycyclohexyl)-5-methyl-1-piperidyl]-2-oxo-acetyl]amino]-3-methyl-2-pyridyl]carbamate E4 (117.00 mg, 246.53 µmol) and tert-butyl N-[5-[[2-[(2S,5R)-2-(4-hydroxycyclohexyl)-5-methyl-1-piperidyl]-2-oxo-acetyl]amino]-3-methyl-2-pyridyl]carbamate E3 (114 mg, 240.21 µmol) in a mixture of water (2 mL) and 1,4-dioxane (2 mL) was stirred at 95° C. for 12 hr, then cooled down and submitted to reverse phase HPLC (column: YMC Triart C18 100×20 mm, 5 um; mobile phase 40-40-65% 0-1-5 min 0.1% NH₃-MeOH, flow: 30 ml/min) to afford Compound 436 N-(6-amino-5-methyl-3-pyridyl)-2-[(2S,5R)-2-(4-hydroxycyclohexyl)-5-methyl-1-piperidyl]-2-oxo-acetamide (48 mg, 128.18 µmol, 50.27% yield), Compound 423 N-(6-amino-5-methyl-3-pyridyl)-2-[(2R,5S)-2-(4-hydroxycyclohexyl)-5-methyl-1-piperidyl]-2-oxo-acetamide (47.8 mg, 127.65 µmol, 50.91% yield), Compound 434 N-(6-amino-5-methyl-3-pyridyl)-2-[(2R,5S)-2-(4-hydroxycyclohexyl)-5-methyl-1-piperidyl]-2-oxo-acetamide (57.7 mg, 154.08 µmol, 62.50% yield) and Compound 431 N-(6-amino-5-methyl-3-pyridyl)-2-[(2S,5R)-2-(4-hydroxycyclohexyl)-5-methyl-1-piperidyl]-2-oxo-acetamide (52.5 mg, 140.20 µmol, 58.36% yield) as white solids.

Compound 423: ¹H NMR (500 MHz, DMSO-d₆) δ (ppm) 0.92-0.98 (m, 3H), 1.11-1.32 (m, 4H), 1.33-1.51 (m, 4H), 1.59-1.65 (m, 3H), 1.81-1.95 (m, 3H), 1.99-2.05 (m, 3H), 2.85-3.22 (m, 1H), 3.36-3.61 (m, 1H), 3.72-3.79 (m, 1H), 3.98-4.29 (m, 2H), 5.53-5.63 (m, 2H), 7.42-7.54 (m, 1H), 7.96-8.10 (m, 1H), 10.24-10.38 (m, 1H).

LCMS(ESI): [M]+ m/z: calcd 374.4; found 375.2; Rt=2.217 min.

Compound 436: ¹H NMR (500 MHz, DMSO-d₆) δ (ppm) 0.90-1.01 (m, 3H), 1.13-1.33 (m, 4H), 1.33-1.51 (m, 4H), 1.58-1.66 (m, 3H), 1.80-1.96 (m, 3H), 1.99-2.08 (m, 3H), 2.81-3.31 (m, 1H), 3.33-3.59 (m, 1H), 3.72-3.78 (m, 1H), 3.97-4.28 (m, 2H), 5.56-5.65 (m, 2H), 7.44-7.51 (m, 1H), 7.99-8.06 (m, 1H), 10.24-10.33 (m, 1H).

LCMS(ESI): [M]+ m/z: calcd 374.4; found 375.2; Rt=2.125 min.

Compound 431: ¹H NMR (500 MHz, DMSO-d₆) δ (ppm) 0.72-0.90 (m, 2H), 0.91-1.00 (m, 3H), 1.05-1.19 (m, 2H), 1.22-1.29 (m, 1H), 1.56 (d, 3H), 1.63-2.01 (m, 7H), 2.01-2.14 (m, 3H), 2.82-3.27 (m, 1H), 3.42-4.02 (m, 1H), 4.03-4.13 (m, 1H), 4.46-4.51 (m, 1H), 5.52-5.67 (m, 2H), 7.43-7.50 (m, 1H), 7.96-8.03 (m, 1H), 10.25-10.33 (m, 1H).

LCMS(ESI): [M]+ m/z: calcd 374.4; found 375.2; Rt=1.941 min.

Compound 434: ¹H NMR (500 MHz, DMSO-d₆) δ (ppm) 0.75-0.90 (m, 2H), 0.91-1.01 (m, 3H), 1.05-1.17 (m, 2H), 1.21-1.30 (m, 1H), 1.41-1.62 (m, 3H), 1.64-2.00 (m, 7H), 2.00-2.13 (m, 3H), 2.82-3.27 (m, 1H), 3.41-4.02 (m, 1H), 4.03-4.13 (m, 1H), 4.46-4.53 (m, 1H), 5.55-5.68 (m, 2H), 7.43-7.51 (m, 1H), 7.98-8.06 (m, 1H), 10.23-10.31 (m, 1H).

LCMS(ESI): [M]+ m/z: calcd 374.4; found 375.2; Rt=2.105 min.

Example 412. The Synthesis of N-(6-amino-5-methylpyridin-3-yl)-2-(2-(3-chloro-5-fluorophenyl)-5-methylpiperidin-1-yl)-2-oxoacetamide (Compound 682 and Compound 659

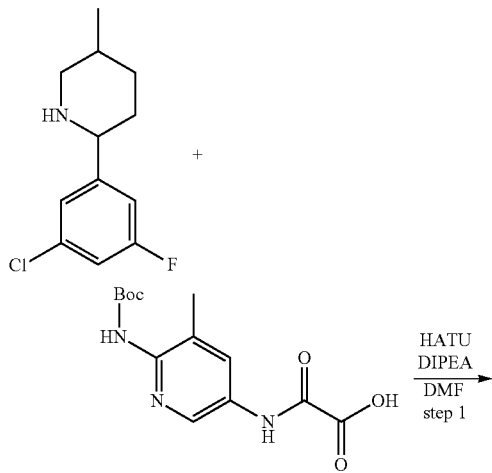

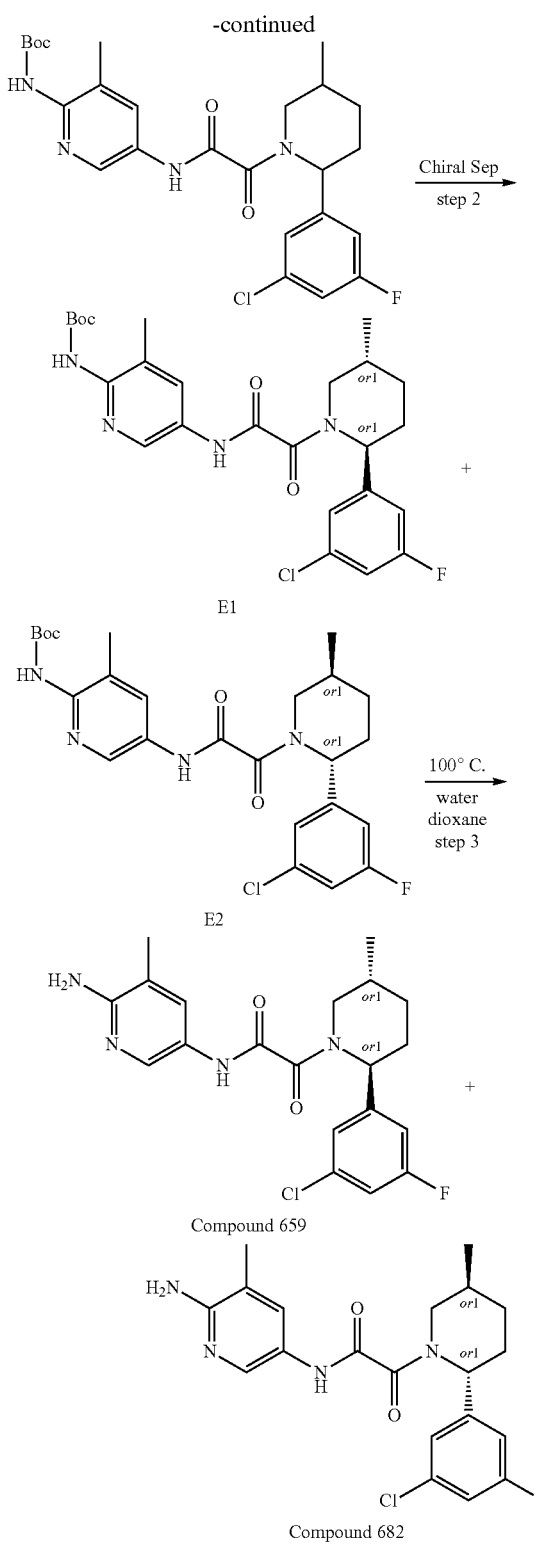

Step 1: Synthesis of tert-butyl (5-(2-(2-(3-chloro-5-fluorophenyl)-5-methylpiperidin-1-yl)-2-oxoacetamido)-3-methylpyridin-2-yl)carbamate DIPEA (393.91 mg, 3.05 mmol, 530.88 µL) was added to the solution of respective 2-[[6-(tert-butoxycarbonylamino)-5-methyl-3-pyridyl]amino]-2-oxo-acetic acid (0.3 g, 1.02 mmol) and 2-(3-chloro-5-fluoro-phenyl)-5-methyl-piperidine (231.34 mg, 1.02 mmol) in DMF (15 mL). The resulting mixture was stirred for 5 min followed by the addition of HATU (424.92 mg, 1.12 mmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 19*100 5 mkm column and H₂O-MeOH as an eluent mixture) to afford pure tert-butyl N-[5-[[2-[2-(3-chloro-5-fluoro-phenyl)-5-methyl-1-piperidyl]-2-oxo-acetyl]amino]-3-methyl-2-pyridyl]carbamate (0.32 g, 633.69 µmol, 62.37% yield).

LCMS(ESI): [M]$^+$ m/z: calcd 504.2; found 505.2; Rt=3.569 min.

Step 2: Chiral Separation

The enantiomers were separated by chiral HPLC (column: IC-II (250*20, 5 mkm), Hexane-MeOH-IPA, 80-15-15, 12 ml/min as mobile phase) to give the two individual enantiomers E1 tert-butyl N-[5-[[2-[(2S,5R)-2-(3-chloro-5-fluoro-phenyl)-5-methyl-1-piperidyl]-2-oxo-acetyl]amino]-3-methyl-2-pyridyl]carbamate (116.9 mg, 231.49 µmol, 36.53% yield) and E2 tert-butyl N-[5-[[2-[(2R,5S)-2-(3-chloro-5-fluoro-phenyl)-5-methyl-1-piperidyl]-2-oxo-acetyl]amino]-3-methyl-2-pyridyl]carbamate (109.4 mg, 216.64 µmol, 34.19% yield).

Ret time for E1 in analytical conditions (column: IC, Hexane-IPA-MeOH, 70-15-15, 0.6 ml/min as mobile phase) 20.40 min and for E2 29.38 min.

E1: LCMS(ESI): [M]$^+$ m/z: calcd 504.2; found 505.2; Rt=1.227 min.

E2: LCMS(ESI): [M]$^+$ m/z: calcd 504.2; found 505.2; Rt=1.224 min.

Step 3: Synthesis of tert-butyl (5-(2-(2-(3-chloro-5-fluorophenyl)-5-methylpiperidin-1-yl)-2-oxoacetamido)-3-methylpyridin-2-yl)carbamate (Compound 659 and Compound 682 tert-butyl N-[5-[[2-[(2R,5S)-2-(3-chloro-5-fluoro-phenyl)-5-methyl-1-piperidyl]-2-oxo-acetyl]amino]-3-methyl-2-pyridyl]carbamate E2 (109.4 mg, 216.64 µmol) and tert-butyl N-[5-[[2-[(2S,5R)-2-(3-chloro-5-fluoro-phenyl)-5-methyl-1-piperidyl]-2-oxo-acetyl]amino]-3-methyl-2-pyridyl]carbamate E1 (116.9 mg, 231.49 µmol) were dissolved in dioxane (2 mL) and water (5 mL) mixture. Then reaction mixture was stirred for 17 hr at 100° C. After the completion of the reaction, monitored by LCMS, the resulting suspension was concentrated under reduced pressure. The obtained solid was subjected to HPLC (Waters Sunfire C18 20*100 5 mkm column and H₂O-MeOH (45-60%)+NH₃ as an eluent mixture) to afford pure N-(6-amino-5-methyl-3-pyridyl)-2-[(2R,5S)-2-(3-chloro-5-fluoro-phenyl)-5-methyl-1-piperidyl]-2-oxo-acetamide (68.6 mg, 169.44 µmol, 78.21% yield) and N-(6-amino-5-methyl-3-pyridyl)-2-[(2S,5R)-2-(3-chloro-5-fluoro-phenyl)-5-methyl-1-piperidyl]-2-oxo-acetamide (48.8 mg, 120.53 µmol, 52.07% yield).

Compound 659: $^1$H NMR (600 MHz, DMSO-d$_6$) δ (ppm) 0.99 (m, 3H), 1.30 (m, 1H), 1.61 (m, 1H), 1.86 (m, 1H), 2.00 (m, 4H), 2.16 (m, 1H), 2.97 (m, 1H), 3.64 (m, 1H), 5.31 (m, 1H), 5.61 (m, 2H), 7.14 (m, 2H), 7.34 (m, 1H), 7.45 (m, 1H), 7.97 (m, 1H), 10.54 (m, 1H).

LCMS(ESI): [M]$^+$ m/z: calcd 404.2; found 405.2; Rt=2.525 min.

Compound 682: $^1$H NMR (600 MHz, DMSO-d$_6$) δ (ppm) 0.99 (m, 3H), 1.30 (m, 1H), 1.60 (m, 1H), 1.88 (m, 1H), 2.00 (m, 4H), 2.17 (m, 1H), 2.98 (m, 1H), 3.73 (m, 1H), 5.31 (m, 1H), 5.61 (m, 2H), 7.14 (m, 2H), 7.34 (m, 1H), 7.45 (d, 1H), 7.97 (m, 1H), 10.54 (m, 1H).

LCMS(ESI): [M]$^+$ m/z: calcd 404.2; found 405.2; Rt=2.494 min.

Example 413. The Synthesis of N-(6-amino-5-methylpyridin-3-yl)-2-(2-(3-chloro-4-(trifluoromethyl)phenyl)-5-methylpiperidin-1-yl)-2-oxoacetamide (Compound 689, Compound 703

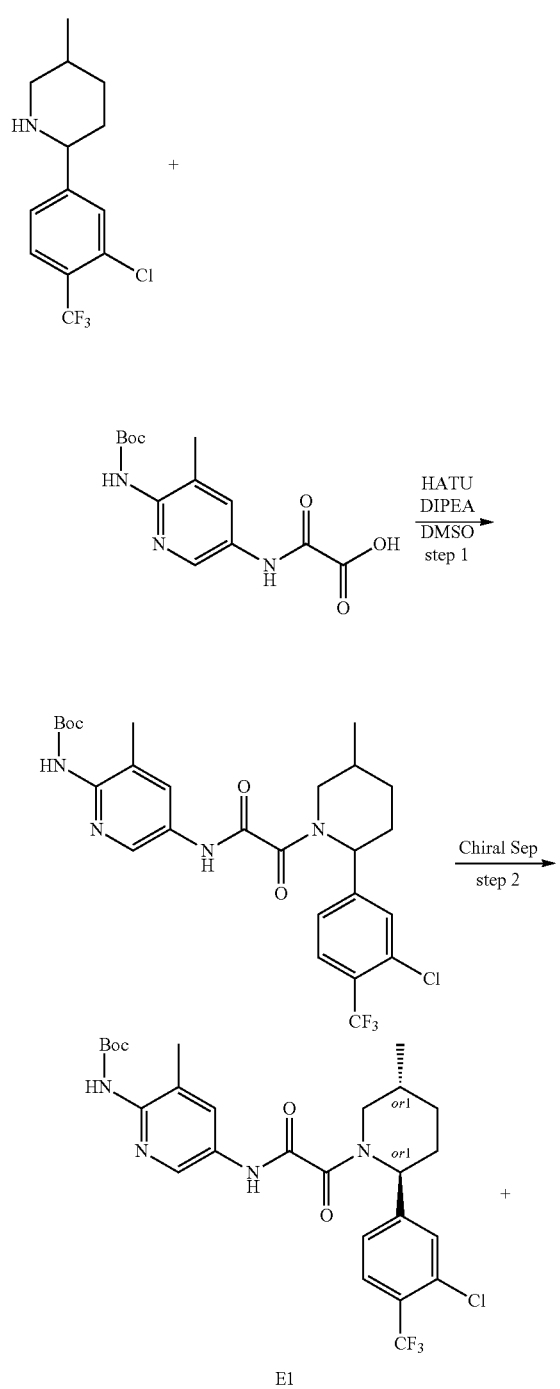

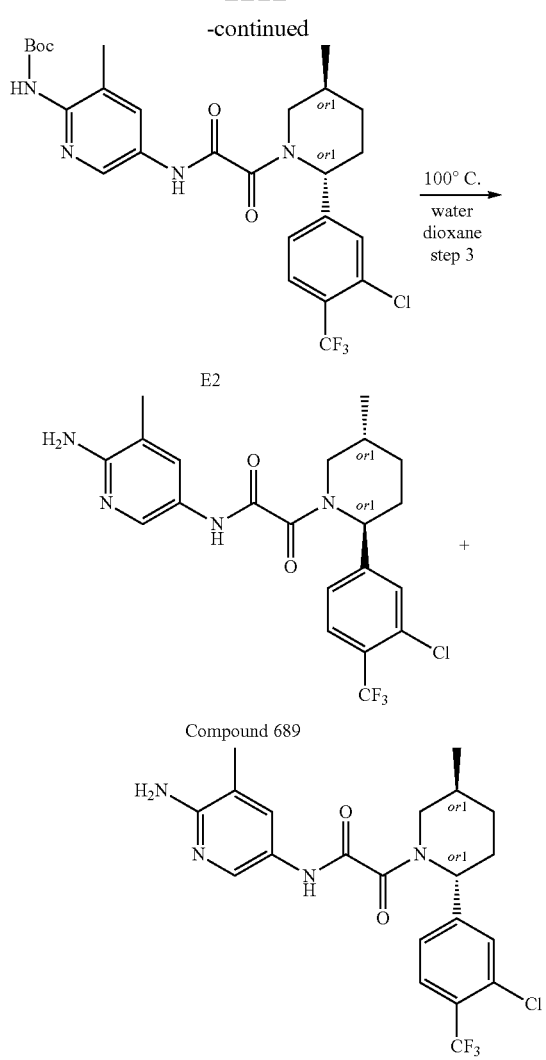

Step 1: Synthesis of tert-butyl (5-(2-(2-(3-chloro-4-(trifluoromethyl)phenyl)-5-methylpiperidin-1-yl)-2-oxoacetamido)-3-methylpyridin-2-yl)carbamate To a stirred solution of (2R,5S)-2-[3-chloro-4-(trifluoromethyl)phenyl]-5-methyl-piperidine (0.9 g, 3.24 mmol), 2-[[6-(tert-butoxycarbonylamino)-5-methyl-3-pyridyl]amino]-2-oxo-acetic acid (1.15 g, 3.89 mmol, HCl) and DIPEA (1.05 g, 8.10 mmol, 1.41 mL) in DMSO (5 mL) was added HATU (1.48 g, 3.89 mmol). The resulting reaction mixture was stirred at 20° C. for 13 hr. Upon completion, the reaction mixture was submitted to reverse phase HPLC (column: SunFire 19*100 mm, 5 mkl; MeOH as an eluent mixture) to afford tert-butyl N-[5-[[2-[(2R,5S)-2-[3-chloro-4-(trifluoromethyl)phenyl]-5-methyl-1-piperidyl]-2-oxo-acetyl]amino]-3-methyl-2-pyridyl]carbamate (0.32 g, 576.59 μmol, 17.79% yield) as light-yellow solid.

LCMS(ESI): [M]$^+$ m/z: calcd 554.2; found 555.2; Rt=1.445 min.

Step 2: Chiral Separation tert-butyl N-[5-[[2-[(2R,5S)-2-[3-chloro-4-(trifluoromethyl)phenyl]-5-methyl-1-piperidyl]-2-oxo-acetyl]amino]-

3-methyl-2-pyridyl]carbamate (0.32 g, 576.59 µmol) was submitted to chiral separation (IA-I (250*20, 5 mkm), Hexane-IPA-MeOH, 60-20-20, 12 ml/min) to afford tert-butyl N-[5-[[2-[(2R,5S)-2-[3-chloro-4-(trifluoromethyl)phenyl]-5-methyl-1-piperidyl]-2-oxo-acetyl]amino]-3-methyl-2-pyridyl]carbamate (0.12 g, 216.22 µmol, 37.50% yield) and tert-butyl N-[5-[[2-[(2S,5R)-2-[3-chloro-4-(trifluoromethyl)phenyl]-5-methyl-1-piperidyl]-2-oxo-acetyl]amino]-3-methyl-2-pyridyl]carbamate (0.1 g, 180.18 µmol, 31.25% yield). Ret time for E1 in analytical conditions (column: IA, Hexane-IPA-MeOH, 60-20-20, 0.6 ml/min as mobile phase) 20.78 min and for E2 15.01 min.

E1: Retention time: 20.78 min
LCMS(ESI): [M]+ m/z: calcd 554.2; found 555.2; Rt=5.656 min.

E2: Retention time: 15.01 min
LCMS(ESI): [M]+ m/z: calcd 554.2; found 555.2; Rt=6.191 min.

Step 3: Synthesis of N-(6-amino-5-methylpyridin-3-yl)-2-(2-(3-chloro-4-(trifluoromethyl)phenyl)-5-methylpiperidin-1-yl)-2-oxoacetamide (Compound 703 and Compound 689 tert-butyl N-[5-[[2-[(2R,5S)-2-[3-chloro-4-(trifluoromethyl)phenyl]-5-methyl-1-piperidyl]-2-oxo-acetyl]amino]-3-methyl-2-pyridyl]carbamate (0.11 g, 198.20 µmol) and tert-butyl N-[5-[[2-[(2S,5R)-2-[3-chloro-4-(trifluoromethyl)phenyl]-5-methyl-1-piperidyl]-2-oxo-acetyl]amino]-3-methyl-2-pyridyl]carbamate (0.1 g, 180.18 µmol) were added to a mixture of water (0.7 mL) and 1,4-dioxane (2 mL) and the reaction mixture was stirred at 80° C. for 16 hr. After cooling down, the solution was concentrated under reduced pressure and the residue was submitted to reverse phase HPLC (column: SunFire 19*100 mm, 5 mkl; water-MeOH as an eluent mixture) to afford N-(6-amino-5-methyl-3-pyridyl)-2-[(2R,5S)-2-[3-chloro-4-(trifluoromethyl)phenyl]-5-methyl-1-piperidyl]-2-oxo-acetamide (0.037 g, 81.34 µmol, 41.04% yield) and N-(6-amino-5-methyl-3-pyridyl)-2-[(2S,5R)-2-[3-chloro-4-(trifluoromethyl)phenyl]-5-methyl-1-piperidyl]-2-oxo-acetamide (0.04 g, 87.94 µmol, 48.80% yield) as a white solid.

Compound 689: $^1$H NMR (600 MHz, DMSO-$d_6$) δ (ppm) 0.99 (m, 3H), 1.31 (m, 1H), 1.61 (m, 1H), 1.88 (m, 1H), 2.00 (m, 3H), 2.14 (m, 2H), 3.01 (m, 1H), 3.65 (m, 1H), 5.59 (m, 3H), 7.45 (m, 2H), 7.61 (m, 1H), 7.85 (m, 1H), 7.97 (m, 1H), 10.53 (m, 1H).

LCMS(ESI): [M]+ m/z: calcd 454.2; found 455.2; Rt=2.501 min.

Compound 703: $^1$H NMR (600 MHz, DMSO-$d_6$) δ (ppm) 0.99 (m, 3H), 1.31 (m, 1H), 1.62 (m, 1H), 1.87 (m, 1H), 2.00 (m, 3H), 2.13 (m, 2H), 3.00 (m, 1H), 3.75 (m, 1H), 5.58 (m, 3H), 7.45 (m, 2H), 7.61 (m, 1H), 7.85 (m, 1H), 7.97 (m, 1H), 10.53 (m, 1H).

LCMS(ESI): [M]+ m/z: calcd 454.2; found 455.2; Rt=2.481 min.

Example 414. The Synthesis of N-(6-amino-5-methyl-3-pyridyl)-2-[(2R,5S)-2-[4-(hydroxymethyl)phenyl]-5-methyl-1-piperidyl]-2-oxo-acetamide (Compound 806) and N-(6-amino-5-methyl-3-pyridyl)-2-[(2S,5R)-2-[4-(hydroxymethyl)phenyl]-5-methyl-1-piperidyl]-2-oxo-acetamide (Compound 802

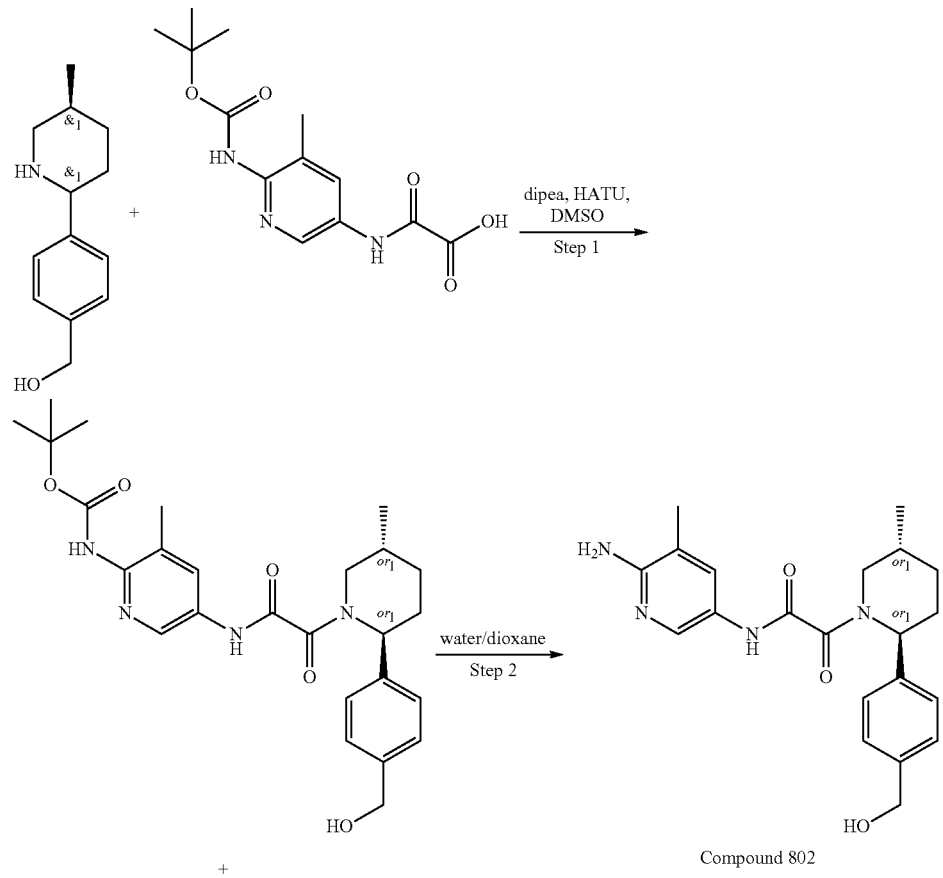

Compound 802

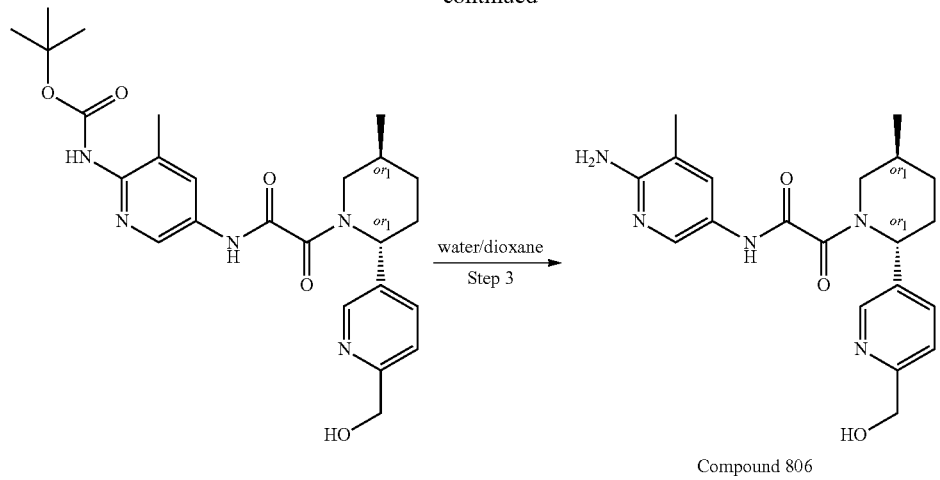

Compound 806

Step 1: Synthesis of tert-butyl N-[5-[[2-[(2R,5)-2-[4-(hydroxymethyl)phenyl]-5-methyl-1-piperidyl]-2-oxo-acetyl]amino]-3-methyl-2-pyridyl]carbamate (P1) and Tert-butyl N-[5-[[2-[(2S,5R)-2-[4-(hydroxymethyl)phenyl]-5-methyl-1-piperidyl]-2-oxo-acetyl]amino]-3-methyl-2-pyridyl]carbamate (P2

2-[[6-(tert-butoxycarbonylamino)-5-methyl-3-pyridyl]amino]-2-oxo-acetic acid (287.67 mg, 974.21 µmol), [4-[(2R,5S)-5-methyl-2-piperidyl]phenyl]methanol (0.2 g, 974.21 µmol) and dipea (377.73 mg, 2.92 mmol, 509.07 µL) were dissolved in DMSO (6 mL) under gentle heating. HATU (444.51 mg, 1.17 mmol) was added in small portions under vigorous stirring and occasional heating. After the reaction was complete, the mixture was purified by HPLC to give racemic product, which was subjected to chiral HPLC to give tert-butyl N-[5-[[2-[(2R,5S)-2-[4-(hydroxymethyl)phenyl]-5-methyl-1-piperidyl]-2-oxo-acetyl]amino]-3-methyl-2-pyridyl]carbamate (30 mg, 62.17 µmol, 6.38% yield) and tert-butyl N-[5-[[2-[(2S,5R)-2-[4-(hydroxymethyl)phenyl]-5-methyl-1-piperidyl]-2-oxo-acetyl]amino]-3-methyl-2-pyridyl]carbamate (39 mg, 80.82 µmol, 8.30% yield)

HPLC conditions: (32-36% 0.9-6 min water-acetonitrile; flow 30 ml/min (loading pump 4 ml/min acetonitrile); target mass 482; column SunFire C18 100×19 mm 5 um (R))

Chiral preparative HPLC conditions:Chiralcel OJ-H (250*20, 5 mkm), Mobile phase: Hexane-IPA-MeOH, 80-10-10; Flow rate: 12 ml/min. 24° C., Wavelength: 205 nm, 215 nm Retention time (isomer 1(SR))=19.9 Retention time (isomer 2(RS))=33.28

P1: LCMS(ESI): [M+H]+ m/z: calcd 482.6; found 483.2; Rt=5.045 min.

RT (Hexane-IPA-MeOH, 80-10-10, 12 ml/min)=11.3442 min.

P2: LCMS(ESI): [M+H]+ m/z: calcd 482.6; found 483.2; Rt=5.043 min.

RT (Hexane-IPA-MeOH, 80-10-10, 12 ml/min)=19.8252 min.

Step 2: The Synthesis of N-(6-amino-5-methyl-3-pyridyl)-2-[(2R,5S)-2-[4-(hydroxymethyl)phenyl]-5-methyl-1-piperidyl]-2-oxo-acetamide (Compound 806 tert-butyl N-[5-[[2-[(2R,5S)-2-[4-(hydroxymethyl)phenyl]-5-methyl-1-piperidyl]-2-oxo-acetyl]amino]-3-methyl-2-pyridyl]carbamate (30 mg, 62.17 µmol) was dissolved in water (1 mL)/dioxane (1 mL) mixture and stirred at reflux overnight. Aliquot shows the full consumption of the starting material; evaporation of the solvents under reduced pressure and purification with HPLC (5-50% 0.5-6.5 min water-acetonitrile; flow 30 ml/min (loading pump 4 ml/min acetonitrile); target mass 382; column SunFire C18 100×19 mm 5 um (R)) results in N-(6-amino-5-methyl-3-pyridyl)-2-[(2R,5S)-2-[4-(hydroxymethyl)phenyl]-5-methyl-1-piperidyl]-2-oxo-acetamide (20 mg, 52.29 µmol, 84.12% yield).

LCMS(ESI): [M+H]+ m/z: calcd 382.2; found 383.4; Rt=1.541 min.

Step 3: The Synthesis of N-(6-amino-5-methyl-3-pyridyl)-2-[(2S,5R)-2-[4-(hydroxymethyl)phenyl]-5-methyl-1-piperidyl]-2-oxo-acetamide (Compound 802 tert-butyl N-[5-[[2-[(2S,5R)-2-[4-(hydroxymethyl)phenyl]-5-methyl-1-piperidyl]-2-oxo-acetyl]amino]-3-methyl-2-pyridyl]carbamate (38 mg, 78.74 µmol) was dissolved in water (1 mL)/dioxane (1 mL) mixture and stirred at reflux overnight. Aliquot shows the full consumption of the starting material; evaporation of the solvents under reduced pressure and purification with HPLC (5-40% 0.5-6.5 min water-acetonitrile; flow 30 ml/min (loading pump 4 ml/min acetonitrile); target mass 382; column SunFire C18 100×19 mm 5 um (R)) results in N-(6-amino-5-methyl-3-pyridyl)-2-[(2S,5R)-2-[4-(hydroxymethyl)phenyl]-5-methyl-1-piperidyl]-2-oxo-acetamide (10 mg, 26.15 µmol, 33.20% yield).

$^1$H NMR (DMSO-$d_6$, 600 MHz): δ (ppm) 0.98-1.03 (m, 3H), 1.27-1.36 (m, 1H), 1.61-1.69 (m, 1H), 1.80-1.91 (m, 1H), 1.97-2.02 (m, 3H), 2.02-2.14 (m, 1H), 2.16-2.27 (m, 1H), 2.68-3.19 (m, 1H), 3.41-4.05 (m, 1H), 4.42-4.50 (m, 2H), 5.09-5.57 (m, 2H), 5.57-5.65 (m, 2H), 7.21-7.24 (m, 1H), 7.24-7.34 (m, 3H), 7.42-7.54 (m, 1H), 7.88-8.05 (m, 1H), 10.41-10.52 (m, 1H).

LCMS(ESI): [M+H]+ m/z: calcd 382.2; found 383.4; Rt=1.752 min.

Example 415. The Synthesis of rac-N-(6-amino-5-methyl-3-pyridyl)-2-[(2S,5R)-2-(4-tert-butylcyclohexyl)-5-methyl-1-piperidyl]-2-oxo-acetamide (Compound 145), N-(6-amino-5-methyl-3-pyridyl)-2-[(2S,5R)-2-(4-tert-butylcyclohexyl)-5-methyl-1-piperidyl]-2-oxo-acetamide (Compound 260) and N-(6-amino-5-methyl-3-pyridyl)-2-[(2R,5S)-2-(4-tert-butylcyclohexyl)-5-methyl-1-piperidyl]-2-oxo-acetamide (Compound 290
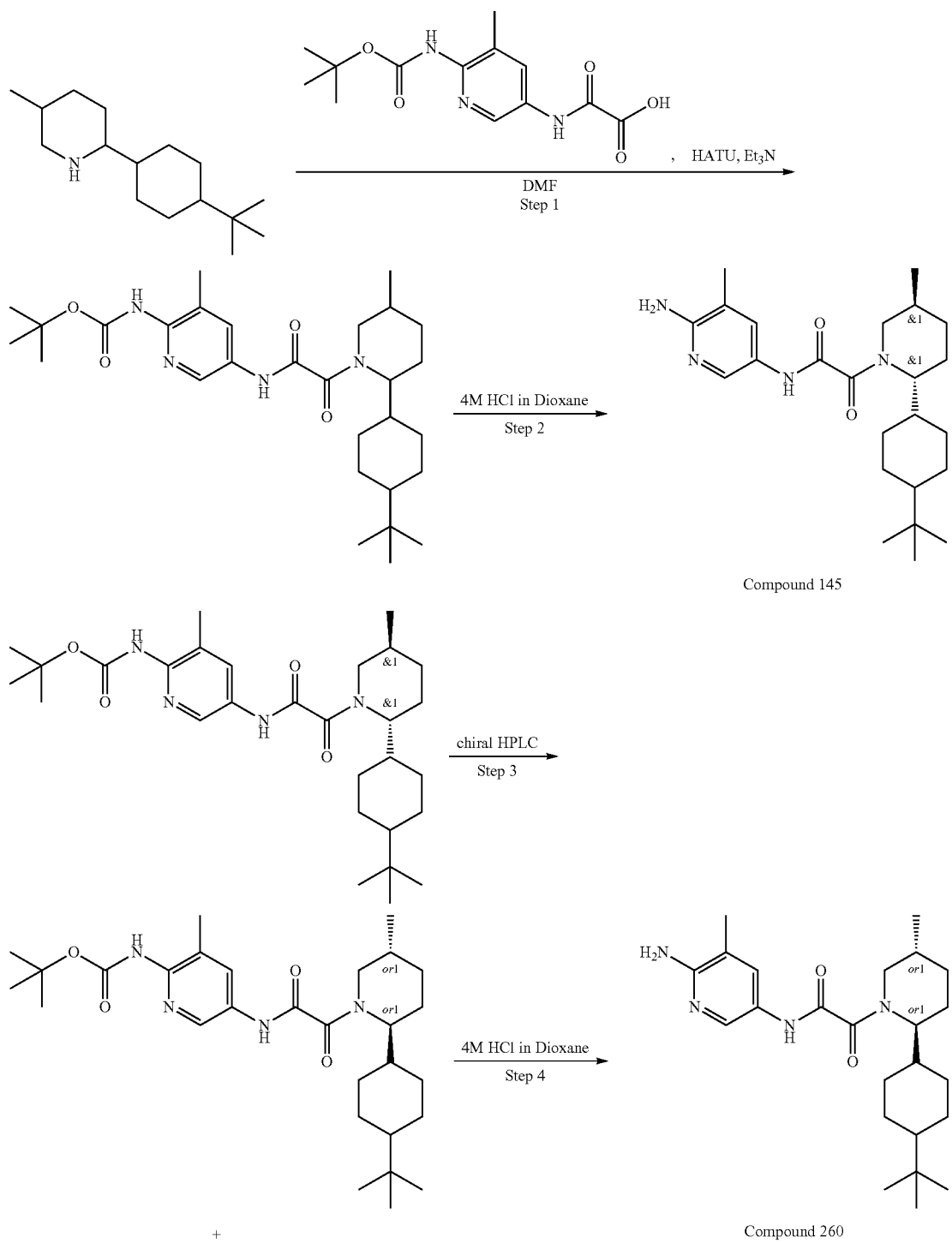

2219

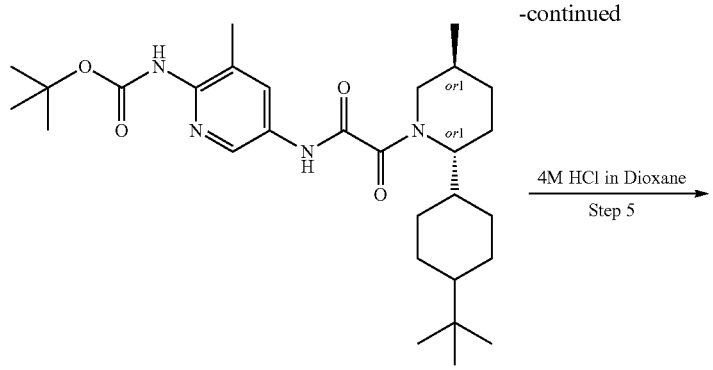

2220

-continued

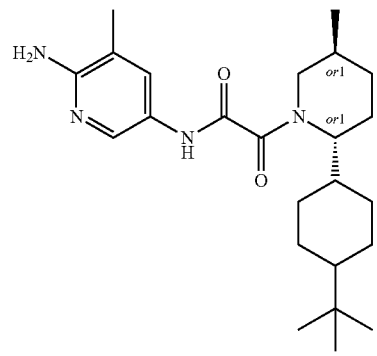

Compound 290

4M HCl in Dioxane
Step 5

Step 1: Synthesis of tert-butyl N-[5-[[2-[2-(4-tert-butylcyclohexyl)-5-methyl-1-piperidyl]-2-oxo-acetyl]amino]-3-methyl-2-pyridyl]carbamate To a stirred solution of 2-[[6-(tert-butoxycarbonylamino)-5-methyl-3-pyridyl]amino]-2-oxo-acetic acid (621.87 mg, 2.11 mmol), 2-(4-tert-butylcyclohexyl)-5-methyl-piperidine (0.5 g, 2.11 mmol) and HATU (880.82 mg, 2.32 mmol) in DMF (1.5 mL) was added Triethylamine (852.40 mg, 8.42 mmol, 1.17 mL). The resulting reaction mixture was stirred at 25° C. for 4 hours. After 4 hours, the reaction mixture was concentrated under reduced pressure and the obtained crude product was purified by reverse phase HPLC (Eluent: 70-70-100%, 0-1-6 min, water-methanol; flow rate: 30 mL/min; loading pump: 4 mL/min, methanol; column: SunFire C18 100×19 mm, 5 um) to give tert-butyl N-[5-[[2-[2-(4-tert-butylcyclohexyl)-5-methyl-1-piperidyl]-2-oxo-acetyl]amino]-3-methyl-2-pyridyl]carbamate (0.25 g, 485.72 μmol, 23.06% yield) as a white solid.

LCMS(ESI): [M+Boc]$^+$ m/z: calcd 514.4; found 515.4; Rt=4.992 min.

Step 2: Synthesis of rac-N-(6-amino-5-methyl-3-pyridyl)-2-[(2S,5R)-2-(4-tert-butylcyclohexyl)-5-methyl-1-piperidyl]-2-oxo-acetamide (Compound 145

A solution of tert-butyl N-[5-[[2-[2-(4-tert-butylcyclohexyl)-5-methyl-1-piperidyl]-2-oxo-acetyl]amino]-3-methyl-2-pyridyl]carbamate (0.1 g, 194.29 μmol) in 4.0 M HCl in dioxane (70.84 mg, 1.94 mmol, 88.55 μL) was stirred at 25° C. for 2 hours. After 2 hours, the reaction mixture was concentrated under reduced pressure and the crude product was purified by reverse phase HPLC (Eluent: 0-5 min, 65-85%, water-methanol (0.1% NH$_3$); flow rate: 30 mL/min; loading pump: 4 mL/min, methanol (0.1% NH$_3$); column: YMC-Actus Triart C18 100*20 mm, 5 um) to obtain rac-N-(6-amino-5-methyl-3-pyridyl)-2-[(2S,5R)-2-(4-tert-butylcyclohexyl)-5-methyl-1-piperidyl]-2-oxo-acetamide (Compound 145, 42 mg, 101.31 μmol, 52.14% yield) as a white solid.

$^1$H NMR (DMSO-d$_6$, 500 MHz): δ (ppm) 0.82 (m, 11H), 0.94 (m, 6H), 1.28 (m, 1H), 1.62 (m, 2H), 1.76 (m, 5H), 1.85 (m, 2H), 2.03 (s, 3H), 2.84 (m, 1H), 3.45 (d, 1H), 4.04 (m, 1H), 5.60 (m, 2H), 7.47 (m, 1H), 8.08 (m, 1H), 10.26 (m, 1H).

LCMS(ESI): [M+H]$^+$ m/z: calcd 414.4; found 415.4; Rt=3.779 min.

Step 3: Chiral Separation of Tert-butyl N-[5-[[2-[(2R,5S)-2-(4-tert-butylcyclohexyl)-5-methyl-1-piperidyl]-2-oxo-acetyl]amino]-3-methyl-2-pyridyl] carbamate and Tert-butyl N-[5-[[2-[(2S,5R)-2-(4-tert-butylcyclohexyl)-5-methyl-1-piperidyl]-2-oxo-acetyl]amino]-3-methyl-2-pyridyl]carbamate rac-tert-butyl N-[5-[[2-[(2R,5S)-2-(4-tert-butylcyclohexyl)-5-methyl-1-piperidyl]-2-oxo-acetyl]amino]-3-methyl-2-pyridyl]carbamate (90 mg, 174.86 μmol) was purified by chiral HPLC (Eluent: Hexane-IPA-MeOH, 60-20-20; column: IC, 250*20 mm, 5 um; flow rate: 12 mL/min) to give tert-butyl N-[5-[[2-[(2R,5S)-2-(4-tert-butylcyclohexyl)-5-methyl-1-piperidyl]-2-oxo-acetyl]amino]-3-methyl-2-pyridyl]carbamate (34 mg, 66.06 μmol, 37.78% yield) and tert-butyl N-[5-[[2-[(2S,5R)-2-(4-tert-butylcyclohexyl)-5-methyl-1-piperidyl]-2-oxo-acetyl]amino]-3-methyl-2-pyridyl]carbamate (26 mg, 50.52 μmol, 28.89% yield) as white solids.

tert-butyl N-[5-[[2-[(2R,5S)-2-(4-tert-butylcyclohexyl)-5-methyl-1-piperidyl]-2-oxo-acetyl]amino]-3-methyl-2-pyridyl]carbamate: LCMS(ESI): [M+H]$^+$ m/z: calcd 514.4; found 515.4; Rt=7.292 min. Chiral HPLC: Rt=7.76 min (Eluent: CO$_2$-MeOH, 60-40; column: IC; flow rate: 2 mL/min).

tert-butyl N-[5-[[2-[(2R,5S)-2-(4-tert-butylcyclohexyl)-5-methyl-1-piperidyl]-2-oxo-acetyl]amino]-3-methyl-2-pyridyl]carbamate: LCMS(ESI): [M+H]$^+$ m/z: calcd 514.4; found 515.2; Rt=7.368 min; Chiral HPLC: Rt=6.39 min (Eluent: CO$_2$-MeOH, 60-40; column: IC; flow rate: 2 mL/min).

Step 4: Synthesis of N-(6-amino-5-methyl-3-pyridyl)-2-[(2S,5R)-2-(4-tert-butylcyclohexyl)-5-methyl-1-piperidyl]-2-oxo-acetamide (Compound 260

To a stirred solution of tert-butyl N-[5-[[2-[(2S,5R)-2-(4-tert-butylcyclohexyl)-5-methyl-1-piperidyl]-2-oxo-acetyl]amino]-3-methyl-2-pyridyl]carbamate (26 mg, 50.52 μmol) in DCM (3 mL) was added 4.0 M HCl in dioxane (18.42 mg, 505.15 μmol, 23.02 μL). The resulting reaction mixture was stirred at 25° C. for 2 hours. After 2 hours, the reaction mixture was concentrated under reduced pressure and the crude product was purified by reverse phase HPLC (Eluent: 0-5 min, 65-100%, water-methanol (0.1% NH$_3$); flow rate: 30 mL/min; loading pump: 4 mL/min, methanol); column: YMC-Actus Triart C18 100*20 mm, 5 um) to obtain N-(6-amino-5-methyl-3-pyridyl)-2-[(2S,5R)-2-(4-tert-butylcyclohexyl)-5-methyl-1-piperidyl]-2-oxo-acetamide (Compound 260, 15 mg, 36.18 μmol, 71.62% yield) as a white solid.

¹H NMR (DMSO-d₆, 600 MHz): δ (ppm) 0.65-0.78 (m, 2H), 0.78-0.82 (m, 9H), 0.82-0.91 (m, 3H), 0.91-0.95 (m, 3H), 0.95-1.04 (m, 1H), 1.20-1.30 (m, 1H), 1.52-1.63 (m, 2H), 1.65-1.77 (m, 4H), 1.78-1.97 (m, 3H), 1.98-2.04 (m, 3H), 2.78-3.27 (m, 1H), 3.44-4.09 (m, 1H), 5.53-5.66 (m, 2H), 7.39-7.48 (m, 1H), 7.95-8.02 (m, 1H), 10.21-10.32 (m, 1H).

LCMS(ESI): [M+H]⁺ m/z: calcd 414.4; found 415.4; Rt=3.926 min.

Example 416. The Synthesis of N-(6-amino-5-methyl-3-pyridyl)-2-[(2R,5R)-2,5-dimethyl-1-piperidyl]-2-oxo-acetamide (Compound 158) and N-(6-amino-5-methyl-3-pyridyl)-2-[(2S,5R)-2,5-dimethyl-1-piperidyl]-2-oxo-acetamide (Compound 168

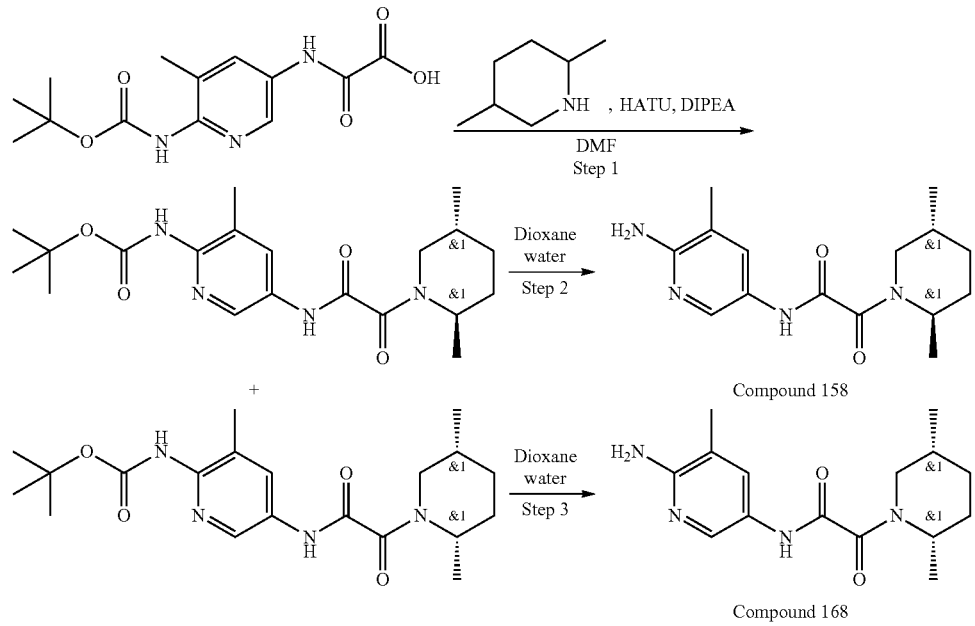

LCMS(ESI): [M+H]⁺ m/z: calcd 414.4; found 415.4; Rt=3.275 min.

Step 5: Synthesis of N-(6-amino-5-methyl-3-pyridyl)-2-[(2R,5S)-2-(4-tert-butylcyclohexyl)-5-methyl-1-piperidyl]-2-oxo-acetamide (Compound 290

To a stirred solution of tert-butyl N-[5-[[2-[(2R,5S)-2-(4-tert-butylcyclohexyl)-5-methyl-1-piperidyl]-2-oxo-acetyl]amino]-3-methyl-2-pyridyl]carbamate (34 mg, 66.06 μmol) in DCM (3 mL) was added 4.0 M HCl in dioxane (24.09 mg, 660.58 μmol, 30.11 μL). The resulting reaction mixture was stirred at 25° C. for 2 hours. After 2 hours, the reaction mixture was concentrated under reduced pressure and the crude product was purified by reverse phase HPLC (Eluent: 0-5 min, 65-100%, water-methanol (0.1% NH₃); flow rate: 30 mL/min; loading pump: 4 mL/min, methanol; column: YMC-Actus Triart C18 100*20 mm, 5 um) to obtain N-(6-amino-5-methyl-3-pyridyl)-2-[(2R,5S)-2-(4-tert-butylcyclohexyl)-5-methyl-1-piperidyl]-2-oxo-acetamide (Compound 290, 15 mg, 36.18 μmol, 54.77% yield) as a white solid.

¹H NMR (DMSO-d₆, 600 MHz): δ (ppm) 0.65-0.78 (m, 2H), 0.78-0.82 (m, 9H), 0.82-0.91 (m, 3H), 0.91-0.95 (m, 3H), 0.95-1.04 (m, 1H), 1.20-1.30 (m, 1H), 1.52-1.63 (m, 2H), 1.65-1.77 (m, 4H), 1.78-1.97 (m, 3H), 1.98-2.04 (m, 3H), 2.78-3.27 (m, 1H), 3.44-4.09 (m, 1H), 5.53-5.66 (m, 2H), 7.39-7.48 (m, 1H), 7.95-8.02 (m, 1H), 10.21-10.32 (m, 1H).

Step 1: Synthesis of tert-butyl N-[5-[[2-[(2R,5R)-2,5-dimethyl-1-piperidyl]-2-oxo-acetyl]amino]-3-methyl-2-pyridyl]carbamate and Tert-butyl N-[5-[[2-[(2S,5R)-2,5-dimethyl-1-piperidyl]-2-oxo-acetyl]amino]-3-methyl-2-pyridyl]carbamate To a stirred solution of 2,5-dimethylpiperidine (0.08 g, 706.71 μmol) and 2-[[6-(tert-butoxycarbonylamino)-5-methyl-3-pyridyl]amino]-2-oxo-acetic acid (208.69 mg, 706.71 μmol) in DMF (10 mL) was added DIPEA (228.34 mg, 1.77 mmol, 307.74 μL). The resulting mixture was stirred for 5 minutes. After 5 minutes, a solution of HATU (282.15 mg, 742.05 μmol) in DMF (2 mL) was added. The reaction mixture was stirred for overnight at room temperature. Upon completion, the resulting suspension was concentrated under reduced pressure. The obtained crude product was subjected to HPLC purification (Column: Waters SunFire C18 19*100 mm, 5 um; Eluent: 40-60% CH₃CN) to afford tert-butyl N-[5-[[2-[(2R,5R)-2,5-dimethyl-1-piperidyl]-2-oxo-acetyl]amino]-3-methyl-2-pyridyl]carbamate (53.9 mg, 138.04 μmol, 19.53% yield) and tert-butyl N-[5-[[2-[(2S,5R)-2,5-dimethyl-1-piperidyl]-2-oxo-acetyl]amino]-3-methyl-2-pyridyl]carbamate (16.6 mg, 42.51 μmol, 6.02% yield) as light-yellow solids.

tert-butyl-N-[5-[[2-[(2R,5R)-2,5-dimethyl-1-piperidyl]-2-oxo-acetyl]amino]-3-methyl-2-pyridyl]carbamate: LCMS (ESI): [M+Boc]⁺ m/z: calcd 390.3; found 391.2; Rt=3.340 min.

tert-butyl-N-[5-[[2-[(2S,5R)-2,5-dimethyl-1-piperidyl]-2-oxo-acetyl]amino]-3-methyl-2-pyridyl]carbamate: LCMS (ESI): [M+Boc]⁺ m/z: calcd 390.3; found 391.2; Rt=3.389 min.

Step 2: Synthesis of N-(6-amino-5-methyl-3-pyridyl)-2-[(2R,5R)-2,5-dimethyl-1-piperidyl]-2-oxo-acetamide (Compound 158 tert-butyl N-[5-[[2-[(2R,5R)-2,5-dimethyl-1-piperidyl]-2-oxo-acetyl]amino]-3-methyl-2-pyridyl]carbamate (53.9 mg, 138.04 μmol) was dissolved in water (5 mL) and dioxane (5 mL). The reaction mixture was stirred for 17 hours at 100° C. Upon completion, the resulting suspension was concentrated under reduced pressure. The obtained crude product was subjected to HPLC purification to afford N-(6-amino-5-methyl-3-pyridyl)-2-[(2R,5R)-2,5-dimethyl-1-piperidyl]-2-oxo-acetamide (Compound 158, 18.5 mg, 63.71 μmol, 46.16% yield) as light-yellow solid.

$^1$H NMR (CDCl$_3$, 400 MHz): δ (ppm) 1.01 (m, 3H), 1.23 (m, 4H), 1.35 (m, 2H), 1.95 (m, 4H), 2.14 (s, 3H), 3.35 (m, 1H), 4.81 (m, 3H), 7.73 (m, 1H), 8.05 (m, 1H), 9.01 (m, 1H).

LCMS(ESI): [M+H]⁺ m/z: calcd 290.2; found 291.4; Rt=2.008 min.

Step 3: Synthesis of N-(6-amino-5-methyl-3-pyridyl)-2-[(2S,5R)-2,5-dimethyl-1-piperidyl]-2-oxo-acetamide (Compound 168 tert-butyl N-[5-[[2-[(2S,5R)-2,5-dimethyl-1-piperidyl]-2-oxo-acetyl]amino]-3-methyl-2-pyridyl]carbamate (16 mg, 40.98 μmol) was dissolved in water (5 mL) and dioxane (2 mL). The reaction mixture was stirred for 17 hours at 100° C. Upon completion, the resulting suspension was concentrated under reduced pressure. The obtained crude product was subjected to HPLC purification (Eluent: 2-10 min, 50-70% water-CH$_3$CN (formic acid as an additive); loading pump: 4 mL/min, CH$_3$CN; Column: Sunfire C18 100×20 mm, 5 um) and freeze dried to afford N-(6-amino-5-methyl-3-pyridyl)-2-[(2S,5R)-2,5-dimethyl-1-piperidyl]-2-oxo-acetamide (Compound 168, 3.5 mg, 12.05 μmol, 29.42% yield) as light-yellow solid.

LCMS(ESI): [M+H]⁺ m/z: calcd 290.2; found 291.2; Rt=2.240 min.

Example 417. The Synthesis of N-(6-amino-5-methyl-3-pyridyl)-2-[(2S,4R)-4-Cyano-2-phenyl-1-piperidyl]-2-oxo-acetamide (Compound 380) and N-(6-amino-5-methyl-3-pyridyl)-2-[(2R,4S)-4-Cyano-2-phenyl-1-piperidyl]-2-oxo-acetamide (Compound 399

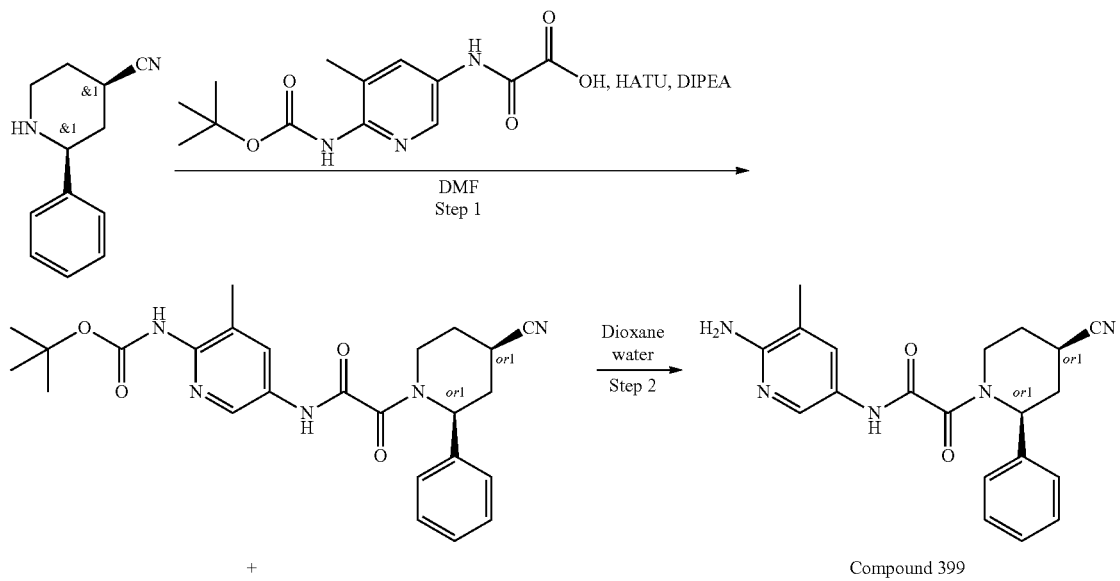

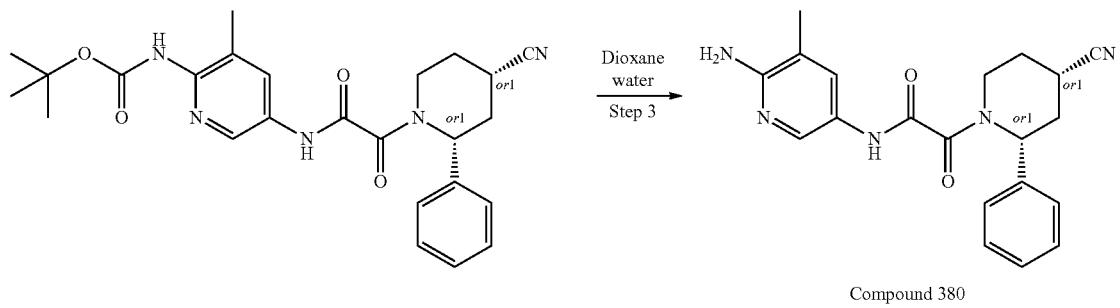

Compound 380

Step 1: Synthesis of tert-butyl N-[5-[[2-[(2S,4R)-4-cyano-2-phenyl-1-piperidyl]-2-oxo-acetyl]amino]-3-methyl-2-pyridyl]carbamate and Tert-butyl N-[5-[[2-[(2R,4S)-4-cyano-2-phenyl-1-piperidyl]-2-oxo-acetyl]amino]-3-methyl-2-pyridyl]carbamate To a stirred solution of 2-[[6-(tert-butoxycarbonylamino)-5-methyl-3-pyridyl]amino]-2-oxo-acetic acid (0.3 g, 1.02 mmol) and (2R,4S)-2-phenylpiperidine-4-carbonitrile (226.27 mg, 1.02 mmol, HCl salt) in DMF (10 mL) was added DIPEA (525.22 mg, 4.06 mmol, 707.84 µL). The resulting reaction mixture was stirred for 5 minutes. After 5 minutes, HATU (424.92 mg, 1.12 mmol) was added. The resulting reaction mixture was then stirred for overnight at room temperature. Upon completion, the resulting suspension was concentrated under reduced pressure and the crude product was purified by reverse phase HPLC to afford rac-tert-butyl N-[5-[[2-[(2S,4R)-4-cyano-2-phenyl-1-piperidyl]-2-oxo-acetyl]amino]-3-methyl-2-pyridyl]carbamate (0.11 g, 237.31 µmol, 23.36% yield) as a light yellow solid. The obtained pure product was subjected to chiral HPLC purification (Column: IB (250×20, 5 um); Eluent: Hexane-MeOH-IPA, 70-15-15; flow rate: 12 mL/min) to get tert-butyl N-[5-[[2-[(2S,4R)-4-cyano-2-phenyl-1-piperidyl]-2-oxo-acetyl]amino]-3-methyl-2-pyridyl]carbamate (36.1 mg) and tert-butyl N-[5-[[2-[(2R,4S)-4-cyano-2-phenyl-1-piperidyl]-2-oxo-acetyl]amino]-3-methyl-2-pyridyl]carbamate (36.8 mg) as light-yellow solids.

tert-butyl N-[5-[[2-[(2S,4R)-4-cyano-2-phenyl-1-piperidyl]-2-oxo-acetyl]amino]-3-methyl-2-pyridyl]carbamate: LCMS(ESI): [M+Boc]$^+$ m/z: calcd 463.2; found 464.4; Rt=3.389 min.

Chiral HPLC: Rt=36.62 min (Column: IB; Eluent: Hexane-MeOH-IPA, 70-15-15; flow rate: 0.6 mL/min).

tert-butyl N-[5-[[2-[(2R,4S)-4-cyano-2-phenyl-1-piperidyl]-2-oxo-acetyl]amino]-3-methyl-2-pyridyl]carbamate: LCMS(ESI): [M+Boc]$^+$ m/z: calcd 463.2; found 464.4; Rt=3.390 min.

Chiral HPLC: Rt=23.36 min (Column: IB; Eluent: Hexane-MeOH-IPA, 70-15-15; flow rate: 0.6 mL/min).

Step 2: Synthesis of N-(6-amino-5-methyl-3-pyridyl)-2-[(2R,4S)-4-cyano-2-phenyl-1-piperidyl]-2-oxo-acetamide (Compound 399 tert-butyl N-[5-[[2-[(2R,4S)-4-cyano-2-phenyl-1-piperidyl]-2-oxo-acetyl]amino]-3-methyl-2-pyridyl]carbamate (36.8 mg, 79.39 µmol) was dissolved in dioxane (2 mL) and water (5 mL). The resulting reaction mixture was stirred for 15 hours at 100° C. Upon completion, the resulting suspension was concentrated under reduced pressure. The obtained crude product was purified by HPLC to afford pure N-(6-amino-5-methyl-3-pyridyl)-2-[(2R,4S)-4-cyano-2-phenyl-1-piperidyl]-2-oxo-acetamide (Compound 399, 16.9 mg, 46.50 µmol, 58.58% yield) as a white solid.

$^1$H NMR (DMSO-d$_6$, 600 MHz): δ (ppm) 1.82-1.87 (m, 1H), 1.93-1.97 (m, 1H), 1.97-2.04 (m, 3H), 2.16-2.23 (m, 1H), 2.60-3.06 (m, 1H), 3.18-3.24 (m, 1H), 3.36-3.47 (m, 1H), 3.79-4.50 (m, 1H), 5.29-5.53 (m, 1H), 5.54-5.69 (m, 2H), 7.21-7.28 (m, 1H), 7.30-7.36 (m, 4H), 7.36-7.54 (m, 1H), 7.84-8.11 (m, 1H), 10.34-10.62 (m, 1H).

LCMS(ESI): [M+H]$^+$ m/z: calcd 363.2; found 364.2; Rt=2.235 min.

Step 3: Synthesis of N-(6-amino-5-methyl-3-pyridyl)-2-[(2S,4R)-4-cyano-2-phenyl-1-piperidyl]-2-oxo-acetamide (Compound 380 tert-butyl N-[5-[[2-[(2S,4R)-4-cyano-2-phenyl-1-piperidyl]-2-oxo-acetyl]amino]-3-methyl-2-pyridyl]carbamate (36.1 mg, 77.88 µmol) was dissolved in water (5 mL) and dioxane (2 mL). The reaction mixture was then stirred for 15 hours at 100° C. Upon completion, the resulting suspension was concentrated under reduced pressure. The obtained crude product was purified by HPLC to afford pure N-(6-amino-5-methyl-3-pyridyl)-2-[(2S,4R)-4-cyano-2-phenyl-1-piperidyl]-2-oxo-acetamide (Compound 380, 18.8 mg, 51.73 µmol, 66.42% yield) as a white solid.

$^1$H NMR (DMSO-d$_6$, 600 MHz): δ (ppm) 1.82-1.87 (m, 1H), 1.95-2.03 (m, 4H), 2.15-2.25 (m, 1H), 2.64-3.05 (m, 1H), 3.18-3.24 (m, 1H), 3.35-3.45 (m, 1H), 3.81-4.44 (m, 1H), 5.31-5.54 (m, 1H), 5.55-5.67 (m, 2H), 7.18-7.27 (m, 1H), 7.31-7.53 (m, 5H), 7.83-8.10 (m, 1H), 10.32-10.63 (m, 1H).

LCMS(ESI): [M+H]$^+$ m/z: calcd 363.2; found 364.2; Rt=2.262 min.

Example 418. The Synthesis of N-(6-amino-5-methyl-3-pyridyl)-2-[(2R,5S)-2-[(1S,3R)-3-hydroxycyclohexyl]-5-methyl-1-piperidyl]-2-oxo-acetamide (Compound 566), N-(6-amino-5-methyl-3-pyridyl)-2-[(2S,5R)-2-[(1R,3S)-3-hydroxycyclohexyl]-5-methyl-1-piperidyl]-2-oxo-acetamide (Compound 567), N-(6-amino-5-methyl-3-pyridyl)-2-[(2R,5S)-2-[(1R,3R)-3-hydroxycyclohexyl]-5-methyl-1-piperidyl]-2-oxo-acetamide (Compound 568) and N-(6-amino-5-methyl-3-pyridyl)-2-[(2S,5R)-2-[(1S,3S)-3-hydroxycyclohexyl]-5-methyl-1-piperidyl]-2-oxo-acetamide (Compound 559

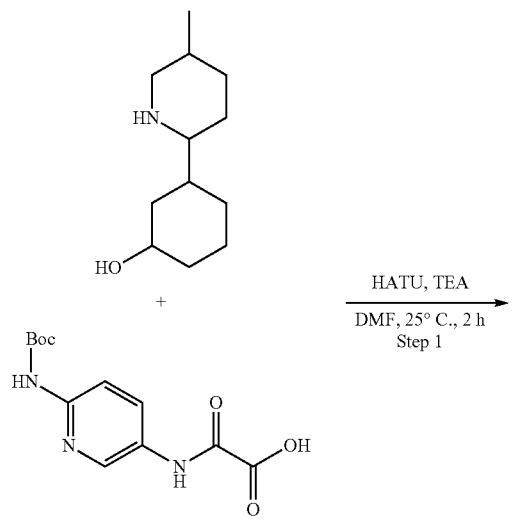

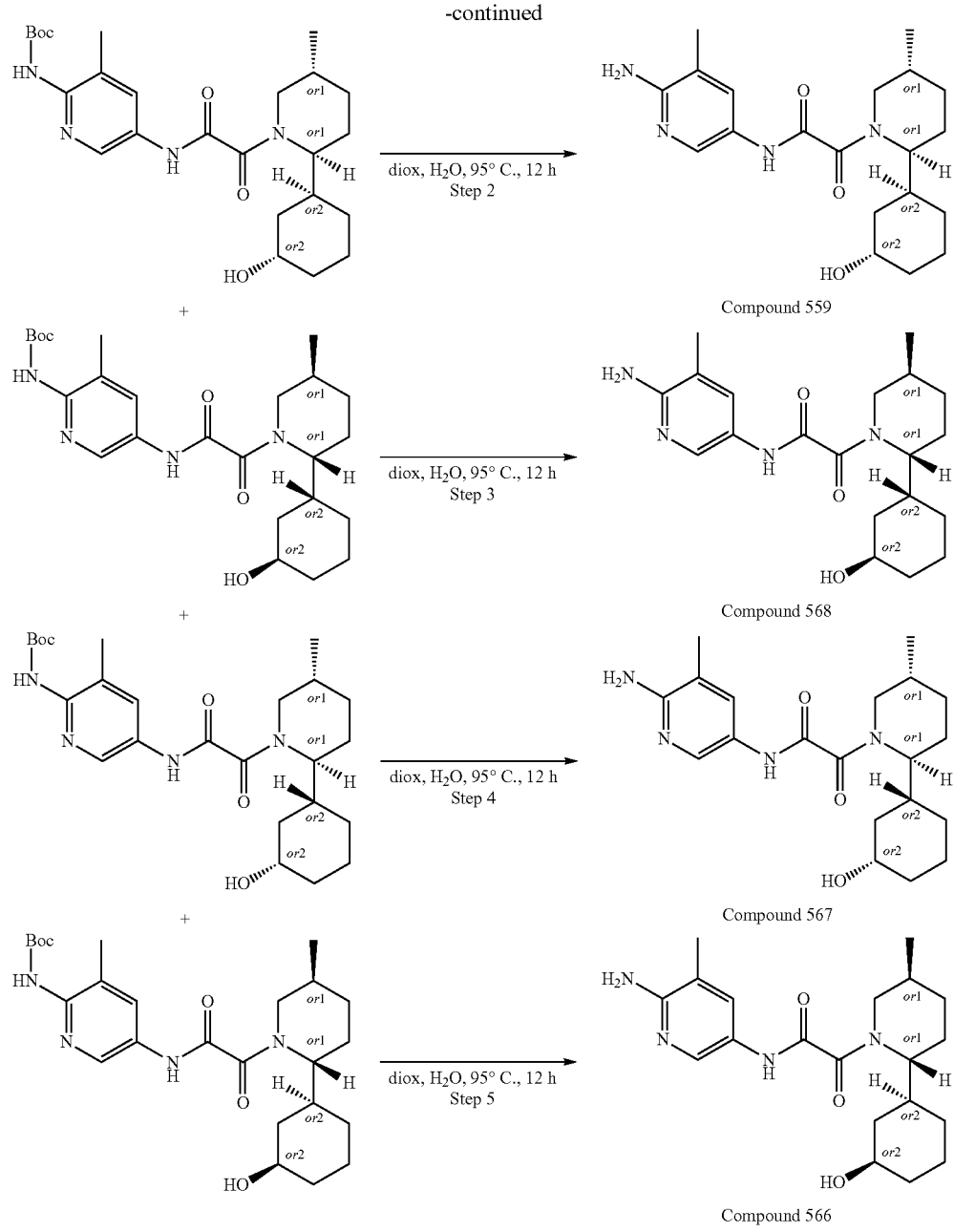

Compound 559

Compound 568

Compound 567

Compound 566

Step 1: The Synthesis of tert-butyl N-[5-[[2-[(2S, 5R)-2-[(1S,3S)-3-hydroxycyclohexyl]-5-methyl-1-piperidyl]-2-oxo-acetyl]amino]-3-methyl-2-pyridyl] carbamate, tert-butyl N-[5-[[2-[(2R,5S)-2-[(1R,3R)-3-hydroxycyclohexyl]-5-methyl-1-piperidyl]-2-oxo-acetyl]amino]-3-methyl-2-pyridyl]carbamate, Tert-butyl N-[5-[[2-[(2S,5R)-2-[(1R,3S)-3-hydroxycyclohexyl]-5-methyl-1-piperidyl]-2-oxo-acetyl]amino]-3-methyl-2-pyridyl]carbamate and Tert-butyl N-[5-[[2-[(2R,5S)-2-[(1S,3R)-3-hydroxy-cyclohexyl]-5-methyl-1-piperidyl]-2-oxo-acetyl] amino]-3-methyl-2-pyridyl]carbamate A mixture of 3-(5-methyl-2-piperidyl)cyclohexanol (550 mg, 2.79 mmol), 2-[[6-(tert-butoxycarbonylamino)-5-methyl-3-pyridyl]amino]-2-oxo-acetic acid (823.09 mg, 2.79 mmol) and triethyl amine (2.82 g, 27.87 mmol, 3.89 mL) in DMF (20 mL) was stirred at 25° C. for 0.25 hr, then HATU (1.06 g, 2.79 mmol) was added in small portions over 0.5 hr. The reaction mixture was stirred at 25° C. for 2 hr, then concentrated in vacuo to 5 ml and submitted to reverse phase HPLC (column: SunFire C18 100×19 mm 5 um, mobile phase: 50-50-80% 0-1-6 min water-methanol, flow rate: 30 ml/min), which afforded two fractions of the product: 259 mg (1st fraction) and 337 mg (2nd fraction) as colorless gums. 1st fraction after HPLC (259 mg) was then submitted to preparative chiral HPLC (column:IC-II (250*20, 5 mkm), mobile phase: Hexane-IPA-MeOH, 70-15-15, flow rate: 12 ml/min) to afford tert-butyl N-[5-[[2-[(2S,5R)-2-[(1S,3S)-3-hydroxycyclohexyl]-5-methyl-1-piperidyl]-2-oxo-acetyl]amino]-3-methyl-2-pyridyl]car-bamate (89 mg, 187.53 μmol, 6.73% yield) (R.T.=30.039 min.) and tert-butyl N-[5-[[2-[(2R,5S)-2-[(1R,3R)-3-hydroxycyclohexyl]-5-methyl-1-piperidyl]-2-oxo-acetyl]amino]-3-methyl-2-pyridyl]carbamate (70 mg, 147.50 µmol, 5.29% yield) (R.T.=34.388 min.) as colorless gums, contained traces of solvents. 2nd fraction after HPLC (337 mg) was submitted to preparative chiral HPLC (column:IC-II (250*20, 5 mkm), mobile phase: Hexane-IPA-MeOH, 70-15-15, flow rate: 12 ml/min) to afford tert-butyl N-[5-[[2-[(2S,5R)-2-[(1R,3S)-3-hydroxycyclohexyl]-5-methyl-1-piperidyl]-2-oxo-acetyl]amino]-3-methyl-2-pyridyl]carbamate (119 mg, 250.74 µmol, 9.00% yield) (R.T.=38.496 min.) and tert-butyl N-[5-[[2-[(2R,5S)-2-[(1S,3R)-3-hydroxycyclohexyl]-5-methyl-1-piperidyl]-2-oxo-acetyl]amino]-3-methyl-2-pyridyl]carbamate (83 mg, 174.89 µmol, 6.27% yield) (R.T.=47.540 min.) as colorless gums, contained traces of solvents. All the products were used directly in the next steps.

1st Fraction: RT (IC, Hexane-IPA-MeOH, 50-25-25, 0.6 mL/min)=15.559 min.

LCMS(ESI): [M+H]+ m/z: calcd 474.2; found 475.2; Rt=4.558 min.

2nd Fraction: RT (IC, Hexane-IPA-MeOH, 50-25-25, 0.6 mL/min)=17.928 min.

LCMS(ESI): [M+H]+ m/z: calcd 474.2; found 475.2; Rt=4.558 min.

3rd Fraction: RT (IC, Hexane-IPA-MeOH, 50-25-25, 0.6 mL/min)=20.008 min.

LCMS(ESI): [M+H]+ m/z: calcd 474.2; found 475.2; Rt=4.896 min.

4th Fraction: RT (IC, Hexane-IPA-MeOH, 50-25-25, 0.6 mL/min)=23.341 min.

LCMS(ESI): [M+H]+ m/z: calcd 474.2; found 475.2; Rt=4.894 min.

Step 2: The Synthesis of N-(6-amino-5-methyl-3-pyridyl)-2-[(2S,5R)-2-[(1S,3S)-3-hydroxycyclohexyl]-5-methyl-1-piperidyl]-2-oxo-acetamide (Compound 559 tert-butyl N-[5-[[2-[(2S,5R)-2-[(1S,3S)-3-hydroxycyclohexyl]-5-methyl-1-piperidyl]-2-oxo-acetyl]amino]-3-methyl-2-pyridyl]carbamate (89 mg, 187.53 µmol) was dissolved in a mixture of 1,4-dioxane (2 mL) and water (2.5 mL). The resulting solution was stirred at 95° C. for 12 hr, then cooled down and submitted to reverse phase HPLC (column: column: YMC-Actus Triart C18 100*20 mml.D. S-5 um, mobile phase: 30-45% 1-6 min water-methanol (NH₃0.1%), flow rate: 30 ml/min) to afford Compound 559 N-(6-amino-5-methyl-3-pyridyl)-2-[(2S,5R)-2-[(1S,3S)-3-hydroxycyclohexyl]-5-methyl-1-piperidyl]-2-oxo-acetamide (51.7 mg, 138.06 µmol, 73.62% yield) as white solid.

¹H NMR (600 MHz, DMSO-d₆) δ 0.57-0.67 (m, 1H), 0.73-0.89 (m, 1H), 0.91-0.95 (m, 3H), 0.95-1.05 (m, 1H), 1.11-1.19 (m, 1H), 1.21-1.30 (m, 1H), 1.42-1.51 (m, 1H), 1.52-1.62 (m, 2H), 1.62-1.68 (m, 1H), 1.74-1.96 (m, 6H), 1.99-2.05 (m, 3H), 2.78-3.24 (m, 1H), 3.37-3.52 (m, 1H), 3.93-4.14 (m, 1H), 4.44-4.55 (m, 1H), 5.54-5.62 (m, 2H), 7.39-7.47 (m, 1H), 7.94-8.03 (m, 1H), 10.23-10.32 (m, 1H).

LCMS(ESI): [M+H]+ m/z: calcd 374.2; found 375.2; Rt=1.588 min.

Step 3: The Synthesis of N-(6-amino-5-methyl-3-pyridyl)-2-[(2R,5S)-2-[(1R,3R)-3-hydroxycyclohexyl]-5-methyl-1-piperidyl]-2-oxo-acetamide (Compound 568 tert-butyl N-[5-[[2-[(2R,5S)-2-[(1R,3R)-3-hydroxycyclohexyl]-5-methyl-1-piperidyl]-2-oxo-acetyl]amino]-3-methyl-2-pyridyl]carbamate (70 mg, 147.50 µmol) was dissolved in a mixture of 1,4-dioxane (2 mL) and water (2.5 mL). The resulting solution was stirred at 95° C. for 12 hr, then cooled down and submitted to reverse phase HPLC (column: column: YMC-Actus Triart C18 100*20 mml.D. S-5 um, mobile phase: 35-60% 1-6 min water-methanol (NH₃0.1%), flow rate: 30 ml/min) to afford Compound 568 N-(6-amino-5-methyl-3-pyridyl)-2-[(2R,5S)-2-[(1R,3R)-3-hydroxycyclohexyl]-5-methyl-1-piperidyl]-2-oxo-acetamide (33 mg, 88.12 µmol, 59.75% yield) as white solid.

¹H NMR (600 MHz, DMSO-d₆) δ 0.54-0.78 (m, 2H), 0.89-0.94 (m, 3H), 0.95-1.04 (m, 1H), 1.11-1.20 (m, 1H), 1.21-1.30 (m, 1H), 1.39-1.51 (m, 1H), 1.51-1.63 (m, 2H), 1.63-1.70 (m, 1H), 1.71-1.99 (m, 6H), 1.99-2.05 (m, 3H), 2.78-3.25 (m, 1H), 3.37-3.51 (m, 1H), 3.94-4.14 (m, 1H), 4.45-4.56 (m, 1H), 5.55-5.61 (m, 2H), 7.40-7.49 (m, 1H), 7.97 (s, 1H), 10.17-10.35 (m, 1H).

LCMS(ESI): [M+H]+ m/z: calcd 374.2; found 375.2; Rt=1.717 min.

Step 4: The Synthesis of N-(6-amino-5-methyl-3-pyridyl)-2-[(2S,5R)-2-[(1R,3S)-3-hydroxycyclohexyl]-5-methyl-1-piperidyl]-2-oxo-acetamide (Compound 567 tert-butyl N-[5-[[2-[(2S,5R)-2-[(1R,3S)-3-hydroxycyclohexyl]-5-methyl-1-piperidyl]-2-oxo-acetyl]amino]-3-methyl-2-pyridyl]carbamate (119 mg, 250.74 µmol) was dissolved in a mixture of 1,4-dioxane (2 mL) and water (2.5 mL. The resulting solution was stirred at 95° C. for 12 hr, then cooled down and submitted to reverse phase HPLC (column: column: YMC-Actus Triart C18 100*20 mml.D. S-5 um, mobile phase: 40-60% 1-6 min water-methanol (NH₃ 0.1%), flow rate: 30 ml/min) to afford Compound 567 N-(6-amino-5-methyl-3-pyridyl)-2-[(2S,5R)-2-[(1R,3S)-3-hydroxycyclohexyl]-5-methyl-1-piperidyl]-2-oxo-acetamide (59 mg, 157.55 µmol, 62.83% yield) as white solid.

¹H NMR (600 MHz, DMSO-d₆) δ 0.54-0.78 (m, 2H), 0.87-1.04 (m, 4H), 1.15-1.29 (m, 2H), 1.54-1.62 (m, 2H), 1.62-1.72 (m, 2H), 1.72-1.83 (m, 3H), 1.84-1.98 (m, 2H), 1.99-2.04 (m, 3H), 2.79-3.28 (m, 1H), 3.36-3.57 (m, 1H), 3.92-4.16 (m, 1H), 4.38-4.50 (m, 1H), 5.55-5.63 (m, 2H), 7.38-7.51 (m, 1H), 7.92-8.02 (m, 1H), 10.20-10.38 (m, 1H).

LCMS(ESI): [M+H]+ m/z: calcd 374.2; found 375.2; Rt=1.929 min.

Step 5: The Synthesis of N-(6-amino-5-methyl-3-pyridyl)-2-[(2R,5S)-2-[(1S,3R)-3-hydroxycyclohexyl]-5-methyl-1-piperidyl]-2-oxo-acetamide (Compound 566 tert-butyl N-[5-[[2-[(2R,5S)-2-[(1S,3R)-3-hydroxycyclohexyl]-5-methyl-1-piperidyl]-2-oxo-acetyl]amino]-3-methyl-2-pyridyl]carbamate (83 mg, 174.89 µmol) was dissolved in a mixture of 1,4-dioxane (2 mL) and water (2.5 mL). The resulting solution was stirred at 95° C. for 12 hr, then cooled down and submitted to reverse phase HPLC (column: column: YMC-Actus Triart C18 100*20 mml.D. S-5 um, mobile phase: 40-60% 1-6 min water-methanol (NH₃0.1%), flow rate: 30 ml/min) to afford Compound 566 N-(6-amino-5-methyl-3-pyridyl)-2-[(2R,5S)-2-[(1S,3R)-3-hydroxycyclohexyl]-5-methyl-1-piperidyl]-2-oxo-acetamide (52 mg, 138.86 µmol, 79.40% yield) as white solid.

¹H NMR (600 MHz, DMSO-d₆) δ 0.52-0.79 (m, 2H), 0.90-0.95 (m, 3H), 0.95-1.03 (m, 1H), 1.14-1.29 (m, 2H), 1.54-1.62 (m, 2H), 1.62-1.71 (m, 2H), 1.71-1.83 (m, 3H), 1.83-1.98 (m, 2H), 1.99-2.05 (m, 3H), 2.79-3.27 (m, 1H), 3.36-3.57 (m, 1H), 3.94-4.14 (m, 1H), 4.39-4.49 (m, 1H), 5.54-5.62 (m, 2H), 7.42-7.50 (m, 1H), 7.96-8.02 (m, 1H), 10.16-10.36 (m, 1H).

LCMS(ESI): [M+H]+ m/z: calcd 374.2; found 375.2; Rt=1.940 min.

Example 419. The Synthesis of N-(6-amino-5-methyl-3-pyridyl)-2-[(2R,5S)-2-(2-methoxy-4-pyridyl)-5-methyl-1-piperidyl]-2-oxo-acetamide (Compound 545) and N-(6-amino-5-methyl-3-pyridyl)-2-[(2S,5R)-2-(2-methoxy-4-pyridyl)-5-methyl-1-piperidyl]-2-oxo-acetamide (Compound 538
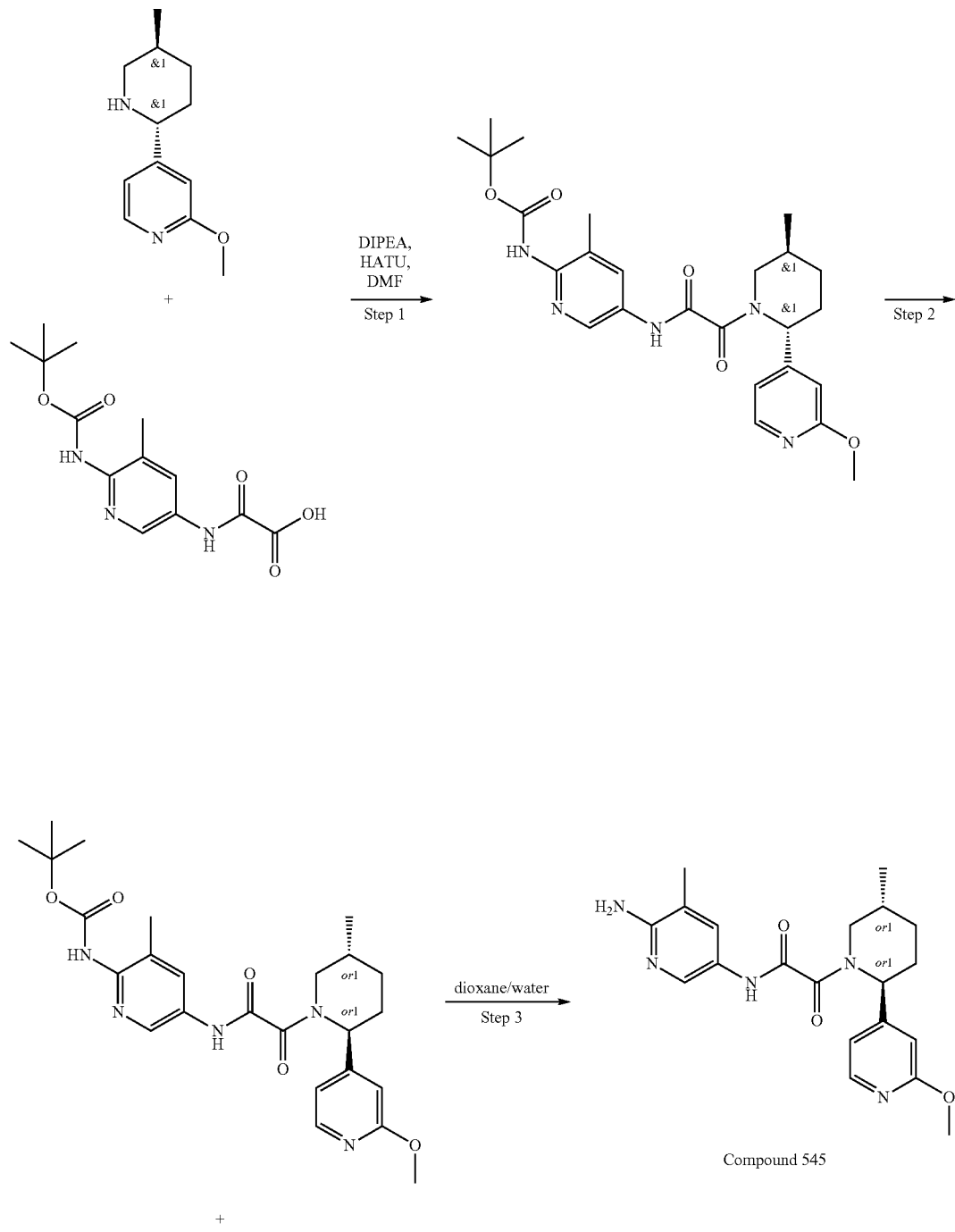

-continued

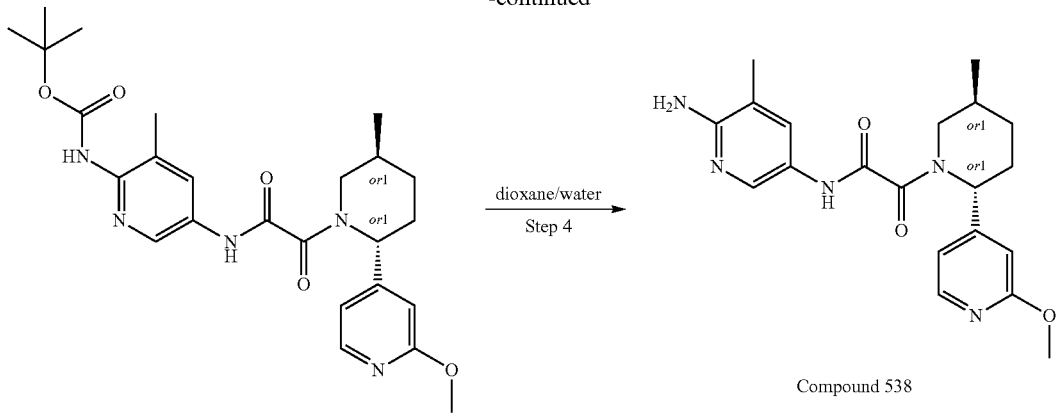

Compound 538

Step 1: Synthesis of tert-butyl N-[5-[[2-[2-(2-methoxy-4-pyridyl)-5-methyl-1-piperidyl]-2-oxo-acetyl]amino]-3-methyl-2-pyridyl]carbamate DIPEA (525.22 mg, 4.06 mmol, 707.84 µL) was added to the solution of respective 2-[[6-(tert-butoxycarbonylamino)-5-methyl-3-pyridyl]amino]-2-oxo-acetic acid (0.4 g, 1.35 mmol) and 2-methoxy-4-(5-methyl-2-piperidyl)pyridine (279.43 mg, 1.35 mmol) in DMF (10 mL). The resulting mixture was stirred for 5 min followed by the addition of the solution of HATU (566.56 mg, 1.49 mmol). Then, the reaction mixture was stirred overnight at room temperature. After the completion of the reaction, monitored by LCMS, the resulting suspension was concentrated under reduced pressure. The obtained solid was subjected to HPLC to afford tert-butyl N-[5-[[2-[2-(2-methoxy-4-pyridyl)-5-methyl-1-piperidyl]-2-oxo-acetyl]amino]-3-methyl-2-pyridyl]carbamate (0.34 g, 703.12 µmol, 51.91% yield).

LCMS(ESI): [M+H]$^+$ m/z: calcd 483.3; found 484.4; Rt=3.696 min.

Step 2: Synthesis of tert-butyl N-[5-[[2-[(2S,5R)-2-(2-methoxy-4-pyridyl)-5-methyl-1-piperidyl]-2-oxo-acetyl]amino]-3-methyl-2-pyridyl]carbamate (P1) and Tert-butyl N-[5-[[2-[(2R,5S)-2-(2-methoxy-4-pyridyl)-5-methyl-1-piperidyl]-2-oxo-acetyl]amino]-3-methyl-2-pyridyl]carbamate (P2 tert-butyl N-[5-[[2-[2-(2-methoxy-4-pyridyl)-5-methyl-1-piperidyl]-2-oxo-acetyl]amino]-3-methyl-2-pyridyl]carbamate (330.0 mg, 682.44 µmol) was chirally separated using IC (100*20, 5 mkm) Chiralpak column, IPA-MeOH, 50-50 as a mobile phase, Flow 10 mL/min) affording P1—tert-butyl N-[5-[[2-[(2S,5R)-2-(2-methoxy-4-pyridyl)-5-methyl-1-piperidyl]-2-oxo-acetyl]amino]-3-methyl-2-pyridyl]carbamate (79.26 mg, 24.02% yield) and P2 tert-butyl N-[5-[[2-[(2R,5S)-2-(2-methoxy-4-pyridyl)-5-methyl-1-piperidyl]-2-oxo-acetyl]amino]-3-methyl-2-pyridyl]carbamate (119.89 mg, 36.33% yield).

P1: LCMS(ESI): [M+H]$^+$ m/z: calcd 483.6; found 484.6; Rt=5.139 min.

RT (IC, IPA-MeOH, 50-50, 0.6 mL/min)=56.1162 min.

P2: LCMS(ESI): [M+H]$^+$ m/z: calcd 483.6; found 484.6; Rt=5.140 min.

RT (IC, IPA-MeOH, 50-50, 0.6 mL/min)=14.6942 min.

Step 3: Synthesis of N-(6-amino-5-methyl-3-pyridyl)-2-[(2R,5S)-2-(2-methoxy-4-pyridyl)-5-methyl-1-piperidyl]-2-oxo-acetamide (Compound 545 tert-butyl N-[5-[[2-[(2R,5S)-2-(2-methoxy-4-pyridyl)-5-methyl-1-piperidyl]-2-oxo-acetyl]amino]-3-methyl-2-pyridyl]carbamate (119.89 mg, 247.93 µmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC to afford pure N-(6-amino-5-methyl-3-pyridyl)-2-[(2R,5S)-2-(2-methoxy-4-pyridyl)-5-methyl-1-piperidyl]-2-oxo-acetamide (67.7 mg, 176.56 µmol, 71.21% yield).

$^1$H NMR (600 MHz, DMSO-d$_6$) δ 0.89-1.05 (m, 3H), 1.25-1.36 (m, 1H), 1.44-1.65 (m, 1H), 1.79-1.91 (m, 1H), 1.97-2.02 (m, 3H), 2.10-2.20 (m, 1H), 2.49-2.49 (m, 1H), 2.68-3.23 (m, 1H), 3.40-4.06 (m, 4H), 5.06-5.51 (m, 1H), 5.54-5.70 (m, 2H), 6.63-6.76 (m, 1H), 6.88-6.99 (m, 1H), 7.39-7.53 (m, 1H), 7.92-8.04 (m, 1H), 8.11-8.21 (m, 1H), 10.44-10.61 (m, 1H).

LCMS(ESI): [M+H]$^+$ m/z: calcd 383.2; found 384.2; Rt=1.929 min.

Step 4: Synthesis of N-(6-amino-5-methyl-3-pyridyl)-2-[(2S,5R)-2-(2-methoxy-4-pyridyl)-5-methyl-1-piperidyl]-2-oxo-acetamide (Compound 538 tert-butyl N-[5-[[2-[(2S,5R)-2-(2-methoxy-4-pyridyl)-5-methyl-1-piperidyl]-2-oxo-acetyl]amino]-3-methyl-2-pyridyl]carbamate (79.26 mg, 163.91 µmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC to afford pure N-(6-amino-5-methyl-3-pyridyl)-2-[(2S,5R)-2-(2-methoxy-4-pyridyl)-5-methyl-1-piperidyl]-2-oxo-acetamide (43.7 mg, 113.97 µmol, 69.53% yield).

$^1$H NMR (600 MHz, DMSO-d$_6$) δ 0.88-1.03 (m, 3H), 1.25-1.38 (m, 1H), 1.49-1.62 (m, 1H), 1.78-1.91 (m, 1H), 1.91-2.13 (m, 4H), 2.13-2.22 (m, 1H), 2.67-3.23 (m, 1H), 3.40-4.10 (m, 4H), 5.02-5.52 (m, 1H), 5.54-5.73 (m, 2H), 6.63-6.74 (m, 1H), 6.86-6.97 (m, 1H), 7.39-7.51 (m, 1H), 7.93-8.04 (m, 1H), 8.09-8.20 (m, 1H), 10.46-10.57 (m, 1H).

LCMS(ESI): [M+H]+ m/z: calcd 383.2; found 384.2; Rt=1.933 m

Example 420. The Synthesis of N-(6-amino-5-methyl-3-pyridyl)-2-[(2S,5S)-4,4-difluoro-2-(4-fluorophenyl)-5-methyl-1-piperidyl]-2-oxo-acetamide (Compound 777) and N-(6-amino-5-methyl-3-pyridyl)-2-[(2R,5R)-4,4-difluoro-2-(4-fluorophenyl)-5-methyl-1-piperidyl]-2-oxo-acetamide (Compound 786

Step 1: Synthesis of rac-tert-butyl (5-(2-((2R,5R)-2-(3,4-difluorophenyl)-4,4-difluoro-5-methylpiperidin-1-yl)-2-oxoacetamido)-3-methylpyridin-2-yl)carbamate (2R,5R)-4,4-difluoro-2-(4-fluorophenyl)-5-methyl-piperidine (0.6 g, 2.62 mmol), TEA (2.65 g, 26.17 mmol, 3.65 mL) and 2-[[6-(tert-butoxycarbonylamino)-5-methyl-3-pyridyl]amino]-2-oxo-acetic acid (772.88 mg, 2.62 mmol) was dissolved in DMF (26 mL) and HATU (1.49 g, 3.93 mmol) was added in one portion, the resulting mixture was stirred for 3 hr at 20° C. The reaction mixture was poured into water and the aqueous phase was extracted with EA (3 times), then the combined organic phase was washed with

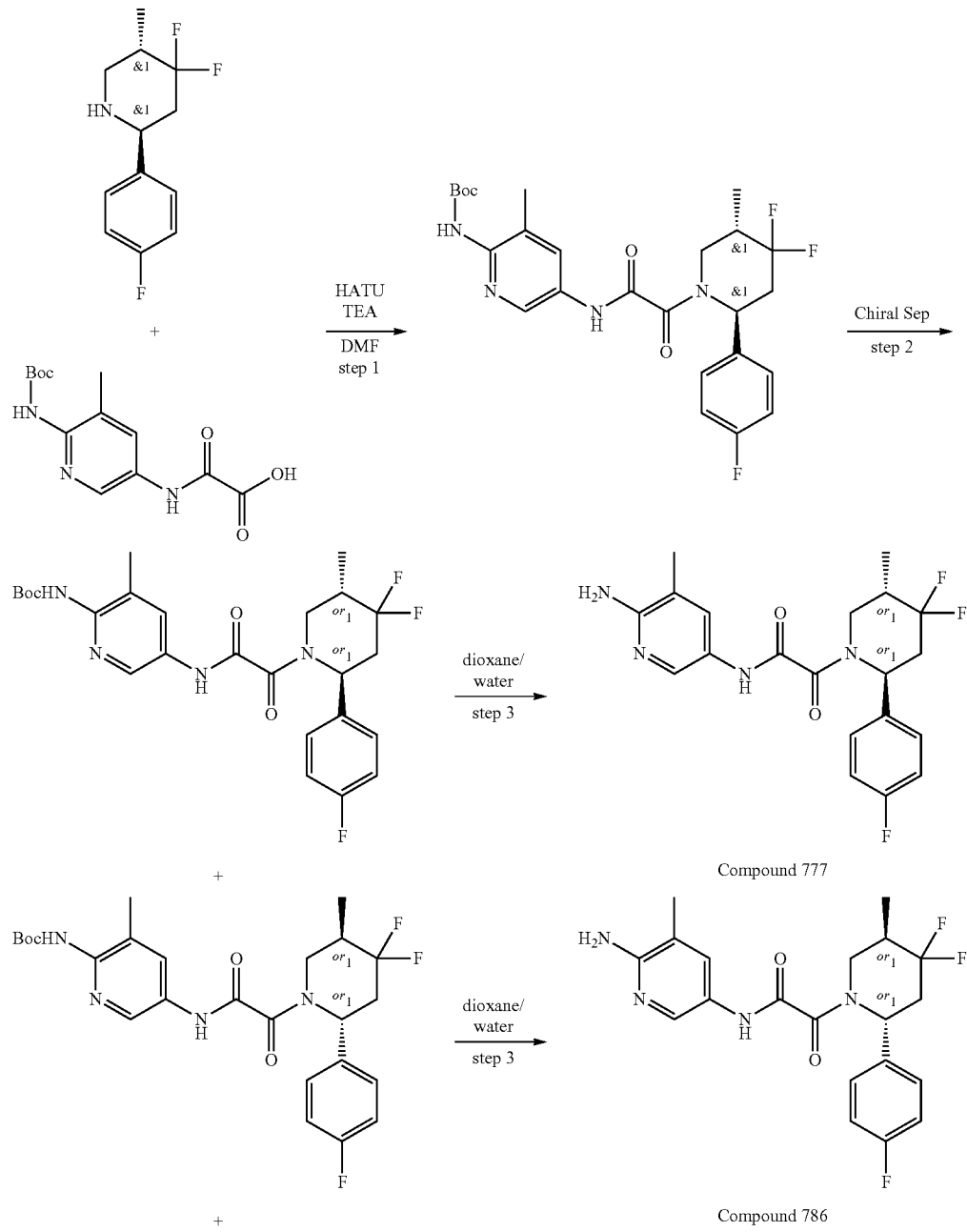

brine (3 times), dried over Na₂SO₄ and concentrated on vacuo. The crude product was purified by reverse phase HPLC (45-60% 2-10 min; water-acetonitrile; 30 ml/min; loading pump 4 ml/min acetonitrile, column SunFire 19*100 mm). The reaction was successful. The desired product (tert-butyl N-[5-[[2-[(2R,5R)-4,4-difluoro-2-(4-fluorophenyl)-5-methyl-1-piperidyl]-2-oxo-acetyl]amino]-3-methyl-2-pyridyl]carbamate (0.23 g, 454.08 μmol, 17.35% yield)) was isolated as a brown solid.

LCMS(ESI): [M+1]⁺ m/z: calcd 506.2; found 507.2; Rt=1.471 min.

Step 2: Chiral Resolution for Tert-butyl N-[5-[[2-[(2R,5R)-4,4-difluoro-2-(4-fluorophenyl)-5-methyl-1-piperidyl]-2-oxo-acetyl]amino]-3-methyl-2-pyridyl]carbamate and Tert-butyl N-[5-[[2-[(2S,5S)-4,4-difluoro-2-(4-fluorophenyl)-5-methyl-4-piperidyl]-2-oxo-acetyl]amino]-3-methyl-2-pyridyl]carbamate Chiral separation was performed using (Column: Chiralpak IC-II (250*20, 5 mkm); Mobile phase: Hexane-IPA-MeOH, 60-20-20, Flow Rate: 12 mL/min; Column Temperature: 24° C.; Wavelength: 205 nm, 258 nm, 290 nm) to give tert-butyl N-[5-[[2-[(2R,5R)-4,4-difluoro-2-(4-fluorophenyl)-5-methyl-1-piperidyl]-2-oxo-acetyl]amino]-3-methyl-2-pyridyl]carbamate (0.097 g, 191.50 μmol, 42.17% yield)—ret. time is 11.162 min and tert-butyl N-[5-[[2-[(2S,5S)-4,4-difluoro-2-(4-fluorophenyl)-5-methyl-1-piperidyl]-2-oxo-acetyl]amino]-3-methyl-2-pyridyl]carbamate (0.089 g, 175.71 μmol, 38.70% yield)—ret. time is 15.271 min.

Step 3: Synthesis of N-(6-amino-5-methyl-3-pyridyl)-2-[(2S,5S)-4,4-difluoro-2-(4-fluorophenyl)-5-methyl-1-piperidyl]-2-oxo-acetamide (Compound 777 tert-butyl N-[5-[[2-[(2S,5S)-4,4-difluoro-2-(4-fluorophenyl)-5-methyl-1-piperidyl]-2-oxo-acetyl]amino]-3-methyl-2-pyridyl]carbamate (0.089 g, 175.71 μmol) was dissolved in mixture of dioxane (3 mL) and water (3 mL) then stirred at 100° C. for 12 hr. The reaction mixture was concentrated on vacuo.

The crude product was purified by HPLC (10-65% 2-10 min; water/MeCN+TFA; 30 ml/min; loading pump 4 ml/min MeCN; column SunFire 19*100 mm). The desired product (N-(6-amino-5-methyl-3-pyridyl)-2-[(2S,5S)-4,4-difluoro-2-(4-fluorophenyl)-5-methyl-1-piperidyl]-2-oxo-acetamide (0.04 g, 98.42 μmol, 56.02% yield)) was obtained as a light-yellow solid.

¹H NMR (600 MHz, DMSO-d₆) δ 1.07 (d, 3H), 1.96-2.05 (m, 3H), 2.12-2.26 (m, 1H), 2.37-2.46 (m, 1H), 2.80-2.89 (m, 1H), 2.95-3.01 (m, OH), 3.38-3.48 (m, 1H), 3.73-4.36 (m, 1H), 5.49-5.63 (m, 1H), 5.63-5.86 (m, 2H), 7.13-7.28 (m, 2H), 7.33-7.41 (m, 2H), 7.41-7.55 (m, 1H), 7.91-8.11 (m, 1H), 10.46-10.68 (m, 1H).

LCMS(ESI): [M+1]⁺ m/z: calcd 406.2; found 407.2; Rt=2.740 min.

Step 4: Synthesis of N-(6-amino-5-methyl-3-pyridyl)-2-[(2R,5R)-4,4-difluoro-2-(4-fluorophenyl)-5-methyl-1-piperidyl]-2-oxo-acetamide (Compound 786 tert-butyl N-[5-[[2-[(2R,5R)-4,4-difluoro-2-(4-fluorophenyl)-5-methyl-1-piperidyl]-2-oxo-acetyl]amino]-3-methyl-2-pyridyl]carbamate (0.097 g, 191.50 μmol) was dissolved in mixture of dioxane (3 mL) and water (3 mL) then stirred at 100° C. for 12 hr. The reaction mixture was concentrated on vacuo.

The crude product was purified by HPLC (10-65% 2-10 min; water/MeCN+TFA; 30 ml/min; loading pump 4 ml/min MeCN; column SunFire 19*100 mm). The desired product (N-(6-amino-5-methyl-3-pyridyl)-2-[(2R,5R)-4,4-difluoro-2-(4-fluorophenyl)-5-methyl-1-piperidyl]-2-oxo-acetamide (0.046 g, 113.19 μmol, 59.11% yield)) was obtained as a light-yellow solid.

¹H NMR (600 MHz, DMSO-d₆) δ 1.07 (d, 3H), 1.96-2.05 (m, 3H), 2.12-2.26 (m, 1H), 2.37-2.46 (m, 1H), 2.80-2.89 (m, 1H), 2.95-3.01 (m, OH), 3.38-3.48 (m, 1H), 3.73-4.36 (m, 1H), 5.49-5.63 (m, 1H), 5.63-5.86 (m, 2H), 7.13-7.28 (m, 2H), 7.33-7.41 (m, 2H), 7.41-7.55 (m, 1H), 7.91-8.11 (m, 1H), 10.46-10.68 (m, 1H).

LCMS(ESI): [M+1]⁺ m/z: calcd 406.2; found 407.2; Rt=2.740 min.

Example 421. The Synthesis of N-(6-amino-5-methyl-3-pyridyl)-2-[(2S,5R)-2-(3,5-Dichlorophenyl)-5-methyl-1-piperidyl]-2-oxo-acetamide (Compound 681) and N-(6-amino-5-methyl-3-pyridyl)-2-[(2R,5S)-2-(3,5-Dichlorophenyl)-5-methyl-1-piperidyl]-2-oxo-acetamide (Compound 660

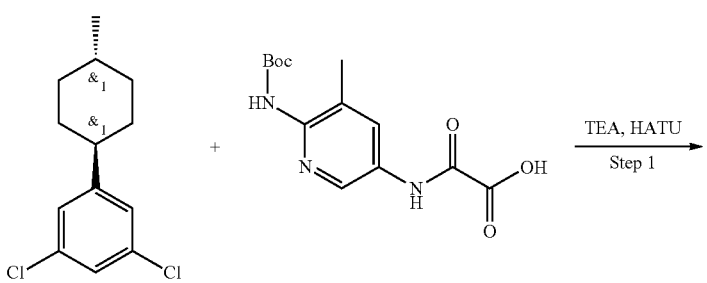

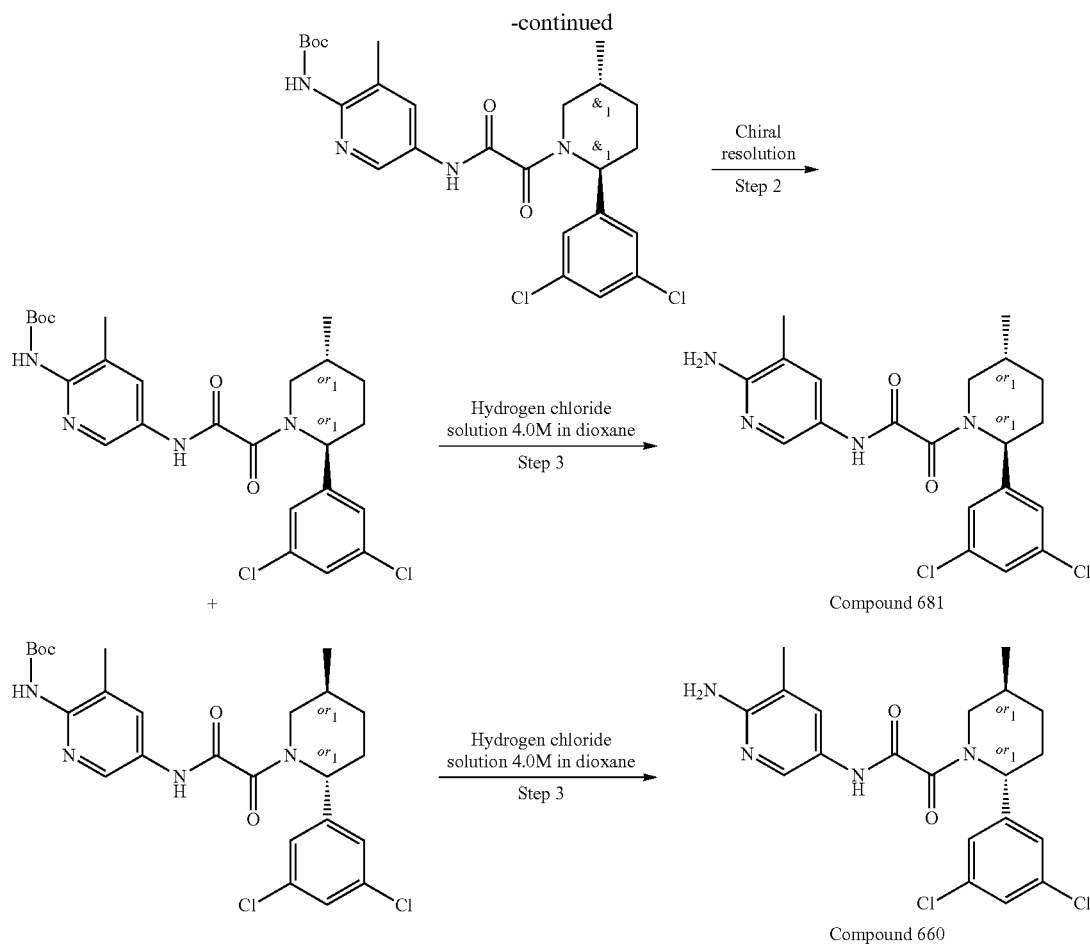

Compound 681

Compound 660

Step 1. Synthesis of tert-butyl N-[5-[[2-[2-(3,5-Dichlorophenyl)-5-methyl-1-piperidyl]-2-oxo-acetyl]amino]-3-methyl-2-pyridyl]carbamate To a solution of methyl 2-[2-(3,5-dichlorophenyl)-5-methyl-1-piperidyl]-2-oxo-acetate (0.88 g, 2.67 mmol) in MeOH (10 mL) was added hydroxysodium (106.59 mg, 2.67 mmol, 50.04 μL) and the resulting mixture was stirred for 1 hr. Then, the solvent was evaporated and the residue was reevaporated with EtOH. After that, solids were dissolved in DMF and HATU (1.01 g, 2.67 mmol) was added followed by tert-butyl N-(5-amino-3-methyl-2-pyridyl)carbamate (595.02 mg, 2.67 mmol) and the resulting mixture was stirred for 12 hr. The resulting mixture was poured into water, extracted 3 times with EtOAc, combined organics were washed with water, brine and evaporated. The residue was subjected to HPLC (60-85%2-7 min water-acetonitrile; flow 30 ml/min (loading pump 4 ml/min; acetonitrile); column SunFire C18 100×19 mm 5 um (R)). tert-butyl N-[5-[[2-[2-(3,5-dichlorophenyl)-5-methyl-1-piperidyl]-2-oxo-acetyl]amino]-3-methyl-2-pyridyl]carbamate (920 mg, 1.76 mmol, 66.20% yield) was obtained as an off-white solid.

$^1$H NMR (500 MHz, CDCl$_3$) δ 1.09 (m, 3H), 1.44 (m, 1H), 1.51 (s, 9H), 1.91-2.18 (m, 4H), 2.34 (m, 3H), 2.97-3.38 (m, 1H), 4.26-4.86 (m, 1H), 5.59-6.42 (m, 1H), 6.91 (m, 1H), 7.16 (m, 2H), 7.26 (m, 1H), 8.08 (m, 1H), 8.39 (m, 1H), 9.47 (m, 1H).

LCMS(ESI): [M+H]$^+$ m/z: calcd 521.2; found 522.2; Rt=4.140 min.

Step 2. Separation for Tert-butyl N-[5-[[2-[(2S,5R)-2-(3,5-Dichlorophenyl)-5-methyl-1-piperidyl]-2-oxo-acetyl]amino]-3-methyl-2-pyridyl]carbamate and Tert-butyl N-[5-[[2-[(2R,5S)-2-(3,5-Dichlorophenyl)-5-methyl-1-piperidyl]-2-oxo-acetyl]amino]-3-methyl-2-pyridyl]carbamate Chiral resolution First: separation of P1 from cis1 impurity and P2 (wasn't separated from cis2 impurity) IC-II (250*20, 5 mkm), Hexane-IPA-MeOH, 80-10-10, 12 ml/min Second: separation of P2 from cis2 impurity AD-H (250*20, 5 mkm), Hexane-EtOH, 80-20, 12 ml/min RT of P1=31.454 min (IC, Hexane-IPA-MeOH, 80-10-10, 0.6 ml/min) RT of P2=44.868 min (IC, Hexane-IPA-MeOH, 80-10-10, 0.6 ml/min).

Step 3. Synthesis of N-(6-amino-5-methyl-3-pyridyl)-2-[(2S,5R)-2-(3,5-Dichlorophenyl)-5-methyl-1-piperidyl]-2-oxo-acetamide (Compound 681

To a solution of tert-butyl N-[5-[[2-[(2S,5R)-2-(3,5-dichlorophenyl)-5-methyl-1-piperidyl]-2-oxo-acetyl]amino]-3-methyl-2-pyridyl]carbamate (271.36 mg, 520.41 μmol) in dioxane (3 mL) was added Hydrogen chloride solution 4.0 M in dioxane (94.87 mg, 2.60 mmol, 118.59 μL) at 21° C.

The resulting mixture was left to stir for 8 hr. The resulting mixture was evaporated to dryness and subjected to HPLC (50% 0.5-6 min water-acetonitrile+NH$_3$; flow 30 ml/min (loading pump 4 ml/min; acetonitrile); column Tiart 100×19 mm 5 um (R)). N-(6-amino-5-methyl-3-pyridyl)-2-[(2S,5R)-2-(3,5-dichlorophenyl)-5-methyl-1-piperidyl]-2-oxo-acetamide (152.5 mg, 361.96 μmol, 69.55% yield) was obtained as an off-white solid. Optic rotatory power: +136.15° (C=0.2 g/100 mL; 21° C.). RT=36.109 min (IC, Hexane-IPA-MeOH, 80-10-10, 0.6 ml/min).

$^1$H NMR (DMSO-d$_6$, 600 MHz): δ (ppm) 0.99 (m, 3H), 1.30 (m, 1H), 1.60 (m, 1H), 1.87 (m, 1H), 2.01 (m, 4H), 2.16 (m, 1H), 2.90 (m, 1H), 3.73 (m, 1H), 5.30 (m, 1H), 5.61 (m, 2H), 7.33 (m, 2H), 7.47 (m, 2H), 7.97 (m, 1H), 10.55 (m, 1H)

LCMS(ESI): [M+H]$^+$ m/z: calcd 420.2; found 421.2; Rt=2.679 min.

Step 4. Synthesis of N-(6-amino-5-methyl-3-pyridyl)-2-[(2R,5S)-2-(3,5-Dichlorophenyl)-5-methyl-1-piperidyl]-2-oxo-acetamide (Compound 660

To a solution of tert-butyl N-[5-[[2-[(2R,5S)-2-(3,5-dichlorophenyl)-5-methyl-1-piperidyl]-2-oxo-acetyl]amino]-3-methyl-2-pyridyl]carbamate (297.59 mg, 570.71 μmol) in dioxane (3 mL) was added Hydrogen chloride solution 4.0 M in dioxane (104.04 mg, 2.85 mmol, 130.05 μL) at 21° C.

The resulting mixture was left to stir for 8 hr. The resulting mixture was evaporated to dryness and subjected to HPLC (50% 0.5-6 min water-acetonitrile+NH$_3$; flow 30 ml/min (loading pump 4 ml/min; acetonitrile); column Tiart 100×19 mm 5 um (R)). N-(6-amino-5-methyl-3-pyridyl)-2-[(2R,5S)-2-(3,5-dichlorophenyl)-5-methyl-1-piperidyl]-2-oxo-acetamide (176.9 mg, 419.87 μmol, 73.57% yield) was obtained as an off-white solid.

Optical rotatory power: −139.95° (C=0.2 g/100 mL; 21° C.)

RT=30.522 min (IC, Hexane-IPA-MeOH, 80-10-10, 0.6 ml/min)

$^1$H NMR (DMSO-d$_6$, 600 MHz): δ (ppm) 0.99 (m, 3H), 1.30 (m, 1H), 1.60 (m, 1H), 1.87 (m, 1H), 2.01 (m, 4H), 2.16 (m, 1H), 2.90 (m, 1H), 3.73 (m, 1H), 5.30 (m, 1H), 5.61 (m, 2H), 7.33 (m, 2H), 7.47 (m, 2H), 7.97 (m, 1H), 10.55 (m, 1H)

LCMS(ESI): [M+H]$^+$ m/z: calcd 420.2; found 421.2; Rt=2.679 min.

Example 422. The Synthesis of Rac N-(6-amino-5-methyl-3-pyridyl)-2-[2-(6-Isoquinolyl)-5-methyl-1-piperidyl]-2-oxo-acetamide (Compound 758), rel-N-(6-amino-5-methyl-3-pyridyl)-2-[(2R,5S)-2-(6-Isoquinolyl)-5-methyl-1-piperidyl]-2-oxo-acetamide (Compound 1002) and rel-N-(6-amino-5-methyl-3-pyridyl)-2-[(2S,5R)-2-(6-Isoquinolyl)-5-methyl-1-piperidyl]-2-oxo-acetamide (Compound 1000

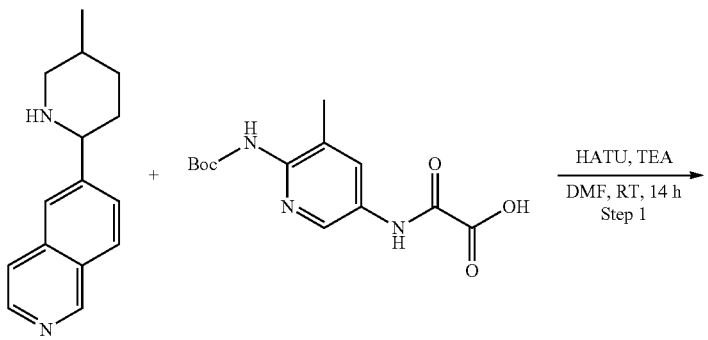

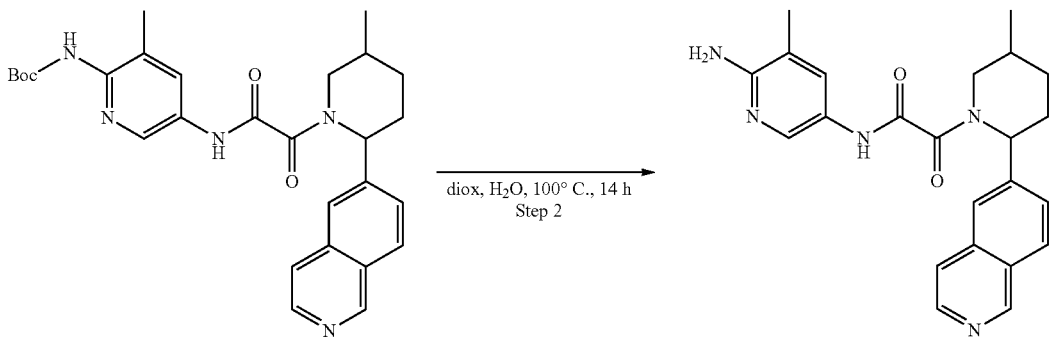

Compound 758

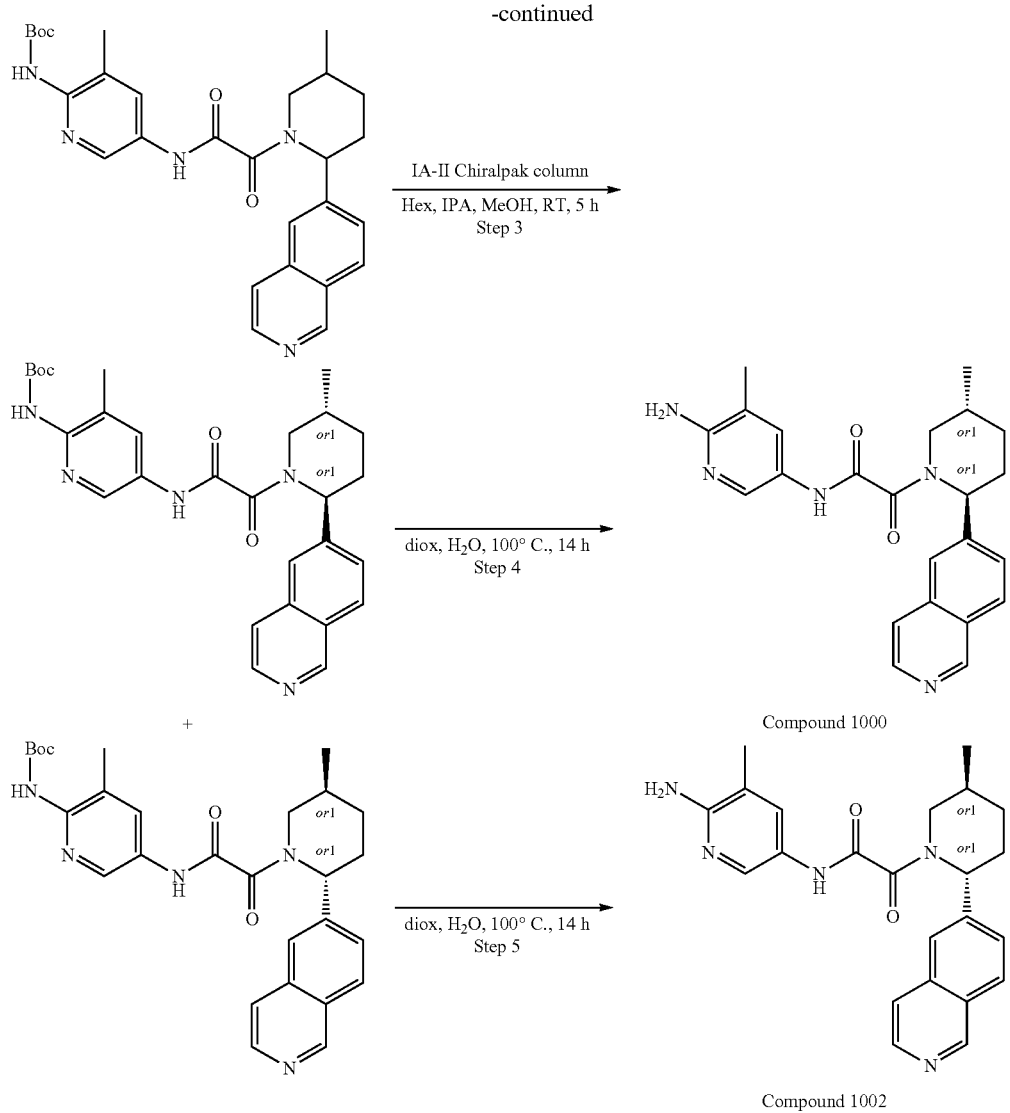

Compound 1000

Compound 1002

Step 1: The Synthesis of tert-butyl (5-(2-(2-(Isoquinolin-6-yl)-5-methylpiperidin-1-yl)-2-oxoacetamido)-3-methylpyridin-2-yl)carbamate 6-(5-methyl-2-piperidyl)isoquinoline (0.32 g, 1.41 mmol) was dissolved in DMF (5 mL) and triethylamine (1.43 g, 14.14 mmol, 1.97 mL) was added, followed by 2-[[6-(tert-butoxycarbonylamino)-5-methyl-3-pyridyl]amino]-2-oxo-acetic acid (417.53 mg, 1.41 mmol). Then the HATU (806.44 mg, 2.12 mmol) was added dropwise and the reaction mixture was stirred overnight. The next day it was evaporated in vacuo and purified by HPLC LCMS(ESI): [M+H]⁺ m/z: calcd 503.2; found 504.4; Rt=1.137 min.

Step 2: The Synthesis of N-(6-amino-5-methyl-3-pyridyl)-2-[2-(6-isoquinolyl)-5-methyl-1-piperidyl]-2-oxo-acetamide (Compound 758 tert-butyl N-[5-[[2-[2-(6-isoquinolyl)-5-methyl-1-piperidyl]-2-oxo-acetyl]amino]-3-methyl-2-pyridyl]carbamate (0.142 g, 281.97 μmol) was dissolved in Dioxane (1.5 mL) and Water (1.5 mL) and stirred overnight at 100° C. The next day it was evaporated in vacuo and purified by HPLC to obtain N-(6-amino-5-methyl-3-pyridyl)-2-[2-(6-isoquinolyl)-5-methyl-1-piperidyl]-2-oxo-acetamide (0.0264 g, 65.43 μmol, 23.20% yield).

$^1$H NMR (600 MHz, DMSO-$d_6$) δ 1.00-1.04 (m, 3H), 1.31-1.47 (m, 1H), 1.66-1.85 (m, 2H), 1.86-1.97 (m, 2H), 1.98-2.09 (m, 3H), 2.09-2.21 (m, 1H), 2.21-2.34 (m, 1H), 2.77-3.27 (m, 1H), 3.48-4.09 (m, 2H), 5.31-5.75 (m, 1H), 5.84-6.16 (m, 1H), 7.57-7.69 (m, 1H), 7.77-7.85 (m, 1H), 7.87-8.04 (m, 1H), 8.10-8.15 (m, 1H), 8.43-8.53 (m, 1H), 9.24-9.31 (m, 1H), 10.56-10.67 (m, 1H).

LCMS(ESI): [M+2H]⁺ m/z: calcd 403.2; found 405.2; Rt=0.834 min.

Step 3: The Synthesis of rel-tert-butyl N-[5-[[2-[(2R,5S)-2-(6-isoquinolyl)-5-methyl-1-piperidyl]-2-oxo-acetyl]amino]-3-methyl-2-pyridyl]carbamate and Rel-tert-butyl N-(5-{2-[(2R,5S)-2-(Isoquinolin-6-yl)-5-methylpiperidin-1-yl]-2-oxoacetamido}-3-methylpyridin-2-yl)carbamate tert-butyl N-[5-[[2-[2-(6-isoquinolyl)-5-methyl-1-piperidyl]-2-oxo-acetyl]amino]-3-methyl-2-pyridyl]carbamate (0.14 g, 278.00 µmol) was chiral separated (Column: Chiralpak IA-II (250*20 mm, 5 mkm) column and Hexane-IPA-MeOH, 60-20-20 as a mobile phase, Flow Rate: 12 mL/min; Column Temperature: 24° C.; Wavelength: 205 nm, 220 nm, 258 nm), to obtain Isomer B tert-butyl N-[5-[[2-[(2R,5S)-2-(6-isoquinolyl)-5-methyl-1-piperidyl]-2-oxo-acetyl]amino]-3-methyl-2-pyridyl]carbamate (55.74 mg, 110.69 µmol, 39.81% yield; RetTime=38.79 min) and Isomer A rel-tert-butyl N-(5-{2-[(2R,5S)-2-(isoquinolin-6-yl)-5-methylpiperidin-1-yl]-2-oxoacetamido}-3-methylpyridin-2-yl)carbamate (0.06222 g, 123.55 µmol, 44.44% yield; RetTime=28.38 min)

Isomer B: RT (IA, Hexane-IPA-MeOH, 60-20-20, 0.6 mL/min)=34.111 min.

LCMS(ESI): [M+2H]$^+$ m/z: calcd 503.2; found 505.2; Rt=2.360 min.

Isomer A: RT (IA, Hexane-IPA-MeOH, 60-20-20, 0.6 mL/min)=26.066 min.

LCMS(ESI): [M+H]$^+$ m/z: calcd 503.2; found 504.2; Rt=2.358 min.

Step 4: The Synthesis of rel-N-(6-amino-5-methyl-3-pyridyl)-2-[(2S,5R)-2-(6-isoquinolyl)-5-methyl-1-piperidyl]-2-oxo-acetamide (Compound 1000 tert-butyl N-[5-[[2-[(2S,5R)-2-(6-isoquinolyl)-5-methyl-1-piperidyl]-2-oxo-acetyl]amino]-3-methyl-2-pyridyl]carbamate (0.06222 g, 123.55 µmol) was dissolved in Dioxane (1 mL) and H$_2$O (1 mL) and stirred overnight at 100° C. The next day it was evaporated in vacuo and purified by HPLC to obtain N-(6-amino-5-methyl-3-pyridyl)-2-[(2S,5R)-2-(6-isoquinolyl)-5-methyl-1-piperidyl]-2-oxo-acetamide (0.0108 g, 26.77 µmol, 21.66% yield).

LCMS(ESI): [M+2H]$^+$ m/z: calcd 403.2; found 405.2; Rt=0.774 min.

Step 5: The Synthesis of rel-N-(6-amino-5-methyl-3-pyridyl)-2-[(2S,5R)-2-(6-Isoquinolyl)-5-methyl-1-piperidyl]-2-oxo-acetamide (Compound 1002 tert-butyl N-[5-[[2-[(2R,5S)-2-(6-isoquinolyl)-5-methyl-1-piperidyl]-2-oxo-acetyl]amino]-3-methyl-2-pyridyl]carbamate (55.74 mg, 110.68 µmol) was dissolved in Dioxane (1 mL) and H$_2$O (1 mL) and stirred overnight at 100° C. The next day it was evaporated in vacuo and purified by HPLC to obtain N-(6-amino-5-methyl-3-pyridyl)-2-[(2R,5S)-2-(6-isoquinolyl)-5-methyl-1-piperidyl]-2-oxo-acetamide (0.0115 g, 28.50 µmol, 25.75% yield).

LCMS(ESI): [M+2H]$^+$ m/z: calcd 403.2; found 405.2; Rt=0.775 min.

Example 423. The Synthesis of rel-N-[3-ethyl-5-[[2-[(2S,5R)-2-(6-isoquinolyl)-5-methyl-1-piperidyl]-2-oxo-acetyl]amino]-2-pyridyl]carbamate (Compound 919) and rel-N-(6-amino-5-ethyl-3-pyridyl)-2-[(2R,5S)-2-(6-isoquinolyl)-5-methyl-1-piperidyl]-2-oxo-acetamide (Compound 929

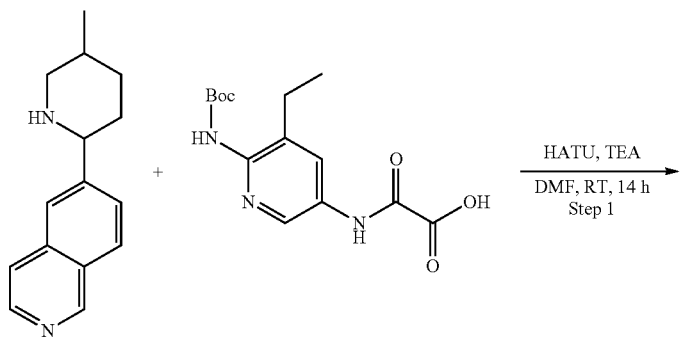

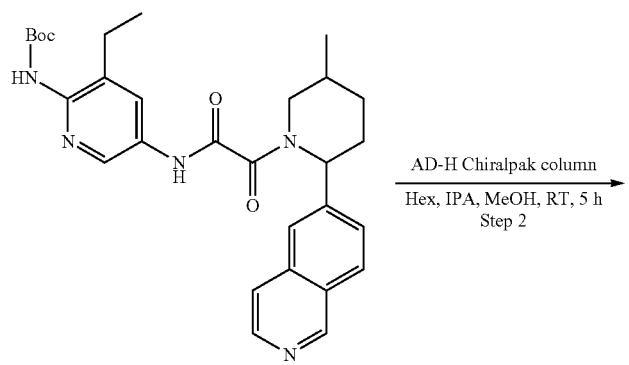

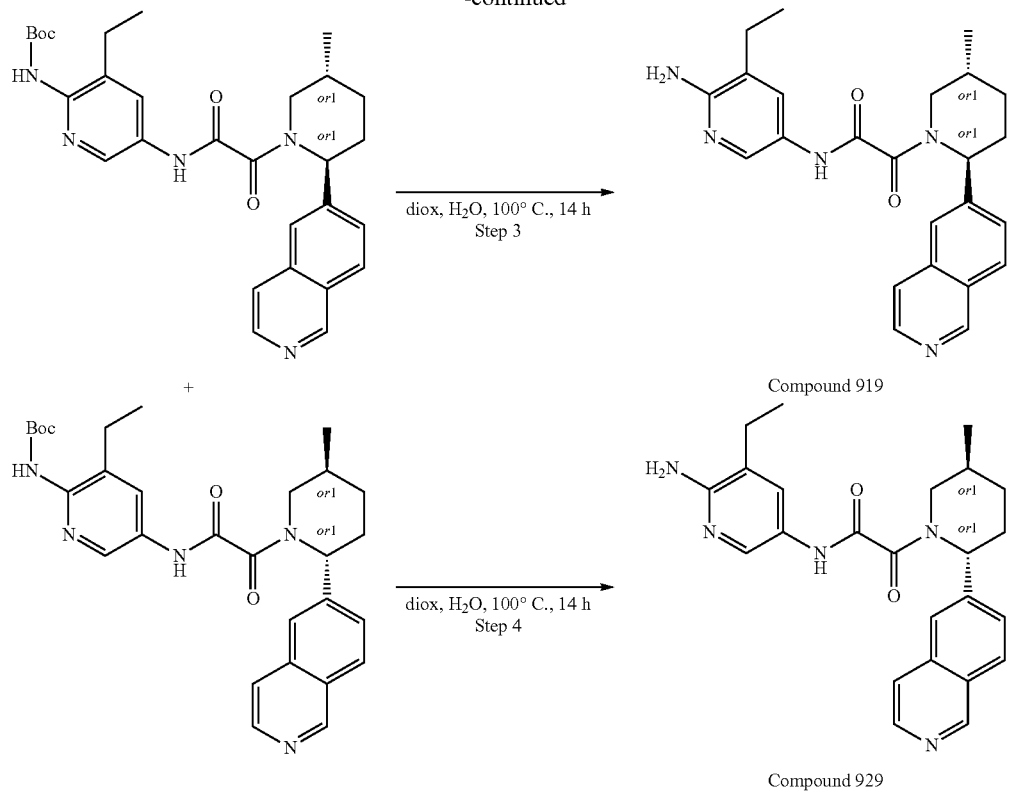

Compound 919

Compound 929

Step 1: The Synthesis of tert-butyl N-[3-ethyl-5-[[2-[2-(6-isoquinolyl)-5-methyl-1-piperidyl]-2-oxo-acetyl]amino]-2-pyridyl]carbamate 6-(5-methyl-2-piperidyl)isoquinoline (0.5 g, 2.21 mmol) was dissolved in DMF (10 mL) and triethylamine (2.24 g, 22.09 mmol, 3.08 mL) was added, followed by 2-[[6-(tert-butoxycarbonylamino)-5-ethyl-3-pyridyl]amino]-2-oxo-acetic acid (683.37 mg, 2.21 mmol). Then the HATU (1.26 g, 3.31 mmol) was added dropwise and the reaction mixture was stirred overnight. The next day it was evaporated in vacuo and purified by HPLC to obtain tert-butyl N-[3-ethyl-5-[[2-[2-(6-isoquinolyl)-5-methyl-1-piperidyl]-2-oxo-acetyl]amino]-2-pyridyl]carbamate (0.13 g, 251.15 μmol, 11.37% yield).
LCMS(ESI): [M+H]+ m/z: calcd 517.2; found 518.2; Rt=0.971 min.

Step 2: The Synthesis of rel-tert-butyl N-[3-ethyl-5-[[2-[(2S,5R)-2-(6-Isoquinolyl)-5-methyl-1-piperidyl]-2-oxo-acetyl]amino]-2-pyridyl]carbamate and Rel-tert-butyl N-[3-ethyl-5-[[2-[(2R,5S)-2-(6-isoquinolyl)-5-methyl-1-piperidyl]-2-oxo-acetyl]amino]-2-pyridyl]carbamate tert-butyl N-[3-ethyl-5-[[2-[2-(6-isoquinolyl)-5-methyl-1-piperidyl]-2-oxo-acetyl]amino]-2-pyridyl]carbamate (0.13 g, 251.15 μmol) was chiral separated (Column: Chiralpak AD-H (250*20 mm, 5 m); Mobile phase: Hexane-IPA-MeOH, 70-15-15 Flow Rate: 12 mL/min; Column Temperature: 24° C.; Wavelength: 210 nm, 225 nm, 254 nm to obtain tert-butyl N-[3-ethyl-5-[[2-[(2S,5R)-2-(6-isoquinolyl)-5-methyl-1-piperidyl]-2-oxo-acetyl]amino]-2-pyridyl]carbamate (0.04 g, 77.28 μmol, 30.77% yield; ret time=22.46 min; Isomer A) and tert-butyl N-[3-ethyl-5-[[2-[(2R,5S)-2-(6-isoquinolyl)-5-methyl-1-piperidyl]-2-oxo-acetyl]amino]-2-pyridyl]carbamate (0.0497 g, 96.02 μmol, 38.23% yield; ret time=26.31 min Isomer B).

isomer A: RT (AD-H, Hexane-IPA-MeOH, 60-20-20, 0.6 mL/min)=19.622 min.
LCMS(ESI): [M+2H]+ m/z: calcd 517.2; found 519.2; Rt=1.167 min.
isomer B: RT (AD-H, Hexane-IPA-MeOH, 60-20-20, 0.6 mL/min)=27.358 min.
LCMS(ESI): [M+2H]+ m/z: calcd 517.2; found 519.2; Rt=1.166 min.

Step 3: The Synthesis of rel-N-[3-ethyl-5-[[2-[(2S,5R)-2-(6-isoquinolyl)-5-methyl-1-piperidyl]-2-oxo-acetyl]amino]-2-pyridyl]carbamate (Compound 919 tert-butyl N-[3-ethyl-5-[[2-[(2S,5R)-2-(6-isoquinolyl)-5-methyl-1-piperidyl]-2-oxo-acetyl]amino]-2-pyridyl]carbamate (0.04 g, 77.28 μmol) was dissolved in H2O (1 mL) and Dioxane (1 mL) and stirred overnight at 100° C. The next day it was evaporated in vacuo and purified by HPLC to obtain rel-N-[3-ethyl-5-[[2-[(2S,5R)-2-(6-isoquinolyl)-5-methyl-1-piperidyl]-2-oxo-acetyl]amino]-2-pyridyl]carbamate (0.0214 g, 51.26 μmol, 66.33% yield).
$^1$H NMR (DMSO-$d_6$, 600 MHz): δ (ppm) 1.07 (m, 6H), 1.37 (m, 1H), 1.71 (m, 1H), 1.89 (m, 1H), 2.38 (m, 4H), 3.03 (m, 1H), 3.80 (m, 1H), 5.67 (m, 3H), 7.45 (m, 1H), 7.64 (m, 1H), 7.81 (m, 1H), 8.01 (m, 3H), 8.48 (m, 1H), 9.27 (m, 1H), 10.55 (m, 1H).
LCMS(ESI): [M+H]+ m/z: calcd 417.2; found 418.2; Rt=1.528 min.

Step 4: The Synthesis of rel-N-(6-amino-5-ethyl-3-pyridyl)-2-[(2R,5S)-2-(6-isoquinolyl)-5-methyl-1-piperidyl]-2-oxo-acetamide (Compound 929 tert-butyl N-[3-ethyl-5-[[2-[(2R,5S)-2-(6-isoquinolyl)-5-methyl-1-piperidyl]-2-oxo-acetyl]amino]-2-pyridyl]carbamate (0.0497 g, 96.02 μmol) was dissolved in H$_2$O (1 mL) and Dioxane (1 mL) and stirred overnight at 100° C. The next day it was evaporated in vacuo and purified by HPLC to obtain rel-N-(6-amino-5-ethyl-3-pyridyl)-2-[(2R,5S)-2-(6-isoquinolyl)-5-methyl-1-piperidyl]-2-oxo-acetamide (0.0249 g, 59.64 μmol, 62.11% yield).

$^1$H NMR (DMSO-d$_6$, 600 MHz): δ (ppm) 1.07 (m, 6H), 1.37 (m, 1H), 1.72 (m, 1H), 1.87 (m, 1H), 2.14 (m, 1H), 2.36 (m, 3H), 2.95 (m, 1H), 3.80 (m, 1H), 5.65 (m, 3H), 7.45 (m, 1H), 7.64 (dd, 1H), 7.81 (m, 1H), 7.90 (m, 1H), 8.03 (m, 1H), 8.12 (m, 1H), 8.48 (m, 1H), 9.27 (m, 1H), 10.54 (m, 1H).

LCMS(ESI): [M+H]$^+$ m/z: calcd 417.2; found 418.2; Rt=1.502 min.

Example 424. The Synthesis of rel-N-(6-amino-5-methyl-3-pyridyl)-2-[(2R,5S)-5-methyl-2-(6-methyl-3-pyridyl)-1-piperidyl]-2-oxo-acetamide (Compound 707) and rel-N-(6-amino-5-methyl-3-pyridyl)-2-[(2S,5R)-5-methyl-2-(6-methyl-3-pyridyl)-1-piperidyl]-2-oxo-acetamide (Compound 687

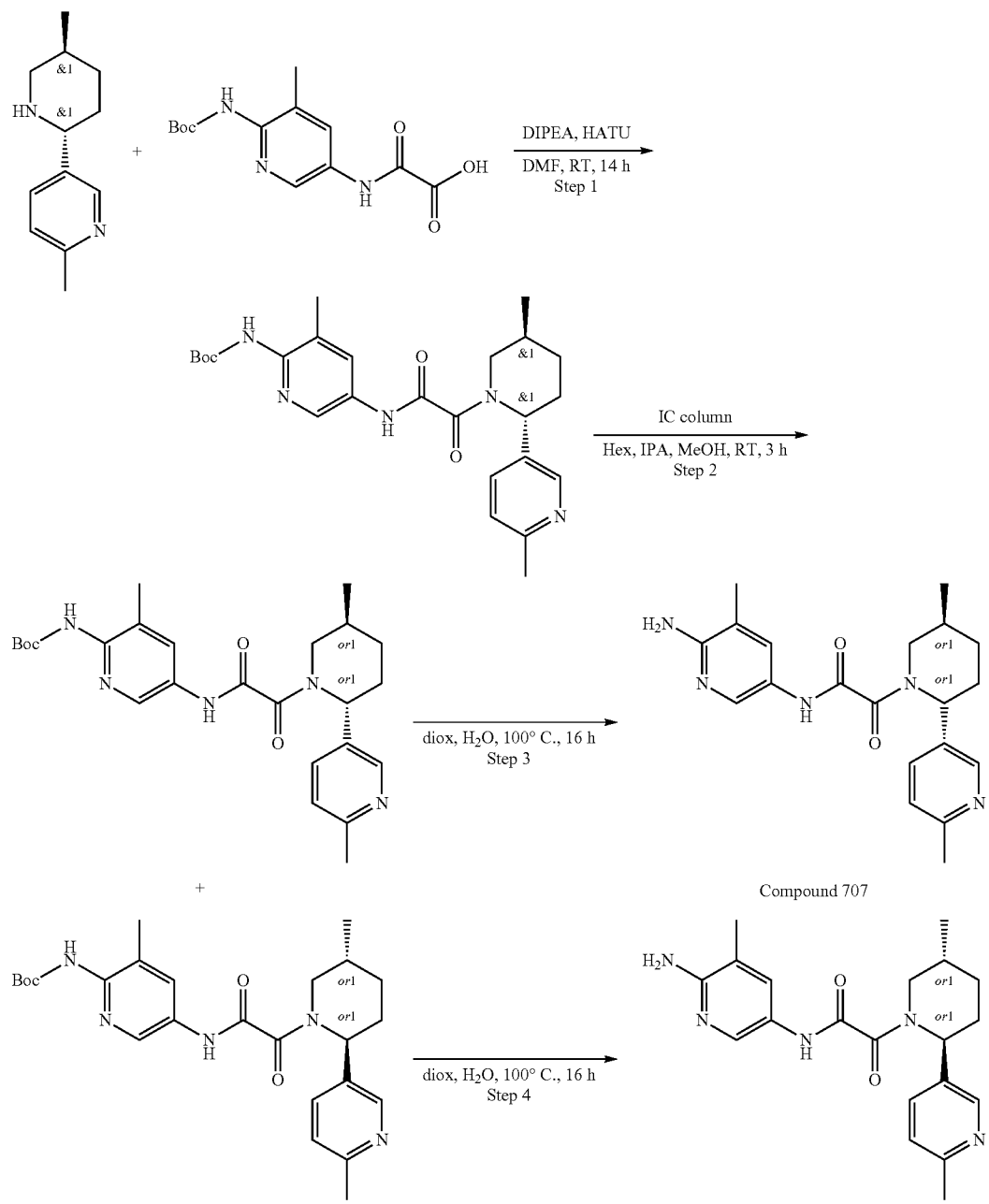

Compound 707

Compound 687

Step 1: The Synthesis of tert-butyl N-[3-methyl-5-[[2-[5-methyl-2-(6-methyl-3-pyridyl)-1-piperidyl]-2-oxo-acetyl]amino]-2-pyridyl]carbamate DIPEA (547.10 mg, 4.23 mmol, 737.33 μL) was added to the solution of respective 2-[[6-(tert-butoxycarbonylamino)-5-methyl-3-pyridyl]amino]-2-oxo-acetic acid (0.5 g, 1.69 mmol) and 2-methyl-5-(5-methyl-2-piperidyl)pyridine (322.20 mg, 1.69 mmol) in DMF (10 mL). The resulting mixture was stirred for 5 min followed by the addition of HATU (708.20 mg, 1.86 mmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and MeOH as an eluent mixture) to afford tert-butyl N-[3-methyl-5-[[2-[5-methyl-2-(6-methyl-3-pyridyl)-1-piperidyl]-2-oxo-acetyl]amino]-2-pyridyl]carbamate (329.8 mg, 705.37 μmol, 41.66% yield).

LCMS(ESI): [M+2H]$^+$ m/z: calcd 467.2; found 469.2; Rt=2.087 min.

Step 2: The Synthesis of rel-tert-butyl N-[3-methy-5-[[2-[(2R,5S)-5-methyl-2-(6-methyl-3-pyridyl)-1-piperidyl]-2-oxo-acetyl]amino]-2-pyridyl]carbamate (P1) and Rel-tert-butyl N-[3-methyl-5-[[2-[(2S,5R)-5-methyl-2-(6-methyl-3-pyridyl)-1-piperidyl]-2-oxo-acetyl]amino]-2-pyridyl]carbamate (P2 tert-butyl N-[3-methyl-5-[[2-[5-methyl-2-(6-methyl-3-pyridyl)-1-piperidyl]-2-oxo-acetyl]amino]-2-pyridyl]carbamate (329.8 mg, 705.37 μmol) was chirally separated using Chiralpak IC-II (250*30 mm, 5 mkm) column and Hexane-IPA-MeOH, 60-20-20 as a mobile phase, Flow 12 mL/min affording rel-tert-butyl N-[3-methyl-5-[[2-[(2R,5S)-5-methyl-2-(6-methyl-3-pyridyl)-1-piperidyl]-2-oxo-acetyl]amino]-2-pyridyl]carbamate (119.4 mg, 36.20% yield; P1) as a beige solid and rel-tert-butyl N-[3-methyl-5-[[2-[(2S,5R)-5-methyl-2-(6-methyl-3-pyridyl)-1-piperidyl]-2-oxo-acetyl]amino]-2-pyridyl]carbamate (110.77 mg, 33.59% yield; P2) also as a beige solid.

P1: RT (Chiralpak IC (250*4.6, 5 mkm), Hexane-IPA-MeOH, 60-20-20, 0.6 mL/min)=60.357 min.

LCMS(ESI): [M+H]$^+$ m/z: calcd 467.2; found 468.2; Rt=2.151 min.

P2: RT (Chiralpak IC (250*4.6, 5 mkm), Hexane-IPA-MeOH, 60-20-20, 0.6 mL/min)=48.066 min.

LCMS(ESI): [M+H]$^+$ m/z: calcd 467.2; found 468.2; Rt=2.168 min.

Step 3: The Synthesis of rel-N-(6-amino-5-methyl-3-pyridyl)-2-[(2R,5S)-5-methyl-2-(6-methyl-3-pyridyl)-1-piperidyl]-2-oxo-acetamide (Compound 707 tert-butyl N-[3-methyl-5-[[2-[(2R,5S)-5-methyl-2-(6-methyl-3-pyridyl)-1-piperidyl]-2-oxo-acetyl]-amino]-2-pyridyl]carbamate (119.14 mg, 254.81 μmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and MeCN+NH$_3$ as an eluent mixture) to afford N-(6-amino-5-methyl-3-pyridyl)-2-[(2R,5S)-5-methyl-2-(6-methyl-3-pyridyl)-1-piperidyl]-2-oxo-acetamide (74.4 mg, 202.48 μmol, 79.46% yield).

$^1$H NMR (DMSO-d$_6$, 600 MHz): δ (ppm) 1.00 (m, 3H), 1.33 (m, 1H), 1.65 (m, 1H), 1.86 (m, 1H), 2.00 (m, 4H), 2.10 (m, 1H), 2.19 (m, 1H), 2.43 (m, 3H), 3.03 (m, 1H), 3.71 (dd, 1H), 5.59 (m, 3H), 7.24 (m, 1H), 7.45 (d, 1H), 7.59 (dd, 1H), 7.97 (m, 1H), 8.39 (m, 1H).

LCMS(ESI): [M+2H]$^+$ m/z: calcd 367.2; found 369.2; Rt=1.071 min.

Step 4: The Synthesis of rel-N-(6-amino-5-methyl-3-pyridyl)-2-[(2S,5R)-5-methyl-2-(6-methyl-3-pyridyl)-1-piperidyl]-2-oxo-acetamide (Compound 687 tert-butyl N-[3-methyl-5-[[2-[(2S,5R)-5-methyl-2-(6-methyl-3-pyridyl)-1-piperidyl]-2-oxo-acetyl]-amino]-2-pyridyl]carbamate (110.77 mg, 236.91 μmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and MeCN+NH$_3$ as an eluent mixture) to afford N-(6-amino-5-methyl-3-pyridyl)-2-[(2S,5R)-5-methyl-2-(6-methyl-3-pyridyl)-1-piperidyl]-2-oxo-acetamide (58.1 mg, 158.12 μmol, 66.74% yield).

$^1$H NMR (DMSO-d$_6$, 600 MHz): δ (ppm) 0.98 (m, 3H), 1.32 (m, 1H), 1.63 (m, 1H), 1.86 (m, 1H), 2.00 (m, 4H), 2.19 (m, 1H), 2.43 (m, 3H), 2.94 (m, 1H), 3.71 (dd, 1H), 5.59 (m, 3H), 7.25 (m, 1H), 7.45 (m, 1H), 7.59 (m, 1H), 7.97 (m, 1H), 8.39 (m, 1H), 10.49 (m, 1H).

LCMS(ESI): [M+2H]$^+$ m/z: calcd 367.2; found 369.4; Rt=1.073 min.

Example 425. The Synthesis of N-(6-amino-5-methylpyridin-3-yl)-2-(5-methyl-2-(1-oxoisoindolin-5-yl)piperidin-1-yl)-2-oxoacetamide (Compound 591 and Compound 581

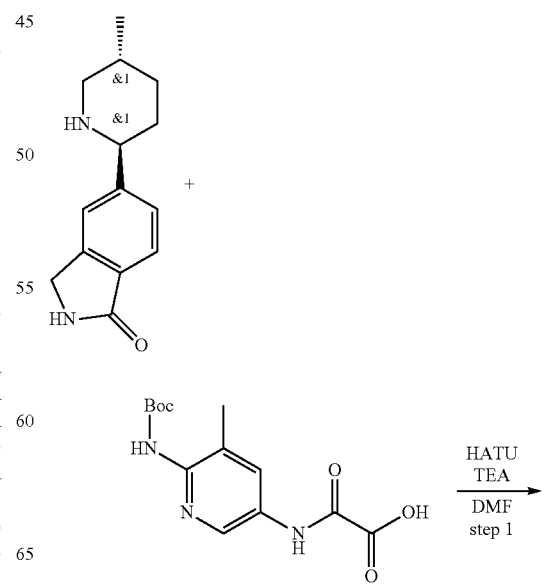

2253
-continued

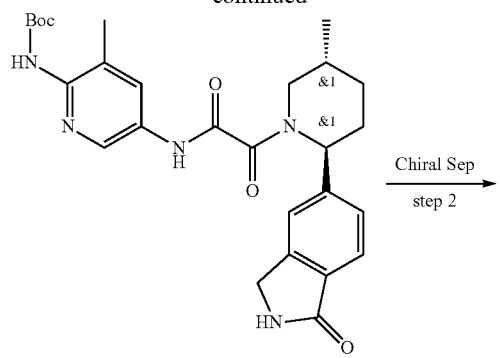

Chiral Sep
step 2

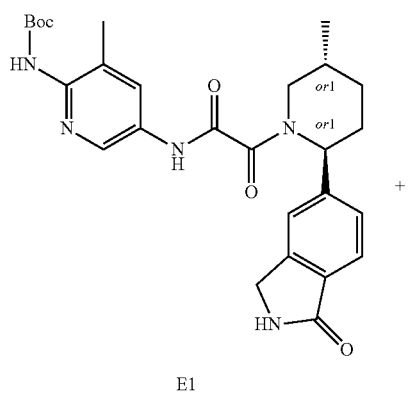

E1

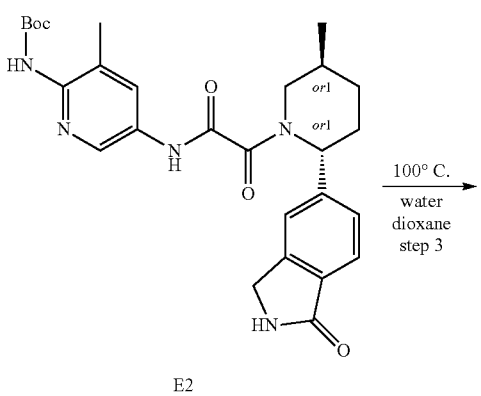

E2

100° C.
water
dioxane
step 3

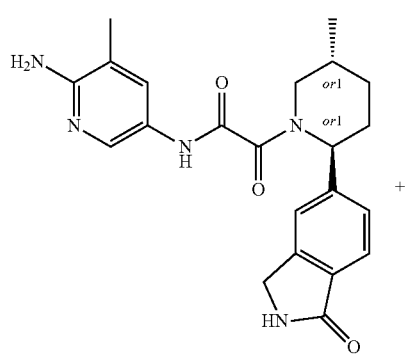

Compound 581

+

2254
-continued

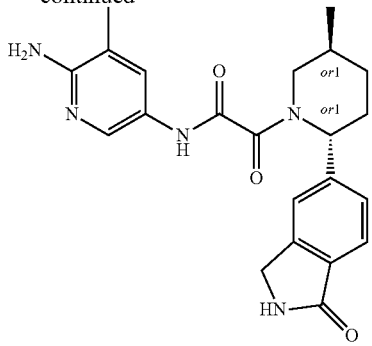

Compound 591

Step 1: Synthesis of rac-tert-butyl (3-methyl-5-(2-((2R,5S)-5-methyl-2-(1-oxoisoindolin-5-yl)piperidin-1-yl)-2-oxoacetamido)pyridin-2-yl)carbamate tert-butyl N-[3-methyl-5-(oxamoylamino)-2-pyridyl]carbamate (511.16 mg, 1.74 mmol) and TEA (1.76 g, 17.37 mmol, 2.42 mL) were dissolved in DMF (12 mL) and cooled to 0° C., HATU (990.59 mg, 2.61 mmol) was added and the mixture was stirred for 15 min at 0° C. 5-[(2R,5S)-5-methyl-2-piperidyl]isoindolin-1-one (0.4 g, 1.74 mmol) was added and the mixture was warmed to rt and stirred for 3 hr. 10 ml of Ethyl acetate was added and organic phase was washed with brine three times. Organic phase was dried over Na$_2$SO$_4$, filtered and concentrated in vacuum at 45° C. to give crude product which was purified by HPLC (90% water-MeOH, 2-10 min, flow: 30 ml/min (loading pump 4 ml/min MeOH) column: TSunFire 100*19 mm, 5 microM) to give tert-butyl N-[3-methyl-5-[[2-[(2R,5S)-5-methyl-2-(1-oxoisoindolin-5-yl)-1-piperidyl]-2-oxo-acetyl]amino]-2-pyridyl]carbamate (0.28 g, 551.64 µmol, 31.76% yield).

LCMS(ESI): [M]$^+$ m/z: calcd 507.2; found 508.2; Rt=1.254 min.

Step 2: Chiral Separation

Chiral separation was performed using Column: Chiralpak IC-1(250*20 mm, 5 mkm); Mobile phase: IPA-MeOH 50-50 Flow Rate: 10 mL/min to give tert-butyl N-[3-methyl-5-[[2-[(2R,5S)-5-methyl-2-(1-oxoisoindolin-5-yl)-1-piperidyl]-2-oxo-acetyl]amino]-2-pyridyl]carbamate (0.068 g, 133.97 µmol, 24.29% yield) and tert-butyl N-[3-methyl-5-[[2-[(2S,5R)-5-methyl-2-(1-oxoisoindolin-5-yl)-1-piperidyl]-2-oxo-acetyl]amino]-2-pyridyl]carbamate (0.089 g, 175.34 µmol, 31.79% yield).

Ret time for E1 in analytical conditions (column: IC, IPA-MeOH, 50-50, 0.6 ml/min as mobile phase) 46.83 min and for E2 22.80 min.

E1: Retention time: 46.83 min
LCMS(ESI): [M]$^+$ m/z: calcd 507.2; found 508.2; Rt=2.851 min.

E2: Retention time: 22.80 min
LCMS(ESI): [M]$^+$ m/z: calcd 507.2; found 508.2; Rt=2.856 min.

Step 3: Synthesis of N-(6-amino-5-methylpyridin-3-yl)-2-(5-methyl-2-(1-oxoisoindolin-5-yl)piperidin-1-yl)-2-oxoacetamide (Compound 581 and Compound 591 tert-butyl N-[3-methyl-5-[[2-[(2R,5S)-5-methyl-2-(1-oxoisoindolin-5-yl)-1-piperidyl]-2-oxo-acetyl]amino]-2- pyridyl]carbamate (0.068 g, 133.97 µmol) and tert-butyl N-[3-methyl-5-[[2-[(2S,5R)-5-methyl-2-(1-oxoisoindolin-5-yl)-1-piperidyl]-2-oxo-acetyl]amino]-2-pyridyl]carbamate (0.089 g, 175.34 µmol) were dissolved in mixture of dioxane (2 mL) and water (2 mL) then stirred at 100° C. for 12 hr. The reaction mixture was concentrated on vacuum at 55° C. to give crude product which was purified by HPLC (0-60% MeCN-water, 2-10 min, flow 30 ml/min (loading pump 4 ml/min MeCN), column: SUNFIRE 100*19 mm) to give N-(6-amino-5-methyl-3-pyridyl)-2-[(2R,5S)-5-methyl-2-(1-oxoisoindolin-5-yl)-1-piperidyl]-2-oxo-acetamide (0.03 g, 73.63 µmol, 54.96% yield) and N-(6-amino-5-methyl-3-pyridyl)-2-[(2S,5R)-5-methyl-2-(1-oxoisoindolin-5-yl)-1-piperidyl]-2-oxo-acetamide (0.034 g, 83.44 µmol, 47.59% yield).

Compound 581: $^1$H NMR (600 MHz, DMSO-d$_6$) δ (ppm) 0.99-1.03 (m, 3H), 1.27-1.36 (m, 1H), 1.61-1.69 (m, 1H), 1.82-1.90 (m, 1H), 1.96-2.03 (m, 3H), 2.05-2.15 (m, 1H), 2.19-2.27 (m, 1H), 2.76-3.24 (m, 1H), 3.33-4.06 (m, 1H), 4.32-4.39 (m, 2H), 5.18-5.60 (m, 1H), 5.60-5.65 (m, 2H), 7.38-7.46 (m, 1H), 7.46-7.56 (m, 2H), 7.61-7.70 (m, 1H), 7.90-8.04 (m, 1H), 8.50 (s, 1H), 10.41-10.54 (m, 1H).

LCMS(ESI): [M]$^+$ m/z: calcd 407.2; found 408.2; Rt=1.669 min.

Compound 591: $^1$H NMR (600 MHz, DMSO-d$_6$) δ (ppm) 0.97-1.04 (m, 3H), 1.27-1.40 (m, 1H), 1.57-1.73 (m, 1H), 1.77-1.94 (m, 1H), 1.94-2.14 (m, 4H), 2.14-2.31 (m, 1H), 2.74-3.26 (m, 1H), 3.47-4.04 (m, 1H), 4.32-4.38 (m, 2H), 5.19-5.59 (m, 1H), 5.60-5.67 (m, 2H), 7.34-7.54 (m, 3H), 7.61-7.71 (m, 1H), 7.87-8.09 (m, 1H), 8.43-8.53 (m, 1H), 10.40-10.53 (m, 1H).

LCMS(ESI): [M]$^+$ m/z: calcd 407.2; found 408.2; Rt=0.921 min.

Example 426. The Synthesis of 4-(1-(2-((6-amino-5-methylpyridin-3-yl)amino)-2-oxoacetyl)-5-methylpiperidin-2-yl)phenyl Acetate (Compound 1087 and Compound 597

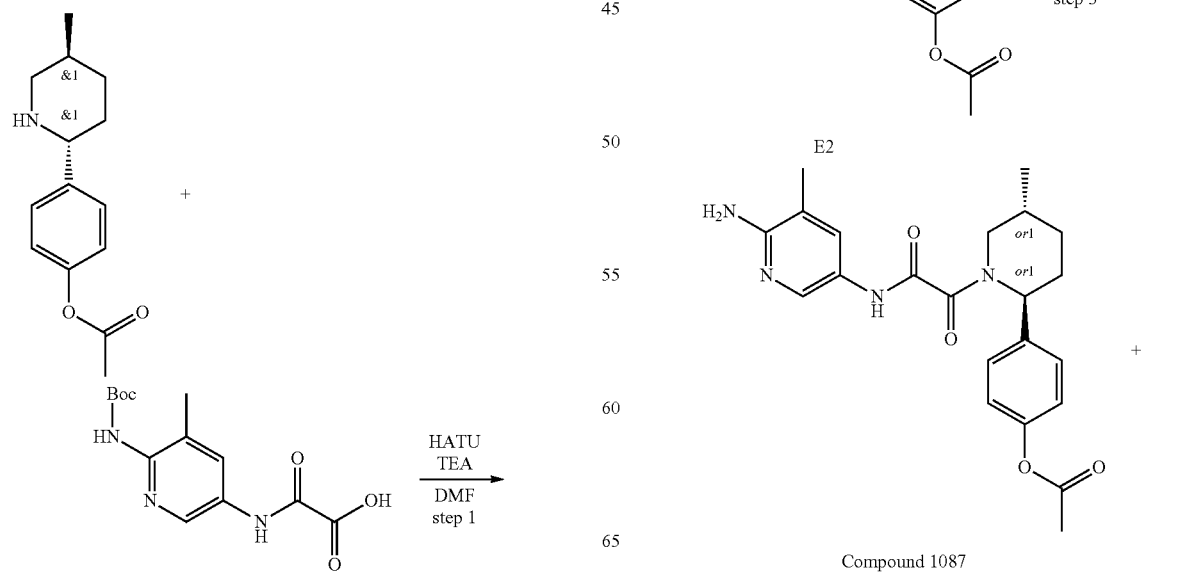

Compound 1087

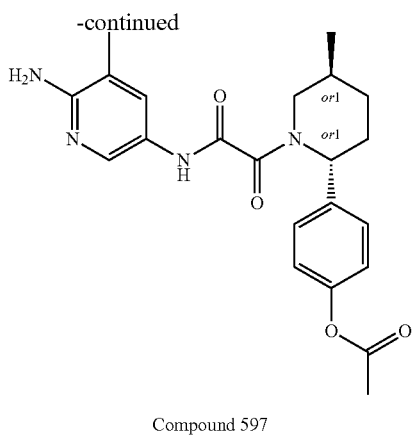

Compound 597

Step 1: Synthesis of rac-4-((2R,5S)-1-(2-(((6-((Tert-butoxycarbonyl)amino)-5-methylpyridin-3-yl)amino)-2-oxoacetyl)-5-methylpiperidin-2-yl)phenyl Acetate tert-butyl N-[3-methyl-5-(oxamoylamino)-2-pyridyl]carbamate (446.56 mg, 1.52 mmol) and TEA (1.54 g, 15.17 mmol, 2.11 mL) were dissolved in DMF (10 mL) and cooled to 0° C., HATU (865.40 mg, 2.28 mmol) was added and the mixture was stirred for 15 min at 0° C. [4-[(2S,5R)-5-methyl-2-piperidyl]phenyl]acetate (0.354 g, 1.52 mmol) was added and the mixture was warmed to rt and stirred for 3 hr. 10 ml of EtOAc was added and organic phase was washed with brine three times. Organic phase was dried over Na$_2$SO$_4$, filtered and concentrated in vacuum at 45° C. to give crude product which was purified by HPLC (55-80% water/MeOH, 2-10 min, (loading pump 4 ml MeOH), column: TRIART 100*20) to give [4-[(2S,5R)-1-[2-[[6-(tert-butoxycarbonylamino)-5-methyl-3-pyridyl]amino]-2-oxo-acetyl]-5-methyl-2-piperidyl]phenyl]acetate (0.177 g, 346.66 µmol, 22.85% yield).

LCMS(ESI): [M]$^+$ m/z: calcd 510.2; found 511.2; Rt=1.238 min.

Step 2: Chiral Separation

Chiral separation was performed using Column: Chiralpak OJ-H-I (250*20, 5 mkm); Mobile phase: Hexane-MeOH-IPA, 60-20-20 Flow Rate: 12 mL/min to give [4-[(2S,5R)-1-[2-[[6-(tert-butoxycarbonylamino)-5-methyl-3-pyridyl]amino]-2-oxo-acetyl]-5-methyl-2-piperidyl]phenyl]acetate (0.048 g, 94.01 µmol, 27.12% yield) and [4-[(2R,5S)-1-[2-[[6-(tert-butoxycarbonylamino)-5-methyl-3-pyridyl]amino]-2-oxo-acetyl]-5-methyl-2-piperidyl]phenyl]acetate (0.047 g, 92.05 µmol, 26.55% yield).

Ret time for E1 in analytical conditions (column: OJ-H, Hexane-IPA-MeOH, 60-20-20, 0.6 ml/min as mobile phase) 14.46 min and for E2 32.46 min.

E1: Retention time: 14.46 min
LCMS(ESI): [M]$^+$ m/z: calcd 510.2; found 511.2; Rt=3.486 min.
E2: Retention time: 32.46 min
LCMS(ESI): [M]$^+$ m/z: calcd 510.2; found 511.2; Rt=3.488 min.

Step 3: Synthesis of 4-(1-(2-((6-amino-5-methylpyridin-3-yl)amino)-2-oxoacetyl)-5-methylpiperidin-2-yl)phenyl Acetate (Compound 1087 and Compound 597

4-[(2S,5R)-1-[2-[[6-(tert-butoxycarbonylamino)-5-methyl-3-pyridyl]amino]-2-oxo-acetyl]-5-methyl-2-piperidyl]phenyl]acetate (0.048 g, 94.01 µmol) and [4-[(2R,5S)-1-[2-[[6-(tert-butoxycarbonylamino)-5-methyl-3-pyridyl]amino]-2-oxo-acetyl]-5-methyl-2-piperidyl]phenyl]acetate (0.047 g, 92.05 µmol) were dissolved in mixture of dioxane (2 mL) and water (2 mL) then stirred at 100° C. for 12 hr. The reaction mixture was concentrated on vacuum at 55° C. to give crude product which was purified by HPLC: 50-60% MeCN-water, 2-10 min, flow 30 ml/min (loading pump 4 ml/min MeCN), column: SUNFIRE 100*19 mm) to give crude product: [4-[(2S,5R)-1-[2-[(6-amino-5-methyl-3-pyridyl)amino]-2-oxo-acetyl]-5-methyl-2-piperidyl]phenyl]acetate (0.009 g, crude) and [4-[(2R,5S)-1-[2-[(6-amino-5-methyl-3-pyridyl)amino]-2-oxo-acetyl]-5-methyl-2-piperidyl]phenyl]acetate (0.014 g, 34.11 µmol, 37.05% yield).

Compound 1087: $^1$H NMR (600 MHz, DMSO-d$_6$) δ (ppm) 0.98-1.03 (m, 3H), 1.28-1.38 (m, 1H), 1.62-1.71 (m, 1H), 1.82-1.93 (m, 1H), 1.96-2.05 (m, 4H), 2.10-2.20 (m, 1H), 2.23-2.26 (m, 3H), 2.67-3.22 (m, 1H), 3.42-4.04 (m, 1H), 5.11-5.57 (m, 1H), 5.57-5.69 (m, 2H), 7.10-7.14 (m, 2H), 7.30-7.39 (m, 2H), 7.43-7.50 (m, 1H), 7.92-8.03 (m, 1H), 10.42-10.55 (m, 1H).

LCMS(ESI): [M]$^+$ m/z: calcd 410.2; found 411.2; Rt=1.104 min.

Compound 597: $^1$H NMR (600 MHz, DMSO-d$_6$) δ (ppm) 0.98-1.03 (m, 3H), 1.28-1.38 (m, 1H), 1.62-1.71 (m, 1H), 1.82-1.93 (m, 1H), 1.96-2.05 (m, 4H), 2.10-2.20 (m, 1H), 2.23-2.26 (m, 3H), 2.67-3.22 (m, 1H), 3.42-4.04 (m, 1H), 5.11-5.57 (m, 1H), 5.57-5.69 (m, 2H), 7.10-7.14 (m, 2H), 7.30-7.39 (m, 2H), 7.43-7.50 (m, 1H), 7.92-8.03 (m, 1H), 10.42-10.55 (m, 1H).

LCMS(ESI): [M]$^+$ m/z: calcd 410.2; found 411.2; Rt=2.323 min.

Example 427. The Synthesis of rel-N-(6-amino-5-methyl-3-pyridyl)-2-[(2S,5R)-5-methyl-2-(4-thiazol-2-ylphenyl)-1-piperidyl]-2-oxo-acetamide (Compound 816) and rel-N-(6-amino-5-methyl-3-pyridyl)-2-[(2R,5S)-5-methyl-2-(4-thiazol-2-ylphenyl)-1-piperidyl]-2-oxo-acetamide (Compound 820

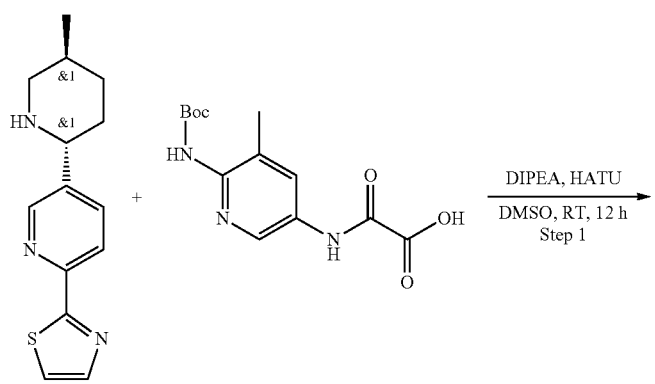

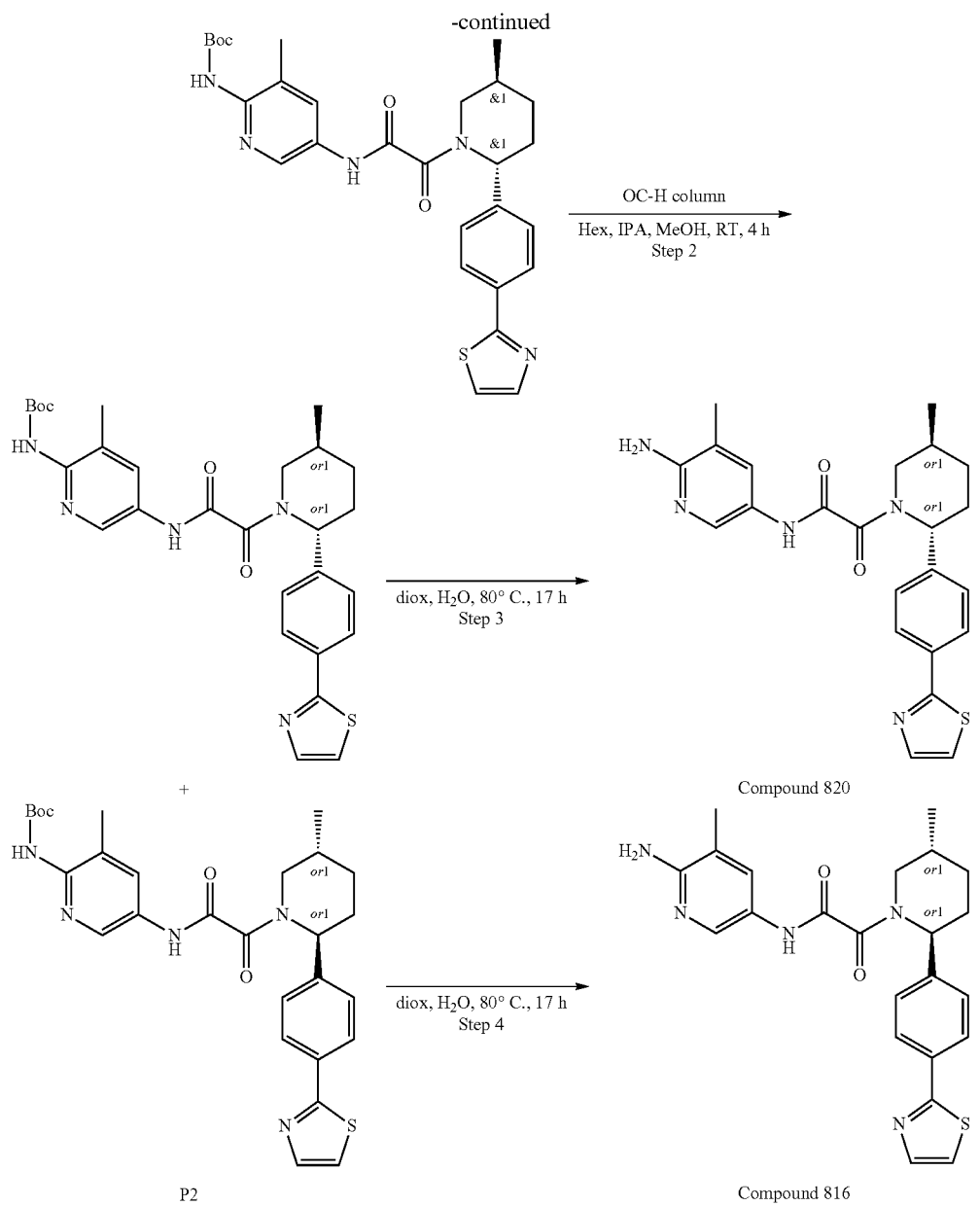

Step 1: The Synthesis of rac-tert-butyl N-[3-methyl-5-[[2-[(2R,5S)-5-methyl-2-(4-thiazol-2-ylphenyl)-1-piperidyl]-2-oxo-acetyl]amino]-2-pyridyl]carbamate To a stirred solution of 2-[4-[(2R,5S)-5-methyl-2-piperidyl]phenyl]thiazole (0.3 g, 1.16 mmol), 2-[[6-(tert-butoxycarbonylamino)-5-methyl-3-pyridyl]amino]-2-oxo-acetic acid (342.85 mg, 1.16 mmol) and DIPEA (300.12 mg, 2.32 mmol, 404.48 μL) in DMSO (7 mL) was added HATU (529.77 mg, 1.39 mmol). The resulting reaction mixture was stirred at 25° C. for 12 hr. Upon completion, the reaction mixture was submitted to reverse phase HPLC to afford rac-tert-butyl N-[3-methyl-5-[[2-[(2R,5S)-5-methyl-2-(4-thiazol-2-ylphenyl)-1-piperidyl]-2-oxo-acetyl]amino]-2-pyridyl]carbamate (0.2 g, 373.37 μmol, 32.16% yield).

HPLC data: 2-10 min 60-90% MeCN/H$_2$O; 30 mL/min (loading pump 4 mL MeCN) column: HILIC, 5 micro LCMS(ESI): [M+H]$^+$ m/z: calcd 535.2; found 536.2; Rt=1.415 min.

Step 2: The Synthesis of rel-tert-butyl N-[3-methyl-5-[[2-[(2R,5S)-5-methyl-2-(4-thiazol-2-ylphenyl)-1-piperidyl]-2-oxo-acetyl]amino]-2-pyridyl]carbamate (P1) and Rel-tert-butyl N-[3-methyl-5-[[2-[(2S,5R)-5-methyl-2-(4-thiazol-2-ylphenyl)-1-piperidyl]-2-oxo-acetyl]amino]-2-pyridyl]carbamate (P2 rac-tert-butyl N-[3-methyl-5-[[2-[(2R,5S)-5-methyl-2-(4-thiazol-2-ylphenyl)-1-piperidyl]-2-oxo-acetyl]amino]-2-pyridyl]carbamate (0.2 g, 373.37 μmol) was submitted to chiral separation to afford P1—rel-tert-butyl N-[3-methyl-5-[[2-[(2R,5S)-5-methyl-2-(4-thiazol-2-ylphenyl)-1-piperidyl]-2-oxo-acetyl]amino]-2-pyridyl]carbamate (0.085 g, 158.68 μmol, 42.50% yield) and P2—rel-tert-butyl N-[3-methyl-5-[[2-[(2S,5R)-5-methyl-2-(4-thiazol-2-ylphenyl)-

1-piperidyl]-2-oxo-acetyl]amino]-2-pyridyl]carbamate (0.072 g, 134.41 μmol, 36.00% yield).

Separation data: Column: Chiralcel OD-H (250*30, 5 mkm), Mobile phase: Hexane-IPA-MeOH, 70-15-15; Flow rate: 28 ml/min. 24° C., Wavelength: 205 nm, 215 nm Retention time P1=13.24; Retention time P2=17.67

P1: RT (OD-H, Hexane-IPA-MeOH, 50-25-25, 0.6 mL/min)=12.231 min.
LCMS(ESI): [M+H]$^+$ m/z: calcd 535.2; found 536.2; Rt=5.623 min.

P2: RT (OD-H, Hexane-IPA-MeOH, 50-25-25, 0.6 mL/min)=9.621 min.
LCMS(ESI): [M+H]$^+$ m/z: calcd 535.2; found 536.2; Rt=5.621 min.

Step 3: The Synthesis of rel-N-(6-amino-5-methyl-3-pyridyl)-2-[(2R,5S)-5-methyl-2-(4-thiazol-2-ylphenyl)-1-piperidyl]-2-oxo-acetamide (Compound 820 rel-tert-butyl N-[3-methyl-5-[[2-[(2R,5S)-5-methyl-2-(4-thiazol-2-ylphenyl)-1-piperidyl]-2-oxo-acetyl]amino]-2-pyridyl]carbamate P1 (0.085 g, 158.68 μmol) was dissolved in a mixture of 1,4-dioxane (2 mL) and water (1 mL) and the mixture was stirred at 80° C. for 17 hr. Upon completion, the reaction mixture was concentrated under reduced pressure and the residue was submitted to reverse phase HPLC to afford rel-N-(6-amino-5-methyl-3-pyridyl)-2-[(2R,5S)-5-methyl-2-(4-thiazol-2-ylphenyl)-1-piperidyl]-2-oxo-acetamide (0.033 g, 75.77 μmol, 47.75% yield).

HPLC data: 50-75% MeOH—2-10 min Flow rate: 30 mL/min; loading pump 4 mL/min MeOH, Column Sun Fire 100×19 mm, 5 mkm $^1$H NMR (dmso, 600 MHz): δ (ppm) 0.98-1.04 (m, 3H), 1.29-1.41 (m, 1H), 1.61-1.73 (m, 1H), 1.80-1.93 (m, 1H), 1.96-2.03 (m, 3H), 2.04-2.18 (m, 1H), 2.18-2.29 (m, 1H), 2.76-3.24 (m, 1H), 3.44-4.06 (m, 1H), 5.17-5.59 (m, 1H), 5.59-5.66 (m, 2H), 7.40-7.47 (m, 2H), 7.47-7.50 (m, 1H), 7.75-7.78 (m, 1H), 7.88-7.91 (m, 1H), 7.91-7.96 (m, 2H), 7.96-8.03 (m, 1H), 10.45-10.55 (m, 1H).

LCMS(ESI): [M+H]$^+$ m/z: calcd 435.2; found 436.2; Rt=1.052 min.

Step 4: The Synthesis of rel-N-(6-amino-5-methyl-3-pyridyl)-2-[(2S,5R)-5-methyl-2-(4-thiazol-2-ylphenyl)-1-piperidyl]-2-oxo-acetamide (Compound 816 rel-tert-butyl N-[3-methyl-5-[[2-[(2S,5R)-5-methyl-2-(4-thiazol-2-ylphenyl)-1-piperidyl]-2-oxo-acetyl]amino]-2-pyridyl]carbamate P2 (0.072 g, 134.41 μmol) was dissolved in a mixture of 1,4-dioxane and water and the mixture was stirred at 80° C. for 17 hr. Upon completion, the reaction mixture was concentrated under reduced pressure and the residue was submitted to reverse phase HPLC to afford rel-N-(6-amino-5-methyl-3-pyridyl)-2-[(2S,5R)-5-methyl-2-(4-thiazol-2-ylphenyl)-1-piperidyl]-2-oxo-acetamide (0.031 g, 71.18 μmol, 52.95% yield).

HPLC data: 50-75% MeOH—2-10 min Flow rate: 30 mL/min; loading pump 4 mL/min MeOH, Column Sun Fire 100×19 mm, 5 mkm $^1$H NMR (dmso, 600 MHz): δ (ppm) 0.97-1.05 (m, 3H), 1.28-1.40 (m, 1H), 1.63-1.71 (m, 1H), 1.82-1.94 (m, 1H), 1.96-2.04 (m, 3H), 2.04-2.17 (m, 1H), 2.19-2.29 (m, 1H), 2.77-3.27 (m, 1H), 3.45-4.06 (m, 1H), 5.18-5.59 (m, 1H), 5.59-5.68 (m, 2H), 7.40-7.47 (m, 2H), 7.47-7.50 (m, 1H), 7.75-7.78 (m, 1H), 7.89-7.91 (m, 1H), 7.92-7.96 (m, 2H), 7.96-8.04 (m, 1H), 10.40-10.64 (m, 1H).

LCMS(ESI): [M+H]$^+$ m/z: calcd 435.2; found 436.2; Rt=1.052 min.

Example 428. The Synthesis of rel-N-(6-amino-5-ethyl-3-pyridyl)-2-[(2R,5S)-5-methyl-2-(4-thiazol-2-ylphenyl)-1-piperidyl]-2-oxo-acetamide (Compound 822) and rel-N-(6-amino-5-ethyl-3-pyridyl)-2-[(2S, 5R)-5-methyl-2-(4-thiazol-2-ylphenyl)-1-piperidyl]-2-oxo-acetamide (Compound 813

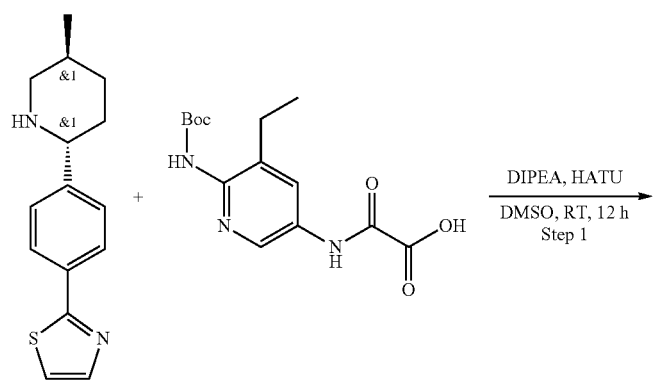

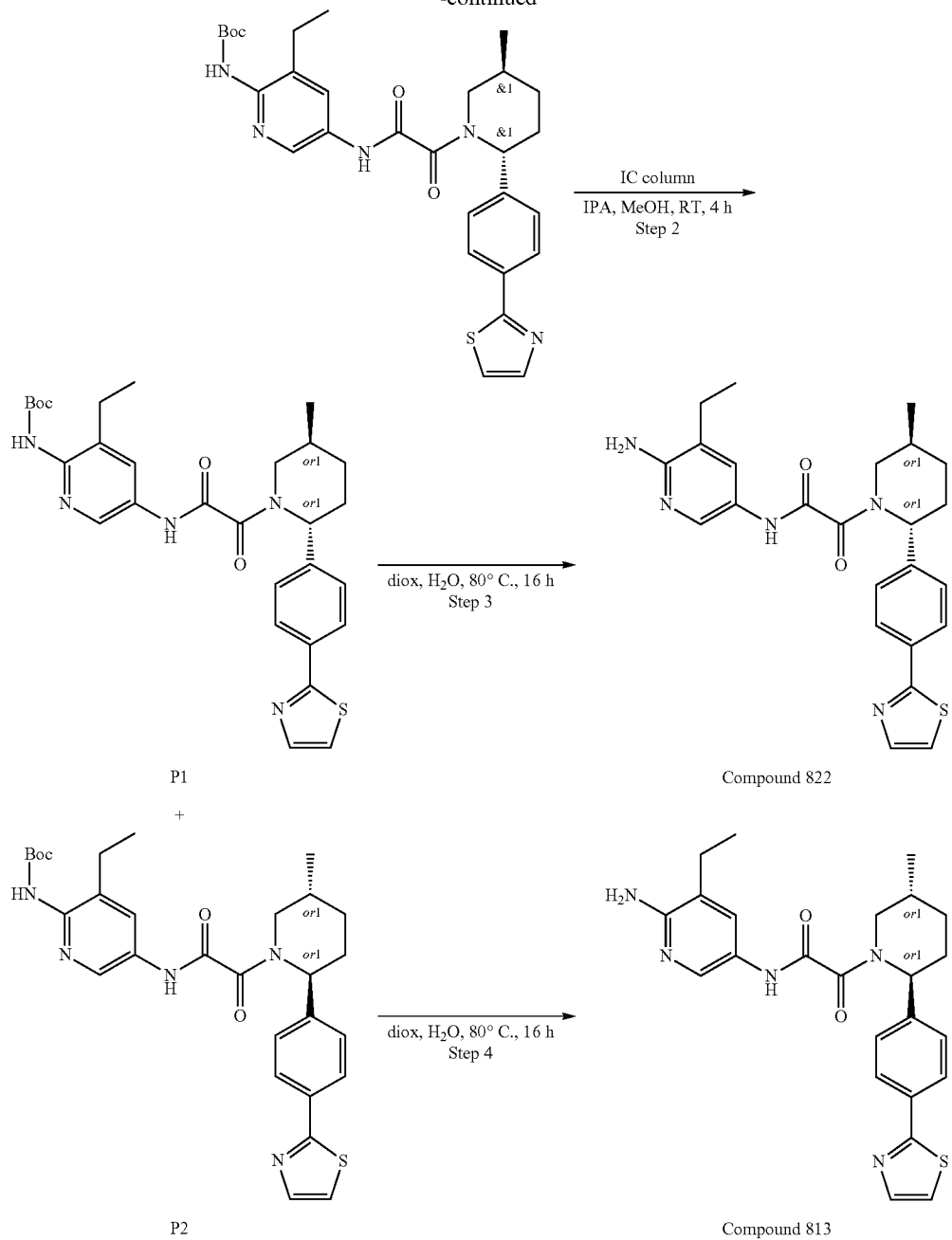

Step 1: The Synthesis of rac-tert-butyl N-[3-ethyl-5-[[2-[(2R,5S)-5-methyl-2-(4-thiazol-2-ylphenyl)-1-piperidyl]-2-oxo-acetyl]amino]-2-pyridyl]carbamate rac-2-[4-[(2R,5S)-5-methyl-2-piperidyl]phenyl]thiazole (0.25 g, 967.56 μmol), 2-[[6-(tert-butoxycarbonylamino)-5-ethyl-3-pyridyl]amino]-2-oxo-acetic acid (299.28 mg, 967.56 μmol), HATU (441.48 mg, 1.16 mmol) and DIPEA (250.10 mg, 1.94 mmol, 337.06 μL) were mixed in DMSO (7 mL) and the reaction mixture was stirred at RT overnight. Upon completion, the reaction mixture was submitted to reverse phase HPLC to afford rac-tert-butyl N-[3-ethyl-5-[[2-[(2R,5S)-5-methyl-2-(4-thiazol-2-ylphenyl)-1-piperidyl]-2-oxo-acetyl]amino]-2-pyridyl]carbamate (0.2 g, 363.85 μmol, 37.60% yield).

HPLC data; 60-95% (MeCN)-2-10 min Flow rate: 30 mL/min; loading pump 4 mL/min MeCN, Column Sun Fire 100×19 mm, 5 mkm LCMS(ESI): [M+H]+ m/z: calcd 459.2; found 550.2; Rt=1.502 min.

Step 2: The Synthesis of rel-tert-butyl N-[3-ethyl-5-[[2-[(2R,5S)-5-methyl-2-(4-thiazol-2-ylphenyl)-1-piperidyl]-2-oxo-acetyl]amino]-2-pyridyl]carbamate (P1) and Rel-tert-butyl N-[3-ethyl-5-[[2-[(2S,5R)-5-methyl-2-(4-thiazol-2-ylphenyl)-1-piperidyl]-2-oxo-acetyl]amino]-2-pyridyl]carbamate (P2 rac-tert-butyl N-[3-ethyl-5-[[2-[(2R,5S)-5-methyl-2-(4-thiazol-2-ylphenyl)-1-piperidyl]-2-oxo-acetyl]amino]-2- pyridyl]carbamate (0.2 g, 363.85 μmol) was submitted to chiral separation to afford rel-tert-butyl N-[3-ethyl-5-[[2-[(2R,5S)-5-methyl-2-(4-thiazol-2-ylphenyl)-1-piperidyl]-2-oxo-acetyl]amino]-2-pyridyl]carbamate P1 (0.067 g, 121.89 μmol, 33.50% yield) and rel-tert-butyl N-[3-ethyl-5-[[2-[(2S,5R)-5-methyl-2-(4-thiazol-2-ylphenyl)-1-piperidyl]-2-oxo-acetyl]amino]-2-pyridyl]carbamate P2 (0.077 g, 140.08 μmol, 38.50% yield). Preparative separation: Sample Info: IC (250*20, 5 mkm), IPA-MeOH, 50-25-25, 10 mL/min P1: RT (IC, IPA-MeOH, 50-50, 0.6 mL/min)=34.861 min. LCMS(ESI): [M+H]⁺ m/z: calcd 549.2; found 550.4; Rt=1.403 min.

P2: RT (IC, IPA-MeOH, 50-50, 0.6 mL/min)=16.318 min. LCMS(ESI): [M+H]⁺ m/z: calcd 549.2; found 550.4; Rt=1.405 min.

Step 3: The Synthesis of rel-N-(6-amino-5-ethyl-3-pyridyl)-2-[(2R,5S)-5-methyl-2-(4-thiazol-2-ylphenyl)-1-piperidyl]-2-oxo-acetamide (Compound 822 rel-tert-butyl N-[3-ethyl-5-[[2-[(2R,5S)-5-methyl-2-(4-thiazol-2-ylphenyl)-1-piperidyl]-2-oxo-acetyl]amino]-2-pyridyl]carbamate P1 (0.067 g, 121.89 μmol) was dissolved in a mixture of 1,4-dioxane (2 mL) and water (1 mL) and the mixture was stirred at 80° C. for 16 hr. Upon completion, the reaction mixture was concentrated under reduced pressure and the residue was submitted to reverse phase HPLC to afford N-(6-amino-5-ethyl-3-pyridyl)-2-[(2R,5S)-5-methyl-2-(4-thiazol-2-ylphenyl)-1-piperidyl]-2-oxo-acetamide (0.0335 g, 74.52 μmol, 61.13% yield).

HPLC data: 50-75% MeOH—2-10 min Flow rate: 30 mL/min; loading pump 4 mL/min MeOH, Column Sun Fire 100×19 mm, 5 mkm ¹H NMR (dmso, 600 MHz): δ (ppm) 0.99-1.04 (m, 3H), 1.04-1.13 (m, 3H), 1.30-1.40 (m, 1H), 1.62-1.71 (m, 1H), 1.82-1.96 (m, 1H), 2.01-2.17 (m, 1H), 2.18-2.30 (m, 1H), 2.36-2.43 (m, 2H), 2.73-3.24 (m, 1H), 3.39-4.09 (m, 1H), 5.17-5.60 (m, 1H), 5.60-5.67 (m, 2H), 7.40-7.47 (m, 2H), 7.47-7.51 (m, 1H), 7.76-7.78 (m, 1H), 7.89-7.92 (m, 1H), 7.92-7.97 (m, 2H), 7.98-8.07 (m, 1H), 10.45-10.59 (m, 1H).

LCMS(ESI): [M+H]⁺ m/z: calcd 449.2; found 450.4; Rt=2.493 min.

Step 4: The Synthesis of rel-N-(6-amino-5-ethyl-3-pyridyl)-2-[(2S,5R)-5-methyl-2-(4-thiazol-2-ylphenyl)-1-piperidyl]-2-oxo-acetamide (Compound 813 rel-tert-butyl N-[3-ethyl-5-[[2-[(2S,5R)-5-methyl-2-(4-thiazol-2-ylphenyl)-1-piperidyl]-2-oxo-acetyl]amino]-2-pyridyl]carbamate P2 (0.077 g, 140.08 μmol) was dissolved in a mixture of 1,4-dioxane (2 mL) water (1 mL)80° C. and water (1 mL) and the mixture was stirred at 80° C. for 16 hr. Upon completion, the reaction mixture was concentrated under reduced pressure and the residue was submitted to reverse phase HPLC to afford rel-N-(6-amino-5-ethyl-3-pyridyl)-2-[(2S,5R)-5-methyl-2-(4-thiazol-2-ylphenyl)-1-piperidyl]-2-oxo-acetamide (0.0364 g, 80.97 μmol, 57.80% yield).

HPLC data: 50-75% MeOH—2-10 min Flow rate: 30 mL/min; loading pump 4 mL/min MeOH, Column Sun Fire 100×19 mm, 5 mkm ¹H NMR (dmso, 600 MHz): δ (ppm) 1.00-1.04 (m, 3H), 1.04-1.15 (m, 3H), 1.29-1.40 (m, 1H), 1.60-1.75 (m, 1H), 1.82-1.94 (m, 1H), 2.03-2.16 (m, 1H), 2.19-2.29 (m, 1H), 2.36-2.43 (m, 2H), 2.72-3.24 (m, 1H), 3.46-4.08 (m, 1H), 5.18-5.60 (m, 1H), 5.60-5.68 (m, 2H), 7.40-7.47 (m, 2H), 7.47-7.51 (m, 1H), 7.75-7.78 (m, 1H), 7.88-7.92 (m, 1H), 7.92-7.97 (m, 2H), 7.98-8.08 (m, 1H), 10.52 (s, 1H).

LCMS(ESI): [M+H]⁺ m/z: calcd 449.2; found 450.4; Rt=min.

Example 429. The Synthesis of N-(6-amino-5-methyl-3-pyridyl)-2-[(2R,5S)-5-methyl-2-(5-methyl-2-pyridyl)-1-piperidyl]-2-oxo-acetamide (Compound 1005) and N-(6-amino-5-methyl-3-pyridyl)-2-[(2R,5R)-5-methyl-2-(5-methyl-2-pyridyl)-1-piperidyl]-2-oxo-acetamide (Compound 982

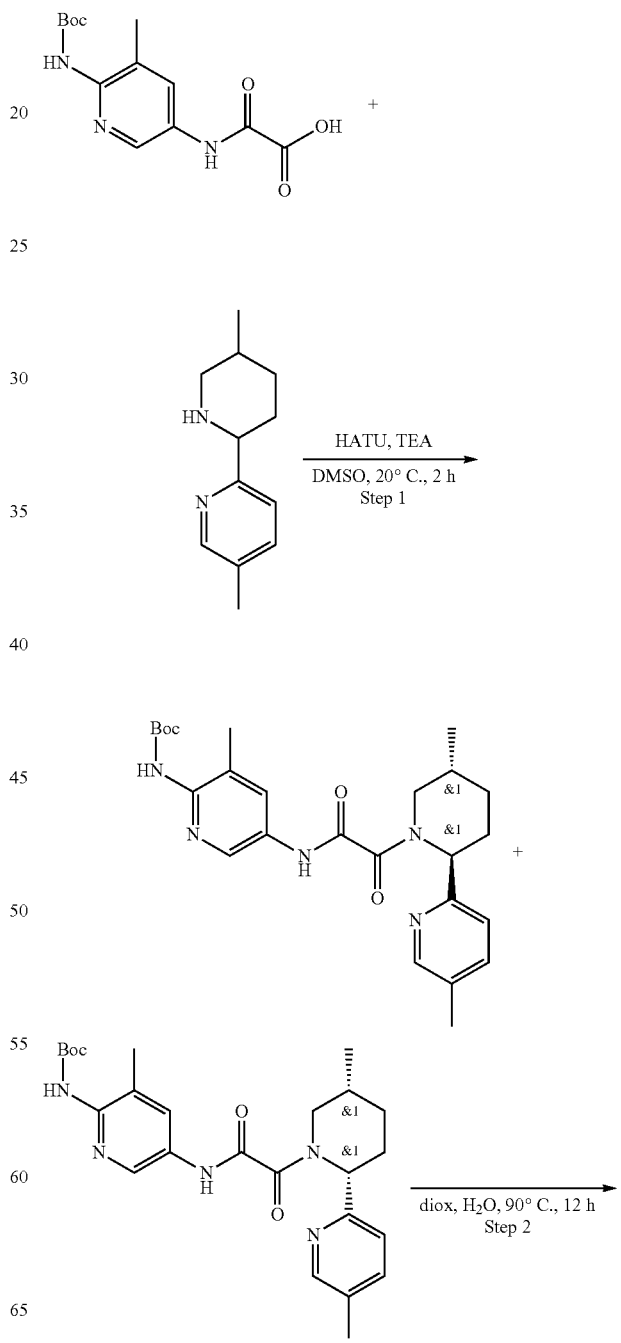

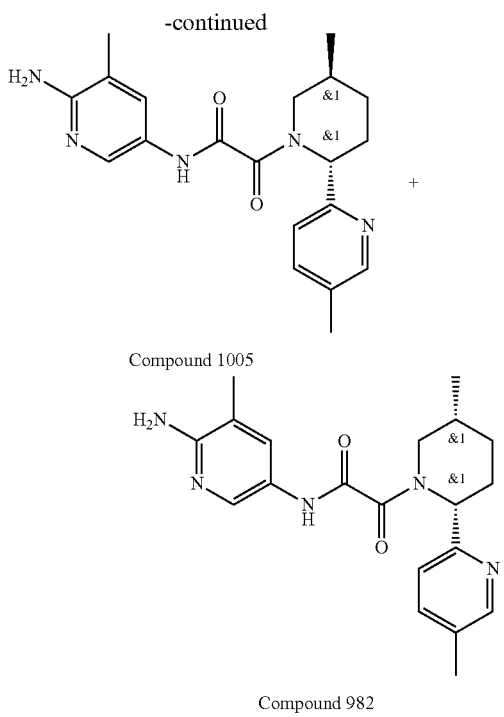

Compound 1005

Compound 982

Step 1: The Synthesis of tert-butyl N-[3-methy-5-[[2-[(2S,5R)-5-methyl-2-(5-methyl-2-pyridyl)-1-piperidyl]-2-oxo-acetyl]amino]-2-pyridyl]carbamate and Tert-butyl N-[3-methyl-5-[[2-[(2R,5R)-5-methyl-2-(5-methyl-2-pyridyl)-1-piperidyl]-2-oxo-acetyl]amino]-2-pyridyl]carbamate 2-[[6-(tert-butoxycarbonylamino)-5-methyl-3-pyridyl]amino]-2-oxo-acetic acid (625.09 mg, 1.58 mmol, $N(C_2H_5)_3$), 5-methyl-2-(5-methyl-2-piperidyl)pyridine (300 mg, 1.58 mmol), HATU (659.41 mg, 1.73 mmol) and TEA (175.49 mg, 1.73 mmol, 241.72 μL) were mixed in DMSO (4 mL) and stirred for 2 hr at 20° C. Reaction mixture was subjected to HPLC.

HPLC data: 2-10 min 20-45% MeCN/H$_2$O 30 mL/min (loading pump 4 mL MeCN) column: SunFire 100*19 mm, 5 microM tert-butyl N-[3-methyl-5-[[2-[(2S,5R)-5-methyl-2-(5-methyl-2-pyridyl)-1-piperidyl]-2-oxo-acetyl]amino]-2-pyridyl]carbamate (90 mg, crude) was obtained.

tert-butyl N-[3-methyl-5-[[2-[(2R,5R)-5-methyl-2-(5-methyl-2-pyridyl)-1-piperidyl]-2-oxo-acetyl]amino]-2-pyridyl]carbamate (367 mg, 784.93 μmol, 49.79% yield) was obtained (mainly cis)

LCMS(ESI): [M+2H]$^+$ m/z: calcd 467.2; found 469.2; Rt=3.031 min.

Step 2: The Synthesis of N-(6-amino-5-methyl-3-pyridyl)-2-[(2R,5S)-5-methyl-2-(5-methyl-2-pyridyl)-1-piperidyl]-2-oxo-acetamide (Compound 1005) and N-(6-amino-5-methyl-3-pyridyl)-2-[(2R,5R)-5-methyl-2-(5-methyl-2-pyridyl)-1-piperidyl]-2-oxo-acetamide (Compound 982 tert-butyl N-[3-methyl-5-[[2-[(2R,5S)-5-methyl-2-(5-methyl-2-pyridyl)-1-piperidyl]-2-oxo-acetyl]amino]-2-pyridyl]carbamate (90 mg, 192.49 μmol) was dissolved in dioxane (1.5 mL) and water (0.5 mL) and stirred overnight at 90° C. Reaction mixture was subjected to HPLC.

HPLC data: 2-10 min 10-50% MeCN+TFA, 30 mL/min (loading pump 4 mL MeCN) column: SunFire 100*19 mm, 5 microM N-(6-amino-5-methyl-3-pyridyl)-2-[(2R,5S)-5-methyl-2-(5-methyl-2-pyridyl)-1-piperidyl]-2-oxo-acetamide (17.3 mg, 47.08 μmol, 24.46% yield) was obtained.

Compound 1005: $^1$H NMR (600 MHz, DMSO-d$_6$) δ 0.97-1.04 (m, 3H), 1.26-1.35 (m, 1H), 1.56-1.66 (m, 1H), 1.78-1.88 (m, 1H), 1.88-1.96 (m, 1H), 1.97-2.04 (m, 3H), 2.24-2.29 (m, 3H), 2.40-2.43 (m, 1H), 2.77-2.97 (m, 1H), 3.52-4.07 (m, 1H), 5.13-5.54 (m, 1H), 5.55-5.63 (m, 2H), 7.15-7.34 (m, 1H), 7.40-7.49 (m, 1H), 7.58-7.64 (m, 1H), 7.93-8.03 (m, 1H), 8.36-8.42 (m, 1H), 10.32-10.54 (m, 1H).

LCMS(ESI): [M+H]$^+$ m/z: calcd 367.2; found 368.2; Rt=1.730 min.

Compound 982: $^1$H NMR (600 MHz, DMSO-d$_6$) δ 0.67-0.81 (m, 3H), 0.96-1.06 (m, 1H), 1.54-1.70 (m, 2H), 1.72-1.90 (m, 1H), 1.99-2.07 (m, 3H), 2.24-2.29 (m, 3H), 2.59-2.72 (m, 2H), 3.61-4.25 (m, 1H), 5.14-5.61 (m, 1H), 5.67-6.29 (m, 2H), 7.16-7.31 (m, 1H), 7.48-7.58 (m, 1H), 7.59-7.64 (m, 1H), 7.97-8.09 (m, 1H), 8.36-8.42 (m, 1H), 10.49-10.75 (m, 1H).

LCMS(ESI): [M+H]$^+$ m/z: calcd 367.2; found 368.2; Rt=1.846 min.

Example 430. The Synthesis of N-(6-amino-5-methylpyridin-3-yl)-2-(2-(3-chlorophenyl)-4,4-difluoro-5-methylpiperidin-1-yl)-2-oxoacetamide (Compound 1074 and Compound 1045

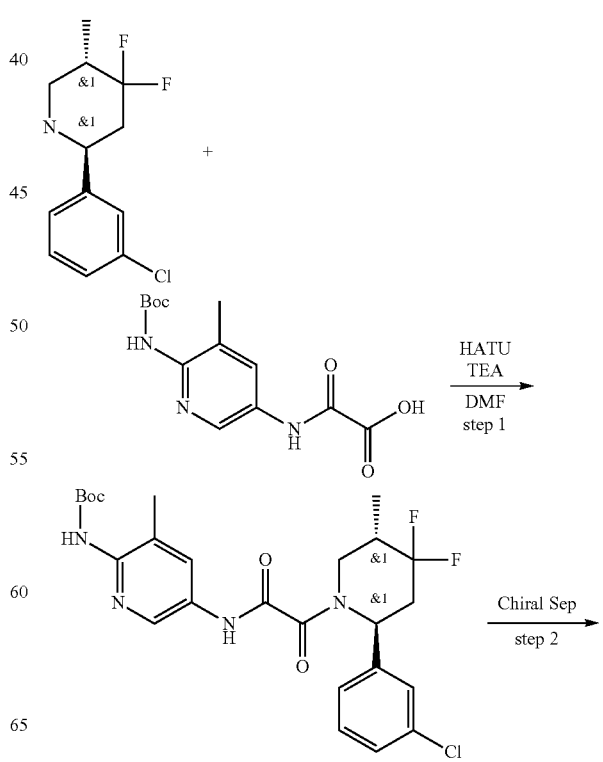

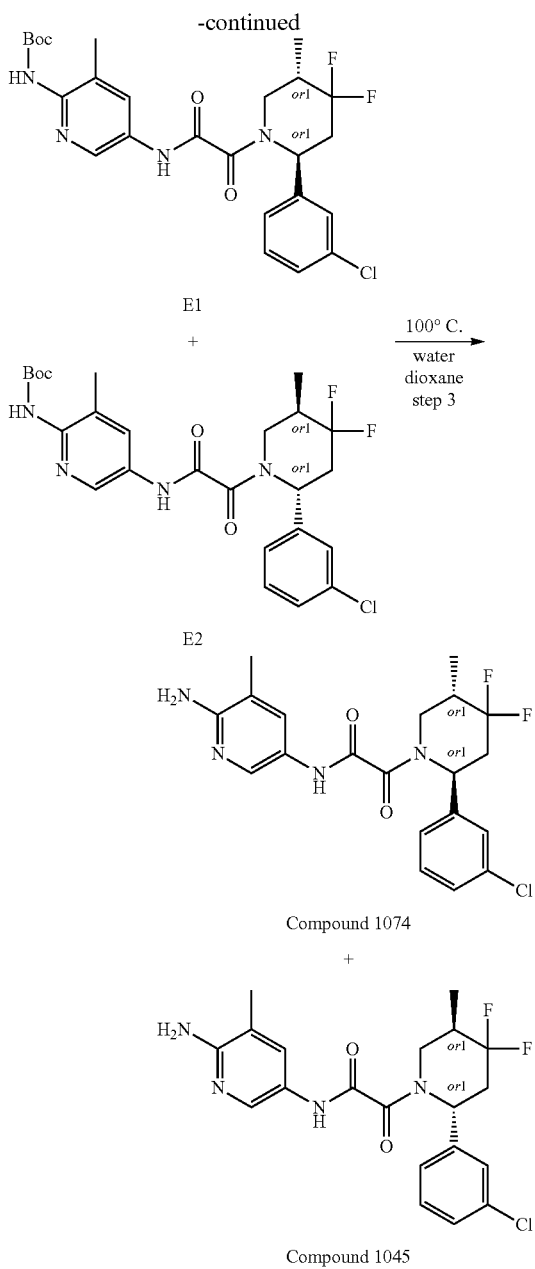

E1

+

E2

→ 100° C.
water
dioxane
step 3

Compound 1074

+

Compound 1045

Step 1: Synthesis of rac-tert-butyl (5-(2-((2S,5R)-2-(3-chlorophenyl)-4,4-difluoro-5-methylpiperidin-1-yl)-2-oxoacetamido)-3-methylpyridin-2-yl)carbamate (2R,5R)-2-(3-chlorophenyl)-4,4-difluoro-5-methyl-piperidine (300 mg, 1.22 mmol), 2-[[6-(tert-butoxycarbonylamino)-5-methyl-3-pyridyl]amino]-2-oxo-acetic acid (360.56 mg, 1.22 mmol), TEA (370.67 mg, 3.66 mmol, 510.56 µL) were mixed in DMF (6 mL) and then HATU (696.40 mg, 1.83 mmol) were added. Resulting mixture were stirred at 25° C. for 12 hr. The solvent was evaporated and the crude precipitate was purified by HPLC (45-90% 2-10 min; water-MeOH 30 ml/min; loading pump MeOH 4 ml/min, target mass 511, column SunFire 19*100 mm 5 um) to obtain tert-butyl N-[5-[[2-[(2R,5R)-2-(3-chlorophenyl)-4,4-difluoro-5-methyl-1-piperidyl]-2-oxo-acetyl]amino]-3-methyl-2-pyridyl]carbamate (102.8 mg, 196.57 µmol, 16.10% yield).

LCMS(ESI): [M]+ m/z: calcd 522.2; found 523.2; Rt=1.372 min.

Step 2: Chiral Separation

The mixture of diastereomers was separated by chiral chromatography (IA-II(250*20.5 mkm), IPA-MeOH, 50-50, 12 ml/min) to obtain tert-butyl N-[5-[[2-[(2S,5R)-2-(3-chlorophenyl)-4,4-difluoro-5-methyl-1-piperidyl]-2-oxo-acetyl]amino]-3-methyl-2-pyridyl]carbamate E1 (33.06 mg, 63.22 µmol, 31.55% yield) with RT=15.17 min and tert-butyl N-[5-[[2-[(2R,5S)-2-(3-chlorophenyl)-4,4-difluoro-5-methyl-1-piperidyl]-2-oxo-acetyl]amino]-3-methyl-2-pyridyl]carbamate E2 (38.78 mg, 74.15 µmol, 37.72% yield) with RT=21.89 min. Ret time for E1 in analytical conditions (column: IC, Hexane-IPA-MeOH, 70-15-15, 0.6 ml/min as mobile phase) 15.08 min and for E2 23.16 min.

E1:Retention time: 15.08 min

LCMS(ESI): [M]+ m/z: calcd 522.2; found 523.2; Rt=3.820 min.

E2: Retention time: 23.16 min

LCMS(ESI): [M]+ m/z: calcd 522.2; found 523.2; Rt=3.818 min.

Step 3: Synthesis of N-(6-amino-5-methylpyridin-3-yl)-2-(2-(3-chlorophenyl)-4,4-difluoro-5-methylpiperidin-1-yl)-2-oxoacetamide (Compound 1074 and Compound 1045

Solutions of tert-butyl N-[5-[[2-[(2S,5R)-2-(3-chlorophenyl)-4,4-difluoro-5-methyl-1-piperidyl]-2-oxo-acetyl]amino]-3-methyl-2-pyridyl]carbamate E1 (33.06 mg, 63.22 µmol) and tert-butyl N-[5-[[2-[(2R,5S)-2-(3-chlorophenyl)-4,4-difluoro-5-methyl-1-piperidyl]-2-oxo-acetyl]amino]-3-methyl-2-pyridyl]carbamate E2 (38.78 mg, 74.15 µmol) in water (2 mL) and dioxane (2 mL) were heated at 100° C. for 12 hr. Solvents were evaporated and resulting precipitate was purified by HPLC (2-10 min 55-65% MeOH 30 ml/min, loading pump 4 ml/minMeOH, target mass 422, column: SunFire 100*19 mm, 5 microM) to obtain N-(6-amino-5-methyl-3-pyridyl)-2-[(2S,5R)-2-(3-chlorophenyl)-4,4-difluoro-5-methyl-1-piperidyl]-2-oxo-acetamide (19.4 mg, 45.88 µmol, 72.57% yield) and N-(6-amino-5-methyl-3-pyridyl)-2-[(2R,5S)-2-(3-chlorophenyl)-4,4-difluoro-5-methyl-1-piperidyl]-2-oxo-acetamide (22.7 mg, 53.68 µmol, 72.39% yield).

Compound 1074: $^1$H NMR (600 MHz, DMSO-$d_6$) δ (ppm) 1.08 (d, 3H), 2.05 (s, 3H), 2.20 (m, 1H), 2.45 (m, 1H), 2.87 (m, 1H), 3.42 (m, 1H), 4.02 (m, 1H), 5.62 (m, 1H), 5.82 (m, 2H), 7.37 (m, 4H), 7.52 (m, 1H), 8.05 (m, 1H), 10.67 (m, 1H).

LCMS(ESI): [M]+ m/z: calcd 422.2; found 423.2; Rt=1.127 min.

Compound 1045: $^1$H NMR (600 MHz, DMSO-$d_6$) δ (ppm) 1.08 (d, 3H), 2.05 (s, 3H), 2.22 (m, 1H), 2.42 (m, 1H), 2.87 (m, 1H), 3.44 (m, 1H), 4.02 (m, 1H), 5.62 (m, 1H), 5.82 (m, 2H), 7.37 (m, 4H), 7.52 (m, 1H), 8.05 (m, 1H), 10.67 (m, 1H).

LCMS(ESI): [M]+ m/z: calcd 422.2; found 423.2; Rt=1.127 min.

Example 431. The Synthesis of N-(6-amino-5-methyl-3-pyridyl)-2-[(2R,5S)-5-methyl-2-(2-methyl-4-pyridyl)-1-piperidyl]-2-oxo-acetamide (Compound 593) and N-(6-amino-5-methyl-3-pyridyl)-2-[(2S,5R)-5-methyl-2-(2-methyl-4-pyridyl)-1-piperidyl]-2-oxo-acetamide (Compound 608 dine (193.32 mg, 1.02 mmol) in DMF (5 mL). The resulting mixture was stirred for 5 min followed by the addition of HATU (424.92 mg, 1.12 mmol). Then, the reaction mixture was stirred overnight at room temperature. After the completion of the reaction, monitored by LCMS, the resulting suspension was concentrated under reduced pressure. The obtained solid was subjected to HPLC (Waters Sunfire C18

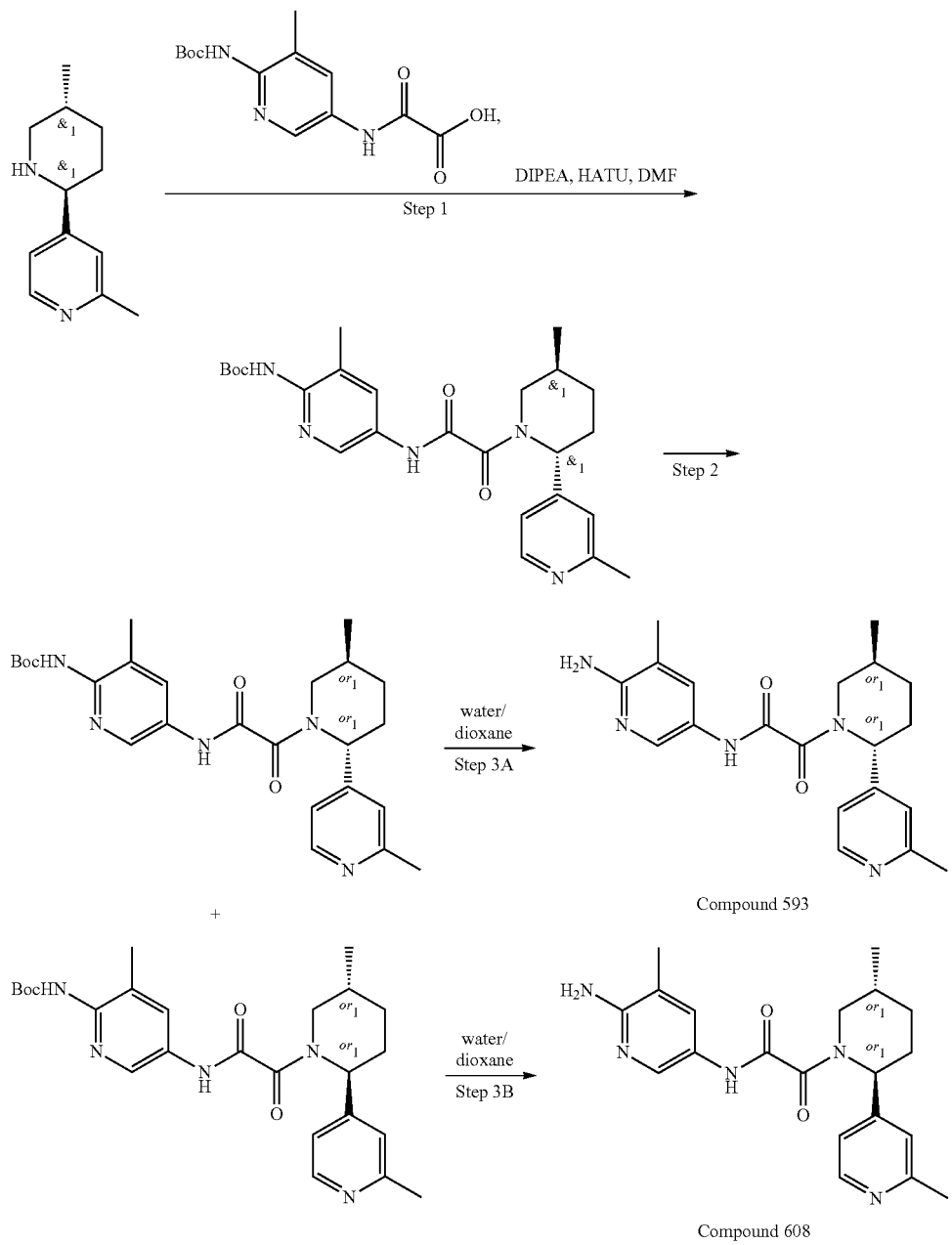

Step 1. The Synthesis of rac-tert-butyl N-[3-methy-5-[[2-[(2S,5R)-5-methyl-2-(2-methyl-4-pyridyl)-1-piperidyl]-2-oxo-acetyl]amino]-2-pyridyl]carbamate DIPEA (525.22 mg, 4.06 mmol, 707.84 μL) was added to the solution of respective 2-[[6-(tert-butoxycarbonylamino)-5-methyl-3-pyridyl]amino]-2-oxo-acetic acid (0.3 g, 1.02 mmol) and 2-methyl-4-[(2R,5S)-5-methyl-2-piperidyl]pyri- 19*100 5 mkm column and H$_2$O-MeCN as an eluent mixture) to afford pure tert-butyl N-[3-methyl-5-[[2-[(2S,5R)-5-methyl-2-(2-methyl-4-pyridyl)-1-piperidyl]-2-oxo-acetyl]amino]-2-pyridyl]carbamate (0.24 g, 513.30 μmol, 50.52% yield).

LCMS(ESI): [M+H]$^+$ m/z: calcd 467.2; found 468.2; Rt=1.845 min.

Step 2. The Synthesis of tert-butyl N-[3-methyl-5-[[2-[(2S,5R)-5-methyl-2-(2-methyl-4-pyridyl)-1-piperidyl]-2-oxo-acetyl]amino]-2-pyridyl]carbamate and Tert-butyl N-[3-methy-5-[[2-[(2R,5S)-5-methyl-2-(2-methyl-4-pyridyl)-1-piperidyl]-2-oxo-acetyl]amino]-2-pyridyl]carbamate Enantiomers were separated in the following condition—Column: Chiral ART Cellulose-SC (250*20, 5 mkm); Mobile phase: Hexane-IPA-MeOH, 50-25-25, Flow Rate: 12 mL/min; Column Temperature: 24° C.; Wavelength: 205 nm, 256 nm, 290 nm), RetTime (isomer cis)=21.53; RetTime (isomers trans)=23.03 min; RetTime (isomers cis)=31.75 min; RetTime (isomer trans)=39.93 min Analytical data: Instrument: Reverse Phase & Gradient: $CO_2$-MeOH, 60-40, 2 ml/min, Column:IC, Rel.Time for trans isomer 1=11.60 min; trans isomer 2=23.98 min;

Step 3A. The Synthesis of N-(6-amino-5-methyl-3-pyridyl)-2-[(2R,5S)-5-methyl-2-(2-methyl-4-pyridyl)-1-piperidyl]-2-oxo-acetamide (Compound 593 tert-butyl N-[3-methyl-5-[[2-[(2R,5S)-5-methyl-2-(2-methyl-4-pyridyl)-1-piperidyl]-2-oxo-acetyl]amino]-2-pyridyl]carbamate (103.22 mg, 220.76 µmol, isomer 2) was dissolved in dioxane (2 mL) and water (5 mL) mixture. Then reaction mixture was stirred for 17 hr at 100° C. After the completion of the reaction, monitored by LCMS, the resulting suspension was concentrated under reduced pressure. The obtained solid was subjected to HPLC (Waters Sunfire C18 20*100 5 mkm column and $H_2O$-MeOH (50-60%) as an eluent mixture) to afford pure N-(6-amino-5-methyl-3-pyridyl)-2-[(2R,5S)-5-methyl-2-(2-methyl-4-pyridyl)-1-piperidyl]-2-oxo-acetamide (48.6 mg, 132.27 µmol, 59.91% yield).

$^1$H NMR (600 MHz, DMSO-$d_6$) δ 0.94-1.03 (m, 3H), 1.26-1.39 (m, 1H), 1.50-1.63 (m, 1H), 1.80-1.92 (m, 1H), 1.97-2.03 (m, 3H), 2.03-2.13 (m, 1H), 2.13-2.23 (m, 1H), 2.49-2.53 (m, 3H), 2.71-3.18 (m, 1H), 3.45-4.08 (m, 1H), 5.08-5.53 (m, 1H), 5.54-5.67 (m, 2H), 7.04-7.13 (m, 1H), 7.13-7.22 (m, 1H), 7.37-7.53 (m, 1H), 7.91-8.06 (m, 1H), 8.35-8.46 (m, 1H), 10.46-10.61 (m, 1H).

LCMS(ESI): [M+H]$^+$ m/z: calcd 367.2; found 368.4; Rt=1.035 min.

Step 3B. The Synthesis of N-(6-amino-5-methyl-3-pyridyl)-2-[(2S,5R)-5-methyl-2-(2-methyl-4-pyridyl)-1-piperidyl]-2-oxo-acetamide (Compound 608 tert-butyl N-[3-methyl-5-[[2-[(2S,5R)-5-methyl-2-(2-methyl-4-pyridyl)-1-piperidyl]-2-oxo-acetyl]amino]-2-pyridyl]carbamate (88.45 mg, 189.17 µmol, isomer 1) was dissolved in dioxane (2 mL) and water (5 mL) mixture. Then reaction mixture was stirred for 17 hr at 100° C. After the completion of the reaction, monitored by LCMS, the resulting suspension was concentrated under reduced pressure. The obtained solid was subjected to HPLC (Waters Sunfire C18 20*100 5 mkm column and $H_2O$-MeOH (50-60%) as an eluent mixture) to afford pure N-(6-amino-5-methyl-3-pyridyl)-2-[(2S,5R)-5-methyl-2-(2-methyl-4-pyridyl)-1-piperidyl]-2-oxo-acetamide (50.6 mg, 137.71 µmol, 72.79% yield)

$^1$H NMR (600 MHz, DMSO-$d_6$) δ 0.94-1.03 (m, 3H), 1.26-1.39 (m, 1H), 1.50-1.63 (m, 1H), 1.80-1.92 (m, 1H), 1.97-2.03 (m, 3H), 2.03-2.13 (m, 1H), 2.13-2.23 (m, 1H), 2.49-2.53 (m, 3H), 2.71-3.18 (m, 1H), 3.45-4.08 (m, 1H), 5.08-5.53 (m, 1H), 5.54-5.67 (m, 2H), 7.04-7.13 (m, 1H), 7.13-7.22 (m, 1H), 7.37-7.53 (m, 1H), 7.91-8.06 (m, 1H), 8.35-8.46 (m, 1H), 10.46-10.61 (m, 1H).

LCMS(ESI): [M+H]$^+$ m/z: calcd 367.2; found 368.4; Rt=1.035 min.

Example 432. The Synthesis of N-(6-amino-5-methylpyridin-3-yl)-2-(5-methyl-2-(pyridin-4-yl) piperidin-1-yl)-2-oxoacetamide (Compound 609 and Compound 592

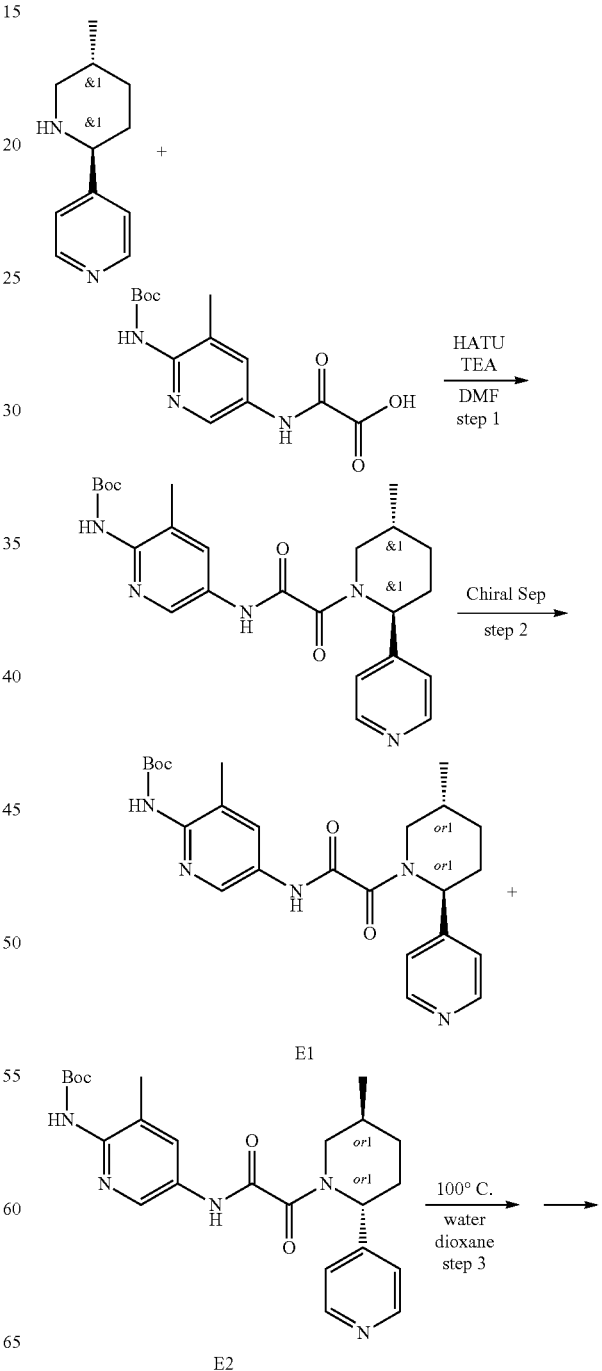

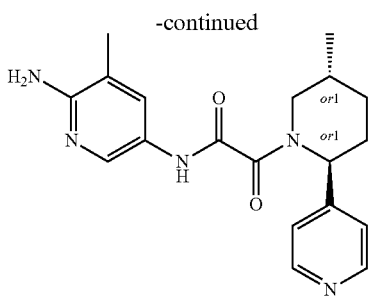

Compound 592

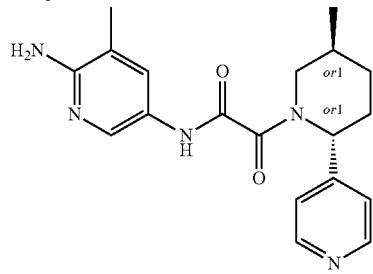

Compound 609

Step 1: Synthesis of rac-tert-butyl (3-methyl-5-(2-((2R,5S)-5-methyl-2-(pyridin-4-yl)piperidin-1-yl)-2-oxoacetamido)pyridin-2-yl)carbamate DIPEA (525.22 mg, 4.06 mmol, 707.84 µL) was added to the solution of respective 2-[[6-(tert-butoxycarbonylamino)-5-methyl-3-pyridyl]amino]-2-oxo-acetic acid (0.3 g, 1.02 mmol) and 4-[(2S,5R)-5-methyl-2-piperidyl]pyridine (179.07 mg, 1.02 mmol) in DMF (5 mL). The resulting mixture was stirred for 5 min followed by the addition of HATU (424.92 mg, 1.12 mmol). Then, the reaction mixture was stirred overnight at rt. After the completion of the reaction, monitored by LCMS, the resulting suspension was concentrated under reduced pressure. The obtained solid was subjected to HPLC (column: Triart 100*20*5 mm, water-MeOH as an eluent mixture) to afford pure tert-butyl N-[3-methyl-5-[[2-[(2S,5R)-5-methyl-2-(4-pyridyl)-1-piperidyl]-2-oxo-acetyl]amino]-2-pyridyl]carbamate (0.24 g, 529.18 µmol, 52.09% yield).

$^1$H NMR (400 MHz, DMSO-$d_{66}$) (ppm) 0.98 (d, 3H), 1.32 (m, 1H), 1.42 (s, 9H), 1.58 (m, 1H), 1.88 (m, 1H), 2.12 (m, 1H), 2.24 (s, 3H), 3.22 (m, 1H), 3.51 (m, 1H), 4.08 (m, 1H), 5.48 (m, 1H), 7.32 (d, 2H), 7.92 (m, 1H), 8.41 (m, 1H), 8.56 (d, 2H), 9.04 (m, 1H), 11.11 (m, 1H).

LCMS(ESI): [M]$^+$ m/z: calcd 453.2; found 454.2; Rt=1.889 min.

Step 2: Chiral Separation

The rac-tert-butyl (3-methyl-5-(2-((2R,5S)-5-methyl-2-(pyridin-4-yl)piperidin-1-yl)-2-oxoacetamido)pyridin-2-yl)carbamate (240.00 mg, 529.18 µmol) was subjected to chiral HPLC purification (Column: ID-H-III (250*20.5 mkm), Eluent: Hexane-IPA-MeOH, 60-20-20, flow rate: 12 mL/min) to give the two individual enantiomers E1 tert-butyl N-[3-methyl-5-[[2-[(2S,5R)-5-methyl-2-(4-pyridyl)-1-piperidyl]-2-oxo-acetyl]amino]-2-pyridyl]carbamate (71.45 mg, 157.54 µmol, 29.77% yield) and E2 tert-butyl N-[3-methyl-5-[[2-[(2R,5S)-5-methyl-2-(4-pyridyl)-1-piperidyl]-2-oxo-acetyl]amino]-2-pyridyl]carbamate (82 mg, 180.80 µmol, 34.17% yield).

Ret time for E1 in analytical conditions (column: IC, IPA-MeOH, 50-50, 0.6 ml/min as mobile phase) 21.25 min and for E2 55.10 min.

E1: Retention time: 38.91 min
LCMS(ESI): [M]$^+$ m/z: calcd 453.2; found 454.2; Rt=1.849 min.

E2:Retention time: 55.10 min
LCMS(ESI): [M]$^+$ m/z: calcd 453.2; found 454.2; Rt=1.842 min.

Step 3: Synthesis of N-(6-amino-5-methylpyridin-3-yl)-2-(5-methyl-2-(Pyridin-4-yl)piperidin-1-yl)-2-oxoacetamide (Compound 609 and Compound 592 tert-butyl N-[3-methyl-5-[[2-[(2S,5R)-5-methyl-2-(4-pyridyl)-1-piperidyl]-2-oxo-acetyl]amino]-2-pyridyl]carbamate (71.45 mg, 157.54 µmol) and tert-butyl N-[3-methyl-5-[[2-[(2R,5S)-5-methyl-2-(4-pyridyl)-1-piperidyl]-2-oxo-acetyl]amino]-2-pyridyl]carbamate (82 mg, 180.80 µmol) were dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (column: Triart 100*20*5 mm, water-MeCN as an eluent mixture) to afford pure N-(6-amino-5-methyl-3-pyridyl)-2-[(2S,5R)-5-methyl-2-(4-pyridyl)-1-piperidyl]-2-oxo-acetamide (44.1 mg, 124.78 µmol, 79.21% yield) and N-(6-amino-5-methyl-3-pyridyl)-2-[(2R,5S)-5-methyl-2-(4-pyridyl)-1-piperidyl]-2-oxo-acetamide (43.8 mg, 123.93 µmol, 68.55% yield).

Compound 609: $^1$H NMR (600 MHz, DMSO-$d_6$) δ (ppm) 0.98-1.04 (m, 3H), 1.25-1.41 (m, 1H), 1.51-1.59 (m, 1H), 1.76-1.91 (m, 1H), 1.92-2.10 (m, 4H), 2.11-2.25 (m, 1H), 2.65-3.24 (m, 1H), 3.41-4.08 (m, 1H), 5.15-5.57 (m, 1H), 5.57-5.69 (m, 2H), 7.25-7.38 (m, 2H), 7.42-7.53 (m, 1H), 7.91-8.05 (m, 1H), 8.51-8.60 (m, 2H), 10.44-10.65 (m, 1H).

LCMS(ESI): [M]$^+$ m/z: calcd 353.2; found 354.2; Rt=0.590 min.

Compound 592: $^1$H NMR (600 MHz, DMSO-$d_6$) δ (ppm) 0.98-1.04 (m, 3H), 1.26-1.40 (m, 1H), 1.46-1.61 (m, 1H), 1.80-1.92 (m, 1H), 1.97-2.13 (m, 4H), 2.15-2.27 (m, 1H), 2.68-3.21 (m, 1H), 3.44-4.07 (m, 1H), 5.15-5.56 (m, 1H), 5.57-5.69 (m, 2H), 7.28-7.36 (m, 2H), 7.42-7.51 (m, 1H), 7.91-8.03 (m, 1H), 8.52-8.59 (m, 2H), 10.48-10.67 (m, 1H).

LCMS(ESI): [M]$^+$ m/z: calcd 353.2; found 354.2; Rt=0.591 min.

Example 433. The Synthesis of rel-N-(6-amino-5-methyl-3-pyridyl)-2-[(2S,5S)-4,4-difluoro-5-methyl-2-(6-methyl-3-pyridyl)-1-piperidyl]-2-oxo-acetamide (Compound 944) and rel-N-(6-amino-5-methyl-3-pyridyl)-2-[(2R,5R)-4,4-difluoro-5-methyl-2-(6-methyl-3-pyridyl)-1-piperidyl]-2-oxo-acetamide (Compound 973

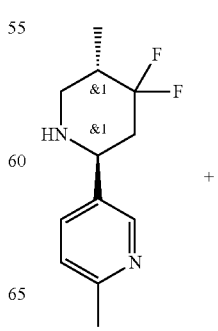

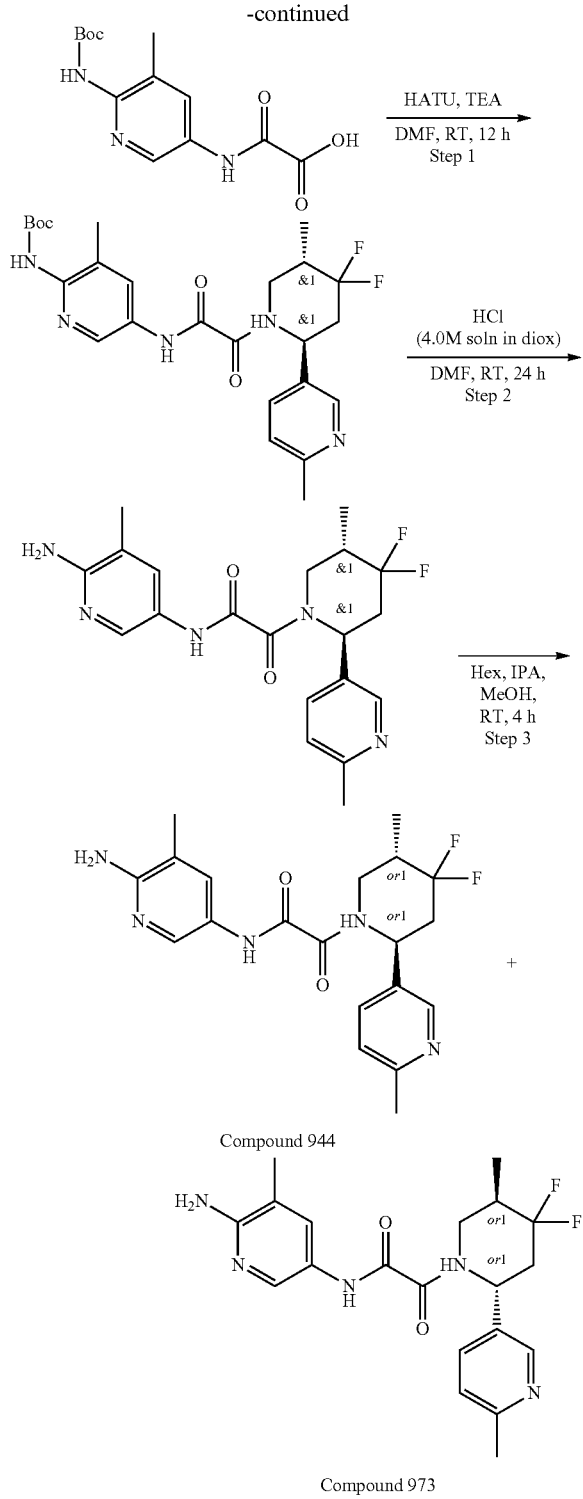

Compound 944

Compound 973

Step 1: The Synthesis of rac-tert-butyl N-[5-[[2-[(2S,5S)-4,4-difluoro-5-methyl-2-(6-methyl-3-pyridyl)-1-piperidyl]-2-oxo-acetyl]amino]-3-methyl-2-pyridyl]carbamate To a solution of 5-[(2S,5S)-4,4-difluoro-5-methyl-2-piperidyl]-2-methyl-pyridine (0.4 g, 1.77 mmol), 2-[[6-(tert-butoxycarbonylamino)-5-methyl-3-pyridyl]amino]-2-oxo-acetic acid (574.23 mg, 1.94 mmol) and triethylamine (894.44 mg, 8.84 mmol, 1.23 mL), HATU (806.62 mg, 2.12 mmol) was added portionwise. The resulting mixture was stirred at 25° C. for 12 hr, taken up with water (50 mL) and extracted with EtOAc (3*20 mL). The combined organic layer was washed with brine (2*25 mL), dried over Na$_2$SO$_4$ and the solvent was removed to give tert-butyl N-[5-[[2-[(2S,5S)-4,4-difluoro-5-methyl-2-(6-methyl-3-pyridyl)-1-piperidyl]-2-oxo-acetyl]amino]-3-methyl-2-pyridyl]carbamate (0.7 g, 1.39 mmol, 78.64% yield).

This compound was used for the next step without further purification.

LCMS(ESI): [M+H]$^+$ m/z: calcd 503.2; found 504.2; Rt=0.950 min.

Step 2: The Synthesis of rac-N-(6-amino-5-methyl-3-pyridyl)-2-[(2S,5S)-4,4-difluoro-5-methyl-2-(6-methyl-3-pyridyl)-1-piperidyl]-2-oxo-acetamide A solution of tert-butyl N-[5-[[2-[(2S,5S)-4,4-difluoro-5-methyl-2-(6-methyl-3-pyridyl)-1-piperidyl]-2-oxo-acetyl]amino]-3-methyl-2-pyridyl]carbamate (0.7 g, 1.39 mmol) and Hydrogen chloride solution 4.0 M in dioxane (10 g, 274.27 mmol, 12.50 mL) in DCM (10 mL) was stirred at 25° C. for 24 hr. The solvent was removed and residue was purified by HPLC: 15-65% 0-5 min H$_2$O/MeOH/0.1% NH$_4$OH, flow: 30 mL/min (loading pump 4 mL/min methanol) target mass 403.44 column: YMC Triart C18 100×20 mm, 5 um) to obtain N-(6-amino-5-methyl-3-pyridyl)-2-[(2S,5S)-4,4-difluoro-5-methyl-2-(6-methyl-3-pyridyl)-1-piperidyl]-2-oxo-acetamide (0.34 g, 842.78 μmol, 60.63% yield).

This compound was used for chiral resolution without HNMR.

LCMS(ESI): [M+H]$^+$ m/z: calcd 403.2; found 404.2; Rt=1.203 min.

Step 3: The Synthesis of rel-N-(6-amino-5-methyl-3-pyridyl)-2-[(2S,5S)-4,4-difluoro-5-methyl-2-(6-methyl-3-pyridyl)-1-piperidyl]-2-oxo-acetamide (Compound 944) and rel-N-(6-amino-5-methyl-3-pyridyl)-2-[(2R,5R)-4,4-difluoro-5-methyl-2-(6-methyl-3-pyridyl)-1-piperidyl]-2-oxo-acetamide (Compound 973 rac-N-(6-amino-5-methyl-3-pyridyl)-2-[(2S,5S)-4,4-difluoro-5-methyl-2-(6-methyl-3-pyridyl)-1-piperidyl]-2-oxo-acetamide (0.34 g, 842.78 μmol) was chirally separated (Chiralpak IA (250*20, 5 mkm), Hexane-IPA-MeOH, 50-25-25, 12 mL/min) to obtain rel-N-(6-amino-5-methyl-3-pyridyl)-2-[(2S,5S)-4,4-difluoro-5-methyl-2-(6-methyl-3-pyridyl)-1-piperidyl]-2-oxo-acetamide (50 mg, 123.94 μmol, 29.41% yield) and rel-N-(6-amino-5-methyl-3-pyridyl)-2-[(2R,5R)-4,4-difluoro-5-methyl-2-(6-methyl-3-pyridyl)-1-piperidyl]-2-oxo-acetamide (65 mg, 161.12 μmol, 38.24% yield).

Compound 944: RT (IC, Hexane-IPA-MeOH, 50-25-25, 0.15 mL/min)=10.430 min.

$^1$H NMR (600 MHz, DMSO-d$_6$) δ 1.02-1.10 (m, 3H), 1.93-2.04 (m, 3H), 2.10-2.24 (m, 1H), 2.37-2.45 (m, 4H), 2.66-3.17 (m, 2H), 3.75-4.30 (m, 1H), 5.52-5.87 (m, 3H), 7.16-7.29 (m, 1H), 7.40-7.54 (m, 1H), 7.56-7.64 (m, 1H), 7.90-8.07 (m, 1H), 8.36-8.42 (m, 1H), 10.46-10.68 (m, 1H).

LCMS(ESI): [M+2H]$^+$ m/z: calcd 403.2; found 405.4; Rt=1.144 min.

Compound 973: RT (IC, Hexane-IPA-MeOH, 50-25-25, 0.15 mL/min)=13.589 min.

2279
¹H NMR (600 MHz, DMSO-d₆) δ 1.03-1.09 (m, 3H), 1.93-2.04 (m, 3H), 2.11-2.22 (m, 1H), 2.38-2.44 (m, 4H), 2.80-3.22 (m, 2H), 3.69-4.30 (m, 1H), 5.53-5.62 (m, 1H), 5.62-5.86 (m, 2H), 7.16-7.28 (m, 1H), 7.40-7.54 (m, 1H), 7.54-7.63 (m, 1H), 7.91-8.06 (m, 1H), 8.34-8.42 (m, 1H), 10.44-10.67 (m, 1H).
LCMS(ESI): [M+2H]⁺ m/z: calcd 403.2; found 405.4; Rt=1.145 min.
Example 434. The Synthesis of N-(6-amino-5-ethylpyridin-3-yl)-2-(4,4-difluoro-2-(1H-indazol-5-yl)-5-methylpiperidin-1-yl)-2-oxoacetamide (Compound 1357 and Compound 1148
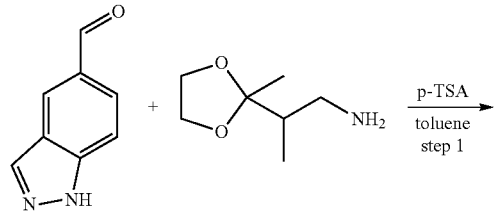
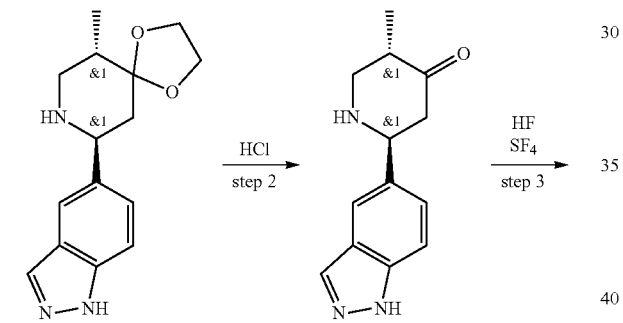
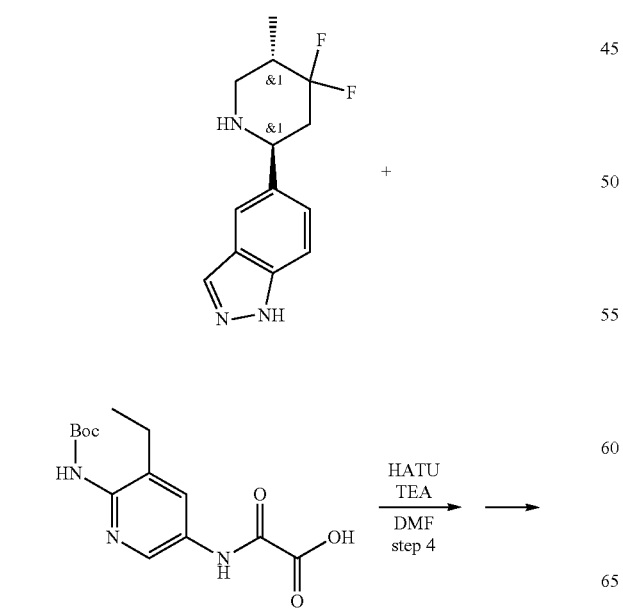
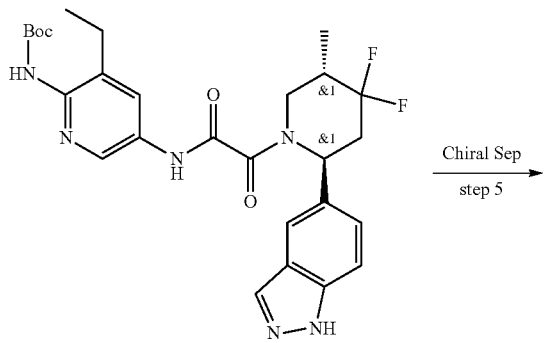
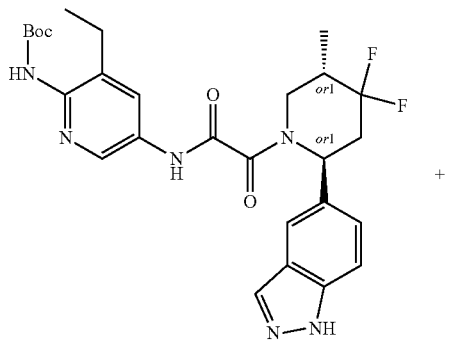
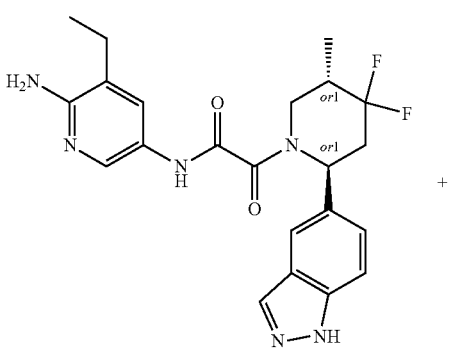
Compound 1357

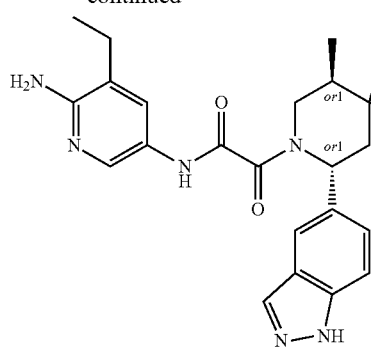

Compound 1148

Step 4: Synthesis of rac-tert-butyl (5-(2-((2R,5R)-4,4-difluoro-2-(1H-indazol-5-yl)-5-methylpiperidin-1-yl)-2-oxoacetamido)-3-ethylpyridin-2-yl)carbamate 5-[(2S,5R)-4,4-difluoro-5-methyl-2-piperidyl]-1H-indazole (0.42 g, 1.67 mmol), TEA (1.69 g, 16.71 mmol, 2.33 mL) and 2-[[6-(tert-butoxycarbonylamino)-5-ethyl-3-pyridyl]amino]-2-oxo-acetic acid (517.02 mg, 1.67 mmol) were dissolved in DMF (18 mL) and HATU (953.32 mg, 2.51 mmol) was added in one portion, the resulting mixture was stirred for 3 hr at 20° C. The reaction mixture was poured into water and the aqueous phase was extracted with EtOAc (3 times), then the combined organic phase was washed with brine (3 times), dried over $Na_2SO_4$ and concentrated on vacuum. The crude product was purified by reverse phase HPLC (2-10 min 55-70% MeOH 30 ml/min, loading pump 4 ml/min MeOH, target mass 542, column: SunFire 19*100 mm, 5 microM). The desired product tert-butyl N-[5-[[2-[(2S,5R)-4,4-difluoro-2-(1H-indazol-5-yl)-5-methyl-1-piperidyl]-2-oxo-acetyl]amino]-3-ethyl-2-pyridyl]carbamate (0.071 g, 130.86 umol, 7.83% yield) was isolated as a light-yellow solid.

LCMS(ESI): [M]+ m/z: calcd 542.2; found 543.2; Rt=1.365 min.

Step 5: Chiral Separation

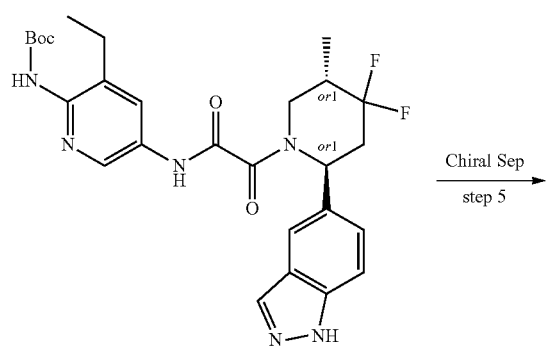

Chiral Sep
step 5

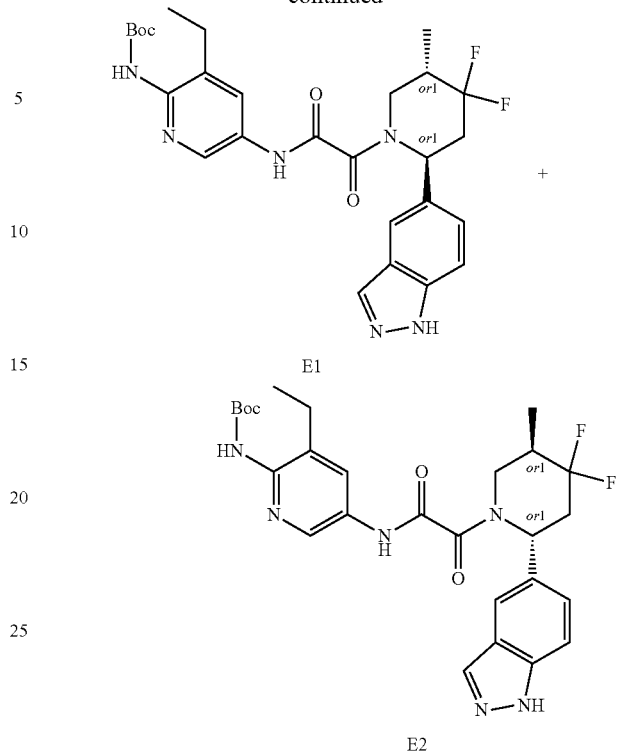

E2

Chiral separation was performed using (Column: Chiralpak IB (250*20, 5 mkm); Mobile phase: Hexane-IPA-MeOH, 70-15-15, Flow Rate: 12 mL/min; Column Temperature: 24° C.; Wavelength: 205 nm, 258 nm, 290 nm) to give tert-butyl N-[5-[[2-[(2S,5R)-4,4-difluoro-2-(1H-indazol-5-yl)-5-methyl-1-piperidyl]-2-oxo-acetyl]amino]-3-ethyl-2-pyridyl]carbamate (0.018 g, 33.18 umol, 25.35% yield)—RT is 12.445 min and tert-butyl N-[5-[[2-[(2R,5S)-4,4-difluoro-2-(1H-indazol-5-yl)-5-methyl-1-piperidyl]-2-oxo-acetyl]amino]-3-ethyl-2-pyridyl]carbamate (0.02 g, 36.86 umol, 28.17% yield)—RT is 13.865 min.

Rel Time for E1 in analytical conditions (column: IB, Hexane-IPA-MeOH, 70-15-15, 0.6 ml/min as mobile phase) 15.37 min and for E2 18.40 min.

E1:
Retention time: 15.37 min
LCMS(ESI): [M]+ m/z: calcd 542.2; found 543.2; Rt=1.306 min.

E2:
Retention time: 18.40 min
LCMS(ESI): [M]+ m/z: calcd 542.2; found 543.2; Rt=1.307 min.

Step 6: Synthesis of N-(6-amino-5-ethylpyridin-3-yl)-2-(4,4-difluoro-2-(1H-indazol-5-yl)-5-methylpiperidin-1-yl)-2-oxoacetamide (Compound 1148 and Compound 1357 tert-butyl N-[5-[[2-[(2R,5R)-4,4-difluoro-2-(1H-indazol-5-yl)-5-methyl-1-piperidyl]-2-oxo-acetyl]amino]-3-ethyl-2-pyridyl]carbamate (0.018 g, 33.18 umol) and tert-butyl N-[5-[[2-[(2S,5S)-4,4-difluoro-2-(1H-indazol-5-yl)-5-methyl-1-piperidyl]-2-oxo-acetyl]amino]-3-ethyl-2-pyridyl]carbamate (0.02 g, 36.86 umol) were dissolved in mixture of dioxane (2 mL) and water (2 mL) then stirred at 100° C. for 12 hr. The reaction mixture was concentrated on vacuum.

The crude product was purified by HPLC (2-10 min 45-60% MeOH 30 ml/min, loading pump 4 ml/min MeOH, target mass 442, column: SunFire 100*19 mm, 5 microM). The desired product N-(6-amino-5-ethyl-3-pyridyl)-2-[(2S,5R)-4,4-difluoro-2-(1H-indazol-5-yl)-5-methyl-1-piperidyl]-2-oxo-acetamide (0.009 g, 20.34 umol, 61.31% yield) and N-(6-amino-5-ethyl-3-pyridyl)-2-[(2R,5S)-4,4-difluoro-2-(1H-indazol-5-yl)-5-methyl-1-piperidyl]-2-oxo-acetamide (0.01 g, 22.60 umol, 61.31% yield) were obtained as a light-yellow solids.

Compound 1357:
LCMS(ESI): [M]f m/z: calcd 442.2; found 443.2; Rt=0.986 min.

Compound 1148:
LCMS(ESI): [M]⁺ m/z: calcd 442.2; found 443.2; Rt=0.987 min.

Example 435. The Synthesis of N-(6-amino-5-methylpyridin-3-yl)-2-(2-(7-fluoro-1H-indazol-5-yl)-5-methylpiperidin-1-yl)-2-oxoacetamide (Compound 1350 and Compound 1191

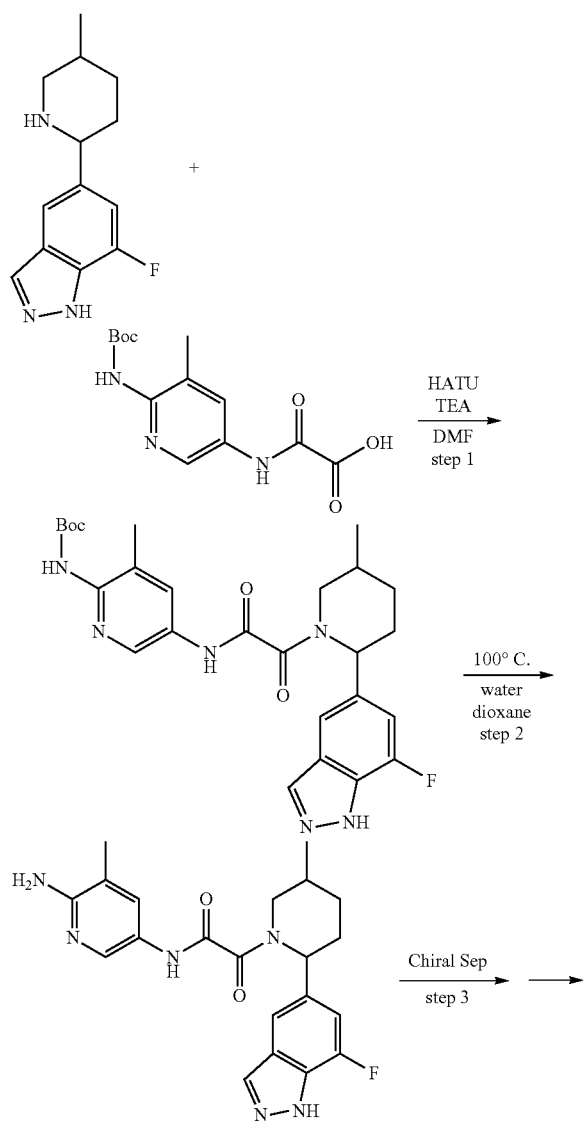

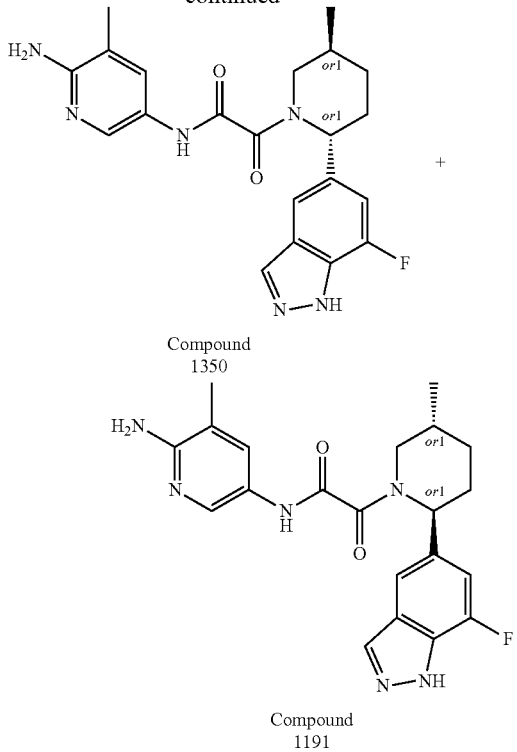

Step 1: Synthesis of tert-butyl (5-(2-(2-(7-Fluoro-1H-indazol-5-yl)-5-methylpiperidin-1-yl)-2-oxoacetamido)-3-methylpyridin-2-yl)carbamate 2-[[6-(tert-butoxycarbonylamino)-5-methyl-3-pyridyl]amino]-2-oxo-acetic acid (1.09 g, 3.69 mmol) and 7-fluoro-5-(5-methyl-2-piperidyl)-1H-indazole (0.86 g, 3.69 mmol) were mixed in DMF (50 mL). The reaction suspension was cooled to 0° C. and HATU (1.54 g, 4.06 mmol) followed by TEA (746.07 mg, 7.37 mmol, 1.03 mL) were added and stirred at rt for 14 hr. The reaction mixture was evaporated in vacuum and poured into water (100 ml) and extracted with EtOAc (2×50 ml). The combined organic extracts were washed with water (2*30 ml), dried over sodium sulphate and evaporated in vacuum to afford product tert-butyl N-[5-[[2-[2-(7-fluoro-1H-indazol-5-yl)-5-methyl-1-piperidyl]-2-oxo-acetyl]amino]-3-methyl-2-pyridyl]carbamate (1.42 g, 2.78 mmol, 75.44% yield).

LCMS(ESI): [M]⁺ m/z: calcd 510.2; found 511.2; Rt=1.284 min.

Step 2: Synthesis of N-(6-amino-5-methylpyridin-3-yl)-2-(2-(7-fluoro-1H-indazol-5-yl)-5-methylpiperidin-1-yl)-2-oxoacetamide Water (10 mL) was added to a stirred solution of tert-butyl N-[5-[[2-[2-(7-fluoro-1H-indazol-5-yl)-5-methyl-1-piperidyl]-2-oxo-acetyl]amino]-3-methyl-2-pyridyl]carbamate (1.42 g, 2.78 mmol) in dioxane (30 mL) at rt. The resulting mixture was stirred at 100° C. for 15 hr, and then evaporated in vacuum and obtained crude product 0.9 g was purified by preparative 35-75% 0-5 min H₂O/MeOH/0.1% NH₄OH, flow: 30 ml/min to afford product N-(6-amino-5-methyl-3-pyridyl)-2-[2-(7-fluoro-1H-indazol-5-yl)-5-methyl-1-piperidyl]-2-oxo-acetamide (0.400 g, 974.55 umol, 35.04% yield).

LCMS(ESI): [M]+ m/z: calcd 410.2; found 411.2; Rt=2.340 min.

Step 3: Chiral Separation (Compound 1350 and Compound 1191

Racemic N-(6-amino-5-methyl-3-pyridyl)-2-[2-(7-fluoro-JH-indazol-5-yl)-5-methyl-1-piperidyl]-2-oxo-acetamide (0.400 g, 974.55 umol) was chiral separated (Column: Chiralcel OD-H (250*20, 5 um), Eluent: Hexane-IPA-MeOH, 50-25-25, flow rate: 12 mL/min) to obtain N-(6-amino-5-methyl-3-pyridyl)-2-[(2R,5S)-2-(7-fluoro-1H-indazol-5-yl)-5-methyl-1-piperidyl]-2-oxo-acetamide (110.40 mg, 268.98 umol, 27.60% yield) and N-(6-amino-5-methyl-3-pyridyl)-2-[(2S,5R)-2-(7-fluoro-JH-indazol-5-yl)-5-methyl-1-piperidyl]-2-oxo-acetamide (0.1061 g, 258.50 umol, 26.53% yield).

Rel Time for Compound 1350 in analytical conditions (column: OD-H, Hexane-IPA-MeOH, 50-25-25, 0.6 ml/min as mobile phase) 17.08 min and for Compound 1191 8.00 min.

Compound 1350:

Retention time: 17.08 min $^1$H NMR (600 MHz, DMSO-d$_6$) δ (ppm) 0.98-1.07 (m, 3H), 1.29-1.40 (m, 1H), 1.69-1.81 (m, 1H), 1.82-1.92 (m, 1H), 1.95-2.04 (m, 3H), 2.06-2.21 (m, 1H), 2.22-2.31 (m, 1H), 2.74-3.28 (m, 1H), 3.43-4.04 (m, 1H), 5.15-5.69 (m, 3H), 7.06-7.26 (m, 1H), 7.40-7.52 (m, 1H), 7.52-7.59 (m, 1H), 7.92-8.05 (m, 1H), 8.15 (s, 1H), 10.47-10.58 (m, 1H), 13.60 (s, 1H). LCMS(ESI): [M]+ m/z: calcd 410.2; found 411.2; Rt=2.486 min.

Compound 1191:

Retention time: 8.00 min $^1$H NMR (600 MHz, DMSO-d$_6$) δ (ppm) 0.98-1.06 (m, 3H), 1.29-1.41 (m, 1H), 1.69-1.80 (m, 1H), 1.82-1.92 (m, 1H), 1.96-2.04 (m, 3H), 2.06-2.20 (m, 1H), 2.23-2.31 (m, 1H), 2.74-3.28 (m, 1H), 3.43-4.04 (m, 1H), 5.13-5.69 (m, 3H), 7.05-7.25 (m, 1H), 7.37-7.52 (m, 1H), 7.52-7.59 (m, 1H), 7.90-8.05 (m, 1H), 8.16 (s, 1H), 10.49-10.59 (m, 1H), 13.60 (s, 1H).

LCMS(ESI): [M]+ m/z: calcd 410.2; found 411.2; Rt=2.482 min.

Example 436. The Synthesis of N-(6-amino-5-methylpyridin-3-yl)-2-(5-methyl-2-(1H-thieno[2,3-c]pyrazol-5-yl)piperidin-1-yl)-2-oxoacetamide (Compound 1392 and Compound 1120

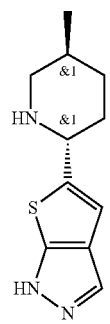

+

-continued

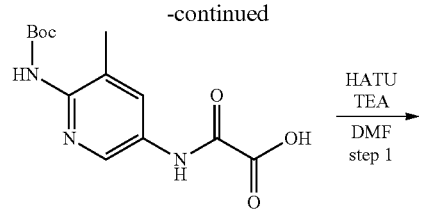

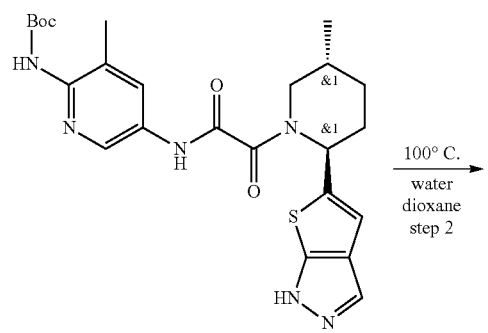

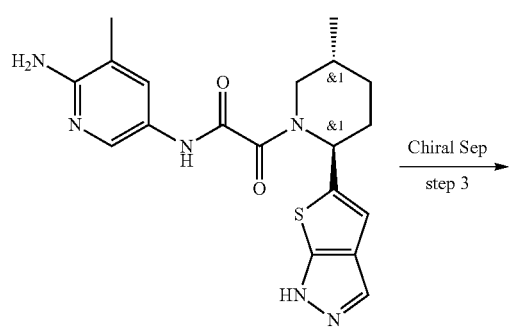

Compound 1120

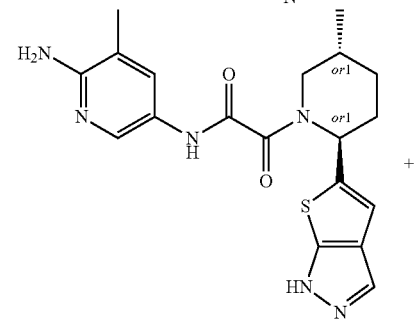

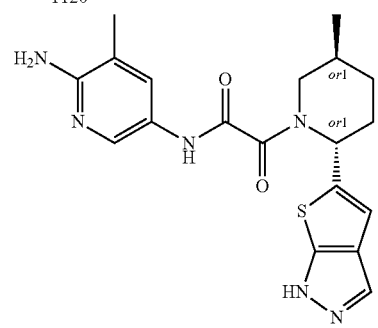

Compound 1392

Step 1: Synthesis of rac-tert-butyl (3-methyl-5-(2-((2R,5S)-5-methyl-2-(1H-thieno[2,3-c]pyrazol-5-yl)piperidin-1-yl)-2-oxoacetamido)pyridin-2-yl)carbamate 2-[[6-(tert-butoxycarbonylamino)-5-methyl-3-pyridyl]amino]-2-oxo-acetic acid (401.32 mg, 1.36 mmol), 5-[(2S,5R)-5-methyl-2-piperidyl]-2H-thieno[2,3-c]pyrazole (300.79 mg, 1.36 mmol) and DIPEA (526.94 mg, 4.08 mmol, 710.16 uL) were dissolved in DMSO (6 mL) under gentle heating. HATU (620.11 mg, 1.63 mmol) was added in small portions under vigorous stirring and occasional heating. After the reaction was complete, the mixture was purified by HPLC (40-90% 0.5-6.5 min water-MeOH; flow 30 ml/min; (loading pump 4 ml/min MeOH); target mass 498; column SunFire C18 100×19 mm 5 um (L)) to give tert-butyl N-[3-methyl-5-[[2-[(2S,5R)-5-methyl-2-(1H-thieno[2,3-c]pyrazol-5-yl)-1-piperidyl]-2-oxo-acetyl]amino]-2-pyridyl]carbamate (80 mg, 160.45 umol, 11.81% yield).

LCMS(ESI): [M]+ m/z: calcd 498.2; found 499.2; Rt=2.857 min.

Step 2: Synthesis of N-(6-amino-5-methylpyridin-3-yl)-2-(5-methyl-2-(1H-Thieno[2,3-c]pyrazol-5-yl)piperidin-1-yl)-2-oxoacetamide tert-butyl N-[3-methyl-5-[[2-[(2S,5R)-5-methyl-2-(1H-thieno[2,3-c]pyrazol-5-yl)-1-piperidyl]-2-oxo-acetyl]amino]-2-pyridyl]carbamate (80 mg, 160.45 umol) was dissolved in dioxane (2 mL) and water (0.5 mL). Obtained solution was stirred at 100° C. for 2 hr; after the reaction was complete, the mixture was subjected to HPLC (18% 0.5-6.5 min water-MeCN; flow 30 ml/min (loading pump 4 ml/min MeCN; target mass 398; column SunFire C18 100×19 mm 5 um (R)) to give N-(6-amino-5-methyl-3-pyridyl)-2-[(2S,5R)-5-methyl-2-(1H-thieno[2,3-c]pyrazol-5-yl)-1-piperidyl]-2-oxo-acetamide (40 mg, 100.38 umol, 62.56% yield).

$^1$H NMR (600 MHz, DMSO-$d_6$) δ (ppm) 0.98 (d, 3H), 1.37-1.48 (m, 1H), 1.83-1.96 (m, 2H), 1.98-2.02 (m, 3H), 2.02-2.17 (m, 2H), 2.91-2.96 (m, 0.4H), 3.34-3.39 (m, 0.6H), 3.44-4.08 (m, 1H), 5.40-5.81 (m, 3H), 6.88-6.98 (m, 1H), 7.46-7.51 (m, 1H), 7.87-8.00 (m, 1H), 8.01 (s, 1H), 10.42-10.64 (m, 1H), 13.29 (s, 1H).

LCMS(ESI): [M]+ m/z: calcd 398.2; found 399.2; Rt=1.722 min.

Step 3: Chiral Separation (Compound 1392 and Compound 1120

Racemate was purification with chiral HPLC (Chiralpak IA (250*20, 5 mkm), Hexane-IPA-MeOH, 50-25-25, 12 ml/min) results in N-(6-amino-5-methyl-3-pyridyl)-2-[(2R,5S)-5-methyl-2-(1H-thieno[2,3-c]pyrazol-5-yl)-1-piperidyl]-2-oxo-acetamide (8 mg, 20.08 umol, 25.02% yield) and N-(6-amino-5-methyl-3-pyridyl)-2-[(2S,5R)-5-methyl-2-(1H-thieno[2,3-c]pyrazol-5-yl)-1-piperidyl]-2-oxo-acetamide (8 mg, 20.08 umol, 25.02% yield). Rel Time for Compound 1392 in analytical conditions (column: IA, Hexane-IPA-MeOH, 50-25-25, 0.6 ml/min as mobile phase) 65.80 min and for Compound 1120 43.62 min.

Compound 1392:
Retention time: 65.80 min
$^1$H NMR (600 MHz, DMSO-$d_6$) δ (ppm) 0.96-1.03 (m, 3H), 1.39-1.44 (m, 1H), 1.86-1.96 (m, 2H), 1.99-2.03 (m, 3H), 2.04-2.19 (m, 2H), 2.90-3.40 (m, 1H), 3.45-4.09 (m, 1H), 5.39-5.81 (m, 3H), 6.89-7.00 (m, 1H), 7.49 (s, 1H), 7.95 (s, 1H), 7.99-8.05 (m, 1H), 10.43-10.53 (m, 1H), 13.29 (s, 1H).

LCMS(ESI): [M]+ m/z: calcd 398.2; found 399.2; Rt=0.803 min.

Compound 1120:
Retention time: 43.62 min
$^1$H NMR (600 MHz, DMSO-$d_6$) δ (ppm) 0.97-1.03 (m, 3H), 1.38-1.45 (m, 1H), 1.84-1.97 (m, 2H), 1.99-2.18 (m, 5H), 2.91-3.40 (m, 1H), 3.44-4.07 (m, 1H), 5.41-5.60 (m, 1H), 5.61-5.79 (m, 2H), 6.87-6.97 (m, 1H), 7.45-7.52 (m, 1H), 7.89-7.97 (m, 1H), 8.02 (d, 1H), 10.43-10.52 (m, 1H), 13.29 (s, 1H).

LCMS(ESI): [M]+ m/z: calcd 398.2; found 399.2; Rt=0.803 min.

Example 437. The Synthesis of N-(6-amino-5-ethyl-3-pyridyl)-2-[(2R,5S)-5-methyl-2-[6-(4-methylpiperazin-1-yl)-3-pyridyl]-1-piperidyl]-2-oxo-acetamide (Compound 1103

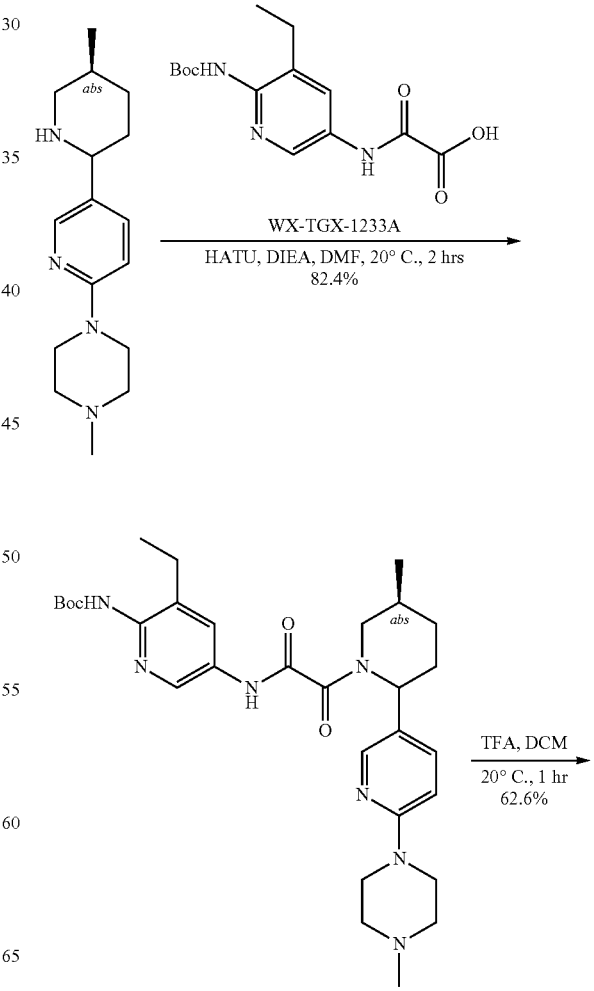

-continued

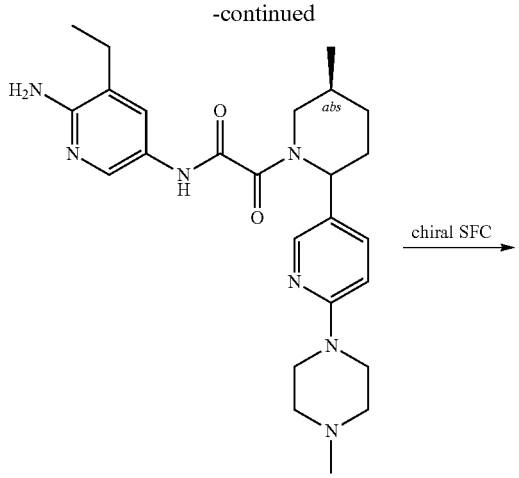

Step 1: Synthesis of tert-butyl N-tert-butoxycarbonyl-N-[3-ethyl-5-[[2-[(5S)-5-methyl-2-[6-(4-methylpiperazin-1-yl)-3-pyridyl]-1-piperidyl]-2-oxo-acetyl]amino]-2-pyridyl]carbamate To a mixture of 1-methyl-4-[5-[(5S)-5-methyl-2-piperidyl]-2-pyridyl]piperazine (40 mg, 0.146 mmol), 2-[[6-[bis(tert-butoxycarbonyl)amino]-5-ethyl-3-pyridyl]amino]-2-oxo-acetic acid (60 mg, 0.146 mmol) and DCM (2 mL) were added HATU (70 mg, 0.184 mmol) and DIPEA (0.1 mL, 0.574 mmol) and the mixture was stirred at 25° C. for 2 hours. The resulting mixture was quenched by addition of water (10 mL) and extracted with EtOAc (10 mL*3). The combined organic layer was washed with saturated NH₄Cl aqueous solution (10 mL*2), brine (10 mL), dried over anhydrous Na₂SO₄, filtered and concentrated under reduced pressure to give a residue which purified by flash chromatography (ISCO©; 12 g AgelaFlash® Silica Flash Column, petroleum ether/EtOAc with EtOAc from 0~20%, Flow Rate: 30 mL/min) to afford tert-butyl N-tert-butoxycarbonyl-N-[3-ethyl-5-[[2-[(5S)-5-methyl-2-[6-(4-methylpiperazin-1-yl)-3-pyridyl]-1-piperidyl]-2-oxo-acetyl]amino]-2-pyridyl]carbamate (80 mg, 82.4% yield) as yellow oil. LCMS (ESI) [M+H]⁺ m/z: calcd 666.3, found 666.3.

Step 2: Synthesis of N-(6-amino-5-ethyl-3-pyridyl)-2-[(5S)-5-methyl-2-[6-(4-methylpiperazin-1-yl)-3-pyridyl]-1-piperidyl]-2-oxo-acetamide To a mixture of tert-butyl N-tert-butoxycarbonyl-N-[3-ethyl-5-[[2-[(5S)-5-methyl-2-[6-(4-methylpiperazin-1-yl)-3-pyridyl]-1-piperidyl]-2-oxo-acetyl]amino]-2-pyridyl]carbamate (80 mg, 0.120 mmol) and DCM (1 mL) was added TFA (1 mL, 13.0 mmol) and the mixture was stirred at 20° C. for 1 hour. The mixture was filtered and concentrated under reduced pressure to give a crude product which was purified by flash chromatography (ISCO®, Column: SepaFlash® Spherical C18, 25 g, 40-60 m, 120A; MeCN/water (0.5% NH₃—H₂O) with MeCN from 0-45%, 25 mL/min, 220 nm) to give N-(6-amino-5-ethyl-3-pyridyl)-2-[(5S)-5-methyl-2-[6-(4-methylpiperazin-1-yl)-3-pyridyl]-1-piperidyl]-2-oxo-acetamide (35 mg, 62.6% yield) as white solid. LCMS (ESI) [M+H]⁺ m/z: calcd 466.2, found 466.2.

Step 3: Synthesis of N-(6-amino-5-ethyl-3-pyridyl)-2-[(2R,5S)-5-methyl-2-[6-(4-methylpiperazin-1-yl)-3-pyridyl]-1-piperidyl]-2-oxo-acetamide (Compound 1103

N-(6-amino-5-ethyl-3-pyridyl)-2-[(5S)-5-methyl-2-[6-(4-methylpiperazin-1-yl)-3-pyridyl]-1-piperidyl]-2-oxo-acetamide (30 mg, 64.4 umol) was purified by chiral SFC (Instrument: Berger, Multigr AM-II; Column: Daicel Chiralcel OD-H (250 mm*30 mm, 5 m); Mobile phase: supercritical CO₂/EtOH (0.1% NH₃—H₂O, v %)=50/50; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give Compound 1103 (peak 2, retention time=5.269 min).

N-(6-amino-5-ethyl-3-pyridyl)-2-[(2R,5S)-5-methyl-2-[6-(4-methylpiperazin-1-yl)-3-pyridyl]-1-piperidyl]-2-oxo-acetamide (21 mg, single known enantiomer with trans relative chemistry, peak 2, retention time=5.269 min, white solid). ¹H NMR (400 MHz, DMSO-d₆) δ ppm 10.22 (s, 1H), 8.08 (br d, J=17.1 Hz, 2H), 7.44-7.56 (m, 2H), 6.81 (d, J=8.8 Hz, 1H), 5.36 (br s, 3H), 3.46-3.57 (m, 5H), 2.40-2.49 (m, 7H), 2.28 (s, 3H), 2.02-2.13 (m, 2H), 1.72-1.96 (m, 2H), 1.35 (br d, J=13.3 Hz, 1H), 1.16 (t, J=7.4 Hz, 3H), 1.05 (d, J=6.8 Hz, 3H); LCMS (ESI) [M+H]⁺ m/z: calcd 466.2, found 466.2. HPLC: 100%@220 nm, 100%@254 nm; 100% ee.

Example 438. The Synthesis of N-(6-amino-5-cyclopropylpyridin-3-yl)-2-(2-(imidazo[1,5-a]pyridin-6-yl)-5-methylpiperidin-1-yl)-2-oxoacetamide (Compound 1336 and Compound 1205

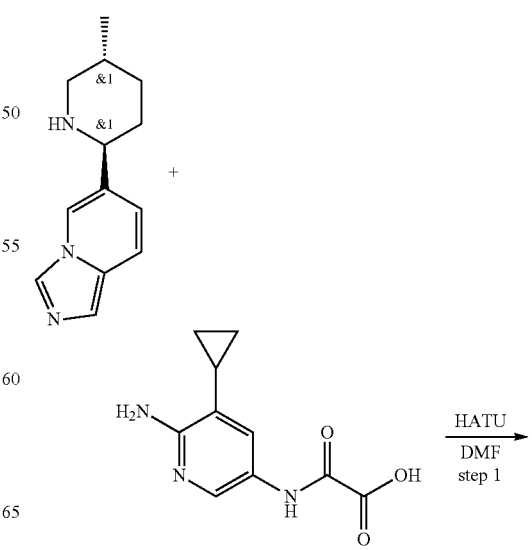

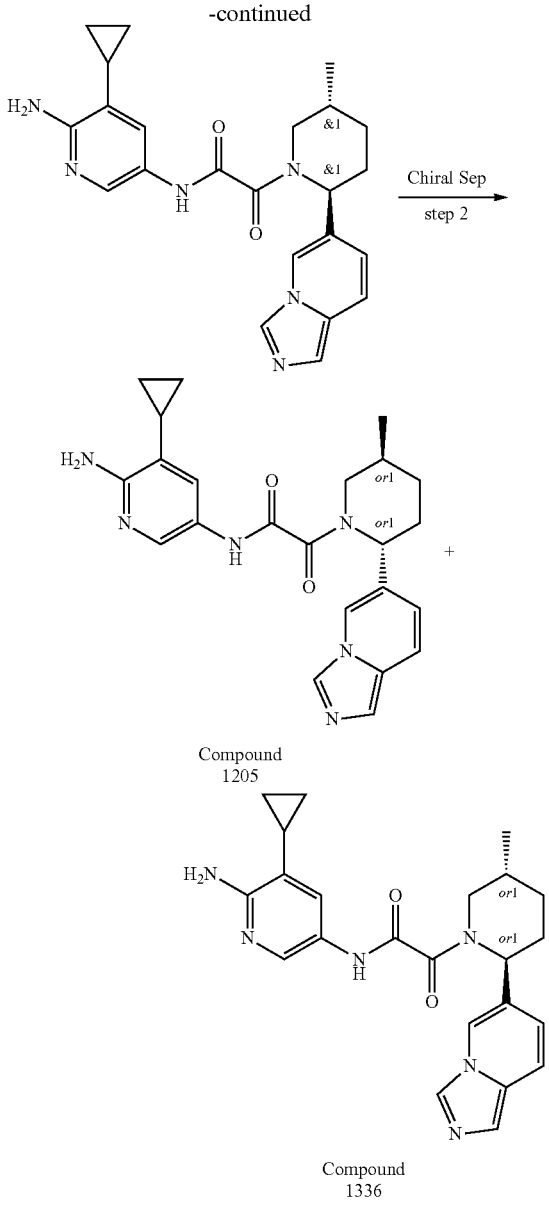

Compound 1205

Compound 1336

Step 1: Synthesis of N-(6-amino-5-cyclopropylpyridin-3-yl)-2-(2-(imidazo[1,5-a]pyridin-6-yl)-5-methylpiperidin-1-yl)-2-oxoacetamide Sodium 2-[(6-amino-5-cyclopropyl-3-pyridyl)amino]-2-oxo-acetate (225.92 mg, 464.48 umol), HATU (229.59 mg, 603.83 umol) were mixed in dry DMF (5 mL) at 21° C. and the resulting mixture was stirred for 15 min. 6-(5-methyl-2-piperidyl)imidazo[1,5-a]pyridine (100 mg, 464.48 umol) was added thereto and the resulting mixture was stirred at 21° C. overnight. The resulting mixture was poured into water, extracted 3 times with EtOAc, combined organics were washed with water, brine, and evaporated. The residue was subjected to HPLC (20-40 0.5-6.5 min water-MeCN; flow 30 ml/min (loading pump 5 ml/min MeCN); column SunFire 100×19 mm 5 um (R)). Two fractions of N-(6-amino-5-cyclopropyl-3-pyridyl)-2-(2-imidazo[1,5-a]pyridin-6-yl-5-methyl-1-piperidyl)-2-oxo-acetamide (56.7 mg, 135.49 umol, 29.17% yield) were obtained: 1st—17 mg (91.41% by LCMS), 2nd—39.7 mg (100% by LCMS).

LCMS(ESI): [M]+ m/z: calcd 418.2; found 419.2; Rt=1.973 min.

Step 2: Chiral Separation (Compound 1336 and Compound 1205

Racemic N-(6-amino-5-cyclopropylpyridin-3-yl)-2-(2-(imidazo[1,5-a]pyridin-6-yl)-5-methyl piperidin-1-yl)-2-oxoacetamide (56.7 mg, 135.49 umol) was chiral separated (Column: Chiralpak IB (250*20 mm, 5 mkm), Hexane-IPA-MeOH, 50-25-25, 12 ml/min) to obtain N-(6-amino-5-cyclopropyl-3-pyridyl)-2-[(2R,5S)-2-imidazo[1,5-a]pyridin-6-yl-5-methyl-1-piperidyl]-2-oxo-acetamide (15.21 mg, 36.34 umol, 26.83% yield) (RT=21.13 min) and N-(6-amino-5-cyclopropyl-3-pyridyl)-2-[(2S,5R)-2-imidazo[1,5-a]pyridin-6-yl-5-methyl-1-piperidyl]-2-oxo-acetamide (16.15 mg, 38.59 umol, 28.48% yield) (RT=10.23 min).

Rel Time for Compound 1336 in analytical conditions (column: IB, Hexane-IPA-MeOH, 50-25-25, 0.6 ml/min as mobile phase) 12.98 min and for Compound 1205 30.65 min.

Compound 1336:

Retention time: 12.98 min $^1$H NMR (600 MHz, DMSO-d$_6$) δ (ppm) 0.44 (m, 2H), 0.87 (m, 2H), 1.01 (m, 3H), 1.35 (m, 1H), 1.65 (m, 1H), 1.99 (m, 4H), 2.82 (m, 1H), 3.76 (dd, 1H), 5.35 (m, 1H), 5.75 (m, 2H), 6.74 (m, 1H), 7.32 (m, 2H), 7.54 (m, 1H), 8.02 (m, 1H), 8.31 (m, 2H), 10.47 (s, 1H).

LCMS(ESI): [M]+ m/z: calcd 418.2; found 419.2; Rt=1.654 min.

Compound 1205:

Retention time: 30.65 min $^1$H NMR (600 MHz, DMSO-d$_6$) δ (ppm) 0.44 (m, 2H), 0.87 (m, 2H), 1.01 (m, 3H), 1.35 (m, 1H), 1.65 (m, 1H), 1.97 (m, 4H), 2.82 (m, 1H), 3.76 (dd, 1H), 5.75 (m, 3H), 6.71 (m, 1H), 7.32 (m, 2H), 7.54 (m, 1H), 8.02 (m, 1H), 8.31 (m, 2H), 10.47 (s, 1H).

LCMS(ESI): [M]+ m/z: calcd 418.2; found 419.2; Rt=1.663 min.

Example 439. The Synthesis of N-(6-amino-5-cyclopropyl-3-pyridyl)-2-[(2S,5R)-2-(1,2-benzothiazol-5-yl)-5-methyl-1-piperidyl]-2-oxo-acetamide (Compound 1400) and N-(6-amino-5-cyclopropyl-3-pyridyl)-2-[(2R,5S)-2-(1,2-benzothiazol-5-yl)-5-methyl-1-piperidyl]-2-oxo-acetamide (Compound 1153

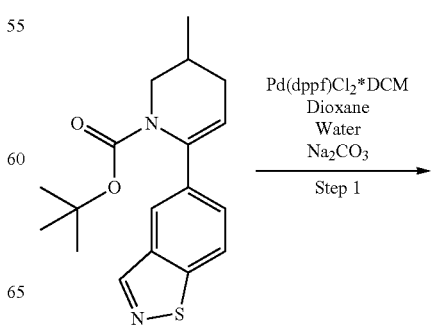

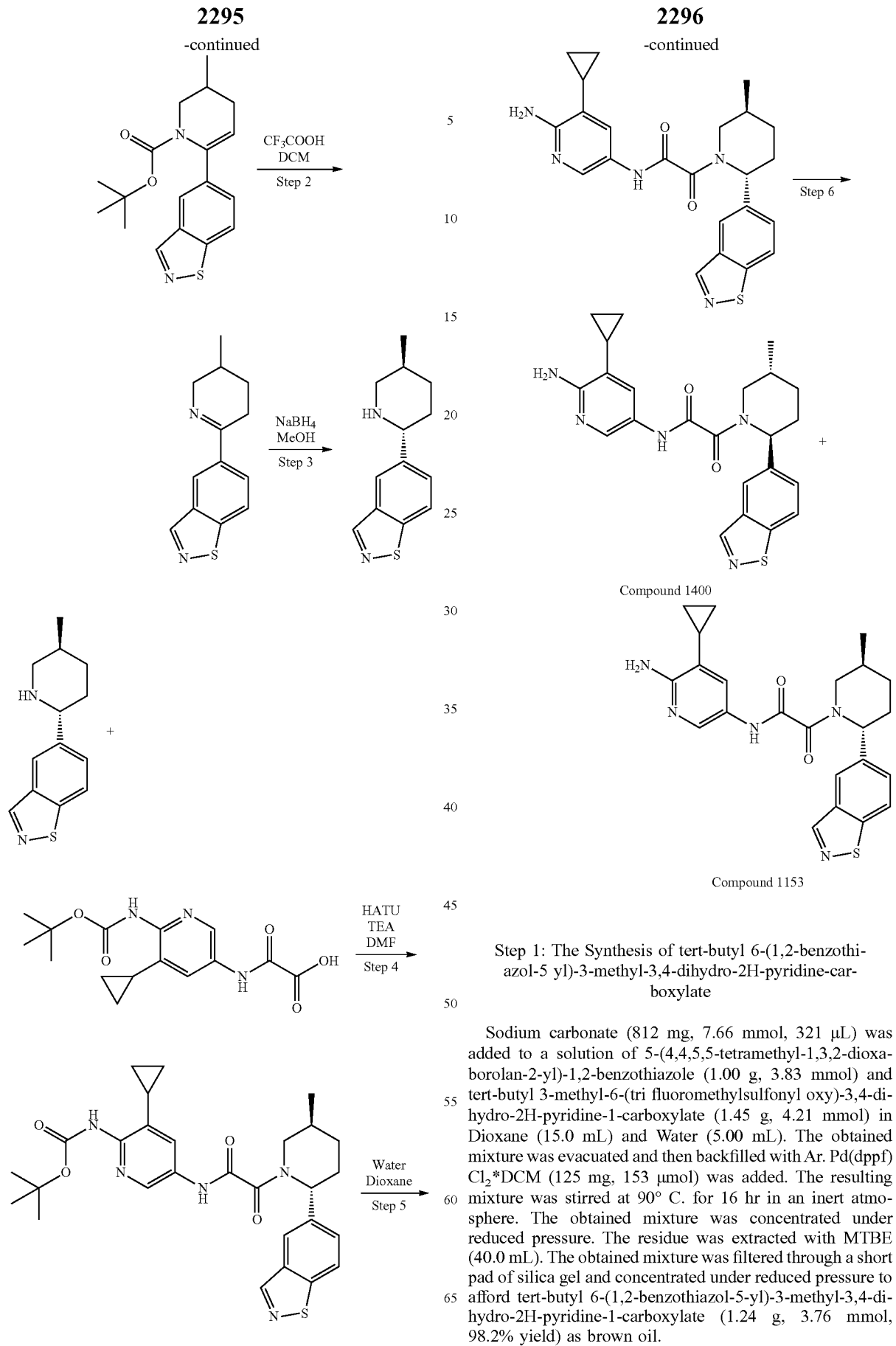

Step 1: The Synthesis of tert-butyl 6-(1,2-benzothi-azol-5 yl)-3-methyl-3,4-dihydro-2H-pyridine-carboxylate Sodium carbonate (812 mg, 7.66 mmol, 321 μL) was added to a solution of 5-(4,4,5,5-tetramethyl-1,3,2-dioxaborolan-2-yl)-1,2-benzothiazole (1.00 g, 3.83 mmol) and tert-butyl 3-methyl-6-(tri fluoromethylsulfonyl oxy)-3,4-dihydro-2H-pyridine-1-carboxylate (1.45 g, 4.21 mmol) in Dioxane (15.0 mL) and Water (5.00 mL). The obtained mixture was evacuated and then backfilled with Ar. Pd(dppf)Cl$_2$*DCM (125 mg, 153 μmol) was added. The resulting mixture was stirred at 90° C. for 16 hr in an inert atmosphere. The obtained mixture was concentrated under reduced pressure. The residue was extracted with MTBE (40.0 mL). The obtained mixture was filtered through a short pad of silica gel and concentrated under reduced pressure to afford tert-butyl 6-(1,2-benzothiazol-5-yl)-3-methyl-3,4-dihydro-2H-pyridine-1-carboxylate (1.24 g, 3.76 mmol, 98.2% yield) as brown oil.

LCMS(ESI): [M+H]$^+$ m/z: calcd 331.17; found 331.2; Rt=1.529.

Step 2: The Synthesis of 5-(3-methyl-2,3,4,5-tetrahydropyridin-6-yl)-1,2-benzothiazole Trifluoroacetic acid (4.29 g, 37.6 mmol, 2.90 mL) was added to a solution of tert-butyl 6-(1,2-benzothiazol-5-yl)-3-methyl-3,4-dihydro-2H-pyridine-1-carboxylate (1.24 g, 3.76 mmol) in Dichloromethane (20.0 mL). The resulting mixture was stirred at 25° C. for 14 hr. The obtained mixture was concentrated under reduced pressure. The residue was diluted with water (40.0 mL) and filtered off. The filtrate was basified with solid K$_2$CO$_3$ to pH≈10. The resulting mixture was extracted with DCM (2×20.0 mL). The organic layers were separated, dried over Na$_2$SO$_4$ and concentrated in vacuo to afford 5-(3-methyl-2,3,4,5-tetrahydropyridin-6-yl)-1,2-benzothiazole (540 mg, 2.34 mmol, 62.4% yield) as yellow gum.

LCMS(ESI): [M+H]$^+$ m/z: calcd 231.11; found 231.0; Rt=0.700.

Step 3: The Synthesis of 5-[(2R,5S)-5-methyl-2-piperidyl]-1,2-benzothiazole

To a stirring solution of 5-(3-methyl-2,3,4,5-tetrahydropyridin-6-yl)-1,2-benzothiazole (540 mg, 2.34 mmol) in Methanol (30.0 mL) Sodium borohydride (133 mg, 3.52 mmol, 124 µL) was added portion-wise. The resulting mixture was stirred at 20° C. for 1.5 hr. The obtained mixture was concentrated under reduced pressure. The residue was partitioned between water (30.0 mL) and DCM (40.0 mL). The organic layer was separated, dried over Na$_2$SO$_4$ and concentrated in vacuo to afford 5-[(2R,5S)-5-methyl-2-piperidyl]-1,2-benzothiazole (460 mg, 1.98 mmol, 84.5% yield) as yellow oil.

LCMS(ESI): [M+H]$^+$ m/z: calcd 233.13; found 233.2; Rt=0.785.

Step 4: The Synthesis of tert-butyl N-[5-[[2-[(2R,5S)-2-(1,2-benzothiazol-5-yl)-5-methyl-1-piperidyl]-2-oxo-acetyl]amino]-3-cyclopropyl-2-pyridyl]carbamate To a stirred mixture of 5-[(2R,5S)-5-methyl-2-piperidyl]-1,2-benzothiazole (230 mg, 990 µmol), 2-[[6-(tert-butoxycarbonylamino)-5-cyclopropyl-3-pyridyl]amino]-2-oxo-acetic acid (318 mg, 990 µmol) and Triethylamine (250 mg, 2.47 mmol, 345 µL) in Dimethylformamide (3.00 mL) HATU (414 mg, 1.09 mmol) was added. The resulting reaction mixture was stirred at 25° C. for 4 hr. The obtained mixture was subjected to HPLC (0-5 min 40-65% water-ACN; flow: 30 mL/min, column: Chromatorex 18 SMB100-5T, 100×19 mm, 5 µm), to afford tert-butyl N-[5-[[2-[(2R,5S)-2-(1,2-benzothiazol-5-yl)-5-methyl-1-piperidyl]-2-oxo-acetyl]amino]-3-cyclopropyl-2-pyridyl]carbamate (74.0 mg, 138 µmol, 13.9% yield) as a white solid.

LCMS(ESI): [M+H]$^+$ m/z: calcd 536.26; found 536; Rt=3.898.

Step 5: The Synthesis of N-(6-amino-5-cyclopropyl-3-pyridyl)-2-[(2R,5S)-2-(1,2-benzothiazol-5-yl)-5-methyl-1-piperidyl]-2-oxo-acetamide Water (1.00 g, 55.5 mmol, 1.00 mL) was added to a solution of tert-butyl N-[5-[[2-[(2R,5S)-2-(1,2-benzothiazol-5-yl)-5-methyl-1-piperidyl]-2-oxo-acetyl]amino]-3-cyclopropyl-2-pyridyl]carbamate (74.0 mg, 138 µmol) in Dioxane (2.00 mL). The resulting mixture was stirred at 90° C. for 16 hr. The obtained mixture was subjected to HPLC (0-5 min 40-90% water-methanol, +0.1% vol. of 25% aq. NH$_3$, 30 mL/min, column: YMC-Actus Triart C18, 100×20 mm, 5 µm), to afford N-(6-amino-5-cyclopropyl-3-pyridyl)-2-[(2R,5S)-2-(1,2-benzothiazol-5-yl)-5-methyl-1-piperidyl]-2-oxo-acetamide (44.0 mg, 101 µmol, 73.1% yield) as a white solid.

LCMS(ESI): [M+H]$^+$ m/z: calcd 436.2; found 436.2; Rt=2.413.

Step 6: The Synthesis of N-(6-amino-5-cyclopropyl-3-pyridyl)-2-[(2S,5R)-2-(1,2-benzothiazol-5-yl)-5-methyl-1-piperidyl]-2-oxo-acetamide and N-(6-amino-5-cyclopropyl-3-pyridyl)-2-[(2R,5S)-2-(1,2-benzothiazol-5-yl)-5-methyl-1-piperidyl]-2-oxo-acetamide N-(6-amino-5-cyclopropyl-3-pyridyl)-2-[(2R,5S)-2-(1,2-benzothiazol-5-yl)-5-methyl-1-piperidyl]-2-oxo-acetamide (44.0 mg, 101 µmol) was subjected to Chiral HPLC (System: Column: Chiralpak IB (250*20 mm, 5 mkm), Mobile phase: Hexane-IPA-MeOH, 50-25-25; Flow rate: 12 mL/min. 24° C., Wavelength: 205 nm, 215 nm) to afford Compound 1400 N-(6-amino-5-cyclopropyl-3-pyridyl)-2-[(2S,5R)-2-(1,2-benzothiazol-5-yl)-5-methyl-1-piperidyl]-2-oxo-acetamide (16.9 mg, 38.8 µmol, 76.8% yield; RetTime=11.112 min(analytical), 13.9 min(preparative).) and Compound 1153 N-(6-amino-5-cyclopropyl-3-pyridyl)-2-[(2R,5S)-2-(1,2-benzothiazol-5-yl)-5-methyl-1-piperidyl]-2-oxo-acetamide (23.0 mg, crude; RetTime=19.536 min (analytical), 23.5 min(preparative)) as white solids.

(Compound 1400):
N-(6-amino-5-cyclopropyl-3-pyridyl)-2-[(2S,5R)-2-(1,2-benzothiazol-5-yl)-5-methyl-1-piperidyl]-2-oxo-acetamide $^1$H NMR (600 MHz, DMSO-d$_6$) δ 10.53-10.43 (m, 1H), 9.12-9.08 (m, 1H), 8.26-8.19 (m, 1H), 8.18-8.13 (m, 1H), 8.09-7.96 (m, 1H), 7.65-7.51 (m, 1H), 7.38-7.24 (m, 1H), 5.79-5.27 (m, 3H), 4.07-3.49 (m, 1H), 3.28-2.78 (m, 1H), 2.35-2.26 (m, 1H), 2.23-2.07 (m, 1H), 1.93-1.84 (m, 1H), 1.75-1.60 (m, 2H), 1.41-1.30 (m, 1H), 1.04-1.00 (m, 3H), 0.91-0.82 (m, 2H), 0.48-0.38 (m, 2H).

LCMS(ESI): [M+H]$^+$ m/z: calcd 436.2; found 436.2; Rt=1.041.

(Compound 1153):
N-(6-amino-5-cyclopropyl-3-pyridyl)-2-[(2R,5S)-2-(1,2-benzothiazol-5-yl)-5-methyl-1-piperidyl]-2-oxo-acetamide $^1$H NMR (600 MHz, DMSO-d$_6$) δ 10.52-10.44 (m, 1H), 9.12-9.07 (m, 1H), 8.26-8.19 (m, 1H), 8.19-8.13 (m, 1H), 8.08-7.95 (m, 1H), 7.64-7.52 (m, 1H), 7.41-7.22 (m, 1H), 5.79-5.28 (m, 3H), 4.07-3.49 (m, 1H), 3.27-2.78 (m, 1H), 2.33-2.26 (m, 1H), 2.23-2.08 (m, 1H), 1.93-1.84 (m, 1H), 1.76-1.61 (m, 2H), 1.40-1.32 (m, 1H), 1.03-1.01 (m, 3H), 0.90-0.82 (m, 2H), 0.49-0.38 (m, 2H).

LCMS(ESI): [M+H]$^+$ m/z: calcd 436.2; found 436.2; Rt=1.060.

Example 440. The Synthesis of N-(6-amino-5-cyclopropyl-3-pyridyl)-2-[(2R,5S)-5-methyl-2-[2-(1-methyl-4-piperidyl)-1,3-benzothiazol-5-yl]-1-piperidyl]-2-oxo-acetamide (Compound 1222) and N-(6-amino-5-cyclopropyl-3-pyridyl)-2-[(2S,5R)-5-methyl-2-[2-(1-methyl-4-piperidyl)-1,3-benzothiazol-5-yl]-1-piperidyl]-2-oxo-acetamide (Compound 1201)

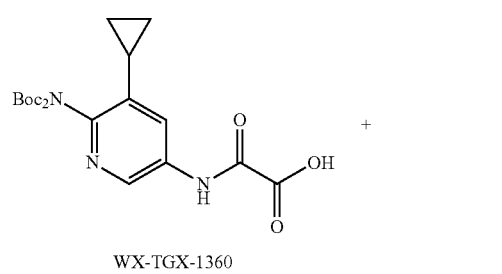

WX-TGX-1360

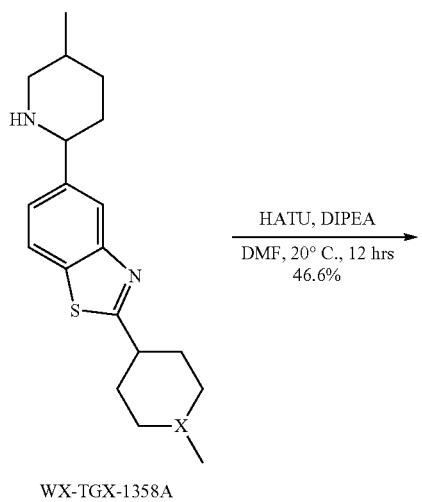

WX-TGX-1358A

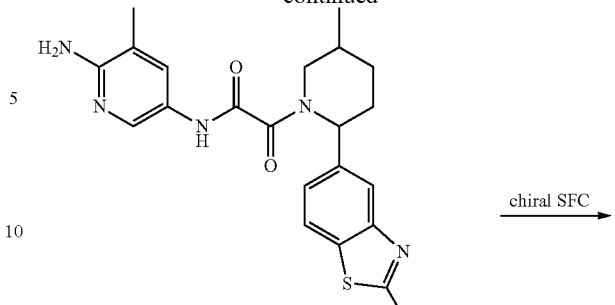

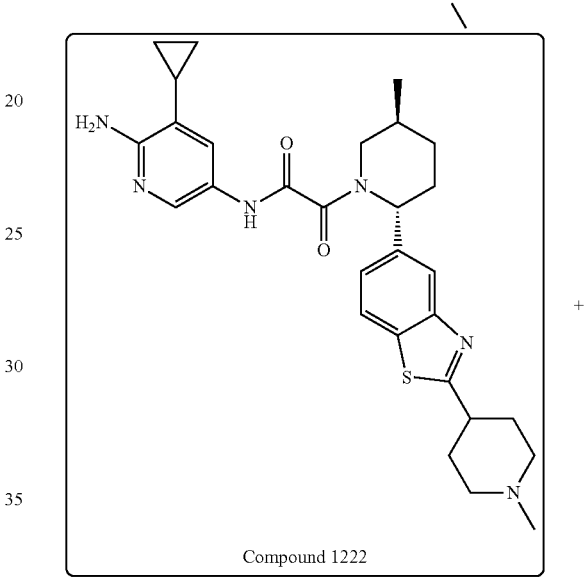

Compound 1222

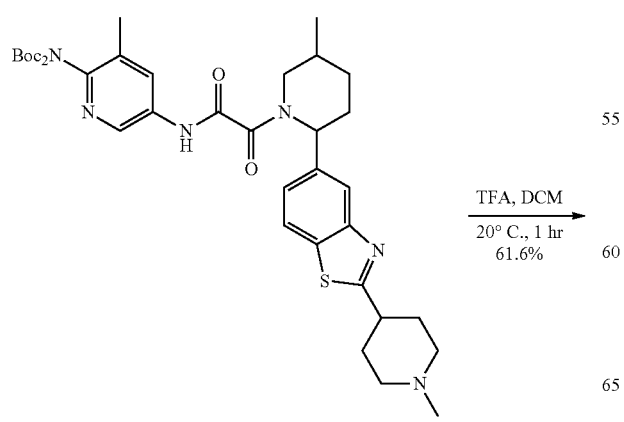

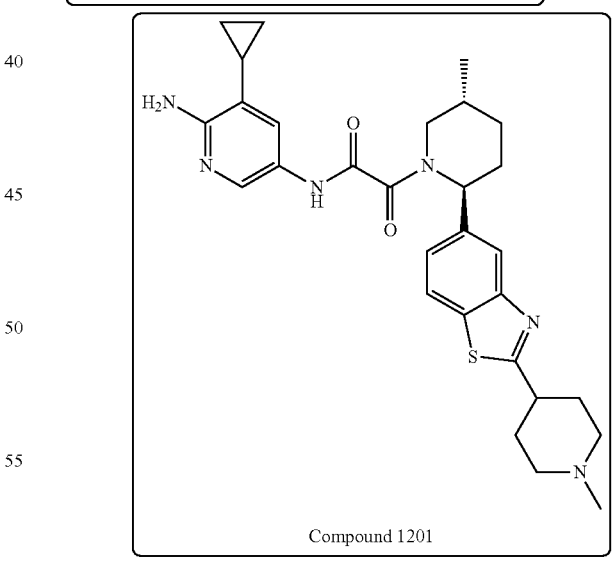

Compound 1201

Step 1: The Synthesis of tert-butyl N-tert-butoxycarbonyl-N-[3-methyl-5-[[2-[5-methyl-2-[2-(1-methyl-4-piperidyl)-1,3-benzothiazol-5-yl]-1-piperidyl]-2-oxo-acetyl]amino]-2-pyridyl]carbamate To a mixture of 2-(1-methyl-4-piperidyl)-5-(5-methyl-2-piperidyl)-1,3-benzothiazole (150 mg, 0.46 mmol), 2-[[6-

[bis(tert-butoxycarbonyl)amino]-5-cyclopropyl-3-pyridyl]amino]-2-oxo-acetic acid (191 mg, 0.45 mmol) in DMF (5 mL) were added DIPEA (371 mg, 2.87 mmol) and HATU (225 mg, 0.59 mmol) and the mixture was stirred at 20° C. for 12 hours. The mixture was diluted with EtOAc (50 mL), washed with brine (20 mL*3), dried over $Na_2SO_4$, filtered and concentrated under reduce pressure to give the crude product. The crude product was purified by flash chromatography (ISCO; 24 g AgelaFlash Silica Flash Column, petroleum ether/EtOAc with EtOAc from 0~50%, flow rate=30 mL/min, 254 nm) to afford tert-butyl N-tert-butoxycarbonyl-N-[3-methyl-5-[[2-[5-methyl-2-[2-(1-methyl-4-piperidyl)-1,3-benzothiazol-5-yl]-1-piperidyl]-2-oxo-acetyl]amino]-2-pyridyl]carbamate (150 mg, 46.6% yield) as a light-yellow solid. LCMS (ESI) [M+H]+ m/z: calcd 733.3, found 733.4.

Step 2: The Synthesis of N-(6-amino-5-methyl-3-pyridyl)-2-[5-methyl-2-[2-(1-methyl-4-piperidyl)-]1,3-benzothiazol-5-yl]-1-piperidyl]-2-oxo-acetamide A solution of tert-butyl N-tert-butoxycarbonyl-N-[3-methyl-5-[[2-[5-methyl-2-[2-(1-methyl-4-piperidyl)-1,3-benzothiazol-5-yl]-1-piperidyl]-2-oxo-acetyl]amino]-2-pyridyl]carbamate (145 mg, 0.21 mmol) in TFA (7.25 mL, 94.1 mmol) and DCM (2 mL) was stirred at 20° C. for 1 hour. The mixture was concentrated under reduce pressure to give the crude product as brown oil. The crude product was further purified by preparative HPLC purification (Instrument: Gilson GX-281 Liquid Handler, Gilson 322 Pump, Gilson 156 UV Detector; Column: Durashell 150×25 mm×5 m; Mobile phase A: water (0.05% $NH_3H_2O$+10 mM $NH_4HCO_3$); Mobile phase B: MeCN; Gradient: B from 36% to 66% in 7.8 min, hold 100% B for 2.0 min; Flow Rate: 25 mL/min; Column Temperature: 30° C.; Wavelength: 220 nm, 254 nm) to afford N-(6-amino-5-methyl-3-pyridyl)-2-[5-methyl-2-[2-(1-methyl-4-piperidyl)-1,3-benzothiazol-5-yl]-1-piperidyl]-2-oxo-acetamide (64 mg, 61.6% yield) as a white solid. LCMS (ESI) [M+H]+ m/z: calcd 533.2, found 533.2.

Step 3: The Synthesis of N-(6-amino-5-cyclopropyl-3-pyridyl)-2-[(2R,5S)-5-methyl-2-[2-(1-methyl-4-piperidyl)-1,3-benzothiazol-5-yl]-1-piperidyl]-2-oxo-acetamide (Compound 1222) and N-(6-amino-5-cyclopropyl-3-pyridyl)-2-[(2S,5R)-5-methyl-2-[2-(1-methyl-4-piperidyl)-1,3-benzothiazol-5-yl]-1-piperidyl]-2-oxo-acetamide (Compound 1201

The N-(6-amino-5-cyclopropyl-3-pyridyl)-2-[5-methyl-2-[2-(1-methyl-4-piperidyl)-1,3-benzothiazol-5-yl]-1-piperidyl]-2-oxo-acetamide (50 mg, 0.094 mmol) was sent to SFC purification (Instrument: Berger, Multigr AM-II; Column: Chiralpak AD 250×30 mm I.D. 5 m; Mobile phase: supercritical $CO_2$/EtOH (0.1% $NH_3$—$H_2O$, v %)=65/35; Flow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1222 (peak 1, retention time=5.166 min) and Compound 1201 (peak 2, retention time=5.951 min).

Compound 1222: N-(6-amino-5-cyclopropyl-3-pyridyl)-2-[(2R,5S)-5-methyl-2-[2-(1-methyl-4-piperidyl)-1,3-benzothiazol-5-yl]-1-piperidyl]-2-oxo-acetamide (23.1 mg, single unknown enantiomer with trans relative chemistry, peak 1, retention time=5.166 min, white solid).

1H NMR (400 MHz, methanol-$d_4$) δ ppm 7.77-8.15 (m, 3H), 7.34-7.62 (m, 1H), 7.21-7.64 (m, 1H), 5.42-5.98 (m, 1H), 3.68-3.87 (m, 1H), 3.67-4.16 (m, 1H), 3.36-3.59 (m, 1H), 3.24 (br s, 1H), 2.84-2.97 (m, 1H), 2.77-3.23 (m, 2H), 2.61-2.83 (m, 1H), 2.20-2.41 (m, 4H), 1.78-2.05 (m, 4H), 1.38-1.75 (m, 2H), 1.16 (br d, J 6.9 Hz, 3H), 0.81-1.03 (m, 2H), 0.41-0.70 (m, 2H); LCMS (ESI) [M+H]+ m/z: calcd 533.1, found 533.2; HPLC: 100% @254 nm; 100.0% ee.

Compound 1201: N-(6-amino-5-cyclopropyl-3-pyridyl)-2-[(2S,5R)-5-methyl-2-[2-(1-methyl-4-piperidyl)-1,3-benzothiazol-5-yl]-1-piperidyl]-2-oxo-acetamide (22.4 mg, single unknown enantiomer with trans relative chemistry, peak 2, retention time=5.951 min, white solid). 1H NMR (400 MHz, methanol-$d_4$) δ ppm 8.12 (br s, 1H), 7.72-8.15 (m, 2H), 7.58 (br s, 1H), 7.20-7.65 (m, 1H), 5.85 (br s, 1H), 5.38-5.56 (m, 1H), 3.72-4.15 (m, 1H), 3.40-3.52 (m, 1H), 3.03 (br d, J=11.1 Hz, 1H), 2.86-3.24 (m, 2H), 2.17-2.40 (m, 8H), 1.82-2.09 (m, 3H), 1.56-1.76 (m, 1H), 1.37-1.55 (m, 1H), 1.07-1.30 (m, 3H), 0.83-1.04 (m, 2H), 0.46-0.72 (m, 2H); LCMS (ESI) [M+H]+ m/z: calcd 533.1, found 533.2; HPLC: 98.82% @254 nm; 100% ee.

Example 441. The Synthesis of N-(6-amino-5-cyclopropyl-3-pyridyl)-2-[(2S,5S)-5-methyl-2-(2-tetrahydropyran-4-yl-1,3-benzothiazol-5-yl)-1-piperidyl]-2-oxo-acetamide (Compound 1258

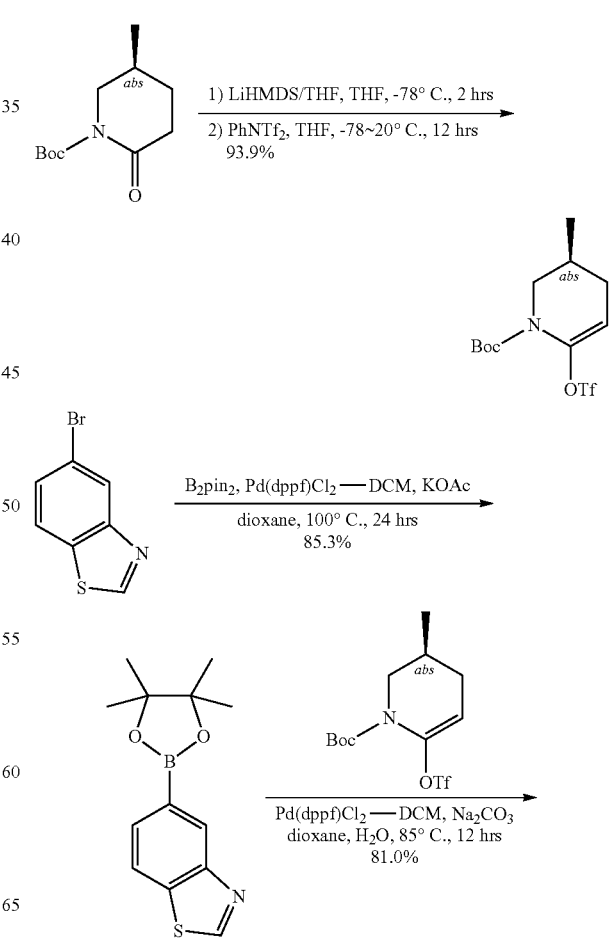

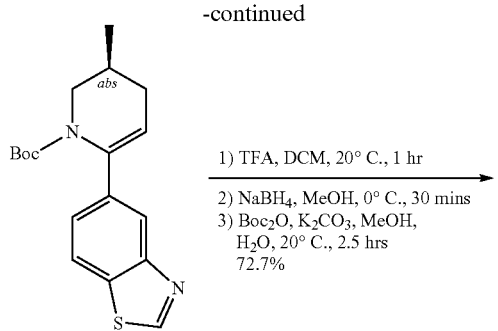
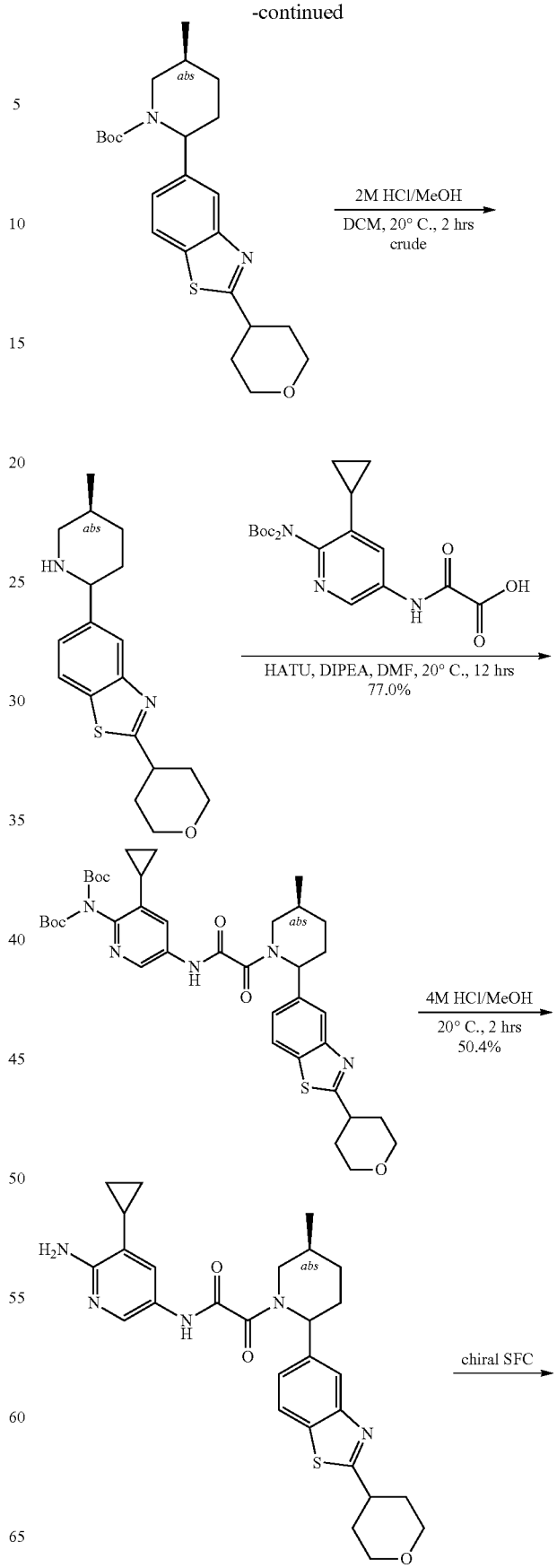

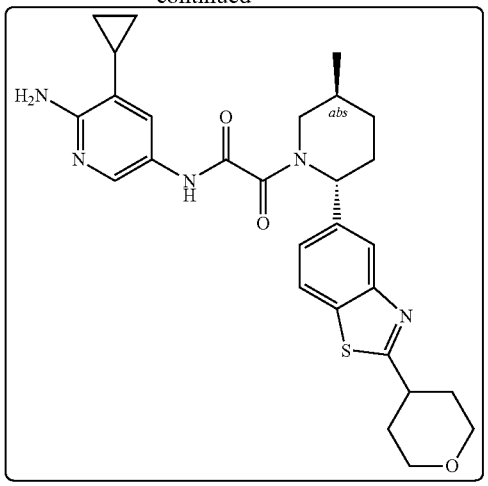

Step 9: Synthesis of tert-butyl N-tert-butoxycarbonyl-N-[3-cyclopropyl-5-[[2-[(5S)-5-methyl-2-(2-tetrahydropyran-4-yl-1,3-benzothiazol-5-yl)-1-piperidyl]-2-oxo-acetyl]amino]-2-pyridyl]carbamate To a mixture of 5-((5S)-5-methyl-2-piperidyl)-2-tetrahydropyran-4-yl-1,3-benzothiazole (70 mg, 0.198 mmol, HCl), [2-[[6-[bis(tert-butoxycarbonyl)amino]-5-cyclopropyl-3-pyridyl]amino]-2-oxo-acetyl]oxysodium (89.8 mg, 0.202 mmol), HATU (80 mg, 0.210 mmol) and DMF (3 mL) was added DIPEA (0.1 mL, 0.574 mmol) and the mixture was stirred at 20° C. for 12 hours. The resulting mixture was quenched by addition of water (10 mL) and extracted with EtOAc (50 mL*3). The combined organic layer was washed with saturated NH$_4$Cl aqueous solution (10 mL*2), brine (10 mL), dried over anhydrous Na$_2$SO$_4$, filtered and concentrated under reduced pressure to give a residue which was purified by flash chromatography (ISCO®; 12 g Agela-Flash® Silica Flash Column, petroleum ether/EtOAc with EtOAc from 0~68%, Flow Rate: 30 mL/min, 254 nm) to afford tert-butyl N-tert-butoxycarbonyl-N-[3-cyclopropyl-5-[[2-[(5S)-5-methyl-2-(2-tetrahydropyran-4-yl-1,3-benzothiazol-5-yl)-1-piperidyl]-2-oxo-acetyl]amino]-2-pyridyl]carbamate (110 mg, 77.0% yield) as yellow solid.

Step 10: Synthesis of tert-butyl N-tert-butoxycarbonyl-N-[3-cyclopropyl-5-[[2-[(5S)-5-methyl-2-(2-tetrahydropyran-4-yl-1,3-benzothiazol-5-yl)-1-piperidyl]-2-oxo-acetyl]amino]-2-pyridyl]carbamate A mixture of tert-butyl N-tert-butoxycarbonyl-N-[3-cyclopropyl-5-[[2-[(5S)-5-methyl-2-(2-tetrahydropyran-4-yl-1,3-benzothiazol-5-yl)-1-piperidyl]-2-oxo-acetyl]amino]-2-pyridyl]carbamate (110 mg, 0.153 mmol) and 4M MeOH/HCl (4 mL, 16 mmol) was stirred at 20° C. for 2 hours. The mixture was added NH$_3$—H$_2$O (1 mL) and concentrated under reduced pressure to give a residue which was purified by preparative HPLC (Instrument: Gilson GX-281 Liquid Handler, Gilson 322 Pump, Gilson 156 UV Detector; Column: Waters Xbridge 150×25 mm×5 m; Mobile phase A: H$_2$O with 0.05% NH$_3$—H$_2$O (v %); Mobile phase B: MeCN; Gradient: B from 35% to 65% in 7.8 min, hold 100% B for 2.5 min; Flow Rate: 25 mL/min; Column Temperature: 30° C.; Wavelength: 220 nm, 254 nm) to afford N-(6-amino-5-cyclopropyl-3-pyridyl)-2-[(5S)-5-methyl-2-[(2-tetrahydropyran-4-yl-1,3-benzothiazol-5-yl)-1-piperidyl]-2-oxo-acetamide (40 mg, 50.4% yield) as white solid.

Step 11: Synthesis of N-(6-amino-5-cyclopropyl-3-pyridyl)-2-[(2S,5S)-5-methyl-2-(2-tetrahydropyran-4-yl-1,3-benzothiazol-5-yl)-1-piperidyl]-2-oxo-acetamide (Compound 1258

N-(6-amino-5-cyclopropyl-3-pyridyl)-2-[(5S)-5-methyl-2-(2-tetrahydropyran-4-yl-1,3-benzothiazol-5-yl)-1-piperidyl]-2-oxo-acetamide (40 mg, 77.0 μmol) was separated by SFC Instrument (Thar 800Q; Daicel Chiralpak IG (250 mm*30 mm, 10 m); Mobile phase: supercritical CO$_2$/EtOH (0.1% NH$_3$—H$_2$O, v %)=60/40; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give N-(6-amino-5-cyclopropyl-3-pyridyl)-2-[(2S,5S)-5-methyl-2-(2-tetrahydropyran-4-yl-1,3-benzothiazol-5-yl)-1-piperidyl]-2-oxo-acetamide (25 mg, single known enantiomer with trans relative chemistry, peak 2, retention time=5.211 min, white solid). $^1$H NMR (400 MHz, methanol-d$_4$) δ ppm 7.73-8.17 (m, 3H), 7.18-7.63 (m, 2H), 5.46-5.89 (m, 1H), 4.00-4.17 (m, 2H), 3.53-3.80 (m, 2H), 3.44 (br d, J=11.6 Hz, 2H), 2.93-3.28 (m, 1H), 1.87-2.40 (m, 8H), 1.57-1.76 (m, 1H), 1.49 (br d, J=11.9 Hz, 1H), 1.16 (br d, J=6.9 Hz, 3H), 0.84-1.04 (m, 2H), 0.49-0.69 (m, 2H); LCMS(ESI) [M+H]$^+$ m/z: calcd 520.2, found 520.2; HPLC: 100%@220 nm, 100%@254 nm; 100% ee.

Example 442. The Synthesis of rel-N-(6-amino-5-cyclopropyl-3-pyridyl)-2-[(2S,5R)-2-(3-chlorophenyl)-5-methyl-1-piperidyl]-2-oxo-acetamide (Compound 1169) and rel-N-(6-amino-5-cyclopropyl-3-pyridyl)-2-[(2R,5S)-2-(3-chlorophenyl)-5-methyl-1-piperidyl]-2-oxo-acetamide (Compound 1119

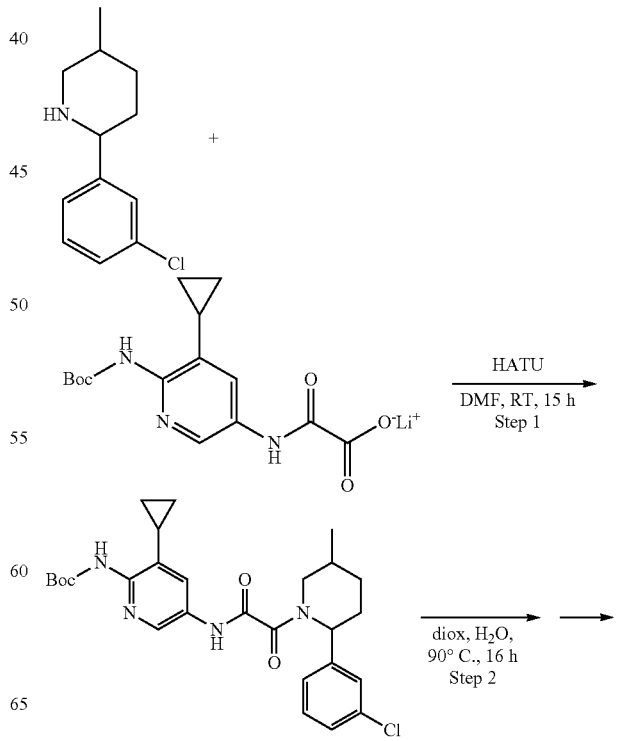

2307

-continued

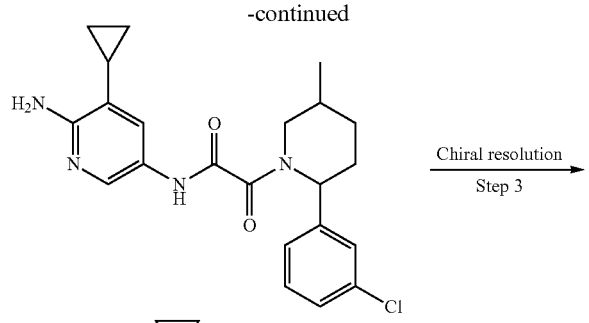

Chiral resolution
Step 3 →

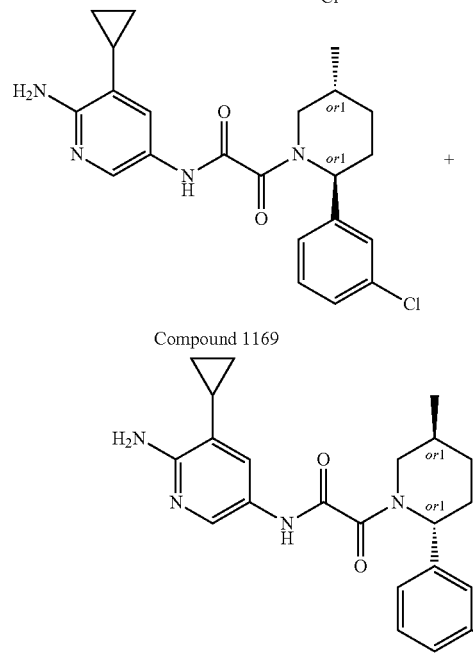

Compound 1169

Compound 1119

Step 1: The Synthesis of tert-butyl N-[5-[[2-[2-(3-chlorophenyl)-5-methyl-1-piperidyl]-2-oxo-acetyl]amino]-3-cyclopropyl-2-pyridyl]carbamate

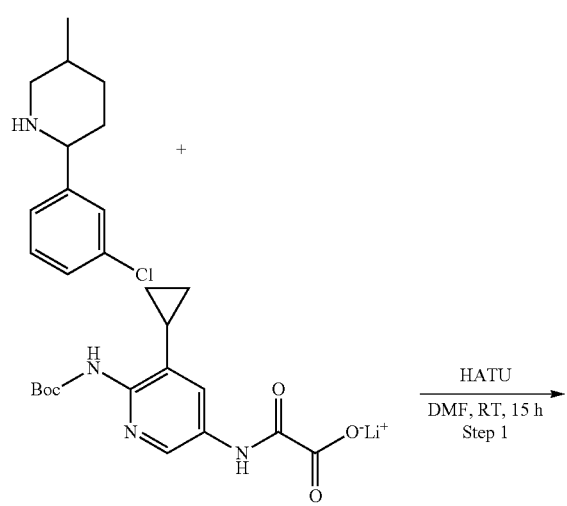

HATU
DMF, RT, 15 h
Step 1 →

2308

-continued

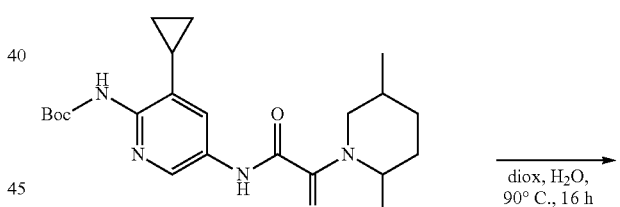

2-(3-chlorophenyl)-5-methyl-piperidine (150 mg, 715.26 umol) and HATU (326.36 mg, 858.31 umol) were mixed in dry DMF (5 mL) at rt and the resulting mixture was stirred for 5 min. HATU (326.36 mg, 858.31 umol) was added thereto and the resulting mixture was stirred at rt for 15 min. The resulting mixture was poured into water, extracted 3 times with EtOAc, combined organics were washed with water, brine and evaporated. The residue was subjected to HPLC (50-100% 0.5-6.5 min water-acetonitrile+FA; flow 30 mL/min (loading pump; 4 mL/min acetonitrile); column SunFire C18 100×19 mm 5 um (R). tert-butyl N-[5-[[2-[2-(3-chlorophenyl)-5-methyl-1-piperidyl]-2-oxo-acetyl]amino]-3-cyclopropyl-2-pyridyl]carbamate (287.9 mg, 561.18 umol, 78.46% yield) was obtained as a brownish gum.

LCMS(ESI): [M+H]$^+$ m/z: calcd 513.2; found 513.2; Rt=3.883 min.

Step 2: The Synthesis of N-(6-amino-5-cyclopropyl-3-pyridyl)-2-[2-(3-chlorophenyl)-5-methyl-1-piperidyl]-2-oxo-acetamide tert-butyl N-[5-[[2-[2-(3-chlorophenyl)-5-methyl-1-piperidyl]-2-oxo-acetyl]amino]-3-cyclopropyl-2-pyridyl]carbamate (287.9 mg, 561.18 umol) was dissolved in water (2 mL)/dioxane (2 mL) mixture and was heated at 90° C. overnight. The resulting mixture was evaporated to dryness to give N-(6-amino-5-cyclopropyl-3-pyridyl)-2-[2-(3-chlorophenyl)-5-methyl-1-piperidyl]-2-oxo-acetamide (0.22 g, 532.80 umol, 94.94% yield) as a yellow solid.

LCMS(ESI): [M+H]⁺ m/z: calcd 413.2; found 413.4; Rt=3.124 min.

Step 3: The Synthesis of rel-N-(6-amino-5-cyclopropyl-3-pyridyl)-2-[(2S,5R)-2-(3-chlorophenyl)-5-methyl-1-piperidyl]-2-oxo-acetamide (Compound 1169) and rel-N-(6-amino-5-cyclopropyl-3-pyridyl)-2-[(2R,5S)-2-(3-chlorophenyl)-5-methyl-1-piperidyl]-2-oxo-acetamide (Compound 1119

The mixture of diastereomers was separated by chiral chromatography in two runs: 1st run (Chiralpak IC-III (250*20, 5 mkm), Hexane-IPA-MeOH, 60-20-20, 12 mL/min) and 2nd run (Chiralpak AD-H-III (250*20 mm, 5 mkm), Hexane-IPA-MeOH, 70-15-15, 12 mL/min) to obtain N-(6-amino-5-cyclopropyl-3-pyridyl)-2-[(2S,5R)-2-(3-chlorophenyl)-5-methyl-1-piperidyl]-2-oxo-acetamide (51.72 mg, 125.26 umol, 21.55% yield) and N-(6-amino-5-cyclopropyl-3-pyridyl)-2-[(2R,5S)-2-(3-chlorophenyl)-5-methyl-1-piperidyl]-2-oxo-acetamide (44.25 mg, 107.17 umol, 18.44% yield).

Preparative:

1st run:

RT for Compound 1169 (Chiralpak IC-III (250*20, 5 mkm), Hexane-IPA-MeOH, 60-20-20, 12 mL/min)=18.792 min; (together with its cis impurity)

RT for Compound 1119 (Chiralpak IC-III (250*20, 5 mkm), Hexane-IPA-MeOH, 60-20-20, 12 mL/min)=25.119 min.

Preparative:

2nd run:

RT for Compound 1169 (Chiralpak AD-H-III (250*20 mm, 5 mkm), Hexane-IPA-MeOH, 70-15-15, 12 mL/min)=41.448 min; (together with its cis impurity)

Compound 1169:

Yield: 51.72 mg (21.55%)

RT (Chiralpak IC (250*4.6, 5 mkm), Hexane-IPA-MeOH, 60-20-20, 0.6 mL/min)=17.466 min.

¹H NMR (500 MHz, dmso) δ 0.40-0.50 (m, 2H), 0.84-0.90 (m, 2H), 0.96-1.05 (m, 3H), 1.24-1.37 (m, 1H), 1.59-1.69 (m, 2H), 1.79-1.91 (m, 1H), 1.99-2.10 (m, 1H), 2.14-2.25 (m, 1H), 2.68-3.25 (m, 1H), 3.45-4.04 (m, 1H), 5.13-5.57 (m, 1H), 5.71-5.80 (m, 2H), 7.23-7.37 (m, 4H), 7.39-7.47 (m, 1H), 7.96-8.10 (m, 1H), 10.46-10.58 (m, 1H).

LCMS(ESI): [M+H]⁺ m/z: calcd 413.2; found 413.2; Rt=2.535 min.

Compound 1119:

Yield: 44.25 mg (18.44%)

RT (Chiralpak IC (250*4.6, 5 mkm), Hexane-IPA-MeOH, 60-20-20, 0.6 mL/min)=22.691 min.

¹H NMR (500 MHz, dmso) δ 0.40-0.50 (m, 2H), 0.82-0.90 (m, 2H), 0.96-1.04 (m, 3H), 1.24-1.38 (m, 1H), 1.54-1.73 (m, 2H), 1.80-1.92 (m, 1H), 1.96-2.08 (m, 1H), 2.11-2.26 (m, 1H), 2.69-3.26 (m, 1H), 3.44-4.06 (m, 1H), 5.13-5.59 (m, 1H), 5.70-5.82 (m, 2H), 7.24-7.37 (m, 4H), 7.38-7.44 (m, 1H), 7.94-8.06 (m, 1H), 10.43-10.57 (m, 1H).

LCMS(ESI): [M+H]⁺ m/z: calcd 413.2; found 413.2; Rt=2.553 min.

Example 443. The Synthesis of rel-N-(6-amino-5-cyclopropylpyridin-3-yl)-2-((2R,5R)-2-(benzo[d]thiazol-5-yl)-4,4-difluoro-5-methylpiperidin-1-yl)-2-oxoacetamide (Compound 1307) and rel-N-(6-amino-5-cyclopropylpyridin-3-yl)-2-((2R,5S)-2-(benzo[d]thiazol-5-yl)-4,4-difluoro-5-methylpiperidin-1-yl)-2-oxoacetamide (Compound 1207

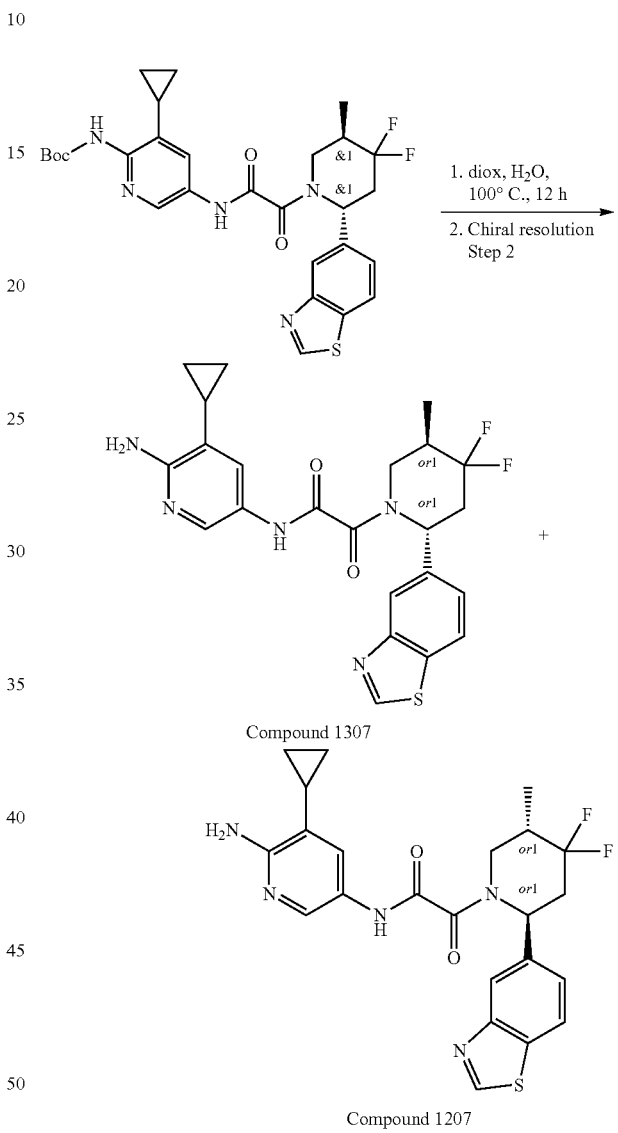

A solution of tert-butyl N-[5-[[2-[(2R,5R)-2-(1,3-benzothiazol-5-yl)-4,4-difluoro-5-methyl-1-piperidyl]-2-oxoacetyl]amino]-3-cyclopropyl-2-pyridyl]carbamate (1.5 g, 2.62 mmol) in Dioxane (15 mL) and Water (15 mL) was heated at 100° C. for 12 hr. Solvents were evaporated and the crude material was purified by HPLC (2-10 min; 20-55% acetonitrile, 30 mL/min (loading pump 4 mL MeCN), column: SunFire 100*19 mm, 5 microM) to obtain racemic mixture. Resulting mixture was purified by chiral chromatography (Chiralpak AS-H (250*20 mm, 5 mkm), Hexane-IPA-MeOH, 60-20-20, 12 mL/min). Racemization on column was observed. Two fraction with different ratio of diastereomers (12%/88%-16.23 mg and 65%/35%-44.05 mg) of N-(6-amino-5-cyclopropyl-3-pyridyl)-2-[(2R,5R)-2-

(1,3-benzothiazol-5-yl)-4,4-difluoro-5-methyl-1-piperidyl]-2-oxo-acetamide (60.28 mg, 127.84 umol, 4.87% yield) was obtained.

Compound 1307:

Yield: 16.23 mg (26.92%)

RT (Chiralpak AS-H (250*4.6, 5 mkm), Hexane-IPA-MeOH, 50-25-25, 0.6 mL/min)=11.576 min (12%), 16.249 min (88%).

$^1$H NMR (600 MHz, dmso) δ 0.37-0.54 (m, 2H), 0.81-0.94 (m, 2H), 1.10 (d, 3H), 1.55-1.73 (m, 1H), 2.14-2.27 (m, 1H), 2.82-3.21 (m, 2H), 3.40-3.58 (m, 1H), 3.84-4.37 (m, 1H), 5.71-6.06 (m, 3H), 7.25-7.43 (m, 1H), 7.47 (d, 1H), 7.97-8.20 (m, 3H), 9.40 (s, 1H), 10.49-10.72 (m, 1H).

LCMS(ESI): [M+H]$^+$ m/z: calcd 472.2; found 472.2; Rt=2.795 min.

Compound 1207:

Yield: 44.05 mg (73.07%)

RT (Chiralpak AS-H (250*4.6, 5 mkm), Hexane-IPA-MeOH, 50-25-25, 0.6 mL/min)=11.576 min (65%), 16.249 min (35%).

$^1$H NMR (600 MHz, dmso) δ 0.53-0.66 (m, 2H), 0.95-1.03 (m, 2H), 1.10 (d, 3H), 1.68-1.82 (m, 1H), 2.19-2.27 (m, 1H), 2.61-3.02 (m, 2H), 3.15-3.58 (m, 1H), 3.93-4.36 (m, 1H), 5.75-6.01 (m, 1H), 7.39-7.73 (m, 4H), 8.01 (s, 1H), 8.11-8.19 (m, 1H), 8.19-8.35 (m, 1H), 9.40 (s, 1H), 10.85-11.19 (m, 1H).

LCMS(ESI): [M+H]$^+$ m/z: calcd 472.2; found 472.2; Rt=2.803 min.

Example 444. The Synthesis of N-(6-amino-5-ethyl-3-pyridyl)-2-[(2S,5S)-5-methyl-2-[2-(1-methyl-4-piperidyl)-1,3-benzothiazol-5-yl]-1-piperidyl]-2-oxo-acetamide (Compound 1143)

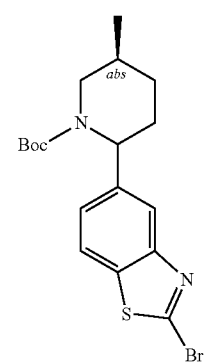

from WX-TGX-1359_001

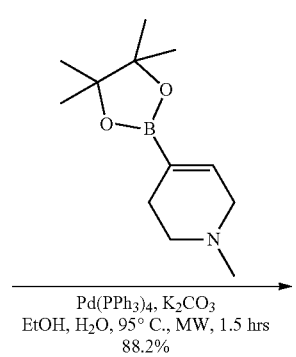

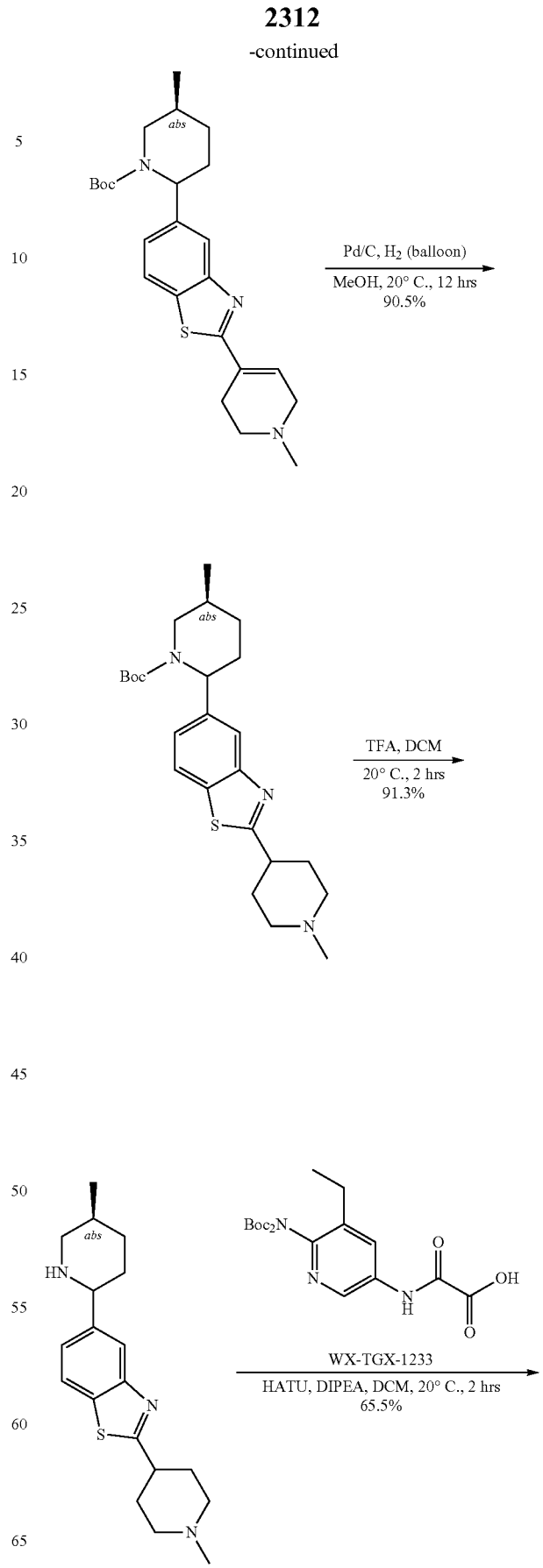

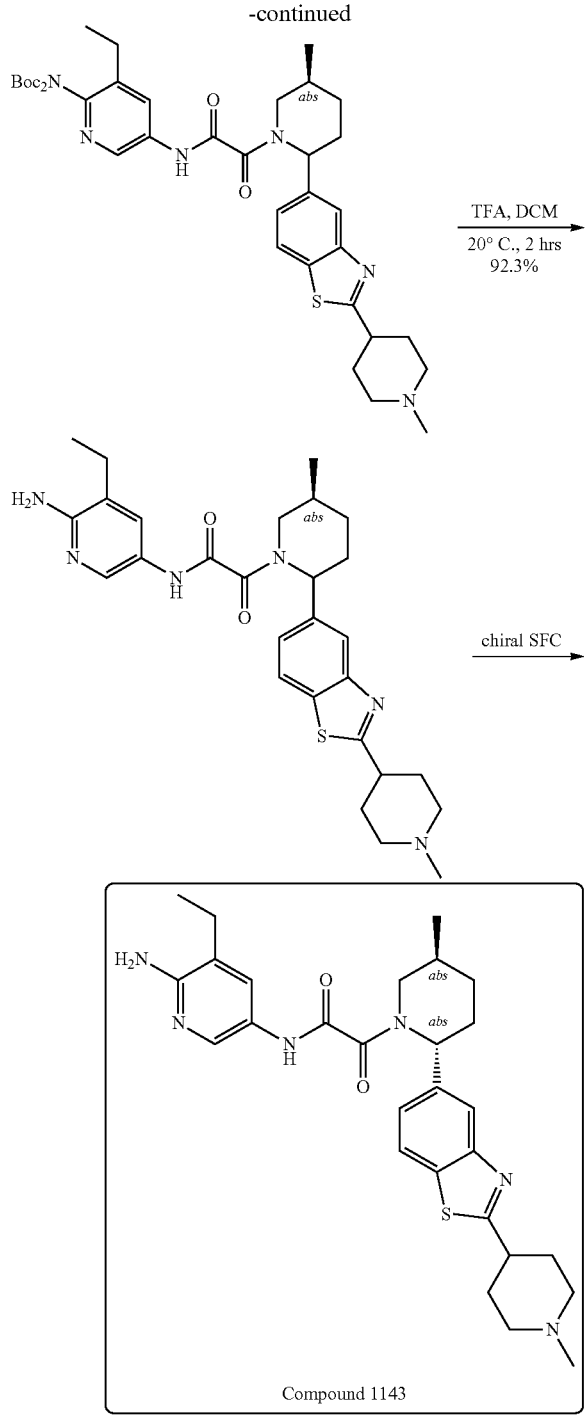

Compound 1143

Step 1: Synthesis of tert-butyl (5S)-5-methyl-2-[2-(1-methyl-3,6-dihydro-2H-pyridin-4-yl)-1,3-benzothiazol-5-yl]piperidine-1-carboxylate A mixture of tert-butyl (5S)-2-(2-bromo-1,3-benzothiazol-5-yl)-5-methyl-piperidine-1-carboxylate (1.2 g, 2.92 mmol), 1-methyl-4-(4,4,5,5-tetramethyl-1,3,2-dioxaborolan-2-yl)-3,6-dihydro-2H-pyridine (700 mg, 3.14 mmol), $K_2CO_3$ (1.20 g, 8.68 mmol), palladium; triphenylphosphane (360 mg, 0.312 mmol), EtOH (10 mL) and $H_2O$ (2 mL) was stirred at 95° C. for 1.5 hours. The resulting mixture was quenched by addition of water (10 mL) and extracted with EtOAc (20 mL*3). The combined organic layer was washed with saturated $NH_4Cl$ aqueous solution (10 mL*2), brine (10 mL), dried over anhydrous $Na_2SO_4$, filtered and concentrated under reduced pressure to give a residue which was purified by flash chromatography (ISCO®; 24 g AgelaFlash® Silica Flash Column, DCM/MeOH with MeOH from 0~20%, Flow Rate: 30 mL/min, 254 nm) to afford tert-butyl (5S)-5-methyl-2-[2-(1-methyl-3,6-dihydro-2H-pyridin-4-yl)-1,3-benzothiazol-5-yl]piperidine-1-carboxylate (1.1 g, 88.2% yield) as yellow solid.

Step 2: Synthesis of tert-butyl (5S)-5-methyl-2-[2-(1-methyl-4-piperidyl)-]1,3-benzothiazol-5-yl]piperidine-1-carboxylate A mixture of tert-butyl (5S)-5-methyl-2-[2-(1-methyl-3,6-dihydro-2H-pyridin-4-yl)-1,3-benzothiazol-5-yl]piperidine-1-carboxylate (1.10 g, 2.57 mmol), Pd/C (1 g, 10 wt % of Pd with 50 wt % of water) and MeOH (5 mL) was stirred at 20° C. for 12 hours under $H_2$ atmosphere (15 psi). The mixture was filtered and concentrated under reduced pressure to give tert-butyl (5S)-5-methyl-2-[2-(1-methyl-4-piperidyl)-1,3-benzothiazol-5-yl]piperidine-1-carboxylate (1 g, 90.5% yield) as black oil.

Step 3: Synthesis of 2-(1-methyl-4-piperidyl)-5-[(5S)-5-methyl-2-piperidyl]-]1,3-benzothiazole A mixture of tert-butyl (5S)-5-methyl-2-[2-(1-methyl-4-piperidyl)-1,3-benzothiazol-5-yl]piperidine-1-carboxylate (1 g, 2.33 mmol), TFA (2 mL, 26.0 mmol) and DCM (10 mL) was stirred at 20° C. for 2 hours. The mixture was concentrated under reduced pressure to give a residue which was mixed with $Na_2CO_3$ solid and MeOH and the mixture was stirred at 20° C. for 1 hour. The mixture was concentrated under reduced pressure to give a residue which was triturated with DCM (100 mL). The mixture was filtered and the filtrate was concentrated under reduced pressure to give 2-(1-methyl-4-piperidyl)-5-[(5S)-5-methyl-2-piperidyl]-1,3-benzothiazole (700 mg, 91.3% yield) as yellow oil

Step 4: Synthesis of tert-butyl N-tert-butoxycarbonyl-N-[3-ethyl-5-[[2-[(5S)-5-methyl-2-[2-(1-methyl-4-piperidyl)-1,3-benzothiazol-5-yl]-1-piperidyl]-2-oxo-acetyl]amino]-2-pyridyl]carbamate A mixture 2-[[6-[bis(tert-butoxycarbonyl)amino]-5-ethyl-3-pyridyl]amino]-2-oxo-acetic acid (130 mg, 0.317 mmol), 2-(1-methyl-4-piperidyl)-5-[(5S)-5-methyl-2-piperidyl]-1,3-benzothiazole (105 mg, 0.319 mmol), HATU (130 mg, 0.342 mmol), DIPEA (0.2 mL, 1.15 mmol) and DCM (20 mL) was stirred at 20° C. for 2 hours. The mixture was filtered and concentrated under reduced pressure to give a residue which was purified by flash chromatography (ISCO®; 24 g AgelaFlash® Silica Flash Column DCM/MeOH with MeOH from 0-20%, Flow Rate: 30 mL/min, 254 nm) to afford tert-butyl N-tert-butoxycarbonyl-N-[3-ethyl-5-[[2-[(5S)-5-methyl-2-[2-(1-methyl-4-piperidyl)-1,3-benzothiazol-5-yl]-1-piperidyl]-2-oxo-acetyl]amino]-2-pyridyl]carbamate (150 mg, 65.5% yield) as yellow oil.

Step 5: Synthesis of N-(6-amino-5-ethyl-3-pyridyl)-2-[(5S)-5-methyl-2-[2-(1-methyl-4-piperidyl)-1,3-benzothiazol-5-yl]-1-piperidyl]-2-oxo-acetamide A mixture of tert-butyl N-tert-butoxycarbonyl-N-[3-ethyl-5-[[2-[(5S)-5-methyl-2-[2-(1-methyl-4-piperidyl)-1,3- benzothiazol-5-yl]-1-piperidyl]-2-oxo-acetyl]amino]-2-pyridyl]carbamate (150 mg, 0.208 mmol), TFA (1 mL, 13.0 mmol) and DCM (2 mL) was stirred at 20° C. for 2 hours. The mixture was concentrated under reduced pressure to give a residue which was purified by preparative HPLC (Instrument: Gilson GX-281 Liquid Handler, Gilson 322 Pump, Gilson 156 UV Detector; Column: Waters Xbridge 150×25 mm×5 m; Mobile phase A: $H_2O$ with 0.05% $NH_3$—$H_2O$ (v %); Mobile phase B: MeCN; Gradient: B from 28% to 58% in 7.8 min, hold 100% B for 2.5 min; Flow Rate: 25 mL/min; Column Temperature: 30° C.; Wavelength: 220 nm, 254 nm) to afford N-(6-amino-5-ethyl-3-pyridyl)-2-[(5S)-5-methyl-2-[2-(1-methyl-4-piperidyl)-1,3-benzothiazol-5-yl]-1-piperidyl]-2-oxo-acetamide (100 mg, 92.3% yield) as white solid.

Step 6: Synthesis of N-(6-amino-5-ethyl-3-pyridyl)-2-[(2S,5S)-5-methyl-2-[2-(1-methyl-4-piperidyl)-1,3-benzothiazol-5-yl]-1-piperidyl]-2-oxo-acetamide (Compound 1143

N-(6-amino-5-ethyl-3-pyridyl)-2-[(5S)-5-methyl-2-[2-(1-methyl-4-piperidyl)-1,3-benzothiazol-5-yl]-1-piperidyl]-2-oxo-acetamide (50 mg, 96.0 μmol) was separated by chiral SFC (Instrument: Thar 800Q; Daicel Chiralpak IG (250 mm*30 mm, 10 m); Mobile phase: supercritical $CO_2$/EtOH (0.1% $NH_3$—$H_2O$, v %)=55/45; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give N-(6-amino-5-ethyl-3-pyridyl)-2-[(2S,5S)-5-methyl-2-[2-(1-methyl-4-piperidyl)-1,3-benzothiazol-5-yl]-1-piperidyl]-2-oxo-acetamide (30 mg, single known enantiomer with trans relative chemistry, peak 2, retention time=5.155 min, white solid). $^1$H NMR (400 MHz, methanol-$d_4$) δ ppm 7.88-8.29 (m, 3H), 7.20-7.88 (m, 2H), 5.44-5.90 (m, 1H), 3.70-4.20 (m, 1H), 3.36-3.52 (m, 1H), 3.17 (br s, 1H), 3.03 (br d, J=11.3 Hz, 2H), 2.12-2.62 (m, 9H), 1.99 (br d, J=11.8 Hz, 4H), 1.41-1.56 (m, 1H), 1.04-1.37 (m, 6H); LCMS (ESI) [M+H]$^+$ m/z: calcd 521.3, found 521.3; HPLC: 99.11%@220 nm, 100%@254 nm; 100% ee.

Example 445. The Synthesis of rel-N-(6-amino-5-cyclopropyl-3-pyridyl)-2-[(2R,4S,5R)-2-(1,3-benzothiazol-5-yl)-4-methoxy-5-methyl-1-piperidyl]-2-oxo-acetamide (Compound 1370) and rel-N-(6-amino-5-cyclopropyl-3-pyridyl)-2-[(2S,4R,5S)-2-(1,3-benzothiazol-5-yl)-4-methoxy-5-methyl-1-piperidyl]-2-oxo-acetamide (Compound 1241

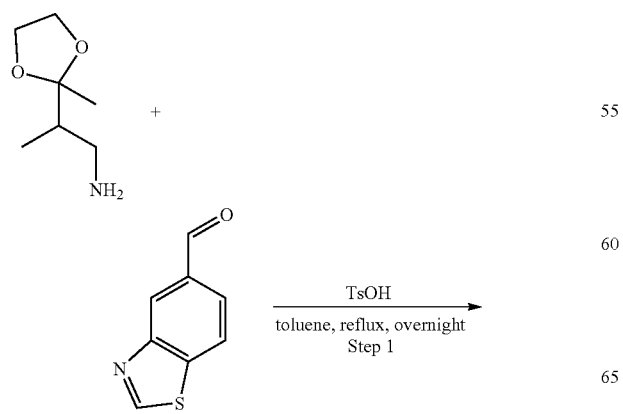

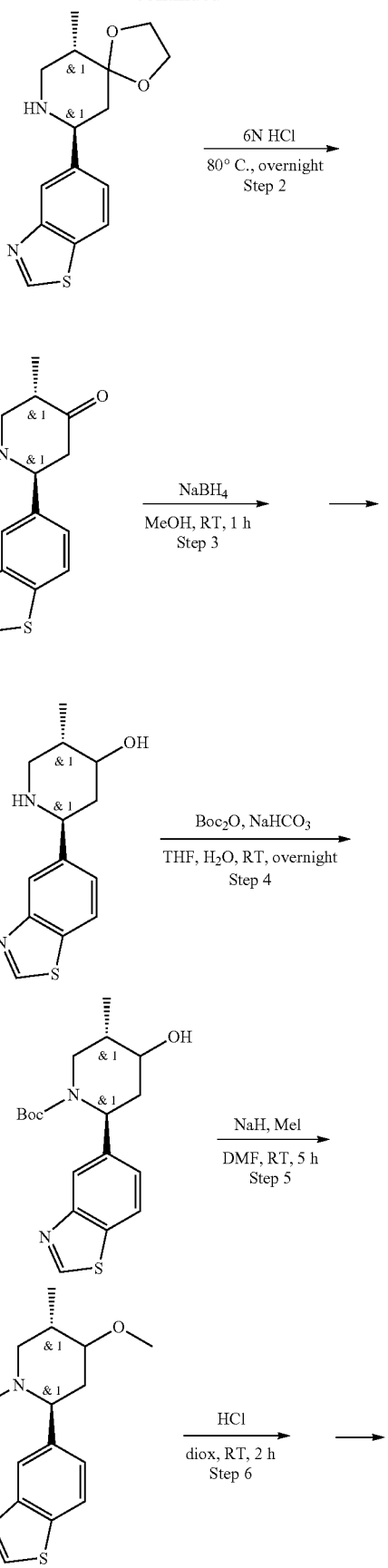

2317

-continued

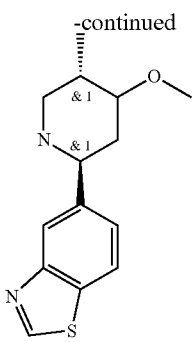

+

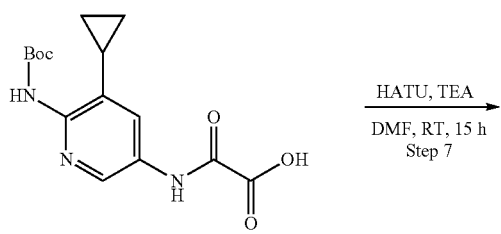

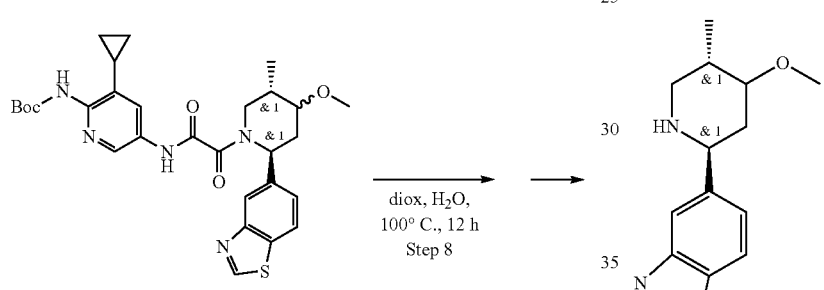

2318

-continued

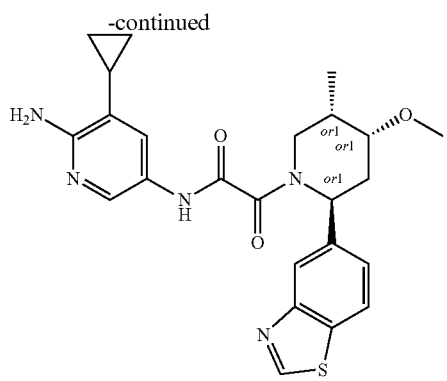

Compound 1241

Step 7: The Synthesis of rac-tert-butyl N-[5-[[2-[(2S,5S)-2-(1,3-benzothiazol-5-yl)-4-methoxy-5-methyl-1-piperidyl]-2-oxo-acetyl]amino]-3-cyclopropyl-2-pyridyl]carbamate

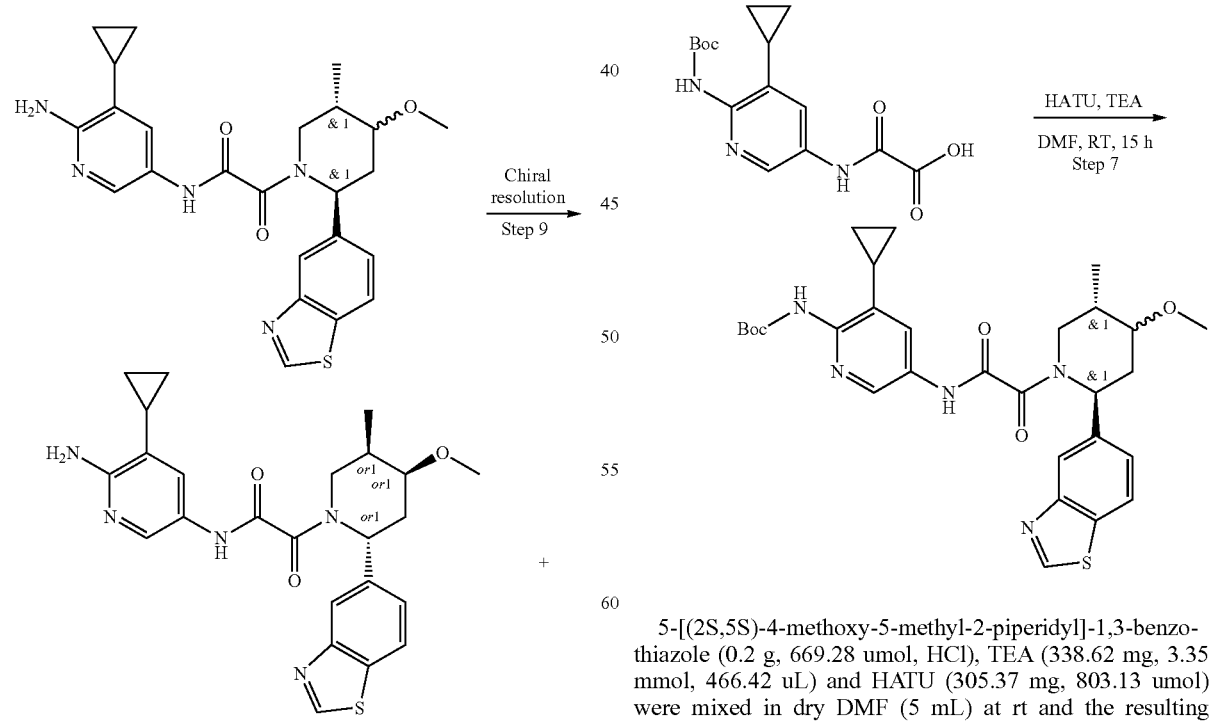

Compound 1370

5-[(2S,5S)-4-methoxy-5-methyl-2-piperidyl]-1,3-benzothiazole (0.2 g, 669.28 umol, HCl), TEA (338.62 mg, 3.35 mmol, 466.42 uL) and HATU (305.37 mg, 803.13 umol) were mixed in dry DMF (5 mL) at rt and the resulting mixture was stirred for 15 min. 2-[[6-(tert-butoxycarbonylamino)-5-cyclopropyl-3-pyridyl]amino]-2-oxo-acetic acid (219.70 mg, 669.28 umol, Li) was added thereto and the resulting mixture was stirred at rt for 12 hr. The resulting mixture was evaporated to dryness to obtain tert-butyl N-[5-[[2-[(2S,5S)-2-(1,3-benzothiazol-5-yl)-4-methoxy-5-methyl-1-piperidyl]-2-oxo-acetyl]amino]-3-cyclopropyl-2-pyridyl]carbamate (670 mg, crude).

LCMS(ESI): [M+H]⁺ m/z: calcd 566.2; found 566.2; Rt=1.373 min.

Step 8: The Synthesis of rac-N-(6-amino-5-cyclopropyl-3-pyridyl)-2-[(2S,5S)-2-(1,3-benzothiazol-5-yl)-4-methoxy-5-methyl-1-piperidyl]-2-oxo-acetamide A solution of rac-tert-butyl N-[5-[[2-[(2S,5S)-2-(1,3-benzothiazol-5-yl)-4-methoxy-5-methyl-1-piperidyl]-2-oxo-acetyl]amino]-3-cyclopropyl-2-pyridyl]carbamate (670 mg, 1.18 mmol) in Dioxane (5 mL) and Water (5 mL) was heated at 100° C. for 12 hr. Solvents were evaporated and resulting precipitate was purified by HPLC (2-10 min 30-55% methanol+NH₃, 30 mL/min (loading pump 4 mL methanol), column: SunFire 100*19 mm, 5 microM) to obtain rac-N-(6-amino-5-cyclopropyl-3-pyridyl)-2-[(2S,5S)-2-(1,3-benzothiazol-5-yl)-4-methoxy-5-methyl-1-piperidyl]-2-oxo-acetamide (33.8 mg, crude).

LCMS(ESI): [M+H]⁺ m/z: calcd 466.2; found 466.2; Rt=0.923 min.

Step 9: The Synthesis of rel-N-(6-amino-5-cyclopropyl-3-pyridyl)-2-[(2R,4S,5R)-2-(1,3-benzothiazol-5-yl)-4-methoxy-5-methyl-1-piperidyl]-2-oxo-acetamide (Compound 1370) and rel-N-(6-amino-5-cyclopropyl-3-pyridyl)-2-[(2S,4R,5S)-2-(1,3-benzothiazol-5-yl)-4-methoxy-5-methyl-1-piperidyl]-2-oxo-acetamide (Compound 1241

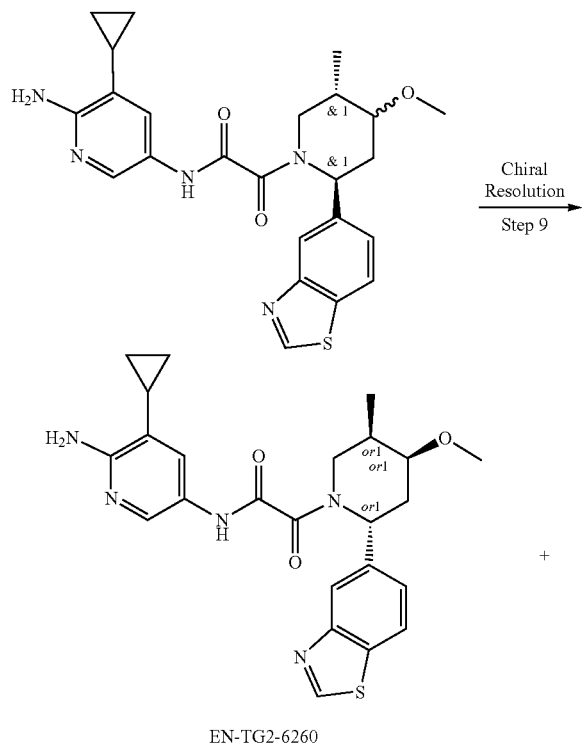

EN-TG2-6260

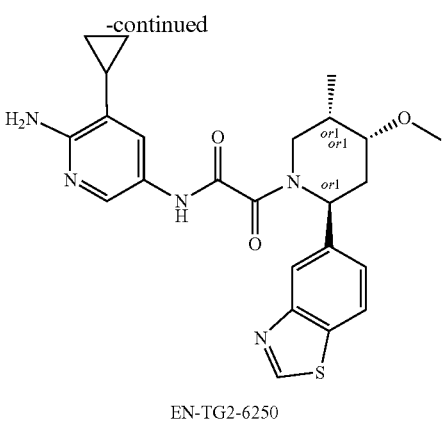

EN-TG2-6250 rac-N-(6-amino-5-cyclopropyl-3-pyridyl)-2-[(2S,5S)-2-(1,3-benzothiazol-5-yl)-4-methoxy-5-methyl-1-piperidyl]-2-oxo-acetamide (33.8 mg, 72.60 umol) was chiral separated (Chiralcel OD-H (250*20, 5 mkm), Hexane-IPA-MeOH, 80-10-10, 12 mL/min) to obtain Compound 1241—rel-N-(6-amino-5-cyclopropyl-3-pyridyl)-2-[(2S,4R,5S)-2-(1,3-benzothiazol-5-yl)-4-methoxy-5-methyl-1-piperidyl]-2-oxo-acetamide (8.75 mg, 18.79 umol, 25.89% yield) and Compound 1370—rel-N-(6-amino-5-cyclopropyl-3-pyridyl)-2-[(2R,4S,5R)-2-(1,3-benzothiazol-5-yl)-4-methoxy-5-methyl-1-piperidyl]-2-oxo-acetamide (12.9 mg, 27.71 umol, 38.17% yield).

Preparative:

RT for Compound 1241 (Chiralcel OD-H (250*20, 5 mkm), Hexane-IPA-MeOH, 80-10-10, 12 mL/min)=58.183 min.

RT for Compound 1370 (Chiralcel OD-H (250*20, 5 mkm), Hexane-IPA-MeOH, 80-10-10, 12 mL/min)=46.633 min.

Compound 1241:

Yield: 8.75 mg (25.89%)

RT (Chiralcel OD-H (250*4.6, 5 mkm), Hexane-IPA-MeOH, 60-20-20, 0.6 mL/min)=18.234 min.

¹H NMR (DMSO-d₆, 600 MHz): δ (ppm) 0.41 (m, 2H), 0.85 (m, 2H), 1.03 (d, 3H), 1.63 (m, 1H), 1.91 (m, 1H), 2.25 (m, 1H), 3.05 (m, 3H), 3.21 (m, 2H), 3.50 (m, 1H), 3.70 (m, 1H), 5.64 (m, 3H), 7.44 (m, 2H), 8.05 (m, 3H), 9.36 (m, 1H), 10.39 (m, 1H).

LCMS(ESI): [M+H]⁺ m/z: calcd 466.2; found 466.2; Rt=0.938 min.

Compound 1370:

Yield: 12.9 mg (38.17%)

RT (Chiralcel OD-H (250*4.6, 5 mkm), Hexane-IPA-MeOH, 60-20-20, 0.6 mL/min)=15.314 min.

¹H NMR (DMSO-d₆, 600 MHz): δ (ppm) 0.41 (m, 2H), 0.85 (m, 2H), 1.03 (d, 3H), 1.63 (m, 1H), 1.91 (m, 1H), 2.25 (m, 1H), 3.05 (m, 3H), 3.20 (m, 2H), 3.50 (m, 1H), 3.71 (m, 1H), 5.64 (m, 3H), 7.44 (m, 2H), 8.05 (m, 3H), 9.36 (m, 1H), 10.39 (m, 1H).

LCMS(ESI): [M+H]⁺ m/z: calcd 466.2; found 466.2; Rt=0.929 min.

Example 446. The Synthesis of N-(6-amino-5-cyclopropyl-3-pyridyl)-2-[(2R,5S)-5-methyl-2-(2-methyl-3,4-dihydro-1H-isoquinolin-6-yl)-1-piperidyl]-2-oxo-acetamide (Compound 1264)
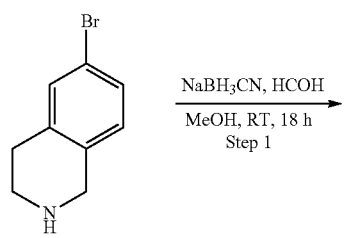
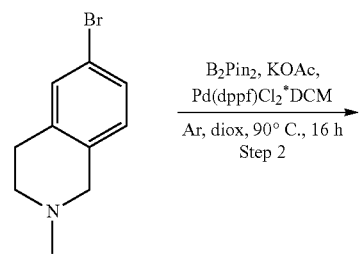
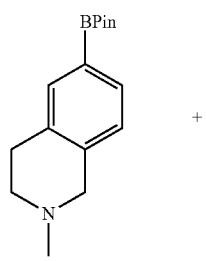
+
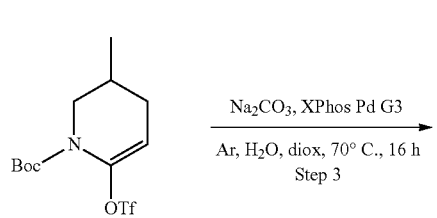
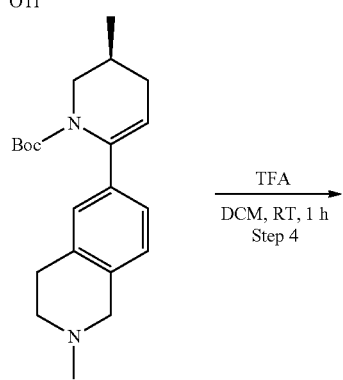
-continued
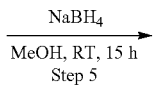
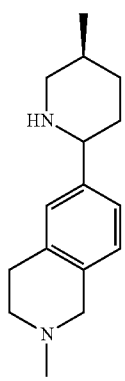
Step 3: The Synthesis of tert-butyl (3S)-3-methyl-6-(2-methyl-3,4-dihydro-1H-isoquinolin-6-yl)-3,4-dihydro-2H-pyridine-1-carboxylate
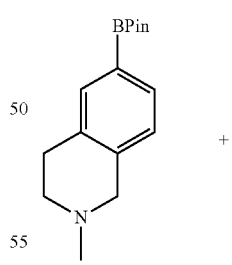
+
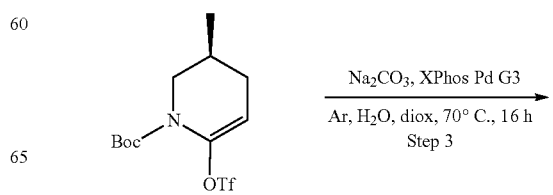

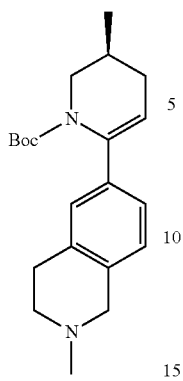

tert-butyl (5S)-5-methyl-2-(trifluoromethylsulfonyloxy) piperidine-1-carboxylate (4.07 g, 11.71 mmol), 2-methyl-6-(4,4,5,5-tetramethyl-1,3,2-dioxaborolan-2-yl)-3,4-dihydro-1H-isoquinoline (3.2 g, 11.71 mmol) and Sodium carbonate (3.72 g, 35.14 mmol, 1.47 mL) were added to a mixture of dioxane (30 mL) and water (10 mL). The resulting mixture was evacuated and then backfilled with argon, this operation was repeated three times, then Pd(dppf)Cl$_2$*DCM (478.30 mg, 585.70 umol) was added under argon. The reaction mixture was stirred under argon at 70° C. for 16 h, then cooled and filtered. The filtercake was washed with 1,4-dioxane (2*20 mL) and discarded. The filtrate was evaporated in vacuo to afford tert-butyl (3S)-3-methyl-6-(2-methyl-3,4-dihydro-1H-isoquinolin-6-yl)-3,4-dihydro-2H-pyridine-1-carboxylate (4 g, 11.68 mmol, 99.71% yield) as brown oil, which was used in next step without purification.

LCMS(ESI): [M+H]$^+$ m/z: calcd 343.2; found 343.2; Rt=1.050 min.

Step 4: The Synthesis of 2-methyl-6-[(3S)-3-methyl-2,3,4,5-tetrahydropyridin-6-yl]-3,4-dihydro-1H-isoquinoline The solution of tert-butyl (3S)-3-methyl-6-(2-methyl-3,4-dihydro-1H-isoquinolin-6-yl)-3,4-dihydro-2H-pyridine-1-carboxylate (4 g, 11.68 mmol) in TFA (19.98 g, 175.20 mmol, 13.50 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 2-methyl-6-[(3S)-3-methyl-2,3,4,5-tetrahydropyridin-6-yl]-3,4-dihydro-1H-isoquinoline (2.3 g, 9.49 mmol, 81.25% yield) as brown oil, which was used directly in the next step.

LCMS(ESI): [M+H]$^+$ m/z: calcd 243.2; found 243.2; Rt=0.219 min.

Step 5: The Synthesis of 2-methyl-6-[(5S)-5-methyl-2-piperidyl]-3,4-dihydro-1H-isoquinoline Sodium Borohydride (718.07 mg, 18.98 mmol, 671.09 uL) was added in one portion to a stirred solution of 2-methyl-6-[(3S)-3-methyl-2,3,4,5-tetrahydropyridin-6-yl]-3,4-dihydro-1H-isoquinoline (2.3 g, 9.49 mmol) in MeOH (20 mL) at 0° C. The resulting mixture was stirred at 25° C. for 15 hr, and then evaporated in vacuo. The residue was diluted with water (20 mL) and extracted with EtOAc (2*40 mL). The combined organic extracts were dried over sodium sulphate and evaporated in vacuo. The obtained oil was subjected to HPLC (Waters Sunfire C18 19*100 5 mkm column and MeCN as an eluent mixture) to afford 2-methyl-6-[(5S)-5-methyl-2-piperidyl]-3,4-dihydro-1H-isoquinoline (0.4 g, 1.64 mmol, 17.25% yield).

LCMS(ESI): [M+H]$^+$ m/z: calcd 245.2; found 245.2; Rt=0.322 min.

Step 6: The Synthesis of tert-butyl N-[3-cyclopropyl-5-[[2-[(2R,5S)-5-methyl-2-(2-methyl-3,4-dihydro-1H-isoquinolin-6-yl)-1-piperidyl]-2-oxo-acetyl]amino]-2-pyridyl]carbamate

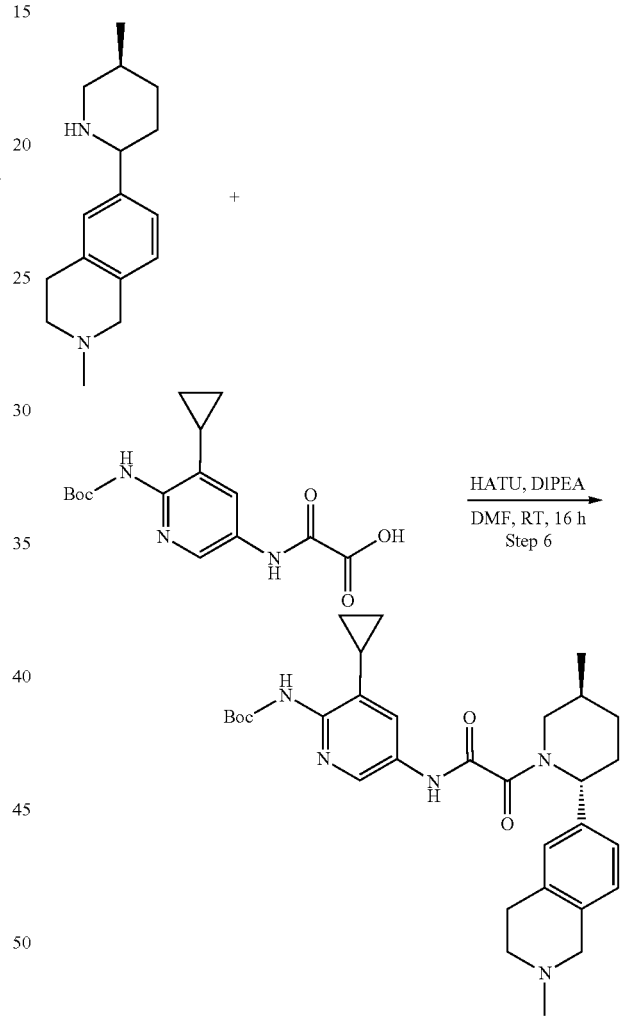

DIPEA (180.74 mg, 1.40 mmol, 243.59 uL) was added to the solution of respective 2-[[6-(tert-butoxycarbonylamino)-5-cyclopropyl-3-pyridyl]amino]-2-oxo-acetate (182.93 mg, 559.39 umol, Li+) and 2-methyl-6-[(5S)-5-methyl-2-piperidyl]-3,4-dihydro-1H-isoquinoline (136.7 mg, 559.39 umol) in DMF (5 mL). The resulting mixture was stirred for 5 min followed by the addition of HATU (233.97 mg, 615.33 umol). Then, the reaction mixture was stirred overnight at rt under Ar. After the completion of the reaction, monitored by LCMS, the resulting suspension was concentrated under reduced pressure. The obtained solid was subjected to HPLC (Waters Sunfire C18 20*100 5 mkm column and MeOH+NH$_3$ as an eluent mixture) to afford tert-butyl N-[3-cyclopropyl-5-[[2-[(2R,5S)-5-methyl-2-(2-methyl-3,4-dihydro-1H-isoquinolin-6-yl)-1-piperidyl]-2-oxo-acetyl]amino]-2-pyridyl]carbamate (106.4 mg, 194.27 μmol, 34.73% yield).

LCMS(ESI): [M+H]+ m/z: calcd 548.2; found 548.4; Rt=2.229 min.

Step 7: The Synthesis of N-(6-amino-5-cyclopropyl-3-pyridyl)-2-[(2R,5S)-5-methyl-2-(2-methyl-3,4-dihydro-1H-isoquinolin-6-yl)-1-piperidyl]-2-oxo-acetamide (Compound 1264

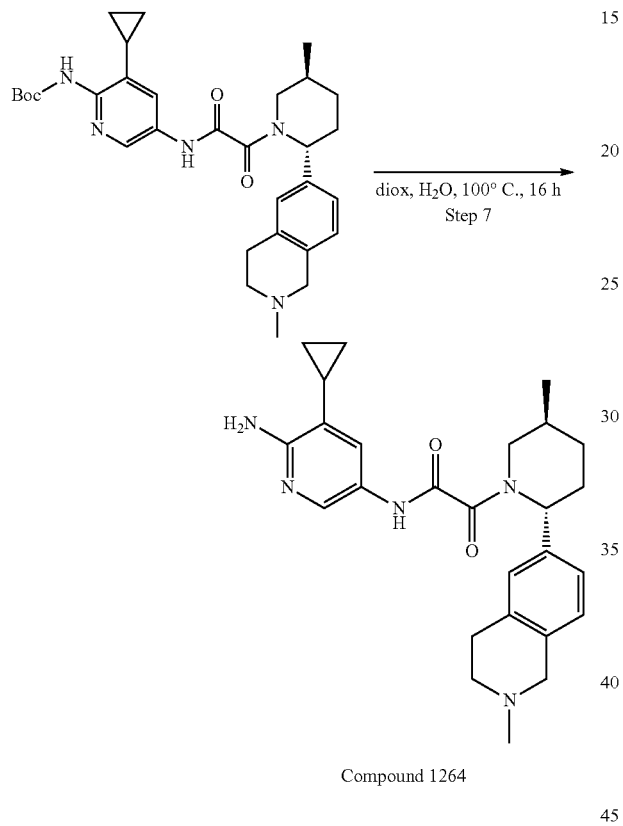

Compound 1264 tert-butyl N-[3-cyclopropyl-5-[[2-[(2R,5S)-5-methyl-2-(2-methyl-3,4-dihydro-1H-isoquinolin-6-yl)-1-piperidyl]-2-oxo-acetyl]amino]-2-pyridyl]carbamate (106.4 mg, 194.27 mol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and water-MeCN+NH₃ as an eluent mixture) to afford N-(6-amino-5-cyclopropyl-3-pyridyl)-2-[(2R,5S)-5-methyl-2-(2-methyl-3,4-dihydro-1H-isoquinolin-6-yl)-1-piperidyl]-2-oxo-acetamide (10.3 mg, 23.01 μmol, 11.85% yield).

¹H NMR (DMSO-d₆, 600 MHz): δ (ppm) 0.41-0.46 (m, 2H), 0.84-1.01 (m, 5H), 1.22-1.35 (m, 2H), 1.61-1.67 (m, 2H), 1.81-2.31 (m, 7H), 2.54-2.57 (m, 2H), 2.73-2.80 (m, 2H), 3.43-3.45 (m, 2H), 5.09-5.75 (m, 4H), 7.01-7.08 (m, 3H), 7.29-7.36 (m, 1H), 10.41-10.47 (m, 1H).

LCMS(ESI): [M+H]+ m/z: calcd 448.2; found 448.4; Rt=1.372 min.

Example 447. The Synthesis of N-(6-amino-5-ethyl-3-pyridyl)-2-[(2R,5S)-5-methyl-2-[2-[(3S)-1-methylpyrrolidin-3-yl]-1,3-benzothiazol-5-yl]-1-piperidyl]-2-oxo-acetamide (Compound 1311) and N-(6-amino-5-ethyl-3-pyridyl)-2-[(2R,5S)-5-methyl-2-[2-[(3R)-1-methylpyrrolidin-3-yl]-1,3-benzothiazol-5-yl]-1-piperidyl]-2-oxo-acetamide (Compound 1308)

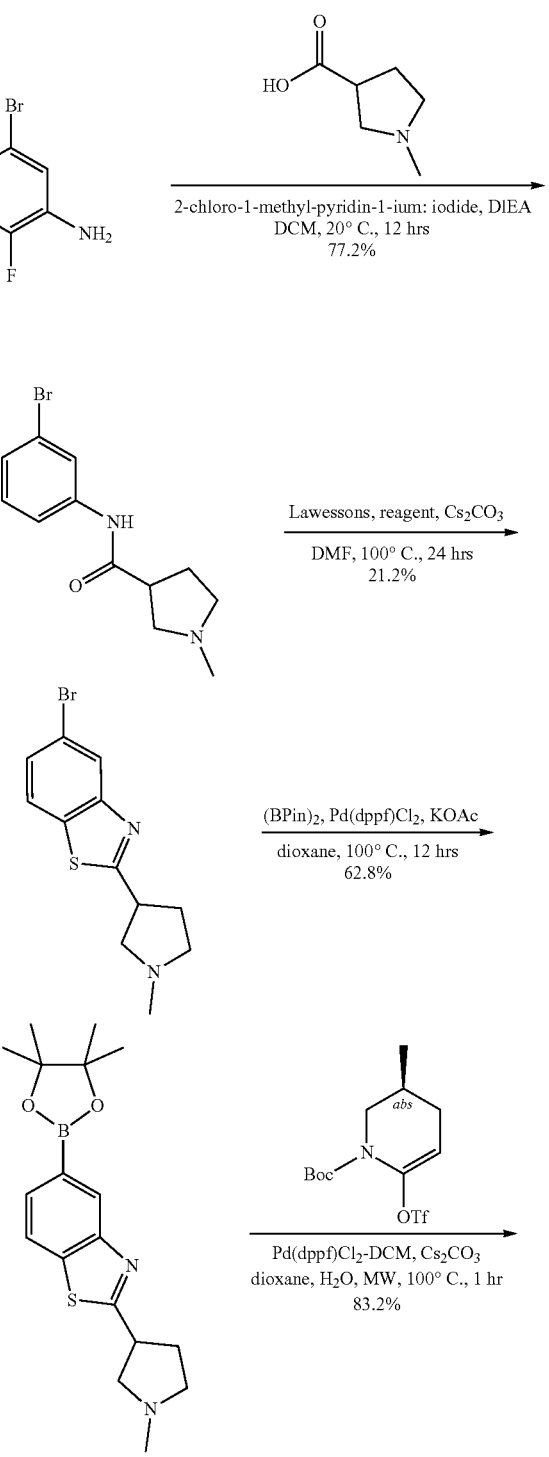

2327
-continued
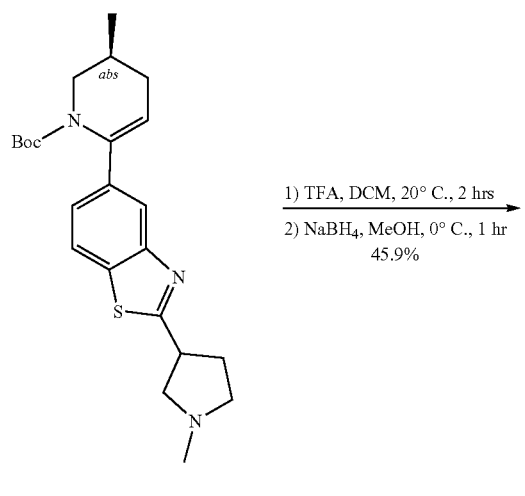
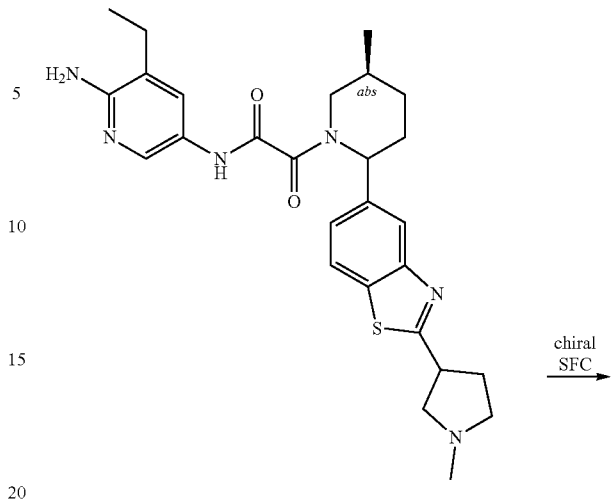
2328
-continued
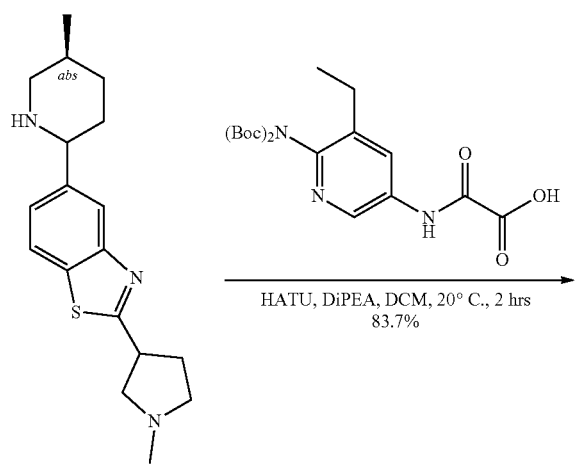
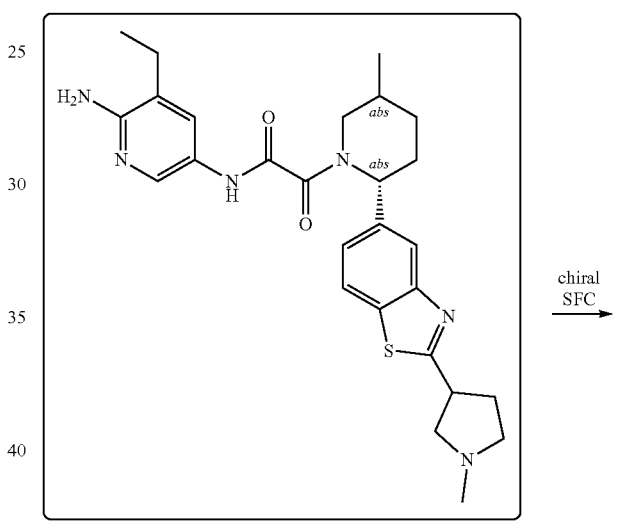
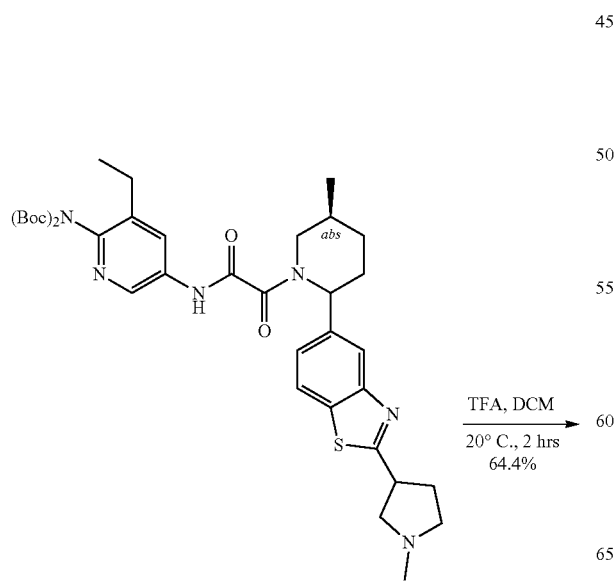
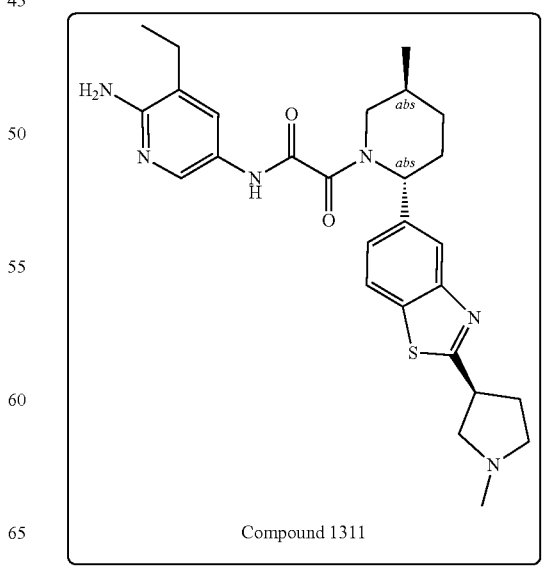
Compound 1311

-continued

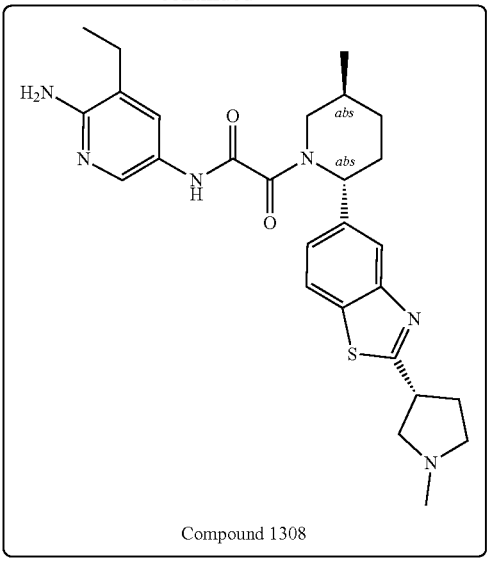 [SMILES: CCc1cc(NC(=O)C(=O)N2C[C@@H](C)CC[C@@H]2c2ccc3sc([C@@H]4CCN(C)C4)nc3c2)cnc1N]

Compound 1308

Step 1: Synthesis of N-(5-bromo-2-fluoro-phenyl)-1-methyl-pyrrolidine-3-carboxamide A mixture of 1-methylpyrrolidine-3-carboxylic acid (1 g, 7.74 mmol), 5-bromo-2-fluoro-aniline (1.47 g, 7.74 mmol), 2-chloro-1-methyl-pyridin-1-ium; iodide (2.4 g, 9.39 mmol) and DCM (12 mL) was added DIPEA (3 g, 23.2 mmol) and the mixture was stirred at 20° C. for 12 hours. The mixture was concentrated under reduced pressure. The residue was purified by flash chromatography (ISCO®; 40 g Agela-Flash® Silica Flash Column, petroleum ether/EtOAc with EtOAc from 0~20%, Flow Rate: 30 mL/min) to afford N-(5-bromo-2-fluoro-phenyl)-1-methyl-pyrrolidine-3-carboxamide (1.8 g, 77.2% yield) as yellow oil. LCMS (ESI) [M+H]$^+$ m/z: calcd 284.0, found 302.9 (M+H$_2$O).

Step 2: Synthesis of 5-bromo-2-(1-methylpyrrolidin-3-yl)-1,3-benzothiazole

A mixture of N-(5-bromo-2-fluoro-phenyl)-1-methyl-pyrrolidine-3-carboxamide (1.8 g, 5.98 mmol), Lawessons reagent (1.46 g, 3.61 mmol) and DMF (20 mL) was added Cs$_2$CO$_3$ (4.93 g, 15.1 mmol) and the mixture was stirred at 100° C. for 24 hours. The resulting mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure to afford a crude product, which was purified by flash chromatography (ISCO®; 24 g Agela-Flash® Silica Flash Column, petroleum ether/EtOAc with EtOAc from 0~100%, Flow Rate: 30 mL/min) to afford crude product, which was further purified by preparative HPLC (Instrument: Gilson GX-281 Liquid Handler, Gilson 322 Pump, Gilson 156 UV Detector; Column: Phenomenex Gemini-NX C18 75*30 mm*3 μm; Mobile phase A: H$_2$O with 10 mM NH$_4$HCO$_3$ (v %); Mobile phase B: MeCN; Gradient: B from 31% to 61% in 7.8 min; hold 100% B for 2 min; Flow Rate: 25 mL/min; Column Temperature: 30° C.; Wavelength: 220 nm, 254 nm) to afford 5-bromo-2-(1-methylpyrrolidin-3-yl)-1,3-benzothiazole (350 mg, 21.2% yield) as yellow solid. LCMS (ESI) [M+H]$^+$ m/z: calcd 299.0, found 299.0.

Step 3: Synthesis of 2-(1-methylpyrrolidin-3-yl)-5-(4,4,5,5-tetramethyl-1,3,2-dioxaborolan-2-yl)-1,3-benzothiazole A mixture of 5-bromo-2-(1-methylpyrrolidin-3-yl)-1,3-benzothiazole (330 mg, 1.11 mmol), KOAc (630 mg, 2.23 mmol), 4,4,5,5-tetramethyl-2-(4,4,5,5-tetramethyl-1,3,2-dioxaborolan-2-yl)-1,3,2-dioxaborolane (430 mg, 1.69 mmol), cyclopentyl(diphenyl)phosphane; dichloropalladium; iron (80 mg, 0.109 mmol) and dioxane (8 mL) was stirred at 100° C. for 12 hours. The resulting mixture was quenched by addition of water (50 mL) and extracted with EtOAc (100 mL*3). The combined organic layer was washed with saturated NH$_4$Cl aqueous solution (50 mL), brine (100 mL), dried over anhydrous Na$_2$SO$_4$, filtered and concentrated under reduced pressure. The residue was purified by flash chromatography (ISCO®; 80 g AgelaFlash® Silica Flash Column, EtOAc/MeOH with MeOH from 0~5%, Flow Rate: 30 mL/min) to afford 2-(1-methylpyrrolidin-3-yl)-5-(4,4,5,5-tetramethyl-1,3,2-dioxaborolan-2-yl)-1,3-benzothiazole (240 mg, 62.8% yield) as brown solid.

$^1$H NMR (400 MHz, methanol-d$_4$) δ ppm 8.30 (s, 1H), 7.96 (d, J=8.0 Hz, 1H), 7.75 (d, J=8.0 Hz, 1H), 4.01-4.10 (m, 1H), 3.35-3.40 (m, 1H), 3.24-3.28 (m, 1H), 3.02-3.10 (m, 2H), 2.64 (s, 3H), 2.54-2.62 (m, 1H), 2.29-2.38 (m, 1H), 1.38 (s, 12H); LCMS (ESI) [M+H]$^+$ m/z: calcd 345.2, found 345.2.

Step 4: Synthesis of tert-butyl (3S)-3-methyl-6-[2-(1-methylpyrrolidin-3-yl)-1,3-benzothiazol-5-yl]-3,4-dihydro-2H-pyridine-1-carboxylate To a mixture of 2-(1-methylpyrrolidin-3-yl)-5-(4,4,5,5-tetramethyl-1,3,2-dioxaborolan-2-yl)-1,3-benzothiazole (200 mg, 0.581 mmol), tert-butyl (3S)-3-methyl-6-(trifluoromethylsulfonyloxy)-3,4-dihydro-2H-pyridine-1-carboxylate (300 mg, 0.869 mmol) in dioxane (1.5 mL) and H$_2$O (0.5 mL) were added Pd(dppf)Cl$_2$-DCM (47 mg, 0.0576 mmol) and Cs$_2$CO$_3$ (280 mg, 0.859 mmol). The resulting mixture was sealed and degassed under vacuum and purged with N$_2$ for three times, and then stirred at 100° C. for 1 hour under microwave. The resulting mixture was quenched by addition of water (30 mL) and extracted with EtOAc (50 mL*3). The combined organic layer was washed with saturated NH$_4$Cl aqueous solution (50 mL), brine (50 mL), dried over anhydrous Na$_2$SO$_4$, filtered and concentrated under reduced pressure. The residue was purified by flash chromatography (ISCO®; 12 g AgelaFlash® Silica Flash Column, DCM/MeOH with MeOH from 0~10%, flow rate=30 mL/min) to afford tert-butyl (3S)-3-methyl-6-[2-(1-methylpyrrolidin-3-yl)-1,3-benzothiazol-5-yl]-3,4-dihydro-2H-pyridine-1-carboxylate (200 mg, 83.2% yield) as yellow solid.

Step 5: Synthesis of 5-[(5S)-5-methyl-2-piperidyl]-2-(1-methylpyrrolidin-3-yl)-1,3-benzothiazole A mixture of tert-butyl (3S)-3-methyl-6-[2-(1-methylpyrrolidin-3-yl)-1,3-benzothiazol-5-yl]-3,4-dihydro-2H-pyridine-1-carboxylate (200 mg, 0.484 mmol), DCM (3 mL) and TFA (2 mL, 26.0 mmol) was stirred at 20° C. for 2 hours. The resulting mixture was concentrated under reduced pressure. The residue was diluted with MeOH (5 mL) and adjusted to pH=6 with saturated Na$_2$CO$_3$, and then NaBH$_4$ (30 mg, 0.793 mmol) was added to the mixture at 0° C. slowly. The resulting mixture was stirred at 0° C. for 1 hour. The mixture was concentrated under reduced pressure. The residue was purified by flash chromatography (Column: SepaFlash® Spherical C18, 40 g, 40-60 m, 120A; MeCN/water (0.05 v % $NH_3$—$H_2O$) with MeCN from 0-50%, 25 mL/min, 220 nm) to give 5-[(5S)-5-methyl-2-piperidyl]-2-(1-methylpyrrolidin-3-yl)-1,3-benzothiazole (70 mg, 45.9% yield) as white solid. LCMS (ESI) [M+H]$^+$ m/z: calcd 316.2, found 316.2.

Step 6: Synthesis of tert-butyl N-tert-butoxycarbonyl-N-[3-ethyl-5-[[2-[(5S)-5-methyl-2-[2-(1-methylpyrrolidin-3-yl)-1,3-benzothiazol-5-yl]-1-piperidyl]-2-oxo-acetyl]amino]-2-pyridyl]carbamate A mixture of 2-[[6-[bis(tert-butoxycarbonyl)amino]-5-ethyl-3-pyridyl]amino]-2-oxo-acetic acid (90 mg, 0.220 mmol), 5-[(5S)-5-methyl-2-piperidyl]-2-(1-methylpyrrolidin-3-yl)-1,3-benzothiazole (70.0 mg, 0.222 mmol), HATU (100 mg, 0.263 mmol) and DIPEA (0.11 mL, 0.632 mmol) in DCM (5 mL) was stirred at 20° C. for 2 hours. The resulting mixture was quenched by addition of water (50 mL) and extracted with DCM (50 mL*3). The combined organic layer was washed with saturated $NH_4Cl$ aqueous solution (50 mL), brine (50 mL), dried over anhydrous $Na_2SO_4$, filtered and concentrated under reduced pressure. The residue was purified by flash chromatography (ISCO®; 4 g AgelaFlash® Silica Flash Column, DCM/MeOH with MeOH from 0~20%, flow rate=30 mL/min, 254 nm) to afford tert-butyl N-tert-butoxycarbonyl-N-[3-ethyl-5-[[2-[(5S)-5-methyl-2-[2-(1-methylpyrrolidin-3-yl)-1,3-benzothiazol-5-yl]-1-piperidyl]-2-oxo-acetyl]amino]-2-pyridyl]carbamate (130 mg, 83.7% yield) as yellow oil. LCMS (ESI) [M+H]$^+$ m/z: calcd 707.4, found 707.4.

Step 7: Synthesis of N-(6-amino-5-ethyl-3-pyridyl)-2-[(5S)-5-methyl-2-[2-(1-methylpyrrolidin-3-yl)-]1,3-benzothiazol-5-yl]-1-piperidyl]-2-oxo-acetamide A mixture of tert-butyl N-tert-butoxycarbonyl-N-[3-ethyl-5-[[2-[(5S)-5-methyl-2-[2-(1-methylpyrrolidin-3-yl)-1,3-benzothiazol-5-yl]-1-piperidyl]-2-oxo-acetyl]amino]-2-pyridyl]carbamate (130 mg, 0.184 mmol), DCM (3 mL) and TFA (2 mL, 26.0 mmol) was stirred at 20° C. for 2 hours. The resulting mixture was adjusted to pH=8 with 28 wt % $NH_3$—$H_2O$, and then the mixture was concentrated under reduced pressure to give a crude product, which was purified by preparative HPLC (Instrument: Gilson GX-281 Liquid Handler, Gilson 322 Pump, Gilson 156 UV Detector; Column: Phenomenex Gemini-NX 80*40 mm*3 μm; Mobile phase A: $H_2O$ with 10 mmol $NH_4HCO_3$ (v %); Mobile phase B: MeCN; Gradient: B from 27% to 57% in 9.5 min, hold 100% B for 2 min; Flow Rate: 25 mL/min; Column Temperature: 30° C.; Wavelength: 220 nm, 254 nm) to afford N-(6-amino-5-ethyl-3-pyridyl)-2-[(5S)-5-methyl-2-[2-(1-methylpyrrolidin-3-yl)-1,3-benzothiazol-5-yl]-1-piperidyl]-2-oxo-acetamide (60 mg, 64.4% yield) as white solid. LCMS (ESI) [M+H]$^+$ m/z: calcd 507.2, found 507.3; HPLC: 96.240%@254 nm; 1000%@254 nm.

Step 8: Synthesis of N-(6-amino-5-ethyl-3-pyridyl)-2-[(2R,5S)-5-methyl-2-[2-(1-methylpyrrolidin-3-yl)-1,3-benzothiazol-5-yl]-1-piperidyl]-2-oxo-acetamide N-(6-amino-5-ethyl-3-pyridyl)-2-[(5S)-5-methyl-2-[2-(1-methylpyrrolidin-3-yl)-1,3-benzothiazol-5-yl]-1-piperidyl]-2-oxo-acetamide (50 mg, 0.0987 mmol) was purified by SFC (Instrument: Berger, Multigr AM-II; Column: Daicel Chiralcel OJ 250 mm×30 mm×10 m; Mobile phase: supercritical $CO_2$/EtOH (0.1% $NH_3$—$H_2O$, v %=70/30; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm). The fraction was concentrated under reduced pressure and then lyophilized for overnight to give N-(6-amino-5-ethyl-3-pyridyl)-2-[(2R,5S)-5-methyl-2-[2-(1-methylpyrrolidin-3-yl)-1,3-benzothiazol-5-yl]-1-piperidyl]-2-oxo-acetamide (45 mg, 90.0% yield, Peak 2, Retention time: 3.415 min, a mixture of two diastereoisomers, white solid, 2.1 mg was delivered). $^1$H NMR (400 MHz, methanol-$d_4$) δ ppm 8.11 (br s, 1H), 7.87-8.00 (m, 2H), 7.65 (br s, 1H), 7.44 (br s, 1H), 5.43-5.90 (m, 1H), 3.88-4.13 (m, 1H), 3.41-3.81 (m, 1H), 3.10-3.21 (m, 1H), 2.92 (br s, 1H), 2.81 (br s, 2H), 2.21-2.59 (m, 10H), 1.95 (br s, 2H), 1.47 (br d, J=12.5 Hz, 1H), 1.10-1.29 (m, 6H); LCMS (ESI) [M+H]$^+$ m/z: calcd 507.2, found 507.3; HPLC: 100%@220 nm, 100%@254 nm.

Step 9: Synthesis of N-(6-amino-5-ethyl-3-pyridyl)-2-[(2R,5S)-5-methyl-2-[2-[(3S)-1-methylpyrrolidin-3-yl]-1,3-benzothiazol-5-yl]-1-piperidyl]-2-oxo-acetamide (Compound 1311) and N-(6-amino-5-ethyl-3-pyridyl)-2-[(2R,5S)-5-methyl-2-[2-[(3R)-1-methylpyrrolidin-3-yl]-1,3-benzothiazol-5-yl]-1-piperidyl]-2-oxo-acetamide (Compound 1308

N-(6-amino-5-ethyl-3-pyridyl)-2-[(2R,5S)-5-methyl-2-[2-(1-methylpyrrolidin-3-yl)-1,3-benzothiazol-5-yl]-1-piperidyl]-2-oxo-acetamide (40 mg, 0.0790 mmol) was separated by chiral SFC (Instrument: Berger, Multigr AM-II; Column: Daicel Chiralcel OJ 250 mm×10 mm×10 m; Mobile phase: supercritical $CO_2$/EtOH (0.1% $NH_3$—$H_2O$, v %)=70/30; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give Compound 1311 and Compound 1308.

Compound 1311: N-(6-amino-5-ethyl-3-pyridyl)-2-[(2R,5S)-5-methyl-2-[2-[(3S)-1-methylpyrrolidin-3-yl]-1,3-benzothiazol-5-yl]-1-piperidyl]-2-oxo-acetamide (17.2 mg, single unknown enantiomer with trans relative chemistry, peak 1, retention time: 6.269 min, white solid). $^1$H NMR (400 MHz, methanol-$d_4$) δ ppm 8.12 (br s, 1H), 7.91-8.01 (m, 2H), 7.65 (br s, 1H), 7.38-7.54 (m, 1H), 5.46-5.87 (m, 1H), 3.93-4.17 (m, 1H), 3.39-3.84 (m, 1H), 3.14 (br d, J=5.3 Hz, 1H), 2.97 (br d, J=5.8 Hz, 2H), 2.20-2.72 (m, 10H), 1.92 (br d, J=12.3 Hz, 2H), 1.47 (br d, J=11.8 Hz, 1H), 1.08-1.31 (m, 6H); LCMS (ESI) [M+H]$^+$ m/z: calcd 507.2, found 507.3; HPLC: 98.34%@254 nm, 99.43%/@254 nm; 96.9% ee.

Compound 1308: N-(6-amino-5-ethyl-3-pyridyl)-2-[(2R,5S)-5-methyl-2-[2-[(3R)-1-methylpyrrolidin-3-yl]-1,3-benzothiazol-5-yl]-1-piperidyl]-2-oxo-acetamide (16.8 mg, single unknown enantiomer with trans relative chemistry, peak 2, retention time: 7.179 min, white solid). $^1$H NMR (400 MHz, methanol-$d_4$) δ ppm 8.11 (br s, 1H), 7.90-8.01 (m, 2H), 7.65 (br s, 1H), 7.40-7.53 (m, 1H), 5.44-5.87 (m, 1H), 3.93 (br s, 1H), 3.41-3.82 (m, 1H), 3.12-3.22 (m, 1H), 2.92 (br s, 1H), 2.76-2.86 (m, 2H), 2.08-2.64 (m, 10H), 1.94 (br s, 2H), 1.47 (br d, J=12.5 Hz, 1H), 1.14 (br d, J=7.0 Hz, 6H); LCMS (ESI) [M+H]$^+$ m/z: calcd 507.2, found 507.3; HPLC: 97.87%/@254 nm, 97.790%@254 nm; 93.2% ee.

Example 448. The Synthesis of N-(6-amino-5-ethyl-3-pyridyl)-2-[(5S)-2-[2-(1,3-dimethyl-4-piperidyl)-1,3-benzothiazol-5-yl]-5-methyl-1-piperidyl]-2-oxo-acetamide (Compound 1382), N-(6-amino-5-ethyl-3-pyridyl)-2-oxo-2-[rac-(2R,5S)-5-methyl-2-[2-[rac-(3R,4R)-1,3-dimethyl-4-piperidyl]-1,3-benzothiazol-5-yl]-1-piperidyl]acetamide (Compound 1131), N-(6-amino-5-ethyl-3-pyridyl)-2-oxo-2-[rac-(2R,5S)-5-methyl-2-[2-[rac-(3S,4S)-1,3-dimethyl-4-piperidyl]-1,3-benzothiazol-5-yl]-1-piperidyl]acetamide (Compound 1373), N-(6-amino-5-ethyl-3-pyridyl)-2-oxo-2-[rac-(2R,5S)-5-methyl-2-[2-[rac-(3S,4R)-1,3-dimethyl-4-piperidyl]-1,3-benzothiazol-5-yl]-1-piperidyl]acetamide (Compound 1227) and N-(6-amino-5-ethyl-3-pyridyl)-2-oxo-2-[rac-(2R,5S)-5-methyl-2-[2-[rac-(3R,4S)-1,3-dimethyl-4-piperidyl]-1,3-benzothiazol-5-yl]-1-piperidyl]acetamide (Compound 1098

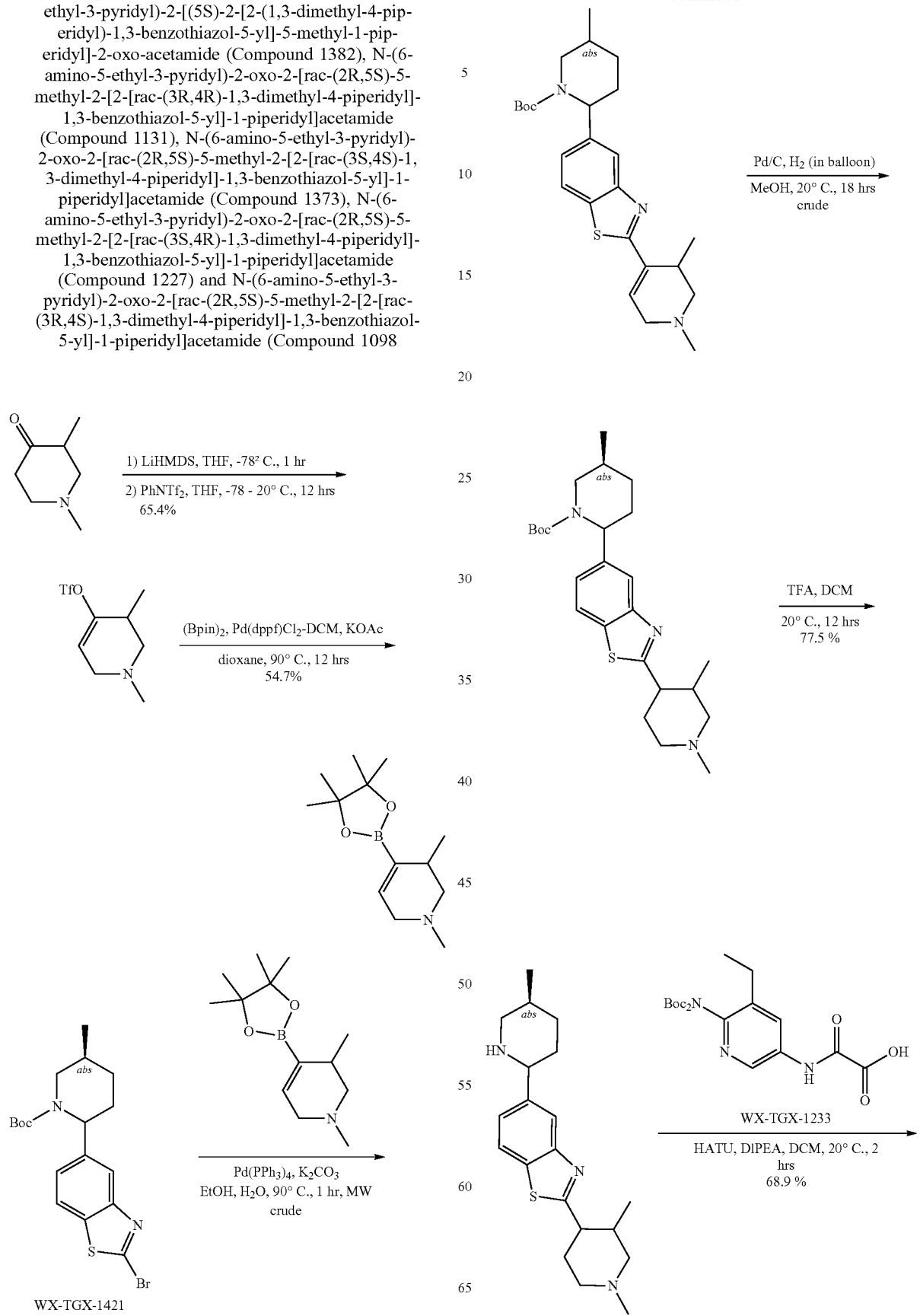

2335
-continued
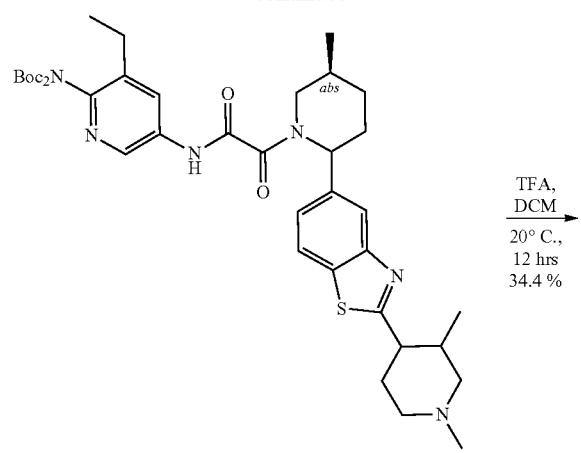
TFA, DCM
20° C.,
12 hrs
34.4 %
2336
-continued
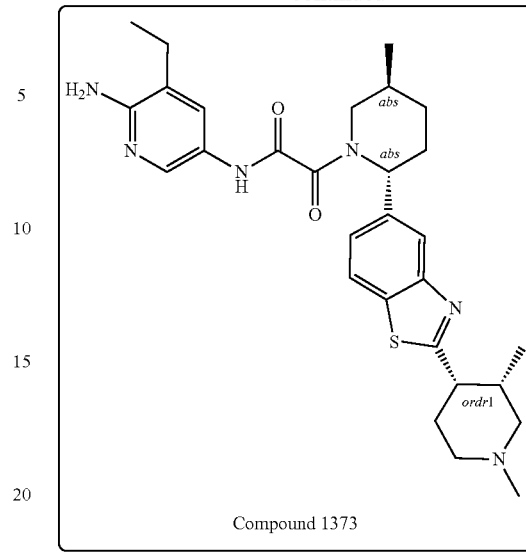
Compound 1373
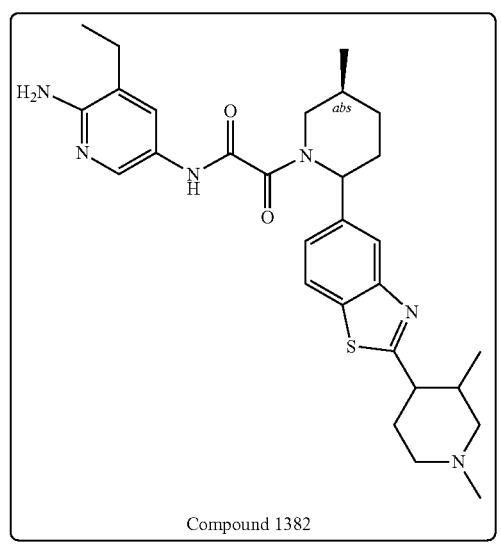
Compound 1382
chiral SFC
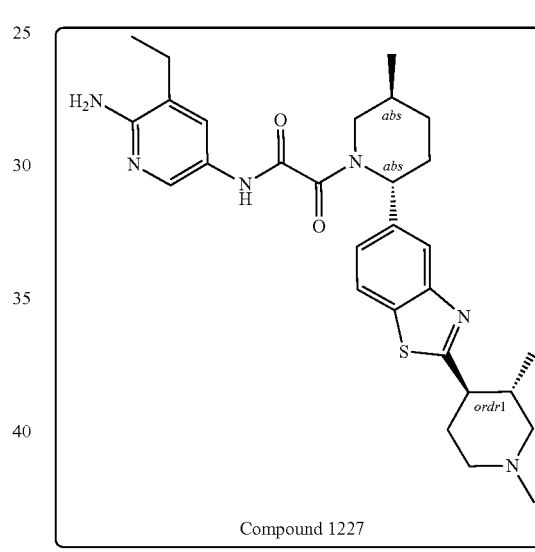
Compound 1227
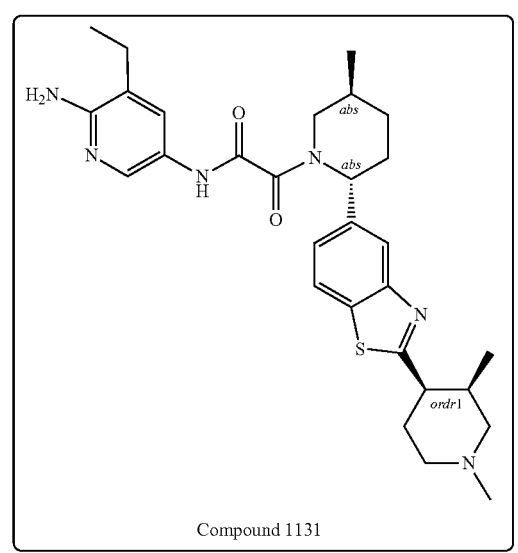
Compound 1131
+
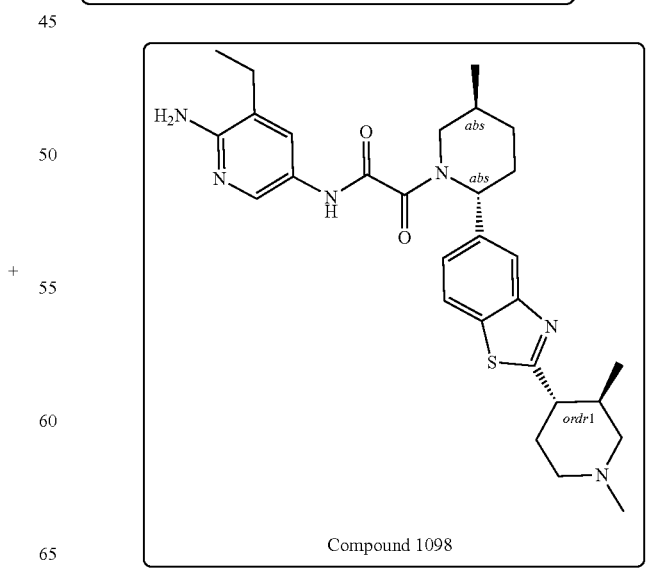
Compound 1098

Step 1: Synthesis of (1,3-dimethyl-3,6-dihydro-2H-pyridin-4-yl)trifluoromethanesulfonate To a mixture of 1,3-dimethylpiperidin-4-one (1.5 g, 0.0118 mol) in THF (10 mL) was sealed and degassed under vacuum and purged with $N_2$ for three times, and then 1M lithium; bis(trimethylsilyl)azanide/THF (17 mL, 17.0 mmol) was added at −78° C. dropwise, the mixture was stirred for 1 hour at −78° C., then PhNTf$_2$ (6.3 g, 0.176 mol) in THF (10 mL) was added. The solution was stirred at 20° C. for 12 hours. The resulting mixture was quenched by addition of water (50 mL) and extracted with EtOAc (50 mL*3). The combined organic layer was washed with saturated NH$_4$Cl aqueous solution (50 mL*2), brine (50 mL), dried over anhydrous Na$_2$SO$_4$, filtered and concentrated under reduced pressure. The residue was purified by flash chromatography (ISCO®; 24 g AgelaFlash® Silica Flash Column, petroleum ether/EtOAc with EtOAc from 0~80%, flow rate=30 mL/min, 254 nm) to afford (1,3-dimethyl-3,6-dihydro-2H-pyridin-4-yl)trifluoromethanesulfonate (2 g, 65.4% yield) as yellow oil. $^1$H NMR (400 MHz, methanol-d$_4$) δ ppm 5.83 (br s, 1H), 3.21-3.28 (m, 1H), 3.06-3.21 (m, 1H), 2.99 (br dd, J=11.5, 5.3 Hz, 1H), 2.80 (br s, 1H), 2.36-2.48 (m, 4H), 1.16 (d, J 7.0 Hz, 3H). LCMS (ESI) [M+H]$^+$ m/z: calcd 260.0, found 260.0.

Step 2: Synthesis of 1,3-dimethyl-4-(4,4,5,5-tetramethyl-1,3,2-dioxaborolan-2-yl)-3,6-dihydro-2H-pyridine To a solution of (1,3-dimethyl-3,6-dihydro-2H-pyridin-4-yl)trifluoromethanesulfonate (2 g, 7.71 mmol), 4,4,5,5-tetramethyl-2-(4,4,5,5-tetramethyl-1,3,2-dioxaborolan-2-yl)-1,3,2-dioxaborolane (2.43 g, 9.56 mmol), cyclopentyl(diphenyl)phosphane; dichloromethane; dichloropalladium; iron (650 mg, 0.796 mmol) in dioxane (20 mL) was added CH$_3$COOK (2.29 g, 0.0233 mol). The resulting mixture was sealed and degassed under vacuum and purged with N$_2$ for three times, and then stirred at 90° C. for 12 hours under N$_2$. The resulting mixture was quenched by addition of water (50 mL) and extracted with EtOAc (50 mL*3). The combined organic layer was washed with saturated NH$_4$Cl aqueous solution (50 mL*2), brine (50 mL), dried over anhydrous Na$_2$SO$_4$, filtered and concentrated under reduced pressure. The residue was purified by flash chromatography (ISCO®; 24 g AgelaFlash® Silica Flash Column, EtOAc/MeOH with MeOH from 0~20%, flow rate=30 mL/min, 254 nm) to afford 1,3-dimethyl-4-(4,4,5,5-tetramethyl-1,3,2-dioxaborolan-2-yl)-3,6-dihydro-2H-pyridine (1 g, 54.7% yield) as brown solid. LCMS (ESI) [M+H]$^+$ m/z: calcd 238.2, found 238.1.

Step 3: Synthesis of tert-butyl (5S)-2-[2-(1,3-dimethyl-3,6-dihydro-2H-pyridin-4-yl)-1,3-benzothiazol-5-yl]-5-methyl-piperidine-1-carboxylate tert-butyl (5S)-2-(2-bromo-1,3-benzothiazol-5-yl)-5-methyl-piperidine-1-carboxylate (300 mg, 0.729 mmol), 1,3-dimethyl-4-(4,4,5,5-tetramethyl-1,3,2-dioxaborolan-2-yl)-3,6-dihydro-2H-pyridine (300 mg, 1.27 mmol), K$_2$CO$_3$ (300 mg, 2.17 mmol), and Pd(PPh$_3$)$_4$ (120 mg, 0.104 mmol) were taken up into a microwave tube in EtOH (10 mL) and H$_2$O (1 mL). The sealed tube was heated at 90° C. for 1 hour in a microwave. The resulting mixture was quenched by addition of water (20 mL) and extracted with EtOAc (20 mL*3). The combined organic layer was washed with saturated NH$_4$Cl aqueous solution (20 mL*2), brine (20 mL), dried over anhydrous Na$_2$SO$_4$, filtered and concentrated under reduced pressure. The residue was purified by flash chromatography (ISCO®; 24 g AgelaFlash® Silica Flash Column, petroleum ether/EtOAc with EtOAc from 0~100%, flow rate=30 mL/min, 254 nm) to afford tert-butyl (5S)-2-[2-(1,3-dimethyl-3,6-dihydro-2H-pyridin-4-yl)-1,3-benzothiazol-5-yl]-5-methyl-piperidine-1-carboxylate (300 mg, crude) as brown oil. LCMS (ESI) [M+H]$^+$ m/z: calcd 442.2, found 442.2.

Step 4: Synthesis of tert-butyl (5S)-2-[2-(1,3-dimethyl-4-piperidyl)-1,3-benzothiazol-5-yl]-5-methyl-piperidine-1-carboxylate To a solution of tert-butyl (5S)-2-[2-(1,3-dimethyl-3,6-dihydro-2H-pyridin-4-yl)-1,3-benzothiazol-5-yl]-5-methyl-piperidine-1-carboxylate (300 mg, 0.679 mmol) in MeOH (4 mL) was added Pd/C (300 mg, 10% Pd/C with 50% of water, wt %). The resulting mixture was sealed and degassed under vacuum and purged with H$_2$ for three times, and then stirred at 20° C. for 18 hours under H$_2$ (in balloon). The resulting mixture was filtered and concentrated under reduced pressure to give tert-butyl (5S)-2-[2-(1,3-dimethyl-4-piperidyl)-1,3-benzothiazol-5-yl]-5-methyl-piperidine-1-carboxylate (250 mg, crude) as yellow oil. LCMS (ESI) [M+H]$^+$ m/z: calcd 442.2, found 444.3.

Step 5: Synthesis of 2-(1,3-dimethyl-4-piperidyl)-5-[(5S)-5-methyl-2-piperidyl]-1,3-benzothiazole To a solution of tert-butyl (5S)-2-[2-(1,3-dimethyl-4-piperidyl)-1,3-benzothiazol-5-yl]-5-methyl-piperidine-1-carboxylate (250 mg, 0.564 mmol) in DCM (6 mL) was added TFA (0.8 mL, 10.4 mmol). The mixture was stirred at 20° C. for 12 hours. The resulting mixture concentrated under reduced pressure to afford 2-(1,3-dimethyl-4-piperidyl)-5-[(5S)-5-methyl-2-piperidyl]-1,3-benzothiazole (150 mg, 77.5% yield) as yellow oil.

Step 6: Synthesis of tert-butyl N-tert-butoxycarbonyl-N-[5-[[2-[(5S)-2-[2-(1,3-dimethyl-4-piperidyl)-1,3-benzothiazol-5-yl]-5-methyl-1-piperidyl]-2-oxo-acetyl]amino]-3-ethyl-2-pyridyl]carbamate To a solution of 2-(1,3-dimethyl-4-piperidyl)-5-[(5S)-5-methyl-2-piperidyl]-1,3-benzothiazole (150 mg, 0.437 mmol), 2-[[6-[bis(tert-butoxycarbonyl)amino]-5-ethyl-3-pyridyl]amino]-2-oxo-acetic acid (170 mg, 0.415 mmol), HATU (225 mg, 0.592 mmol) in DCM (4 mL) was added N-ethyl-N-isopropyl-propan-2-amine (0.4 mL, 2.30 mmol). The mixture was stirred at 20° C. for 2 hours. The resulting mixture was quenched by addition of water (100 mL) and extracted with EtOAc (100 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®; 12 g AgelaFlash® Silica Flash Column, EtOAc/MeOH with MeOH from 0~20%, flow rate=30 mL/min, 254 nm) to afford tert-butyl N-tert-butoxycarbonyl-N-[5-[[2-[(5S)-2-[2-(1,3-dimethyl-4-piperidyl)-1,3-benzothiazol-5-yl]-5-methyl-1-piperidyl]-2-oxo-acetyl]amino]-3-ethyl-2-pyridyl]

carbamate (200 mg, 68.9% yield) as yellow oil. LCMS (ESI) [M+H]+ m/z: calcd 735.4, found 735.4.

Step 7: Synthesis of N-(6-amino-5-ethyl-3-pyridyl)-2-[(5S)-2-[2-(1,3-dimethyl-4-piperidyl)-1,3-benzothiazol-5-yl]-5-methyl-1-piperidyl]-2-oxo-acetamide (Compound 1382

To a solution of tert-butyl N-tert-butoxycarbonyl-N-[5-[[2-[(5S)-2-[2-(1,3-dimethyl-4-piperidyl)-1,3-benzothiazol-5-yl]-5-methyl-1-piperidyl]-2-oxo-acetyl]amino]-3-ethyl-2-pyridyl]carbamate (200 mg, 0.272 mmol) in DCM (4 mL) was added TFA (0.02 mL, 0.272 mmol). The mixture was stirred at 20° C. for 12 hours. The resulting mixture was concentrated under reduced pressure. The residue was purified by preparative HPLC (Instrument: Gilson GX-281 Liquid Handler, Gilson 322 Pump, Gilson 156 UV Detector; Column: Phenomenex Gemini NX 80×40 mm×3 m; Mobile phase A: H$_2$O with 10 mmol NH$_4$HCO$_3$ (v %); Mobile phase B: MeCN; Gradient: B from 35% to 65% in 9.5 min, hold 100% B for 1 min; Flow Rate: 25 mL/min; Column Temperature: 30° C.; Wavelength: 220 nm, 254 nm) to afford N-(6-amino-5-ethyl-3-pyridyl)-2-[(5S)-2-[2-(1,3-dimethyl-4-piperidyl)-1,3-benzothiazol-5-yl]-5-methyl-1-piperidyl]-2-oxo-acetamide (50 mg, 34.4% yield) as white solid. $^1$H NMR (400 MHz, methanol-d$_4$) δ ppm 7.88-8.17 (m, 3H), 7.36-7.71 (m, 2H), 5.43-5.91 (m, 1H), 3.67-4.20 (m, 1H), 3.43 (br s, 1H), 2.72-3.20 (m, 3H), 1.82-2.63 (m, 15H), 1.20-1.52 (m, 3H), 1.15 (br d, J=6.8 Hz, 3H), 0.84-0.97 (m, 3H); LCMS (ESI) [M+H]+ m/z: calcd 535.3, found 535.3; HPLC: 1000%@220 nm, 1000%@254 nm.

Step 8: Synthesis of N-(6-amino-5-ethyl-3-pyridyl)-2-oxo-2-[rac-(2R,5S)-5-methyl-2-[2-[rac-(3R,4R)-1,3-dimethyl-4-piperidyl]-1,3-benzothiazol-5-yl]-1-piperidyl]acetamide (Compound 1131), N-(6-amino-5-ethyl-3-pyridyl)-2-oxo-2-[rac-(2R,5S)-5-methyl-2-[2-[rac-(3S,4S)-1,3-dimethyl-4-piperidyl]-1,3-benzothiazol-5-yl]-1-piperidyl]acetamide (Compound 1373), N-(6-amino-5-ethyl-3-pyridyl)-2-oxo-2-[rac-(2R,5S)-5-methyl-2-[2-[rac-(3S,4R)-1,3-dimethyl-4-piperidyl]-1,3-benzothiazol-5-yl]-1-piperidyl]acetamide (Compound 1227) and N-(6-amino-5-ethyl-3-pyridyl)-2-oxo-2-[rac-(2R,5S)-5-methyl-2-[2-[rac-(3R,4S)-1,3-dimethyl-4-piperidyl]-1,3-benzothiazol-5-yl]-1-piperidyl]acetamide (Compound 1098

N-(6-amino-5-ethyl-3-pyridyl)-2-[(5S)-2-[2-(1,3-dimethyl-4-piperidyl)-1,3-benzothiazol-5-yl]-5-methyl-1-piperidyl]-2-oxo-acetamide (50 mg, 0.0935 mmol) was purified by chiral SFC (Instrument: Thar800Q; Column: daicel chiralcel OJ 250×30 mm I.D. 10 m; Mobile phase: supercritical CO$_2$/EtOH (0.1% NH$_3$·H$_2$O, v %)=75/25; Flow Rate: 70 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford two product.
Peak 1 was further purified by chiral SFC (Instrument: ACSSH-CO; Column: daicel chiralcel IC 250×30 mm*5 m; Mobile phase: supercritical hexane/IPA (0.1% NH$_3$—H$_2$O, v %)=70/30;
Flow Rate: 25 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1131 and Compound 1373.

Compound 1131: N-(6-amino-5-ethyl-3-pyridyl)-2-oxo-2-[rac-(2R,5S)-5-methyl-2-[2-[rac-(3R,4R)-1,3-dimethyl-4-piperidyl]-1,3-benzothiazol-5-yl]-1-piperidyl]acetamide (peak 1, retention time=4.028 min, single unknown enantiomer, white solid). $^1$H NMR (400 MHz, methanol-d$_4$) δ ppm 8.41-8.81 (m, 1H), 7.86-8.11 (m, 3H), 7.35-7.51 (m, 1H), 5.44-5.91 (m, 1H), 3.39-4.20 (m, 7H), 3.14 (br d, J=11.5 Hz, 1H), 3.00 (br d, J=12.0 Hz, 2H), 2.13-2.61 (m, 14H), 1.98 (br d, J=12.0 Hz, 5H), 1.47 (br d, J=12.0 Hz, 1H), 1.14 (d, J=7.0 Hz, 3H); LCMS (ESI) [M+H]+ m/z: calcd 535.3, found 535.3; HPLC: 96.510%@220 nm, 96.00%/@254 nm; 96.7% ee.

Compound 1373: N-(6-amino-5-ethyl-3-pyridyl)-2-oxo-2-[rac-(2R,5S)-5-methyl-2-[2-[rac-(3S,4S)-1,3-dimethyl-4-piperidyl]-1,3-benzothiazol-5-yl]-1-piperidyl]acetamide (peak 2, retention time=4.169 min, single unknown enantiomer, white solid). $^1$H NMR (400 MHz, methanol-d$_4$) δ ppm 8.41-8.81 (m, 1H), 7.86-8.11 (m, 3H), 7.35-7.51 (m, 1H), 5.44-5.91 (m, 1H), 3.39-4.20 (m, 7H), 3.14 (br d, J=11.5 Hz, 1H), 3.00 (br d, J=12.0 Hz, 2H), 2.13-2.61 (m, 14H), 1.98 (br d, J=12.0 Hz, 5H), 1.47 (br d, J=12.0 Hz, 1H), 1.14 (d, J=7.0 Hz, 3H); LCMS (ESI) [M+H]+ m/z: calcd 535.3, found 535.3; HPLC: 96.75%/@220 nm, 96.89%/@254 nm; 74.6% ee.

Peak 2 was further purified by chiral SFC (Instrument: Berger, Multigr AM-II; Column: daicel chiralcel AD 250×30 mm*10 m; Mobile phase: supercritical CO$_2$/EtOH (0.1% NH$_3$—H$_2$O, v %)=50/50; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1227 and Compound 1098.

Compound 1227: N-(6-amino-5-ethyl-3-pyridyl)-2-oxo-2-[rac-(2R,5S)-5-methyl-2-[2-[rac-(3S,4R)-1,3-dimethyl-4-piperidyl]-1,3-benzothiazol-5-yl]-1-piperidyl]acetamide (peak 3, retention time=4.648 min, single unknown enantiomer, white solid). $^1$H NMR (400 MHz, methanol-d$_4$) δ ppm 7.90-8.21 (m, 3H), 7.29-7.78 (m, 2H), 5.84 (br s, 1H), 3.67-4.19 (m, 1H), 3.37-3.55 (m, 1H), 2.72-3.18 (m, 2H), 1.80-2.61 (m, 12H), 1.47 (br d, J 11.3 Hz, 1 H), 1.07-1.35 (m, 6H), 0.92 (br s, 3H); LCMS (ESI) [M+H]+ m/z: calcd 535.3, found 535.3; HPLC: 97.75%@220 nm, 100%@254 nm; 98.8% ee.

Compound 1098: N-(6-amino-5-ethyl-3-pyridyl)-2-oxo-2-[rac-(2R,5S)-5-methyl-2-[2-[rac-(3R,4S)-1,3-dimethyl-4-piperidyl]-1,3-benzothiazol-5-yl]-1-piperidyl]acetamide (peak 4, retention time=4.689 min, single unknown enantiomer, white solid). $^1$H NMR (400 MHz, methanol-d$_4$) δ ppm 7.86-8.17 (m, 3H), 7.32-7.72 (m, 2H), 5.45-5.90 (m, 1H), 3.69-4.18 (m, 1H), 3.37-3.49 (m, 1H), 2.95-3.20 (m, 1H), 2.82 (br d, J=9.5 Hz, 1H), 1.88-2.59 (m, 14H), 1.47 (br d, J 12.0 Hz, 1H), 1.22-1.31 (m, 2H), 1.15 (d, J 6.8 Hz, 3H), 0.93 (br d, J 5.5 Hz, 3H); LCMS (ESI) [M+H]+ m/z: calcd 535.3, found 535.3; HPLC: 96.27%@220 nm, 100%@254 nm; 100% ee.

Example 449. The Synthesis of N-(6-amino-5-ethyl-3-pyridyl)-2-[(2R,5S)-5-methyl-2-[2-(8-methyl-8-azabicyclo[3.2.1]octan-3-yl)-1,3-benzothiazol-5-yl]-1-piperidyl]-2-oxo-acetamide (Compound 1187
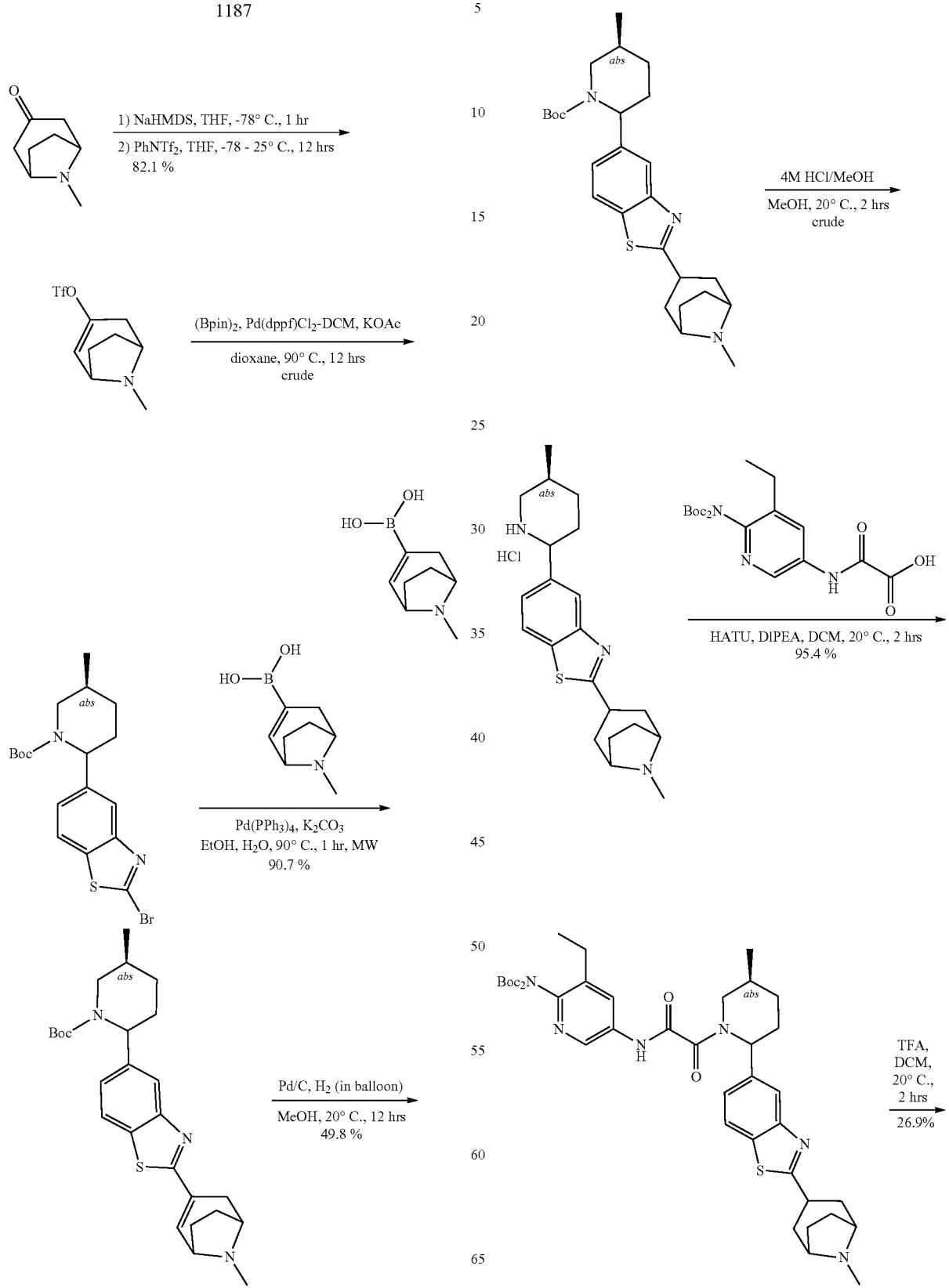

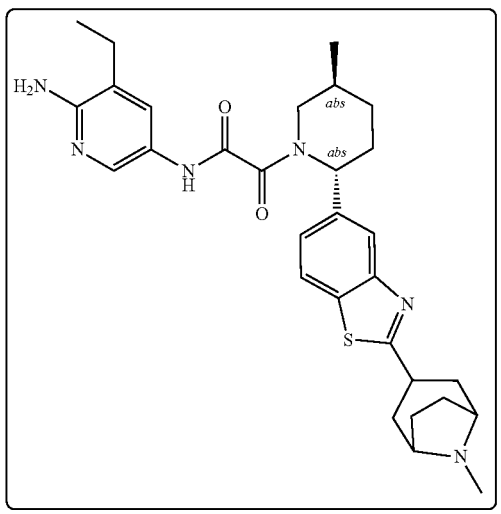

Step 1: Synthesis of (8-methyl-8-azabicyclo[3.2.1]
oct-3-en-3-yl)trifluoromethanesulfonate To a mixture of 8-methyl-8-azabicyclo[3.2.1]octan-3-one (1 g, 7.18 mmol) in THF (20 mL) was sealed and degassed under vacuum and purged with $N_2$ for three times, and then 1M LiHMDS/THF (13 mL, 13.0 mmol) was added at −78° C. dropwise, and the mixture was stirred 1 hour at −78° C. Then a solution of PhNTf$_2$ (3.85 g, 10.8 mmol) in THF (20 mL) was added. The solution was stirred at 25° C. for 12 hours. The resulting mixture was quenched by addition of saturated NH$_4$Cl aqueous solution (100 mL) and extracted with EtOAc (100 mL*3). The combined organic layer was washed with saturated NH$_4$Cl aqueous solution (100 mL), brine (100 mL), dried over anhydrous Na$_2$SO$_4$, filtered and concentrated under reduced pressure. The residue was purified by flash chromatography (ISCO®; 25 g AgelaFlash® Silica Flash Column, petroleum ether/EtOAc with EtOAc from 0~60%, flow rate=60 mL/min, 12) to afford (8-methyl-8-azabicyclo[3.2.1]oct-3-en-3-yl)trifluoromethanesulfonate (1.6 g, 82.1% yield) as brown oil. $^1$H NMR (400 MHz, methanol-d$_4$) δ ppm 5.95 (br d, J=5.4 Hz, 1H), 3.52 (t, J=5.7 Hz, 1H), 3.44 (br dd, J=6.1, 4.9 Hz, 1H), 2.85 (br dd, J=17.5, 3.1 Hz, 1H), 2.40 (s, 3H), 2.15-2.26 (m, 1H), 1.95-2.12 (m, 3H), 1.68 (ddd, J=12.9, 9.2, 6.5 Hz, 1H); LCMS (ESI) [M+H]$^+$ m/z: calcd 272.0, found 272.0.

Step 2: Synthesis of (8-methyl-8-azabicyclo[3.2.1]
oct-3-en-3-yl) boronic acid

To a solution of (8-methyl-8-azabicyclo[3.2.1]oct-3-en-3-yl)trifluoromethanesulfonate (1.6 g, 5.90 mmol), 4,4,5,5-tetramethyl-2-(4,4,5,5-tetramethyl-1,3,2-dioxaborolan-2-yl)-1,3,2-dioxaborolane (1.86 g, 7.31 mmol), cyclopentyl(diphenyl)phosphane; dichloromethane; dichloropalladium; iron (430 mg, 0.527 mmol) in dioxane (20 mL) was added CH$_3$COOK (1.75 g, 17.8 mmol). The resulting mixture was sealed and degassed under vacuum and purged with $N_2$ for three times. Then the mixture was stirred at 90° C. for 12 hours under $N_2$ atmosphere. The resulting mixture was quenched by addition of water (100 mL) and extracted with EtOAc (100 mL*3). The combined water layer was concentrated under reduced pressure to give crude product, which was dissolved with DCM/MeOH (10:1) (100 mL). Then the solution was filtered and the filtrate was concentrated under reduced pressure to give (8-methyl-8-azabicyclo[3.2.1]oct-3-en-3-yl)boronic acid (2 g, crude) as yellow solid. LCMS (ESI) [M+H]$^+$ m/z: calcd 168.1, found 168.1.

Step 3: Synthesis of tert-butyl (5S)-5-methyl-2-[2-(8-methyl-8-azabicyclo[3.2.1]oct-3-en-3-yl)-1,3-benzothiazol-5-yl]piperidine-1-carboxylate To a mixture of tert-butyl (5S)-2-(2-bromo-1,3-benzothiazol-5-yl)-5-methyl-piperidine-1-carboxylate (300 mg, 0.729 mmol), (8-methyl-8-azabicyclo[3.2.1]oct-3-en-3-yl) boronic acid (1.5 g, 8.98 mmol) in EtOH (6 mL) and H$_2$O (2 mL) were added Pd(PPh$_3$)$_4$ (80 mg, 0.0692 mmol) and K$_2$CO$_3$ (300 mg, 2.17 mmol). The resulting mixture was stirred at 90° C. for 1 hour in microwave. The resulting mixture was concentrated under reduced pressure. The residue was purified by flash chromatography (ISCO®; 12 g AgelaFlash® Silica Flash Column, EtOAc/MeOH with MeOH from 0~20%, flow rate=60 mL/min, 254 nm) to afford tert-butyl (5S)-5-methyl-2-[2-(8-methyl-8-azabicyclo[3.2.1]oct-3-en-3-yl)-1,3-benzothiazol-5-yl]piperidine-1-carboxylate (300 mg, 90.7% yield) as brown oil. LCMS (ESI) [M+H]$^+$ m/z: calcd 454.2, found 454.2.

Step 4: Synthesis of tert-butyl (5S)-5-methyl-2-[2-(8-methyl-8-azabicyclo[3.2.1]octan-3-yl)-1,3-benzothiazol-5-yl]piperidine-1-carboxylate A mixture of tert-butyl (5S)-5-methyl-2-[2-(8-methyl-8-azabicyclo[3.2.1]oct-3-en-3-yl)-1,3-benzothiazol-5-yl]piperidine-1-carboxylate (300 mg, 0.661 mmol), Pd/C (50 mg, 10% of Pd with 50% of water, wt %) and MeOH (10 mL) was stirred at 20° C. for 12 hours under hydrogen (in balloon). The resulting mixture was filtered and concentrated under reduced pressure. The residue was purified by preparative HPLC (Instrument: Gilson GX-281 Liquid Handler, Gilson 322 Pump, Gilson 156 UV Detector; Column: Welch Xtimate C18 150*25 mm*5 µm; Mobile phase A: H$_2$O with 0.225% FA (v %); Mobile phase B: MeOH; Gradient: B from 45% to 75% in 9.5 min, hold 100% B for 2 min; Flow Rate: 25 mL/min; Column Temperature: 30° C.; Wavelength: 220 nm, 254 nm) to afford tert-butyl (5S)-5-methyl-2-[2-(8-methyl-8-azabicyclo[3.2.1]octan-3-yl)-1,3-benzothiazol-5-yl]piperidine-1-carboxylate (150 mg, 49.8% yield) as white solid. LCMS (ESI) [M+H]$^+$ m/z: calcd 456.3, found 456.2.

Step 5: Synthesis of 2-(8-methyl-8-azabicyclo[3.2.1]octan-3-yl)-5-[(5S)-5-methyl-2-piperidyl]-1,3-benzothiazole A mixture of tert-butyl (5S)-5-methyl-2-[2-(8-methyl-8-azabicyclo[3.2.1]octan-3-yl)-1,3-benzothiazol-5-yl]piperidine-1-carboxylate (150 mg, 0.329 mmol), MeOH (3 mL) and 4M HCl/MeOH (3 mL, 12.0 mmol) was stirred at 20° C. for 2 hours. The resulting mixture was concentrated under reduced pressure to give 2-(8-methyl-8-azabicyclo[3.2.1]octan-3-yl)-5-[(5S)-5-methyl-2-piperidyl]-1,3-benzothiazole (110 mg, crude, HCl) as white solid. LCMS (ESI) [M+H]$^+$ m/z: calcd 356.2, found 356.1.

Step 6: Synthesis of tert-butyl N-tert-butoxycarbonyl-N-[3-ethyl-5-[[2-[(5S)-5-methyl-2-[2-(8-methyl-8-azabicyclo[3.2.1]octan-3-yl)-1,3-benzothiazol-5-yl]-1-piperidyl]-2-oxo-acetyl]amino]-2-pyridyl]carbamate To a mixture of 2-(8-methyl-8-azabicyclo[3.2.1]octan-3-yl)-5-[(5S)-5-methyl-2-piperidyl]-1,3-benzothiazole (110 mg, 0.281 mmol, HCl), 2-[[6-[bis(tert-butoxycarbonyl)amino]-5-ethyl-3-pyridyl]amino]-2-oxo-acetic acid (120 mg, 0.293 mmol) in DCM (5 mL) were added HATU (130 mg, 0.342 mmol) and DIPEA (0.25 mL, 1.44 mmol). The resulting mixture was stirred at 20° C. for 2 hours. The resulting mixture was concentrated under reduced pressure. The residue was purified by flash chromatography (ISCO®; 12 g AgelaFlash® Silica Flash Column, EtOAc/MeOH with MeOH from 0~40%, flow rate=30 mL/min, 254 nm) to afford tert-butyl N-tert-butoxycarbonyl-N-[3-ethyl-5-[[2-[(5S)-5-methyl-2-[2-(8-methyl-8-azabicyclo[3.2.1]octan-3-yl)-1,3-benzothiazol-5-yl]-1-piperidyl]-2-oxo-acetyl]amino]-2-pyridyl]carbamate (200 mg, 95.4% yield) as yellow oil. LCMS (ESI) [M+H]$^+$ m/z: calcd 747.4, found 747.5.

Step 7: Synthesis of N-(6-amino-5-ethyl-3-pyridyl)-2-[(2R,5S)-5-methyl-2-[2-(8-methyl-8-azabicyclo[3.2.1]octan-3-yl)-1,3-benzothiazol-5-yl]-1-piperidyl]-2-oxo-acetamide (Compound 1187)

A mixture of tert-butyl N-tert-butoxycarbonyl-N-[3-ethyl-5-[[2-[(5S)-5-methyl-2-[2-(8-methyl-8-azabicyclo[3.2.1]octan-3-yl)-1,3-benzothiazol-5-yl]-1-piperidyl]-2-oxo-acetyl]amino]-2-pyridyl]carbamate (200 mg, 0.268 mmol), DCM (3 mL) and TFA (3 mL, 38.9 mmol) was stirred at 20° C. for 2 hours. The resulting mixture was adjusted to pH=9 with saturated NaHCO$_3$ solution, and then the mixture was concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80*40 mm*3 μm; Mobile phase A: H$_2$O with 10 mmol NH$_4$HCO$_3$ (v %); Mobile phase B: MeCN; Gradient: B from 22% to 52% in 9.5 min, hold 100% B for 1 min; Flow Rate: 25 mL/min; Column Temperature: 30° C.; Wavelength: 220 nm, 254 nm) to afford N-(6-amino-5-ethyl-3-pyridyl)-2-[(2R,5S)-5-methyl-2-[2-(8-methyl-8-azabicyclo[3.2.1]octan-3-yl)-1,3-benzothiazol-5-yl]-1-piperidyl]-2-oxo-acetamide (39.4 mg, 26.9% yield) as white solid. $^1$H NMR (400 MHz, methanol-d$_4$) δ ppm 8.01-8.21 (m, 1H), 7.86-8.01 (m, 2H), 7.61-7.85 (m, 1H), 7.37-7.51 (m, 1H), 5.44-5.86 (m, 1H), 3.69-4.13 (m, 1H), 3.54 (br s, 1H), 3.33-3.46 (m, 3H), 2.51 (br d, J=6.9 Hz, 2H), 2.38 (s, 5H), 2.17-2.25 (m, 2H), 1.99-2.15 (m, 4H), 1.78-1.96 (m, 4H), 1.40-1.55 (m, 1H), 1.17-1.33 (m, 3H), 1.14 (br d, J=6.9 Hz, 3H); LCMS (ESI) [M+H]$^+$ m/z: calcd 547.3, found 547.3; HPLC: 100%@220 nm, 99.11%@254 nm; 96.8% ee.

Example 450. The Synthesis of N-(6-amino-5-ethyl-3-pyridyl)-2-oxo-2-[rac-(2R,5S)-5-methyl-2-[4-[rac-(3aS,7aS)-5-methyl-3,3a,4,6,7,7a-hexahydro-1H-pyrrolo[3,4-c]pyridin-2-yl]phenyl]-1-piperidyl]acetamide (Compound 1167) and N-(6-amino-5-ethyl-3-pyridyl)-2-oxo-2-[rac-(2R,5S)-5-methyl-2-[4-[rac-(3aR,7aR)-5-methyl-3,3a,4,6,7,7a-hexahydro-1H-pyrrolo[3,4-c]pyridin-2-yl]phenyl]-1-piperidyl]acetamide (Compound 1287

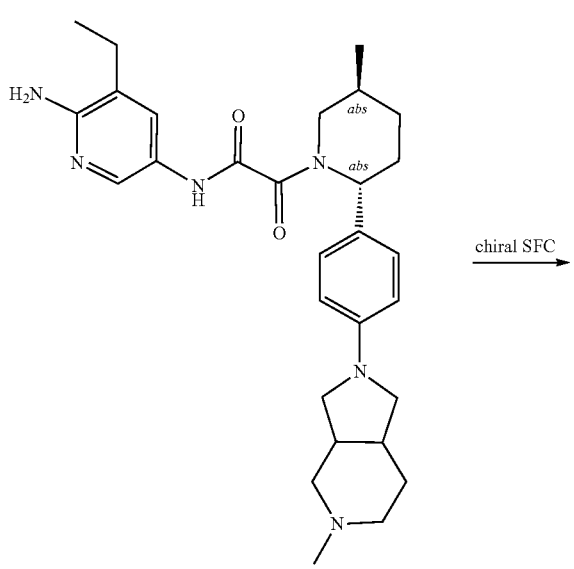

chiral SFC →

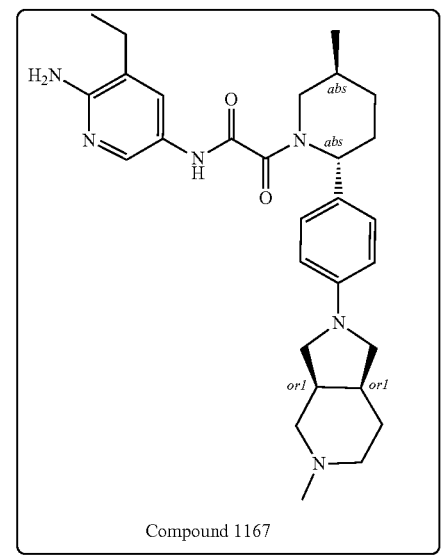

Compound 1167

+

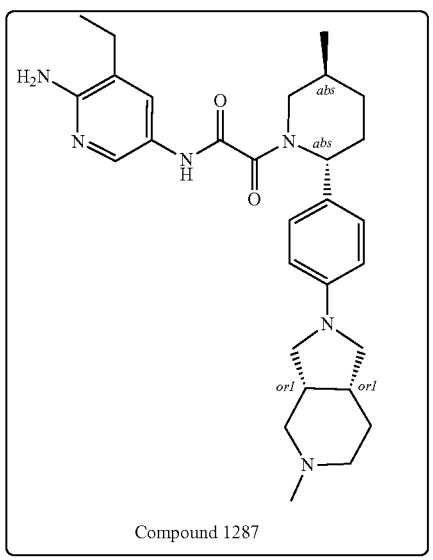

Compound 1287

N-(6-amino-5-ethyl-3-pyridyl)-2-oxo-2-[rac-(2R,5S)-5-methyl-2-[4-(5-methyl-3,3a,4,6,7,7a-hexahydro-1H-pyrrolo[3,4-c]pyridin-2-yl)phenyl]-1-piperidyl]acetamide (50 mg, 0.0991 mmol) was purified by chiral SFC (Instrument: Berger, Multigr AM-II; Column: Daicel chiralpak AS (250 mm*30 mm*5 μm); Mobile phase: supercritical Hexane-IPA (0.1% NH$_3$, MeOH v %)=60/40; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm). The fraction was concentrated under reduced pressure and then lyophilized for overnight to give Compound 1167 and Compound 1287.

Compound 1167: N-(6-amino-5-ethyl-3-pyridyl)-2-oxo-2-[rac-(2R,5S)-5-methyl-2-[4-[rac-(3aS,7aS)-5-methyl-3,3a,4,6,7,7a-hexahydro-1H-pyrrolo[3,4-c]pyridin-2-yl]phenyl]-1-piperidyl]acetamide (11 mg, single unknown enantiomer, Peak 2, Retention time: 1.337 min, white solid). $^1$H NMR (400 MHz, methanol-d$_4$) δ ppm 7.93-8.13 (m, 1H), 7.49-7.69 (m, 1H), 7.16 (br d, J=8.3 Hz, 2H), 6.48-6.60 (m, 2H), 5.58-5.74 (m, 1H), 3.60-4.00 (m, 1H), 3.23 (br s, 3H), 2.40-2.64 (m, 7H), 2.28 (s, 6H), 1.91 (br d, J=10.5 Hz, 3H), 1.72 (br s, 2H), 1.23-1.44 (m, 5H), 1.11 (br d, J=6.9 Hz, 3H); LCMS (ESI) [M+H]$^+$ m/z: calcd 505.3, found 505.4; HPLC: 98.690%@220 nm, 99.230%@254 nm; 100% ee.

Compound 1287: N-(6-amino-5-ethyl-3-pyridyl)-2-oxo-2-[rac-(2R,5S)-5-methyl-2-[4-[rac-(3aR,7aR)-5-methyl-3,3a,4,6,7,7a-hexahydro-1H-pyrrolo[3,4-c]pyridin-2-yl]phenyl]-1-piperidyl]acetamide (13.2 mg, single unknown enantiomer, Peak 3, Retention time: 2.427 min, white solid). $^1$H NMR (400 MHz, methanol-d$_4$) δ ppm 7.92-8.19 (m, 1H), 7.43-7.69 (m, 1H), 7.08-7.23 (m, 2H), 6.31-6.64 (m, 2H), 5.12-5.74 (m, 1H), 3.55-4.26 (m, 1H), 3.08-3.27 (m, 3H), 2.35-2.75 (m, 8H), 2.17-2.33 (m, 5H), 1.90 (br d, J=7.8 Hz, 3H), 1.70 (br d, J=8.8 Hz, 2H), 1.18-1.48 (m, 5H), 1.11 (br d, J=6.8 Hz, 3H); LCMS (ESI) [M+H]$^+$ m/z: calcd 505.3, found 505.3; HPLC: 1000%@254 nm, 99.050%@254 nm; 98.6% ee.

Example 451. The Synthesis of N-(6-amino-5-cyclopropylpyridin-3-yl)-2-((2S,5R)-5-methyl-2-(2-methyl-2H-indazol-6-yl)piperidin-1-yl)-2-oxoacetamide (Compound 1043

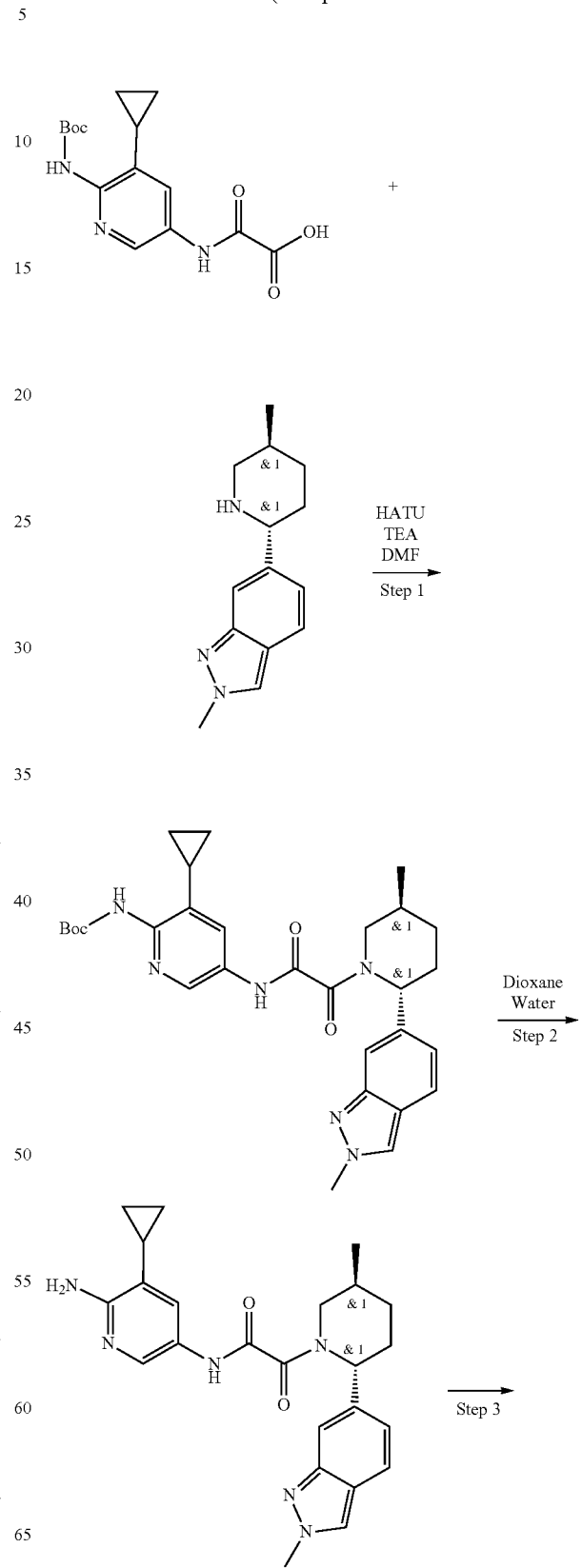

-continued

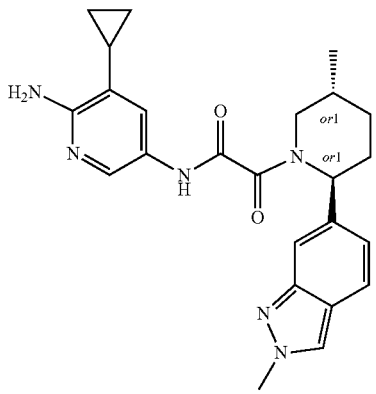

Compound 1403

+

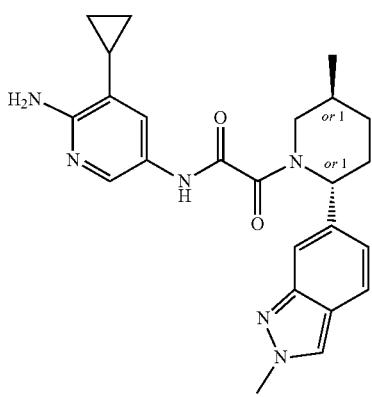

ent-Compound 1403

Step 1: The Synthesis of tert-butyl N-[3-cyclopropyl-5-[[2-[(2R,5S)-5-methyl-2-(2-methylindazol-6-yl)-1-piperidyl]-2-oxo-acetyl]amino]-2-pyridyl]carbamate 2-[[6-(tert-butoxycarbonylamino)-5-cyclopropyl-3-pyridyl]amino]-2-oxo-acetic acid (0.32 g, 996 μmol) was added to a mixture of 2-methyl-6-[(2R,5S)-5-methyl-2-piperidyl]indazole (228 mg, 996 μmol) and Triethylamine (504 mg, 4.98 mmol, 694 μL) in DMFA (4.00 mL). The resulting mixture was stirred for 10 min. HATU (454 mg, 1.20 mmol) was added and stirring was continued at 25° C. for 17 hr. The obtained mixture was concentrated in vacuo. The residue was subjected to HPLC (0-5 min 40-90% water-MeOH; flow: 30 mL/min, column: Chromatorex 18 SMB100-5T, 100×19 mm, 5 μm) to afford tert-butyl N-[3-cyclopropyl-5-[[2-[(2R,5S)-5-methyl-2-(2-methylindazol-6-yl)-1-piperidyl]-2-oxo-acetyl]amino]-2-pyridyl]carbamate (0.164 g, crude) as a yellow solid.

LCMS(ESI): [M+H]+ m/z: calcd 533.32; found 533.2; Rt=3.460.

Step 2: The Synthesis of N-(6-amino-5-cyclopropyl-3-pyridyl)-2-[(2R,5S)-5-methyl-2-(2-methylindazol-6-yl)-1-piperidyl]-2-oxo-acetamide Tert-butyl N-[3-cyclopropyl-5-[[2-[(2R,5S)-5-methyl-2-(2-methylindazol-6-yl)-1-piperidyl]-2-oxo-acetyl]amino]-2-pyridyl]carbamate (0.12 g, 225 μmol) was dissolved in a mixture of Water (2.00 mL) and Dioxane (2.00 mL). The resulting mixture was allowed to stir at 100° C. for 20 hr. The obtained mixture was subjected to HPLC (0-5 min 30-80% water-methanol, +0.1% vol. of 25% aq. NH₃, 30 mL/min, column: YMC-Actus Triart C18, 100×20 mm, 5 μm) to afford N-(6-amino-5-cyclopropyl-3-pyridyl)-2-[(2R,5S)-5-methyl-2-(2-methylindazol-6-yl)-1-piperidyl]-2-oxo-acetamide (0.04 g, 90.2 μmol, 40.0% yield) as a yellow solid.

LCMS(ESI): [M+H]+ m/z: calcd 433.26; found 433.4; Rt=2.443.

Step 3: The Synthesis of N-(6-amino-5-cyclopropylpyridin-3-yl)-2-((2S,5R)-5-methyl-2-(2-methyl-2H-indazol-6-yl)piperidin-1-yl)-2-oxoacetamide N-(6-amino-5-cyclopropyl-3-pyridyl)-2-[(2R,5S)-5-methyl-2-(2-methylindazol-6-yl)-1-piperidyl]-2-oxo-acetamide (0.04 g, 90.2 μmol) was subjected to chiral chromatography (Chiralpak As-H (250*20, 5 mkm), Hexane-IPA-MeOH, 50-25-25, 12 mL/min) to afford N-(6-amino-5-cyclopropylpyridin-3-yl)-2-((2S,5R)-5-methyl-2-(2-methyl-2H-indazol-6-yl)piperidin-1-yl)-2-oxoacetamide (0.01786 g, 41.29 μmol, 4.47% yield)

Preparative:

RT for ent-Compound 1403 (Chiralpak As-H (250*20, 5 mkm), Hexane-IPA-MeOH, 50-25-25, 12 mL/min)=10.623

RT for Compound 1403 (Chiralpak As-H (250*20, 5 mkm), Hexane-IPA-MeOH, 50-25-25, 12 mL/min)=15.580.

Analytical: RT for Compound 1403 Chiralpak As-H (250*4.6, 5 mkm), Hexane-IPA-MeOH, 50-25-25, 0.6 mL/min)=9.495.

¹H NMR (600 MHz, DMSO-d₆) δ 0.35-0.51 (m, 2H), 0.81-0.92 (m, 2H), 0.96-1.08 (m, 3H), 1.29-1.42 (m, 1H), 1.61-1.80 (m, 2H), 1.82-1.94 (m, 1H), 1.98-2.19 (m, 1H), 2.20-2.36 (m, 1H), 2.75-3.25 (m, 1H), 3.45-4.05 (m, 1H), 4.14 (s, 3H), 5.14-5.66 (m, 1H), 5.67-5.79 (m, 2H), 6.89-7.08 (m, 1H), 7.27-7.43 (m, 1H), 7.44-7.53 (m, 1H), 7.63-7.74 (m, 1H), 7.95-8.09 (m, 1H), 8.28 (s, 1H), 10.40-10.57 (m, 1H).

LCMS(ESI): [M+H]+ m/z: calcd 433.26; found 433.2; Rt=0.955.

Analytical: RT for ent-Compound 1403 (Chiralpak As-H (250*4.6, 5 mkm), Hexane-IPA-MeOH, 50-25-25, 0.6 mL/min)=13.320.

¹H NMR (600 MHz, dmso) δ 0.39-0.50 (m, 2H), 0.82-0.91 (m, 2H), 0.99-1.05 (m, 3H), 1.31-1.42 (m, 1H), 1.61-1.81 (m, 2H), 1.82-1.93 (m, 1H), 2.01-2.21 (m, 1H), 2.23-2.33 (m, 1H), 2.78-3.25 (m, 1H), 3.46-4.03 (m, 1H), 4.14 (s, 3H), 5.20-5.67 (m, 1H), 5.69-5.79 (m, 2H), 6.91-7.08 (m, 1H), 7.26-7.40 (m, 1H), 7.46-7.53 (m, 1H), 7.63-7.71 (m, 1H), 7.97-8.09 (m, 1H), 8.28 (s, 1H), 10.40-10.57 (m, 1H).

LCMS(ESI): [M+H]+ m/z: calcd 433.26; found 433.2; Rt=0.955.

2351

Example 452. The Synthesis of N-(6-amino-5-cyclopropyl-3-pyridyl)-2-[(2S,5R)-2-[2-[2-(dimethylamino)ethyl]indazol-5-yl]-5-methyl-1-piperidyl]-2-oxo-acetamide (Compound 1156) and N-(6-amino-5-cyclopropyl-3-pyridyl)-2-[(2R,5S)-2-[2-[2-(dimethylamino)ethyl]indazol-5-yl]-5-methyl-1-piperidyl]-2-oxo-acetamide (ent-Compound 1156

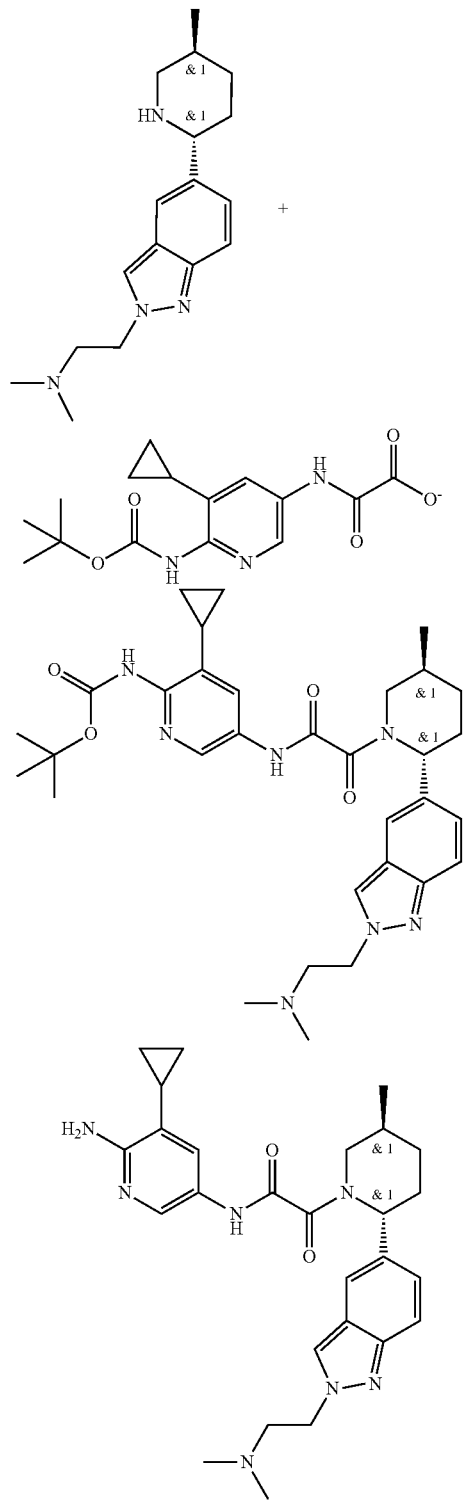

2352

-continued

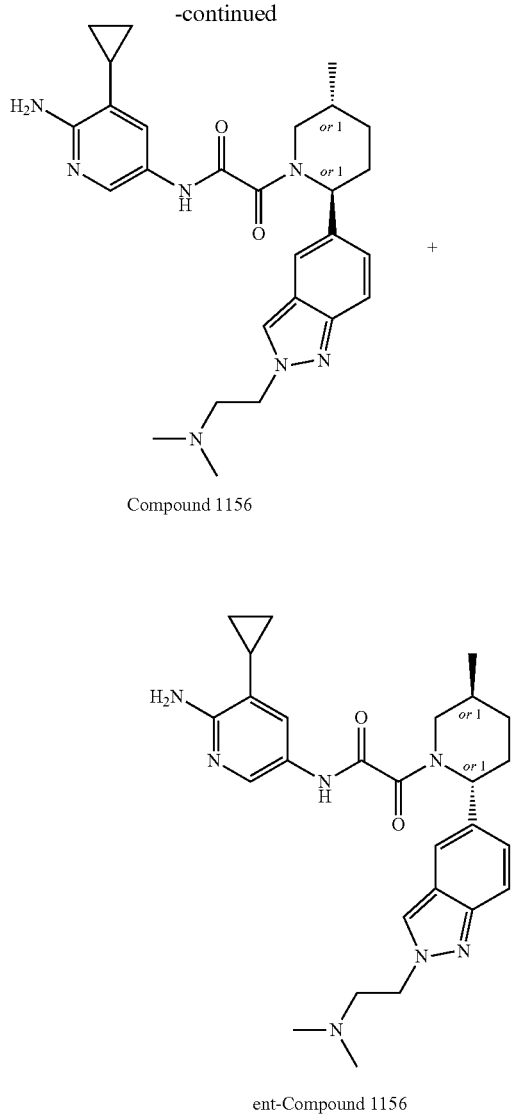

Step 1: The Synthesis of tert-butyl N-[3-cyclopropyl-5-[[2-[(2R,5S)-2-[2-[2-(dimethylamino)ethyl]indazol-5-yl]-5-methyl-1-piperidyl]-2-oxo-acetyl]amino]-2-pyridyl]carbamate To a stirred mixture of N,N-dimethyl-2-[5-[(2R,5S)-5-methyl-2-piperidyl]indazol-2-yl]ethanamine (200 mg, 505 µmol, 3HCl salt), 2-[[6-(tert-butoxycarbonylamino)-5-cyclopropyl-3-pyridyl]amino]-2-oxo-acetate (174 mg, 531 µmol, Li+salt) and Triethylamine (256 mg, 2.53 mmol, 352 µL) in Dimethylformamide (2.50 mL) HATU (211 mg, 556 µmol) was added. The reaction mixture was stirred at 20° C. for 4 hr. The obtained mixture was subjected to HPLC (0-5 min 50-100% water-ACN; flow: 30 mL/min, column: Chromatorex 18 SMB100-5T, 100×19 mm, 5 µm) to afford tert-butyl N-[3-cyclopropyl-5-[[2-[(2R,5S)-2-[2-[2-(dimethylamino)ethyl]indazol-5-yl]-5-methyl-1-piperidyl]-2-oxo-acetyl]amino]-2-pyridyl]carbamate (179 mg, 303 µmol, 60.1% yield) as a light-yellow solid.

LCMS(ESI): [M−H]+ m/z: calcd 588.39; found 588.0; Rt=2.360.

Step 2: The Synthesis of N-(6-amino-5-cyclopropyl-3-pyridyl)-2-[(2R,5S)-2-[2-[2-(dimethylamino)ethyl]indazol-5-yl]-5-methyl-1-piperidyl]-2-oxo-acetamide Water (1.00 g, 55.5 mmol, 1.00 mL) was added to a solution of tert-butyl N-[3-cyclopropyl-5-[[2-[(2R,5S)-2-[2-[2-(dimethylamino)ethyl]indazol-5-yl]-5-methyl-1-piperidyl]-2-oxo-acetyl]amino]-2-pyridyl]carbamate (179 mg, 304 µmol) in Dioxane (2.00 mL). The resulting mixture was stirred at 95° C. for 15 hr. The obtained mixture was subjected to HPLC (0-1-6 min 40-40-85% water-methanol, +0.1% vol. of 25% aq. NH₃, 30 mL/min, column: XBridge BEH C18, 100×20 mm, 5 µm) to afford N-(6-amino-5-cyclopropyl-3-pyridyl)-2-[(2R,5S)-2-[2-[2-(dimethylamino)ethyl]indazol-5-yl]-5-methyl-1-piperidyl]-2-oxo-acetamide (101 mg, 206 µmol, 67.9% yield) as a white solid.

LCMS(ESI): [M−H]⁺ m/z: calcd 488.33; found 488.2; Rt=1.773.

Step 3: The Synthesis of N-(6-amino-5-cyclopropyl-3-pyridyl)-2-[(2S,5R)-2-[2-[2-(dimethylamino)ethyl]indazol-5-yl]-5-methyl-1-piperidyl]-2-oxo-acetamide and N-(6-amino-5-cyclopropyl-3-pyridyl)-2-[(2R,5S)-2-[2-[2-(dimethylamino)ethyl]indazol-5-yl]-5-methyl-1-piperidyl]-2-oxo-acetamide N-(6-amino-5-cyclopropyl-3-pyridyl)-2-[(2R,5S)-2-[2-[2-(dimethylamino)ethyl]indazol-5-yl]-5-methyl-1-piperidyl]-2-oxo-acetamide (101 mg, 206 µmol) was subjected to Chiral HPLC (Column: CHIRALCEL OJ-H 250*20, 5um, Mobile phase: Hexane-IPA-MeOH, 50-25-25, Flow rate: 10 mL/min, 10 mg/inj., 10 injections, V=4 L) to afford: N-(6-amino-5-cyclopropyl-3-pyridyl)-2-[(2S,5R)-2-[2-[2-(dimethylamino)ethyl]indazol-5-yl]-5-methyl-1-piperidyl]-2-oxo-acetamide (38.0 mg, 77.6 µmol, 75.3% yield) Compound 1156, with ret.time=13.490 min(analytical), 16.023 min(preparative) and N-(6-amino-5-cyclopropyl-3-pyridyl)-2-[(2R,5S)-2-[2-[2-(dimethylamino)ethyl]indazol-5-yl]-5-methyl-1-piperidyl]-2-oxo-acetamide (34.0 mg, 69.4 µmol, 67.3% yield) ent-Compound 1156, with ret.time=25.422 min(analytical), 29.223 min(preparative) as white solids.

(Compound 1156): N-(6-amino-5-cyclopropyl-3-pyridyl)-2-[(2S,5R)-2-[2-[2-(dimethylamino)ethyl]indazol-5-yl]-5-methyl-1-piperidyl]-2-oxo-acetamide ¹H NMR (600 MHz, DMSO-d₆) δ 0.37-0.49 (m, 2H), 0.81-0.90 (m, 2H), 1.00-1.07 (m, 3H), 1.29-1.43 (m, 1H), 1.58-1.70 (m, 1H), 1.72-1.82 (m, 1H), 1.82-1.95 (m, 1H), 2.01-2.14 (m, 1H), 2.16 (s, 6H), 2.21-2.31 (m, 1H), 2.76 (t, 2H), 2.78-3.26 (m, 1H), 3.45-4.07 (m, 1H), 4.48 (t, 2H), 5.16-5.67 (m, 1H), 5.67-5.80 (m, 2H), 7.05-7.25 (m, 1H), 7.28-7.42 (m, 1H), 7.54-7.69 (m, 2H), 7.97-8.10 (m, 1H), 8.25-8.37 (m, 1H), 10.47 (br s, 1H).

LCMS(ESI): [M+H]⁺ m/z: calcd 490.33; found 490.2; Rt=1.640.

(ent-Compound 1156): N-(6-amino-5-cyclopropyl-3-pyridyl)-2-[(2R,5S)-2-[2-[2-(dimethylamino)ethyl]indazol-5-yl]-5-methyl-1-piperidyl]-2-oxo-acetamide ¹H NMR (600 MHz, DMSO-d₆) δ 0.37-0.49 (m, 2H), 0.81-0.91 (m, 2H), 0.96-1.06 (m, 3H), 1.30-1.39 (m, 1H), 1.61-1.70 (m, 1H), 1.72-1.82 (m, 1H), 1.82-1.96 (m, 1H), 2.00-2.13 (m, 1H), 2.17 (s, 6H), 2.22-2.33 (m, 1H), 2.74-2.82 (m, 2H), 2.88-3.26 (m, 1H), 3.44-4.04 (m, 1H), 4.49 (t, 2H), 5.13-5.68 (m, 1H), 5.68-5.87 (m, 2H), 7.10-7.27 (m, 1H), 7.27-7.44 (m, 1H), 7.50-7.64 (m, 2H), 7.97-8.15 (m, 1H), 8.25-8.37 (m, 1H), 10.41-10.54 (m, 1H).

LCMS(ESI): [M+H]⁺ m/z: calcd 490.33; found 490.2; Rt=1.641.

Example 453. The Synthesis of N-(6-amino-5-cyclopropyl-3-pyridyl)-2-[(2S,5R)-2-[1-[2-(dimethylamino)ethyl]indazol-5-yl]-5-methyl-1-piperidyl]-2-oxo-acetamide (Compound 1249) and N-(6-amino-5-cyclopropyl-3-pyridyl)-2-[(2R,5S)-2-[1-[2-(dimethylamino)ethyl]indazol-5-yl]-5-methyl-1-piperidyl]-2-oxo-acetamide (ent-Compound 1249

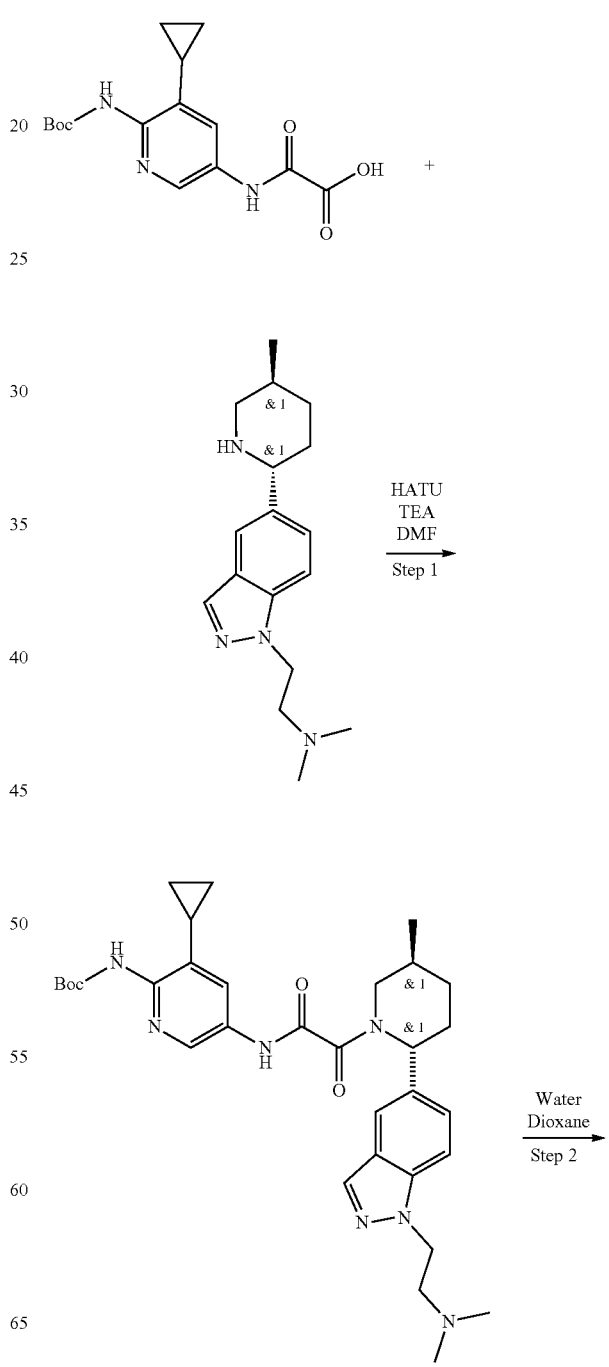

-continued

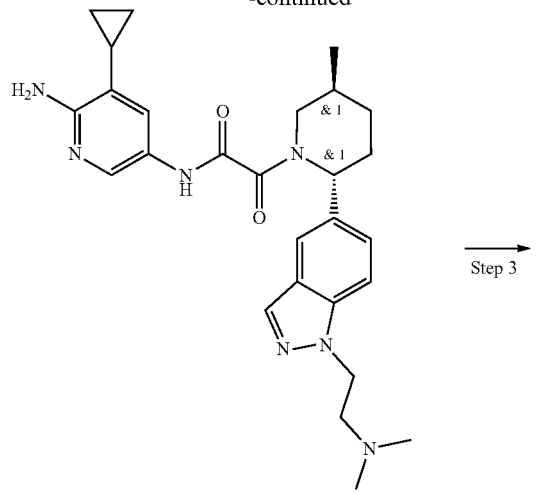

Compound 1249

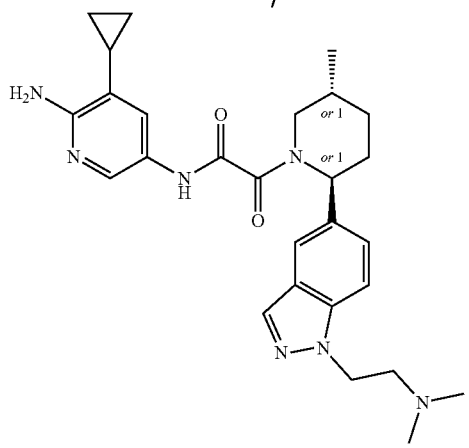

ent-Compound 1249

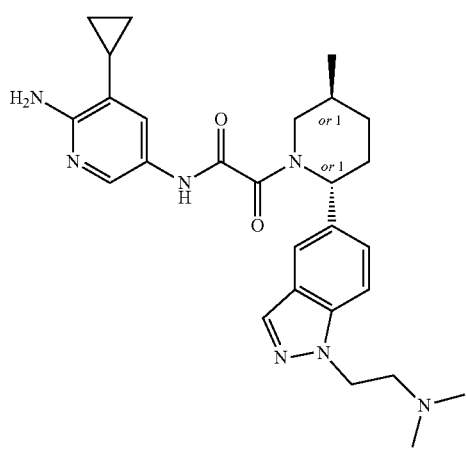

Step 1: The Synthesis of tert-butyl N-[3-cyclopropyl-5-[[2-[(2R,5S)-2-[1-[2-(dimethylamino)ethyl]indazol-5-yl]-5-methyl-1-piperidyl]-2-oxo-acetyl]amino]-2-pyridyl]carbamate To a stirred mixture of N,N-dimethyl-2-[5-[(2R,5S)-5-methyl-2-piperidyl]indazol-1-yl]ethanamine (200 mg, 505 µmol, 3HCl salt), 2-[[6-(tert-butoxycarbonylamino)-5-cyclopropyl-3-pyridyl]amino]-2-oxo-acetate (174 mg, 531 µmol, Li+) and Triethylamine (256 mg, 2.53 mmol, 352 µL) in Dimethylformamide (2.50 mL) HATU (211 mg, 556 µmol) was added. The reaction mixture was stirred at 20° C. for 4 hr. The obtained mixture was subjected to HPLC (0-5 min 50-50-80% water-methanol, +0.1% vol. of 25% aq. NH$_3$, 30 mL/min, column: YMC-Actus Triart C18, 100×20 mm, 5 µm), to afford tert-butyl N-[3-cyclopropyl-5-[[2-[(2R,5S)-2-[1-[2-(dimethylamino)ethyl]indazol-5-yl]-5-methyl-1-piperidyl]-2-oxo-acetyl]amino]-2-pyridyl]carbamate (220 mg, 373 µmol, 73.8% yield) as a light-yellow solid.

LCMS(ESI): [M+H]$^+$ m/z: calcd 590.39; found 590.2; Rt=2.586.

Step 2: The Synthesis of N-(6-amino-5-cyclopropyl-3-pyridyl)-2-[(2R,5S)-2-[1-[2-(dimethylamino)ethyl]indazol-5-yl]-5-methyl-1-piperidyl]-2-oxoacetamide Water (1.00 g, 55.5 mmol, 1.00 mL) was added to a solution of tert-butyl N-[3-cyclopropyl-5-[[2-[(2R,5S)-2-[1-[2-(dimethylamino)ethyl]indazol-5-yl]-5-methyl-1-piperidyl]-2-oxo-acetyl]amino]-2-pyridyl]carbamate (220 mg, 373 µmol) in Dioxane (2.00 mL). The resulting mixture was stirred at 95° C. for 15 hr. The obtained mixture was subjected to HPLC (0-5 min 50-90% water-methanol, +0.1% vol. of 25% aq. NH$_3$, 30 mL/min, column: YMC-Actus Triart C18, 100×20 mm, 5 µm) to afford N-(6-amino-5-cyclopropyl-3-pyridyl)-2-[(2R,5S)-2-[1-[2-(dimethylamino)ethyl]indazol-5-yl]-5-methyl-1-piperidyl]-2-oxoacetamide (126 mg, 257 µmol, 68.9% yield) as a white solid.

LCMS(ESI): [M+H]$^+$ m/z: calcd 490.33; found 490.2; Rt=2.033.

Step 3: The Synthesis of N-(6-amino-5-cyclopropyl-3-pyridyl)-2-[(2S,5R)-2-[1-[2-(dimethylamino)ethyl]indazol-5-yl]-5-methyl-1-piperidyl]-2-oxoacetamide (Compound 1249) and N-(6-amino-5-cyclopropyl-3-pyridyl)-2-[(2R,5S)-2-[1-[2-(dimethylamino)ethyl]indazol-5-yl]-5-methyl-1-piperidyl]-2-oxo-acetamide (Ent-Compound 1249

N-(6-amino-5-cyclopropyl-3-pyridyl)-2-[(2R,5S)-2-[1-[2-(dimethylamino)ethyl]indazol-5-yl]-5-methyl-1-piperidyl]-2-oxo-acetamide (126 mg, 257 µmol) was subjected to Chiral HPLC (Chiralcel OJ-H 250*20, 5-I Hexane-IPA-MeOH, 60-20-20, 12 mL/min, 0.36 L(15 mg)/inj., 8 inj.) to afford N-(6-amino-5-cyclopropyl-3-pyridyl)-2-[(2S,5R)-2-[1-[2-(dimethylamino)ethyl]indazol-5-yl]-5-methyl-1-piperidyl]-2-oxo-acetamide (48.0 mg, 98.0 µmol, 76.2% yield) Compound 1249, with ret.time=12.828 min(analytical), 16.18 min(preparative) and N-(6-amino-5-cyclopropyl-3-pyridyl)-2-[(2R,5S)-2-[1-[2-(dimethylamino)ethyl]indazol-5-yl]-5-methyl-1-piperidyl]-2-oxo-acetamide (29.0 mg, 59.2 µmol, 46.0% yield) ent-Compound 1249, with ret.time=18.201 min(analytical), 22.28 min(preparative) as white solids.

Compound 1249: N-(6-amino-5-cyclopropyl-3-pyridyl)-2-[(2S,5R)-2-[1-[2-(dimethylamino)ethyl]indazol-5-yl]-5-methyl-1-piperidyl]-2-oxo-acetamide $^1$H NMR (600 MHz, DMSO-d$_6$) δ 0.37-0.51 (m, 2H), 0.82-0.93 (m, 2H), 1.00-1.05 (m, 3H), 1.30-1.41 (m, 1H), 1.60-1.71 (m, 1H), 1.72-1.82 (m, 1H), 1.83-1.93 (m, 1H), 2.01-2.13 (m, 1H), 2.14 (s, 6H), 2.25-2.35 (m, 1H), 2.64-2.71 (m, 2H), 2.77-3.27 (m, 1H), 3.44-4.06 (m, 1H), 4.39-4.52 (m, 2H), 5.18-5.70 (m, 1H), 5.70-5.82 (m, 2H), 7.25-

7.34 (m, 1H), 7.34-7.44 (m, 1H), 7.64-7.70 (m, 2H), 7.98-8.10 (m, 2H), 10.44-10.60 (m, 1H).

LCMS(ESI): [M−H]+ m/z: calcd 488.33; found 488.2; Rt=1.801. ent-Compound 1249: N-(6-amino-5-cyclopropyl-3-pyridyl)-2-[(2R,5S)-2-[1-[2-(dimethylamino)ethyl]indazol-5-yl]-5-methyl-1-piperidyl]-2-oxo-acetamide $^1$H NMR (600 MHz, DMSO-d$_6$) δ 0.38-0.48 (m, 2H), 0.82-0.91 (m, 2H), 0.98-1.07 (m, 3H), 1.29-1.43 (m, 1H), 1.60-1.76 (m, 2H), 1.83-1.92 (m, 1H), 2.05-2.19 (m, 1H), 2.25-2.33 (m, 1H), 2.49-2.57 (m, 6H), 2.70-2.96 (m, 1H), 2.99-3.20 (m, 2H), 3.43-4.05 (m, 1H), 4.62 (s, 2H), 5.21-5.71 (m, 1H), 5.71-5.83 (m, 2H), 7.26-7.46 (m, 2H), 7.67-7.77 (m, 2H), 7.96-8.12 (m, 2H), 10.44-10.56 (m, 1H).

LCMS(ESI): [M−H]+ m/z: calcd 488.33; found 488.2; Rt=1.812.

Example 454. The Synthesis of N-(6-amino-5-methyl-3-pyridyl)-2-[(2S,5R)-2-[3-[2-(dimethylamino)ethyl]benzothiophen-5-yl]-5-methyl-1-piperidyl]-2-oxo-acetamide (Compound 1142

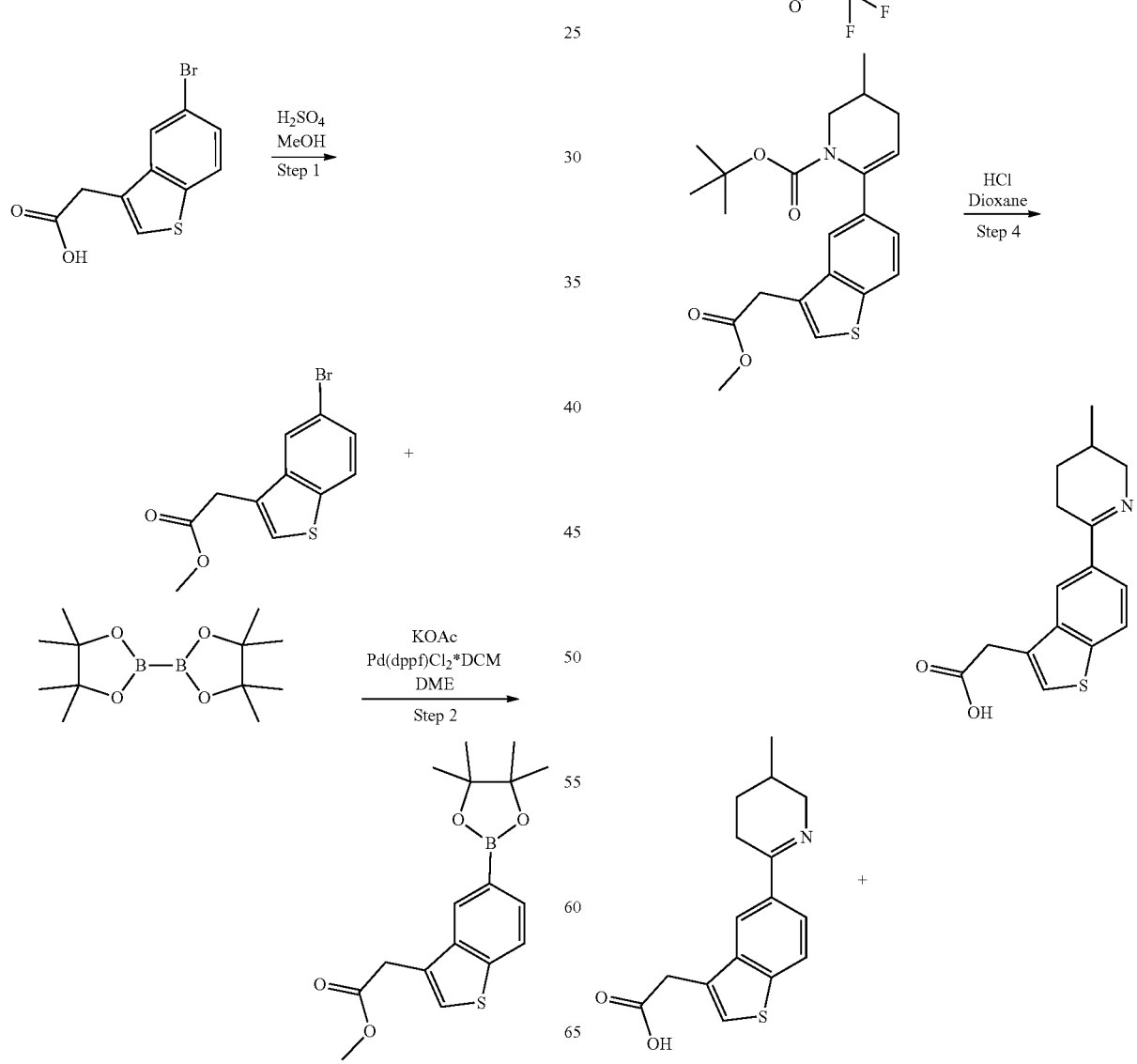

2359
-continued

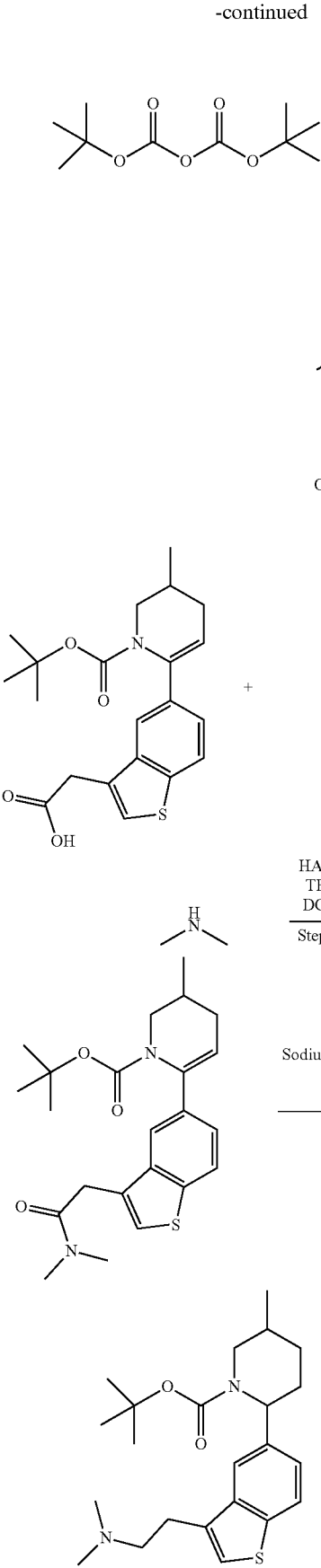

2360
-continued

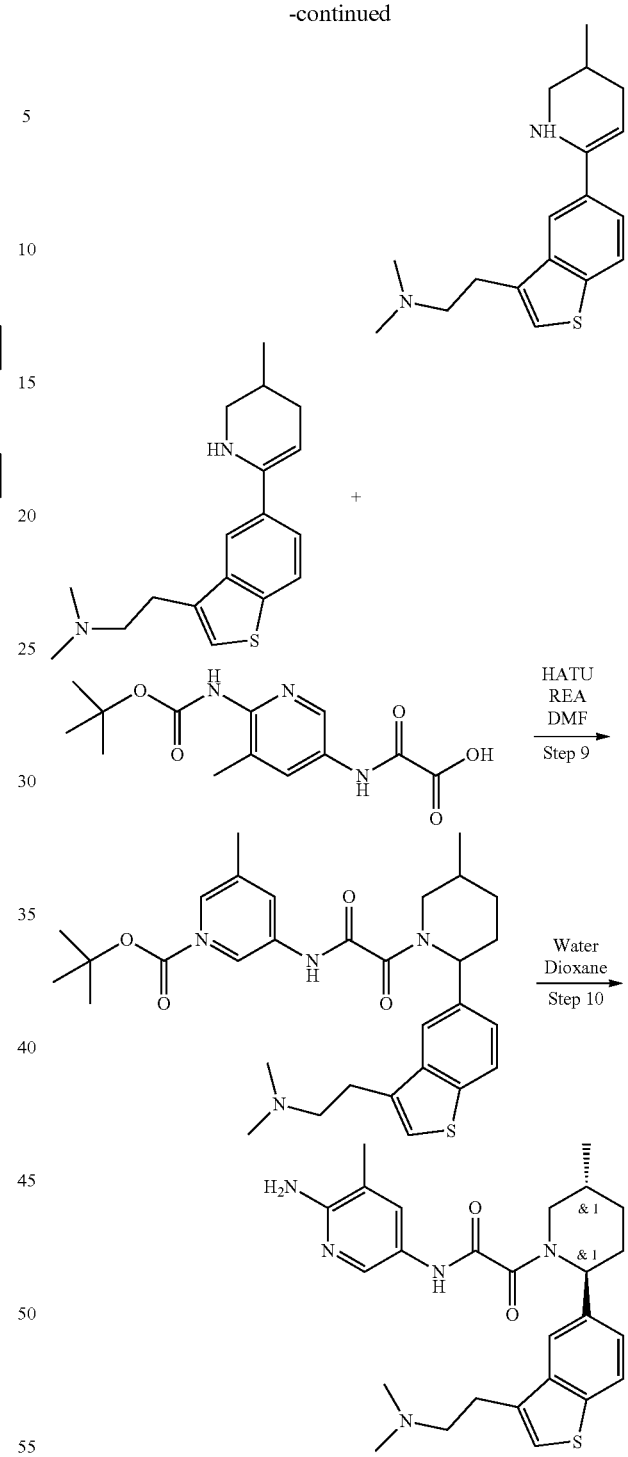

Step 1: The Synthesis of methyl 2-(5-bromobenzothiophen-3-yl)acetate 2-(5-bromobenzothiophen-3-yl)acetic acid (0.50 g, 1.84 mmol was dissolved in dry methanol (20.0 mL) and Sulfuric acid (1.00 g, 10.2 mmol) was added. The reaction mixture was heated at 75° C. for 12 hr. The obtained mixture was concentrated in vacuo. The residue was treated with water and filtered. The precipitate was dissolved in EA (50.0 mL), washed with aq. solution of NaHCO$_3$, dried over Na$_2$SO$_4$ and concentrated in vacuo to afford methyl 2-(5-bromobenzothiophen-3-yl)acetate (0.60 g, crude) as a yellow solid.

$^1$H NMR (500 MHz, DMSO-$d_6$) δ 3.62 (s, 3H), 3.97 (s, 2H), 7.49-7.52 (m, 1H), 7.68 (s, 1H), 7.68-7.72 (m, 2H).

Step 2: The Synthesis of methyl 2-[5-(4,4,5,5-tetramethyl-1,3,2-dioxaborolan-2-yl)benzothiophen-3-yl]acetate To a stirred solution of methyl 2-(5-bromobenzothiophen-3-yl)acetate (0.39 g, 1.35 mmol) and 4,4,4',4',5,5,5',5'-Octamethyl-2,2'-bi(1,3,2-dioxaborolane) (326 mg, 1.29 mmol) in DME (25.0 mL) Potassium Acetate (266 mg, 2.71 mmol, 169 µL) was added. The resulting suspension was evacuated and backfilled with argon. The reaction mixture was stirred at 50° C. for 1 hr. [1,1'-Bis(diphenylphosphino)ferrocene]palladium(II) dichloride (99.1 mg, 135 µmol) was added. The reaction mixture was stirred at 80° C. for 6 hr. The obtained mixture was concentrated under reduced pressure. The residue was dissolved in CHCl$_3$, filtered through a pad of silica and the filtrate was concentrated in vacuo to afford methyl 2-[5-(4,4,5,5-tetramethyl-1,3,2-dioxaborolan-2-yl)benzothiophen-3-yl]acetate (170 mg, 512 µmol, 37.8% yield) as light-yellow gum.

LCMS(ESI): [M+H]$^+$ m/z: calcd 333.15; found; Rt=4.046.

Step 3: The Synthesis of tert-butyl 6-[3-(2-methoxy-2-oxo-ethyl)benzothiophen-5-yl]-3-methyl-3,4-dihydro-2H-pyridine-1-carboxylate To a stirred solution of methyl 2-[5-(4,4,5,5-tetramethyl-1,3,2-dioxaborolan-2-yl)benzothiophen-3-yl]acetate (19.3 g, 34.8 mmol) and tert-butyl 3-methyl-6-(trifluoromethylsulfonyloxy)-3,4-dihydro-2H-pyridine-1-carboxylate (11.8 g, 34.1 mmol) in water (100 mL) and dioxane (250 mL) Sodium carbonate (7.37 g, 69.5 mmol, 2.91 mL) was added. The resulting suspension was evacuated and then backfilled with argon. The obtained mixture was stirred at 50° C. for 1 hr. [1,1'-Bis(diphenylphosphino)ferrocene]palladium(II) dichloride (1.27 g, 1.74 mmol) was added. The reaction mixture was stirred at 80° C. for 18 hr. The obtained mixture was concentrated under reduced pressure, dissolved in CHCl$_3$, dried over Na$_2$SO$_4$, filtered through a pad of silica and the filtrate was concentrated in vacuo to afford tert-butyl 6-[3-(2-methoxy-2-oxo-ethyl)benzothiophen-5-yl]-3-methyl-3,4-dihydro-2H-pyridine-1-carboxylate (15.4 g, crude) as brown gum.

LCMS(ESI): [M+H]$^+$ m/z: calcd 402.2; found; Rt=4.557.

Step 4: The Synthesis of 2-[5-(3-methyl-2,3,4,5-tetrahydropyridin-6-yl)benzothiophen-3-yl]acetic Acid A solution of tert-butyl 6-[3-(2-methoxy-2-oxo-ethyl)benzothiophen-5-yl]-3-methyl-3,4-dihydro-2H-pyridine-1-carboxylate (15.4 g, 24.9 mmol) in dioxane (150 mL) and hydrogen chloride, 20% (100 mL) was stirred at 21° C. for 15 hr. The reaction mixture was concentrated in vacuo to afford 2-[5-(3-methyl-2,3,4,5-tetrahydropyridin-6-yl)benzothiophen-3-yl]acetic acid (12.7 g, crude, HCl salt) as brown gum.

LCMS(ESI): [M+H]$^+$ m/z: calcd 288.10; found 288.2; Rt=2.133.

Step 5: The Synthesis of 2-[5-(1-tert-butoxycarbonyl-5-methyl-2-piperidyl)benzothiophen-3-yl]acetic acid To an ice cold solution of 2-[5-(3-methyl-2,3,4,5-tetrahydropyridin-6-yl)benzothiophen-3-yl]acetic acid (12.5 g, 23.9 mmol, HCl salt) in MeOH (250 mL) sodium borohydride (1.81 g, 47.9 mmol, 1.69 mL) was added. The resulting mixture was left to stir overnight at r.t. The obtained mixture was acidified with 1N HCl to pH=3-4. Sodium hydroxide, pearl (1.91 g, 47.9 mmol, 899 µL) in MeOH (250 mL) and water (50.0 mL) was added, followed by Di-tert-butyl dicarbonate (5.22 g, 23.9 mmol, 5.49 mL). The reaction mixture was left to stir overnight. The obtained mixture was concentrated in vacuo. The residue was partitioned with EtOAc/water. The obtained mixture was extracted with EtOAc (100 mL). Water was acidified to pH=1 and extracted with DCM twice. The combined organics were washed with brine, dried over Na$_2$SO$_4$, and concentrated in vacuo to afford 2-[5-(1-tert-butoxycarbonyl-5-methyl-2-piperidyl)benzothiophen-3-yl]acetic acid (9.15 g, 23.5 mmol, 98.2% yield) as a beige solid.

LCMS(ESI): [M-boc]$^+$ m/z: calcd 290.2; found 290.2; Rt=4.087.

Step 6: The Synthesis of tert-butyl 2-[3-[2-(dimethylamino)-2-oxo-ethyl]benzothiophen-5-yl]-5-methyl-piperidine-1-carboxylate 2-[5-(1-tert-butoxycarbonyl-5-methyl-2-piperidyl)benzothiophen-3-yl]acetic acid (1.00 g, 2.57 mmol), HATU (1.17 g, 3.08 mmol) and TEA (779 mg, 7.70 mmol, 1.07 mL) were mixed in dry DCM (25.0 mL) at rt. The resulting mixture was stirred for 15 min. Dimethylamine (419 mg, 5.13 mmol, 540 µL, HCl salt) was added. The resulting mixture was stirred at rt overnight. The obtained mixture was washed with water, brine and concentrated in vacuo to afford tert-butyl 2-[3-[2-(dimethylamino)-2-oxo-ethyl]benzothiophen-5-yl]-5-methyl-piperidine-1-carboxylate (1.30 g, crude) as a brown gum.

LCMS(ESI): [M+H]$^+$ m/z: calcd 417.26; found; Rt=4.352.

Step 7: The Synthesis of tert-butyl 2-[3-[2-(dimethylamino)ethyl]benzothiophen-5-yl]-5-methyl-piperidine-1-carboxylate To a solution of tert-butyl 2-[3-[2-(dimethylamino)-2-oxo-ethyl]benzothiophen-5-yl]-5-methyl-piperidine-1-carboxylate (1.10 g, 2.64 mmol) in THF (25.0 mL) Sodium bis(2-methoxyethoxy)aluminumhydride (3.05 g, 10.6 mmol, 3.02 mL, 70% purity) was added in an inert atmosphere. After stirring at rt for 12 hr, the resulting mixture was quenched with 1 N NaOH, extracted with MTBE (2×25.0 mL), dried, and concentrated in vacuo to dryness to afford tert-butyl 2-[3-[2-(dimethylamino)ethyl]benzothiophen-5-yl]-5-methyl-piperidine-1-carboxylate (1.10 g, crude) as brownish gum.

LCMS(ESI): [M+H]$^+$ m/z: calcd 403.29; found 403.2; Rt=3.089.

Step 8: The Synthesis of N,N-dimethyl-2-[5-(5-methyl-2-piperidyl)benzothiophen-3-yl]ethanamine To a solution of tert-butyl 2-[3-[2-(dimethylamino)ethyl]benzothiophen-5-yl]-5-methyl-piperidine-1-carboxylate (1.21 g, 3.01 mmol) in MeOH (25.0 mL) Hydrogen chloride solution 4.0 M in dioxane (4.00 g, 110 mmol, 5.00 mL) was added at 21° C. The resulting mixture was stirred for 12 hr. The obtained mixture was concentrated in vacuo to afford N,N-dimethyl-2-[5-(5-methyl-2-piperidyl)benzothiophen-3-yl]ethanamine (0.90 g, 2.40 mmol, 79.2%) as a beige solid.

LCMS(ESI): [M+H]+ m/z: calcd 303.23; found 303.2; Rt=1.129.

Step 9: The Synthesis of tert-butyl N-[5-[[2-[2-[3-[2-(dimethylamino)ethyl]benzothiophen-5-yl]-5-methyl-1-piperidyl]-2-oxo-acetyl]amino]-3-methyl-2-pyridyl]carbamate N,N-dimethyl-2-[5-(5-methyl-2-piperidyl)benzothiophen-3-yl]ethanamine (0.45 g, 1.20 mmol, 2HCl salt), HATU (456 mg, 1.20 mmol) and TEA (607 mg, 5.99 mmol, 835 µL) were mixed in dry DMF (5.00 mL) at rt. The resulting mixture was stirred for 15 min. 2-[[6-(tert-butoxycarbonylamino)-5-methyl-3-pyridyl]amino]-2-oxo-acetic acid (354 mg, 1.20 mmol) was added thereto and stirring was continued at rt overnight. The obtained mixture was poured into water and extracted 3 times with EtOAc. The combined organics were washed with water, brine and concentrated in vacuo. The residue was subjected to HPLC (0.5-6.5 min 63% water-acetonitrile+NH3, 30 mL/min (loading pump 4 mL; acetonitrile) column: YMC-ACTUS TRIART C18 100*20 5 microM) to afford tert-butyl N-[5-[[2-[2-[3-[2-(dimethylamino)ethyl]benzothiophen-5-yl]-5-methyl-1-piperidyl]-2-oxo-acetyl]amino]-3-methyl-2-pyridyl]carbamate (159 mg, 274 µmol, 22.9% yield) as a beige solid.

LCMS(ESI): [M+H]+ m/z: calcd 580.34; found 580.4; Rt=3.059.

Step 10: The Synthesis of N-(6-amino-5-methyl-3-pyridyl)-2-[(2S,5R)-2-[3-[2-(dimethylamino)ethyl]benzothiophen-5-yl]-5-methyl-1-piperidyl]-2-oxo-acetamide (Compound 1141)

Tert-butyl N-[5-[[2-[2-[3-[2-(dimethylamino)ethyl]benzothiophen-5-yl]-5-methyl-1-piperidyl]-2-oxo-acetyl]amino]-3-methyl-2-pyridyl]carbamate (159 mg, 274 µmol) was dissolved in water (2.00 mL)/dioxane (2.00 mL). The reaction mixture was heated at 90° C. overnight. The obtained mixture was concentrated in vacuo to dryness. The residue was subjected to HPLC (1st run: 45-70% 0.5-6.5 min water-acetonitrile+NH3; flow 30 mL/min (loading pump 4 ml/min acetonitrile); column xbridge C18 100×19 mm 5 um (R); 2nd run: 10-40% 0.5-6.5 min water-ACN+FA; flow 30 ml/min (loading pump 4 mL/min acn); column SunFire C18 100×19 mm 5 um (R)) to afford N-(6-amino-5-methyl-3-pyridyl)-2-[(2S,5R)-2-[3-[2-(dimethylamino)ethyl]benzothiophen-5-yl]-5-methyl-1-piperidyl]-2-oxo-acetamide (61.4 mg, 128 µmol, 46.7% yield) as a beige solid.

1H NMR (600 MHz, DMSO-d6) δ 1.01-1.06 (m, 3H), 1.32-1.42 (m, 1H), 1.66-1.79 (m, 1H), 1.81-1.92 (m, 1H), 1.95-2.04 (m, 3H), 2.06-2.18 (m, 1H), 2.22-2.26 (m, 6H), 2.27-2.34 (m, 1H), 2.58-2.65 (m, 2H), 2.93-3.00 (m, 2H), 3.28-3.30 (m, 1H), 3.65-4.11 (m, 1H), 5.25-5.60 (m, 1H), 5.59-5.77 (m, 2H), 7.28-7.39 (m, 1H), 7.39-7.53 (m, 2H), 7.67-7.73 (m, 1H), 7.92-8.07 (m, 2H), 10.46-10.59 (m, 1H).

LCMS(ESI): [M+H]+ m/z: calcd 480.28; found 480.4; Rt=2.171.

Scheme D. Synthesis of Compounds of Formula 4

Compounds of Formula 4 are compounds of Formula (I), (Ia) and (Ib) wherein R1 is H, R2 is —C(=O)NH2, R3, R4 and R8 are H, R7 is -Me General Procedure 4

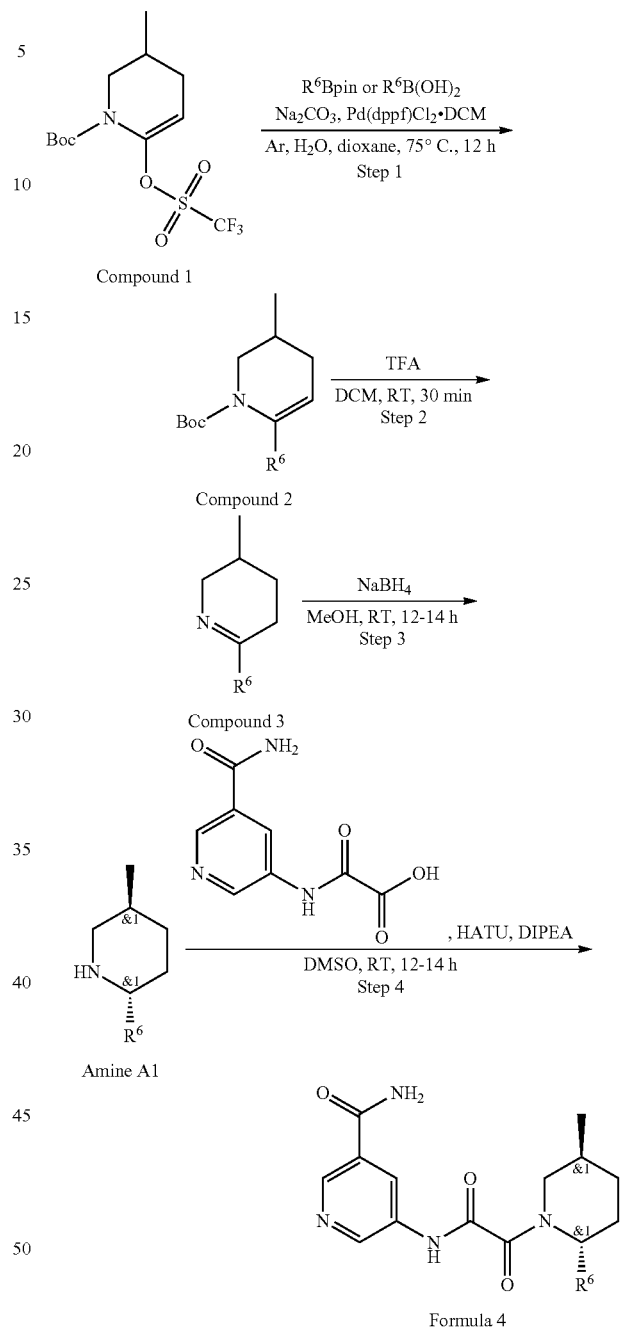

Step 1: Compound 1 (1.0 eq), corresponding boronic acid (1.25 eq), sodium carbonate (3 eq), Pd(dppf)Cl2*DCM (0.04 eq), water (1 mL) and 1,4-dioxane (2 mL) were placed in 8 ml vial and charged with Ar in glove box. The reaction mixture was stirred at 75° C. for 12 hr. After cooling to RT, water (4 mL) was added into vial and the mixture was extracted with DCM. Separated organic layer was concentrated to afford crude compound 2 which was used in the next step without additional purification.

Step 2: To a solution of crude compound 2 in DCM (0.5 mL), TFA (0.5 mL) was added. The reaction mixture was stirred at RT for 30 min. Then, the resulting mixture was evaporated and the residue was dissolved in DCM (5 mL). The organic layer was washed twice with aqueous solution of NaOH and concentrated under reduced pressure to afford crude compound 3 which was used in the next step without purification.

Step 3: NaBH₄ (1.1 eq) was added in one portion to a solution of crude compound 3 (1 eq) in methanol (4 mL). The reaction mixture was stirred overnight and evaporated. The residue was dissolved in DCM (5 mL) and washed with water twice. The organic layer was concentrated in vacuo to afford crude Amine A1 which was used in the next step without purification.

Exemplary coupling procedure 1: The amine A1 (~1 eq), 2-((5-carbamoylpyridin-3-yl)amino)-2-oxoacetic acidtriethylammonium salt (~1.1 eq), HATU (1.1 eq), DIPEA (1.5 eq) were stirred in DMSO overnight. After LCMS confirmation of presence of the desired product, the reaction mixture was submitted to HPLC (Sunfire C18 19*100 5 mkm column, H₂O-MeOH as a mobile phase, Flow 15 ml/min, RunTime 5 min) to afford pure compounds of Formula 4.

Exemplary coupling procedure 2: 2-[(5-carbamoyl-3-pyridyl)amino]-2-oxo-acetic acid (~1 eq), HATU (~1.1 eq) and Triethylamine (~3 eq) were mixed in dry DMF at 21° C. and the resulting mixture was stirred for 12 hr. Amine A1 (~1 eq) was added thereto and the resulting mixture was stirred at 21° C. overnight. The resulting mixture was poured into water, extracted 3 times with EtOAc, combined organics were washed with water, brine and evaporated. The residue was subjected to HPLC (e.g., (0-5 min 20-70% water-methanol (NH₃ 0.1%), flow 30 ml/min to (loading pump 4 ml/min methanol (NH₃ 0.1%)), column: YMC-Actus Triart C18 100*20 mml.D. S-5 um) provide compounds of Formula 4.

Following the above procedure, variations of starting materials the library was produced. The molar ratio of the reagents and reaction conditions were kept the same in each reaction of the series. The yields and the LC-MS and NMR description of the final products are presented on the following pages. All boronic acids and pinacolates are commercial Enamine stock.

Example 455. The Synthesis of rac-5-{2-[(2R,5S)-2-(4-fluoro-3-methylphenyl)-5-methylpiperidin-1-yl]-2-oxoacetamido}pyridine-3-carboxamide (Compound 131

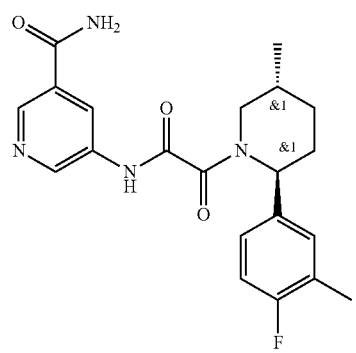

Compound 131

Prepared by general procedure 1. Yield: 12.8 mg, 9.18% ¹H NMR (500 MHz, CDCl₃) δ 1.11 (m, 3H), 1.40 (m, 2H), 1.89 (m, 1H), 2.00 (m, 2H), 2.18 (m, 2H), 2.28 (m, 3H), 3.40 (m, 1H), 5.97 (m, 1H), 7.00 (m, 1H), 7.08 (m, 2H), 8.92 (m, 2H), 9.53 (m, 1H). LCMS(ESI): [M+H]⁺ m/z: calcd 398.2; found 399.2; Rt=3.381 min.

Example 456. The Synthesis of rac-5-{2-[(2R,5S)-2-(6-methoxypyridin-3-yl)-5-methylpiperidin-1-yl]-2-oxoacetamido}pyridine-3-carboxamide (Compound 128

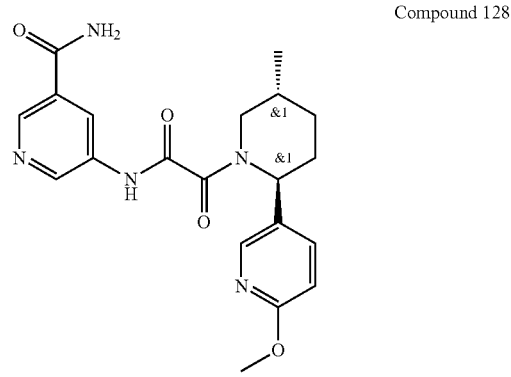

Compound 128

Prepared by general procedure 1. Yield: 6.1 mg, 4.38% ¹H NMR (500 MHz, CDCl₃) δ 1.12 (m, 3H), 1.45 (m, 1H), 1.98 (m, 2H), 2.23 (m, 2H), 3.36 (m, 1H), 3.96 (m, 3H), 4.57 (m, 1H), 6.34 (m, 1H), 6.79 (m, 1H), 7.54 (m, 1H), 8.16 (s, 1H), 8.69 (s, 1H), 8.90 (s, 1H), 8.99 (s, 1H), 9.74 (m, 1H). LCMS(ESI): [M+H]⁺ m/z: calcd 397.2; found 398.2; Rt=2.770 min.

Example 457. The Synthesis of rac-5-{2-[(2R,5S)-2-(3,5-dimethylphenyl)-5-methylpiperidin-1-yl]-2-oxoacetamido}pyridine-3-carboxamide (Compound 118

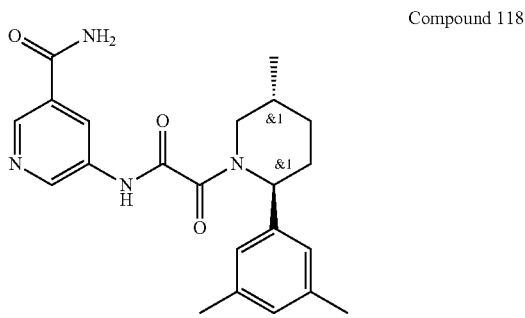 [SMILES: Cc1cc(C)cc([C@@H]2CC[C@@H](C)CN2C(=O)C(=O)Nc2cncc(C(N)=O)c2)c1]

Compound 118

Prepared by general procedure 1. Yield: 5.2 mg, 3.77% ¹H NMR (500 MHz, CDCl₃) δ 1.12 (m, 3H), 1.39 (m, 1H), 1.99 (m, 3H), 2.23 (m, 2H), 2.33 (m, 6H), 3.44 (m, 1H), 4.83 (m, 1H), 6.03 (m, 2H), 6.90 (m, 3H), 8.69 (m, 1H), 8.94 (m, 2H), 9.79 (m, 1H). LCMS(ESI): [M+H]⁺ m/z: calcd 394.2; found 395.4; Rt=3.518 min.

Example 458. The Synthesis of rac-5-{2-[(2R,5S)-2-(3,4-difluorophenyl)-5-methylpiperidin-1-yl]-2-oxoacetamido}pyridine-3-carboxamide (Compound 263

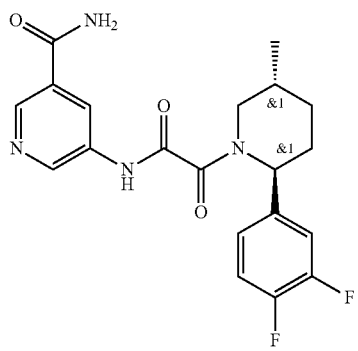

Compound 263

Prepared by general procedure 1. Yield: 8.3 mg, 5.89% $^1$H NMR (600 MHz, DMSO-d$_6$) δ 0.96-1.07 (m, 3H), 1.26-1.38 (m, 1H), 1.59-1.69 (m, 1H), 1.81-1.94 (m, 1H), 2.00-2.14 (m, 1H), 2.14-2.29 (m, 1H), 2.78-3.26 (m, 1H), 3.45-4.05 (m, 1H), 5.06-5.65 (m, 1H), 7.10-7.23 (m, 1H), 7.33-7.50 (m, 2H), 7.51-7.68 (m, 1H), 8.10-8.23 (m, 1H), 8.42-8.53 (m, 1H), 8.70-8.80 (m, 1H), 8.81-8.93 (m, 1H), 11.17-11.33 (m, 1H). LCMS(ESI): [M+H]$^+$ m/z: calcd 402.2; found 403.2; Rt=3.123 min.

Example 459. The Synthesis of rac-5-{2-[(2R,5S)-2-(3-chloro-4-fluorophenyl)-5-methylpiperidin-1-yl]-2-oxoacetamido}pyridine-3-carboxamide (Compound 338

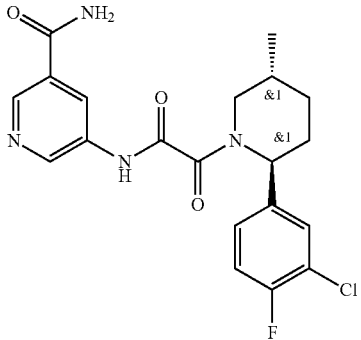

Compound 338

Prepared by general procedure 1. Yield: 1.7 mg, 1.16% LCMS(ESI): [M+H]$^+$ m/z: calcd 418.2; found 419.2; Rt=1.308 min Example 460. The Synthesis of rac-5-{2-[(2R,5S)-2-[4-Fluoro-3-(trifluoromethyl)phenyl]-5-methylpiperidin-1-yl]-2-oxoacetamido}pyridine-3-carboxamide (Compound 255)

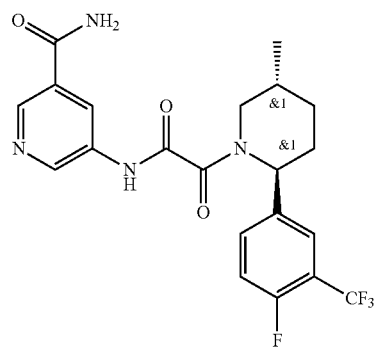

Compound 255

Prepared by general procedure 1. Yield: 17.7 mg, 11.18% $^1$H NMR (600 MHz, DMSO-d$_6$) δ 0.86-1.07 (m, 3H), 1.21-1.42 (m, 1H), 1.60-1.71 (m, 1H), 1.84-1.98 (m, 1H), 2.04-2.31 (m, 2H), 2.73-3.28 (m, 1H), 3.45-4.04 (m, 1H), 5.15-5.71 (m, 1H), 7.48-7.72 (m, 4H), 8.07-8.22 (m, 1H), 8.39-8.56 (m, 1H), 8.72-8.80 (m, 1H), 8.80-8.97 (m, 1H), 11.17-11.36 (m, 1H). LCMS(ESI): [M+H]$^+$ m/z: calcd 452.2; found 453.2; Rt=1.281 min.

Example 461. The Synthesis of rac-5-{2-[(2R,5S)-2-[4-(difluoromethoxy)phenyl]-5-methylpiperidin-1-yl]-2-oxoacetamido}pyridine-3-carboxamide (Compound 271

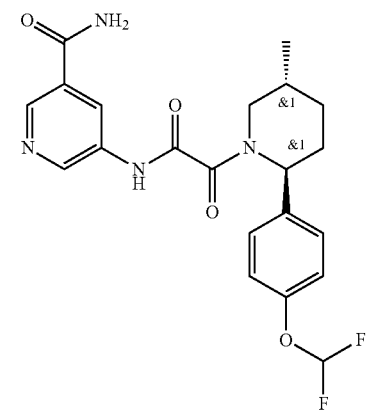

Compound 271

Prepared by general procedure 1. Yield: 13.3 mg, 8.79% $^1$H R (600 MHz, DMSO-d$_6$) δ 0.96-1.04 (m, 3H), 1.28-1.40 (m, 1H), 1.62-1.69 (m, 1H), 1.82-1.95 (m, 1H), 2.02-2.14 (m, 1H), 2.16-2.29 (m, 1H), 2.75-3.24 (m, 1H), 3.46-4.04 (m, 1H), 5.10-5.60 (m, 1H), 7.06-7.33 (m, 3H), 7.34-7.41 (m, 2H), 7.53-7.65 (m, 1H), 8.10-8.20 (m, 1H), 8.42-8.51 (m, 1H), 8.70-8.80 (m, 1H), 8.81-8.93 (m, 1H), 11.13-11.35 (m, 1H). LCMS(ESI): [M+H]$^+$ m/z: calcd 432.2; found 433.2; Rt=3.218 min.

Example 462. The Synthesis of rac-5-{2-[(2R,5S)-5-methyl-2-[4-(oxan-4-yloxy)phenyl]piperidin-1-yl]-2-oxoacetamido}pyridine-3-carboxamide (Compound 269

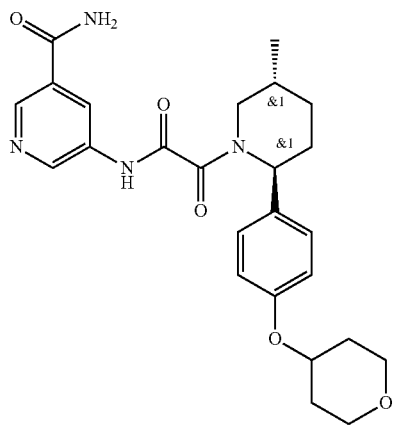
Compound 269

Prepared by general procedure. Yield: 8.1 mg, 4.96% $^1$H NMR (600 MHz, DMSO-$d_6$) δ 0.98-1.03 (m, 3H), 1.27-1.36 (m, 1H), 1.49-1.57 (m, 2H), 1.65-1.73 (m, 1H), 1.79-1.89 (m, 1H), 1.90-1.97 (m, 2H), 1.98-2.12 (m, 1H), 2.14-2.22 (m, 1H), 2.79-3.21 (m, 1H), 3.40-3.49 (m, 3H), 3.80-3.98 (m, 2H), 4.48-4.59 (m, 1H), 5.02-5.60 (m, 1H), 6.92-7.00 (m, 2H), 7.18-7.28 (m, 2H), 7.55-7.66 (m, 1H), 8.10-8.21 (m, 1H), 8.41-8.53 (m, 1H), 8.67-8.80 (m, 1H), 8.81-8.93 (m, 1H), 11.08-11.35 (m, 1H). LCMS(ESI): [M+H]$^+$ m/z: calcd 466.2; found 467.2; Rt=3.057 min.

Example 463. The Synthesis of rac-5-{2-[(2R,5S)-5-methyl-2-[4-(oxolan-3-yloxy)phenyl]piperidin-1-yl]-2-oxoacetamido}pyridine-3-carboxamide (Compound 264

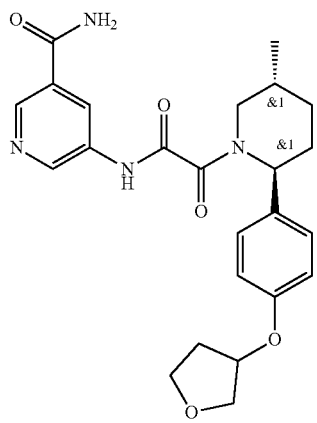
Compound 264

Prepared by general procedure 1. Yield: 5.4 mg, 3.41% $^1$H NMR (600 MHz, DMSO-$d_6$) δ 0.98-1.04 (m, 3H), 1.28-1.38 (m, 1H), 1.63-1.73 (m, 1H), 1.82-1.95 (m, 2H), 1.97-2.13 (m, 1H), 2.15-2.23 (m, 2H), 2.77-3.23 (m, 1H), 3.40-3.70 (m, 1H), 3.73-4.00 (m, 4H), 4.95-5.04 (m, 1H), 5.05-5.63 (m, 1H), 6.87-6.94 (m, 2H), 7.19-7.26 (m, 2H), 7.55-7.64 (m, 1H), 8.11-8.20 (m, 1H), 8.40-8.51 (m, 1H), 8.71-8.80 (m, 1H), 8.81-8.94 (m, 1H), 11.13-11.28 (m, 1H). LCMS (ESI): [M+H]$^+$ m/z: calcd 452.2; found 453.2; Rt=2.921 min.

Example 464. The Synthesis of rac-5-{2-[(2R,5S)-2-(6-fluoropyridin-3-yl)-5-methylpiperidin-1-yl]-2-oxoacetamido}pyridine-3-carboxamide (Compound 276

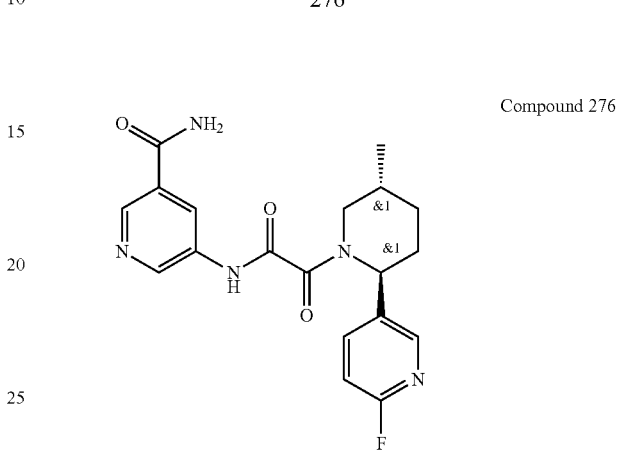
Compound 276

Prepared by general procedure 1. Yield: 14.9 mg, 11.05% $^1$H NMR (600 MHz, DMSO-$d_6$) δ 0.80-1.07 (m, 3H), 1.28-1.41 (m, 1H), 1.62-1.70 (m, 1H), 1.81-1.96 (m, 1H), 1.99-2.15 (m, 1H), 2.15-2.27 (m, 1H), 2.70-3.25 (m, 1H), 3.48-4.23 (m, 1H), 5.21-5.78 (m, 1H), 7.15-7.30 (m, 1H), 7.49-7.64 (m, 1H), 7.87-8.00 (m, 1H), 8.07-8.26 (m, 2H), 8.36-8.52 (m, 1H), 8.65-8.78 (m, 1H), 8.78-8.94 (m, 1H), 11.21 (br s, 1H). LCMS(ESI): [M+H]$^+$ m/z: calcd 385.3; found 386.2; Rt=2.738 min.

Example 465. The Synthesis of rac-5-{2-[(2R,5S)-5-methyl-2-[4-(trifluoromethoxy)phenyl]piperidin-1-yl]-2-oxoacetamido}pyridine-3-carboxamide (Compound 250

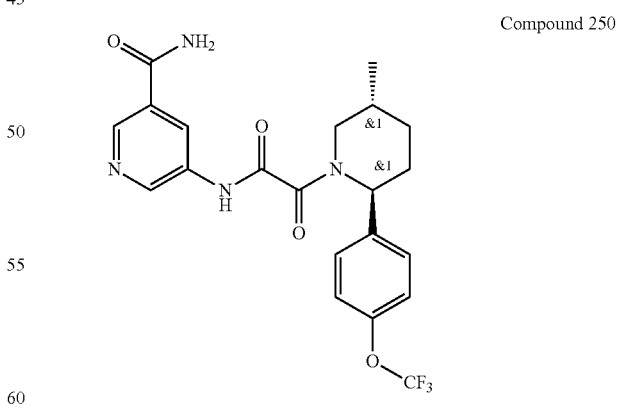
Compound 250

Prepared by general procedure 1. Yield: 10.3 mg, 6.53% $^1$H NMR (600 MHz, DMSO-$d_6$) δ 0.97-1.11 (m, 3H), 1.27-1.41 (m, 1H), 1.57-1.70 (m, 1H), 1.82-1.98 (m, 1H), 1.98-2.14 (m, 1H), 2.14-2.29 (m, 1H), 2.79-3.20 (m, 1H), 3.38-4.08 (m, 1H), 5.09-5.71 (m, 1H), 7.34-7.40 (m, 2H), 7.42-7.49 (m, 2H), 7.54-7.65 (m, 1H), 8.08-8.20 (m, 1H), 8.41-8.51 (m, 1H), 8.72-8.79 (m, 1H), 8.81-8.92 (m, 1H), 11.13-11.31 (m, 1H). LCMS(ESI): [M+H]⁺ m/z: calcd 450.2; found 451.2; Rt=1.299 min.

Example 466. The Synthesis of rac-5-{2-[(2R,5S)-2-[4-(cyclopropylmethyl)phenyl]-5-methylpiperidin-1-yl]-2-oxoacetamido}pyridine-3-carboxamide (Compound 273

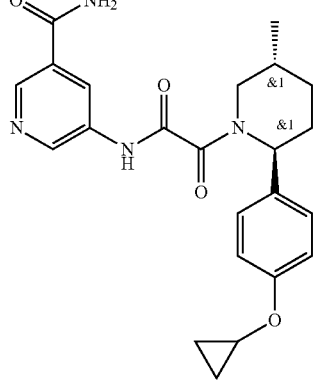

Compound 273

Prepared by general procedure 1. Yield: 12.4 mg, 8.42% ¹H NMR (600 MHz, DMSO-d₆) δ 0.14-0.19 (m, 2H), 0.41-0.47 (m, 2H), 0.88-0.97 (m, 1H), 0.97-1.06 (m, 3H), 1.23-1.38 (m, 1H), 1.60-1.72 (m, 1H), 1.77-1.95 (m, 1H), 1.98-2.16 (m, 1H), 2.16-2.29 (m, 1H), 2.43-2.45 (m, 1H), 2.49-2.52 (m, 1H), 2.74-3.20 (m, 1H), 3.45-4.04 (m, 1H), 5.08-5.63 (m, 1H), 7.19-7.27 (m, 4H), 7.49-7.64 (m, 1H), 8.05-8.28 (m, 1H), 8.38-8.54 (m, 1H), 8.68-8.79 (m, 1H), 8.80-8.93 (m, 1H), 11.22 (br s, 1H). LCMS(ESI): [M+H]⁺ m/z: calcd 420.2; found 421.4; Rt=3.738 min.

Example 467. The Synthesis of rac-5-{2-[(2R,5S)-2-(4-cyanophenyl)-5-methylpiperidin-1-yl]-2-oxoacetamido}pyridine-3-carboxamide (Compound 246

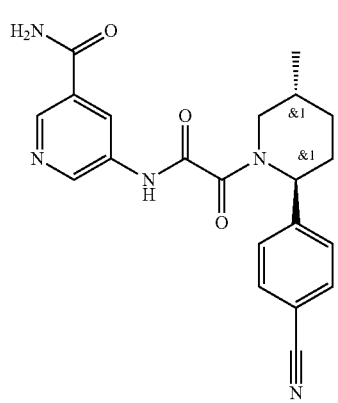

Compound 246

Prepared by general procedure 1. Yield: 8.0 mg, 5.34% ¹H NMR (600 MHz, DMSO-d₆) δ 0.87-1.06 (m, 3H), 1.26-1.41 (m, 1H), 1.56-1.65 (m, 1H), 1.66-1.89 (m, 1H), 1.89-2.13 (m, 1H), 2.15-2.28 (m, 1H), 2.73-3.25 (m, 1H), 3.47-4.31 (m, 1H), 5.22-5.77 (m, 1H), 7.50-7.56 (m, 2H), 7.56-7.64 (m, 1H), 7.83-7.89 (m, 2H), 8.11-8.21 (m, 1H), 8.42-8.53 (m, 1H), 8.72-8.79 (m, 1H), 8.81-8.92 (m, 1H), 11.18-11.32 (m, 1H). LCMS(ESI): [M+H]⁺ m/z: calcd 391.2; found 392.2; Rt=1.017 min.

Example 468. The Synthesis of rac-5-{2-[(2R,5S)-2-[4-chloro-3-(trifluoromethyl)phenyl]-5-methylpiperidin-1-yl]-2-oxoacetamido}pyridine-3-carboxamide (Compound 337

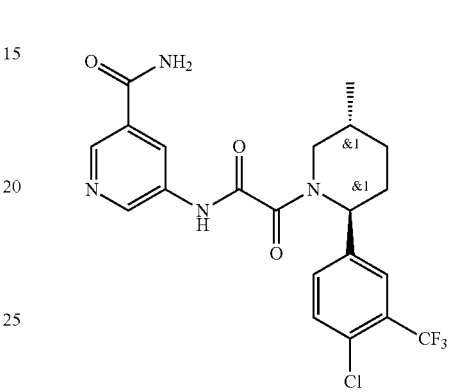

Compound 337

Prepared by general procedure 1. Yield: 14.7 mg, 8.96% ¹H NMR (600 MHz, DMSO-d₆) δ 1.03 (m, 3H), 1.35 (m, 3H), 1.72 (m, 1H), 1.86 (m, 1H), 2.01 (m, 1H), 2.14 (m, 1H), 2.74 (m, 1H), 3.00 (m, 1H), 3.42 (m, 2H), 4.22 (m, 1H), 4.87 (m, 1H), 5.27 (m, 1H), 6.69 (m, 1H), 7.02 (m, 1H), 7.14 (m, 1H), 7.59 (m, 1H), 8.14 (m, 1H), 8.46 (m, 1H), 8.75 (m, 1H), 8.85 (m, 1H), 11.17 (m, 1H). LCMS(ESI): [M+H]⁺ m/z: calcd 468.2; found 469.2; Rt=3.388 min.

Example 469. The Synthesis of rac-5-{2-[(2R,5S)-5-methyl-2-[4-(1H-pyrazol-1-yl)phenyl]piperidin-1-yl]-2-oxoacetamido}pyridine-3-carboxamide (Compound 256

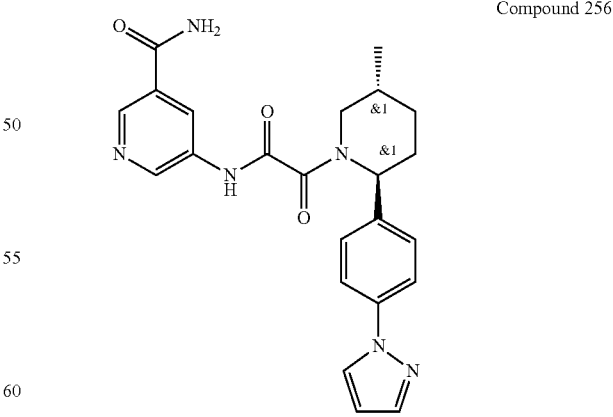

Compound 256

Prepared by general procedure 1. Yield: 10.8 mg, 7.2% ¹H NMR (600 MHz, DMSO-d₆) δ 0.99-1.08 (m, 3H), 1.29-1.44 (m, 1H), 1.64-1.75 (m, 1H), 1.84-1.96 (m, 1H), 2.04-2.19 (m, 1H), 2.20-2.32 (m, 1H), 2.77-3.17 (m, 1H), 3.47-4.06 (m, 1H), 5.17-5.74 (m, 1H), 6.50-6.55 (m, 1H), 7.41-7.49

(m, 2H), 7.55-7.64 (m, 1H), 7.67-7.75 (m, 1H), 7.80-7.87 (m, 2H), 8.10-8.21 (m, 1H), 8.43-8.53 (m, 2H), 8.71-8.80 (m, 1H), 8.83-8.94 (m, 1H), 11.05-11.39 (m, 1H). LCMS (ESI): [M+H]⁺ m/z: calcd 432.2; found 433.2; Rt=3.037 min.

Example 470. The Synthesis of rac-5-{2-[(2R,5S)-2-(4-cyano-3-cyclopropylphenyl)-5-methylpiperidin-1-yl]-2-oxoacetamido}pyridine-3-carboxamide (Compound 244

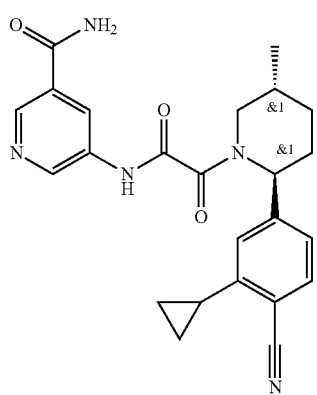

Compound 244

Prepared by general procedure 1. Yield: 2.9 mg, 1.93% ¹H NMR (600 MHz, DMSO-d₆) δ 0.75-0.84 (m, 2H), 0.97-1.15 (m, 5H), 1.23-1.38 (m, 1H), 1.51-1.63 (m, 1H), 1.81-1.93 (m, 1H), 1.99-2.27 (m, 3H), 2.75-3.23 (m, 1H), 3.42-4.06 (m, 1H), 5.13-5.65 (m, 1H), 6.89-6.99 (m, 1H), 7.21-7.33 (m, 1H), 7.54-7.67 (m, 1H), 7.70-7.83 (m, 1H), 8.08-8.21 (m, 1H), 8.39-8.57 (m, 1H), 8.68-8.79 (m, 1H), 8.79-8.93 (m, 1H), 11.12-11.35 (m, 1H). LCMS(ESI): [M+H]⁺ m/z: calcd 431.2; found 432.2; Rt=1.306 min.

Example 471. The Synthesis of rac-5-{2-[(2R,5S)-2-{4-[(1H-imidazol-1-yl)methyl]phenyl}-5-methylpiperidin-1-yl]-2-oxoacetamido}pyridine-3-carboxamide (Compound 238

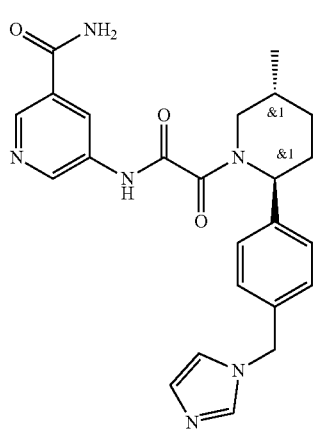

Compound 238

Prepared by general procedure 1. Yield: 26.6 mg, 17.02% ¹H NMR (600 MHz, DMSO-d₆) δ 0.98-1.08 (m, 3H), 1.26-1.40 (m, 1H), 1.58-1.68 (m, 1H), 1.81-1.91 (m, 1H), 2.00-2.26 (m, 2H), 2.74-3.24 (m, 1H), 3.43-4.03 (m, 1H), 5.13-5.57 (m, 3H), 7.25-7.28 (m, 1H), 7.29 (s, 2H), 7.30-7.35 (m, 1H), 7.55-7.65 (m, 1H), 7.91-7.98 (m, 1H), 8.08-8.22 (m, 1H), 8.40-8.51 (m, 1H), 8.61-8.66 (m, 1H), 8.71-8.79 (m, 1H), 8.81-8.92 (m, 1H), 11.12-11.28 (m, 1H). LCMS(ESI): [M+H]⁺ m/z: calcd 446.2; found 447.2; Rt=0.809 min.

Example 472. The Synthesis of rac-5-{2-[(2R,5S)-5-methyl-2-{4-[(1H-1,2,4-triazol-1-yl)methyl]phenyl}piperidin-1-yl]-2-oxoacetamido}pyridine-3-carboxamide (Compound 252)

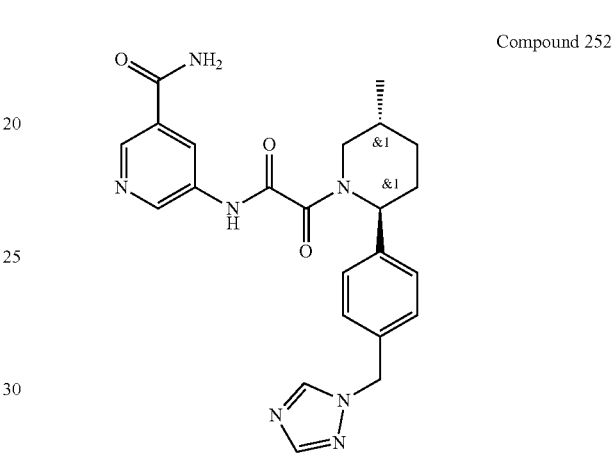

Compound 252

Prepared by general procedure 1. Yield: 22.2 mg, 14.17% ¹H NMR (600 MHz, DMSO-d₆) δ 0.98-1.08 (m, 3H), 1.26-1.40 (m, 1H), 1.58-1.68 (m, 1H), 1.81-1.91 (m, 1H), 2.00-2.26 (m, 2H), 2.74-3.24 (m, 1H), 3.43-4.03 (m, 1H), 5.13-5.57 (m, 3H), 7.25-7.28 (m, 1H), 7.29 (s, 2H), 7.30-7.35 (m, 1H), 7.55-7.65 (m, 1H), 7.91-7.98 (m, 1H), 8.08-8.22 (m, 1H), 8.40-8.51 (m, 1H), 8.61-8.66 (m, 1H), 8.71-8.79 (m, 1H), 8.81-8.92 (m, 1H), 11.12-11.28 (m, 1H). LCMS(ESI): [M+H]⁺ m/z: calcd 447.2; found 448.2; Rt=1.008 min.

Example 473. The Synthesis of rac-5-{2-[(2R,5S)-2-(3,4-dichlorophenyl)-5-methylpiperidin-1-yl]-2-oxoacetamido}pyridine-3-carboxamide (Compound 243

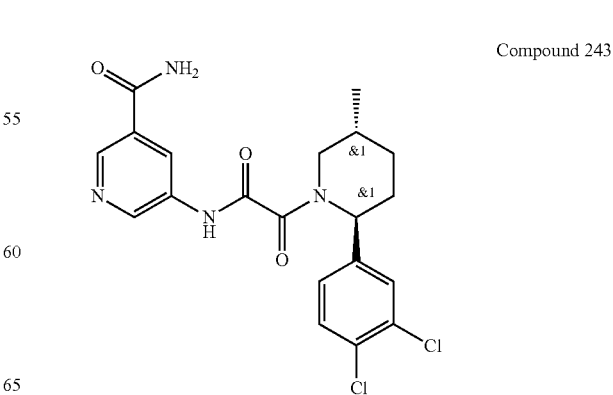

Compound 243

Prepared by general procedure 1. Yield: 13.4 mg, 8.79% $^1$H NMR (600 MHz, DMSO-$d_6$) δ 0.93-1.08 (m, 3H), 1.24-1.42 (m, 1H), 1.56-1.70 (m, 1H), 1.78-1.97 (m, 1H), 2.01-2.28 (m, 2H), 2.76-3.25 (m, 1H), 3.43-4.09 (m, 1H), 5.12-5.58 (m, 1H), 7.27-7.36 (m, 1H), 7.51-7.56 (m, 1H), 7.56-7.62 (m, 1H), 7.62-7.70 (m, 1H), 8.10-8.20 (m, 1H), 8.42-8.52 (m, 1H), 8.71-8.80 (m, 1H), 8.80-8.93 (m, 1H), 11.09-11.34 (m, 1H). LCMS(ESI): [M+2H]$^+$ m/z: calcd 435.3; found 437.1; Rt=1.336 min.

Example 474. The Synthesis of rac-5-{2-[(2R,5S)-2-(4-chloro-3-fluorophenyl)-5-methylpiperidin-1-yl]-2-oxoacetamido}pyridine-3-carboxamide (Compound 327

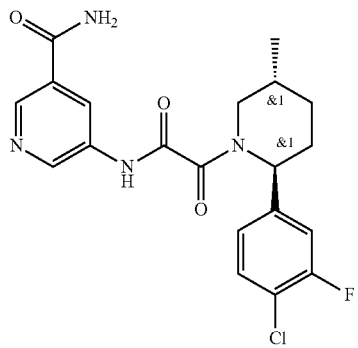

Compound 327

Prepared by general procedure 1. Yield: 7.0 mg, 4.78% $^1$H NMR (600 MHz, DMSO-$d_6$) δ 1.01 (m, 3H), 1.32 (m, 1H), 1.63 (m, 1H), 1.88 (m, 1H), 2.10 (m, 2H), 2.90 (m, 1H), 3.84 (m, 1H), 5.35 (m, 1H), 7.19 (m, 1H), 7.36 (m, 1H), 7.60 (m, 2H), 8.15 (m, 1H), 8.46 (m, 1H), 8.76 (m, 1H), 8.87 (m, 1H), 11.24 (m, 1H). LCMS(ESI): [M+H]$^+$ m/z: calcd 418.2; found 419.2; Rt=1.311 min.

Example 475. The Synthesis of rac-5-{2-[(2R,5S)-2-(3-fluorophenyl)-5-methylpiperidin-1-yl]-2-oxoacetamido}pyridine-3-carboxamide (Compound 247

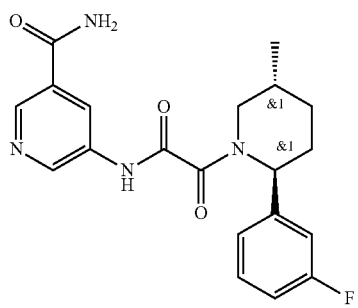

Compound 247

Prepared by general procedure 1. Yield: 9.8 mg, 7.28% $^1$H NMR (600 MHz, DMSO-$d_6$) δ 0.95-1.08 (m, 3H), 1.29-1.43 (m, 1H), 1.59-1.71 (m, 1H), 1.81-1.95 (m, 1H), 2.00-2.15 (m, 1H), 2.17-2.29 (m, 1H), 2.74-3.25 (m, 1H), 3.46-4.08 (m, 1H), 5.13-5.69 (m, 1H), 7.05-7.22 (m, 3H), 7.37-7.50 (m, 1H), 7.54-7.66 (m, 1H), 8.09-8.22 (m, 1H), 8.41-8.54 (m, 1H), 8.70-8.80 (m, 1H), 8.80-8.93 (m, 1H), 11.29 (br s, 1H). LCMS(ESI): [M+H]$^+$ m/z: calcd 384.2; found 385.2; Rt=1.235 min.

Example 476. The Synthesis of rac-5-{2-[(2R,5S)-2-[3-(difluoromethyl)phenyl]-5-methylpiperidin-1-yl]-2-oxoacetamido}pyridine-3-carboxamide (Compound 268

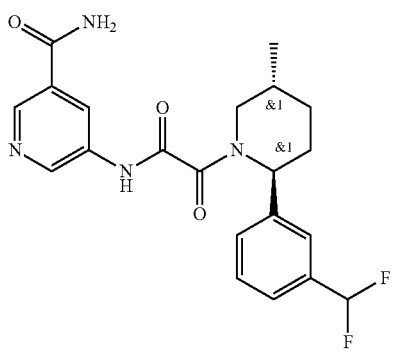

Compound 268

Prepared by general procedure 1. Yield: 7.6 mg, 5.21% $^1$H NMR (600 MHz, DMSO-$d_6$) δ 0.98-1.07 (m, 3H), 1.28-1.39 (m, 1H), 1.60-1.69 (m, 1H), 1.82-1.95 (m, 1H), 2.04-2.17 (m, 1H), 2.18-2.30 (m, 1H), 2.74-3.25 (m, 1H), 3.51-4.10 (m, 1H), 5.18-5.75 (m, 1H), 6.90-7.15 (m, 1H), 7.45-7.67 (m, 5H), 8.09-8.22 (m, 1H), 8.41-8.55 (m, 1H), 8.69-8.81 (m, 1H), 8.81-8.98 (m, 1H), 11.19-11.34 (m, 1H). LCMS (ESI): [M+H]$^+$ m/z: calcd 416.2; found 417.2; Rt=3.096 min.

Example 477. The Synthesis of rac-5-{2-[(2R,5S)-2-(3-cyclobutylphenyl)-5-methylpiperidin-1-yl]-2-oxoacetamido}pyridine-3-carboxamide (Compound 261

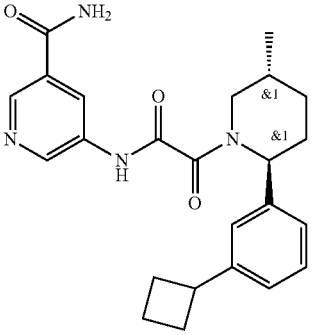

Compound 261

Prepared by general procedure 1. Yield: 1.8 mg, 1.22% LCMS(ESI): [M+H]$^+$ m/z: calcd 420.2; found 421.2; Rt=1.386 min.

Example 478. The Synthesis of rac-5-{2-[(2R,5S)-5-methyl-2-[3-(trifluoromethoxy)phenyl]piperidin-1-yl]-2-oxoacetamido}pyridine-3-carboxamide (Compound 279

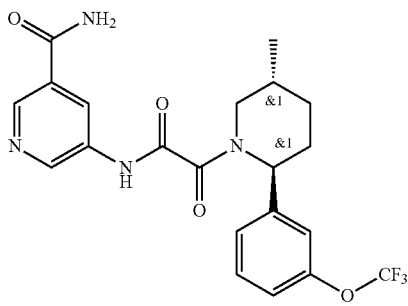

Compound 279

Prepared by general procedure 1. Yield: 19.6 g, 12.43% $^1$H NMR (600 MHz, DMSO-d$_6$) δ 0.97-1.07 (m, 3H), 1.28-1.42 (m, 1H), 1.58-1.68 (m, 1H), 1.83-1.96 (m, 1H), 2.01-2.16 (m, 1H), 2.16-2.30 (m, 1H), 2.71-3.24 (m, 1H), 3.47-4.07 (m, 1H), 5.19-5.70 (m, 1H), 7.23-7.32 (m, 2H), 7.34-7.44 (m, 1H), 7.50-7.61 (m, 2H), 8.10-8.21 (m, 1H), 8.39-8.53 (m, 1H), 8.70-8.80 (m, 1H), 8.80-8.92 (m, 1H), 11.17-11.38 (m, 1H). LCMS(ESI): [M+H]$^+$ m/z: calcd 450.2; found 451.2; Rt=3.477 min.

Example 479. The Synthesis of rac-5-{2-[(2R,5S)-2-(2,3-dihydro-1H-inden-5-yl)-5-methylpiperidin-1-yl]-2-oxoacetamido}pyridine-3-carboxamide (Compound 277

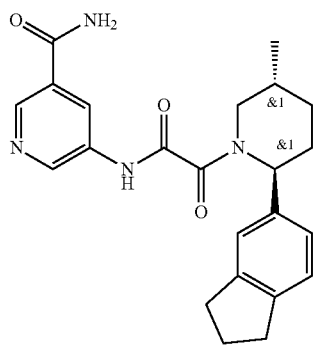

Compound 277

Prepared by general procedure 1. Yield: 4.8 mg, 3.73% $^1$H NMR (600 MHz, DMSO-d$_6$) δ 0.98-1.07 (m, 3H), 1.27-1.38 (m, 1H), 1.62-1.74 (m, 1H), 1.79-1.91 (m, 1H), 1.95-2.12 (m, 3H), 2.15-2.23 (m, 1H), 2.77-2.85 (m, 4H), 3.23-3.27 (m, 1H), 3.46-4.01 (m, 1H), 4.99-5.62 (m, 1H), 7.02-7.10 (m, 1H), 7.14-7.24 (m, 2H), 7.50-7.68 (m, 1H), 8.06-8.22 (m, 1H), 8.38-8.53 (m, 1H), 8.69-8.79 (m, 1H), 8.79-9.01 (m, 1H), 11.02-11.40 (m, 1H). LCMS(ESI): [M+H]$^+$ m/z: calcd 406.2; found 407.2; Rt=3.466 min.

Example 480. The Synthesis of rac-5-{2-[(2R,5S)-2-(1-benzofuran-6-yl)-5-methylpiperidin-1-yl]-2-oxoacetamido}pyridine-3-carboxamide (Compound 241

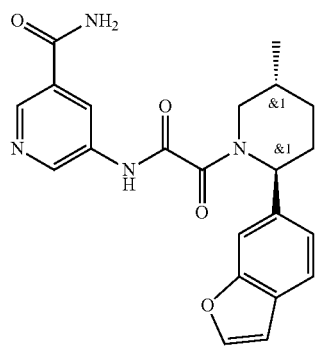

Compound 241

Prepared by general procedure 1. Yield: 10.0 mg, 7.03% $^1$H NMR (600 MHz, DMSO-d$_6$) δ 1.01-1.06 (m, 3H), 1.28-1.39 (m, 1H), 1.69-1.77 (m, 1H), 1.83-1.94 (m, 1H), 2.05-2.20 (m, 1H), 2.26-2.34 (m, 1H), 2.81-3.21 (m, 1H), 3.47-4.06 (m, 1H), 5.18-5.75 (m, 1H), 6.90-6.95 (m, 1H), 7.20-7.28 (m, 1H), 7.52-7.56 (m, 1H), 7.56-7.62 (m, 1H), 7.62-7.68 (m, 1H), 7.95-8.00 (m, 1H), 8.09-8.22 (m, 1H), 8.42-8.53 (m, 1H), 8.70-8.80 (m, 1H), 8.82-8.93 (m, 1H), 11.11-11.39 (m, 1H). LCMS(ESI): [M+H]$^+$ m/z: calcd 406.2; found 407.1; Rt=1.248 min.

Example 481. The Synthesis of rac-5-{2-[(2R,5S)-2-(2,3-dihydro-1-benzofuran-6-yl)-5-methylpiperidin-1-yl]-2-oxoacetamido}pyridine-3-carboxamide (Compound 405

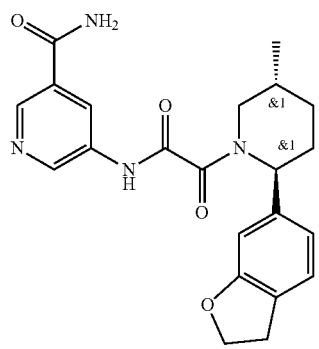

Compound 405

Prepared by general procedure 1. Yield: 8.8 mg, 6.0% $^1$H NMR (500 MHz, DMSO) δ 1.00-1.05 (m, 3H), 1.26-1.38 (m, 1H), 1.66-1.78 (m, 1H), 1.84-1.96 (m, 1H), 1.97-2.10 (m, 1H), 2.15-2.25 (m, 1H), 2.82-3.14 (m, 2H), 3.46-4.04 (m, 1H), 4.23-4.59 (m, 3H), 5.05-5.60 (m, 1H), 6.68-6.77 (m, 1H), 6.77-6.88 (m, 1H), 7.17-7.31 (m, 1H), 7.56-7.69 (m, 1H), 8.10-8.26 (m, 1H), 8.43-8.56 (m, 1H), 8.72-8.83 (m, 1H), 8.84-8.96 (m, 1H), 11.08-11.38 (m, 1H). LCMS (ESI): [M+H]$^+$ m/z: calcd 408.2; found 409.2; Rt=3.179 min.

Example 482. The Synthesis of rac-5-{2-[(2R,5S)-2-(3-cyanophenyl)-5-methylpiperidin-1-yl]-2-oxoacetamido}pyridine-3-carboxamide (Compound 239

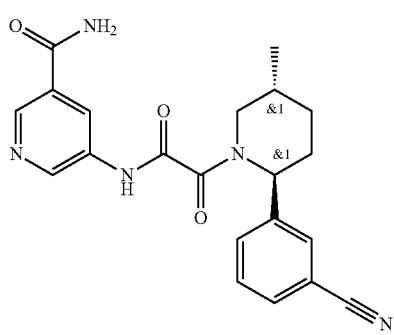

Compound 239

Prepared by general procedure 1. Yield: 14.5 mg, 10.58%
¹H NMR (600 MHz, DMSO-d₆) δ 0.83-1.08 (m, 3H), 1.23-1.39 (m, 1H), 1.56-1.70 (m, 1H), 1.82-1.97 (m, 1H), 2.00-2.19 (m, 1H), 2.19-2.35 (m, 1H), 2.73-3.26 (m, 1H), 3.48-4.06 (m, 1H), 5.12-5.72 (m, 1H), 7.56-7.71 (m, 3H), 7.72-7.81 (m, 2H), 8.09-8.21 (m, 1H), 8.40-8.54 (m, 1H), 8.72-8.80 (m, 1H), 8.80-8.94 (m, 1H), 11.15-11.39 (m, 1H). LCMS(ESI): [M+H]⁺ m/z: calcd 391.2; found 392.2; Rt=1.169 min.

Example 483. The Synthesis of rac-5-{2-[(2R,5S)-2-(1,3-dioxaindan-5-yl)-5-methylpiperidin-1-yl]-2-oxoacetamido}pyridine-3-carboxamide (Compound 270

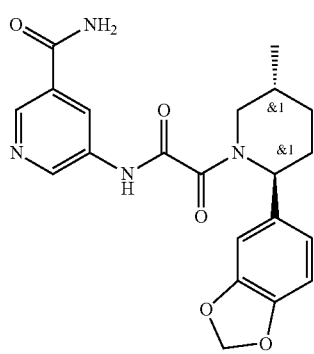

Compound 270

Prepared by general procedure 1. Yield: 2.4 mg, 1.67% LCMS(ESI): [M+H]⁺ m/z: calcd 410.2; found 411.0; Rt=1.181 min.

Example 484. The Synthesis of rac-5-{2-[(2R,5S)-5-methyl-2-[3-(trifluoromethyl)phenyl]piperidin-1-yl]-2-oxoacetamido}pyridine-3-carboxamide (Compound 265

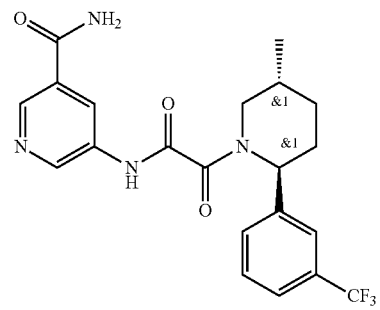

Compound 265

Prepared by general procedure 1. Yield: 11.7 mg, 7.69%
¹H NMR (600 MHz, DMSO-d₆) δ 0.98-1.08 (m, 3H), 1.28-1.42 (m, 1H), 1.57-1.70 (m, 1H), 1.82-1.96 (m, 1H), 2.03-2.19 (m, 1H), 2.19-2.32 (m, 1H), 2.70-3.24 (m, 1H), 3.50-4.07 (m, 1H), 5.22-5.76 (m, 1H), 7.57-7.72 (m, 5H), 8.08-8.19 (m, 1H), 8.38-8.53 (m, 1H), 8.67-8.78 (m, 1H), 8.78-8.93 (m, 1H), 11.29 (br s, 1H) LCMS(ESI): [M+H]⁺ m/z: calcd 434.2; found 435.2; Rt=3.373 min.

Example 485. The Synthesis of rac-5-{2-[(2R,5S)-2-(3,4-dihydro-2H-1-Benzopyran-6-yl)-5-methylpiperidin-1-yl]-2-oxoacetamido}pyridine-3-carboxamide (Compound 341

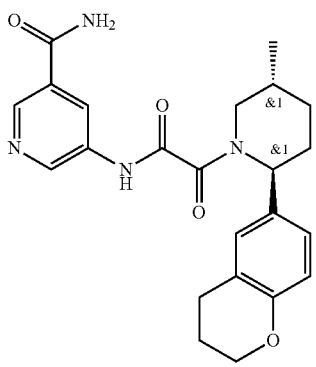

Compound 341

Prepared by general procedure 1. Yield: 10.2 mg, 6.90%
¹H NMR (600 MHz, DMSO-d₆) δ 1.00 (m, 3H), 1.31 (m, 1H), 1.70 (m, 1H), 1.88 (m, 3H), 2.01 (m, 1H), 2.14 (m, 1H), 2.71 (m, 2H), 3.03 (m, 1H), 3.68 (m, 1H), 4.08 (m, 2H), 5.26 (m, 1H), 6.70 (m, 1H), 6.98 (m, 2H), 7.59 (m, 1H), 8.15 (m, 1H), 8.46 (m, 1H), 8.75 (m, 1H), 8.85 (m, 1H), 11.19 (m, 1H).

LCMS(ESI): [M+H]⁺ m/z: calcd 422.2; found 423.2; Rt=3.122 min.

Example 486. The Synthesis of rac-5-{2-[(2R,5S)-5-methyl-2-[6-(methylamino)pyridin-3-yl]piperidin-1-yl]-2-oxoacetamido}pyridine-3-carboxamide (Compound 209

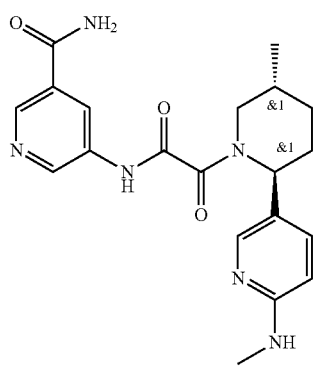

Compound 209

Prepared by general procedure 1. Yield: 18.3 mg, 13.19% $^1$H NMR (DMSO-$d_6$, 500 MHz): δ (ppm) 1.03 (m, 3H), 1.34 (m, 1H), 1.94 (m, 4H), 2.75 (m, 3H), 3.10 (m, 1H), 3.68 (m, 1H), 5.26 (m, 1H), 6.46 (m, 2H), 7.35 (m, 1H), 7.61 (m, 1H), 7.96 (m, 1H), 8.17 (m, 1H), 8.48 (m, 1H), 8.78 (m, 1H), 8.89 (m, 1H), 11.19 (m, 1H) LCMS(ESI): [M+H]$^+$ m/z: calcd 396.2; found 397.2; Rt=0.782 min.

Example 487. The Synthesis of rac-5-{2-[(2R,5S)-2-(6-aminopyridin-3-yl)-5-methylpiperidin-1-yl]-2-oxoacetamido}pyridine-3-carboxamide (Compound 224

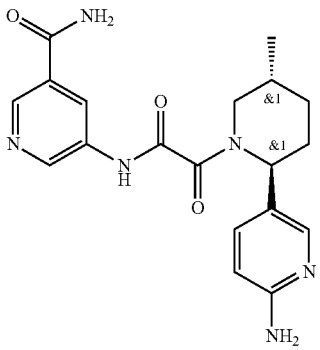

Compound 224

Prepared by general procedure 1. Yield: 6.7 mg, 5.01% $^1$H NMR (DMSO-$d_6$, 500 MHz): δ (ppm) 1.02 (m, 3H), 1.34 (m, 1H), 1.96 (m, 4H), 3.01 (m, 1H), 3.61 (m, 1H), 5.25 (m, 1H), 5.88 (s, 2H), 6.45 (m, 1H), 7.34 (m, 1H), 7.61 (m, 1H), 7.87 (s, 1H), 8.17 (m, 1H), 8.48 (m, 1H), 8.77 (m, 1H), 8.88 (m, 1H) LCMS(ESI): [M+H]$^+$ m/z: calcd 382.2; found 383.1; Rt=0.742 min.

Example 488. The Synthesis of rac-5-{2-[(2R,5S)-5-methyl-2-[4-(4-methyl-1H-pyrazol-1-yl)phenyl]piperidin-1-yl]-2-oxoacetamido}pyridine-3-carboxamide (Compound 218

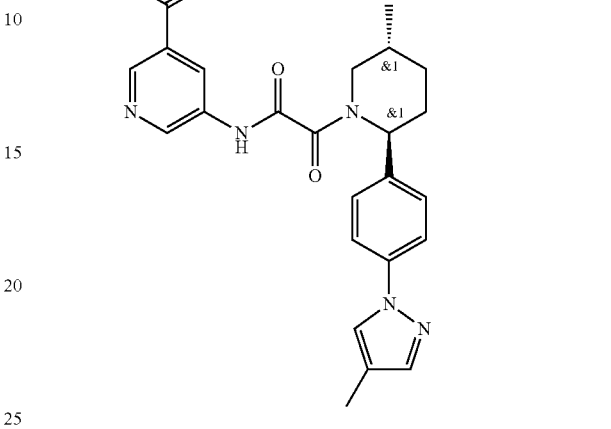

Compound 218

Prepared by general procedure 1. Yield: 20.8 mg, 13.31% $^1$H NMR (DMSO-$d_6$, 500 MHz): δ (ppm) 1.05 (m, 3H), 1.37 (m, 1H), 1.71 (m, 1H), 1.92 (m, 1H), 2.10 (s, 4H), 2.26 (m, 1H), 3.05 (m, 1H), 3.78 (m, 1H), 5.42 (m, 1H), 7.44 (m, 2H), 7.58 (m, 2H), 7.79 (m, 2H), 8.17 (m, 1H), 8.26 (m, 1H), 8.50 (m, 1H), 8.78 (m, 1H), 8.90 (m, 1H), 11.29 (s, 1H) LCMS (ESI): [M+H]$^+$ m/z: calcd 446.2; found 447.2; Rt=1.234 min.

Example 489. The Synthesis of rac-5-{2-[(2R,5S)-5-methyl-2-[6-(pyrrolidin-1-yl)pyridin-3-yl]piperidin-1-yl]-2-oxoacetamido}pyridine-3-carboxamide (Compound 207

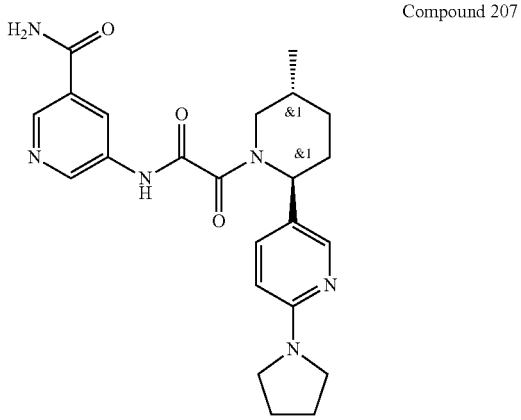 [SMILES: C[C@@H]1CC[C@@H](c2ccc(N3CCCC3)nc2)N(C(=O)C(=O)Nc2cncc(C(N)=O)c2)C1]

Compound 207

Prepared by general procedure 1. Yield: 10.9 mg, 7.13% $^1$H NMR (DMSO-$d_6$, 600 MHz): δ (ppm) 1.00 (m, 3H), 1.32 (m, 1H), 1.89 (m, 6H), 2.05 (m, 2H), 3.10 (m, 1H), 3.35 (s, 4H), 3.61 (m, 1H), 5.25 (m, 1H), 6.41 (m, 1H), 7.41 (m, 1H), 7.59 (m, 1H), 8.01 (m, 1H), 8.14 (m, 1H), 8.44 (m, 1H), 8.75 (m, 1H), 8.85 (m, 1H), 11.15 (m, 1H) LCMS(ESI): [M+H]$^+$ m/z: calcd 436.2; found 437.2; Rt=0.866 min.

Example 490. The Synthesis of rac-5-{2-[(2R,5S)-2-(4-Fluoro-3-methoxyphenyl)-5-methylpiperidin-1-yl]-2-oxoacetamido}pyridine-3-carboxamide (Compound 222

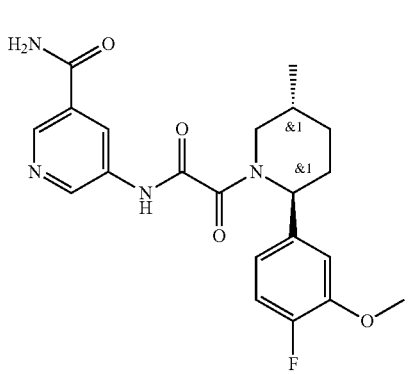

Compound 222

Prepared by general procedure 1. Yield: 2.2 mg, 1.52% ¹H NMR (DMSO-d₆, 500 MHz): δ (ppm) 1.03 (m, 3H), 1.34 (m, 1H), 1.71 (m, 1H), 1.92 (m, 1H), 2.16 (m, 3H), 3.71 (m, 4H), 5.34 (m, 1H), 6.90 (m, 1H), 7.05 (m, 1H), 7.21 (m, 1H), 7.63 (m, 1H), 8.17 (m, 1H), 8.49 (m, 1H), 8.77 (m, 1H), 8.87 (m, 1H), 11.27 (s, 1H) LCMS(ESI): [M+H]⁺ m/z: calcd 414.2; found 415.2; Rt=1.219 min.

Example 491. The Synthesis of rac-5-{2-[(2R,5S)-5-methyl-2-{4-[(Morpholin-4-yl)methyl]phenyl}piperidin-1-yl]-2-oxoacetamido}pyridine-3-carboxamide (Compound 213)

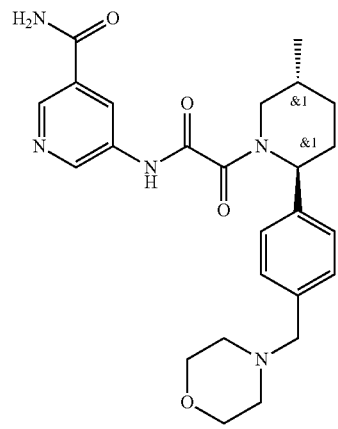

Compound 213

Prepared by general procedure 1. Yield: 20.4 mg, 12.52% ¹H NMR (DMSO-d₆, 500 MHz): δ (ppm) 1.04 (m, 3H), 1.35 (m, 1H), 1.69 (m, 1H), 1.89 (m, 1H), 2.14 (m, 2H), 2.33 (m, 4H), 2.96 (m, 1H), 3.44 (m, 3H), 3.55 (m, 4H), 5.38 (m, 1H), 7.31 (m, 4H), 7.61 (m, 1H), 8.16 (m, 1H), 8.48 (m, 1H), 8.83 (m, 2H), 11.22 (m, 1H). LCMS(ESI): [M+H]⁺ m/z: calcd 465.2; found 466.2; Rt=0.854 min.

Example 492. The Synthesis of rac-5-{2-[(2R,5S)-2-(4-chloro-3-methylphenyl)-5-methylpiperidin-1-yl]-2-oxoacetamido}pyridine-3-carboxamide (Compound 173

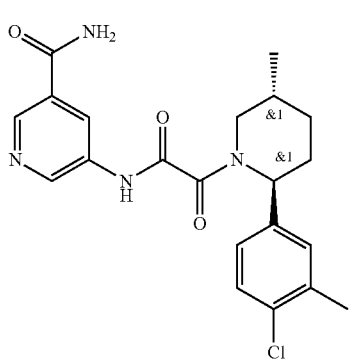

Compound 173

Prepared by general procedure 1. Yield: 12.8 mg, 8.81% LCMS(ESI): [M+H]⁺ m/z: calcd 414.2; found 415.2; Rt=1.359 min.

Example 493. The Synthesis of rac-5-{2-[(2R,5S)-2-[3-(3,5-dimethyl-1H-pyrazol-1-yl)phenyl]-5-methylpiperidin-1-yl]-2-oxoacetamido}pyridine-3-carboxamide (Compound 153

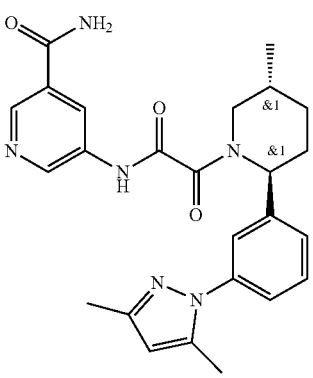

Compound 153

Prepared by general procedure 1. Yield: 15.1 mg, 9.37% ¹H NMR (DMSO-d₆, 600 MHz): δ (ppm) 1.03 (dd, 3H), 1.34 (m, 1H), 1.67 (m, 1H), 1.98 (m, 2H), 2.15 (m, 3H), 2.25 (m, 4H), 2.82 (m, 1H), 3.77 (m, 1H), 6.05 (m, 2H), 7.36 (m, 3H), 7.51 (m, 1H), 7.59 (m, 1H), 8.14 (m, 1H), 8.47 (m, 1H), 8.76 (m, 1H), 8.86 (m, 1H), 11.26 (m, 1H). LCMS(ESI): [M+H]⁺ m/z: calcd 460.2; found 461.2; Rt=1.160 min.

Example 494. The Synthesis of rac-5-{2-[(2R,5S)-5-methyl-2-[3-methyl-4-(oxolan-3-yloxy)phenyl]piperidin-1-yl]-2-oxoacetamido}pyridine-3-carboxamide (Compound 171

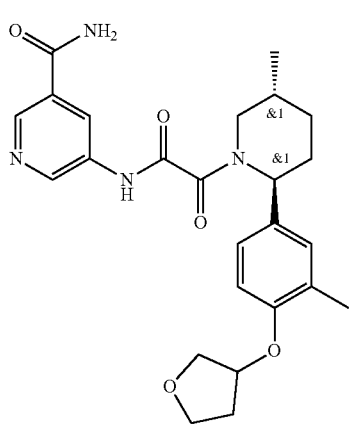

Compound 171

Prepared by general procedure 1. Yield: 21.6 mg, 12.23% $^1$H NMR (DMSO-d$_6$, 600 MHz): δ (ppm) 1.01 (m, 3H), 1.33 (m, 1H), 1.69 (m, 1H), 1.92 (m, 3H), 2.11 (m, 3H), 2.19 (m, 2H), 3.03 (m, 1H), 3.76 (m, 5H), 4.97 (m, 1H), 6.88 (m, 1H), 7.08 (m, 2H), 7.58 (m, 1H), 8.14 (m, 1H), 8.46 (m, 1H), 8.80 (m, 2H), 11.19 (m, 1H) LCMS(ESI): [M+H]$^+$ m/z: calcd 466.3; found 467.2; Rt=1.175 min.

Example 495. The Synthesis of rac-5-{2-[(2R,5S)-5-methyl-2-(2-methyl-2,3-dihydro-1-Benzofuran-5-yl)piperidin-1-yl]-2-oxoacetamido}pyridine-3-carboxamide (Compound 151)

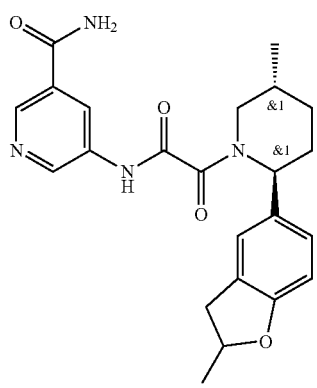

Compound 151

Prepared by general procedure 1. Yield: 22.4 mg, 15.15% $^1$H NMR (DMSO-d$_6$, 500 MHz): δ (ppm) 1.03 (m, 3H), 1.37 (m, 4H), 1.75 (m, 1H), 1.89 (m, 1H), 2.11 (m, 2H), 2.89 (m, 2H), 3.70 (m, 1H), 4.88 (m, 1H), 5.29 (m, 1H), 6.71 (dd, 1H), 7.04 (m, 1H), 7.16 (m, 1H), 7.60 (m, 1H), 8.16 (m, 1H), 8.48 (m, 1H), 8.77 (m, 1H), 8.88 (m, 1H), 11.19 (m, 1H). LCMS(ESI): [M+H]$^+$ m/z: calcd 422.2; found 423.2; Rt=1.263 min.

Example 496. The Synthesis of rac-5-{2-[(2R,5S)-5-methyl-2-(2-methylquinolin-6-yl)piperidin-1-yl]-2-oxoacetamido}pyridine-3-carboxamide (Compound 167

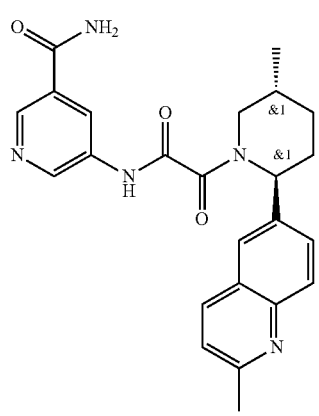

Compound 167

Prepared by general procedure 1. Yield: 18.2 mg, 12.05% $^1$H NMR (DMSO-d$_6$, 400 MHz): δ (ppm) 1.07 (m, 3H), 1.41 (m, 1H), 1.85 (m, 2H), 2.30 (m, 2H), 2.65 (m, 4H), 3.82 (m, 1H), 5.58 (m, 1H), 7.42 (m, 1H), 7.70 (m, 2H), 7.93 (m, 2H), 8.24 (m, 2H), 8.50 (m, 1H), 8.84 (m, 2H), 11.30 (m, 1H). LCMS(ESI): [M+H]$^+$ m/z: calcd 431.2; found 432.2; Rt=0.859 min.

Example 497. The Synthesis of rac-5-{2-[(2R,5S)-2-(3-Fluoro-4-methylphenyl)-5-methylpiperidin-1-yl]-2-oxoacetamido}pyridine-3-carboxamide (Compound 162

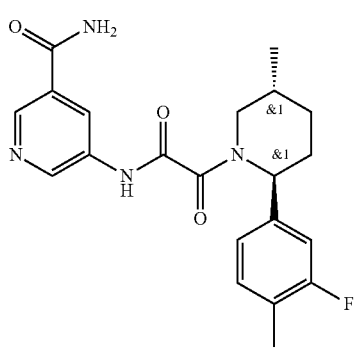

Compound 162

Prepared by general procedure 1. Yield: 8.6 mg, 6.17% $^1$H NMR (DMSO-d$_6$, 500 MHz): δ (ppm) 1.03 (m, 3H), 1.34 (m, 1H), 1.67 (m, 1H), 1.89 (m, 1H), 2.03 (m, 1H), 2.21 (m, 4H), 3.02 (m, 1H), 3.75 (m, 1H), 5.35 (m, 1H), 7.08 (m, 2H), 7.31 (m, 1H), 7.61 (m, 1H), 8.17 (m, 1H), 8.48 (m, 1H), 8.83 (m, 2H), 11.25 (m, 1H). LCMS(ESI): [M+H]$^+$ m/z: calcd 398.2; found 399.2; Rt=1.189 min.

Example 498. The Synthesis of rac-5-{2-[(2R,5S)-2-(3,4-dimethylphenyl)-5-methylpiperidin-1-yl]-2-oxoacetamido}pyridine-3-carboxamide (Compound 180

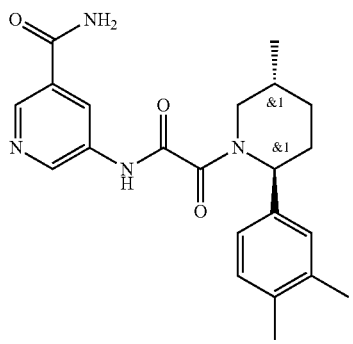

Compound 180

Prepared by general procedure 1. Yield: 13.1 mg, 9.49% $^1$H NMR (DMSO-d$_6$, 600 MHz): δ (ppm) 1.01 (m, 3H), 1.31 (m, 1H), 1.66 (m, 1H), 1.86 (m, 1H), 2.03 (m, 1H), 2.18 (m, 7H), 3.08 (m, 1H), 3.71 (m, 1H), 5.31 (m, 1H), 7.07 (m, 3H), 7.58 (m, 1H), 8.14 (m, 1H), 8.46 (m, 1H), 8.80 (m, 2H), 11.20 (m, 1H). LCMS(ESI): [M+H]$^+$ m/z: calcd 394.2; found 395.2; Rt=1.274 min.

Example 499. The Synthesis of rac-5-{2-[(2R,5S)-2-(3-chloro-4-methylphenyl)-5-methylpiperidin-1-yl]-2-oxoacetamido}pyridine-3-carboxamide (Compound 179

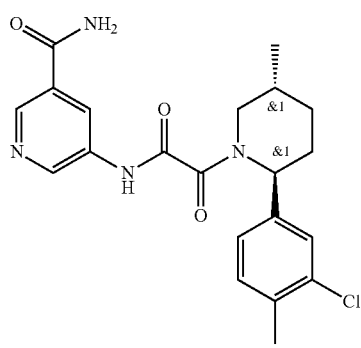

Compound 179

Prepared by general procedure 1. Yield: 25.4 mg, 17.49% $^1$H NMR (DMSO-d$_6$, 500 MHz): δ (ppm) 1.03 (m, 3H), 1.34 (m, 1H), 1.65 (m, 1H), 1.90 (m, 1H), 2.11 (m, 2H), 2.31 (m, 3H), 2.80 (m, 1H), 3.48 (m, 1H), 5.35 (m, 1H), 7.21 (m, 1H), 7.36 (m, 2H), 7.61 (d, 1H), 8.17 (m, 1H), 8.48 (m, 1H), 8.83 (m, 2H), 11.26 (s, 1H). LCMS(ESI): [M+H]$^+$ m/z: calcd 414.2; found 415.4; Rt=1.319 min.

Example 500. The Synthesis of rac-5-{2-[(2R,5S)-2-(3,5-difluorophenyl)-5-methylpiperidin-1-yl]-2-oxoacetamido}pyridine-3-carboxamide (Compound 416

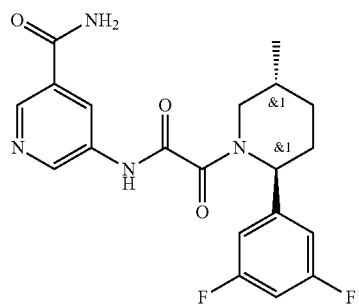

Compound 416

Prepared by general procedure 1. Yield: 3.4 mg, 2.35% $^1$H NMR (500 MHz, DMSO-d$_6$) δ 0.99-1.08 (m, 3H), 1.21-1.37 (m, 1H), 1.60-1.75 (m, 1H), 1.82-1.99 (m, 1H), 2.07-2.22 (m, 1H), 2.79-3.26 (m, 1H), 3.52-4.11 (m, 1H), 5.12-5.68 (m, 1H), 6.95-7.11 (m, 2H), 7.10-7.25 (m, 1H), 7.45-7.65 (m, 2H), 8.08-8.30 (m, 1H), 8.37-8.60 (m, 1H), 8.71-8.83 (m, 1H), 8.83-9.02 (m, 1H), 11.21-11.45 (m, 1H). LCMS (ESI): [M+H]$^+$ m/z: calcd 402.2; found 403.0; Rt=1.209 min.

Example 501. The Synthesis of rac-5-{2-[(2R,5S)-2-(3,5-Dichlorophenyl)-5-methylpiperidin-1-yl]-2-oxoacetamido}pyridine-3-carboxamide (Compound 206

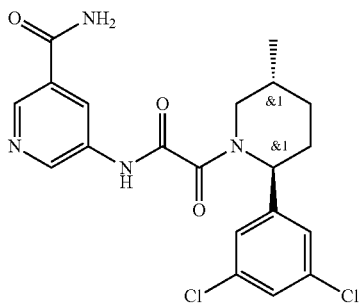

Compound 206

Prepared by general procedure 1. Yield: 2.5 mg, 1.64% $^1$H NMR (DMSO-d$_6$, 500 MHz): δ (ppm) 1.03 (m, 3H), 1.35 (m, 1H), 1.65 (m, 1H), 1.91 (m, 1H), 2.15 (m, 2H), 3.52 (m, 1H), 3.87 (m, 1H), 5.37 (m, 1H), 7.36 (m, 2H), 7.58 (m, 2H), 8.17 (m, 1H), 8.51 (m, 1H), 8.83 (m, 2H), 11.31 (m, 1H). LCMS(ESI): [M+H]$^+$ m/z: calcd 435.2; found 436.2; Rt=1.377 min.

Example 502. The Synthesis of rac-5-{2-[(2R,5S)-2-(3-amino-4-chlorophenyl)-5-methylpiperidin-1-yl]-2-oxoacetamido}pyridine-3-carboxamide (Compound 280

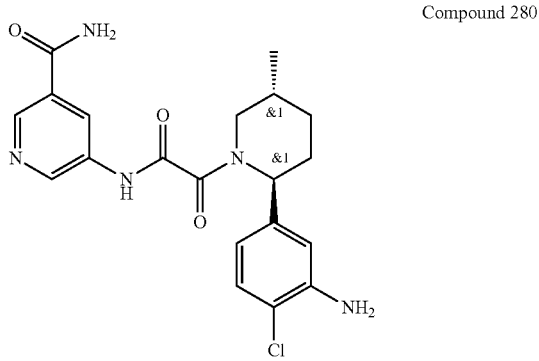 [SMILES: C[C@@H]1CC[C@@H](c2ccc(Cl)c(N)c2)N(C(=O)C(=O)Nc2cncc(C(N)=O)c2)C1]

Compound 280

Prepared by general procedure 1. Yield: 4.9 mg, 3.37% $^1$H NMR (600 MHz, DMSO-d$_6$) δ 0.92-1.06 (m, 3H), 1.25-1.37 (m, 1H), 1.64-1.75 (m, 1H), 1.81-1.95 (m, 1H), 1.95-2.12 (m, 2H), 2.81-3.25 (m, 1H), 3.46-4.03 (m, 1H), 5.02-5.29 (m, 1H), 5.29-5.51 (m, 2H), 6.45-6.54 (m, 1H), 6.73-6.83 (m, 1H), 7.11-7.20 (m, 1H), 7.52-7.63 (m, 1H), 8.08-8.21 (m, 1H), 8.43-8.53 (m, 1H), 8.71-8.79 (m, 1H), 8.83-8.93 (m, 1H), 10.73-11.52 (m, 1H). LCMS(ESI): [M+H]$^+$ m/z: calcd 415.2; found 416.2; Rt=1.199 min.

Example 503. The Synthesis of rac-5-{2-[(2R,5S)-2-(4-cyclobutylphenyl)-5-methylpiperidin-1-yl]-2-oxoacetamido}pyridine-3-carboxamide (Compound 406

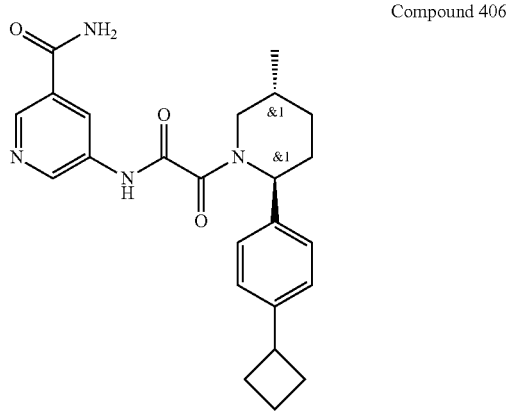 [SMILES: C[C@@H]1CC[C@@H](c2ccc(C3CCC3)cc2)N(C(=O)C(=O)Nc2cncc(C(N)=O)c2)C1]

Compound 406

Prepared by general procedure 1. Yield: 27.1 mg, 15.5% $^1$H NMR (500 MHz, DMSO) δ 1.01-1.06 (m, 3H), 1.28-1.42 (m, 1H), 1.66-1.75 (m, 1H), 1.76-1.90 (m, 2H), 1.91-2.04 (m, 2H), 2.04-2.15 (m, 3H), 2.18-2.34 (m, 3H), 2.80-3.29 (m, 1H), 3.50-4.06 (m, 1H), 5.12-5.65 (m, 1H), 7.22-7.31 (m, 4H), 7.55-7.70 (m, 1H), 8.05-8.28 (m, 1H), 8.45-8.58 (m, 1H), 8.75-8.85 (m, 1H), 8.85-8.97 (m, 1H), 11.09-11.39 (m, 1H). LCMS(ESI): [M+H]$^+$ m/z: calcd 420.2; found 421.2; Rt=1.420 min.

Example 504. The Synthesis of rac-5-{2-[(2R,5S)-5-methyl-2-[4-(trifluoromethyl)phenyl]piperidin-1-yl]-2-oxoacetamido}pyridine-3-carboxamide (Compound 251

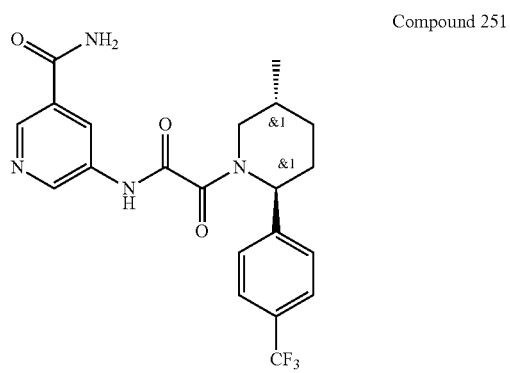 [SMILES: C[C@@H]1CC[C@@H](c2ccc(C(F)(F)F)cc2)N(C(=O)C(=O)Nc2cncc(C(N)=O)c2)C1]

Compound 251

Prepared by general procedure 1. Yield: 3.4 mg, 2.27% $^1$H NMR (600 MHz, DMSO-d$_6$) δ 0.96-1.07 (m, 3H), 1.27-1.40 (m, 1H), 1.57-1.68 (m, 1H), 1.82-1.96 (m, 1H), 2.05-2.18 (m, 1H), 2.19-2.31 (m, 1H), 2.73-3.25 (m, 1H), 3.46-4.12 (m, 1H), 5.18-5.80 (m, 1H), 7.50-7.57 (m, 2H), 7.58-7.65 (m, 1H), 7.69-7.79 (m, 2H), 8.07-8.23 (m, 1H), 8.41-8.55 (m, 1H), 8.71-8.80 (m, 1H), 8.81-8.95 (m, 1H), 11.16-11.33 (m, 1H). LCMS(ESI): [M+H]$^+$ m/z: calcd 434.2; found 435.0; Rt=1.366 min.

Example 505. The Synthesis of rac-5-{2-[(2R,5S)-2-(4-methoxyphenyl)-5-methylpiperidin-1-yl]-2-oxoacetamido}pyridine-3-carboxamide (Compound 228

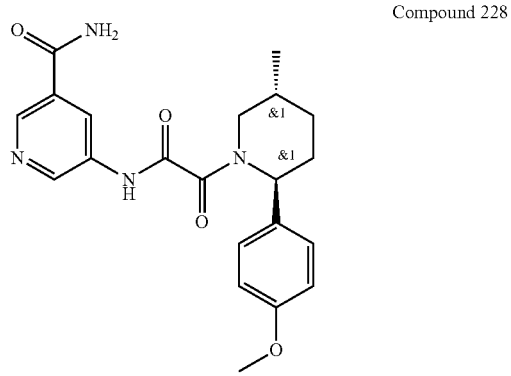 [SMILES: COc1ccc([C@@H]2CC[C@@H](C)CN2C(=O)C(=O)Nc2cncc(C(N)=O)c2)cc1]

Compound 228

Prepared by general procedure 1. Yield: 2.1 mg, 1.51% $^1$H NMR (DMSO-d$_6$, 500 MHz): δ (ppm) 1.03 (m, 3H), 1.35 (m, 1H), 1.80 (m, 3H), 2.02 (m, 1H), 2.19 (m, 1H), 3.64 (m, 4H), 5.34 (m, 1H), 6.95 (m, 2H), 7.26 (m, 2H), 7.61 (m, 1H), 8.16 (m, 1H), 8.48 (m, 1H), 8.77 (m, 1H), 8.89 (m, 1H), 11.26 (s, 1H). LCMS(ESI): [M+H]$^+$ m/z: calcd 396.2; found 397.2; Rt=1.195 min.

Example 506. The Synthesis of rac-5-{2-[(2R,5S)-2-(3,5-dimethoxyphenyl)-5-methylpiperidin-1-yl]-2-oxoacetamido}pyridine-3-carboxamide (Compound 428

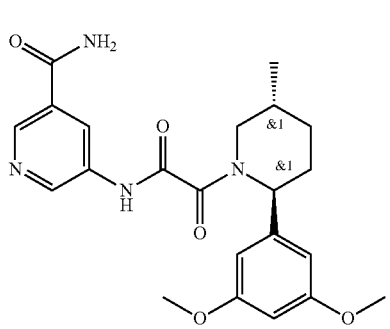

Compound 428

Prepared by general procedure 1. Yield: 14.7 mg, 7.2% $^1$H NMR (500 MHz, DMSO-d$_6$) δ 0.91-1.10 (m, 3H), 1.28-1.41 (m, 1H), 1.62-1.75 (m, 1H), 1.84-1.97 (m, 1H), 1.99-2.11 (m, 1H), 2.14-2.24 (m, 1H), 2.83-3.20 (m, 1H), 3.44-3.52 (m, 0.7H), 3.68-3.80 (m, 6H), 3.97-4.07 (m, 0.3H), 5.08-5.61 (m, 1H), 6.33-6.55 (m, 3H), 7.55-7.69 (m, 1H), 8.11-8.23 (m, 1H), 8.42-8.55 (m, 1H), 8.73-8.82 (m, 1H), 8.83-8.93 (m, 1H), 11.18-11.42 (m, 1H). LCMS(ESI): [M+H]$^+$ m/z: calcd 426.2; found 427.0; Rt=3.024 min.

Example 507. The Synthesis of rac-5-{2-[(2R,5S)-2-(2-methoxypyridin-4-yl)-5-methylpiperidin-1-yl]-2-oxoacetamido}pyridine-3-carboxamide (Compound 225

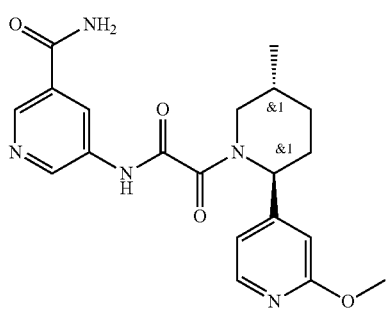

Compound 225

Prepared by general procedure 1. Yield: 1.3 mg, 0.94% LCMS(ESI): [M+H]$^+$ m/z: calcd 397.2; found 398.2; Rt=1.088 min.

Example 508. The Synthesis of rac-5-{2-[(2R,5S)-2-(4-carbamoylphenyl)-5-methylpiperidin-1-yl]-2-oxoacetamido}pyridine-3-carboxamide (Compound 220

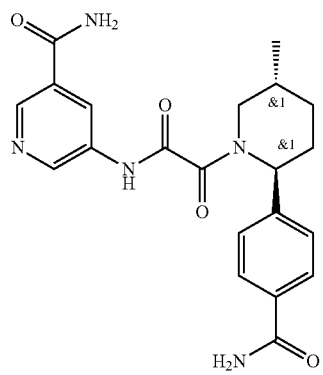

Compound 220

Prepared by general procedure 1. Yield: 16.7 mg, 11.65% $^1$H NMR (DMSO-d$_6$, 500 MHz): δ (ppm) 1.04 (m, 3H), 1.38 (m, 1H), 1.66 (m, 1H), 1.89 (m, 1H), 2.17 (m, 2H), 3.02 (m, 1H), 3.79 (m, 1H), 5.43 (m, 1H), 7.40 (m, 3H), 7.61 (m, 1H), 7.89 (m, 2H), 7.97 (m, 1H), 8.17 (m, 1H), 8.49 (m, 1H), 8.78 (m, 1H), 8.89 (m, 1H), 11.27 (m, 1H).

LCMS(ESI): [M+H]$^+$ m/z: calcd 409.2; found 410.2; Rt=0.944 min.

Example 509. The Synthesis of rac-5-{2-[(2R,5S)-2-(3-methoxyphenyl)-5-methylpiperidin-1-yl]-2-oxoacetamido}pyridine-3-carboxamide (Compound 214

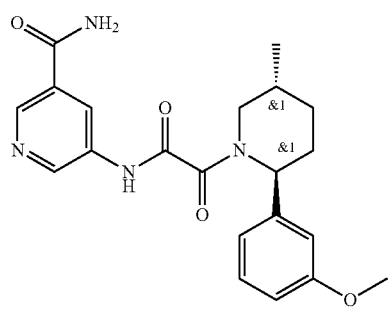

Compound 214

Prepared by general procedure 1. Yield: 19.1 mg, 13.76% $^1$H NMR (DMSO-d$_6$, 500 MHz): δ (ppm) 1.04 (m, 3H), 1.34 (m, 1H), 1.68 (m, 1H), 1.90 (m, 1H), 2.14 (m, 3H), 3.66 (m, 4H), 5.36 (m, 1H), 6.89 (m, 3H), 7.33 (m, 1H), 7.61 (m, 1H), 8.17 (m, 1H), 8.49 (m, 1H), 8.83 (m, 2H), 11.27 (s, 1H). LCMS(ESI): [M+H]$^+$ m/z: calcd 396.2; found 397.2; Rt=1.177 min.

Example 510. The Synthesis of rac-5-{2-[(2R,5S)-2-(3-Fluoro-4-methoxyphenyl)-5-methylpiperidin-1-yl]-2-oxoacetamido}pyridine-3-carboxamide (Compound 208

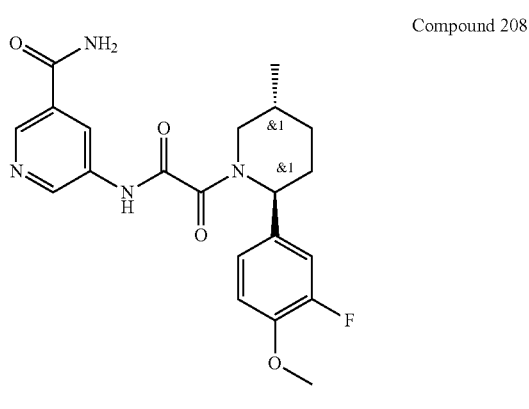 [SMILES: COc1ccc([C@@H]2CC[C@@H](C)CN2C(=O)C(=O)Nc2cncc(C(N)=O)c2)cc1F]

Compound 208

Prepared by general procedure 1. Yield: 24.1 mg, 16.61% $^1$H NMR (DMSO-d$_6$, 500 MHz): δ (ppm) 1.03 (m, 3H), 1.34 (m, 1H), 1.68 (m, 1H), 1.89 (m, 1H), 2.10 (m, 2H), 2.79 (m, 1H), 3.70 (m, 4H), 5.32 (m, 1H), 7.15 (m, 3H), 7.61 (m, 1H), 8.17 (m, 1H), 8.48 (m, 1H), 8.78 (m, 1H), 8.89 (m, 1H), 11.25 (m, 1H). LCMS(ESI): [M+H]$^+$ m/z: calcd 414.2; found 415.2; Rt=1.181 min.

Example 511. The Synthesis of rac-5-{2-[(2R,5S)-2-(3,4-dimethoxyphenyl)-5-methylpiperidin-1-yl]-2-oxoacetamido}pyridine-3-carboxamide (Compound 230

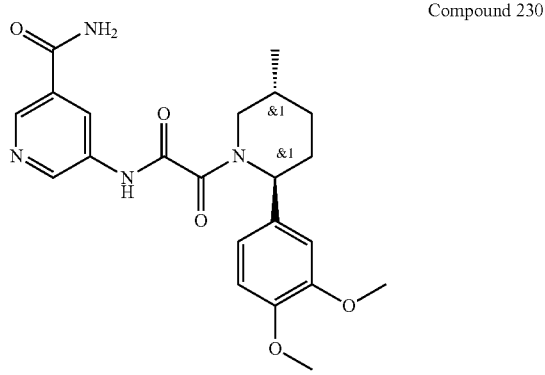 [SMILES: COc1ccc([C@@H]2CC[C@@H](C)CN2C(=O)C(=O)Nc2cncc(C(N)=O)c2)cc1OC]

Compound 230

Prepared by general procedure 1. Yield: 12.4 mg, 8.31% $^1$H NMR (DMSO-d$_6$, 500 MHz): δ (ppm) 1.03 (m, 3H), 1.35 (m, 1H), 1.72 (m, 1H), 1.89 (m, 1H), 2.07 (m, 1H), 2.20 (m, 1H), 2.97 (m, 1H), 3.74 (m, 7H), 5.33 (m, 1H), 6.91 (m, 3H), 7.61 (m, 1H), 8.17 (m, 1H), 8.49 (m, 1H), 8.77 (m, 1H), 8.88 (m, 1H), 11.25 (m, 1H). LCMS(ESI): [M+H]$^+$ m/z: calcd 426.2; found 427.2; Rt=1.142 min.

Example 512. The Synthesis of rac-5-{2-[(2R,5S)-2-(3-chlorophenyl)-5-methylpiperidin-1-yl]-2-oxoacetamido}pyridine-3-carboxamide (Compound 174

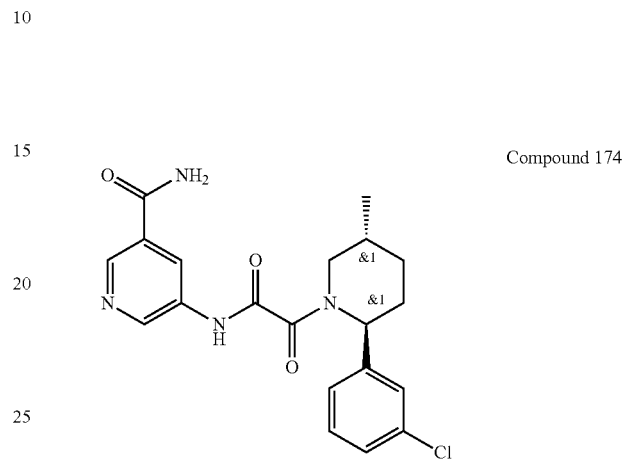

Compound 174

Prepared by general procedure 1. Yield: 5.7 mg, 4.06% $^1$H NMR (DMSO-d$_6$, 400 MHz): δ (ppm) 1.04 (m, 3H), 1.35 (m, 1H), 1.66 (m, 1H), 1.92 (m, 1H), 2.14 (m, 2H), 3.03 (m, 1H), 3.78 (m, 1H), 5.39 (m, 1H), 7.39 (m, 4H), 7.62 (m, 1H), 8.18 (m, 1H), 8.50 (m, 1H), 8.84 (m, 2H), 11.29 (m, 1H). LCMS(ESI): [M+H]$^+$ m/z: calcd 400.2; found 401.2; Rt=1.250 min.

Example 513. The Synthesis of rac-5-{2-[(2R,5S)-2-(3-carbamoylphenyl)-5-methylpiperidin-1-yl]-2-oxoacetamido}pyridine-3-carboxamide (Compound 125

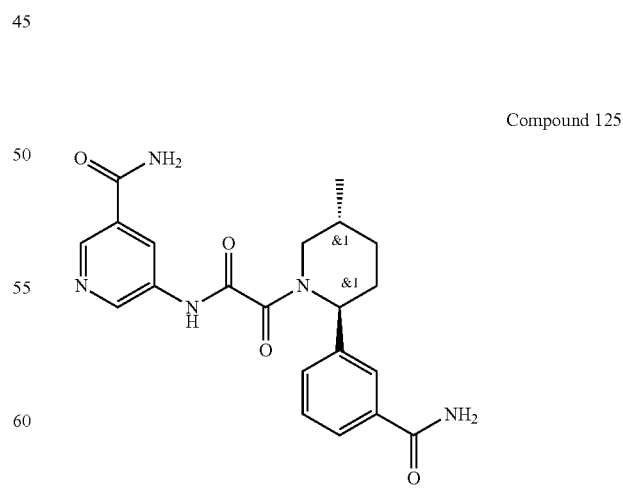

Compound 125

Prepared by general procedure. Yield: 2.9 mg, 2.02% LCMS(ESI): [M+H]$^+$ m/z: calcd 409.2; found 410.4; Rt=2.455 min.

Example 514. The Synthesis of rac-5-{2-[(2R,5S)-5-methyl-2-[4-(Oxan-4-yloxy)phenyl]piperidin-1-yl]-2-oxoacetamido}pyridine-3-carboxamide (Compound 269

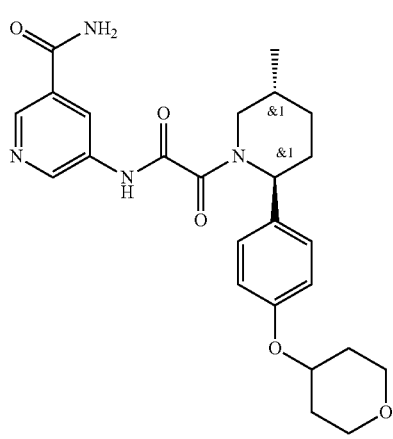

Compound 269

Prepared by general procedure. Yield: 8.1 mg, 4.96% $^1$H NMR (600 MHz, DMSO-d$_6$) δ 0.98-1.03 (m, 3H), 1.27-1.36 (m, 1H), 1.49-1.57 (m, 2H), 1.65-1.73 (m, 1H), 1.79-1.89 (m, 1H), 1.90-1.97 (m, 2H), 1.98-2.12 (m, 1H), 2.14-2.22 (m, 1H), 2.79-3.21 (m, 1H), 3.40-3.49 (m, 3H), 3.80-3.98 (m, 2H), 4.48-4.59 (m, 1H), 5.02-5.60 (m, 1H), 6.92-7.00 (m, 2H), 7.18-7.28 (m, 2H), 7.55-7.66 (m, 1H), 8.10-8.21 (m, 1H), 8.41-8.53 (m, 1H), 8.67-8.80 (m, 1H), 8.81-8.93 (m, 1H), 11.08-11.35 (m, 1H).

LCMS(ESI): [M+H]$^+$ m/z: calcd 466.2; found 467.2; Rt=3.057 min.

Example 515. The Synthesis of rac-5-{2-[(2R,5S)-2-(5-Fluoropyridin-3-yl)-5-methylpiperidin-1-yl]-2-oxoacetamido}pyridine-3-carboxamide (Compound 248

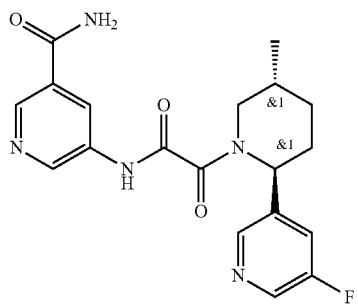

Compound 248

Prepared by general procedure. Yield: 7.3 mg, 5.41% $^1$H NMR (600 MHz, DMSO-d$_6$) δ 0.84-1.09 (m, 3H), 1.28-1.40 (m, 1H), 1.61-1.74 (m, 1H), 1.84-1.97 (m, 1H), 2.01-2.18 (m, 1H), 2.18-2.32 (m, 1H), 2.76-3.26 (m, 1H), 3.46-4.08 (m, 1H), 5.25-5.76 (m, 1H), 7.56-7.64 (m, 1H), 7.64-7.73 (m, 1H), 8.15 (d, 1H), 8.42-8.53 (m, 3H), 8.70-8.80 (m, 1H), 8.82-8.93 (m, 1H), 11.20-11.31 (m, 1H).

LCMS(ESI): [M+H]$^+$ m/z: calcd 385.3; found 386.1; Rt=1.031 min.

Example 516. The Synthesis of rac-5-{2-[(2R,5S)-5-methyl-2-(Quinolin-3-yl)piperidin-1-yl]-2-oxoacetamido}pyridine-3-carboxamide (Compound 257

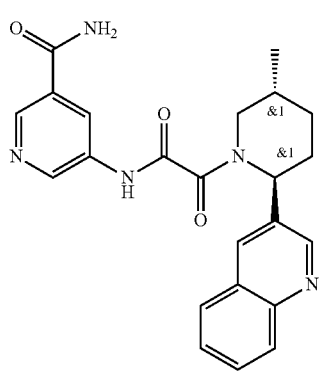

Compound 257

Prepared by general procedure. Yield: 6.6 mg, 4.52% $^1$H NMR (600 MHz, DMSO-d$_6$) δ 0.82-1.13 (m, 3H), 1.31-1.50 (m, 1H), 1.71-1.81 (m, 1H), 1.85-1.99 (m, 1H), 2.06-2.34 (m, 1H), 2.65-3.23 (m, 1H), 3.32-3.38 (m, 1H), 3.56-4.11 (m, 1H), 5.39-5.97 (m, 1H), 7.47-7.64 (m, 2H), 7.69-7.79 (m, 1H), 7.96-8.03 (m, 2H), 8.07-8.19 (m, 1H), 8.26-8.34 (m, 1H), 8.38-8.55 (m, 1H), 8.64-8.79 (m, 1H), 8.79-8.88 (m, 1H), 8.88-8.94 (m, 1H), 11.03-11.68 (m, 1H).

LCMS(ESI): [M+H]$^+$ m/z: calcd 417.2; found 418.0; Rt=1.045 min.

Example 517. The Synthesis of rac-5-{2-[(2R,5S)-2-{Imidazo[1,2-a]pyridin-6-yl}-5-methylpiperidin-1-yl]-2-oxoacetamido}pyridine-3-carboxamide (Compound 234

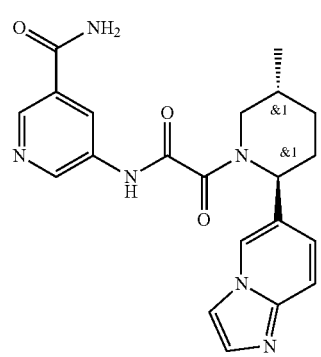

Compound 234

Prepared by general procedure. Yield: 6.7 mg, 4.71% $^1$H NMR (600 MHz, DMSO-d$_6$) δ 0.95-1.15 (m, 3H), 1.30-1.47 (m, 1H), 1.80-2.01 (m, 2H), 2.02-2.24 (m, 2H), 2.83-3.27 (m, 1H), 3.46-4.07 (m, 1H), 5.15-5.76 (m, 1H), 6.86-7.27 (m, 1H), 7.51-7.64 (m, 3H), 7.87-7.96 (m, 1H), 8.08-8.21 (m, 1H), 8.44-8.58 (m, 2H), 8.71-8.79 (m, 1H), 8.81-8.94 (m, 1H), 11.25 (br s, 1H).

LCMS(ESI): [M+H]$^+$ m/z: calcd 406.2; found 407.1; Rt=0.800 min.

Example 518. The Synthesis of rac-5-{2-[(2R,5S)-5-methyl-2-{[1,2,4]triazolo[4,3-a]pyridin-6-yl}piperidin-1-yl]-2-oxoacetamido}pyridine-3-carboxamide (Compound 272

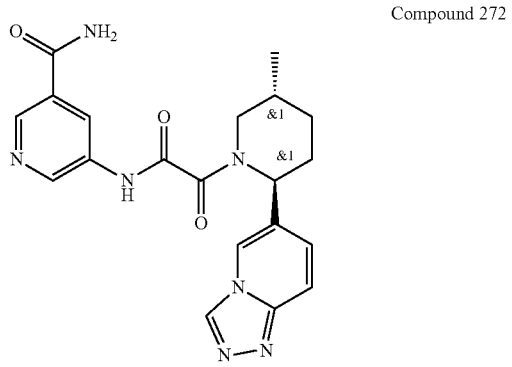 [SMILES: C[C@@H]1CC[C@@H](c2ccc3nncn3c2)N(C(=O)C(=O)Nc2cncc(C(N)=O)c2)C1]

Compound 272

Prepared by general procedure. Yield: 5.2 mg, 3.65% $^1$H NMR (600 MHz, DMSO-$d_6$) δ 0.98-1.07 (m, 3H), 1.31-1.42 (m, 1H), 1.81-1.96 (m, 2H), 2.05-2.20 (m, 2H), 2.74-3.15 (m, 1H), 3.50-4.07 (m, 1H), 5.17-5.64 (m, 1H), 7.23-7.48 (m, 1H), 7.49-7.62 (m, 1H), 7.74-7.86 (m, 1H), 8.06-8.18 (m, 1H), 8.37-8.49 (m, 1H), 8.52-8.59 (m, 1H), 8.64-8.75 (m, 1H), 8.76-8.92 (m, 1H), 9.15-9.23 (m, 1H), 11.24 (br s, 1H).

LCMS(ESI): [M+H]$^+$ m/z: calcd 407.2; found 408.2; Rt=2.016 min.

Example 519. The Synthesis of rac-5-{2-[(2R,5S)-2-(2,3-dihydro-1-Benzofuran-5-yl)-5-methylpiperidin-1-yl]-2-oxoacetamido}pyridine-3-carboxamide (Compound 282

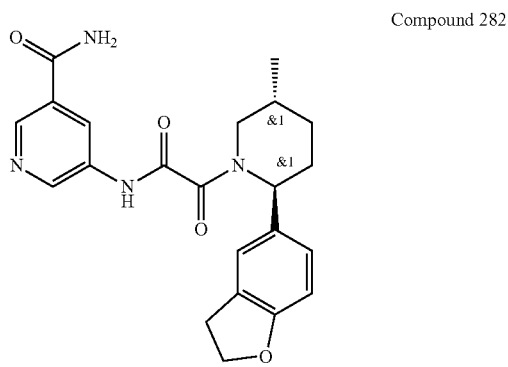 [SMILES: C[C@@H]1CC[C@@H](c2ccc3c(c2)CCO3)N(C(=O)C(=O)Nc2cncc(C(N)=O)c2)C1]

Compound 282

Prepared by general procedure. Yield: 7.3 mg, 5.11% $^1$H NMR (600 MHz, DMSO-$d_6$) δ 0.96-1.06 (m, 3H), 1.25-1.37 (m, 1H), 1.67-1.79 (m, 1H), 1.80-1.94 (m, 1H), 1.98-2.11 (m, 1H), 2.12-2.23 (m, 1H), 2.81-3.11 (m, 1H), 3.13-3.24 (m, 2H), 3.42-3.98 (m, 1H), 4.44-4.53 (m, 2H), 4.96-5.66 (m, 1H), 6.65-6.82 (m, 1H), 6.98-7.08 (m, 1H), 7.13-7.24 (m, 1H), 7.53-7.66 (m, 1H), 8.07-8.23 (m, 1H), 8.41-8.54 (m, 1H), 8.71-8.79 (m, 1H), 8.79-8.96 (m, 1H), 11.05-11.31 (m, 1H).

LCMS(ESI): [M+H]$^+$ m/z: calcd 408.2; found 409.4; Rt=2.925 min.

Example 520. The Synthesis of rac-5-{2-[(2R,5S)-5-methyl-2-{1-methyl-11H-pyrazolo[4,3-b]pyridin-6-yl}piperidin-1-yl]-2-oxoacetamido}pyridine-3-carboxamide (Compound 178)

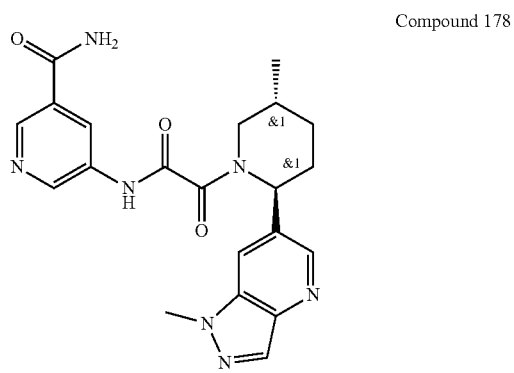 [SMILES: C[C@@H]1CC[C@@H](c2cnc3cnn(C)c3c2)N(C(=O)C(=O)Nc2cncc(C(N)=O)c2)C1]

Compound 178

Prepared by general procedure. Yield: 14.1 mg, 9.56% $^1$H NMR (DMSO-$d_6$, 600 MHz): δ (ppm) 1.04 (m, 3H), 1.37 (m, 1H), 1.78 (m, 1H), 1.91 (m, 1H), 2.18 (m, 1H), 2.33 (m, 1H), 2.95 (m, 1H), 3.46 (m, 1H), 4.07 (m, 3H), 5.57 (m, 1H), 7.58 (m, 1H), 8.16 (m, 3H), 8.48 (m, 2H), 8.80 (m, 2H), 11.24 (m, 1H)

LCMS(ESI): [M+H]$^+$ m/z: calcd 421.2; found 422.0; Rt=1.003 min.

Example 521. The Synthesis of rac-5-{2-[(2R,5S)-5-methyl-2-(8-methylquinolin-3-yl)piperidin-1-yl]-2-oxoacetamido}pyridine-3-carboxamide (Compound 215

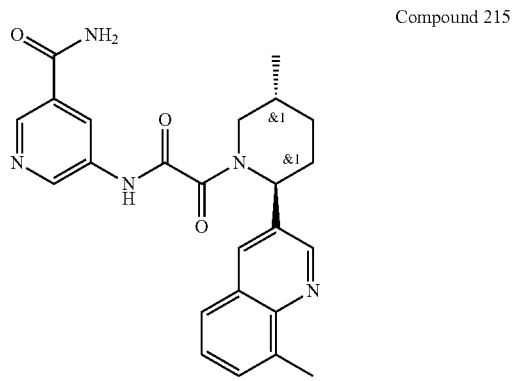 [SMILES: Cc1cccc2cc([C@@H]3CC[C@@H](C)CN3C(=O)C(=O)Nc3cncc(C(N)=O)c3)cnc12]

Compound 215

Prepared by general procedure. Yield: 3.8 mg, 2.52% $^1$H NMR (DMSO-$d_6$, 500 MHz): δ (ppm) 1.07 (m, 3H), 1.42 (m, 1H), 1.79 (m, 1H), 1.94 (m, 1H), 2.22 (m, 1H), 2.38 (m, 2H), 2.72 (m, 3H), 3.82 (m, 1H), 5.64 (m, 1H), 7.51 (m, 1H), 7.61 (m, 2H), 7.83 (m, 1H), 8.24 (m, 2H), 8.49 (m, 1H), 8.77 (m, 1H), 8.90 (m, 2H), 11.29 (m, 1H)

LCMS(ESI): [M+H]$^+$ m/z: calcd 431.2; found 432.2; Rt=1.137 min.

Example 522. The Synthesis of rac-5-{2-[(2R,5S)-5-methyl-2-[5-(1H-pyrazol-1-yl)pyridin-3-yl]piperidin-1-yl]-2-oxoacetamido}pyridine-3-carboxamide (Compound 226

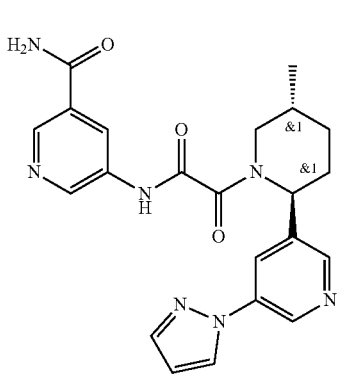

Compound 226

Prepared by general procedure. Yield: 20.5 mg, 13.51%
$^1$H NMR (DMSO-d$_6$, 500 MHz): δ (ppm) 1.06 (m, 3H), 1.38 (m, 1H), 1.72 (m, 1H), 1.96 (m, 1H), 2.22 (m, 2H), 3.40 (m, 1H), 3.75 (m, 1H), 5.53 (m, 1H), 6.62 (m, 1H), 7.61 (m, 1H), 7.83 (m, 1H), 8.17 (m, 2H), 8.50 (m, 2H), 8.64 (m, 1H), 8.78 (m, 1H), 8.88 (m, 1H), 9.03 (m, 1H), 11.29 (m, 1H)
LCMS(ESI): [M+H]$^+$ m/z: calcd 433.2; found 434.2; Rt=1.031 min.

Example 523. The Synthesis of rac-5-{2-[(2R,5S)-5-methyl-2-[2-(trifluoromethyl)pyridin-4-yl]piperidin-1-yl]-2-oxoacetamido}pyridine-3-carboxamide (Compound 221

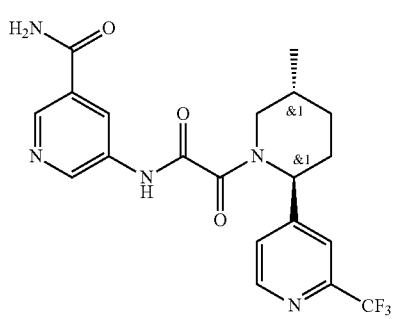

Compound 221

Prepared by general procedure. Yield: 19.2 mg, 12.60%
$^1$H NMR (DMSO-d$_6$, 500 MHz): δ (ppm) 1.04 (m, 3H), 1.36 (m, 1H), 1.58 (m, 1H), 1.92 (m, 1H), 2.23 (m, 2H), 2.80 (m, 1H), 3.83 (m, 1H), 5.49 (m, 1H), 7.65 (m, 2H), 7.79 (m, 1H), 8.17 (d, 1H), 8.49 (m, 1H), 8.81 (m, 3H), 11.33 (s, 1H).
LCMS(ESI): [M+H]$^+$ m/z: calcd 435.2; found 436.2; Rt=1.173 min.

Example 524. The Synthesis of rac-5-{2-[(2R,5S)-2-[4-(3,5-dimethyl-1H-pyrazol-1-yl)phenyl]-5-methylpiperidin-1-yl]-2-oxoacetamido}pyridine-3-carboxamide (Compound 157

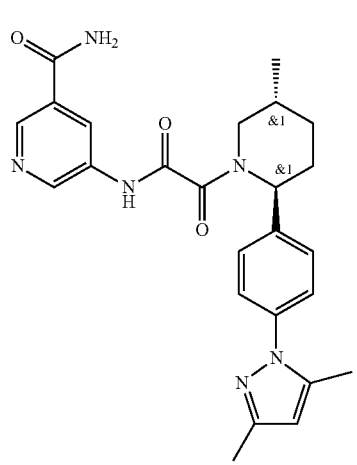

Compound 157

Prepared by general procedure. Yield: 15.5 mg, 9.62% $^1$H NMR (DMSO-d$_6$, 500 MHz): δ (ppm) 1.06 (m, 3H), 1.38 (m, 1H), 1.72 (m, 1H), 2.05 (m, 2H), 2.17 (m, 3H), 2.29 (m, 4H), 2.98 (m, 1H), 3.80 (m, 1H), 5.86 (m, 2H), 7.43 (m, 1H), 7.50 (m, 3H), 7.61 (m, 1H), 8.17 (m, 1H), 8.50 (m, 1H), 8.78 (m, 1H), 8.90 (m, 1H), 11.26 (m, 1H).
LCMS(ESI): [M+H]$^+$ m/z: calcd 460.3; found 461.2; Rt=1.129 min.

Example 525. The Synthesis of rac-5-{2-[(2R,5S)-5-methyl-2-(3,4,5-trifluorophenyl)piperidin-1-yl]-2-oxoacetamido}pyridine-3-carboxamide (Compound 403)

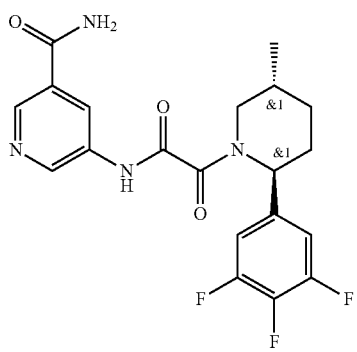

Compound 403

Prepared by general procedure. Yield: 2.2 mg, 1.45% LCMS(ESI): [M+H]$^+$ m/z: calcd 420.2; found 421.2; Rt=1.247 min.

Example 526. The Synthesis of rac-5-{2-[(2R,5S)-2-[4-(1-hydroxycyclobutyl)phenyl]-5-methylpiperidin-1-yl]-2-oxoacetamido}pyridine-3-carboxamide (Compound 259

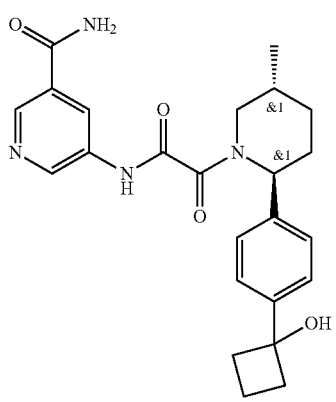

Compound 259

Prepared by general procedure. Yield: 11.3 mg, 7.54% $^1$H NMR (600 MHz, DMSO-$d_6$) δ 0.74-1.07 (m, 3H), 1.28-1.40 (m, 1H), 1.55-1.74 (m, 2H), 1.81-1.94 (m, 2H), 1.97-2.17 (m, 1H), 2.17-2.31 (m, 3H), 2.31-2.37 (m, 2H), 2.77-3.25 (m, 1H), 3.44-4.05 (m, 1H), 5.12-5.68 (m, 2H), 7.24-7.34 (m, 2H), 7.43-7.51 (m, 2H), 7.53-7.65 (m, 1H), 8.08-8.22 (m, 1H), 8.42-8.55 (m, 1H), 8.71-8.80 (m, 1H), 8.81-8.94 (m, 1H), 11.15-11.34 (m, 1H).

LCMS(ESI): [M+3H]$^+$ m/z: calcd 436.2; found 439.2; Rt=1.201 min.

LCMS(ESI): [M+H]$^+$ m/z: calcd 416.2; found 417.4; Rt=3.108 min.

Example 527. The Synthesis of rac-5-{2-[(2R,5S)-2-(3-Cyano-4-methoxyphenyl)-5-methylpiperidin-1-yl]-2-oxoacetamido}pyridine-3-carboxamide (Compound 237

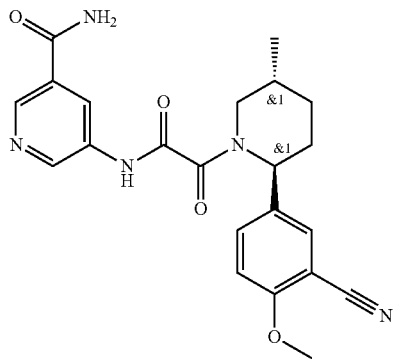

Compound 237

Prepared by general procedure. Yield: 8.5 mg, 5.76% $^1$H NMR (600 MHz, DMSO-$d_6$) δ 0.96-1.07 (m, 3H), 1.25-1.38 (m, 1H), 1.59-1.68 (m, 1H), 1.82-1.93 (m, 1H), 2.00-2.11 (m, 1H), 2.16-2.26 (m, 1H), 2.78-3.23 (m, 1H), 3.44-3.49 (m, 0.6H), 3.86-3.92 (m, 3H), 3.95-4.00 (m, 0.4H), 4.98-5.61 (m, 1H), 7.19-7.31 (m, 1H), 7.56-7.68 (m, 3H), 8.10-8.20 (m, 1H), 8.40-8.52 (m, 1H), 8.70-8.79 (m, 1H), 8.80-8.93 (m, 1H), 11.18-11.34 (m, 1H).

LCMS(ESI): [M+H]$^+$ m/z: calcd 421.2; found 422.2; Rt=2.961 min.

Example 528. The Synthesis of rac-5-{2-[(2R,5S)-2-[5-methoxy-6-(trifluoromethyl)pyridin-3-yl]-5-methylpiperidin-1-yl]-2-oxoacetamido}pyridine-3-carboxamide (Compound 223)

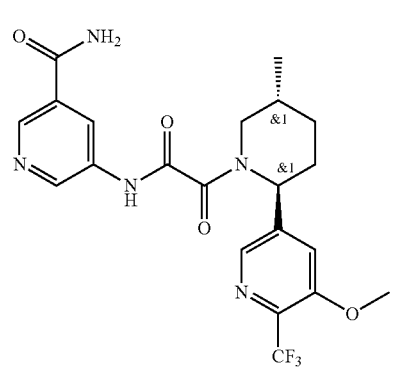

Compound 223

Prepared by general procedure. Yield: 15.4 mg, 9.45% $^1$H NMR (DMSO-$d_6$, 500 MHz): δ (ppm) 1.05 (m, 3H), 1.36 (m, 1H), 1.70 (m, 1H), 1.94 (m, 1H), 2.20 (m, 2H), 3.50 (m, 2H), 3.96 (m, 3H), 5.48 (m, 1H), 7.63 (m, 2H), 8.22 (m, 2H), 8.49 (m, 1H), 8.83 (m, 2H), 11.28 (m, 1H).

LCMS(ESI): [M+H]$^+$ m/z: calcd 465.2; found 466.2; Rt=1.193 min.

Example 529. The Synthesis of rac-rac-5-{2-[(2R, 5S)-2-(4-chloro-3-methoxyphenyl)-5-methylpiperidin-1-yl]-2-oxoacetamido}pyridine-3-carboxamide (Compound 114

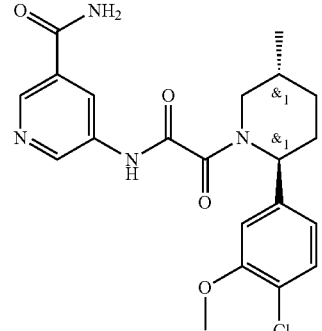

Compound 114

Prepared by general procedure. Yield: 16 mg, 10.7% $^1$H NMR (500 MHz, CDCl$_3$) δ 1.11 (m, 3H), 1.39 (m, 2H), 2.00 (m, 2H), 2.22 (m, 2H), 3.46 (m, 1H), 3.90 (m, 3H), 4.43 (m, 1H), 5.95 (m, 1H), 6.84 (m, 2H), 7.34 (m, 1H), 8.85 (m, 2H), 9.50 (m, 1H).

LCMS(ESI): [M+H]$^+$ m/z: calcd 430.2; found 431.2; Rt=3.356 min.

Example 530. The Synthesis of 2-methoxy-5-[[2-[(2R,5S)-5-methyl-2-[2-(1-methyl-4-piperidyl)-1,3-benzothiazol-5-yl]-1-piperidyl]-2-oxo-acetyl]amino]pyridine-3-carboxamide (Compound 1126

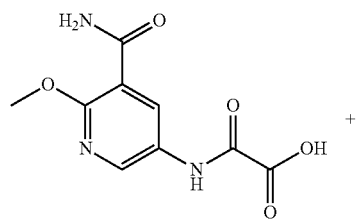
+
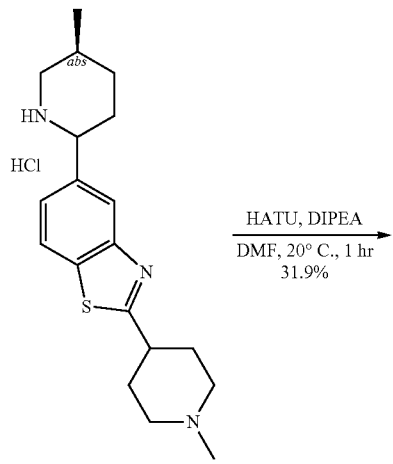

HATU, DIPEA
DMF, 20° C., 1 hr
31.9%

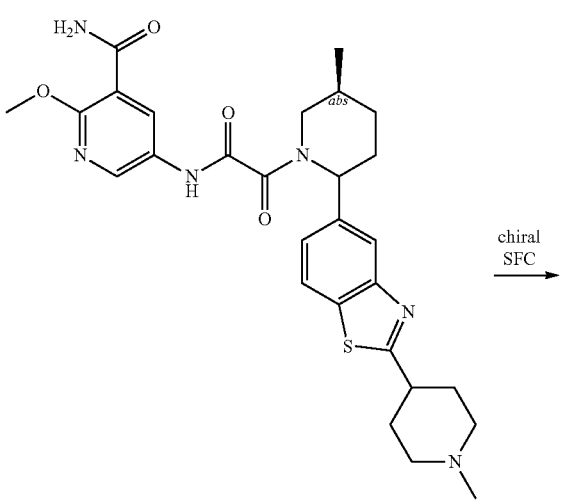

chiral SFC

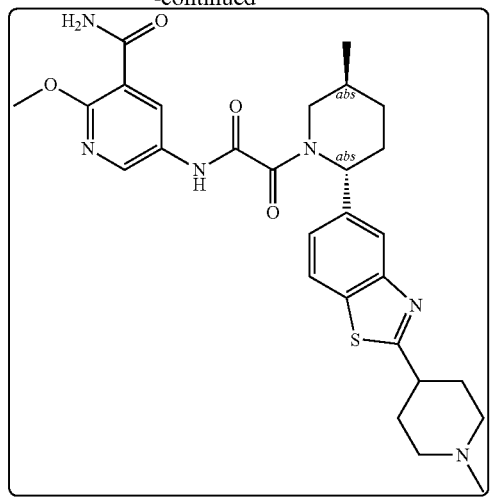

Step 1: Synthesis of 2-methoxy-5-[[2-[(5S)-5-methyl-2-[2-(1-methyl-4-piperidyl)-1,3-benzothiazol-5-yl]-1-piperidyl]-2-oxo-acetyl]amino]pyridine-3-carboxamide To a mixture of 2-[(5-carbamoyl-6-methoxy-3-pyridyl)amino]-2-oxo-acetic acid (489 mg, 2.04 mmol), 2-(1-methyl-4-piperidyl)-5-[(5S)-5-methyl-2-piperidyl]-1,3-benzothiazole (500 mg, 1.37 mmol, HCl) and HATU (856 mg, 2.25 mmol) in DMF (5 mL) was added DIPEA (1.1 mL, 6.32 mmol). The mixture was stirred at 20° C. for 1 hour. The mixture was purified by preparative HPLC purification (Instrument: Gilson GX-281 Liquid Handler, Gilson 322 Pump, Gilson 156 UV Detector; Column: Phenomenex Gemini-NX 80×40 mm×3 m; Mobile phase A: $H_2O$ with 10 mmol $NH_4HCO_3$ (v %); Mobile phase B: MeCN; Gradient: B from 18% to 48% in 9.5 min, hold 100% B for 2.0 min; Flow Rate: 25 mL/min; Column Temperature: 30° C.; Wavelength: 220 nm, 254 nm) to give 2-methoxy-5-[[2-[(5S)-5-methyl-2-[2-(1-methyl-4-piperidyl)-1,3-benzothiazol-5-yl]-1-piperidyl]-2-oxo-acetyl]amino]pyridine-3-carboxamide (240 mg, 31.9% yield) as white dry powder. LCMS (ESI) $[M+H]^+$ m/z: calcd 551.2; found 551.3.

Step 2: Synthesis of 2-methoxy-5-[[2-[(2R,5S)-5-methyl-2-[2-(1-methyl-4-piperidyl)-1,3-benzothiazol-5-yl]-1-piperidyl]-2-oxo-acetyl]amino]pyridine-3-carboxamide (Compound 1126

2-methoxy-5-[[2-[(5S)-5-methyl-2-[2-(1-methyl-4-piperidyl)-1,3-benzothiazol-5-yl]-1-piperidyl]-2-oxo-acetyl]amino]pyridine-3-carboxamide (240 mg, 0.436 mmol) was separated by chiral SFC (Instrument: SFC-80Q; Column: Daicel Chiralpak OD-H 250×30 mm I.D. 5 m; Mobile phase: supercritical $CO_2$/EtOH (0.1% $NH_3$—$H_2O$, v %)=40/60; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1126.

Compound 1126: 2-methoxy-5-[[2-[(2R,5S)-5-methyl-2-[2-(1-methyl-4-piperidyl)-1,3-benzothiazol-5-yl]-1-piperidyl]-2-oxo-acetyl]amino]pyridine-3-carboxamide (160 mg, 66.7% yield, peak 2, retention time=2.600 min, single known enantiomer with trans relative chemistry, white dry powder). $^1$H NMR (400 MHz, methanol-$d_4$) δ ppm 8.35-

8.73 (m, 2H), 7.88-8.01 (m, 2H), 7.39-7.50 (m, 1H), 5.41-5.90 (m, 1H), 3.93-4.19 (m, 4H), 3.77 (d, J=13.8 Hz, 1H), 3.43 (d, J=14.1 Hz, 1H), 2.96-3.27 (m, 4H), 2.13-2.43 (m, 10H), 1.87-2.07 (m, 4H), 1.46 (d, J=12.3 Hz, 1H), 1.14 (d, J=7.0 Hz, 3H); LCMS (ESI) [M+H]⁺ m/z: calcd 551.2, found 551.2; HPLC: 98.13%/@220 nm, 99.22%/@254 nm; 99.7% ee.

Example 531. The Synthesis of 5-[[2-[(2R,5S)-5-methyl-2-[2-(1-methyl-4-piperidyl)-1,3-benzothiazol-5-yl]-1-piperidyl]-2-oxo-acetyl]amino]pyridine-3-carboxamide (Compound 1255

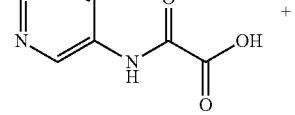

+

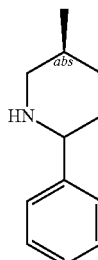

HATU, DIPEA, DMF
20° C., 2 hrs
50.6%
→

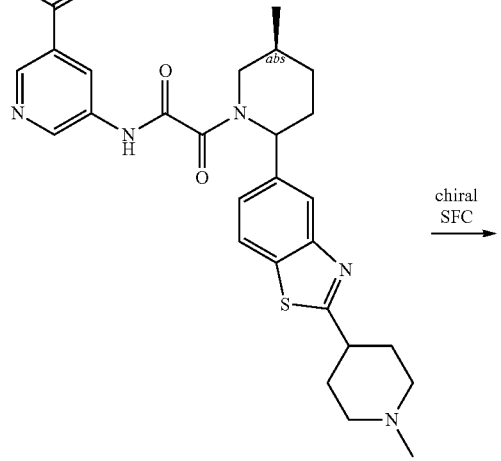

chiral SFC →

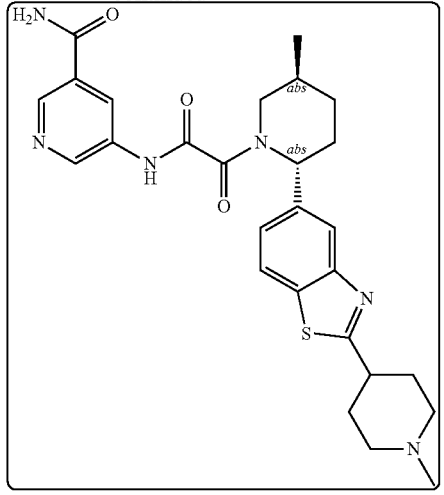

Step 1: Synthesis of 5-[[2-[(5S)-5-methyl-2-[2-(1-methyl-4-piperidyl)-1,3-benzothiazol-5-yl]-1-piperidyl]-2-oxo-acetyl]amino]pyridine-3-carboxamide A mixture of 2-[(5-carbamoyl-3-pyridyl)amino]-2-oxo-acetic acid (50.0 mg, 0.239 mmol), 2-(1-methyl-4-piperidyl)-5-[(5S)-5-methyl-2-piperidyl]-1,3-benzothiazole (50 mg, 0.152 mmol), HATU (70 mg, 0.184 mmol) and DIPEA (0.08 mL, 0.459 mmol) in DMF (3 mL) was stirred at 20° C. for 2 hours. The mixture was concentrated under reduced pressure to give a crude product, which was purified by preparative HPLC (Instrument: Gilson GX-281 Liquid Handler, Gilson 322 Pump, Gilson 156 UV Detector; Column: Phenomenex Gemini-NX 80*40 mm*3 m; Mobile phase A: H₂O with 0.05% NH₃—H₂O+10 mM NH₄HCO₃ (v %); Mobile phase B: MeCN; Gradient: B from 26% to 56% in 9.5 min, hold 100% B for 2 min; Flow Rate: 25 mL/min; Column Temperature: 30° C.; Wavelength: 220 nm, 254 nm) to afford 5-[[2-[(5S)-5-methyl-2-[2-(1-methyl-4-piperidyl)-1,3-benzothiazol-5-yl]-1-piperidyl]-2-oxo-acetyl]amino]pyridine-3-carboxamide (40 mg, 50.6% yield) as a yellow oil. LCMS (ESI) [M+H]⁺ m/z: calcd 521.2, found 521.2.

Step 2: Synthesis of 5-[[2-[(2R,5S)-5-methyl-2-[2-(1-methyl-4-piperidyl)-]1,3-benzothiazol-5-yl]-]-piperidyl]-2-oxo-acetyl]amino]pyridine-3-carboxamide (Compound 1255

5-[[2-[(5S)-5-methyl-2-[2-(1-methyl-4-piperidyl)-1,3-benzothiazol-5-yl]-1-piperidyl]-2-oxo-acetyl]amino]pyridine-3-carboxamide (40 mg, 0.0768 mmol) was purified by SFC (Instrument: Berger, Multigr AM-II; Column: Daicel Chiralcel OD-H 250 mm×30 mm×5 m; Mobile phase: supercritical CO₂/EtOH (0.1% NH₃—H₂O, v %)=50/50; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford 5-[[2-[(2R,5S)-5-methyl-2-[2-(1-methyl-4-piperidyl)-1,3-benzothiazol-5-yl]-1-piperidyl]-2-oxo-acetyl]amino]pyridine-3-carboxamide (21 mg, single known enantiomer with trans relative chemistry, peak 2, retention time: 6.929 min, white solid). ¹H NMR (400 MHz, methanol-d₄) δ ppm 8.32-9.17 (m, 3H), 7.84-8.07 (m, 2H), 7.46 (br s, 1H), 5.44-5.89 (m, 1H), 3.77-4.07 (m, 1H), 3.46 (br d, J=13.4 Hz, 2H), 3.02-3.21 (m, 2H), 2.18-2.43 (m, 9H), 1.98 (br s, 4H), 1.50 (br s, 1H), 1.15 (br d, J=6.6 Hz, 3H); LCMS (ESI) [M+H]+ m/z: calcd 521.2, found 521.3; HPLC: 1000%@220 nm, 1000%@254 nm; 100% ee, 99.5% de.

Example 532. The Synthesis of 2-methoxy-5-(2-((2R,5S)-5-methyl-2-(3-(4-methylpiperazin-1-yl)phenyl)piperidin-1-yl)-2-oxoacetamido)nicotinamide (Compound 1277

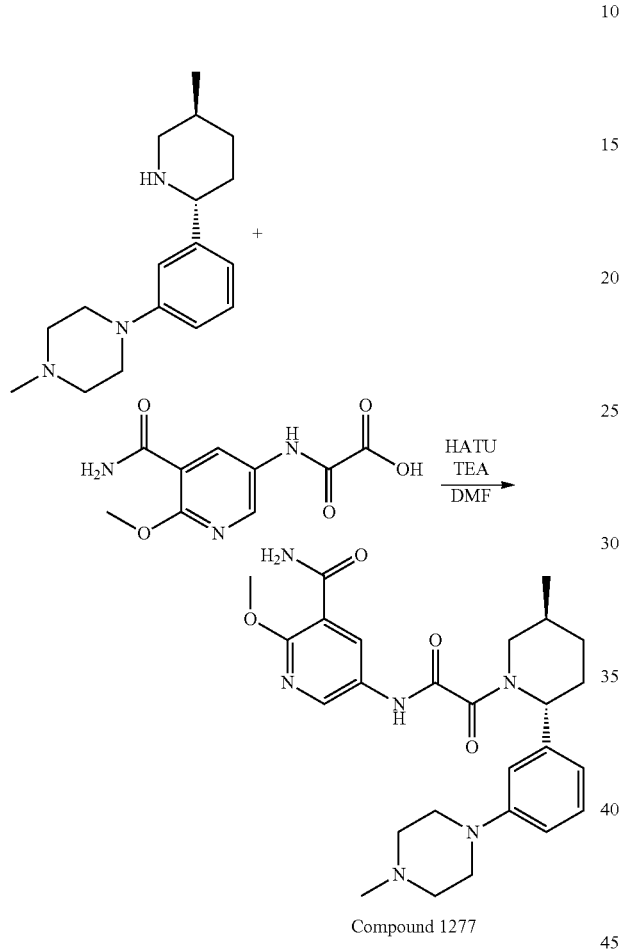

Compound 1277

1-methyl-4-[3-[(2R,5S)-5-methyl-2-piperidyl]phenyl]piperazine (115 mg, 420.61 µmol), 2-[(5-carbamoyl-6-methoxy-3-pyridyl)amino]-2-oxo-acetic acid (100.60 mg, 420.61 µmol) and TEA (425.61 mg, 4.21 mmol, 586.24 µL) were mixed together in DMF (5 mL). HATU (239.89 mg, 630.91 µmol) was added thereto and the resulting mixture was stirred at 20° C. for 16 hr, and then submitted to reverse phase HPLC (2-10 min 50-70% MeOH+NH3 flow 30 mL/min (loading pump 4 mL MeOH), column: sun fire c18) to afford 2-methoxy-5-[[2-oxo-2-[(2R,5S)-5-methyl-2-[3-(4-methylpiperazin-1-yl)phenyl]-1-piperidyl]acetyl]amino]pyridine-3-carboxamide (64 mg, 129.40 µmol, 30.77% yield).

1H NMR (600 MHz, DMSO-d6) δ (ppm) 1.10 (m, 3H), 1.27-1.41 (m, 1H), 1.60-1.77 (m, 1H), 1.82-1.94 (m, 1H), 1.97-2.15 (m, 1H), 2.15-2.27 (m, 4H), 2.40-2.46 (m, 4H), 2.78-2.83 (m, 0.3H), 3.04-3.16 (m, 4H), 3.23-3.27 (m, 0.7H), 3.40-3.49 (m, 0.7H), 3.91-3.99 (m, 3H), 3.99-4.04 (m, 0.3H), 5.08-5.64 (m, 1H), 6.69-6.78 (m, 1H), 6.78-6.86 (m, 2H), 7.16-7.26 (m, 1H), 7.65-7.79 (m, 2H), 8.38-8.49 (m, 1H), 8.49-8.60 (m, 1H), 10.94-11.12 (m, 1H).

LCMS(ESI): [M]+ m/z: calcd 494.2; found 495.2; Rt=2.246 min.

Example 533. The Synthesis of 5-(2-((2R,5S)-2-(3-chloro-4-(2-(dimethylamino)ethyl)phenyl)-5-methylpiperidin-1-yl)-2-oxoacetamido)-2-methoxynicotinamide (Compound 1341

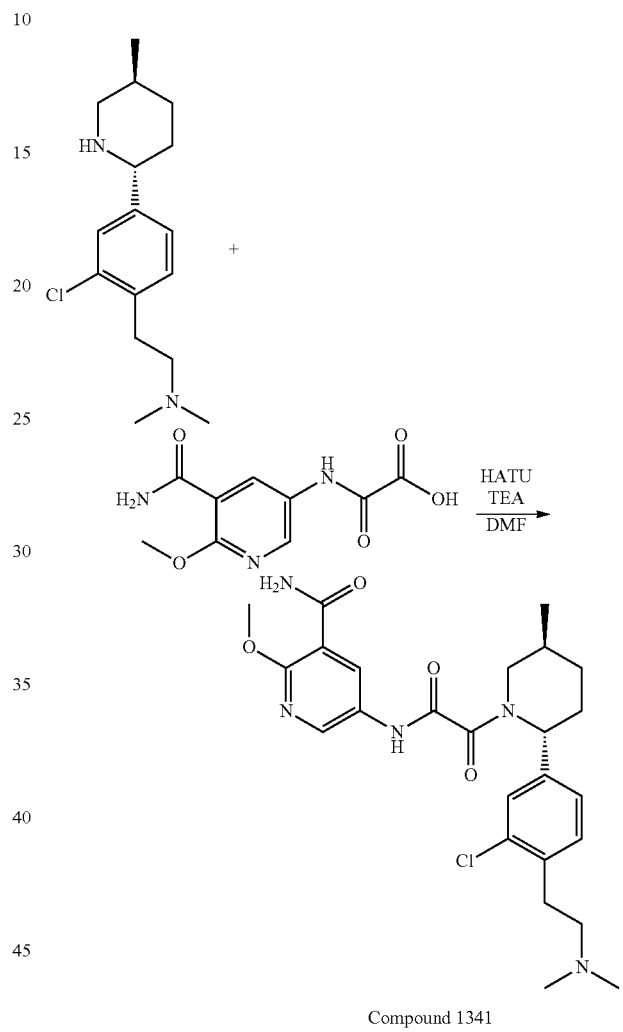

Compound 1341

2-[(5-carbamoyl-6-methoxy-3-pyridyl)amino]-2-oxo-acetic acid (71.54 mg, 299.11 mol) and 2-[2-chloro-4-[rac-(2R,5S)-5-methyl-2-piperidyl]phenyl]-N,N-dimethyl-ethanamine (0.07 g, 249.26 µmol) were mixed in DMF (10 mL). The reaction suspension was cooled to 20° C. and HATU (113.73 mg, 299.11 µmol) followed by TEA (75.67 mg, 747.77 µmol, 104.22 L) were added and stirred at ambient temperature for 13 hr. The reaction mixture was evaporated in vacuum and obtained crude product 0.3 g was purified by preparative 30-90% 0-5 min H2O/MeOH/0.1% NH4OH, flow: 30 mL/min to afford product 2-methoxy-5-[[2-oxo-2-[rac-(2R,5S)-2-[3-chloro-4-[2-(dimethylamino)ethyl]phenyl]-5-methyl-1-piperidyl]acetyl]amino]pyridine-3-carboxamide (0.0179 g, 35.66 µmol, 14.31% yield).

1H NMR (600 MHz, DMSO-d6) δ (ppm) 1.03 (d, 3H), 1.34 (m, 1H), 1.64 (m, 1H), 1.86 (m, 1H), 2.01 (m, 1H), 2.18 (s, 6H), 2.42 (m, 2H), 2.79 (m, 3H), 3.23 (m, 1H), 3.46 (m, 1H), 3.98 (s, 3H), 5.53 (m, 1H), 7.20 (m, 1H), 7.35 (m, 1H), 7.40 (m, 1H), 7.72 (m, 2H), 8.46 (m, 1H), 8.56 (m, 1H), 11.09 (m, 1H).

LCMS(ESI): [M]⁺ m/z: calcd 502.2; found 503.2; Rt=2.589 min.

Example 534. The Synthesis of 5-(2-((2R,5S)-2-(3-(2-(dimethylamino)ethoxy)phenyl)-5-methylpiperidin-1-yl)-2-oxoacetamido)-2-methoxynicotinamide (Compound 1352

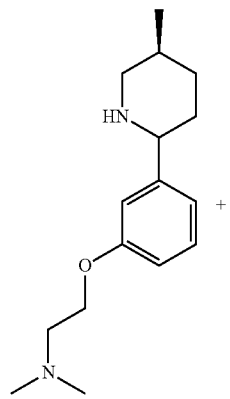

+

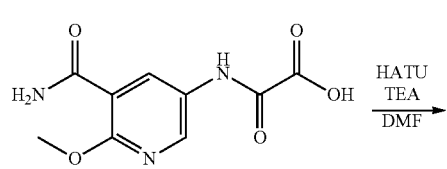

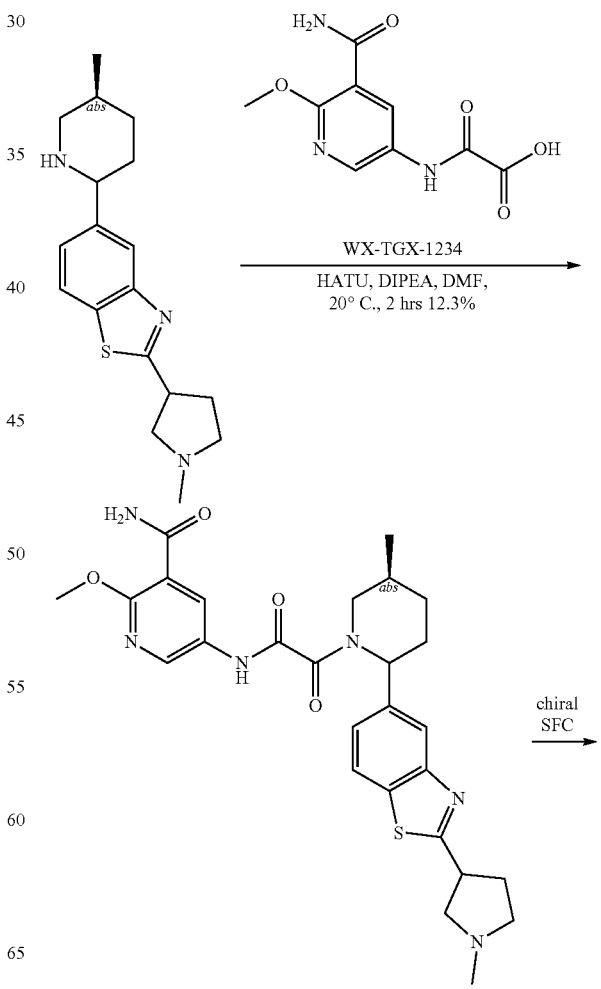

Compound 1352

N,N-dimethyl-2-[3-[(2R,5S)-5-methyl-2-piperidyl]phenoxy]ethanamine (200 mg, 762.23 μmol), 2-[(5-carbamoyl-6-methoxy-3-pyridyl)amino]-2-oxo-acetic acid (182.31 mg, 762.23 μmol) and TEA (385.65 mg, 3.81 mmol, 531.20 μL) were mixed in DMF (2 mL) and HATU (347.79 mg, 914.67 μmol) was added thereto. The resulting mixture was stirred overnight. The reaction mixture was submitted to HPLC and purified (2-10 min 40-65% MeOH+NH₃, 30 mL/min (loading pump 4 mL MeOH+NH₃) column: SunFire 100*19 mm, 5 microM) to obtain 2-methoxy-5-[[2-oxo-2-[(2R,5S)-2-[3-[2-(dimethylamino)ethoxy]phenyl]-5-methyl-1-piperidyl]acetyl]amino]pyridine-3-carboxamide (36.4 mg, 75.28 μmol, 9.88% yield) and 2-methoxy-5-[[2-oxo-2-[(2R,5S)-2-[3-[2-(dimethylamino)ethoxy]phenyl]-5-methyl-1-piperidyl]acetyl]amino]pyridine-3-carboxamide (124.7 mg, 257.88 μmol, 33.83% yield).

¹H NMR (600 MHz, DMSO-d₆) δ (ppm) 0.95-1.08 (m, 3H), 1.27-1.40 (m, 1H), 1.61-1.71 (m, 1H), 1.83-1.94 (m, 1H), 1.98-2.12 (m, 1H), 2.17-2.21 (m, 6H), 2.55-2.62 (m, 3H), 2.77-3.25 (m, 1H), 3.36-3.49 (m, 1H), 3.91-3.98 (m, 3H), 4.00-4.06 (m, 2H), 5.09-5.65 (m, 1H), 6.80-6.94 (m, 3H), 7.24-7.33 (m, 1H), 7.67-7.81 (m, 2H), 8.38-8.48 (m, 1H), 8.48-8.60 (m, 1H), 10.96-11.14 (m, 1H).

LCMS(ESI): [M]⁺ m/z: calcd 483.2; found 484.2; Rt=2.191 min.

Example 535. The Synthesis of 2-methoxy-5-[[2-oxo-2-[rac-(2R,5S)-5-methyl-2-[2-[rac-(3S)-1-methylpyrrolidin-3-yl]-1,3-benzothiazol-5-yl]-1-piperidyl]acetyl]amino]pyridine-3-carboxamide (Compound 1260) and 2-methoxy-5-[[2-oxo-2-[rac-(2R,5S)-5-methyl-2-[2-[rac-(3R)-1-methylpyrrolidin-3-yl]-1,3-benzothiazol-5-yl]-1-piperidyl]acetyl]amino]pyridine-3-carboxamide (Compound 1278

2411

-continued

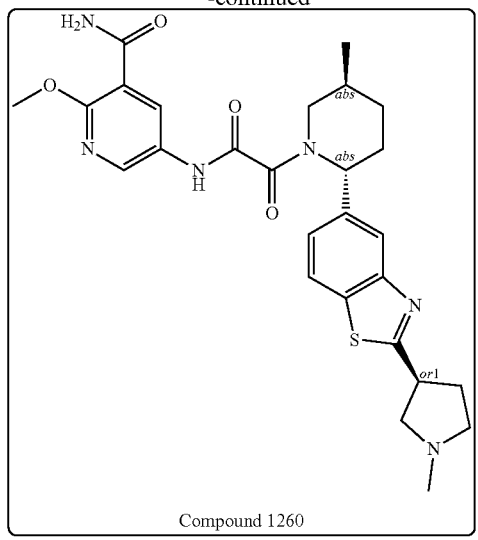

Compound 1260

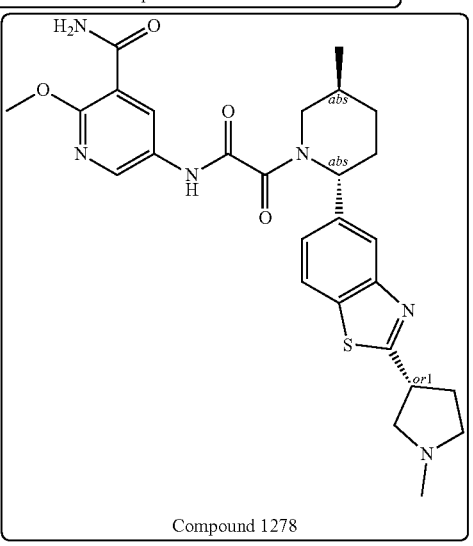

Compound 1278

Step 1: Synthesis of 2-methoxy-5-[[2-oxo-2-[rac-(5S)-5-methyl-2-[2-(1-methylpyrrolidin-3-yl)-1,3-benzothiazol-5-yl]-1-piperidyl]acetyl]amino]pyridine-3-carboxamide

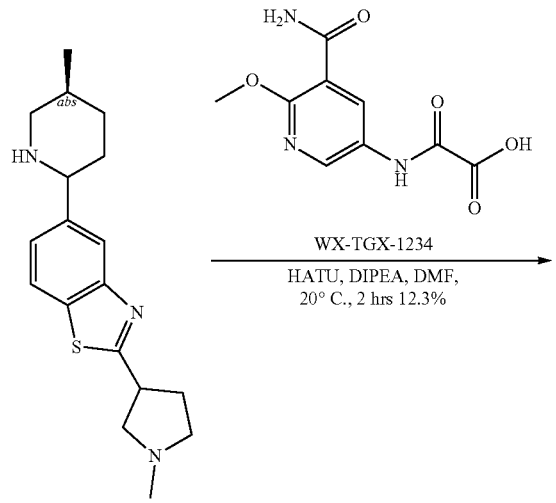

2412

-continued

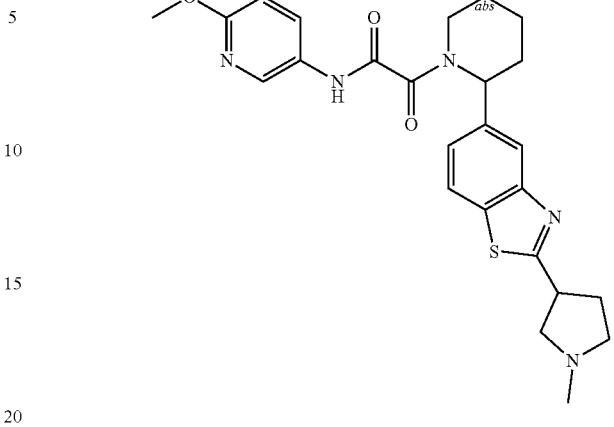

To a mixture of 2-[(5-carbamoyl-6-methoxy-3-pyridyl)amino]-2-oxo-acetic acid (400 mg, 1.67 mmol), 2-(1-methylpyrrolidin-3-yl)-5-[rac-(5S)-5-methyl-2-piperidyl]-1,3-benzothiazole (500 mg, 1.58 mmol) in DMF (6 mL) were added HATU (760 mg, 2.00 mmol) and DIPEA (0.87 mL, 4.99 mmol). The resulting mixture was stirred at 20° C. for 2 hours. The mixture was concentrated under reduced pressure. The residue was purified by preparative HPLC (Instrument: Gilson GX-281 Liquid Handler, Gilson 322 Pump, Gilson 156 UV Detector; Column: Phenomenex Gemini-NX 80*40 mm*3 μm; Mobile phase A: $H_2O$ with 10 mmol $NH_4HCO_3$ (v %); Mobile phase B: MeCN; Gradient: B from 28% to 58% in 9.5 min, hold 100% B for 2 min; Flow Rate: 25 mL/min; Column Temperature: 30° C.; Wavelength: 220 nm, 254 nm) to afford 2-methoxy-5-[[2-oxo-2-[rac-(5S)-5-methyl-2-[2-(1-methylpyrrolidin-3-yl)-1,3-benzothiazol-5-yl]-1-piperidyl]acetyl]amino]pyridine-3-carboxamide (110 mg, 12.3% yield) as yellow solid. HPLC: 89.17%@220 nm, 93.200%@254 nm.

Step 2: Synthesis of 2-methoxy-5-[[2-oxo-2-[rac-(2R,5S)-5-methyl-2-[2-[rac-(3S)-1-methylpyrrolidin-3-yl]-1,3-benzothiazol-5-yl]-1-piperidyl]acetyl]amino]pyridine-3-carboxamide (Compound 1260) and 2-methoxy-5-[[2-oxo-2-[rac-(2R,5S)-5-methyl-2-[2-[rac-(3R)-1-methylpyrrolidin-3-yl]-1,3-benzothiazol-5-yl]-1-piperidyl]acetyl]amino]pyridine-3-carboxamide (Compound 1278

2-methoxy-5-[[2-oxo-2-[rac-(5S)-5-methyl-2-[2-(1-methylpyrrolidin-3-yl)-1,3-benzothiazol-5-yl]-1-piperidyl]acetyl]amino]pyridine-3-carboxamide (110 mg, 0.205 mmol) was purified by SFC (Instrument: Berger, multigr AM-II; Column: Daicel chiralpak IC 250 mm×30 mm×5 m; Mobile phase: supercritical $CO_2$/MeOH-MeCN (0.1% $NH_3$—$H_2O$, v %)=50/50; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm). The fraction was concentrated under reduced pressure and then lyophilized for overnight to give Compound 1260 and Compound 1278.

Compound 1260: 2-methoxy-5-[[2-oxo-2-[rac-(2R,5S)-5-methyl-2-[2-[rac-(3S)-1-methylpyrrolidin-3-yl]-1,3-benzothiazol-5-yl]-1-piperidyl]acetyl]amino]pyridine-3-carboxamide (30.5 mg, single unknown enantiomer, Peak 1, Retention time: 3.854 min, white solid). $^1$H NMR (400 MHz, methanol-$d_4$) δ ppm 8.57-8.72 (m, 1H), 8.34-8.54 (m, 1H), 7.87-8.00 (m, 2H), 7.42 (br d, J=7.9 Hz, 1H), 5.41-5.87 (m, 1H), 4.00-4.16 (m, 3H), 3.91 (br s, 1H), 3.76 (br d, J=13.6 Hz, 1H), 3.43 (br d, J=12.9 Hz, 1H), 3.15 (br s, 1H), 2.74-2.94 (m, 3H), 2.43 (s, 4H), 2.19-2.38 (m, 3H), 1.94 (br s, 2H), 1.46 (br d, J=11.9 Hz, 1H), 1.14 (br d, J=6.6 Hz, 3H); LCMS (ESI) [M+H]$^+$ m/z: calcd 537.2, found 537.2; HPLC: 99.360%@220 nm, 1000%@254 nm; 98.6% ee.

Compound 1278: 2-methoxy-5-[[2-oxo-2-[rac-(2R,5S)-5-methyl-2-[2-[rac-(3R)-1-methylpyrrolidin-3-yl]-1,3-benzothiazol-5-yl]-1-piperidyl]acetyl]amino]pyridine-3-carboxamide (31.5 mg, single unknown enantiomer, Peak 2, Retention time: 7.108 min, white solid). $^1$H NMR (400 MHz, methanol-$d_4$) δ ppm 8.58-8.75 (m, 1H), 8.33-8.54 (m, 1H), 7.80-8.08 (m, 2H), 7.34-7.52 (m, 1H), 5.37-5.93 (m, 1H), 3.99-4.17 (m, 3H), 3.90 (br s, 1H), 3.76 (br d, J=14.3 Hz, 1H), 3.43 (br d, J=14.1 Hz, 1H), 3.10-3.24 (m, 1H), 2.73-2.95 (m, 3H), 2.43 (s, 4H), 2.17-2.38 (m, 3H), 1.94 (br s, 2H), 1.46 (br d, J=12.8 Hz, 1H), 1.14 (br d, J=6.3 Hz, 3H); LCMS (ESI) [M+H]$^+$ m/z: calcd 537.2, found 537.2; HPLC: 98.900%@220 nm, 1000%@254 nm; 98.7% ee.

Scheme E Synthesis of compounds of Formula 5

Compounds of Formula 5 are compounds of Formula (I) wherein $R^1$, $R^2$, $R^3$, $R^{4'}$ $R^6$, $R^7$, and $R^8$ are as described herein General Procedure 5

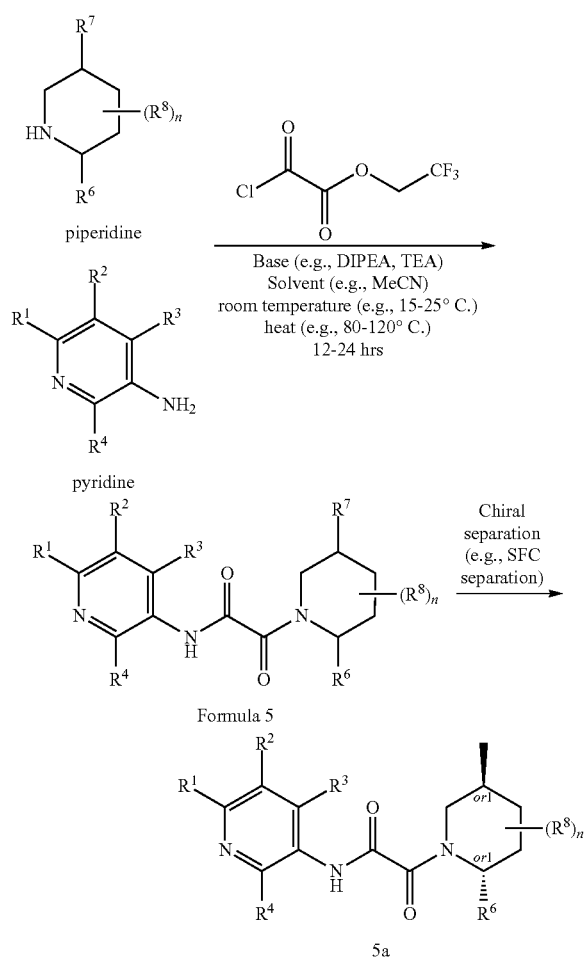

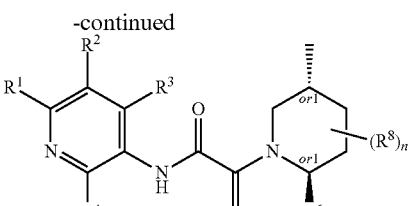

5b

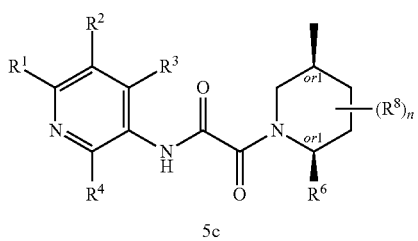

5c

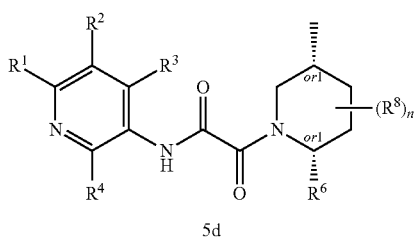

5d

Note that the separation step is optional and used in certain cases to separate the cis/trans diastereomers, and in certain cases to separate distinct enantiomers, as described in the detailed procedures. In certain instances, the starting piperidine is in a defined cis or trans configuration—in those instances, the chiral separation step results only in two of the four enantiomers depicted General Library Procedure DIPEA (1.5 equiv+1.0 equiv if salt forms of reactants were used) was added to the solution of pyridine reactant (1.0 equiv) in MeCN (0.7 mL). The resulting mixture was stirred for 30 min at room temperature followed by the dropwise addition of 2,2,2-trifluoroethyl 2-chloro-2-oxoacetate (1.0 equiv). Then, the mixture was stirred for additional 30 min and the piperidine reactant (1.1 equiv) was added. The reaction mixture was stirred for 1 h at room temperature and then for 16 h at 100° C. After that, the resulting mixture was allowed to cool to room temperature and MeOH (2.0 mL) was added. The suspension was stirred until the clear solution was observed and SiliaMetS DMT (Dimercaptotriazine) (50.0 mg) was added. The obtained suspension was stirred for 30 min at room temperature and filtered off. The filtrate was concentrated under reduced pressure and the residue was re-dissolved in DMSO (0.5 mL). The resulting solution was subjected to HPLC (Agilent 1260 Infinity systems equipped with DAD and mass-detector; Waters SunFire C18 OBD Prep Column, 100 A, 5 mkm, 19*100 mm with SunFire C18 Prep Guard Cartridge, 100 A, 10 mkm, 19*100 mm; MeOH—H$_2$O as a mobile phase, Run Time 5 min) to afford a product of formula 5.

Example 536. 2-[(2S,5R)-5-methyl-2-phenyl-1-piperidyl]-N-(5-methyl-3-pyridyl)-2-oxo-acetamide (Compound 2), 2-(5-methyl-2-phenyl-1-piperidyl)-N-(5-methyl-3-pyridyl)-2-oxo-acetamide (Compound 3), 2-[(2S,5S)-5-methyl-2-phenyl-1-piperidyl]-N-(5-methyl-3-pyridyl)-2-oxo-acetamide (Compound 5

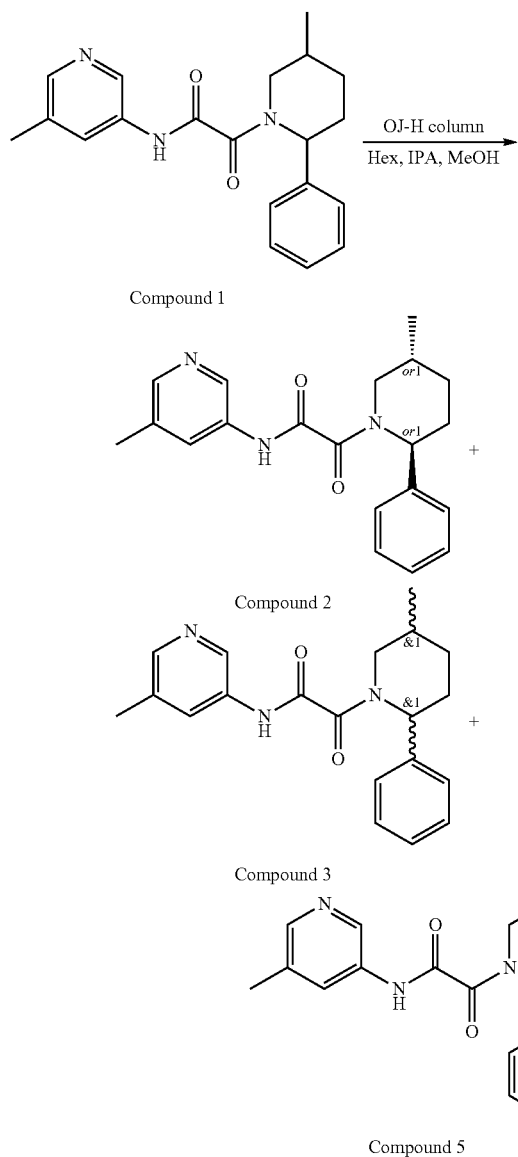

2-(5-methyl-2-phenylpiperidin-1-yl)-N-(5-methylpyridin-3-yl)-2-oxoacetamide (Compound 1) was prepared by the general library procedure. Yield: 11.3 mg (11.3%).

$^1$H NMR (500 MHz, DMSO-d$_6$) δ 1.11 (m, 3H), 1.42 (m, 1H), 1.80 (m, 1H), 1.91 (m, 1H), 2.14 (m, 1H), 2.25 (m, 1H), 2.33 (m, 3H), 2.81 (m, 0.4H), 3.28 (m, 0.6H), 4.11 (m, 1H), 5.48 (m, 1H), 7.24 (m, 1H), 7.34 (m, 4H), 7.95 (m, 1H), 8.07 (m, 1H), 8.56 (m, 1H), 10.88 (m, 1H).

LCMS(ESI): [M+H]$^+$ m/z: calcd 337.2; found 338.2; Rt=3.157 min.

Chiral Separation Conditions: Instrument: Preparative Agilent HPLC 1200 (DAD); Reverse Phase & Gradient: Hexane-IPA-MeOH, 70-15-15, 12 mL/min Column: CHIRALPAK OJ-H, 250*20 mm, 5 μm; Injection Volume: 600 mL Three products were observed: 2-[(2S,5R)-5-methyl-2-phenyl-1-piperidyl]-N-(5-methyl-3-pyridyl)-2-oxo-acetamide (6.35 mg, 18.82 μmol, 12.12% yield) (Compound 2; beige solid), 2-(5-methyl-2-phenyl-1-piperidyl)-N-(5-methyl-3-pyridyl)-2-oxo-acetamide (3.54 mg, 10.49 μmol, 6.76% yield) (grey solid), 2-[(2S,5S)-5-methyl-2-phenyl-1-piperidyl]-N-(5-methyl-3-pyridyl)-2-oxo-acetamide (10.16 mg, 30.11 μmol, 19.39% yield) (beige solid).

2-(5-methyl-2-phenyl-1-piperidyl)-N-(5-methyl-3-pyridyl)-2-oxo-acetamide Compound 3 (was obtained as mixture of diastereomers):

$^1$H NMR (500 MHz, CDCl$_3$) δ 0.87 (m, 3H), 1.30 (m, 1H), 1.79 (m, 2H), 2.04 (m, 1H), 2.36 (m, 3H), 2.53 (m, 1H), 2.66 (m, 1H), 4.64 (m, 1H), 6.23 (m, 1H), 7.30 (m, 3H), 7.40 (m, 2H), 8.06 (m, 1H), 8.26 (m, 1H), 8.51 (m, 1H), 9.27 (m, 1H).

LCMS(ESI): [M+2H]$^+$ m/z: calcd 337.18; found 339.03; Rt=4.808 min.

RT (OJ-H, Hexane-IPA-MeOH, 70-15-15, 0.6 mL/min)=10.295 min.

2-[(2S,5S)-5-methyl-2-phenyl-1-piperidyl]-N-(5-methyl-3-pyridyl)-2-oxo-acetamide Compound 5 (10.16 mg, 30.11 μmol, 19.39% yield):

$^1$H NMR (500 MHz, CDCl$_3$) δ 0.99 (m, 3H), 1.35 (m, 1H), 1.80 (m, 1H), 2.01 (m, 1H), 2.24 (m, 1H), 2.37 (m, 3H), 2.61 (m, 1H), 3.21 (m, 1H), 4.53 (m, 1H), 6.20 (m, 1H), 7.30 (m, 3H), 7.39 (m, 2H), 8.06 (m, 1H), 8.25 (m, 1H), 8.50 (m, 1H), 9.29 (m, 1H).

LCMS(ESI): [M+2H]$^+$ m/z: calcd 337.18; found 339.03; Rt=4.743 min.

RT (OJ-H, Hexane-IPA-MeOH, 70-15-15, 0.6 mL/min)=28.230 min.

2-[(2S,5R)-5-methyl-2-phenyl-1-piperidyl]-N-(5-methyl-3-pyridyl)-2-oxo-acetamide Compound 2:

$^1$H NMR (500 MHz, CDCl$_3$) δ 1.12 (d, 3H), 1.42 (m, 1H), 1.95 (m, 2H), 2.27 (m, 2H), 2.36 (m, 3H), 3.21 (m, 1H), 4.56 (m, 1H), 6.16 (m, 1H), 7.30 (m, 3H), 7.39 (m, 2H), 8.04 (m, 1H), 8.25 (m, 1H), 8.50 (m, 1H), 9.33 (m, 1H).

LCMS(ESI): [M+2H]$^+$ m/z: calcd 337.18; found 339.03; Rt=4.740 min.

RT (OJ-H, Hexane-IPA-MeOH, 70

Example 537. Chiral Separation of N-(5-methyl-3-pyridyl)-2-[(2R)-2-(m-tolyl)-1-piperidyl]-2-oxo-acetamide and N-(5-methyl-3-pyridyl)-2-[(2S)-2-(m-tolyl)-1-piperidyl]-2-oxo-acetamide (Compound 4 and Compound 6

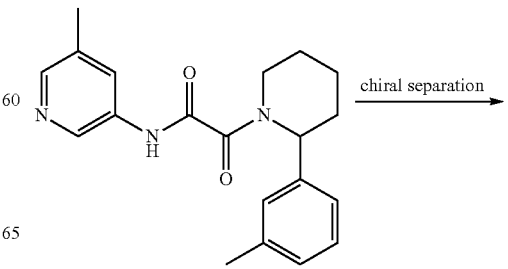

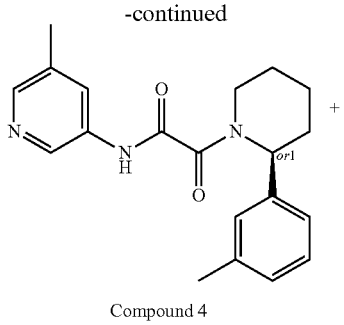

Compound 4

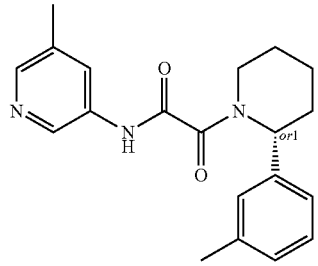

Compound 6

N-(5-methyl-3-pyridyl)-2-[2-(m-tolyl)-1-piperidyl]-2-oxo-acetamide (34.6 mg, 102.54 μmol) (prepared through the general procedure) was subjected to chiral chromatography (Column: Chiralpak OJ-H 250×30 mm, 5 um; Mobile phase: CO₂-MeOH, 60-40; flow Rate: 80 mL/min; Column Temperature: 40° C.; Wavelength: 225 nm) to obtain N-(5-methyl-3-pyridyl)-2-[(2R)-2-(m-tolyl)-1-piperidyl]-2-oxo-acetamide (12.42 mg, Compound 4) and N-(5-methyl-3-pyridyl)-2-[(2S)-2-(m-tolyl)-1-piperidyl]-2-oxo-acetamide Compound 6.

N-(5-methyl-3-pyridyl)-2-[(2R)-2-(m-tolyl)-1-piperidyl]-2-oxo-acetamide (Compound 4)

¹H NMR (DMSO+CCl₄, 500 MHz): δ (ppm) 1.60 (m, 2H), 1.68 (m, 2H), 1.94 (m, 1H), 2.35 (m, 6H), 2.45 (m, 1H), 3.05 (m, 1H), 4.07 (m, 1H), 5.46 (m, 1H), 7.04 (m, 1H), 7.10 (m, 2H), 7.24 (m, 1H), 7.98 (m, 1H), 8.08 (m, 1H), 8.55 (m, 1H), 10.91 (m, 1H).

LCMS(ESI): [M+H]⁺ m/z: calcd 337.2; found 338.0; Rt=4.543 min.

Chiral HPLC: Rt=3.864 min (Column: CHIRALPAK OJ-H, 150×4.6 mm, 5 μm; Mobile phase: CO₂-MeOH, 60-40; Flow Rate: 2.0 mL/min).

N-(5-methyl-3-pyridyl)-2-[(2S)-2-(m-tolyl)-1-piperidyl]-2-oxo-acetamide (Compound 6

¹H NMR (DMSO+CCl₄, 500 MHz) δ (ppm) 1.58 (m, 2H), 1.68 (m, 2H), 1.97 (m, 1H), 2.35 (m, 6H), 2.46 (m, 1H), 3.04 (m, 1H), 4.07 (m, 1H), 5.46 (m, 1H), 7.04 (m, 1H), 7.10 (m, 2H), 7.24 (m, 1H), 8.00 (m, 1H), 8.08 (m, 1H), 8.55 (m, 1H), 10.91 (m, 1H).

LCMS(ESI): [M+H]⁺ m/z: calcd 337.2; found 338.0; Rt=4.542 min.

Chiral HPLC: Rt=5.894 min (Column: CHIRALPAK OJ-H, 150×4.6 mm, 5 μm; Mobile phase: CO₂-MeOH, 60-40; Flow Rate: 2.0 mL/min)

Scheme F—Synthesis of Compounds of Formula 6

Compounds of Formula 6 are are compounds of Formula (I) wherein R¹, R², R³, R⁴, R⁶, R⁷, and R⁸ are as described herein.

General Procedure 6

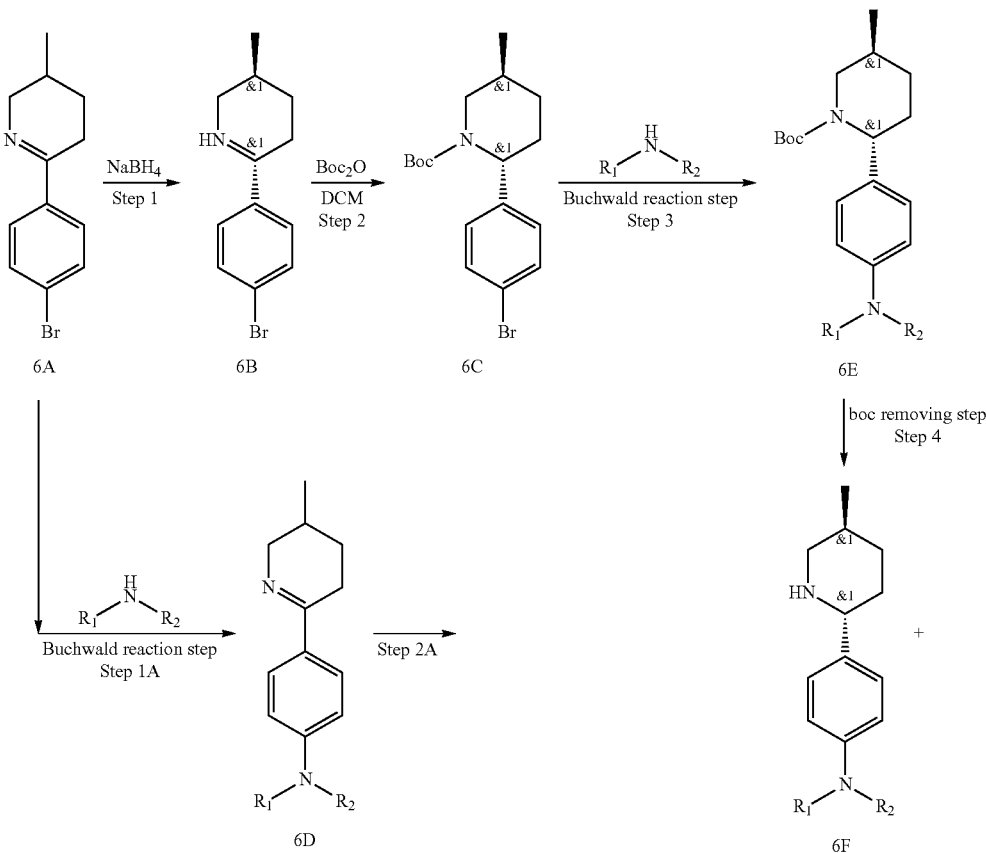

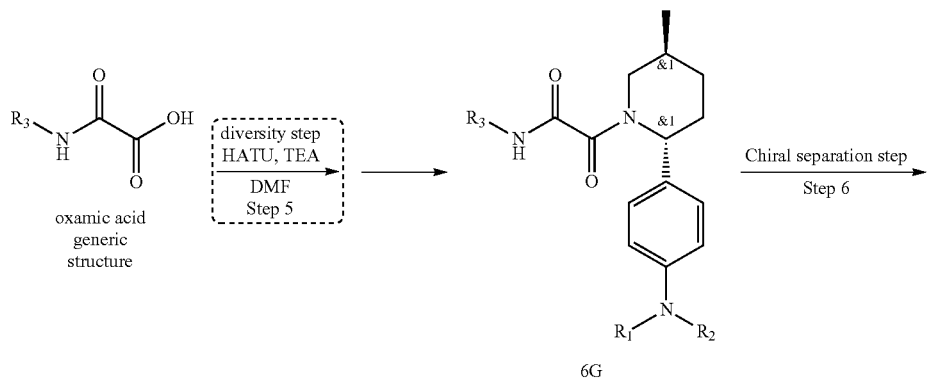

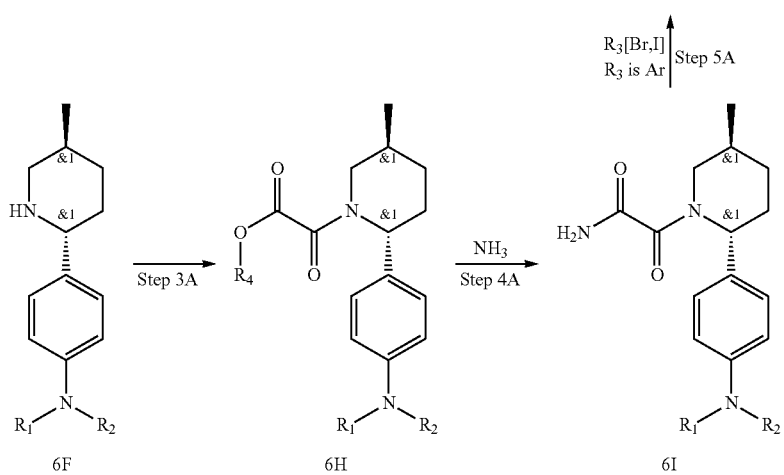

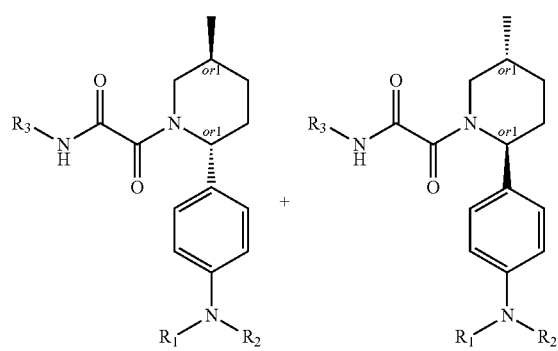

Step 1: The Synthesis of 6B

To a solution of 6A (1.0 equiv), Sodium Borohydride (1.0 equiv) was added portionwise at 0° C. The resulting mixture was stirred for 2 hr at room temperature and the volatiles were removed in vacuo. The residue was diluted with water (2 mL) and extracted with DCM (3*4 mL). Organic layer was dried over $Na_2SO_4$ and solvent was removed in vacuo to obtain 6B.

Step 1A: The Synthesis of 3.1D

To a stirred solution of 6A (1.0 equiv) in Solvent (5 mL) was added Base (2.5 equiv). The resulting suspension was degassed with argon. Ligand (0.05 equiv) and Pd cat (0.05 eqiv) was added. The reaction mixture was stirred at 70 . . . 100° C. for 14 . . . 36 hr. After the completion of the reaction (monitored by LCMS), the resulting mixture was allowed to cool to the room temperature, filtered through a thin layer of $SiO_2$ and washed with solvent (2 mL). The volatiles were removed in vacuo and the residue was subjected for purification to afford 6D.

Buchwald Reaction Step:

| Method: | Pd cat | Base | Ligand | Inert atm | Solvent | Temperature | Time |
|---|---|---|---|---|---|---|---|
| A | $Pd_2(dba)_3$ | $Cs_2CO_3$ | XanthPhos | Ar | dioxane | 100° C. | 18 h |
| B | $Pd_2(dba)_3$ | K t-butoxide | CyJohnPhos | Ar | toluene | 100° C. | 16 h |
| C | $Pd(OAc)_2$ | $Cs_2CO_3$ | XanthPhos | Ar | dioxane | 100° C. | 15-36 h |

Step 2: The Synthesis of 6C 6B (1.0 equiv) was dissolved in DCM (5 mL) and the solution of Di-tert-butyl dicarbonate (1.02 equiv) in DCM (2 mL) was added dropwise (vigorous gas evolution!). The resulting mixture was stirred at 25° C. for 4 hr. Then, volatiles were removed under reduced pressure to afford Compounds and Methods of Use

Step 2A: The Synthesis of 6F

To a solution of 6D (1.0 equiv), Sodium Borohydride (1.0 equiv) was added portionwise at 0° C. The resulting mixture was stirred for 2 hr at room temperature and the volatiles were removed in vacuo. The residue was diluted with water (2 mL) and extracted with DCM (3*4 mL). Organic layer was dried over $Na_2SO_4$ and solvent was removed in vacuo to obtain 6F.

Step 3: The Synthesis of 6E

To a stirred solution of 6C (1.0 equiv) in Solvent (5 mL) was added Base (2.5 equiv). The resulting suspension was degassed with argon. Ligand (0.05 equiv) and Pd cat (0.05 eqiv) was added. The reaction mixture was stirred at 70 . . . 100° C. for 14 . . . 36 hr. After the completion of the reaction (monitored by LCMS), the resulting mixture was allowed to cool to the room temperature, filtered through a thin layer of $SiO_2$ and washed with solvent (2 mL). The volatiles were removed in vacuo and the residue was subjected for purification to afford 6E.

Buchwald Reaction Step:

| Method: | Pd cat | Base | Ligand | Inert atm | Solvent | Temperature | Time |
|---|---|---|---|---|---|---|---|
| A | $Pd_2(dba)_3$ | $Cs_2CO_3$ | XanthPhos | Ar | dioxane | 100° C. | 16-24 h |
| B | Pd G4 RuPhos | LiHMDS | RuPhos | Ar | THF | 70° C. | 18 h |
| C | $Pd(OAc)_2$ | $Cs_2CO_3$ | XanthPhos | Ar | dioxane | 100° C. | 15-36 h |
| D | Pd G4 RuPhos | $Cs_2CO_3$ | RuPhos | Ar | dioxane | 100° C. | 16 h |
| E | $Pd(OAc)_2$ | $Cs_2CO_3$ | RuPhos | Ar | dioxane | 100° C. | 15 h |
| F | $Pd_2(dba)_3$ | Na t-butoxide | CyJohnPhos | Ar | toluene | 80° C. | 16 h |

Step 3A: The Synthesis of 6H

A solution benzyl 2-chloro-2-oxo-acetate (1.1 equiv) in MeCN (2 mL) was added dropwise at 0° C. to a stirred solution of 6F (1.0 equiv) and DIPEA (2.5 equiv) in MeCN (4 mL). The reaction mixture was allowed to warm to 25° C. and stirred for 12 hr. Then, the volatiles were evaporated in vacuo. The residue was subjected to HPLC purification to afford 6I.

Step 4: The Synthesis 6F 6E (1.0 equiv) was dissolved in Solvent (2 . . . 10 mL) and Acid (50.0 equiv) was added. The reaction mixture was stirred at room temperature for 1 . . . 4 h. The solvent was removed in vacuo to obtain 6F.

Boc-Removing Step:

| Method | Acid | Solvent | Temperature | Time |
|---|---|---|---|---|
| A | HCl (4.0M soln in diox) | MeOH | RT | 30 min . . . 12 h |
| B | TFA | DCM | 20 . . . 50° C. | 1 h |
| C | $H_2O$ | Dioxane | 100° C. | 12 . . . 16 h |

Step 4A: The Synthesis 6I

The solution of 6H (1.0 equiv) was mixed with Ammonia solution in MeOH (20.0 equiv) and heated at 45° C. for 12 hours. Then, the volatiles were removed in vacuo to afford 6I.

Step 5: The Synthesis 6G 6F (1.0 equiv), oxamic acid (1.0 equiv) and TEA (2.5 eq+1.0 eq per each acid eq, if amine salt used) or DIPEA (2.5 eq+1.0 eq per each acid eq, if amine salt used) were mixed together in DMF or DMS+SO. HATU (1.5 eq) was added thereto and the resulting mixture was stirred overnight. The reaction mixture was concentrated in vacuo and the residue was purified by HPLC to obtain 6G.

Step 5A: The Synthesis of 6G 6I (1.0 equiv), $R_3I$ (1.0 equiv), CuI (0.2 equiv), CuI (0.2 equiv), $N^1,N^2$-dimethylcyclohexane-1,2-diamine (0.2 equiv) and $Cs_2CO_3$ were mixed together in dioxane (6 mL) under an Ar atmosphere. The reaction mixture was stirred at 100° C. for 48 h. Then, the mixture was allowed to cool to the room temperature and filtered off. The filtrate was subjected to HPLC to afford 6G.

Example 538. The Synthesis of rac-N-(6-amino-5-ethyl-3-pyridyl)-2-[(2S,5R)-5-methyl-2-[4-(4-methylpiperazin-1-yl)phenyl]-1-piperidyl]-2-oxo-acetamide (Compound 1209), rel-N-(6-amino-5-ethyl-3-pyridyl)-2-[(2R,5S)-5-methyl-2-[4-(4-methylpiperazin-1-yl)phenyl]-1-piperidyl]-2-oxo-acetamide (Compound 1371) and rel-N-(6-amino-5-ethyl-3-pyridyl)-2-[(2S,5R)-5-methyl-2-[4-(4-methylpiperazin-1-yl)phenyl]-1-piperidyl]-2-oxo-acetamide (Compound 1116

Step 1: The Synthesis of rac-N-(6-amino-5-ethyl-3-pyridyl)-2-[(2S,5R)-5-methyl-2-[4-(4-methylpiperazin-1-yl)phenyl]-1-piperidyl]-2-oxo-acetamide (Compound 1209

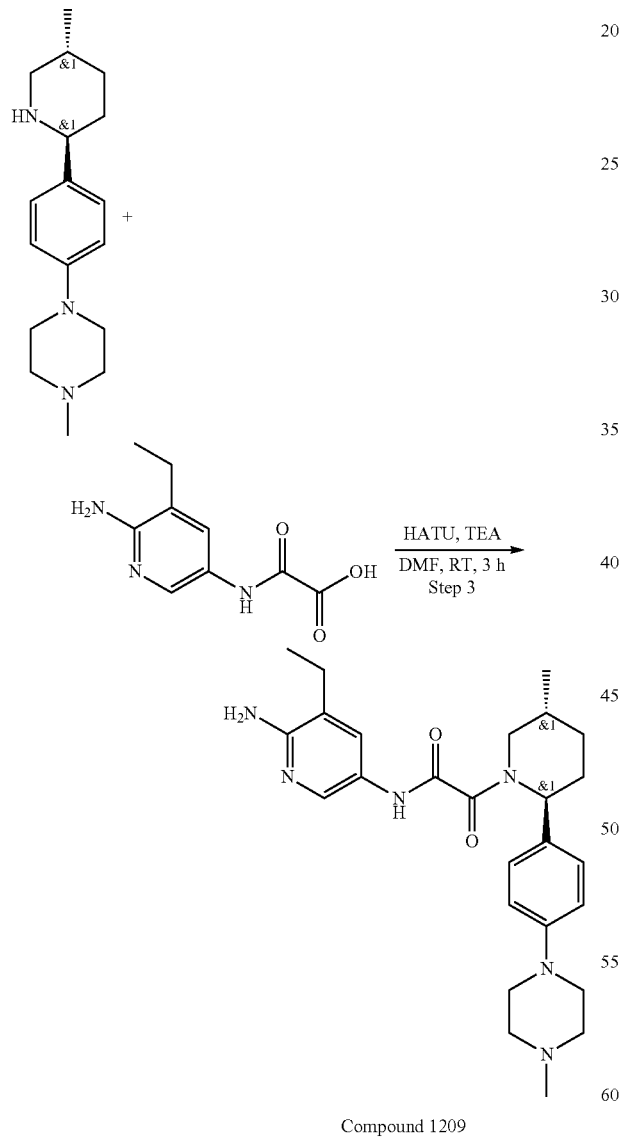

Compound 1209

Prepared by General Procedure Scheme F Step 5
HPLC conditions: 45-60% 0-5 min H$_2$O/MeOH/0.10% NH$_4$OH, flow: 30 mL/min (loading pump 4 mL/min methanol); YMC Triart C18 100×20 mm, 5 um Yield: 0.4 g (33.63%)

$^1$H NMR (600 MHz, dmso) δ 0.98-1.13 (m, 6H), 1.26-1.37 (m, 1H), 1.60-1.74 (m, 1H), 1.78-1.91 (m, 1H), 1.92-2.18 (m, 2H), 2.20 (s, 3H), 2.34-2.39 (m, 2H), 2.40-2.44 (m, 4H), 2.70 (d, 0.5H), 3.07-3.12 (m, 4H), 3.17 (d, 0.5H), 3.37-4.00 (m, 1H), 5.01-5.55 (m, 1H), 5.57-5.67 (m, 2H), 6.88-6.97 (m, 2H), 7.09-7.19 (m, 2H), 7.43-7.52 (m, 1H), 7.98-8.09 (m, 1H), 10.44-10.54 (m, 1H).

LCMS(ESI): [M+H]$^+$ m/z: calcd 465.2; found 465.2; Rt=1.937 min.

Step 2: The Synthesis of rel-N-(6-amino-5-ethyl-3-pyridyl)-2-[(2R,5S)-5-methyl-2-[4-(4-methylpiperazin-1-yl)phenyl]-1-piperidyl]-2-oxo-acetamide (Compound 1371) and rel-N-(6-amino-5-ethyl-3-pyridyl)-2-[(2S,5R)-5-methyl-2-[4-(4-methylpiperazin-1-yl)phenyl]-1-piperidyl]-2-oxo-acetamide (Compound 1116

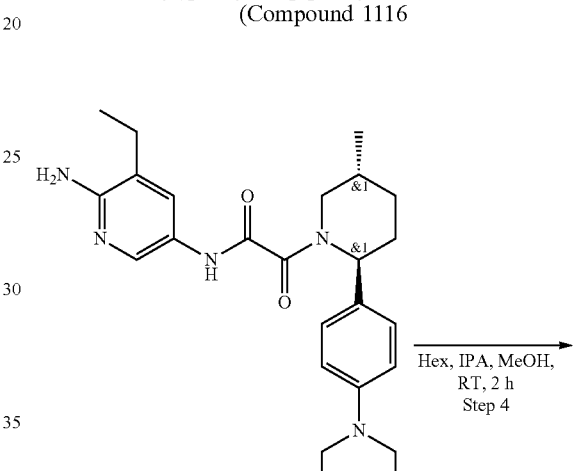

Compound 1209

Compound 1371

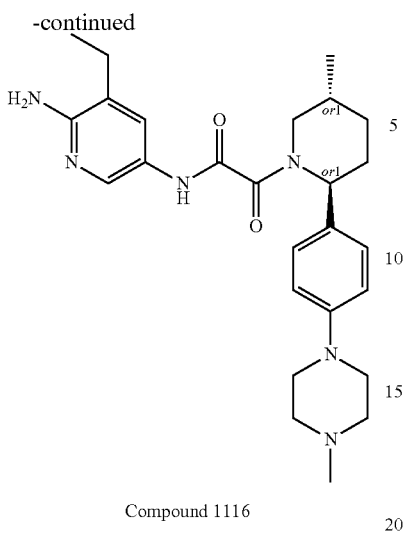

Compound 1116

Prepared by General Procedure Scheme F Step 6

Chiral separation conditions: Chiralpak AS-H (250*20, 5 mkm), Hexane-IPA-MeOH, 80-10-10, 12 mL/min, Inj Volume: 200.000 µl; Column Temperature: 24° C.; Wavelength: 205 nm, 264 nm), RetTime for Compound 1371=88.90 min and RetTime for Compound 1116=62.12 min Compound 1371:

Yield: 140.0 mg (35.0%)

RT (Chiralpak IA (250*4.6 mm, 5 mkm), MeOH-IPA, 50-50, 0.8 mL/min)=48.14 min.

$^{1}$H NMR (600 MHz, dmso) δ 0.99-1.34 (m, 7H), 1.65-2.20 (m, 8H), 2.35-2.42 (m, 4H), 2.70 (m, 1H), 3.05-3.18 (m, 4H), 3.40 (d, 1H), 3.97 (d, 1H), 5.05-5.63 (m, 3H), 6.90-6.93 (m, 2H), 7.11-7.18 (m, 2H), 7.46-7.49 (d, 1H), 8.01-8.05 (d, 1H), 10.49 (m, 1H).

LCMS(ESI): [M+2H]$^{+}$ m/z: calcd 466.2; found 466.2; Rt=0.830 min.

Compound 1116:

Yield: 190.0 mg (47.5%)

RT (Chiralpak IA (250*4.6 mm, 5 mkm), MeOH-IPA, 50-50, 0.8 mL/min)=32.53 min.

$^{1}$H NMR (600 MHz, dmso) δ 0.99-1.34 (m, 7H), 1.67-2.20 (m, 8H), 2.35-2.43 (m, 4H), 2.70 (m, 1H), 3.06-3.19 (m, 4H), 3.40 (d, 1H), 3.97 (d, 1H), 5.04-5.63 (m, 3H), 6.90-6.93 (m, 2H), 7.11-7.19 (m, 2H), 7.46-7.49 (d, 1H), 8.01-8.05 (d, 1H), 10.49 (m, 1H).

LCMS(ESI): [M+2H]$^{+}$ m/z: calcd 466.2; found 466.2; Rt=0.826 min.

Example 539. The Synthesis of N-[6-amino-5-(oxetan-3-yl)-3-pyridyl]-2-[(2R,5S)-2-(1,3-benzothiazol-5-yl)-5-methyl-1-piperidyl]-2-oxo-acetamide (Compound 1356

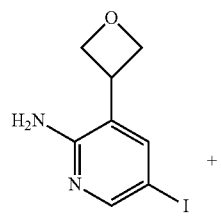 +

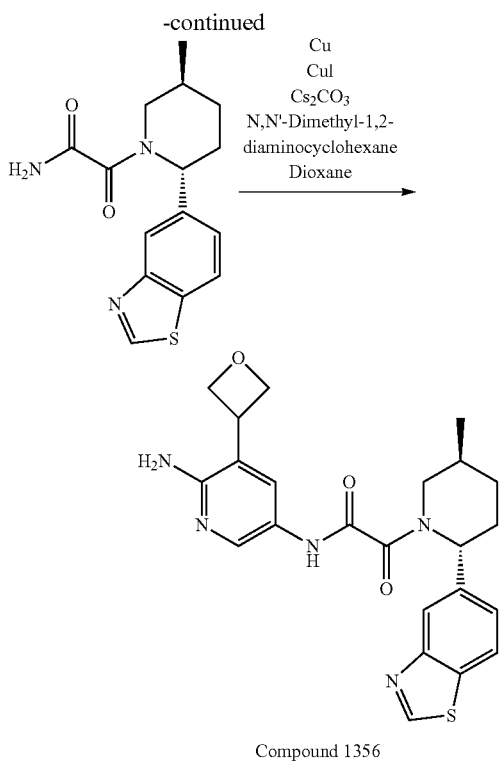

Compound 1356

2-[(2R,5S)-2-(1,3-benzothiazol-5-yl)-5-methyl-1-piperidyl]-2-oxo-acetamide (140 mg, 362 µmol) was added to a mixture of 5-iodo-3-(oxetan-3-yl)pyridin-2-amine (100 mg, 362 mol), Cu (11.5 mg, 181 µmol), copper (I) iodide (6.90 mg, 36.2 µmol, 1.23 µL) and Cesium carbonate (236 mg, 724 µmol) in dioxane (2.00 mL). The resulting mixture was allowed to stir at 100° C. for 18 hr. The obtained mixture was filtered through a pad of Celite and concentrated in vacuo. The residue was subjected to HPLC (0.5-6.5 min 20-0% water-ACN, +0.1% vol. of 25% aq. NH$_3$, 30 mL/min, column: XBridge, 100×19 mm, 5 µm). The obtained material (44.3 mg) was subjected to chiral HPLC (1st run—Chiralcel OJ-H (250*21, 5 mkm), Hexane-IPA-MeOH, 50-25-25, 12 mL/min, main peak at 38.717 min; 2nd run—Chiralpak IA 11 (250*21, 5 mkm), IPA-MeOH, 50-50, 10 mL/min) to afford Compound 1356 (20.7 mg, 99+ee, after two runs).

Analytical: RT for Compound 1356 (Chiralcel OJ-H (250*4.6 mm, 5 mkm), Hexane-IPA-MeOH, 50-25-25, 0.6 mL/min)-39.803 min.

$^{1}$H NMR (600 MHz, DMSO-d$_6$): δ (ppm) 0.92-1.06 (m, 3H), 1.22-1.41 (m, 2H), 1.72-1.92 (m, 2H), 2.08-2.33 (m, 2H), 2.80-2.83 (m, 1H), 3.86-4.56 (m, 3H), 4.87-4.95 (m, 2H), 5.35-5.74 (m, 3H), 7.43-7.76 (m, 3H), 8.02-8.19 (m, 2H), 9.39-9.41 (m, 1H), 10.61-10.67 (m, 1H)

LCMS(ESI): [M+H]$^{+}$ m/z: calcd 452.19; found 452.0; Rt=0.824.

$^{1}$H NMR (600 MHz, DMSO-d$_6$) δ 1.03-1.06 (m, 3H), 1.33-1.41 (m, 1H), 1.71-1.91 (m, 2H), 2.09-2.37 (m, 2H), 3.53-4.24 (m, 3H), 4.47-4.56 (m, 2H), 4.87-4.95 (m, 2H), 5.36-5.73 (m, 3H), 7.43-7.51 (m, 1H), 7.68-7.76 (m, 1H), 8.02-8.19 (m, 3H), 9.39 (s, 1H), 10.61-10.67 (d, 1H).

Example 540. The Synthesis of rac-N-(6-amino-5-methyl-3-pyridyl)-2-[(2R,5S)-5-methyl-2-[4-(4-methylpiperazin-1-yl)phenyl]-1-piperidyl]-2-oxo-acetamide (Compound 1105), rel-N-(6-amino-5-methyl-3-pyridyl)-2-[(2S,5R)-5-methyl-2-[4-(4-methylpiperazin-1-yl)phenyl]-1-piperidyl]-2-oxo-acetamide (Compound 1193) and rel-N-(6-amino-5-methyl-3-pyridyl)-2-[(2R,5S)-5-methyl-2-[4-(4-methylpiperazin-1-yl)phenyl]-1-piperidyl]-2-oxo-acetamide (Compound 1328
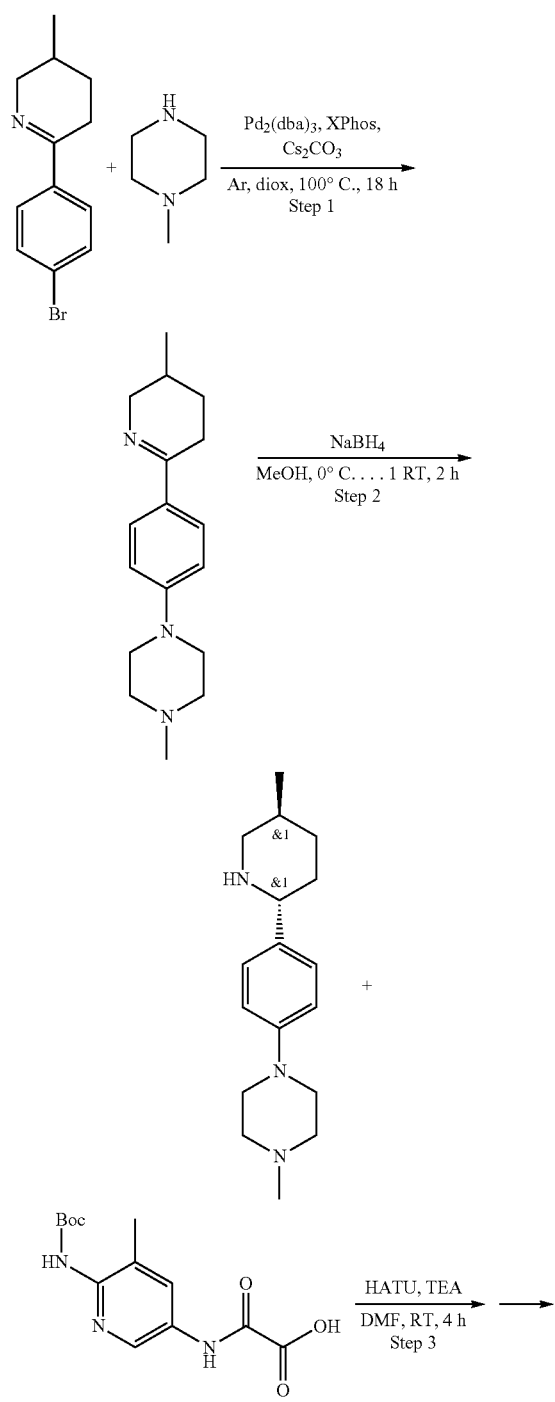
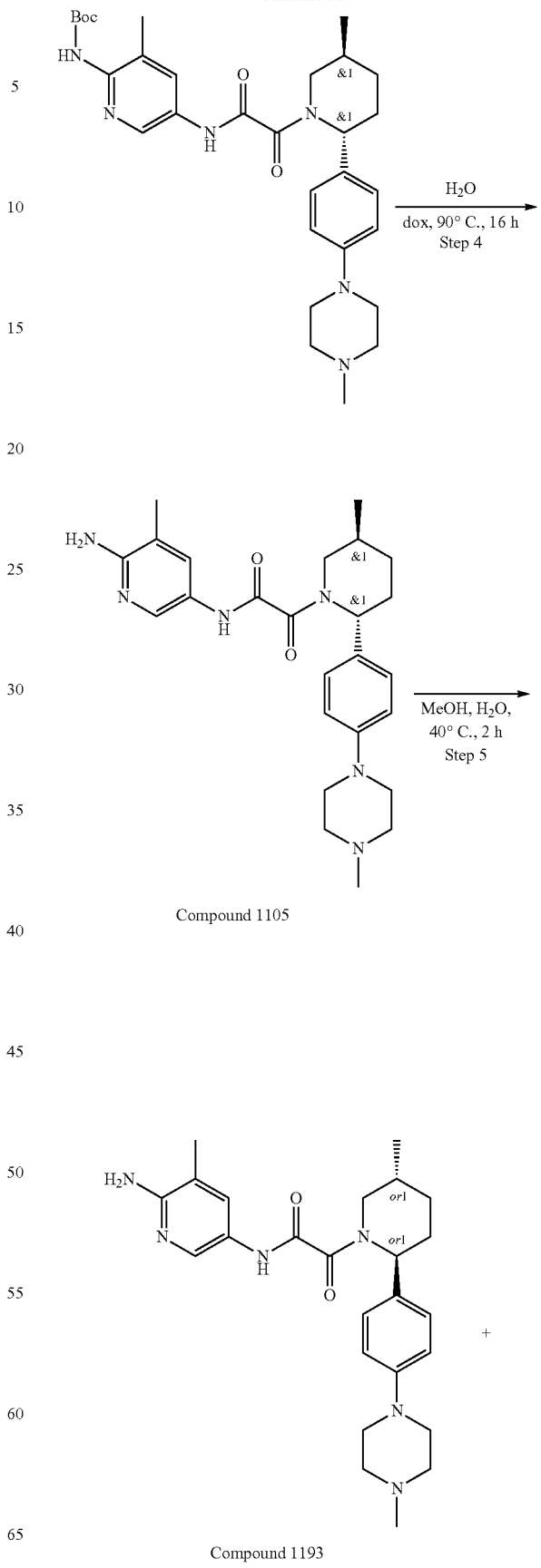
Compound 1105
Compound 1193

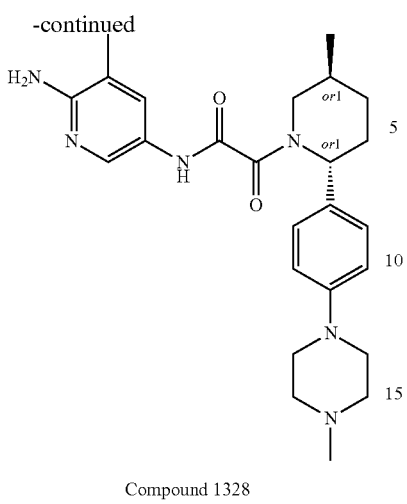

Compound 1328

Step 1: The Synthesis of 1-methyl-4-(4-(5-methyl-3,4,5,6-tetrahydropyridin-2-yl)phenyl)piperazine Prepared by general procedure 6 Step 1A.
Yield: 4.0 g (74.33%)
LCMS(ESI): [M+H]$^+$ m/z: calcd 272.2; found 272.2; Rt=0.608 min.

Step 2: The Synthesis of rac-1-methyl-4-[4-[(2S,5R)-5-methyl-2-piperidyl]phenyl]piperazine Prepared by general procedure 6 Step 2A
Yield: 3.7 g (91.82%)
LCMS(ESI): [M+H]$^+$ m/z: calcd 274.4; found 374.4; Rt=0.464 min.

Step 3: The Synthesis of rac-tert-butyl N-[3-methy-5-[[2-[(2R,5S)-5-methyl-2-[4-(4-methylpiperazin-1-yl)phenyl]-1-piperidyl]-2-oxo-acetyl]amino]-2-pyridyl]carbamate Prepared by general procedure 6 Step 5
HPLC conditions: 40-90% 0-5 min H$_2$O/MeOH/0.1% NH$_4$OH, flow: 30 mL/min; column:
YMC Triart C18 100×20 mm, 5 um
Yield: 260.0 mg (43.91%)
LCMS(ESI): [M+H]$^+$ m/z: calcd 552.4; found 552.4; Rt=2.770 min.

Step 4: The Synthesis of rac-N-(6-amino-5-methyl-3-pyridyl)-2-[(2R,5S)-5-methyl-2-[4-(4-methylpiperazin-1-yl)phenyl]-1-piperidyl]-2-oxo-acetamide (Compound 1105

Prepared by general procedure 6 step 6
HPLC conditions: 30-50% 0-6 min H$_2$O/MeCN/0.1% NH$_4$OH, flow: 30 mL/min; column:
YMC Triart C18 100×20 mm, 5 um
Yield: 154.0 mg (72.39%)
LCMS(ESI): [M+H]$^+$ m/z: calcd 451.2; found 451.2; Rt=1.320 min.

Step 5: The Synthesis of rel-N-(6-amino-5-methyl-3-pyridyl)-2-[(2S,5R)-5-methyl-2-[4-(4-methylpiperazin-1-yl)phenyl]-1-piperidyl]-2-oxo-acetamide (Compound 1193) and rel-N-(6-amino-5-methyl-3-pyridyl)-2-[(2R,5S)-5-methyl-2-[4-(4-methylpiperazin-1-yl)phenyl]-1-piperidyl]-2-oxo-acetamide (Compound 1328

Prepared by General Procedure 6 Step 7
Chiral separation conditions: Chiralpak IB (250*20 mm, 10 mkm); Mobile phase: CO$_2$-MeOH, 60-40. Flow Rate: 80 mL/min; Column Temperature: 40° C.; Wavelength: 215 nm.
RetTime (Compound 1193)=12.65 min; RetTime (Compound 1328)=16.12 min Compound 1193:
Yield: 49.14 mg (34.90%).
RT (Chiralpak IA, IPA-MeOH, 50-50, 1.0 mL/min)=26.336 min.
$^1$H NMR (DMSO-d$_6$, 600 MHz): δ (ppm) 1.00 (m, 3H), 1.31 (m, 1H), 1.67 (m, 1H), 1.84 (m, 1H), 2.01 (m, 4H), 2.21 (m, 4H), 2.45 (m, 4H), 3.11 (m, 5H), 3.68 (dd, 1H), 5.57 (m, 3H), 6.92 (m, 2H), 7.15 (m, 2H), 7.46 (m, 1H), 7.99 (m, 1H), 10.47 (m, 1H).
LCMS(ESI): [M+2H]$^+$ m/z: calcd 452.2; found 452.2; Rt=1.619 min.

Compound 1328:
Yield: 45.07 mg (32.01%).
RT (Chiralpak IA, IPA-MeOH, 50-50, 1.0 mL/min)=34.522 min.
$^1$H NMR (DMSO-d$_6$, 600 MHz): δ (ppm) 1.00 (m, 3H), 1.31 (m, 1H), 1.66 (m, 1H), 1.84 (m, 1H), 2.01 (m, 4H), 2.20 (m, 4H), 2.42 (m, 5H), 3.15 (m, 4H), 3.68 (m, 1H), 5.57 (m, 3H), 6.92 (m, 2H), 7.15 (dd, 2H), 7.46 (m, 1H), 8.00 (m, 1H), 10.46 (m, 1H).
LCMS(ESI): [M+2H]$^+$ m/z: calcd 452.2; found 452.2; Rt=1.619 min.

Example 541. The Synthesis of rel-N-(6-amino-5-ethyl-3-pyridyl)-2-[(2R,5S)-2-[4-(4-ethylpiperazin-1-yl)phenyl]-5-methyl-1-piperidyl]-2-oxo-acetamide (Compound 1360) and rel-N-(6-amino-5-ethyl-3-pyridyl)-2-[(2S,5R)-2-[4-(4-ethylpiperazin-1-yl)phenyl]-5-methyl-1-piperidyl]-2-oxo-acetamide (Compound 1097

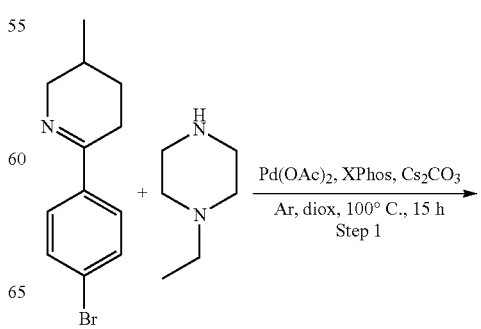

2431
-continued

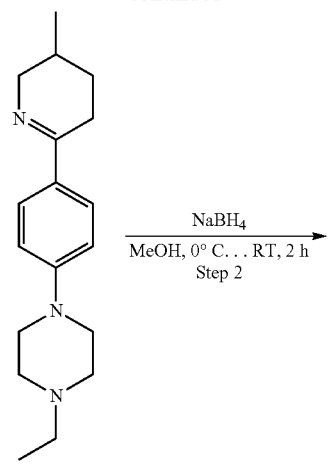

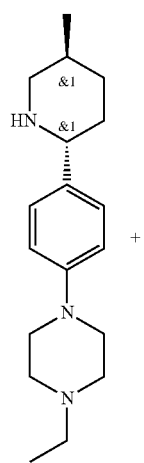

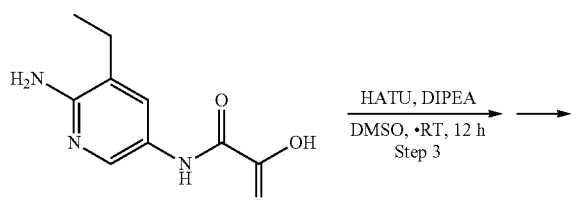

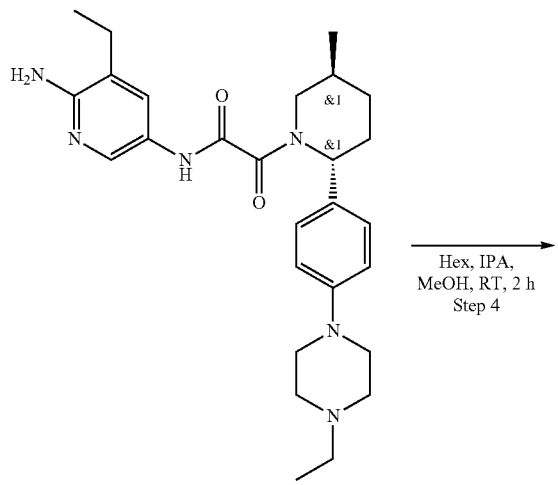

2432
-continued

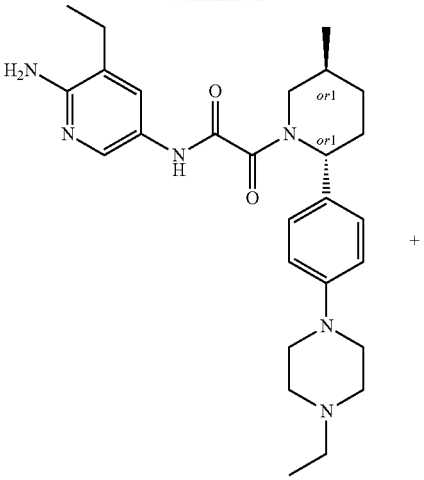

Compound 1360

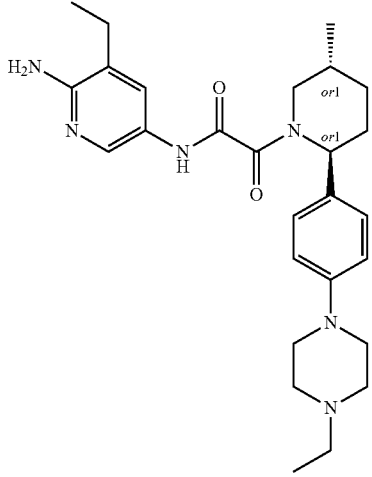

Compound 1097

Step 1: The Synthesis of 1-ethyl-4-[4-(3-methyl-2,3,4,5-tetrahydropyridin-6-yl)phenyl]piperazine Prepared by General Procedure 6 Step 1A (Method C)
Yield: 0.65 g (crude)
LCMS(ESI): [M+H]$^+$ m/z: calcd 286.2; found 286.2; Rt=0.617 min.

Step 2: The Synthesis of rac-1-ethyl-4-[4-[(2R,5S)-5-methyl-2-piperidyl]phenyl]piperazine Prepared by General Procedure 6 Step 2A
Yield: 0.39 g (95.62%)
LCMS(ESI): [M+H]$^+$ m/z: calcd 288.2; found 288.2; Rt=0.606 min.

Step 3: The Synthesis of rac-N-(6-amino-5-ethyl-3-pyridyl)-2-[(2R,5S)-2-[4-(4-ethylpiperazin-1-yl)phenyl]-5-methyl-1-piperidyl]-2-oxo-acetamide Prepared by General Procedure 6 Step 5
HPLC conditions: 2-10 min 40-100% MeCN/H$_2$O 30 mL/min (loading pump 4 mL MeCN column; SunFire 100*19 mm, 5 microM Yield: 0.18 g (18.25%)
LCMS(ESI): [M+H]⁺ m/z: calcd 480.2; found 480.2; Rt=0.781 min.

Step 4: The Synthesis of rel-N-(6-amino-5-ethyl-3-pyridyl)-2-[(2R,5S)-2-[4-(4-ethylpiperazin-1-yl)phenyl]-5-methyl-1-piperidyl]-2-oxo-acetamide (Compound 1360) and rel-N-(6-amino-5-ethyl-3-pyridyl)-2-[(2S,5R)-2-[4-(4-ethylpiperazin-1-yl)phenyl]-S-methyl-1-piperidyl]-2-oxo-acetamide (Compound 1097

Prepared by General Procedure Scheme F Step 6
Chiral separation conditions: Chiralpak AS-H (250*20 mm; 5 m); Mobile phase: Hexane-IPA
MeOH, 70-15-15 Flow Rate: 12 mL/min; Column Temperature: 20° C.; Wavelength: 205 nm, RetTime (isomer A)=11.37 min; RetTime (isomer B)=19.30 min Compound 1360:
Yield: 42.0 mg (23.33%)
RT (Chiralpak AS-H (250*20 mm; 5 m), Hexane-IPA-MeOH, 60-20-20, Flow Rate: 0.6 mL/min)=12.74 min.
¹H NMR (600 MHz, cd₃od) δ 1.11 (d, 3H), 1.14-1.27 (m, 6H), 1.39-1.46 (m, 1H), 1.85-1.99 (m, 2H), 2.08-2.28 (m, 2H), 2.45-2.53 (m, 4H), 2.61-2.67 (m, 4H), 3.00-3.38 (m, 5H), 3.61-4.08 (m, 1H), 5.21-5.71 (m, 1H), 6.93-7.03 (m, 2H), 7.20-7.28 (m, 2H), 7.49-7.66 (m, 1H), 7.94-8.12 (m, 1H).
LCMS(ESI): [M+H]⁺ m/z: calcd 479.4; found 479.4; Rt=2.042 min.

Compound 1097:
Yield: 42.0 mg (23.33%)
RT (Chiralpak AS-H (250*20 mm; 5 m), Hexane-IPA-MeOH, 60-20-20, Flow Rate: 0.6 mL/min)=8.94 min.
¹H NMR (600 MHz, dmso) δ 0.99-1.03 (m, 6H), 1.06-1.13 (m, 3H), 1.26-1.36 (m, 1H), 1.62-1.73 (m, 1H), 1.79-1.90 (m, 1H), 1.93-2.10 (m, 1H), 2.12-2.22 (m, 1H), 2.34-2.41 (m, 4H), 2.49-2.53 (m, 4H), 2.67-3.20 (m, 5H), 3.37-4.00 (m, 1H), 5.00-5.55 (m, 1H), 5.57-5.66 (m, 2H), 6.89-6.95 (m, 2H), 7.10-7.19 (m, 2H), 7.44-7.52 (m, 1H), 7.98-8.07 (m, 1H), 10.38-10.53 (m, 1H).
LCMS(ESI): [M+H]⁺ m/z: calcd 479.4; found 479.4; Rt=2.035 min.

Example 542. The Synthesis of rel-N-(6-amino-5-ethyl-3-pyridyl)-2-[(2R,5S)-2-[4-(4-isopropylpiperazin-1-yl)phenyl]-5-methyl-1-piperidyl]-2-oxo-acetamide (Compound 1208) and rel-N-(6-amino-5-ethyl-3-pyridyl)-2-[(2S,5R)-2-[4-(4-isopropylpiperazin-1-yl)phenyl]-5-methyl-1-piperidyl]-2-oxo-acetamide (Compound 1234

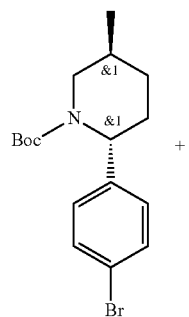

+

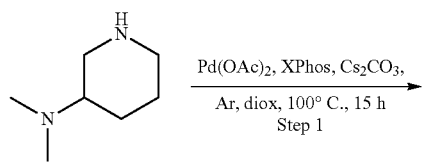

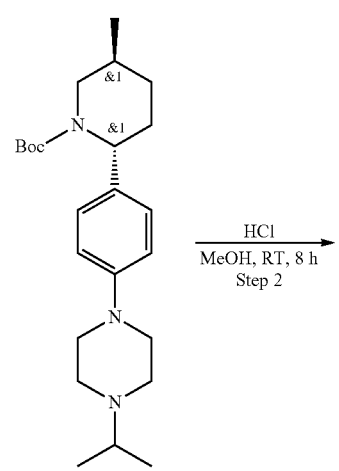

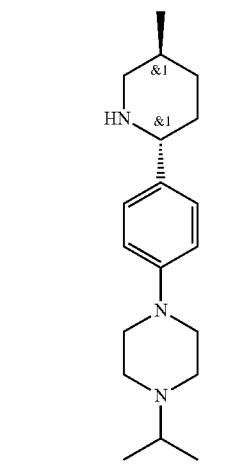

+

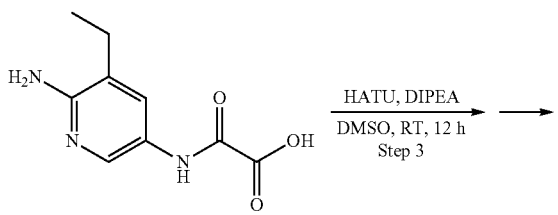

-continued

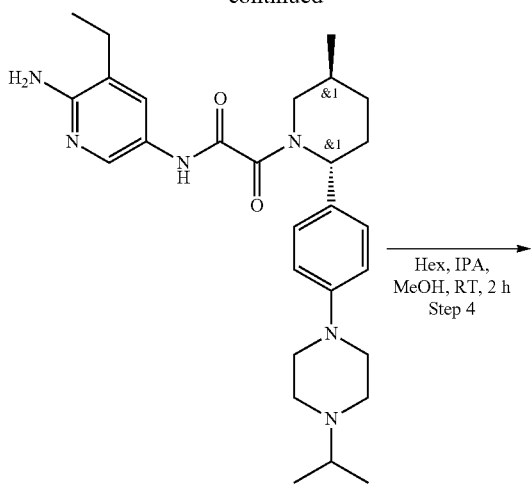

Compound 1208

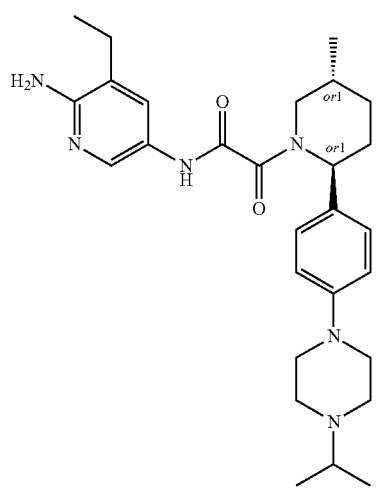

Compound 1234

Step 1: The Synthesis of rac-tert-butyl (2R,5S)-2-[4-(4-isopropylpiperazin-1-yl)phenyl]-5-methyl-piperidine-1-carboxylate Prepared by General Procedure Scheme F Step 3 (Method C)
Yield: 0.7 g (crude)
LCMS(ESI): [M+H]⁺ m/z: calcd 402.2; found 402.2; Rt=1.054 min.

Step 2: The Synthesis of rac-1-isopropyl-4-[4-[(2R,5S)-5-methyl-2-piperidyl]phenyl]piperazine Prepared by General Procedure Scheme F Step 4 (Method A)
Yield: 0.58 g (88.88%, 2HCl)
LCMS(ESI): [M+H]⁺ m/z: calcd 302.2; found 302.2; Rt=0.671 min.

Step 3: The Synthesis of rac-N-(6-amino-5-ethyl-3-pyridyl)-2-[(2R,5S)-2-[4-(4-isopropylpiperazin-1-yl)phenyl]-5-methyl-1-piperidyl]-2-oxo-acetamide Prepared by General Procedure Scheme F Step 5
HPLC conditions: 2-10 min 50-100% methanol/water; Flow 30 mL/min; loading pump 4 mL/min methanol; column SunFire 19*100 mm
Yield: 0.178 g (18.78%)
LCMS(ESI): [M+H]⁺ m/z: calcd 493.2; found 493.2; Rt=0.854 min.

Step 4: The Synthesis of rel-N-(6-amino-5-ethyl-3-pyridyl)-2-[(2R,5S)-2-[4-(4-isopropylpiperazin-1-yl)phenyl]-5-methyl-1-piperidyl]-2-oxo-acetamide (Compound 1208) and Rel-N-(6-amino-5-ethyl-3-pyridyl)-2-[(2S,5R)-2-[4-(4-isopropylpiperazin-1-yl)phenyl]-5-methyl-1-piperidyl]-2-oxo-acetamide (Compound 1234

Prepared by General Procedure Scheme F Step 6
Chiral separation conditions: Chiralpak AS-H (250*20, 5 mkm), Hexane-IPA-MeOH, 70-15-15, Flow 12 mL/min; RetTime=10.582 min. and RetTime=16.370 min.
Compound 1208:
Yield: 72.8 mg (40.90%)
RT (Chiralpak AS-H (250*20, 5 mkm), Hexane-IPA-MeOH, 50-25-25, 0.6 mL/min)=7.584 min.
¹H NMR (DMSO-d₆, 500 MHz): δ (ppm) 0.99 (m, 9H), 1.09 (m, 3H), 1.30 (m, 1H), 1.68 (m, 1H), 1.85 (m, 1H), 1.91 (m, 1H), 2.12 (m, 2H), 2.38 (m, 2H), 2.55 (m, 4H), 2.69 (m, 1H), 3.09 (m, 5H), 3.68 (dd, 1H), 5.58 (m, 3H), 6.92 (m, 2H), 7.15 (m, 2H), 7.48 (m, 1H), 8.03 (m, 1H), 10.47 (m, 1H).
LCMS(ESI): [M+H]⁺ m/z: calcd 493.2; found 493.2; Rt=1.815 min.
Compound 1234:
Yield: 61.9 mg (34.78%)
RT (Chiralpak AS-H (250*20, 5 mkm), Hexane-IPA-MeOH, 50-25-25, 0.6 mL/min)=9.703 min.
¹H NMR (DMSO-d₆, 500 MHz): δ (ppm) 0.99 (m, 9H), 1.09 (m, 3H), 1.30 (m, 1H), 1.68 (m, 1H), 1.85 (m, 1H), 1.91 (m, 1H), 2.12 (m, 2H), 2.38 (m, 2H), 2.55 (m, 4H), 2.69 (m, 1H), 3.09 (m, 5H), 3.68 (dd, 1H), 5.58 (m, 3H), 6.92 (m, 2H), 7.15 (m, 2H), 7.48 (m, 1H), 8.03 (m, 1H), 10.47 (m, 1H).

LCMS(ESI): [M+H]+ m/z: calcd 493.2; found 493.2; Rt=1.814 min.
Example 543. The Synthesis of rel-N-(6-amino-5-ethyl-3-pyridyl)-2-[(2S,5R)-5-methyl-2-[4-(2-methyl-2,9-diazaspiro[5.5]undecan-9-yl)phenyl]-1-piperidyl]-2-oxo-acetamide (Compound 1269) and rel-N-(6-amino-5-ethyl-3-pyridyl)-2-[(2R,5S)-5-methyl-2-[4-(2-methyl-2,9-diazaspiro[5.5]undecan-9-yl)phenyl]-1-piperidyl]-2-oxo-acetamide (Compound 1243
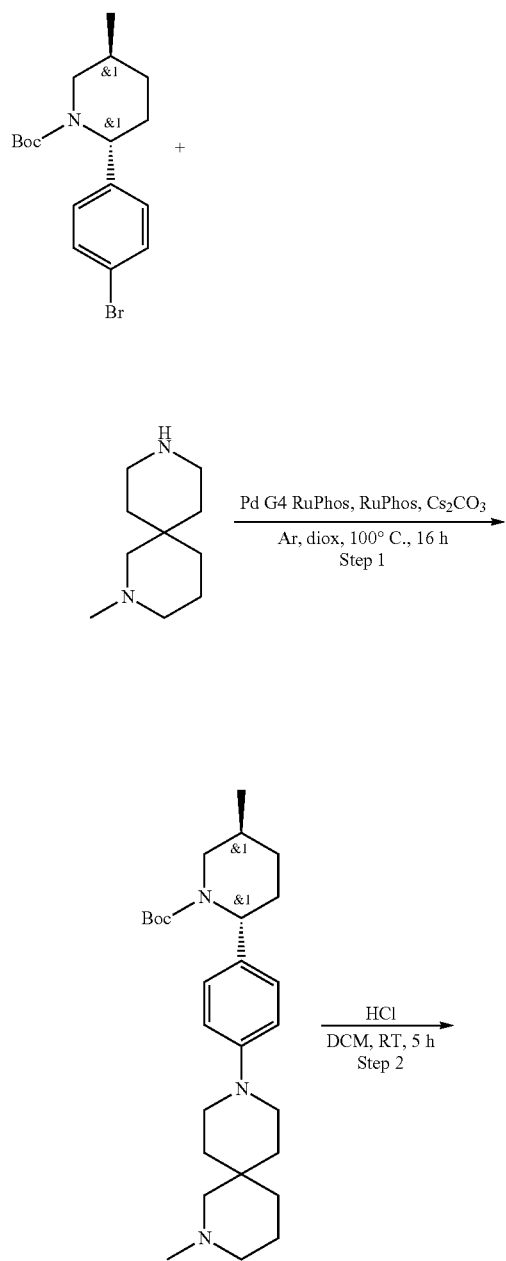
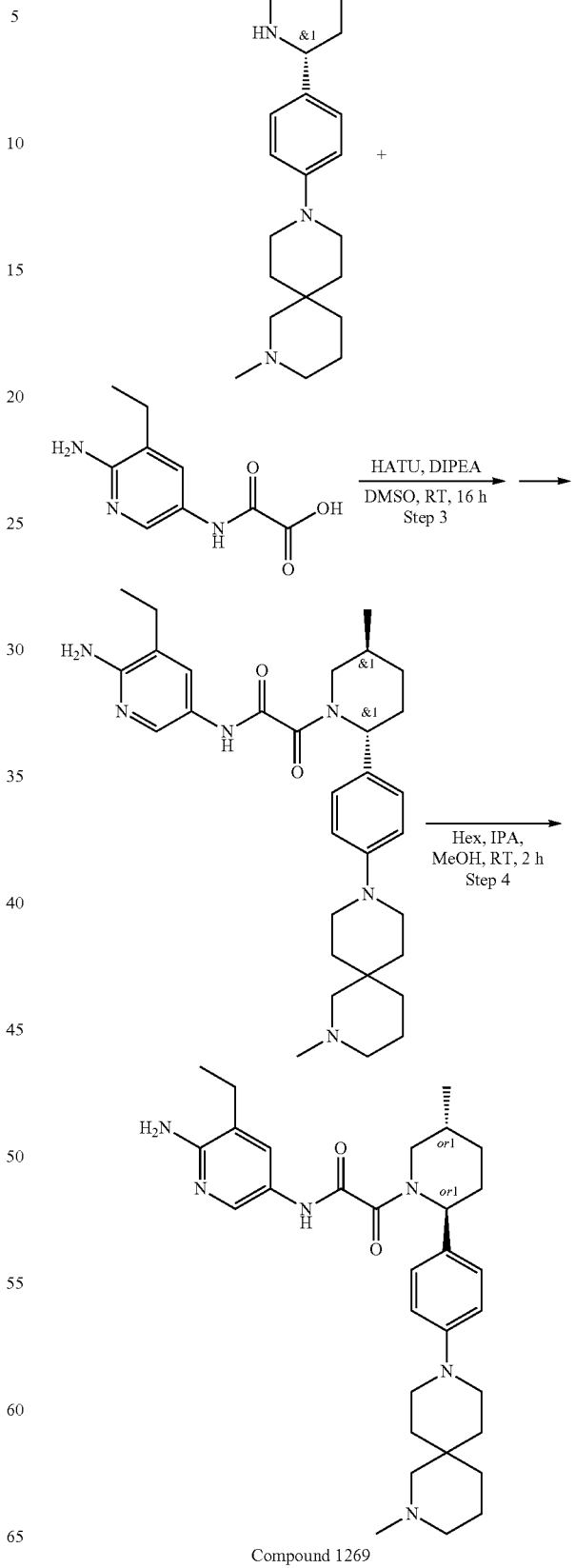
Compound 1269

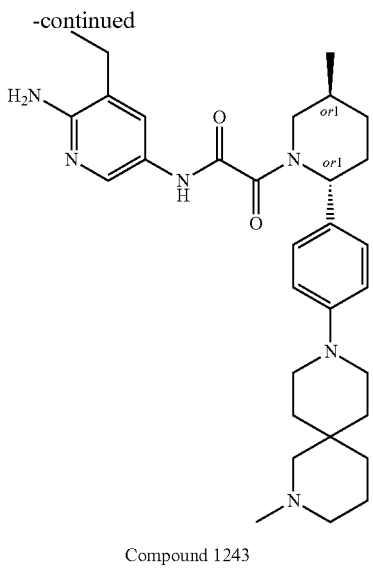

Compound 1243

Step 1: The Synthesis of tert-butyl (2S,5R)-5-methyl-2-[4-(2-methyl-2,9-diazaspiro[5.5]undecan-9-yl)phenyl]piperidine-1-carboxylate Prepared by General Procedure Scheme F Step 3 (Method B)
HPLC conditions: 60-88% 0-6 min H$_2$O/MeOH/0.1% NH$_4$OH, flow: 30 mL/min (loading pump 4 mL/min methanol); column: YMC Triart C18 100×20 mm, 5 um
Yield: 42.0 mg (6.74%)
LCMS(ESI): [M+H]$^+$ m/z: calcd 442.4; found 442.4; Rt=2.592 min.

Step 2: The Synthesis of rac-2-methyl-9-[4-[(2S,5R)-5-methyl-2-piperidyl]phenyl]-2,9-diazaspiro[5.5]undecane Prepared by General Procedure Scheme F Step 4 (Method A)
Yield: 43.0 mg (99.37%, 3HCl)
LCMS(ESI): [M+H]$^+$ m/z: calcd 342.4; found 342.4; Rt=1.466 min.

Step 3: The Synthesis of rac-N-(6-amino-5-ethyl-3-pyridyl)-2-[(2S,5R)-5-methyl-2-[4-(2-methyl-2,9-diazaspiro[5.5]undecan-9-yl)phenyl]-1-piperidyl]-2-oxo-acetamide Prepared by General Procedure Scheme F Step 5
HPLC conditions: 60-100% 0-5 min H$_2$O/MeOH/0.10% NH$_4$OH, flow: 30 mL/min (loading pump 4 mL/min methanol); column: YMC Triart C18 100×20 mm, 5 um
Yield: 14.0 mg (20.87%)
LCMS(ESI): [M+H]$^+$ m/z: calcd 533.2; found 533.2; Rt=2.228 min.

Step 4: The Synthesis of rel-N-(6-amino-5-ethyl-3-pyridyl)-2-[(2S,5R)-5-methyl-2-[4-(2-methyl-2,9-diazaspiro[5.5]undecan-9-yl)phenyl]-1-piperidyl]-2-oxo-acetamide (Compound 1269) and Rel-N-(6-amino-5-ethyl-3-pyridyl)-2-[(2R,5S)-5-methyl-2-[4-(2-methyl-2,9-diazaspiro[5.5]undecan-9-yl)phenyl]-1-piperidyl]-2-oxo-acetamide (Compound 1243

Prepared by General Procedure Scheme F Step 6
Chiral separation conditions: Chiralpak IB (250*20 mm, 5 mkm), Hexane-IPA-MeOH, 50-25-25, Flow 12 mL/min; Inj Volume: 200.000 μl; Column Temperature: 24° C.; Wavelength: 205 nm, 264 nm), RetTime (Compound 1269)=16.655 min and RetTime (Compound 1243)=21.256 min Compound 1269:
Yield: 3.8 mg (38.00%)
RT (Chiralpak IB (250*20 mm, 5 mkm), Hexane-IPA-MeOH, 50-25-25, 0.6 mL/min)=16.655 min.
$^1$H NMR (600 MHz, dmso) δ 0.99-1.11 (m, 6H), 1.22-1.31 (m, 3H), 1.52-1.67 (m, 6H), 1.81-2.15 (m, 8H), 2.39-2.40 (m, 2H), 2.69-2.71 (m, 1H), 3.11-3.18 (m, 6H), 3.39-3.98 (m, 2H), 5.04-5.63 (m, 3H), 6.90-6.93 (m, 2H), 7.10-7.16 (m, 2H), 7.46-7.49 (d, 1H), 8.01-8.05 (d, 1H), 10.45-10.49 (d, 1H).
LCMS(ESI): [M+H]$^+$ m/z: calcd 533.2; found 533.2; Rt=0.752 min.

Compound 1243:
Yield: 2.8 mg (28.00%)
RT (Chiralpak IB (250*20 mm, 5 mkm), Hexane-IPA-MeOH, 50-25-25, 0.6 mL/min)=21.256 min.
$^1$H NMR (600 MHz, dmso) δ 0.99-1.22 (m, 6H), 1.22-1.29 (m, 3H), 1.51-1.67 (m, 6H), 1.82-2.16 (m, 8H), 2.40 (m, 2H), 2.69-2.71 (m, 2H), 3.10-3.18 (m, 5H), 3.39-3.98 (m, 2H), 5.04-5.63 (m, 3H), 6.90-6.93 (m, 2H), 7.10-7.16 (m, 2H), 7.46-7.49 (d, 1H), 8.07-8.05 (d, 1H), 10.45-10.49 (d, 1H).
LCMS(ESI): [M+H]$^+$ m/z: calcd 533.2; found 533.2; Rt=0.758 min.

Example 544. The Synthesis of N-(6-amino-5-ethylpyridin-3-yl)-2-[(2R,5S)-2-[4-(4-{[ethyl(methyl)amino]methyl}piperidin-1-yl)phenyl]-5-methylpiperidin-1-yl]-2-oxoacetamide (Compound 1232

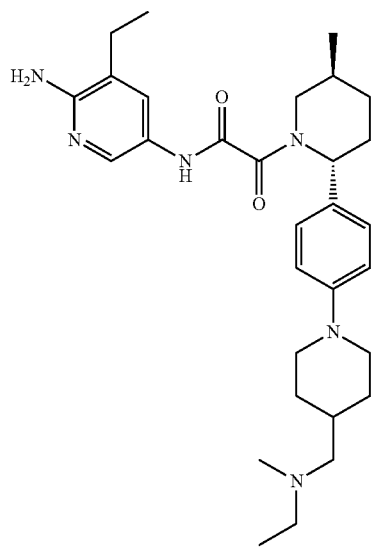 [SMILES: CCc1cc(NC(=O)C(=O)N2C[C@@H](C)CC[C@@H]2c2ccc(N3CCC(CN(C)CC)CC3)cc2)cnc1N]

Yield: 13.70 mg; 26.30%.
$^1$H NMR (600 MHz, dmso) δ 0.94-0.96 (m, 3H), 0.98-1.03 (m, 3H), 1.08-1.18 (m, 5H), 1.23-1.38 (m, 1H), 1.54-1.60 (m, 1H), 1.63-1.72 (m, 1H), 1.73-1.77 (m, 2H), 1.80-1.90 (m, 1H), 1.92-2.06 (m, 1H), 2.11 (s, 6H), 2.14-2.22 (m, 1H), 2.28-2.33 (m, 2H), 2.39-2.41 (m, 1H), 2.60-2.65 (m, 2H), 2.72-3.20 (m, 1H), 3.38-3.43 (m, 0.7H), 3.62-3.66 (m, 2H), 3.93-4.01 (m, 0.3H), 5.02-5.57 (m, 1H), 5.58-5.66 (m, 2H), 6.88-6.93 (m, 2H), 7.09-7.17 (m, 2H), 7.44-7.52 (m, 1H), 7.99-8.07 (m, 1H), 10.39-10.56 (m, 1H).

LCMS(ESI): [M+H]⁺ m/z: calcd 521.4; found 521.4; Rt=2.050 min.

Example 545. The Synthesis of N-(6-amino-5-ethylpyridin-3-yl)-2-[(2R,5S)-5-methyl-2-(4-{4-[(Pyrrolidin-1-yl)methyl]piperidin-1-yl}Phenyl)piperidin-1-yl]-2-oxoacetamide (Compound 1276

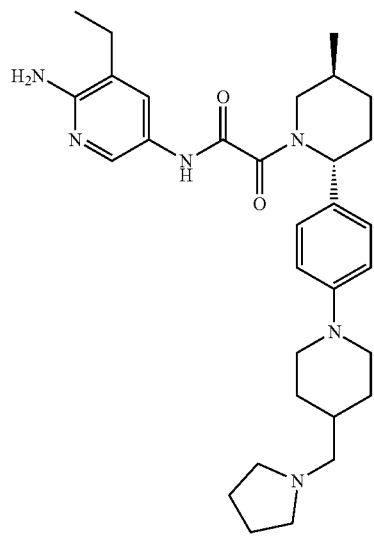 [SMILES: CCc1cc(NC(=O)C(=O)N2C[C@@H](C)CC[C@@H]2c2ccc(N3CCC(CN4CCCC4)CC3)cc2)cnc1N]

Yield: 22.70 mg; 21.30%.

¹H NMR (600 MHz, dmso) δ 0.97-1.03 (m, 3H), 1.07-1.13 (m, 3H), 1.15-1.22 (m, 2H), 1.27-1.36 (m, 1H), 1.50-1.74 (m, 7H), 1.75-2.22 (m, 6H), 2.24-2.28 (m, 2H), 2.38-2.41 (m, 5H), 2.62-2.73 (m, 1H), 3.13-3.99 (m, 4H), 5.00-5.53 (m, 1H), 5.55-5.65 (m, 2H), 6.88-6.94 (m, 2H), 7.07-7.19 (m, 2H), 7.44-7.52 (m, 1H), 7.99-8.09 (m, 1H), 10.43-10.53 (m, 1H).

LCMS(ESI): [M+2H]⁺ m/z: calcd 534.4; found 534.4; Rt=1.677 min.

Example 546. The Synthesis of rac-N-(6-amino-5-ethyl-3-pyridyl)-2-[(2R,5S)-5-methyl-2-[4-(2-methyl-5-oxa-2,8-diazaspiro[3.5]nonan-8-yl)phenyl]-1-piperidyl]-2-oxo-acetamide (Compound 1329), rel-N-(6-amino-5-ethyl-3-pyridyl)-2-[(2S,5R)-5-methyl-2-[4-(2-methyl-5-oxa-2,8-diazaspiro[3.5]nonan-8-yl)phenyl]-1-piperidyl]-2-oxo-acetamide (Compound 1150) and rel-N-(6-amino-5-ethyl-3-pyridyl)-2-[(2R,5S)-5-methyl-2-[4-(2-methyl-5-oxa-2,8-diazaspiro[3.5]nonan-8-yl)phenyl]-1-piperidyl]-2-oxo-acetamide (Compound 1339

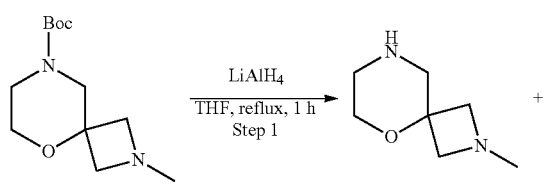

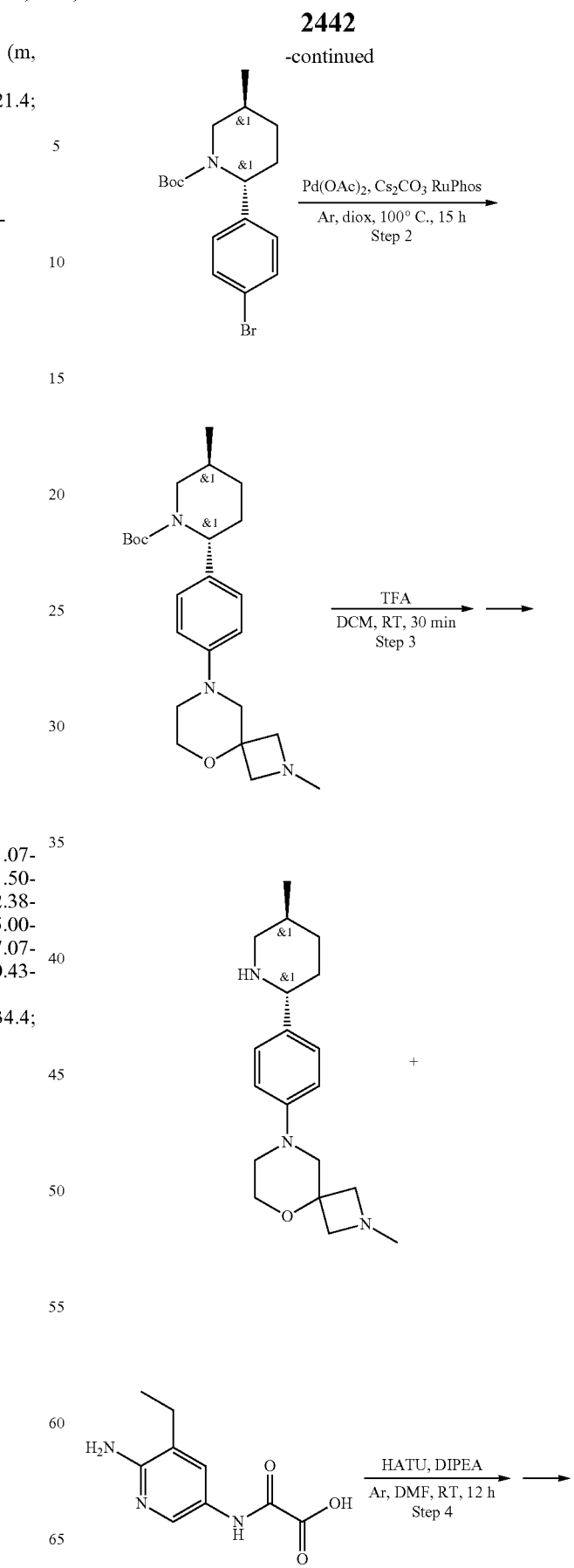

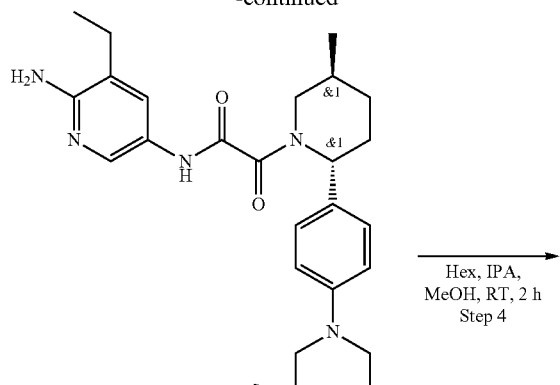

Compound 1329

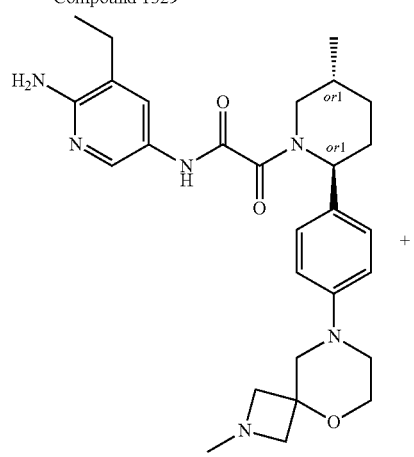

Compound 1150

Compound 1339

Step 1: The Synthesis of rac-2-methyl-5-oxa-2,8-diazaspiro[3.5]nonane

LiAlH₄ (374.08 mg, 9.86 mmol) was suspended in THF (50 mL) and the solution of tert-butyl 5-oxa-2,8-diazaspiro[3.5]nonane-2-carboxylate (1.5 g, 6.57 mmol) tert-butyl 5-oxa-2,8-diazaspiro[3.5]nonane-2-carboxylate (1.5 g, 6.57 mmol) in THF (50 mL) was added dropwise. After the addition was completed, the reaction mixture refluxed for 1 hr and then allowed to cool to r.t. Water (10 mL) was carefully added dropwise to the precooled reaction mixture. The resulting mixture was stirred for 30 min and filtered. A filter cake was rinsed with THF (3*40 mL) and the filtrate was concentrated in vacuo to obtain crude 2-methyl-5-oxa-2,8-diazaspiro[3.5]nonane (1.2 g, 8.44 mmol, 128.43% yield). The obtained material was used in the next step without purification.

Yield: 1.2 g (crude)

$^1$H NMR (500 MHz, CDCl₃) δ (ppm) 1.23 (m, 1H), 2.35 (s, 3H), 2.77-2.97 (m, 4H), 3.41-3.43 (m, 2H), 3.55-3.57 (m, 2H), 4.84 (s, 2H).

Step 2: The Synthesis of rac-tert-butyl (2R,5S)-5-methyl-2-[4-(2-methyl-2,6-diazaspiro[3.5]nonan-6-yl)phenyl]piperidine-1-carboxylate Prepared by General Procedure Scheme F Step 3 (Method E)

Yield: 0.1 g (48.12%)

LCMS(ESI): [M+H]⁺ m/z: calcd 416.4; found 416.4; Rt=1.064 min.

Step 3: The Synthesis of rac-2-methyl-8-[4-[(2R,5S)-5-methyl-2-piperidyl]phenyl]-5-oxa-2,8-diazaspiro[3.5]nonane Prepared by General Procedure Scheme F Step 4 (Method B)

Yield: 0.12 g (crude)

LCMS(ESI): [M+H]⁺ m/z: calcd 316.2; found 316.2; Rt=0.700 min.

Step 4: The Synthesis of rac-N-(6-amino-5-ethyl-3-pyridyl)-2-[(2R,5S)-5-methyl-2-[4-(2-methyl-5-oxa-2,8-diazaspiro[3.5]nonan-8-yl)phenyl]-1-piperidyl]-2-oxo-acetamide (Compound 1329

Prepared by General Procedure Scheme F Step 5

HPLC conditions: 40-50% 2-10 min; water/MeCN; Flow 30 mL/min; loading pump 4 mL/min MeCN; column Sun-Fire 19*100 mm, 5 um Yield: 28.0 mg (14.53%)

$^1$H NMR (DMSO-d₆, 600 MHz): δ (ppm) 0.71-0.78 (m, 1H), 0.99-1.13 (m, 5H), 1.29-2.20 (m, 5H), 2.32-2.40 (m, 4H), 2.89-2.90 (m, 2H), 3.03 (m, 2H), 3.13-3.18 (m, 3H), 3.38-3.42 (m, 3H), 3.64-4.19 (m, 3H), 5.05-5.63 (m, 3H), 6.93-6.97 (m, 2H), 7.15-7.21 (m, 2H), 7.46-7.51 (m, 1H), 7.99-8.16 (m, 1H), 10.47-10.54 (m, 1H).

LCMS(ESI): [M+H]⁺ m/z: calcd 507.4; found 507.4; Rt=2.217 min.

Step 5: The Synthesis of rel-N-(6-amino-5-ethyl-3-pyridyl)-2-[(2S,5R)-5-methyl-2-[4-(2-methyl-5-oxa-2,8-diazaspiro[3.5]nonan-8-yl)phenyl]-1-piperidyl]-2-oxo-acetamide (Compound 1150) and rel-N-(6-amino-5-ethyl-3-pyridyl)-2-[(2R,5S)-5-methyl-2-[4-(2-methyl-5-oxa-2,8-diazaspiro[3.5]nonan-8-yl)phenyl]-1-piperidyl]-2-oxo-acetamide (Compound 1339

Prepared by General Procedure Scheme F Step 6

Chiral separation conditions: Chiracel OD-H (250*20 mm, 5 mkm); Mobile phase: Hexane-IPA-MeOH, 80-10-10;

Flow=12 mL/min; Column Temperature: 24° C.; Wavelength: 205 nm; RetTime (isomer A)=63.71 min, RetTime (isomer B)=85.15 min.

Compound 1339:
Yield: 12.21 mg (48.84%)
RT (Chiracel OD-H (250*20 mm, 5 mkm); Hexane-IPA-MeOH, 80-10-10; 0.6 mL/min)=75.345 min.
$^1$H NMR (600 MHz, dmso) δ 0.97-1.04 (m, 3H), 1.05-1.14 (m, 3H), 1.32 (t, 1H), 1.68 (d, 1H), 1.85 (d, 1H), 2.03 (d, 1H), 2.16 (d, 1H), 2.35 (s, 3H), 2.40 (d, 3H), 2.69-3.06 (m, 5H), 3.19 (d, 3H), 3.38-4.02 (m, 6H), 5.30 (d, 1H), 5.62 (d, 2H), 6.95 (dd, 2H), 7.18 (dd, 2H), 7.44-7.52 (m, 1H), 8.03 (d, 1H), 10.48 (d, 1H).
LCMS(ESI): [M+H]$^+$ m/z: calcd 507.2; found 507.2; Rt=0.886 min.

Compound 1150:
Yield: 11.18 mg (44.72%)
RT (Chiracel OD-H (250*20 mm, 5 mkm); Hexane-IPA-MeOH, 80-10-10; 0.6 mL/min)=59.883 min.
$^1$H NMR (600 MHz, dmso) δ 0.99-1.13 (m, 6H), 1.27-1.37 (m, 1H), 1.63-1.72 (m, 1H), 1.79-1.90 (m, 1H), 1.92-2.22 (m, 2H), 2.36-2.39 (m, 4H), 2.70-3.07 (m, 5H), 3.13-3.22 (m, 3H), 3.42-3.98 (m, 5H), 5.02-5.57 (m, 1H), 5.58-5.66 (m, 2H), 6.93-6.99 (m, 2H), 7.13-7.23 (m, 2H), 7.44-7.52 (m, 1H), 7.99-8.09 (m, 1H), 10.44-10.53 (m, 1H).
LCMS(ESI): [M+2H]$^+$ m/z: calcd 508.4; found 508.4; Rt=0.883 min.

Example 547. The Synthesis of N-(6-amino-5-ethylpyridin-3-yl)-2-((2R,5S)-2-(3-(2-(dimethylamino)propoxy)phenyl)-5-methylpiperidin-1-yl)-2-oxoacetamide (Compound 1290)

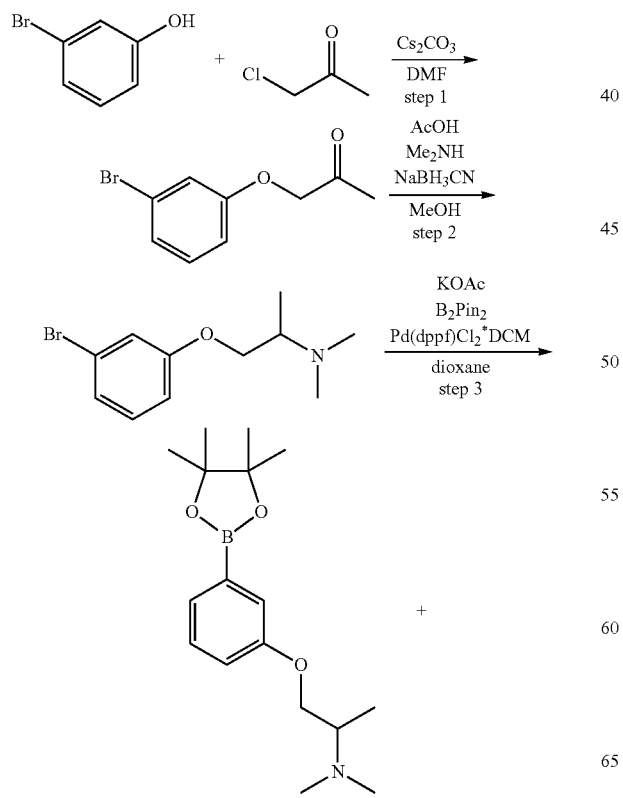

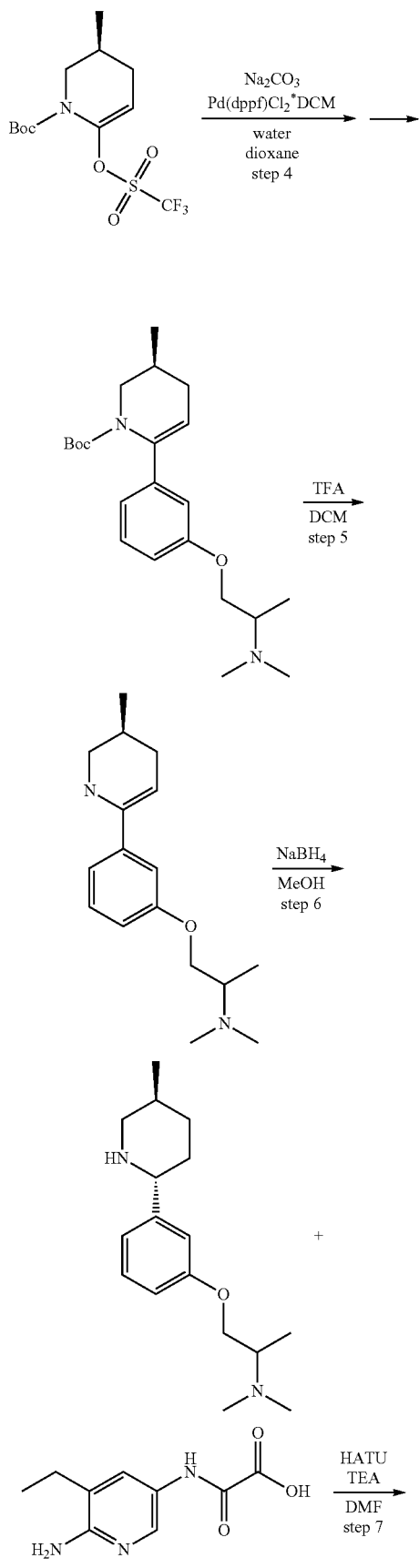

Compound 1290

Step 1: Synthesis of 1-(3-bromophenoxy)propan-2-one 3-bromophenol (6.6 g, 38.15 mmol) and cesium carbonate (21.13 g, 64.85 mmol) was dissolved in DMF (70 mL) and stirred for 15 min at rt. 1-chloropropan-2-one (5.29 g, 57.22 mmol, 4.56 mL) was added and the resulting mixture stirred overnight at rt.

LCMS(ESI): [M]⁺ m/z: calcd 229.2; found 230.2; Rt=1.253 min.

Step 2: Synthesis of 1-(3-bromophenoxy)-N,N-dimethylpropan-2-amine

N-methylmethanamine (4.92 g, 43.65 mmol, 6.35 mL) and acetic acid (2.62 g, 43.65 mmol, 2.50 mL) were added to the solution of 1-(3-bromophenoxy)propan-2-one (5 g, 21.83 mmol) in MeOH (50 mL). Resulting mixture was stirred at 20° C. for 1 hr before sodium cyan borohydride (2.74 g, 43.65 mmol) was added thereto. After that, stirring was continued for 16 hr. Then, solvent was removed under reduced pressure and residue was partitioned between 10% aq. K₂CO₃ solution (30 ml) and DCM (80 ml). Organic layer was separated, dried over solid K₂CO₃ and concentrated under reduced pressure, purified by FCC (Companion comb flash; 40 g SiO₂,CHCl₃-MeCN from 0~100%, flow rate=40 mL/min, cv=15) to obtained 1-(3-bromophenoxy)-N,N-dimethyl-propan-2-amine (1 g, 3.87 mmol, 17.75% yield).

LCMS(ESI): [M]⁺ m/z: calcd 258.2; found 259.2; Rt=0.877 min.

Step 3: Synthesis of N,N-dimethyl-1-(3-(4,4,5,5-tetramethyl-1,3,2-dioxaborolan-2-yl)phenoxy)propan-2-amine A mixture of 1-(3-bromophenoxy)-N,N-dimethyl-propan-2-amine (872 mg, 3.38 mmol), 4,4,5,5-tetramethyl-2-(4,4,5,5-tetramethyl-1,3,2-dioxaborolan-2-yl)-1,3,2-dioxaborolane (857.76 mg, 3.38 mmol) and potassium acetate (663.00 mg, 6.76 mmol, 422.29 μL) in dioxane (10 mL) was evacuated and then backfilled with argon. This operation was repeated two times, then Pd(dppf)Cl₂*DCM (247.16 mg, 337.78 μmol) was added and the reaction mixture was stirred under argon at 90° C. for 12 hr, then cooled down and filtered. The filter cake was washed with dioxane (2*50 ml) and discarded. The filtrate was concentrated in vacuum to afford crude N,N-dimethyl-1-[3-(4,4,5,5-tetramethyl-1,3,2-dioxaborolan-2-yl)phenoxy]propan-2-amine as brown oil, which was used directly in the step.

Step 4: Synthesis of (3S)-tert-butyl 6-(3-(2-(dimethylamino)propoxy)phenyl)-3-methyl-3,4-dihydropyridine-1(2H)-carboxylate N,N-dimethyl-1-[3-(4,4,5,5-tetramethyl-1,3,2-dioxaborolan-2-yl)phenoxy]propan-2-amine (1.56 g, 5.10 mmol), tert-butyl (3S)-3-methyl-6-(trifluoromethylsulfonyloxy)-3,4-dihydro-2H-pyridine-1-carboxylate (1.76 g, 5.10 mmol) and sodium carbonate (1.08 g, 10.21 mmol, 427.35 μL) were mixed in a mixture of dioxane (9 mL) and water (3 mL) and the resulting mixture was evacuated and backfilled three times with argon. Pd(dppf)Cl₂*DCM (208.43 mg, 255.23 μmol) was added to the previous mixture and the resulting mixture was heated at 90° C. overnight. The reaction mixture was diluted with water (30 ml) and the resulting mixture was extracted with EtOAc (2*30 ml). Combined organic layers were washed with brine (30 ml), dried over sodium sulfate, filtered and concentrated in vacuum to obtain tert-butyl (3S)-6-[3-[2-(dimethylamino)propoxy]phenyl]-3-methyl-3,4-dihydro-2H-pyridine-1-carboxylate (1.63 g, 4.34 mmol, 85.11% yield).

LCMS(ESI): [M]⁺ m/z: calcd 374.2; found 375.2; Rt=1.313 min.

Step 5: Synthesis of N,N-dimethyl-1-(3-((S)-5-methyl-3,4,5,6-tetrahydropyridin-2-yl)phenoxy)propan-2-amine tert-butyl (3S)-6-[3-[2-(dimethylamino)propoxy]phenyl]-3-methyl-3,4-dihydro-2H-pyridine-1-carboxylate (1.63 g, 4.35 mmol) was dissolved in DCM (6 mL) and TFA (6 mL) was added thereto. The resulting mixture was stirred for 1 hr. The reaction mixture was concentrated in vacuum. Aq. K₂CO₃ solution (12 g in 40 ml of water) was added to the residue and the resulting mixture was extracted with DCM (2*40 ml). Combined organic layers were dried over sodium sulfate, filtered and concentrated in vacuum to obtain N,N-dimethyl-1-[3-[(3S)-3-methyl-2,3,4,5-tetrahydropyridin-6-yl]phenoxy]propan-2-amine (1 g, 3.64 mmol, 83.73% yield).

LCMS(ESI): [M]⁺ m/z: calcd 274.2; found 275.2; Rt=0.590 min.

Step 6: Synthesis of N,N-dimethyl-1-(3-((2R,5S)-5-methylpiperidin-2-yl)phenoxy)propan-2-amine N,N-dimethyl-1-[3-[(3S)-3-methyl-2,3,4,5-tetrahydropyridin-6-yl]phenoxy]propan-2-amine (1 g, 3.64 mmol) was dissolved in MeOH (20 mL) and sodium borohydride (413.62 mg, 10.93 mmol, 385.12 μL) was added portion wise. The resulting mixture was stirred overnight. Water (10 ml) was added to the reaction mixture and the resulting mixture was concentrated in vacuum. The residue was diluted with water (30 ml) and the resulting mixture was extracted with DCM (2*40 ml). Combined organic layers were dried over sodium sulfate, filtered and concentrated in vacuum to obtain N,N-dimethyl-1-[3-[(2R,5S)-5-methyl-2-piperidyl]phenoxy]propan-2-amine (1.03 g, crude).

LCMS(ESI): [M]⁺ m/z: calcd 276.2; found 277.2; Rt=0.672 min.

Step 7: Synthesis of N-(6-amino-5-ethylpyridin-3-yl)-2-((2R,5S)-2-(3-(2-(dimethylamino)propoxy)phenyl)-5-methylpiperidin-1-yl)-2-oxoacetamide (Compound 1290

N,N-dimethyl-1-[3-[(2R,5S)-5-methyl-2-piperidyl]phenoxy]propan-2-amine (328 mg, 1.19 mmol), 2-[(6-amino-5-ethyl-3-pyridyl)amino]-2-oxo-acetic acid (248.24 mg, 1.19 mmol) and TEA (600.37 mg, 5.93 mmol, 826.95 µL) were mixed together in DMF (3 mL) and HATU (541.43 mg, 1.42 mmol) was added thereto. The resulting mixture was stirred overnight. The reaction mixture was submitted to HPLC and purified (2-10 min 30-60% MeOH+NH$_3$30 ml/min (loading pump 4 ml MeOH), column: SunFire 100*19 mm, 5 microM) to obtain N-(6-amino-5-ethyl-3-pyridyl)-2-oxo-2-[(2R,5S)-2-[3-[2-(dimethylamino)propoxy]phenyl]-5-methyl-1-piperidyl]acetamide (15.7 mg, 33.58 µmol, 2.83% yield) and N-(6-amino-5-ethyl-3-pyridyl)-2-oxo-2-[(2R,5S)-2-[3-[2-(dimethylamino)propoxy]phenyl]-5-methyl-1-piperidyl]acetamide (32.7 mg, 69.93 µmol, 5.89% yield).

$^1$H NMR (600 MHz, DMSO-d$_6$) δ (ppm) 0.98-1.03 (m, 6H), 1.06-1.13 (m, 3H), 1.27-1.38 (m, 1H), 1.58-1.71 (m, 1H), 1.80-1.93 (m, 1H), 1.95-2.18 (m, 2H), 2.19-2.22 (m, 6H), 2.36-2.42 (m, 2H), 2.73-3.26 (m, 2H), 3.44-4.05 (m, 3H), 5.10-5.55 (m, 1H), 5.57-5.67 (m, 2H), 6.77-6.94 (m, 3H), 7.21-7.32 (m, 1H), 7.42-7.54 (m, 1H), 7.97-8.09 (m, 1H), 10.47

10.58 (m, 1H).

LCMS(ESI): [M]$^+$ m/z: calcd 467.2; found 468.2; Rt=2.156 min.

Example 548. The Synthesis of N-(6-amino-5-ethylpyridin-3-yl)-2-((2R,5)-5-methyl-2-(2-(1-methylpiperidin-4-yl)imidazo[1,2-a]pyridin-7-yl)piperidin-1-yl)-2-oxoacetamide (Compound 1274

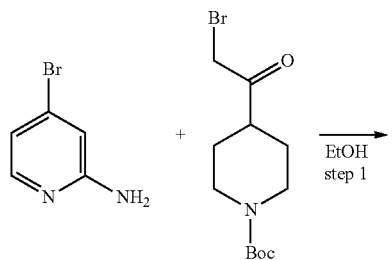

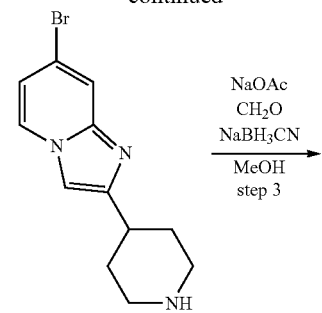

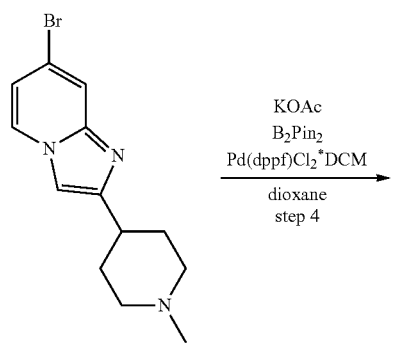

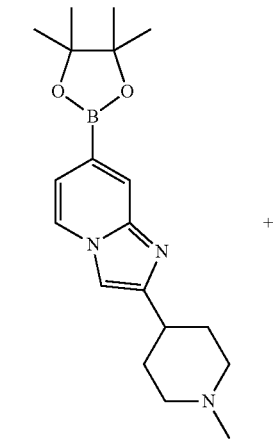

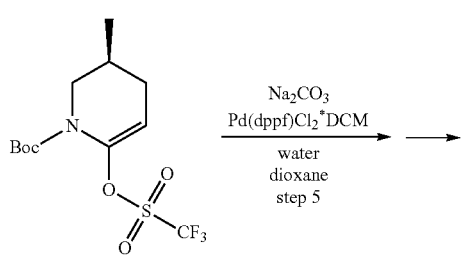

2451

-continued

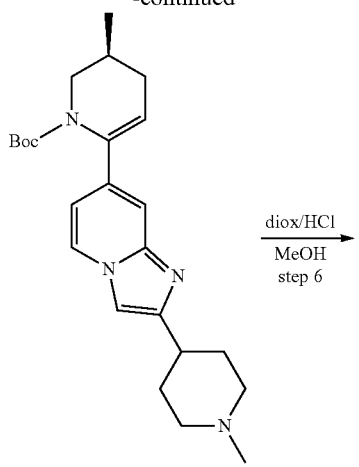

diox/HCl
MeOH
step 6

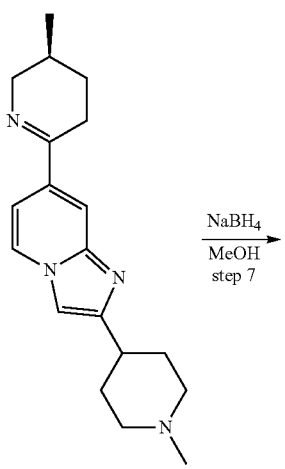

NaBH₄
MeOH
step 7

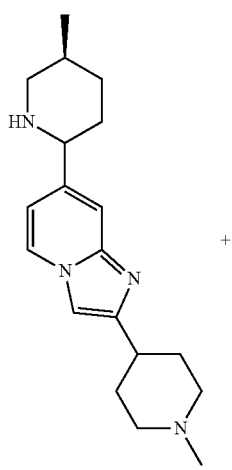

+

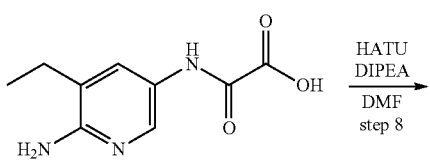

HATU
DIPEA
DMF
step 8

2452

-continued

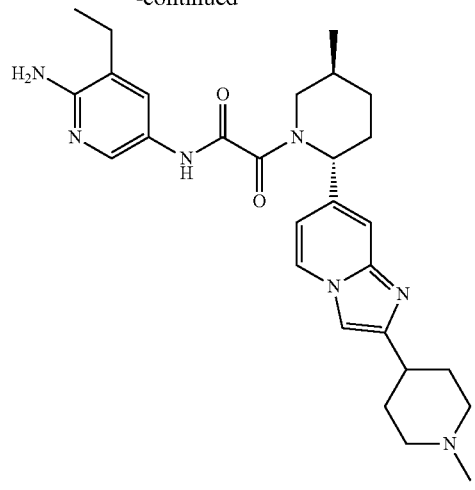

EN-TG2-7340

Step 1: Synthesis of tert-butyl 4-(7-bromoimidazo [1,2-a]pyridin-2-yl)piperidine-1-carboxylate 4-bromopyridin-2-amine (2.83 g, 16.33 mmol) and tert-butyl 4-(2-bromoacetyl)piperidine-1-carboxylate (5 g, 16.33 mmol) was dissolved in EtOH (50 mL) and it was refluxed for 16 hr. Then it was evaporated to afford tert-butyl 4-(7-bromoimidazo[1,2-a]pyridin-2-yl)piperidine-1-carboxylate (5.6 g, 14.73 mmol, 90.18% yield).

LCMS(ESI): $[M]^+$ m/z: calcd 380.2; found 381.2; Rt=0.950 min.

Step 2: Synthesis of 7-bromo-2-(Piperidin-4-yl) imidazo[1,2-a]pyridine tert-butyl 4-(7-bromoimidazo[1,2-a]pyridin-2-yl)piperidine-1-carboxylate (5.6 g, 14.73 mmol) was dissolved in MeOH (50 mL) and diox/HCl (14.73 mmol, 6 mL) was added. Then reaction mixture was stirred at rt for 4 hr and it was filtered on. The solid was dried to afford 7-bromo-2-(4-piperidyl)imidazo[1,2-a]pyridine (4.9 g, 13.88 mmol, 94.24% yield, 2HCl).

LCMS(ESI): $[M]^+$ m/z: calcd 280.2; found 281.2; Rt=0.339 min.

Step 3: Synthesis of 7-bromo-2-(1-methylpiperidin-4-yl)imidazo[1,2-a]pyridine

Formaldehyde, 37% w/w aq. soln., stab. with 7-8% MeOH (833.38 mg, 27.76 mmol, 769.51 µL) and sodium acetate (2.28 g, 27.76 mmol, 1.49 mL) were added to the solution of 7-bromo-2-(4-piperidyl)imidazo[1,2-a]pyridine (4.9 g, 13.88 mmol, 2HCl) in MeOH (77.88 mL). Resulting mixture was stirred at 20° C. for 1 hour before sodium cyan borohydride (1.74 g, 27.76 mmol) was added thereto. After that, stirring was continued for 16 hr. Then, solvent was removed under reduced pressure and residue was partitioned between 15% aq. $K_2CO_3$ solution (30 ml) and DCM (50 ml). Organic layer was separated, dried over solid $Na_2SO_4$ and concentrated under reduced pressure, leaving 7-bromo-2-(1-methyl-4-piperidyl)imidazo[1,2-a]pyridine (4 g, 13.60 mmol, 97.98% yield).

LCMS(ESI): [M]⁺ m/z: calcd 294.2; found 295.2; Rt=0.256 min.

Step 4: Synthesis of 2-(1-methylpiperidin-4-yl)-7-(4,4,5,5-tetramethyl-1,3,2-dioxaborolan-2-yl)imidazo[1,2-a]pyridine To a solution of 7-bromo-2-(1-methyl-4-piperidyl)imidazo[1,2-a]pyridine (4 g, 13.60 mmol) was added potassium acetate (2.67 g, 27.19 mmol, 1.70 mL) and bis(pinacolato) diboron (3.45 g, 13.60 mmol). The reaction mixture was degassed and Pd(dppf)Cl₂*DCM (555.18 mg, 679.83 µmol) added in one portion. The mixture was further degassed with Ar and heated at 90° C. for 16 hr. After this time the reaction mixture was allowed to cool to rt, filtered and the solvent removed in vacuum to afford 2-(1-methyl-4-piperidyl)-7-(4,4,5,5-tetramethyl-1,3,2-dioxaborolan-2-yl)imidazo[1,2-a] pyridine (4.6 g, 13.48 mmol, 99.14% yield).

LCMS(ESI): [M]⁺ m/z: calcd 341.2; found 342.2; Rt=0.209 min.

Step 5: Synthesis of (S)-tert-butyl 3-methyl-6-(2-(1-methylpiperidin-4-yl)imidazo[1,2-a]pyridin-7-yl)-3,4-dihydropyridine-1(2H)-carboxylate tert-butyl (3S)-3-methyl-6-(trifluoromethylsulfonyloxy)-3,4-dihydro-2H-pyridine-1-carboxylate (6.98 g, 20.22 mmol), 2-(1-methyl-4-piperidyl)-7-(4,4,5,5-tetramethyl-1,3,2-dioxaborolan-2-yl)imidazo[1,2-a]pyridine (4.6 g, 13.48 mmol) and sodium carbonate (4.29 g, 40.44 mmol, 1.69 mL) was added to a mixture of dioxane (58.95 mL) and water (19.65 mL). The resulting mixture was evacuated and then backfilled with argon, this operation was repeated three times, then Pd(dppf)Cl₂*DCM (550.40 mg, 673.98 µmol) was added under argon. The reaction mixture was stirred under argon at 70° C. for 16 hr, then cooled and filtered. The filter cake was washed with dioxane (2*20 ml) and discarded. The filtrate was evaporated in vacuum to afford tert-butyl (3S)-3-methyl-6-[2-(1-methyl-4-piperidyl)imidazo[1,2-a]pyridin-7-yl]-3,4-dihydro-2H-pyridine-1-carboxylate (5 g, 12.18 mmol, 90.35% yield) as brown oil, which was used in next step without purification.

LCMS(ESI): [M]⁺ m/z: calcd 410.2; found 411.2; Rt=0.928 min.

Step 6: Synthesis of (S)-7-(5-methyl-3,4,5,6-tetrahydropyridin-2-yl)-2-(1-methylpiperidin-4-yl)imidazo[1,2-a]pyridine tert-butyl (3S)-3-methyl-6-[2-(1-methyl-4-piperidyl)imidazo[1,2-a]pyridin-7-yl]-3,4-dihydro-2H-pyridine-1-carboxylate (5 g, 12.18 mmol) was dissolved in MeOH (50 mL) and diox/HCl (10.96 mmol, 5 mL) was added thereto. Then it was stirred at rt for 2 hr. The reaction mixture was evaporated to afford 2-(1-methyl-4-piperidyl)-7-[(3S)-3-methyl-2,3,4,5-tetrahydropyridin-6-yl]imidazo[1,2-a]pyridine (3.8 g, 9.91 mmol, 81.39% yield, 2HCl).

LCMS(ESI): [M]⁺ m/z: calcd 310.2; found 311.2; Rt=0.581 min.

Step 7: Synthesis of 7-((5S)-5-methylpiperidin-2-yl)-2-(1-methylpiperidin-4-yl)imidazo[1,2-a]pyridine To a stirred solution of 2-(1-methyl-4-piperidyl)-7-[(3S)-3-methyl-2,3,4,5-tetrahydropyridin-6-yl]imidazo[1,2-a] pyridine (3.8 g, 9.91 mmol, 2HCl) in MeOH (50 mL) was added sodium borohydride (750.03 mg, 19.82 mmol, 698.35 µL) at 0° C. The resulting reaction mixture was stirred at 25° C. for 16 hr. Upon completion, the reaction mixture was concentrated under reduced pressure, then quenched with water 20 mL and 50 ml EtOAc. The combined organic phase was washed with Brine 20 mL, dried over Na₂SO₄ and concentrated under reduced pressure to obtain 2-(1-methyl-4-piperidyl)-7-[(2R,5S)-5-methyl-2-piperidyl]imidazo[1,2-a]pyridine (2.5 g, 8.00 mmol, 80.72% yield), which was used in next step without farther purification.

LCMS(ESI): [M]⁺ m/z: calcd 312.2; found 313.2; Rt=0.255 min.

Step 8: Synthesis of N-(6-amino-5-ethylpyridin-3-yl)-2-((2R,5S)-5-methyl-2-(2-(1-methylpiperidin-4-yl)imidazo[1,2-a]pyridin-7-yl)piperidin-1-yl)-2-oxoacetamide (Compound 1274)

DIPEA (308.90 mg, 2.39 mmol, 416.30 µL) was added to the solution of respective 2-[(6-amino-5-ethyl-3-pyridyl) amino]-2-oxo-acetic acid (0.2 g, 956.02 µmol) and 2-(1-methyl-4-piperidyl)-7-[(2R,5S)-5-methyl-2-piperidyl]imidazo[1,2-a]pyridine (298.71 mg, 956.02 µmol) in DMF (19.58 mL). The resulting mixture was stirred for 5 min followed by the addition of HATU (399.86 mg, 1.05 mmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and MeCN+FA as an eluent mixture) to afford N-(6-amino-5-ethyl-3-pyridyl)-2-oxo-2-[(2R,5S)-5-methyl-2-[2-(1-methyl-4-piperidyl)imidazo[1,2-a]pyridin-7-yl]-1-piperidyl]acetamide (21.9 mg, 39.84 µmol, 4.17% yield, HCOOH).

¹H NMR (600 MHz, DMSO-d₆) δ (ppm) 0.99-1.14 (m, 6H), 1.30-1.39 (m, 1H), 1.66-1.74 (m, 3H), 1.76-2.18 (m, 7H), 2.19-2.27 (m, 4H), 2.35-2.42 (m, 1H), 2.62-2.65 (m, 1H), 2.76-2.91 (m, 3H), 3.93-4.07 (m, 1H), 5.13-5.58 (m, 1H), 5.58-5.67 (m, 2H), 6.71-6.86 (m, 1H), 7.33-7.54 (m, 2H), 7.62-7.69 (m, 1H), 7.99-8.09 (m, 1H), 8.40-8.45 (m, 1H), 10.50-10.64 (m, 1H).

LCMS(ESI): [M]⁺ m/z: calcd 503.2; found 504.2; Rt=1.336 min.

Example 549. The Synthesis of N-(6-amino-5-ethylpyridin-3-yl)-2-((2R,5)-5-methyl-2-(3-(((R)-1-methylpyrrolidin-3-yl)methoxy)phenyl)piperidin-1-yl)-2-oxoacetamide (Compound 1178

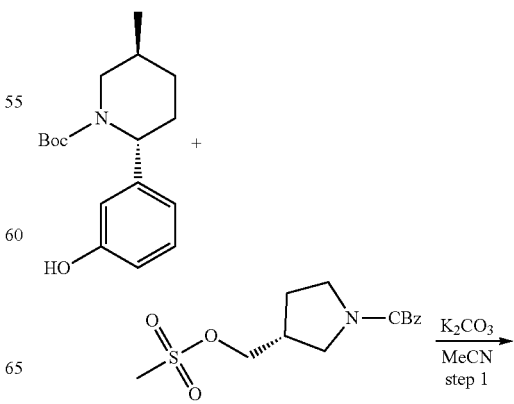

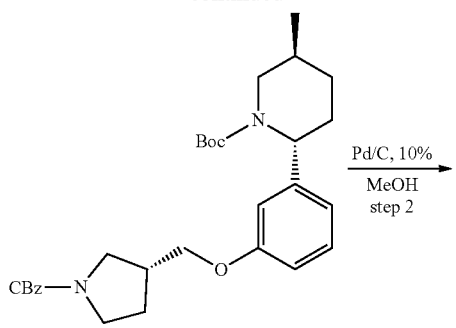

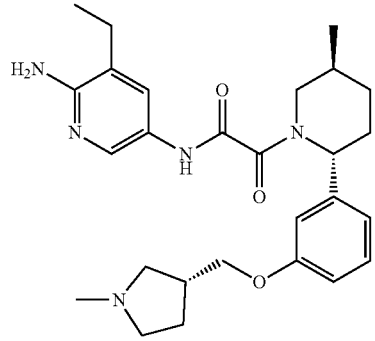

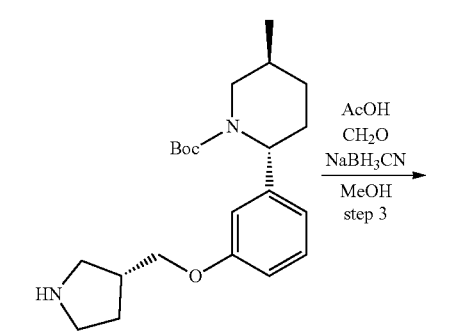

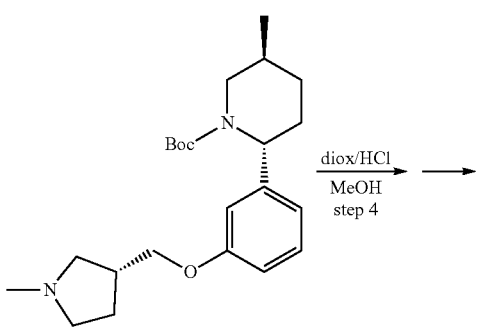

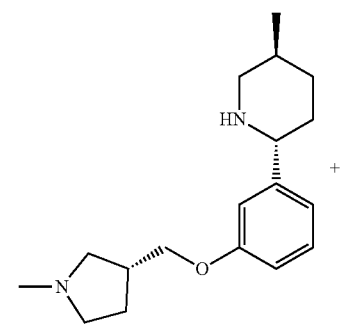

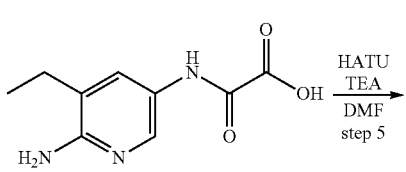

Step 1: Synthesis of (2R,5S)-tert-butyl 2-(3-(((R)-1-((benzyloxy)carbonyl)pyrrolidin-3-yl)methoxy)phenyl)-5-methylpiperidine-1-carboxylate tert-butyl (2R,5S)-2-(3-hydroxyphenyl)-5-methyl-piperidine-1-carboxylate (0.9 g, 3.09 mmol), benzyl (3R)-3-(methylsulfonyloxymethyl)pyrrolidine-1-carboxylate (1.26 g, 4.02 mmol) and potassium carbonate, anhydrous, 99% (853.78 mg, 6.18 mmol, 372.83 μL) was mixed together in MeCN (19.63 mL) and heated at 81° C. for 36 hr. The reaction mixture was concentrated on vacuum. The obtained residue was dissolved in EtOAc/H$_2$O, the EtOAc layer was separated and the aqueous layer was extracted twice with EtOAc. The combined organic layers was dried over Na$_2$SO$_4$, filtered and concentrated on vacuum. The crude product was purified by FCC (MTBE in hexanes form 0% to 100%). tert-butyl (2R,5S)-5-methyl-2-[3-[[(3R)-1-benzyloxycarbonylpyrrolidin-3-yl]methoxy]phenyl]piperidine-1-carboxylate (0.25 g, 491.50 mol, 15.91% yield) was obtained as a light-yellow gum.

LCMS(ESI): [M−Boc]$^+$ m/z: calcd 408.2; found 409.2; Rt=1.814 min.

Step 2: Synthesis of (2R,5S)-tert-butyl 5-methyl-2-(3-((R)-pyrrolidin-3-ylmethoxy)phenyl)piperidine-1-carboxylate A solution of tert-butyl (2R,5S)-5-methyl-2-[3-[[(3R)-1-benzyloxycarbonylpyrrolidin-3-yl]methoxy]phenyl]piperidine-1-carboxylate (0.25 g, 491.50 μmol) in MeOH (10 mL) was hydrogenated over Pd/C (10%) (0.075 g, 491.50 μmol) under H$_2$ (1 atm) at 20° C. for 12 hr. The reaction mixture was filtered, the filter cake was washed with MeOH and the filtrate was concentrated under reduced pressure. The obtained product was use in the next step without further purification. tert-butyl (2R,5S)-5-methyl-2-[3-[[(3R)-pyrrolidin-3-yl]methoxy]phenyl]piperidine-1-carboxylate (0.21 g, crude) was obtained as a light-yellow gum.

LCMS(ESI): [M]f m/z: calcd 374.2; found 375.2; Rt=1.241 min.

Step 3: Synthesis of (2R,5S)-tert-butyl 5-methyl-2-(3-(((R)-1-methylpyrrolidin-3-yl)methoxy)phenyl)piperidine-1-carboxylate tert-butyl (2R,5S)-5-methyl-2-[3-[[(3R)-pyrrolidin-3-yl]methoxy]phenyl]piperidine-1-carboxylate (0.21 g, 560.72 μmol), formaldehyde, 37% w/w aq. soln., stab. with 7-8%

MeOH (25.25 mg, 841.09 µmol, 23.32 µL) and acetic acid (67.35 mg, 1.12 mmol, 64.20 µL) was dissolved in MeOH (5 mL) and stirred for 1 hr then sodium cyan borohydride (105.71 mg, 1.68 mmol) was added portion wise at cooling with ice+water and the reaction mixture was stirred for 12 hr. Solvent was evaporated, obtained residue was dissolved in Na$_2$CO$_3$(aq) and extracted with DCM (3*50 ml), DCM layer was dried over Na$_2$SO$_4$, filtered and evaporated on vacuum. The obtained product was used in the next step without further purification. tert-butyl (2R,5S)-5-methyl-2-[3-[[(3R)-1-methylpyrrolidin-3-yl]methoxy]phenyl]piperidine-1-carboxylate (0.21 g, 540.48 µmol, 96.39% yield) was obtained as a light-yellow gum.

LCMS(ESI): [M]$^+$ m/z: calcd 388.2; found 389.2; Rt=0.954 min.

Step 4: Synthesis of (2R,5S)-5-methyl-2-(3-(((R)-1-methylpyrrolidin-3-yl)methoxy)phenyl)piperidine tert-butyl (2R,5S)-5-methyl-2-[3-[[(3R)-1-methylpyrrolidin-3-yl]methoxy]phenyl]piperidine-1-carboxylate (0.21 g, 540.48 µmol) was dissolved in a mixture of MeOH (7 mL) and diox/HCl (7 mL). The resulting clear solution was stirred for 4 hr at 20° C. The reaction mixture was concentrated on vacuum. (2R,5S)-5-methyl-2-[3-[[(3R)-1-methylpyrrolidin-3-yl]methoxy]phenyl]piperidine (0.2 g, crude, 2HCl) was obtained as a light-yellow gum.

LCMS(ESI): [M]$^+$ m/z: calcd 288.2; found 289.2; Rt=0.601 min.

Step 5: Synthesis of N-(6-amino-5-ethylpyridin-3-yl)-2-((2R,5S)-5-methyl-2-(3-(((R)-1-methylpyrrolidin-3-yl)methoxy)phenyl)piperidin-1-yl)-2-oxoacetamide (Compound 1178

(2R,5S)-5-methyl-2-[3-[[(3R)-1-methylpyrrolidin-3-yl]methoxy]phenyl]piperidine (0.2 g, 553.48 µmol, 2HCl), TEA (392.05 mg, 3.87 mmol, 540.01 µL) and 2-[(6-amino-5-ethyl-3-pyridyl)amino]-2-oxo-acetic acid (115.79 mg, 553.48 µmol) was dissolved in DMF (5 mL) and HATU (231.50 mg, 608.83 µmol) was added in one portion, the resulting mixture was stirred for 3 hr at 20° C. The reaction mixture was submitted to HPLC (2-10 min 60-85% MeOH+ NH$_3$ flow 30 ml/min (loading pump 4 ml MeOH), column: SunFire C18). N-(6-amino-5-ethyl-3-pyridyl)-2-oxo-2-[(2R,5S)-5-methyl-2-[3-[[(3R)-1-methylpyrrolidin-3-yl]methoxy]phenyl]-1-piperidyl]acetamide (0.099 g, 206.42 µmol, 37.29% yield) was obtained as a light-yellow solid.

$^1$H NMR (600 MHz, DMSO-d$_6$) δ (ppm) 0.71-1.04 (m, 3H), 1.07-1.16 (m, 3H), 1.24-1.37 (m, 1H), 1.42-1.52 (m, 1H), 1.61-1.73 (m, 1H), 1.80-1.96 (m, 2H), 1.97-2.14 (m, 1H), 2.14-2.20 (m, 1H), 2.21 (s, 3H), 2.29-2.45 (m, 5H), 2.51-2.52 (m, 2H), 2.73-3.24 (m, 1H), 3.42-3.47 (m, 0.7H), 3.78-3.87 (m, 2H), 3.99-4.05 (m, 0.3H), 5.03-5.57 (m, 1H), 5.57-5.69 (m, 2H), 6.77-6.94 (m, 3H), 7.23-7.32 (m, 1H), 7.42-7.55 (m, 1H), 7.98-8.10 (m, 1H), 10.47 (br s, 1H).

LCMS(ESI): [M]$^+$ m/z: calcd 479.2; found 480.2; Rt=0.754 min.

Example 550. The Synthesis of N-(6-amino-5-ethylpyridin-3-yl)-2-((2R,5S)-5-methyl-2-(3-((1-methylpiperidin-4-yl)methoxy)phenyl)piperidin-1-yl)-2-oxoacetamide (Compound 1348

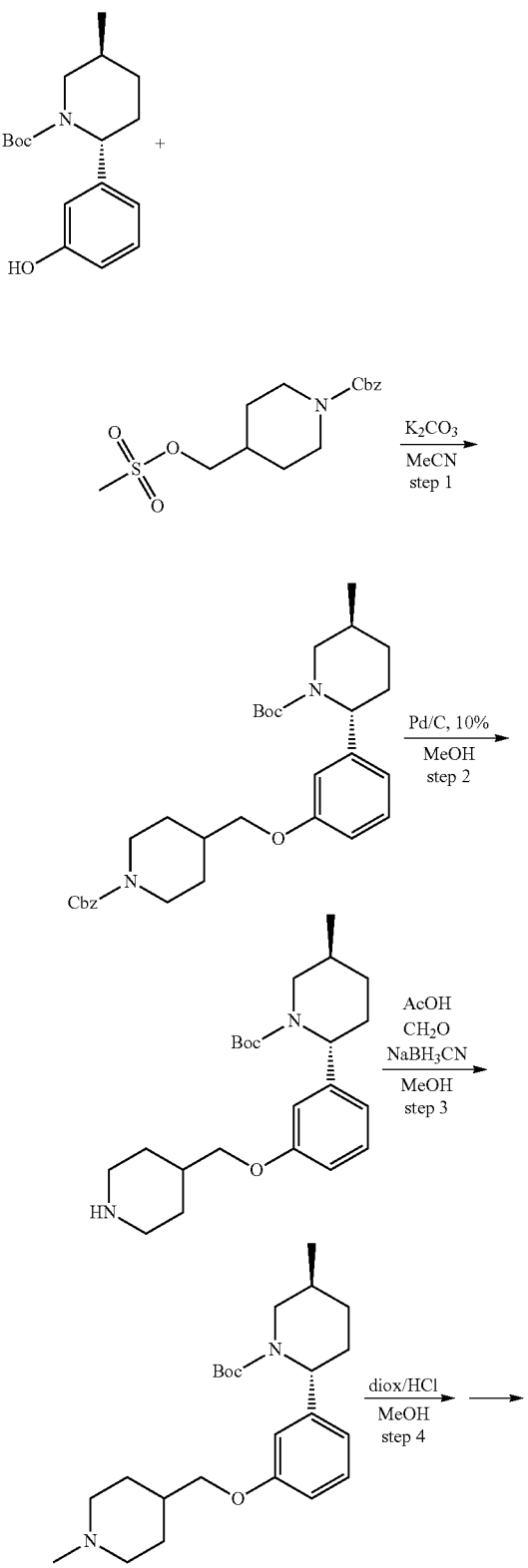

2459
-continued

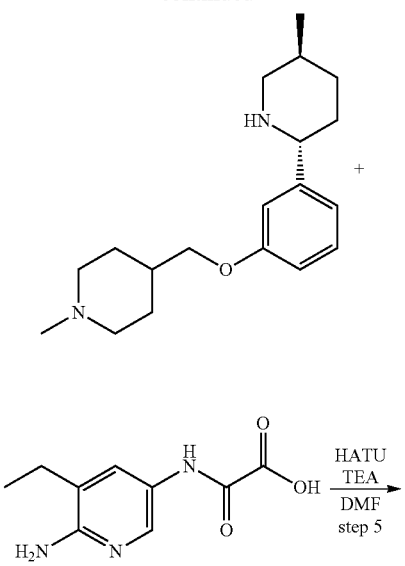

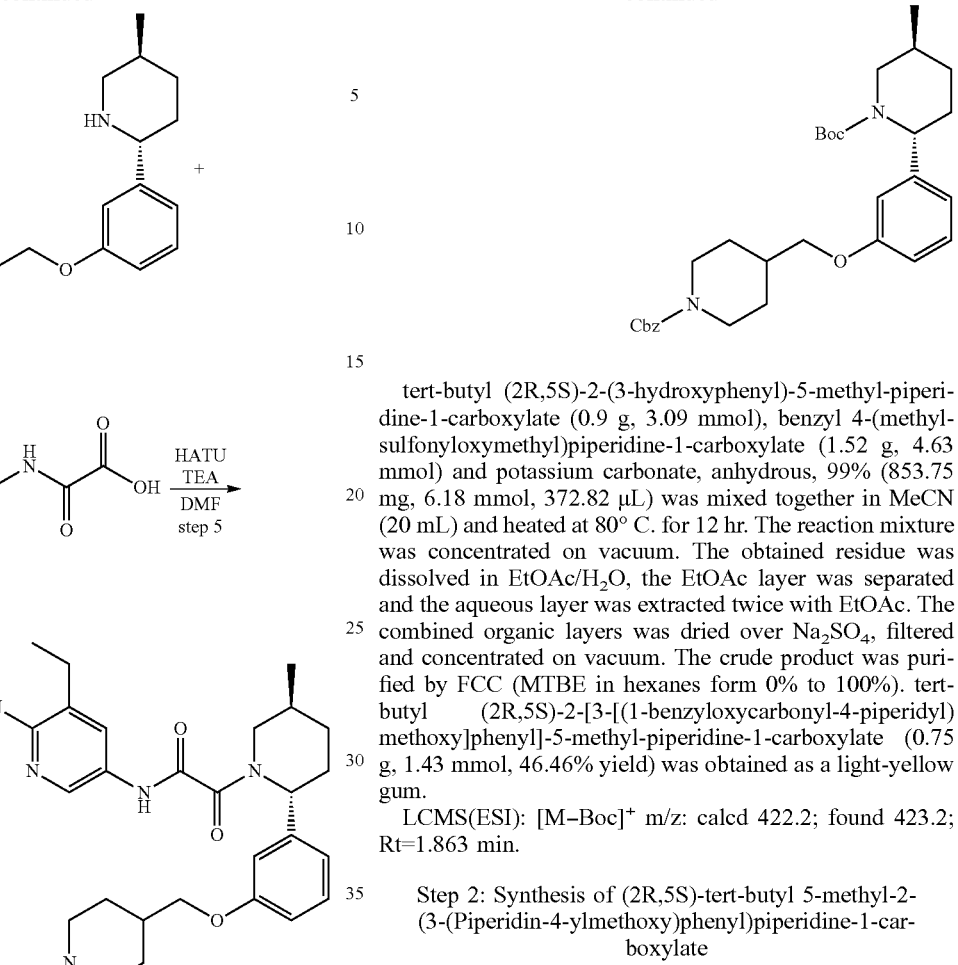

Compound 1348

Step 1: Synthesis of (2R,5S)-tert-butyl 2-(3-((1-((benzyloxy)carbonyl)piperidin-4-yl)methoxy)phenyl)-5-methylpiperidine-1-carboxylate

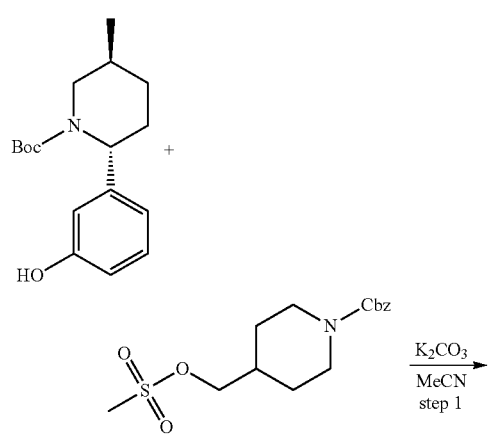

2460
-continued tert-butyl (2R,5S)-2-(3-hydroxyphenyl)-5-methyl-piperidine-1-carboxylate (0.9 g, 3.09 mmol), benzyl 4-(methylsulfonyloxymethyl)piperidine-1-carboxylate (1.52 g, 4.63 mmol) and potassium carbonate, anhydrous, 99% (853.75 mg, 6.18 mmol, 372.82 µL) was mixed together in MeCN (20 mL) and heated at 80° C. for 12 hr. The reaction mixture was concentrated on vacuum. The obtained residue was dissolved in EtOAc/H$_2$O, the EtOAc layer was separated and the aqueous layer was extracted twice with EtOAc. The combined organic layers was dried over Na$_2$SO$_4$, filtered and concentrated on vacuum. The crude product was purified by FCC (MTBE in hexanes form 0% to 100%). tert-butyl (2R,5S)-2-[3-[(1-benzyloxycarbonyl-4-piperidyl)methoxy]phenyl]-5-methyl-piperidine-1-carboxylate (0.75 g, 1.43 mmol, 46.46% yield) was obtained as a light-yellow gum.

LCMS(ESI): [M−Boc]$^+$ m/z: calcd 422.2; found 423.2; Rt=1.863 min.

Step 2: Synthesis of (2R,5S)-tert-butyl 5-methyl-2-(3-(Piperidin-4-ylmethoxy)phenyl)piperidine-1-carboxylate A solution of tert-butyl (2R,5S)-2-[3-[(1-benzyloxycarbonyl-4-piperidyl)methoxy]phenyl]-5-methyl-piperidine-1-carboxylate (0.75 g, 1.43 mmol) in MeOH (10 mL) was hydrogenated over Pd/C (10%) (0.1 g, 1.43 mmol) under H$_2$ (1 atm) at 20° C. for 12 hr. The reaction mixture was filtered, the filter cake was washed with MeOH and the filtrate was concentrated under reduced pressure. The obtained product was use in the next step without further purification. tert-butyl (2R,5S)-5-methyl-2-[3-(4-piperidyl methoxy)phenyl] piperidine-1-carboxylate (0.61 g, crude) was obtained as a light-yellow gum.

LCMS(ESI): [M]$^+$ m/z: calcd 388.2; found 389.2; Rt=1.269 min.

Step 3: Synthesis of (2R,5S)-tert-butyl 5-methyl-2-(3-((1-methylpiperidin-4-yl)methoxy)phenyl)piperidine-1-carboxylate tert-butyl (2R,5S)-5-methyl-2-[3-(4-piperidylmethoxy) phenyl]piperidine-1-carboxylate (0.61 g, 1.57 mmol), formaldehyde, 37% w/w aq. soln., stab. with 7-8% MeOH (70.71 mg, 2.35 mmol, 65.29 µL) and acetic acid (188.56 mg, 3.14 mmol, 179.75 µL) was dissolved in MeOH (10 mL) and stirred for 1 hr then sodium cyan borohydride (295.98 mg, 4.71 mmol) was added portion wise at cooling with ice+ water and the reaction mixture was stirred for 12 hr. Solvent was evaporated, obtained residue was dissolved in Na$_2$CO$_3$ (aq) and extracted with DCM (3*50 ml), DCM layer was dried over Na$_2$SO$_4$, filtered and evaporated on vacuum. The obtained product was used in the next step without further purification. tert-butyl (2R,5S)-5-methyl-2-[3-[(1-methyl-4-piperidyl)methoxy]phenyl]piperidine-1-carboxylate (0.41 g, 1.02 mmol, 64.87% yield) was obtained as a light-yellow gum.

LCMS(ESI): [M]+ m/z: calcd 402.2; found 403.2; Rt=0.967 min.

Step 4: Synthesis of 1-methyl-4-((3-((2R,5S)-5-methylpiperidin-2-yl)phenoxy)methyl)piperidine tert-butyl (2R,5S)-5-methyl-2-[3-[(1-methyl-4-piperidyl)methoxy]phenyl]piperidine-1-carboxylate (0.41 g, 1.02 mmol) was dissolved in a mixture of MeOH (7 mL) and dioxane (HCl) (7 mL). The resulting clear solution was stirred for 4 hr at 20° C. The reaction mixture was concentrated on vacuum. 1-methyl-4-[[3-[(2R,5S)-5-methyl-2-piperidyl]phenoxy]methyl]piperidine (0.3 g, 799.20 µmol, 78.47% yield, 2HCl) was obtained as a light-yellow solid.

LCMS(ESI): [M]+ m/z: calcd 302.2; found 303.2; Rt=0.631 min.

Step 5: Synthesis of N-(6-amino-5-ethylpyridin-3-yl)-2-((2R,5S)-5-methyl-2-(3-((1-methylpiperidin-4-yl)methoxy)phenyl)piperidin-1-yl)-2-oxoacetamide (Compound 1348

1-methyl-4-[[3-[(2R,5S)-5-methyl-2-piperidyl]phenoxy]methyl]piperidine (0.3 g, 799.20 µmol, 2HCl), TEA (566.10 mg, 5.59 mmol, 779.75 µL) and 2-[(6-amino-5-ethyl-3-pyridyl)amino]-2-oxo-acetic acid (167.19 mg, 799.20 µmol) was dissolved in DMF (5 mL) and HATU (334.27 mg, 879.12 µmol) was added in one portion, the resulting mixture was stirred for 3 hr at 20° C. The reaction mixture was submitted to HPLC (2-10 min 60-80% MeOH+NH₃ flow 30 ml/min (loading pump 4 ml MeOH), column: SunFire C18). N-(6-amino-5-ethyl-3-pyridyl)-2-oxo-2-[(2R,5S)-5-methyl-2-[3-[(1-methyl-4-piperidyl)methoxy]phenyl]-1-piperidyl]acetamide (0.153 g, 309.94 µmol, 38.78% yield) was obtained as a light-yellow solid.

¹H NMR (600 MHz, DMSO-d₆) δ (ppm) 0.76-1.03 (m, 3H), 1.06-1.14 (m, 3H), 1.22-1.37 (m, 3H), 1.62-1.75 (m, 4H), 1.80-1.85 (m, 2H), 1.86-2.11 (m, 2H), 2.12 (s, 3H), 2.14-2.26 (m, 1H), 2.37-2.44 (m, 2H), 2.73-2.80 (m, 2.3H), 3.21-3.25 (m, 0.7H), 3.43-3.48 (m, 0.7H), 3.76-3.84 (m, 2H), 3.99-4.06 (m, 0.3H), 5.08-5.57 (m, 1H), 5.58-5.68 (m, 2H), 6.76-6.91 (m, 3H), 7.22-7.32 (m, 1H), 7.43-7.54 (m, 1H), 7.97-8.12 (m, 1H), 10.21 (br s, 1H).

LCMS(ESI): [M]+ m/z: calcd 493.2; found 494.2; Rt=0.773 min.

Example 551. The Synthesis of N-(6-amino-5-ethylpyridin-3-yl)-2-((2R,5)-5-methyl-2-(3-(((S)-1-methylpyrrolidin-3-yl)methoxy)phenyl)piperidin-1-yl)-2-oxoacetamide (Compound 1179

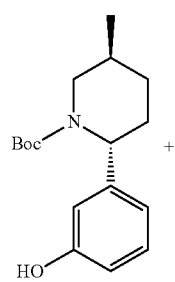

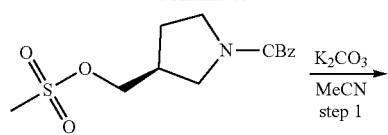

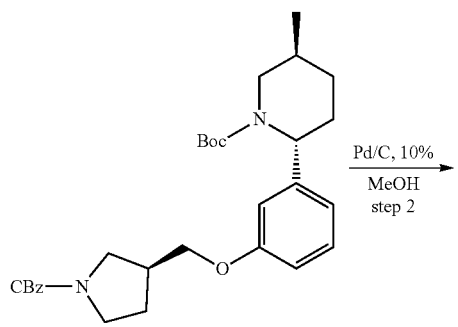

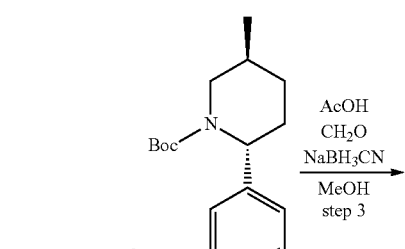

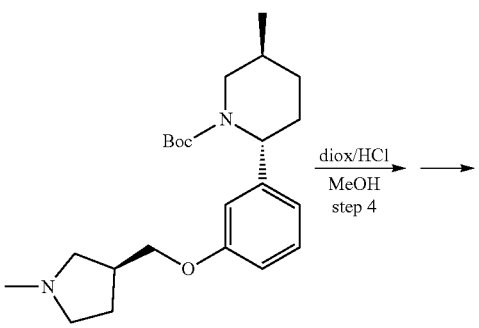

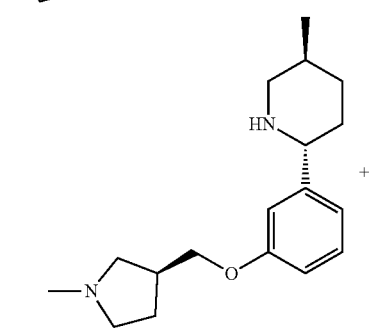

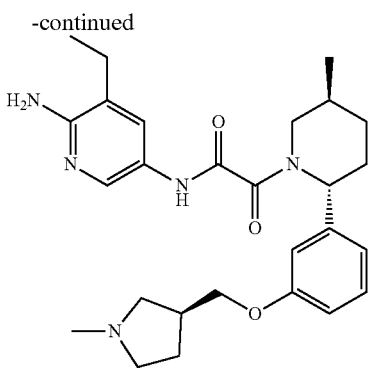

Step 1: Synthesis of (2R,5S)-tert-butyl 2-(3-(((S)-1-((benzyloxy)carbonyl)pyrrolidin-3-yl)methoxy)phenyl)-5-methylpiperidine-1-carboxylate tert-butyl (2R,5S)-2-(3-hydroxyphenyl)-5-methyl-piperidine-1-carboxylate (0.9 g, 3.09 mmol), benzyl (3S)-3-(methylsulfonyloxymethyl)pyrrolidine-1-carboxylate (1.26 g, 4.02 mmol) and potassium carbonate, anhydrous, 99% (853.78 mg, 6.18 mmol, 372.83 μL) was mixed together in MeCN (19.92 mL) and heated at 81° C. for 36 hr. The reaction mixture was concentrated on vacuum. The obtained residue was dissolved in EtOAc/H$_2$O, the EtOAc layer was separated and the aqueous layer was extracted twice with EtOAc. The combined organic layers was dried over Na$_2$SO$_4$, filtered and concentrated on vacuum. The crude product was purified by FCC (MTBE in hexanes form 0% to 100%). tert-butyl (2R,5S)-5-methyl-2-[3-[[(3S)-1-benzyloxycarbonylpyrrolidin-3-yl]methoxy]phenyl]piperidine-1-carboxylate (0.25 g, 491.50 mol, 15.91% yield) was obtained as a light-yellow gum.

LCMS(ESI): [M–Boc]$^+$ m/z: calcd 408.2; found 409.2; Rt=1.814 min.

Step 2: Synthesis of (2R,5S)-tert-butyl 5-methyl-2-(3-((S)-pyrrolidin-3-ylmethoxy)phenyl)piperidine-1-carboxylate A solution of tert-butyl (2R,5S)-5-methyl-2-[3-[[(3S)-1-benzyloxycarbonylpyrrolidin-3-yl]methoxy]phenyl]piperidine-1-carboxylate (0.25 g, 491.50 μmol) in MeOH (10 mL) was hydrogenated over Pd/C (10%) (0.075 g, 491.50 μmol) under H$_2$ (1 atm) at 20° C. for 12 hr. The reaction mixture was filtered, the filter cake was washed with MeOH and the filtrate was concentrated under reduced pressure. The obtained product was use in the next step without further purification. tert-butyl (2R,5S)-5-methyl-2-[3-[[(3S)-pyrrolidin-3-yl]methoxy]phenyl]piperidine-1-carboxylate (0.21 g, crude) was obtained as a light-yellow gum.

LCMS(ESI): [M]$^+$ m/z: calcd 374.2; found 375.2; Rt=1.249 min.

Step 3: Synthesis of (2R,5S)-tert-butyl 5-methyl-2-(3-(((S)-1-methylpyrrolidin-3-yl)methoxy)phenyl)piperidine-1-carboxylate tert-butyl (2R,5S)-5-methyl-2-[3-[[(3S)-pyrrolidin-3-yl]methoxy]phenyl]piperidine-1-carboxylate (0.21 g, 560.72 μmol), formaldehyde, 37% w/w aq. soln., stab. with 7-8% MeOH (25.25 mg, 841.09 μmol, 23.32 μL) and acetic acid (67.35 mg, 1.12 mmol, 64.20 μL) was dissolved in MeOH (5 mL) and stirred for 1 hr then sodium cyan borohydride (105.71 mg, 1.68 mmol) was added portion wise at cooling with ice+water and the reaction mixture was stirred for 12 hr. Solvent was evaporated, obtained residue was dissolved in Na$_2$CO$_3$(aq) and extracted with DCM (3*50 ml), DCM layer was dried over Na$_2$SO$_4$, filtered and evaporated on vacuum. The obtained product was used in the next step without further purification. tert-butyl (2R,5S)-5-methyl-2-[3-[[(3S)-1-methylpyrrolidin-3-yl]methoxy]phenyl]piperidine-1-carboxylate (0.21 g, 540.48 μmol, 96.39% yield) was obtained as a light-yellow gum.

LCMS(ESI): [M]$^+$ m/z: calcd 388.2; found 389.2; Rt=0.956 min.

Step 4: Synthesis of (2R,5S)-5-methyl-2-(3-(((S)-1-methylpyrrolidin-3-yl)methoxy)phenyl)piperidine tert-butyl (2R,5S)-5-methyl-2-[3-[[(3S)-1-methylpyrrolidin-3-yl]methoxy]phenyl]piperidine-1-carboxylate (0.21 g, 540.48 μmol) was dissolved in a mixture of MeOH (7 mL) and dioxane (HCl) (7 mL). The resulting clear solution was stirred for 12 hr at 20° C. The reaction mixture was concentrated on vacuum. (2R,5S)-5-methyl-2-[3-[[(3S)-1-methylpyrrolidin-3-yl]methoxy]phenyl]piperidine (0.18 g, 498.13 μmol, 92.16% yield, 2HCl) was obtained as a light-yellow solid.

LCMS(ESI): [M]$^+$ m/z: calcd 288.2; found 289.2; Rt=0.604 min.

Step 5: Synthesis of N-(6-amino-5-ethylpyridin-3-yl)-2-((2R,5S)-5-methyl-2-(3-(((S)-1-methylpyrrolidin-3-yl)methoxy)phenyl)piperidin-1-yl)-2-oxoacetamide (Compound 1179

(2R,5S)-5-methyl-2-[3-[[(3S)-1-methylpyrrolidin-3-yl]methoxy]phenyl]piperidine (0.18 g, 498.13 μmol, 2HCl), TEA (352.84 mg, 3.49 mmol, 486.01 μL) and 2-[(6-amino-5-ethyl-3-pyridyl)amino]-2-oxo-acetic acid (104.21 mg, 498.13 μmol) was dissolved in DMF (5 mL) and HATU (208.35 mg, 547.95 μmol) was added in one portion, the resulting mixture was stirred for 3 hr at 20° C. The reaction mixture was submitted to HPLC (2-10 min 60-85% MeOH+NH$_3$ flow 30 ml/min (loading pump 4 ml MeOH), column: SunFire C18). N-(6-amino-5-ethyl-3-pyridyl)-2-oxo-2-[(2R,5S)-5-methyl-2-[3-[[(3S)-1-methylpyrrolidin-3-yl]methoxy]phenyl]-1-piperidyl]acetamide (0.078 g, 162.63 μmol, 32.65% yield) was obtained as a light-yellow solid.

$^1$H NMR (600 MHz, DMSO-d$_6$) δ (ppm) 0.75-1.02 (m, 3H), 1.07-1.15 (m, 3H), 1.26-1.38 (m, 1H), 1.42-1.55 (m, 1H), 1.58-1.73 (m, 1H), 1.80-1.95 (m, 2H), 1.98-2.11 (m, 1H), 2.11-2.20 (m, 1H), 2.21 (s, 3H), 2.29-2.43 (m, 5H), 2.50-2.52 (m, 2H), 2.72-2.77 (m, 0.3H), 3.20-3.26 (m, 0.7H), 3.42-3.50 (m, 0.7H), 3.76-3.86 (m, 2H), 3.97-4.05 (m, 0.3H), 5.07-5.59 (m, 1H), 5.59-5.69 (m, 2H), 6.75-6.95 (m, 3H), 7.23-7.34 (m, 1H), 7.41-7.55 (m, 1H), 7.96-8.13 (m, 1H), 10.45 (br s, 1H).

LCMS(ESI): [M]$^+$ m/z: calcd 479.2; found 480.2; Rt=2.217 min.

Scheme G—Synthesis of Compounds of Formula 7

Compounds of Formula 7 are are compounds of Formula (I) wherein R$^1$, R$^2$, R$^3$, R$^4$, R$^6$, R$^7$, and R$^8$ are as described herein.

General Procedure 7

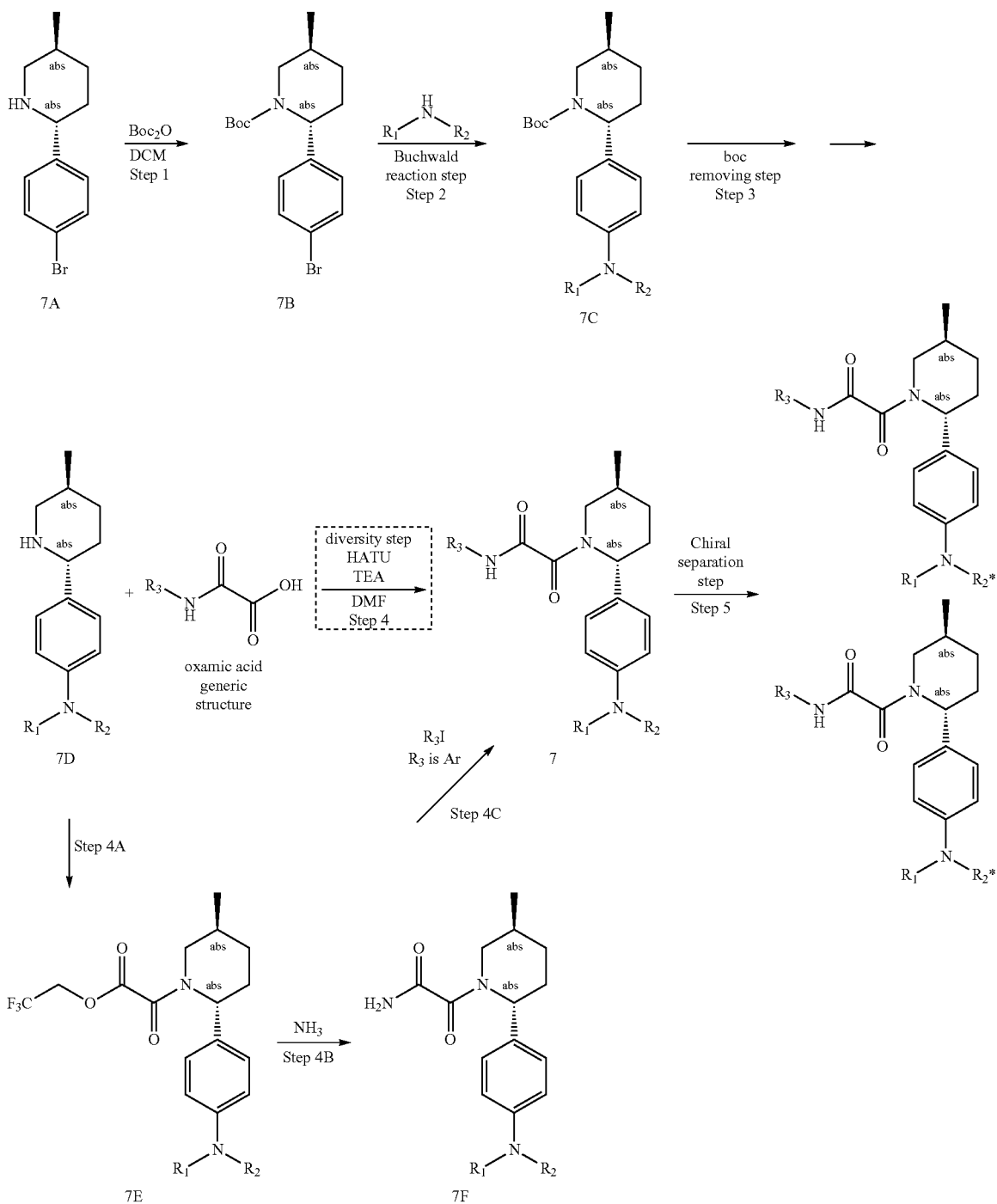

Step 1: The Synthesis of 7B 7A (1.0 equiv) was dissolved in DCM (280 mL) and a solution of di-tert-butyl dicarbonate (1.02 equiv) in DCM (20 mL) was added dropwise (vigorous gas evolution!). The resulting mixture was stirred at 20° C. for 4 hr. Then, the volatiles were removed under reduced pressure, affording crude product which was purified by FCC (CHCl$_3$-MeCN from 100%-0% to 0%-100%) to give tert-butyl (2R,5S)-2-(4-bromophenyl)-5-methyl-piperidine-1-carboxylate (7B).

Step 2: The Synthesis of 7C

To a stirred solution of tert-butyl (2R,5S)-2-(4-bromophenyl)-5-methyl-piperidine-1-carboxylate (7B; 1.0 equiv) and respective amine (1.0 equiv) in Solvent (5 mL) was added Base (2.5 equiv). The resulting suspension was degassed with argon. Ligand (0.05 equiv) and Pd cat (0.05 eqiv) was added. The reaction mixture was stirred at 65 ... 100° C. for 15 ... 48 hr. After the completion of the reaction (monitored by LCMS), the resulting mixture was allowed to cool to the room temperature, filtered through a thin layer of $SiO_2$ and washed with solvent (2 mL). The volatiles were removed in vacuo and the residue was subjected for purification to afford 7C.

Buchwald Reaction Step:

| Method | Pd cat | Base | Ligand | Inert atm | Solvent | Temperature | Time | Purification conditions |
|---|---|---|---|---|---|---|---|---|
| A | $Pd_2(dba)_3$ | $Cs_2CO_3$ | XanthPhos | Ar | dioxane | 100° C. | 16-48 h | Column Chromatography (chloroform-MeOH 10:1) |
| B | Pd G4 RuPhos | LIHMDS | RuPhos | Ar | THF | 65° C. | 18 h | Product was directly used in the next step |
| C | $Pd_2(dba)_3$ | LIHMDS | RuPhos | Ar | THF | 65° C. | 18 h | HPLC (60 - 60 - 100% 0 - 1 - 6 min $H_2O$/MeOH/0.1% $NH_4OH$) |
| D | $Pd_2(dba)_3$ | Na t-butoxide | BrettPhos | Ar | dioxane | 100° C. | 16 h | column chromatography ($CHCl_3$—MeOH, 10:1) or FCC (MeOH in MTBE from 0% to 100%) |
| E | $Pd(OAc)_2$ | $Cs_2CO_3$ | RuPhos | Ar | dioxane | 100° C. | 15 h | Product was directly used in the next step |
| F | $Pd_2(dba)_3$ | $Cs_2CO_3$ | BrettPhos | Ar | dioxane | 100° C. | 16 h | HPLC chromatography (65 - 65 - 80% 0 - 1 - 6 min $H_2O$/MeCN/0.1% $NH_4OH$) |

Step 3: The Synthesis of 7D 7C was dissolved in Solvent (2 ... 10 mL) and Acid (50.0 equiv) was added. The reaction mixture was stirred at room temperature for 1 ... 4 h. The solvent was removed in vacuo to obtain 7D.

Boc Removing Step:

| Method | Acid | Solvent | Temperature | Time | Work-up and Purification |
|---|---|---|---|---|---|
| A | HCl (4.0M soln in diox) | MeOH | RT | 4 h | The residue was triturated with MTBE-MeCN mixture, filtered and the solvents were removed under reduced pressure. |
| B | TFA | DCM | RT | 1 h | The reaction mixture was carefully poured into $K_2CO_3$ solution (10 g of $K_2CO_3$ in 30 mL of water) and the resulting mixture was extracted with DCM (2*40 mL). Combined organic layers were washed with water (30 mL), dried over $Na_2SO_4$, filtered and concentrated in vacuo. |

Step 4: The Synthesis of 7

7D (1.0 equiv), oxamic acid (1.0 equiv) and TEA (2.5 eq+1.0 eq per each acid eq, if amine salt used) were mixed together in DMF. HATU (1.5 eq) was added thereto and the resulting mixture was stirred overnight. The reaction mixture was concentrated in vacuo and the residue was purified by HPLC to obtain 7.

Step 4A: The Synthesis of 7E 7D (1.0 equiv) and TEA (1.2 equiv) were dissolved in THF and cooled to 0° C., following by the dropwise addition of 2,2,2-trifluoroethyl 2-chloro-2-oxo-acetate (1.1 equiv) and the reaction mixture was stirred for 2 hr at 0° C. The mixture (7E) was used in the next step without further purification.

Step 4B: The Synthesis of 7E

Through a solution of 7E (1.0 equiv) in THF (50 mL), ammonia (50.0 equiv) was bubbled at 20° C. for 10 min. The mixture was stirred for 2 hr, evaporated in vacuo and triturated with MTBE-MeCN. The precipitate was filtered and dried to give 7F.

Step 4C: The Synthesis of 7

7F (1.0 equiv), $R_3I$ (1.0 equiv), CuI (0.2 equiv), CuI (0.2 equiv), $N^1,N^2$-dimethylcyclohexane-1,2-diamine (0.2 equiv) and $Cs_2CO_3$ were mixed together in dioxane (6 mL) under an Ar atmosphere. The reaction mixture was stirred at 100° C. for 48 h. Then, the mixture was allowed to cool to the room temperature and filtered off. The filtrate was subjected to HPLC to afford 7.

Example 552. The Synthesis of N-(6-amino-5-ethyl-3-pyridyl)-2-[(2R,5S)-5-methyl-2-[4-(9-methyl-2,9-diazaspiro[5.5]undecan-2-yl)phenyl]-1-piperidyl]-2-oxo-acetamide (Compound 1401

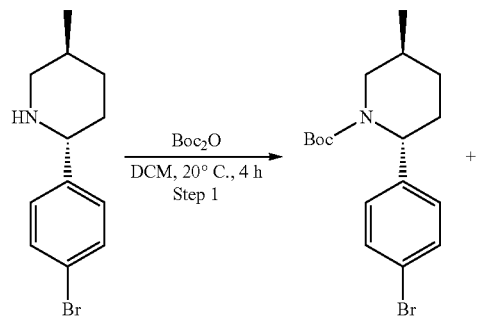

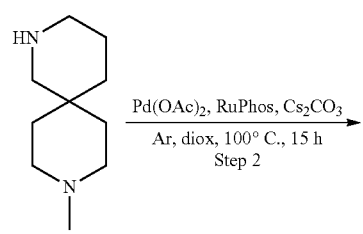

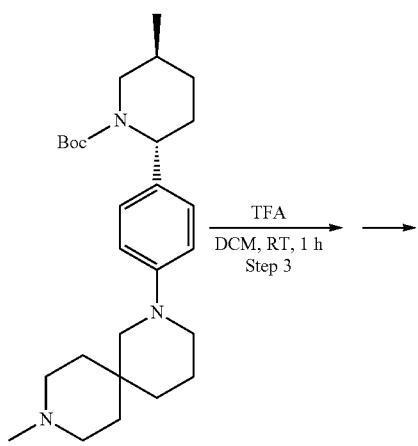

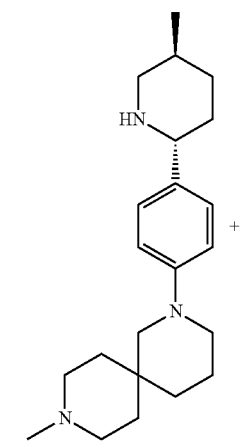

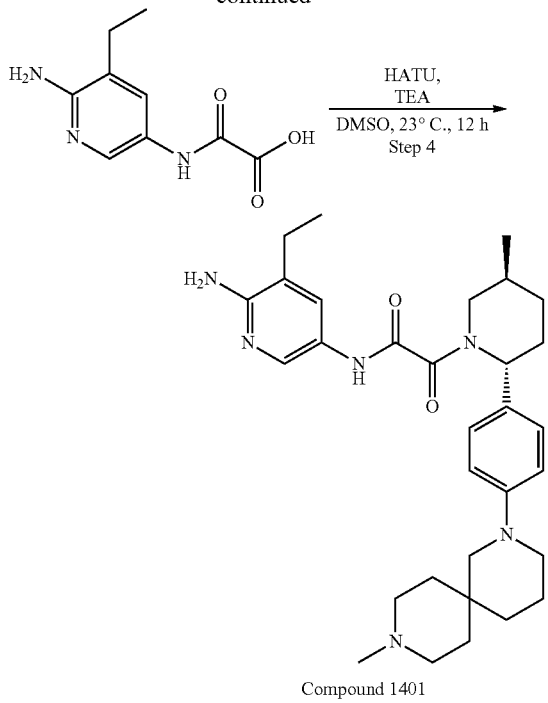

Compound 1401

Step 1: The Synthesis of tert-butyl (5S)-2-(4-bromophenyl)-5-methyl-piperidine-1-carboxylate Prepared by General Procedure 7.
Yield: 14 g (87.34%)
LCMS(ESI): [M−Boc]+ m/z: calcd 254.0; found 254.0; Rt=1.539 min.

Step 2: The Synthesis of tert-butyl (2R,5S)-5-methyl-2-[4-(9-methyl-2,9-diazaspiro[5.5]undecan-2-yl)phenyl]piperidine-1-carboxylate Prepared by General Procedure 7
Yield: 105.0 mg (crude)
LCMS(ESI): [M+H]+ m/z: calcd 442.4; found 442.4; Rt=1.159 min.

Step 3: The Synthesis of 9-methyl-2-[4-[(2R,5S)-5-methyl-2-piperidyl]phenyl]-2,9-diazaspiro[5.5]undecane Prepared by General Procedure Scheme 7
Yield: 96.0 mg (crude)
LCMS(ESI): [M+H]+ m/z: calcd 342.2; found 342.2; Rt=0.754 min.

Step 4: The Synthesis of N-(6-amino-5-ethyl-3-pyridyl)-2-[(2R,5S)-5-methyl-2-[4-(9-methyl-2,9-diazaspiro[5.5]undecan-2-yl)phenyl]-1-piperidyl]-2-oxo-acetamide (Compound 1401

Prepared by General Procedure Scheme G Step 4
Yield: 10.5 mg (7.01%).
HPLC conditions: 2-10 min 40-65% Water-MeOH-0.1% NH4OH; 30 mL/min; loading pump MeOH-0.1% NH4OH 4 mL/min; column SunFire 19*100 mm, 5 mkm ¹H NMR (600 MHz, dmso) δ 0.88-1.03 (m, 3H), 1.04-1.15 (m, 4H), 1.26-1.35 (m, 1H), 1.36-1.44 (m, 4H), 1.48-1.54 (m, 2H), 1.59-1.64 (m, 2H), 1.64-1.76 (m, 1H), 1.77-1.91 (m, 1H), 1.92-2.10 (m, 1H), 2.11-2.19 (m, 4H), 2.20-2.26 (m, 2H), 2.26-2.33 (m, 2H), 2.39-2.42 (m, 1H), 2.70-2.74 (m, 0.4H), 2.89-2.94 (m, 2H), 3.01-3.08 (m, 2H), 3.16-3.22 (m, 0.6H), 3.50-3.98 (m, 1H), 5.02-5.59 (m, 1H), 5.59-5.69 (m, 2H), 6.85-6.93 (m, 2H), 7.08-7.21 (m, 2H), 7.40-7.55 (m, 1H), 7.97-8.10 (m, 1H), 10.42-10.51 (m, 1H).

LCMS(ESI): [M+H]⁺ m/z: calcd 533.4; found 533.4; Rt=1.961 min.

Example 553. The Synthesis of rel-2-[(2R,5S)-2-[4-[(4aR,8aS)-1-methyl-2,3,4,4a,5,7,8,8a-octahydro-1,6-naphthyridin-6-yl]phenyl]-5-methyl-1-piperidyl]-N-(6-amino-5-ethyl-3-pyridyl)-2-oxo-acetamide (Compound 1111) and Rel-2-[(2R,5S)-2-[4-[(4aS,8aR)-1-methyl-2,3,4,4a,5,7,8,8a-octahydro-1,6-naphthyridin-6-yl]phenyl]-5-methyl-1-piperidyl]-N-(6-amino-5-ethyl-3-pyridyl)-2-oxo-acetamide (Compound 1132

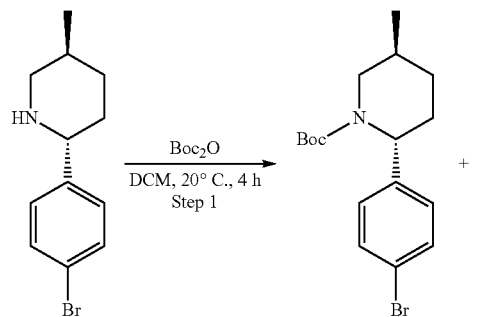

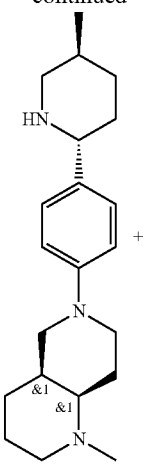

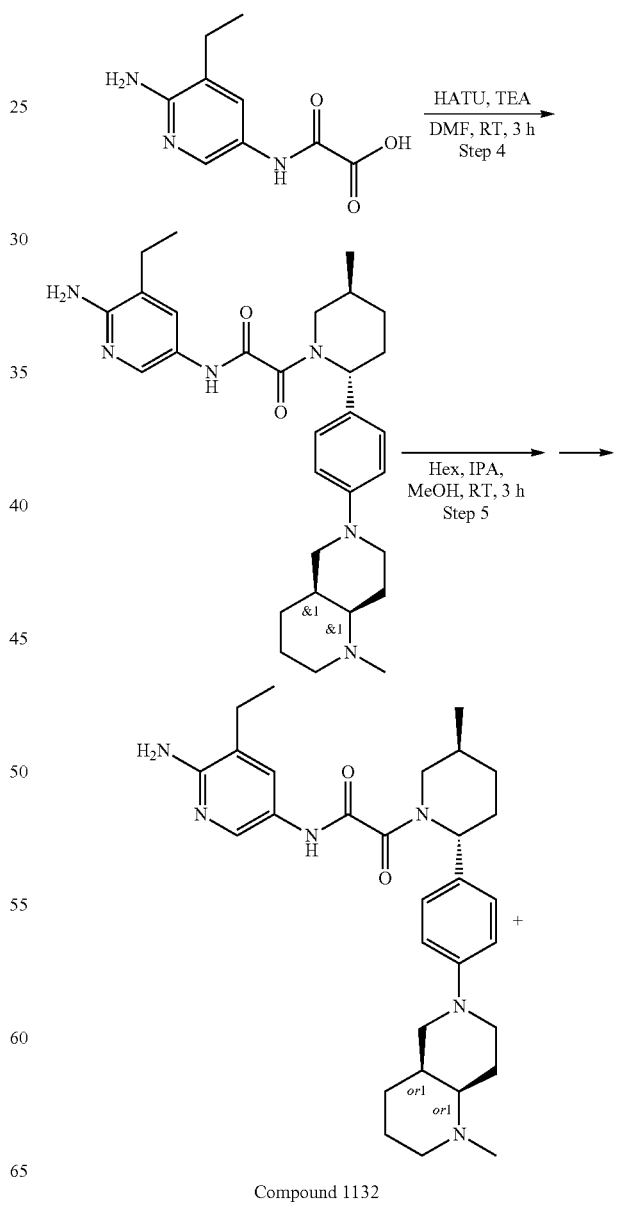

Compound 1132

-continued

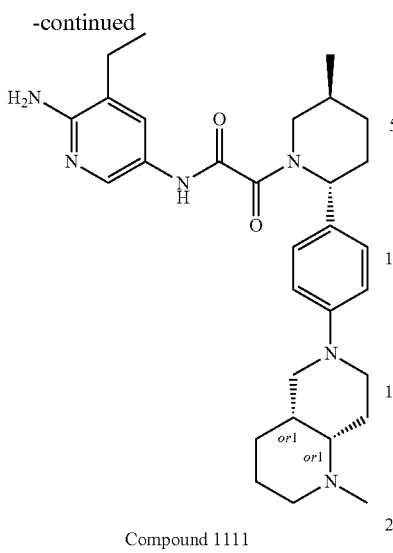

Compound 1111

Step 1: The Synthesis of tert-butyl (5S)-2-(4-bromophenyl)-5-methyl-piperidine-1-carboxylate Prepared by general procedure Scheme G Step 1 Yield: 14 g (87.34%)

LCMS(ESI): [M–Boc]+ m/z: calcd 254.0; found 254.0; Rt=1.539 min.

Step 2: The Synthesis of tert-butyl (2R,5S)-2-[4-[(4aS,8aR)-1-methyl-2,3,4,4a,5,7,8,8a-octahydro-1,6-naphthyridin-6-yl]phenyl]-5-methyl-piperidine-1-carboxylate Prepared by General Procedure Scheme G Step 2 (Method B)

Yield: 0.8 g (crude)

LCMS(ESI): [M+H]+ m/z: calcd 428.4; found 428.4; Rt=1.268 min.

Step 3: The Synthesis of (4aS,8aR)-1-methyl-6-[4-[(2R,5S)-5-methyl-2-piperidyl]phenyl]-2,3,4,4a,5,7,8,8a-octahydro-1,6-naphthyridine Prepared by General Procedure Scheme G Step 3 (Method A)

Yield: 0.7 g (85.64%)

LCMS(ESI): [M+H]+ m/z: calcd 328.4; found 328.4; Rt=0.666 min.

Step 4: The Synthesis of 2-[(2R,5S)-2-[4-[(4aS,8aR)-1-methyl-2,3,4,4a,5,7,8,8a-octahydro-1,6-naphthyridin-6-yl]phenyl]-5-methyl-1-piperidyl]-N-(6-amino-5-ethyl-3-pyridyl)-2-oxo-acetamide Prepared by General Procedure 7 Step 4

Yield: 340.0 mg (40.91%)

HPLC conditions: 40-40-90% 0-1-6 min H$_2$O/MeOH/0.1% NH$_4$OH, flow: 30 mL/min (loading pump 4 mL/min methanol); YMC Triart C18 100×20 mm, 5 um LCMS(ESI): [M+H]+ m/z: calcd 519.2; found 519.2; Rt=2.452 min.

Step 5: The Synthesis of rel-2-[(2R,5S)-2-[4-[(4aR,8aS)-1-methyl-2,3,4,4a,5,7,8,8a-octahydro-1,6-naphthyridin-6-yl]phenyl]-5-methyl-1-piperidyl]-N-(6-amino-5-ethyl-3-pyridyl)-2-oxo-acetamide (Compound 1111) and Rel-2-[(2R,5S)-2-[4-[(4aS,8aR)-1-methy-2,3,4,4a,5,7,8,8a-octahydro-1,6-naphthyridin-6-yl]phenyl]-5-methyl-1-piperidyl]-N-(6-amino-5-ethyl-3-pyridyl)-2-oxo-acetamide (Compound 1132

Prepared by General Procedure 7 Step 5
Compound 1132: Yield: 103 mg (60.59%).
Compound 1111: Yield: 94 mg (55.29%).
Chiral Separation conditions: Column: Chiralpak IB (250*20 mm, 5 mkm) Mobile phase: Hexane-IPA-MeOH, 50-25-25 Flow rate: 12 mL/min; m=0.25 g, injection 37, 6.75 mg/inj, V=11.11, 15.4 h.
Compound 1111:
RT (Chiralpak IB (250*4.6, 5 mkm), Hexane-IPA-MeOH, 50-25-25, 0.6 mL/min)=16.35 min.
$^1$H NMR (600 MHz, DMSO-d$_6$) δ (ppm) 0.97-1.04 (m, 3H), 1.07-1.14 (m, 3H), 1.27-1.35 (m, 1H), 1.40-1.73 (m, 7H), 1.80-2.33 (m, 10H), 2.37-2.42 (m, 2H), 2.64-3.24 (m, 5H), 3.38-4.00 (m, 1H), 5.02-5.54 (m, 1H), 5.58-5.66 (m, 2H), 6.87-6.94 (m, 2H), 7.07-7.18 (m, 2H), 7.44-7.52 (m, 1H), 8.00-8.09 (m, 1H), 10.40-10.55 (m, 1H).
LCMS(ESI): [M]+ m/z: calcd 518.0; found 518.0; Rt=2.214 min.
Compound 1132:
RT (Chiralpak IB (250*4.6, 5 mkm), Hexane-IPA-MeOH, 50-25-25, 0.6 mL/min)=19.69 min.
$^1$H NMR (600 MHz, DMSO-d$_6$) δ (ppm) 0.97-1.03 (m, 3H), 1.07-1.13 (m, 3H), 1.27-1.73 (m, 8H), 1.80-2.26 (m, 9H), 2.37-2.43 (m, 2H), 2.61-3.26 (m, 6H), 3.37-4.00 (m, 1H), 5.01-5.54 (m, 1H), 5.57-5.66 (m, 2H), 6.87-6.94 (m, 2H), 7.06-7.17 (m, 2H), 7.44-7.52 (m, 1H), 7.99-8.09 (m, 1H), 10.40-10.53 (m, 1H).
LCMS(ESI): [M+H]+ m/z: calcd 519.4; found 519.4; Rt=2.216 min.

The Synthesis of rel-2-[(2R,5S)-2-[4-[(4aR,8aS)-7-methyl-1,3,4,4a,5,6,8,8a-octahydro-2,7-naphthyridin-2-yl]phenyl]-5-methyl-1-piperidyl]-N-(6-amino-5-ethyl-3-pyridyl)-2-oxo-acetamide (Compound 1204) and Rel-2-[(2R,5S)-2-[4-[(4aS,8aR)-7-methyl-1,3,4,4a,5,6,8,8a-octahydro-2,7-naphthyridin-2-yl]phenyl]-5-methyl-1-piperidyl]-N-(6-amino-5-ethyl-3-pyridyl)-2-oxo-acetamide (Compound 1144

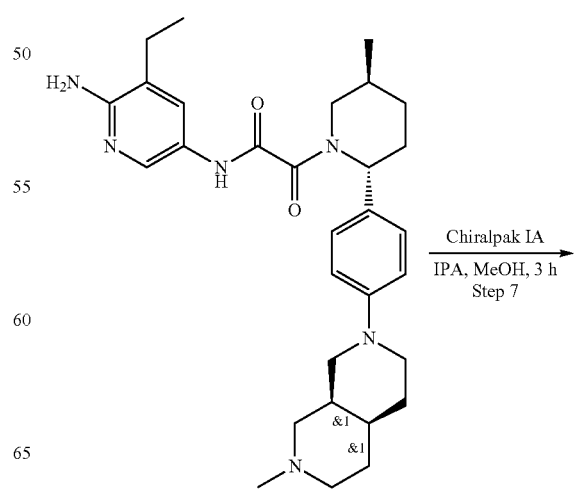

2475

-continued

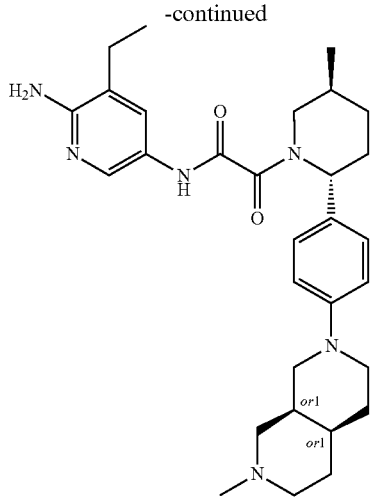

Compound 1204

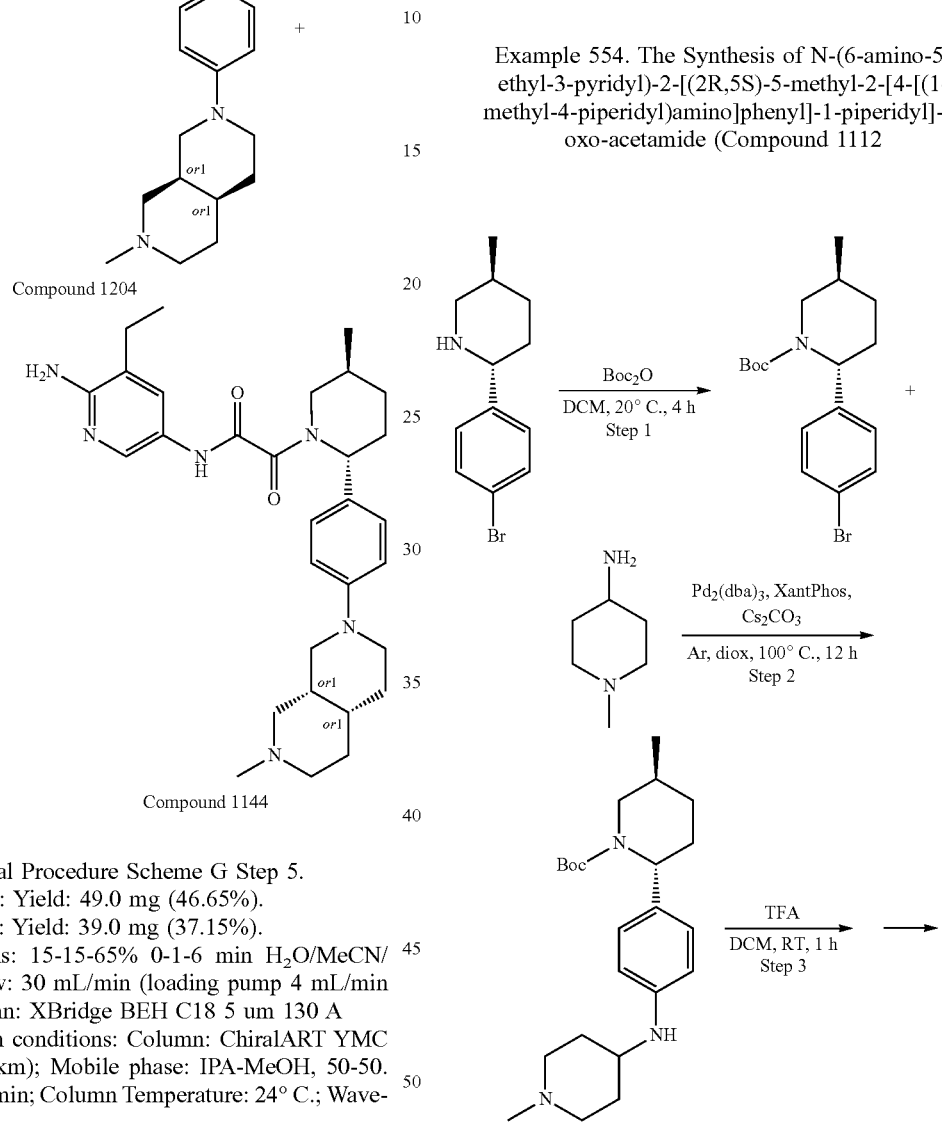

Compound 1144

Prepared by General Procedure Scheme G Step 5.
Compound 1204: Yield: 49.0 mg (46.65%).
Compound 1144: Yield: 39.0 mg (37.15%).
HPLC conditions: 15-15-65% 0-1-6 min $H_2O$/MeCN/ 0.1% $NH_4OH$, flow: 30 mL/min (loading pump 4 mL/min acetonitrile); column: XBridge BEH C18 5 um 130 A
Chiral separation conditions: Column: ChiralART YMC (250*20 mm, 5 mkm); Mobile phase: IPA-MeOH, 50-50. Flow Rate: 12 mL/min; Column Temperature: 24° C.; Wavelength: 205 nm
Compound 1204:
$^1$H NMR (600 MHz, dmso) δ 0.94-1.05 (m, 3H), 1.06-1.13 (m, 3H), 1.26-1.36 (m, 1H), 1.37-1.78 (m, 7H), 1.80-1.91 (m, 2H), 1.93-2.10 (m, 5H), 2.12-2.21 (m, 2H), 2.32-2.42 (m, 3H), 2.70-3.26 (m, 5H), 3.36-4.00 (m, 1H), 4.99-5.54 (m, 1H), 5.54-5.65 (m, 2H), 6.86-6.94 (m, 2H), 7.07-7.17 (m, 2H), 7.43-7.53 (m, 1H), 7.97-8.10 (m, 1H), 10.47 (s, 1H).
RT (Chiralpak IA (250*4.6, 5 mkm), IPA-MeOH, 50-50, 0.6 mL/min)=26.19 min.
LCMS(ESI): $[M+H]^+$ m/z: calcd 519.2; found 519.2; Rt=1.704 min.
Compound 1144:
$^1$H NMR (600 MHz, dmso) δ 0.97-1.03 (m, 3H), 1.07-1.13 (m, 3H), 1.27-1.35 (m, 1H), 1.40-1.75 (m, 7H), 1.81-

1.97 (m, 3H), 2.02-2.22 (m, 7H), 2.33-2.42 (m, 2H), 2.69-3.25 (m, 5H), 3.38-3.99 (m, 1H), 5.00-5.54 (m, 1H), 5.56-5.65 (m, 2H), 6.85-6.92 (m, 2H), 7.06-7.18 (m, 2H), 7.42-7.54 (m, 1H), 7.98-8.09 (m, 1H), 10.39-10.55 (m, 1H).
RT (Chiralpak IA (250*4.6, 5 mkm), IPA-MeOH, 50-50, 0.6 mL/min)=20.31 min.
LCMS(ESI): $[M+H]^+$ m/z: calcd 519.2; found 519.2; Rt=1.703 min.

Example 554. The Synthesis of N-(6-amino-5-ethyl-3-pyridyl)-2-[(2R,5S)-5-methyl-2-[4-[(1-methyl-4-piperidyl)amino]phenyl]-1-piperidyl]-2-oxo-acetamide (Compound 1112

2477  
-continued

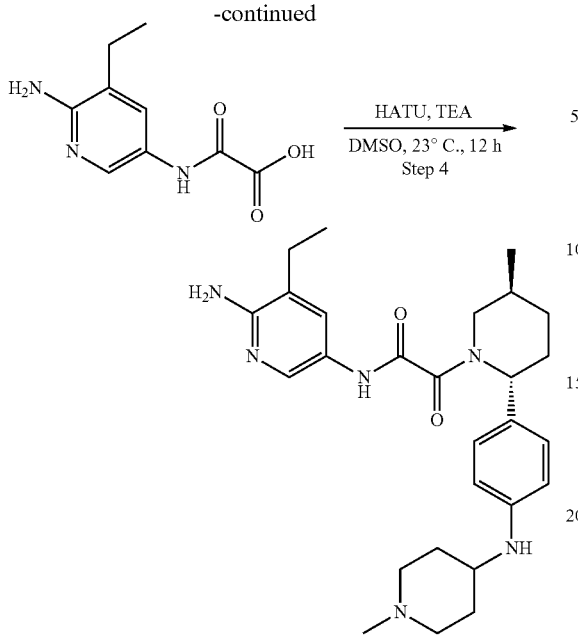

Step 2: The Synthesis of tert-butyl (2R,5S)-5-methyl-2-[4-[(l-methyl-4-piperidyl)amino]phenyl]piperidine-1-carboxylate Prepared by general procedure Scheme G Step 2. Yield: 94.0 mg (9.55%)
LCMS(ESI): [M+H]$^+$ m/z: calcd 388.2; found 388.2; Rt=1.075 min.

Step 3: The Synthesis of 1-methyl-N-[4-[(2R,5S)-5-methyl-2-piperidyl]phenyl]piperidin-4-amine Prepared by general procedure Scheme G Step 3 (Method B). Yield: 150.0 mg (crude)
LCMS(ESI): [M+H]$^+$ m/z: calcd 288.2; found 288.2; Rt=0.583 min.

Step 4: The Synthesis of N-(6-amino-5-ethyl-3-pyridyl)-2-[(2R,5S)-5-methyl-2-[4-[(l-methyl-4-piperidyl)amino]phenyl]-1-piperidyl]-2-oxo-acetamide (Compound 1112

Prepared by general procedure Scheme G Step 4. Yield: 42.5 mg (35.56%) HPLC conditions: 2-10 min 30-45% water-MeOH-0.11% NH$_4$OH; 30 mL/min; loading pump MeOH-0.11% NH$_4$OH; 4 mL/min; column SunFire 19*100 mm, 5 mkm
$^1$H NMR (dmso, 600 MHz): δ (ppm) 0.71-0.78 (m, 1H), 0.98-1.13 (m, 5H), 1.27-1.36 (m, 3H), 1.59-1.99 (m, 7H), 2.14 (s, 3H), 2.35-2.41 (m, 2H), 2.68-2.70 (m, 2H), 3.12-3.19 (m, 1H), 3.36-4.14 (m, 3H), 5.37-5.62 (m, 4H), 6.54-6.57 (m, 2H), 6.96-7.03 (m, 2H), 7.46-7.51 (m, 1H), 7.99-8.07 (m, 1H), 10.27 (m, 1H).
LCMS(ESI): [M+H]$^+$ m/z: calcd 479.2; found 479.2; Rt=0.841 min.

Scheme H Synthesis of Compounds of Formula 8

Compounds of Formula 8 are are compounds of Formula (I) wherein R$^1$, R$^2$, R$^3$, R$^{4'}$ R$^6$, R$^7$, and R$^8$ are as described herein.

2478  
General Procedure 8

Scheme H

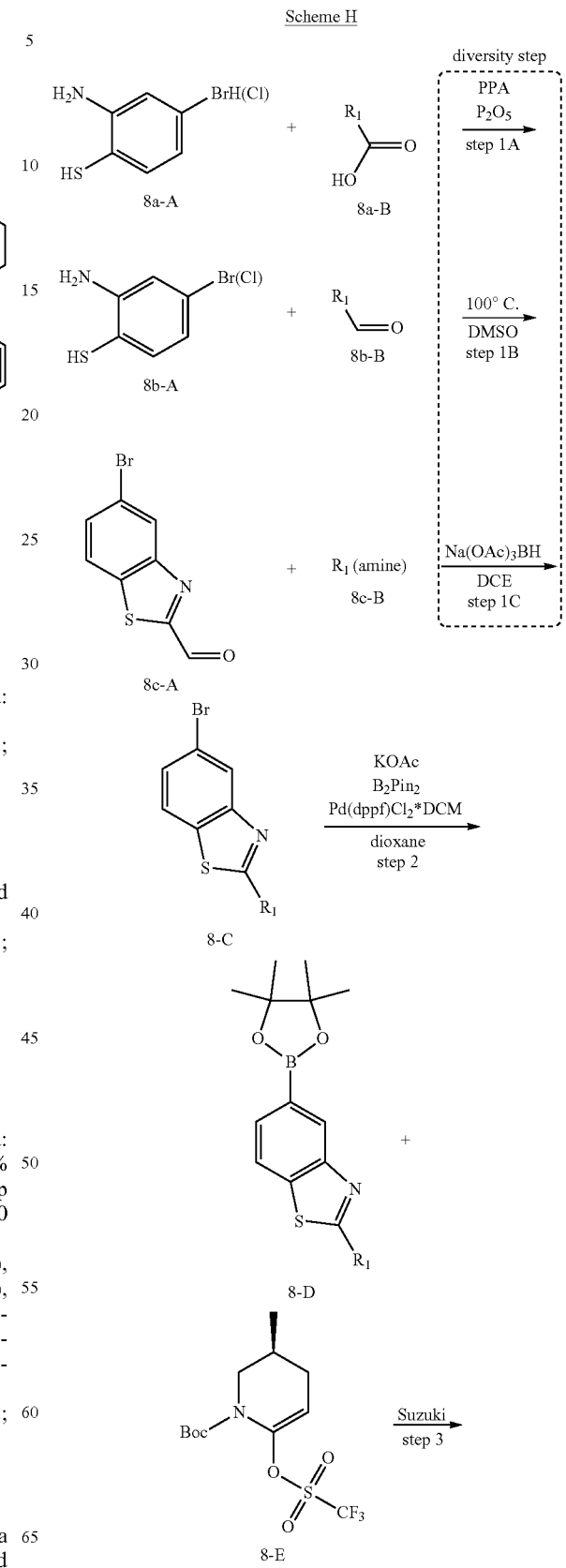

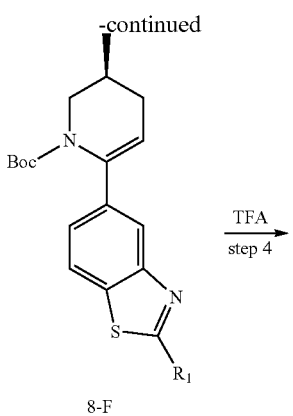

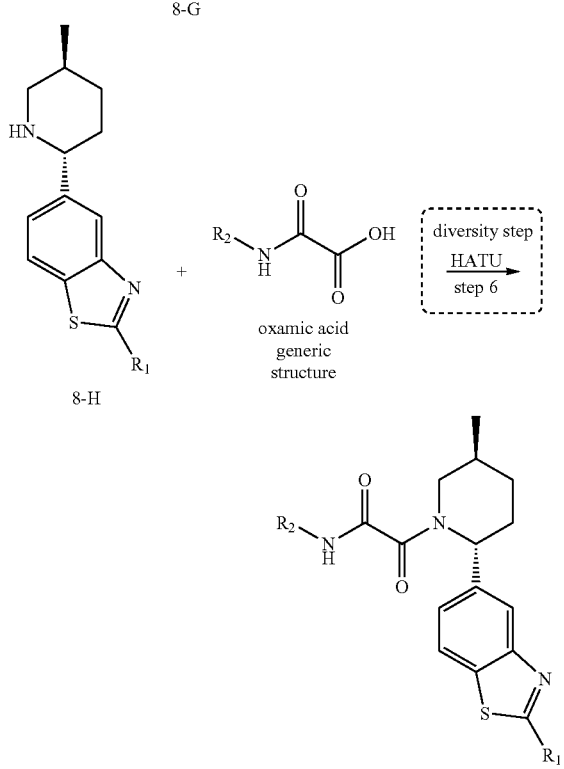

Formula 8

Step 1A: Synthesis of 8-C

Phosphoric acid (4 eq) and phosphorus pentoxide (4 eq) were mixed together. The reaction suspension was stirred at rt for 10 min, then 8a-A (1 eq) followed by 8a-B (1.2 eq) were added under Ar. The solution was stirred at 110° C. for 18 hr then it was triturated with water, basified (NaOH, 10% aq.) to pH=10, extracted with DCM twice, dried and evaporated in vacuum to give 8-C.

Step 1B: Synthesis of 8-C

To the stirred solution of 8b-A (1 eq) in DMSO 8b-B (1 eq) was added. The resulting mixture was stirred at 100° C. for 14 hr. The reaction mixture was poured into cold water and extracted with MTBE twice. Combined organic layers were washed with water and brine, dried over $Na_2SO_4$. MTBE was evaporated in vacuum to give 8-C.

Step 1C: Synthesis of 8-C

To the stirred solution of 8c-A (1 eq) in the 1,2-dichloroethane 8c-B (2 eq) was added and allowed to stir at 25° C. for 2 hr, sodium (trisacetoxy) borohydride (2 eq) was added. The reaction mixture was stirred at 25° C. for 16 hr. After completion, the reaction mixture was evaporated, quenched with water and neutralized by $K_2CO_3$ to pH=10. The aqueous phase was extracted with $CHCl_3$ twice. The combined organic phase was dried over $Na_2SO_4$ and evaporated under reduced pressure to afford 8-C. (TEA 1.5 eq per each acid eq, if amine salt used, was added to the solution of respective amine)

Step 2: Synthesis of 8-D

8-C(1 eq), $B_2Pin_2$ (1.1 eq) and KOAc (2 eq) were mixed in dioxane. The resulting mixture was evacuated and then backfilled with argon, this operation was repeated three times, then Pd(dppf)$Cl_2$*DCM (0.05 eq) was added under argon. The reaction mixture was stirred under argon at 90° C. for 14 hr, then cooled and filtered. The filter cake was washed with dioxane twice. The solvent was evaporated to afford 8-D.

Step 3: Synthesis of 8-F

8-D (1 eq), tert-butyl (3S)-3-methyl-6-(trifluoromethylsulfonyloxy)-3,4-dihydro-2H-pyridine-1-carboxylate (1.2 eq), sodium carbonate (3 eq) were mixed together in dioxane-water mixture (3:1). The resulting mixture was evacuated and then backfilled with argon. This operation was repeated two times, then Pd(dppf)$Cl_2$*DCM (819.86 mg, 1.00 mmol) was added and the reaction mixture was stirred under argon at 90° C. overnight, then cooled down and concentrated in vacuum. The residue was diluted with MTBE and stirred for 0.5 hr. After the most of the residue had dissolved, anhydrous sodium sulphate was added, and the resulting mixture was filtered. The filter cake was additionally washed with MTBE (5*50 ml) and discarded. The filtrate was concentrated in vacuum to afford 8-F.

Step 4: Synthesis of 8-G

A solution of 8-F (1 eq) in TFA (15 eq) was stirred at rt for 1 hr, and then concentrated in vacuum. Cold water was added to the residue, and the resulting mixture was extracted with DCM twice. The DCM layer was discarded, and the aqueous layer was basified to pH 11. The resulting mixture was extracted with DCM twice. The combined organic extracts were dried over sodium sulphate and concentrated in vacuum to afford 8-G.

Step 5: Synthesis of 8-H

8-G (1 eq) was dissolved in MeOH and the resulting solution was cooled to 0° C. in an ice bath. Sodium borohydride (2 eq) was added portion wise to the previous solution. After addition completed, the reaction mixture was allowed to warm to rt and stirred overnight. Water was added to the reaction mixture and the resulting mixture was concentrated in vacuum. The residue was diluted with water and the resulting mixture was extracted with DCM twice, dried over $Na_2SO_4$, filtered and evaporated to obtain 8-H.

Step 6A: Synthesis of Formula 8

8-H (1 eq), oxamic acid (1 eq) and TEA (2.5 eq+1.0 eq per each acid eq, if amine salt used) were mixed together in DMF. HATU (1.5 eq) was added thereto and the resulting mixture was stirred overnight. The reaction mixture was concentrated in vacuum and the residue was purified by HPLC to obtain Formula 8.

Step 6B: Synthesis of Formula 8

DIPEA (2.5 eq+1.0 eq per each acid eq, if amine salt used) was added to the solution of respective amine or it salt (8-H) (1 eq) and oxamic acid (1 eq) in DMF. The resulting mixture was stirred for 5 min followed by the addition of the solution of HATU (1.1 eq) in DMF. Then, the reaction mixture was stirred overnight at rt. After the completion of the reaction, monitored by LCMS, the resulting suspension was concentrated under reduced pressure. The obtained filtrate was subjected to HPLC (Waters SunFire C18 19*100 5 mkm column and $H_2O$-MeOH as a mobile phase) to afford pure product (Formula 8).

Example 555. The Synthesis of N-(6-amino-5-methylpyridin-3-yl)-2-((2R,5S)-5-methyl-2-(2-(1-methyl-1H-imidazol-4-yl)benzo[d]thiazol-5-yl)piperidin-1-yl)-2-oxoacetamide (Compound 1280

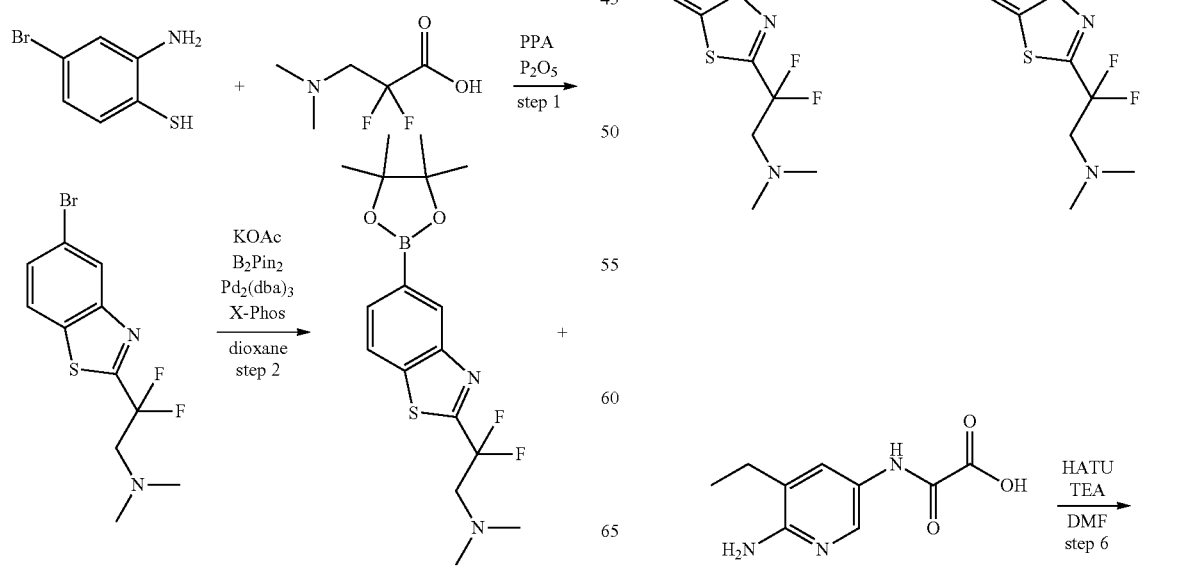

-continued

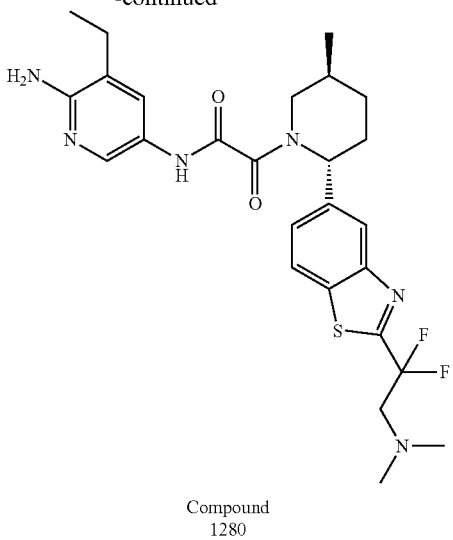

Compound 1280

Step 1: Synthesis of 2-(5-bromobenzo[d]thiazol-2-yl)-2,2-difluoro-N,N-dimethylethanamine Prepared by general procedure scheme H step 1A. Yield: 8.3 g of crude.

LCMS(ESI): [M]+ m/z: calcd 321.2; found 322.2; Rt=1.068 min.

Step 2: Synthesis of 2,2-difluoro-N,N-dimethyl-2-(5-(4,4,5,5-tetramethyl-1,3,2-dioxaborolan-2-yl)benzo[d]thiazol-2-yl)ethanamine 2-(5-bromo-1,3-benzothiazol-2-yl)-2,2-difluoro-N,N-dimethyl-ethanamine (8.3 g, 25.84 mmol), 4,4,5,5-tetramethyl-2-(4,4,5,5-tetramethyl-1,3,2-dioxaborolan-2-yl)-1,3,2-dioxaborolane (7.87 g, 31.01 mmol) and potassium acetate (5.07 g, 51.68 mmol, 3.23 mL) were mixed together in dioxane (100 mL). Reaction flask was evacuated and refilled with argon 3 times. Then, XPhos (2.46 g, 5.17 mmol) and tris(dibenzylideneacetone)dipalladium (0) (1.18 g, 1.29 mmol) were added under stream of argon. Resulting mixture was stirred at 100° C. for 16 hr. Then, it was concentrated under reduced pressure and residue was purified by gradient column chromatography (SiO$_2$, CHCl$_3$/MTBE), affording 2,2-difluoro-N,N-dimethyl-2-[5-(4,4,5,5-tetramethyl-1,3,2-dioxaborolan-2-yl)-1,3-benzothiazol-2-yl]ethanamine (8.8 g, 23.90 mmol, 92.47% yield).

LCMS(ESI): [M]+ m/z: calcd 368.2; found 369.2; Rt=1.076 min.

Step 3: Synthesis of (S)-tert-butyl 6-(2-(2-(dimethylamino)-1,1-difluoroethyl)benzo[d]thiazol-5-yl)-3-methyl-3,4-dihydropyridine-1(2H)-carboxylate Prepared by general procedure scheme H step 3. Yield: 2.22 g (88.77%).

LCMS(ESI): [M]+ m/z: calcd 437.2; found 438.2; Rt=1.299 min.

Step 4: Synthesis of (S)-2,2-difluoro-N,N-dimethyl-2-(5-(5-methyl-3,4,5,6-tetrahydropyridin-2-yl)benzo[d]thiazol-2-yl)ethanamine Prepared by general procedure scheme H step 4. Yield: 1.14 g (66.59%).

LCMS(ESI): [M]+ m/z: calcd 337.2; found 338.2; Rt=0.586 min.

Step 5: Synthesis of 2,2-difluoro-N,N-dimethyl-2-(5-((2R,5S)-5-methylpiperidin-2-yl)benzo[d]thiazol-2-yl)ethanamine Prepared by general procedure scheme H step 5. Yield: 1.04 g (90.69%).

LCMS(ESI): [M]+ m/z: calcd 339.2; found 340.2; Rt=0.771 min.

Step 6: Synthesis of N-(6-amino-5-methylpyridin-3-yl)-2-((2R,5S)-5-methyl-2-(2-(1-methyl-1H-imidazol-4-yl)benzo[d]thiazol-5-yl)piperidin-1-yl)-2-oxoacetamide (Compound 1280)

Prepared by general procedure scheme H step 6A. Yield: 133 mg (56.72%).

HPLC conditions: Column: YMC Triart C18 100*20 mm, 5 microM; 0-5 min 40-100% water-MeOH+0.1% NH$_4$OH, flow: 30 ml/min; (loading pump 4 ml/min MeOH).

$^1$H NMR (600 MHz, DMSO-d$_6$) δ (ppm) 1.02-1.07 (t, 3H), 1.11-1.14 (m, 3H), 1.32-1.41 (m, 1H), 1.67-1.71 (m, 2H), 1.86-1.90 (m, 1H), 2.06-2.13 (m, 1H), 2.17-2.23 (m, 6H), 2.34-2.41 (m, 3H), 2.78-2.81 (m, 1H), 3.49-4.07 (m, 2H), 5.32-5.72 (m, 3H), 7.43-7.60 (m, 2H), 7.99-8.11 (m, 2H), 8.22-8.26 (m, 1H), 10.54-10.59 (m, 1H).

LCMS(ESI): [M]+ m/z: calcd 530.2; found 531.2; Rt=2.162 min.

Example 556. The Synthesis of N-(6-amino-5-ethylpyridin-3-yl)-2-((2R,5S)-2-(2-((Ethyl(Isopropyl)amino)methyl)benzo[d]thiazol-5-yl)-5-methylpiperidin-1-yl)-2-oxoacetamide (Compound 1380

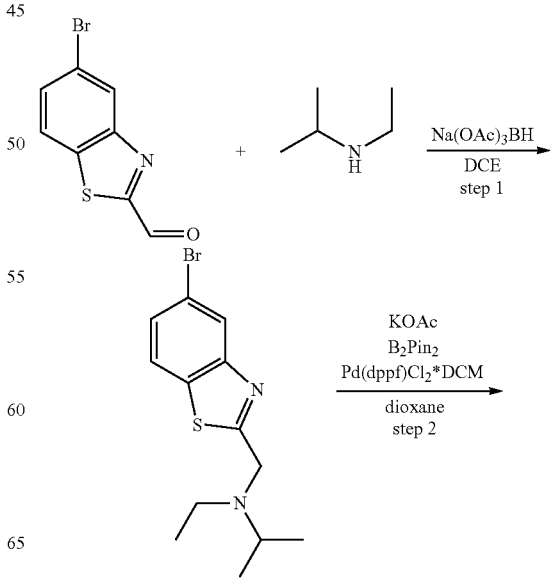

-continued

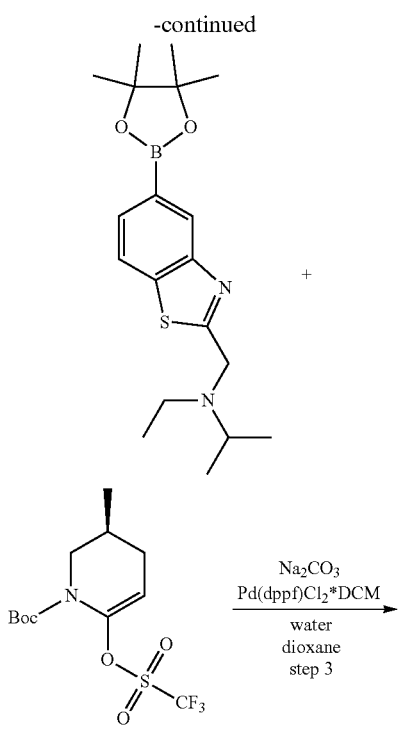

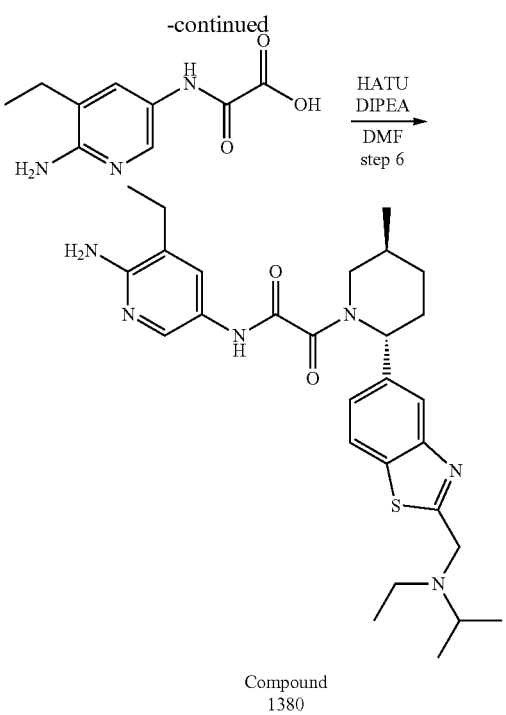

Compound 1380

Step 1: Synthesis of N-((5-bromobenzo[d]thiazol-2-yl)methyl)-N-ethylpropan-2-amine Prepared by general procedure scheme H step 1C. Yield: 1.2 g (92.74%).
LCMS(ESI): [M]+ m/z: calcd 313.2; found 314.2; Rt=1.016 min.

Step 2: Synthesis of N-ethyl-N-((5-(4,4,5,5-tetramethyl-1,3,2-dioxaborolan-2-yl)benzo[d]thiazol-2-yl)methyl)propan-2-amine Prepared by general procedure scheme H step 2. Yield: 1.3 g of crude.
LCMS(ESI): [M]f m/z: calcd 360.2; found 361.2; Rt=1.192 min.

Step 3: Synthesis of (S)-tert-butyl 6-(2-((Ethyl(Isopropyl)amino)methyl)benzo[d]thiazol-5-yl)-3-methyl-3,4-dihydropyridine-1(2H)-carboxylate Prepared by general procedure scheme H step 3. Yield: 0.65 g (41.94%).
CC conditions: The crude product was purified by silica gel with CHCl$_3$/EtOAc as an eluent mixture.
LCMS(ESI): [M]+ m/z: calcd 429.2; found 430.2; Rt=1.340 min.

Step 4: Synthesis of (S)—N-ethyl-N-((5-(5-methyl-3,4,5,6-tetrahydropyridin-2-yl)benzo[d]thiazol-2-yl)methyl)propan-2-amine The stirred solution of tert-butyl (3S)-6-[2-[[ethyl(isopropyl)amino]methyl]-1,3-benzothiazol-5-yl]-3-methyl-3,4-dihydro-2H-pyridine-1-carboxylate (650.00 mg, 1.51 mmol) in MeOH (10 mL) and diox/HCl (5 mL) was allowed to stir at 25° C. for 16 hr. Upon completion, the reaction mixture was evaporated, the crude product was quenched with water (20 mL) and neutralized by NaHCO$_3$ to pH=8. The aqueous phase was extracted with CHCl$_3$ (2*20 mL). The combined organic phase was dried over Na$_2$SO$_4$ and concentrated under reduced pressure. The desired product N-ethyl-N-[[5-[(3S)-3-methyl-2,3,4,5-tetrahydropyridin-6-yl]-1,3-benzothiazol-2-yl]methyl]propan-2-amine (0.49 g, 1.49 mmol, 98.29% yield) was isolated.

LCMS(ESI): [M]f m/z: calcd 329.2; found 330.2; Rt=0.483 min.

Step 5: Synthesis of N-ethyl-N-((5-((2R,5S)-5-methylpiperidin-2-yl)benzo[d]thiazol-2-yl)methyl)propan-2-amine Prepared by General Procedure Scheme H Step 5. Yield: 0.49 g (99.39%).

LCMS(ESI): [M]f m/z: calcd 331.2; found 332.2; Rt=0.777 min.

Step 6: Synthesis of N-(6-amino-5-ethylpyridin-3-yl)-2-((2R,5S)-2-(2-((Ethyl(Isopropyl)amino)methyl)benzo[d]thiazol-5-yl)-5-methylpiperidin-1-yl)-2-oxoacetamide (Compound 1380

Prepared by general procedure scheme H step 6B. Yield: 48 mg (30.44%).

HPLC conditions: Column: XBridge C18 100*19 mm, 5 microM; 0-5 min 60-80% water-MeOH+0.1% NH$_4$OH, flow: 30 ml/min; (loading pump 4 ml/min MeCN).

$^1$H NMR (600 MHz, DMSO-d$_6$) δ (ppm) 1.02-1.06 (m, 10H), 1.11-1.13 (t, 3H), 1.32-1.39 (m, 1H), 1.69-1.71 (m, 2H), 1.85-1.89 (m, 1H), 2.06-2.20 (m, 2H), 2.27-2.41 (m, 3H), 2.56-2.79 (m, 3H), 2.98-3.02 (m, 1H), 3.47-4.05 (m, 3H), 5.27-5.69 (m, 3H), 7.31-7.51 (m, 2H), 7.80-7.83 (d, 1H), 7.99-8.07 (m, 2H), 10.55 (br s, 1H).

LCMS(ESI): [M]$^+$ m/z: calcd 522.2; found 523.2; Rt=1.999 min.

Example 557. The Synthesis of N-(6-amino-5-ethylpyridin-3-yl)-2-((2R,5S)-5-methyl-2-(2-(Pyridin-3-yl)benzo[d]thiazol-5-yl)piperidin-1-yl)-2-oxoacetamide (Compound 1200

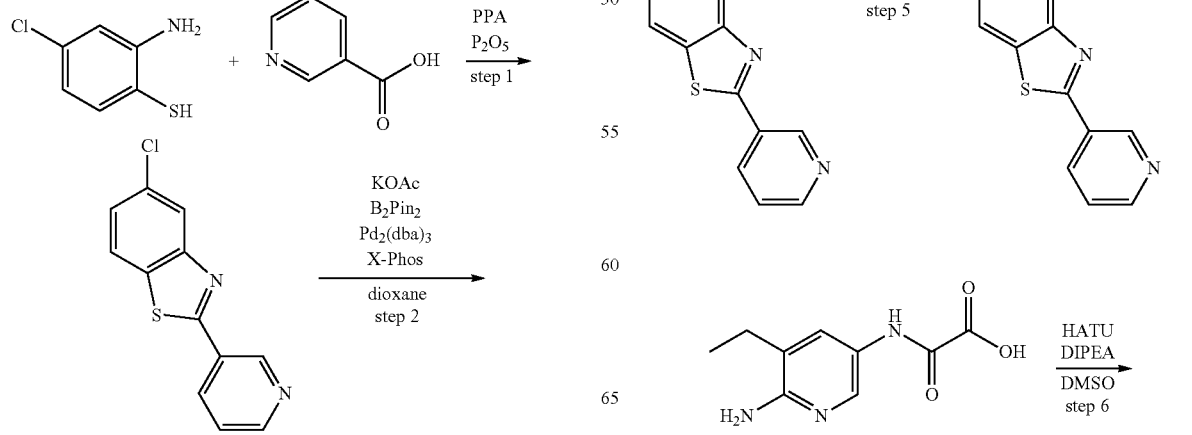

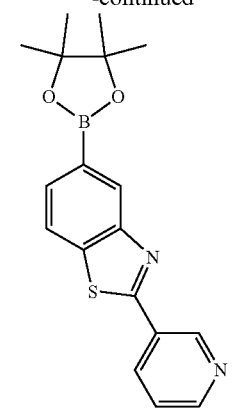

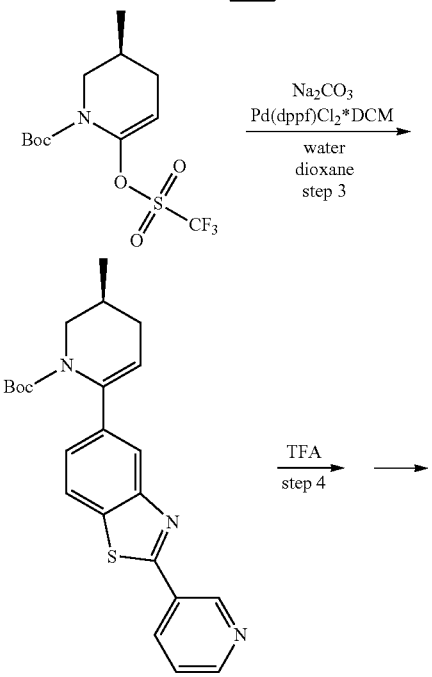

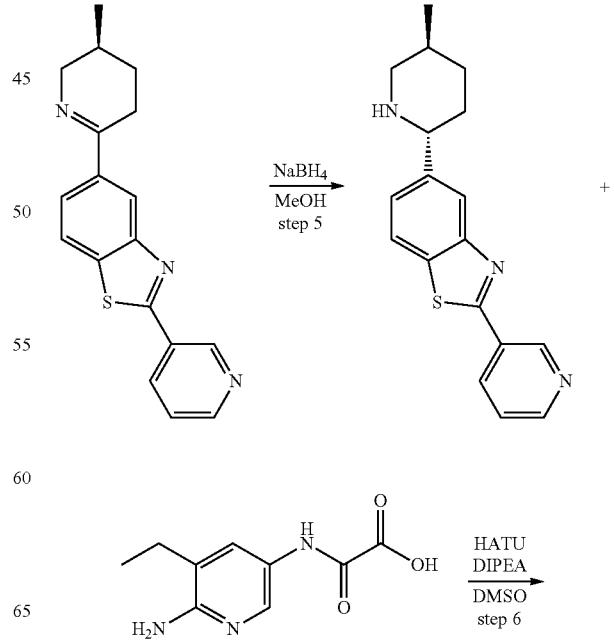

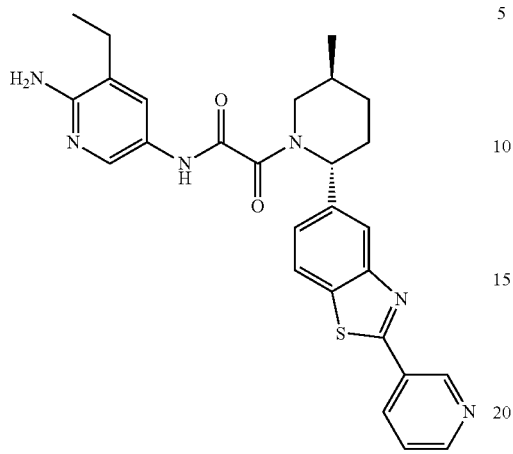

Step 6: Synthesis of N-(6-amino-5-ethylpyridin-3-yl)-2-((2R,5S)-5-methyl-2-(2-(Pyridin-3-yl)benzo[d]thiazol-5-yl)piperidin-1-yl)-2-oxoacetamide (Compound 1200

Prepared by general procedure scheme H step 6B. Yield: 18.9 mg (12.37%).

HPLC conditions: Column: SunFire C18 100*19 mm, 5 microM; 2-10 min 50-75% MeOH+NH$_3$, flow: 30 ml/min; (loading pump 4 ml/min MeOH).

$^1$H NMR (600 MHz, DMSO-d$_6$) δ (ppm) 1.03-1.06 (t, 3H), 1.12-1.14 (m, 3H), 1.34-1.42 (m, 1H), 1.70-1.75 (m, 1H), 1.88-1.96 (m, 1H), 2.11-2.29 (m, 1H), 2.30-2.35 (m, 1H), 2.40-2.48 (m, 1H), 2.81-2.8 (m, 1H), 3.50-4.08 (m, 2H), 5.33-5.73 (m, 3H), 7.36-7.62 (m, 3H), 8.00-8.08 (m, 2H), 8.21-8.22 (m, 1H), 8.43-8.46 (m, 1H), 8.74-8.75 (d, 1H), 9.25-9.27 (m, 1H), 10.57 (br s, 1H).

LCMS(ESI): [M]$^+$ m/z: calcd 500.2; found 501.2; Rt=2.793 min.

Example 558. The Synthesis of N-(6-amino-5-ethylpyridin-3-yl)-2-((2R,5S)-2-(2-((Isopropyl(methyl)amino)methyl)benzo[d]thiazol-5-yl)-5-methylpiperidin-1-yl)-2-oxoacetamide (Compound 1303

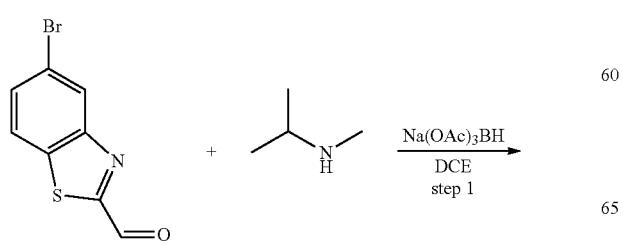

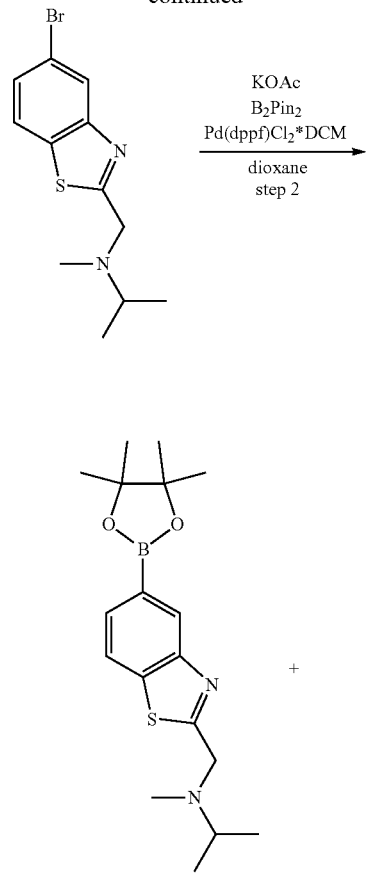

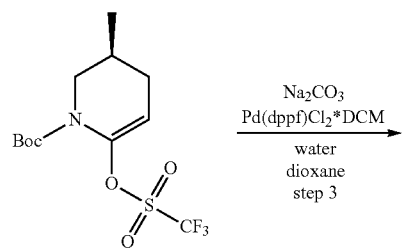

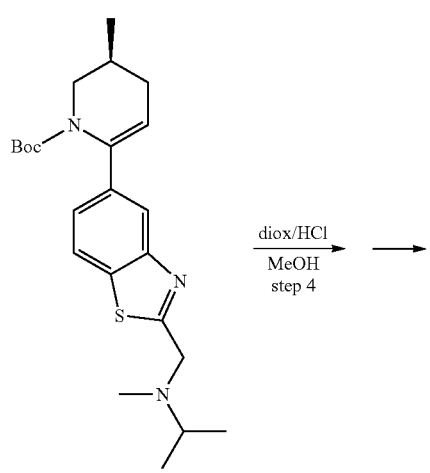

-continued

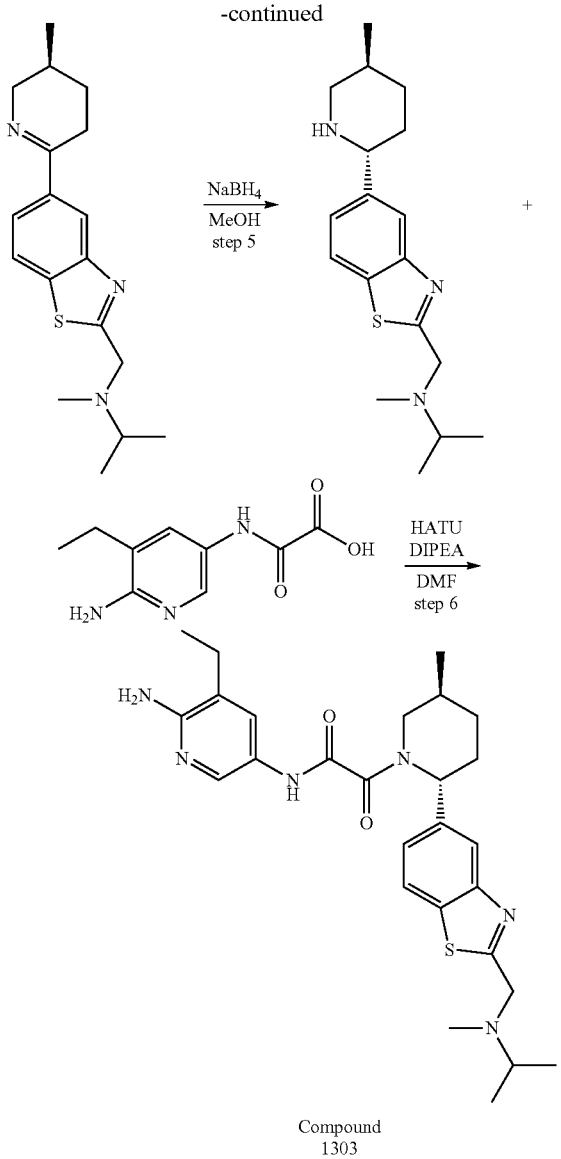

Compound 1303

Step 1: Synthesis of N-((5-bromobenzo[d]thiazol-2-yl)methyl)-N-methylpropan-2-amine Prepared by general procedure scheme H step 1C. Yield: 1.2 g (97.09%).
LCMS(ESI): [M]+ m/z: calcd 299.2; found 300.2; Rt=0.789 min.

Step 2: Synthesis of N-methyl-N-((5-(4,4,5,5-tetramethyl-1,3,2-dioxaborolan-2-yl)benzo[d]thiazol-2-yl)methyl)propan-2-amine Prepared by general procedure scheme H step 2. Yield: 1.3 g of crude.
LCMS(ESI): [M]+ m/z: calcd 346.2; found 347.2; Rt=0.917 min.

Step 3: Synthesis of (S)-tert-butyl 6-(2-((Isopropyl (methyl)amino)methyl)benzo[d]thiazol-5-yl)-3-methyl-3,4-dihydropyridine-1(2H)-carboxylate Prepared by general procedure scheme H step 3. Yield: 0.6 g (38.46%).

CC conditions: The crude product was purified by silica gel with CHCl₃/EtOAc as an eluent mixture.
LCMS(ESI): [M]+ m/z: calcd 415.2; found 416.2; Rt=1.292 min.

Step 4: Synthesis of (S)—N-methyl-N-((5-(5-methyl-3,4,5,6-tetrahydropyridin-2-yl)benzo[d]thiazol-2-yl)methyl)propan-2-amine The stirred solution of tert-butyl (3S)-6-[2-[[isopropyl(methyl)amino]methyl]-1,3-benzothiazol-5-yl]-3-methyl-3,4-dihydro-2H-pyridine-1-carboxylate (600.00 mg, 1.44 mmol) in MeOH (10 mL) and diox/HCl (5 mL) was allowed to stir at 25° C. for 16 hr. Upon completion, the reaction mixture was evaporated, the crude product was quenched with water (20 mL) and neutralized by NaHCO₃ to pH=8. The aqueous phase was extracted with CHCl₃ (2*20 mL). The combined organic phase was dried over Na₂SO₄ and concentrated under reduced pressure. The desired product N-methyl-N-[[5-[(3S)-3-methyl-2,3,4,5-tetrahydropyridin-6-yl]-1,3-benzothiazol-2-yl]methyl]propan-2-amine (0.45 g, 1.43 mmol, 98.80% yield) was isolated.
LCMS(ESI): [M]+ m/z: calcd 315.2; found 316.2; Rt=0.395 min.

Step 5: Synthesis of N-methyl-N-((5-((2R,5S)-5-methylpiperidin-2-yl)benzo[d]thiazol-2-yl)methyl)propan-2-amine Prepared by general procedure scheme H step 5. Yield: 0.45 g (99.37%).
LCMS(ESI): [M]+ m/z: calcd 317.2; found 318.2; Rt=0.744 min.

Step 6: Synthesis of N-(6-amino-5-ethylpyridin-3-yl)-2-((2R,5S)-2-(2-((Isopropyl(methyl)amino) methyl)benzo[d]thiazol-5-yl)-5-methylpiperidin-1-yl)-2-oxoacetamide (Compound 1303

Prepared by general procedure scheme H step 6B. Yield: 62 mg (38.70%).
HPLC conditions: Column: XBridge C18 100*19 mm, 5 microM; 0-5 min 50-80% water-MeOH+0.1% NH₄OH, flow: 30 ml/min; (loading pump 4 ml/min MeCN).
¹H NMR (500 MHz, DMSO-d₆) δ (ppm) 1.03-1.14 (m, 12H), 1.32-1.40 (m, 1H), 1.67-1.71 (m, 1H), 1.85-1.89 (m, 1H), 2.08 (m, 1H), 2.18-2.26 (m, 4H), 2.34-2.41 (m, 2H), 2.77-2.95 (m, 2H), 3.47-4.05 (m, 3H), 5.28-5.69 (m, 3H), 7.32-7.51 (m, 2H), 7.82-7.86 (d, 1H), 7.99-8.07 (m, 2H), 10.52-10.57 (m, 1H).
LCMS(ESI): [M]+ m/z: calcd 508.2; found 509.2; Rt=1.915 min.

Example 559. The Synthesis of N-(6-amino-5-ethylpyridin-3-yl)-2-((2R,5)-5-methyl-2-(2-(morpholinomethyl)benzo[d]thiazol-5-yl)piperidin-1-yl)-2-oxoacetamide (Compound 1092

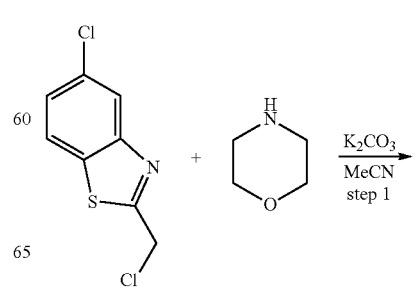

-continued

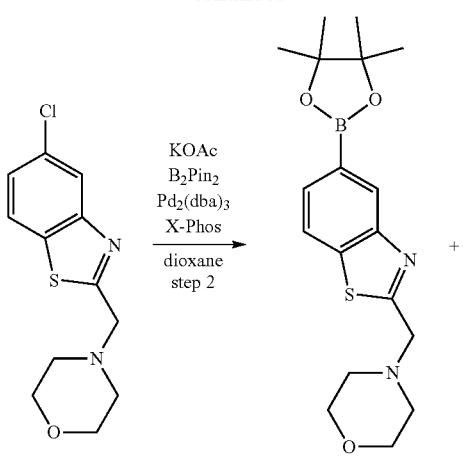

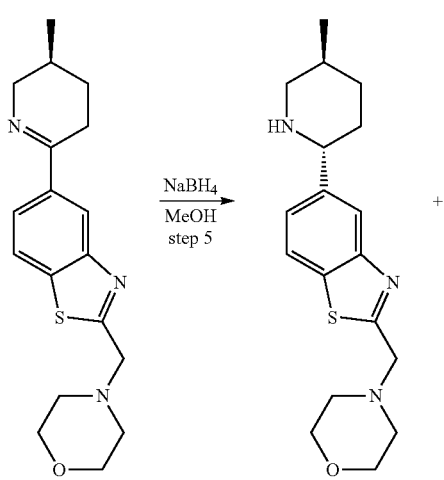

-continued

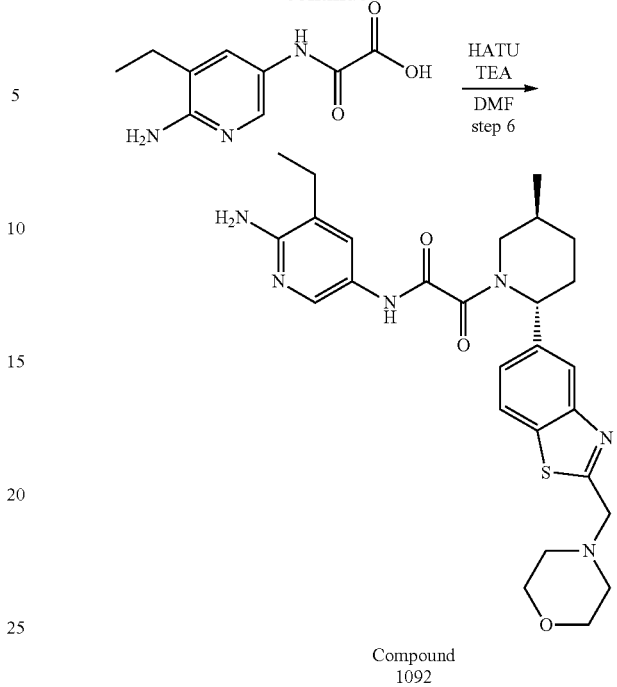

Compound 1092

Step 1: Synthesis of 4-((5-chlorobenzo[d]thiazol-2-yl)methyl)morpholine

To a solution of 5-chloro-2-(chloromethyl)-1,3-benzothiazole (5 g, 22.92 mmol) and morpholine (2.00 g, 22.92 mmol, 2.01 mL) in MeCN (50 mL) was added potassium carbonate (6.34 g, 45.85 mmol, 2.77 mL). The reaction mixture was then stirred for 24 hr at 70° C., then evaporated in vacuum. The residue was diluted with water (50 mL) and extracted with DCM (2*50 mL). The combined organic extracts were dried over sodium sulphate and evaporated in vacuum to afford 4-[(5-chloro-1,3-benzothiazol-2-yl)methyl]morpholine (6 g, 22.32 mmol, 97.38% yield).

LCMS(ESI): [M]$^+$ m/z: calcd 268.2; found 269.2; Rt=0.918 min.

Step 2: Synthesis of 4-((5-(4,4,5,5-tetramethyl-1,3,2-dioxaborolan-2-yl)benzo[d]thiazol-2-yl)methyl)morpholine Potassium acetate (4.38 g, 44.65 mmol, 2.79 mL) was added to a solution of 4-[(5-chloro-1,3-benzothiazol-2-yl)methyl]morpholine (6 g, 22.32 mmol) and 4,4,5,5-tetramethyl-2-(4,4,5,5-tetramethyl-1,3,2-dioxaborolan-2-yl)-1,3,2-dioxaborolane (6.24 g, 24.56 mmol) in dioxane (100 mL). Reaction flask was evacuated and refilled with argon 3 times. Then tris(dibenzylideneacetone)dipalladium(0) (1.02 g, 1.12 mmol) and XPhos (2.13 g, 4.46 mmol) was added under stream of argon. Resulting mixture was stirred at 90° C. for 18 hr under inert atmosphere. Then, it was cooled, diluted with EtOAc (100 mL) and filtered off. The filtrate was concentrated under reduced pressure and the residue was purified by silica gel flash chromatography eluting with a 0 to 100 percent CHCl$_3$-MeCN gradient to give 4-[[5-(4,4,5,5-tetramethyl-1,3,2-dioxaborolan-2-yl)-1,3-benzothiazol-2-yl]methyl]morpholine (8 g, 22.21 mmol, 99.46% yield).

LCMS(ESI): [M]⁺ m/z: calcd 360.2; found 361.2; Rt=1.128 min.

Step 3: Synthesis of (S)-tert-butyl 3-methyl-6-(2-(morpholinomethyl)benzo[d]thiazol-5-yl)-3,4-dihydropyridine-1(2H)-carboxylate Prepared by general procedure 8. Yield: 12 g of crude.
LCMS(ESI): [M]⁺ m/z: calcd 429.2; found 430.2; Rt=1.299 min.

Step 4: Synthesis of (S)-4-((5-(5-methyl-3,4,5,6-tetrahydropyridin-2-yl)benzo[d]thiazol-2-yl)methyl)morpholine Prepared by general procedure scheme 8. Yield: 5 g of crude.
LCMS(ESI): [M]⁺ m/z: calcd 329.2; found 330.2; Rt=0.774 min.

Step 5: Synthesis of 4-((5-((2R,5S)-5-methylpiperidin-2-yl)benzo[d]thiazol-2-yl)methyl)morpholine Prepared by general procedure scheme H step 5. Yield: 4 g of crude.
LCMS(ESI): [M]⁺ m/z: calcd 331.2; found 332.2; Rt=0.798 min.

Step 6: Synthesis of N-(6-amino-5-ethylpyridin-3-yl)-2-((2R,5S)-5-methyl-2-(2-(morpholinomethyl)benzo[d]thiazol-5-yl)piperidin-1-yl)-2-oxoacetamide (Compound 1092

Prepared by general procedure scheme 8. Yield: 90 mg (31.20%).
HPLC conditions: Column: YMC Triart C18 100*20 mm, 5 microM; 0-1-5 min 35-35-60% water-MeCN+0.1% NH₄OH, flow: 30 ml/min; (loading pump 4 ml/min MeCN).
¹H NMR (600 MHz, DMSO-d₆) δ (ppm) 1.02-1.06 (t, 3H), 1.11-1.13 (m, 3H), 1.32-1.39 (m, 2H), 1.69-1.89 (m, 3H), 2.05-2.20 (m, 2H), 2.27-2.41 (m, 3H), 2.52-2.54 (m, 2H), 2.77-2.79 (m, 1H), 3.47-3.61 (m, 4H), 3.91-4.05 (m, 2H), 5.28-5.69 (m, 3H), 7.35-7.51 (m, 2H), 7.86-8.07 (m, 3H), 10.55 (br s, 1H).
LCMS(ESI): [M]⁺ m/z: calcd 522.2; found 523.2; Rt=2.102 min.

Example 560. The Synthesis of N-(6-amino-5-ethylpyridin-3-yl)-2-((2R,5S)-2-(2-(hydroxymethyl)benzo[d]thiazol-5-yl)-5-methylpiperidin-1-yl)-2-oxoacetamide (Compound 1152)

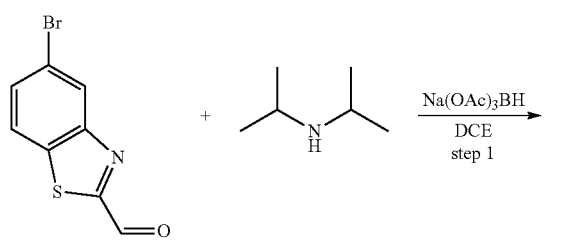

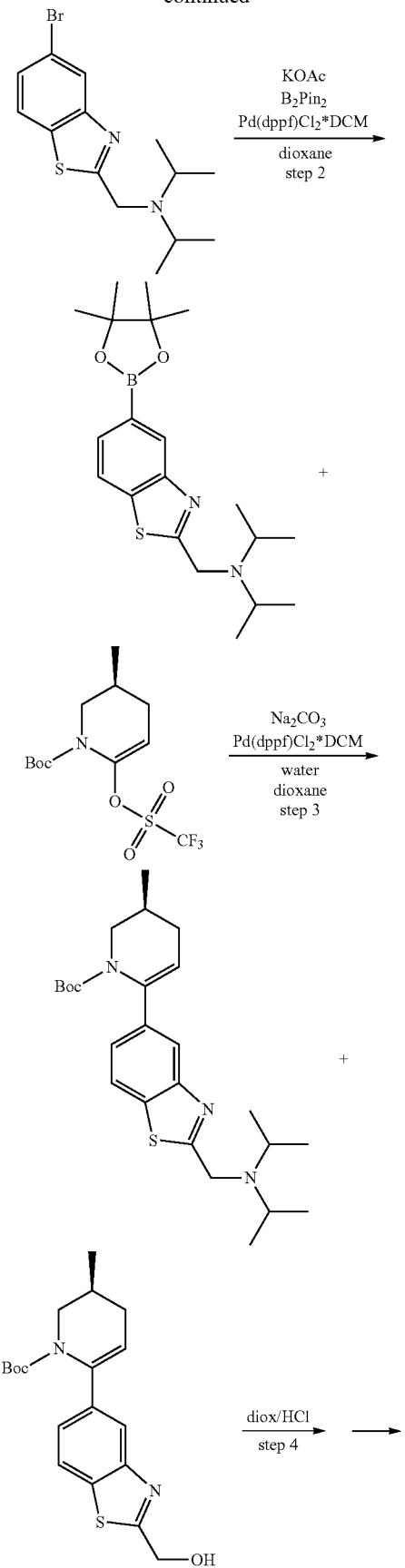

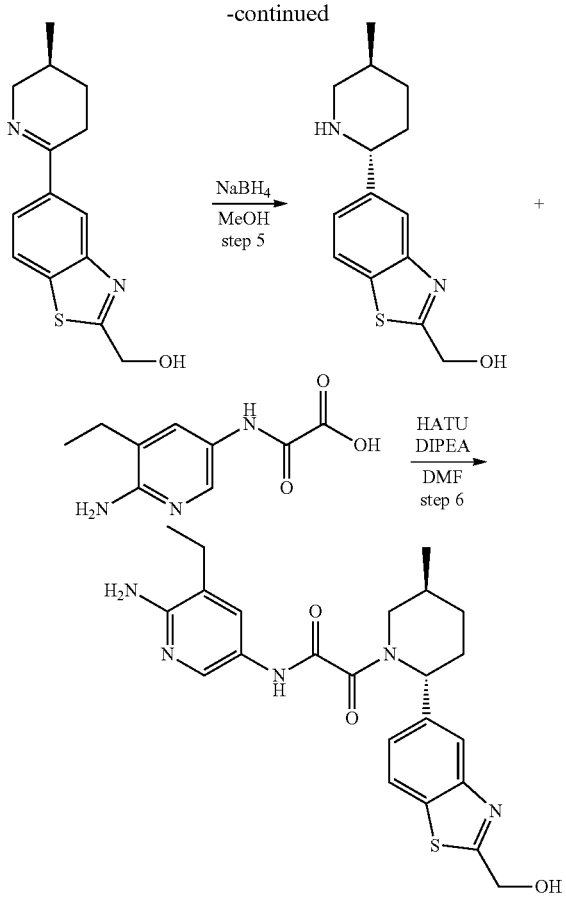

Step 1: Synthesis of N-((5-bromobenzo[d]thiazol-2-yl)methyl)-N-Isopropylpropan-2-amine Prepared by general procedure scheme H step 1C. Yield: 0.8 g (59.18%).
LCMS(ESI): [M]+ m/z: calcd 327.2; found 328.2; Rt=1.122 min.

Step 2: Synthesis of N-isopropyl-N-((5-(4,4,5,5-tetramethyl-1,3,2-dioxaborolan-2-yl)benzo[d]thiazol-2-yl)methyl)propan-2-amine Prepared by general procedure scheme H step 2. Yield: 1.1 g of crude.
LCMS(ESI): [M]+ m/z: calcd 374.2; found 375.2; Rt=1.196 min.

Step 3: Synthesis of (S)-tert-butyl 6-(2-(hydroxymethyl)benzo[d]thiazol-5-yl)-3-methyl-3,4-dihydropyridine-1(2H)-carboxylate N-isopropyl-N-[[5-(4,4,5,5-tetramethyl-1,3,2-dioxaborolan-2-yl)-1,3-benzothiazol-2-yl]methyl]propan-2-amine (1.1 g, 2.94 mmol) and tert-butyl (3S)-3-methyl-6-(trifluoromethylsulfonyloxy)-3,4-dihydro-2H-pyridine-1-carboxylate (1.12 g, 3.23 mmol) were mixed in dioxane (30 mL). The resulting mixture was evacuated and then backfilled with argon, this operation was repeated three times, then sodium carbonate (934.33 mg, 8.82 mmol, 369.01 L) in water (10 mL) and Pd(dppf)Cl$_2$*DCM (119.98 mg, 146.92 µmol) were added under argon. The reaction mixture was stirred under argon at 90° C. for 12 hr. Then the reaction mixture was cooled and evaporated in vacuum, poured into water (100 ml) and extracted with EtOAc (3×20 ml). The combined organic extracts were washed with water (2*10 ml), dried over sodium sulphate and evaporated in vacuum to afford crude product that was purified by column chromatography in system CHCl$_3$/MeOH (1:1) to afford two fractions: tert-butyl (3S)-6-[2-[(diisopropylamino)methyl]-1,3-benzothiazol-5-yl]-3-methyl-3,4-dihydro-2H-pyridine-1-carboxylate (0.95 g, 2.14 mmol, 72.87% yield) and tert-butyl (3S)-6-[2-(hydroxymethyl)-1,3-benzothiazol-5-yl]-3-methyl-3,4-dihydro-2H-pyridine-1-carboxylate (0.1 g, 277.42 µmol, 9.44% yield).
LCMS(ESI): [M]+ m/z: calcd 360.2; found 361.2; Rt=1.423 min.

Step 4: Synthesis of (S)-(5-(5-methyl-3,4,5,6-tetrahydropyridin-2-yl)benzo[d]thiazol-2-yl)methanol tert-butyl (3S)-6-[2-(hydroxymethyl)-1,3-benzothiazol-5-yl]-3-methyl-3,4-dihydro-2H-pyridine-1-carboxylate (0.1 g, 277.42 µmol) was dissolved in the diox/HCl (50 mL) and resulting reaction mixture was stirred at 25° C. for 12 hr. Then the solvent was evaporated dryness, the residue was diluted by water (20 ml.) and the resulting aqueous phase was washed by DCM (3*20 mL). Then NaHCO$_3$ was added to alkaline reaction and this aqueous phase was extracted by DCM (3*30 mL), dried over Na$_2$SO$_4$ and evaporated under reduced pressure to give pure [5-[(3S)-3-methyl-1,2,3,4-tetrahydropyridin-6-yl]-1,3-benzothiazol-2-yl]methanol (0.04 g, 153.64 mol, 55.38% yield).
LCMS(ESI): [M]+ m/z: calcd 260.2; found 261.2; Rt=0.514 min.

Step 5: Synthesis of (5-((2R,5S)-5-methylpiperidin-2-yl)benzo[d]thiazol-2-yl)methanol Prepared by general procedure scheme H step 5. Yield: 40 mg of crude.
LCMS(ESI): [M]+ m/z: calcd 262.2; found 263.2; Rt=0.813 min.

Step 6: Synthesis of N-(6-amino-5-ethylpyridin-3-yl)-2-((2R,5S)-2-(2-(hydroxymethyl)benzo[d]thiazol-5-yl)-5-methylpiperidin-1-yl)-2-oxoacetamide (Compound 1152)

Prepared by general procedure scheme H step 6B. Yield: 28.8 mg (41.65%).
HPLC conditions: Column: XBridge C18 100*19 mm, 5 microM; 0-5 min 25-75% water-MeOH+0.1% NH$_4$OH, flow: 30 ml/min; (loading pump 4 ml/min MeCN).
Then the product N-(6-amino-5-ethyl-3-pyridyl)-2-[(2R,5S)-2-[2-(hydroxymethyl)-1,3-benzothiazol-5-yl]-5-methyl-1-piperidyl]-2-oxo-acetamide (0.0288 g, 63.50 µmol, 41.65% yield) was purificated by chiral chromatography to get the more pure product N-(6-amino-5-ethyl-3-pyridyl)-2-[(2R,5S)-2-[2-(hydroxymethyl)-1,3-benzothiazol-5-yl]-5-methyl-1-piperidyl]-2-oxo-acetamide (13.81 mg, 30.45 µmol, 19.97% yield) as 2$^{nd}$ lot—Compound 1152.
The conditions of chiral chromatography:
Chiralcel OD-H (250*20 mm, 5 mkm), Hexane-IPA-MeOH, 80-10-10, 10 ml/min.
$^1$H NMR (600 MHz, DMSO-d$_6$) δ (ppm) 0.75-1.05 (m, 3H), 1.06-1.14 (m, 3H), 1.28-1.44 (m, 1H), 1.67-1.75 (m, 1H), 1.82-1.94 (m, 1H), 2.03-2.22 (m, 1H), 2.25-2.37 (m, 2H), 2.39-2.44 (m, 1H), 2.75-3.28 (m, 1H), 3.47-F1 (m, 1H), 4.82-4.87 (m, 2H), 5.26-5.61 (m, 1H), 5.61-5.75 (m, 2H), 6.29 (br s, 1H), 7.32-7.43 (m, 1H), 7.43-7.55 (m, 1H), 7.83-7.90 (m, 1H), 7.97-8.12 (m, 2H), 10.55 (br s, 1H).

LCMS(ESI): [M]⁺ m/z: calcd 453.2; found 454.2; Rt=2.154 min.

Example 561. Synthesis of N-(6-amino-5-methylpyridin-3-yl)-2-((2R,5S)-5-methyl-2-(2-(tetrahydrofuran-3-yl)benzo[d]thiazol-5-yl)piperidin-1-yl)-2-oxoacetamide (Compound 1145)

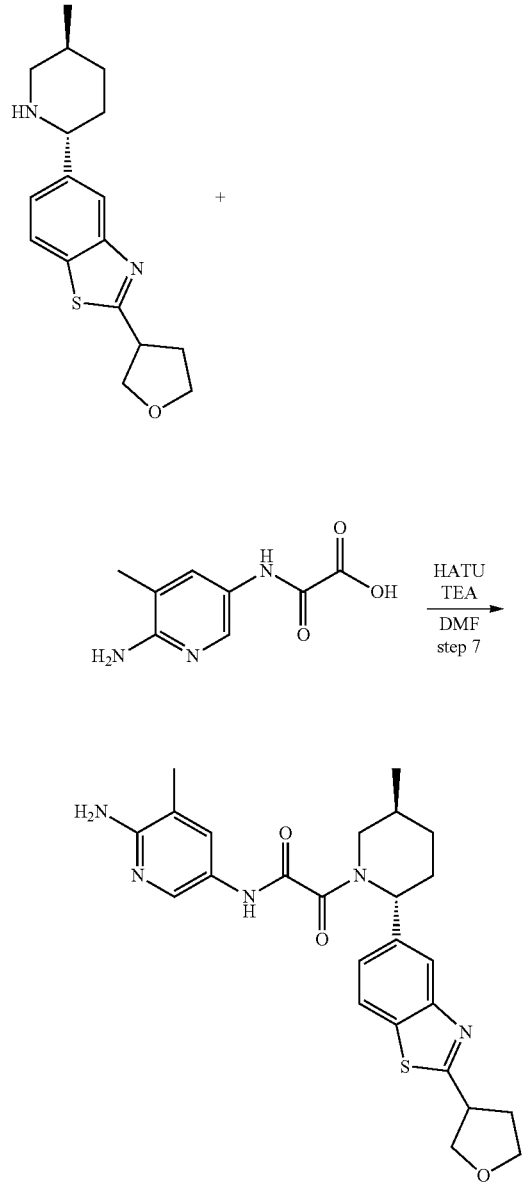

Prepared by general procedure scheme H step 6A. Yield: 200 mg (50.45%).

HPLC conditions: Column: XBridge C18 100*19 mm, 5 microM; 0-1-6 min 40-40-75% water-MeOH+0.1% NH₄OH, flow: 30 ml/min; (loading pump 4 ml/min MeOH).

¹H NMR (600 MHz, DMSO-d₆) δ (ppm) 1.03 (m, 3H), 1.36 (m, 1H), 1.70 (m, 1H), 1.87 (m, 1H), 1.99 (m, 3H), 2.25 (m, 2H), 2.42 (m, 2H), 2.96 (dd, 1H), 3.64 (m, 2H), 4.03 (m, 4H), 5.63 (m, 3H), 7.41 (m, 2H), 7.91 (m, 1H), 8.04 (m, 2H), 10.54 (m, 1H).

LCMS(ESI): [M]⁺ m/z: calcd 479.2; found 480.2; Rt=1.254 min.

Example 562. The Synthesis of N-(6-amino-5-methylpyridin-3-yl)-2-((2R,5S)-5-methyl-2-(2-(1-methyl-1H-imidazol-2-yl)benzo[d]thiazol-5-yl)piperidin-1-yl)-2-oxoacetamide (Compound 1186)

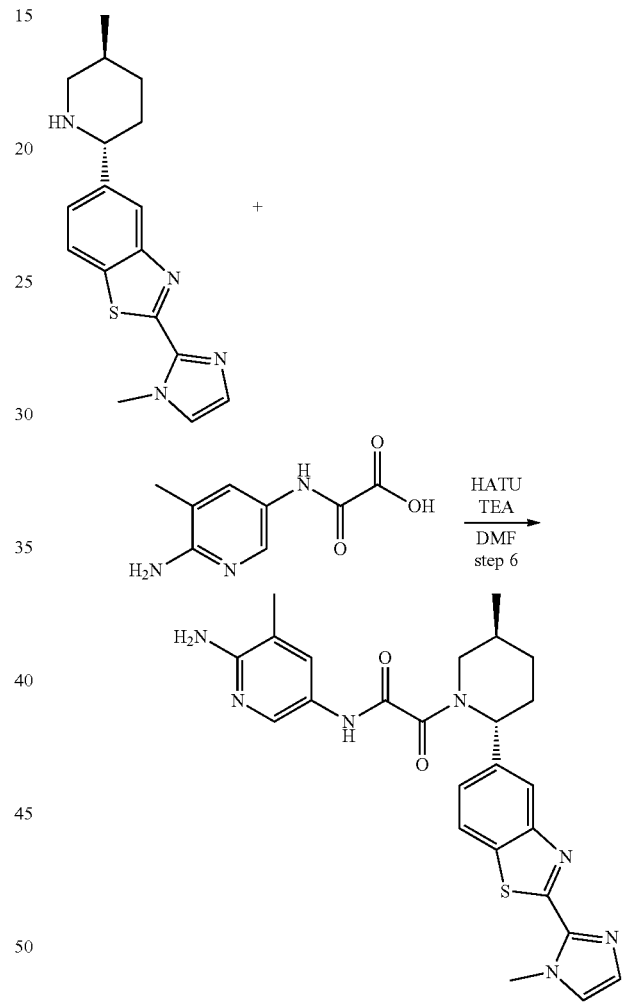

Prepared by general procedure scheme H step 6A. Yield: 199 mg (50.80%).

HPLC conditions: Column: YMC Triart C18 100*20 mm, 5 microM; 0-1-5 min 20-20-45% water-MeCN+0.1% NH₄OH, flow: 30 ml/min; (loading pump 4 ml/min MeCN).

¹H NMR (600 MHz, DMSO-d₆) δ (ppm) 1.03-1.05 (m, 3H), 1.34-1.40 (m, 1H), 1.73 (m, 1H), 1.87-2.19 (m, 5H), 2.30-2.33 (m, 1H), 3.40-3.52 (m, 2H), 4.05-4.33 (m, 4H), 5.58-5.71 (m, 2H), 7.13 (s, 1H), 7.41-7.50 (m, 3H), 7.92-8.13 (m, 3H), 10.53-10.58 (m, 1H).

LCMS(ESI): [M]⁺ m/z: calcd 489.2; found 490.2; Rt=2.879 min.

Example 563. Synthesis of 2-((2R,5S)-2-(2-(1-acetylpiperidin-4-yl)benzo[d]thiazol-5-yl)-5-methylpiperidin-1-yl)-N-(6-amino-5-methylpyridin-3-yl)-2-oxoacetamide (Compound 1093
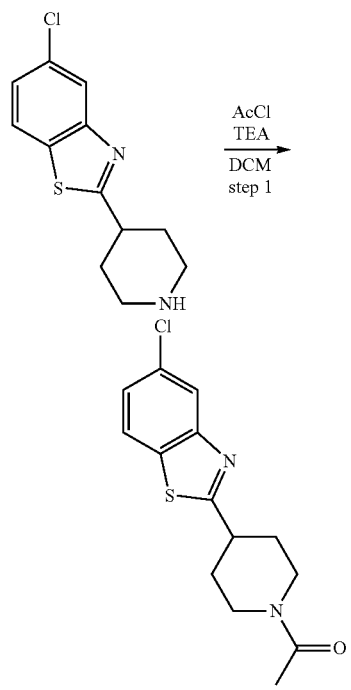
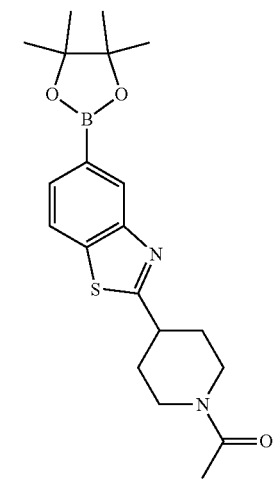
-continued
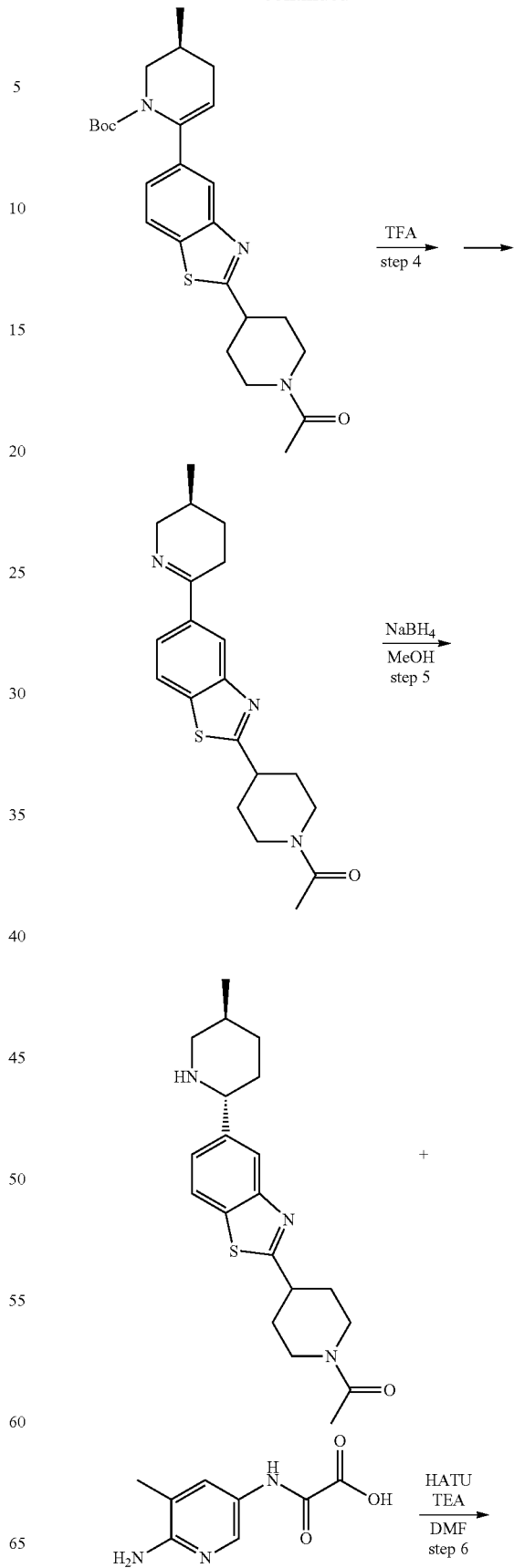

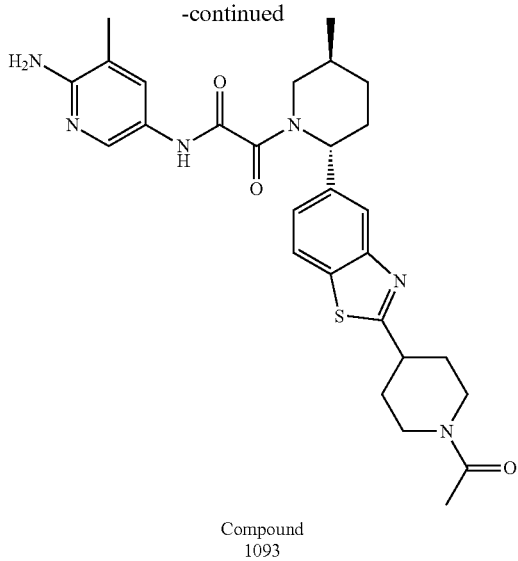

Compound 1093

Step 1: Synthesis of 1-(4-(5-chlorobenzo[d]thiazol-2-yl)piperidin-1-yl)ethanone Acetyl chloride (931.68 mg, 11.87 mmol, 722.23 uL) was added dropwise to a stirred solution of 5-chloro-2-(4-piperidyl)-1,3-benzothiazole (2.5 g, 9.89 mmol) and TEA (1.50 g, 14.84 mmol, 2.07 mL) in DCM (75 mL) at 0° C. The resulting mixture was stirred at 0° C. for 2 hr, then washed with water (25 ml). The organic layer was separated, dried over sodium sulphate and concentrated in vacuum to afford 1-[4-(5-chloro-1,3-benzothiazol-2-yl)-1-piperidyl]ethanone (2.8 g, 9.50 mmol, 96.03% yield) as light-yellow solid.

LCMS(ESI): $[M]^+$ m/z: calcd 294.2; found 295.2; Rt=1.357 min.

Step 2: Synthesis of 1-(4-(5-(4,4,5,5-tetramethyl-1,3,2-dioxaborolan-2-yl)benzo[d]thiazol-2-yl)piperidin-1-yl)ethanone A mixture of 1-[4-(5-chloro-1,3-benzothiazol-2-yl)-1-piperidyl]ethanone (2.3 g, 7.80 mmol), 4,4,5,5-tetramethyl-2-(4,4,5,5-tetramethyl-1,3,2-dioxaborolan-2-yl)-1,3,2-dioxaborolane (2.18 g, 8.58 mmol) and potassium acetate (1.53 g, 15.60 mmol, 975.39 uL) in dioxane (100 mL) was evacuated and then backfilled with argon. This operation was repeated two times, then tris(1,5-diphenylpenta-1,4-dien-3-one)dipalladium (357.22 mg, 390.10 umol) and dicyclohexyl[2',4',6'-tris(propan-2-yl)-[1,1'-biphenyl]-2-yl]phosphane (743.87 mg, 1.56 mmol) were added under argon, and the reaction mixture was stirred at 95° C. for 18 hr. The reaction mixture was cooled down and concentrated in vacuum. The residue was purified by column chromatography on silica gel using chloroform/ethyl acetate gradient (0-100% ethyl acetate) to afford 1-[4-[5-(4,4,5,5-tetramethyl-1,3,2-dioxaborolan-2-yl)-1,3-benzothiazol-2-yl]-1-piperidyl]ethanone (2.3 g, 5.95 mmol, 76.31% yield) as light-yellow solid.

LCMS(ESI): $[M]^+$ m/z: calcd 386.2; found 387.2; Rt=1.347 min.

Step 3: Synthesis of (S)-tert-butyl 6-(2-(1-acetylpiperidin-4-yl)benzo[d]thiazol-5-yl)-3-methyl-3,4-dihydropyridine-1(2H)-carboxylate Prepared by general procedure scheme 8. Yield: 2.2 g (81.10%).

CC conditions: The crude product was purified by silica gel with CHCl$_3$/EtOAc as an eluent mixture.

LCMS(ESI): $[M]^+$ m/z: calcd 455.2; found 456.2; Rt=1.546 min.

Step 4: Synthesis of (S)-1-(4-(5-(5-methyl-3,4,5,6-tetrahydropyridin-2-yl)benzo[d]thiazol-2-yl)piperidin-1-yl)ethanone Prepared by general procedure 8. Yield: 1.2 g (69.91%).

LCMS(ESI): $[M]^+$ m/z: calcd 355.2; found 356.2; Rt=0.730 min.

Step 5: Synthesis of 1-(4-(5-((2R,5S)-5-methylpiperidin-2-yl)benzo[d]thiazol-2-yl)piperidin-1-yl)ethanone Prepared by general procedure scheme H step 5. Yield: 0.7 g (58%).

LCMS(ESI): $[M]^+$ m/z: calcd 357.2; found 358.2; Rt=0.750 min.

Step 6: Synthesis of 2-((2R,5S)-2-(2-(1-acetylpiperidin-4-yl)benzo[d]thiazol-5-yl)-5-methylpiperidin-1-yl)-N-(6-amino-5-methylpyridin-3-yl)-2-oxoacetamide (Compound 1093)

Prepared by general procedure 8. Yield: 48 mg (8.02%).

HPLC conditions: Column: YMC Triart C18 100*20 mm, 5 microM; 0-1-6 min 30-30-50% water-MeCN+0.1% NH$_4$OH, flow: 30 ml/min; (loading pump 4 ml/min MeCN).

$^1$H NMR (500 MHz, DMSO-d$_6$) δ (ppm) 1.03 (m, 3H), 1.35 (m, 1H), 1.59 (m, 1H), 1.73 (m, 2H), 1.87 (m, 1H), 2.03 (m, 6H), 2.11 (m, 3H), 2.31 (m, 1H), 2.76 (m, 1H), 3.19 (m, 2H), 3.40 (m, 2H), 3.68 (dd, 1H), 4.22 (dd, 1H), 5.56 (m, 3H), 7.43 (m, 2H), 7.88 (m, 1H), 8.00 (m, 1H), 8.09 (m, 1H), 10.56 (m, 1H).

LCMS(ESI): $[M]^+$ m/z: calcd 534.2; found 535.2; Rt=2.699 min.

Example 564. The Synthesis of N-(6-amino-5-methylpyridin-3-yl)-2-((2R,5S)-5-methyl-2-(2-(1-methyl-1H-imidazol-4-yl)benzo[d]thiazol-5-yl)piperidin-1-yl)-2-oxoacetamide (Compound 1214

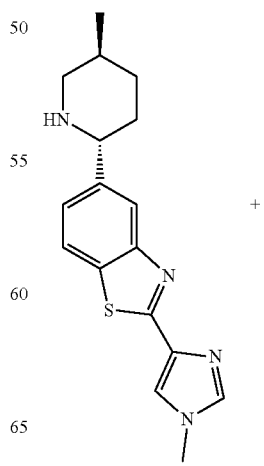

+

2505

-continued

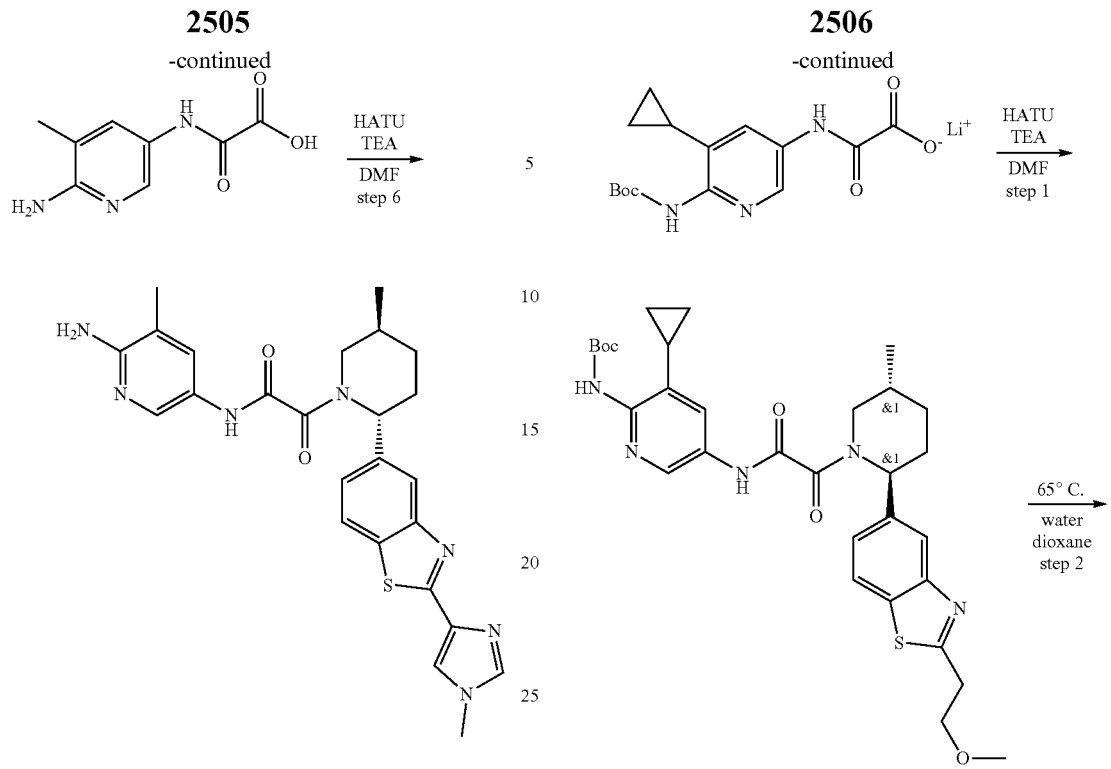

Prepared by general procedure scheme H step 6A. Yield: 267 mg (57.10%).

HPLC conditions: Column: Chromatorex C18 100*19 mm, 5 microM; 0-5 min 20-70% water-MeOH, flow: 30 ml/min; (loading pump 4 ml/min MeOH).

$^1$H NMR (600 MHz, DMSO-$d_6$) δ (ppm) 1.02-1.05 (m, 3H), 1.69-2.37 (m, 8H), 2.79-2.81 (m, 1H), 3.47-4.06 (m, 4H), 5.27-5.70 (m, 3H), 7.31-7.55 (m, 2H), 7.78-8.06 (m, 5H), 10.52-10.62 (m, 1H).

LCMS(ESI): [M]$^+$ m/z: calcd 489.2; found 490.2; Rt=2.455 min.

Example 565. The Synthesis of N-(6-amino-5-cyclopropylpyridin-3-yl)-2-(2-(2-(2-methoxyethyl)benzo[d]thiazol-5-yl)-5-methylpiperidin-1-yl)-2-oxoacetamide (Compound 1176 and Compound 1332

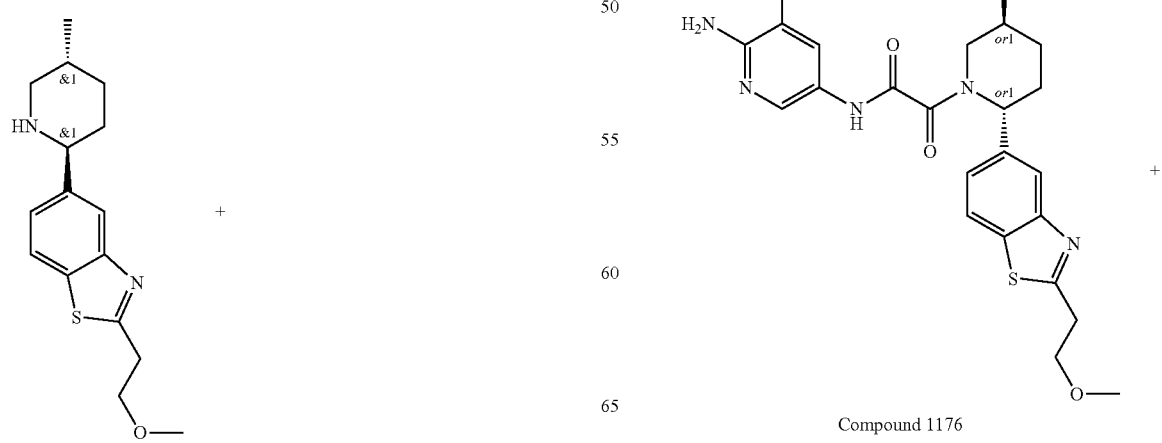

Compound 1176

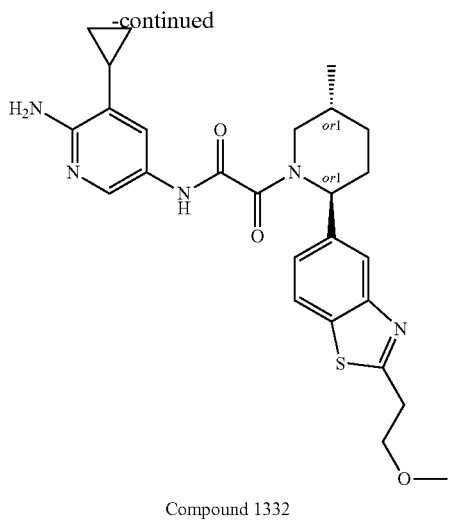

Compound 1332

Step 1: Synthesis of rac-tert-butyl (3-cyclopropyl-5-(2-((2R,5S)-2-(2-(2-methoxyethyl)benzo[d]thiazol-5-yl)-5-methylpiperidin-1-yl)-2-oxoacetamido)pyridin-2-yl)carbamate Prepared by general procedure scheme H step 6A. Yield: 0.7 g of crude.

LCMS(ESI): [M]+ m/z: calcd 534.2; found 535.2; Rt=2.624 min.

Step 2: Synthesis of N-(6-amino-5-methylpyridin-3-yl)-2-(2-(2-(2-methoxyethyl)benzo[d]thiazol-5-yl)-5-methylpiperidin-1-yl)-2-oxoacetamide The solution of tert-butyl N-[3-cyclopropyl-5-[[2-[(2R,5S)-2-[2-(2-methoxyethyl)-1,3-benzothiazol-5-yl]-5-methyl-1-piperidyl]-2-oxo-acetyl]amino]-2-pyridyl]carbamate (0.7 g, 1.18 mmol) in dioxane (6 mL) and water (3 mL) was stirred for 64 hr at 65° C. and the solvents were evaporated in vacuum. The residue was subjected to RP-HPLC (column: XBridge BEH C18 5 um 130 A; 45-45-80% 0-1-6 min H$_2$O/MeOH/0.1% NH$_4$OH, flow: 30 ml/min as mobile phase) to give N-(6-amino-5-cyclopropyl-3-pyridyl)-2-[(2R,5S)-2-[2-(2-methoxyethyl)-1,3-benzothiazol-5-yl]-5-methyl-1-piperidyl]-2-oxo-acetamide (158 mg, 320.08 umol, 27.15% yield).

LCMS(ESI): [M]+ m/z: calcd 493.2; found 494.2; Rt=2.452 min.

Step 3: Chiral Separation (Compound 1176 and Compound 1332

Racemic N-(6-amino-5-methylpyridin-3-yl)-2-(2-(2-(2-methoxyethyl)benzo[d]thiazol-5-yl)-5-methylpiperidin-1-yl)-2-oxoacetamide (158 mg, 320.08 μmol) was chiral separated (Column: Chiralpak IC-III (250*20, 5 mkm), IPA-MeOH, 50-50, 10 ml/min) to obtain N-(6-amino-5-cyclopropyl-3-pyridyl)-2-[(2R,5S)-2-[2-(2-methoxyethyl)-1,3-benzothiazol-5-yl]-5-methyl-1-piperidyl]-2-oxo-acetamide (60 mg, 121.55 umol, 75.95% yield) (RT=24.22) and N-(6-amino-5-cyclopropyl-3-pyridyl)-2-[(2S,5R)-2-[2-(2-methoxyethyl)-1,3-benzothiazol-5-yl]-5-methyl-1-piperidyl]-2-oxo-acetamide (57 mg, 115.47 umol, 72.15% yield) (RT=38.03).

Rel Time for Compound 1176 in analytical conditions (column: IC, IPA-MeOH, 50-50, 0.6 ml/min as mobile phase) 18.91 min and for Compound 1332 29.26 min.

Compound 1176:

Retention time: 18.91 min $^1$H NMR (600 MHz, DMSO-d$_6$) δ (ppm) 0.36-0.53 (m, 2H), 0.82-0.91 (m, 2H), 0.99-1.07 (m, 3H), 1.30-1.42 (m, 1H), 1.57-1.75 (m, 2H), 1.82-1.91 (m, 1H), 2.06-2.23 (m, 1H), 2.26-2.36 (m, 1H), 2.75-3.26 (m, 1H), 3.27 (s, 3H), 3.31-3.34 (m, 2H), 3.44-3.52 (m, 0.6H), 3.72-3.79 (m, 2H), 4.02-4.07 (m, 0.4H), 5.25-5.70 (m, 1H), 5.70-5.82 (m, 2H), 7.24-7.46 (m, 2H), 7.83-7.90 (m, 1H), 7.96-8.10 (m, 2H), 10.46-10.66 (m, 1H).

LCMS(ESI): [M]+ m/z: calcd 493.2; found 494.2; Rt=2.609 min

Compound 1332:

Retention time: 29.26 min $^1$H NMR (600 MHz, DMSO-d$_6$) δ (ppm) 0.38-0.52 (m, 2H), 0.81-0.91 (m, 2H), 1.00-1.07 (m, 3H), 1.31-1.42 (m, 1H), 1.59-1.75 (m, 2H), 1.79-1.95 (m, 1H), 2.06-2.22 (m, 1H), 2.26-2.35 (m, 1H), 2.76-3.26 (m, 1H), 3.27 (s, 3H), 3.31-3.34 (m, 2H), 3.44-3.53 (m, 0.6H), 3.71-3.80 (m, 2H), 4.02-4.06 (m, 0.4H), 5.25-5.70 (m, 1H), 5.70-5.84 (m, 2H), 7.27-7.43 (m, 2H), 7.82-7.92 (m, 1H), 7.96-8.10 (m, 2H), 10.46-10.57 (m, 1H).

LCMS(ESI): [M]+ m/z: calcd 493.2; found 494.2; Rt=2.605 min.

Example 566. The Synthesis of 2-((2R,5S)-2-(2-((Dimethylamino)methyl)benzo[d]thiazol-5-yl)-5-methylpiperidin-1-yl)-2-oxo-N-(5-oxo-5,6,7,8-tetrahydro-1,6-naphthyridin-3-yl)acetamide (Compound 1354

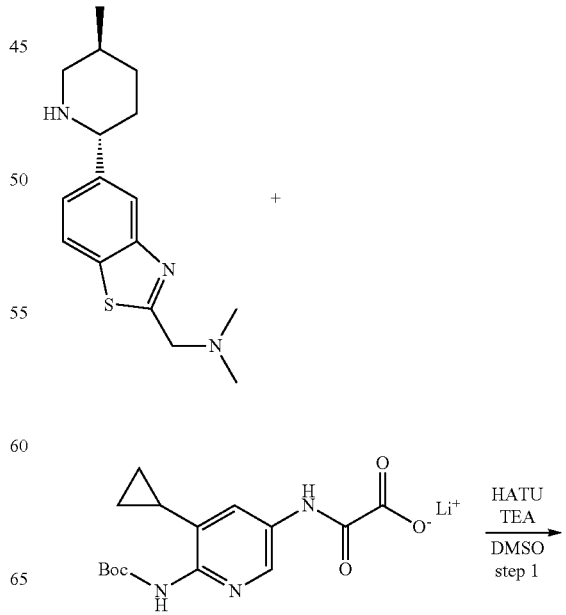

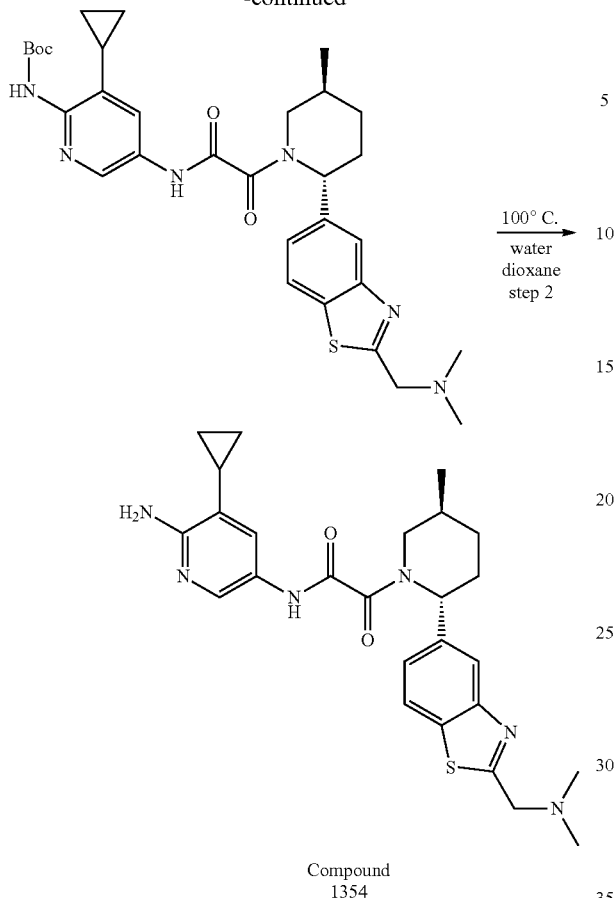

Compound 1354

Step 1: Synthesis of tert-butyl (3-cyclopropyl-5-(2-((2R,5S)-2-(2-((Dimethylamino)methyl)benzo[d]thiazol-5-yl)-5-methylpiperidin-1-yl)-2-oxoacetamido)pyridin-2-yl)carbamate Prepared by general procedure scheme H step 6A. Yield: 268 mg of crude.

HPLC conditions: Column: SunFire C18 100*19 mm, 5 microM; 2-10 min 50-80% MeOH+NH$_3$; (loading pump 4 ml/min MeOH+NH$_3$).

LCMS(ESI): [M]$^+$ m/z: calcd 592.2; found 593.2; Rt=1.029 min.

Step 2: Synthesis of 2-((2R,5S)-2-(2-((Dimethylamino)methyl)benzo[d]thiazol-5-yl)-5-methylpiperidin-1-yl)-2-oxo-N-(5-oxo-5,6,7,8-tetrahydro-1,6-naphthyridin-3-yl)acetamide (Compound 1354)

tert-butyl N-[3-cyclopropyl-5-[[2-[(2R,5S)-2-[2-[(dimethylamino)methyl]-1,3-benzothiazol-5-yl]-5-methyl-1-piperidyl]-2-oxo-acetyl]amino]-2-pyridyl]carbamate (73 mg, 87.44 umol) was dissolved in mixture of water (1 mL) and dioxane (1 mL) and heated with stirring at 100° C. for 12 hr. Crude product was dissolved in DMSO and subjected to HPLC (SYSTEM 2-10 min 30-55% MeCN+NH$_3$ flow 30 ml/min (loading pump 4 ml/min), Column Sun Fire C18 100*19 mm). N-(6-amino-5-cyclopropyl-3-pyridyl)-2-[(2R,5S)-2-[2-[(dimethylamino)methyl]-1,3-benzothiazol-5-yl]-5-methyl-1-piperidyl]-2-oxo-acetamide (19.8 mg, 40.19 umol, 45.97% yield) was obtained.

$^1$H NMR (500 MHz, DMSO-d$_6$) δ (ppm) 0.38-0.51 (m, 2H), 0.82-0.91 (m, 2H), 0.98-1.06 (m, 3H), 1.28-1.41 (m, 1H), 1.58-1.73 (m, 2H), 1.81-1.93 (m, 1H), 2.04-2.20 (m, 1H), 2.25-2.32 (m, 7H), 2.75-3.26 (m, 1H), 3.45-4.09 (m, 3H), 5.26-5.70 (m, 1H), 5.72-5.82 (m, 2H), 7.26-7.46 (m, 2H), 7.82-7.90 (m, 1H), 7.96-8.08 (m, 2H), 10.43-10.60 (m, 1H).

LCMS(ESI): [M]$^+$ m/z: calcd 492.2; found 493.2; Rt=1.651 min.

Example 567. The Synthesis of rac-N-(6-amino-5-methylpyridin-3-yl)-2-((2R,5S)-5-methyl-2-(2-(1-methyl-1H-pyrazol-4-yl)benzo[d]thiazol-5-yl)piperidin-1-yl)-2-oxoacetamide (Compound 1104

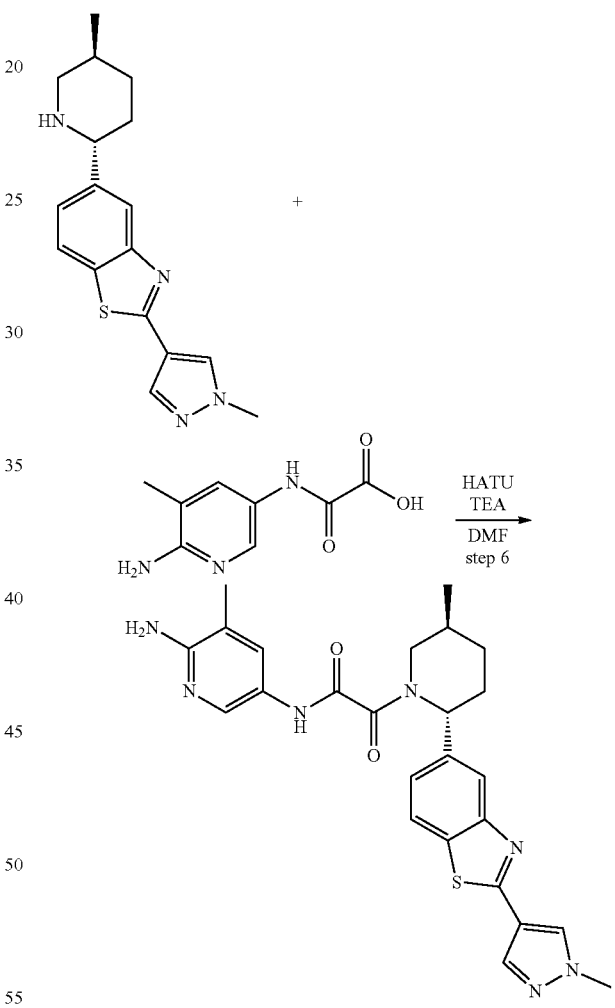

Prepared by general procedure 8 step 6A. Yield: 88.4 mg (20.15%).

HPLC conditions: Column: YMC Triart C18 100*20 mm, 5 microM; 0-5 min 30-70% water-MeCN+0.1% NH$_4$OH, flow: 30 ml/min; (loading pump 4 ml/min MeCN).

Compound 1104:

$^1$H NMR (500 MHz, DMSO-d$_6$) δ (ppm) 1.03 (m, 3H), 1.38 (m, 1H), 1.72 (m, 1H), 1.86 (m, 1H), 2.00 (m, 3H), 2.26 (m, 2H), 3.92 (m, 5H), 5.64 (m, 3H), 7.40 (m, 2H), 7.95 (m, 4H), 8.48 (m, 1H), 10.58 (s, 1H).

LCMS(ESI): [M]⁺ m/z: calcd 489.2; found 490.2; Rt=2.469 min.

Example 568. The Synthesis of N-(6-amino-5-methylpyridin-3-yl)-2-((2R,5S)-2-(2-(1-cyclopropylpiperidin-4-yl)benzo[d]thiazol-5-yl)-5-methylpiperidin-1-yl)-2-oxoacetamide (Compound 1181

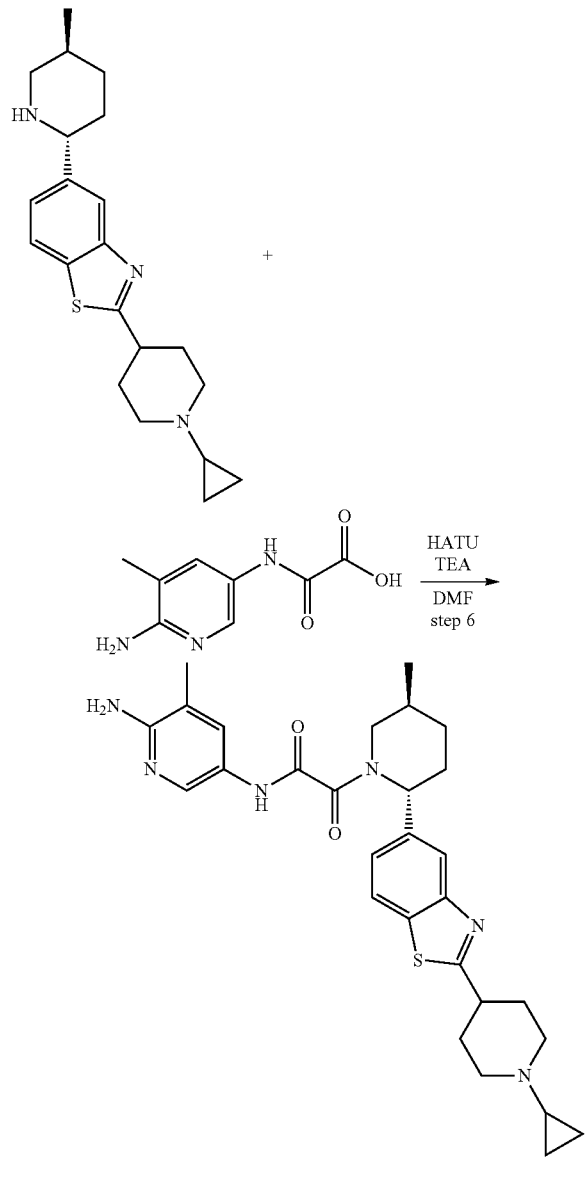

Prepared by general procedure scheme H step 6A. Yield: 53 mg (12.63%).

HPLC conditions: Column: YMC Triart C18 100*20 mm, 5 microM; 0-5 min 50-100% water-MeOH+0.1% NH₄OH, flow: 30 ml/min; (loading pump 4 ml/min MeOH).

¹H NMR (600 MHz, DMSO-d₆) δ (ppm) 0.30 (m, 2H), 0.41 (m, 2H), 1.03 (m, 3H), 1.35 (m, 1H), 1.62 (m, 1H), 1.70 (m, 3H), 1.87 (m, 1H), 2.05 (m, 5H), 2.32 (m, 3H), 2.89 (m, 3H), 3.09 (m, 1H), 3.75 (dd, 1H), 5.63 (m, 3H), 7.34 (d, 1H), 7.41 (m, 1H), 7.50 (s, 1H), 7.98 (m, 3H), 10.55 (s, 1H).

LCMS(ESI): [M]⁺ m/z: calcd 532.2; found 533.2; Rt=2.114 min.

Example 569. The Synthesis of N-(6-amino-5-methylpyridin-3-yl)-2-((2R,5)-5-methyl-2-(2-(4-methylpiperazin-1-yl)benzo[d]thiazol-5-yl)piperidin-1-yl)-2-oxoacetamide (Compound 1158

Step 1: Synthesis of (S)-tert-butyl 6-(benzo[d]thiazol-5-yl)-3-methyl-3,4-dihydropyridine-1(2H)-carboxylate

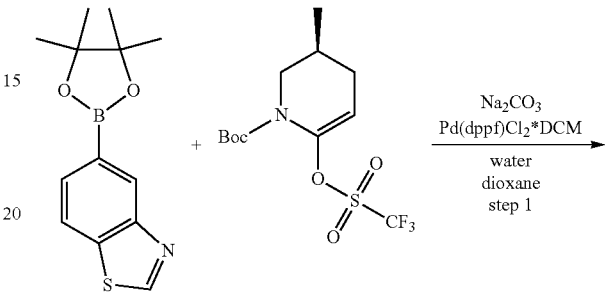

Prepared by general procedure scheme H step 3. Yield: 3 g (45.56%).

CC conditions: The crude product was purified by silica gel with hexane/MTBE as an eluent mixture.

LCMS(ESI): [M]⁺ m/z: calcd 329.2; found 330.2; Rt=1.635 min.

Step 2: Synthesis of (S)-5-(5-methyl-3,4,5,6-tetrahydropyridin-2-yl)benzo[d]thiazole

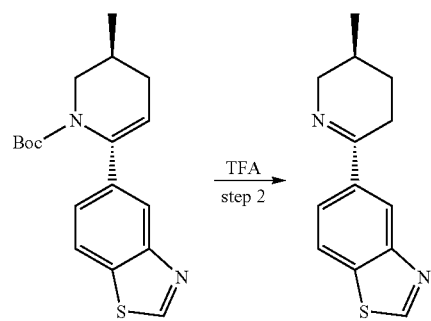

Prepared by general procedure scheme H step 4. Yield: 2 g (95.77%).

LCMS(ESI): [M]⁺ m/z: calcd 229.2; found 230.2; Rt=0.783 min.

Step 3: Synthesis of 5-((2R,5S)-5-methylpiperidin-2-yl)benzo[d]thiazole

Prepared by general procedure scheme H step 5. Yield: 2 g (99.13%).

LCMS(ESI): [M]⁺ m/z: calcd 231.2; found 232.2; Rt=0.795 min.

Step 4: Synthesis of (2R,5S)-tert-butyl 2-(benzo[d]thiazol-5-yl)-5-methylpiperidine-1-carboxylate

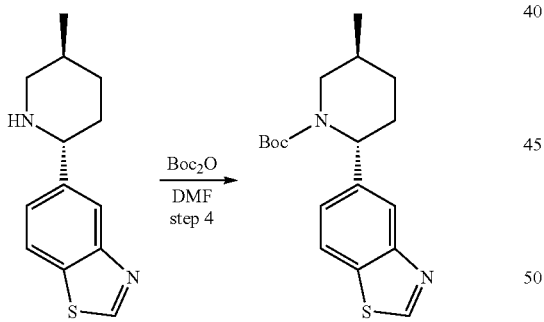

Di-tert-butyl dicarbonate (493.15 mg, 2.26 mmol, 518.56 μL) was added in one portion to a stirred solution of 5-[(2R,5S)-5-methyl-2-piperidyl]-1,3-benzothiazole (0.5 g, 2.15 mmol) in DCM (15 mL) at 25° C. The resulting mixture was stirred at 25° C. for 1 hr, and then concentrated in vacuum to afford tert-butyl (2R,5S)-2-(1,3-benzothiazol-5-yl)-5-methyl-piperidine-1-carboxylate (800 mg, crude) as brown gum, which crystallized on standing to give brown solid.

LCMS(ESI): [M]⁺ m/z: calcd 332.2; found 333.2; Rt=3.995 min.

Step 5: Synthesis of (2R,5S)-tert-butyl 2-(2-bromobenzo[d]thiazol-5-yl)-5-methylpiperidine-1-carboxylate

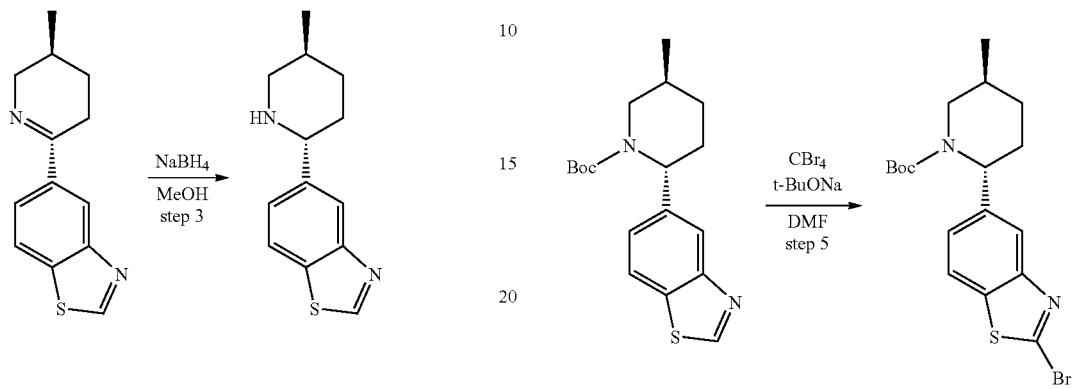

Sodium tert-butoxide (563.68 mg, 5.87 mmol) was added in one portion to a stirred solution of tert-butyl (2R,5S)-2-(1,3-benzothiazol-5-yl)-5-methyl-piperidine-1-carboxylate (650 mg, 1.96 mmol) and carbon tetrabromide (778.05 mg, 2.35 mmol, 227.50 μL) in DMF (10 mL) at 25° C. (slightly exothermic reaction!). The resulting mixture was stirred at 25° C. for 12 hr, then diluted with water (15 ml) and extracted with MTBE (3*15 ml). The combined organic extracts were washed with water (2*5 ml), dried over sodium sulphate and concentrated in vacuum to afford tert-butyl (2R,5S)-2-(2-bromo-1,3-benzothiazol-5-yl)-5-methyl-piperidine-1-carboxylate (750 mg, 1.82 mmol, 93.25% yield) as brown solid, which was directly used in the next step.

LCMS(ESI): [M]⁺ m/z: calcd 411.2; found 412.2; Rt=4.734 min.

Step 6: Synthesis of (2R,5S)-tert-butyl 5-methyl-2-(2-(4-methylpiperazin-1-yl)benzo[d]thiazol-5-yl)piperidine-1-carboxylate

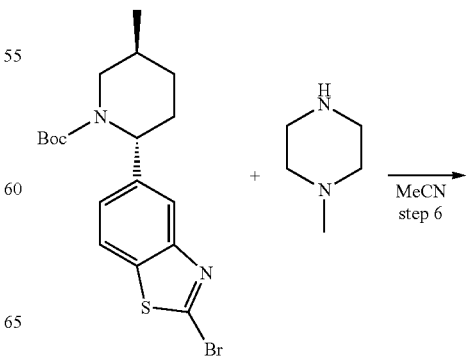

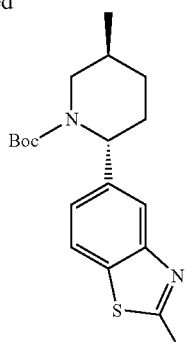

1-methylpiperazine (852.22 mg, 8.51 mmol, 943.77 μL) was added in one portion at 25° C. to a solution of tert-butyl (2R,5S)-2-(2-bromo-1,3-benzothiazol-5-yl)-5-methyl-piperidine-1-carboxylate (700 mg, 1.70 mmol) in MeCN (20 mL). The resulting mixture was stirred at 70° C. for 8 hr, then cooled down and concentrated in vacuum. The residue was basified to pH 11 with 10% aqueous sodium hydroxide solution and extracted with DCM (2*25 ml). The combined organic extracts were dried over sodium sulphate and concentrated in vacuum to afford tert-butyl (2R,5S)-5-methyl-2-[2-(4-methylpiperazin-1-yl)-1,3-benzothiazol-5-yl]piperidine-1-carboxylate (750 mg, crude) as brown solid, which was used directly in the next step.

LCMS(ESI): [M]⁺ m/z: calcd 430.2; found 431.2; Rt=3.638 min.

Step 7: Synthesis of 2-(4-methylpiperazin-1-yl)-5-((2R,5S)-5-methylpiperidin-2-yl)benzo[d]thiazole

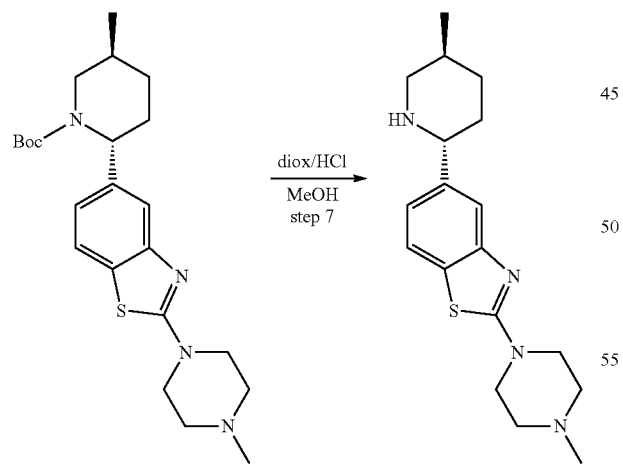

Hydrogen chloride solution 4.0 M in dioxane (31.50 g, 120.09 mmol, 39.38 mL, 13.9% purity) was added in one portion to a stirred solution of tert-butyl (2R,5S)-5-methyl-2-[2-(4-methylpiperazin-1-yl)-1,3-benzothiazol-5-yl]piperidine-1-carboxylate (775.25 mg, 1.80 mmol) in MeOH (25.01 mL). The resulting mixture was stirred at 25° C. for 1 hr, and then evaporated to dryness in vacuum to afford crude 2-(4-methylpiperazin-1-yl)-5-[(2R,5S)-5-methyl-2-piperidyl]-1,3-benzothiazole (900 mg, crude, 3HCl) as brown solid, which was used directly in the next step.

LCMS(ESI): [M]⁺ m/z: calcd 330.2; found 331.2; Rt=0.544 min.

Step 8: The Synthesis of N-(6-amino-5-methylpyridin-3-yl)-2-((2R,5S)-5-methyl-2-(2-(4-methylpiperazin-1-yl)benzo[d]thiazol-5-yl)piperidin-1-yl)-2-oxoacetamide (Compound 1158

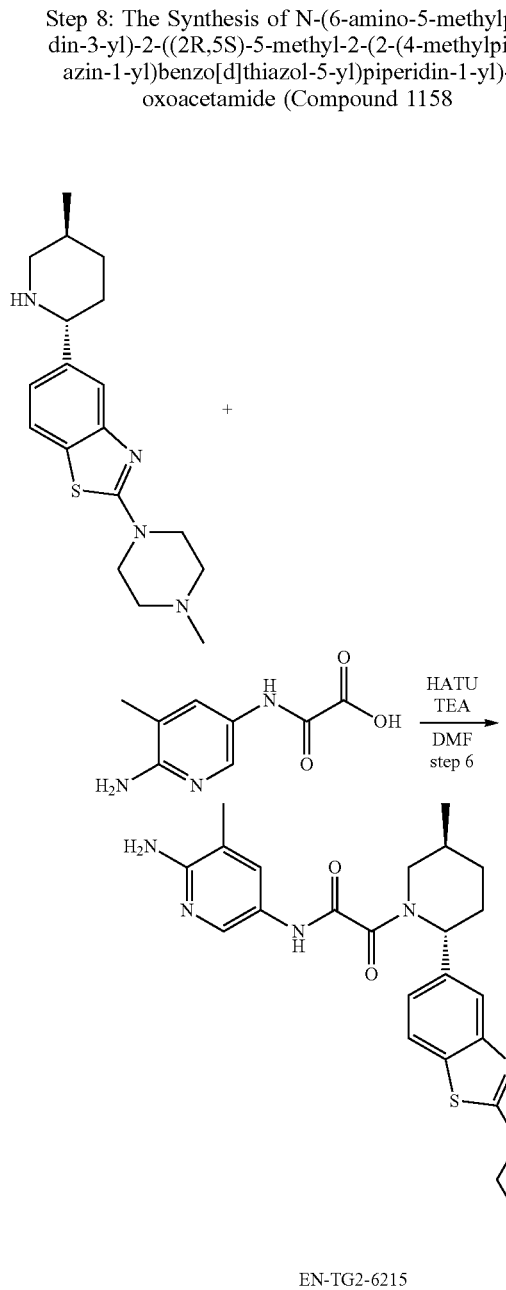

EN-TG2-6215

Prepared by general procedure scheme H step 6A. Yield: 83 mg (18.01%).

HPLC conditions: Column: YMC Triart C18 100*20 mm, 5 microM; 0-1-5 min 30-30-65% water-MeCN+0.1% NH₄OH; (loading pump 4 ml/min MeCN).

¹H NMR (600 MHz, DMSO-d₆) δ (ppm) 1.02 (m, 3H), 1.34 (m, 1H), 1.71 (m, 1H), 1.86 (m, 1H), 2.03 (m, 3H), 2.13 (m, 1H), 2.21 (s, 4H), 2.42 (t, 4H), 3.01 (dd, 1H), 3.52 (m, 5H), 5.60 (m, 3H), 7.04 (dd, 1H), 7.43 (m, 2H), 7.75 (m, 1H), 8.01 (m, 1H), 10.52 (m, 1H).

LCMS(ESI): [M]+ m/z: calcd 507.2; found 508.2; Rt=1.998 min.

Example 570. The Synthesis of N-(6-amino-5-methylpyridin-3-yl)-2-((2R,5)-5-methyl-2-(2-(oxetan-3-yl)benzo[d]thiazol-5-yl)piperidin-1-yl)-2-oxoacetamide (Compound 1266

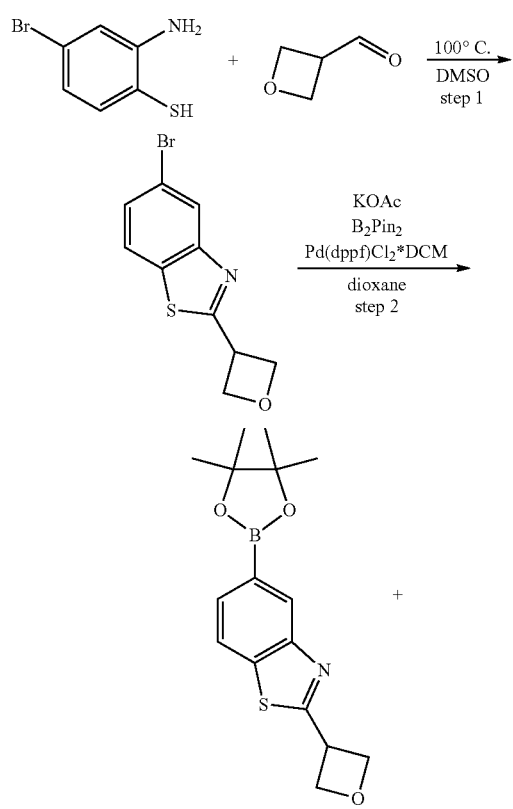

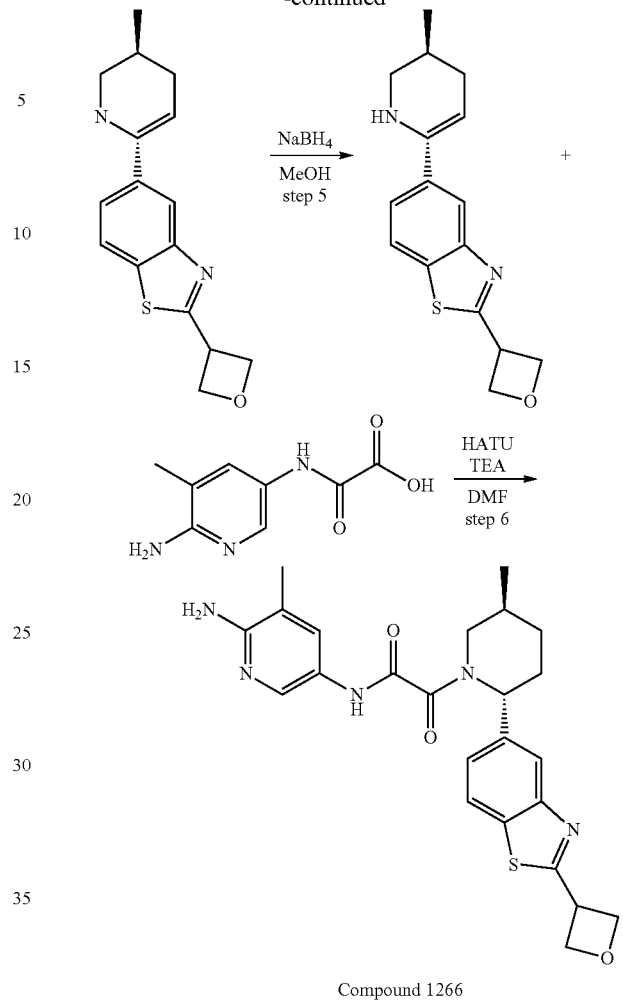

Step 1: Synthesis of 5-bromo-2-(oxetan-3-yl)benzo[d]thiazole

Prepared by general procedure scheme H step 1B. Yield: 2.7 g of crude.
LCMS(ESI): [M]+ m/z: calcd 270.2; found 271.2; Rt=1.154 min.

Step 2: Synthesis of 2-(oxetan-3-yl)-5-(4,4,5,5-tetramethyl-1,3,2-dioxaborolan-2-yl)benzo[d]thiazole Prepared by general procedure scheme H step 2. Yield: 1.6 g (50.47%).
CC conditions: The crude product was purified by silica gel with cyclohexane/MTBE as an eluent mixture.
LCMS(ESI): [M]+ m/z: calcd 317.2; found 318.2; Rt=1.507 min.

Step 3: Synthesis of (S)-tert-butyl 3-methyl-6-(2-(oxetan-3-yl)benzo[d]thiazol-5-yl)-3,4-dihydropyridine-1(2H)-carboxylate Prepared by general procedure scheme H step 3. Yield: 1.2 g (61.55%).
CC conditions: The crude product was purified by silica gel with hexane/MTBE as an eluent mixture.

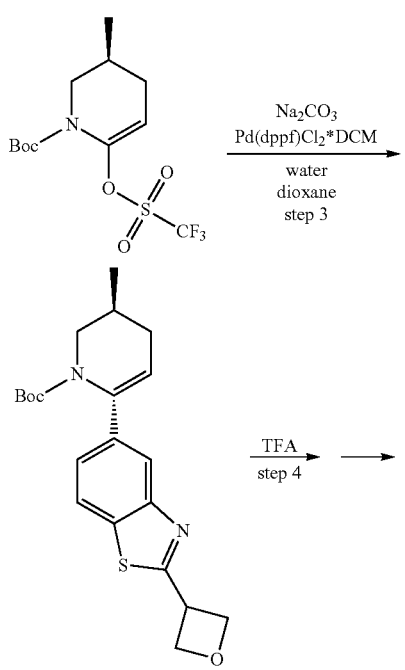

2519

LCMS(ESI): [M]+ m/z: calcd 386.2; found 387.2; Rt=1.534 min.

Step 4: Synthesis of (S)-5-(5-methyl-3,4,5,6-tetrahydropyridin-2-yl)-2-(oxetan-3-yl)benzo[d]thiazole Prepared by general procedure scheme H step 4. Yield: 0.33 g (89.07%).
LCMS(ESI): [M]+ m/z: calcd 286.2; found 287.2; Rt=0.853 min.

Step 5: Synthesis of 5-((2R,5S)-5-methylpiperidin-2-yl)-2-(oxetan-3-yl)benzo[d]thiazole Prepared by general procedure scheme H step 5. Yield: 0.21 g (63.19%).
LCMS(ESI): [M]+ m/z: calcd 288.2; found 289.2; Rt=0.904 min.

Step 6: The Synthesis of N-(6-amino-5-methylpyridin-3-yl)-2-((2R,5S)-5-methyl-2-(2-(oxetan-3-yl)benzo[d]thiazol-5-yl)piperidin-1-yl)-2-oxoacetamide (Compound 1266)

Prepared by general procedure scheme H step 6A. Yield: 101 mg (29.79%).
HPLC conditions: Column: Chromatorex C18 100*19 mm, 5 microM; 0-1-6 min 25-25-50% water-MeCN, flow: 30 ml/min; (loading pump 4 ml/min MeCN).
$^1$H NMR (600 MHz, DMSO-$d_6$) δ (ppm) 1.03 (m, 3H), 1.36 (m, 1H), 1.71 (m, 1H), 1.87 (m, 1H), 2.00 (m, 3H), 2.14 (m, 1H), 2.31 (m, 1H), 2.79 (m, 1H), 3.76 (dd, 1H), 4.75 (m, 1H), 4.83 (m, 2H), 5.00 (m, 2H), 5.64 (m, 3H), 7.43 (m, 2H), 7.98 (m, 2H), 8.10 (m, 1H), 10.56 (m, 1H).
LCMS(ESI): [M]+ m/z: calcd 465.2; found 466.2; Rt=2.604 min.

Example 571. The Synthesis of N-(6-amino-5-methylpyridin-3-yl)-2-((2R,5S)-5-methyl-2-(2-(2-Morpholinoethyl)benzo[d]thiazol-5-yl)piperidin-1-yl)-2-oxoacetamide (Compound 1387)

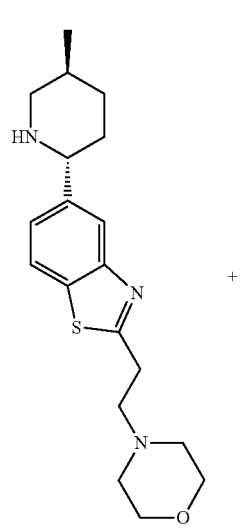

+

2520

-continued

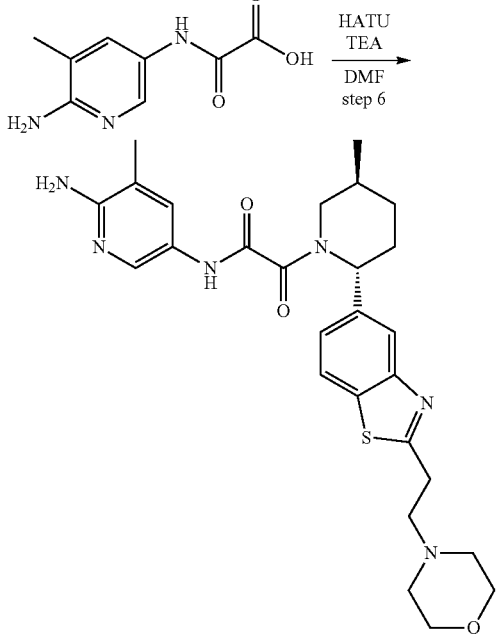

Compound 1387

Prepared by general procedure scheme H step 6A. Yield: 211 mg (42.27%).
HPLC conditions: Column: YMC Triart C18 100*20 mm, 5 microM; 0-5 min 35-35-70% water-MeOH+0.1% NH$_4$OH, flow: 30 ml/min; (loading pump 4 ml/min MeOH).
$^1$H NMR (600 MHz, DMSO-$d_6$) δ (ppm) 1.02 (m, 3H), 1.34 (m, 1H), 1.70 (m, 1H), 1.87 (m, 1H), 2.00 (m, 3H), 2.13 (m, 1H), 2.30 (m, 2H), 2.46 (m, 4H), 2.75 (t, 2H), 3.25 (t, 2H), 3.55 (m, 5H), 5.63 (m, 3H), 7.40 (m, 2H), 7.95 (m, 3H), 10.54 (m, 1H).
LCMS(ESI): [M]+ m/z: calcd 522.2; found 523.2; Rt=2.140 min.

Example 572. The Synthesis of N-(6-amino-5-methylpyridin-3-yl)-2-((2R,5S)-2-(2-(1-(2-Fluoroethyl)piperidin-4-yl)benzo[d]thiazol-5-yl)-5-methylpiperidin-1-yl)-2-oxoacetamide (Compound 1114)

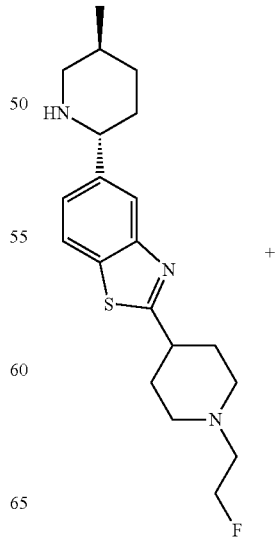

+

2521

-continued

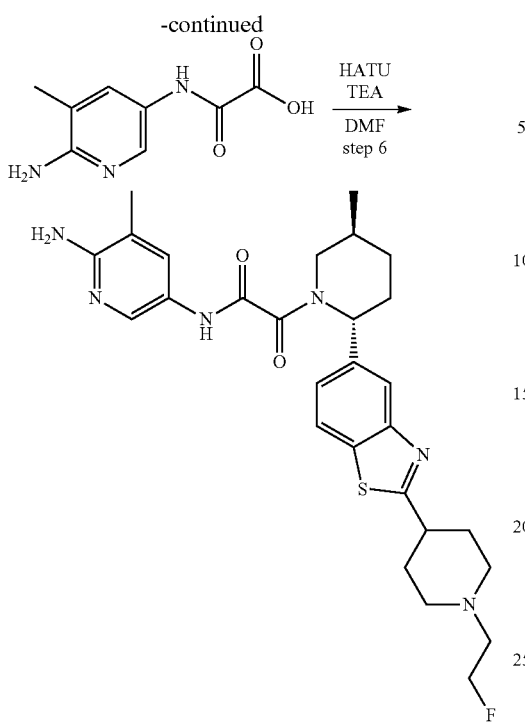

Prepared by general procedure scheme H step 6A. Yield: 109 mg (33.25%).

HPLC conditions: Column: YMC Triart C18 100*20 mm, 5 microM; 0-1-5 min 30-30-45% water-MeCN+0.1% NH$_4$OH, flow: 30 ml/min; (loading pump 4 ml/min MeCN).

$^1$H NMR (600 MHz, DMSO-d$_6$) δ (ppm) 1.03 (m, 3H), 1.35 (m, 1H), 1.70 (m, 1H), 1.81 (m, 4H), 2.00 (m, 3H), 2.08 (m, 2H), 2.20 (t, 2H), 2.31 (m, 1H), 2.64 (m, 2H), 3.02 (m, 4H), 3.75 (dd, 1H), 4.49 (t, 1H), 4.57 (t, 1H), 5.63 (m, 3H), 7.40 (m, 2H), 7.98 (m, 3H), 10.54 (m, 1H).

LCMS(ESI): [M]$^+$ m/z: calcd 538.2; found 539.2; Rt=2.191 min.

Example 573. The Synthesis of N-(6-amino-5-cyclopropylpyridin-3-yl)-2-(2-(2-(2-(dimethylamino)ethyl)benzo[d]thiazol-5-yl)-5-methylpiperidin-1-yl)-2-oxoacetamide (Compound 1331 and Compound 1218

2522

-continued

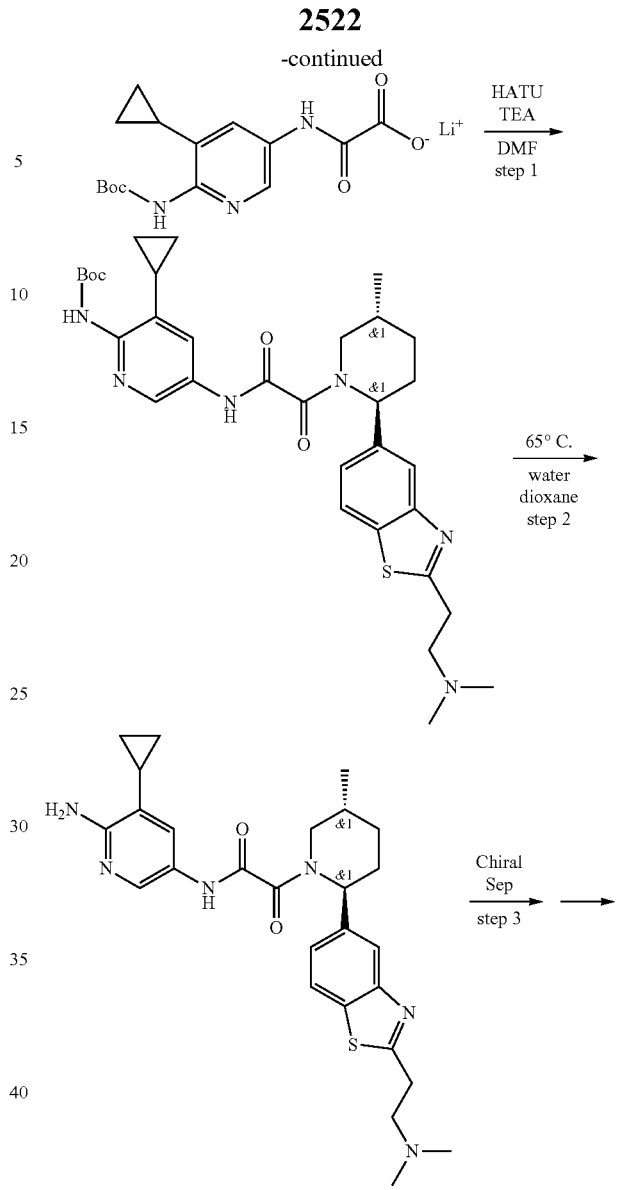

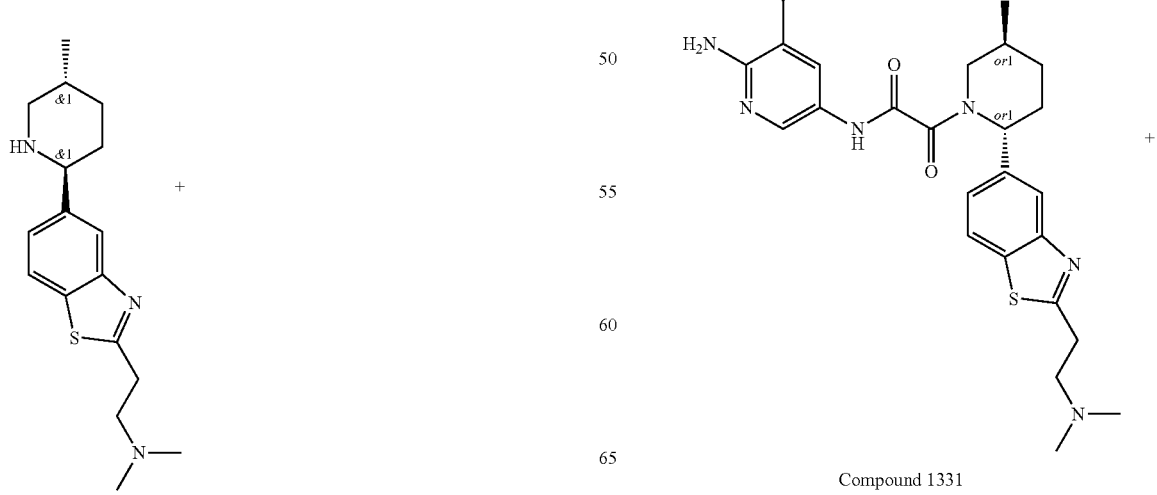

Compound 1331

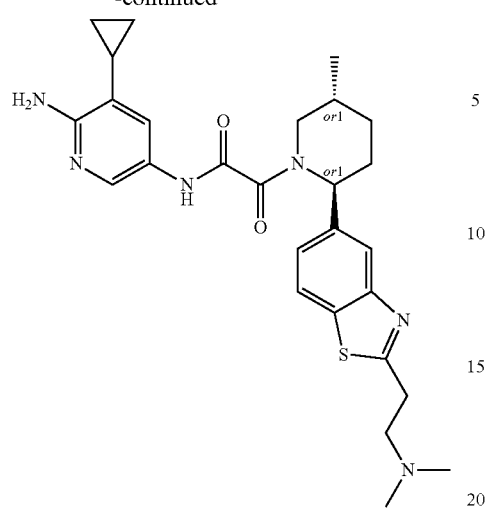

Compound 1218

Step 1: Synthesis of rac-tert-butyl (3-cyclopropyl-5-(2-((2R,5S)-2-(2-(2-(dimethylamino)ethyl)benzo[d]thiazol-5-yl)-5-methylpiperidin-1-yl)-2-oxoacetamido)pyridin-2-yl)carbamate Prepared by general procedure scheme H step 6A. Yield: 223 g (33.29%).

HPLC conditions: Column: YMC Triart C18 100*20 mm, 5 microM; 0-2-5 min 50-50-85% water-MeCN+0.1% NH$_4$OH, flow: 30 ml/min; (loading pump 4 ml/min MeCN).

LCMS(ESI): [M]$^+$ m/z: calcd 606.2; found 607.2; Rt=2.835 min.

Step 2: Synthesis of N-(6-amino-5-cyclopropylpyridin-3-yl)-2-(2-(2-(2-(dimethylamino)ethyl)benzo[d]thiazol-5-yl)-5-methylpiperidin-1-yl)-2-oxoacetamide The solution of tert-butyl N-[3-cyclopropyl-5-[[2-[(2R,5S)-2-[2-[2-(dimethylamino)ethyl]-1,3-benzothiazol-5-yl]-5-methyl-1-piperidyl]-2-oxo-acetyl]amino]-2-pyridyl]carbamate (223 mg, 367.52 umol) in dioxane (2 mL) and water (1 mL) was stirred for 48 hr at 65° C. and the solvents were evaporated in vacuum. The residue was purified by RP-HPLC (column: YMC Triart C18 100×20 mm, 5 um; 35-65% 0-5 min H$_2$O/MeCN/0.1% NH$_4$OH, flow: 30 ml/min, flow: 30 ml/min) to give N-(6-amino-5-cyclopropyl-3-pyridyl)-2-[(2R,5S)-2-[2-[2-(dimethylamino)ethyl]-1,3-benzothiazol-5-yl]-5-methyl-1-piperidyl]-2-oxo-acetamide (84 mg, 165.79 umol, 45.11% yield).

LCMS(ESI): [M]$^+$ m/z: calcd 506.2; found 507.2; Rt=1.869 min.

Step 3: Chiral Separation (Compound 1331 and Compound 1218

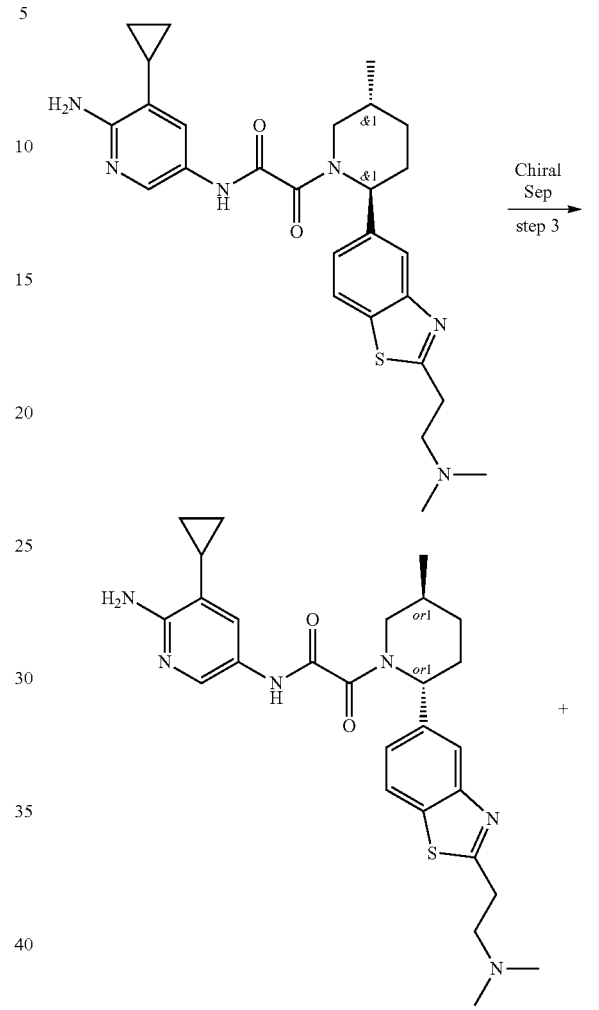

EN-TG2-6001

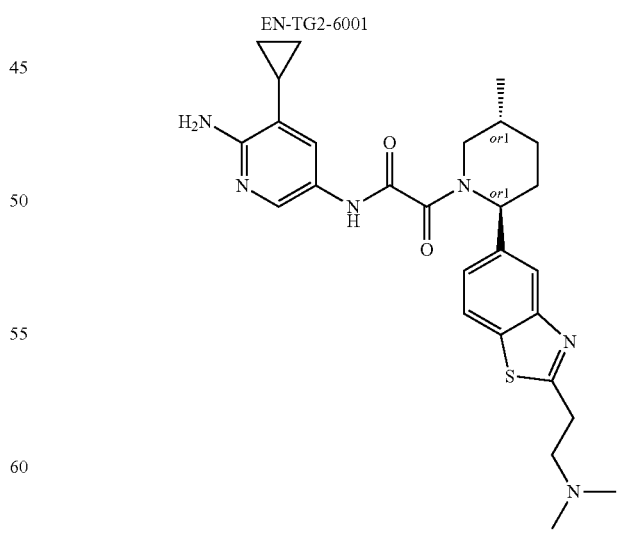

EN-TG2-6024

Racemic N-(6-amino-5-cyclopropylpyridin-3-yl)-2-(2-(2-(2-(dimethylamino)ethyl)benzo[d]thiazol-5-yl)-5-methylpiperidin-1-yl)-2-oxoacetamide (84 mg, 165.79 μmol) was chiral separated (Column: Chiralpak AS-H (250*20, 5 mkm), Hexane-IPA-MeOH, 70-15-15, 12 ml/min then another column for the first one: Chiralcel OJ-H (250*30, 5 mkm), Hexane-IPA-MeOH, 70-15-15, 12 ml/min) to obtain N-(6-amino-5-cyclopropyl-3-pyridyl)-2-[(2R,5S)-2-[2-[2-(dimethylamino)ethyl]-1,3-benzothiazol-5-yl]-5-methyl-1-piperidyl]-2-oxo-acetamide (31 mg, 61.18 umol, 73.81% yield) (RT=27.27) and N-(6-amino-5-cyclopropyl-3-pyridyl)-2-[(2S,5R)-2-[2-[2-(dimethylamino)ethyl]-1,3-benzothiazol-5-yl]-5-methyl-1-piperidyl]-2-oxo-acetamide (27 mg, 53.29 umol, 64.29% yield) (RT=15.45).

Rel Time for Compound 1331 in analytical conditions (column: AS-H, Hexane-IPA-MeOH, 70-15-15, 0.6 ml/min as mobile phase) 21.46 min and for Compound 1218 13.49 min.

Compound 1331:
  Retention time: 21.46 min
  $^1$H NMR (600 MHz, DMSO-$d_6$) δ (ppm) 0.36-0.49 (m, 2H), 0.82-0.90 (m, 2H), 0.99-1.06 (m, 3H), 1.31-1.43 (m, 1H), 1.60-1.72 (m, 2H), 1.81-1.90 (m, 1H), 2.03-2.17 (m, 1H), 2.21 (s, 6H), 2.27-2.34 (m, 1H), 2.66-2.72 (m, 2H), 2.76-3.20 (m, 1H), 3.21-3.26 (m, 2H), 3.34-4.08 (m, 1H), 5.25-5.70 (m, 1H), 5.71-5.83 (m, 2H), 7.27-7.35 (m, 1H), 7.36-7.41 (m, 1H), 7.80-7.89 (m, 1H), 7.98-8.02 (m, 1H), 8.03-8.08 (m, 1H), 10.45-10.64 (m, 1H).
  LCMS(ESI): [M]$^+$ m/z: calcd 506.2; found 507.2; Rt=1.812 min.

Compound 1218:
  Retention time: 13.49 min
  $^1$H NMR (600 MHz, DMSO-$d_6$) δ (ppm) 0.38-0.49 (m, 2H), 0.80-0.92 (m, 2H), 0.98-1.06 (m, 3H), 1.29-1.40 (m, 1H), 1.60-1.75 (m, 2H), 1.79-1.91 (m, 1H), 2.03-2.17 (m, 1H), 2.20 (s, 6H), 2.26-2.34 (m, 1H), 2.66-2.74 (m, 2H), 2.74-3.19 (m, 1H), 3.19-3.23 (m, 2H), 3.37-4.08 (m, 1H), 5.26-5.70 (m, 1H), 5.70-5.82 (m, 2H), 7.22-7.36 (m, 1H), 7.36-7.42 (m, 1H), 7.81-7.89 (m, 1H), 7.96-8.14 (m, 2H), 10.45-10.57 (m, 1H).
  LCMS(ESI): [M]$^+$ m/z: calcd 506.2; found 507.2; Rt=1.806 min.

Example 574. The Synthesis of N-(6-amino-5-methylpyridin-3-yl)-2-((2R,5S)-5-methyl-2-(2-(2-(pyrrolidin-1-yl)ethyl)benzo[d]thiazol-5-yl)piperidin-1-yl)-2-oxoacetamide (Compound 1296)

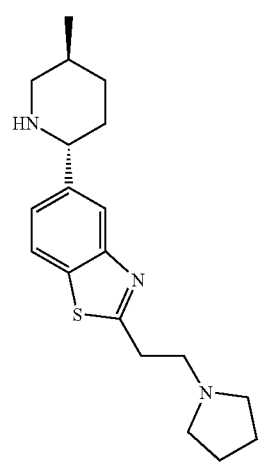

+

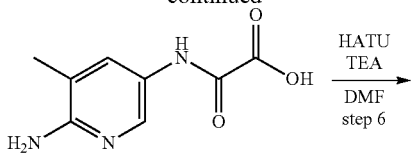

-continued

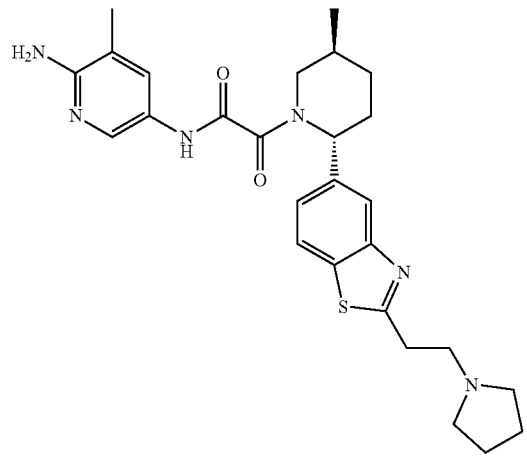

Compound 1296

Prepared by general procedure scheme H step 6A. Yield: 100 mg (40.02%).

HPLC conditions: Column: XBridge C18 100*19 mm, 5 microM; 0-5 min 30-55% water-MeCN+0.1% NH$_4$OH; (loading pump 4 ml/min MeCN).

$^1$H NMR (600 MHz, DMSO-$d_6$) δ (ppm) 0.99-1.07 (m, 3H), 1.29-1.41 (m, 1H), 1.64-1.75 (m, 5H), 1.79-1.93 (m, 1H), 1.95-2.04 (m, 3H), 2.07-2.22 (m, 1H), 2.25-2.36 (m, 1H), 2.50-2.53 (m, 4H), 2.75-2.80 (m, 0.3H), 2.81-2.90 (m, 2H), 3.20-3.28 (m, 2.7H), 3.43-4.07 (m, 1H), 5.22-5.59 (m, 1H), 5.59-5.73 (m, 2H), 7.31-7.41 (m, 1H), 7.42-7.53 (m, 1H), 7.79-7.91 (m, 1H), 7.94-8.07 (m, 2H), 10.45-10.67 (m, 1H).

LCMS(ESI): [M]$^+$ m/z: calcd 506.2; found 507.2; Rt=2.173 min.

Example 575. Synthesis of N-(6-amino-5-methylpyridin-3-yl)-2-((2R,5S)-2-(2-(1-(2,2-difluoroethyl)piperidin-4-yl)benzo[d]thiazol-5-yl)-5-methylpiperidin-1-yl)-2-oxoacetamide (Compound 1377)

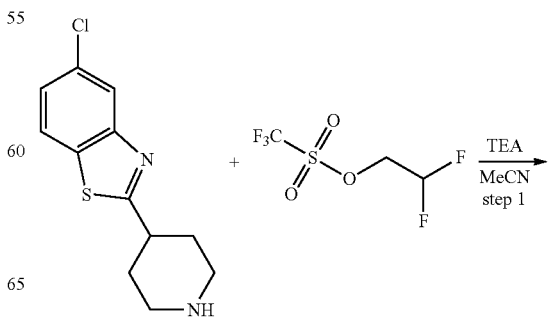

2527
-continued

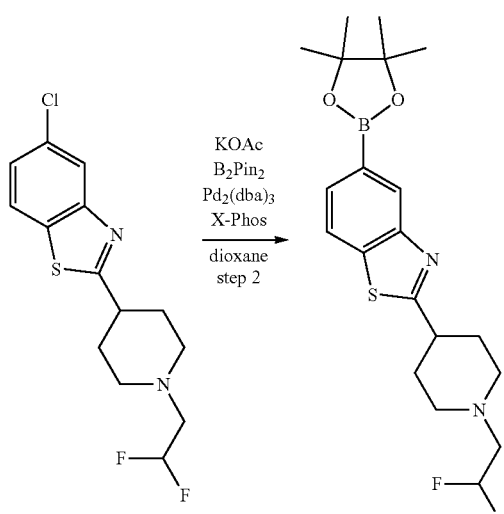

2528
-continued

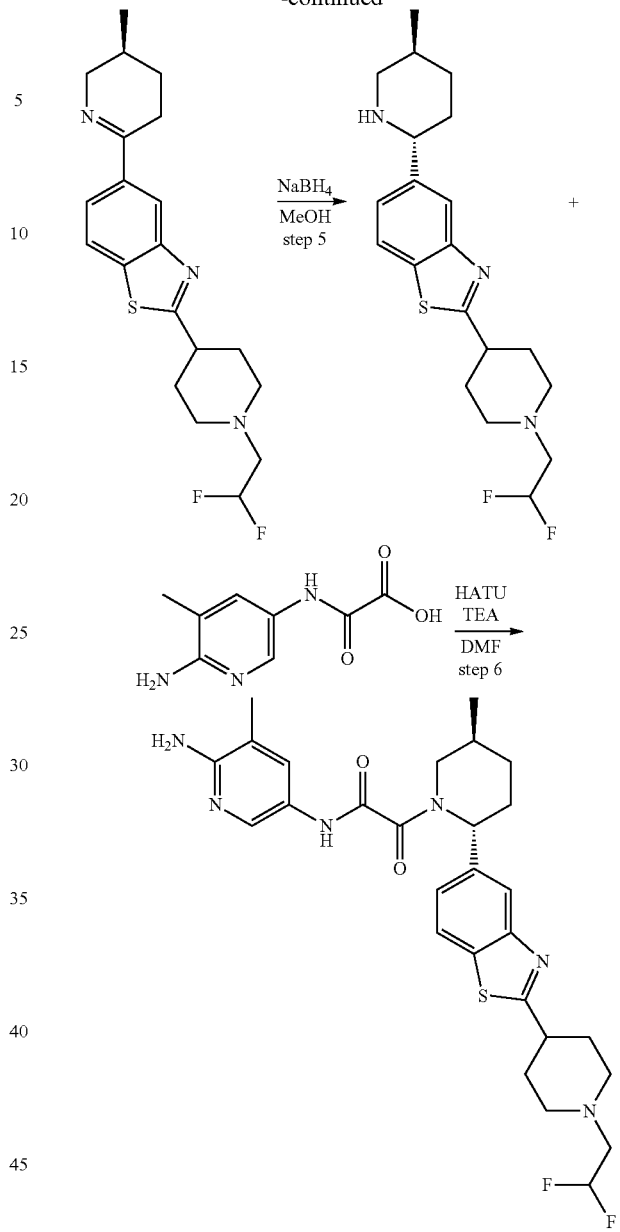

Compound 1377

Step 1: Synthesis of 5-chloro-2-(1-(2,2-difluoro-ethyl)piperidin-4-yl)benzo[d]thiazole A mixture of 5-chloro-2-(4-piperidyl)-1,3-benzothiazole (3.6 g, 11.05 mmol, 2HCl), 2,2-difluoroethyl trifluoromethanesulfonate (2.84 g, 13.26 mmol) and TEA (5.59 g, 55.27 mmol, 7.70 mL) in MeCN (100 mL) was stirred at 60° C. for 72 hr, then cooled down and concentrated in vacuum. The residue was diluted with water (50 ml) and basified to pH 11 with 10% aqueous sodium hydroxide solution. The resulting mixture was extracted with MTBE (250 ml). The organic layer was washed with water (50 ml), dried over sodium sulphate and concentrated in vacuum to afford crude 5-chloro-2-[1-(2,2-difluoroethyl)-4-piperidyl]-1,3-benzothiazole (3 g, 9.47 mmol, 85.67% yield) as brown solid, which was used directly in the next step.

LCMS(ESI): [M]+ m/z: calcd 316.2; found 317.2; Rt=2.015 min.

Step 2: Synthesis of 2-(1-(2,2-difluoroethyl)piperidin-4-yl)-5-(4,4,5,5-tetramethyl-1,3,2-dioxaborolan-2-yl)benzo[d]thiazole A mixture of 5-chloro-2-[1-(2,2-difluoroethyl)-4-piperidyl]-1,3-benzothiazole (3 g, 9.47 mmol), 4,4,5,5-tetramethyl-2-(4,4,5,5-tetramethyl-1,3,2-dioxaborolan-2-yl)-1,3,2-dioxaborolane (2.65 g, 10.42 mmol) and potassium acetate (1.86 g, 18.94 mmol, 1.18 mL) in dioxane (100 mL) was evacuated and then backfilled with argon. This operation was repeated two times, then tris(1,5-diphenylpenta-1,4-dien-3-one)dipalladium (433.58 mg, 473.49 umol) and dicyclohexyl[2',4',6'-tris(propan-2-yl)-[1,1'-biphenyl]-2-yl]phosphane (902.89 mg, 1.89 mmol) were added under argon, and the reaction mixture was stirred at 95° C. for 18 hr. The reaction mixture was cooled down and concentrated in vacuum. The residue was purified by column chromatography on silica gel using hexane/ethyl acetate gradient (0-100% ethyl acetate) to afford 2-[1-(2,2-difluoroethyl)-4-piperidyl]-5-(4,4,5,5-tetramethyl-1,3,2-dioxaborolan-2-yl)-1,3-benzothiazole (1.5 g, 3.67 mmol, 38.79% yield) as beige solid.

LCMS(ESI): [M]+ m/z: calcd 408.2; found 409.2; Rt=0.989 min.

Step 3: Synthesis of (S)-tert-butyl 6-(2-(1-(2,2-difluoroethyl)piperidin-4-yl)benzo[d]thiazol-5-yl)-3-methyl-3,4-dihydropyridine-1(2H)-carboxylate Prepared by general procedure scheme H step 3. Yield: 0.9 g (51.29%).
CC conditions: The crude product was purified by silica gel with hexane/MTBE as an eluent mixture.
LCMS(ESI): [M]+ m/z: calcd 477.2; found 478.2; Rt=1.120 min.

Step 4: Synthesis of (S)-2-(1-(2,2-difluoroethyl)piperidin-4-yl)-5-(5-methyl-3,4,5,6-tetrahydropyridin-2-yl)benzo[d]thiazole Prepared by general procedure scheme H step 4. Yield: 0.67 g (9F9%).
LCMS(ESI): [M]+ m/z: calcd 377.2; found 378.2; Rt=0.707 min.

Step 5: Synthesis of 2-(1-(2,2-difluoroethyl)piperidin-4-yl)-5-((2R,5S)-5-methylpiperidin-2-yl)benzo[d]thiazole Prepared by general procedure scheme H step 5. Yield: 0.55 g (81.65%).
LCMS(ESI): [M]+ m/z: calcd 379.2; found 380.2; Rt=0.744 min.

Step 6: Synthesis of N-(6-amino-5-methylpyridin-3-yl)-2-((2R,5S)-2-(2-(1-(2,2-difluoroethyl)piperidin-4-yl)benzo[d]thiazol-5-yl)-5-methylpiperidin-1-yl)-2-oxoacetamide (Compound 1377

Prepared by general procedure scheme H step 6A. Yield: 109 mg (29.72%).
HPLC conditions: Column: YMC Triart C18 100*20 mm, 5 microM; 0-1-6 min 30-30-50% water-MeCN+0.1% NH4OH, flow: 30 ml/min; (loading pump 4 ml/min MeCN).

1H NMR (500 MHz, DMSO-d6) δ (ppm) 0.99-1.06 (m, 3H), 1.26-1.41 (m, 1H), 1.63-1.94 (m, 5H), 1.96-2.04 (m, 3H), 2.05-2.11 (m, 3H), 2.13-2.29 (m, 1H), 2.33-2.37 (m, 2H), 2.72-2.78 (m, 2H), 2.96-3.00 (m, 2H), 3.07-3.14 (m, 1H), 3.35-4.10 (m, 1H), 5.26-5.62 (m, 1H), 5.62-5.72 (m, 2H), 6.14 (tt, 1H), 7.34-7.53 (m, 2H), 7.85-7.93 (m, 1H), 7.95-8.08 (m, 2H), 10.50-10.58 (m, 1H).

LCMS(ESI): [M]+ m/z: calcd 556.2; found 557.2; Rt=2.426 min.

Example 576. The Synthesis of N-(6-amino-5-methylpyridin-3-yl)-2-((2R,5S)-2-(2-(1-ethylpiperidin-4-yl)benzo[d]thiazol-5-yl)-5-methylpiperidin-1-yl)-2-oxoacetamide (Compound 1335)

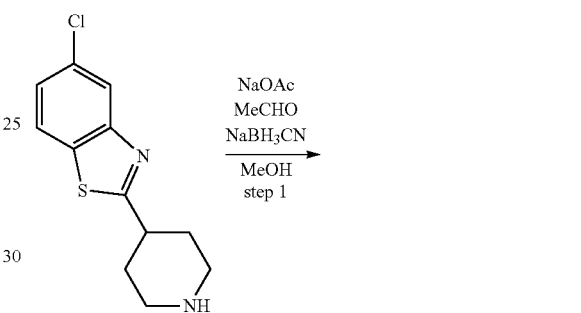

-continued

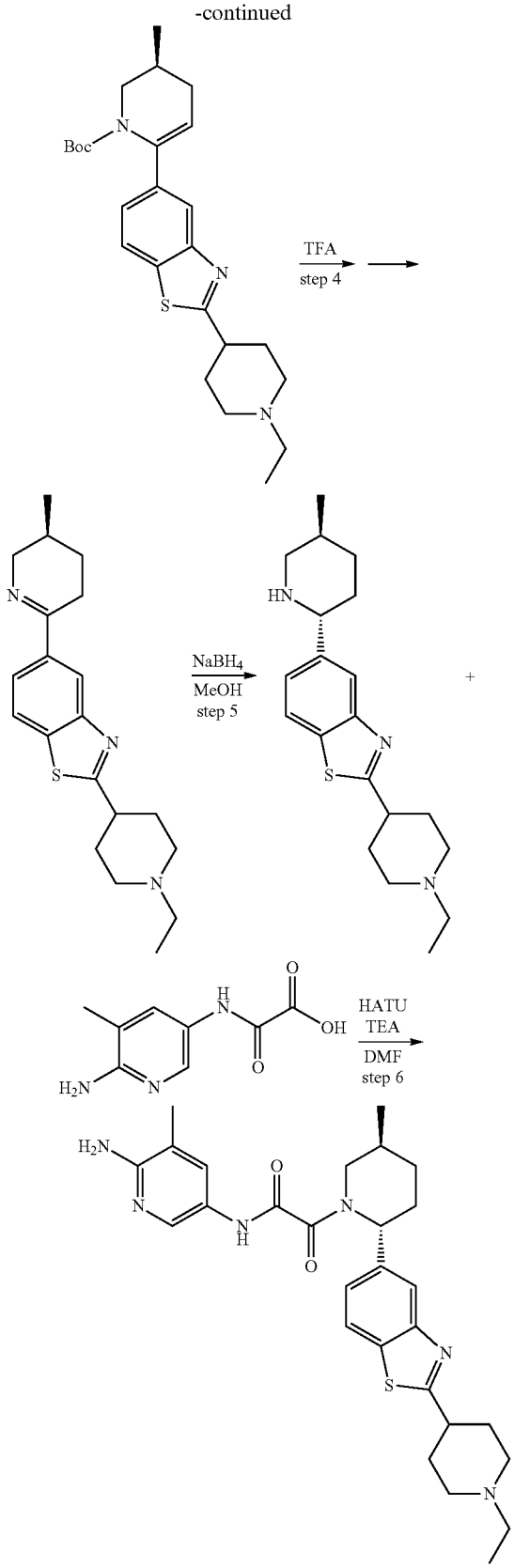

Compound 1335

Step 1: Synthesis of 5-chloro-2-(Piperidin-4-yl)benzo[d]thiazole

Phosphorus (V) pentoxide (50 g, 352.25 mmol) was added portion wise with stirring to a phosphoric acid (60 g, 612.27 mmol, 35.29 mL). The resulting mixture was stirred at 80-90° C. until clear solution formed, then piperidine-4-carboxylic acid (15 g, 116.14 mmol) and 2-amino-4-chloro-benzenethiol (18.54 g, 116.14 mmol) were added in one portion under argon and the resulting mixture was stirred under argon at 160° C. for 15 hr, then cooled down and diluted with water (500 ml). The resulting precipitate was filtered, transferred to a beaker and basified to pH 11 with 10% aqueous sodium hydroxide solution. The resulting mixture was extracted with DCM (2*250 ml). The combined organic extracts were dried over sodium sulphate, then hydrogen chloride solution 4.0 M in dioxane (157.50 g, 600.44 mmol, 150 mL, 13.9% purity) was slowly added to a dry dichloromethane solution of the product. The resulting precipitate was filtered, washed with DCM (3*50 ml) and dried in vacuum to afford 5-chloro-2-(4-piperidyl)-1,3-benzothiazole (22 g, 67.55 mmol, 58.16% yield, 2HCl) as green solid, which was used directly in the next step.

LCMS(ESI): [M]+ m/z: calcd 252.2; found 253.2; Rt=0.963 min.

Step 1: Synthesis of 5-chloro-2-(1-ethylpiperidin-4-yl)benzo[d]thiazole

Acetaldehyde (973.88 mg, 22.11 mmol, 790.23 uL) was added in one portion at 25° C. to a stirred mixture of 5-chloro-2-(4-piperidyl)-1,3-benzothiazole (4 g, 12.28 mmol, 2HCl) and sodium acetate, anhydrous (2.52 g, 30.70 mmol, 1.65 mL) in MeOH (100 mL). The resulting mixture was stirred at 25° C. for 2 hr, then sodium cyan borohydride (1.54 g, 24.56 mmol) was added in one portion at 25° C. The reaction mixture was stirred at 25° C. for 12 hr, LCMS showed only presence of starting material. More acetaldehyde (1.08 g, 24.56 mmol) was added, and the reaction mixture was stirred at 25° C. for 24 hr, and then concentrated in vacuum. The residue was diluted with water (40 ml) and basified to pH 10-11 with 10% aqueous sodium hydroxide solution. The resulting mixture was extracted with MTBE (2*150 ml). The combined organic extracts were dried over sodium sulphate and concentrated in vacuum to afford 5-chloro-2-(1-ethyl-4-piperidyl)-1,3-benzothiazole (2.4 g, 8.55 mmol, 69.59% yield) as light-yellow solid, which was used directly in the next step.

LCMS(ESI): [M]+ m/z: calcd 280.2; found 281.2; Rt=2.381 min.

Step 2: Synthesis of 2-(1-ethylpiperidin-4-yl)-5-(4,4,5,5-tetramethyl-1,3,2-dioxaborolan-2-yl)benzo[d]thiazole A mixture of 5-chloro-2-(1-ethyl-4-piperidyl)-1,3-benzothiazole (2.4 g, 8.55 mmol), 4,4,5,5-tetramethyl-2-(4,4,5,5-tetramethyl-1,3,2-dioxaborolan-2-yl)-1,3,2-dioxaborolane (2.39 g, 9.40 mmol) and potassium acetate (1.68 g, 17.09 mmol, 1.07 mL) in dioxane (100 mL) was evacuated and then backfilled with argon. This operation was repeated two times, then tris(1,5-diphenylpenta-1,4-dien-3-one)dipalladium (391.31 mg, 427.33 umol) and dicyclohexyl[2',4',6'-tris(propan-2-yl)-[1,1'-biphenyl]-2-yl]phosphane (814.86 mg, 1.71 mmol) were added under argon, and the reaction mixture was stirred at 95° C. for 18 hr. The reaction mixture was cooled down and concentrated in vacuum. The residue was purified by column chromatography on silica gel using MTBE/MeOH gradient (0-100% MeOH) to afford 2-(1-ethyl-4-piperidyl)-5-(4,4,5,5-tetramethyl-1,3,2-dioxaborolan-2-yl)-1,3-benzothiazole (1.2 g, 3.22 mmol, 37.71% yield) as light-brown solid.

LCMS(ESI): [M]+ m/z: calcd 372.2; found 373.2; Rt=1.181 min.

Step 3: Synthesis of (S)-tert-butyl 6-(2-(1-ethylpiperidin-4-yl)benzo[d]thiazol-5-yl)-3-methyl-3,4-dihydropyridine-1(2H)-carboxylate Prepared by general procedure scheme H step 3. Yield: 1.4 g of crude.

LCMS(ESI): [M]+ m/z: calcd 441.2; found 442.2; Rt=2.481 min.

Step 4: Synthesis of (S)-2-(1-ethylpiperidin-4-yl)-5-(5-methyl-3,4,5,6-tetrahydropyridin-2-yl)benzo[d]thiazole Prepared by general procedure scheme H step 4. Yield: 250 mg of crude.

LCMS(ESI): [M]+ m/z: calcd 341.2; found 342.2; Rt=0.567 min.

Step 5: Synthesis of 2-(1-ethylpiperidin-4-yl)-5-((2R,5S)-5-methylpiperidin-2-yl)benzo[d]thiazole Prepared by general procedure scheme H step 5. Yield: 130 mg (51.69%).

LCMS(ESI): [M]+ m/z: calcd 343.2; found 344.2; Rt=0.610 min.

Step 6: Synthesis of N-(6-amino-5-methylpyridin-3-yl)-2-((2R,5S)-2-(2-(1-ethylpiperidin-4-yl)benzo[d]thiazol-5-yl)-5-methylpiperidin-1-yl)-2-oxoacetamide (Compound 1335

Prepared by general procedure scheme H step 6A. Yield: 13 mg (6.60%).

HPLC conditions: Column: YMC Triart C18 100*20 mm, 5 microM; 0-5 min 30-80% water-MeCN+0.1% NH₄OH, flow: 30 ml/min; (loading pump 4 ml/min MeCN).

¹H NMR (600 MHz, DMSO-d₆) δ (ppm) 0.99-1.03 (m, 5H), 1.32-1.39 (m, 2H), 1.69-2.09 (m, 10H), 2.28-2.37 (m, 3H), 2.77-3.10 (m, 5H), 3.46-3.48 (m, 1H), 4.03-4.05 (m, 1H), 5.27-5.69 (m, 3H), 7.34-7.50 (m, 2H), 7.86-8.06 (m, 3H), 10.52-10.57 (m, 1H).

LCMS(ESI): [M]+ m/z: calcd 520.2; found 521.2; Rt=1.879 min.

Example 577. The Synthesis of N-(6-amino-5-methylpyridin-3-yl)-2-((2R,5S)-5-methyl-2-(2-(1-(oxetan-3-yl)piperidin-4-yl)benzo[d]thiazol-5-yl)piperidin-1-yl)-2-oxoacetamide (Compound 1268

Step 1: Synthesis of 5-chloro-2-(1-(oxetan-3-yl)piperidin-4-yl)benzo[d]thiazole

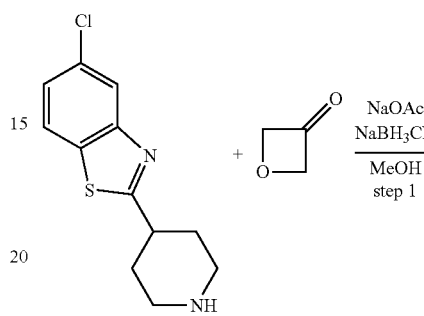

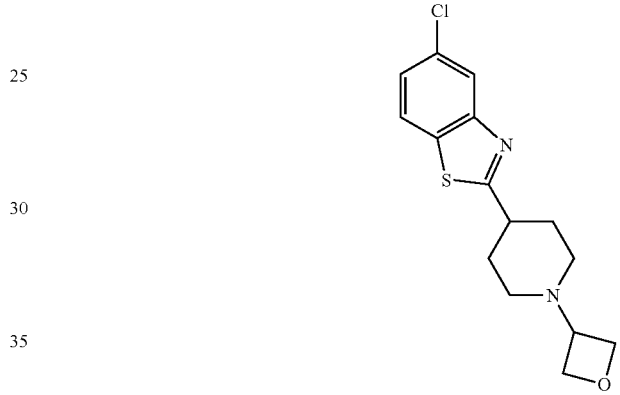

Oxetan-3-one (1.33 g, 18.42 mmol, 1.19 mL) was added in one portion at 25° C. to a stirred mixture of 5-chloro-2-(4-piperidyl)-1,3-benzothiazole (4 g, 12.28 mmol, 2HCl) and sodium acetate, anhydrous (2.52 g, 30.70 mmol, 1.65 mL) in MeOH (100 mL). The resulting mixture was stirred at 25° C. for 2 hr, then sodium cyanoborohydride (1.54 g, 24.56 mmol) was added in one portion. The reaction mixture was stirred at 25° C. for 15 hr, then concentrated to dryness in vacuum. The residue was diluted with water (40 ml) and basified to pH 10-11 with 10% aqueous sodium hydroxide solution. The resulting mixture was extracted with DCM (2*75 ml). The combined organic extracts were dried over sodium sulphate and concentrated in vacuum to afford 5-chloro-2-[1-(oxetan-3-yl)-4-piperidyl]-1,3-benzothiazole (3.5 g, 11.33 mmol, 92.28% yield) as green solid, which was used directly in the next step.

LCMS(ESI): [M]+ m/z: calcd 308.2; found 309.2; Rt=1.776 min.

Step 2: Synthesis of 2-(1-(oxetan-3-yl)piperidin-4-yl)-5-(4,4,5,5-tetramethyl-1,3,2-dioxaborolan-2-yl)benzo[d]thiazole A mixture of 5-chloro-2-[1-(oxetan-3-yl)-4-piperidyl]-1,3-benzothiazole (3.5 g, 11.33 mmol), 4,4,5,5-tetramethyl-2-(4,4,5,5-tetramethyl-1,3,2-dioxaborolan-2-yl)-1,3,2-dioxaborolane (3.17 g, 12.47 mmol) and potassium acetate (2.22 g, 22.67 mmol, 1.42 mL) in dioxane (100 mL) was evacuated and then backfilled with argon. This operation was repeated two times, then tris(1,5-diphenylpenta-1,4-dien-3-one)dipalladium (518.90 mg, 566.66 umol) and dicyclohexyl[2',4',6'-tris(propan-2-yl)-[1,1'-biphenyl]-2-yl]phosphane (1.08 g, 2.27 mmol) were added under argon, and the reaction mixture was stirred at 95° C. for 36 hr. The reaction mixture was cooled down and concentrated in vacuum. The residue was purified by column chromatography on silica gel using chloroform/MeCN gradient (0-100% MeCN) to afford 2-[1-(oxetan-3-yl)-4-piperidyl]-5-(4,4,5,5-tetramethyl-1,3,2-dioxaborolan-2-yl)-1,3-benzothiazole (2.6 g, 6.49 mmol, 57.30% yield) as green solid.

LCMS(ESI): [M]+ m/z: calcd 400.2; found 401.2; Rt=1.113 min.

Step 3: Synthesis of (S)-tert-butyl 3-methyl-6-(2-(1-(oxetan-3-yl)piperidin-4-yl)benzo[d]thiazol-5-yl)-3,4-dihydropyridine-1(2H)-carboxylate Prepared by general procedure scheme H step 3. Yield: 2.7 g (88.52%).

CC conditions: The crude product was purified by silica gel with CHCl₃/MeCN gradient (0-100% MeCN) as an eluent mixture.

LCMS(ESI): [M]+ m/z: calcd 469.2; found 470.2; Rt=1.233 min.

Step 4: Synthesis of (S)-5-(5-methyl-3,4,5,6-tetrahydropyridin-2-yl)-2-(1-(oxetan-3-yl)piperidin-4-yl)benzo[d]thiazole Prepared by general procedure scheme H step 4. Yield: 900 mg of crude.

LCMS(ESI): [M]+ m/z: calcd 369.2; found 370.2; Rt=0.484 min.

Step 5: Synthesis of 5-((2R,5S)-5-methylpiperidin-2-yl)-2-(1-(oxetan-3-yl)piperidin-4-yl)benzo[d]thiazole Prepared by general procedure scheme H step 5. Yield: 650 mg (71.83%).

LCMS(ESI): [M]+ m/z: calcd 371.2; found 372.2; Rt=0.625 min.

Step 6: The Synthesis of N-(6-amino-5-methylpyridin-3-yl)-2-((2R,5S)-5-methyl-2-(2-(1-(oxetan-3-yl)piperidin-4-yl)benzo[d]thiazol-5-yl)piperidin-1-yl)-2-oxoacetamide (Compound 1268

Prepared by general procedure scheme H step 6A. Yield: 117 mg (31.69%).

HPLC conditions: Column: YMC Triart C18 100*20 mm, 5 microM; 0-1-5 min 20-20-45% water-MeCN+0.1% NH₄OH; (loading pump 4 ml/min MeCN).

¹H NMR (600 MHz, DMSO-d₆) δ (ppm) 1.02-1.04 (m, 3H), 1.32-1.39 (m, 1H), 1.66-1.70 (m, 3H), 1.79-2.31 (m, 8H), 2.76-2.78 (m, 3H), 3.10-3.14 (m, 1H), 3.40-3.48 (m, 2H), 4.040 (m, 1H), 4.42-4.54 (dt, 4H), 5.27 (m, 1H), 5.58-5.69 (m, 3H), 7.34-7.50 (m, 2H), 7.86-8.07 (m, 3H), 10.52-10.57 (m, 1H).

LCMS(ESI): [M]+ m/z: calcd 548.2; found 549.2; Rt=2.201 min.

Example 578. The Synthesis of N-(6-amino-5-methylpyridin-3-yl)-2-((2R,5S)-5-methyl-2-(2-(1-methyl-2-oxopiperidin-4-yl)benzo[d]thiazol-5-yl)piperidin-1-yl)-2-oxoacetamide (Compound 1333)

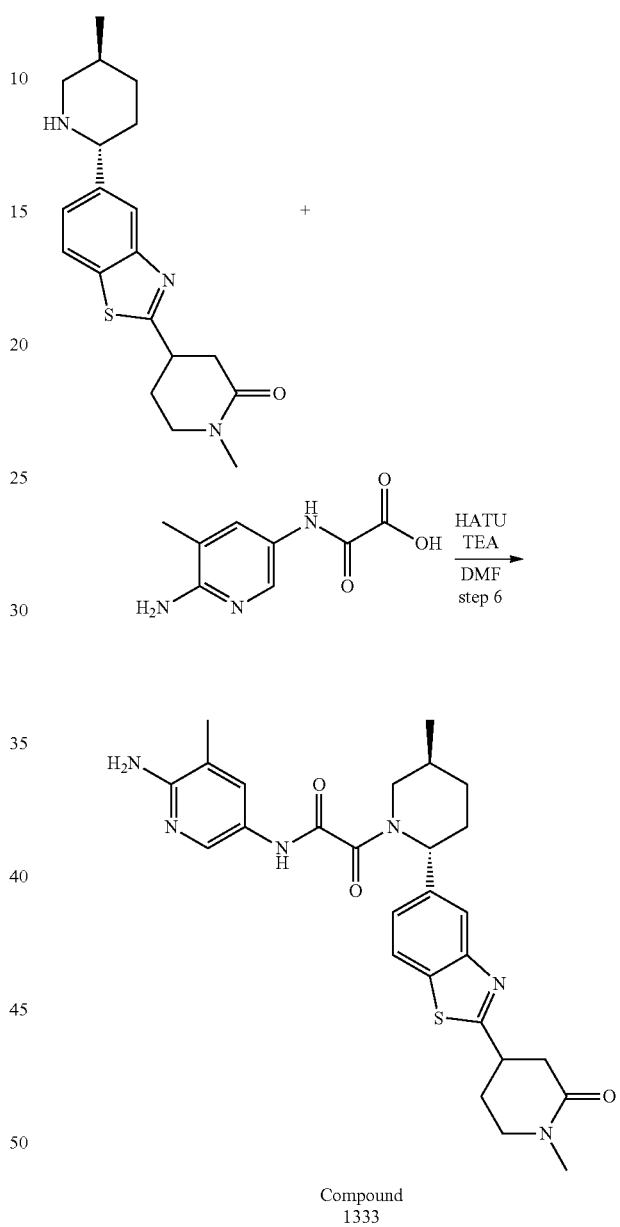

Compound 1333

Prepared by general procedure scheme H step 6A. Yield: 63.4 mg (11.95%).

HPLC conditions: Column: YMC Triart C18 100*20 mm, 5 microM; 0-1-6 min 40-40-65% water-MeOH+0.1% NH₄OH, flow: 30 ml/min; (loading pump 4 ml/min MeOH).

¹H NMR (600 MHz, DMSO-d₆) δ (ppm) 1.02-1.04 (m, 3H), 1.31-1.39 (m, 1H), 1.69-1.71 (m, 1H), 1.84-2.31 (m, 9H), 2.60-2.82 (m, 5H), 3.39-4.05 (m, 4H), 5.27-5.69 (m, 3H), 7.36-7.50 (m, 2H), 7.88-8.09 (m, 3H), 10.52-10.56 (m, 1H).

LCMS(ESI): [M]+ m/z: calcd 520.2; found 521.2; Rt=2.359 min.

2537

Example 579. The Synthesis of N-(6-amino-5-eth-ylpyridin-3-yl)-2-((2R,5S)-5-methyl-2-(2-(1-(oxetan-3-yl)piperidin-4-yl)benzo[d]thiazol-5-yl)piperidin-1-yl)-2-oxoacetamide (Compound 1224)

2538

LCMS(ESI): [M]+ m/z: calcd 562.2; found 563.2; Rt=1.926 min.

Example 580. The Synthesis of N-(6-amino-5-eth-ylpyridin-3-yl)-2-((2R,5S)-5-methyl-2-(2-(1-methyl-2-oxopiperidin-4-yl)benzo[d]thiazol-5-yl)piperidin-1-yl)-2-oxoacetamide (Compound 1110, Compound 1256 and Compound 1136

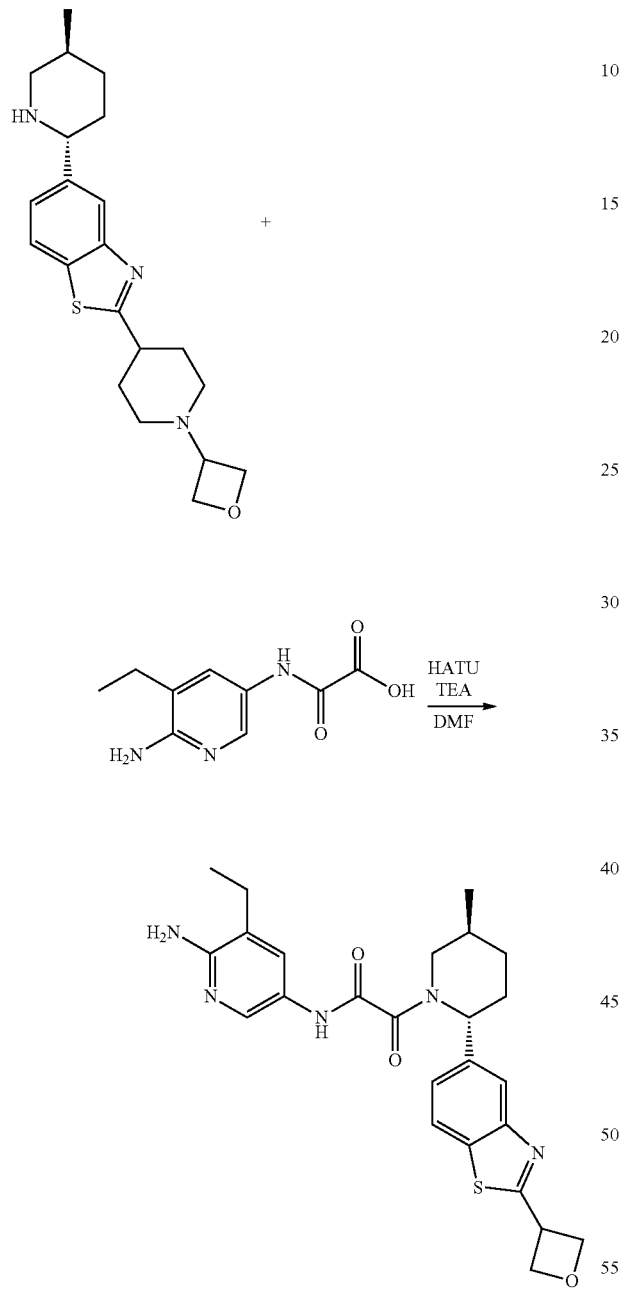

Compound 1110

Prepared by general procedure scheme H step 6A. Yield: 96 mg (42.26%).

HPLC conditions: Column: XBridge C18 100*19 mm, 5 microM; 0-5 min 20-45% water-MeCN+0.1% NH₄OH; (loading pump 4 ml/min MeCN).

¹H NMR (600 MHz, DMSO-d₆) δ (ppm) 1.02-1.14 (m, 6H), 1.32-1.39 (m, 1H), 1.69-1.97 (m, 6H), 2.09-2.11 (m, 3H), 2.28-2.40 (m, 3H), 2.76-2.77 (m, 2H), 3.12 (m, 1H), 3.40-4.06 (m, 3H), 4.42-4.54 (m, 4H), 5.28-5.69 (m, 3H), 7.34-7.51 (m, 2H), 7.86-8.07 (m, 3H), 10.52-10.58 (m, 1H).

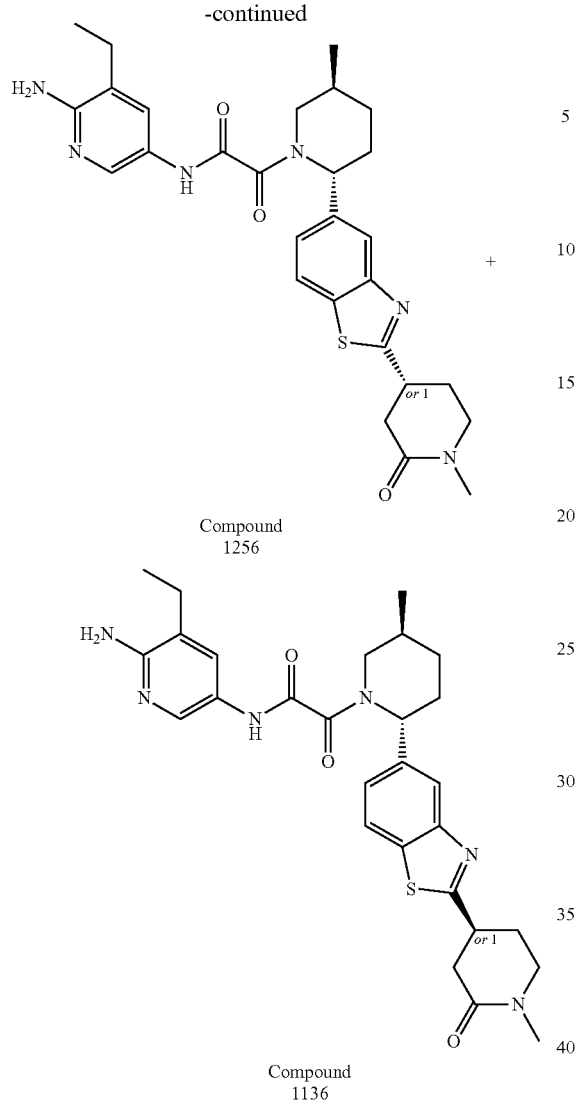

Compound 1256

Compound 1136

Step 1: Synthesis of 4-(5-chlorobenzo[d]thiazol-2-yl)-1-methylpiperidin-2-one

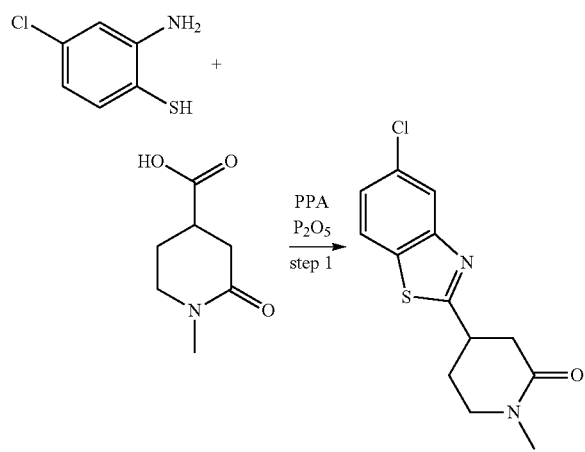

Prepared by general procedure scheme H step 1A. Yield: 3.1 g (35.25%).

CC conditions: The crude product was purified by silica gel with CHCl$_3$/MTBE (gradient 10-100% MTBE) as an eluent mixture.

LCMS(ESI): [M]$^+$ m/z: calcd 280.2; found 281.2; Rt=1.118 min.

Step 2: Synthesis of 1-methyl-4-(5-(4,4,5,5-tetramethyl-1,3,2-dioxaborolan-2-yl)benzo[d]thiazol-2-yl)piperidin-2-one

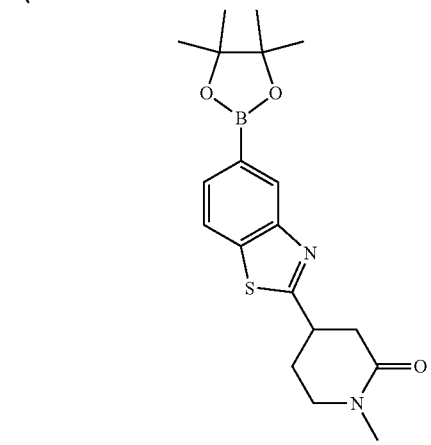

tris(Dibenzylideneacetone)dipalladium(0) (303.31 mg, 331.23 umol) and XPhos (631.61 mg, 1.32 mmol) was added to a solution of 4-(5-chloro-1,3-benzothiazol-2-yl)-1-methyl-piperidin-2-one (3.1 g, 11.04 mmol) and 4,4,5,5-tetramethyl-2-(4,4,5,5-tetramethyl-1,3,2-dioxaborolan-2-yl)-1,3,2-dioxaborolane (3.64 g, 14.35 mmol) in dioxane (100 mL). Reaction flask was evacuated and refilled with argon 3 times. Then potassium acetate (2.17 g, 22.08 mmol, 1.38 mL) was added under stream of argon. Resulting mixture was stirred at 100° C. for 12 hr under inert atmosphere, then cooled and evaporated in vacuum poured into water (200 ml) and extracted with DCM (2×100 ml), dried over sodium sulphate and evaporated in vacuum to leave 5 g of crude product, 5 g of which was purification by column chromatography on silica gel using CHCl$_3$/MeCN gradient (10-100% MeCN) to afford 1-methyl-4-[5-(4,4,5,5-tetramethyl-1,3,2-dioxaborolan-2-yl)-1,3-benzothiazol-2-yl]piperidin-2-one (3 g, 8.06 mmol, 72.99% yield).

LCMS(ESI): [M]$^+$ m/z: calcd 372.2; found 373.2; Rt=1.299 min.

Step 3: Synthesis of (3S)-tert-butyl 3-methyl-6-(2-(1-methyl-2-oxopiperidin-4-yl)benzo[d]thiazol-5-yl)-3,4-dihydropyridine-1(2H)-carboxylate

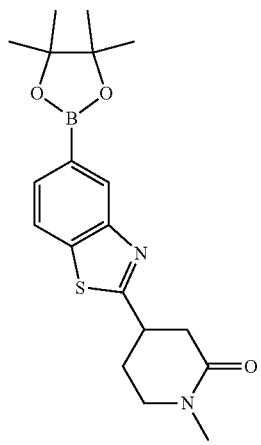

+

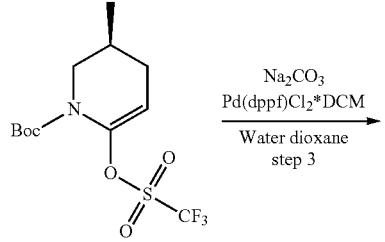

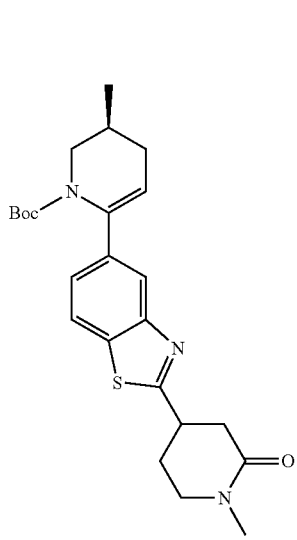

Prepared by general procedure scheme H step 3. Yield: 3 g of crude.

LCMS(ESI): [M]⁺ m/z: calcd 441.2; found 442.2; Rt=4.017 min.

Step 4: Synthesis of 1-methyl-4-(5-((S)-5-methyl-3,4,5,6-tetrahydropyridin-2-yl)benzo[d]thiazol-2-yl)piperidin-2-one

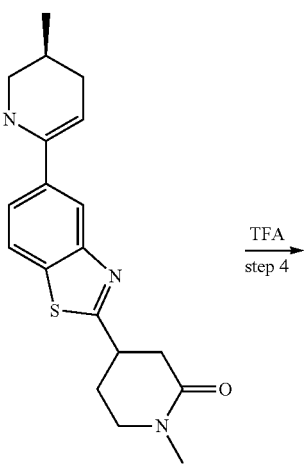

TFA
step 4
→

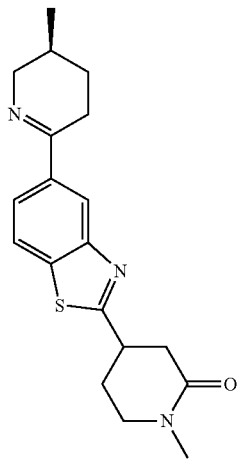

Prepared by general procedure 8 step 4. Yield: 1.1 g of crude.

LCMS(ESI): [M]⁺ m/z: calcd 341.2; found 342.2; Rt=0.860 min.

Step 5: Synthesis of 1-methyl-4-(5-((2R,5S)-5-methylpiperidin-2-yl)benzo[d]thiazol-2-yl)piperidin-2-one

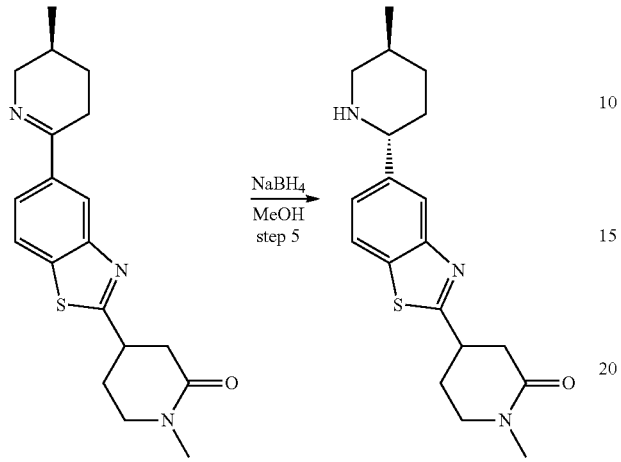

Prepared by general procedure 8 step 5. Yield: 0.7 g of crude.
LCMS(ESI): [M]+ m/z: calcd 343.2; found 344.2; Rt=0.706 min.

Step 6: Synthesis of N-(6-amino-5-ethylpyridin-3-yl)-2-((2R,5S)-5-methyl-2-(2-(1-methyl-2-oxopiperidin-4-yl)benzo[d]thiazol-5-yl)piperidin-1-yl)-2-oxoacetamide Prepared by general procedure scheme H step 6A. Yield: 48 mg (15.42%).
HPLC conditions: Column: YMC Triart C18 100*20 mm, 5 microM; 0-1-6 min 30-30-75% water-MeOH+0.1% NH₄OH; (loading pump 4 ml/min MeOH).
Compound 1110:
¹H NMR (600 MHz, DMSO-d₆) δ (ppm) 1.02-1.13 (m, 6H), 1.32-1.39 (m, 1H), 1.69-1.90 (m, 2H), 2.08-2.19 (m, 2H), 2.31-2.40 (m, 3H), 2.59-2.82 (m, 5H), 3.40-4.06 (m, 4H), 5.27-5.69 (m, 3H), 7.36-7.51 (m, 2H), 7.88-8.16 (m, 3H), 10.53-10.59 (m, 1H).
LCMS(ESI): [M]+ m/z: calcd 534.2; found 535.2; Rt=2.632 min.

Step 7: Chiral Separation (Compound 1256 and Compound 1136

Racemic N-(6-amino-5-ethyl-3-pyridyl)-2-[(2R,5S)-5-methyl-2-[2-(1-methyl-2-oxo-4-piperidyl)-1,3-benzothiazol-5-yl]-1-piperidyl]-2-oxo-acetamide (0.068 g, 127.18 μmol) was chiral separated (Column: Chiralpak OJ-H (250-20 mm-5 m); Mobile phase: Hexane-IPA-MeOH, 70-15-15 Flow Rate: 15 mL/min) to obtain N-(6-amino-5-ethyl-3-pyridyl)-2-[(2R,5S)-5-methyl-2-[2-(1-methyl-2-oxo-4-piperidyl)-1,3-benzothiazol-5-yl]-1-piperidyl]-2-oxo-acetamide (0.02603 g, 48.68 μmol, 38.28% yield) and N-(6-amino-3-pyridyl)-2-[(2S,5R)-5-methyl-2-[2-(trifluoromethyl)-1,3-benzothiazol-5-yl]-1-piperidyl]-2-oxo-acetamide (0.05775 g, 124.60 umol, 50.22% yield).
Rel Time for Compound 1256 in analytical conditions (column: OJ-H, Hexane-IPA-MeOH, 60-20-20, 0.6 ml/min as mobile phase) 31.50 min and for Compound 1136 38.37 min.

Compound 1256:
Retention time: 31.50 min
¹H NMR (600 MHz, DMSO-d₆) δ (ppm) 1.01-1.14 (m, 6H), 1.32-1.40 (m, 1H), 1.65-1.74 (m, 1H), 1.84-1.92 (m, 1H), 2.05-2.18 (m, 2H), 2.28-2.43 (m, 5H), 2.58-2.81 (m, 3H), 2.82 (s, 3H), 3.36-3.44 (m, 1H), 3.46-4.07 (m, 2H), 5.25-5.73 (m, 3H), 7.34-7.53 (m, 2H), 7.87-7.95 (m, 1H), 7.96-8.12 (m, 2H), 10.50-10.61 (m, 1H).
LCMS(ESI): [M]+ m/z: calcd 534.2; found 535.2; Rt=2.624 min.
Compound 1136:
Retention time: 38.37 min
¹H NMR (600 MHz, DMSO-d₆) δ (ppm)
LCMS(ESI): [M]+ m/z: calcd 534.2; found 535.2; Rt=2.627 min.

Example 581. The Synthesis of N-(6-amino-5-ethylpyridin-3-yl)-2-((2R,5S)-2-(2-(1-(2-Fluoroethyl)piperidin-4-yl)benzo[d]thiazol-5-yl)-5-methylpiperidin-1-yl)-2-oxoacetamide (Compound 1174

Step 1: Synthesis of 5-chloro-2-(1-(2-Fluoroethyl)piperidin-4-yl)benzo[d]thiazole A mixture of 5-chloro-2-(4-piperidyl)-1,3-benzothiazole (5 g, 15.35 mmol, 2HCl), 2-fluoroethyl methanesulfonate (2.29 g, 16.12 mmol) and TEA (6.21 g, 61.41 mmol, 8.56 mL) in MeCN (100 mL) was stirred at 50° C. for 24 hr. The LCMS of the aliquot showed 61% conversion. 2-Fluoroethyl methanesulfonate (2.18 g, 15.35 mmol) and TEA (4.66 g, 46.06 mmol, 6.42 mL) were added to the reaction mixture and it was stirred at 60° C. for 72 hr, then cooled down and concentrated in vacuum. The residue was diluted with water (50 ml) and basified to pH 11 with 10% aqueous sodium hydroxide solution. The resulting mixture was extracted with MTBE (250 ml). The organic layer was washed with water (50 ml), dried over sodium sulphate and concentrated in vacuum to afford 5-chloro-2-[1-(2-fluoroethyl)-4-piperidyl]-1,3-benzothiazole (3.3 g, 11.04 mmol, 71.94% yield) as brown solid.

LCMS(ESI): [M]⁺ m z: calcd 298.2; found 299.2; Rt 1.812 min.

Step 2: Synthesis of 2-(1-(2-Fluoroethyl)piperidin-4-yl)-5-(4,4,5,5-tetramethyl-1,3,2-dioxaborolan-2-yl)benzo[d]thiazole

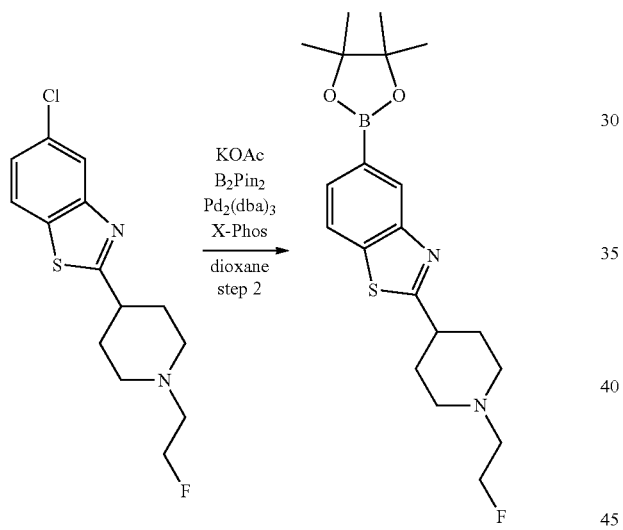

A mixture of 5-chloro-2-[1-(2-fluoroethyl)-4-piperidyl]-1,3-benzothiazole (3.3 g, 11.04 mmol), 4,4,5,5-tetramethyl-2-(4,4,5,5-tetramethyl-1,3,2-dioxaborolan-2-yl)-1,3,2-dioxaborolane (3.08 g, 12.15 mmol) and potassium acetate (2.17 g, 22.09 mmol, 1.38 mL) in dioxane (100 mL) was evacuated and then backfilled with argon. This operation was repeated two times, then tris(1,5-diphenylpenta-1,4-dien-3-one)dipalladium (505.66 mg, 552.20 umol) and dicyclohexyl[2',4',6'-tris(propan-2-yl)-[1,1'-biphenyl]-2-yl]phosphane (1.05 g, 2.21 mmol) were added under argon, and the reaction mixture was stirred at 95° C. for 18 hr. The reaction mixture was cooled down and concentrated in vacuum. The residue was purified by column chromatography on silica gel using MeCN/MeOH gradient (0-100% MeOH) to afford 2-[1-(2-fluoroethyl)-4-piperidyl]-5-(4,4,5,5-tetramethyl-1,3,2-dioxaborolan-2-yl)-1,3-benzothiazole (2.8 g, 7.17 mmol, 64.95% yield) as light-yellow solid.

LCMS(ESI): [M]⁺ m/z: calcd 390.2; found 391.2; Rt=1.011 min.

Step 3: Synthesis of (S)-tert-butyl 6-(2-(1-(2-Fluoroethyl)piperidin-4-yl)benzo[d]thiazol-5-yl)-3-methyl-3,4-dihydropyridine-1(2H)-carboxylate

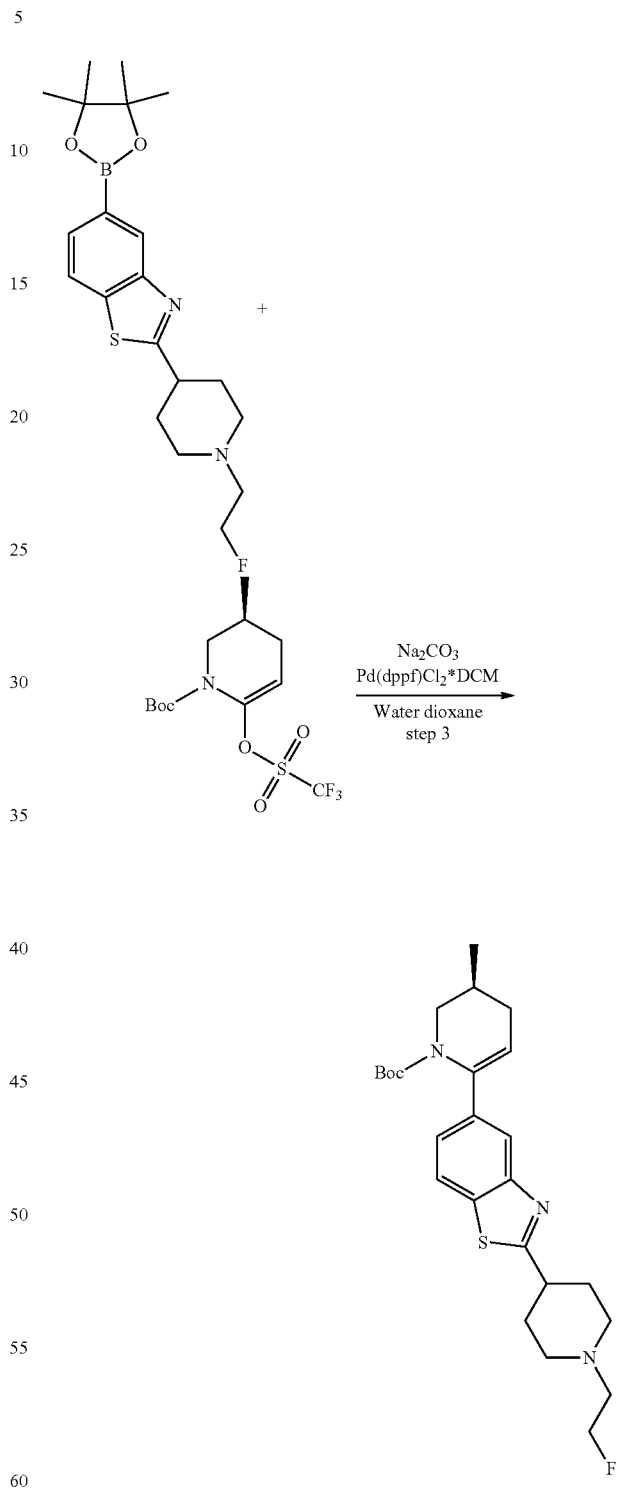

Prepared by general procedure scheme H step 3. Yield: 2 g (60.66%).

CC conditions: The crude product was purified by silica gel with CHCl₃/MeCN as an eluent mixture.

LCMS(ESI): [M]⁺ m/z: calcd 459.2; found 460.2; Rt=1.248 min.

Step 4: Synthesis of (S)-2-(1-(2-Fluoroethyl)piperidin-4-yl)-5-(5-methyl-3,4,5,6-tetrahydropyridin-2-yl)benzo[d]thiazole

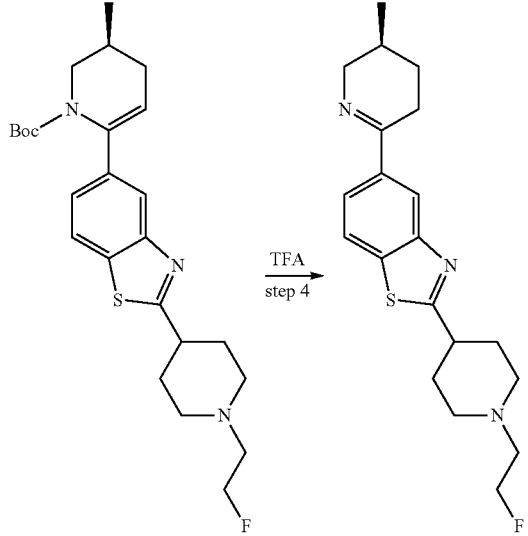 [SMILES: C[C@H]1CC=C(c2ccc3sc(C4CCN(CCF)CC4)nc3c2)N(C(=O)OC(C)(C)C)C1 ; C[C@H]1CCC(c2ccc3sc(C4CCN(CCF)CC4)nc3c2)=NC1]

Prepared by general procedure scheme H step 4. Yield: 760 mg (48.58%).

LCMS(ESI): [M]+ m/z: calcd 359.2; found 360.2; Rt=0.574 min.

Step 5: Synthesis of 2-(1-(2-Fluoroethyl)piperidin-4-yl)-5-((2R,5S)-5-methylpiperidin-2-yl)benzo[d]thiazole

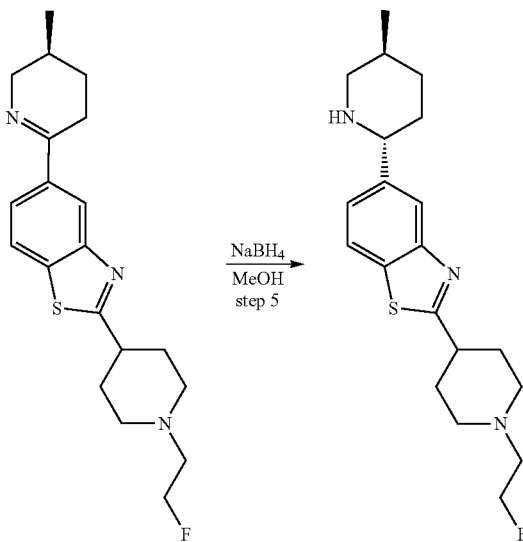 [SMILES: C[C@H]1CCC(c2ccc3sc(C4CCN(CCF)CC4)nc3c2)=NC1 ; "NaBH4" ; C[C@H]1CC[C@H](c2ccc3sc(C4CCN(CCF)CC4)nc3c2)NC1]

Prepared by general procedure scheme H step 5. Yield: 620 mg (81.12%). LCMS(ESI): [M]+ m/z: calcd 361.2; found 362.2; Rt=0.724 min.

The Synthesis of N-(6-amino-5-ethylpyridin-3-yl)-2-((2R,5S)-2-(2-(1-(2-Fluoroethyl)piperidin-4-yl)benzo[d]thiazol-5-yl)-5-methylpiperidin-1-yl)-2-oxoacetamide (Compound 1174)

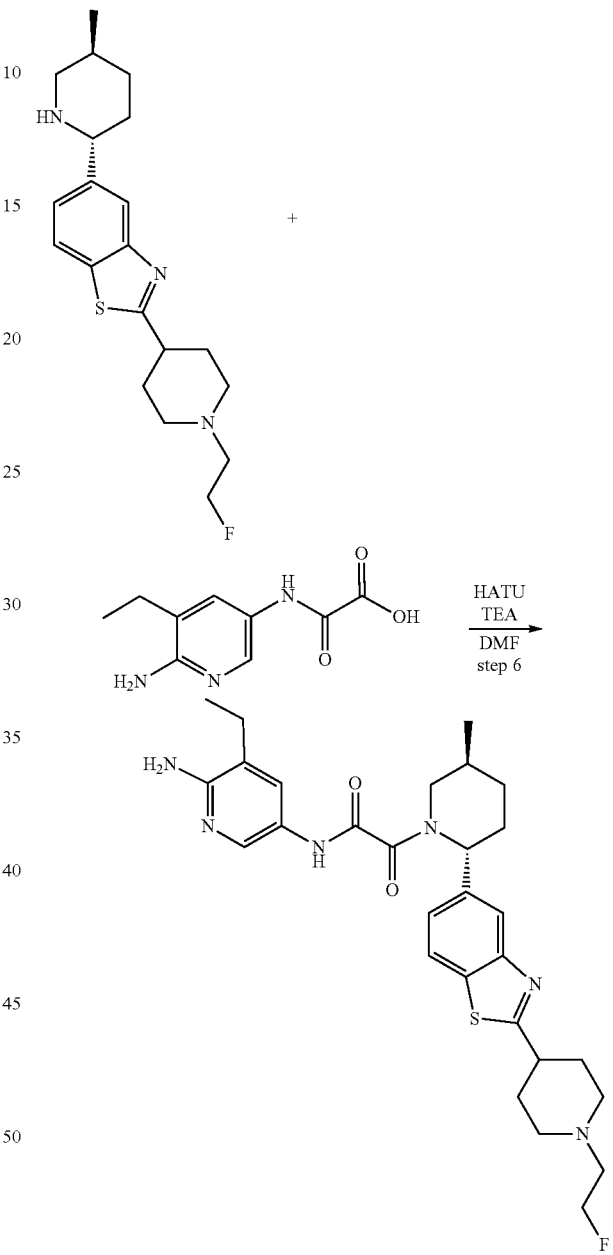

Prepared by general procedure scheme H step 6A. Yield: 70.6 mg (30.79%).

HPLC conditions: Column: YMC Triart C18 100*20 mm, 5 microM; 0-1-5 min 50-50-60% water-MeOH+0.1% NH$_4$OH; (loading pump 4 ml/min MeOH).

$^1$H NMR (600 MHz, DMSO-d$_6$) δ (ppm) 1.02-1.13 (m, 6H), 1.32-1.39 (m, 1H), 1.69-1.89 (m, 4H), 2.07-2.22 (m, 5H), 2.28-2.41 (m, 3H), 2.60-2.67 (m, 2H), 2.77-2.97 (m, 3H), 3.07-3.11 (m, 1H), 3.46-4.05 (m, 1H), 4.48-4.58 (dt, 2H), 5.27-5.69 (m, 3H), 7.34-7.51 (m, 2H), 7.86-7.90 (d, 1H), 7.99-8.07 (m, 2H), 10.53-10.58 (d, 1H).

LCMS(ESI): [M]+ m/z: calcd 552.2; found 553.2; Rt=2.212 min.

Example 582. The Synthesis of N-(6-amino-5-ethylpyridin-3-yl)-2-((2R,5S)-2-(2-(1-(2,2-difluoroethyl)piperidin-4-yl)benzo[d]thiazol-5-yl)-5-methylpiperidin-1-yl)-2-oxoacetamide (Compound 1304)

Step 1: Synthesis of 5-chloro-2-(1-(2,2-difluoroethyl)piperidin-4-yl)benzo[d]thiazole

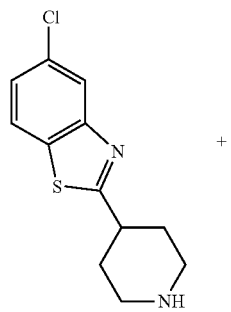

+

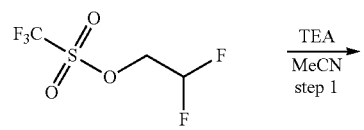

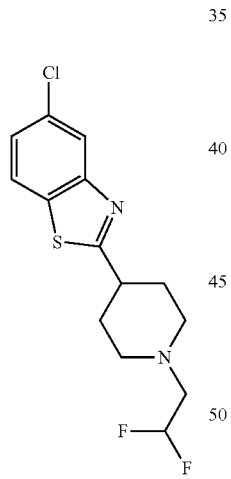

A mixture of 5-chloro-2-(4-piperidyl)-1,3-benzothiazole (3.6 g, 11.05 mmol, 2HCl), 2,2-difluoroethyl trifluoromethanesulfonate (2.84 g, 13.26 mmol) and TEA (5.59 g, 55.27 mmol, 7.70 mL) in MeCN (100 mL) was stirred at 60° C. for 72 hr, then cooled down and concentrated in vacuum. The residue was diluted with water (50 ml) and basified to pH 11 with 10% aqueous sodium hydroxide solution. The resulting mixture was extracted with MTBE (250 ml). The organic layer was washed with water (50 ml), dried over sodium sulphate and concentrated in vacuum to afford crude 5-chloro-2-[1-(2,2-difluoroethyl)-4-piperidyl]-1,3-benzothiazole (3 g, 9.47 mmol, ⁸5.67% yield) as brown solid, which was used directly in the next step.

LCMS(ESI): [M]+ m/z: calcd 316.2; found 317.2; Rt=2.015 min.

Step 2: Synthesis of 2-(1-(2,2-difluoroethyl)piperidin-4-yl)-5-(4,4,5,5-tetramethyl-1,3,2-dioxaborolan-2-yl)benzo[d]thiazole

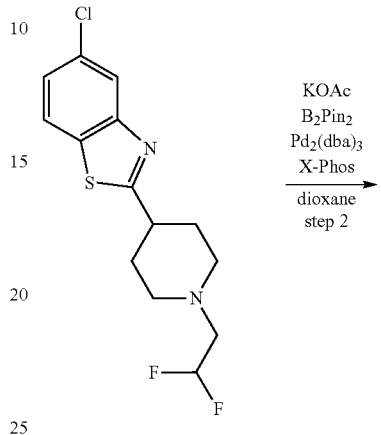

A mixture of 5-chloro-2-[1-(2,2-difluoroethyl)-4-piperidyl]-1,3-benzothiazole (3 g, 9.47 mmol), 4,4,5,5-tetramethyl-2-(4,4,5,5-tetramethyl-1,3,2-dioxaborolan-2-yl)-1,3,2-dioxaborolane (2.65 g, 10.42 mmol) and potassium acetate (1.86 g, 18.94 mmol, 1.18 mL) in dioxane (100 mL) was evacuated and then backfilled with argon. This operation was repeated two times, then tris(1,5-diphenylpenta-1,4-dien-3-one)dipalladium (433.58 mg, 473.49 umol) and dicyclohexyl[2',4',6'-tris(propan-2-yl)-[1,1'-biphenyl]-2-yl]phosphane (902.89 mg, 1.89 mmol) were added under argon, and the reaction mixture was stirred at 95° C. for 18 hr. The reaction mixture was cooled down and concentrated in vacuum. The residue was purified by column chromatography on silica gel using hexane/ethyl acetate gradient (0-100% ethyl acetate) to afford 2-[1-(2,2-difluoroethyl)-4-piperidyl]-5-(4,4,5,5-tetramethyl-1,3,2-dioxaborolan-2-yl)-1,3-benzothiazole (1.5 g, 3.67 mmol, 38.79% yield) as beige solid.

LCMS(ESI): [M]+ m/z: calcd 408.2; found 409.2; Rt=0.989 min.

2555

Step 3: Synthesis of (S)-tert-butyl 6-(2-(1-(2,2-difluoroethyl)piperidin-4-yl)benzo[d]thiazol-5-yl)-3-methyl-3,4-dihydropyridine-1(2H)-carboxylate

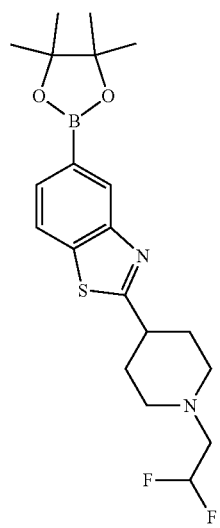

+

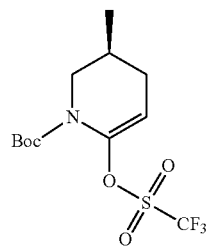

Na₂CO₃
Pd(dppf)Cl₂*DCM
water
dioxane
step 3

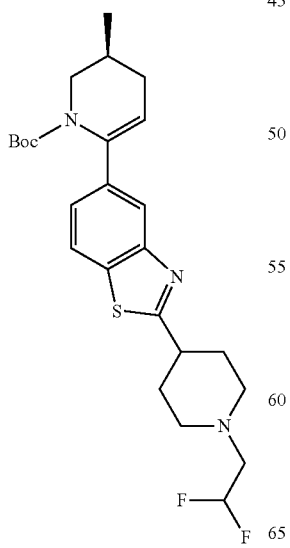

2556

Prepared by general procedure scheme H step 3. Yield: 0.9 g (51.29%).

CC conditions: The crude product was purified by silica gel with hexane/MTBE as an eluent mixture.

LCMS(ESI): [M]⁺ m/z: calcd 477.2; found 478.2; Rt=1.120 min.

Step 4: Synthesis of (S)-2-(1-(2,2-difluoroethyl)piperidin-4-yl)-5-(5-methyl-3,4,5,6-tetrahydropyridin-2-yl)benzo[d]thiazole

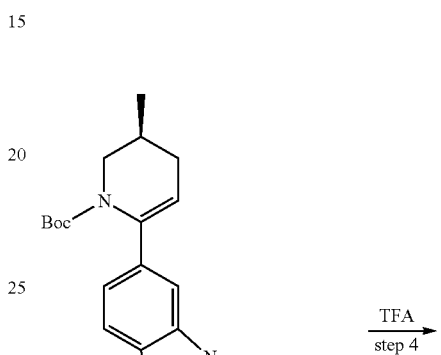

TFA
step 4

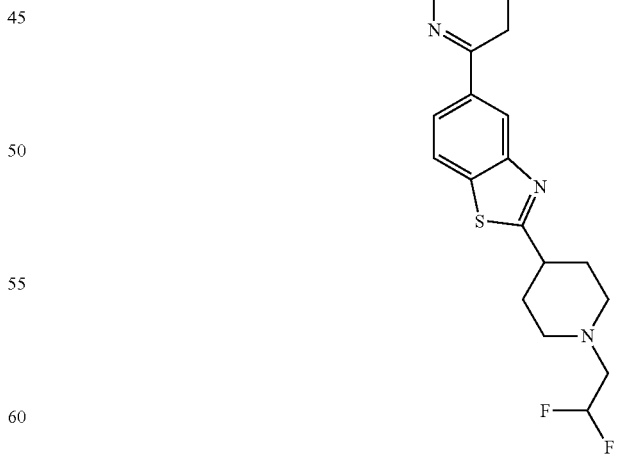

Prepared by general procedure scheme H step 4. Yield: 0.67 g (94.19%).

LCMS(ESI): [M]⁺ m/z: calcd 377.2; found 378.2; Rt=0.707 min.

2557

Step 5: Synthesis of 2-(1-(2,2-difluoroethyl)piperidin-4-yl)-5-((2R,5S)-5-methylpiperidin-2-yl)benzo[d]thiazole

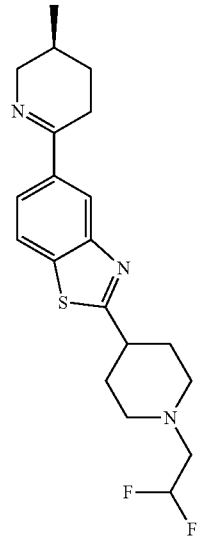

Prepared by general procedure scheme H step 5. Yield: 0.55 g (81.65%).

LCMS(ESI): [M]+ m/z: calcd 379.2; found 380.2; Rt=0.744 min.

2558

Step 6: The Synthesis of N-(6-amino-5-ethylpyridin-3-yl)-2-((2R,5S)-2-(2-(1-(2,2-difluoroethyl)piperidin-4-yl)benzo[d]thiazol-5-yl)-5-methylpiperidin-1-yl)-2-oxoacetamide (Compound 1304)

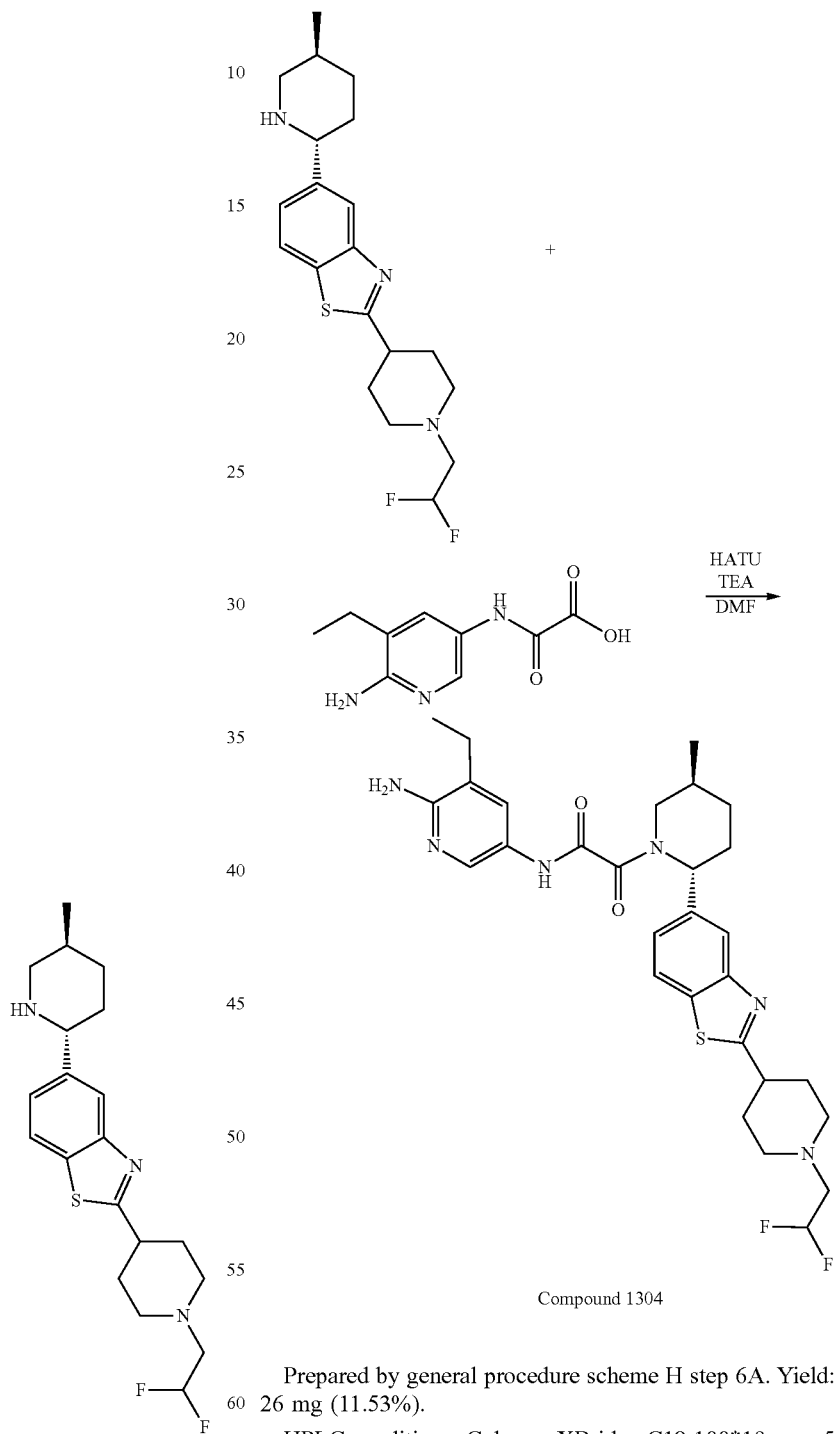

Compound 1304

Prepared by general procedure scheme H step 6A. Yield: 26 mg (11.53%).

HPLC conditions: Column: XBridge C18 100*19 mm, 5 microM; 0-5 min 30-55% water-MeCN+0.1% NH$_4$OH; (loading pump 4 ml/min MeOH).

$^1$H NMR (600 MHz, DMSO-d$_6$) δ (ppm) 1.02-1.13 (m, 6H), 1.32-1.39 (m, 1H), 1.69-1.90 (m, 4H), 2.06-2.18 (m, 3H), 2.28-2.40 (m, 4H), 2.72-2.78 (m, 3H), 2.97-3.10 (m, 3H), 3.47-4.05 (m, 2H), 5.28-5.69 (m, 3H), 6.04-6.23 (m, 1H), 7.34-7.51 (m, 2H), 7.86-8.07 (m, 3H), 10.53-10.58 (m, 1H).

LCMS(ESI): [M]⁺ m/z: calcd 570.2; found 571.2; Rt=2.104 min.

Example 583. Synthesis of rac-N,N-dimethyl-2-(5-((2R,5S)-5-methylpiperidin-2-yl)benzo[d]thiazol-2-yl)ethanamine Step 1: Synthesis of 2-(5-bromobenzo[d]thiazol-2-yl)-N,N-dimethylethanamine

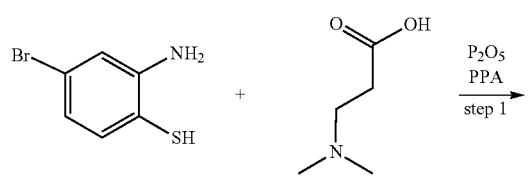

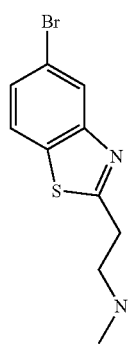

Prepared by general procedure scheme J step 1A. Yield: 1 g (11.18%).

CC conditions: The crude product was purified by silica gel with CHCl₃/MeOH as an eluent mixture.

LCMS(ESI): [M]⁺ m/z: calcd 285.2; found 286.2; Rt=0.824 min.

Step 2: Synthesis of N,N-dimethyl-2-(5-(4,4,5,5-tetramethyl-1,3,2-dioxaborolan-2-yl)benzo[d]thiazol-2-yl)ethanamine

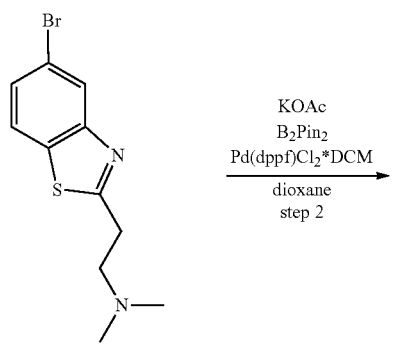

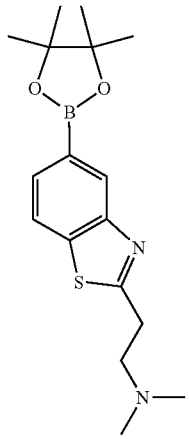

Prepared by general procedure scheme J step 2. Yield: 1.1 g of crude

LCMS(ESI): [M]⁺ m/z: calcd 332.2; found 333.2; Rt=1.004 min.

Step 3: Synthesis of tert-butyl 6-(2-(2-(dimethylamino)ethyl)benzo[d]thiazol-5-yl)-3-methyl-3,4-dihydropyridine-1(2H)-carboxylate

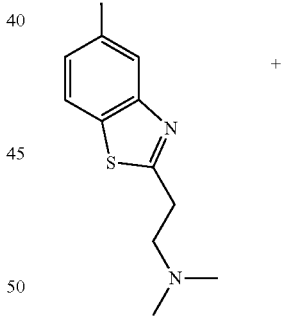

+

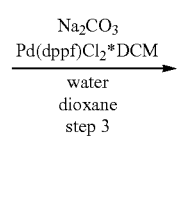

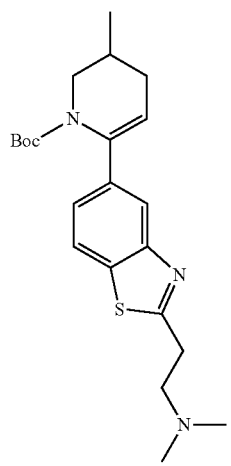

Prepared by general procedure scheme J step 3. Yield: 1.5 g of crude.
LCMS(ESI): [M]+ m/z: calcd 401.2; found 402.2; Rt=1.064 min.

Step 4: Synthesis of N,N-dimethyl-2-(5-(5-methyl-3,4,5,6-tetrahydropyridin-2-yl)benzo[d]thiazol-2-yl)ethanamine

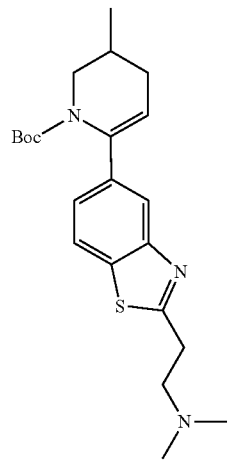

TFA
step 4
→

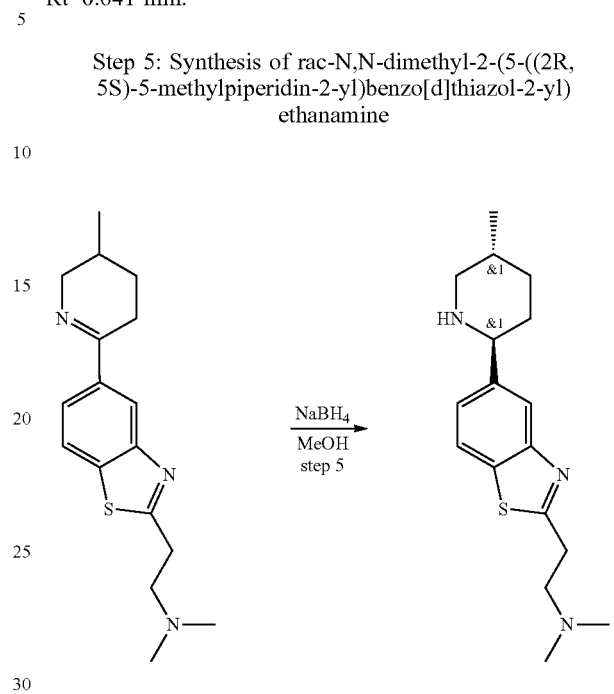

Prepared by general procedure scheme J step 4. Yield: 1.3 g of crude.
LCMS(ESI): [M]+ m/z: calcd 301.2; found 302.2; Rt=0.641 min.

Step 5: Synthesis of rac-N,N-dimethyl-2-(5-((2R,5S)-5-methylpiperidin-2-yl)benzo[d]thiazol-2-yl)ethanamine Prepared by general procedure scheme H step 5. Yield: 1.2 g of crude.
LCMS(ESI): [M]+ m/z: calcd 303.2; found 304.2; Rt=0.486 min.

Example 584. The Synthesis of N-(6-amino-5-ethylpyridin-3-yl)-2-((2R,5S)-5-methyl-2-(2-(2-(pyrrolidin-1-yl)ethyl)benzo[d]thiazol-5-yl)piperidin-1-yl)-2-oxoacetamide (Compound 1095)

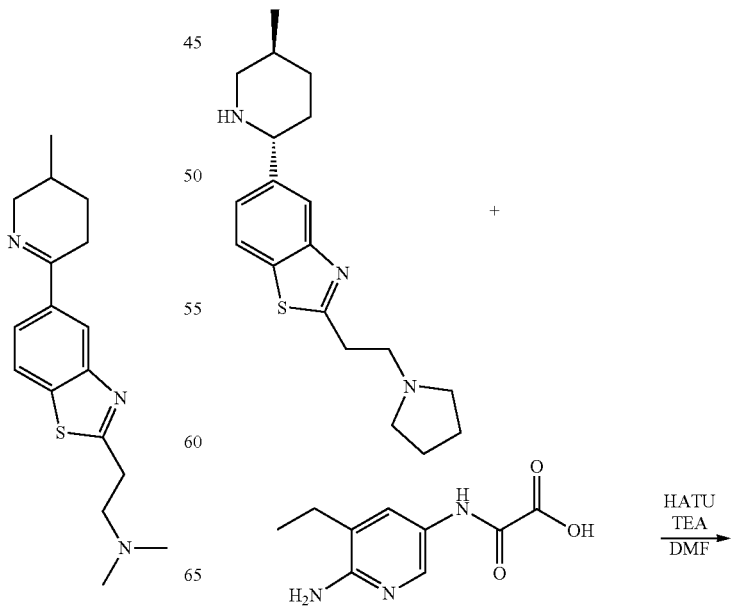

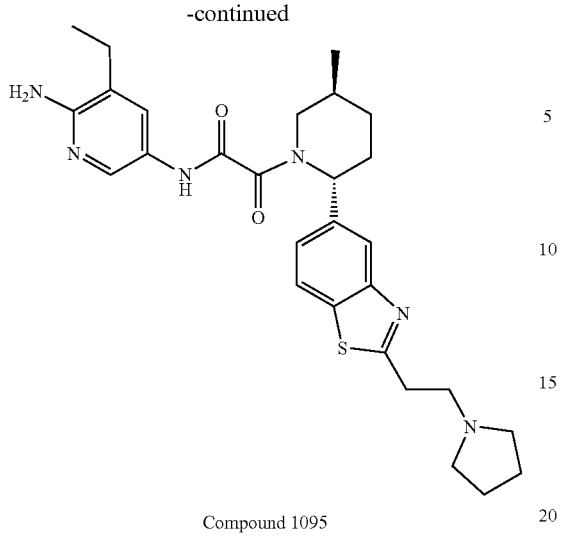

Compound 1095

Prepared by general procedure 8. Yield: 33 mg (21.42%).

HPLC conditions: Column: YMC Triart C18 100*19 mm, 5 microM; 0-1-5 min 30-30-65% water-MeCN+0.1% NH₄OH; (loading pump 4 ml/min MeCN).

Compound 1095:

¹H NMR (600 MHz, DMSO-$d_6$) δ (ppm) 1.02-1.14 (m, 6H), 1.32-1.40 (m, 2H), 1.68 (m, 5H), 1.85-1.90 (m, 2H), 2.06-2.37 (m, 5H), 2.76-2.86 (m, 3H), 3.24 (m, 2H), 3.47-4.05 (m, 2H), 5.28-5.69 (m, 3H), 7.32-7.51 (m, 2H), 7.84-7.88 (d, 1H), 8.00-8.07 (m, 2H), 10.51-10.56 (d, 1H).

LCMS(ESI): [M]⁺ m/z: calcd 520.2; found 521.2; Rt=1.944 min.

Example 585. The Synthesis of 2-((2R,5S)-5-methyl-2-(2-(1-methylpiperidin-4-yl)benzo[d]thiazol-5-yl)piperidin-1-yl)-N-(6-methyl-5-(oxetan-3-yl)pyridin-3-yl)-2-oxoacetamide (Compound 1309)

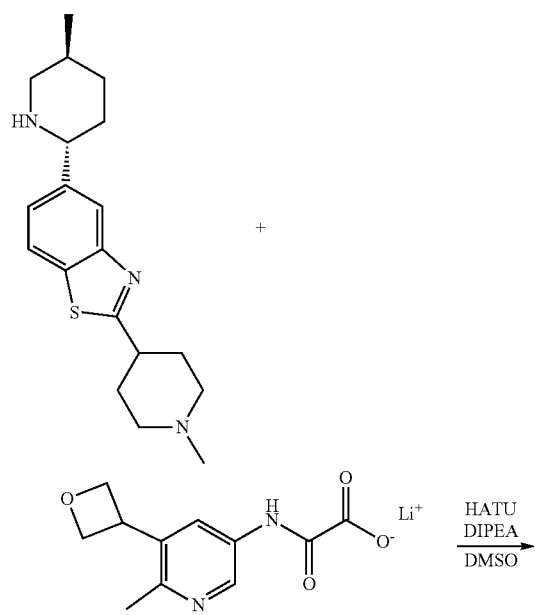

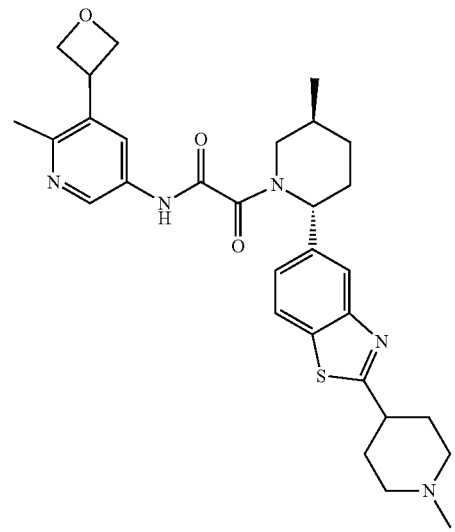

Compound 1309

Prepared by general procedure scheme H step 6B. Yield: 9 mg (5.31%).

HPLC conditions: Column: SunFire C18 100*19 mm, 5 microM; 2-10 min 50-100% MeOH; (loading pump 4 ml/min MeOH).

2-[(2R,5S)-5-methyl-2-[2-(1-methyl-4-piperidyl)-1,3-benzothiazol-5-yl]-1-piperidyl]-N-[6-methyl-5-(oxetan-3-yl)-3-pyridyl]-2-oxo-acetamide was purified by chiral HPLC: (Column: Chiralcel OD-H (250*20 mm, 5 mkm), Hexane-IPA-MeOH, 50-25-25, 12 ml/min) to obtain 2-[(2R,5S)-5-methyl-2-[2-(1-methyl-4-piperidyl)-1,3-benzothiazol-5-yl]-1-piperidyl]-N-[6-methyl-5-(oxetan-3-yl)-3-pyridyl]-2-oxo-acetamide (0.009 g, 16.43 μmol, 5.31% yield).

Rel Time for Compound 1309 in analytical conditions (column: OD-H, Hexane-IPA-MeOH, 50-25-25, 0.6 ml/min as mobile phase) 17.78 min.

¹H NMR (600 MHz, DMSO-$d_6$) δ (ppm) 0.98-1.08 (m, 3H), 1.27-1.42 (m, 1H), 1.66-1.77 (m, 1H), 1.77-2.00 (m, 3H), 2.08-2.21 (m, 3H), 2.22-2.28 (m, 3H), 2.28-2.36 (m, 3H), 2.45-2.46 (m, 3H), 2.82-3.09 (m, 3H), 3.09-3.22 (m, 1H), 3.54-4.07 (m, 1H), 4.36-4.50 (m, 1H), 4.52-4.67 (m, 2H), 4.86-4.99 (m, 2H), 5.27-5.75 (m, 1H), 7.34-7.46 (m, 1H), 7.85-7.97 (m, 1H), 7.98-8.12 (m, 2H), 8.52-8.67 (m, 1H), 10.84-11.29 (m, 1H).

LCMS(ESI): [M]⁺ m/z: calcd 547.2; found 548.2; Rt=2.313 min.

2565

Example 586. The Synthesis of N-(5,6-dimethylpyridin-3-yl)-2-((2R,5S)-5-methyl-2-(2-(1-methylpiperidin-4-yl)benzo[d]thiazol-5-yl)piperidin-1-yl)-2-oxoacetamide (Compound 1137)

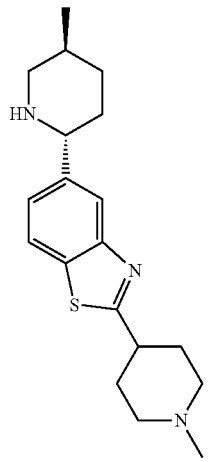

+

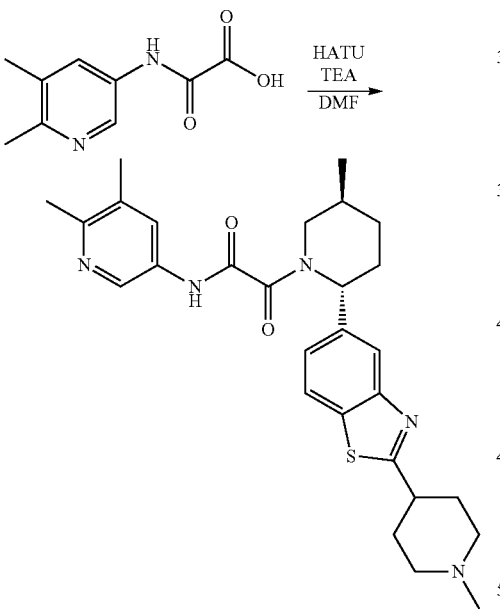

Prepared by general procedure scheme H step 6A. Yield: 47 mg (27.84%).

HPLC conditions: Column: XBridge C18 100*19 mm, 5 microM; 0-1-6 min 10-10-60% water-MeCN+0.1% NH$_4$OH; (loading pump 4 ml/min MeCN).

$^1$H NMR (600 MHz, DMSO-d$_6$) δ (ppm) 1.00-1.07 (m, 3H), 1.29-1.42 (m, 1H), 1.64-1.75 (m, 1H), 1.76-1.92 (m, 3H), 1.99-2.13 (m, 5H), 2.17-2.25 (m, 6H), 2.31-2.39 (m, 4H), 2.50-2.51 (m, 1H), 2.80-2.85 (m, 2H), 3.00-3.10 (m, 1H), 3.43-4.06 (m, 1H), 5.22-5.76 (m, 1H), 7.32-7.44 (m, 1H), 7.72-7.85 (m, 1H), 7.85-7.94 (m, 1H), 8.02-8.09 (m, 1H), 8.39-8.55 (m, 1H), 10.79-11.14 (m, 1H).

LCMS(ESI): [M]$^+$ m/z: calcd 505.2; found 506.2; Rt=1.873 min.

2566

Example 587. Synthesis of N-(6-amino-5-ethylpyridin-3-yl)-2-((2R,5S)-5-methyl-2-(2-(1-methyl-1H-pyrazol-5-yl)benzo[d]thiazol-5-yl)piperidin-1-yl)-2-oxoacetamide (Compound 1389

Step 1: Synthesis of 5-chloro-2-(1-methyl-1H-pyrazol-5-yl)benzo[d]thiazole

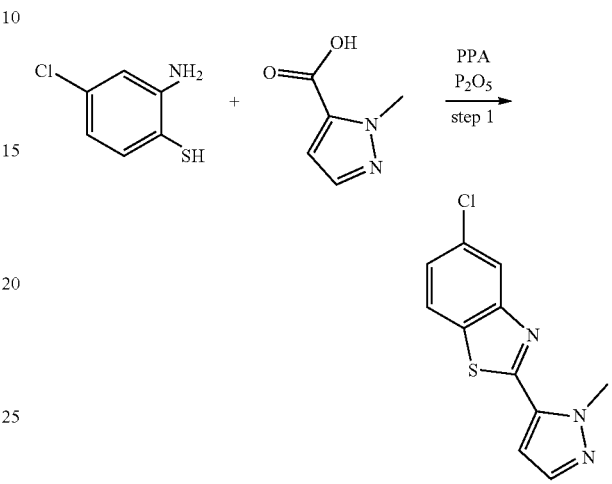

Prepared by general procedure scheme H step 1A. Yield: 8 g (96.96%).

LCMS(ESI): [M]$^+$ m/z: calcd 249.2; found 250.2; Rt=1.539 min.

Step 2: Synthesis of 2-(1-methyl-1H-pyrazol-5-yl)-5-(4,4,5,5-tetramethyl-1,3,2-dioxaborolan-2-yl)benzo[d]thiazole

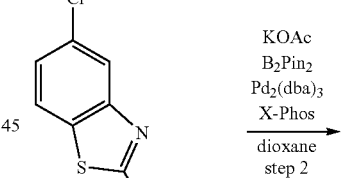

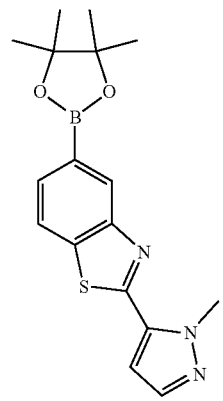

Potassium acetate (6.29 g, 64.07 mmol, 4.01 mL) was added to a solution of 5-chloro-2-(2-methylpyrazol-3-yl)-1,3-benzothiazole (8.00 g, 32.04 mmol) and 4,4,5,5-tetramethyl-2-(4,4,5,5-tetramethyl-1,3,2-dioxaborolan-2-yl)-1,3,2-dioxaborolane (8.95 g, 35.24 mmol) in dioxane (100 mL). Reaction flask was evacuated and refilled with argon 3 times. Then tris(dibenzylideneacetone)dipalladium(0) (1.47 g, 1.60 mmol) and X-Phos (3.05 g, 6.41 mmol) was added under stream of argon. Resulting mixture was stirred at 90° C. for 18 hr under inert atmosphere. Then, it was cooled, diluted with EtOAc (200 mL) and filtered off. The filtrate was concentrated under reduced pressure and the residue was purified by silica gel flash chromatography eluting with a 0 to 100 percent chloroform-MTBE gradient to give 2-(2-methylpyrazol-3-yl)-5-(4,4,5,5-tetramethyl-1,3,2-dioxaborolan-2-yl)-1,3-benzothiazole (6.7 g, 19.63 mmol, 61.29% yield).

LCMS(ESI): [M]$^+$ m/z: calcd 341.2; found 342.2; Rt=1.600 min.

Step 3: Synthesis of (S)-tert-butyl 3-methyl-6-(2-(1-methyl-1H-pyrazol-5-yl)benzo[d]thiazol-5-yl)-3,4-dihydropyridine-1(2H)-carboxylate Prepared by general procedure scheme H step 3. Yield: 12 g of crude.

LCMS(ESI): [M]$^+$ m/z: calcd 410.2; found 411.2; Rt=1.654 min.

Step 4: Synthesis of (S)-2-(1-methyl-1H-pyrazol-5-yl)-5-(5-methyl-3,4,5,6-tetrahydropyridin-2-yl)benzo[d]thiazole

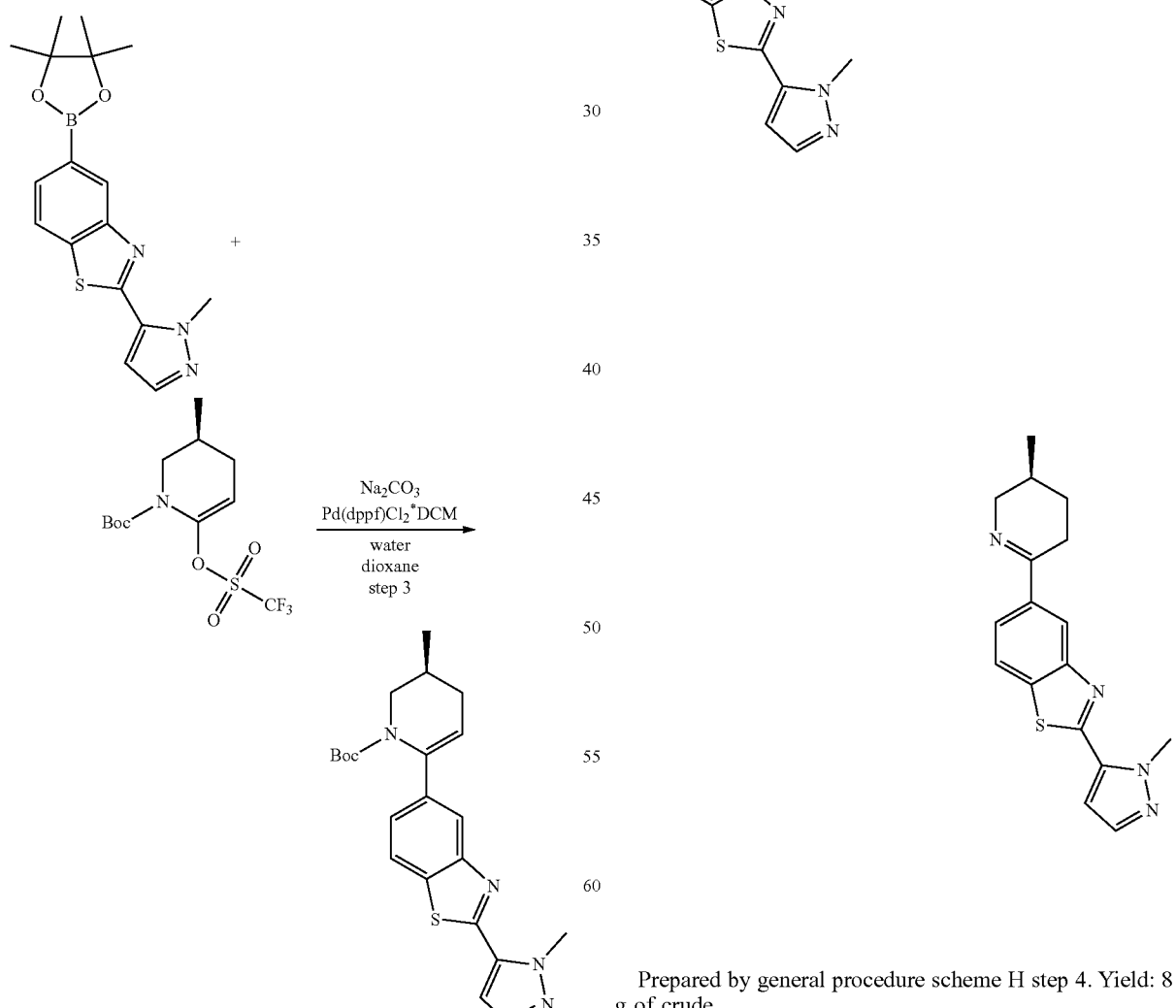

Prepared by general procedure scheme H step 4. Yield: 8 g of crude.

LCMS(ESI): [M]$^+$ m/z: calcd 310.2; found 311.2; Rt=0.983 min.

Step 5: Synthesis of 2-(1-methyl-1H-pyrazol-5-yl)-5-((2R,5S)-5-methylpiperidin-2-yl)benzo[d]thiazole

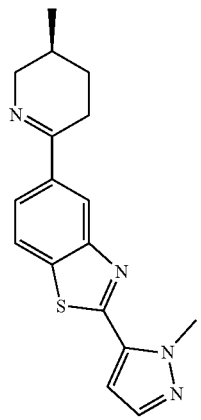

Prepared by general procedure scheme H step 5. Yield: 8 g (99.35%).

LCMS(ESI): [M]+ m/z: calcd 312.2; found 313.2; Rt=0.967 min.

Step 6: Synthesis of N-(6-amino-5-ethylpyridin-3-yl)-2-((2R,5S)-5-methyl-2-(2-(1-methyl-1H-pyrazol-5-yl)benzo[d]thiazol-5-yl)piperidin-1-yl)-2-oxoacetamide (Compound 1389)

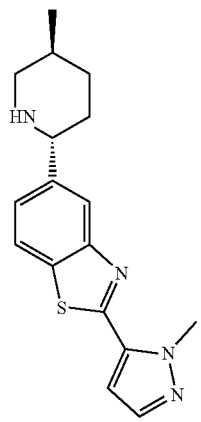

+

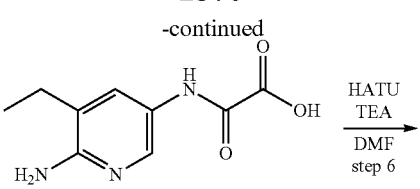

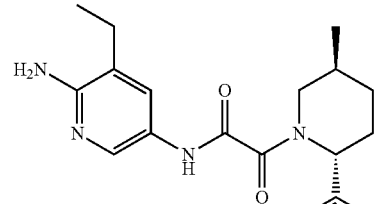

Compound 1389

Prepared by general procedure scheme H step 6A. Yield: 28 mg (4.34%).

HPLC conditions: Column:YMC Triart C18 100*20 mm, 5 microM; 0-1-6 min 10-10-65% water-MeCN+0.1% NH$_4$OH, flow: 30 ml/min; (loading pump 4 ml/min MeCN).

$^1$H NMR (600 MHz, DMSO-d$_6$) δ (ppm) 1.04-1.19 (m, 6H), 1.29-1.50 (m, 1H), 1.67-1.81 (m, 1H), 1.84-2.00 (m, 1H), 2.07-2.28 (m, 1H), 2.34-2.47 (m, 3H), 2.82-3.26 (m, 1H), 3.51-4.15 (m, 1H), 4.30 (s, 3H), 5.31-5.61 (m, 1H), 5.60-5.79 (m, 2H), 6.96-7.03 (m, 1H), 7.43-7.50 (m, 1H), 7.50-7.56 (m, 1H), 7.57-7.65 (m, 1H), 7.98-8.11 (m, 2H), 8.13-8.24 (m, 1H), 10.49-10.66 (m, 1H).

LCMS(ESI): [M]+ m/z: calcd 503.2; found 504.2; Rt=2.867 min.

Example 588. The Synthesis of N-(5-chloro-6-methylpyridin-3-yl)-2-((2R,5S)-5-methyl-2-(2-(1-methylpiperidin-4-yl)benzo[d]thiazol-5-yl)piperidin-1-yl)-2-oxoacetamide (Compound 1102)

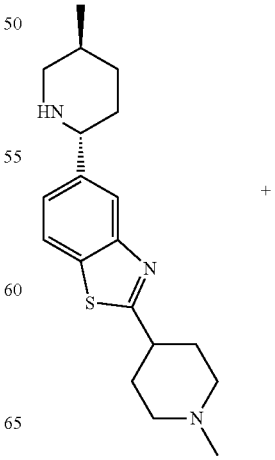

+

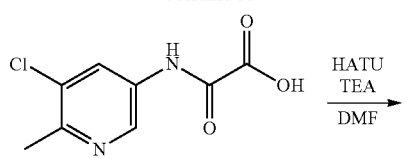

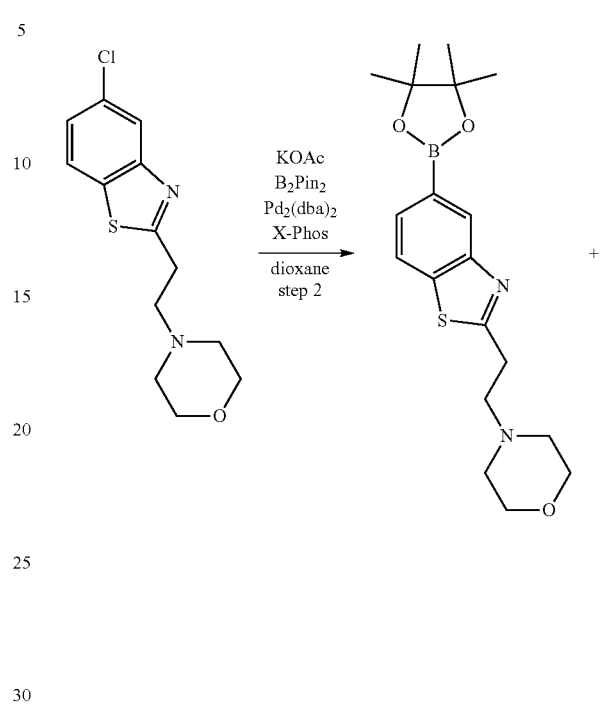

Prepared by general procedure scheme H step 6A. Yield: 113 mg (39.32%).

HPLC conditions: Column: YMC Triart C18 100*20 mm, 5 microM; 0-1-6 min 60-90% water-MeOH+0.1% NH$_4$OH; (loading pump 4 ml/min MeOH).

$^1$H NMR (600 MHz, DMSO-d$_6$) δ (ppm) 0.99-1.07 (m, 3H), 1.30-1.40 (m, 1H), 1.69-1.92 (m, 4H), 2.00-2.13 (m, 5H), 2.18 (s, 3H), 2.28-2.35 (m, 1H), 2.50 (s, 3H), 2.80-3.09 (m, 4H), 3.48-4.04 (m, 1H), 5.28-5.73 (m, 1H), 7.32-7.42 (m, 1H), 7.86-7.92 (m, 1H), 8.00-8.25 (m, 2H), 8.52-8.69 (m, 1H), 11.14-11.34 (m, 1H).

LCMS(ESI): [M]$^+$ m/z: calcd 526.2; found 527.2; Rt=3.173 min.

Example 589. The Synthesis of N-(6-amino-5-ethylpyridin-3-yl)-2-((2R,5S)-5-methyl-2-(2-(2-Morpholinoethyl)benzo[d]thiazol-5-yl)piperidin-1-yl)-2-oxoacetamide (Compound 1248)

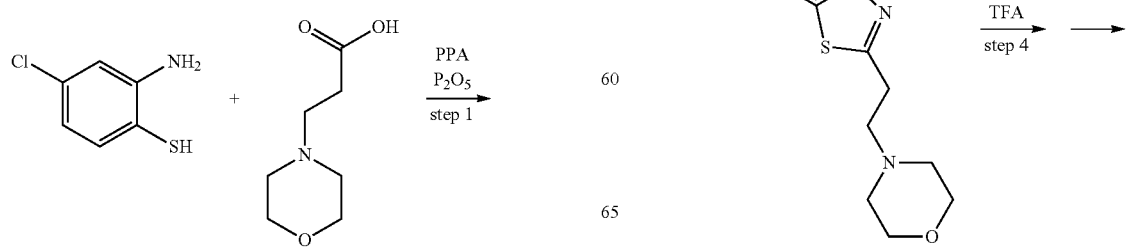

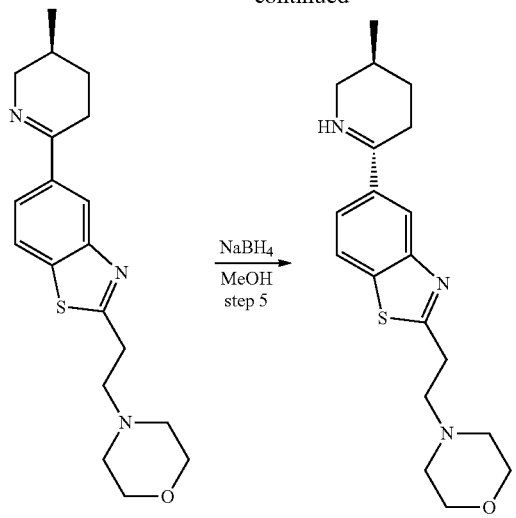

Step 1: Synthesis of 4-(2-(5-chlorobenzo[d]thiazol-2-yl)ethyl)morpholine

Prepared by general procedure scheme H step 1A. Yield: 3.5 g (39.52%).
CC conditions: The crude product was purified by silica gel with CHCl$_3$/MeCN as an eluent mixture.
LCMS(ESI): [M]$^+$ m/z: calcd 282.2; found 283.2; Rt=0.916 min.

Step 2: Synthesis of 4-(2-(5-(4,4,5,5-tetramethyl-1,3,2-dioxaborolan-2-yl)benzo[d]thiazol-2-yl)ethyl)morpholine Potassium acetate (2.43 g, 24.75 mmol, 1.55 mL) was added to a solution of 4-[2-(5-chloro-1,3-benzothiazol-2-yl)ethyl]morpholine (3.5 g, 12.38 mmol) and 4,4,5,5-tetramethyl-2-(4,4,5,5-tetramethyl-1,3,2-dioxaborolan-2-yl)-1,3,2-dioxaborolane (3.46 g, 13.61 mmol) in dioxane (40 mL). Reaction flask was evacuated and refilled with argon 3 times. Then tris(dibenzylideneacetone)dipalladium(0) (566.68 mg, 618.84 umol) and XPhos (1.18 g, 2.48 mmol) was added under stream of argon. Resulting mixture was stirred at 90° C. for 18 hr under inert atmosphere. Then, it was cooled, diluted with EtOAc (200 mL) and washed with Na$_2$CO$_3$ (50 mL, sat. aq.). Organic layer was dried over Na$_2$SO$_4$, concentrated under reduced pressure and the residue was purified by silica gel flash chromatography eluting with a 0 to 100 percent chloroform-MeCN gradient to afford product 4-[2-[5-(4,4,5,5-tetramethyl-1,3,2-dioxaborolan-2-yl)-1,3-benzothiazol-2-yl]ethyl]morpholine (2.1 g, 5.61 mmol, 45.33% yield).
LCMS(ESI): [M]$^+$ m/z: calcd 374.2; found 375.2; Rt=0.889 min.

Step 3: Synthesis of (S)-tert-butyl 3-methyl-6-(2-(2-Morpholinoethyl)benzo[d]thiazol-5-yl)-3,4-dihydropyridine-1(2H)-carboxylate Prepared by general procedure scheme H step 3. Yield: 3.5 g of crude.
LCMS(ESI): [M]$^+$ m/z: calcd 443.2; found 444.2; Rt=1.080 min.

Step 4: Synthesis of (S)-4-(2-(5-(5-methyl-3,4,5,6-tetrahydropyridin-2-yl)benzo[d]thiazol-2-yl)ethyl)morpholine Prepared by general procedure scheme H step 4. Yield: 3.5 g of crude.
LCMS(ESI): [M]$^+$ m/z: calcd 343.2; found 344.2; Rt=0.501 min.

Step 5: Synthesis of 4-(2-(5-((2R,5S)-5-methylpiperidin-2-yl)benzo[d]thiazol-2-yl)ethyl)morpholine Prepared by general procedure scheme H step 5. Yield: 2 g of crude.
LCMS(ESI): [M]$^+$ m/z: calcd 345.2; found 346.2; Rt=0.551 min.

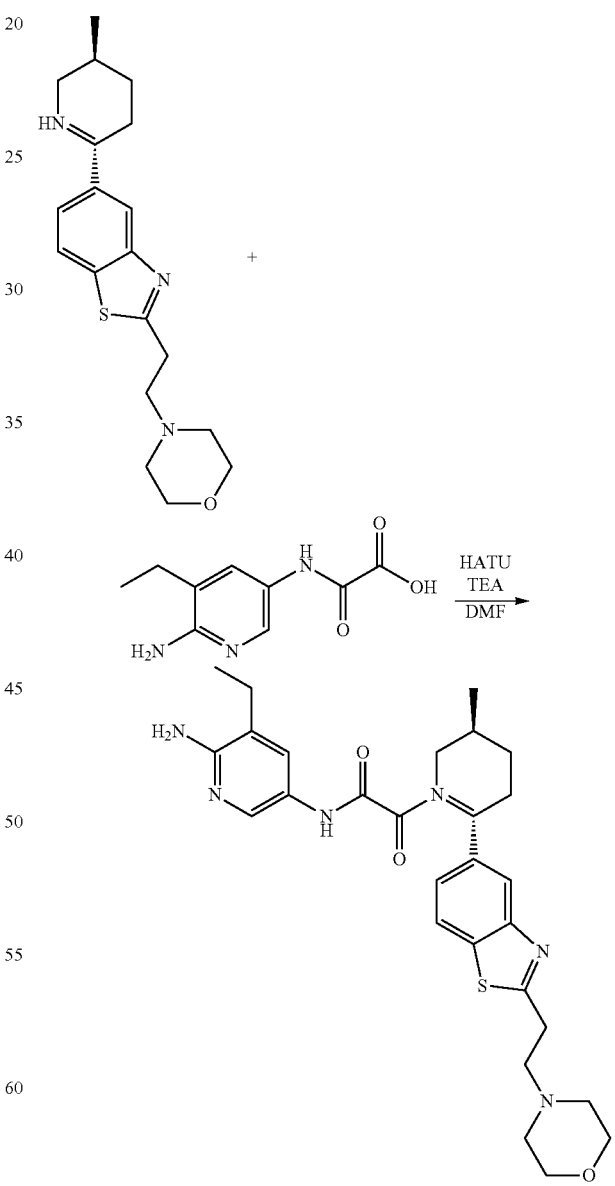

Prepared by general procedure scheme H step 6A. Yield: 92 mg (39.48%).

HPLC conditions: Column: XBridge C18 100*19 mm, 5 microM; 0-5 min 15-65% water-MeCN+0.1% NH₄OH; (loading pump 4 ml/min MeCN).

¹H NMR (600 MHz, DMSO-d₆) δ (ppm) 1.02-1.14 (m, 6H), 1.32-1.41 (m, 1H), 1.65-1.73 (m, 1H), 1.82-1.91 (m, 1H), 2.05-2.46 (m, 8H), 2.73-2.76 (m, 2H), 3.24-3.27 (m, 2H), 3.45-4.06 (m, 6H), 5.28-5.71 (m, 3H), 7.30-7.42 (m, 1H), 7.43-7.54 (m, 1H), 7.82-7.90 (m, 1H), 7.97-8.09 (m, 2H), 10.46-10.64 (m, 1H).

LCMS(ESI): [M]⁺ m/z: calcd 536.2; found 537.2; Rt=2.116 min.

Example 590. The Synthesis of N-(6-amino-5-ethylpyridin-3-yl)-2-((2R,5S)-5-methyl-2-(2-(4-methylpiperazin-1-yl)benzo[d]thiazol-5-yl)piperidin-1-yl)-2-oxoacetamide (Compound 1244)

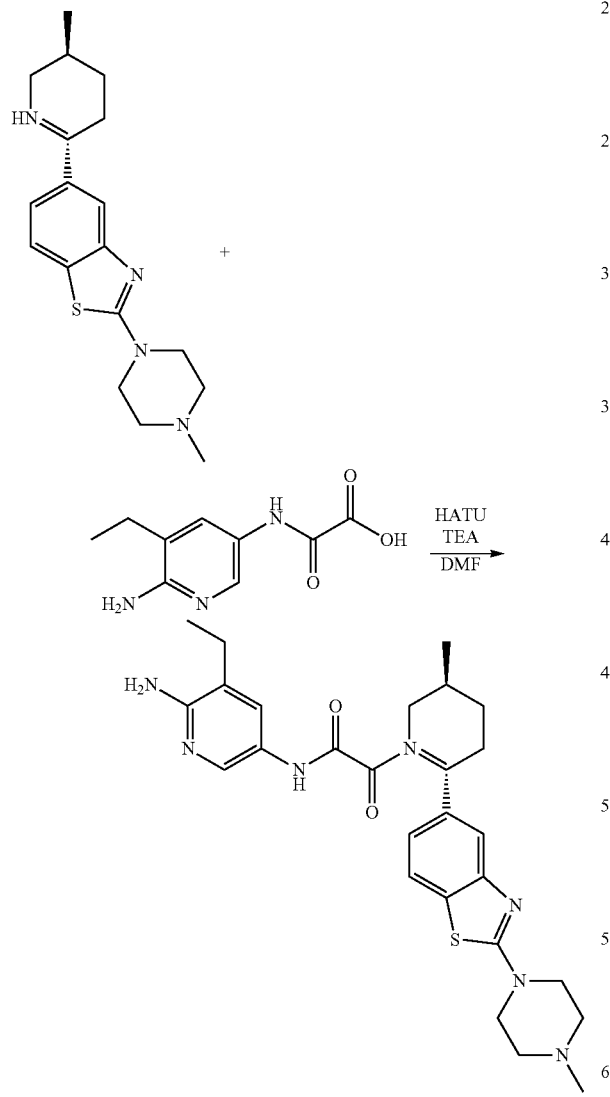

Prepared by general procedure scheme H step 6A. Yield: 42.6 mg (17.96%).

HPLC conditions: Column: YMC Triart C18 100*20 mm, 5 microM; 0-1-6 min 10-10-60% water-MeCN+0.1% NH₄OH; (loading pump 4 ml/min MeOH).

¹H NMR (600 MHz, DMSO-d₆) δ (ppm) 0.99-1.05 (m, 3H), 1.06-1.13 (m, 3H), 1.29-1.40 (m, 1H), 1.65-1.74 (m, 1H), 1.81-1.91 (m, 1H), 2.01-2.15 (m, 1H), 2.21 (s, 3H), 2.23-2.31 (m, 1H), 2.33-2.40 (m, 2H), 2.41-2.43 (m, 4H), 2.73-3.27 (m, 1H), 3.46-4.01 (m, 5H), 5.18-5.66 (m, 3H), 7.00-7.09 (m, 1H), 7.36-7.52 (m, 2H), 7.72-7.78 (m, 1H), 7.99-8.08 (m, 1H), 10.48-10.60 (m, 1H).

LCMS(ESI): [M]⁺ m/z: calcd 521.2; found 522.2; Rt=2.333 min.

Example 591. The Synthesis of N-(6-amino-5-ethylpyridin-3-yl)-2-((2R,5S)-5-methyl-2-(2-(2-methyl-2-azaspiro[3.3]heptan-6-yl)benzo[d]thiazol-5-yl)piperidin-1-yl)-2-oxoacetamide (Compound 1283)

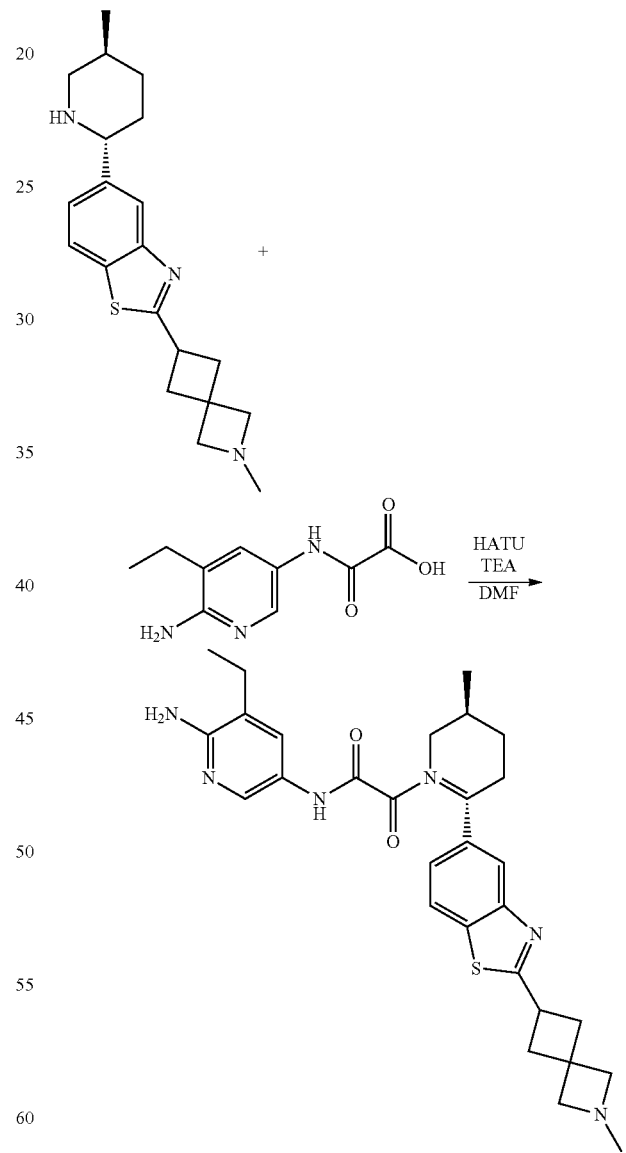

Compound 1283

Prepared by general procedure scheme H step 6A. Yield: 83 mg (26.61%).

HPLC conditions: Column: YMC Triart C18 100*20 mm, 5 microM; 0-1-5 min 20-20-60% water-MeCN+0.1% NH₄OH; (loading pump 4 ml/min MeCN).

¹H NMR (500 MHz, DMSO-d₆) δ (ppm) 1.00-1.14 (m, 6H), 1.31-1.41 (m, 1H), 1.65-1.74 (m, 1H), 1.82-1.91 (m, 1H), 2.00-2.25 (m, 5H), 2.27-2.35 (m, 2H), 2.39-2.43 (m, 2H), 2.55-2.60 (m, 2H), 3.04 (s, 2H), 3.20 (s, 2H), 3.38-4.06 (m, 3H), 5.26-5.70 (m, 3H), 7.31-7.41 (m, 1H), 7.42-7.54 (m, 1H), 7.83-7.91 (m, 1H), 7.96-8.10 (m, 2H), 10.44-10.71 (m, 1H).

LCMS(ESI): [M]⁺ m/z: calcd 532.2; found 533.2; Rt=2.002 min.

Example 592. The Synthesis of N-(6-amino-5-ethylpyridin-3-yl)-2-((2R,5S)-2-(2-((Dimethylamino)methyl)benzo[d]thiazol-5-yl)-5-methylpiperidin-1-yl)-2-oxoacetamide (Compound 1325)

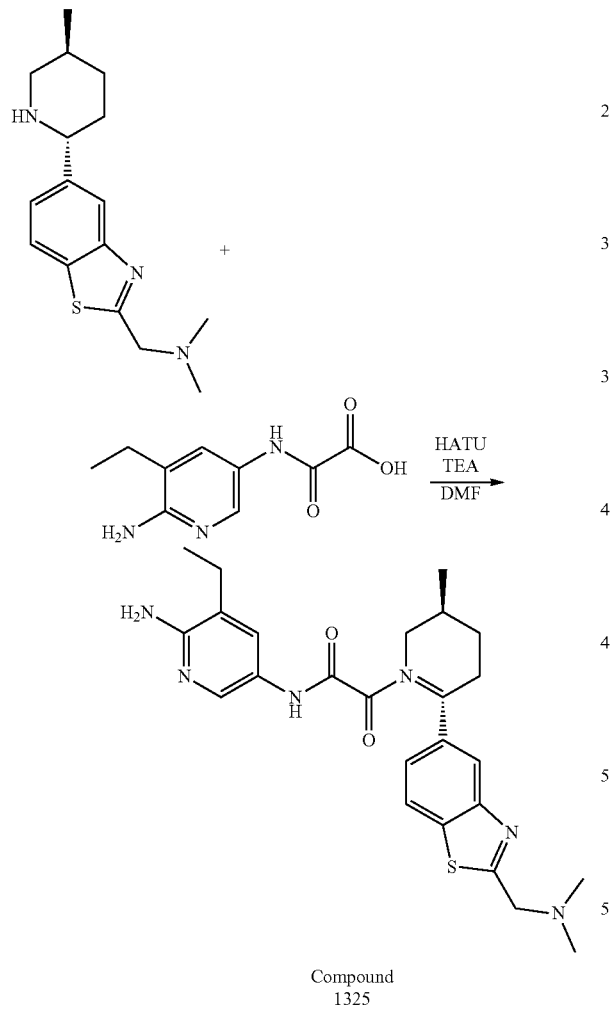

Compound 1325

Prepared by general procedure scheme H step 6A. Yield: 54.9 mg (17.20%).

HPLC conditions: Column: SunFire C18 100*19 mm, 5 microM; 2-10 min 10-50% MeCN+FA; (loading pump 4 ml/min MeCN).

¹H NMR (600 MHz, DMSO-d₆) δ (ppm) 1.01-1.14 (m, 6H), 1.31-1.41 (m, 1H), 1.65-1.74 (m, 1H), 1.83-1.93 (m, 1H), 2.05-2.22 (m, 1H), 2.25-2.36 (m, 8H), 2.39-2.42 (m, 1H), 2.77-3.27 (m, 1H), 3.47-4.05 (m, 3H), 5.24-5.62 (m, 1H), 5.62-5.72 (m, 2H), 7.32-7.55 (m, 2H), 7.82-7.92 (m, 1H), 7.97-8.12 (m, 2H), 10.49-10.62 (m, 1H).

LCMS(ESI): [M]⁺ m/z: calcd 480.2; found 481.2; Rt=1.782 min.

Example 593. The Synthesis of N-(6-amino-5-ethylpyridin-3-yl)-2-((2R,5S)-5-methyl-2-(2-(1-methylazetidin-3-yl)benzo[d]thiazol-5-yl)piperidin-1-yl)-2-oxoacetamide (Compound 1151)

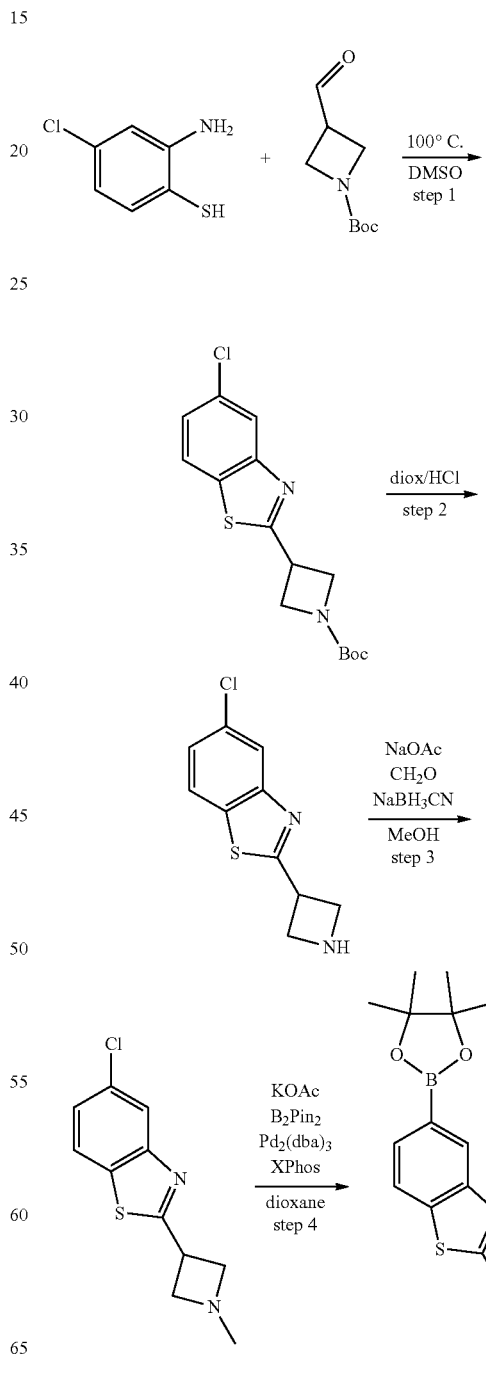

2579

-continued

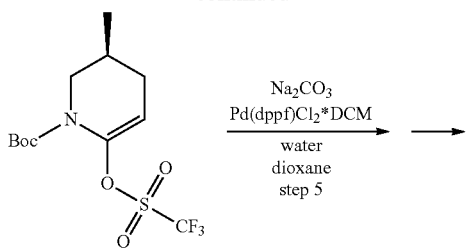

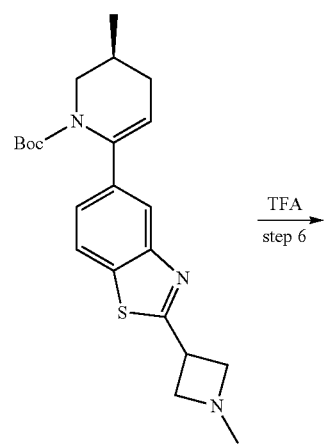

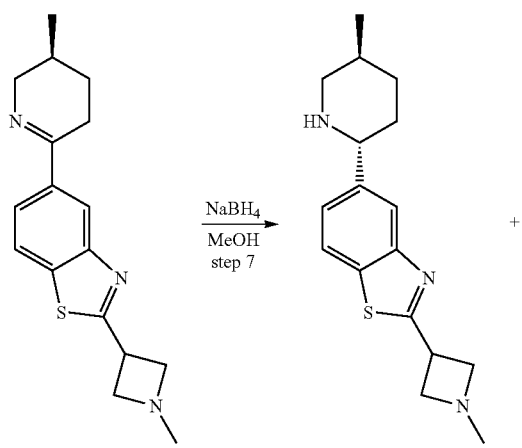

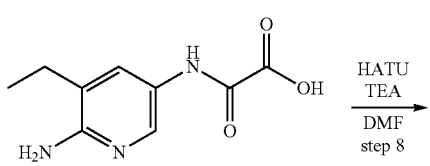

2580

-continued

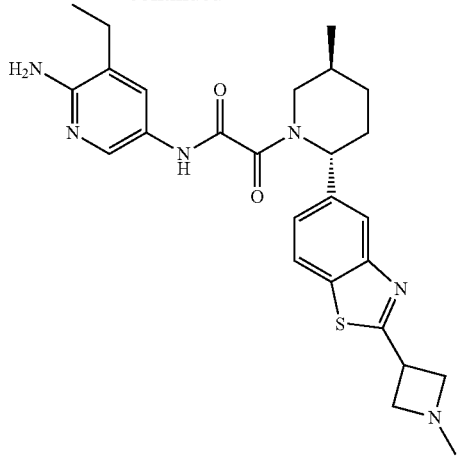

Step 1: Synthesis of tert-butyl 3-(5-chlorobenzo[d]thiazol-2-yl)azetidine-1-carboxylate Prepared by general procedure scheme H step 1B. Yield: 1.5 g (14.74%).
CC conditions: The crude product was purified by silica gel with hexane/MTBE as an eluent mixture.
LCMS(ESI): [M]⁺ m/z: calcd 324.2; found 325.2; Rt=1.591 min.

Step 2: Synthesis of 2-(Azetidin-3-yl)-5-chlorobenzo[d]thiazole tert-butyl 3-(5-chloro-1,3-benzothiazol-2-yl)azetidine-1l-carboxyl ate (2 g, 6.16 mmol) was treated with hydrogen chloride solution 4.0 M in dioxane (10.67 g, 292.55 mmol, 13.33 mL). The resulting mixture was stirred at 25° C. for 12 hr. Precipitate was filtered and additionally washed with MTBE. Then dried in vacuum to give 2-(azetidin-3-yl)-5-chloro-1,3-benzothiazole (2 g, crude, HCl).
LCMS(ESI): [M]⁺ m/z: calcd 224.2; found 225.2; Rt=0.570 min.

Step 3: Synthesis of 5-chloro-2-(1-methylazetidin-3-yl)benzo[d]thiazole

To the stirred solution of 2-(azetidin-3-yl)-5-chloro-1,3-benzothiazole (3 g, 11.49 mmol, HCl) in MeOH (24.06 mL) formaldehyde, 37% w/w aq. soln., stab. with 7-8% MeOH (1.40 g, 17.23 mmol, 1.29 mL, 37% purity) and sodium acetate, anhydrous (2.36 g, 28.72 mmol, 1.54 mL) were added. The resulting mixture was stirred for 2 hr at 25° C. Then Sodium cyan borohydride (1.44 g, 22.97 mmol) was added portion wise. The resulting mixture was stirred at 25° C. for 12 hr. Methanol was evaporated. The residue was diluted with water (50 ml) and extracted with DCM (3*25 ml). Combined organic layers were dried over Na₂SO₄. DCM was evaporated in vacuum to give 5-chloro-2-(1-methylazetidin-3-yl)-1,3-benzothiazole (2.3 g, 9.63 mmol, 83.87% yield).
LCMS(ESI): [M]⁺ m/z: calcd 238.2; found 239.2; Rt=1.608 min.

Step 4: Synthesis of 2-(1-methylazetidin-3-yl)-5-(4,4,5,5-tetramethyl-1,3,2-dioxaborolan-2-yl)benzo[d]thiazole 5-chloro-2-(1-methylazetidin-3-yl)-1,3-benzothiazole (2.3 g, 9.63 mmol), 4,4,5,5-tetramethyl-2-(4,4,5,5-tetramethyl-1,3,2-dioxaborolan-2-yl)-1,3,2-dioxaborolane (2.69 g, 10.60 mmol) and potassium acetate (1.89 g, 19.27 mmol, 1.20 mL) were mixed in dioxane (40 mL). The resulting mixture was evacuated and then backfilled with argon, this operation was repeated three times, then tris(dibenzylideneacetone)dipalladium (0) (441.11 mg, 481.70 μmol) was added under argon. The reaction mixture was stirred under argon at 90° C. for 14 hr, then cooled and concentrated under reduce pressure. The residue was purified by column chromatography to afford 2-(1-methylazetidin-3-yl)-5-(4,4,5,5-tetramethyl-1,3,2-dioxaborolan-2-yl)-1,3-benzothiazole (0.6 g, 1.82 mmol, 18.86% yield).

LCMS(ESI): [M]$^+$ m/z: calcd 330.2; found 331.2; Rt=0.942 min.

Step 5: Synthesis of (S)-tert-butyl 3-methyl-6-(2-(1-methylazetidin-3-yl)benzo[d]thiazol-5-yl)-3,4-dihydropyridine-1(2H)-carboxylate Prepared by general procedure scheme H step 3. Yield: 0.8 g of crude LCMS(ESI): [M]$^+$ m/z: calcd 399.2; found 400.2; Rt=1.232 min.

Step 6: Synthesis of (S)-5-(5-methyl-3,4,5,6-tetrahydropyridin-2-yl)-2-(1-methylazetidin-3-yl)benzo[d]thiazole Prepared by general procedure scheme H step 4. Yield: 0.5 g (83.4%).

LCMS(ESI): [M]$^+$ m/z: calcd 299.2; found 300.2; Rt=0.497 min.

Step 7: Synthesis of 2-(1-methylazetidin-3-yl)-5-((2R,5S)-5-methylpiperidin-2-yl)benzo[d]thiazole Prepared by general procedure scheme H step 5. Yield: 0.35 g of crude.

LCMS(ESI): [M]$^+$ m/z: calcd 301.2; found 302.2; Rt=0.556 min.

Step 8: The Synthesis of N-(6-amino-5-ethylpyridin-3-yl)-2-((2R,5S)-5-methyl-2-(2-(1-methylazetidin-3-yl)benzo[d]thiazol-5-yl)piperidin-1-yl)-2-oxoacetamide (Compound 1151

Prepared by general procedure scheme H step 6A. Yield: 29 mg (12.68%).

HPLC conditions: Column: YMC Triart C18 100*20 mm, 5 microM; 0-1-6 min 10-10-50% water-MeCN+0.1% NH$_4$OH, flow: 30 ml/min; (loading pump 4 ml/min MeCN)

$^1$H NMR (600 MHz, DMSO-d$_6$) δ (ppm) 1.01-1.15 (m, 6H), 1.30-1.41 (m, 1H), 1.64-1.75 (m, 1H), 1.81-1.91 (m, 1H), 2.05-2.21 (m, 1H), 2.22-2.32 (m, 4H), 2.32-2.36 (m, 1H), 2.39-2.42 (m, 1H), 2.76-3.27 (m, 1H), 3.32-3.36 (m, 2H), 3.46-4.09 (m, 4H), 5.24-5.72 (m, 3H), 7.33-7.55 (m, 2H), 7.84-7.92 (m, 1H), 7.96-8.11 (m, 2H), 10.50-10.65 (m, 1H).

LCMS(ESI): [M]$^+$ m/z: calcd 492.2; found 493.2; Rt=2.240 min.

Example 594. The Synthesis of N-(6-amino-5-ethylpyridin-3-yl)-2-((2R,5S)-5-methyl-2-(2-(tetrahydro-2H-pyran-4-yl)benzo[d]thiazol-5-yl)piperidin-1-yl)-2-oxoacetamide (Compound 1231)

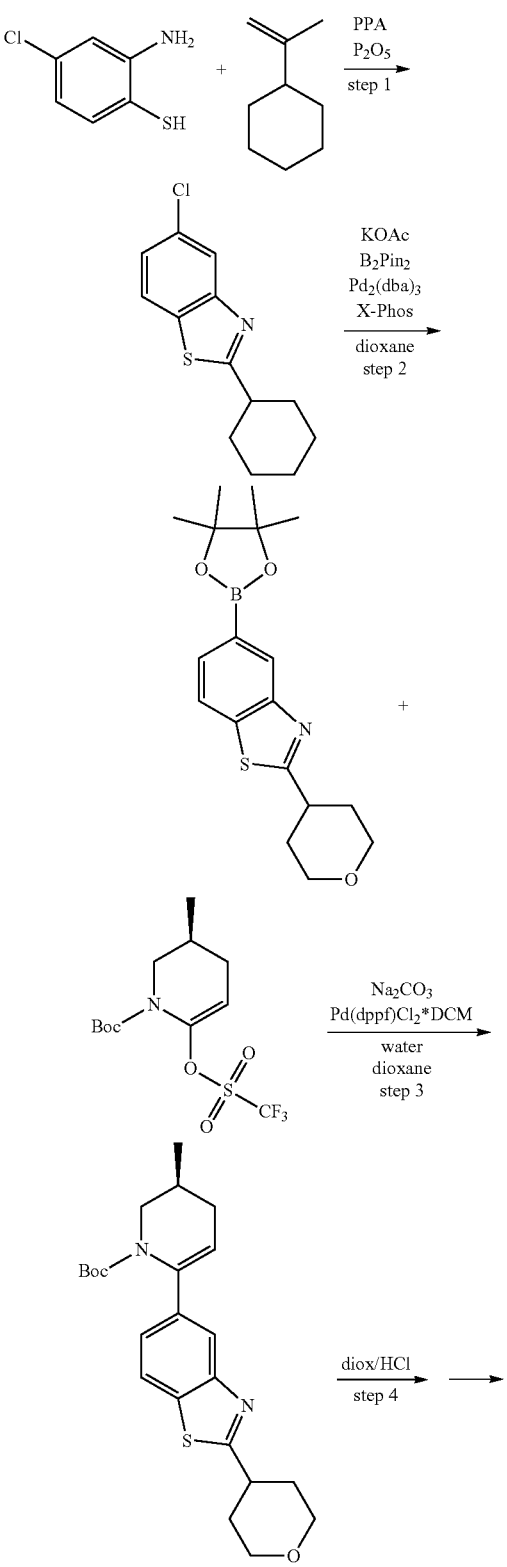

2583
-continued

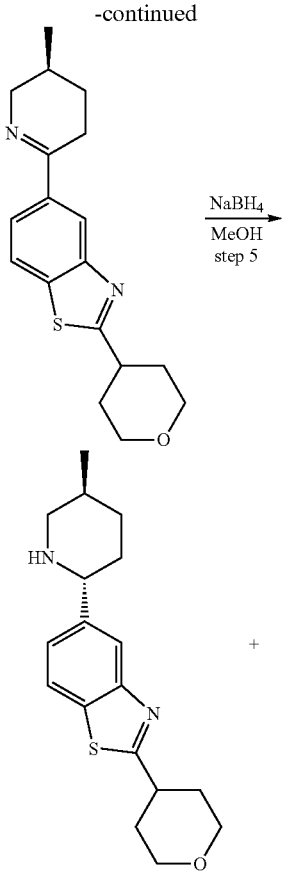

2584

Step 1: Synthesis of 5-chloro-2-(tetrahydro-2H Pyran-4 yl)benzo[d]thiazole

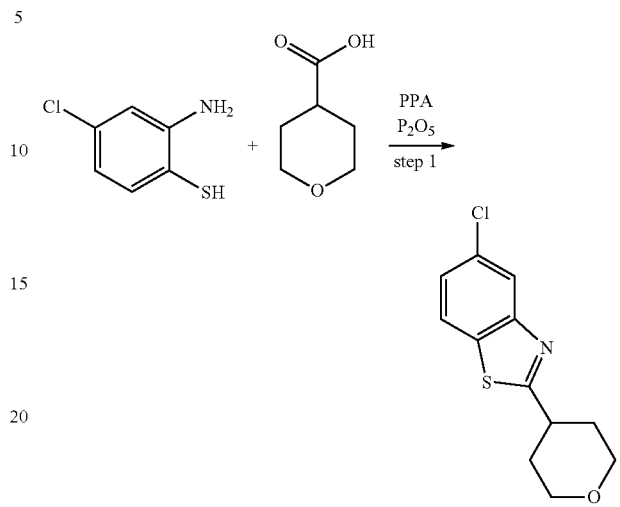

Prepared by general procedure scheme H step 1A. Yield: 1.3 g (81.78%).

LCMS(ESI): [M]$^+$ m/z: calcd 253.2; found 254.2; Rt=1.258 min.

Step 2: Synthesis of 2-(tetrahydro-2H-pyran-4-yl)-5-(4,4,5,5-tetramethyl-1,3,2-dioxaborolan-2-yl) benzo[d]thiazole

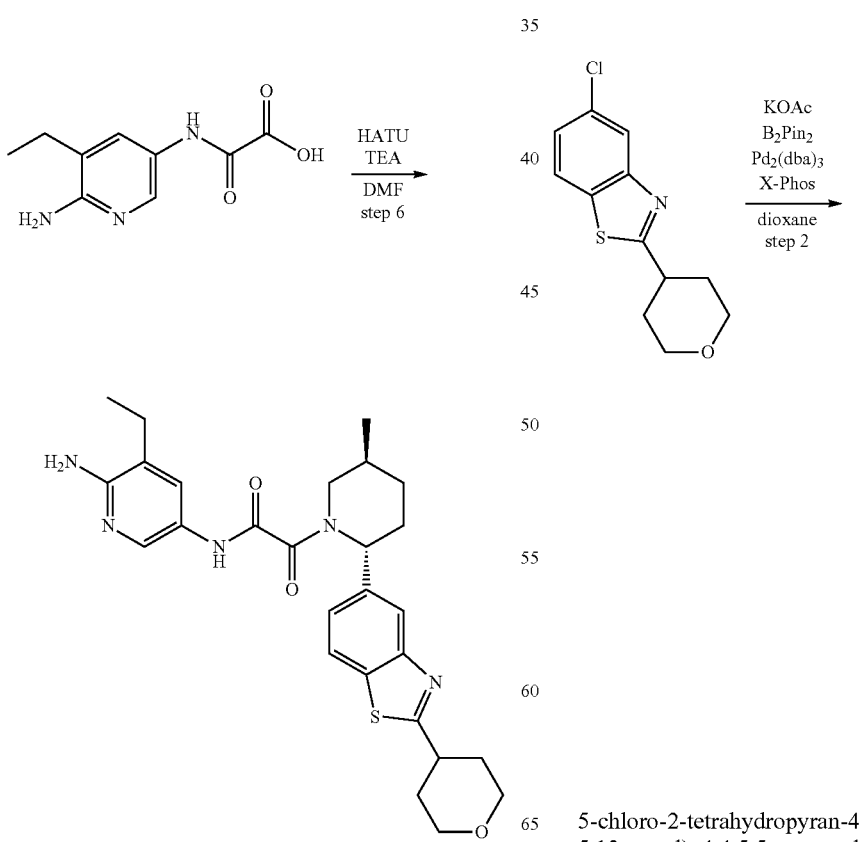

5-chloro-2-tetrahydropyran-4-yl-1,3-benzothiazole (1.3 g, 5.12 mmol), 4,4,5,5-tetramethyl-2-(4,4,5,5-tetramethyl-1,3,2-dioxaborolan-2-yl)-1,3,2-dioxaborolane (1.30 g, 5.12 mmol), tris(dibenzylideneacetone)dipalladium (0) (703.71 mg, 768.48 µmol) and dicyclohexyl-[2-(2,4,6-triisopropylphenyl)phenyl]phosphane (293.08 mg, 614.78 µmol) were mixed in dioxane (40 mL). The resulting mixture was evacuated and then backfilled with argon, this operation was repeated three times. Potassium acetate (1.01 g, 10.25 mmol, 640.51 µL) was added and the reaction mixture was stirred under argon at 100° C. for 12 hr. Then the reaction mixture was cooled and filtered through thin pad of silica. The filter cake was washed with dioxane (2*10 ml) and discarded. Obtained crude 2-tetrahydropyran-4-yl-5-(4,4,5,5-tetramethyl-1,3,2-dioxaborolan-2-yl)-1,3-benzothiazole (1.72 g, 4.98 mmol, 97.24% yield) was used in the next step without purification.

LCMS(ESI): [M]$^+$ m/z: calcd 345.2; found 346.2; Rt=1.607 min.

Step 3: Synthesis of (S)-tert-butyl 3-methyl-6-(2-(tetrahydro-2H-pyran-4-yl)benzo[d]thiazol-5-yl)-3,4-dihydropyridine-1(2H)-carboxylate

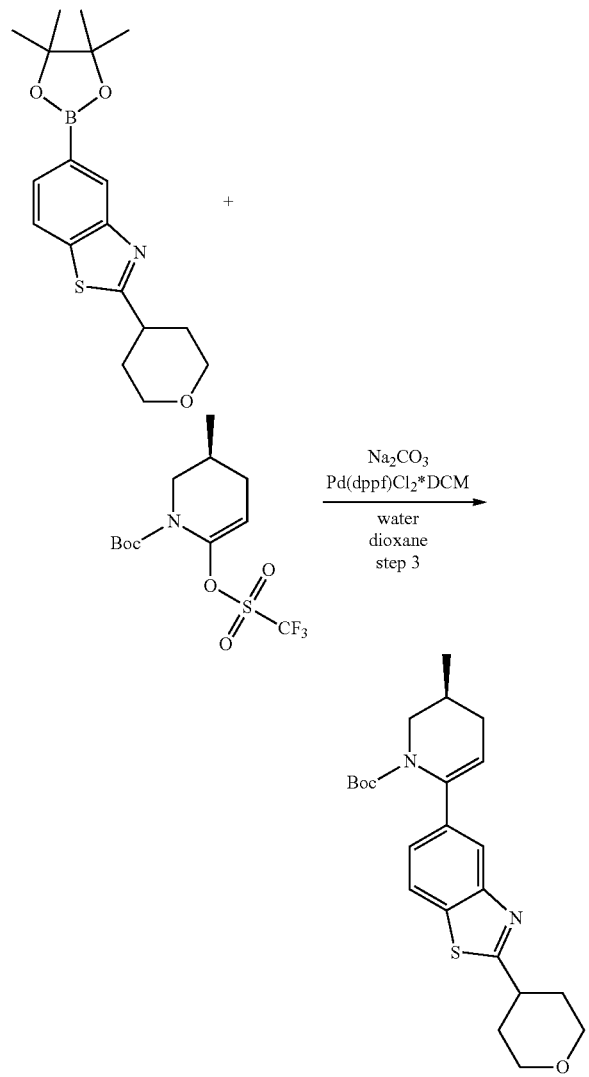

Prepared by general procedure scheme H step 3. Yield: 1.14 g of crude.

LCMS(ESI): [M]$^+$ m/z: calcd 414.2; found 415.2; Rt=1.540 min.

Step 4: Synthesis of (S)-5-(5-methyl-3,4,5,6-tetrahydropyridin-2-yl)-2-(tetrahydro-2H-pyran-4-yl)benzo[d]thiazole

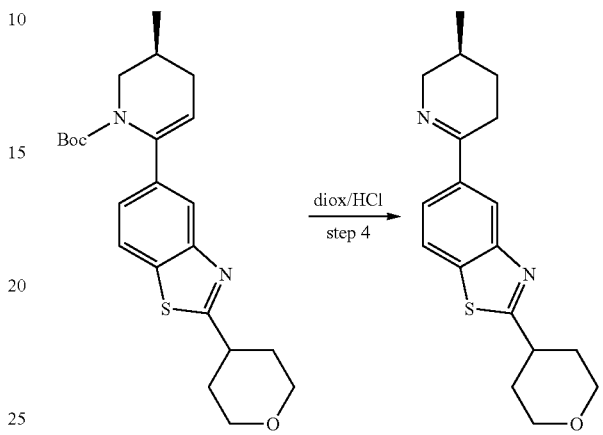

tert-butyl(3S)-3-methyl-6-(2-tetrahydropyran-4-yl-1,3-benzothiazol-5-yl)-3,4-dihydro-2H-pyridine-1-carboxylate (1.14 g, 2.75 mmol) was dissolved in the diox/HCl (10 mL) and the reaction mixture was stirred at 25° C. for 12 hr. After the completion the solvent was evaporated under reduced pressure, the residue was dissolved in the 10 mL of water, the aqueous solution was washed by DCM (3*20 mL). NaHCO$_3$ was added to alkaline reaction and this solution was extracted by DCM (3*30 mL). This organic phase was dried over Na$_2$SO$_4$ and evaporated under reduced pressure to give crude 5-[(3S)-3-methyl-2,3,4,5-tetrahydropyridin-6-yl]-2-tetrahydropyran-4-yl-1,3-benzothiazole (0.07 g, 222.62 µmol, 8.11% yield) that was used in the next step.

LCMS(ESI): [M]$^+$ m/z: calcd 314.2; found 315.2; Rt=0.969 min.

Step 5: Synthesis of 5-((2R,5S)-5-methylpiperidin-2-yl)-2-(tetrahydro-2H-pyran-4-yl)benzo[d]thiazole

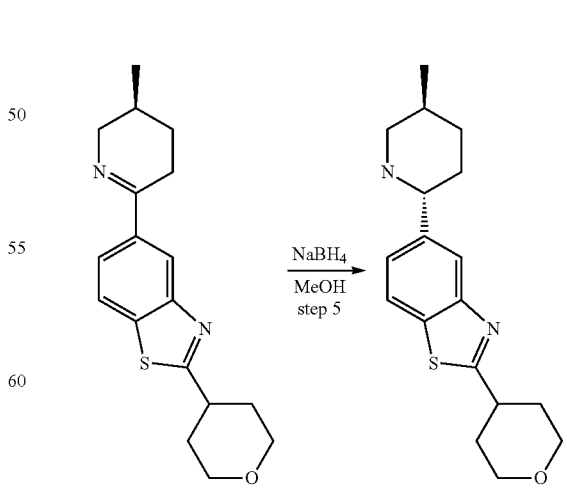

Prepared by general procedure scheme H step 5. Yield: 50 mg (67.81%).

LCMS(ESI): [M]+ m/z: calcd 316.2; found 317.2; Rt=0.895 min.

Step 6: Synthesis of N-(6-amino-5-ethylpyridin-3-yl)-2-((2R,5S)-5-methyl-2-(2-(tetrahydro-2H-pyran-4-yl)benzo[d]thiazol-5-yl)piperidin-1-yl)-2-oxoacetamide (Compound 1231

Prepared by general procedure scheme H step 6B. Yield: 20.95 mg (7.26%).
HPLC conditions: Column: XBridge C18 100*19 mm, 5 microM; 0-5 min 50-50-65% water-MeOH+0.1% NH₄OH, flow: 30 ml/min; (loading pump 4 ml/min MeOH).
$^1$H NMR (600 MHz, DMSO-$d_6$) δ (ppm) 1.01-1.05 (m, 3H), 1.06-1.15 (m, 3H), 1.29-1.41 (m, 1H), 1.66-1.75 (m, 1H), 1.79-1.91 (m, 3H), 1.96-2.12 (m, 3H), 2.17-2.36 (m, 2H), 2.39-2.42 (m, 1H), 2.76-3.22 (m, 1H), 3.36-3.42 (m, 1H), 3.46-4.06 (m, 5H), 5.26-5.71 (m, 3H), 7.34-7.53 (m, 2H), 7.86-7.93 (m, 1H), 7.97-8.09 (m, 2H), 10.55 (s, 1H).
LCMS(ESI): [M]+ m/z: calcd 507.2; found 508.2; Rt=2.996 min.

Example 595. Synthesis of N-(6-amino-5-ethylpyridin-3-yl)-2-((2R,5)-5-methyl-2-(2-(1,2,2-trimethylpiperidin-4-yl)benzo[d]thiazol-5-yl)piperidin-1-yl)-2-oxoacetamide (Compound 1125

Step 1: Synthesis of 5-chloro-2-(2,2-dimethylpiperidin-4-yl)benzo[d]thiazole

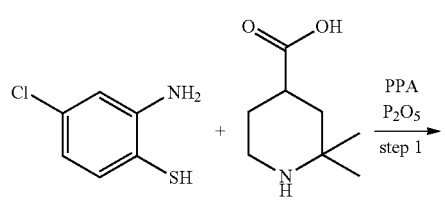

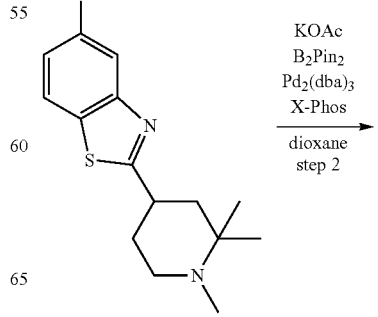

Prepared by general procedure scheme H step 1A. Yield: 6.8 g (77.52%).
CC conditions: The crude product was purified by silica gel with MTBE/MeOH as an eluent mixture.
LCMS(ESI): [M]+ m/z: calcd 280.2; found 281.2; Rt=0.859 min.

Step 2: Synthesis of 5-chloro-2-(1,2,2-trimethylpiperidin-4-yl)benzo[d]thiazole

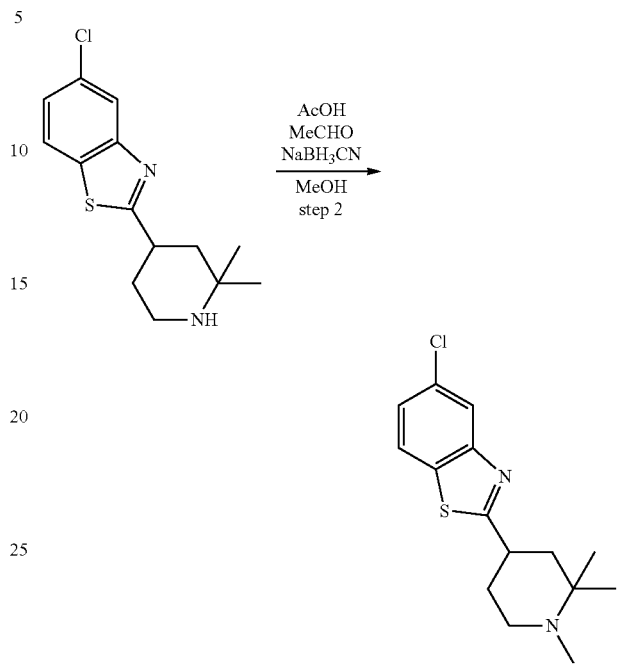

Formaldehyde, 37% w/w aq. soln., stab. with 7-8% MeOH (577.47 mg, 19.23 mmol, 533.21 µL) and acetic acid (1.15 g, 19.23 mmol, 1.10 mL) were added to the solution of 5-chloro-2-(2,2-dimethyl-4-piperidyl)-1,3-benzothiazole (2.7 g, 9.61 mmol) in MeOH (60 mL). Resulting mixture was stirred at 20° C. for 1 hr before sodium cyan borohydride (1.21 g, 19.23 mmol) was added thereto. After that, stirring was continued for 16 hr. Then, solvent was removed under reduced pressure and residue was partitioned between 10% aq. K₂CO₃ solution (20 ml) and DCM (40 ml). Organic layer was separated, dried over solid K₂CO₃ and concentrated under reduced pressure, leaving 5-chloro-2-(1,2,2-trimethyl-4-piperidyl)-1,3-benzothiazole (2.7 g, 9.16 mmol, 95.24% yield).
LCMS(ESI): [M]+ m/z: calcd 294.2; found 295.2; Rt=1.019 min.

Step 3: Synthesis of 5-(4,4,5,5-tetramethyl-1,3,2-dioxaborolan-2-yl)-2-(1,2,2-trimethylpiperidin-4-yl)benzo[d]thiazole

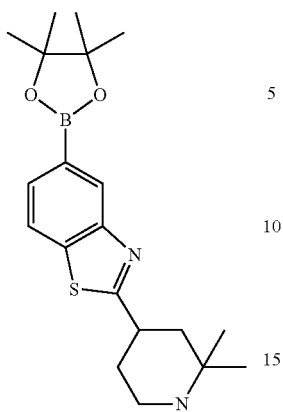

5-chloro-2-(1,2,2-trimethyl-4-piperidyl)-1,3-benzothiazole (2.7 g, 9.16 mmol), 4,4,5,5-tetramethyl-2-(4,4,5,5-tetramethyl-1,3,2-dioxaborolan-2-yl)-1,3,2-dioxaborolane (2.67 g, 10.53 mmol) and potassium acetate (1.80 g, 18.31 mmol, 1.14 mL) were mixed together in dioxane (50 mL). Reaction flask was evacuated and refilled with argon 3 times. Then, XPhos (873.10 mg, 1.83 mmol) and tris(dibenzylideneacetone)dipalladium (0) (419.28 mg, 457.87 μmol) were added under stream of argon. Resulting mixture was stirred at 100° C. for 16 hr. Then, it was concentrated under reduced pressure and residue was purified by gradient column chromatography (SiO$_2$, MTBE/MeOH), affording 5-(4,4,5,5-tetramethyl-1,3,2-dioxaborolan-2-yl)-2-(1,2,2-trimethyl-4-piperidyl)-1,3-benzothiazole (1.96 g, 5.07 mmol, 55.40% yield).

LCMS(ESI): [M]$^+$ m/z: calcd 386.2; found 387.2; Rt=1.101 min.

Step 4: Synthesis of (3S)-tert-butyl 3-methyl-6-(2-(1,2,2-trimethylpiperidin-4-yl)benzo[d]thiazol-5-yl)-3,4-dihydropyridine-1(2H)-carboxylate

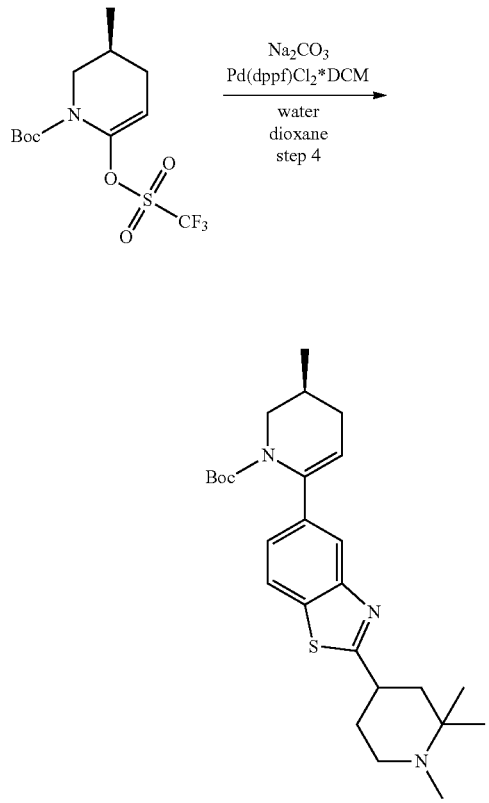

Prepared by general procedure scheme H step 3. Yield: 2.5 g of crude.

LCMS(ESI): [M]$^+$ m/z: calcd 455.2; found 456.2; Rt=1.357 min.

Step 5: Synthesis of 5-((S)-5-methyl-3,4,5,6-tetrahydropyridin-2-yl)-2-(1,2,2-trimethylpiperidin-4-yl)benzo[d]thiazole

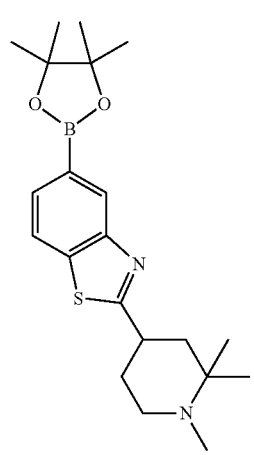

+

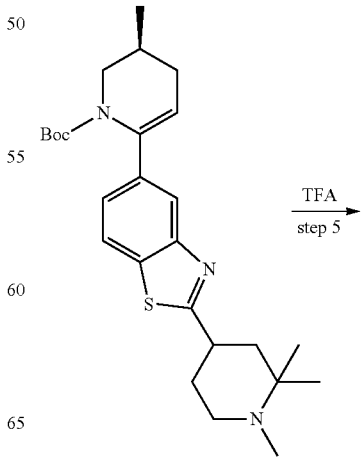

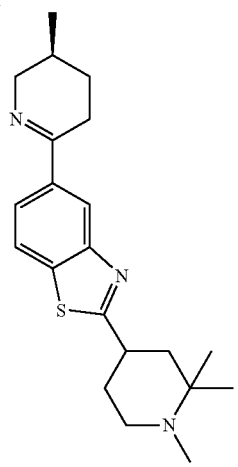

Prepared by general procedure scheme H step 4. Yield: 1.6 g of crude.
LCMS(ESI): [M]+ m/z: calcd 355.2; found 356.2; Rt=0.716 min.

Step 6: Synthesis of 5-((2R,5S)-5-methylpiperidin-2-yl)-2-(1,2,2-trimethylpiperidin-4-yl)benzo[d]thiazole

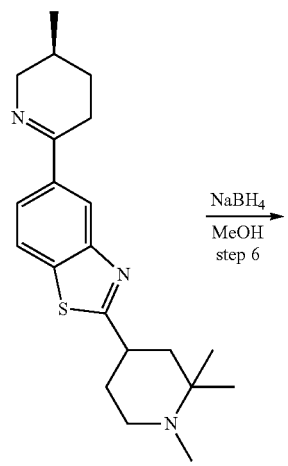

NaBH₄
MeOH
step 6

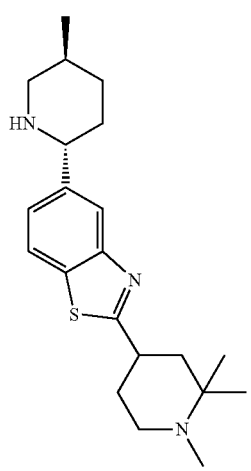

Prepared by general procedure scheme H step 5. Yield: 1.2 g (74.58%).
LCMS(ESI): [M]+ m/z: calcd 357.2; found 358.2; Rt=0.715 min.

Step 7: Synthesis of N-(6-amino-5-ethylpyridin-3-yl)-2-((2R,5S)-5-methyl-2-(2-(1,2,2-trimethylpiperidin-4-yl)benzo[d]thiazol-5-yl)piperidin-1-yl)-2-oxoacetamide (Compound 1125)

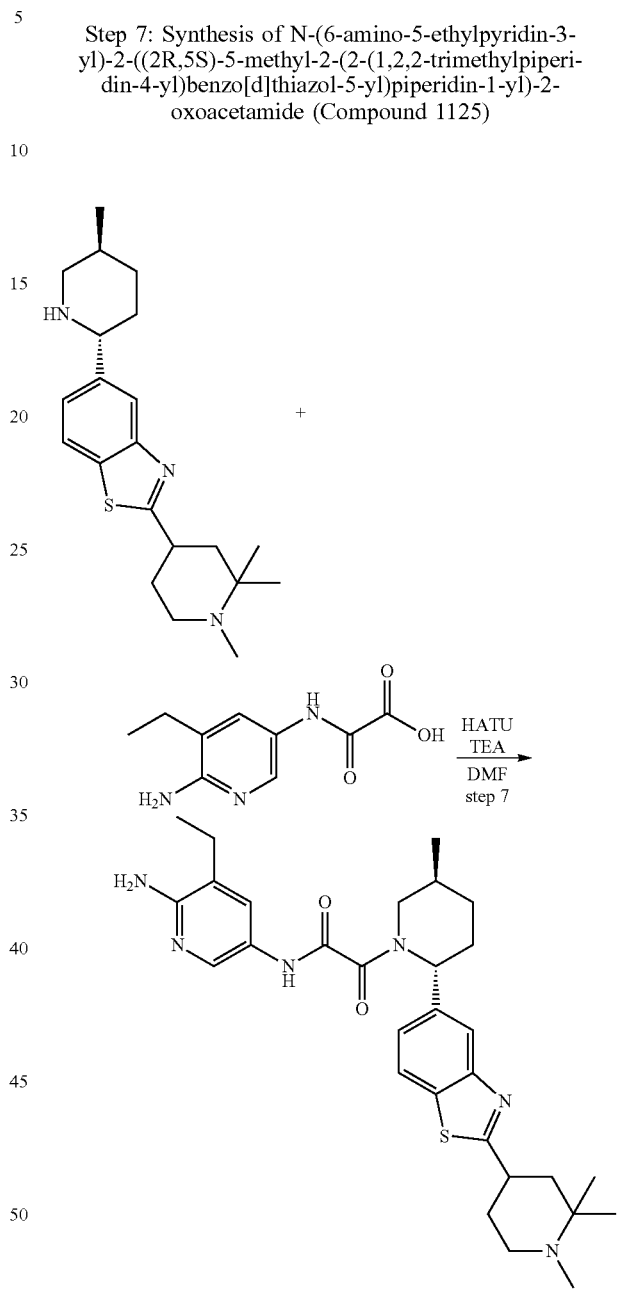

Prepared by general procedure scheme H step 6A. Yield: 94 mg (24.65%).
HPLC conditions: Column: YMC Triart C18 100*20 mm, 5 microM; 0-1-5 min 50-50-90% water-MeOH+0.1% NH₄OH, flow: 30 ml/min; (loading pump 4 ml/min MeOH).
$^1$H NMR (600 MHz, DMSO-d$_6$) δ (ppm) 0.88-1.00 (m, 4H), 1.00-1.08 (m, 4H), 1.09-1.14 (m, 5H), 1.29-1.42 (m, 1H), 1.62 (t, 1H), 1.67-1.76 (m, 2H), 1.82-1.90 (m, 2H), 1.99-2.13 (m, 2H), 2.15 (s, 3H), 2.17-2.36 (m, 2H), 2.39-2.42 (m, 1H), 2.54-2.63 (m, 2H), 2.74-3.27 (m, 1H), 3.46-4.07 (m, 1H), 5.23-5.71 (m, 3H), 7.31-7.42 (m, 1H), 7.42-7.52 (m, 1H), 7.83-7.89 (m, 1H), 7.95-8.11 (m, 2H), 10.43-10.66 (m, 1H).

LCMS(ESI): [M]⁺ m/z: calcd 548.2; found 549.2; Rt=2.034 min.

Example 596. The Synthesis of N-(6-amino-5-ethylpyridin-3-yl)-2-((2R,5S)-2-(2-(1-ethylpiperidin-4-yl)benzo[d]thiazol-5-yl)-5-methylpiperidin-1-yl)-2-oxoacetamide (Compound 1252)

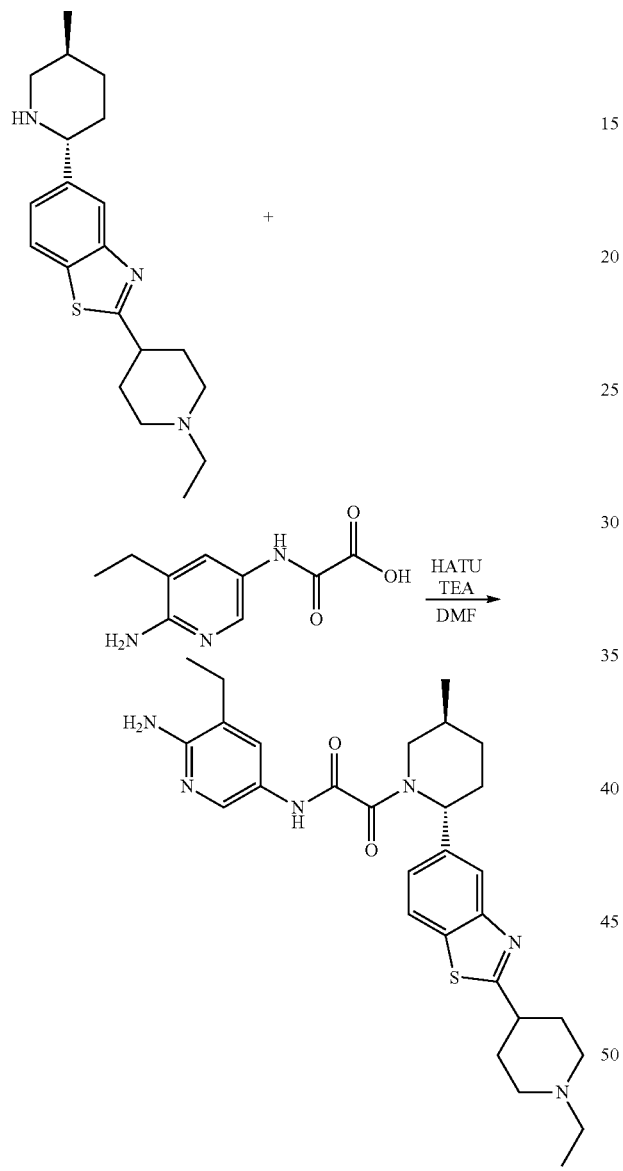

Prepared by general procedure scheme H step 6A. Yield: 93 mg (49.79%).

HPLC conditions: Column: XBridge C18 100*19 mm, 5 microM; 0-5 min 45-90% water-MeOH+0.1% NH₄OH; (loading pump 4 ml/min MeOH).

¹H NMR (600 MHz, DMSO-d₆) δ (ppm) 0.98-1.13 (m, 9H), 1.31-1.41 (m, 1H), 1.66-1.80 (m, 3H), 1.82-1.92 (m, 1H), 2.00-2.10 (m, 5H), 2.31-2.36 (m, 3H), 2.41 (q, 1H), 2.74-3.28 (m, 5H), 3.43-4.09 (m, 1H), 5.21-5.72 (m, 3H), 7.31-7.43 (m, 1H), 7.43-7.56 (m, 1H), 7.82-7.95 (m, 1H), 7.98-8.10 (m, 2H), 10.50-10.64 (m, 1H).

LCMS(ESI): [M]⁺ m/z: calcd 534.2; found 535.2; Rt=1.967 min.

Example 597. Synthesis of N-(6-amino-5-ethylpyridin-3-yl)-2-((2R,5S)-5-methyl-2-(2-(1,2,2,6,6-Pentamethylpiperidin-4-yl)benzo[d]thiazol-5-yl)piperidin-1-yl)-2-oxoacetamide (Compound 1340)

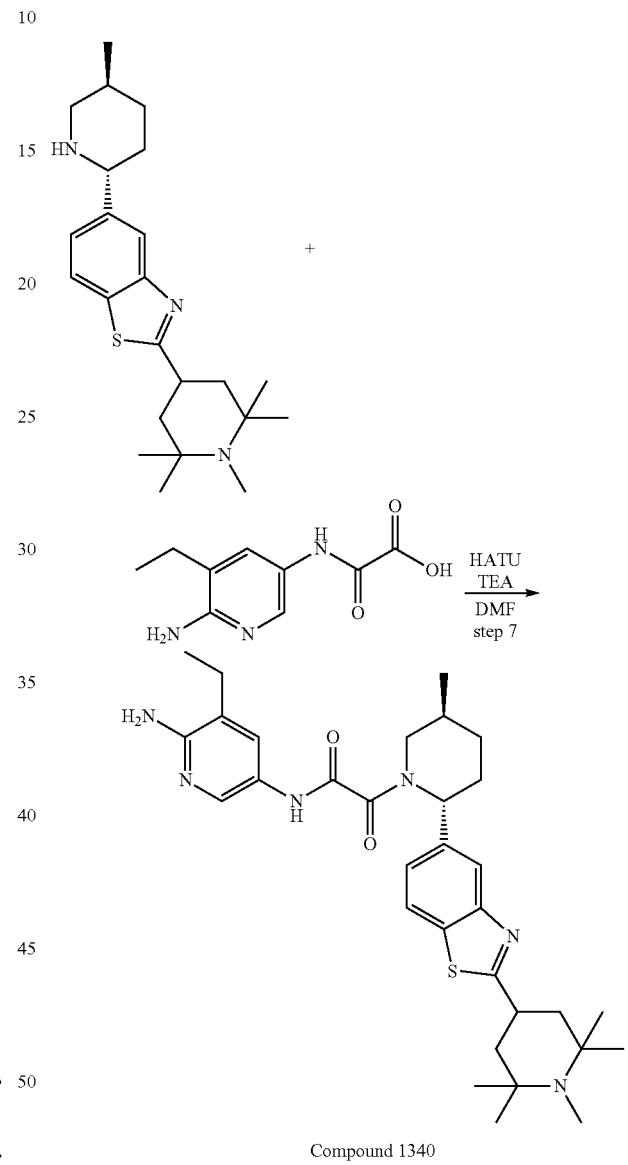

Compound 1340

Prepared by general procedure scheme H step 6A. Yield: 83 mg (28.75%).

HPLC conditions: Column: YMC Triart C18 100*20 mm, 5 microM; 0-1-6 min 50-50-90% water-MeOH+0.1% NH₄OH, flow: 30 ml/min; (loading pump 4 ml/min MeOH).

¹H NMR (600 MHz, DMSO-d₆) δ (ppm) 0.99-1.10 (m, 11H), 1.11-1.15 (m, 8H), 1.28-1.40 (m, 1H), 1.60-1.75 (m, 3H), 1.81-1.92 (m, 1H), 1.92-1.97 (m, 2H), 2.05-2.19 (m, 1H), 2.21 (s, 3H), 2.28-2.35 (m, 1H), 2.39-2.43 (m, 1H), 2.76-3.28 (m, 1H), 3.46-4.07 (m, 2H), 5.23-5.73 (m, 3H), 7.32-7.43 (m, 1H), 7.43-7.53 (m, 1H), 7.85-7.93 (m, 1H), 7.98-8.09 (m, 2H), 10.51-10.63 (m, 1H).

LCMS(ESI): [M]+ m/z: calcd 576.2; found 577.2; Rt=2.156 min.
Example 598. Synthesis of N-(6-amino-5-ethylpyridin-3-yl)-2-((2R,5S)-5-methyl-2-(2-(4-methylmorpholin-2-yl)benzo[d]thiazol-5-yl)piperidin-1-yl)-2-oxoacetamide (Compound 1275)
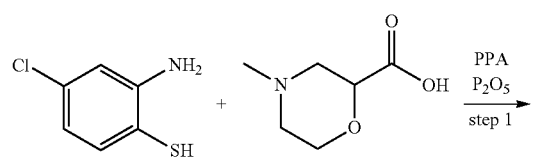
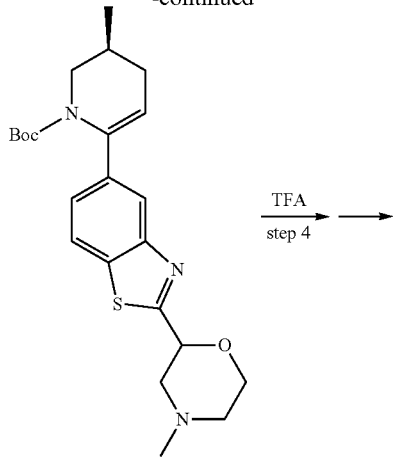
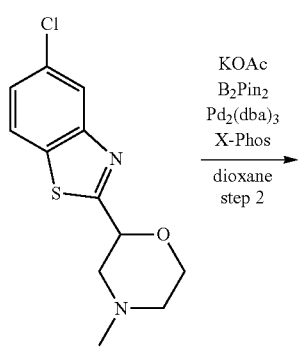
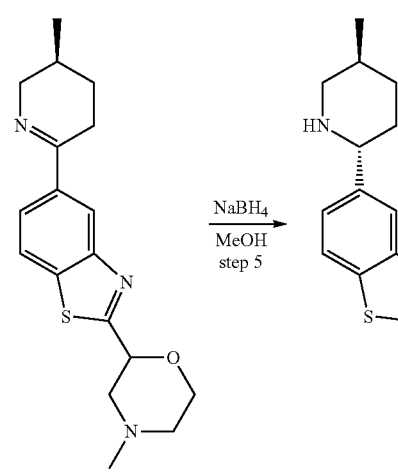
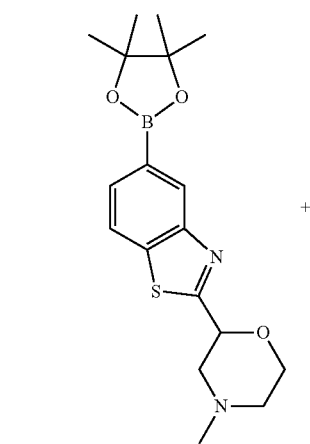
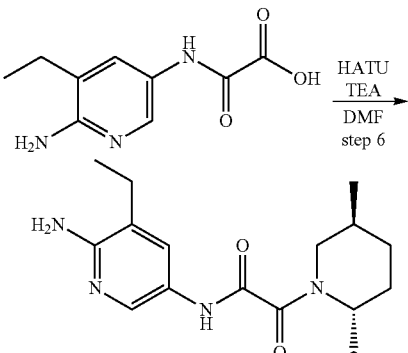
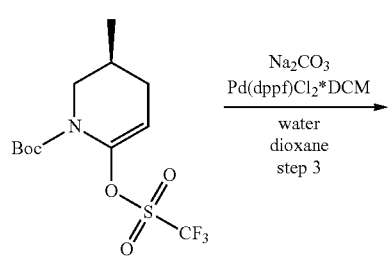
Compound 1275

Step 1: Synthesis of 2-(5-chlorobenzo[d]thiazol-2-yl)-4-methylmorpholine

Prepared by general procedure scheme H step 1A. Yield: 11.5 g of crude.
LCMS(ESI): [M]+ m/z: calcd 268.2; found 269.2; Rt=0.966 min.

Step 2: Synthesis of 4-methyl-2-(5-(4,4,5,5-tetramethyl-1,3,2-dioxaborolan-2-yl)benzo[d]thiazol-2-yl)morpholine 2-(5-chloro-1,3-benzothiazol-2-yl)-4-methyl-morpholine (11.5 g, 42.79 mmol), 4,4,5,5-tetramethyl-2-(4,4,5,5-tetramethyl-1,3,2-dioxaborolan-2-yl)-1,3,2-dioxaborolane (11.95 g, 47.07 mmol) and potassium acetate (8.40 g, 85.58 mmol, 5.35 mL) were mixed in dioxane (150 mL). The resulting mixture was evacuated and then backfilled with argon, this operation was repeated three times, then tris(dibenzylideneacetone)dipalladium (0) (1.57 g, 1.71 mmol) and XPhos (3.26 g, 6.85 mmol) was added under argon. The reaction mixture was stirred under argon at 95° C. for 18 hr, then cooled, filtered and concentrated under reduce pressure. The residue was purified by gradient chromatography (MTBE-MeOH) to give 4-methyl-2-[5-(4,4,5,5-tetramethyl-1,3,2-dioxaborolan-2-yl)-1,3-benzothiazol-2-yl]morpholine (11 g, 30.53 mmol, 71.36% yield).
LCMS(ESI): [M]+ m/z: calcd 360.2; found 361.2; Rt=1.012 min.

Step 3: Synthesis of (3S)-tert-butyl 3-methyl-6-(2-(4-methylmorpholin-2-yl)benzo[d]thiazol-5-yl)-3,4-dihydropyridine-1(2H)-carboxylate Prepared by general procedure scheme H step 3. Yield: 3 g of crude.
LCMS(ESI): [M]+ m/z: calcd 429.2; found 430.2; Rt=1.232 min.

Step 4: Synthesis of 4-methyl-2-(5-((S)-5-methyl-3,4,5,6-tetrahydropyridin-2-yl)benzo[d]thiazol-2-yl)morpholine Prepared by general procedure scheme H step 4. Yield: 1.3 g of crude.
LCMS(ESI): [M]+ m/z: calcd 329.2; found 330.2; Rt=0.673 min.

Step 5: Synthesis of 4-methyl-2-(5-((2R,5S)-5-methylpiperidin-2-yl)benzo[d]thiazol-2-yl)morpholine Prepared by general procedure scheme H step 5. Yield: 0.9 g of crude.
LCMS(ESI): [M]+ m/z: calcd 331.2; found 332.2; Rt=0.695 min.

Step 6: Synthesis of N-(6-amino-5-ethylpyridin-3-yl)-2-((2R,5S)-5-methyl-2-(2-(4-methylmorpholin-2-yl)benzo[d]thiazol-5-yl)piperidin-1-yl)-2-oxoacetamide (Compound 1275

Prepared by general procedure scheme H step 6A. Yield: 35 mg (8.88%).
HPLC conditions: Column: XBridge C18 100*19 mm, 5 microM; 0-1-6 min 10-10-60% water-MeCN+0.1% NH4OH, flow: 30 ml/min; (loading pump 4 ml/min MeOH).

$^1$H NMR (500 MHz, DMSO-d$_6$) δ (ppm) 1.00-1.05 (m, 3H), 1.06-1.16 (m, 3H), 1.66-1.76 (m, 1H), 1.81-1.89 (m, 1H), 2.01-2.22 (m, 4H), 2.24 (s, 3H), 2.27-2.35 (m, 2H), 2.38-2.42 (m, 2H), 2.67-2.78 (m, 1H), 3.15-3.27 (m, 1H), 3.43-3.52 (m, 0.6H), 3.75-3.82 (m, 1H), 3.94-4.10 (m, 1.4H), 4.86-4.96 (m, 1H), 5.27-5.62 (m, 1H), 5.64-5.73 (m, 2H), 7.36-7.44 (m, 1H), 7.45-7.54 (m, 1H), 7.87-7.95 (m, 1H), 7.96-8.08 (m, 1H), 8.08-8.16 (m, 1H), 10.46-10.62 (m, 1H).
LCMS(ESI): [M]+ m/z: calcd 522.2; found 523.2; Rt=1.536 min.

Example 599. The Synthesis of N-(6-amino-5-ethylpyridin-3-yl)-2-((2R,5S)-5-methyl-2-(2-(4-methylmorpholin-2-yl)benzo[d]thiazol-5-yl)piperidin-1-yl)-2-oxoacetamide (Compound 1134 and Compound 1203

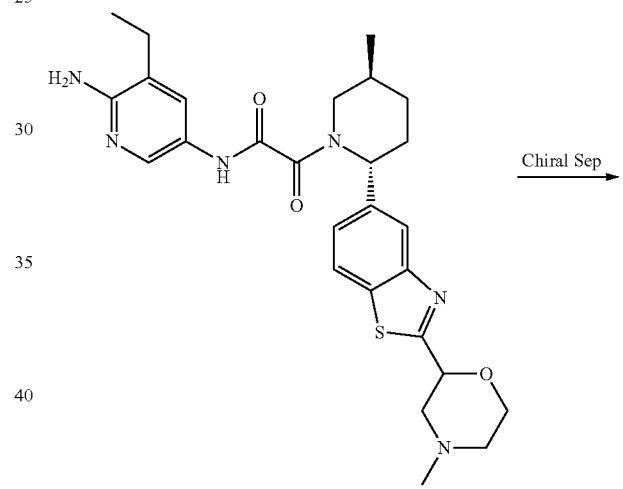

Chiral Sep →

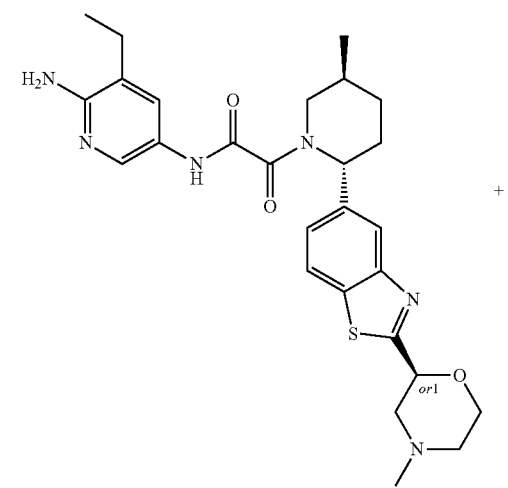

Compound 1134

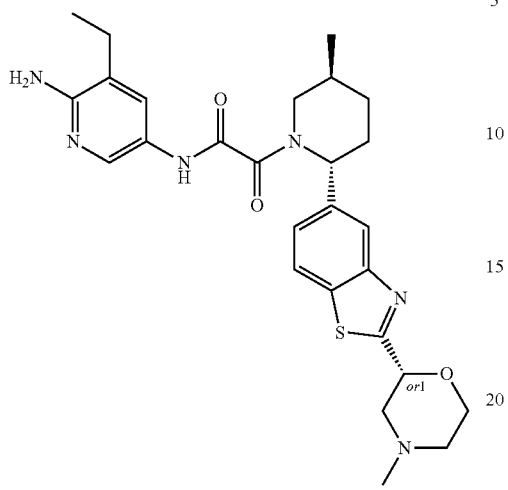

Compound 1202

Racemic N-(6-amino-5-ethyl-3-pyridyl)-2-[(2R,5S)-5-methyl-2-[2-(4-methylmorpholin-2-yl)-1,3-benzothiazol-5-yl]-1-piperidyl]-2-oxo-acetamide (74 mg, 141.58 μmol) was chiral separated (Column: Chiralpak 1C 50*20, 5-III Mobile phase: IPA-MeOH, 50-50 Flow rate: 10 mL/min) to obtain N-(6-amino-5-ethyl-3-pyridyl)-2-oxo-2-[(2R,5S)-5-methyl-2-[2-[(2S)-4-methylmorpholin-2-yl]-1,3-benzothiazol-5-yl]-1-piperidyl]acetamide (16 mg, 30.61 μmol, 43.24% yield) (RT=30.24 min) and N-(6-amino-5-ethyl-3-pyridyl)-2-oxo-2-[(2R,5S)-5-methyl-2-[2-[(2R)-4-methylmorpholin-2-yl]-1,3-benzothiazol-5-yl]-1-piperidyl]acetamide (19 mg, 36.35 mol, 51.35% yield) (RT=41.35 min).

Rel Time for Compound 1134 in analytical conditions (column: 1C, IPA-MeOH, 50-50, 0.6 mL/min as mobile phase) 22.27 min and for Compound 1202 29.82 min.

Compound 1134: Retention time: 22.27 min $^1$H NMR (600 MHz, DMSO-d$_6$) δ (ppm) 1.01-1.14 (m, 6H), 1.30-1.42 (m, 1H), 1.64-1.74 (m, 1H), 1.78-2.05 (m, 2H), 2.06-2.23 (m, 2H), 2.23-2.39 (m, 7H), 2.39-2.43 (m, 2H), 2.73-2.88 (m, 1H), 3.34-3.52 (m, 1H), 3.75-3.88 (m, 1H), 4.02-4.12 (m, 1H), 4.93-5.29 (m, 1H), 5.69-5.82 (m, 2H), 7.38-7.46 (m, 1H), 7.46-7.55 (m, 1H), 7.86-7.95 (m, 1H), 7.99-8.09 (m, 1H), 8.09-8.15 (m, 1H), 10.47-10.70 (m, 1H).

LCMS(ESI): [M+1]$^+$ m/z: calcd 522.2; found 523.2; Rt=1.949 min.

Compound 1202: Retention time: 29.82 min $^1$H NMR (600 MHz, DMSO-d$_6$) δ (ppm) 1.01-1.14 (m, 6H), 1.30-1.42 (m, 1H), 1.64-1.74 (m, 1H), 1.78-2.05 (m, 2H), 2.06-2.23 (m, 2H), 2.23-2.39 (m, 7H), 2.39-2.43 (m, 2H), 2.73-2.88 (m, 1H), 3.34-3.52 (m, 1H), 3.75-3.88 (m, 1H), 4.02-4.12 (m, 1H), 4.93-5.29 (m, 1H), 5.69-5.82 (m, 2H), 7.38-7.46 (m, 1H), 7.46-7.55 (m, 1H), 7.86-7.95 (m, 1H), 7.99-8.09 (m, 1H), 8.09-8.15 (m, 1H), 10.47-10.70 (m, 1H).

LCMS(ESI): [M+1]$^+$ m/z: calcd 522.2; found 523.2; Rt=1.951 min.

Example 600. Synthesis of N-(6-amino-5-ethylpyridin-3-yl)-2-((2R,5S)-2-(2-(3-(dimethylamino)propyl)benzo[d]thiazol-5-yl)-5-methylpiperidin-1-yl)-2-oxoacetamide (Compound 1262)

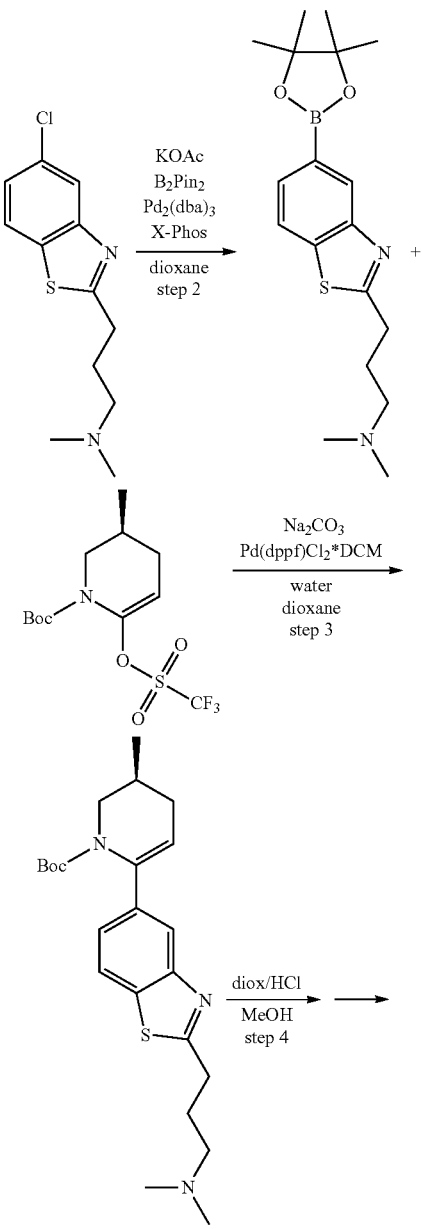

-continued

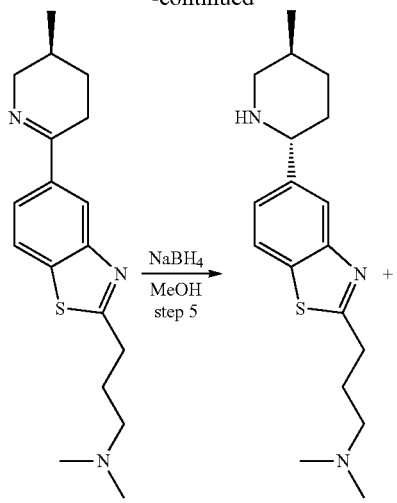

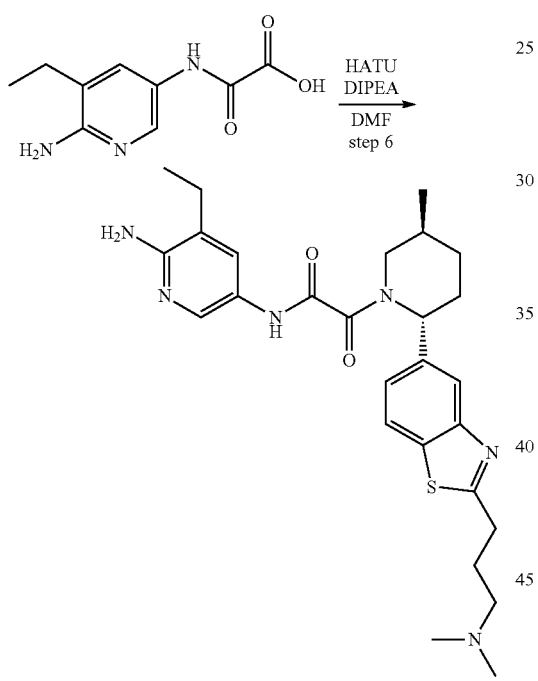

Step 1: Synthesis of 3-(5-chlorobenzo[d]thiazol-2-yl)-N,N-dimethylpropan-1-amine The stirred solution of 2-amino-4-chloro-benzenethiol (1 g, 6.26 mmol) and 4-(dimethylamino)butanoic acid (1.3 g, 7.76 mmol, HCl) in PPA (5 mL) was allowed to stir at 120° C. for 16 hr. Upon completion, the reaction mixture was quenched with water (100 mL) and neutralized by NaOH to pH=8. The aqueous phase was extracted with EtOAc (2*20 mL). The combined organic phase was dried over Na$_2$SO$_4$ and concentrated under reduced pressure. The desired product 3-(5-chloro-1,3-benzothiazol-2-yl)-N,N-dimethyl-propan-1-amine (1.2 g, 4.71 mmol, 75.19% yield) was isolated.

LCMS(ESI): [M]$^+$ m/z: calcd 254.2; found 255.2; Rt=0.909 min.

Step 2: Synthesis of N,N-dimethyl-3-(5-(4,4,5,5-tetramethyl-1,3,2-dioxaborolan-2-yl)benzo[d]thiazol-2-yl)propan-1-amine To a stirred solution of 3-(5-chloro-1,3-benzothiazol-2-yl)-N,N-dimethyl-propan-1-amine (0.6 g, 2.35 mmol) and 4,4,5,5-tetramethyl-2-(4,4,5,5-tetramethyl-1,3,2-dioxaborolan-2-yl)-1,3,2-dioxaborolane (0.6 g, 2.36 mmol) in dioxane (10 mL) were added Pd$_2$dba$_3$ (0.4 g, 436.82 µmol) and XPhos (0.4 g, 839.10 µmol). The resulting suspension was degassed with argon at 50° C. for 0.5 hr. Potassium acetate (0.5 g, 5.09 mmol, 318.47 µL) was added. The reaction mixture was stirred at 100° C. for 16 hr. Upon completion, the reaction mixture was concentrated under reduced pressure, quenched with water (20 mL), the aqueous phase was extracted with CHCl$_3$ (2*20 mL). The organic phase was extracted with 10% HCl (2*40 ml). The aqueous phase was neutralized by NaHCO$_3$ to pH=8, extracted with CHCl$_3$ (2*20 mL). The organic phase was dried over Na$_2$SO$_4$ and evaporated in vacuum. The desired product N,N-dimethyl-3-[5-(4,4,5,5-tetramethyl-1,3,2-dioxaborolan-2-yl)-1,3-benzothiazol-2-yl]propan-1-amine (0.8 g, 2.31 mmol, 98.10% yield) was isolated.

LCMS(ESI): [M]$^+$ m/z: calcd 346.2; found 347.2; Rt=0.940 min.

Step 3: Synthesis of (S)-tert-butyl 6-(2-(3-(dimethylamino)propyl)benzo[d]thiazol-5-yl)-3-methyl-3,4-dihydropyridine-1(2H)-carboxylate Prepared by general procedure scheme H step 3. Yield: 0.4 g of crude.

CC conditions: The crude product was purified by silica gel with EtOAc/MeOH as an eluent mixture.

LCMS(ESI): [M]$^+$ m/z: calcd 415.2; found 416.2; Rt=1.033 min.

Step 4: Synthesis of (S)—N,N-dimethyl-3-(5-(5-methyl-3,4,5,6-tetrahydropyridin-2-yl)benzo[d]thiazol-2-yl)propan-1-amine The stirred solution of tert-butyl (3S)-6-[2-[3-(dimethylamino)propyl]-1,3-benzothiazol-5-yl]-3-methyl-3,4-dihydro-2H-pyridine-1-carboxylate (400.00 mg, 962.49 µmol) in MeOH (10 mL) and diox/HCl (10 mL) was allowed to stir at 25° C. for 16 hr. Upon completion, the reaction mixture was evaporated, the crude product was quenched with water (20 mL) and neutralized by NaHCO$_3$ to pH=8. The aqueous phase was extracted with CHCl$_3$ (2*20 mL). The combined organic phase was dried over Na$_2$SO$_4$ and concentrated under reduced pressure. The desired product N,N-dimethyl-3-[5-[(3S)-3-methyl-2,3,4,5-tetrahydropyridin-6-yl]-1,3-benzothiazol-2-yl]propan-1-amine (0.3 g, 950.95 µmol, 98.80% yield) was isolated.

LCMS(ESI): [M]$^+$ m/z: calcd 315.2; found 316.2; Rt=0.671 min.

Step 5: Synthesis of N,N-dimethyl-3-(5-((2R,5S)-5-methylpiperidin-2-yl)benzo[d]thiazol-2-yl)propan-1-amine Prepared by general procedure scheme H step 5. Yield: 0.3 g of crude.

LCMS(ESI): [M]$^+$ m/z: calcd 317.2; found 318.2; Rt=0.754 min.

Step 6: Synthesis of N-(6-amino-5-ethylpyridin-3-yl)-2-((2R,5S)-2-(2-(3-(dimethylamino)propyl)benzo[d]thiazol-5-yl)-5-methylpiperidin-1-yl)-2-oxoacetamide (Compound 1262

Prepared by general procedure scheme H step 6B. Yield: 27 mg (5.62%).

HPLC conditions: Column: YMC Triart C18 100*20 mm, 5 microM; 0-1-6 min 30-30-80% water-MeOH+0.1% NH₄OH, flow: 30 ml/min; (loading pump 4 ml/min MeOH).

$^1$H NMR (600 MHz, DMSO-d$_6$) δ (ppm) 1.01-1.17 (m, 6H), 1.28-1.42 (m, 1H), 1.66-1.76 (m, 1H), 1.83-1.95 (m, 3H), 2.06-2.19 (m, 7H), 2.21-2.33 (m, 3H), 2.33-2.45 (m, 2H), 2.77-3.27 (m, 3H), 3.45-4.07 (m, 1H), 5.23-5.72 (m, 3H), 7.33-7.42 (m, 1H), 7.42-7.54 (m, 1H), 7.82-7.93 (m, 1H), 7.96-8.11 (m, 2H), 10.49-10.63 (m, 1H).

LCMS(ESI): [M]⁺ m/z: calcd 508.2; found 509.2; Rt=2.054 min.

Example 601. Synthesis of N-(6-amino-5-ethylpyridin-3-yl)-2-((2R,5S)-5-methyl-2-(2-(1-methylpiperidin-3-yl)benzo[d]thiazol-5-yl)piperidin-1-yl)-2-oxoacetamide (Compound 1388)

Prepared by general procedure scheme H step 6A. Yield: 32 mg (6.75%).

HPLC conditions: Column: YMC Triart C18 100*20 mm, 5 microM; 0-1-6 min 45-45-80% water-MeOH+0.1% NH₄OH, flow: 30 ml/min; (loading pump 4 ml/min MeOH).

$^1$H NMR (600 MHz, DMSO-d$_6$) δ (ppm) 1.01-1.14 (m, 6H), 1.29-1.40 (m, 1H), 1.55-1.65 (m, 2H), 1.67-1.76 (m, 2H), 1.83-1.92 (m, 1H), 2.00-2.19 (m, 3H), 2.22 (s, 3H), 2.23-2.33 (m, 2H), 2.34-2.44 (m, 2H), 2.61-3.07 (m, 4H), 3.44-4.07 (m, 1H), 5.24-5.73 (m, 3H), 7.33-7.54 (m, 2H), 7.84-7.92 (m, 1H), 7.97-8.18 (m, 2H), 10.49-10.60 (m, 1H).

LCMS(ESI): [M]⁺ m/z: calcd 520.2; found 521.2; Rt=2.114 min.

Example 602. Synthesis of N-(6-amino-5-ethylpyridin-3-yl)-2-((2R,5S)-5-methyl-2-(2-((2R,4r,6S)-1,2,6-trimethylpiperidin-4-yl)benzo[d]thiazol-5-yl)piperidin-1-yl)-2-oxoacetamide (Compound 1261)

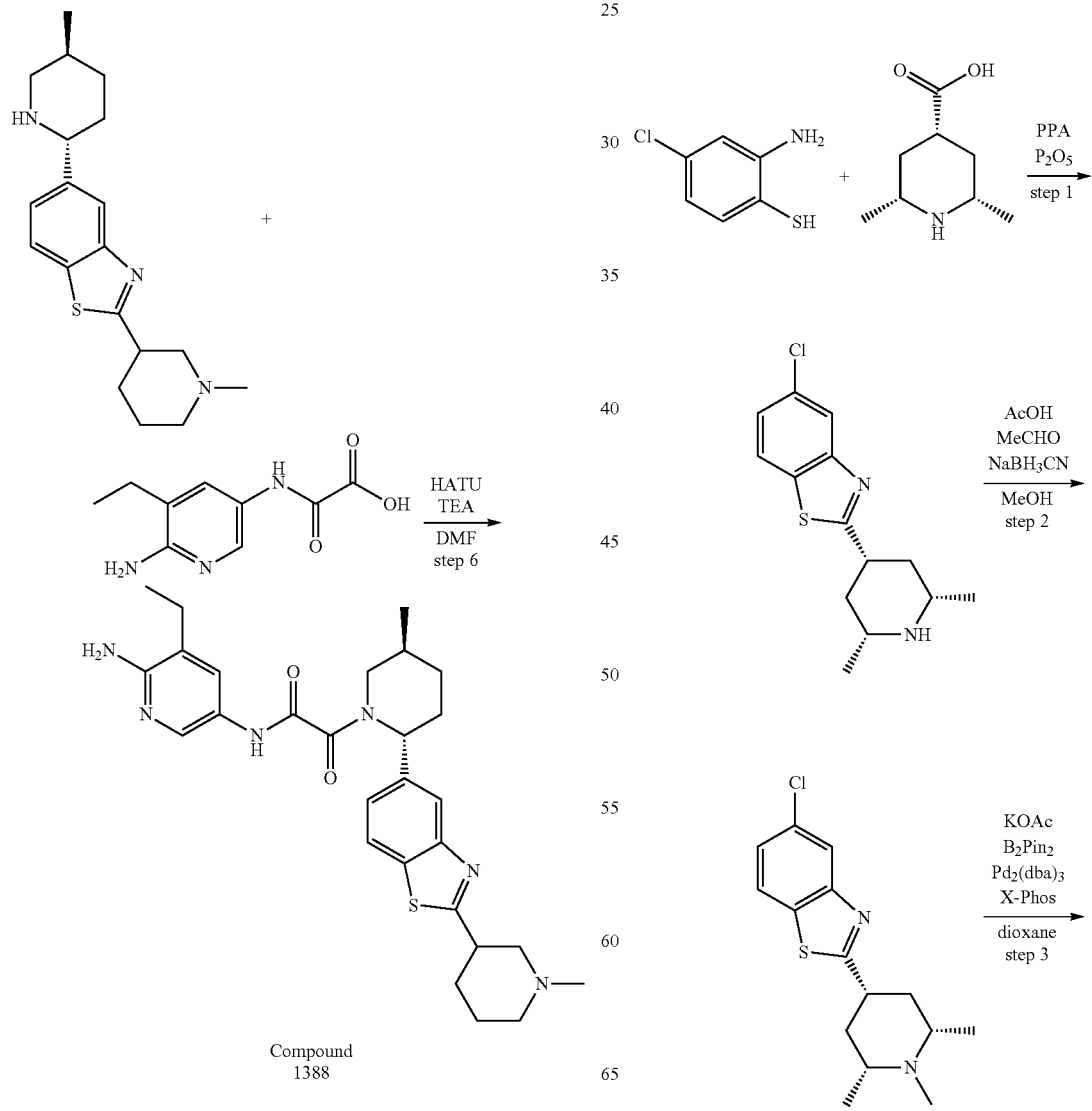

Compound 1388

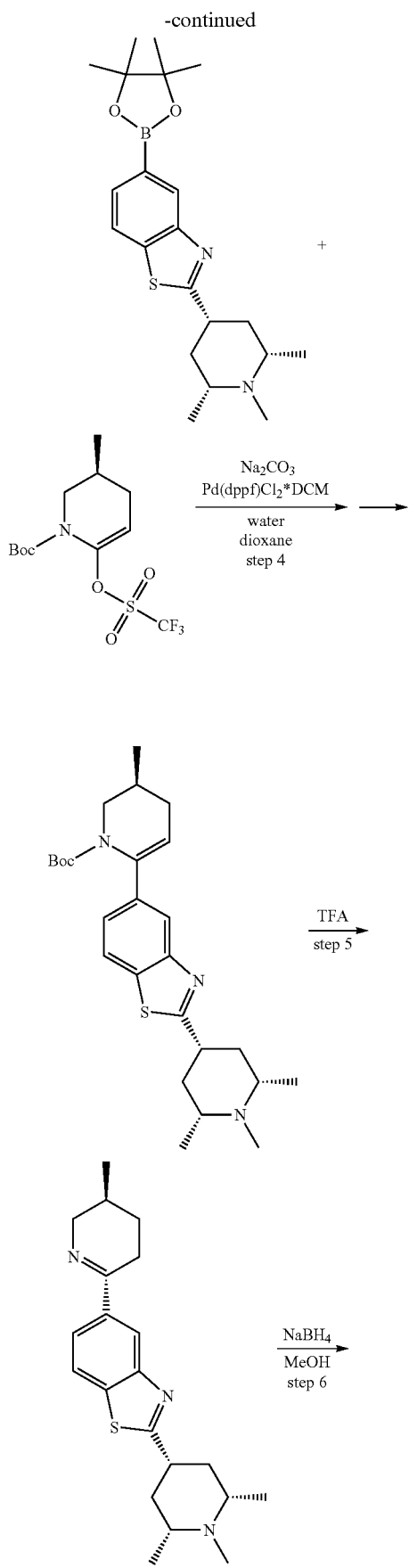

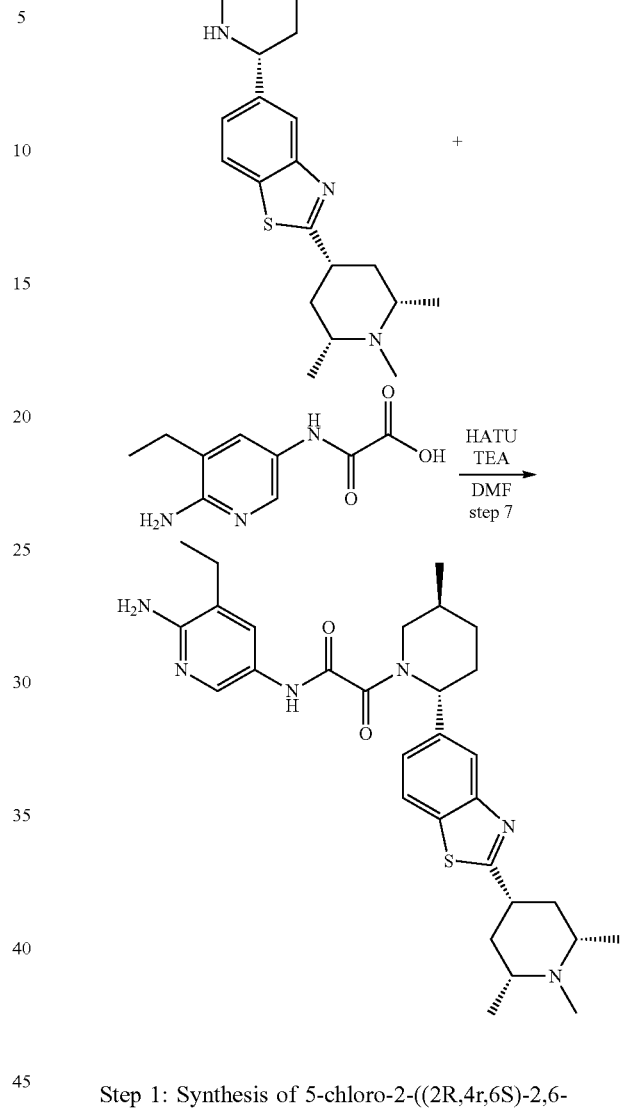

Step 1: Synthesis of 5-chloro-2-((2R,4r,6S)-2,6-dimethylpiperidin-4-yl)benzo[d]thiazole Prepared by general procedure scheme H step 1A. Yield: 5.5 g (91.96%).

LCMS(ESI): [M]+ m/z: calcd 280.2; found 281.2; Rt=1.025 min.

Step 2: Synthesis of 5-chloro-2-((2R,4r,6S)-1,2,6-trimethylpiperidin-4-yl)benzo[d]thiazole Formaldehyde, 37% w/w aq. soln., stab. with 7-8% MeOH (1.18 g, 39.17 mmol, 1.09 mL) and acetic acid (2.35 g, 39.17 mmol, 2.24 mL) were added to the solution of 5-chloro-2-[(2R,6S)-2,6-dimethyl-4-piperidyl]-1,3-benzothiazole (5.5 g, 19.59 mmol) in MeOH (80 mL). Resulting mixture was stirred at 20° C. for 1 hr before sodium cyan borohydride (2.46 g, 39.17 mmol) was added thereto. After that, stirring was continued for 16 hr. Then, solvent was removed under reduced pressure and residue was partitioned between 10% aq. $K_2CO_3$ solution (40 ml) and DCM (60 ml). Organic layer was separated, dried over solid $K_2CO_3$ and concentrated under reduced pressure, leaving 5-chloro-2-[(2R,6S)-1,2,6-trimethyl-4-piperidyl]-1,3-benzothiazole (5.8 g, crude).

LCMS(ESI): [M]+ m/z: calcd 294.2; found 295.2; Rt=1.020 min.

Step 3: Synthesis of 5-(4,4,5,5-tetramethyl-1,3,2-dioxaborolan-2-yl)-2-((2R,4r,6S)-1,2,6-trimethylpiperidin-4-yl)benzo[d]thiazole 5-chloro-2-[(2R,6S)-1,2,6-trimethyl-4-piperidyl]-1,3-benzothiazole (5.8 g, 19.67 mmol) 4,4,5,5-tetramethyl-2-(4,4,5,5-tetramethyl-1,3,2-dioxaborolan-2-yl)-1,3,2-dioxaborolane (5.74 g, 22.62 mmol) and potassium acetate (3.86 g, 39.34 mmol, 2.46 mL) were mixed together in dioxane (80 mL). Reaction flask was evacuated and refilled with argon 3 times. Then, XPhos (1.88 g, 3.93 mmol) and tris(dibenzylideneacetone)dipalladium (0) (900.68 mg, 983.58 μmol) were added under stream of argon. Resulting mixture was stirred at 100° C. for 16 hr. Then, it was concentrated under reduced pressure and residue was purified by gradient column chromatography (SiO₂, MTBE/MeOH), affording 5-(4,4,5,5-tetramethyl-1,3,2-dioxaborolan-2-yl)-2-[(2R,6S)-1,2,6-trimethyl-4-piperidyl]-1,3-benzothiazole (4.95 g, 12.81 mmol, 65.13% yield).

LCMS(ESI): [M]+ m/z: calcd 386.2; found 387.2; Rt=1.060 min.

Step 4: Synthesis of (S)-tert-butyl 3-methyl-6-(2-((2R,4r,6S)-1,2,6-trimethylpiperidin-4-yl)benzo[d]thiazol-5-yl)-3,4-dihydropyridine-1(2H)-carboxylate Prepared by general procedure scheme H step 3. Yield: 3.7 g of crude.
LCMS(ESI): [M]+ m/z: calcd 455.2; found 456.2; Rt=3.417 min.

Step 5: Synthesis of 5-((S)-5-methyl-3,4,5,6-tetrahydropyridin-2-yl)-2-((2R,4r,6S)-1,2,6-trimethylpiperidin-4-yl)benzo[d]thiazole Prepared by general procedure scheme H step 4. Yield: 1.27 g of crude.
LCMS(ESI): [M]+ m/z: calcd 355.2; found 356.2; Rt=0.696 min.

Step 6: Synthesis of 5-((2R,5S)-5-methylpiperidin-2-yl)-2-((2R,4r,6S)-1,2,6-trimethylpiperidin-4-yl)benzo[d]thiazole Prepared by general procedure scheme H step 5. Yield: 0.93 g (72.82%).
LCMS(ESI): [M]+ m/z: calcd 357.2; found 358.2; Rt=0.762 min.

Step 7: Synthesis of N-(6-amino-5-ethylpyridin-3-yl)-2-((2R,5S)-5-methyl-2-(2-((2R,4r,6S)-1,2,6-trimethylpiperidin-4-yl)benzo[d]thiazol-5-yl)piperidin-1-yl)-2-oxoacetamide (Compound 1261)

Prepared by general procedure scheme H step 6A. Yield: 42 mg (12.77%).
HPLC conditions: Column: YMC Triart C18 100*20 mm, 5 microM; 0-1-5 min 50-50-90% water-MeOH+0.1% NH₄OH, flow: 30 ml/min; (loading pump 4 ml/min MeOH). N-(6-amino-5-ethylpyridin-3-yl)-2-((2R,5S)-5-methyl-2-(2-((2R,4r,6S)-1,2,6-trimethylpiperidin-4-yl)benzo[d]thiazol-5-yl)piperidin-1-yl)-2-oxoacetamide was purified by chiral HPLC: (Column: Chiralpak IC-III (250*20 mm, 5 mkm); Mobile phase: IPA-MeOH, 50-50. Flow Rate: 12 mL/min) to obtain N-(6-amino-5-ethylpyridin-3-yl)-2-((2R,5S)-5-methyl-2-(2-((2R,4r,6S)-1,2,6-trimethylpiperidin-4-yl)benzo[d]thiazol-5-yl)piperidin-1-yl)-2-oxoacetamide (42 mg, 78.55 μmol, 12.77% yield).

Rel Time for Compound 1261 in analytical conditions (column: 1C, IPA-MeOH, 50-50, 0.6 ml/min as mobile phase) 31.03 min.

Retention time: 31.03 min

¹H NMR (600 MHz, DMSO-d₆) δ (ppm) 1.03 (t, 3H), 1.05-1.14 (m, 9H), 1.29-1.40 (m, 1H), 1.52 (q, 2H), 1.65-1.74 (m, 1H), 1.82-1.91 (m, 1H), 2.00-2.12 (m, 3H), 2.17 (s, 3H), 2.18-2.21 (m, 2H), 2.27-2.43 (m, 3H), 2.75-3.28 (m, 2H), 3.44-4.07 (m, 1H), 5.26-5.75 (m, 3H), 7.31-7.54 (m, 2H), 7.84-7.93 (m, 1H), 7.97-8.11 (m, 2H), 10.48-10.61 (m, 1H).

LCMS(ESI): [M]+ m/z: calcd 548.2; found 549.2; Rt=2.176 min.

Example 603. The Synthesis of N-(5-ethyl-6-methylpyridin-3-yl)-2-((2R,5S)-5-methyl-2-(2-(1-methylpiperidin-4-yl)benzo[d]thiazol-5-yl)piperidin-1-yl)-2-oxoacetamide (Compound 1100)

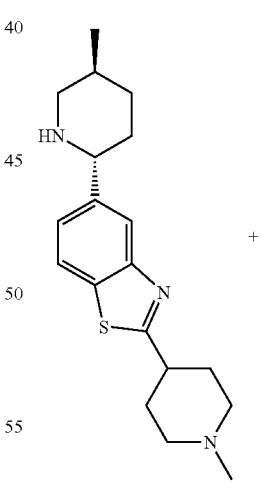

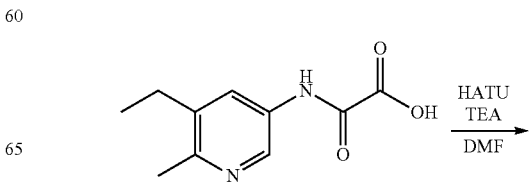

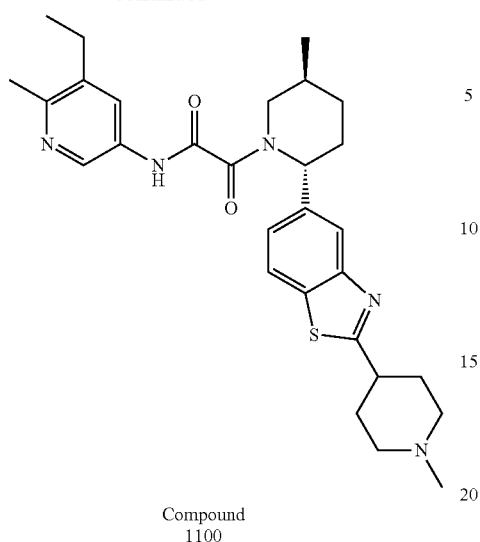

Compound 1100

Prepared by general procedure scheme H step 6A. Yield: 51 mg (16.17%).

HPLC conditions: Column: YMC Triart C18 100*20 mm, 5 microM; 0-6 min 50-85% water-MeOH+0.1% NH$_4$OH; (loading pump 4 ml/min MeOH).

Compound 1100:

$^1$H NMR (600 MHz, DMSO-d$_6$) δ (ppm) 0.99-1.08 (m, 3H), 1.08-1.19 (m, 3H), 1.30-1.41 (m, 1H), 1.64-1.88 (m, 4H), 1.90-2.10 (m, 5H), 2.18 (s, 3H), 2.26-2.35 (m, 1H), 2.36-2.42 (m, 3H), 2.52-2.62 (m, 3H), 2.81-2.85 (m, 2H), 3.00-3.10 (m, 1H), 3.44-4.08 (m, 1H), 5.25-5.82 (m, 1H), 7.32-7.43 (m, 1H), 7.76-7.91 (m, 2H), 8.01-8.10 (m, 1H), 8.43-8.59 (m, 1H), 10.91-11.08 (m, 1H).

LCMS(ESI): [M]$^+$ m/z: calcd 519.2; found 520.2; Rt=2.263 min.

Example 604. The Synthesis of N-(6-amino-5-eth-ylpyridin-3-yl)-2-((2R,5S)-2-(2-(3-((Dimethyl-amino)methyl)oxetan-3-yl)benzo[d]thiazol-5-yl)-5-methylpiperidin-1-yl)-2-oxoacetamide (Compound 1165)

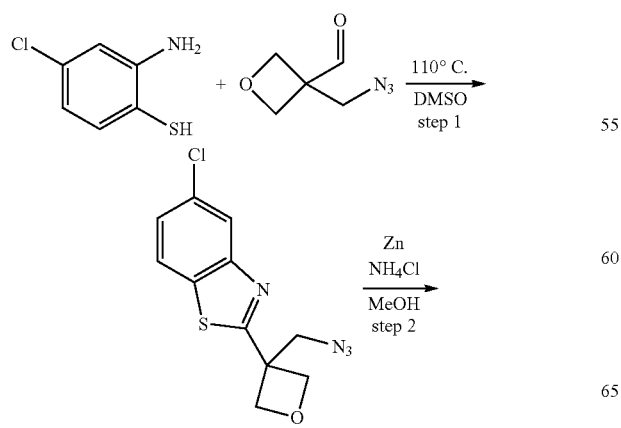

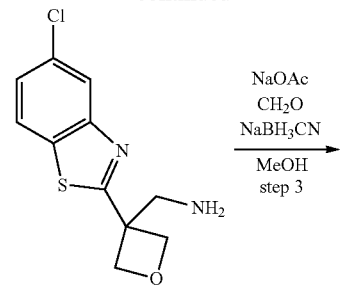

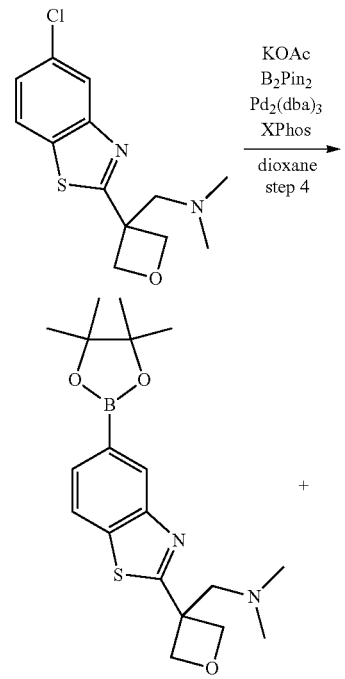

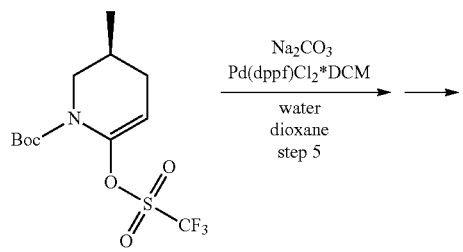

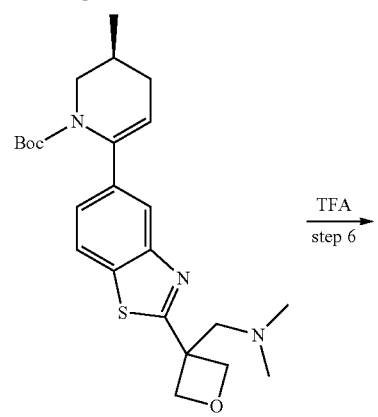

-continued

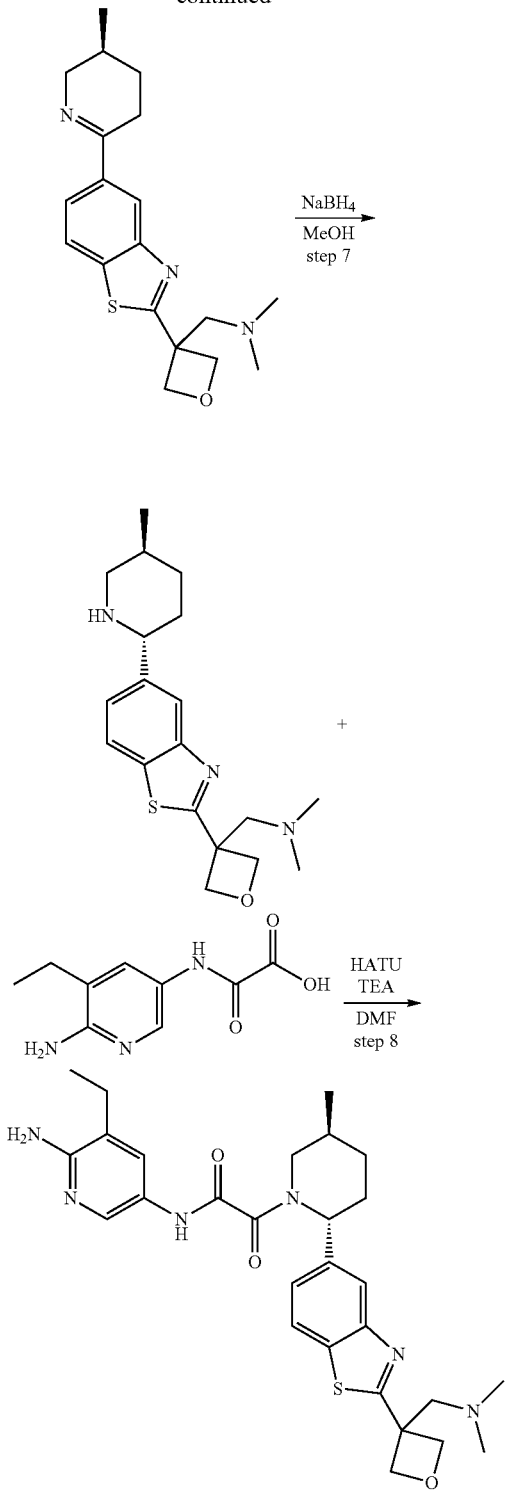

Step 1: Synthesis of 2-(3-(Azidomethyl)oxetan-3-yl)-5-chlorobenzo[d]thiazole

Prepared by general procedure scheme H step 1B. Yield: 11 g of crude

LCMS(ESI): [M]⁺ m/z: calcd 280.2; found 281.2; Rt=3.578 min.

Step 2: Synthesis of (3-(5-chlorobenzo[d]thiazol-2-yl)oxetan-3-yl)methanamine

Crude MTBE solution of 2-[3-(azidomethyl)oxetan-3-yl]-5-chloro-1,3-benzothiazole (11 g, 39.18 mmol) (approximately 50 mL) was diluted with methanol (100 mL) and ammonium chloride (12.58 g, 235.10 mmol, 8.22 mL) was added. Zinc (7.69 g, 117.55 mmol) dust was added potion wise with stirring at 25° C. to the above mixture. The reaction mixture was stirred at 25° C. for 12 hr, and then filtered. The filter cake was washed with MeOH (2*25 mL) and discarded. The combined filtrate was concentrated in vacuum. The residue was diluted with MTBE (100 mL) and extracted with 5% aqueous sodium hydrogen sulphate solution (100 mL). The resulting aqueous solution of amine hydrogen sulphate was then basified to pH 11 with 10% aqueous sodium hydroxide solution and extracted with DCM (2*50 mL). The combined organic extracts were dried over sodium sulphate and concentrated in vacuum to afford crude [3-(5-chloro-1,3-benzothiazol-2-yl)oxetan-3-yl]methanamine (1.2 g, 4.71 mmol, 12.02% yield) as light-yellow gum, which was used directly in the next step.

LCMS(ESI): [M]⁺ m/z: calcd 254.2; found 255.2; Rt=1.985 min.

Step 3: Synthesis of 1-(3-(5-chlorobenzo[d]thiazol-2-yl)oxetan-3-yl)-N,N-dimethylmethanamine Formaldehyde, 37% w/w aq. soln., stab. with 7-8% MeOH (946.16 mg, 11.66 mmol, 873.64 µL, 37% purity) and acetic acid (518.63 mg, 8.64 mmol, 494.41 µL) were added to a stirred solution of [3-(5-chloro-1,3-benzothiazol-2-yl)oxetan-3-yl]methanamine (1.1 g, 4.32 mmol) in MeOH (30.49 mL) at 25° C. The resulting mixture was stirred at 25° C. for 1 hr, then sodium cyanoborohydride (542.73 mg, 8.64 mmol) was added in one portion at 25° C. (foaming!). The reaction mixture was stirred at 25° C. for 12 hr, and then concentrated in vacuum. The residue was diluted with 10% aqueous sodium hydroxide solution (20 mL) and extracted with DCM (2*20 mL). The combined organic extracts were dried over sodium sulphate and concentrated in vacuum to afford crude 1-[3-(5-chloro-1,3-benzothiazol-2-yl)oxetan-3-yl]-N,N-dimethylmethanamine (1.3 g, crude) as light-yellow gum, which was used directly in the next step.

LCMS(ESI): [M]f m/z: calcd 282.2; found 283.2; Rt=1.530 min.

Step 4: Synthesis of N,N-dimethyl-1-(3-(5-(4,4,5,5-tetramethyl-1,3,2-dioxaborolan-2-yl)benzo[d]thiazol-2-yl)oxetan-3-yl)methanamine A mixture of 1-[3-(5-chloro-1,3-benzothiazol-2-yl)oxetan-3-yl]-N,N-dimethylmethanamine (1.4 g, 4.95 mmol), 4,4,5,5-tetramethyl-2-(4,4,5,5-tetramethyl-1,3,2-dioxaborolan-2-yl)-1,3,2-dioxaborolane (1.38 g, 5.45 mmol) and potassium acetate (971.72 mg, 9.90 mmol, 618.93 µL) in dioxane (35 mL) was evacuated and then backfilled with argon. This operation was repeated two times, then tris(1,5-diphenylpenta-1,4-dien-3-one)dipalladium (226.67 mg, 247.53 µmol) and dicyclohexyl[2',4',6'-tris(propan-2-yl)-[1,1'-biphenyl]-2-yl]phosphane (472.02 mg, 990.14 µmol) were added under argon, and the reaction mixture was stirred at 95° C. for 18 hr. The reaction mixture was cooled down and filtered. The filter cake was washed with dioxane (2*10 mL) and discarded. The combined filtrate was concentrated in vacuum. The residue was diluted with DCM (30 mL) and extracted with a solution of sodium hydrogen sulphate (1.19 g, 9.90 mmol) in water (20 mL) (repeated two times). The combined aqueous layer was basified to pH 10 with 10% aqueous sodium hydroxide solution and back-extracted with DCM (3*25 mL). Evaporation of both DCM extracts does not showed desired product. It seemed like boronic ester hydrolyzed in aqueous media and remained in aqueous phase as boronic acid. The combined water layer (approximately 100 mL) contained N,N-dimethyl-1-[3-[5-(4,4,5,5-tetramethyl-1,3,2-dioxaborolan-2-yl)-1,3-benzothiazol-2-yl]oxetan-3-yl]methanamine (1.85 g, 4.94 mmol, 100.00% yield) (theoretical amount of product, most likely in boronic acid form) was used directly in the next step.

LCMS(ESI): [M]$^+$ m/z: calcd 374.2; found 375.2; Rt=2.586 min.

Step 5: Synthesis of (S)-tert-butyl 6-(2-(3-((Dimethylamino)methyl)oxetan-3-yl)benzo[d]thiazol-5-yl)-3-methyl-3,4-dihydropyridine-1(2H)-carboxylate Prepared by general procedure scheme H step 3. Yield: 1.3 g of crude.

LCMS(ESI): [M]$^+$ m/z: calcd 443.2; found 444.2; Rt=1.279 min.

Step 6: Synthesis of (S)—N,N-dimethyl-1-(3-(5-(5-methyl-3,4,5,6-tetrahydropyridin-2-yl)benzo[d]thiazol-2-yl)oxetan-3-yl)methanamine Step 7: Synthesis of N,N-dimethyl-1-(3-(5-((2R,5S)-5-methylpiperidin-2-yl)benzo[d]thiazol-2-yl)oxetan-3-yl)methanamine Prepared by general procedure scheme H step 5. Yield: 330 mg (72.91%).

LCMS(ESI): [M]$^+$ m/z: calcd 345.2; found 346.2; Rt=0.574 min.

Step 8: Synthesis of N-(6-amino-5-ethylpyridin-3-yl)-2-((2R,5S)-2-(2-(3-((Dimethylamino)methyl)oxetan-3-yl)benzo[d]thiazol-5-yl)-5-methylpiperidin-1-yl)-2-oxoacetamide (Compound 1165

Prepared by general procedure scheme H step 6A. Yield: 47 mg (23.27%).

HPLC conditions: Column: YMC Triart C18 100*20 mm, 5 microM; 0-1-6 min 30-30-60% water-MeCN+0.1% NH$_4$OH, flow: 30 mL/min; (loading pump 4 mL/min MeCN).

$^1$H NMR (600 MHz, DMSO-d$_6$) δ (ppm) 1.02-1.14 (m, 6H), 1.31-1.43 (m, 1H), 1.67-1.77 (m, 1H), 1.85-1.93 (m, 1H), 2.04-2.31 (m, 8H), 2.33-2.43 (m, 2H), 2.78-3.26 (m, 3H), 3.47-4.09 (m, 1H), 4.74 (d, 2H), 4.95 (d, 2H), 5.28-5.74 (m, 3H), 7.36-7.44 (m, 1H), 7.45-7.54 (m, 1H), 7.92-8.10 (m, 3H), 10.37 (s, 1H).

LCMS(ESI): [M]$^+$ m/z: calcd 536.2; found 537.2; Rt=1.983 min.

Example 605. The Synthesis of N-(6-amino-5-ethyl-3-pyridyl)-2-oxo-2-[rac-(2R,4S,5R)-2-[3-[2-(dimethylamino)ethoxy]phenyl]-4-methoxy-5-methyl-1-piperidyl]acetamide (Compound 1139) and N-(6-amino-5-ethyl-3-pyridyl)-2-oxo-2-[rac-(2R,4R,5R)-2-[3-[2-(dimethylamino)ethoxy]phenyl]-4-methoxy-5-methyl-1-piperidyl]acetamide (Compound 1172)

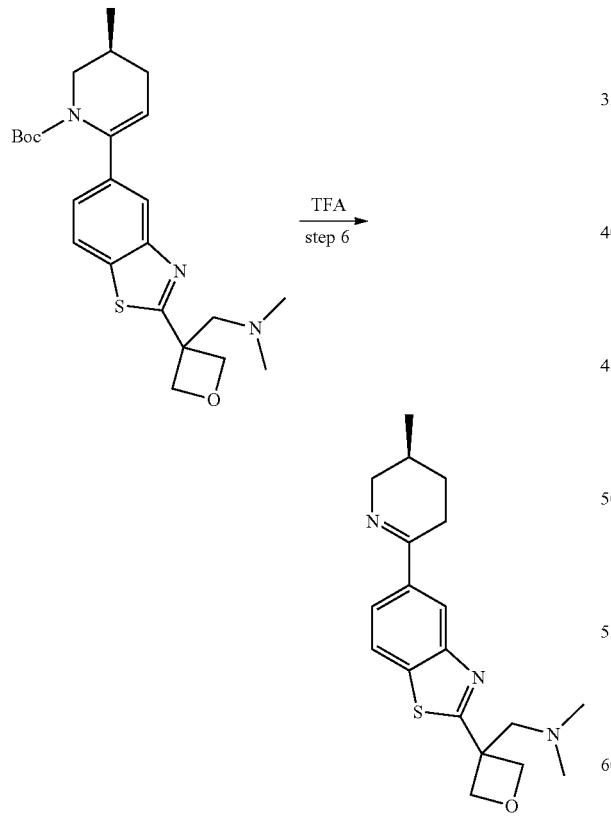

Prepared by general procedure scheme H step 4. Yield: 450 mg of crude.

LCMS(ESI): [M]$^+$ m/z: calcd 343.2; found 344.2; Rt=0.624 min.

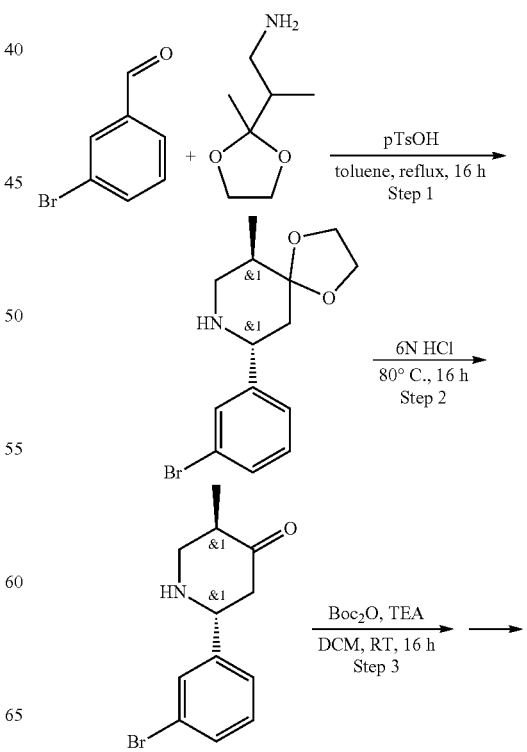

2615
-continued
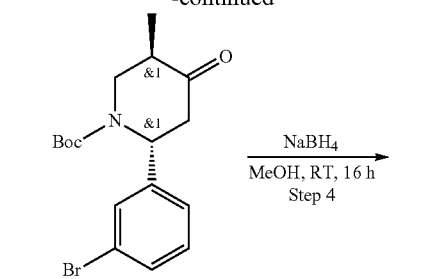
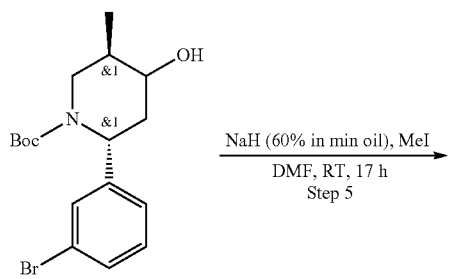
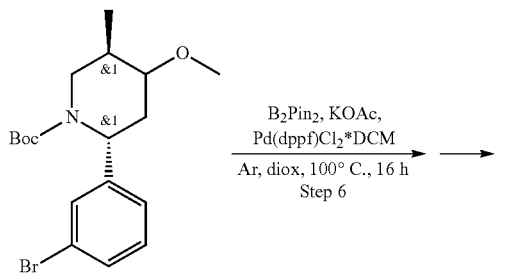
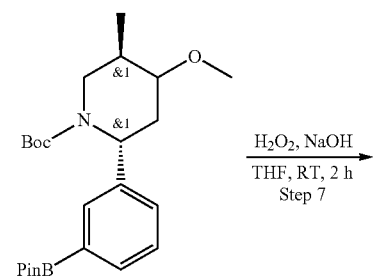
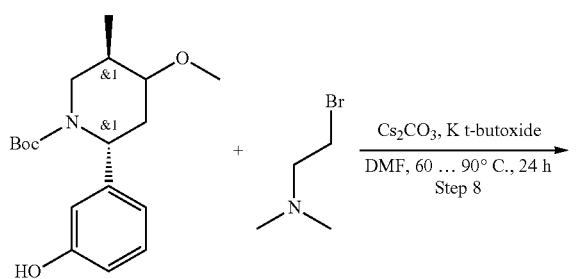
2616
-continued
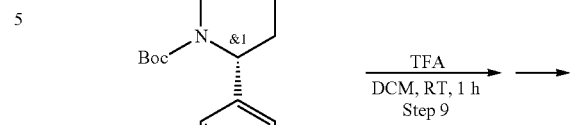
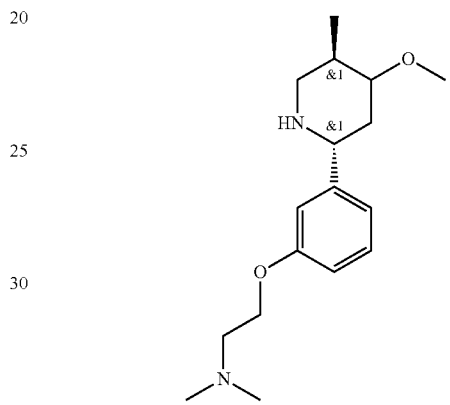
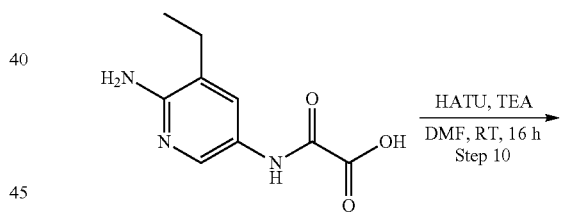
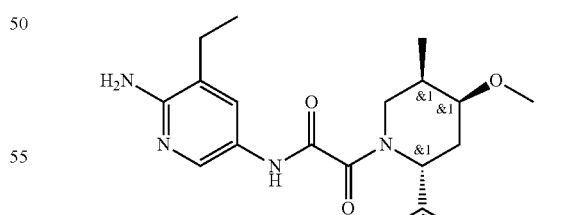
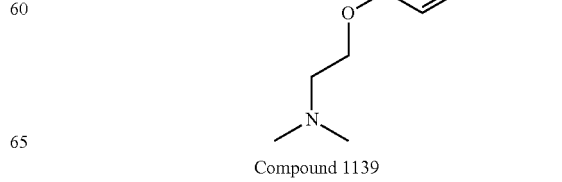
Compound 1139

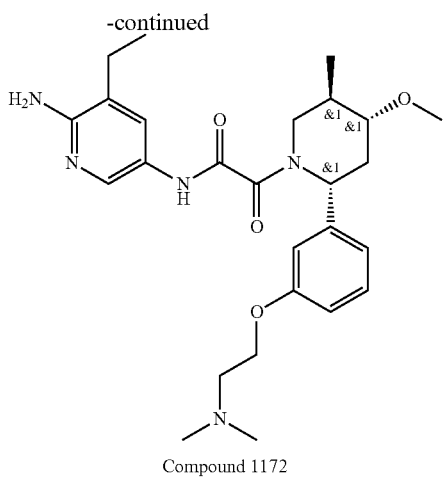

Compound 1172

Step 1: The Synthesis of rac-(6R,9R)-9-(3-bromophenyl)-6-methyl-1,4-dioxa-8-azaspiro[4.5]decane 3-bromobenzaldehyde (2.80 g, 15.15 mmol, 1.77 mL) and 2-(2-methyl-1,3-dioxolan-2-yl)propan-1-amine (2.2 g, 15.15 mmol) were dissolved in Toluene (35 mL) and p-Toluenesulfonic acid monohydrate (8.65 g, 45.45 mmol, 6.97 mL) was added. The resulting mixture was refluxed under Dean-Stark trap overnight. The reaction mixture was cooled and basified with aq. $K_2CO_3$ solution (10 g in 60 mL of water). The resulting mixture was extracted with EtOAc (2*75 mL) and combined organic layers were washed with brine (50 mL), dried over sodium sulfate, filtered, and concentrated in vacuo. The residue was dissolved in $CHCl_3$ (75 mL) and the resulting solution was extracted with aq. $NaHSO_4$ solution (2.5 g in 25 mL, twice). Combined aqueous layers were washed with $CHCl_3$ (2*45 mL) and basified with aq. $K_2CO_3$ solution (10 g in 30 mL of water). The resulting mixture was extracted with $CHCl_3$(2*50 mL) and combined organic layers were dried over $Na_2SO_4$, filtered, and concentrated in vacuo to obtain rac-(6R,9R)-9-(3-bromophenyl)-6-methyl-1,4-dioxa-8-azaspiro[4.5]decane (2.5 g, 8.01 mmol, 52.85% yield).

LCMS(ESI): [M+H]$^+$ m/z: calcd 312.0; found 312.0; Rt=0.804 min.

Step 2: The Synthesis of rac-(2R,5R)-2-(3-bromophenyl)-5-methyl-Piperidin-4-one rac-(6R,9R)-9-(3-bromophenyl)-6-methyl-1,4-dioxa-8-azaspiro[4.5]decane (2.5 g, 8.01 mmol) was dissolved in 6N HCl (40 mL) and the resulting mixture was heated at 80° C. overnight. The reaction mixture was cooled, transferred to a separation funnel, and washed with EtOAc (2*40 mL). The aqueous layer was neutralized with $K_2CO_3$. The resulting mixture was extracted with EtOAc (2*50 mL) and combined organic layers were dried over sodium sulfate, filtered, and concentrated in vacuo to obtain rac-(2R,5R)-2-(3-bromophenyl)-5-methyl-piperidin-4-one (1.56 g, 5.83 mmol, 72.84% yield).

LCMS(ESI): [M+H]$^+$ m/z: calcd 268.0; found 268.0; Rt=0.668 min.

Step 3: The Synthesis of tert-butyl rac-(2R,5R)-2-(3-bromophenyl)-5-methyl-4-oxo-piperidine-1-carboxylate rac-(2R,5R)-2-(3-bromophenyl)-5-methyl-piperidin-4-one (1.56 g, 5.83 mmol) and Triethylamine (885.30 mg, 8.75 mmol, 1.22 mL) were dissolved in DCM (20 mL) and a solution of Di-tert-butyl dicarbonate (1.46 g, 6.71 mmol, 1.54 mL) in DCM (5 mL) was added dropwise. The resulting mixture was stirred overnight. The reaction mixture was concentrated in vacuo and the residue was re-dissolved in DCM (50 mL). The resulting solution was washed with aq. $NaHSO_4$ solution (45 mL), dried over $Na_2SO_4$, filtered and concentrated in vacuo. The residue was purified by column chromatography (gradient EtOAc in hexane, from 0 to 50%) to obtain tert-butyl rac-(2R,5R)-2-(3-bromophenyl)-5-methyl-4-oxo-piperidine-1-carboxylate (377 mg, 1.02 mmol, 17.55% yield) and tert-butyl rac-(2R,5R)-2-(3-bromophenyl)-5-methyl-4-oxo-piperidine-1-carboxylate (1.14 g, 3.09 mmol, 52.98% yield).

$^1$H NMR (500 MHz, DMSO-$d_6$) δ (ppm) 1.16 (d, 3H), 1.45 (s, 9H), 2.45 (m, 1H), 2.84-2.92 (m, 2H), 3.64 (m, 1H), 3.77 (m, 1H), 5.48 (m, 1H), 7.14-7.18 (m, 2H), 7.36 (s, 1H).

LCMS(ESI): [M−tBu]$^+$ m/z: calcd 314.2; found 314.2; Rt=1.536 min.

Step 4: The Synthesis of tert-butyl rac-(2R,5R)-2-(3-bromophenyl)-4-hydroxy-5-methyl-piperidine-1-carboxylate tert-butyl rac-(2R,5R)-2-(3-bromophenyl)-5-methyl-4-oxo-piperidine-1-carboxylate (1.14 g, 3.09 mmol) was dissolved in MeOH (15 mL) and the resulting solution was cooled to 0° C. in an ice bath. Sodium Borohydride (175.36 mg, 4.64 mmol, 163.28 µL) was added to the previous solution and the resulting mixture was allowed to warm to room temperature and stirred overnight. Water (10 mL) was added and the resulting mixture was concentrated in vacuo. The resulting mixture was extracted with DCM (2*35 mL) and combined organic layers were washed with water (10 mL), dried over sodium sulfate, filtered and concentrated in vacuo to obtain tert-butyl rac-(2R,5R)-2-(3-bromophenyl)-4-hydroxy-5-methyl-piperidine-1-carboxylate (1.15 g, crude).

LCMS(ESI): [M−Boc]$^+$ m/z: calcd 272.0; found 272.0; Rt=1.416 min.

Step 5: The Synthesis of tert-butyl rac-(2R,5R)-2-(3-bromophenyl)-4-methoxy-5-methyl-piperidine-1-carboxylate tert-butyl rac-(2R,5R)-2-(3-bromophenyl)-4-hydroxy-5-methyl-piperidine-1-carboxylate (1.15 g, 3.09 mmol) was dissolved in DMF (10 mL) and Sodium hydride (in oil dispersion) 60% dispersion in mineral oil (355.45 mg, 9.28 mmol, 60% purity) was added portionwise. The resulting mixture was stirred for 1 hr and Methyl iodide (1.32 g, 9.28 mmol, 577.51 µL) was added in one portion. The resulting mixture was stirred overnight. The reaction mixture was poured into water (50 mL) and the resulting mixture was extracted with MTBE (2*50 mL). Combined organic layers were washed with water (3*50 mL), brine (50 mL), dried over sodium sulfate, filtered and concentrated in vacuo to obtain tert-butyl rac-(2R,5R)-2-(3-bromophenyl)-4-methoxy-5-methyl-piperidine-1-carboxylate (1.26 g, crude).

LCMS(ESI): [M−tBu]$^+$ m/z: calcd 328.2; found 328.2; Rt=1.667 min.

Step 6: The Synthesis of tert-butyl rac-(2R,5R)-4-methoxy-5-methyl-2-[3-(4,4,5,5-tetramethyl-1,3,2-dioxaborolan-2-yl)phenyl]piperidine-1-carboxylate tert-butyl rac-(2R,5R)-2-(3-bromophenyl)-4-methoxy-5-methyl-piperidine-1-carboxylate (1.26 g, 3.27 mmol) and 4,4,5,5-tetramethyl-2-(4,4,5,5-tetramethyl-1,3,2-dioxaborolan-2-yl)-1,3,2-dioxaborolane (871.42 mg, 3.43 mmol) were mixed in Dioxane (16 mL) and Potassium Acetate (801.88 mg, 8.17 mmol, 510.75 µL) was added thereto. The resulting mixture was evacuated and backfilled three times with argon and Pd(dppf)Cl$_2$—CH$_2$Cl$_2$ (133.45 mg, 163.41 µmol) was added. The resulting mixture was heated at 100° C. overnight. The reaction mixture was concentrated in vacuo and water (35 mL) was added to the residue. The resulting mixture was extracted with MTBE (2*50 mL) and combined organic layers were washed with water (25 mL), brine (25 mL), dried over Na$_2$SO$_4$, filtered and concentrated in vacuo to obtain tert-butyl rac-(2R,5R)-4-methoxy-5-methyl-2-[3-(4,4,5,5-tetramethyl-1,3,2-dioxaborolan-2-yl)phenyl]piperidine-1-carboxylate (1.79 g, crude).

LCMS(ESI): [M+H]$^+$ m/z: calcd 377.2; found 377.2; Rt=4.523 min.

Step 7: The Synthesis of tert-butyl rac-(2R,5R)-2-(3-hydroxyphenyl)-4-methoxy-5-methyl-piperidine-1-carboxylate tert-butyl rac-(2R,5R)-4-methoxy-5-methyl-2-[3-(4,4,5,5-tetramethyl-1,3,2-dioxaborolan-2-yl)phenyl]piperidine-1-carboxylate (1.79 g, 4.14 mmol) was dissolved in THF (16 mL) and Hydrogen peroxide 35% (603.56 mg, 6.21 mmol, 548.69 µL, 35% purity) was carefully added thereto. After addition completed, the resulting mixture was stirred for 1 hr and aq. solution of Sodium hydroxide, pearl (264.96 mg, 6.62 mmol, 124.39 µL) was added. After addition completed, the resulting mixture was stirred for 1 hr. The reaction mixture was acidified with citric acid and the resulting mixture was transferred to a separation funnel. An organic layer was separated and the aqueous layer was extracted with MTBE (2*50 mL). Combined organic layers were washed with aq. sodium sulfite, dried over Na$_2$SO$_4$, filtered and concentrated in vacuo to obtain tert-butyl rac-(2R,5R)-2-(3-hydroxyphenyl)-4-methoxy-5-methyl-piperidine-1-carboxylate (1.51 g, crude) which was used in the next step without purification.

LCMS(ESI): [M−Boc]$^+$ m/z: calcd 222.2; found 222.2; Rt=1.362 min.

Step 8: The Synthesis of tert-butyl rac-(2R,5R)-2-[3-[2-(dimethylamino)ethoxy]phenyl]-4-methoxy-5-methyl-piperidine-1-carboxylate tert-butyl rac-(2R,5R)-2-(3-hydroxyphenyl)-4-methoxy-5-methyl-piperidine-1-carboxylate (1.51 g, 4.71 mmol), 2-bromo-N,N-dimethyl-ethanamine (5.49 g, 23.55 mmol, HBr) and Cesium carbonate (7.67 g, 23.55 mmol) were mixed together in DMF (15 mL) and the resulting mixture was heated at 60° C. overnight. The reaction mixture was poured into water (50 mL) and the resulting mixture was extracted with EtOAc (3*50 mL). Combined organic layers were washed with water (3*50 mL), brine (50 mL), dried over Na$_2$SO$_4$, filtered, and concentrated in vacuo. The residue (1.109 g) was re-dissolved in DMF (15 mL) and Potassium tert-butoxide (2.38 g, 21.20 mmol) was added there followed by addition of 2-bromo-N,N-dimethyl-ethanamine; HBr (2.19 g, 9.42 mmol). The resulting mixture was heated at 90° C. overnight. 5% of starting material has left by LCMS of aliquot. 1.1 g of 2-bromo-N,N-dimethyl-ethanamine (HBr) and 1.2 g of Potassium tert-butoxide were added to the reaction mixture and the resulting mixture was heated at 90° C. overnight. The reaction mixture was poured into water (50 mL) and the resulting mixture was extracted with MTBE (3*50 mL). Combined organic layers were washed with water (3*50 mL), brine (50 mL), dried over Na$_2$SO$_4$, filtered, and concentrated in vacuo to obtain tert-butyl rac-(2R,5R)-2-[3-[2-(dimethylamino)ethoxy]phenyl]-4-methoxy-5-methyl-piperidine-1-carboxylate (1.05 g, 2.67 mmol, 56.79% yield).

LCMS(ESI): [M+H]$^+$ m/z: calcd 393.2; found 393.2; Rt=1.015 min.

Step 9: The Synthesis of N,N-dimethyl-2-[3-[rac-(2R,5R)-4-methoxy-5-methyl-2-piperidyl]phenoxy]ethanamine tert-butyl rac-(2R,5R)-2-[3-[2-(dimethylamino)ethoxy]phenyl]-4-methoxy-5-methyl-piperidine-1-carboxylate (1.05 g, 2.67 mmol) was dissolved in DCM (4 mL) and TFA (4 mL) was added. The resulting mixture was stirred for 1 hr. The reaction mixture was poured into aq. K$_2$CO$_3$ solution (10 g in 45 mL of water) and the resulting mixture was extracted with DCM (2*45 mL). Combined organic layers were dried over Na$_2$SO$_4$, filtered and concentrated in vacuo to obtain N,N-dimethyl-2-[3-[rac-(2R,5R)-4-methoxy-5-methyl-2-piperidyl]phenoxy]ethanamine (851 mg, crude).

LCMS(ESI): [M+H]$^+$ m/z: calcd 293.2; found 293.2; Rt=0.474 min.

Step 10: The Synthesis of N-(6-amino-5-ethyl-3-pyridyl)-2-oxo-2-[rac-(2R,4S,5R)-2-[3-[2-(dimethylamino)ethoxy]phenyl]-4-methoxy-5-methyl-1-piperidyl]acetamide (Compound 1139) and N-(6-amino-5-ethyl-3-pyridyl)-2-oxo-2-[rac-(2R,4R,5R)-2-[3-[2-(dimethylamino)ethoxy]phenyl]-4-methoxy-5-methyl-1-piperidyl]acetamide (Compound 1172

N,N-dimethyl-2-[3-[rac-(2R,5R)-4-methoxy-5-methyl-2-piperidyl]phenoxy]ethanamine (334 mg, 1.14 mmol), 2-[(6-amino-5-ethyl-3-pyridyl)amino]-2-oxo-acetic acid (238.95 mg, 1.14 mmol) and Triethylamine (577.90 mg, 5.71 mmol, 796.01 µL) were mixed together in DMF (3 mL) and HATU (521.16 mg, 1.37 mmol) was added thereto. The resulting mixture was stirred overnight. The reaction mixture was submitted to HPLC and purified (2-10 min; 0-25% water/MeOH+NH$_3$ 30 mL/min; loading pump 4 mL/min MeOH+NH$_3$; column SunFire 19*100 mm, 5 um) to obtain N-(6-amino-5-ethyl-3-pyridyl)-2-oxo-2-[rac-(2R,4S,5R)-2-[3-[2-(dimethylamino)ethoxy]phenyl]-4-methoxy-5-methyl-1-piperidyl]acetamide (101.7 mg, 210.30 mol, 18.41% yield) and N-(6-amino-5-ethyl-3-pyridyl)-2-oxo-2-[rac-(2R,4R,5R)-2-[3-[2-(dimethylamino)ethoxy]phenyl]-4-methoxy-5-methyl-1-piperidyl]acetamide (54 mg, 111.66 mol, 9.78% yield).

Compound 1139: Yield: 101.7 mg (18.41%) nLCMS (ESI): [M+H]$^+$ m/z: calcd 485.2; found 485.2; Rt=1.806 min.

Compound 1172: Yield: 54.0 mg (9.78%) LCMS(ESI): [M+H]$^+$ m/z: calcd 485.2; found 485.2; Rt=1.813 min.

Example 606. The Synthesis of N-(5,6-dimethylpyridin-3-yl)-2-((2R,5S)-5-methyl-2-(2-(1-methylazetidin-3-yl)benzo[d]thiazol-5-yl)piperidin-1-yl)-2-oxoacetamide (Compound 1123)

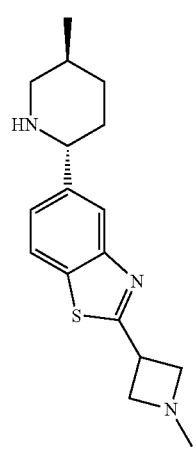

+

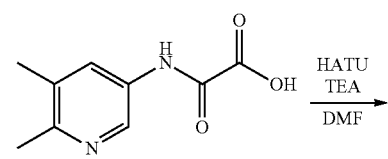

Prepared by general procedure scheme H step 6A. Yield: 47.5 mg (13.63%).

HPLC conditions: Column: XBridge C18 100*19 mm, 5 microM; 0-5 min 30-80% water-MeOH+0.1% NH$_4$OH; (loading pump 4 mL/min MeOH).

$^1$H NMR (500 MHz, dmso) δ 1.01-1.06 (m, 3H), 1.30-1.41 (m, 1H), 1.66-1.76 (m, 1H), 1.81-1.92 (m, 1H), 2.04-2.14 (m, 1H), 2.15-2.32 (m, 8H), 2.34-2.39 (m, 3H), 2.78-3.06 (m, 1H), 3.44-4.06 (m, 5H), 5.24-5.76 (m, 1H), 7.34-7.45 (m, 1H), 7.72-7.85 (m, 1H), 7.87-7.94 (m, 1H), 8.02-8.10 (m, 1H), 8.40-8.54 (m, 1H), 10.81-11.10 (m, 1H).

LCMS(ESI): [M]$^+$ m/z: calcd 477.2; found 478.2; Rt=2.209 min.

Example 607. The Synthesis of N-(6-amino-5-ethylpyridin-3-yl)-2-((2R,5S)-5-methyl-2-(2-(1,2,2-trimethylpiperidin-4-yl)benzo[d]thiazol-5-yl)piperidin-1-yl)-2-oxoacetamides (Compound 1183, Compound 1397 and Compound 1129

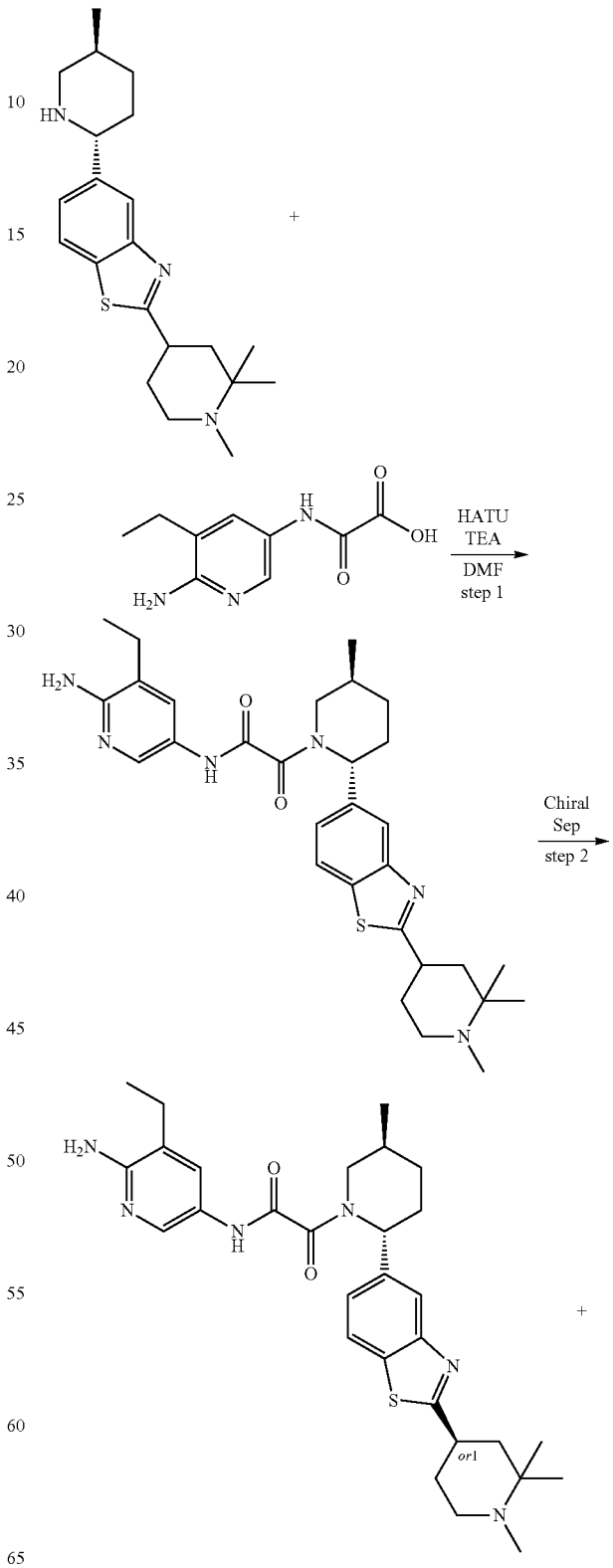

Compound 1129

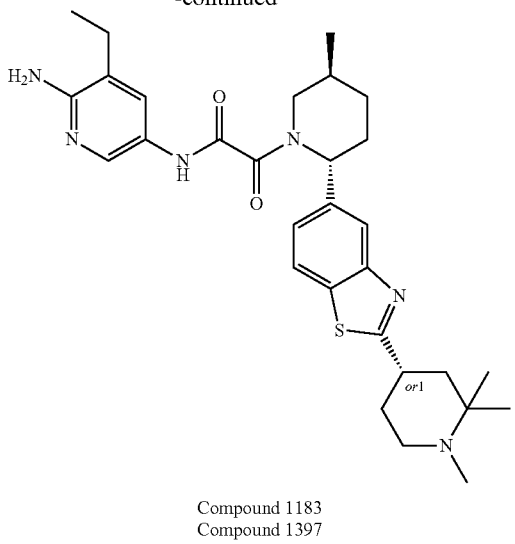

Compound 1183
Compound 1397

Step 1: Synthesis of N-(6-amino-5-ethylpyridin-3-yl)-2-((2R,5S)-5-methyl-2-(2-(1,2,2-trimethylpiperidin-4-yl)benzo[d]thiazol-5-yl)piperidin-1-yl)-2-oxoacetamide Prepared by general procedure scheme H step 6A. Yield: 94 mg (24.65%).

HPLC conditions: Column: YMC Triart C18 100*20 mm, 5 microM; 0-1-5 min 50-50-90% water-MeOH+0.1% NH$_4$OH, flow: 30 mL/min; (loading pump 4 mL/min MeOH).

LCMS(ESI): [M]$^+$ m/z: calcd 548.2; found 549.2; Rt=1.860 min.

Step 2: Chiral Separation (Compound 1183, Compound 1397 and Compound 1129

Racemic N-(6-amino-5-ethylpyridin-3-yl)-2-((2R,5S)-5-methyl-2-(2-(1,2,2-trimethylpiperidin-4-yl)benzo[d]thiazol-5-yl)piperidin-1-yl)-2-oxoacetamide (0.079 g, 147.74 mol) was chiral separated (Column: Chiralpak IA (250×20 mm, 5 mkm); Mobile phase: Hexane-IPA-MeOH, 40-30-30 Flow Rate: 12 mL/min) to obtain N-(6-amino-5-ethylpyridin-3-yl)-2-((2R,5S)-5-methyl-2-(2-(rel-(S)-1,2,2-trimethylpiperidin-4-yl)benzo[d]thiazol-5-yl)piperidin-1-yl)-2-oxoacetamide (0.0364 g, 68.07 μmol, 92.15% yield) (RT=45.37) and N-(6-amino-5-ethylpyridin-3-yl)-2-((2R,5S)-5-methyl-2-(2-(rel-(R)-1,2,2-trimethylpiperidin-4-yl)benzo[d]thiazol-5-yl)piperidin-1-yl)-2-oxoacetamide (0.0389 g, 72.75 μmol, 98.48% yield) (RT=34.77).

Rel Time for Compound 1183 in analytical conditions (column: IA, Hexane-IPA-MeOH, 40-30-30, 0.6 mL/min as mobile phase) 46.41 min, and for Compound 1129 35.14 min.

30 mg of Compound 1183 was further purified by Chiral HPLC (Column: Chiralcel OD-H (250*20 mm, 5 mkm); Mobile phase: Hexane-IPA-MeOH 70-15-15; Flow Rate: 12 mL/min), affording N-(6-amino-5-ethylpyridin-3-yl)-2-((2R,5S)-2-(2-((S)-2,2-dimethylpiperidin-4-yl)benzo[d]thiazol-5-yl)-5-methylpiperidin-1-yl)-2-oxoacetamide (19 mg, 35.53 μmol, 48.10% yield) (RT=17.56).

Rel Time for Compound 1397 in analytical conditions (column: OD-H, Hexane-IPA-MeOH, 60-20-20, 0.6 mL/min as mobile phase) 13.69 min.

Compound 1183: $^1$H NMR (500 MHz, dmso) δ 0.98-1.05 (m, 6H), 1.06-1.16 (m, 6H), 1.30-1.41 (m, 1H), 1.62-1.77 (m, 3H), 1.82-1.94 (m, 2H), 1.99-2.11 (m, 2H), 2.20 (s, 3H), 2.25-2.35 (m, 2H), 2.38-2.43 (m, 2H), 2.56-2.71 (m, 2H), 2.75-3.20 (m, 1H), 3.45-4.07 (m, 1H), 5.25-5.60 (m, 1H), 5.62-5.74 (m, 2H), 7.31-7.42 (m, 1H), 7.42-7.56 (m, 1H), 7.83-7.92 (m, 1H), 7.95-8.12 (m, 2H), 10.51-10.63 (m, 1H).

LCMS(ESI): [M+1]$^+$ m/z: calcd 548.2; found 549.2; Rt=0.755 min.

Compound 1397: $^1$H NMR (500 MHz, dmso) δ 0.98-1.05 (m, 6H), 1.06-1.16 (m, 6H), 1.30-1.41 (m, 1H), 1.62-1.77 (m, 3H), 1.82-1.94 (m, 2H), 1.99-2.11 (m, 2H), 2.20 (s, 3H), 2.25-2.35 (m, 2H), 2.38-2.43 (m, 2H), 2.56-2.71 (m, 2H), 2.75-3.20 (m, 1H), 3.45-4.07 (m, 1H), 5.25-5.60 (m, 1H), 5.62-5.74 (m, 2H), 7.31-7.42 (m, 1H), 7.42-7.56 (m, 1H), 7.83-7.92 (m, 1H), 7.95-8.12 (m, 2H), 10.51-10.63 (m, 1H).

LCMS(ESI): [M]$^+$ m/z: calcd 548.2; found 549.2; Rt=2.426 min.

Compound 1129: $^1$H NMR (600 MHz, DMSO-d$_6$) δ (ppm) 0.97-1.00 (m, 3H), 1.02-1.09 (m, 4H), 1.09-1.15 (m, 5H), 1.29-1.42 (m, 1H), 1.60-1.78 (m, 3H), 1.83-1.93 (m, 2H), 1.99-2.16 (m, 2H), 2.16 (s, 3H), 2.21-2.37 (m, 2H), 2.39-2.43 (m, 1H), 2.52-2.58 (m, 2H), 2.60-2.67 (m, 1H), 2.77-3.24 (m, 1H), 3.48-4.07 (m, 1H), 5.19-5.62 (m, 1H), 5.61-5.72 (m, 2H), 7.31-7.43 (m, 1H), 7.42-7.57 (m, 1H), 7.84-7.92 (m, 1H), 7.97-8.11 (m, 2H), 10.48-10.66 (m, 1H).

LCMS(ESI): [M]$^+$ m/z: calcd 548.2; found 549.2; Rt=2.257 min.

Example 608. The Synthesis of N-(5,6-dimethylpyridin-3-yl)-2-((2R,53)-5-methyl-2-(2-(1,2,2-trimethylpiperidin-4-yl)benzo[d]thiazol-5-yl)piperidin-1-yl)-2-oxoacetamide (Compound 1215 and Compound 1113

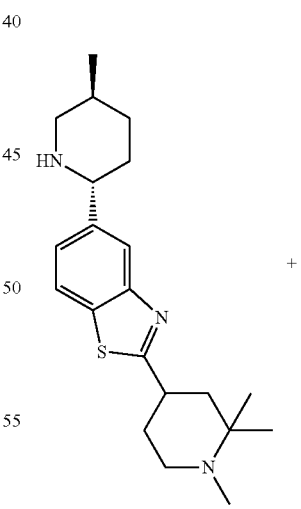

+

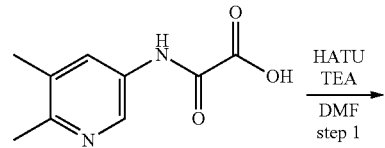

HATU
TEA
DMF
step 1

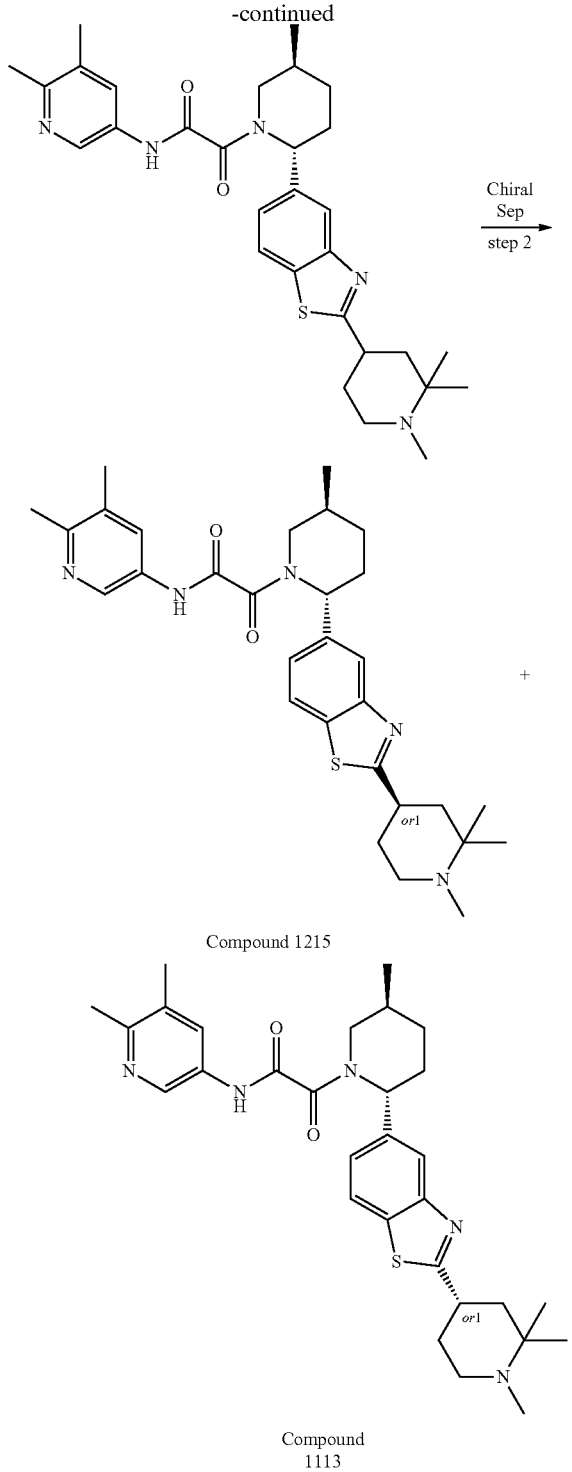

Compound 1215

Compound 1113

Step 1: Synthesis of N-(5,6-dimethylpyridin-3-yl)-2-((2R,5S)-5-methyl-2-(2-(1,2,2-trimethylpiperidin-4-yl)benzo[d]thiazol-5-yl)piperidin-1-yl)-2-oxoacetamide Prepared by general procedure scheme H step 6A. Yield: 81 mg (36.18%).

HPLC conditions: Column: XBridge C18 100*19 mm, 5 microM; 0-6 min 60-75% water-MeOH+0.1% NH$_4$OH, flow: 30 mL/min; (loading pump 4 mL/min MeCN).

LCMS(ESI): [M]$^+$ m/z: calcd 533.2; found 534.2; Rt=1.881 min.

Step 2: Chiral Separation (Compound 1215 and Compound 1113

Racemic N-(5,6-dimethyl-3-pyridyl)-2-oxo-2-[rac-(2R, 5S)-5-methyl-2-[2-(1,2,2-trimethyl-4-piperidyl)-1,3-benzothiazol-5-yl]-1-piperidyl]acetamide (0.081 g, 151.76 μmol) was chiral separated (Column: Chiralpak IA-III (250-20 mm-5 m); Mobile phase: IPA-MeOH, 50-50 Flow Rate: 12 mL/min) to obtain N-(5,6-dimethyl-3-pyridyl)-2-oxo-2-[(2R,5S)-5-methyl-2-[2-[(4R)-1,2,2-trimethyl-4-piperidyl]-1,3-benzothiazol-5-yl]-1-piperidyl]acetamide (0.031 g, 58.08 μmol, 38.27% yield) and N-(5,6-dimethyl-3-pyridyl)-2-oxo-2-[(2R,5S)-5-methyl-2-[2-[(4S)-1,2,2-trimethyl-4-piperidyl]-1,3-benzothiazol-5-yl]-1-piperidyl]acetamide (0.05775 g, 124.60 umol, 50.22% yield).

Rel Time for Compound 1215 in analytical conditions (column: IA, IPA-MeOH, 50-50, 0.6 mL/min as mobile phase) 61.75 min and for Compound 1113 27.05 min.

Compound 1215: Retention time: 61.75 min $^1$H NMR (600 MHz, DMSO-d$_6$) δ (ppm) 0.98 (s, 3H), 1.00-1.06 (m, 3H), 1.10 (s, 3H), 1.30-1.41 (m, 1H), 1.59-1.65 (m, 1H), 1.66-1.77 (m, 2H), 1.83-1.92 (m, 2H), 1.98-2.13 (m, 2H), 2.15 (s, 3H), 2.16-2.25 (m, 3H), 2.28-2.38 (m, 4H), 2.52-2.62 (m, 3H), 2.80-3.26 (m, 1H), 3.44-4.05 (m, 1H), 5.23-5.74 (m, 1H), 7.32-7.44 (m, 1H), 7.71-7.84 (m, 1H), 7.85-7.92 (m, 1H), 8.00-8.08 (m, 1H), 8.39-8.53 (m, 1H), 10.72-11.13 (m, 1H).

LCMS(ESI): [M]$^+$ m/z: calcd 533.2; found 534.2; Rt=2.106 min.

Compound 1113: Retention time: 27.05 min $^1$H NMR (600 MHz, DMSO-d$_6$) δ (ppm) 0.98 (s, 3H), 1.00-1.07 (m, 3H), 1.11 (s, 3H), 1.30-1.41 (m, 1H), 1.58-1.65 (m, 1H), 1.65-1.76 (m, 2H), 1.81-1.93 (m, 2H), 1.98-2.13 (m, 2H), 2.14-2.19 (m, 4H), 2.24 (s, 2H), 2.29-2.38 (m, 4H), 2.52-2.62 (m, 3H), 2.81-3.27 (m, 1H), 3.43-4.05 (m, 1H), 5.23-5.73 (m, 1H), 7.33-7.43 (m, 1H), 7.72-7.84 (m, 1H), 7.86-7.92 (m, 1H), 8.01-8.08 (m, 1H), 8.39-8.55 (m, 1H), 10.69-11.19 (m, 1H).

LCMS(ESI): [M]$^+$ m/z: calcd 533.2; found 534.2; Rt=2.108 min.

Example 609. The Synthesis of N-(6-amino-5-ethylpyridin-3-yl)-2-((2R,5S)-2-(2-((R)-2-(dimethylamino)propyl)benzo[d]thiazol-5-yl)-5-methylpiperidin-1-yl)-2-oxoacetamide (Compound 1198)

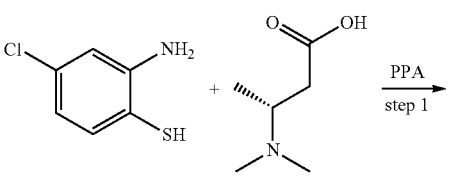

-continued

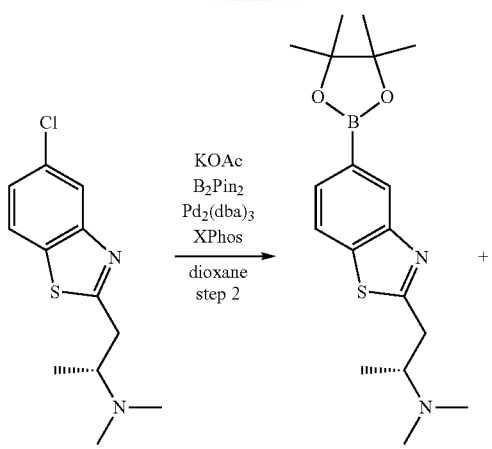

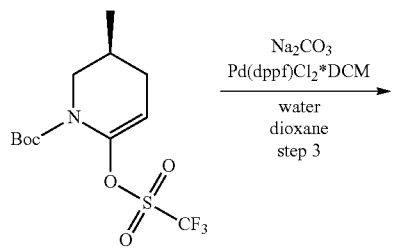

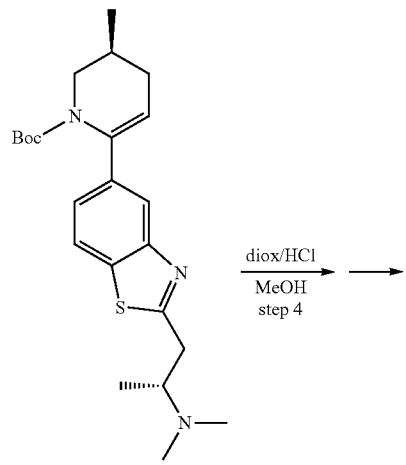

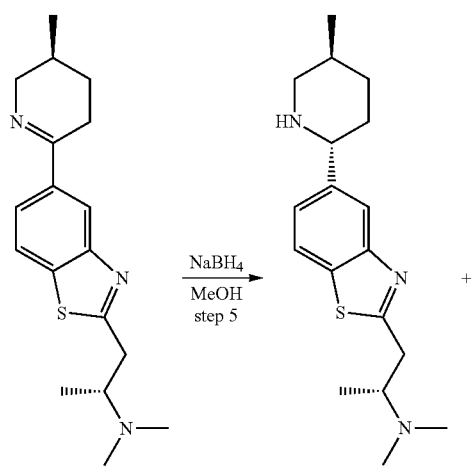

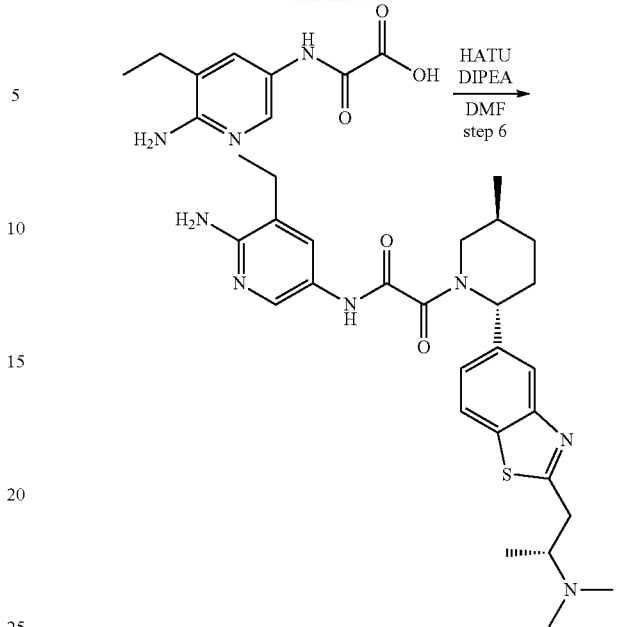

Step 1: Synthesis of (R)-1-(5-chlorobenzo[d]thi-azol-2-yl)-N,N-dimethylpropan-2-amine The stirred solution of (3R)-3-(dimethylamino)butanoic acid (1 g, 7.62 mmol) and 2-amino-4-chloro-benzenethiol (1 g, 6.26 mmol) in PPA (5 mL) was allowed to stir at 120° C. for 24 hr. Upon completion, the reaction mixture was quenched with water (50 mL) and neutralized by NaOH to pH=8. The aqueous phase was extracted with EtOAc (2*20 mL). The combined organic phase was dried over $Na_2SO_4$ and concentrated under reduced pressure. The crude product was purified by silica gel column chromatography using MeOH/EtOAc (1:5, v:v) as eluent (Rt=0.2) to afford (2R)-1-(5-chloro-1,3-benzothiazol-2-yl)-N,N-dimethyl-propan-2-amine (0.7 g, 2.75 mmol, 43.86% yield). The desired product (2R)-1-(5-chloro-1,3-benzothiazol-2-yl)-N,N-dimethyl-propan-2-amine (0.7 g, 2.75 mmol, 43.86% yield) was isolated.

LCMS(ESI): $[M]^+$ m/z: calcd 254.2; found 255.2; Rt=0.934 min.

Step 2: Synthesis of (R)—N,N-dimethyl-1-(5-(4,4,5,5-tetramethyl-1,3,2-dioxaborolan-2-yl)benzo[d]thiazol-2-yl)propan-2-amine To a stirred solution of (2R)-1-(5-chloro-1,3-benzothi-azol-2-yl)-N,N-dimethyl-propan-2-amine (0.7 g, 2.75 mmol) and 4,4,5,5-tetramethyl-2-(4,4,5,5-tetramethyl-1,3,2-dioxaborolan-2-yl)-1,3,2-dioxaborolane (0.7 g, 2.76 mmol) in dioxane (30 mL) were added $Pd_2(dba)_3$ (0.5 g, 546.03 µmol) and XPhos (0.5 g, 1.05 mmol). The resulting suspension was degassed with argon at 50° C. for 0.5 hr. Potassium acetate (0.55 g, 5.60 mmol, 350.32 µL) was added. The reaction mixture was stirred at 100° C. for 16 hr. Upon completion, the reaction mixture was concentrated under reduced pressure, quenched with water (50 mL), the aqueous phase was extracted with $CHCl_3$ (2*50 mL). The organic phase was extracted with 10% HCl (2*50 mL). The aqueous phase was neutralized by $NaHCO_3$ to pH=8, extracted with $CHCl_3$ (2*50 mL). The organic phase was dried over Na₂SO₄ and evaporated in vacuum. The desired product (2R)—N,N-dimethyl-1-[5-(4,4,5,5-tetramethyl-1,3,2-dioxaborolan-2-yl)-1,3-benzothiazol-2-yl]propan-2-amine (0.4 g, 1.16 mmol, 42.04% yield) was isolated.

LCMS(ESI): [M]⁺ m/z: calcd 346.2; found 347.2; Rt=1.182 min.

Step 3: Synthesis of (S)-tert-butyl 6-(2-((R)-2-(dimethylamino)propyl)benzo[d]thiazol-5-yl)-3-methyl-3,4-dihydropyridine-1(2H)-carboxylate Prepared by general procedure scheme H step 3. Yield: 0.48 g of crude.

LCMS(ESI): [M]⁺ m/z: calcd 415.2; found 416.2; Rt=1.151 min.

Step 4: Synthesis of (R)—N,N-dimethyl-1-(5-((S)-5-methyl-3,4,5,6-tetrahydropyridin-2-yl)benzo[d]thiazol-2-yl)propan-2-amine The stirred solution of tert-butyl rac-(3S)-3-methyl-6-[2-[rac-(2R)-2-(dimethylamino)propyl]-1,3-benzothiazol-5-yl]-3,4-dihydro-2H-pyridine-1-carboxylate (0.48 g, 1.15 mmol) in MeOH (10 mL) and diox/HCl (5 mL) was allowed to stir at 25° C. for 16 hr. Upon completion, the reaction mixture was evaporated, the crude product was quenched with water (20 mL) and neutralized by NaHCO₃ to pH=8. The aqueous phase was extracted with CHCl₃ (2*20 mL). The combined organic phase was dried over Na₂SO₄ and concentrated under reduced pressure. The desired product rac-(2R)—N,N-dimethyl-1-[5-[rac-(3S)-3-methyl-2,3,4,5-tetrahydropyridin-6-yl]-1,3-benzothiazol-2-yl]propan-2-amine (0.36 g, 1.14 mmol, 98.80% yield) was isolated.

LCMS(ESI): [M]⁺ m/z: calcd 315.2; found 316.2; Rt=0.478 min.

Step 5: Synthesis of (R)—N,N-dimethyl-1-(5-((2R,5S)-5-methylpiperidin-2-yl)benzo[d]thiazol-2-yl)propan-2-amine Prepared by general procedure scheme H step 5. Yield: 0.36 g of crude.

LCMS(ESI): [M]⁺ m/z: calcd 317.2; found 318.2; Rt=0.697 min.

Step 6: Synthesis of N-(6-amino-5-ethylpyridin-3-yl)-2-((2R,5S)-2-(2-((R)-2-(dimethylamino)propyl)benzo[d]thiazol-5-yl)-5-methylpiperidin-1-yl)-2-oxoacetamide (Compound 1198

Prepared by general procedure scheme H step 6B. Yield: 24 mg (8.32%).

HPLC conditions: Column: XBridge C18 100*19 mm, 5 microM; 0-5 min 35-60% water-MeCN+0.1% NH₄OH, flow: 30 mL/min; (loading pump 4 mL/min MeOH).

¹H NMR (600 MHz, DMSO-d₆) δ (ppm) 0.95-1.09 (m, 6H), 1.30-1.42 (m, 1H), 1.66-1.75 (m, 1H), 1.83-1.93 (m, 1H), 2.05-2.34 (m, 8H), 2.81-3.27 (m, 4H), 3.48-4.09 (m, 4H), 5.27-5.74 (m, 1H), 7.28-7.42 (m, 1H), 7.65-7.77 (m, 2H), 7.83-7.90 (m, 1H), 7.99-8.05 (m, 1H), 8.39-8.60 (m, 2H), 10.99-11.15 (m, 1H).

LCMS(ESI): [M]⁺ m/z: calcd 508.2; found 509.2; Rt=1.854 min.

Example 610. The Synthesis of 5-(2-((2R,5S)-2-(2-((R)-2-(dimethylamino)propyl)benzo[d]thiazol-5-yl)-5-methylpiperidin-1-yl)-2-oxoacetamido)-2-methoxynicotinamide (Compound 1317)

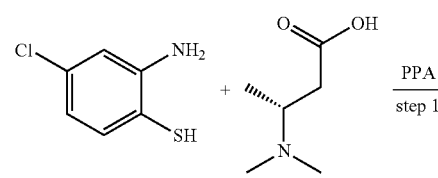

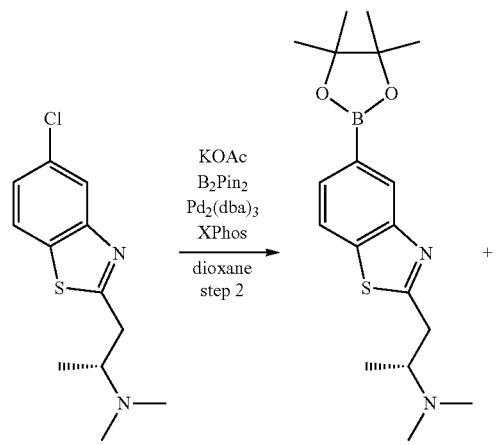

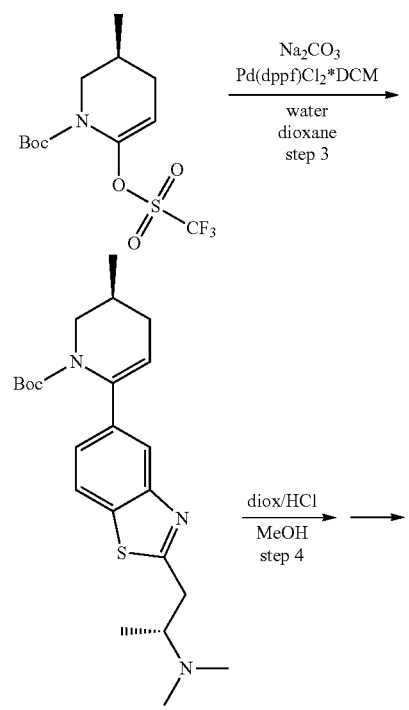

2631
-continued

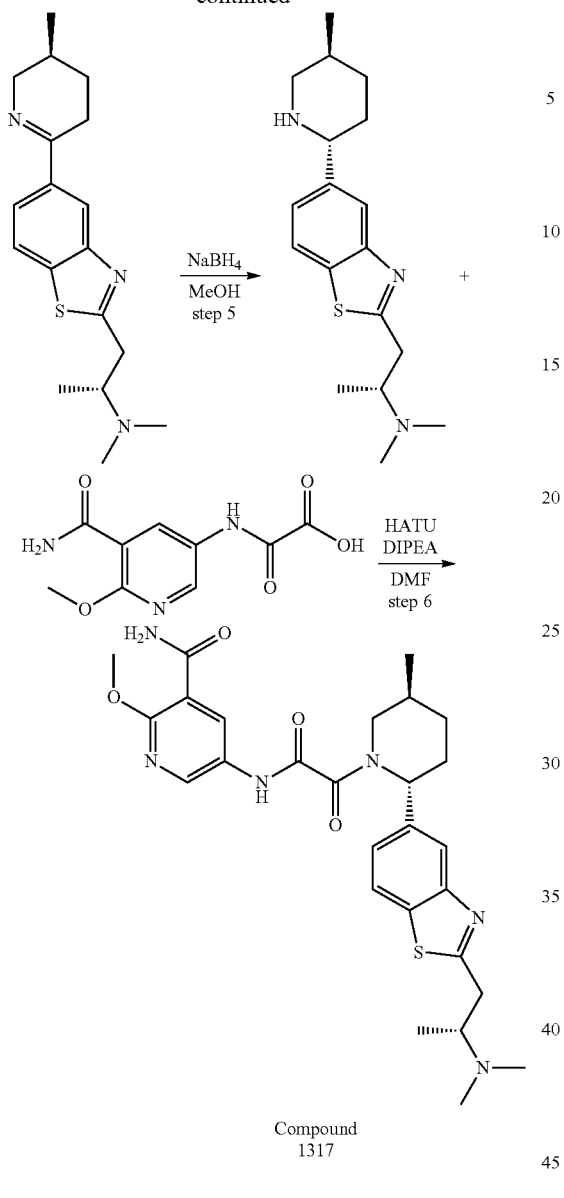

Compound 1317

Step 6: Synthesis of 5-(2-((2R,5S)-2-(2-((R)-2-(dimethylamino)propyl)benzo[d]thiazol-5-yl)-5-methylpiperidin-1-yl)-2-oxoacetamido)-2-methoxynicotinamide (Compound 1317

Prepared by general procedure scheme H step 6B. Yield: 22 mg (6.60%).

HPLC conditions: Column: XBridge C18 100*19 mm, 5 microM; 0-5 min 40-80% water-MeOH+0.1% $NH_4OH$, flow: 30 mL/min; (loading pump 4 mL/min MeOH).

Product was purified by chiral HPLC from cis-impurity (Column: Chiralpak 1C (250*20 mm, 5 mkm); Mobile phase: IPA-MeOH, 50-50. Flow Rate: 10 mL/min) (RT=54.03 min).

Compound 1317: Retention time: 39.98 min

LCMS(ESI): $[M]^+$ m/z: calcd 538.2; found 539.2; Rt=2.215 min.

2632

Example 611. The Synthesis of N-(6-amino-5-ethylpyridin-3-yl)-2-((2R,5)-2-(2-(1,4-dimethylpiperidin-4-yl)benzo[d]thiazol-5-yl)-5-methylpiperidin-1-yl)-2-oxoacetamide (Compound 1171)

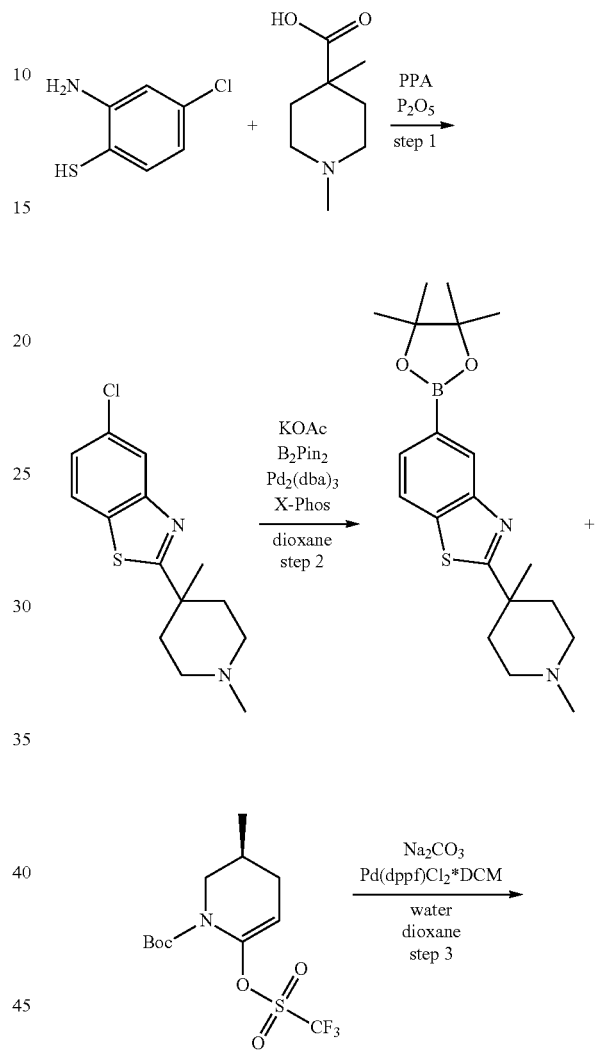

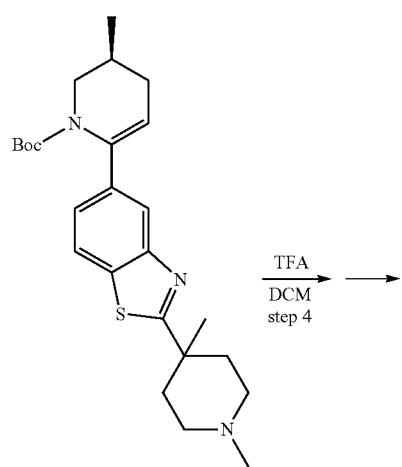

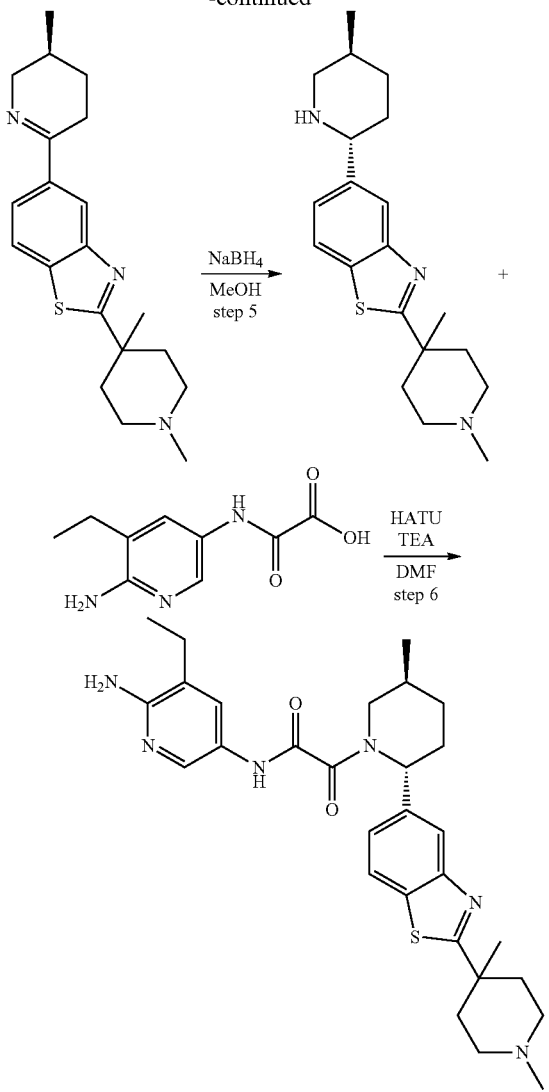

Step 1: Synthesis of 5-chloro-2-(1,4-dimethylpiperidin-4-yl)benzo[d]thiazoleamine Prepared by general procedure scheme H step 1A. Yield: 3 g (41.38%).

CC conditions: The crude product was purified by silica gel with MeCN/MeOH (gradient 10-100% MeOH) as an eluent mixture.

LCMS(ESI): [M]+ m/z: calcd 280.2; found 281.2; Rt=1.529 min.

Step 2: Synthesis of 2-(1,4-dimethylpiperidin-4-yl)-5-(4,4,5,5-tetramethyl-1,3,2-dioxaborolan-2-yl)benzo[d]thiazole tris(Dibenzylideneacetone)dipalladium(0) (652.18 mg, 712.21 µmol) and XPhos (1.36 g, 2.85 mmol) was added to a solution of 5-chloro-2-(1,4-dimethyl-4-piperidyl)-1,3-benzothiazole (4 g, 14.24 mmol) and 4,4,5,5-tetramethyl-2-(4,4,5,5-tetramethyl-1,3,2-dioxaborolan-2-yl)-1,3,2-dioxaborolane (4.70 g, 18.52 mmol) in dioxane (60.00 mL). Reaction flask was evacuated and refilled with argon 3 times. Then potassium acetate (2.80 g, 28.49 mmol, 1.78 mL) was added under stream of argon. Resulting mixture was stirred at 100° C. for 15 hr under inert atmosphere, then cooled and evaporated in vacuum poured into water (120 mL) and extracted with DCM (2×50 mL), dried over sodium sulphate and evaporated in vacuum to afford 2-(1,4-dimethyl-4-piperidyl)-5-(4,4,5,5-tetramethyl-1,3,2-dioxaborolan-2-yl)-1,3-benzothiazole (0.9 g, 2.42 mmol, 16.97% yield).

LCMS(ESI): [M]+ m/z: calcd 372.2; found 373.2; Rt=3.119 min.

Step 3: Synthesis of (S)-tert-butyl 6-(2-(1,4-dimethylpiperidin-4-yl)benzo[d]thiazol-5-yl)-3-methyl-3,4-dihydropyridine-1(2H)-carboxylate Prepared by general procedure scheme H step 3. Yield: 1.3 g of crude.

LCMS(ESI): [M]+ m/z: calcd 441.2; found 442.2; Rt=1.289 min.

Step 4: Synthesis of (S)-2-(1,4-dimethylpiperidin-4-yl)-5-(5-methyl-3,4,5,6-tetrahydropyridin-2-yl)benzo[d]thiazole Prepared by general procedure scheme H step 4. Yield: 0.7 g of crude.

LCMS(ESI): [M]+ m/z: calcd 341.2; found 342.2; Rt=0.724 min.

Step 5: Synthesis of 2-(1,4-dimethylpiperidin-4-yl)-5-((2R,5S)-5-methylpiperidin-2-yl)benzo[d]thiazole Prepared by general procedure scheme H step 5. Yield: 0.55 g of crude.

LCMS(ESI): [M]+ m/z: calcd 343.2; found 344.2; Rt=1.772 min.

Step 6: Synthesis of N-(6-amino-5-ethylpyridin-3-yl)-2-((2R,5S)-2-(2-(1,4-dimethylpiperidin-4-yl)benzo[d]thiazol-5-yl)-5-methylpiperidin-1-yl)-2-oxoacetamide (Compound 1171

Prepared by general procedure scheme H step 6A. Yield: 31.4 mg (13.45%).

HPLC conditions: Column: XBridge C18 100*19 mm, 5 microM; 0-6 min 35-70% water-MeCN+0.1% NH4OH, flow: 30 mL/min; (loading pump 4 mL/min MeOH).

1H NMR (600 MHz, dmso) 6 0.98-1.06 (m, 3H), 1.06-1.15 (m, 3H), 1.31-1.40 (m, 4H), 1.67-1.75 (m, 1H), 1.78-1.93 (m, 3H), 2.01-2.11 (m, 1H), 2.12-2.17 (m, 3H), 2.17-2.32 (m, 5H), 2.32-2.38 (m, 2H), 2.38-2.44 (m, 2H), 2.77-3.26 (m, 1H), 3.43-4.11 (m, 1H), 5.26-5.61 (m, 1H), 5.62-5.75 (m, 2H), 7.35-7.43 (m, 1H), 7.43-7.53 (m, 1H), 7.85-7.93 (m, 1H), 7.98-8.11 (m, 2H), 10.49-10.68 (m, 1H).

LCMS(ESI): [M]+ m/z: calcd 534.2; found 535.2; Rt=2.430 min.

Example 612. The Synthesis of N-(6-amino-5-ethylpyridin-3-yl)-2-((2R,5S)-5-methyl-2-(2-(tetrahydrofuran-3-yl)benzo[d]thiazol-5-yl)piperidin-1-yl)-2-oxoacetamide (Compound 1242)

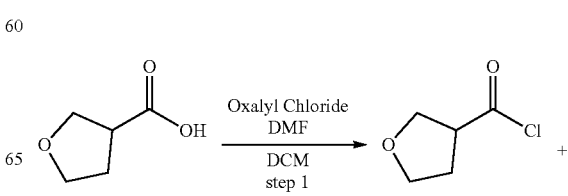

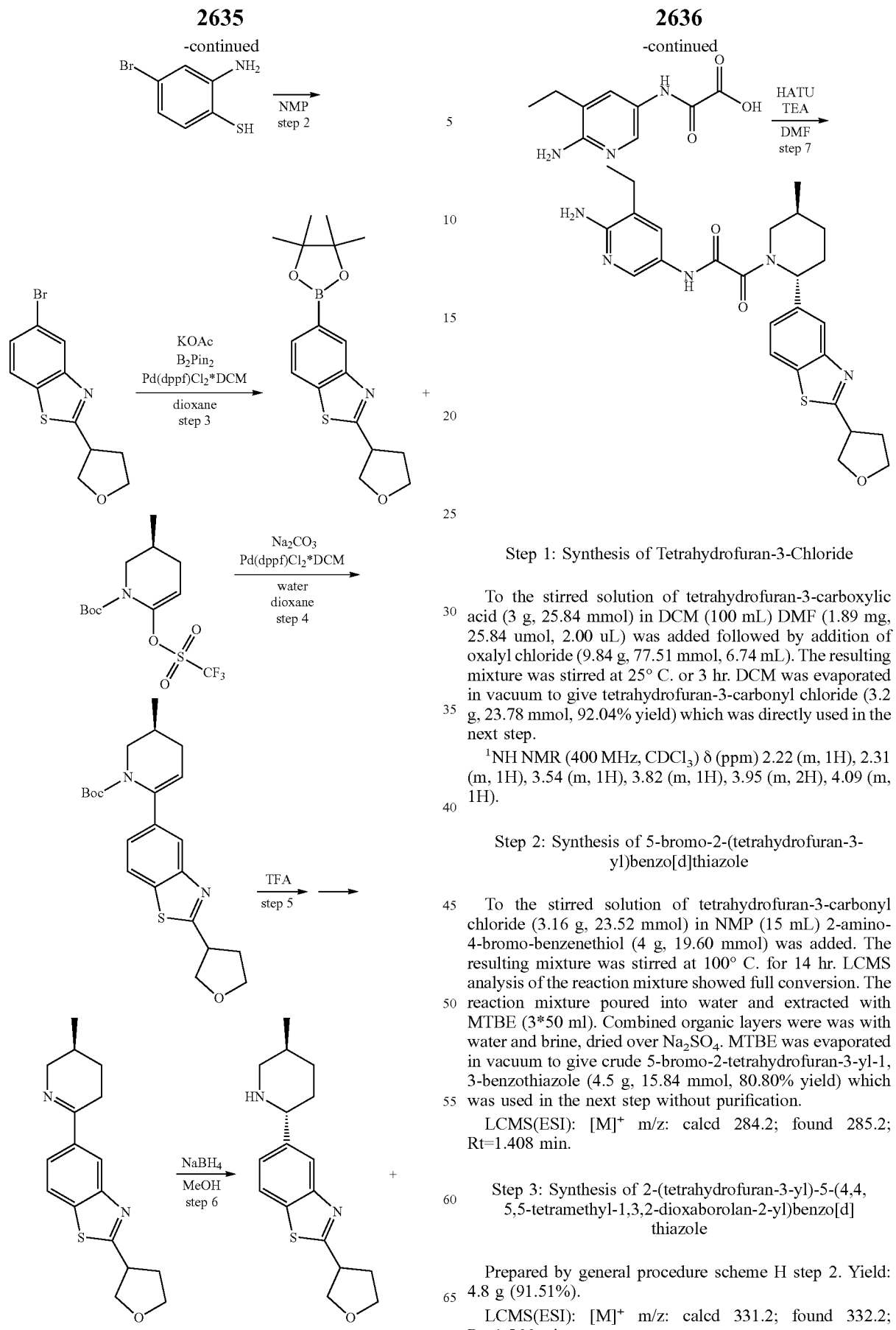

Step 1: Synthesis of Tetrahydrofuran-3-Chloride

To the stirred solution of tetrahydrofuran-3-carboxylic acid (3 g, 25.84 mmol) in DCM (100 mL) DMF (1.89 mg, 25.84 umol, 2.00 uL) was added followed by addition of oxalyl chloride (9.84 g, 77.51 mmol, 6.74 mL). The resulting mixture was stirred at 25° C. or 3 hr. DCM was evaporated in vacuum to give tetrahydrofuran-3-carbonyl chloride (3.2 g, 23.78 mmol, 92.04% yield) which was directly used in the next step.

$^1$NH NMR (400 MHz, CDCl$_3$) δ (ppm) 2.22 (m, 1H), 2.31 (m, 1H), 3.54 (m, 1H), 3.82 (m, 1H), 3.95 (m, 2H), 4.09 (m, 1H).

Step 2: Synthesis of 5-bromo-2-(tetrahydrofuran-3-yl)benzo[d]thiazole

To the stirred solution of tetrahydrofuran-3-carbonyl chloride (3.16 g, 23.52 mmol) in NMP (15 mL) 2-amino-4-bromo-benzenethiol (4 g, 19.60 mmol) was added. The resulting mixture was stirred at 100° C. for 14 hr. LCMS analysis of the reaction mixture showed full conversion. The reaction mixture poured into water and extracted with MTBE (3*50 ml). Combined organic layers were was with water and brine, dried over Na$_2$SO$_4$. MTBE was evaporated in vacuum to give crude 5-bromo-2-tetrahydrofuran-3-yl-1, 3-benzothiazole (4.5 g, 15.84 mmol, 80.80% yield) which was used in the next step without purification.

LCMS(ESI): [M]$^+$ m/z: calcd 284.2; found 285.2; Rt=1.408 min.

Step 3: Synthesis of 2-(tetrahydrofuran-3-yl)-5-(4,4,5,5-tetramethyl-1,3,2-dioxaborolan-2-yl)benzo[d]thiazole Prepared by general procedure scheme H step 2. Yield: 4.8 g (91.51%).

LCMS(ESI): [M]$^+$ m/z: calcd 331.2; found 332.2; Rt=1.566 min.

Step 4: Synthesis of (3S)-tert-butyl 3-methyl-6-(2-(tetrahydrofuran-3-yl)benzo[d]thiazol-5-yl)-3,4-dihydropyridine-1(2H)-carboxylate Prepared by general procedure scheme H step 3. Yield: 0.5 g (8.61%).
CC conditions: The crude product was purified by silica gel with hexane/MTBE as an eluent mixture.
LCMS(ESI): [M]⁺ m/z: calcd 400.2; found 401.2; Rt=1.562 min.

Step 5: Synthesis of 5-((S)-5-methyl-3,4,5,6-tetrahydropyridin-2-yl)-2-(tetrahydrofuran-3-yl)benzo[d]thiazole Prepared by general procedure scheme H step 4. Yield: 350 mg (93.33%).
LCMS(ESI): [M]⁺ m/z: calcd 300.2; found 301.2; Rt=0.774 min.

Step 6: Synthesis of 5-((2R,5S)-5-methylpiperidin-2-yl)-2-(tetrahydrofuran-3-yl)benzo[d]thiazole Prepared by general procedure scheme H step 5. Yield: 0.25 g (70.95%).
LCMS(ESI): [M]⁺ m/z: calcd 302.2; found 303.2; Rt=0.787 min.

Step 7: The Synthesis of N-(6-amino-5-ethylpyridin-3-yl)-2-((2R,5S)-5-methyl-2-(2-(tetrahydrofuran-3-yl)benzo[d]thiazol-5-yl)piperidin-1-yl)-2-oxoacetamide (Compound 1242

Prepared by general procedure scheme H step 6A. Yield: 127 mg (38.91%).
HPLC conditions: Column: YMC Triart C18 100*20 mm, 5 microM; 0-5 min 50-100% water-MeOH+0.1% NH₄OH; (loading pump 4 mL/min MeOH).
¹H NMR (600 MHz, dmso) δ 1.00-1.05 (m, 3H), 1.06-1.15 (m, 3H), 1.30-1.41 (m, 1H), 1.65-1.75 (m, 1H), 1.81-1.93 (m, 1H), 2.04-2.18 (m, 1H), 2.20-2.32 (m, 2H), 2.32-2.36 (m, 1H), 2.39-2.44 (m, 2H), 2.76-3.27 (m, 1H), 3.34-3.51 (m, 1H), 3.80-3.85 (m, 1H), 3.90-3.98 (m, 3H), 4.07-4.13 (m, 1H), 5.26-5.61 (m, 1H), 5.61-5.75 (m, 2H), 7.33-7.43 (m, 1H), 7.43-7.55 (m, 1H), 7.84-7.92 (m, 1H), 7.97-8.09 (m, 2H), 10.49-10.71 (m, 1H).
LCMS(ESI): [M]⁺ m/z: calcd 493.2; found 494.2; Rt=2.640 min.

Example 613. The Synthesis of N-(5,6-dimethylpyridin-3-yl)-2-((2R,5S)-5-methyl-2-(2-(1,2,2,6,6-Pentamethylpiperidin-4-yl)benzo[d]thiazol-5-yl)piperidin-1-yl)-2-oxoacetamide (Compound 1315

Step 1: Synthesis of 5-chloro-2-(2,2,6,6-tetramethylpiperidin-4-yl)benzo[d]thiazole (Compound 1315)

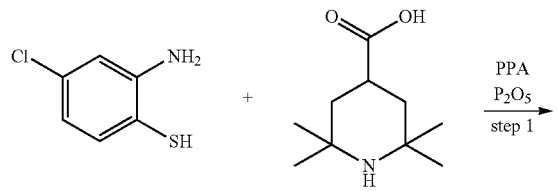

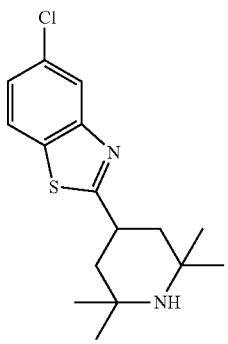

Prepared by general procedure scheme H step 1A. Yield: 3.75 g (40.80%).
CC conditions: The crude product was purified by silica gel with MTBE/MeOH as an eluent mixture.
LCMS(ESI): [M]⁺ m/z: calcd 308.2; found 309.2; Rt=1.063 min.

Step 2: Synthesis of 5-chloro-2-(1,2,2,6,6-Pentamethylpiperidin-4-yl)benzo[d]thiazole

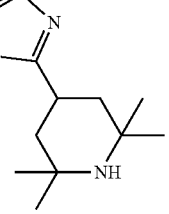

K₂SO₃
TosOMe
MeCN
step 2

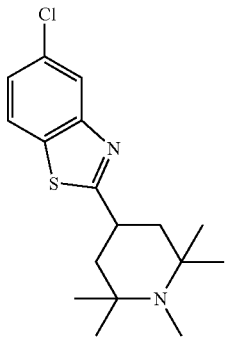

Methyl tosylate (2.35 g, 12.64 mmol, 1.91 mL) and potassium carbonate (3.18 g, 22.99 mmol, 1.39 mL) were added to the solution of 5-chloro-2-(2,2,6,6-tetramethyl-4-piperidyl)-1,3-benzothiazole (3.55 g, 11.49 mmol) in MeCN (50 mL). Resulting mixture was stirred at 80° C. for 48 hr. Then, solvent was removed under reduced pressure. Residue was suspended in MTBE (60 ml), filtered and concentrated in vacuum, leaving 5-chloro-2-(1,2,2,6,6-pentamethyl-4-piperidyl)-1,3-benzothiazole (3.89 g, crude).

LCMS(ESI): [M]⁺ m/z: calcd 322.2; found 323.2; Rt=1.071 min.

Step 3: Synthesis of 2-(1,2,2,6,6-Pentamethylpiperidin-4-yl)-5-(4,4,5,5-tetramethyl-1,3,2-dioxaborolan-2-yl)benzo[d]thiazole

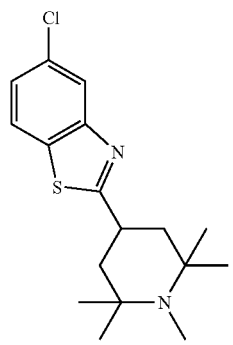

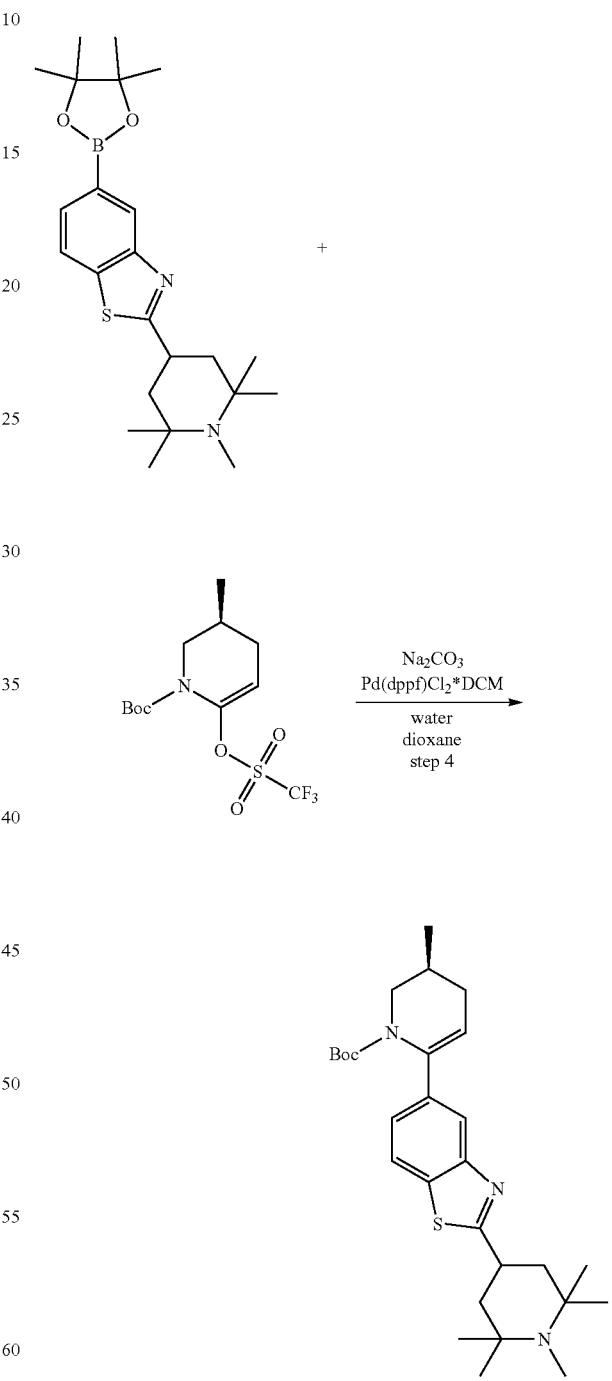

5-chloro-2-(1,2,2,6,6-pentamethyl-4-piperidyl)-1,3-benzothiazole (3.89 g, 12.05 mmol), 4,4,5,5-tetramethyl-2-(4,4,5,5-tetramethyl-1,3,2-dioxaborolan-2-yl)-1,3,2-dioxaborolane (3.52 g, 13.85 mmol) and potassium acetate (2.36 g, 24.09 mmol, 1.51 mL) were mixed together in dioxane (60 mL). Reaction flask was evacuated and refilled with argon 3 times. Then, XPhos (1.15 g, 2.41 mmol) and tris(dibenzylideneacetone)dipalladium (0) (551.60 mg, 602.36 μmol) were added under stream of argon. Resulting mixture was stirred at 100° C. for 16 hr. Then, it was concentrated under reduced pressure and residue was purified by gradient column chromatography (SiO₂, MTBE/MeOH), affording 2-(1,2,2,6,6-pentamethyl-4-piperidyl)-5-(4,4,5,5-tetramethyl-1,3,2-dioxaborolan-2-yl)-1,3-benzothiazole (3 g, 7.24 mmol, 60.09% yield).

LCMS(ESI): [M]⁺ m/z: calcd 414.2; found 415.2; Rt=1.144 min.

Step 4: Synthesis of (S)-tert-butyl 3-methyl-6-(2-(1,2,2,6,6-Pentamethylpiperidin-4-yl)benzo[d]thiazol-5-1-3,4-dihydropyridine-1(2H)-carboxylate Prepared by general procedure scheme H step 3. Yield: 3.6 g of crude.

LCMS(ESI): [M]⁺ m/z: calcd 483.2; found 484.2; Rt=1.398 min.

Step 5: Synthesis of (S)-5-(5-methyl-3,4,5,6-tetra-hydropyridin-2-yl)-2-(1,2,2,6,6-Pentamethylpiperidin-4-yl)benzo[d]thiazole

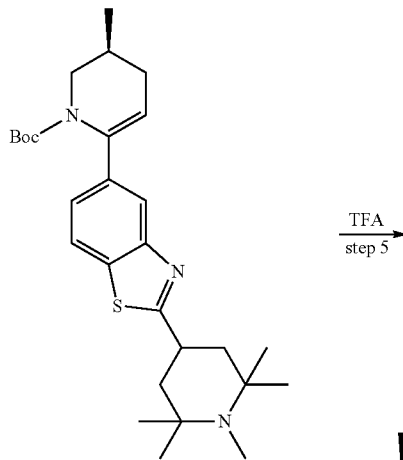

TFA
step 5

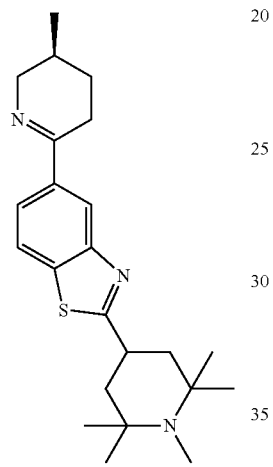

Prepared by general procedure scheme H step 4. Yield: 1.2 g of crude.
LCMS(ESI): [M]+ m/z: calcd 383.2; found 384.2; Rt=0.753 min.

Step 6: Synthesis of 5-((2R,5S)-5-methylpiperidin-2-yl)-2-(1,2,2,6,6-Pentamethylpiperidin-4-yl)benzo[d]thiazole

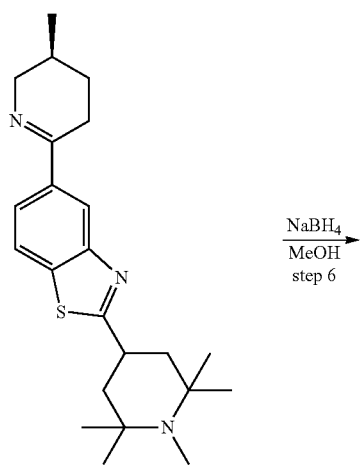

NaBH₄
MeOH
step 6

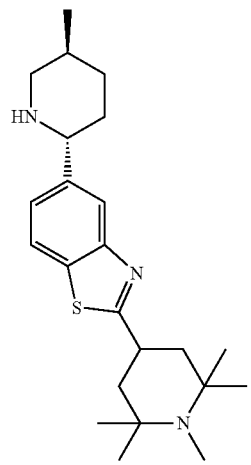

Prepared by general procedure scheme H step 5. Yield: 0.92 g of crude.
LCMS(ESI): [M]+ m/z: calcd 385.2; found 386.2; Rt=0.796 min.

The Synthesis of N-(5,6-dimethylpyridin-3-yl)-2-((2R,5S)-5-methyl-2-(2-(1,2,2,6,6-Pentamethylpiperidin-4-yl)benzo[d]thiazol-5-yl)piperidin-1-yl)-2-oxoacetamide (Compound 1315)

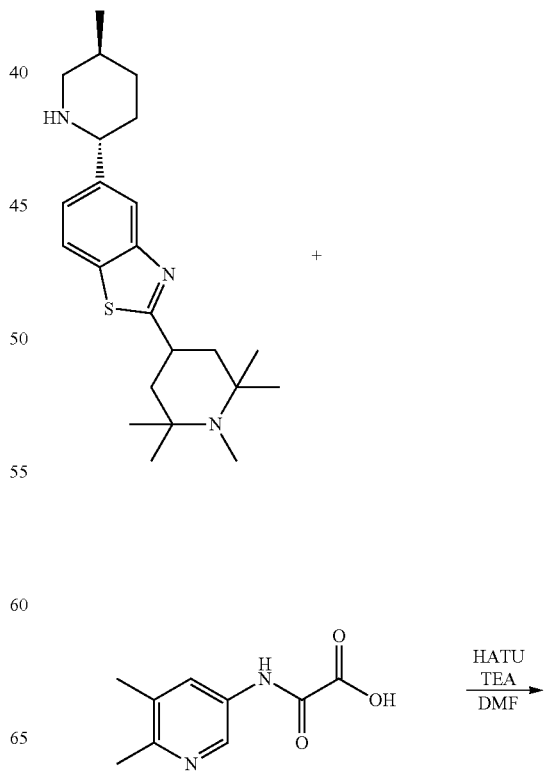

HATU
TEA
DMF

-continued

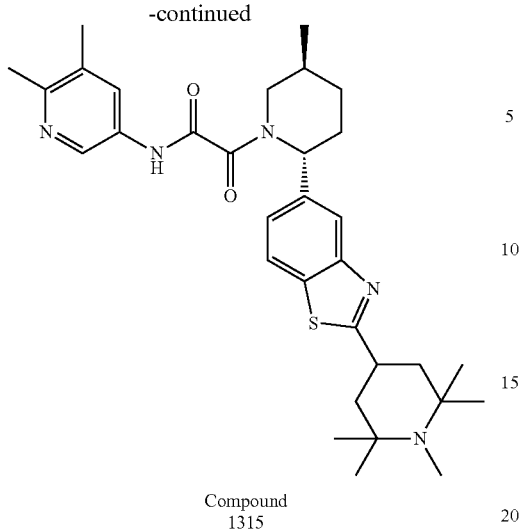

Compound 1315

Prepared by general procedure scheme H step 6A. Yield: 33.7 mg (14.30%).

HPLC conditions: Column: YMC Triart C18 100*20 mm, 5 microM; 0-1-6 min 70-70-85% water-MeOH+0.1% NH₄OH; (loading pump 4 mL/min MeOH).

¹H NMR (600 MHz, DMSO-d₆) δ (ppm) 1.01-1.06 (m, 3H), 1.06-1.09 (m, 6H), 1.10-1.14 (m, 6H), 1.31-1.41 (m, 1H), 1.59-1.76 (m, 3H), 1.82-1.98 (m, 3H), 2.07-2.19 (m, 2H), 2.21 (s, 3H), 2.24 (s, 2H), 2.28-2.38 (m, 4H), 2.80-3.28 (m, 1H), 3.43-4.05 (m, 2H), 5.24-5.73 (m, 1H), 7.34-7.44 (m, 1H), 7.71-7.85 (m, 1H), 7.85-7.92 (m, 1H), 8.02-8.09 (m, 1H), 8.37-8.54 (m, 1H), 10.90-11.03 (m, 1H).

LCMS(ESI): [M]⁺ m/z: calcd 561.2; found 562.2; Rt=2.465 min.

Example 614. The Synthesis of N-(6-amino-5-ethylpyridin-3-yl)-2-((2R,5S)-2-(2-((3-(dimethylamino)oxetan-3-yl)methyl)benzo[d]thiazol-5-yl)-5-methylpiperidin-1-yl)-2-oxoacetamide (Compound 1399)

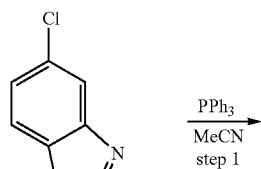

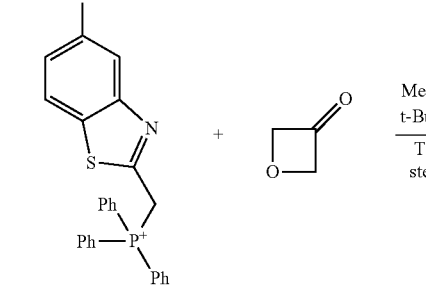

-continued

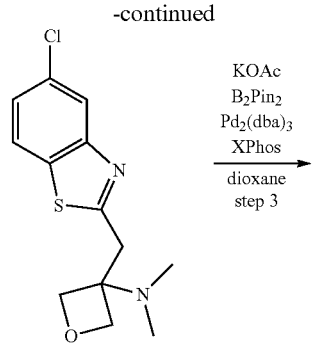

KOAc
B₂Pin₂
Pd₂(dba)₃
XPhos
—————
dioxane
step 3

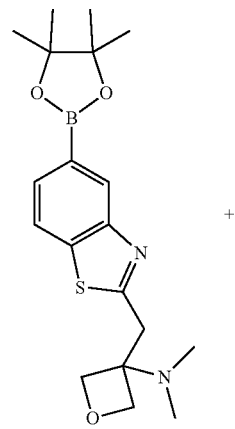

+

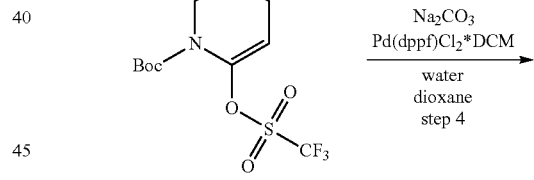

Na₂CO₃
Pd(dppf)Cl₂*DCM
—————
water
dioxane
step 4

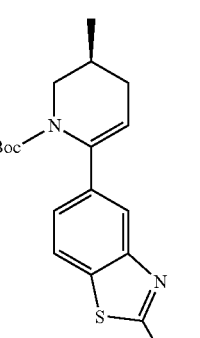

TFA
———
DCM
step 5

-continued

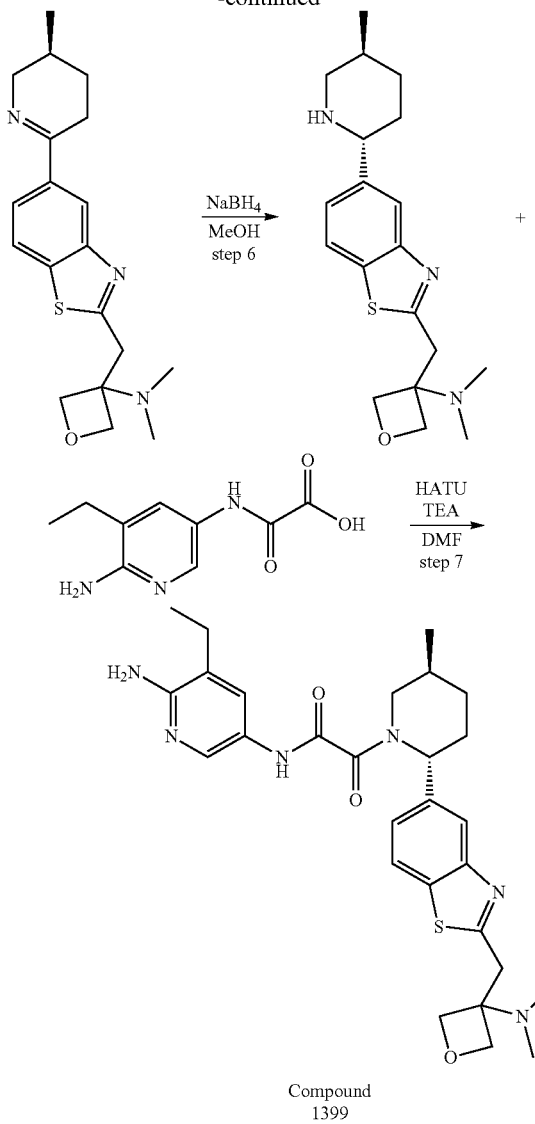

Compound 1399

Step 1: Synthesis of ((5-chlorobenzo[d]thiazol-2-yl)methyl)triphenylphosphonium

Triphenylphosphane (4.01 g, 15.29 mmol) was added to the solution of 5-chloro-2-(chloromethyl)-1,3-benzothiazole (2.9 g, 13.30 mmol) in MeCN (50 mL). Resulting mixture was stirred at 80° C. for 24 hr. Then, solvent was removed under reduced pressure. Residue was triturated with cold MTBE (60 mL). Precipitated brown solid was filtered and dried, affording (5-chloro-1,3-benzothiazol-2-yl)methyl-triphenyl-phosphonium (5.16 g, 10.74 mmol, 80.78% yield, Cl⁻).

LCMS(ESI): [M]⁺ m/z: calcd 480.2; found 481.2; Rt=1.358 min.

Step 2: Synthesis of 3-((5-chlorobenzo[d]thiazol-2-yl)methyl)-N,N-dimethyloxetan-3-amine Potassium tert-butoxide (991.15 mg, 8.83 mmol) was added to the suspension of (5-chloro-1,3-benzothiazol-2-yl)methyl-triphenyl-phosphonium (4.16 g, 8.66 mmol, Cl⁻) in THF (80 mL). After 2.5 hr stirring at 20° C., oxetan-3-one (686.44 mg, 9.53 mmol, 610.71 μL) was added thereto and resulting mixture was stirred for 2.5 hr more. Then, Dimethylamine solution 17% in THF (9.19 g, 34.64 mmol, 17% purity) was added and resulting mixture was stirred at 50° C. for 18 hr. After that, solvent was removed under reduced pressure and solid residue was thoroughly extracted with 5% aq. NaHSO₄ solution (2×60 mL). Insoluble triphenylphosphine oxide was filtered off and filtrate was washed with DCM (20 mL). Aqueous layer was separated and basified with solid K₂CO₃ to pH≈10-11. Resulting cloudy solution was extracted with DCM (3×30 mL). Combined organic layers were dried over solid K₂CO₃ and concentrated under reduced pressure, affording 3-[(5-chloro-1,3-benzothiazol-2-yl)methyl]-N,N-dimethyl-oxetan-3-amine (2.6 g, crude).

LCMS(ESI): [M]⁺ m/z: calcd 282.2; found 283.2; Rt=0.962 min.

Step 3: Synthesis of N,N-dimethyl-3-((5-(4,4,5,5-tetramethyl-1,3,2-dioxaborolan-2-yl)benzo[d]thiazol-2-yl)methyl)oxetan-3-amine 3-[(5-chloro-1,3-benzothiazol-2-yl)methyl]-N,N-dimethyl-oxetan-3-amine (2.6 g, 9.19 mmol), 4,4,5,5-tetramethyl-2-(4,4,5,5-tetramethyl-1,3,2-dioxaborolan-2-yl)-1,3,2-dioxaborolane (2.80 g, 11.03 mmol) and potassium acetate (1.80 g, 18.39 mmol, 1.15 mL) were mixed together in dioxane (50 mL). Reaction flask was evacuated and refilled with argon 3 times. Then, tris(dibenzylideneacetone)dipalladium (0) (420.96 mg, 459.71 μmol) and XPhos (876.60 mg, 1.84 mmol) were added under stream of argon. Resulting mixture was stirred at 100° C. for 18 hr. Then, it was concentrated under reduced pressure and residue was extracted with MTBE (2×30 mL). Resulting MTBE solution was extracted with solution of sodium hydrogen sulfate (3.31 g, 27.58 mmol) in water (50 mL). Aqueous layer was separated and filtered through a paper filter to remove cloudiness. Resulting clear solution was used in next step as is.

LCMS(ESI): [M]⁺ m/z: calcd 374.2; found 375.2; Rt=1.172 min.

Step 4: Synthesis of (S)-tert-butyl 6-(2-((3-(dimethylamino)oxetan-3-yl)methyl)benzo[d]thiazol-5-yl)-3-methyl-3,4-dihydropyridine-1(2H)-carboxylate Prepared by general procedure scheme H step 3. Yield: 3.73 g of crude.

LCMS(ESI): [M]⁺ m/z: calcd 443.2; found 444.2; Rt=1.264 min.

Step 5: Synthesis of (S)—N,N-dimethyl-3-((5-(5-methyl-3,4,5,6-tetrahydropyridin-2-yl)benzo[d]thiazol-2-yl)methyl)oxetan-3-amine Prepared by general procedure scheme H step 4. Yield: 0.7 g of crude.

LCMS(ESI): [M]⁺ m/z: calcd 343.2; found 344.2; Rt=0.636 min.

Step 6: Synthesis of N,N-dimethyl-3-((5-((2R,5S)-5-methylpiperidin-2-yl)benzo[d]thiazol-2-yl)methyl)oxetan-3-amine Prepared by general procedure scheme H step 5. Yield: 0.57 g of crude.

LCMS(ESI): [M]+ m/z: calcd 345.2; found 346.2; Rt=0.575 min.

Step 7: Synthesis of N-(6-amino-5-ethylpyridin-3-yl)-2-((2R,5S)-2-(2-((3-(dimethylamino)oxetan-3-yl)methyl)benzo[d]thiazol-5-yl)-5-methylpiperidin-1-yl)-2-oxoacetamide (Compound 1399

Prepared by general procedure scheme H step 6A. Yield: 53.9 mg (30.44%).
HPLC conditions: Column: YMC Triart C18 100*20 mm, 5 microM; 0-1-5 min 10-10-45% water-MeCN+0.1% NH$_4$OH, flow: 30 mL/min; (loading pump 4 mL/min MeCN).
$^1$H NMR (600 MHz, DMSO-d$_6$) δ (ppm) 0.97-1.05 (m, 3H), 1.06-1.16 (m, 3H), 1.30-1.41 (m, 1H), 1.66-1.76 (m, 1H), 1.83-1.92 (m, 1H), 2.04-2.35 (m, 9H), 2.39-2.43 (m, 1H), 2.74-3.28 (m, 1H), 3.42-4.11 (m, 3H), 4.40-4.50 (m, 2H), 4.50-4.60 (m, 2H), 5.24-5.72 (m, 3H), 7.32-7.55 (m, 2H), 7.84-7.93 (m, 1H), 7.97-8.11 (m, 2H), 10.48-10.65 (m, 1H).
LCMS(ESI): [M]+ m/z: calcd 536.2; found 537.2; Rt=2.147 min.

Example 615. The Synthesis of N-(6-amino-5-ethylpyridin-3-yl)-2-((2R,5)-5-methyl-2-(2-(4-methylmorpholin-3-yl)benzo[d]thiazol-5-yl)piperidin-1-yl)-2-oxoacetamide (Compound 1245)

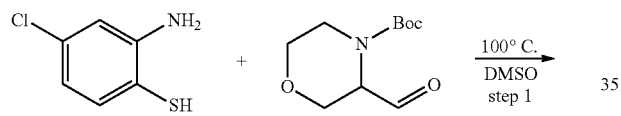

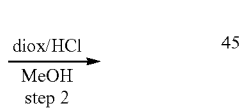

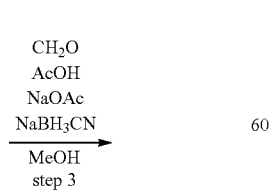

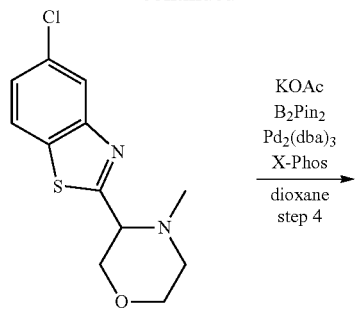

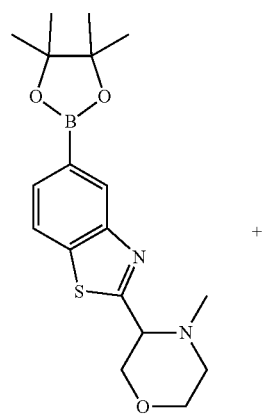

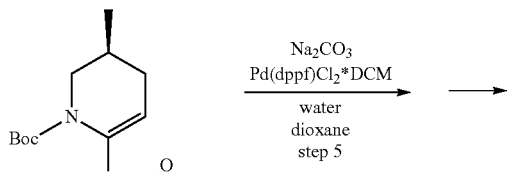

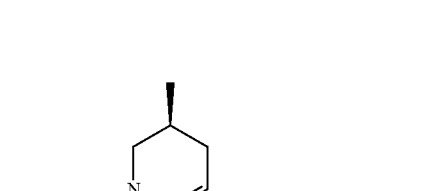

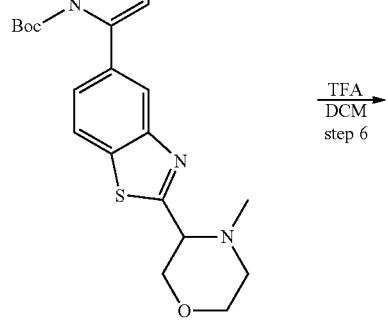

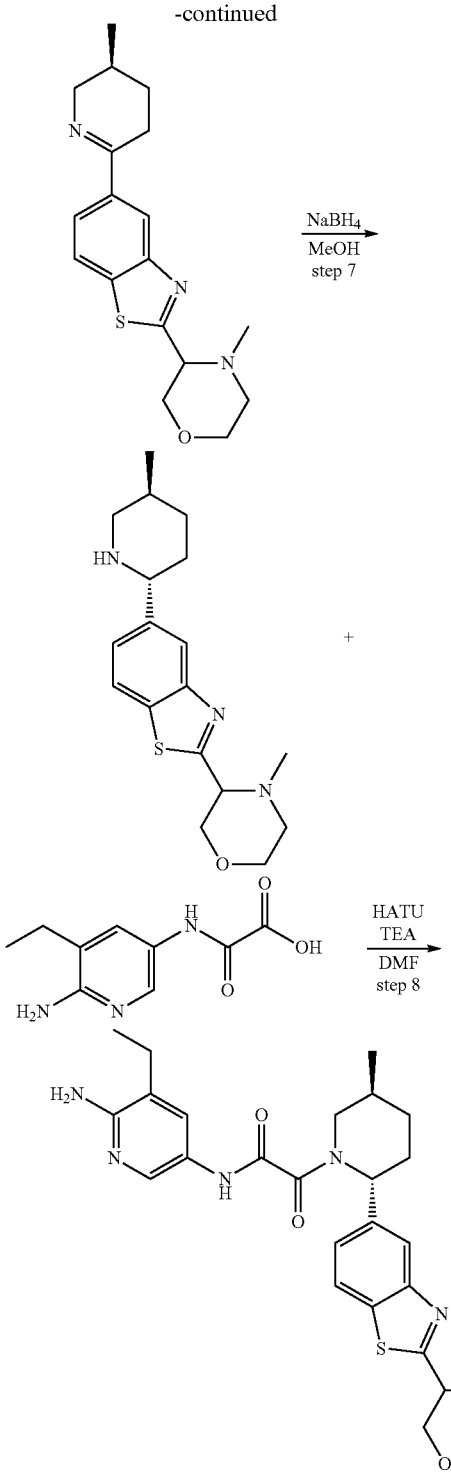

Step 2: Synthesis of tert-butyl 3-(5-chlorobenzo[d]thiazol-2yl)morpholine-4-carboxylate Prepared by general procedure scheme H step 1B. Yield: 2.2 g (14.140%).

CC conditions: The crude product was purified by silica gel with Hexane/MTBE (gradient 10-100% MTBE) as an eluent mixture.

LCMS(ESI): [M]$^+$ m/z: calcd 354.2; found 355.2; Rt=1.582 min.

Step 2: Synthesis of 3-(5-chlorobenzo[d]thiazol-2-yl)morpholine

Hydrogen chloride solution 4.0 M in dioxane (800.00 mg, 21.94 mmol, 1 mL) was added to a solution of tert-butyl 3-(5-chloro-1,3-benzothiazol-2-yl)morpholine-4-carboxylate (0.2 g, 563.62 µmol) in MeOH (10 mL). The reaction mixture was stirred at 20° C. for 7 hr, then evaporated and added to MTBE (10 mL) the resulting precipitate was filtered off, washed with MTBE (10 mL) and dried to afford 3-(5-chloro-1,3-benzothiazol-2-yl)morpholine (0.1 g, 343.41 mol, 60.93% yield, HCl).

LCMS(ESI): [M]$^+$ m/z: calcd 254.2; found 255.2; Rt=0.746 min.

Step 3: Synthesis of 3-(5-chlorobenzo[d]thiazol-2-yl)-4-methylmorpholine 3-(5-chloro-1,3-benzothiazol-2-yl)morpholine (1.3 g, 4.46 mmol, HCl) was dissolved in MeOH (29.00 mL) and sodium acetate, anhydrous (439.47 mg, 5.36 mmol, 287.61 µL), formaldehyde, 37% w/w aq. soln., stab. with 7-8% MeOH (268.13 mg, 8.93 mmol, 247.58 µL), was added of AcOH (536.19 mg, 8.93 mmol, 511.14 µL) was added thereto and reaction mixture was stirred at rt hr. Then sodium cyan borohydride (561.08 mg, 8.93 mmol) was added portion wise. The resulting mixture was stirred at 0° C. for 7 hr, and then evaporated in vacuum. The residue was diluted with 100 mL NaOH (10%) and extracted with DCM (2*30 mL). The combined organic extracts were dried over sodium sulphate and evaporated in vacuum to afford tert-butyl 4-fluoro-4-(hydroxymethyl)piperidine-1-carboxylate (5.6 g, 24.01 mmol, 83.10% yield).

LCMS(ESI): [M]$^+$ m/z: calcd 268.2; found 269.2; Rt=2.096 min.

Step 4: Synthesis of 4-methyl-3-(5-(4,4,5,5-tetramethyl-1,3,2-dioxaborolan-2-yl)benzo[d]thiazol-2-yl) morpholine tris(Dibenzylideneacetone)dipalladium(0) (238.50 mg, 260.45 µmol) and XPhos (496.65 mg, 1.04 mmol) was added to a solution of 3-(5-chloro-1,3-benzothiazol-2-yl)-4-methyl-morpholine (1.4 g, 5.21 mmol) and 4,4,5,5-tetramethyl-2-(4,4,5,5-tetramethyl-1,3,2-dioxaborolan-2-yl)-1,3,2-dioxaborolane (1.72 g, 6.77 mmol) in dioxane (29.35 mL). Reaction flask was evacuated and refilled with argon 3 times. Then potassium acetate (1.53 g, 15.63 mmol, 976.85 µL) was added under stream of argon. Resulting mixture was stirred at 100° C. for 12 hr under inert atmosphere, then cooled and evaporated in vacuum poured into water (200 mL) and extracted with DCM (2×30 mL), dried over sodium sulphate and evaporated in vacuum to leave 1.8 g of crude product, 1.8 g of which was purification by column chromatography on silica gel using Hexane/MTBE gradient (10-100% MTBE) to afford 4-methyl-3-[5-(4,4,5,5-tetramethyl-1,3,2-dioxaborolan-2-yl)-1,3-benzothiazol-2-yl]morpholine (1.1 g, 3.05 mmol, 58.61% yield).

LCMS(ESI): [M]$^+$ m/z: calcd 360.2; found 361.2; Rt=2.608 min.

Step 5: Synthesis of (3S)-tert-butyl 3-methyl-6-(2-(4-methylmorpholin-3-yl)benzo[d]thiazol-5-yl)-3,4-dihydropyridine-1(2H)-carboxylate Prepared by general procedure scheme H step 3. Yield: 1.4 g of crude.

LCMS(ESI): [M]⁺ m/z: calcd 429.2; found 430.2; Rt=3.782 min.

Step 6: Synthesis of 4-methyl-3-(5-((S)-5-methyl-3,4,5,6-tetrahydropyridin-2-yl)benzo[d]thiazol-2-yl)morpholine Prepared by general procedure scheme H step 4. Yield: 0.7 g of crude.
LCMS(ESI): [M]⁺ m/z: calcd 329.2; found 330.2; Rt=0.635 min.

Step 7: Synthesis of 4-methyl-3-(5-((2R,5S)-5-methylpiperidin-2-yl)benzo[d]thiazol-2-yl)morpholine Prepared by general procedure scheme H step 5. Yield: 0.6 g (85.19%).
LCMS(ESI): [M]⁺ m/z: calcd 331.2; found 332.2; Rt=0.828 min.

Step 8: Synthesis of N-(6-amino-5-ethylpyridin-3-yl)-2-((2R,5S)-5-methyl-2-(2-(4-methylmorpholin-3-yl)benzo[d]thiazol-5-yl)piperidin-1-yl)-2-oxoacetamide (Compound 1245

Prepared by general procedure scheme H step 6A. Yield: 57.4 mg (18.20%).
HPLC conditions: Column: XBridge C18 100*19 mm, 5 microM; 0-6 min 40-90% water-MeOH+0.1% NH₄OH, flow: 30 mL/min; (loading pump 4 mL/min MeCN).
¹H NMR (600 MHz, dmso) δ 1.00-1.05 (m, 3H), 1.05-1.14 (m, 3H), 1.30-1.40 (m, 1H), 1.65-1.74 (m, 1H), 1.82-1.93 (m, 1H), 2.07-2.21 (m, 4H), 2.25-2.36 (m, 2H), 2.40-2.43 (m, 1H), 2.76-3.27 (m, 2H), 3.38-4.08 (m, 7H), 5.26-5.71 (m, 3H), 7.37-7.44 (m, 1H), 7.44-7.54 (m, 1H), 7.88-7.94 (m, 1H), 7.97-8.12 (m, 2H), 10.42-10.65 (m, 1H).
LCMS(ESI): [M]⁺ m/z: calcd 522.2; found 523.2; Rt=2.532 min.

Example 616. The Synthesis of N-(6-amino-5-ethylpyridin-3-yl)-2-((2R,5S)-2-(2-(2-(dimethylamino)propan-2-yl)benzo[d]thiazol-5-yl)-5-methylpiperidin-1-yl)-2-oxoacetamide (Compound 1250)

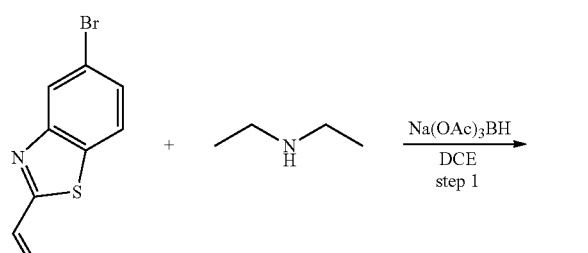

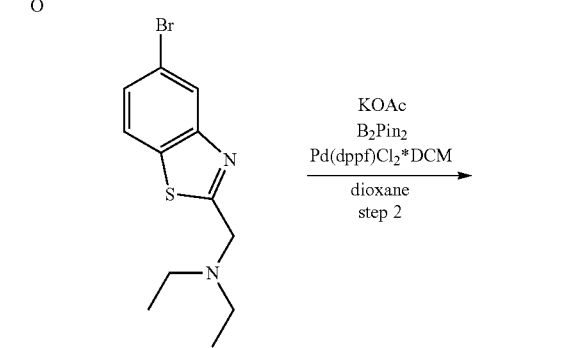

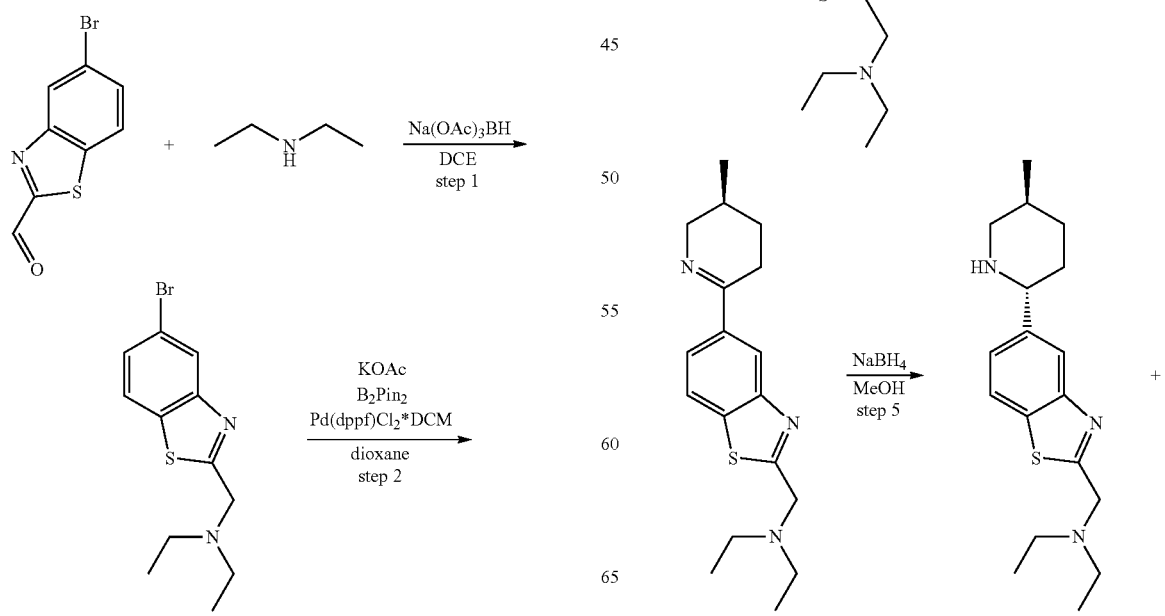

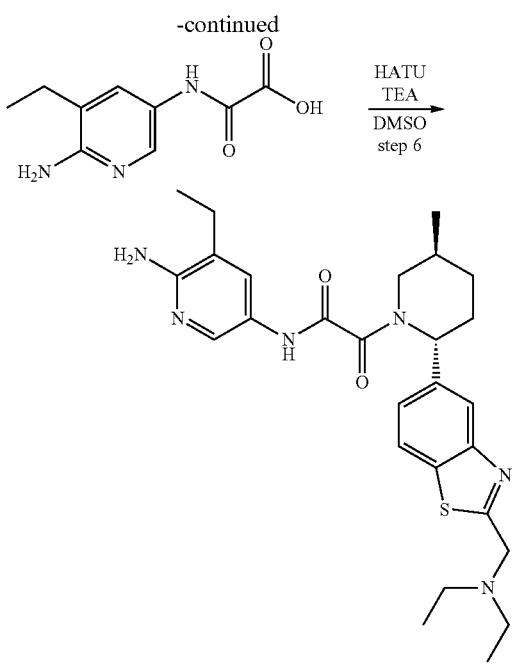

Step 1: Synthesis of N-((5-bromobenzo[d]thiazol-2-yl)methyl)-N-ethylethanamine

Prepared by general procedure scheme H step 1C. Yield: 4.1 g of crude.
LCMS(ESI): [M]$^+$ m/z: calcd 299.2; found 300.2; Rt=0.785 min.

Step 2: Synthesis of N-ethyl-N-((5-(4,4,5,5-tetramethyl-1,3,2-dioxaborolan-2-yl)benzo[d]thiazol-2-yl)methyl)ethanamine Prepared by general procedure scheme H step 2. Yield: 4.2 g of crude.
LCMS(ESI): [M]$^+$ m/z: calcd 346.2; found 347.2; Rt=1.030 min.

Step 3: Synthesis of (S)-tert-butyl 6-(2-((diethylamino)methyl)benzo[d]thiazol-5-yl)-3-methyl-3,4-dihydropyridine-1(2H)-carboxylate Prepared by general procedure scheme H step 3. Yield: 1.2 g (36.07%).
CC conditions: The crude product was purified by silica gel with MTBE/MeOH as an eluent mixture.
LCMS(ESI): [M]$^+$ m/z: calcd 415.2; found 416.2; Rt=1.264 min.

Step 4: Synthesis of (S)—N-ethyl-N-((5-(5-methyl-3,4,5,6-tetrahydropyridin-2-yl)benzo[d]thiazol-2-yl)methyl)ethanamine Prepared by general procedure scheme H step 4. Yield: 0.67 g of crude.
LCMS(ESI): [M]$^+$ m/z: calcd 315.2; found 316.2; Rt=0.225 min.

Step 5: Synthesis of N-ethyl-N-((5-((2R,5S)-5-methylpiperidin-2-yl)benzo[d]thiazol-2-yl)methyl)ethanamine Prepared by general procedure scheme H step 5. Yield: 0.62 g (91.95%).
LCMS(ESI): [M]$^+$ m/z: calcd 317.2; found 318.2; Rt=0.697 min.

Step 6: Synthesis of N-(6-amino-5-ethylpyridin-3-yl)-2-((2R,5S)-2-(2-(2-(dimethylamino)propan-2-yl)benzo[d]thiazol-5-yl)-5-methylpiperidin-1-yl)-2-oxoacetamide (Compound 1250

Prepared by general procedure scheme H step 6A. Yield: 20.8 mg (11.91%).
HPLC conditions: Column: SunFire C18 100*19 mm, 5 microM; 2-10 min 40-55% water-MeCN+FA, flow: 30 mL/min; (loading pump 4 mL/min MeCN).
$^1$H NMR (600 MHz, dmso) δ 0.99-1.05 (m, 9H), 1.05-1.14 (m, 3H), 1.30-1.41 (m, 1H), 1.66-1.75 (m, 1H), 1.82-1.92 (m, 1H), 2.05-2.23 (m, 1H), 2.27-2.35 (m, 1H), 2.40 (q, 1H), 2.57-2.63 (m, 5H), 2.75-3.00 (m, 1H), 3.45-4.07 (m, 3H), 5.23-5.73 (m, 3H), 7.30-7.41 (m, 1H), 7.42-7.55 (m, 1H), 7.81-7.87 (m, 1H), 7.98-8.05 (m, 1H), 8.06-8.21 (m, 1H), 10.49-10.59 (m, 1H).
LCMS(ESI): [M]$^+$ m/z: calcd 508.2; found 509.2; Rt=2.151 min.

Example 617. The Synthesis of 2-((2R,5)-5-methyl-2-(2-(1-methylpiperidin-4-yl)benzo[d]thiazol-5-yl)piperidin-1-yl)-N-(6-methyl-5-(trifluoromethyl)pyridin-3-yl)-2-oxoacetamide (Compound 1300)

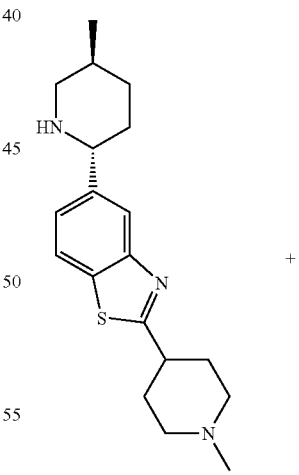

+

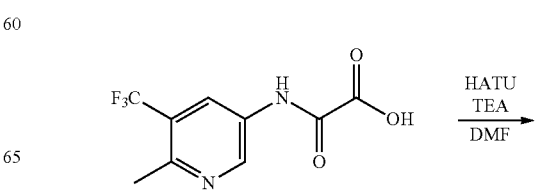

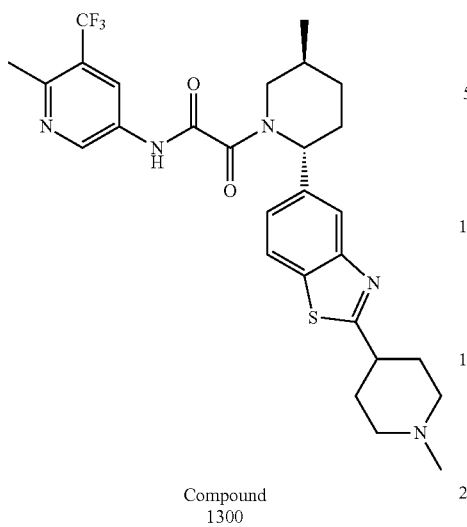

Compound
1300

Prepared by general procedure scheme H step 6A. Yield: 58 mg (20.85%).

HPLC conditions: Column: XBridge C18 100*19 mm, 5 microM; 0-5 min 40-90% water-MeOH+0.1% NH$_4$OH; (loading pump 4 mL/min MeCN).

$^1$H NMR (600 MHz, DMSO-d$_6$) δ (ppm) 0.99-1.07 (m, 3H), 1.31-1.40 (m, 1H), 1.68-1.76 (m, 1H), 1.77-1.84 (m, 2H), 1.84-1.95 (m, 1H), 1.98-2.11 (m, 5H), 2.18 (s, 3H), 2.29-2.34 (m, 1H), 2.54-2.60 (m, 3H), 2.78-3.12 (m, 4H), 3.51-4.04 (m, 1H), 5.28-5.75 (m, 1H), 7.32-7.42 (m, 1H), 7.88 (s, 1H), 8.00-8.11 (m, 1H), 8.31-8.51 (m, 1H), 8.82-8.98 (m, 1H), 11.24

11.49 (m, 1H).

LCMS(ESI): [M]$^+$ m/z: calcd 559.2; found 560.2; Rt=3.137 min.

Example 618. The Synthesis of 5-(2-((2R,5)-5-methyl-2-(2-(1-methylpiperidin-4-yl)benzo[d]thiazol-5-yl)piperidin-1-yl)-2-oxoacetamido)-2-(trifluoromethoxy)nicotinamide (Compound 1337)

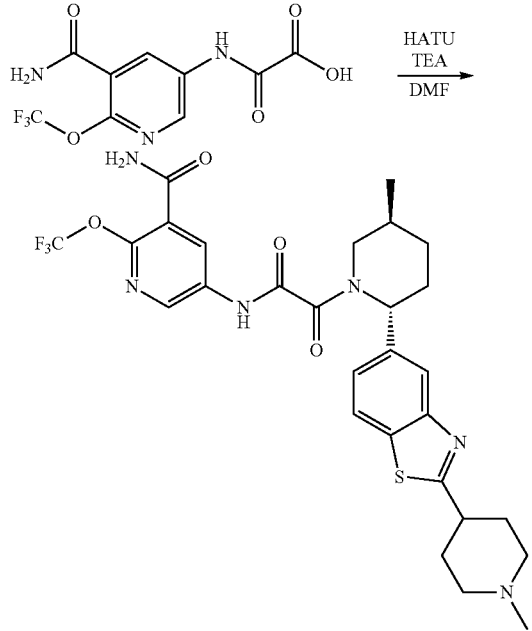

Compound
1337

Prepared by general procedure scheme H step 6A. Yield: 78 mg (31.65%).

HPLC conditions: Column: XBridge C18 100*19 mm, 5 microM; 0-5 min 30-80% water-MeOH+0.1% NH$_4$OH; (loading pump 4 mL/min MeOH).

$^1$H NMR (600 MHz, DMSO-d$_6$) δ (ppm) 0.95-1.09 (m, 3H), 1.31-1.43 (m, 1H), 1.66-1.75 (m, 1H), 1.75-1.93 (m, 3H), 1.93-2.16 (m, 5H), 2.18 (s, 3H), 2.28-2.37 (m, 1H), 2.78-2.87 (m, 2.3H), 2.98-3.08 (m, 1H), 3.31-3.37 (m, 0.7H), 3.45-4.12 (m, 1H), 5.15-5.76 (m, 1H), 7.30-7.43 (m, 1H), 7.71-7.83 (m, 1H), 7.85-7.91 (m, 1H), 7.91-8.02 (m, 1H), 8.02-8.10 (m, 1H), 8.27-8.41 (m, 1H), 8.50-8.68 (m, 1H), 11.16-11.59 (m, 1H).

LCMS(ESI): [M+1]$^+$ m/z: calcd 604.2; found 605.2; Rt=2.888 min.

Example 619. The Synthesis of 2-methyl-5-(2-((2R, 5S)-5-methyl-2-(2-(1-methylpiperidin-4-yl)benzo[d]thiazol-5-yl)piperidin-1-yl)-2-oxoacetamido)nicotinamide (Compound 1326)

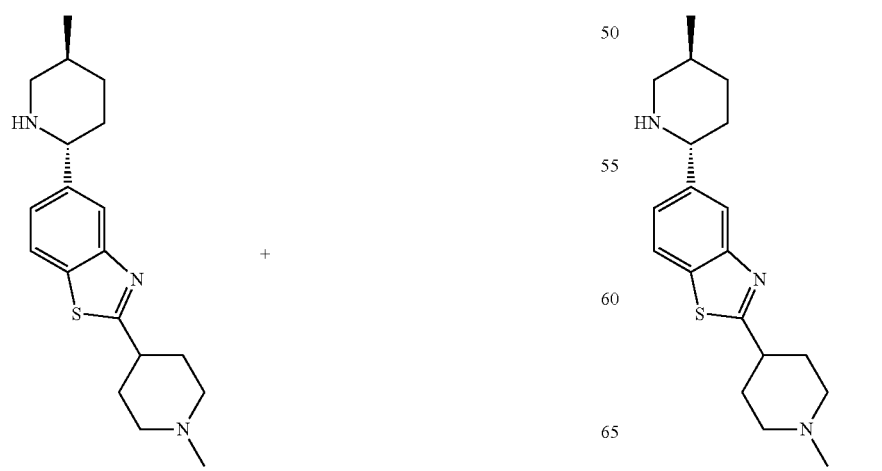

+

2657

-continued

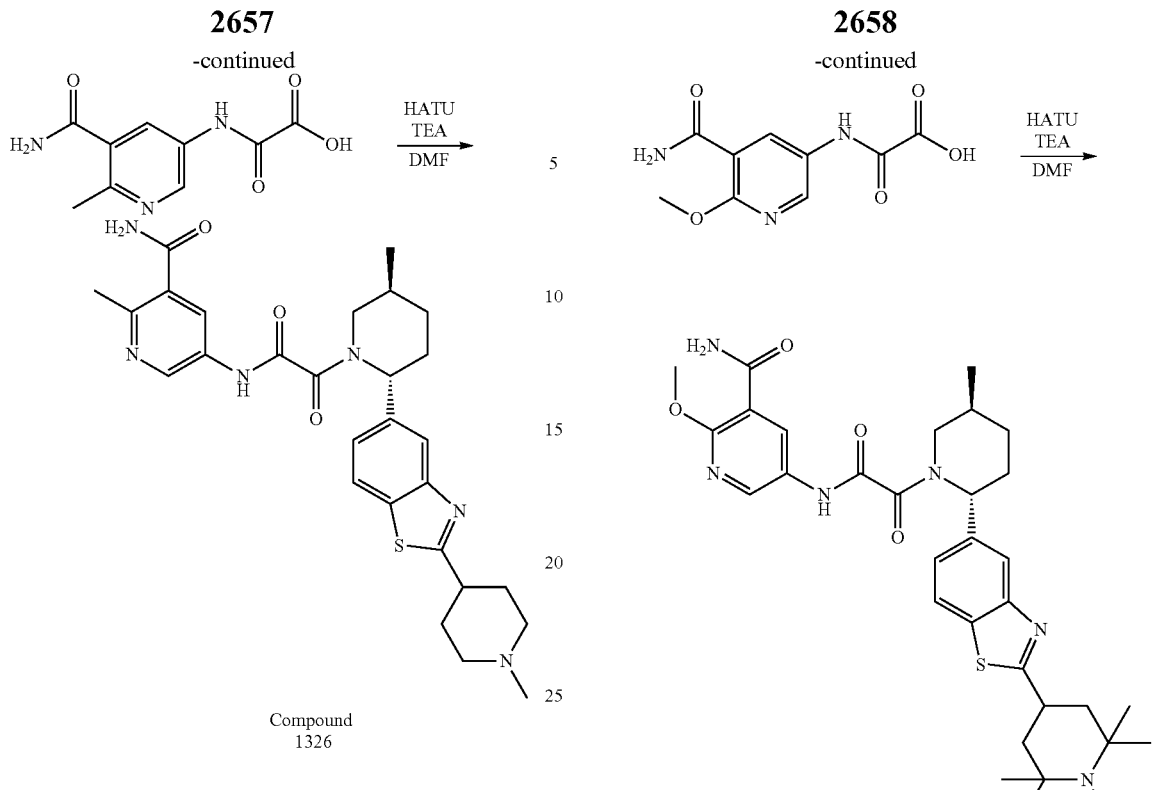

Compound 1326

Prepared by general procedure scheme H step 6A. Yield: 103 mg (47.27%).

HPLC conditions: Column: YMC Triart C18 100*20 mm, 5 microM; 0-5 min 15-50% water-MeCN+0.1% NH$_4$OH; (loading pump 4 mL/min MeCN).

$^1$H NMR (600 MHz, DMSO-d$_6$) δ (ppm) 0.96-1.09 (m, 3H), 1.30-1.43 (m, 1H), 1.65-1.74 (m, 1H), 1.75-1.95 (m, 3H), 1.98-2.12 (m, 5H), 2.18 (s, 3H), 2.28-2.35 (m, 1H), 2.43-2.47 (m, 3H), 2.81-2.86 (m, 2H), 3.02-3.11 (m, 1H), 3.32-3.38 (m, 1H), 3.45-4.09 (m, 1H), 5.22-5.73 (m, 1H), 7.32-7.44 (m, 1H), 7.48-7.60 (m, 1H), 7.82-7.89 (m, 1H), 7.89-7.94 (m, 1H), 7.96-8.10 (m, 2H), 8.57-8.79 (m, 1H), 10.80 (br s, 1H).

LCMS(ESI): [M+1]$^+$ m/z: calcd 534.2; found 535.2; Rt=2.375 min.

Example 620. The Synthesis of 2-methoxy-5-(2-((2R,5S)-5-methyl-2-(2-(1,2,2,6,6-Pentamethylpiperidin-4-yl)benzo[d]thiazol-5-yl)piperidin-1-yl)-2-oxoacetamido)nicotinamide (Compound 1108)

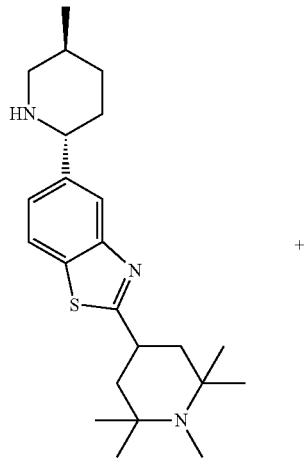

+

2658

-continued

Prepared by general procedure 8 step 6A. Yield: 64.1 mg (27.16%).

HPLC conditions: Column: YMC Triart C18 100*20 mm, 5 microM; 0-1-6 min 65-65-80% water-MeOH+0.1% NH$_4$OH; (loading pump 4 mL/min MeOH).

$^1$H NMR (600 MHz, DMSO-d$_6$) δ (ppm) 1.01-1.06 (m, 3H), 1.06-1.09 (m, 6H), 1.10-1.15 (m, 6H), 1.32-1.41 (m, 1H), 1.59-1.67 (m, 2H), 1.67-1.75 (m, 1H), 1.81-1.98 (m, 3H), 2.04-2.19 (m, 1H), 2.19-2.23 (m, 3H), 2.27-2.37 (m, 1H), 2.80-3.28 (m, 1H), 3.44-3.55 (m, 1.7H), 3.90-3.97 (m, 3H), 4.01-4.05 (m, 0.3H), 5.22-5.76 (m, 1H), 7.33-7.44 (m, 1H), 7.64-7.78 (m, 2H), 7.86-7.92 (m, 1H), 8.03-8.09 (m, 1H), 8.33-8.63 (m, 2H), 10.90-11.19 (m, 1H).

LCMS(ESI): [M]$^+$ m/z: calcd 606.2; found 607.2; Rt=2.453 min.

Example 621. The Synthesis of N-(6-amino-5-ethylpyridin-3-yl)-2-((2R,5)-2-(2-(1,4-dimethyl-5-oxopiperazin-2-yl)benzo[d]thiazol-5-yl)-5-methylpiperidin-1-yl)-2-oxoacetamide (Compound 1231)

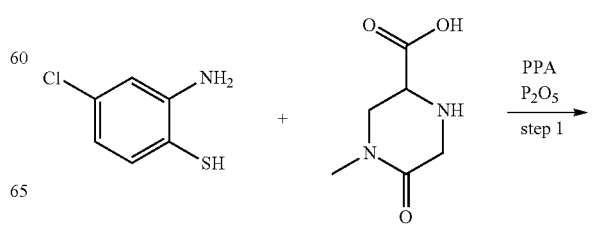

2659
-continued
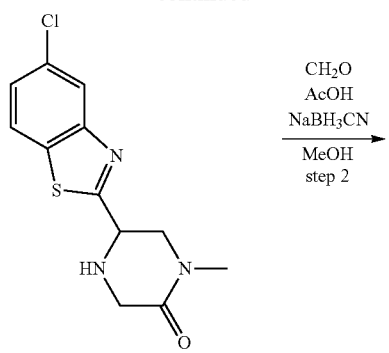
CH₂O
AcOH
NaBH₃CN
———————→
MeOH
step 2
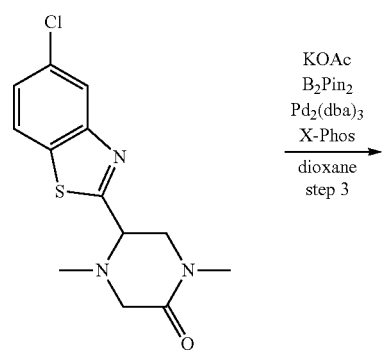
KOAc
B₂Pin₂
Pd₂(dba)₃
X-Phos
———————→
dioxane
step 3
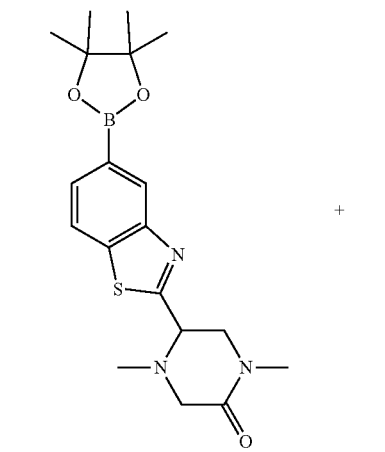
+
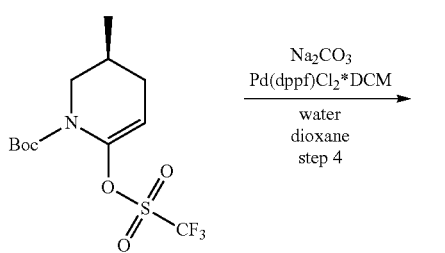
Na₂CO₃
Pd(dppf)Cl₂*DCM
———————————→
water
dioxane
step 4
2660
-continued
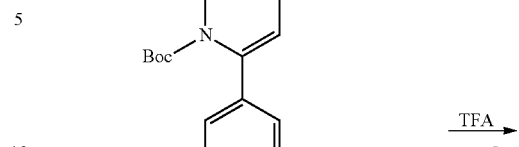
TFA
———→
step 5
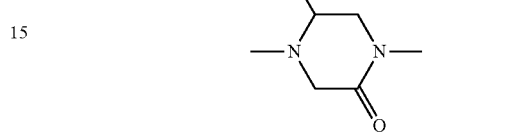
NaBH₄
————→
MeOH
step 6
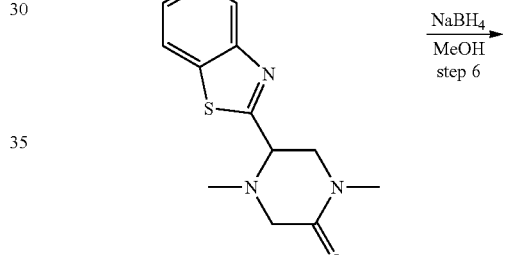
+
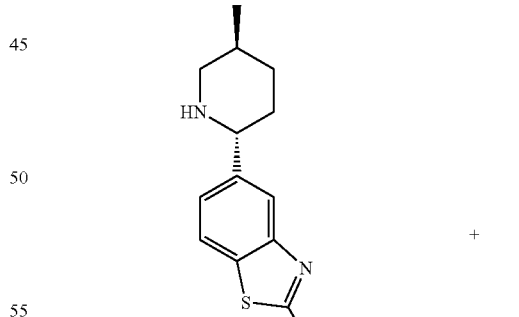
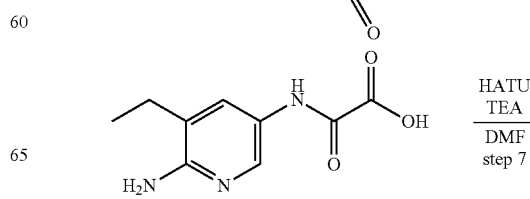
HATU
TEA
———→
DMF
step 7

-continued

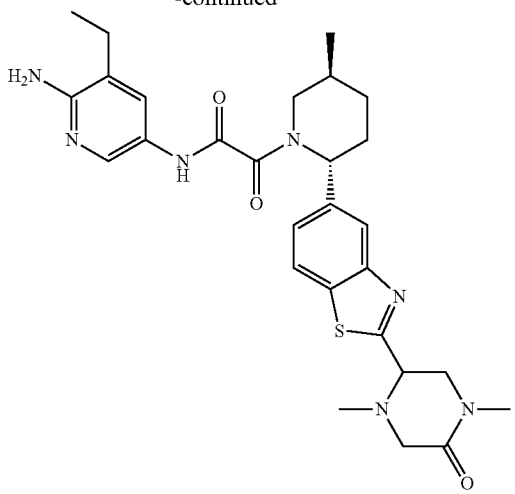

Step 1: Synthesis of 5-(5-chlorobenzo[d]thiazol-2-yl)-1-methylpiperazin-2-one Prepared by general procedure scheme H step 1A. Yield: 9.5 g of crude.
LCMS(ESI): [M]+ m/z: calcd 281.2; found 282.2; Rt=0.885 min.

Step 2: Synthesis of 5-(5-chlorobenzo[d]thiazol-2-yl)-1,4-dimethylpiperazin-2-one A mixture of 5-(5-chloro-1,3-benzothiazol-2-yl)-1-methyl-piperazin-2-one (8.5 g, 30.17 mmol), formaldehyde (3.43 g, 42.23 mmol, 3.16 mL) and acetic acid (3.62 g, 60.33 mmol, 3.45 mL) in MeOH (170 mL) was stirred at rt for 2 hr. To the mixture was added sodium cyan borohydride (3.79 g, 60.33 mmol) in one portion. The mixture was stirred at 20° C. for 18 hr, then concentrated in vacuum. The residue was basified to pH=9 ($K_2CO_3$ 10% aq.) and extracted with DCM (2*90 mL). The combined organic extracts were dried over sodium sulphate and evaporated in vacuum to afford 5-(5-chloro-1,3-benzothiazol-2-yl)-1,4-dimethyl-piperazin-2-one (9 g, crude).
LCMS(ESI): [M]+ m/z: calcd 295.2; found 296.2; Rt=1.098 min.

Step 3: Synthesis of 1,4-dimethyl-5-(5-(4,4,5,5-tetramethyl-1,3,2-dioxaborolan-2-yl)benzo[d]thiazol-2-yl)piperazin-2-one Potassium acetate (6.17 g, 62.88 mmol, 3.93 mL) was added to a solution of 5-(5-chloro-1,3-benzothiazol-2-yl)-1,4-dimethyl-piperazin-2-one (9.3 g, 31.44 mmol) and 4,4,5,5-tetramethyl-2-(4,4,5,5-tetramethyl-1,3,2-dioxaborolan-2-yl)-1,3,2-dioxaborolane (8.78 g, 34.59 mmol) in dioxane (48.09 mL). Reaction flask was evacuated and refilled with argon 3 times. Then tris(dibenzylideneacetone)dipalladium (0) (1.44 g, 1.57 mmol) and XPhos (3.00 g, 6.29 mmol) was added under stream of argon. Resulting mixture was stirred at 90° C. for 18 hr under inert atmosphere. Then, it was cooled, diluted with EtOAc (200 mL) and washed with $Na_2CO_3$ (50 mL, sat. aq.). Organic layer was dried over $Na_2SO_4$, concentrated under reduced pressure and the residue was purified by silica gel flash chromatography eluting with a 0 to 100 percent $CHCl_3$-MeCN gradient to afford product 1,4-dimethyl-5-[5-(4,4,5,5-tetramethyl-1,3,2-dioxaborolan-2-yl)-1,3-benzothiazol-2-yl]piperazin-2-one (8.8 g, 22.72 mmol, 72.27% yield).
LCMS(ESI): [M]+ m/z: calcd 387.2; found 388.2; Rt=1.213 min.

Step 4: Synthesis of (3S)-tert-butyl 6-(2-(1,4-dimethyl-5-oxopiperazin-2-yl)benzo[d]thiazol-5-yl)-3-methyl-3,4-dihydropyridine-1(2H)-carboxylate Prepared by general procedure scheme H step 3. Yield: 17 g of crude.
LCMS(ESI): [M]+ m/z: calcd 456.2; found 457.2; Rt=1.371 min.

Step 5: Synthesis of 1,4-dimethyl-5-(5-((S)-5-methyl-3,4,5,6-tetrahydropyridin-2-yl)benzo[d]thiazol-2-yl)piperazin-2-one Prepared by general procedure scheme H step 4. Yield: 7 g of crude.
LCMS(ESI): [M]+ m/z: calcd 356.2; found 357.2; Rt=0.646 min.

Step 6: Synthesis of 1,4-dimethyl-5-(5-((2R,5S)-5-methylpiperidin-2-yl)benzo[d]thiazol-2-yl)piperazin-2-one Prepared by general procedure scheme H step 5. Yield: 4 g of crude.
LCMS(ESI): [M]+ m/z: calcd 358.2; found 359.2; Rt=0.746 min.

Step 7: Synthesis of N-(6-amino-5-ethylpyridin-3-yl)-2-((2R,5S)-2-(2-(1,4-dimethyl-5-oxopiperazin-2-yl)benzo[d]thiazol-5-yl)-5-methylpiperidin-1-yl)-2-oxoacetamide (Compound 1231)

Prepared by general procedure scheme H step 6A. Yield: 81 mg (26.41%).
HPLC conditions: Column: XBridge C18 100*19 mm, 5 microM; 0-5 min 30-80% water-MeOH+0.1% $NH_4OH$, flow: 30 mL/min; (loading pump 4 mL/min MeOH).
$^1$H NMR (600 MHz, dmso) δ 1.02-1.06 (m, 3H), 1.06-1.16 (m, 3H), 1.30-1.43 (m, 1H), 1.65-1.74 (m, 1H), 1.81-1.91 (m, 1H), 2.07-2.20 (m, 1H), 2.27-2.32 (m, 4H), 2.32-2.36 (m, 1H), 2.37-2.44 (m, 2H), 2.78-2.82 (m, 0.3H), 2.86-2.88 (m, 3H), 3.19-3.28 (m, 1.7H), 3.44-3.53 (m, 0.7H), 3.71-3.78 (m, 2H), 4.03-4.07 (m, 0.3H), 4.32-4.46 (m, 1H), 5.24-5.61 (m, 1H), 5.62-5.73 (m, 2H), 7.40-7.55 (m, 2H), 7.89-7.96 (m, 1H), 7.98-8.07 (m, 1H), 8.10-8.17 (m, 1H), 10.49-10.62 (m, 1H).
LCMS(ESI): [M]+ m/z: calcd 549.2; found 550.2; Rt=2.332 min.

Example 622. The Synthesis of N-(6-amino-5-ethylpyridin-3-yl)-2-((2R,5S)-5-methyl-2-(2-(2-(methyl(Oxetan-3-yl)amino)ethyl)benzo[d]thiazol-5-yl)piperidin-1-yl)-2-oxoacetamide (Compound 1195)

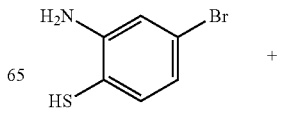
+

2663
-continued
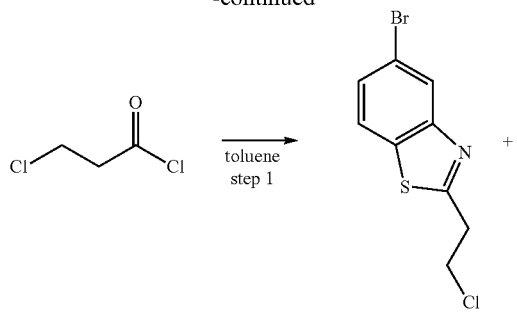
toluene
step 1
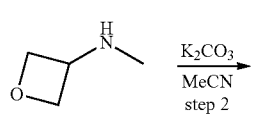
K$_2$CO$_3$
MeCN
step 2
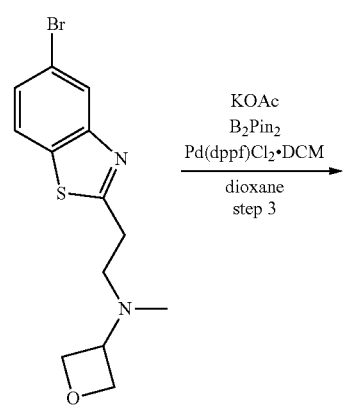
KOAc
B$_2$Pin$_2$
Pd(dppf)Cl$_2$·DCM
dioxane
step 3
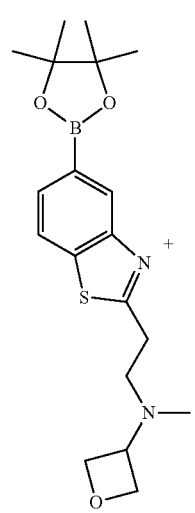
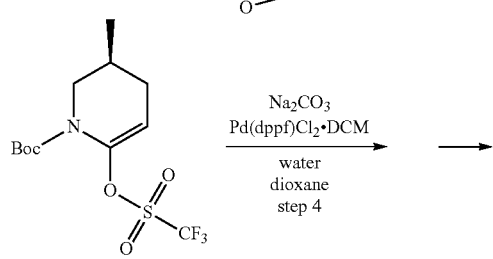
Na$_2$CO$_3$
Pd(dppf)Cl$_2$·DCM
water
dioxane
step 4
2664
-continued
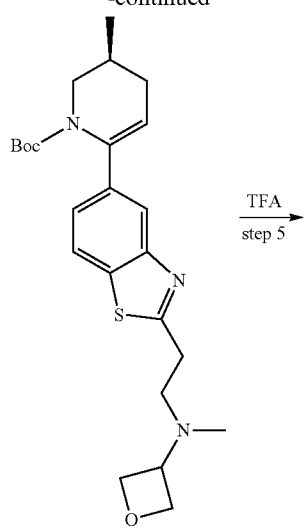
TFA
step 5
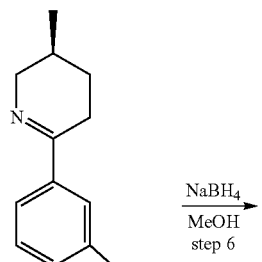
NaBH$_4$
MeOH
step 6
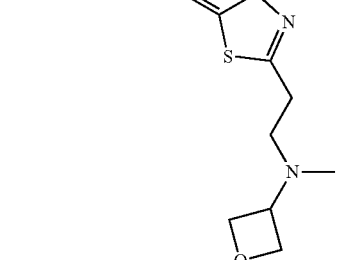
+
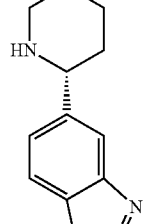
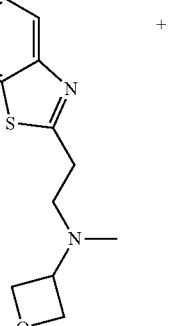
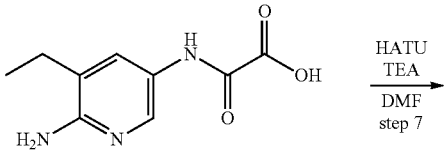
HATU
TEA
DMF
step 7

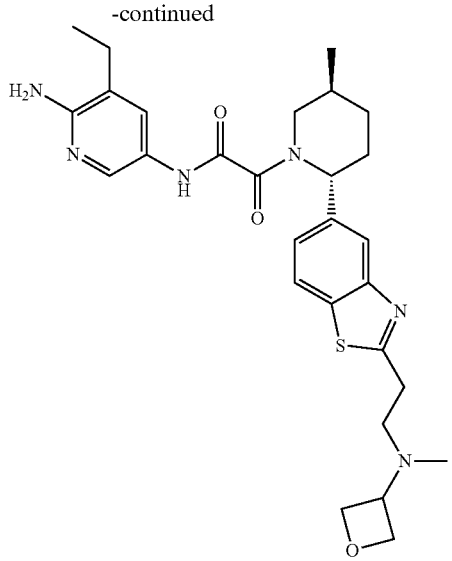

Step 1: Synthesis of 5-bromo-2-(2-chloroethyl) benzo[d]thiazole

To a solution of 2-amino-4-bromo-benzenethiol (1 g, 4.90 mmol, 170.94 uL) in toluene (15 mL), 3-chloropropanoyl chloride (684.34 mg, 5.39 mmol, 514.54 μL) was added drop wise over a 15 min period during which an off-white precipitate was formed. The reaction mixture was stirred at rt for 13 hr. Then it was triturated with water, neutralized (NaHCO₃, 5% aq.) to pH7, extracted with DCM (2×50 mL), dried and evaporated in vacuum to afford product 5-bromo-2-(2-chloroethyl)-1,3-benzothiazole (1.3 g, 4.70 mmol, 95.93% yield).

LCMS(ESI): [M]⁺ m/z: calcd 276.2; found 377.2; Rt=1.505 min.

Step 2: Synthesis of N-(2-(5-bromobenzo[d]thiazol-2-yl)ethyl)-N-methyloxetan-3-amine To a solution of 5-bromo-2-(2-chloroethyl)-1,3-benzothiazole (4.9 g, 17.72 mmol) and N-methyloxetan-3-amine (2.58 g, 19.49 mmol) in MeCN (60 mL) was added potassium carbonate-granular (6.12 g, 44.29 mmol, 2.67 mL). The reaction mixture was then stirred for 5 day at 40° C., then evaporated in vacuum. The residue was diluted with water (50 mL) and extracted with DCM (2*50 mL). The combined organic extracts were dried over sodium sulphate and evaporated in vacuum to afford N-[2-(5-bromo-1,3-benzothiazol-2-yl)ethyl]-N-methyl-oxetan-3-amine (6 g, crude).

LCMS(ESI): [M]⁺ m/z: calcd 327.2; found 328.2; Rt=0.781 min.

Step 3: Synthesis of N-methyl-N-(2-(5-(4,4,5,5-tetramethyl-1,3,2-dioxaborolan-2-yl)benzo[d]thiazol-2-yl)ethyl)oxetan-3-amine Prepared by general procedure scheme H step 2. Yield: 16 g of crude.

LCMS(ESI): [M]⁺ m/z: calcd 374.2; found 375.2; Rt=1.006 min.

Step 4: Synthesis of (S)-tert-butyl 3-methyl-6-(2-(2-(methyl(Oxetan-3-yl)amino)ethyl)benzo[d]thiazol-5-yl)-3,4-dihydropyridine-1(2H)-carboxylate Prepared by general procedure scheme H step 3. Yield: 22 g of crude.

LCMS(ESI): [M]⁺ m/z: calcd 443.2; found 444.2; Rt=1.083 min.

Step 5: Synthesis of (S)—N-methyl-N-(2-(5-(5-methyl-3,4,5,6-tetrahydropyridin-2-yl)benzo[d]thiazol-2-yl)ethyl)oxetan-3-amine Prepared by general procedure scheme H step 4. Yield: 5.5 g of crude.

LCMS(ESI): [M]⁺ m/z: calcd 343.2; found 344.2; Rt=0.640 min.

Step 6: Synthesis of N-methyl-N-(2-(5-((2R,5S)-5-methylpiperidin-2-yl)benzo[d]thiazol-2-yl)ethyl)oxetan-3-amine Prepared by general procedure scheme H step 5. Yield: 4 g of crude.

LCMS(ESI): [M]⁺ m/z: calcd 345.2; found 346.2; Rt=0.707 min.

Step 7: Synthesis of N-(6-amino-5-ethylpyridin-3-yl)-2-((2R,5S)-5-methyl-2-(2-(2-(methyl(Oxetan-3-yl)amino)ethyl)benzo[d]thiazol-5-yl)piperidin-1-yl)-2-oxoacetamide (Compound 1195

Prepared by general procedure scheme H step 6A. Yield: 5.7 mg (1.83%).

HPLC conditions: Column: XBridge C18 100*19 mm, 5 microM; 0-6 min 35-80% water-MeOH+0.1% NH₄OH, flow: 30 mL/min; (loading pump 4 mL/min MeOH).

¹H 1H NMR (600 MHz, dmso) 6 1.02-1.06 (m, 3H), 1.06-1.15 (m, 3H), 1.31-1.41 (m, 1H), 1.66-1.75 (m, 1H), 1.83-1.93 (m, 1H), 2.14 (s, 3H), 2.15-2.36 (m, 2H), 2.37-2.43 (m, 2H), 2.65-2.69 (m, 2H), 2.76-3.08 (m, 1H), 3.20-3.24 (m, 2H), 3.46-3.50 (m, 0.7H), 3.57-3.61 (m, 1H), 4.02-4.07 (m, 0.3H), 4.40 (t, 2H), 4.50 (t, 2H), 5.26-5.61 (m, 1H), 5.61-5.73 (m, 2H), 7.33-7.42 (m, 1H), 7.42-7.54 (m, 1H), 7.83-7.92 (m, 1H), 7.97-8.09 (m, 2H), 9.33 (br s, 1H).

LCMS(ESI): [M]⁺ m/z: calcd 536.2; found 537.2; Rt=2.164 min.

Example 623. The Synthesis of N-(6-amino-5-ethylpyridin-3-yl)-2-((2R,53)-5-methyl-2-(2-(1-methyl-1H-imidazol-2-yl)benzo[d]thiazol-5-yl)piperidin-1-yl)-2-oxoacetamide (Compound 1192

Step 1: Synthesis of 5-chloro-2-(1-methyl-1H-imidazol-2-yl)benzo[d]thiazole

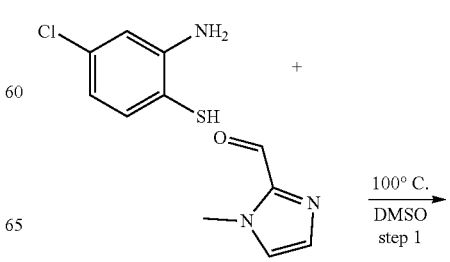

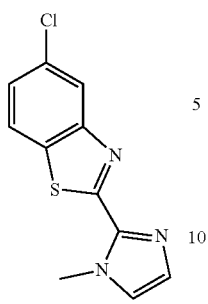

Prepared by general procedure scheme H step 1B. Yield: 13 g (95.54%).

LCMS(ESI): [M]⁺ m/z: calcd 249.2; found 250.2; Rt=3.165 min.

Step 2: Synthesis of 2-(1-methyl-1H-imidazol-2-yl)-5-(4,4,5,5-tetramethyl-1,3,2-dioxaborolan-2-yl)benzo[d]thiazole

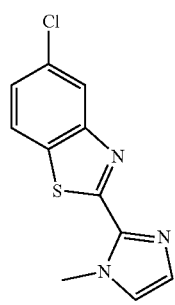

A mixture of 5-chloro-2-(1-methylimidazol-2-yl)-1,3-benzothiazole (5 g, 20.02 mmol), 4,4,5,5-tetramethyl-2-(4,4,5,5-tetramethyl-1,3,2-dioxaborolan-2-yl)-1,3,2-dioxaborolane (5.59 g, 22.02 mmol) and potassium acetate (3.93 g, 40.05 mmol, 2.50 mL) in dioxane (100 mL) was evacuated and then backfilled with argon. This operation was repeated two times, then tris(1,5-diphenylpenta-1,4-dien-3-one)dipalladium (916.75 mg, 1.00 mmol) and dicyclohexyl[2',4',6'-tris(propan-2-yl)-[1,1'-biphenyl]-2-yl]phosphane (1.91 g, 4.00 mmol) were added under argon, and the reaction mixture was stirred at 95° C. for 18 hr. The reaction mixture was cooled down and concentrated in vacuum. The residue was purified by column chromatography on silica gel using hexane/MTBE gradient (0-100% MTBE) to afford 2-(1-methylimidazol-2-yl)-5-(4,4,5,5-tetramethyl-1,3,2-dioxaborolan-2-yl)-1,3-benzothiazole (7 g, crude) as purple solid.

LCMS(ESI): [M]⁺ m/z: calcd 341.2; found 342.2; Rt=1.567 min.

Step 3: Synthesis of (S)-tert-butyl 3-methyl-6-(2-(1-methyl-1H-imidazol-2-yl)benzo[d]thiazol-5-yl)-3,4-dihydropyridine-1(2H)-carboxylate

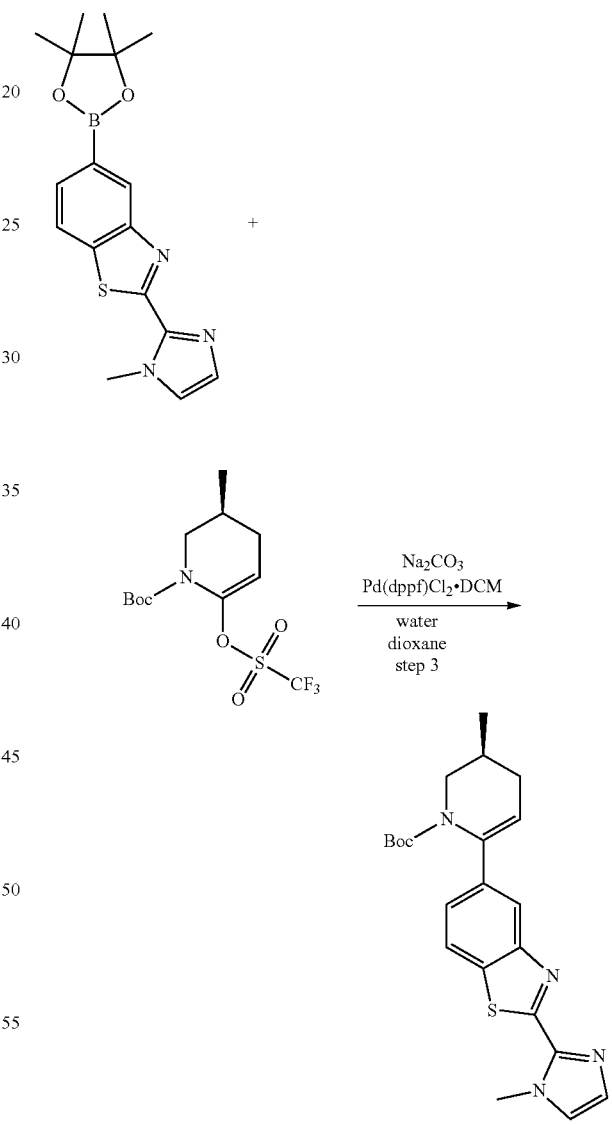

Prepared by general procedure scheme H step 3. Yield: 1.6 g (53.20%).

CC conditions: The crude product was purified by silica gel with hexane/MTBE (gradient 0-100% MTBE) as an eluent mixture.

LCMS(ESI): [M]⁺ m/z: calcd 410.2; found 411.2; Rt=1.510 min.

Step 4: Synthesis of (S)-2-(1-methyl-1H-imidazol-2-yl)-5-(5-methyl-3,4,5,6-tetrahydropyridin-2-yl)benzo[d]thiazole

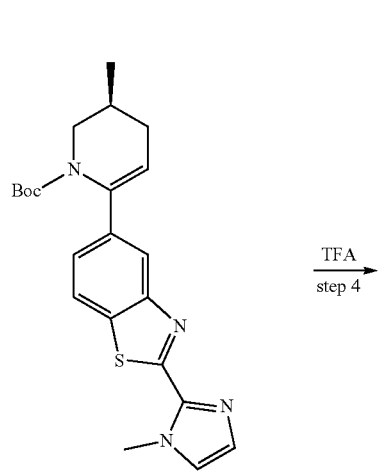

TFA
step 4

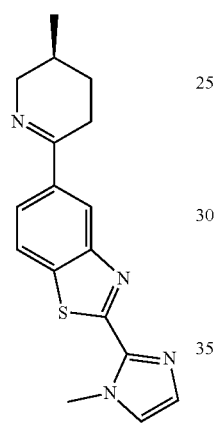

Prepared by general procedure scheme H step 4. Yield: 1.1 g (90.92%).

LCMS(ESI): [M]⁺ m/z: calcd 310.2; found 311.2; Rt=0.916 min.

Step 5: Synthesis of 2-(1-methyl-1H-imidazol-2-yl)-5-((2R,5S)-5-methylpiperidin-2-yl)benzo[d]thiazole

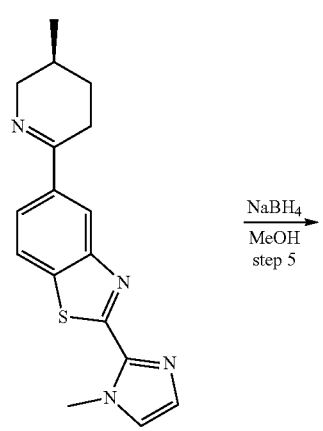

NaBH₄
MeOH
step 5

-continued

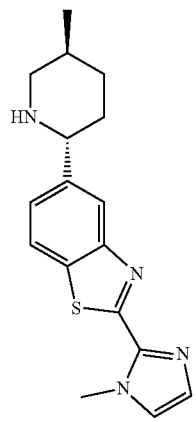

Prepared by general procedure scheme H step 5. Yield: 0.9 g (81.29%).

LCMS(ESI): [M]⁺ m/z: calcd 312.2; found 313.2; Rt=0.806 min.

Step 6: The Synthesis of N-(6-amino-5-ethylpyridin-3-yl)-2-((2R,5S)-5-methyl-2-(2-(1-methyl-1H-imidazol-2-yl)benzo[d]thiazol-5-yl)piperidin-1-yl)-2-oxoacetamide (Compound 1192)

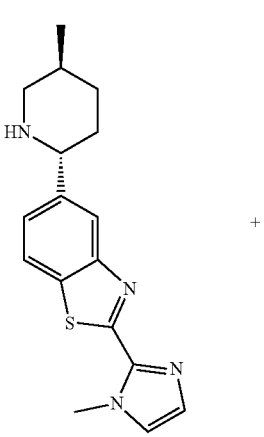

+

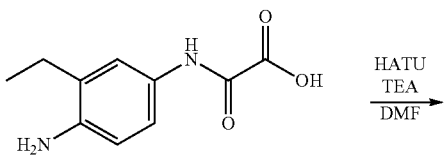

HATU
TEA
DMF

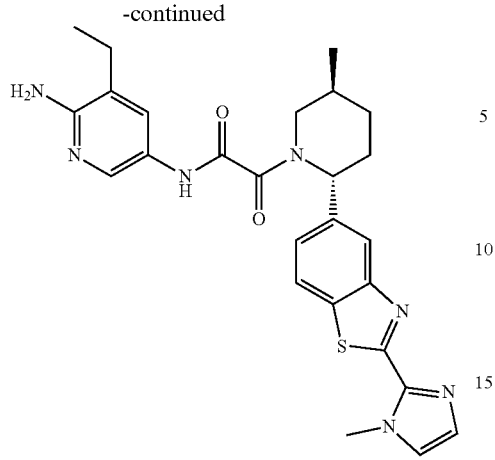

Prepared by general procedure scheme H step 6A. Yield: 93 mg (38.46%).

HPLC conditions: Column: XBridge C18 100*19 mm, 5 microM; 0-1-6 min 10-10-60% water-MeCN+0.1% NH₄OH; (loading pump 4 ml/min MeCN).

¹H NMR (600 MHz, DMSO-d₆) δ (ppm) 1.03-1.14 (m, 6H), 1.34-1.41 (m, 1H), 1.73 (m, 1H), 1.87-2.20 (m, 3H), 2.30-2.41 (m, 2H), 2.81-2.83 (m, 1H), 3.33-3.52 (m, 1H), 4.16 (s, 3H), 5.30-5.72 (m, 3H), 7.13 (s, 1H), 7.41-7.52 (m, 3H), 7.92-8.13 (m, 3H), 10.54-10.60 (m, 1H).

LCMS(ESI): [M]⁺ m/z: calcd 503.2; found 504.2; Rt=2.408 min.

Example 624. The Synthesis of N-(6-amino-5-ethylpyridin-3-yl)-2-((2R,5S)-2-(2-(1-(dimethylamino)propan-2-yl)benzo[d]thiazol-5-yl)-5-methylpiperidin-1-yl)-2-oxoacetamide (Compound 1324)

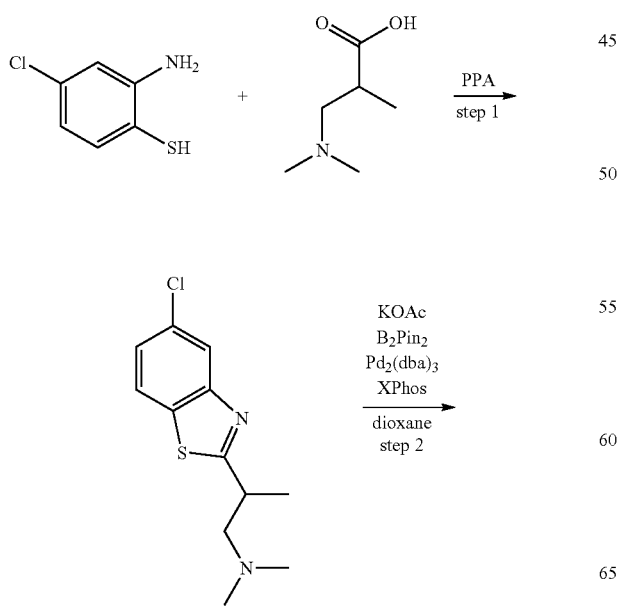

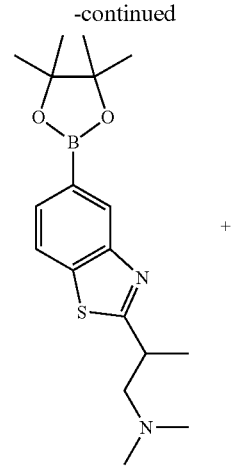

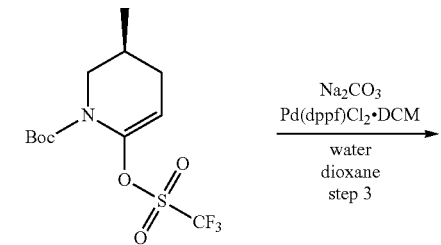

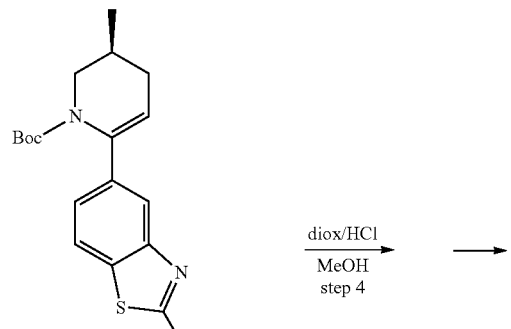

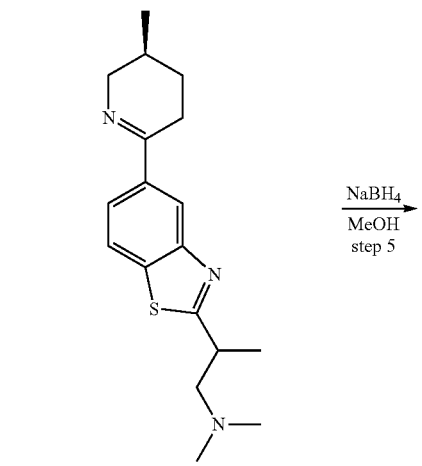

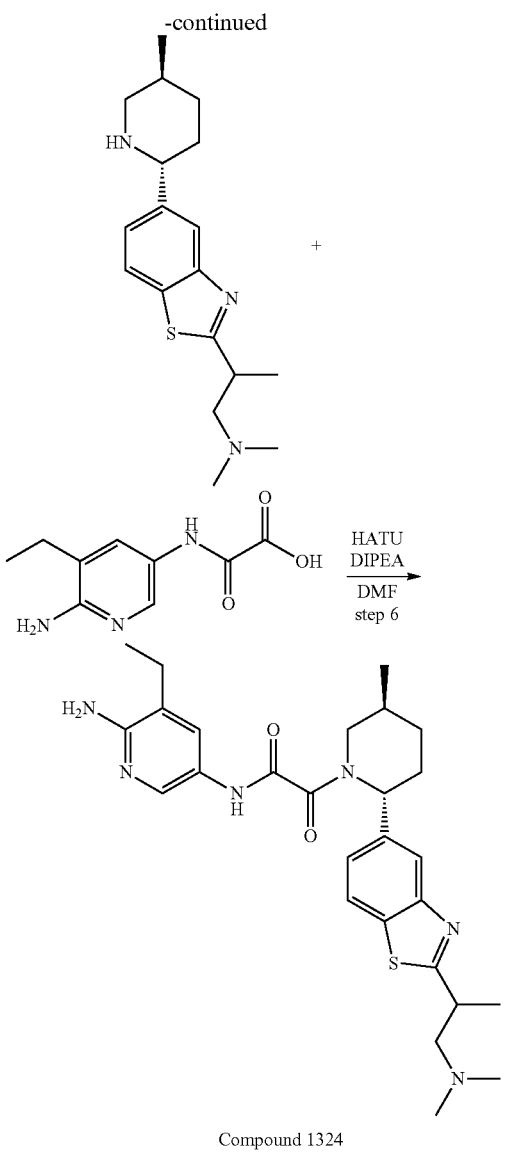

Compound 1324

Step 1: Synthesis of 2-(5-chlorobenzo[d]thiazol-2-yl)-N,N-dimethylpropan-1-amine The stirred solution of 2-amino-4-chloro-benzenethiol (1.5 g, 9.40 mmol) and 2-amino-4-chloro-benzenethiol (1.5 g, 9.40 mmol) in PPA (10 mL) was allowed to stir at 140° C. for 16 hr. Upon completion, the reaction mixture was quenched with water (200 mL) and neutralized by NaOH to pH=8. The aqueous phase was extracted with EtOAc (2*20 mL). The combined organic phase was dried over $Na_2SO_4$ and concentrated under reduced pressure. The desired product 2-(5-chloro-1,3-benzothiazol-2-yl)-N,N-dimethyl-propan-1-amine (1.5 g, 5.89 mmol, 62.66% yield) was isolated.

LCMS(ESI): $[M]^+$ m/z: calcd 254.2; found 255.2; Rt=0.672 min.

Step 2: Synthesis of N,N-dimethyl-2-(5-(4,4,5,5-tetramethyl-1,3,2-dioxaborolan-2-yl)benzo[d]thiazol-2-yl)propan-1-amine To a stirred solution of 2-(5-chloro-1,3-benzothiazol-2-yl)-N,N-dimethyl-propan-1-amine (1.5 g, 5.89 mmol) and 4,4,5,5-tetramethyl-2-(4,4,5,5-tetramethyl-1,3,2-dioxaborolan-2-yl)-1,3,2-dioxaborolane (1.50 g, 5.89 mmol) in dioxane (30 mL) were added $Pd_2(dba)_3$ (1.08 g, 1.18 mmol) and XPhos (1.12 g, 2.35 mmol). The resulting suspension was degassed with argon at 50° C. for 0.5 hr. Potassium acetate (1.2 g, 12.23 mmol, 764.33 μL) was added. The reaction mixture was stirred at 100° C. for 16 hr. Upon completion, the reaction mixture was concentrated under reduced pressure, quenched with water (50 mL), the aqueous phase was extracted with $CHCl_3$ (2*50 mL). The organic phase was extracted with 10% HCl (2*50 mL). The aqueous phase was neutralized by $NaHCO_3$ to pH=8, extracted with $CHCl_3$ (2*50 mL). The organic phase was dried over $Na_2SO_4$ and evaporated in vacuum. The desired product N,N-dimethyl-2-[5-(4,4,5,5-tetramethyl-1,3,2-dioxaborolan-2-yl)-1,3-benzothiazol-2-yl]propan-1-amine (1.4 g, 4.04 mmol, 68.67% yield) was isolated.

LCMS(ESI): $[M]^+$ m/z: calcd 346.2; found 347.2; Rt=1.121 min.

Step 3: Synthesis of (3S)-tert-butyl 6-(2-(1-(dimethylamino)propan-2-yl)benzo[d]thiazol-5-yl)-3-methyl-3,4-dihydropyridine-1(2H)-carboxylate Prepared by general procedure scheme H step 3. Yield: 0.7 g of crude.

LCMS(ESI): $[M]^+$ m/z: calcd 415.2; found 416.2; Rt=1.238 min.

Step 4: Synthesis of N,N-dimethyl-2-(5-((S)-5-methyl-3,4,5,6-tetrahydropyridin-2-yl)benzo[d]thiazol-2-yl)propan-1-amine The stirred solution of tert-butyl (3S)-6-[2-[2-(dimethylamino)-1-methyl-ethyl]-1,3-benzothiazol-5-yl]-3-methyl-3,4-dihydro-2H-pyridine-1-carboxylate (700.00 mg, 1.68 mmol) in MeOH (10 mL) and diox/HCl (10 mL) was allowed to stir at 25° C. for 16 hr. Upon completion, the reaction mixture was evaporated, the crude product was quenched with water (20 mL) and neutralized by $NaHCO_3$ to pH=8. The aqueous phase was extracted with $CHCl_3$ (2*20 mL). The combined organic phase was dried over $Na_2SO_4$ and concentrated under reduced pressure. The desired product N,N-dimethyl-2-[5-[(3S)-3-methyl-2,3,4,5-tetrahydropyridin-6-yl]-1,3-benzothiazol-2-yl]propan-1-amine (0.5 g, 1.58 mmol, 94.10% yield) was isolated.

LCMS(ESI): $[M]^+$ m/z: calcd 315.2; found 316.2; Rt=0.666 min.

Step 5: Synthesis of N,N-dimethyl-2-(5-((2R,5S)-5-methylpiperidin-2-yl)benzo[d]thiazol-2-yl)propan-1-amine Prepared by general procedure scheme H step 5. Yield: 0.5 g of crude.

LCMS(ESI): $[M]^+$ m/z: calcd 317.2; found 318.2; Rt=0.471 min.

Step 6: Synthesis of N-(6-amino-5-ethylpyridin-3-yl)-2-((2R,5S)-2-(2-(1-(dimethylamino)propan-2-yl)benzo[d]thiazol-5-yl)-5-methylpiperidin-1-yl)-2-oxoacetamide (Compound 1324

Prepared by general procedure scheme H step 6B. Yield: 17 mg (10.61%).

HPLC conditions: Column: XBridge C18 100*19 mm, 5 microM; 0-5 min 40-90% water-MeOH+0.1% NH₄OH, flow: 30 mL/min; (loading pump 4 mL/min MeOH).
¹H NMR (600 MHz, DMSO-d₆) δ (ppm) 0.98-1.05 (m, 3H), 1.06-1.16 (m, 3H), 1.30-1.44 (m, 4H), 1.66-1.77 (m, 1H), 1.79-1.96 (m, 1H), 2.04-2.11 (m, 1H), 2.15-2.23 (m, 6H), 2.26-2.36 (m, 1H), 2.38-2.47 (m, 3H), 2.61-2.67 (m, 1H), 2.78-3.25 (m, 1H), 3.42-4.09 (m, 2H), 5.24-5.60 (m, 1H), 5.60-5.73 (m, 2H), 7.32-7.42 (m, 1H), 7.43-7.54 (m, 1H), 7.82-7.92 (m, 1H), 7.96-8.11 (m, 2H), 10.32-10.69 (m, 1H).
LCMS(ESI): [M]⁺ m/z: calcd 508.2; found 509.2; Rt=1.563 min.
Example 625. The Synthesis of N-(6-amino-5-ethylpyridin-3-yl)-2-((2R,5S)-5-methyl-2-(2-(1-(3,3,3-trifluoropropyl)piperidin-4-yl)benzo[d]thiazol-5-yl)piperidin-1-yl)-2-oxoacetamide (Compound 1124)
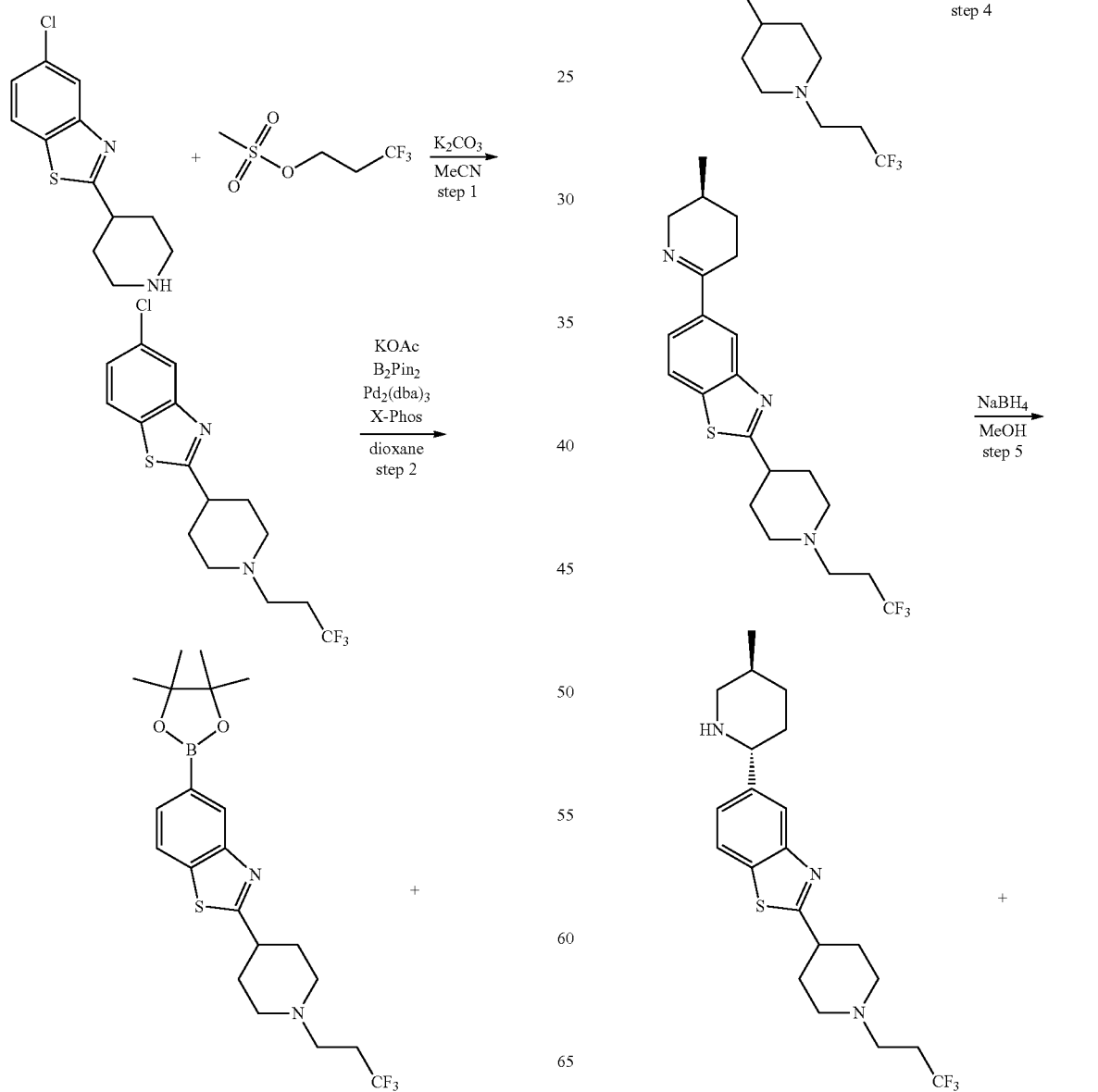

-continued

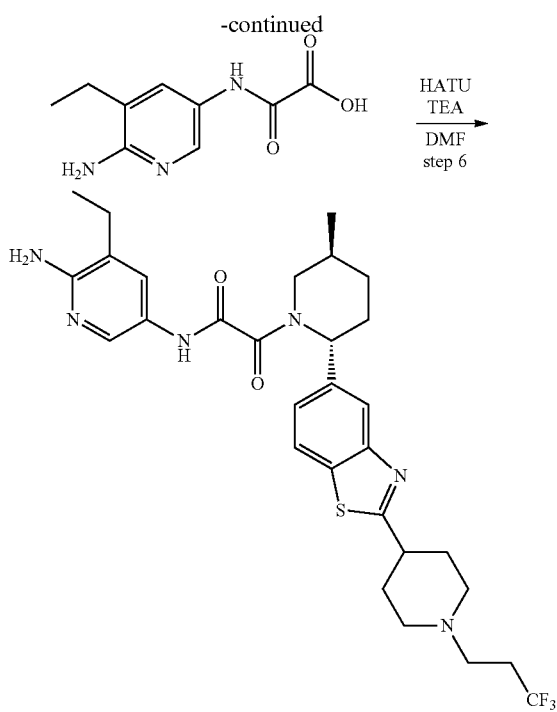

Step 1: Synthesis of 5-chloro-2-(1-(3,3,3-trifluoropropyl)piperidin-4-yl)benzo[d]thiazole Potassium carbonate (3.83 g, 27.69 mmol, 1.67 mL) was added to the solution of 5-chloro-2-(4-piperidyl)-1,3-benzothiazole (3.5 g, 13.85 mmol) and 3,3,3-trifluoropropyl methanesulfonate (3.73 g, 19.39 mmol) in MeCN (80 mL). Resulting mixture was stirred at 80° C. for 72 hr. Then, it was concentrated under reduced pressure and residue was partitioned between water (30 mL) and MTBE (50 mL). Organic layer was separated, dried over Na$_2$SO$_4$ and evaporated in vacuum, affording 5-chloro-2-[1-(3,3,3-trifluoropropyl)-4-piperidyl]-1,3-benzothiazole (5.5 g, crude).

LCMS(ESI): [M]$^+$ m/z: calcd 348.2; found 349.2; Rt=1.055 min.

Step 2: Synthesis of 5-(4,4,5,5-tetramethyl-1,3,2-dioxaborolan-2-yl)-2-(1-(3,3,3-trifluoropropyl)piperidin-4-yl)benzo[d]thiazole 5-chloro-2-[1-(3,3,3-trifluoropropyl)-4-piperidyl]-1,3-benzothiazole (6.33 g, 18.13 mmol), 4,4,5,5-tetramethyl-2-(4,4,5,5-tetramethyl-1,3,2-dioxaborolan-2-yl)-1,3,2-dioxaborolane (5.53 g, 21.76 mmol) and potassium acetate (3.56 g, 36.27 mmol, 2.27 mL) were mixed together in dioxane (100 mL). Reaction flask was evacuated and refilled with argon 3 times. Then, tris(dibenzylideneacetone)dipalladium (0) (830.24 mg, 906.66 µmol) and XPhos (1.73 g, 3.63 mmol) was added under stream of argon. Resulting mixture was stirred at 100° C. for 16 hr. Then, it was concentrated under reduced pressure and residue was purified by gradient column chromatography (SiO$_2$, CHCl$_3$/MeCN), affording 5-(4,4,5,5-tetramethyl-1,3,2-dioxaborolan-2-yl)-2-[1-(3,3,3-trifluoropropyl)-4-piperidyl]-1,3-benzothiazole (1.7 g, 3.86 mmol, 21.29% yield).

LCMS(ESI): [M]$^+$ m/z: calcd 440.2; found 441.2; Rt=1.192 min.

Step 3: Synthesis of (S)-tert-butyl 3-methyl-6-(2-(1-(3,3,3-trifluoropropyl)piperidin-4-yl)benzo[d]thiazol-5-yl)-3,4-dihydropyridine-1(2H)-carboxylate Prepared by general procedure scheme H step 3. Yield: 1.97 g of crude.

LCMS(ESI): [M]$^+$ m/z: calcd 509.2; found 510.2; Rt=1.225 min.

Step 4: Synthesis of (S)-5-(5-methyl-3,4,5,6-tetrahydropyridin-2-yl)-2-(1-(3,3,3-trifluoropropyl)piperidin-4-yl)benzo[d]thiazole Prepared by general procedure scheme H step 4. Yield: 1.16 g of crude.

LCMS(ESI): [M]$^+$ m/z: calcd 409.2; found 410.2; Rt=0.746 min.

Step 5: Synthesis of 5-((2R,5S)-5-methylpiperidin-2-yl)-2-(1-(3,3,3-trifluoropropyl)piperidin-4-yl)benzo[d]thiazole Prepared by general procedure scheme H step 5. Yield: 830 mg of crude.

LCMS(ESI): [M]$^+$ m/z: calcd 411.2; found 422.2; Rt=0.640 min.

Step 6: Synthesis of N-(6-amino-5-ethylpyridin-3-yl)-2-((2R,5S)-5-methyl-2-(2-(1-(3,3,3-trifluoropropyl)piperidin-4-yl)benzo[d]thiazol-5-yl)piperidin-1-yl)-2-oxoacetamide (Compound 1124)

Prepared by general procedure scheme H step 6A. Yield: 41 mg (26.66%).

HPLC conditions: Column: YMC Triart C18 100*20 mm, 5 microM; 0-6 min 50-90% water-MeOH+0.1% NH$_4$OH, flow: 30 mL/min; (loading pump 4 mL/min MeOH).

$^1$H NMR (600 MHz, DMSO-d$_6$) δ (ppm) 0.68-1.04 (m, 3H), 1.05-1.16 (m, 3H), 1.28-1.41 (m, 1H), 1.65-1.73 (m, 1H), 1.75-1.82 (m, 2H), 1.83-1.94 (m, 1H), 2.03-2.17 (m, 5H), 2.24-2.36 (m, 2H), 2.38-2.47 (m, 3H), 2.53-2.56 (m, 2H), 2.91-2.99 (m, 2H), 3.06-3.15 (m, 1H), 3.22-3.28 (m, 1H), 3.35-4.09 (m, 1H), 5.24-5.60 (m, 1H), 5.61-5.74 (m, 2H), 7.31-7.43 (m, 1H), 7.43-7.55 (m, 1H), 7.85-7.92 (m, 1H), 7.96-8.11 (m, 2H), 10.39-10.63 (m, 1H).

LCMS(ESI): [M]$^+$ m/z: calcd 602.2; found 603.2; Rt=2.347 min.

Example 626. The Synthesis of 2-methoxy-5-(2-((2R,5S)-5-methyl-2-(2-(2-methyl-2-azaspiro[3.3]heptan-6-yl)benzo[d]thiazol-5-yl)piperidin-1-yl)-2-oxoacetamido)nicotinamide (Compound 1236)

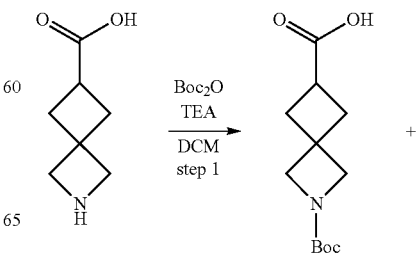

-continued
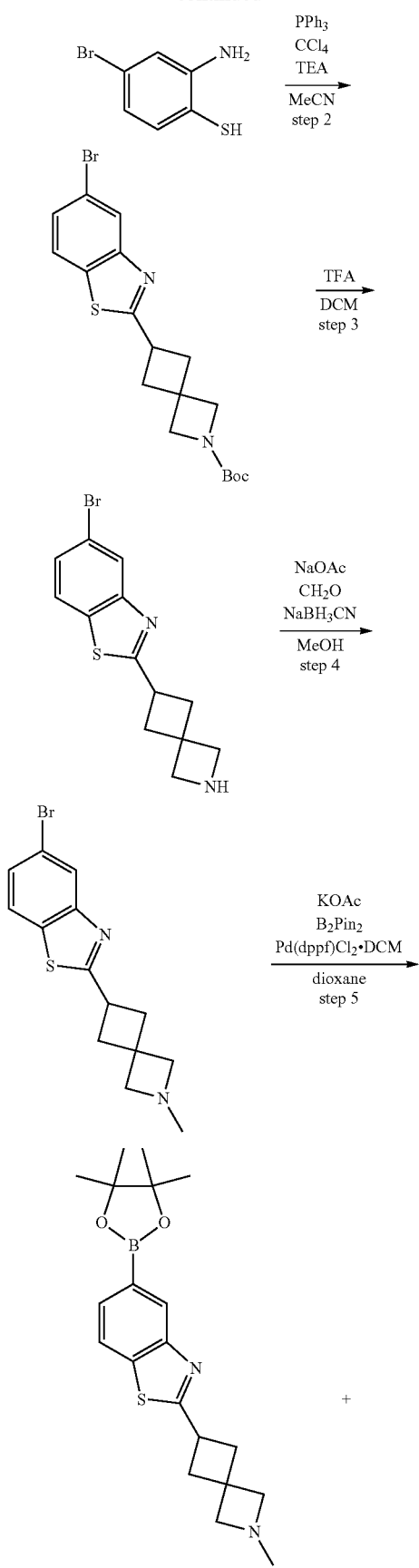
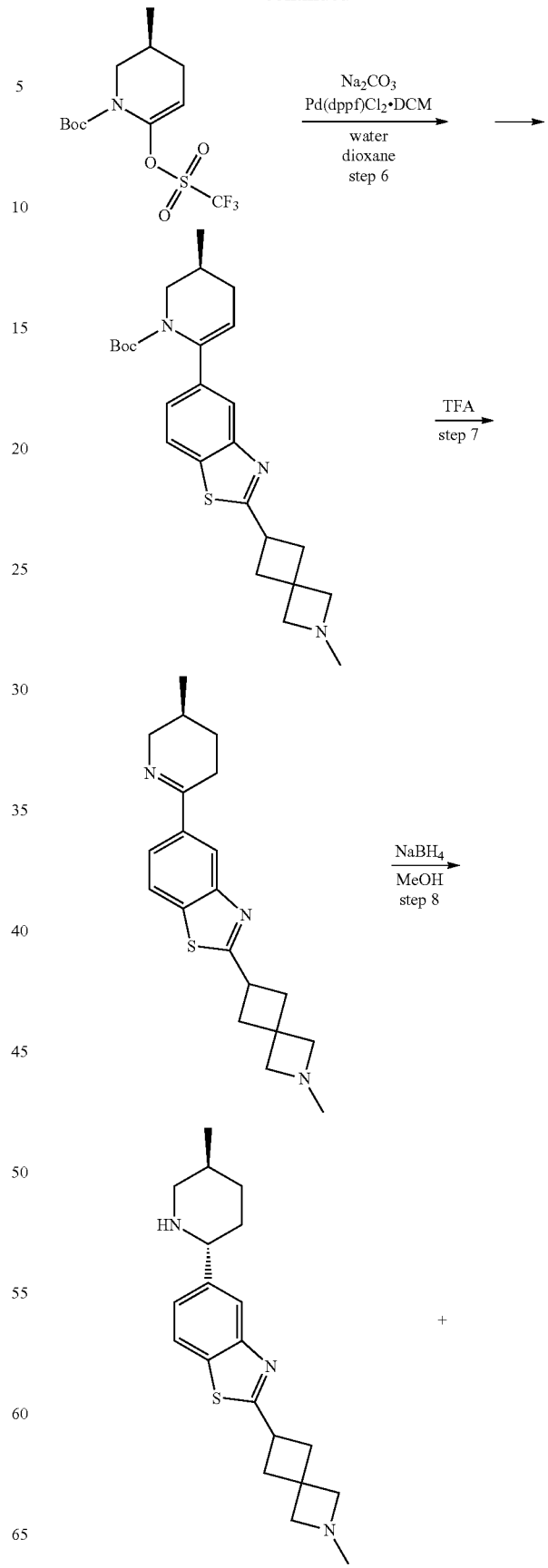

-continued

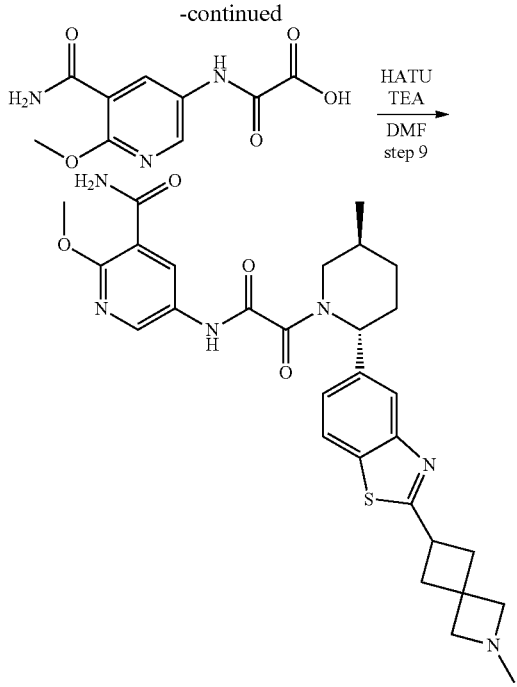

Step 1: Synthesis of 2-(tert-butoxycarbonyl)-2-azaspiro[3.3]heptane-6-carboxylic acid Di-tert-butyl dicarbonate (7.88 g, 36.12 mmol, 8.29 mL) was added dropwise to the suspension of 2-azaspiro[3.3]heptane-6-carboxylic acid (6.11 g, 34.40 mmol, HCl) in DCM (102.40 mL) and TEA (8.70 g, 85.99 mmol, 11.99 mL). Resulting reaction mixture was stirred at 20° C. for 16 hr. Then, 10% aq. NaHSO₄ solution (80 mL) was added and stirring was continued for 5 min. After that, organic layer was separated, dried over Na₂SO₄ and concentrated under reduced pressure, leaving 2-tert-butoxycarbonyl-2-azaspiro[3.3]heptane-6-carboxylic acid (8.8 g, crude).

$^1$H NMR (400 MHz, CDCl$_3$) δ (ppm) 1.41 (s, 9H), 1.51 (m, 1H), 2.43 (m, 4H), 3.00 (m, 1H), 3.90 (m, 4H).

Step 2: Synthesis of tert-butyl 6-(5-bromobenzo[d]thiazol-2-yl)-2-azaspiro[3.3]heptane-2-carboxylate Triphenylphosphine (516.35 mg, 1.97 mmol) was added in one portion to the solution of 2-tert-butoxycarbonyl-2-azaspiro[3.3]heptane-6-carboxylic acid (190 mg, 787.46 µmol), 2-amino-4-bromo-benzenethiol (160.71 mg, 787.46 µmol), carbon tetrachloride (795.00 mg, 5.17 mmol, 0.5 mL) and TEA (398.41 mg, 3.94 mmol, 548.78 µL). Resulting reaction mixture was briefly warmed up to approximately 50-60° C. due to exothermic reaction. After that, it was stirred at 20° C. for 18 hr. Then, volatiles were removed under reduced pressure and residue was triturated with MTBE (100 mL). Resulting light precipitate was filtered off. Filtrate was concentrated under reduced pressure and residue was purified by gradient column chromatography (SiO₂, Hexane/EtOAc), affording tert-butyl 6-(5-bromo-1,3-benzothiazol-2-yl)-2-azaspiro[3.3]heptane-2-carboxylate (4.6 g, 11.24 mmol, 31.53% yield).

LCMS(ESI): [M]⁺ m/z: calcd 409.2; found 410.2; Rt=1.581 min.

Step 3: Synthesis of 5-bromo-2-(2-azaspiro[3.3]heptan-6-yl)benzo[d]thiazole

Trifluoroacetic acid (12.81 g, 112.38 mmol, 8.66 mL) was added to the solution of tert-butyl 6-(5-bromo-1,3-benzothiazol-2-yl)-2-azaspiro[3.3]heptane-2-carboxylate (4.6 g, 11.24 mmol) in DCM (60 mL). Resulting mixture was stirred at 20° C. for 5 hr. Then, it was concentrated under reduced pressure, leaving 2-(2-azaspiro[3.3]heptan-6-yl)-5-bromo-1,3-benzothiazole (5 g, crude, TFA).

LCMS(ESI): [M]⁺ m/z: calcd 309.2; found 310.2; Rt=0.830 min.

Step 4: Synthesis of 5-bromo-2-(2-methyl-2-azaspiro[3.3]heptan-6-yl)benzo[d]thiazole Formaldehyde, 37% w/w aq. soln., stab. with 7-8% MeOH (711.21 mg, 23.68 mmol, 656.70 µL) and sodium acetate (1.94 g, 23.68 mmol, 1.27 mL) were added to the solution of 2-(2-azaspiro[3.3]heptan-6-yl)-5-bromo-1,3-benzothiazole (5 g, 11.84 mmol, TFA) in MeOH (60 mL). Resulting mixture was stirred at 20° C. for 1 hr before sodium cyan borohydride (1.49 g, 23.68 mmol) was added thereto. After that, stirring was continued for 16 hr. Then, solvent was removed under reduced pressure and residue was partitioned between 15% aq. K₂CO₃ solution (30 mL) and DCM (50 mL). Organic layer was separated, dried over solid K₂CO₃ and concentrated under reduced pressure, leaving 5-bromo-2-(2-methyl-2-azaspiro[3.3]heptan-6-yl)-1,3-benzothiazole (3.8 g, 11.76 mmol, 99.27% yield).

LCMS(ESI): [M]⁺ m/z: calcd 323.2; found 324.2; Rt=1.079 min.

Step 5: Synthesis of 2-(2-methyl-2-azaspiro[3.3]heptan-6-yl)-5-(4,4,5,5-tetramethyl-1,3,2-dioxaborolan-2-yl)benzo[d]thiazole Prepared by general procedure scheme H step 2. Yield: 1.5 g (34.46%).

CC conditions: The crude product was purified by silica gel with MTBE/MeOH as an eluent mixture.

LCMS(ESI): [M]⁺ m/z: calcd 370.2; found 371.2; Rt=2.997 min.

Step 6: Synthesis of (S)-tert-butyl 3-methyl-6-(2-(2-methyl-2-azaspiro[3.3]heptan-6-yl)benzo[d]thiazol-5-yl)-3,4-dihydropyridine-1(2H)-carboxylate Prepared by general procedure scheme H step 3. Yield: 1.2 g of crude.

LCMS(ESI): [M]⁺ m/z: calcd 439.2; found 440.2; Rt=1.166 min.

Step 7: Synthesis of (S)-5-(5-methyl-3,4,5,6-tetrahydropyridin-2-yl)-2-(2-methyl-2-azaspiro[3.3]heptan-6-yl)benzo[d]thiazole Prepared by general procedure scheme H step 4. Yield: 700 mg of crude.

LCMS(ESI): [M]⁺ m/z: calcd 339.2; found 340.2; Rt=0.774 min.

Step 8: Synthesis of 2-(2-methyl-2-azaspiro[3.3]heptan-6-yl)-5-((2R,5S)-5-methylpiperidin-2-yl)benzo[d]thiazole Prepared by general procedure scheme H step 5. Yield: 600 mg (72.91%).

LCMS(ESI): [M]+ m/z: calcd 341.2; found 342.2; Rt=0.770 min.

Step 9: Synthesis of 2-methoxy-5-(2-((2R,5S)-5-methyl-2-(2-(2-methyl-2-azaspiro[3.3]heptan-6-yl)benzo[d]thiazol-5-yl)piperidin-1-yl)-2-oxoacetamido)nicotinamide (Compound 1236

Prepared by general procedure scheme H step 6A. Yield: 42 mg (16.99%).

HPLC conditions: Column: XBridge C18 100*19 mm, 5 microM; 0-5 min 40-85% water-MeOH+0.1% NH$_4$OH, flow: 30 mL/min; (loading pump 4 mL/min MeOH).

$^1$H NMR (600 MHz, DMSO-d$_6$) δ (ppm) 0.97-1.09 (m, 3H), 1.32-1.42 (m, 1H), 1.66-1.76 (m, 1H), 1.83-1.93 (m, 1H), 2.05-2.24 (m, 4H), 2.27-2.35 (m, 1H), 2.40-2.46 (m, 2H), 2.56-2.84 (m, 3H), 3.05 (s, 2H), 3.21 (s, 2H), 3.46-4.08 (m, 5H), 5.25-5.73 (m, 1H), 7.31-7.42 (m, 1H), 7.61-7.78 (m, 2H), 7.83-7.91 (m, 1H), 7.98-8.07 (m, 1H), 8.40-8.63 (m, 2H), 10.98-11.16 (m, 1H).

LCMS(ESI): [M]+ m/z: calcd 562.2; found 563.2; Rt=2.487 min.

Example 627. The Synthesis of N-(6-amino-5-ethylpyridin-3-yl)-2-((2R,5S)-2-(2-(1-(dimethylamino)ethyl)benzo[d]thiazol-5-yl)-5-methylpiperidin-1-yl)-2-oxoacetamide (Compound 1316 and Compound 1188

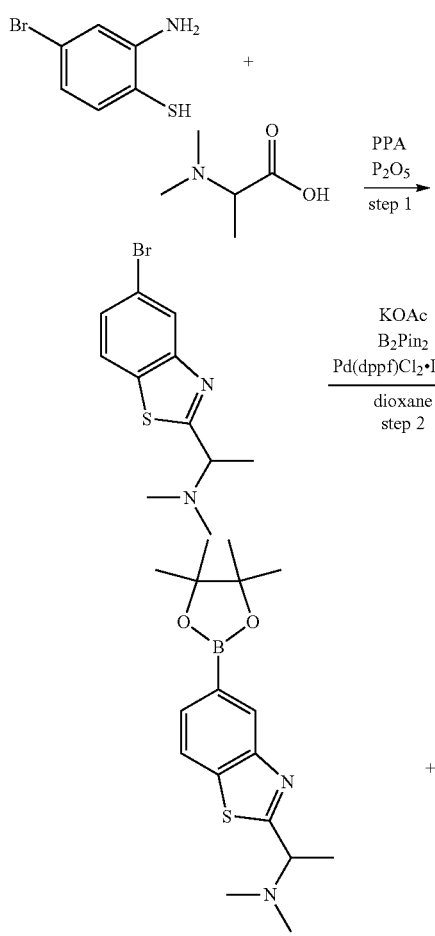

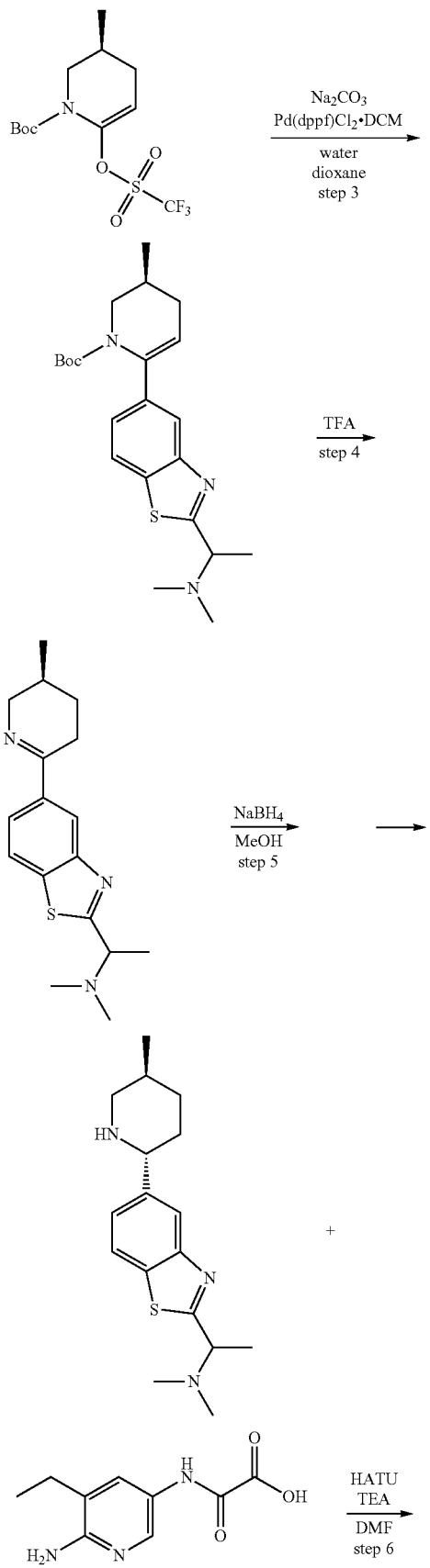

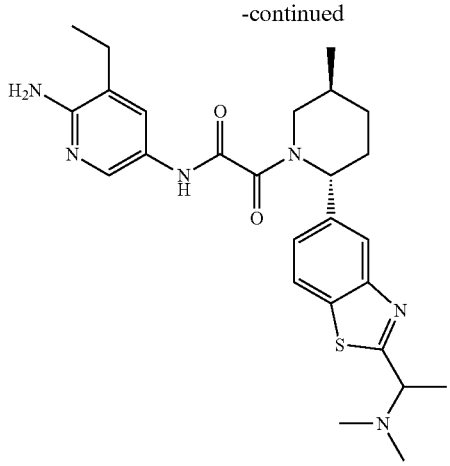

Compound 1316

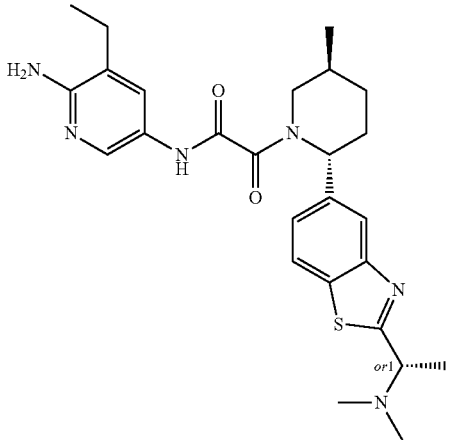

Compound 1188

Step 1: Synthesis of 1-(5-bromobenzo[d]thiazol-2-yl)-N,N-dimethylethanamine

Prepared by general procedure scheme H step 1A. Yield: 2.5 g (89.45%).

LCMS(ESI): [M]$^+$ m/z: calcd 285.2; found 286.2; Rt=0.759 min.

Step 2: Synthesis of N,N-dimethyl-1-(5-(4,4,5,5-tetramethyl-1,3,2-dioxaborolan-2-yl)benzo[d]thiazol-2-yl)ethanamine Prepared by general procedure scheme H step 2. Yield: 2.9 g (99.57%).

LCMS(ESI): [M]$^+$ m/z: calcd 332.2; found 333.2; Rt=1.123 min.

Step 3: Synthesis of (3S)-tert-butyl 6-(2-(1-(dimethylamino)ethyl)benzo[d]thiazol-5-yl)-3-methyl-3,4-dihydropyridine-1(2H)-carboxylate Prepared by general procedure scheme H step 3. Yield: 4 g of crude.

LCMS(ESI): [M]$^+$ m/z: calcd 401.2; found 402.2; Rt=1.198 min.

Step 4: Synthesis of N,N-dimethyl-1-(5-((S)-5-methyl-3,4,5,6-tetrahydropyridin-2-yl)benzo[d]thiazol-2-yl)ethanamine Prepared by general procedure scheme H step 4. Yield: 4 g of crude.

LCMS(ESI): [M]$^+$ m/z: calcd 301.2; found 302.2; Rt=0.560 min.

Step 5: Synthesis of N,N-dimethyl-1-(5-((2R,5S)-5-methylpiperidin-2-yl)benzo[d]thiazol-2-yl)ethanamine Prepared by general procedure scheme H step 5. Yield: 4 g of crude.

LCMS(ESI): [M]$^+$ m/z: calcd 303.2; found 304.2; Rt=0.509 min.

Step 6: Synthesis of N-(6-amino-5-ethylpyridin-3-yl)-2-((2R,5S)-2-(2-(1-(dimethylamino)ethyl)benzo[d]thiazol-5-yl)-5-methylpiperidin-1-yl)-2-oxoacetamide Prepared by general procedure scheme H step 6A. Yield: 81 mg (29.67%).

HPLC conditions: Column: XBridge C18 100*19 mm, 5 microM; 0-1-6 min 15-15-65% water-MeCN+0.1% NH$_4$OH, flow: 30 mL/min; (loading pump 4 mL/min MeOH).

LCMS(ESI): [M]$^+$ m/z: calcd 494.2; found 495.2; Rt=2.099 min.

Step 7: Chiral Separation (Compound 1316 and Compound 1188

Racemic N-(6-amino-5-ethyl-3-pyridyl)-2-[(2R,5S)-2-[2-[1-(dimethylamino)ethyl]-1,3-benzothiazol-5-yl]-5-methyl-1-piperidyl]-2-oxo-acetamide (81 mg, 163.75 umol) was chiral separated (Column: Chiralpak AD-H III (250*20 mm, 5 mkm); Hexane-IPA-MeOH, 50-25-25. Flow Rate: 10 mL/min) to obtain N-(6-amino-5-ethyl-3-pyridyl)-2-[(2R,5S)-2-[2-[(1R)-1-(dimethylamino)ethyl]-1,3-benzothiazol-5-yl]-5-methyl-1-piperidyl]-2-oxo-acetamide (22.3 mg, 45.08 μmol, 55.06% yield) (RT=75.09 min) and N-(6-amino-5-ethyl-3-pyridyl)-2-[(2R,5S)-2-[2-[(1S)-1-(dimethylamino)ethyl]-1,3-benzothiazol-5-yl]-5-methyl-1-piperidyl]-2-oxo-acetamide (25 mg, 50.54 μmol, 61.73% yield) (RT=91.19 min).

Rel Time for Compound 1316 in analytical conditions (column: AD-H, Hexane-IPA-MeOH, 50-25-25, 0.6 mL/min as mobile phase) 58.24 min and for Compound 1188 72.96 min.

Compound 1316:Retention time: 58.24 min $^1$H NMR (600 MHz, DMSO-d$_6$) δ (ppm) 1.02-1.14 (m, 6H), 1.31-1.38 (m, 1H), 1.39-1.42 (m, 3H), 1.66-1.75 (m, 1H), 1.83-1.92 (m, 1H), 2.04-2.21 (m, 1H), 2.27 (s, 6H), 2.29-2.35 (m, 1H), 2.38-2.42 (m, 1H), 2.76-3.29 (m, 2H), 3.47-4.06 (m, 2H), 5.25-5.72 (m, 3H), 7.32-7.43 (m, 1H), 7.43-7.53 (m, 1H), 7.84-7.91 (m, 1H), 7.97-8.11 (m, 2H), 10.50-10.62 (m, 1H).

LCMS(ESI): [M]$^+$ m/z: calcd 494.2; found 495.2; Rt=2.102 min.

Compound 1188: Retention time: 72.96 min $^1$H NMR (600 MHz, DMSO-d$_6$) δ (ppm) 1.02-1.15 (m, 6H), 1.31-1.38 (m, 1H), 1.39-1.44 (m, 3H), 1.67-1.74 (m, 1H), 1.82-1.92 (m, 1H), 2.06-2.22 (m, 1H), 2.24-2.36 (m, 8H), 2.39-2.42 (m, 1H), 2.76-3.25 (m, 1H), 3.46-4.08 (m, 2H), 5.24-5.72 (m, 3H), 7.33-7.42 (m, 1H), 7.43-7.53 (m, 1H), 7.84-7.91 (m, 1H), 7.97-8.09 (m, 2H), 10.49-10.61 (m, 1H).

LCMS(ESI): [M]$^+$ m/z: calcd 494.2; found 495.2; Rt=2.109 min.

Example 628. The Synthesis of N-(6-amino-5-ethylpyridin-3-yl)-2-((2R,5S)-2-(2-(2-(dimethylamino)propyl)benzo[d]thiazol-5-yl)-5-methylpiperidin-1-yl)-2-oxoacetamide (Compound 1345)

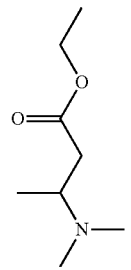 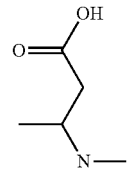

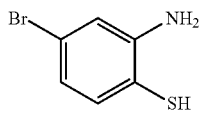

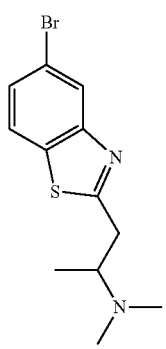

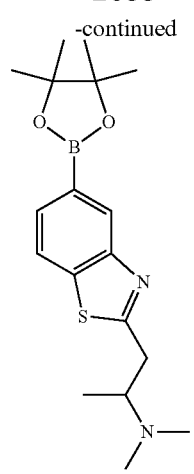

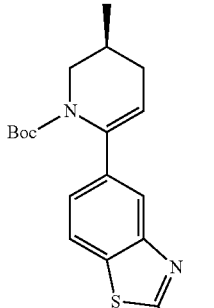

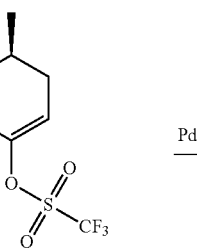

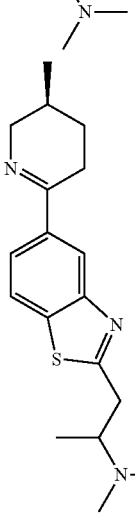

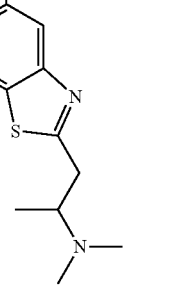

-continued

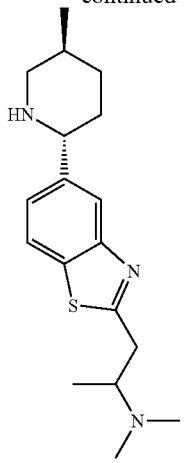

+

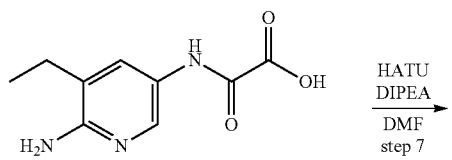

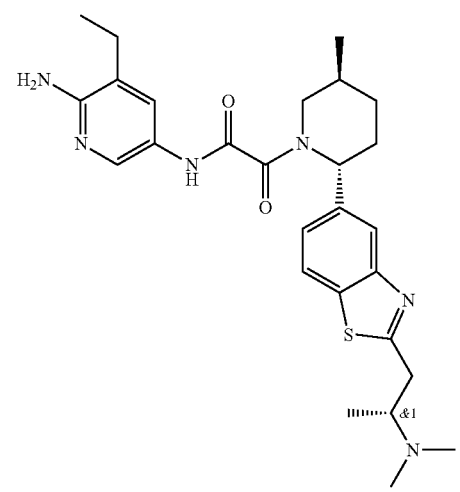

Compound 1345

Step 1: Synthesis of 3-(dimethylamino)butanoic acid

The stirred solution of ethyl 3-(dimethylamino)butanoate (0.5 g, 3.14 mmol) in HCl(15%) (5 mL) was allowed to stir at 90° C. for 2 hr. Upon completion, the reaction mixture was concentrated under reduced pressure. The desired product 3-(dimethylamino)butanoic acid (0.4 g, 2.39 mmol, 75.99% yield, HCl) was isolated.

$^1$H NMR (500 MHz, CDCl$_3$) δ (ppm) 1.25 (d, 3H), 2.64 (s, 6H), 2.97 (m, 1H), 3.56 (m, 1H), 4.77 (m, 2H), 10.91 (m, 1H).

Step 2: Synthesis of 1-(5-bromobenzo[d]thiazol-2-yl)-N,N-dimethylpropan-2-amine

The stirred solution of 3-(dimethylamino)butanoic acid (0.4 g, 2.39 mmol, HCl) and 2-amino-4-bromo-benzenethiol (0.5 g, 2.45 mmol) in PPA (5 mL) was allowed to stir at 140° C. for 16 hr. Upon completion, the reaction mixture was quenched with water (50 mL) and neutralized by NaOH to pH=8. The aqueous phase was extracted with EtOAc (2*20 mL). The combined organic phase was dried over Na$_2$SO$_4$ and concentrated under reduced pressure. The desired product 1-(5-bromo-1,3-benzothiazol-2-yl)-N,N-dimethyl-propan-2-amine (0.6 g, 2.01 mmol, 84.03% yield) was isolated.

LCMS(ESI): [M]$^+$ m/z: calcd 299.2; found 300.2; Rt=0.938 min.

Step 3: Synthesis of N,N-dimethyl-1-(5-(4,4,5,5-tetramethyl-1,3,2-dioxaborolan-2-yl)benzo[d]thiazol-2-yl)propan-2-amine Prepared by general procedure scheme H step 2. Yield: 0.3 g (56.64%).

CC conditions: The crude product was purified by silica gel with EtOAc/MeOH as an eluent mixture.

LCMS(ESI): [M]$^+$ m/z: calcd 264.2; found 265.2; Rt=0.536 min.

Step 4: Synthesis of (3S)-tert-butyl 6-(2-(2-(dimethylamino)propyl)benzo[d]thiazol-5-yl)-3-methyl-3,4-dihydropyridine-1(2H)-carboxylate Prepared by general procedure scheme H step 3. Yield: 0.3 g (63.56%).

LCMS(ESI): [M]$^+$ m/z: calcd 415.2; found 416.2; Rt=0.992 min.

Step 5: Synthesis of N,N-dimethyl-1-(5-((S)-5-methyl-3,4,5,6-tetrahydropyridin-2-yl)benzo[d]thiazol-2-yl)propan-2-amine The stirred solution of tert-butyl (3S)-6-[2-[2-(dimethylamino)propyl]-1,3-benzothiazol-5-yl]-3-methyl-3,4-dihydro-2H-pyridine-1-carboxylate (0.3 g, 721.86 μmol) in MeOH (15 mL) and diox/HCl (5 mL) was allowed to stir at 25° C. for 4 hr. Upon completion, the reaction mixture was evaporated, the crude product was quenched with water (20 mL) and neutralized by NaHCO$_3$ to pH=8. The aqueous phase was extracted with CHCl$_3$ (2*20 mL). The combined organic phase was dried over Na$_2$SO$_4$ and concentrated under reduced pressure. The desired product N,N-dimethyl-1-[5-[(3S)-3-methyl-2,3,4,5-tetrahydropyridin-6-yl]-1,3-benzothiazol-2-yl]propan-2-amine (0.22 g, 697.36 μmol, 96.61% yield) was isolated.

LCMS(ESI): [M]$^+$ m/z: calcd 315.2; found 316.2; Rt=0.655 min.

Step 6: Synthesis of N,N-dimethyl-1-(5-((2R,5S)-5-methylpiperidin-2-yl)benzo[d]thiazol-2-yl)propan-2-amine Prepared by general procedure scheme H step 5. Yield: 0.22 g of crude.
LCMS(ESI): [M]⁺ m/z: calcd 317.2; found 318.2; Rt=0.445 min.

Step 7: Synthesis of N-(6-amino-5-ethylpyridin-3-yl)-2-((2R,5S)-2-(2-(2-(dimethylamino)propyl)benzo[d]thiazol-5-yl)-5-methylpiperidin-1-yl)-2-oxoacetamide (Compound 1345

Prepared by general procedure scheme H step 6B. Yield: 38 mg (10.78%).
HPLC conditions: Column: XBridge C18 100*19 mm, 5 microM; 0-1-6 min 35-50% water-MeCN+0.1% NH₄OH, flow: 30 ml/min; (loading pump 4 ml/min MeOH).
¹H NMR (600 MHz, DMSO-d₆) δ (ppm) 0.98-1.14 (m, 9H), 1.29-1.41 (m, 1H), 1.64-1.75 (m, 1H), 1.81-1.93 (m, 1H), 2.02-2.19 (m, 1H), 2.21 (s, 6H), 2.28-2.34 (m, 1H), 2.39-2.43 (m, 1H), 2.76-3.27 (m, 5H), 3.46-4.07 (m, 1H), 5.24-5.71 (m, 3H), 7.30-7.40 (m, 1H), 7.42-7.52 (m, 1H), 7.81-7.89 (m, 1H), 7.97-8.08 (m, 2H), 10.41 (s, 1H).
LCMS(ESI): [M]⁺ m/z: calcd 508.2; found 509.2; Rt=2.166 min.

Example 629. The Synthesis of 5-(2-((2R,5S)-2-(2-(1-cyclopropylpiperidin-4-yl)benzo[d]thiazol-5-yl)-5-methylpiperidin-1-yl)-2-oxoacetamido)-2-methoxynicotinamide (Compound 1219

Step 1: Synthesis of 5-chloro-2-(1-cyclopropylpiperidin-4-yl)benzo[d]thiazole

Prepared by general procedure scheme H step 1A. Yield: 8 g (90.63%).
LCMS(ESI): [M]⁺ m/z: calcd 292.2; found 293.2; Rt=0.848 min.

Step 2: Synthesis of 2-(1-cyclopropylpiperidin-4-yl)-5-(4,4,5,5-tetramethyl-1,3,2-dioxaborolan-2-yl)benzo[d]thiazole

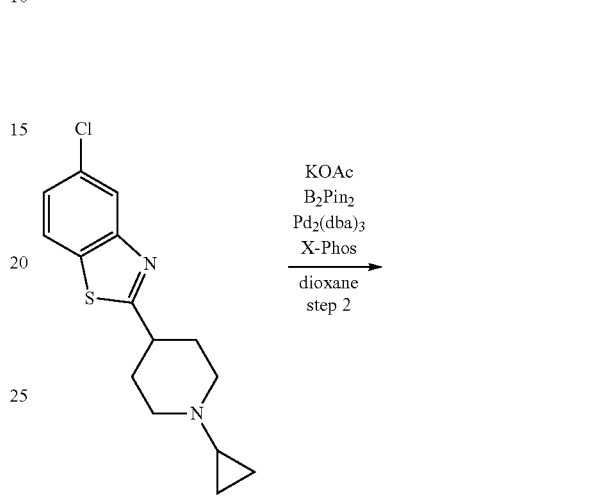

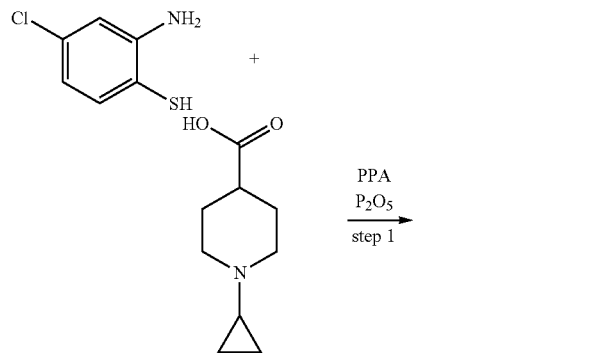

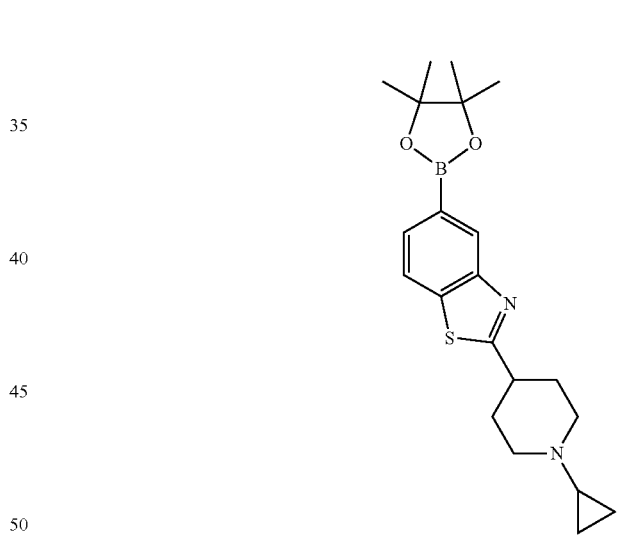

5-chloro-2-(1-cyclopropyl-4-piperidyl)-1,3-benzothiazole (4 g, 13.66 mmol), 4,4,5,5-tetramethyl-2-(4,4,5,5-tetramethyl-1,3,2-dioxaborolan-2-yl)-1,3,2-dioxaborolane (3.82 g, 15.03 mmol) and potassium acetate (2.68 g, 27.32 mmol, 1.71 mL) were mixed in dioxane (70 mL). The resulting mixture was evacuated and then backfilled with argon, this operation was repeated three times, then tris(dibenzylideneacetone)dipalladium (0) (625.43 mg, 683.00 umol) was added under argon. The reaction mixture was stirred under argon at 90° C. for 14 hr, then cooled and concentrated under reduce pressure. The residue was purified by column chromatography to afford 2-(1-cyclopropyl-4-piperidyl)-5-(4,4,5,5-tetramethyl-1,3,2-dioxaborolan-2-yl)-1,3-benzothiazole (2.4 g, 6.24 mmol, 45.71% yield).
LCMS(ESI): [M]⁺ m/z: calcd 384.2; found 385.2; Rt=1.026 min.

2693

Step 3: Synthesis of (S)-tert-butyl 6-(2-(1-cyclopropylpiperidin-4-yl)benzo[d]thiazol-5-yl)-3-methyl-3,4-dihydropyridine-1(2H)-carboxylate

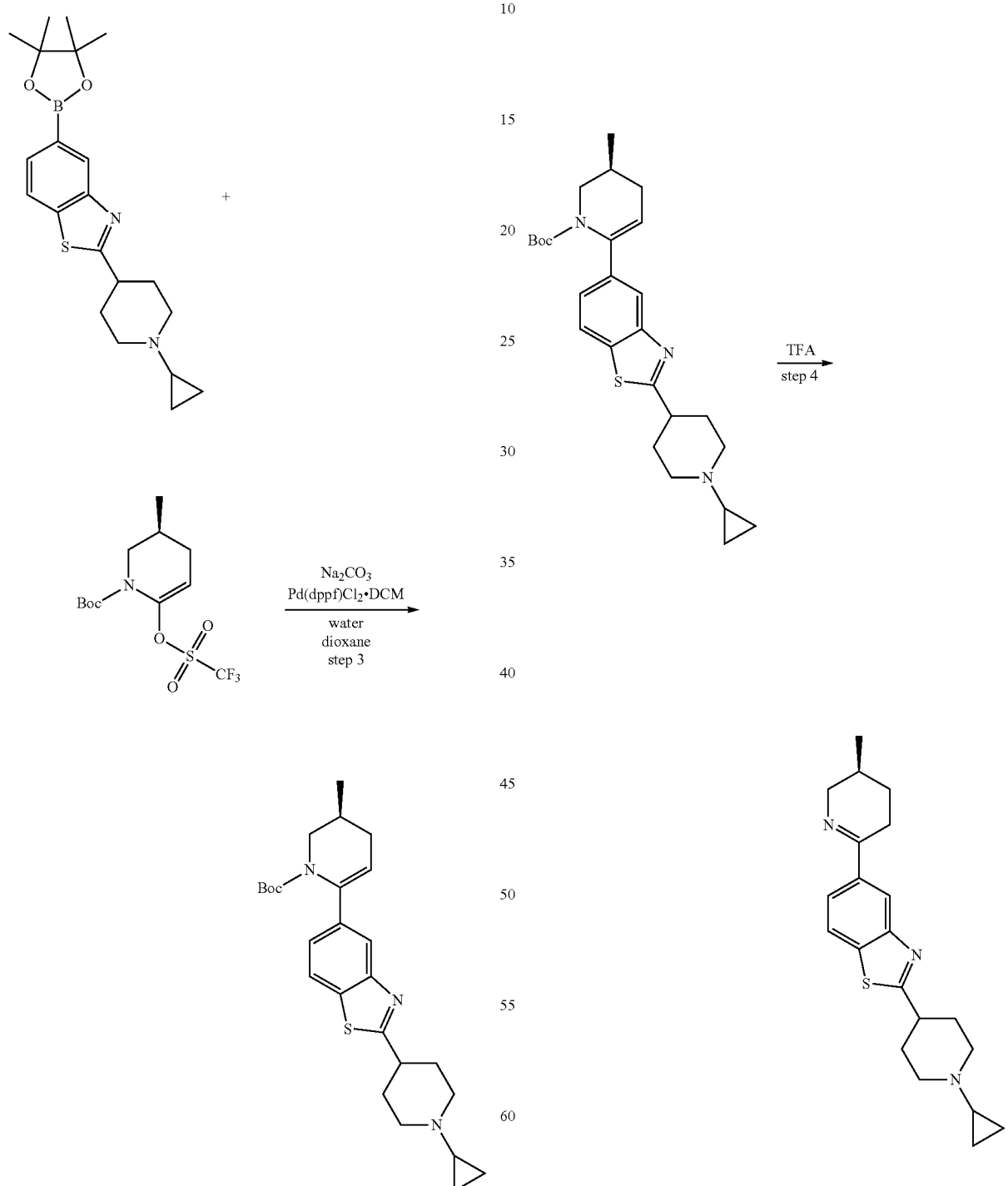

Prepared by general procedure scheme H step 3. Yield: 0.6 g (29.90%).

2694

CC conditions: The crude product was purified by silica gel with Hexane/EtOAc as an eluent mixture.

LCMS(ESI): [M]$^+$ m/z: calcd 453.2; found 454.2; Rt=1.372 min.

Step 4: Synthesis of (S)-2-(1-cyclopropylpiperidin-4-yl)-5-(5-methyl-3,4,5,6-tetrahydropyridin-2-yl)benzo[d]thiazole Prepared by general procedure scheme H step 4. Yield: 0.3 g of crude.

LCMS(ESI): [M]$^+$ m/z: calcd 353.2; found 354.2; Rt=0.719 min.

2695

Step 5: Synthesis of 2-(1-cyclopropylpiperidin-4-yl)-5-((2R,5S)-5-methylpiperidin-2-yl)benzo[d]thiazole

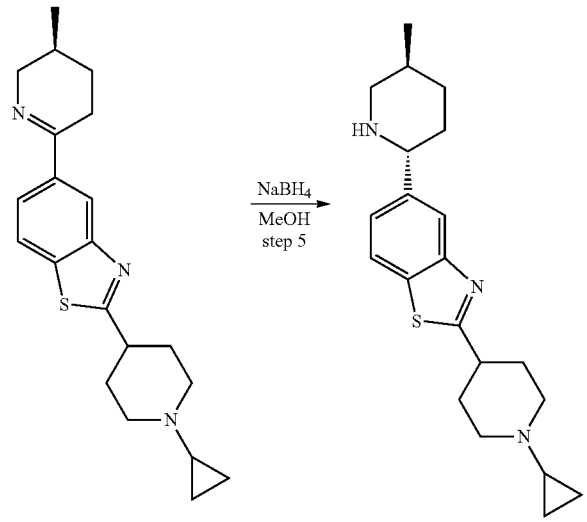 [SMILES: C[C@H]1CCC(c2ccc3sc(C4CCN(C5CC5)CC4)nc3c2)=NC1 ; "NaBH4" ; C[C@H]1CC[C@H](c2ccc3sc(C4CCN(C5CC5)CC4)nc3c2)NC1]

Prepared by general procedure scheme H step 5. Yield: 0.28 g of crude.

LCMS(ESI): [M]⁺ m/z: calcd 355.2; found 356.2; Rt=0.751 min.

Step 6: The Synthesis of 5-(2-((2R,5S)-2-(2-(1-cyclopropylpiperidin-4-yl)benzo[d]thiazol-5-yl)-5-methylpiperidin-1-yl)-2-oxoacetamido)-2-methoxynicotinamide (Compound 1219)

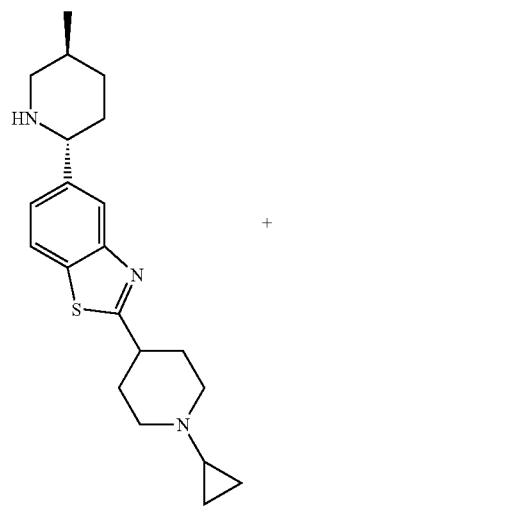

+

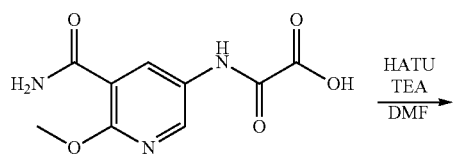

2696

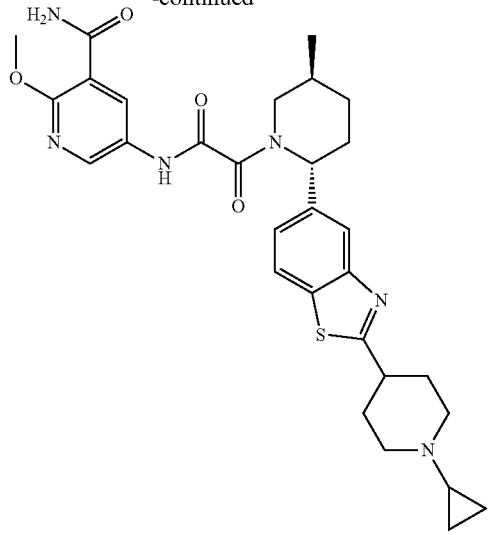

Prepared by general procedure scheme H step 6A. Yield: 30 mg (13.21%).

HPLC conditions: Column: XBridge C18 100*19 mm, 5 microM; 0-55 min 40-90% water-MeOH+0.1% NH₄OH; (loading pump 4 ml/min MeOH).

5-[[2-[(2R,5S)-2-[2-(1-cyclopropyl-4-piperidyl)-1,3-benzothiazol-5-yl]-5-methyl-1-piperidyl]-2-oxo-acetyl]amino]-2-methoxy-pyridine-3-carboxamide was purified by chiral HPLC: (Column: Chiralpak 1B (250*30 mm, 5 mkm), Mobile phase: Hexane-IPA-MeOH, 60-20-20; Flow rate: 12 ml/min) to obtain 5-[[2-[(2R,5S)-2-[2-(1-cyclopropyl-4-piperidyl)-1,3-benzothiazol-5-yl]-5-methyl-1-piperidyl]-2-oxo-acetyl]amino]-2-methoxy-pyridine-3-carboxamide (30 mg, 52.02 μmol, 13.21% yield).

Rel Time for Compound 1219 in analytical conditions (column: 1B, Hexane-IPA-MeOH, 50-25-25, 0.6 ml/min as mobile phase) 15.85 min.

Compound 1219: Retention time: 15.85 min

¹H NMR (600 MHz, DMSO-d₆) δ (ppm) 0.26-0.32 (m, 2H), 0.38-0.44 (m, 2H), 1.00-1.07 (m, 3H), 1.30-1.42 (m, 1H), 1.58-1.64 (m, 1H), 1.66-1.75 (m, 3H), 1.82-1.93 (m, 1H), 2.02-2.22 (m, 3H), 2.27-2.35 (m, 3H), 2.81-3.28 (m, 4H), 3.47-4.06 (m, 4H), 5.26-5.73 (m, 1H), 7.33-7.43 (m, 1H), 7.66-7.77 (m, 2H), 7.85-7.90 (m, 1H), 8.01-8.09 (m, 1H), 8.38-8.60 (m, 2H), 10.92-11.19 (m, 1H).

LCMS(ESI): [M]⁺ m/z: calcd 576.2; found 577.2; Rt=2.630 min.

Example 630. The Synthesis of N-(6-amino-5-ethylpyridin-3-yl)-2-((2R,5S)-5-methyl-2-(2-(Pyridin-2-yl)benzo[d]thiazol-5-yl)piperidin-1-yl)-2-oxoacetamide (Compound 1238)

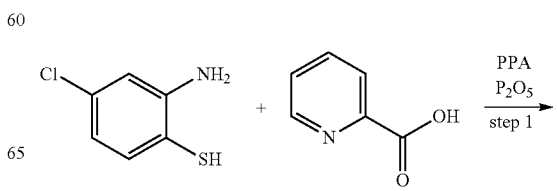

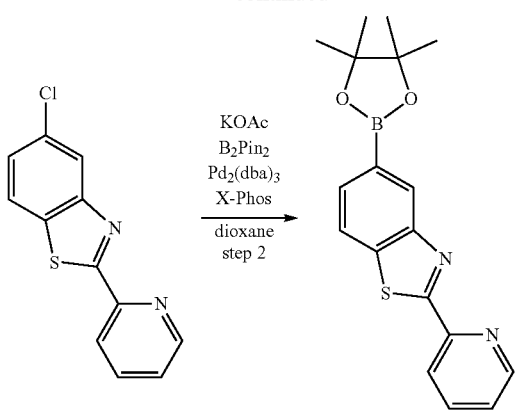

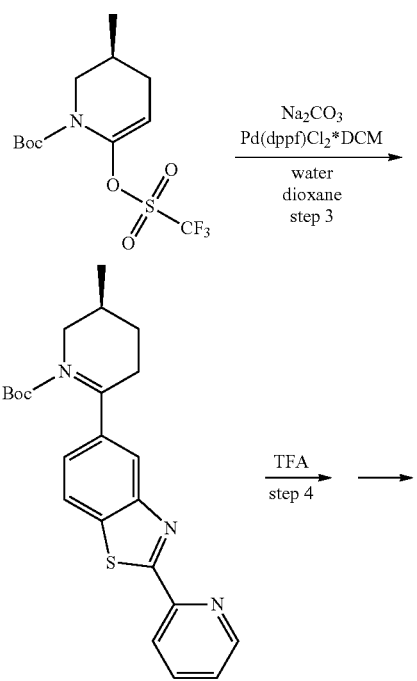

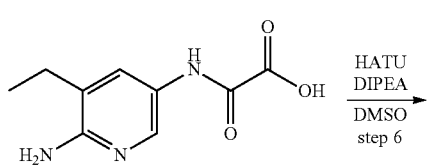

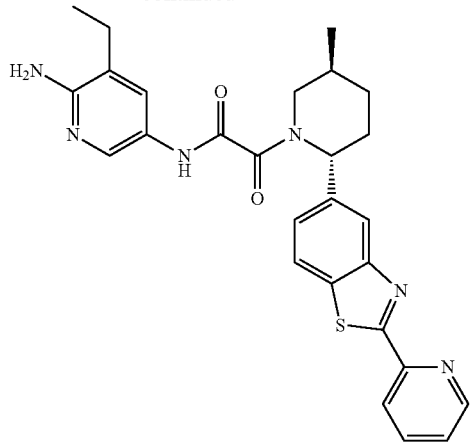

Step 1: Synthesis of 5-chloro-2-(Pyridin-2-yl)benzo[d]thiazole

Prepared by general procedure scheme H step 1A. Yield: 1.3 g (28.04%).
LCMS(ESI): [M]+ m/z: calcd 246.2; found 247.2; Rt=1.228 min.

Step 2: Synthesis of 2-(Pyridin-2-yl)-5-(4,4,5,5-tetramethyl-1,3,2-dioxaborolan-2-yl)benzo[d]thiazole 5-chloro-2-(2-pyridyl)-1,3-benzothiazole (1.2 g, 4.86 mmol), 4,4,5,5-tetramethyl-2-(4,4,5,5-tetramethyl-1,3,2-dioxaborolan-2-yl)-1,3,2-dioxaborolane (1.36 g, 5.35 mmol) and potassium acetate (954.69 mg, 9.73 mmol, 608.08 μL) were mixed in dioxane (19.82 mL). The resulting mixture was evacuated and then backfilled with argon, this operation was repeated three times, then tris(dibenzylideneacetone)dipalladium (0) (222.70 mg, 243.20 μmol) was added under argon. The reaction mixture was stirred under argon at 90° C. for 14 hr, then cooled and concentrated under reduce pressure. The residue was purified by column chromatography (SiO2, CHCl3-MeCN from 0-100%, flow rate=70 mL/min, cv=8.8) to afford 2-(2-pyridyl)-5-(4,4,5,5-tetramethyl-1,3,2-dioxaborolan-2-yl)-1,3-benzothiazole (0.45 g, 1.33 mmol, 27.35% yield).
LCMS(ESI): [M]+ m/z: calcd 338.2; found 339.2; Rt=1.596 min.

Step 3: Synthesis of (S)-tert-butyl 3-methyl-6-(2-(Pyridin-2-yl)benzo[d]thiazol-5-yl)-3,4-dihydropyridine-1(2H)-carboxylate Prepared by general procedure scheme H step 3. Yield: 0.47 g of crude.
LCMS(ESI): [M]+ m/z: calcd 407.2; found 408.2; Rt=1.660 min.

Step 4: Synthesis of (S)-5-(5-methyl-3,4,5,6-tetrahydropyridin-2-yl)-2-(Pyridin-2-yl)benzo[d]thiazole Prepared by general procedure scheme H step 4. Yield: 0.35 g (98.72%).
LCMS(ESI): [M]+ m/z: calcd 307.2; found 308.2; Rt=0.836 min.

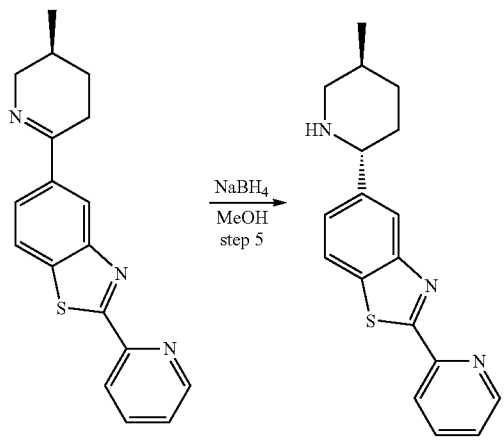

Step 5: Synthesis of 5-((2R,5S)-5-methylpiperidin-2-yl)-2-(Pyridin-2-yl)benzo[d]thiazole Prepared by general procedure scheme H step 5. Yield: 0.35 g of crude.
LCMS(ESI): [M]+ m/z: calcd 309.2; found 310.2; Rt=0.986 min.

Step 6: Synthesis of N-(6-amino-5-ethylpyridin-3-yl)-2-((2R,5S)-5-methyl-2-(2-(Pyridin-2-yl)benzo[d]thiazol-5-yl)piperidin-1-yl)-2-oxoacetamide (Compound 1238)

Prepared by general procedure scheme H step 6B. Yield: 17.5 mg (7.49%).
HPLC conditions: Column: SunFire C18 100*19 mm, 5 microM; 2-10 min 0-100% MeCN+FA, flow: 30 ml/min; (loading pump 4 ml/min MeCN).
$^1$H NMR (600 MHz, DMSO-$d_6$) δ (ppm) 1.03-1.15 (m, 6H), 1.31-1.44 (m, 1H), 1.70-1.77 (m, 1H), 1.86-1.96 (m, 1H), 2.09-2.26 (m, 1H), 2.30-2.35 (m, 1H), 2.38-2.44 (m, 2H), 2.81-3.22 (m, 1H), 3.48-4.10 (m, 1H), 5.30-5.77 (m, 3H), 7.43-7.48 (m, 1H), 7.48-7.55 (m, 1H), 7.55-7.61 (m, 1H), 7.98-8.09 (m, 3H), 8.13-8.21 (m, 1H), 8.28-8.35 (m, 1H), 8.70-8.76 (m, 1H), 10.52-10.64 (m, 1H).
LCMS(ESI): [M]+ m/z: calcd 500.2; found 501.2; Rt=2.553 min.

Example 631. The Synthesis of N-(6-amino-5-ethylpyridin-3-yl)-2-((2R,5S)-2-(2-(3-(dimethylamino)cyclobutyl)benzo[d]thiazol-5-yl)-5-methylpiperidin-1-yl)-2-oxoacetamide (Compound 1101)

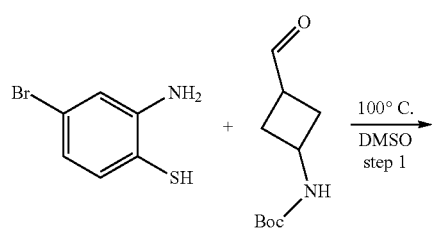

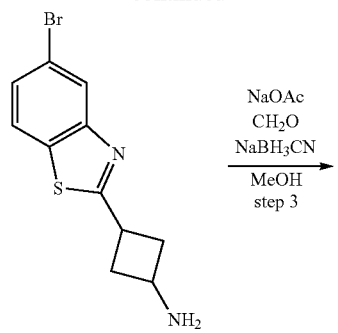

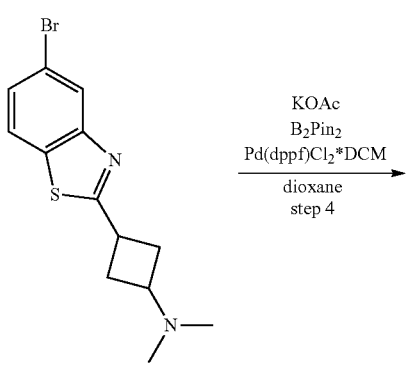

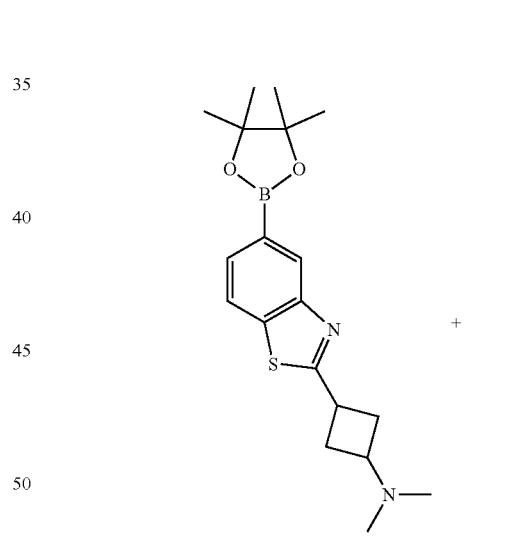

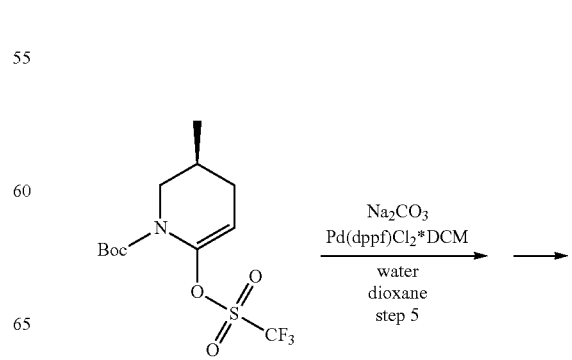

2701
-continued

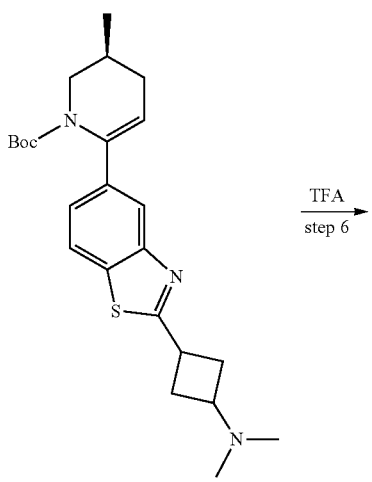

TFA
step 6 →

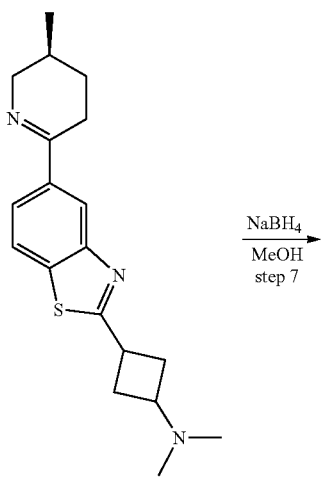

NaBH₄
MeOH
step 7 →

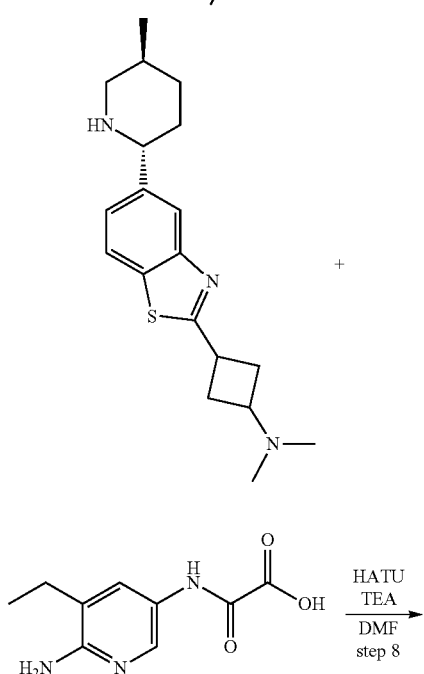

HATU
TEA
DMF
step 8 →

2702
-continued

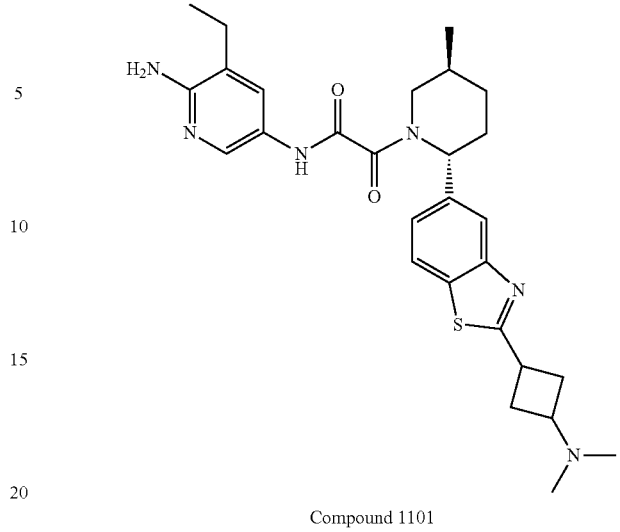

Compound 1101

Step 1: Synthesis of tert-butyl (3-(5-bromobenzo[d]thiazol-2-yl)cyclobutyl)carbamate Prepared by general procedure 8 step 1B. Yield: 5 g (53.24%).
LCMS(ESI): [M]⁺ m/z: calcd 383.2; found 384.2; Rt=1.402 min.

Step 2: Synthesis of 3-(5-bromobenzo[d]thiazol-2-yl)cyclobutanamine tert-butyl N-[3-(5-bromo-1,3-benzothiazol-2-yl)cyclobutyl]carbamate (5 g, 13.04 mmol) was treated with hydrogen chloride solution 4.0 M in dioxane (24.00 g, 658.26 mmol, 30 mL). The resulting mixture was stirred at 25° C. for 14 hr. Precipitate was filtered and additionally washed with MTBE. Then dried in vacuum to give 3-(5-bromo-1,3-benzothiazol-2-yl)cyclobutanamine (4 g, 12.51 mmol, 95.93% yield, HCl).
LCMS(ESI): [M]⁺ m/z: calcd 284.2; found 285.2; Rt=0.931 min.

Step 3: Synthesis of 3-(5-bromobenzo[d]thiazol-2-yl)-N,N-dimethylcyclobutanamine To the stirred solution of 3-(5-bromo-1,3-benzothiazol-2-yl)cyclobutanamine (4 g, 12.51 mmol, HCl) in MeOH (71.00 mL) formaldehyde, 37% w/w aq. soln., stab. with 7-8% MeOH (2.54 g, 31.28 mmol, 2.34 mL, 37% purity) and sodium acetate, anhydrous (2.57 g, 31.28 mmol, 1.68 mL) were added. The resulting mixture was stirred for 2 hr at 25° C. Then Sodium cyan borohydride (1.57 g, 25.03 mmol) was added portion wise. The resulting mixture was stirred at 25° C. for 12 hr. MeOH was evaporated. The residue was diluted with water (100 ml) and extracted with DCM (3*50 ml). Combined organic layers were dried over Na₂SO₄. DCM was evaporated in vacuum to give 3-(5-bromo-1,3-benzothiazol-2-yl)-N,N-dimethylcyclobutanamine (3.9 g, crude).
LCMS(ESI): [M]⁺ m/z: calcd 311.2; found 312.2; Rt=0.829 min.

Step 4: Synthesis of N,N-dimethyl-3-(5-(4,4,5,5-tetramethyl-1,3,2-dioxaborolan-2-yl)benzo[d]thiazol-2-yl)cyclobutanamine Prepared by general procedure Scheme H step 2. Yield: 4 g of crude.

LCMS(ESI): [M]⁺ m/z: calcd 358.2; found 359.2; Rt=1.029 min.

Prepared by general procedure Scheme H step 3. Yield: 7 g of crude.

LCMS(ESI): [M]⁺ m/z: calcd 427.2; found 428.2; Rt=1.057 min.

Step 6: Synthesis of (S)—N,N-dimethyl-3-(5-(5-methyl-3,4,5,6-tetrahydropyridin-2-yl)benzo[d]thiazol-2-yl)cyclobutanamine Prepared by general procedure Scheme H step 4. Yield: 3 g of crude.

LCMS(ESI): [M]⁺ m/z: calcd 327.2; found 328.2; Rt=0.635 min.

Step 7: Synthesis of N,N-dimethyl-3-(5-((2R,5S)-5-methylpiperidin-2-yl)benzo[d]thiazol-2-yl)cyclobutanamine Prepared by general procedure Scheme H step 5. Yield: 80 mg (2.65%).

HPLC conditions: Column: Chromatorex C18 100*19 mm, 5 microM; 0-1-6 min 45-45-85% water-MeOH, flow: 30 ml/min; (loading pump 4 ml/min MeOH).

LCMS(ESI): [M]⁺ m/z: calcd 329.2; found 330.2; Rt=1.324 min.

Step 8: Synthesis of N-(6-amino-5-ethylpyridin-3-yl)-2-((2R,5S)-2-(2-(3-(dimethylamino)cyclobutyl)benzo[d]thiazol-5-yl)-5-methylpiperidin-1-yl)-2-oxoacetamide (Compound 1101

Prepared by general procedure 8 step 6A. Yield: 5 mg (1.61%).

HPLC conditions: Column: YMC Triart C18 100*20 mm, 5 microM; 0-1-6 min 60-60-70% water-MeOH+0.1% NH₄OH, flow: 30 ml/min; (loading pump 4 ml/min MeOH).

¹H NMR (600 MHz, DMSO-d₆) δ (ppm) 1.02-1.14 (m, 6H), 1.32-1.39 (m, 1H), 1.65-1.75 (m, 1H), 1.81-1.93 (m, 1H), 2.04 (s, 6H), 2.09-2.14 (m, 2H), 2.26-2.36 (m, 2H), 2.39-2.42 (m, 2H), 2.54-2.56 (m, 2H), 2.65-2.71 (m, 1H), 2.77-2.97 (m, 1H), 3.45-4.07 (m, 2H), 5.24-5.71 (m, 3H), 7.32-7.41 (m, 1H), 7.42-7.53 (m, 1H), 7.85-7.91 (m, 1H), 7.98-8.09 (m, 2H), 10.56 (s, 1H).

LCMS(ESI): [M]⁺ m/z: calcd 520.2; found 521.2; Rt=2.206 min.

Example 632. The Synthesis of N-(6-amino-5-ethylpyridin-3-yl)-2-((2R,5S)-5-methyl-2-(2-(1-methylpyrrolidin-2-yl)benzo[d]thiazol-5-yl)piperidin-1-yl)-2-oxoacetamide (Compound 1282)

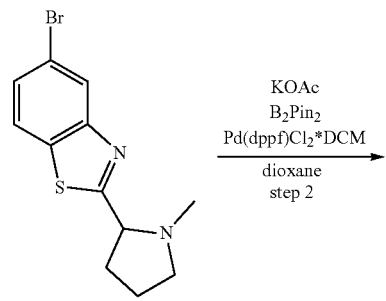

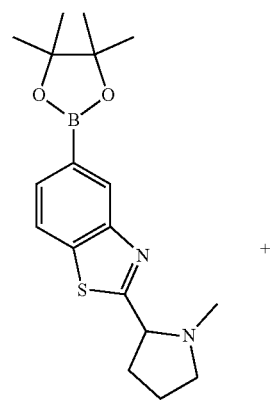

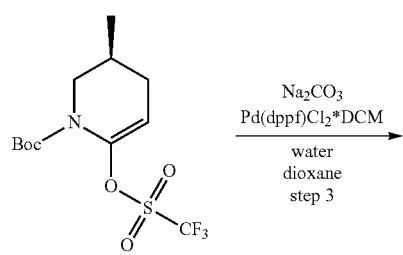

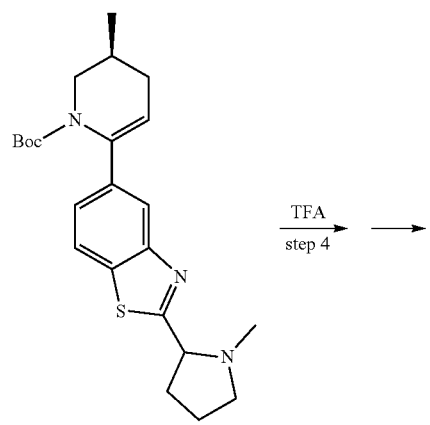

2705

-continued

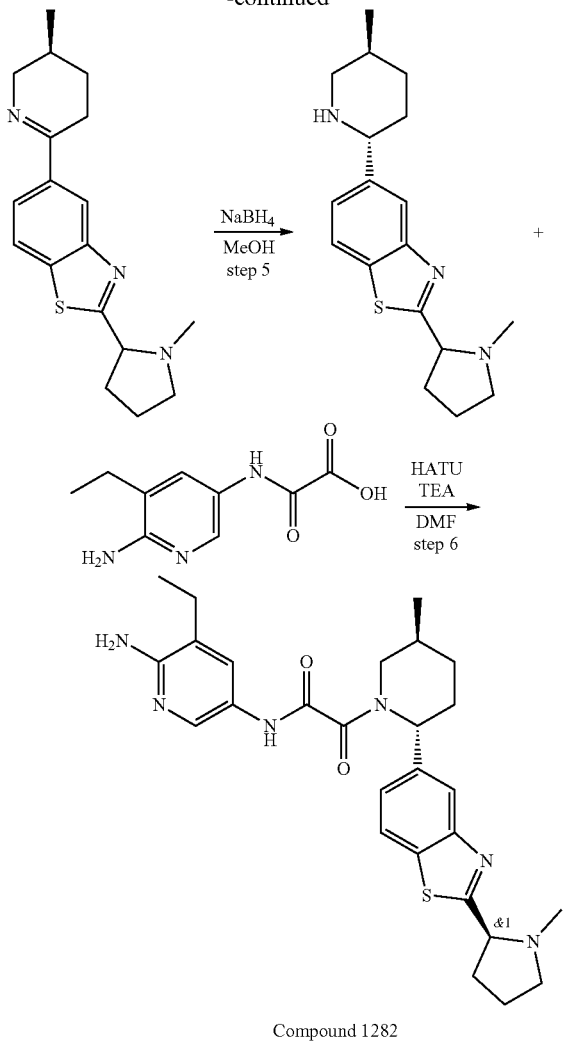

Compound 1282

Step 1: Synthesis of 5-bromo-2-(1-methylpyrrolidin-2-yl)benzo[d]thiazole

Prepared by general procedure scheme H step 1A. Yield: 2.8 g (97.34%).
LCMS(ESI): [M]+ m/z: calcd 297.2; found 298.2; Rt=0.958 min.

Step 2: Synthesis of 2-(1-methylpyrrolidin-2-yl)-5-(4,4,5,5-tetramethyl-1,3,2-dioxaborolan-2-yl)benzo[d]thiazole Prepared by general procedure scheme H step 2. Yield: 3.2 g of crude.
LCMS(ESI): [M]+ m/z: calcd 344.2; found 345.2; Rt=1.005 min.

Step 3: Synthesis of (3S)-tert-butyl 3-methyl-6-(2-(1-methylpyrrolidin-2-yl)benzo[d]thiazol-5-yl)-3,4-dihydropyridine-1(2H)-carboxylate Prepared by general procedure scheme H step 3. Yield: 5 g of crude.

2706

LCMS(ESI): [M]+ m/z: calcd 413.2; found 414.2; Rt=1.143 min.

Step 4: Synthesis of 5-((S)-5-methyl-3,4,5,6-tetrahydropyridin-2-yl)-2-(1-methylpyrrolidin-2-yl)benzo[d]thiazole Prepared by general procedure scheme H step 4. Yield: 1.2 g (31.67%).
LCMS(ESI): [M]+ m/z: calcd 313.2; found 314.2; Rt=0.624 min.

Step 5: Synthesis of 5-((2R,5S)-5-methylpiperidin-2-yl)-2-(1-methylpyrrolidin-2-yl)benzo[d]thiazole Prepared by general procedure scheme H step 5. Yield: 0.85 g (70.38%).
LCMS(ESI): [M]+ m/z: calcd 315.2; found 316.2; Rt=0.664 min.

Step 6: Synthesis of N-(6-amino-5-ethylpyridin-3-yl)-2-((2R,5S)-5-methyl-2-(2-(1-methylpyrrolidin-2-yl)benzo[d]thiazol-5-yl)piperidin-1-yl)-2-oxoacetamide (Compound 1282

Prepared by general procedure scheme H step 6A. Yield: 140 mg (34.87%).
HPLC conditions: Column: XBridge C18 100*19 mm, 5 microM; 0-5 min 40-90% water-MeOH+0.1% NH4OH, flow: 30 ml/min; (loading pump 4 ml/min MeOH).
This substance was chiral separated (Column: Chiral ART Cellulose-SC (250*20 mm, 5 mkm); Mobile phase: Hexane-IPA-MeOH, 70-15-15. Flow Rate: 12 mL/min).
$^1$H NMR (400 MHz, DMSO-d$_6$) δ (ppm) 1.02-1.06 (m, 3H), 1.06-1.16 (m, 3H), 1.29-1.44 (m, 1H), 1.67-1.91 (m, 5H), 2.08-2.25 (m, 1H), 2.26-2.35 (m, 2H), 2.37 (s, 3H), 2.38-2.40 (m, 1H), 2.40-2.46 (m, 2H), 2.77-3.30 (m, 2H), 3.32-4.12 (m, 2H), 5.24-5.62 (m, 1H), 5.62-5.78 (m, 2H), 7.29-7.43 (m, 1H), 7.43-7.56 (m, 1H), 7.82-7.89 (m, 1H), 7.98-8.11 (m, 2H), 10.56 (s, 1H).
LCMS(ESI): [M]+ m/z: calcd 506.2; found 507.2; Rt=1.629 min.

Example 633. The Synthesis of N-(6-amino-5-ethylpyridin-3-yl)-2-((2R,5S)-2-(2-(1-cyclopropylpiperidin-4-yl)benzo[d]thiazol-5-yl)-5-methylpiperidin-1-yl)-2-oxoacetamide (Compound 1330)

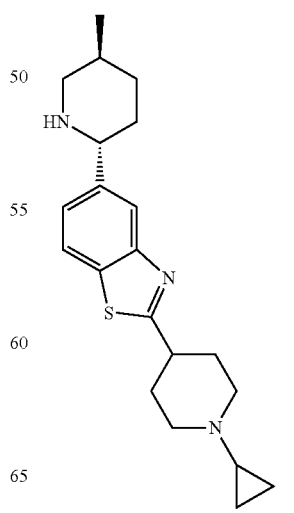

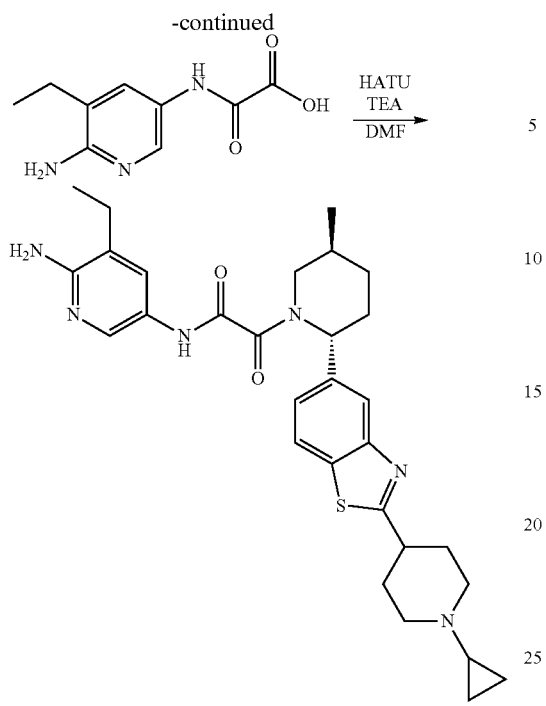

Compound 1330

Prepared by general procedure scheme H step 6A. Yield: 30 mg (8.31%).

HPLC conditions: Column: XBridge C18 100*19 mm, 5 microM; 0-1-6 min 60-60-80% water-MeOH+0.1% NH$_4$OH; (loading pump 4 ml/min MeOH).

N-(6-amino-5-ethyl-3-pyridyl)-2-[(2R,5S)-2-[2-(1-cyclopropyl-4-piperidyl)-1,3-benzothiazol-5-yl]-5-methyl-1-piperidyl]-2-oxo-acetamide was purified by chiral HPLC: (Column: Chiralpak IC-III (250*20 mm, 5 mkm); Mobile phase: IPA-MeOH, 50-50. Flow Rate: 12 mL/min) to obtain N-(6-amino-5-ethyl-3-pyridyl)-2-[(2R,5S)-2-[2-(1-cyclopropyl-4-piperidyl)-1,3-benzothiazol-5-yl]-5-methyl-1-piperidyl]-2-oxo-acetamide (22 mg, 40.24 µmol, 3.58% yield).

Rel Time for Compound 1330 in analytical conditions (column: 1C, IPA-MeOH, 50-50, 0.6 ml/min as mobile phase) 30.27 min.

$^1$H NMR (600 MHz, DMSO-d$_6$) δ (ppm) 0.30-0.41 (m, 4H), 1.02-1.13 (m, 6H), 1.31-1.39 (m, 1H), 1.62-1.71 (m, 3H), 1.84-1.89 (m, 2H), 2.05-2.07 (m, 3H) 2.30-2.41 (m, 4H), 2.77-2.79 (m, 1H), 2.99-3.10 (m, 3H), 3.47-4.05 (m, 2H), 5.27-5.69 (m, 3H), 7.33-7.51 (m, 2H), 7.85-7.89 (d, 1H), 7.99-8.06 (m, 2H), 10.52-10.58 (m, 1H).

LCMS(ESI): [M]$^+$ m/z: calcd 546.2; found 547.2; Rt=1.974 min.

Example 634. The Synthesis of N-(6-amino-5-ethylpyridin-3-yl)-2-((2R,5S)-5-methyl-2-(2-(Pyridin-4-yl)benzo[d]thiazol-5-yl)piperidin-1-yl)-2-oxoacetamide (Compound 1194)

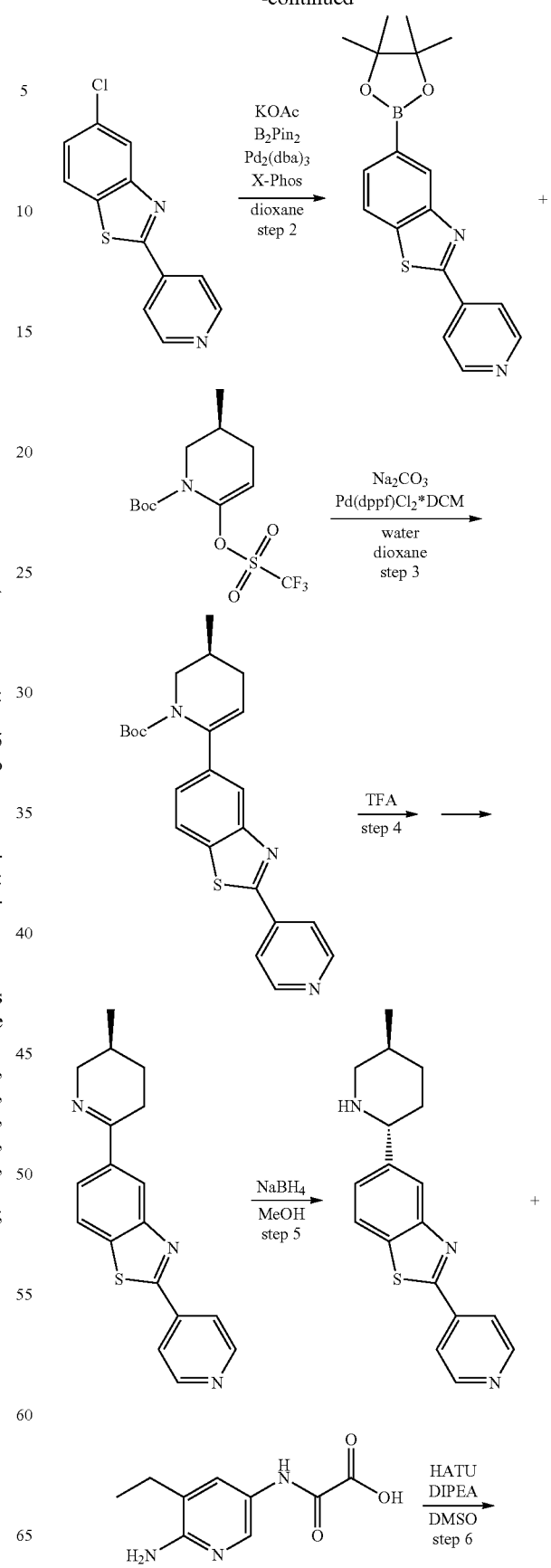

-continued

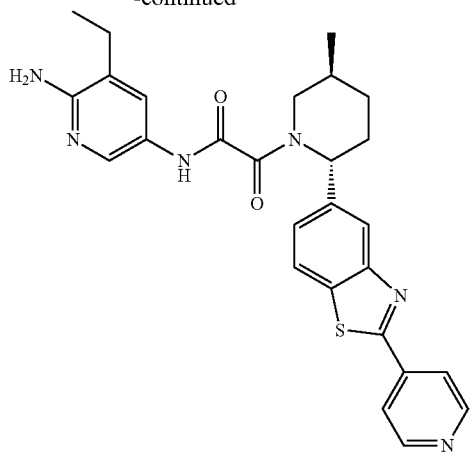

Step 1: Synthesis of 5-chloro-2-(Pyridin-4-yl)benzo[d]thiazole

Prepared by general procedure scheme H step 1A. Yield: 0.25 g (5.39%).

CC conditions: The crude product was purified by silica gel with hexane/IPA as an eluent mixture.

LCMS(ESI): [M]+ m/z: calcd 246.2; found 247.2; Rt=1.182 min.

Step 2: Synthesis of 2-(Pyridin-4-yl)-5-(4,4,5,5-tetramethyl-1,3,2-dioxaborolan-2-yl)benzo[d]thiazole 5-chloro-2-(4-pyridyl)-1,3-benzothiazole (0.3 g, 1.22 mmol), 4,4,5,5-tetramethyl-2-(4,4,5,5-tetramethyl-1,3,2-dioxaborolan-2-yl)-1,3,2-dioxaborolane (339.66 mg, 1.34 mmol) and potassium acetate (238.67 mg, 2.43 mmol, 152.02 µL) were mixed in dioxane (20.27 mL). The resulting mixture was evacuated and then backfilled with argon, this operation was repeated three times, then tris(dibenzylideneacetone)dipalladium (0) (55.67 mg, 60.80 µmol) was added under argon. The reaction mixture was stirred under argon at 90° C. for 14 hr, then cooled and concentrated under reduce pressure. The residue was purified by column chromatography (column: SunFire 100*19 mm, 5 microM; 2-10 min 50-100% MeCN 30 ml/min (loading pump 4 ml MeCN)) to afford [2-(4-pyridyl)-1,3-benzothiazol-5-yl]boronic acid (0.06 g, 234.29 µmol, 19.27% yield).

LCMS(ESI): [M]+ m/z: calcd 338.2; found 339.2; Rt=1.341 min.

Step 3: Synthesis of (S)-tert-butyl 3-methyl-6-(2-(Pyridin-4-yl)benzo[d]thiazol-5-yl)-3,4-dihydropyridine-1(2H)-carboxylate Prepared by general procedure scheme H step 3. Yield: 96 mg of crude.

LCMS(ESI): [M]+ m/z: calcd 407.2; found 408.2; Rt=1.323 min.

Step 4: Synthesis of (S)-5-(5-methyl-3,4,5,6-tetrahydropyridin-2-yl)-2-(Pyridin-4-yl)benzo[d]thiazole Prepared by general procedure scheme H step 4. Yield: 75 mg of crude.

LCMS(ESI): [M]+ m/z: calcd 307.2; found 308.2; Rt=0.755 min.

Step 5: Synthesis of 5-((2R,5S)-5-methylpiperidin-2-yl)-2-(Pyridin-4-yl)benzo[d]thiazole Prepared by general procedure scheme H step 5. Yield: 69 mg of crude.

LCMS(ESI): [M]+ m/z: calcd 309.2; found 310.2; Rt=0.770 min.

Step 6: Synthesis of N-(6-amino-5-ethylpyridin-3-yl)-2-((2R,5S)-5-methyl-2-(2-(Pyridin-4-yl)benzo[d]thiazol-5-yl)piperidin-1-yl)-2-oxoacetamide (Compound 1194)

Prepared by general procedure scheme H step 6B. Yield: 10 mg (15.28%).

HPLC conditions: Column: SunFire C18 100*19 mm, 5 microM; 2-10 min 50-75% MeOH+NH₃, flow: 30 ml/min; (loading pump 4 ml/min MeOH).

¹H NMR (600 MHz, DMSO-d₆) δ (ppm) 1.03-1.05 (t, 3H), 1.12-1.14 (m, 3H), 1.34-1.42 (m, 2H), 1.72-1.74 (m, 2H), 1.87-1.92 (m, 2H), 2.32-2.37 (m, 1H), 2.40-2.42 (m, 1H), 3.50-4.08 (m, 1H), 5.33-5.73 (m, 3H), 7.43-7.56 (m, 2H), 8.03-8.08 (m, 4H), 8.24 (m, 1H), 8.78-8.79 (m, 2H), 10.51 (br s, 1H).

LCMS(ESI): [M]+ m/z: calcd 500.2; found 501.2; Rt=2.663 min.

Example 635. The Synthesis of 5-(2-((2R,5)-2-(2-(1-ethylpiperidin-4-yl)benzo[d]thiazol-5-yl)-5-methylpiperidin-1-yl)-2-oxoacetamido)-2-methoxynicotinamide (Compound 1164)

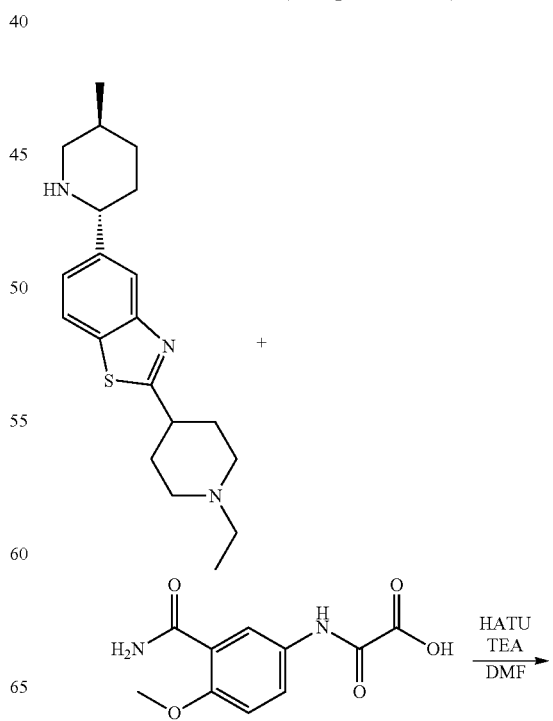

2711

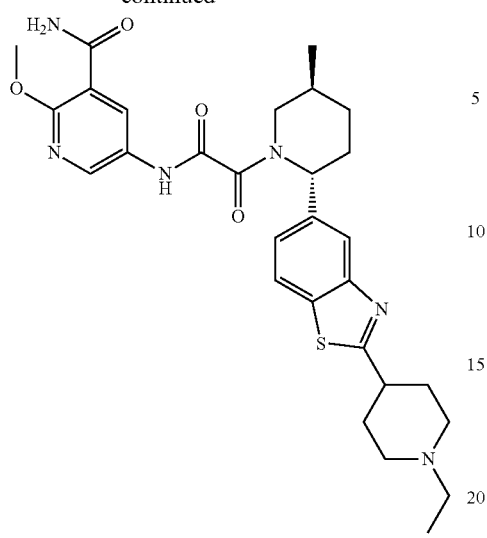

Prepared by general procedure scheme H step 6A. Yield: 65 mg (39.54%).

HPLC conditions: Column: YMC Triart C18 100*20 mm, 5 microM; 0-1-6 min 40-40-80% water-MeOH+0.1% NH$_4$OH; (loading pump 4 ml/min MeOH).

$^1$H NMR (600 MHz, DMSO-d$_6$) δ (ppm) 0.99-1.03 (m, 6H), 1.32-1.40 (m, 1H), 1.71-1.90 (m, 4H), 2.01-2.19 (m, 6H), 2.29-2.37 (m, 3H), 2.83-2.94 (m, 2H), 3.06-3.11 (m, 1H), 3.49-4.05 (m, 4H), 5.29-5.70 (m, 1H), 7.35-7.42 (dd, 1H), 7.68-7.75 (m, 2H), 7.87-7.89 (m, 1H), 8.03-8.07 (m, 1H), 8.41-8.58 (m, 2H), 11.02-11.10 (m, 1H).

LCMS(ESI): [M]$^+$ m/z: calcd 564.2; found 565.2; Rt=2.643 min.

Example 636. The Synthesis of 5-(2-((2R,5)-2-(2-((Dimethylamino)methyl)benzo[d]thiazol-5-yl)-5-methylpiperidin-1-yl)-2-oxoacetamido)-2-methoxynicotinamide (Compound 1162)

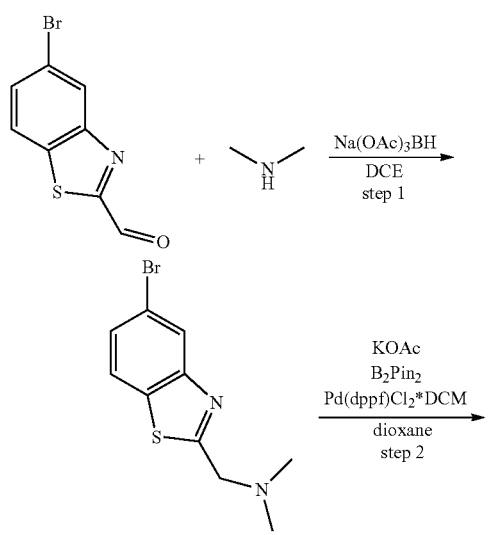

2712

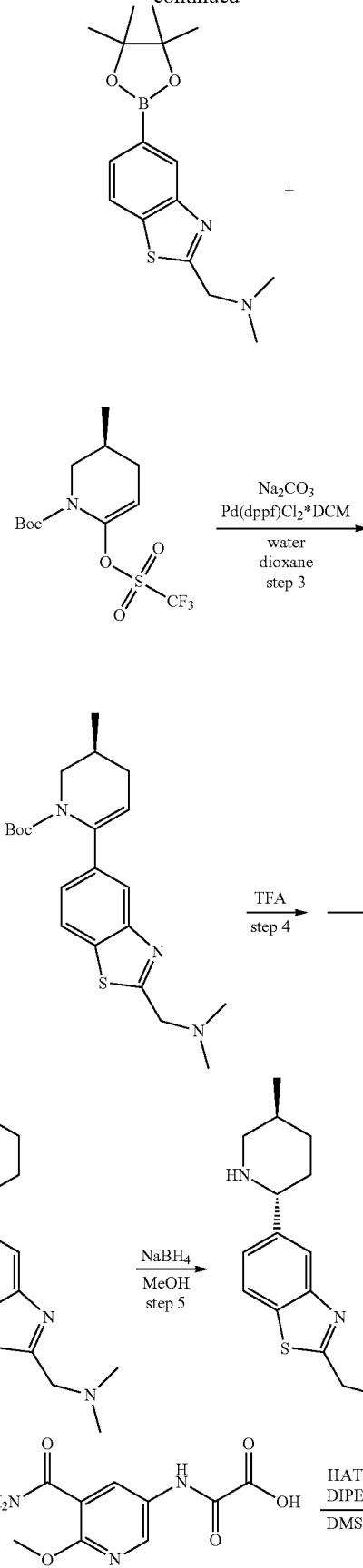

-continued

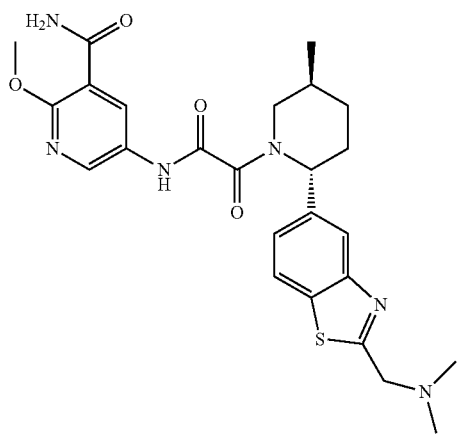

Step 1: Synthesis of 1-(5-bromobenzo[d]thiazol-2-yl)-N,N-dimethylmethanamine Prepared by general procedure scheme H step 1C. Yield: 3.7 g (82.58%).

LCMS(ESI): $[M]^+$ m/z: calcd 271.2; found 272.2; Rt=0.801 min.

Step 2: Synthesis of N,N-dimethyl-1-(5-(4,4,5,5-tetramethyl-1,3,2-dioxaborolan-2-yl)benzo[d]thiazol-2-yl)methanamine Prepared by general procedure scheme H step 2. Yield: 12.91 g (70.07%).

CC conditions: The crude product was purified by silica gel with DCM/MeCN (gradient) as an eluent mixture.

LCMS(ESI): $[M]^+$ m/z: calcd 318.2; found 319.2; Rt=0.758 min.

Step 3: Synthesis of (S)-tert-butyl 6-(2-((Dimethylamino)methyl)benzo[d]thiazol-5-yl)-3-methyl-3,4-dihydropyridine-1(2H)-carboxylate Prepared by general procedure scheme H step 3. Yield: 3.5 g of crude.

LCMS(ESI): $[M]^+$ m/z: calcd 387.2; found 388.2; Rt=1.192 min.

Step 4: Synthesis of (S)—N,N-dimethyl-1-(5-(5-methyl-3,4,5,6-tetrahydropyridin-2-yl)benzo[d]thiazol-2-yl)methanamine Prepared by general procedure scheme H step 4. Yield: 3.04 g of crude.

LCMS(ESI): $[M]^+$ m/z: calcd 287.2; found 288.2; Rt=0.602 min.

Step 5: Synthesis of N,N-dimethyl-1-(5-((2R,5S)-5-methylpiperidin-2-yl)benzo[d]thiazol-2-yl)methanamine Prepared by general procedure scheme H step 5. Yield: 2.5 g of crude.

LCMS(ESI): $[M]^+$ m/z: calcd 289.2; found 290.2; Rt=0.686 min.

Step 6: The Synthesis of 5-(2-((2R,5S)-2-(2-((Dimethylamino)methyl)benzo[d]thiazol-5-yl)-5-methylpiperidin-1-yl)-2-oxoacetamido)-2-methoxynicotinamide (Compound 1162

Prepared by general procedure scheme H step 6B. Yield: 68.4 mg (38.77%).

HPLC conditions: Column: SunFire C18 100*19 mm, 5 microM; 2-10 min 25-30% water-MeOH+NH₃; (loading pump 4 ml/min MeOH+NH₃).

$^1$H NMR (600 MHz, DMSO-$d_6$) δ (ppm) 1.02-1.06 (m, 3H), 1.33-1.40 (m, 1H), 1.71-1.73 (m, 1H), 1.86-1.91 (m, 1H), 2.06-2.21 (m, 2H), 2.30 (s, 6H), 3.49-3.51 (m, 1H), 3.85-4.05 (m, 5H), 5.29-5.73 (m, 2H), 7.36-7.42 (m, 1H), 7.68-7.74 (m, 2H), 7.87-7.88 (m, 1H), 8.03-8.07 (m, 1H), 8.40-8.58 (m, 2H), 11.04 (br s, 1H).

LCMS(ESI): $[M]^+$ m/z: calcd 510.2; found 511.2; Rt=2.168 min.

Example 637. The Synthesis of 2-methoxy-5-(2-((2R,53)-5-methyl-2-(2-(2-(pyrrolidin-1-yl)ethyl)benzo[d]thiazol-5-yl)piperidin-1-yl)-2-oxoacetamido)nicotinamide (Compound 1288)

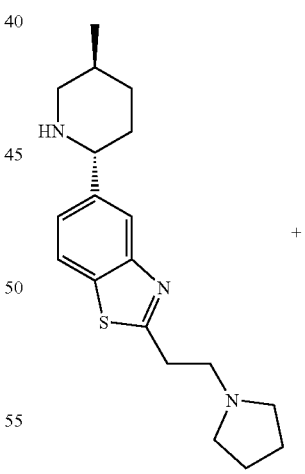

+

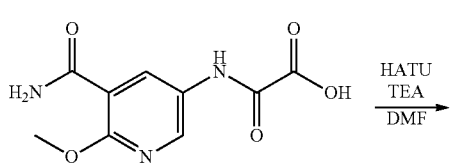

2715

-continued

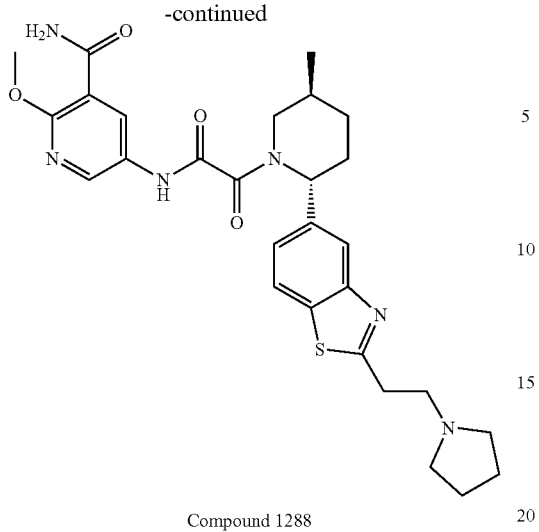

Compound 1288

Prepared by general procedure scheme H step 6A. Yield: 26.7 mg (23.85%).

HPLC conditions: Column: YMC Triart C18 100*20 mm, 5 microM; 0-1-6 min 50-50-80% water-MeOH+0.1% NH₄OH; (loading pump 4 ml/min MeOH).

¹H NMR (600 MHz, DMSO-d₆) δ (ppm) 0.99-1.16 (m, 4H), 1.32-1.39 (m, 2H), 1.68 (m, 4H), 1.85-1.91 (m, 2H), 2.08-2.37 (m, 2H), 2.84-2.86 (m, 2H), 3.23-3.26 (m, 3H), 3.49-3.73 (m, 2H), 3.86-4.20 (m, 4H), 4.48-4.95 (m, 1H), 5.30-5.79 (m, 2H), 7.24-7.54 (m, 1H), 7.69-7.88 (m, 2H), 8.00-8.05 (m, 1H), 8.31-8.68 (m, 1H), 11.02-11.11 (m, 1H).

LCMS(ESI): [M]⁺ m/z: calcd 550.2; found 551.2; Rt=2.099 min.

Example 638. The Synthesis of N-(imidazo[1,2-a]pyridin-7-yl)-2-((2R,5)-5-methyl-2-(2-(1-methylpiperidin-4-yl)benzo[d]thiazol-5-yl)piperidin-1-yl)-2-oxoacetamide (Compound 1301)

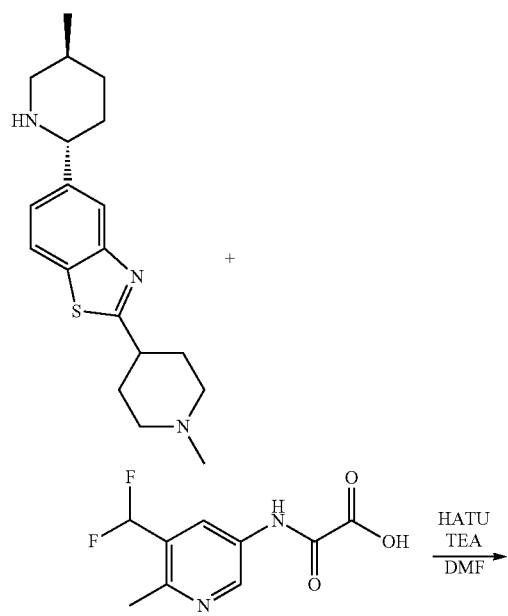

2716

-continued

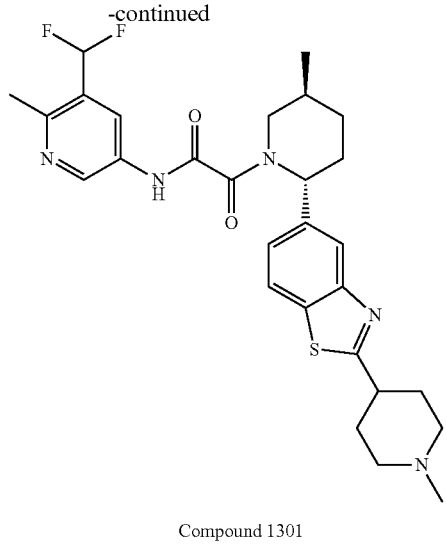

Compound 1301

Prepared by general procedure scheme H step 6A. Yield: 86 mg (47.56%).

HPLC conditions: Column: XBridge C18 100*19 mm, 5 microM; 0-5 min 15-65% water-MeCN+0.1% NH₄OH; (loading pump 4 ml/min MeCN).

¹H NMR (600 MHz, DMSO-d₆) δ (ppm) 0.97-1.07 (m, 3H), 1.30-1.41 (m, 1H), 1.64-1.74 (m, 1H), 1.77-1.93 (m, 3H), 1.99-2.14 (m, 5H), 2.18 (s, 3H), 2.29-2.36 (m, 1H), 2.49-2.51 (m, 3H), 2.80-2.86 (m, 2H), 3.01-3.09 (m, 1H), 3.31-3.33 (m, 1H), 3.36-4.07 (m, 1H), 5.27-5.82 (m, 1H), 7.06-7.31 (m, 1H), 7.34-7.44 (m, 1H), 7.86-7.91 (m, 1H), 8.01-8.09 (m, 1H), 8.19-8.35 (m, 1H), 8.69-8.83 (m, 1H), 11.13-11.40 (m, 1H).

LCMS(ESI): [M]⁺ m/z: calcd 541.2; found 542.2; Rt=2.872 min.

Example 639. Synthesis of rac-2-(2-methoxyethyl)-5-((2R,5S)-5-methylpiperidin-2-yl)benzo[d]thiazole Step 1: Synthesis of 5-bromo-2-(2-methoxyethyl)benzo[d]thiazole

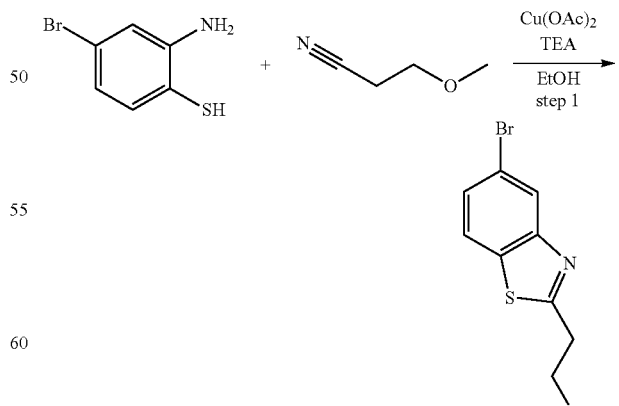

2-amino-4-bromo-benzenethiol (5.5 g, 26.95 mmol, 170.94 uL), 3-methoxypropanenitrile (3.44 g, 40.42 mmol, 3.67 mL), copper(II) acetate (489.49 mg, 2.69 mmol), TEA (2.73 g, 26.95 mmol, 3.76 mL) were dissolved in EtOH (100 mL). The mixture was stirred at 70° C. (oil bath temperature) for 13 hr. After the reaction was finished (monitored by LCMS), the mixture was cooled to rt and quenched with aqueous Na$_2$CO$_3$, and the crude product was extracted with EtOAc. The organic extracts were concentrated in vacuum, and the resulting residue was purified by column chromatography on silica gel with hexane/EtOAc as eluent to afford 5-bromo-2-(2-methoxyethyl)-1,3-benzothiazole (2.75 g, 10.10 mmol, 37.49% yield).

LCMS(ESI): [M]$^+$ m/z: calcd 272.2; found 273.2; Rt=1.369 min.

Step 2: Synthesis of 2-(2-methoxyethyl)-5-(4,4,5,5-tetramethyl-1,3,2-dioxaborolan-2-yl)benzo[d]thiazole

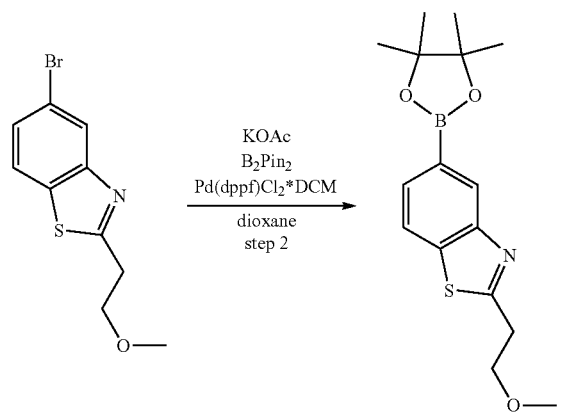

Prepared by general procedure scheme J step 2. Yield: 3.2 g of crude.

LCMS(ESI): [M]$^+$ m/z: calcd 319.2; found 320.2; Rt=1.562 min.

Step 3: Synthesis of tert-butyl 6-(2-(2-methoxyethyl)benzo[d]thiazol-5-yl)-3-methyl-3,4-dihydropyridine-1(2H)-carboxylate

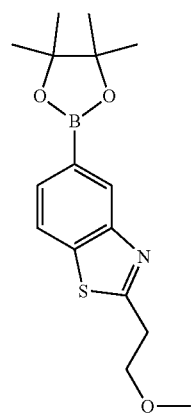

+

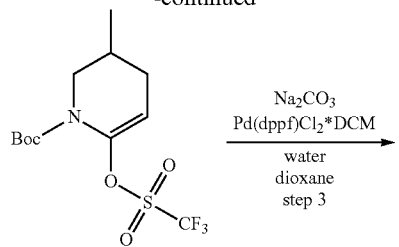

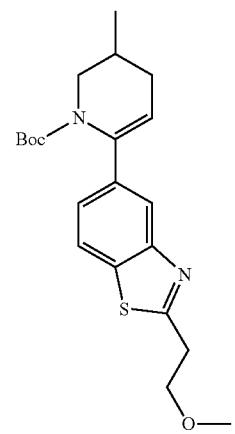

Prepared by general procedure scheme J step 3. Yield: 3.2 g of crude.

LCMS(ESI): [M]$^+$ m/z: calcd 388.2; found 389.2; Rt=1.577 min.

Step 4: Synthesis of 2-(2-methoxyethyl)-5-(5-methyl-3,4,5,6-tetrahydropyridin-2-yl)benzo[d]thiazole

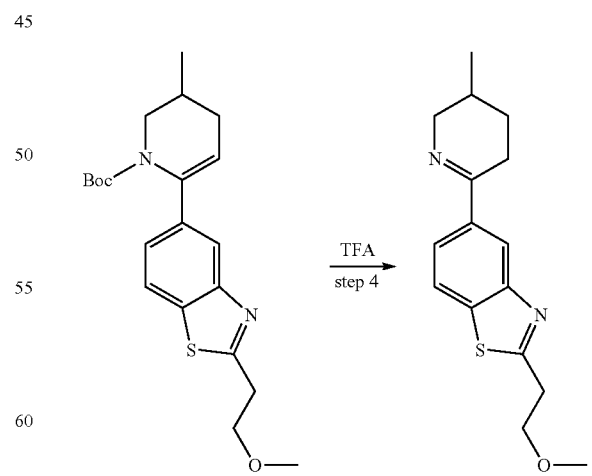

Prepared by general procedure scheme J step 4. Yield: 3.2 g of crude.

LCMS(ESI): [M]$^+$ m/z: calcd 288.2; found 289.2; Rt=0.764 min.

Step 5: Synthesis of rac-2-(2-methoxyethyl)-5-((2R, 5S)-5-methylpiperidin-2-yl)benzo[d]thiazole
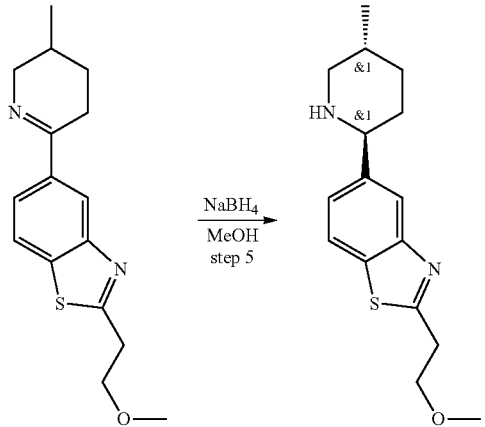 [SMILES: COCCc1nc2cc(C3=NCC(C)CC3)ccc2s1 ; "NaBH4" ; COCCc1nc2cc([C@@H]3CC[C@@H](C)CN3)ccc2s1]
Prepared by general procedure scheme H step 5. Yield: 3 g of crude.
LCMS(ESI): [M]⁺ m/z: calcd 290.2; found 291.2; Rt=0.877 min.
Example 640. The Synthesis of N-(6-amino-5-ethylpyridin-3-yl)-2-((2R,5S)-2-(2-(3-(dimethylamino)bicyclo[1.1.1]pentan-1-yl)benzo[d]thiazol-5-yl)-5-methylpiperidin-1-yl)-2-oxoacetamide (Compound 1404)
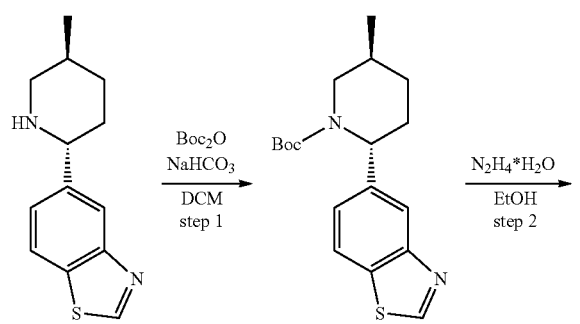
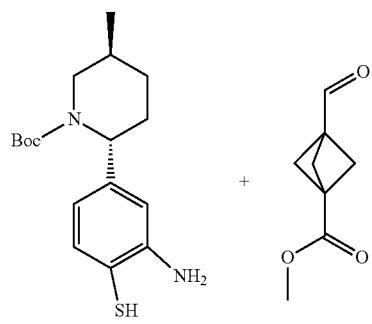
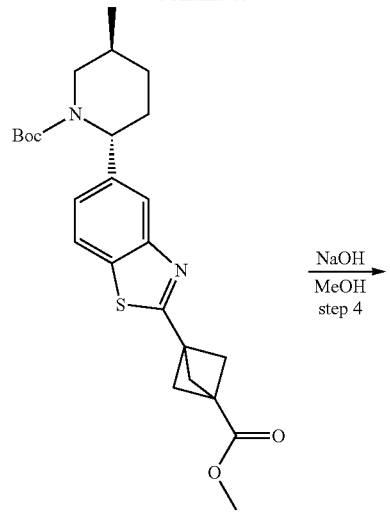
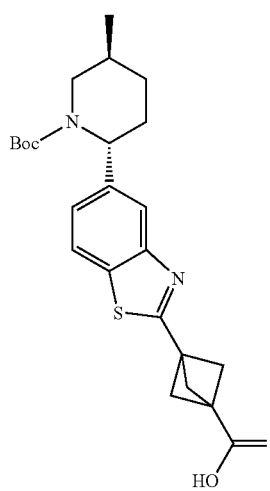
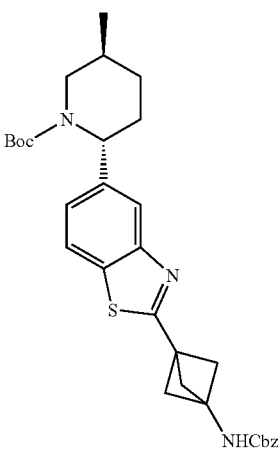

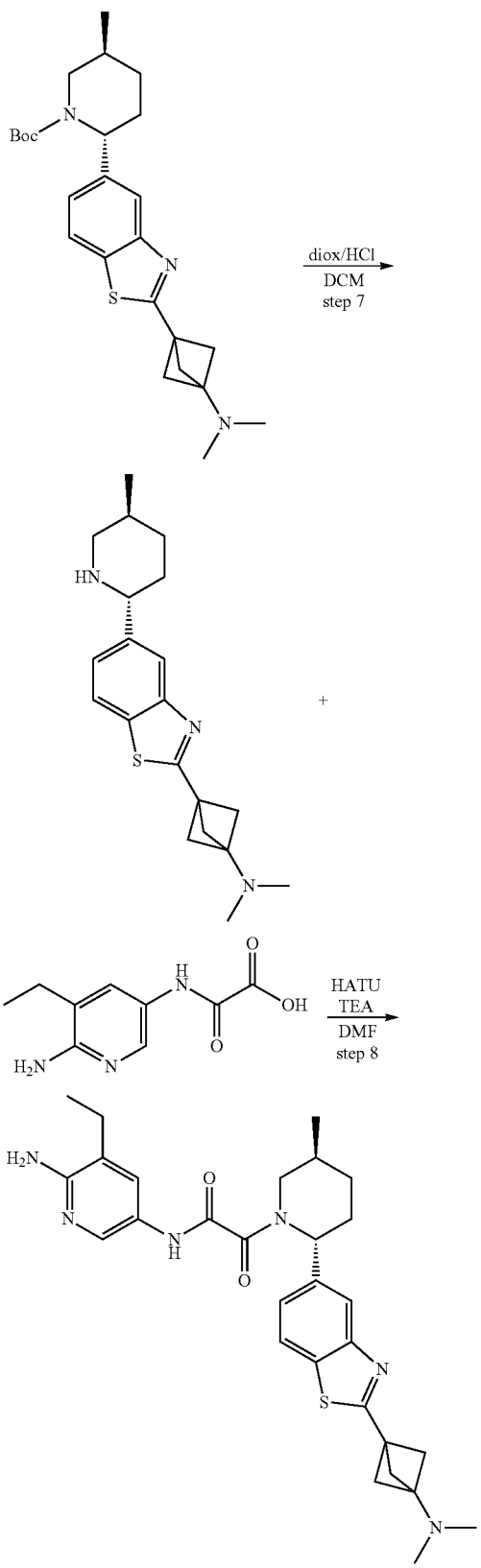

Compound 1404

Step 1: Synthesis of (2R,5S)-tert-butyl 2-(benzo[d]thiazol-5-yl)-5-methylpiperidine-1-carboxylate To a solution of 5-[(2R,5S)-5-methyl-2-piperidyl]-1,3-benzothiazole (3 g, 7.80 mmol) and sodium bicarbonate (1.97 g, 23.41 mmol, 910.82 µL) in DCM (22.89 mL) was added di-tert-butyl bicarbonate (1.70 g, 7.80 mmol, 1.79 mL) portion wise at rt. When the gas evolution ceased was washed with 10% aq. NaHCO$_3$ and brine, dried over Na$_2$SO$_4$ and evaporated to dryness to give tert-butyl (2R,5S)-2-(1,3-benzothiazol-5-yl)-5-methyl-piperidine-1-carboxylate (2.3 g, 6.92 mmol, 88.67% yield) as a yellow solid.

$^1$H NMR (400 MHz, CDCl$_3$) δ (ppm) 1.04 (d, 3H), 1.34 (m, 1H), 1.44 (s, 9H), 1.79 (m, 2H), 2.11 (m, 2H), 3.03 (m, 1H), 3.75 (m, 1H), 5.46 (m, 1H), 7.33 (d, 1H), 7.88 (d, 1H), 8.01 (s, 1H), 8.90 (s, 1H).

Step 2: Synthesis of (2R,5S)-tert-butyl 2-(3-amino-4-Mercaptophenyl)-5-methylpiperidine-1-carboxylate To a solution of tert-butyl (2R,5S)-2-(1,3-benzothiazol-5-yl)-5-methyl-piperidine-1-carboxylate (3.1 g, 9.32 mmol) in EtOH (50 mL) was added hydrazine monohydrate (4.67 g, 93.24 mmol, 4.55 mL) under Ar atmosphere at rt. The reaction mixture was then stirred at reflux overnight. Note: the top of the condenser is capped with a rubber septum and a balloon with argon is connected through the needle to equalize pressure. The reaction progress was monitored by LCMS. Note: product can be found as a sulfide or disulfide on the LCMS, because sulfide can be oxidized to disulfide during the LCMS process. The resulting mixture was then cooled, evaporated and partitioned between water and EtOAc. The organic phase was washed with brine, dried over Na$_2$SO$_4$ and concentrated in vacuum to afford the tert-butyl (2R,5S)-2-(3-amino-4-sulfanyl-phenyl)-5-methyl-piperidine-1-carboxylate (3 g, 9.30 mmol, 99.77% yield) as a brown oil.

LCMS(ESI): [M]$^+$ m/z: calcd 322.2; found 323.2; Rt=4.134 min.

Step 3: Synthesis of (2R,5S)-tert-butyl 2-(2-(3-(methoxycarbonyl)bicyclo[1.1.1]pentan-1-yl)benzo[d]thiazol-5-yl)-5-methylpiperidine-1-carboxylate Prepared by general procedure scheme H step 1B. Yield: 2.5 g of crude.

LCMS(ESI): [M]$^+$ m/z: calcd 456.2; found 457.2; Rt=4.909 min.

Step 4: Synthesis of 3-(5-((2R,5S)-1-(tert-butoxycarbonyl)-5-methylpiperidin-2-yl)benzo[d]thiazol-2-yl)bicyclo[1.1.1]Pentane-1-carboxylic acid To a solution of tert-butyl (2R,5S)-2-[2-(3-methoxycarbonyl-1-bicyclo[1.1.1]pentanyl)-1,3-benzothiazol-5-yl]-5-methyl-piperidine-1-carboxylate (2.5 g, 5.48 mmol) in MeOH (50 mL) was added sodium hydroxide, pearl (437.99 mg, 10.95 mmol, 205.63 µL) and the resulting mixture was left to stir at rt for 18 hr. Then the resulting mixture was evaporated to dryness, dissolved in water, acidified to pH=1, and extracted with EtOAc twice, organics were washed with brine, dried over Na$_2$SO$_4$, and evaporated. 3-[5-[(2R,5S)-1-tert-butoxycarbonyl-5-methyl-2-piperidyl]-1,3-benzothiazol-2-yl]bicyclo[1.1.1]pentane-1-carboxylic acid (1.9 g, 4.29 mmol, 78.41% yield) was obtained as a beige solid.

¹H NMR (400 MHz, DMSO-d₆) δ (ppm) 0.97 (d, 3H), 1.29 (m, 1H), 1.38 (s, 9H), 1.40 (m, 2H), 1.52 (m, 1H), 1.80 (m, 1H), 2.07 (m, 2H), 2.43 (m, 4H), 2.99 (m, 1H), 3.63 (m, 1H), 5.30 (m, 1H), 7.28 (d, 1H), 7.79 (s, 1H), 8.03 (d, 1H), 12.57 (bds, 1H).

Step 5: Synthesis of (2R,5S)-tert-butyl 2-(2-(3-(((benzyloxy)carbonyl)amino)bicyclo[1.1.1]pentan-1-yl)benzo[d]thiazol-5-yl)-5-methylpiperidine-1-carboxylate To a solution of 3-[5-[(2R,5S)-1-tert-butoxycarbonyl-5-methyl-2-piperidyl]-1,3-benzothiazol-2-yl]bicyclo[1.1.1]pentane-1-carboxylic acid (1.7 g, 3.84 mmol), TEA (427.56 mg, 4.23 mmol, 588.93 µL) in toluene (50 mL) was added diphenylphosphoryl azide (1.06 g, 3.84 mmol, 830.40 µL) and benzyl alcohol (498.47 mg, 4.61 mmol, 477.00 µL) and the resulting mixture was stirred at 90° C. overnight. The reaction mixture was evaporated, dissolved in aq. K₂CO₃/DCM mixture, water was back-extracted with DCM, combined organics were washed with brine, dried and evaporated to give tert-butyl (2R,5S)-2-[2-[3-(benzyloxycarbonylamino)-1-bicyclo[1.1.1]pentanyl]-1,3-benzothiazol-5-yl]-5-methyl-piperidine-1-carboxylate (2 g, crude) as a dark-yellow gum.

LCMS(ESI): [M]⁺ m/z: calcd 547.2; found 548.2; Rt=4.770 min.

Step 6: Synthesis of (2R,5S)-tert-butyl 2-(2-(3-(dimethylamino)bicyclo[1.1.1]pentan-1-yl)benzo[d]thiazol-5-yl)-5-methylpiperidine-1-carboxylate To a solution of tert-butyl (2R,5S)-2-[2-[3-(benzyloxycarbonylamino)-1-bicyclo[1.1.1]pentanyl]-1,3-benzothiazol-5-yl]-5-methyl-piperidine-1-carboxylate (2 g, 3.65 mmol) and formaldehyde, 37% w/w aq. soln., stab. with 7-8% MeOH (328.93 mg, 10.95 mmol, 303.72 µL) in MeOH (50 mL) in three-necked round-bottomed flask was added palladium, 10% on carbon, type 487, dry (38.86 mg, 365.16 µmol). The reaction flask was evacuated and backfilled with hydrogen (368.04 mg, 182.58 mmol) and the mixture was left to stir for 72 hr. Filtration through a thin pad of silica gel followed by concentration and drying under vacuum afforded residue which was purified by CC (Interchim; 80 g SiO₂, chloroform/MeCN with MeCN from 0~100% further MeCN/MeOH with MeOH from 0~20% flow rate=60 mL/min, Rv=29-33 CV) to give tert-butyl (2R,5S)-2-[2-[3-(dimethylamino)-1-bicyclo[1.1.1]pentanyl]-1,3-benzothiazol-5-yl]-5-methyl-piperidine-1-carboxylate (0.34 g, 769.88 µmol, 21.08% yield) as a yellow oil.

LCMS(ESI): [M]⁺ m/z: calcd 441.2; found 442.2; Rt=1.568 min.

Step 7: Synthesis of N,N-dimethyl-3-(5-((2R,5S)-5-methylpiperidin-2-yl)benzo[d]thiazol-2-yl)bicyclo[1.1.1]pentan-1-amine To a solution of tert-butyl (2R,5S)-2-[2-[3-(dimethylamino)-1-bicyclo[1.1.1]pentanyl]-1,3-benzothiazol-5-yl]-5-methyl-piperidine-1-carboxylate (100 mg, 113.22 µmol) in DCM (5 mL) was added hydrogen chloride solution 4.0 M in dioxane (20.64 mg, 566.09 µmol, 25.80 µL) at 21° C. The resulting mixture was left to stir for 6 hr. The resulting mixture was evaporated to dryness and was used in the next step without further purification.

LCMS(ESI): [M]⁺ m/z: calcd 341.2; found 342.2; Rt=1.225 min.

Step 8: Synthesis of N-(6-amino-5-ethylpyridin-3-yl)-2-((2R,5S)-2-(2-(3-(dimethylamino)bicyclo[1.1.1]pentan-1-yl)benzo[d]thiazol-5-yl)-5-methylpiperidin-1-yl)-2-oxoacetamide (Compound 1404

Prepared by general procedure scheme H step 6A. Yield: 14.4 mg (24.62%).

HPLC conditions: Column: XBridge C18 100*19 mm, 5 microM; 0.5-6.5 min 30-55% water-MeCN+NH₃, flow: 30 ml/min; (loading pump 4 ml/min MeCN).

¹H NMR (600 MHz, DMSO-d₆) δ (ppm) 0.99-1.05 (m, 3H), 1.05-1.15 (m, 3H), 1.27-1.40 (m, 1H), 1.62-1.75 (m, 1H), 1.81-1.92 (m, 1H), 2.02-2.13 (m, 1H), 2.15 (s, 6H), 2.17 (s, 6H), 2.27-2.34 (m, 1H), 2.39-2.45 (m, 2H), 2.77-3.14 (m, 1H), 3.48-4.06 (m, 1H), 5.27-5.61 (m, 1H), 5.62-5.73 (m, 2H), 7.32-7.43 (m, 1H), 7.42-7.55 (m, 1H), 7.86-7.96 (m, 1H), 7.97-8.13 (m, 2H), 10.53 (br s, 1H).

LCMS(ESI): [M]⁺ m/z: calcd 532.2; found 533.2; Rt=2.240 min.

Example 641. The Synthesis of N-(6-amino-5-ethylpyridin-3-yl)-2-((2R,5S)-2-(2-(1-((Dimethylamino)methyl)cyclopropyl)benzo[d]thiazol-5-yl)-5-methylpiperidin-1-yl)-2-oxoacetamide (Compound 1347)

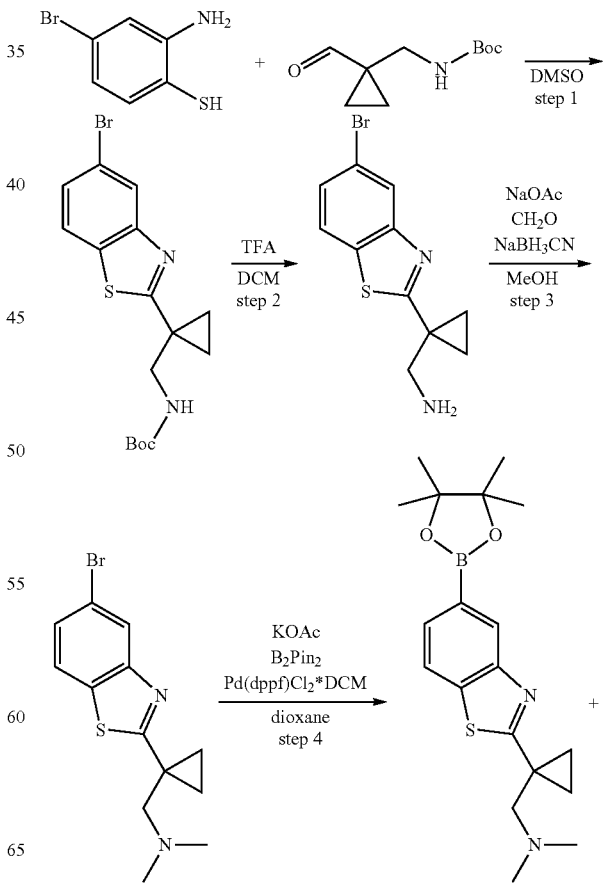

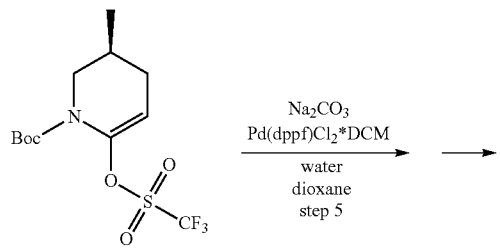

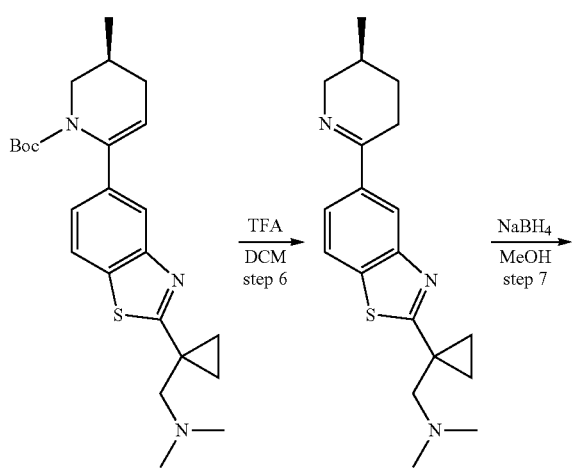

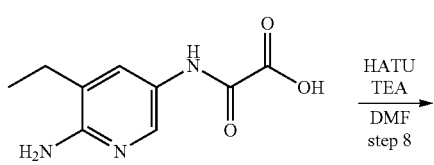

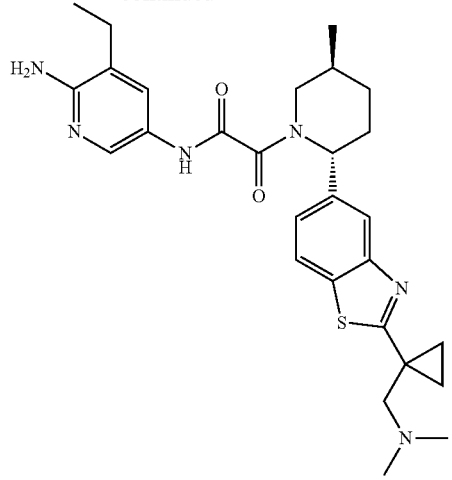

Compound 1374

Step 1: Synthesis of tert-butyl ((1-(5-bromobenzo[d]thiazol-2-yl)cyclopropyl)methyl)carbamate Prepared by general procedure scheme H step 1B. Yield: 5.2 g (92.29%)

LCMS(ESI): [M]⁺ m/z: calcd 383.2; found 384.2; Rt=1.648 min.

Step 2: Synthesis of (1-(5-bromobenzo[d]thiazol-2-yl)cyclopropyl)methanamine

TFA (22.20 g, 194.70 mmol, 15 mL) was added in one portion to a stirred solution of tert-butyl N-[[1-(5-bromo-1,3-benzothiazol-2-yl)cyclopropyl]methyl]carbamate (2.7 g, 7.04 mmol) in DCM (30 mL) at 25° C. The resulting solution was stirred at 25° C. for 0.5 hr, and then concentrated in vacuum. The residue was diluted with ice cold water (50 ml) and basified to pH 11 with 10% aqueous sodium hydroxide solution. The resulting mixture was extracted with DCM (2*50 ml). The combined organic extracts were dried over sodium sulfate and concentrated in vacuum to afford crude [1-(5-bromo-1,3-benzothiazol-2-yl)cyclopropyl]methanamine (1.9 g, 6.71 mmol, 95.25% yield) as red gum, which was used directly in the next step.

LCMS(ESI): [M]⁺ m/z: calcd 383.2; found 384.2; Rt=0.862 min.

Step 3: Synthesis of 1-(1-(5-bromobenzo[d]thiazol-2-yl)cyclopropyl)-N,N-dimethylmethanamine Formaldehyde, 37% w/w aq. soln., stab. with 7-8% MeOH (1.6 g, 19.71 mmol, 1.48 mL, 37% purity) and acetic acid (805.79 mg, 13.42 mmol, 768.15 µL) were added to a stirred solution of [1-(5-bromo-1,3-benzothiazol-2-yl)cyclopropyl]methanamine (1.9 g, 6.71 mmol) in MeOH (60 mL) at 25° C. The resulting mixture was stirred at 25° C. for 1 hr, then sodium cyan borohydride (843.23 mg, 13.42 mmol) was added in one portion at 25° C. (foaming!). The reaction mixture was stirred at 25° C. for 18 hr, and then concentrated in vacuum. The residue was diluted with 10% aqueous sodium hydroxide solution (40 ml) and extracted with DCM (2*30 ml). The combined organic extracts were dried over sodium sulphate and concentrated in vacuum to afford crude 1-[1-(5-bromo-1,3-benzothiazol-2-yl)cyclopropyl]-N,N-dimethylmethanamine (1.9 g, 6.10 mmol, 90.99% yield) as light-brown gum, which was used directly in the next step.

LCMS(ESI): [M]+ m/z: calcd 311.2; found 312.2; Rt=2.196 min.

Step 4: Synthesis of N,N-dimethyl-1-(1-(5-(4,4,5,5-tetramethyl-1,3,2-dioxaborolan-2-yl)benzo[d]thiazol-2-yl)cyclopropyl)methanamine Prepared by general procedure scheme H step 2. Yield: 2.19 g of crude.

LCMS(ESI): [M]+ m/z: calcd 358.2; found 359.2; Rt=3.096 min.

Step 5: Synthesis of (S)-tert-butyl 6-(2-(1-((Dimethylamino)methyl)cyclopropyl)benzo[d]thiazol-5-yl)-3-methyl-3,4-dihydropyridine-1(2H)-carboxylate Prepared by general procedure scheme H step 3. Yield: 3.9 g of crude.

LCMS(ESI): [M]+ m/z: calcd 427.2; found 428.2; Rt=1.315 min.

Step 6: Synthesis of (S)—N,N-dimethyl-1-(1-(5-(5-methyl-3,4,5,6-tetrahydropyridin-2-yl)benzo[d]thiazol-2-yl)cyclopropyl)methanamine Prepared by general procedure scheme H step 4. Yield: 0.85 g of crude.

LCMS(ESI): [M]+ m/z: calcd 327.2; found 328.2; Rt=0.616 min.

Step 7: Synthesis of N,N-dimethyl-1-(1-(5-((2R,5S)-5-methylpiperidin-2-yl)benzo[d]thiazol-2-yl)cyclopropyl)methanamine Prepared by general procedure scheme H step 5. Yield: 0.67 g (78.34%).

LCMS(ESI): [M]+ m/z: calcd 329.2; found 330.2; Rt=0.685 min.

Step 8: Synthesis of N-(6-amino-5-ethylpyridin-3-yl)-2-((2R,5S)-2-(2-(1-((Dimethylamino)methyl)cyclopropyl)benzo[d]thiazol-5-yl)-5-methylpiperidin-1-yl)-2-oxoacetamide (Compound 1347

Prepared by general procedure scheme H step 6A. Yield: 62 mg (35.67%).

HPLC conditions: Column: XBridge C18 100*19 mm, 5 microM; 0-5 min 50-100% water-MeOH+0.1% NH4OH, flow: 30 ml/min; (loading pump 4 ml/min MeOH).

1H NMR (600 MHz, DMSO-d6) δ (ppm) 1.09 (m, 8H), 1.39 (m, 3H), 1.69 (m, 1H), 1.86 (m, 1H), 2.12 (m, 1H), 2.25 (s, 6H), 2.36 (m, 2H), 2.62 (m, 3H), 2.76 (m, 1H), 3.85 (m, 1H), 5.64 (m, 3H), 7.31 (m, 1H), 7.47 (m, 1H), 7.76 (m, 1H), 7.99 (m, 2H), 10.54 (m, 1H).

LCMS(ESI): [M]+ m/z: calcd 520.2; found 521.2; Rt=1.924 min.

Example 642. The Synthesis of N-(6-amino-5-ethylpyridin-3-yl)-2-(2-methyl-6-(2-(1-methylpiperidin-4-yl)benzo[b]thiophen-5-yl)piperidin-1-yl)-2-oxoacetamide (Compound 1395 and Compound 1173

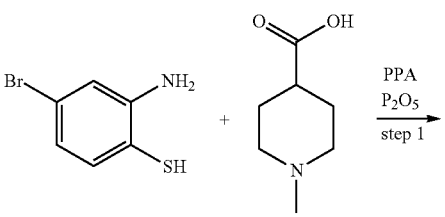

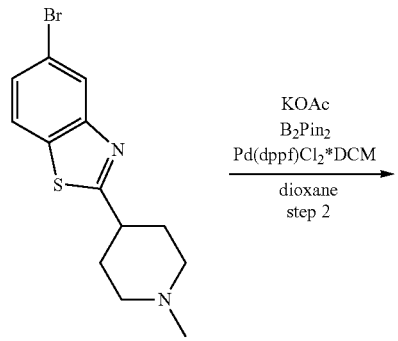

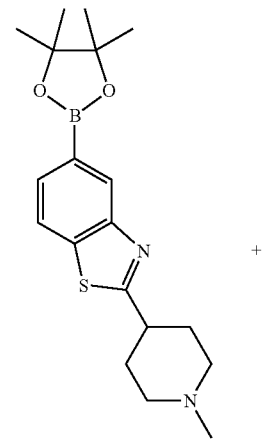

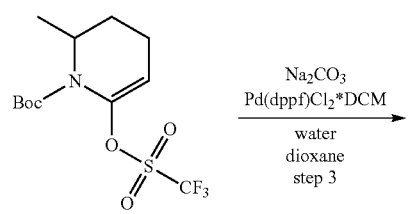

2729
-continued
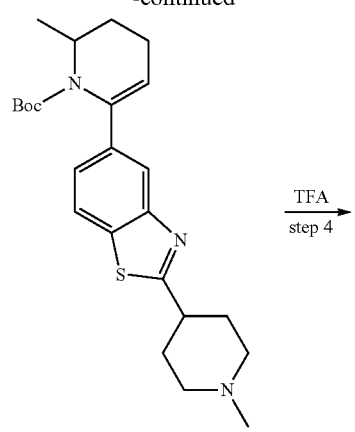
TFA
step 4
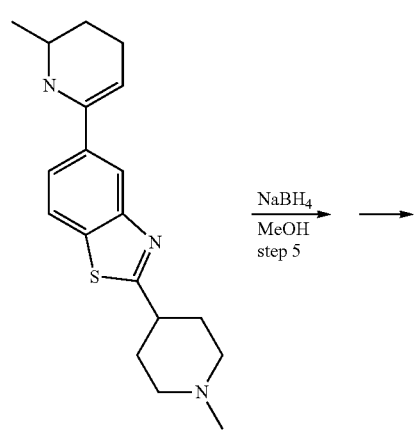
NaBH₄
MeOH
step 5
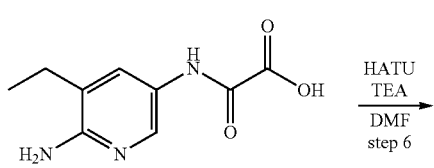
HATU
TEA
DMF
step 6
2730
-continued
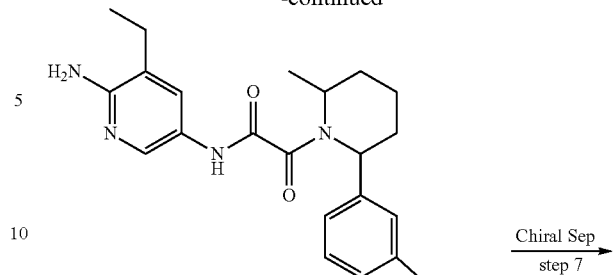
Chiral Sep
step 7
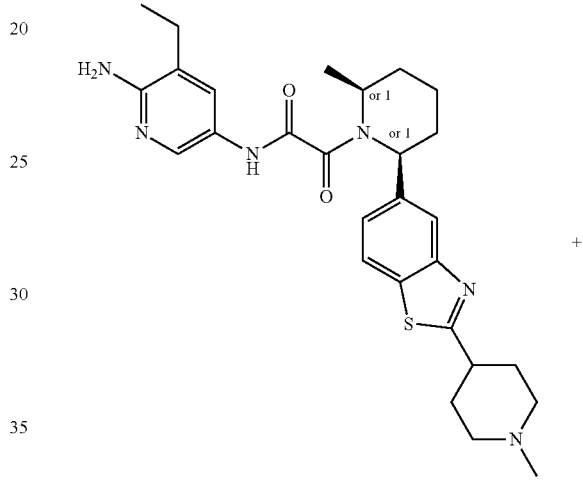
Compound 1173
+
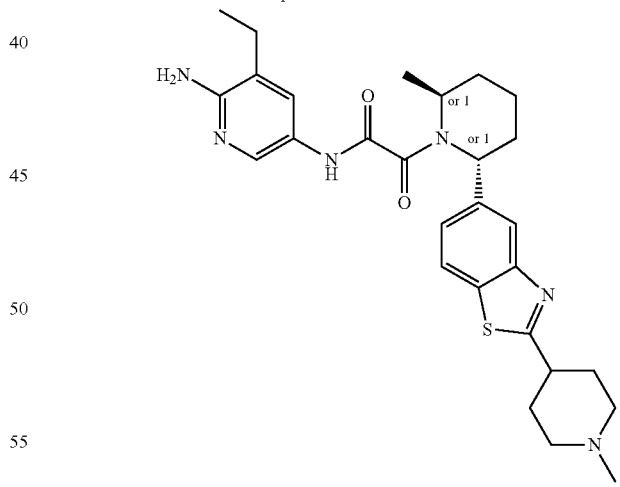
Compound 1395
Step 1: Synthesis of 5-bromo-2-(1-methylpiperidin-4-yl)benzo[d]thiazole
To phosphoric acid (7.82 g, 79.80 mmol, 4.60 mL) was added phosphorous (V) pentoxide (9.20 g, 64.82 mmol, 4.00 mL) the resulting mixture was stirred at 80° C. for 0.25 hr. Then 1-methylpiperidine-4-carboxylic acid (2.02 g, 11.27 mmol, HCl) and 2-amino-4-bromo-benzenethiol (2.3 g, 11.27 mmol) was added and the resulting mixture was stirred at 160° C. for 13 hr. The mixture was cooled, diluted with ice-cooled water (150 ml). The pH of the solution was adjusted to 10 with NaOH and extracted with DCM (3*40 ml). The combined organic layer was dried over Na$_2$SO$_4$ and evaporated in vacuum to give 5-bromo-2-(1-methyl-4-piperidyl)-1,3-benzothiazole (3.5 g, 11.25 mmol, 99.78% yield).

LCMS(ESI): [M]$^+$ m/z. calcd 311.2; found 312.2; Rt=0.774 min.

Step 2: Synthesis of 2-(1-methylpiperidin-4-yl)-5-(4,4,5,5-tetramethyl-1,3,2-dioxaborolan-2-yl)benzo[d]thiazole 5-bromo-2-(1-methyl-4-piperidyl)-1,3-benzothiazole (3.5 g, 11.25 mmol), 4,4,5,5-tetramethyl-2-(4,4,5,5-tetramethyl-1,3,2-dioxaborolan-2-yl)-1,3,2-dioxaborolane (2.86 g, 11.25 mmol) and potassium acetate (2.21 g, 22.49 mmol, 1.41 mL) were mixed in dioxane (70 mL). The resulting mixture was evacuated and then backfilled with argon, this operation was repeated three times, then Pd(dppf)Cl$_2$*DCM (459.17 mg, 562.27 µmol) was added under argon. The reaction mixture was stirred under argon at 90° C. for 13 hr, then cooled and filtered. The filter cake was washed with dioxane (2*20 ml) and discarded. Obtained solution of 2-(1-methyl-4-piperidyl)-5-(4,4,5,5-tetramethyl-1,3,2-dioxaborolan-2-yl)-1,3-benzothiazole (3.9 g, 10.88 mmol, 96.79% yield) was used directly in the next step.

LCMS(ESI): [M]$^+$ m/z: calcd 358.2; found 359.2; Rt=0.962 min.

Step 3: Synthesis of tert-butyl 2-methyl-6-(2-(1-methylpiperidin-4-yl)benzo[d]thiazol-5-yl)-3,4-dihydropyridine-1(2H)-carboxylate Sodium carbonate (2.31 g, 21.77 mmol, 911.25 µL) was added to a solution of 2-(1-methyl-4-piperidyl)-5-(4,4,5,5-tetramethyl-1,3,2-dioxaborolan-2-yl)-1,3-benzothiazole (3.9 g, 10.88 mmol) and tert-butyl 2-methyl-6-(trifluoromethylsulfonyloxy)-3,4-dihydro-2H-pyridine-1-carboxylate (3.76 g, 10.88 mmol) in dioxane (80 mL) and H$_2$O (10 mL). Reaction flask was evacuated and refilled with argon 3 times. Then, Pd(dppf)Cl$_2$*DCM (444.44 mg, 544.23 µmol) was added under stream of argon. Resulting mixture was stirred at 90° C. for 14 hr under inert atmosphere. Reaction solution was decanted and concentrated under reduce pressure. The residue was diluted with MTBE (250 ml). The resulting cloudy solution was decanted from oily residue. MTBE was evaporated in vacuum to give tert-butyl 2-methyl-6-[2-(1-methyl-4-piperidyl)-1,3-benzothiazol-5-yl]-3,4-dihydro-2H-pyridine-1-carboxylate (5 g, crude).

LCMS(ESI): [M]$^+$ m/z: calcd 427.2; found 428.2; Rt=1.226 min.

Step 4: Synthesis of 5-(6-methyl-3,4,5,6-tetrahydropyridin-2-yl)-2-(1-methylpiperidin-4-yl)benzo[d]thiazole tert-butyl 2-methyl-6-[2-(1-methyl-4-piperidyl)-1,3-benzothiazol-5-yl]-3,4-dihydro-2H-pyridine-1-carboxylate (5 g, 11.69 mmol) was diluted with TFA (13.33 g, 116.93 mmol, 9.01 mL). The resulting mixture was stirred at 25° C. for 1 hr. TFA was evaporated in vacuum. The residue was diluted with water (150 ml) and the resulting cloudy solution was decanted from oily residue, then basified with NaHCO$_3$. Product was extracted with DCM (3*50 ml). Combined organic layers were dried over Na$_2$SO$_4$. DCM was evaporated in vacuum to give 2-(1-methyl-4-piperidyl)-5-(2-methyl-2,3,4,5-tetrahydropyridin-6-yl)-1,3-benzothiazole (3 g, 9.16 mmol, 78.34% yield).

LCMS(ESI): [M]$^+$ m/z: calcd 327.2; found 328.2; Rt=0.658 min.

Step 5: Synthesis of 5-(6-methylpiperidin-2-yl)-2-(1-methylpiperidin-4-yl)benzo[d]thiazole To the stirred solution of 2-(1-methyl-4-piperidyl)-5-(2-methyl-2,3,4,5-tetrahydropyridin-6-yl)-1,3-benzothiazole (3 g, 9.16 mmol) in MeOH (15 mL) sodium borohydride (346.55 mg, 9.16 mmol, 322.67 µL) was added portion wise. The reaction mixture was stirred at 25° C. for 1 hr. MeOH was evaporated in vacuum. The residue was diluted with water (50 ml) and extracted with DCM (3*30 ml). Combined organic layer were washed with brine dried over Na$_2$SO$_4$. DCM was evaporated to give 2-(1-methyl-4-piperidyl)-5-(6-methyl-2-piperidyl)-1,3-benzothiazole (2.3 g, 6.98 mmol, 76.20% yield).

LCMS(ESI): [M]$^+$ m/z: calcd 329.2; found 330.2; Rt=0.682 min.

Step 6: Synthesis of N-(6-amino-5-ethylpyridin-3-yl)-2-(2-methyl-6-(2-(1-methylpiperidin-4-yl)benzo[b]thiophen-5-yl)piperidin-1-yl)-2-oxoacetamide To the solution of 1-methyl-4-[5-(6-methyl-2-piperidyl)benzothiophen-2-yl]piperidine (500.00 mg, 747.32 µmol, 2HCl), 2-[(6-amino-5-ethyl-3-pyridyl)amino]-2-oxo-acetic acid (187.61 mg, 896.78 µmol) and TEA (378.11 mg, 3.74 mmol, 520.81 µL) in DMF (3 mL) HATU (312.57 mg, 822.05 µmol) was added portion wise. Mixture was stirred at 25° C. for 1.5 hr.

Reaction mixture submitted for HPLC (SYSTEM 40-70% 0-5 min H$_2$O/MeOH/0.1% NH$_4$OH, flow: 30 ml/min (loading pump 4 ml/min MeOH) target mass 521 column: YMC Triart C18 100×20 mm, 5 um) to give N-(6-amino-5-ethyl-3-pyridyl)-2-[2-methyl-6-[2-(1-methyl-4-piperidyl)benzothiophen-5-yl]-1-piperidyl]-2-oxo-acetamide (94 mg, 180.87 µmol, 24.20% yield).

LCMS(ESI): [M]$^+$ m/z: calcd 519.2; found 520.2; Rt=1.816 min.

Step 7: Chiral Separation (Compound 1173 and Compound 1395

Racemic N-(6-amino-5-ethyl-3-pyridyl)-2-[2-methyl-6-[2-(1-methyl-4-piperidyl)benzothiophen-5-yl]-1-piperidyl]-2-oxo-acetamide (94 mg, 180.87 µmol) was chiral separated (Column: Chiralpak IA-II (250*20 mm, 5 mkm); Mobile phase: IPA-MeOH, 50-50. Flow Rate: 10 mL/min) to obtain N-(6-amino-5-ethyl-3-pyridyl)-2-[(2S,6S)-2-methyl-6-[2-(1-methyl-4-piperidyl)benzothiophen-5-yl]-1-piperidyl]-2-oxo-acetamide (19 mg, 36.56 µmol, 80.85% yield) and N-(6-amino-5-ethyl-3-pyridyl)-2-[(2S,6R)-2-methyl-6-[2-(1-methyl-4-piperidyl)benzothiophen-5-yl]-1-piperidyl]-2-oxo-acetamide (10 mg, 19.24 µmol, 42.55% yield).

Rel Time for Compound 1173 in analytical conditions (column: OD-H, Hexane-IPA-MeOH, 50-25-25, 0.6 ml/min as mobile phase) 10.09 min and for Compound 1395 11.36 min.

Compound 1173:

Retention time: 10.09 min $^1$H NMR (600 MHz, DMSO-$d_6$) δ (ppm) 0.68-0.81 (m, 3H), 1.07-1.16 (m, 3H), 1.44-1.57 (m, 1H), 1.58-1.67 (m, 1H), 1.71-1.91 (m, 5H), 2.04-2.18 (m, 4H), 2.23 (s, 3H), 2.35-2.44 (m, 2H), 2.62-2.70 (m, 1H), 2.83-2.97 (m, 2H), 3.03-3.12 (m, 1H), 4.06-4.84 (m, 1H), 5.14-5.63 (m, 1H), 5.63-5.92 (m, 2H), 7.39-7.55 (m, 2H), 7.95-8.09 (m, 3H), 10.58 (s, 1H).

LCMS(ESI): [M]$^+$ m/z: calcd 520.2; found 521.2; Rt=1.706 min.

Compound 1395:

Retention time: 11.36 min $^1$H NMR (600 MHz, DMSO-$d_6$) δ (ppm) 0.99-1.14 (m, 3H), 1.34-1.40 (m, 3H), 1.40-1.50 (m, 1H), 1.50-1.59 (m, 1H), 1.62-1.77 (m, 2H), 1.77-1.87 (m, 2H), 2.02-2.12 (m, 3H), 2.12-2.36 (m, 7H), 2.39-2.43 (m, 1H), 2.82-3.13 (m, 3H), 4.12-4.41 (m, 1H), 5.31-5.40 (m, 1H), 5.47-5.71 (m, 2H), 7.07-7.53 (m, 2H), 7.73-7.78 (m, 0.5H), 7.84 (s, 1H), 7.93-8.02 (m, 1H), 8.05-8.11 (m, 0.5H), 10.10-10.52 (m, 1H).

LCMS(ESI): [M]$^+$ m/z: calcd 520.2; found 521.2; Rt=1.645 min.

Example 643. The Synthesis of 2-((2R,5S)-2-(2-(1-azabicyclo[2.2.1]heptan-4-yl)benzo[d]thiazol-5-yl)-5-methylpiperidin-1-yl)-N-(6-amino-5-ethylpyridin-3-yl)-2-oxoacetamide (Compound 1298)

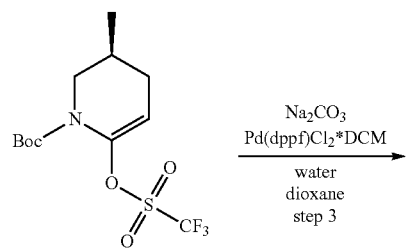

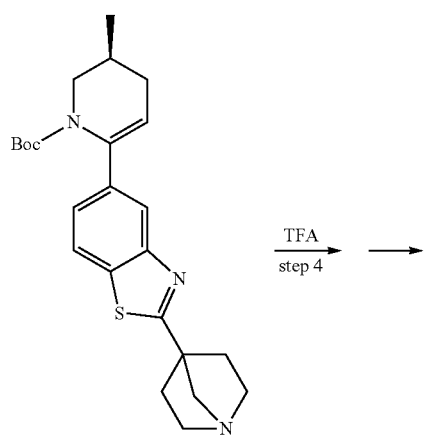

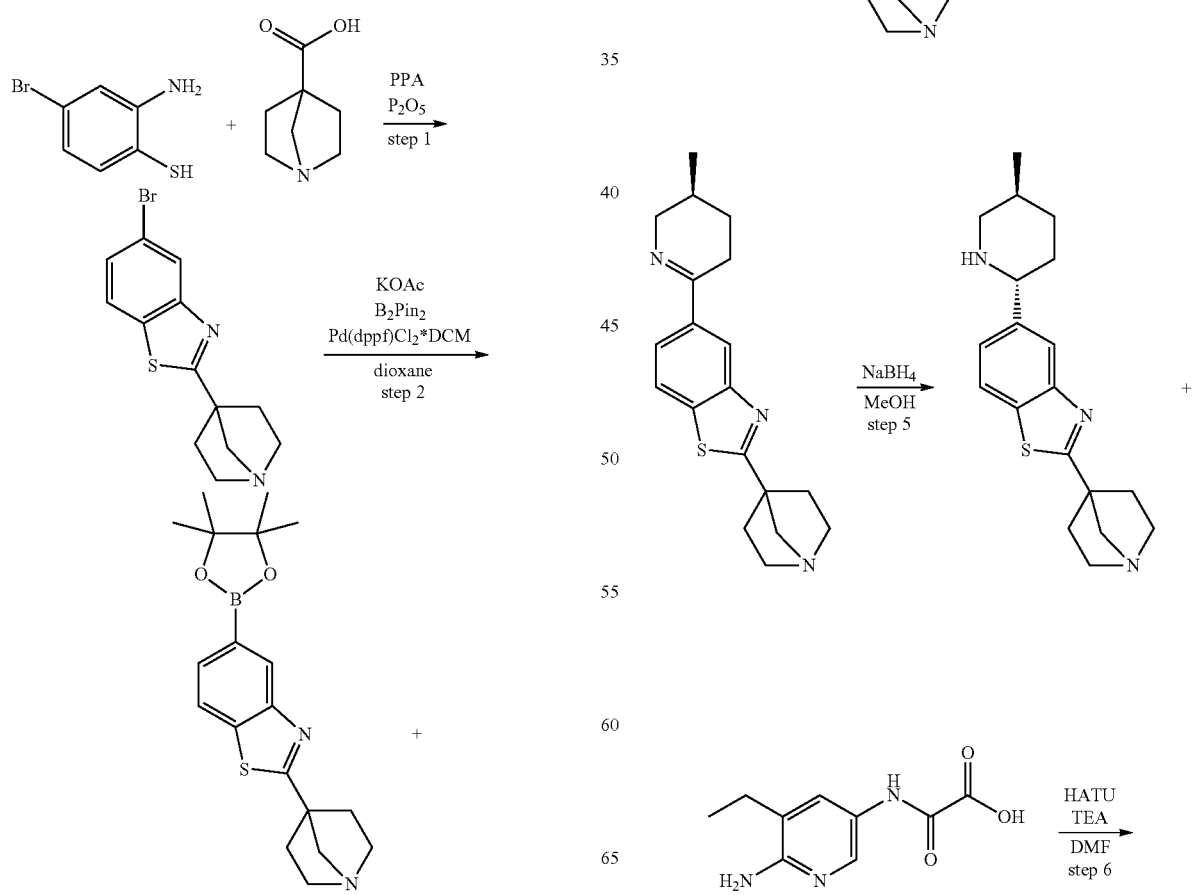

2735

-continued

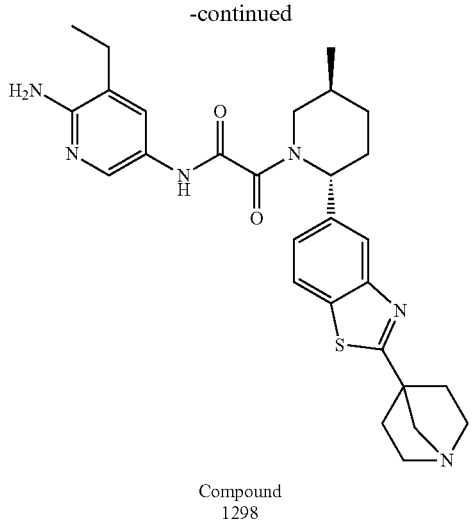

Compound 1298

Step 1: Synthesis of 2-(1-azabicyclo[2.2.1]heptan-4-yl)-5-bromobenzo[d]thiazole

Prepared by general procedure scheme H step 1A. Yield: 3.5 g (92.4%).
LCMS(ESI): [M]+ m/z: calcd 309.2; found 310.2; Rt=0.961 min.

Step 2: Synthesis of 2-(1-azabicyclo[2.2.1]heptan-4-yl)-5-(4,4,5,5-tetramethyl-1,3,2-dioxaborolan-2-yl)benzo[d]thiazole Prepared by general procedure scheme H step 2. Yield: 4 g of crude.
LCMS(ESI): [M]+ m/z: calcd 356.2; found 357.2; Rt=1.025 min.

Step 3: Synthesis of (S)-tert-butyl 6-(2-(1-azabicyclo[2.2.1]heptan-4-yl)benzo[d]thiazol-5-yl)-3-methyl-3,4-dihydropyridine-1(2H)-carboxylate Prepared by general procedure scheme H step 3. Yield: 8 g of crude.
LCMS(ESI): [M]+ m/z: calcd 425.2; found 426.2; Rt=1.254 min.

Step 4: Synthesis of (S)-2-(1-azabicyclo[2.2.1]heptan-4-yl)-5-(5-methyl-3,4,5,6-tetrahydropyridin-2-yl)benzo[d]thiazole Prepared by general procedure scheme H step 4. Yield: 6 g of crude.
LCMS(ESI): [M]+ m/z: calcd 325.2; found 326.2; Rt=0.683 min.

Step 5: Synthesis of 2-(1-azabicyclo[2.2.1]heptan-4-yl)-5-((2R,5S)-5-methylpiperidin-2-yl)benzo[d]thiazole Prepared by general procedure scheme H step 5. Yield: 2 g of crude.

2736

LCMS(ESI): [M]+ m/z: calcd 327.2; found 328.2; Rt=0.709 min.

Step 6: Synthesis of 2-((2R,5S)-2-(2-(1-azabicyclo[2.2.1]heptan-4-yl)benzo[d]thiazol-5-yl)-5-methylpiperidin-1-yl)-N-(6-amino-5-ethylpyridin-3-yl)-2-oxoacetamide (Compound 1298

Prepared by general procedure scheme H step 6A. Yield: 71 mg (37.36%).
HPLC conditions: Column: YMC Triart C18 100*20 mm, 5 microM; 0-1-5 min 50-80% water-MeOH+0.1% NH4OH, flow: 30 ml/min; (loading pump 4 ml/min MeOH).
Cis-impurity was removed by chiral HPLC (Chiralpak IA-III (250*20, 5 mkm), IPA-MeOH, 50-50, 10 ml/min).
$^1$H NMR (DMSO-d$_6$, 500 MHz): δ (ppm) 1.02 (m, 3H), 1.08 (m, 3H), 1.35 (m, 1H), 1.72 (m, 3H), 1.86 (m, 1H), 2.11 (m, 3H), 2.33 (m, 2H), 2.40 (m, 1H), 2.66 (m, 5H), 3.00 (m, 2H), 3.86 (m, 1H), 5.64 (m, 3H), 7.41 (m, 2H), 7.89 (m, 1H), 8.04 (m, 2H), 10.51 (s, 1H)
LCMS(ESI): [M+1]+ m/z: calcd 518.2; found 519.2; Rt=2.109 min.

Example 644. The Synthesis of N-(6-amino-5-ethylpyridin-3-yl)-2-((2R,5S)-5-methyl-2-(2-((1R,5S,6s)-3-methyl-3-azabicyclo[3.1.0]hexan-6-yl)benzo[d]thiazol-5-yl)piperidin-1-yl)-2-oxoacetamide (Compound 1366)

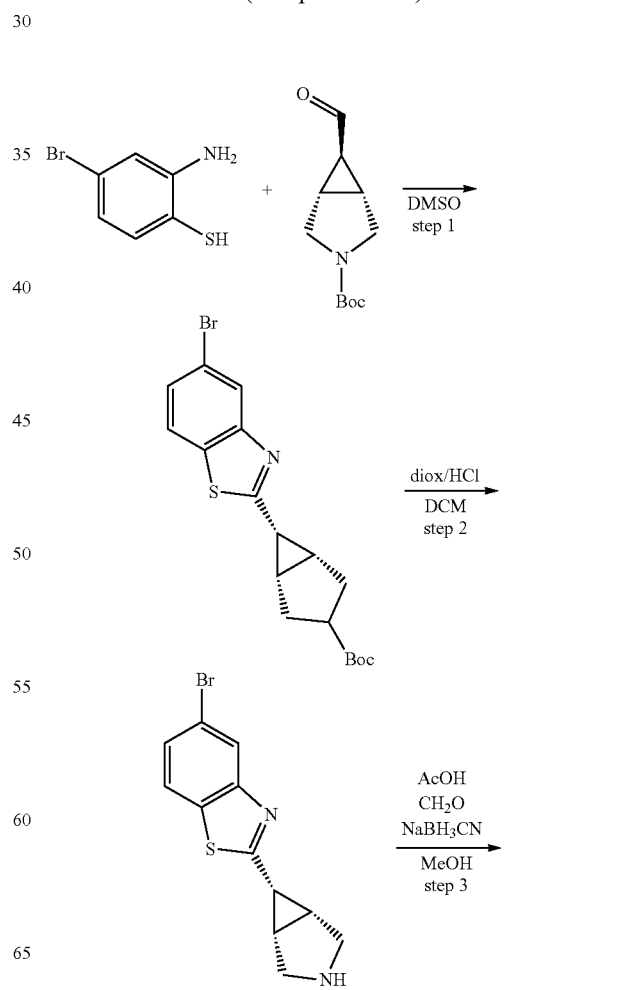

2737
-continued
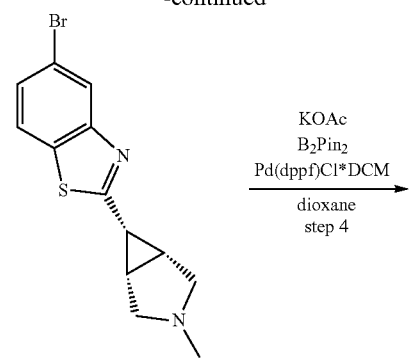
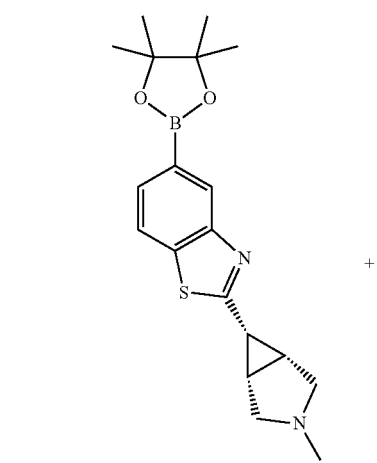
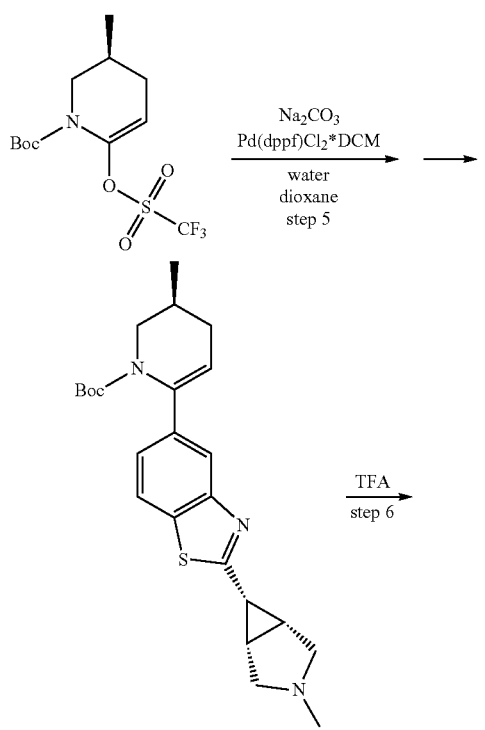
2738
-continued
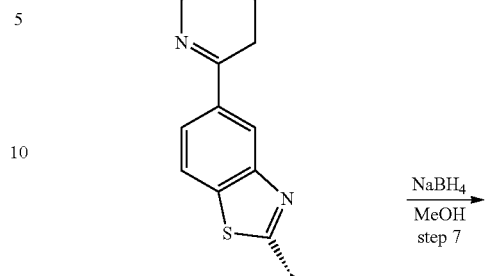
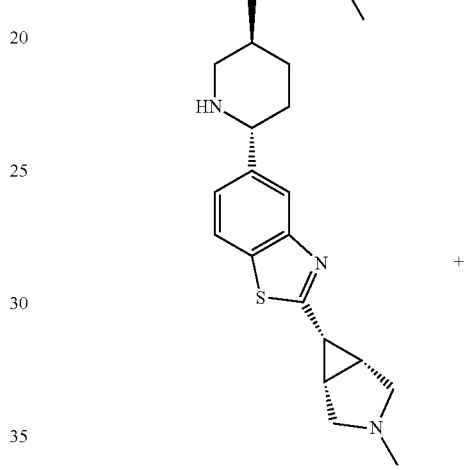
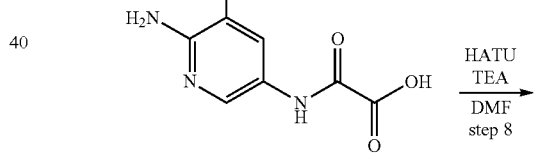
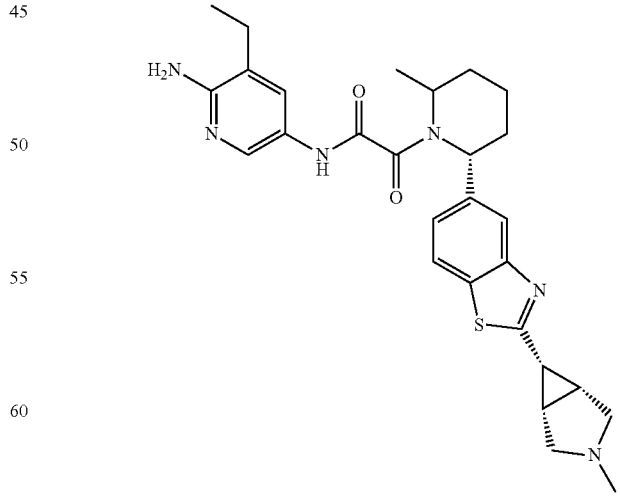
Compound 1366

Step 1: Synthesis of (1R,5S,6s)-tert-butyl 6-(5-bromobenzo[d]thiazol-2-yl)bicyclo[3.1.0]hexane-3-carboxylate Prepared by general procedure scheme H step 1B. Yield: 1.5 g of crude.
LCMS(ESI): [M]$^+$ m/z: calcd 395.2; found 396.2; Rt=1.692 min.

Step 2: Synthesis of 2-((1R,5S,6s)-3-azabicyclo[3.1.0]hexan-6-yl)-5-bromobenzo[d]thiazole To a stirred solution of tert-butyl($^1$R,$^5$S)-6-(5-bromo-1,3-benzothiazol-2-yl)-3-azabicyclo[3.1.0]hexane-3-carboxylate (2.3 g, 5.82 mmol) in DCM (10 mL) were added diox/HCl (6.9 mL) respectively at 25° C. The resulting reaction mixture was stirred at 25° C. for 12 hr. Upon completion, the reaction mixture was concentrated under reduced pressure. Then HCl salt of product was dissolved in 20 ml water, 10% Na$_2$CO$_3$ was added (20 ml), extracted with DCM (20 ml twice). Organic layer was dried over Na$_2$SO$_4$ and evaporated. The desired product 5-bromo-2-[($^1$R,$^5$S)-3-azabicyclo[3.1.0]hexan-6-yl]-1,3-benzothiazole (1.9 g, crude) was isolated as yellow color state.
LCMS(ESI): [M]$^+$ m/z: calcd 295.2; found 296.2; Rt=0.820 min.

Step 3: Synthesis of 5-bromo-2-((1R,5S,6s)-3-methyl-3-azabicyclo[3.1.0]hexan-6-yl)benzo[d]thiazole To a stirred solution of 5-bromo-2-[($^1$R,$^5$S)-3-azabicyclo[3.1.0]hexan-6-yl]-1,3-benzothiazole (1.9 g, 6.44 mmol) in MeOH (100 mL) were added formaldehyde, 37% in aq. soln. (289.89 mg, 9.65 mmol, 267.67 µL) and acetic acid (773.03 mg, 12.87 mmol, 736.92 µL), after 30 minutes sodium cyan borohydride (606.71 mg, 9.65 mmol) was added respectively at 25° C. The resulting reaction mixture was stirred at 25° C. for 14 hr. Upon completion, the reaction mixture was concentrated under reduced pressure, then extracted with DCM/water (100 ml/50 ml). Organic phase was dried over Na$_2$SO$_4$, evaporated to obtain crude product as yellow color state. The desired product 5-bromo-2-[($^1$R,$^5$S)-3-methyl-3-azabicyclo[3.1.0]hexan-6-yl]-1,3-benzothiazole (1.7 g, 5.50 mmol, 85.42% yield) was isolated as yellow color state.
LCMS(ESI): [M]$^+$ m/z: calcd 309.2; found 310.2; Rt=0.951 min.

Step 4: Synthesis of 2-((1R,5S,6s)-3-methyl-3-azabicyclo[3.1.0]hexan-6-yl)-5-(4,4,5,5-tetramethyl-1,3,2-dioxaborolan-2-yl)benzo[d]thiazole Prepared by general procedure scheme H step 2. Yield: 1.6 g of crude.
LCMS(ESI): [M]$^+$ m/z: calcd 356.2; found 357.2; Rt=1.081 min.

Step 5: Synthesis of (S)-tert-butyl 3-methyl-6-(2-((1R,5S,6s)-3-methyl-3-azabicyclo[3.1.0]hexan-6-yl)benzo[d]thiazol-5-yl)-3,4-dihydropyridine-1(2H)-carboxylate Prepared by general procedure scheme H step 3. Yield: 1.7 g of crude.
LCMS(ESI): [M]$^+$ m/z: calcd 425.2; found 426.2; Rt=1.191 min.

Step 6: Synthesis of 5-((S)-5-methyl-3,4,5,6-tetrahydropyridin-2-yl)-2-((1R,5S,6s)-3-methyl-3-azabicyclo[3.1.0]hexan-6-yl)benzo[d]thiazole Prepared by general procedure scheme H step 4. Yield: 0.434 g of crude.
LCMS(ESI): [M]$^+$ m/z: calcd 325.2; found 326.2; Rt=0.633 min.

Step 7: Synthesis of 2-((1R,5S,6r)-3-methyl-3-azabicyclo[3.1.0]hexan-6-yl)-5-((2R,5S)-5-methylpiperidin-2-yl)benzo[d]thiazole Prepared by general procedure scheme H step 5. Yield: 0.187 g (42.82%).
LCMS(ESI): [M]$^+$ m/z: calcd 327.2; found 328.2; Rt=0.707 min.

Step 8: Synthesis of N-(6-amino-5-ethylpyridin-3-yl)-2-((2R,5S)-5-methyl-2-(2-((1R,5S,6s)-3-methyl-3-azabicyclo[3.1.0]hexan-6-yl)benzo[d]thiazol-5-yl)piperidin-1-yl)-2-oxoacetamide (Compound 1366

Prepared by general procedure scheme H step 6B. Yield: 49 mg (28.65%).
HPLC conditions: Column: XBridge C18 100*19 mm, 5 microM; 0-5 min 40-90% water-MeOH+0.1% NH$_4$OH, flow: 30 ml/min; (loading pump 4 ml/min MeOH).
$^1$H NMR (600 MHz, DMSO-d$_6$) δ (ppm) 0.95-1.05 (m, 3H), 1.05-1.16 (m, 3H), 1.27-1.39 (m, 1H), 1.64-1.73 (m, 1H), 1.81-1.91 (m, 1H), 2.02-2.12 (m, 1H), 2.12-2.16 (m, 2H), 2.26 (s, 3H), 2.33-2.37 (m, 3H), 2.37-2.44 (m, 2H), 2.70 (s, 1H), 2.73-2.79 (m, 0.3H), 3.06-3.10 (m, 2H), 3.24-3.27 (m, 0.7H), 3.38-3.52 (m, 0.7H), 4.01-4.06 (m, 0.3H), 5.24-5.60 (m, 1H), 5.60-5.71 (m, 2H), 7.25-7.38 (m, 1H), 7.41-7.58 (m, 1H), 7.72-7.85 (m, 1H), 7.92-8.12 (m, 2H), 10.48-10.65 (m, 1H).
LCMS(ESI): [M]$^+$ m/z: calcd 518.2; found 519.2; Rt=2.146 min.

Example 645. The Synthesis of N-(6-amino-5-ethylpyridin-3-yl)-2-((2R,5S)-2-(2-(4-methoxy-1-methylpiperidin-4-yl)benzo[d]thiazol-5-yl)-5-methylpiperidin-1-yl)-2-oxoacetamide (Compound 1118)

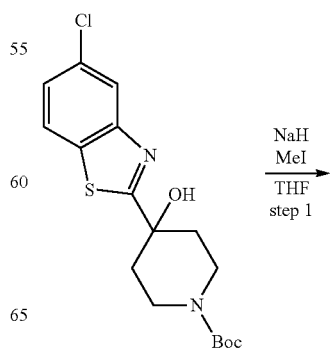

2741
-continued
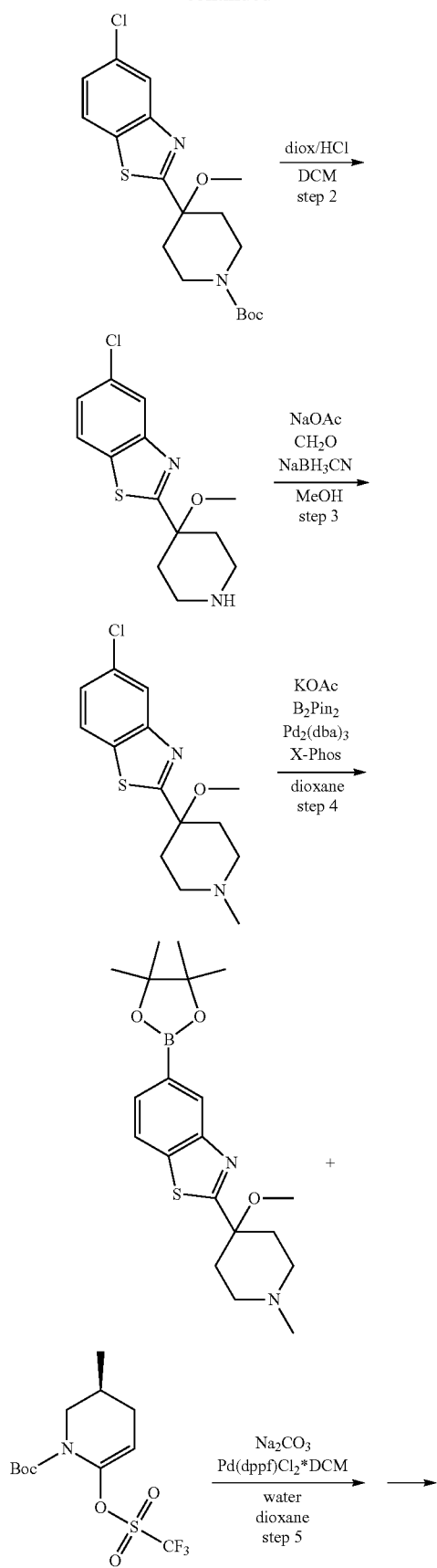
2742
-continued
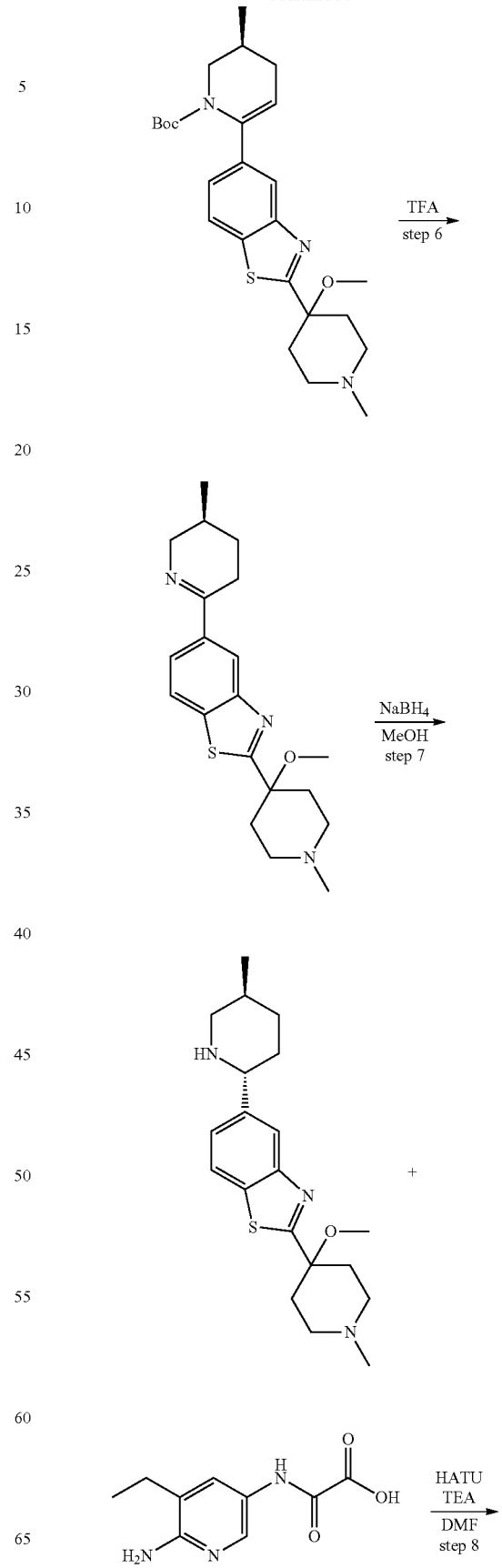

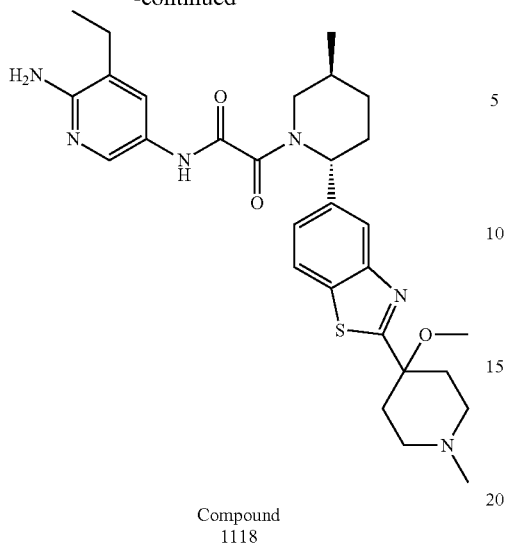

Compound 1118

Step 1: Synthesis of tert-butyl 4-(5-chlorobenzo[d]thiazol-2-yl)-4-methoxypiperidine-1-carboxylate To the stirred solution of tert-butyl 4-(5-chloro-1,3-benzothiazol-2-yl)-4-hydroxy-piperidine-1-carboxylate (7 g, 18.98 mmol) in THF (79.82 mL) sodium hydride (in oil dispersion) 60% dispersion in mineral oil (872.54 mg, 20.87 mmol, 55% purity) was added portion wise at 0° C. The resulting mixture was stirred at 0° C. for 40 min. iodomethane (3.10 g, 21.82 mmol, 1.36 mL) was added dropwise and the resulting mixture was stirred at 25° C. for 12 hr. The reaction mixture was poured into water (150 ml) and product was extracted with MTBE (3*50 ml). Combined organic layers were washed with water (2*30 ml) dried over Na$_2$SO$_4$. Solvents were evaporated in vacuum to give tert-butyl 4-(5-chloro-1,3-benzothiazol-2-yl)-4-methoxy-piperidine-1-carboxylate (7 g, 18.28 mmol, 96.34% yield).

LCMS(ESI): [M−t-Bu]$^+$ m/z: calcd 326.2; found 327.2; Rt=1.608 min.

Step 2: Synthesis of 5-chloro-2-(4-methoxypiperidin-4-yl)benzo[d]thiazole

To the stirred solution of tert-butyl 4-(5-chloro-1,3-benzothiazol-2-yl)-4-methoxy-piperidine-1-carboxylate (7 g, 18.28 mmol) in DCM (50 mL) hydrogen chloride solution 4.0 M in dioxane (40.00 g, 1.10 mol, 50 mL) was added. The resulting mixture was stirred at 25° C. for 14 hr. Solvents were evaporated in vacuum. The residue was diluted with MTBE (50 ml). Solid was filtered, washed with MTBE, then dried in vacuum to give 5-chloro-2-(4-methoxy-4-piperidyl)-1,3-benzothiazole (3.3 g, 10.34 mmol, 56.54% yield, HCl).

LCMS(ESI): [M]$^+$ m/z: calcd 282.2; found 283.2; Rt=1.003 min.

Step 3: Synthesis of 5-chloro-2-(4-methoxy-1-methylpiperidin-4-yl)benzo[d]thiazole To the stirred solution of 5-chloro-2-(4-methoxy-4-piperidyl)-1,3-benzothiazole (3 g, 9.40 mmol, HCl) in MeOH (100 mL) formaldehyde, 37% w/w aq. soln., stab. with 7-8% MeOH (1.14 g, 14.10 mmol, 1.06 mL, 37% purity) and sodium acetate, anhydrous (1.54 g, 18.79 mmol, 1.01 mL) were added. The resulting mixture was stirred for 2 hr at 25° C. Then Sodium cyan borohydride (708.61 mg, 11.28 mmol) was added portion wise. The resulting mixture was stirred at 25° C. for 12 hr. Methanol was evaporated. The residue was diluted with water (70 ml) and extracted with DCM (3*30 ml). Combined organic layers were washed with sat. K$_2$CO$_3$ solution and dried over Na$_2$SO$_4$. DCM was evaporated in vacuum to give 5-chloro-2-(4-methoxy-1-methyl-4-piperidyl)-1,3-benzothiazole (2.1 g, 7.08 mmol, 75.29% yield).

LCMS(ESI): [M]$^+$ m/z: calcd 296.2; found 297.2; Rt=2.139 min.

Step 4: Synthesis of 2-(4-methoxy-1-methylpiperidin-4-yl)-5-(4,4,5,5-tetramethyl-1,3,2-dioxaborolan-2-yl)benzo[d]thiazole 5-chloro-2-(4-methoxy-1-methyl-4-piperidyl)-1,3-benzothiazole (2.1 g, 7.08 mmol), 4,4,5,5-tetramethyl-2-(4,4,5,5-tetramethyl-1,3,2-dioxaborolan-2-yl)-1,3,2-dioxaborolane (1.98 g, 7.78 mmol) and potassium acetate (1.39 g, 14.15 mmol, 884.52 µL) were mixed in dioxane (30 mL). The resulting mixture was evacuated and then backfilled with argon, this operation was repeated three times, then tris(dibenzylideneacetone)dipalladium (0) (323.94 mg, 353.76 µmol) and X-Phos (337.29 mg, 707.51 µmol) were added under argon. The reaction mixture was stirred under argon at 90° C. for 14 hr. The reaction mixture was cooled down and filtered. The filter cake was washed with dioxane (2*10 ml) and discarded. The combined filtrate was concentrated in vacuum. The residue was diluted with MTBE (50 ml) and extracted with a NaHSO$_4$ water solution (20 ml) (repeated 3 times). The combined aqueous layer was basified to pH 10 with 10% aqueous sodium hydroxide to give water solution of 2-(4-methoxy-1-methyl-4-piperidyl)-5-(4,4,5,5-tetramethyl-1,3,2-dioxaborolan-2-yl)-1,3-benzothiazole (2.6 g, 6.70 mmol, 94.63% yield) which was used directly in the next step.

LCMS(ESI): [M]$^+$ m/z: calcd 388.2; found 389.2; Rt=1.067 min.

Step 5: Synthesis of (S)-tert-butyl 6-(2-(4-methoxy-1-methylpiperidin-4-yl)benzo[d]thiazol-5-yl)-3-methyl-3,4-dihydropyridine-1(2H)-carboxylate Prepared by general procedure scheme H step 3. Yield: 1.9 g of crude.

LCMS(ESI): [M]$^+$ m/z: calcd 457.2; found 458.2; Rt=1.403 min.

Step 6: Synthesis of (S)-2-(4-methoxy-1-methylpiperidin-4-yl)-5-(5-methyl-3,4,5,6-tetrahydropyridin-2-yl)benzo[d]thiazole Prepared by general procedure scheme H step 4. Yield: 0.76 g of crude.

LCMS(ESI): [M]$^+$ m/z: calcd 357.2; found 358.2; Rt=0.719 min.

Step 7: Synthesis of 2-(4-methoxy-1-methylpiperidin-4-yl)-5-((2R,5S)-5-methylpiperidin-2-yl)benzo[d]thiazole Prepared by general procedure scheme H step 5. Yield: 0.5 g of crude.

LCMS(ESI): [M]+ m/z: calcd 359.2; found 360.2; Rt=0.754 min.

Step 8: Synthesis of N-(6-amino-5-ethylpyridin-3-yl)-2-((2R,5S)-2-(2-(4-methoxy-1-methylpiperidin-4-yl)benzo[d]thiazol-5-yl)-5-methylpiperidin-1-yl)-2-oxoacetamide (Compound 1118)

Prepared by general procedure scheme H step 6A. Yield: 56 mg (24.37%).

HPLC conditions: Column:YMC Triart C18 100*20 mm, 5 microM; 0-5 min 45-75% water-MeOH+0.1% NH$_4$OH, flow: 30 ml/min; (loading pump 4 ml/min MeOH).

Compound 1118:

$^1$H NMR (600 MHz, DMSO-d$_6$) δ (ppm) 1.01-1.05 (m, 3H), 1.06-1.14 (m, 3H), 1.31-1.39 (m, 1H), 1.68-1.73 (m, 1H), 1.84-1.92 (m, 1H), 2.03-2.09 (m, 3H), 2.11-2.16 (m, 2H), 2.18 (s, 3H), 2.25-2.32 (m, 3H), 2.38-2.43 (m, 2H), 2.55-2.59 (m, 2H), 2.77-3.06 (m, 1H), 3.11 (s, 3H), 3.46-4.08 (m, 1H), 5.28-5.73 (m, 3H), 7.37-7.45 (m, 1H), 7.45-7.56 (m, 1H), 7.89-7.96 (m, 1H), 7.98-8.14 (m, 2H), 10.52-10.63 (m, 1H).

LCMS(ESI): [M]+ m/z: calcd 550.2; found 551.2; Rt=1.726 min.

Example 646. The Synthesis of 5-(2-((2R,5S)-2-(2-(1-((Dimethylamino)methyl)cyclopropyl)benzo[d]thiazol-5-yl)-5-methylpiperidin-1-yl)-2-oxoacetamido)-2-methoxynicotinamide (Compound 1109)

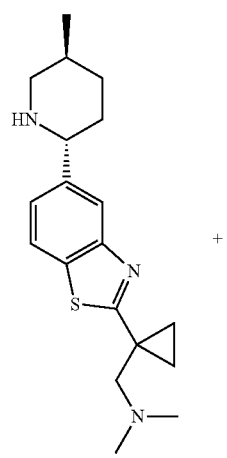

+

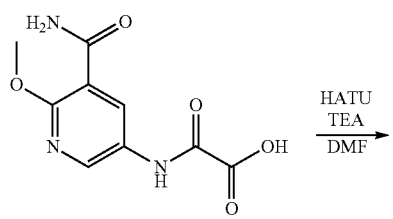

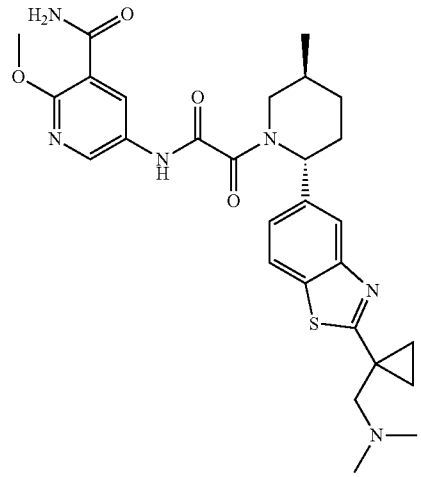

Prepared by general procedure 8 step 6A. Yield: 197 mg (21.43%).

HPLC conditions: Column: YMC Triart C18 100*20 mm, 5 microM; 0-1-6 min 50-80% water-MeOH+0.1% NH$_4$OH, flow: 30 ml/min; (loading pump 4 ml/min MeOH).

It was then additionally purified using preparative chiral HPLC (column:Chiralcel OD-H (250*20 mm, 5 mkm); mobile phase: Hexane-IPA-MeOH, 60-20-20; flow rate: 12 ml/min) to afford Compound 1109 2-methoxy-5-[[2-oxo-2-[(2R,5S)-2-[2-[1-[(dimethylamino)methyl]cyclopropyl]-1,3-benzothiazol-5-yl]-5-methyl-1-piperidyl]acetyl]amino]pyridine-3-carboxamide (197 mg, 357.75 μmol, 21.43% yield) (RT=16.790 min) as white solid.

$^1$H NMR (600 MHz, DMSO-d$_6$) δ (ppm) 0.97-1.08 (m, 5H), 1.31-1.41 (m, 1H), 1.41-1.47 (m, 2H), 1.67-1.76 (m, 1H), 1.84-1.96 (m, 1H), 2.01-2.36 (m, 8H), 2.58-2.65 (m, 2H), 2.78-3.24 (m, 1H), 3.47-4.04 (m, 4H), 5.19-5.71 (m, 1H), 7.25-7.38 (m, 1H), 7.65-8.03 (m, 4H), 8.38-8.59 (m, 2H), 10.96-11.15 (m, 1H).

LCMS(ESI): [M]+ m/z: calcd 550.2; found 551.2; Rt=2.439 min.

Example 647. The Synthesis of N-(6-amino-5-ethylpyridin-3-yl)-2-((2R,5S)-2-(2-(4-Fluoro-1-methylpiperidin-4-yl)benzo[d]thiazol-5-yl)-5-methylpiperidin-1-yl)-2-oxoacetamide (Compound 1160)

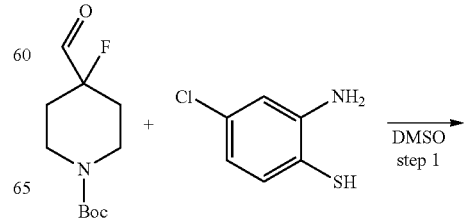

2747
-continued
2748
-continued
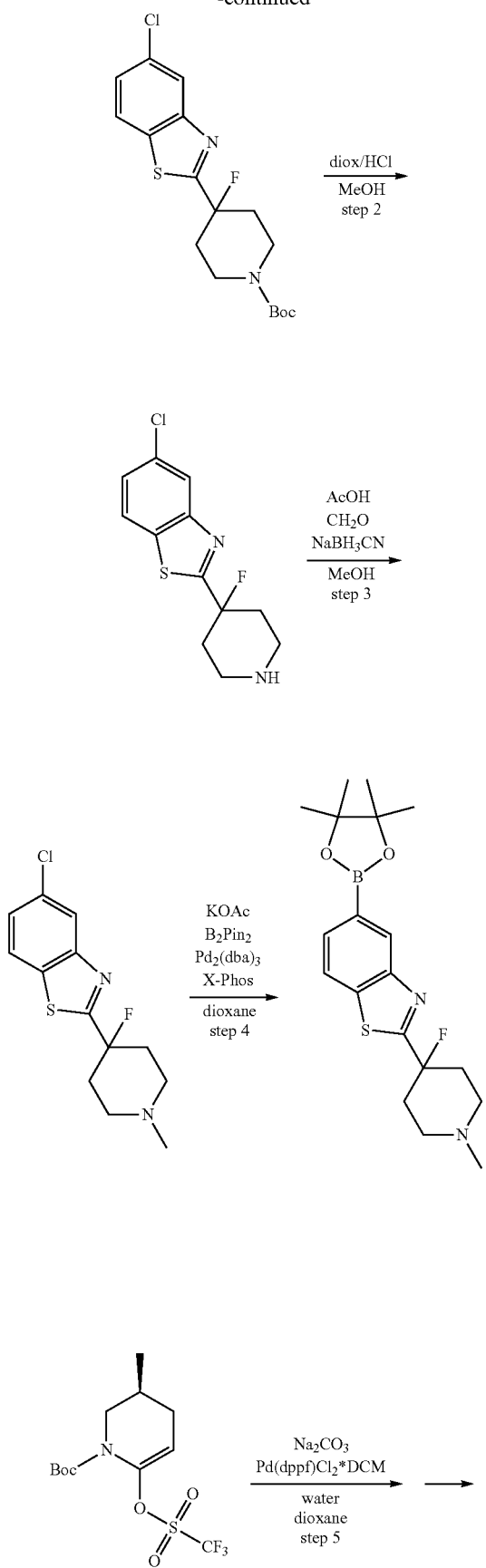
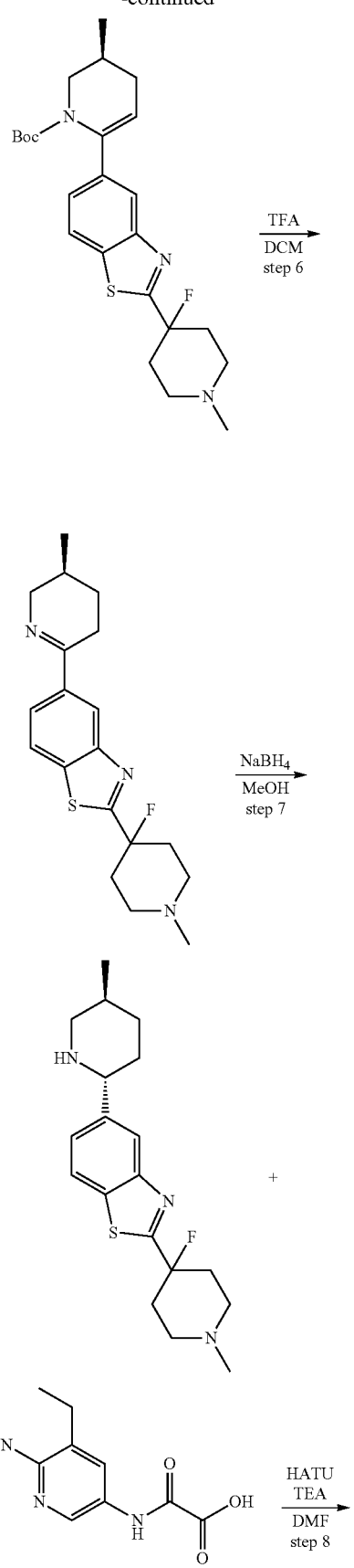

-continued

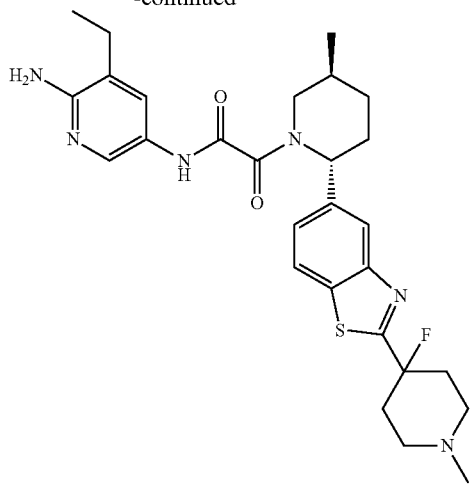

Step 1: Synthesis of tert-butyl 4-(5-chlorobenzo[d]thiazol-2-yl)-4-Fluoropiperidine-1-carboxylate Prepared by general procedure scheme H step 1B. Yield: 0.8 g of crude.
LCMS(ESI): [M−t-Bu]+ m/z: calcd 314.2; found 315.2; Rt=1.721 min.

Step 2: Synthesis of 5-chloro-2-(4-Fluoropiperidin-4-yl)benzo[d]thiazole

Hydrogen chloride solution 4.0 M in dioxane (1.60 g, 43.88 mmol, 2 mL) was added to a solution of tert-butyl 4-(5-chloro-1,3-benzothiazol-2-yl)-4-fluoro-piperidine-1-carboxylate (0.8 g, 2.16 mmol) in MeOH (20 mL). The reaction mixture was stirred at 0° C. for 6 hr, then evaporated and added to MTBE (40 ml) the resulting precipitate was filtered off, washed with MTBE (30 ml) and dried to afford 5-chloro-2-(4-fluoro-4-piperidyl)-1,3-benzothiazole (0.5 g, 1.63 mmol, 75.45% yield, HCl).
LCMS(ESI): [M]+ m/z: calcd 270.2; found 271.2; Rt=1.483 min.

Step 3: Synthesis of 5-chloro-2-(4-Fluoro-1-methylpiperidin-4-yl)benzo[d]thiazole Formaldehyde, 37% w/w aq. soln., stab. with 7-8% MeOH (146.62 mg, 4.88 mmol, 135.39 µL) and acetic acid (293.20 mg, 4.88 mmol, 279.50 µL) were added to the solution of 5-chloro-2-(4-fluoro-4-piperidyl)-1,3-benzothiazole (0.5 g, 1.63 mmol, HCl) and sodium acetate, anhydrous (146.86 mg, 1.79 mmol, 96.12 µL) in MeOH (21.02 mL). Resulting mixture was stirred at 0° C. for 1 hr before sodium cyan borohydride (204.55 mg, 3.26 mmol) was added thereto. After that, stirring was continued for 6 hr. Then, solvent was removed under reduced pressure and residue was partitioned between 10% aq. $K_2CO_3$ solution (20 ml) and DCM (40 ml). Organic layer was separated, dried over solid $K_2CO_3$ and concentrated under reduced pressure, leaving 5-chloro-2-(4-fluoro-1-methyl-4-piperidyl)-1,3-benzothiazole (0.5 g, crude).
$^1$H NMR (500 MHz, DMSO-$d_6$) δ (ppm) 2.12 (m, 2H), 2.45 (s, 3H), 2.52 (m, 4H), 2.75 (m, 2H), 7.54 (d, 1H), 8.14 (s, 1H), 8.19 (d, 1H).

Step 4: Synthesis of 2-(4-Fluoro-1-methylpiperidin-4-yl)-5-(4,4,5,5-tetramethyl-1,3,2-dioxaborolan-2-yl)benzo[d]thiazole tris(Dibenzylideneacetone)dipalladium(0) (80.39 mg, 87.79 µmol) and X-Phos (167.40 mg, 351.15 µmol) was added to a solution of 5-chloro-2-(4-fluoro-1-methyl-4-piperidyl)-1,3-benzothiazole (0.5 g, 1.76 mmol) and 4,4,5,5-tetramethyl-2-(4,4,5,5-tetramethyl-1,3,2-dioxaborolan-2-yl)-1,3,2-dioxaborolane (579.60 mg, 2.28 mmol) in dioxane (20 mL). Reaction flask was evacuated and refilled with argon 3 times. Then potassium acetate (172.31 mg, 1.76 mmol, 109.75 µL) was added under stream of argon. Resulting mixture was stirred at 90° C. for 15 hr under inert atmosphere, then cooled and evaporated in vacuum poured into water (200 ml) and extracted with DCM (2×30 ml), dried over sodium sulphate and evaporated in vacuum to leave 0.6 g of crude product, 0.6 g of which was purification by column chromatography on silica gel using MeCN gradient (10-100% MeCN) to afford 2-(4-fluoro-1-methyl-4-piperidyl)-5-(4,4,5,5-tetramethyl-1,3,2-dioxaborolan-2-yl)-1,3-benzothiazole (0.16 g, 425.20 µmol, 24.22% yield).
LCMS(ESI): [M]+ m/z: calcd 376.2; found 377.2; Rt=1.181 min.

Step 5: Synthesis of (S)-tert-butyl 6-(2-(4-Fluoro-1-methylpiperidin-4-yl)benzo[d]thiazol-5-yl)-3-methyl-3,4-dihydropyridine-1(2H)-carboxylate Prepared by general procedure scheme H step 3. Yield: 0.3 g of crude.
LCMS(ESI): [M]+ m/z: calcd 445.2; found 446.2; Rt=3.023 min.

Step 6: Synthesis of (S)-2-(4-Fluoro-1-methylpiperidin-4-yl)-5-(5-methyl-3,4,5,6-tetrahydropyridin-2-yl)benzo[d]thiazole Prepared by general procedure scheme H step 4. Yield: 0.2 g of crude.
LCMS(ESI): [M]+ m/z: calcd 345.2; found 346.2; Rt=1.379 min.

Step 7: Synthesis of 2-(4-Fluoro-1-methylpiperidin-4-yl)-5-((2R,5S)-5-methylpiperidin-2-yl)benzo[d]thiazole Prepared by general procedure scheme H step 5. Yield: 0.12 g of crude.
LCMS(ESI): [M]+ m/z: calcd 347.2; found 348.2; Rt=1.802 min.

Step 8: Synthesis of N-(6-amino-5-ethylpyridin-3-yl)-2-((2R,5S)-2-(2-(4-Fluoro-1-methylpiperidin-4-yl)benzo[d]thiazol-5-yl)-5-methylpiperidin-1-yl)-2-oxoacetamide (Compound 1160)

Prepared by general procedure scheme H step 6A. Yield: 6.4 mg (2.74%).
HPLC conditions: Column:YMC Triart C18 100*20 mm, 5 microM; 0-1-6 min 60-60-85% water-MeOH+0.1% $NH_4OH$, flow: 30 ml/min; (loading pump 4 ml/min MeOH).
$^1$H NMR (600 MHz, DMSO-$d_6$) δ (ppm) 1.02-1.06 (m, 6H), 1.30-1.41 (m, 1H), 1.64-1.73 (m, 1H), 1.83-1.92 (m, 1H), 2.10-2.20 (m, 3H), 2.22-2.36 (m, 8H), 2.38-2.42 (m, 2H), 2.70-2.93 (m, 3H), 3.45-4.08 (m, 1H), 5.26-5.74 (m, 3H), 7.40-7.45 (m, 1H), 7.49-7.53 (m, 1H), 7.94-8.07 (m, 2H), 8.13-8.19 (m, 1H), 10.49-10.63 (m, 1H).
LCMS(ESI): [M]+ m/z: calcd 538.2; found 539.2; Rt=2.357 min.
Example 648. The Synthesis of 5-(2-((2R,5S)-2-(2-(3-((Dimethylamino)methyl)oxetan-3-yl)benzo[d]thiazol-5-yl)-5-methylpiperidin-1-yl)-2-oxoacetamido)-2-methoxynicotinamide (Compound 1155)
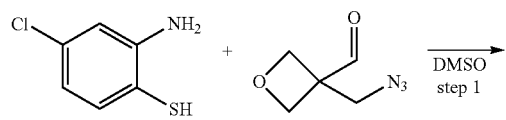
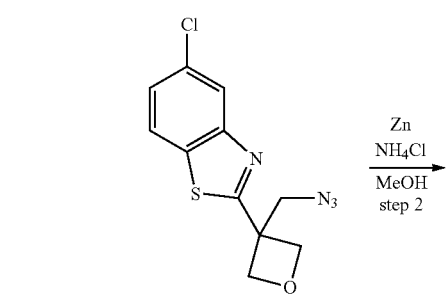
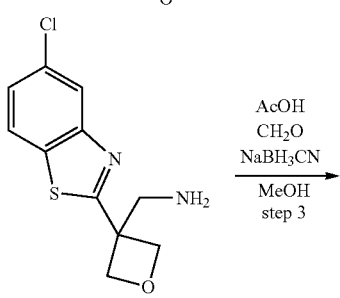
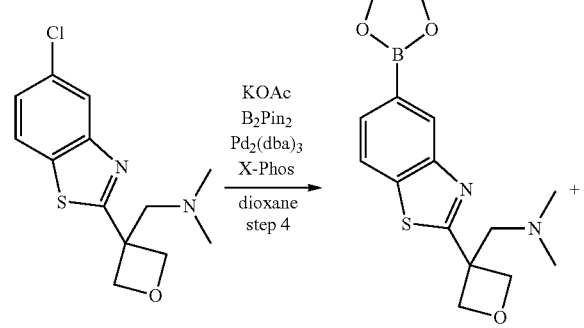
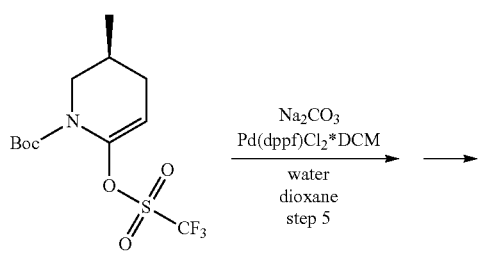
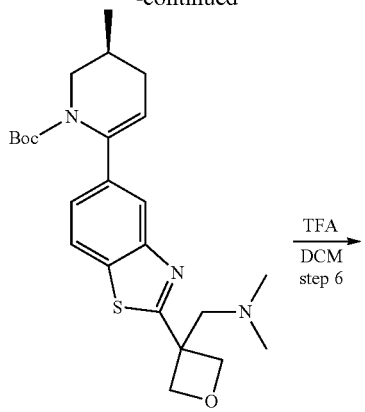
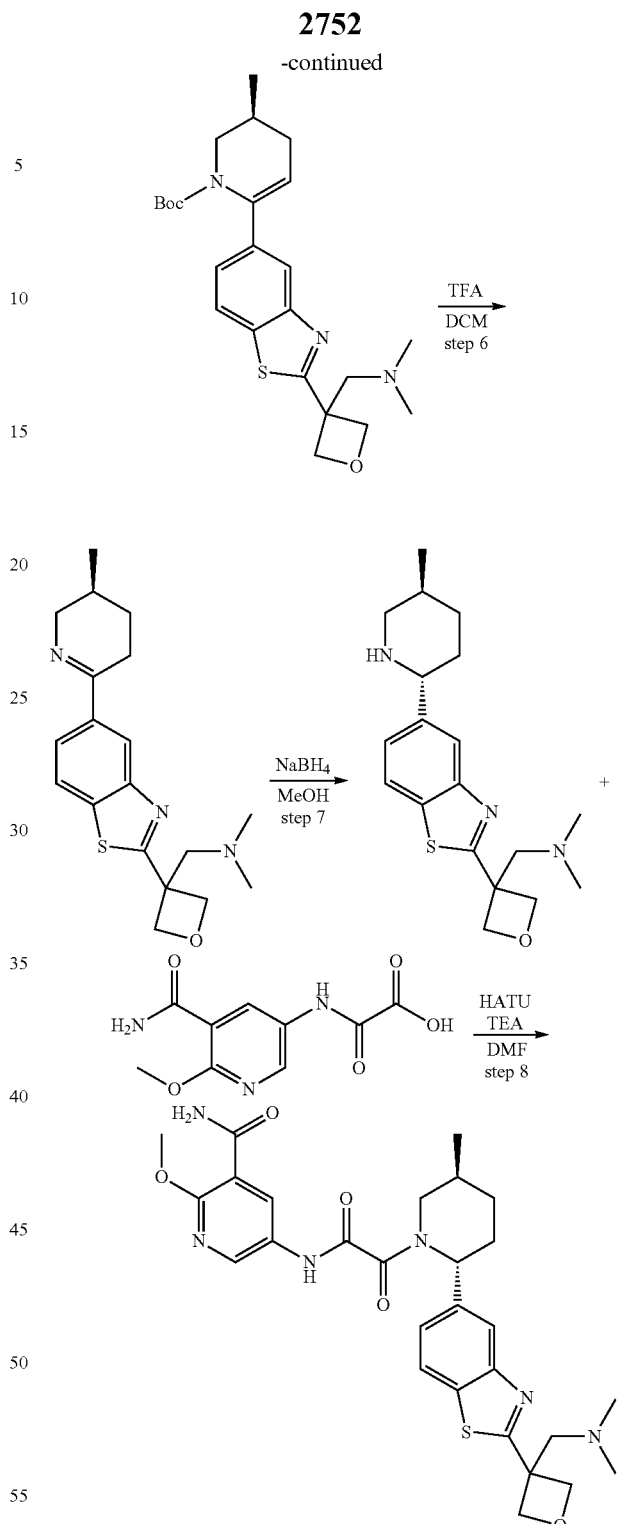
Step 1: Synthesis of 2-(3-(Azidomethyl)oxetan-3-yl)-5-chlorobenzo[d]thiazole
Prepared by general procedure scheme H step 1B. Yield: 11 g of crude.
LCMS(ESI): [M]+ m/z: calcd 280.2; found 281.2; Rt=3.578 min.

Step 2: Synthesis of (3-(5-chlorobenzo[d]thiazol-2-yl)oxetan-3-yl)methanamine Crude MTBE solution of 2-[3-(azidomethyl)oxetan-3-yl]-5-chloro-1,3-benzothiazole (11 g, 39.18 mmol) (approximately 50 ml) was diluted with MeOH (100 mL) and ammonium chloride (12.58 g, 235.10 mmol, 8.22 mL) was added. Zinc (7.69 g, 117.55 mmol) dust was added potion wise with stirring at 25° C. to the above mixture. The reaction mixture was stirred at 25° C. for 12 hr, and then filtered. The filter cake was washed with MeOH (2*25 ml) and discarded. The combined filtrate was concentrated in vacuum. The residue was diluted with MTBE (100 ml) and extracted with 5% aqueous sodium hydrogen sulphate solution (100 ml). The resulting aqueous solution of amine hydrogen sulphate was then basified to pH 11 with 10% aqueous sodium hydroxide solution and extracted with DCM (2*50 ml). The combined organic extracts were dried over sodium sulphate and concentrated in vacuum to afford crude [3-(5-chloro-1,3-benzothiazol-2-yl)oxetan-3-yl]methanamine (1.2 g, 4.71 mmol, 12.02% yield) as light-yellow gum, which was used directly in the next step.

LCMS(ESI): [M]+ m/z: calcd 254.2; found 255.2; Rt=1.985 min.

Step 3: Synthesis of 1-(3-(5-chlorobenzo[d]thiazol-2-yl)oxetan-3-yl)-N,N-dimethylmethanamine Formaldehyde, 37% w/w aq. soln., stab. with 7-8% MeOH (946.16 mg, 11.66 mmol, 873.64 µL, 37% purity) and acetic acid (518.63 mg, 8.64 mmol, 494.41 µL) were added to a stirred solution of [3-(5-chloro-1,3-benzothiazol-2-yl)oxetan-3-yl]methanamine (1.1 g, 4.32 mmol) in MeOH (30.49 mL) at 25° C. The resulting mixture was stirred at 25° C. for 1 hr, then sodium cyan borohydride (542.73 mg, 8.64 mmol) was added in one portion at 25° C. (foaming!). The reaction mixture was stirred at 25° C. for 12 hr, and then concentrated in vacuum. The residue was diluted with 10% aqueous sodium hydroxide solution (20 ml) and extracted with DCM (2*20 ml). The combined organic extracts were dried over sodium sulphate and concentrated in vacuum to afford crude 1-[3-(5-chloro-1,3-benzothiazol-2-yl)oxetan-3-yl]-N,N-dimethylmethanamine (1.3 g, crude) as light-yellow gum, which was used directly in the next step.

LCMS(ESI): [M]+ m/z: calcd 282.2; found 283.2; Rt=1.530 min.

Step 4: Synthesis of N,N-dimethyl-1-(3-(5-(4,4,5,5-tetramethyl-1,3,2-dioxaborolan-2-yl)benzo[d]thiazol-2-yl)oxetan-3-yl)methanamine A mixture of 1-[3-(5-chloro-1,3-benzothiazol-2-yl)oxetan-3-yl]-N,N-dimethylmethanamine (1.4 g, 4.95 mmol), 4,4,5,5-tetramethyl-2-(4,4,5,5-tetramethyl-1,3,2-dioxaborolan-2-yl)-1,3,2-dioxaborolane (1.38 g, 5.45 mmol) and potassium acetate (971.72 mg, 9.90 mmol, 618.93 µL) in dioxane (35 mL) was evacuated and then backfilled with argon. This operation was repeated two times, then tris(1,5-diphenylpenta-1,4-dien-3-one)dipalladium (226.67 mg, 247.53 µmol) and dicyclohexyl[2',4',6'-tris(propan-2-yl)-[1,1'-biphenyl]-2-yl]phosphane (472.02 mg, 990.14 µmol) were added under argon, and the reaction mixture was stirred at 95° C. for 18 hr. The reaction mixture was cooled down and filtered. The filter cake was washed with dioxane (2*10 ml) and discarded. The combined filtrate was concentrated in vacuum. The residue was diluted with DCM (30 ml) and extracted with a solution of sodium hydrogen sulphate (1.19 g, 9.90 mmol) in water (20 ml) (repeated two times). The combined aqueous layer was basified to pH 10 with 10% aqueous sodium hydroxide solution and back-extracted with DCM (3*25 ml). Evaporation of both DCM extracts does not showed desired product. It seemed like boronic ester hydrolyzed in aqueous media and remained in aqueous phase as boronic acid. The combined water layer (approximately 100 ml) contained N,N-dimethyl-1-[3-[5-(4,4,5,5-tetramethyl-1,3,2-dioxaborolan-2-yl)-1,3-benzothiazol-2-yl]oxetan-3-yl]methanamine (1.85 g, 4.94 mmol, 100.00% yield) (theoretical amount of product, most likely in boronic acid form) was used directly in the next step.

LCMS(ESI): [M]+ m/z: calcd 374.2; found 375.2; Rt=2.586 min.

Step 5: Synthesis of (S)-tert-butyl 6-(2-(3-((Dimethylamino)methyl)oxetan-3-yl)benzo[d]thiazol-5-yl)-3-methyl-3,4-dihydropyridine-1(2H)-carboxylate Prepared by general procedure scheme H step 3. Yield: 1.3 g of crude.

LCMS(ESI): [M]+ m/z: calcd 443.2; found 444.2; Rt=1.279 min.

Step 6: Synthesis of (S)—N,N-dimethyl-1-(3-(5-(5-methyl-3,4,5,6-tetrahydropyridin-2-yl)benzo[d]thiazol-2-yl)oxetan-3-yl)methanamine Prepared by general procedure scheme H step 4. Yield: 0.45 g of crude.

LCMS(ESI): [M]+ m/z: calcd 343.2; found 344.2; Rt=0.624 min.

Step 7: Synthesis of N,N-dimethyl-1-(3-(5-((2R,5S)-5-methylpiperidin-2-yl)benzo[d]thiazol-2-yl)oxetan-3-yl)methanamine Prepared by general procedure scheme H step 5. Yield: 0.33 g (72.91%).

LCMS(ESI): [M]+ m/z: calcd 345.2; found 346.2; Rt=0.574 min.

Step 8: Synthesis of 5-(2-((2R,5S)-2-(2-(3-((Dimethylamino)methyl)oxetan-3-yl)benzo[d]thiazol-5-yl)-5-methylpiperidin-1-yl)-2-oxoacetamido)-2-methoxynicotinamide (Compound 1155

Prepared by general procedure scheme H step 6A. Yield: 27.3 mg (11.1%).

HPLC conditions: Column:YMC Triart C18 100*20 mm, 5 microM; 0-1-5 min 20-60% water-MeCN+0.1% NH$_4$OH, flow: 30 ml/min; (loading pump 4 ml/min MeOH).

$^1$H NMR (600 MHz, DMSO-d$_6$) δ (ppm) 1.01-1.09 (m, 3H), 1.32-1.42 (m, 1H), 1.70-1.77 (m, 1H), 1.84-1.94 (m, 1H), 2.08 (s, 6H), 2.11-2.36 (m, 2H), 2.83-3.37 (m, 3H), 3.50-4.09 (m, 4H), 4.70-4.78 (m, 2H), 4.91-4.97 (m, 2H), 5.28-5.75 (m, 1H), 7.37-7.46 (m, 1H), 7.66-7.78 (m, 2H), 7.93-7.99 (m, 1H), 8.04-8.12 (m, 1H), 8.41-8.49 (m, 1H), 8.49-8.60 (m, 1H), 10.97-11.20 (m, 1H).

LCMS(ESI): [M]+ m/z: calcd 566.2; found 567.2; Rt=2.625 min.

2755
Example 649. The Synthesis of N-(6-amino-5-ethylpyridin-3-yl)-2-((5S)-5-methyl-2-(2-(3-methyl-3-azabicyclo[3.2.0]heptan-6-yl)benzo[d]thiazol-5-yl)piperidin-1-yl)-2-oxoacetamide (Compound 1147)
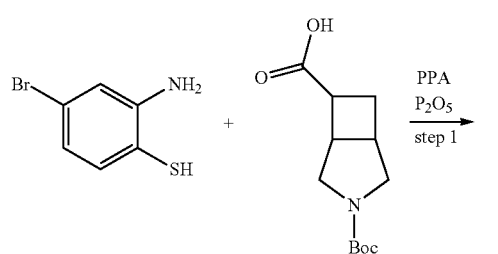
step 1: PPA, $P_2O_5$
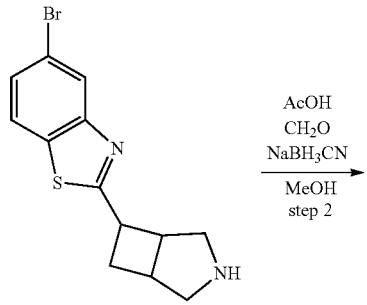
step 2: AcOH, $CH_2O$, $NaBH_3CN$, MeOH
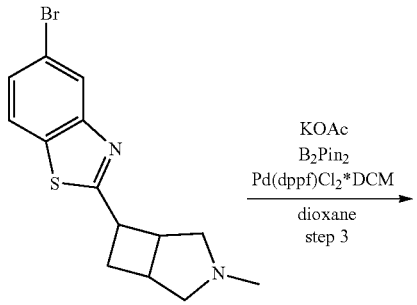
step 3: KOAc, $B_2Pin_2$, Pd(dppf)$Cl_2$*DCM, dioxane
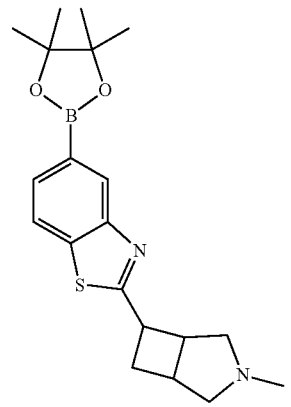
+
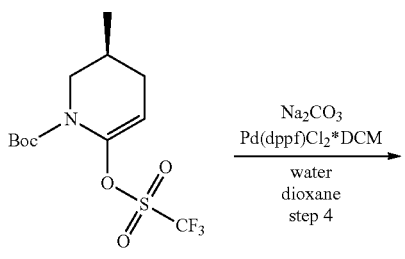
step 4: $Na_2CO_3$, Pd(dppf)$Cl_2$*DCM, water, dioxane
2756
-continued
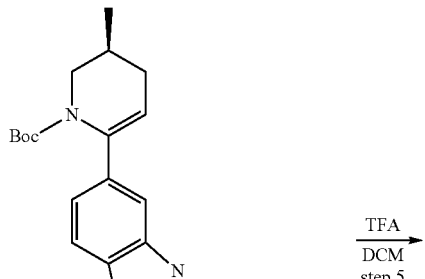
step 5: TFA, DCM
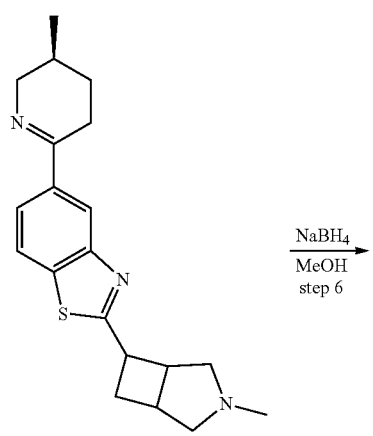
step 6: $NaBH_4$, MeOH
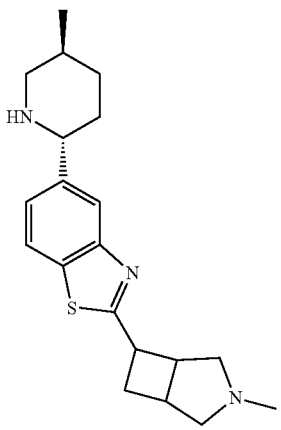
+
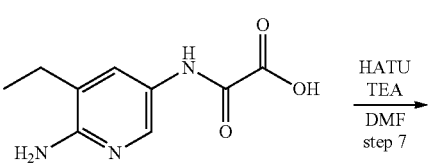
step 7: HATU, TEA, DMF

2757

-continued

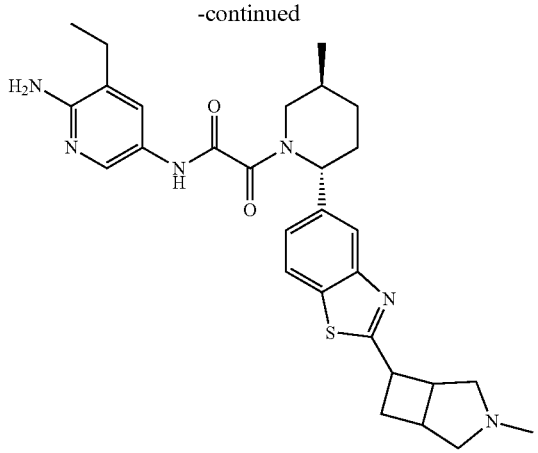

Step 1: Synthesis of 2-(3-azabicyclo[3.2.0]heptan-6-yl)-5-bromobenzo[d]thiazole

Prepared by general procedure scheme H step 1A. Yield: 2.3 g (89.73%).
LCMS(ESI): [M]+ m/z: calcd 309.2; found 310.2; Rt=0.815 min.

Step 2: Synthesis of 5-bromo-2-(3-methyl-3-azabicyclo[3.2.0]heptan-6-yl)benzo[d]thiazole Formaldehyde, 37% w/w aq. soln., stab. with 7-8% MeOH (783.90 mg, 26.11 mmol, 723.82 µL) and acetic acid (893.33 mg, 14.88 mmol, 851.60 µL) were added to a stirred solution of 2-(3-azabicyclo[3.2.0]heptan-6-yl)-5-bromo-1,3-benzothiazole (2.3 g, 7.44 mmol) in MeOH (60.07 mL) at 25° C. The resulting mixture was stirred at 25° C. for 0.5 hr, then sodium cyan borohydride (934.83 mg, 14.88 mmol) was added in one portion at 25° C. (foaming!). The reaction mixture was stirred at 25° C. for 17 hr, and then concentrated in vacuum. The residue was diluted with 10% aqueous sodium hydroxide solution (20 ml) and extracted with DCM (2*20 ml). The combined organic extracts were dried over sodium sulphate and concentrated in vacuum to afford crude 5-bromo-2-(3-methyl-3-azabicyclo[3.2.0]heptan-6-yl)-1,3-benzothiazole (1.5 g, 4.64 mmol, 62.39% yield).
LCMS(ESI): [M]+ m/z: calcd 323.2; found 324.2; Rt=0.840 min.

Step 3: Synthesis of 2-(3-methyl-3-azabicyclo[3.2.0]heptan-6-yl)-5-(4,4,5,5-tetramethyl-1,3,2-dioxaborolan-2-yl)benzo[d]thiazole Prepared by general procedure scheme H step 2. Yield: 1 g of crude.
LCMS(ESI): [M]+ m/z: calcd 370.2; found 371.2; Rt=0.886 min.

Step 4: Synthesis of (3S)-tert-butyl 3-methyl-6-(2-(3-methyl-3-azabicyclo[3.2.0]heptan-6-yl)benzo[d]thiazol-5-yl)-3,4-dihydropyridine-1(2H)-carboxylate Prepared by general procedure scheme H step 3. Yield: 1.4 g of crude.
LCMS(ESI): [M]+ m/z: calcd 439.2; found 440.2; Rt=1.366 min.

2758

Step 5: Synthesis of 5-((S)-5-methyl-3,4,5,6-tetrahydropyridin-2-yl)-2-(3-methyl-3-azabicyclo[3.2.0]heptan-6-yl)benzo[d]thiazole Prepared by general procedure scheme H step 4. Yield: 1 g of crude.
LCMS(ESI): [M]+ m/z: calcd 339.2; found 340.2; Rt=0.697 min.

Step 6: Synthesis of 2-(3-methyl-3-azabicyclo[3.2.0]heptan-6-yl)-5-((2R,5S)-5-methylpiperidin-2-yl)benzo[d]thiazole Prepared by general procedure scheme H step 5. Yield: 0.7 g of crude.
LCMS(ESI): [M]+ m/z: calcd 341.2; found 342.2; Rt=0.658 min.

Step 7: Synthesis of N-(6-amino-5-ethylpyridin-3-yl)-2-((5S)-5-methyl-2-(2-(3-methyl-3-azabicyclo[3.2.0]heptan-6-yl)benzo[d]thiazol-5-yl)piperidin-1-yl)-2-oxoacetamide (Compound 1147)

Prepared by general procedure scheme H step 6A. Yield: 12.7 mg (6.26%).
HPLC conditions: Column: YMC Triart C18 100*20 mm, 5 microM; 0-1-6 min 60-60-85% water-MeOH+0.1% NH4OH, flow: 30 ml/min; (loading pump 4 ml/min MeOH).
$^1$H NMR (600 MHz, DMSO-$d_6$) δ (ppm) 1.02-1.14 (m, 6H), 1.30-1.39 (m, 1H), 1.67-1.73 (m, 1H), 1.82-2.15 (m, 5H), 2.17-2.32 (m, 4H), 2.39-2.43 (m, 2H), 2.67-2.98 (m, 4H), 3.06-3.21 (m, 2H), 3.46-4.11 (m, 2H), 5.25-5.73 (m, 3H), 7.31-7.41 (m, 1H), 7.43-7.53 (m, 1H), 7.82-7.92 (m, 1H), 7.97-8.10 (m, 2H), 10.49-10.63 (m, 1H).
LCMS(ESI): [M]+ m/z: calcd 532.2; found 533.2; Rt=2.075 min.

Example 650. The Synthesis of N-(6-amino-5-ethylpyridin-3-yl)-2-((2R,5S)-5-methyl-2-(2-(3-methyl-3-azabicyclo[3.1.1]heptan-1-yl)benzo[d]thiazol-5-yl)piperidin-1-yl)-2-oxoacetamide (Compound 1212)

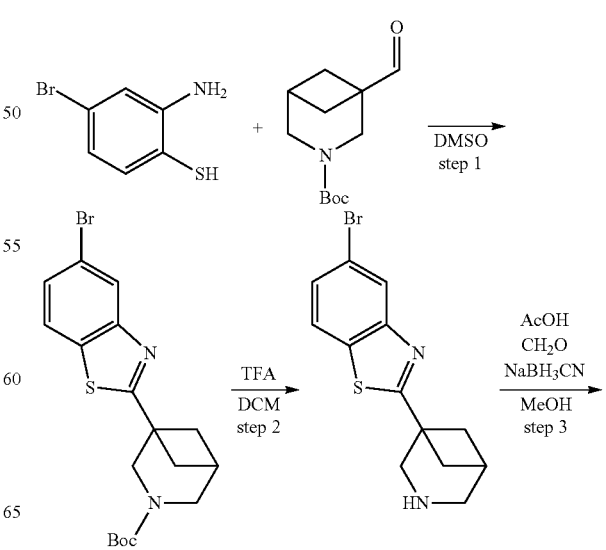

2759
-continued

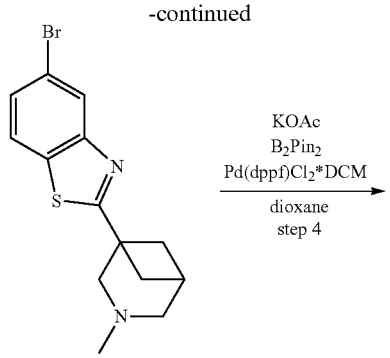

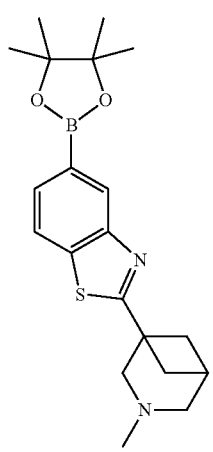

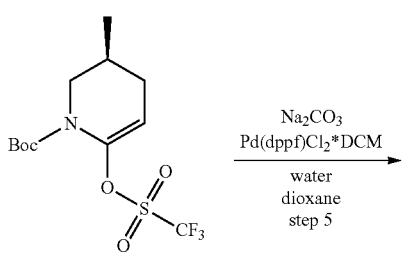

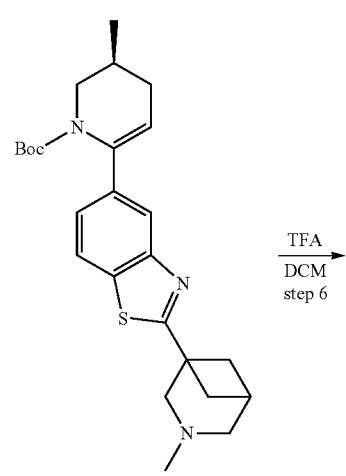

2760
-continued

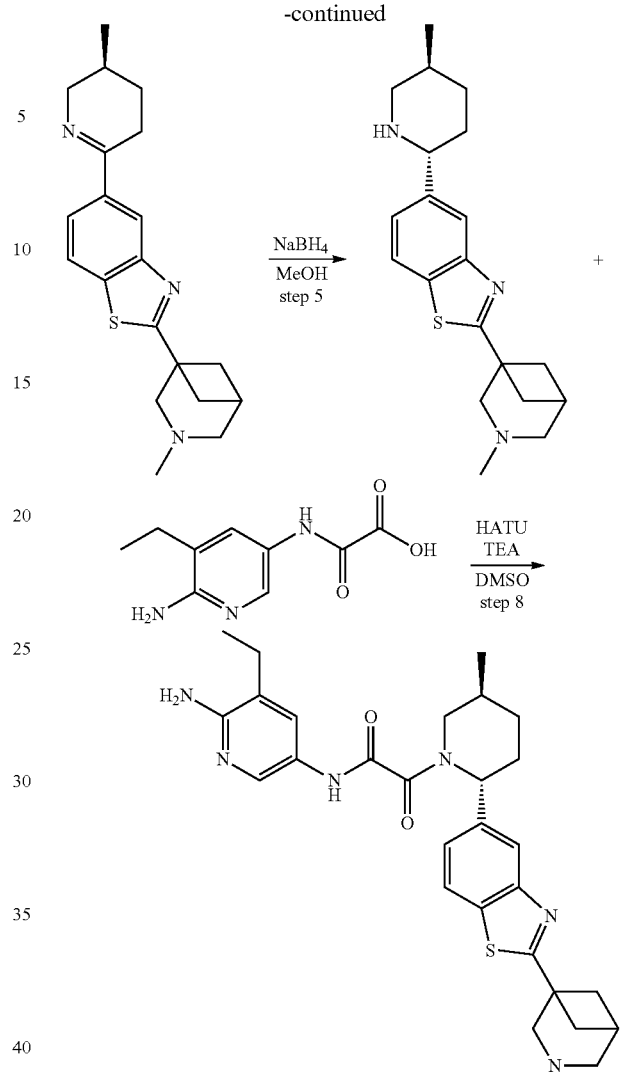

Step 1: Synthesis of tert-butyl 1-(5-bromobenzo[d]thiazol-2-yl)-3-azabicyclo[3.1.1]heptane-3-carboxylate Prepared by general procedure scheme H step 1B. Yield: 1.3 g of crude.

LCMS(ESI): [M–t-Bu]$^+$ m/z: calcd 353.2; found 354.2; Rt=1.756 min.

Step 2: Synthesis of 2-(3-azabicyclo[3.1.1]heptan-1-yl)-5-bromobenzo[d]thiazole tert-butyl 1-(5-bromo-1,3-benzothiazol-2-yl)-3-azabicyclo[3.1.1]heptane-3-carboxylate (1.3 g, 3.18 mmol) was dissolved in DCM (10 mL) and TFA (10 mL) was added. The mixture was stirred for 2 hr at 25° C. Then it was evaporated, dissolved in water and Na$_2$CO$_3$ was added. The mixture was extracted with DCM twice, the combined organic phase was dried over Na$_2$SO$_4$ and concentrated under reduced pressure to obtain 2-(3-azabicyclo[3.1.1]heptan-1-yl)-5-bromo-1,3-benzothiazole (930 mg, crude).

LCMS(ESI): [M]⁺ m/z: calcd 309.2; found 310.2; Rt=1.021 min.

Step 3: Synthesis of 5-bromo-2-(3-methyl-3-azabicyclo[3.1.1]heptan-1-yl)benzo[d]thiazole 2-(3-azabicyclo[3.1.1]heptan-1-yl)-5-bromo-1,3-benzothiazole (930 mg, 3.01 mmol) was dissolved in MeOH (30 mL) and acetic acid (361.22 mg, 6.02 mmol, 344.34 µL), 2-(3-azabicyclo[3.1.1]heptan-1-yl)-5-bromo-1,3-benzothiazole (930 mg, 3.01 mmol), sodium cyan borohydride (283.50 mg, 4.51 mmol) were added sequentially. The reaction was mixed at 25° C. for 12 hr. The reaction mixture was evaporated. Water was added and it was extracted with DCM twice. The combined organic phase was washed with brine, dried over Na₂SO₄ and concentrated under reduced pressure to obtain 5-bromo-2-(3-methyl-3-azabicyclo[3.1.1]heptan-1-yl)-1,3-benzothiazole (950 mg, crude).

LCMS(ESI): [M]⁺ m/z: calcd 323.2; found 324.2; Rt=0.835 min.

Step 4: Synthesis of 2-(3-methyl-3-azabicyclo[3.1.1]heptan-1-yl)-5-(4,4,5,5-tetramethyl-1,3,2-dioxaborolan-2-yl)benzo[d]thiazole Prepared by general procedure scheme H step 2. Yield: 1.8 g of crude.
LCMS(ESI): [M]⁺ m/z: calcd 370.2; found 371.2; Rt=1.041 min.

Step 5: Synthesis of (S)-tert-butyl 3-methyl-6-(2-(3-methyl-3-azabicyclo[3.1.1]heptan-1-yl)benzo[d]thiazol-5-yl)-3,4-dihydropyridine-1(2H)-carboxylate Prepared by general procedure scheme H step 3. Yield: 0.94 g of crude.
LCMS(ESI): [M]⁺ m/z: calcd 439.2; found 440.2; Rt=1.288 min.

Step 6: Synthesis of (S)-5-(5-methyl-3,4,5,6-tetrahydropyridin-2-yl)-2-(3-methyl-3-azabicyclo[3.1.1]heptan-1-yl)benzo[d]thiazole Prepared by general procedure scheme H step 4. Yield: 0.8 g of crude.
LCMS(ESI): [M]⁺ m/z: calcd 339.2; found 340.2; Rt=0.768 min.

Step 7: Synthesis of 2-(3-methyl-3-azabicyclo[3.1.1]heptan-1-yl)-5-((2R,5S)-5-methylpiperidin-2-yl)benzo[d]thiazole Prepared by general procedure scheme H step 5. Yield: 0.65 g (78.34%).

Step 8: Synthesis of N-(6-amino-5-ethylpyridin-3-yl)-2-((2R,5S)-5-methyl-2-(2-(3-methyl-3-azabicyclo[3.1.1]heptan-1-yl)benzo[d]thiazol-5-yl)piperidin-1-yl)-2-oxoacetamide (Compound 1212)

Prepared by general procedure scheme H step 6B. Yield: 19.7 mg (19.43%).
HPLC conditions: Column: SunFire C18 100*19 mm, 5 microM; 2-10 min 40-50% MeOH+NH₃, flow: 30 ml/min; (loading pump 4 ml/min MeOH).
¹H NMR (600 MHz, DMSO-d₆) δ (ppm) 0.98-1.05 (m, 3H), 1.05-1.15 (m, 3H), 1.29-1.41 (m, 1H), 1.62-1.76 (m, 1H), 1.82-1.93 (m, 1H), 1.96-2.00 (m, 2H), 2.04-2.23 (m, 1H), 2.25-2.36 (m, 4H), 2.38 (s, 3H), 2.40-2.43 (m, 2H), 2.75-2.78 (m, 0.3H), 2.79 (s, 2H), 3.02-3.12 (m, 2H), 3.24-3.27 (m, 0.7H), 3.47-4.05 (m, 1H), 5.25-5.61 (m, 1H), 5.61-5.74 (m, 2H), 7.33-7.43 (m, 1H), 7.42-7.54 (m, 1H), 7.86-7.93 (m, 1H), 7.97-8.11 (m, 2H), 10.56 (br s, 1H).

LCMS(ESI): [M]⁺ m/z: calcd 532.2; found 533.2; Rt=0.990 min.

Example 651. The Synthesis of N-(6-amino-5-ethylpyridin-3-yl)-2-((2R,5S)-5-methyl-2-(2-((3aR,5r,6aS)-2-methyloctahydrocyclopenta[c]pyrrol-5-yl)benzo[d]thiazol-5-yl)piperidin-1-yl)-2-oxoacetamide (Compound 1338)

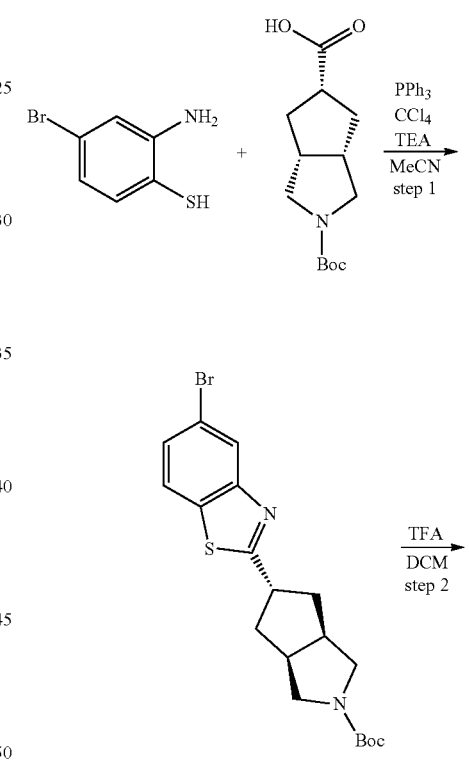

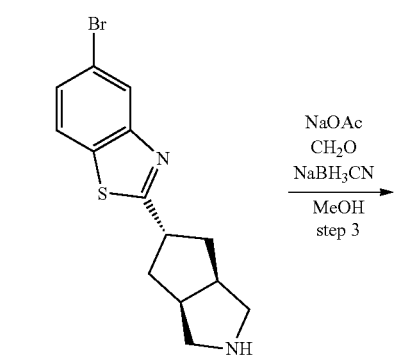

2763
-continued
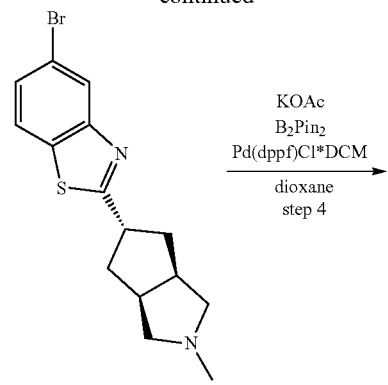
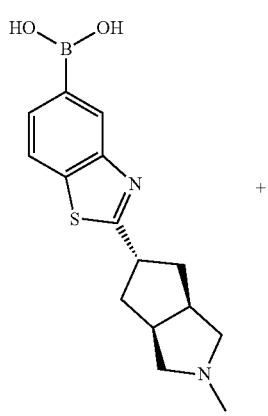
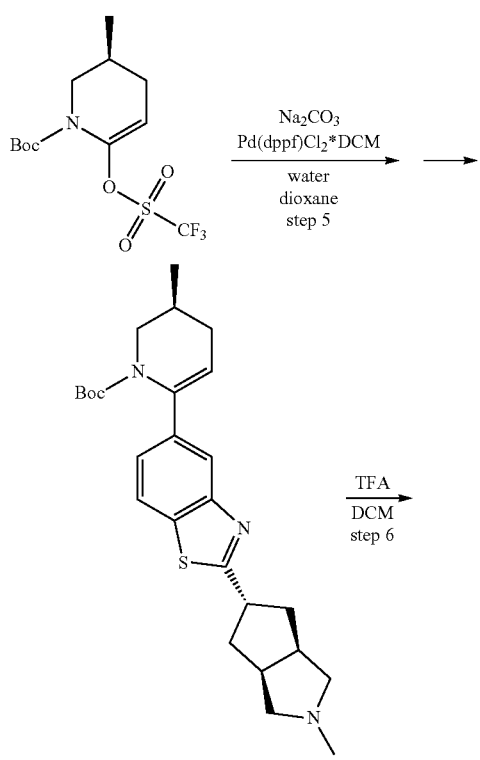
2764
-continued
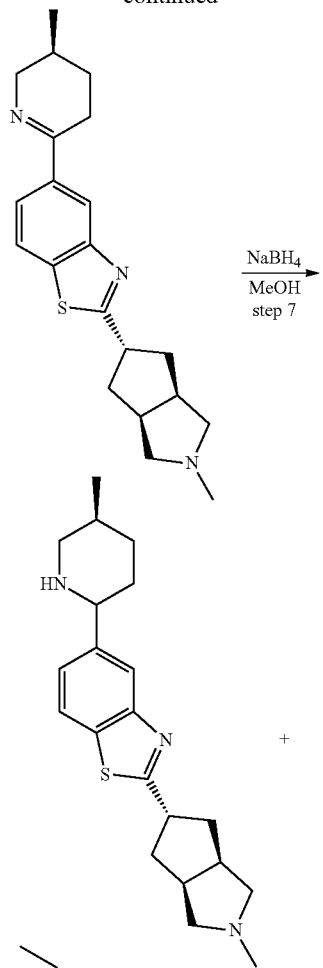
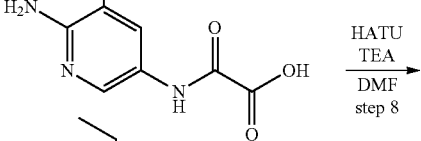
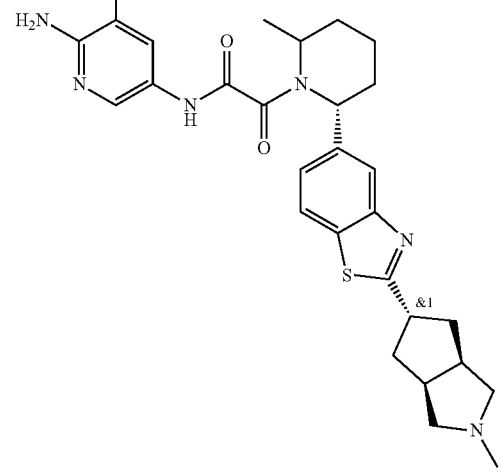
Compound 1338

Step 1: Synthesis of (3aR,5s,6aS)-tert-butyl 5-(5-bromobenzo[d]thiazol-2-yl)hexahydrocyclopenta[c]pyrrole-2(1H)-carboxylate Triphenylphosphine (6.17 g, 23.52 mmol) was added in one portion to the solution of (3aR,6aS)-2-tert-butoxycarbonyl-3,3a,4,5,6,6a-hexahydro-1H-cyclopenta[c]pyrrole-5-carboxylic acid (2.50 g, 9.80 mmol), 2-amino-4-bromobenzenethiol (2 g, 9.80 mmol), carbon tetrachloride (8.74 g, 56.84 mmol) and TEA (4.96 g, 49.00 mmol, 6.83 mL). Resulting reaction mixture was briefly warmed up to approximately 50-60° C. due to exothermic reaction. After that, it was stirred at 20° C. for 18 hr. Then, volatiles were removed under reduced pressure and residue was triturated with MTBE (100 ml). Resulting light precipitate was filtered off. Filtrate was concentrated under reduced pressure and residue was purified by gradient column chromatography (SiO$_2$, Hexane/MTBE), affording tert-butyl 5-(5-bromo-1,3-benzothiazol-2-yl)-3,3a,4,5,6,6a-hexahydro-1H-cyclopenta[c]pyrrole-2-carboxylate (1.55 g, 3.66 mmol, 37.36% yield).

LCMS(ESI): [M–t-Bu]$^+$ m/z: calcd 367.2; found 368.2; Rt=1.737 min.

Step 2: Synthesis of 5-bromo-2-((3aR,5s,6aS)-octahydrocyclopenta[c]Pyrrol-5-yl)benzo[d]thiazole TFA (4.17 g, 36.61 mmol, 2.82 mL) was added to the solution of tert-butyl 5-(5-bromo-1,3-benzothiazol-2-yl)-3,3a,4,5,6,6a-hexahydro-1H-cyclopenta[c]pyrrole-2-carboxylate (1.55 g, 3.66 mmol) in DCM (7.18 mL). Resulting mixture was stirred at 20° C. for 5 hr. Then, it was concentrated under reduced pressure, leaving 5-bromo-2-[(3aR,6aS)-1,2,3,3a,4,5,6,6a-octahydrocyclopenta[c]pyrrol-5-yl]-1,3-benzothiazole (1.2 g, 2.75 mmol, 75.13% yield, TFA).

LCMS(ESI): [M]$^+$ m/z: calcd 324.2; found 325.2; Rt=0.999 min.

Step 3: Synthesis of 5-bromo-2-((3aR,5s,6aS)-2-methyloctahydrocyclopenta[c]Pyrrol-5-yl)benzo[d]thiazole Formaldehyde, 37% w/w aq. soln., stab. with 7-8% MeOH (222.93 mg, 7.42 mmol, 205.85 µL) and sodium acetate (609.07 mg, 7.42 mmol, 398.60 µL) were added to the solution of 5-bromo-2-[(3aR,6aS)-1,2,3,3a,4,5,6,6a-octahydrocyclopenta[c]pyrrol-5-yl]-1,3-benzothiazole (1.2 g, 3.71 mmol) in MeOH (19.40 mL). Resulting mixture was stirred at 20° C. for 1 hr before sodium cyan borohydride (466.58 mg, 7.42 mmol) was added thereto. After that, stirring was continued for 16 hr. Then, solvent was removed under reduced pressure and residue was partitioned between 15% aq. K$_2$CO$_3$ solution (30 ml) and DCM (50 ml). Organic layer was separated, dried over solid K$_2$CO$_3$ and concentrated under reduced pressure, leaving 5-bromo-2-[(3aR,6aS)-2-methyl-3,3a,4,5,6,6a-hexahydro-1H-cyclopenta[c]pyrrol-5-yl]-1,3-benzothiazole (1.2 g, 3.56 mmol, 95.84% yield).

LCMS(ESI): [M]$^+$ m/z: calcd 337.2; found 338.2; Rt=0.918 min.

Step 4: Synthesis of (2-((3aR,5s,6aS)-2-methyloctahydrocyclopenta[c]Pyrrol-5-yl)benzo[d]thiazol-5-yl) boronic acid Prepared by general procedure scheme H step 2. Yield: 0.5 g of crude.

LCMS(ESI): [M]$^+$ m/z: calcd 302.2; found 303.2; Rt=0.618 min.

Step 5: Synthesis of (S)-tert-butyl 3-methyl-6-(2-((3aR,5s,6aS)-2-methyloctahydrocyclopenta[c]Pyrrol-5-yl)benzo[d]thiazol-5-yl)-3,4-dihydropyridine-1(2H)-carboxylate (Compound 1338

Prepared by general procedure scheme H step 3. Yield: 0.7 g of crude.

LCMS(ESI): [M]$^+$ m/z: calcd 453.2; found 454.2; Rt=1.152 min.

Step 6: Synthesis of 5-((S)-5-methyl-3,4,5,6-tetrahydropyridin-2-yl)-2-((3aR,5s,6aS)-2-methyloctahydrocyclopenta[c]Pyrrol-5-yl)benzo[d]thiazole Prepared by general procedure scheme H step 4. Yield: 0.5 g of crude.

LCMS(ESI): [M]$^+$ m/z: calcd 353.2; found 354.2; Rt=0.603 min.

Step 7: Synthesis of 2-((3aR,5s,6aS)-2-methyloctahydrocyclopenta[c]Pyrrol-5-yl)-5-((2R,5S)-5-methylpiperidin-2-yl)benzo[d]thiazole Prepared by general procedure scheme H step 5. Yield: 0.3 g of crude.

LCMS(ESI): [M]$^+$ m/z: calcd 355.2; found 356.2; Rt=0.710 min.

Step 8: Synthesis of N-(6-amino-5-ethylpyridin-3-yl)-2-((2R,5S)-5-methyl-2-(2-((3aR,5r,6aS)-2-methyloctahydrocyclopenta[c]Pyrrol-5-yl)benzo[d]thiazol-5-yl)piperidin-1-yl)-2-oxoacetamide (Compound 1338

Prepared by general procedure scheme H step 6B. Yield: 7.4 mg (2.61%).

HPLC conditions: Column: SunFire C18 100*19 mm, 5 microM; 0-5 min 50-100% water-MeCN+FA, flow: 30 ml/min; (loading pump 4 ml/min MeOH).

$^1$H NMR (600 MHz, DMSO-d$_6$) δ (ppm) 1.00-1.05 (m, 3H), 1.06-1.14 (m, 3H), 1.27-1.40 (m, 1H), 1.58-1.76 (m, 3H), 1.79-2.05 (m, 3H), 2.07-2.13 (m, 2H), 2.19-2.23 (m, 3H), 2.25-2.36 (m, 3H), 2.38-2.43 (m, 3H), 2.60-2.75 (m, 3H), 2.76-2.89 (m, 1H), 3.71-4.05 (m, 1H), 5.25-5.71 (m, 3H), 7.30-7.42 (m, 1H), 7.42-7.55 (m, 1H), 7.80-7.92 (m, 1H), 7.97-8.08 (m, 2H), 10.49-10.59 (m, 1H).

LCMS(ESI): [M+1]$^+$ m/z: calcd 546.2; found 547.2; Rt=2.250 min.

Example 652. The Synthesis of 2-methoxy-5-(2-((2R,5S)-5-methyl-2-(2-((S)-1-methylpiperidin-3-yl)benzo[d]thiazol-5-yl)piperidin-1-yl)-2-oxoacetamido)nicotinamide (Compound 1359)

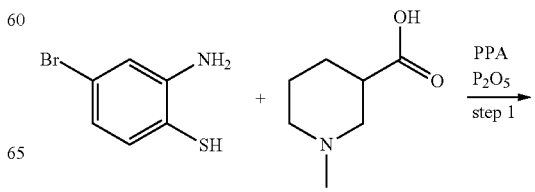

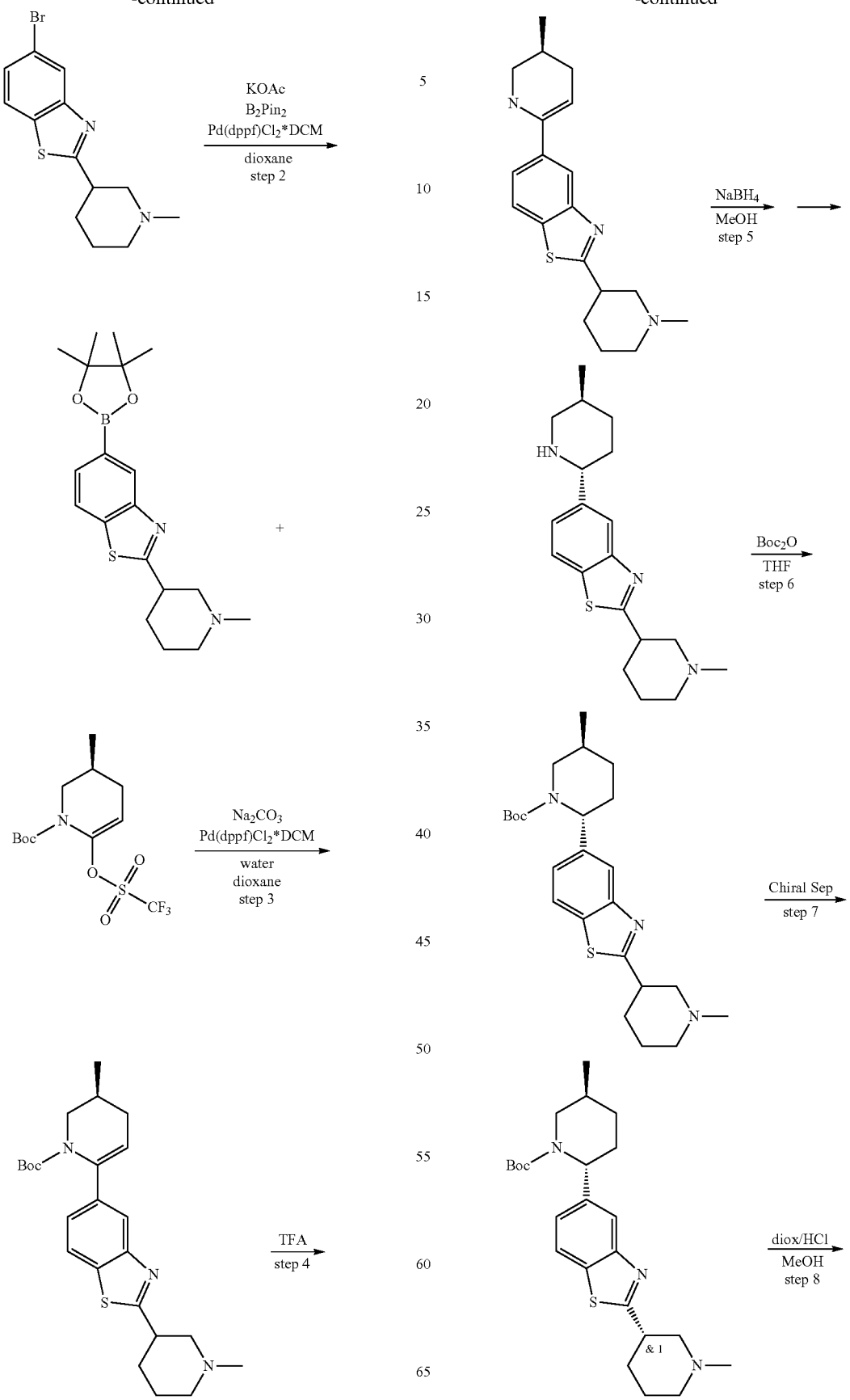

-continued

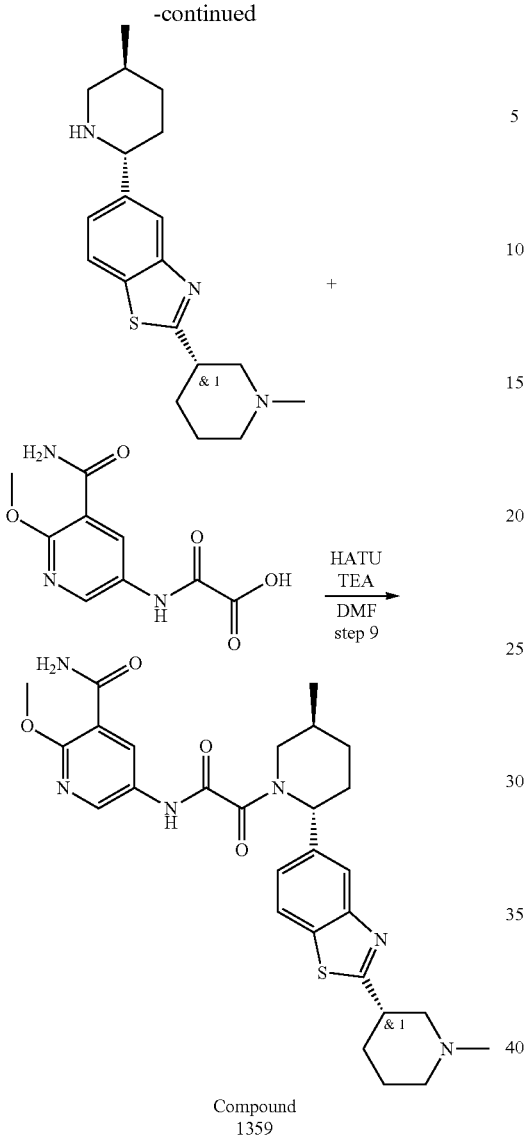

Compound 1359

Step 1: Synthesis of 5-bromo-2-(1-methylpiperidin-3-yl)benzo[d]thiazole

Prepared by general procedure scheme H step 1A. Yield: 4.3 g (93.99%).
LCMS(ESI): [M]+ m/z: calcd 311.2; found 312.2; Rt=0.990 min.

Step 2: Synthesis of 2-(1-methylpiperidin-3-yl)-5-(4,4,5,5-tetramethyl-1,3,2-dioxaborolan-2-yl)benzo[d]thiazole Prepared by general procedure scheme H step 2. Yield: 4.9 g of crude.
LCMS(ESI): [M]+ m/z: calcd 358.2; found 359.2; Rt=0.965 min.

Step 3: Synthesis of (3S)-tert-butyl 3-methyl-6-(2-(1-methylpiperidin-3-yl)benzo[d]thiazol-5-yl)-3,4-dihydropyridine-1(2H)-carboxylate Prepared by general procedure scheme H step 3. Yield: 5.8 g of crude.

LCMS(ESI): [M]+ m/z: calcd 427.2; found 428.2; Rt=1.150 min.

Step 4: Synthesis of 5-((S)-5-methyl-3,4,5,6-tetrahydropyridin-2-yl)-2-(1-methylpiperidin-3-yl)benzo[d]thiazole Prepared by general procedure scheme H step 4. Yield: 3 g of crude.
LCMS(ESI): [M]+ m/z: calcd 327.2; found 328.2; Rt=0.656 min.

Step 5: Synthesis of 5-((2R,5S)-5-methylpiperidin-2-yl)-2-(1-methylpiperidin-3-yl)benzo[d]thiazole Prepared by general procedure scheme H step 5. Yield: 1.8 g (59.63%).
LCMS(ESI): [M]+ m/z: calcd 329.2; found 330.2; Rt=0.491 min.

Step 6: Synthesis of (2R,5S)-tert-butyl 5-methyl-2-(2-(1-methylpiperidin-3-yl)benzo[d]thiazol-5-yl)piperidine-1-carboxylate To a solution of 2-(1-methyl-3-piperidyl)-5-[(2R,5S)-5-methyl-2-piperidyl]-1,3-benzothiazole (1.5 g, 4.55 mmol) in THF (4 mL), di-tert-butyl dicarbonate (993.53 mg, 4.55 mmol, 1.04 mL) was added. The resulting mixture was stirred at 25° C. for 3 hr and purified by HPLC (Device (Mobile Phase, Column): SYSTEM 55-95% 0-5 min H2O/MeCN/0.1% NH4OH, flow: 30 ml/min (loading pump 4 ml/min MeCN) target mass 429 column: XBridge BEH C18 5 um 130A) to obtain tert-butyl (2R,5S)-5-methyl-2-[2-(1-methyl-3-piperidyl)-1,3-benzothiazol-5-yl]piperidine-1-carboxylate (0.99 g, 2.30 mmol, 50.62% yield).
LCMS(ESI): [M]+ m/z: calcd 429.2; found 430.2; Rt=3.390 min.

Step 7: Chiral Separation

Racemic tert-butyl (2R,5S)-5-methyl-2-[2-(1-methyl-3-piperidyl)-1,3-benzothiazol-5-yl]piperidine-1-carboxylate (0.99 g, 2.30 mmol) was chiral separated (Column: Chiralpak AD-H-III (250*20 mm, 5 mkm), Hexane—IPA-MeOH, 80-10-10, 12 ml/min) to obtain tert-butyl (2R,5S)-5-methyl-2-[2-[(3S)-1-methyl-3-piperidyl]-1,3-benzothiazol-5-yl]piperidine-1-carboxylate (384 mg, 893.82 µmol, 77.58% yield).
Rel Time for this isomer in analytical conditions (column: AD-H, Hexane-IPA-MeOH, 80-10-10, 0.8 ml/min as mobile phase) 11.83 min.
LCMS(ESI): [M]+ m/z: calcd 429.2; found 430.2; Rt=1.099 min.

Step 8: Synthesis of 5-((2R,5S)-5-methylpiperidin-2-yl)-2-((S)-1-methylpiperidin-3-yl)benzo[d]thiazole A solution of tert-butyl (2R,5S)-5-methyl-2-[2-[(3S)-1-methyl-3-piperidyl]-1,3-benzothiazol-5-yl]piperidine-1-carboxylate (384 mg, 893.82 µmol) in MeOH (4 mL) and hydrogen chloride solution 4.0 M in dioxane (325.89 mg, 8.94 mmol, 407.37 µL) was stirred at 25° C. for 3 hr. The solvent was evaporated to give 5-[(2R,5S)-5-methyl-2-piperidyl]-2-[(3S)-1-methyl-3-piperidyl]-1,3-benzothiazole (392 mg, 893.17 µmol, 99.93% yield, 3HCl).

Step 9: Synthesis of 2-methoxy-5-(2-((2R,5S)-5-methyl-2-((S)-1-methylpiperidin-3-yl)benzo[d]thiazol-5-yl)piperidin-1-yl)-2-oxoacetamido)nicotinamide (Compound 1359

Prepared by general procedure scheme H step 6A. Yield: 77 mg (62.62%).

HPLC conditions: Column:XBridge C18 100*20 mm, 5 microM; 0-1-6 min 40-40-90% water-MeOH+0.1% NH$_4$OH, flow: 30 ml/min; (loading pump 4 ml/min MeOH).

$^1$H NMR (DMSO-d$_6$, 500 MHz): δ (ppm) 1.04 (m, 3H), 1.36 (m, 1H), 1.59 (m, 2H), 1.71 (m, 2H), 1.88 (m, 1H), 2.06 (m, 3H), 2.21 (s, 3H), 2.29 (m, 2H), 2.63 (m, 2H), 2.93 (m, 2H), 3.79 (m, 4H), 5.49 (d, 1H), 7.38 (dd, 1H), 7.72 (m, 2H), 7.88 (m, 1H), 8.05 (dd, 1H), 8.55 (m, 2H), 11.04 (s, 1H)

LCMS(ESI): [M]$^+$ m/z: calcd 550.2; found 551.2; Rt=2.550 min.

Scheme I Synthesis of Compounds of Formula 9

Compounds of Formula 9 are are compounds of Formula (I) wherein R$^1$, R$^2$, R$^3$, R$^4$, R$^6$ R$^7$, and R$^8$ are as described herein.

General Procedure 9

Scheme I

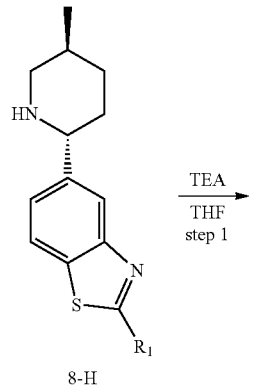

8-H

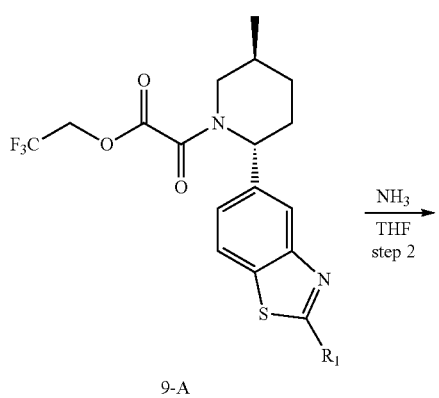

9-A

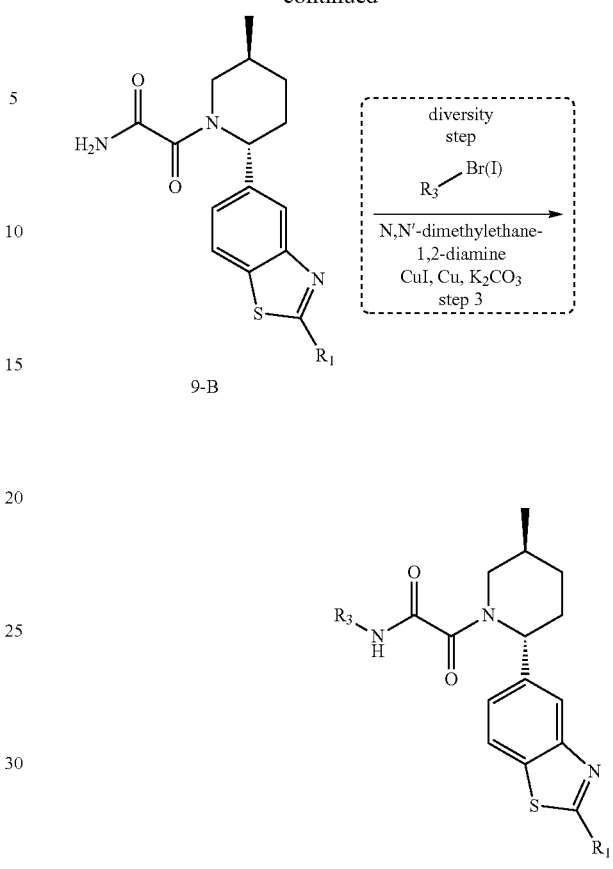

9-B

Formula 9

Step 1: Synthesis of 9-A

8-H was described in scheme H.

8-H (1 eq) and TEA (1.1 eq) were dissolved in THF and cooled to 0° C., following by the dropwise addition of 2,2,2-trifluoroethyl 2-chloro-2-oxo-acetate (1.1 eq) under Ar and the reaction mixture was stirred for 12 hr at rt and evaporated under reduced pressure to give 9-A which was used in the next step without further purification.

Step 2: Synthesis of 9-B

To a solution of 9-A (1 eq) in THF (10 mL), ammonia (1 eq) was bubbled through for 10 min at 0° C. The reaction mixture was then stirred for 18 hr at rt. The reaction mixture was filtered off and the filtrate was evaporated in vacuum to give 9-B which was used in the next step without further purification.

Step 3A: Synthesis of Formula 9

9-B (1 eq), R$_3$Br (1.1 eq), Cu (1 eq), CuI (1 eq), K$_2$CO$_3$ (2 eq) and N,N-dimethylcyclohexane-1,2-diamine (1.5 eq) were mixed in dioxane under argon, and then stirred overnight at 95° C. for 24 hr in vial. The residue was purified by HPLC to obtain pure product (Formula 9).

Example 653. The Synthesis of N-(6-amino-5-(oxetan-3-yl)pyridin-3-yl)-2-((2R,5S)-5-methyl-2-(2-(1-methylpiperidin-4-yl)benzo[d]thiazol-5-yl)piperidin-1-yl)-2-oxoacetamide (Compound 1334)

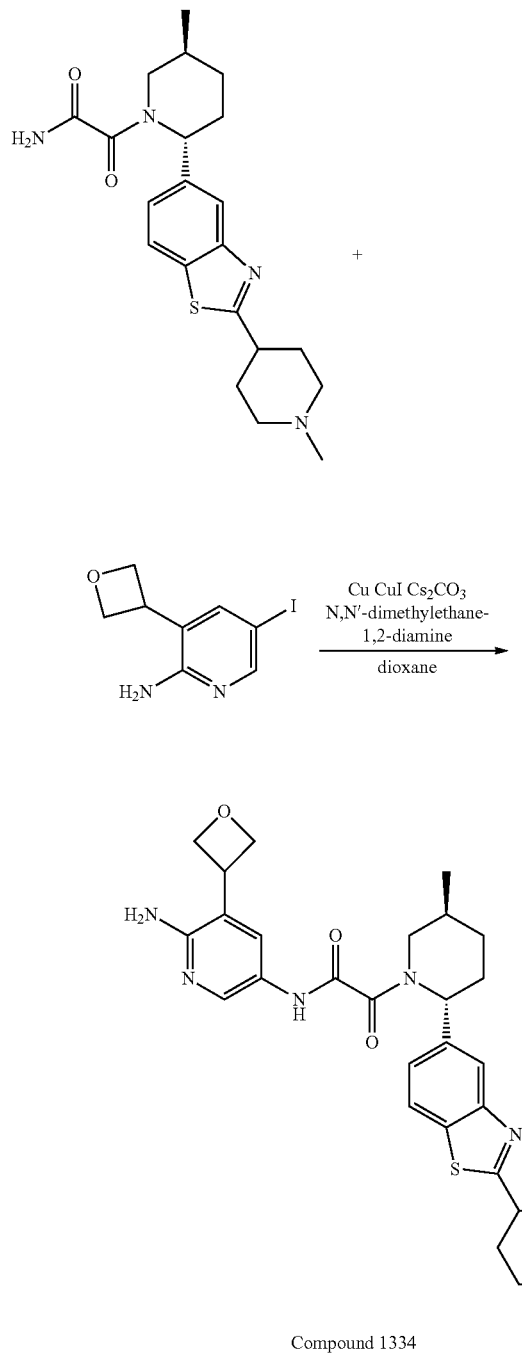

Compound 1334

Prepared by general procedure scheme 9 step 3A. Yield: 67.6 mg (30.46%).

HPLC conditions: Column: XBridge C18 100*19 mm, 5 microM; 0-6 min 15-35% water-MeCN+0.1% NH$_4$OH; (loading pump 4 ml/min MeCN).

rac-Compound 1334:

$^1$H NMR (600 MHz, DMSO-d$_6$) δ (ppm) 1.03-1.05 (d, 3H), 1.32-1.40 (m, 1H), 1.70-1.90 (m, 4H), 2.01-2.07 (m, 4H), 2.18 (s, 3H), 2.29-2.31 (m, 1H), 2.82-3.07 (m, 3H), 3.51-4.24 (m, 4H), 4.47-4.54 (m, 2H), 4.88-4.95 (m, 2H), 5.31-5.70 (m, 3H), 7.34-7.42 (m, 1H), 7.68-7.90 (m, 2H), 8.03-8.14 (m, 2H), 10.61-10.67 (d, 1H).

LCMS(ESI): [M]$^+$ m/z: calcd 548.2; found 549.2; Rt=1.834 min. N-[6-amino-5-(oxetan-3-yl)-3-pyridyl]-2-[(2R,5S)-5-methyl-2-[2-(1-methyl-4-piperidyl)-1,3-benzothiazol-5-yl]-1-piperidyl]-2-oxo-acetamide was purified by chiral HPLC: (Column: Chiralpak AS-H (250×20 mm, 5 mkm); Mobile phase: Hexane-IPA-MeOH, 60-20-20; Flow Rate: 13 mL/min) to obtain N-[6-amino-5-(oxetan-3-yl)-3-pyridyl]-2-[(2R,5S)-5-methyl-2-[2-(1-methyl-4-piperidyl)-1,3-benzothiazol-5-yl]-1-piperidyl]-2-oxo-acetamide (52 mg, 94.77 μmol, 22.33% yield) (RT=11.43 min).

Rel Time for Compound 1334 in analytical conditions (column: AS-H, Hexane-IPA-MeOH, 50-25-25, 0.6 ml/min as mobile phase) 10.48 min.

Compound 1334:

Retention time: 10.48 min $^1$H NMR (600 MHz, DMSO-d$_6$) δ (ppm) 1.02-1.04 (m, 3H), 1.34-1.39 (m, 1H), 1.70 (m, 1H), 1.79-1.86 (m, 3H), 2.03-2.07 (m, 4H), 2.18 (s, 3H), 2.29-2.37 (m, 1H), 2.60 (m, 1H), 2.82-2.84 (m, 2H), 3.05 (m, 1H), 3.51-3.53 (m, 1H), 4.04-4.23 (m, 2H), 4.48-4.54 (m, 2H), 4.88-4.93 (m, 2H), 5.31-5.70 (m, 3H), 7.34-7.42 (m, 1H), 7.68-7.76 (d, 1H), 7.87-7.90 (d, 1H), 8.03-8.07 (m, 1H), 8.14 (s, 1H), 10.60-10.67 (m, 1H).

LCMS(ESI): [M]$^+$ m/z: calcd 548.2; found 549.2; Rt=1.806 min.

Example 654. The Synthesis of N-(6-amino-5-(oxetan-3-yl)pyridin-3-yl)-2-((2R,5S)-5-methyl-2-(2-(2-(pyrrolidin-1-yl)ethyl)benzo[d]thiazol-5-yl)piperidin-1-yl)-2-oxoacetamide (Compound 1379)

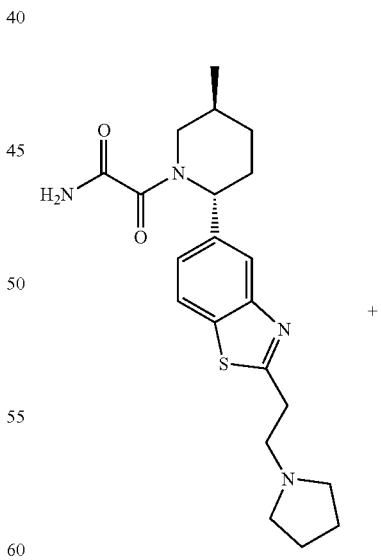

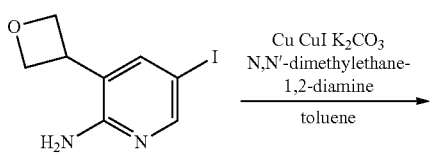

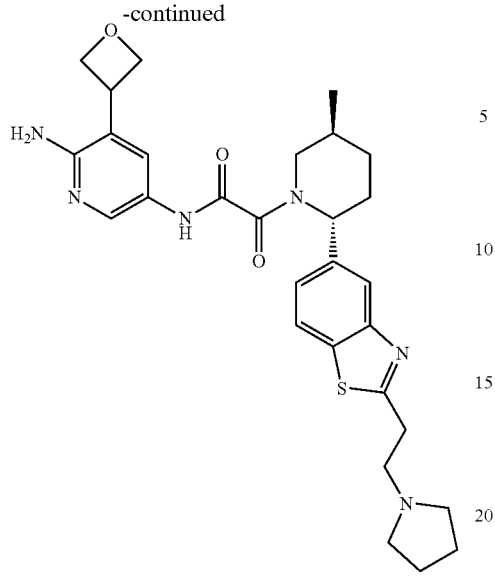

Compound 1379

Prepared by general procedure scheme 9 step 3A. Yield: 15.9 mg (7.25%).

HPLC conditions: Column: YMC Triart C18 100*20 mm, 5 microM; 0-1-6 min 10-10-65% water-MeCN+0.1% NH$_4$OH; (loading pump 4 ml/min MeCN).

$^1$H NMR (600 MHz, DMSO-d$_6$) δ (ppm) 0.94-1.14 (m, 3H), 1.30-1.48 (m, 1H), 1.66-1.69 (m, 3H), 1.69-1.76 (m, 2H), 1.83-1.95 (m, 1H), 2.02-2.29 (m, 1H), 2.29-2.37 (m, 1H), 2.44-2.47 (m, 2H), 2.53-2.58 (m, 2H), 2.77-2.82 (m, 0.3H), 2.83-2.88 (m, 2H), 3.21-3.26 (m, 2H), 3.26-3.28 (m, 0.7H), 3.41-4.07 (m, 1H), 4.13-4.29 (m, 1H), 4.43-4.59 (m, 2H), 4.87-4.99 (m, 2H), 5.25-5.61 (m, 1H), 5.61-5.75 (m, 2H), 7.30-7.45 (m, 1H), 7.65-7.80 (m, 1H), 7.82-7.93 (m, 1H), 7.99-8.06 (m, 1H), 8.06-8.19 (m, 1H), 10.54-10.77 (m, 1H).

LCMS(ESI): [M]$^+$ m/z: calcd 548.2; found 549.2; Rt=2.110 min.

Example 655. The Synthesis of N-(6-amino-5-methoxypyridin-3-yl)-2-((2R,5)-5-methyl-2-(2-(1-methylpiperidin-4-yl)benzo[d]thiazol-5-yl)piperidin-1-yl)-2-oxoacetamide (Compound 1203)

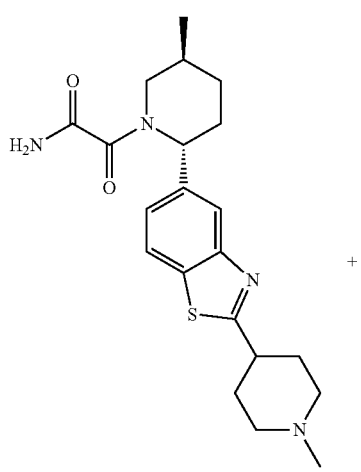

+

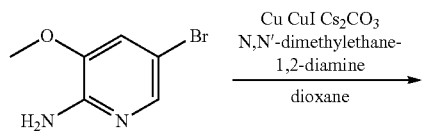

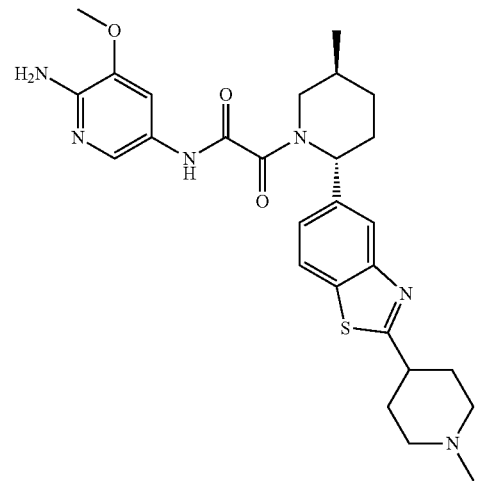

Prepared by general procedure scheme 9 step 3A. Yield: 55 mg (42.15%).

$^1$H NMR (500 MHz, DMSO-d$_6$) δ (ppm) 1.01-1.06 (m, 3H), 1.31-1.42 (m, 1H), 1.65-1.74 (m, 1H), 1.78-1.93 (m, 3H), 1.99-2.11 (m, 5H), 2.18 (s, 3H), 2.24-2.36 (m, 1H), 2.83 (d, 2H), 3.00-3.28 (m, 2H), 3.49-4.06 (m, 4H), 5.27-5.72 (m, 3H), 7.28-7.44 (m, 2H), 7.72-7.83 (m, 1H), 7.85-7.92 (m, 1H), 8.02-8.08 (m, 1H), 10.48-10.70 (m, 1H).

LCMS(ESI): [M]$^+$ m/z: calcd 522.2; found 523.2; Rt=2.451 min.

The initial lot was purified on chiral HPLC using the following conditions:

Column: Chiralpak IC-III (250*20 mm, 5 mkm); Mobile phase: MeOH-IPA 50-50 Flow Rate: 11 mL/min, RT=45.776 min.

Compound 1203:

$^1$H NMR (500 MHz, DMSO-d$_6$) δ (ppm) 1.02-1.05 (m, 3H), 1.32-1.40 (m, 2H), 1.69-1.88 (m, 4H), 2.01-2.07 (m, 4H), 2.18 (s, 3H), 2.29-2.37 (m, 1H), 2.82-2.84 (m, 2H), 3.03-3.07 (m, 1H), 3.49-4.05 (m, 5H), 5.30-5.70 (m, 3H), 7.31-7.42 (m, 2H), 7.74-7.91 (m, 2H), 8.04-8.07 (m, 1H), 10.59-10.56 (d, 1H).

LCMS(ESI): [M]$^+$ m/z: calcd 522.2; found 523.2; Rt=1.852 min.

Scheme J—Synthesis of Compounds of Formula 10

Compounds of Formula 10 are are compounds of Formula (I) wherein R$^1$, R$^2$, R$^3$, R$^4$, R$^6$ R$^7$, and R$^8$ are as described herein.

General Procedure 10
Scheme J
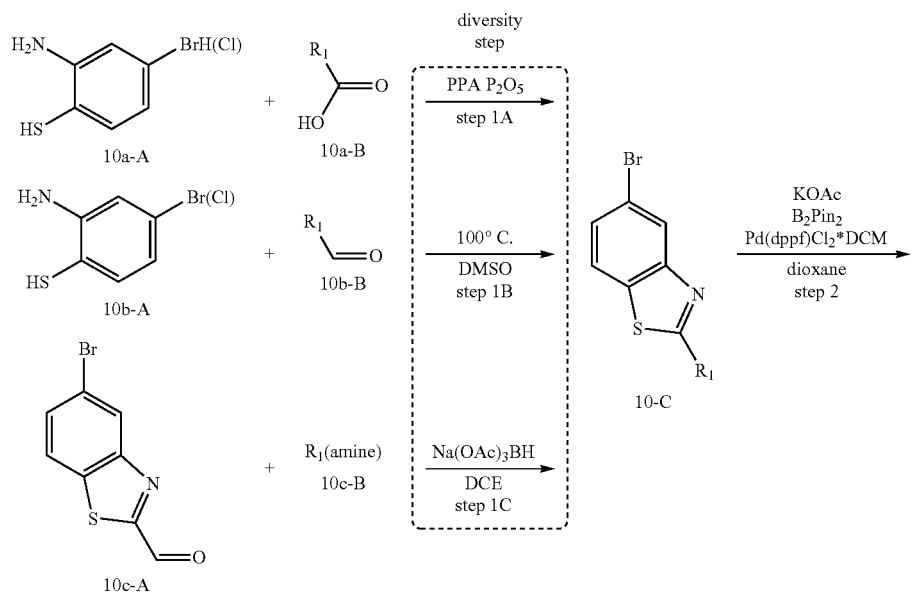
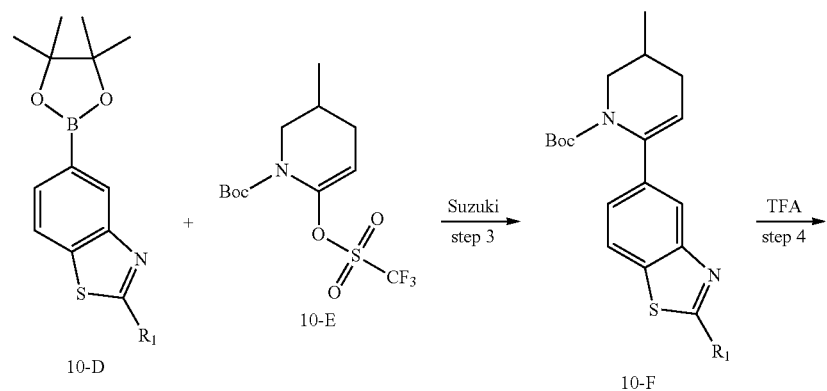
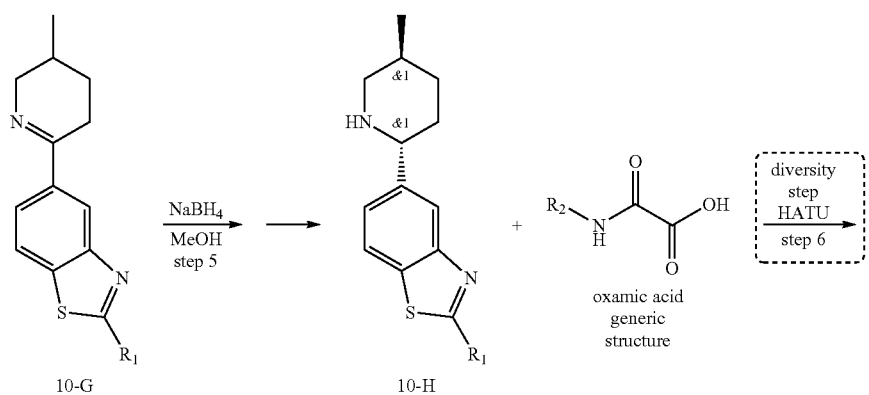

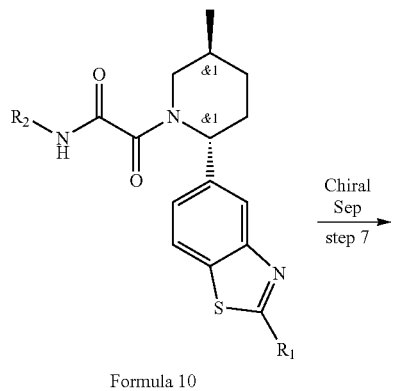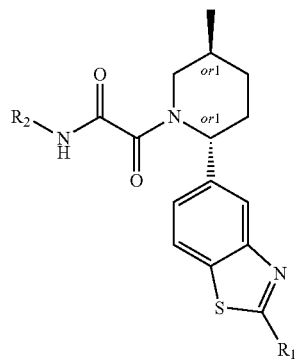

Formula 10    Formula 10-1    Formula 10-2

Step 1A: Synthesis of 10-C

Phosphoric acid (4 eq) and phosphorus pentoxide (4 eq) were mixed together. The reaction suspension was stirred at rt for 10 min, then 10a-A (1 eq) followed by 10a-B (1.2 eq) were added under Ar. The solution was stirred at 110° C. for 18 hr then it was triturated with water, basidified (NaOH, 10% aq.) to pH=10, extracted with DCM twice, dried and evaporated in vacuum to give 10-C.

Step 1B: Synthesis of 10-C

To the stirred solution of 10b-A (1 eq) in DMSO 4.1b-B (1 eq) was added. The resulting mixture was stirred at 100° C. for 14 hr. The reaction mixture was poured into cold water and extracted with MTBE twice. Combined organic layers were washed with water and brine, dried over $Na_2SO_4$. MTBE was evaporated in vacuum to give 10-C.

Step 1C: Synthesis of 10-C

To the stirred solution of 10c-A (1 eq) in the 1,2-dichloroethane 10c-B (2 eq) was added and allowed to stir at 25° C. for 2 hr, sodium (trisacetoxy) borohydride (2 eq) was added. The reaction mixture was stirred at 25° C. for 16 hr. After completion, the reaction mixture was evaporated, quenched with water and neutralized by $K_2CO_3$ to pH=10. The aqueous phase was extracted with $CHCl_3$ twice. The combined organic phase was dried over $Na_2SO_4$ and evaporated under reduced pressure to afford 10-C. (TEA 1.5 eq per each acid eq, if amine salt used, was added to the solution of respective amine)

Step 2: Synthesis of 10-D

10-C(1 eq), $B_2Pin_2$ (1.1 eq) and KOAc (2 eq) were mixed in dioxane. The resulting mixture was evacuated and then backfilled with argon, this operation was repeated three times, then Pd(dppf)$Cl_2$*DCM (0.05 eq) was added under argon. The reaction mixture was stirred under argon at 90° C. for 14 hr, then cooled and filtered. The filter cake was washed with dioxane twice.
The solvent was evaporated to afford 10-D.

Step 3: Synthesis of 10-F

10-D (1 eq), tert-butyl 3-methyl-6-(trifluoromethylsulfonyloxy)-3,4-dihydro-2H-pyridine-1-carboxylate (1.2 eq), sodium carbonate (3 eq) were mixed together in dioxane-water mixture (3:1). The resulting mixture was evacuated and then backfilled with argon. This operation was repeated two times, then Pd(dppf)$Cl_2$*DCM (819.86 mg, 1.00 mmol) was added and the reaction mixture was stirred under argon at 90° C. overnight, then cooled down and concentrated in vacuum. The residue was diluted with MTBE and stirred for 0.5 hr. After the most of the residue had dissolved, anhydrous sodium sulphate was added, and the resulting mixture was filtered. The filter cake was additionally washed with MTBE (5*50 ml) and discarded. The filtrate was concentrated in vacuum to afford 10-F.

Step 4: Synthesis of 10-G

A solution of 10-F (1 eq) in TFA (15 eq) was stirred at rt for 1 hr, and then concentrated in vacuum. Cold water was added to the residue, and the resulting mixture was extracted with DCM twice. The DCM layer was discarded, and the aqueous layer was basified to pH 11. The resulting mixture was extracted with DCM twice. The combined organic extracts were dried over sodium sulphate and concentrated in vacuum to afford 10-G.

Step 5: Synthesis of 10-H

10-G (1 eq) was dissolved in MeOH and the resulting solution was cooled to 0° C. in an ice bath. Sodium borohydride (2 eq) was added portion wise to the previous solution. After addition completed, the reaction mixture was allowed to warm to rt and stirred overnight. Water was added to the reaction mixture and the resulting mixture was concentrated in vacuum. The residue was diluted with water and the resulting mixture was extracted with DCM twice, dried over $Na_2SO_4$, filtered and evaporated to obtain 10-H.

Step 6A: Synthesis of Formula 10

10-H (1 eq), oxamic acid (1 eq) and TEA (2.5 eq+1.0 eq per each acid eq, if amine salt used) were mixed together in DMF. HATU (1.5 eq) was added thereto and the resulting mixture was stirred overnight. The reaction mixture was concentrated in vacuum and the residue was purified by HPLC to obtain Formula 10.

Step 6B: Synthesis of Formula 10

DIPEA (2.5 eq+1.0 eq per each acid eq, if amine salt used) was added to the solution of respective amine or it salt (10-H) (1 eq) and oxamic acid (1 eq) in DMF. The resulting mixture was stirred for 5 min followed by the addition of the solution of HATU (1.1 eq) in DMF. Then, the reaction mixture was stirred overnight at rt. After the completion of the reaction, monitored by LCMS, the resulting suspension was concentrated under reduced pressure. The obtained filtrate was subjected to HPLC (Waters SunFire C18 19*100 5 mkm column and H$_2$O-MeOH as a mobile phase) to afford pure product (Formula 10).

Example 656. rac-2-(2-methoxyethyl)-5-((2R,5S)-5-methylpiperidin-2-yl)benzo[d]thiazole

Step 1: Synthesis of 5-bromo-2-(2-methoxyethyl)benzo[d]thiazole

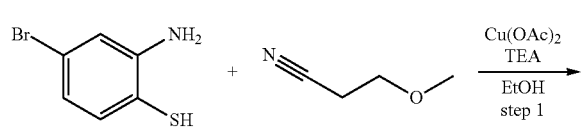

2-amino-4-bromo-benzenethiol (5.5 g, 26.95 mmol, 170.94 uL), 3-methoxypropanenitrile (3.44 g, 40.42 mmol, 3.67 mL), copper(II) acetate (489.49 mg, 2.69 mmol), TEA (2.73 g, 26.95 mmol, 3.76 mL) were dissolved in EtOH (100 mL). The mixture was stirred at 70° C. (oil bath temperature) for 13 hr. After the reaction was finished (monitored by LCMS), the mixture was cooled to rt and quenched with aqueous Na$_2$CO$_3$, and the crude product was extracted with EtOAc. The organic extracts were concentrated in vacuum, and the resulting residue was purified by column chromatography on silica gel with hexane/EtOAc as eluent to afford 5-bromo-2-(2-methoxyethyl)-1,3-benzothiazole (2.75 g, 10.10 mmol, 37.49% yield).

LCMS(ESI): [M]$^+$ m/z: calcd 272.2; found 273.2; Rt=1.369 min.

Step 2: Synthesis of 2-(2-methoxyethyl)-5-(4,4,5,5-tetramethyl-1,3,2-dioxaborolan-2-yl)benzo[d]thiazole

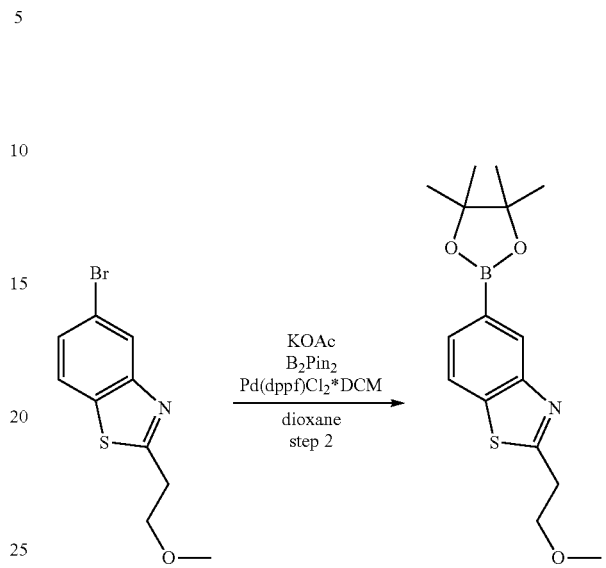

Prepared by general procedure scheme J step 2. Yield: 3.2 g of crude.

LCMS(ESI): [M]$^+$ m/z: calcd 319.2; found 320.2; Rt=1.562 min.

Step 3: Synthesis of tert-butyl 6-(2-(2-methoxyethyl)benzo[d]thiazol-5-yl)-3-methyl-3,4-dihydropyridine-1(2H)-carboxylate

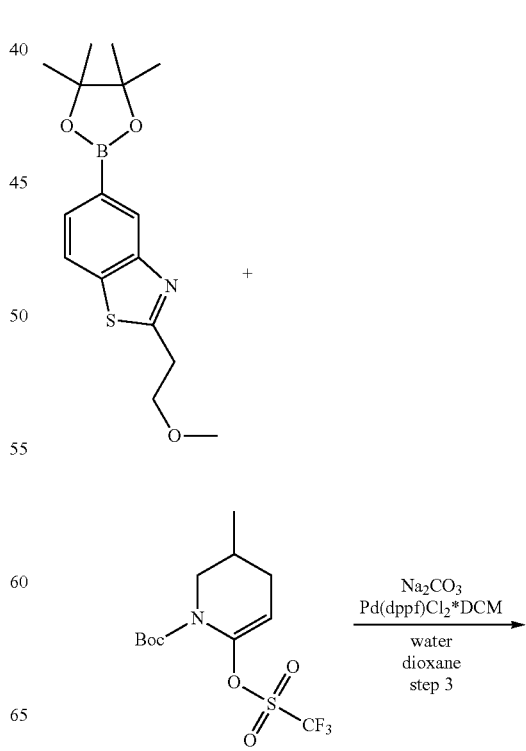

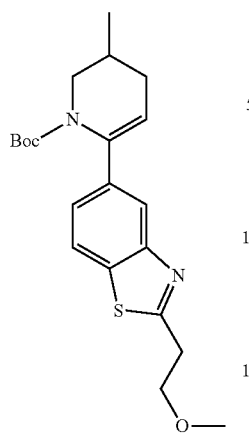

Prepared by general procedure scheme J step 3. Yield: 3.2 g of crude.

LCMS(ESI): [M]+ m/z: calcd 388.2; found 389.2; Rt=1.577 min.

Step 4: Synthesis of 2-(2-methoxyethyl)-5-(5-methyl-3,4,5,6-tetrahydropyridin-2-yl)benzo[d]thiazole

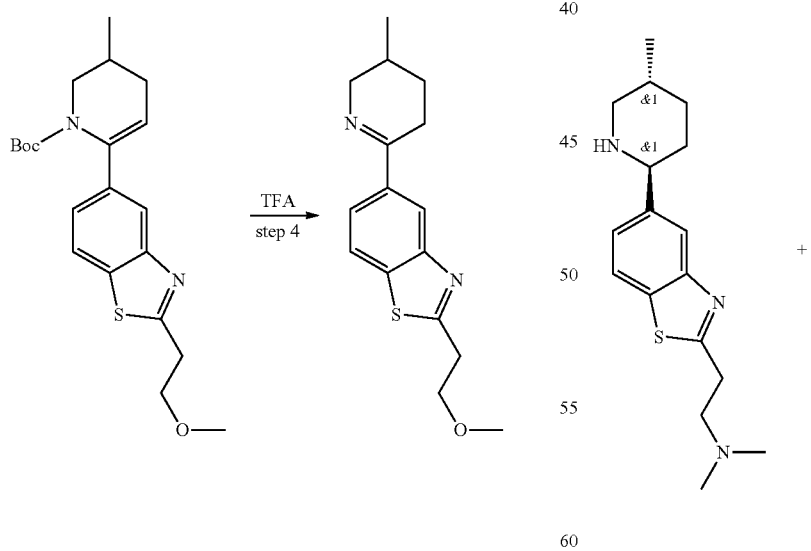

Prepared by general procedure scheme J step 4. Yield: 3.2 g of crude.

LCMS(ESI): [M]+ m/z: calcd 288.2; found 289.2; Rt=0.764 min.

Step 5: Synthesis of rac-2-(2-methoxyethyl)-5-((2R,5S)-5-methylpiperidin-2-yl)benzo[d]thiazole

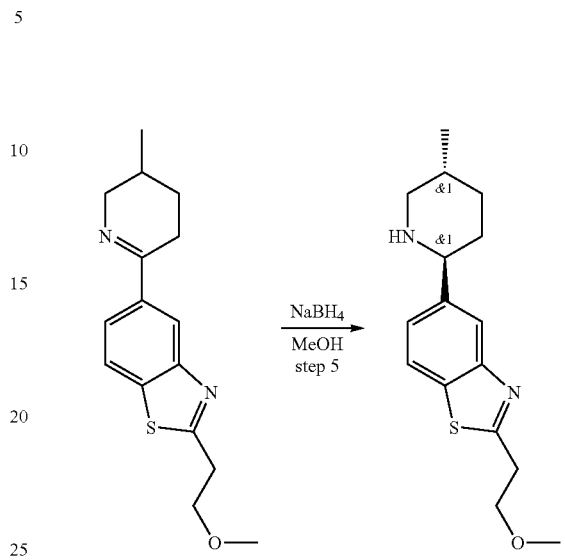

Prepared by general procedure Scheme J step 5. Yield: 3 g of crude.

LCMS(ESI): [M]+ m/z: calcd 290.2; found 291.2; Rt=0.877 min.

Example 657. The Synthesis of N-(6-amino-5-methylpyridin-3-yl)-2-(2-(2-(2-(dimethylamino)ethyl)benzo[d]thiazol-5-yl)-5-methylpiperidin-1-yl)-2-oxoacetamide (Compound 1279 and Ent-Compound 1279

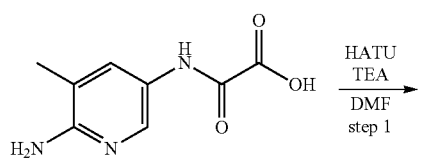

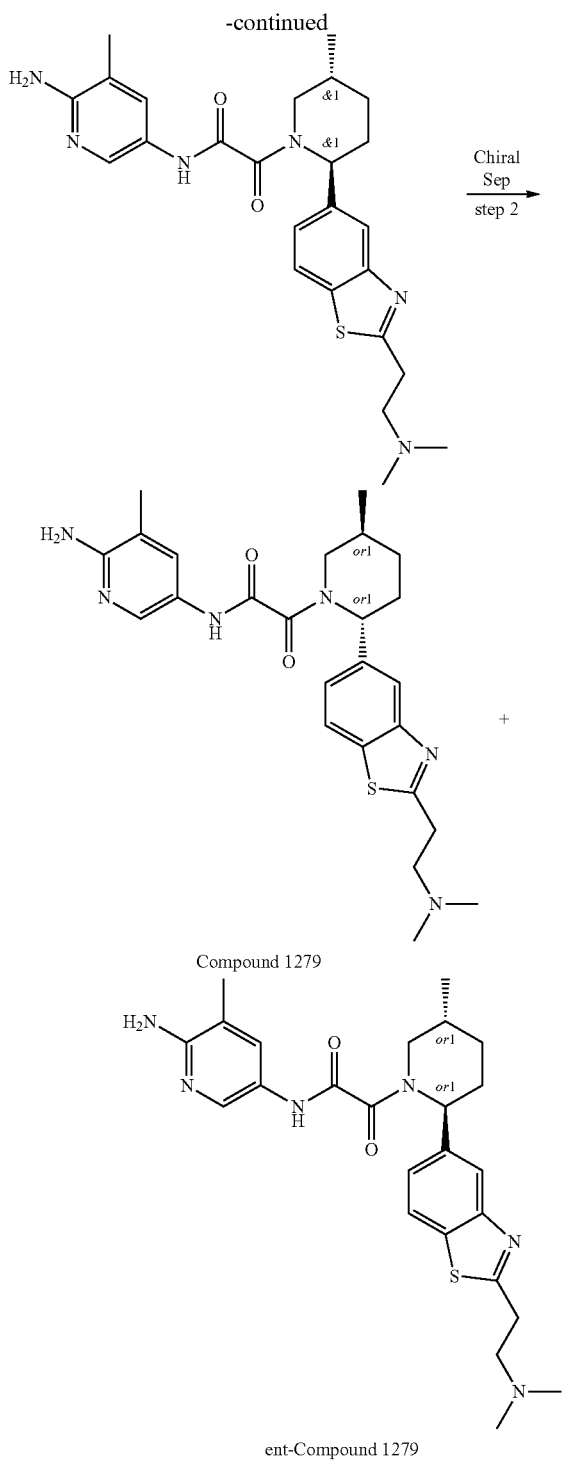

Compound 1279 ent-Compound 1279

Step 1: Synthesis of N-(6-amino-5-methylpyridin-3-yl)-2-(2-(2-(2-(dimethylamino)ethyl)benzo[d]thiazol-5-yl)-5-methylpiperidin-1-yl)-2-oxoacetamide Prepared by general procedure scheme J step 6A. Yield: 57 mg (9.67%).

HPLC conditions: Column: YMC Triart C18 100*20 mm, 5 microM; 0-5 min 30-55% water-MeCN+0.10% NH$_4$OH, flow: 30 ml/min; (loading pump 4 ml/min MeCN).

LCMS(ESI): [M]$^+$ m/z: calcd 480.2; found 481.2; Rt=1.828 min.

Step 2: Chiral Separation (Compound 1279 and ent-Compound 1279

Racemic N-(6-amino-5-methylpyridin-3-yl)-2-(2-(2-(2-(dimethylamino)ethyl)benzo[d]thiazol-5-yl)-5-methylpiperidin-1-yl)-2-oxoacetamide (57 mg, 118.60 umol) was chiral separated (Column: Chiralpak IA-II (250*20, 5 mkm), MeOH-IPA, 50-50, 10 ml/min) to obtain N-(6-amino-5-methyl-3-pyridyl)-2-[(2S,5R)-2-[2-[2-(dimethylamino)ethyl]-1,3-benzothiazol-5-yl]-5-methyl-1-piperidyl]-2-oxo-acetamide (18.7 mg, 38.91 umol, 65.61% yield) (RT=33.47 min) and N-(6-amino-5-methyl-3-pyridyl)-2-[(2R,5S)-2-[2-[2-(dimethylamino)ethyl]-1,3-benzothiazol-5-yl]-5-methyl-1-piperidyl]-2-oxo-acetamide (20 mg, 41.61 umol, 70.18% yield) (RT=57.96 min).

Rel Time for ent-Compound 1279 in analytical conditions (column: OJ-H, Hexane-IPA-MeOH, 60-20-20, 0.6 ml/min as mobile phase) 15.71 min and for Compound 1279 37.52 min. ent-Compound 1279:

Retention time: 15.71 min $^1$H NMR (600 MHz, DMSO-d$_6$) δ (ppm) 1.02-1.04 (m, 3H), 1.22-1.40 (m, 2H), 1.66-1.90 (m, 3H), 2.04-2.37 (m, 9H), 2.68-2.78 (m, 2H), 3.20-3.23 (m, 2H), 3.47 (d, 1H), 4.03 (d, 1H), 5.27-5.69 (m, 3H), 7.32-7.50 (m, 2H), 7.84-8.04 (m, 3H), 10.56 (m, 1H).

LCMS(ESI): [M]$^+$ m/z: calcd 480.2; found 481.2; Rt=1.818 min.

Compound 1279:

Retention time: 37.52 min $^1$H NMR (600 MHz, DMSO-d$_6$) δ (ppm) 1.02-1.04 (m, 3H), 1.22-1.39 (m, 2H), 1.66-1.71 (m, 2H), 1.84-2.32 (m, 10H), 2.69 (m, 1H), 3.21 (m, 3H), 3.47 (d, 1H), 4.04 (d, 1H), 5.27-5.69 (m, 3H), 7.32-7.50 (m, 2H), 7.84-8.04 (m, 3H), 10.56 (m, 1H).

LCMS(ESI): [M]$^+$ m/z: calcd 480.2; found 481.2; Rt=1.818 min.

Example 658. The Synthesis of N-(6-amino-5-methylpyridin-3-yl)-2-(2-(2-(methoxymethyl)benzo[d]thiazol-5-yl)-5-methylpiperidin-1-yl)-2-oxoacetamide (Compound 1211 and Ent-Compound 1211

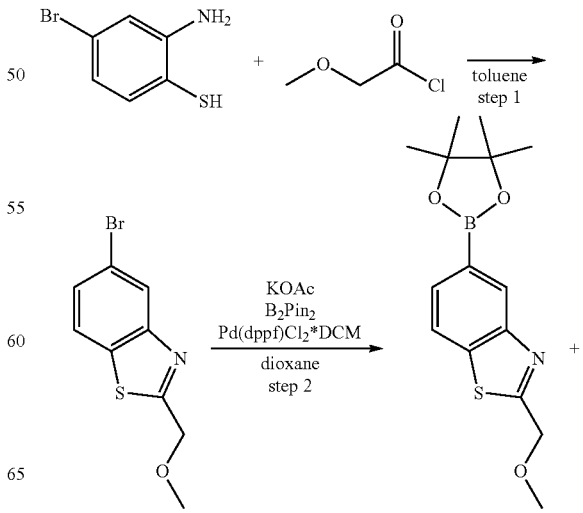

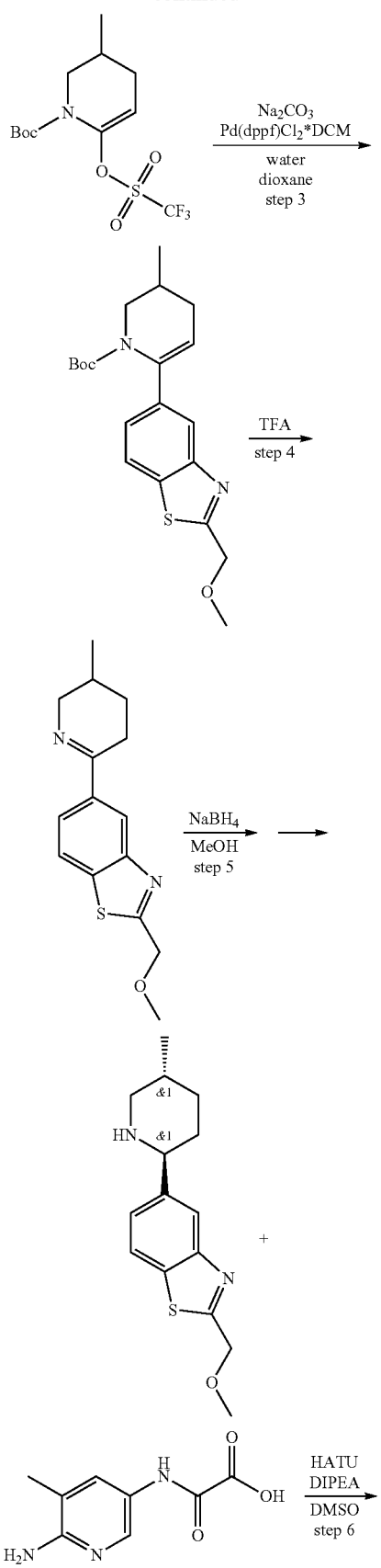
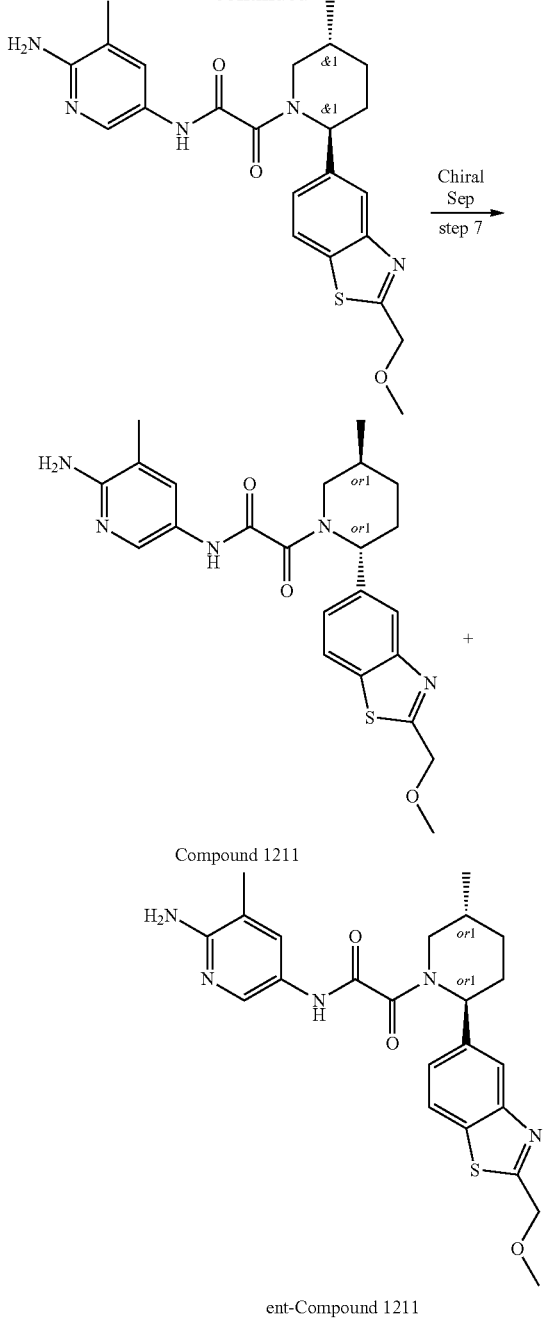
Step 6: Synthesis of N-(6-amino-5-methylpyridin-3-yl)-2-(2-(2-(methoxymethyl)benzo[d]thiazol-5-yl)-5-methylpiperidin-1-yl)-2-oxoacetamide
Prepared by general procedure scheme J step 6B. Yield: 26.5 mg (12.82%).
HPLC conditions: Column: SunFire C18 100*19 mm, 5 microM; 2-10 min 0-100% MeCN+FA, flow: 30 ml/min; (loading pump 4 ml/min MeCN).
$^1$H NMR (600 MHz, DMSO-$d_6$) δ (ppm) 1.01-1.04 (m, 3H), 1.33-1.40 (m, 2H), 1.68-1.73 (m, 1H), 1.86-1.92 (m, 2H), 2.12 (m, 2H), 2.18 (s, 3H), 3.44 (s, 3H), 4.01 (m, 1H), 4.84 (m, 2H), 5.26 (m, 1H), 5.70 (m, 1H), 7.38 (d, 1H), 7.83 (s, 1H), 7.89 (m, 1H), 8.08 (m, 1H), 8.30 (s, 1H), 11.01 (m, 1H).

LCMS(ESI): [M]+ m/z: calcd 453.2; found 454.2; Rt=2.765 min.

Step 7: Chiral Separation (Compound 1211 and ent-Compound 1211

Racemic N-(6-amino-5-methyl-3-pyridyl)-2-[(2S,5R)-2-[2-(methoxymethyl)-1,3-benzothiazol-5-yl]-5-methyl-1-piperidyl]-2-oxo-acetamide (53 mg, 116.85 umol) was chiral separated (Column: Chiral ART (250*20 mm, 5 mkm); Mobile phase: IPA-MeOH, 50-50; Flow Rate: 12 ml/min) to obtain N-(6-amino-5-methyl-3-pyridyl)-2-[(2S,5R)-2-[2-(methoxymethyl)-1,3-benzothiazol-5-yl]-5-methyl-1-piperidyl]-2-oxo-acetamide (17.8 mg, 39.25 umol, 33.58% yield) (RT=13.11 min) and N-(6-amino-5-methyl-3-pyridyl)-2-[(2R,5S)-2-[2-(methoxymethyl)-1,3-benzothiazol-5-yl]-5-methyl-1-piperidyl]-2-oxo-acetamide (18 mg, 39.69 umol, 33.96% yield) (RT=17.54 min).

Rel Time for ent-Compound 1211 in analytical conditions (column: 1C, IPA-MeOH, 50-50, 0.6 ml/min as mobile phase) 17.95 min and for Compound 1211 24.51 min.

ent-Compound 1211:

Retention time: 17.95 min

¹H NMR (600 MHz, DMSO-d₆) δ (ppm) 10.58-10.49 (m, 1H), 8.13-8.07 (m, 1H), 8.05-7.88 (m, 2H), 7.51-7.36 (m, 2H), 5.74-5.25 (m, 3H), 4.85-4.81 (m, 2H), 4.06-3.45 (m, 1H), 3.44 (s, 3H), 3.19-2.76 (m, 1H), 2.35-2.27 (m, 1H), 2.20-2.08 (m, 1H), 2.05-1.96 (m, 3H), 1.91-1.83 (m, 1H), 1.73-1.66 (m, 1H), 1.41-1.31 (m, 1H), 1.04-1.01 (m, 3H).

LCMS(ESI): [M]+ m/z: calcd 453.2; found 454.2; Rt=2.540 min.

Compound 1211:

Retention time: 24.51 min

¹H NMR (600 MHz, DMSO-d₆) δ (ppm) 10.59-10.49 (m, 1H), 8.13-7.88 (m, 3H), 7.52-7.36 (m, 2H), 5.73-5.26 (m, 3H), 4.86-4.80 (m, 2H), 4.06-3.46 (m, 1H), 3.44 (s, 3H), 3.25-2.75 (m, 1H), 2.36-2.25 (m, 1H), 2.24-2.07 (m, 1H), 2.06-1.96 (m, 3H), 1.93-1.82 (m, 1H), 1.76-1.64 (m, 1H), 1.41-1.30 (m, 1H), 1.04-1.00 (m, 3H).

LCMS(ESI): [M]+ m/z: calcd 453.2; found 454.2; Rt=2.549 min.

Example 659. The Synthesis of N-(6-amino-5-methylpyridin-3-yl)-2-(2-(2-((Dimethylamino)methyl)benzo[d]thiazol-5-yl)-5-methylpiperidin-1-yl)-2-oxoacetamide (Compound 1106, Compound 1122 and Ent-Compound 1122

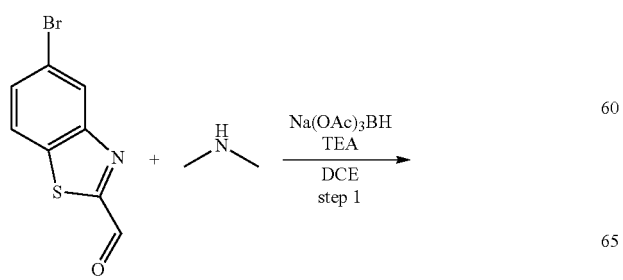

-continued

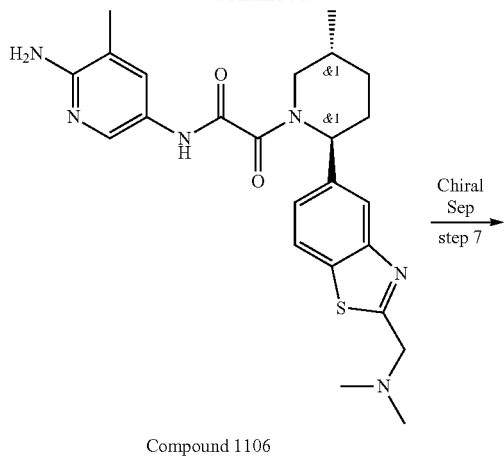

Compound 1106

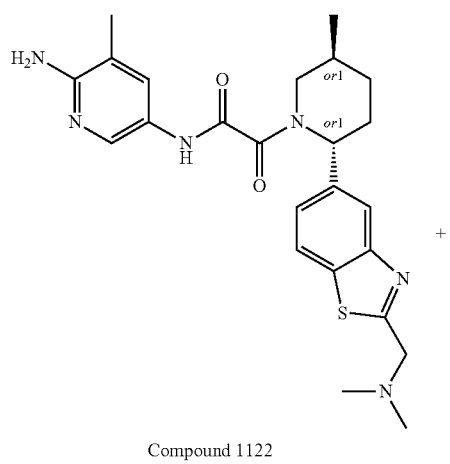

Compound 1122

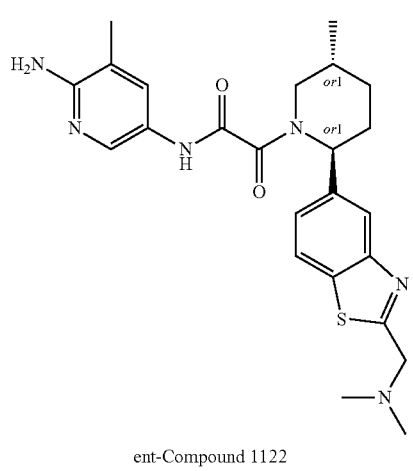

ent-Compound 1122

Step 6: Synthesis of N-(6-amino-5-methylpyridin-3-yl)-2-(2-(2-((Dimethylamino)methyl)benzo[d]thiazol-5-yl)-5-methylpiperidin-1-yl)-2-oxoacetamide (Compound 1106

Prepared by general procedure 10 step 6A. Yield: 27 mg (9.97%).

HPLC conditions: Column: SunFire C18 100*19 mm, 5 microM; 2-8 min 50-75% water-MeCN+NH₃, flow: 30 ml/min; (loading pump 4 ml/min MeCN).

$^1$H NMR (600 MHz, DMSO-$d_6$) δ (ppm) 0.71-0.78 (m, 2H), 1.03 (m, 3H), 1.32-1.39 (m, 1H), 1.67-1.73 (m, 2H), 1.85 (m, 1H), 1.97 (m, 1H), 2.08 (m, 2H), 2.30 (m, 6H), 2.78 (m, 1H), 3.86 (m, 3H), 5.62 (m, 2H), 7.34-7.54 (m, 2H), 7.85 (s, 1H), 7.88-8.06 (m, 2H), 10.51 (m, 1H).

LCMS(ESI): [M]⁺ m/z: calcd 466.2; found 467.2; Rt=2.007 min.

Step 7: Chiral Separation (Compound 1122 and ent-Compound 1122

Racemic N-(6-amino-5-methyl-3-pyridyl)-2-[(2S,5R)-2-[2-[(dimethylamino)methyl]-1,3-benzothiazol-5-yl]-5-methyl-1-piperidyl]-2-oxo-acetamide (60 mg, 128.59 umol) was chiral separated (Column: Chiralpak AS-H (250*20 mm, 5 mkm); Mobile phase: Hexane-MeOH-IPA, 60-20-20; Flow Rate: 12 ml/min) to obtain N-(6-amino-5-methyl-3-pyridyl)-2-[(2S,5R)-2-[2-[(dimethylamino)methyl]-1,3-benzothiazol-5-yl]-5-methyl-1-piperidyl]-2-oxo-acetamide (18.9 mg, 40.51 umol, 31.50% yield) (RT=11.78 min) and N-(6-amino-5-methyl-3-pyridyl)-2-[(2R,5S)-2-[2-[(dimethylamino)methyl]-1,3-benzothiazol-5-yl]-5-methyl-1-piperidyl]-2-oxo-acetamide (18.6 mg, 39.86 umol, 31.00% yield) (RT=18.73 min).

Rel Time for ent-Compound 1122 in analytical conditions (column: AS-H, Hexane-IPA-MeOH, 50-25-25, 0.6 ml/min as mobile phase) 11.73 min and for Compound 1122 8.74 min.

ent-Compound 1122:

Retention time: 11.73 min $^1$H NMR (600 MHz, DMSO-$d_6$) δ (ppm) 10.57-10.49 (m, 1H), 8.09-7.95 (m, 2H), 7.91-7.83 (m, 1H), 7.54-7.32 (m, 2H), 5.74-5.25 (m, 3H), 4.05-3.45 (m, 3H), 3.25-2.75 (m, 1H), 2.30 (s, 6H), 2.29-2.05 (m, 2H), 2.05-1.95 (m, 3H), 1.93-1.82 (m, 1H), 1.75-1.66 (m, 1H), 1.41-1.29 (m, 1H), 1.05-1.00 (m, 3H).

LCMS(ESI): [M]⁺ m/z: calcd 466.2; found 467.2; Rt=1.458 min.

Compound 1122:

Retention time: 8.74 min $^1$H NMR (600 MHz, DMSO-$d_6$) δ (ppm) 10.57-10.47 (m, 1H), 8.08-7.94 (m, 2H), 7.91-7.83 (m, 1H), 7.52-7.32 (m, 2H), 5.71-5.24 (m, 3H), 4.05-3.44 (m, 3H), 3.28-2.76 (m, 1H), 2.30 (s, 6H), 2.28-2.06 (m, 2H), 2.04-1.96 (m, 3H), 1.91-1.84 (m, 1H), 1.76-1.67 (m, 1H), 1.40-1.31 (m, 1H), 1.04-1.01 (m, 3H).

LCMS(ESI): [M]⁺ m/z: calcd 466.2; found 467.2; Rt=1.460 min.

Example 660. The Synthesis of N-(6-amino-5-ethylpyridin-3-yl)-2-(2-(2-(2-(dimethylamino)ethyl)benzo[d]thiazol-5-yl)-5-methylpiperidin-1-yl)-2-oxoacetamide (Compound 1196 and Compound 1133

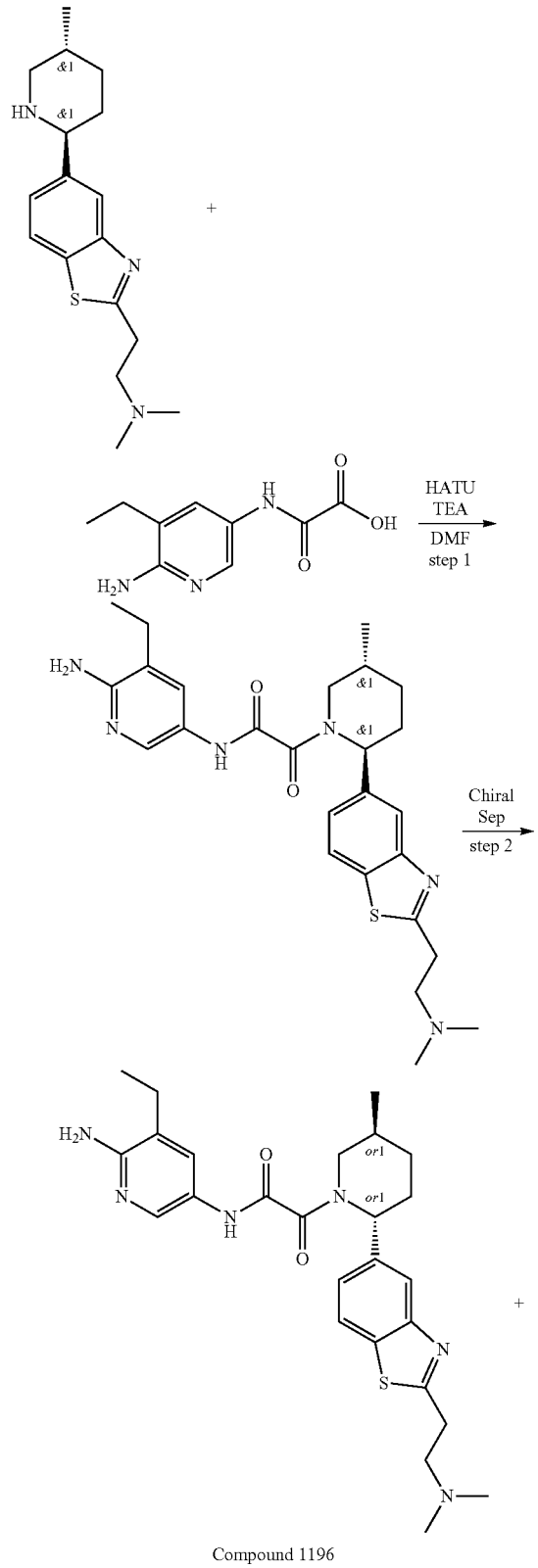

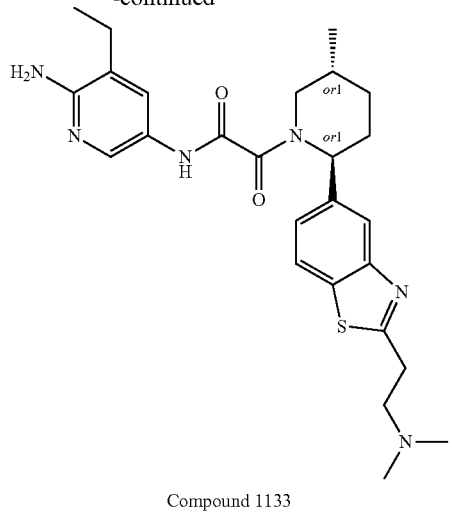

Compound 1133

Step 1: Synthesis of N-(6-amino-5-ethylpyridin-3-yl)-2-(2-(2-(2-(dimethylamino)ethyl)benzo[d]thiazol-5-yl)-5-methylpiperidin-1-yl)-2-oxoacetamide Prepared by general procedure scheme J step 6A. Yield: 264 mg (48.35%).

HPLC conditions: Column: XBridge C18 100*19 mm, 5 microM; 0-1-5 min 35-35-65% water-MeCN+0.1% NH$_4$OH, flow: 30 ml/min; (loading pump 4 ml/min MeCN).

LCMS(ESI): [M]$^+$ m/z: calcd 494.2; found 495.2; Rt=1.955 min.

Step 2: Chiral Separation (Compound 1196 and Compound 1133

Racemic N-(6-amino-5-ethylpyridin-3-yl)-2-(2-(2-(2-(dimethylamino)ethyl)benzo[d]thiazol-5-yl)-5-methylpiperidin-1-yl)-2-oxoacetamide (264 mg, 533.71 umol) was chiral separated (Column: Chirapak IC-III (250*20 mm, 5 mkm), IPA-MeOH, 50-50, 10 ml/min) to obtain N-(6-amino-5-ethyl-3-pyridyl)-2-[(2R,5S)-2-[2-[2-(dimethylamino)ethyl]-1,3-benzothiazol-5-yl]-5-methyl-1-piperidyl]-2-oxo-acetamide (60 mg, 121.30 umol, 45.45% yield) (RT=34.84 min) and N-(6-amino-5-ethyl-3-pyridyl)-2-[(2S,5R)-2-[2-[2-(dimethylamino)ethyl]-1,3-benzothiazol-5-yl]-5-methyl-1-piperidyl]-2-oxo-acetamide (53 mg, 107.15 umol, 40.15% yield) (RT=24.54 min).

Rel Time for Compound 1196 in analytical conditions (column: 1C, IPA-MeOH, 50-50, 0.6 ml/min as mobile phase) 34.84 min and for Compound 1133 12.90 min.

Compound 1196:

Retention time: 34.84 min $^1$H NMR (600 MHz, DMSO-d$_6$) δ (ppm) 1.00-1.05 (m, 3H), 1.06-1.16 (m, 3H), 1.31-1.41 (m, 1H), 1.66-1.76 (m, 1H), 1.82-1.92 (m, 1H), 2.04-2.18 (m, 1H), 2.23 (s, 6H), 2.26-2.32 (m, 1H), 2.32-2.36 (m, 1H), 2.40-2.43 (m, 1H), 2.68-2.76 (m, 2H), 2.76-3.27 (m, 3H), 3.35-4.08 (m, 1H), 5.26-5.61 (m, 1H), 5.61-5.73 (m, 2H), 7.30-7.42 (m, 1H), 7.43-7.56 (m, 1H), 7.81-7.91 (m, 1H), 7.99-8.03 (m, 1H), 8.03-8.09 (m, 1H), 10.49-10.60 (m, 1H).

LCMS(ESI): [M]$^+$ m/z: calcd 494.2; found 495.2; Rt=1.745 min.

Compound 1133:

Retention time: 12.90 min

¹H NMR (600 MHz, DMSO-d₆) δ (ppm) 1.00-1.05 (m, 3H), 1.06-1.16 (m, 3H), 1.30-1.42 (m, 1H), 1.63-1.77 (m, 1H), 1.80-1.94 (m, 1H), 2.03-2.18 (m, 1H), 2.20 (s, 6H), 2.27-2.33 (m, 1H), 2.36-2.44 (m, 2H), 2.65-2.72 (m, 2H), 2.74-3.27 (m, 3H), 3.36-4.11 (m, 1H), 5.26-5.61 (m, 1H), 5.61-5.75 (m, 2H), 7.31-7.42 (m, 1H), 7.42-7.54 (m, 1H), 7.78-7.89 (m, 1H), 7.98-8.03 (m, 1H), 8.03-8.11 (m, 1H), 10.51-10.66 (m, 1H).

LCMS(ESI): [M]⁺ m/z: calcd 494.2; found 495.2; Rt=1.730 min.

Example 661. Synthesis of N-(6-amino-5-methylpyridin-3-yl)-2-(2-(2-ethylbenzo[d]thiazol-5-yl)-5-methylpiperidin-1-yl)-2-oxoacetamide (Compound 1184)

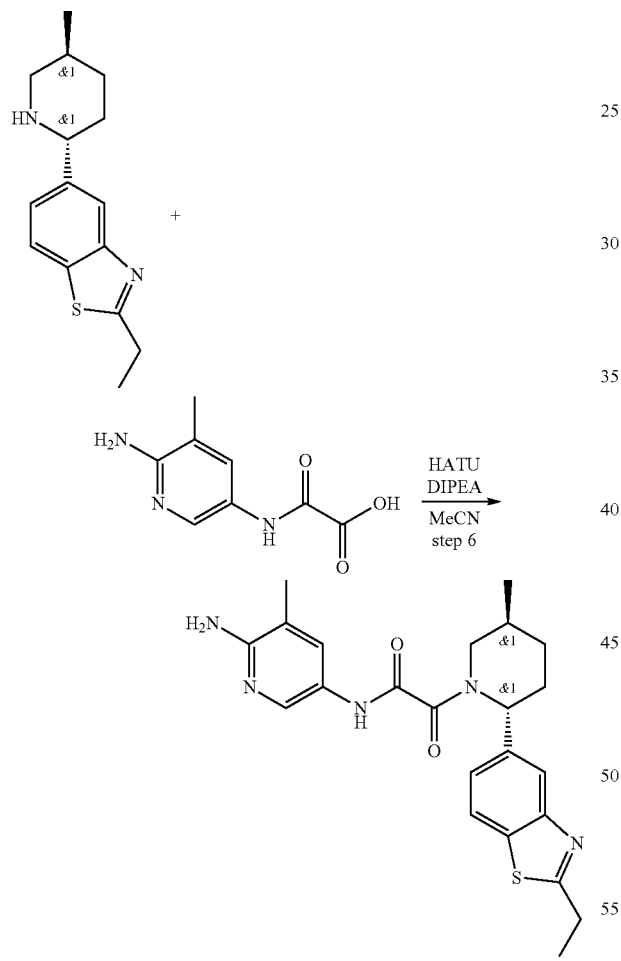

Prepared by general procedure scheme J step 6B. Yield: 49 mg (14.58%).

HPLC conditions: Column: YMC Triart C18 100*20 mm, 5 microM; 0-6 min 40-65% water-MeCN+0.1% NH₄OH, flow: 30 ml/min; (loading pump 4 ml/min MeOH).

¹H NMR (600 MHz, DMSO-d₆) δ (ppm) 1.02 (m, 3H), 1.36 (m, 4H), 1.70 (m, 1H), 1.87 (m, 1H), 2.04 (m, 3H), 2.25 (m, 2H), 3.00 (m, 3H), 3.85 (m, 1H), 5.63 (m, 3H), 7.40 (m, 2H), 7.96 (m, 3H), 10.54 (m, 1H).

LCMS(ESI): [M]⁺ m/z: calcd 437.2; found 438.2; Rt=2.168 min.

Example 662. The Synthesis of 5-(2-(2-(2-(2-(dimethylamino)ethyl)benzo[d]thiazol-5-yl)-5-methylpiperidin-1-yl)-2-oxoacetamido)nicotinamide (Compound 1355, Compound 1128 and Compound 1254

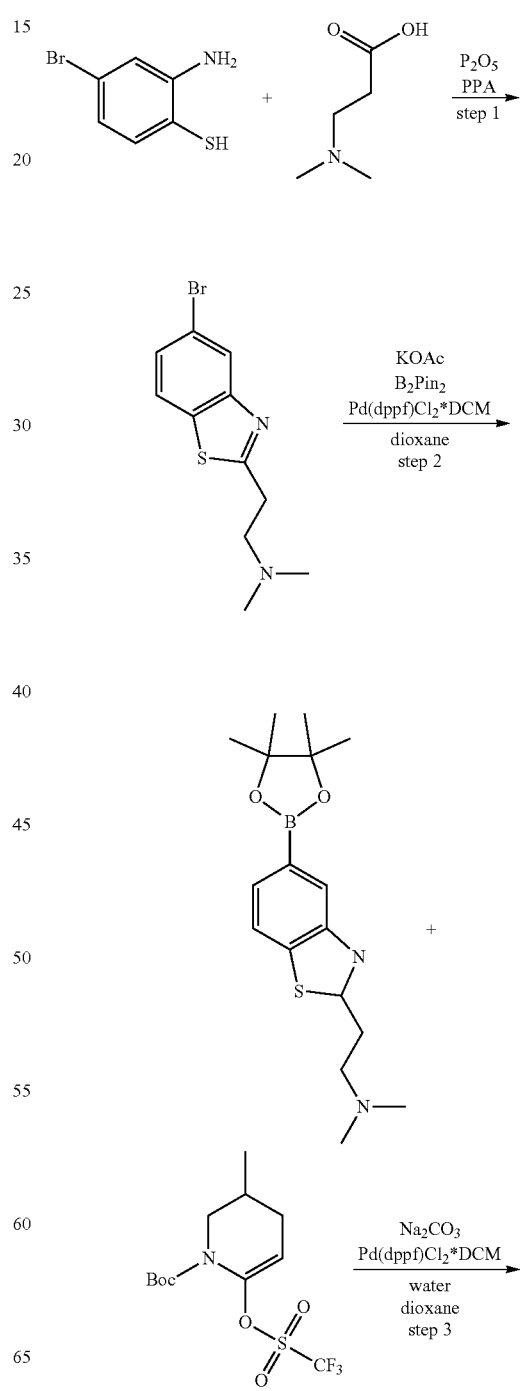

2797
-continued
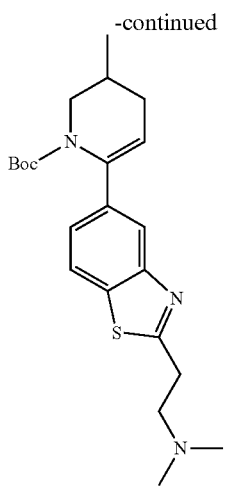
TFA
step 4
→
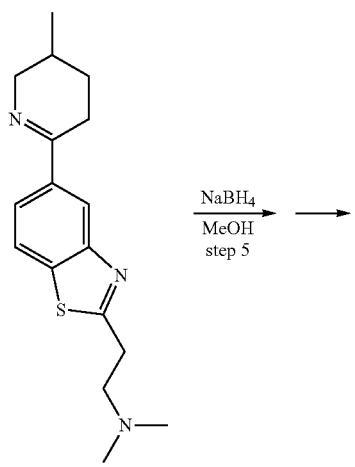
NaBH₄
MeOH
step 5
→
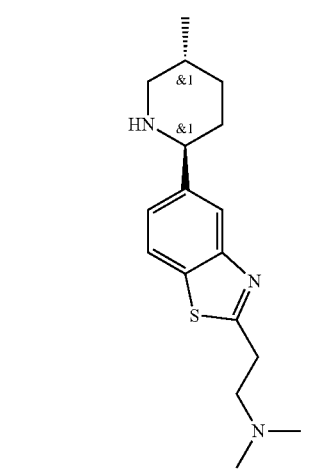
+
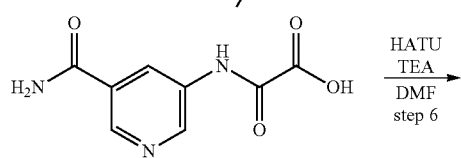
HATU
TEA
DMF
step 6
→
2798
-continued
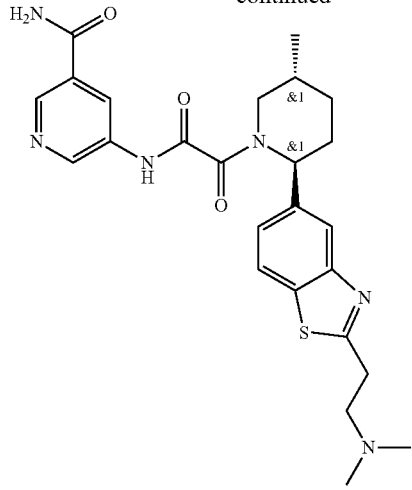
Compound 1355
Chiral Sep
step 7
→
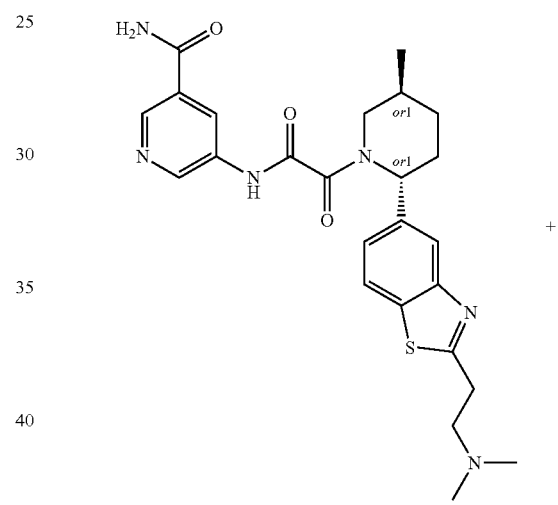
Compound 1128
+
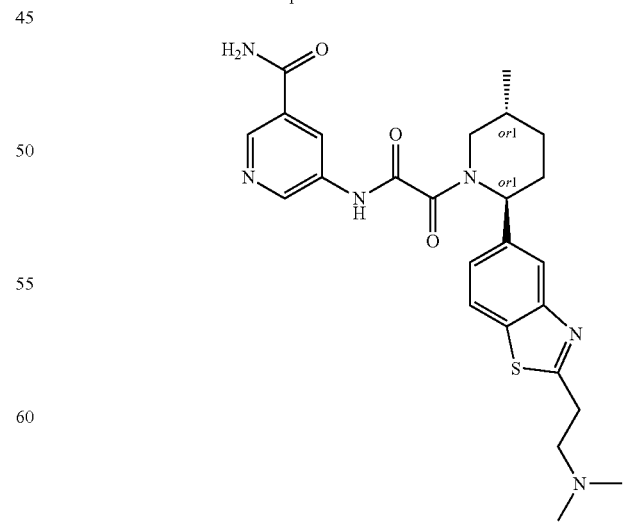
Compound 1254

Step 6: Synthesis of 5-(2-(2-(2-(2-(dimethylamino) ethyl)benzo[d]thiazol-5-yl)-5-methylpiperidin-1-yl)-2-oxoacetamido)nicotinamide (Compound 1355

Prepared by general procedure scheme J step 6A. Yield: 20 mg (6.14%).

HPLC conditions: Column: YMC Triart C18 100*20 mm, 5 microM; 0-5 min 15-40% water-MeCN+0.1% $NH_4OH$, flow: 30 ml/min; (loading pump 4 ml/min MeCN).

Compound 1355:

$^1H$ NMR (600 MHz, DMSO-$d_6$) δ (ppm) 1.03-1.04 (m, 3H), 1.33-1.40 (m, 2H), 1.68-1.99 (m, 3H), 2.08-2.30 (m, 6H), 2.67-2.85 (m, 2H), 3.19-3.23 (m, 2H), 3.50-4.05 (m, 2H), 5.30-5.70 (m, 2H), 7.34-7.42 (m, 1H), 7.53-7.59 (m, 1H), 7.86-7.89 (m, 1H), 8.00-8.16 (m, 2H), 8.40-8.51 (m, 1H), 8.69-8.90 (m, 2H).

LCMS(ESI): [M]$^+$ m/z: calcd 494.2; found 495.2; Rt=1.914 min.

Step 7: Chiral Separation (Compound 1128 and Compound 1254

Racemic 5-(2-(2-(2-(2-(dimethylamino)ethyl)benzo[d] thiazol-5-yl)-5-methylpiperidin-1-yl)-2-oxoacetamido)nicotinamide (235 mg, 475.12 umol) was chiral separated (Column: Chiralcel OJ-H-II (250*20 mm, 5 mkm), Hexane-IPA-MeOH, 50-25-25, 12 ml/min) to obtain 5-[[2-[(2R,5S)-2-[2-[2-(dimethylamino)ethyl]-1,3-benzothiazol-5-yl]-5-methyl-1-piperidyl]-2-oxo-acetyl]amino]pyridine-3-carboxamide (90 mg, 181.96 umol, 76.60% yield) (RT=29.78 min) and 5-[[2-[(2S,5R)-2-[2-[2-(dimethylamino)ethyl]-1,3-benzothiazol-5-yl]-5-methyl-1-piperidyl]-2-oxo-acetyl]amino]pyridine-3-carboxamide (86 mg, 173.88 umol, 73.19% yield) (RT=14.44 min).

Rel Time for Compound 1128 in analytical conditions (column: OJ-H, Hexane-IPA-MeOH, 50-25-25, 0.6 ml/min as mobile phase) 22.93 min and for Compound 1254 11.34 min.

Compound 1128:

Retention time: 22.93 min $^1H$ NMR (600 MHz, DMSO-$d_6$) δ (ppm) 1.05 (m, 3H), 1.37 (m, 1H), 1.72 (m, 1H), 1.89 (m, 1H), 2.08 (m, 1H), 2.20 (m, 6H), 2.31 (m, 1H), 2.68 (m, 3H), 3.22 (m, 2H), 3.77 (dd, 1H), 5.50 (m, 1H), 7.38 (dd, 1H), 7.58 (m, 1H), 7.87 (m, 1H), 8.03 (m, 1H), 8.14 (m, 1H), 8.47 (m, 1H), 8.81 (m, 2H), 11.08 (s, 1H).

LCMS(ESI): [M]$^+$ m/z: calcd 494.2; found 495.2; Rt=2.340 min.

Compound 1254

Retention time: 11.34 min $^1H$ NMR (600 MHz, DMSO-$d_6$) δ (ppm) 1.05 (m, 3H), 1.37 (m, 1H), 1.72 (m, 1H), 1.89 (m, 1H), 2.09 (m, 1H), 2.20 (m, 6H), 2.31 (m, 1H), 2.68 (m, 2H), 3.21 (m, 3H), 3.52 (m, 1H), 5.30 (s, 1H), 7.38 (dd, 1H), 7.59 (d, 1H), 7.87 (m, 1H), 8.03 (dd, 1H), 8.15 (d, 1H), 8.49 (m, 1H), 8.77 (m, 1H), 8.89 (m, 1H), 11.28 (m, 1H).

LCMS(ESI): [M]$^+$ m/z: calcd 494.2; found 495.2; Rt=2.370 min.

Example 663. The Synthesis of N-(6-amino-5-ethylpyridin-3-yl)-2-(2-(2-(2-methoxyethyl)benzo[d] thiazol-5-yl)-5-methylpiperidin-1-yl)-2-oxoacetamide (Compound 1375 and Compound 1386

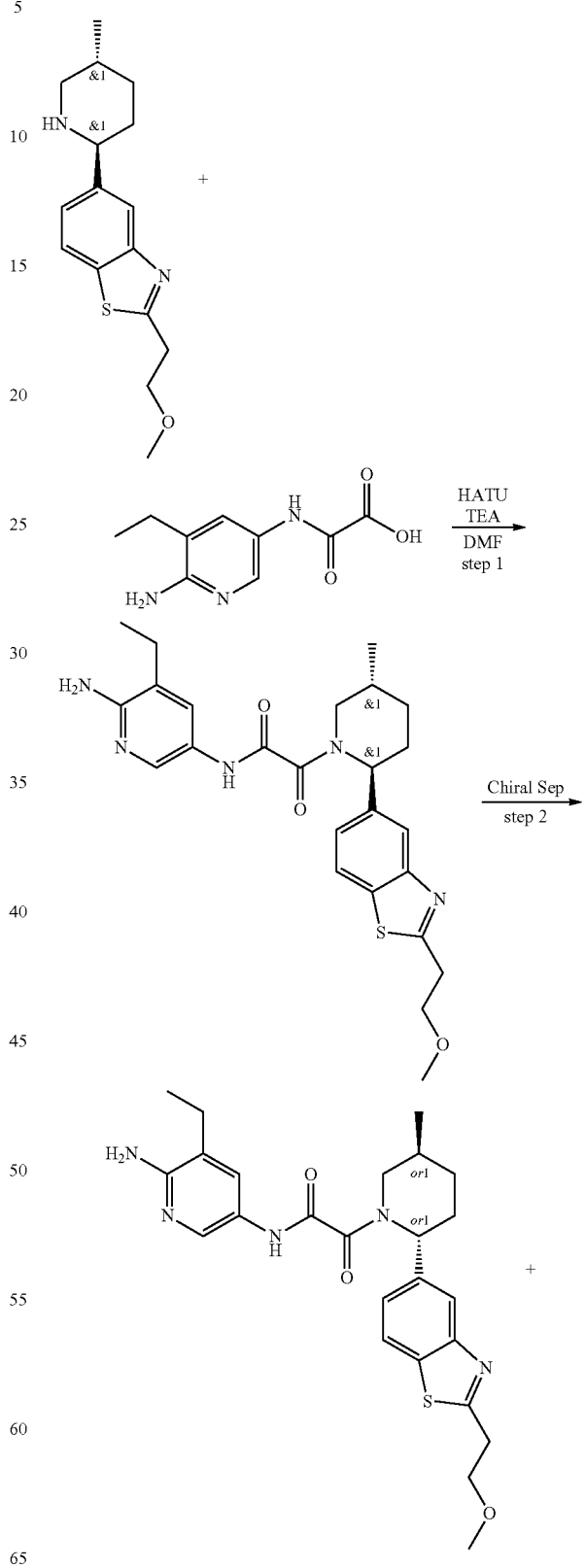

Compound 1386

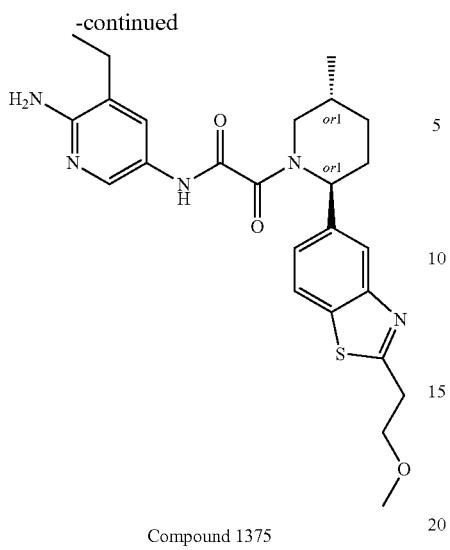

Compound 1375

Step 1: Synthesis of N-(6-amino-5-ethylpyridin-3-yl)-2-(2-(2-(2-methoxyethyl)benzo[d]thiazol-5-yl)-5-methylpiperidin-1-yl)-2-oxoacetamide Prepared by general procedure scheme J step 6A. Yield: 207 mg (62.41%).

HPLC conditions: Column: XBridge C18 100*19 mm, 5 microM; 0-5 min 5-55% water-MeCN+0.10% NH$_4$OH, flow: 30 ml/min; (loading pump 4 ml/min MeCN).

LCMS(ESI): [M]$^+$ m/z: calcd 481.2; found 482.2; Rt=2.923 min.

Step 2: Chiral Separation (Compound 1375 and Compound 1386

Racemic N-(6-amino-5-ethylpyridin-3-yl)-2-(2-(2-(2-methoxyethyl)benzo[d]thiazol-5-yl)-5-methylpiperidin-1-yl)-2-oxoacetamide (170 mg, 352.98 umol) was chiral separated (Column: ChiralART YMC (250*20 mm, 5 mkm), IPA-MeOH, 50-50, 10 ml/min) to obtain N-(6-amino-5-ethyl-3-pyridyl)-2-[(2S,5R)-2-[2-(2-methoxyethyl)-1,3-benzothiazol-5-yl]-5-methyl-1-piperidyl]-2-oxo-acetamide (53 mg, 110.05 μmol, 62.35% yield) (RT=14.57 min) and N-(6-amino-5-ethyl-3-pyridyl)-2-[(2R,5S)-2-[2-(2-methoxyethyl)-1,3-benzothiazol-5-yl]-5-methyl-1-piperidyl]-2-oxo-acetamide (55 mg, 114.20 μmol, 64.71% yield) (RT=18.81 min).Rel Time for Compound 1375 in analytical conditions (column: 1C, IPA-MeOH, 50-50, 0.6 ml/min as mobile phase) 16.50 min and for Compound 1386 22.49 min.

Compound 1375:
Retention time: 16.50 min
$^1$H NMR (600 MHz, DMSO-d$_6$) δ (ppm) 1.00-1.05 (m, 3H), 1.05-1.15 (m, 3H), 1.30-1.42 (m, 1H), 1.64-1.75 (m, 1H), 1.81-1.95 (m, 1H), 2.03-2.37 (m, 3H), 2.39-2.42 (m, 1H), 2.75-3.28 (m, 4H), 3.31-3.35 (m, 2H), 3.43-4.09 (m, 3H), 5.25-5.75 (m, 3H), 7.32-7.43 (m, 1H), 7.43-7.53 (m, 1H), 7.82-7.92 (m, 1H), 7.97-8.09 (m, 2H), 10.51-10.62 (m, 1H).

LCMS(ESI): [M]$^+$ m/z: calcd 481.2; found 482.2; Rt=2.642 min.

Compound 1386:
Retention time: 22.49 min
$^1$H NMR (600 MHz, DMSO-d$_6$) δ (ppm) 1.01-1.06 (m, 3H), 1.06-1.15 (m, 3H), 1.30-1.39 (m, 1H), 1.62-1.75 (m, 1H), 1.81-1.92 (m, 1H), 2.03-2.36 (m, 3H), 2.39-2.43 (m, 1H), 2.75-3.28 (m, 4H), 3.31-3.34 (m, 2H), 3.45-4.06 (m, 3H), 5.24-5.72 (m, 3H), 7.31-7.43 (m, 1H), 7.43-7.54 (m, 1H), 7.82-7.92 (m, 1H), 7.98-8.08 (m, 2H), 10.50-10.62 (m, 1H).

LCMS(ESI): [M]$^+$ m/z: calcd 481.2; found 482.2; Rt=2.658 min.

Example 664. The Synthesis of N-(6-amino-5-(trifluoromethyl)pyridin-3-yl)-2-((2R,5S)-5-methyl-2-(2-(1-methylpiperidin-4-yl)benzo[d]thiazol-5-yl)piperidin-1-yl)-2-oxoacetamide (Compound 1117)

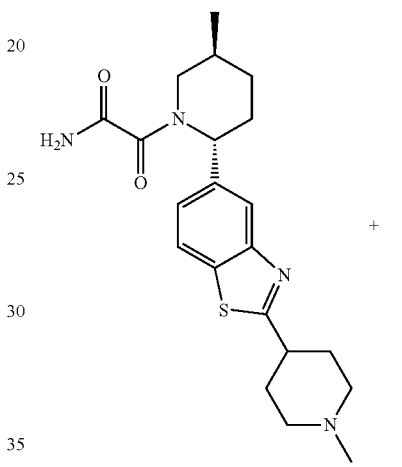

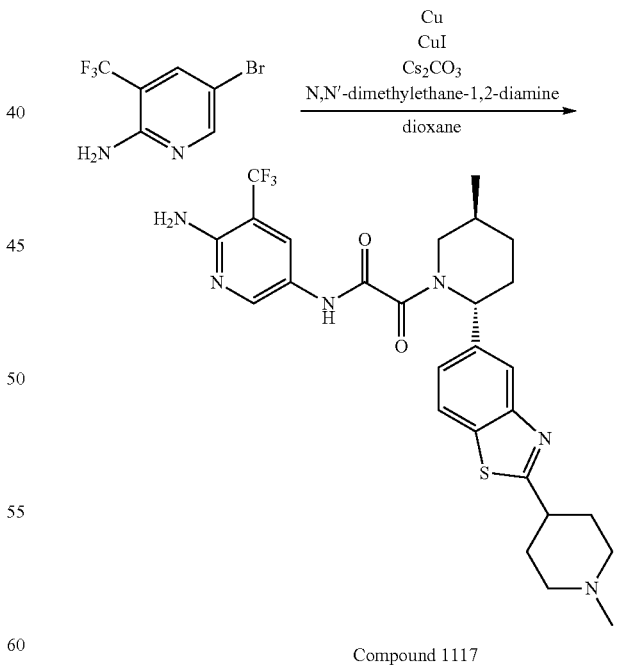

Compound 1117

Prepared by general procedure Scheme J step 3A. Yield: 31 mg (13.18%).

HPLC conditions: Column:XBridge C18 100*19 mm, 5 microM; 0-5 min 25-45% water-MeCN+0.1% NH$_4$OH, flow: 30 ml/min; (loading pump 4 ml/min MeCN).

Compound 1117:

$^1$H NMR (600 MHz, DMSO-$d_6$) δ (ppm) 0.97-1.07 (m, 3H), 1.28-1.41 (m, 1H), 1.66-1.74 (m, 1H), 1.76-1.91 (m, 3H), 2.04-2.09 (m, 4H), 2.10-2.24 (m, 4H), 2.26-2.34 (m, 1H), 2.83-2.87 (m, 2H), 3.04-3.09 (m, 1H), 3.26-3.31 (m, 1H), 3.52-4.06 (m, 1H), 5.29-5.75 (m, 1H), 6.32-6.42 (m, 2H), 7.32-7.42 (m, 1H), 7.85-7.89 (m, 1H), 7.98-8.12 (m, 2H), 8.34-8.47 (m, 1H), 10.81-10.96 (m, 1H).

LCMS(ESI): [M]$^+$ m/z: calcd 560.2; found 561.2; Rt=2.547 min.

Example 665. The Synthesis of N-(6-amino-5-ethylpyridin-3-yl)-2-((2R,5S)-2-(2-(2-(dimethylamino)propan-2-yl)benzo[d]thiazol-5-yl)-5-methylpiperidin-1-yl)-2-oxoacetamide (Compound 1237)

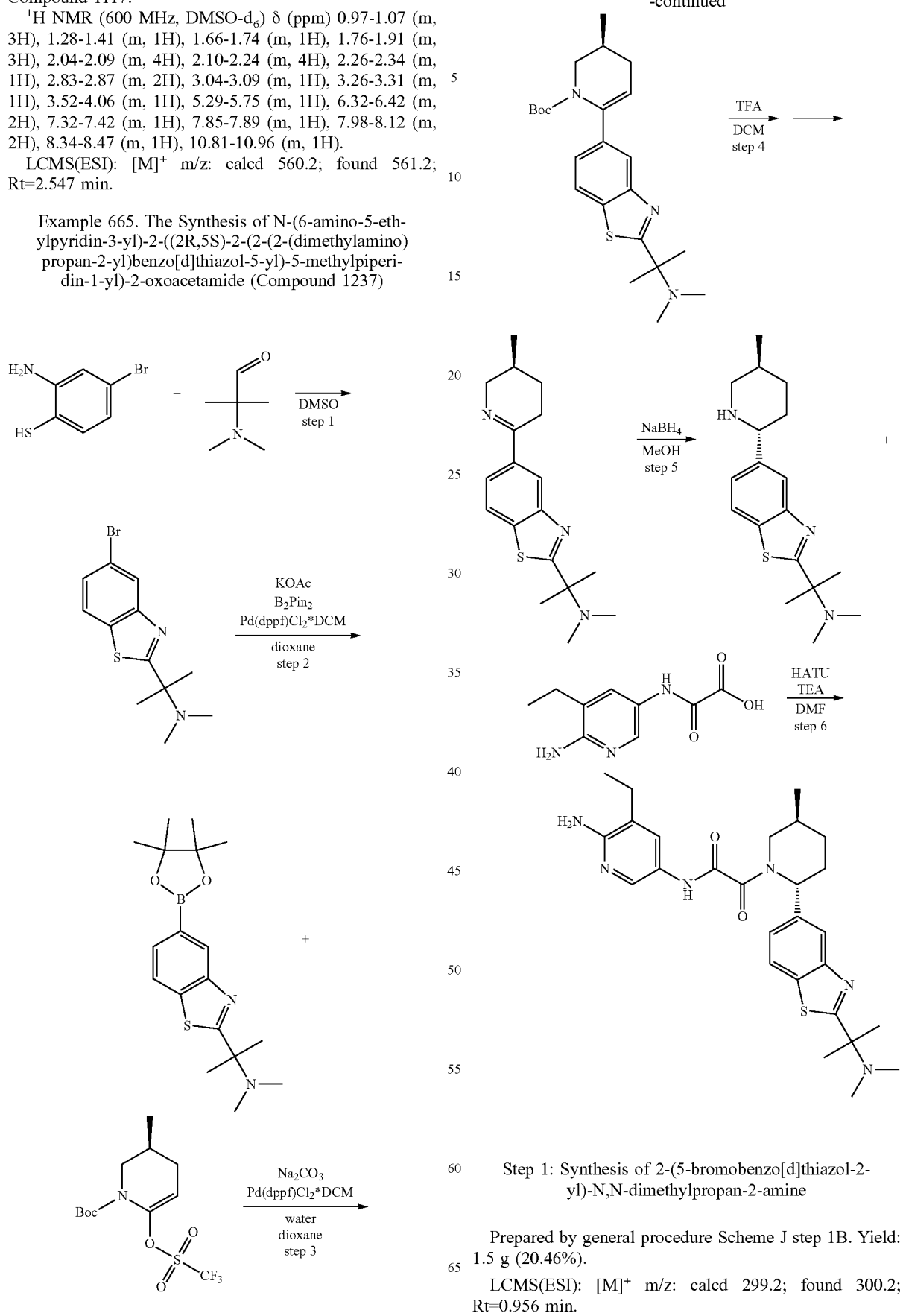

Step 1: Synthesis of 2-(5-bromobenzo[d]thiazol-2-yl)-N,N-dimethylpropan-2-amine

Prepared by general procedure Scheme J step 1B. Yield: 1.5 g (20.46%).

LCMS(ESI): [M]$^+$ m/z: calcd 299.2; found 300.2; Rt=0.956 min.

Step 2: Synthesis of N,N-dimethyl-2-(5-(4,4,5,5-tetramethyl-1,3,2-dioxaborolan-2-yl)benzo[d]thiazol-2-yl)propan-2-amine Prepared by general procedure Scheme J step 2. Yield: 1.74 g of crude.
LCMS(ESI): [M]$^+$ m/z: calcd 346.2; found 347.2; Rt=0.945 min.

Step 3: Synthesis of (S)-tert-butyl 6-(2-(2-(dimethylamino)propan-2-yl)benzo[d]thiazol-5-yl)-3-methyl-3,4-dihydropyridine-1(2H)-carboxylate Prepared by general procedure Scheme J step 3. Yield: 3 g of crude.
LCMS(ESI): [M]$^+$ m/z: calcd 415.2; found 416.2; Rt=1.041 min.

Step 4: Synthesis of (S)—N,N-dimethyl-2-(5-(5-methyl-3,4,5,6-tetrahydropyridin-2-yl)benzo[d]thiazol-2-yl)propan-2-amine Prepared by general procedure Scheme J step 4. Yield: 0.44 g of crude.
LCMS(ESI): [M]$^+$ m/z: calcd 315.2; found 316.2; Rt=0.524 min.

Step 5: Synthesis of N,N-dimethyl-2-(5-((2R,5S)-5-methylpiperidin-2-yl)benzo[d]thiazol-2-yl)propan-2-amine Prepared by general procedure Scheme J step 5. Yield: 0.36 g (81.30%).
LCMS(ESI): [M]$^+$ m/z: calcd 317.2; found 318.2; Rt=0.535 min.

Step 6: Synthesis of N-(6-amino-5-ethylpyridin-3-yl)-2-((2R,5S)-2-(2-(2-(dimethylamino)propan-2-yl)benzo[d]thiazol-5-yl)-5-methylpiperidin-1-yl)-2-oxoacetamide (Compound 1237

Prepared by general procedure Scheme J step 6A. Yield: 54.7 mg (34.14%).
HPLC conditions: Column: YMC Triart C18 100*20 mm, 5 microM; 0-1-6 min 50-50-90% water-MeOH+0.1% NH$_4$OH, flow: 30 mL/min; (loading pump 4 mL/min MeOH).
$^1$H NMR (600 MHz, dmso) 6 1.00-1.06 (m, 3H), 1.06-1.19 (m, 3H), 1.28-1.40 (m, 1H), 1.42 (s, 6H), 1.62-1.76 (m, 1H), 1.83-1.95 (m, 1H), 2.03-2.18 (m, 1H), 2.22 (s, 6H), 2.26-2.33 (m, 1H), 2.36-2.44 (m, 2H), 2.76-3.29 (m, 1H), 3.43-4.10 (m, 1H), 5.18-5.61 (m, 1H), 5.61-5.73 (m, 2H), 7.31-7.42 (m, 1H), 7.42-7.57 (m, 1H), 7.82-7.91 (m, 1H), 7.98-8.14 (m, 2H), 10.43-10.65 (m, 1H).
LCMS(ESI): [M]$^+$ m/z: calcd 508.2; found 509.2; Rt=1.645 min.

Scheme K Synthesis of Compounds of Formula 11

Compounds of Formula 11 are are compounds of Formula (I) wherein R$^1$, R$^2$, R$^3$, R$^4$, R$^6$ R$^7$, and R$^8$ are as described herein.

General Procedure 11

Scheme K

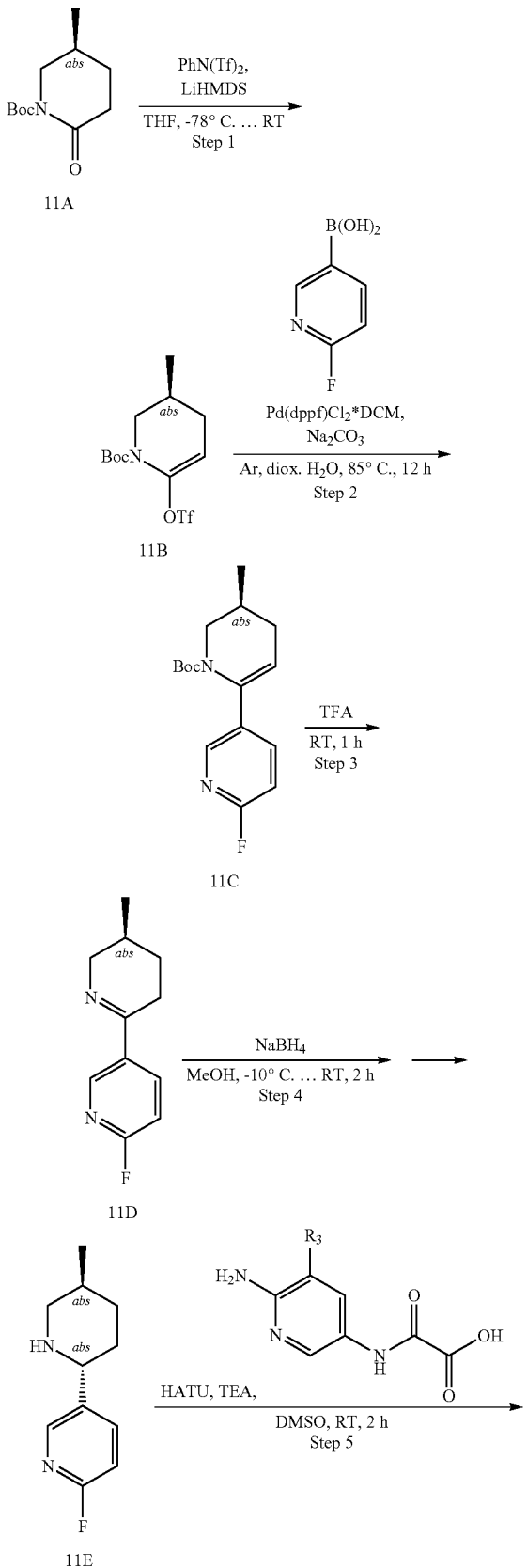

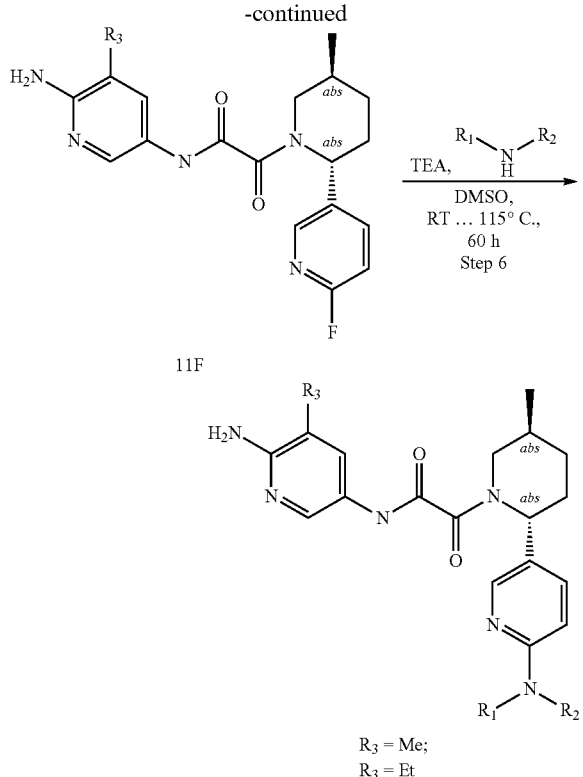

R₃ = Me;
R₃ = Et

Formula 11

Step 1: The Synthesis of 11B

LiHMDS (1.3 equiv; 1.08 M in THF/ethylbenzene) was added dropwise under argon to a cooled to −78° C. solution of 11A (1.0 equiv) in THF (400 mL). The resulting solution was stirred at −78° C. for 1.5 hr following by the addition of 1,1,1-trifluoro-N-phenyl-N-(trifluoromethylsulfonyl)methanesulfonamide (1.05 equiv). The reaction mixture was allowed to warm slowly (cooling bath was not removed!) to 25° C. and stirred for 12 hr. Then, the mixture was diluted with water (100 mL) and MTBE (700 mL). The organic layer was separated, the aqueous layer was additionally extracted with MTBE (200 mL). The combined organic extracts were washed with 10% aqueous sodium hydroxide solution (2*100 mL), dried over potassium carbonate (250 g) and concentrated in vacuo. The residue was diluted with hexane/MTBE mixture (4/1,500 ml, repeated 8 times) and stirred for 30 min. The resulting cloudy solution was decanted from oily residue, filtered through a short pad of silica gel (150 mL of dry silica gel) and evaporated in vacuo to afford 11B.

Step 2: The Synthesis of 11C 11B (1.0 equiv), (6-fluoro-3-pyridyl)boronic acid (1.38 equiv) and Sodium carbonate (3.05 equiv) were added to a mixture of 1,4-dioxane (100 mL) and water (30 mL). The resulting mixture was evacuated and then backfilled with argon, this operation was repeated three times, then Pd(dppf)Cl₂*DCM (0.05 equiv) was added under argon. The reaction mixture was stirred under argon at 85° C. for 18 hr. The resulting mixture was allowed to cool to the room temperature and filtered. The filtercake was washed with dioxane (2*50 mL) and discarded. The filtrate was concentrated in vacuo, and the residue was twice purified by column chromatography on silica gel using hexane/MTBE gradient (0-100% MTBE) to afford 11C.

Step 3: The Synthesis of 11D

A solution of 11C (1.0 equiv) in Trifluoroacetic acid (50.0 mL) was stirred at 25° C. for 1 hr, and then concentrated in vacuo. Crushed ice (10 g) was added to the residue, and the resulting mixture was basified to pH 10 with 10% aqueous potassium carbonate solution and extracted with dichloromethane (2*100.0 mL). The combined organic extracts were dried over sodium sulphate and concentrated under reduced pressure to afford 11D.

Step 4: The Synthesis of 11E

Sodium Borohydride (2.14 equiv) was added in one portion to a stirred solution 11D (1.0 equiv) in methanol (50 mL) at −10° C. The resulting mixture was stirred at −10° C. for 30 min, and was allowed to warm to 25° C. and stirred for 1 hr. The reaction mixture was concentrated in vacuo, the residue was diluted with water (30.0 mL) and extracted with dichloromethane (2*100.0 mL). The combined organic extracts were dried over sodium sulphate and concentrated in vacuo to afford 11E.

Step 5: The Synthesis of 11F

HATU (1.15 equiv) was added in small portions over 30 min to a stirred mixture of 11E (1.0 equiv), 2-[(6-amino-5-methyl/ethyl-3-pyridyl)amino]-2-oxo-acetic acid (1.25 equiv) and triethyl amine (6.0 equiv) in DMSO (22.0 mL) at 25° C. The resulting mixture was stirred at 25° C. for 2 hr. The mixture was analyzed with LCMS and the reaction mixture was used directly in the next step.

Step 6: The Synthesis of Formula 9

Method A:

Respective amine (2.5 equiv) was added to the reaction mixture from previous step containing 11F (1.0 equiv). The resulting mixture was stirred in sealed vial at 115° C. for 40-61 hr (LCMS control). Then, the mixture was allowed to cool to the room temperature and submitted to reverse phase HPLC to afford Formula 9.

Method B:

Respective amine (2.5 equiv) and triethylamine (2.0 equiv) were added to a stirred mixture of 11E (1.0 equiv). The resulting mixture was stirred in sealed vial at 115° C. for 60 hr, then cooled down and poured in cold water (40 mL). The resulting mixture was allowed to stand for 0.5 hr. The resulting precipitate was filtered, washed with water (3*5 mL) and then dissolved in dichloromethane (30 mL). The solution was dried over sodium sulphate and concentrated in vacuo. The residue was dissolved in dry dichloromethane (10 mL) and Hydrogen chloride solution 4.0 M in dioxane (60.0 equiv) was added in one portion. The resulting mixture was stirred at 25° C. for 0.5 hr, and then evaporated to dryness in vacuo. The residue was submitted to reverse phase HPLC to afford Formula 9.

2809

Example 666. The Synthesis of N-(6-amino-5-methyl-3-pyridyl)-2-[(2R,5S)-5-methyl-2-[6-[Methyl-(1-methyl-4-piperidyl)amino]-3-pyridyl]-1-piperidyl]-2-oxo-acetamide (Compound 1225)

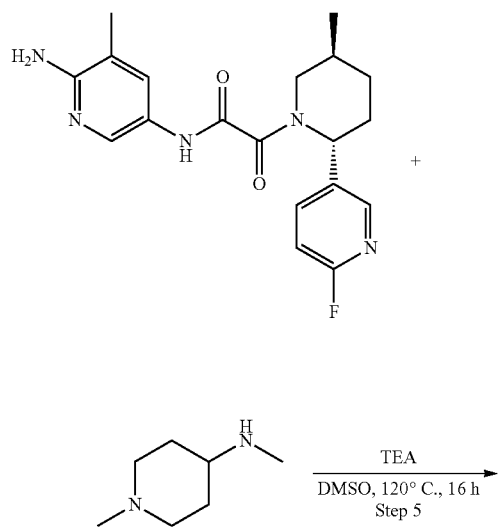

Prepared by General Procedure Scheme K Step 6 (Method A)

HPLC conditions: column: XBridge BEH C18 5 um 130 A; mobile phase: 30-30-75% 0-1-6 min H$_2$O/MeOH/0.1% NH$_4$OH; flow rate: 30 mL/min (loading pump 4 mL/min methanol)

Yield: 106.0 mg (28.70%)

$^1$H NMR (600 MHz, dmso) δ 1.00 (m, 3H), 1.29-1.36 (m, 2H), 1.48 (m, 2H), 1.70-1.74 (m, 3H), 1.94-1.99 (m, 2H), 2.03 (s, 3H), 2.15 (m, 3H), 2.80 (m, 5H), 3.92-3.94 (m, 1H), 4.38 (m, 2H), 5.01 (m, 1H), 5.49 (m, 1H), 5.61 (m, 2H), 6.58-6.62 (m, 1H), 7.39-7.48 (m, 2H), 7.97-8.02 (m, 2H), 10.46 (m, 1H).

LCMS(ESI): [M+2H]$^+$ m/z: calcd 481.2; found 481.2; Rt=1.552 min.

2810

Example 667. The Synthesis of N-(6-amino-5-ethyl-3-pyridyl)-2-[(2R,5S)-2-[6-[(3S)-3,4-dimethylpiperazin-1-yl]-3-pyridyl]-5-methyl-1-piperidyl]-2-oxo-acetamide (Compound 1289) and N-(6-amino-5-ethyl-3-pyridyl)-2-[(2R,5S)-2-[6-[(3R)-3,4-dimethylpiperazin-1-yl]-3-pyridyl]-5-methyl-1-piperidyl]-2-oxo-acetamide (Compound 1263

Step 1: The Synthesis of N-(6-amino-5-ethyl-3-pyridyl)-2-[(2R,5S)-2-(6-Fluoro-3-pyridyl)-5-methyl-1-piperidyl]-2-oxo-acetamide

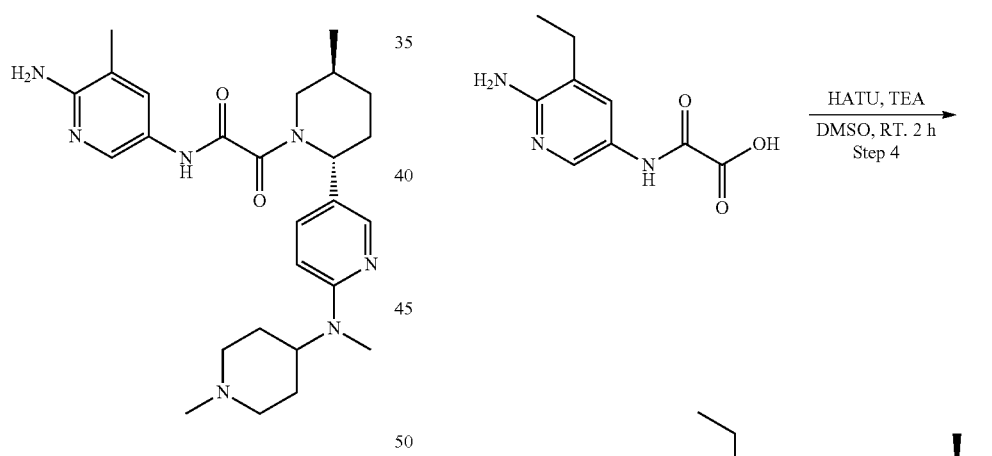

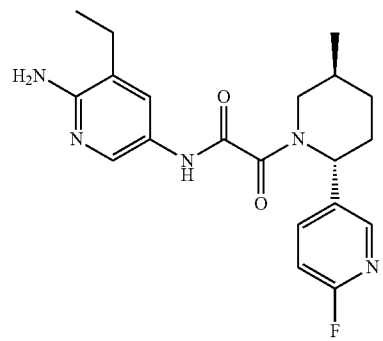

Prepared by General Procedure Scheme K Step 5

Yield: 1.79 g (crude)

LCMS(ESI): [M+H]$^+$ m/z: calcd 386.2; found 386.2; Rt=2.227 min.

2811

Step 2: The Synthesis of N-(6-amino-5-ethyl-3-pyridyl)-2-[(2R,5S)-2-[6-(3,4-dimethylpiperazin-1-yl)-3-pyridyl]-5-methyl-1-piperidyl]-2-oxo-acetamide

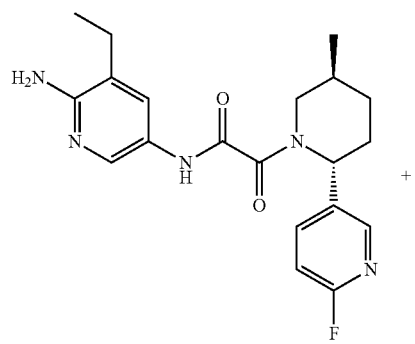

+

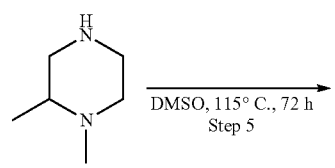

DMSO, 115° C., 72 h
Step 5

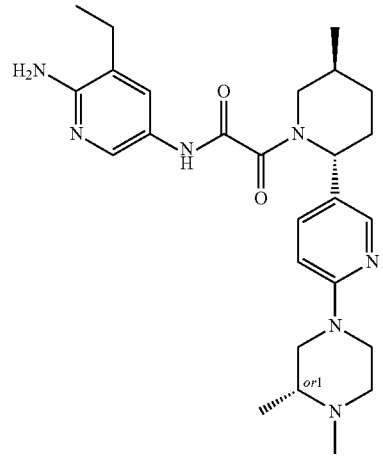

Prepared by General Procedure Scheme K Step 6 (Method A)

HPLC conditions: column: YMC Triart C18 100×20 mm, 5 um; mobile phase: 30-30-45% 0-2-5 min H$_2$O/Acetonitrile/0.1% NH$_4$OH, flow rate: 30 mL/min; (loading pump 4 mL/min methanol)

Yield: 285 mg (60.27%)

LCMS(ESI): [M+H]$^+$ m/z: calcd 480.4; found 480.4; Rt=1.782 min.

2812

Step 3: The Synthesis of N-(6-amino-5-ethyl-3-pyridyl)-2-[(2R,5S)-2-[6-[(3S)-3,4-dimethylpiperazin-1-yl]-3-pyridyl]-5-methyl-1-piperidyl]-2-oxo-acetamide (Compound 1289) and N-(6-amino-5-ethyl-3-pyridyl)-2-[(2R,5S)-2-[6-[(3R)-3,4-dimethylpiperazin-1-yl]-3-pyridyl]-5-methyl-1-piperidyl]-2-oxo-acetamide (Compound 1263)

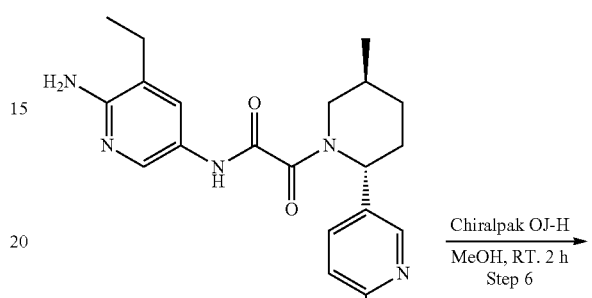

Chiralpak OJ-H
MeOH, RT. 2 h
Step 6

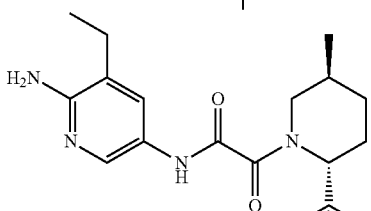

+

Compound 1289

Compound 1263

Prepared by General Procedure Scheme K Step 7

Chiral separation conditions: Chiralcel OJ-H, 250*20 mm, 5 mkm, MeOH, 100%, 18 mL/min, Inj Volume: 200.000 μl; Column Temperature: 25° C.; Wavelength: 205 nm, 264 nm), RetTime (isomer A)=21.799 min; RetTime (isomer B)=57.625 min Compound 1289:

Yield: 46.0 mg (36.80%)

RT (Chiralcel OJ-H, 250*20 mm, 5 mkm, Hex-IPA-MeOH, 50-25-25, 0.6 mL/min)=48.548 min.

$^1$H NMR (DMSO-$d_6$, 600 MHz): δ (ppm) 1.01 (m, 6H), 1.09 (m, 3H), 1.32 (m, 1H), 1.70 (m, 1H), 1.85 (m, 1H), 1.95 (m, 2H), 2.12 (m, 2H), 2.18 (s, 3H), 2.39 (m, 2H), 2.91 (m, 4H), 3.69 (m, 1H), 4.04 (m, 2H), 5.58 (m, 3H), 6.83 (m, 1H), 7.45 (m, 2H), 8.03 (m, 2H), 10.47 (s, 1H)

LCMS(ESI): [M+2H]$^+$ m/z: calcd 481.2; found 481.2; Rt=1.804 min.

Compound 1263:

Yield: 52.0 mg (41.60%)

RT (Chiralcel OJ-H, 250*20 mm, 5 mkm, Hex-IPA-MeOH, 50-25-25, 0.6 mL/min)=81.723 min.

$^1$H NMR (DMSO-$d_6$, 600 MHz): δ (ppm) 1.01 (m, 6H), 1.10 (m, 3H), 1.32 (m, 1H), 1.70 (m, 1H), 1.87 (m, 1H), 2.00 (m, 2H), 2.11 (m, 1H), 2.18 (s, 3H), 2.39 (m, 3H), 2.88 (m, 4H), 3.67 (dd, 1H), 4.03 (m, 2H), 5.58 (m, 3H), 6.83 (t, 1H), 7.45 (m, 2H), 8.03 (m, 2H), 10.48 (s, 1H).

LCMS(ESI): [M+H]$^+$ m/z: calcd 480.2; found 480.4; Rt=1.810 min.

Example 668. The Synthesis of N-(6-amino-5-ethyl-3-pyridyl)-2-[(2R,5S)-5-methyl-2-[6-[(1-methyl-4-piperidyl)amino]-3-pyridyl]-1-piperidyl]-2-oxo-acetamide (Compound 1306)

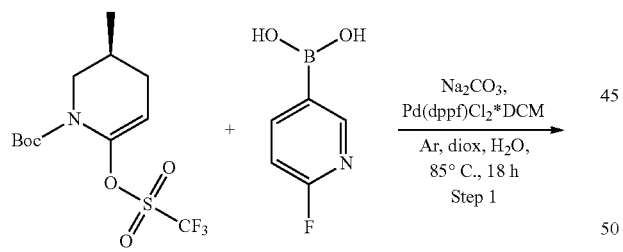

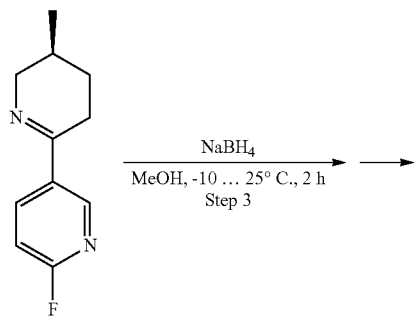

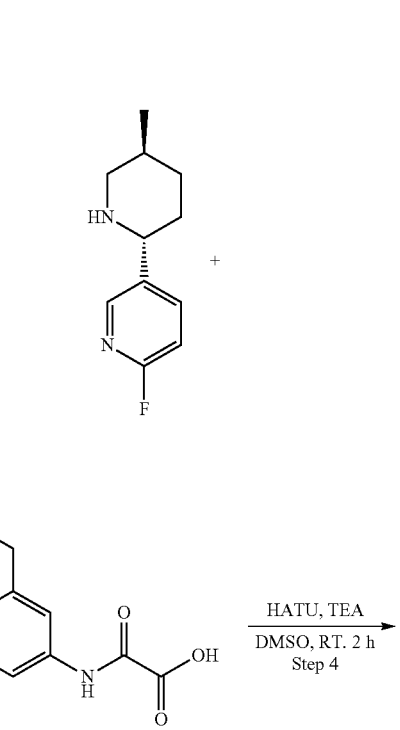

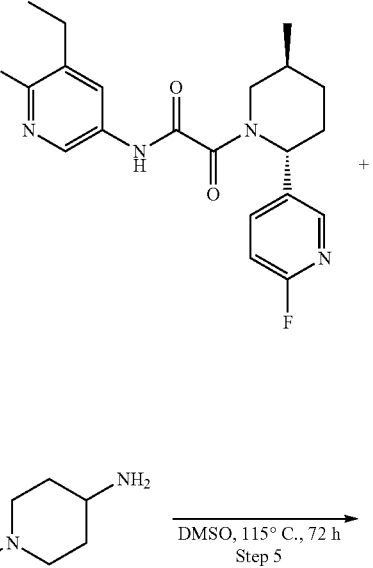

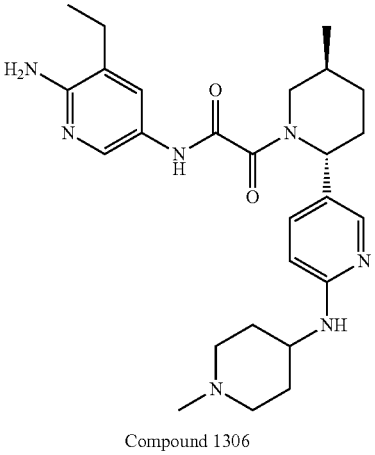 [SMILES: CCc1cc(NC(=O)C(=O)N2C[C@@H](C)CC[C@@H]2c2ccc(NC3CCN(C)CC3)nc2)cnc1N]

Compound 1306

Step 1: The Synthesis of tert-butyl (3S)-6-(6-Fluoro-3-pyridyl)-3-methyl-3,4-dihydro-2H-pyridine-1-carboxylate Prepared by General Procedure Scheme K Step 2
Yield: 3.0 g (44.30%)
LCMS(ESI): [M+H]+ m/z: calcd 293.2; found 293.2; Rt=1.500 min.

Step 2: The Synthesis of 2-Fluoro-5-[(3S)-3-methyl-2,3,4,5-tetrahydropyridin-6-yl]pyridine Prepared by General Procedure Scheme K Step 3
Yield: 1.9 g (96.32%)
LCMS(ESI): [M+H]+ m/z: calcd 193.2; found 193.2; Rt=0.634 min.

Step 3: The Synthesis of 2-Fluoro-5-[(2R,5S)-5-methyl-2-piperidyl]pyridine

Prepared by General Procedure Scheme K Step 4
Yield: 1.8 g (93.75%)
LCMS(ESI): [M+H]+ m/z: calcd 195.2; found 195.2; Rt=0.544 min.

Step 4: The Synthesis of N-(6-amino-5-ethyl-3-pyridyl)-2-[(2R,5S)-2-(6-Fluoro-3-pyridyl)-5-methyl-1-piperidyl]-2-oxo-acetamide Prepared by General Procedure Scheme K Step 5
Yield: 1.79 g (crude)
LCMS(ESI): [M+H]+ m/z: calcd 386.2; found 386.2; Rt=2.227 min.

Step 5: The Synthesis of N-(6-amino-5-ethyl-3-pyridyl)-2-[(2R,5S)-5-methyl-2-[6-[(1-methyl-4-piperidyl)amino]-3-pyridyl]-1-piperidyl]-2-oxo-acetamide (Compound 1306

Prepared by General Procedure Scheme K Step 6 (Method A)
HPLC conditions: column: YMC Triart C18 100×20 mm, 5 um; mobile phase: 5-95% 0-5 min $H_2O$/MeOH/0.1% $NH_4OH$, flow rate: 30 mL/min; (loading pump 4 mL/min methanol)
Yield: 83.0 mg (26.68%)
$^1$H NMR (600 MHz, DMSO-$d_6$) δ (ppm)
LCMS(ESI): [M+H]+ m/z: calcd 480.2; found 480.2; Rt=1.488 min.

Scheme L Synthesis of Compounds of Formula 12

Compounds of Formula 11 are are compounds of Formula (I) wherein $R^1$, $R^2$, $R^3$, $R^4$, $R^6$ R7, and $R^8$ are as described herein.
General Procedure 12

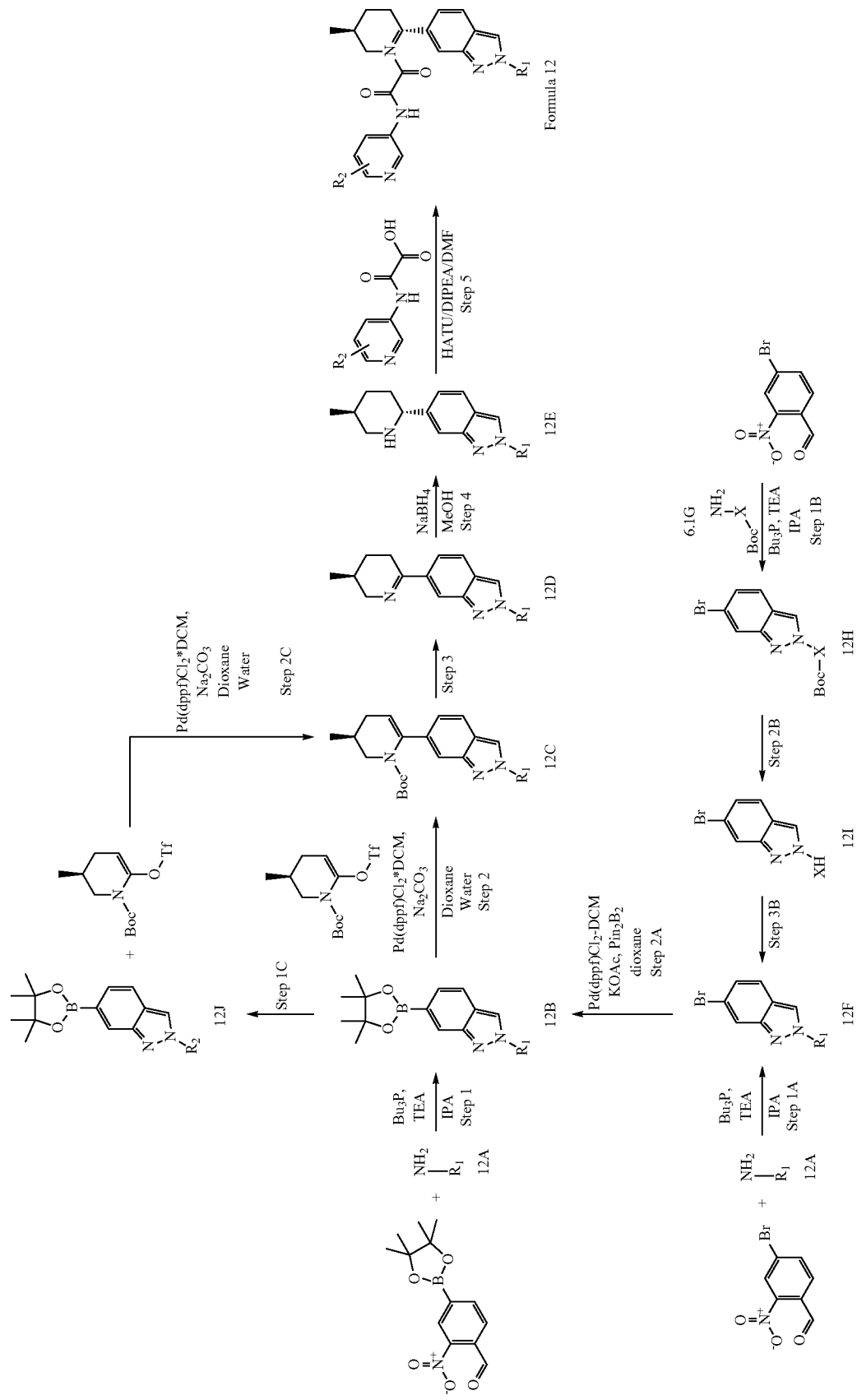

Step 1: General Procedure for 12B 2-nitro-5-(4,4,5,5-tetramethyl-1,3,2-dioxaborolan-2-yl) benzaldehyde (1.0 equiv.) and 12A (1.0 equiv., or it's salt) were dissolved in i-PrOH (140 mL). The resulting mixture was stirred at 80° C. for 2 hours following by the addition of tri-n-butyl phosphine (Bu$_3$P, 3.0 equiv.). The reaction mixture was stirred under reflux for 2 hours. Then, the volatiles were removed in vacuo. The residue was dissolved in DCM and washed with water. The organic layer separated, dried over Na$_2$SO$_4$ and concentrated under reduced pressure. The residue was purified by flash chromatography to afford 12B.

Step 1A: General Procedure for 12F 5-bromo-2-nitro-benzaldehyde (1.0 equiv.) and 12A (1.0 equiv.) were dissolved in i-PrOH (400.0 mL). The resulting mixture was stirred at 80° C. for 2 hr following by the addition of tri-n-butyl phosphine (3.0 equiv.). The reaction mixture was refluxed additionally for 16 hr. Then the reaction mixture was evaporated under reduced pressure and purified by flash chromatography to afford 12F.

Step 1B: General Procedure for 12H 5-bromo-2-nitro-benzaldehyde (1.0 equiv.) and 12G (1.0 equiv.) were dissolved in i-PrOH (80.0 mL). The resulting mixture was stirred at 80° C. for 2 hr and tri-n-butyl phosphine (3.0 equiv.) was added. The reaction mixture was refluxed additionally for 16 hr. Then the reaction mixture was evaporated under reduced pressure and purified by flash chromatography to afford 12H.

Step 1C: General Procedure for 12J

Potassium carbonate, anhydrous, 99% (3.0 equiv.) and iodomethane (1.7 equiv) were added to the solution of 12B (1.0 equiv.) in MeCN (appr. 45.0 mL). The resulting mixture was stirred at 25° C. for 16 hr. Then, solvent was removed under reduced pressure. The residue was diluted with water (40.0 mL) and the resulting mixture was extracted with DCM to 12J.

Step 2: General Procedure for 12C 12B (1.0 equiv.), tert-butyl rac-(3S)-3-methyl-6-(trifluoromethylsulfonyloxy)-3,4-dihydro-2H-pyridine-1-carboxylate (1.01 equiv.), sodium carbonate (3.0 equiv.) and Pd(dppf)Cl$_2$ DCM (0.05 equiv.) were stirred in a mixture of 1,4-dioxane (6.0 mL) and water (2.0 mL) under inert atmosphere at 85° C. for 15 hr. Upon completion, the reaction mixture was cooled down, diluted with water and extracted with DCM. The organic layer was separated, dried over Na$_2$SO$_4$ and concentrated under reduced pressure to afford 12C. The obtained material was used in the next step without an additional purification.

Step 2A: General Procedure for 12B 12F (1.0 equiv.), B$_2$Pin$_2$ (1.1 equiv.) and Potassium Acetate (2.0 equiv) were mixed together in 1.4-dioxane (appr. 20.0 mL). The resulting mixture was evacuated and then backfilled with argon, this operation was repeated three times, then Pd(dppf)$_2$Cl$_2$ DCM (993.01 mg, 1.22 mmol) was added under argon. The reaction mixture was stirred under argon atmosphere at 90° C. for 14 hr. Then the mixture was allowed to cool to the room temperature and the volatiles were removed in vacuo to afford 12B.

Step 2B: General Procedure for 12I 12H (1.0 equiv.) was dissolved in a mixture of TFA (1.0 mL) and DCM (1.0 mL). The reaction mixture was stirred at room temperature for 30 minutes. Then, the mixture was concentrated in vacuo to 12I. The obtained material was used in the next step without an additional purification.

Step 2C: General Procedure for Formula 12

Sodium carbonate (2.0 equiv.) was added to a solution of 12J (1.0 equiv.) and tert-butyl rac-(5S)-5-methyl-2-(trifluoromethylsulfonyloxy)piperidine-1-carboxylate (1.1 equiv.) in Water (appr. 15.0 mL) and 1,4-dioxane (appr. 50.0 mL). Reaction flask was evacuated and refilled with argon 3 times. Then, Pd(dppf)Cl$_2$CH$_2$Cl$_2$ (0.05 equiv.) was added under stream of argon. The resulting mixture was stirred at 90° C. for 15 hr under inert atmosphere. Upon completion of the reaction, water (appr. 50.0 mL) was added. The resulting mixture was extracted with EtOAc (3*20.0 mL). The combined organic layers were dried over Na$_2$SO$_4$, filtered and concentrated in vacuo to obtain 12C. The obtained material was used in the next step without an additional purification.

Step 3: General Procedure for 12D

Method A:
12C (1.0 equiv.) was dissolved in a mixture of TFA (1.0 mL) and DCM (1.0 mL). The reaction mixture was stirred at room temperature for 30 minutes. Then, the mixture was concentrated in vacuo to 12D. The obtained material was used in the next step without an additional purification.
Method B:
12C (1.0 equiv.) was dissolved in a mixture of HCl (4.0 M solution in dioxane, 1.0 mL) and MeOH (1.0 mL). The reaction mixture was stirred at room temperature overnight. Then, the mixture was concentrated in vacuo to 12D. The obtained material was used in the next step without an additional purification.

Step 3B: General Procedure for 12F

To a solution of 12I (1.0 equiv.), acetic acid (1.0 equiv.) and Formaldehyde, 37% in aq. soln., ACS, 36.5-38.0%, stab. with 10-15% methanol (1.0 equiv.) in DCM (appr. 25.0 mL), Sodium triacetoxyborohydride (1.0 equiv.) was added. The resulting mixture was stirred at 25° C. for 16 hr. Then, the solvent was removed in vacuo. The residue was poured in H$_2$O (50.0 mL) and extracted with EtOAc (2×20.0 mL). The combined organic extracts were washed with brine (2*20.0 mL), dried over sodium sulphate and evaporated in vacuo to afford 12F.

Step 4: General Procedure for 12E

Sodium Borohydride (2.0 equiv) was portionwise added to the solution of 12D (1.0 equiv.) in MeOH (5.0 mL). The reaction mixture was stirred at room temperature for 17 hours. Then, the mixture was acidified with HCl (4.0 M solution in dioxane) to pH 5 and the volatiles were removed in vacuo to afford 12E. The obtained material was used in the next step without an additional purification.

Step 5: General Procedure for Formula 12

HATU (1.4 equiv.) was added to the stirred solution of 12E (1.0 equiv), corresponding acid (1.1 equiv) and DIPEA (10.0 equiv) in DMSO (appr. 6.0 mL). The resulting reaction mixture was stirred at 25° C. for 4 hr. Upon completion, the reaction mixture was submitted to reverse phase HPLC to afford Formula 12.
Example 669. The Synthesis of N-(6-amino-5-ethyl-3-pyridyl)-2-[(2R,5S)-5-methyl-2-[2-(1-methyl-4-piperidyl)indazol-5-yl]-1-piperidyl]-2-oxo-acetamide (Compound 1321)
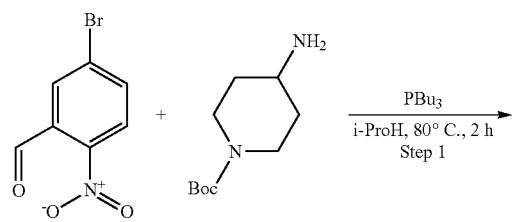
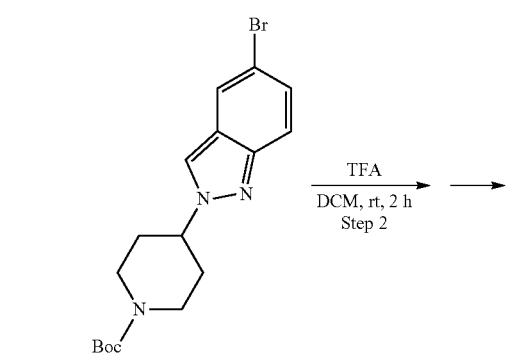
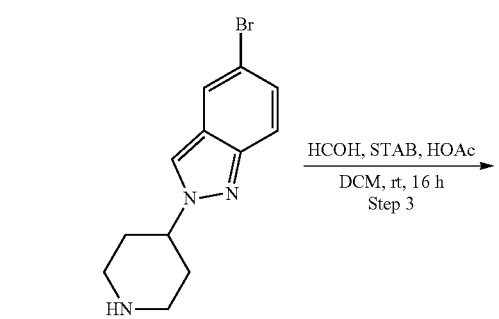
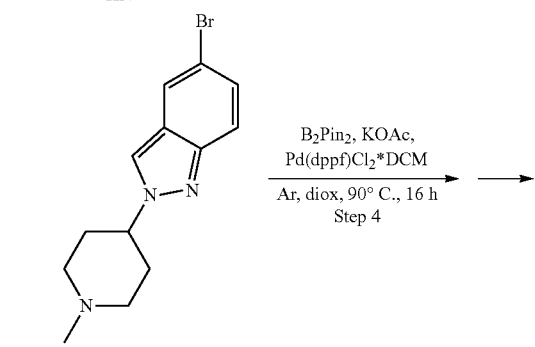
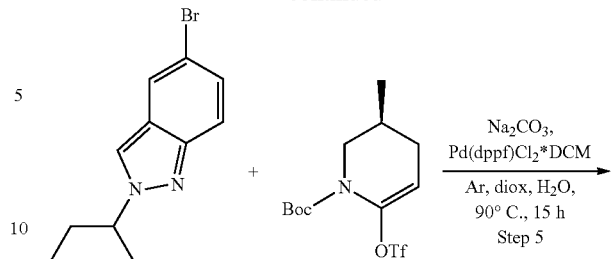
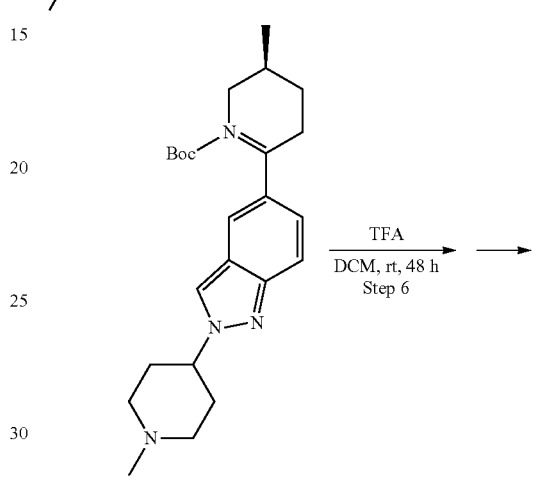
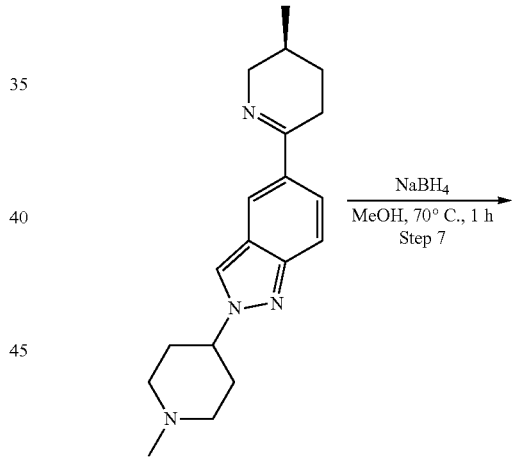
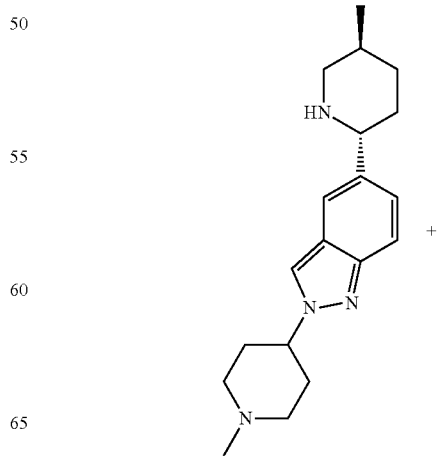

-continued

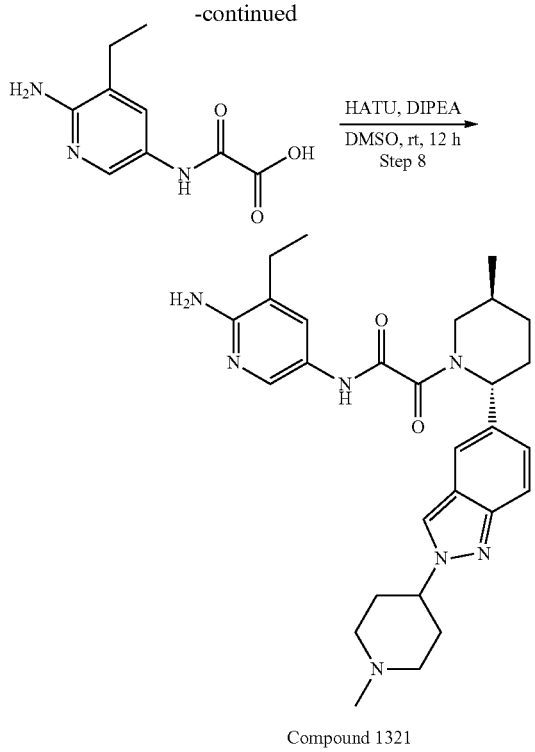

Compound 1321

Step 1: The Synthesis of tert-butyl 4-(5-bromoindazol-2-yl)piperidine-1-carboxylate Prepared by General Procedure Scheme L Step 1B
FCC conditions: Interchim; 120 g SiO$_2$, HEX-ETOAC from 0~100%, flow rate=70 mL/min,
cv=10.4
Yield: 4.2 g (84.68%)
LCMS(ESI): [M+H]$^+$ m/z: calcd 382.0; found 382.0; Rt=1.402 min.

Step 2: The Synthesis of 5-bromo-2-(4-piperidyl)indazole

Prepared by General Procedure Scheme L Step 2B
Yield: 0.42 g (38.01%)
LCMS(ESI): [M+H]$^+$ m/z: calcd 280.0; found 280.0; Rt=0.895 min.

Step 3: The Synthesis of 5-bromo-2-(1-methyl-4-piperidyl)indazole

Prepared by General Procedure Scheme L Step 3B
Yield: 0.42 g (88.88%)
LCMS(ESI): [M+H]$^+$ m/z: calcd 294.0; found 294.0; Rt=0.880 min.

Step 4: The Synthesis of 2-(1-methyl-4-piperidyl)-5-(4,4,5,5-tetramethyl-1,3,2-dioxaborolan-2-yl)indazole Prepared by General Procedure Scheme L Step 2A
Yield: 0.45 g (crude)
LCMS(ESI): [M+H]$^+$ m/z: calcd 342.2; found 342.2; Rt=0.916 min.

Step 5: The Synthesis of tert-butyl (3S)-3-methyl-6-[2-(1-methyl-4-piperidyl)indazol-5-yl]-3,4-dihydro-2H-pyridine-1-carboxylate Prepared by General Procedure Scheme L Step 2
Yield: 0.38 g (crude)
LCMS(ESI): [M+H]$^+$ m/z: calcd 411.2; found 411.2; Rt=1.048 min.

Step 6: The Synthesis of 2-(1-methyl-4-piperidyl)-5-[(3S)-3-methyl-2,3,4,5-tetrahydropyridin-6-yl]indazole Prepared by General Procedure Scheme L Step 3 (Method A)
Yield: 0.25 g (87.01%)
LCMS(ESI): [M+H]$^+$ m/z: calcd 311.2; found 311.2; Rt=0.881 min.

Step 7: The Synthesis of 2-(1-methyl-4-piperidyl)-5-[(2R,5S)-5-methyl-2-piperidyl]indazole Prepared by General Procedure Scheme L Step 4
Yield: 0.22 g (crude)

Step 8: The Synthesis of N-(6-amino-5-ethyl-3-pyridyl)-2-[(2R,5S)-5-methyl-2-[2-(1-methyl-4-piperidyl)indazol-5-yl]-1-piperidyl]-2-oxo-acetamide (Compound 1321

Prepared by General Procedure Scheme L Step 5
HPLC conditions: 2-15 min 40-60% methanol+NH$_3$, flow 30 mL/min (loading pump 4 mL/min methanol), column: SunFire 100*19 mm, 5 microM and 2-10 min 0-30% acetonitrile+FA flow 30 mL/min (loading pump 4 mL/min acetonitrile), Column Sun Fire C18 100*19 mm
Yield: 0.006 g (1.69%)
$^1$H NMR (600 MHz, dmso) δ 0.85-1.04 (m, 3H), 1.06-1.14 (m, 3H), 1.31-1.41 (m, 1H), 1.69-1.93 (m, 2H), 2.03-2.13 (m, 7H), 2.22 (s, 3H), 2.23-2.34 (m, 1H), 2.37-2.43 (m, 2H), 2.75-2.78 (m, OH), 2.87-2.90 (m, 2H), 3.19-3.22 (m, 1H), 3.49-4.03 (m, 1H), 4.37-4.47 (m, 1H), 5.15-5.70 (m, 3H), 7.12-7.29 (m, 1H), 7.41-7.54 (m, 1H), 7.57-7.64 (m, 2H), 7.97-8.10 (m, 1H), 8.35-8.40 (m, 1H), 10.45-10.69 (m, 1H).
LCMS(ESI): [M+H]$^+$ m/z: calcd 504.2; found 504.2; Rt=1.976 min.

Example 670. The Synthesis of 2-methoxy-5-[[2-oxo-2-[rac-(2R,5S)-5-methyl-2-[2-(1-methyl-4-piperidyl)indazol-5-yl]-1-piperidyl]acetyl]amino]pyridine-3-carboxamide (Compound 1115)

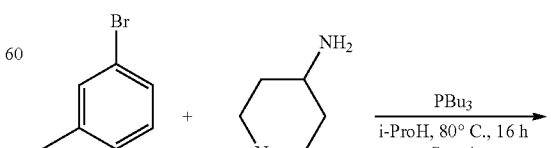

2825
-continued

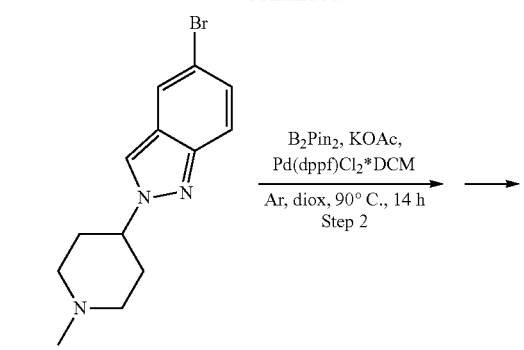

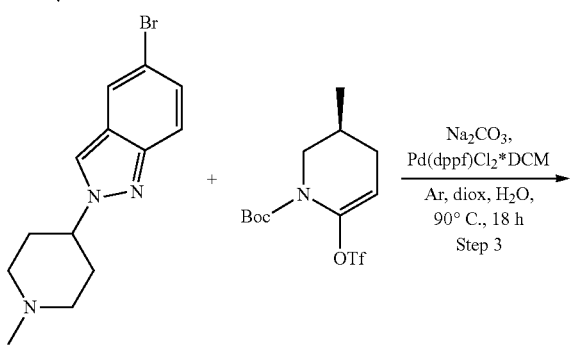

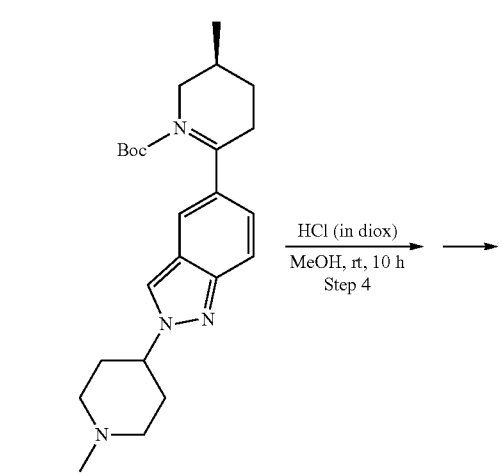

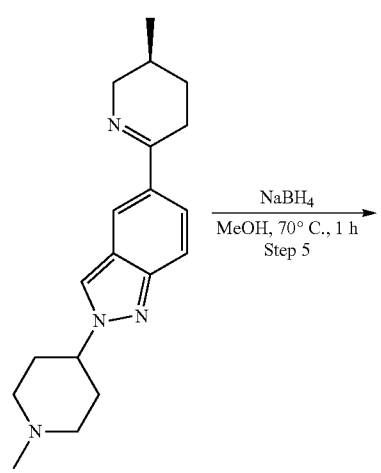

2826
-continued

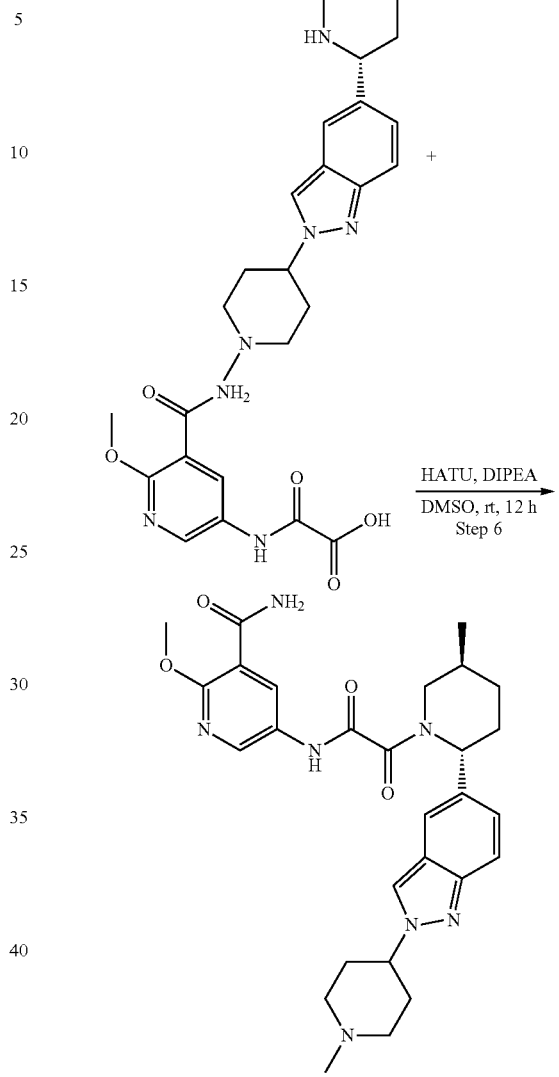

Step 1: The Synthesis of
5-bromo-2-(1-methyl-4-piperidyl)indazole

Prepared by General Procedure Scheme L Step 1A
 Yield: 20 g (78.19%)
 LCMS(ESI): [M+H]$^+$ m/z: calcd 295.0; found 295.0; Rt=0.785 min.

Step 2: The Synthesis of 2-(1-methyl-4-piperidyl)-5-(4,4,5,5-tetramethyl-1,3,2-dioxaborolan-2-yl)indazole Prepared by General Procedure Scheme L Step 1
 FCC conditions: Interchim; 330 g SiO$_2$, MTBE-MeOH from 0-100%, flow rate=100 mL/min, cv=9.4
 Yield: 9.0 g (77.59%)
 LCMS(ESI): [M+H]$^+$ m/z: calcd 342.2; found 342.2; Rt=0.799 min.

Step 3: The Synthesis of tert-butyl (3S)-3-methyl-6-[2-(1-methyl-4-piperidyl)indazol-5-yl]-3,4-dihydro-2H-pyridine-1-carboxylate Prepared by General Procedure Scheme L Step 2
 FCC conditions: Interchim; 120 g SiO$_2$, MTBE-MeOH from 0~100%, flow rate=70 mL/min,
  cv=15.3
 Yield: 6.0 g (55.41%)
 LCMS(ESI): [M+H]$^+$ m/z: calcd 411.2; found 411.5; Rt=1.019 min.

Step 4: The Synthesis of 2-(1-methyl-4-piperidyl)-5-[(3S)-3-methyl-2,3,4,5-tetrahydropyridin-6-yl]indazole Prepared by General Procedure Scheme L Step 3 (Method B)
 Yield: 1.2 g (79.35%)
 LCMS(ESI): [M+H]$^+$ m/z: calcd 311.2; found 311.2; Rt=0.769 min.

Step 5: The Synthesis of 2-(1-methyl-4-piperidyl)-5-[(2R,5S)-5-methyl-2-piperidyl]indazole Prepared by General Procedure Scheme L Step 4
 Yield: 3.2 g (79.48%)
 LCMS(ESI): [M+H]$^+$ m/z: calcd 313.2; found 313.2; Rt=0.664 min.

Step 6: The Synthesis of 2-methoxy-5-[[2-oxo-2-[rac-(2R,5S)-5-methyl-2-[2-(1-methyl-4-piperidyl)indazol-5-yl]-1-piperidyl]acetyl]amino]pyridine-3-carboxamide (Compound 1115

Prepared by General Procedure Scheme L Step 5
 HPLC conditions: 2-10 min 30-100% methanol flow 30 mL/min (loading pump 4 mL/min methanol), Column Sun Fire C18 100*19 mm
 Yield: 0.088 g (35.52%)
 $^1$H NMR (600 MHz, dmso) 6 1.01-1.05 (m, 3H), 1.30-1.40 (m, 1H), 1.73-1.94 (m, 2H), 1.96-2.33 (m, 11H), 2.80-2.90 (m, 2H), 3.40-4.34 (m, 5H), 4.38-4.47 (m, 1H), 5.17-5.75 (m, 1H), 7.07-7.30 (m, 1H), 7.55-7.64 (m, 2H), 7.66-7.80 (m, 2H), 8.31-8.63 (m, 3H), 10.94 (s, 1H).
 LCMS(ESI): [M+H]$^+$ m/z: calcd 534.2; found 534.2; Rt=1.820 min.

Example 671. The Synthesis of N-(6-amino-5-ethyl-3-pyridyl)-2-oxo-2-[rac-(2R,5S)-5-methyl-2-[2-[rac-(3S)-1-methylpyrrolidin-3-yl]indazol-5-yl]-1-piperidyl]acetamide (Compound 1091)

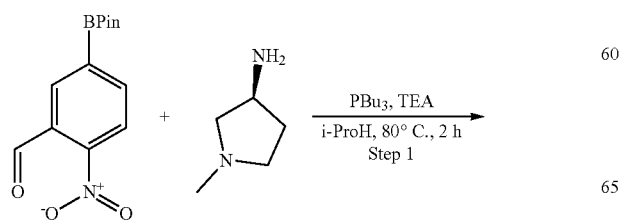

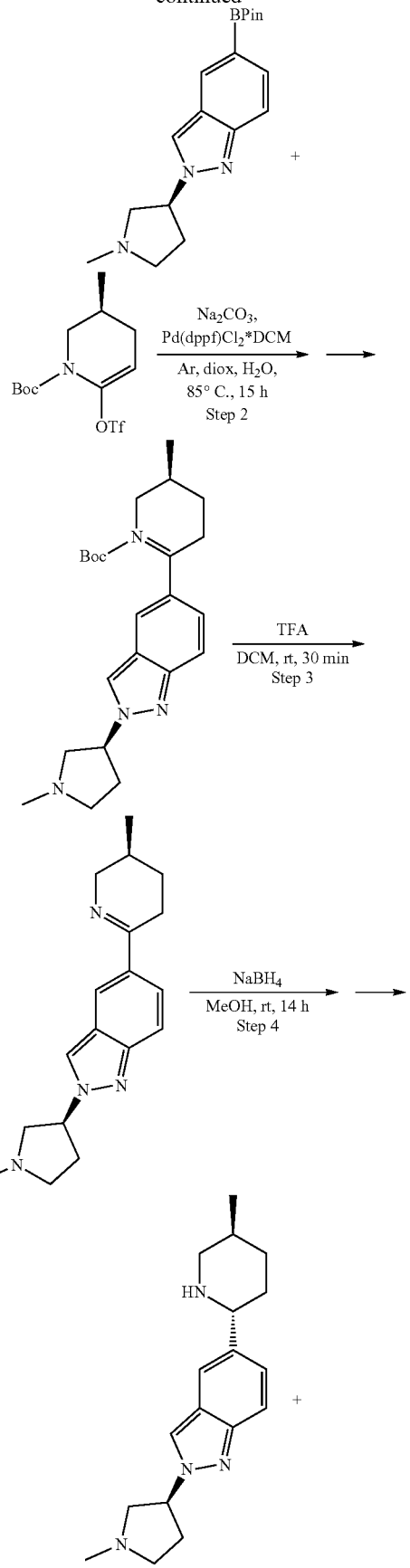

Step 4: The Synthesis of 5-[rac-(2R,5S)-5-methyl-2-piperidyl]-2-[rac-(3S)-1-methylpyrrolidin-3-yl] indazole Prepared by General Procedure 12

Yield: 1.5 g (crude, 2HCl)

LCMS(ESI): [M+H]+ m/z: calcd 299.2; found 299.2; Rt=0.680 min.

Step 5: The Synthesis of N-(6-amino-5-ethyl-3-pyridyl)-2-oxo-2-[rac-(2R,5S)-5-methyl-2-[2-[rac-(3S)-1-methylpyrrolidin-3-yl]indazol-5-yl]-1-piperidyl]acetamide (Compound 1091

Prepared by General Procedure 12

HPLC conditions: 2-10 min 40-100% methanol+NH3 flow 30 mL/min (loading pump 4 mL/min methanol), Column Sun Fire C18 100*19 mm Yield: 0.057 g, (14.41%)

$^{1}$H NMR (600 MHz, dmso) δ 1.00-1.14 (m, 6H), 1.29-1.40 (m, 1H), 1.72-1.92 (m, 2H), 2.02-2.25 (m, 3H), 2.30 (s, 3H), 2.38-2.44 (m, 2H), 2.52-2.54 (m, 1H), 2.75-3.24 (m, 5H), 3.43-4.04 (m, 1H), 5.15-5.68 (m, 4H), 7.12-7.27 (m, 1H), 7.42-7.53 (m, 1H), 7.56-7.64 (m, 2H), 7.97-8.08 (m, 1H), 8.36-8.42 (m, 1H), 10.51 (s, 1H).

LCMS(ESI): [M+H]+ m/z: calcd 490.2; found 490.4; Rt=2.198 min.

Example 672. The Synthesis of N-(6-amino-5-ethyl-3-pyridyl)-2-oxo-2-[rac-(2R,5S)-5-methyl-2-[2-[rac-(3R)-1-methylpyrrolidin-3-yl]indazol-5-yl]-1-piperidyl]acetamide (Compound 1398)

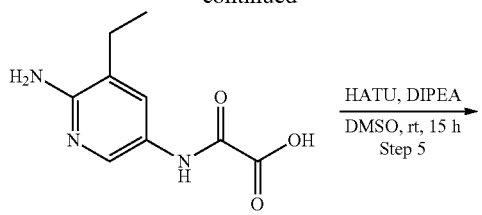

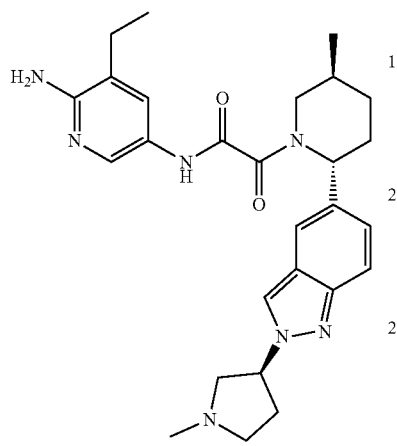

Step 1: The Synthesis of 2-[rac-(3S)-1-methylpyrrolidin-3-yl]-5-(4,4,5,5-tetramethyl-1,3,2-dioxaborolan-2-yl)indazole Prepared by General Procedure 12

FCC conditions: Interchim; 120 g SiO2, MTBE-MeOH from 0~100%, flow rate=70 mL/min, cv=13.9

Yield: 2.6 g (31.45%)

LCMS(ESI): [M+H]+ m/z: calcd 328.2; found 328.2; Rt=0.904 min.

Step 2: The Synthesis of tert-butyl rac-(3S)-3-methyl-6-[2-[rac-(3S)-1-methylpyrrolidin-3-yl]indazol-5-yl]-3,4-dihydro-2H-pyridine-1-carboxylate Prepared by General Procedure 12

Yield: 2.0 g (crude)

LCMS(ESI): [M+H]+ m/z: calcd 397.2; found 397.2; Rt=1.189 min.

Step 3: The Synthesis of 2-[rac-(3S)-1-methylpyrrolidin-3-yl]-5-[rac-(3S)-3-methyl-2,3,4,5-tetrahydropyridin-6-yl]indazole Prepared by General Procedure 12

Yield: 1.55 g (crude)

LCMS(ESI): [M+H]+ m/z: calcd 297.2; found 297.2; Rt=0.668 min.

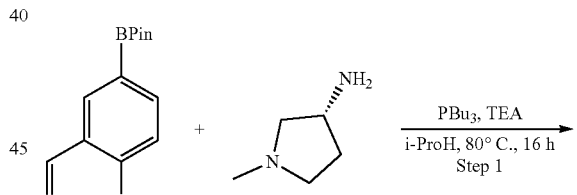

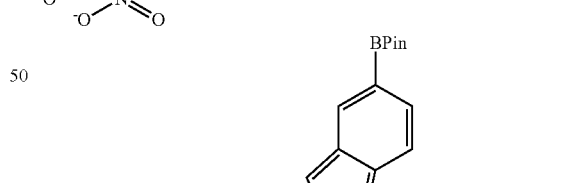

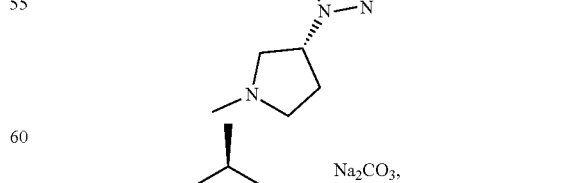

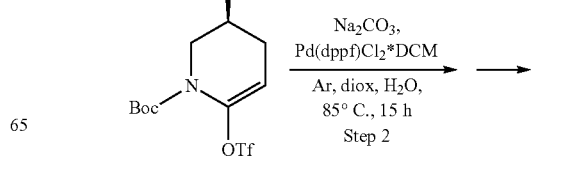

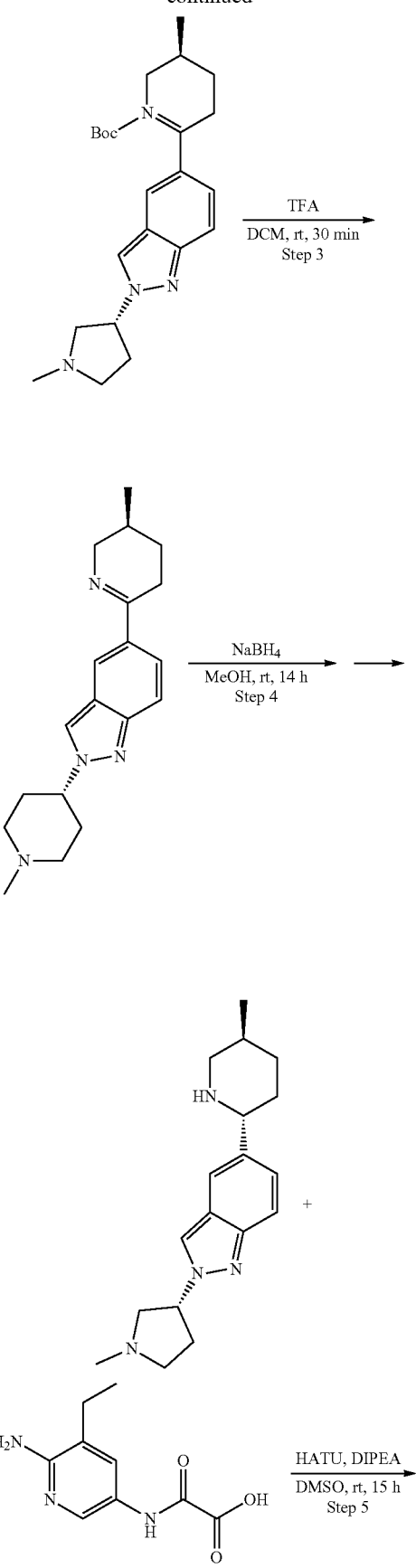

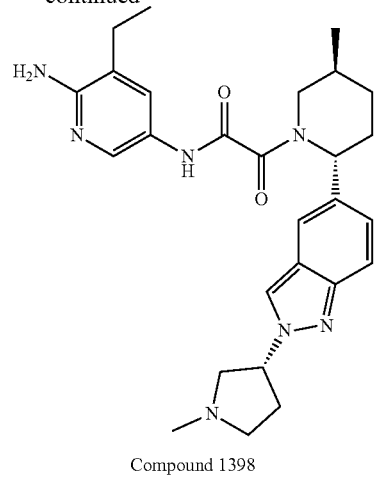

Compound 1398

Step 1: The Synthesis of 2-[rac-(3R)-1-methylpyrrolidin-3-yl]-5-(4,4,5,5-tetramethyl-1,3,2-dioxaborolan-2-yl)indazole Prepared by General Procedure Scheme L Step 1

FCC conditions: Interchim; 120 g SiO$_2$, MTBE-MeOH from 0-100%, flow rate=70 mL/min, cv=13.7

Yield: 3.6 g (43.55%)

LCMS(ESI): [M+H]$^+$ m/z: calcd 328.2; found 328.2; Rt=0.897 min.

Step 2: The Synthesis of tert-butyl rac-(3S)-3-methyl-6-[2-[rac-(3R)-1-methylpyrrolidin-3-yl]indazol-5-yl]-3,4-dihydro-2H-pyridine-1-carboxylate Prepared by General Procedure Scheme L Step 2

Yield: 3.5 g (crude)

LCMS(ESI): [M+H]$^+$ m/z: calcd 397.2; found 397.4; Rt=1.010 min.

Step 3: The Synthesis of 2-[rac-(3R)-1-methylpyrrolidin-3-yl]-5-[rac-(3S)-3-methyl-2,3,4,5-tetrahydropyridin-6-yl]indazole Prepared by General Procedure Scheme L Step 3 (Method A)

Yield: 2.0 g (crude)

LCMS(ESI): [M+H]$^+$ m/z: calcd 297.2; found 297.1; Rt=0.380 min.

Step 4: The Synthesis of 5-[rac-(2R,5S)-5-methyl-2-piperidyl]-2-[rac-(3R)-1-methylpyrrolidin-3-yl]indazole Prepared by General Procedure Scheme L Step 4

Yield: 1.9 g (crude, 2 HCl)

LCMS(ESI): [M+H]$^+$ m/z: calcd 299.2; found 299.0; Rt=0.675 min.

2833

Step 5: The Synthesis of N-(6-amino-5-ethyl-3-pyridyl)-2-oxo-2-[rac-(2R,5S)-5-methyl-2-[2-[rac-(3R)-1-methylpyrrolidin-3-yl]indazol-5-yl]-1-piperidyl]acetamide (Compound 1398

Prepared by General Procedure Scheme L Step 5

HPLC conditions: 2-10 min 50-70% methanol+NH$_3$ flow 30 mL/min (loading pump 4 mL/min methanol), column: sun fire C18

Yield: 0.06 g (15.17%)

$^1$H NMR (DMSO-d$_6$, 600 MHz): δ (ppm) 1.02 (m, 3H), 1.10 (m, 3H), 1.35 (m, 1H), 1.82 (m, 2H), 2.06 (m, 1H), 2.19 (m, 2H), 2.30 (s, 3H), 2.38 (m, 3H), 2.53 (m, 2H), 2.84 (m, 2H), 2.93 (m, 1H), 3.83 (m, 1H), 5.41 (m, 4H), 7.20 (m, 1H), 7.54 (m, 3H), 8.03 (m, 1H), 8.39 (m, 1H), 10.50 (m, 1H).

LCMS(ESI): [M+H]$^+$ m/z: calcd 490.2; found 490.4; Rt=1.708 min.

Example 673. The Synthesis of N-(6-amino-5-ethyl-3-pyridyl)-2-oxo-2-[rac-(2R,5S)-5-methyl-2-[2-(1-methylazetidin-3-yl)indazol-5-yl]-1-piperidyl]acetamide (Compound 1239)

2834

-continued

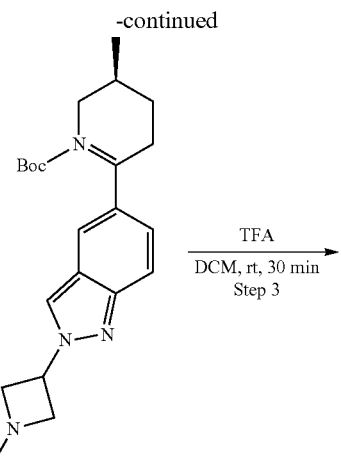

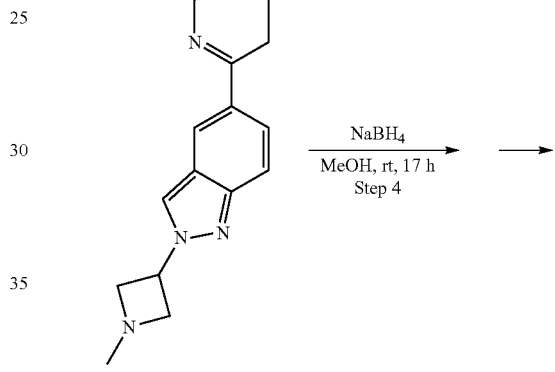

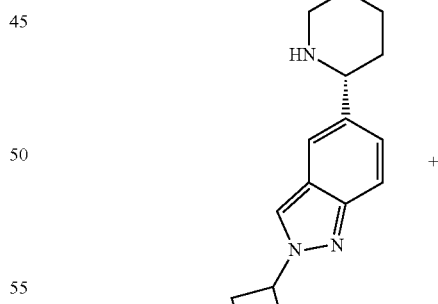

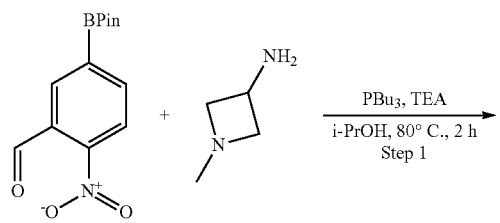

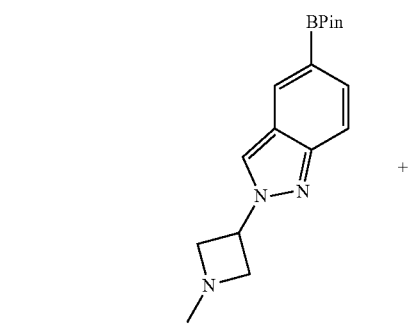

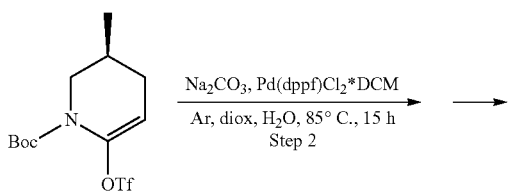

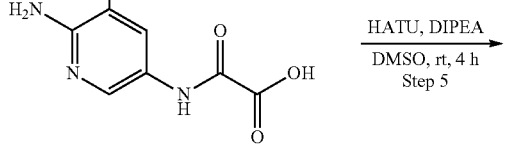

2835

-continued

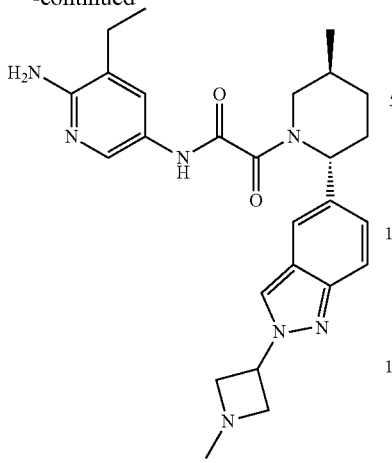

Step 1: The Synthesis of 2-(1-methylazetidin-3-yl)-5-(4,4,5,5-tetramethyl-1,3,2-dioxaborolan-2-yl)indazole Prepared by General Procedure Scheme L Step 1
FCC conditions: Interchim; 120 g SiO$_2$,MTBE-MeOH from 0~100%, flow rate=70 mL/min, cv=8.1
Yield: 3.0 g (37.91%)
LCMS(ESI): [M+H]$^+$ m/z: calcd 314.2; found 314.2; Rt=0.898 min.

Step 2: The Synthesis of tert-butyl rac-(3S)-3-methyl-6-[2-(1-methylazetidin-3-yl)indazol-5-yl]-3,4-dihydro-2H-pyridine-1-carboxylate Prepared by General Procedure Scheme L Step 2
Yield: 0.7 g (crude)
LCMS(ESI): [M+H]$^+$ m/z: calcd 383.0; found 383.0; Rt=1.179 min.

Step 3: The Synthesis of 2-(1-methylazetidin-3-yl)-5-[rac-(3S)-3-methyl-2,3,4,5-tetrahydropyridin-6-yl]indazole Prepared by General Procedure Scheme L Step 3 (Method A)
Yield: 0.6 g (crude)
LCMS(ESI): [M+H]$^+$ m/z: calcd 283.2; found 283.5; Rt=0.371 min.

Step 4: The Synthesis of 2-(1-methylazetidin-3-yl)-5-[rac-(2R,5S)-5-methyl-2-piperidyl]indazole Prepared by General Procedure Scheme L Step 4
Yield: 0.6 g (79.03%, 2HCl)
LCMS(ESI): [M+H]$^+$ m/z: calcd 285.2; found 285.2; Rt=0.660 min.

Step 5: The Synthesis of N-(6-amino-5-ethyl-3-pyridyl)-2-oxo-2-[rac-(2R,5S)-5-methyl-2-[2-(1-methylazetidin-3-yl)indazol-5-yl]-1-piperidyl]acetamide (Compound 1239

Prepared by General Procedure Scheme L Step 5
HPLC conditions: 2-10 min 50-60% methanol+NH$_3$ flow 30 mL/min (loading pump 4 mL/min methanol), Column Sun Fire C18 100*19 mm

2836

Yield: 0.047 g (5.89%)
$^1$H NMR (600 MHz, dmso) δ 0.99-1.05 (m, 3H), 1.06-1.13 (m, 3H), 1.29-1.42 (m, 1H), 1.66-1.79 (m, 1H), 1.81-1.90 (m, 1H), 2.02-2.18 (m, 1H), 2.21-2.29 (m, 1H), 2.34 (s, 3H), 2.38-2.44 (m, 2H), 2.76-3.19 (m, 1H), 3.48-4.03 (m, 5H), 5.21-5.28 (m, 1H), 5.54-5.68 (m, 3H), 7.15-7.29 (m, 1H), 7.42-7.52 (m, 1H), 7.59-7.65 (m, 2H), 7.98-8.08 (m, 1H), 8.41-8.48 (m, 1H), 10.51 (s, 1H).
LCMS(ESI): [M+2H]$^+$ m/z: calcd 477.2; found 477.4; Rt=2.184 min.

Example 674. The Synthesis of N-(6-amino-5-ethyl-3-pyridyl)-2-oxo-2-[rac-(2R,5S)-5-methyl-2-[2-[rac-(3R)-1-methyl-3-piperidyl]indazol-5-yl]-1-piperidyl]acetamide (Compound 1270)

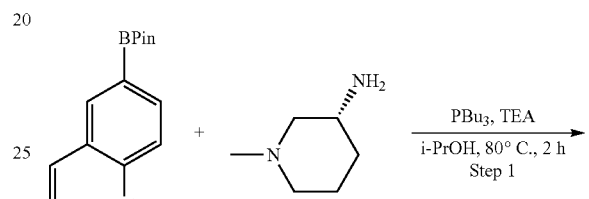

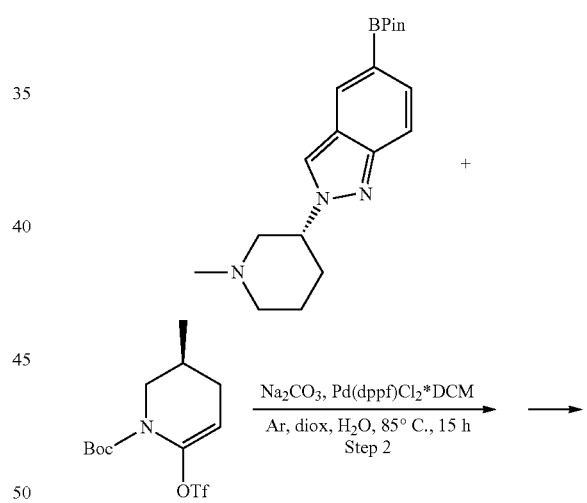

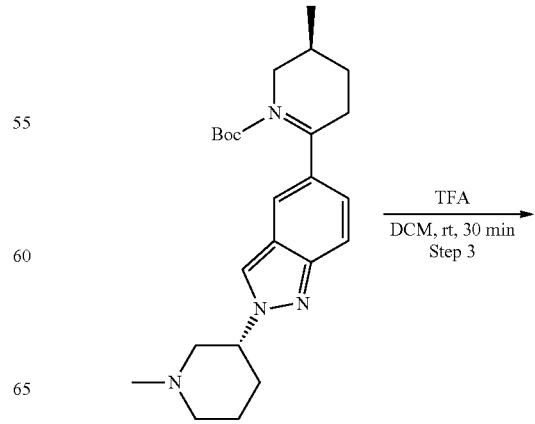

2837

-continued

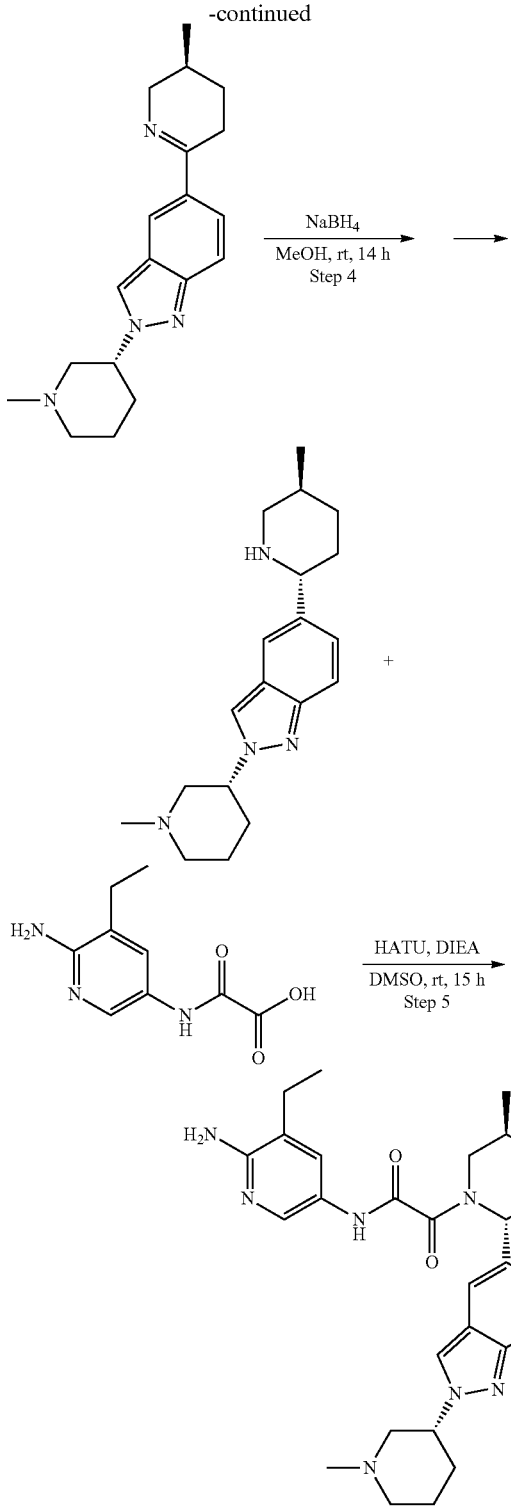

2838 cv=6
Yield: 3 g (34.80%)
LCMS(ESI): [M+H]$^+$ m/z: calcd 342.2; found 342.2; Rt=0.926 min.

Step 2: The Synthesis of tert-butyl rac-(3S)-3-methyl-6-[2-[rac-(3R)-1-methyl-3-piperidyl]indazol-5-yl]-3,4-dihydro-2H-pyridine-1-carboxylate Prepared by General Procedure Scheme L Step 2
Yield: 0.7 g (crude)
LCMS(ESI): [M+H]$^+$ m/z: calcd 411.4; found 411.4; Rt=0.870 min.

Step 3: The Synthesis of 2-[rac-(3R)-1-methyl-3-piperidyl]-5-[rac-(3S)-3-methyl-2,3,4,5-tetrahydro-pyridin-6-yl]indazole Prepared by General Procedure Scheme L Step 3 (Method A)
Yield: 0.45 g (crude)
LCMS(ESI): [M+H]$^+$ m/z: calcd 311.2; found 311.2; Rt=0.660 min.

Step 4: The Synthesis of 5-[rac-(2R,5S)-5-methyl-2-piperidyl]-2-[rac-(3R)-1-methyl-3-piperidyl]indazole Prepared by General Procedure Scheme L Step 4
Yield: 0.5 g (crude, 2HCl)
LCMS(ESI): [M+H]$^+$ m/z: calcd 313.2; found 313.2; Rt=0.687 min.

Step 5: The Synthesis of N-(6-amino-5-ethyl-3-pyridyl)-2-oxo-2-[rac-(2R,5S)-5-methyl-2-[2-[rac-(3R)-1-methyl-3-piperidyl]indazol-5-yl]-1-piperidyl]acetamide (Compound 1270

Prepared by General Procedure Scheme L Step 5
HPLC conditions: 2-10 min 50-100% methanol+NH$_3$ flow 30 mL/min (loading pump 4 mL/min methanol), column: sun fire C18
Yield: 0.018 g (2.75%)
$^1$H NMR (600 MHz, dmso) δ 0.99-1.05 (m, 3H), 1.05-1.15 (m, 4H), 1.29-1.41 (m, 1H), 1.61-1.95 (m, 6H), 1.98-2.09 (m, 3H), 2.21-2.29 (m, 4H), 2.66-3.03 (m, 4H), 3.43-4.03 (m, 1H), 4.55-4.63 (m, 1H), 5.15-5.66 (m, 3H), 7.12-7.26 (m, 1H), 7.41-7.53 (m, 1H), 7.55-7.64 (m, 2H), 7.97-8.10 (m, 1H), 8.40-8.46 (m, 1H), 10.44-10.56 (m, 1H).
LCMS(ESI): [M+H]$^+$ m/z: calcd 504.2; found 504.4; Rt=2.092 min.

Example 675. The Synthesis of N-(6-amino-5-ethyl-3-pyridyl)-2-oxo-2-[rac-(2R,5S)-5-methyl-2-[2-[rac-(3S)-1-methyl-3-piperidyl]indazol-5-yl]-1-piperidyl]acetamide (Compound 1271)

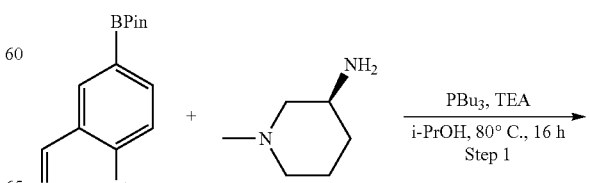

Step 1: The Synthesis of 2-[rac-(3R)-1-methyl-3-piperidyl]-5-(4,4,5,5-tetramethyl-1,3,2-dioxaborolan-2-yl)indazole Prepared by General Procedure Scheme L Step 1
FCC conditions: Interchim; 120 g SiO$_2$, MTBE-MeOH from 0-100%, flow rate=70 mL/min,

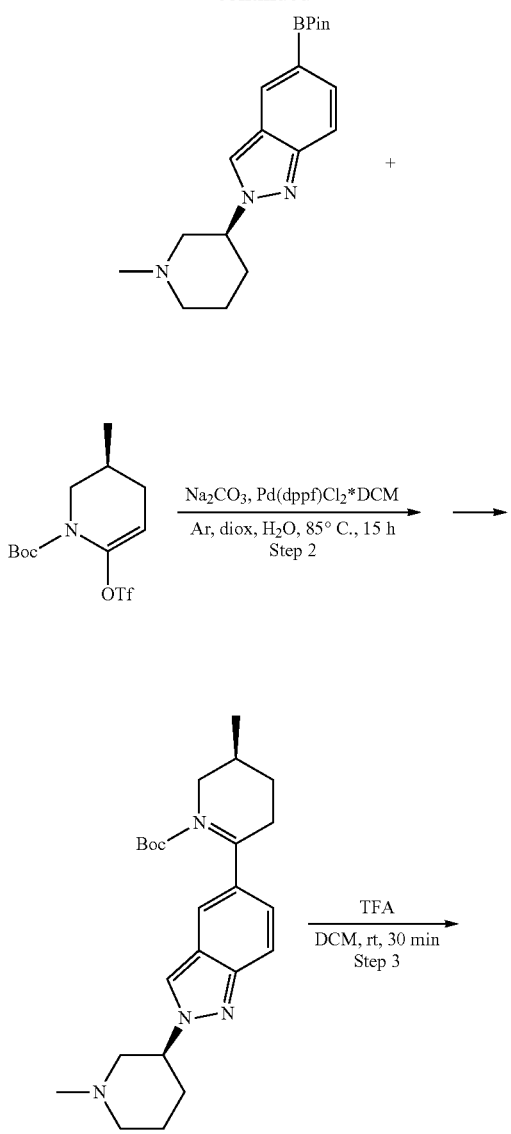

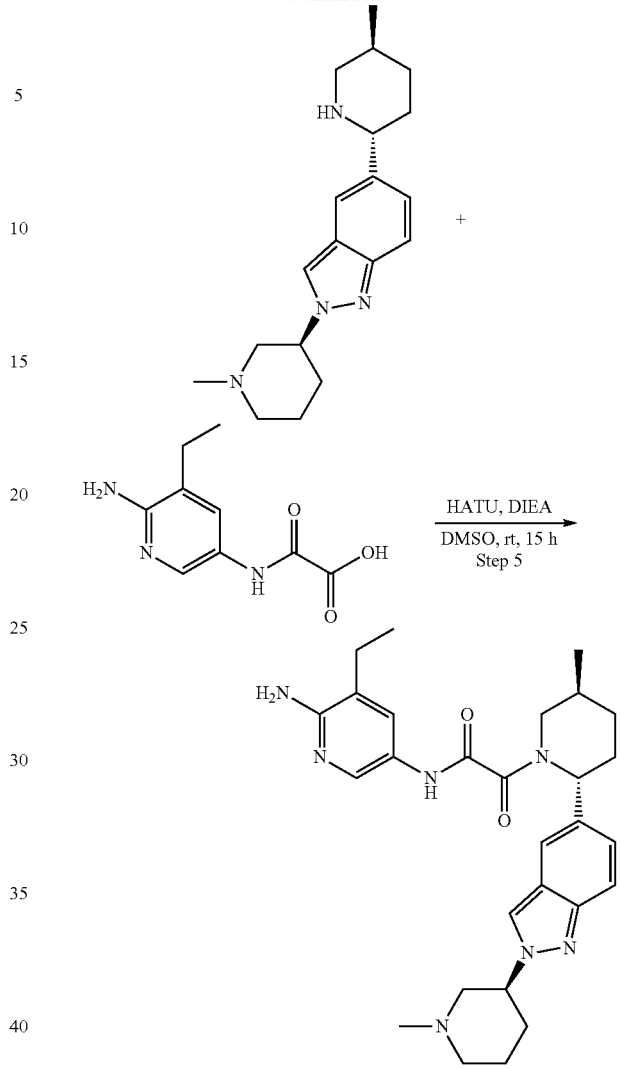

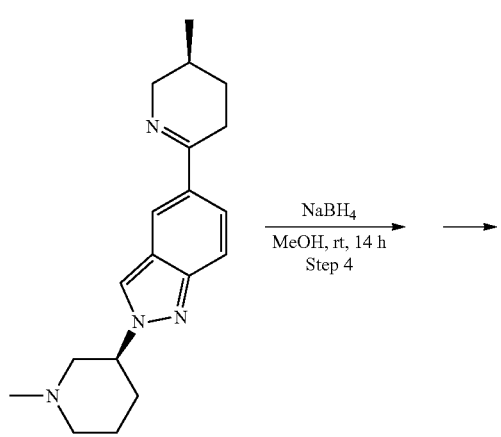

Step 1: The Synthesis of 2-[rac-(3S)-1-methyl-3-piperidyl]-5-(4,4,5,5-tetramethyl-1,3,2-dioxaborolan-2-yl)indazole Prepared by General Procedure Scheme L Step 1

FCC conditions: Interchim; 120 g SiO$_2$, MTBE-MeOH from 0~100%, flow rate=70 mL/min, cv=6

Yield: 3.1 g (35.96%)

LCMS(ESI): [M+H]$^+$ m/z: calcd 342.2; found 342.2; Rt=1.132 min.

Step 2: The Synthesis of tert-butyl rac-(3S)-3-methyl-6-[2-[rac-(3S)-1-methyl-3-piperidyl]indazol-5-yl]-3,4-dihydro-2H-pyridine-1-carboxylate Prepared by General Procedure Scheme L Step 2

Yield: 1.2 g (crude)

LCMS(ESI): [M+H]$^+$ m/z: calcd 411.2; found 411.2; Rt=1.062 min.

Step 3: The Synthesis of 2-[rac-(3S)-1-methyl-3-piperidyl]-5-[rac-(3S)-3-methyl-2,3,4,5-tetrahydropyridin-6-yl]indazole Prepared by General Procedure Scheme L Step 3 (Method A)

Yield: 0.7 g (crude)

LCMS(ESI): [M+H]$^+$ m/z: calcd 311.2; found 311.2; Rt=0.937 min.

Step 4: The Synthesis of 5-[rac-(2R,5S)-5-methyl-2-piperidyl]-2-[rac-(3S)-1-methyl-3-piperidyl]indazole Prepared by General Procedure Scheme L Step 4

Yield: 0.5 g (crude, 2HCl)

LCMS(ESI): [M+H]$^+$ m/z: calcd 313.2; found 313.2; Rt=0.345 min.

Step 5: The Synthesis of N-(6-amino-5-ethyl-3-pyridyl)-2-oxo-2-[rac-(2R,5S)-5-methyl-2-[2-[rac-(3S)-1-methyl-3-piperidyl]indazol-5-yl]-1-piperidyl]acetamide (Compound 1271

Prepared by General Procedure Scheme L Step 5

HPLC conditions: 2-10 min 50-65% methanol+NH$_3$ flow 30 mL/min (loading pump 4 mL/min methanol), column: sun fire C18

Yield: 0.06 g (14.75%)

$^1$H NMR (DMSO-d$_6$, 600 MHz): δ (ppm) 1.07 (m, 6H), 1.33 (m, 1H), 1.69 (m, 3H), 1.89 (m, 3H), 2.04 (m, 3H), 2.15 (m, 1H), 2.22 (s, 4H), 2.40 (m, 3H), 2.74 (m, 1H), 3.03 (m, 1H), 3.83 (m, 1H), 4.89 (m, 1H), 5.61 (m, 2H), 7.20 (m, 1H), 7.54 (m, 3H), 8.03 (m, 1H), 8.43 (m, 1H), 10.42 (s, 1H).

LCMS(ESI): [M+2H]$^+$ m/z: calcd 505.2; found 505.2; Rt=1.707 min.

Example 676. The Synthesis of 2-methoxy-5-[[2-oxo-2-[rac-(2R,5S)-5-methyl-2-[2-[rac-(3R)-1-methylpyrrolidin-3-yl]indazol-5-yl]-1-piperidyl]acetyl]amino]pyridine-3-carboxamide (Compound 1141)

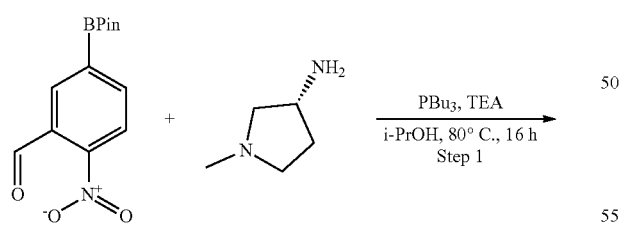

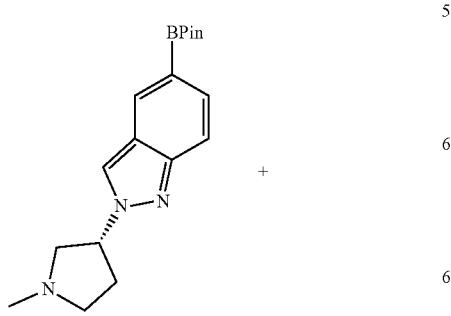

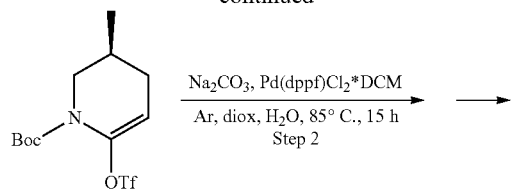

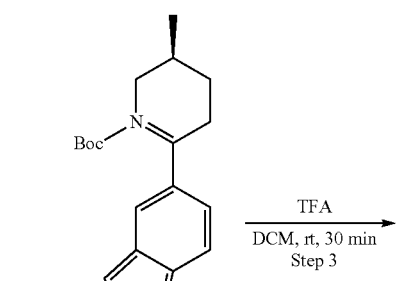

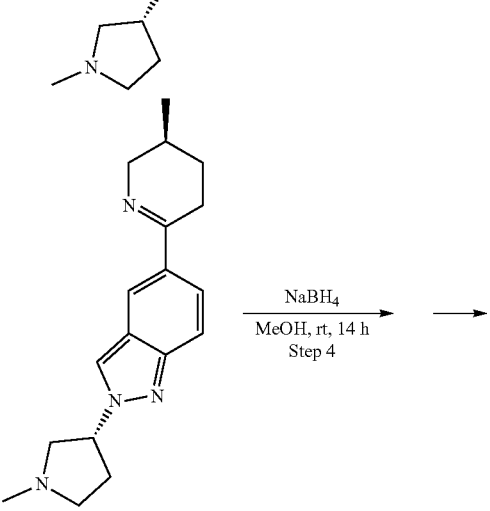

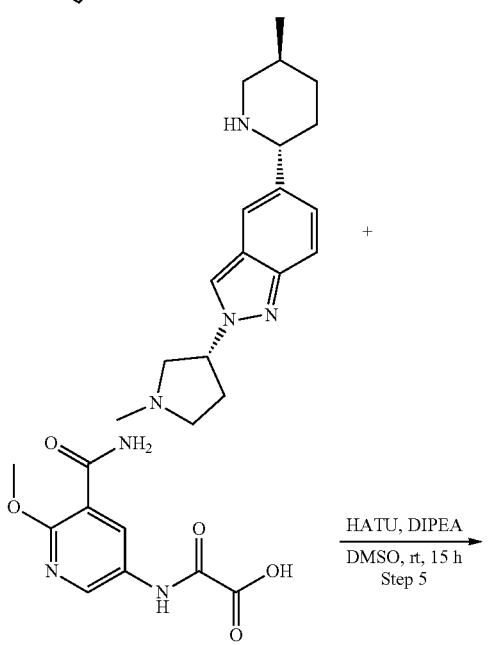

2843

-continued

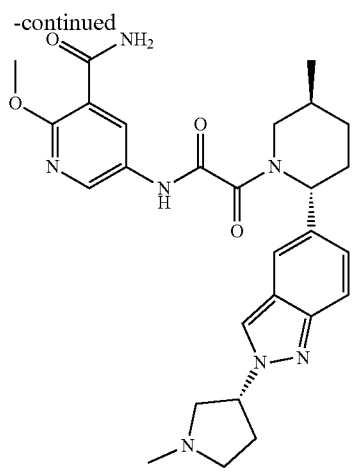

Step 1: The Synthesis of 2-[rac-(3R)-1-methylpyrrolidin-3-yl]-5-(4,4,5,5-tetramethyl-1,3,2-dioxaborolan-2-yl)indazole Prepared by General Procedure Scheme L Step 1

FCC conditions: Interchim; 120 g SiO$_2$, MTBE-MeOH from 0-100%, flow rate=70 mL/min, cv=13.7

Yield: 3.6 g (43.55%)

LCMS(ESI): [M+H]$^+$ m/z: calcd 328.2; found 328.2; Rt=0.897 min.

Step 2: The Synthesis of tert-butyl rac-(3S)-3-methyl-6-[2-[rac-(3R)-1-methylpyrrolidin-3-yl]indazol-5-yl]-3,4-dihydro-2H-pyridine-1-carboxylate Prepared by General Procedure Scheme L Step 2

Yield: 3.5 g (crude)

LCMS(ESI): [M+H]$^+$ m/z: calcd 397.2; found 397.4; Rt=1.010 min.

Step 3: The Synthesis of 2-[rac-(3R)-1-methylpyrrolidin-3-yl]-5-[rac-(3S)-3-methyl-2,3,4,5-tetrahydropyridin-6-yl]indazole Prepared by General Procedure Scheme L Step 3 (Method A)

Yield: 2.0 g (crude)

LCMS(ESI): [M+H]$^+$ m/z: calcd 297.2; found 297.1; Rt=0.380 min.

Step 4: The Synthesis of 5-[rac-(2R,5S)-5-methyl-2-piperidyl]-2-[rac-(3R)-1-methylpyrrolidin-3-yl]indazole Prepared by General Procedure Scheme L Step 4

Yield: 1.9 g (crude, 2 HCl)

LCMS(ESI): [M+H]$^+$ m/z: calcd 299.2; found 299.0; Rt=0.675 min.

2844

Step 5: The Synthesis of 2-methoxy-5-[[2-oxo-2-[rac-(2R,5S)-5-methyl-2-[2-[rac-(3R)-1-methylpyrrolidin-3-yl]indazol-5-yl]-1-piperidyl]acetyl]amino]pyridine-3-carboxamide (Compound 1141

Prepared by General Procedure Scheme L Step 5

HPLC conditions: 2-10 min 45-60% methanol+NH$_3$ flow 30 mL/min (loading pump 4 mL/min methanol), column: sun fire C18

Yield: 0.02 g (9.53%)

$^1$H NMR (600 MHz, dmso) 6 0.96-1.09 (m, 3H), 1.30-1.40 (m, 1H), 1.57-2.07 (m, 3H), 2.11-2.26 (m, 2H), 2.31 (s, 3H), 2.78-3.23 (m, 5H), 3.47-4.00 (m, 5H), 5.14-5.68 (m, 2H), 7.13-7.28 (m, 1H), 7.55-7.63 (m, 2H), 7.68-7.76 (m, 2H), 8.35-8.59 (m, 3H), 10.94-11.13 (m, 1H).

LCMS(ESI): [M+H]$^+$ m/z: calcd 520.2; found 520.4; Rt=2.407 min.

Example 677. The Synthesis of 2-methoxy-5-[[2-oxo-2-[rac-(2R,5S)-5-methyl-2-[2-[rac-(3S)-1-methylpyrrolidin-3-yl]indazol-5-yl]-1-piperidyl]acetyl]amino]pyridine-3-carboxamide (Compound 1318)

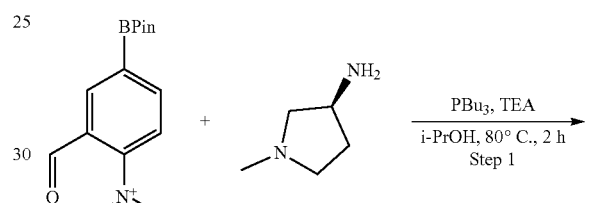

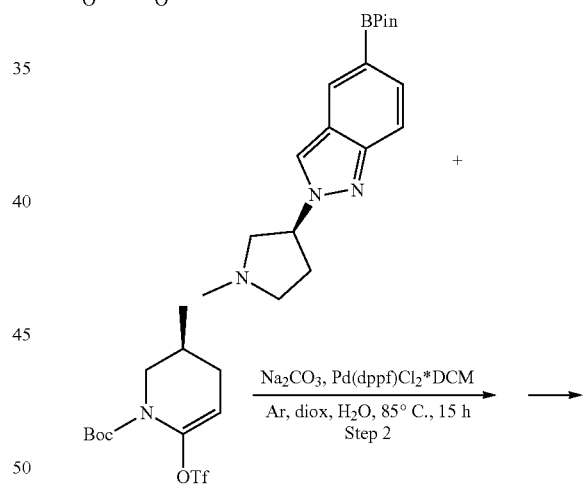

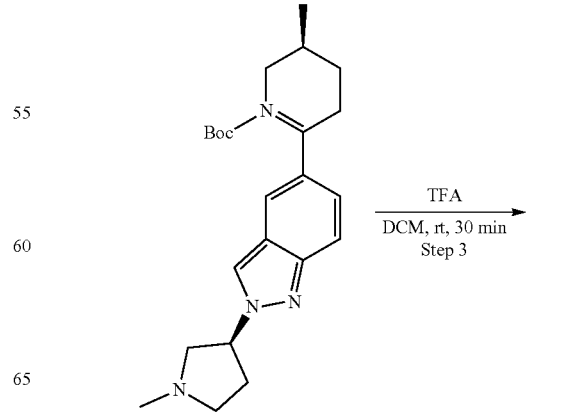

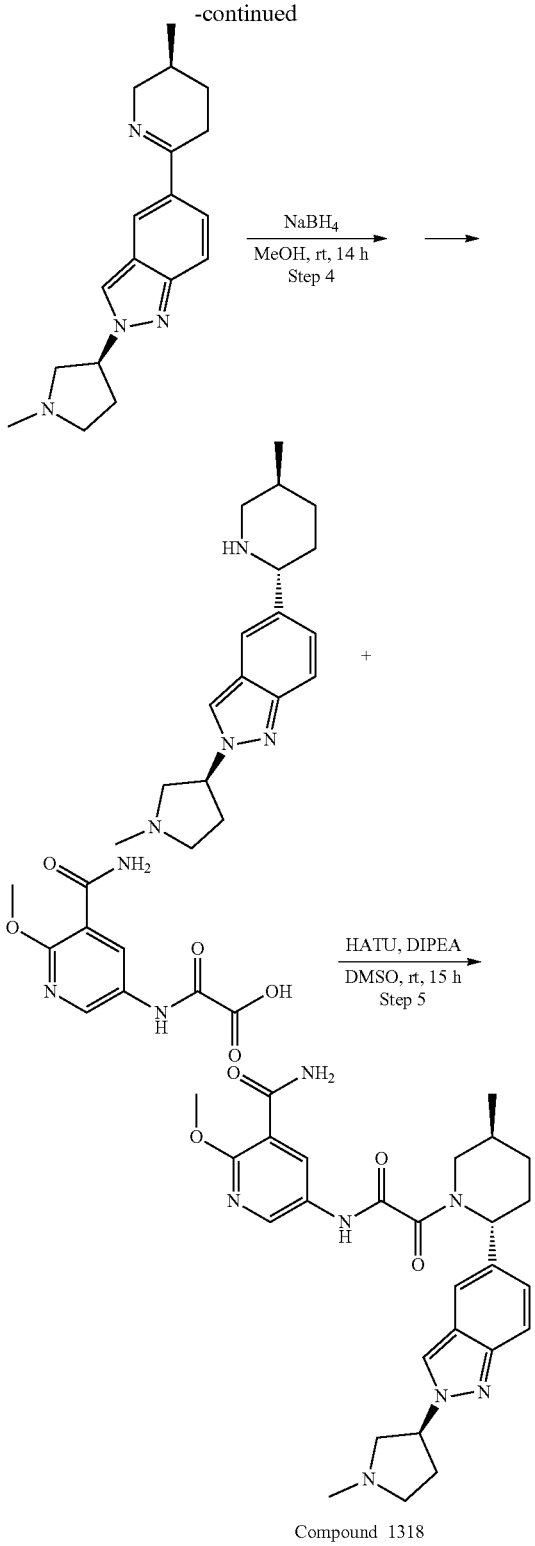

Compound 1318

Step 1: The Synthesis of 2-[rac-(3S)-1-methylpyrrolidin-3-yl]-5-(4,4,5,5-tetramethyl-1,3,2-dioxaborolan-2-yl)indazole Prepared by General Procedure Scheme L Step 1
FCC conditions: Interchim; 120 g SiO$_2$, MTBE-MeOH from 0~100%, flow rate=70 mL/min, cv=13.9

Yield: 2.6 g (31.45%)
LCMS(ESI): [M+H]$^+$ m/z: calcd 328.2; found 328.2; Rt=0.904 min.

Step 2: The Synthesis of tert-butyl rac-(3S)-3-methyl-6-[2-[rac-(3S)-1-methylpyrrolidin-3-yl]indazol-5-yl]-3,4-dihydro-2H-pyridine-1-carboxylate Prepared by General Procedure Scheme L Step 2
Yield: 2.0 g (crude)
LCMS(ESI): [M+H]$^+$ m/z: calcd 397.2; found 397.2; Rt=1.189 min.

Step 3: The Synthesis of 2-[rac-(3S)-1-methylpyrrolidin-3-yl]-5-[rac-(3S)-3-methyl-2,3,4,5-tetrahydropyridin-6-yl]indazole Prepared by General Procedure Scheme L Step 3 (Method A)
Yield: 1.55 g (crude)
LCMS(ESI): [M+H]$^+$ m/z: calcd 297.2; found 297.2; Rt=0.668 min.

Step 4: The Synthesis of 5-[rac-(2R,5S)-5-methyl-2-piperidyl]-2-[rac-(3S)-1-methylpyrrolidin-3-yl] indazole Prepared by General Procedure Scheme L Step 4
Yield: 1.5 g (crude, 2HCl)
LCMS(ESI): [M+H]$^+$ m/z: calcd 299.2; found 299.2; Rt=0.680 min.

Step 5: The Synthesis of 2-methoxy-5-[[2-oxo-2-[rac-(2R,5S)-5-methyl-2-[2-[rac-(3S)-1-methylpyrrolidin-3-yl]indazol-5-yl]-1-piperidyl]acetyl]amino]pyridine-3-carboxamide (Compound 1318

Prepared by General Procedure Scheme L Step 5
HPLC conditions: 2-10 min 50-65% methanol+NH$_3$ flow 30.0 mL/min (loading pump 4 mL/min methanol), column: SunFire C18
Yield: 0.017 g (8.10%)
$^1$H NMR (600 MHz, dmso) δ 0.99-1.07 (m, 3H), 1.29-1.40 (m, 1H), 1.72-1.83 (m, 1H), 1.83-1.94 (m, 1H), 2.03-2.27 (m, 3H), 2.30 (s, 3H), 2.75-3.20 (m, 5H), 3.46-4.03 (m, 5H), 5.13-5.68 (m, 2H), 7.13-7.27 (m, 1H), 7.55-7.65 (m, 2H), 7.67-7.76 (m, 2H), 8.36-8.42 (m, 1H), 8.43-8.68 (m, 2H), 10.93-11.10 (m, 1H).
LCMS(ESI): [M+H]$^+$ m/z: calcd 520.2; found 520.2; Rt=2.393 min.

Example 678. The Synthesis of N-(6-amino-5-ethyl-3-pyridyl)-2-oxo-2-[rac-(2R,5S)-5-methyl-2-[2-(1,2,2,6,6-Pentamethyl-4-piperidyl)indazol-5-yl]-1-piperidyl]acetamide (Compound 1140)

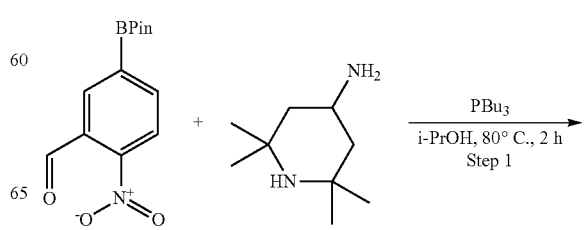

2847
-continued
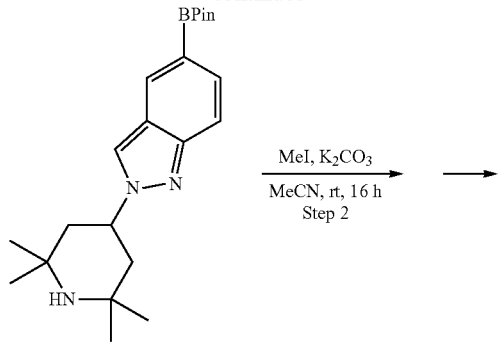
2848
-continued
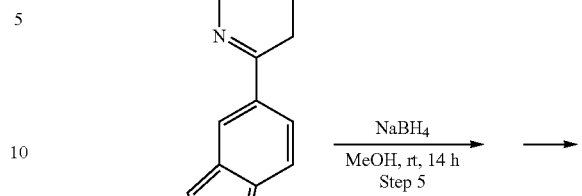
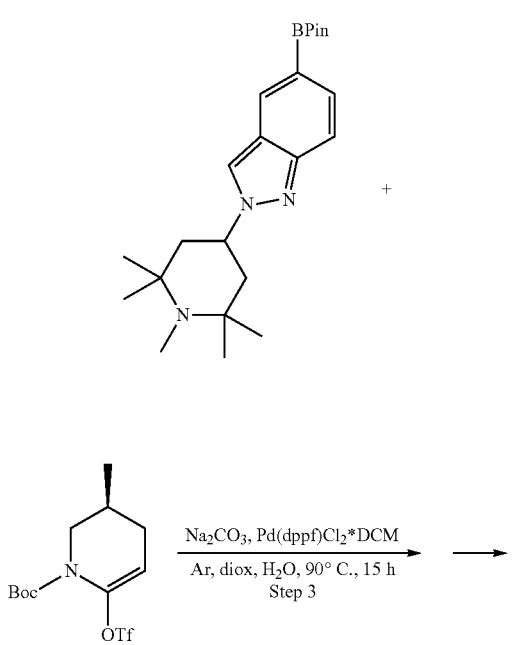
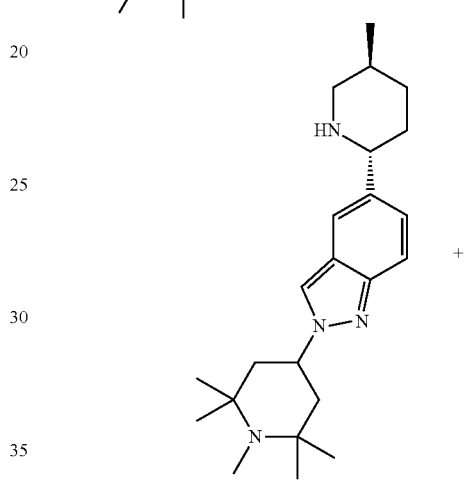
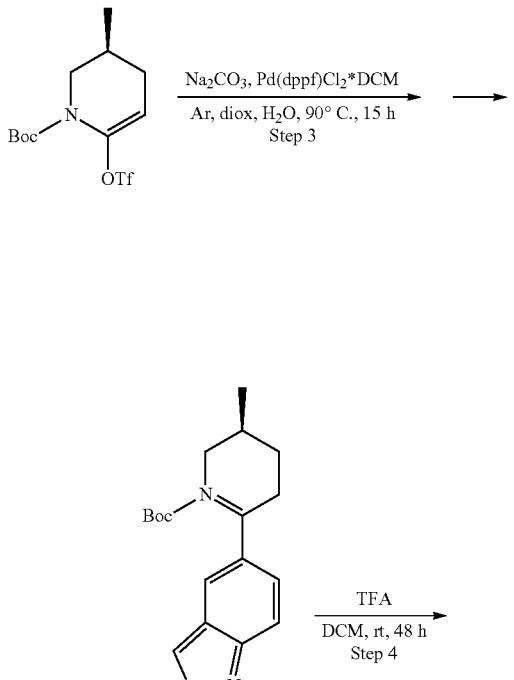
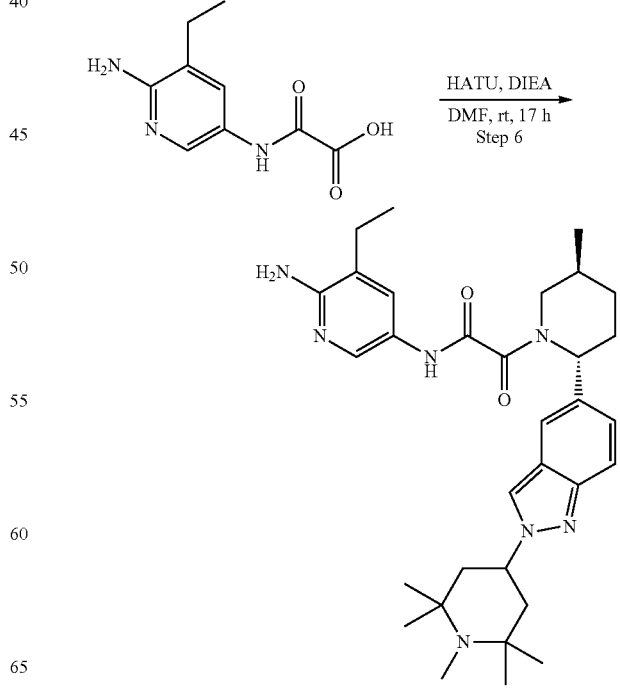

Step 1: The Synthesis of 5-(4,4,5,5-tetramethyl-1,3,2-dioxaborolan-2-yl)-2-(2,2,6,6-tetramethyl-4-piperidyl)indazole Prepared by General Procedure Scheme L Step 1
Yield: 2.8 g (crude)
LCMS(ESI): [M+H]$^+$ m/z: calcd 384.2; found 384.2; Rt=1.133 min.

Step 2: The Synthesis of 2-(1,2,2,6,6-Pentamethyl-4-piperidyl)-5-(4,4,5,5-tetramethyl-1,3,2-dioxaborolan-2-yl)indazole Prepared by General Procedure Scheme L Step 1C
Yield: 3.0 g (crude)
LCMS(ESI): [M+H]$^+$ m/z: calcd 398.2; found 398.1; Rt=1.152 min.

Step 3: The Synthesis of tert-butyl rac-(3S)-3-methyl-6-[2-(1,2,2,6,6-Pentamethyl-4-piperidyl)indazol-5-yl]-3,4-dihydro-2H-pyridine-1-carboxylate Prepared by General Procedure Scheme L Step 2C
Yield: 3.5 g (crude)
LCMS(ESI): [M+H]$^+$ m/z: calcd 467.2; found 467.2; Rt=1.232 min.

Step 4: The Synthesis of 2-(1,2,2,6,6-Pentamethyl-4-piperidyl)-5-[rac-(3S)-3-methyl-1,2,3,4-tetrahydropyridin-6-yl]indazole Prepared by General Procedure Scheme L Step 3 (Method A)
Yield: 1.1 g (crude)
LCMS(ESI): [M+H]$^+$ m/z: calcd 367.2; found 367.2; Rt=0.725 min.

Step 5: The Synthesis of 2-(1,2,2,6,6-Pentamethyl-4-piperidyl)-5-[rac-(2R,5S)-5-methyl-2-piperidyl]indazole Prepared by General Procedure Scheme L Step 4
Yield: 1.3 g (crude)
LCMS(ESI): [M+H]$^+$ m/z: calcd 369.2; found 369.2; Rt=0.756 min.

Step 6: The Synthesis of N-(6-amino-5-ethyl-3-pyridyl)-2-oxo-2-[rac-(2R,5S)-5-methyl-2-[2-(1,2,2,6,6-Pentamethyl-4-piperidyl)indazol-5-yl]-1-piperidyl]acetamide (Compound 1140

Prepared by General Procedure Scheme L Step 5
HPLC conditions: column: XBridge C18 100×19 mm 5 um; mobile phase: 35-35-60% 0-1-6 min H$_2$O/MeCN/0.1% NH$_4$OH, flow rate: 30 mL/min (loading pump 4 mL/min MeCN)
Yield: 78.2 mg (25.74%)
$^1$H NMR (600 MHz, dmso) 6 0.86-1.09 (m, 6H), 1.10-1.12 (m, 6H), 1.13-1.16 (m, 6H), 1.32-1.46 (m, 2H), 1.75-2.07 (m, 7H), 2.11-2.19 (m, 1H), 2.21-2.24 (m, 3H), 2.39-2.43 (m, 1H), 2.76-3.23 (m, 1H), 3.45-4.05 (m, 1H), 4.78-4.90 (m, 1H), 5.14-5.71 (m, 3H), 7.11-7.28 (m, 1H), 7.41-7.54 (m, 1H), 7.57-7.74 (m, 2H), 7.98-8.11 (m, 1H), 8.36-8.45 (m, 1H), 10.52 (s, 1H).
LCMS(ESI): [M+2H]$^+$ m/z: calcd 561.2; found 561.1; Rt=2.193 min.

Scheme M—Synthesis of Compounds of Formula 13

Compounds of Formula 11 are are compounds of Formula (I) wherein R$^1$, R$^2$, R$^3$, R$^4$, R$^6$ R7, and R$^8$ are as described herein.
General Procedure 13

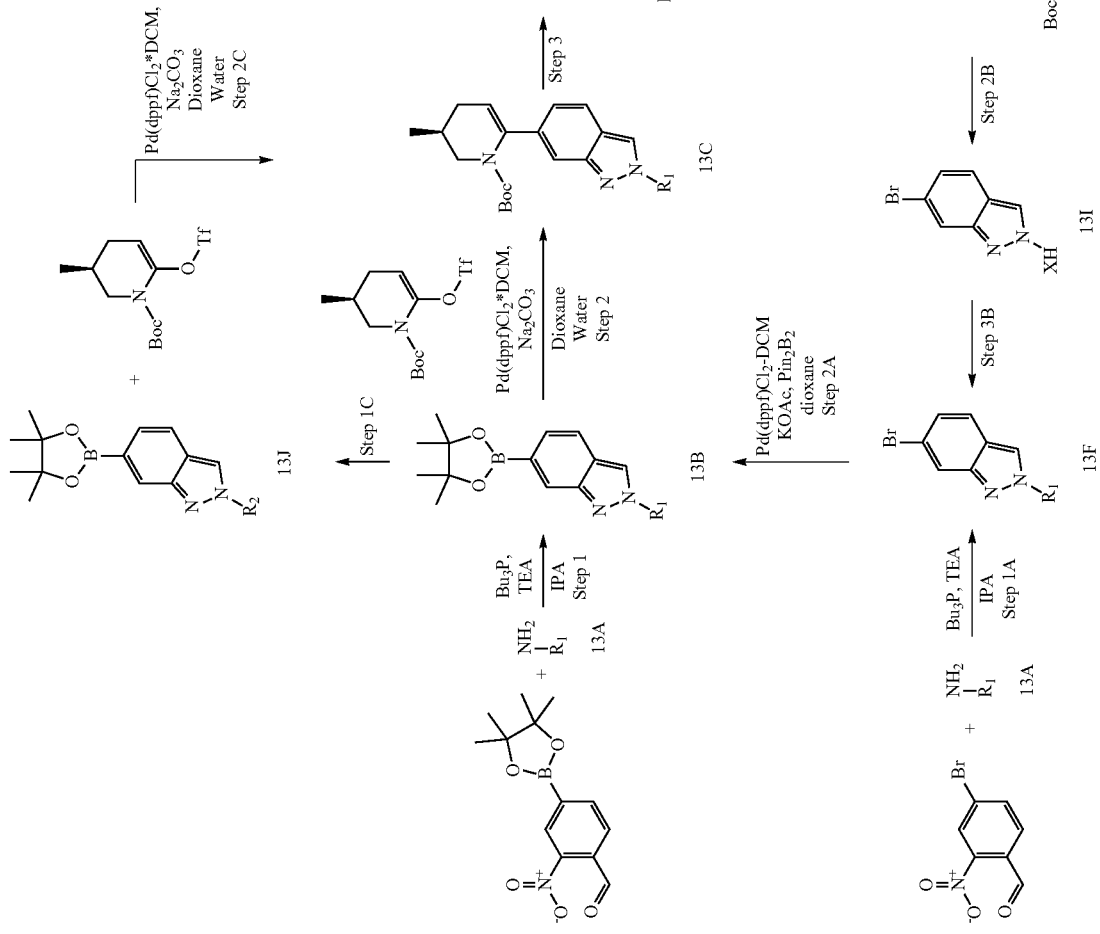

Step 1: General Procedure for 13B 2-nitro-5-(4,4,5,5-tetramethyl-1,3,2-dioxaborolan-2-yl) benzaldehyde (1.0 equiv.) and 13A (1.0 equiv., or it's salt) were dissolved in i-PrOH (140 mL). The resulting mixture was stirred at 80° C. for 2 hours following by the addition of tri-n-butyl phosphine (Bu$_3$P, 3.0 equiv.). The reaction mixture was stirred under reflux for 2 hours. Then, the volatiles were removed in vacuo. The residue was dissolved in DCM and washed with water. The organic layer separated, dried over Na$_2$SO$_4$ and concentrated under reduced pressure. The residue was purified by flash chromatography to afford 13B.

Step 1A: General Procedure for 13F 5-bromo-2-nitro-benzaldehyde (1.0 equiv.) and 13A (1.0 equiv.) were dissolved in i-PrOH (400.0 mL). The resulting mixture was stirred at 80° C. for 2 hr following by the addition of tri-n-butyl phosphine (3.0 equiv.). The reaction mixture was refluxed additionally for 16 hr.

Then the reaction mixture was evaporated under reduced pressure and purified by flash chromatography to afford 13F.

Step 1B: General Procedure for 13H 5-bromo-2-nitro-benzaldehyde (1.0 equiv.) and 13G(1.0 equiv.) were dissolved in i-PrOH (80.0 mL). The resulting mixture was stirred at 80° C. for 2 hr and tri-n-butyl phosphine (3.0 equiv.) was added. The reaction mixture was refluxed additionally for 16 hr. Then the reaction mixture was evaporated under reduced pressure and purified by flash chromatography to afford 13H.

Step 1C: General Procedure for 13J

Potassium carbonate, anhydrous, 99% (3.0 equiv.) and iodomethane (1.7 equiv) were added to the solution of 13B (1.0 equiv.) in MeCN (appr. 45.0 mL). The resulting mixture was stirred at 25° C. for 16 hr. Then, solvent was removed under reduced pressure. The residue was diluted with water (40.0 mL) and the resulting mixture was extracted with DCM to 13J.

Step 2: General Procedure for 13C 13B (1.0 equiv.), tert-butyl rac-(3S)-3-methyl-6-(trifluoromethylsulfonyloxy)-3,4-dihydro-2H-pyridine-1-carboxylate (1.01 equiv.), sodium carbonate (3.0 equiv.) and Pd(dppf)Cl$_2$ DCM (0.05 equiv.) were stirred in a mixture of 1,4-dioxane (6.0 mL) and water (2.0 mL) under inert atmosphere at 85° C. for 15 hr. Upon completion, the reaction mixture was cooled down, diluted with water and extracted with DCM. The organic layer was separated, dried over Na$_2$SO$_4$ and concentrated under reduced pressure to afford 13C. The obtained material was used in the next step without an additional purification.

Step 2A: General Procedure for 13B 13F (1.0 equiv.), B$_2$Pin$_2$ (1.1 equiv.) and Potassium Acetate (2.0 equiv) were mixed together in 1.4-dioxane (appr. 20.0 mL). The resulting mixture was evacuated and then backfilled with argon, this operation was repeated three times, then Pd(dppf)$_2$Cl$_2$ DCM (993.01 mg, 1.22 mmol) was added under argon. The reaction mixture was stirred under argon atmosphere at 90° C. for 14 hr. Then the mixture was allowed to cool to the room temperature and the volatiles were removed in vacuo to afford 13B.

Step 2B: General Procedure for 13I 13H (1.0 equiv.) was dissolved in a mixture of TFA (1.0 mL) and DCM (1.0 mL). The reaction mixture was stirred at room temperature for 30 minutes. Then, the mixture was concentrated in vacuo to 13I. The obtained material was used in the next step without an additional purification.

Step 2C: General Procedure for 13C

Sodium carbonate (2.0 equiv.) was added to a solution of 13J (1.0 equiv.) and tert-butyl rac-(5S)-5-methyl-2-(trifluoromethylsulfonyloxy)piperidine-1-carboxylate (1.1 equiv.) in Water (appr. 15.0 mL) and 1,4-dioxane (appr. 50.0 mL). Reaction flask was evacuated and refilled with argon 3 times. Then, Pd(dppf)Cl$_2$CH$_2$Cl$_2$ (0.05 equiv.) was added under stream of argon. The resulting mixture was stirred at 90° C. for 15 hr under inert atmosphere. Upon completion of the reaction, water (appr. 50.0 mL) was added. The resulting mixture was extracted with EtOAc (3*20.0 mL). The combined organic layers were dried over Na$_2$SO$_4$, filtered and concentrated in vacuo to obtain 13C. The obtained material was used in the next step without an additional purification.

Step 3: General Procedure for 13D

Method A:
13C (1.0 equiv.) was dissolved in a mixture of TFA (1.0 mL) and DCM (1.0 mL). The reaction mixture was stirred at room temperature for 30 minutes. Then, the mixture was concentrated in vacuo to 13D. The obtained material was used in the next step without an additional purification.
Method B:
13C (1.0 equiv.) was dissolved in a mixture of HCl (4.0 M solution in dioxane, 1.0 mL) and MeOH (1.0 mL). The reaction mixture was stirred at room temperature overnight. Then, the mixture was concentrated in vacuo to 13D. The obtained material was used in the next step without an additional purification.

Step 3B: General Procedure for 13F

To a solution of 13I (1.0 equiv.), acetic acid (1.0 equiv.) and Formaldehyde, 37% in aq. soln., ACS, 36.5-38.0%, stab. with 10-15% methanol (1.0 equiv.) in DCM (appr. 25.0 mL), Sodium triacetoxyborohydride (1.0 equiv.) was added. The resulting mixture was stirred at 25° C. for 16 hr. Then, the solvent was removed in vacuo. The residue was poured in H$_2$O (50.0 mL) and extracted with EtOAc (2×20.0 mL). The combined organic extracts were washed with brine (2*20.0 mL), dried over sodium sulphate and evaporated in vacuo to afford 13F.

Step 4: General Procedure for 13E

Sodium Borohydride (2.0 equiv) was portionwise added to the solution of 13D (1.0 equiv.) in MeOH (5.0 mL). The reaction mixture was stirred at room temperature for 17 hours. Then, the mixture was acidified with HCl (4.0M solution in dioxane) to pH 5 and the volatiles were removed in vacuo to afford 13E. The obtained material was used in the next step without an additional purification.

Step 5: General Procedure for Formula 13

HATU (1.4 equiv.) was added to the stirred solution of 13E (1.0 equiv), corresponding acid (1.1 equiv) and DIPEA (10.0 equiv) in DMSO (appr. 6.0 mL). The resulting reaction mixture was stirred at 25° C. for 4 hr. The resulting mixture was submitted to reverse phase HPLC to afford Formula E.

Example 679. The Synthesis of N-(6-amino-5-ethyl-3-pyridyl)-2-oxo-2-[rac-(2R,5S)-5-methyl-2-[2-(1,2,2,6,6-Pentamethyl-4-piperidyl)indazol-6-yl]-1-piperidyl]acetamide (Compound 1295

Step 1: The Synthesis of 6-bromo-2-(2,2,6,6-tetramethyl-4-piperidyl)indazole

Prepared by General Procedure Scheme M Step 1A
Yield: 3.6 g (82.08%)
LCMS(ESI): [M+H]+ m/z: calcd 336.2; found 336.2; Rt=1.061 min.

Step 2: The Synthesis of 6-bromo-2-(1,2,2,6,6-Pentamethyl-4-piperidyl)indazole

Prepared by General Procedure Scheme M Step 1C
Yield: 2.7 g (72.0%)
LCMS(ESI): [M+H]+ m/z: calcd 352.2; found 350.2; Rt=1.015 min.

Step 3: The Synthesis of 2-(1,2,2,6,6-Pentamethyl-4-piperidyl)-6-(4,4,5,5-tetramethyl-1,3,2-dioxaborolan-2-yl)indazole Prepared by General Procedure Scheme M Step 2A
Yield: 1.8 g (58.77%)
LCMS(ESI): [M+H]+ m/z: calcd 398.2; found 398.0; Rt=1.118 min.

Step 4: The Synthesis of tert-butyl rac-(3S)-3-methyl-6-[2-(1,2,2,6,6-Pentamethyl-4-piperidyl)indazol-6-yl]-3,4-dihydro-2H-pyridine-1-carboxylate Prepared by General Procedure Scheme M Step 2
Yield: 2.0 g (crude)
LCMS(ESI): [M+H]+ m/z: calcd 467.2; found 467.4; Rt=1.276 min.

Step 5: The Synthesis of 2-(1,2,2,6,6-Pentamethyl-4-piperidyl)-6-[rac-(3S)-3-methyl-1,2,3,4-tetrahydropyridin-6-yl]indazole Prepared by General Procedure Scheme M Step 3 (Method A)
Yield: 0.9 g (57.29%)
LCMS(ESI): [M+H]+ m/z: calcd 367.2; found 367.2; Rt=0.727 min.

Step 6: The Synthesis of 2-(1,2,2,6,6-Pentamethyl-4-piperidyl)-6-[rac-(2R,5S)-5-methyl-2-piperidyl]indazole Prepared by General Procedure Scheme M Step 4
Yield: 0.8 g (93.60%)
LCMS(ESI): [M+H]+ m/z: calcd 369.2; found 369.2; Rt=0.767 min.

Step 7: The Synthesis of N-(6-amino-5-ethyl-3-pyridyl)-2-oxo-2-[rac-(2R,5S)-5-methyl-2-[2-(1,2,2,6,6-Pentamethyl-4-piperidyl)indazol-6-yl]-1-piperidyl]acetamide (Compound 1295

Prepared by General Procedure Scheme M Step 5
HPLC conditions: column: XBridge C18 100×19 mm 5 um; mobile phase: 50-100% 0-5 min H2O/MeOH/0.1% NH4OH, flow rate: 30 mL/min (loading pump 4 mL/min MeCN)
Yield: 79.9 mg (35.07%)
1H NMR (600 MHz, dmso) δ 1.02-1.07 (m, 3H), 1.10-1.17 (m, 15H), 1.31-1.43 (m, 1H), 1.69-1.80 (m, 1H), 1.82-1.92 (m, 1H), 1.93-2.00 (m, 4H), 2.02-2.12 (m, 1H), 2.13-2.22 (m, 1H), 2.22 (s, 3H), 2.37-2.45 (m, 2H), 2.78-3.10 (m, 1H), 3.43-4.07 (m, 1H), 4.79-4.89 (m, 1H), 5.19-5.70 (m, 3H), 6.94-7.09 (m, 1H), 7.41-7.53 (m, 2H), 7.64-7.71 (m, 1H), 7.97-8.10 (m, 1H), 8.41 (s, 1H), 10.36-10.71 (m, 1H).
LCMS(ESI): [M+H]+ m/z: calcd 560.2; found 560.2; Rt=2.166 min.

Example 680. The Synthesis of 2-methoxy-5-[[2-oxo-2-[rac-(2R,5S)-5-methyl-2-[2-(1-methyl-4-piperidyl)indazol-6-yl]-1-piperidyl]acetyl]amino]pyridine-3-carboxamide (Compound 1299)

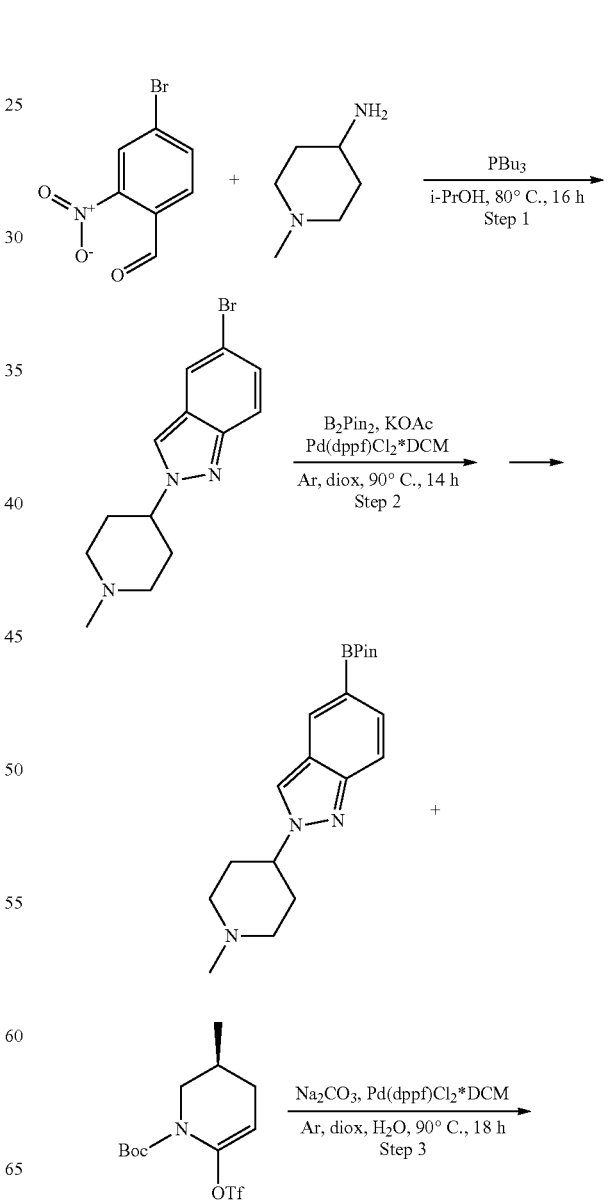

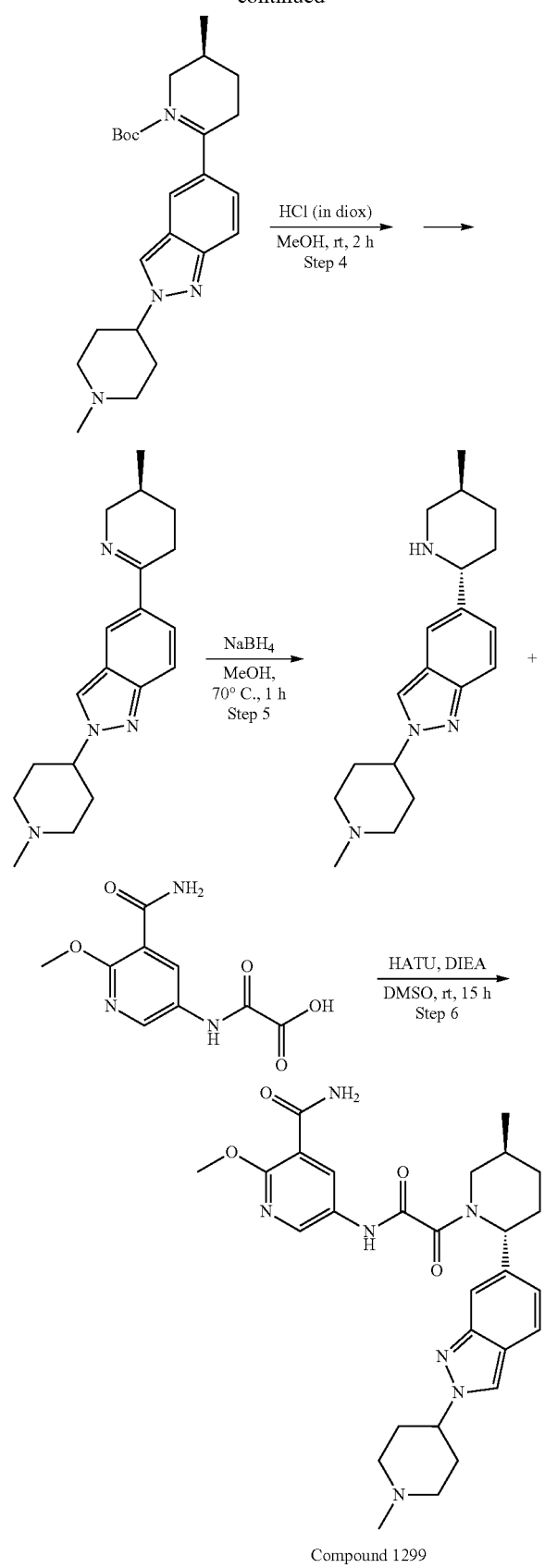

Compound 1299

Step 1: The Synthesis of
6-bromo-2-(1-methyl-4-piperidyl)indazole

Prepared by General Procedure Scheme M Step 1A
FCC conditions: Interchim; 330 g SiO$_2$, MTBE-MeOH from 0~ 100%, flow rate=100 mL/min, cv=10
Yield: 38.0 g (74.28%)
LCMS(ESI): [M+2H]$^+$ m/z: calcd 296.2; found 296.2; Rt=0.808 min.

Step 2: The Synthesis of 2-(1-methyl-4-piperidyl)-6-(4,4,5,5-tetramethyl-1,3,2-dioxaborolan-2-yl)indazole Prepared by General Procedure Scheme M Step 2A
FCC conditions: Interchim; 120 g SiO$_2$, MTBE-MeOH from 0~ 100%, flow rate=70 mL/min,
cv=7
Yield: 21.0 g (47.64%)
LCMS(ESI): [M+H]$^+$ m/z: calcd 342.2; found 342.0; Rt=1.045 min.

Step 3: The Synthesis of tert-butyl rac-(3S)-3-methyl-6-[2-(1-methyl-4-piperidyl)indazol-6-yl]-3,4-dihydro-2H-pyridine-1-carboxylate Prepared by General Procedure Scheme M Step 2
FCC conditions: Interchim; 120 g SiO$_2$, MTBE-MeOH from 0~ 100%, flow rate=70 mL/min,
cv=11
Yield: 9.0 g (74.81%)
LCMS(ESI): [M+H]$^+$ m/z: calcd 411.2; found 411.4; Rt=1.165 min.

Step 4: The Synthesis of 2-(1-methyl-4-piperidyl)-6-[rac-(3S)-3-methyl-2,3,4,5-tetrahydropyridin-6-yl]indazole Prepared by General Procedure Scheme M Step 3 (Method B)
Yield: 6.0 g (71.40%, 2HCl)
LCMS(ESI): [M+H]$^+$ m/z: calcd 311.2; found 311.2; Rt=0.578 min.

Step 5: The Synthesis of 2-(1-methyl-4-piperidyl)-6-[rac-(2R,5S)-5-methyl-2-piperidyl]indazole Prepared by General Procedure Scheme M Step 4
Yield: 4.9 g (crude)
LCMS(ESI): [M+H]$^+$ m/z: calcd 313.2; found 313.2; Rt=0.543 min.

Step 6: The Synthesis of 2-methoxy-5-[[2-oxo-2-[rac-(2R,5S)-5-methyl-2-[2-(1-methyl-4-piperidyl)indazol-6-yl]-1-piperidyl]acetyl]amino]pyridine-3-carboxamide (Compound 1299

Prepared by General Procedure Scheme M Step 5
HPLC conditions: 2-10 min 50-100% Water-MeOH+NH$_3$ flow 30 mL/min (loading pump 4 mL methanol), column: sun fire C18
Yield: 0.22 g (44.40%)
$^1$H NMR (600 MHz, dmso) δ 0.73-1.06 (m, 3H), 1.27-1.43 (m, 1H), 1.65-1.82 (m, 1H), 1.82-1.94 (m, 1H), 2.02-2.15 (m, 7H), 2.21 (s, 3H), 2.24-2.34 (m, 1H), 2.80-3.13 (m, 3H), 3.46-3.51 (m, 0.7H), 3.91-3.97 (m, 3H), 4.01-4.05 (m, 0.3H), 4.38-4.45 (m, 1H), 5.17-5.73 (m, 1H), 6.95-7.10 (m, 1H), 7.53 (s, 1H), 7.64-7.73 (m, 2H), 7.74 (s, 1H), 8.35-8.39 (m, 1H), 8.39-8.49 (m, 1H), 8.49-8.64 (m, 1H), 10.76 (br s, 1H).
LCMS(ESI): [M+H]+ m/z: calcd 534.2; found 534.2; Rt=2.454 min.
Example 681. The Synthesis of N-(6-amino-5-ethyl-3-pyridyl)-2-oxo-2-[rac-(2R,5S)-5-methyl-2-[2-(1-methyl-4-piperidyl)-3-oxo-Isoindolin-5-yl]-1-piperidyl]acetamide (Compound 1272)
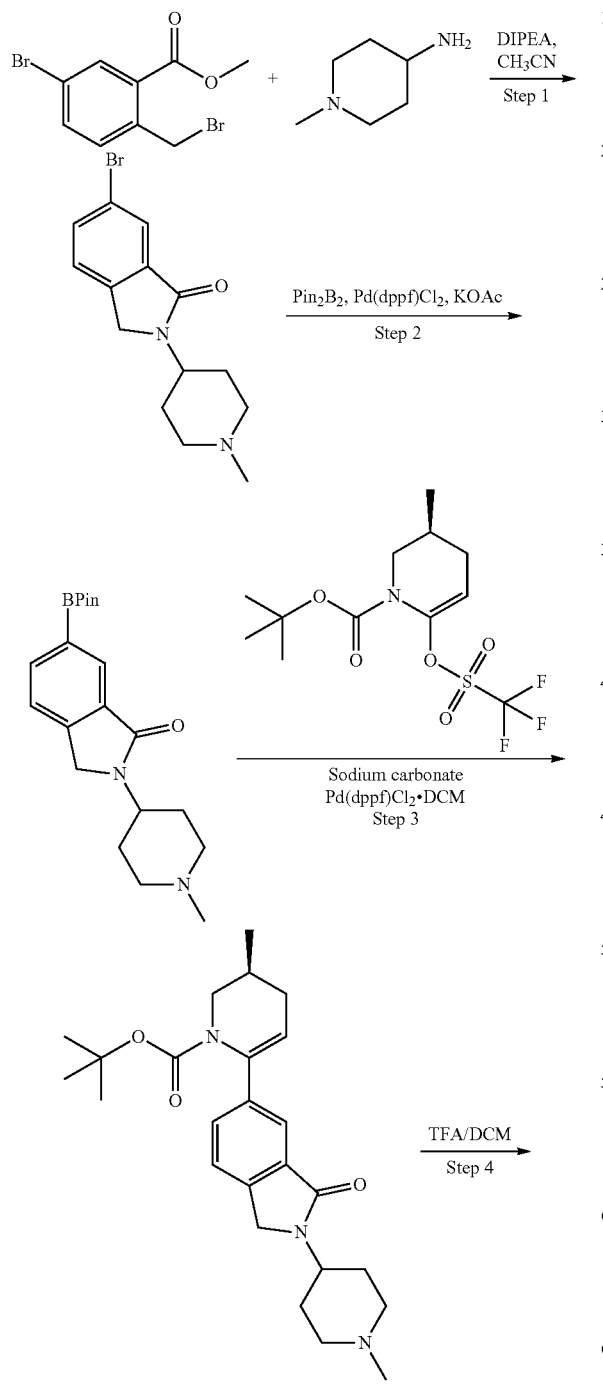
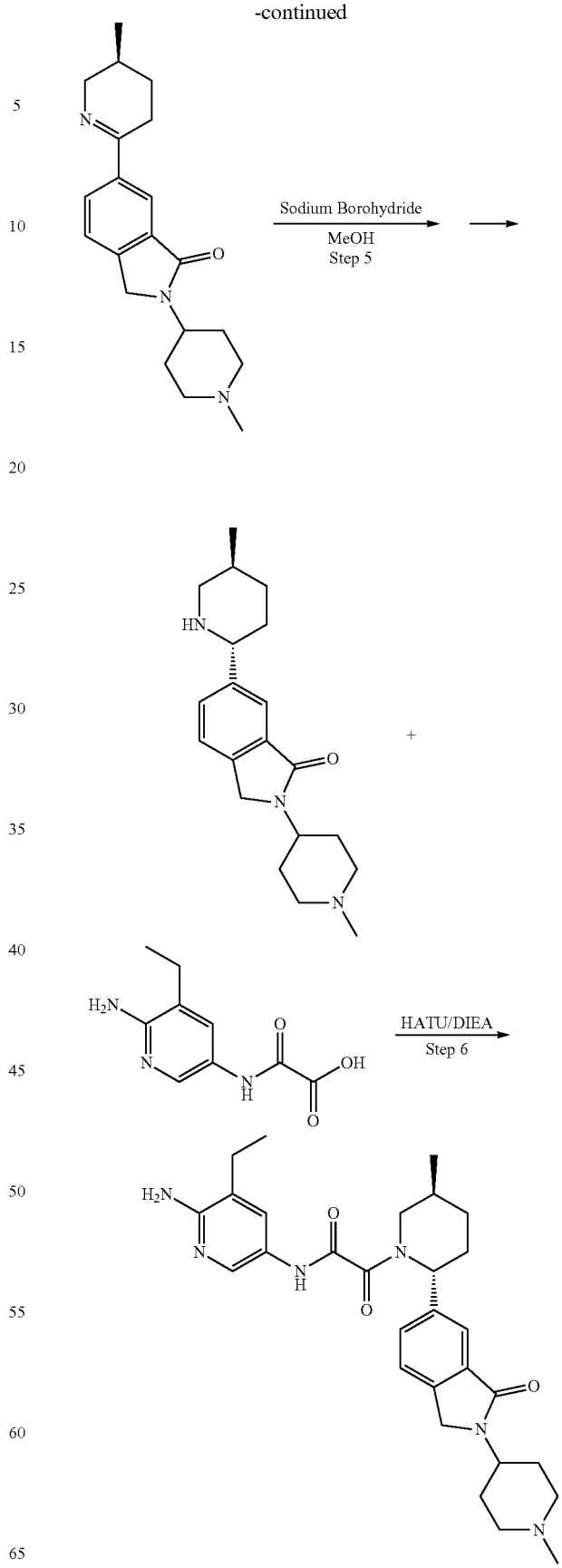

Step 1: 6-bromo-2-(1-methyl-4-piperidyl)isoindolin-1-one methyl 5-bromo-2-(bromomethyl)benzoate (5 g, 16.24 mmol) and 1-methylpiperidin-4-amine (1.85 g, 16.24 mmol) was dissolved in MeCN (69.35 mL), DIPEA (4.20 g, 32.47 mmol, 5.66 mL) was added thereto. This mixture was refluxed for 24 hr. Then it was evaporated and purified by CC (SiO$_2$, MTBE/MeOH was used as an eluent mixture) to afford 6-bromo-2-(1-methyl-4-piperidyl)isoindolin-1-one (1.3 g, 4.20 mmol, 25.90% yield).

LCMS(ESI): [M+1]$^+$ m/z: calcd 309.2; found 311.0; Rt=0.845 min.

Step 2: 2-(1-methyl-4-piperidyl)-6-(4,4,5,5-tetramethyl-1,3,2-dioxaborolan-2-yl)isoindolin-1-one To a solution of 6-bromo-2-(1-methyl-4-piperidyl)isoindolin-1-one (1.3 g, 4.20 mmol) was added Potassium acetate (825.26 mg, 8.41 mmol, 525.64 μL) and Bis(pinacolato) diboron (1.07 g, 4.20 mmol). The reaction mixture was degassed and Pd(dppf)Cl2·DCM (171.67 mg, 210.22 μmol) added in one portion. The mixture was further degassed with Ar and heated at 90° C. for 16 hr. After this time the reaction mixture was allowed to cool to rt, filtered and the solvent removed in vacuo to afford 2-(1-methyl-4-piperidyl)-6-(4,4,5,5-tetramethyl-1,3,2-dioxaborolan-2-yl)isoindolin-1-one (1.50 g, 4.21 mmol, 100.00% yield).

LCMS(ESI): [M+1]$^+$ m/z: calcd 356.2; found 357.2; Rt=0.869 min.

Step 3: Tert-butyl (3S)-3-methyl-6-[2-(1-methyl-4-piperidyl)-3-oxo-Isoindolin-5-yl]-3,4-dihydro-2H-pyridine-1-carboxylate tert-butyl (3S)-3-methyl-6-(trifluoromethylsulfonyloxy)-3,4-dihydro-2H-pyridine-1-carboxylate (1.45 g, 4.21 mmol), 2-(1-methyl-4-piperidyl)-6-(4,4,5,5-tetramethyl-1,3,2-dioxaborolan-2-yl)isoindolin-1-one (1.5 g, 4.21 mmol) and Sodium carbonate (1.34 g, 12.63 mmol, 528.73 μL) was added to a mixture of dioxane (29.60 mL) and water (9.87 mL). The resulting mixture was evacuated and then backfilled with argon, this operation was repeated three times, then Pd(dppf)Cl2·DCM (171.92 mg, 210.52 μmol) was added under argon. The reaction mixture was stirred under argon at 70° C. for 16 hr, then cooled and filtered. The filtercake was washed with 1,4-dioxane (2*20 ml) and discarded. The filtrate was evaporated in vacuo to afford tert-butyl (3S)-3-methyl-6-[2-(1-methyl-4-piperidyl)-3-oxo-isoindolin-5-yl]-3,4-dihydro-2H-pyridine-1-carboxylate (1.58 g, 3.71 mmol, 88.18% yield) as brown oil, which was used in next step without purification.

LCMS(ESI): [M+1]$^+$ m/z: calcd 425.2; found 426.4; Rt=1.146 min.

Step 4: 2-(1-methyl-4-piperidyl)-6-[(3S)-3-methyl-2,3,4,5-tetrahydropyridin-6-yl]isoindolin-1-one The solution of tert-butyl (3S)-3-methyl-6-[2-(1-methyl-4-piperidyl)-3-oxo-isoindolin-5-yl]-3,4-dihydro-2H-pyridine-1-carboxylate (1.58 g, 3.71 mmol) in TFA (6.35 g, 55.69 mmol, 4.29 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 2-(1-methyl-4-piperidyl)-6-[(3S)-3-methyl-2,3,4,5-tetrahydropyridin-6-yl]isoindolin-1-one (1.18 g, 3.63 mmol, 97.66% yield) as brown oil, which was used directly in the next step.

LCMS(ESI): [M+1]$^+$ m/z: calcd 325.2; found 326.0; Rt=0.596 min.

Step 5: The synthesis of 2-(1-methyl-4-piperidyl)-6-[(5S)-5-methyl-2-piperidyl]isoindolin-1-one To a stirred solution of 2-(1-methyl-4-piperidyl)-6-[(3S)-3-methyl-2,3,4,5-tetrahydropyridin-6-yl]isoindolin-1-one (1.18 g, 3.63 mmol) in MeOH (19.74 mL) was added Sodium Borohydride (274.35 mg, 7.25 mmol, 255.44 μL) at 0° C. The resulting reaction mixture was stirred at 25° C. for 16 hr. Upon completion, the reaction mixture was concentrated under reduced pressure, then quenched with water 20 mL and 50 ml EtOAc. The combined organic phase was washed with Brine 20 mL, dried over Na$_2$SO$_4$ and concentrated under reduced pressure to obtain 2-(1-methyl-4-piperidyl)-6-[(5S)-5-methyl-2-piperidyl]isoindolin-1-one (1.1 g, 3.36 mmol, 92.65% yield), which was used in next step without farther purification.

LCMS(ESI): [M+1]$^+$ m/z: calcd 327.2; found 328.2; Rt=0.656 min.

Step 6: The Synthesis of N-(6-amino-5-ethyl-3-pyridyl)-2-oxo-2-[(2R,5S)-5-methyl-2-[2-(1-methyl-4-piperidyl)-3-oxo-Isoindolin-5-yl]-1-piperidyl]acetamide (Compound 1272

DIPEA (308.90 mg, 2.39 mmol, 416.30 μL) was added to the solution of respective 2-[(6-amino-5-ethyl-3-pyridyl)amino]-2-oxo-acetic acid (0.2 g, 956.02 μmol) and 2-(1-methyl-4-piperidyl)-6-[(2R,5S)-5-methyl-2-piperidyl]isoindolin-1-one (313.06 mg, 956.02 μmol) in DMF (19.58 mL). The resulting mixture was stirred for 5 min followed by the addition of HATU (399.86 mg, 1.05 mmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and water-MeOH+NH$_3$ as an eluent mixture) to afford N-(6-amino-5-ethyl-3-pyridyl)-2-oxo-2-[(2R,5S)-5-methyl-2-[2-(1-methyl-4-piperidyl)-3-oxo-isoindolin-5-yl]-1-piperidyl]acetamide (54.9 mg, 105.85 μmol, 11.07% yield).

$^1$H NMR (600 MHz, dmso) δ 0.98-1.04 (m, 3H), 1.06-1.13 (m, 3H), 1.30-1.38 (m, 1H), 1.62-1.70 (m, 3H), 1.77-1.87 (m, 3H), 2.01-2.12 (m, 3H), 2.21-2.29 (m, 4H), 2.35-2.41 (m, 2H), 2.73-2.91 (m, 3H), 3.96-4.06 (m, 2H), 4.41-4.45 (m, 2H), 5.22-5.65 (m, 3H), 7.42-7.54 (m, 2H), 7.57-7.59 (m, 1H), 7.60-7.63 (m, 1H), 7.98-8.08 (m, 1H), 10.53-10.58 (m, 1H).

LCMS(ESI): [M+1]$^+$ m/z: calcd 518.6; found 517.2; Rt=1.935 min.

Example 682. The Synthesis of N-(6-amino-5-ethyl-3-pyridyl)-2-oxo-2-[rac-(2R,5S)-5-methyl-2-[2-(1-methyl-4-piperidyl)indazol-6-yl]-1-piperidyl]acetamide (Compound 1096)
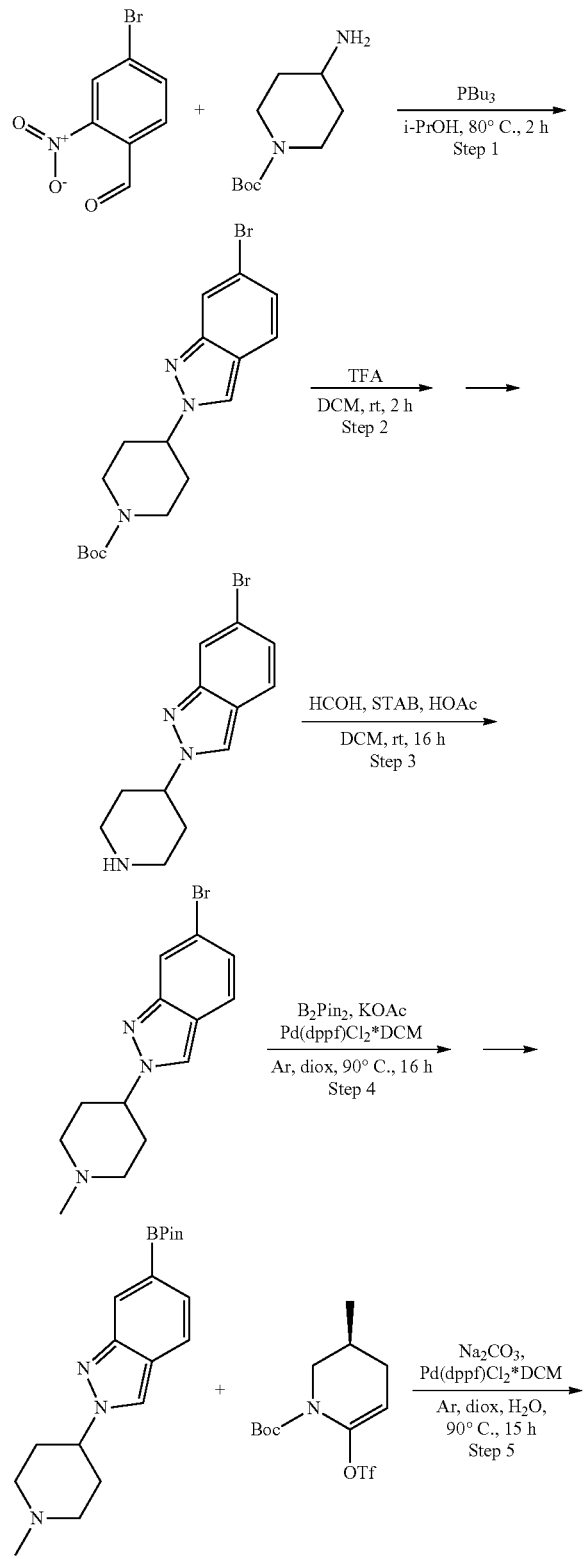
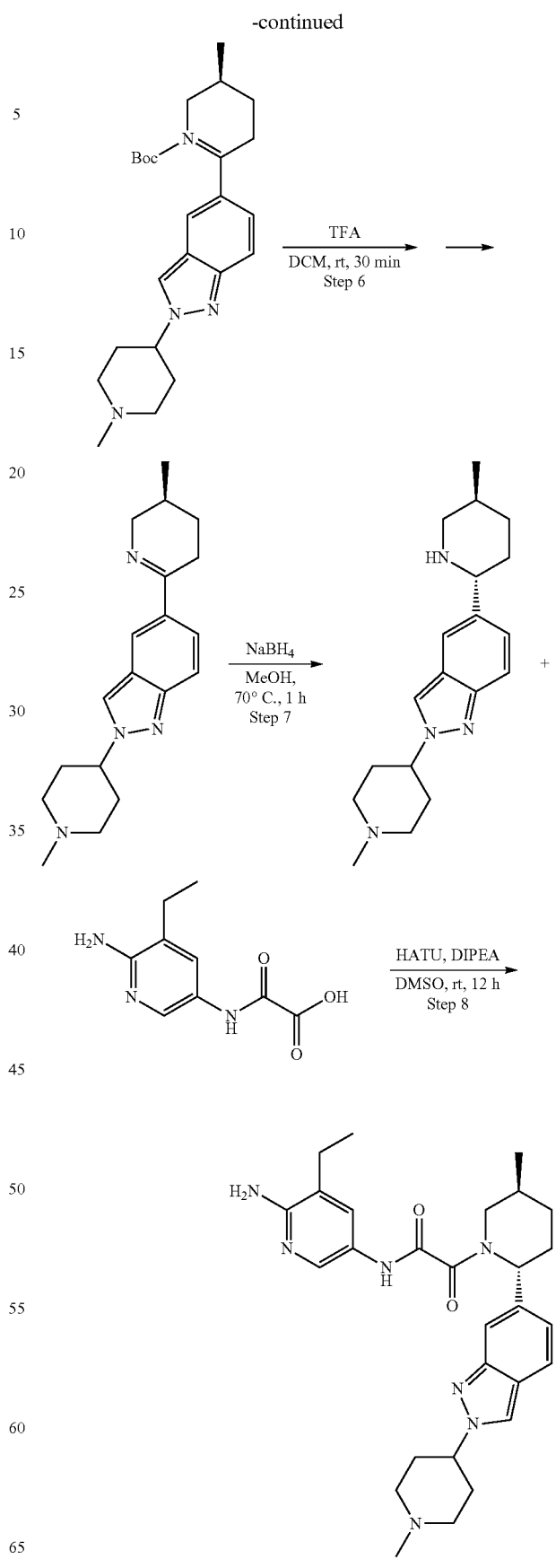

Step 1: The Synthesis of tert-butyl 4-(6-bromoindazol-2-yl)piperidine-1-carboxylate Prepared by general procedure 13. Step 1B
FCC conditions: Interchim 120 g SiO₂, HEX-EtOAc from 0~100%, flow rate=70 mL/min, cv=17.1
Yield: 2.98 g (60.08%)
LCMS(ESI): [M+H]⁺ m/z: calcd 380.2; found 380.0; Rt=1.540 min.

Step 2: The Synthesis of 6-bromo-2-(4-piperidyl)indazole

Prepared by general procedure 13. Step 2B
Yield: 0.57 g (77.37%)
LCMS(ESI): [M+H]⁺ m/z: calcd 282.2; found 282.2; Rt=0.770 min.

Step 3: The Synthesis of 6-bromo-2-(1-methyl-4-piperidyl)indazole

Prepared by general procedure 13. Step 3B
Yield: 0.27 g (45.11%)
LCMS(ESI): [M+H]⁺ m/z: calcd 294.2; found 294.0; Rt=0.866 min.

Step 4: The Synthesis of 2-(1-methyl-4-piperidyl)-6-(4,4,5,5-tetramethyl-1,3,2-dioxaborolan-2-yl)indazole Prepared by general procedure 13. Step 2A
Yield: 0.35 g (84.35%)
LCMS(ESI): [M+H]⁺ m/z: calcd 342.2; found 342.2; Rt=0.947 min.

Step 5: The Synthesis of tert-butyl rac-(3S)-3-methyl-6-[2-(1-methyl-4-piperidyl)indazol-6-yl]-3,4-dihydro-2H-pyridine-1-carboxylate Prepared by general procedure 13. Step 2
HPLC conditions: 2-10 min 20-100% water-methanol+FA; flow 30 mL/min (loading pump 4 mL/min methanol), Column Sun Fire C18 100*19 mm
Yield: 0.07 g (16.62%)
LCMS(ESI): [M+H]⁺ m/z: calcd 411.2; found 411.2; Rt=0.910 min.

Step 6: The Synthesis of 2-(1-methyl-4-piperidyl)-6-[rac-(3S)-3-methyl-2,3,4,5-tetrahydropyridin-6-yl]indazole Prepared by general procedure 13. Step 3 (Method A)
Yield: 0.05 g (94.46%)
LCMS(ESI): [M+H]⁺ m/z: calcd 311.2; found 311.2; Rt=0.542 min.

Step 7: The Synthesis of 2-(1-methyl-4-piperidyl)-6-[rac-(2R,5S)-5-methyl-2-piperidyl]indazole Prepared by general procedure 13. Step 4
Yield: 0.041 g (81.47%)
LCMS(ESI): [M+H]⁺ m/z: calcd 313.2; found 313.2; Rt=0.613 min.

Step 8: The Synthesis of N-(6-amino-5-ethyl-3-pyridyl)-2-oxo-2-[rac-(2R,5S)-5-methyl-2-[2-(1-methyl-4-piperidyl)indazol-6-yl]-1-piperidyl]acetamide (Compound 1096

Prepared by General Procedure 13. Step 5
HPLC conditions: 2-10 min 40-100% water-methanol+NH₃ 30 ml/min (loading pump 4 ml methanol), column: sun fire c18
Yield: 8.2 mg (21.92%)
¹H NMR (600 MHz, dmso) δ 0.74-1.05 (m, 3H), 1.05-1.17 (m, 3H), 1.29-1.40 (m, 1H), 1.70-1.81 (m, 1H), 1.82-1.92 (m, 1H), 2.01-2.15 (m, 7H), 2.21 (s, 3H), 2.26-2.35 (m, 1H), 2.37-2.44 (m, 2H), 2.75-3.21 (m, 3H), 3.45-4.07 (m, 1H), 4.34-4.48 (m, 1H), 5.17-5.76 (m, 3H), 6.91-7.08 (m, 1H), 7.42-7.57 (m, 2H), 7.62-7.71 (m, 1H), 7.98-8.12 (m, 1H), 8.37 (s, 1H), 10.53 (br s, 1H).
LCMS(ESI): [M+H]⁺ m/z: calcd 504.2; found 504.2; Rt=1.667 min.

FURTHER EXAMPLES

Example 683. The Synthesis of N-(6-amino-5-methylpyridin-3-yl)-2-oxo-2-(2-(Thiophen-2-yl)piperidin-1-yl)acetamide (Compound 9)

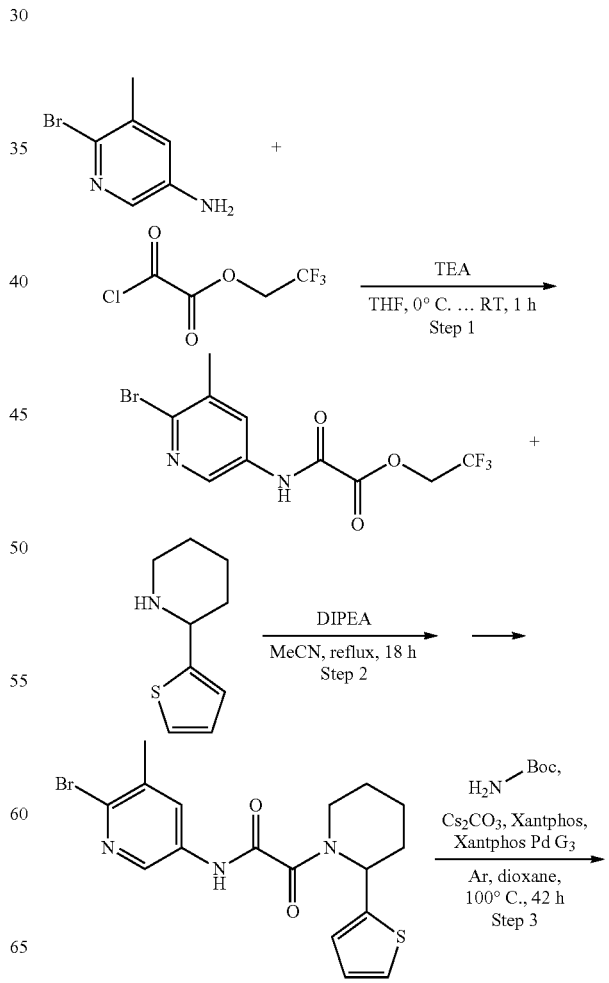

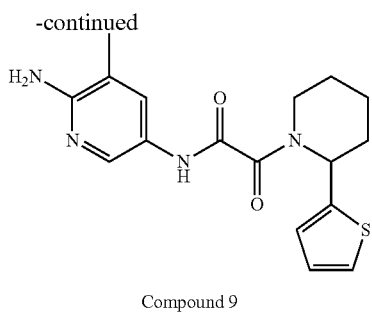

Compound 9

Step 1: The Synthesis of 2,2,2-trifluoroethyl 2-[(6-bromo-5-methyl-3-pyridyl)amino]-2-oxo-acetate To a solution of 6-bromo-5-methyl-pyridin-3-amine (5 g, 26.73 mmol) and triethylamine (2.71 g, 26.73 mmol, 3.73 mL) in THF (250 mL) was added 2,2,2-trifluoroethyl 2-chloro-2-oxo-acetate (5.09 g, 26.73 mmol) at 0° C. After stirring at rt for 1 hr, the resulting mixture were filtered and evaporated to dryness to give 2,2,2-trifluoroethyl 2-[(6-bromo-5-methyl-3-pyridyl)amino]-2-oxo-acetate (9 g, 26.39 mmol, 98.71% yield) as a beige solid and was used in the next step without further purification.
$^1$H NMR (500 MHz, DMSO-$d_6$) δ 2.33 (s, 3H), 4.99 (q, 2H), 8.13 (s, 1H), 8.59 (s, 1H), 11.28 (s, 1H).
LCMS(ESI): [M+H]$^+$ m/z: calcd 341.0; found 342.2; Rt=1.277 min.

Step 2: The Synthesis of N-(6-bromo-5-methylpyridin-3-yl)-2-oxo-2-(2-Thiophen-2-ylpiperidin-1-yl)acetamide To a solution of 2,2,2-trifluoroethyl 2-[(6-bromo-5-methyl-3-pyridyl)amino]-2-oxo-acetate (3 g, 8.80 mmol) and 2-(2-thienyl)piperidine (1.47 g, 7.22 mmol, HCl) in acetonitrile (50 mL) was added DIPEA (3.41 g, 26.40 mmol, 4.60 mL). The resulting mixture was heated to reflux for 18 hr. The reaction mixture was evaporated to dryness and subjected to column chromatography (Companion combiflash; 120 g SiO$_2$, petroleum ether/ethyl acetate with ethyl acetate from 10~35%, flow rate=85 mL/min, Rv=6 CV). N-(6-bromo-5-methylpyridin-3-yl)-2-oxo-2-(2-thiophen-2-ylpiperidin-1-yl)acetamide (1.5 g, 3.67 mmol, 41.75% yield) was obtained as a pale-yellow gum.
$^1$H NMR (400 MHz, CDCl$_3$) δ 1.56 (m, 5H), 1.76 (m, 1H), 2.36 (m, 4H), 3.22 (m, 1H), 4.80 (m, 1H), 6.05 (m, 1H), 6.93 (m, 2H), 8.05 (m, 1H), 8.33 (d, 1H), 9.32 (d, 1H).
LCMS(ESI): [M+H]$^+$ m/z: calcd 407.0; found 408.0; Rt=1.426 min.

Step 3: The Synthesis of N-(6-amino-5-methylpyridin-3-yl)-2-oxo-2-(2-(Thiophen-2-yl)piperidin-1-yl)acetamide (Compound 9

To the mixture of N-(6-bromo-5-methyl-3-pyridyl)-2-oxo-2-[2-(2-thienyl)-1-piperidyl]acetamide (0.5 g, 1.22 mmol), tert-butyl carbamate (286.90 mg, 2.45 mmol) and cesium carbonate (797.97 mg, 2.45 mmol) in dioxane (10 mL) under Ar, were added XantPhos (35.43 mg, 61.23 μmol) and XantPhos Pd G3 (87.10 mg, 91.84 μmol). The mixture was heated at 100° C. for 42 hr. The final mixture was filtered and evaporated to give tert-butyl N-[3-methyl-5-[[2-oxo-2-[2-(2-thienyl)-1-piperidyl]acetyl]amino]-2-pyridyl]carbamate (0.95 g, crude). The obtained solid was dissolved in HCl (4.0 M soln in dioxane, 2 ml) and stirred for 1 h. Then, the mixture was concentrated in vacuo. The residue was subjected to HPLC (SunFire C18 19*100 5 mkm column; 25-70% H$_2$O-MeCN, 10 min, flow: 30 mL/min, loading pump 4 ml/min MeCN) to afford N-(6-amino-5-methyl-3-pyridyl)-2-oxo-2-[2-(2-thienyl)-1-piperidyl]acetamide (0.007 g, 20.32 μmol, 1.66% yield) as yellow oil.
$^1$H NMR (400 MHz, CD$_3$OD) δ 1.69 (m, 2H), 1.78 (m, 2H), 2.00 (m, 1H), 2.13 (m, 3H), 2.33 (m, 1H), 2.65 (s, 3H), 3.01 (m, 1H), 4.07 (m, 1H), 5.86 (m, 1H), 7.01 (m, 2H), 7.35 (m, 1H), 7.59 (m, 1H), 8.06 (m, 1H).
LCMS(ESI): [M+H]$^+$ m/z: calcd 344.1; found 345.2; Rt=0.982 min.

Example 684. The Synthesis of N-(6-amino-5-methyl-3-pyridyl)-2-oxo-2-[(2S)-2-(2-thienyl)-1-piperidyl]acetamide (Compound 24) and N-(6-amino-5-methyl-3-pyridyl)-2-oxo-2-[(2R)-2-(2-thienyl)-1-piperidyl]acetamide (Compound 22)

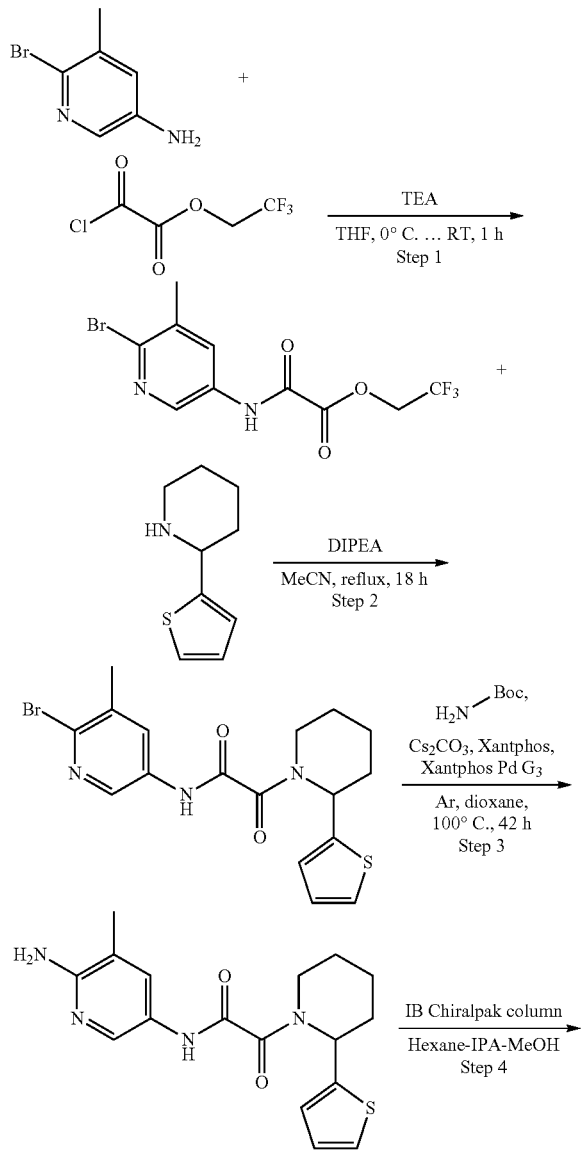

Compound 9

-continued

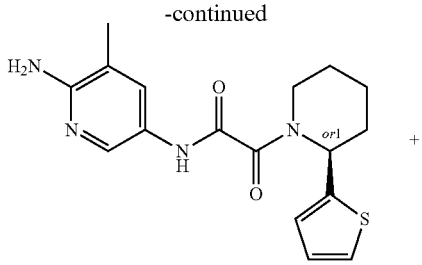

Compound 24

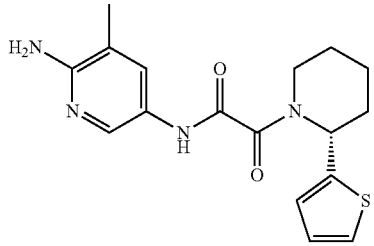

Compound 22

Steps 1-3 are the Same as for Compound 9

Step 4: The Synthesis of N-(6-amino-5-methyl-3-pyridyl)-2-oxo-2-[(2S)-2-(2-thienyl)-1-piperidyl]acetamide (Compound 24) and N-(6-amino-5-methyl-3-pyridyl)-2-oxo-2-[(2R)-2-(2-thienyl)-1-piperidyl]acetamide (Compound 22

Chiral separation was performed using 1B (250*20, 5 mkm) Chiralpak column, Hexane-IPA-MeOH, 90-5-5, Flow 15 ml/min affording Compound 24—N-(6-amino-5-methyl-3-pyridyl)-2-oxo-2-[(2S)-2-(2-thienyl)-1-piperidyl]acetamide (8.84 mg, 32.74% yield; RT=54.098 min) and Compound 22—N-(6-amino-5-methyl-3-pyridyl)-2-oxo-2-[(2R)-2-(2-thienyl)-1-piperidyl]acetamide (9.35 mg, 34.63% yield; RT=51.528 min).

Compound 22: RT (IB, Hexane-IPA-MeOH, 90-5-5, 0.6 ml/min)=50.937 min.

$^1$H NMR (500 MHz, CDCl$_3$) δ 1.76 (m, 4H), 1.84 (m, 1H), 2.05 (m, 1H), 2.15 (m, 3H), 2.33 (m, 1H), 3.08 (m, 1H), 4.40 (m, 2H), 4.73 (m, 1H), 6.43 (m, 1H), 6.95 (m, 1H), 7.00 (m, 1H), 7.78 (m, 1H), 8.07 (m, 1H), 9.01 (m, 1H).

LCMS(ESI): [M+H]$^+$ m/z: calcd 344.1; found 345.0; Rt=3.711 min.

Compound 24: RT (IB, Hexane-IPA-MeOH, 90-5-5, 0.6 ml/min)=46.420 min.

$^1$H NMR (500 MHz, CDCl$_3$) δ 1.76 (m, 4H), 1.84 (m, 1H), 2.05 (m, 1H), 2.15 (m, 3H), 2.33 (m, 1H), 3.10 (m, 1H), 4.40 (m, 2H), 4.74 (m, 1H), 6.43 (m, 1H), 6.95 (m, 1H), 7.00 (m, 1H), 7.78 (m, 1H), 8.07 (m, 1H), 9.00 (m, 1H).

LCMS(ESI): [M+H]$^+$ m/z: calcd 344.1; found 345.0; Rt=3.707 min.

Example 685. Synthesis of N-(6-amino-5-methyl-3-pyridyl)-2-[(2R,6R)-2-methyl-6-phenyl-1-piperidyl]-2-oxo-acetamide (Compound 415) and N-(6-amino-5-methyl-3-pyridyl)-2-[(2S,6S)-2-methyl-6-phenyl-1-piperidyl]-2-oxo-acetamide (Compound 417)

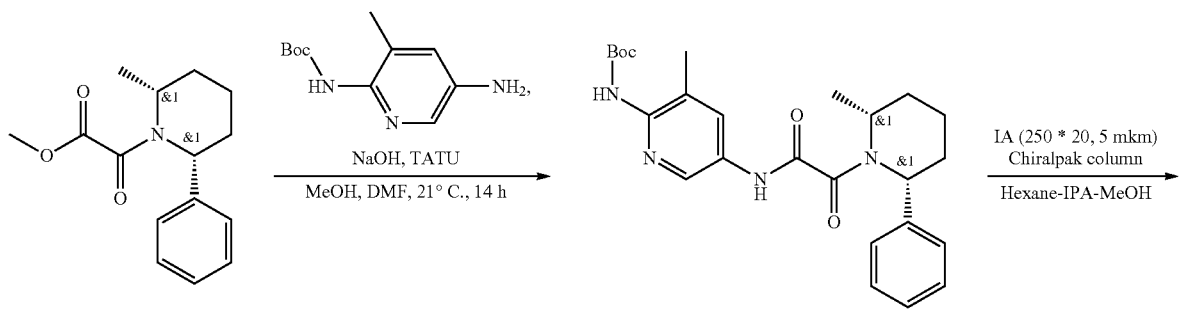

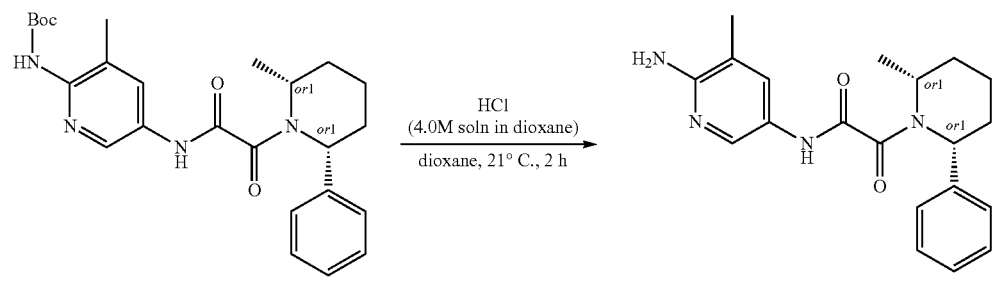

Compound 415

+

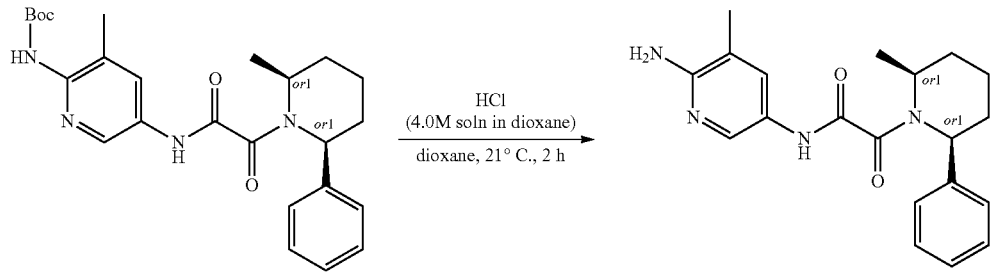

Compound 417

Step 1: Synthesis of tert-butyl N-[3-methyl-5-[[2-[(2R,6R)-2-methyl-6-phenyl-1-piperidyl]-2-oxo-acetyl]amino]-2-pyridyl]carbamate To a solution of methyl 2-[(2R,6R)-2-methyl-6-phenyl-1-piperidyl]-2-oxo-acetate (0.74 g, 2.83 mmol) in MeOH (10 mL), sodium hydroxide, pearl (113.26 mg, 2.83 mmol, 53.18 µL) was added and the resulting mixture was stirred for 1 hr. Then, the solvent was evaporated and the residue was re-evaporated with EtOH. After that, solids were dissolved in DMF and TATU (1.09 g, 3.40 mmol) was added followed by tert-butyl N-(5-amino-3-methyl-2-pyridyl)carbamate (632.26 mg, 2.83 mmol) and the resulting mixture was stirred for 12 hr. The reaction mixture was poured into water, extracted 3 times with EtOAc. The combined organics were washed with water, brine and evaporated. The residue was subjected to HPLC (40-60% 0.5-5 min; water(hcl)-acetonitrile 30 mL/min; loading pump 4 mL/min; column SunFire 19*100 mm). tert-butyl N-[3-methyl-5-[[2-[(2R,6R)-2-methyl-6-phenyl-1-piperidyl]-2-oxo-acetyl]amino]-2-pyridyl]carbamate (0.2964 g, 654.96 µmol, 23.13% yield) was obtained as a white solid. $^1$H NMR (500 MHz, CDCl$_3$) δ 0.94 (m, 3H), 1.52 (s, 9H), 1.87 (m, 4H), 2.31 (s, 3H), 2.59 (m, 1H), 5.02 (m, 1H), 6.78 (m, 1H), 7.25 (m, 2H), 7.34 (m, 3H), 8.09 (s, 1H), 8.37 (s, 1H), 9.33 (m, 1H).

LCMS(ESI): [M+H]$^+$ m/z: calcd 452.2; found 453.2; Rt=1.427 min.

Step 2: Chiral Resolution of Tert-butyl N-[3-methy-5-[[2-[(2R,6R)-2-methyl-6-phenyl-1-piperidyl]-2-oxo-acetyl]amino]-2-pyridyl]carbamate Chiral resolution was performed using IA (250*20, 5 mkm) Chiralpak column; Hexane-IPA-MeOH 70-15-15 as a mobile phase; Flow rate 12 mL/min; affording tert-butyl N-[3-methyl-5-[[2-[(2R,6R)-2-methyl-6-phenyl-1-piperidyl]-2-oxo-acetyl]amino]-2-pyridyl]carbamate (147.1 mg, 325.05 µmol, 49.63% yield) (RT (IA, Hexane-IPA-MeOH, 50-25-25, 0.6 mL/min)=9.7692 min) and tert-butyl N-[3-methyl-5-[[2-[(2S,6S)-2-methyl-6-phenyl-1-piperidyl]-2-oxo-acetyl]amino]-2-pyridyl]carbamate (123.99 mg, 273.98 µmol, 41.83% yield) (RT (IA, Hexane-IPA-MeOH, 50-25-25, 0.6 mL/min)=16.8562 min. RT (IA, Hexane-IPA-MeOH, 50-25-25, 0.6 mL/min)=9.7692 min. $^1$H NMR (500 MHz, CDCl$_3$) δ 0.94 (m, 3H), 1.25 (m, 1H), 1.49 (s, 9H), 1.64 (m, 2H), 1.96 (m, 3H), 2.30 (s, 3H), 2.61 (m, 1H), 5.02 (m, 1H), 6.82 (m, 1H), 7.32 (m, 2H), 7.38 (m, 3H), 8.10 (s, 1H), 8.41 (s, 1H), 9.38 (m, 1H). LCMS(ESI): [M+2H]$^+$ m/z: calcd 452.2; found 454.2; Rt=5.688 mi

Step 3: Synthesis of N-(6-amino-5-methyl-3-pyridyl)-2-[(2R,6R)-2-methyl-6-phenyl-1-piperidyl]-2-oxo-acetamide (Compound 415

To a solution of tert-butyl N-[3-methyl-5-[[2-[(2R,6R)-2-methyl-6-phenyl-1-piperidyl]-2-oxo-acetyl]amino]-2-pyridyl]carbamate (147.1 mg, 325.05 µmol) in dioxane (5 mL), hydrogen chloride solution 4.0 M in dioxane (59.26 mg, 1.63 mmol, 74.07 µL) was added at 21° C. The resulting mixture was left to stir for 2 hr. The resulting mixture was evaporated to dryness and subjected to HPLC (C18 column, H$_2$O-MeCN, 30-50% MeCN, 30 mL/min) to obtain N-(6-amino-5-methyl-3-pyridyl)-2-[(2R,6R)-2-methyl-6-phenyl-1-piperidyl]-2-oxo-acetamide (40.84 mg, 115.88 µmol, 35.65% yield) as a white solid. $^1$H NMR (500 MHz, DMSO-d$_6$) δ (ppm) 0.65-0.80 (m, 3H), 1.49-1.57 (m, 1H), 1.57-1.67 (m, 1H), 1.70-1.84 (m, 3H), 2.01-2.13 (m, 3H), 4.05-4.75 (m, 1H), 5.13-5.73 (m, 3H), 7.16-7.42 (m, 5H), 7.42-7.60 (m, 2H), 7.91-8.19 (m, 1H), 10.38-10.63 (m, 1H). LCMS(ESI): [M+H]$^+$ m/z: calcd 352.2; found 353.2; Rt=2.577 min.

Step 4: Synthesis of N-(6-amino-5-methyl-3-pyridyl)-2-[(2S,6S)-2-methyl-6-phenyl-1-piperidyl]-2-oxo-acetamide (Compound 417

To a solution of tert-butyl N-[3-methyl-5-[[2-[(2S,6S)-2-methyl-6-phenyl-1-piperidyl]-2-oxo-acetyl]amino]-2-pyridyl]carbamate (123.99 mg, 273.98 µmol) in dioxane (5 mL), hydrogen chloride solution 4.0 M in dioxane (49.95 mg, 1.37 mmol, 62.44 µL) was added at 21° C. The resulting mixture was left to stir for 2 hr. The resulting mixture was evaporated to dryness and subjected to HPLC (C18 column, H$_2$O-MeCN, 30-50% MeCN, 30 mL/min) affording N-(6-amino-5-methyl-3-pyridyl)-2-[(2S,6S)-2-methyl-6-phenyl-1-piperidyl]-2-oxo-acetamide (48.4 mg, 137.33 µmol, 50.12% yield) as a white solid. $^1$H NMR (500 MHz, DMSO-d6) δ (ppm) 0.64-0.86 (m, 3H), 1.46-1.57 (m, 1H), 1.57-1.66 (m, 1H), 1.70-1.97 (m, 3H), 1.99-2.10 (m, 3H), 2.56-2.60 (m, 1H), 3.91-4.84 (m, 1H), 5.06-5.76 (m, 3H), 7.22-7.30 (m, 1H), 7.33-7.41 (m, 3H), 7.40-7.62 (m, 2H), 7.91-8.15 (m, 1H), 10.39-10.65 (m, 1H).

LCMS(ESI): [M+H]$^+$ m/z: calcd 352.2; found 353.2; Rt=2.569 min.

Example 686. Synthesis of N-(6-amino-5-methyl-3-pyridyl)-2-[rac-(2R,6R)-2-methyl-6-phenyl-1-piperidyl]-2-oxo-acetamide (Compound 112)

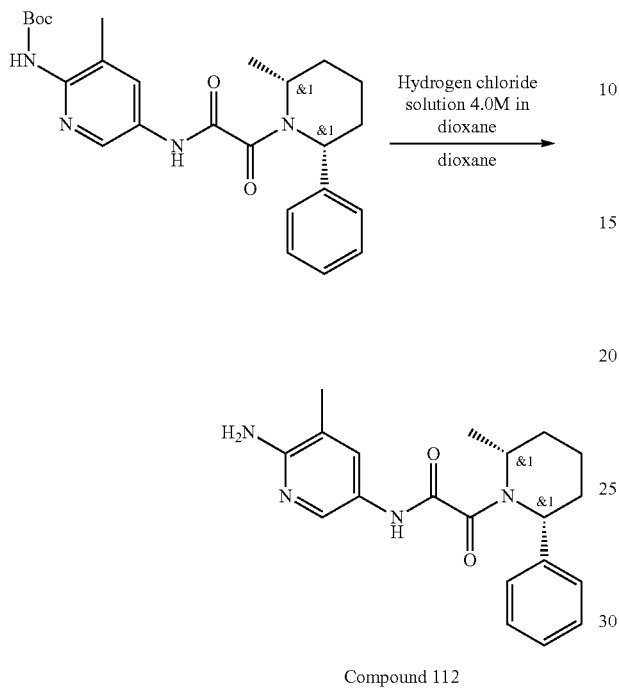

Compound 112

To a solution of tert-butyl N-[3-methyl-5-[[2-[(2R,6R)-2-methyl-6-phenyl-1-piperidyl]-2-oxo-acetyl]amino]-2-pyridyl]carbamate (141.73 mg, 234.89 μmol) (prepared as described in Example 685) in dioxane (2 mL) was added Hydrogen chloride solution 4.0 M in dioxane (400.00 mg, 10.97 mmol, 0.5 mL) at 21° C. The resulting mixture was left to stir for 6 hr. The resulting mixture was evaporated to dryness and purified by HPLC (2-7 min, 40-90 min, R1 30 mL/min; Sunfire C18, 100×19×5 um; loading pump: 5 mL/min R1) to give N-(6-amino-5-methyl-3-pyridyl)-2-[(2R,6R)-2-methyl-6-phenyl-1-piperidyl]-2-oxo-acetamide (17.7 mg, 50.22 μmol, 21.38% yield) as a white solid. $^1$H NMR (DMSO-d$_6$, 500 MHz): δ (ppm) 0.91 (m, 5H), 1.54 (m, 3H), 1.79 (m, 3H), 2.10 (m, 3H), 4.77 (m, 1H), 6.09 (m, 2H), 7.40 (m, 6H), 8.19 (m, 1H), 10.71 (s, 1H) LCMS(ESI): [M+H]$^+$ m/z: calcd 352.2; found 353.2; Rt=2.737 min.

Example 687. The Synthesis of 5-(2-(2-cyclopentylpiperidin-1-yl)-2-oxoacetamido)nicotinamide (Compound 240)

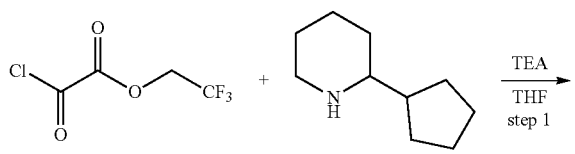

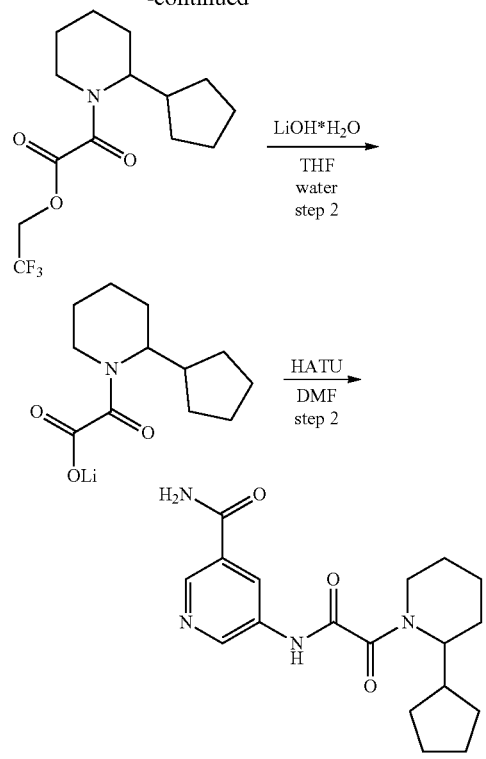

Compound 240

Step 1: Synthesis of 2,2,2-trifluoroethyl 2-(2-cyclopentylpiperidin-1-yl)-2-oxoacetate 2,2,2-trifluoroethyl 2-chloro-2-oxo-acetate (1.14 g, 5.98 mmol) was added dropwise to the solution of 2-cyclopentyl-5-methyl-piperidine (1 g, 5.98 mmol) and TEA (604.88 mg, 5.98 mmol, 833.16 μL) in THF (30 mL) at −10° C. The resulting mixture was left to warm to rt and stirred for 12 hr. The resulting precipitate was filtered off. The filtrate was evaporated to obtain 2,2,2-trifluoroethyl 2-(2-cyclopentyl-5-methyl-1-piperidyl)-2-oxo-acetate (2 g, crude) which was used in next step without purification.

$^1$H NMR (400 MHz, DMSO-d$_6$) δ (ppm) 1.25 (m, 6H), 1.68 (m, 8H), 3.14 (m, 1H), 3.26 (m, 1H), 3.59 (m, 1H), 4.15 (m, 1H), 5.05 (m, 2H). LCMS(ESI): [M+1]$^+$ m/z: calcd 307.3; found 308.2; Rt=1.548 min.

Step 2: Synthesis of Lithium 2-(2-cyclopentylpiperidin-1-yl)-2-oxoacetate

Lithium hydroxide monohydrate, 98% (261.18 mg, 6.22 mmol, 172.97 μL) was added to the solution of 2,2,2-trifluoroethyl 2-(2-cyclopentyl-1-piperidyl)-2-oxo-acetate (1.91 g, 6.22 mmol) in water (2 mL) and THF (20 mL) and the resulting mixture was stirred at 20° C. for 12 hr. The resulting mixture was evaporated to dryness to obtain [2-(2-cyclopentyl-1-piperidyl)-2-oxo-acetyl]oxylithium (1.3 g, 5.62 mmol, 90.33% yield) which was used in next step without purification.

$^1$H NMR (400 MHz, DMSO-d$_6$) δ (ppm) 1.25 (m, 6H), 1.68 (m, 8H), 2.36 (m, 1H), 3.27 (m, 1H), 3.89 (m, 1H), 4.13 (m, 1H). LCMS(ESI): [M+1]$^+$ m/z: calcd 225.3; found 226.2; Rt=1.121 min.

Step 3: Synthesis of 5-(2-(2-cyclopentylpiperidin-1-yl)-2-oxoacetamido)nicotinamide

[2-(2-cyclopentyl-1-piperidyl)-2-oxo-acetyl]oxylithium (0.5 g, 2.16 mmol) was mixed with HATU (904.46 mg, 2.38 mmol) in DMF (5 mL) and the resulting mixture was stirred at 20° C. for 10 min followed by addition of 5-aminopyridine-3-carboxamide (296.56 mg, 2.16 mmol). The resulting mixture was stirred at 20° C. for 12 hr. The resulting solution was subjected to HPLC (column SunFire 19*100 mm, water-MeCN as mobile phase) to obtain 5-[[2-(2-cyclopentyl-1-piperidyl)-2-oxo-acetyl]amino]pyridine-3-carboxamide (0.194 g, 563.29 μmol, 26.05% yield).

$^1$H NMR (600 MHz, DMSO-d$_6$) δ (ppm) 0.98-1.23 (m, 2H), 1.33-1.42 (m, 1H), 1.42-1.78 (m, 12H), 2.75-3.19 (m, 1H), 3.49-3.60 (m, 1H), 4.18-4.25 (m, 1H), 7.50-7.65 (m, 1H), 8.09-8.18 (m, 1H), 8.43-8.55 (m, 1H), 8.73-8.78 (m, 1H), 8.83-8.92 (m, 1H), 11.02-11.12 (m, 1H). LCMS(ESI): [M+1]$^+$ m/z: calcd 344.4; found 345.2; Rt=3.146 min.

Example 688. The Synthesis of N-methyl-4-(5-methyl-1-(2-((5-methylpyridin-3-yl)amino)-2-oxoacetyl)piperidin-2-yl)benzamide (Compound 92)

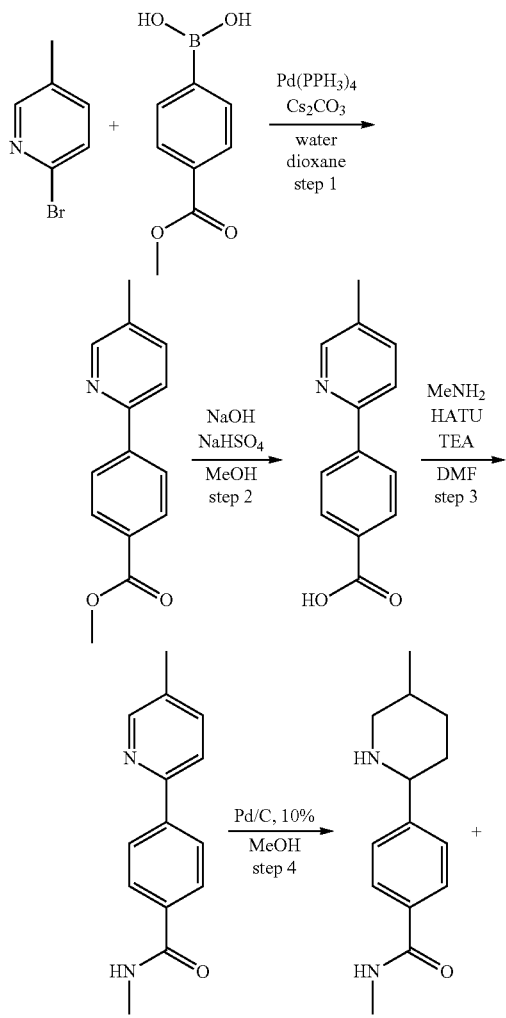

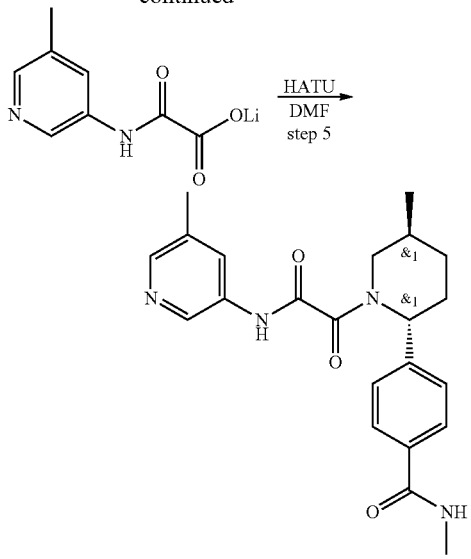

Compound 92

Step 1: Synthesis of methyl 4-(5-methylpyridin-2-yl)benzoate 2-bromo-5-methyl-pyridine (1.82 g, 10.57 mmol) and (4-methoxycarbonylphenyl)boronic acid (2 g, 11.11 mmol) were dissolved in dioxane (40 mL) and water (5 mL). Cesium carbonate (8.23 g, 25.26 mmol) was added thereto. Then, Palladium (0)tetrakis(triphenylphosphine) (583.73 mg, 505.15 μmol) was added and reaction flask was quickly evacuated and refilled with argon. Resulting mixture was stirred at 65° C. for 12 hr. After that, it was cooled and evaporated. The residue was partitioned between EtOAc (100 ml) and water (100 ml). The organic phase was collected, dried over Na$_2$SO$_4$ and evaporated. The residue was subjected to column chromatography to obtain methyl 4-(5-methyl-2-pyridyl)benzoate (0.3 g, 1.32 mmol, 13.07% yield).

$^1$H NMR (500 MHz, DMSO-d$_6$) δ (ppm) 2.35 (s, 3H), 3.87 (s, 3H), 7.74 (d, 1H), 7.96 (d, 1H), 8.04 (d, 2H), 8.20 (d, 2H), 8.55 (s, 1H).

LCMS(ESI): [M]$^+$ m/z: calcd 227.2; found 228.2; Rt=1.255 min.

Step 2: Synthesis of 4-(5-methylpyridin-2-yl)benzoic acid

Sodium hydroxide, pearl (105.60 mg, 2.64 mmol, 49.58 μL) was added to the solution of methyl 4-(5-methyl-2-pyridyl)benzoate (0.3 g, 1.32 mmol) in MeOH (20 mL) and the resulting mixture was heated at 65° C. for 12 hr. The resulting solution was cooled to r.t. and evaporated. The residue was partitioned between DCM (10 ml) and water (10 ml). The aqueous layer was collected and acidified with sodium hydrogensulfate (316.98 mg, 2.64 mmol). The resulting mixture was extracted with EtOAc (2×30 ml). The combined organic layer was evaporated to obtain 4-(5-methyl-2-pyridyl)benzoic acid (0.28 g, 1.31 mmol, 99.47% yield).

$^1$H NMR (500 MHz, DMSO-d$_6$) δ (ppm) 2.32 (s, 3H), 7.65 (d, 1H), 7.83 (d, 1H), 7.93 (m, 4H), 8.48 (s, 1H).

LCMS(ESI): [M]+ m/z: calcd 213.2; found 214.2; Rt=0.881 min.

Step 3: Synthesis of N-methyl-4-(5-methylpyridin-2-yl)benzamide 4-(5-methyl-2-pyridyl)benzoic acid (0.28 g, 1.31 mmol), methanamine (177.32 mg, 2.63 mmol, 197.24 μL, HCl), HATU (549.22 mg, 1.44 mmol) and triethylamine (465.06 mg, 4.60 mmol, 640.58 μL) were mixed in DMF (5 mL) and the resulting mixture was stirred at 20° C. for 12 hr. The resulting mixture was partitioned between EtOAc (50 ml) and water (50 ml). The organic layer was collected, washed with water, brine and evaporated. The residue was subjected to column chromatography to obtain N-methyl-4-(5-methyl-2-pyridyl)benzamide (0.2 g, 883.89 μmol, 67.31% yield).

$^1$H NMR (500 MHz, DMSO-$d_6$) δ (ppm) 2.34 (s, 3H), 2.80 (d, 3H), 7.71 (d, 1H), 7.93 (m, 3H), 8.13 (d, 2H), 8.50 (m, 2H).

LCMS(ESI): [M]+ m/z: calcd 226.2; found 227.2; Rt=0.783 min.

Step 4: Synthesis of N-methyl-4-(5-methylpiperidin-2-yl)benzamide

Palladium, 10% on carbon, Type 487, dry (1.88 mg, 17.68 μmol) was added to the solution of N-methyl-4-(5-methyl-2-pyridyl)benzamide (0.2 g, 883.89 μmol) in MeOH (30 mL) and the resulting mixture was hydrogenated at 50 atm. pressure and 50° C. for 72 hr. After consumption of starting material (H-NMR control) the resulting mixture was cooled to r.t. and filtered. The filtrate was evaporated to dryness. The residue was subjected to HPLC (column SunFire 100*19 mm 5 um, water-MeCN+NH$_3$ as eluent mixture) to obtain N-methyl-4-(5-methyl-2-piperidyl)benzamide (0.012 g, 51.65 μmol, 5.84% yield).

$^1$H NMR (500 MHz, DMSO-$d_6$) δ (ppm)

LCMS(ESI): [M]+ m/z: calcd 232.3; found 233.2; Rt=1.556 min.

Step 5: Synthesis of N-methyl-4-(5-methyl-1-(2-((5-methylpyridin-3-yl)amino)-2-oxoacetyl)piperidin-2-yl)benzamide (Compound 92

[2-[(5-methyl-3-pyridyl)amino]-2-oxo-acetyl]oxylithium (9.61 mg, 51.65 μmol) and HATU (19.64 mg, 51.65 μmol) were mixed in DMF (2 mL) and the resulting mixture was stirred at 20° C. for 20 min followed by addition of N-methyl-4-(5-methyl-2-piperidyl)benzamide (0.012 g, 51.65 μmol) and the resulting mixture was stirred at 20° C. for 12 hr. The resulting mixture was subjected to HPLC (column SunFire 100*19 mm 5 um, water-MeCN as eluent mixture) to obtain N-methyl-4-[5-methyl-1-[2-[(5-methyl-3-pyridyl)amino]-2-oxo-acetyl]-2-piperidyl]benzamide (0.005 g, 12.68 μmol, 24.54% yield).

$^1$H NMR (500 MHz, CDCl$_3$) δ (ppm) 1.12 (m, 3H), 1.41 (m, 1H), 2.00 (m, 2H), 2.25 (m, 2H), 2.38 (m, 3H), 3.20 (m, 4H), 4.47 (m, 1H), 6.18 (m, 2H), 7.36 (d, 2H), 7.78 (d, 2H), 8.13 (m, 1H), 8.25 (m, 1H), 8.62 (m, 1H), 9.57 (m, 1H).

LCMS(ESI): [M]+ m/z: calcd 394.5; found 395.2; Rt=2.496 min.

Example 689. The Synthesis of N-methyl-3-[(2R,5S)-5-methyl-1-[2-[(5-methyl-3-pyridyl)amino]-2-oxo-acetyl]-2-piperidyl]benzamide (Compound 48)

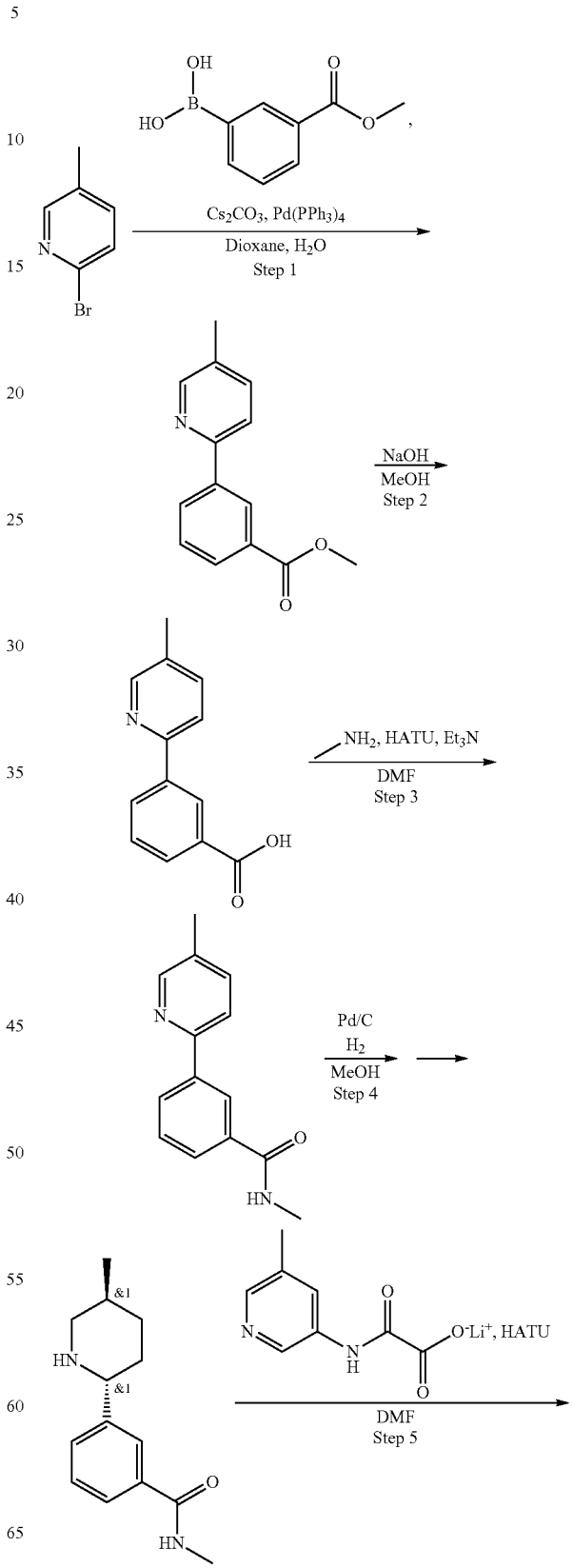

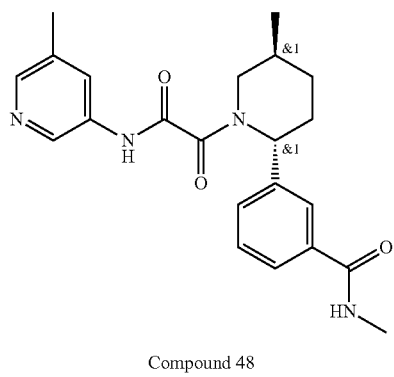

Compound 48

Step 1: Synthesis of methyl 3-(5-methyl-2-pyridyl)benzoate

To a stirred solution of 2-bromo-5-methyl-pyridine (2 g, 11.63 mmol) and (3-methoxycarbonylphenyl)boronic acid (2.30 g, 12.79 mmol) in dioxane (40 mL) and water (4 mL) was added cesium carbonate (9.47 g, 29.07 mmol). The resulting suspension was degassed with argon. Palladium (0)tetrakis(triphenylphosphine) (671.75 mg, 581.32 μmol) was added. The reaction mixture was stirred at 65° C. for 12 hours. Upon completion, the reaction mixture was filtered and the filtrate was evaporated in vacuo. The residue was partitioned between EtOAc (100 mL) and water (100 mL). The organic phase was dried over $Na_2SO_4$, filtered and concentrated under reduced pressure. The crude product was purified by column chromatography to obtain methyl 3-(5-methyl-2-pyridyl)benzoate (1 g, 4.40 mmol, 37.85% yield).

$^1$H NMR (DMSO-$d_6$, 500 MHz): δ (ppm) 2.35 (s, 3H), 3.89 (s, 3H), 7.63 (t, 1H), 7.72 (d, 1H), 7.93 (d, 1H), 7.99 (d, 1H), 8.32 (m, 1H), 8.54 (s, 1H), 8.67 (s, 1H).

Step 2: Synthesis of 3-(5-methyl-2-pyridyl)benzoic acid

To a stirred solution of methyl 3-(5-methyl-2-pyridyl) benzoate (1 g, 4.40 mmol) in MeOH (20 mL) was added Sodium hydroxide (352.00 mg, 8.80 mmol). The resulting reaction mixture was stirred at 65° C. for 12 hours. Upon completion, the reaction mixture was allowed to cool to room temperature and concentrated under reduced pressure. The obtained residue was partitioned between DCM (10 mL) and water (10 mL). The aqueous layer was acidified with sodium hydrogensulfate (1.06 g, 8.80 mmol). The resulting mixture was extracted with EtOAc (2×30 mL). The combined organic layer was dried over $Na_2SO_4$, filtered and concentrated under reduced pressure to obtain 3-(5-methyl-2-pyridyl)benzoic acid (0.9 g, 4.22 mmol, 95.92% yield).

$^1$H NMR (DMSO-$d_6$, 500 MHz): δ (ppm) 2.34 (s, 3H), 7.59 (t, 1H), 7.72 (d, 1H), 7.96 (m, 2H), 8.27 (d, 1H), 8.53 (s, 1H), 8.64 (s, 1H), 13.05 (brs, 1H).

Step 3: Synthesis of N-methyl-3-(5-methyl-2-pyridyl)benzamide

To a stirred solution of 3-(5-methyl-2-pyridyl)benzoic acid (1 g, 4.69 mmol), methanamine (HCl salt, 633.28 mg, 9.38 mmol) and HATU (1.96 g, 5.16 mmol) in DMF (5 mL) was added Triethylamine (1.66 g, 16.41 mmol, 2.29 mL). The resulting reaction mixture was stirred at 20° C. for 12 hours. After 12 hours, the reaction mixture was partitioned between EtOAc (50 mL) and water (50 mL). The organic layer was washed with water, brine, dried over $Na_2SO_4$ and concentrated under reduced pressure. The crude product was purified by column chromatography to obtain N-methyl-3-(5-methyl-2-pyridyl)benzamide (1.05 g, 4.64 mmol, 98.95% yield).

$^1$H NMR (DMSO-$d_6$, 500 MHz): δ (ppm) 2.35 (s, 3H), 2.81 (d, 3H), 7.55 (t, 1H), 7.74 (m, 1H), 7.85 (d, 1H), 7.93 (m, 1H), 8.18 (d, 1H), 8.52 (m, 3H).

LCMS(ESI): [M+H]$^+$ m/z: calcd 226.1; found 227.2; Rt=0.852 min.

Step 4: Synthesis of N-methyl-3-(5-methyl-2-piperidyl)benzamide

A solution of N-methyl-3-(5-methyl-2-pyridyl)benzamide (1.05 g, 4.64 mmol) in MeOH (30 mL) was hydrogenated over Palladium, 10% on carbon, Type 487, dry (493.83 mg, 4.64 mmol) under 50 atm $H_2$ pressure at 50° C. for 52 hours. Upon completion, the reaction mixture was filtered; the residue was washed with MeOH. The filtrate was concentrated under reduced pressure and the crude product was purified by reverse phase HPLC (Eluent: water-acetonitrile, 0-10%, 0.5-6 min; flow rate: 30 mL/min; loading pump: 4 mL/min, acetonitrile; column: SunFire 100*19 mm, 5 um) to obtain N-methyl-3-(5-methyl-2-piperidyl)benzamide (210 mg).

LCMS(ESI): [M+H]$^+$ m/z: calcd 232.2; found 233.2; Rt=1.668 min.

Step 5: Synthesis of N-methyl-3-[(2R,5S)-5-methyl-1-[2-[(5-methyl-3-pyridyl)amino]-2-oxo-acetyl]-2-piperidyl]benzamide (Compound 48

To a stirred solution of [2-[(5-methyl-3-pyridyl)amino]-2-oxo-acetyl]oxylithium (104.13 mg, 559.57 μmol) and HATU (212.77 mg, 559.57 μmol) in DMF (3 mL) was added N-methyl-3-(5-methyl-2-piperidyl)benzamide (0.13 g, 559.57 μmol). The resulting reaction mixture was stirred at 20° C. for 12 hours. The resulting mixture was subjected to reverse phase HPLC purification (Eluent: water-acetonitrile, 20-25%, 0.5-6 min; flow rate: 30 mL/min; loading pump: 4 mL/min, acetonitrile; column: SunFire 100*19 mm, 5 um) to obtain N-methyl-3-[(2R,5S)-5-methyl-1-[2-[(5-methyl-3-pyridyl)amino]-2-oxo-acetyl]-2-piperidyl]benzamide (Compound 48, 40.10 mg, 101.66 μmol, 18.17% yield) as an off-white solid.

$^1$H NMR (DMSO-$d_6$+CCl$_4$, 400 MHz): δ (ppm) 1.12 (m, 3H), 1.43 (m, 1H), 1.92 (m, 2H), 2.15 (m, 1H), 2.35 (m, 3H), 2.84 (m, 3H), 3.03 (m, 1H), 3.30 (m, 1H), 3.88 (m, 1H), 5.49 (m, 1H), 7.44 (m, 2H), 7.74 (m, 2H), 7.97 (m, 1H), 8.08 (m, 1H), 8.25 (m, 1H), 8.55 (m, 1H), 10.92 (m, 1H).

LCMS(ESI): [M+H]$^+$ m/z: calcd 394.2; found 395.2; Rt=1.013 min.

Example 690. The Synthesis of N-(6-amino-4,5-dimethylpyridin-3-yl)-2-(2-(4-hydroxyphenyl)-5-methylpiperidin-1-yl)-2-oxoacetamide (Compound 383, Compound 391
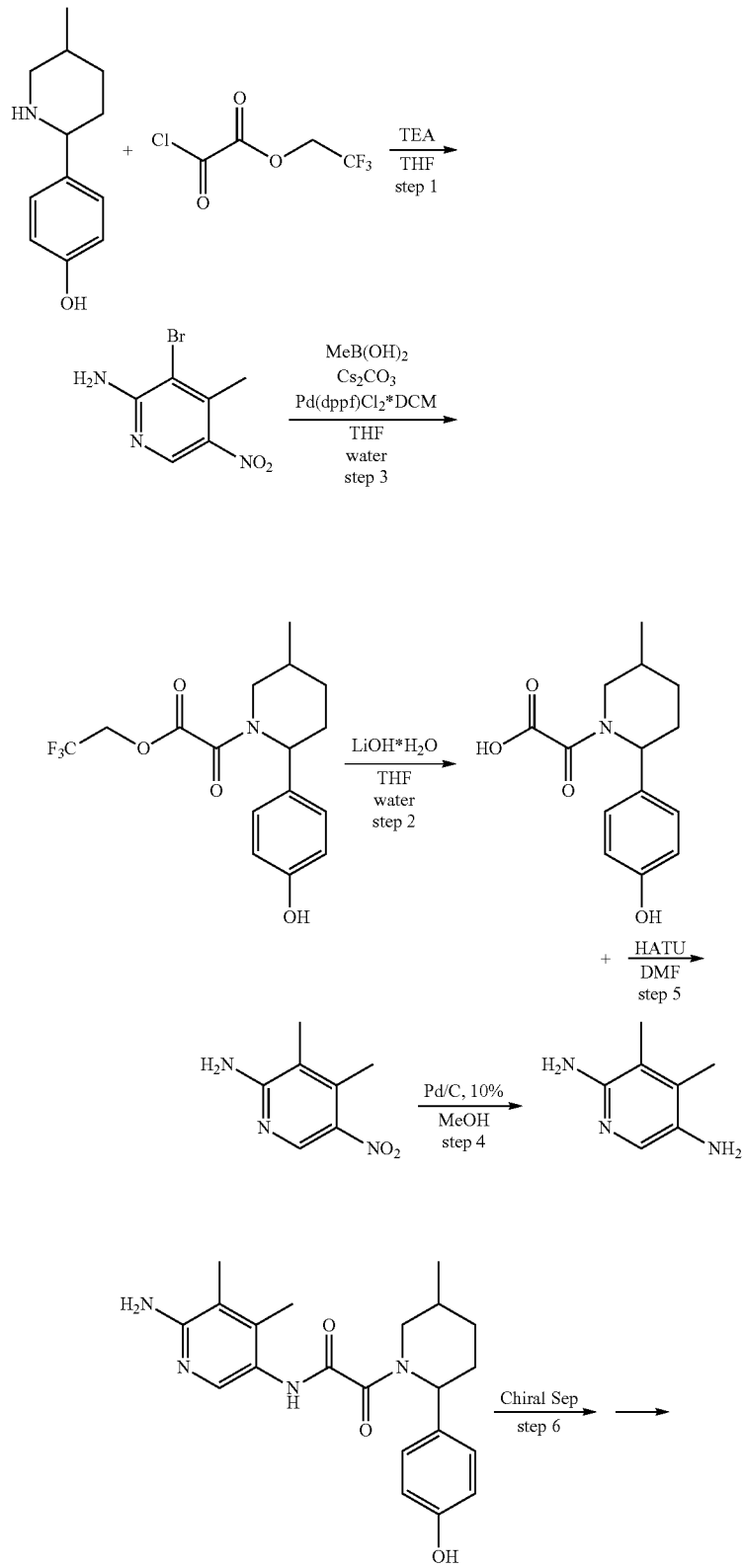

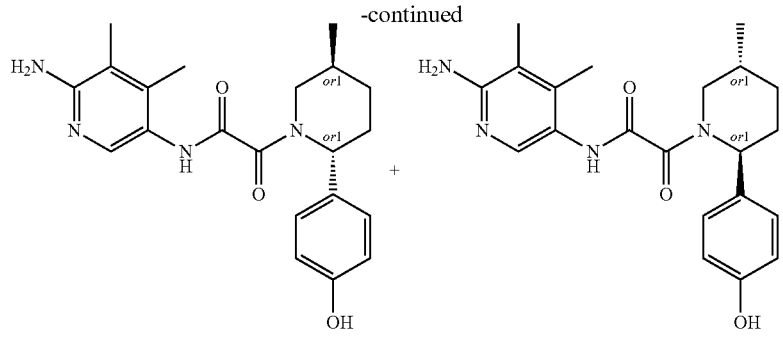

Compound 383          Compound 391

Step 1: Synthesis of 2,2,2-trifluoroethyl 2-(2-(4-hydroxyphenyl)-5-methylpiperidin-1-yl)-2-oxoacetate 2,2,2-trifluoroethyl 2-chloro-2-oxo-acetate (996.01 mg, 5.23 mmol) was added dropwise to the solution of 4-(5-methyl-2-piperidyl)phenol (1 g, 5.23 mmol) and TEA (529.05 mg, 5.23 mmol, 728.71 µL) in THF (20 mL) at −40° C. The resulting mixture was left to warm to rt and stirred for 12 hr. The resulting precipitate was filtered off. The filtrate was evaporated to obtain 2,2,2-trifluoroethyl 2-[2-(4-hydroxyphenyl)-5-methyl-1-piperidyl]-2-oxo-acetate (1.2 g, 3.48 mmol, 66.47% yield) which was used in next step without purification.

$^1$H NMR (400 MHz, DMSO-d$_6$) δ (ppm) 0.92 (d, 3H), 1.28 (m, 1H), 1.67 (m, 1H), 1.89 (m, 1H), 2.11 (m, 1H), 3.18 (m, 1H), 3.79 (m, 2H), 4.62 (m, 1H), 5.04 (m, 2H), 6.77 (m, 2H), 7.05 (m, 2H), 9.44 (m, 1H). LCMS(ESI): [M]$^+$ m/z: calcd 345.2; found 346.2; Rt=1.354 min Step 2: Synthesis of 2-(2-(4-hydroxyphenyl)-5-methylpiperidin-1-yl)-2-oxoacetic acid Lithium hydroxide monohydrate, 98% (145.83 mg, 3.48 mmol, 96.57 µL) was added to the solution of 2,2,2-trifluoroethyl 2-[2-(4-hydroxyphenyl)-5-methyl-1-piperidyl]-2-oxo-acetate (1.2 g, 3.48 mmol) in THF (20 mL) and water (2 mL) and the resulting mixture was stirred at 20° C. for 12 hr. The resulting mixture was evaporated to dryness to obtain 2-[2-(4-hydroxyphenyl)-5-methyl-1-piperidyl]-2-oxo-acetic acid (0.8 g, 2.96 mmol, 85.19% yield, Li*) which was used in next step without purification.

$^1$H NMR (500 MHz, DMSO-d$_6$) δ (ppm) 0.98 (d, 3H), 1.18 (m, 1H), 1.38 (m, 1H), 1.98 (m, 3H), 2.84 (m, 1H), 3.12 (m, 1H), 4.65 (m, 1H), 5.04 (m, 1H), 6.78 (m, 2H), 7.17 (m, 2H), 9.55 (m, 1H). LCMS(ESI): [M]$^+$ m/z: calcd 263.2; found 264.2; Rt=0.885 min.

Step 3: Synthesis of 3,4-dimethyl-5-nitropyridin-2-amine 3-bromo-4-methyl-5-nitro-pyridin-2-amine (5 g, 15.98 mmol, HBr) and methylboronic acid (4.78 g, 79.89 mmol) were dissolved in THF (100 mL) and water (10 mL). Caesium carbonate (33.84 g, 103.85 mmol) was added thereto. Then, Pd(dppf)Cl$_2$*DCM (798.86 µmol) was added and reaction flask was quickly evacuated and refilled with argon. Resulting mixture was stirred at 80° C. for 12 hr. After that, it was cooled and evaporated. The residue was partitioned between EtOAc (100 ml) and water (100 ml). The organic phase was collected, dried over Na$_2$SO$_4$ and evaporated to obtain 3,4-dimethyl-5-nitro-pyridin-2-amine (2 g, 11.96 mmol, 74.88% yield).

$^1$H NMR (400 MHz, CDCl$_3$) δ (ppm) 2.64 (s, 3H), 2.99 (s, 3H), 7.65 (bds, 2H), 9.16 (s, 1H). LCMS(ESI): [M]$^+$ m/z: calcd 167.2; found 168.2; Rt=0.881 min.

Step 4: Synthesis of 3,4-dimethylpyridine-2,5-Diamine

Palladium, 10% on carbon, Type 487, dry (636.62 mg, 5.98 mmol) was added to the solution of 3,4-dimethyl-5-nitro-pyridin-2-amine (1 g, 5.98 mmol) in MeOH (30 mL) and the resulting mixture was hydrogenated at 50 atm pressure and 20° C. for 12 hr. The resulting mixture was filtered and evaporated to obtain 3,4-dimethylpyridine-2,5-diamine (0.7 g, 5.10 mmol, 85.30% yield), which was used in next step without purification.

$^1$H NMR (400 MHz, DMSO-d$_6$) δ (ppm) 1.90 (s, 3H), 1.93 (s, 3H), 4.01 (bds, 2H), 4.60 (bds, 2H), 7.27 (s, 1H). LCMS(ESI): [M]$^+$ m/z: calcd 137.2; found 138.2; Rt=min.

Step 5: Synthesis of N-(6-amino-4,5-dimethylpyridin-3-yl)-2-(2-(4-hydroxyphenyl)-5-methylpiperidin-1-yl)-2-oxoacetamide 2-[2-(4-hydroxyphenyl)-5-methyl-1-piperidyl]-2-oxo-acetic acid (0.4 g, 1.48 mmol, Li+) was mixed with HATU (562.83 mg, 1.48 mmol) in DMF (5 mL) and the resulting mixture was stirred at 20° C. for 10 min followed by addition of 3,4-dimethylpyridine-2,5-diamine (203.06 mg, 1.48 mmol). The resulting mixture was stirred at 20° C. for 12 hr. The resulting solution was subjected to HPLC (column: TRIART 100*20, 5 microM, water/ACN+NH$_3$ as eluent mixture) to obtain N-(6-amino-4,5-dimethyl-3-pyridyl)-2-[2-(4-hydroxyphenyl)-5-methyl-1-piperidyl]-2-oxo-acetamide (0.057 g, 149.04 µmol, 10.07% yield).

$^1$H NMR (500 MHz, DMSO-d$_6$) δ (ppm) LCMS(ESI): [M]$^+$ m/z: calcd 382.5; found 383.2; Rt=0.811 min.

Step 6: Chiral Separation (Compound 383 and Compound 391

N-(6-amino-4,5-dimethyl-3-pyridyl)-2-[2-(4-hydroxyphenyl)-5-methyl-1-piperidyl]-2-oxo-acetamide (57 mg, 149.04 µmol) was separated using Chiralpak OD-H 250*30, 5 mkm column; Hexane-IPA-MeOH, 70-15-15 as a mobile phase; Flow rate 30 mL/min; Injection Volume: 900 mkl; affording Compound 383—N-(6-amino-4,5-dimethyl-3-pyridyl)-2-[(2R,5S)-2-(4-hydroxyphenyl)-5-methyl-1-piperidyl]-2-oxo-acetamide (21 mg, 54.91 µmol, 36.84% yield)

(RT (OD-H, Hexane-IPA-MeOH, 60-20-20, 0.6 ml/min) =14.05 min) as a yellow solid and Compound 391—N-(6-amino-4,5-dimethyl-3-pyridyl)-2-[(2S,5R)-2-(4-hydroxy-phenyl)-5-methyl-1-piperidyl]-2-oxo-acetamide (22 mg, 57.52 μmol, 38.60% yield) (RT (OD-H, Hexane-IPA-MeOH, 60-20-20, 0.6 ml/min)=8.29 min) as a yellow solid.

Compound 383: Retention time: 14.05 min $^1$H NMR (600 MHz, DMSO-d$_6$) δ (ppm) 0.98-1.04 (m, 3H), 1.26-1.34 (m, 1H), 1.65-1.73 (m, 1H), 1.83 (d, 1H), 1.87-2.04 (m, 7H), 2.11-2.19 (m, 1H), 2.70-3.13 (m, 1H), 3.40-4.02 (m, 1H), 4.97-5.54 (m, 1H), 5.56-5.85 (m, 2H), 6.67-6.80 (m, 2H), 7.02-7.22 (m, 2H), 7.43-7.68 (m, 1H), 9.16-9.45 (m, 1H), 9.48-10.14 (m, 1H).

LCMS(ESI): [M]$^+$ m/z: calcd 382.4; found 383.2; Rt=1.974 min.

Compound 391: Retention time: 8.29 min $^1$H NMR (600 MHz, DMSO-d$_6$) δ (ppm) 0.91-1.06 (m, 3H), 1.18-1.38 (m, 1H), 1.59-1.74 (m, 1H), 1.76-1.87 (m, 1H), 1.87-2.04 (m, 7H), 2.08-2.20 (m, 1H), 2.66-3.18 (m, 1H), 3.41-4.00 (m, 1H), 5.00-5.55 (m, 1H), 5.57-5.85 (m, 2H), 6.71-6.78 (m, 2H), 7.03-7.19 (m, 2H), 7.46-7.67 (m, 1H), 9.16-9.38 (m, 1H), 9.51-10.14 (m, 1H).

LCMS(ESI): [M]$^+$ m/z: calcd 382.4; found 383.2; Rt=1.980 min.

Example 691. The Synthesis of 2-methoxy-5-(2-oxo-2-(2-phenylpiperidin-1-yl)acetamido)nicotinamide (Compound 138, Compound 199 and Compound 202

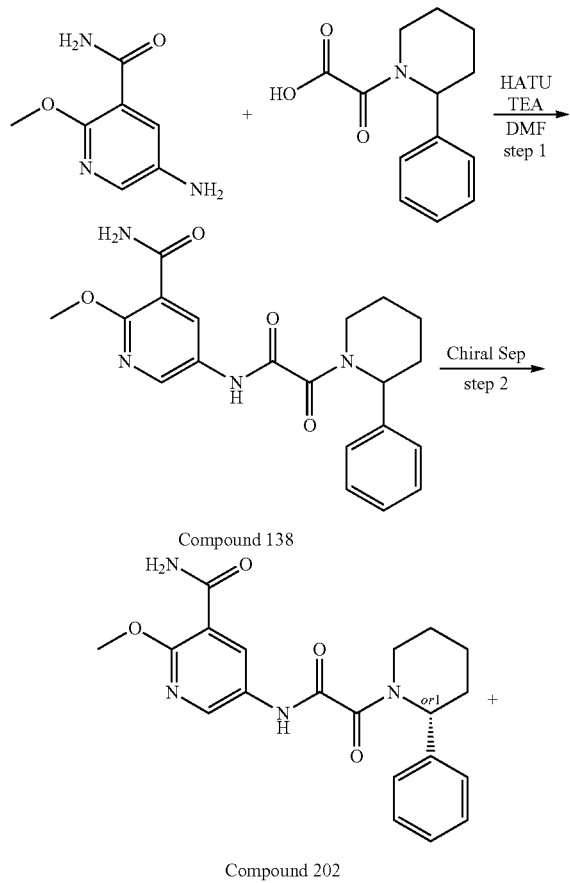

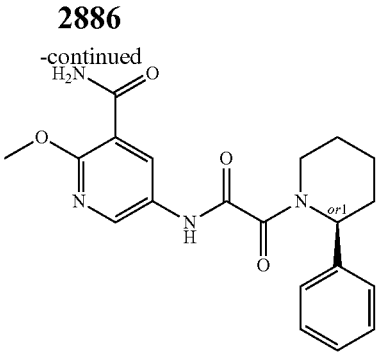

Compound 199

Step 1: Synthesis of 2-methoxy-5-(2-oxo-2-(2-phenylpiperidin-1-yl)acetamido)nicotinamide (Compound 138

DIPEA (138.52 mg, 1.07 mmol, 186.68 μL) was added to the solution of respective 2-oxo-2-(2-phenyl-1-piperidyl) acetic acid (0.1 g, 428.70 μmol) and 5-amino-2-methoxy-pyridine-3-carboxamide (71.66 mg, 428.70 μmol) in DMF (10 mL). The resulting mixture was stirred for 5 min followed by the addition of the solution of HATU (179.31 mg, 471.57 μmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC to afford pure 2-methoxy-5-[[2-oxo-2-(2-phenyl-1-piperidyl)acetyl]amino]pyridine-3-carboxamide (117.4 mg, 307.00 μmol, 71.61% yield).

$^1$H NMR (400 MHz, DMSO-d$_6$) δ (ppm) 1.44 (m, 2H), 1.61 (m, 2H), 1.92 (m, 1H), 3.00 (m, 2H), 3.96 (m, 4H), 5.69 (m, 1H), 7.33 (m, 3H), 7.41 (m, 2H), 7.73 (m, 1H), 7.77 (m, 1H), 8.51 (m, 1H), 8.57 (m, 1H), 11.08 (m, 1H).

LCMS(ESI): [M]$^+$ m/z: calcd 382.4; found 383.2; Rt=3.030 min.

Step 2: Chiral Separation (Compound 199 and Compound 202

2-methoxy-5-[[2-oxo-2-(2-phenyl-1-piperidyl)acetyl]amino]pyridine-3-carboxamide (46.2 mg, 120.81 μmol) was separated using Chiralpak 1B 250*20, 5 mkm column; CO$_2$-MeOH, 70-30 as a mobile phase; Flow rate 2 mL/min; affording Compound 199-2-methoxy-5-[[2-oxo-2-[(2R)-2-phenyl-1-piperidyl]acetyl]amino]pyridine-3-carboxamide (22 mg, 57.53 μmol, 47.62% yield) (RT=7.02 min) as a beige solid and Compound 202-2-methoxy-5-[[2-oxo-2-[(2S)-2-phenyl-1-piperidyl]acetyl]amino]pyridine-3-carboxamide (24.15 mg, 63.15 μmol, 52.27% yield) (RT=7.71 min) as a beige solid.

Compound 199: Retention time: 7.02 min $^1$H NMR (400 MHz, DMSO-d$_6$) δ (ppm) 1.53 (m, 4H), 1.87 (m, 1H), 3.01 (m, 1H), 3.70 (m, 1H), 3.95 (m, 3H), 4.23 (m, 1H), 5.44 (m, 1H), 7.37 (m, 5H), 7.76 (m, 2H), 8.52 (m, 2H), 11.09 (m, 1H).

LCMS(ESI): [M]$^+$ m/z: calcd 382.2; found 383.2; Rt=3.359 min.

Compound 202: Retention time: 7.71 min $^1$H NMR (400 MHz, DMSO-d$_6$) δ (ppm) 1.55 (m, 4H), 1.83 (m, 1H), 3.01 (m, 1H), 3.70 (m, 1H), 3.95 (m, 3H), 4.30 (m, 1H), 5.45 (m, 1H), 7.37 (m, 5H), 7.75 (m, 2H), 8.53 (m, 2H), 11.09 (m, 1H).

LCMS(ESI): [M]+ m/z: calcd 382.2; found 383.2; Rt=3.360 min.

Example 692. The Synthesis of N-(5-(hydroxymethyl)pyridin-3-yl)-2-oxo-2-(2-phenylpiperidin-1-yl)acetamide (Compound 136) and N-(5-formylpyridin-3-yl)-2-oxo-2-(2-phenylpiperidin-1-yl)acetamide (Compound 147)

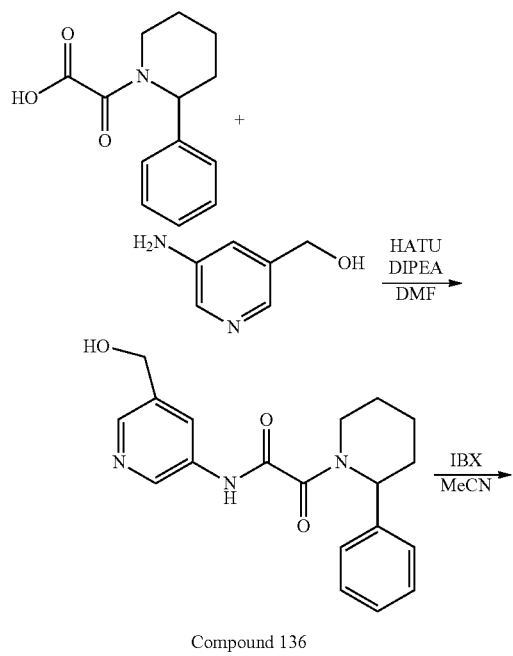

Compound 136

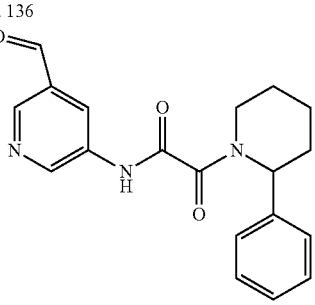

Compound 147

Step 1: Synthesis of N-(5-(hydroxymethyl)pyridin-3-yl)-2-oxo-2-(2-phenylpiperidin-1-yl)acetamide (Compound 136

DIPEA (138.52 mg, 1.07 mmol, 186.68 µL) was added to the solution of respective 2-oxo-2-(2-phenyl-1-piperidyl)acetic acid (0.1 g, 428.70 µmol) and (5-amino-3-pyridyl)methanol (53.22 mg, 428.70 µmol) in DMF (10 mL). The resulting mixture was stirred for 5 min followed by the addition of the solution of HATU (179.31 mg, 471.57 µmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC to afford pure N-[5-(hydroxymethyl)-3-pyridyl]-2-oxo-2-(2-phenyl-1-piperidyl)acetamide (0.1 g, 294.65 µmol, 68.73% yield).

$^1$H NMR (600 MHz, DMSO-d$_6$) δ (ppm) 1.42 (m, 2H), 1.61 (m, 2H), 1.82 (m, 1H), 2.98 (m, 2H), 3.96 (m, 1H), 4.49 (m, 2H), 5.42 (m, 2H), 7.26 (m, 1H), 7.33 (m, 2H), 7.39 (m, 2H), 8.05 (m, 1H), 8.24 (m, 1H), 8.64 (m, 1H), 11.10 (m, 1H). LCMS(ESI): [M]+ m/z: calcd 339.4; found 340.2; Rt=2.490 min.

Step 2: Synthesis of N-(5-Formylpyridin-3-yl)-2-oxo-2-(2-phenylpiperidin-1-yl)acetamide (Compound 147

N-[5-(hydroxymethyl)-3-pyridyl]-2-oxo-2-(2-phenyl-1-piperidyl)acetamide (84.4 mg, 248.68 µmol) and 2-iodoxybenzoic acid (90.53 mg, 323.29 µmol) were dissolved in MeCN (10 mL) and stirred at reflux for 3 hr. The resulting solution was allowed to cool down to rt and filtered through filter paper. The solvent was evaporated under reduced pressure. The solid residue was purified with HPLC using water-MeOH as a mobile phase to afford to N-(5-formyl-3-pyridyl)-2-oxo-2-(2-phenyl-1-piperidyl)acetamide (14.6 mg, 43.28 µmol, 17.40% yield).

$^1$H NMR (400 MHz, CDCl$_3$) δ (ppm) 1.63 (m, 2H), 2.01 (m, 2H), 2.50 (m, 1H), 2.99 (m, 1H), 3.70 (m, 1H), 4.68 (m, 1H), 6.19 (m, 1H), 7.27 (m, 3H), 7.36 (m, 2H), 8.72 (m, 1H), 8.86 (m, 1H), 9.01 (m, 1H), 9.76 (m, 1H), 10.10 (m, 1H). LCMS(ESI): [M]+ m/z: calcd 337.4; found 338.2; Rt=3.284 min.

Example 693. The Synthesis of N-(5,6-dimethylpyridin-3-yl)-2-oxo-2-(2-phenylpiperidin-1-yl)acetamide (Compound 139, Compound 189 and Compound 188

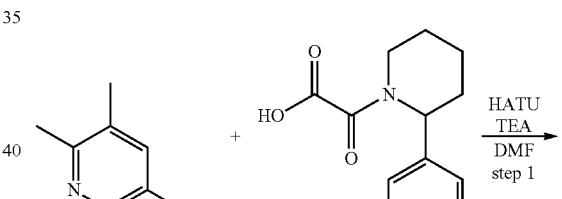

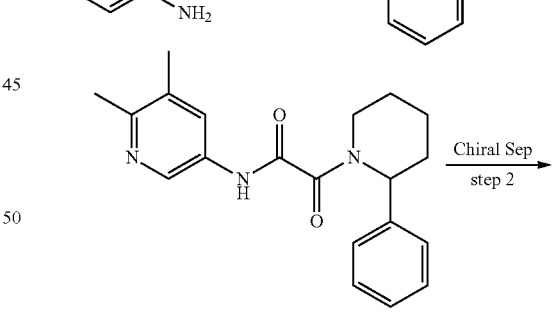

Compound 139

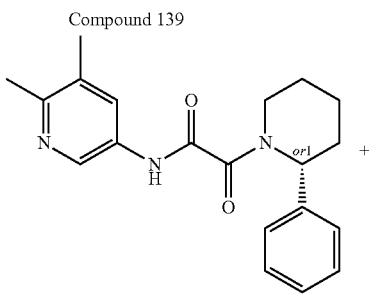

Compound 189

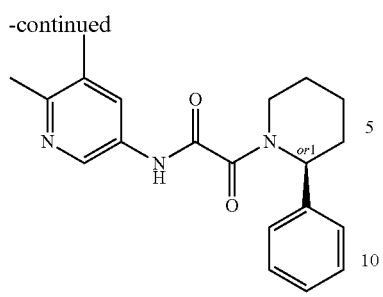

Compound 188

Step 1: Synthesis of N-(5,6-dimethylpyridin-3-yl)-2-oxo-2-(2-phenylpiperidin-1-yl)acetamide (Compound 139

DIPEA (138.52 mg, 1.07 mmol, 186.68 μL) was added to the solution of respective 5,6-dimethylpyridin-3-amine (52.37 mg, 428.70 μmol) and 2-oxo-2-(2-phenyl-1-piperidyl)acetic acid (0.1 g, 428.70 μmol) in DMF (10 mL). The resulting mixture was stirred for 5 min followed by the addition of the solution of HATU (179.31 mg, 471.57 μmol) in DMF (2 mL). Then, the reaction mixture was stirred overnight at rt. After the completion of the reaction, monitored by LCMS, the resulting suspension was concentrated under reduced pressure. The obtained solid was subjected to HPLC (Waters SunFire C18 19*100 5 mkm column and 40-60% MeCN as a mobile phase to afford pure N-(5,6-dimethyl-3-pyridyl)-2-oxo-2-(2-phenyl-1-piperidyl)acetamide (99.6 mg, 295.19 μmol, 68.86% yield).

$^1$H NMR (400 MHz, DMSO-d$_6$+CCl$_4$) δ (ppm) 1.44 (m, 2H), 1.62 (m, 2H), 1.82 (m, 1H), 2.23 (m, 3H), 2.37 (m, 3H), 2.98 (m, 2H), 3.67 (m, 1H), 5.68 (m, 1H), 7.33 (m, 3H), 7.41 (m, 2H), 7.86 (m, 1H), 8.53 (m, 1H), 10.97 (m, 1H).

LCMS(ESI): [M]$^+$ m/z: calcd 337.4; found 338.2; Rt=2.510 min.

Step 2: Chiral Separation (Compound 189 and Compound 188

N-(5,6-dimethyl-3-pyridyl)-2-oxo-2-(2-phenyl-1-piperidyl)acetamide (52.93 mg, 156.87 μmol) was separated using Chiralpak OJ-H 250*20, 5 mkm column; Hexane-IPA-MeOH, 60-20-20 as a mobile phase; Flow rate 12 mL/min; Injection Volume: 900 mkl; affording Compound 189—N-(5,6-dimethyl-3-pyridyl)-2-oxo-2-[(2R)-2-phenyl-1-piperidyl]acetamide (26.84 mg, 79.55 μmol, 50.71% yield) (RT (OJ-H, Hexane-IPA-MeOH, 60-20-20, 0.6 ml/min)=24.48 min) as a beige solid and Compound 188—N-(5,6-dimethyl-3-pyridyl)-2-oxo-2-[(2S)-2-phenyl-1-piperidyl]acetamide (26.09 mg, 77.32 μmol, 49.29% yield) (RT (OJ-H, Hexane-IPA-MeOH, 60-20-20, 0.6 ml/min)=10.69 min) as a beige solid.

Compound 189: Retention time: 24.48 min $^1$H NMR (600 MHz, DMSO-d$_6$) δ (ppm) 1.49 (m, 4H), 1.85 (m, 1H), 2.20 (m, 3H), 2.34 (m, 3H), 2.43 (m, 1H), 2.96 (m, 1H), 4.02 (m, 1H), 5.39 (m, 1H), 7.33 (m, 5H), 7.80 (m, 1H), 8.46 (m, 1H), 10.94 (m, 1H).

LCMS(ESI): [M]$^+$ m/z: calcd 337.2; found 338.2; Rt=3.802 min.

Compound 188: Retention time: 10.69 min $^1$H NMR (600 MHz, DMSO-d$_6$) δ (ppm) 1.51 (m, 4H), 1.83 (m, 1H), 2.20 (m, 3H), 2.34 (m, 3H), 2.43 (m, 1H), 2.96 (m, 1H), 4.12 (m, 1H), 5.40 (m, 1H), 7.34 (m, 5H), 7.80 (m, 1H), 8.46 (m, 1H), 10.93 (m, 1H).

LCMS(ESI): [M]$^+$ m/z: calcd 337.2; found 338.2; Rt=3.808 min.

Example 694. The Synthesis of N-hydroxy-5-(2-oxo-2-(2-phenylpiperidin-1-yl)acetamido)nicotinamide (Compound 378)

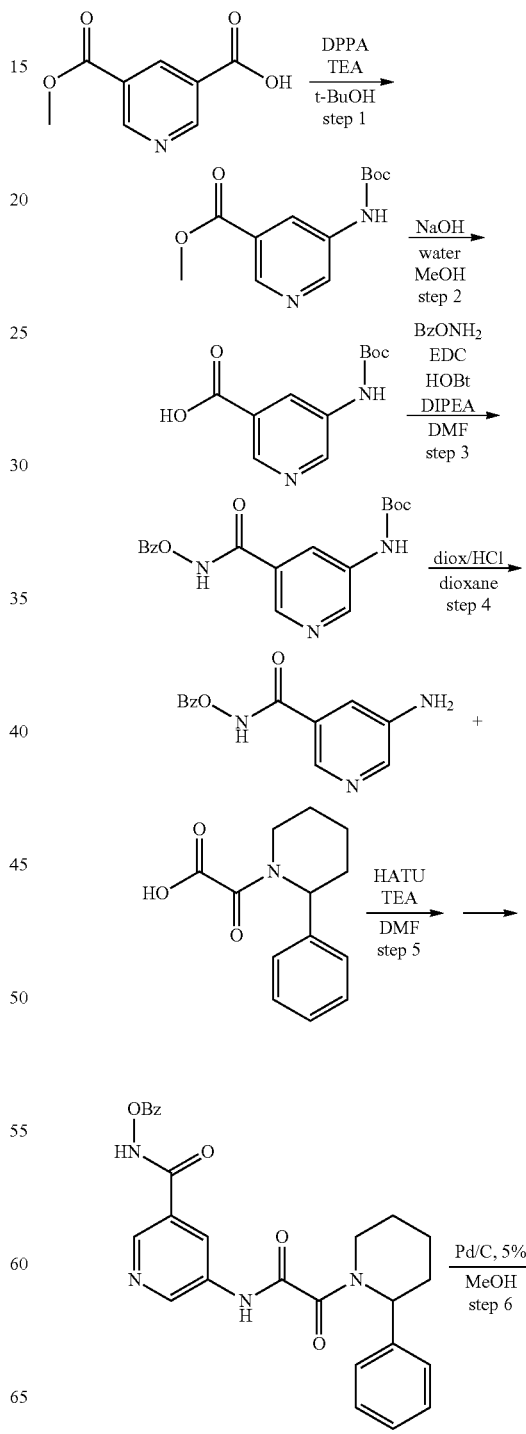

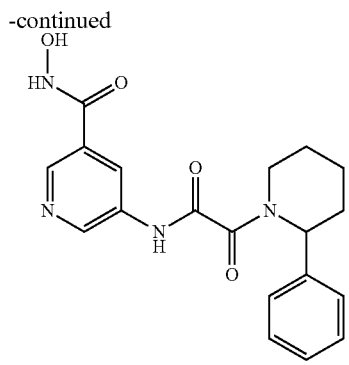

Compound 378

Step 1: Synthesis of methyl 5-((Tert-butoxycarbonyl)amino)Nicotinate

A portion of 5-methoxycarbonylpyridine-3-carboxylic acid (4.23 g, 23.35 mmol) was dissolved in dry tert-butanol (98.25 g, 1.33 mol, 125 mL) and treated sequentially with TEA, 99% (3.54 g, 35.03 mmol, 4.88 mL) and diphenyl phosphoryl azide (8.52 g, 35.03 mmol). The mixture was refluxed for 8 hr. Solvent was removed under reduced pressure and the residue was partitioned between water and DCM. The layers were separated and the aqueous phase was extracted twice with DCM. The combined organic phases were dried and concentrated to produce methyl 5-(tert-butoxycarbonylamino)pyridine-3-carboxylate (8 g, crude) used without further purification.

$^1$H NMR (400 MHz, CDCl$_3$) δ (ppm) 1.49 (s, 9H), 3.96 (s, 3H), 8.49 (s, 1H), 8.69 (s, 1H), 8.84 (s, 1H), 12.06 (bds, 1H).

LCMS(ESI): [M]$^+$ m/z: calcd 252.2; found 253.2; Rt=1.216 min.

Step 2: Synthesis of 5-((Tert-butoxycarbonyl)amino)Nicotinic acid

Methyl 5-(tert-butoxycarbonylamino)pyridine-3-carboxylate (8 g, 31.71 mmol) was dissolved in MeOH (128 mL) and water (32 mL), sodium hydroxide, pearl (1.90 g, 47.57 mmol, 893.25 µL) was added one portion, mixture was stirred 8 h at rt the mixture was concentrated the residue was treated with 1 N HCl until the resultant slurry reached pH 3. The residue was collected and washed with water, dried. The crude was subjected to CC (SiO$_2$, gradient ACN/CHCl$_3$) to produce 5-(tert-butoxycarbonylamino)pyridine-3-carboxylic acid (1.1 g, 4.62 mmol, 14.56% yield).

$^1$H NMR (400 MHz, DMSO-d$_6$) δ (ppm) 1.49 (s, 9H), 8.48 (s, 1H), 8.69 (s, 1H), 8.78 (s, 1H), 9.82 (bds, 1H).

LCMS(ESI): [M]$^+$ m/z: calcd 238.2; found 239.2; Rt=0.964 min.

Step 3: Synthesis of tert-butyl (5-((Benzoyloxy)carbamoyl)pyridin-3-yl)carbamate 5-(tert-butoxycarbonylamino)pyridine-3-carboxylic acid (0.2 g, 839.49 µmol) was dissolved in DMF (4 mL) and O-benzylhydroxylamine (200.99 mg, 1.26 mmol, HCl) EDC (321.86 mg, 1.68 mmol), HOBt (124.78 mg, 923.44 µmol) and DIPEA (336.35 mg, 2.60 mmol, 453.30 µL) were added one portion. The mixture was stirred at rt, for 8 hr and controlled by LCMS. The mixture was diluted with EtOAc (30 mL) and washed with brine (3*10 mL), dried Na$_2$SO$_4$ and concentrated to produce tert-butyl N-[5-(benzyloxycarbamoyl)-3-pyridyl]carbamate (0.3 g, crude) used without further purification.

$^1$H NMR (500 MHz, CDCl$_3$) δ (ppm) 1.49 (s, 9H), 4.84 (s, 2H), 5.45 (bds, 2H), 7.40 (m, 5H), 8.01 (s, 1H), 8.57 (s, 1H), 8.65 (s, 1H).

LCMS(ESI): [M]$^+$ m/z: calcd 343.2; found 344.2; Rt=1.221 min.

Step 4: Synthesis of 5-amino-N-(Benzoyloxy)nicotinamide tert-butyl N-[5-(benzyloxycarbamoyl)-3-pyridyl]carbamate (0.3 g, 873.68 µmol) was dissolved in dioxane (1 mL) and hydrogen chloride solution 4.0 M in dioxane (318.55 mg, 8.74 mmol, 398.19 µL) was added, mixture was stirred at rt, for 4 hr and concentrated, to produce 5-amino-N-benzyloxy-pyridine-3-carboxamide (0.3 g, crude, HCl) used without further purification.

LCMS(ESI): [M]$^+$ m/z: calcd 243.2; found 244.2; Rt=0.780 min.

Step 5: Synthesis of N-(Benzoyloxy)-5-(2-oxo-2-(2-phenylpiperidin-1-yl)acetamido)nicotinamide A solution of 5-amino-N-benzyloxy-pyridine-3-carboxamide (0.3 g, 1.07 mmol, HCl), 2-oxo-2-(2-phenyl-1-piperidyl)acetic acid (250.17 mg, 1.07 mmol), TEA (325.58 mg, 3.22 mmol, 448.45 µL) and HATU (611.69 mg, 1.61 mmol) in DMF (5 mL) was stirred at 25° C. for 12 hr. The reaction mixture was diluted with EtOAc (30 ml), washed with brine (3×30 ml). The organic layer was dried over Na$_2$SO$_4$, filtered and concentrated under vacuum. The crude was subjected to HPLC (30-55% 2-7 min; water-MecN; 30 ml/min; column SunFire 19*100 mm) to produce N-benzyloxy-5-[[2-oxo-2-(2-phenyl-1-piperidyl)acetyl]amino]pyridine-3-carboxamide (24.4 mg, 53.22 µmol, 4.96% yield).

LCMS(ESI): [M]$^+$ m/z: calcd 458.4; found 459.2; Rt=1.349 min.

Step 6: Synthesis of N-hydroxy-5-(2-oxo-2-(2-phenylpiperidin-1-yl)acetamido)nicotinamide (Compound 378

N-benzyloxy-5-[[2-oxo-2-(2-phenyl-1-piperidyl)acetyl]amino]pyridine-3-carboxamide (24.4 mg, 53.22 µmol) was dissolved in MeOH (2 mL) and palladium, 5% on activated carbon paste, 5R437 (1.13 mg, 10.64 µmol) was added. The mixture was vacuumed and balloon with hydrogen was added. The mixture was controlled by LCMS. The mixture was filtered and solution was subjected to HPLC(10-50% 0.5-6.5 min; water-MeCN; 30 ml/min; column SunFire 19*100 mm) to produce N-[5-(hydroxycarbamoyl)-3-pyridyl]-2-oxo-2-(2-phenyl-1-piperidyl)acetamide (4.1 mg, 11.13 µmol, 20.91% yield).

LCMS(ESI): [M]$^+$ m/z: calcd 368.2; found 369.2; Rt=2.523 min.

Example 695. The Synthesis of N-(6-amino-4,5-dimethylpyridin-3-yl)-2-(5-methyl-2-phenylpiperidin-1-yl)-2-oxoacetamide (Compound 368, Compound 367

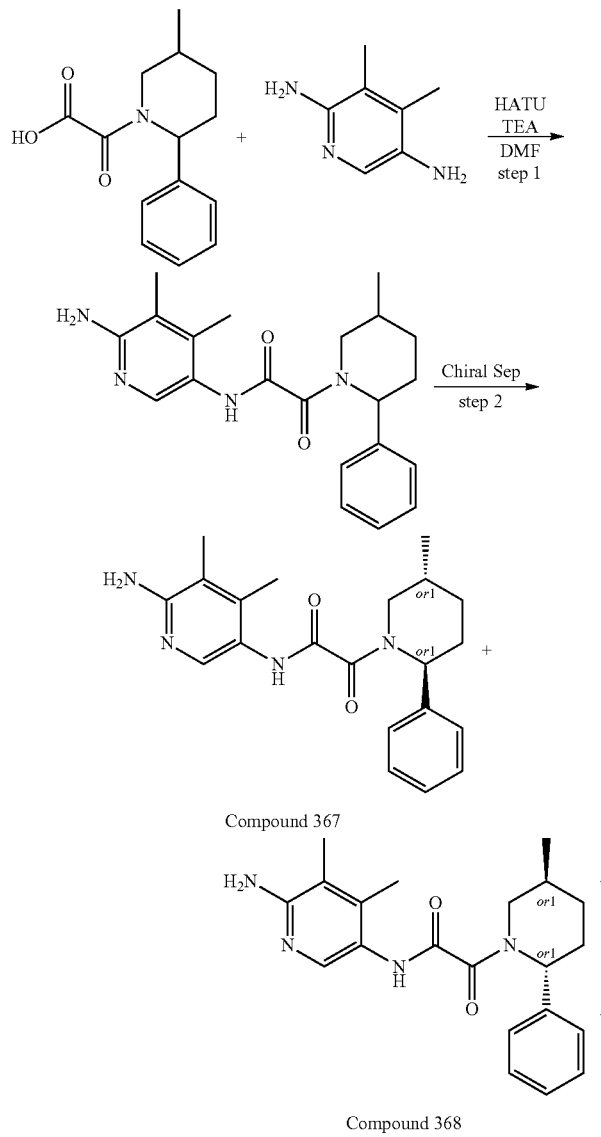

Compound 367

Compound 368

Step 1: Synthesis of N-(6-amino-4,5-dimethylpyridin-3-yl)-2-(5-methyl-2-phenylpiperidin-1-yl)-2-oxoacetamide 2-(5-methyl-2-phenyl-1-piperidyl)-2-oxo-acetic acid (0.4 g, 1.57 mmol, Li+) was mixed with HATU (598.25 mg, 1.57 mmol) in DMF (5 mL) and the resulting mixture was stirred at 20° C. for 10 min followed by addition of 3,4-dimethylpyridine-2,5-diamine (215.84 mg, 1.57 mmol) (prepared as above). The resulting mixture was stirred at 20° C. for 12 hr. The resulting solution was subjected to HPLC (2-10 min 45-60% water+$NH_3$/MeOH+$NH_3$ (loading pump 4 ml MeOH+$NH_3$); column: TRIART 100*20 5 microM) to obtain N-(6-amino-4,5-dimethyl-3-pyridyl)-2-(5-methyl-2-phenyl-1-piperidyl)-2-oxo-acetamide (0.19 g, 518.48 μmol, 32.95% yield).

$^1$H NMR (400 MHz, DMSO-$d_6$) δ (ppm)
LCMS(ESI): [M]$^+$ m/z: calcd 366.2; found 367.2; Rt=1.082 min.

Step 2: Chiral Separation (Compound 368, Compound 368 and Compound 367

N-(6-amino-4,5-dimethyl-3-pyridyl)-2-(5-methyl-2-phenyl-1-piperidyl)-2-oxo-acetamide (190 mg, 518.48 μmol) was separated using Chiralpak IA-II 250*20, 5 mkm column; Hexane-IPA-MeOH, 40-30-30 as a mobile phase; Flow rate 11 mL/min; Injection Volume: 900 mkl; affording Compound 368 and Compound 368—N-(6-amino-4,5-dimethyl-3-pyridyl)-2-[(2R,5S)-5-methyl-2-phenyl-1-piperidyl]-2-oxo-acetamide (83 mg, 226.49 μmol, 43.68% yield) (RT (OJ-H, Hexane-IPA-MeOH, 60-20-20, 0.6 ml/min)=12.09 min) as a yellow solid and Compound 367—N-(6-amino-4,5-dimethyl-3-pyridyl)-2-[(2S,5R)-5-methyl-2-phenyl-1-piperidyl]-2-oxo-acetamide (68.49 mg, 186.90 μmol, 36.05% yield) (RT (OJ-H, Hexane-IPA-MeOH, 60-20-20, 0.6 ml/min)=15.44 min) as a yellow solid. The sample was repurified in the following conditions: Column: Chiralpak OJ-H; Mobile phase: Hexane-MeOH-IPA, 70-15-15, 13 mL/min; 45 mg of pure Compound 368.

Compound 368: Retention time: 12.09 min
$^1$H NMR (600 MHz, DMSO-$d_6$) δ (ppm) 0.94-1.06 (m, 3H), 1.27-1.38 (m, 1H), 1.38-1.85 (m, 2H), 1.85-2.07 (m, 7H), 2.12-2.25 (m, 1H), 2.68-3.24 (m, 1H), 3.35-4.07 (m, 1H), 5.12-5.57 (m, 1H), 5.58-6.47 (m, 2H), 7.07-7.26 (m, 1H), 7.26-7.42 (m, 4H), 7.46-7.68 (m, 1H), 9.47-10.19 (m, 1H).
LCMS(ESI): [M]$^+$ m/z: calcd 366.2; found 367.2; Rt=2.550 min.

Compound 367: Retention time: 15.44 min
$^1$H NMR (600 MHz, DMSO-$d_6$) δ (ppm) 0.95-1.07 (m, 3H), 1.24-1.39 (m, 1H), 1.40-1.85 (m, 2H), 1.86-2.12 (m, 7H), 2.12-2.27 (m, 1H), 2.53-2.73 (m, 1H), 2.89-3.24 (m, 1H), 3.41-4.13 (m, 1H), 5.10-5.57 (m, 1H), 5.57-5.89 (m, 2H), 7.12-7.26 (m, 1H), 7.27-7.31 (m, 1H), 7.35-7.38 (m, 2H), 7.38-7.69 (m, 1H), 9.39-10.29 (m, 1H).
LCMS(ESI): [M]$^+$ m/z: calcd 366.2; found 367.2; Rt=2.544 min.

Example 696. The Synthesis of N-(6-amino-4,5-dimethylpyridin-3-yl)-2-(2-methyl-6-phenylpiperidin-1-yl)-2-oxoacetamide (Compound 425, Compound 439

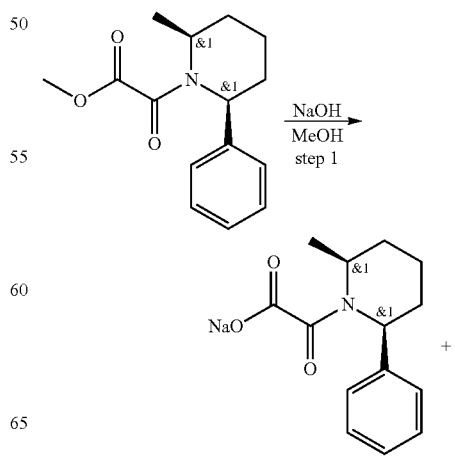

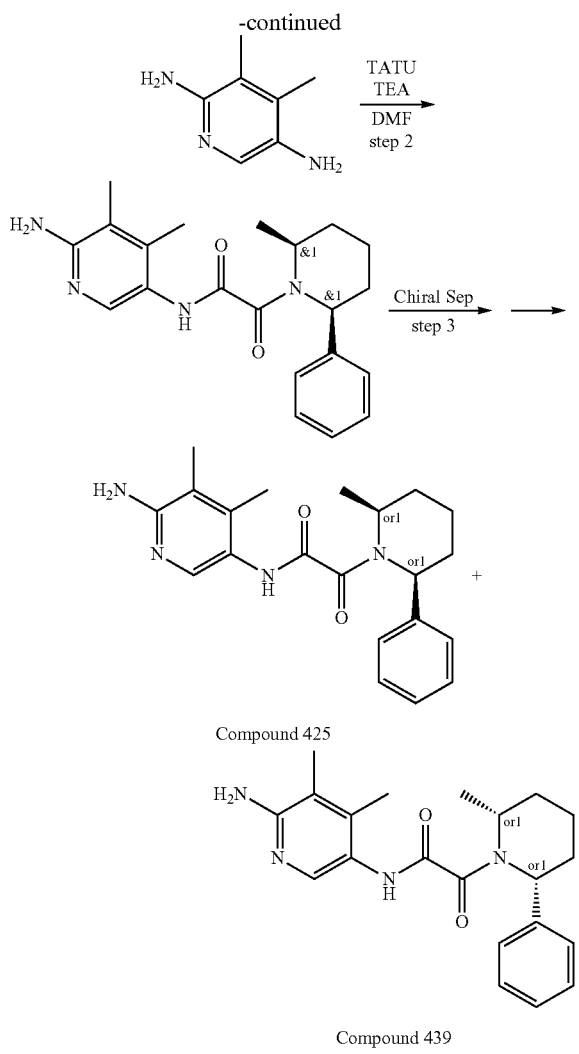

Compound 425

Compound 439

Step 1: Synthesis of Sodium rac-2-((2R,6R)-2-methyl-6-phenylpiperidin-1-yl)-2-oxoacetate To a solution of methyl 2-[(2R,6R)-2-methyl-6-phenyl-1-piperidyl]-2-oxo-acetate (0.92 g, 3.52 mmol) in MeOH (25 mL) was added sodium hydroxide, pearl (154.90 mg, 3.87 mmol, 72.72 μL) and the resulting mixture was left to stir at rt for hr. Then the resulting mixture was evaporated to dryness and used as a sodium salt ([2-[(2R,6R)-2-methyl-6-phenyl-1-piperidyl]-2-oxo-acetyl]oxysodium (0.9 g, 3.34 mmol, 94.94% yield) in the next step.

$^1$H NMR (500 MHz, CDCl$_3$) δ (ppm)

LCMS(ESI): [M]$^+$ m/z: calcd 247.2; found 248.2; Rt=1.181 min.

Step 2: Synthesis of N-(6-amino-4,5-dimethylpyridin-3-yl)-2-(2-methyl-6-phenylpiperidin-1-yl)-2-oxoacetamide

[2-[(2R,6R)-2-methyl-6-phenyl-1-piperidyl]-2-oxo-acetyl]oxysodium (0.45, 1.67 mmol), TATU (645.88 mg, 2.01 mmol) and TEA (169.11 mg, 1.67 mmol, 232.93 μL) were mixed in dry DMF (8 mL) at 21° C. and the resulting mixture was stirred for 15 min. 3,4-dimethylpyridine-2,5-diamine (229.26 mg, 1.67 mmol) (prepared as above) was added thereto and the resulting mixture was stirred at 21° C. overnight. The resulting mixture was poured into water, extracted 3 times with EtOAc, combined organics were washed with water, brine and evaporated. The residue was subjected to HPLC (0.5-6.5 min; water-MeOH (+NH$_3$); 30 ml/min; loading pump 4 ml/min R1; column YMC-Actus Triat 20*100 mm). N-(6-amino-4,5-dimethyl-3-pyridyl)-2-[(2R,6R)-2-methyl-6-phenyl-1-piperidyl]-2-oxo-acetamide (122.3 mg, 333.74 μmol, 19.97% yield) was obtained as a brown solid.

$^1$H NMR (500 MHz, CDCl$_3$) δ (ppm) 0.92 (d, 3H), 1.87 (m, 3H), 2.08 (s, 3H), 2.18 (s, 3H), 2.58 (m, 1H), 4.46 (m, 2H), 4.97 (m, 1H), 6.17 (m, 1H), 7.24 (m, 2H), 7.36 (m, 5H), 8.05 (s, 1H), 8.59 (s, 1H).

LCMS(ESI): [M]$^+$ m/z: calcd 366.2; found 367.2; Rt=0.954 min.

Step 3: Chiral Separation (Compound 425 and Compound 439

N-(6-amino-4,5-dimethyl-3-pyridyl)-2-[(2R,6R)-2-methyl-6-phenyl-1-piperidyl]-2-oxo-acetamide (120 mg, 327.46 μmol) was separated using Chiralpak OJ-H 250*20, 5 mkm column; Hexane-IPA-MeOH, 60-20-20 as a mobile phase; Flow rate 12 mL/min; Injection Volume: 900 mkl; affording Compound 425—N-(6-amino-4,5-dimethyl-3-pyridyl)-2-[(2S,6S)-2-methyl-6-phenyl-1-piperidyl]-2-oxo-acetamide (52.57 mg, 143.46 μmol, 43.81% yield) (RT (OJ-H, Hexane-IPA-MeOH, 60-20-20, 0.6 ml/min)=31.68 min) as a white solid and Compound 439—N-(6-amino-4,5-dimethyl-3-pyridyl)-2-[(2R,6R)-2-methyl-6-phenyl-1-piperidyl]-2-oxo-acetamide (50.39 mg, 137.51 μmol, 41.99% yield) (RT (OJ-H, Hexane-IPA-MeOH, 60-20-20, 0.6 ml/min)=13.17 min) as a white solid.

Compound 425

Retention time: 31.68 min $^1$H NMR (500 MHz, DMSO-d$_6$) δ (ppm) 0.67-0.91 (m, 3H), 1.47-1.62 (m, 2H), 1.68-1.85 (m, 3H), 1.87-2.16 (m, 7H), 3.99-4.86 (m, 1H), 5.07-5.62 (m, 1H), 5.62-5.91 (m, 2H), 7.25 (t, 1H), 7.30-7.38 (m, 2H), 7.38-7.52 (m, 2H), 7.52-7.70 (m, 1H), 9.54-10.21 (m, 1H).

LCMS(ESI): [M]$^+$ m/z: calcd 366.2; found 367.2; Rt=3.980 min.

Compound 439: Retention time: 13.17 min $^1$H NMR (500 MHz, DMSO-d$_6$) δ (ppm) 0.62-0.84 (m, 3H), 1.48-1.64 (m, 2H), 1.65-1.84 (m, 3H), 1.85-2.20 (m, 7H), 3.94-4.78 (m, 1H), 5.13-5.61 (m, 1H), 5.62-5.83 (m, 2H), 7.22-7.28 (t, 1H), 7.30-7.38 (m, 2H), 7.38-7.54 (m, 2H), 7.57-7.72 (m, 1H), 9.49-10.27 (m, 1H).

LCMS(ESI): [M]$^+$ m/z: calcd 366.2; found 367.2; Rt=3.971 min.

Example 697. The Synthesis of 5-(2-(2-methyl-6-phenylpiperidin-1-yl)-2-oxoacetamido)nicotinamide (Compound 278, Compound 274

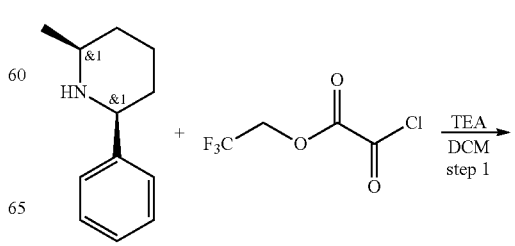

-continued

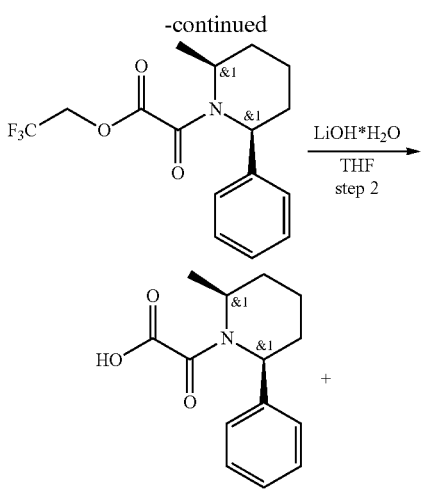

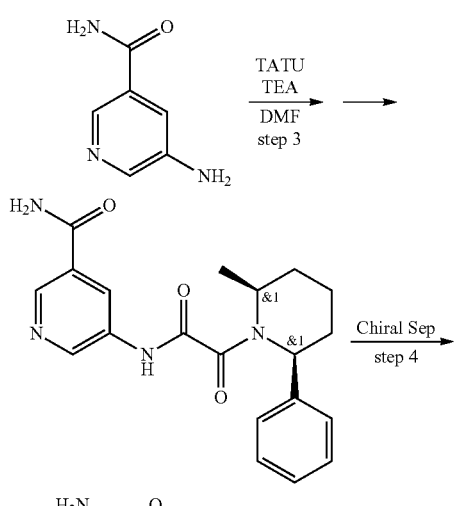

Compound 274

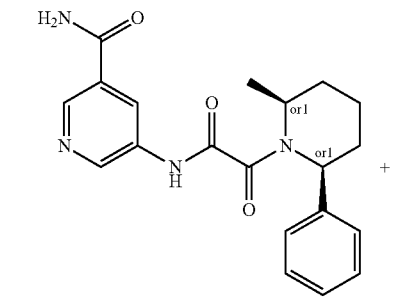

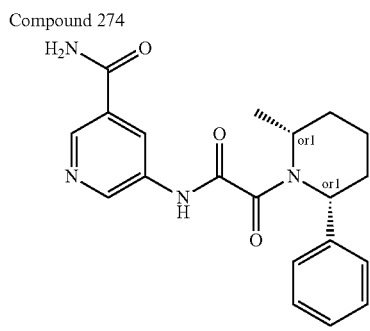

Compound 278

Step 1: Synthesis of rac-2,2,2-trifluoroethyl 2-((2S,6S)-2-methyl-6-phenylpiperidin-1-yl)-2-oxoacetate To a solution of (2S,6S)-2-methyl-6-phenyl-piperidine (0.23 g, 1.31 mmol) in DCM (10 mL) was added TEA (159.35 mg, 1.57 mmol, 219.48 μL) followed by 2,2,2-trifluoroethyl 2-chloro-2-oxo-acetate (274.99 mg, 1.44 mmol) at 0° C. under an inert atmosphere. After 1 hr, the reaction mixture was quenched with water, DCM was dried and evaporated to give 2,2,2-trifluoroethyl 2-[(2S,6S)-2-methyl-6-phenyl-1-piperidyl]-2-oxo-acetate (0.43 g, 1.31 mmol, 99.50% yield) as a yellow solid.

$^1$H NMR (500 MHz, CDCl$_3$) δ (ppm) 0.84 (d, 3H), 1.68 (m, 2H), 1.96 (m, 2H), 2.58 (d, 1H), 3.11 (m, 1H), 3.82 (m, 1H), 4.76 (m, 2H), 5.89 (m, 1H), 7.26 (m, 1H), 7.37 (m, 4H).

LCMS(ESI): [M]$^+$ m/z: calcd 329.2; found 330.2; Rt=1.532 min.

Step 2: Synthesis of rac-2-((2S,6S)-2-methyl-6-phenylpiperidin-1-yl)-2-oxoacetic acid To a solution of 2,2,2-trifluoroethyl 2-[(2S,6S)-2-methyl-6-phenyl-1-piperidyl]-2-oxo-acetate (0.43 g, 1.31 mmol) in THF (25 mL) was added lithium hydroxide hydrate (65.75 mg, 1.57 mmol, 43.54 μL) and the resulting mixture was left to stir at rt for hr. Then the resulting mixture was evaporated to dryness, dissolved in water, washed with DCM three times. Water was acidified to pH=1 and extracted with EtOAc twice, organics were washed with brine, dried over Na$_2$SO$_4$ and evaporated. 2-[(2S,6S)-2-methyl-6-phenyl-1-piperidyl]-2-oxo-acetic acid (0.26 g, 1.05 mmol, 80.52% yield) was obtained as a pale-yellow solid.

$^1$H NMR (500 MHz, CDCl$_3$) δ (ppm) 0.88 (d, 3H), 1.68 (m, 2H), 1.96 (m, 3H), 2.61 (d, 1H), 4.68 (m, 1H), 5.89 (m, 1H), 7.36 (m, 5H), 7.87 (m, 1H).

LCMS(ESI): [M]$^+$ m/z: calcd 247.2; found 248.2; Rt=1.028 min.

Step 3: Synthesis of 5-(2-(2-methyl-6-phenylpiperidin-1-yl)-2-oxoacetamido)nicotinamide 2-[(2S,6S)-2-methyl-6-phenyl-1-piperidyl]-2-oxo-acetic acid (0.26 g, 1.05 mmol), TATU (372.49 mg, 1.16 mmol) and TEA (212.78 mg, 2.10 mmol, 293.09 μL) were mixed in dry DMF (15 mL) at 21° C. and the resulting mixture was stirred for 15 min. 5-aminopyridine-3-carboxamide (144.19 mg, 1.05 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (2-7 min 25-50% MeCN, 30 ml/min Sunfire c18 5 μM). 5-[[2-[(2S,6S)-2-methyl-6-phenyl-1-piperidyl]-2-oxo-acetyl]amino]pyridine-3-carboxamide (166.2 mg, 453.59 μmol, 43.14% yield) was obtained as a yellowish solid.

$^1$H NMR (400 MHz, CDCl$_3$) δ (ppm) 0.91 (d, 3H), 1.61 (m, 2H), 1.91 (m, 3H), 2.55 (m, 2H), 4.88 (m, 1H), 6.42 (m, 2H), 7.36 (m, 5H), 8.68 (s, 1H), 8.87 (s, 1H), 9.04 (s, 1H), 9.91 (s, 1H), LCMS(ESI): [M]$^+$ m/z: calcd 366.2; found 367.2; Rt=1.233 min.

Step 4: Chiral Separation (Compound 278 and Compound 274

5-[[2-[(2S,6S)-2-methyl-6-phenyl-1-piperidyl]-2-oxo-acetyl]amino]pyridine-3-carboxamide (166.2 mg, 453.59

μmol) was separated using Chiralpak AS-H 250*20, 5 mkm column; CO₂-MeOH, 60-40 as a mobile phase; Flow rate 2 mL/min; affording Compound 278-5-[[2-[(2R,6R)-2-methyl-6-phenyl-1-piperidyl]-2-oxo-acetyl]amino]pyridine-3-carboxamide (47.87 mg, 130.64 μmol, 28.80% yield) (RT=4.54 min) as a beige solid and Compound 274-5-[[2-[(2S,6S)-2-methyl-6-phenyl-1-piperidyl]-2-oxo-acetyl]amino]pyridine-3-carboxamide (51.47 mg, 140.36 μmol, 30.94% yield) (RT=3.59 min) as a beige solid.

Compound 278: Retention time: 4.54 min

¹H NMR (600 MHz, DMSO-d₆) δ (ppm) 0.64-0.82 (m, 3H), 1.48-1.55 (m, 1H), 1.55-1.67 (m, 1H), 1.69-1.96 (m, 3H), 2.53-2.62 (m, 1H), 3.98-4.83 (m, 1H), 5.05-5.82 (m, 1H), 7.19-7.29 (m, 1H), 7.30-7.50 (m, 4H), 7.56-7.68 (m, 1H), 8.09-8.25 (m, 1H), 8.40-8.54 (m, 1H), 8.69-8.80 (m, 1H), 8.80-8.97 (m, 1H), 11.25 (s, 1H).

LCMS(ESI): [M]⁺ m/z: calcd 366.2; found 367.2; Rt=3.046 min.

Compound 274: Retention time: 3.59 min

¹H NMR (600 MHz, DMSO-d₆) δ (ppm) 0.66-0.86 (m, 3H), 1.46-1.55 (m, 1H), 1.55-1.63 (m, 1H), 1.70-1.92 (m, 3H), 2.55-2.64 (m, 1H), 4.00-4.80 (m, 1H), 5.05-5.80 (m, 1H), 7.17-7.28 (m, 1H), 7.31-7.52 (m, 4H), 7.54-7.67 (m, 1H), 8.08-8.22 (m, 1H), 8.42-8.54 (m, 1H), 8.68-8.80 (m, 1H), 8.80-8.96 (m, 1H), 11.25 (s, 1H).

LCMS(ESI): [M]⁺ m/z: calcd 366.2; found 367.2; Rt=3.048 min.

Example 698. The Synthesis of rac-5-[[2-[(2R,3R,6S)-2,3-dimethyl-6-phenyl-1-piperidyl]-2-oxo-acetyl]amino]pyridine-3-carboxamide, rac-5-[[2-[(2R,3R,6R)-2,3-dimethyl-6-phenyl-1-piperidyl]-2-oxo-acetyl]amino]pyridine-3-carboxamide and rac-5-[[2-[(2S,3R,6S)-2,3-dimethyl-6-phenyl-1-piperidyl]-2-oxo-acetyl]amino]pyridine-3-carboxamide (Compound 154, Compound 163 and Compound 181); Chiral Separation to 5-[[2-[(2S,3S,6R)-2,3-dimethyl-6-phenyl-1-piperidyl]-2-oxo-acetyl]amino]pyridine-3-carboxamide and 5-[[2-[(2R,3R,63)-2,3-dimethyl-6-phenyl-1-piperidyl]-2-oxo-acetyl]amino]pyridine-3-carboxamide (Compound 435 and Compound 433); Chiral Separation to -[[2-[(2S,3R,63)-2,3-dimethyl-6-phenyl-1-piperidyl]-2-oxo-acetyl]amino]pyridine-3-carboxamide and 5-[[2-[(2R,3S,6R)-2,3-dimethyl-6-phenyl-1-piperidyl]-2-oxo-acetyl]amino]pyridine-3-carboxamide (Compound 482 and Compound 483

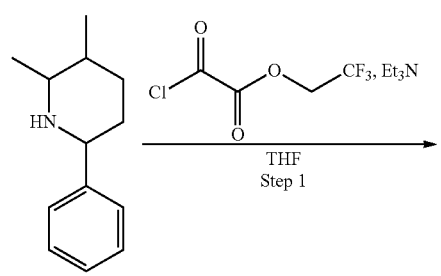

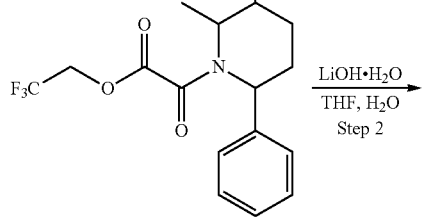

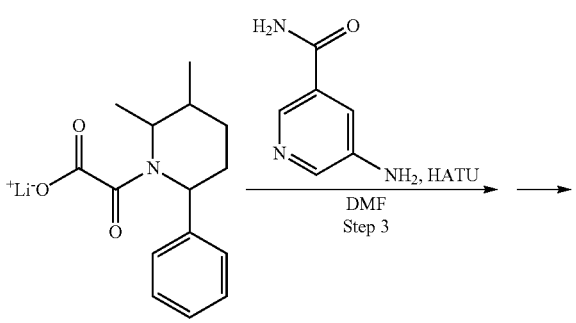

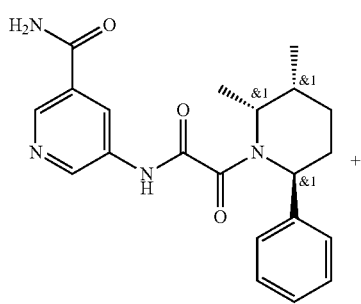

Compound 154

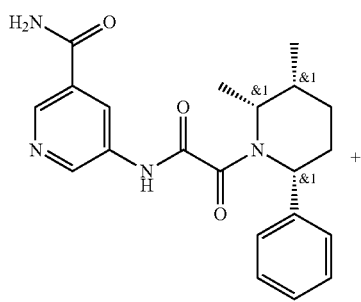

Compound 163

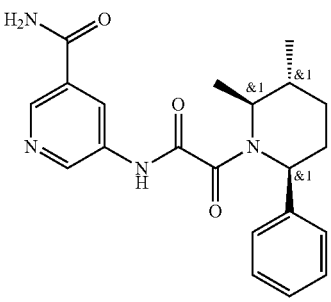

Compound 181

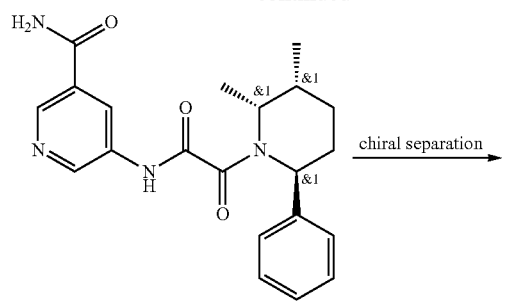

Compound 154

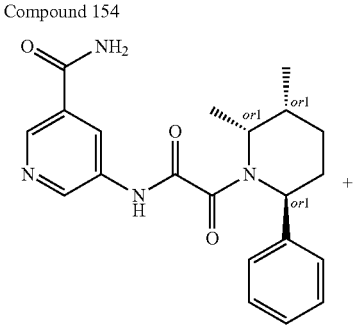

Compound 435

Compound 433

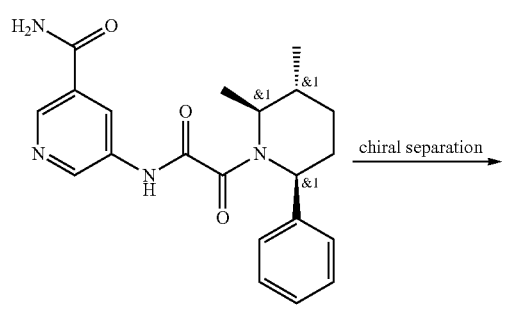

Compound 181

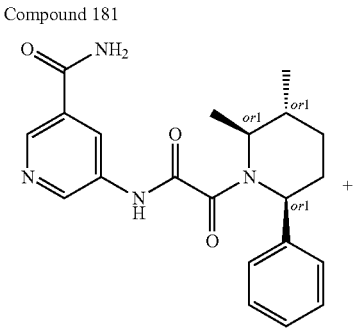

Compound 482

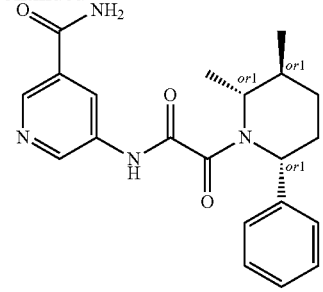

Compound 483

Step 1: Synthesis of 2,2,2-trifluoroethyl 2-(2,3-dimethyl-6-phenyl-1-piperidyl)-2-oxo-acetate To a stirred solution of 2,3-dimethyl-6-phenyl-piperidine (0.5 g, 2.64 mmol) and triethylamine (267.28 mg, 2.64 mmol, 368.15 μL) in THF (10 mL) at −10° C., 2,2,2-trifluoroethyl 2-chloro-2-oxo-acetate (503.19 mg, 2.64 mmol) was added dropwise. The resulting reaction mixture was allowed to warm to room temperature and stirred for 12 hours at the same temperature. After 12 hours, the reaction mixture was filtered and the filtrate was concentrated under reduced pressure to obtain 2,2,2-trifluoroethyl 2-(2,3-dimethyl-6-phenyl-1-piperidyl)-2-oxo-acetate (0.8 g, crude). The crude product was used for the next step reaction without any further purification.

LCMS(ESI): [M+H]⁺ m/z: calcd 343.2; found 344.0; Rt=1.571 min.

Step 2: Synthesis of [2-(2,3-dimethyl-6-phenyl-1-piperidyl)-2-oxo-acetyl]oxylithium To a stirred solution of 2,2,2-trifluoroethyl 2-(2,3-dimethyl-6-phenyl-1-piperidyl)-2-oxo-acetate (0.8 g, 2.33 mmol) in water (2 mL) and THF (20 mL) was added, Lithium hydroxide monohydrate, 98% (97.78 mg, 2.33 mmol). The resulting reaction mixture was stirred at 20° C. for 24 hours. After 24 hours, the reaction mixture was evaporated to dryness to obtain [2-(2,3-dimethyl-6-phenyl-1-piperidyl)-2-oxo-acetyl]oxylithium (0.5 g, crude), which was used for the next step reaction without any further purification.

LCMS(ESI): [M+H]⁺ m/z: calcd 261.1; found 262.2; Rt=1.109 min.

Step 3: Synthesis of rac-5-[[2-[(2R,3R,6S)-2,3-dimethyl-6-phenyl-1-piperidyl]-2-oxo-acetyl]amino]pyridine-3-carboxamide, rac-5-[[2-[(2R,3R,6R)-2,3-dimethyl-6-phenyl-1-piperidyl]-2-oxo-acetyl]amino]pyridine-3-carboxamide and rac-5-[[2-[(2S,3R,6S)-2,3-dimethyl-6-phenyl-1-piperidyl]-2-oxo-acetyl]amino]pyridine-3-carboxamide (Compound 154, Compound 163 and Compound 181

To a stirred solution of [2-(2,3-dimethyl-6-phenyl-1-piperidyl)-2-oxo-acetyl]oxylithium (0.5 g, 1.87 mmol) in DMF (5 mL) was added HATU (711.38 mg, 1.87 mmol). The resulting reaction mixture was stirred at 20° C. for 10 minutes. After 10 minutes, 5-aminopyridine-3-carboxamide (256.58 mg, 1.87 mmol) was added and the resulting reaction mixture was allowed to stir at 20° C. for 12 hours. The resulting reaction mixture was purified by reverse phase HPLC (Mobile phase: 0.5-6.5 min; water-acetonitrile, flow rate: 30 mL/min; loading pump: 4 mL/min, acetonitrile; column: SunFire 19*100 mm, 5 um) to obtain rac-5-[[2-[(2R,3R,6S)-2,3-dimethyl-6-phenyl-1-piperidyl]-2-oxo-acetyl]amino]pyridine-3-carboxamide (Compound 154, 27.7 mg), rac-5-[[2-[(2R,3R,6R)-2,3-dimethyl-6-phenyl-1-piperidyl]-2-oxo-acetyl]amino]pyridine-3-carboxamide (Compound 163, 24.30 mg) and rac-5-[[2-[(2S,3R,6S)-2,3-dimethyl-6-phenyl-1-piperidyl]-2-oxo-acetyl]amino]pyridine-3-carboxamide (Compound 181, 35.2 mg) as yellow solid.

Compound 154:

$^1$H NMR (DMSO-$d_6$, 400 MHz): δ (ppm) 0.85 (m, 3H), 1.26 (m, 3H), 1.48 (m, 1H), 1.95 (m, 1H), 2.23 (m, 3H), 4.30 (m, 1H), 5.20 (m, 1H), 7.28 (m, 5H), 7.62 (m, 1H), 8.43 (m, 3H), 8.88 (m, 1H), 10.98 (m, 1H).

LCMS(ESI): [M+H]$^+$ m/z: calcd 380.2; found 381.2; Rt=1.199 min.

Compound 163:

$^1$H NMR (DMSO-$d_6$, 400 MHz): δ (ppm) 0.54 (m, 3H), 0.80 (m, 3H), 1.57 (m, 2H), 2.62 (m, 2H), 4.07 (m, 1H), 5.44 (m, 1H), 7.26 (m, 1H), 7.39 (m, 4H), 7.57 (m, 1H), 8.18 (m, 1H), 8.50 (m, 1H), 8.83 (m, 2H), 11.30 (m, 1H).

LCMS(ESI): [M+H]$^+$ m/z: calcd 380.2; found 381.2; Rt=1.222 min.

Compound 181:

$^1$H NMR (DMSO-$d_6$, 400 MHz): δ (ppm) 0.82 (m, 3H), 1.00 (m, 3H), 1.35 (m, 1H), 1.70 (m, 1H), 2.13 (m, 3H), 3.99 (m, 1H), 5.41 (m, 1H), 7.32 (m, 5H), 7.66 (m, 1H), 8.20 (m, 1H), 8.51 (m, 1H), 8.84 (m, 2H), 11.29 (s, 1H).

LCMS(ESI): [M+H]$^+$ m/z: calcd 380.2; found 381.2; Rt=1.215 min.

Step 4: Chiral Separation of 5-[[2-[(2S,3S,6R)-2,3-dimethyl-6-phenyl-1-piperidyl]-2-oxo-acetyl]amino]pyridine-3-carboxamide and 5-[[2-[(2R,3R,6S)-2,3-dimethyl-6-phenyl-1-piperidyl]-2-oxo-acetyl]amino]pyridine-3-carboxamide rac-5-[[2-[(2R,3R,6S)-2,3-dimethyl-6-phenyl-1-piperidyl]-2-oxo-acetyl]amino]pyridine-3-carboxamide (Compound 154) was subjected to chiral separation (Column: Chiralpak 1C-I, 250*20 mm, 5 um; Mobile phase: Hexane-IPA-MeOH, 50-25-25 Flow Rate: 12 mL/min) to obtain (Compound 435) and (Compound 433) as yellow solid.

Compound 435: LCMS(ESI): [M+H]$^+$ m/z: calcd 380.2; found 381.2; Rt=3.039 min.

Chiral HPLC: Rt=18.22 min (Column: IA; Mobile phase: Hexane-MeOH-IPA, 60-20-20; Flow Rate: 0.6 mL/min).

Compound 433: LCMS(ESI): [M+H]$^+$ m/z: calcd 380.2; found 381.2; Rt=3.030 min

Chiral HPLC: Rt=17.00 min (Column: IA; Mobile phase: Hexane-MeOH-IPA, 60-20-20; Flow Rate: 0.6 mL/min).

Step 5: Chiral Separation of 5-[[2-[(2S,3R,6S)-2,3-dimethyl-6-phenyl-1-piperidyl]-2-oxo-acetyl]amino]pyridine-3-carboxamide and 5-[[2-[(2R,3S,6R)-2,3-dimethyl-6-phenyl-1-piperidyl]-2-oxo-acetyl]amino]pyridine-3-carboxamide (Compound 482 and Compound 483 rac-5-[[2-[(2S,3R,6S)-2,3-dimethyl-6-phenyl-1-piperidyl]-2-oxo-acetyl]amino]pyridine-3-carboxamide (Compound 181) was subjected to chiral separation (Chiralpak OJ, 250*30 mm, 20 um; Mobile phase: CO$_2$-MeOH, 60-40; Flow Rate: 90 mL/min) to obtain (Compound 482) and (Compound 483) as yellow solid.

Compound 482: LCMS(ESI): [M+H]$^+$ m/z: calcd 380.2; found 381.2; Rt=4.815 min.

Chiral HPLC: Rt=2.61 min (Column: OJ-H; Mobile phase: CO$_2$-MeOH, 60-40; Flow Rate: 2.0 mL/min).

Compound 483: LCMS(ESI): [M+H]$^+$ m/z: calcd 380.2; found 381.2; Rt=4.817 min.

Chiral HPLC: Rt=4.13 min (Column: OJ-H; Mobile phase: CO$_2$-MeOH, 60-40; Flow Rate: 2.0 mL/min).

Example 699. The Synthesis of N-(5,6-dimethyl-3-pyridyl)-2-[(2S,5R)-5-methyl-2-phenyl-1-piperidyl]-2-oxo-acetamide (Compound 254) and N-(5,6-dimethyl-3-pyridyl)-2-[(2R,5S)-5-methyl-2-phenyl-1-piperidyl]-2-oxo-acetamide (Compound 258)

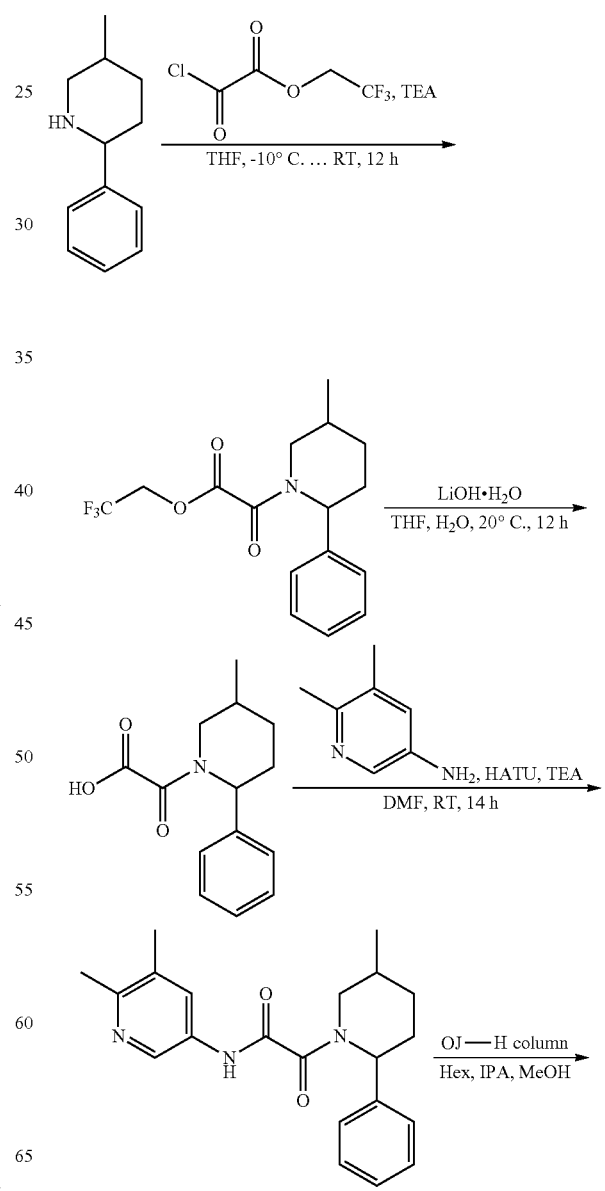

-continued

Compound 254

Compound 258

Step 1: The Synthesis of 2,2,2-trifluoroethyl 2-(5-methyl-2-phenyl-1-piperidyl)-2-oxo-acetate 2,2,2-trifluoroethyl 2-chloro-2-oxo-acetate (5.43 g, 28.53 mmol) was added dropwise to the solution of 5-methyl-2-phenyl-piperidine (5 g, 28.53 mmol) and triethylamine (2.89 g, 28.53 mmol, 3.98 mL) in THF (50 mL) at −10° C. The resulting mixture was left to warm to r.t. and stirred for 12 hr. The resulting precipitate was filtered off. The filtrate was evaporated to obtain 2,2,2-trifluoroethyl 2-(5-methyl-2-phenyl-1-piperidyl)-2-oxo-acetate (9 g, 27.33 mmol, 95.80% yield) which was used in next step without purification.

$^1$H NMR (400 MHz, DMSO-d$_6$) δ 1.19 (m, 3H), 1.33 (m, 1H), 1.91 (m, 4H), 3.10 (m, 2H), 5.10 (m, 3H), 7.19 (d, 1H), 7.21 (d, 1H), 7.40 (m, 3H).

LCMS(ESI): [M+H]$^+$ m/z: calcd 329.1; found 330.1; Rt=1.496 min.

Step 2: The Synthesis of 2-(5-methyl-2-phenyl-1-piperidyl)-2-oxo-acetic acid Lithium hydroxide (654.50 mg, 27.33 mmol) was added to the solution of 2,2,2-trifluoroethyl 2-(5-methyl-2-phenyl-1-piperidyl)-2-oxo-acetate (9 g, 27.33 mmol) in THF (100 mL) and water (10 mL). The resulting mixture was stirred at 20° C. for 12 hr. Then, the mixture was evaporated to dryness to obtain 2-(5-methyl-2-phenyl-1-piperidyl)-2-oxo-acetic acid (5 g, 19.67 mmol, 71.96% yield, Li+) which was used in next step without purification.

$^1$H NMR (400 MHz, DMSO-d$_6$) δ 1.13 (m, 3H), 1.30 (m, 1H), 1.63 (m, 2H), 2.01 (m, 2H), 3.56 (m, 2H), 5.04 (m, 1H), 7.16 (m, 3H), 7.32 (m, 2H).

LCMS(ESI): Acid[M+H]$^+$ m/z: calcd 247.1.1; found 248.2; Rt=1.133 min.

Step 3: The Synthesis of N-(5,6-dimethyl-3-pyridyl)-2-[(2S,5R)-5-methyl-2-phenyl-1-piperidyl]-2-oxo-acetamide DIPEA (261.32 mg, 2.02 mmol, 352.18 μL) was added to the solution of respective 2-(5-methyl-2-phenyl-1-piperidyl)-2-oxo-acetic acid (0.2 g, 808.77 μmol) and 5,6-dimethylpyridin-3-amine (98.81 mg, 808.77 μmol) in DMF (5 mL). The resulting mixture was stirred for 5 min followed by the addition of the solution of HATU (338.27 mg, 889.65 μmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC (Waters SunFire C18 19*100 mm 5 mkm column, H$_2$O-MeOH as a mobile phase) to afford pure N-(5,6-dimethyl-3-pyridyl)-2-[(2S,5R)-5-methyl-2-phenyl-1-piperidyl]-2-oxo-acetamide (70 mg, 199.18 μmol, 24.63% yield).

LCMS(ESI): [M+H]$^+$ m/z: calcd 351.2; found 352.4; Rt=2.702 min.

Step 4: The Synthesis of N-(5,6-dimethyl-3-pyridyl)-2-[(2S,5R)-5-methyl-2-phenyl-1-piperidyl]-2-oxo-acetamide (Compound 254) and N-(5,6-dimethyl-3-pyridyl)-2-[(2R,5S)-5-methyl-2-phenyl-1-piperidyl]-2-oxo-acetamide (Compound 258

Chiral Separation Conditions: Reverse Phase & Gradient: Hexane-IPA-MeOH, 70-15-15, 12 ml/min Column:OJ-H (250*20, 5 mkm); Rel.Time for Compound 254 15.77 min Rel.Time for Compound 258 10.18 min Compound 254: RT (OJ-H, Hexane-IPA-MeOH, 60-20-20, 0.6 mL/min)=15.778 min.

$^1$H NMR (600 MHz, DMSO-d$_6$) δ 0.96-1.04 (m, 3H), 1.26-1.36 (m, 1H), 1.59-1.72 (m, 1H), 1.80-1.94 (m, 1H), 1.99-2.14 (m, 1H), 2.16-2.25 (m, 4H), 2.32-2.37 (m, 3H), 2.72-3.23 (m, 1H), 3.40-4.07 (m, 1H), 5.11-5.62 (m, 1H), 7.23-7.28 (m, 1H), 7.28-7.31 (m, 1H), 7.31-7.38 (m, 2H), 7.38-7.41 (m, 1H), 7.70-7.86 (m, 1H), 8.37-8.60 (m, 1H), 10.85-11.01 (m, 1H).

LCMS(ESI): [M+H]$^+$ m/z: calcd 351.2; found 352.2; Rt=4.089 min.

Compound 258: RT (OJ-H, Hexane-IPA-MeOH, 60-20-20, 0.6 mL/min)=10.184 min.

$^1$H NMR (600 MHz, DMSO-d$_6$) δ 0.98-1.04 (m, 3H), 1.28-1.38 (m, 1H), 1.59-1.70 (m, 1H), 1.81-1.93 (m, 1H), 2.00-2.16 (m, 1H), 2.17-2.26 (m, 4H), 2.32-2.38 (m, 3H), 2.73-3.25 (m, 1H), 3.41-4.05 (m, 1H), 5.03-5.68 (m, 1H), 7.23-7.28 (m, 1H), 7.28-7.31 (m, 1H), 7.31-7.38 (m, 2H), 7.38-7.41 (m, 1H), 7.73-7.86 (m, 1H), 8.36-8.54 (m, 1H), 10.84-11.00 (m, 1H).

LCMS(ESI): [M+H]$^+$ m/z: calcd 351.2; found 352.2; Rt=4.081 min.

Example 700. The Synthesis of 2-methyl-5-[[2-[(2R,5S)-5-methyl-2-phenyl-1-piperidyl]-2-oxo-acetyl]amino]pyridine-3-carboxamide (Compound 200) and 2-methyl-5-[[2-[(2S,5R)-5-methyl-2-phenyl-1-piperidyl]-2-oxo-acetyl]amino]pyridine-3-carboxamide (Compound 196)

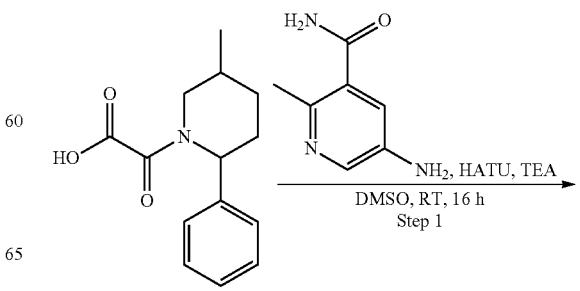

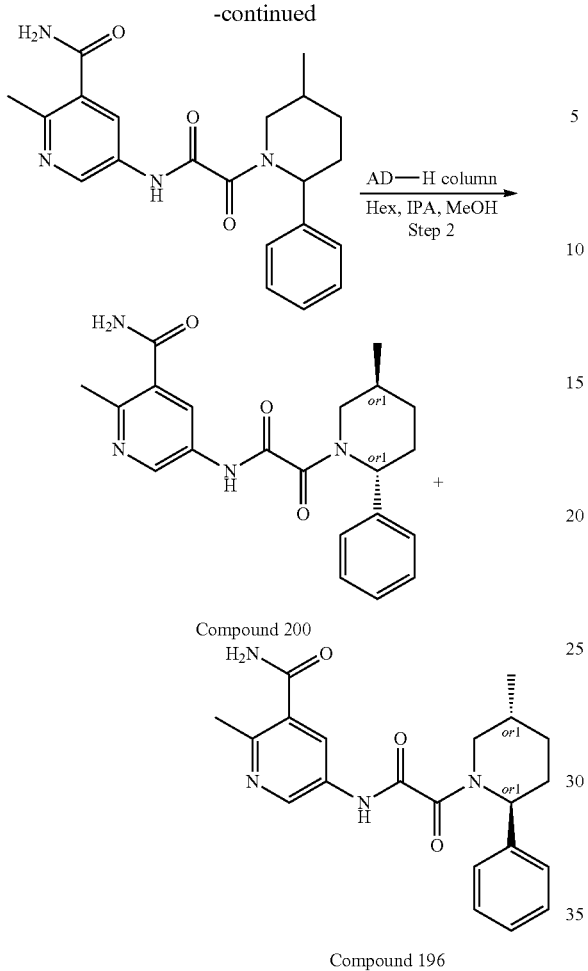

Compound 200

Compound 196

Step 1: The Synthesis of 2-methyl-5-[[2-(5-methyl-2-phenyl-1-piperidyl)-2-oxo-acetyl]amino]pyridine-3-carboxamide 5-amino-2-methyl-pyridine-3-carboxamide (213.95 mg, 1.42 mmol), 2-(5-methyl-2-phenyl-1-piperidyl)-2-oxo-acetic acid (350 mg, 1.42 mmol), HATU (591.97 mg, 1.56 mmol), and TEA (157.54 mg, 1.56 mmol, 217.00 μL) were mixed in DMSO (5 mL). The reaction mixture was stirred at RT for 16 hr. The solution in DMSO was subjected to HPLC (2-10 min 35-60% water-MeCN+NH₃ (loading pump 4 ml MeCN+NH₃); column: TRIART 100*20 5 microM) to afford 2-methyl-5-[[2-(5-methyl-2-phenyl-1-piperidyl)-2-oxo-acetyl]amino]pyridine-3-carboxamide (302 mg, 793.82 μmol, 56.09% yield). The final product after HPLC was obtained in three fractions. Fraction 1 and 2 was subjected to chiral separation on the next step.

LCMS(ESI): [M+H]⁺ m/z: calcd 380.2; found 381.2; Rt=3.064 min.

Step 2: The Synthesis of 2-methyl-5-[[2-[(2R,5S)-5-methyl-2-phenyl-1-piperidyl]-2-oxo-acetyl]amino]pyridine-3-carboxamide (Compound 200) and 2-methyl-5-[[2-[(2S,5R)-5-methyl-2-phenyl-1-piperidyl]-2-oxo-acetyl]amino]pyridine-3-carboxamide (Compound 196

2-methyl-5-[[2-(5-methyl-2-phenyl-1-piperidyl)-2-oxo-acetyl]amino]pyridine-3-carboxamide (142.3 mg, 374.04 μmol) was chirally separated (Sample Info: AD-H, Hexane-IPA-MeOH, 60-20-20, 0.6 ml/min) affording Compound 200-2-methyl-5-[[2-[(2R,5S)-5-methyl-2-phenyl-1-piperidyl]-2-oxo-acetyl]amino]pyridine-3-carboxamide (46.9 mg, 123.28 μmol, 32.96% yield) and Compound 196-2-methyl-5-[[2-[(2S,5R)-5-methyl-2-phenyl-1-piperidyl]-2-oxo-acetyl]amino]pyridine-3-carboxamide (35.7 mg, 142.30 μmol, 25.09% yield).

Compound 196: RT (AD-H, Hexane-IPA-MeOH, 60-20-20, 0.6 mL/min)=29.9 min.

¹H NMR (dmso, 600 MHz): δ (ppm) 1.01 (m, 3H), 1.33 (m, 1H), 1.66 (m, 1H), 1.87 (m, 1H), 2.05 (m, 1H), 2.22 (m, 1H), 2.51 (m, 3H), 3.08 (m, 1H), 3.73 (m, 1H), 5.37 (m, 1H), 7.27 (t, 1H), 7.30 (d, 1H), 7.37 (m, 3H), 7.54 (m, 1H), 7.88 (m, 1H), 8.01 (m, 1H), 8.69 (m, 1H), 11.10 (m, 1H).

LCMS(ESI): [M+H]⁺ m/z: calcd 380.2; found 381.2; Rt=4.332 min.

Compound 200: RT (AD-H, Hexane-IPA-MeOH, 60-20-20, 0.6 mL/min)=12.8 min.

¹H NMR (dmso, 600 MHz): δ (ppm) 1.01 (m, 3H), 1.33 (m, 1H), 1.65 (m, 1H), 1.84 (m, 1H), 2.00 (m, 1H), 2.18 (m, 1H), 2.44 (m, 3H), 2.99 (m, 1H), 3.73 (m, 1H), 5.37 (m, 1H), 7.27 (t, 1H), 7.30 (d, 1H), 7.38 (m, 3H), 7.54 (m, 1H), 7.87 (m, 1H), 8.01 (m, 1H), 8.68 (m, 1H), 11.10 (m, 1H).

LCMS(ESI): [M+H]⁺ m/z: calcd 380.2; found 381.2; Rt=4.330 min.

Example 701. The Synthesis of N-(6-amino-5-methylpyridin-3-yl)-2-(5-methyl-2-(4-(trifluoromethyl)phenyl)piperidin-1-yl)-2-oxoacetamide (Compound 548, Compound 575

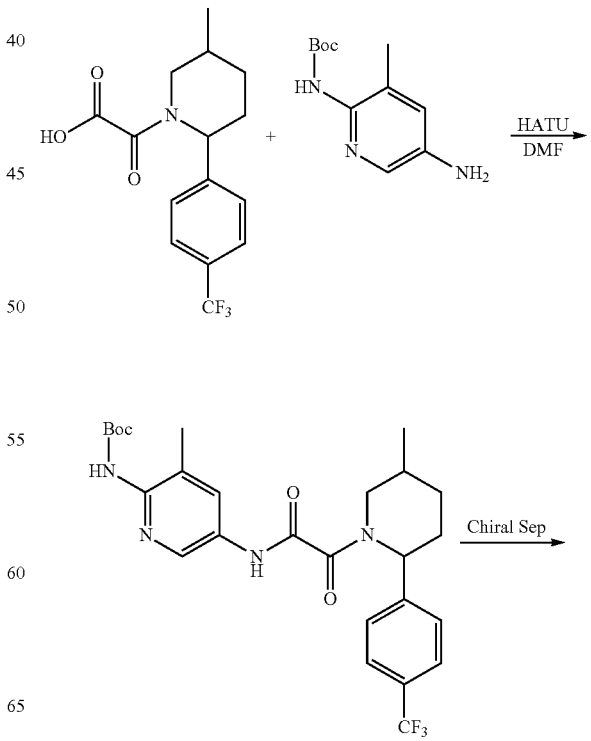

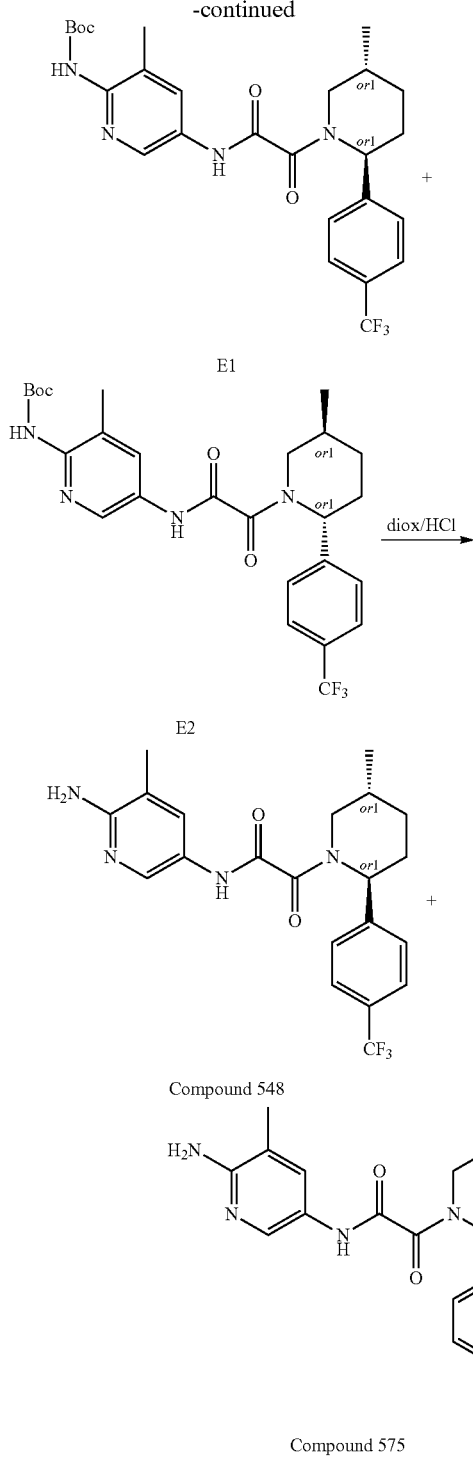

Compound 548

Compound 575

Step 1: Synthesis of tert-butyl (3-methyl-5-(2-(5-methyl-2-(4-(trifluoromethyl)phenyl)piperidin-1-yl)-2-oxoacetamido)pyridin-2-yl)carbamate 2-[5-methyl-2-[4-(trifluoromethyl)phenyl]-1-piperidyl]-2-oxo-acetic acid (0.3 g, 931.02 µmol, Li+) was mixed with HATU (389.40 mg, 1.02 mmol) in DMF (5 mL) and the resulting mixture was stirred at 20° C. for 10 min followed by addition of tert-butyl N-(5-amino-3-methyl-2-pyridyl) carbamate (207.87 mg, 931.02 µmol). The resulting mixture was stirred at 20° C. for 12 hr. The resulting solution was subjected to HPLC (column: SunFire 19*100 mm, 5 mkl; water-MeCN as an eluent mixture) to obtain tert-butyl N-[3-methyl-5-[[2-[5-methyl-2-[4-(trifluoromethyl)phenyl]-1-piperidyl]-2-oxo-acetyl]amino]-2-pyridyl]carbamate (0.1555 g, 298.73 µmol, 32.09% yield).

LCMS(ESI): [M]+ m/z: calcd 520.2; found 521.2; Rt=4.261 min.

Step 2: Chiral Separation tert-butyl N-[3-methyl-5-[[2-[5-methyl-2-[4-(trifluoromethyl)phenyl]-1-piperidyl]-2-oxo-acetyl]amino]-2-pyridyl] carbamate (217.2 mg, 417.26 µmol) was separated using Chiralpak IC 200*20, 5 mkm column; Hexane-IPA-MeOH, 80-10-10 as a mobile phase; Flow rate 15 mL/min; Injection Volume: 300 mkl; affording E1—tert-butyl N-[3-methyl-5-[[2-[(2S,5R)-5-methyl-2-[4-(trifluoromethyl)phenyl]-1-piperidyl]-2-oxo-acetyl]amino]-2-pyridyl]carbamate (52.94 mg, 101.70 µmol, 24.37% yield) (RT=21.62 min) and E2—tert-butyl N-[3-methyl-5-[[2-[(2R,5S)-5-methyl-2-[4-(trifluoromethyl)phenyl]-1-piperidyl]-2-oxo-acetyl]amino]-2-pyridyl]carbamate (61.88 mg, 118.88 µmol, 28.49% yield) (RT=25.74 min). Ret time for E1 in analytical conditions (column: 1C-3, Hexane-IPA-MeOH, 80-10-10, 0.155 ml/min as mobile phase) 15.75 min and for E2 19.80 min.

E1: Retention time: 15.75 min
LCMS(ESI): [M]+ m/z: calcd 520.2; found 521.2; Rt=1.301 min.
E2: Retention time: 19.80 min
LCMS(ESI): [M]+ m/z: calcd 520.2; found 521.2; Rt=1.302 min.

Step 3: Synthesis of N-(6-amino-5-methylpyridin-3-yl)-2-(5-methyl-2-(4-(trifluoromethyl)phenyl)piperidin-1-yl)-2-oxoacetamide (Compound 548 and Compound 575 tert-butyl N-[3-methyl-5-[[2-[(2R,5S)-5-methyl-2-[4-(trifluoromethyl)phenyl]-1-piperidyl]-2-oxo-acetyl]amino]-2-pyridyl]carbamate (61.88 mg, 118.88 µmol) and tert-butyl N-[3-methyl-5-[[2-[(2S,5R)-5-methyl-2-[4-(trifluoromethyl)phenyl]-1-piperidyl]-2-oxo-acetyl]amino]-2-pyridyl] carbamate (0.05294 g, 101.70 µmol) were dissolved in water (3 mL) and dioxane (1 mL) and the resulting mixture was heated to 100° C. for 12 hr. The resulting mixture was cooled to rt and subjected to HPLC (column: SunFire 19*100 mm, 5 mkl; water-MeCN as an eluent mixture) to obtain N-(6-amino-5-methyl-3-pyridyl)-2-[(2R,5S)-5-methyl-2-[4-(trifluoromethyl)phenyl]-1-piperidyl]-2-oxo-acetamide (0.022 g, 52.33 µmol, 44.02% yield) and N-(6-amino-5-methyl-3-pyridyl)-2-[(2S,5R)-5-methyl-2-[4-(trifluoromethyl)phenyl]-1-piperidyl]-2-oxo-acetamide (0.0255 g, 60.65 µmol, 59.64% yield).

Compound 548: ¹H NMR (600 MHz, DMSO-d₆) δ (ppm) 0.98-1.05 (m, 3H), 1.26-1.40 (m, 1H), 1.56-1.67 (m, 1H), 1.81-1.92 (m, 1H), 1.96-2.03 (m, 3H), 2.03-2.15 (m, 1H), 2.16-2.29 (m, 1H), 2.70-3.23 (m, 1H), 3.45-4.08 (m, 1H), 5.20-5.67 (m, 3H), 7.40-7.49 (m, 1H), 7.50-7.59 (m, 2H), 7.71-7.77 (m, 2H), 7.93-8.04 (m, 1H), 10.30-10.61 (m, 1H).

LCMS(ESI): [M]+ m/z: calcd 420.2; found 421.2; Rt=2.728 min.

Compound 575: ¹H NMR (600 MHz, DMSO-d₆) δ (ppm) 0.97-1.03 (m, 3H), 1.24-1.39 (m, 1H), 1.55-1.67 (m, 1H), 1.75-1.93 (m, 1H), 1.94-2.03 (m, 3H), 2.03-2.15 (m, 1H), 2.16-2.29 (m, 1H), 2.75-3.24 (m, 1H), 3.46-4.06 (m, 1H), 5.19-5.64 (m, 3H), 7.41-7.49 (m, 1H), 7.49-7.60 (m, 2H), 7.69-7.80 (m, 2H), 7.90-8.06 (m, 1H), 10.45-10.55 (m, 1H).
LCMS(ESI): [M]⁺ m/z: calcd 420.2; found 421.2; Rt=2.647 min.

Example 702. The Synthesis of 5-(2-(5-methyl-2-(4-(trifluoromethyl)phenyl)piperidin-1-yl)-2-oxoacetamido)nicotinamide (Compound 511, Compound 508

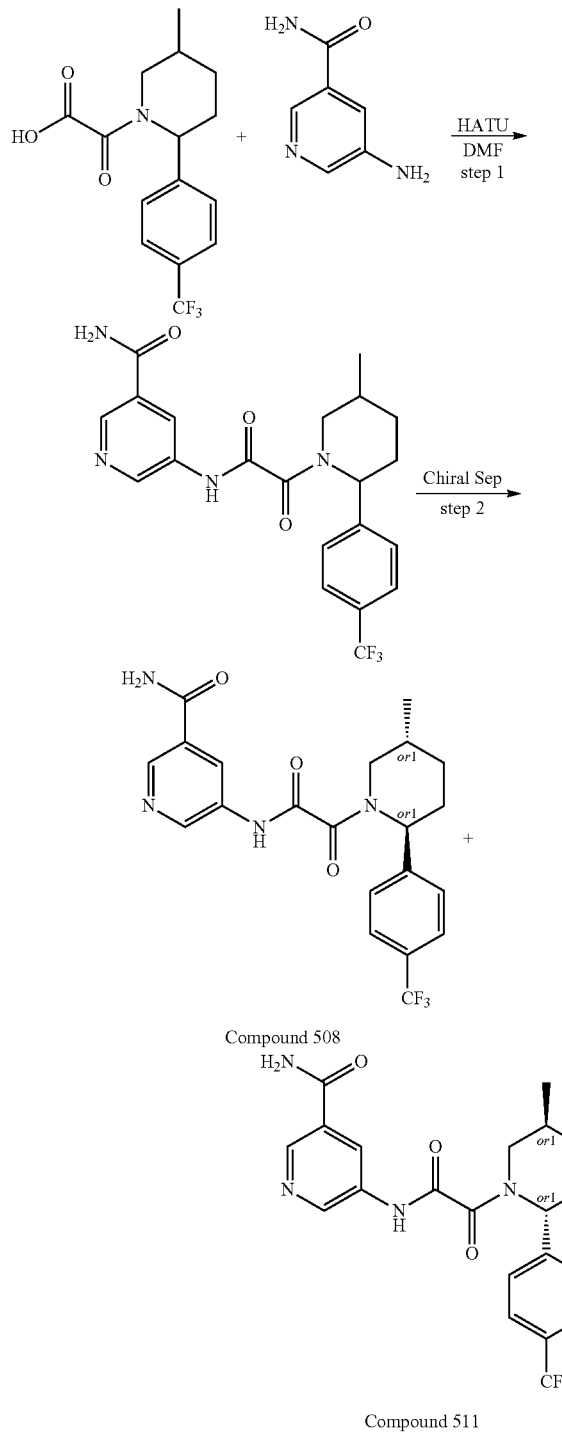

Compound 508

Compound 511

Step 1: Synthesis of 5-(2-(5-methyl-2-(4-(trifluoromethyl)phenyl)piperidin-1-yl)-2-oxoacetamido)nicotinamide 2-[5-methyl-2-[4-(trifluoromethyl)phenyl]-1-piperidyl]-2-oxo-acetic acid (0.3 g, 931.02 μmol, Li+) was mixed with HATU (389.40 mg, 1.02 mmol) in DMF (5 mL) and the resulting mixture was stirred at 20° C. for 10 min followed by addition of 5-aminopyridine-3-carboxamide (127.68 mg, 931.02 μmol). The resulting mixture was stirred at 20° C. for 12 hr. The resulting solution was subjected to HPLC (column: SunFire 19*100 mm, 5 mkl; water-MeCN as an eluent mixture) to obtain 5-[[2-[5-methyl-2-[4-(trifluoromethyl) phenyl]-1-piperidyl]-2-oxo-acetyl]amino]pyridine-3-carboxamide (0.1145. g, 263.58 μmol, 28.31% yield).
LCMS(ESI): [M]⁺ m/z: calcd 434.2; found 435.2; Rt=3.492 min.

Step 2: Chiral Separation (Compound 511 and Compound 508

5-[[2-[5-methyl-2-[4-(trifluoromethyl)phenyl]-1-piperidyl]-2-oxo-acetyl]amino]pyridine-3-carboxamide (114.5 mg, 263.58 μmol) was separated using Chiralpak IC 250*20, 5 mkm column; Hexane-IPA-MeOH, 60-20-20 as a mobile phase; Flow rate 12 mL/min; Injection Volume: 300 mkl; affording Compound 511-5-[[2-[(2S,5R)-5-methyl-2-[4-(trifluoromethyl)phenyl]-1-piperidyl]-2-oxo-acetyl]amino]pyridine-3-carboxamide (50.03 mg, 115.17 μmol, 43.69% yield) (RT=22.82 min) and Compound 508-5-[[2-[(2R,5S)-5-methyl-2-[4-(trifluoromethyl)phenyl]-1-piperidyl]-2-oxo-acetyl]amino]pyridine-3-carboxamide (58.4 mg, 134.43 μmol, 51% yield) (RT=38.04 min). Ret time for Compound 511 in analytical conditions (column: 1C-3, Hexane-IPA-MeOH, 60-20-20, 0.6 ml/min as mobile phase) 16.70 min and for Compound 508 27.34 min.

Compound 511: Retention time: 16.70 min
¹H NMR (600 MHz, DMSO-d₆) δ (ppm) 1.00-1.04 (m, 3H), 1.27-1.40 (m, 1H), 1.58-1.69 (m, 1H), 1.83-1.95 (m, 1H), 2.01-2.18 (m, 1H), 2.18-2.30 (m, 1H), 2.78-3.27 (m, 1H), 3.50-4.09 (m, 1H), 5.20-5.68 (m, 1H), 7.50-7.65 (m, 3H), 7.68-7.83 (m, 2H), 8.05-8.19 (m, 1H), 8.42-8.55 (m, 1H), 8.70-8.81 (m, 1H), 8.81-8.97 (m, 1H), 11.15-11.36 (m, 1H).
LCMS(ESI): [M]⁺ m/z: calcd 434.2; found 435.2; Rt=2.927 min.

Compound 508: Retention time: 27.34 min
¹H NMR (600 MHz, DMSO-d₆) δ (ppm) 0.98-1.05 (m, 3H), 1.28-1.40 (m, 1H), 1.58-1.71 (m, 1H), 1.83-1.94 (m, 1H), 2.03-2.18 (m, 1H), 2.18-2.28 (m, 1H), 2.74-3.26 (m, 1H), 3.49-4.10 (m, 1H), 5.22-5.88 (m, 1H), 7.50-7.64 (m, 3H), 7.69-7.79 (m, 2H), 8.08-8.24 (m, 1H), 8.40-8.54 (m, 1H), 8.72-8.81 (m, 1H), 8.81-8.94 (m, 1H), 11.11-11.40 (m, 1H).
LCMS(ESI): [M]⁺ m/z: calcd 434.2; found 435.2; Rt=2.929 min.

Example 703. The Synthesis of 5-(2-(2-(4-Fluoro-3-methylphenyl)-5-methylpiperidin-1-yl)-2-oxoacetamido)nicotinamide (Compound 307, Compound 293

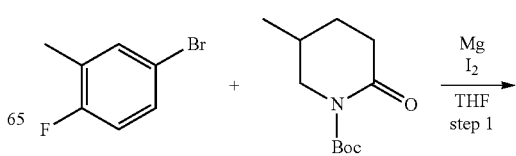

-continued

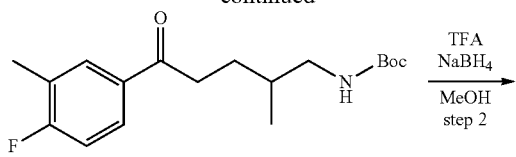

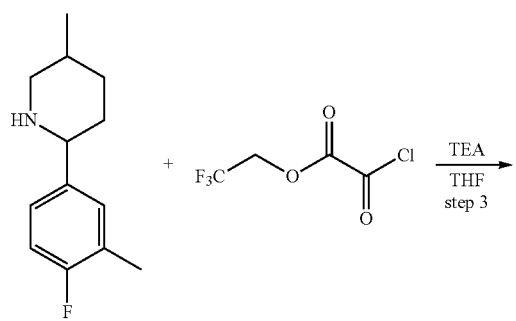

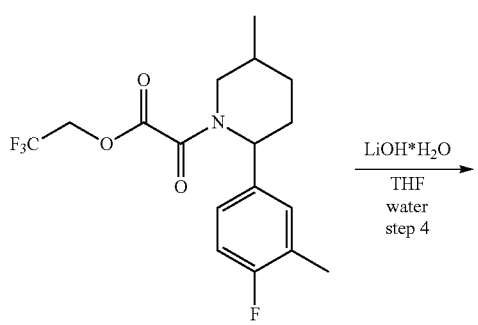

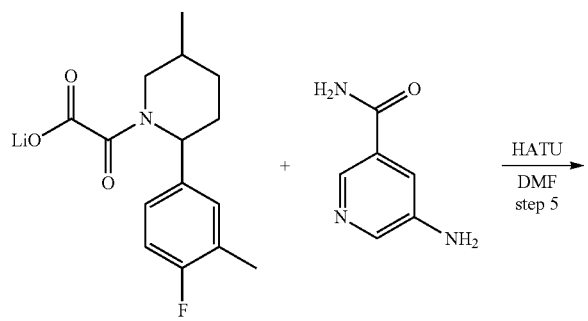

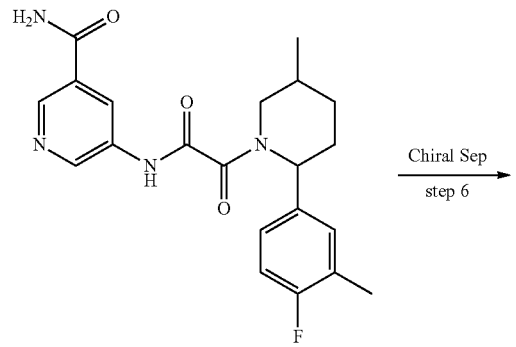

-continued

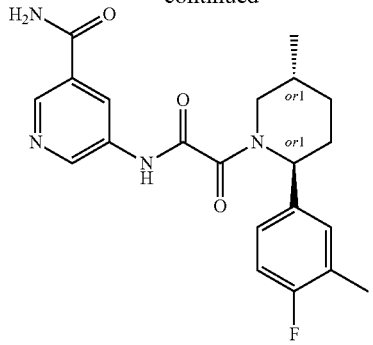

Compound 307

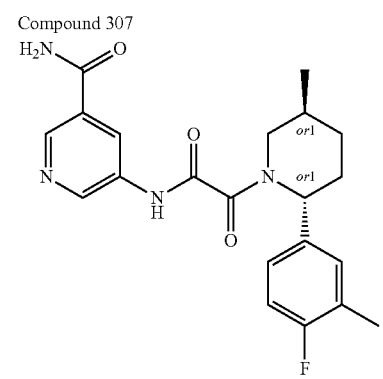

Compound 293

Step 1: Synthesis of tert-butyl (5-(4-Fluoro-3-methylphenyl)-2-methyl-5-oxopentyl)carbamate tert-butyl 5-methyl-2-oxo-piperidine-1-carboxylate (5.64 g, 26.45 mmol) (15% in THF solution) was cooled to rt and added dropwise to the solution of 4-bromo-1-fluoro-2-methyl-benzene (5 g, 26.45 mmol, 3.36 mL) in THF (50 mL) at −78° C. The resulting mixture was left to warm to rt and then poured into NH₄Cl aq. solution. The resulting mixture was extracted with EtOAc (2×40 ml). The combined organic extracts were washed with brine, dried over Na₂SO₄ and evaporated to obtain tert-butyl N-[5-(4-fluoro-3-methyl-phenyl)-2-methyl-5-oxo-pentyl]carbamate (5 g, 15.46 mmol, 58.45% yield), which was used in next step without purification.

$^1$H NMR (400 MHz, DMSO-d$_6$) δ (ppm) 0.98 (d, 3H), 1.49 (s, 9H), 1.85 (m, 4H), 2.22 (s, 3H), 2.95 (m, 2H), 3.80 (m, 1H), 5.55 (m, 1H), 7.12 (m, 3H).

LCMS(ESI): [M−Boc]$^+$ m/z: calcd 223.2; found 224.2; Rt=1.556 min.

Step 2: Synthesis of 2-(4-Fluoro-3-methylphenyl)-5-methylpiperidine tert-butyl N-[5-(4-fluoro-3-methyl-phenyl)-2-methyl-5-oxo-pentyl]carbamate (5 g, 15.46 mmol) was dissolved in trifluoroacetic acid (44.07 g, 386.52 mmol, 29.78 mL) and the resulting mixture was stirred for 1 hr. 50% aq. NaOH solution was added thereto to pH 11-12. The resulting mixture was extracted with DCM (4×40 ml) the combined organic layer was evaporated to dryness. The residue was dissolved in MeOH (50 mL) and sodium borohydride (584.92 mg, 15.46 mmol, 546.65 μL) was added. The resulting mixture was stirred at 20° C. for 12 hr and evaporated. 50% aq. NaOH solution was added to the residue. The resulting mixture was extracted with DCM (4×40 ml) the combined organic layer was evaporated to dryness to obtain 2-(4-fluoro-3-methyl-phenyl)-5-methyl-piperidine (1.4 g, 6.75 mmol, 43.68% yield) which was used in next step without purification.

$^1$H NMR (400 MHz, DMSO-d$_6$) δ (ppm) 0.82 (d, 3H), 1.46 (m, 1H), 1.50 (m, 1H), 1.66 (m, 1H), 1.76 (m, 1H), 2.19 (m, 2H), 2.25 (s, 3H), 2.98 (d, 1H), 3.40 (d, 1H), 4.17 (bds, 1H), 7.00 (m, 1H), 7.22 (m, 2H).

LCMS(ESI): [M]$^+$ m/z: calcd 207.2; found 208.2; Rt=0.950 min.

Step 3: Synthesis of 2,2,2-trifluoroethyl 2-(2-(4-Fluoro-3-methylphenyl)-5-methylpiperidin-1-yl)-2-oxoacetate 2,2,2-trifluoroethyl 2-chloro-2-oxo-acetate (919.04 mg, 4.82 mmol) was added dropwise to the solution of 2-(4-fluoro-3-methyl-phenyl)-5-methyl-piperidine (1 g, 4.82 mmol) and TEA (488.17 mg, 4.82 mmol, 672.40 µL) in THF (20 mL) at −10° C. The resulting mixture was left to warm to rt and stirred for 12 hr. The resulting precipitate was filtered off. The filtrate was evaporated to obtain 2,2,2-trifluoroethyl 2-[2-(4-fluoro-3-methyl-phenyl)-5-methyl-1-piperidyl]-2-oxo-acetate (1.7 g, 4.70 mmol, 97.52% yield) which was used in next step without purification.

$^1$H NMR (400 MHz, DMSO-d$_6$) δ (ppm) 0.96 (d, 3H), 1.45 (m, 2H), 1.68 (m, 2H), 1.98 (m, 2H), 2.25 (s, 3H), 3.09 (m, 1H), 3.62 (s, 2H), 5.13 (m, 1H), 7.20 (m, 3H).

LCMS(ESI): [M]$^+$ m/z: calcd 361.2; found 362.2; Rt=1.645 min.

Step 4: Synthesis of Lithium 2-(2-(4-Fluoro-3-methylphenyl)-5-methylpiperidin-1-yl)-2-oxoacetate Lithium hydroxide monohydrate, 98% (197.43 mg, 4.70 mmol, 130.75 µL) was added to the solution of 2,2,2-trifluoroethyl 2-[2-(4-fluoro-3-methyl-phenyl)-5-methyl-1-piperidyl]-2-oxo-acetate (1.7 g, 4.70 mmol) in water (3 mL) and THF (30 mL) and the resulting mixture was stirred at 20° C. for 12 hr. The resulting mixture was evaporated to dryness to obtain [2-[2-(4-fluoro-3-methyl-phenyl)-5-methyl-1-piperidyl]-2-oxo-acetyl]oxylithium (1 g, 3.51 mmol, 74.52% yield) which was used in next step without purification.

$^1$H NMR (400 MHz, DMSO-d$_6$) δ (ppm)

LCMS(ESI): [M]$^+$ m/z: calcd 285.2; found 286.2; Rt=min.

Step 5: Synthesis of 5-(2-(2-(4-Fluoro-3-methylphenyl)-5-methylpiperidin-1-yl)-2-oxoacetamido)nicotinamide

[2-[2-(4-Fluoro-3-methyl-phenyl)-5-methyl-1-piperidyl]-2-oxo-acetyl]oxylithium (0.3 g, 1.05 mmol) was mixed with HATU (399.91 mg, 1.05 mmol) in DMF (5 mL) and the resulting mixture was stirred at 20° C. for 10 min followed by addition of 5-aminopyridine-3-carboxamide (144.24 mg, 1.05 mmol). The resulting mixture was stirred at 20° C. for 12 hr. The resulting solution was subjected to HPLC (Waters Sunfire C18 19*100 5 mkm column and MeCN-water as an eluent mixture) to obtain 5-[[2-[2-(4-fluoro-3-methyl-phenyl)-5-methyl-1-piperidyl]-2-oxo-acetyl]amino]pyridine-3-carboxamide (0.1354 g, 339.83 µmol, 32.31% yield).

$^1$H NMR (400 MHz, DMSO-d$_6$) δ (ppm)

LCMS(ESI): [M]$^+$ m/z: calcd 398.2; found 399.2; Rt=3.091 min.

Step 6: Chiral Separation (Compound 307 and Compound 293

5-(2-(2-(4-fluoro-3-methylphenyl)-5-methylpiperidin-1-yl)-2-oxoacetamido)nicotinamide (135.4 mg, 339.83 µmol) was separated using Chiralpak 1C-I 250*20, 5 mkm column; Hexane-IPA-MeOH, 50-5-25 as a mobile phase; Flow rate 10 mL/min; Injection Volume: 900 mkl; affording Compound 307-5-[[2-[(2S,5R)-2-(4-fluoro-3-methyl-phenyl)-5-methyl-1-piperidyl]-2-oxo-acetyl]amino]pyridine-3-carboxamide (41 mg, 102.90 µmol, 30.28% yield) (RT (IC-3, Hexane-IPA-MeOH, 50-25-25, 0.155 ml/min)=9.67 min) as a yellow solid and Compound 293-5-[[2-[(2R,5S)-2-(4-fluoro-3-methyl-phenyl)-5-methyl-1-piperidyl]-2-oxo-acetyl]amino]pyridine-3-carboxamide (60.8 mg, 143.91 µmol, 35.87% yield) (RT (IC-3, Hexane-IPA-MeOH, 50-25-25, 0.155 ml/min)=15.26 min) as a yellow solid.

Compound 307: Retention time: 9.67 min $^1$H NMR (500 MHz, DMSO-d$_6$) δ (ppm) 1.00-1.05 (m, 3H), 1.30-1.42 (m, 1H), 1.63-1.74 (m, 1H), 1.84-1.96 (m, 1H), 2.01-2.15 (m, 1H), 2.16-2.27 (m, 4H), 2.80-3.19 (m, 1H), 3.47-4.03 (m, 1H), 5.07-5.61 (m, 1H), 7.11-7.29 (m, 3H), 7.57-7.69 (m, 1H), 8.10-8.23 (m, 1H), 8.43-8.56 (m, 1H), 8.74-8.83 (m, 1H), 8.83-9.00 (m, 1H), 11.16-11.32 (m, 1H).

LCMS(ESI): [M]$^+$ m/z: calcd 398.2; found 399.2; Rt=3.274 min.

Compound 293: Retention time: 15.26 min $^1$H NMR (500 MHz, DMSO-d$_6$) δ (ppm) 1.01-1.06 (m, 3H), 1.23-1.41 (m, 1H), 1.63-1.79 (m, 1H), 1.84-1.96 (m, 1H), 2.00-2.12 (m, 1H), 2.16-2.28 (m, 4H), 2.79-3.24 (m, 1H), 3.49-4.05 (m, 1H), 5.08-5.62 (m, 1H), 7.11-7.30 (m, 3H), 7.53-7.68 (m, 1H), 8.07-8.29 (m, 1H), 8.41-8.53 (m, 1H), 8.74-8.82 (m, 1H), 8.82-8.94 (m, 1H), 11.15-11.35 (m, 1H).

LCMS(ESI): [M]$^+$ m/z: calcd 398.2; found 399.2; Rt=3.264 min.

Example 704. The Synthesis of 5-[[2-[(2S,5R)-5-methyl-2-(m-tolyl)-1-piperidyl]-2-oxo-acetyl]amino]pyridine-3-carboxamide and 5-[[2-[(2R,53)-5-methyl-2-(m-tolyl)-1-piperidyl]-2-oxo-acetyl]amino]pyridine-3-carboxamide (Compound 227 and Compound 219

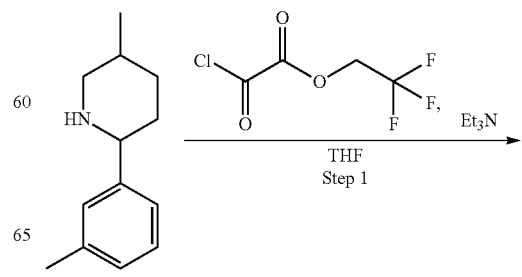

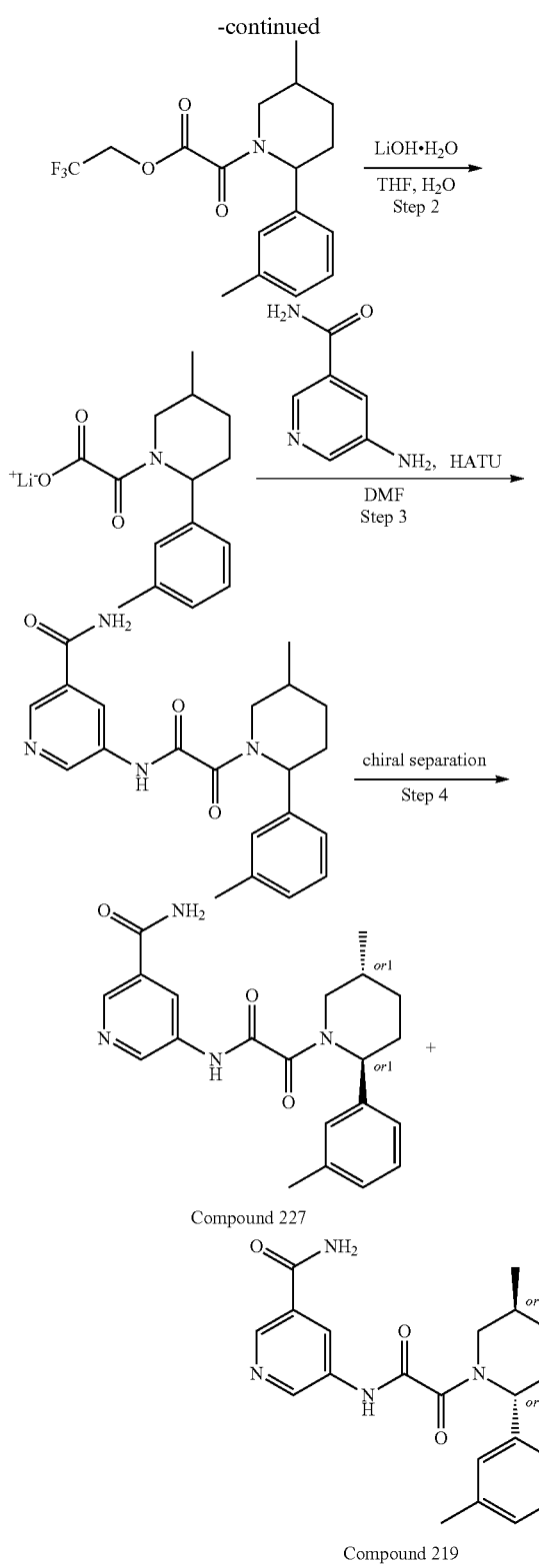

Synthesis of tert-butyl N-[2-methyl-5-(m-tolyl)-5-oxo-pentyl]carbamate

To a stirred solution of 5-methyl-2-(m-tolyl)piperidine (1 g, 5.28 mmol) and Triethylamine (534.56 mg, 5.28 mmol, 736.31 μL) in THF (30 mL) at −10° C., 2,2,2-trifluoroethyl 2-chloro-2-oxo-acetate (1.01 g, 5.28 mmol) was added dropwise. The resulting reaction mixture was allowed to warm to room temperature and stirred for 12 hours at the same temperature. After 12 hours, the reaction mixture was filtered. The filtrate was concentrated under reduced pressure to obtain 2,2,2-trifluoroethyl 2-[5-methyl-2-(m-tolyl)-1-piperidyl]-2-oxo-acetate (1.6 g, 4.66 mmol, 88.21% yield). The crude product was used for the next step reaction without any further purification.

LCMS(ESI): [M+H]+ m/z: calcd 343.2; found 344.2; Rt=1.590 min.

Step 2: Synthesis of [2-[5-methyl-2-(m-tolyl)-1-piperidyl]-2-oxo-acetyl]oxylithium To a stirred solution of 2,2,2-trifluoroethyl 2-[5-methyl-2-(m-tolyl)-1-piperidyl]-2-oxo-acetate (1.6 g, 4.66 mmol) in THF (20 mL) and water (2 mL) was added Lithium hydroxide monohydrate, 98% (195.55 mg, 4.66 mmol). The resulting reaction mixture was allowed to stir at 20° C. for 12 hours. Upon completion, the reaction mixture was concentrated under reduced pressure to obtain [2-[5-methyl-2-(m-tolyl)-1-piperidyl]-2-oxo-acetyl]oxylithium (0.9 g, 3.37 mmol, 72.27% yield). The crude product was used for the next step reaction without any further purification.

LCMS(ESI): [M+H]+ m/z: calcd 261.1; found 262.2; Rt=1.110 min.

Step 3: Synthesis of 5-[[2-[5-methyl-2-(m-tolyl)-1-piperidyl]-2-oxo-acetyl]amino]pyridine-3-carboxamide To a stirred solution of [2-[5-methyl-2-(m-tolyl)-1-piperidyl]-2-oxo-acetyl]oxylithium (0.3 g, 1.12 mmol) in DMF (5 mL) was added HATU (426.83 mg, 1.12 mmol). The resulting reaction mixture was stirred at 20° C. for 10 minutes. After 10 minutes, 5-aminopyridine-3-carboxamide (153.95 mg, 1.12 mmol) was added. The resulting reaction mixture was stirred at 20° C. for 12 hours. The resulting reaction mixture was subjected to reverse phase HPLC purification (Eluent: water-acetonitrile, 28%, 0.5-6.5 min; flow rate: 30 mL/min; loading pump: 4 mL/min; column: SunFire 19*100 mm, 5 um) to obtain 5-[[2-[5-methyl-2-(m-tolyl)-1-piperidyl]-2-oxo-acetyl]amino]pyridine-3-carboxamide (0.0844 g, 221.85 μmol, 19.76% yield).

LCMS(ESI): [M+H]+ m/z: calcd 380.2; found 381.2; Rt=3.375 min.

Chiral Separation of 5-[[2-[(2S,5R)-5-methyl-2-(m-tolyl)-1-piperidyl]-2-oxo-acetyl]amino]pyridine-3-carboxamide and 5-[[2-[(2R,5S)-5-methyl-2-(m-tolyl)-1-piperidyl]-2-oxo-acetyl]amino]pyridine-3-carboxamide (Compound 227 and Compound 219

5-[[2-[5-methyl-2-(m-tolyl)-1-piperidyl]-2-oxo-acetyl]amino]pyridine-3-carboxamide (0.084 g, 220.80 μmol) was subjected to chiral chromatography (Column: Chiralpak IA II, 250*20 mm, 5 um, Eluent: Hexane-MeOH-IPA, 70-15-15, flow rate: 12 mL/min) to give 5-[[2-[(2S,5R)-5-methyl-2-(m-tolyl)-1-piperidyl]-2-oxo-acetyl]amino]pyridine-3-carboxamide (Compound 227, 33 mg) and 5-[[2-[(2R,5S)-5-methyl-2-(m-tolyl)-1-piperidyl]-2-oxo-acetyl]amino]pyridine-3-carboxamide (Compound 219, 31 mg) as yellow solid.

Compound 227: $^1$H NMR (DMSO-$d_6$, 400 MHz): δ (ppm) 1.05 (m, 3H), 1.35 (m, 1H), 1.71 (m, 1H), 1.89 (m, 1H), 2.04 (m, 1H), 2.21 (m, 1H), 2.32 (m, 3H), 3.13 (m, 1H), 3.76 (m, 1H), 5.36 (m, 1H), 7.18 (m, 4H), 7.63 (m, 1H), 8.18 (m, 1H), 8.50 (m, 1H), 8.83 (m, 2H), 11.26 (m, 1H).
LCMS(ESI): [M+H]⁺ m/z: calcd 380.2; found 381.4; Rt=3.232 min.
Chiral HPLC: Rt=24.77 min (Column: IA; Eluent: Hexane-MeOH-IPA, 70-15-15; Flow Rate: 0.6 mL/min).
Compound 219: ¹H NMR (DMSO-d₆, 400 MHz): δ (ppm) 1.04 (m, 3H), 1.36 (m, 1H), 1.69 (m, 1H), 1.90 (m, 1H), 2.13 (m, 2H), 2.32 (m, 3H), 3.11 (m, 1H), 3.76 (m, 1H), 5.36 (m, 1H), 7.13 (m, 3H), 7.27 (m, 1H), 7.63 (m, 1H), 8.18 (m, 1H), 8.50 (m, 1H), 8.78 (m, 1H), 8.89 (m, 1H), 11.26 (m, 1H).
LCMS(ESI): [M+H]⁺ m/z: calcd 380.2; found 381.2; Rt=3.248 min.
Chiral HPLC: Rt=31.95 min (Column: IA; Eluent: Hexane-MeOH-IPA, 70-15-15; Flow Rate: 0.6 mL/min).

Example 705. The Synthesis of 5-(2-(5-methyl-2-(3-(trifluoromethyl)phenyl)piperidin-1-yl)-2-oxoacetamido)nicotinamide (Compound 509, Compound 510

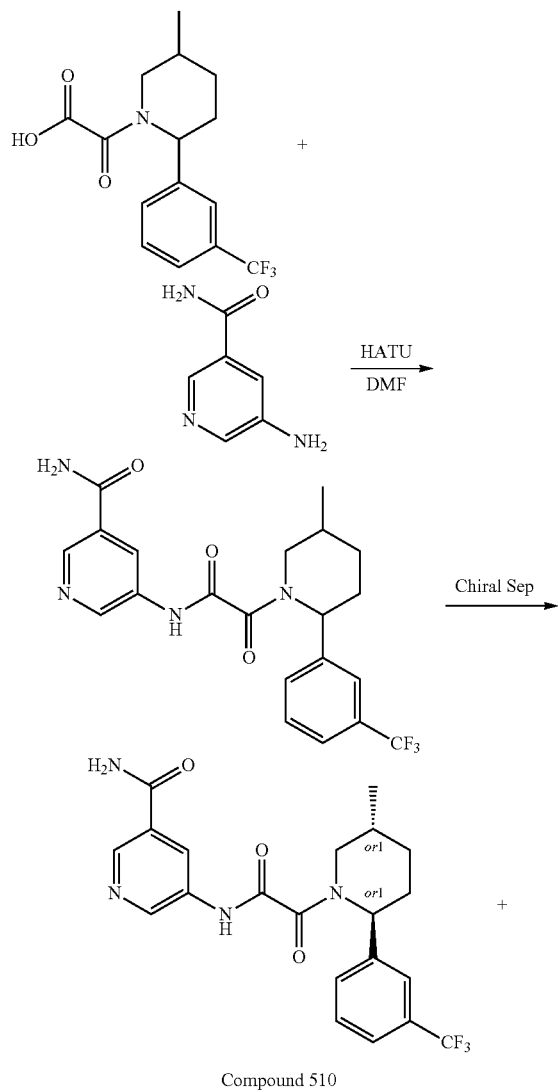

Compound 510

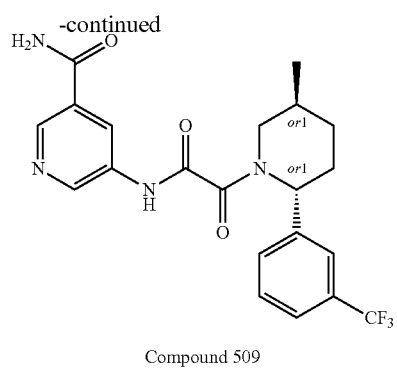

Compound 509

Step 1: Synthesis of 5-(2-(5-methyl-2-(3-(trifluoromethyl)phenyl)piperidin-1-yl)-2-oxoacetamido)nicotinamide 2-[5-methyl-2-[3-(trifluoromethyl)phenyl]-1-piperidyl]-2-oxo-acetic acid (0.3 g, 931.02 μmol, Li+) was mixed with HATU (354.00 mg, 931.02 μmol) in DMF (5 mL) and the resulting mixture was stirred at 20° C. for 10 min followed by addition of 5-aminopyridine-3-carboxamide (127.68 mg, 931.02 μmol). The resulting mixture was stirred at 20° C. for 12 hr. The resulting solution was subjected to HPLC (column: SunFire 19*100 mm, 5 mkl; water-MeCN as an eluent mixture) to obtain 5-[[2-[5-methyl-2-[3-(trifluoromethyl)phenyl]-1-piperidyl]-2-oxo-acetyl]amino]pyridine-3-carboxamide (0.166 g, 382.13 μmol, 41.04% yield).
LCMS(ESI): [M]⁺ m/z: calcd 434.2; found 435.2; Rt=3.308 min.

Step 2: Chiral Separation (Compound 509 and Compound 510

5-[[2-[5-methyl-2-[3-(trifluoromethyl)phenyl]-1-piperidyl]-2-oxo-acetyl]amino]pyridine-3-carboxamide (166 mg, 382.13 μmol) was separated using Chiralpak 1C-I 250*20, 5 mkm column; Hexane-IPA-MeOH, 60-20-20 as a mobile phase; Flow rate 12 mL/min; Injection Volume: 400 mkl; affording Compound 509-5-[[2-[(2R,5S)-5-methyl-2-[3-(trifluoromethyl)phenyl]-1-piperidyl]-2-oxo-acetyl]amino]pyridine-3-carboxamide (60.41 mg, 139.06 μmol, 36.39% yield) (RT=22.68 min) and Compound 510-5-[[2-[(2S,5R)-5-methyl-2-[3-(trifluoromethyl)phenyl]-1-piperidyl]-2-oxo- acetyl]amino]pyridine-3-carboxamide (54.87 mg, 166 μmol, 33.05% yield) (RT=15.63 min). Ret time for Compound 509 in analytical conditions (column: 1C, Hexane-IPA-MeOH, 60-20-20, 0.6 ml/min as mobile phase) 23.08 min and for Compound 510 15.71 min.
Compound 509: Retention time: 23.08 min
¹H NMR (600 MHz, DMSO-d₆) δ (ppm) 0.99-1.06 (m, 3H), 1.27-1.38 (m, 1H), 1.56-1.66 (m, 1H), 1.84-1.96 (m, 1H), 2.06-2.18 (m, 1H), 2.20-2.30 (m, 1H), 2.74-3.28 (m, 1H), 3.49-4.07 (m, 1H), 5.20-5.64 (m, 1H), 7.57-7.69 (m, 5H), 8.06-8.25 (m, 1H), 8.41-8.56 (m, 1H), 8.68-8.80 (m, 1H), 8.80-8.93 (m, 1H), 11.21-11.32 (m, 1H).
LCMS(ESI): [M]⁺ m/z: calcd 434.2; found 435.2; Rt=3.363 min.
Compound 510: Retention time: 15.71 min
¹H NMR (600 MHz, DMSO-d₆) δ (ppm) 0.98-1.06 (m, 3H), 1.27-1.41 (m, 1H), 1.57-1.67 (m, 1H), 1.85-1.95 (m, 1H), 2.06-2.20 (m, 1H), 2.20-2.32 (m, 1H), 2.74-3.27 (m, 1H), 3.48-4.10 (m, 1H), 5.24-5.65 (m, 1H), 7.55-7.70 (m, 5H), 8.07-8.22 (m, 1H), 8.38-8.53 (m, 1H), 8.69-8.80 (m, 1H), 8.80-8.94 (m, 1H), 11.17-11.37 (m, 1H).

LCMS(ESI): [M]⁺ m/z: calcd 434.2; found 435.2; Rt=3.367 min.

Example 706. The Synthesis of N-(6-amino-5-methylpyridin-3-yl)-2-(5-methyl-2-(3-(trifluoromethyl)phenyl)piperidin-1-yl)-2-oxoacetamide (Compound 507, Compound 496

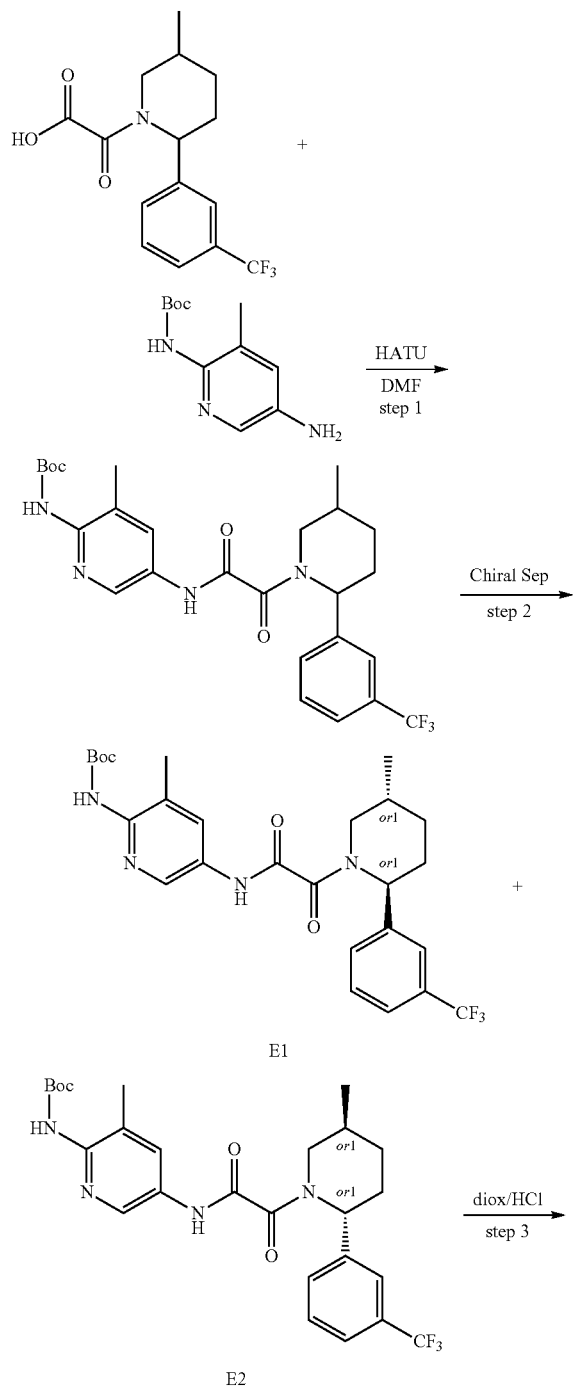

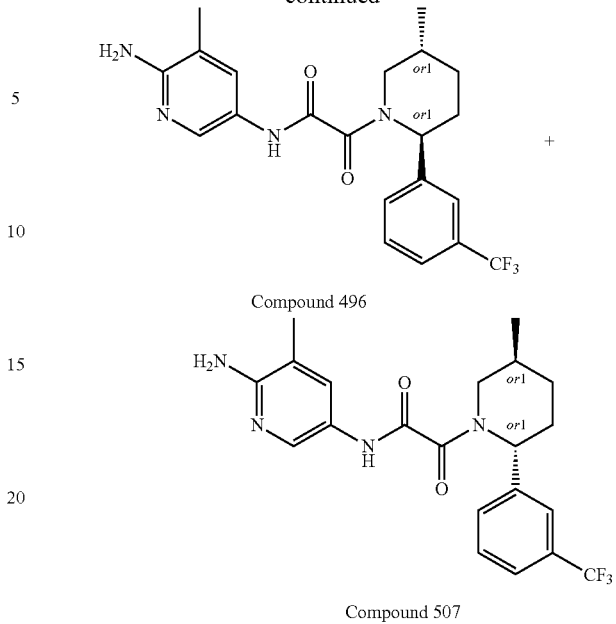

Compound 496

Compound 507

Step 1: Synthesis of tert-butyl (3-methyl-5-(2-(5-methyl-2-(3-(trifluoromethyl)phenyl)piperidin-1-yl)-2-oxoacetamido)pyridin-2-yl)carbamate 2-[5-methyl-2-[3-(trifluoromethyl)phenyl]-1-piperidyl]-2-oxo-acetic acid (0.3 g, 931.02 μmol, Li+) was mixed with HATU (389.40 mg, 1.02 mmol) in DMF (5 mL) and the resulting mixture was stirred at 20° C. for 10 min followed by addition of tert-butyl N-(5-amino-3-methyl-2-pyridyl) carbamate (207.87 mg, 931.02 μmol). The resulting mixture was stirred at 20° C. for 12 hr. The resulting solution was subjected to HPLC (column: SunFire 19*100 mm, 5 mkl; water-MeCN as an eluent mixture) to obtain tert-butyl N-[3-methyl-5-[[2-[5-methyl-2-[3-(trifluoromethyl)phenyl]-1-piperidyl]-2-oxo-acetyl]amino]-2-pyridyl]carbamate (323.90 mg, 622.24 μmol, 66.83% yield).

LCMS(ESI): [M]⁺ m/z: calcd 520.2; found 521.2; Rt=4.245 min.

Step 2: Chiral Separation tert-butyl N-[3-methyl-5-[[2-[5-methyl-2-[3-(trifluoromethyl)phenyl]-1-piperidyl]-2-oxo-acetyl]amino]-2-pyridyl]carbamate (323.9 mg, 620.51 μmol) was separated using Chiralpak IC 250*20, 5 mkm column; Hexane-IPA-MeOH, 80-10-10 as a mobile phase; Flow rate 12 mL/min; Injection Volume: 200 mkl; affording E1—tert-butyl N-[3-methyl-5-[[2-[(2S,5R)-5-methyl-2-[3-(trifluoromethyl)phenyl]-1-piperidyl]-2-oxo-acetyl]amino]-2-pyridyl]carbamate (132.86 mg, 255.23 μmol, 41.13% yield) (RT=39.76 min) and E2-tert-butyl N-[3-methyl-5-[[2-[(2R,5S)-5-methyl-2-[3-(trifluoromethyl)phenyl]-1-piperidyl]-2-oxo-acetyl]amino]-2-pyridyl]carbamate (107.18 mg, 205.90 μmol, 33.18% yield) (RT=32.18 min). Ret time for E1 in analytical conditions (column: 1C, Hexane-IPA-MeOH, 80-10-10, 0.6 ml/min as mobile phase) 25.79 min and for E2 23.60 min.

E1: Retention time: 25.79 min

LCMS(ESI): [M]⁺ m/z: calcd 520.2; found 521.2; Rt=6.125 min.

E2: Retention time: 23.60 min
LCMS(ESI): [M]⁺ m/z: calcd 520.2; found 521.2; Rt=6.199 min.

Step 3: Synthesis of N-(6-amino-5-methylpyridin-3-yl)-2-(5-methyl-2-(3-(trifluoromethyl)phenyl)piperidin-1-yl)-2-oxoacetamide (Compound 507 and Compound 496 tert-butyl N-[3-methyl-5-[[2-[(2R,5S)-5-methyl-2-[3-(trifluoromethyl)phenyl]-1-piperidyl]-2-oxo-acetyl]amino]-2-pyridyl]carbamate (0.107 g, 205.55 µmol) and tert-butyl N-[3-methyl-5-[[2-[(2S,5R)-5-methyl-2-[3-(trifluoromethyl)phenyl]-1-piperidyl]-2-oxo-acetyl]amino]-2-pyridyl]carbamate (0.132 g, 253.58 µmol) were dissolved in diox/HCl (3 mL) and the resulting mixture was stirred at 20° C. for 12 hr. The resulting mixture was evaporated and the residue was subjected to HPLC (column: Triart 20*100 mm, 5 mkl; water-MeOH+NH₃ as an eluent mixture) to obtain N-(6-amino-5-methyl-3-pyridyl)-2-[(2R,5S)-5-methyl-2-[3-(trifluoromethyl)phenyl]-1-piperidyl]-2-oxo-acetamide (0.0582 g, 138.43 µmol, 67.34% yield) and N-(6-amino-5-methyl-3-pyridyl)-2-[(2S,5R)-5-methyl-2-[3-(trifluoromethyl)phenyl]-1-piperidyl]-2-oxo-acetamide (0.0156 g, 37.11 µmol, 14.63% yield).

Compound 507: LCMS(ESI): [M]⁺ m/z: calcd 420.2; found 421.2; Rt=1.063 min.

Compound 496: LCMS(ESI): [M]⁺ m/z: calcd 420.2; found 421.2; Rt=1.072 min.

Example 707. The Synthesis of N-(6-amino-5-methyl-3-pyridyl)-2-[(2R,5S)-2-(3-chloro-4-Fluoro-phenyl)-5-methyl-1-piperidyl]-2-oxo-acetamide (Compound 606) and N-(6-amino-5-methyl-3-pyridyl)-2-[(2S,5R)-2-(3-chloro-4-Fluoro-phenyl)-5-methyl-1-piperidyl]-2-oxo-acetamide (Compound 596)

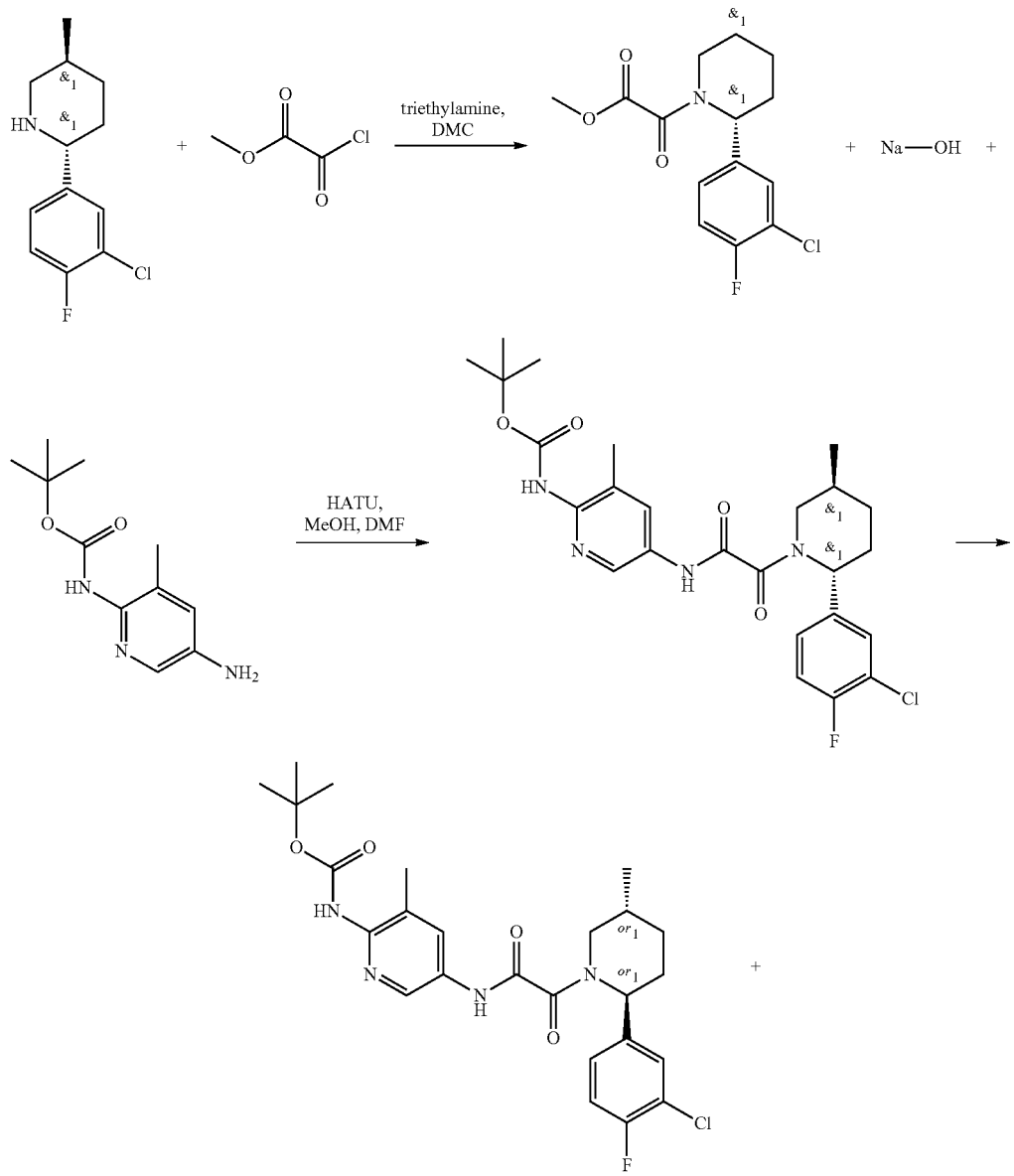

-continued

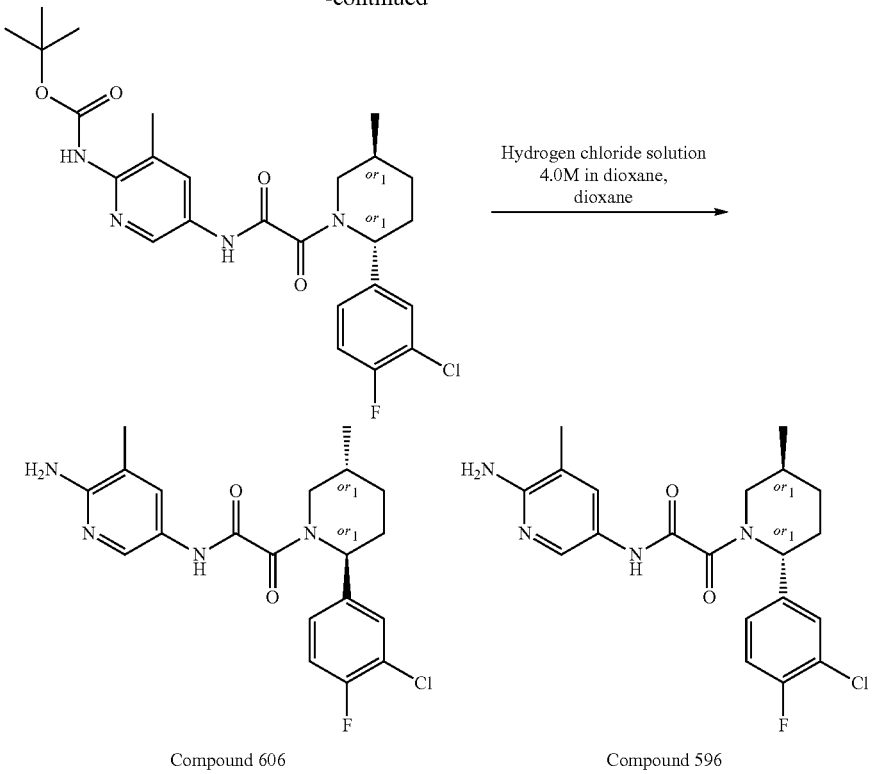

Compound 606

Compound 596

Step 1: Synthesis of methyl 2-[2-(3-chloro-4-Fluoro-phenyl)-5-methyl-1-piperidyl]-2-oxo-acetate To a solution of 2-(3-chloro-4-fluoro-phenyl)-5-methyl-piperidine (0.5 g, 2.20 mmol) and triethylamine (266.63 mg, 2.63 mmol, 367.27 μL) in DCM was added methyl 2-chloro-2-oxo-acetate (295.90 mg, 2.42 mmol) at 0° C. After stirring at rt for 1 hr the resulting mixture were diluted with $Et_2O$ and filtered and then evaporated to dryness to give methyl 2-[2-(3-chloro-4-fluoro-phenyl)-5-methyl-1-piperidyl]-2-oxo-acetate (0.75 g, crude) as a yellow solid, which was used in the next step without further purification.

$^1$H NMR ($CDCl_3$, 500 MHz): δ 1.08 (d, 3H), 1.47 (m, 1H), 1.79 (m, 1H), 1.94 (m, 1H), 2.17-2.24 (m, 2H), 3.23 (dd, 2H), 3.80-3.91 (two singlet, 3H), 5.72 (s, 1H), 7.17-7.29 (m, 3H).

LCMS(ESI): $[M+H]^+$ m/z: calcd 313.1; found 314.2; Rt=1.453 min.

Step 2: Synthesis of tert-butyl N-[5-[[2-[2-(3-chloro-4-Fluoro-phenyl)-5-methyl-1-piperidyl]-2-oxo-acetyl]amino]-3-methyl-2-pyridyl]carbamate To a solution of methyl 2-[2-(3-chloro-4-fluoro-phenyl)-5-methyl-1-piperidyl]-2-oxo-acetate (0.75 g, 2.39 mmol) in MeOH (12.50 mL) was added hydroxysodium (105.17 mg, 2.63 mmol, 49.38 μL) and the resulting mixture was stirred for 1 hr. Then, the solvent was evaporated and the residue was reevaporated with EtOH. After that, solids were dissolved in DMF and HATU (908.91 mg, 2.39 mmol) was added followed by tert-butyl N-(5-amino-3-methyl-2-pyridyl)carbamate (533.71 mg, 2.39 mmol) and the resulting mixture was stirred for 12 hr. The resulting mixture was poured into water, extracted 3 times with EtOAc, combined organics were washed with water, brine and evaporated. The residue was subjected to HPLC (55-80% 2-7 min water-acetonitrile; flow: 30 ml/min; (loading pump 4 ml/min, acetonitrile); column: SunFire C18 100×19 mm 5 um). Two fraction of tert-butyl N-[5-[[2-[2-(3-chloro-4-fluoro-phenyl)-5-methyl-1-piperidyl]-2-oxo-acetyl]amino]-3-methyl-2-pyridyl]carbamate (654.6 mg, 1.30 mmol, 54.23% yield) were obtained: 385.7 mg (100% by LCMS, almost single diastereomer) and 268.9 mg (100% by LCMS, 3:1=trans/cis).

$^1$H NMR ($CDCl_3$, 400 MHz): δ 1.06 (m, 3H), 1.47 (m, 10H), 1.79 (m, 1H), 1.94 (m, 1H), 2.17-2.24 (m, 2H), 3.23 (dd, 2H), 3.80-3.91 (two singlet, 3H), 5.72 (s, 1H), 7.17-7.29 (m, 3H).

LCMS(ESI): $[M+H]^+$ m/z: calcd 504.2; found 505.4; Rt=3.312 min.

Step 3: Synthesis of tert-butyl N-[5-[[2-[(2R,5S)-2-(3-chloro-4-Fluoro-phenyl)-5-methyl-1-piperidyl]-2-oxo-acetyl]amino]-3-methyl-2-pyridyl]carbamate (P1) and Tert-butyl N-[5-[[2-[(2S,5R)-2-(3-chloro-4-Fluoro-phenyl)-5-methyl-1-piperidyl]-2-oxo-acetyl]amino]-3-methyl-2-pyridyl]carbamate (P2 tert-butyl N-[5-[[2-[2-(3-chloro-4-fluoro-phenyl)-5-methyl-1-piperidyl]-2-oxo-acetyl]amino]-3-methyl-2-pyridyl]carbamate (385.7 mg, 763.79 μmol) was chirally separated (Column: Chiralpak 1C (250*20 mm, 5 mkm); Hexane-IPA-MeOH, 70-15-15 as a mobile phase; Flow Rate: 14 mL/min; Column Temperature: 20° C.; Wavelength: 205 nm) affording rel-tert-butyl N-[5-[[2-[(2R,5S)-2-(3-chloro-4-fluoro-phenyl)-5-methyl-1-piperidyl]-2-oxo-acetyl]amino]-3-methyl-2-pyridyl]carbamate (106.44 mg, 27.60% yield; P1) and rel-tert-butyl N-[5-[[2-[(2S,5R)-2-(3- chloro-4-fluoro-phenyl)-5-methyl-1-piperidyl]-2-oxo-acetyl]amino]-3-methyl-2-pyridyl]carbamate (131.29 mg, 34.04% yield; P2).

P2: LCMS(ESI): [M+H]⁺ m/z: calcd 504.9; found 505.2; Rt=6.158 min.

RT (IA-3, Hexane-IPA-MeOH, 70-15-15, 14 ml/min)=29.07 min

P1: LCMS(ESI): [M−BOC]⁺ m/z: calcd 504.9; found 449.2; Rt=6.163 min.

RT (IA-3, Hexane-IPA-MeOH, 70-15-15, 14 ml/min)=25.61 min.

Step 4: The Synthesis of N-(6-amino-5-methyl-3-pyridyl)-2-[(2R,5S)-2-(3-chloro-4-Fluoro-phenyl)-5-methyl-1-piperidyl]-2-oxo-acetamide (Compound 606

To a solution of tert-butyl N-[5-[[2-[(2R,5S)-2-(3-chloro-4-fluoro-phenyl)-5-methyl-1-piperidyl]-2-oxo-acetyl]amino]-3-methyl-2-pyridyl]carbamate (106.44 mg, 210.78 μmol) in dioxane (2 mL) was added Hydrogen chloride solution 4.0M in dioxane (38.43 mg, 1.05 mmol, 48.03 μL) at 21° C. The resulting mixture was left to stir for 2 hr. The resulting mixture was evaporated to dryness and subjected to HPLC (40-100% 2-7 min water-MeOH-NH₃; flow: 30 mL/min; (loading pump 4 mL/min, MeOH+NH₃); column: ymc-actus triat 100*19 mm 5 um (L)). N-(6-amino-5-methyl-3-pyridyl)-2-[(2R,5S)-2-(3-chloro-4-fluoro-phenyl)-5-methyl-1-piperidyl]-2-oxo-acetamide (43.6 mg, 107.69 μmol, 51.09% yield) was obtained as a white solid.

¹H NMR (600 MHz, DMSO-d₆) δ 0.97-1.01 (m, 3H), 1.24-1.37 (m, 1H), 1.59-1.68 (m, 1H), 1.81-1.93 (m, 1H), 1.95-2.07 (m, 4H), 2.12-2.24 (m, 1H), 2.69-3.26 (m, 1H), 3.42-4.03 (m, 1H), 5.09-5.54 (m, 1H), 5.58-5.66 (m, 2H), 7.26-7.37 (m, 1H), 7.39-7.46 (m, 2H), 7.46-7.54 (m, 1H), 7.92-8.04 (m, 1H), 10.38-10.60 (m, 1H).

LCMS(ESI): [M+H]⁺ m/z: calcd 404.1; found 405.2; Rt=2.663 min.

Step 6: The Synthesis of N-(6-amino-5-methyl-3-pyridyl)-2-[(2S,5R)-2-(3-chloro-4-Fluoro-phenyl)-5-methyl-1-piperidyl]-2-oxo-acetamide (Compound 596

To a solution of tert-butyl N-[5-[[2-[(2S,5R)-2-(3-chloro-4-fluoro-phenyl)-5-methyl-1-piperidyl]-2-oxo-acetyl]amino]-3-methyl-2-pyridyl]carbamate (131.29 mg, 259.99 μmol) in dioxane (2 mL) was added Hydrogen chloride solution 4.0 M in dioxane (47.40 mg, 1.30 mmol, 59.25 μL) at 21° C. The resulting mixture was left to stir for 2 hr. The resulting mixture was evaporated to dryness and subjected to HPLC (40-100% 2-7 min water-MeOH-NH₃; flow: 30 ml/min; (loading pump 4 ml/min, MeOH+NH₃); column: ymc-actus triat 100×19 mm 5 um (L)). N-(6-amino-5-methyl-3-pyridyl)-2-[(2S,5R)-2-(3-chloro-4-fluoro-phenyl)-5-methyl-1-piperidyl]-2-oxo-acetamide (55.7 mg, 137.58 μmol, 52.92% yield) was obtained as a white solid.

¹H NMR (600 MHz, DMSO-d₆) δ 0.96-1.02 (m, 3H), 1.24-1.38 (m, 1H), 1.56-1.71 (m, 1H), 1.81-1.92 (m, 1H), 1.96-2.10 (m, 4H), 2.11-2.25 (m, 1H), 2.68-3.24 (m, 1H), 3.41-4.04 (m, 1H), 5.08-5.54 (m, 1H), 5.55-5.69 (m, 2H), 7.27-7.37 (m, 1H), 7.39-7.46 (m, 2H), 7.46-7.53 (m, 1H), 7.93-8.04 (m, 1H), 10.45-10.65 (m, 1H).

LCMS(ESI): [M+H]⁺ m/z: calcd 404.1; found 405.2; Rt=2.654 min.

Example 708. The Synthesis of 2-amino-5-[[2-oxo-2-(2-phenyl-1-piperidyl)acetyl]amino]pyridine-3-carboxamide (Compound 126)

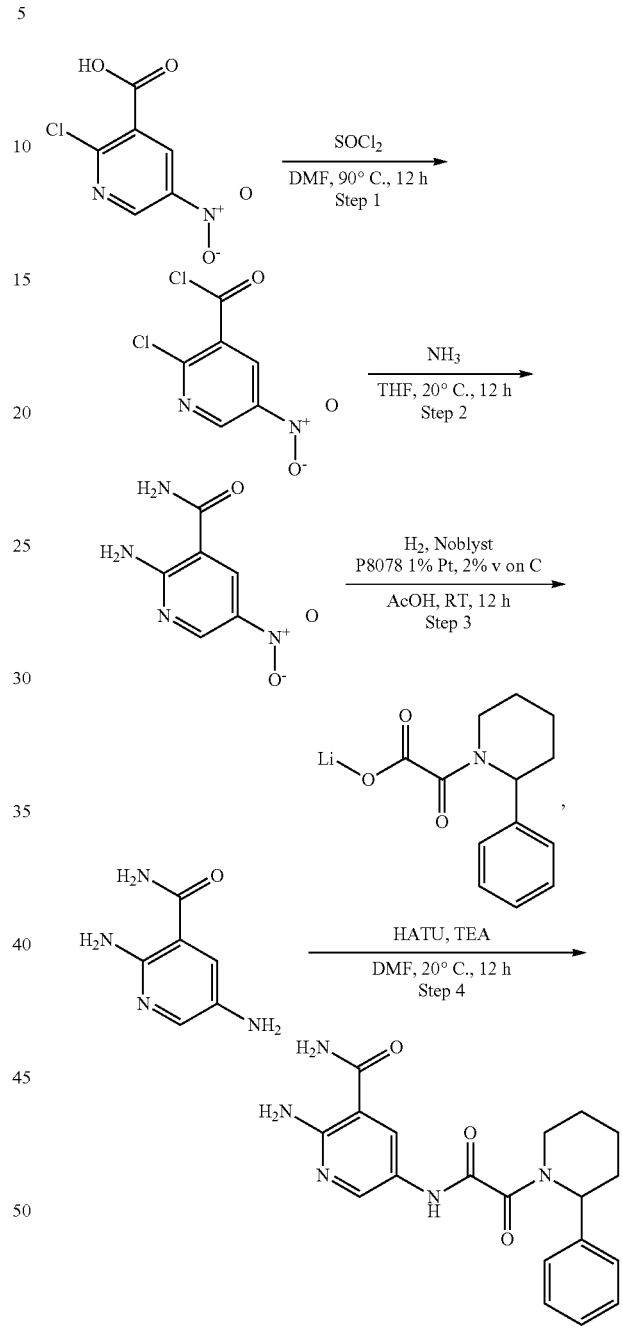

Compound 126

Step 1: The Synthesis of 2-chloro-5-nitro-pyridine-3-carbonyl chloride 2-chloro-5-nitro-pyridine-3-carboxylic acid (5.00 g, 24.69 mmol) was mixed with thionyl chloride (29.37 g, 246.85 mmol). 3 drops of DMF were added and the resulting mixture was heated at 90° C. with intensively stirring for 12 hr. The excess of thionyl chloride was removed in vacuo to obtain 2-chloro-5-nitro-pyridine-3-carbonyl chloride (5 g, 22.62 mmol, 91.65% yield) which was used in next step without purification.

$^1$H NMR (400 MHz, CDCl$_3$) δ 9.09 (s, 1H), 9.38 (s, 1H).

LCMS(ESI): [M+H]$^+$ m/z: calcd 219.9; found 221.0; Rt=0.431 min.

Step 2: The Synthesis of
2-amino-5-nitro-pyridine-3-carboxamide 2-chloro-5-nitro-pyridine-3-carbonyl chloride (5 g, 22.62 mmol) was dissolved in THF (100 mL). Ammonia (385.31 mg, 22.62 mmol) was passed through solution for 10 minutes and the resulting mixture was stirred at 20° C. for 12 hr. LCMS of aliquote showed 63% of desired product. The reaction mixture was evaporated to dryness. 50 ml of saturated aqueous solution of ammonia was added. The resulting mixture was stirred at 20° C. for another 12 hr. The obtained precipitate was filtered on, washed with water, and dried to obtain 2-amino-5-nitro-pyridine-3-carboxamide (2.25 g, crude), which was used in next step without purification.

$^1$H NMR (400 MHz, DMSO-d$_6$) δ 7.64 (m, 2H), 8.39 (m, 2H), 8.79 (s, 1H), 8.96 (s, 1H).

LCMS(ESI): [M+H]$^+$ m/z: calcd 182.0; found 183.0; Rt=0.643 min.

Step 3: The Synthesis of
2,5-Diaminopyridine-3-carboxamide

The solution of 2-amino-5-nitro-pyridine-3-carboxamide (1 g, 5.49 mmol) in AcOH (3 mL) was hydrogenated at 1 atm pressure using Noblyst P8078 1% Pt, 2% V on carbon (54.90 μmol) as catalyst for 12 hr. The resulting mixture was filtered and filtrate evaporated to obtain crude product (1.5 g) in acetate form with excess of acetic acid. 0.4 g of this material was re-dissolved in 6N HCl and evaporated to dryness to obtain 2,5-diaminopyridine-3-carboxamide (0.3 g, 1.33 mmol, 24.28% yield, 2HCl) which was used in next step without purification.

LCMS(ESI): [M+H]$^+$ m/z: calcd 152.1; found 153.2; Rt=0.169 min.

Step 4: The Synthesis of 2-amino-5-[[2-oxo-2-(2-phenyl-1-piperidyl)acetyl]amino]pyridine-3-carboxamide (EN-TG-3082

[2-oxo-2-(2-phenyl-1-piperidyl)acetyl]oxylithium (318.82 mg, 1.33 mmol) was mixed with HATU (557.48 mg, 1.47 mmol) and triethylamine (337.19 mg, 3.33 mmol, 464.44 μL) in DMF (5 mL). The resulting mixture was stirred at 20° C. for 10 min followed by the addition of 2,5-diaminopyridine-3-carboxamide (0.3 g, 1.33 mmol, 2HCl). The resulting mixture was stirred at 20° C. for 12 hr. The obtained solution was subjected to HPLC (16 Water-MeOH+NH$_3$; 20-55% Water-MeOH+NH$_3$ as a mobile phase; Waters SunFire C18 19*100 5 mkm column, Flow 12 ml/min) to obtain 2-amino-5-[[2-oxo-2-(2-phenyl-1-piperidyl)acetyl]amino]pyridine-3-carboxamide (0.0579 g, 157.59 μmol, 11.82% yield).

$^1$H NMR (400 MHz, DMSO-d$_6$) δ 1.52 (m, 4H), 1.90 (m, 1H), 2.99 (m, 1H), 3.40 (m, 1H), 3.75 (m, 1H), 5.46 (m, 1H), 7.02 (m, 2H), 7.31 (m, 3H), 7.40 (m, 3H), 7.99 (m, 1H), 8.09 (m, 1H), 8.18 (m, 1H), 10.68 (m, 1H).

LCMS(ESI): [M+H]$^+$ m/z: calcd 367.2; found 368.2; Rt=2.596 min.

Example 709. The Synthesis of N-(4-amino-5-methylpyridin-3-yl)-2-oxo-2-(2-phenylpiperidin-1-yl)acetamide (Compound 184)

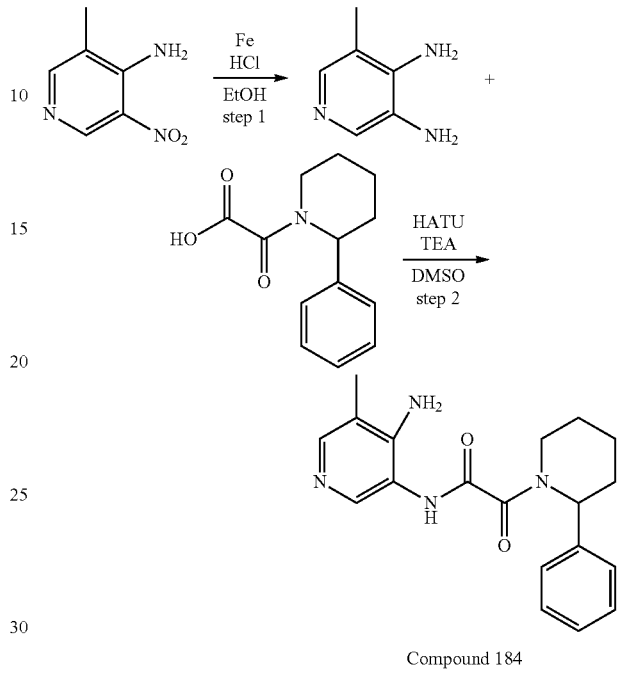

Compound 184

Step 1: Synthesis of 5-methylpyridine-3,4-Diamine 3-methyl-5-nitro-pyridin-4-amine (0.5 g, 3.27 mmol), powder of Fe (0.72 g, 12.89 mmol, 91.60 μL) and 5 ml HCl were mixed in ethanol (25 mL) and refluxed for 2 h. The ethanol was distilled. The resulting suspension was diluted with water and the pH was adjusted to 13 by addition of 2N NaOH. Extraction with ethyl acetate, drying of the combined organic phases of anhydrous sodium sulphate and evaporation of the solvent afforded 5-methylpyridine-3,4-diamine (90 mg, crude).

LCMS(ESI): [M]$^+$ m/z: calcd 123.3; found 124.2; Rt=0.225 min.

Step 2: Synthesis of N-(4-amino-5-methylpyridin-3-yl)-2-oxo-2-(2-phenylpiperidin-1-yl)acetamide 5-methylpyridine-3,4-diamine (90 mg, 365.39 μmol), 2-oxo-2-(2-phenyl-1-piperidyl)acetic acid (45.00 mg, 192.92 μmol), HATU (138.93 mg, 365.39 μmol) and TEA (36.97 mg, 365.39 μmol, 50.93 μL) were mixed in DMSO (1 mL). Solution in DMSO without isolation of needed compound was subjected to HPLC (column: SUNFIRE C18 100*19 mm, 5 microM and MeCN+FA as a mobile phase) to afford pure N-(4-amino-5-methyl-3-pyridyl)-2-oxo-2-(2-phenyl-1-piperidyl)acetamide (15.2 mg, 44.92 μmol, 12.29% yield).

$^1$H NMR (400 MHz, CDCl$_3$) δ (ppm) 1.66 (m, 5H), 2.02 (m, 1H), 2.14 (m, 3H), 2.42 (m, 1H), 2.90 (m, 1H), 4.16 (m, 1H), 5.64 (m, 1H), 6.35 (m, 2H), 7.35 (m, 4H), 7.78 (m, 1H), 8.39 (m, 1H), 8.58 (s, 1H).

LCMS(ESI): [M]$^+$ m/z: calcd 338.4; found 339.2; Rt=2.527 min.

The Synthesis of N-(2-amino-5-methylpyridin-3-yl)-2-oxo-2-(2-phenylpiperidin-1-yl)acetamide (Compound 160

TEA (1.23 g, 12.18 mmol, 1.70 mL) was added to a stirred mixture of 5-methylpyridine-2,3-diamine (150 mg, 1.22 mmol), 2-oxo-2-(2-phenyl-1-piperidyl)acetic acid (284.11 mg, 1.22 mmol) and HATU (509.42 mg, 1.34 mmol) in DMF (5 mL). The reaction mixture was stirred at 25° C. for 2 hr, then directly purified by reverse phase HPLC (column: YMC-Actus Triart C18 100*20 mml.D. S-5 um) using 0-5 min 30-75% water-methanol ($NH_3$ 0.1%) to afford N-(2-amino-5-methyl-3-pyridyl)-2-oxo-2-(2-phenyl-1-piperidyl)acetamide (156 mg, 460.99 µmol, 37.85% yield) as brown solid.

$^1$H NMR (500 MHz, DMSO-$d_6$) δ (ppm) 1.53 (m, 4H), 1.89 (m, 1H), 2.11 (m, 3H), 3.00 (m, 1H), 3.99 (m, 1H), 5.58 (m, 3H), 7.36 (m, 6H), 7.62 (m, 2H), 10.10 (m, 1H).

LCMS(ESI): [M]$^+$ m/z: calcd 338.4; found 339.2; Rt=2.530 min.

Example 710. He Synthesis of N-(6-amino-5-methyl-3-pyridyl)-2-[(2R,5S)-2-[4-(difluoromethyl)phenyl]-5-methyl-1-piperidyl]-2-oxo-acetamide (Compound 410) and N-(6-amino-5-methyl-3-pyridyl)-2-[(2S,5R)-2-[4-(difluoromethyl)phenyl]-5-methyl-1-piperidyl]-2-oxo-acetamide (Compound 419)

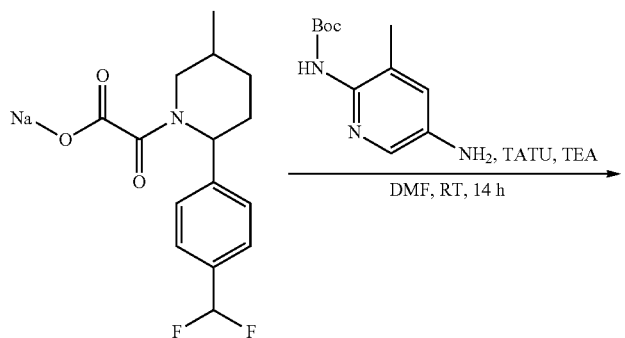

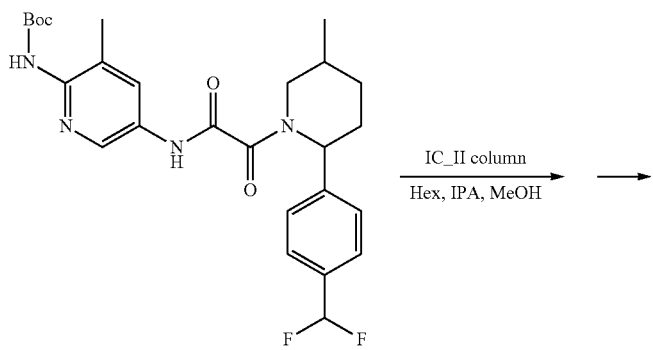

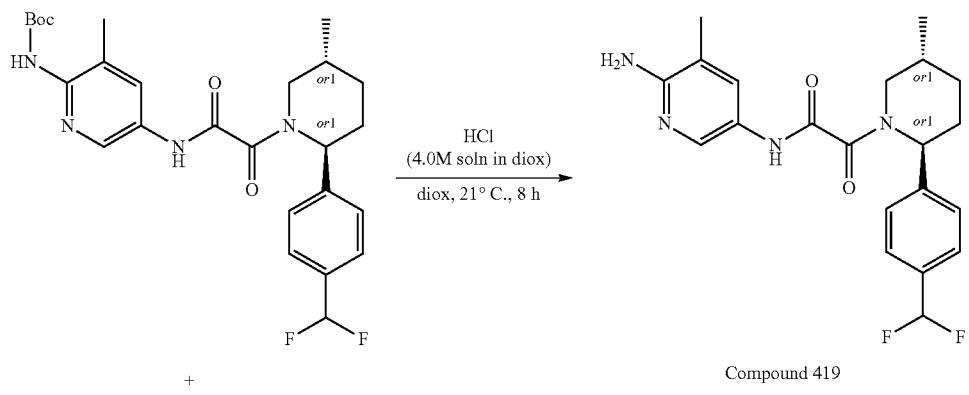

Compound 419

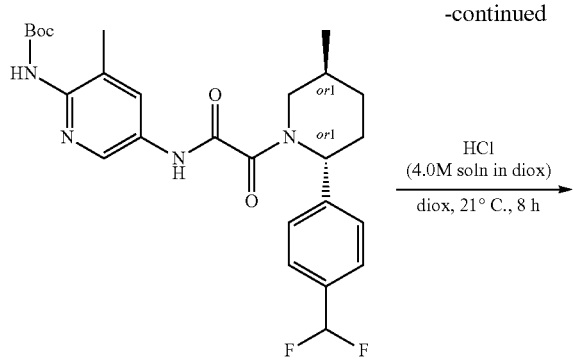
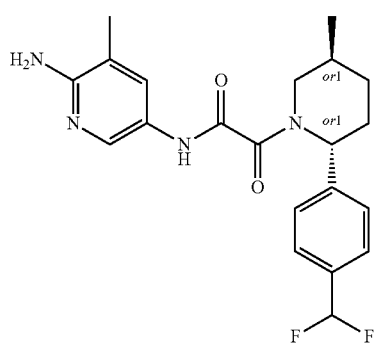

Compound 410

Step 1: The Synthesis of tert-butyl N-[5-[[2-[2-[4-(difluoromethyl)phenyl]-5-methyl-1-piperidyl]-2-oxo-acetyl]amino]-3-methyl-2-pyridyl]carbamate

[2-[2-[4-(difluoromethyl)phenyl]-5-methyl-1-piperidyl]-2-oxo-acetyl]oxysodium (0.45 g, 1.41 mmol), TATU (544.72 mg, 1.69 mmol) (prepared as above) and triethylamine (142.62 mg, 1.41 mmol, 196.45 µL) were mixed in dry DMF (5 mL) at 21° C. and the resulting mixture was stirred for 15 min. tert-butyl N-(5-amino-3-methyl-2-pyridyl)carbamate (314.68 mg, 1.41 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (50-75% 2-7 min; water-acetonitrile 30 ml/min; loading pump: acetonitrile 4 ml/min; column SunFire 19*100 mm). tert-butyl N-[5-[[2-[2-[4-(difluoromethyl)phenyl]-5-methyl-1-piperidyl]-2-oxo-acetyl]amino]-3-methyl-2-pyridyl]carbamate (0.44 g, 875.53 µmol, 62.12% yield) was obtained as a pale-yellow gum.

$^1$H NMR (400 MHz, CDCl$_3$) δ 1.07 (d, 3H), 1.48 (s, 9H), 1.97 (m, 4H), 2.28 (m, 5H), 3.20 (m, 1H), 4.80 (m, 1H), 5.77 (m, 2H), 7.36 (m, 2H), 7.50 (m, 2H), 8.02 (s, 1H), 8.32 (m, 1H), 9.33 (m, 1H).

LCMS(ESI): [M+H]$^+$ m/z: calcd 502.2; found 503.2; Rt=1.341 min.

Step 2: The Synthesis of tert-butyl N-[5-[[2-[(2R,5S)-2-[4-(difluoromethyl)phenyl]-5-methyl-1-piperidyl]-2-oxo-acetyl]amino]-3-methyl-2-pyridyl]carbamate and Tert-butyl N-[5-[[2-[(2S,5R)-2-[4-(difluoromethyl)phenyl]-5-methyl-1-piperidyl]-2-oxo-acetyl]amino]-3-methyl-2-pyridyl]carbamate Chiral resolution 1C—II (250*20, 5 mkm), Hexane-IPA-MeOH, 60-20-20, 12 ml/min Isomer 1—RT of tert-butyl N-[5-[[2-[(2R,5S)-2-[4-(difluoromethyl)phenyl]-5-methyl-1-piperidyl]-2-oxo-acetyl]amino]-3-methyl-2-pyridyl]carbamate (83.83 mg, 166.81 µmol, 20.55% yield) 18.493 (IC, Hexane-IPA-MeOH, 50-25-25, 0.6 ml/min).

Isomer 2—RT of tert-butyl N-[5-[[2-[(2R,5S)-2-[4-(difluoromethyl)phenyl]-5-methyl-1-piperidyl]-2-oxo-acetyl]amino]-3-methyl-2-pyridyl]carbamate (83.83 mg, 166.81 µmol, 20.55% yield) 14.346 min (IC, Hexane-IPA-MeOH, 50-25-25, 0.6 ml/min).

Isomer 1:
LCMS(ESI): [M+H]$^+$ m/z: calcd 502.2; found 503.2; Rt=5.806 min.
Isomer 2:
LCMS(ESI): [M+H]$^+$ m/z: calcd 502.2; found 503.2; Rt=5.806 min.

Step 3: The Synthesis of N-(6-amino-5-methyl-3-pyridyl)-2-[(2R,5S)-2-[4-(difluoromethyl)phenyl]-5-methyl-1-piperidyl]-2-oxo-acetamide (Compound 419

To a solution of tert-butyl N-[5-[[2-[(2R,5S)-2-[4-(difluoromethyl)phenyl]-5-methyl-1-piperidyl]-2-oxo-acetyl]amino]-3-methyl-2-pyridyl]carbamate (83.83 mg, 166.81 µmol) in dioxane (2 mL) was added Hydrogen chloride solution 4.0 M in dioxane (30.41 mg, 834.04 µmol, 38.01 µL) at 21° C. The resulting mixture was left to stir for 8 hr. The resulting mixture was evaporated to dryness and subjected to HPLC (C18, H$_2$O-MeCN, 34-50% MeCN, 30 ml/min). N-(6-amino-5-methyl-3-pyridyl)-2-[(2R,5S)-2-[4-(difluoromethyl)phenyl]-5-methyl-1-piperidyl]-2-oxo-acetamide (24.32 mg, 60.43 µmol, 36.23% yield) was obtained as a white solid.

$^1$H NMR (500 MHz, DMSO-d$_6$) δ 0.99-1.05 (m, 3H), 1.27-1.44 (m, 1H), 1.57-1.70 (m, 1H), 1.81-1.93 (m, 1H), 1.97-2.10 (m, 4H), 2.17-2.28 (m, 1H), 2.71-3.17 (m, 1H), 3.49-4.14 (m, 1H), 5.22-5.67 (m, 3H), 6.92-7.17 (m, 1H), 7.44-7.54 (m, 3H), 7.57-7.66 (m, 2H), 7.94-8.11 (m, 1H), 10.45-10.65 (m, 1H).

LCMS(ESI): [M+H]$^+$ m/z: calcd 402.2; found 403.0; Rt=2.740 min.

Step 4: The Synthesis of N-(6-amino-5-methyl-3-pyridyl)-2-[(2S,5R)-2-[4-(difluoromethyl)phenyl]-5-methyl-1-piperidyl]-2-oxo-acetamide (Compound 410

To a solution of tert-butyl N-[5-[[2-[(2S,5R)-2-[4-(difluoromethyl)phenyl]-5-methyl-1-piperidyl]-2-oxo-acetyl]amino]-3-methyl-2-pyridyl]carbamate (87.01 mg, 173.14 µmol) in dioxane (2 mL) was added Hydrogen chloride solution 4.0 M in dioxane (31.56 mg, 865.68 µmol, 39.45 µL) at 21° C. The resulting mixture was left to stir for 8 hr. The resulting mixture was evaporated to dryness and subjected to HPLC (50-100% 0.5-6 min; water-MeOH+NH$_3$ 30 ml/min; loading pump MeOH+NH$_3$ 4 ml/min; column xbridge 20*100 mm; and then C18, H$_2$O-MeCN, 34-50% MeCN, 30 ml/min). N-(6-amino-5-methyl-3-pyridyl)-2-[(2S,5R)-2-[4-(difluoromethyl)phenyl]-5-methyl-1-piperidyl]-2-oxo-acetamide (33.34 mg, 82.85 μmol, 47.85% yield) was obtained as a white solid.

$^1$H NMR (500 MHz, DMSO-d$_6$) δ 1.00-1.11 (m, 3H), 1.30-1.41 (m, 1H), 1.57-1.76 (m, 1H), 1.83-1.95 (m, 1H), 1.97-2.12 (m, 4H), 2.13-2.30 (m, 1H), 2.72-3.23 (m, 1H), 3.48-4.14 (m, 1H), 5.20-5.67 (m, 3H), 6.88-7.15 (m, 1H), 7.42-7.53 (m, 3H), 7.56-7.66 (m, 2H), 7.85-8.12 (m, 1H), 10.47-10.65 (m, 1H).

LCMS(ESI): [M+H]$^+$ m/z: calcd 402.2; found 403.0; Rt=2.753 min.

Example 711. The Synthesis of N-(6-amino-5-methyl-3-pyridyl)-2-[(2R,5S)-2-(3-chlorophenyl)-5-methyl-1-piperidyl]-2-oxo-acetamide (Compound 283) and Synthesis of N-(6-amino-5-methyl-3-pyridyl)-2-[(2S,5R)-2-(3-chlorophenyl)-5-methyl-1-piperidyl]-2-oxo-acetamide Compound 284

Step 2: Synthesis of methyl 2-[2-(3-chlorophenyl)-5-methyl-1-piperidyl]-2-oxo-acetate To a solution of 2-(3-chlorophenyl)-5-methyl-1-piperidine (0.5 g, 2.38 mmol) and triethylamine (265.38 mg, 2.62 mmol, 365.54 d) in DCM (25 mL) was added methyl 2-choro-2-oxo-acetate (292.08 mg, 2.38 mmol) at 0° C. After stirring at rt for 1 hr the resulting mixture were filtered and evaporated to dryness to give methyl 2-[2-(3-chlorophenyl)-5-methyl-1-piperidyl]-2-oxo-acetate (0.9 g, crude) as a yellow solid, which was used in the next step without further purification.

$^1$H NMR (400 MHz, CDCl$_3$) δ 0.789-1.07 (m, 3H), 1.37 (m, 2H), 1.56-2.00 (m, 2H), 2.16 (m, 1H), 2.84-3.08 (m, 1H), 3.20 (dd, 1H), 3.79-3.88 (m, 3H), 4.83 (s, 0.5H), 6.71 (s, 0.5H), 7.24 (in, 4H)

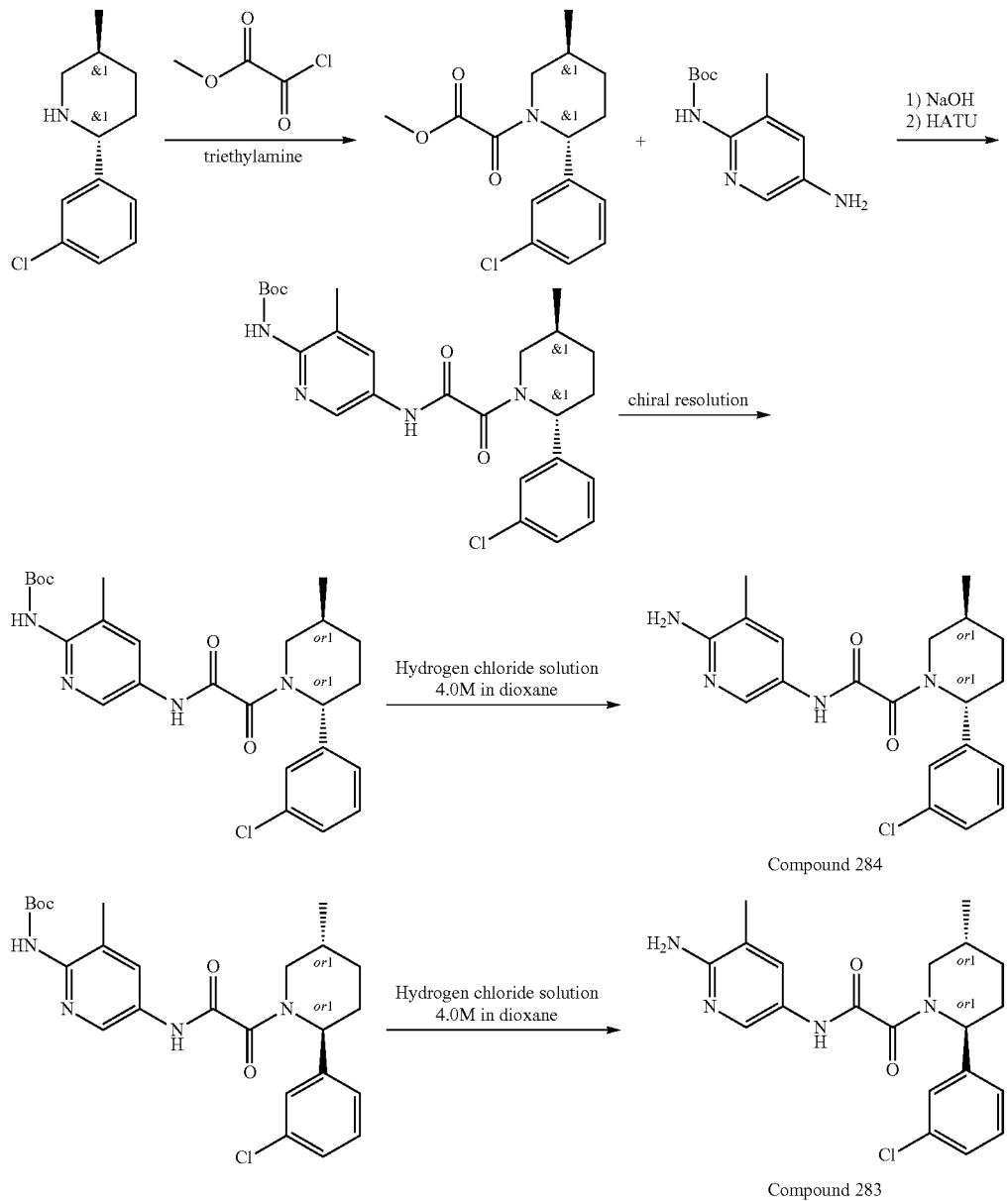

Compound 284

Compound 283

LCMS(ESI): [M+H]⁺ m/z: calcd 295.2; found 296.2; Rt=1.443 min.

Step 2: Synthesis of tert-butyl N-[5-[[2-[2-(3-chlorophenyl)-5-methyl-1-piperidyl]-2-oxo-acetyl]amino]-3-methyl-2-pyridyl]carbamate To a solution of methyl 2-[2-(3-chlorophenyl)-5-methyl-1-piperidyl]-2-oxo-acetate (0.9 g, 3.04 mmol) in MeOH (12.50 mL) was added hydroxysodium (121.71 mg, 3.04 mmol, 57.14 µL) and the resulting mixture was stirred for 1 hr. Then, the solvent was evaporated and the residue was reevaporated with EtOH. After that, solids were dissolved in DMIF and HATU (1.16 g, 3.04 mmol) was added followed by tert-butyl N-(5-amino-3-methyl-2-pyridyl)carbamate (679.41 mg, 3.04 mmol) and the resulting mixture was stirred for 12 hr. The resulting mixture was poured into water, extracted 3 times with EtOAc, combined organics were washed with water, brine and evaporated. The residue was subjected to HPLC (50-75% 2-7 min; water-acetonitrile; 30 ml/min; loading pump 4 ml/min; acetonitrile; column SunFire 19*100 mm). Two fraction of tert-butyl N-[5-[[2-[2-(3-chlorophenyl)-5-methyl-1-piperidyl]-2-oxo-acetyl]amino]-3-methyl-2-pyridyl]carbamate (495.2 mg, 1.02 mmol, 33.42% yield) were obtained: 131 mg (80.66% by LCMS, single diastereomer) and 364.2 mg (94.21% by LCMS, ~4:1 mixture of diastereomers).

¹H NMR (400 MHz, CDCl₃) δ 0.85-1.07 (m, 3H), 1.36 (m, 1H), 1.48 (s, 9H), 1.85 (m, 1H), 1.99 (m, 1H), 2.15 (m, 1H), 2.29 (s, 3H), 2.96-3.33 (m, 1H), 3.76 (s, 1H), 4.24-4.80 (m, 1H), 5.73-6.41 (m, 1H), 6.80 (m, 1H), 7.15-7.25 (m, 4H), 8.03 (s, 1H), 8.34-8.36 (m, 1H), 9.41 (m, 1H).

LCMS(ESI): [M+H]⁺ m/z: calcd 486.2; found 487.2; Rt=3.523 min.

Step 3: Synthesis of tert-butyl N-[5-[[2-[(2S,5R)-2-(3-chlorophenyl)-5-methyl-1-piperidyl]-2-oxo-acetyl]amino]-3-methyl-2-pyridyl]carbamate and Tert-butyl N-[5-[[2-[(2R,5S)-2-(3-chlorophenyl)-5-methyl-1-piperidyl]-2-oxo-acetyl]amino]-3-methyl-2-pyridyl]carbamate The racemate was separated in the following conditions: Column: IC-II (250*20, 5 mkm), Mobile phase: Hexane-IPA-MeOH, 60-20-20; Flow rate: 14 ml/min. 24° C., Wavelength: 205 nm, 215 nm RT of tert-butyl N-[5-[[2-[(2S,5R)-2-(3-chlorophenyl)-5-methyl-1-piperidyl]-2-oxo-acetyl]amino]-3-methyl-2-pyridyl]carbamate (133.55 mg, 274.24 µmol, 36.67% yield) =27.9 min and RT of tert-butyl N-[5-[[2-[(2R,5S)-2-(3-chlorophenyl)-5-methyl-1-piperidyl]-2-oxo-acetyl]amino]-3-methyl-2-pyridyl]carbamate (0.14 g, 287.48 µmol, 38.44% yield)=20.6 min.

Step 4: Synthesis N-(6-amino-5-methyl-3-pyridyl)-2-[(2R,5S)-2-(3-chlorophenyl)-5-methyl-1-piperidyl]-2-oxo-acetamide (Compound 283

To a solution of tert-butyl N-[5-[[2-[(2R,5S)-2-(3-chlorophenyl)-5-methyl-1-piperidyl]-2-oxo-acetyl]amino]-3-methyl-2-pyridyl]carbamate (133.55 mg, 274.24 µmol) in dioxane (2 mL) was added Hydrogen chloride solution 4.0 M in dioxane (49.99 mg, 1.37 mmol, 62.49 µL) at 21° C. The resulting mixture was left to stir for 1 hr. The resulting mixture was evaporated to dryness and subjected to HPLC (50-100% 2-7 min water-acetonitrile; flow 30 ml/min (loading pump 4 ml/min; MeOH+NH₃); column YMC-actus triat 100×19 mm 5 um). N-(6-amino-5-methyl-3-pyridyl)-2-[(2R,5S)-2-(3-chlorophenyl)-5-methyl-1-piperidyl]-2-oxo-acetamide (56.8 mg, 146.82 µmol, 53.54% yield) was obtained as a white solid (in two fraction).

¹H NMR (600 MHz, DMSO-d₆) δ 0.94-1.02 (m, 3H), 1.25-1.38 (m, 1H), 1.56-1.66 (m, 1H), 1.81-1.91 (m, 1H), 1.91-2.06 (m, 4H), 2.14-2.24 (m, 1H), 2.70-3.22 (m, 1H), 3.33-4.05 (m, 1H), 5.09-5.56 (m, 1H), 5.57-5.64 (m, 2H), 7.21-7.37 (m, 3H), 7.37-7.42 (m, 1H), 7.42-7.50 (m, 1H), 7.93-8.04 (m, 1H), 10.45-10.58 (m, 1H).

LCMS(ESI): [M+H]⁺ m/z: calcd 386.2; found 387.2; Rt=2.528 min.

Step 5: Synthesis of N-(6-amino-5-methyl-3-pyridyl)-2-[(2S,5R)-2-(3-chlorophenyl)-5-methyl-1-piperidyl]-2-oxo-acetamide (Compound 284

To a solution of tert-butyl N-[5-[[2-[(2S,5R)-2-(3-chlorophenyl)-5-methyl-1-piperidyl]-2-oxo-acetyl]amino]-3-methyl-2-pyridyl]carbamate (140.00 mg, 287.48 µmol) in dioxane (2 mL) was added Hydrogen chloride solution 4.0 M in dioxane (52.41 mg, 1.44 mmol, 65.51 µL) at 21° C. The resulting mixture was left to stir for 1 hr. The resulting mixture was evaporated to dryness and subjected to HPLC (40-65% 2-7 min water-acetonitrile; flow 30 ml/min (loading pump 4 ml/min; acetonitrile); column SunFire C18 100×19 mm 5 um). N-(6-amino-5-methyl-3-pyridyl)-2-[(2S,5R)-2-(3-chlorophenyl)-5-methyl-1-piperidyl]-2-oxo-acetamide (40.7 mg, 105.20 µmol, 36.59% yield) was obtained as a white solid (in two fraction).

¹H NMR (600 MHz, DMSO-d₆) δ 0.95-1.04 (m, 3H), 1.25-1.38 (m, 1H), 1.56-1.66 (m, 1H), 1.79-1.92 (m, 1H), 1.94-2.11 (m, 4H), 2.13-2.26 (m, 1H), 2.70-3.22 (m, 1H), 3.43-4.05 (m, 1H), 5.11-5.56 (m, 1H), 5.56-5.66 (m, 2H), 7.18-7.42 (m, 4H), 7.42-7.50 (m, 1H), 7.91-8.04 (m, 1H), 10.47-10.58 (m, 1H).

LCMS(ESI): [M+H]⁺ m/z: calcd 386.2; found 387.2; Rt=1.615 min.

Example 712. The Synthesis of 5-[[2-[(2S,5R)-2-[4-(difluoromethyl)phenyl]-5-methyl-1-piperidyl]-2-oxo-acetyl]amino]pyridine-3-carboxamide (Compound 358) and 5-[[2-[(2R,5S)-2-[4-(difluoromethyl)phenyl]-5-methyl-1-piperidyl]-2-oxo-acetyl]amino]pyridine-3-carboxamide (Compound 359)

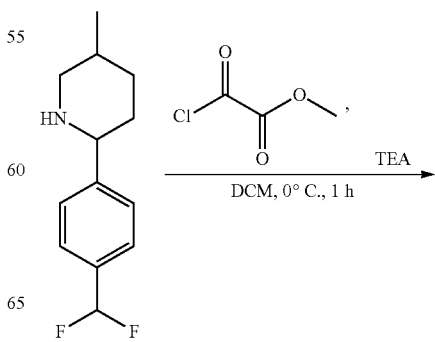

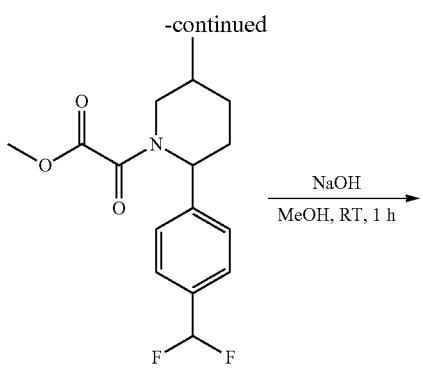

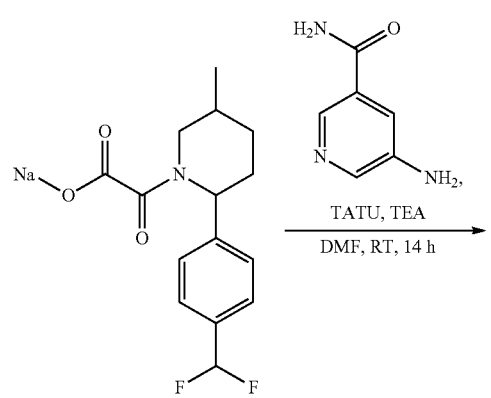

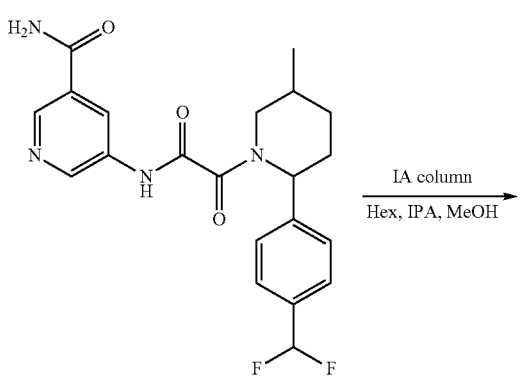

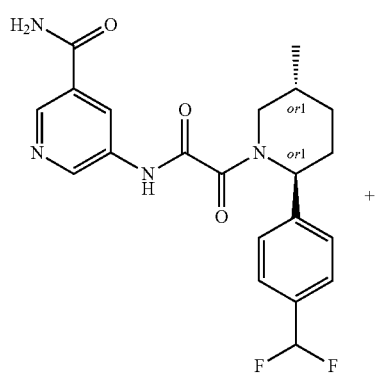

Compound 358

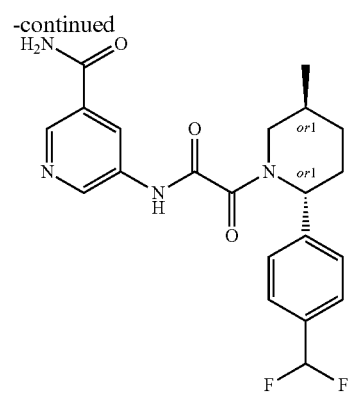

Compound 359

Step 1: The Synthesis of methyl 2-[2-[4-(difluoromethyl)phenyl]-5-methyl-1-piperidyl]-2-oxo-acetate To a solution of 2-[4-(difluoromethyl)phenyl]-5-methyl-piperidine (0.63 g, 2.80 mmol) and triethylamine (339.58 mg, 3.36 mmol, 467.74 µL) in DCM (15 mL) was added methyl 2-chloro-2-oxo-acetate (376.86 mg, 3.08 mmol) at 0° C. After stirring at rt for 1 hr, the resulting mixture were filtered and evaporated to dryness to give methyl 2-[2-[4-(difluoromethyl)phenyl]-5-methyl-1-piperidyl]-2-oxo-acetate (0.88 g, crude) as a yellow solid, which was used in the next step without further purification.

$^1$H NMR (400 MHz, CDCl$_3$) δ 1.08 (d, 3H), 1.44 (m, 2H), 1.80 (m, 2H), 2.17 (m, 2H), 3.20 (m, 1H), 3.89 (s, 3H), 5.78 (m, 2H), 7.34 (m, 2H), 7.51 (m, 2H).

LCMS(ESI): [M+H]$^+$ m/z: calcd 311.2; found 312.0; Rt=1.426 min.

Step 2: The Synthesis of [2-[2-[4-(difluoromethyl)phenyl]-5-methyl-1-piperidyl]-2-oxo-acetyl]oxysodium To a solution of methyl 2-[2-[4-(difluoromethyl)phenyl]-5-methyl-1-piperidyl]-2-oxo-acetate (0.88 g, 2.83 mmol) in MeOH (10 mL) was added sodium hydroxide (124.36 mg, 3.11 mmol, 58.39 µL) and the resulting mixture was left to stir at rt for hr. Then the resulting mixture was evaporated to dryness to give [2-[2-[4-(difluoromethyl)phenyl]-5-methyl-1-piperidyl]-2-oxo-acetyl]oxysodium (0.9 g, 2.82 mmol, 99.72% yield) which was used as a sodium salt in the next step.

LCMS(ESI): [M+H]$^+$ m/z: calcd 297.1; found 298.2; Rt=1.537 min.

Step 3: The Synthesis of 5-[[2-[2-[4-(difluoromethyl)phenyl]-5-methyl-1-piperidyl]-2-oxo-acetyl]amino]pyridine-3-carboxamide

[2-[2-[4-(difluoromethyl)phenyl]-5-methyl-1-piperidyl]-2-oxo-acetyl]oxysodium (0.45 g, 1.41 mmol), TATU (544.72 mg, 1.69 mmol) and triethylamine (142.62 mg, 1.41 mmol, 196.45 µL) were mixed in dry DMF (5 mL) at 21° C. and the resulting mixture was stirred for 1 hr. 5-aminopyridine-3-carboxamide (193.29 mg, 1.41 mmol) was added thereto and the resulting mixture was stirred at 21° C. overnight. The resulting mixture was poured into water, extracted 3 times with EtOAc, combined organics were washed with water, brine and evaporated. The residue was subjected to HPLC (30-65% 2-7 min; water-MeOH (+NH₃); 30 ml/min; loading pump 4 ml/min; acetonitrile; column xbridge 19*100 mm). 5-[[2-[2-[4-(difluoromethyl)phenyl]-5-methyl-1-piperidyl]-2-oxo-acetyl]amino]pyridine-3-carboxamide (156.2 mg, 375.10 μmol, 26.61% yield) was obtained as a yellow gum.

¹H NMR (400 MHz, CDCl₃) δ 0.95 (m, 3H), 1.39 (m, 1H), 1.77 (m, 4H), 2.20 (m, 2H), 3.37 (m, 1H), 4.30 (m, 1H), 5.77 (m, 2H), 7.37 (m, 2H), 7.49 (m, 2H), 8.60 (m, 1H), 8.81 (s, 1H), 9.01 (m, 1H), 9.87 (s, 1H).

LCMS(ESI): [M+H]⁺ m/z: calcd 416.2; found 417.2; Rt=1.136 min.

Step 4: The Synthesis of 5-[[2-[(2S,5R)-2-[4-(difluoromethyl)phenyl]-5-methyl-1-piperidyl]-2-oxo-acetyl]amino]pyridine-3-carboxamide (Compound 358) and 5-[[2-[(2R,5S)-2-[4-(difluoromethyl)phenyl]-5-methyl-1-piperidyl]-2-oxo-acetyl]amino]pyridine-3-carboxamide (Compound 359

Chiral resolution: IA (250*20, 5 mkm), Hexane-IPA-MeOH, 50-25-25, 12 ml/min

RT of 5-[[2-[(2S,5R)-2-[4-(difluoromethyl)phenyl]-5-methyl-1-piperidyl]-2-oxo-acetyl]amino]pyridine-3-carboxamide (62.76 mg, 150.71 μmol, 40.18% yield) 24.9482 min (IA, Hexane-IPA-MeOH, 50-25-25, 0.6 ml/min)

RT of 5-[[2-[(2R,5S)-2-[4-(difluoromethyl)phenyl]-5-methyl-1-piperidyl]-2-oxo-acetyl]amino]pyridine-3-carboxamide (65.89 mg, 158.23 μmol, 42.18% yield) 33.4822 min (IA, Hexane-IPA-MeOH, 50-25-25, 0.6 ml/min)

Compound 358: ¹H NMR (600 MHz, DMSO-d₆) δ 1.00-1.04 (m, 3H), 1.28-1.38 (m, 1H), 1.60-1.68 (m, 1H), 1.82-1.95 (m, 1H), 2.05-2.18 (m, 1H), 2.19-2.30 (m, 1H), 2.75-3.24 (m, 1H), 3.38-4.11 (m, 1H), 5.19-5.67 (m, 1H), 6.90-7.12 (m, 1H), 7.43-7.51 (m, 2H), 7.55-7.65 (m, 3H), 8.09-8.20 (m, 1H), 8.41-8.52 (m, 1H), 8.71-8.80 (m, 1H), 8.81-8.93 (m, 1H), 11.13-11.39 (m, 1H).

LCMS(ESI): [M+H]⁺ m/z: calcd 416.2; found 417.2; Rt=3.134 min.

Compound 359: ¹H NMR (600 MHz, DMSO-d₆) δ 1.00-1.04 (m, 3H), 1.28-1.38 (m, 1H), 1.60-1.68 (m, 1H), 1.82-1.95 (m, 1H), 2.05-2.18 (m, 1H), 2.19-2.30 (m, 1H), 2.75-3.24 (m, 1H), 3.38-4.11 (m, 1H), 5.19-5.67 (m, 1H), 6.90-7.12 (m, 1H), 7.43-7.51 (m, 2H), 7.55-7.65 (m, 3H), 8.09-8.20 (m, 1H), 8.41-8.52 (m, 1H), 8.71-8.80 (m, 1H), 8.81-8.93 (m, 1H), 11.13-11.39 (m, 1H).

LCMS(ESI): [M+H]⁺ m/z: calcd 416.2; found 417.2; Rt=3.135 min.

Example 713. The Synthesis of 4-amino-5-[[2-oxo-2-(2-phenyl-1-piperidyl)acetyl]amino]pyridine-3-carboxamide (Compound 119)

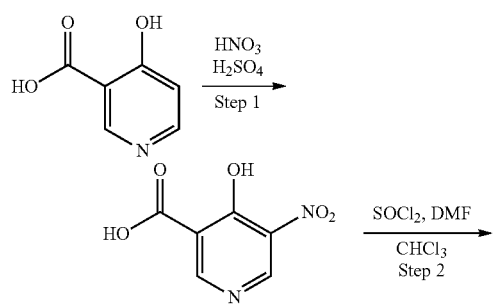

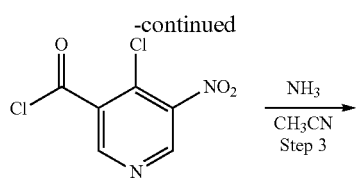

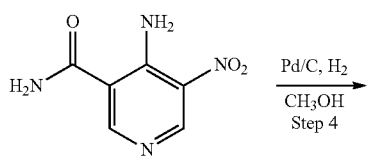

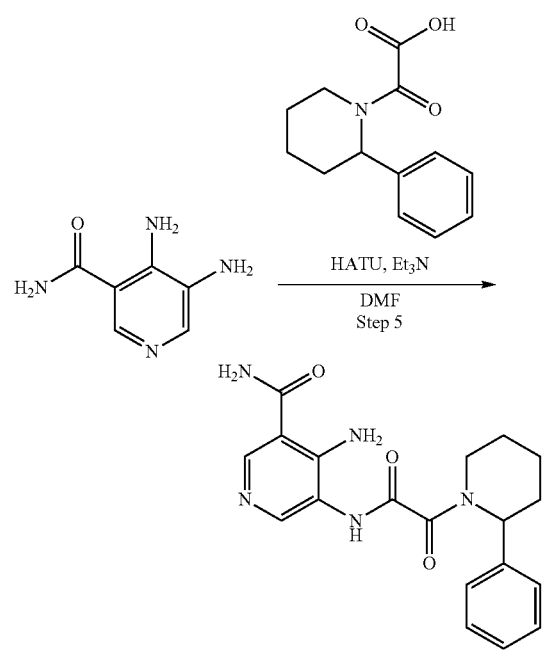

Compound 119

Step 1: Synthesis of 4-hydroxy-5-nitro-pyridine-3-carboxylic acid

Nitric acid (18.36 g, 291.37 mmol, 12 mL) was added dropwise to a stirred solution of 4-hydroxypyridine-3-carboxylic acid (6 g, 43.13 mmol) in sulfuric acid (50 mL) at 0° C. The resulting mixture was stirred at 100° C. for 24 hours. After 24 hours, the reaction mixture was allowed to cool and poured into crushed ice (500 g). The precipitated solid was filtered, washed with water (5×20 mL) and dried in vacuo to obtain 4-hydroxy-5-nitro-pyridine-3-carboxylic acid (4.90 g, 26.62 mmol, 61.71% yield) as a white solid. The crude product was used directly in the next step.

LCMS(ESI): [M−H]⁻ m/z: calcd 184.0; found 183.0; Rt=0.508 min.

Step 2: Synthesis of 4-chloro-5-nitro-pyridine-3-carbonyl chloride

To a stirred suspension of 4-hydroxy-5-nitro-pyridine-3-carboxylic acid (4.90 g, 26.62 mmol) and dimethyl forma mide (194.54 mg, 2.66 mmol, 206.08 µL) in chloroform (100 mL) was added Thionyl chloride (31.66 g, 266.15 mmol). The resulting reaction mixture was stirred at 70° C. for 24 hours. The resulting solution was then concentrated under reduced pressure to obtain crude product 4-chloro-5-nitro-pyridine-3-carbonyl chloride (5.80 g, 26.24 mmol, 98.61% yield) as a light-yellow oil, which was used directly in the next step.

$^1$H NMR (CDCl$_3$, 400 MHz): δ (ppm) 9.17 (s, 1H), 9.33 (s, 1H).

Step 3: Synthesis of 4-amino-5-nitro-pyridine-3-carboxamide

Gaseous ammonia was bubbled through the solution of 4-chloro-5-nitro-pyridine-3-carbonyl chloride (5.80 g, 26.24 mmol) in acetonitrile (100 mL) at 0° C. The color of reaction mixture was immediately turned from colorless to yellow. The cooling bath was removed and ammonia was further bubbled at 25° C. for 1 hour. The precipitated solid was filtered, washed with acetonitrile (2×20 mL) and water (2×20 mL), and dried in vacuo to afford 4-amino-5-nitro-pyridine-3-carboxamide (3.80 g, 20.86 mmol, 79.50% yield) as a yellow solid.

LCMS(ESI): [M+H]$^+$ m/z: calcd 182.0; found 183.0; Rt=0.499 min.

Step 4: Synthesis of 4,5-Diaminopyridine-3-carboxamide

A solution of 4-amino-5-nitro-pyridine-3-carboxamide (500 mg, 2.75 mmol) in methanol (20 mL) was hydrogenated over Palladium, 10% on carbon (200 mg, 2.75 mmol) under hydrogen atmosphere at 25° C. for 12 hours. After 12 hours, the catalyst was filtered and the filter cake was washed with methanol (2×20 mL). The filtrate was concentrated under reduced pressure to obtain 4,5-diaminopyridine-3-carboxamide (350 mg, 2.30 mmol, 83.79% yield) as a white solid.

$^1$H NMR (DMSO-d$_6$, 400 MHz): δ (ppm) 4.71 (s, 2H), 6.80 (s, 2H), 7.16 (s, 1H), 7.66 (s, 1H), 7.80 (s, 1H), 8.05 (d, 1H).

Step 5: Synthesis of 4-amino-5-[[2-oxo-2-(2-phenyl-1-piperidyl)acetyl]amino]pyridine-3-carboxamide (Compound 119

To a stirred mixture of 4,5-diaminopyridine-3-carboxamide (200 mg, 1.31 mmol), 2-oxo-2-(2-phenyl-1-piperidyl) acetic acid (306.61 mg, 1.31 mmol) and HATU (549.78 mg, 1.45 mmol) in DMF (10 mL) was added triethyl amine (1.33 g, 13.14 mmol, 1.83 mL). The resulting reaction mixture was stirred at 25° C. for 2 hours. After 2 hours, the reaction mixture was concentrated under reduced pressure and the residue was purified by reverse phase HPLC (Eluent: 25-70%, water-methanol (0.1% NH$_3$); column: SunFire C18 100*19 mm, 5 um) to afford 4-amino-5-[[2-oxo-2-(2-phenyl-1-piperidyl)acetyl]amino]pyridine-3-carboxamide (Compound 119, 26 mg, 70.77 µmol, 5.38% yield) as an off-white solid.

LCMS(ESI): [M+H]$^+$ m/z: calcd 367.2; found 368.4; Rt=2.198 min.

Example 714. The Synthesis of 5-[[2-[(2R,4S)-4-acetamido-2-phenyl-1-piperidyl]-2-oxo-acetyl]amino]pyridine-3-carboxamide (Compound 745)

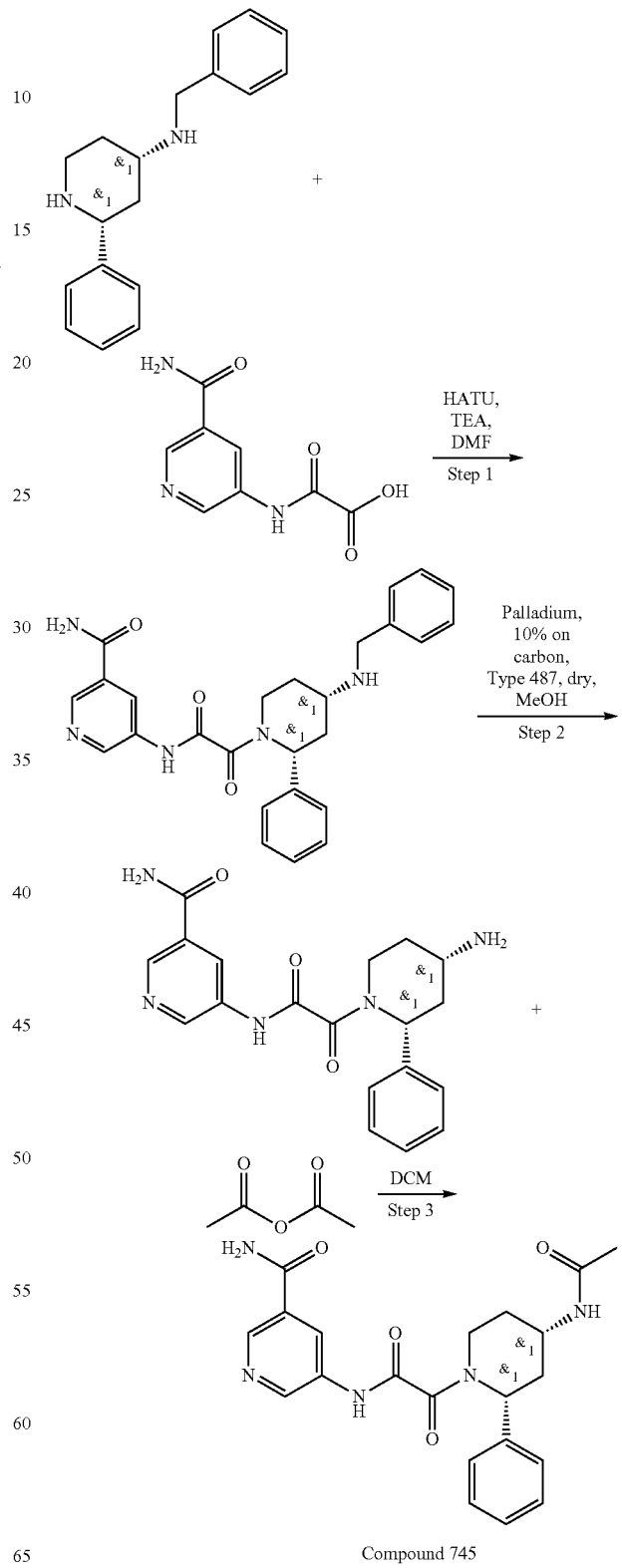

Compound 745

Step 1: Synthesis of 5-[[2-[(2R,4S)-4-(Benzylamino)-2-phenyl-1-piperidyl]-2-oxo-acetyl]amino]pyridine-3-carboxamide (2R,4S)—N-benzyl-2-phenyl-piperidin-4-amine (0.5 g, 1.47 mmol, 2HCl), 2-[(5-carbamoyl-3-pyridyl)amino]-2-oxo-acetic acid (308.22 mg, 1.25 mmol, HCl) and triethylamine (671.01 mg, 6.63 mmol, 924.26 μL) were mixed in DMF (5 mL). HATU (616.34 mg, 1.62 mmol) was added thereto in small portions with intensive stirring and the resulting mixture was stirred at 20° C. for 12 hr. The reaction mixture was subjected to HPLC to obtain 5-[[2-[(2R,4S)-4-(benzylamino)-2-phenyl-1-piperidyl]-2-oxo-acetyl]amino]pyridine-3-carboxamide (0.1896 g, 414.41 μmol, 28.12% yield).

HPLC conditions: 24% 0.5-6.5 min water-acetonitrile; flow: 30 ml/min; (loading pump 4 ml/min acetonitrile); target mass 457; column SunFire 100×19 mm 5 um (L)

$^1$H NMR (DMSO-$d_6$, 400 MHz): 1.75 (m, 2H), 2.21 (m, 2H), 2.95 (m, 1H), 3.20 (s, 2H), 3.66 (m, 4H), 4.13 (m, 1H), 5.16 (m, 1H), 7.40 (m, 9H), 8.30 (m, 4H), 11.28 (m, 1H).

LCMS(ESI): [M+H]$^+$ m/z: calcd 457.2; found 458.2; Rt=1.263 min.

Step 2: Synthesis of 5-[[2-[(2R,4S)-4-amino-2-phenyl-1-piperidyl]-2-oxo-acetyl]amino]pyridine-3-carboxamide The solution of 5-[[2-[(2R,4S)-4-(benzylamino)-2-phenyl-1-piperidyl]-2-oxo-acetyl]amino]pyridine-3-carboxamide (0.1896 g, 414.41 μmol) in MeOH (10 mL) was hydrogenated at 1 atm pressure using Palladium, 10% on carbon, Type 487, dry (2.21 mg, 20.72 μmol) as catalyst for 24 hr. The resulting mixture was filtered and filtrate evaporated to dryness to obtain 5-[[2-[(2R,4S)-4-amino-2-phenyl-1-piperidyl]-2-oxo-acetyl]amino]pyridine-3-carboxamide (0.12 g, 326.62 μmol, 78.82% yield) which was used in next step without purification.

LCMS(ESI): [M+H]$^+$ m/z: calcd 367.2; found 368.0; Rt=0.746 min.

Step 3: The of 5-[[2-[(2R,4S)-4-acetamido-2-phenyl-1-piperidyl]-2-oxo-acetyl]amino]pyridine-3-carboxamide (Compound 745

5-[[2-[(2R,4S)-4-amino-2-phenyl-1-piperidyl]-2-oxo-acetyl]amino]pyridine-3-carboxamide (0.12 g, 326.62 μmol) was mixed with acetyl acetate (66.69 mg, 653.24 μmol, 61.75 μL) in DCM (5 mL) and the resulting mixture was stirred at 20° C. for 12 hr. The resulting mixture was evaporated and the residue was subjected to HPLC to obtain 5-[[2-[(2R,4S)-4-acetamido-2-phenyl-1-piperidyl]-2-oxo-acetyl]amino]pyridine-3-carboxamide (33.30 mg, 81.33 μmol, 24.90% yield)

HPLC conditions: 0-10% 0.5-6.5 min water-acetonitrile; flow 30 ml/min; (loading pump 4 ml/min acetonitrile); target mass 409; column SunFire C18 100×19 mm 5 um (L)

$^1$H NMR (400 MHz, TFA) δ 3.02-3.25 (m, 2H), 3.25-3.34 (m, 3H), 3.36-3.75 (m, 3H), 3.76-3.96 (m, 1H), 4.84-5.15 (m, 1H), 5.45-6.19 (m, 3H), 6.73-7.24 (m, 1H), 8.34-8.45 (m, 3H), 8.47-8.58 (m, 3H), 10.26-10.51 (m, 2H), 10.62-10.88 (m, 1H).

LCMS(ESI): [M+H]$^+$ m/z: calcd 409.2; found 410.4; Rt=1.411 min.

Example 715. The Synthesis of 2-[(2R,4S)-4-acetamido-2-phenyl-1-piperidyl]-N-(6-amino-5-methyl-3-pyridyl)-2-oxo-acetamide (Compound 831)

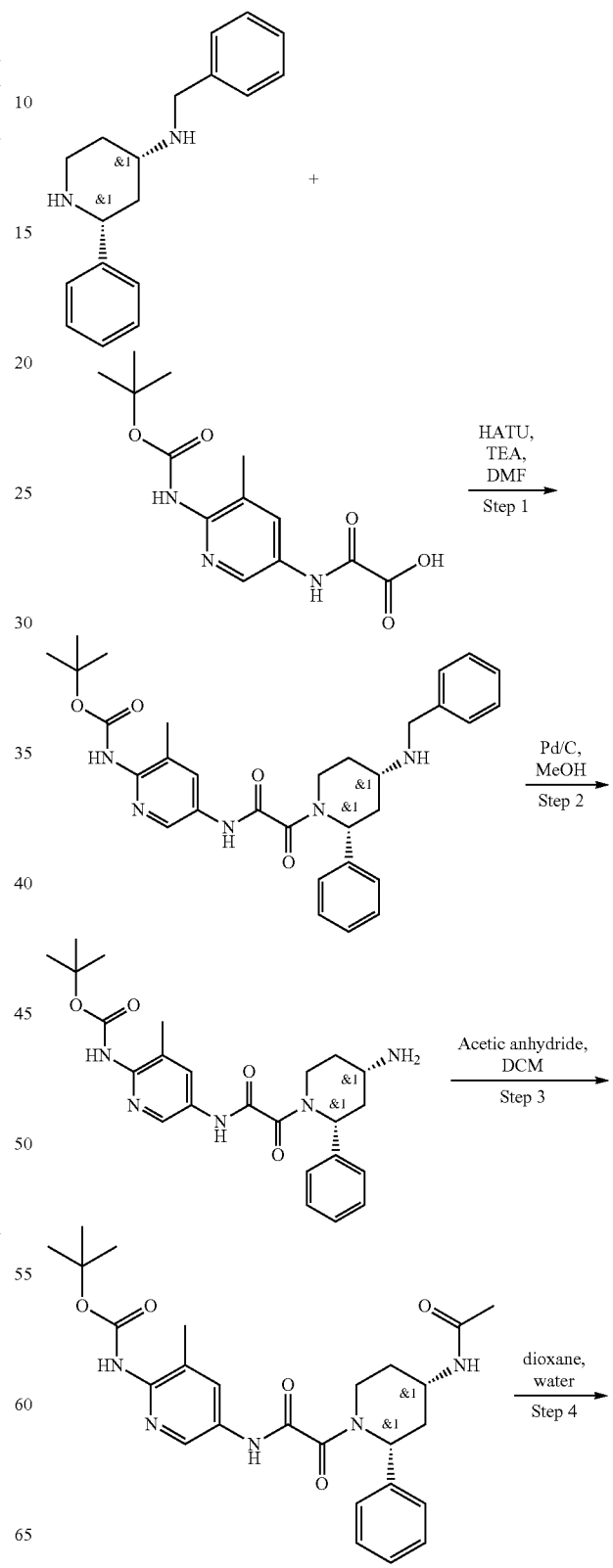

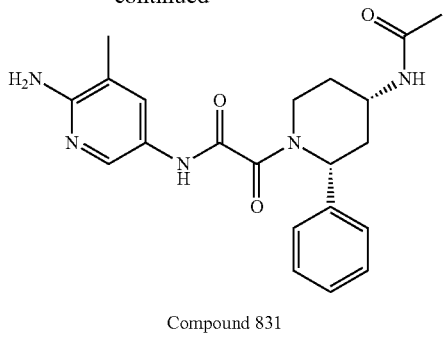

Compound 831

Step 1: Synthesis of tert-butyl N-[5-[[2-[(2R,4S)-4-(Benzylamino)-2-phenyl-1-piperidyl]-2-oxo-acetyl]amino]-3-methyl-2-pyridyl]carbamate (2R,4S)—N-benzyl-2-phenyl-piperidin-4-amine (392.54 mg, 1.47 mmol, 2HCl), 2-[[6-(tert-butoxycarbonylamino)-5-methyl-3-pyridyl]amino]-2-oxo-acetic acid (435.14 mg, 1.47 mmol) and DIPEA (761.81 mg, 5.89 mmol, 1.03 mL) were dissolved in DMSO (5 mL) under gentle heating. HATU (672.37 mg, 1.77 mmol) was added in small portions under vigorous stirring and occasional heating. After the reaction was complete, the mixture was purified by HPLC to give tert-butyl N-[5-[[2-[(2R,4S)-4-(benzylamino)-2-phenyl-1-piperidyl]-2-oxo-acetyl]amino]-3-methyl-2-pyridyl]carbamate (0.5 g, 919.70 µmol, 62.41% yield).

HPLC conditions: (2-4 58-62% 0.5-6.5 min water-MeOH+NH₃; flow 30 ml/min; (loading pump 4 ml/min MeOH); target mass 543; column SunFire C18 100×19 mm 5 um (L)).

LCMS(ESI): [M+H]⁺ m/z: calcd 543.3; found 544.0; Rt=2.183 min.

Step 2: Synthesis of tert-butyl N-[5-[[2-[(2R,4S)-4-amino-2-phenyl-1-piperidyl]-2-oxo-acetyl]amino]-3-methyl-2-pyridyl]carbamate tert-butyl N-[5-[[2-[(2R,4S)-4-(benzylamino)-2-phenyl-1-piperidyl]-2-oxo-acetyl]amino]-3-methyl-2-pyridyl]carbamate (80.00 mg, 147.15 µmol) was dissolved in MeOH (5 mL), followed by the addition of Pd/C (1.79 mg, 14.72 µmol). Obtained mixture was stirred under hydrogen atmosphere (1 atm) overnight. After the reaction was complete, the solids was filtered off and the organic solvents was evaporated to give tert-butyl N-[5-[[2-[(2R,4S)-4-amino-2-phenyl-1-piperidyl]-2-oxo-acetyl]amino]-3-methyl-2-pyridyl]carbamate (60 mg, 132.29 µmol, 89.90% yield).

LCMS(ESI): [M+H]⁺ m/z: calcd 453.3; found 454.2; Rt=0.982 min.

Step 3: The of Tert-butyl N-[5-[[2-[(2R,4S)-4-acetamido-2-phenyl-1-piperidyl]-2-oxo-acetyl]amino]-3-methyl-2-pyridyl]carbamate tert-butyl N-[5-[[2-[(2R,4S)-4-amino-2-phenyl-1-piperidyl]-2-oxo-acetyl]amino]-3-methyl-2-pyridyl]carbamate (30 mg, 66.15 µmol) was dissolved in DCM (3 mL) followed by the addition of Acetic anhydride (8.10 mg, 79.38 µmol, 7.50 µL). After the reaction was completed, the organic solvent was evaporated under reduced pressure to give tert-butyl N-[5-[[2-[(2R,4S)-4-acetamido-2-phenyl-1-piperidyl]-2-oxo-acetyl]amino]-3-methyl-2-pyridyl]carbamate (60 mg, crude) which was used in the next step without purification.

LCMS(ESI): [M+H]⁺ m/z: calcd 409.2; found 410.4; Rt=1.411 min.

Step 4: Synthesis of 2-[(2R,4S)-4-acetamido-2-phenyl-1-piperidyl]-N-(6-amino-5-methyl-3-pyridyl)-2-oxo-acetamide (Compound 831 tert-butyl N-[5-[[2-[(2R,4S)-4-acetamido-2-phenyl-1-piperidyl]-2-oxo-acetyl]amino]-3-methyl-2-pyridyl]carbamate (60 mg, 60.54 µmol) was dissolved in H₂O (1 mL)/dioxane (2 mL) mixture and stirred at reflux overnight. Aliquot shows the full consumption of the starting material; evaporation of the solvents under reduced pressure and purification with HPLC (10-60% 0.5-7.5 min water-MeOH+NH₃ flow 30 ml/min (loading pump 4 ml/min MeCN) target mass 396 column: sunfire C18 100*19 mm 5 um) results in 2-[(2R,4S)-4-acetamido-2-phenyl-1-piperidyl]-N-(6-amino-5-methyl-3-pyridyl)-2-oxo-acetamide (10 mg, 25.29 µmol, 41.77% yield).

¹H NMR (600 MHz, DMSO-d₆) δ 1.43-1.55 (m, 4H), 1.94-2.07 (m, 5H), 2.26-2.35 (m, 1H), 3.47-3.59 (m, 1H), 3.67-3.79 (m, 1H), 3.82-4.27 (m, 1H), 5.13-5.35 (m, 1H), 5.52-5.66 (m, 2H), 7.17-7.24 (m, 3H), 7.28-7.34 (m, 2H), 7.34-7.56 (m, 2H), 7.80-8.07 (m, 1H), 10.26-10.56 (m, 1H).

LCMS(ESI): [M+H]⁺ m/z. calcd 395.2; found 396.4; Rt=1.286 min.

Example 716. The Synthesis of N-(6-amino-5-methyl-3-pyridyl)-2-[(2S,4S)-4-(dimethylamino)-2-phenyl-1-piperidyl]-2-oxo-acetamide (Compound 975) and N-(6-amino-5-methyl-3-pyridyl)-2-[(2R,4S)-4-(dimethylamino)-2-phenyl-1-piperidyl]-2-oxo-acetamide (Compound 906)

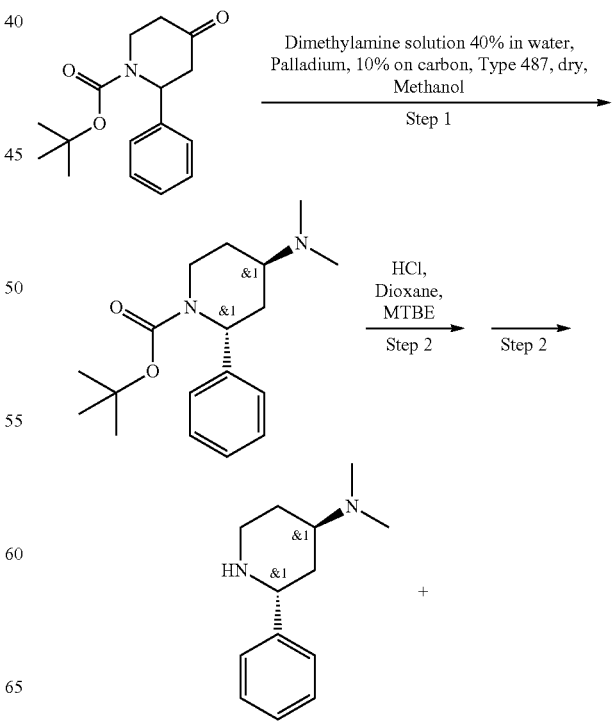

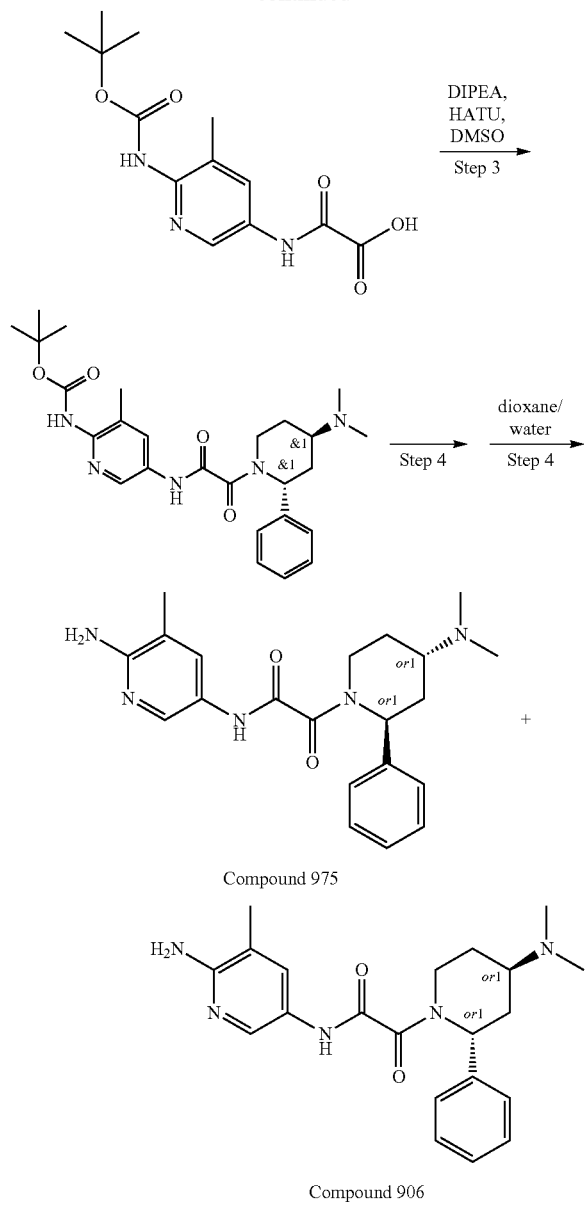

Compound 975

Compound 906

Step 1: Synthesis of tert-butyl 4-(dimethylamino)-2-phenyl-piperidine-1-carboxylate tert-butyl 4-oxo-2-phenyl-piperidine-1-carboxylate (0.5 g, 1.82 mmol) was dissolved in Methanol (20 mL)/Dimethylamine solution 40% in water (818.68 mg, 18.16 mmol, 1.06 mL) mixture and hydrogenated under Hydrogen atmosphere in autoclave. After the reaction was complete, the solid was filtered off and the organic solvent was evaporated to dryness, resulting in crude tert-butyl 4-(dimethylamino)-2-phenyl-piperidine-1-carboxylate (0.6 g, 1.97 mmol, 108.54% yield) which was used in the next step without purification.

Note: mixture of diastereomers was obtained.

LCMS(ESI): [M+H]+ m/z: calcd 304.3; found 305.2; Rt=0.986 min.

Step 2: Synthesis of N,N-dimethyl-2-phenyl-Piperidin-4-amine tert-butyl 4-(dimethylamino)-2-phenyl-piperidine-1-carboxylate (0.6 g, 1.97 mmol) was dissolved in diox (3 mL), following by the addition of HCl (10 M, 1.97 mL) and stirring overnight. After the reaction was complete, the obtained solid was filtered, washed with MTBE (10 mL) and dried on air to give N,N-dimethyl-2-phenyl-piperidin-4-amine (0.4 g, 1.44 mmol, 73.21% yield, 2HCl).

$^1$H NMR (DMSO-$d_6$, 400 MHz): 2.10 (m, 4H), 2.37 (s, 3H), 2.41 (s, 3H), 2.62 (m, 2H), 4.32 (m, 1H), 7.43 (m, 5H), 9.97 (m, 2H), 11.43 (s, 1H).

Step 3: Synthesis of tert-butyl N-[5-[[2-[4-(dimethylamino)-2-phenyl-1-piperidyl]-2-oxo-acetyl]amino]-3-methyl-2-pyridyl]carbamate 2-[[6-(tert-butoxycarbonylamino)-5-methyl-3-pyridyl]amino]-2-oxo-acetic acid (426.05 mg, 1.44 mmol), N,N-dimethyl-2-phenyl-piperidin-4-amine (0.4 g, 1.44 mmol, 2HCl) and DIPEA (559.41 mg, 4.33 mmol, 753.93 µL) were dissolved in DMSO (6 mL) under gentle heating. HATU (658.33 mg, 1.73 mmol) was added in small portions under vigorous stirring and occasional heating. After the reaction was complete, the mixture was purified by HPLC 24% 0.5-6.5 min water-acetonitrile+NH$_3$; flow 30 ml/min (loading pump 4 ml/min acetonitrile); target mass 481; column XBridge 100×19 mm 5 um (R)) to give tert-butyl N-[5-[[2-[4-(dimethylamino)-2-phenyl-1-piperidyl]-2-oxo-acetyl]amino]-3-methyl-2-pyridyl]carbamate (0.55 g, 1.14 mmol, 79.15% yield).

LCMS(ESI): [M+H]+ m/z: calcd 481.3; found 482.2; Rt=1.952 min.

Step 4: The Synthesis of N-(6-amino-5-methyl-3-pyridyl)-2-[(2S,4S)-4-(dimethylamino)-2-phenyl-1-piperidyl]-2-oxo-acetamide (Compound 975) and N-(6-amino-5-methyl-3-pyridyl)-2-[(2R,4S)-4-(dimethylamino)-2-phenyl-1-piperidyl]-2-oxo-acetamide (Compound 906 tert-butyl N-[5-[[2-[4-(dimethylamino)-2-phenyl-1-piperidyl]-2-oxo-acetyl]amino]-3-methyl-2-pyridyl]carbamate (0.5 g, 1.04 mmol) was dissolved in dioxane (5 mL)/water (1 mL) mixture and stirred at reflux overnight. Aliquot shows the full consumption of the starting material; evaporation of the solvents under reduced pressure and purification with HPLC (5-40% 0.5-6.5 min water-acetonitrile; flow 30 ml/min (loading pump 4 ml/min acetonitrile); target mass 382; column SunFire C18 100×19 mm 5 um (R)) results in N-(6-amino-5-methyl-3-pyridyl)-2-[(2S,4S)-4-(dimethylamino)-2-phenyl-1-piperidyl]-2-oxo-acetamide (140 mg, 367.00 µmol, 35.35% yield) and N-(6-amino-5-methyl-3-pyridyl)-2-[(2R,4S)-4-(dimethylamino)-2-phenyl-1-piperidyl]-2-oxo-acetamide (90 mg, 235.93 µmol, 22.72% yield) Relative configuration was determined by 2D NMR.

Compound 975: $^1$H NMR (600 MHz, DMSO-$d_6$) δ 1.54-1.64 (m, 1H), 1.70-1.79 (m, 1H), 1.93-1.97 (m, 1H), 1.97-2.04 (m, 3H), 2.05-2.12 (m, 6H), 2.11-2.24 (m, 3H), 3.43-3.61 (m, 1H), 3.77-4.30 (m, 1H), 4.95-5.21 (m, 1H), 5.47-5.69 (m, 2H), 7.14-7.33 (m, 5H), 7.49 (s, 1H), 7.66-8.10 (m, 1H), 9.93-10.50 (m, 1H).

LCMS(ESI): [M+H]+ m/z: calcd 381.3; found 382.4; Rt=0.846 min.

Compound 906: $^1$H NMR (DMSO-$d_6$, 600 MHz): δ (ppm) 1.36 (m, 1H), 1.70 (m, 2H), 2.00 (m, 4H), 2.15 (d, 6H), 2.27 (m, 1H), 2.86 (m, 1H), 4.05 (m, 1H), 5.66 (m, 3H), 7.29 (m, 3H), 7.38 (m, 2H), 7.47 (m, 1H), 7.99 (m, 1H), 10.54 (s, 1H).

LCMS(ESI): [M+H]⁺ m/z: calcd 381.3; found 382.2; Rt=1.061 min.

Example 717. The Synthesis of 5-[[2-[(2R,5S)-2-(4-fluorophenyl)-5-methyl-1-piperidyl]-2-oxo-acetyl]amino]-2-(trifluoromethoxy)pyridine-3-carboxamide (Compound 1039)

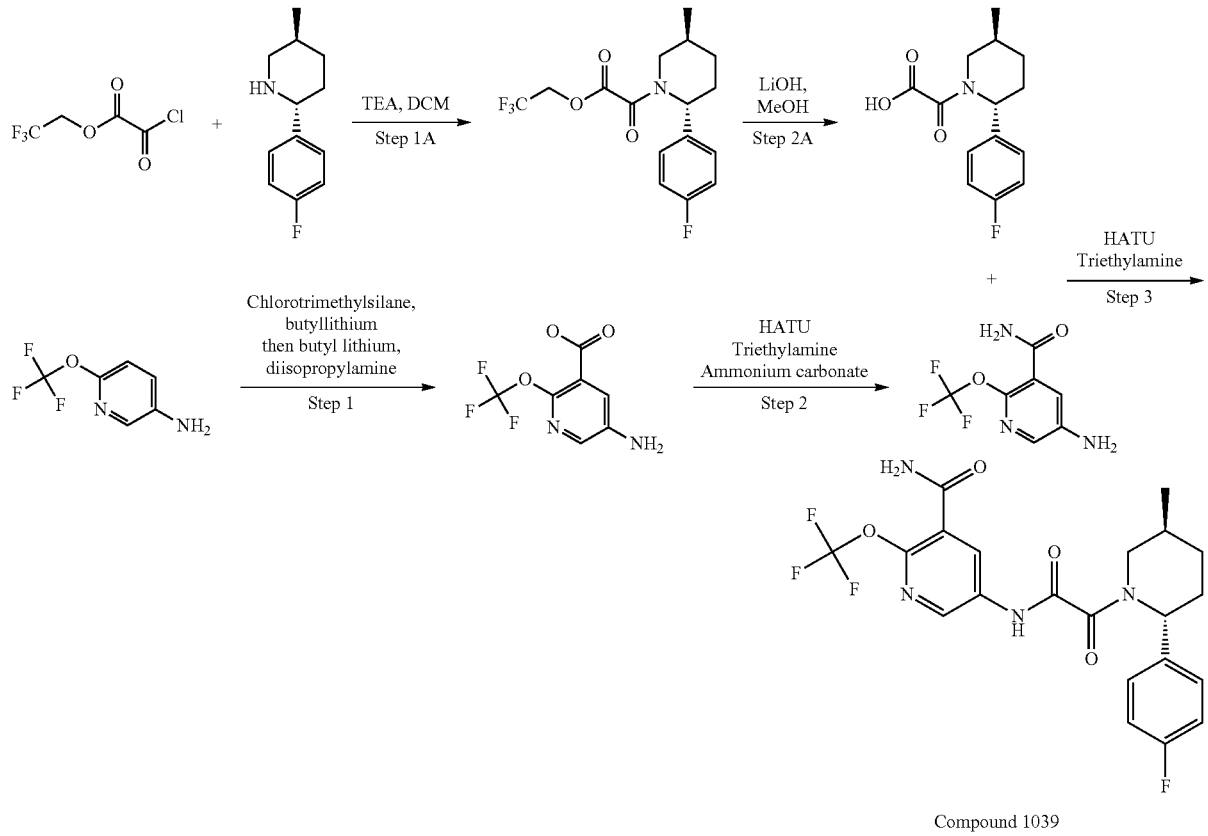

Compound 1039

Step 1A. Synthesis of 2,2,2-trifluoroethyl 2-[(2R,5S)-2-(4-fluorophenyl)-5-methyl-1-piperidyl]-2-oxo-acetate To a solution of (2R,5S)-2-(4-fluorophenyl)-5-methyl-piperidine (3.00 g, 15.52 mmol) (Intermediate 4A) and TEA (1.88 g, 18.63 mmol, 2.60 mL) in DCM (50 mL) was added 2,2,2-trifluoroethyl 2-chloro-2-oxo-acetate (3.25 g, 17.08 mmol) at 0° C. After stirring at rt for 1 hr the resulting mixture was filtered and evaporated to dryness to give 2,2,2-trifluoroethyl 2-[(2R,5S)-2-(4-fluorophenyl)-5-methyl-1-piperidyl]-2-oxo-acetate (5.72 g, crude) as a yellow gum, which was used in the next step without further purification.

¹H NMR (CDCl₃, 400 MHz): δ (ppm) 1.06 (m, 3H), 1.43 (m, 1H), 1.86-2.00 (m, 2H), 2.17 (m, 2H), 2.89 (dd, 0.3H, rotameric), 3.08 (m, 1H), 3.30 (dd, 0.7H), 4.09 (d, 0.3H), 4.58 (m, 1H), 4.77 (m, 1H), 5.73 (s, 0.7H), 7.04 (m, 2H), 7.20 (m, 2H).

LCMS(ESI): [M+1]⁺ m/z: calcd 347.1; found 348.2; Rt=3.756 min.

Step 2A. Synthesis of 2-[(2R,5S)-2-(4-fluorophenyl)-5-methyl-1-piperidyl]-2-oxo-acetic acid To a solution of 2,2,2-trifluoroethyl 2-[(2R,5S)-2-(4-fluorophenyl)-5-methyl-1-piperidyl]-2-oxo-acetate (3.81 g, 10.97 mmol) in MeOH (50 mL) was added Lithium hydroxide monohydrate, 98% (598.45 mg, 14.26 mmol, 396.33 μL) and the resulting mixture was left to stir at rt for 1 hr. Then the resulting mixture was evaporated to dryness, dissolved in water, water was acidified to pH=1 and extracted with DCM twice, organics were washed with brine, dried over Na₂SO₄ and evaporated. 2-[(2R,5S)-2-(4-fluorophenyl)-5-methyl-1-piperidyl]-2-oxo-acetic acid (2.5 g, 9.42 mmol, 85.91% yield) was obtained as a white solid.

¹H NMR (CDCl₃, 400 MHz): δ (ppm) 1.06 (m, 3H), 1.40 (m, 1H), 1.83 (m, 1H), 1.95 (m, 1H), 2.18 (m, 2H), 2.90-3.30 (two doublets, 1H, rotameric), 4.18 (m, 1H), 5.79 (m, 1H), 7.04 (t, 2H), 7.23 (m, 2H).

LCMS(ESI): [M+1]⁺ m/z: calcd 265.1; found 266.2; Rt=1.212 min.

Step 1 Synthesis of 2-benzyloxy-5-bromo-pyridine

At −78° C., butyllithium (1.20 g, 18.75 mmol, 7.51 mL) was added dropwise to a solution of 6-(trifluoromethoxy)pyridin-3-amine (1.67 g, 9.38 mmol) in THF (20 mL) followed after 1 min by Chlorotrimethylsilane (2.14 g, 19.69 mmol, 2.50 mL). The reaction mixture was allowed to reach 25 0C for 2 hr before being filtrated onto a pad of celite. The solvent was removed and the crude oil was distilled under vacuum (101-103° C./1 mbar) to afford 6-(trifluoromethoxy)-N,N-bis(trimethylsilyl)pyridin-3-amine (2.93 g, crude). At 0° C. butyl lithium (1.18 g, 18.43 mmol, 7.38 mL) was added dropwise to a solution of diisopropylamine (1.95 g, 19.31 mmol, 2.72 mL) in THF (56 mL). At −78 0° C., a solution of 6-(trifluoromethoxy)-N,N-bis(trimethylsilyl)pyridin-3-amine (2.83 g, 8.78 mmol) in THF (2 mL) was added dropwise and the reaction mixture was stirred for 1 h at this temperature. Then $CO_2$ was sparged into solution through drying vessel with sulfuric acid for 15 min. After 30 min at −78° C. the solution was allowed to rt. The solvent was evaporated. Resulting crude material was purified by column chromatography (MTBE/Methanol) to obtain 5-amino-2-(trifluoromethoxy)pyridine-3-carboxylic acid (0.1 g, 450.20 µmol, 5.13% yield)

$^1$H NMR (500 MHz, DMSO-$d_6$) δ (ppm) 5.20-5.30 (brs, 2H), 7.35 (s, 1H), 7.65 (s, 1H).

LCMS(ESI): [M+1]$^+$ m/z: calcd 222.0; found 223.0; Rt=0.641 min.

Step 2. Synthesis of 5-amino-2-(trifluoromethoxy)pyridine-3-carboxamide 5-amino-2-(trifluoromethoxy)pyridine-3-carboxylic acid (90 mg, 405.18 µmol), Ammonium carbonate (116.80 mg, 1.22 mmol), Triethylamine (205.00 mg, 2.03 mmol, 282.37 µL) were mixed in DMF (2 mL) and then HATU (231.09 mg, 607.78 µmol) were added. Resulting mixture were stirred at 25° C. for 13 hr. The solvent was evaporated to obtain crude product that was purified by HPLC (35-55% (Methanol)-2-10 min Flow rate: 30 ml/min) to obtain 5-amino-2-(trifluoromethoxy)pyridine-3-carboxamide (18.9 mg, 85.47 µmol, 21.09% yield)

$^1$H NMR (400 MHz, CDCl$_3$) δ (ppm) 5.19 (d, 1H), 5.37 (s, 2H), 5.65 (d, 1H), 6.63 (m, 1H), 6.78 (d, 1H), 7.24-7.63 (m, 5), 7.71 (d, 1H), 8.19 (s, 1H).

LCMS(ESI): [M+1]$^+$ m/z: calcd 221.0; found 222.0; Rt=0.727 min.

Step 3. Synthesis of 5-[[2-[(2R,5S)-2-(4-fluorophenyl)-5-methyl-1-piperidyl]-2-oxo-acetyl]amino]-2-(trifluoromethoxy)pyridine-3-carboxamide (Compound 1039

5-amino-2-(trifluoromethoxy)pyridine-3-carboxamide (0.154 g, 696.40 µmol), 2-[(2R,5S)-2-(4-fluorophenyl)-5-methyl-1-piperidyl]-2-oxo-acetic acid (184.74 mg, 696.40 µmol), Triethylamine (704.69 mg, 6.96 mmol, 970.65 µL) were mixed in DMF (5 mL) and then HATU (397.19 mg, 1.04 mmol) were added. Resulting mixture were stirred at 25° C. for 12 hr. The solvent was evaporated and resulting mixture was stirred with SiliaMetS® DMT (50 mg) in methanol (10 ml). The mixture was filtered and evaporated under reduce pressure. Resulting crude material was purified by HPLC (2-10 min 50-100% Methanol/H$_2$O) to obtain 5-[[2-[(2R,5S)-2-(4-fluorophenyl)-5-methyl-1-piperidyl]-2-oxo-acetyl]amino]-2-(trifluoromethoxy)pyridine-3-carboxamide (104.80 mg, 223.74 µmol, 32.13% yield)

$^1$H NMR (dmso, 600 MHz): δ (ppm) 0.97-1.06 (m, 3H), 1.27-1.39 (m, 1H), 1.59-1.73 (m, 1H), 1.82-1.94 (m, 1H), 2.00-2.13 (m, 1H), 2.14-2.24 (m, 1H), 2.74-3.23 (m, 1H), 3.44-4.07 (m, 1H), 5.11-5.65 (m, 1H), 7.16-7.26 (m, 2H), 7.30-7.40 (m, 2H), 7.74-7.85 (m, 1H), 7.91-8.04 (m, 1H), 8.29-8.37 (m, 1H), 8.54-8.67 (m, 1H), 11.23-11.60 (m, 1H).

LCMS(ESI): [M+1]$^+$ m/z: calcd 468.0; found 469.0; Rt=3.289 min.

Example 718. The Synthesis of Rac 5-[[2-[(2R,5S)-2-(4-fluorophenyl)-5-methyl-1-piperidyl]-2-oxo-acetyl]amino]-2-(trifluoromethoxy)pyridine-3-carboxamide (Compound 818)

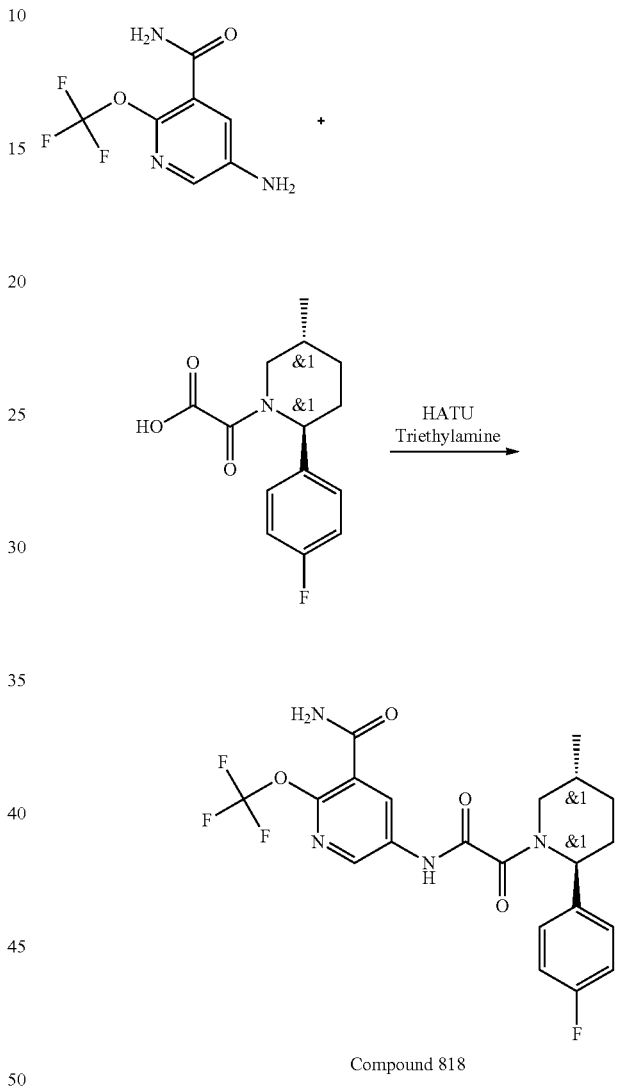

Compound 818

5-amino-2-(trifluoromethoxy)pyridine-3-carboxamide (18.9 mg, 85.47 µmol) (prepared as above), rac 2-[(2R,5S)-2-(4-fluorophenyl)-5-methyl-1-piperidyl]-2-oxo-acetic acid (22.67 mg, 85.47 µmol) (prepared in a manner similar to the above procedure for the enantiopure material), Triethylamine (43.24 mg, 427.34 µmol, 59.56 µL) were mixed in DMF (2 mL) and then HATU (48.75 mg, 128.20 µmol) were added. Resulting mixture were stirred at 25° C. for 11 hr. The solvent was evaporated and resulting mixture was stirred with SiliaMetS® DMT (50 mg) in methanol (10 ml). The mixture was filtered and evaporated under reduce pressure. Resulting crude material was purified by HPLC (2-10 min 50-100% Methanol/H$_2$O) to obtain rac 5-[[2-[(2R,5S)-2-(4-fluorophenyl)-5-methyl-1-piperidyl]-2-oxo-acetyl]amino]-2-(trifluoromethoxy)pyridine-3-carboxamide (14.1 mg, 30.10 µmol, 35.22% yield)

¹H NMR (dmso, 600 MHz): δ (ppm) 0.97-1.06 (m, 3H), 1.27-1.39 (m, 1H), 1.59-1.73 (m, 1H), 1.82-1.94 (m, 1H), 2.00-2.13 (m, 1H), 2.14-2.24 (m, 1H), 2.74-3.23 (m, 1H), 3.44-4.07 (m, 1H), 5.11-5.65 (m, 1H), 7.16-7.26 (m, 2H), 7.30-7.40 (m, 2H), 7.74-7.85 (m, 1H), 7.91-8.04 (m, 1H), 8.29-8.37 (m, 1H), 8.54-8.67 (m, 1H), 11.23-11.60 (m, 1H).

LCMS(ESI): [M+1]⁺ m/z: calcd 468.0; found 469.0; Rt=3.289 min.

Example 719. The Synthesis of N-(5-chloro-6-methylpyridin-3-yl)-2-(2-(4-fluorophenyl)-5-methylpiperidin-1-yl)-2-oxoacetamide (Compound 622)

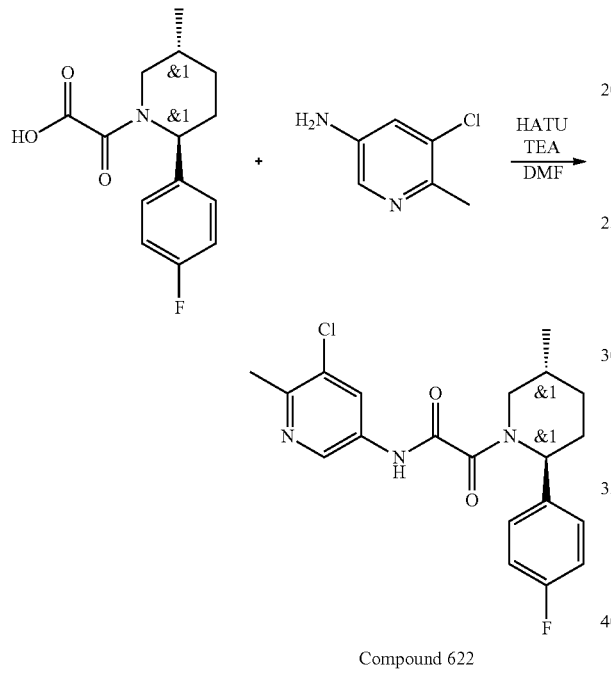

Compound 622

Example 720. The Synthesis of N-(6-amino-5-(difluoromethyl)pyridin-3-yl)-2-(2-(4-fluorophenyl)-5-methylpiperidin-1-yl)-2-oxoacetamide (Compound 867)

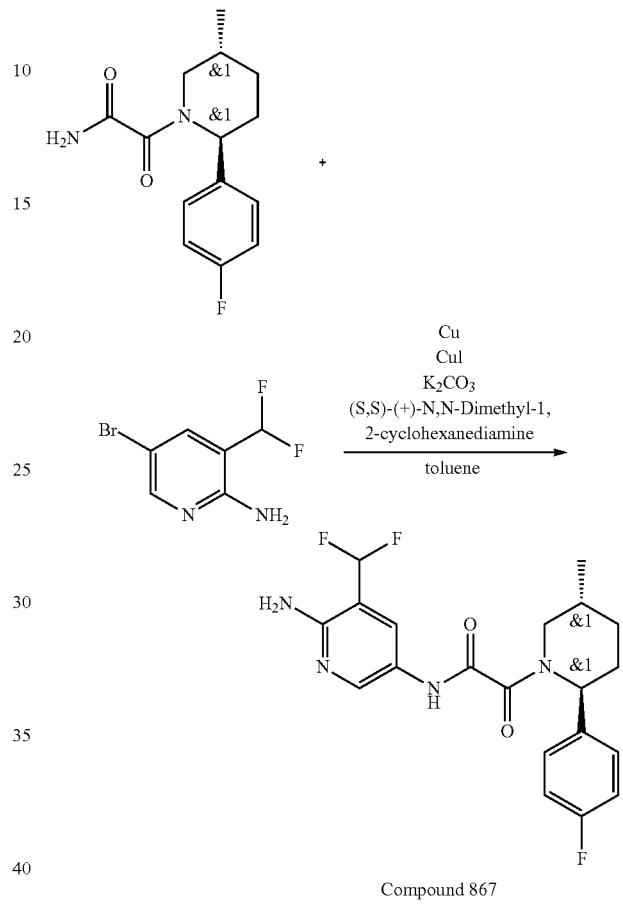

Compound 867 rac-2-[(2S,5R)-2-(4-fluorophenyl)-5-methyl-1-piperidyl]-2-oxo-acetic acid (300.00 mg, 1.13 mmol) (prepared in a manner similar to that described above for the enantiopure material), 5-chloro-6-methyl-pyridin-3-amine (161.25 mg, 1.13 mmol) and TEA (1.14 g, 11.31 mmol, 1.58 mL) were mixed together in DMF (5 mL). HATU (644.99 mg, 1.70 mmol) was added to the previous mixture and the resulting mixture was stirred for 18 hr. The reaction mixture was concentrated in vacuum and the residue was purified by HPLC (2-10 min 50-60% water/MeOH (loading pump 4 ml MeOH) column: TRIART 100*20 5 microM) to obtain N-(5-chloro-6-methyl-3-pyridyl)-2-[(2S,5R)-2-(4-fluorophenyl)-5-methyl-1-piperidyl]-2-oxo-acetamide (0.1985 g, 509.17 µmol, 45.02% yield).

Compound 622: ¹H NMR (600 MHz, DMSO-d₆) δ (ppm) 0.68-1.02 (m, 3H), 1.22-1.38 (m, 1H), 1.61-1.71 (m, 1H), 1.80-1.95 (m, 1H), 1.98-2.13 (m, 1H), 2.13-2.30 (m, 1H), 2.42-2.46 (m, 3H), 2.73-3.26 (m, 1H), 3.43-4.25 (m, 1H), 5.08-5.67 (m, 1H), 7.15-7.28 (m, 2H), 7.30-7.40 (m, 2H), 8.11-8.27 (m, 1H), 8.53-8.69 (m, 1H), 11.05-11.34 (m, 1H).

LCMS(ESI): [M]⁺ m/z: calcd 389.2; found 390.2; Rt=1.504 min.

2-[(2R,5S)-2-(4-fluorophenyl)-5-methyl-1-piperidyl]-2-oxo-acetamide (590 mg, 2.23 mmol), 5-bromo-3-(difluoromethyl)pyridin-2-amine (497.86 mg, 2.23 mmol), copper (70.93 mg, 1.12 mmol), copper (I) iodide (42.52 mg, 223.24 µmol, 7.56 µL), (S,S)-(+)-N,N'-dimethyl-1,2-cyclohexane-diamine (31.75 mg, 223.24 µmol, 35.20 µL) and potassium carbonate (617.05 mg, 4.46 mmol, 269.45 µL) were mixed together in toluene (12 mL). Stream of argon was bubbled through reaction mixture for 2 min before it was stirred in a sealed flask at 105° C. for 18 hr. Then, it was diluted with ethyl acetate (20 ml) and 5% aq. NH₃ solution (15 ml). Resulting biphasic mixture was filtered through a florisil pad. Organic layer was separated, dried over Na₂SO₄ and concentrated under reduced pressure. Residue was purified by HPLC(1-st run: 50-70% 0-5 min H₂O/MeOH/0.1% NH₄OH, flow: 30 ml/min; 2-nd run: 50-60% 0-6 min H₂O/MeOH/0.1% NH₄OH, flow: 30 ml/min; column: YMC Triart C18 100×20 mm, 5 um), affording N-[6-amino-5-(difluoromethyl)-3-pyridyl]-2-[(2R,5S)-2-(4-fluorophenyl)-5-methyl-1-piperidyl]-2-oxo-acetamide (190 mg, 467.52 µmol, 20.94% yield). Compound 867: ¹H NMR (600 MHz, DMSO-d₆) δ (ppm) 0.72-1.05 (m, 3H), 1.21-1.38 (m, 1H), 1.58-1.69 (m, 1H), 1.78-1.93 (m, 1H), 1.96-2.08 (m, 1H), 2.09-2.26 (m, 1H), 2.71-3.20 (m, 1H), 3.47-4.05 (m, 1H), 5.09-5.68 (m, 1H), 6.10-6.23 (m, 2H), 6.87-7.13 (m, 1H), 7.14-7.25 (m, 2H), 7.30-7.42 (m, 2H), 7.87-8.00 (m, 1H), 8.20-8.32 (m, 1H), 10.64-10.91 (m, 1H).

LCMS(ESI): [M]+ m/z: calcd 406.2; found 407.2; Rt=2.966 min.

Example 721. The Synthesis of N-(6-amino-5-(trifluoromethyl)pyridin-3-yl)-2-(2-(4-fluorophenyl)-5-methylpiperidin-1-yl)-2-oxoacetamide (Compound 872)

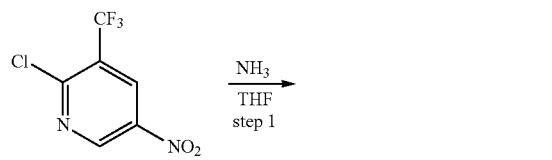

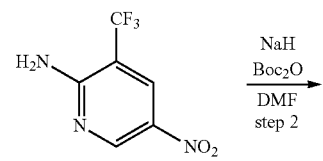

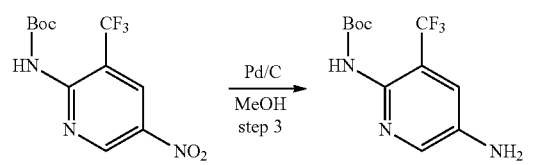

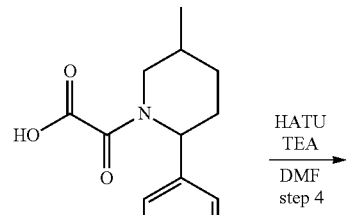

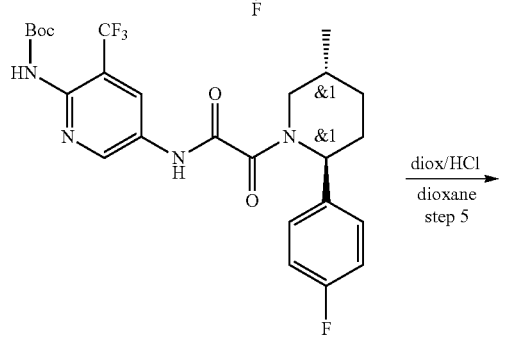

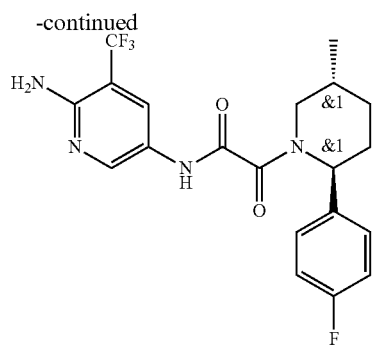

Compound 872

Step 1: Synthesis of 5-nitro-3-(trifluoromethyl)pyridin-2-amine

A solution of 2-chloro-5-nitro-3-(trifluoromethyl)pyridine (4.5 g, 19.86 mmol) and ammonia (338.29 mg, 19.86 mmol) solution in THF (50 mL) was stirred at rt for 14 hr. After completion of the reaction, the reaction mixture was filtered and concentrated under vacuum to give 5-nitro-3-(trifluoromethyl)pyridin-2-amine (3.5 g, crude) as a white solid.

$^1$H NMR (400 MHz, DMSO-d$_6$) δ (ppm) 7.96 (bds, 2H), 8.35 (s, 1H), 9.01 (s, 1H). LCMS(ESI): [M]+ m/z: calcd 207.2; found 208.2; Rt=0.985 min.

Step 2: Synthesis of tert-butyl (5-nitro-3-(trifluoromethyl)pyridin-2-yl)carbamate To a solution of 5-nitro-3-(trifluoromethyl)pyridin-2-amine (3.5 g, 16.90 mmol) in DMF (15 mL), sodium hydride (in oil dispersion) 60% dispersion in mineral oil (743.50 mg, 18.59 mmol, 60% purity) was added portion wise at 0° C. The resulting mixture was stirred for 0.5 hr (to the end of gas evolution) and a solution of di-tert-butyl dicarbonate (4.06 g, 18.59 mmol, 4.27 mL) in DMF (5 mL) was added dropwise. The resulting mixture was stirred at 25° C. for 16 hr. The mixture was quenched with water (1000 mL), extracted 3 times with water, combined organics were washed with water, brine, dried and evaporated to give tert-butyl N-[5-nitro-3-(trifluoromethyl)-2-pyridyl]carbamate (6.8 g, crude) as a brown solid which was used in the next step without further purification.

$^1$H NMR (400 MHz, DMSO-d$_6$) δ (ppm) 1.42 (s, 9H), 8.69 (s, 1H), 9.35 (s, 1H), 10.12 (s, 1H). LCMS(ESI): [M]+ m/z: calcd 307.2; found 308.2; Rt=1.222 min.

Step 3: Synthesis of tert-butyl (5-amino-3-(trifluoromethyl)pyridin-2-yl)carbamate To a solution of tert-butyl N-[5-nitro-3-(trifluoromethyl)-2-pyridyl]carbamate (0.65 g, 2.12 mmol) in MeOH (25 mL) in three-necked round-bottomed flask was added Pd/C (0.06 g, 2.12 mmol). The reaction flask was evacuated and back-filled with molecular hydrogen (4.26 mg, 2.12 mmol) and the mixture was left to stir overnight. Filtration through a thin pad of silica gel followed by concentration and drying under vacuum afforded tert-butyl N-[5-amino-3-(trifluoromethyl)-2-pyridyl]carbamate (0.5 g, 1.80 mmol, 85.24% yield) as a beige solid.

$^1$H NMR (500 MHz, DMSO-d$_6$) δ (ppm) 1.38 (s, 9H), 5.78 (bds, 2H), 7.23 (s, 1H), 7.97 (s, 1H), 8.73 (s, 1H). LCMS(ESI): [M]+ m/z: calcd 277.2; found 278.2; Rt=1.091 min.

Step 4: Synthesis of rac-tert-butyl (5-(2-((2R,5S)-2-(4-fluorophenyl)-5-methylpiperidin-1-yl)-2-oxoacetamido)-3-(trifluoromethyl)pyridin-2-yl)carbamate tert-butyl N-[5-amino-3-(trifluoromethyl)-2-pyridyl]carbamate (252.91 mg, 912.24 µmol), TEA (184.62 mg, 1.82 mmol, 254.30 µL) and HATU (346.86 mg, 912.24 µmol) were mixed in dry DMF (5 mL) at 21° C. and the resulting mixture was stirred for 15 min. 2-[2-(4-fluorophenyl)-5-methyl-1-piperidyl]-2-oxo-acetic acid (0.242 g, 912.24 µmol) was added thereto and the resulting mixture was stirred at 21° C. overnight. The resulting mixture was poured into water, extracted 3 times with EtOAc, combined organics were washed with water, brine and evaporated. The residue was subjected to HPLC (50-75% 2-7 min water-MeCN flow 30 ml/min (loading pump 4 ml/min acn; column sunfire 100×19 mm 5 um (R)). tert-butyl N-[5-[[2-[2-(4-fluorophenyl)-5-methyl-1-piperidyl]-2-oxo-acetyl]amino]-3-(trifluoromethyl)-2-pyridyl]carbamate (256.7 mg, 489.41 µmol, 53.65% yield) was obtained as an off-white solid (cis impurity is present).

$^1$H NMR (500 MHz, DMSO-$d_6$) δ (ppm) 1.38 (s, 9H), 5.78 (bds, 2H), 7.23 (s, 1H), 7.97 (s, 1H), 8.73 (s, 1H). LCMS(ESI): [M]$^+$ m/z: calcd 524.2; found 525.2; Rt=4.018 min.

Step 5: Synthesis of N-(6-amino-5-(trifluoromethyl)pyridin-3-yl)-2-(2-(4-fluorophenyl)-5-methylpiperidin-1-yl)-2-oxoacetamide (Compound 872

To a solution of tert-butyl N-[5-[[2-[(2S,5R)-2-(4-fluorophenyl)-5-methyl-1-piperidyl]-2-oxo-acetyl]amino]-3-(trifluoromethyl)-2-pyridyl]carbamate (0.2567 g, 489.41 µmol) in dioxane (5 mL) was added Hydrogen chloride solution 4.0 M in dioxane (89.22 mg, 2.45 mmol, 111.53 µL) at 21° C. The resulting mixture was left to stir for 2 hr. The resulting mixture was evaporated to dryness and subjected to HPLC (40-65% 2-7 min water-MeCN; flow 30 ml/min; (loading pump 4 ml/min MeCN); column sunfire 100×19 mm 5 um (L)). N-[6-amino-5-(trifluoromethyl)-3-pyridyl]-2-[(2S,5R)-2-(4-fluorophenyl)-5-methyl-1-piperidyl]-2-oxo-acetamide (114.2 mg, 269.09 µmol, 54.98% yield) was obtained as a beige solid in three fractions: 1st—29.5 mg (100% by LCMS, single diastereomer); 2nd—70.4 mg (84.06% by LCMS, 15.94% of cis-); 3rd—14.3 mg (59.51% by LCMS, 40.49% of cis-).

Compound 872: $^1$H NMR (600 MHz, DMSO-$d_6$) δ (ppm) 0.96-1.03 (m, 3H), 1.20-1.37 (m, 1H), 1.59-1.70 (m, 1H), 1.80-1.94 (m, 1H), 1.99-2.13 (m, 1H), 2.13-2.24 (m, 1H), 2.70-3.20 (m, 1H), 3.44-4.02 (m, 1H), 5.12-5.60 (m, 1H), 6.32-6.41 (m, 2H), 7.15-7.24 (m, 2H), 7.27-7.40 (m, 2H), 7.96-8.11 (m, 1H), 8.32-8.45 (m, 1H), 10.70-10.93 (m, 1H).

LCMS(ESI): [M]$^+$ m/z: calcd 424.2; found 425.2; Rt=3.503 min.

The Synthesis of N-(6-amino-5-methoxypyridin-3-yl)-2-(2-(4-fluorophenyl)-5-methylpiperidin-1-yl)-2-oxoacetamide (Compound 979)

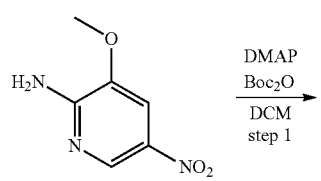

Step 1: Synthesis of tert-butyl (3-methoxy-5-nitropyridin-2-yl)carbamate 3-methoxy-5-nitro-pyridin-2-amine (2.00 g, 11.82 mmol), tert-butoxycarbonyl tert-butyl carbonate (3.87 g, 17.74 mmol, 4.07 mL) and DMAP (72.23 mg, 591.23 µmol) were refluxed in DCM (50 mL) for 16 hr. After cooling down, the reaction mixture was washed with water, dried over Na$_2$SO$_4$ and concentrated in vacuum to afford tert-butyl N-(3-methoxy-5-nitro-2-pyridyl)carbamate (1.2 g, crude) which was used in the next step without purification.

LCMS(ESI): [M]$^+$ m/z: calcd 269.2; found 270.2; Rt=1.128 min.

Step 2: Synthesis of tert-butyl (5-amino-3-methoxypyridin-2-yl)carbamate

Crude tert-butyl N-(3-methoxy-5-nitro-2-pyridyl)carbamate (250.00 mg, 928.49 µmol) was dissolved in MeOH (20 mL) followed by addition of ammonium chloride (695.33 mg, 13.00 mmol, 454.46 µL) and zinc (425.00 mg, 6.50 mmol, 59.52 µL) in one portion. The reaction mixture was stirred at 23° C. for 48 hr and then filtered. The filtrate was concentrated under reduced pressure and the residue was dissolved in a mixture of DCM and water. The organic layer was separated, dried over $Na_2SO_4$ and concentrated on rotary evaporator to afford tert-butyl N-(5-amino-3-methoxy-2-pyridyl)carbamate (0.18 g, crude) which was used in the next step without purification.

LCMS(ESI): $[M]^+$ m/z: calcd 239.2; found 240.2; Rt=0.906 min.

Step 3: Synthesis of rac-tert-butyl (5-(2-((2R,5S)-2-(4-fluorophenyl)-5-methylpiperidin-1-yl)-2-oxoacetamido)-3-methoxypyridin-2-yl)carbamate To a stirred solution of tert-butyl N-(5-amino-3-methoxy-2-pyridyl)carbamate (0.18 g, 752.29 µmol), 2-[(2R,5S)-2-(4-fluorophenyl)-5-methyl-1-piperidyl]-2-oxo-acetic acid (199.57 mg, 752.29 µmol) and DIPEA (97.23 mg, 752.29 µmol, 131.03 µL) in DMSO (2 mL) was added HATU (286.04 mg, 752.29 µmol). The resulting reaction mixture was stirred at 25° C. for 14 hr. Upon completion, the reaction mixture was diluted with water and extracted with DCM. The organic layer was separated, dried over $Na_2SO_4$ and concentrated under reduced pressure to afford tert-butyl N-[5-[[2-[(2R,5S)-2-(4-fluorophenyl)-5-methyl-1-piperidyl]-2-oxo-acetyl]amino]-3-methoxy-2-pyridyl]carbamate (0.3 g, crude) which was used in the next step without purification.

LCMS(ESI): $[M]^+$ m/z: calcd 486.2; found 487.2; Rt=1.331 min.

Step 4: Synthesis of N-(6-amino-5-methoxypyridin-3-yl)-2-(2-(4-fluorophenyl)-5-methylpiperidin-1-yl)-2-oxoacetamide (Compound 979 tert-butyl N-[5-[[2-[(2R,5S)-2-(4-fluorophenyl)-5-methyl-1-piperidyl]-2-oxo-acetyl]amino]-3-methoxy-2-pyridyl]carbamate (0.3 g, 616.61 µmol) was dissolved in a mixture of water (1 mL) and 1,4-dioxane (2.5 mL) and the reaction mixture was stirred at 80° C. for 17 hr. After cooling down, the reaction mixture was concentrated under reduced pressure and the residue was submitted to reverse phase HPLC (2-10 min 0-100% MeOH/water+FA, 30 ml/min (loading pump 4 ml MeOH); column: SunFire 100*19 mm, 5 microM) to afford N-(6-amino-5-methoxy-3-pyridyl)-2-[(2R,5S)-2-(4-fluorophenyl)-5-methyl-1-piperidyl]-2-oxo-acetamide (0.056 g, 144.92 µmol, 23.50% yield).

Compound 979: $^1$H NMR (600 MHz, DMSO-$d_6$) δ (ppm) 0.97-1.05 (m, 3H), 1.25-1.39 (m, 1H), 1.59-1.71 (m, 1H), 1.80-1.92 (m, 1H), 1.97-2.13 (m, 1H), 2.13-2.25 (m, 1H), 2.69-3.21 (m, 1H), 3.43-3.47 (m, 0.6H), 3.70-3.77 (m, 3H), 3.96-4.04 (m, 0.4H), 5.13-5.56 (m, 1H), 5.56-5.64 (m, 2H), 7.16-7.24 (m, 2H), 7.28-7.34 (m, 2H), 7.34-7.41 (m, 1H), 7.71-7.81 (m, 1H), 10.47-10.64 (m, 1H).

LCMS(ESI): $[M]^+$ m/z: calcd 386.2; found 387.2; Rt=2.282 min.

Example 722. The Synthesis of 2-(difluoromethoxy)-5-(2-(2-(4-fluorophenyl)-5-methylpiperidin-1-yl)-2-oxoacetamido)nicotinamide (Compound 889)

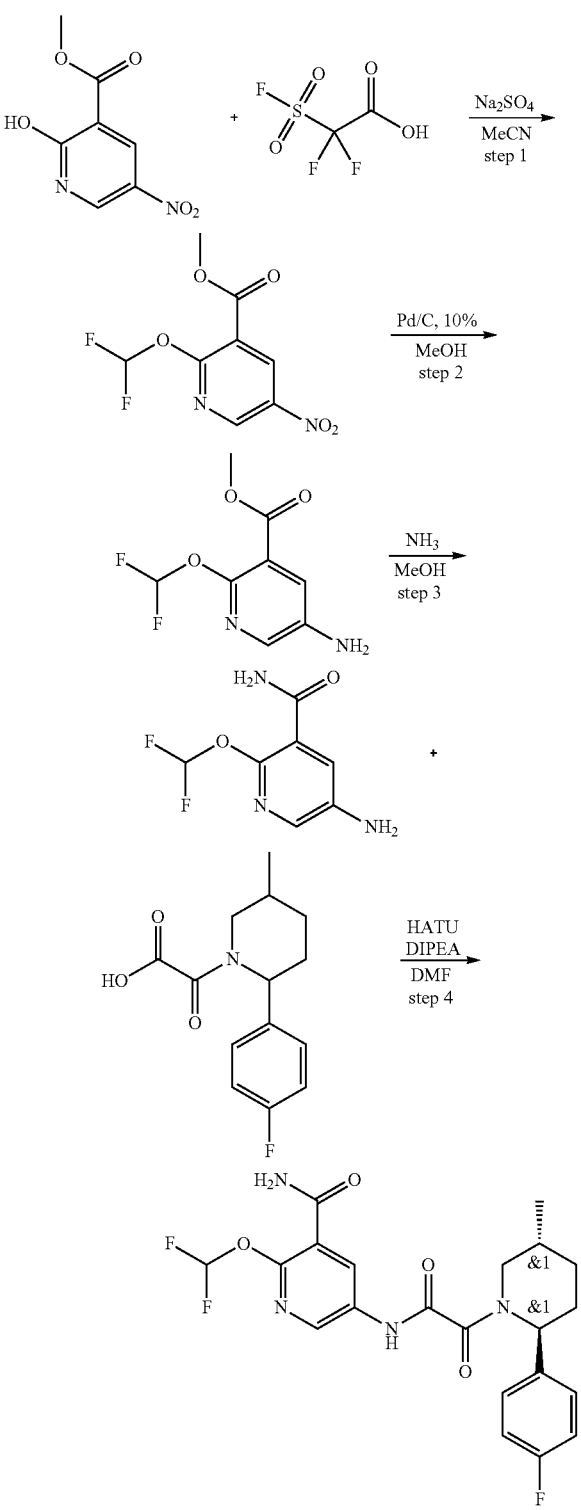

Compound 889

Step 1: Synthesis of methyl 2-(difluoromethoxy)-5-nitronicotinate

To a stirred solution of methyl 2-hydroxy-5-nitro-pyridine-3-carboxylate (5 g, 25.24 mmol) in anhydrous MeCN (100 mL) were added 2,2-difluoro-2-fluorosulfonyl-acetic acid (22.47 g, 126.18 mmol, 13.06 mL) and sodium sulfate (11.95 g, 50.47 mmol, 4.46 mL, 60% purity), and the mixture was stirred at rt for 120 hr under a nitrogen atmosphere. The reaction was quenched by addition of saturated aqueous NaHCO$_3$, and the mixture was extracted with ethyl acetate. The organic layer was washed with brine, dried over sodium sulfate, and concentrated. The residue was purified by CC (Companion combiflash; 120 g SiO$_2$, chloroform/MeCN with MeCN from 0~5%, flow rate=85 mL/min, Rv=2-2.5 CV) to give methyl 2-(difluoromethoxy)-5-nitro-pyridine-3-carboxylate (1 g, 4.03 mmol, 15.97% yield) as a light-yellow solid.

$^1$H NMR (400 MHz, DMSO-d$_6$) δ (ppm) 3.90 (s, 3H), 7.78 (t, 1H), 8.91 (s, 1H), 9.23 (s, 1H). LCMS(ESI): [M]$^+$ m/z: calcd 248.2; found 249.2; Rt=1.249 min.

Step 2: Synthesis of methyl 5-amino-2-(difluoromethoxy)Nicotinate

To a solution of methyl 2-(difluoromethoxy)-5-nitro-pyridine-3-carboxylate (0.91 g, 3.67 mmol) in MeOH (25 mL) in three-necked round-bottomed flask was added Palladium, 10% on carbon (91.00 mg, 855.10 μmol). The reaction flask was evacuated and backfilled with molecular hydrogen (7.39 mg, 3.67 mmol) and the mixture was left to stir overnight. Filtration through a thin pad of silica gel afforded a methanolic solution that was used in the next step without evaporation. Mass was calculated as if the yield was 80%.

LCMS(ESI): [M]$^+$ m/z: calcd 218.2; found 219.2; Rt=0.780 min.

Step 3: Synthesis of 5-amino-2-(difluoromethoxy)nicotinamide

An ammonia (49.96 mg, 2.93 mmol) was bubbled through a solution of methyl 5-amino-2-(difluoromethoxy)pyridine-3-carboxylate (0.64 g, 2.93 mmol). After 16 hr the reaction mixture was evaporated to dryness to give 5-amino-2-(difluoromethoxy)pyridine-3-carboxamide (700 mg, crude) as a beige solid which was used in the next step without further purification.

$^1$H NMR (500 MHz, DMSO-d$_6$) δ (ppm) 5.35 (bds, 2H), 7.44 (m, 5H). LCMS(ESI): [M]$^+$ m/z: calcd 203.2; found 204.2; Rt=0.644 min.

Step 4: Synthesis of 2-(difluoromethoxy)-5-(2-(2-(4-fluorophenyl)-5-methylpiperidin-1-yl)-2-oxoacetamido)nicotinamide (Compound 889

5-amino-2-(difluoromethoxy)pyridine-3-carboxamide (114.87 mg, 565.44 μmol), HATU (215.00 mg, 565.44 μmol) and TEA (57.22 mg, 565.44 μmol, 78.81 μL) were mixed in dry DMF (5 mL) at rt and the resulting mixture was stirred for 15 min. 2-[2-(4-fluorophenyl)-5-methyl-1-piperidyl]-2-oxo-acetic acid (0.15 g, 565.44 μmol) was added thereto and the resulting mixture was stirred at rt overnight. The resulting mixture was poured into water, extracted 3 times with EtOAc, combined organics were washed with water, brine and evaporated. The residue was subjected to HPLC (35-60% 0.5-6 min water-MeCN; flow 30 ml/min (loading pump 4 ml/min; MeCN); column SunFire 100×19 mm 5 um (R)).

Three fractions were obtained: 1st—13.4 mg (94.68% trans-, 5.32% cis-), 2nd—37.3 mg (90.84% trans-; 9.16% cis-), 3rd—13.5 mg (68.57% trans-, 31.43% cis-) as a beige solids.

Compound 889: $^1$H NMR (500 MHz, DMSO-d$_6$) δ (ppm) 1.01 (m, 3H), 1.32 (m, 1H), 1.66 (m, 1H), 1.89 (m, 1H), 2.14 (m, 2H), 3.23 (m, 1H), 3.74 (m, 1H), 5.36 (m, 1H), 7.22 (m, 2H), 7.35 (m, 2H), 7.67 (m, 3H), 8.32 (d, 1H), 8.54 (d, 1H), 11.23 (m, 1H).

LCMS(ESI): [M]$^+$ m/z: calcd 450.2; found 451.2; Rt=3.172 min.

Example 723. The Synthesis of N-(5-(difluoromethyl)-6-methoxypyridin-3-yl)-2-(2-(4-fluorophenyl)-5-methylpiperidin-1-yl)-2-oxoacetamide (Compound 1057)

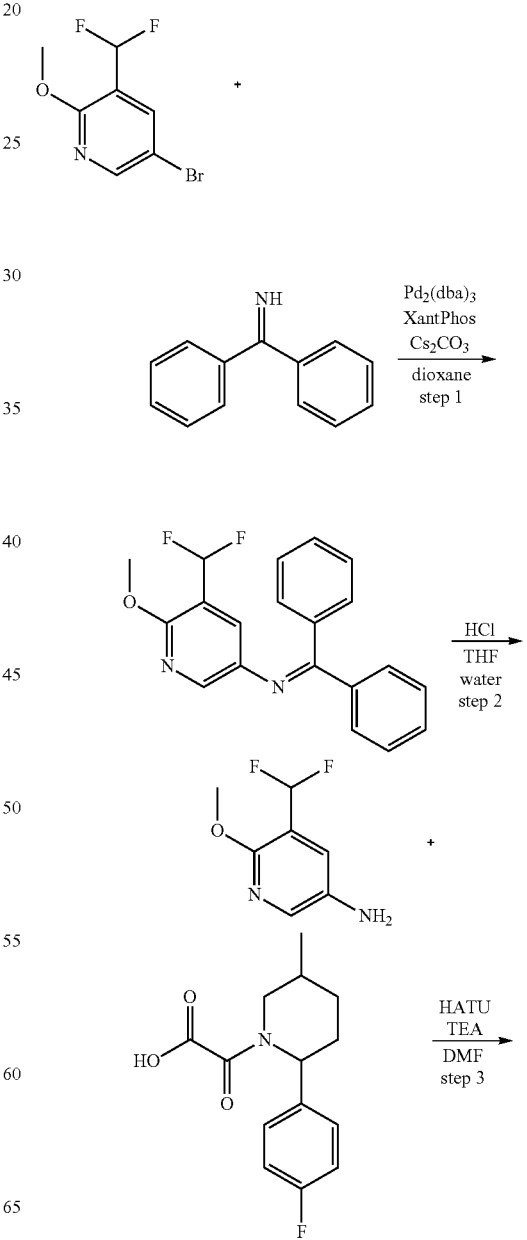

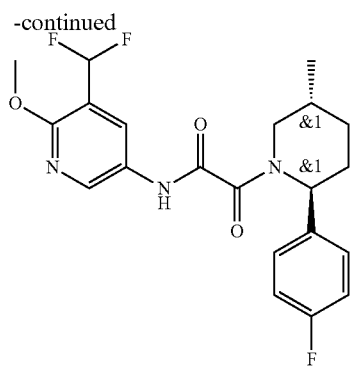

Compound 1057

Step 1: Synthesis of 5-(difluoromethyl)-N-(Diphenylmethylene)-6-methoxypyridin-3-amine A mixture of 5-bromo-3-(difluoromethyl)-2-methoxypyridine (1 g, 4.20 mmol), diphenylmethanimine (837.53 mg, 4.62 mmol, 775.49 µL), Xantphos (729.26 mg, 1.26 mmol), Pd$_2$(dba)$_3$ (192.36 mg, 210.06 µmol) and cesium carbonate (4.11 g, 12.60 mmol) in dioxane (50 mL) was degassed by bubbling argon into the mixture for several minutes. The reaction mixture was stirred at 90° C. for 12 hr under Ar atmosphere. The reaction mixture was cooled to rt and filtered. The filtrate was concentrated in vacuum and the residue was diluted with water. The mixture was extracted with ethyl acetate. The combined organic layers were washed with water, dried over Na$_2$SO$_4$, filtered and concentrated to give N-[5-(difluoromethyl)-6-methoxy-3-pyridyl]-1,1-diphenyl-methanimine (1.65 g, crude) which was used in the next step without further purification.

$^1$H NMR (400 MHz, CDCl$_3$) δ (ppm) 3.89 (s, 3H), 6.69 (t, 1H), 7.32 (m, 10H), 7.74 (m, 2H). LCMS(ESI): [M]$^+$ m/z: calcd 338.2; found 339.2; Rt=1.549 min.

Step 2: Synthesis of 5-(difluoromethyl)-6-methoxypyridin-3-amine

Hydrochloric acid, 36% w/w aq. soln. (8.00 g, 219.41 mmol, 10 mL) was added to a solution of N-[5-(difluoromethyl)-6-methoxy-3-pyridyl]-1,1-diphenyl-methanimine (1.65 g, 4.88 mmol) in THF (20 mL) and water (10 mL). Resulting mixture was stirred at 20° C. for 15 hr. Then, it was diluted with water (20 ml) and extracted with MTBE (2×20 ml). Organic layers were collected and discarded. Aqueous layer was basified to pH≈10-11 with solid K$_2$CO$_3$ and extracted with DCM (4×10 ml). Combined DCM layers were dried over K$_2$CO$_3$ and concentrated under reduced pressure, affording 5-(difluoromethyl)-6-methoxy-pyridin-3-amine (0.64 g, 3.68 mmol, 75.36% yield) as a red oil.

$^1$H NMR (400 MHz, CDCl$_3$) δ (ppm) 3.52 (bds, 2H), 3.89 (s, 3H), 6.77 (t, 1H), 7.25 (s, 1H), 7.72 (s, 1H).

LCMS(ESI): [M]$^+$ m/z: calcd 174.2; found 175.2; Rt=0.744 min.

Step 3: Synthesis of N-(5-(difluoromethyl)-6-methoxypyridin-3-yl)-2-(2-(4-fluorophenyl)-5-methylpiperidin-1-yl)-2-oxoacetamide (Compound 1057

5-(difluoromethyl)-6-methoxy-pyridin-3-amine (0.05 g, 287.11 µmol), HATU (109.17 mg, 287.11 µmol) and TEA (29.05 mg, 287.11 µmol, 40.02 µL) were mixed in dry DMF (5 mL) at rt and the resulting mixture was stirred for 15 min. 2-[(2R,5S)-2-(4-fluorophenyl)-5-methyl-1-piperidyl]-2-oxo-acetic acid (76.17 mg, 287.11 µmol) was added thereto and the resulting mixture was stirred at rt overnight. The resulting mixture was poured into water, extracted 3 times with EtOAc, combined organics were washed with water, brine and evaporated. The residue was subjected to HPLC (1st run: 45-70% 0.5-6.5 min water-MeCN; flow 30 ml/min (loading pump 4 ml/min; MeCN); column SunFire C18 100×19 mm 5 um (R), 2nd run: 50-100% 0.5-6.5 min water-MeOH; flow 30 ml/min (loading pump 4 ml/min MeOH); column xbridge C18 100×19 mm 5 um (R)). N-[5-(difluoromethyl)-6-methoxy-3-pyridyl]-2-[(2R,5S)-2-(4-fluorophenyl)-5-methyl-1-piperidyl]-2-oxo-acetamide (63.5 mg, 150.68 µmol, 52.48% yield) was obtained as a yellow gum.

Compound 1057: $^1$H NMR (600 MHz, DMSO-d$_6$) δ (ppm) 1.01 (d, 3H), 1.32 (m, 1H), 1.66 (m, 1H), 1.91 (m, 1H), 2.03 (m, 1H), 2.17 (m, 1H), 3.21 (m, 1H), 3.48 (m, 1H), 3.92 (s, 3H), 5.48 (m, 1H), 7.03 (m, 1H), 7.21 (m, 2H), 7.35 (m, 2H), 8.23 (m, 1H), 8.55 (m, 1H), 11.12 (m, 1H).

LCMS(ESI): [M]$^+$ m/z: calcd 421.2; found 422.2; Rt=3.962 min.

Example 724. The Synthesis of N-(6-amino-5-cyclopropyl-3-pyridyl)-2-[(2R,5S)-2-(4-fluorophenyl)-5-methyl-1-piperidyl]-2-oxo-acetamide (Compound 989)

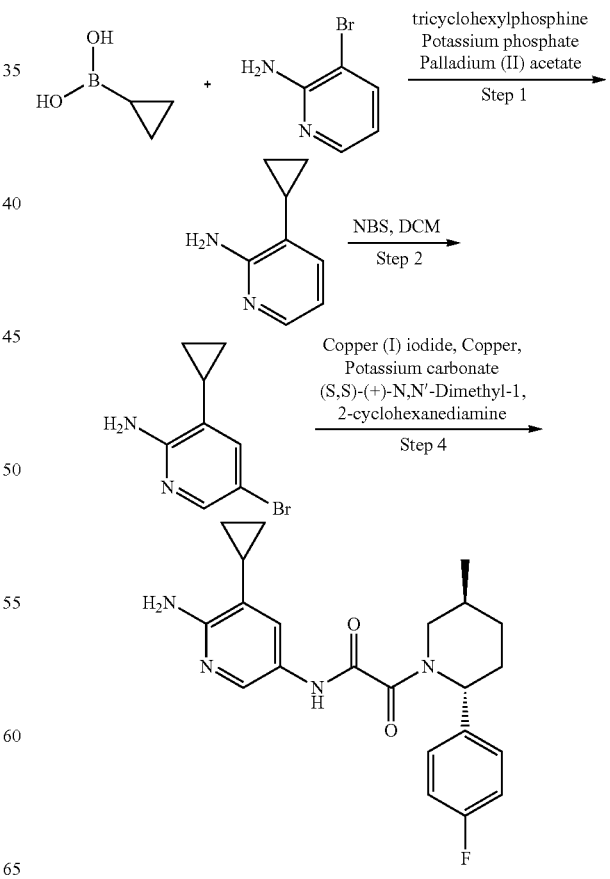

Compound 989

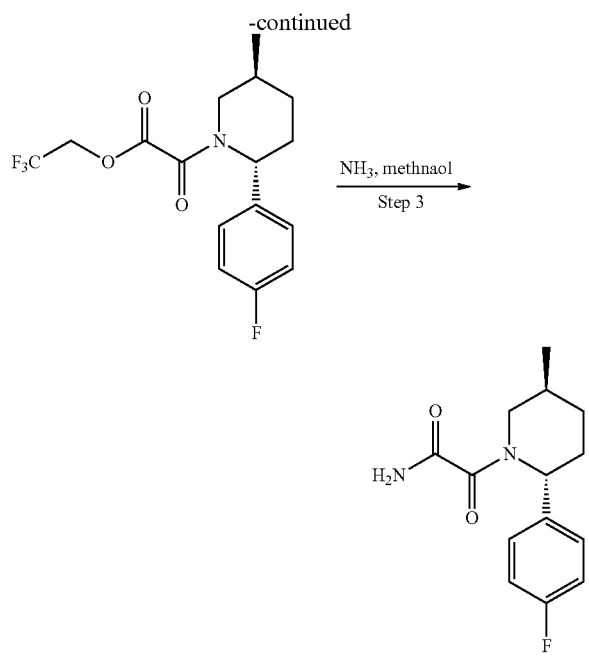

Step 1. Synthesis of 3-cyclopropylpyridin-2-amine

To a solution of 3-bromopyridin-2-amine (50 g, 289.00 mmol) in toluene (500 mL) and water (100 mL) were added Cyclopropyl boronic acid (32.27 g, 375.70 mmol), tricyclohexylphosphine (8.10 g, 28.90 mmol), Potassium phosphate tribasic anhydrous (184.03 g, 867.00 mmol) and Palladium (II) acetate (3.24 g, 14.45 mmol). The reaction mixture was purged with Ar for 2 min and heated to 90° C. for 16 h and subsequently concentrated to dryness in vacuo. The resulting viscous mass was diluted with water and extracted with MTBE (3×500 mL). The combined organic layers were dried over sodium sulfate and concentrated to dryness in vacuo. 3-cyclopropylpyridin-2-amine (59 g, crude) was obtained as a brown oil, which was used in the next step without further purification.

$^1$H NMR (500 MHz, CDCl$_3$) δ (ppm) 0.57 (m, 2H), 0.92 (m, 2H), 1.61 (m, 1H), 4.88 (brs, 2H), 6.58 (m, 1H), 7.23 (m, 1H), 7.94 (m, 1H).

LCMS(ESI): [M+1]$^+$ m/z: calcd 134.1; found 135.2; Rt=0.609 min.

Step 2. Synthesis of 5-bromo-3-cyclopropyl-pyridin-2-amine

NBS (50.87 g, 285.81 mmol, 24.22 mL) was added portion-wise to a solution of 3-cyclopropylpyridin-2-amine (59 g, 285.81 mmol) in dry DCM and the reaction mixture was stirred at r.t. for 3 h. It was washed with water (1×) and the aqueous layer re-extracted with dichloromethane (3×). The combined organic extracts were washed with brine (1×) and dried (Na$_2$SO$_4$). The solvent was removed under reduced pressure to give a residue which was purified by CC (Interchim; 800 g SiO$_2$, chloroform/acetonitrile with acetonitrile from 0~40%, flow rate=150 mL/min, Rv=5-6 CV) to give 5-bromo-3-cyclopropyl-pyridin-2-amine (30.4 g, 142.67 mmol, 49.92% yield) as a brown solid.

$^1$H NMR (500 MHz, CDCl$_3$) δ (ppm) 0.59 (m, 2H), 0.94 (m, 2H), 1.59 (m, 1H), 4.78 (brs, 2H), 7.32 (s, 1H), 7.96 (s, 1H).

LCMS(ESI): [M+1]$^+$ m/z: calcd 212.1; found 213.2; Rt=0.834 min.

Step 3. Synthesis of tert-butyl 6-[5-[tert-butoxycarbonyl(methyl)amino]-2-pyridyl]-3-methyl-3,4-dihydro-2H-pyridine-1-carboxylate ammonia (93.66 mg, 5.50 mmol) was bubbled through a solution of 2,2,2-trifluoroethyl 2-[(2R,5S)-2-(4-fluorophenyl)-5-methyl-1-piperidyl]-2-oxo-acetate (1.91 g, 5.50 mmol) (prepared as described above) in MeOH (50 mL) at rt. After 1 hr the resulting mixture was evaporated to dryness and reevaporated with benzene. 2-[(2R,5S)-2-(4-fluorophenyl)-5-methyl-1-piperidyl]-2-oxo-acetamide (1.35 g, crude) was obtained as a white semi-solid.

$^1$H NMR (500 MHz, DMSO) δ (ppm) 0.98 (m, 3H), 1.32 (m, 1H), 1.65-1.97 (m, 3H), 2.60 (m, 1H), 3.14 (d, 1H), 3.39-3.96 (m, 1H), 5.04 and 5.51 (two singles rotamers, 1H), 7.21 (m, 3H), 7.29 (m, 1H), 7.72 (m, 1H), 8.21 (m, 1H).

LCMS(ESI): [M+1]$^+$ m/z: calcd 264.1; found 265.2; Rt=2.369 min.

Step 4. Synthesis of N-(6-amino-5-cyclopropyl-3-pyridyl)-2-[(2R,5S)-2-(4-fluorophenyl)-5-methyl-1-piperidyl]-2-oxo-acetamide (Compound 989

2-[(2R,5S)-2-(4-fluorophenyl)-5-methyl-1-piperidyl]-2-oxo-acetamide (0.1 g, 378.37 μmol), 5-bromo-3-cyclopropyl-pyridin-2-amine (120.93 mg, 567.55 μmol), Copper (12.02 mg, 189.18 μmol), Copper (I) iodide (7.21 mg, 37.84 μmol, 1.28 μL), (S,S)-(+)-N,N'-dimethyl-1,2-cyclohexanediamine (5.38 mg, 37.84 μmol, 5.97 μL) and Potassium carbonate (104.59 mg, 756.73 μmol, 45.67 μL) were mixed together in Toluene (12 mL). Stream of argon was bubbled through reaction mixture for 2 min before it was stirred in a sealed flask at 105° C. for 18 hr. Then, it was diluted with ethyl acetate (20 ml) and 5% aq. NH$_3$ solution (15 ml), Resulting biphasic mixture was filtered through a florisil pad. Organic layer was separated, dried over Na$_2$SO$_4$ and concentrated under reduced pressure. Residue was purified by HPLC(35-60% 0.5-6.5 min water-acetonitrile; flow 30 ml/min (loading pump 4 ml/min acetonitrile); column SunFire C18 100×19 mm 5 um (R)), affording N-(6-amino-5-cyclopropyl-3-pyridyl)-2-[(2R,5S)-2-(4-fluorophenyl)-5-methyl-1-piperidyl]-2-oxo-acetamide (2.7 mg, 6.81 μmol, 1.80% yield) as a yellow gum.

LCMS(ESI): [M+1]$^+$ m/z: calcd 396.2; found 397.2; Rt=2.41 min.

Example 725. The Synthesis of N-(6-amino-5-(difluoromethoxy)pyridin-3-yl)-2-(2-(4-fluorophenyl)-5-methylpiperidin-1-yl)-2-oxoacetamide (Compound 1026)

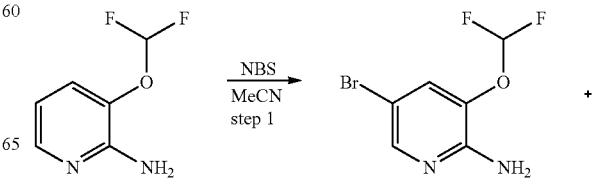

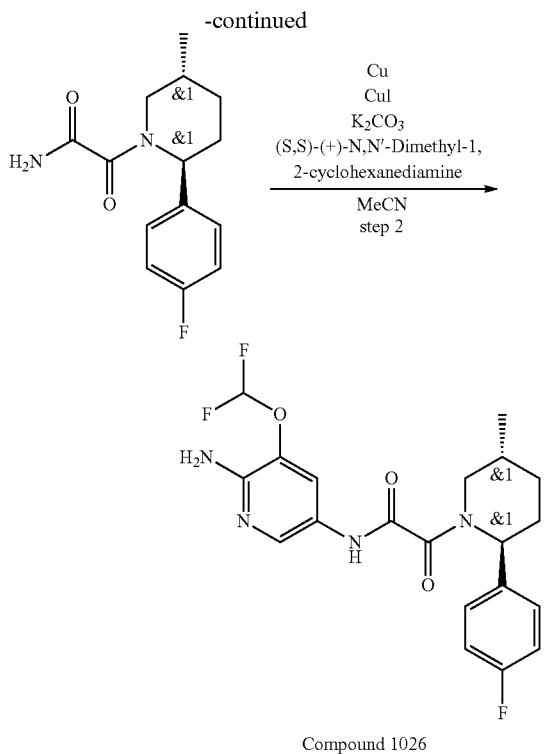

Compound 1026

Step 1: Synthesis of 5-bromo-3-(difluoromethoxy)pyridin-2-amine

To the stirred solution of 3-(difluoromethoxy)pyridin-2-amine (3 g, 18.74 mmol) in MeCN (25 mL) N-bromosuccinimide (3.50 g, 19.67 mmol, 1.67 mL) was added. The resulting mixture was stirred 25° C. for 12 hr. MeCN was evaporated under reduce pressure. The residue was diluted with water (50 ml) and extracted with EtOAc (2*50 ml). Combined organic layer were washed with water and brine, dried over $Na_2SO_4$. EtOAc was evaporated under reduce pressure to give 5-bromo-3-(difluoromethoxy)pyridin-2-amine (4 g, 16.74 mmol, 89.32% yield).

$^1$H NMR (500 MHz, $CDCl_3$) δ (ppm) 4.75 (bds, 2H), 6.52 (t, 1H), 7.41 (s, 1H), 7.98 (s, 1H). LCMS(ESI): [M]$^+$ m/z: calcd 239.2; found 240.2; Rt=1.192 min.

Step 2: Synthesis of N-(6-amino-5-(difluoromethoxy)pyridin-3-yl)-2-(2-(4-fluorophenyl)-5-methylpiperidin-1-yl)-2-oxoacetamide (Compound 1026)

A mixture of 5-bromo-3-(difluoromethoxy)pyridin-2-amine (0.2 g, 836.76 μmol), 2-[(2R,5S)-2-(4-fluorophenyl)-5-methyl-1-piperidyl]-2-oxo-acetamide (221.15 mg, 836.76 μmol) (prepared as shown above), copper (I) iodide (31.87 mg, 167.35 μmol, 5.67 μL), potassium carbonate, anhydrous, 99% (231.30 mg, 1.67 mmol, 101.00 μL), $N^1,N^2$-dimethylcyclohexane-1,2-diamine (23.80 mg, 167.35 μmol), copper (2.66 mg, 41.84 μmol) and MeCN (10 mL) in 100 ml single-neck round bottom flask equipped with a reflux condenser and glass stopper was evacuated and then backfilled with argon. The reaction mixture was then stirred with a reflux condenser under argon at 100° C. for 36 hr. The reaction mixture was then purified by reverse phase HPLC (50-65% 0-6 min $H_2O$/MeOH/0.1% $NH_4OH$, flow: 30 ml/min (loading pump 4 ml/min MeOH) target mass 423 column: YMC Triart C18 100×20 mm, 5 um) to give N-[6-amino-5-(difluoromethoxy)-3-pyridyl]-2-[(2R,5S)-2-(4-fluorophenyl)-5-methyl-1-piperidyl]-2-oxo-acetamide (19 mg, 44.98 μmol, 5.38% yield).

Compound 1026: $^1$H NMR (600 MHz, DMSO-$d_6$) δ (ppm) 0.98 (d, 3H), 1.31 (m, 1H), 2.01 (m, 3H), 3.20 (m, 1H), 3.65 (m, 2H), 5.53 (m, 1H), 5.98 (m, 2H), 7.18 (m, 1H), 7.21 (m, 2H), 7.31 (m, 2H), 7.68 (m, 1H), 8.07 (m, 1H), 10.74 (s, 1H).

LCMS(ESI): [M]$^+$ m/z: calcd 422.2; found 423.2; Rt=2.925 min.

Example 726. The Synthesis of N-(6-amino-5-isopropylpyridin-3-yl)-2-(2-(4-fluorophenyl)-5-methylpiperidin-1-yl)-2-oxoacetamide (Compound 993)

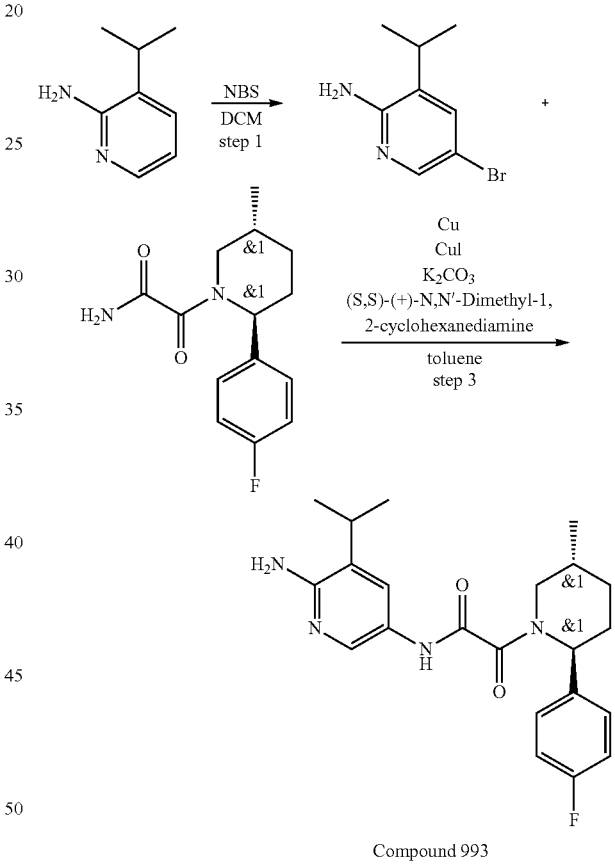

Compound 993

Step 1: Synthesis of 5-bromo-3-isopropylpyridin-2-amine

NBS (1.37 g, 7.71 mmol, 653.42 μL) was added, in one portion, to a solution of 3-isopropylpyridin-2-amine (1 g, 7.34 mmol) in dry DCM (25 mL) and the reaction mixture was stirred at rt for 2 hr. It was washed with water and the aqueous layer re-extracted with dichloromethane. The combined organic extracts were washed with brine and dried $Na_2SO_4$. The solvent was removed under reduced pressure to give crude 5-bromo-3-isopropyl-pyridin-2-amine (1.44 g, crude) as a brown solid.

$^1$H NMR (400 MHz, CDCl$_3$) δ (ppm) 1.26 (d, 6H), 2.73 (m, 1H), 5.02 (bds, 2H), 7.45 (s, 1H), 7.96 (s, 1H). LCMS (ESI): [M]$^+$ m/z: calcd 215.2; found 216.2; Rt=0.902 min.

Step 2: Synthesis of N-(6-amino-5-Isopropylpyridin-3-yl)-2-(2-(4-fluorophenyl)-5-methylpiperidin-1-yl)-2-oxoacetamide (Compound 993

2-[(2R,5S)-2-(4-fluorophenyl)-5-methyl-1-piperidyl]-2-oxo-acetamide (0.1 g, 378.37 μmol), 5-bromo-3-isopropyl-pyridin-2-amine (81.38 mg, 378.37 μmol), copper (12.02 mg, 189.18 μmol), copper (I) iodide (7.21 mg, 37.84 μmol, 1.28 μL), (S,S)-(+)-N,N'-dimethyl-1,2-cyclohexanediamine (5.38 mg, 37.84 μmol, 5.97 μL) and potassium carbonate (104.59 mg, 756.73 μmol, 45.67 μL) were mixed together in toluene (12 mL). Stream of argon was bubbled through reaction mixture for 2 min before it was stirred in a sealed flask at 105° C. for 18 hr. Then, it was diluted with ethyl acetate (20 ml) and 5% aq. NH$_3$ solution (15 ml). Resulting biphasic mixture was filtered through a celite pad. Organic layer was separated, dried over Na$_2$SO$_4$ and concentrated under reduced pressure. Residue was purified by HPLC(40-70 0.5-6.5 min water-MeCN; flow 30 ml/min (loading pump 4 ml/min; MeCN); column SunFire C18 100×19 mm 5 um (R)), affording N-(6-amino-5-isopropyl-3-pyridyl)-2-[(2R, 5S)-2-(4-fluorophenyl)-5-methyl-1-piperidyl]-2-oxo-acetamide (7.4 mg, 18.57 μmol, 4.91% yield) as a yellow gum. Two fractions were obtained: 1st—1.7 mg (93.81% by LCMS); 2nd—5.7 mg (96.8% of trans-; 3.2% of cis-).

Compound 993: $^1$H NMR (600 MHz, DMSO-d$_6$) δ (ppm) 0.96-1.04 (m, 3H), 1.06-1.15 (m, 6H), 1.26-1.38 (m, 1H), 1.59-1.71 (m, 1H), 1.79-1.94 (m, 1H), 1.96-2.12 (m, 1H), 2.13-2.26 (m, 1H), 2.67-2.74 (m, 0.3H), 2.84-2.91 (m, 1H), 3.17-3.22 (m, 0.7H), 3.44-4.05 (m, 1H), 5.11-5.60 (m, 1H), 5.61-5.71 (m, 2H), 7.17-7.24 (m, 2H), 7.31-7.41 (m, 2H), 7.47-7.57 (m, 1H), 7.98-8.11 (m, 1H), 10.39-1 Compound 0.69 (m, 1H).

LCMS(ESI): [M]$^+$ m/z: calcd 398.2; found 399.2; Rt=2.635 min.

Example 727. The Synthesis of N-(5-ethyl-6-methylpyridin-3-yl)-2-(2-(4-fluorophenyl)-5-methylpiperidin-1-yl)-2-oxoacetamide (Compound 779)

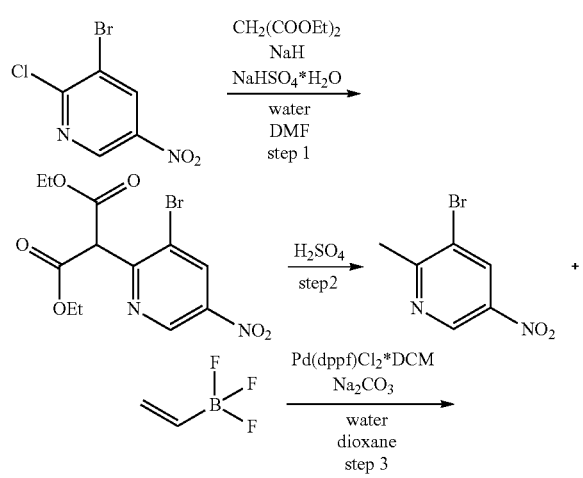

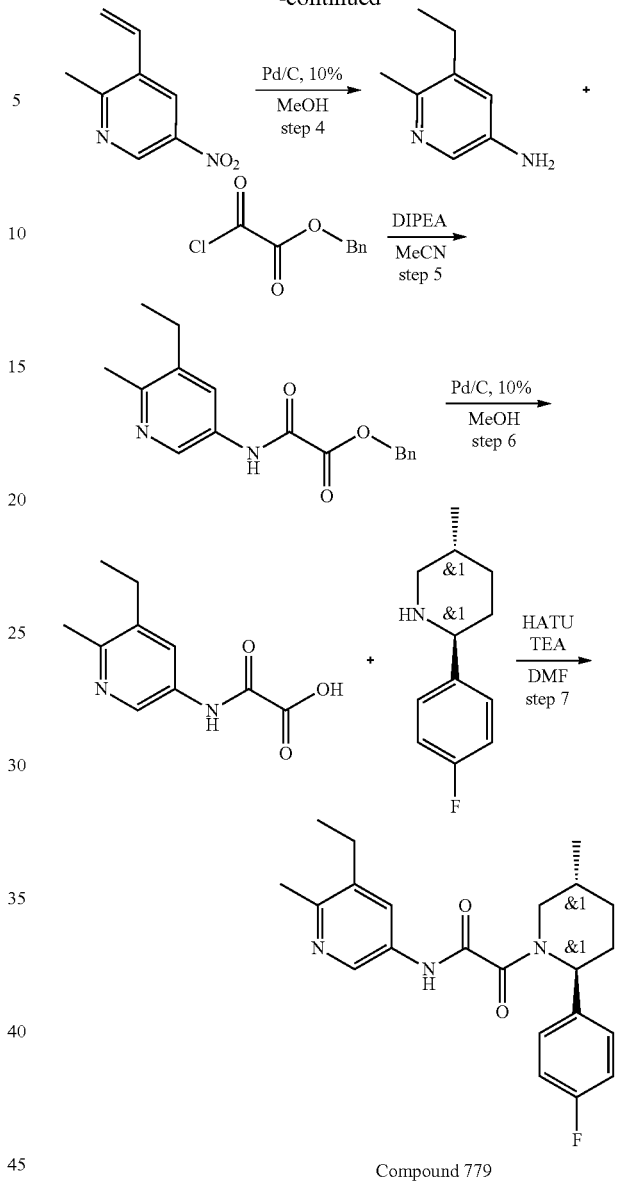

Compound 779

Step 1: Synthesis of Diethyl 2-(3-bromo-5-nitropyridin-2-yl)malonate

Diethyl propanedioate (20.24 g, 126.35 mmol, 19.09 mL) was added dropwise to a suspension of sodium hydride (in oil dispersion) 60% dispersion in mineral oil (5.81 g, 145.30 mmol, 60% purity) in DMF (200 mL). After H$_2$ evolution ceased, 3-bromo-2-chloro-5-nitro-pyridine (15 g, 63.17 mmol) was added portion wise during 30 minutes. Resulting mixture was stirred at 20° C. for 15 hr. Then, it was poured into ice-cold solution of sodium hydrogen sulfate monohydrate (21.81 g, 157.94 mmol) in water (800 mL). Resulting mixture was extracted with ethyl acetate (2×250 ml). Organic layer was separated and washed successively with water (2×150 ml) and brine (100 ml), dried over Na$_2$SO$_4$ and concentrated under reduced pressure. Residue was diluted with cold (−5-0° C.) hexane (150 ml). Precipitated orange solid was collected by filtration and dried, affording diethyl 2-(3-bromo-5-nitro-2-pyridyl)propanedioate (21.8 g, 60.36 mmol, 95.55% yield).

¹H NMR (500 MHz, CDCl₃) δ (ppm) 1.30 (t, 6H), 4.31 (m, 4H), 5.28 (s, 1H), 8.68 (s, 1H), 9.33 (s, 1H). LCMS (ESI): [M]⁺ m/z: calcd 361.2; found 362.2; Rt=1.373 min.

Step 2: Synthesis of
3-bromo-2-methyl-5-nitropyridine

Diethyl 2-(3-bromo-5-nitro-2-pyridyl)propanedioate (21.8 g, 60.36 mmol) was suspended in Sulfuric acid (10%) (214.00 g, 218.19 mmol, 200 mL, 10% purity) and resulting mixture was stirred at 110° C. for 5 hr. Then, it was cooled and extracted with DCM (3×60 ml). Combined organic layers were dried over Na₂SO₄ and concentrated under reduced pressure, affording 3-bromo-2-methyl-5-nitro-pyridine (12.5 g, 57.60 mmol, 95.42% yield).

¹H NMR (500 MHz, CDCl₃) δ (ppm) 2.78 (s, 3H), 8.58 (s, 1H), 9.22 (s, 1H). LCMS(ESI): [M]⁺ m/z: calcd 217.2; found 218.2; Rt=1.188 min.

Step 3: Synthesis of
2-methyl-5-nitro-3-vinylpyridine

Sodium carbonate (7.33 g, 69.12 mmol, 2.90 mL) was added to a solution of 3-bromo-2-methyl-5-nitro-pyridine (6 g, 27.65 mmol) and trifluoro(vinyl)boranuide (5.18 g, 38.71 mmol, K⁺) in dioxane (80 mL) and water (30 mL). Reaction flask was evacuated and refilled with argon 3 times. Then, Pd(dppf)Cl₂*DCM (903.11 mg, 1.11 mmol) was added under stream of argon. Resulting mixture was stirred at 90° C. for 24 hr under inert atmosphere. Then, it was concentrated under reduced pressure and residue was extracted with 50:50 mixture hexane/MTBE (100 ml). Obtained solution was filtered through a short pad of silica gel and evaporated under reduced pressure, affording 2-methyl-5-nitro-3-vinyl-pyridine (3.2 g, 19.49 mmol, 70.51% yield).

¹H NMR (500 MHz, CDCl₃) δ (ppm) 2.69 (s, 3H), 5.61 (d, 1H), 5.86 (d, 1H), 6.92 (m, 1H), 8.47 (s, 1H), 9.20 (s, 1H). LCMS(ESI): [M]⁺ m/z: calcd 164.2; found 165.2; Rt=1.132 min.

Step 4: Synthesis of
5-ethyl-6-methylpyridin-3-amine

Palladium, 10% on carbon (400 mg, 375.87 μmol, 10% purity) was added to a solution of 2-methyl-5-nitro-3-vinyl-pyridine (3.2 g, 19.49 mmol) in MeOH (60 mL). Reaction flask was evacuated and backfilled with hydrogen (785.88 mg, 389.86 mmol) from attached balloon. Resulting mixture was stirred at 20° C. for 16 hr. Then, catalyst was filtered off and filtrate was concentrated under reduced pressure, affording 5-ethyl-6-methyl-pyridin-3-amine (2.6 g, 19.09 mmol, 97.93% yield).

¹H NMR (400 MHz, CDCl₃) δ (ppm) 1.15 (t, 3H), 2.38 (s, 3H), 2.52 (m, 2H), 3.45 (m, 2H), 6.77 (s, 1H), 7.82 (s, 1H). LCMS(ESI): [M]⁺ m/z: calcd 136.2; found 137.2; Rt=0.568 min.

Step 5: Synthesis of Benzyl 2-((5-ethyl-6-methylpyridin-3-yl)amino)-2-oxoacetate A solution of benzyl 2-chloro-2-oxo-acetate (4.17 g, 21.00 mmol) in MeCN (15 mL) was added dropwise at 0° C. to a stirred solution of 5-ethyl-6-methyl-pyridin-3-amine (2.6 g, 19.09 mmol) and N,N-diisopropylethylamine (2.96 g, 22.91 mmol, 3.99 mL) in MeCN (30 mL). The reaction mixture was allowed to warm to 25° C. and stirred for 4 hr, then evaporated in vacuum. The residue was diluted with water (60 ml) and stirred for 0.5 hr. The precipitate was filtered, washed successively with water (2×30 ml) and hexane (30 ml), and air-dried to afford benzyl 2-[(5-ethyl-6-methyl-3-pyridyl)amino]-2-oxo-acetate (5.06 g, 16.96 mmol, 88.84% yield) as light-brown solid.

¹H NMR (500 MHz, DMSO-d₆) δ (ppm) 1.15 (t, 3H), 2.41 (s, 3H), 2.59 (m, 2H), 5.33 (s, 2H), 7.46 (m, 5H), 7.88 (s, 1H), 8.62 (s, 1H), 10.94 (s, 1H). LCMS(ESI): [M]⁺ m/z: calcd 298.2; found 299.2; Rt=1.002 min.

Step 6: Synthesis of 2-((5-ethyl-6-methylpyridin-3-yl)amino)-2-oxoacetic acid

A mixture of benzyl 2-[(5-ethyl-6-methyl-3-pyridyl)amino]-2-oxo-acetate (5.06 g, 16.96 mmol) and palladium, 10% on carbon (0.6 g, 563.80 μmol, 10% purity) in MeOH (100 mL) was stirred under atmosphere of hydrogen at 20° C. for 12 hr. Then, TEA (3.43 g, 33.92 mmol, 4.73 mL) was added and stirring was continued for 5 minutes. Catalyst was filtered off, and filtrate was evaporated to dryness under reduced pressure, affording 2-[(5-ethyl-6-methyl-3-pyridyl)amino]-2-oxo-acetic acid (5.06 g, 16.35 mmol, 96.42% yield, Et₃N).

¹H NMR (400 MHz, DMSO-d₆) δ (ppm) 1.13 (t, 3H), 2.34 (s, 3H), 2.52 (m, 2H), 7.88 (s, 1H), 8.59 (s, 1H), 10.13 (s, 1H).

LCMS(ESI): [M]⁺ m/z: calcd 208.2; found 209.2; Rt=0.636 min.

Step 7: Synthesis of N-(5-ethyl-6-methylpyridin-3-yl)-2-(2-(4-fluorophenyl)-5-methylpiperidin-1-yl)-2-oxoacetamide (Compound 779

To a stirred mixture of 2-[(5-ethyl-6-methyl-3-pyridyl)amino]-2-oxo-acetic acid (128 mg, 413.70 μmol, Et₃N), (2R,5S)-2-(4-fluorophenyl)-5-methyl-piperidine (80 mg, 413.95 μmol) and TEA (62.79 mg, 620.55 μmol, 86.49 μL) in DMF (2 mL) was added HATU (173.03 mg, 455.07 μmol). The resulting reaction mixture was stirred at 20° C. for 4 hr. Then, it was subjected to HPLC (Column: YMC Triart C18 100×20 mm, 5 um 50-90% 0-5 min; H₂O-MeOH (0.1% NH₃), flow: 30 ml/min) and subsequently to Chiral HPLC (Column: Chiralpak AD-H (250×20 mm, 5 um); Mobile phase: Hexane-IPA-MeOH, 50-25-25 Flow Rate: 12 mL/min; Column Temperature: 24° C.), affording N-(5-ethyl-6-methyl-3-pyridyl)-2-[(2R,5S)-2-(4-fluorophenyl)-5-methyl-1-piperidyl]-2-oxo-acetamide (96 mg, 250.35 μmol, 60.52% yield).

Compound 779: ¹H NMR (600 MHz, DMSO-d₆) δ (ppm) 0.96-1.03 (m, 3H), 1.08-1.17 (m, 3H), 1.27-1.38 (m, 1H), 1.59-1.71 (m, 1H), 1.81-1.91 (m, 1H), 1.98-2.13 (m, 1H), 2.14-2.24 (m, 1H), 2.36-2.42 (m, 3H), 2.50-2.58 (m, 2H), 2.70-3.25 (m, 1H), 3.38-4.04 (m, 1H), 5.07-5.62 (m, 1H), 7.15-7.26 (m, 2H), 7.31-7.42 (m, 2H), 7.75-7.85 (m, 1H), 8.37-8.57 (m, 1H), 10.83-11.03 (m, 1H).

LCMS(ESI): [M]⁺ m/z: calcd 383.2; found 384.2; Rt=1.088 min.

Example 728. The Synthesis of N-(6-amino-5-methylpyridin-3-yl)-2-(5-methyl-2-(5-(1-(tetrahydro-2H-pyran-2-yl)-1H-pyrazol-5-yl)thiophen-2-yl)piperidin-1-yl)-2-oxoacetamide (Compound 556 and Compound 577

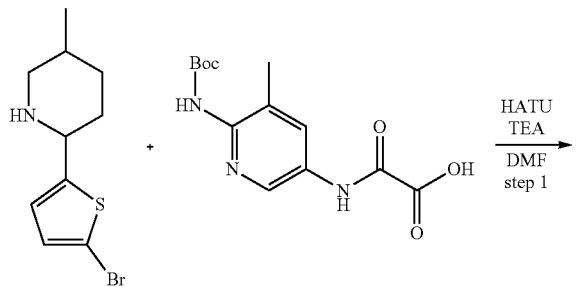

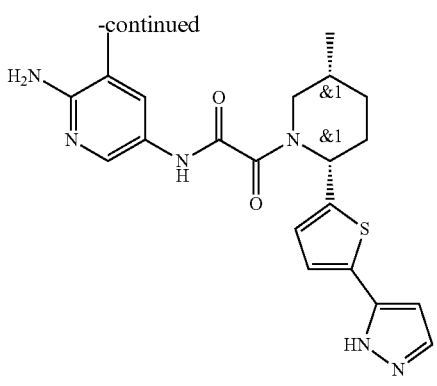

Compound 577

Step 1: Synthesis of tert-butyl (5-(2-(2-(5-bromothiophen-2-yl)-5-methylpiperidin-1-yl)-2-oxoacetamido)-3-methylpyridin-2-yl)carbamate 2-(5-bromo-2-thienyl)-5-methyl-piperidine (0.35 g, 1.35 mmol) (prepared as described in the synthesis of intermediate 3C) and 2-[[6-(tert-butoxycarbonylamino)-5-methyl-3-pyridyl]amino]-2-oxo-acetic acid (397.21 mg, 1.35 mmol) were mixed in DMF (30 mL). The reaction suspension was cooled to 20° C. and HATU (511.47 mg, 1.35 mmol) followed by TEA (136.12 mg, 1.35 mmol, 187.49 µL) were added and stirred at ambient temperature for 15 hr. The reaction mixture was evaporated in vacuum and poured into water (200 ml) and extracted with EtOAc (2×60 ml). The combined organic extracts were washed with water (2*30 ml), dried over sodium sulphate and evaporated in vacuum to afford product tert-butyl N-[5-[[2-[2-(5-bromo-2-thienyl)-5-methyl-1-piperidyl]-2-oxo-acetyl]amino]-3-methyl-2-pyridyl]carbamate (0.5 g, 930.29 µmol, 69.16% yield).

$^1$H NMR (400 MHz, CDCl$_3$) δ (ppm) 1.26 (d, 3H), 1.49 (s, 9H), 2.02 (s, 3H), 2.27 (m, 4H), 2.77 (m, 1H), 3.69 (m, 1H), 4.76 (m, 2H), 6.71 (m, 2H), 6.93 (m, 1H), 8.04 (m, 1H), 8.32 (m, 1H), 9.20 (m, 1H).

LCMS(ESI): [M]m/z: calcd 537.2; found 538.2; Rt=1.443 min.

Step 2: Synthesis of rac-tert-butyl (3-methyl-5-(2-((2R,5S)-5-methyl-2-(5-(1-(tetrahydro-2H-pyran-2-yl)-1H-pyrazol-5-yl)thiophen-2-yl)piperidin-1-yl)-2-oxoacetamido)pyridin-2-yl)carbamate tert-butyl N-[5-[[2-[2-(5-bromo-2-thienyl)-5-methyl-1-piperidyl]-2-oxo-acetyl]amino]-3-methyl-2-pyridyl]carbamate (0.5 g, 930.29 µmol) and 1-tetrahydropyran-2-yl-5-(4,4,5,5-tetramethyl-1,3,2-dioxaborolan-2-yl)pyrazole (258.76 mg, 930.29 µmol) were mixed together in water (2 mL). The resulting mixture was evacuated and then backfilled with argon, this operation was repeated three times, then sodium carbonate (197.20 mg, 1.86 mmol, 77.95 µL) in water (2 mL) and [1,1'-bis(diphenylphosphino)ferrocene]dichloropalladium(II), complex with DCM (37.99 mg, 46.51 µmol) were added under argon. The reaction mixture was stirred under argon at 100° C. for 18 hr, then cooled and evaporated in vacuum poured into water (50 ml) and extracted with EtOAc (2×20 ml). The combined organic extracts were washed with water (2*10 ml), dried over sodium sulphate and evaporated in vacuum to afford product tert-butyl N-[3-methyl-5-[[2-[5-methyl-2-[5-(2-tetrahydropyran-2-ylpyrazol-3-yl)-2-thienyl]-1-piperidyl]-2-oxo-acetyl]amino]-2-pyridyl]carbamate (0.63 g, crude).

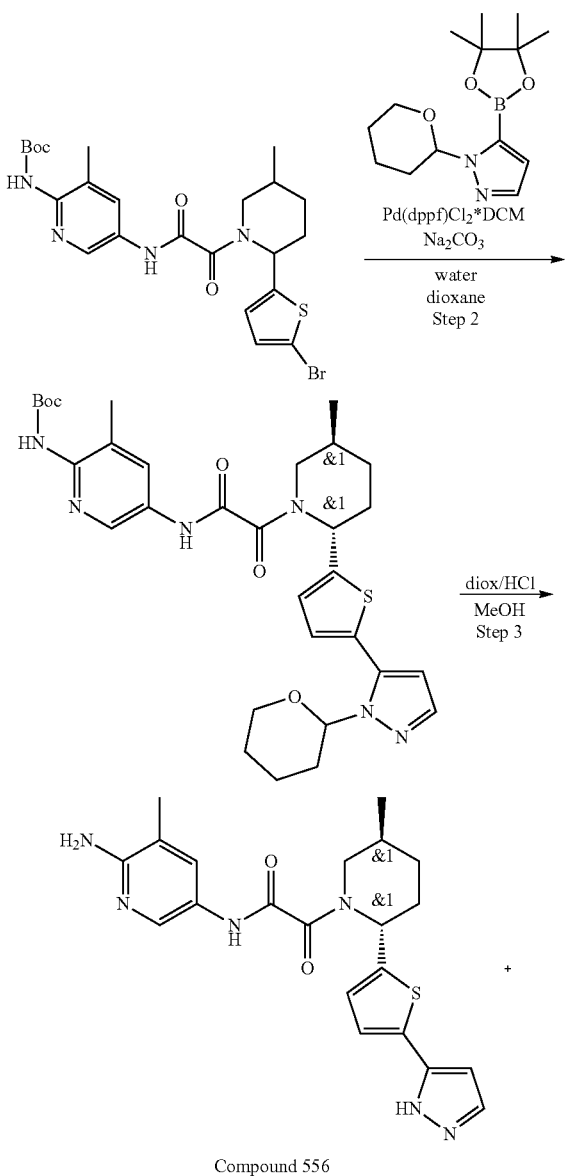

Compound 556

2977

$^1$H NMR (400 MHz, CDCl$_3$) δ (ppm) 1.09 (d, 3H), 1.23 (s, 9H), 1.57 (m, 5H), 2.02 (s, 3H), 3.36 (m, 1H), 3.68 (m, 4H), 4.09 (m, 4H), 4.36 (m, 2H), 5.34 (m, 2H), 6.93 (m, 2H), 7.72 (m, 3H), 8.04 (m, 1H), 9.04 (m, 1H).

LCMS(ESI): [M−Boc]$^+$ m/z: calcd 508.2; found 509.2; Rt=1.054 min.

Step 3: Synthesis of N-(6-amino-5-methylpyridin-3-yl)-2-(5-methyl-2-(5-(1-(tetrahydro-2H-pyran-2-yl)-1H-pyrazol-5-yl)thiophen-2-yl)piperidin-1-yl)-2-oxoacetamide (Compound 556 and Compound 577

Hydrogen chloride solution 4.0 M in dioxane (2.40 g, 65.82 mmol, 3 mL) was added to a solution of tert-butyl N-[3-methyl-5-[[2-[5-methyl-2-[5-(2-tetrahydropyran-2-yl)pyrazol-3-yl)-2-thienyl]-1-piperidyl]-2-oxo-acetyl] amino]-2-pyridyl]carbamate (0.63 g, 1.03 mmol) in MeOH (20 mL). The reaction mixture was stirred at 25° C. for 14 hr, then evaporated in vacuum and obtained crude product 0.36 g was purified by preparative 50-100% 0-9.5 min water-MeOH (NH$_3$0.1%), flow 30 ml/min to afford products N-(6-amino-5-methyl-3-pyridyl)-2-[(2R,5S)-5-methyl-2-[5-(1H-pyrazol-5-yl)-2-thienyl]-1-piperidyl]-2-oxo-acetamide (0.0159 g, 37.45 μmol, 3.62% yield) and N-(6-amino-5-methyl-3-pyridyl)-2-[(2R,5R)-5-methyl-2-[5-(1H-pyrazol-5-yl)-2-thienyl]-1-piperidyl]-2-oxo-acetamide (0.0045 g, 10.60 μmol, 1.02% yield).

Compound 556: $^1$H NMR (600 MHz, DMSO-d$_6$) δ (ppm) 0.75-1.00 (m, 3H), 1.27-1.43 (m, 1H), 1.64-1.93 (m, 2H), 1.97-2.04 (m, 4H), 2.05-2.29 (m, 1H), 2.59-2.96 (m, 1H), 3.44-4.23 (m, 1H), 5.36-5.81 (m, 3H), 6.86-6.93 (m, 1H), 7.03-7.10 (m, 1H), 7.45-7.52 (m, 1H), 7.66-7.75 (m, 1H), 7.97-8.06 (m, 2H), 10.43-10.53 (m, 1H), 12.95 (s, 1H).

LCMS(ESI): [M]$^+$ m/z: calcd 424.2; found 425.2; Rt=0.873 min.

Compound 577: $^1$H NMR (600 MHz, DMSO-d$_6$) δ (ppm) 0.84 (d, 3H), 1.85 (m, 1H), 1.97 (m, 1H), 2.00 (s, 3H), 2.17 (m, 1H), 3.03 (m, 1H), 3.13 (m, 1H), 5.68 (m, 2H), 5.91 (m, 1H), 6.53 (d, 1H), 6.85 (d, 1H), 7.01 (d, 1H), 7.59 (m, 1H), 7.70 (s, 1H), 8.00 (s, 1H), 8.16 (d, 1H), 8.88 (t, 1H), 10.34 (s, 1H), 12.96 (s, 1H).

LCMS(ESI): [M]$^+$ m/z: calcd 424.2; found 425.2; Rt=2.092 min.

Example 729. The Synthesis of 2-(1'-acetyl-5-methyl-[2,4'-bipiperidin]-1-yl)-N-(6-amino-5-methylpyridin-3-yl)-2-oxoacetamide (Compound 737), N-(6-amino-5-methylpyridin-3-yl)-2-(5-methyl-[2,4'-bipiperidin]-1-yl)-2-oxoacetamide (Compound 708) and 1-(2-(((6-amino-5-methylpyridin-3-yl)amino)-2-oxoacetyl)-N,5-dimethyl-[2,4'-bipiperidine]-1'-carboxamide (Compound 781)

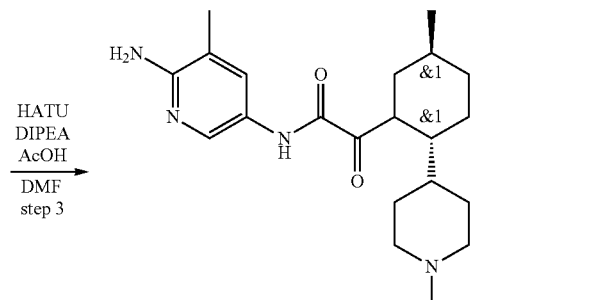

Compound 737

2978

-continued

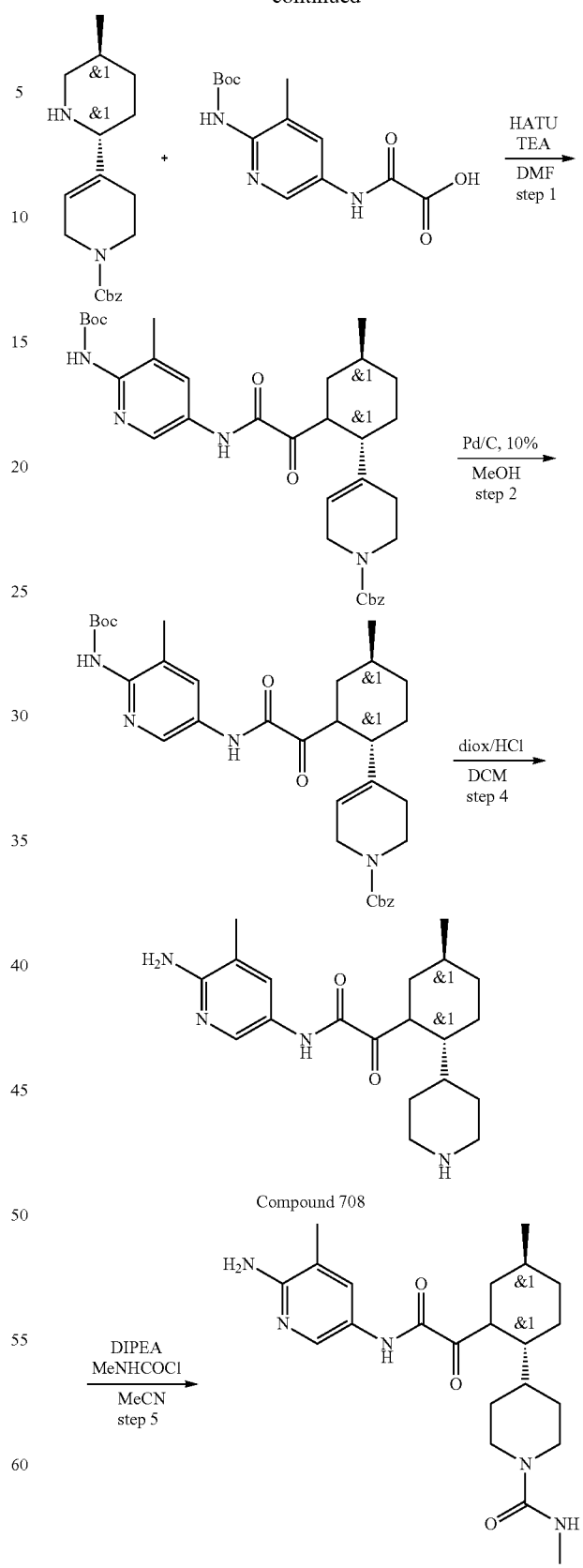

Step 1: Synthesis of rac-benzyl 4-((2R,5S)-1-(2-((6-((Tert-butoxycarbonyl)amino)-5-methylpyridin-3-yl)amino)-2-oxoacetyl)-5-methylpiperidin-2-yl)-5,6-dihydropyridine-1(2H)-carboxylate HATU (3.39 g, 8.91 mmol) was added portion wise at rt to a suspension of 2-[[6-(tert-butoxycarbonylamino)-5-methyl-3-pyridyl]amino]-2-oxo-acetic acid (2.63 g, 8.91 mmol), benzyl 4-[(2R,5S)-5-methyl-2-piperidyl]-3,6-dihydro-2H-pyridine-1-carboxylate (7 g, 8.91 mmol) and DIPEA (6.91 g, 53.43 mmol, 9.31 mL) in DMF (100 mL). The clear solution was stirred at 25° C. for 32 hr and the solvents were evaporated in vacuum. The residue was dissolved in EtOAc (300 mL), washed with water (5×100 mL), evaporated in vacuum and purified by silica gel flash chromatography eluting with a 0 to 100 percent MTBE-chloroform gradient to give benzyl 4-[(2R,5S)-1-[2-[[6-(tert-butoxycarbonylamino)-5-methyl-3-pyridyl]amino]-2-oxo-acetyl]-5-methyl-2-piperidyl]-3,6-dihydro-2H-pyridine-1-carboxylate (3.3 g, 5.58 mmol, 62.63% yield).

$^1$H NMR (400 MHz, DMSO-$d_6$) δ (ppm) 1.06 (d, 3H), 1.39 (s, 9H), 2.14 (m, 8H), 2.36 (m, 4H), 3.89 (m, 4H), 4.36 (m, 1H), 5.06 (s, 2H), 5.86 (m, 1H), 7.31 (m, 5H), 7.86 (m, 1H), 8.38 (m, 1H), 9.03 (m, 1H), 10.89 (m, 1H).

LCMS(ESI): [M]$^+$ m/z: calcd 591.2; found 592.2; Rt=1.390 min.

Step 2: Synthesis of rac-tert-butyl (3-methyl-5-(2-((2R,5S)-5-methyl-[2,4'-bipiperidin]-1-yl)-2-oxoacetamido)pyridin-2-yl)carbamate To a solution of benzyl 4-[(2R,5S)-1-[2-[[6-(tert-butoxycarbonylamino)-5-methyl-3-pyridyl]amino]-2-oxo-acetyl]-5-methyl-2-piperidyl]-3,6-dihydro-2H-pyridine-1-carboxylate (3.5 g, 5.92 mmol) in MeOH (350 mL) was added palladium, 10% on carbon (629.50 mg, 5.92 mmol). The reaction was put under an atmosphere of hydrogen (1 bar) and stirred vigorously at 45° C. After 48 hr, the catalyst was removed by filtration, and the filtrate was concentrated in vacuum to give tert-butyl N-[3-methyl-5-[[2-[(2R,5S)-5-methyl-2-(4-piperidyl)-1-piperidyl]-2-oxo-acetyl]amino]-2-pyridyl]carbamate (2.5 g, 5.44 mmol, 91.96% yield).

$^1$H NMR (500 MHz, DMSO-$d_6$) δ (ppm) 0.92 (d, 3H), 1.36 (s, 3H), 1.41 (s, 9H), 1.96 (m, 4H), 2.19 (m, 4H), 2.96 (m, 3H), 3.14 (m, 4H), 4.26 (m, 1H), 7.91 (m, 2H), 8.38 (m, 1H), 9.02 (m, 2H), 11.05 (m, 1H).

LCMS(ESI): [M]$^+$ m/z: calcd 459.2; found 460.2; Rt=1.014 min.

Step 3: Synthesis of 2-(1'-acetyl-5-methyl-[2,4'-bipiperidin]-1-yl)-N-(6-amino-5-methylpyridin-3-yl)-2-oxoacetamide (Compound 737

HATU (413.67 mg, 1.09 mmol) was added portion wise at rt to a suspension of tert-butyl N-[3-methyl-5-[[2-[(2R,5S)-5-methyl-2-(4-piperidyl)-1-piperidyl]-2-oxo-acetyl]amino]-2-pyridyl]carbamate (0.5 g, 1.09 mmol), acetic acid (65.33 mg, 1.09 mmol, 62.22 μL) and DIPEA (843.64 mg, 6.53 mmol, 1.14 mL) in DMF (50 mL). The clear solution was stirred at 25° C. for 32 hr and the solvents were evaporated in vacuum. The residue was purified by RP-HPLC (column: YMC-Actus Triart C18 100*20 mm.D. S-5 um; 25-65% 0-5 min water-MeOH (NH$_3$0.1%), flow 30 ml/min) to give tert-butyl N-[5-[[2-[(2R,5S)-2-(1-acetyl-4-piperidyl)-5-methyl-1-piperidyl]-2-oxo-acetyl]amino]-3-methyl-2-pyridyl]carbamate (26 mg, 51.83 μmol, 4.76% yield) and Compound 737 2-[(2R,5S)-2-(1-acetyl-4-piperidyl)-5-methyl-1-piperidyl]-N-(6-amino-5-methyl-3-pyridyl)-2-oxo-acetamide (222 mg, 552.93 μmol, 50.82% yield).

Compound 737: $^1$H NMR (600 MHz, DMSO-$d_6$) δ (ppm) 0.94 (m, 3H), 0.96 (m, 1H), 1.33 (m, 1H), 1.61 (m, 2H), 1.85 (m, 2H), 1.95 (m, 7H), 2.11 (m, 2H), 2.91 (m, 3H), 3.70 (m, 3H), 4.05 (m, 1H), 4.36 (m, 1H), 5.59 (s, 2H), 7.44 (m, 1H), 7.97 (m, 1H), 10.28 (m, 1H).

LCMS(ESI): [M]$^+$ m/z: calcd 401.2; found 402.2; Rt=1.215 min.

Step 4: Synthesis of N-(6-amino-5-methylpyridin-3-yl)-2-(5-methyl-[2,4'-bipiperidin]-1-yl)-2-oxoacetamide (Compound 708

Hydrogen chloride solution 4.0 M in dioxane (1.98 g, 7.62 mmol, 1.89 mL, 14% purity) was carefully added at r.t. to a solution of tert-butyl N-[3-methyl-5-[[2-[(2R,5S)-5-methyl-2-(4-piperidyl)-1-piperidyl]-2-oxo-acetyl]amino]-2-pyridyl]carbamate (0.35 g, 761.56 μmol) in DCM (3.5 mL). The reaction mixture was then stirred for 12 hr at rt and the solvents were evaporated in vacuum. The residue was subjected to RP-HPLC (column: YMC Triart C18 100×20 mm, 5 um; 40-60% 0-5 min 0.10% NH$_3$-MeOH as mobile phase) to give Compound 708 N-(6-amino-5-methyl-3-pyridyl)-2-[(2R,5S)-5-methyl-2-(4-piperidyl)-1-piperidyl]-2-oxo-acetamide (62 mg, 172.48 μmol, 22.65% yield).

Compound 708: $^1$H NMR (600 MHz, DMSO-$d_6$) δ (ppm) 0.93 (m, 5H), 1.27 (m, 1H), 1.41 (m, 1H), 1.58 (m, 3H), 1.85 (m, 4H), 2.00 (m, 3H), 2.37 (m, 2H), 2.88 (m, 3H), 3.46 (m, 1H), 4.03 (m, 1H), 5.58 (m, 2H), 7.45 (m, 1H), 7.98 (m, 1H), 10.27 (m, 1H).

LCMS(ESI): [M]$^+$ m/z: calcd 359.2; found 360.2; Rt=0.997 min.

Step 5: Synthesis of 1-(2-((6-amino-5-methylpyridin-3-yl)amino)-2-oxoacetyl)-N,5-dimethyl-[2,4'-bipiperidine]-1'-carboxamide (Compound 781

DIPEA (140.61 mg, 1.09 mmol, 189.50 μL) was added portion wise at rt to a suspension of tert-butyl N-[3-methyl-5-[[2-[(2R,5S)-5-methyl-2-(4-piperidyl)-1-piperidyl]-2-oxo-acetyl]amino]-2-pyridyl]carbamate (0.5 g, 1.09 mmol), DIPEA (140.61 mg, 1.09 mmol, 189.50 μL) in ACN (50 mL). The clear solution was stirred at 25° C. for 18 hr and the solvents were evaporated in vacuum. The residue was purified by RP-HPLC (column: YMC-Actus Triart C18 100*20 mml.D. S-5 um; 0-5 min 30-50% water-MeOH (NH$_3$ 0.1%), flow 30 ml/min as mobile phase then another column: C18 water-ACN 5-95% 30 ml/min as mobile phase) to give Compound 781 4-[(2R,5S)-1-[2-[(6-amino-5-methyl-3-pyridyl)amino]-2-oxo-acetyl]-5-methyl-2-piperidyl]-N-methyl-piperidine-1-carboxamide (38 mg, 91.23 μmol, 8.39% yield).

Compound 781: $^1$H NMR (600 MHz, DMSO-$d_6$) δ (ppm) 0.74-0.92 (m, 2H), 0.92-0.97 (m, 3H), 1.22-1.32 (m, 1H), 1.38-1.48 (m, 1H), 1.48-1.74 (m, 3H), 1.74-1.99 (m, 3H), 1.99-2.08 (m, 4H), 2.51-2.57 (m, 4H), 2.83-3.28 (m, 1H), 3.32-3.49 (m, 1H), 3.84-4.14 (m, 3H), 5.55-5.63 (m, 2H), 6.29-6.37 (m, 1H), 7.40-7.49 (m, 1H), 7.94-8.02 (m, 1H), 10.24-10.36 (m, 1H).

LCMS(ESI): [M]+ m/z: calcd 416.2; found 417.2; Rt=1.658 min.
Example 730. The Synthesis of rac-2-[(2R,5S)-2-[4-(Acetamidomethyl)phenyl]-5-methyl-1-piperidyl]-N-(6-amino-5-methyl-3-pyridyl)-2-oxo-acetamide (Compound 1036)
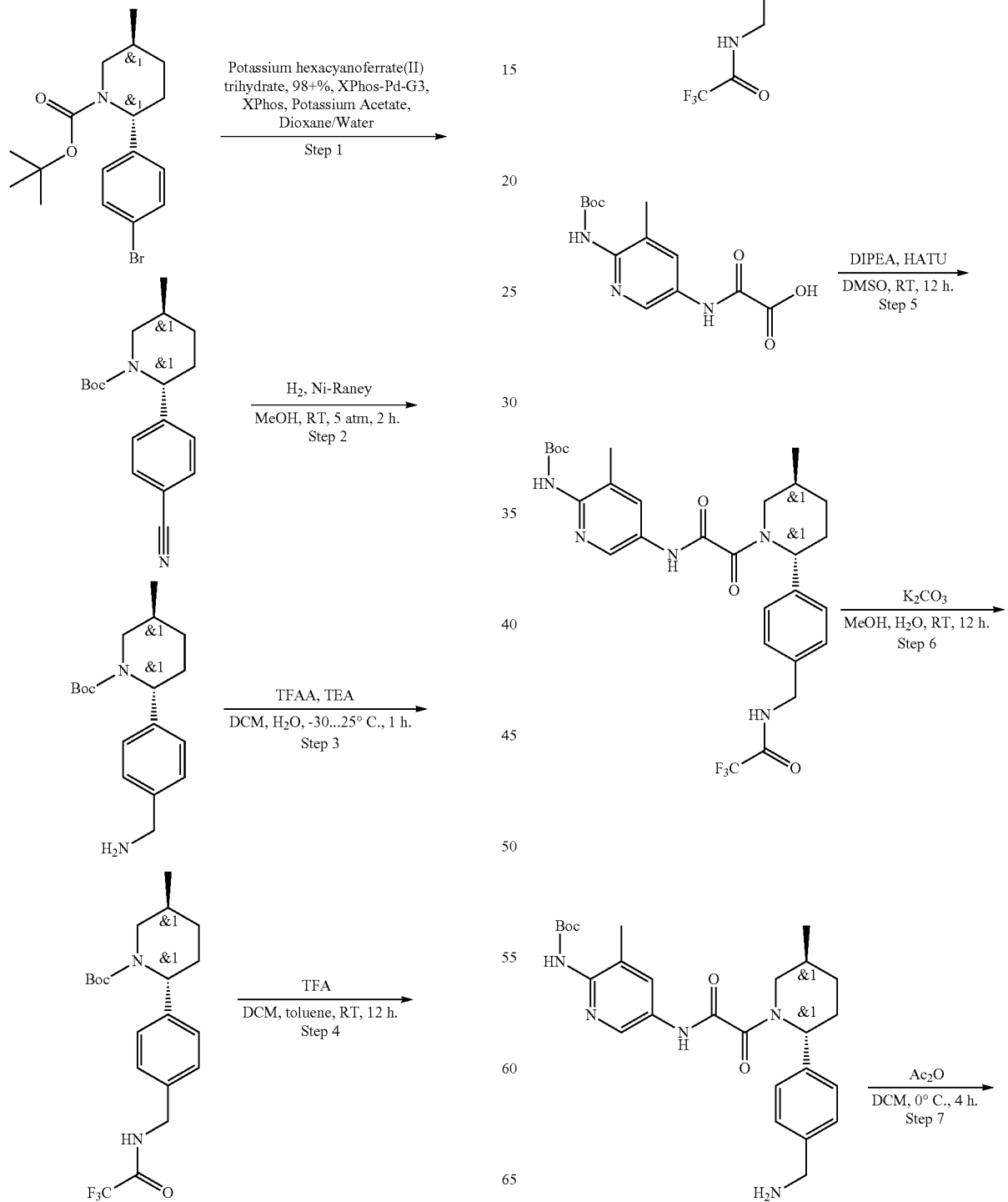

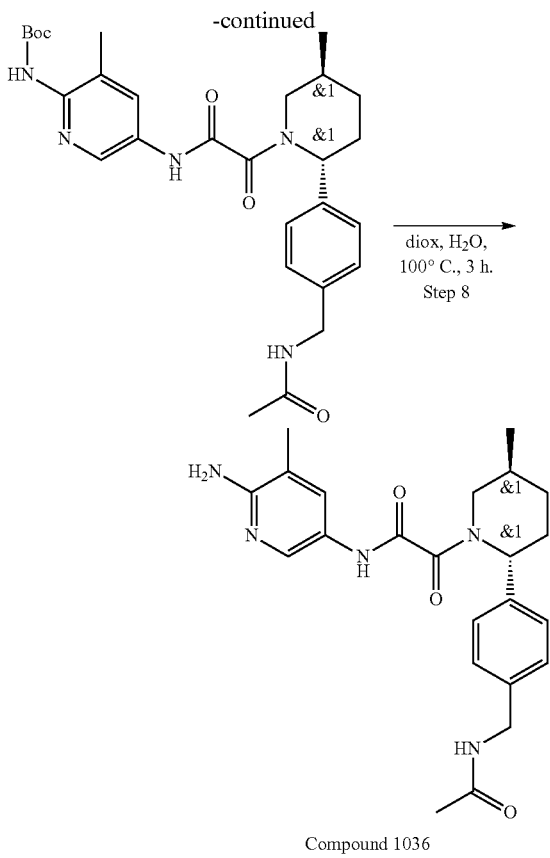

Compound 1036

Step 1: Synthesis of tert-butyl (2R,5S)-2-(4-cyanophenyl)-5-methyl-piperidine-1-carboxylate Potassium hexacyanoferrate(II) trihydrate, 98+% (741.85 mg, 1.01 mmol, 401.00 μL) and Potassium Acetate (24.76 mg, 252.27 μmol, 15.77 μL) were added to a solution of tert-butyl (2R,5S)-2-(4-bromophenyl)-5-methyl-piperidine-1-carboxylate (715 mg, 2.02 mmol) in Dioxane (5 mL) and Water (5 mL). Reaction flask was evacuated and refilled with argon for 3 times. XPhos-Pd-G3 (17.08 mg, 20.18 μmol) and XPhos (9.62 mg, 20.18 μmol) were added thereto under stream of argon and resulting mixture was stirred at 100° C. for 2 hr. Then, volatiles were removed under reduced pressure and residue was redissolved in ethyl acetate (20 ml). This solution was filtered through a short pad of silicagel and evaporated in vacuo, affording tert-butyl (2R,5S)-2-(4-cyanophenyl)-5-methyl-piperidine-1-carboxylate (887 mg, crude).

$^1$H NMR (CDCl$_3$, 500 MHz): 1.05 (d, 3H), 1.30 (m, 1H), 1.43 (s, 9H), 1.65 (m, 1H), 1.84 (m, 1H), 1.96 (m, 1H), 2.15 (m, 1H), 2.99 (m, 1H), 3.70 (m, 1H), 5.28 (s, 1H), 7.34 (m, 2H), 7.62 (m, 2H).

LCMS(ESI): [M+H]$^+$ m/z: calcd 300.2; found 301.8; Rt=1.619 min.

Step 2: The Synthesis of rac-tert-butyl (2R,5S)-2-[4-(Aminomethyl)phenyl]-5-methyl-piperidine-1-carboxylate rac-tert-butyl (2R,5S)-2-(4-cyanophenyl)-5-methyl-piperidine-1-carboxylate (0.9 g, 3.00 mmol) was added to the suspension of Nickel-Raney (149.80 μmol) in MeOH (20 mL) and stirred for 2 hr at rt in autoclave under Hydrogen atmosphere. After the reaction was complete, the mixture was filtered off and evaporated under reduced pressure to give tert-butyl (2R,5S)-2-[4-(aminomethyl)phenyl]-5-methyl-piperidine-1-carboxylate (1 g, crude) which was used in the next step without purification.

LCMS(ESI): [M+H]$^+$ m/z: calcd 247.0; found 247.0; Rt=1.573 min.

Step 3: The Synthesis of rac-tert-butyl (2R,5S)-5-methyl-2-[4-[[(2,2,2-trifluoroacetyl)amino]methyl]phenyl]piperidine-1-carboxylate rac-tert-butyl (2R,5S)-2-[4-(aminomethyl)phenyl]-5-methyl-piperidine-1-carboxylate (1 g, 3.28 mmol) was dissolved in DCM (20 mL) and cooled to −30° C. followed by the addition of triethylamine (498.59 mg, 4.93 mmol, 686.77 μL) and TFAA (827.91 mg, 3.94 mmol, 555.65 μL) in a dropwise manner. After additional stirring for 15 min, the was quenched with H$_2$O (2 mL), and the organic layer was washed with 10% aq NaHCO$_3$. Drying of the organic solvent over Na$_2$SO$_4$ and evaporation under reduced pressure results in rac-tert-butyl (2R,5S)-5-methyl-2-[4-[[(2,2,2-trifluoroacetyl)amino]methyl]phenyl]piperidine-1-carboxylate (1.1 g, 2.75 mmol, 83.63% yield).

LCMS(ESI): [M−Boc]$^+$ m/z: calcd 300.2; found 301.2; Rt=1.602 min.

Step 4: The Synthesis of rac-2,2,2-trifluoro-N-[[4-[(2R,5S)-5-methyl-2-piperidyl]phenyl]methyl]acetamide rac-tert-butyl (2R,5S)-5-methyl-2-[4-[[(2,2,2-trifluoroacetyl)amino]methyl]phenyl]piperidine-1-carboxylate (1.1 g, 2.75 mmol) was dissolved in DCM (30 mL), followed by the addition of TFA (3.13 g, 27.47 mmol, 2.12 mL) and additional stirring for 12 hr. After the reaction was complete, the organic solvent was evaporated under reduced pressure and the mixture was re-evaporated with toluene (100 mL) to give crude rac-2,2,2-trifluoro-N-[[4-[(2R,5S)-5-methyl-2-piperidyl]phenyl]methyl]acetamide (1.3 g, crude, TFA) which was used in the next step without purification.

LCMS(ESI): [M+H]$^+$ m/z: calcd 300.2; found 301.0; Rt=0.795 min.

Step 5: The Synthesis of rac-tert-butyl N-[3-methy-5-[[2-[(2R,5S)-5-methyl-2-[4-[[(2,2,2-trifluoroacetyl)amino]methyl]phenyl]-1-piperidyl]-2-oxoacetyl]amino]-2-pyridyl]carbamate 2-[[6-(tert-butoxycarbonylamino)-5-methyl-3-pyridyl]amino]-2-oxo-acetic acid (287.67 mg, 974.21 μmol), rac-2,2,2-trifluoro-N-[[4-[(2R,5S)-5-methyl-2-piperidyl]phenyl]methyl]acetamide (292.57 mg, 974.21 μmol) and DIPEA (377.73 mg, 2.92 mmol, 509.07 μL) were dissolved in DMSO (6 mL) under gentle heating. HATU (444.51 mg, 1.17 mmol) was added in small portions under vigorous stirring and occasional heating. After the reaction was complete, the mixture was purified by HPLC to give racemic product, which was subjected to chiral HPLC to give rac-tert-butyl N-[3-methyl-5-[[2-[(2R,5S)-5-methyl-2-[4-[[(2,2,2-trifluoroacetyl)amino]methyl]phenyl]-1-piperidyl]-2-oxoacetyl]amino]-2-pyridyl]carbamate (60 mg, 103.88 μmol, 10.66% yield).

HPLC conditions: (42% 0.5-6.5 min water-acetonitrile; flow 30 mL/min (loading pump 4 mL/min acetonitrile); target mass 577; column SunFire C18 100×19 mm 5 um (R))

LCMS(ESI): [M+H]⁺ m/z: calcd 577.2; found 578.2; Rt=3.417 min.

Step 6: The Synthesis of rac-tert-butyl N-[5-[[2-[(2R,5S)-2-[4-(Aminomethyl)phenyl]-5-methyl-1-piperidyl]-2-oxo-acetyl]amino]-3-methyl-2-pyridyl]carbamate rac-tert-butyl N-[3-methyl-5-[[2-[(2R,5S)-5-methyl-2-[4-[[(2,2,2-trifluoroacetyl)amino]methyl]-phenyl]-1-piperidyl]-2-oxo-acetyl]amino]-2-pyridyl]carbamate (60 mg, 103.88 μmol) was dissolved in MeOH (5 mL)/H₂O (1 mL) mixture, followed by the addition of Potassium carbonate, anhydrous, 99% (71.78 mg, 519.40 μmol, 31.35 μL). After stirring for 72 hr, the organic solvent was evaporated to dryness and the crude residue was partitioned between DCM (6 mL) and water (1 mL). The water layer was discarded; the organic layer was divided in 2 parts, which was used for the synthesis of 2 targets.

LCMS(ESI): [M+H]⁺ m/z: calcd 481.2; found 482.4; Rt=0.894 min.

Step 7: The Synthesis of rac-tert-butyl N-[5-[[2-[(2R,5S)-2-[4-(Acetamidomethyl)phenyl]-5-methyl-1-piperidyl]-2-oxo-acetyl]amino]-3-methyl-2-pyridyl]carbamate The previously obtained solution of rac-tert-butyl N-[5-[[2-[(2R,5S)-2-[4-(aminomethyl)phenyl]-5-methyl-1-piperidyl]-2-oxo-acetyl]amino]-3-methyl-2-pyridyl]carbamate (25 mg, 51.91 μmol) in DCM was cooled to 0° C. and the Acetic anhydride (5.30 mg, 51.91 μmol, 4.91 μL) was added in one portion. After the reaction was complete, the organic solvent was evaporated to dryness and the crude residue was used in the next step without purification.

LCMS(ESI): [M+H]⁺ m/z: calcd 523.2; found 524.4; Rt=0.674 min.

Step 8: The Synthesis of rac-2-[(2R,5S)-2-[4-(Acetamidomethyl)phenyl]-5-methyl-1-piperidyl]-N-(6-amino-5-methyl-3-pyridyl)-2-oxo-acetamide (Compound 1036 rac-tert-butyl N-[5-[[2-[(2R,5S)-2-[4-(acetamidomethyl)phenyl]-5-methyl-1-piperidyl]-2-oxo-acetyl]amino]-3-methyl-2-pyridyl]carbamate (25 mg, 47.74 μmol) was dissolved in dioxane (2 mL) and H₂O (0.5 mL) and stirred at 100° C. for 3 hr. After the reaction was complete, the crude RM was subjected to HPLC (12-14% 0.5-6.5 min water-acetonitrile+NH₃; flow 30 mL/min (loading pump 4 mL/min acetonitrile); target mass 423; column XBridge 100×19 mm 5 um (R)) to give rac-2-[(2R,5S)-2-[4-(acetamidomethyl)phenyl]-5-methyl-1-piperidyl]-N-(6-amino-5-methyl-3-pyridyl)-2-oxo-acetamide (7 mg, 16.53 μmol, 34.62% yield).

¹H NMR (600 MHz, DMSO-d₆) δ 0.95-1.02 (m, 3H), 1.26-1.37 (m, 1H), 1.59-1.67 (m, 1H), 1.79-1.87 (m, 4H), 1.97-2.10 (m, 4H), 2.15-2.25 (m, 1H), 2.66-3.21 (m, 1H), 3.40-4.03 (m, 1H), 4.18-4.23 (m, 2H), 5.07-5.56 (m, 1H), 5.56-5.65 (m, 2H), 7.20-7.31 (m, 4H), 7.41-7.52 (m, 1H), 7.93-8.04 (m, 1H), 8.26-8.32 (m, 1H), 10.47 (s, 1H).

LCMS(ESI): [M+H]⁺ m/z: calcd 423.2; found 424.4; Rt=1.634 min.

Example 731. The Synthesis of rac-N-(6-amino-5-methyl-3-pyridyl)-2-[(2R,5S)-5-methyl-2-(3-thienyl)-1-piperidyl]-2-oxo-acetamide (Compound 977)

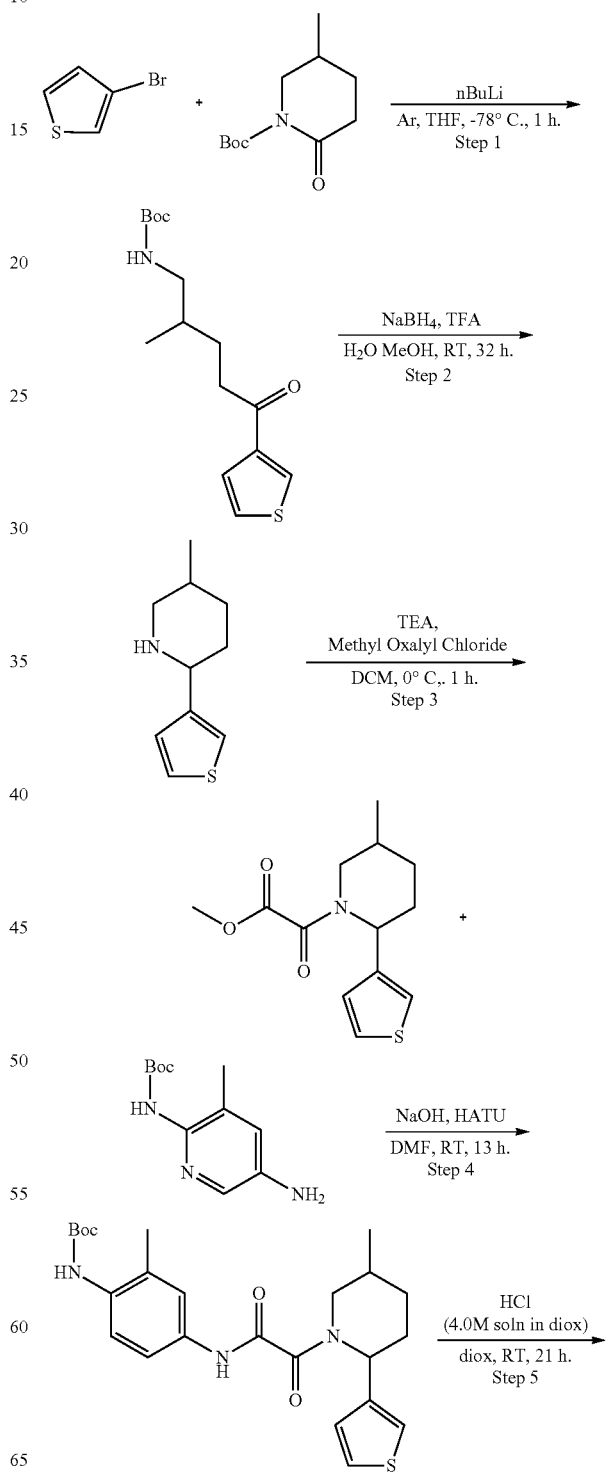

-continued

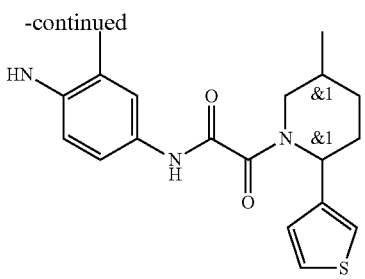

Compound 977

Step 1: The Synthesis of tert-butyl N-[2-methyl-5-oxo-5-(3-thienyl)pentyl]carbamate To a solution of 3-bromothiophene (5 g, 30.67 mmol, 2.91 mL) in THF (50 mL) was added n-butyllithium (8.54 g, 30.67 mmol, 12.33 mL, 23% purity) at −78° C. under Ar atmosphere. After 1 hr, the resulting mixture was added dropwise to a solution of tert-butyl 5-methyl-2-oxo-piperidine-1-carboxylate (5.45 g, 25.56 mmol) in THF at −78° C. After that, it allowed warming to rt. The resulting mixture was quenched with aq NH₄Cl, water was extracted with EtOAc, combined organics were washed with brine, dried and evaporated. tert-butyl N-[2-methyl-5-oxo-5-(3-thienyl) pentyl]carbamate (6.55 g, crude) was obtained as a light-yellow oil and was used in the next step without further purification.

Step 2: The Synthesis of 5-methyl-2-(3-thienyl)piperidine tert-butyl N-[2-methyl-5-oxo-5-(3-thienyl)pentyl]carbamate (6.55 g, 22.02 mmol) was dissolved in TFA (7.53 g, 66.07 mmol, 5.09 mL) and the resulting reaction mixture was stirred for 1 hour. After 1 hour, 50% aq. NaOH solution was added to the reaction mixture till pH=13-14. The resulting mixture was extracted with DCM (4×20 mL). The combined organic phase was dried over MgSO₄ and concentrated under reduced pressure. The obtained residue was dissolved in water (25 mL) and MeOH (100 mL) and Sodium Borohydride (833.19 mg, 22.02 mmol, 778.69 μL) was added portionwise. The resulting reaction mixture was stirred under argon atmosphere at 21° C. for 16 hours. After 16 hours, the reaction mixture was acidified with 1-2M HCl until the pH was 1-3 and stirred for 30 minutes. Then, 50% aq. NaOH solution was added till pH=13-14. The resulting mixture was extracted with DCM (4×100 mL). The combined organic phase was dried over Na₂SO₄ and concentrated under reduced pressure. The residue was purified by CC (Companion combiflash; 220 g SiO₂, chloroform/acetonitrile with acetonitrile from 10 to 100% further acetonitrile/methanol with methanol from 0 to 25% flow rate=85 mL/min, Rv=14 CV) to obtain 5-methyl-2-(3-thienyl)piperidine (0.15 g, 827.37 μmol, 3.76% yield) as a light-yellow oil. The crude product was used for the next step reaction without any further purification.

LCMS(ESI): [M+H]⁺ m/z: calcd 181.2; found 182.0; Rt=0.637 min.

Step 3: The Synthesis of methyl 2-[5-methyl-2-(3-thienyl)-1-piperidyl]-2-oxo-acetate To a solution of 5-methyl-2-(3-thienyl)piperidine (0.15 g, 827.37 μmol) and triethylamine (100.47 mg, 992.84 μmol, 138.38 μL) in DCM (25 mL) was added methyl 2-chloro-2-oxo-acetate (111.49 mg, 910.11 μmol) at 0° C. After stirring at rt for 1 hr the resulting mixture were filtered and evaporated to dryness to give methyl 2-[5-methyl-2-(3-thienyl)-1-piperidyl]-2-oxo-acetate (200 mg, crude) as a brownish oil, which was used in the next step without further purification.

LCMS(ESI): [M+H]⁺ m/z: calcd 267.2; found 268.2; Rt=1.305 min.

Step 4: The Synthesis of tert-butyl N-[3-methyl-5-[[2-[5-methyl-2-(3-thienyl)-1-piperidyl]-2-oxo-acetyl]amino]-2-pyridyl]carbamate To a solution of methyl 2-[5-methyl-2-(3-thienyl)-1-piperidyl]-2-oxo-acetate (200 mg, 748.10 μmol) in MeOH (5 mL) was added Sodium hydroxide, pearl (29.92 mg, 748.10 μmol, 14.05 μL) and the resulting mixture was stirred for 1 hr. Then, the solvent was evaporated and the residue was re-evaporated with EtOH. After that, solids were dissolved in DMF and HATU (284.45 mg, 748.10 μmol) was added followed by tert-butyl N-(5-amino-3-methyl-2-pyridyl)carbamate (167.03 mg, 748.10 μmol) and the resulting mixture was stirred for 12 hr. The resulting mixture was poured into water, extracted 3 times with EtOAc, combined organics were washed with water, brine and evaporated. The residue was subjected to HPLC (45-70% 0.5-6.5 min water-acetonitrile; flow 30 mL/min (loading pump 4 mL/min acetonitrile); column SunFire C18 100×19 mm 5 um (R)) to give tert-butyl N-[3-methyl-5-[[2-[5-methyl-2-(3-thienyl)-1-piperidyl]-2-oxo-acetyl]amino]-2-pyridyl]carbamate (91.8 mg, 200.19 μmol, 26.76% yield) as an off-white solid.

LCMS(ESI): [M+H]⁺ m/z: calcd 458.2; found 459.2; Rt=3.517 min.

Step 5: The Synthesis of rac-N-(6-amino-5-methyl-3-pyridyl)-2-[(2R,5S)-5-methyl-2-(3-thienyl)-1-piperidyl]-2-oxo-acetamide (Compound 977

To a solution of tert-butyl N-[3-methyl-5-[[2-[5-methyl-2-(3-thienyl)-1-piperidyl]-2-oxo-acetyl]amino]-2-pyridyl] carbamate (91.8 mg, 200.19 μmol) in dioxane (5 mL) was added Hydrogen chloride solution 4.0M in dioxane (36.49 mg, 1.00 mmol, 45.62 μL) at 21° C. The resulting mixture was left to stir for 21 hr. The resulting mixture was evaporated to dryness and subjected to HPLC (0-30% 0.5-6.5 min water-acetonitrile; flow 30 mL/min (loading pump 4 mL/min water); column SunFire C18 100×19 mm 5 um (R)). N-(6-amino-5-methyl-3-pyridyl)-2-[(2R,5S)-5-methyl-2-(3-thienyl)-1-piperidyl]-2-oxo-acetamide (17.2 mg, 47.98 μmol, 23.97% yield) was obtained as a yellow solid.

¹H NMR (600 MHz, DMSO-d₆) δ 0.97-1.04 (m, 3H), 1.31-1.42 (m, 1H), 1.65-1.80 (m, 1H), 1.82-1.93 (m, 1H), 1.96-2.09 (m, 1H), 2.11-2.14 (m, 3H), 2.73-3.16 (m, 1H), 3.39-4.01 (m, 2H), 5.07-5.64 (m, 1H), 6.96-7.05 (m, 1H), 7.05-7.33 (m, 2H), 7.34-7.41 (m, 1H), 7.51-7.59 (m, 1H), 7.74 (s, 1H), 8.17-8.23 (m, 1H), 10.75-11.03 (m, 1H).

LCMS(ESI): [M+H]⁺ m/z: calcd 358.2; found 359.2; Rt=2.187 min.

Example 732. The Synthesis of 2-ethyl-5-(2-(5-methyl-2-phenylpiperidin-1-yl)-2-oxoacetamido)nicotinamide (Compound 747)

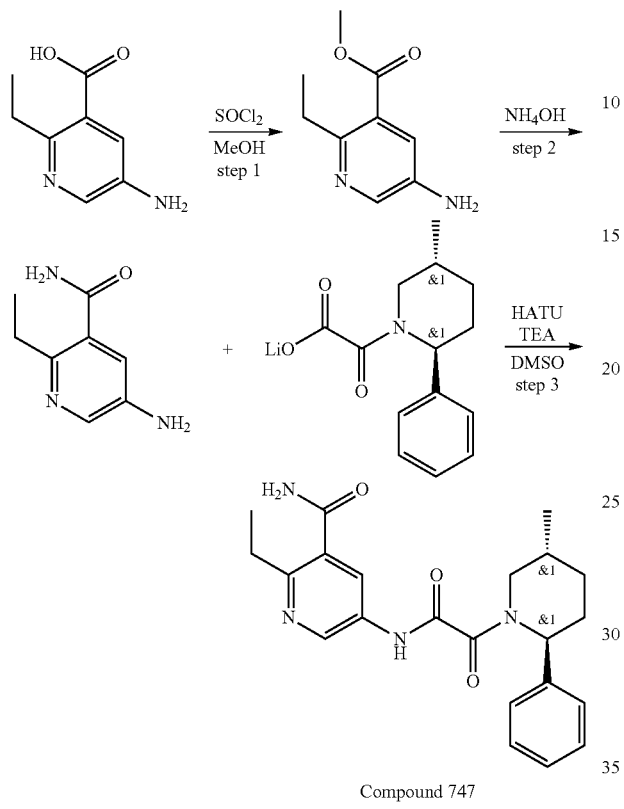

Compound 747

Step 1: Synthesis of methyl 5-amino-2-ethylnicotinate

To a stirred solution of 5-amino-2-ethyl-pyridine-3-carboxylic acid (1.05 g, 6.32 mmol) in MeOH (20 mL), thionyl chloride (826.89 mg, 6.95 mmol, 504.20 µL) was added dropwise at 20° C. The mixture was refluxed for 16 hr at 70° C. The mixture was cooled, concentrated in vacuum to give methyl 5-amino-2-ethyl-pyridine-3-carboxylate (1.25 g, 5.77 mmol, 91.31% yield, HCl).

$^1$H NMR (400 MHz, DMSO-$d_6$) δ (ppm) 1.16 (t, 3H), 3.06 (m, 2H), 3.85 (s, 3H), 6.45 (m, 2H), 8.01 (s, 1H), 8.04 (s, 1H). LCMS(ESI): [M]$^+$ m/z: calcd 180.2; found 181.2; Rt=0.465 min.

Step 2: Synthesis of 5-amino-2-ethylnicotinamide

Methyl 5-amino-2-ethyl-pyridine-3-carboxylate (1.1 g, 5.08 mmol, HCl) was dissolved in ammonium hydroxide, 28% NH$_3$ (5.40 g, 154.07 mmol, 6 mL) and heated overnight at 70° C. Reaction mixture was evaporated and subjected to HPLC (2-10 min 0-60% acn/H$_2$O 30 ml/min (loading pump 4 ml MeCN) column: SunFire 100*19 mm, 5 micro). 5-amino-2-ethyl-pyridine-3-carboxamide (220 mg, 1.33 mmol, 26.23% yield) was obtained.

$^1$H NMR (400 MHz, DMSO-$d_6$) δ (ppm) 1.12 (t, 3H), 2.68 (m, 2H), 5.28 (m, 2H), 6.89 (s, 1H), 7.32 (s, 1H), 7.78 (s, 1H), 7.92 (s, 1H). LCMS(ESI): [M]$^+$ m/z: calcd 165.2; found 166.2; Rt=0.141 min.

Step 3: Synthesis of 2-ethyl-5-(2-(5-methyl-2-phenylpiperidin-1-yl)-2-oxoacetamido)nicotinamide (Compound 747

5-amino-2-ethyl-pyridine-3-carboxamide (220 mg, 1.33 mmol), [2-[(2S,5R)-5-methyl-2-phenyl-1-piperidyl]-2-oxo-acetyl]oxylithium (337.24 mg, 1.33 mmol), HATU (557.02 mg, 1.46 mmol) and TEA (336.91 mg, 3.33 mmol, 464.06 µL) were mixed in DMSO (4 mL) and stirred for 1 hr. Solution in DMSO was subjected to HPLC (2-10 min 45-60% water/MeCN (loading pump 4 ml MeCN) column: TRIART 100*20 5 microM). 2-ethyl-5-[[2-[(2S,5R)-5-methyl-2-phenyl-1-piperidyl]-2-oxo-acetyl]amino]pyridine-3-carboxamide (303.3 mg, 768.89 µmol, 57.73% yield).

Compound 747: $^1$H NMR (600 MHz, DMSO-$d_6$) δ (ppm) 0.98-1.03 (m, 3H), 1.14 (dt, 3H), 1.33 (dd, 1H), 1.66 (d, 1H), 1.87 (d, 1H), 2.01-2.16 (m, 1H), 2.17-2.29 (m, 1H), 2.73-2.81 (m, 2H), 3.22-3.26 (m, 1H), 3.37-4.06 (m, 1H), 5.09-5.64 (m, 1H), 7.22-7.31 (m, 2H), 7.33-7.43 (m, 3H), 7.49-7.60 (m, 1H), 7.84-7.94 (m, 1H), 7.94-8.02 (m, 1H), 8.66-8.78 (m, 1H), 11.03-11.25 (m, 1H).

LCMS(ESI): [M]$^+$ m/z: calcd 394.2; found 395.2; Rt=1.088 min.

Example 733. The Synthesis of N-(6-amino-5-methylpyridin-3-yl)-2-(2-(3,5-difluorophenyl)-5-methylpiperidin-1-yl)-2-oxoacetamide (Compound 712 and Compound 734

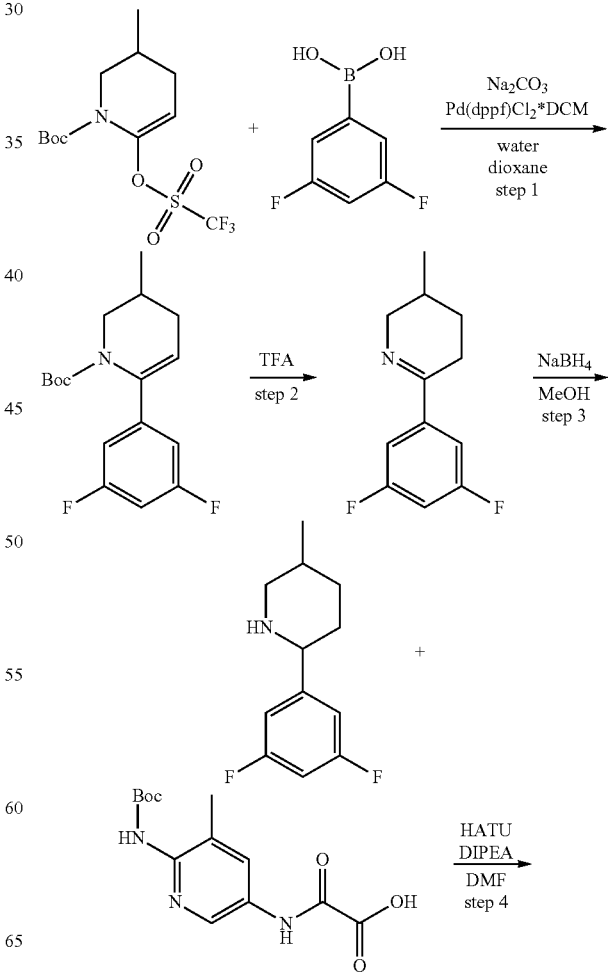

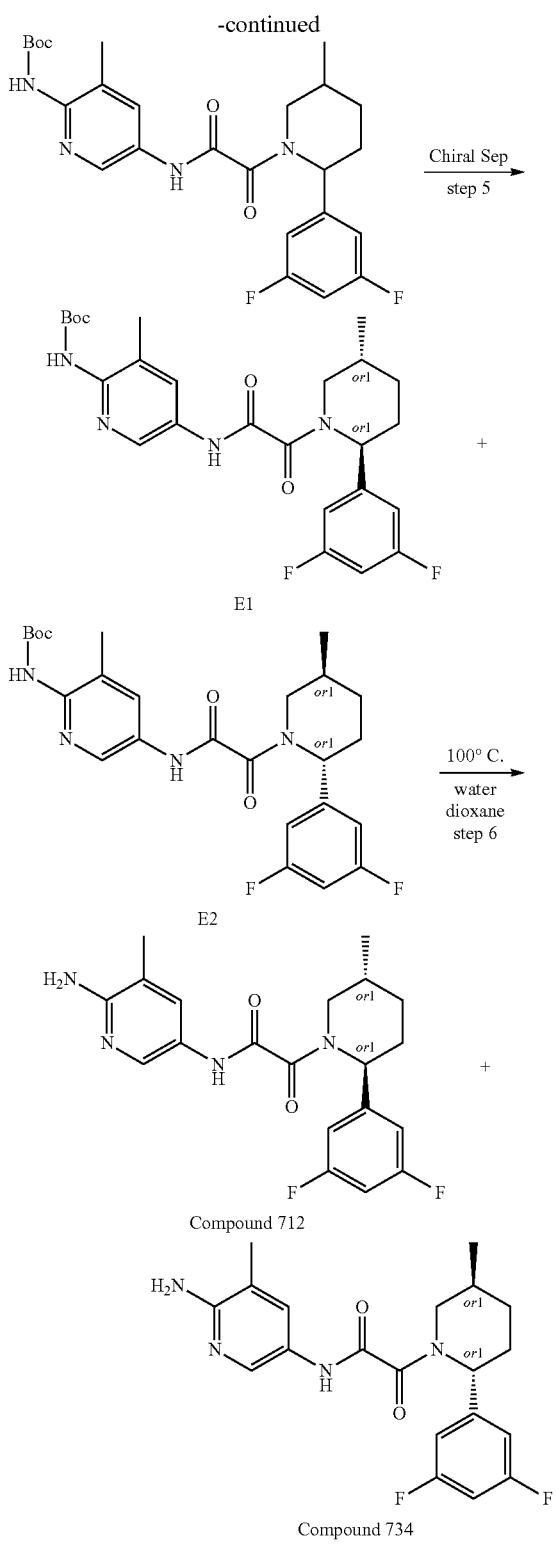

E1

E2

Compound 712

Compound 734

Step 1: Synthesis of tert-butyl 6-(3,5-difluorophenyl)-3-methyl-3,4-dihydropyridine-1(2H)-carboxylate tert-butyl 3-methyl-6-(trifluoromethylsulfonyloxy)-3,4-dihydro-2H-pyridine-1-carboxylate (5 g, 14.48 mmol), (3,5-difluorophenyl)boronic acid (2.29 g, 14.48 mmol) and sodium carbonate (4.60 g, 43.44 mmol, 1.82 mL) were added to a mixture of water (15 mL) and dioxane (45 mL). The resulting mixture was evacuated and then backfilled with argon, this operation was repeated three times, then Pd(dppf)Cl$_2$*DCM (591.19 mg, 723.94 µmol) was added under argon. The reaction mixture was stirred under argon at 70° C. for 14 hr, then cooled and filtered. The filtercake was washed with 1,4-dioxane (2*20 ml) and discarded. The filtrate was evaporated in vacuo to afford tert-butyl 6-(3,5-difluorophenyl)-3-methyl-3,4-dihydro-2H-pyridine-1-carboxylate (4 g, 12.93 mmol, 89.31% yield) as brown oil, which was used in next step without purification.

$^1$H NMR (400 MHz, DMSO-d$_6$) δ (ppm) 0.89 (d, 3H), 1.04 (s, 9H), 1.81 (m, 1H), 2.33 (m, 1H), 2.96 (m, 1H), 3.80 (d, 1H), 5.46 (m, 1H), 6.87 (m, 2H), 7.06 (m, 1H), 7.53 (m, 1H). LCMS(ESI): [M−Boc]$^+$ m/z: calcd 209.2; found 210.2; Rt=1.626 min.

Step 2: Synthesis of 6-(3,5-difluorophenyl)-3-methyl-2,3,4,5-tetrahydropyridine

The solution of tert-butyl 6-(3,5-difluorophenyl)-3-methyl-3,4-dihydro-2H-pyridine-1-carboxylate (4 g, 12.93 mmol) in TFA (22.12 g, 193.96 mmol, 14.94 mL) was stirred at 25° C. for 1 hr, and then evaporated in vacuo. Crushed ice (15 g) was added to the residue and pH was adjusted to 10 with a 10% aqueous solution of sodium hydroxide. The resulting mixture was extracted with dichloromethane (2*30 ml). The combined organic extracts were dried over sodium sulphate and evaporated in vacuo to afford 6-(3,5-difluorophenyl)-3-methyl-1,2,3,4-tetrahydropyridine (2.5 g, 11.95 mmol, 92.41% yield) as brown oil, which was used directly in the next step.

$^1$H NMR (400 MHz, DMSO-d$_6$) δ (ppm) 0.93 (d, 3H), 1.36 (m, 1H), 1.77 (m, 2H), 2.80 (m, 1H), 3.21 (m, 1H), 3.82 (d, 1H), 4.31 (m, 1H), 7.20 (m, 1H), 7.34 (m, 1H), 8.39 (m, 1H). LCMS(ESI): [M]$^+$ m/z: calcd 209.2; found 210.2; Rt=0.832 min.

Step 3: Synthesis of 2-(3,5-difluorophenyl)-5-methylpiperidine

Sodium borohydride (723.26 mg, 19.12 mmol, 675.94 µL) was added in one portion to a stirred solution of 6-(3,5-difluorophenyl)-3-methyl-1,2,3,4-tetrahydropyridine (2 g, 9.56 mmol) in MeOH (25 mL) at 0° C. The resulting mixture was stirred at 25° C. for 2 hr, and then evaporated in vacuum. The residue was diluted with water (20 ml) and extracted with DCM (2*40 ml). The combined organic extracts were dried over sodium sulphate and evaporated in vacuo. The obtained oil was subjected to HPLC (Waters Sunfire C18 19*100 5 mkm column and H$_2$O-MeOH+HCl as an eluent mixture) to afford 2-(3,5-difluorophenyl)-5-methyl-piperidine (0.85 g, 3.43 mmol, 35.90% yield, HCl).

$^1$H NMR (400 MHz, DMSO-d$_6$) δ (ppm) 0.88 (d, 3H), 1.27 (m, 1H), 1.84 (m, 3H), 2.07 (m, 1H), 2.62 (m, 1H), 3.19 (d, 1H), 4.18 (m, 1H), 7.24 (m, 1H), 7.42 (m, 2H), 9.53 (m, 1H). LCMS(ESI): [M]$^+$ m/z: calcd 211.2; found 212.2; Rt=1.447 min.

Step 4: Synthesis of tert-butyl (5-(2-(2-(3,5-difluorophenyl)-5-methylpiperidin-1-yl)-2-oxoacetamido)-3-methylpyridin-2-yl)carbamate DIPEA (615.66 mg, 4.76 mmol, 829.73 µL) was added to the solution of respective 2-(3,5-difluorophenyl)-5-methyl-piperidine (0.295 g, 1.19 mmol, HCl) and 2-[[6-(tert-butoxycarbonylamino)-5-methyl-3-pyridyl]amino]-2-oxo-acetic acid (351.66 mg, 1.19 mmol) in DMF (10 mL). The resulting mixture was stirred for 5 min followed by the addition of HATU (498.10 mg, 1.31 mmol). Then, the reaction mixture was stirred overnight at room temperature. After the completion of the reaction, monitored by LCMS, the resulting suspension was concentrated under reduced pressure. The obtained solid was subjected to HPLC (Waters Sunfire C18 20*100 5 mkm column and H$_2$O-MeCN as an eluent mixture) to afford tert-butyl N-[5-[[2-[2-(3,5-difluorophenyl)-5-methyl-1-piperidyl]-2-oxo-acetyl]amino]-3-methyl-2-pyridyl]carbamate (0.32 g, 655.03 µmol, 55.00% yield).

$^1$H NMR (400 MHz, DMSO-d$_6$) δ (ppm) 0.98 (d, 3H), 1.25 (m, 2H), 1.39 (s, 9H), 1.59 (m, 1H), 1.87 (m, 1H), 2.04 (m, 1H), 2.13 (s, 3H), 3.24 (m, 1H), 3.46 (m, 1H), 5.51 (m, 1H), 7.03 (m, 3H), 7.88 (m, 1H), 8.39 (m, 1H), 9.03 (m, 1H), 11.03 (m, 1H). LCMS(ESI): [M]$^+$ m/z: calcd 488.2; found 489.2; Rt=3.673 min.

Step 5: Chiral Separation

The enantiomers were separated by chiral HPLC (column: 1C (250*20, 5 mkm), CO2-MeOH, 55-45, 15 ml/min as mobile phase) to give the two individual enantiomers E1 tert-butyl N-[5-[[2-[(2S,5R)-2-(3,5-difluorophenyl)-5-methyl-1-piperidyl]-2-oxo-acetyl]amino]-3-methyl-2-pyridyl]carbamate (50.82 mg, 104.03 µmol, 15.88% yield) and E2 tert-butyl N-[5-[[2-[(2R,5S)-2-(3,5-difluorophenyl)-5-methyl-1-piperidyl]-2-oxo-acetyl]amino]-3-methyl-2-pyridyl]carbamate (32.01 mg, 65.52 µmol, 10% yield).

Ret time for E1 in analytical conditions (column: 1C, CO$_2$-MeOH, 60-40, 2 ml/min as mobile phase) 5.90 min and for E2 4.60 min.

E1: LCMS(ESI): [M]$^+$ m/z: calcd 488.2; found 489.2; Rt=1.478 min.

E2: LCMS(ESI): [M]$^+$ m/z: calcd 488.2; found 489.2; Rt=1.479 min.

Step 6: Synthesis of N-(6-amino-5-methylpyridin-3-yl)-2-(2-(3,5-difluorophenyl)-5-methylpiperidin-1-yl)-2-oxoacetamide (Compound 712 and Compound 734 tert-butyl N-[5-[[2-[(2R,5S)-2-(3,5-difluorophenyl)-5-methyl-1-piperidyl]-2-oxo-acetyl]amino]-3-methyl-2-pyridyl]carbamate (32.01 mg, 65.52 µmol) and tert-butyl N-[5-[[2-[(2S,5R)-2-(3,5-difluorophenyl)-5-methyl-1-piperidyl]-2-oxo-acetyl]amino]-3-methyl-2-pyridyl]carbamate (50.82 mg, 104.03 µmol) were dissolved in water (5 mL) and dioxane (2 mL) mixture. Then reaction mixture was stirred for 17 hr at 100° C. After the completion of the reaction, monitored by LCMS, the resulting suspension was concentrated under reduced pressure. The obtained solid was subjected to HPLC (Waters Sunfire C18 20*100 5 mkm column and H$_2$O-MeOH (100-50%)+FA as an eluent mixture) to afford pure N-(6-amino-5-methyl-3-pyridyl)-2-[(2R,5S)-2-(3,5-difluorophenyl)-5-methyl-1-piperidyl]-2-oxo-acetamide (10.7 mg, 27.55 µmol, 42.04% yield) and N-(6-amino-5-methyl-3-pyridyl)-2-[(2S,5R)-2-(3,5-difluorophenyl)-5-methyl-1-piperidyl]-2-oxo-acetamide (24.7 mg, 63.59 µmol, 61.13% yield).

Compound 712: $^1$H NMR (600 MHz, DMSO-d$_6$) δ (ppm) 0.99 (m, 3H), 1.30 (m, 1H), 1.61 (m, 1H), 1.84 (m, 1H), 2.00 (m, 4H), 2.17 (m, 1H), 2.72 (m, 1H), 3.72 (m, 1H), 5.57 (m, 3H), 7.05 (m, 3H), 7.45 (m, 1H), 7.97 (m, 1H), 10.52 (m, 1H).

LCMS(ESI): [M]$^+$ m/z: calcd 388.2; found 389.2; Rt=2.308 min.

Compound 734: $^1$H NMR (600 MHz, DMSO-d$_6$) δ (ppm) 0.99 (m, 3H), 1.31 (m, 1H), 1.60 (m, 1H), 1.86 (m, 1H), 2.00 (m, 4H), 2.19 (m, 1H), 2.71 (m, 1H), 3.62 (m, 1H), 5.57 (m, 3H), 7.05 (m, 3H), 7.45 (m, 1H), 7.97 (m, 1H), 10.52 (m, 1H).

LCMS(ESI): [M]$^+$ m/z: calcd 388.2; found 389.2; Rt=2.319 min.

Example 734. The Synthesis of 5-(2-(5-methyl-2-(2-methyl-2,3-dihydrobenzofuran-5-yl)piperidin-1-yl)-2-oxoacetamido)nicotinamide (Compound 329, Compound 376, Compound 345, Compound 377

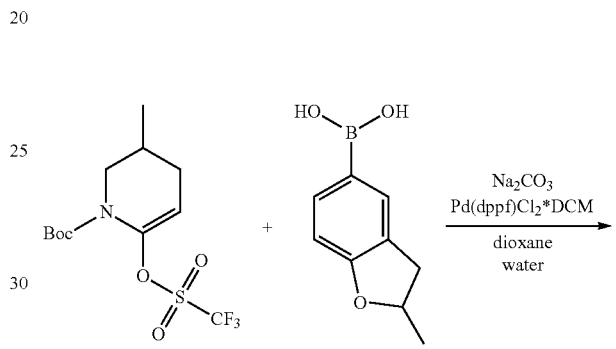

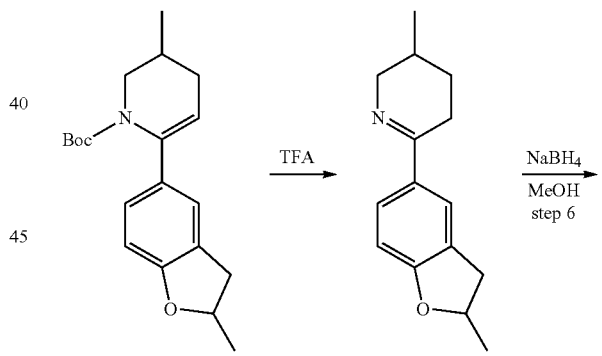

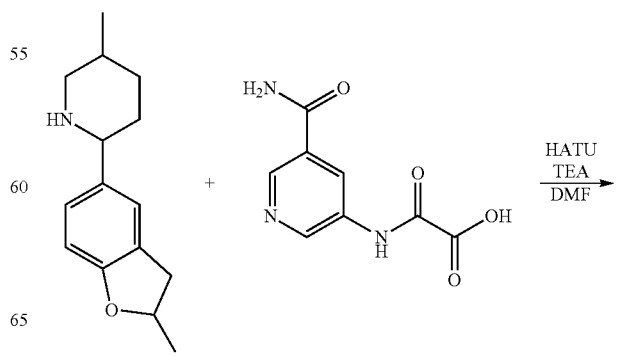

2995
-continued

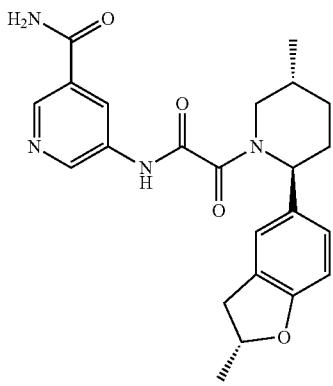

Compound 329

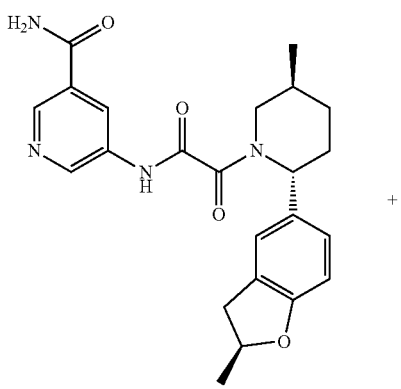

Compound 376

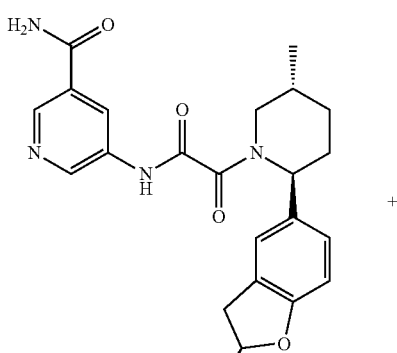

Compound 345

2996
-continued

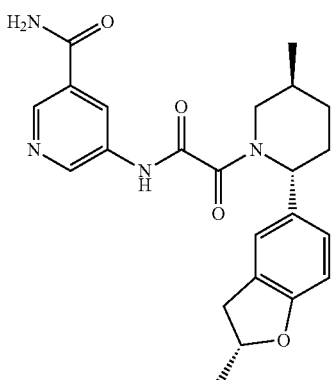

Compound 377

Step 1: Synthesis of tert-butyl 3-methyl-6-(2-methyl-2,3-dihydrobenzofuran-5-yl)-3,4-dihydro-pyridine-1(2H)-carboxylate tert-butyl 3-methyl-6-(trifluoromethylsulfonyloxy)-3,4-dihydro-2H-pyridine-1-carboxylate (4.5 g, 13.03 mmol), (2-methyl-2,3-dihydrobenzofuran-5-yl)boronic acid (2.78 g, 15.64 mmol) and sodium carbonate (4.14 g, 39.09 mmol, 1.64 mL) were added to a mixture of 1,4-dioxane (60 mL) and water (20 mL). The resulting mixture was evacuated and then backfilled with argon, this operation was repeated three times, then Pd(dppf)Cl$_2$ DCM (425.33 mg, 521.23 μmol) was added under argon. The reaction mixture was stirred under argon at 75° C. for 12 hr, then cooled and filtered. The filtercake was washed with 1,4-dioxane (2*20 ml) and discarded. The filtrate was evaporated in vacuo and the residue was purified by column chromatography on silica gel using hexane/MTBE gradient (0-100% MTBE) to afford tert-butyl 3-methyl-6-(2-methyl-2,3-dihydrobenzofuran-5-yl)-3,4-dihydro-2H-pyridine-1-carboxylate (1.1 g, 3.34 mmol, 25.62% yield) as light-yellow gum.

$^1$H NMR (400 MHz, CDCl$_3$) δ (ppm) 1.02 (d, 3H), 1.12 (s, 9H), 1.48 (d, 3H), 1.86 (m, 2H), 2.39 (d, 1H), 2.96 (m, 2H), 3.30 (m, 1H), 4.08 (d, 1H), 4.93 (m, 1H), 5.20 (m, 1H), 6.67 (d, 1H), 7.05 (d, 1H), 7.09 (s, 1H).

LCMS(ESI): [M−Boc]$^+$ m/z: calcd 229.2; found 230.2; Rt=1.798 min.

Step 2: Synthesis of 5-(2-(5-methyl-2-(2-methyl-2,3-dihydrobenzofuran-5-yl)piperidin-1-yl)-2-oxoacetamido)nicotinamide (Compound 329, Compound 376 and Compound 345, Compound 377

HATU (328.73 mg, 864.56 μmol) was added in one portion to a stirred mixture of 5-methyl-2-(2-methyl-2,3-dihydrobenzofuran-5-yl)piperidine (200 mg, 864.56 μmol), 2-[(5-carbamoyl-3-pyridyl)amino]-2-oxo-acetic acid (268.31 mg, 864.56 μmol) and TEA (87.48 mg, 864.56 μmol, 120.50 μL) in DMF (10 mL) at 25° C. The reaction mixture was stirred at 25° C. for 2 hr, then concentrated in vacuo to approximately 5 ml and submitted to reverse phase HPLC (column: YMC Triart C18 100×20 mm, 5 um; mobile phase 45-75% 0-5 min 0.1% NH$_3$-MeOH, flow: 30 ml/min) to afford 100 mg of racemic amide as light-yellow gum, which was then submitted to chiral HPLC (Column: Chiralpak OJ-H (250*20 mm, 5 mkm); Mobile phase: Hexane-IPA-MeOH, 40-30-30 Flow Rate: 10 mL/min; Column Temperature: 24° C.; Wavelength: 205 nm, 236 nm) to afford first two enantiomers as a mixture (rt=14.67 and 16.566 min respectively) and two crude enantiomers with R.T. 36.105 and 68.199 min respectively. A mixture of first two enantiomers with R.T.=14.67 and 16.566 min respectively was then again repurified by chiral HPLC (Column: Chiralpak OJ-H (250*20 mm, 5 mkm); Mobile phase: Hexane-IPA-MeOH, 70-15-15 Flow Rate: 12 mL/min; Column Temperature: 24° C.; Wavelength: 205 nm, 236 nm) to afford Compound 329 5-[[2-[(2S,5R)-5-methyl-2-[(2R)-2-methyl-2,3-dihydrobenzofuran-5-yl]-1-piperidyl]-2-oxo-acetyl]amino]pyridine-3-carboxamide (16.8 mg, 39.77 μmol, 4.60% yield) (R.T.=25.258 min) as white solid, and Compound 345 5-[[2-[(2S,5R)-5-methyl-2-[(2S)-2-methyl-2,3-dihydrobenzofuran-5-yl]-1-piperidyl]-2-oxo-acetyl]amino]pyridine-3-carboxamide (17.6 mg, 41.66 μmol, 4.82% yield) (R.T.=31.452 min) as white solid. Crude third enantiomer with R.T. 36.105 (87% purity by LCMS) was purified by reverse phase HPLC (column C18, mobile phase H$_2$O-MeCN, 35-60% MeCN, flow rate 30 ml/min) to afford Compound 376 5-[[2-[(2R,5S)-5-methyl-2-[(2S)-2-methyl-2,3-dihydrobenzofuran-5-yl]-1-piperidyl]-2-oxo-acetyl]amino]pyridine-3-carboxamide (14.5 mg, 34.32 μmol, 3.97% yield). Fourth enantiomer with R.T.=68.199 min was submitted without further purification as Compound 377 5-[[2-[(2R,5S)-5-methyl-2-[(2R)-2-methyl-2,3-dihydrobenzofuran-5-yl]-1-piperidyl]-2-oxo-acetyl]amino]pyridine-3-carboxamide (17.1 mg, 40.48 μmol, 4.68% yield). Ret time for Compound 329 in analytical conditions (column: OJ-H, CO$_2$-MeOH, 60-40, 2 ml/min as mobile phase) 3.66 min, for Compound 376 5.68 min, for Compound 345 4.09 min and for Compound 377 8.90 min.

Compound 329: Retention time: 3.66 min
$^1$H NMR (600 MHz, DMSO-d$_6$) δ (ppm) 1.01 (m, 3H), 1.29 (m, 1H), 1.35 (m, 3H), 1.71 (m, 1H), 1.87 (m, 1H), 1.97 (m, 1H), 2.14 (m, 1H), 2.77 (m, 1H), 3.24 (m, 1H), 3.52 (m, 2H), 4.87 (m, 1H), 5.27 (m, 1H), 6.68 (m, 1H), 7.02 (m, 1H), 7.14 (m, 1H), 7.59 (m, 1H), 8.14 (m, 1H), 8.46 (m, 1H), 8.75 (m, 1H), 8.85 (m, 1H), 11.18 (m, 1H).
LCMS(ESI): [M]$^+$ m/z: calcd 422.2; found 423.2; Rt=3.143 min.

Compound 376: Retention time: 5.68 min
$^1$H NMR (600 MHz, DMSO-d$_6$) δ (ppm) 0.98-1.04 (m, 3H), 1.19-1.32 (m, 2H), 1.32-1.39 (m, 3H), 1.69-1.78 (m, 1H), 1.82-1.93 (m, 1H), 1.99-2.10 (m, 1H), 2.12-2.21 (m, 1H), 2.67-2.79 (m, 1H), 2.83-3.22 (m, 1H), 3.32-3.99 (m, 1H), 4.79-4.95 (m, 1H), 4.99-5.54 (m, 1H), 6.65-6.75 (m, 1H), 6.98-7.05 (m, 1H), 7.11-7.18 (m, 1H), 7.52-7.63 (m, 1H), 8.09-8.21 (m, 1H), 8.43-8.51 (m, 1H), 8.71-8.81 (m, 1H), 8.81-8.94 (m, 1H), 11.07-11.29 (m, 1H).
LCMS(ESI): [M]$^+$ m/z: calcd 422.2; found 423.2; Rt=3.184 min.

Compound 345: Retention time: 4.09 min
$^1$H NMR (600 MHz, DMSO-d$_6$) δ (ppm) 1.03 (m, 3H), 1.35 (m, 3H), 1.72 (m, 1H), 1.86 (m, 1H), 2.01 (m, 1H), 2.14 (m, 1H), 2.74 (m, 1H), 3.00 (m, 1H), 3.42 (m, 2H), 4.22 (m, 1H), 4.87 (m, 1H), 5.27 (m, 1H), 6.69 (m, 1H), 7.02 (m, 1H), 7.14 (m, 1H), 7.59 (m, 1H), 8.14 (m, 1H), 8.46 (m, 1H), 8.75 (m, 1H), 8.85 (m, 1H), 11.17 (m, 1H).
LCMS(ESI): [M]$^+$ m/z: calcd 422.2; found 423.2; Rt=3.139 min.

Compound 377: Retention time: 8.90 min
$^1$H NMR (500 MHz, DMSO-d$_6$) δ (ppm) 0.97-1.03 (m, 3H), 1.19-1.32 (m, 2H), 1.33-1.41 (m, 3H), 1.69-1.78 (m, 1H), 1.83-1.93 (m, 1H), 1.97-2.10 (m, 1H), 2.13-2.20 (m, 1H), 2.69-2.79 (m, 1H), 2.79-3.24 (m, 1H), 3.39-3.97 (m, 1H), 4.83-4.92 (m, 1H), 5.00-5.55 (m, 1H), 6.64-6.73 (m, 1H), 6.98-7.06 (m, 1H), 7.11-7.18 (m, 1H), 7.56-7.66 (m, 1H), 8.09-8.20 (m, 1H), 8.41-8.51 (m, 1H), 8.71-8.78 (m, 1H), 8.81-8.92 (m, 1H), 11.06-11.31 (m, 1H).
LCMS(ESI): [M]$^+$ m/z: calcd 422.2; found 423.2; Rt=3.184 min.

Example 735. The Synthesis of 2-[(2S,5S)-5-ethyl-2-phenyl-1-piperidyl]-N-(5-methyl-3-pyridyl)-2-oxo-acetamide, 2-[(2S,5R)-5-ethyl-2-phenyl-1-piperidyl]-N-(5-methyl-3-pyridyl)-2-oxo-acetamide and 2-[(2R,5S)-5-ethyl-2-phenyl-1-piperidyl]-N-(5-methyl-3-pyridyl)-2-oxo-acetamide (Compound 20, Compound 17 and Compound 18

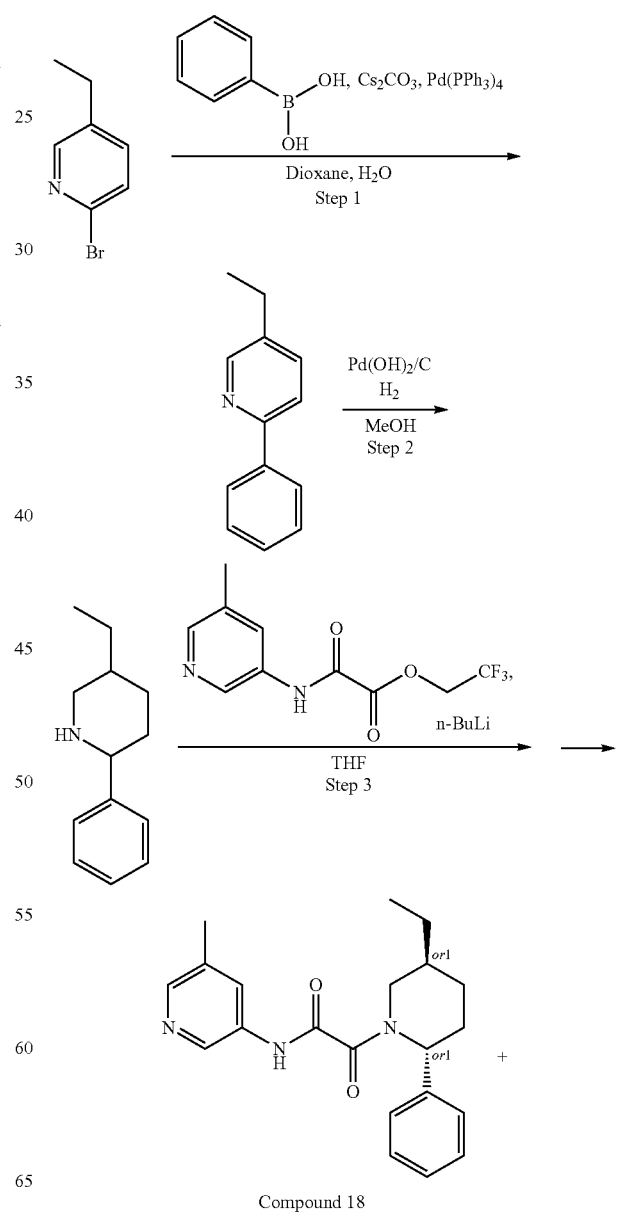

Compound 18

-continued

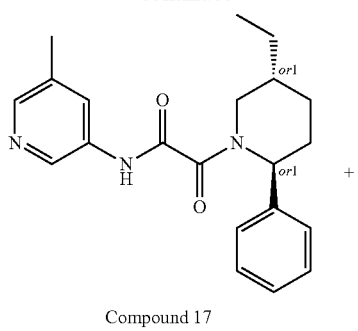

Compound 17

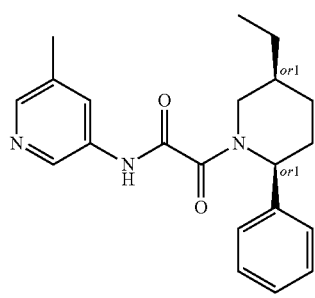

Compound 20

Step 1: Synthesis of 5-ethyl-2-phenyl-pyridine

To a stirred solution of 2-bromo-5-ethyl-pyridine (1 g, 5.37 mmol) and phenylboronic acid (655.36 mg, 5.37 mmol) in dioxane (10 mL) was added cesium carbonate (5.25 g, 16.12 mmol). The resulting suspension was degassed with argon.

Tetrakis(triphenylphosphine)palladium(0) (620 mg, 0.537 mmol) was added. The reaction mixture was stirred at 65° C. for overnight. Upon completion, the reaction mixture was filtered and the filtrate was evaporated in vacuo to obtain an oily residue. The residue was purified by reverse phase HPLC (49% water-acetonitrile; 0.5-6.5 min; flow rate: 30 mL/min; loading pump: 4 mL/min, acetonitrile; column: SunFire 100*19 mm, 5 um) to give product 5-ethyl-2-phenyl-pyridine (0.56 g, 3.06 mmol, 56.86% yield) as yellow oil.

$^1$H NMR (DMSO-$d_6$, 400 MHz): δ (ppm) 1.22 (t, 3H), 2.65 (q, 2H), 7.44 (m, 3H), 7.71 (dd, 1H), 7.87 (d, 1H), 8.06 (d, 2H), 8.53 (d, 1H).

LCMS(ESI): [M+H]$^+$ m/z: calcd 183.1; found 184.2; Rt=2.645 min.

Step 2: Synthesis of 5-ethyl-2-phenyl-piperidine

A solution of 5-ethyl-2-phenyl-pyridine (0.5 g, 2.73 mmol) in MeOH (20 mL) was hydrogenated over 5% Pd(OH)$_2$ on carbon (16.84 mg, 136.43 μmol) under 100 atm H$_2$ pressure at 50° C. for 18 hours. Upon completion, the reaction mixture was filtered, the residue was washed with MeOH (10 mL) and the filtrate was concentrated under reduced pressure to obtain 5-ethyl-2-phenyl-piperidine (0.38 g, 2.01 mmol, 73.57% yield). The crude product was used for the next step without any further purification.

Step 3: Synthesis of 2-[(2S,5S)-5-ethyl-2-phenyl-1-piperidyl]-N-(5-methyl-3-pyridyl)-2-oxo-acetamide, 2-[(2S,5R)-5-ethyl-2-phenyl-1-piperidyl]-N-(5-methyl-3-pyridyl)-2-oxo-acetamide and 2-[(2R,5S)-5-ethyl-2-phenyl-1-piperidyl]-N-(5-methyl-3-pyridyl)-2-oxo-acetamide (Compound 20, Compound 17 and Compound 18

To a stirred solution of 5-ethyl-2-phenyl-piperidine (0.38 g, 2.01 mmol) in THF (10 mL) at −78° C., n-butyllithium (2.5M in Hexane, 385.76 mg, 6.02 mmol, 2.4 mL) was added under argon atmosphere. The resulting mixture was stirred at the same temperature for 5 minutes. After 5 minutes, 2,2,2-trifluoroethyl 2-[(5-methyl-3-pyridyl)amino]-2-oxo-acetate (526.32 mg, 2.01 mmol) dissolved in THF (10 mL) was added to the reaction mixture. The resulting mixture was allowed to warm to room temperature and stirred for overnight at the same temperature. Upon completion, MeOH (5 mL) was added and the reaction mixture was evaporated in vacuo. The obtained crude residue was purified by reverse phase HPLC (Eluent: 44% water-acetonitrile, 0.5-6.5 min; flow rate: 30 mL/min; loading pump: 4 mL/min, acetonitrile; column: SunFire 100*19 mm, 5 um) and chiral column chromatography (column: IA, 250*20 mm, 5 um, Eluent: Hexane-MeOH-IPA, 80-10-10, flow rate: 12 mL/min) to give product 2-[(2S,5S)-5-ethyl-2-phenyl-1-piperidyl]-N-(5-methyl-3-pyridyl)-2-oxo-acetamide (Compound 20) (2 mg, 5.69 μmol, 2.83e-1% yield), 2-[(2S,5R)-5-ethyl-2-phenyl-1-piperidyl]-N-(5-methyl-3-pyridyl)-2-oxo-acetamide (Compound 17) (24 mg, 68.29 μmol, 3.40% yield) and 2-[(2R,5S)-5-ethyl-2-phenyl-1-piperidyl]-N-(5-methyl-3-pyridyl)-2-oxo-acetamide (Compound 18) (28 mg, 79.67 μmol, 3.97% yield) as yellow solid.

Compound 18: $^1$H NMR (DMSO-$d_6$, 500 MHz): δ (ppm) 0.92 (m, 3H), 1.44 (m, 1H), 1.50 (m, 1H), 1.61 (m, 2H), 1.74 (m, 1H), 2.16 (m, 2H), 2.33 (m, 3H), 2.76 (m, 0.4H) 3.26 (m, 0.6H), 3.99 (m, 1H), 5.46 (m, 1H), 7.24 (m, 1H), 7.30 (m, 1H), 7.36 (m, 3H), 7.96 (m, 1H), 8.07 (m, 1H), 8.56 (m, 1H), 10.86 (m, 1H).

LCMS(ESI): [M+H]$^+$ m/z: calcd 351.2; found 352.0; Rt=4.946 min.

Chiral HPLC: Rt=24.87 min (Column: IA; Mobile phase: Hexane-MeOH-IPA, 80-10-10; Flow Rate: 0.8 mL/min).

Compound 17: $^1$H NMR (DMSO-$d_6$, 500 MHz): δ (ppm) 0.92 (m, 3H), 1.44 (m, 1H), 1.50 (m, 1H), 1.61 (m, 2H), 1.74 (m, 1H), 2.16 (m, 2H), 2.33 (m, 3H), 2.76 (m, 0.4H), 3.26 (m, 0.6H), 3.99 (m, 1H), 5.46 (m, 1H), 7.24 (m, 1H), 7.30 (m, 1H), 7.36 (m, 3H), 7.96 (m, 1H), 8.07 (m, 1H), 8.56 (m, 1H), 10.86 (m, 1H).

LCMS(ESI): [M+H]$^+$ m/z: calcd 351.2; found 352.0; Rt=4.996 min.

Chiral HPLC: Rt=32.61 min (Column: IA; Mobile phase: Hexane-MeOH-IPA, 80-10-10; Flow Rate: 0.8 mL/min).

Compound 20: LCMS(ESI): [M+H]$^+$ m/z: calcd 351.2; found 352.0; Rt=5.027 min.

Chiral HPLC: Rt=17.96 min (Column: IA; Mobile phase: Hexane-MeOH-IPA, 80-10-10; Flow Rate: 0.8 mL/min).

3001

Example 736. The Synthesis of 5-(2-(5-ethyl-2-phenylpiperidin-1-yl)-2-oxoacetamido)nicotinamide (Compound 547, Compound 576 and Compound 565

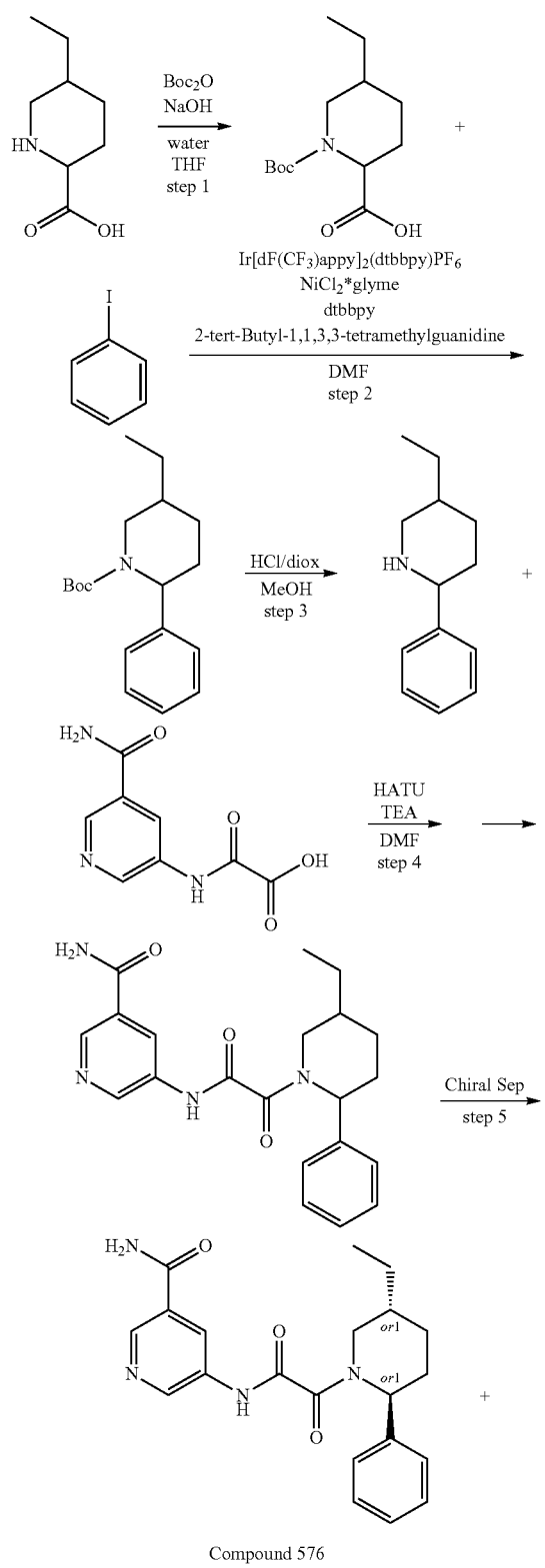

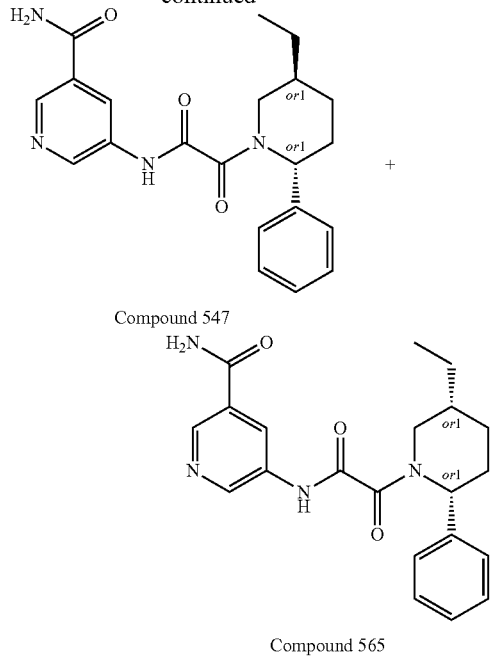

Compound 547

Compound 565

Step 1: Synthesis of 1-(tert-butoxycarbonyl)-5-ethylpiperidine-2-carboxylic acid 5-ethylpiperidine-2-carboxylic acid (5 g, 25.82 mmol, HCl) was dissolved in water (50 mL) and sodium hydroxide, pearl (4.13 g, 103.27 mmol, 1.94 mL) was added thereto. The resulting mixture was diluted with THF (50 mL) and di-tert-butyl dicarbonate (8.45 g, 38.73 mmol, 8.89 mL) was added dropwise to the previous mixture. The reaction mixture was stirred for 18 hr. The reaction mixture was concentrated in vacuo and the residue was diluted with water (50 ml). The resulting mixture was washed with MTBE (3*50 ml) and then was acidified with NaHSO$_4$. The resulting mixture was extracted with DCM (3*50 ml) and combined organic layers were dried over Na$_2$SO$_4$, filtered and evaporated to obtain 1-tert-butoxycarbonyl-5-ethyl-piperidine-2-carboxylic acid (4.03 g, 15.65 mmol, 60.62% yield).

$^1$H NMR (500 MHz, DMSO-d$_6$) δ (ppm) 0.87 (m, 3H), 1.26 (m, 2H), 1.38 (s, 9H), 1.48 (m, 3H), 1.79 (m, 2H), 3.06 (m, 1H), 3.68 (m, 1H), 4.53 (m, 1H), 12.55 (bds, 1H).

LCMS(ESI): [M−Boc]$^+$ m/z: calcd 157.2; found 158.2; Rt=1.289 min.

Step 2: Synthesis of tert-butyl 5-ethyl-2-phenylpiperidine-1-carboxylate

Ir[dF(CF$_3$)ppy]2(dtbbpy)PF$_6$ (43.60 mg, 38.86 μmol), NiCl$_2$·glyme (85.39 mg, 388.61 μmol) and dtbbpy (156.45 mg, 582.92 μmol) were mixed together in DMF (50 mL). 1-tert-butoxycarbonyl-5-ethyl-piperidine-2-carboxylic acid (1 g, 3.89 mmol), 2-tert-butyl-1,1,3,3-tetramethylguanidine (665.62 mg, 3.89 mmol) and iodobenzene (792.80 mg, 3.89 mmol, 433.22 μL) were added to the previous mixture and the resulting mixture was degassed for 15 min by spurging with argon. The vial was sealed, wrapped with parafilm and placed into blue LED photoreactor. The reaction mixture was stirred at 50° C. for 48 hr. The reaction mixture was concentrated in vacuo and water (50 ml) was added to the residue. The resulting mixture was extracted with EtOAc (2*50 ml). Combined organic layers were washed with water (3*50 ml), brine, dried over Na₂SO₄, filtered and evaporated. The residue was purified by HPLC (2-10 min 50-70% MeOH/H₂O 30 ml/min (loading pump 4 ml MeOH), column: SunFire 100*19 mm, 5 microM) to obtain tert-butyl 5-ethyl-2-phenyl-piperidine-1-carboxylate (0.2822 g, 975.08 µmol, 25.09% yield) and tert-butyl 5-ethyl-2-phenyl-piperidine-1-carboxylate (112.20 mg, 387.68 µmol, 9.98% yield).

¹H NMR (400 MHz, DMSO-d₆) δ (ppm) 0.89 (t, 3H), 1.08 (m, 1H), 1.40 (s, 9H), 1.61 (m, 1H), 1.79 (m, 1H), 1.97 (m, 1H), 2.28 (m, 2H), 2.90 (d, 1H), 3.77 (d, 1H), 3.96 (m, 1H), 5.25 (m, 1H), 7.22 (m, 3H), 7.36 (m, 2H).

LCMS(ESI): [M−Boc]⁺ m/z: calcd 189.2; found 190.2; Rt=1.550 min.

Step 3: Synthesis of 5-ethyl-2-phenylpiperidine tert-butyl 5-ethyl-2-phenyl-piperidine-1-carboxylate (0.464 g, 1.60 mmol) was dissolved in MeOH (5 mL) and hydrogen chloride solution 4.0 M in dioxane (584.56 mg, 16.03 mmol, 730.70 µL) was added thereto. The resulting mixture was stirred for 18 hr and then evaporated to dryness to obtain 5-ethyl-2-phenyl-piperidine (0.337 g, 1.49 mmol, 93.11% yield, HCl).

¹H NMR (500 MHz, DMSO-d₆) δ (ppm) 0.90 (d, 3H), 1.68 (m, 6H), 2.72 (m, 1H), 3.06 (m, 1H), 3.26 (m, 1H), 4.22 (m, 1H), 7.42 (m, 3H), 7.54 (m, 2H), 9.52 (m, 1H).

LCMS(ESI): [M]⁺ m/z: calcd 189.2; found 190.2; Rt=0.775 min.

Step 4: Synthesis of 5-(2-(5-ethyl-2-phenylpiperidin-1-yl)-2-oxoacetamido)nicotinamide 5-ethyl-2-phenyl-piperidine (0.337 g, 1.49 mmol, HCl), 2-[(5-carbamoyl-3-pyridyl)amino]-2-oxo-acetic acid (366.65 mg, 1.49 mmol, HCl) and TEA (1.51 g, 14.93 mmol, 2.08 mL) were mixed together in DMF (6 mL) and HATU (851.39 mg, 2.24 mmol) was added thereto. The reaction mixture was stirred for 18 hr. The reaction mixture was concentrated in vacuo and the residue was purified by HPLC (2-10 min 50-70% MeOH/H₂O 30 ml/min (loading pump 4 ml MeOH), column: SunFire 100*19 mm, 5 microM) to obtain 5-[[2-(5-ethyl-2-phenyl-1-piperidyl)-2-oxo-acetyl]amino]pyridine-3-carboxamide (0.2344 g, 616.13 µmol, 41.27% yield)

¹H NMR (500 MHz, DMSO-d₆) δ (ppm) 0.82 (m, 3H), 1.22 (m, 2H), 1.86 (m, 4H), 2.70 (m, 1H), 3.18 (m, 2H), 3.68 (m, 1H), 4.32 (m, 1H), 5.55 (m, 1H), 7.34 (m, 4H), 7.58 (m, 1H), 8.22 (m, 1H), 8.48 (m, 1H), 8.76 (m, 1H), 11.38 (m, 1H).

LCMS(ESI): [M]⁺ m/z: calcd 380.2; found 381.2; Rt=1.129 min.

Step 5: Chiral Separation (Compound 547, Compound 576 and Compound 565

5-[[2-(5-ethyl-2-phenyl-1-piperidyl)-2-oxo-acetyl]amino]pyridine-3-carboxamide (0.2344 g, 616.13 µmol) was chirally separated (cis-/trans-separation: C18, 19*100, H₂O-ACN, 70-30, 30 ml/min, 10 injections, 23 mg/injection, RetTime=15.166; trans-isomers separation: Chiralpak IA II (250*20 mm,5 mkm) Hexane-IPA-MeOH, 50-25-25, 13 ml/min, 2 injections, 20 mg/injection, RetTime=20.247) to obtain 5-[[2-[(2S,5R)-5-ethyl-2-phenyl-1-piperidyl]-2-oxo-acetyl]amino]pyridine-3-carboxamide (0.02606 g, 68.50 µmol, 11.12% yield).

5-[[2-(5-ethyl-2-phenyl-1-piperidyl)-2-oxo-acetyl]amino]pyridine-3-carboxamide (0.2344 g, 616.13 µmol) was chirally separated (cis-/trans-separation: C18, 19*100, H₂O-ACN, 70-30, 30 ml/min, 10 injections, 23 mg/injection, RetTime=15.166; trans-isomers separation: Chiralpak IA II (250*20 mm,5 mkm) Hexane-IPA-MeOH, 50-25-25, 13 ml/min, 2 injections, 20 mg/injection, RetTime=34.381) to obtain 5-[[2-[(2R,5S)-5-ethyl-2-phenyl-1-piperidyl]-2-oxo-acetyl]amino]pyridine-3-carboxamide (0.02981 g, 78.36 µmol, 12.72% yield).

5-[[2-(5-ethyl-2-phenyl-1-piperidyl)-2-oxo-acetyl]amino]pyridine-3-carboxamide (0.2344 g, 616.13 µmol) was chirally separated (C18, 19*100, H₂O-ACN, 70-30, 30 ml/min, 10 injections, 23 mg/injection, RetTime=18.860) to obtain 5-[[2-[(2R,5R)-5-ethyl-2-phenyl-1-piperidyl]-2-oxo-acetyl]amino]pyridine-3-carboxamide (97.35 mg, 255.89 µmol, 41.53% yield).

Compound 547: Retention time: 34.38 min

¹H NMR (600 MHz, DMSO-d₆) δ (ppm) 0.74-0.94 (m, 3H), 1.32-1.47 (m, 2H), 1.47-1.57 (m, 2H), 1.59-1.68 (m, 1H), 1.91-2.09 (m, 1H), 2.14-2.28 (m, 1H), 2.75-3.23 (m, 1H), 3.59-4.20 (m, 1H), 5.10-5.61 (m, 1H), 7.23-7.29 (m, 1H), 7.29-7.32 (m, 1H), 7.32-7.42 (m, 3H), 7.54-7.70 (m, 1H), 8.05-8.20 (m, 1H), 8.40-8.55 (m, 1H), 8.70-8.80 (m, 1H), 8.80-8.96 (m, 1H), 11.06-11.38 (m, 1H).

LCMS(ESI): [M]⁺ m/z: calcd 380.2; found 381.2; Rt=1.077 min.

Compound 576: Retention time: 20.25 min

¹H NMR (600 MHz, DMSO-d₆) δ (ppm) 0.71-0.93 (m, 3H), 1.30-1.48 (m, 2H), 1.48-1.58 (m, 2H), 1.59-1.69 (m, 1H), 1.92-2.10 (m, 1H), 2.14-2.27 (m, 1H), 2.74-3.26 (m, 1H), 3.56-4.26 (m, 1H), 5.12-5.59 (m, 1H), 7.23-7.29 (m, 1H), 7.29-7.32 (m, 1H), 7.32-7.41 (m, 3H), 7.53-7.67 (m, 1H), 8.09-8.22 (m, 1H), 8.39-8.53 (m, 1H), 8.70-8.80 (m, 1H), 8.81-8.94 (m, 1H), 11.01-11.46 (m, 1H).

LCMS(ESI): [M]⁺ m/z: calcd 380.2; found 381.2; Rt=1.073 min.

Compound 565: Retention time: 18.86 min

¹H NMR (600 MHz, DMSO-d₆) δ (ppm) 0.71-0.85 (m, 3H), 0.99-1.13 (m, 3H), 1.41-1.57 (m, 1H), 1.69-1.75 (m, 1H), 1.84-1.96 (m, 1H), 2.54-2.63 (m, 2H), 3.64-4.36 (m, 1H), 5.14-5.76 (m, 1H), 7.24-7.29 (m, 1H), 7.29-7.32 (m, 1H), 7.32-7.36 (m, 1H), 7.36-7.42 (m, 2H), 7.53-7.66 (m, 1H), 8.11-8.20 (m, 1H), 8.39-8.54 (m, 1H), 8.70-8.80 (m, 1H), 8.80-8.96 (m, 1H), 11.26 (s, 1H).

LCMS(ESI): [M]⁺ m/z: calcd 380.2; found 381.2; Rt=2.860 min.

Example 737. The Synthesis of 5-[[2-[(2S,5R)-2-(6-Fluoro-1H-indazol-5-yl)-5-methyl-1-piperidyl]-2-oxo-acetyl]amino]pyridine-3-carboxamide (Compound 571) and 5-[[2-[(2R,5S)-2-(6-Fluoro-1H-indazol-5-yl)-5-methyl-1-piperidyl]-2-oxo-acetyl]amino]pyridine-3-carboxamide (Compound 553)

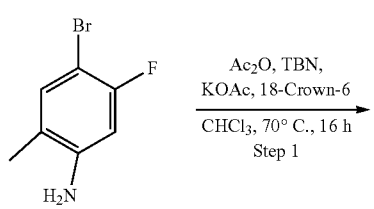

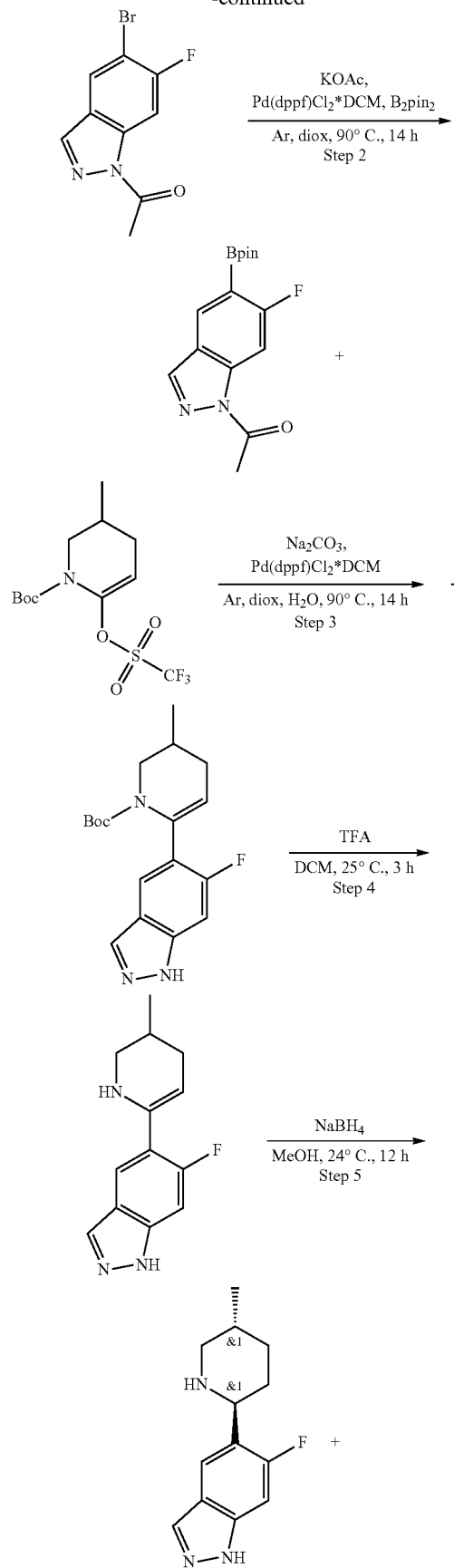

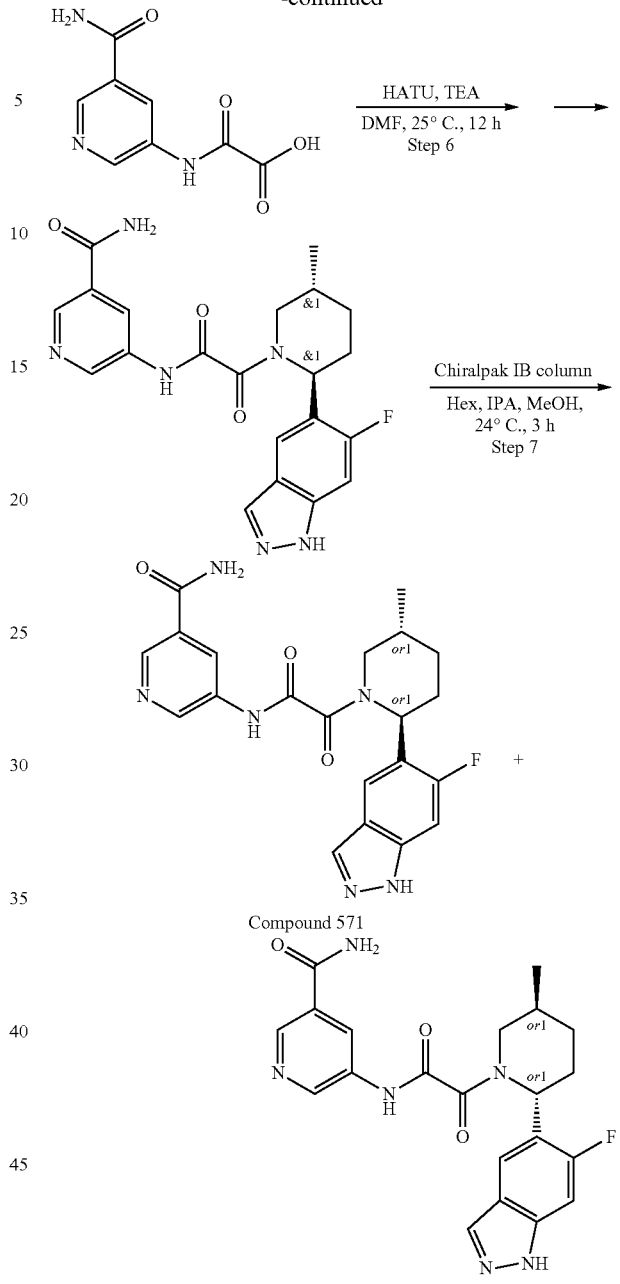

Compound 571

Compound 553

Step 1: The Synthesis of
1-(5-bromo-6-fluoro-1H-indazol-1-yl)ethanone

Acetic anhydride (10.01 g, 98.02 mmol, 9.27 mL) was added to a suspension of 4-bromo-5-fluoro-2-methyl-aniline (10 g, 49.01 mmol) in chloroform (100 mL) under ice-bath cooling and the mixture stirred at RT for 5 min. Potassium Acetate (5.29 g, 53.91 mmol, 3.37 mL), a solution of 18-crown-6 (25.91 g, 98.02 mmol, 21.96 mL) in chloroform (30 mL) and tert-butyl nitrite (10.61 g, 102.92 mmol, 12.24 mL) were then added and the mixture heated at 75° C. for 16 hr. The dark brown mixture was then cooled, DCM (20 mL) was added and the organic layer was washed with saturated aqueous sodium bicarbonate solution. The crude product was purified by column chromatography.

¹H NMR (400 MHz, CDCl₃) δ 2.76 (s, 3H), 7.92 (s, 1H), 8.04 (s, 1H), 8.23 (s, 1H).

Step 2: The Synthesis of 1-[6-fluoro-5-(4,4,5,5-tetramethyl-1,3,2-dioxaborolan-2-yl)indazol-1-yl]ethanone Potassium Acetate (1.68 g, 17.12 mmol, 1.07 mL) was added a solution of 1-(5-bromo-6-fluoro-indazol-1-yl)ethanone (2 g, 7.78 mmol) in dioxane (20 mL), followed by addition of bis(pinacolato)diboron (2.17 g, 8.56 mmol) and Pd(dppf)Cl₂ (284.64 mg, 389.02 μmol). The resulting solution was stirred overnight at 90° C. under Ar. The resulting mixture was concentrated under vacuum, diluted with EtOAc, filtered and evaporated. Resulting crude precipitate was purified by column chromatography (Hexane/MTBE, Flow Rate: 85 ml/min) to obtain 1-[6-fluoro-5-(4,4,5,5-tetramethyl-1,3,2-dioxaborolan-2-yl)indazol-1-yl]ethanone (1.29 g, 4.24 mmol, 54.52% yield).

¹H NMR (500 MHz, CDCl₃) δ 1.40 (s, 12H), 2.79 (s, 3H), 8.10 (s, 1H), 8.11 (s, 1H), 8.13 (s, 1H).

Step 3: The Synthesis of tert-butyl 6-(6-Fluoro-1H-indazol-5-yl)-3-methyl-3,4-dihydro-2H-pyridine-1-carboxylate To a solution of potassium carbonate (1.76 g, 12.73 mmol, 768.01 μL) in water (15 mL) was added to a solution of tert-butyl 3-methyl-6-(trifluoromethylsulfonyloxy)-3,4-dihydro-2H-pyridine-1-carboxylate (1.46 g, 4.24 mmol) in dioxane (15 mL), followed by addition of 1-[6-fluoro-5-(4,4,5,5-tetramethyl-1,3,2-dioxaborolan-2-yl)indazol-1-yl]ethanone (1.29 g, 4.24 mmol) and Pd(dppf)Cl₂ (155.18 mg, 212.08 μmol). The resulting mixture was stirred overnight at 90° C. under Ar. The resulting mixture was concentrated under vacuum, diluted with EtOAc, filtered and evaporated. The crude product was purified by HPLC (2-10 min 10-50% MeCN, 30 ml/min) to obtain tert-butyl 6-(6-fluoro-1H-indazol-5-yl)-3-methyl-3,4-dihydro-2H-pyridine-1-carboxylate (1.8 g, crude).

LCMS(ESI): [M+H]⁺ m/z: calcd 331.2; found 332.2; Rt=1.312 min.

Step 4: The Synthesis of 6-Fluoro-5-(3-methyl-2,3,4,5-tetrahydropyridin-6-yl)-1H-indazole A solution of tert-butyl 6-(6-fluoro-1H-indazol-5-yl)-3-methyl-3,4-dihydro-2H-pyridine-1-carboxylate (1.8 g, 5.43 mmol) in TFA (10 mL) and DCM (10 mL) was stirred at 25° C. for 3 hr. Potassium carbonate saturated aq. solution was added to the solution (50 ml) and then extracted with DCM (2×50 ml). Organic phase was dried over sodium sulfate, filtered and evaporated to obtain 6-fluoro-5-(3-methyl-2,3,4,5-tetrahydropyridin-6-yl)-1H-indazole (1.45 g, crude). The obtained product was used in the next step without an additional work-up.

Step 5: The Synthesis of 6-Fluoro-5-[(2S,5R)-5-methyl-2-piperidyl]-1H-indazole Sodium Borohydride (170.79 mg, 4.51 mmol, 159.61 μL) was added portionwise to a solution of 6-fluoro-5-(3-methyl-2,3,4,5-tetrahydropyridin-6-yl)-1H-indazole (1.45 g, 3.76 mmol) in Methanol (15 mL). The mixture was stirred at rt for 12 hr. Water (50 ml) was added and resulting mixture was extracted with EtOAc (2×50 ml). Organic phase was dried over sodium sulfate, filtered and evaporated to obtain 6-fluoro-5-[(2S,5R)-5-methyl-2-piperidyl]-1H-indazole (753 mg, crude).

¹H NMR (500 MHz, CDCl₃) δ 0.94 (d, 3H), 1.25 (m, 2H), 1.58 (m, 2H), 1.93 (m, 2H), 2.51 (m, 1H), 3.20 (m, 1H), 3.93 (m, 1H), 7.10 (s, 1H), 7.86 (s, 1H), 7.99 (s, 1H), 10.51 (m, 1H).

LCMS(ESI): [M+H]⁺ m/z: calcd 233.2; found 234.0; Rt=0.802 min.

Step 6: The Synthesis of 5-[[2-[(2S,5R)-2-(6-Fluoro-1H-indazol-5-yl)-5-methyl-1-piperidyl]-2-oxo-acetyl]amino]pyridine-3-carboxamide 6-Fluoro-5-[(2S,5R)-5-methyl-2-piperidyl]-1H-indazole (450 mg, 1.93 mmol), 2-[(5-carbamoyl-3-pyridyl)amino]-2-oxo-acetic acid (473.80 mg, 1.93 mmol, HCl), triethylamine (975.97 mg, 9.64 mmol, 1.34 mL) were mixed in DMF (10 mL) and then HATU (1.10 g, 2.89 mmol) were added. Resulting mixture were stirred at 25° C. for 12 hr. The mixture was evaporated under reduce pressure and purified with HPLC (2-10 min 30-100% methanol/H₂O, 30 ml/min) to obtain 5-[[2-[(2S,5R)-2-(6-fluoro-1H-indazol-5-yl)-5-methyl-1-piperidyl]-2-oxo-acetyl]amino]pyridine-3-carboxamide (127.3 mg, 299.93 μmol, 15.55% yield).

LCMS(ESI): [M+H]⁺ m/z: calcd 424.2; found 425.2; Rt=1.081 min.

Step 7: The Synthesis of 5-[[2-[(2S,5R)-2-(6-Fluoro-1H-indazol-5-yl)-5-methyl-1-piperidyl]-2-oxo-acetyl]amino]pyridine-3-carboxamide (Compound 571) and 5-[[2-[(2R,5S)-2-(6-Fluoro-1H-indazol-5-yl)-5-methyl-1-piperidyl]-2-oxo-acetyl]amino]pyridine-3-carboxamide (Compound 553

The mixture of diastereomers was separated by chiral chromatography (Chiralpak 1B 250*20, 5 B Hexane-IPA-MeOH, 50-25-25, 15 ml/min 0.1131) to obtain Compound 571—5-[[2-[(2S,5R)-2-(6-fluoro-1H-indazol-5-yl)-5-methyl-1-piperidyl]-2-oxo-acetyl]amino]pyridine-3-carboxamide (49.4 mg, 116.39 μmol, 38.81% yield) (RT=9.988) and Compound 553—5-[[2-[(2R,5S)-2-(6-fluoro-1H-indazol-5-yl)-5-methyl-1-piperidyl]-2-oxo-acetyl]amino]pyridine-3-carboxamide (46.71 mg, 110.05 μmol, 36.69% yield) (RT=14.543).

Compound 571: ¹H NMR (600 MHz, DMSO-d₆) δ 0.93-1.02 (m, 3H), 1.18-1.42 (m, 1H), 1.82-1.91 (m, 1H), 1.91-2.07 (m, 2H), 2.10-2.27 (m, 1H), 3.37-3.67 (m, 1H), 3.69-3.97 (m, 1H), 5.44-5.55 (m, 1H), 7.19-7.41 (m, 1H), 7.49-7.65 (m, 1H), 7.68-7.83 (m, 1H), 7.90-8.24 (m, 2H), 8.26-8.57 (m, 1H), 8.60-8.93 (m, 2H), 10.70-11.34 (m, 1H), 12.95-13.22 (m, 1H).

LCMS(ESI): [M+H]⁺ m/z: calcd 424.2; found 425.2; Rt=2.168 min.

Compound 553: ¹H NMR (600 MHz, DMSO-d₆) δ 0.99-1.02 (m, 3H), 1.19-1.39 (m, 1H), 1.82-1.91 (m, 1H), 1.93-2.10 (m, 2H), 2.11-2.26 (m, 1H), 3.38-3.65 (m, 1H), 3.71-3.97 (m, 1H), 5.46-5.55 (m, 1H), 7.18-7.38 (m, 1H), 7.50-7.64 (m, 1H), 7.70-7.81 (m, 1H), 7.97-8.19 (m, 2H), 8.28-8.54 (m, 1H), 8.61-8.93 (m, 2H), 10.81-11.31 (m, 1H), 12.91 13.20 (m, 1H).

LCMS(ESI): [M+H]⁺ m/z: calcd 424.2; found 425.2; Rt=2.168 min.

Example 738. The Synthesis of 5-[[2-[(2R,5S)-2-(3-Fluoro-4-hydroxy-phenyl)-5-methyl-1-piperidyl]-2-oxo-acetyl]amino]pyridine-3-carboxamide and 5-[[2-[(2S,5R)-2-(3-Fluoro-4-hydroxy-phenyl)-5-methyl-1-piperidyl]-2-oxo-acetyl]amino]pyridine-3-carboxamide (Compound 355 and Compound 354

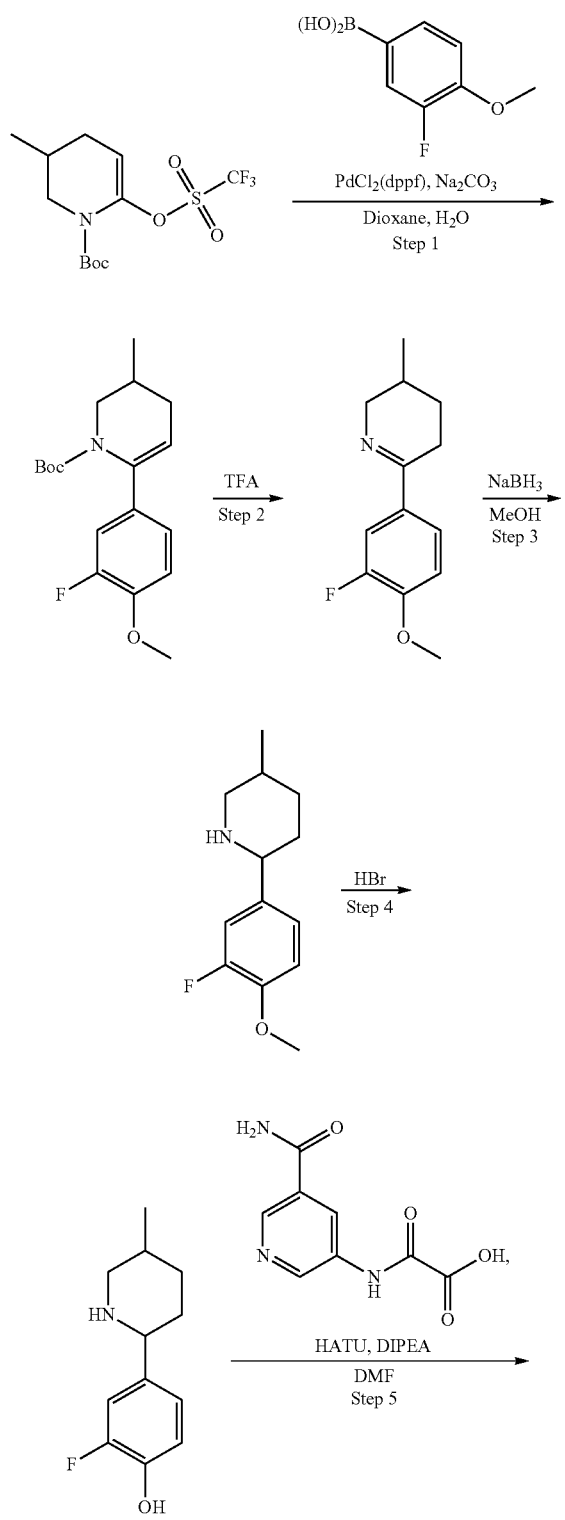

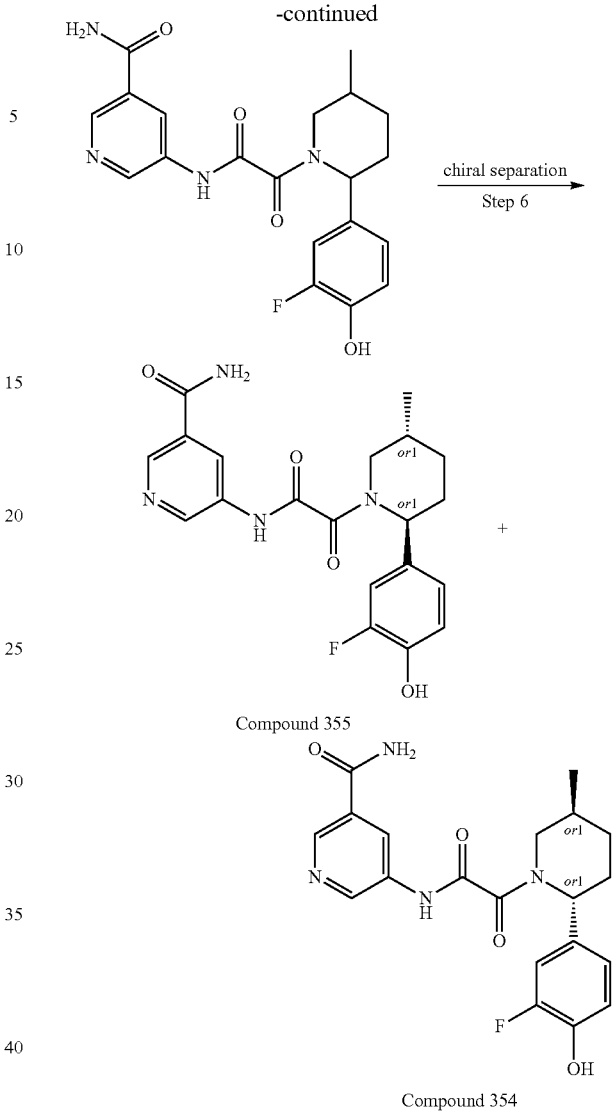

Step 1: Synthesis of tert-butyl 6-(3-Fluoro-4-methoxy-phenyl)-3-methyl-3,4-dihydro-2H-pyridine-1-carboxylate A stirring suspension of tert-butyl 3-methyl-6-(trifluoromethylsulfonyloxy)-3,4-dihydro-2H-pyridine-1-carboxylate (3.8 g, 11.00 mmol), (3-fluoro-4-methoxy-phenyl)boronic acid (1.87 g, 11.00 mmol) and Sodium carbonate (3.50 g, 33.01 mmol, 1.38 mL) in 1,4-dioxane (30 mL) and water (10 mL) was purged with argon for 10 minutes. After 10 minutes, Pd(dppf)Cl$_2$CH$_2$Cl$_2$ (450 mg, 550.19 μmol) was added under argon. The reaction mixture was stirred under argon at 70° C. for 13 hours. After 13 hours, the reaction mixture was cooled to room temperature and filtered. The filter cake was washed with 1,4-dioxane (2×20 mL) and discarded. The filtrate was evaporated under reduced pressure to obtain tert-butyl 6-(3-fluoro-4-methoxy-phenyl)-3-methyl-3,4-dihydro-2H-pyridine-1-carboxylate (3 g, 9.33 mmol, 84.83% yield) as yellow oil. The crude product was used in next step reaction without any further purification. LCMS(ESI): [M+Boc]$^+$ m/z: calcd 321.2; found 266.0 (t-Bu cleaved product mass); Rt=1.528 min Step 2: Synthesis of 6-(3-fluoro-4-methoxy-phenyl)-3-methyl-2,3,4,5-tetrahydropyridine Trifluoroacetic acid (21.29 g, 186.69 mmol, 14.38 mL) was added to tert-butyl 6-(3-fluoro-4-methoxy-phenyl)-3-methyl-3,4-dihydro-2H-pyridine-1-carboxylate (3 g, 9.33 mmol) and the resulting reaction mixture was stirred at 25° C. for 1 hour. After 1 hour, the reaction mixture was concentrated under reduced pressure. The obtained residue was dissolved in 20 mL ice-cold water and 10% NaOH solution was added drop wise till pH=10. The resulting suspension was extracted with dichloromethane (2×30 mL). The combined organic phase was dried over $Na_2SO_4$ and concentrated under reduced pressure to obtain 6-(3-fluoro-4-methoxy-phenyl)-3-methyl-2,3,4,5-tetrahydropyridine (1.5 g, 6.78 mmol, 72.62% yield) as a yellow gum, which was used directly in the next step.

LCMS(ESI): $[M+H]^+$ m/z: calcd 221.2; found 222.2; Rt=0.828 min.

Step 3: Synthesis of 2-(3-Fluoro-4-methoxy-phenyl)-5-methyl-piperidine

Sodium Borohydride (512.94 mg, 13.56 mmol) was added in one portion at 0° C. to a stirred solution of 6-(3-fluoro-4-methoxy-phenyl)-3-methyl-2,3,4,5-tetrahydropyridine (1.5 g, 6.78 mmol) in methanol (30 mL). The reaction mixture was stirred at 0° C. for 1 hour. After 1 hour, the reaction mixture was concentrated under reduced pressure. The obtained residue was dissolved in water (20 mL) and extracted with dichloromethane (2×40 mL). The combined organic phase was dried over $Na_2SO_4$ and concentrated under reduced pressure. The obtained crude product was purified by column chromatography to obtain 2-(3-fluoro-4-methoxy-phenyl)-5-methyl-piperidine (0.8 g, 3.58 mmol, 52.85% yield).

LCMS(ESI): $[M+H]^+$ m/z: calcd 223.2; found 224.1; Rt=0.873 min.

Step 4: Synthesis of 2-Fluoro-4-(5-methyl-2-piperidyl)phenol

A mixture of 2-(3-fluoro-4-methoxy-phenyl)-5-methyl-piperidine (0.4 g, 1.79 mmol) in HBr (1.48 g, 18.27 mmol, 992.26 µL) was stirred at 100° C. for 24 hours. The resulting reaction mixture was evaporated in vacuo. The obtained crude product was subjected to HPLC purification to afford 2-fluoro-4-(5-methyl-2-piperidyl)phenol (0.26 g, 1.24 mmol, 69.36% yield) as a brown gum.

LCMS(ESI): $[M+H]^+$ m/z: calcd 209.2; found 210.4; Rt=1.766 min.

Step 5: Synthesis of rac-5-[[2-[(2S,5R)-2-(3-Fluoro-4-hydroxy-phenyl)-5-methyl-1-piperidyl]-2-oxo-acetyl]amino]pyridine-3-carboxamide To a stirred solution of 2-fluoro-4-(5-methyl-2-piperidyl)phenol (0.26 g, 1.24 mmol), 2-[(5-carbamoyl-3-pyridyl)amino]-2-oxo-acetic acid (259.88 mg, 1.06 mmol, HCl salt) and DIPEA (562.04 mg, 4.35 mmol, 757.46 µL) in DMF (10 mL) at 25° C. was added HATU (519.67 mg, 1.37 mmol) portion wise. The resulting reaction mixture was stirred at 25° C. Upon completion, the reaction mixture was concentrated under reduced pressure to obtain the crude product, which was purified by reverse phase HPLC to afford rac-5-[[2-[(2S,5R)-2-(3-fluoro-4-hydroxy-phenyl)-5-methyl-1-piperidyl]-2-oxo-acetyl]amino]pyridine-3-carboxamide (0.15 g, 374.62 µmol, 30.15% yield) as a light-yellow solid.

LCMS(ESI): $[M+H]^+$ m/z: calcd 400.2; found 401.2; Rt=2.593 min.

Step 6: Chiral Separation of 5-[[2-[(2R,5S)-2-(3-Fluoro-4-hydroxy-phenyl)-5-methyl-1-piperidyl]-2-oxo-acetyl]amino]pyridine-3-carboxamide and 5-[[2-[(2S,5R)-2-(3-Fluoro-4-hydroxy-phenyl)-5-methyl-1-piperidyl]-2-oxo-acetyl]amino]pyridine-3-carboxamide (Compound 355 and Compound 354 rac-5-[[2-[(2S,5R)-2-(3-fluoro-4-hydroxy-phenyl)-5-methyl-1-piperidyl]-2-oxo-acetyl]amino]pyridine-3-carboxamide was subjected to chiral HPLC purification (Column: Chiralpak IA-I (250×20 mm, 5 um); Mobile phase: Hexane-IPA-MeOH, 75-15-15; Flow rate: 12 mL/min) to afford 5-[[2-[(2R,5S)-2-(3-fluoro-4-hydroxy-phenyl)-5-methyl-1-piperidyl]-2-oxo-acetyl]amino]pyridine-3-carboxamide (Compound 355, 54.5 mg) and 5-[[2-[(2S,5R)-2-(3-fluoro-4-hydroxy-phenyl)-5-methyl-1-piperidyl]-2-oxo-acetyl]amino]pyridine-3-carboxamide (Compound 354, 54.6 mg) as beige solids.

Compound 355:
$^1$H NMR (DMSO-$d_6$, 600 MHz): δ (ppm) 0.99-1.03 (m, 3H), 1.28-1.35 (m, 1H), 1.63-1.73 (m, 1H), 1.81-1.94 (m, 1H), 1.97-2.06 (m, 1H), 2.10-2.18 (m, 1H), 2.71-3.21 (m, 1H), 3.41-4.02 (m, 1H), 5.00-5.53 (m, 1H), 6.90-6.99 (m, 2H), 7.01-7.15 (m, 1H), 7.53-7.66 (m, 1H), 8.10-8.19 (m, 1H), 8.42-8.50 (m, 1H), 8.73-8.81 (m, 1H), 8.81-8.91 (m, 1H), 9.77-9.83 (m, 1H), 11.17-11.28 (m, 1H).

LCMS(ESI): $[M+H]^+$ m/z: calcd 400.2; found 401.4; Rt=2.596 min.

Chiral HPLC: Rt=12.14 min (Column: IA; Mobile phase: Hexane-IPA-MeOH, 50-25-25; Flow Rate: 0.6 mL/min).

Compound 354:
$^1$H NMR (DMSO-$d_6$, 600 MHz): δ (ppm) 0.98-1.02 (m, 3H), 1.27-1.37 (m, 1H), 1.63-1.73 (m, 1H), 1.82-1.92 (m, 1H), 1.94-2.04 (m, 1H), 2.11-2.17 (m, 1H), 2.75-3.21 (m, 1H), 3.36-4.00 (m, 1H), 5.01-5.52 (m, 1H), 6.91-6.97 (m, 2H), 7.02-7.14 (m, 1H), 7.54-7.65 (m, 1H), 8.12-8.24 (m, 1H), 8.43-8.51 (m, 1H), 8.71-8.81 (m, 1H), 8.81-8.90 (m, 1H), 9.80 (s, 1H), 11.16-11.31 (m, 1H).

LCMS(ESI): $[M+H]^+$ m/z: calcd 400.2; found 401.4; Rt=2.605 min.

Chiral HPLC: Rt=16.37 min (Column: IA; Mobile phase: Hexane-IPA-MeOH, 50-25-25; Flow Rate: 0.6 mL/min).

Example 739. The Synthesis of N-(6-amino-5-methyl-3-pyridyl)-2-[(2R,5S)-5-methyl-2-[6-(trifluoromethyl)-3-pyridyl]-1-piperidyl]-2-oxo-acetamide (Compound 1012) and N-(6-amino-5-methyl-3-pyridyl)-2-[(2S,5R)-5-methyl-2-[6-(trifluoromethyl)-3-pyridyl]-1-piperidyl]-2-oxo-acetamide (Compound 1015)

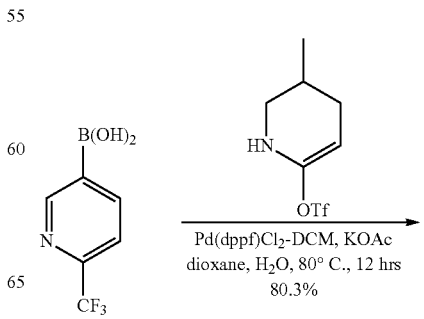

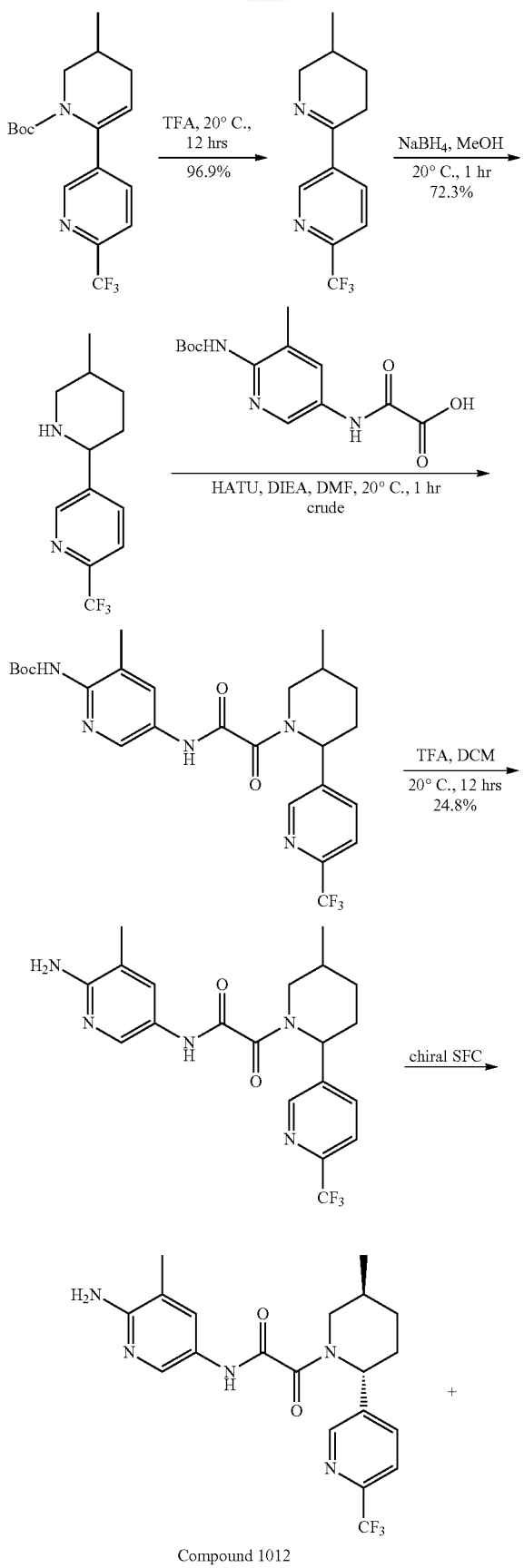

Compound 1012

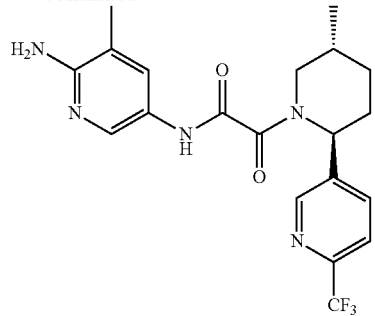

Compound 1015

Step 1: Synthesis of tert-butyl 3-methyl-6-[6-(trifluoromethyl)-3-pyridyl]-3,4-dihydro-2H-pyridine-1-carboxylate To a round bottom flask were added [6-(trifluoromethyl)-3-pyridyl]boronic acid (500 mg, 2.62 mmol), tert-butyl 3-methyl-6-(trifluoromethylsulfonyloxy)-3,4-dihydro-2H-pyridine-1-carboxylate (1.00 g, 2.90 mmol), Pd(dppf)Cl$_2$-DCM (450 mg, 0.551 mmol), Na$_2$CO$_3$ (850 mg, 8.02 mmol), H$_2$O (5 mL) and Dioxane (20 mL). The mixture was degassed and backfilled with nitrogen for three times and then stirred for 12 hours at 80° C. under nitrogen. The resulting mixture was quenched by addition of water (30 mL) and extracted with EtOAc (50 mL*3). The combined organic layer was washed with brine (20 mL), dried over anhydrous Na$_2$SO$_4$, filtered and concentrated under reduced pressure. The residue was purified by flash chromatography (ISCO®; 20 g AgelaFlash® Silica Flash Column, petroleum ether/EtOAc with EtOAc from 0~40%, Flow rate: 30 mL/min) to afford tert-butyl 3-methyl-6-[6-(trifluoromethyl)-3-pyridyl]-3,4-dihydro-2H-pyridine-1-carboxylate (720 mg, 80.3% yield) as yellow solid. $^1$H NMR (400 MHz, chloroform-d) δ ppm 8.65 (d, J=1.5 Hz, 1H), 7.73 (dd, J=8.1, 1.5 Hz, 1H), 7.62 (d, J=8.1 Hz, 1H), 5.44 (t, J=3.7 Hz, 1H), 4.08 (br dd, J=12.5, 2.8 Hz, 1H), 3.05 (dd, J=12.5, 9.5 Hz, 1H), 2.38-2.54 (m, 1H), 1.98-2.17 (m, 1H), 1.84-1.97 (m, 1H), 1.12 (br s, 9H), 1.05 (d, J=6.6 Hz, 3H); $^{19}$F NMR (377 MHz, chloroform-d) δ ppm-67.63.

Step 2: Synthesis of 5-(3-methyl-2,3,4,5-tetrahydropyridin-6-yl)-2-(trifluoromethyl)pyridine To a solution of tert-butyl 3-methyl-6-[6-(trifluoromethyl)-3-pyridyl]-3,4-dihydro-2H-pyridine-1-carboxylate (700 mg, 2.04 mmol) in DCM (2 mL) was added TFA (2 mL, 26.0 mmol). The mixture was stirred at 20° C. for 12 hours. The resulting mixture was quenched by addition of saturated NaHCO$_3$ aqueous solution (30 mL) and extracted with DCM (20 mL*3). The combined organic layer was dried over anhydrous Na$_2$SO$_4$, filtered and concentrated under reduced pressure to afford 5-(3-methyl-2,3,4,5-tetrahydropyridin-6-yl)-2-(trifluoromethyl)pyridine (480 mg, 96.9% yield) as yellow solid. LCMS (ESI) [M+H]$^+$ m/z: calcd 243.1, found 243.1.

Step 3: Synthesis of 5-(5-methyl-2-piperidyl)-2-(trifluoromethyl)pyridine

To a solution of 5-(3-methyl-2,3,4,5-tetrahydropyridin-6-yl)-2-(trifluoromethyl)pyridine (480 mg, 1.98 mmol) in MeOH (20 mL) was added NaBH₄ (120 mg, 3.17 mmol). The mixture was stirred at 20° C. for 1 hour. The resulting mixture was quenched by addition of saturated NH₄Cl aqueous solution (20 mL) and extracted with EtOAc (30 mL*3). The combined organic layer was dried over anhydrous Na₂SO₄, filtered and concentrated under reduced pressure to afford 5-(5-methyl-2-piperidyl)-2-(trifluoromethyl)pyridine (350 mg, 72.3% yield) as yellow solid. LCMS (ESI) [M+H]⁺ m/z: calcd 245.1, found 245.1.

Step 4: Synthesis of tert-butyl N-[3-methyl-5-[[2-[5-methyl-2-[6-(trifluoromethyl)-3-pyridyl]-1-piperidyl]-2-oxo-acetyl]amino]-2-pyridyl]carbamate To a solution of 2-[[6-(tert-butoxycarbonylamino)-5-methyl-3-pyridyl]amino]-2-oxo-acetic acid (150 mg, 0.508 mmol) and 5-(5-methyl-2-piperidyl)-2-(trifluoromethyl)pyridine (150 mg, 0.614 mmol) in DCM (3 mL) were added HATU (200 mg, 0.526 mmol) and DIPEA (0.3 mL, 1.72 mmol). The mixture was stirred at 20° C. for 1 hour. The resulting mixture was quenched by addition of water (100 mL) and extracted with EtOAc (100 mL*3). The combined organic layer was washed with saturated NH₄Cl aqueous solution (100 mL*2), brine (100 mL), dried over anhydrous Na₂SO₄, filtered and concentrated under reduced pressure to afford tert-butyl N-[3-methyl-5-[[2-[5-methyl-2-[6-(trifluoromethyl)-3-pyridyl]-1-piperidyl]-2-oxo-acetyl]amino]-2-pyridyl]carbamate (250 mg, crude) as yellow oil. LCMS (ESI) [M+H]⁺ m/z: calcd 522.2, found 522.3.

Step 5: Synthesis of N-(6-amino-5-methyl-3-pyridyl)-2-[5-methyl-2-[6-(trifluoromethyl)-3-pyridyl]-1-piperidyl]-2-oxo-acetamide To a solution of tert-butyl N-[3-methyl-5-[[2-[5-methyl-2-[6-(trifluoromethyl)-3-pyridyl]-1-piperidyl]-2-oxo-acetyl]amino]-2-pyridyl]carbamate (250 mg, 0.479 mmol) in DCM (1 mL) was added TFA (1 mL, 13.0 mmol). The mixture was stirred at 20° C. for 12 hours. The resulting mixture was quenched by addition of saturated NaHCO₃ aqueous solution (30 mL) and extracted with DCM (30 mL*3). The combined organic layer was dried over anhydrous Na₂SO₄, filtered and concentrated under reduced pressure. The residue was purified by preparative HPLC (Instrument: Gilson GX-281 Liquid Handler, Gilson 322 Pump, Gilson 156 UV Detector; Column: Waters Xbridge 150×50 mm×10 m; Mobile phase A: H₂O with 0.04% ammonia hydroxide (v %)+10 mmol NH₄HCO₃); Mobile phase B: MeCN; Gradient: B from 29% to 59% in 9.5 min, hold 100% B for 2 min; Flow Rate: 25 mL/min; Column Temperature: 30° C.; Wavelength: 220 nm, 254 nm) to afford N-(6-amino-5-methyl-3-pyridyl)-2-[5-methyl-2-[6-(trifluoromethyl)-3-pyridyl]-1-piperidyl]-2-oxo-acetamide (50 mg, 24.8% yield) as white solid.
LCMS (ESI) [M+H]⁺ m/z: calcd 422.2, found 422.2.

Step 6: Synthesis of N-(6-amino-5-methyl-3-pyridyl)-2-[(2R,5S)-5-methyl-2-[6-(trifluoromethyl)-3-pyridyl]-1-piperidyl]-2-oxo-acetamide (Compound 1012) and N-(6-amino-5-methyl-3-pyridyl)-2-[(2S,5R)-5-methyl-2-[6-(trifluoromethyl)-3-pyridyl]-1-piperidyl]-2-oxo-acetamide (Compound 1015

N-(6-amino-5-methyl-3-pyridyl)-2-[5-methyl-2-[6-(trifluoromethyl)-3-pyridyl]-1-piperidyl]-2-oxo-acetamide (60 mg, 0.142 mmol) was separated by chiral SFC (Instrument: Thar80; Column: Daicel Chiralcel OJ (250 mm*30 mm, 10 μm); Mobile phase: supercritical CO₂/EtOH (0.1% NH₃—H₂O, v %)=55/45; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm to afford Compound 1012 (peak 2, retention time: 2.081 min) and Compound 1015 (peak 3, retention time: 3.816 min).

Compound 1012: N-(6-amino-5-methyl-3-pyridyl)-2-[(2R,5S)-5-methyl-2-[6-(trifluoromethyl)-3-pyridyl]-1-piperidyl]-2-oxo-acetamide (29 mg, single unknown enantiomer with trans relative chemistry, peak 2, retention time=2.081 min, white solid). ¹H NMR (400 MHz, DMSO-d₆) δ ppm 10.25 (br s, 1H), 8.75 (s, 1H), 8.02 (br d, J=5.3 Hz, 2H), 7.87 (d, J=8.0 Hz, 1H), 7.49 (br s, 1H), 5.55 (br s, 1H), 5.36 (br s, 2H), 3.18-3.95 (m, 2H), 2.19 (br s, 2H), 2.06 (s, 3H), 1.95 (br s, 1H), 1.68-1.80 (m, 1H), 1.31-1.42 (m, 1H), 1.06 (d, J=7.0 Hz, 3H); ¹⁹F NMR (376 MHz, DMSO-d₆) δ ppm-66.25; LCMS (ESI) [M+H]⁺ m/z: calcd 422.2; found 422.1; HPLC: 100% @254 nm; 100% ee.

Compound 1015: N-(6-amino-5-methyl-3-pyridyl)-2-[(2S,5R)-5-methyl-2-[6-(trifluoromethyl)-3-pyridyl]-1-piperidyl]-2-oxo-acetamide (29 mg, single unknown enantiomer with trans relative chemistry, peak 3, retention time=3.816 min, white solid). ¹H NMR (400 MHz, DMSO-d₆) δ ppm 10.30 (br s, 1H), 8.75 (s, 1H), 7.99-8.10 (m, 2H), 7.87 (d, J=8.3 Hz, 1H), 7.52 (br s, 1H), 5.55 (br s, 2H), 3.74 (s, 2H), 3.10-3.15 (m, 1H), 2.19 (br s, 2H), 2.07 (s, 3H), 1.95 (br s, 1H), 1.66-1.80 (m, 1H), 1.31-1.43 (m, 1H), 1.06 (d, J=7.0 Hz, 3H); ¹⁹F NMR (376 MHz, DMSO-d₆) δ ppm-66.25; LCMS (ESI) [M+H]⁺ m/z: calcd 422.2, found 422.1; HPLC: 100% @254 nm; 100% ee.

Example 740. The Synthesis of N-(6-amino-5-methyl-3-pyridyl)-2-[(2R,5S)-2-(6-ethyl-3-pyridyl)-5-methyl-1-piperidyl]-2-oxo-acetamide (Compound 1016) and N-(6-amino-5-methyl-3-pyridyl)-2-[(2S,5R)-2-(6-ethyl-3-pyridyl)-5-methyl-1-piperidyl]-2-oxo-acetamide (Compound 1013)

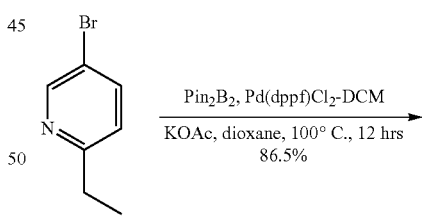

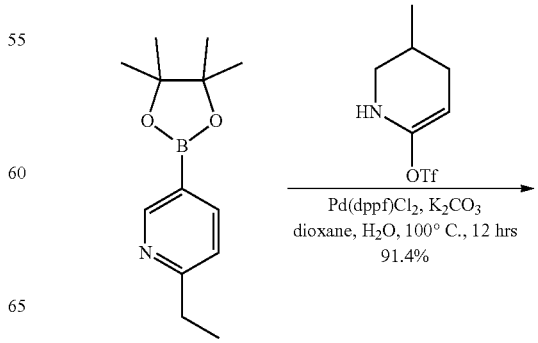

-continued

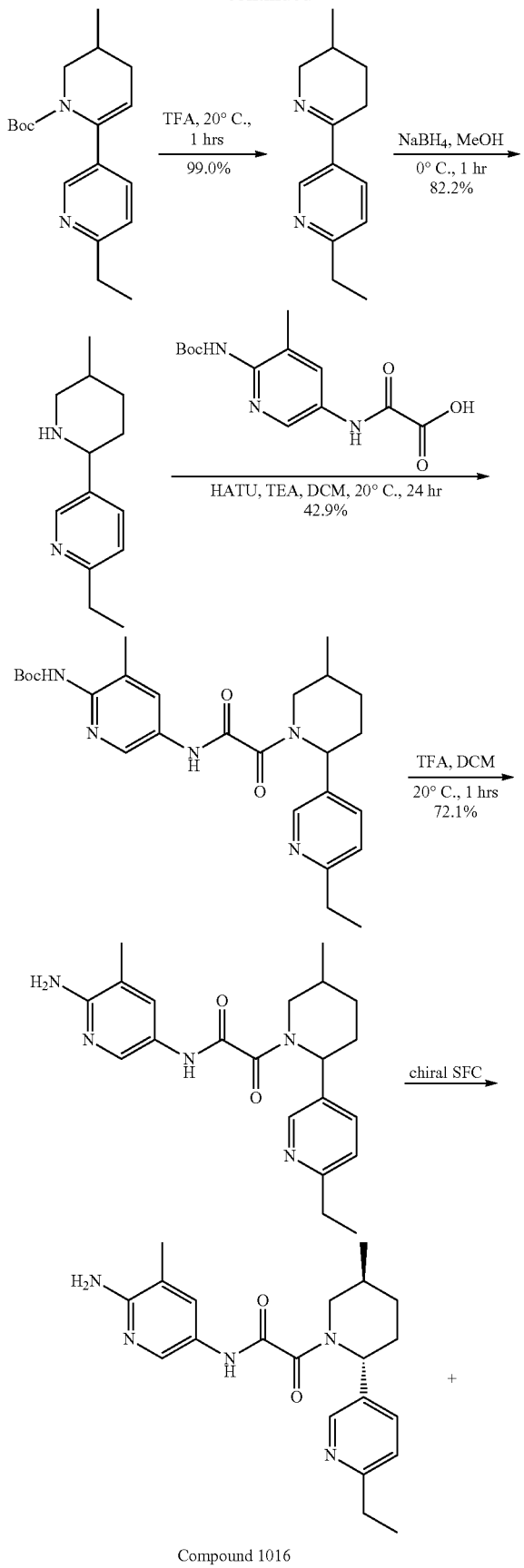

Compound 1016

-continued

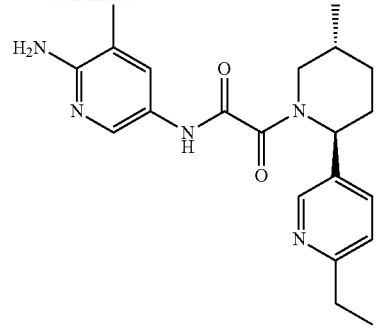

Compound 1013

Step 1: Synthesis of 2-ethyl-5-(4,4,5,5-tetramethyl-1,3,2-dioxaborolan-2-yl)pyridine A mixture of 5-bromo-2-ethyl-pyridine (4.8 g, 25.8 mmol), 4,4,5,5-tetramethyl-2-(4,4,5,5-tetramethyl-1,3,2-dioxaborolan-2-yl)-1,3,2-dioxaborolane (7.2 g, 28.4 mmol), Pd(dppf)Cl$_2$-DCM (632 mg, 0.774 mmol), KOAc (7.6 g, 77.5 mmol) in dioxane (150 mL) was stirred at 100° C. for 12 hours under nitrogen. The resulting mixture was quenched by addition of water (100 mL) and extracted with EtOAc (100 mL*3). The combined organic layer was washed with brine (100 mL), dried over anhydrous Na$_2$SO$_4$, filtered and concentrated under reduced pressure to give a crude product, which was purified by flash chromatography (ISCO®; 40 g AgelaFlash® Silica Flash Column, petroleum ether/EtOAc with EtOAc from 0~55%, 40 mL/min, 254 nm) to afford 2-ethyl-5-(4,4,5,5-tetramethyl-1,3,2-dioxaborolan-2-yl)pyridine (5.2 g, 86.5% yield) as a brown oil. $^1$H NMR (400 MHz, CDCl$_3$) δ ppm 8.86 (s, 1H), 7.98 (dd, J=7.7, 1.6 Hz, 1H), 7.16 (d, J=7.8 Hz, 1H), 2.84 (d, J=7.6 Hz, 2H), 1.35 (s, 12H), 1.30 (t, J=7.7 Hz, 3H); LCMS (ESI) [M+H]$^+$ m/z: calcd 234.2, found 234.1.

Step 2: Synthesis of tert-butyl 6-(6-ethyl-3-pyridyl)-3-methyl-3,4-dihydro-2H-pyridine-1-carboxylate A mixture of tert-butyl 3-methyl-6-(trifluoromethylsulfonyloxy)-3,4-dihydro-2H-pyridine-1-carboxylate (1 g, 2.90 mmol), 2-ethyl-5-(4,4,5,5-tetramethyl-1,3,2-dioxaborolan-2-yl)pyridine (1.5 g, 6.43 mmol), Pd(dppf)Cl$_2$ (106 mg, 0.145 mmol), K$_2$CO$_3$ (1.2 g, 8.68 mmol), dioxane (20 mL) and H$_2$O (5 mL) was stirred at 100° C. for 12 hours under nitrogen. The resulting mixture was quenched by addition of water (30 mL) and extracted with EtOAc (30 mL*3). The combined organic layer was washed with brine (100 mL*3), dried over anhydrous Na$_2$SO$_4$, filtered and concentrated under reduced pressure to give a crude product, which was purified by flash chromatography (ISCO®; 25 g SepaFlash® Silica Flash Column, petroleum ether/EtOAc with EtOAc from 0~15%, 35 mL/min, 254 nm) to afford tert-butyl 6-(6-ethyl-3-pyridyl)-3-methyl-3,4-dihydro-2H-pyridine-1-carboxylate (800 mg, 91.4% yield) as a white solid. $^1$H NMR (400 MHz, CDCl$_3$) δ ppm 8.45 (d, J=1.8 Hz, 1H), 7.48 (dd, J=8.1, 2.3 Hz, 1H), 7.09 (d, J=8.0 Hz, 1H), 5.31 (t, J=3.6 Hz, 1H), 4.03-4.11 (m, 1H), 3.00 (dd, J=12.4, 9.6 Hz, 1H), 2.82 (q, J=7.5 Hz, 2H), 2.35-2.48 (m, 1H), 1.80-1.99 (m, 2H), 1.29 (t, J=7.6 Hz, 3H), 1.10 (s, 9H), 1.02 (d, J=6.6 Hz, 3H); LCMS (ESI) [M+H]$^+$ m/z: calcd 303.2, found 303.2.

Step 3: Synthesis of 2-ethyl-5-(3-methyl-2,3,4,5-tetrahydropyridin-6-yl)pyridine A solution of tert-butyl 6-(6-ethyl-3-pyridyl)-3-methyl-3,4-dihydro-2H-pyridine-1-carboxylate (800 mg, 2.65 mmol) in TFA (3.3 mL, 42.8 mmol) was stirred at 20° C. for 1 hour. The mixture was evaporated in vacuo. Crushed ice (10 g) was added to the residue and pH was adjusted to 8 with 10 wt % aqueous solution of NaOH. The resulting mixture was extracted with EtOAc (20 mL*3). The combined organic layer was dried over anhydrous $Na_2SO_4$, filtered and concentrated under reduced pressure to give 2-ethyl-5-(3-methyl-2,3,4,5-tetrahydropyridin-6-yl)pyridine (530 mg, 99.0% yield) as a yellow solid, which was directly used without further purification. $^1H$ NMR (400 MHz, methanol-$d_4$) δ ppm 8.75 (d, J=2.0 Hz, 1H), 8.06 (dd, J=8.2, 2.4 Hz, 1H), 7.36 (d, J=8.3 Hz, 1H), 3.87-3.96 (m, 1H), 3.22 (dd, J=17.4, 9.9 Hz, 1H), 2.80-2.91 (m, 3H), 1.96 (d, J=12.5 Hz, 1H), 1.69-1.83 (m, 1H), 1.37-1.46 (m, 1H), 1.27-1.33 (m, 4H), 1.02 (d, J=6.5 Hz, 3H); LCMS (ESI) [M+H]$^+$ m/z: calcd 203.1, found 203.2.

Step 4: Synthesis of 2-ethyl-5-(5-methyl-2-piperidyl)pyridine $NaBH_4$ (149 mg, 3.94 mmol) was added in one portion to a stirred solution of 2-ethyl-5-(3-methyl-2,3,4,5-tetrahydropyridin-6-yl)pyridine (530 mg, 2.62 mmol) in MeOH (10 mL) at 0° C. The resulting mixture was stirred at 0° C. for 1 hour. The mixture was evaporated in vacuo. The residue was diluted with water (50 mL) and extracted with DCM (30 mL*3). The combined organic layer was dried over anhydrous $Na_2SO_4$, filtered and concentrated under reduced pressure to give 2-ethyl-5-(5-methyl-2-piperidyl)pyridine (440 mg, 82.2% yield) as a yellow oil, which was directly used without further purification. $^1H$ NMR (400 MHz, methanol-$d_4$) δ ppm 8.42 (d, J=2.0 Hz, 1H), 7.76 (dd, J=8.0, 2.3 Hz, 1H), 7.29 (d, J=8.0 Hz, 1H), 3.59 (dd, J=11.5, 2.5 Hz, 1H), 3.04-3.12 (m, 1H), 2.79 (q, J=7.5 Hz, 2H), 2.39 (t, J=11.5 Hz, 1H), 1.88-1.96 (m, 1H), 1.82 (dq, J=13.2, 3.1 Hz, 1H), 1.54-1.72 (m, 2H), 1.25-1.30 (m, 4H), 0.92 (d, J=6.5 Hz, 3H); LCMS (ESI) [M+H]$^+$ m/z: calcd 205.2, found 205.2.

Step 5: Synthesis of tert-butyl N-[5-[[2-[2-(6-ethyl-3-pyridyl)-5-methyl-1-piperidyl]-2-oxo-acetyl]amino]-3-methyl-2-pyridyl]carbamate To a stirred solution of 2-[[6-(tert-butoxycarbonylamino)-5-methyl-3-pyridyl]amino]-2-oxo-acetic acid (100 mg, 0.339 mmol) and 2-ethyl-5-(5-methyl-2-piperidyl)pyridine (83 mg, 0.406 mmol) in DCM (5 mL) were added HATU (129 mg, 0.339 mmol) and TEA (0.14 mL, 1.00 mmol) at 20° C. The resulting reaction mixture was stirred at 20° C. for 12 hours. The reaction didn't get full conversion on LCMS. HATU (129 mg, 0.339 mmol) and TEA (0.14 mL, 1.00 mmol) was added, and the mixture was stirred at 20° C. for another 12 hours. The reaction mixture was concentrated under reduced pressure and poured into water (10 mL). The aqueous layer was extracted with EtOAc (15 mL*2). The combined organic phase was washed with brine (50 mL*2), dried over anhydrous $Na_2SO_4$, filtered and concentrated under reduced pressure to give a crude product, which was purified by flash chromatography (ISCO®; 4 g*3 SepaFlash® Silica Flash Column, petroleum ether/EtOAc with EtOAc from 0~85%, 25 mL/min, 254 nm) to afford tert-butyl N-[5-[[2-[2-(6-ethyl-3-pyridyl)-5-methyl-1-piperidyl]-2-oxo-acetyl]amino]-3-methyl-2-pyridyl]carbamate (70 mg, 42.9% yield) as a colorless oil. LCMS (ESI) [M+H]$^+$ m/z: calcd 482.3, found 382.3 (Boc cleaved mass).

Step 6: Synthesis of N-(6-amino-5-methyl-3-pyridyl)-2-[2-(6-ethyl-3-pyridyl)-5-methyl-1-piperidyl]-2-oxo-acetamide To a solution of tert-butyl N-[5-[[2-[2-(6-ethyl-3-pyridyl)-5-methyl-1-piperidyl]-2-oxo-acetyl]amino]-3-methyl-2-pyridyl]carbamate (70 mg, 0.145 mmol) in DCM (2 mL) was added TFA (0.25 mL, 3.24 mmol) at 20° C. The resulting reaction mixture was stirred at 20° C. for 1 hour. The resulting mixture was adjusted pH=8 with saturated $NaHCO_3$ aqueous solution, and concentrated under reduced pressure to give a crude product, which was purified by flash chromatography (ISCO®; 4 g*2 SepaFlash® Silica Flash Column, DCM/MeOH with MeOH from 0~7%, 25 mL/min, 254 nm) to afford N-(6-amino-5-methyl-3-pyridyl)-2-[2-(6-ethyl-3-pyridyl)-5-methyl-1-piperidyl]-2-oxo-acetamide (40 mg, 72.1% yield) as a colorless oil. LCMS (ESI) [M+H]$^+$ m/z: calcd 382.2, found 382.2; racemic.

Step 7: Synthesis of N-(6-amino-5-methyl-3-pyridyl)-2-[(2R,5S)-2-(6-ethyl-3-pyridyl)-5-methyl-1-piperidyl]-2-oxo-acetamide (Compound 1016) and N-(6-amino-5-methyl-3-pyridyl)-2-[(2S,5R)-2-(6-ethyl-3-pyridyl)-5-methyl-1-piperidyl]-2-oxo-acetamide (Compound 1013

N-(6-amino-5-methyl-3-pyridyl)-2-[2-(6-ethyl-3-pyridyl)-5-methyl-1-piperidyl]-2-oxo-acetamide (40 mg, 0.105 mmol) was separated by chiral SFC (Instrument: Sepiatec Prep SFC100; Column: Daicel Chiralpak 1C 250× 30 mm I.D. 10 m; Mobile phase: supercritical $CO_2$/EtOH (0.1% $NH_3$—$H_2O$, v %)=55/45; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1016 and Compound 1013.

Compound 1016: N-(6-amino-5-methyl-3-pyridyl)-2-[(2R,5S)-2-(6-ethyl-3-pyridyl)-5-methyl-1-piperidyl]-2-oxo-acetamide (30.9 mg, single unknown enantiomer with trans relative stereochemistry, peak 2, retention time=2.802 min, white dry powder). $^1H$ NMR (400 MHz, DMSO-$d_6$) δ ppm 10.23 (brs, 1H), 8.46 (s, 1H), 8.02 (s, 1H), 7.63 (d, J=7.5 Hz, 1H), 7.49 (s, 1H), 7.25 (d, J=8.3 Hz, 1H), 5.24-5.61 (m, 3H), 2.76 (q, J=7.5 Hz, 2H), 1.98-2.24 (m, 6H), 1.93 (s, 1H), 1.68-1.79 (m, 1H), 1.31-1.39 (m, 1H), 1.24 (t, J=7.5 Hz, 4H), 1.05 (d, J=7.0 Hz, 3H); LCMS (ESI) [M+H]$^+$ m/z: calcd 382.2, found 382.2; HPLC: 100% @254 nm; 100% ee; 98.2% de.

Compound 1013: N-(6-amino-5-methyl-3-pyridyl)-2-[(2S,5R)-2-(6-ethyl-3-pyridyl)-5-methyl-1-piperidyl]-2-oxo-acetamide (30.8 mg, single unknown enantiomer with trans relative stereochemistry, peak 4, retention time=3.896 min, white dry powder). $^1H$ NMR (400 MHz, DMSO-$d_6$) δ ppm 10.23 (brs, 1H), 8.46 (s, 1H), 8.02 (s, 1H), 7.63 (d, J=7.8 Hz, 1H), 7.49 (s, 1H), 7.25 (d, J=8.3 Hz, 1H), 5.30-5.54 (m, 3H), 2.76 (q, J=7.5 Hz, 2H), 1.98-2.23 (m, 6H), 1.88-1.97 (m, 1H), 1.69-1.79 (m, 1H), 1.31-1.39 (m, 1H), 1.24 (t, J=7.5 Hz, 4H), 1.05 (d, J=7.0 Hz, 3H); LCMS (ESI) [M+H]⁺ m/z: calcd 382.2, found 382.2; HPLC: 98.970% @254 nm; 100% ee; 100% de.

Example 741. The Synthesis of N-(6-amino-5-methyl-3-pyridyl)-2-[(2R,5S)-2-[6-(difluoromethyl)-3-pyridyl]-5-methyl-1-piperidyl]-2-oxo-acetamide and N-(6-amino-5-methyl-3-pyridyl)-2-[(2S,5R)-2-[6-(difluoromethyl)-3-pyridyl]-5-methyl-1-piperidyl]-2-oxo-acetamide (Compound 1018) and (Compound 1011)

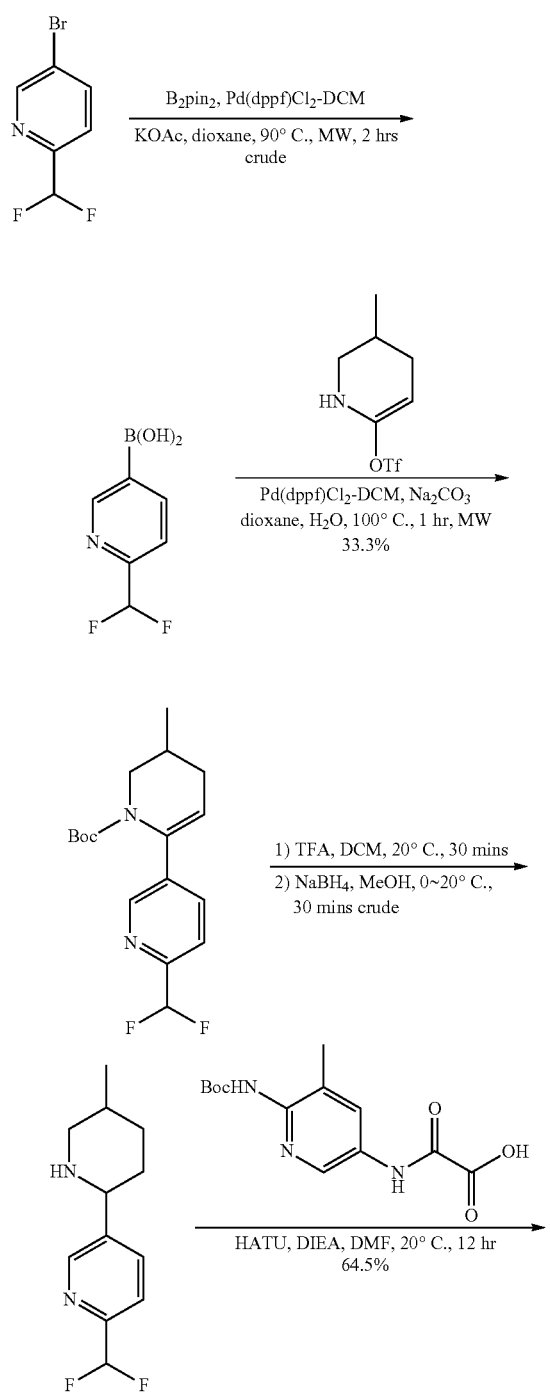

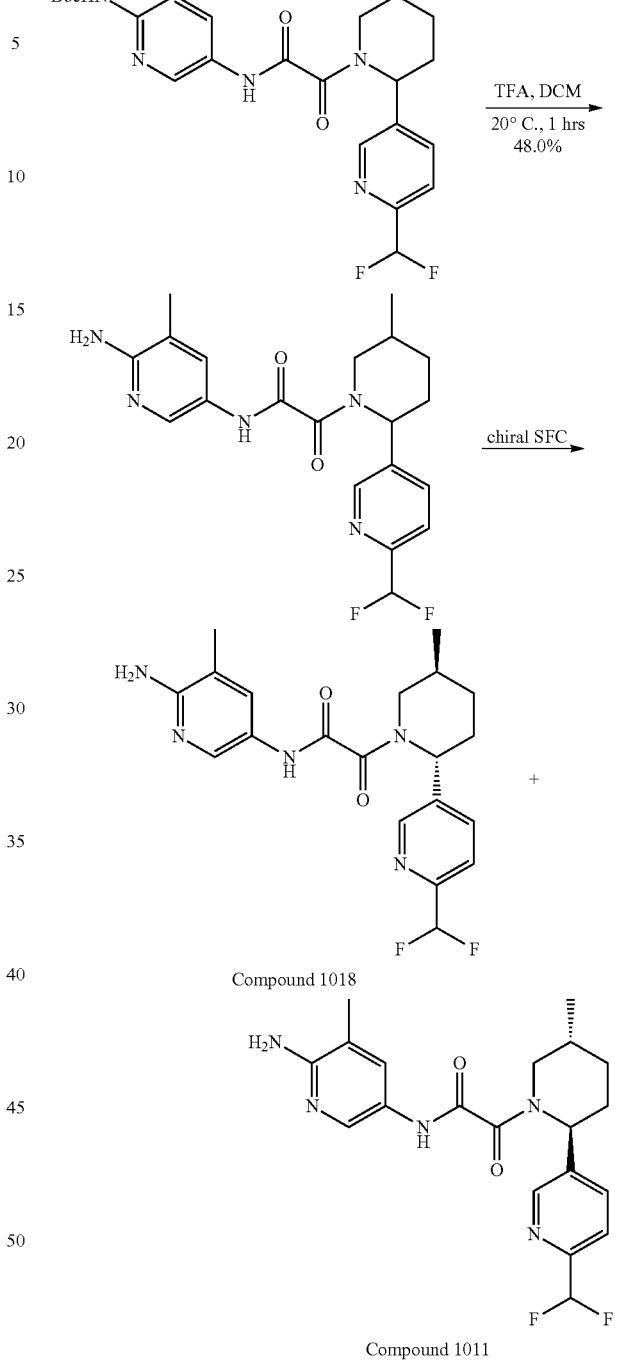

Compound 1018

Compound 1011

Step 1: Synthesis of [6-(difluoromethyl)-3-pyridyl]boronic acid

To a solution of 5-bromo-2-(difluoromethyl)pyridine (1 g, 4.81 mmol), 4,4,5,5-tetramethyl-2-(4,4,5,5-tetramethyl-1,3,2-dioxaborolan-2-yl)-1,3,2-dioxaborolane (1.55 g, 6.10 mmol), $CH_3COOK$ (1.03 g, 10.5 mmol) in dioxane (10 mL) was added Pd(dppf)Cl₂-DCM (200 mg, 0.245 mmol). The mixture was stirred at 90° C. for 2 hours under microwave.

The resulting mixture was concentrated under reduced pressure to give [6-(difluoromethyl)-3-pyridyl]boronic acid (1.5 g, crude) as black oil.

Step 2: Synthesis of tert-butyl 6-[6-(difluoromethyl)-3-pyridyl]-3-methyl-3,4-dihydro-2H-pyridine-1-carboxylate A mixture of [6-(difluoromethyl)-3-pyridyl]boronic acid (800 mg, 4.63 mmol), tert-butyl 3-methyl-6-(trifluoromethylsulfonyloxy)-3,4-dihydro-2H-pyridine-1-carboxylate (1.5 g, 4.34 mmol), $Na_2CO_3$ (1.50 g, 14.2 mmol), Pd(dppf)$Cl_2$-DCM (200 mg, 0.245 mmol), dioxane (10 mL) and $H_2O$ (2 mL) was stirred at 100° C. for 1 hour under microwave. The resulting mixture was quenched by addition of water (10 mL) and extracted with EtOAc (50 mL*3). The combined organic layer was washed with saturated $NH_4Cl$ aqueous solution (50 mL*2), brine (10 mL), dried over anhydrous $Na_2SO_4$, filtered and concentrated under reduced pressure to give residue which was purified by flash chromatography (ISCO®; 12 g AgelaFlash® Silica Flash Column, petroleum ether/EtOAc with EtOAc from 0~13%, Flow Rate: 30 mL/min, 254 nm) to afford tert-butyl 6-[6-(difluoromethyl)-3-pyridyl]-3-methyl-3,4-dihydro-2H-pyridine-1-carboxylate (500 mg, 33.3% yield) as white solid. $^1$H NMR (400 MHz, chloroform-d) δ ppm 8.58 (d, J=1.51 Hz, 1H), 7.71 (dd, J=8.03, 2.01 Hz, 1H), 7.57 (d, J=8.03 Hz, 1H), 6.45-6.83 (m, 1H), 5.41 (t, J=3.76 Hz, 1H), 4.08 (dd, J=12.42, 2.89 Hz, 1H), 3.04 (dd, J=12.42, 9.41 Hz, 1H), 2.32-2.53 (m, 1H), 1.96-2.11 (m, 1H), 1.84-1.96 (m, 1H), 1.65 (s, 1H), 1.06-1.24 (m, 9H), 1.04 (d, J=6.53 Hz, 3H); $^{19}$F NMR (376 MHz, chloroform-d) 6 ppm-115.056 ppm.

Step 3: Synthesis of 2-(difluoromethyl)-5-(5-methyl-2-piperidyl)pyridine

A mixture of tert-butyl 6-[6-(difluoromethyl)-3-pyridyl]-3-methyl-3,4-dihydro-2H-pyridine-1-carboxylate (400 mg, 1.23 mmol), TFA (2 mL, 26.0 mmol) and DCM (5 mL) was stirred at 20° C. for 30 minutes. Then the mixture was quenched by addition of water (10 mL) and extracted with EtOAc (10 mL*3). The combined organic layer was washed with saturated $NH_4Cl$ aqueous solution (10 mL*2), brine (10 mL), dried over anhydrous $Na_2SO_4$, filtered and concentrated under reduced pressure. The residue was dissolved in MeOH (5 mL) and $NaBH_4$ (200 mg, 5.29 mmol) was added at 0° C. then the mixture was stirred at 20° C. for 30 minutes. The resulting mixture was adjusted pH=8-9 with $Na_2CO_3$ solution and extracted with DCM (50 mL*3). The combined organic layer was washed with saturated $NH_4Cl$ aqueous solution (10 mL*2), brine (10 mL), dried over anhydrous $Na_2SO_4$, filtered and concentrated under reduced pressure to give 2-(difluoromethyl)-5-(5-methyl-2-piperidyl)pyridine (300 mg, crude) as yellow solid. LCMS (ESI) [M+H]$^+$ m/z: calcd 227.2, found 227.2.

Step 4: Synthesis of tert-butyl N-[5-[[2-[2-[6-(difluoromethyl)-3-pyridyl]-5-methyl-1-piperidyl]-2-oxo-acetyl]amino]-3-methyl-2-pyridyl]carbamate To a mixture of 2-[[6-(tert-butoxycarbonylamino)-5-methyl-3-pyridyl]amino]-2-oxo-acetic acid (100 mg, 0.339 mmol) and 2-(difluoromethyl)-5-(5-methyl-2-piperidyl)pyridine (100 mg, 0.442 mmol) in DCM (5 mL) was added HATU (150 mg, 0.394 mmol) and DIPEA (297 mg, 2.30 mmol) and the mixture was stirred at 20° C. for 12 hours. The resulting mixture was quenched by addition of water (10 mL) and extracted with EtOAc (50 mL*3). The combined organic layer was washed with saturated $NH_4Cl$ aqueous solution (10 mL*2), brine (10 mL), dried over anhydrous $Na_2SO_4$, filtered and concentrated under reduced pressure. The residue was purified by flash chromatography (ISCO®; 12 g AgelaFlash® Silica Flash Column, petroleum ether/EtOAc with EtOAc from 0~50%, Flow Rate: 30 mL/min) to afford tert-butyl N-[5-[[2-[2-[6-(difluoromethyl)-3-pyridyl]-5-methyl-1-piperidyl]-2-oxo-acetyl]amino]-3-methyl-2-pyridyl]carbamate (110 mg, 64.5% yield) as yellow solid. LCMS (ESI) [M+H]$^+$ m/z: calcd 504.2, found 504.2.

Step 5: Synthesis of N-(6-amino-5-methyl-3-pyridyl)-2-[2-[6-(difluoromethyl)-3-pyridyl]-5-methyl-1-piperidyl]-2-oxo-acetamide A mixture of tert-butyl N-[5-[[2-[2-[6-(difluoromethyl)-3-pyridyl]-5-methyl-1-piperidyl]-2-oxo-acetyl]amino]-3-methyl-2-pyridyl]carbamate (130 mg, 0.258 mmol), TFA (1.19 g, 10.4 mmol) and DCM (3 mL) was stirred at 20° C. for 1 hour. The resulting mixture was adjusted pH=7-8 with $NH_3$—$H_2O$ and concentrated under reduced pressure to give a crude product which was purified by flash chromatography (Column: SepaFlash® Spherical C18, 25 g, 40-60 m, 120A; MeCN/water (0.5% $NH_3$—$H_2O$) with MeCN from 0-45%, 25 mL/min, 254 nm) to give N-(6-amino-5-methyl-3-pyridyl)-2-[2-[6-(difluoromethyl)-3-pyridyl]-5-methyl-1-piperidyl]-2-oxo-acetamide (50 mg, 48.0% yield) as yellow solid. LCMS (ESI) [M+H]$^+$ m/z: calcd 404.3, found 404.2.

Step 6: Synthesis of N-(6-amino-5-methyl-3-pyridyl)-2-[(2R,5S)-2-[6-(difluoromethyl)-3-pyridyl]-5-methyl-1-piperidyl]-2-oxo-acetamide and N-(6-amino-5-methyl-3-pyridyl)-2-[(2S,5R)-2-[6-(difluoromethyl)-3-pyridyl]-5-methyl-1-piperidyl]-2-oxo-acetamide (Compound 1018) and (Compound 1011

N-(6-amino-5-methyl-3-pyridyl)-2-[2-[6-(difluoromethyl)-3-pyridyl]-5-methyl-1-piperidyl]-2-oxo-acetamide (49 mg, 0.121 mmol) was purified by SFC (Instrument: Berger, Multigr AM-II; Column: Daicel Chiralpak AD (250 mm*30 mm, 10 μm); Mobile phase: supercritical $CO_2$/EtOH (0.1% $NH_3$—$H_2O$, v %)=50/50; Flow Rate: 60 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to give Compound 1018 and Compound 1011.

Compound 1018: N-(6-amino-5-methyl-3-pyridyl)-2-[(2R,5S)-2-[6-(difluoromethyl)-3-pyridyl]-5-methyl-1-piperidyl]-2-oxo-acetamide (20 mg, single unknown enantiomer with trans relative chemistry, peak 3, retention time=2.434 min, white solid). $^1$H NMR (400 MHz, DMSO-d$_6$) δ ppm 10.26 (br s, 1H), 8.67 (s, 1H), 7.89-8.06 (m, 2H), 7.70 (d, J=8.03 Hz, 1H), 7.49 (br s, 1H), 6.68-7.05 (m, 1H), 5.54 (br s, 1H), 5.36 (br s, 2H), 3.06 (br s, 1H), 2.19 (br s, 2H), 2.01-2.09 (m, 3H), 1.95 (br s, 1H), 1.64-1.78 (m, 1H), 1.37 (br d, J=9.54 Hz, 1H), 1.06 (d, J=7.03 Hz, 3H); $^{19}$F NMR (376 MHz, DMSO-d$_6$) δ ppm-115.086 ppm; LCMS (ESI) [M+H]$^+$ m/z: calcd 404.3, found 404.3; HPLC 100% @254 nm; 100% ee; 98.3% de.

Compound 1011: N-(6-amino-5-methyl-3-pyridyl)-2-[(2S,5R)-2-[6-(difluoromethyl)-3-pyridyl]-5-methyl-1-piperidyl]-2-oxo-acetamide (20 mg, single unknown enantiomer with trans relative chemistry, peak 4, retention time=2.890 min, white solid). $^1$H NMR (400 MHz, DMSO-d$_6$) δ ppm 10.25 (br s, 1H), 8.67 (s, 1H), 8.03 (br s, 1H), 7.94 (br d, J=6.78 Hz, 1H), 7.70 (d, J=8.28 Hz, 1H), 7.50 (br s, 1H), 6.70-7.08 (m, 1H), 5.54 (br s, 1H), 5.36 (br s, 2H), 3.04 (br d, J=5.52 Hz, 2H), 2.19 (br s, 2H), 2.07 (s, 3H), 1.95 (br s, 1H), 1.67-1.80 (m, 1H), 1.37 (br d, J=8.53 Hz, 1H), 1.06 (d, J=7.03 Hz, 3H); $^{19}$F NMR (376 MHz, DMSO-d$_6$) δ ppm-115.085 ppm; LCMS (ESI) [M+H]$^+$ m/z: calcd 404.3, found 404.3; HPLC: 1000% @254 nm; 99.8% ee; 99.6% de.

Example 742. The Synthesis of N-(6-amino-5-methyl-3-pyridyl)-2-[(2S,5R)-5-methyl-2-[6-(4-methylpiperazin-1-yl)-3-pyridyl]-1-piperidyl]-2-oxo-acetamide (Compound 1017) and N-(6-amino-5-methyl-3-pyridyl)-2-[(2R,5S)-5-methyl-2-[6-(4-methylpiperazin-1-yl)-3-pyridyl]-1-piperidyl]-2-oxo-acetamide (Compound 1014)

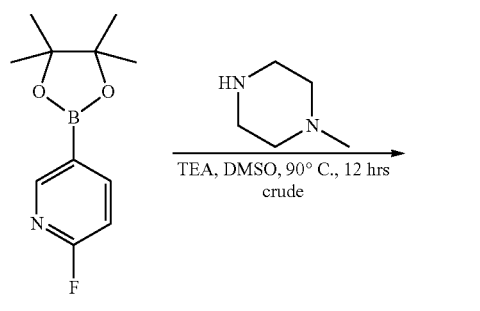

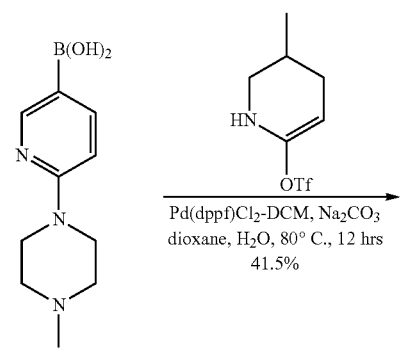

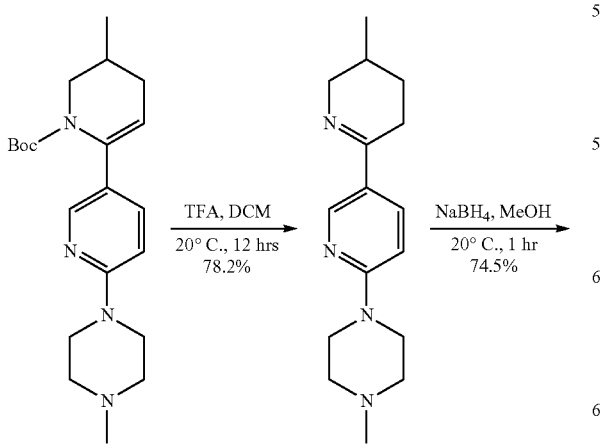

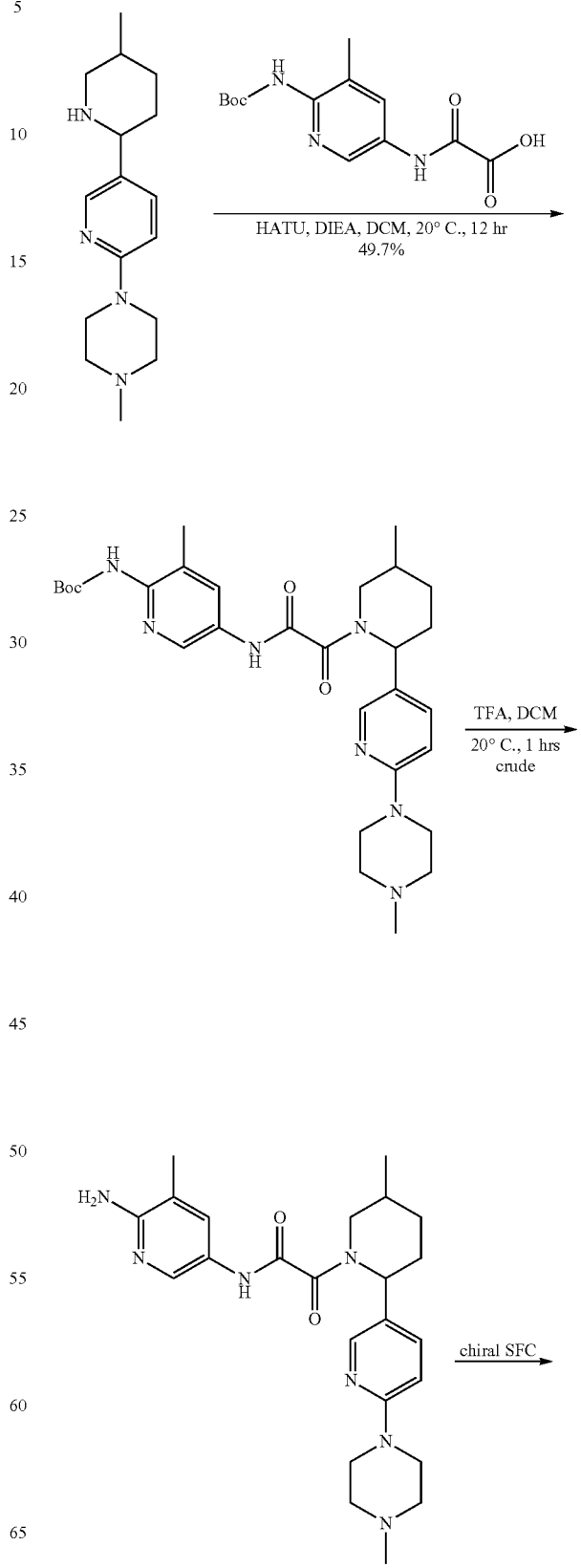

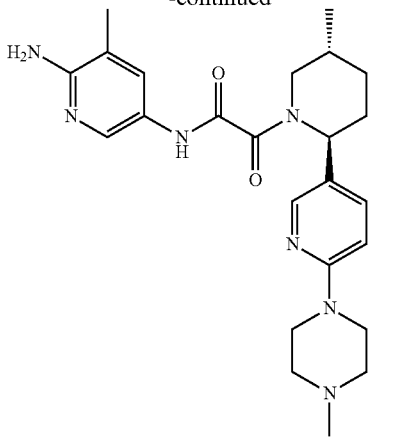

Compound 1017

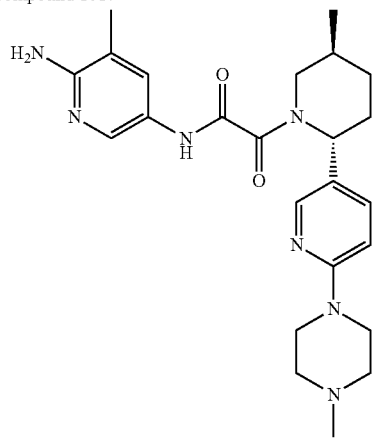

Compound 1014

Step 1: Synthesis of [6-(4-methylpiperazin-1-yl)-3-pyridyl]boronic acid

To a solution of 2-fluoro-5-(4,4,5,5-tetramethyl-1,3,2-dioxaborolan-2-yl)pyridine (3 g, 0.013 mol), 1-methylpiperazine (2 g, 0.020 mol) in DMSO (10 mL) was added TEA (5.8 mL, 0.041 mol). The mixture was stirred at 90° C. for 12 hours. The resulting mixture was quenched by addition of water (50 mL) and extracted with EtOAc (50 mL*3). The combined organic layer was washed with saturated NH$_4$Cl aqueous solution (50 mL*2), brine (50 mL), dried over anhydrous Na$_2$SO$_4$, filtered and concentrated under reduced pressure to give [6-(4-methylpiperazin-1-yl)-3-pyridyl]boronic acid (2.5 g, crude) as white solid.

Step 2: Synthesis of tert-butyl 3-methyl-6-[6-(4-methylpiperazin-1-yl)-3-pyridyl]-3,4-dihydro-2H-pyridine-1-carboxylate A mixture of [6-(4-methylpiperazin-1-yl)-3-pyridyl]boronic acid (1 g, 4.52 mmol), tert-butyl 3-methyl-6-(trifluoromethylsulfonyloxy)-3,4-dihydro-2H-pyridine-1-carboxylate (1.2 g, 3.47 mmol), Pd(dppf)Cl$_2$-DCM (175 mg, 0.214 mmol), Na$_2$CO$_3$ (1.47 g, 0.014 mol), dioxane (3 mL) and H$_2$O (1 mL) were stirred at 80° C. for 12 hours under nitrogen. The resulting mixture was quenched by addition of water (20 mL) and extracted with EtOAc (20 mL*3). The combined organic layer was washed with saturated NH$_4$Cl aqueous solution (20 mL*2), brine (20 mL), dried over anhydrous Na$_2$SO$_4$, filtered and concentrated under reduced pressure. The residue was purified by flash chromatography (ISCO®; 25 g AgelaFlash® Silica Flash Column DCM/MeOH with MeOH from 0-10%, flow rate=30 mL/min, 254 nm) to afford tert-butyl 3-methyl-6-[6-(4-methylpiperazin-1-yl)-3-pyridyl]-3,4-dihydro-2H-pyridine-1-carboxylate (700 mg, 41.5% yield) as brown oil. $^1$H NMR (400 MHz, methanol-d$_4$) δ ppm 8.01 (s, 1H), 7.46 (br d, J 8.5 Hz, 1H), 6.81 (br d, J 8.8 Hz, 1H), 5.29 (br s, 1H), 3.94 (br dd, J=12.4, 2.4 Hz, 1H), 3.54 (br s, 4H), 3.08 (br dd, J 12.2, 9.2 Hz, 1H), 2.57 (br d, J 4.3 Hz, 4H), 2.27-2.48 (m, 4H), 1.79-2.01 (m, 2H), 1.15 (s, 9H), 1.02 (br d, J 6.5 Hz, 3H).

Step 3: Synthesis of 1-methyl-4-[5-(3-methyl-1,2,3,4-tetrahydropyridin-6-yl)-2-pyridyl]piperazine To a solution of tert-butyl 3-methyl-6-[6-(4-methylpiperazin-1-yl)-3-pyridyl]-3,4-dihydro-2H-pyridine-1-carboxylate (700 mg, 1.88 mmol) in DCM (2 mL) was added TFA (2.0 mL, 0.026 mol). The mixture was stirred at 20° C. for 12 hours. The resulting mixture was adjusted to pH=8 with saturated NaHCO$_3$ aqueous solution and extracted with DCM (50 mL*3). The combined organic layer was washed with brine (50 mL), dried over anhydrous Na$_2$SO$_4$, filtered and concentrated under reduced pressure to give 1-methyl-4-[5-(3-methyl-1,2,3,4-tetrahydropyridin-6-yl)-2-pyridyl]piperazine (400 mg, 78.2% yield) as off-white solid.

Step 4: Synthesis of 1-methyl-4-[5-(5-methyl-2-piperidyl)-2-pyridyl]piperazine To a solution of 1-methyl-4-[5-(3-methyl-1,2,3,4-tetrahydropyridin-6-yl)-2-pyridyl]piperazine (400 mg, 1.47 mmol) in MeOH (2 mL) was added NaBH$_4$ (120 mg, 3.17 mmol). The mixture was stirred at 20° C. for 1 hour. The resulting mixture was concentrated under reduced pressure to remove MeOH and quenched by addition of water (30 mL), extracted with EtOAc (30 mL*3). The combined organic layer was washed with saturated NH$_4$Cl aqueous solution (30 mL*2), brine (100 mL), dried over anhydrous Na$_2$SO$_4$, filtered and concentrated under reduced pressure to give 1-methyl-4-[5-(5-methyl-2-piperidyl)-2-pyridyl]piperazine (300 mg, 74.5% yield) as yellow solid. $^1$H NMR (400 MHz, methanol-d$_4$) δ ppm 8.08 (d, J 2.0 Hz, 1H), 7.60 (dd, J 8.8, 2.5 Hz, 1H), 6.81 (d, J 8.8 Hz, 1H), 3.44-3.57 (m, 5H), 3.05 (br dd, J=11.9, 1.9 Hz, 1H), 2.55 (t, J=5.1 Hz, 4H), 2.36-2.43 (m, 1H), 2.33 (s, 3H), 1.73-1.97 (m, 2H), 1.53-1.70 (m, 2H), 1.15-1.32 (m, 1H), 0.91 (d, J 6.5 Hz, 3H).

Step 5: Synthesis of tert-butyl N-[3-methyl-5-[[2-[5-methyl-2-[6-(4-methylpiperazin-1-yl)-3-pyridyl]-1-piperidyl]-2-oxo-acetyl]amino]-2-pyridyl]carbamate To a solution of 2-[[6-(tert-butoxycarbonylamino)-5-methyl-3-pyridyl]amino]-2-oxo-acetic acid (50 mg, 0.169 mmol), 1-methyl-4-[5-(5-methyl-2-piperidyl)-2-pyridyl]piperazine (50 mg, 0.182 mmol) in DCM (4 mL) were added HATU (100 mg, 0.263 mmol) and DIEA (100 µL, 0.573 mmol). The mixture was stirred at 20° C. for 2 hours. The resulting mixture was quenched by addition of water (20 mL) and extracted with DCM (20 mL*3). The combined organic layer was washed with saturated NH$_4$Cl aqueous solution (100 mL*2), brine (100 mL), dried over anhydrous Na$_2$SO$_4$, filtered and concentrated under reduced pressure. The residue was purified by flash chromatography (ISCO®;

12 g AgelaFlash® Silica Flash Column, MeOH/EtOAc with EtOAc from 0~60%, flow rate=30 mL/min, 254 nm) to afford tert-butyl N-[3-methyl-5-[[2-[5-methyl-2-[6-(4-methylpiperazin-1-yl)-3-pyridyl]-1-piperidyl]-2-oxo-acetyl]amino]-2-pyridyl]carbamate (50 mg, 49.7% yield) as light-yellow oil.

Step 6: Synthesis of N-[3-methyl-5-[[2-[5-methyl-2-[6-(4-methylpiperazin-1-yl)-3-pyridyl]-1-piperidyl]-2-oxo-acetyl]amino]-2-pyridyl]carbamate To a solution of tert-butyl N-[3-methyl-5-[[2-[5-methyl-2-[6-(4-methylpiperazin-1-yl)-3-pyridyl]-1-piperidyl]-2-oxo-acetyl]amino]-2-pyridyl]carbamate (50 mg, 0.091 mmol) in DCM (2 mL) was added TFA (160 µL, 2.12 mmol). The mixture was stirred at 20° C. for 1 hour. The resulting mixture was filtered and concentrated under reduced pressure to give N-[3-methyl-5-[[2-[5-methyl-2-[6-(4-methylpiperazin-1-yl)-3-pyridyl]-1-piperidyl]-2-oxo-acetyl]amino]-2-pyridyl]carbamate (40 mg) as white solid.

Step 7: Synthesis of N-(6-amino-5-methyl-3-pyridyl)-2-[(2S,5R)-5-methyl-2-[6-(4-methylpiperazin-1-yl)-3-pyridyl]-1-piperidyl]-2-oxo-acetamide (Compound 1017) and N-(6-amino-5-methyl-3-pyridyl)-2-[(2R,5S)-5-methyl-2-[6-(4-methylpiperazin-1-yl)-3-pyridyl]-1-piperidyl]-2-oxo-acetamide (Compound 1014

N-[3-methyl-5-[[2-[5-methyl-2-[6-(4-methylpiperazin-1-yl)-3-pyridyl]-1-piperidyl]-2-oxo-acetyl]amino]-2-pyridyl]carbamate (40 mg) was purified by chiral SFC 1 (Instrument: Berger, Multigr AM-II; Column: Chiralpak AD 250× 30 mm I.D. 20 m; Mobile phase: supercritical $CO_2$/EtOH (0.1% $NH_3$—$H_2O$, v %)=60/40; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1017 (mixed with one diastereoisomer, peak 2, retention time=5.910 min) of Compound 1014 (peak 3, retention time=6.357 min).

Compound 1014: N-(6-amino-5-methyl-3-pyridyl)-2-[(2R,5S)-5-methyl-2-[6-(4-methylpiperazin-1-yl)-3-pyridyl]-1-piperidyl]-2-oxo-acetamide (29 mg, single unknown enantiomer with trans relative chemistry, peak 3, retention time=6.357 min, white solid). $^1$H NMR (400 MHz, DMSO-$d_4$) δ ppm 10.19 (br s, 1H), 7.94-8.20 (m, 2H), 7.44-7.53 (m, 2H), 6.78 (d, J 8.8 Hz, 1H), 5.34 (br s, 3H), 3.36-3.61 (m, 5H), 2.34-2.46 (m, 5H), 2.23 (s, 3H), 2.00-2.13 (m, 5H), 1.72-1.96 (m, 2H), 1.34 (br d, J 12.5 Hz, 1H), 1.04 (d, J=7.0 Hz, 3H); LCMS (ESI) [M+H]$^+$ m/z: calcd 452.2, found 452.3; HPLC: 99.50%/@254 nm; 97.9% ee.

Compound 1017: N-(6-amino-5-methyl-3-pyridyl)-2-[(2S,5R)-5-methyl-2-[6-(4-methylpiperazin-1-yl)-3-pyridyl]-1-piperidyl]-2-oxo-acetamide (mixed with one diastereoisomer, peak 2, retention time=5.910 min) was further separated with chiral SFC 2 (Instrument: SFC-80Q; Column: Daicel Chiralpak 1C 250×30 mm I.D. 10 m; Mobile phase: supercritical $CO_2$/EtOH (0.1% $NH_3$—$H_2O$, v %)=55/45; Flow Rate: 80 mL/min; Column Temperature: 38° C.; Nozzle Pressure: 100 bar; Nozzle Temperature: 60° C.; Evaporator Temperature: 20° C.; Trimmer Temperature: 25° C.; Wavelength: 220 nm) to afford Compound 1017: N-(6-amino-5-methyl-3-pyridyl)-2-[(2S,5R)-5-methyl-2-[6-(4-methylpiperazin-1-yl)-3-pyridyl]-1-piperidyl]-2-oxo-acetamide (30 mg, single unknown enantiomer with trans relative stereochemistry, peak 2, retention time=3.832 min, white solid). $^1$H NMR (400 MHz, DMSO-$d_6$) δ ppm 10.08 (br s, 1H), 7.92-8.26 (m, 2H), 7.49 (br s, 2H), 6.79 (d, J 8.8 Hz, 1H), 5.34 (br s, 3H), 3.34-3.63 (m, 5H), 2.35-2.45 (m, 5H), 2.23 (s, 3H), 2.01-2.13 (m, 5H), 1.71-1.96 (m, 2H), 1.34 (br d, J 13.3 Hz, 1H), 1.04 (d, J 7.0 Hz, 3H); LCMS (ESI) [M+H]$^+$ m/z: calcd 452.2, found 452.3; HPLC: 100% @254 nm; 100.0% ee.

Example 743. The Synthesis of 5-[[2-[(2S,5R)-2-(4-hydroxy-3-isopropyl-phenyl)-5-methyl-1-piperidyl]-2-oxo-acetyl]amino]pyridine-3-carboxamide (Compound 552)

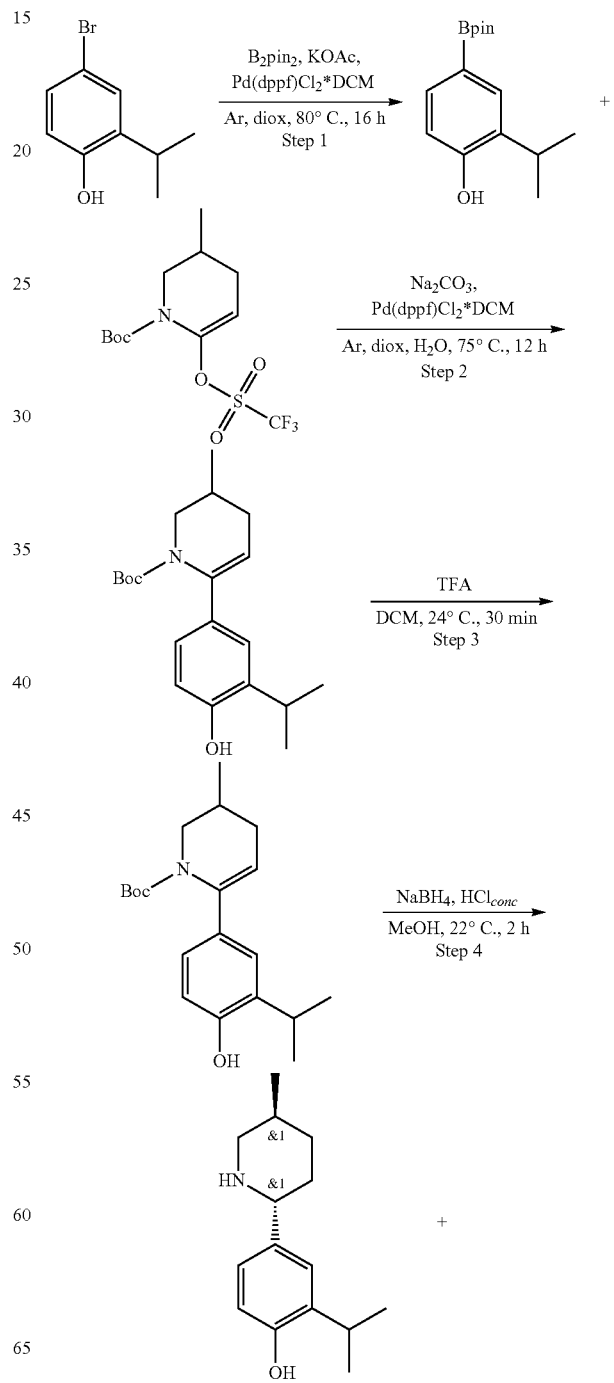

-continued

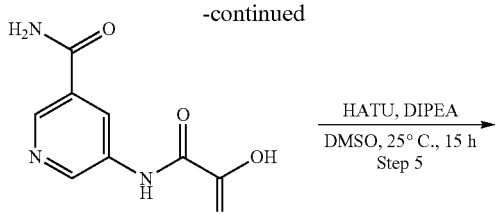

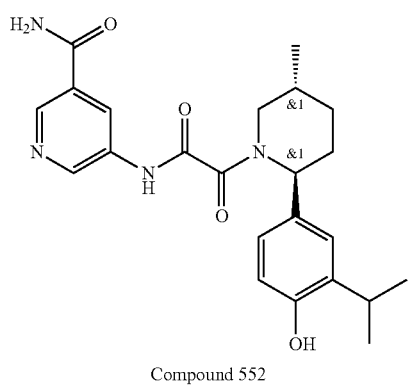 [SMILES: CC(C)c1cc([C@@H]2CC[C@@H](C)CN2C(=O)C(=O)Nc2cncc(C(N)=O)c2)ccc1O]

Compound 552

Step 1: The Synthesis of 2-isopropyl-4-(4,4,5,5-tetramethyl-1,3,2-dioxaborolan-2-yl)phenol 4-bromo-2-isopropyl-phenol (10 g, 46.49 mmol), 4,4,5,5-tetramethyl-2-(4,4,5,5-tetramethyl-1,3,2-dioxaborolan-2-yl)-1,3,2-dioxaborolane (12.6 g, 49.62 mmol), Potassium Acetate (18.25 g, 185.97 mmol, 11.63 mL) and Pd(dppf)Cl$_2$ DCM (1.54 g, 1.86 mmol) were mixed up in 1,4-dioxane (200 mL) and stirred under inert atmosphere at 80° C. for 16 hr. The reaction mixture was diluted with water (500 mL) and extracted with DCM (3×200 mL). The organic layers were combined, dried over Na$_2$SO$_4$ and concentrated in vacuo. Crude material was submitted to column chromatography to afford 2-isopropyl-4-(4,4,5,5-tetramethyl-1,3,2-dioxaborolan-2-yl)phenol (7.5 g, 28.61 mmol, 61.54% yield).

LCMS(ESI): [M+H]$^+$ m/z: calcd 262.2; found 263.2; Rt=1.333 min.

Step 2: The Synthesis of tert-butyl 6-(4-hydroxy-3-isopropyl-phenyl)-3-methyl-3,4-dihydro-2H-pyridine-1-carboxylate 2-isopropyl-4-(4,4,5,5-tetramethyl-1,3,2-dioxaborolan-2-yl)phenol (3 g, 11.44 mmol), tert-butyl 3-methyl-6-(trifluoromethylsulfonyloxy)-3,4-dihydro-2H-pyridine-1-carboxylate (3.16 g, 9.16 mmol), Sodium carbonate (3.64 g, 34.33 mmol, 1.44 mL) and Pd(dppf)Cl$_2$ DCM (378.43 mg, 457.75 µmol) were dissolved in a mixture of 1,4-dioxane (25 mL) and water (9 mL). The reaction mixture was stirred under argon atmosphere at 75° C. for 12 hr. After cooling down, the reaction mixture was diluted with water and extracted with DCM (3×40 mL). The combined extracts were dried over Na$_2$SO$_4$, concentrated in vacuo and the residue was submitted to column chromatography to afford tert-butyl 6-(4-hydroxy-3-isopropyl-phenyl)-3-methyl-3,4-dihydro-2H-pyridine-1-carboxylate (0.8 g, 2.41 mmol, 21.09% yield).

$^1$H NMR (400 MHz, CDCl$_3$) δ 0.93 (d, 3H), 0.99 (s, 9H), 1.05 (m, 6H), 1.81 (m, 2H), 2.13 (m, 1H), 2.98 (m, 1H), 3.81 (m, 1H), 5.02 (m, 1H), 6.34 (d, 1H), 6.45 (d, 1H), 6.98 (s, 1H), 9.02 (s, 1H).

Step 3: The Synthesis of 2-isopropyl-4-(3-methyl-2,3,4,5-tetrahydropyridin-6-yl)phenol tert-butyl 6-(4-hydroxy-3-isopropyl-phenyl)-3-methyl-3,4-dihydro-2H-pyridine-1-carboxylate (0.3 g, 905.12 µmol) was added to a mixture of TFA (1.48 g, 12.98 mmol, 1 mL) and DCM (1 mL). The reaction mixture was stirred for 0.5 hr and concentrated in vacuo to afford 2-isopropyl-4-(3-methyl-2,3,4,5-tetrahydropyridin-6-yl)phenol (0.2 g, crude, TFA) which was used directly in the next step without purification.

LCMS(ESI): [M+H]$^+$ m/z: calcd 231.2; found 232.2; Rt=0.988 min.

Step 4: The Synthesis of 2-isopropyl-4-[(2S,5R)-5-methyl-2-piperidyl]phenol

Crude 2-isopropyl-4-(3-methyl-2,3,4,5-tetrahydropyridin-6-yl)phenol (0.2 g, 580.81 µmol, TFA) was dissolved in methanol (3 mL) and Sodium Borohydride (26.37 mg, 696.97 µmol, 24.64 µL) was added in one portion with stirring. When LCMS of the reaction mixture showed the completion of the reaction, an excess of HCl dioxane solution was added and the reaction mixture was concentrated under reduced pressure to afford 2-isopropyl-4-[(2S,5R)-5-methyl-2-piperidyl]phenol (0.18 g, crude) which was used in the next step without purification.

LCMS(ESI): [M+H]$^+$ m/z: calcd 233.2; found 234.2; Rt=0.791 min.

Step 5: The Synthesis of 5-[[2-[(2S,5R)-2-(4-hydroxy-3-isopropyl-phenyl)-5-methyl-1-piperidyl]-2-oxo-acetyl]amino]pyridine-3-carboxamide (Compound 552

Crude 2-isopropyl-4-[(2S,5R)-5-methyl-2-piperidyl]phenol (0.18 g, 667.14 µmol, HCl), 2-[(5-carbamoyl-3-pyridyl)amino]-2-oxo-acetic acid (167.45 mg, 800.57 µmol), HATU (304.40 mg, 800.57 µmol) and DIPEA (742.00 mg, 5.74 mmol, 1 mL) were mixed up in DMSO (3 mL) and stirred at 25° C. for 15 hr. After completion of the reaction, the reaction mixture was submitted to HPLC to afford 5-[[2-[(2S,5R)-2-(4-hydroxy-3-isopropyl-phenyl)-5-methyl-1-piperidyl]-2-oxo-acetyl]amino]pyridine-3-carboxamide (0.166 g, 391.06 µmol, 58.62% yield).

HPLC data: 2-10 min 40-60% water+NH$_3$/MeOH+NH$_3$ (loading pump 4 ml MeOH+NH$_3$)column: TRIART 100*20 5 microM Inj. volume 1500.000 $^1$H NMR (600 MHz, DMSO-d$_6$) δ 0.98-1.03 (m, 3H), 1.08-1.16 (m, 6H), 1.26-1.36 (m, 1H), 1.63-1.76 (m, 1H), 1.80-1.92 (m, 1H), 1.96-2.11 (m, 1H), 2.11-2.20 (m, 1H), 2.77-3.24 (m, 2H), 3.39-4.02 (m, 1H), 4.99-5.59 (m, 1H), 6.70-6.81 (m, 1H), 6.85-6.97 (m, 1H), 6.98-7.05 (m, 1H), 7.53-7.67 (m, 1H), 8.06-8.19 (m, 1H), 8.41-8.51 (m, 1H), 8.69-8.78 (m, 1H), 8.81-8.93 (m, 1H), 9.21 (s, 1H), 10.99-11.44 (m, 1H).

LCMS(ESI): [M+H]$^+$ m/z: calcd 424.2; found 425.2; Rt=2.662 min.

Example 744. The Synthesis of 5-[[2-[(2S,5R)-2-(4-hydroxy-3,5-dimethyl-phenyl)-5-methyl-1-piperidyl]-2-oxo-acetyl]amino]pyridine-3-carboxamide and 5-[[2-[(2R,5S)-2-(4-hydroxy-3,5-dimethyl-phenyl)-5-methyl-1-piperidyl]-2-oxo-acetyl]amino]pyridine-3-carboxamide (Compound 335 and Compound 326

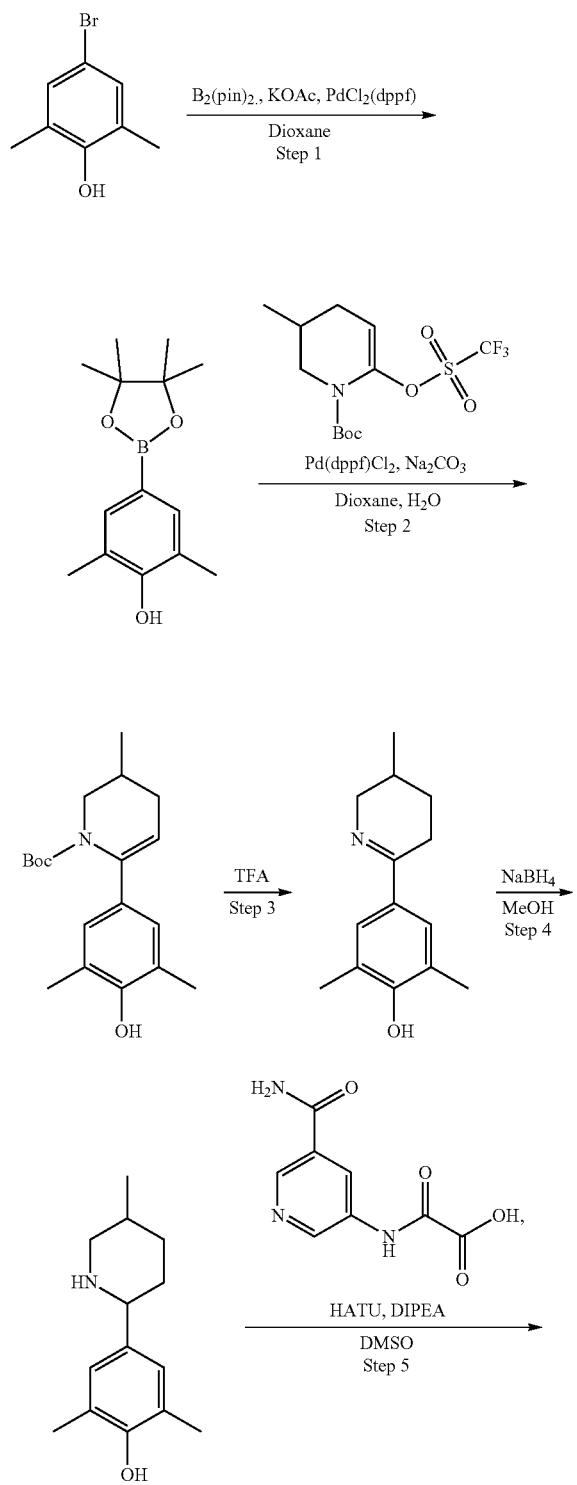

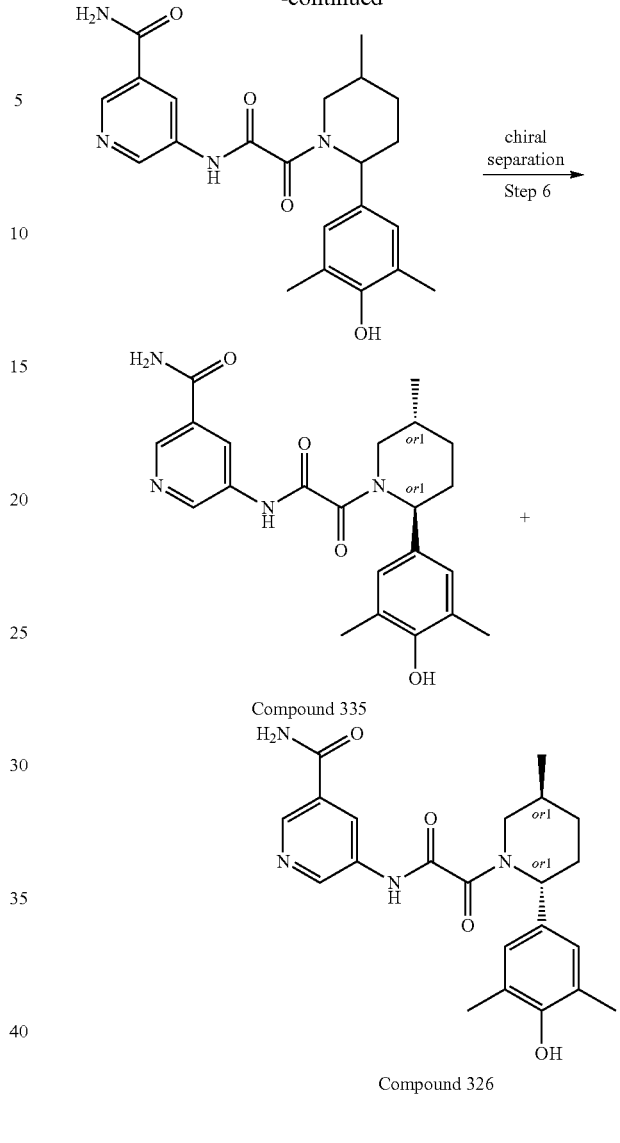

Step 1: Synthesis of 2,6-dimethyl-4-(4,4,5,5-tetramethyl-1,3,2-dioxaborolan-2-yl)phenol A stirring solution of 4-bromo-2,6-dimethyl-phenol (18.7 g, 93.01 mmol), 4,4,5,5-tetramethyl-2-(4,4,5,5-tetramethyl-1,3,2-dioxaborolan-2-yl)-1,3,2-dioxaborolane (28.34 g, 111.61 mmol) and KOAc (27.38 g, 279.02 mmol, 17.44 mL) in 1,4-dioxane (400 mL) was purged with argon for 10 minutes. After 10 minutes, Pd(dppf)Cl$_2$CH$_2$Cl$_2$ (1.5 g, 1.84 mmol) was added under argon. The reaction mixture was stirred under argon at 100° C. for 16 hours. The reaction mixture was then cooled to room temperature, filtered and the filtrate was concentrated under reduced pressure. The obtained crude product was purified by flash chromatography (SiO$_2$, Eluent: CHCl$_3$:acetonitrile) to give 2,6-dimethyl-4-(4,4,5,5-tetramethyl-1,3,2-dioxaborolan-2-yl)phenol (10.4 g, 41.91 mmol, 45.07% yield).

LCMS(ESI): [M–H]$^-$ m/z: calcd 248.2; found 247.2; Rt=1.475 min.

Step 2: Synthesis of tert-butyl 6-(4-hydroxy-3,5-dimethyl-phenyl)-3-methyl-3,4-dihydro-2H-pyridine-1-carboxylate A stirring solution of tert-butyl 3-methyl-6-(trifluoromethylsulfonyloxy)-3,4-dihydro-2H-pyridine-1-carboxylate (1.11 g, 3.22 mmol), 2,6-dimethyl-4-(4,4,5,5-tetramethyl-1,3,2-dioxaborolan-2-yl)phenol (1 g, 4.03 mmol) and Sodium carbonate (1.03 g, 9.67 mmol, 405.21 μL) in 1,4-dioxane (7.5 mL) and water (2.5 mL) was purged with argon. Then, Pd(dppf)Cl$_2$CH$_2$Cl$_2$ (131.55 mg, 161.21 μmol) was added under argon. The reaction mixture was stirred under argon at 75° C. for 40 hours. After 40 hours, the reaction mixture was allowed to cool to room temperature and filtered. The filter cake was washed with 1,4-dioxane (10 mL) and discarded. The filtrate was washed with water and extracted with DCM. The combined organic phase was dried over Na$_2$SO$_4$ and concentrated under reduced pressure to obtain tert-butyl 6-(4-hydroxy-3,5-dimethyl-phenyl)-3-methyl-3,4-dihydro-2H-pyridine-1-carboxylate (1.15 g, crude).

LCMS(ESI): [M+H]$^+$ m/z: calcd 317.2; found 318.2; Rt=1.594 min.

Step 3: Synthesis of 2,6-dimethyl-4-(3-methyl-2,3,4,5-tetrahydropyridin-6-yl)phenol tert-butyl 6-(4-hydroxy-3,5-dimethyl-phenyl)-3-methyl-3,4-dihydro-2H-pyridine-1-carboxylate (1.15 g, crude) was dissolved in Trifluoroacetic acid (4.44 g, 38.94 mmol, 3 mL) and stirred for 16 hours at room temperature. After 16 hours, the reaction mixture was concentrated under reduced pressure to get dark-brown oil. The obtained crude product was treated with aqueous NaOH solution and then neutralized with NaHSO$_4$ to pH=4-5. The resulting suspension was extracted with DCM. The organic layer was dried over Na$_2$SO$_4$ and concentrated under vacuo to give 2,6-dimethyl-4-(3-methyl-2,3,4,5-tetrahydropyridin-6-yl)phenol (0.5 g, crude). The crude product was used in the next step reaction without any further purification.

LCMS(ESI): [M+H]$^+$ m/z: calcd 203.2; found 204.2; Rt=0.680 min.

Step 4: Synthesis of 2,6-dimethyl-4-(5-methyl-2-piperidyl)phenol

Sodium Borohydride (87.05 mg, 2.30 mmol) was added portion wise at 0° C. to a stirred solution of 2,6-dimethyl-4-(3-methyl-2,3,4,5-tetrahydropyridin-6-yl)phenol (0.5 g, 2.30 mmol) in methanol (10 mL). The reaction mixture was stirred at the room temperature for 1 hour. After 1 hour, the reaction mixture was concentrated under reduced pressure, the residue was diluted with water and extracted with DCM (2×25 mL). The combined organic phase was dried over Na$_2$SO$_4$ and evaporated in vacuo to obtain 2,6-dimethyl-4-(5-methyl-2-piperidyl)phenol (0.4 g, crude).

LCMS(ESI): [M+H]$^+$ m/z: calcd 219.2; found 220.2; Rt=0.780 min.

Step 5: Synthesis of 5-[[2-[2-(4-hydroxy-3,5-dimethyl-phenyl)-5-methyl-1-piperidyl]-2-oxo-acetyl]amino]pyridine-3-carboxamide To a stirred solution of 2,6-dimethyl-4-(5-methyl-2-piperidyl)phenol (0.4 g, 1.82 mmol), 2-[(5-carbamoyl-3-pyridyl)amino]-2-oxo-acetic acid (283.31 mg, 912.88 μmol, Et$_3$N salt) and HATU (416.85 mg, 1.10 mmol) in DMSO (4 mL) was added DIPEA (120.39 mg, 931.48 μmol, 162.24 μL). The reaction mixture was stirred at 25° C. for 16 hours. After 16 hours, the reaction mixture was purified by reverse phase HPLC (Eluent: 2-10 min, 0-85%, MeOH/H$_2$O; flow rate: 30 mL/min; loading pump: 4 mL, MeOH; column: SunFire C18 100×19 mm, 5 um) to obtain 5-[[2-[2-(4-hydroxy-3,5-dimethyl-phenyl)-5-methyl-1-piperidyl]-2-oxo-acetyl]amino]pyridine-3-carboxamide (60 mg, 146.18 μmol, 8.01% yield).

LCMS(ESI): [M+H]$^+$ m/z: calcd 410.2; found 411.2; Rt=2.913 min.

Step 6: Chiral Separation of 5-[[2-[(2S,5R)-2-(4-hydroxy-3,5-dimethyl-phenyl)-5-methyl-1-piperidyl]-2-oxo-acetyl]amino]pyridine-3-carboxamide and 5-[[2-[(2R,5S)-2-(4-hydroxy-3,5-dimethyl-phenyl)-5-methyl-1-piperidyl]-2-oxo-acetyl]amino]pyridine-3-carboxamide (Compound 335 and Compound 326

5-[[2-[2-(4-hydroxy-3,5-dimethyl-phenyl)-5-methyl-1-piperidyl]-2-oxo-acetyl]amino]pyridine-3-carboxamide (60 mg, 146.18 μmol) was subjected to chiral HPLC purification (Column: Chiralpak 1C (250×20 mm, 5 um); Mobile phase: CO$_2$-MeOH, 60-40; Flow Rate: 40 mL/min) to get 5-[[2-[(2S,5R)-2-(4-hydroxy-3,5-dimethyl-phenyl)-5-methyl-1-piperidyl]-2-oxo-acetyl]amino]pyridine-3-carboxamide (Compound 335, 18.7 mg) and 5-[[2-[(2R,5S)-2-(4-hydroxy-3,5-dimethyl-phenyl)-5-methyl-1-piperidyl]-2-oxo-acetyl]amino]pyridine-3-carboxamide (Compound 326, 19.7 mg) as light-brown solids.

Compound 335:
$^1$H NMR (DMSO-d$_6$, 600 MHz): δ (ppm) 1.00 (m, 3H), 1.31 (m, 1H), 1.70 (m, 1H), 1.85 (m, 1H), 1.95 (m, 1H), 2.07 (m, 1H), 2.15 (m, 6H), 3.02 (m, 1H), 3.68 (m, 1H), 5.23 (m, 1H), 6.84 (m, 2H), 7.59 (m, 1H), 8.16 (m, 2H), 8.47 (m, 1H), 8.75 (m, 1H), 8.85 (m, 1H), 11.21 (m, 1H).

LCMS(ESI): [M+H]$^+$ m/z: calcd 410.2; found 411.2; Rt=4.399 min.

Chiral HPLC: Rt=5.29 min (Column: 1C; Mobile phase: CO$_2$-MeOH, 60-40; Flow Rate: 0.6 mL/min).

Compound 326:
$^1$H NMR (DMSO-d$_6$, 600 MHz): δ (ppm) 1.00 (m, 3H), 1.30 (m, 1H), 1.72 (m, 1H), 1.85 (m, 1H), 2.00 (m, 1H), 2.13 (m, 8H), 2.92 (m, 1H), 3.68 (m, 1H), 5.23 (m, 1H), 6.86 (m, 1H), 7.59 (m, 1H), 8.16 (m, 2H), 8.47 (m, 1H), 8.75 (m, 1H), 8.85 (m, 1H), 11.21 (m, 1H).

LCMS(ESI): [M+H]$^+$ m/z: calcd 410.2; found 411.2; Rt=4.398 min.

Chiral HPLC: Rt=6.28 min (Column: 1C; Mobile phase: CO$_2$-MeOH, 60-40; Flow Rate: 0.6 mL/min).

Example 745. The Synthesis of rac-5-[[2-[(2S,5R)-2-(4-chlorophenyl)-5-methyl-1-piperidyl]-2-oxo-acetyl]amino]pyridine-3-carboxamide (Compound 212), Rel-5-[[2-[(2S,5R)-2-(4-chlorophenyl)-5-methyl-1-piperidyl]-2-oxo-acetyl]amino]pyridine-3-carboxamide (Compound 570) and Rel-5-[[2-[(2R,5S)-2-(4-chlorophenyl)-5-methyl-1-piperidyl]-2-oxo-acetyl]amino]pyridine-3-carboxamide (Compound 569)

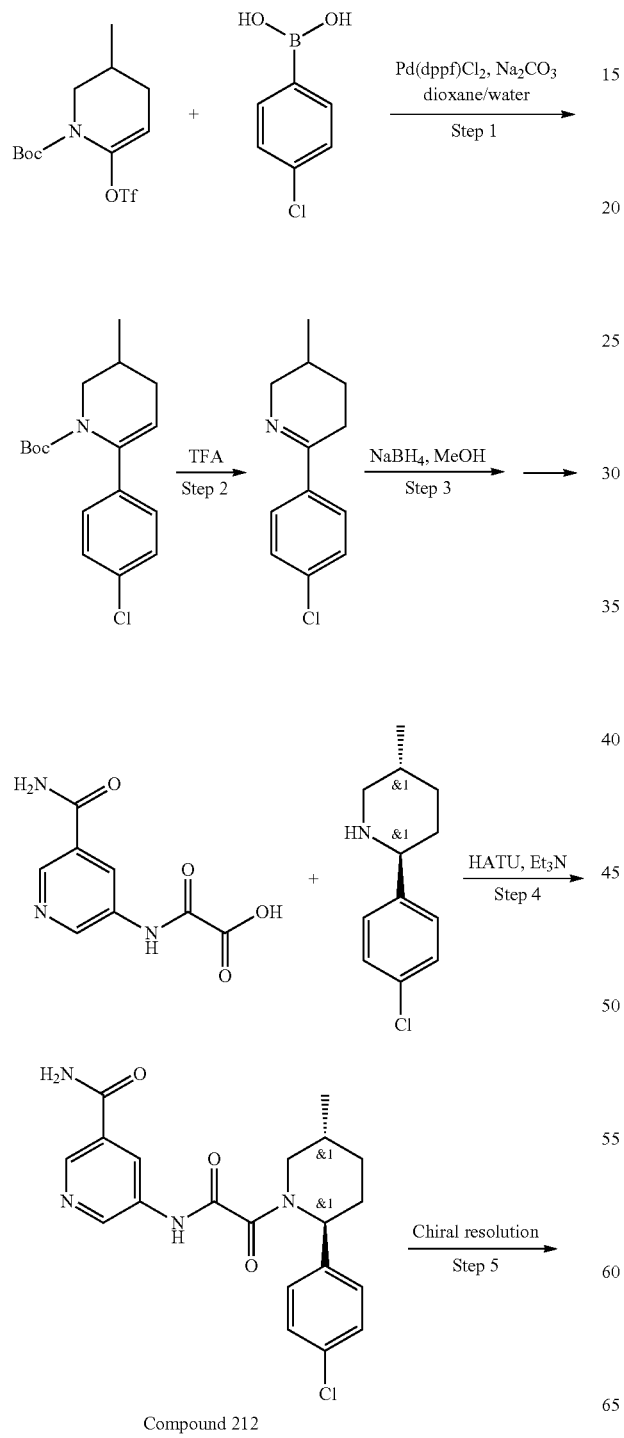

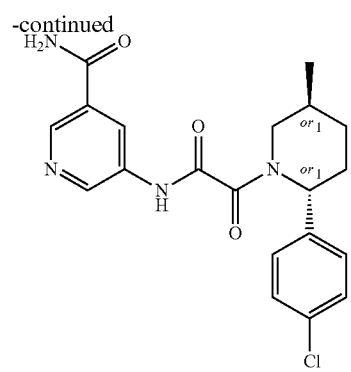

Compound 569

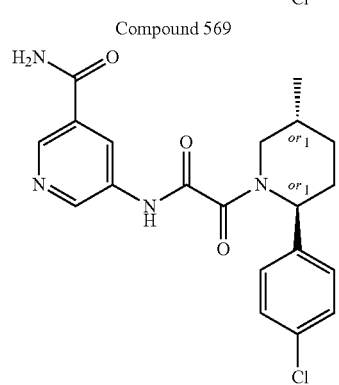

Compound 570

Step 1: Synthesis of tert-butyl 6-(4-chlorophenyl)-3-methyl-3,4-dihydro-2H-pyridine-1-carboxylate tert-butyl 3-methyl-6-(trifluoromethylsulfonyloxy)-3,4-dihydro-2H-pyridine-1-carboxylate (6 g, 17.37 mmol), (4-chlorophenyl)boronic acid (3.53 g, 22.59 mmol) and Sodium carbonate (5.52 g, 52.12 mmol, 2.18 mL) were added to a mixture of 1,4-dioxane (90 mL) and water (30 mL). The resulting mixture was evacuated and then back-filled with argon, this operation was repeated three times, then Pd(dppf)Cl2·DCM (567.10 mg, 694.98 µmol) was added under argon. The reaction mixture was stirred under argon at 70° C. for 12 hr, then cooled and filtered. The filtercake was washed with 1,4-dioxane (2*20 ml) and discarded. The filtrate was evaporated in vacuo, and the residue was purified by column chromatography on silica gel using hexane/MTBE gradient (0-70% MTBE) to afford tert-butyl 6-(4-chlorophenyl)-3-methyl-3,4-dihydro-2H-pyridine-1-carboxylate (3.2 g, 10.40 mmol, 59.83% yield) as white solid.

$^1$H NMR (CDCl$_3$, 400 MHz): δ 0.98 (d, 3H), 1.08 (s, 9H), 1.78 (m, 1H), 1.98 (m, 1H), 2.38 (m, 1H), 2.97 (t, 1H), 4.02 (d, 1H), 5.26 (s, 1H), 7.24 (m, 4H).

LCMS(ESI): [M−tBu]$^+$ m/z: calcd 307.8; found 252.0; Rt=1.829 min.

Step 2: Synthesis of 6-(4-chlorophenyl)-3-methyl-2,3,4,5-tetrahydropyridine tert-butyl 6-(4-chlorophenyl)-3-methyl-3,4-dihydro-2H-pyridine-1-carboxylate (3.2 g, 10.40 mmol) was dissolved in Trifluoroacetic acid (22.56 g, 197.87 mmol, 15.24 mL). The resulting solution was stirred at 25° C. for 1 hr, then crushed ice was added (20 g) and pH was adjusted to 10 with a solution of Sodium hydroxide, pearl (10.40 g, 259.90 mmol, 4.88 mL) in water (50 ml). The resulting cloudy solution was transferred to a separatory funnel and extracted with dichloromethane (2*50 ml). The combined organic extracts were washed with water (20 ml), dried over sodium sulphate and evaporated in vacuo to afford 6-(4-chlorophenyl)-3-methyl-2,3,4,5-tetrahydropyridine (2.1 g, 10.11 mmol, 97.26% yield) as yellow gum.

$^1$H NMR (CDCl$_3$, 500 MHz): δ 1.0 (d, 3H), 1.30 (m, 1H), 1.70 (m, 1H), 1.95 (m, 1H), 2.50 (m, 1H), 2.70 (d, 1H), 3.20 (m, 1H), 4.00 (d, 1H), 7.33 (d, 2H), 7.73 (d, 2H).

LCMS(ESI): [M+1]$^+$ m/z: calcd 207.0; found 208.0; Rt=0.89 min.

Step 3: Synthesis of 2-(4-chlorophenyl)-5-methyl-piperidine

Sodium Borohydride (764.98 mg, 20.22 mmol, 714.94 μL) was added in one portion to a stirred solution of 6-(4-chlorophenyl)-3-methyl-2,3,4,5-tetrahydropyridine (2.1 g, 10.11 mmol) in methanol (20 mL) at 0° C. The resulting mixture was stirred at 0° C. for 1 hr, and then evaporated in vacuo. The residue was diluted with water (20 ml) and extracted with dichloromethane (2*40 ml). The combined organic extracts were dried over sodium sulphate and evaporated in vacuo to afford 2-(4-chlorophenyl)-5-methyl-piperidine (1.9 g, 9.06 mmol, 89.61% yield) as colorless oil, which was used directly in the next step.

$^1$H NMR (CDCl$_3$, 400 MHz): δ 0.80 (d, 3H), 1.15 (m, 1H), 1.45 (m, 1H), 1.60 (brs, 1H), 1.75 (m, 1H), 1.85 (m, 1H), 2.38 (t, 1H), 3.11 (d, 1H), 3.50 (d, 1H), 7.30 (m, 4H).

LCMS(ESI): [M+1]$^+$ m/z: calcd 209.2; found 210.2; Rt=0.861 min.

Step 4: Synthesis of 5-[[2-[(2S,5R)-2-(4-chlorophenyl)-5-methyl-1-piperidyl]-2-oxo-acetyl]amino]pyridine-3-carboxamide (Compound 212

Triethyl amine (1.21 g, 11.92 mmol, 1.66 mL) was added to a mixture of 2-(4-chlorophenyl)-5-methyl-piperidine (250 mg, 1.19 mmol) (crude from previous step), 2-[(5-carbamoyl-3-pyridyl)amino]-2-oxo-acetic acid (369.96 mg, 1.19 mmol, N(C2H5)3) and HATU (498.60 mg, 1.31 mmol) in DMF (4 mL). The reaction mixture was stirred at 25° C. for 12 hr, then submitted to reverse phase HPLC (column: YMC-Triart C18 100×20 mm 5 um, mobile phase: 35-75% 1-6 min 0.1% NH$_3$-methanol) to afford Compound 212 5-[[2-[(2S,5R)-2-(4-chlorophenyl)-5-methyl-1-piperidyl]-2-oxo-acetyl]amino]pyridine-3-carboxamide (173 mg, 431.57 μmol, 36.20% yield) as white solid.

$^1$H NMR (DMSO-d$_6$, 500 MHz): δ (ppm) 1.03 (m, 3H), 1.34 (m, 1H), 1.66 (m, 1H), 1.91 (d, 1H), 2.14 (m, 2H), 3.01 (m, 1H), 3.76 (m, 1H), 5.38 (d, 1H), 7.41 (m, 4H), 7.61 (m, 1H), 8.17 (m, 1H), 8.48 (m, 1H), 8.83 (m, 2H), 11.25 (m, 1H).

LCMS(ESI): [M+1]$^+$ m/z: calcd 400.2; found 401.2; Rt=3.189 min Step 5: Synthesis of rel-5-[[2-[(2S,5R)-2-(4-chlorophenyl)-5-methyl-1-piperidyl]-2-oxo-acetyl]amino] pyridine-3-carboxamide (Compound 570) and re-5-[[2-[(2R,5S)-2-(4-chlorophenyl)-5-methyl-1-piperidyl]-2-oxo-acetyl]amino]pyridine-3-carboxamide (Compound 569) 5-[[2-[(2S,5R)-2-(4-chlorophenyl)-5-methyl-1-piperidyl]-2-oxo-acetyl]amino]pyridine-3-carboxamide (150 mg, 374.20 μmol) was chirally separated (System:Column: IA-I (250*20, 5 mkm), Mobile phase: Hexane-IPA-MeOH, 50-25-25; Flow rate: 13 ml/min. 24° C., Wavelength: 205 nm, 215 nm)

Rt1=14.03—cis-impurity

Rt2=20.5—Compound 569

Rt3=27.1—Compound 570)

to obtain Compound 570—5-[[2-[(2S,5R)-2-(4-chlorophenyl)-5-methyl-1-piperidyl]-2-oxo-acetyl]amino]pyridine-3-carboxamide (59.69 mg, 148.91 μmol, 39.79% yield) (RT (IA, Hexane-IPA-MeOH, 50-25-25, 0.6 ml/min) =30.693 min) as a beige solid and Compound 569-5-[[2-[(2R,5S)-2-(4-chlorophenyl)-5-methyl-1-piperidyl]-2-oxo-acetyl]amino]pyridine-3-carboxamide (65.53 mg, 163.47 μmol, 43.69% yield) (RT (IA, Hexane-IPA-MeOH, 50-25-25, 0.6 ml/min)=23.405 min) as a beige solid.

Compound 569: 1H NMR (600 MHz, DMSO-d$_6$) δ 0.98-1.07 (m, 3H), 1.26-1.40 (m, 1H), 1.56-1.70 (m, 1H), 1.82-1.97 (m, 1H), 2.00-2.13 (m, 1H), 2.14-2.25 (m, 1H), 2.76-3.25 (m, 1H), 3.43-4.06 (m, 1H), 5.11-5.63 (m, 1H), 7.30-7.40 (m, 2H), 7.39-7.48 (m, 2H), 7.54-7.65 (m, 1H), 8.09-8.20 (m, 1H), 8.43-8.52 (m, 1H), 8.72-8.80 (m, 1H), 8.81-8.93 (m, 1H), 11.13-11.40 (m, 1H).

LCMS(ESI): [M+1]$^+$ m/z: calcd 400.2; found 401.2; Rt=2.845 min

Compound 570: 1H NMR (600 MHz, DMSO-d$_6$) δ 0.99-1.07 (m, 3H), 1.27-1.36 (m, 1H), 1.56-1.70 (m, 1H), 1.82-1.95 (m, 1H), 2.02-2.14 (m, 1H), 2.14-2.23 (m, 1H), 2.73-3.24 (m, 1H), 3.45-4.04 (m, 1H), 5.10-5.66 (m, 1H), 7.29-7.39 (m, 2H), 7.40-7.49 (m, 2H), 7.54-7.67 (m, 1H), 8.08-8.22 (m, 1H), 8.40-8.51 (m, 1H), 8.68-8.80 (m, 1H), 8.80-8.94 (m, 1H), 11.13-11.34 (m, 1H).

LCMS(ESI): [M+1]$^+$ m/z: calcd 400.2; found 401.2; Rt=2.845 min.

Example 746. The Synthesis of N-(6-amino-5-methylpyridin-3-yl)-2-(4-Isobutyryl-2-(2-oxo-1,2,3,4-tetrahydroquinolin-6-yl)piperidin-1-yl)-2-oxoacetamide (Compound 854 and Compound 853

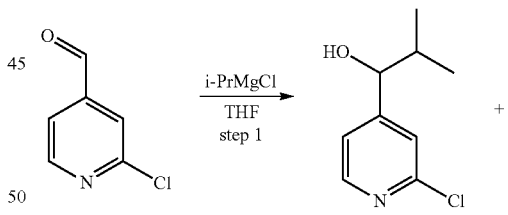

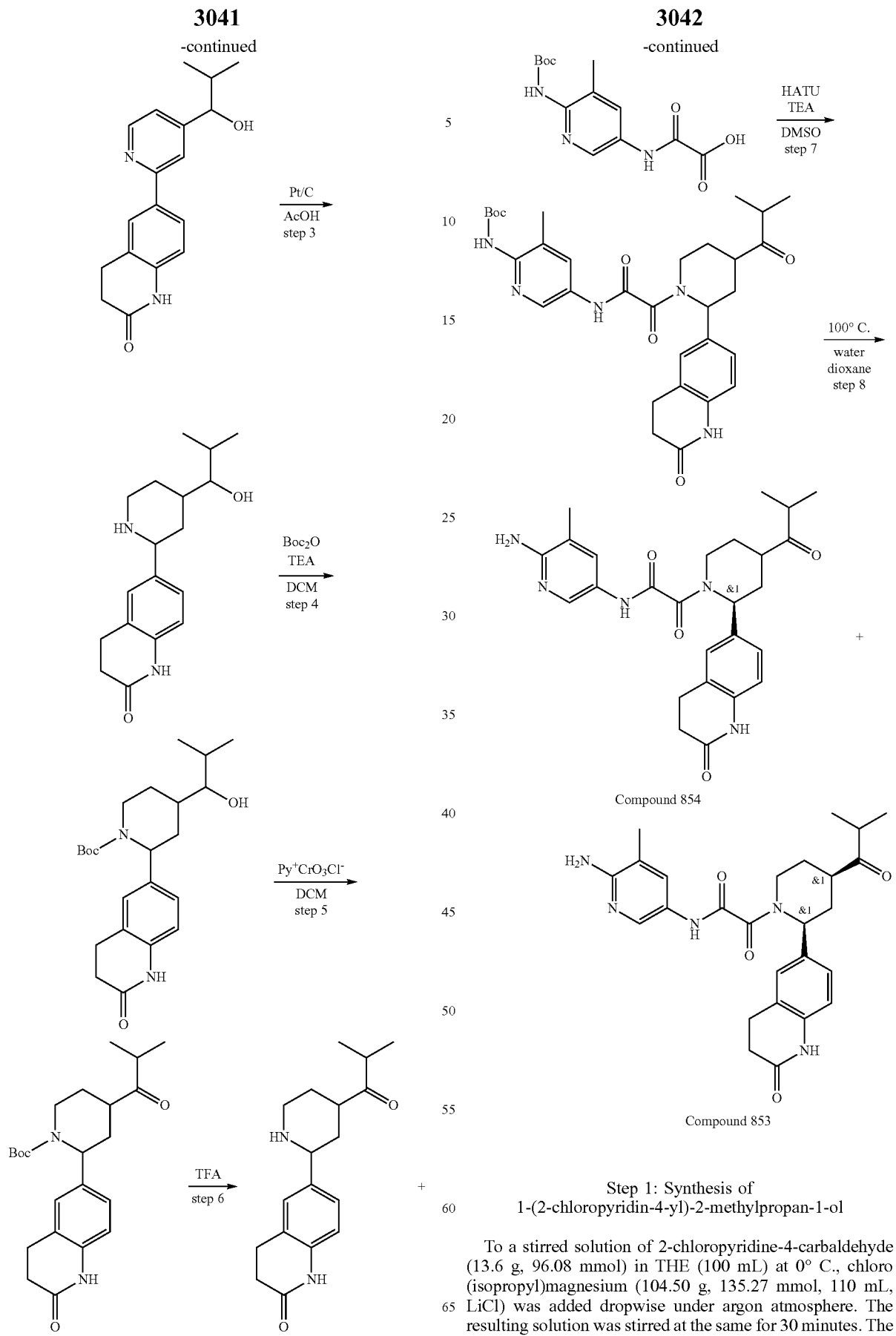
Compound 854
Compound 853
Step 1: Synthesis of
1-(2-chloropyridin-4-yl)-2-methylpropan-1-ol
To a stirred solution of 2-chloropyridine-4-carbaldehyde (13.6 g, 96.08 mmol) in THF (100 mL) at 0° C., chloro (isopropyl)magnesium (104.50 g, 135.27 mmol, 110 mL, LiCl) was added dropwise under argon atmosphere. The resulting solution was stirred at the same for 30 minutes. The reaction mixture was allowed to warm to rt and stirred for 12 h at 20° C. The reaction mixture was quenched with saturated NH₄Cl aq. solution and extracted with MTBE. The organic layer dried over Na₂SO₄, filtered and evaporated under reduced pressure. The crude product was purified by column chromatography (gradient chloroform-acetonitrile, flow rate: 65 ml/min) to obtain 1-(2-chloro-4-pyridyl)-2-methyl-propan-1-ol (4.6 g, 24.78 mmol, 25.79% yield).

$^1$H NMR (500 MHz, DMSO-d$_6$) δ (ppm) 0.70 (d, 6H), 1.68 (m, 1H), 4.15 (m, 1H), 5.18 (m, 1H), 7.14 (m, 2H), 8.12 (s, 1H). LCMS(ESI): [M]⁺ m/z: calcd 185.2; found 186.2; Rt=0.991 min.

Step 2: Synthesis of 6-(4-(1-hydroxy-2-methylpropyl)pyridin-2-yl)-3,4-dihydroquinolin-2(1H)-one To a stirred solution of 6-(4,4,5,5-tetramethyl-1,3,2-dioxaborolan-2-yl)-3,4-dihydro-1H-quinolin-2-one (6.62 g, 24.24 mmol), 1-(2-chloro-4-pyridyl)-2-methyl-propan-1-ol (4.5 g, 24.24 mmol) and sodium carbonate (7.71 g, 72.72 mmol, 3.05 mL) in mixture of dioxane (90 mL) and water (90 mL) under argon Pd(dppf)Cl₂*DCM (1.19 g, 1.45 mmol) was added. The reaction mixture was heated at 80° C. for 12 hr. Then reaction mixture was diluted with water and extracted with DCM, dried over Na₂SO₄ and concentrated under reduced pressure. The obtained crude product was purified by column chromatography (gradient hexane:CHCl₃) to afford 6-[4-(1-hydroxy-2-methyl-propyl)-2-pyridyl]-3,4-dihydro-1H-quinolin-2-one (1.8 g, 6.07 mmol, 25.06% yield).

$^1$H NMR (500 MHz, DMSO-d$_6$) δ (ppm) 0.94 (d, 6H), 1.98 (m, 1H), 2.42 (m, 2H), 3.06 (m, 2H), 4.28 (m, 1H), 5.24 (m, 1H), 6.86 (m, 1H), 7.18 (m, 1H), 7.66 (m, 1H), 7.91 (m, 2H), 8.48 (m, 1H), 10.22 (m, 1H). LCMS(ESI): [M]⁺ m/z: calcd 296.2; found 297.2; Rt=0.852 min.

Step 3: Synthesis of 6-(4-(1-hydroxy-2-methylpropyl)piperidin-2-yl)-3,4-dihydroquinolin-2(1H)-one 6-[4-(1-hydroxy-2-methyl-propyl)-2-pyridyl]-3,4-dihydro-1H-quinolin-2-one (900 mg, 3.04 mmol) was dissolved in CH₃COOH (25 mL). Starting material was hydrogenated over Pt/C (200 mg) under pressure H₂ (3.04 mmol) 40 atm at 20° C. for 16 hr. Then 200 mg of Evonik Pt/C catalyst was added and reaction mixture was hydrogenated under the same pressure at 20° C. for the next 24 hr. Then 250 mg of Evonik Pt/C catalyst was added and reaction mixture was hydrogenated under the same pressure at 20° C. for the next 24 hr. Reaction mixture was filtered and concentrated in vacuum to obtain 6-[4-(1-hydroxy-2-methyl-propyl)-2-piperidyl]-3,4-dihydro-1H-quinolin-2-one (1.2 g, crude, CH₃COOH).

LCMS(ESI): [M]⁺ m/z: calcd 302.2; found 303.2; Rt=0.871 min.

Step 4: Synthesis of tert-butyl 4-(1-hydroxy-2-methylpropyl)-2-(2-oxo-1,2,3,4-tetrahydroquinolin-6-yl)piperidine-1-carboxylate 6-[4-(1-hydroxy-2-methyl-propyl)-2-piperidyl]-3,4-dihydro-1H-quinolin-2-one (1.5 g, 4.96 mmol, CH₃COOH) and TEA (1.51 g, 14.88 mmol, 2.07 mL) were mixed in DCM (40 mL), cooled with ice-water bath and Boc₂O (1.19 g, 5.46 mmol, 1.25 mL) in 5 ml of DCM was added dropwise, then stirred overnight. Reaction mixture was washed with water, dried over Na₂SO₄ and concentrated in vacuum to give tert-butyl 4-(1-hydroxy-2-methyl-propyl)-2-(2-oxo-3,4-dihydro-1H-quinolin-6-yl)piperidine-1-carboxylate (2.2 g, crude).

$^1$H NMR (500 MHz, DMSO-d$_6$) δ (ppm) 0.80 (d, 6H), 1.21 (s, 9H), 1.36 (m, 1H), 1.64 (m, 4H), 2.39 (m, 2H), 2.81 (m, 2H), 3.13 (m, 1H), 3.81 (m, 1H), 4.31 (m, 1H), 4.58 (m, 1H), 6.75 (d, 1H), 6.95 (d, 1H), 6.99 (s, 1H), 9.98 (s, 1H). LCMS(ESI): [M–Boc]⁺ m/z: calcd 302.2; found 303.2; Rt=1.389 min.

Step 5: Synthesis of tert-butyl 4-Isobutyryl-2-(2-oxo-1,2,3,4-tetrahydroquinolin-6-yl)piperidine-1-carboxylate tert-butyl 4-(1-hydroxy-2-methyl-propyl)-2-(2-oxo-3,4-dihydro-1H-quinolin-6-yl)piperidine-1-carboxylate (1 g, 2.48 mmol) was dissolved in dry DCM (30 mL). Pyridinium chlorochromate (1.07 g, 4.97 mmol) was added and reaction mixture was stirred overnight at 20° C. Reaction mixture was washed with water and then evaporated to dryness. tert-butyl 4-(2-methylpropanoyl)-2-(2-oxo-3,4-dihydro-1H-quinolin-6-yl)piperidine-1-carboxylate (1.5 g, crude) was obtained.

LCMS(ESI): [M–Boc]⁺ m/z: calcd 300.2; found 301.2; Rt=1.249 min.

Step 6: Synthesis of 6-(4-Isobutyrylpiperidin-2-yl)-3,4-dihydroquinolin-2(1H)-one tert-butyl 4-(2-methylpropanoyl)-2-(2-oxo-3,4-dihydro-H-quinolin-6-yl)piperidine-1-carboxylate (1.5 g, 3.75 mmol) was dissolved in TFA (10 g, 3.75 mmol) and stirred overnight. Then reaction mixture was concentrated in vacuum to dryness. Crude product was treated with aqueous solution of sodium bicarbonate and needed product was extracted with EA, dried over Na₂SO₄ and evaporated in vacuum to give 6-[4-(2-methylpropanoyl)-2-piperidyl]-3,4-dihydro-1H-quinolin-2-one (200 mg, crude).

LCMS(ESI): [M]⁺ m/z: calcd 300.2; found 301.2; Rt=0.809 min.

Step 7: Synthesis of tert-butyl (5-(2-(4-Isobutyryl-2-(2-oxo-1,2,3,4-tetrahydroquinolin-6-yl)piperidin-1-yl)-2-oxoacetamido)-3-methylpyridin-2-yl)carbamate 6-[4-(2-methylpropanoyl)-2-piperidyl]-3,4-dihydro-1H-quinolin-2-one (200 mg, 665.79 µmol), 2-[[6-(tert-butoxycarbonylamino)-5-methyl-3-pyridyl]amino]-2-oxo-acetic acid (196.60 mg, 665.79 µmol), HATU (303.78 mg, 798.95 µmol) and TEA (134.74 mg, 1.33 mmol, 185.60 µL) were mixed in DMSO (2 mL) and stirred overnight at 20° C. Solution in DMSO was subjected to HPLC (50-75% R1-2-10 min Flow rate: 30 ml/min; loading pump 4 ml/min MeOH Column Sun Fire 100×19 mm, 5 mkm). tert-butyl N-[3-methyl-5-[[2-[4-(2-methylpropanoyl)-2-(2-oxo-3,4-dihydro-1H-quinolin-6-yl)-1-piperidyl]-2-oxo-acetyl]amino]-2-pyridyl]carbamate (109 mg, 188.69 µmol, 28.34% yield) was obtained.

LCMS(ESI): [M]⁺ m/z: calcd 577.2; found 578.2; Rt=2.935 min.

Step 8: Synthesis of N-(6-amino-5-methylpyridin-3-yl)-2-(4-Isobutyryl-2-(2-oxo-1,2,3,4-tetrahydroquinolin-6-yl)piperidin-1-yl)-2-oxoacetamide (Compound 854 and Compound 853 tert-butyl N-[3-methyl-5-[[2-[4-(2-methylpropanoyl)-2-(2-oxo-3,4-dihydro-1H-quinolin-6-yl)-1-piperidyl]-2-oxoacetyl]amino]-2-pyridyl]carbamate (109 mg, 188.69 μmol) was dissolved in mixture of dioxane (1.5 mL) and water (0.5 mL) and stirred overnight at 100° C. for 12 hr. Solution was subjected to HPLC (2-10 min 10-40% MeCN/H₂O 30 ml/min (loading pump 4 ml MeCN) column: SunFire C18, 5 micro). N-(6-amino-5-methyl-3-pyridyl)-2-[(2S)-4-(2-methylpropanoyl)-2-(2-oxo-3,4-dihydro-1H-quinolin-6-yl)-1-piperidyl]-2-oxo-acetamide (25.8 mg, 54.03 μmol, 28.63% yield) and N-(6-amino-5-methyl-3-pyridyl)-2-[(2S,4R)-4-(2-methylpropanoyl)-2-(2-oxo-3,4-dihydro-1H-quinolin-6-yl)-1-piperidyl]-2-oxo-acetamide (25.5 mg, 53.40 μmol, 28.30% yield) were obtained.

Compound 854: ¹H NMR (600 MHz, DMSO-d₆) δ (ppm) 0.91-0.98 (m, 6H), 1.71-1.76 (m, 1H), 1.78-1.89 (m, 1H), 1.98-2.04 (m, 3H), 2.16-2.32 (m, 1H), 2.39-2.44 (m, 2H), 2.80-2.88 (m, 3H), 2.93-3.06 (m, 1H), 3.40-3.72 (m, 1H), 3.76-4.35 (m, 1H), 5.05-5.58 (m, 1H), 5.59-5.75 (m, 2H), 6.64-6.86 (m, 1H), 6.86-7.05 (m, 1H), 7.04-7.18 (m, 2H), 7.41-7.54 (m, 1H), 7.91-8.17 (m, 1H), 9.98-10.08 (m, 1H), 10.37-10.58 (m, 1H).

LCMS(ESI): [M]⁺ m/z: calcd 477.2; found 478.2; Rt=1.783 min.

Compound 853: ¹H NMR (600 MHz, DMSO-d₆) δ (ppm) 0.88-1.00 (m, 6H), 1.69-1.77 (m, 1H), 1.79-1.87 (m, 1H), 1.87-1.98 (m, 2H), 1.98-2.06 (m, 3H), 2.14-2.35 (m, 2H), 2.36-2.45 (m, 2H), 2.81-2.87 (m, 2H), 2.91-3.04 (m, 1H), 3.43-3.90 (m, 1H), 5.03-5.08 (m, 1H), 5.49-5.65 (m, 2H), 6.67-6.79 (m, 1H), 6.93-7.12 (m, 2H), 7.11-7.55 (m, 1H), 7.58-8.14 (m, 1H), 9.95-10.51 (m, 2H).

LCMS(ESI): [M]⁺ m/z: calcd 477.2; found 478.2; Rt=1.775 min.

Example 747. The Synthesis of N-(5-methyl-3-pyridyl)-2-[(2S,5R)-5-methyl-2-tetralin-6-yl-1-piperidyl]-2-oxo-acetamide (Compound 80)

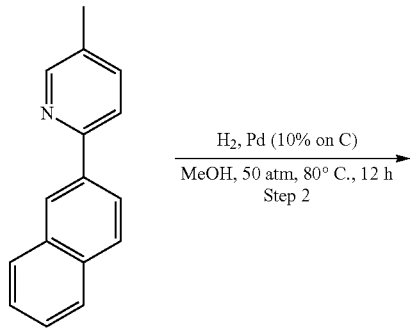

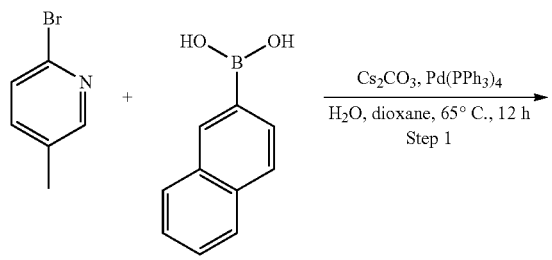

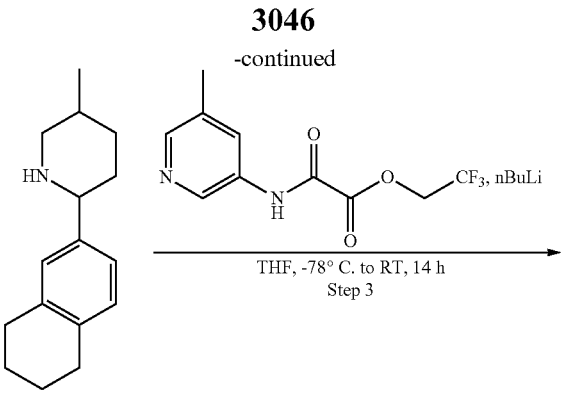

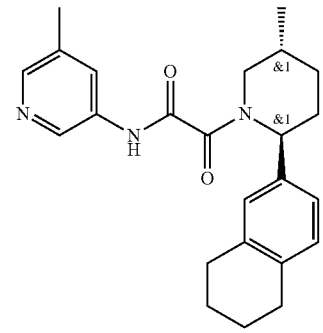

Compound 80

Step 1: The Synthesis of 5-methyl-2-(Naphthalen-2-yl)pyridine 2-bromo-5-methylpyridine (3 g, 17.44 mmol) and naphthalen-2-ylboronic acid (3.60 g, 20.93 mmol) were dissolved in the mixture of dioxane (40 mL) and water (4 mL). The resulting mixture was stirred for 5 min followed by the addition of caesium carbonate (14.21 g, 43.60 mmol) and tetrakis(triphenylphosphane)palladium(0) (87.20 μmol). Then, the reaction flask was quickly evacuated and refilled with argon. The resulting mixture was stirred at 65° C. for 12 hr. After that, it was cooled and evaporated. The residue was partitioned between EtOAc (100 mL) and water (100 mL). The organic phase was collected, dried over Na₂SO₄ and evaporated. The residue was subjected to column chromatography to obtain 5-methyl-2-(naphthalen-2-yl)pyridine (0.7 g, 3.19 mmol, 18.30% yield).

¹H NMR (400 MHz, CDCl₃) δ 2.388 (s, 3H), 7.46 (m, 2H), 7.59 (d, 1H), 7.77 (m, 1H), 7.84 (m, 1H), 7.92 (m, 2H), 8.11 (m, 1H), 8.44 (d, 1H), 8.56 (s, 1H). LCMS(ESI): [M+H]⁺ m/z: calcd 219.1; found 220.2; Rt=1.217 min.

Step 2: The Synthesis of 5-methyl-2-tetralin-6-yl-piperidine

Palladium, 10% on carbon, type 487, dry (33.97 mg, 319.23 μmol) was added to the solution of 5-methyl-2-(2-naphthyl)pyridine (0.7 g, 3.19 mmol) in MeOH (10 mL). The resulting mixture was hydrogenated at 50 atm. pressure and 80° C. for 12 hr. After consumption of starting material (HNMR control), the resulting mixture was cooled to r.t. and filtered. The filtrate was evaporated to dryness to obtain 5-methyl-2-tetralin-6-yl-piperidine (0.35 g, 1.53 mmol, 47.80% yield).

¹H NMR (400 MHz, DMSO-d₆) δ 0.82 (m, 3H), 1.15 (m, 1H), 1.34 (m, 1H), 1.62 (m, 2H), 1.76 (m, 6H), 2.28 (m, 1H), 2.61 (m, 4H), 2.98 (m, 1H), 3.48 (m, 1H), 6.94 (m, 1H), 7.10 (m, 2H).

LCMS(ESI): [M+H]⁺ m/z: calcd 229.1; found 230.2; Rt=1.01 min.

Step 3: The Synthesis of N-(5-methyl-3-pyridyl)-2-[(2S,5R)-5-methyl-2-tetralin-6-yl-1-piperidyl]-2-oxo-acetamide (Compound 80

Butyllithium (195.50 mg, 3.05 mmol) (2.5M in Hexane) was dropwise added to the solution of 5-methyl-2-tetralin-6-yl-piperidine (350.00 mg, 1.53 mmol) in THF (30 mL) at −78° C. The resulting mixture was stirred for 5 min, followed by the addition of 2,2,2-trifluoroethyl 2-[(5-methyl-3-pyridyl)amino]-2-oxo-acetate (400.09 mg, 1.53 mmol). The resulting mixture was left to warm to r.t. and stirred at that temperature for 12 hr. NH₄Cl (0.6 g) aq. solution was added. The resulting mixture was evaporated to dryness. The residue (1 g) was purified HPLC (58% 0.5-6.5 min; water-acetonitrile as a mobile phase; flow 30 mL/min; (loading pump 4 mL/min acetonitrile); target mass 391; column SunFire 100*19 mm 5 um) to obtain N-(5-methyl-3-pyridyl)-2-[(2S,5R)-5-methyl-2-tetralin-6-yl-1-piperidyl]-2-oxo-acetamide (0.027 g, 68.96 μmol, 4.52% yield).

¹H NMR (400 MHz, DMSO-d₆) δ 1.03 (m, 3H), 1.33 (m, 1H), 1.72 (m, 5H), 1.94 (m, 2H), 2.19 (m, 1H), 2.28 (m, 3H), 2.70 (m, 4H), 2.89 (m, 1H), 3.43 (m, 1H), 5.30 (m, 1H), 7.03 (m, 3H), 7.91 (m, 1H), 8.17 (m, 1H), 8.59 (m, 1H), 11.03 (m, 1H).

LCMS(ESI): [M+H]⁺ m/z: calcd 391.2; found 392.4; Rt=3.68 min.

Example 748. The Synthesis of rac-N-(6-amino-5-methylpyridin-3-yl)-2-((2R,5S)-5-methyl-2-(2-methylpyrimidin-5-yl)piperidin-1-yl)-2-oxoacetamide (Compound 107)

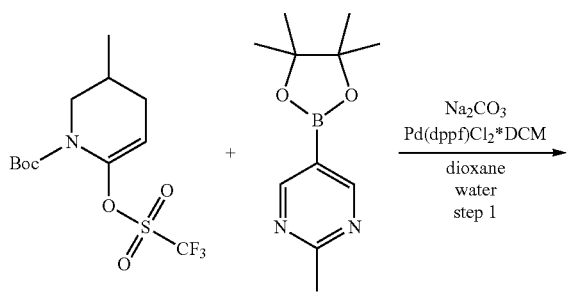

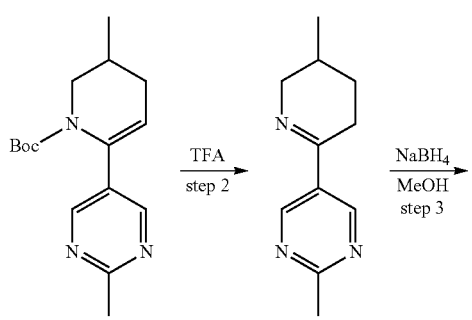

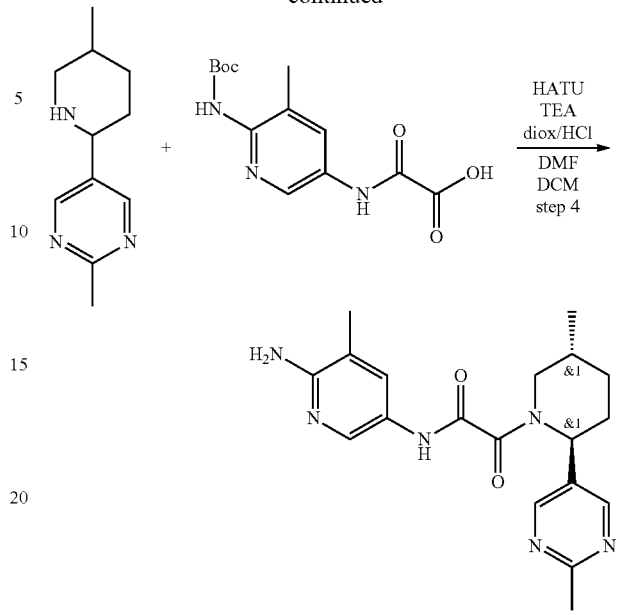

Compound 107

Step 1: Synthesis of tert-butyl 3-methyl-6-(2-methylpyrimidin-5-yl)-3,4-dihydropyridine-1(2H)-carboxylate tert-butyl 3-methyl-6-(trifluoromethylsulfonyloxy)-3,4-dihydro-2H-pyridine-1-carboxylate (9 g, 26.06 mmol), 2-methyl-5-(4,4,5,5-tetramethyl-1,3,2-dioxaborolan-2-yl) pyrimidine (7.17 g, 32.58 mmol) and sodium carbonate (8.29 g, 78.19 mmol, 3.28 mL) were added to a mixture of 1,4-dioxane (75 mL) and water (25 mL). The resulting mixture was evacuated and then backfilled with argon, this operation was repeated three times, then Pd(dppf)Cl₂*DCM (850.65 mg, 1.04 mmol) was added under argon. The reaction mixture was stirred under argon at 70° C. for 12 hr, then cooled and filtered. The filtercake was washed with 1,4-dioxane (2*20 ml) and discarded. The filtrate was evaporated in vacuo, and the residue was purified by column chromatography on silica gel using dichloromethane/MTBE gradient (0-100% MTBE) to afford tert-butyl 3-methyl-6-(2-methylpyrimidin-5-yl)-3,4-dihydro-2H-pyridine-1-carboxylate (4.5 g, 15.55 mmol, 59.67% yield) as light-brown solid.

¹H NMR (500 MHz, CDCl₃) δ (ppm) 0.98 (d, 3H), 1.22 (s, 9H), 1.98 (m, 1H), 2.03 (m, 1H), 2.42 (m, 1H), 2.73 (s, 3H), 3.06 (m, 1H), 4.07 (d, 1H), 5.36 (m, 1H), 8.52 (s, 2H).

LCMS(ESI): [M+1]⁺ m/z: calcd 289.3; found 290.2; Rt=1.389 min.

Step 2: Synthesis of 2-methyl-5-(5-methyl-3,4,5,6-tetrahydropyridin-2-yl)pyrimidine tert-butyl 3-methyl-6-(2-methylpyrimidin-5-yl)-3,4-dihydro-2H-pyridine-1-carboxylate (1.6 g, 5.53 mmol) was dissolved in trifluoroacetic acid (12 g, 105.24 mmol, 8.11 mL). The resulting solution was stirred at 25° C. for 1 hr, then crushed ice was added (20 g) and pH was adjusted to 10 with a solution of sodium hydroxide, pearl (6.63 g, 165.88 mmol, 3.11 mL) in water (50 ml). The resulting cloudy solution was transferred to a separatory funnel and extracted with dichloromethane (2*50 ml). The combined organic extracts were washed with water (20 ml), dried over sodium sulphate and evaporated in vacuo to afford 2-methyl-5-(3-methyl-2,3,4,5-tetrahydropyridin-6-yl)pyrimidine (0.9 g, 4.76 mmol, 86.01% yield) as yellow solid.

$^1$H NMR (400 MHz, CDCl$_3$) δ (ppm) 0.98 (d, 3H), 1.42 (m, 1H), 1.68 (m, 1H), 1.95 (m, 1H), 2.52 (m, 1H), 2.68 (m, 1H), 2.76 (s, 3H), 3.27 (m, 1H), 4.04 (m, 1H), 8.98 (s, 2H).

LCMS(ESI): [M+1]$^+$ m/z: calcd 189.2; found 190.2; Rt=0.682 min.

Step 3: Synthesis of 2-methyl-5-(5-methylpiperidin-2-yl)pyrimidine

Sodium borohydride (107.95 mg, 2.85 mmol, 100.88 µL) was added in one portion to a stirred solution of 2-methyl-5-(3-methyl-2,3,4,5-tetrahydropyridin-6-yl)pyrimidine (0.9 g, 4.76 mmol) in methanol (15 mL) at 0° C. The resulting mixture was stirred at 0° C. for 1 hr, and then evaporated in vacuo. The residue was diluted with water (20 ml) and extracted with dichloromethane (2*40 ml). The combined organic extracts were dried over sodium sulphate and evaporated in vacuo to afford 2-methyl-5-(5-methyl-2-piperidyl) pyrimidine (0.82 g, 4.29 mmol, 90.15% yield) as yellow solid, which was used directly in the next step.

$^1$H NMR (400 MHz, CDCl$_3$) δ (ppm) 0.88 (d, 3H), 1.21 (m, 1H), 1.68 (m, 5H), 2.39 (m, 1H), 2.71 (s, 3H), 3.15 (m, 1H), 3.57 (m, 1H), 8.65 (s, 2H).

LCMS(ESI): [M+1]$^+$ m/z: calcd 191.2; found 192.2; Rt=0.634 min.

Step 4: Synthesis of rac-N-(6-amino-5-methylpyridin-3-yl)-2-((2R,5S)-5-methyl-2-(2-methylpyrimidin-5-yl)piperidin-1-yl)-2-oxoacetamide (Compound 107

TEA (1.16 g, 11.50 mmol, 1.60 mL) was added to a mixture of 2-methyl-5-(5-methyl-2-piperidyl)pyrimidine (220 mg, 1.15 mmol), 2-[[6-(tert-butoxycarbonylamino)-5-methyl-3-pyridyl]amino]-2-oxo-acetic acid (339.64 mg, 1.15 mmol) and HATU (481.07 mg, 1.27 mmol) in DMF (15 mL). The reaction mixture was stirred at 25° C. for 1 hr, and then evaporated in vacuo. The residue was dissolved in DCM (20 mL) and hydrogen chloride solution 4.0 M in dioxane (15.09 g, 57.51 mmol, 18.86 mL, 13.9% purity) was added. The resulting mixture was stirred at 25° C. for 1 hr, and then again evaporated in vacuo. The residue was purified by reverse phase HPLC (column: YMC Triart C18 100×20 mm, 5 um) using 30-40% 0-5 min 0.10% NH$_3$-methanol as mobile phase for first HPLC, and 30-35% 0-6 min 0.1% NH$_3$-MeCN for second HPLC to afford Compound 107 N-(6-amino-5-methyl-3-pyridyl)-2-[(2S,5R)-5-methyl-2-(2-methylpyrimidin-5-yl)-1-piperidyl]-2-oxo-acetamide (20 mg, 54.28 µmol, 4.72% yield) as white solid.

$^1$H NMR (400 MHz, CDCl$_3$) δ (ppm) 1.08 (m, 3H), 1.42 (m, 1H), 1.79 (m, 1H), 1.99 (m, 1H), 2.12 (m, 5H), 2.69 (s, 3H), 3.07 (m, 1H), 4.63 (m, 3H), 6.07 (m, 1H), 7.67 (s, 1H), 8.01 (s, 1H), 8.55 (m, 2H), 9.27 (m, 1H).

LCMS(ESI): [M+1]$^+$ m/z: calcd 368.4; found 369.2; Rt=1.992 min.

Example 749. The Synthesis of rac-N-(6-amino-5-methylpyridin-3-yl)-2-((2R,53)-5-methyl-2-(Pyrimidin-5-yl)piperidin-1-yl)-2-oxoacetamide (Compound 109)

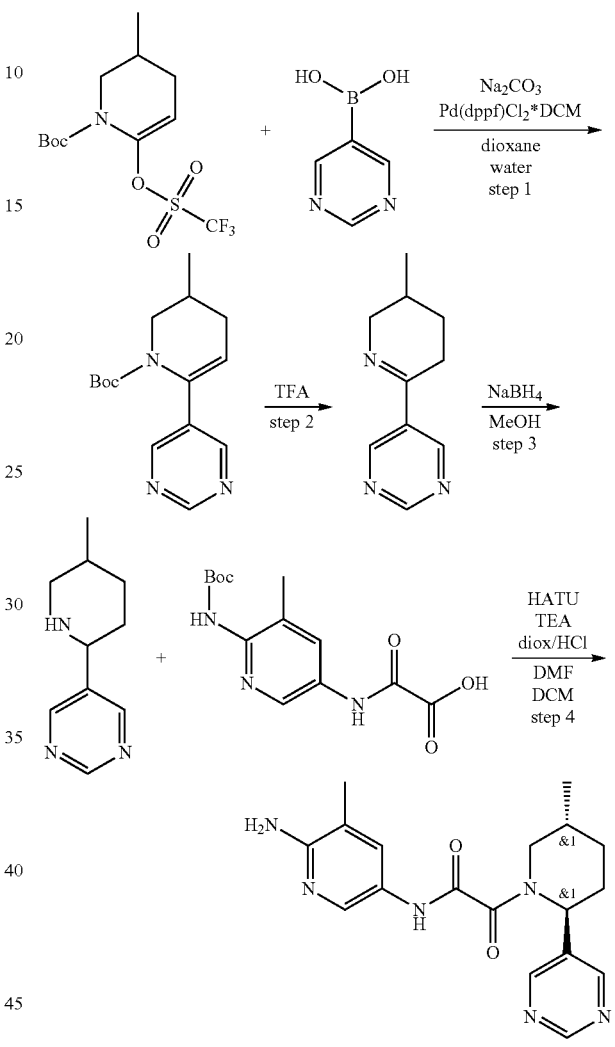

Compound 109

Step 1: Synthesis of tert-butyl 3-methyl-6-(Pyrimidin-5-yl)-3,4-dihydropyridine-1(2H)-carboxylate tert-butyl 3-methyl-6-(trifluoromethylsulfonyloxy)-3,4-dihydro-2H-pyridine-1-carboxylate (7 g, 20.27 mmol), pyrimidin-5-ylboronic acid (3.27 g, 26.35 mmol) and sodium carbonate (6.45 g, 60.81 mmol, 2.55 mL) were added to a mixture of 1,4-dioxane (90 mL) and water (30 mL). The resulting mixture was evacuated and then back-filled with argon, this operation was repeated three times, then Pd(dppf)Cl$_2$*DCM (827.02 mg, 1.01 mmol) was added under argon. The reaction mixture was stirred under argon at 75° C. for 12 hr, then cooled and filtered. The filtercake was washed with 1,4-dioxane (2*20 ml) and discarded. The filtrate was evaporated in vacuo, and the residue was purified by column chromatography on silica gel using DCM/MTBE gradient (0-100% MTBE) to afford tert-butyl 3-methyl-6- pyrimidin-5-yl-3,4-dihydro-2H-pyridine-1-carboxylate (3.3 g, 11.98 mmol, 59.13% yield) as light-brown solid.

$^1$H NMR (500 MHz, CDCl$_3$) δ (ppm) 1.03 (d, 3H), 1.21 (s, 9H), 1.98 (m, 1H), 2.04 (m, 1H), 2.42 (m, 1H), 3.07 (m, 1H), 4.08 (m, 1H), 5.41 (d, 1H), 8.64 (s, 2H), 9.09 (s, 1H). LCMS(ESI): [M+1]$^+$ m/z: calcd 275.3; found 276.2; Rt=1.371 min.

Step 2: Synthesis of 5-(5-methyl-3,4,5,6-tetrahydro-pyridin-2-yl)pyrimidine tert-butyl 3-methyl-6-pyrimidin-5-yl-3,4-dihydro-2H-pyridine-1-carboxylate (1.7 g, 6.17 mmol) was dissolved in trifluoroacetic acid (14.08 g, 123.48 mmol, 9.51 mL). The resulting solution was stirred at 25° C. for 1 hr, then crushed ice was added (20 g) and pH was adjusted to 10 with a solution of sodium hydroxide, pearl (7.41 g, 185.22 mmol, 3.48 mL) in water (50 ml). The resulting cloudy solution was transferred to a separatory funnel and extracted with dichloromethane (2*50 ml). The combined organic extracts were washed with water (20 ml), dried over sodium sulphate and evaporated in vacuo to afford 5-(3-methyl-2,3,4,5-tetrahydropyridin-6-yl)pyrimidine (1 g, 5.71 mmol, 92.43% yield) as yellow oil, which was used directly in the next step.

$^1$H NMR (500 MHz, CDCl$_3$) δ (ppm) 1.02 (d, 3H), 1.46 (m, 1H), 1.69 (m, 1H), 1.95 (m, 1H), 2.59 (m, 1H), 2.75 (m, 1H), 3.28 (m, 1H), 4.05 (m, 1H), 9.08 (s, 2H), 9.21 (s, 1H). LCMS(ESI): [M+1]$^+$ m/z: calcd 175.2; found 176.2; Rt=0.555 min.

Step 3: Synthesis of 5-(5-methylpiperidin-2-yl)pyrimidine

Sodium borohydride (129.53 mg, 3.42 mmol, 121.06 μL) was added in one portion to a stirred solution of 5-(3-methyl-2,3,4,5-tetrahydropyridin-6-yl)pyrimidine (1 g, 5.71 mmol) in methanol (15 mL) at 0° C. The resulting mixture was stirred at 0° C. for 1 hr, and then evaporated in vacuo. The residue was diluted with water (20 ml) and extracted with DCM (2*40 ml). The combined organic extracts were dried over sodium sulphate and evaporated in vacuo to afford 5-(5-methyl-2-piperidyl)pyrimidine (0.8 g, 4.51 mmol, 79.09% yield) as yellow solid, which was used directly in the next step.

$^1$H NMR (500 MHz, CDCl$_3$) δ (ppm) 0.88 (d, 3H), 1.21 (m, 1H), 1.68 (m, 5H), 2.44 (m, 1H), 3.17 (m, 1H), 3.61 (m, 1H), 8.75 (s, 2H), 9.11 (s, 1H). LCMS(ESI): [M+1]$^+$ m/z: calcd 177.2; found 178.2; Rt=0.573 min.

Step 4: Synthesis of rac-N-(6-amino-5-methylpyridin-3-yl)-2-((2R,5S)-5-methyl-2-(Pyrimidin-5-yl)piperidin-1-yl)-2-oxoacetamide (Compound 109

TEA (1.43 g, 14.10 mmol, 1.97 mL) was added to a mixture of 5-(5-methyl-2-piperidyl)pyrimidine (0.25 g, 1.41 mmol), 2-[[6-(tert-butoxycarbonylamino)-5-methyl-3-pyridyl]amino]-2-oxo-acetic acid (458.15 mg, 1.55 mmol) and HATU (589.93 mg, 1.55 mmol) in DMF (15 mL). The reaction mixture was stirred at 25° C. for 1 hr, and then evaporated in vacuo. The residue was dissolved in DCM (20 mL) and hydrogen chloride solution 4.0 M in dioxane (18.50 g, 70.52 mmol, 23.12 mL, 13.9% purity) was added. The resulting mixture was stirred at 25° C. for 1 hr, and then again evaporated in vacuo. The residue was purified by reverse phase HPLC (column: YMC Triart C18 100×20 mm, 5 um) using 30-30-50% 0-1-5 min 0.1% NH$_3$-methanol as mobile phase to afford Compound 109 N-(6-amino-5-methyl-3-pyridyl)-2-[(2S,5R)-5-methyl-2-pyrimidin-5-yl-1-piperidyl]-2-oxo-acetamide (80 mg, 225.73 μmol, 16.00% yield) as light-yellow foam.

$^1$H NMR (400 MHz, CDCl$_3$) δ (ppm) 1.10 (m, 3H), 1.44 (m, 1H), 1.84 (m, 1H), 2.01 (m, 1H), 2.11 (m, 3H), 2.24 (m, 2H), 3.08 (m, 1H), 4.69 (m, 3H), 6.16 (m, 1H), 7.69 (s, 1H), 8.03 (s, 1H), 8.69 (m, 2H), 9.18 (m, 2H).
LCMS(ESI): [M+1]$^+$ m/z: calcd 354.4; found 355.2; Rt=1.830 min.

Example 750. The Synthesis of N-(6-amino-5-methyl-3-pyridyl)-2-[(2R,5S)-2-[4-(1-hydroxy-1-methyl-ethyl)phenyl]-5-methyl-1-piperidyl]-2-oxo-acetamide (Compound 672)

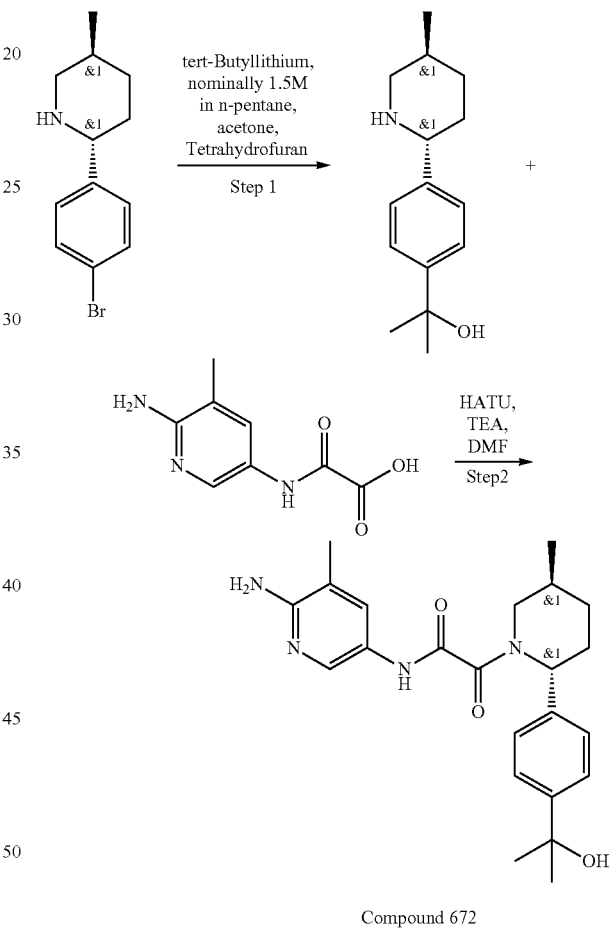

Compound 672

Step 1: Synthesis of 2-[4-[(2R,5S)-5-methyl-2-piperidyl]phenyl]propan-2-ol

To a stirred solution of (2R,5S)-2-(4-bromophenyl)-5-methyl-piperidine (300 mg, 1.18 mmol) in Tetrahydrofuran (10 mL) at −80° C., tert-butyllithium, nominally 1.5M in n-pentane (1.65 g, 3.78 mmol, 2.52 mL, 14.7% purity) was added dropwise under argon atmosphere. The resulting solution was stirred at the same temperature for 40 min minutes. Then, acetone (274.21 mg, 4.72 mmol, 346.66 μL) was added to the solution dropwise. The resulting reaction mixture was allowed to warm to room temperature and quenched with 20% aq. NH$_4$Cl solution (15 ml). Resulting mixture was extracted with ethyl acetate (20 ml). Organic layer was separated, dried over Na$_2$SO$_4$ and evaporated under reduced pressure, affording 2-[4-[(2R,5S)-5-methyl-2-piperidyl]phenyl]propan-2-ol (290 mg, crude).

$^1$H NMR (CDCl$_3$, 400 MHz): 0.85 (d, 3H), 1.28 (m, 2H), 1.23 (s, 3H), 1.55 (s, 3H), 1.88 (m, 1H), 1.87 (m, 2H), 2.39 (t, 1H), 2.60 (s, 1H), 3.10 (m, 1H), 3.53 (m, 1H), 7.34 (m, 2H), 7.42 (m, 2H), NH is not observed.

LCMS(ESI): [M+H]$^+$ m/z: calcd 233.2; found 234.2; Rt=0.843 min.

Step 2: Synthesis of N-(6-amino-5-methyl-3-pyridyl)-2-[(2R,5S)-2-[4-(1-hydroxy-1-methyl-ethyl)phenyl]-5-methyl-1-piperidyl]-2-oxo-acetamide (Compound 672

To a stirred mixture of 2-[4-[(2R,5S)-5-methyl-2-piperidyl]phenyl]propan-2-ol (290 mg, 1.24 mmol), 2-[(6-amino-5-methyl-3-pyridyl)amino]-2-oxo-acetic acid (260 mg, 1.33 mmol) and Triethylamine (251.51 mg, 2.49 mmol, 346.44 µL) in Dimethylformamide (3 mL) was added HATU (519.80 mg, 1.37 mmol). The resulting reaction mixture was stirred at 20° C. for 4 hr. Then, it was subjected to HPLC (Column: YMC-Actus Triart C18 100*20 mm I.D. S-5 um; 0-5 min 20-70% water-MeOH(NH$_3$ 0.1%), flow 30 ml/min), affording N-(6-amino-5-methyl-3-pyridyl)-2-[(2R,5S)-2-[4-(1-hydroxy-1-methyl-ethyl)phenyl]-5-methyl-1-piperidyl]-2-oxo-acetamide (200 mg, 487.20 µmol, 39.20% yield).

$^1$H NMR (DMSO-d$_6$, 600 MHz): δ (ppm) 1.00 (m, 3H), 1.39 (m, 8H), 1.67 (m, 1H), 1.85 (m, 1H), 1.97 (m, 4H), 2.21 (m, 1H), 2.70 (m, 1H), 3.61 (m, 1H), 4.95 (s, 1H), 5.57 (m, 3H), 7.23 (m, 2H), 7.46 (m, 3H), 7.98 (m, 1H), 10.47 (m, 1H)

LCMS(ESI): [M+H]$^+$ m/z: calcd 410.3; found 411.2; Rt=1.475 min.

Example 751. The Synthesis of N-(6-amino-5-methyl-3-pyridyl)-2-[(2R,5S)-2-[4-(1-hydroxyethyl)phenyl]-5-methyl-1-piperidyl]-2-oxo-acetamide (Compound 956)

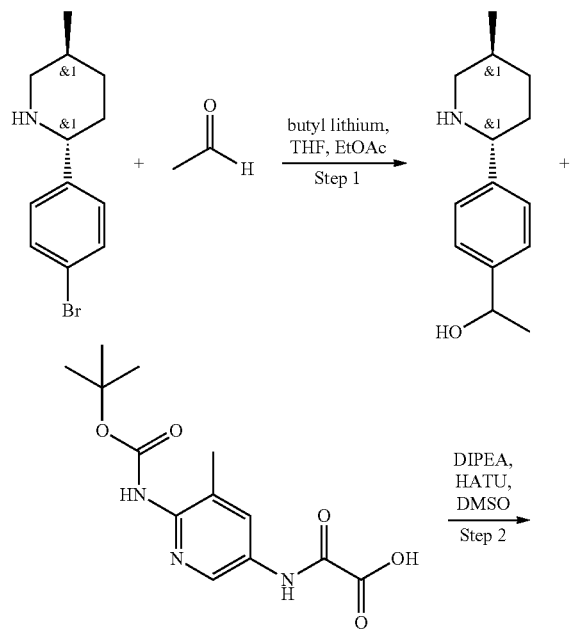

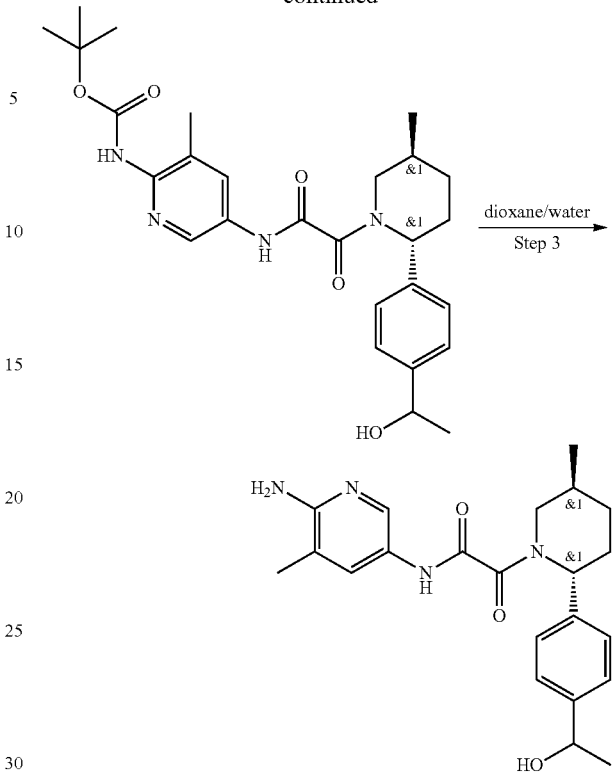

Compound 956

Step 1: Synthesis of 1-[4-[(2R,5S)-5-methyl-2-piperidyl]phenyl]ethanol (2R,5S)-2-(4-bromophenyl)-5-methyl-piperidine (0.5 g, 1.97 mmol) was dissolved in THF (10 mL) and cooled to, followed by the addition of butyl lithium (2.5 M, 786.89 µL) and stirring for 10 min. After short delay, acetaldehyde (173.32 mg, 3.93 mmol) was added in one portion and the reaction mixture was slowly warmed to 0° C., poured on sat aq NH$_4$Cl and extracted with EtOAc (20 mL). Evaporation of the organic solvents results in crude 1-[4-[(2R,5S)-5-methyl-2-piperidyl]phenyl]ethanol (0.5 g, crude) which was used in the next step without purification.

LCMS(ESI): [M+H]$^+$ m/z: calcd 219.2; found 220.2; Rt=0.701 min.

Step 2: Synthesis of tert-butyl N-[5-[[2-[(2R,5S)-2-[4-(1-hydroxyethyl)phenyl]-5-methyl-1-piperidyl]-2-oxo-acetyl]amino]-3-methyl-2-pyridyl]carbamate 2-[[6-(tert-butoxycarbonylamino)-5-methyl-3-pyridyl]amino]-2-oxo-acetic acid (419.24 mg, 1.42 mmol), 1-[4-[(2R,5S)-5-methyl-2-piperidyl]phenyl]ethanol (311.39 mg, 1.42 mmol, 185.76 µL) and DIPEA (550.47 mg, 4.26 mmol, 741.88 µL) were dissolved in DMSO (6 mL) under gentle heating. HATU (647.81 mg, 1.70 mmol) was added in small portions under vigorous stirring and occasional heating. After the reaction was complete, the mixture was purified by HPLC (34-40% 0.5-5.5 min water-acetonitrile; flow 30 ml/min (loading pump 4 ml/min acetonitrile); target mass 496; column SunFire C18 100×19 mm 5 um (R)) to give tert-butyl N-[5-[[2-[(2R,5S)-2-[4-(1-hydroxyethyl)phenyl]-

5-methyl-1-piperidyl]-2-oxo-acetyl]amino]-3-methyl-2-pyridyl]carbamate (90 mg, 181.23 µmol, 12.76% yield).

LCMS(ESI): [M+H]⁺ m/z: calcd 496.3; found 497.2; Rt=3.130 min.

Step 3: Synthesis of N-(6-amino-5-methyl-3-pyridyl)-2-[(2R,5S)-2-[4-(1-hydroxyethyl)phenyl]-5-methyl-1-piperidyl]-2-oxo-acetamide (Compound 956 tert-butyl N-[5-[[2-[(2R,5S)-2-[4-(1-hydroxyethyl)phenyl]-5-methyl-1-piperidyl]-2-oxo-acetyl]amino]-3-methyl-2-pyridyl]carbamate (80 mg, 136.93 µmol) was dissolved in dioxane (3 mL) and h2o (1 mL). Obtained solution was stirred at 100° C. for 3 hr; after the reaction was complete, the mixture was subjected to HPLC (19% 0.5-6.5 min water-acetonitrile; flow 30 ml/min (loading pump 4 ml/min acetonitrile); target mass 396; column SunFire C18 100×19 mm 5 um (R)) to give N-(6-amino-5-methyl-3-pyridyl)-2-[(2R,5S)-2-[4-(1-hydroxyethyl)phenyl]-5-methyl-1-piperidyl]-2-oxo-acetamide (35 mg, 88.28 µmol, 64.47% yield)

¹H NMR (600 MHz, DMSO-d₆) δ 0.97-1.01 (m, 3H), 1.27-1.33 (m, 4H), 1.60-1.67 (m, 1H), 1.80-1.90 (m, 1H), 1.95-2.04 (m, 4H), 2.15-2.25 (m, 1H), 2.67-3.21 (m, 1H), 3.39-4.03 (m, 1H), 4.67-5.10 (m, 2H), 5.55 (s, 1H), 5.56-5.63 (m, 2H), 7.19-7.28 (m, 2H), 7.29-7.35 (m, 2H), 7.41-7.50 (m, 1H), 7.93-8.04 (m, 1H), 10.47 (s, 1H).

LCMS(ESI): [M+H]⁺ m/z: calcd 396.3; found 397.2; Rt=1.997 min.

Example 752. The Synthesis of N-(6-amino-5-methylpyridin-3-yl)-2-((2R,5S)-5-methyl-2-(3,4,5-trifluorophenyl)piperidin-1-yl)-2-oxoacetamide (Compound 478)

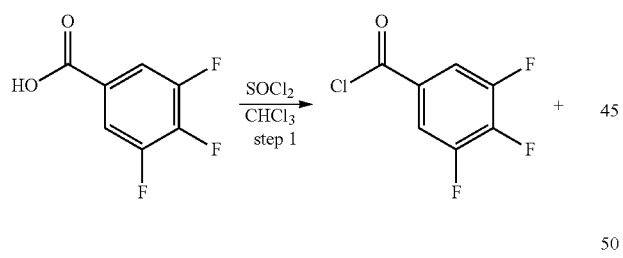

Step 1: Synthesis of 3,4,5-trifluorobenzoyl chloride 3,4,5-trifluorobenzoic acid (25 g, 141.97 mmol) was added portions to a stirred solution thionyl chloride (50.67 g, 425.91 mmol) in CHCl₃ (100 mL). The resulting mixture was stirred at 68° C. for 15 hr, and then evaporated in vacuo. The residue was poured in hexane (200 ml) and filtrated. The filtrated were dried and evaporated in vacuo to afford 3,4,5-trifluorobenzoyl chloride (22.1 g, 113.60 mmol, 80.02% yield).

$^1$H NMR (400 MHz, CDCl$_3$) δ (ppm) 7.79 (s, 2H).

LCMS(ESI): [M]$^+$ m/z: calcd 194.2; found 195.2; Rt=1.205 min.

Step 2: Synthesis of (5S)-tert-butyl 5-methyl-2-oxo-3-(3,4,5-trifluorobenzoyl)piperidine-1-carboxylate To a solution of tert-butyl (5S)-5-methyl-2-oxo-piperidine-1-carboxylate (4.1 g, 19.22 mmol) in THF (100 mL) at −78° C. was added sodium bis(trimethylsilyl)amide, 98% (7.76 g, 42.29 mmol, 27 mL) dropwise under Ar atmosphere. The resulting mixture was left to stir for 1 hr. 3,4,5-trifluorobenzoyl chloride (4.11 g, 21.15 mmol) was added dropwise to the t-boc-lactam maintaining the internal temperature below −70° C. The solution was warmed to room temperature and was added sodium bisulfate (10.16 g, 84.59 mmol) in water (20 mL) dropwise. The aqueous layer was extracted 3×50 mL with EtOAc and the organic layers combined, dried over Na$_2$SO$_4$, filtered and concentrated in vacuo. tert-butyl (5S)-5-methyl-2-oxo-3-(3,4,5-trifluorobenzoyl)piperidine-1-carboxylate (10.2 g, crude) was obtained as a yellow oil and was used in the next step without further purification.

$^1$H NMR (400 MHz, CDCl$_3$) δ (ppm) 1.02 (d, 3H), 1.56 (s, 9H), 2.24 (m, 3H), 3.26 (m, 2H), 3.96 (m, 1H), 7.17 (s, 1H), 7.72 (s, 1H).

LCMS(ESI): [M−Boc]$^+$ m/z: calcd 271.2; found 272.2; Rt=1.617 min.

Step 3: Synthesis of (S)-3-methyl-6-(3,4,5-trifluorophenyl)-2,3,4,5-tetrahydropyridine tert-butyl (5S)-5-methyl-2-oxo-3-(3,4,5-trifluorobenzoyl)piperidine-1-carboxylate (10.2 g, 27.47 mmol) was dissolved in hydrogen chloride (40 mL) and CH$_3$COOH (30 mL) was added portion wise. After addition was complete, resulting mixture was stirred at 110° C. for 16 hr. Then, solvents were removed under reduced pressure and residue was partitioned between 1N HCl (150 ml) and DCM (30 ml). Organic layer was separated and discarded. Aqueous layer was basified to ph≈9 with 10% NaHCO$_3$ and extracted with DCM (2×60 ml). DCM solution was separated, dried over K$_2$CO$_3$ and evaporated under reduced pressure, affording (3S)-3-methyl-6-(3,4,5-trifluorophenyl)-2,3,4,5-tetrahydropyridine (4.2 g, 18.48 mmol, 67.29% yield).

Step 4: Synthesis of (2R,5S)-5-methyl-2-(3,4,5-trifluorophenyl)piperidine

Sodium borohydride (1.40 g, 36.97 mmol, 1.31 mL) was added in one portion to a stirred solution of (3S)-3-methyl-6-(3,4,5-trifluorophenyl)-2,3,4,5-tetrahydropyridine (4.2 g, 18.48 mmol) in MeOH (50 mL) at 0° C. The resulting mixture was stirred at 0° C. for 4 hr, and then evaporated in vacuo. The residue was diluted with water (20 mL) and extracted with DCM (2*50 mL). The combined organic extracts were dried over sodium sulphate and evaporated in vacuo to afford (2R,5S)-5-methyl-2-(3,4,5-trifluorophenyl)piperidine (4.1 g, 17.89 mmol, 96.76% yield).

$^1$H NMR (500 MHz, CDCl$_3$) δ (ppm) 0.88 (d, 3H), 1.14 (m, 1H), 1.48 (m, 1H), 1.65 (m, 2H), 1.87 (m, 2H), 2.38 (t, 1H), 3.13 (d, 1H), 3.49 (d, 1H), 7.02 (s, 2H).

LCMS(ESI): [M]$^+$ m/z: calcd 229.2; found 230.2; Rt=0.618 min.

Step 5: Synthesis of tert-butyl (3-methyl-5-(2-(5-methyl-2-(3,4,5-trifluorophenyl)piperidin-1-yl)-2-oxoacetamido)pyridin-2-yl)carbamate 2-[[6-(tert-butoxycarbonylamino)-5-methyl-3-pyridyl]amino]-2-oxo-acetic acid (5.28 g, 17.89 mmol) and 5-methyl-2-(3,4,5-trifluorophenyl)piperidine (4.1 g, 17.89 mmol) were mixed in DMF (100 mL). The reaction suspension was cooled to 0° C. and HATU (8.84 g, 23.25 mmol) followed by TEA (5.43 g, 53.66 mmol, 7.48 mL) were added and stirred at ambient temperature for 14 hr. The reaction mixture was evaporated in vacuo and poured into water (300 ml) and extracted with EtOAc (2×100 ml). The combined organic extracts were washed with water (2*50 ml), dried over sodium sulphate and evaporated in vacuo to leave 8.2 g of crude product, 8.2 g of which was purification by column chromatography on silica gel using hexane/MTBE gradient (10-100% MTBE) to afford product tert-butyl N-[3-methyl-5-[[2-[5-methyl-2-(3,4,5-trifluorophenyl)-1-piperidyl]-2-oxo-acetyl]amino]-2-pyridyl]carbamate (5.5 g, 10.86 mmol, 60.71% yield).

$^1$H NMR (400 MHz, CDCl$_3$) δ (ppm) 1.12 (d, 3H), 1.56 (s, 9H), 1.98 (m, 1H), 2.24 (s, 3H), 2.36 (m, 5H), 3.12 (m, 1H), 4.68 (m, 1H), 6.20 (m, 1H), 6.98 (m, 2H), 8.32 (m, 2H), 9.48 (m, 1H).

LCMS(ESI): [M]$^+$ m/z: calcd 506.2; found 507.2; Rt=1.477 min.

Step 6: Chiral Separation

The tert-butyl N-[3-methyl-5-[[2-[5-methyl-2-(3,4,5-trifluorophenyl)-1-piperidyl]-2-oxo-acetyl]amino]-2-pyridyl]carbamate (10.5 g, 20.73 mmol) (with ~10% cis izomer) was subjected to chiral HPLC purification (Column: AD-H III (250*30 mm, 20 um), Eluent:CO$_2$-MeOH, 60-40, 90 ml/min make up flow rate −30 ml/min) to obtain pure product tert-butyl N-[3-methyl-5-[[2-[(2R,5S)-5-methyl-2-(3,4,5-trifluorophenyl)-1-piperidyl]-2-oxo-acetyl]amino]-2-pyridyl]carbamate (6.1 g, 12.04 mmol, 58.10% yield) as a white solid.

Retention time: 5.59 min $^1$H NMR (500 MHz, CDCl$_3$) δ (ppm) 1.09 (d, 3H), 1.41 (m, 1H), 1.56 (s, 9H), 1.86 (m, 1H), 2.04 (m, 2H), 2.28 (m, 1H), 2.31 (s, 3H), 3.26 (m, 1H), 4.68 (m, 1H), 6.20 (m, 1H), 6.71 (m, 1H), 6.90 (m, 2H), 8.03 (m, 1H), 8.38 (m, 1H), 9.32 (m, 1H).

LCMS(ESI): [M]$^+$ m/z: calcd 506.2; found 507.2; Rt=1.354 min.

Step 7: Synthesis of N-(6-amino-5-methylpyridin-3-yl)-2-((2R,5S)-5-methyl-2-(3,4,5-trifluorophenyl)piperidin-1-yl)-2-oxoacetamide (Compound 478

Water (50 mL) was added to a stirred solution of tert-butyl N-[3-methyl-5-[[2-[(2R,5S)-5-methyl-2-(3,4,5-trifluorophenyl)-1-piperidyl]-2-oxo-acetyl]amino]-2-pyridyl]carbamate (6.1 g, 12.04 mmol) in dioxane (100 mL) at rt. The resulting mixture was stirred at 95° C. for 15 hr, and then evaporated in vacuo to leave 4.75 g of crude product, 4.75 g of which was purification by column chromatography on silica gel using MTBE/MeOH gradient (10-100% MeOH) to afford pure product 4.3 g, which was diluted with MeOH, evaporated in rotary evaporator at 30° C. and then dried under oil pump (0.5 mm Hg) at 35° C. for 12 hr to obtain pure product 5-[[2-[(2R,5S)-2-(4-fluorophenyl)-5-methyl-1-piperidyl]-2-oxo-acetyl]amino]pyridine-3-carboxamide (23.4 g, 60.87 mmol, 66.29% yield) Compound 478 as a white solid. a21D=+103.2 (EtOH, 0.25 M)

$^1$H NMR (600 MHz, DMSO-$d_6$) δ (ppm) 0.96-1.01 (m, 3H), 1.25-1.36 (m, 1H), 1.56-1.69 (m, 1H), 1.81-1.93 (m, 1H), 1.97-2.09 (m, 4H), 2.11-2.23 (m, 1H), 2.72-3.24 (m, 1H), 3.38-4.02 (m, 1H), 5.05-5.49 (m, 1H), 5.57-5.66 (m, 2H), 7.20-7.32 (m, 2H), 7.42-7.50 (m, 1H), 7.93-8.02 (m, 1H), 10.42-10.60 (m, 1H).

LCMS(ESI): [M]$^+$ m/z: calcd 406.2; found 407.2; Rt=1.752 min.

Example 753. The Synthesis of N-(6-amino-5-methyl-3-pyridyl)-2-[2-(1-methylbenzimidazol-4-yl)-1-piperidyl]-2-oxo-acetamide (Compound 132)

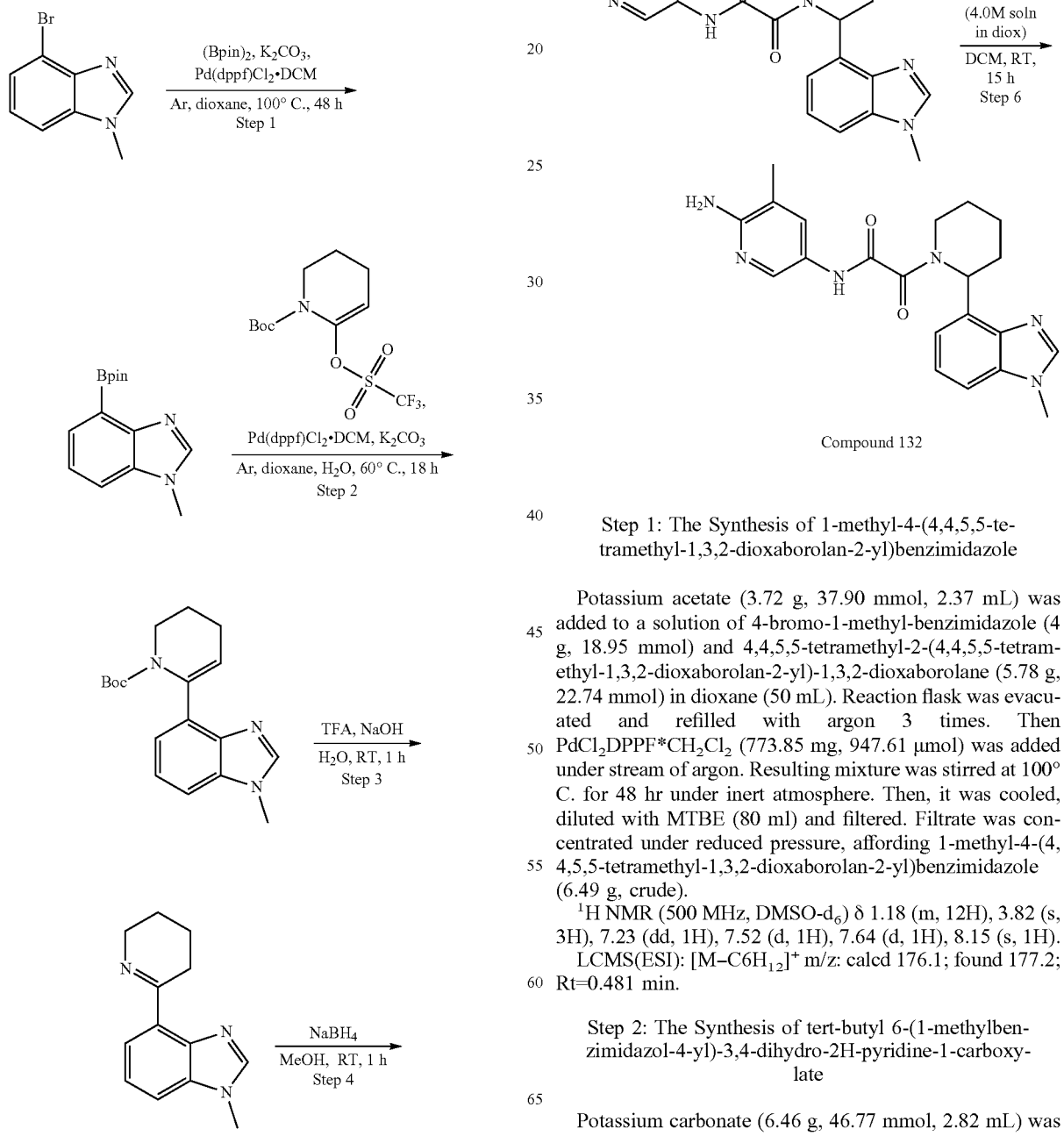

Compound 132

Step 1: The Synthesis of 1-methyl-4-(4,4,5,5-tetramethyl-1,3,2-dioxaborolan-2-yl)benzimidazole Potassium acetate (3.72 g, 37.90 mmol, 2.37 mL) was added to a solution of 4-bromo-1-methyl-benzimidazole (4 g, 18.95 mmol) and 4,4,5,5-tetramethyl-2-(4,4,5,5-tetramethyl-1,3,2-dioxaborolan-2-yl)-1,3,2-dioxaborolane (5.78 g, 22.74 mmol) in dioxane (50 mL). Reaction flask was evacuated and refilled with argon 3 times. Then PdCl$_2$DPPF*CH$_2$Cl$_2$ (773.85 mg, 947.61 µmol) was added under stream of argon. Resulting mixture was stirred at 100° C. for 48 hr under inert atmosphere. Then, it was cooled, diluted with MTBE (80 ml) and filtered. Filtrate was concentrated under reduced pressure, affording 1-methyl-4-(4,4,5,5-tetramethyl-1,3,2-dioxaborolan-2-yl)benzimidazole (6.49 g, crude).

$^1$H NMR (500 MHz, DMSO-$d_6$) δ 1.18 (m, 12H), 3.82 (s, 3H), 7.23 (dd, 1H), 7.52 (d, 1H), 7.64 (d, 1H), 8.15 (s, 1H).
LCMS(ESI): [M–C$_6$H$_{12}$]$^+$ m/z: calcd 176.1; found 177.2; Rt=0.481 min.

Step 2: The Synthesis of tert-butyl 6-(1-methylbenzimidazol-4-yl)-3,4-dihydro-2H-pyridine-1-carboxylate Potassium carbonate (6.46 g, 46.77 mmol, 2.82 mL) was added to a solution of 1-methyl-4-(4,4,5,5-tetramethyl-1,3, 2-dioxaborolan-2-yl)benzimidazole (6.49 g, 15.59 mmol) and tert-butyl 6-(trifluoromethylsulfonyloxy)-3,4-dihydro-2H-pyridine-1-carboxylate (6.18 g, 17.15 mmol) in Dioxane (50 mL) and Water (15 mL). Reaction flask was evacuated and refilled with argon 3 times. Then, PdCl$_2$DPPF*CH$_2$Cl$_2$ (636.51 mg, 779.43 μmol) was added under stream of argon. Resulting mixture was stirred at 60° C. for 18 hr under inert atmosphere. Then, solvent was removed under reduced pressure and residue was purified by column chromatography (RediSep Column: 330 g; 22-38% chloroform-MeCN; flow fate: 90 ml/min), affording tert-butyl 6-(1-methylbenzimidazol-4-yl)-3,4-dihydro-2H-pyridine-1-carboxylate (4.1 g, 13.08 mmol, 83.92% yield).

$^1$H NMR (500 MHz, DMSO-d$_6$) δ 1.02 (s, 9H), 1.24 (m, 1H), 1.40 (m, 1H), 1.66 (m, 2H), 1.95 (s, 3H), 2.37 (m, 1H), 3.83 (m, 1H), 5.75 (m, 1H), 7.26 (m, 3H), 7.84 (s, 1H).

LCMS(ESI): [M+H]$^+$ m/z: calcd 313.2; found 314.2; Rt=0.986 min.

Step 3: The Synthesis of 1-methyl-4-(2,3,4,5-tetrahydropyridin-6-yl)benzimidazole tert-butyl 6-(1-methylbenzimidazol-4-yl)-3,4-dihydro-2H-pyridine-1-carboxylate (4.1 g, 13.08 mmol) was dissolved in trifluoroacetic acid (22.38 g, 196.24 mmol, 15.12 mL). Resulting solution was stirred at 25° C. for 1 hr. Then, it was poured into ice-cold solution of sodium hydroxide (10.47 g, 261.65 mmol, 4.91 mL) in water (150 ml). Resulting mixture was extracted with DCM (4*30 ml). After drying over Na$_2$SO$_4$, solvent was removed under reduced pressure, affording 1-methyl-4-(2,3,4,5-tetrahydropyridin-6-yl)benzimidazole (2.1 g, 9.85 mmol, 75.26% yield).

$^1$H NMR (400 MHz, CDCl$_3$) δ 1.21 (m, 1H), 1.74 (m, 2H), 1.88 (m, 2H), 2.30 (m, 1H), 3.09 (m, 1H), 3.88 (s, 3H), 5.27 (m, 1H), 7.31 (m, 2H), 7.57 (d, 1H), 7.87 (s, 1H).

LCMS(ESI): [M+H]$^+$ m/z: calcd 213.1; found 214.2; Rt=0.818 min.

Step 4: The Synthesis of 1-methyl-4-(2-piperidyl)benzimidazole 1-methyl-4-(2,3,4,5-tetrahydropyridin-6-yl)benzimidazole (2.1 g, 9.85 mmol) was dissolved in methanol (40 mL), and sodium borohydride (744.97 mg, 19.69 mmol, 696.23 μL) was added portionwise during 20 min. After addition was complete, resulting mixture was stirred at 25° C. for 1 hr. Then, it was concentrated under reduced pressure and residue was partitioned between water (20 ml) and EtOAc (40 ml). Organic layer was separated, dried over Na$_2$SO$_4$ and acidified with 4M Diox/HCl. Resulting precipitate was filtered and dried, affording 1-methyl-4-(2-piperidyl)benzimidazole (2.18 g, 7.56 mmol, 76.82% yield, 2HCl).

$^1$H NMR (400 MHz, DMSO-d$_6$) δ 1.04 (m, 1H), 1.85 (m, 6H), 3.10 (m, 1H), 3.42 (m, 1H), 4.05 (s, 3H), 5.12 (m, 1H), 7.66 (dd, 1H), 7.95 (m, 2H), 9.57 (s, 1H), 10.01 (m, 2H).

LCMS(ESI): [M+H]$^+$ m/z: calcd 215.1; found 216.1; Rt=0.748 min.

Step 5: The Synthesis of tert-butyl N-[3-methyl-5-[[2-[2-(1-methylbenzimidazol-4-yl)-1-piperidyl]-2-oxo-acetyl]amino]-2-pyridyl]carbamate 2-[[6-(tert-butoxycarbonylamino)-5-methyl-3-pyridyl]amino]-2-oxo-acetic acid (205.74 mg, 696.72 μmol), HATU (291.41 mg, 766.39 μmol) and triethylamine (352.51 mg, 3.48 mmol, 485.55 μL) were mixed together in dimethylformamide (1.5 mL) and 1-methyl-4-(2-piperidyl)benzimidazole (150 mg, 696.72 μmol, 2HCl) was added. Resulting mixture was stirred at 25° C. for 15 hr. Then, it was diluted with water (10 ml) and extracted with ethyl acetate (2*15 ml). Organic layer was washed with water (3*10 ml) and brine (20 ml), dried over Na$_2$SO$_4$ and concentrated in vacuo, affording tert-butyl N-[3-methyl-5-[[2-[2-(1-methylbenzimidazol-4-yl)-1-piperidyl]-2-oxo-acetyl]amino]-2-pyridyl]carbamate (170 mg, 345.13 μmol, 49.54% yield).

LCMS(ESI): [M+2H]$^+$ m/z: calcd 492.2; found 494.2; Rt=1.048 min.

Step 6: The Synthesis of N-(6-amino-5-methyl-3-pyridyl)-2-[2-(1-methylbenzimidazol-4-yl)-1-piperidyl]-2-oxo-acetamide (Compound 132

Hydrogen chloride solution 4.0M in dioxane (1.52 g, 4.16 mmol, 1.5 mL, 10% purity) was added to a solution of tert-butyl N-[3-methyl-5-[[2-[2-(1-methylbenzimidazol-4-yl)-1-piperidyl]-2-oxo-acetyl]amino]-2-pyridyl]carbamate (170 mg, 345.13 μmol) in Dichloromethane (2 mL). Resulting mixture was stirred at 25° C. for 15 hr. Then, it was concentrated under reduced pressure and residue was subjected to HPLC (column: YMC-Actus Triart C18 100*20 mm, 5 um; 0-5 min 20-70% water-methanol (NH$_3$ 0.1%), flow 30 ml/min), affording N-(6-amino-5-methyl-3-pyridyl)-2-[2-(1-methylbenzimidazol-4-yl)-1-piperidyl]-2-oxo-acetamide (26 mg, 66.25 μmol, 19.20% yield).

$^1$H NMR (400 MHz, DMSO-d$_6$) δ 1.30 (m, 2H), 1.61 (m, 2H), 1.91 (m, 1H), 2.01 (m, 3H), 2.91 (m, 1H), 3.47 (m, 1H), 3.85 (m, 3H), 4.15 (m, 1H), 5.76 (m, 3H), 7.10 (m, 1H), 7.28 (m, 1H), 7.50 (m, 2H), 7.98 (m, 1H), 8.24 (m, 1H), 10.70 (d, 1H).

LCMS(ESI): [M+H]$^+$ m/z: calcd 392.2; found 393.2; Rt=1.766 min.

Example 754. The Synthesis of N-(6-amino-5-methyl-3-pyridyl)-2-[2-(1H-benzimidazol-4-yl)-1-piperidyl]-2-oxo-acetamide (Compound 142)

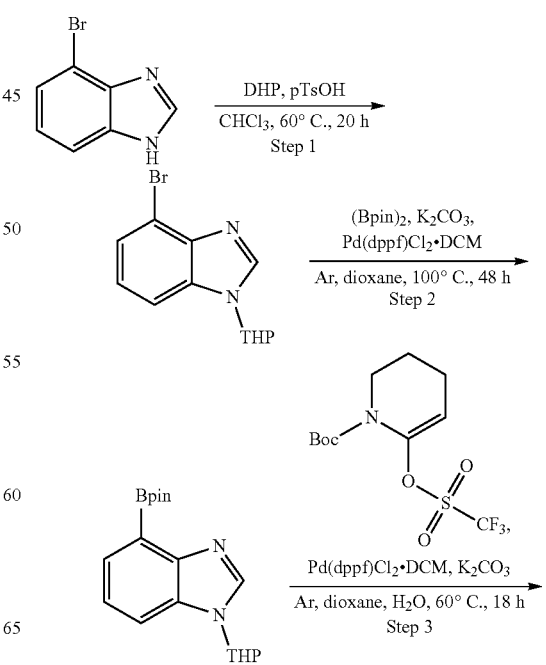

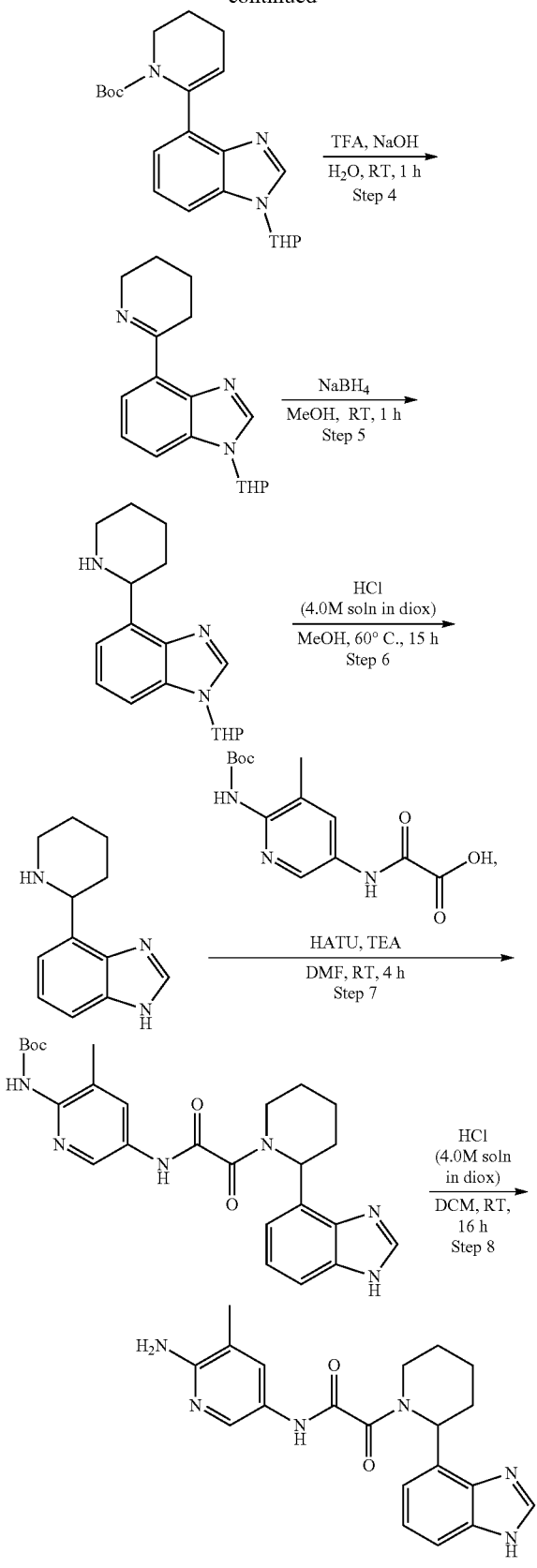

Compound 142

Step 1: The Synthesis of 4-bromo-1-tetrahydropyran-2-yl-benzimidazole

Dihydropyran (3.84 g, 45.68 mmol, 4.15 mL) and p-Toluenesulfonic acid monohydrate (144.81 mg, 761.30 μmol, 116.78 μL) were added to a suspension of 4-bromo-1H-benzimidazole (3 g, 15.23 mmol) in Chloroform (50 mL). The resulting mixture was stirred at 60° C. for 20 hr. Then, it was cooled to r.t. and excess of solid NaHCO$_3$ was added with vigorous stirring followed by 1 ml of water. When C02 evolution ceased, mixture was filtered through a pad of silica. Filtrate was concentrated under reduced pressure and residue was triturated with cold Hexane (30 ml). Resulting solid was filtered and dried, affording 4-bromo-1-tetrahydropyran-2-yl-benzimidazole (3.76 g, 13.37 mmol, 87.84% yield).

$^1$H NMR (500 MHz, CDCl$_3$) δ 1.76 (m, 4H), 2.13 (m, 3H), 3.75 (m, 1H), 4.12 (m, 1H), 5.48 (m, 1H), 7.17 (dd, 1H), 7.48 (m, 2H), 8.12 (s, 1H).

LCMS(ESI): [M+H]$^+$ m/z: calcd 280.0; found 281.2; Rt=1.127 min.

Step 2: The Synthesis of 1-tetrahydropyran-2-yl-4-(4,4,5,5-tetramethyl-1,3,2-dioxaborolan-2-yl)benzimidazole Potassium acetate (2.63 g, 26.75 mmol, 1.67 mL) was added to a solution of 4-bromo-1-tetrahydropyran-2-yl-benzimidazole (3.76 g, 13.37 mmol) and 4,4,5,5-tetramethyl-2-(4,4,5,5-tetramethyl-1,3,2-dioxaborolan-2-yl)-1,3,2-dioxaborolane (4.08 g, 16.05 mmol) in dioxane (30 mL). Reaction flask was evacuated and refilled with argon 3 times. Then PdCl$_2$DPPF*CH$_2$Cl$_2$ (436.86 mg, 534.95 μmol) was added under stream of argon. Resulting mixture was stirred at 100° C. for 48 hr under inert atmosphere. Then, it was cooled, diluted with MTBE (50 ml) and filtered. Filtrate was concentrated under reduced pressure, affording 1-tetrahydropyran-2-yl-4-(4,4,5,5-tetramethyl-1,3,2-dioxaborolan-2-yl)benzimidazole (6.09 g, crude).

LCMS(ESI): [M–THP]$^+$ m/z: calcd 244.2; found 247.2; Rt=0.827 min.

Step 3: The Synthesis of tert-butyl 6-(1-tetrahydropyran-2-ylbenzimidazol-4-yl)-3,4-dihydro-2H-pyridine-1-carboxylate Potassium carbonate (3.19 g, 23.06 mmol, 1.39 mL) was added to a solution of 1-tetrahydropyran-2-yl-4-(4,4,5,5-tetramethyl-1,3,2-dioxaborolan-2-yl)benzimidazole (5.74 g, 11.53 mmol) and tert-butyl 6-(trifluoromethylsulfonyloxy)-3,4-dihydro-2H-pyridine-1-carboxylate (4.98 g, 13.84 mmol) in Dioxane (50 mL) and Water (10 mL). Reaction flask was evacuated and refilled with argon 3 times. Then, PdCl$_2$DPPF*CH$_2$Cl$_2$ (376.71 mg, 461.30 μmol) was added under stream of argon. Resulting mixture was stirred at 60° C. for 18 hr under inert atmosphere. Then, solvent was removed under reduced pressure and residue was purified by column chromatography (RediSep Column: 220 g; 0-20% chloroform-MeCN; flow fate: 85 ml/min), affording tert-butyl 6-(1-tetrahydropyran-2-ylbenzimidazol-4-yl)-3,4-dihydro-2H-pyridine-1-carboxylate (3.4 g, 8.87 mmol, 76.88% yield).

$^1$H NMR (400 MHz, CDCl$_3$) δ 0.81 (s, 9H), 1.21 (m, 2H), 1.66 (m, 4H), 1.92 (m, 2H), 2.06 (m, 2H), 2.33 (m, 1H), 3.72 (m, 1H), 3.82 (m, 1H), 4.10 (m, 1H), 5.47 (m, 1H), 5.66 (s, 1H), 7.19 (m, 2H), 7.36 (d, 1H), 8.01 (s, 1H).

LCMS(ESI): [M+H]$^+$ m/z: calcd 383.2; found 384.2; Rt=1.205 min.

Step 4: The Synthesis of 1-tetrahydropyran-2-yl-4-(2,3,4,5-tetrahydropyridin-6-yl)benzimidazole tert-butyl 6-(1-tetrahydropyran-2-ylbenzimidazol-4-yl)-3,4-dihydro-2H-pyridine-1-carboxylate (3.4 g, 8.87 mmol) was dissolved in trifluoroacetic acid (15.16 g, 132.99 mmol, 10.25 mL). Resulting solution was stirred at 25° C. for 1 hr. Then, it was poured into ice-cold solution of Sodium hydroxide (7.09 g, 177.32 mmol, 3.33 mL) in water (150 ml). Resulting mixture was extracted with DCM (4*30 ml). After drying over Na$_2$SO$_4$, solvent was removed under reduced pressure, affording 1-tetrahydropyran-2-yl-4-(2,3,4,5-tetrahydropyridin-6-yl)benzimidazole (2 g, 7.06 mmol, 79.61% yield).

LCMS(ESI): [M+H]$^+$ m/z: calcd 283.2; found 284.2; Rt=0.906 min.

Step 5: The Synthesis of 4-(2-piperidyl)-1-tetrahydropyran-2-yl-benzimidazole 1-tetrahydropyran-2-yl-4-(2,3,4,5-tetrahydropyridin-6-yl)benzimidazole (2 g, 7.06 mmol) was dissolved in methanol (40 mL), and Sodium Borohydride (534.04 mg, 14.12 mmol, 499.11 µL) was added portionwise during 20 min. After addition was complete, resulting mixture was stirred at 25° C. for 1 hr. Then, it was concentrated under reduced pressure and residue was partitioned between water (20 ml) and EtOAc (40 ml). Organic layer was separated, dried over Na$_2$SO$_4$ and acidified with 4M Diox/HCl. Resulting precipitate was filtered and dried, affording 4-(2-piperidyl)-1-tetrahydropyran-2-yl-benzimidazole (2.3 g, 6.42 mmol, 90.95% yield, 2HCl).

$^1$H NMR (500 MHz, DMSO-d$_6$) δ 1.15 (m, 1H), 1.82 (m, 2H), 1.98 (m, 5H), 3.09 (m, 2H), 3.39 (m, 2H), 3.79 (m, 1H), 3.99 (m, 1H), 5.02 (m, 1H), 5.17 (m, 1H), 5.89 (m, 1H), 7.66 (m, 2H), 7.92 (m, 2H), 9.55 (m, 2H), 9.74 (s, 1H), 10.04 (m, 1H).

LCMS(ESI): [M+H]$^+$ m/z: calcd 285.2; found 286.2; Rt=0.883 min.

Step 6: The Synthesis of 4-(2-piperidyl)-1H-benzimidazole

Hydrogen chloride solution 4.0 M in dioxane (3.03 g, 8.31 mmol, 3 mL, 10% purity) was added to a solution of 4-(2-piperidyl)-1-tetrahydropyran-2-yl-benzimidazole (2.3 g, 6.42 mmol, 2HCl) in methanol (30 mL). Resulting solution was stirred at 60° C. for 15 hr. Then, solvent was removed under reduced pressure and residue was triturated with ethyl acetate (20 ml). Resulting precipitate was filtered and dried, affording 4-(2-piperidyl)-1H-benzimidazole (1.6 g, 5.84 mmol, 90.91% yield, 2HCl).

$^1$H NMR (400 MHz, DMSO-d$_6$) δ 1.85 (m, 6H), (m, 2H), 3.40 (m, 2H), 5.14 (m, 1H), 7.63 (dd, 1H), 7.85 (d, 1H), 7.95 (d, 1H), 9.56 (m, 1H), 9.67 (s, 1H), 9.95 (m, 1H).

LCMS(ESI): [M+H]$^+$ m/z: calcd 201.1; found 202.2; Rt=0.623 min.

Step 7: The Synthesis of tert-butyl N-[5-[[2-[2-(1H-benzimidazol-4-yl)-1-piperidyl]-2-oxo-acetyl]amino]-3-methyl-2-pyridyl]carbamate 2-[[6-(tert-butoxycarbonylamino)-5-methyl-3-pyridyl]amino]-2-oxo-acetic acid (269.24 mg, 911.78 µmol), HATU (381.35 mg, 1.00 mmol) and Triethylamine (461.32 mg, 4.56 mmol, 635.42 µL) were mixed together in Dimethylformamide (2 mL) and 4-(2-piperidyl)-1H-benzimidazole (250 mg, 911.78 µmol, 2HCl) was added. Resulting mixture was stirred at 25° C. for 4 hr. Then, it was subjected to HPLC (Column: YMC Triart C18 100*20 mm, 5 um; 40-40-90% 0-1-6 min 0.1% NH$_3$-methanol, flow: 30 ml/min), affording tert-butyl N-[5-[[2-[2-(1H-benzimidazol-4-yl)-1-piperidyl]-2-oxo-acetyl]amino]-3-methyl-2-pyridyl]carbamate (128 mg, 267.48 µmol, 29.34% yield).

LCMS(ESI): [M+2H]$^+$ m/z: calcd 478.2; found 480.2; Rt=2.824 min.

Step 8: The Synthesis of N-(6-amino-5-methyl-3-pyridyl)-2-[2-(1H-benzimidazol-4-yl)-1-piperidyl]-2-oxo-acetamide (Compound 142

Hydrogen chloride solution 4.0 M in dioxane (1.46 g, 4.01 mmol, 1.45 mL, 10% purity) was added to a solution of tert-butyl N-[5-[[2-[2-(1H-benzimidazol-4-yl)-1-piperidyl]-2-oxo-acetyl]amino]-3-methyl-2-pyridyl]carbamate (128 mg, 267.48 µmol) in Dichloromethane (2 mL). Resulting mixture was stirred at 25° C. for 16 hr. Then, it was concentrated under reduced pressure and residue was subjected to HPLC (column: YMC-Actus Triart C18 100*20 mm, 5 um; 0-5 min 20-45% water-acetonitrile (NH$_3$ 0.1%), flow 30 ml/min.), affording N-(6-amino-5-methyl-3-pyridyl)-2-[2-(1H-benzimidazol-4-yl)-1-piperidyl]-2-oxo-acetamide (51 mg, 134.77 µmol, 50.38% yield).

$^1$H NMR (600 MHz, DMSO-d$_6$) δ 1.25 (m, 1H), 1.47 (m, 1H), 1.56 (m, 1H), 1.64 (m, 1H), 1.90 (m, 1H), 1.98 (m, 3H), 3.03 (m, 1H), 3.44 (m, 1H), 4.04 (m, 1H), 5.58 (m, 3H), 7.07 (m, 1H), 7.19 (m, 1H), 7.46 (m, 2H), 7.94 (m, 1H), 8.24 (m, 1H), 10.54 (m, 1H), 12.38 (m, 1H).

LCMS(ESI): [M+2H]$^+$ m/z: calcd 378.2; found 380.2; Rt=0.734 min.

Example 755. The Synthesis of N-(6-amino-5-methyl-3-pyridyl)-2-oxo-2-[2-(2-oxoindolin-4-yl)-1-piperidyl]acetamide (Compound 116)

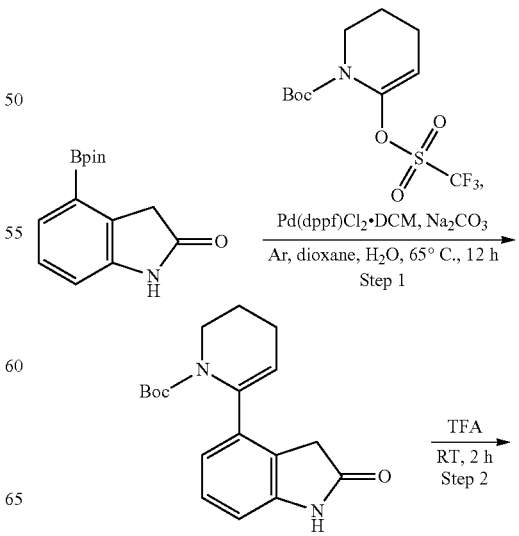

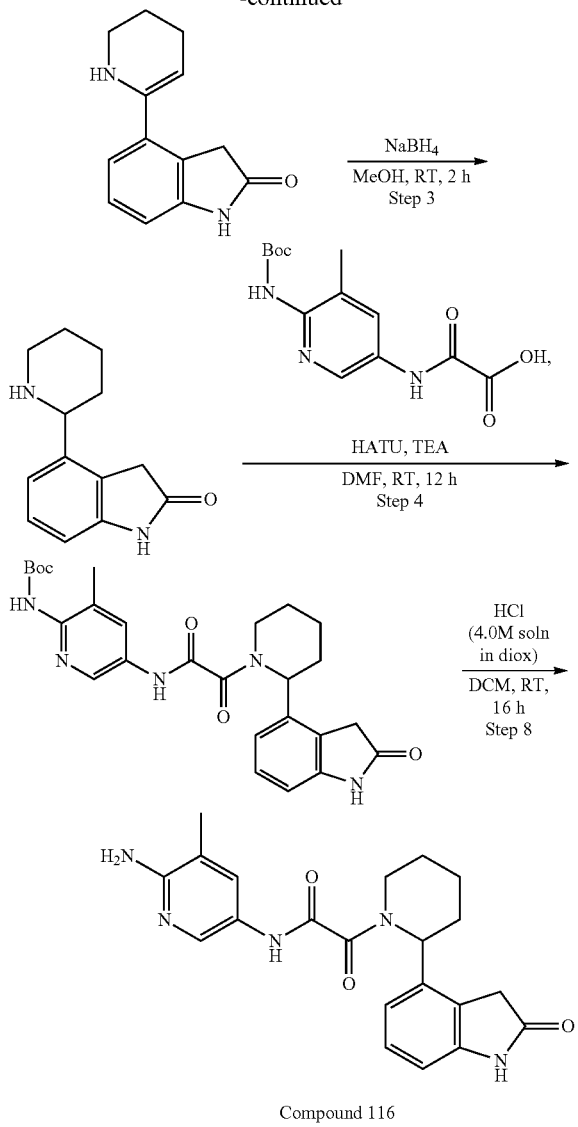

Compound 116

Step 1: The Synthesis of tert-butyl 6-(2-oxoindolin-4-yl)-3,4-dihydro-2H-pyridine-1-carboxylate A suspension of tert-butyl 6-(trifluoromethylsulfonyloxy)-3,4-dihydro-2H-pyridine-1-carboxylate (8 g, 24.15 mmol), 4-(4,4,5,5-tetramethyl-1,3,2-dioxaborolan-2-yl)indolin-2-one (5.96 g, 23.00 mmol), and sodium carbonate (7.31 g, 68.99 mmol, 2.89 mL) in Dioxane (100 mL) and Water (20 mL) was degassed and refilled with Ar three time. To this solution, Pd(dppf)Cl$_2$*DCM (939.00 mg, 1.15 mmol) was added. The resulting mixture was degassed, refilled with Ar and stirred at 65° C. for 12 hr. The precipitate was filtered off, washed with dioxane (50 ml). The solvent was evaporated in vacuo and residue was taken up with water 150 ml and extracted with EtOAc (2*100 ml). The combined organic layer was washed with brine (100 ml), dried over Na$_2$SO$_4$ and evaporated to obtain crude product (9 g). The crude product was purified by gradient chromatography (SiO$_2$; hexane-EtOAc) to obtain tert-butyl 6-(2-oxoindolin-4-yl)-3,4-dihydro-2H-pyridine-1-carboxylate (4.2 g, 13.36 mmol, 58.09% yield).

$^1$H NMR (500 MHz, DMSO-d$_6$) δ 1.00 (s, 9H), 1.21 (m, 2H), 1.84 (m, 2H), 2.25 (m, 2H), 3.62 (m, 2H), 5.24 (s, 1H), 6.68 (d, 1H), 6.76 (d, 1H), 7.07 (dd, 1H), 10.27 (s, 1H).

LCMS(ESI): [M−Boc]$^+$ m/z: calcd 214.2; found 215.2; Rt=1.330 min.

Step 2: The Synthesis of 4-(2,3,4,5-tetrahydropyridin-6-yl)indolin-2-one tert-butyl 6-(2-oxoindolin-4-yl)-3,4-dihydro-2H-pyridine-1-carboxylate (4.2 g, 13.36 mmol) was dissolved in trifluoroacetic acid (1.52 g, 13.36 mmol, 1.03 mL). The resulting mixture was stirred at 25° C. for 2 hr (to the end of gas evolution). The pH of the solution was adjusted to 8 with 10% NaOH solution and extracted with DCM (3*70 ml). The combined organic layer was washed with brine (50 ml), dried over Na$_2$SO$_4$ and evaporated in vacuo to obtain 4-(2,3,4,5-tetrahydropyridin-6-yl)indolin-2-one (2.5 g, 11.67 mmol, 87.34% yield).

$^1$H NMR (400 MHz, DMSO-d$_6$) δ 1.56 (m, 2H), 1.72 (m, 2H), 2.53 (m, 2H), 3.58 (s, 2H), 3.73 (m, 2H), 6.83 (dd, 1H), 7.21 (m, 2H), 10.37 (s, 1H).

LCMS(ESI): [M+H]$^+$ m/z: calcd 214.2; found 215.2; Rt=0.513 min.

Step 3: The Synthesis of 4-(2-piperidyl)indolin-2-one

To a solution of 4-(2,3,4,5-tetrahydropyridin-6-yl)indolin-2-one (2.5 g, 11.67 mmol) in Methanol (50 mL), sodium borohydride (441.43 mg, 11.67 mmol, 412.55 μL) was added portionwise at 0° C. The resulting mixture was stirred at ambient temperature for 2 hr and evaporated. The residue was taken up with water (50 ml) and extracted with DCM (3*50 ml). The combined organic layer was washed with brine (2*40 ml), dried over Na$_2$SO$_4$ and evaporated in vacuo to obtain 4-(2-piperidyl)indolin-2-one (1.9 g, 8.78 mmol, 75.29% yield).

LCMS(ESI): [M+H]$^+$ m/z: calcd 216.2; found 217.2; Rt=0.599 min.

Step 4: The Synthesis of tert-butyl N-[3-methyl-5-[[2-oxo-2-[2-(2-oxoindolin-4-yl)-1-piperidyl]acetyl]amino]-2-pyridyl]carbamate To a suspension of 4-(2-piperidyl)indolin-2-one (0.3 g, 1.39 mmol), 2-[[6-(tert-butoxycarbonylamino)-5-methyl-3-pyridyl]amino]-2-oxo-acetic acid (409.60 mg, 1.39 mmol) and HATU (527.42 mg, 1.39 mmol) in DMF (3 mL), triethylamine (701.80 mg, 6.94 mmol, 966.67 μL) was added. The resulting mixture was stirred at ambient temperature for 12 h, taken up with water (40 ml) and extracted with EtOAc (3*20 ml). The combined organic layer was washed with brine (3*20 ml), dried over Na$_2$SO$_4$ and evaporated to obtain tert-butyl N-[3-methyl-5-[[2-oxo-2-[2-(2-oxoindolin-4-yl)-1-piperidyl]acetyl]amino]-2-pyridyl]carbamate (0.6 g, crude). This compound was used for the next step without purification.

$^1$H NMR (500 MHz, DMSO-d$_6$) δ 1.43 (s, 9H), 1.65 (m, 4H), 2.18 (s, 3H), 2.29 (m, 2H), 2.68 (m, 2H), 3.50 (m, 2H), 5.54 (m, 1H), 6.76 (dd, 1H), 7.01 (d, 1H), 7.21 (d, 1H), 7.95 (s, 1H), 8.45 (s, 1H), 9.05 (s, 1H), 10.42 (s, 1H), 11.00 (s, 1H).

LCMS(ESI): [M−Boc]$^+$ m/z: calcd 393.2; found 394.2; Rt=1.191 min.

Step 5: The Synthesis of N-(6-amino-5-methyl-3-pyridyl)-2-oxo-2-[2-(2-oxoindolin-4-yl)-1-piperidyl]acetamide (Compound 116

To a solution of tert-butyl N-[3-methyl-5-[[2-oxo-2-[2-(2-oxoindolin-4-yl)-1-piperidyl]acetyl]amino]-2-pyridyl]carbamate (0.6 g, 1.22 mmol) in DCM (20 mL), hydrogen chloride solution 4.0 M in dioxane (8.00 g, 219.41 mmol, 10 mL) was added. The resulting mixture was stirred at 25° C. for 12 hr and evaporated in vacuo to obtain crude product (0.8 g). The crude product was purified by HPLC (40-40-80% 0-1-6 min 0.1% $NH_3$-methanol, flow: 30 ml/min (loading pump 4 ml/min methanol) target mass 393 column: YMC Triart C18 100*20 mm, 5 um) to give N-(6-amino-5-methyl-3-pyridyl)-2-oxo-2-[2-(2-oxoindolin-4-yl)-1-piperidyl]acetamide (115 mg, 292.30 μmol, 24.04% yield).

$^1$H NMR (500 MHz, DMSO+$CCl_4$) δ 1.54 (m, 1H), 1.65 (m, 3H), 1.83 (m, 1H), 2.02 (m, 3H), 2.31 (m, 1H), 3.06 (m, 1H), 3.46 (m, 2H), 3.99 (m, 1H), 5.54 (m, 1H), 5.62 (m, 2H), 6.77 (m, 1H), 6.96 (m, 1H), 7.21 (m, 1H), 7.46 (m, 1H), 7.99 (m, 1H), 10.41 (m, 1H), 10.48 (m, 1H).

LCMS(ESI): [M+H]$^+$ m/z: calcd 393.2; found 394.2; Rt=1.995 min.

Example 756. The Synthesis of N-(6-amino-5-methyl-3-pyridyl)-2-[(2S,5R)-5-methyl-2-(2-oxoindolin-4-yl)-1-piperidyl]-2-oxo-acetamide (Compound 714)

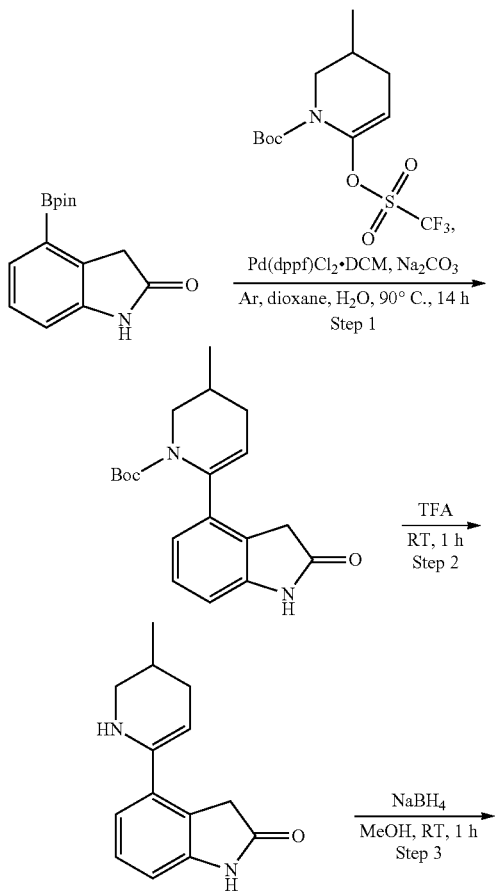

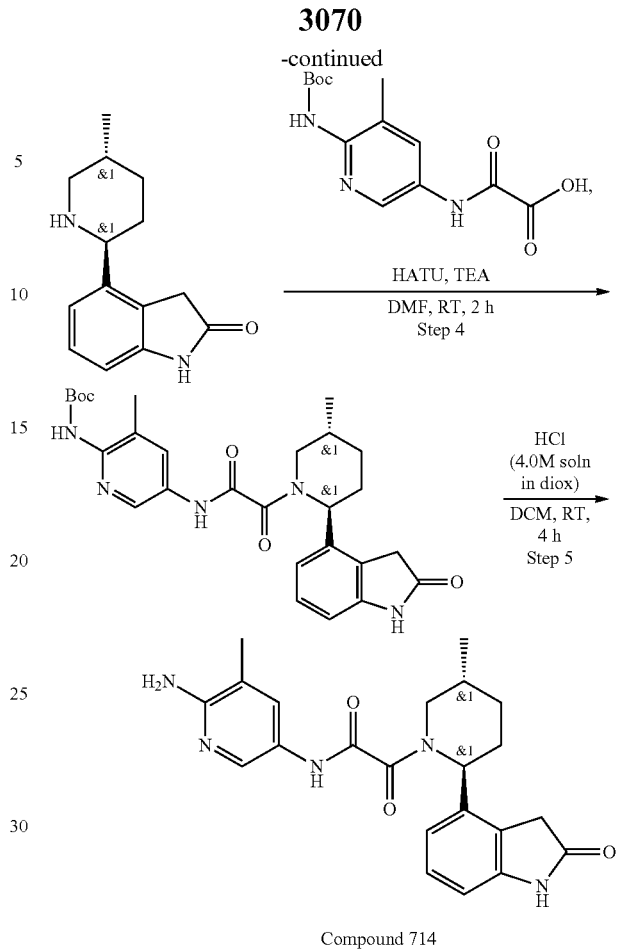

Compound 714

Step 1: The Synthesis of tert-butyl 3-methyl-6-(2-oxoindolin-4-yl)-3,4-dihydro-2H-pyridine-1-carboxylate Sodium carbonate (4.91 g, 46.31 mmol, 1.94 mL) was added to a solution of tert-butyl 3-methyl-6-(trifluoromethylsulfonyloxy)-3,4-dihydro-2H-pyridine-1-carboxylate (8.80 g, 25.47 mmol) and 4-(4,4,5,5-tetramethyl-1,3,2-dioxaborolan-2-yl)indolin-2-one (6 g, 23.16 mmol) in Dioxane (90 mL) and Water (30 mL). The reaction flask was evacuated and refilled with argon 3 times. Then, Pd(dppf)$Cl_2$*DCM (945.52 mg, 1.16 mmol) was added under stream of argon. The resulting mixture was stirred at 90° C. for 14 hr under inert atmosphere. Then, the mixture was evaporated to give crude product (21 g) which was purified by gradient column chromatography ($SiO_2$; Hexane-MeOH) to give tert-butyl 3-methyl-6-(2-oxoindolin-4-yl)-3,4-dihydro-2H-pyridine-1-carboxylate (5.2 g, 15.83 mmol, 68.38% yield).

$^1$H NMR (500 MHz, $CDCl_3$) δ 1.04 (s, 9H), 1.28 (m, 2H), 1.33 (d, 3H), 1.46 (m, 1H), 1.86 (m, 1H), 2.04 (m, 1H), 3.47 (m, 2H), 5.25 (s, 1H), 6.77 (d, 1H), 6.95 (d, 1H), 7.16 (dd, 1H), 8.30 (s, 1H).

LCMS(ESI): [M−Boc]$^+$ m/z: calcd 228.2; found 229.2; Rt=1.376 min.

Step 2: The Synthesis of 4-(3-methyl-2,3,4,5-tetrahydropyridin-6-yl)indolin-2-one To the tert-butyl 3-methyl-6-(2-oxoindolin-4-yl)-3,4-dihydro-2H-pyridine-1-carboxylate (2 g, 6.09 mmol) trifluoroacetic acid (6.94 g, 60.90 mmol, 4.69 mL) was added and the reaction mixture was stirred at 25° C. for 1 hr. TFA was evaporated. The residue was diluted with chloroform and evaporated to dryness to give 4-(3-methyl-2,3,4,5-tetrahydropyridin-6-yl)indolin-2-one (1.1 g, crude).

¹H NMR (400 MHz, CDCl₃) δ 1.05 (m, 2H), 1.43 (m, 3H), 2.12 (m, 1H), 3.19 (m, 1H), 3.41 (m, 2H), 3.82 (m, 2H), 4.05 (m, 1H), 7.24 (m, 2H), 7.41 (dd, 1H), 9.43 (s, 1H).

LCMS(ESI): [M+H]⁺ m/z: calcd 228.1; found 229.2; Rt=0.683 min.

Step 3: The Synthesis of 4-[(2S,5R)-5-methyl-2-piperidyl]indolin-2-one

To the pre-cooled (0° C.) solution of 4-(3-methyl-2,3,4,5-tetrahydropyridin-6-yl)indolin-2-one (1.1 g, 4.82 mmol) in MeOH (15 mL) sodium borohydride (218.75 mg, 5.78 mmol, 204.44 µL) was added portionwise. The reaction mixture was then stirred at 25° C. for 1 hr. MeOH was evaporated, the residue was re-dissolved in MeOH (5 ml) and HCl (4.0 M solution in dioxane, 5 ml) was added. The mixture was stirred for 15 min and solvents were evaporated to give crude solid. The product which was washed with THF (2*10 ml), dried in vacuo to give 4-[(2S,5R)-5-methyl-2-piperidyl]indolin-2-one (2.1 g, crude, HCl).

Product contains about 17% of NaCl.

¹H NMR (500 MHz, DMSO-d₆) δ 0.93 (m, 2H), 1.03 (m, 2H), 1.28 (m, 2H), 1.86 (m, 2H), 3.58 (m, 1H), 3.78 (m, 3H), 4.01 (m, 2H), 6.84 (d, 1H), 7.24 (dd, 1H), 7.37 (d, 1H), 9.58 (m, 1H), 10.56 (s, 1H).

LCMS(ESI): [M+H]⁺ m/z: calcd 230.1; found 231.2; Rt=0.611 min.

Step 4: The Synthesis of tert-butyl N-[3-methy-5-[[2-[(2S,5R)-5-methyl-2-(2-oxoindolin-4-yl)-1-piperidyl]-2-oxo-acetyl]amino]-2-pyridyl]carbamate To the solution of 4-[(2S,5R)-5-methyl-2-piperidyl]indolin-2-one (330 mg, 1.24 mmol, HCl), 2-[[6-(tert-butoxycarbonylamino)-5-methyl-3-pyridyl]amino]-2-oxo-acetic acid (365.29 mg, 1.24 mmol) and triethylamine (876.23 mg, 8.66 mmol, 1.21 mL) in DMF (4 mL), HATU (517.40 mg, 1.36 mmol) was added portionwise. The mixture was stirred at 25° C. for 2 hr. The reaction mixture was diluted with water (50 ml) and product was extracted with EtOAc (3*25 ml). The combined organic layer were washed with water, brine and dried over Na₂SO₄. The solvent was evaporated to give tert-butyl N-[3-methyl-5-[[2-[(2S,5R)-5-methyl-2-(2-oxoindolin-4-yl)-1-piperidyl]-2-oxo-acetyl]amino]-2-pyridyl]carbamate (260 mg, 512.23 µmol, 41.41% yield).

¹H NMR (400 MHz, DMSO-d₆) δ 0.96 (m, 3H), 1.13 (m, 1H), 1.40 (s, 9H), 1.95 (m, 2H), 2.14 (m, 3H), 2.65 (m, 5H), 2.85 (m, 1H), 3.98 (m, 1H), 5.31 (m, 1H), 6.71 (d, 1H), 6.94 (d, 1H), 7.16 (dd, 1H), 7.91 (m, 1H), 8.40 (m, 1H), 9.02 (s, 1H), 10.38 (m, 1H).

LCMS(ESI): [M+H]⁺ m/z: calcd 507.2; found 508.2; Rt=1.242 min.

Step 5: The Synthesis of N-(6-amino-5-methyl-3-pyridyl)-2-[(2S,5R)-5-methyl-2-(2-oxoindolin-4-yl)-1-piperidyl]-2-oxo-acetamide (Compound 714

To the stirred solution of tert-butyl N-[3-methyl-5-[[2-[(2S,5R)-5-methyl-2-(2-oxoindolin-4-yl)-1-piperidyl]-2-oxo-acetyl]amino]-2-pyridyl]carbamate (260 mg, 512.23 µmol) in DCM (10 mL), hydrogen chloride solution 4.0 M in dioxane (186.77 mg, 5.12 mmol, 233.46 µL) was added.

The reaction mixture was stirred at 25° C. for 4 hr. Solvents were evaporated in vacuo to give crude product (250 mg) which was purified by reverse phase HPLC (0-5 min 15-65% water-methanol (NH₃ 0.1%), flow 30 ml/min (loading pump 4 ml/min methanol (NH₃0.1%)), target mass 407.48 column: YMC-Actus Triart C18 100*20 mm1.D. S-5 um) to give N-(6-amino-5-methyl-3-pyridyl)-2-[(2S,5R)-5-methyl-2-(2-oxoindolin-4-yl)-1-piperidyl]-2-oxo-acetamide (44 mg, 107.98 µmol, 21.08% yield).

¹H NMR (DMSO-d₆, 600 MHz): δ (ppm) 0.98 (m, 3H), 1.24 (m, 1H), 1.98 (m, 7H), 3.45 (m, 3H), 5.46 (m, 3H), 6.69 (m, 1H), 6.94 (m, 1H), 7.17 (m, 1H), 7.35 (m, 1H), 7.89 (m, 1H), 10.43 (m, 2H).

LCMS(ESI): [M+H]⁺ m/z: calcd 407.2; found 408.2; Rt=1.816 min.

Example 757. The Synthesis of N-(6-amino-5-methyl-3-pyridyl)-2-[2-(1,3-benzothiazol-4-yl)-1-piperidyl]-2-oxo-acetamide (Compound 129)

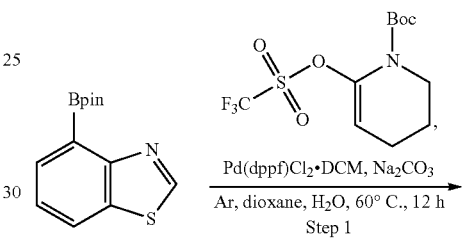

Pd(dppf)Cl₂·DCM, Na₂CO₃
Ar, dioxane, H₂O, 60° C., 12 h
Step 1

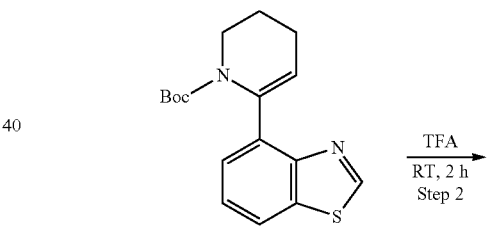

TFA
RT, 2 h
Step 2

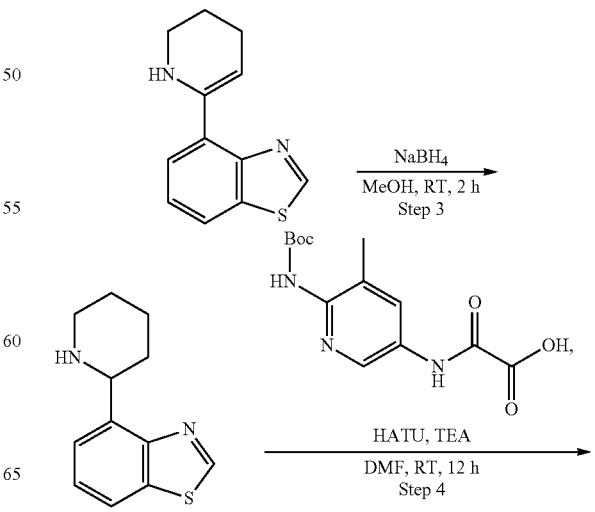

NaBH₄
MeOH, RT, 2 h
Step 3

HATU, TEA
DMF, RT, 12 h
Step 4

-continued

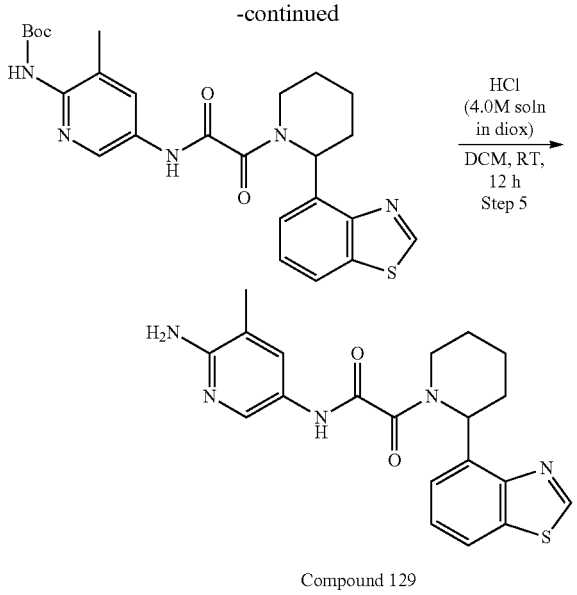

Compound 129

Step 1: The Synthesis of tert-butyl 6-(1,3-benzothiazol-4-yl)-3,4-dihydro-2H-pyridine-1-carboxylate A suspension of tert-butyl 6-(trifluoromethylsulfonyloxy)-3,4-dihydro-2H-pyridine-1-carboxylate (9.5 g, 28.67 mmol), 4-(4,4,5,5-tetramethyl-1,3,2-dioxaborolan-2-yl)-1,3-benzothiazole (7.13 g, 27.31 mmol), and sodium carbonate (8.68 g, 81.93 mmol, 3.43 mL) in Dioxane (100 mL) and Water (25 mL) was degassed and refilled with Ar three time. To this solution, Pd(dppf)Cl$_2$*DCM (1.12 g, 1.37 mmol) was added. The resulting mixture was degassed, refilled with Ar and stirred at 60° C. for 12 hr. The precipitate was filtered off, washed with dioxane (50 ml). The solvent was evaporated in vacuo and residue was taken up with water 150 ml and extracted with EtOAc (2*100 ml). The combined organic layer was washed with brine (100 ml), dried over Na$_2$SO$_4$ and evaporated to obtain crude product (9 g). The crude product was purified by gradient chromatography (SiO$_2$, hexane—EtOAc) to obtain tert-butyl 6-(1,3-benzothiazol-4-yl)-3,4-dihydro-2H-pyridine-1-carboxylate (3.5 g, 11.06 mmol, 40.50% yield).

$^1$H NMR (500 MHz, DMSO-d$_6$) δ 0.89 (s, 9H), 1.92 (m, 2H), 2.33 (m, 2H), 3.74 (m, 2H), 5.36 (m, 1H), 7.36 (m, 2H), 7.94 (d, 1H), 9.21 (s, 1H).

LCMS(ESI): [M−Boc]$^+$ m/z: calcd 216.2; found 217.2; Rt=1.540 min.

Step 2: The Synthesis of 4-(2,3,4,5-tetrahydropyridin-6-yl)-1,3-benzothiazole tert-butyl 6-(1,3-benzothiazol-4-yl)-3,4-dihydro-2H-pyridine-1-carboxylate (3.5 g, 11.06 mmol) was dissolved in trifluoroacetic acid (12.61 g, 110.61 mmol, 8.52 mL). The resulting mixture was stirred at 25° C. for 2 hr (to the end of gas evolution). The pH of the solution was adjusted to 8 with 10% NaOH solution and extracted with DCM (3*70 ml). The combined organic layer was washed with brine (50 ml), dried over Na$_2$SO$_4$ and evaporated in vacuo to obtain 4-(2,3,4,5-tetrahydropyridin-6-yl)-1,3-benzothiazole (2.3 g, 10.63 mmol, 96.13% yield).

$^1$H NMR (500 MHz, DMSO-d$_6$) δ 1.64 (m, 2H), 1.76 (m, 2H), 2.91 (m, 2H), 3.73 (m, 2H), 7.47 (dd, 1H), 7.59 (d, 1H), 8.17 (d, 1H), 9.41 (s, 1H).

LCMS(ESI): [M+H]$^+$ m/z: calcd 216.2; found 217.2; Rt=0.727 min.

Step 3: The Synthesis of 4-(2-piperidyl)-1,3-benzothiazole

To a solution of 4-(2,3,4,5-tetrahydropyridin-6-yl)-1,3-benzothiazole (2.3 g, 10.63 mmol) in MeOH (50 mL), sodium borohydride (402.29 mg, 10.63 mmol, 375.97 µL) was added portionwise at 0° C. The resulting mixture was stirred at ambient temperature for 2 hr and evaporated. The residue was taken up with water (50 ml) and extracted with DCM (3*50 ml). The combined organic layer was washed with brine (2*40 ml), dried over Na$_2$SO$_4$ and evaporated in vacuo to obtain 4-(2-piperidyl)-1,3-benzothiazole (1.75 g, 8.02 mmol, 75.38% yield).

$^1$H NMR (400 MHz, DMSO-d$_6$) δ 1.48 (m, 4H), 1.88 (m, 2H), 2.74 (m, 1H), 3.11 (m, 1H), 4.46 (m, 1H), 7.44 (dd, 1H), 7.50 (d, 1H), 8.00 (d, 1H), 9.37 (s, 1H), NH is not observed.

LCMS(ESI): [M+H]$^+$ m/z: calcd 218.1; found 219.0; Rt=0.877 min.

Step 4: The Synthesis of tert-butyl N-[5-[[2-[2-(1,3-benzothiazol-4-yl)-1-piperidyl]-2-oxo-acetyl]amino]-3-methyl-2-pyridyl]carbamate To a suspension of 4-(2-piperidyl)-1,3-benzothiazole (0.4 g, 1.83 mmol), 2-[[6-(tert-butoxycarbonylamino)-5-methyl-3-pyridyl]amino]-2-oxo-acetic acid (541.03 mg, 1.83 mmol) and HATU (696.66 mg, 1.83 mmol) in DMF (3 mL), triethylamine (927.00 mg, 9.16 mmol, 1.28 mL) was added. The resulting mixture was stirred at ambient temperature for 12 h, taken up with water (40 ml) and extracted with EtOAc (3*20 ml). The combined organic layer was washed with brine (3*20 ml), dried over Na$_2$SO$_4$ and evaporated to obtain tert-butyl N-[5-[[2-[2-(1,3-benzothiazol-4-yl)-1-piperidyl]-2-oxo-acetyl]amino]-3-methyl-2-pyridyl]carbamate (0.9 g, crude). This compound was used for the next step without purification.

$^1$H NMR (400 MHz, DMSO-d$_6$) δ 1.43 (s, 9H), 1.59 (m, 2H), 1.74 (m, 2H), 1.98 (m, 2H), 2.19 (s, 3H), 2.68 (m, 2H), 3.67 (m, 1H), 3.93 (m, 1H), 7.41 (m, 2H), 8.12 (m, 1H), 8.46 (m, 1H), 9.07 (m, 1H), 9.44 (m, 1H), 11.02 (m, 1H)

LCMS(ESI): [M+H]$^+$ m/z: calcd 495.2; found 496.2; Rt=1.316 min.

Step 5: The Synthesis of N-(6-amino-5-methyl-3-pyridyl)-2-[2-(1,3-benzothiazol-4-yl)-1-piperidyl]-2-oxo-acetamide (Compound 129

To a solution of tert-butyl N-[5-[[2-[2-(1,3-benzothiazol-4-yl)-1-piperidyl]-2-oxo-acetyl]amino]-3-methyl-2-pyridyl]carbamate (0.9 g, 1.82 mmol) in DCM (20 mL), hydrogen chloride solution 4.0 M in dioxane (8.00 g, 219.41 mmol, 10 mL) was added. The resulting mixture was stirred at 25° C. for 12 hr and evaporated in vacuo to obtain crude product (0.8 g). The crude product was purified by HPLC (40/60% 0-4 min 0.10% NH$_3$-methanol, flow: 30 ml/min (loading pump 4 ml/min methanol) target mass 395 column: YMC Triart C18 100*20 mm, 5 um) to give N-(6-amino-5-methyl-3-pyridyl)-2-[2-(1,3-benzothiazol-4-yl)-1-piperidyl]-2-oxo-acetamide (311 mg, 786.39 µmol, 43.30% yield).

$^1$H NMR (500 MHz, DMSO+CCl$_4$) δ 1.31 (m, 1H), 1.63 (m, 2H), 1.75 (m, 1H), 2.06 (m, 3H), 2.65 (m, 1H), 3.10 (m,

1H), 3.66 (m, 1H), 4.20 (m, 1H), 5.69 (m, 2H), 6.09 (m, 1H), 7.34 (m, 1H), 7.51 (m, 2H), 7.98 (m, 1H), 8.10 (m, 1H), 9.40 (m, 1H), 10.40 (m, 1H).

LCMS(ESI): [M+H]$^+$ m/z: calcd 395.1; found 396.2; Rt=2.325 min.

Example 758. The Synthesis of N-(6-amino-5-methyl-3-pyridyl)-2-[2-(1,3-Benzoxazol-4-yl)-1-piperidyl]-2-oxo-acetamide (Compound 140)

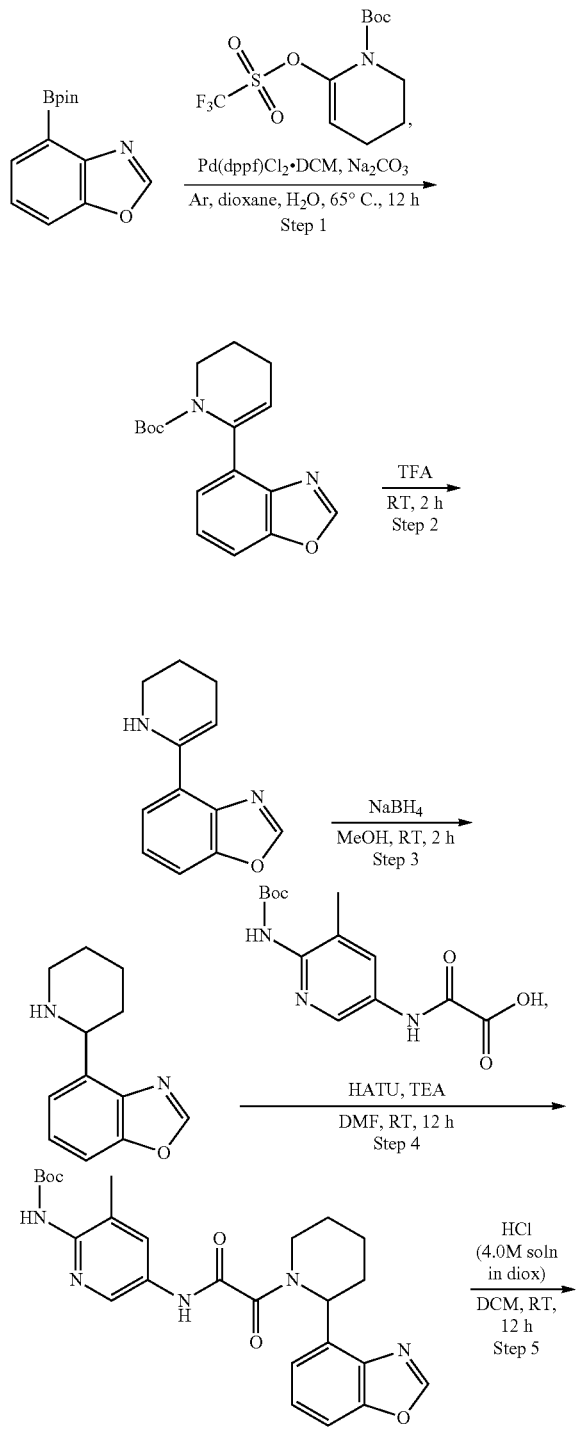

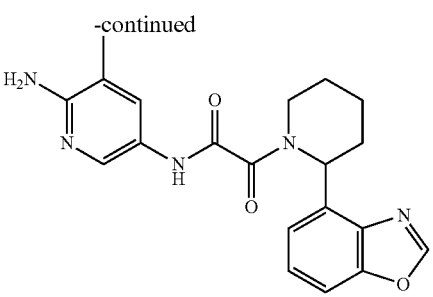

Compound 140

Step 1: The Synthesis of tert-butyl 6-(1,3-Benzoxazol-4-yl)-3,4-dihydro-2H-pyridine-1-carboxylate A suspension of tert-butyl 6-(trifluoromethylsulfonyloxy)-3,4-dihydro-2H-pyridine-1-carboxylate (9.5 g, 28.67 mmol), 4-(4,4,5,5-tetramethyl-1,3-dioxolan-2-yl)-1,3-benzoxazole (6.95 g, 28.11 mmol), and sodium carbonate (8.94 g, 84.34 mmol, 3.53 mL) in Dioxane (100 mL) and Water (25 mL) was degassed and refilled with an Ar three time. To this solution, Pd(dppf)Cl$_2$*DCM (918.29 mg, 1.12 mmol) was added. The resulting mixture was degassed, refilled with Ar and stirred at 65° C. for 12 hr. The precipitate was filtered off, washed with dioxane (50 ml). The solvent was evaporated in vacuo and the residue was taken up with water 150 ml and extracted with EtOAc (2*100 ml). The combined organic layer was washed with brine (100 ml), dried over Na$_2$SO$_4$ and evaporated to obtain crude product (9 g). The crude product was purified by gradient chromatography (SiO$_2$, hexane-EtOAc) to obtain tert-butyl 6-(1,3-benzoxazol-4-yl)-3,4-dihydro-2H-pyridine-1-carboxylate (3.5 g, 11.65 mmol, 41.45% yield).

$^1$H NMR (500 MHz, DMSO-d$_6$) δ 0.85 (s, 9H), 1.89 (m, 2H), 2.35 (m, 2H), 3.71 (m, 2H), 5.59 (m, 1H), 7.20 (d, 1H), 7.30 (dd, 1H), 7.49 (d, 1H), 8.50 (s, 1H).

LCMS(ESI): [M−Boc]$^+$ m/z: calcd 200.1; found 201.2; Rt=1.482 min.

Step 2: The Synthesis of 4-(2,3,4,5-tetrahydropyridin-6-yl)-1,3-Benzoxazole tert-butyl 6-(1,3-benzoxazol-4-yl)-3,4-dihydro-2H-pyridine-1-carboxylate (3.5 g, 11.65 mmol) was dissolved in trifluoroacetic acid (14.80 g, 129.80 mmol, 10 mL). The resulting mixture was stirred at 25° C. for 2 hr (to the end of gas evolution). The pH of the solution was adjusted to 8 with 10% NaOH solution and extracted with DCM (3*70 ml). The combined organic layer was washed with brine (50 ml), dried over Na$_2$SO$_4$ and evaporated in vacuo to obtain 4-(2,3,4,5-tetrahydropyridin-6-yl)-1,3-benzoxazole (2.05 g, 10.24 mmol, 87.86% yield).

$^1$H NMR (500 MHz, CDCl$_3$) δ 1.73 (m, 2H), 1.88 (m, 2H), 3.00 (m, 2H), 3.89 (m, 2H), 7.39 (dd, 1H), 7.58 (d, 1H), 7.69 (d, 1H), 8.09 (s, 1H).

Step 3: The Synthesis of 4-(2-piperidyl)-1,3-Benzoxazole

To a solution of 4-(2,3,4,5-tetrahydropyridin-6-yl)-1,3-benzoxazole (2.05 g, 10.24 mmol) in MeOH, sodium borohydride (387.33 mg, 10.24 mmol, 361.99 μL) was added portionwise at 0° C. The resulting mixture was stirred at ambient temperature for 2 hr and evaporated. The residue was taken up with water (50 ml) and extracted with DCM (3*50 ml). The combined organic layer was washed with brine (2*40 ml), dried over Na₂SO₄ and evaporated in vacuo to obtain 4-(2-piperidyl)-1,3-benzoxazole (1.45 g, crude).

¹H NMR (500 MHz, DMSO-d₆) δ 1.44 (m, 4H), 1.85 (m, 2H), 2.70 (m, 1H), 3.10 (m, 1H), 4.15 (m, 1H), 7.39 (m, 2H), 7.59 (d, 1H), 8.69 (s, 1H), NH is not observed.

LCMS(ESI): [M+H]⁺ m/z: calcd 202.1; found 203.2; Rt=0.666 min.

Step 4: The Synthesis of tert-butyl N-[5-[[2-[2-(1,3-Benzoxazol-4-yl)-1-piperidyl]-2-oxo-acetyl]amino]-3-methyl-2-pyridyl]carbamate To a suspension of 4-(2-piperidyl)-1,3-benzoxazole (0.4 g, 1.98 mmol), 2-[[6-(tert-butoxycarbonylamino)-5-methyl-3-pyridyl]amino]-2-oxo-acetic acid (584.01 mg, 1.98 mmol) and HATU (751.99 mg, 1.98 mmol) in DMF (3 mL), triethylamine (1.00 g, 9.89 mmol, 1.38 mL) was added. The resulting mixture was stirred at ambient temperature for 12 hr, taken up with water (40 ml) and extracted with EtOAc (3*20 ml). The combined organic layer was washed with brine (3*20 ml), dried over Na₂SO₄ and evaporated to obtain tert-butyl N-[5-[[2-[2-(1,3-benzoxazol-4-yl)-1-piperidyl]-2-oxo-acetyl]amino]-3-methyl-2-pyridyl]carbamate (0.8 g, crude). This compound was used for the next step without purification.

¹H NMR (400 MHz, DMSO-d₆) δ 1.45 (s, 9H), 1.64 (m, 4H), 2.19 (s, 3H), 2.95 (m, 2H), 3.89 (m, 1H), 5.69 (m, 1H), 5.98 (m, 1H), 6.99 (d, 1H), 7.25 (dd, 1H), 7.48 (d, 1H), 8.19 (s, 1H), 8.31 (s, 1H), 8.79 (s, 1H), 9.07 (s, 1H), 11.02 (m, 1H).

LCMS(ESI): [M+H]⁺ m/z: calcd 479.2; found 480.2; Rt=1.21 min.

Step 5: The Synthesis of N-(6-amino-5-methyl-3-pyridyl)-2-[2-(1,3-benzoxazol-4-yl)-1-piperidyl]-2-oxo-acetamide (Compound 140)

To a solution of tert-butyl N-[5-[[2-[2-(1,3-benzoxazol-4-yl)-1-piperidyl]-2-oxo-acetyl]amino]-3-methyl-2-pyridyl]carbamate (0.8 g, 1.67 mmol) in DCM (20 mL), hydrogen chloride solution 4.0 M in dioxane (8.00 g, 219.41 mmol, 10 mL) was added. The resulting mixture was stirred at 25° C. for 12 hr and evaporated in vacuo to obtain crude product (0.8 g). The crude product was purified by HPLC (0-5 min 30-80% water-methanole (NH₃ 0.1%), flow 30 ml/min (loading pump 4 ml/min methanole (NH₃ 0.1%)) column: YMC-Actus Triart C18 100*20 mm I.D. S-5 um) to give N-(6-amino-5-methyl-3-pyridyl)-2-[2-(1,3-benzoxazol-4-yl)-1-piperidyl]-2-oxo-acetamide (250 mg, 658.92 μmol, 39.50% yield).

¹H NMR (400 MHz, DMSO-d₆) δ 1.29 (m, 1H), 1.62 (m, 3H), 2.01 (m, 4H), 2.99 (m, 1H), 3.41 (m, 1H), 4.02 (m, 1H), 5.62 (m, 3H), 7.26 (m, 1H), 7.49 (m, 2H), 7.71 (m, 1H), 8.07 (m, 1H), 8.79 (m, 1H), 10.52 (s, 1H).

LCMS(ESI): [M+H]⁺ m/z: calcd 397.2; found; Rt=0.939 min.

Example 759. The Synthesis of N-(6-amino-5-methyl-3-pyridyl)-2-[(2S,5R)-2-(3,3-dimethylcyclohexyl)-5-methyl-1-piperidyl]-2-oxo-acetamide (Compound 150)

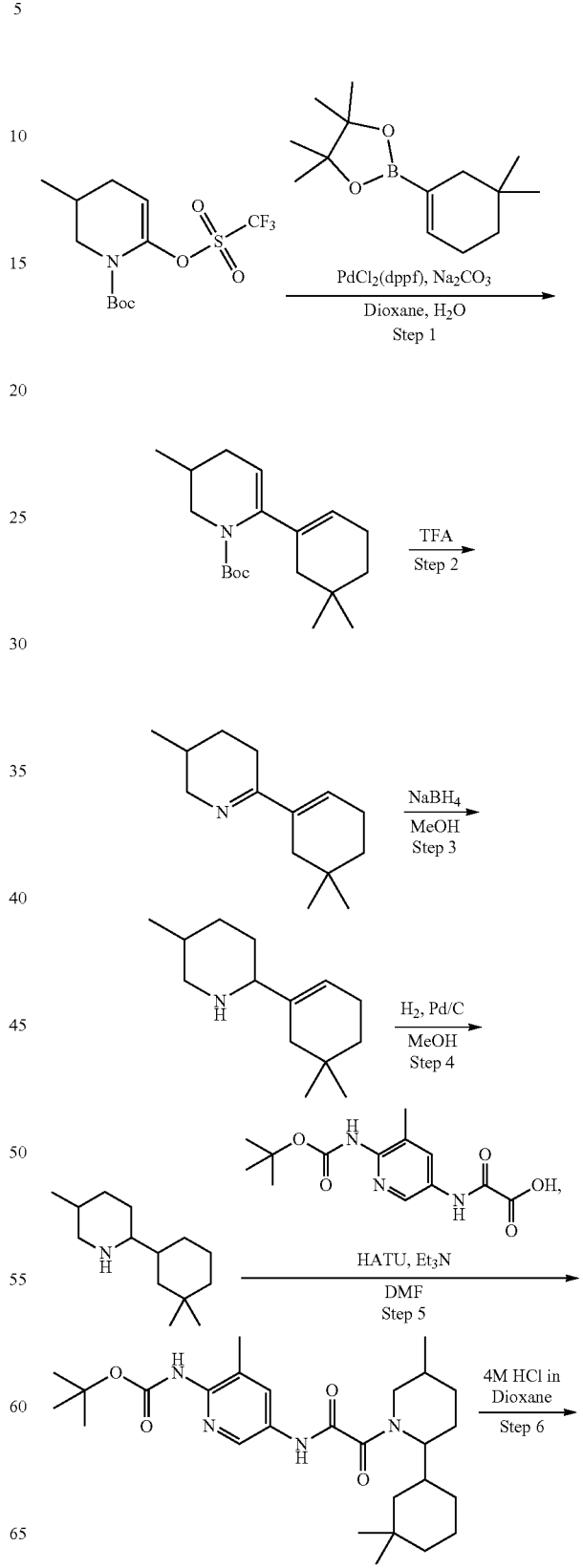

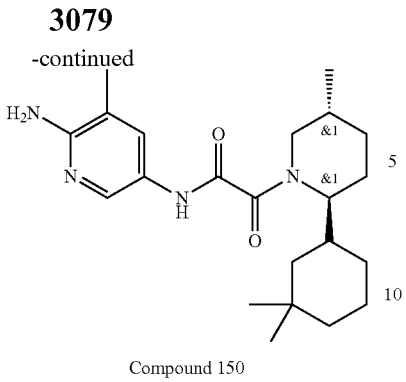

Compound 150

Step 1: Synthesis of tert-butyl 6-(5,5-dimethylcyclohexen-1-yl)-3-methyl-3,4-dihydro-2H-pyridine-1-carboxylate To a stirred solution of tert-butyl 3-methyl-6-(trifluoromethylsulfonyloxy)-3,4-dihydro-2H-pyridine-1-carboxylate (8.04 g, 23.29 mmol) and 2-(5,5-dimethylcyclohexen-1-yl)-4,4,5,5-tetramethyl-1,3,2-dioxaborolane (5 g, 21.17 mmol) in Dioxane (90 mL) was added a solution of Sodium carbonate (6.73 g, 63.52 mmol, 2.66 mL) in Water (30 mL). The resulting mixture was purged with argon. Then, Pd(dppf)Cl$_2$ (864.50 mg, 1.06 mmol) was added and the resulting reaction mixture was stirred at 80° C. for 14 hours. After 14 hours, the reaction mixture was concentrated under reduced pressure and the residue was purified by column chromatography to obtain product tert-butyl 6-(5,5-dimethylcyclohexen-1-yl)-3-methyl-3,4-dihydro-2H-pyridine-1-carboxylate (1.70 g, 5.57 mmol, 26.29%) as colorless oil.

LCMS(ESI): [M+Boc]$^+$ m/z: calcd 305.3; found 250.2 (t-Bu cleaved product mass); Rt=1.954 min.

Step 2: Synthesis of 6-(5,5-dimethylcyclohexen-1-yl)-3-methyl-2,3,4,5-tetrahydropyridine A mixture of tert-butyl 6-(5,5-dimethylcyclohexen-1-yl)-3-methyl-3,4-dihydro-2H-pyridine-1-carboxylate (1.7 g, 5.57 mmol) and Trifluoroacetic acid (20 g, 175.41 mmol, 13.51 mL) was stirred at 25° C. for 3 hours. After 3 hours, 20% aqueous solution of NaOH (15 g) was added dropwise. The resulting suspension was extracted with DCM (2×100 mL). The combined organic layer was washed with water (100 mL), brine, dried over Na$_2$SO$_4$ and concentrated under reduced pressure to get product 6-(5,5-dimethylcyclohexen-1-yl)-3-methyl-2,3,4,5-tetrahydropyridine (1.2 g, crude) as colorless oil. The crude product was used in the next step reaction without any further purification.

LCMS(ESI): [M+H]$^+$ m/z: calcd 205.2; found 206.2; Rt=1.018 min.

Step 3: Synthesis of 2-(5,5-dimethylcyclohexen-1-yl)-5-methyl-piperidine

To a stirred solution of 6-(5,5-dimethylcyclohexen-1-yl)-3-methyl-2,3,4,5-tetrahydropyridine (1.2 g, 5.84 mmol) in MeOH (25 mL) was added Sodium Borohydride (221.09 mg, 5.84 mmol). The resulting reaction mixture was stirred at 25° C. for 4 hours. After 4 hours, the reaction mixture was concentrated under reduced pressure. The obtained residue was diluted with water (70 mL) and extracted with DCM (2×100 mL). The combined organic layer was washed with brine, dried over Na$_2$SO$_4$ and concentrated under reduced pressure to obtain 2-(5,5-dimethylcyclohexen-1-yl)-5-methyl-piperidine (0.9 g, 4.34 mmol, 74.27% yield) as a light-yellow oil. The crude product was used in the next step reaction without any further purification.

LCMS(ESI): [M+H]$^+$ m/z: calcd 207.3; found 208.2; Rt=1.058 min.

Step 4: Synthesis of 2-(3,3-dimethylcyclohexyl)-5-methyl-piperidine

A solution of 2-(5,5-dimethylcyclohexen-1-yl)-5-methyl-piperidine (0.9 g, 4.34 mmol) in MeOH (25 mL) was hydrogenated over Palladium, 10% on carbon, Type 487, dry (0.1 g, 939.67 µmol) at 25° C. for 72 hours under hydrogen atmosphere. After 72 hours, the reaction mixture was filtered, the filter cake was washed with MeOH and the filtrate was evaporated to give 2-(3,3-dimethylcyclohexyl)-5-methyl-piperidine (0.6 g, 2.87 mmol, 66.02% yield) as a yellow oil. The crude product was used in the next step reaction without any further purification.

LCMS(ESI): [M+H]$^+$ m/z: calcd 209.3; found 210.2; Rt=1.016 min.

Step 5: Synthesis of tert-butyl N-[5-[[2-[2-(3,3-dimethylcyclohexyl)-5-methyl-1-piperidyl]-2-oxo-acetyl]amino]-3-methyl-2-pyridyl]carbamate To a stirred solution of 2-[[6-(tert-butoxycarbonylamino)-5-methyl-3-pyridyl]amino]-2-oxo-acetic acid (423.11 mg, 1.43 mmol), 2-(3,3-dimethylcyclohexyl)-5-methyl-piperidine (0.3 g, 1.43 mmol) and HATU (599.30 mg, 1.58 mmol) in DMF (1 mL) was added Triethylamine (579.97 mg, 5.73 mmol, 798.86 µL). The resulting reaction mixture was stirred at 25° C. for 4 hours. After 4 hours, the reaction mixture was purified by reverse phase HPLC (Eluent: 50-100%, 0-6 min, water-acetonitrile; flow rate: 30 mL/min; loading pump: 4 mL/min, acetonitrile; column: SunFire C18 100×19 mm 5 um) to give tert-butyl N-[5-[[2-[2-(3,3-dimethylcyclohexyl)-5-methyl-1-piperidyl]-2-oxo-acetyl]amino]-3-methyl-2-pyridyl]carbamate (0.19 g, 390.43 µmol, 27.25% yield).

LCMS(ESI): [M+H]$^+$ m/z: calcd 486.4; found 487.4; Rt=4.673 min.

Step 6: Synthesis of N-(6-amino-5-methyl-3-pyridyl)-2-[(2S,5R)-2-(3,3-dimethylcyclohexyl)-5-methyl-1-piperidyl]-2-oxo-acetamide (Compound 150

A mixture of tert-butyl N-[5-[[2-[2-(3,3-dimethylcyclohexyl)-5-methyl-1-piperidyl]-2-oxo-acetyl]amino]-3-methyl-2-pyridyl]carbamate (0.14 g, 287.68 µmol) and 4M Hydrogen chloride solution in dioxane (104.89 mg, 2.88 mmol, 131.12 µL) was stirred at 25° C. for 2 hours. After 2 hours, the reaction mixture was purified by reverse phase HPLC (Eluent: 0-1-6 min, 65-65-70%, water-0.1% NH$_3$—methanol; flow rate: 30 mL/min; loading pump: 4 mL/min; column: YMC-Triart C18 100×20 mm, 5 um) to give N-(6-amino-5-methyl-3-pyridyl)-2-[(2S,5R)-2-(3,3-dimethylcyclohexyl)-5-methyl-1-piperidyl]-2-oxo-acetamide (Compound 150, 25 mg, 64.68 µmol, 22.48% yield) as an off-white solid.

$^1$H NMR (CDCl$_3$, 400 MHz): δ (ppm) 0.87 (m, 8H), 1.01 (m, 3H), 1.35 (m, 4H), 1.61 (m, 3H), 1.82 (m, 2H), 1.99 (m, 3H), 2.12 (s, 3H), 3.08 (m, 1H), 4.23 (m, 1H), 4.50 (m, 2H), 4.73 (m, 1H), 7.71 (m, 1H), 8.04 (m, 1H), 9.06 (m, 1H).

LCMS(ESI): [M+H]⁺ m/z: calcd 386.3; found 387.2; Rt=3.476 min.

Example 760. The Synthesis of N-(6-amino-5-methyl-3-pyridyl)-2-oxo-2-[2-[3-(trifluoromethyl)-1-bicyclo[1.1.1]pentanyl]-1-piperidyl]acetamide and N-(6-amino-5-methyl-3-pyridyl)-2-oxo-2-(2-sec-butyl-1-piperidyl)acetamide (Compound 217 and Compound 232

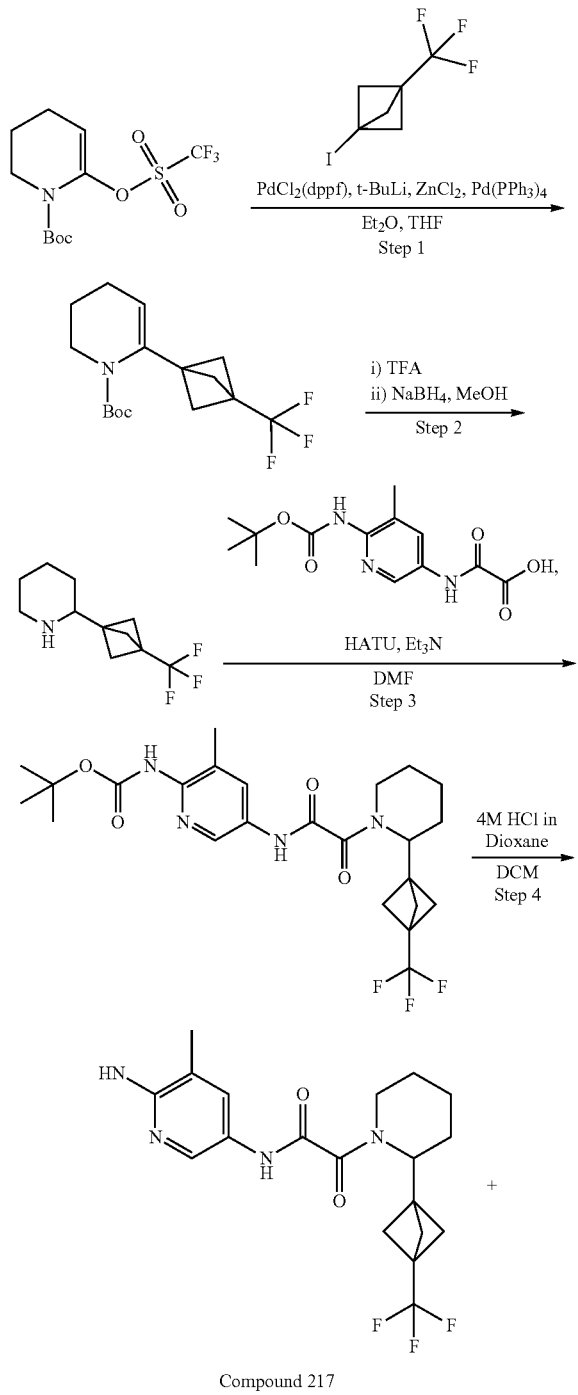

Compound 232

Step 1: Synthesis of tert-butyl 6-[3-(trifluoromethyl)-1-bicyclo[1.1.1]pentanyl]-3,4-dihydro-2H-pyridine-1-carboxylate 3-iodo-1-(trifluoromethyl)bicyclo[1.1.1]pentane (2 g, 7.63 mmol) was dissolved in Diethyl ether (20 mL) and cooled to −78° C. under argon atmosphere. tert-butyllithium (18% in pentane) (5.70 g, 16.03 mmol, 8.44 mL) was added dropwise via syringe while keeping the temperature below −70° C. The resulting solution was stirred at −70° C. for 1 hour. After 1 hour, a solution of Zinc chloride (anhydrous) (1.14 g, 8.40 mmol) in tetrahydrofuran (10 mL) was added dropwise. The resulting reaction mixture was allowed to warm up to room temperature and stirred for 1 hour at the same temperature. After that, tert-butyl 6-(trifluoromethyl-sulfonyloxy)-3,4-dihydro-2H-pyridine-1-carboxylate (2.53 g, 7.63 mmol) was added and the resulting mixture was heated to 50° C. until most of the diethyl ether was evaporated. The obtained residue was diluted with tetrahydrofuran (20 mL) and divided into 2 equal portions. To the first portion Pd(dppf)Cl₂·CH₂Cl₂ (62.34 mg, 76.33 μmol) was added and To the second portion Tetrakis(triphenylphosphine)palladium(0), 99.8% (metals basis), Pd 9% min (88.21 mg, 76.33 μmol) was added. Both resulting mixtures were stirred at 60° C. for 15 hours. GCMS and NMR indicated better conversion in case of Pd(dppf)Cl₂·CH₂Cl₂. The reaction (1ˢᵗ portion) mixture was quenched with saturated K₂CO₃ solution (4 mL) and stirred for 5 minutes. After 5 minutes, the organic layer was separated, dried over K₂CO₃ and concentrated under reduced pressure to obtain affording tert-butyl 6-[3-(trifluoromethyl)-1-bicyclo[1.1.1]pentanyl]-3,4-dihydro-2H-pyridine-1-carboxylate (1.1 g, 3.47 mmol, 90.82% yield) as brown oil.

GCMS: m/z: calcd 317.2; found 317.2; Rt=8.316 min.

Step 2: Synthesis of 2-[3-(trifluoromethyl)-1-bicyclo[1.1.1]pentanyl]piperidine Trifluoroacetic acid (13.20 g, 115.80 mmol, 8.92 mL) was added to tert-butyl 6-[3-(trifluoromethyl)-1-bicyclo[1.1.1]pentanyl]-3,4-dihydro-2H-pyridine-1-carboxylate (1.05 g, 3.31 mmol) and the resulting solution was stirred for 30 minutes at the room temperature. After 30 minutes, the reaction mixture was concentrated under reduced pressure and the obtained residue was dissolved in methanol (20 mL). Sodium Borohydride (1.00 g, 26.47 mmol, 935.90 μL) was added portionwise during 10 minutes. The resulting reaction mixture was stirred at 20° C. for 1 hour and then concentrated under reduced pressure. The obtained residue was partitioned between 2N HCl (30 mL) and MTBE (20 mL). The aqueous layer was basified to pH=10 with K₂CO₃, and extracted with DCM (3×15 mL). The combined organic layer was dried over K₂CO₃ and evaporated in vacuo to obtain 2-[3-(trifluoromethyl)-1-bicyclo[1.1.1]pentanyl]piperidine (200 mg, 912.22 μmol, 27.57% yield) as yellow oil. The crude product was used in the next step reaction without any further purification.

LCMS(ESI): [M+H]⁺ m/z: calcd 219.2; found 220.2; Rt=0.957 min.

Step 3: Synthesis of tert-butyl N-[3-methyl-5-[[2-oxo-2-[2-[3-(trifluoromethyl)-1-bicyclo[1.1.1]pentanyl]-1-piperidyl]acetyl]amino]-2-pyridyl]carbamate To a stirred solution of 2-[[6-(tert-butoxycarbonylamino)-5-methyl-3-pyridyl]amino]-2-oxo-acetic acid (296.31 mg, 1.00 mmol), HATU (398.88 mg, 1.05 mmol) and Triethylamine (184.61 mg, 1.82 mmol, 254.29 μL) in Dimethylformamide (3 mL) was added 2-[3-(trifluoromethyl)-1-bicyclo[1.1.1]pentanyl]piperidine (200 mg, 912.22 μmol). The resulting mixture was stirred at 20° C. for 15 hours. After 15 hours, the reaction mixture was diluted with water (15 mL) and extracted with ethyl acetate (2×15 mL). The combined organic layer was washed with water (3×10 mL) and brine (20 mL), dried over Na₂SO₄ and concentrated in vacuo to get tert-butyl N-[3-methyl-5-[[2-oxo-2-[2-[3-(trifluoromethyl)-1-bicyclo[1.1.1]pentanyl]-1-piperidyl]acetyl]amino]-2-pyridyl]carbamate (390 mg, 785.47 μmol, 86.11% yield) as a brown gum. The crude product was used in the next step reaction without any further purification.

LCMS(ESI): [M+Boc]⁺ m/z: calcd 496.3; found 497.2; Rt=1.388 min.

Step 4: Synthesis of N-(6-amino-5-methyl-3-pyridyl)-2-oxo-2-[2-[3-(trifluoromethyl)-1-bicyclo[1.1.1]pentanyl]-1-piperidyl]acetamide and N-(6-amino-5-methyl-3-pyridyl)-2-oxo-2-(2-sec-butyl-1-piperidyl)acetamide (Compound 217 and Compound 232

4.0 M Hydrogen chloride in dioxane (2.86 g, 7.85 mmol, 3.58 mL) was added to a stirred solution of tert-butyl N-[3-methyl-5-[[2-oxo-2-[2-[3-(trifluoromethyl)-1-bicyclo[1.1.1]pentanyl]-1-piperidyl]acetyl]amino]-2-pyridyl]carbamate (390 mg, 785.46 μmol) in Dichloromethane (5 mL). The resulting reaction mixture was stirred at 20° C. for 4 hours. After 4 hours, the reaction mixture was diluted with DCM (30 mL) and 10% aq. K₂CO₃ solution (20 mL) was added. The organic layer was separated, dried over Na₂SO₄ and concentrated under reduced pressure. The obtained residue was subjected to HPLC purification (Eluent: 0-50-75%, 0-1-6 min, 0.1% NH₃—methanol; flow rate 30 mL/min; Column: YMC Triart C18 100×20 mm, 5 um) to afford N-(6-amino-5-methyl-3-pyridyl)-2-oxo-2-[2-[3-(trifluoromethyl)-1-bicyclo[1.1.1]pentanyl]-1-piperidyl]acetamide (Compound 217, 111 mg, 280.02 μmol, 35.65% yield) and N-(6-amino-5-methyl-3-pyridyl)-2-oxo-2-(2-sec-butyl-1-piperidyl)acetamide (Compound 232, 52 mg, 163.31 μmol, 20.79% yield) as white solids.

Compound 217 ¹H NMR (DMSO-d₆, 500 MHz): δ (ppm) 1.35 (m, 1H), 1.65 (m, 5H), 2.01 (m, 9H), 2.96 (m, 1H), 4.02 (m, 2H), 5.62 (s, 2H), 7.48 (s, 1H), 8.00 (m, 1H), 10.33 (m, 1H).

LCMS(ESI): [M+H]⁺ m/z: calcd 396.2; found 397.2; Rt=2.654 min.

Compound 232 ¹H NMR (DMSO-d₆, 500 MHz): δ (ppm) 0.80 (d, 3H), 0.91 (t, 3H), 1.26-1.51 (m, 3H), 1.51-1.75 (m, 6H), 1.95-2.06 (m, 3H), 2.75-3.21 (m, 1H), 3.50-3.98 (m, 1H), 4.14-4.69 (m, 1H), 5.52-5.82 (m, 2H), 6.95-7.51 (m, 1H), 7.56-8.09 (m, 1H), 9.65-10.45 (m, 1H).

LCMS(ESI): [M+H]⁺ m/z: calcd 318.2; found 319.2; Rt=2.463 min.

Example 761. The Synthesis of N-(6-amino-5-methyl-3-pyridyl)-2-[(2R,5S)-5-methyl-2-(2-oxo-4-piperidyl)-1-piperidyl]-2-oxo-acetamide and N-(6-amino-5-methyl-3-pyridyl)-2-[(2S,5S)-5-methyl-2-(2-oxo-4-piperidyl)-1-piperidyl]-2-oxo-acetamide (Compound 156 and Compound 159

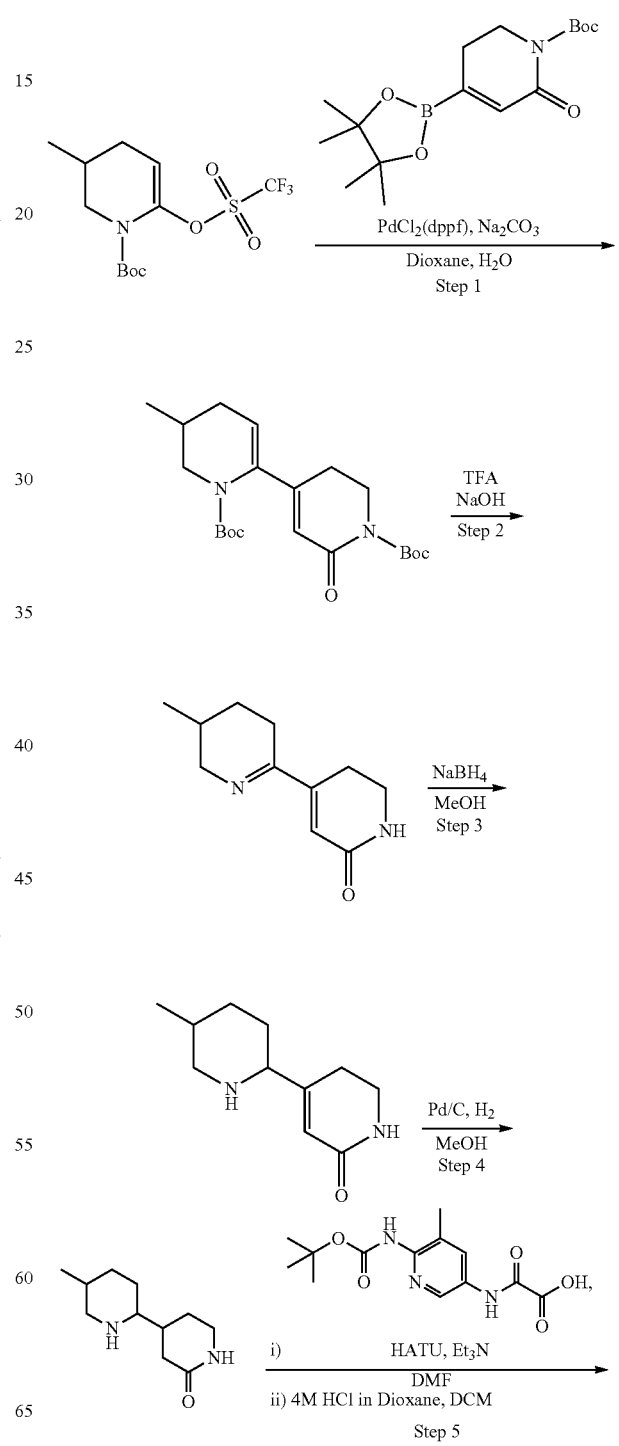

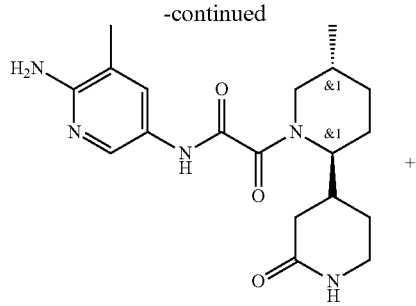

Compound 156

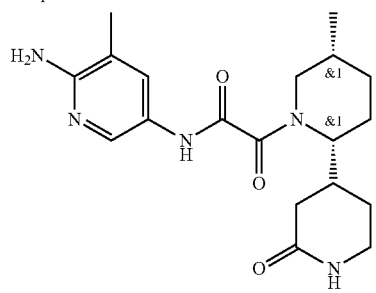

Compound 159

Step 1: Synthesis of tert-butyl 4-(1-tert-butoxycarbonyl-3-methyl-3,4-dihydro-2H-pyridin-6-yl)-6-oxo-2,3-dihydropyridine-1-carboxylate A stirring solution of tert-butyl 3-methyl-6-(trifluoromethylsulfonyloxy)-3,4-dihydro-2H-pyridine-1-carboxylate (4.00 g, 11.58 mmol), tert-butyl 6-oxo-4-(4,4,5,5-tetramethyl-1,3,2-dioxaborolan-2-yl)-2,3-dihydropyridine-1-carboxylate (3.74 g, 11.58 mmol) and Sodium carbonate (3.68 g, 34.75 mmol) in 1,4-dioxane (75 mL) and Water (25 mL) was purged with argon. Then, Pd(dppf)Cl$_2$ (378.07 mg, 463.32 µmol) was added under argon. The reaction mixture was stirred under argon at 65° C. for 12 hours After 12 hours, the reaction mixture was cooled and filtered. The filter cake was washed with 1.4-dioxane (2×20 mL) and discarded. The filtrate was evaporated in vacuo and the residue was purified by column chromatography (SiO$_2$, Eluent: 0-100% MTBE in Hexane) to afford tert-butyl 4-(1-tert-butoxycarbonyl-3-methyl-3,4-dihydro-2H-pyridin-6-yl)-6-oxo-2,3-dihydropyridine-1-carboxylate (3.00 g, 7.64 mmol, 65.99% yield) as light-brown oil.

LCMS(ESI): [M+Boc]$^+$ m/z: calcd 392.2; found 338.2 (t-Bu cleaved product mass); Rt=1.591 min.

Step 2: Synthesis of 4-(3-methyl-2,3,4,5-tetrahydropyridin-6-yl)-2,3-dihydro-1H-pyridin-6-one tert-butyl 4-(1-tert-butoxycarbonyl-3-methyl-3,4-dihydro-2H-pyridin-6-yl)-6-oxo-2,3-dihydropyridine-1-carboxylate (1 g, 2.55 mmol) was dissolved in Trifluoroacetic acid (11.62 g, 101.91 mmol, 7.85 mL). The resulting reaction mixture was stirred at 25° C. for 1 hour. After 1 hour, crushed ice was added (20 g) and pH was adjusted to 10 with a solution of Sodium hydroxide, pearl (4.59 g, 114.65 mmol, 2.15 mL) in water (35 mL). The resulting suspension was extracted with dichloromethane (2×50 mL). The combined organic phase was dried over Na$_2$SO$_4$ and evaporated under reduced pressure to afford 4-(3-methyl-2,3,4,5-tetrahydropyridin-6-yl)-2,3-dihydro-1H-pyridin-6-one (0.35 g, 1.82 mmol, 71.45% yield) as white solid.

LCMS(ESI): [M+H]$^+$ m/z: calcd 192.2; found 193.2; Rt=0.325 min.

Step 3: Synthesis of 4-(5-methyl-2-piperidyl)-2,3-dihydro-1H-pyridin-6-one

Sodium Borohydride (344.34 mg, 9.10 mmol) was added portion wise at 0° C. to a stirred solution of 4-(3-methyl-2,3,4,5-tetrahydropyridin-6-yl)-2,3-dihydro-1H-pyridin-6-one (0.35 g, 1.82 mmol) in methanol (10 mL). The reaction mixture was stirred at 0° C. for 1 hour. After 1 hour, the cooling bath was removed and the reaction mixture was allowed to warm to 25° C. The reaction mixture was stirred for 12 hours at the same temperature. After 12 hours, the reaction mixture was concentrated under reduced pressure, the residue was diluted with chloroform (50 mL), stirred for 30 min and filtered. The filtrate was evaporated in vacuo to afford 4-(5-methyl-2-piperidyl)-2,3-dihydro-1H-pyridin-6-one (0.27 g, 1.39 mmol, 76.34% yield) as light-yellow gum, which was used directly in the next step LCMS(ESI): [M+H]$^+$ m/z: calcd 194.2; found 195.2; Rt=0.581 min.

Step 4: Synthesis of 4-(5-methyl-2-piperidyl)piperidin-2-one

A solution of 4-(5-methyl-2-piperidyl)-2,3-dihydro-1H-pyridin-6-one (0.27 g, 1.39 mmol) in methanol (20 mL) was hydrogenated over Palladium, 10% on carbon (0.5 g) under hydrogen atmosphere at 25° C. for 12 hours. Upon completion, the reaction mixture was filtered, the filter cake was washed with methanol (10 mL) and the filtrate was concentrated under reduced pressure to afford 4-(5-methyl-2-piperidyl)piperidin-2-one (0.23 g, 1.17 mmol, 84.31% yield) as light-yellow gum, which was used directly in the next step LCMS(ESI): [M+H]$^+$ m/z: calcd 196.2; found 197.4; Rt=0.628 min.

Step 5: Synthesis of N-(6-amino-5-methyl-3-pyridyl)-2-[(2R,5S)-5-methyl-2-(2-oxo-4-piperidyl)-1-piperidyl]-2-oxo-acetamide and N-(6-amino-5-methyl-3-pyridyl)-2-[(2S,5S)-5-methyl-2-(2-oxo-4-piperidyl)-1-piperidyl]-2-oxo-acetamide (Compound 156 and Compound 159

To a stirred solution of 4-(5-methyl-2-piperidyl)piperidin-2-one (230 mg, 1.17 mmol), 2-[[6-(tert-butoxycarbonylamino)-5-methyl-3-pyridyl]amino]-2-oxo-acetic acid (346.01 mg, 1.17 mmol) and HATU (445.53 mg, 1.17 mmol) in DMF (5 mL) was added triethyl amine (1.19 g, 11.72 mmol, 1.63 mL). The reaction mixture was stirred at 25° C. for 1 hour. After 1 hour, the reaction mixture was concentrated under reduced pressure and the residue was purified by reverse phase HPLC (Eluent: $^{30}$—$^{65}$%, 0-6 min, water-methanol; column: SunFire C18 100×19 mm, 5 um) to afford two fractions.

1$^{st}$ fraction after HPLC (34 mg): was dissolved in dichloromethane (2 mL) and 4.0 M Hydrogen chloride in dioxane (2.10 g, 8.01 mmol, 2 mL, 13.9% purity) was added. The resulting reaction mixture was stirred at 25° C. for 1 hour. After 1 hour, the reaction mixture was concentrated in vacuo and the residue was purified by reverse phase HPLC (Eluent: 5-35%, 0-5 min, 0.1% NH$_3$-acetonitrile; column: YMC Triart C18 100×20 mm, 5 um) to obtain N-(6-amino-5-methyl-3-pyridyl)-2-[(2S,5S)-5-methyl-2-(2-oxo-4-piperidyl)-1-piperidyl]-2-oxo-acetamide (Compound 159, 20 mg, 53.55 µmol, 4.57% yield) as a white solid.

2nd fraction after HPLC (94 mg): was dissolved in dichloromethane (2 mL) and 4.0 M Hydrogen chloride in dioxane (2.10 g, 8.01 mmol, 2 mL, 13.9% purity) was added. The resulting reaction mixture was stirred at 25° C. for 1 hour. After 1 hour, the reaction mixture was concentrated in vacuo and the residue was purified by reverse phase HPLC (Eluent: 5-40%, 0-5 min, 0.1% NH$_3$-acetonitrile; column: YMC Triart C18 100×20 mm, 5 um) to obtain N-(6-amino-5-methyl-3-pyridyl)-2-[(2R,5S)-5-methyl-2-(2-oxo-4-piperidyl)-1-piperidyl]-2-oxo-acetamide (Compound 156, 59 mg, 157.99 µmol, 13.48% yield) as a white solid.

Compound 156: $^1$H NMR (DMSO-d$_6$, 500 MHz): δ (ppm) 0.96 (m, 3H), 1.26 (m, 2H), 1.77 (m, 5H), 2.06 (m, 5H), 2.40 (m, 1H), 2.79 (m, 1H), 3.15 (m, 2H), 4.11 (m, 1H), 5.61 (m, 2H), 7.48 (m, 2H), 7.96 (m, 1H), 10.38 (m, 1H).

LCMS(ESI): [M+H]$^+$ m/z: calcd 373.2; found 374.2; Rt=2.091 min.

Compound 159: $^1$H NMR (DMSO-d$_6$, 500 MHz): δ (ppm) 0.96 (m, 3H), 1.21 (m, 2H), 1.78 (m, 7H), 2.03 (s, 3H), 2.29 (m, 3H), 3.13 (m, 3H), 4.10 (m, 1H), 5.61 (s, 2H), 7.48 (m, 2H), 8.00 (s, 1H), 10.32 (m, 1H).

LCMS(ESI): [M+H]$^+$ m/z: calcd 373.2; found 374.2; Rt=1.918 min.

Example 762. The Synthesis of N-(6-amino-5-methylpyridin-3-yl)-2-(5-methyl-2-(5-oxopyrrolidin-3-yl)piperidin-1-yl)-2-oxoacetamide (Compound 210)

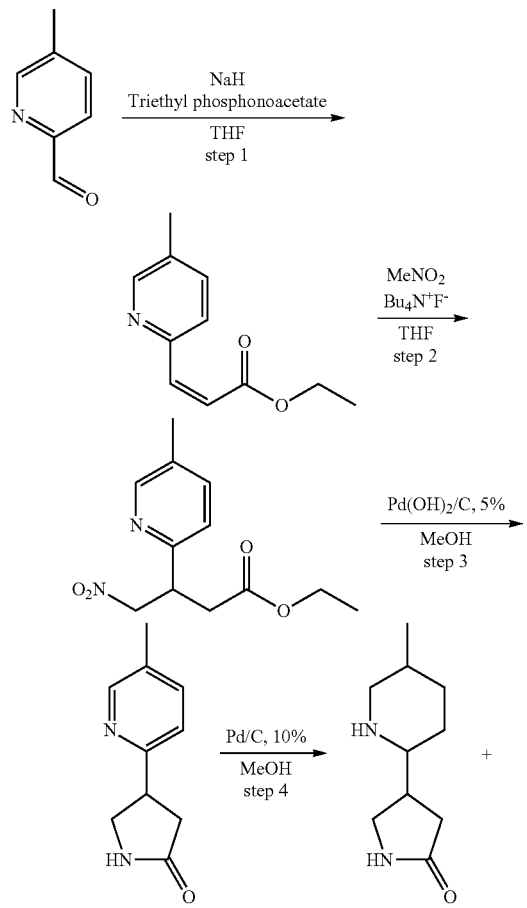

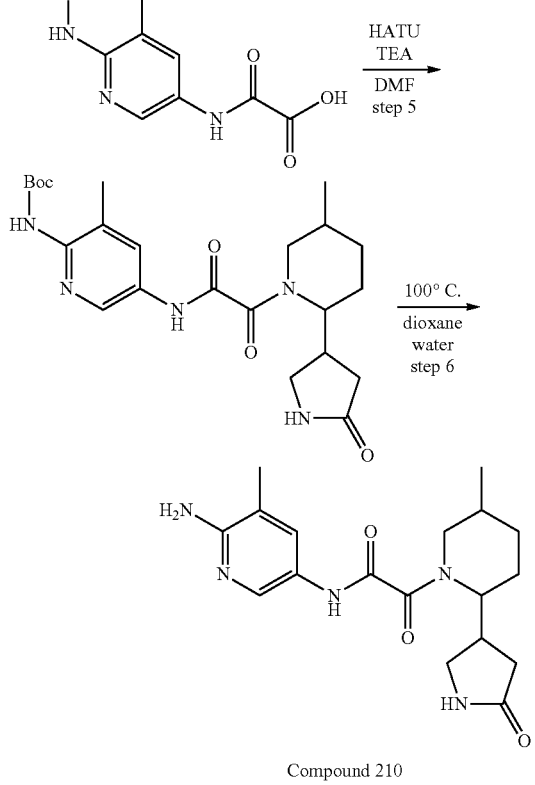

Compound 210

Step 1: Synthesis of Ethyl 3-(5-methylpyridin-2-yl)acrylate

Triethyl phosphonoacetate (10.18 g, 45.40 mmol, 9.01 mL) was added dropwise to a suspension of sodium hydride (in oil dispersion) 60% dispersion in mineral oil (1.73 g, 43.34 mmol) in THF (100 mL). After stirring at ambient temperature for 1 hr, 5-methylpyridine-2-carbaldehyde (5 g, 41.28 mmol) in THF (10 mL) was added dropwise. Resulting solution was stirred for the night. THE was evaporated and the mixture was diluted with DCM (100 ml) and washed with water (2×50 ml). The organic phase was dried over sodium sulfate, filtered and evaporated to obtain ethyl 3-(5-methyl-2-pyridyl)prop-2-enoate (7.7 g, 40.27 mmol, 97.56% yield).

$^1$H NMR (500 MHz, CDCl$_3$) δ (ppm) 1.31 (t, 3H), 2.34 (s, 3H), 4.24 (m, 2H), 6.82 (d, 1H), 7.32 (d, 1H), 7.48 (d, 1H), 7.63 (d, 1H), 8.45 (s, 1H).

LCMS(ESI): [M]$^+$ m/z: calcd 191.2; found 192.2; Rt=1.083 min.

Step 2: Synthesis of Ethyl 3-(5-methylpyridin-2-yl)-4-nitrobutanoate

A solution of ethyl 3-(5-methyl-2-pyridyl)prop-2-enoate (7.7 g, 40.27 mmol), nitromethane (7.37 g, 120.80 mmol, 6.53 mL) and tetrabutylammonium fluoride, 1M in THE (2.11 g, 8.05 mmol, 2.33 mL) in THF (77 mL) was refluxed for 12 hr. The solvent was evaporated under reduced pressure. Resulting material was diluted with MTBE (200 ml) and washed with brine (2×50 ml). Organic phase was dried over sodium sulfate, filtered and evaporated to obtain ethyl 3-(5-methyl-2-pyridyl)-4-nitro-butanoate (10 g, 39.64 mmol, 98.45% yield).

¹H NMR (400 MHz, CDCl₃) δ (ppm) 1.16 (t, 3H), 2.27 (s, 3H), 2.75 (m, 2H), 4.04 (m, 2H), 4.79 (m, 2H), 7.11 (d, 1H), 7.40 (d, 1H), 8.32 (s, 1H).
LCMS(ESI): [M]⁺ m/z: calcd 252.2; found 253.2; Rt=1.172 min.

Step 3: Synthesis of 4-(5-methylpyridin-2-yl)pyrrolidin-2-one

Ethyl 3-(5-methyl-2-pyridyl)-4-nitro-butanoate (9.5 g, 37.66 mmol) and palladium hydroxide on carbon 5% (464.82 mg, 3.77 mmol) were mixtured in methanol (100 mL). The mixture was stirred in autoclave at 70° C. in atmosphere of H₂ (50 atm) for 24 hr. The reaction mixture was cooled to rt, filtered and the solvent was evaporated in vacuo. Resulting crude material was purified by column chromatography (80 g SiO₂, MTBE/MeOH from 0~95%, flow rate=60 mL/min, Rt=16 min) to obtain 4-(5-methyl-2-pyridyl)pyrrolidin-2-one (0.5 g, 2.84 mmol, 7.53% yield).
¹H NMR (400 MHz, CDCl₃) δ (ppm) 2.29 (s, 3H), 2.67 (m, 1H), 3.59 (m, 1H), 3.78 (m, 2H), 6.21 (m, 2H), 7.06 (d, 1H), 7.42 (d, 1H), 8.37 (s, 1H).
LCMS(ESI): [M]⁺ m/z: calcd 176.2; found 177.2; Rt=0.477 min.

Step 4: Synthesis of 4-(5-methylpiperidin-2-yl)pyrrolidin-2-one 4-(5-methyl-2-pyridyl)pyrrolidin-2-one (0.4 g, 2.27 mmol) and palladium, 10% on carbon, type 487, dry (24.16 mg, 227.00 μmol) JM catalyst (A402028-10) were mixtured in methanol (4 mL). The mixture was stirred in autoclave at 70° C. in atmosphere of H₂ (50 atm) for 100 hr. The reaction mixture was cooled to rt, filtered and the solvent was evaporated in vacuo to obtain 4-(5-methyl-2-piperidyl)pyrrolidin-2-one (450 mg, crude).
¹H NMR (500 MHz, CDCl₃) δ (ppm) 0.86 (d, 3H), 1.70 (m, 9H), 2.45 (m, 2H), 3.05 (m, 1H), 3.20 (m, 1H), 3.43 (m, 1H), 5.75 (bds, 1H).
LCMS(ESI): [M]⁺ m/z: calcd 182.2; found 183.2; Rt=0.261 min.

Step 5: Synthesis of tert-butyl (3-methyl-5-(2-(5-methyl-2-(5-oxopyrrolidin-3-yl)piperidin-1-yl)-2-oxoacetamido)pyridin-2-yl)carbamate 4-(5-methyl-2-piperidyl)pyrrolidin-2-one (200 mg, 1.10 mmol), 2-[[6-(tert-butoxycarbonylamino)-5-methyl-3-pyridyl]amino]-2-oxo-acetic acid (324.03 mg, 1.10 mmol), TEA (555.19 mg, 5.49 mmol, 764.72 μL) were mixed in DMF (5 mL) and then HATU (625.85 mg, 1.65 mmol) were added. Resulting mixture were stirred at 25° C. for 12 hr. The mixture was evaporated under reduce pressure and purified with HPLC (2-10 min 10-50% MeOH, 30 ml/min) to obtain tert-butyl N-[3-methyl-5-[[2-[5-methyl-2-(5-oxopyrrolidin-3-yl)-1-piperidyl]-2-oxo-acetyl]amino]-2-pyridyl]carbamate (77.1 mg, crude).
LCMS(ESI): [M]⁺ m/z: calcd 459.5; found 460.2; Rt=1.065 min.

Step 6: Synthesis of N-(6-amino-5-methylpyridin-3-yl)-2-(5-methyl-2-(5-oxopyrrolidin-3-yl)piperidin-1-yl)-2-oxoacetamide (Compound 210

The solution of tert-butyl N-[3-methyl-5-[[2-[5-methyl-2-(5-oxopyrrolidin-3-yl)-1-piperidyl]-2-oxo-acetyl]amino]-2-pyridyl]carbamate (77.1 mg, 167.78 μmol) in dioxane (2 mL) and water (2 mL) was heated at 100° C. for 12 hr. The mixture was evaporated under reduce pressure and purified by HPLC (2-10 min 10-50% water-MeOH+NH₃) to obtain N-(6-amino-5-methyl-3-pyridyl)-2-[5-methyl-2-(5-oxopyrrolidin-3-yl)-1-piperidyl]-2-oxo-acetamide (18.2 mg, 50.64 μmol, 30.18% yield).
¹H NMR (400 MHz, CDCl₃) δ (ppm) 1.02 (m, 3H), 1.40 (m, 2H), 1.90 (m, 2H), 2.10 (m, 5H), 2.28 (m, 2H), 3.10 (m, 3H), 4.43 (m, 3H), 4.90 (m, 1H), 6.47 (m, 1H), 7.68 (m, 1H), 8.00 (m, 1H), 9.50 (m, 1H).
LCMS(ESI): [M]⁺ m/z: calcd 359.4; found 360.2; Rt=0.790 min.

Example 763. The Synthesis of rac-N-(6-amino-5-methylpyridin-3-yl)-2-oxo-2-((2R,5S)-2-phenyl-5-(trifluoromethyl)piperidin-1-yl)acetamide (Compound 177)

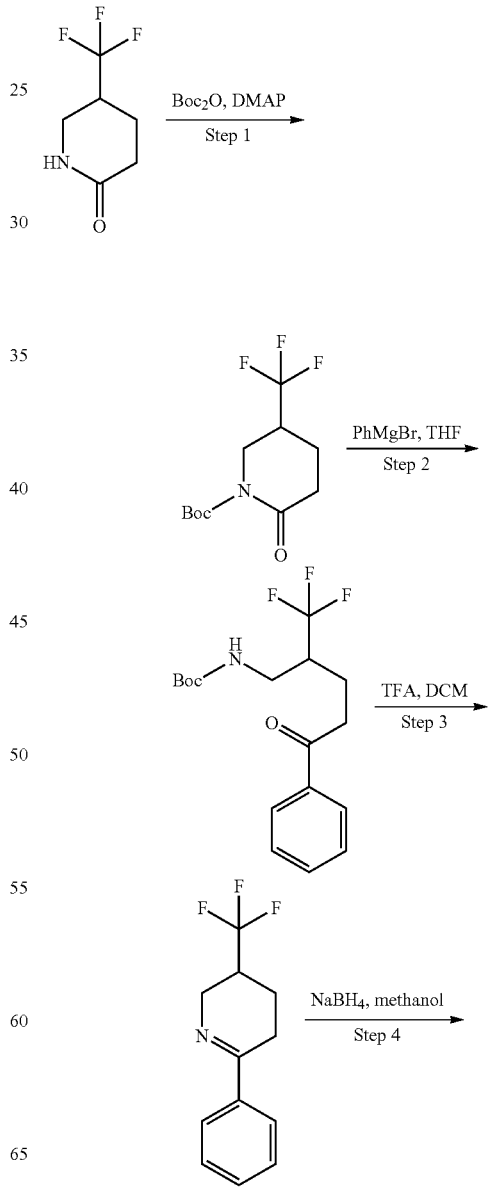

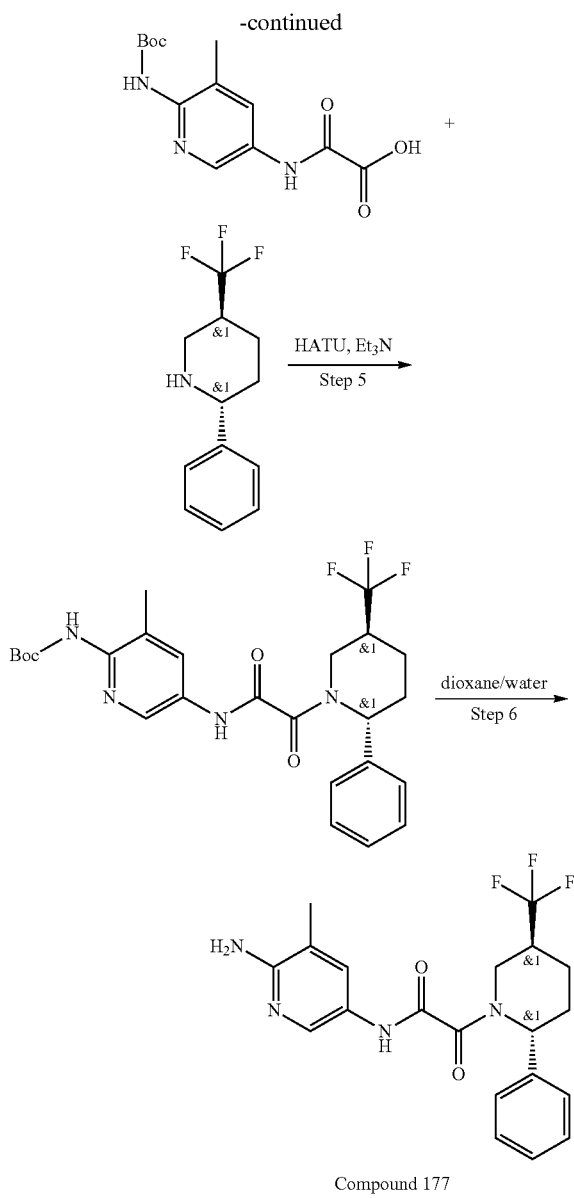

Compound 177

Step 1: Synthesis of tert-butyl 2-oxo-5-(trifluoromethyl)piperidine-1-carboxylate Di-tert-butyl dicarbonate (11.06 g, 50.68 mmol, 11.63 mL) was added dropwise to a solution of 5-(trifluoromethyl)piperidin-2-one (7.7 g, 46.07 mmol) and 4-dimethylaminopyridine (281.43 mg, 2.30 mmol, 4.89 mL) in Acetonitrile (140 mL). Resulting solution was stirred for 12 hr at 25° C. Then the solvent was evaporated and resulting crude material was diluted with EtOAc (100 ml) and washed with saturated sodium hydrocarbonate solution (2×100 ml). Organic phase was dried over sodium sulfate and evaporated under reduced pressure to obtain tert-butyl 2-oxo-5-(trifluoromethyl)piperidine-1-carboxylate (11.18 g, 41.83 mmol, 90.80% yield) $^1$H NMR (CDCl$_3$, 400 MHz): δ 1.53 (s, 9H), 1.93 (m, 1H), 2.13 (m, 1H), 2.50 (m, 1H), 2.65 (m, 1H), 3.75 (m, 1H), 4.02 (m, 1H).

LCMS(ESI): [M−tBu+1]$^+$ m/z: calcd 267.2; found 212.0; Rt=1.277 min.

Step 2: Synthesis of tert-butyl N-[5-oxo-5-phenyl-2-(trifluoromethyl)pentyl]carbamate Phenyl magnesium bromide (9.10 g, 50.20 mmol) (62.75 ml, 0.8M solution in THF) was added to a solution of tert-butyl 2-oxo-5-(trifluoromethyl)piperidine-1-carboxylate (11.18 g, 41.83 mmol) in THF (200 mL) at −78° C. under inert atmosphere. Resulting solution was stirred at −78° C. for 1 hr before being warmed to rt and stirred for 12 h. The reaction was diluted with MTBE (500 ml) and slowly quenched with 100 mL of saturated ammonium chloride aqueous solution. The organic phase was washed with a saturated sodium bicarbonate aqueous solution (2×200 ml). The combined aqueous fractions were back extracted two times with MTBE. The combined organic fractions were dried over sodium sulfate, and concentrated by rotary evaporation to obtain crude material that was purified with column chromatography (120 g SiO$_2$, hexane/MTBE with MTBE from 0~15%, flow rate=80 mL/min, RC 9CV) to obtain tert-butyl N-[5-oxo-5-phenyl-2-(trifluoromethyl)pentyl]carbamate (5.5 g, 15.93 mmol, 38.07% yield)
$^1$H NMR (CDCl$_3$, 400 MHz): δ 1.41 (s, 9H), 1.92 (m, 1H), 2.05 (m, 1H), 2.42 (m, 1H), 3.16 (m, 2H), 3.30 (m, 1H), 3.41 (m, 1H), 4.86 (brs, 1H), 7.44 (t, 2H), 7.55 (t, 1H), 7.95 (d, 2H).

LCMS(ESI): [M−Boc]$^+$ m/z: calcd 345.3; found 246.2; Rt=1,502 min.

Step 3: Synthesis of 6-phenyl-3-(trifluoromethyl)-2,3,4,5-tetrahydropyridine A solution of tert-butyl N-[5-oxo-5-phenyl-2-(trifluoromethyl)pentyl]carbamate (5.5 g, 15.93 mmol) in TFA (25 mL) and DCM (25 mL) was stirred at 25° C. for 2 hr. Sodium sulfate saturated aq. solution was added to the solution (50 ml) and then extracted with DCM (2×50 ml). Organic phase was dried over sodium sulfate, filtered and evaporated to obtain 6-phenyl-3-(trifluoromethyl)-2,3,4,5-tetrahydropyridine (3.5 g, 15.40 mmol, 96.72% yield)
$^1$H NMR (CDCl$_3$, 500 MHz): δ 1.83 (m, 1H), 2.19 (m, 1H), 2.40 (m, 1H), 2.64 (m, 1H), 2.91 (m, 1H), 3.75 (m, 1H), 4.23 (d, 1H), 7.42 (m, 3H), 7.77 (d, 2H) Step 4: Synthesis of 2-phenyl-5-(trifluoromethyl)piperidine Sodium borohydride (1.17 g, 30.81 mmol, 1.09 mL) was added portionwise to a solution of 6-phenyl-3-(trifluoromethyl)-2,3,4,5-tetrahydropyridine (3.5 g, 15.40 mmol) in methanol (70 mL). The mixture was stirred at rt for 12 hr. Water (50 ml) was added and resulting mixture was extracted with EtOAc (2×50 ml). Organic phase was dried over sodium sulfate, filtered and evaporated to obtain 2-phenyl-5-(trifluoromethyl)piperidine (3.3 g, 14.40 mmol, 93.46% yield).
$^1$H NMR (400 MHz, CDCl$_3$) δ 1.59 (m, 2H), 1.73 (brs, 1H), 1.92 (m, 1H), 2.15 (m, 1H), 2.35 (m, 1H), 2.82 (t, 1H), 3.39 (d, 1H), 3.61 (d, 1H), 7.34 (m, 5H).

GCMS [M]$^+$ m/z: calcd 229.2; found 229.1; Rt=6.295 min.

Step 5: Synthesis of tert-butyl N-[3-methyl-5-[[2-oxo-2-[2-phenyl-5-(trifluoromethyl)-1-piperidyl]acetyl]amino]-2-pyridyl]carbamate 2-phenyl-5-(trifluoromethyl)piperidine (200 mg, 872.44 µmol), 2-[[6-(tert-butoxycarbonylamino)-5-methyl-3-pyridyl]amino]-2-oxo-acetic acid (257.63 mg, 872.44 µmol), triethylamine (441.41 mg, 4.36 mmol, 608.01 µL) were mixed in DMF (5 mL) and then HATU (497.59 mg, 1.31 mmol) were added. Resulting mixture were stirred at 25° C. for 12 hr. The mixture was evaporated under reduce pressure and purified with HPLC (2-10 min 10-50% R1, 30 ml/min) to obtain tert-butyl N-[3-methyl-5-[[2-oxo-2-[2-phenyl-5-(trifluoromethyl)-1-piperidyl]acetyl]amino]-2-pyridyl]carbamate (94.6 mg, 186.77 μmol, 21.41% yield)

$^1$H NMR (400 MHz, CDCl$_3$) δ 1.48 (s, 9H), 1.50-2.10 (m, 4H), 2.22 (m, 4H), 2.34 (m, 1H), 3.57 (m, 0.5H), 4.79 (m, 0.5H), 5.66 (m, 1H), 6.66 (m, 1H), 7.26 (m, 5H), 7.98 (s, 1H), 8.33 (s, 1H), 9.20 (m, 1H).

LCMS(ESI): [M+1]$^+$ m/z: calcd 506.2; found 507.2; Rt=1,436 min.

Step 6: Synthesis of rac-N-(6-amino-5-methylpyridin-3-yl)-2-oxo-2-((2R,5S)-2-phenyl-5-(trifluoromethyl)piperidin-1-yl)acetamide (Compound 177

The solution of tert-butyl N-[3-methyl-5-[[2-oxo-2-[2-phenyl-5-(trifluoromethyl)-1-piperidyl]acetyl]amino]-2-pyridyl]carbamate (94.6 mg, 186.77 μmol) in Dioxane (2 mL) and Water (2 mL) was heated at 100° C. for 12 hr. The solvents were evaporated to dryness. The crude material was purified with HPLC (30-40% water-acetonitrile, 10 min, flow 30 ml/min) to rac-N-(6-amino-5-methylpyridin-3-yl)-2-oxo-2-((2R,5S)-2-phenyl-5-(trifluoromethyl)piperidin-1-yl)acetamide (54.2 mg, 133.37 μmol, 71.41% yield)

$^1$H NMR (DMSO-d$_6$, 500 MHz): δ (ppm) 1.76 (m, 2H), 2.00 (m, 3H), 2.18 (m, 2H), 2.81 (m, 1H), 3.56 (m, 1H), 4.50 (m, 1H), 5.39 (m, 1H), 5.61 (m, 2H), 7.36 (m, 6H), 7.96 (m, 1H), 10.40 (m, 1H).

LCMS(ESI): [M+1]$^+$ m/z: calcd 406.2; found 407.0; Rt=1.001 min.

Example 764. The Synthesis of 1-(2-((6-amino-5-methylpyridin-3-yl)amino)-2-oxoacetyl)-6-phenylpiperidine-3-carboxamide (Compound 315, Compound 328

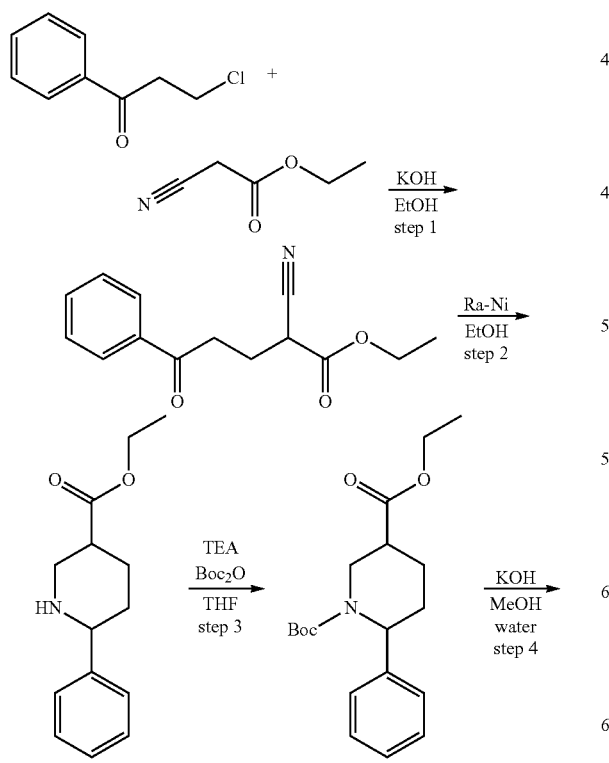

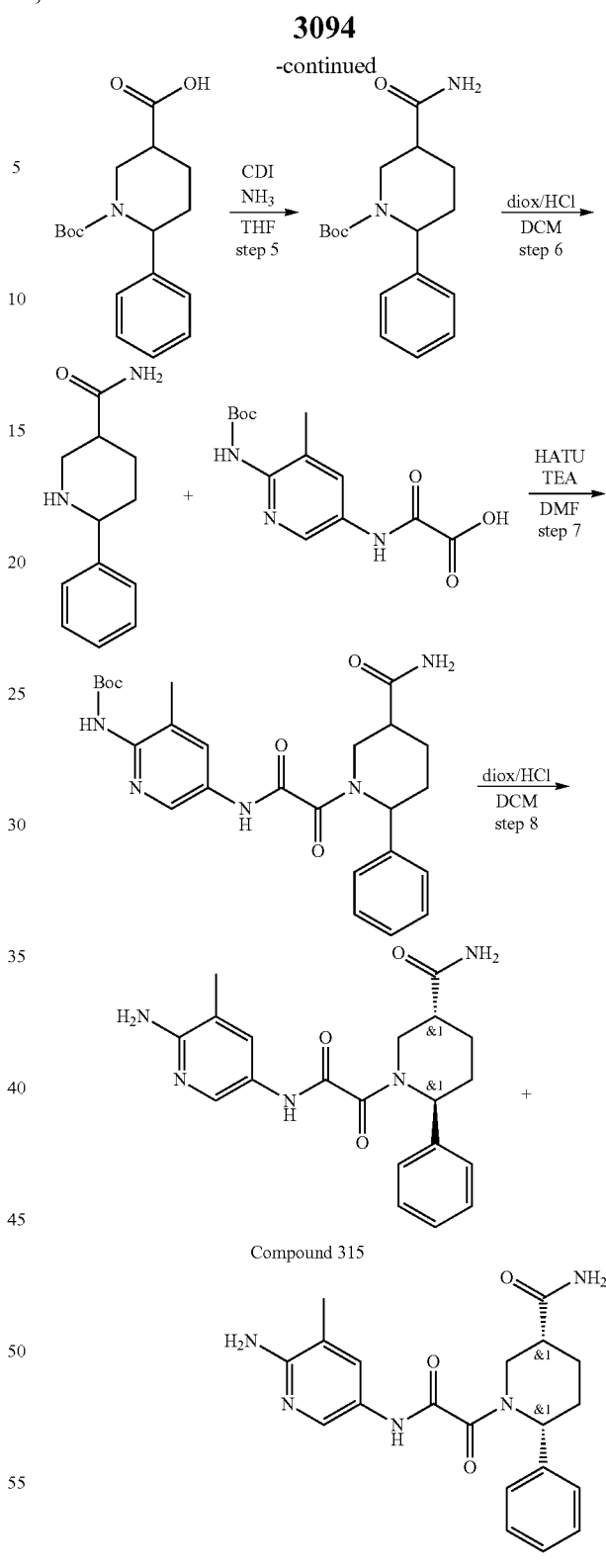

Compound 315

Compound 328

Step 1: Synthesis of Ethyl 2-Cyano-5-oxo-5-phenylpentanoate

KOH (9.98 g, 177.92 mmol, 4.89 mL) was added to EtOH (200 mL). After homogenization ethyl 2-cyanoacetate (80.50 g, 711.66 mmol, 75.94 mL) was added and after 5 min 3-chloro-1-phenyl-propan-1-one (20 g, 118.61 mmol) was added. The reaction mixture was stirred at 25° C. for 2 hr. Solvent was evaporated an the residue (60 g) was purified by comn chromatography to give mixture of product with ethyl 2-cyanoacetate. Ethyl 2-cyanoacetate was removed by distillation in vacuo to give ethyl 2-cyano-5-oxo-5-phenyl-pentanoate (18 g, 73.39 mmol, 61.87% yield).

$^1$H NMR (500 MHz, CDCl$_3$) δ (ppm) 1.32 (t, 3H), 2.32 (m, 1H), 2.48 (m, 1H), 3.26 (t, 2H), 3.81 (t, 1H), 4.29 (m, 2H), 7.48 (t, 2H), 7.59 (t, 1H), 7.96 (d, 2H).

LCMS(ESI): [M+1]$^+$ m/z: calcd 245.2; found 246.2; Rt=1.306 min.

Step 2: Synthesis of Ethyl 6-phenylpiperidine-3-carboxylate

Ethyl 2-cyano-5-oxo-5-phenyl-pentanoate (2 g, 8.15 mmol) were dissolved in EtOH (80 mL) and Raney Nickel in water (300 mg, 3.50 mmol) was added. The reaction mixture was heated at 70° C. in high pressure vessel at 50 atm H$_2$ pressure for 48 hr. The catalyst was filtered off, washed with MeOH and the solvent was evaporated, the residue was dried to give ethyl 6-phenylpiperidine-3-carboxylate (1.5 g, crude).

LCMS(ESI): [M+1]$^+$ m/z: calcd 233.2; found 234.2; Rt=0.947 min.

Step 3: Synthesis of 1-tert-butyl 3-ethyl 6-phenylpiperidine-1,3-Dicarboxylate To a suspension of ethyl 6-phenylpiperidine-3-carboxylate (1.5 g, 6.43 mmol) in THF (30 mL), TEA (1.63 g, 16.07 mmol, 2.24 mL) and di-tert-butyl dicarbonate (1.54 g, 7.07 mmol, 1.62 mL) were added. The reaction mixture was stirred at 25° C. for 12 hr and evaporated. The residue was dissolved in water and extracted with DCM. The organic extract was dried over Na$_2$SO$_4$ and evaporated to give 01-tert-butyl 03-ethyl 6-phenylpiperidine-1,3-dicarboxylate (1.9 g, crude) as slightly yellow oil.

$^1$H NMR (500 MHz, CDCl$_3$) δ (ppm) 1.25 (t, 3H), 1.43 (s, 9H), 1.92 (m, 2H), 2.49 (m, 1H), 2.78 (t, 1H), 3.03 (m, 1H), 4.15 (m, 2H), 4.28 (m, 1H), 4.48 (m, 1H), 5.33 (m, 1H), 7.23 (m, 5H).

LCMS(ESI): [M−Boc]$^+$ m/z: calcd 233.4; found 234.2; Rt=0.846 min.

Step 4: Synthesis of 1-(tert-butoxycarbonyl)-6-phenylpiperidine-3-carboxylic acid To the solution of 01-tert-butyl 03-ethyl 6-phenylpiperidine-1,3-dicarboxylate (1.9 g, 5.70 mmol) in MeOH (25 mL)/H$_2$O (10 mL) potassium hydroxide (639.44 mg, 11.40 mmol, 313.45 µL) was added and the reaction mixture was stirred at 25° C. for 13 hr. Mixture was evaporated to dryness. The residue (water solution) was acidified with sodium bisulfate to slightly acidic pH. Product was extracted with EtOAc (3*30 ml), dried over Na$_2$SO$_4$. EtOAc was evaporated to give 1-tert-butoxycarbonyl-6-phenyl-piperidine-3-carboxylic acid (1 g, crude).

$^1$H NMR (400 MHz, CDCl$_3$) δ (ppm) 1.45 (s, 9H), 1.97 (m, 2H), 2.48 (m, 1H), 2.92 (t, 1H), 2.96 (m, 1H), 4.28 (m, 1H), 4.45 (m, 1H), 5.30 (m, 1H), 7.25 (m, 5H). LCMS(ESI): [M−Boc]$^+$ m/z: calcd 205.4; found 206.2; Rt=1.384 min.

Step 5: Synthesis of tert-butyl 5-carbamoyl-2-phenylpiperidine-1-carboxylate To the stirred solution of 1-tert-butoxycarbonyl-6-phenyl-piperidine-3-carboxylic acid (1 g, 3.27 mmol) in THF (30 mL) carbonyldiimidazole (690.29 mg, 4.26 mmol) was added and the reaction mixture was stirred at 50° C. for 1.5 hr. Ammonia was bubbled through reaction mixture for 30 min. The reaction mixture was stirred at 25° C. for 30 min. THF was evaporated. The residue was diluted with water (40 ml), product was extracted with EtOAc (50 ml). Organic layer was dried over Na$_2$SO$_4$. EtOAc was evaporated to give tert-butyl 5-carbamoyl-2-phenyl-piperidine-1-carboxylate (1.2 g, crude).

$^1$H NMR (500 MHz, CDCl$_3$) δ (ppm) 1.45 (s, 9H), 1.73 (m, 2H), 2.48 (m, 1H), 2.87 (t, 1H), 3.03 (m, 1H), 4.34 (m, 1H), 5.42 (m, 1H), 5.65 (m, 1H), 7.25 (m, 5H), 9.55 (m, 2H).

LCMS(ESI): [M−Boc]$^+$ m/z: calcd 204.2; found 205.2; Rt=1.333 min.

Step 6: Synthesis of 6-phenylpiperidine-3-carboxamide

To the solution of tert-butyl 5-carbamoyl-2-phenyl-piperidine-1-carboxylate (0.7 g, 2.30 mmol) in DCM (7 mL) hydrogen chloride solution 4.0 M in dioxane (838.50 mg, 23.00 mmol, 1.05 mL) was added and the resulting mixture was stirred at 25° C. for 1.5 hr. Solvents were evaporated to give 6-phenylpiperidine-3-carboxamide (0.5 g, crude, HCl).

$^1$H NMR (500 MHz, DMSO-d$_6$) δ (ppm) 1.95 (m, 3H), 3.25 (m, 4H), 4.28 (m, 1H), 7.48 (m, 5H), 7.63 (m, 2H), 9.17 (m, 1H).

LCMS(ESI): [M+1]$^+$ m/z: calcd 204.2; found 205.2; Rt=0.619 min.

Step 7: Synthesis of tert-butyl (5-(2-(5-carbamoyl-2-phenylpiperidin-1-yl)-2-oxoacetamido)-3-methylpyridin-2-yl)carbamate To the solution of 6-phenylpiperidine-3-carboxamide (0.5 g, 2.08 mmol, HCl), 2-[[6-(tert-butoxycarbonylamino)-5-methyl-3-pyridyl]amino]-2-oxo-acetic acid (613.33 mg, 2.08 mmol) and HATU (868.72 mg, 2.28 mmol) in DMF (8 mL) triethylamine (840.70 mg, 8.31 mmol, 1.16 mL) was added. Mixture was stirred at 25° C. for 2 hr. Mixture was diluted with water (30 ml) and extracted with EtOAc (3*50 ml). Combined organic layers were washed with water (3*50 ml) and brine, then dried over Na$_2$SO$_4$ and evaporated to give tert-butyl N-[5-[[2-(5-carbamoyl-2-phenyl-1-piperidyl)-2-oxo-acetyl]amino]-3-methyl-2-pyridyl]carbamate (0.5 g, crude).

LCMS(ESI) [M+1]$^+$ m/z: calcd 481.5; found 482.2; Rt=1.138 min.

Step 8: Synthesis of 1-(2-((6-amino-5-methylpyridin-3-yl)amino)-2-oxoacetyl)-6-phenylpiperidine-3-carboxamide (Compound 315 and Compound 328

To the solution of tert-butyl N-[5-[[2-(5-carbamoyl-2-phenyl-1-piperidyl)-2-oxo-acetyl]amino]-3-methyl-2-pyridyl]carbamate (0.5 g, 1.04 mmol) in DCM (5 mL) hydrogen chloride solution 4.0 M in dioxane (378.58 mg, 10.38 mmol, 473.23 µL) was added and the resulting mixture was stirred at 25° C. for 2 hr. Solvents were evaporated. The residue was purified by reverse phase HPLC (30-30-40% 0-1-6 min 0.1% NH$_3$-methanol, flow: 30 ml/min (loading pump 4 ml/min methanol) target mass 381 column: YMC Triart C18 100×20 mm, 5 um) to give (3R,6R)-1-[2-[(6-amino-5-methyl-3-pyridyl)amino]-2-oxo-acetyl]-6-phenyl-piperidine-3-carboxamide (78 mg, 204.50 µmol, 19.69% yield) and (3R,6S)-1-[2-[(6-amino-5-methyl-3-pyridyl)

amino]-2-oxo-acetyl]-6-phenyl-piperidine-3-carboxamide (21 mg, 55.06 µmol, 5.30% yield).

Compound 315: $^1$H NMR (400 MHz, CDCl$_3$) δ (ppm) 2.08 (m, 3H), 2.18 (m, 1H), 2.33 (m, 1H), 2.52 (m, 1H), 3.19 (m, 1H), 4.45 (m, 2H), 4.91 (m, 1H), 5.85 (m, 1H), 6.16 (m, 1H), 7.31 (m, 8H), 7.69 (m, 1H), 8.07 (m, 1H), 9.47 (m, 1H).

LCMS(ESI): [M+1]$^+$ m/z: calcd 381.4; found 382.2; Rt=1.751 min.

Compound 328: $^1$H NMR (600 MHz, DMSO-d$_6$) δ (ppm) 1.47 (m, 1H), 1.84 (m, 2H), 2.00 (m, 3H), 2.96 (m, 2H), 3.99 (m, 1H), 5.50 (m, 3H), 6.87 (m, 1H), 7.29 (m, 3H), 7.34 (m, 1H), 7.39 (m, 3H), 7.48 (m, 1H), 8.00 (d, 1H), 10.57 (s, 1H).

LCMS(ESI): [M+1]$^+$ m/z: calcd 381.4; found 382.2; Rt=1.678 min.

Example 765. The Synthesis of 1-(2-((6-amino-5-methylpyridin-3-yl)amino)-2-oxoacetyl)-N-methyl-6-phenylpiperidine-3-carboxamide (Compound 249, Compound 253

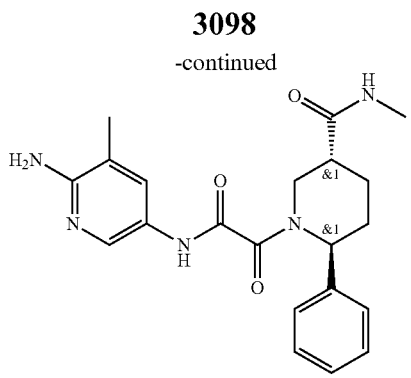

Compound 249

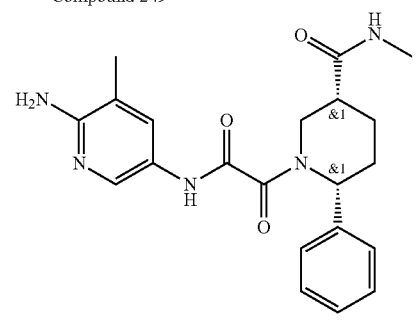

Compound 253

Step 1: Synthesis of tert-butyl 5-(methylcarbamoyl)-2-phenylpiperidine-1-carboxylate To the stirred solution of 1-tert-butoxycarbonyl-6-phenyl-piperidine-3-carboxylic acid (prepared as described above) (3 g, 9.82 mmol) in THF (100 mL) carbonyldiimidazole (2.07 g, 12.77 mmol) was added and the reaction mixture was stirred at 50° C. for 1.5 hr. Methyl amine was bubbled through reaction mixture for 30 min. The reaction mixture was stirred at 25° C. for 30 min. THF was evaporated. The residue was diluted with water (150 ml), product was extracted with EtOAc (2*100 ml). Organic layer was dried over Na$_2$SO$_4$. EtOAc was evaporated to give tert-butyl 5-(methylcarbamoyl)-2-phenyl-piperidine-1-carboxylate (2 g, crude).

LCMS(ESI): [M−Boc]$^+$ m/z: calcd 218.2; found 219.2; Rt=1.360 min.

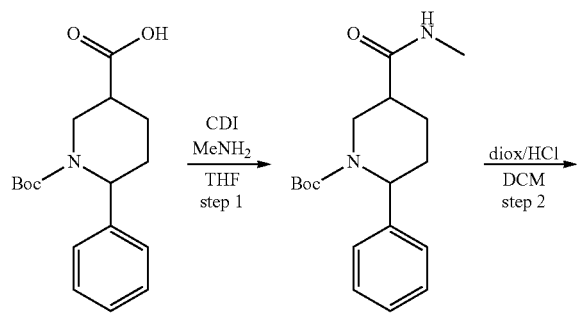

Step 2: Synthesis of N-methyl-6-phenylpiperidine-3-carboxamide

To the solution of tert-butyl 5-(methylcarbamoyl)-2-phenyl-piperidine-1-carboxylate (0.7 g, 2.20 mmol) in DCM (7 mL) hydrogen chloride solution 4.0 M in dioxane (801.57 mg, 21.98 mmol, 1.00 mL) was added and the resulting mixture was stirred at 25° C. for 2 hr. Solvents were evaporated to give N-methyl-6-phenyl-piperidine-3-carboxamide (0.5 g, crude, HCl).
$^1$H NMR (500 MHz, DMSO-d$_6$) δ (ppm) 1.28 (m, 1H), 1.55 (m, 2H), 1.97 (m, 2H), 2.83 (m, 2H), 3.55 (d, 3H), 4.29 (m, 1H), 7.44 (m, 5H), 8.15 (m, 1H), 8.43 (m, 1H).

LCMS(ESI): [M+1]$^+$ m/z: calcd 218.2; found 219.2; Rt=0.656 min.

Step 3: Synthesis of tert-butyl (3-methyl-5-(2-(5-(methylcarbamoyl)-2-phenylpiperidin-1-yl)-2-oxoacetamido)pyridin-2-yl)carbamate

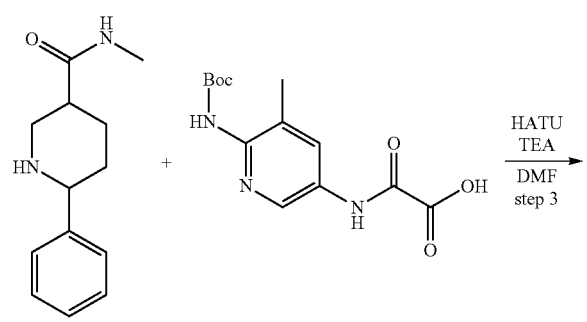

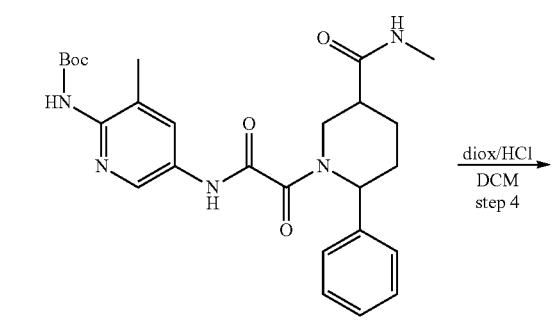

To the solution of N-methyl-6-phenyl-piperidine-3-carboxamide (0.5 g, 2.29 mmol), 2-[[6-(tert-butoxycarbonylamino)-5-methyl-3-pyridyl]amino]-2-oxo-acetic acid (676.36 mg, 2.29 mmol) and HATU (870.91 mg, 2.29 mmol) in DMF (2 mL) triethylamine (231.77 mg, 2.29 mmol, 319.25 µL) was added. Mixture was stirred at 25° C. for 2 hr. Mixture was diluted with water (30 ml) and extracted with EtOAc (3*50 ml). Combined organic layers were washed with water (3*50 ml) and brine, then dried over Na$_2$SO$_4$ and evaporated to give tert-butyl N-[3-methyl-5-[[2-[5-(methylcarbamoyl)-2-phenyl-1-piperidyl]-2-oxo-acetyl]amino]-2-pyridyl]carbamate (0.8 g, crude).

LCMS(ESI): [M+1]$^+$ m/z: calcd 495.5; found 496.2; Rt=1.183 min.

Step 4: Synthesis of 1-(2-((6-amino-5-methylpyridin-3-yl)amino)-2-oxoacetyl)-N-methyl-6-phenylpiperidine-3-carboxamide (Compound 249 and Compound 253

To the solution of tert-butyl N-[3-methyl-5-[[2-[5-(methylcarbamoyl)-2-phenyl-1-piperidyl]-2-oxo-acetyl]amino]-2-pyridyl]carbamate (0.8 g, 1.61 mmol) in DCM (15 mL) hydrogen chloride solution 4.0 M in dioxane (58.86 mg, 1.61 mmol, 73.57 µL) was added and the resulting mixture was stirred at 25° C. for 1.5 hr. Solvents were evaporated and the residue was submitted for reverse phase HPLC (30-30-50% 0-1-6 min 0.1% NH$_3$-methanol, flow: 30 ml/min (loading pump 4 ml/min methanol)) to give 2 fractions: 1st: 100 mg (100% LCMS); (2D-NMR: cis-isomer) and 2nd: 71 mg (98.5% LCMS); (2D-NMR: trans-isomer).

Compound 249: LCMS(ESI): [M]$^+$ m/z: calcd 395.4; found 396.2; Rt=1.916 min.

Compound 253: LCMS(ESI): [M]$^+$ m/z: calcd 395.4; found 396.2; Rt=1.916 min.

Example 766. The Synthesis of rac-5-(2-oxo-2-((2R,5S)-2-phenyl-5-(1H-pyrazol-5-yl)piperidin-1-yl)acetamido)nicotinamide (Compound 669)

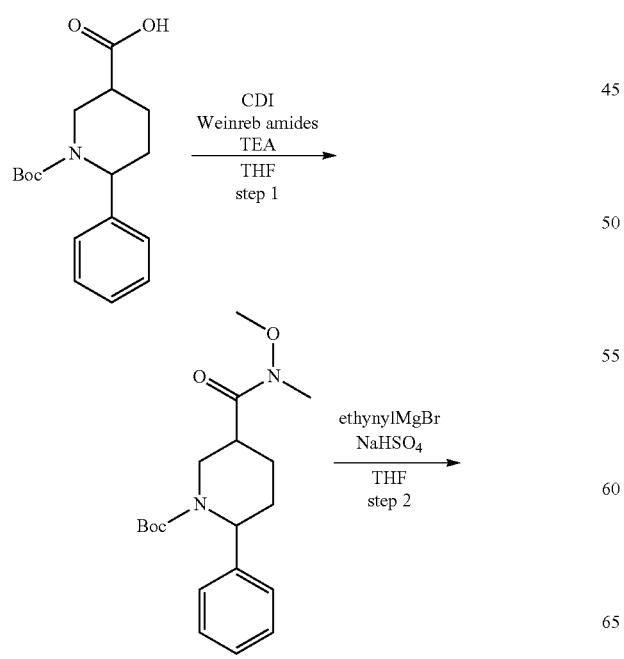

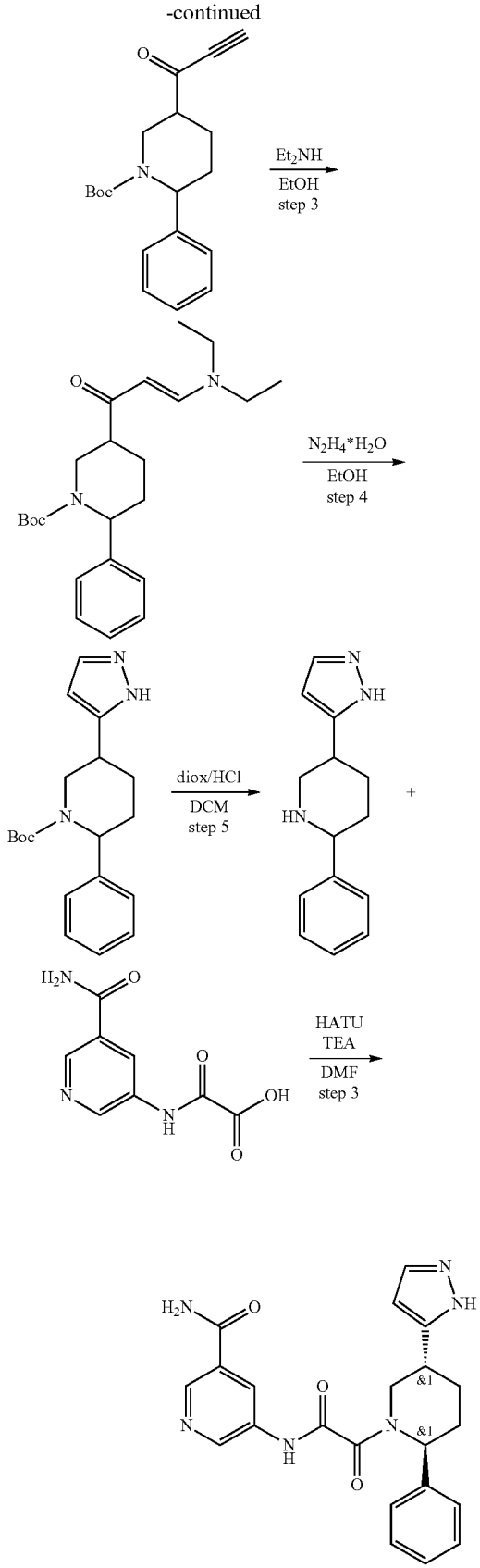

Compound 669

Step 1: Synthesis of tert-butyl 5-(methoxy(methyl) carbamoyl)-2-phenylpiperidine-1-carboxylate To the stirred solution of 1-tert-butoxycarbonyl-6-phenyl-piperidine-3-carboxylic acid (13.5 g, 44.21 mmol) (prepared as described above) in THF (200 mL) CDI (9.32 g, 57.47 mmol) was added and the reaction mixture was stirred at 25° C. for 2 hr. N,O-dimethylhydroxylamine hydrochloride (6.04 g, 61.89 mmol) was added followed by addition of triethylamine (6.26 g, 61.89 mmol, 8.63 mL). The reaction mixture was stirred at 25° C. for 15 hr. Tetrahydrofurane was evaporated. The residue was diluted with DCM (200 ml) and washed with water (3*100 ml). Organic layer was dried over $Na_2SO_4$. DCM was evaporated to give tert-butyl 5-[methoxy(methyl)carbamoyl]-2-phenyl-piperidine-1-carboxylate (20 g, crude) which was used in the next step without further purification.

$^1$H NMR (500 MHz, $CDCl_3$) δ (ppm) 1.48 (s, 9H), 1.75 (m, 2H), 1.84 (m, 2H), 2.48 (m, 1H), 2.88 (m, 1H), 3.68 (s, 3H), 3.72 (s, 3H), 4.72 (m, 1H), 5.41 (m, 1H), 7.24 (m, 5H).

LCMS(ESI): [M−Boc]$^+$ m/z: calcd 248.2; found 249.2; Rt=1.366 min.

Step 2: Synthesis of tert-butyl 2-phenyl-5-propioloylpiperidine-1-carboxylate To the stirred ethynylmagnesium bromide solution 0.5 M in THF (9.27 g, 71.75 mmol, 143 mL) at −30° C. the solution of tert-butyl 5-[methoxy(methyl)carbamoyl]-2-phenyl-piperidine-1-carboxylate (5 g, 14.35 mmol) in THF (70 mL) was added dropwise. The reaction mixture was slowly heated to room temperature and stirred for 12 hr. The reaction mixture was added to intensively stirred (previously prepared) $NaHSO_4$ solution (17.2 g in 170 ml of water) and stirred at 25° C. for 4 hr. Organic phase was separated. Water phase was extracted with DCM (2*60 ml). Combined organic phases were washed with water, brine and dried over $Na_2SO_4$. Solvents were evaporated in vacuo to give tert-butyl 2-phenyl-5-prop-2-ynoyl-piperidine-1-carboxylate (3.5 g, 11.17 mmol, 77.83% yield).

$^1$H NMR (400 MHz, $CDCl_3$) δ (ppm) 1.46 (s, 9H), 1.82 (m, 2H), 2.02 (m, 1H), 2.45 (m, 1H), 2.66 (m, 1H), 2.77 (m, 1H), 3.21 (m, 1H), 4.39 (m, 1H), 5.43 (m, 1H), 7.28 (m, 5H).

LCMS(ESI): [M−Boc]$^+$ m/z: calcd 213.2; found 214.2; Rt=1.507 min.

Step 3: Synthesis of tert-butyl 5-(3-(diethylamino) acryloyl)-2-phenylpiperidine-1-carboxylate To the tert-butyl 2-phenyl-5-prop-2-ynoyl-piperidine-1-carboxylate (3.5 g, 11.17 mmol) solution of diethylamine (1.23 g, 16.75 mmol, 1.74 mL) in ethanol (100 mL) was added and the reaction mixture was stirred at 25° C. for 1.5 hr. Ethanol was evaporated in vacuo to give tert-butyl 5-[(E)-3-(diethylamino)prop-2-enoyl]-2-phenyl-piperidine-1-carboxylate (3.5 g, crude).

$^1$H NMR (400 MHz, $CDCl_3$) δ (ppm) 1.18 (m, 6H), 1.42 (s, 9H), 1.67 (m, 2H), 1.88 (m, 3H), 2.44 (m, 2H), 2.79 (m, 1H), 3.18 (m, 4H), 5.05 (m, 1H), 7.27 (m, 5H), 7.50 (m, 1H).

LCMS(ESI): [M−Boc]$^+$ m/z: calcd 286.2; found 287.2; Rt=1.520 min.

Step 4: Synthesis of tert-butyl 2-phenyl-5-(1H-pyrazol-5-yl)piperidine-1-carboxylate To the stirred solution of tert-butyl 5-[(E)-3-(diethylamino)prop-2-enoyl]-2-phenyl-piperidine-1-carboxylate (1 g, 2.59 mmol) in ethanol (30 mL) hydrazine hydrate solution 55% in water (35% hydrazine) (518.05 mg, 5.17 mmol, 502.97 μL, 50% purity) was added and resulting mixture was stirred at 78° C. for 24 hr. Ethanol was evaporated. The residue was diluted with water (100 ml) and extracted with ethyl acetate (2*50 ml). Combined organic layers were dried over $Na_2SO_4$. EtOAc was evaporated to give tert-butyl 2-phenyl-5-(1H-pyrazol-5-yl)piperidine-1-carboxylate (700 mg, crude).

$^1$H NMR (500 MHz, $CDCl_3$) δ (ppm) 1.49 (s, 9H), 1.74 (m, 2H), 2.08 (m, 2H), 2.48 (m, 1H), 2.79 (m, 1H), 2.98 (m, 1H), 4.34 (m, 1H), 5.52 (m, 1H), 6.04 (m, 1H), 7.35 (m, 5H), 7.43 (m, 1H).

LCMS(ESI): [M−Boc]$^+$ m/z: calcd 227.2; found 228.2; Rt=1.406 min.

Step 5: Synthesis of 2-phenyl-5-(1H-pyrazol-5-yl)piperidine

To the stirred solution of tert-butyl 2-phenyl-5-(1H-pyrazol-5-yl)piperidine-1-carboxylate (700 mg, 2.14 mmol) in DCM (5 mL) hydrogen chloride solution 4.0 M in dioxane (779.51 mg, 21.38 mmol, 974.39 μL) was added. The reaction mixture was stirred at 25° C. for 3 hr. Solvents were evaporated in vacuo to give 2-phenyl-5-(1H-pyrazol-5-yl) piperidine (700 mg, crude, 2HCl).

$^1$H NMR (500 MHz, DMSO-$d_6$) δ (ppm) 1.68 (m, 1H), 1.87 (m, 1H), 2.09 (m, 3H), 3.39 (m, 2H), 4.42 (m, 1H), 6.33 (m, 1H), 7.46 (m, 5H), 7.76 (m, 1H), 8.49 (m, 1H), 10.03 (m, 1H).

LCMS(ESI): [M+1]$^+$ m/z: calcd 227.2; found 228.2; Rt=0.860 min.

Step 6: Synthesis of rac-5-(2-oxo-2-((2R,5S)-2-phenyl-5-(1H-pyrazol-5-yl)piperidin-1-yl)acetamido)nicotinamide (Compound 669)

To the solution of 2-phenyl-5-(1H-pyrazol-5-yl)piperidine (300 mg, 999.25 μmol, 2HCl), 2-[(5-carbamoyl-3-pyridyl)amino]-2-oxo-acetic acid (209.00 mg, 673.44 μmol, Et$_3$N) and triethylamine (707.80 mg, 6.99 mmol, 974.93 μL) in DMF (3 mL) HATU (417.94 mg, 1.10 mmol) was added portionwise. Mixture was stirred at 25° C. for 2 hr. The reaction mixture was purified by reverse phase HPLC (20-70% 0-5 min Water/MeOH+FA, flow: 30 ml/min (loading pump 4 ml/min methanol) target mass 419 column: Chromatorex 18 SMB100-5T 100×19 mm 5 u) to give 5-[[2-oxo-2-[(2S,5R)-2-phenyl-5-(1H-pyrazol-5-yl)-1-piperidyl] acetyl]amino]pyridine-3-carboxamide (97 mg, 231.81 μmol, 23.20% yield).

$^1$H NMR (600 MHz, DMSO-$d_6$) δ (ppm) 1.52 (m, 1H), 1.96 (m, 1H), 2.59 (m, 1H), 2.86 (m, 1H), 3.00 (m, 1H), 4.23 (m, 2H), 5.52 (m, 1H), 6.00 (m, 1H), 7.28 (m, 3H), 7.40 (m, 3H), 7.48 (m, 1H), 7.62 (m, 1H), 8.15 (m, 1H), 8.51 (m, 1H), 8.75 (m, 1H), 8.91 (m, 1H), 11.3 (m, 1H).

LCMS(ESI): [M]$^+$ m/z: calcd 418.4; found 419.2; Rt=2.052 min.

Example 767. The Synthesis of 5-(2-(5-(hydroxymethyl)-2-phenylpiperidin-1-yl)-2-oxoacetamido)nicotinamide (Compound 266, Compound 285

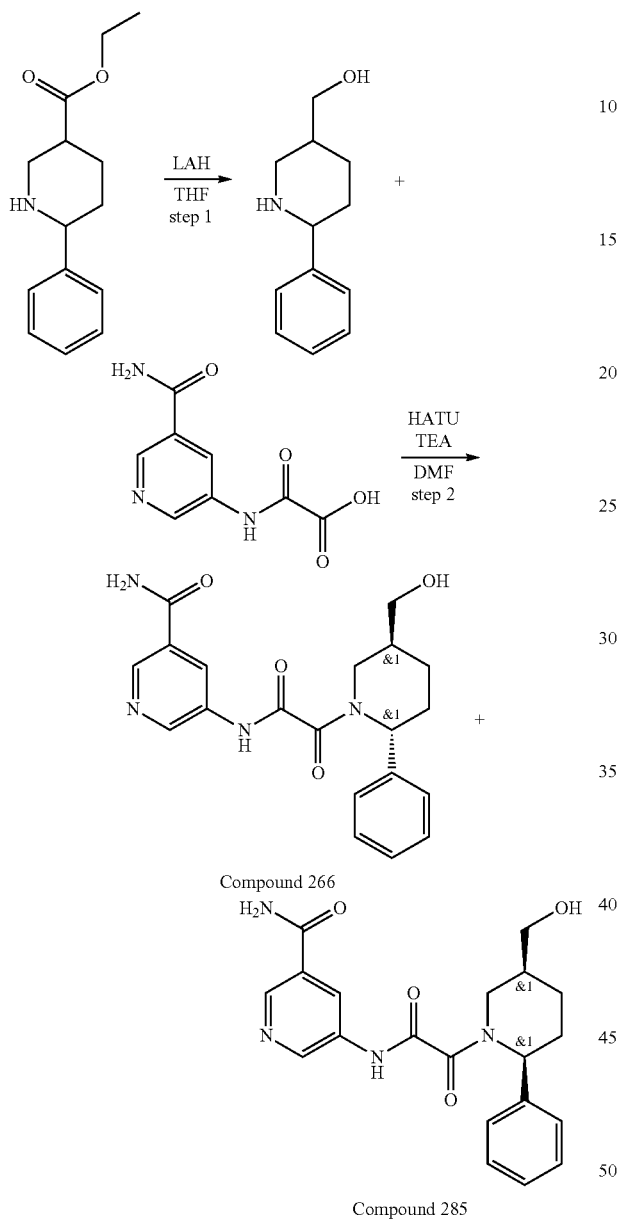

Compound 266

Compound 285

Step 1: Synthesis of (6-phenylpiperidin-3-yl)methanol

To the pre-cooled (−10° C.) stirred solution of ethyl 6-phenylpiperidine-3-carboxylate (2 g, 8.57 mmol) (prepared as described above) in THF (50 mL) lithium aluminium hydride (325.36 mg, 8.57 mmol) was added portionwise. The reaction mixture was stirred at 25° C. for 1.5 hr. The reaction mixture was quenched with 20% water solution in THF. The obtained precipitate was filtered and the residue was washed with hot THF. The combined filtrate was evaporated under reduced pressure to give (6-phenyl-3-piperidyl)methanol (1.7 g, crude).

$^1$H NMR (500 MHz, DMSO-$d_6$) δ (ppm) 1.95 (m, 4H), 2.32 (m, 1H), 2.82 (m, 1H), 3.48 (m, 1H), 3.63 (m, 2H), 3.95 (m, 1H), 4.04 (m, 1H), 7.32 (m, 5H).

LCMS(ESI): [M]$^+$ m/z: calcd 191.2; found 192.2; Rt=0.724 min.

Step 2: Synthesis of 5-(2-(5-(hydroxymethyl)-2-phenylpiperidin-1-yl)-2-oxoacetamido)nicotinamide (Compound 266 and Compound 285

To the solution of (6-phenyl-3-piperidyl)methanol (0.4 g, 2.09 mmol), 2-[(5-carbamoyl-3-pyridyl)amino]-2-oxo-acetic acid (513.66 mg, 2.09 mmol, HCl) and HATU (874.69 mg, 2.30 mmol) in DMF (4.5 mL) triethylamine (1.06 g, 10.46 mmol, 1.46 mL) was added. Mixture was stirred at 25° C. for 2 hr. Mixture was submitted for reverse phase HPLC (0-5 min 0-40% water-methanol (NH$_3$ 0.1%), flow 30 ml/min (loading pump 4 ml/min methanol (NH$_3$ 0.1%)) to give 3 fractions: 1st: 97 mg (96% LCMS)-(2D studies: cis-isomer), 2nd: 68 mg (96% LCMS)-(2D studies: trans-isomer), 3d: 40 mg (mixture of diastereomers).

Compound 266: LCMS(ESI): [M]$^+$ m/z: calcd 382.4; found 383.2; Rt=2.569 min.

Compound 285: LCMS(ESI): [M]$^+$ m/z: calcd 382.4; found 383.2; Rt=2.525 min.

Example 768. The Synthesis of 5-[[2-[(2R,5S)-5-methyl-2-(6-oxo-1H-pyridin-3-yl)-1-piperidyl]-2-oxo-acetyl]amino]pyridine-3-carboxamide and 5-[[2-[(2S,5R)-5-methyl-2-(6-oxo-1H-pyridin-3-yl)-1-piperidyl]-2-oxo-acetyl]amino]pyridine-3-carboxamide, 5-[[2-[(2R,5R)-5-methyl-2-(6-oxo-1H-pyridin-3-yl)-1-piperidyl]-2-oxo-acetyl]amino]pyridine-3-carboxamide and 5-[[2-[(2S,5S)-5-methyl-2-(6-oxo-1H-pyridin-3-yl)-1-piperidyl]-2-oxo-acetyl]amino]pyridine-3-carboxamide (Compound 350, Compound 351, Compound 401 and Compound 402

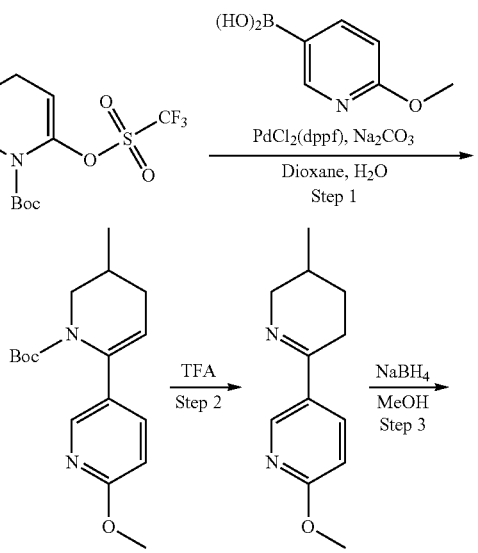

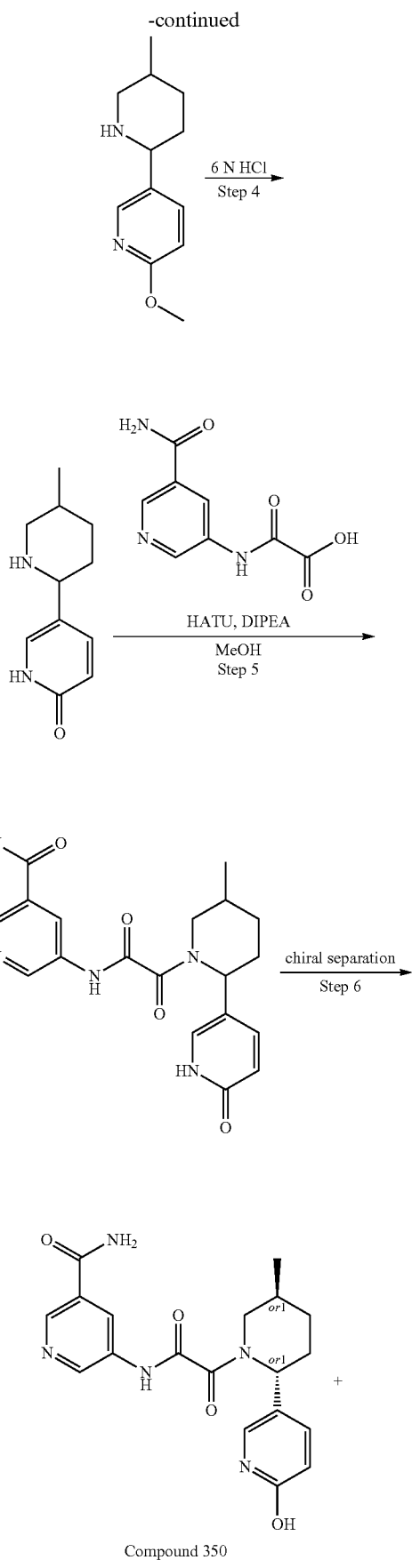

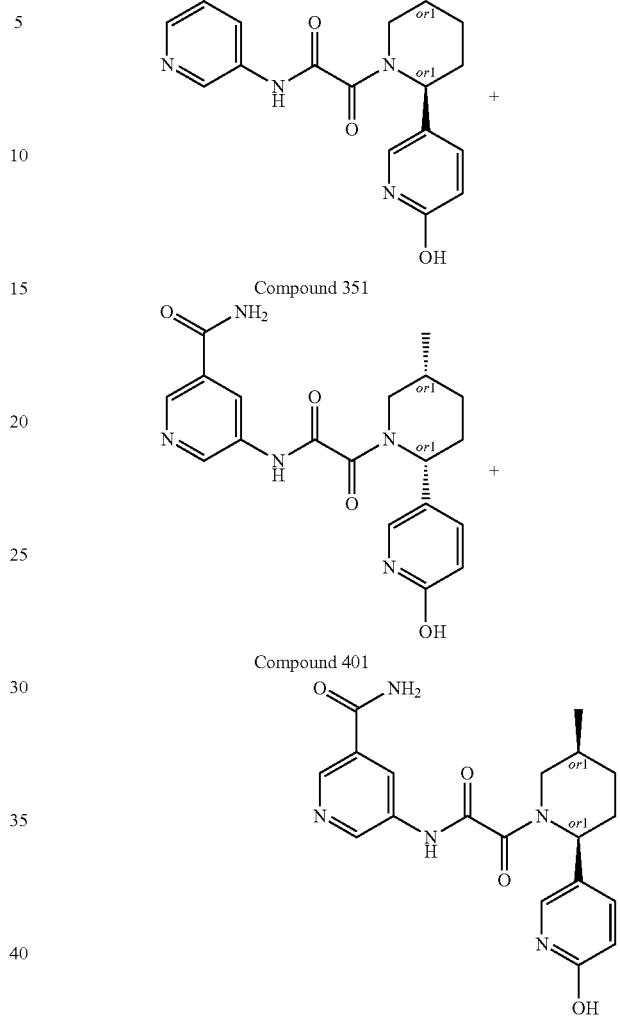

Compound 351

Compound 401

Compound 402

Step 1: Synthesis of tert-butyl 6-(6-methoxy-3-pyridyl)-3-methyl-3,4-dihydro-2H-pyridine-1-carboxylate A stirring suspension of tert-butyl 3-methyl-6-(trifluoromethylsulfonyloxy)-3,4-dihydro-2H-pyridine-1-carboxylate (10 g, 26.06 mmol), (6-methoxy-3-pyridyl)boronic acid (3.99 g, 26.06 mmol) and Sodium carbonate (8.29 g, 78.19 mmol, 3.28 mL) in 1,4-dioxane (120 mL) and water (40 mL) was purged with argon for 10 minutes. After 10 minutes, Pd(dppf)Cl$_2$CH$_2$Cl$_2$ (956.99 mg, 1.17 mmol) was added under argon. The reaction mixture was stirred under argon at 90° C. for 18 hours. After 18 hours, the reaction mixture was cooled to room temperature and filtered. The filter cake was washed with ethyl acetate (4×50 mL) and discarded. The filtrate was evaporated under reduced pressure, and the crude residue was purified by column chromatography (SiO$_2$, 0-100% MTBE in hexane) to obtain tert-butyl 6-(6-methoxy-3-pyridyl)-3-methyl-3,4-dihydro-2H-pyridine-1-carboxylate (3.60 g, 11.83 mmol, 45.38% yield) as light-yellow solid.

LCMS(ESI): [M+H]⁺ m/z: calcd 304.2; found 305.2; Rt=1.528 min.

Step 2: Synthesis of 2-methoxy-5-(3-methyl-2,3,4,5-tetrahydropyridin-6-yl)pyridine Trifluoroacetic acid (11.99 g, 105.13 mmol, 8.10 mL) was added to tert-butyl 6-(6-methoxy-3-pyridyl)-3-methyl-3,4-dihydro-2H-pyridine-1-carboxylate (1.60 g, 5.26 mmol) and the resulting reaction mixture was stirred at 25° C. for 1 hour. After 1 hour, the reaction mixture was concentrated under reduced pressure to obtain light yellow liquid residue. The obtained residue was dissolved in 20 mL ice-cold water and 10% NaOH solution was added drop wise till pH=9-10. The resulting suspension was extracted with dichloromethane (3×20 mL). The combined organic phase was washed with water (10 mL), dried over Na₂SO₄ and concentrated under reduced pressure to obtain 2-methoxy-5-(3-methyl-2,3,4,5-tetrahydropyridin-6-yl)pyridine (1.30 g, crude) as a light yellow solid. The crude product was used in the next step reaction without any further purification.

LCMS(ESI): [M+H]⁺ m/z: calcd 204.2; found 205.2; Rt=0.728 min.

Step 3: Synthesis of 2-methoxy-5-(5-methyl-2-piperidyl)pyridine

Sodium Borohydride (325.15 mg, 8.59 mmol) was added portion wise at 0° C. to a stirred solution of 2-methoxy-5-(3-methyl-2,3,4,5-tetrahydropyridin-6-yl)pyridine (1.30 g, 5.73 mmol) in methanol (15 mL). The reaction mixture was stirred at the room temperature for 2 hours. After 2 hours, the reaction mixture was concentrated under reduced pressure to obtain light yellow liquid residue. The obtained residue was dissolved in water (20 mL) and extracted with dichloromethane (3×25 mL). The combined organic phase was washed with water (2×10 mL), dried over Na₂SO₄ and concentrated under reduced pressure to obtain crude product 2-methoxy-5-(5-methyl-2-piperidyl)pyridine (1.00 g, 4.85 mmol, 84.61% yield) as a yellow liquid. The crude product was used in the next step reaction without any further purification.

LCMS(ESI): [M+H]⁺ m/z: calcd 206.2; found 207.2; Rt=0.668 min.

Step 4: Synthesis of 5-(5-methyl-2-piperidyl)-1H-pyridin-2-one

A solution of 2-methoxy-5-(5-methyl-2-piperidyl)pyridine (0.3 g, 1.45 mmol) in 6N aqueous hydrochloric acid (10 mL) was stirred at 95° C. for 48 hours. After 48 hours, the reaction mixture was allowed to cool to room temperature and evaporated in vacuo to afford 5-(5-methyl-2-piperidyl)-1H-pyridin-2-one (320 mg, 1.40 mmol, 96.20% yield, HCl salt) as a yellow solid.

The crude product was used directly in the next step reaction.

LCMS(ESI): [M+H]⁺ m/z: calcd 192.2; found 193.2; Rt=0.591 min.

Step 5: Synthesis of 5-[[2-[5-methyl-2-(6-oxo-1H-pyridin-3-yl)-1-piperidyl]-2-oxo-acetyl]amino]pyridine-3-carboxamide To a stirred solution of 5-(5-methyl-2-piperidyl)-1H-pyridin-2-one (300 mg, 1.31 mmol, HCl salt), 2-[(5-carbamoyl-3-pyridyl)amino]-2-oxo-acetic acid (407.07 mg, 1.31 mmol, Et₃N salt) and N,N-Diisopropylethylamine (847.61 mg, 6.56 mmol, 1.14 mL) in DMF (10 mL) at 25° C. was added HATU (598.48 mg, 1.57 mmol) portion wise. The resulting reaction mixture was stirred at 25° C. for 72 hours. After 72 hours, a sample was submitted for LCMS analysis. LCMS indicated ~20% of desired product mass. The reaction mixture was concentrated under reduced pressure to obtain the crude product, which was purified by reverse phase HPLC (Eluent: 0-5 min, 10-25% water-methanol+formic acid; column: SunFire C18 100×19 mm, 5 um; flow rate: 30 mL/min; loading pump: 4 mL/min, methanol) to get product 5-[[2-[5-methyl-2-(6-oxo-1H-pyridin-3-yl)-1-piperidyl]-2-oxo-acetyl]amino]pyridine-3-carboxamide (120 mg, 312.99 μmol, 23.86% yield) as a yellow gum.

LCMS(ESI): [M+H]⁺ m/z: calcd 383.2; found 384.2; Rt=2.035 min.

Step 6: Chiral Separation of 5-[[2-[(2R,5S)-5-methyl-2-(6-oxo-1H-pyridin-3-yl)-1-piperidyl]-2-oxo-acetyl]amino]pyridine-3-carboxamide and 5-[[2-[(2S,5R)-5-methyl-2-(6-oxo-1H-pyridin-3-yl)-1-piperidyl]-2-oxo-acetyl]amino]pyridine-3-carboxamide, 5-[[2-[(2R,5R)-5-methyl-2-(6-oxo-1H-pyridin-3-yl)-1-piperidyl]-2-oxo-acetyl]amino]pyridine-3-carboxamide and 5-[[2-[(2S,5S)-5-methyl-2-(6-oxo-1H-pyridin-3-yl)-1-piperidyl]-2-oxo-acetyl]amino]pyridine-3-carboxamide (Compound 350, Compound 351, Compound 401 and Compound 402

5-[[2-[5-methyl-2-(6-oxo-1H-pyridin-3-yl)-1-piperidyl]-2-oxo-acetyl]amino]pyridine-3-carboxamide (120 mg, 312.99 μmol) was subjected to chiral HPLC purification (Column: Chiralpak AD-H-III (250×20 mm, 5 um); Mobile phase: Hexane-IPA-MeOH, 60-20-20; Flow rate: 14 mL/min) to afford 5-[[2-[(2S,5S)-5-methyl-2-(6-oxo-1H-pyridin-3-yl)-1-piperidyl]-2-oxo-acetyl]amino]pyridine-3-carboxamide (Compound 402, 5.6 mg, 14.61 μmol, 4.67% yield), 5-[[2-[(2R,5R)-5-methyl-2-(6-oxo-1H-pyridin-3-yl)-1-piperidyl]-2-oxo-acetyl]amino]pyridine-3-carboxamide (Compound 401, 5.6 mg, 14.61 μmol, 4.67% yield), 5-[[2-[(2S,5R)-5-methyl-2-(6-oxo-1H-pyridin-3-yl)-1-piperidyl]-2-oxo-acetyl]amino]pyridine-3-carboxamide (Compound 351, 44 mg, 114.76 μmol, 36.67% yield) and 5-[[2-[(2R,5S)-5-methyl-2-(6-oxo-1H-pyridin-3-yl)-1-piperidyl]-2-oxo-acetyl]amino]pyridine-3-carboxamide (Compound 350, 62 mg, 161.71 μmol, 51.67% yield) as off-white solids.

Compound 350: ¹H NMR (DMSO-d₆, 600 MHz): δ (ppm) 1.00-1.03 (m, 3H), 1.26-1.35 (m, 1H), 1.69-1.76 (m, 1H), 1.84-1.91 (m, 1H), 1.93-2.06 (m, 2H), 2.81-3.23 (m, 1H), 3.39-3.93 (m, 1H), 4.88-5.38 (m, 1H), 6.29-6.40 (m, 1H), 7.17-7.24 (m, 1H), 7.33-7.48 (m, 1H), 7.56-7.64 (m, 1H), 8.11-8.18 (m, 1H), 8.42-8.50 (m, 1H), 8.73-8.79 (m, 1H), 8.83-8.90 (m, 1H), 11.12-11.26 (m, 1H), 11.60 (s, 1H).

LCMS(ESI): [M+H]⁺ m/z: calcd 383.2; found 384.0; Rt=3.340 min.

Chiral HPLC: Rt=20.45 min (Column: AD-H; Mobile phase: Hexane-IPA-MeOH, 50-25-25; Flow Rate: 0.6 mL/min).

Compound 351: ¹H NMR (DMSO-d₆, 500 MHz): δ (ppm) 0.97-1.02 (m, 3H), 1.25-1.38 (m, 1H), 1.68-1.76 (m, 1H), 1.79-1.91 (m, 1H), 1.91-1.98 (m, 1H), 1.99-2.03 (m, 1H), 2.79-3.23 (m, 1H), 3.36-3.96 (m, 1H), 4.86-5.38 (m, 1H), 6.29-6.40 (m, 1H), 7.20 (s, 1H), 7.31-7.46 (m, 1H), 7.54-7.64 (m, 1H), 8.08-8.21 (m, 1H), 8.43-8.50 (m, 1H), 8.71-8.81 (m, 1H), 8.82-8.91 (m, 1H), 11.15-11.34 (m, 1H), 11.60 (s, 1H).

LCMS(ESI): [M+H]⁺ m/z: calcd 383.2; found 384.0; Rt=3.338 min.

Chiral HPLC: Rt=15.45 min (Column: AD-H; Mobile phase: Hexane-IPA-MeOH, 50-25-25; Flow Rate: 0.6 mL/min).

Compound 401: $^1$H NMR (DMSO-$d_6$, 600 MHz): δ (ppm) 0.75-0.84 (m, 3H), 1.11-1.18 (m, 1H), 1.57-1.69 (m, 2H), 1.71-1.87 (m, 1H), 2.26-2.29 (m, 1H), 2.51-2.58 (m, 1H), 3.54-4.18 (m, 1H), 4.88-5.45 (m, 1H), 6.34-6.42 (m, 1H), 7.16-7.21 (m, 1H), 7.30-7.43 (m, 1H), 7.57-7.65 (m, 1H), 8.11-8.22 (m, 1H), 8.44-8.50 (m, 1H), 8.74-8.79 (m, 1H), 8.82-8.90 (m, 1H), 11.07-11.39 (m, 1H), 11.62 (s, 1H).

LCMS(ESI): [M+H]⁺ m/z: calcd 383.2; found 384.0; Rt=3.311 min.

Chiral HPLC: Rt=12.57 min (Column: AD-H; Mobile phase: Hexane-IPA-MeOH, 50-25-25; Flow Rate: 0.6 mL/min).

Compound 402:

$^1$H NMR (DMSO-$d_6$, 600 MHz): δ (ppm) 0.73-0.84 (m, 3H), 1.10-1.17 (m, 1H), 1.57-1.70 (m, 2H), 1.73-1.85 (m, 1H), 2.13-2.19 (m, 0.6H), 2.25-2.30 (m, 1H), 2.54-2.58 (m, 0.4H), 3.42-4.19 (m, 1H), 4.87-5.48 (m, 1H), 6.32-6.42 (m, 1H), 7.14-7.24 (m, 1H), 7.32-7.46 (m, 1H), 7.56-7.65 (m, 1H), 8.10-8.22 (m, 1H), 8.44-8.54 (m, 1H), 8.71-8.80 (m, 1H), 8.82-8.91 (m, 1H), 11.20-11.33 (m, 1H), 11.62 (br s, 1H).

LCMS(ESI): [M+H]⁺ m/z: calcd 383.2; found 384.0; Rt=3.313 min.

Chiral HPLC: Rt=9.96 min (Column: AD-H; Mobile phase: Hexane-IPA-MeOH, 50-25-25; Flow Rate: 0.6 mL/min).

Example 769. The Synthesis of 5-[[2-[(2S,5R)-2-(3-hydroxycyclopentyl)-5-methyl-1-piperidyl]-2-oxo-acetyl]amino]pyridine-3-carboxamide (Compound 517)

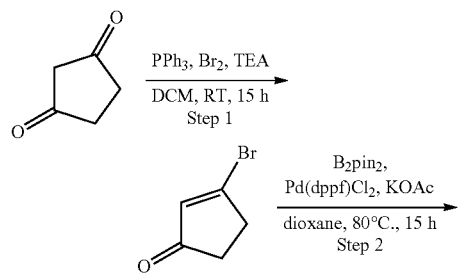

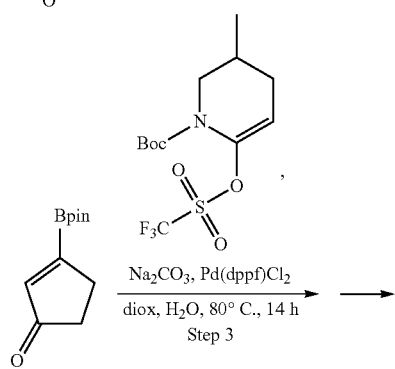

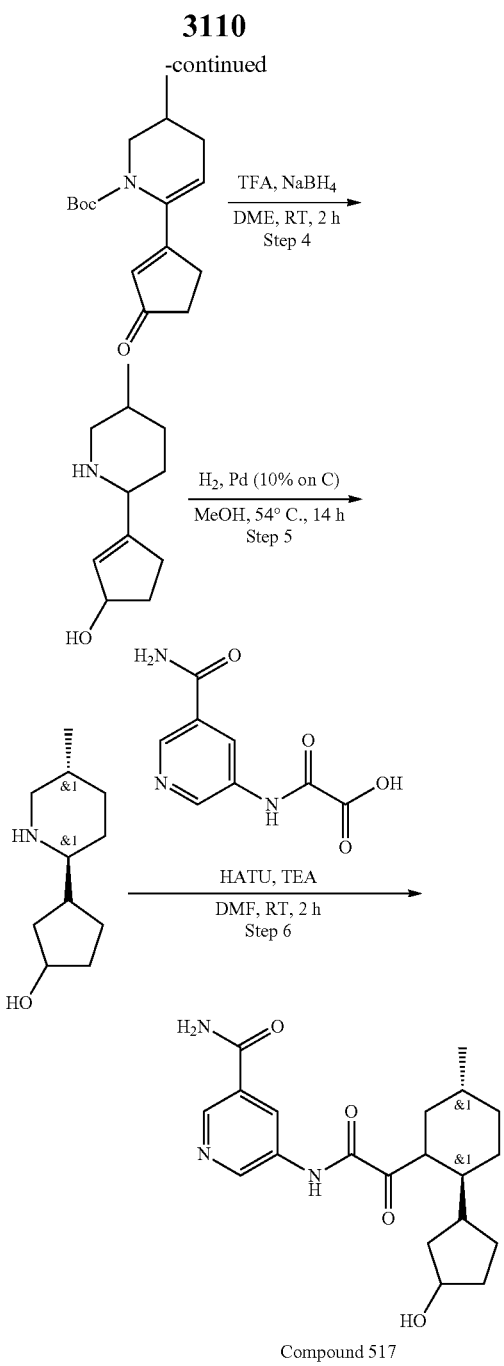

Step 1: The Synthesis of 3-bromocyclopent-2-en-1-one

To a stirred solution of Triphenylphosphine (6.42 g, 24.46 mmol) in DCM (50 mL), bromine (3.26 g, 20.39 mmol, 2.19 mL) was added at 0° C. The reaction mixture was stirred at same temperature for 45 min. Then, the solution of cyclopentane-1,3-dione (2 g, 20.39 mmol) and triethylamine (2.48 g, 24.46 mmol, 3.41 mL) in DCM (50 mL) was added. The reaction mixture was stirred at 25° C. for 15 hr. DCM was evaporated to give crude product which was purified by flash-chromatography with Hexane (two times). Hexane was evaporated to give 3-bromocyclopent-2-en-1-one (0.5 g, 3.11 mmol, 15.23% yield).

¹H NMR (500 MHz, CDCl₃) δ 2.54 (m, 2H), 2.98 (m, 2H), 8.41 (s, 1H).
GCMS(EI): [M+H]⁺ m/z: calcd 161.0; found 160.0; Rt=4.321 min.

Step 2: The Synthesis of 3-(4,4,5,5-tetramethyl-1,3,2-dioxaborolan-2-yl)cyclopent-2-en-1-one To a solution of 3-bromocyclopent-2-en-1-one (0.5 g, 3.11 mmol) in Dioxane (15 mL), 4,4,5,5-tetramethyl-2-(4,4,5,5-tetramethyl-1,3,2-dioxaborolan-2-yl)-1,3,2-dioxaborolane (1.58 g, 6.21 mmol), Pd(dppf)Cl₂ (126.81 mg, 155.28 μmol) and potassium acetate (914.39 mg, 9.32 mmol, 582.41 μL) were added. The resulting mixture was stirred for 15 h at 80° C. The solution was cooled to room temperature, diluted with water (40 ml) and extracted with dichloromethane (2*50 ml). The collected organic layers were dried over Na₂SO₄, filtered. DCM was evaporated to give 3-(4,4,5,5-tetramethyl-1,3,2-dioxaborolan-2-yl)cyclopent-2-en-1-one (0.8 g, crude).
¹H NMR (500 MHz, CDCl₃) δ 1.31 (m, 8H), 2.34 (m, 2H), 2.75 (m, 2H), 3.69 (s, 4H), 6.62 (s, 1H).
LCMS(ESI): [M+H]⁺ m/z: calcd 208.1; found 209.2; Rt=0.269 min.

Step 3: The Synthesis of tert-butyl 3-methyl-6-(3-oxocyclopenten-1-yl)-3,4-dihydro-2H-pyridine-1-carboxylate To the stirred solution of 3-(4,4,5,5-tetramethyl-1,3,2-dioxaborolan-2-yl)cyclopent-2-en-1-one (7 g, 33.64 mmol) and tert-butyl 3-methyl-6-(trifluoromethylsulfonyloxy)-3,4-dihydro-2H-pyridine-1-carboxylate (11.62 g, 33.64 mmol) in dioxane (150 mL), solution of sodium carbonate (10.70 g, 100.93 mmol, 4.23 mL) in water (50 mL) was added. The resulting mixture was evacuated and then backfilled with argon, this operation was repeated three times. Pd(dppf)Cl₂ (1.37 g, 1.68 mmol) was added and the reaction mixture was stirred at 80° C. for 14 hr. Reaction mixture was filtered, solvent was evaporated. The residue was purified by gradient chromatography to give tert-butyl 3-methyl-6-(3-oxocyclopenten-1-yl)-3,4-dihydro-2H-pyridine-1-carboxylate (2.5 g, 9.01 mmol, 26.79% yield).
¹H NMR (500 MHz, CDCl₃) δ 1.01 (d, 3H), 1.40 (s, 9H), 0.97 (m, 1H), 1.99 (m, 1H), 2.49 (m, 3H), 2.89 (m, 1H), 2.77 (m, 1H), 2.92 (m, 1H), 3.92 (m, 1H), 5.76 (s, 1H), 6.04 (s, 1H).
LCMS(ESI): [M−tBu]⁺ m/z: calcd 221.2; found 222.2; Rt=1.258 min.

Step 4: The Synthesis of 3-(5-methyl-2-piperidyl)cyclopent-2-en-1-ol

To the tert-butyl 3-methyl-6-(3-oxocyclopenten-1-yl)-3,4-dihydro-2H-pyridine-1-carboxylate (1.9 g, 6.85 mmol), trifluoroacetic acid (7.81 g, 68.50 mmol, 5.28 mL) was added and the reaction mixture was stirred at 25° C. for 1.5 hr. TFA was evaporated. The residue was diluted with DME (40 mL) and sodium borohydride (1.30 g, 34.25 mmol, 1.21 mL) was added portionwise at 0° C. The reaction mixture was stirred at 25° C. for 1.5 hr and was then quenched with methanol (5 ml). Solvents were evaporated. the residue was washed with 10% NaOH solution and extracted with DCM (2*50 ml). Organic layer were combined, dried over Na₂SO₄. DCM was evaporated to give 3-(5-methyl-2-piperidyl)cyclopent-2-en-1-ol (0.85 g, crude).

LCMS(ESI): [M+H]⁺ m/z: calcd 181.2; found 182.2; Rt=0.698 min.

Step 5: The Synthesis of 3-(5-methyl-2-piperidyl)cyclopentanol

To the stirred solution of 3-(5-methyl-2-piperidyl)cyclopent-2-en-1-ol (0.85 g, 4.69 mmol) in MeOH (40 mL), Palladium, 10% on carbon, Type 487, dry (0.6 g, 5.64 mmol) was added. The reaction flask was evacuated and refilled by Hydrogen. The reaction mixture was stirred at 54° C. for 14 hr under Hydrogen atmosphere. The reaction mixture was filtered through SiO₂. Methanol was evaporated to give 3-(5-methyl-2-piperidyl)cyclopentanol (0.45 g, 2.46 mmol, 52.36% yield) which was used in the next step without further purification.
¹H NMR (500 MHz, CDCl₃) δ 0.81 (d, 3H), 1.22 (m, 6H), 2.17 (m, 8H), 2.28 (m, 2H), 3.01 (m, 1H), 4.33 (m, 1H).
LCMS(ESI): [M+H]⁺ m/z: calcd 183.2; found 184.2; Rt=0.524 min.

Step 6: The Synthesis of 5-[[2-[(2S,5R)-2-(3-hydroxycyclopentyl)-5-methyl-1-piperidyl]-2-oxoacetyl]amino]pyridine-3-carboxamide (Compound 517)

To the solution of 3-[(2R,5S)-5-methyl-2-piperidyl]cyclopentanol (0.35 g, 1.91 mmol), 2-[(5-carbamoyl-3-pyridyl)amino]-2-oxo-acetic acid (592.62 mg, 1.91 mmol, Et₃N) and triethylamine (1.35 g, 13.37 mmol, 1.86 mL) in DMF (4 mL), HATU (798.67 mg, 2.10 mmol) was added portionwise. Mixture was stirred at 25° C. for 2 hr. LCMS analysis of the reaction mixture showed 45% of product. Reaction mixture was submitted for reverse phase HPLC (10-10-60% 0-1-5 min 0.10% NH₃-methanol, flow: 30 ml/min (loading pump 4 ml/min methanol) target mass 374 column: YMC Triart C18 100*20 mm, 5 um) to give 5-[[2-[(2S,5R)-2-(3-hydroxycyclopentyl)-5-methyl-1-piperidyl]-2-oxo-acetyl]amino]pyridine-3-carboxamide (66 mg, 176.27 μmol, 9.23% yield) as mixture of diastereomers around C—OH.
LCMS(ESI): [M+H]⁺ m/z: calcd 374.2; found 375.2; Rt=1.846 min.

Example 770. The Synthesis of 5-[[2-oxo-2-[2-phenyl-5-(trifluoromethoxy)-1-piperidyl]acetyl]amino]pyridine-3-carboxamide (Compound 411)

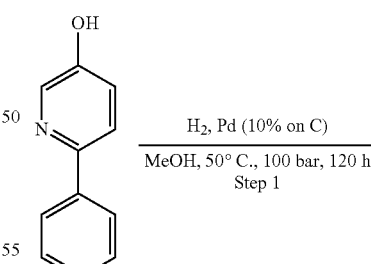

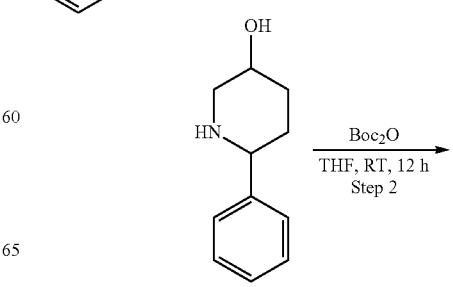

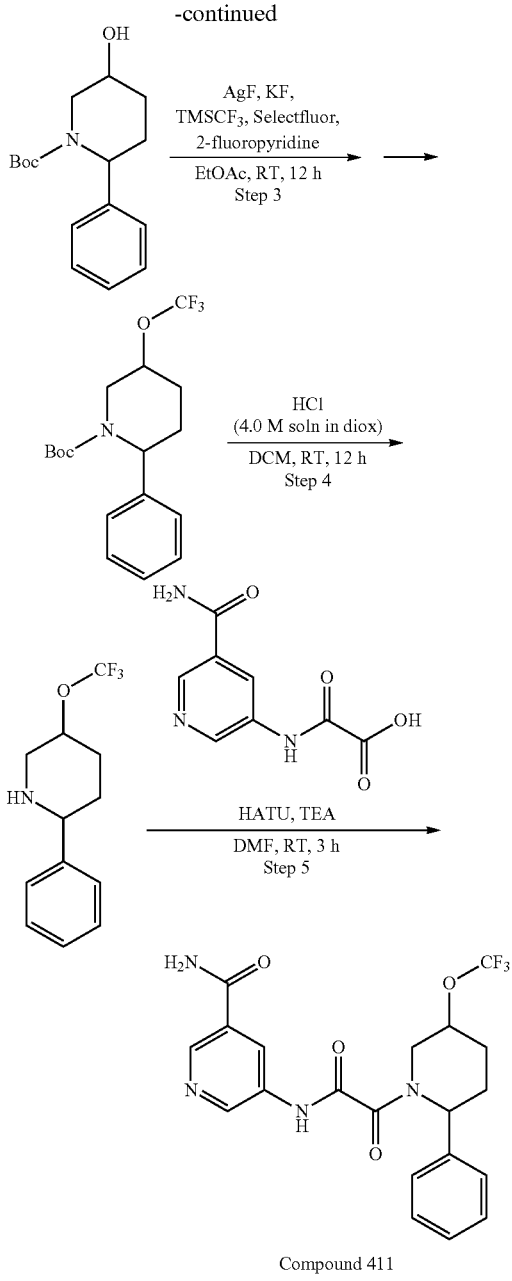

Compound 411

Step 1: The Synthesis of 6-phenylpiperidin-3-ol 6-phenylpyridin-3-ol (8.00 g, 46.73 mmol) were dissolved in MeOH (250 mL) and Palladium, 10% on carbon, Type 487, dry (2.49 g, 2.34 mmol, 10% purity) was added. The reaction mixture was heated at 50° C. in high pressure vessel at 100 bar $H_2$ pressure for 120 hr. The catalyst was filtered off, washed with MeOH and the solvent was evaporated to give 6-phenylpiperidin-3-ol (8.1 g, 45.70 mmol, 97.80% yield).

This compound was used for the next step without purification.

$^1$H NMR (500 MHz, DMSO-$d_6$) δ 1.33 (m, 2H), 1.69 (m, 2H), 1.94 (m, 1H), 2.35 (m, 1H), 3.98 (m, 1H), 3.44 (m, 2H), 7.27 (m, 5H).

LCMS(ESI): [M+H]$^+$ m/z: calcd 177.2; found 178.2; Rt=0.656 min.

Step 2: The Synthesis of tert-butyl 5-hydroxy-2-phenyl-piperidine-1-carboxylate To a solution of 6-phenylpiperidin-3-ol (8.1 g, 45.70 mmol) in THF (150 mL), di-tert-butyl dicarbonate (10.47 g, 47.99 mmol, 11.01 mL) was added. The resulting mixture was stirred at 25° C. for 12 hr, evaporated, taken up with water (30 ml), extracted with DCM (3*50 ml), dried over $Na_2SO_4$ and evaporated in vacuo to obtain crude product, which was purified by gradient chromatography (hexane—MTBE) to obtain tert-butyl 5-hydroxy-2-phenyl-piperidine-1-carboxylate (2 g, 7.21 mmol, 15.78% yield) and fraction with purity 87% by GCMS (4 g).

The structure of pure fraction was proved as trans—using 2D NMR.

$^1$H NMR (400 MHz, CDCl$_3$) δ

LCMS(ESI): [M+H]$^+$ m/z: calcd 227.2; found 228.0; Rt=1.342 min.

Step 3: The Synthesis of tert-butyl 2-phenyl-5-(trifluoromethoxy)piperidine-1-carboxylate To a reaction flask equipped with a stir bar and covered with aluminum foil were added tert-butyl 5-hydroxy-2-phenyl-piperidine-1-carboxylate (0.55 g, 1.98 mmol), silver triflate (1.53 g, 5.95 mmol), potassium fluoride (460.82 mg, 7.93 mmol) and 1-chloromethyl-4-fluoro-1,4-diazoniabicyclo[2.2.2]octane bis(tetrafluoroborate) (1.05 g, 2.97 mmol) under Ar atmosphere. Then EtOAc (10 mL), 2-fluoropyridine (577.59 mg, 5.95 mmol, 511.14 μL) and trifluoromethyltrimethylsilane (845.91 mg, 5.95 mmol, 945.16 μL) were added dropwise successively while keeping the inner temperature below 30° C. using a water bath. The reaction mixture was stirred at 25° C. for 12 hr. The resulting mixture was filtered through a plug of silica and the filtrate (80 ml) was washed with brine (3*50 ml), dried over $Na_2SO_4$ and evaporated in vacuo to obtain crude tert-butyl 2-phenyl-5-(trifluoromethoxy)piperidine-1-carboxylate (0.7 g, crude).

This compound was used for the next step without purification.

$^1$H NMR (400 MHz, CDCl$_3$) δ 1.43 (m, 9H), 1.69 (m, 2H), 1.91 (m, 2H), 2.90 (m, 1H), 4.28 (m, 1H), 5.45 (m, 1H), 7.20 (m, 3H), 7.35 (m, 2H).

LCMS(ESI): [M−Boc]$^+$ m/z: calcd 245.2; found 246.2; Rt=1.446 min.

Step 4: The Synthesis of 2-phenyl-5-(trifluoromethoxy)piperidine

To a solution of tert-butyl 2-phenyl-5-(trifluoromethoxy) piperidine-1-carboxylate (0.7 g, 2.03 mmol) in DCM (15 mL), hydrogen chloride solution 4.0 M in dioxane (6.40 g, 175.53 mmol, 8 mL) was added. The resulting mixture was stirred at 25° C. for 12 hr and evaporated in vacuo to give 2-phenyl-5-(trifluoromethoxy)piperidine (0.7 g, crude, HCl). This compound was used for the next step without purification.

$^1$H NMR (400 MHz, DMSO-$d_6$) δ 1.72 (m, 2H), 3.67 (m, 2H), 3.90 (m, 3H), 4.28 (m, 1H), 4.98 (m, 1H), 7.16 (m, 1H), 7.38 (m, 2H), 7.58 (m, 2H).

LCMS(ESI): [M+H]$^+$ m/z: calcd 245.2; found 246.0; Rt=0.897 min.

Step 5: The Synthesis of 5-[[2-oxo-2-[2-phenyl-5-(trifluoromethoxy)-1-piperidyl]acetyl]amino]pyridine-3-carboxamide (Compound 411

To a solution of 2-phenyl-5-(trifluoromethoxy)piperidine (0.7 g, 2.00 mmol), 2-[(5-carbamoyl-3-pyridyl)amino]-2-oxo-acetic acid (490.76 mg, 2.00 mmol, HCl) and Triethylamine (1.01 g, 9.99 mmol, 1.39 mL), HATU (835.69 mg, 2.20 mmol) was added. The resulting mixture was stirred at 25° C. for 3 hr and subjected to HPLC: 20-45% 0-5 min water-acetonitrile+0.1% FA flow 30 ml/min (loading pump 4 ml/min acetonitrile+0.1% FA), target mass 436.39 column: XBridge C18 100×19 mm 5 um) to give 5-[[2-oxo-2-[2-phenyl-5-(trifluoromethoxy)-1-piperidyl]acetyl]amino]pyridine-3-carboxamide (10 mg, 22.92 μmol, 1.15% yield).

$^1$H NMR (500 MHz, DMSO) δ 1.72-1.93 (m, 2H), 2.08-2.27 (m, 1H), 2.38-2.42 (m, 1H), 2.88-3.28 (m, 1H), 4.06-4.15 (m, 0.6H), 4.54-4.59 (m, 0.4H), 4.61-4.76 (m, 1H), 5.37-5.87 (m, 1H), 7.31-7.47 (m, 5H), 7.56-7.73 (m, 1H), 8.11-8.22 (m, 1H), 8.44-8.59 (m, 1H), 8.69-8.84 (m, 1H), 8.84-8.98 (m, 1H), 11.23-11.42 (m, 1H).

LCMS(ESI): [M+H]$^+$ m/z: calcd 436.2; found 437.2; Rt=3.108 min.

Example 771. The Synthesis of 5-[[2-[(2S,5R)-5-(difluoromethoxy)-2-phenyl-1-piperidyl]-2-oxo-acetyl]amino]pyridine-3-carboxamide (Compound 379) and 5-[[2-[(2R,5R)-5-(difluoromethoxy)-2-phenyl-1-piperidyl]-2-oxo-acetyl]amino]pyridine-3-carboxamide (Compound 400)

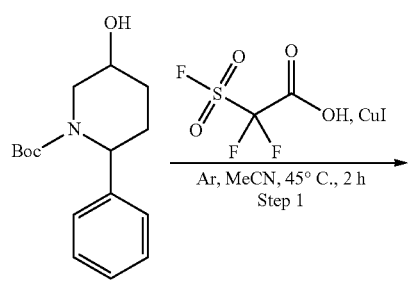

Step 1: The Synthesis of tert-butyl 5-(difluoromethoxy)-2-phenyl-piperidine-1-carboxylate tert-butyl 5-hydroxy-2-phenyl-piperidine-1-carboxylate (0.6 g, 2.16 mmol) (prepared as described above) and copper(I) iodide (82.40 mg, 432.65 μmol, 14.66 μL) was dissolved in ACN (30 mL) and heated to 45° C. under Argon atmosphere. To this solution, a solution of 2,2-difluoro-2-fluorosulfonyl-acetic acid (770.50 mg, 4.33 mmol, 447.97 μL) in ACN (3 ml) was added dropwise over 10 min. The resulting mixture was stirred at 45° C. for 1.5 hr and additional solution of 2,2-difluoro-2-fluorosulfonyl-acetic acid (770.50 mg, 4.33 mmol, 447.97 μL) in ACN (3 ml) was added dropwise over 10 min. The resulting mixture was stirred at 45° C. for 12 hour and evaporated in vacuo. The residue was diluted with DCM (75 ml) and saturated aqueous sodium bicarbonate (75 ml). The organic layer was separated, washed with brine (50 ml), dried over Na$_2$SO$_4$ and evaporated to give tert-butyl 5-(difluoromethoxy)-2-phenyl-piperidine-1-carboxylate (0.7 g, crude). This compound was used for the next step without purification.

¹H NMR (400 MHz, CDCl₃) δ 1.45 (s, 9H), 1.65 (m, 2H), 2.14 (m, 1H), 2.29 (m, 2H), 2.60 (m, 1H), 2.88 (m, 1H), 4.22 (m, 2H), 7.24 (m, 5H).

LCMS(ESI): [M−Boc]⁺ m/z: calcd 227.2; found 228.2; Rt=0.847 min.

Step 2: The Synthesis of
5-(difluoromethoxy)-2-phenyl-piperidine

To a solution of tert-butyl 5-(difluoromethoxy)-2-phenyl-piperidine-1-carboxylate (0.7 g, 2.14 mmol) in DCM (15 mL), hydrogen chloride solution 4.0 M in dioxane (8.00 g, 219.41 mmol, 10 mL) was added. The resulting mixture was stirred at 25° C. for 3 hr and evaporated in vacuo to give 5-(difluoromethoxy)-2-phenyl-piperidine (0.5 g, crude, HCl). This compound was used for the next step without purification.

¹H NMR (500 MHz, CDCl₃) δ 1.67 (m, 2H), 1.82 (m, 2H), 2.16 (m, 2H), 2.90 (2, 1H), 4.24 (m, 2H), 7.25 (m, 5H).

LCMS(ESI): [M+H]⁺ m/z: calcd 227.1; found 228.2; Rt=0.740 min.

Step 3: The Synthesis of 5-[[2-[(2S,5R)-5-(difluoromethoxy)-2-phenyl-1-piperidyl]-2-oxo-acetyl] amino]pyridine-3-carboxamide (Compound 379) and 5-[[2-[(2R,5R)-5-(difluoromethoxy)-2-phenyl-1-piperidyl]-2-oxo-acetyl]amino]pyridine-3-carboxamide (Compound 400

To a solution of 5-(difluoromethoxy)-2-phenyl-piperidine (0.5 g, 1.90 mmol, HCl), 2-[(5-carbamoyl-3-pyridyl) amino]-2-oxo-acetic acid (465.70 mg, 1.90 mmol, HCl) and triethylamine (959.29 mg, 9.48 mmol, 1.32 mL), HATU (793.01 mg, 2.09 mmol) was added. The resulting mixture was stirred at 25° C. for 3 hr and subjected to HPLC: 0-5 min 15-40% water-acetonitrile+0.1% TFA, flow 30 ml/min (loading pump 4 ml/min acetonitrile+0.1% TFA), target mass 418.40 column: SunFire C18 100*19 mm 5 um) to give 5-[[2-[(2S,5R)-5-(difluoromethoxy)-2-phenyl-1-piperidyl]-2-oxo-acetyl]amino]pyridine-3-carboxamide (34 mg, 81.26 µmol, 5.36% yield).

Compound 379: ¹H NMR (600 MHz, DMSO-d₆) δ 1.62-1.71 (m, 1H), 1.71-1.81 (m, 1H), 2.07-2.24 (m, 1H), 2.29-2.35 (m, 1H), 2.82-3.21 (m, 1H), 3.97-4.52 (m, 2H), 5.26-5.77 (m, 1H), 6.50-6.92 (m, 1H), 7.23-7.31 (m, 1H), 7.31-7.33 (m, 1H), 7.33-7.36 (m, 1H), 7.37-7.45 (m, 2H), 7.52-7.66 (m, 1H), 8.09-8.18 (m, 1H), 8.43-8.53 (m, 1H), 8.71-8.80 (m, 1H), 8.83-8.92 (m, 1H), 11.15-11.39 (m, 1H).

LCMS(ESI): [M+H]⁺ m/z: calcd 418.2; found 419.2; Rt=2.811 min.

Compound 400: ¹H NMR (600 MHz, DMSO-d₆) δ 1.41-1.49 (m, 1H), 1.90-2.06 (m, 2H), 2.40-2.45 (m, 1H), 2.54-2.56 (m, 0.4H), 2.81-2.86 (m, 0.6H), 3.98-4.20 (m, 1H), 4.31-4.51 (m, 1H), 5.17-5.66 (m, 1H), 6.48-6.91 (m, 1H), 7.15-7.30 (m, 1H), 7.31-7.34 (m, 1H), 7.35-7.38 (m, 1H), 7.39-7.43 (m, 2H), 7.55-7.67 (m, 1H), 8.10-8.22 (m, 1H), 8.42-8.54 (m, 1H), 8.72-8.81 (m, 1H), 8.81-8.95 (m, 1H), 11.29-11.33 (m, 1H).

LCMS(ESI): [M+H]⁺ m/z: calcd 418.2; found 419.2; Rt=3.015 min.

Example 772. The Synthesis of 5-[[2-[(2R,5S)-5-hydroxy-2-phenyl-1-piperidyl]-2-oxo-acetyl]amino] pyridine-3-carboxamide (Compound 349

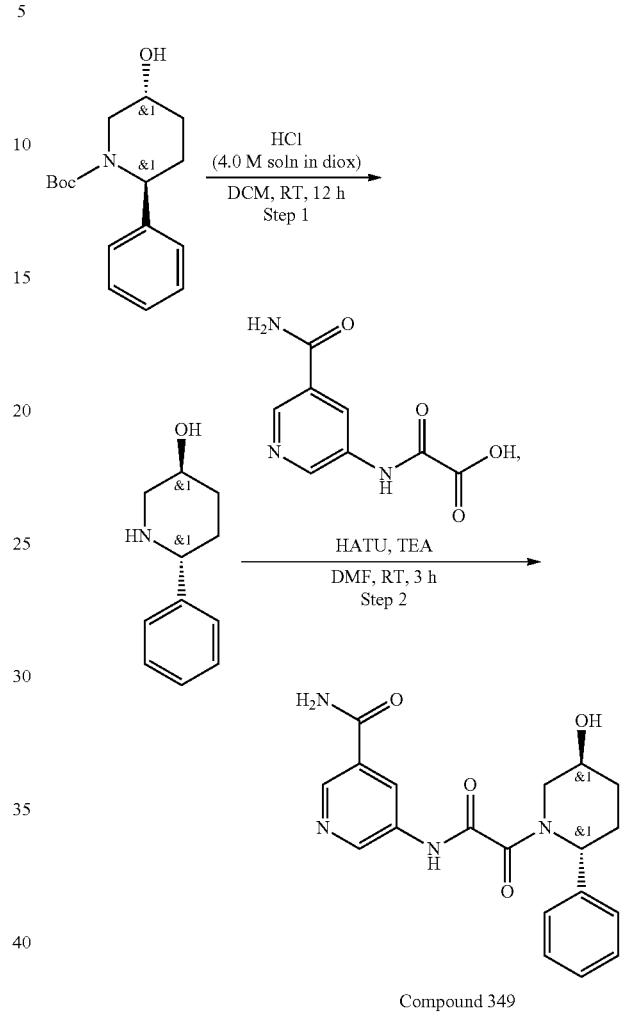

Compound 349

Step 1: The Synthesis of
(3S,6R)-6-phenylpiperidin-3-ol

The structure of boc-protected amine from the previous examples was proved as trans-.

A solution of tert-butyl (2R,5S)-5-hydroxy-2-phenyl-piperidine-1-carboxylate (500.00 mg, 1.80 mmol) in hydrogen chloride solution 4.0 M in dioxane (6.40 g, 175.53 mmol, 8 mL) was stirred at 25° C. for 3 hr and evaporated in vacuo to obtain (3S,6R)-6-phenylpiperidin-3-ol (0.3 g, 1.40 mmol, 77.87% yield, HCl).

¹H NMR (400 MHz, DMSO-d₆) δ 1.55 (m, 1H), 1.95 (m, 3H), 2.74 (m, 1H), 3.23 (m, 1H), 4.02 (m, 1H), 4.19 (m, 1H), 7.41 (m, 3H), 7.59 (m, 2H), 9.46 (m, 1H), 9.85 (m, 1H).

LCMS(ESI): [M+H]⁺ m/z: calcd 177.1; found 178.2; Rt=0.662 min.

Step 2: The Synthesis of 5-[[2-[(2R,5S)-5-hydroxy-2-phenyl-1-piperidyl]-2-oxo-acetyl]amino]pyridine-3-carboxamide (Compound 349

To a solution of (3S,6R)-6-phenylpiperidin-3-ol (290.28 mg, 1.64 mmol, HCl), 2-[(5-carbamoyl-3-pyridyl)amino]-2- oxo-acetic acid (402.27 mg, 1.64 mmol, HCl) and triethylamine (828.64 mg, 8.19 mmol, 1.14 mL), HATU (685.01 mg, 1.80 mmol) was added. The resulting mixture was stirred at 25° C. for 3 hr and subjected to HPLC: 20-20-65% 0-1-6 min 0.2% TFA-methanol, flow: 30 ml/min (loading pump 4 ml/min methanol) target mass 368 column: YMC Triart C18 100*20 mm, 5 um) to give 5-[[2-[(2R,5S)-5-hydroxy-2-phenyl-1-piperidyl]-2-oxo-acetyl]amino]pyridine-3-carboxamide (250 mg, 678.64 μmol, 41.44% yield). The structure of boc-protected amine was proved as trans-.

$^1$H NMR (600 MHz, DMSO-d$_6$) δ 1.44-1.64 (m, 2H), 2.09-2.27 (m, 2H), 2.65-3.13 (m, 1H), 3.67-4.33 (m, 2H), 4.73-4.95 (m, 1H), 5.19-5.73 (m, 2H), 7.24-7.29 (m, 1H), 7.29-7.34 (m, 2H), 7.35-7.42 (m, 2H), 7.54-7.63 (m, 1H), 8.08-8.21 (m, 1H), 8.44-8.57 (m, 1H), 8.69-8.78 (m, 1H), 8.81-8.95 (m, 1H), 11.01-11.33 (m, 1H).

LCMS(ESI): [M+H]$^+$ m/z: calcd 368.2; found 369.2; Rt=2.375 min.

Example 773. The Synthesis of 5-[[2-oxo-2-[(2S, 5S)-2-phenyl-5-(2,2,2-trifluoroethyl)-1-piperidyl]acetyl]amino]pyridine-3-carboxamide (Compound 342) and 5-[[2-oxo-2-[(2R,5S)-2-phenyl-5-(2,2,2-trifluoroethyl)-1-piperidyl]acetyl]amino]pyridine-3-carboxamide (Compound 318)

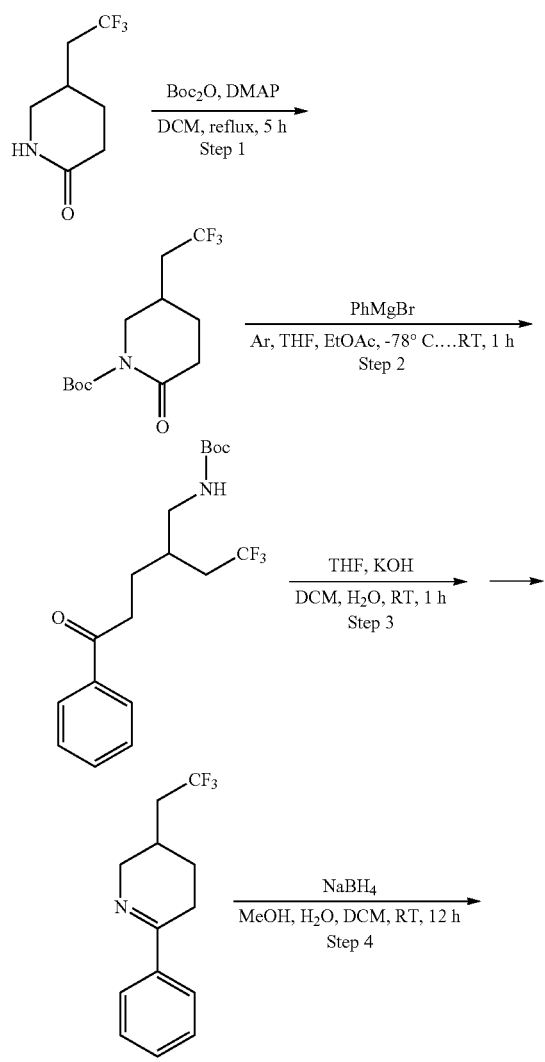

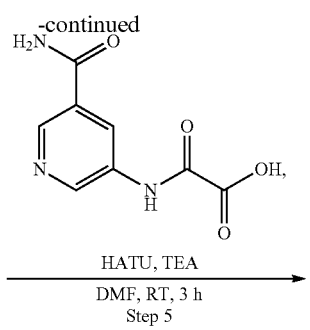

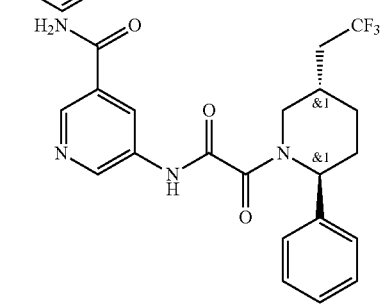

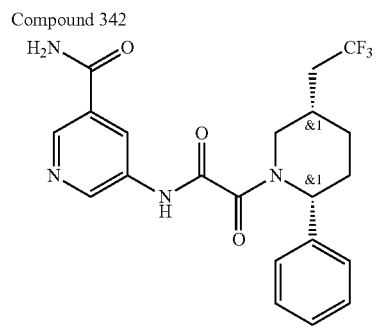

Compound 342

Compound 318

Step 1: The Synthesis of tert-butyl 2-oxo-5-(2,2,2-trifluoroethyl)piperidine-1-carboxylate The solution of tert-butoxycarbonyl tert-butyl carbonate (15.06 g, 69.00 mmol, 15.84 mL) in DCM (25.00 mL) was slowly (for 5 hr) added to the refluxed solution of 5-(2,2,2-trifluoroethyl)piperidin-2-one (5 g, 27.60 mmol) and DMAP (33.72 mg, 276.01 μmol) in DCM (25.00 mL). Aliquote shows ~50% conversion to the desired product; another 1 eq of tert-butoxycarbonyl tert-butyl carbonate (15.06 g, 69.00 mmol, 15.84 mL) was added in analoguous manner. After the reaction was complete, the organic solvents was evaporated to give tert-butyl 2-oxo-5-(2,2,2-trifluoroethyl)piperidine-1-carboxylate (8.2 g, crude) which was used in the next step without purification.

$^1$H NMR (500 MHz, DMSO-d$_6$) δ 1.38 (s, 9H), 1.55 (m, 1H), 1.82 (m, 1H), 2.18 (m, 1H), 2.39 (m, 4H), 3.41 (m, 1H), 3.62 (m, 1H).

Step 2: The Synthesis of tert-butyl N-[5-oxo-5-phenyl-2-(2,2,2-trifluoroethyl)pentyl]carbamate tert-butyl 2-oxo-5-(2,2,2-trifluoroethyl)piperidine-1-carboxylate (1 g, 3.56 mmol) was dissolved in THF (5.00 mL) and cooled to −78° C. under Ar. The solution of bromo (phenyl)magnesium (644.62 mg, 3.56 mmol, 1.4 mL) was added dropwise and the reaction mixture was warmed to rt. After 30 min, the reaction was quenched with excess sat aq NH$_4$Cl, and extracted with EtOAc (15 mL). Evaporation of the solvent results in tert-butyl N-[5-oxo-5-phenyl-2-(2,2,2-trifluoroethyl)pentyl]carbamate (0.8 g, crude).

$^1$H NMR (400 MHz, CDCl$_3$) δ 1.46 (m, 9H), 1.83 (m, 7H), 3.05 (m, 4H), 4.77 (m, 1H), 7.45 (m, 3H), 7.95 (s, 2H).

LCMS(ESI): [M−Boc]$^+$ m/z: calcd 259.2; found 260.2; Rt=1.406 min.

Step 3: The Synthesis of 6-phenyl-3-(2,2,2-trifluoroethyl)-2,3,4,5-tetrahydropyridine tert-butyl N-[5-oxo-5-phenyl-2-(2,2,2-trifluoroethyl)pentyl]carbamate (3 g, 8.35 mmol) was dissolved in DCM (20 mL), followed by the addition of TFA (2.86 g, 25.04 mmol, 1.93 mL). After the reaction was complete (concluded by HNMR), the reaction mixture was neutralized with 50% aq KOH (4.68 g, 83.48 mmol, 2.30 mL). The mixture was extracted with DCM (50 mL), organic solvent was dried over Na$_2$SO$_4$ and evaporated to give 6-phenyl-3-(2,2,2-trifluoroethyl)-2,3,4,5-tetrahydropyridine (1.3 g, 5.39 mmol, 64.55% yield).

$^1$H NMR (500 MHz, CDCl$_3$) δ 1.55 (m, 1H), 2.11 (m, 4H), 2.64 (m, 1H), 2.84 (m, 1H), 3.45 (m, 1H), 4.11 (m, 1H), 7.40 (m, 3H), 7.78 (m, 2H).

Step 4: The Synthesis of 2-phenyl-5-(2,2,2-trifluoroethyl)piperidine 6-phenyl-3-(2,2,2-trifluoroethyl)-2,3,4,5-tetrahydropyridine (1.3 g, 5.39 mmol)6-phenyl-3-(2,2,2-trifluoroethyl)-2,3,4,5-tetrahydropyridine (1.3 g, 5.39 mmol) was dissolved in MeOH (20 mL) and H$_2$O (5 mL) and cooled to 25° C. Sodium Borohydride (407.73 mg, 10.78 mmol, 381.05 µL) was added in portions to obtained mixture and additionally stirred overnight. After the reaction was complete, the reaction mixture was acidified with 10% aq HCl to pH 2, washed with MTBE (2*10 mL), basified with 10% aq NaOH to pH 10 and extracted with DCm (30 mL). Evaporation of the solvent result in pure 2-phenyl-5-(2,2,2-trifluoroethyl)piperidine (1 g, 4.11 mmol, 76.29% yield) as mixture of cis- and trans- (20:80) isomers.

$^1$H NMR (400 MHz, CDCl$_3$) δ 1.31 (m, 1H), 1.44 (m, 1H), 1.71 (m, 1H), 1.94 (m, 4H), 2.51 (m, 1H), 3.01 (m, 1H), 3.22 (m, 1H), 3.48 (m, 1H), 7.28 (m, 5H).

Step 5: The Synthesis of 5-[[2-oxo-2-[(2S,5S)-2-phenyl-5-(2,2,2-trifluoroethyl)-1-piperidyl]acetyl]amino]pyridine-3-carboxamide (Compound 342) and 5-[[2-oxo-2-[(2R,5S)-2-phenyl-5-(2,2,2-trifluoroethyl)-1-piperidyl]acetyl]amino]pyridine-3-carboxamide (Compound 31)

DIPEA (368.33 mg, 2.85 mmol, 496.41 µL) was added to the solution of respective 2-[(5-carbamoyl-3-pyridyl)amino]-2-oxo-acetic acid (0.2 g, 814.27 µmol, HCl) and 2-phenyl-5-(2,2,2-trifluoroethyl)piperidine (198.08 mg, 814.27 µmol) in DMF (10 mL). The resulting mixture was stirred for 5 min followed by the addition of the solution of HATU (340.57 mg, 895.69 µmol) in DMF (2 mL). Then, the reaction mixture was stirred overnight at room temperature. After the completion of the reaction, monitored by LCMS, the resulting suspension was concentrated under reduced pressure. The obtained solid was subjected to HPLC (Waters Sunfire C18 19*100 5 mkm column and H$_2$O-MeCN as a mobile phase) to afford pure trans 5-[[2-oxo-2-[(2S,5S)-2-phenyl-5-(2,2,2-trifluoroethyl)-1-piperidyl]acetyl]amino]pyridine-3-carboxamide (0.18 g, 414.35 µmol, 50.89% yield) and cis 5-[[2-oxo-2-[(2R,5S)-2-phenyl-5-(2,2,2-trifluoroethyl)-1-piperidyl]acetyl]amino]pyridine-3-carboxamide (30.2 mg, 69.52 µmol, 8.54% yield) diastereomers.

Compound 342: $^1$H NMR (600 MHz, DMSO-d$_6$) δ 1.54 (m, 1H), 1.67 (m, 1H), 1.97 (m, 1H), 2.09 (m, 1H), 2.27 (m, 1H), 2.43 (m, 1H), 2.79 (m, 1H), 4.01 (m, 1H), 5.39 (m, 1H), 7.27 (m, 1H), 7.31 (m, 2H), 7.36 (m, 1H), 7.40 (m, 2H), 7.60 (m, 1H), 8.15 (m, 1H), 8.45 (m, 1H), 8.76 (m, 1H), 8.86 (m, 1H), 11.25 (m, 1H).

LCMS(ESI): [M+H]$^+$ m/z: calcd 434.2; found 435.2; Rt=3.262 min.

Compound 318: $^1$H NMR (600 MHz, DMSO-d$_6$) δ 1.25 (m, 1H), 1.77 (m, 1H), 1.88 (m, 1H), 1.98 (m, 1H), 2.08 (m, 2H), 2.70 (m, 2H), 4.07 (m, 1H), 5.50 (m, 1H), 7.28 (m, 1H), 7.30 (m, 1H), 7.35 (m, 1H), 7.40 (m, 2H), 7.60 (m, 1H), 8.15 (m, 1H), 8.46 (m, 1H), 8.77 (m, 1H), 8.86 (m, 1H), 11.29 (m, 1H).

LCMS(ESI): [M+H]$^+$ m/z: calcd 434.2; found 435.2; Rt=3.217 min.

Example 774. The Synthesis of rac-5-[[2-[(2R,5S)-2-(3-hydroxycyclobutyl)-5-methyl-1-piperidyl]-2-oxo-acetyl]amino]pyridine-3-carboxamide (Compound 413) and rac-5-[[2-[(2R,5S)-2-(3-hydroxycyclobutyl)-5-methyl-1-piperidyl]-2-oxo-acetyl]amino]pyridine-3-carboxamide (Compound 407)

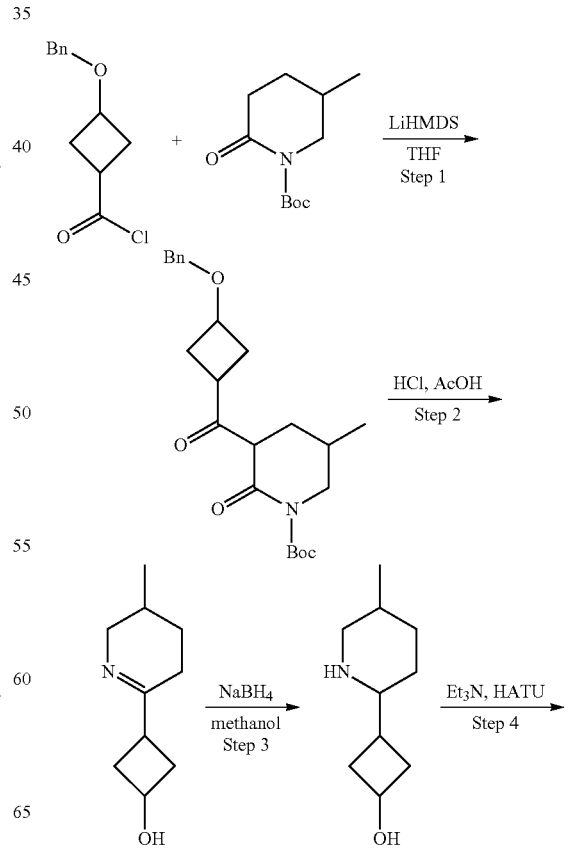

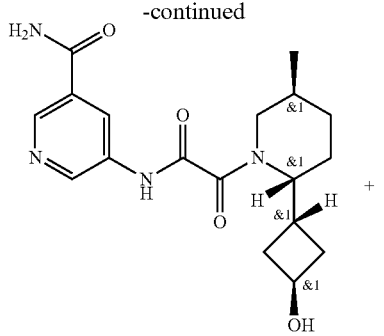

Compound 413

Compound 407

Step 1: Synthesis of tert-butyl 3-(3-benzyloxycyclobutanecarbonyl)-5-methyl-2-oxo-piperidine-1-carboxylate To the pre-cooled (−78° C.) solution of tert-butyl 5-methyl-2-oxo-piperidine-1-carboxylate (3.6 g, 16.88 mmol) in THF (100 mL) LiHMDS (35.45 mmol, 33.5 mL) was added dropwise. The resulting mixture was stirred at −78° C. for 1 hr. The solution of 3-benzyloxycyclobutanecarbonyl chloride (3.79 g, 16.88 mmol) was added in one portion. The reaction mixture was allowed to warm to room temperature and stirred at that temperature for 4 hr. The reaction mixture was quenched with NaHSO$_4$ (10 g; 10% solution) and extracted with DCM (2*100 ml). Organic layers was washed with water, dried over Na$_2$SO$_4$. DCM was evaporated to give tert-butyl 3-(3-benzyloxycyclobutanecarbonyl)-5-methyl-2-oxo-piperidine-1-carboxylate (8 g, crude)

$^1$H NMR (CDCl$_3$, 400 MHz): δ 0.95 (s, 3H), 1.20 (m, 2H), 1.45 (m, 9H), 1.90 (m, 2H), 2.10-2.25 (m, 4H), 3.00 (m, 2H), 3.75 (m, 1H), 3.95 (m, 1H), 4.42 (m, 2H), 7.31 (m, 5H).

LCMS(ESI): [M−Boc]$^+$ m/z: calcd 401.2; found 302.2; Rt=1.447 min.

Step 2: Synthesis of 3-(5-methyl-2-piperidyl)cyclobutanol tert-butyl 3-(3-benzyloxycyclobutanecarbonyl)-5-methyl-2-oxo-piperidine-1-carboxylate (2 g, 4.98 mmol) was dissolved in AcOH (25 mL) and Hydrogen chloride water solution (1.82 g, 4.98 mmol, 25 mL, 10% purity) was added portionwise. After addition was complete, resulting mixture was stirred at 100° C. for 14 hr. Then, solvents were removed under reduced pressure and residue was partitioned between 1 N HCl (5 ml) and DCM (20 ml). Organic layer was separated and discarded. Aqueous layer was basified to ph≈10 with 10% NaOH and extracted with EtOAc (2×30 ml). EtOAc solution was separated, dried over Na$_2$SO$_4$ and evaporated under reduced pressure, affording 3-(3-methyl-2,3,4,5-tetrahydropyridin-6-yl)cyclobutanol (300 mg, 1.79 mmol, 36.01% yield). Crude product was used in the next step without further purification.

$^1$H NMR (CDCl$_3$, 400 MHz): δ 0.90 (m, 3H), 1.10-1.20 (m, 1H), 1.50 (m, 1H), 1.70 (m, 1H), 1.85-2.20 (m, 4H), 2.30-2.50 (m, 3H), 2.95 (m, 1H), 3.25-3.40 (brs, 1H), 3.68 (d, 1H), 4.13 (m, 1H).

LCMS(ESI): [M+1]$^+$ m/z: calcd 257.2; found 258.2; Rt=0.803 min.

Step 3: Synthesis of 3-(5-methyl-2-piperidyl)cyclobutanol

To a solution of 3-(3-methyl-2,3,4,5-tetrahydropyridin-6-yl)cyclobutanol (0.45 g, 2.69 mmol) in MeOH (10 mL), Sodium Borohydride (101.79 mg, 2.69 mmol, 95.13 µL) was added portionwise at 25° C. The resulting mixture was stirred at 25° C. for 2 hr and evaporated in vacuo. The residue was treated with Hydrogen chloride dioxane solution. Then dioxane was evaporated. Precipitate was washed with THF, dried in vacuo to give 3-(5-methyl-2-piperidyl)cyclobutanol (300 mg, crude, HCl)

$^1$H NMR (CDCl$_3$, 400 MHz): δ 0.90 (d, 3H), 1.00-1.10 (m, 1H), 1.20-1.30 (m, 1H), 1.40-1.50 (m, 1H), 1.60-2.00 (m, 5H), 2.10-2.40 (m, 3H), 2.80 (m, 1H), 3.00 (m, 1H), 3.50 (brs, 1H), 3.83 (m, 1H), 9.00 (brs, 1H), 9.40 (brs, 1H).

LCMS(ESI): [M+1]$^+$ m/z: calcd 169.2; found 170.2; Rt=0.645 min.

Step 4: The Synthesis of rac-5-[[2-[(2R,5S)-2-(3-hydroxycyclobutyl)-5-methyl-1-piperidyl]-2-oxo-acetyl]amino]pyridine-3-carboxamide (Compound 413) and rac-5-[[2-[(2R,5S)-2-(3-hydroxycyclobutyl)-5-methyl-1-piperidyl]-2-oxo-acetyl]amino]pyridine-3-carboxamide (Compound 407

To the solution of 3-(5-methyl-2-piperidyl)cyclobutanol (0.3 g, 1.46 mmol, HCl), 2-[(5-carbamoyl-3-pyridyl)amino]-2-oxo-acetic acid (358.18 mg, 1.46 mmol, HCl) and Triethylamine (1.48 g, 14.58 mmol, 2.03 mL) in DMF (3 mL) HATU (609.92 mg, 1.60 mmol) was added portionwise. Mixture was stirred at 25° C. for 2 hr. The reaction mixture was submitted for HPLC (10-10-40% 0-1-6 min 0.1% NH$_3$-methanol, flow: 30 ml/min (loading pump 4 ml/min methanol) target mass 360 column: YMC Triart C18 100×20 mm, 5 um) to give 5-[[2-[(2R,5S)-2-(3-hydroxycyclobutyl)-5-methyl-1-piperidyl]-2-oxo-acetyl]amino]pyridine-3-carboxamide (12 mg, 33.30 µmol, 2.28% yield) and 5-[[2-[(2R,5S)-2-(3-hydroxycyclobutyl)-5-methyl-1-piperidyl]-2-oxo-acetyl]amino]pyridine-3-carboxamide (100 mg, 277.46 µmol, 19.03% yield) 0.5-[[2-[(2R,5S)-2-(3-hydroxycyclobutyl)-5-methyl-1-piperidyl]-2-oxo-acetyl]amino]pyridine-3-carboxamide (12 mg, 33.30 µmol, 2.28% yield) Compound 413:

$^1$H NMR (500 MHz, DMSO) δ 0.89-1.00 (m, 3H), 1.21-1.33 (m, 1H), 1.35-1.48 (m, 1H), 1.64-1.80 (m, 1H), 1.80-1.89 (m, 3H), 1.91-2.15 (m, 3H), 2.71-2.81 (m, 1H), 2.85-3.25 (m, 1H), 3.41-3.47 (m, 1H), 3.78-4.01 (m, 1H), 4.22-4.44 (m, 1H), 4.94-5.05 (m, 1H), 7.57-7.65 (m, 1H), 8.14-8.21 (m, 1H), 8.45-8.57 (m, 1H), 8.72-8.83 (m, 1H), 8.86-8.94 (m, 1H), 11.10 (br s, 1H).

LCMS(ESI): [M+1]$^+$ m/z: calcd 360.2; found 361.2; Rt=2.180 min.

Compound 407:

¹H NMR (500 MHz, DMSO) δ 0.90-1.01 (m, 3H), 1.24-1.45 (m, 3H), 1.47-1.68 (m, 2H), 1.68-2.04 (m, 3H), 2.19-2.23 (m, 1H), 2.28-2.33 (m, 1H), 2.93-3.25 (m, 1H), 3.41-3.78 (m, 1H), 3.82-3.93 (m, 1H), 3.97-4.45 (m, 1H), 4.88-5.03 (m, 1H), 7.54-7.70 (m, 1H), 8.11-8.24 (m, 1H), 8.44-8.57 (m, 1H), 8.72-8.85 (m, 1H), 8.87-8.97 (m, 1H), 11.00-11.17 (m, 1H).

LCMS(ESI): [M+1]⁺ m/z: calcd 360.2; found 361.2; Rt=2.336 min.

Example 775. The Synthesis of 5-(2-(5-methyloctahydroisoquinolin-2(1B)-yl)-2-oxoacetamido)nicotinamide (Compound 515, Compound 536

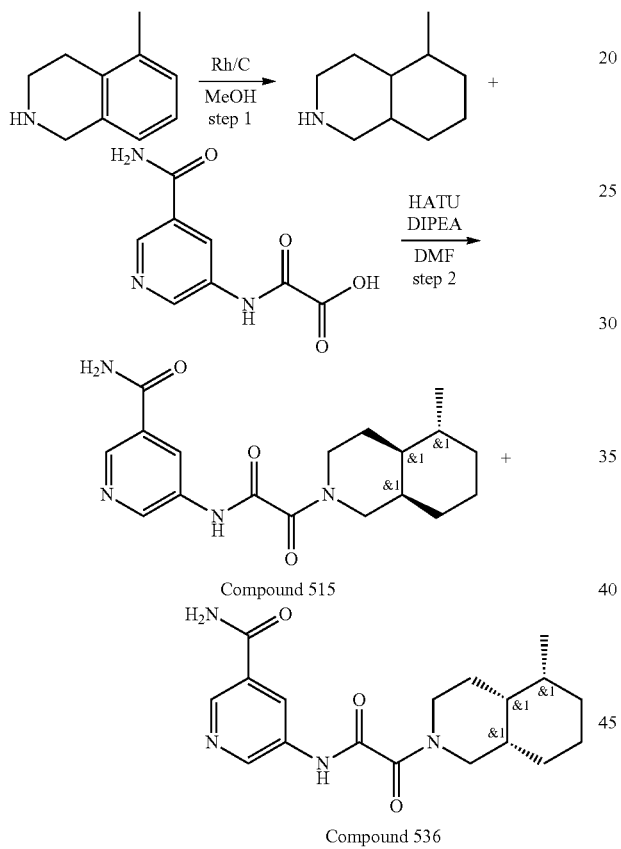

Compound 515

Compound 536

Step 1: Synthesis of 5-methyldecahydroisoquinoline 5-methyl-1,2,3,4-tetrahydroisoquinoline (0.5 g, 2.72 mmol, HCl) was dissolved in MeOH and hydrogenated under high pressure for 48 hr. After the reaction was complete, the catalyst was filtered off and evaporation of the organic solvent results in 5-methyl-1,2,3,4,4a,5,6,7,8,8a-decahydroisoquinoline (0.3 g, 1.58 mmol, 58.09% yield, HCl) which was used in the next step without purification.

¹H NMR (500 MHz, DMSO-d₆) δ (ppm) 0.86 (d, 3H), 1.52 (m, 7H), 2.92 (m, 4H), 3.28 (m, 2H), 4.16 (m, 2H), 8.45 (m, 1H).

LCMS(ESI): [M]⁺ m/z: calcd 153.2; found 154.2; Rt=0.723 min.

Step 2: Synthesis of 5-(2-(5-methyloctahydroisoquinolin-2(1H)-yl)-2-oxoacetamido)nicotinamide (Compound 515, and Compound 536

5-methyl-1,2,3,4,4a,5,6,7,8,8a-decahydroisoquinoline (0.35 g, 1.84 mmol, HCl), 2-[(5-carbamoyl-3-pyridyl)amino]-2-oxo-acetic acid (385.85 mg, 1.84 mmol, TEA) and DIPEA (715.27 mg, 5.53 mmol, 963.98 µL) were dissolved in DMF (6 mL) under gentle heating. HATU (841.73 mg, 2.21 mmol) was added in small portions under vigorous stirring and occasional heating. After the reaction was complete, the mixture was purified by HPLC (21% 0.5-6.5 min; water-MeCN; 30 ml/min; loading pump 4 ml/minMeCN; target mass 344; column SunFire 19*100 mm) and repurified (11-18% 0.5-5 min; water-MeCN+NH₃ 30 ml/min; loading pump MeCN 4 ml/min; target mass 344 column Triart 19*100 mm) to give 5-[[2-[(4aS,5R,8aR)-5-methyl-3,4,4a,5,6,7,8,8a-octahydro-1H-isoquinolin-2-yl]-2-oxo-acetyl]amino]pyridine-3-carboxamide (5 mg, 14.52 µmol, 7.87e-1% yield) in 4 fractions. The structure of the amine core was not proved; relative configuration was assigned due to 1D H-NMR.

Compound 515: ¹H NMR (600 MHz, DMSO-d₆) δ (ppm) 0.83-0.92 (m, 4H), 0.95-1.07 (m, 2H), 1.06-1.32 (m, 3H), 1.32-1.42 (m, 1H), 1.52-1.77 (m, 3H), 1.83-1.98 (m, 1H), 2.25-2.32 (m, 0.5H), 2.58-2.66 (m, 0.5H), 2.66-2.74 (m, 0.5H), 3.02-3.08 (m, 0.5H), 3.74-4.07 (m, 1H), 4.21-4.54 (m, 1H), 7.29 (s, 1H), 7.96 (s, 1H), 8.41-8.48 (m, 1H), 8.70 (s, 1H), 8.86 (s, 1H), 10.87 (s, 1H).

LCMS(ESI): [M]⁺ m/z: calcd 344.2; found 345.2; Rt=2.642 min.

Compound 536: ¹H NMR (600 MHz, DMSO-d₆) δ (ppm) 0.79-0.86 (m, 3H), 0.97-1.05 (m, 1H), 1.17-1.31 (m, 3H), 1.35-1.52 (m, 3H), 1.54-1.65 (m, 2H), 1.68-1.86 (m, 2H), 2.63-2.85 (m, 1H), 2.97-3.24 (m, 1H), 3.56-3.90 (m, 1H), 4.10-4.45 (m, 1H), 7.59 (s, 1H), 8.14 (s, 1H), 8.43-8.50 (m, 1H), 8.74-8.77 (m, 1H), 8.82-8.88 (m, 1H), 11.05 (s, 1H).

LCMS(ESI): [M]⁺ m/z: calcd 344.2; found 345.2; Rt=2.445 min.

Example 776. The Synthesis of 5-(2-(2,5-dimethyl-2-phenylpiperidin-1-yl)-2-oxoacetamido)nicotinamide (Compound 521)

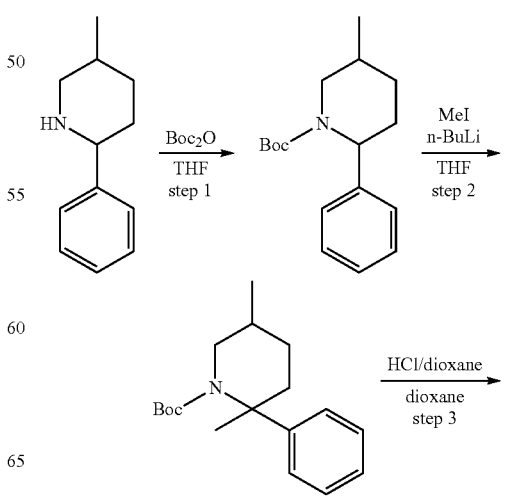

-continued

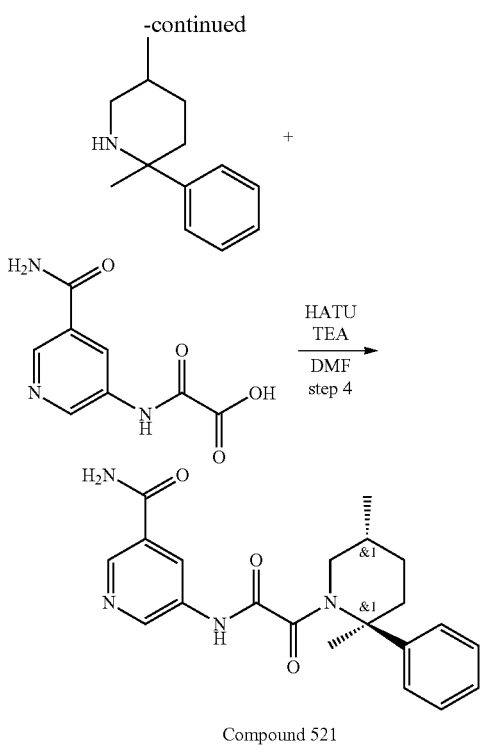

Compound 521

Step 1: Synthesis of tert-butyl 5-methyl-2-phenylpiperidine-1-carboxylate 5-methyl-2-phenyl-piperidine (1 g, 5.71 mmol) was dissolved in THF (20 mL) followed by the addition of boc₂O (1.25 g, 5.71 mmol, 1.31 mL) in a dropwise manner. After 1 hr, evaporation of the solvent and purification by CC (Companion combiflash; 40 g $SiO_2$; chloroform/MeCN with MeCN from 0 to 10%, flow rate=40 ml/min, Rv=3-8 cv.) results in tert-butyl 5-methyl-2-phenyl-piperidine-1-carboxylate (1.1 g, 3.99 mmol, 70.01% yield).

$^1$H NMR (400 MHz, $CDCl_3$) δ (ppm) 1.06 (d, 3H), 1.21 (m, 1H), 1.46 (s, 9H), 1.86 (m, 2H), 2.08 (m, 2H), 2.98 (d, 1H), 3.86 (d, 1H), 5.24 (m, 1H), 7.28 (m, 5H).

LCMS(ESI): [M−Boc]⁺ m/z: calcd 175.4; found 176.2; Rt=1.617 min.

Step 2: Synthesis of tert-butyl 2,5-dimethyl-2-phenylpiperidine-1-carboxylate tert-butyl 5-methyl-2-phenyl-piperidine-1-carboxylate (0.4 g, 1.45 mmol) was dissolved in THF (5 mL) and cooled to −40° C. under Ar. Butyl lithium (2.5 M, 697.21 µL) was added in a dropwise manner keeping the temperature below −35° C. and additionally stirred for 30 min at the same temperature. Intermediate aliquote (quenched with deuteromethanol $CD_3OD$) shows ~80% conversion to lithiated product. The reaction mixture was cooled to −78° C. and iodomethane (618.50 mg, 4.36 mmol, 271.27 µL) was added in one portion and the reaction mixture was warmed to rt, followed by additional stirring for 2 hr. The reaction mixture was quenched with excess sat aq $NH_4Cl$ and extracted with EtOAc twice. Combined organic layers was dried over $Na_2SO_4$ and evaporated under reduced pressure to give tert-butyl 2,5-dimethyl-2-phenyl-piperidine-1-carboxylate (0.33 g, crude) which was used in the next step without purification.

$^1$H NMR (400 MHz, $CDCl_3$) δ (ppm) 1.06 (d, 3H), 1.21 (s, 3H), 1.46 (s, 9H), 1.58 (m, 2H), 2.98 (m, 1H), 3.12 (m, 1H), 3.86 (m, 1H), 4.12 (m, 1H), 5.24 (m, 1H), 7.28 (m, 5H).

LCMS(ESI): [M−Boc]⁺ m/z: calcd 189.4; found 190.2; Rt=1.758 min.

Step 3: Synthesis of 2,5-dimethyl-2-phenylpiperidine tert-butyl 2,5-dimethyl-2-phenyl-piperidine-1-carboxylate (0.3 g, 1.04 mmol) was dissolved in dioxane (5 mL), followed by the addition of the solution of HCl (377.95 mg, 10.37 mmol, 472.44 µL) in dioxane (5 mL). After the reaction was complete, the organic solvents was evaporated, and the crude product was re-evaporated with MeOH (10 mL) and toluene (10 mL) to give 2,5-dimethyl-2-phenyl-piperidine (0.2 g, 885.91 µmol, 85.46% yield, HCl), which was used in the next step without purification.

$^1$H NMR (400 MHz, DMSO-$d_6$) δ (ppm) 0.98 (d, 3H), 1.42 (s, 3H), 1.92 (m, 4H), 2.12 (m, 1H), 2.56 (m, 3H), 7.58 (m, 5H).

Step 4: Synthesis of 5-(2-(2,5-dimethyl-2-phenylpiperidin-1-yl)-2-oxoacetamido)nicotinamide (Compound 521

2-[(5-carbamoyl-3-pyridyl)amino]-2-oxo-acetic acid (185.30 mg, 885.91 µmol, TEA), 2,5-dimethyl-2-phenyl-piperidine (0.2 g, 885.91 µmol, HCl) and DIPEA (343.48 mg, 2.66 mmol, 462.92 µL) were dissolved in DMF (6 mL) under gentle heating. HATU (404.22 mg, 1.06 mmol) was added in small portions under vigorous stirring and occasional heating. After the reaction was complete, the mixture was purified by HPLC (23% 0.5-6.5 min water-MeCN; flow: 30 ml/min; (loading pump 4 ml/minMeCN); target mass 380; column: SunFire C18 100×19 mm 5 um (L)) to give 5-[[2-[(2R,5S)-2,5-dimethyl-2-phenyl-1-piperidyl]-2-oxo-acetyl]amino]pyridine-3-carboxamide (27 mg, 70.97 µmol, 8.01% yield). Structure of the amine core was confirmed by 2D-NMR spectroscopy.

$^1$H NMR (600 MHz, DMSO-$d_6$) δ (ppm) 0.93 (d, 3H), 1.11-1.19 (m, 1H), 1.48-1.59 (m, 1H), 1.66-1.74 (m, 1H), 1.81 (s, 3H), 1.86-1.99 (m, 2H), 3.08-3.19 (m, 1H), 3.54-3.63 (m, 1H), 7.12-7.20 (m, 1H), 7.25-7.34 (m, 4H), 7.60 (s, 1H), 8.15 (s, 1H), 8.49 (s, 1H), 8.76 (s, 1H), 8.89 (d, 1H), 10.97 (s, 1H).

LCMS(ESI): [M]⁺ m/z: calcd 380.4; found 381.2; Rt=2.619 min.

Example 777. The Synthesis of 5-[[2-[(2R,5S)-2-(3-tert-butyl-4-hydroxy-phenyl)-5-methyl-1-piperidyl]-2-oxo-acetyl]amino]pyridine-3-carboxamide (Compound 610)

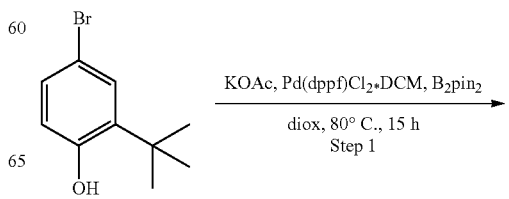

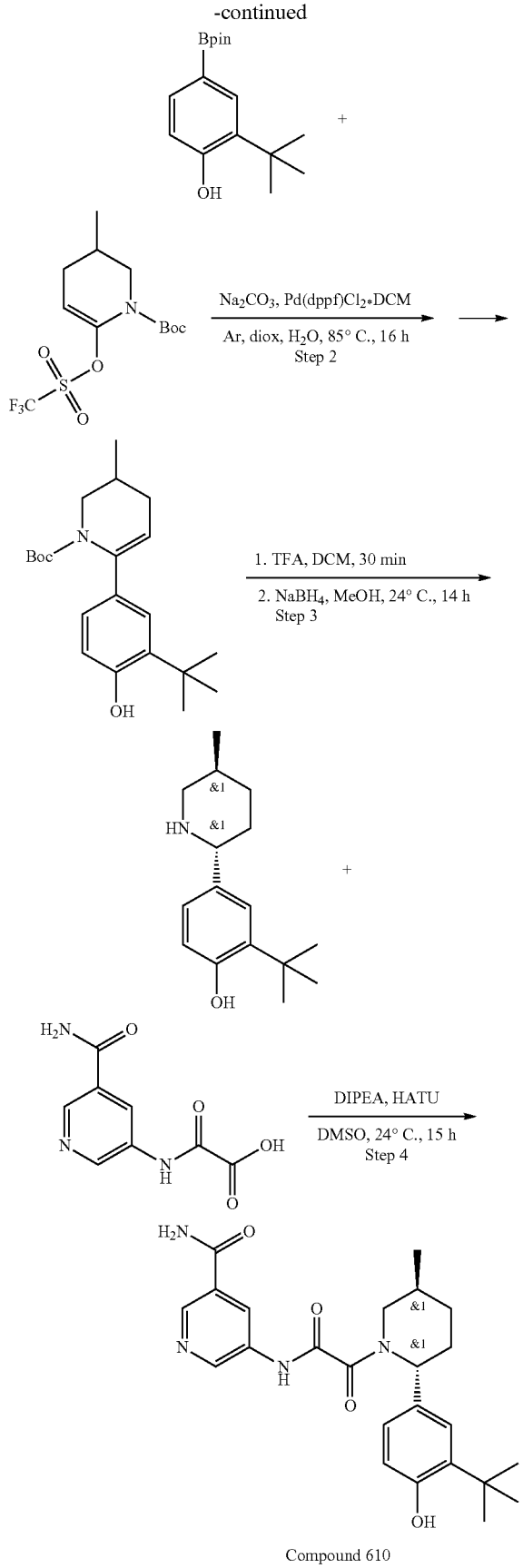

Compound 610

Step 1: The Synthesis of 2-tert-butyl-4-(4,4,5,5-tetramethyl-1,3,2-dioxaborolan-2-yl)phenol 4-bromo-2-tert-butyl-phenol (15 g, 65.47 mmol), 4,4,5,5-tetramethyl-2-(4,4,5,5-tetramethyl-1,3,2-dioxaborolan-2-yl)-1,3,2-dioxaborolane (17.79 g, 70.05 mmol), dry Potassium Acetate (25.70 g, 261.88 mmol, 16.37 mL), Pd(dppf)Cl$_2$*DCM (2.71 g, 3.27 mmol) and 1,4-dioxane (200 mL) were placed in 3-neck round bottom flask under Argon atmosphere and stirred at 80° C. for 15 hr. After cooling down, the reaction mixture was diluted with water (500 mL) and extracted with DCM. The organic layer was separated, dried over Na$_2$SO$_4$ and concentrated under reduced pressure. The resulting residue was submitted to flash column chromatography to afford 2-tert-butyl-4-(4,4,5,5-tetramethyl-1,3,2-dioxaborolan-2-yl)phenol (12 g, 43.45 mmol, 66.37% yield).

Chromatography data: RediSep Column: 330 g, Run length: 18.7 CV, Flow Rate: 100 ml/min Solvent A: CHCl$_3$; Solvent B: acetonitrile $^1$H NMR (400 MHz, DMSO-d$_6$) δ 1.19 (s, 12H), 1.27 (s, 9H), 6.63 (d, 1H), 7.22 (d, 1H), 7.38 (s, 1H), 9.35 (s, 1H).

Step 2: The Synthesis of tert-butyl 6-(3-tert-butyl-4-hydroxy-phenyl)-3-methyl-3,4-dihydro-2H-pyridine-1-carboxylate 2-tert-butyl-4-(4,4,5,5-tetramethyl-1,3,2-dioxaborolan-2-yl)phenol (6.8 g, 24.62 mmol), tert-butyl 3-methyl-6-(trifluoromethylsulfonyloxy)-3,4-dihydro-2H-pyridine-1-carboxylate (6.80 g, 19.70 mmol), Sodium carbonate (7.83 g, 73.87 mmol, 3.09 mL) and Pd(dppf)Cl$_2$*DCM (814.21 mg, 984.87 μmol) were added to a mixture of 1,4-dioxane (50 mL) and water (20 mL). The reaction mixture was stirred at 85° C. for 85° C. under argon atmosphere. After cooling down, the reaction mixture was diluted with water (100 mL) and extracted with DCM. The organic layer was separated, dried over Na$_2$SO$_4$ and concentrated under reduced pressure to afford tert-butyl 6-(3-tert-butyl-4-hydroxy-phenyl)-3-methyl-3,4-dihydro-2H-pyridine-1-carboxylate (5 g, crude) which was used in the next step without purification.

LCMS(ESI): [M−tBu]$^+$ m/z: calcd 289.2; found 290.2; Rt=1.532 min.

Step 3: The Synthesis of 2-tert-butyl-4-[(2R,5S)-5-methyl-2-piperidyl]phenol tert-butyl 6-(3-tert-butyl-4-hydroxy-phenyl)-3-methyl-3,4-dihydro-2H-pyridine-1-carboxylate (2.3 g, 4.39 mmol) was dissolved in a mixture of TFA (7.40 g, 64.90 mmol, 5 mL) and DCM (5 mL) and stirred at RT for 0.5 hr. The reaction mixture was concentrated on a rotary evaporator (bath temperature 45 C) to afford crude azomethine, which was used directly in the next step. The crude material from the previous step was dissolved in methanol (50 mL) followed by the addition of Sodium Borohydride (216.11 mg, 5.71 mmol, 201.97 μL) in one portion. The reaction mixture was stirred at RT overnight and acidified with HCl/dioxane solution. The resulting solution was concentrated under reduced pressure to afford 2-tert-butyl-4-[(2R,5S)-5-methyl-2-piperidyl]phenol which was used in the next step without purification.

LCMS(ESI): [M+H]$^+$ m/z: calcd 247.2; found 248.2; Rt=0.783 min.

Step 4: The Synthesis of 5-[[2-[(2R,5S)-2-(3-tert-butyl-4-hydroxy-phenyl)-5-methyl-1-piperidyl]-2-oxo-acetyl]amino]pyridine-3-carboxamide (Compound 610

2-tert-butyl-4-[(2R,5S)-5-methyl-2-piperidyl]phenol (500.00 mg, 1.03 mmol), 2-[(5-carbamoyl-3-pyridyl)amino]-2-oxo-acetic acid (237.17 mg, 1.13 mmol, TEA) and DIPEA (742.00 mg, 5.74 mmol, 1 mL) were dissolved in DMSO (5 mL) followed by addition of HATU (509.54 mg, 1.34 mmol). The reaction mixture was stirred at RT for 15 hr and then submitted to HPLC to afford 5-[[2-[(2R,5S)-2-(3-tert-butyl-4-hydroxy-phenyl)-5-methyl-1-piperidyl]-2-oxo-acetyl]amino]pyridine-3-carboxamide (0.07 g, 159.63 μmol, 15.49% yield).

HPLC data: 2-10 min 50-60% MeCN/H$_2$O 30 ml/min (loading pump 4 ml MeCN) column:

SunFire 100*19 mm, 5 micro; Sample Info: 2-10 min 50-60% water/MeCN+NH$_3$ (loading pump 4 ml MeCN+NH$_3$) column: TRIART 100*20 5 microM $^1$H NMR (600 MHz, DMSO-d$_6$) δ 0.95-1.07 (m, 3H), 1.25-1.36 (m, 10H), 1.63-1.79 (m, 1H), 1.79-1.94 (m, 1H), 1.96-2.09 (m, 1H), 2.09-2.18 (m, 1H), 2.74-3.26 (m, 1H), 3.37-3.98 (m, 1H), 5.01-5.58 (m, 1H), 6.69-6.81 (m, 1H), 6.90-7.01 (m, 1H), 7.01-7.12 (m, 1H), 7.50-7.65 (m, 1H), 8.08-8.21 (m, 1H), 8.40-8.55 (m, 1H), 8.67-8.79 (m, 1H), 8.79-8.92 (m, 1H), 9.28 (s, 1H), 11.02-11.32 (m, 1H).

LCMS(ESI): [M+H]$^+$ m/z: calcd 438.2; found 439.2; Rt=3.087 min.

Example 778. The Synthesis of 5-[[2-[(2R,5S)-2-(3-ethyl-4-hydroxy-phenyl)-5-methyl-1-piperidyl]-2-oxo-acetyl]amino]pyridine-3-carboxamide (Compound 642)

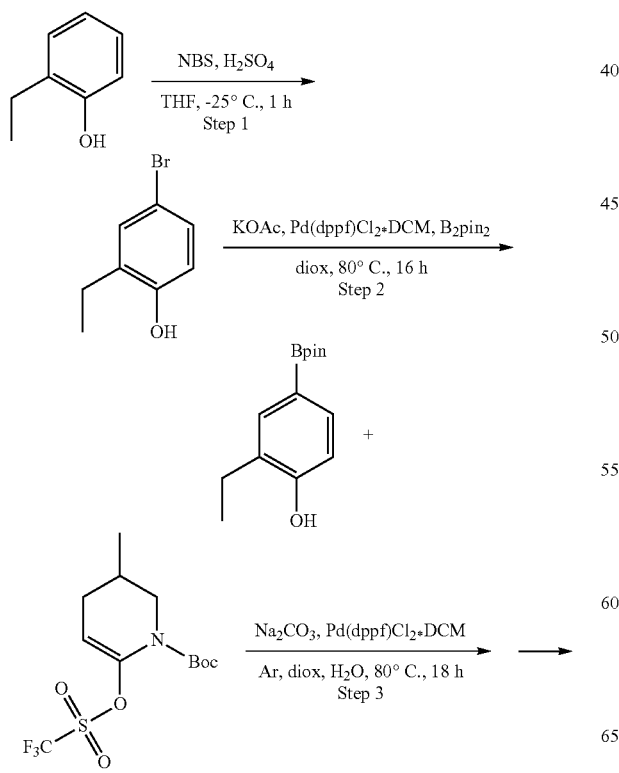

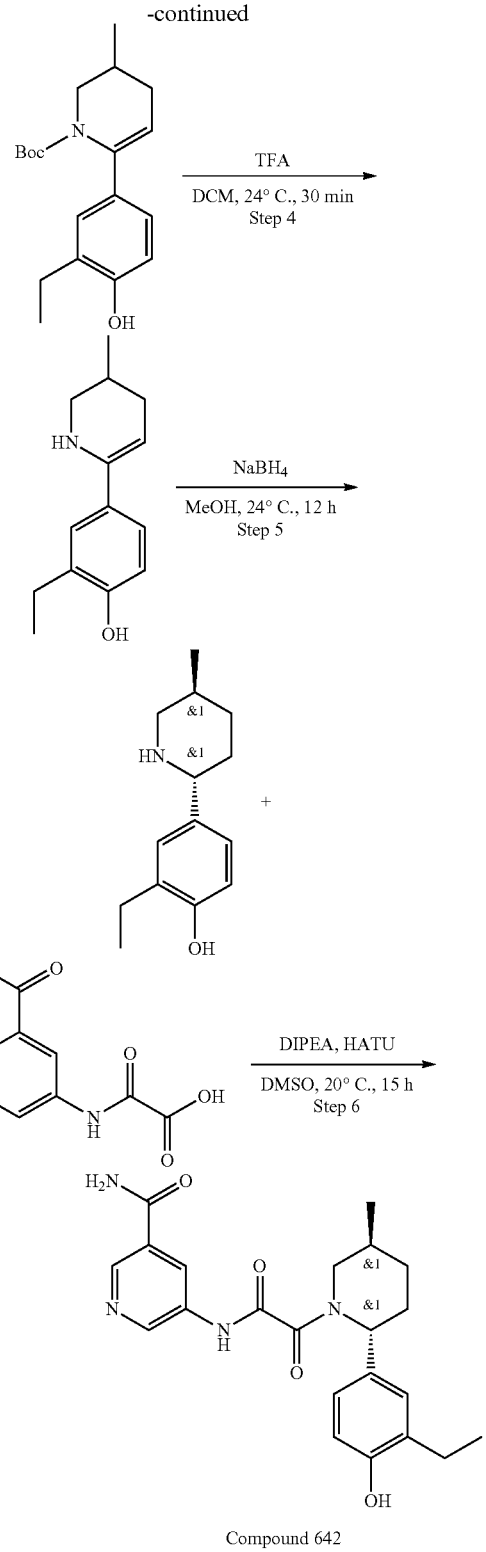

Compound 642

Step 1: The Synthesis of 4-bromo-2-ethyl-Phenol 2-ethylphenol (14 g, 114.60 mmol, 13.73 mL) and sulfuric acid (224.80 mg, 2.29 mmol) were dissolved in THF (500 mL) and the mixture was cooled down to −25° C. NBS (21.21 g, 119.18 mmol) was added portion-wise with stirring at −25° C. and the reaction mixture was stirred for 1 hr at this temperature and then left to warm up to RT for 2 hr. The reaction mixture was concentrated under reduced pressure and dissolved in ethyl acetate. The organic layer was washed with NaHCO$_3$ solution, NaHSO$_3$ solution, water, dried over Na$_2$SO$_4$ and concentrated on a rotary evaporator to afford 4-bromo-2-ethyl-phenol (18 g, crude) which was used in the next step without purification.

$^1$H NMR (400 MHz, DMSO-d$_6$) δ 1.10 (t, 3H), 2.49 (q, 2H), 6.72 (d, 1H), 7.12 (d, 1H), 7.19 (s, 1H), 9.55 (s, 1H).

Step 2: The Synthesis of 2-ethyl-4-(4,4,5,5-tetramethyl-1,3,2-dioxaborolan-2-yl)phenol 4-bromo-2-ethyl-phenol (18 g, 80.57 mmol), 4,4,5,5-tetramethyl-2-(4,4,5,5-tetramethyl-1,3,2-dioxaborolan-2-yl)-1,3,2-dioxaborolane (22.51 g, 88.63 mmol), Potassium Acetate (31.63 g, 322.29 mmol, 20.15 mL) and Pd(dppf)Cl$_2$·DCM (3.33 g, 4.03 mmol) were mixed in 1,4-dioxane (400 mL) and the reaction mixture was stirred under argon atmosphere at 80° C. for 16 hr. After completion of the reaction, the reaction mixture was cooled down, diluted with water and extracted with DCM. The organic layer was separated, dried over Na$_2$SO$_4$ and concentrated under reduced pressure. The resulting residue was submitted to flash column chromatography to afford 2-ethyl-4-(4,4,5,5-tetramethyl-1,3,2-dioxaborolan-2-yl)phenol (10 g, 40.30 mmol, 50.02% yield). Chromatography data: RediSep Column: 330 g, Run length: 25.0 CV, Flow Rate: 100 ml/min, Solvent A: CHCl$_3$, Solvent B: acetonitrile.

$^1$H NMR (400 MHz, DMSO-d$_6$) δ 1.10 (t, 3H), 1.14 (s, 12H), 2.49 (q, 2H), 6.67 (d, 1H), 7.26 (d, 1H), 7.33 (s, 1H), 9.39 (s, 1H).

LCMS(ESI): [M+H]$^+$ m/z: calcd 247.2; found 248.2; Rt=1.447 min.

Step 3: The Synthesis of tert-butyl 6-(3-ethyl-4-hydroxy-phenyl)-3-methyl-3,4-dihydro-2H-pyridine-1-carboxylate 2-ethyl-4-(4,4,5,5-tetramethyl-1,3,2-dioxaborolan-2-yl)phenol (2.5 g, 10.08 mmol), tert-butyl 3-methyl-6-(trifluoromethylsulfonyloxy)-3,4-dihydro-2H-pyridine-1-carboxylate (2.78 g, 8.06 mmol), Sodium carbonate (3.20 g, 30.23 mmol, 1.27 mL) and Pd(dppf)Cl$_2$·DCM (333.19 mg, 403.02 µmol) were added to a mixture of 1,4-dioxane (20 mL) and water (10 mL) and the reaction mixture was stirred under argon atmosphere at 80° C. for 18 hr. After cooling down, the reaction mixture was diluted with water and extracted with DCM. The organic layer was separated, dried over Na$_2$SO$_4$ and filtered through a small pad of silica gel. The filtrate was concentrated under reduced pressure to afford tert-butyl 6-(3-ethyl-4-hydroxy-phenyl)-3-methyl-3,4-dihydro-2H-pyridine-1-carboxylate (2 g, crude) which was used in the next step without purification.

LCMS(ESI): [M−tBu]$^+$ m/z: calcd 261.2; found 262.2; Rt=1.585 min.

Step 4: The Synthesis of 2-ethyl-4-(3-methyl-2,3,4,5-tetrahydropyridin-6-yl)phenol tert-butyl 6-(3-ethyl-4-hydroxy-phenyl)-3-methyl-3,4-dihydro-2H-pyridine-1-carboxylate (2 g, 2.90 mmol) was dissolved in a mixture of TFA (7.40 g, 64.90 mmol, 5 mL) and DCM (5 mL) and the reaction mixture was stirred at RT for 0.5 hr and concentrated under reduced pressure to afford 2-ethyl-4-(3-methyl-2,3,4,5-tetrahydropyridin-6-yl)phenol (1.36 g, crude) which was used in the next step without purification.

LCMS(ESI): [M+H]$^+$ m/z: calcd 217.2; found 218.4; Rt=0.919 min.

Step 5: The Synthesis of 2-ethyl-4-[(2R,5S)-5-methyl-2-piperidyl]phenol

Crude 2-ethyl-4-(3-methyl-2,3,4,5-tetrahydropyridin-6-yl)phenol (1.36 g, 2.38 mmol) was dissolved in methanol (30 mL) and Sodium Borohydride (0.2 g, 5.29 mmol, 186.92 µL) was added in one portion. The reaction mixture was stirred at RT for 12 hr and then acidified with HCl-dioxane solution. The resulting solution was concentrated under reduced pressure to afford 2-ethyl-4-[(2R,5S)-5-methyl-2-piperidyl]phenol (1.3 g, crude, HCl) which was used in the next step without purification.

LCMS(ESI): [M+H]$^+$ m/z: calcd 219.2; found 220.2; Rt=0.901 min.

Step 6: The Synthesis of 5-[[2-[(2R,5S)-2-(3-ethyl-4-hydroxy-phenyl)-5-methyl-1-piperidyl]-2-oxo-acetyl]amino]pyridine-3-carboxamide (Compound 642

2-ethyl-4-[(2R,5S)-5-methyl-2-piperidyl]phenol (0.2 g, 265.85 µmol, HCl), 2-[(5-carbamoyl-3-pyridyl)amino]-2-oxo-acetic acid (78.36 mg, 319.02 µmol, HCl) and DIPEA (742.00 mg, 5.74 mmol, 1 mL) were added to DMSO (1.5 mL) followed by addition of HATU (141.52 mg, 372.19 µmol). The reaction mixture was stirred at 20° C. for 15 hr. After completion of the reaction (LCMS control) the reaction mixture was submitted to HPLC to afford 5-[[2-[(2R,5S)-2-(3-ethyl-4-hydroxy-phenyl)-5-methyl-1-piperidyl]-2-oxo-acetyl]amino]pyridine-3-carboxamide (0.021 g, 51.16 µmol, 19.24% yield) in two fractions: fraction_1 (8 mg, 100% by LCMS) and fraction (14 mg, 98% by LCMS).

HPLC data:
Sample Info: 2-10 min 60-85% water/MeOH+NH$_3$ (loading pump 4 ml MeOH+NH$_3$) column:
TRIART 100*20 mm 5 microM $^1$H NMR (DMSO-d$_6$, 600 MHz): δ (ppm) 1.05 (m, 6H), 1.31 (m, 1H), 1.72 (m, 1H), 1.84 (m, 1H), 2.01 (m, 1H), 2.14 (m, 1H), 2.52 (m, 2H), 2.92 (m, 1H), 3.58 (m, 1H), 5.27 (m, 1H), 6.74 (m, 1H), 6.98 (m, 2H), 7.57 (m, 1H), 8.13 (m, 1H), 8.46 (m, 1H), 8.73 (m, 1H), 8.96 (m, 2H), 11.20 (s, 1H)

LCMS(ESI): [M+H]$^+$ m/z: calcd 410.2; found 411.4; Rt=2.425 min.

Example 779. The Synthesis of 2-(2-(1H-indazol-6-yl)-5-methylpiperidin-1-yl)-N-(6-amino-5-methylpyridin-3-yl)-2-oxoacetamide (Compound 613 and Compound 636

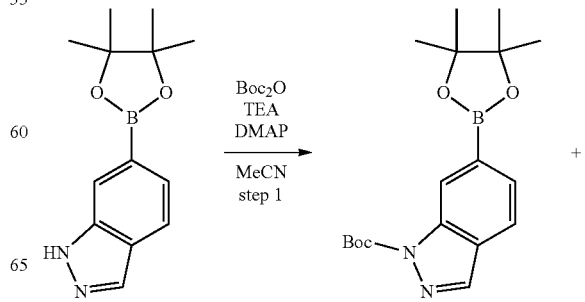

3135
-continued
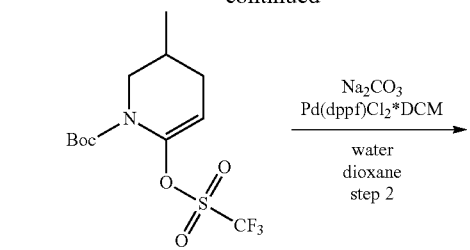
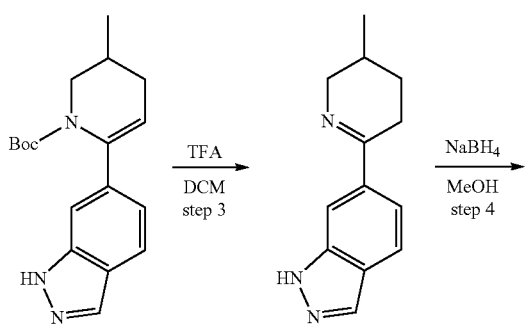
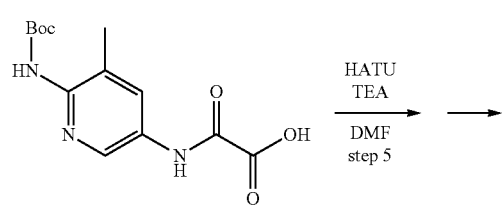
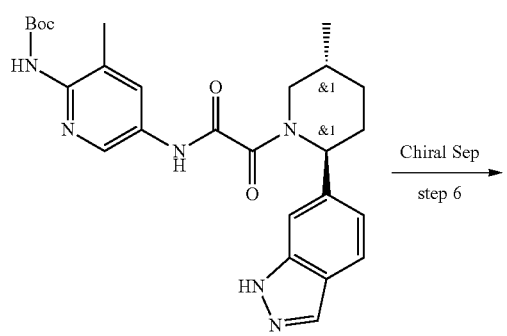
3136
-continued
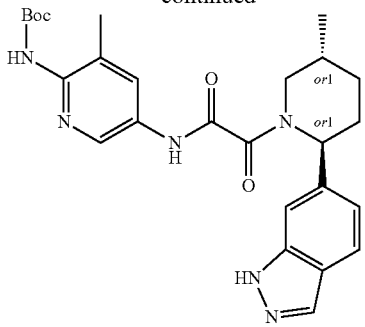
E1
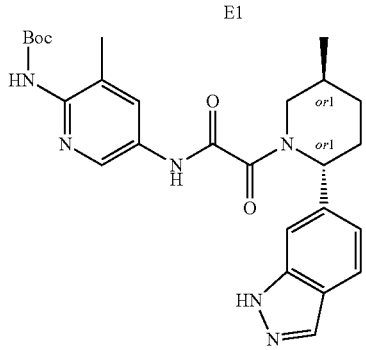
E2
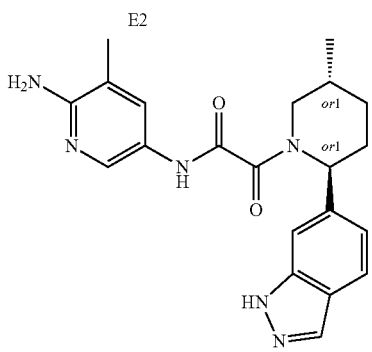
Compound 613
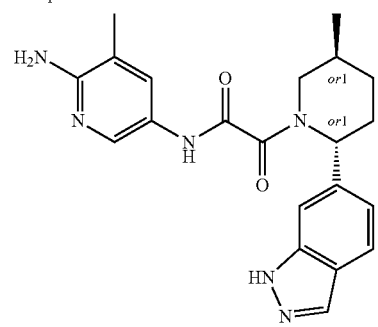
Compound 636
Step 1: Synthesis of tert-butyl 6-(4,4,5,5-tetramethyl-1,3,2-dioxaborolan-2-yl)-1H-indazole-1-carboxylate
To a stirred mixture of 6-(4,4,5,5-tetramethyl-1,3,2-dioxaborolan-2-yl)-1H-indazole (2.00 g, 8.19 mmol), TEA (1.04 g, 10.24 mmol, 1.43 mL) in MeCN (20 mL) was added di-tert-butyl dicarbonate (1.97 g, 9.01 mmol, 2.07 mL) at ambient temperature, followed by DMAP (100.10 mg, 819.35 μmol) then the reaction mixture was stirred at 70° C. for 12 hr. The reaction mixture was concentrated on vacuum and obtained residue was dissolved in DCM, washed with NaHSO₄(aq), NaHCO₃(aq), brine then dried over Na₂SO₄, filtered and concentrated on vacuum to give tert-butyl 6-(4,4,5,5-tetramethyl-1,3,2-dioxaborolan-2-yl)indazole-1-carboxylate (1 g, 2.91 mmol, 35.46% yield) which was used in the next step without further purification.

¹H NMR (400 MHz, DMSO-d₆) δ (ppm) 1.29 (s, 12H), 1.62 (s, 9H), 7.59 (m, 1H), 7.83 (m, 1H), 8.40 (m, 1H), 8.48 (m, 1H). Step 2: Synthesis of tert-butyl 6-(1H-indazol-6-yl)-3-methyl-3,4-dihydropyridine-1(2H)-carboxylate tert-butyl 6-(4,4,5,5-tetramethyl-1,3,2-dioxaborolan-2-yl)indazole-1-carboxylate (1.87 g, 5.43 mmol), tert-butyl 3-methyl-6-(trifluoromethylsulfonyloxy)-3,4-dihydro-2H-pyridine-1-carboxylate (2.06 g, 5.98 mmol) and sodium carbonate (1.15 g, 10.87 mmol, 455.19 μL) were mixed together in a mixture of dioxane (30 mL) and water (10 mL). The flask was evacuated and backfilled three times with argon and dichloro(1,1'-bis(diphenylphosphanyl)ferrocene)palladium(II)*DCM (221.75 mg, 271.63 μmol) was added thereto. The reaction mixture was heated at 85° C. for 12 hr. The reaction mixture was diluted with EtOAc/water, organic phase was separated, the aqueous phase was washed with additional EtOAc, combined organic phase was dried over Na₂SO₄, filtered and concentrated on vacuo to give tert-butyl 6-(1-tert-butoxycarbonyl-3-methyl-3,4-dihydro-2H-pyridin-6-yl)indazole-1-carboxylate (2.2 g, 5.32 mmol, 97.93% yield) which was used in the next step without further purification.

LCMS(ESI): [M−Boc]⁺ m/z: calcd 313.2; found 314.2; Rt=1.464 min.

Step 3: Synthesis of 6-(5-methyl-3,4,5,6-tetrahydropyridin-2-yl)-1H-indazole tert-butyl 6-(1-tert-butoxycarbonyl-3-methyl-3,4-dihydro-2H-pyridin-6-yl)indazole-1-carboxylate (3.4 g, 8.22 mmol) was dissolved in a mixture of DCM (12 mL) and TFA (12 mL) then stirred ar rt for 1 hr. The reaction mixture was neutralized with 20% aq. solution of NaOH, obtained solution was diluted with DCM, the organic phase was separated and the aqueous layer was washed with additional DCM. The organic phase was dried over Na₂SO₄, filtered and concentrated on vacuo to give 6-(3-methyl-2,3,4,5-tetrahydropyridin-6-yl)-1H-indazole (1.15 g, 5.39 mmol, 65.58% yield) which was used in the next step without further purification.

¹H NMR (400 MHz, DMSO-d₆) δ (ppm) 0.91 (d, 3H), 1.27 (m, 1H), 1.61 (m, 1H), 1.83 (m, 1H), 2.59 (m, 1H), 2.78 (m, 1H), 3.12 (m, 1H), 3.83 (m, 1H), 7.43 (d, 1H), 7.50 (d, 1H), 7.84 (s, 1H), 7.89 (s, 1H). LCMS(ESI): [M]⁺ m/z: calcd 213.2; found 214.2; Rt=0.878 min.

Step 4: Synthesis of rac-6-((2R,5S)-5-methylpiperidin-2-yl)-1H-indazole 6-(5-methyl-3,4,5,6-tetrahydropyridin-2-yl)-1H-indazole (1.15 g, 5.39 mmol) was dissolved in MeOH (15 mL) and sodium borohydride (1.02 g, 26.96 mmol, 953.24 μL) was added portion wise under cooling with ice water. The reaction mixture was heated to rt and stirred for 12 hr. NH₄Cl (aq.) was added and MeOH was evaporated, aqueous layer was extracted with DCM (3*30 ml) and combined organic layer was dried over Na₂SO₄, filtered and evaporated on vacuo at 45° C. to give rac-6-((2R,5S)-5-methylpiperidin-2-yl)-1H-indazole (0.36 g, 1.67 mmol, ³1.01% yield) which was used in the next step without further purification.

¹H NMR (400 MHz, DMSO-d₆) δ (ppm) 0.80 (d, 3H), 1.07 (m, 1H), 1.34 (m, 1H), 1.49 (m, 1H), 1.73 (m, 2H), 2.25 (m, 1H), 2.35 (m, 1H), 2.97 (m, 1H), 3.54 (m, 2H), 7.05 (d, 1H), 7.43 (s, 1H), 7.58 (d, 1H), 7.93 (s, 1H). LCMS(ESI): [M]⁺ m/z: calcd 215.2; found 216.2; Rt=1.035 min.

Step 5: Synthesis of rac-tert-butyl (5-(2-((2R,5S)-2-(1H-indazol-6-yl)-5-methylpiperidin-1-yl)-2-oxoacetamido)-3-methylpyridin-2-yl)carbamate tert-butyl N-[3-methyl-5-(oxamoylamino)-2-pyridyl]carbamate (492.12 mg, 1.67 mmol) and TEA (1.69 g, 16.72 mmol, 2.33 mL) were dissolved in DMF (10 mL) and cooled to 0° C., HATU (953.69 mg, 2.51 mmol) was added and the mixture was stirred for 15 min at 0° C. 6-[(2S,5R)-5-methyl-2-piperidyl]-1H-indazole (0.36 g, 1.67 mmol) was added and the mixture was warmed to rt and stirred for 3 hr. 10 ml of Ethyl acetate was added and organic phase was washed with brine three times. Organic phase was dried over Na₂SO₄, filtered and concentrated in vacuum at 45° C. to give crude product which was purified by HPLC (40-60% water/MeOH, 2-10 min, (loading pump 4 ml MeOH), column: TRIART 100*20) to give tert-butyl N-[5-[[2-[(2S,5R)-2-(1H-indazol-6-yl)-5-methyl-1-piperidyl]-2-oxo-acetyl]amino]-3-methyl-2-pyridyl]carbamate (0.07 g, 142.11 μmol, 8.50% yield).

LCMS(ESI): [M]⁺ m/z: calcd 492.2; found 493.2; Rt=1.120 min.

Step 6: Chiral Separation

Chiral separation was performed using Column: Chiralpak OD-H (250*30 mm, 5 mkm); Mobile phase: Hexane-IPA-MeOH 50-25-25 Flow Rate: 20 mL/min to give 1st enantiomer as mixture of cis- and trans-isomers and tert-butyl (5-(2-(2-(1H-indazol-6-yl)-5-methylpiperidin-1-yl)-2-oxoacetamido)-3-methylpyridin-2-yl)carbamate (0.02 g, 40.60 μmol, 28.57% yield) as pure enantiomer.

The mixture of cis- and trans-isomers was separated using Chiralpak 1B (250*20 mm, 5 mkm); Mobile phase: Hexane-EtOH 90-10 Flow Rate: 14 mL/min to give tert-butyl (5-(2-(2-(1H-indazol-6-yl)-5-methylpiperidin-1-yl)-2-oxoacetamido)-3-methylpyridin-2-yl)carbamate (0.014 g, 28.42 μmol, 20.00% yield) as pure enantiomer (trans).

Ret time for E1 in analytical conditions (column: OD-H, Hexane-IPA-MeOH 50-25-25, 0.6 ml/min as mobile phase) 29.09 min and for E2 15.60 min.

E1: LCMS(ESI): [M]⁺ m/z: calcd 492.2; found 493.2; Rt=4.930 min.

E2: LCMS(ESI): [M]⁺ m/z: calcd 492.2; found 493.2; Rt=4.941 min.

Step 7: Synthesis of 2-(2-(1H-indazol-6-yl)-5-methylpiperidin-1-yl)-N-(6-amino-5-methylpyridin-3-yl)-2-oxoacetamide (Compound 613 and Compound 636 tert-butyl N-[5-[[2-[(2S,5R)-2-(1H-indazol-6-yl)-5-methyl-1-piperidyl]-2-oxo-acetyl]amino]-3-methyl-2-pyridyl]carbamate (0.014 g, 28.42 μmol) and tert-butyl N-[5-[[2-[(2R,5S)-2-(1H-indazol-6-yl)-5-methyl-1-piperidyl]-2-oxo-acetyl]amino]-3-methyl-2-pyridyl]carbamate (0.02 g, 40.60 μmol) were dissolved in mixture of dioxane (2 mL) and water (2 mL) then stirred at 100° C. for 12 hr.

The reaction mixture was concentrated on vacuum at 55° C. to give crude product which was purified by HPLC (0.1% FA/MeCN, 5-95% MeCN, 6 min, column: Zorbax Eclipse-plus C18 4.6*100 mm, 3.5 mkm) to give N-(6-amino-5-methyl-3-pyridyl)-2-[(2S,5R)-2-(1H-indazol-6-yl)-5-methyl-1-piperidyl]-2-oxo-acetamide (0.001 g, 2.55 μmol, 8.97% yield) and N-(6-amino-5-methyl-3-pyridyl)-2-[(2R,5S)-2-(1H-indazol-6-yl)-5-methyl-1-piperidyl]-2-oxo-acetamide (0.001 g, 2.55 μmol, 6.28% yield).

Compound 613: $^1$H NMR (600 MHz, DMSO-$d_6$) δ (ppm) 0.98 (d, 3H), 1.07 (m, 1H), 1.36 (m, 2H), 1.86 (m, 2H), 2.24 (s, 3H), 2.28 (m, 2H), 4.18 (m, 1H), 5.68 (m, 2H), 7.16 (m, 1H), 7.48 (m, 2H), 7.78 (m, 1H), 8.03 (m, 2H), 10.56 (m, 1H), 13.02 (m, 1H).

LCMS(ESI): [M]$^+$ m/z: calcd 392.2; found 393.2; Rt=3.623 min.

Compound 636: $^1$H NMR (600 MHz, DMSO-$d_6$) δ (ppm) 0.98 (d, 3H), 1.07 (m, 1H), 1.36 (m, 2H), 1.86 (m, 2H), 2.24 (s, 3H), 2.28 (m, 2H), 4.18 (m, 1H), 5.68 (m, 2H), 7.16 (m, 1H), 7.48 (m, 2H), 7.78 (m, 1H), 8.03 (m, 2H), 10.56 (m, 1H), 13.02 (m, 1H).

LCMS(ESI): [M]$^+$ m/z: calcd 392.2; found 393.2; Rt=3.599 min.

Example 780. The Synthesis of 5-[[2-[(2R,5S)-2-(2-cyanophenyl)-5-methyl-1-piperidyl]-2-oxo-acetyl]amino]pyridine-3-carboxamide (Compound 664)

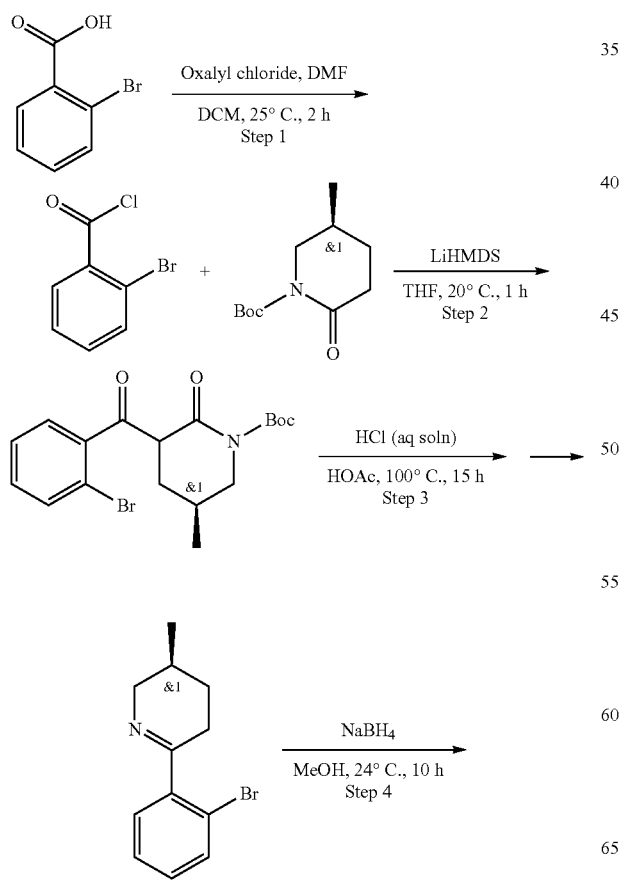

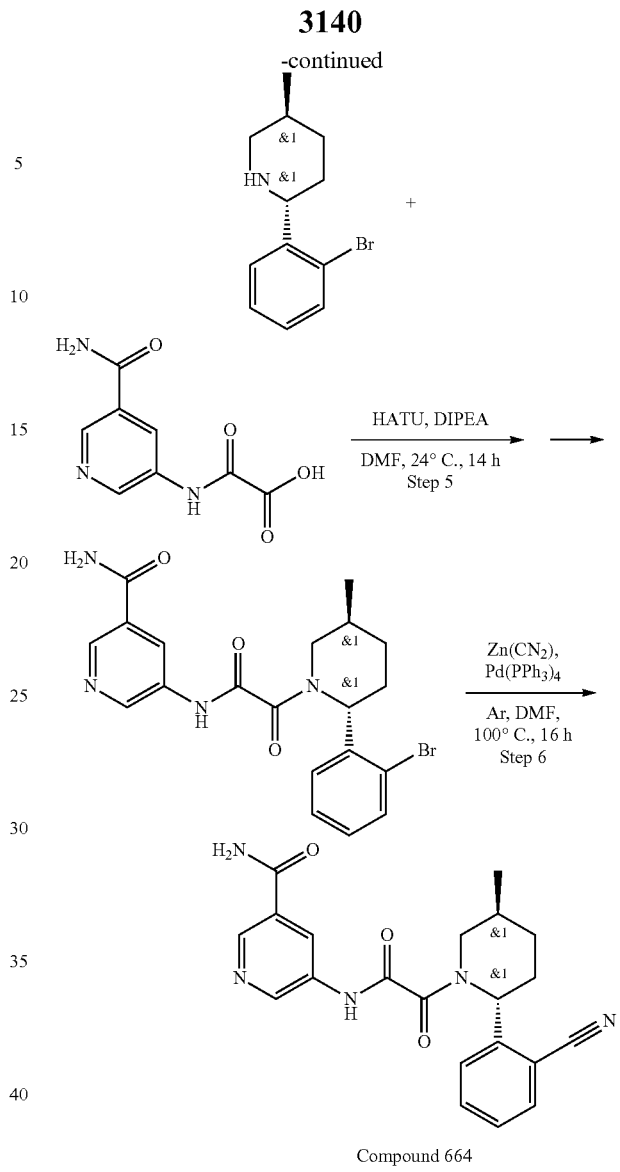

Compound 664

Step 1: The Synthesis of 2-bromobenzoyl chloride 2-bromobenzoic acid (5 g, 24.87 mmol) and oxalyl chloride (4.74 g, 37.31 mmol, 3.24 mL) were suspended in DCM (50 mL). DMF (1.82 g, 24.87 mmol, 1.93 mL) was added thereto in 3 portions. Resulting mixture was stirred at 25° C. for 2 hr. When gas evolution ceased, resulting clear solution was concentrated under reduced pressure. Residue was redissolved in hexane (150 ml), filtered and evaporated in vacuo, afford to 2-bromobenzoyl chloride (5 g, 22.78 mmol, 91.60% yield).

$^1$H NMR (500 MHz, DMSO-$d_6$) δ 7.44 (m, 2H), 7.71 (m, 2H).

GCMS: m/z: calcd 217.0; found 214.0; Rt=7.52 min.

Step 2: The Synthesis of tert-butyl 3-(2-bromobenzoyl)-5-methyl-2-oxo-piperidine-1-carboxylate Lithium bis(trimethylsilyl)amide (3.20 g, 19.14 mmol) was added dropwise to a precooled solution of tert-butyl 5-methyl-2-oxo-piperidine-1-carboxylate (1.94 g, 9.11 mmol) in THF (50 mL) at −78° C. After addition was complete, it was stirred at the same temperature for 1 h. After that, 2-bromobenzoyl chloride (2 g, 9.11 mmol) was added in one portion and cooling bath was removed. Resulting mixture was slowly warmed up to 20° C. and stirred at this temperature for 1 hr. Then, it was quenched with 15% aq. NaHSO₄ (50 ml) and extracted with ethyl acetate (100 ml). Organic layer was washed with 20% aq. NaCl (2×50 ml), dried over Na₂SO₄ and evaporated under reduced pressure to afford tert-butyl 3-(2-bromobenzoyl)-5-methyl-2-oxo-piperidine-1-carboxylate (3.5 g, 8.83 mmol, 96.92% yield).

¹H NMR (500 MHz, DMSO-d₆) δ 0.85 (d, 3H), 1.47 (m, 8H), 1.80 (m, 1H), 1.91 (m, 2H), 3.13 (m, 1H), 3.29 (m, 2H), 3.72 (m, 1H), 7.18 (m, 1H), 7.25 (m, 1H), 7.49 (d, 1H), 7.72 (d, 1H).

LCMS(ESI): [M−tBu]⁺ m/z: calcd 339.1; found 340.2; Rt=1.519 min.

Step 3: The Synthesis of 6-(2-bromophenyl)-3-methyl-2,3,4,5-tetrahydropyridine tert-butyl 3-(2-bromobenzoyl)-5-methyl-2-oxo-piperidine-1-carboxylate (3.5 g, 8.83 mmol) was dissolved in AcOH (26 mL) and Hydrochloric acid, 36% w/w aq. soln. (20.93 g, 574.10 mmol, 26.17 mL) was added portionwise (a lot of foam is produced). After addition was complete, resulting mixture was stirred at 100° C. for 15 hr. Then, solvents were removed under reduced pressure and residue was partitioned between 1 N HCl (100 ml) and DCM (200 ml). Organic layer was separated and discarded. Aqueous layer was basified to pH 10 with 10% NaOH and extracted with DCM (2×100 ml). DCM solution was separated, dried over Na₂SO₄ and evaporated under reduced pressure to afford 6-(2-bromophenyl)-3-methyl-2,3,4,5-tetrahydropyridine (1.2 g, 4.76 mmol, 53.88% yield).

¹H NMR (400 MHz, DMSO-d₆) δ 0.91 (d, 3H), 1.32 (m, 1H), 1.65 (m, 1H), 1.77 (m, 1H), 2.39 (m, 2H), 3.08 (m, 1H), 3.75 (m, 1H), 7.23 (m, 2H), 7.35 (m, 1H), 7.57 (d, 1H).

LCMS(ESI): [M+H]⁺ m/z: calcd 251.0; found 252.2; Rt=0.812 min.

Step 4: The Synthesis of 2-(2-bromophenyl)-5-methyl-piperidine

Sodium Borohydride (360.10 mg, 9.52 mmol, 336.54 μL) was added in one portion to a stirred solution of 6-(2-bromophenyl)-3-methyl-2,3,4,5-tetrahydropyridine (1.2 g, 4.76 mmol) in MeOH (10 mL) at 0° C. The resulting mixture was stirred for 10 hr, and then evaporated in vacuo. The residue was diluted with water (20 ml) and extracted with dichloromethane (2*40 ml). The combined organic extracts were dried over sodium sulphate and evaporated in vacuo. The obtained oil was subjected to afford 2-(2-bromophenyl)-5-methyl-piperidine (0.8 g, 3.15 mmol, 66.14% yield).

¹H NMR (400 MHz, DMSO-d₆) δ 0.80 (d, 3H), 1.09 (m, 2H), 1.51 (m, 1H), 1.76 (m, 2H), 2.23 (m, 1H), 2.96 (m, 1H), 3.28 (m, 1H), 3.74 (m, 1H), 7.12 (dd, 1H), 7.33 (dd, 1H), 7.50 (d, 1H), 7.56 (d, 1H).

LCMS(ESI): [M+H]⁺ m/z: calcd 253.0; found 254.0; Rt=0.800 min.

Step 5: The Synthesis of 5-[[2-[2-(2-bromophenyl)-5-methyl-1-piperidyl]-2-oxo-acetyl]amino]pyridine-3-carboxamide DIPEA (610.20 mg, 4.72 mmol, 822.37 μL) was added to the solution of respective 2-(2-bromophenyl)-5-methyl-piperidine (0.3 g, 1.18 mmol) and 2-[(5-carbamoyl-3-pyridyl)amino]-2-oxo-acetic acid (246.88 mg, 1.01 mmol, HCl) in DMF (5 mL). The resulting mixture was stirred for 5 min followed by the addition of HATU (493.68 mg, 1.30 mmol). Then, the reaction mixture was stirred overnight at room temperature. After the completion of the reaction, monitored by LCMS, the resulting suspension was concentrated under reduced pressure. The obtained solid was subjected to HPLC (Waters Sunfire C18 19*100 5 mkm column and H₂O-MeOH+NH₃ as an eluent mixture) to afford pure 5-[[2-[2-(2-bromophenyl)-5-methyl-1-piperidyl]-2-oxo-acetyl]amino]pyridine-3-carboxamide (0.4 g, 898.25 μmol, 76.10% yield).

LCMS(ESI): [M+3H]⁺ m/z: calcd 444.1; found 447.0; Rt=1.261 min.

Step 6: The Synthesis of 5-[[2-[(2R,5S)-2-(2-cyanophenyl)-5-methyl-1-piperidyl]-2-oxo-acetyl]amino]pyridine-3-carboxamide (Compound 664

A suspension of 5-[[2-[2-(2-bromophenyl)-5-methyl-1-piperidyl]-2-oxo-acetyl]amino]pyridine-3-carboxamide (40 mg, 89.83 μmol) and Zinc Cyanide (21.10 mg, 179.65 μmol, 11.40 μL) in DMF (5 mL) was degassed and refilled with Ar three time. To this solution, Palladium (0)tetrakis(triphenylphosphine) (10.38 mg, 8.98 μmol) was added. The resulting mixture was degassed, refilled with Ar and stirred at 100° C. for 16 hr. After the completion of the reaction, monitored by LCMS, the resulting suspension was concentrated under reduced pressure. The obtained solid was subjected to HPLC (Waters Sunfire C18 19*100 5 mkm column and H₂O-MeCN as an eluent mixture) to afford pure 5-[[2-[(2R,5S)-2-(2-cyanophenyl)-5-methyl-1-piperidyl]-2-oxo-acetyl]amino]pyridine-3-carboxamide (3.5 mg, 8.94 μmol, 9.95% yield).

¹H NMR (DMSO-d₆, 600 MHz): δ (ppm) 0.93 (m, 4H), 1.10 (m, 1H), 1.86 (m, 2H), 2.07 (m, 1H), 3.77 (m, 2H), 5.34 (m, 1H), 7.46 (m, 1H), 7.56 (m, 1H), 7.61 (m, 1H), 7.70 (m, 1H), 7.84 (m, 1H), 8.16 (m, 1H), 8.49 (m, 1H), 8.76 (m, 1H), 8.86 (m, 1H), 11.19 (m, 1H). LCMS(ESI): [M+H]⁺ m/z: calcd 391.4; found 392.4; Rt=2.286 min.

Example 781. The Synthesis of 5-[[2-[(2S,5R)-2-(2-methoxyphenyl)-5-methyl-1-piperidyl]-2-oxo-acetyl]amino]pyridine-3-carboxamide (Compound 558)

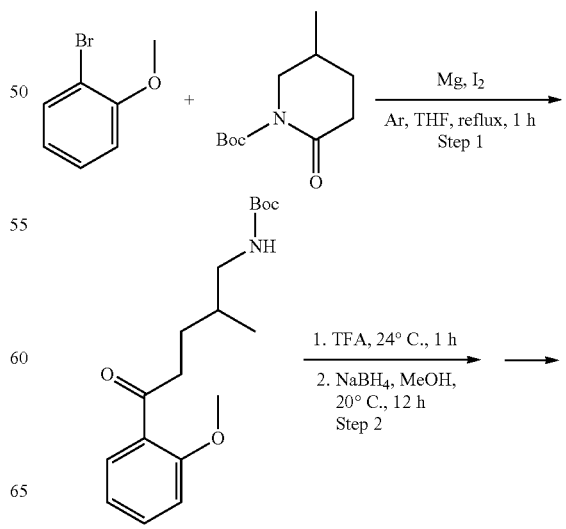

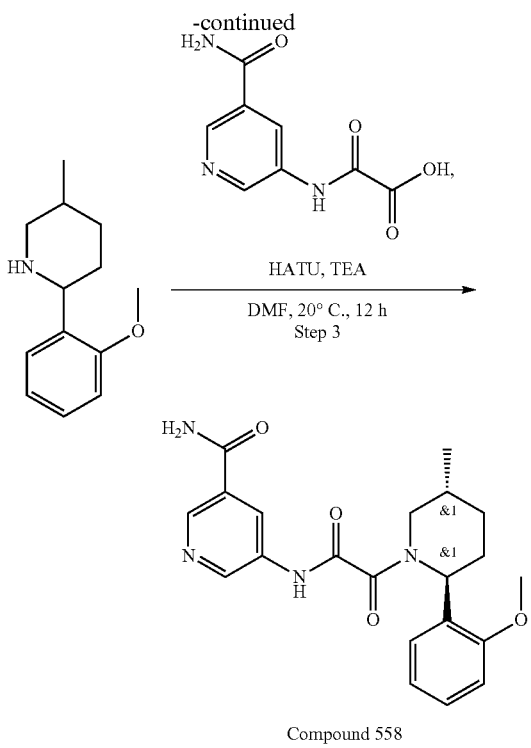

Compound 558

Step 1: The Synthesis of tert-butyl N-[5-(2-methoxyphenyl)-2-methyl-5-oxo-pentyl]carbamate 1-bromo-2-methoxy-benzene (5 g, 26.73 mmol, 3.33 mL) was added to the mixture of THF (30 mL) and Magnesium (649.75 mg, 26.73 mmol, 373.42 μL) under argon atmosphere. iodine (67.85 mg, 267.33 μmol) was added thereto and the resulting mixture was heated to reflux for 1 h. The resulting mixture was cooled to r.t. and added dropwise to the solution of tert-butyl 5-methyl-2-oxo-piperidine-1-carboxylate (5.70 g, 26.73 mmol) in THF (30 mL) at −78° C. The resulting mixture was left to warm to r.t. and then poured into aq. NH$_4$Cl solution. The resulting mixture was extracted with EtOAc (2×40 ml). The combined organic extracts were washed with brine, dried over Na$_2$SO$_4$ and evaporated to obtain tert-butyl N-[5-(2-methoxyphenyl)-2-methyl-5-oxo-pentyl]carbamate (7 g, 21.78 mmol, 81.47% yield), which was used in next step without purification.

LCMS(ESI): [M+H]$^+$ m/z: calcd 221.2; found 222.2; Rt=1.364 min.

Step 2: The Synthesis of 2-(2-methoxyphenyl)-5-methyl-piperidine tert-butyl N-[5-(2-methoxyphenyl)-2-methyl-5-oxo-pentyl]carbamate (7 g, 21.78 mmol) was dissolved in Trifluoroacetic acid (24.83 g, 217.79 mmol, 16.78 mL) and the resulting mixture was stirred for 1 hr. 50% aq. NaOH solution was added thereto to pH 11-12. The resulting mixture was extracted with CH$_2$Cl$_2$ (4×40l) the combined organic layer was evaporated to dryness. The residue was redissolved in MeOH (50 mL) and Sodium Borohydride (823.96 mg, 21.78 mmol, 770.05 μL) was added. The resulting mixture was stirred at 20° C. for 12 hr and evaporated. 50% aq. NaOH solution was added to the residue. The resulting mixture was extracted with CH$_2$C12 (4×40 ml) the combined organic layer was evaporated to dryness to obtain 2-(2-methoxyphenyl)-5-methyl-piperidine (3 g, 14.61 mmol, 67.10% yield) which was used in next step without purification.

$^1$H NMR (500 MHz, DMSO-d$_6$) δ 1.10 (d, 3H), 1.22 (m, 1H), 1.48 (m, 2H), 1.52 (m, 2H), 1.76 (m, 2H), 2.98 (m, 1H) 3.75 (s, 3H), 3.77 (m, 1H), 6.88 (m, 2H), 7.15 (dd, 1H), 7.40 (d, 1H).

LCMS(ESI): [M+H]$^+$ m/z: calcd 205.2; found 206.2; Rt=0.762 min.

Step 3: The Synthesis of 5-[[2-[(2S,5R)-2-(2-methoxyphenyl)-5-methyl-1-piperidyl]-2-oxo-acetyl]amino]pyridine-3-carboxamide (Compound 558

2-(2-methoxyphenyl)-5-methyl-piperidine (0.2 g, 974.21 μmol) was mixed with HATU (407.46 mg, 1.07 mmol) in DMF (4 mL) and the resulting mixture was stirred at 20° C. for 10 min followed by addition of 2-[(5-carbamoyl-3-pyridyl)amino]-2-oxo-acetic acid (239.28 mg, 974.21 μmol, HCl). The resulting mixture was stirred at 20° C. for 12 hr. The resulting solution was subjected to HPLC to obtain 5-[[2-[(2S,5R)-2-(2-methoxyphenyl)-5-methyl-1-piperidyl]-2-oxo-acetyl]amino]pyridine-3-carboxamide (0.0874 g, 220.46 μmol, 22.63% yield)

HPLC conditions: 23% 0.5-6.5 min water-acetonitrile; flow: 30 ml/min; (loading pump 4 ml/min acetonitrile); target mass 396; column: SunFire C18 100×19 mm 5 um (L)

$^1$H NMR (600 MHz, DMSO-d$_6$) δ 0.95-1.00 (m, 3H), 1.07-1.38 (m, 1H), 1.67-1.97 (m, 2H), 1.98-2.04 (m, 1H), 2.05-2.21 (m, 1H), 3.14-3.20 (m, 0.4H), 3.55-3.59 (m, 0.6H), 3.60-3.92 (m, 4H), 5.37-5.56 (m, 1H), 6.83-7.03 (m, 2H), 7.12-7.32 (m, 2H), 7.52-7.64 (m, 1H), 8.09-8.20 (m, 1H), 8.36-8.51 (m, 1H), 8.71-8.93 (m, 2H), 10.70-11.33 (m, 1H).

LCMS(ESI): [M+H]$^+$ m/z: calcd 396.2; found 397.2; Rt=2.608 min.

Example 782. The Synthesis of 5-[[2-[(2R,5S)-2-(2-fluorophenyl)-5-methyl-1-piperidyl]-2-oxo-acetyl]amino]pyridine-3-carboxamide (Compound 595)

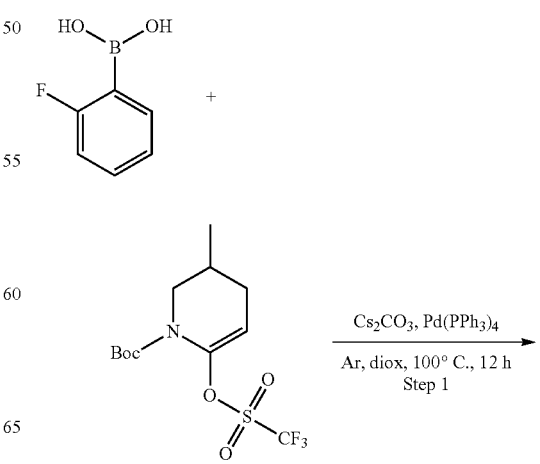

-continued

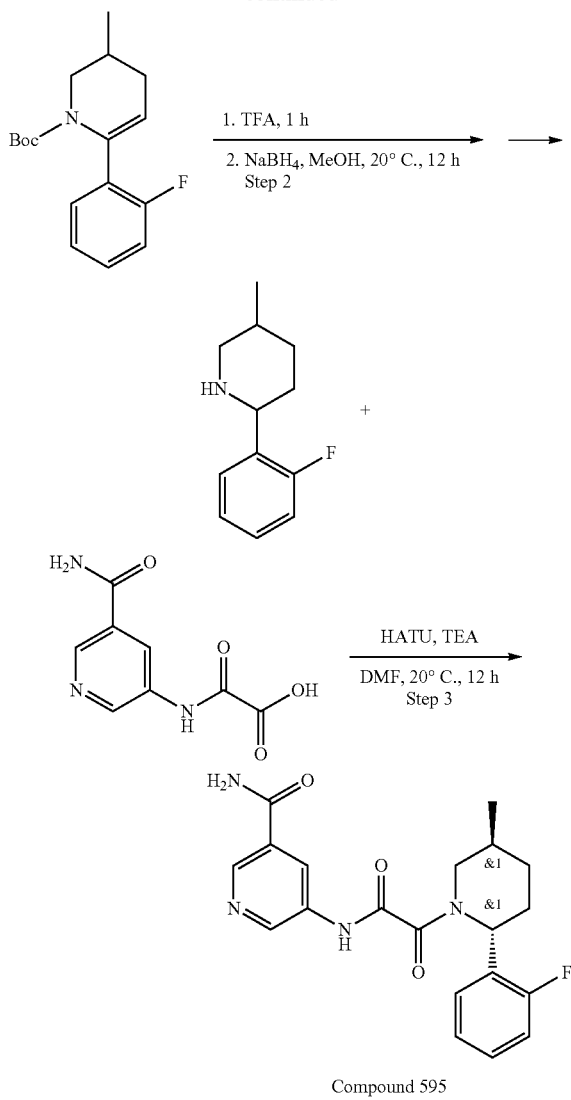

Compound 595

Step 1: The Synthesis of tert-butyl 6-(2-fluorophenyl)-3-methyl-3,4-dihydro-2H-pyridine-1-carboxylate (2-fluorophenyl)boronic acid (1 g, 7.15 mmol), tert-butyl 3-methyl-6-(trifluoromethylsulfonyloxy)-3,4-dihydro-2H-pyridine-1-carboxylate (2.71 g, 7.86 mmol) and caesium carbonate (6.99 g, 21.44 mmol) were mixed in Dioxane (30 mL) under argon atmosphere. Tetrakis(triphenylphosphine) palladium(0), 99.8% (metals basis), Pd 9% min (247.76 mg, 214.41 µmol) was added and the resulting mixture was heated to 100° C. for 12 hr. The resulting mixture was cooled to r.t. and evaporated in vacuo. The residue was partitioned between EtOAc (50 ml) and water (50 ml). The organic phase was collected, washed with brine, dried over sodium sulfate and evaporated to obtain tert-butyl 6-(2-fluorophenyl)-3-methyl-3,4-dihydro-2H-pyridine-1-carboxylate (2.5 g, crude) which was used in next step without purification.

LCMS(ESI): [M−tBu]+ m/z: calcd 235.0; found 236.0; Rt=1.359 min.

Step 2: The Synthesis of 2-(2-fluorophenyl)-5-methyl-piperidine tert-butyl 6-(2-fluorophenyl)-3-methyl-3,4-dihydro-2H-pyridine-1-carboxylate (2.5 g, 8.58 mmol) was dissolved in Trifluoroacetic acid (9.78 g, 85.80 mmol, 6.61 mL) and the resulting mixture was stirred for 1 hr. 50% aq. NaOH solution was added thereto to pH 11-12. The resulting mixture was extracted with $CH_2Cl_2$ (4×40l) the combined organic layer was evaporated to dryness. The residue was redissolved in MeOH (20 mL) and Sodium Borohydride (324.62 mg, 8.58 mmol, 303.38 µL) was added. The resulting mixture was stirred at 20° C. for 12 hr and evaporated. 50% aq. NaOH solution was added to the residue. The resulting mixture was extracted with $CH_2Cl2$ (4×40 ml) the combined organic layer was evaporated to dryness to obtain 2-(2-fluorophenyl)-5-methyl-piperidine (1 g, crude) which was used in next step without purification.

LCMS(ESI): [M+H]+ m/z: calcd 193.2; found 194.0; Rt=0.698 min.

Step 3: The Synthesis of 5-[[2-[(2R,5S)-2-(2-fluorophenyl)-5-methyl-1-piperidyl]-2-oxo-acetyl]amino]pyridine-3-carboxamide (Compound 595

2-(2-fluorophenyl)-5-methyl-piperidine (0.2 g, 1.03 mmol), 2-[(5-carbamoyl-3-pyridyl)amino]-2-oxo-acetic acid (254.19 mg, 1.03 mmol, HCl) and triethylamine (261.80 mg, 2.59 mmol, 360.60 µL) were mixed in DMF (5 mL). HATU (432.84 mg, 1.14 mmol) was added thereto in small portions with intensive stirring and the resulting mixture was stirred at 20° C. for 12 hr. The resulting mixture was subjected to HPLC to obtain 5-[[2-[(2R,5S)-2-(2-fluorophenyl)-5-methyl-1-piperidyl]-2-oxo-acetyl]amino]pyridine-3-carboxamide (0.0709 g, 184.44 µmol, 17.82% yield).

HPLC conditions:
23% 0.5-6.5 min water-acetonitrile; flow 30 ml/min (loading pump 4 ml/min; acetonitrile); target mass 384; column SunFire C18 100×19 mm 5 um (R)

$^1$H NMR (400 MHz, DMSO-$d_6$) δ 0.89-1.10 (m, 3H), 1.14-1.46 (m, 1H), 1.73-1.98 (m, 2H), 1.99-2.24 (m, 1.7H), 3.19-3.29 (m, 0.3H), 3.57-4.06 (m, 2H), 5.43-5.52 (m, 1H), 7.03-7.25 (m, 2H), 7.26-7.43 (m, 2H), 7.54-7.69 (m, 1H), 8.09-8.29 (m, 1H), 8.33-8.59 (m, 1H), 8.73-9.00 (m, 2H), 10.71-11.46 (m, 1H).

LCMS(ESI): [M+H]+ m/z: calcd 384.2; found 385.2; Rt=2.588 min.

Example 783. The Synthesis of 5-[[2-[(4S,4aR,8aR)-4-methyl-3,4,4a,5,6,7,8,8a-octahydro-1H-isoquinolin-2-yl]-2-oxo-acetyl]amino]pyridine-3-carboxamide (Compound 541), 5-[[2-[(4S,4aR,8aS)-4-methyl-3,4,4a,5,6,7,8,8a-octahydro-1H-isoquinolin-2-yl]-2-oxo-acetyl]amino]pyridine-3-carboxamide (Compound 543) and 5-[[2-[(4S,4aS,8aS)-4-methyl-3,4,4a,5,6,7,8,8a-octahydro-1H-isoquinolin-2-yl]-2-oxo-acetyl]amino]pyridine-3-carboxamide (Compound 542)

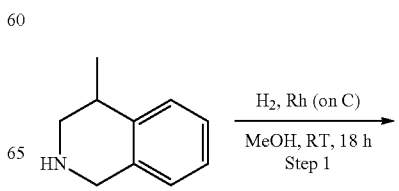

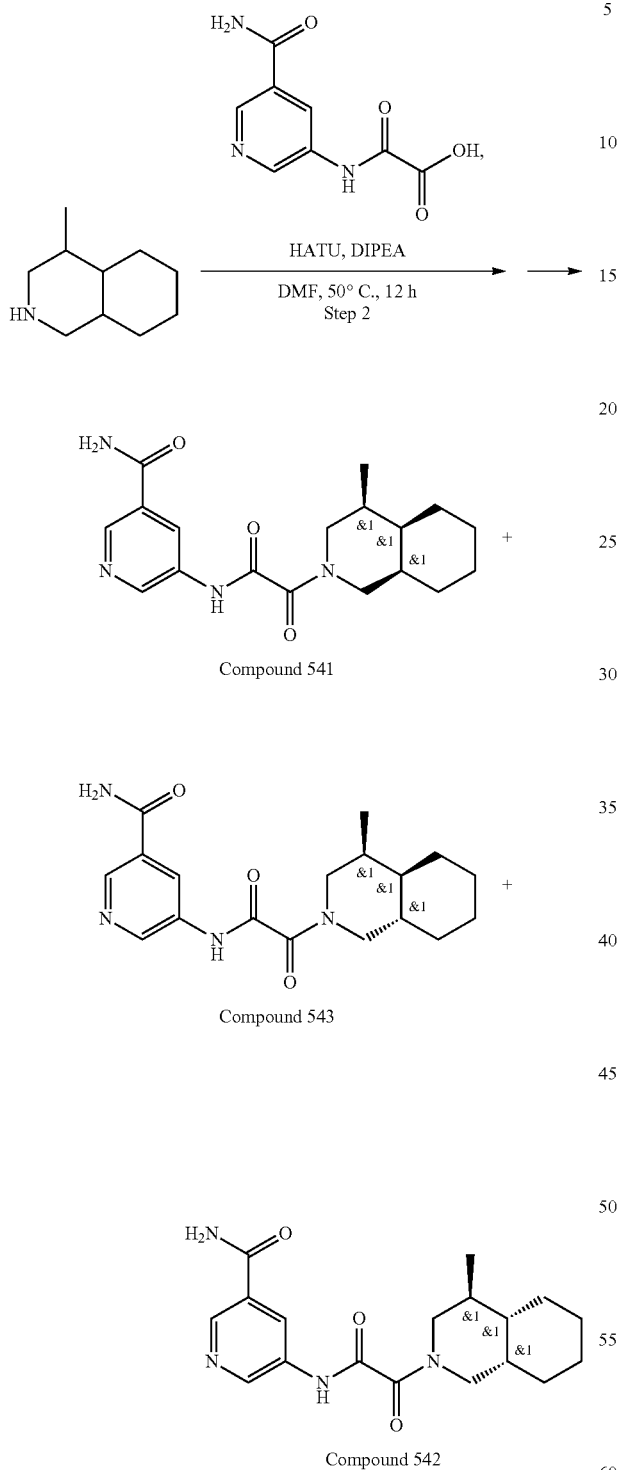

Compound 541

Compound 543

Compound 542

Step 1: The Synthesis of 4-methyl-1,2,3,4,4a,5,6,7,8,8a-decahydroisoquinoline 4-methyl-1,2,3,4-tetrahydroisoquinoline (1 g, 5.44 mmol, HCl) was dissolved in MeOH (20 mL) and hydrogenated under high pressure for 18 hr. After the reaction was completed, the catalyst was filtered off. The filtrate was evaporated under reduced pressure to afford 4-methyl-1,2,3,4,4a,5,6,7,8,8a-decahydroisoquinoline (1.1 g, crude, HCl) which was used in the next step without purification.

$^1$H NMR (400 MHz, DMSO-$d_6$) δ 0.89 (d, 3H), 1.65 (m, 11H), 2.92 (m, 4H), 9.03 (m, 1H)

LCMS(ESI): [M+H]$^+$ m/z: calcd 153.2; found 154.2; Rt=0.674 min.

Step 2: The Synthesis of 5-[[2-[(4S,4aR,8aR)-4-methyl-3,4,4a,5,6,7,8,8a-octahydro-1H-isoquinolin-2-yl]-2-oxo-acetyl]amino]pyridine-3-carboxamide (Compound 541), 5-[[2-[(4S,4aR,8aS)-4-methyl-3,4,4a,5,6,7,8,8a-octahydro-1H-isoquinolin-2-yl]-2-oxo-acetyl]amino]pyridine-3-carboxamide (Compound 543) and 5-[[2-[(4S,4aS,8aS)-4-methyl-3,4,4a,5,6,7,8,8a-octahydro-1H-isoquinolin-2-yl]-2-oxo-acetyl]amino]pyridine-3-carboxamide (Compound 542

4-methyl-1,2,3,4,4a,5,6,7,8,8a-decahydroisoquinoline (0.2 g, 1.05 mmol, HCl), 2-[(5-carbamoyl-3-pyridyl)amino]-2-oxo-acetic acid (220.49 mg, 1.05 mmol) and HATU (521.07 mg, 1.37 mmol) were dissolved in DMF (7 mL) under gentle heating. DIPEA (408.73 mg, 3.16 mmol, 550.85 μL) was added in small portions under vigorous stirring and occasional heating. After the reaction was complete, the mixture was purified by HPLC (0.5-6.5 min; water-acetonitrile; 30 ml/min; loading pump 4 ml/min acetonitrile; target mass 344; column SunFire 19*100 mm) to give 5-[[2-[(4S,4aR,8aR)-4-methyl-3,4,4a,5,6,7,8,8a-octahydro-1H-isoquinolin-2-yl]-2-oxo-acetyl]amino]pyridine-3-carboxamide (50 mg, 145.18 μmol, 13.77% yield) in 4 fractions.

Compound 541: $^1$H NMR (600 MHz, DMSO-$d_6$) δ 0.76-0.88 (m, 3H), 1.10-1.35 (m, 3H), 1.36-1.44 (m, 3H), 1.44-1.62 (m, 2H), 1.65-1.91 (m, 4H), 2.82-3.00 (m, 1H), 3.39-3.67 (m, 1H), 3.94-4.27 (m, 1H), 7.59 (s, 1H), 8.15 (s, 1H), 8.43-8.53 (m, 1H), 8.75 (s, 1H), 8.80-8.89 (m, 1H), 11.08 (s, 1H).

LCMS(ESI): [M+H]$^+$ m/z: calcd 344.2; found 345.2; Rt=2.938 min.

Compound 543: $^1$H NMR (600 MHz, DMSO-$d_6$) δ 0.77-0.88 (m, 3H), 1.19-1.36 (m, 5H), 1.43-1.50 (m, 2H), 1.59-1.72 (m, 2H), 1.74-1.92 (m, 3H), 2.72-3.06 (m, 1H), 3.56-3.69 (m, 1H), 3.96-4.10 (m, 1H), 7.59 (s, 1H), 8.14 (s, 1H), 8.45-8.51 (m, 1H), 8.74-8.78 (m, 1H), 8.83-8.89 (m, 1H), 11.05 (s, 1H).

LCMS(ESI): [M+H]$^+$ m/z: calcd 344.2; found 345.2; Rt=2.901 min.

Compound 542: $^1$H NMR (600 MHz, DMSO-$d_6$) δ 0.74-0.99 (m, 6H), 1.11-1.24 (m, 3H), 1.23-1.46 (m, 1H), 1.46-1.62 (m, 1H), 1.62-1.81 (m, 2H), 1.88 (t, 1H), 2.34-2.40 (m, 1H), 2.78 (t, 1H), 3.58-3.73 (m, 1H), 4.15-4.31 (m, 1H), 7.59 (s, 1H), 8.15 (s, 1H), 8.47 (s, 1H), 8.75 (s, 1H), 8.84 (s, 1H), 11.08 (s, 1H).

LCMS(ESI): [M+H]$^+$ m/z: calcd 344.2; found 345.2; Rt=3.014 min.

Example 784. The Synthesis of 2-[(2S,5S)-2-(3-acetamidocyclobutyl)-5-methyl-1-piperidyl]-N-(6-amino-5-methyl-3-pyridyl)-2-oxo-acetamide (Compound 562), the Synthesis of 2-[(2R,5R)-2-(3-acetamidocyclobutyl)-5-methyl-1-piperidyl]-N-(6-amino-5-methyl-3-pyridyl)-2-oxo-acetamide (Compound 564) and the Synthesis of 2-[(2R,5S)-2-(3-acetamidocyclobutyl)-5-methyl-1-piperidyl]-N-(6-amino-5-methyl-3-pyridyl)-2-oxo-acetamide (Compound 563)
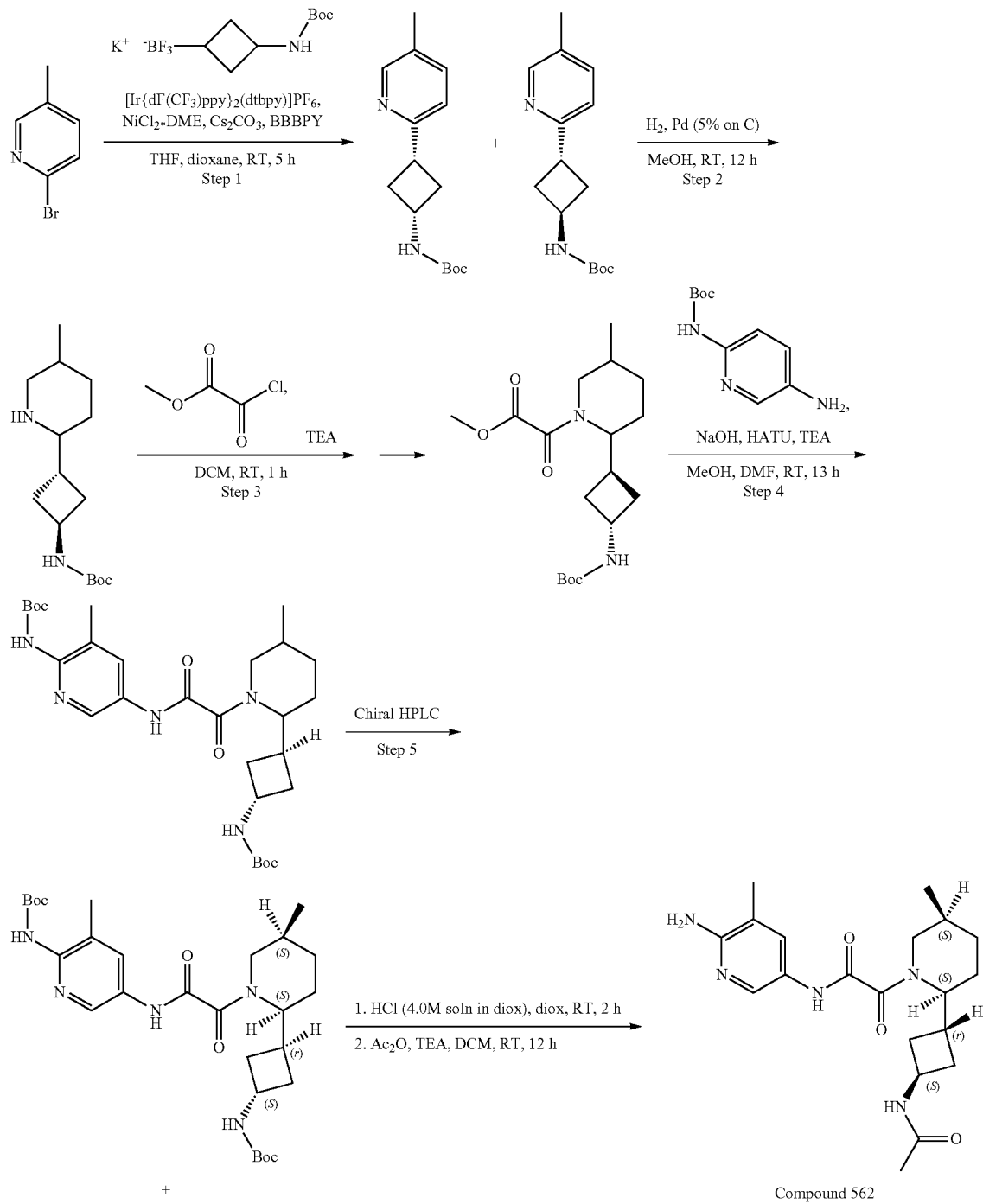

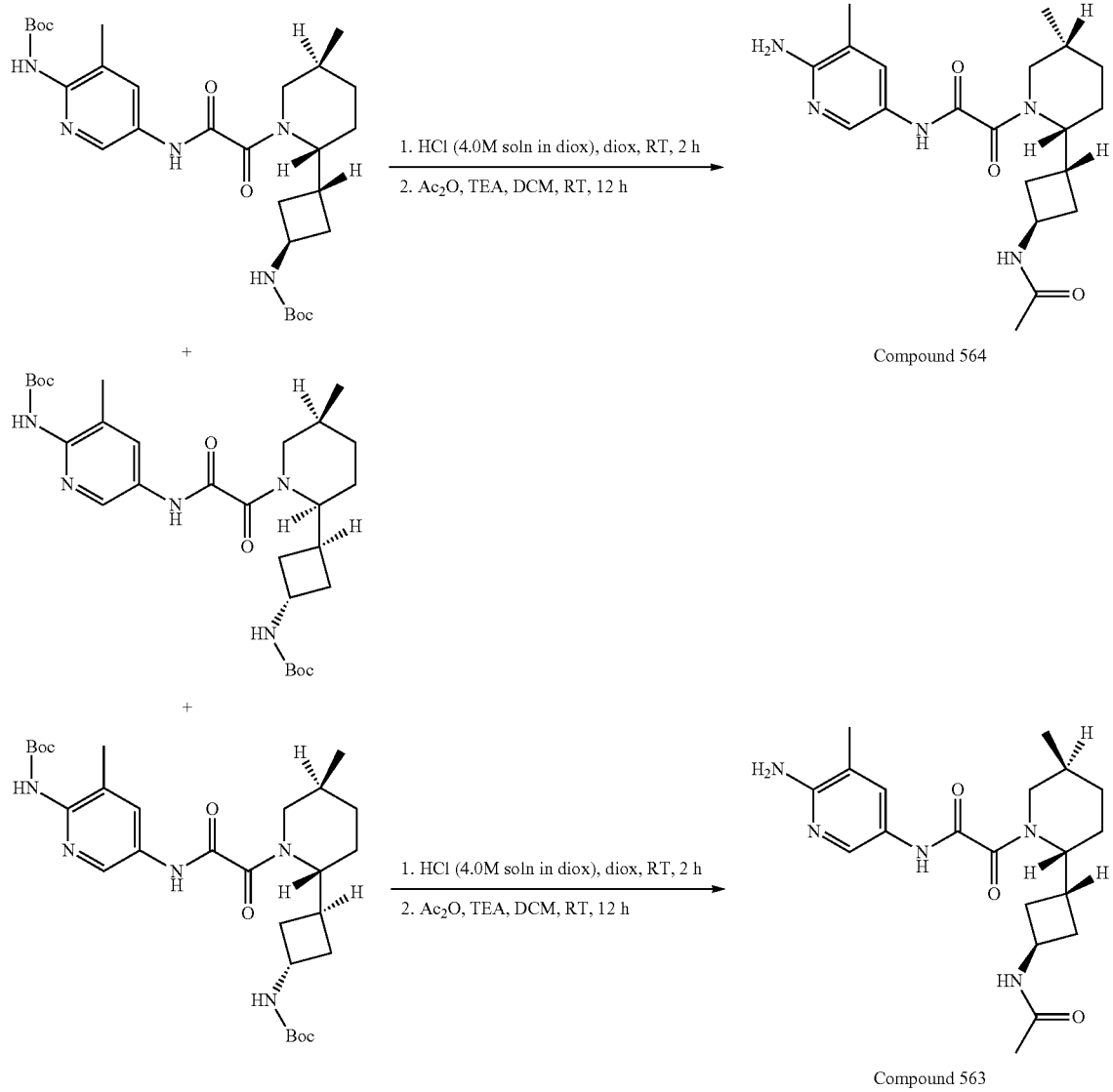

Step 1: The Synthesis of tert-butyl N-[3-(5-methyl-2-pyridyl)cyclobutyl]carbamate and tert-butyl N-[3-(5-methyl-2-pyridyl)cyclobutyl]carbamate To a glass vial equipped with a teflon-coated magnetic stir bar was added 4,4'-Di-tert-butyl-2,2'-dipyridyl (232.43 mg, 866.01 μmol) and NiCl$_2$DME (190.28 mg, 866.01 μmol) and THF (10 mL). The vial was capped and the resulting suspension was heated briefly with a heat gun until the nickel and ligand were fully solubilized, yielding a pale green solution. The solvent was removed under vacuum to give a fine coating of the ligated nickel complex (pale evergreen in color). Once dry, 2-bromo-5-methyl-pyridine (2.98 g, 17.32 mmol) (liquid aryl bromides were added with solvent), potassium; [3-(tert-butoxycarbonylamino)cyclobutyl]-trifluoro-boranuide (4.8 g, 17.32 mmol), [Ir{dF (CF$_3$)ppy}$_2$(dtbpy)]PF$_6$ (485.79 mg, 433.01 μmol) and cesium carbonate (8.46 g, 25.98 mmol) were added in succession. The vial was capped, purged and evacuated four times. Under an inert atmosphere, dioxane (80 mL) was introduced. The vial containing all the reagents was further sealed with parafilm and stirred for 5 h approximately 4 cm away from two 26 W fluorescent light bulbs. Then, the crude reaction mixture was filtered through an approximately 2 cm*2 cm cylindrical plug of celite, washing with EtOAc (10-20 mL). The resulting solution was concentrated and the residue was purified by column chromatography (Companion combiflash, 220 g SiO$_2$, petroleum ether/MtBE with MtBE from 10-50%, flow rate=100 mL/min, Rv=11 CV). Diastereomers were separated on SFC (Column: Chiralpak 1C (250*20 mm, 5 mkm); Mobile phase: CO$_2$-MeOH, 90-10. Flow Rate: 40 mL/min; Column Temperature: 40° C.; Wavelength: 215 nm. RetTime (cis)=6.84 min; RetTime (trans)=8.89 min). tert-butyl N-[3-(5-methyl-2-pyridyl)cyclobutyl]carbamate (414.64 mg, 1.58 mmol, 9.13% yield) and tert-butyl N-[3-(5-methyl-2-pyridyl)cyclobutyl]carbamate (622.9 mg, 2.37 mmol, 13.71% yield) were obtained as a white solids.

Cis: $^1$H NMR (400 MHz, CDCl$_3$) δ 1.39 (s, 9H), 2.11 (m, 2H), 2.24 (s, 3H), 2.70 (m, 2H), 3.16 (m, 1H), 4.13 (m, 1H), 4.96 (m, 1H), 6.97 (d, 1H), 7.33 (d, 1H), 8.34 (s, 1H).

LCMS(ESI): [M+H]$^+$ m/z: calcd 262.2; found 263.2; Rt=3.491 min.

Trans: ¹H NMR (400 MHz, CDCl₃) δ 1.39 (s, 9H), 2.26 (m, 5H), 2.61 (m, 2H), 3.54 (m, 1H), 4.29 (m, 1H), 4.85 (m, 1H), 7.05 (d, 1H), 7.37 (d, 1H), 8.34 (s, 1H).

LCMS(ESI): [M+H]⁺ m/z: calcd 262.2; found 263.2; Rt=3.482 min.

Step 2: The Synthesis of tert-butyl N-[3-(5-methyl-2-piperidyl)cyclobutyl]carbamate To a solution of tert-butyl N-[3-(5-methyl-2-pyridyl)cyclobutyl]carbamate (622.9 mg, 2.37 mmol) in MeOH (25 mL) in three-necked round-bottomed flask was added Pd, 5% on C, Type 5R39 (0.05 g)a. The reaction flask was evacuated and backfilled with molecular hydrogen (239.31 mg, 118.72 mmol) and the mixture was left to stir overnight. The reaction progress was monitored by LCMS and HNMR. Filtration through a thin pad of silica gel followed by concentration and drying under vacuum affording tert-butyl N-[3-(5-methyl-2-piperidyl)cyclobutyl]carbamate (0.54 g, 2.01 mmol, 84.74% yield) as a yellow oil (a mixture of diastereomers).

¹H NMR (500 MHz, CDCl₃) δ 0.93 (m, 4H), 1.44 (s, 9H), 1.57 (m, 2H), 1.79 (m, 2H), 1.96 (m, 2H), 2.17 (m, 4H), 2.75 (m, 2H), 3.08 (m, 1H), 4.13 (m, 1H), 4.79 (m, 1H).

LCMS(ESI): [M+H]⁺ m/z: calcd 268.2; found 269.4; Rt=1.995 min.

Step 3: The Synthesis of methyl 2-[2-[3-(tert-butoxycarbonylamino)cyclobutyl]-5-methyl-1-piperidyl]-2-oxo-acetate To a solution of tert-butyl N-[3-(5-methyl-2-piperidyl)cyclobutyl]carbamate (0.54 g, 2.01 mmol) and triethylamine (244.31 mg, 2.41 mmol, 336.51 µL) in DCM (25 mL) was added methyl 2-chloro-2-oxo-acetate (271.13 mg, 2.21 mmol) at 0° C. After stirring at rt for 1 hr, the resulting mixture were filtered and evaporated to dryness to give methyl 2-[2-[3-(tert-butoxycarbonylamino)cyclobutyl]-5-methyl-1-piperidyl]-2-oxo-acetate (0.64 g, crude) as a yellow solid, which was used in the next step without further purification.

LCMS(ESI): [M−tBu]⁺ m/z: calcd 298.2; found 299.0; Rt=1.256 min.

Step 4: The Synthesis of tert-butyl N-[5-[[2-[2-[3-(tert-butoxycarbonylamino)cyclobutyl]-5-methyl-1-piperidyl]-2-oxo-acetyl]amino]-3-methyl-2-pyridyl]carbamate To a solution of methyl 2-[2-[3-(tert-butoxycarbonylamino)cyclobutyl]-5-methyl-1-piperidyl]-2-oxo-acetate (0.64 g, 1.81 mmol) in MeOH (25 mL) was added Sodium hydroxide, pearl (79.44 mg, 1.99 mmol, 37.30 µL). The resulting mixture was stirred for 1 hr. Then, the solvent was evaporated and the residue was re-evaporated with EtOH. After that, solids were dissolved in DMF (15 mL) and HATU (686.57 mg, 1.81 mmol) was added followed by tert-butyl N-(5-amino-3-methyl-2-pyridyl)carbamate (403.15 mg, 1.81 mmol) and the resulting mixture was stirred for 12 hr. The resulting mixture was poured into water, extracted 3 times with EtOAc, combined organics were washed with water, brine and evaporated. The residue was subjected to HPLC (40-65% 2-7 min; water-acetonitrile 30 ml/min; loading pump: acetonitrile; 4 ml/min; column SunFire 19*100 mm). tert-butyl N-[5-[[2-[2-[3-(tert-butoxycarbonylamino)cyclobutyl]-5-methyl-1-piperidyl]-2-oxo-acetyl]amino]-3-methyl-2-pyridyl]carbamate (490.7 mg, 899.26 µmol, 49.80% yield) was obtained as a mixture of diastereomers. White solid.

¹H NMR (400 MHz, CDCl₃) δ 1.00 (d, 3H), 1.41 (s, 9H), 1.49 (s, 9H), 1.85 (m, 7H), 2.29 (s, 3H), 2.95 (m, 2H), 4.18 (m, 1H), 4.71 (m, 2H), 5.27 (m, 1H), 6.78 (m, 1H), 8.10 (s, 1H), 8.36 (s, 1H), 9.39 (m, 1H).

LCMS(ESI): [M+H]⁺ m/z: calcd 545.3; found 546.4; Rt=3.718 min.

Step 5: Chiral Separation of Tert-butyl N-[5-[[2-[2-[3-(tert-butoxycarbonylamino)cyclobutyl]-5-methyl-1-piperidyl]-2-oxo-acetyl]amino]-3-methyl-2-pyridyl]carbamate Two sequent purifications were performed: 1ˢᵗ SFC. P1 was separated from a mixture of P2 and P4 were obtained. P3 was lost on this step. 1C (250*20, 5 mkm), CO₂-MeOH, 70-30, 40 ml/min; Fow=15 ml/min; 2ⁿᵈ HPLC. P2 was separated from P4 IA-II (250*20, 5 mkm), Hexane-IPA-MeOH, 50-25-25, 12 ml/min RT of tert-butyl N-[5-[[2-[(2S,5S)-2-[3-(tert-butoxycarbonylamino)cyclobutyl]-5-methyl-1-piperidyl]-2-oxo-acetyl]amino]-3-methyl-2-pyridyl]carbamate (138.86 mg, 254.48 µmol, 28.30% yield)=12.854 min (IC, CO₂-MeOH, 70-30, 2.0 ml/min)

LCMS(ESI): [M+H]⁺ m/z: calcd 545.3; found 546.2; Rt=5.646 min.

RT of tert-butyl N-[5-[[2-[(2R,5R)-2-[3-(tert-butoxycarbonylamino)cyclobutyl]-5-methyl-1-piperidyl]-2-oxo-acetyl]amino]-3-methyl-2-pyridyl]carbamate (97.02 mg, 177.80 µmol, 19.77% yield)=32.773 min (IA, Hexane-IPA-MeOH, 50-25-25, 0.6 ml/min)

LCMS(ESI): [M+H]⁺ m/z: calcd 545.3; found 546.2; Rt=5.631 min.

RT of tert-butyl N-[5-[[2-[(2R,5S)-2-[3-(tert-butoxycarbonylamino)cyclobutyl]-5-methyl-1-piperidyl]-2-oxo-acetyl]amino]-3-methyl-2-pyridyl]carbamate (25.36 mg, 46.48 µmol, 5.17% yield)=9.201 min (IA, Hexane-IPA-MeOH, 50-25-25, 0.6 ml/min)

LCMS(ESI): [M+H]⁺ m/z: calcd 545.3; found 546.2; Rt 5.696=min.

The Synthesis of 2-[(2S,5S)-2-(3-acetamidocyclobutyl)-5-methyl-1-piperidyl]-N-(6-amino-5-methyl-3-pyridyl)-2-oxo-acetamide (Compound 562

To a solution of tert-butyl N-[5-[[2-[(2S,5S)-2-[3-(tert-butoxycarbonylamino)cyclobutyl]-5-methyl-1-piperidyl]-2-oxo-acetyl]amino]-3-methyl-2-pyridyl]carbamate (138.86 mg, 254.48 µmol) in dioxane (2 mL) was added hydrogen chloride solution 4.0 M in dioxane (46.39 mg, 1.27 mmol, 57.99 µL). The resulting mixture was stirred for 2 hr. The reaction mixture was evaporated to dryness and suspended in DCM (10 mL) and triethylamine (257.50 mg, 2.54 mmol, 354.69 µL) was added. The reaction mixture was left to stir overnight. The resulting mixture was evaporated and subjected to HPLC (5-30 2-7 min water-acetonitrile; flow: 30 ml/min; (loading pump 4 ml/min; acetonitrile); column: SunFire C18 100*19 mm 5 um (L)) to afford 2-[(2S,5S)-2-(3-acetamidocyclobutyl)-5-methyl-1-piperidyl]-N-(6-amino-5-methyl-3-pyridyl)-2-oxo-acetamide (63.6 mg, 164.14 µmol, 64.50% yield) as a white solid.

¹H NMR (600 MHz, DMSO-d₆) δ 0.88-0.96 (m, 3H), 1.21-1.29 (m, 1H), 1.33-1.42 (m, 1H), 1.61-1.73 (m, 1H), 1.73-1.78 (m, 3H), 1.78-2.00 (m, 6H), 2.00-2.05 (m, 3H), 2.72-3.24 (m, 2H), 3.33-3.87 (m, 1H), 3.91-4.53 (m, 2H), 5.54-5.65 (m, 2H), 7.41-7.49 (m, 1H), 7.93-8.01 (m, 1H), 8.03-8.13 (m, 1H), 10.20-10.36 (m, 1H).

LCMS(ESI): [M+H]⁺ m/z: calcd 387.2; found 388.4; Rt=1.334 min.

The Synthesis of 2-[(2R,5R)-2-(3-acetamidocyclobutyl)-5-methyl-1-piperidyl]-N-(6-amino-5-methyl-3-pyridyl)-2-oxo-acetamide (Compound 564

To a solution of tert-butyl N-[5-[[2-[(2R,5R)-2-[3-(tert-butoxycarbonylamino)cyclobutyl]-5-methyl-1-piperidyl]-2-oxo-acetyl]amino]-3-methyl-2-pyridyl]carbamate (97.02 mg, 177.80 µmol) in dioxane (2 mL) was added Hydrogen chloride solution 4.0 M in dioxane (32.41 mg, 889.00 µmol, 40.52 µL) and the resulting mixture was stirred for 2 hr. The reaction mixture was evaporated to dryness and suspended in DCM (10 mL) and triethylamine (179.92 mg, 1.78 mmol, 247.82 µL) was added. The reaction mixture was left to stir overnight. The resulting mixture was evaporated and subjected to HPLC (5-30 2-7 min water-acetonitrile; flow: 30 ml/min; (loading pump 4 ml/min; acetonitrile); column: SunFire C18 100*19 mm 5 um (L)) to afford 2-[(2R,5R)-2-(3-acetamidocyclobutyl)-5-methyl-1-piperidyl]-N-(6-amino-5-methyl-3-pyridyl)-2-oxo-acetamide (42.6 mg, 109.94 µmol, 61.83% yield) as a white solid.

¹H NMR (600 MHz, DMSO-d₆) δ 0.88-0.95 (m, 3H), 1.20-1.27 (m, 1H), 1.32-1.40 (m, 1H), 1.61-1.72 (m, 1H), 1.73-1.77 (m, 3H), 1.78-1.98 (m, 6H), 2.00-2.05 (m, 3H), 2.70-3.20 (m, 2H), 3.33-3.85 (m, 1H), 3.91-4.53 (m, 2H), 5.55-5.63 (m, 2H), 7.41-7.49 (m, 1H), 7.95-8.01 (m, 1H), 8.05-8.11 (m, 1H), 10.24-10.38 (m, 1H).

LCMS(ESI): [M+H]⁺ m/z: calcd 387.2; found 388.4; Rt=1.339 min.

The Synthesis of 2-[(2R,5S)-2-(3-acetamidocyclobutyl)-5-methyl-1-piperidyl]-N-(6-amino-5-methyl-3-pyridyl)-2-oxo-acetamide (Compound 563

To a solution of tert-butyl N-[5-[[2-[(2R,5S)-2-[3-(tert-butoxycarbonylamino)cyclobutyl]-5-methyl-1-piperidyl]-2-oxo-acetyl]amino]-3-methyl-2-pyridyl]carbamate (25.36 mg, 46.48 µmol) in dioxane (1 mL) was added Hydrogen chloride solution 4.0 M in dioxane (8.47 mg, 232.38 µmol, 10.59 µL). The resulting mixture was stirred for 2 hr. The reaction mixture was evaporated to dryness and suspended in DCM (5 mL) and triethylamine (47.03 mg, 464.75 µmol, 64.78 µL) was added. The reaction mixture was left to stir overnight. The resulting mixture was evaporated and subjected to HPLC (5-30 2-7 min water-acetonitrile; flow: 30 ml/min; (loading pump 4 ml/min; acetonitrile); column: SunFire C18 100*19 mm 5 um (L)) to obtain 2-[(2R,5S)-2-(3-acetamidocyclobutyl)-5-methyl-1-piperidyl]-N-(6-amino-5-methyl-3-pyridyl)-2-oxo-acetamide (10 mg, 25.81 µmol, 55.53% yield) as a white solid.

¹H NMR (500 MHz, DMSO-d₆+CCl₄) δ 0.80-0.93 (m, 3H), 1.22-1.31 (m, 1H), 1.45-1.64 (m, 4H), 1.72-1.79 (m, 3H), 1.83-2.02 (m, 4H), 2.03-2.06 (m, 3H), 2.08-2.30 (m, 1H), 2.68-2.85 (m, 1H), 3.40-3.87 (m, 1H), 3.98-4.16 (m, 1H), 4.24-4.59 (m, 1H), 5.56-5.69 (m, 2H), 7.42-7.60 (m, 1H), 7.98-8.05 (m, 1H), 8.06-8.15 (m, 1H), 10.28-10.49 (m, 1H).

LCMS(ESI): [M+H]⁺ m/z: calcd 387.2; found 388.4; Rt=1.621 min.

Example 785. The Synthesis of N-(6-amino-5-methylpyridin-3-yl)-2-(2-(6-aminospiro[3.3]heptan-2-yl)-5-methylpiperidin-1-yl)-2-oxoacetamide (Compound 773)

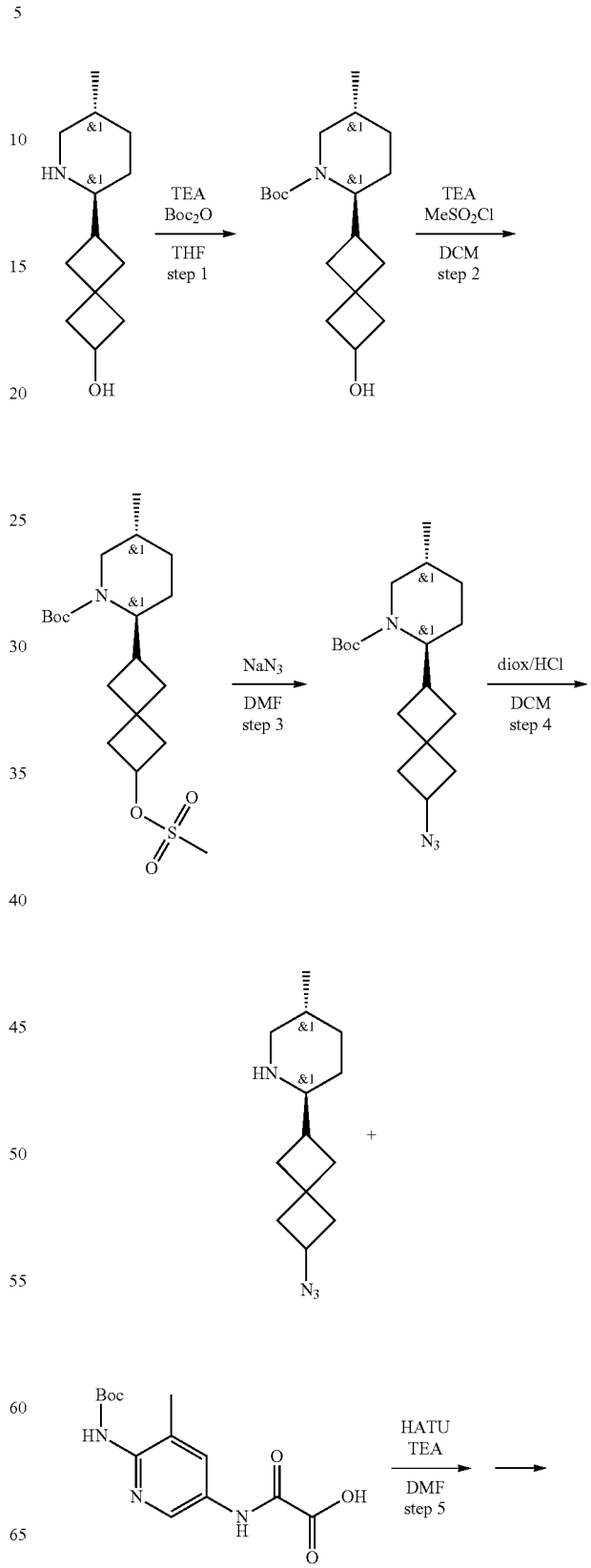

-continued

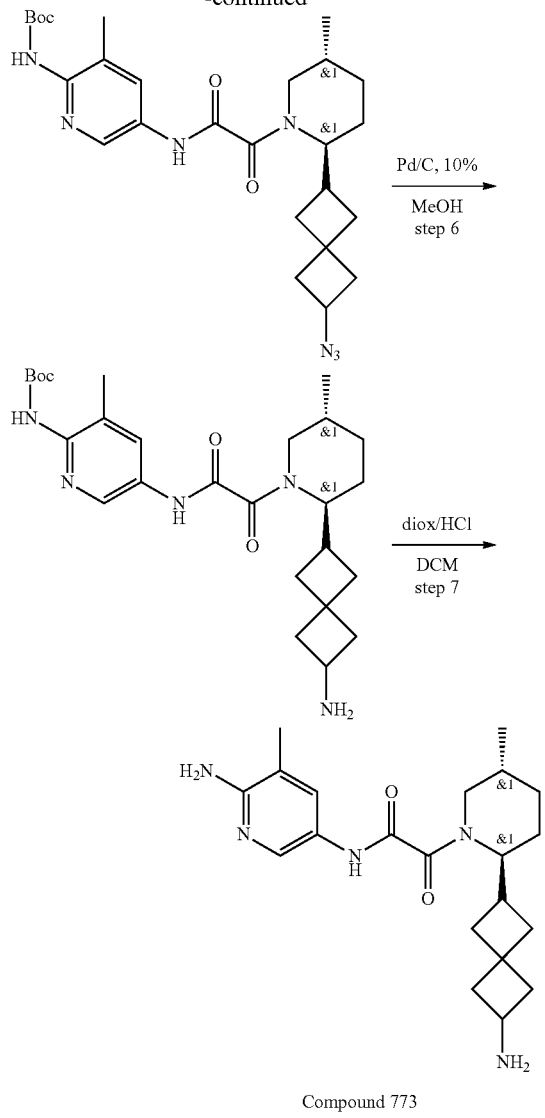

Compound 773

Step 1: Synthesis of rac-(2R,5S)-tert-butyl 2-(6-hydroxyspiro[3.3]heptan-2-yl)-5-methylpiperidine-1-carboxylate To a solution of 6-[(2R,5S)-5-methyl-2-piperidyl]spiro[3.3]heptan-2-ol (3.5 g, 16.72 mmol) in THF (100 mL), TEA (3.38 g, 33.44 mmol, 4.66 mL) was added followed by addition of di-tert-butyl dicarbonate (3.65 g, 16.72 mmol, 3.84 mL). The reaction mixture was stirred at 25° C. for 13 hr and evaporated. The residue was taken up with water (150 ml) and extracted with DCM (3*70 ml). The organic extract was washed with water and brine, then dried over Na$_2$SO$_4$ and evaporated to give tert-butyl (2R,5S)-2-(2-hydroxyspiro[3.3]heptan-6-yl)-5-methyl-piperidine-1-carboxylate (4.8 g, crude) as yellow oil.

$^1$H NMR (500 MHz, CDCl$_3$) δ (ppm) 0.86 (d, 3H), 1.43 (m, 3H), 1.51 (s, 9H), 1.88 (m, 9H), 2.26 (m, 1H), 2.42 (m, 1H), 2.62 (m, 1H), 2.89 (m, 1H), 3.65 (m, 1H), 4.14 (m, 2H).

LCMS(ESI): [M−Boc]$^+$ m/z: calcd 209.4; found 210.2; Rt=1.494 min.

Step 2: Synthesis of rac-(2R,5S)-tert-butyl 5-methyl-2-(6-((methylsulfonyl)oxy)spiro[3.3]heptan-2-yl)piperidine-1-carboxylate To a solution of tert-butyl (2R,5S)-2-(2-hydroxyspiro[3.3]heptan-6-yl)-5-methyl-piperidine-1-carboxylate (4.8 g, 15.51 mmol) in DCM (150 mL), TEA (2.35 g, 23.27 mmol, 3.24 mL) was added followed by addition of methanesulfonyl chloride (1.25 g, 10.91 mmol, 844.59 µL). The reaction mixture was stirred at 25° C. for 12 hr. The reaction mixture was washed with water (3*100 ml). The organic extract was washed with brine, then dried over Na$_2$SO$_4$ and evaporated to give tert-butyl (2R,5S)-5-methyl-2-(2-methylsulfonyloxyspiro[3.3]heptan-6-yl)piperidine-1-carboxylate (5.6 g, crude) as yellow oil.

$^1$H NMR (500 MHz, CDCl$_3$) δ (ppm) 0.93 (d, 3H), 1.24 (m, 2H), 1.43 (s, 9H), 1.69 (m, 3H), 1.93 (m, 2H), 2.12 (m, 1H), 2.26 (m, 2H), 2.46 (m, 2H), 2.54 (m, 2H), 2.88 (m, 1H), 2.94 (s, 3H), 3.65 (m, 1H), 4.05 (m, 1H), 4.86 (m, 1H).

LCMS(ESI): [M−Boc]$^+$ m/z: calcd 287.4; found 288.2; Rt=1.658 min.

Step 3: Synthesis of rac-(2R,5S)-tert-butyl 2-(6-azidospiro[3.3]heptan-2-yl)-5-methylpiperidine-1-carboxylate To the solution of tert-butyl (2R,5S)-5-methyl-2-(2-methylsulfonyloxyspiro[3.3]heptan-6-yl)piperidine-1-carboxylate (3 g, 7.74 mmol) in DMF (10 mL), sodium azide (1.51 g, 23.22 mmol, 816.10 µL) was added. The reaction mixture was stirred at 90° C. for 48 hr. The reaction mixture was diluted with water (80 ml) and product was extracted with EtOAc (2*100 ml). Combined organic layers were washed with water (3*50 ml) and brine, dried over Na$_2$SO$_4$. EtOAc was evaporated to give crude tert-butyl (2R,5S)-2-(2-azidospiro[3.3]heptan-6-yl)-5-methyl-piperidine-1-carboxylate (2 g, 5.98 mmol, 77.25% yield).

$^1$H NMR (500 MHz, CDCl$_3$) δ (ppm) 0.92 (d, 3H), 1.25 (m, 2H), 1.43 (s, 9H), 1.75 (m, 5H), 2.03 (m, 3H), 2.22 (m, 1H), 2.38 (m, 1H), 2.65 (m, 1H), 2.93 (m, 2H), 3.68 (m, 2H), 4.04 (m, 1H).

LCMS(ESI): [M−Boc]$^+$ m/z: calcd 234.4; found 235.2; Rt=1.510 min.

Step 4: Synthesis of rac-(2R,5S)-2-(6-azidospiro[3.3]heptan-2-yl)-5-methylpiperidine To the solution of tert-butyl (2S,5R)-2-(2-azidospiro[3.3]heptan-6-yl)-5-methyl-piperidine-1-carboxylate (1.8 g, 5.38 mmol) in DCM (15 mL) hydrogen chloride solution 4.0M in dioxane (1.96 g, 53.82 mmol, 2.45 mL) was added portion wise. Mixture was stirred at 25° C. for 12 hr. The reaction mixture was evaporated to give (2S,5R)-2-(2-azidospiro[3.3]heptan-6-yl)-5-methyl-piperidine (0.8 g, 2.95 mmol, 54.89% yield, HCl).

LCMS(ESI): [M]$^+$ m/z: calcd 234.4; found 235.2; Rt=1.085 min.

Step 5: Synthesis of rac-tert-butyl (5-(2-((2R,5S)-2-(6-azidospiro[3.3]heptan-2-yl)-5-methylpiperidin-1-yl)-2-oxoacetamido)-3-methylpyridin-2-yl)carbamate To the solution of (2S,5R)-2-(2-azidospiro[3.3]heptan-6-yl)-5-methyl-piperidine (0.80. g, 2.95 mmol, HCl), 2-[[6-(tert-butoxycarbonylamino)-5-methyl-3-pyridyl]amino]-2-oxo-acetic acid (872.35 mg, 2.95 mmol) and TEA (2.09 g, 20.68 mmol, 2.88 mL) in DMF (3 mL) HATU (1.24 g, 3.25 mmol) was added portionwise. Mixture was stirred at 25° C. for 2 hr. The reaction mixture was diluted with water (50 ml) and product was extracted with EtOAc (3*25 ml). Combined organic layer were washed with water, brine and dried over $Na_2SO_4$. Solvent was evaporated to give tert-butyl N-[5-[[2-[(2S,5R)-2-(2-azidospiro[3.3]heptan-6-yl)-5-methyl-1-piperidyl]-2-oxo-acetyl]amino]-3-methyl-2-pyridyl]carbamate (1.5 g, crude).

LCMS(ESI): [M]+ m/z: calcd 511.4; found 512.2; Rt=0.849 min.

Step 6: Synthesis of rac-tert-butyl (5-(2-((2R,5S)-2-(6-aminospiro[3.3]heptan-2-yl)-5-methylpiperidin-1-yl)-2-oxoacetamido)-3-methylpyridin-2-yl)carbamate A mixture of tert-butyl N-[5-[[2-[(2S,5R)-2-(2-azidospiro[3.3]heptan-6-yl)-5-methyl-1-piperidyl]-2-oxo-acetyl]amino]-3-methyl-2-pyridyl]carbamate (1.5 g, 2.93 mmol) and palladium, 10% on carbon, Type 487, dry (312.01 mg, 2.93 mmol) in MeOH (50 mL) was stirred under atmosphere of hydrogen at 25° C. for 15 hr. The catalyst was filtered off, the filtrate was evaporated in vacuo. Th residue was taken up with water (50 ml) and extracted with DCM (2*50 ml). The organic layer was washed with brine (40 ml), dried over $Na_2SO_4$ to afford tert-butyl N-[5-[[2-[(2S,5R)-2-(2-aminospiro[3.3]heptan-6-yl)-5-methyl-1-piperidyl]-2-oxo-acetyl]amino]-3-methyl-2-pyridyl]carbamate (1 g, crude).

$^1$H NMR (500 MHz, $CDCl_3$) δ (ppm) 0.99 (d, 3H), 2.26 (m, 2H), 1.49 (s, 9H), 1.85 (m, 18H), 2.86 (s, 3H), 4.54 (m, 1H), 7.26 (m, 1H), 8.02 (m, 1H), 8.35 (m, 1H).

LCMS(ESI): [M]+ m/z: calcd 485.4; found 486.2; Rt=1.084 min.

Step 7: Synthesis of N-(6-amino-5-methylpyridin-3-yl)-2-(2-(6-aminospiro[3.3]heptan-2-yl)-5-methylpiperidin-1-yl)-2-oxoacetamide (Compound 773

To the stirred solution of tert-butyl N-[5-[[2-[(2S,5R)-2-(2-aminospiro[3.3]heptan-6-yl)-5-methyl-1-piperidyl]-2-oxo-acetyl]amino]-3-methyl-2-pyridyl]carbamate (0.6 g, 1.24 mmol) in DCM (10 mL) hydrogen chloride solution 4.0 M in dioxane (450.49 mg, 12.36 mmol, 563.11 μL) was added. The reaction mixture was stirred at 25° C. for 12 hr. The solvents were evaporated. The residue was purified by reverse phase HPLC (30-65% 0-5 min $H_2O$/MeOH 0.1% $NH_4OH$, flow: 30 ml/min (loading pump 4 ml/min MeOH) column: YMC Triart C18 100×20 mm, 5 um) to give N-(6-amino-5-methyl-3-pyridyl)-2-[(2S,5R)-2-(2-aminospiro[3.3]heptan-6-yl)-5-methyl-1-piperidyl]-2-oxo-acetamide (28 mg, 72.63 μmol, 5.88% yield) as mixture of diastereomers.

$^1$H NMR (600 MHz, DMSO-$d_6$) δ (ppm) 0.85-0.93 (m, 3H), 1.19-1.32 (m, 2H), 1.39-1.51 (m, 1H), 1.51-1.60 (m, 2H), 1.61-1.72 (m, 2H), 1.73-1.84 (m, 3H), 1.86-1.98 (m, 2H), 1.98-2.01 (m, 3H), 2.01-2.16 (m, 2H), 2.20-2.30 (m, 1H), 2.65-2.86 (m, 2H), 2.97-3.13 (m, 1H), 3.23-3.26 (m, 0.6H), 3.67-3.73 (m, 0.4H), 3.90-4.40 (m, 1H), 5.56-5.62 (m, 2H), 7.40-7.49 (m, 1H), 7.94-8.04 (m, 1H), 10.18-10.44 (m, 1H).

LCMS(ESI): [M]+ m/z: calcd 385.4; found 386.2; Rt=1.211 min.

Example 786. The Synthesis of 6-(1-(2-((6-amino-5-methylpyridin-3-yl)amino)-2-oxoacetyl)-5-methylpiperidin-2-yl)spiro[3.3]heptane-2-carboxamide (Compound 812)

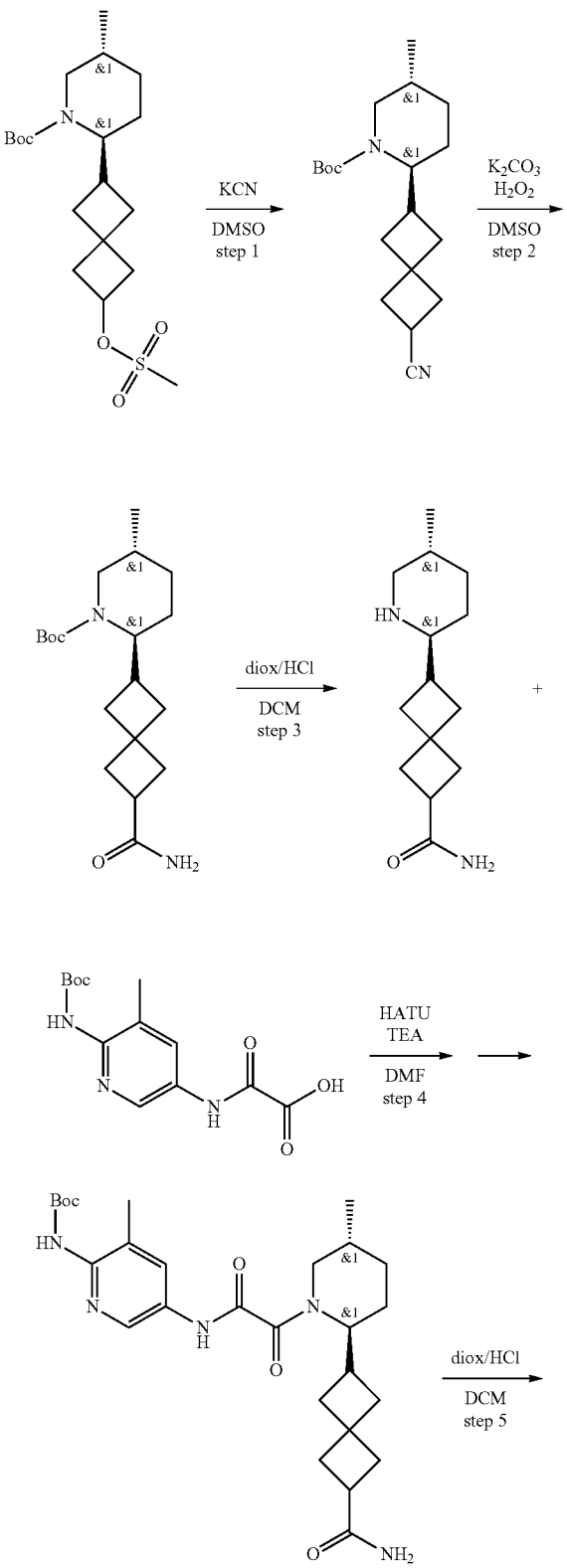

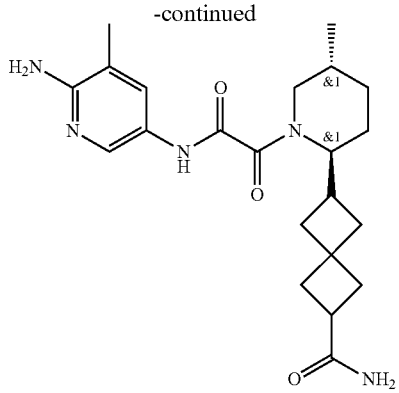

Compound 812

Step 1: Synthesis of rac-(2R,5S)-tert-butyl 2-(6-cyanospiro[3.3]heptan-2-yl)-5-methylpiperidine-1-carboxylate To the solution of tert-butyl (2R,5S)-5-methyl-2-(2-methylsulfonyloxyspiro[3.3]heptan-6-yl)piperidine-1-carboxylate (1.5 g, 3.87 mmol) in DMSO (7 mL), potassium cyanide (756.17 mg, 11.61 mmol) was added. The reaction mixture was stirred at 85° C. for 36 hr. The reaction mixture was diluted with water (70 ml) and product was extracted with EtOAc (2*40 ml). Combined organic layers were washed with water (3*30 ml) and brine, dried over Na₂SO₄. EtOAc was evaporated to give crude tert-butyl (2R,5S)-2-(6-cyanospiro[3.3]heptan-2-yl)-5-methyl-piperidine-1-carboxylate (1 g, 3.14 mmol, 81.13% yield).

¹H NMR (400 MHz, CDCl₃) δ (ppm) 0.91 (d, 3H), 1.31 (m, 3H), 1.42 (s, 9H), 1.67 (m, 5H), 1.96 (m, 1H), 2.05 (m, 1H), 2.30 (m, 4H), 2.59 (m, 1H), 2.86 (m, 1H), 3.65 (m, 1H), 4.08 (m, 1H).

LCMS(ESI): [M−Boc]⁺ m/z: calcd 218.4; found 219.2; Rt=1.606 min.

Step 2: Synthesis of rac-(2R,5S)-tert-butyl 2-(6-carbamoylspiro[3.3]heptan-2-yl)-5-methylpiperidine-1-carboxylate To the stirred solution of tert-butyl (2R,5S)-2-(6-cyanospiro[3.3]heptan-2-yl)-5-methyl-piperidine-1-carboxylate (900 mg, 2.83 mmol) and potassium carbonate, anhydrous, 99% (781.19 mg, 5.65 mmol, 341.13 µL) in DMSO (6 mL), hydrogen peroxide 35% (2.97 g, 87.32 mmol, 2.70 mL) was added dropwise at 60° C. The reaction mixture was stirred at 80° C. for 24 hr. The reaction mixture was diluted with water (25 ml) and extracted with EtOAc (3*25 ml). Combined organic layers were dried over Na₂SO₄. Solvent was evaporated in vacuo to give tert-butyl (2R,5S)-2-(2-carbamoylspiro[3.3]heptan-6-yl)-5-methyl-piperidine-1-carboxylate (1 g, crude).

LCMS(ESI): [M−Boc]⁺ m/z: calcd 236.4; found 237.2; Rt=1.407 min.

Step 3: Synthesis of rac-6-((2R,5S)-5-methylpiperidin-2-yl)spiro[3.3]heptane-2-carboxamide To the stirred solution of tert-butyl (2R,5S)-2-(2-carbamoylspiro[3.3]heptan-6-yl)-5-methyl-piperidine-1-carboxylate (1 g, 2.97 mmol) in DCM (10 mL) hydrogen chloride solution 4.0 M in dioxane (1.08 g, 29.72 mmol, 1.35 mL) was added. The reaction mixture was stirred at 25° C. for 12 hr. The solvents were evaporated to dryness to give 6-[(2R,5S)-5-methyl-2-piperidyl]spiro[3.3]heptane-2-carboxamide (0.7 g, crude, HCl).

¹H NMR (400 MHz, DMSO-d₆) δ (ppm) 0.83 (d, 3H), 1.23 (m, 2H), 1.87 (m, 8H), 2.14 (m, 2H), 2.46 (m, 3H), 2.73 (m, 2H), 2.95 (m, 1H), 5.45 (m, 2H), 9.04 (m, 1H).

LCMS(ESI): [M]⁺ m/z: calcd 236.4; found 237.2; Rt=0.545 min.

Step 4: Synthesis of rac-tert-butyl (5-(2-((2R,5S)-2-(6-carbamoylspiro[3.3]heptan-2-yl)-5-methylpiperidin-1-yl)-2-oxoacetamido)-3-methylpyridin-2-yl)carbamate To the solution of 6-[(2R,5S)-5-methyl-2-piperidyl]spiro[3.3]heptane-2-carboxamide (0.7 g, 2.96 mmol), 2-[[6-(tert-butoxycarbonylamino)-5-methyl-3-pyridyl]amino]-2-oxo-acetic acid (874.56 mg, 2.96 mmol) and TEA (2.10 g, 20.73 mmol, 2.89 mL) in DMF (3 mL) HATU (1.24 g, 3.26 mmol) was added portion wise. Mixture was stirred at 25° C. for 2 hr. The reaction mixture was diluted with water (50 ml) and product was extracted with EtOAc (3*25 ml). Combined organic layer were washed with water, brine and dried over Na₂SO₄. Solvent was evaporated to give tert-butyl N-[5-[[2-[(2R,5S)-2-(2-carbamoylspiro[3.3]heptan-6-yl)-5-methyl-1-piperidyl]-2-oxo-acetyl]amino]-3-methyl-2-pyridyl]carbamate (1 g, crude).

¹H NMR (400 MHz, CDCl₃) δ (ppm) 0.98 (d, 3H), 1.23 (m, 4H), 1.47 (s, 9H), 1.86 (m, 6H), 2.02 (m, 2H), 2.27 (s, 3H), 2.85 (m, 4H), 2.98 (m, 2H), 3.27 (m, 1H), 4.57 (m, 1H), 6.73 (m, 1H), 8.01 (m, 1H), 8.32 (m, 1H), 9.45 (m, 1H).

LCMS(ESI): [M]⁺ m/z: calcd 513.4; found 514.2; Rt=1.244 min.

Step 5: Synthesis of 6-(1-(2-((6-amino-5-methylpyridin-3-yl)amino)-2-oxoacetyl)-5-methylpiperidin-2-yl)spiro[3.3]heptane-2-carboxamide (Compound 812

To the stirred solution of tert-butyl N-[5-[[2-[(2R,5S)-2-(2-carbamoylspiro[3.3]heptan-6-yl)-5-methyl-1-piperidyl]-2-oxo-acetyl]amino]-3-methyl-2-pyridyl]carbamate (1 g, 1.95 mmol) in DCM (10 mL) hydrogen chloride solution 4.0 M in dioxane (709.87 mg, 19.47 mmol, 887.34 µL) was added. The reaction mixture was stirred at 25° C. for 2 hr. The solvents were evaporated. The residue was purified by reverse phase HPLC (15-15-40% 0-1-6 min H₂O/ACN/0.1% NH₄OH, flow: 30 ml/min (loading pump 4 ml/min MeOH) target mass 413.52 column: YMC Triart C18 100×20 mm, 5 um) to give 6-[(2R,5S)-1-[2-[(6-amino-5-methyl-3-pyridyl)amino]-2-oxo-acetyl]-5-methyl-2-piperidyl]spiro[3.3]heptane-2-carboxamide (40 mg, 96.73 µmol, 4.97% yield). Also was collected 2 more fractions on HPLC: 1st: 58 mg (95% LCMS); 2nd: 36 mg (99% LCMS).

¹H NMR (600 MHz, DMSO-d₆) δ (ppm) 0.86-0.94 (m, 3H), 1.20-1.32 (m, 2H), 1.40-1.66 (m, 2H), 1.68-1.84 (m, 4H), 1.89-1.93 (m, 1H), 1.94-2.00 (m, 2H), 2.00-2.02 (m, 3H), 2.03-2.13 (m, 2H), 2.64-3.01 (m, 4H), 3.63-3.98 (m, 1H), 4.32-5.06 (m, 1H), 5.55-5.66 (m, 2H), 6.60-7.08 (m, 1H), 7.39-7.50 (m, 1H), 7.91-8.07 (m, 1H), 10.24-10.43 (m, 1H).

LCMS(ESI): [M]⁺ m/z: calcd 413.4; found 414.2; Rt=1.746 min.

Example 787. The Synthesis of N-(6-amino-5-methylpyridin-3-yl)-2-(5-methyl-2-(spiro[3.3]heptan-2-yl)piperidin-1-yl)-2-oxoacetamide (Compound 692)

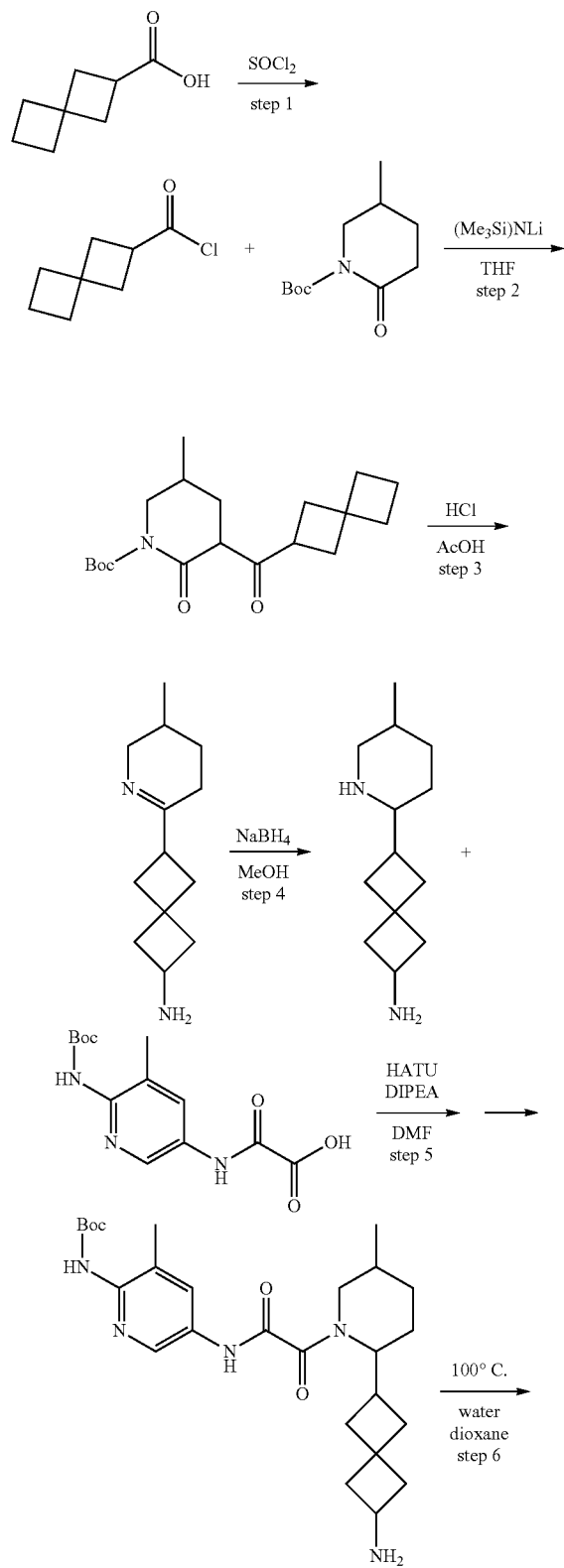

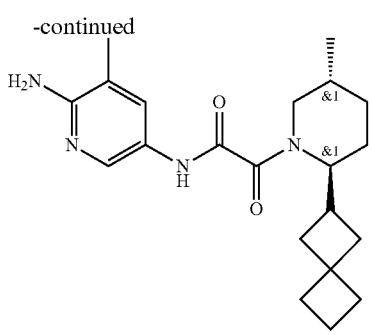

Compound 692

Step 1: Synthesis of Spiro[3.3]heptane-2-carbonyl chloride

Spiro[3.3]heptane-2-carboxylic acid (1 g, 7.13 mmol) in thionyl chloride (8.49 g, 71.34 mmol) was stirred at reflux for 12 hr. Then reaction mixture was evaporated in vacuo to afford spiro[3.3]heptane-2-carbonyl chloride (0.9 g, 5.67 mmol, 79.53% yield), which was used in next step without purification.

$^1$H NMR (500 MHz, DMSO-$d_6$) δ (ppm) 1.73 (m, 2H), 1.85 (m, 2H), 1.97 (m, 2H), 2.11 (m, 4H), 2.86 (m, 1H).

GCMS: calcd 158.4; found 158.2; Rt=4.384 min.

Step 2: Synthesis of tert-butyl 5-methyl-2-oxo-3-(spiro[3.3]heptane-2-carbonyl)piperidine-1-carboxylate Lithium bis(trimethylsilyl)amide (2.09 g, 12.48 mmol) was added dropwise to a precooled solution of tert-butyl 5-methyl-2-oxo-piperidine-1-carboxylate (1.21 g, 5.67 mmol) in THF (20 mL) at −78° C. After addition was complete, it was stirred at the same temperature for 1 hr. After that, spiro[3.3]heptane-2-carbonyl chloride (0.9 g, 5.67 mmol) was added in one portion and cooling bath was removed. Resulting mixture was slowly warmed up to 25° C. and stirred at this temperature for 1 hr. Then, it was quenched with 15% aq. NaHSO$_4$ (50 ml) and extracted with ethyl acetate (100 ml). Organic layer was washed with 20% aq. NaCl (2×50 ml), dried over Na$_2$SO$_4$ and evaporated under reduced pressure, afford to tert-butyl 5-methyl-2-oxo-3-(spiro[3.3]heptane-2-carbonyl)piperidine-1-carboxylate (1.6 g, 4.77 mmol, 84.07% yield).

$^1$H NMR (500 MHz, DMSO-$d_6$) δ (ppm) 0.91 (d, 3H), 1.40 (s, 9H), 1.53 (m, 1H), 1.76 (m, 6H), 1.95 (m, 4H), 2.07 (m, 4H), 3.04 (m, 1H), 3.62 (m, 1H).

LCMS(ESI): [M−Boc]$^+$ m/z: calcd 235.4; found 236.2; Rt=1.570 min.

Step 3: Synthesis of 6-(5-methyl-3,4,5,6-tetrahydropyridin-2-yl)spiro[3.3]heptan-2-amine tert-butyl 5-methyl-2-oxo-3-(spiro[3.3]heptane-2-carbonyl)piperidine-1-carboxylate (1.6 g, 4.77 mmol) was dissolved in AcOH (16 mL) and hydrochloric acid, 36% w/w aq. soln. (12.87 g, 352.97 mmol, 16.09 mL) was added portion wise (a lot of foam is produced). After addition was complete, resulting mixture was stirred at 100° C. for 15 hr. Then, solvents were removed under reduced pressure and residue was partitioned between 1 N HCl (100 ml) and DCM (200 ml). Organic layer was separated and discarded. Aqueous layer was basified to pH 10 with 10% NaOH and extracted with DCM (2×100 ml). DCM solution was separated, dried over $Na_2SO_4$ and evaporated under reduced pressure, afford to 3-methyl-6-spiro[3.3]heptan-2-yl-2,3,4,5-tetrahydropyridine (0.2 g, 1.05 mmol, 21.92% yield).

$^1$H NMR (500 MHz, DMSO-$d_6$) δ (ppm) 0.84 (d, 3H), 1.10 (m, 1H), 1.45 (m, 1H), 1.64 (m, 1H), 1.76 (m, 4H), 1.98 (m, 8H), 2.73 (m, 1H), 2.84 (m, 1H), 3.56 (d, 1H).

LCMS(ESI): [M]$^+$ m/z: calcd 191.4; found 192.2; Rt=0.872 min.

Step 4: Synthesis of 6-(5-methylpiperidin-2-yl)spiro[3.3]heptan-2-amine

Sodium borohydride (79.10 mg, 2.09 mmol, 73.93 µL) was added in one portion to a stirred solution of 3-methyl-6-spiro[3.3]heptan-2-yl-2,3,4,5-tetrahydropyridine (0.2 g, 1.05 mmol) in MeOH (5 mL) at 0° C. The resulting mixture was stirred for 15 hr, and then evaporated in vacuo. The residue was diluted with water (20 ml) and extracted with dichloromethane (2*40 ml). The combined organic extracts were dried over sodium sulphate and evaporated in vacuo. The obtained oil was subjected to afford 5-methyl-2-spiro[3.3]heptan-2-yl-piperidine (0.16 g, 827.61 µmol, 79.17% yield).

$^1$H NMR (500 MHz, DMSO-$d_6$) δ (ppm) 0.75 (d, 3H), 0.88 (m, 2H), 1.33 (m, 1H), 1.49 (m, 1H), 1.65 (m, 3H), 1.75 (m, 4H), 1.94 (m, 6H), 2.03 (m, 1H), 2.11 (m, 1H), 2.84 (d, 1H).

LCMS(ESI): [M]$^+$ m/z: calcd 193.4; found 194.2; Rt=0.827 min.

Step 5: Synthesis of tert-butyl (5-(2-(2-(6-aminospiro[3.3]heptan-2-yl)-5-methylpiperidin-1-yl)-2-oxoacetamido)-3-methylpyridin-2-yl)carbamate DIPEA (320.89 mg, 2.48 mmol, 432.46 µL) was added to the solution of respective 5-methyl-2-spiro[3.3]heptan-2-yl-piperidine (0.16 g, 827.61 µmol) and 2-[[6-(tert-butoxycarbonylamino)-5-methyl-3-pyridyl]amino]-2-oxo-acetic acid (244.39 mg, 827.61 µmol) in DMF (5 mL). The resulting mixture was stirred for 5 min followed by the addition of HATU (346.15 mg, 910.37 µmol). Then, the reaction mixture was stirred overnight at rt. After the completion of the reaction, monitored by LCMS, the resulting suspension was concentrated under reduced pressure. The obtained solid was subjected to HPLC (Waters Sunfire C18 20*100 5 mkm column and $H_2O$-MeCN as an eluent mixture) to afford pure tert-butyl N-[3-methyl-5-[[2-(5-methyl-2-spiro[3.3]heptan-2-yl-1-piperidyl)-2-oxo-acetyl]amino]-2-pyridyl]carbamate (0.22 g, 467.49 µmol, 56.49% yield).

LCMS(ESI): [M]$^+$ m/z: calcd 470.4; found 471.2; Rt=4.127 min.

Step 6: Synthesis of N-(6-amino-5-methylpyridin-3-yl)-2-(5-methyl-2-(spiro[3.3]heptan-2-yl)piperidin-1-yl)-2-oxoacetamide (Compound 692 tert-butyl N-[3-methyl-5-[[2-(5-methyl-2-spiro[3.3]heptan-2-yl-1-piperidyl)-2-oxo-acetyl]amino]-2-pyridyl]carbamate (0.22 g, 467.49 µmol) was dissolved in dioxane (2 mL) and water (5 mL) mixture. Then reaction mixture was stirred for 16 hr at 100° C. After the completion of the reaction, monitored by LCMS, the resulting suspension was concentrated under reduced pressure. The obtained solid was subjected to HPLC (Waters Sunfire C18 20*100 5 mkm column and $H_2O$-MeCN (45-60%)+FA as an eluent mixture) to afford pure N-(6-amino-5-methyl-3-pyridyl)-2-[(2R,5S)-5-methyl-2-spiro[3.3]heptan-2-yl-1-piperidyl]-2-oxo-acetamide (101.7 mg, 274.50 µmol, 58.72% yield).

$^1$H NMR (600 MHz, DMSO-$d_6$) δ (ppm) 0.90 (d, 3H), 1.27 (m, 2H), 1.78 (m, 13H), 2.00 (s, 4H), 2.69 (m, 1H), 3.69 (m, 1H), 4.09 (m, 1H), 5.58 (m, 2H), 7.44 (d, 1H), 7.98 (d, 1H), 10.29 (m, 1H).

LCMS(ESI): [M]$^+$ m/z: calcd 370.4; found 371.2; Rt=2.890 min.

Example 788. The Synthesis of 5-[[2-[(2S,6S)-2-methyl-6-[6-(methylamino)-3-pyridyl]-1-piperidyl]-2-oxo-acetyl]amino]pyridine-3-carboxamide (Compound 561)

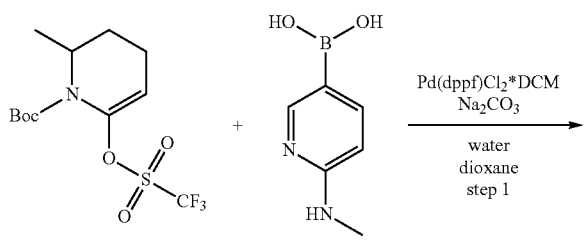

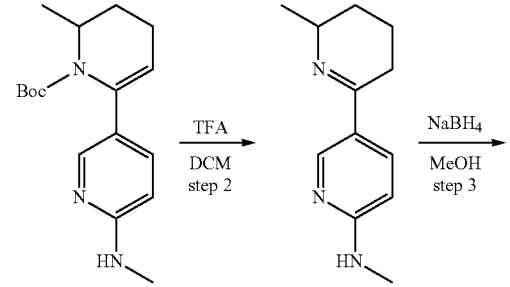

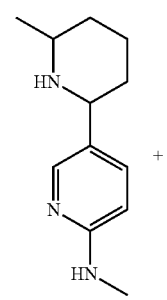

+

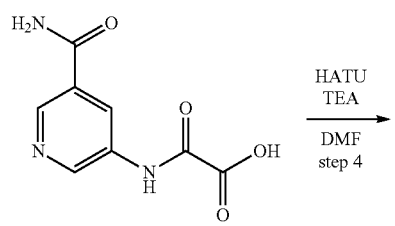

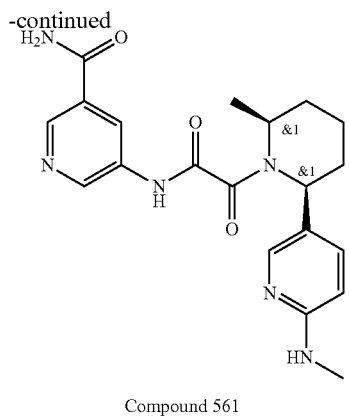

Compound 561

Step 1: Synthesis of tert-butyl 6-methyl-6'-(methylamino)-5,6-dihydro-[2,3'-bipyridine]-1(4H)-carboxylate tert-butyl 2-methyl-6-(trifluoromethylsulfonyloxy)-3,4-dihydro-2H-pyridine-1-carboxylate (7 g, 20.27 mmol), [6-(methylamino)-3-pyridyl]boronic acid (4.20 g, 22.30 mmol, HCl) and sodium carbonate (6.45 g, 60.81 mmol, 2.55 mL) were mixed together in a mixture of dioxane (75 mL) and water (25 mL). The mixture was evacuated and backfilled three times with argon and [1,1'-bis(diphenylphosphino)ferrocene]dichloropalladium(II), complex with DCM (1.66 g, 2.03 mmol) was added thereto. The reaction mixture was heated at 90° C. for 18 hr. The reaction mixture was cooled to rt and diluted with water (50 ml). The resulting mixture was extracted with EtOAc (3*100 ml) and combined organic layers were washed with brine, dried over Na₂SO₄, filtered and evaporated. The residue was purified by column chromatography to obtain tert-butyl 2-methyl-6-[6-(methylamino)-3-pyridyl]-3,4-dihydro-2H-pyridine-1-carboxylate (3.98 g, 13.12 mmol, 64.72% yield).

$^1$H NMR (500 MHz, CDCl$_3$) δ (ppm) 1.17 (s, 9H), 1.21 (d, 3H), 1.67 (m, 1H), 1.92 (m, 1H), 2.22 (m, 2H), 2.93 (d, 3H), 4.61 (bds, 1H), 4.72 (m, 1H), 5.24 (m, 1H), 6.36 (d, 1H), 7.33 (d, 1H), 8.03 (s, 1H).

LCMS(ESI): [M]$^+$ m/z: calcd 303.2; found 304.2; Rt=1.071 min.

Step 2: Synthesis of N, 6-dimethyl-3,4,5,6-tetrahydro-[2,3'-bipyridin]-6'-amine tert-butyl 2-methyl-6-[6-(methylamino)-3-pyridyl]-3,4-dihydro-2H-pyridine-1-carboxylate (3.98 g, 13.12 mmol) was dissolved in DCM (16 mL) and TFA (16 mL) was added thereto. The resulting mixture was stirred for 1 hr. The reaction mixture was carefully poured into a solution of K₂CO₃ (35 g) and the resulting mixture was extracted with DCM (2*100 ml). Combined organic layers were dried over Na₂SO₄, filtered and evaporated to obtain N-methyl-5-(2-methyl-2,3,4,5-tetrahydropyridin-6-yl)pyridin-2-amine (2.1 g, 10.33 mmol, 78.75% yield).

$^1$H NMR (500 MHz, CDCl$_3$) δ (ppm) 1.22 (m, 1H), 1.30 (d, 3H), 1.70 (m, 1H), 1.87 (m, 2H), 2.46 (m, 1H), 2.57 (m, 1H), 2.93 (d, 3H), 3.64 (m, 1H), 4.73 (m, 1H), 6.38 (d, 1H), 8.05 (d, 1H), 8.43 (s, 1H).

LCMS(ESI): [M]$^+$ m/z: calcd 203.2; found 204.2; Rt=0.557 min.

Step 3: Synthesis of N-methyl-5-(6-methylpiperidin-2-yl)pyridin-2-amine

N-methyl-5-(2-methyl-2,3,4,5-tetrahydropyridin-6-yl)pyridin-2-amine (2.1 g, 10.33 mmol) was dissolved in MeOH (30 mL) and sodium borohydride (1.17 g, 30.99 mmol, 1.10 mL) was added portion wise. The resulting mixture was stirred for 18 hr. The reaction mixture was concentrated in vacuum and water (30 ml) was added to the residue. The resulting mixture was extracted with DCM (2*50 ml) and combined organic layers were dried over Na₂SO₄, filtered and evaporated to obtain N-methyl-5-(6-methyl-2-piperidyl)pyridin-2-amine (2.07 g, 10.09 mmol, 97.70% yield).

$^1$H NMR (400 MHz, CDCl$_3$) δ (ppm) 1.08 (d, 3H), 1.16 (m, 1H), 1.42 (m, 2H), 1.63 (m, 3H), 1.82 (m, 1H), 2.76 (m, 1H), 2.89 (d, 3H), 3.51 (m, 1H), 4.44 (m, 1H), 6.35 (d, 1H), 7.51 (d, 1H), 8.01 (s, 1H).

LCMS(ESI): [M]$^+$ m/z: calcd 205.2; found 206.2; Rt=0.265 min.

Step 4: Synthesis of 5-[[2-[(2S,6S)-2-methyl-6-[6-(methylamino)-3-pyridyl]-1-piperidyl]-2-oxo-acetyl]amino]pyridine-3-carboxamide (Compound 561

N-methyl-5-(6-methyl-2-piperidyl)pyridin-2-amine (0.25 g, 1.22 mmol), 2-[(5-carbamoyl-3-pyridyl)amino]-2-oxoacetic acid (299.10 mg, 1.22 mmol, HCl) and TEA (1.23 g, 12.18 mmol, 1.70 mL) were mixed together in DMF (6 mL) and HATU (694.53 mg, 1.83 mmol) was added thereto. The resulting mixture was stirred for 18 hr. The reaction mixture was concentrated in vacuum and the residue was purified by HPLC (2-10 min 40-60% water/MeCN (loading pump 4 ml MeCN)column: TRIART 100*20 5 microM) to obtain 5-[[2-[(2S,6S)-2-methyl-6-[6-(methylamino)-3-pyridyl]-1-piperidyl]-2-oxo-acetyl]amino]pyridine-3-carboxamide (0.0114 g, 28.76 µmol, 2.36% yield) and N-(5-carbamoyl-3-pyridyl)-N'-methyl-N'-[5-(6-methyl-2-piperidyl)-2-pyridyl]oxamide (23.60 mg, 59.53 µmol, 4.89% yield). Compound 561:

$^1$H NMR (600 MHz, DMSO-d$_6$) δ (ppm) 1.31-1.36 (m, 3H), 1.43-1.60 (m, 2H), 1.62-1.75 (m, 2H), 1.87-2.20 (m, 2H), 2.55-2.75 (m, 3H), 4.11-4.29 (m, 1H), 4.82-5.19 (m, 1H), 6.19-6.43 (m, 2H), 7.22-7.34 (m, 1H), 7.48-7.62 (m, 1H), 7.80-7.94 (m, 1H), 8.03-8.17 (m, 1H), 8.20-8.52 (m, 1H), 8.61-8.91 (m, 2H), 10.42-11.31 (m, 1H).

LCMS(ESI): [M]$^+$ m/z: calcd 396.2; found 397.2; Rt=1.248 min.

Example 789. The Synthesis of 5-(2-(5-methyl-2-(4,5,6,7-tetrahydro-1H-indazol-5-yl)piperidin-1-yl)-2-oxoacetamido)piperidine-3-carboxamide (Compound 755)

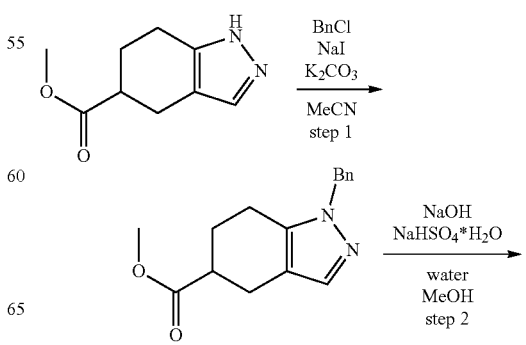

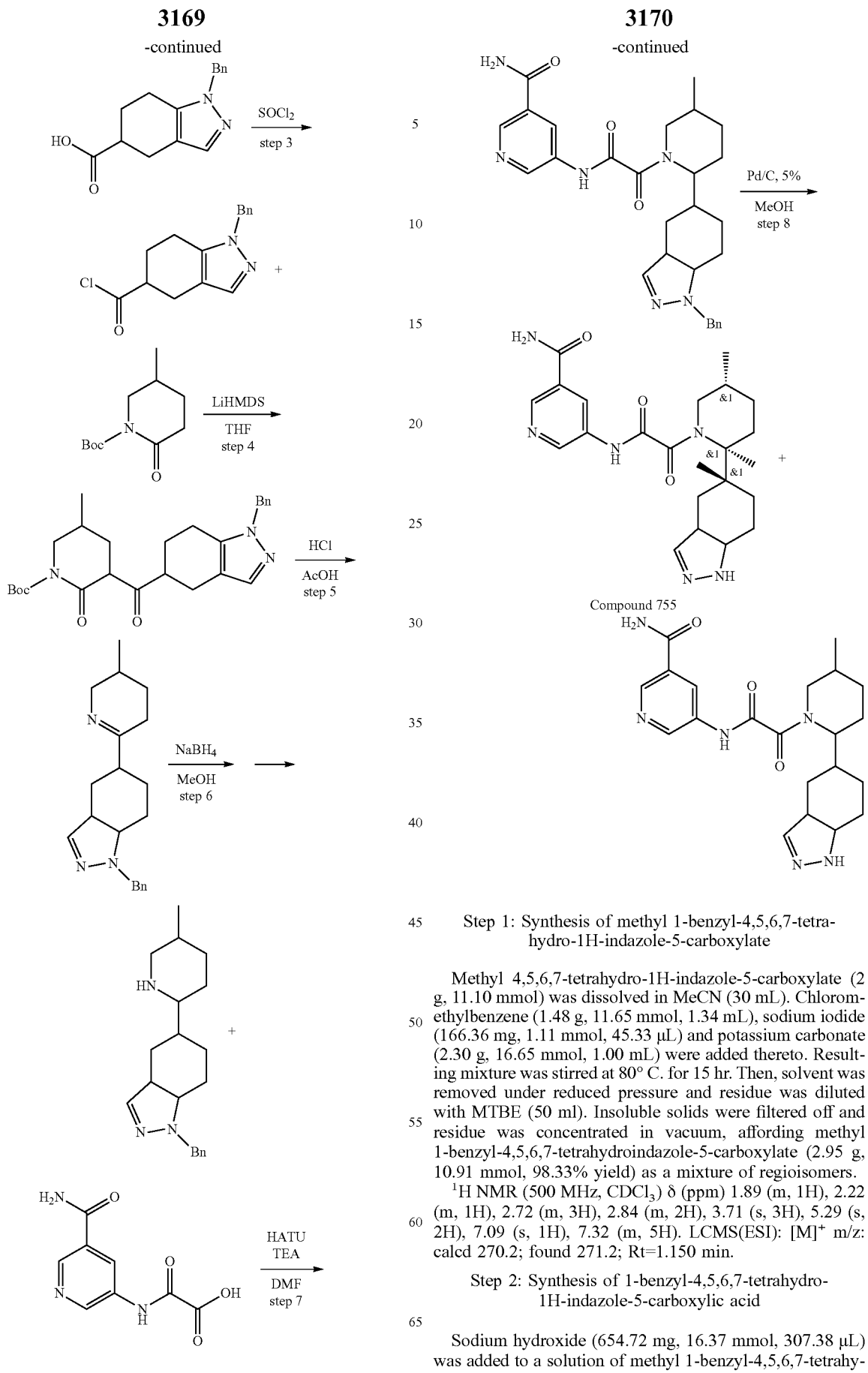

Step 1: Synthesis of methyl 1-benzyl-4,5,6,7-tetrahydro-1H-indazole-5-carboxylate Methyl 4,5,6,7-tetrahydro-1H-indazole-5-carboxylate (2 g, 11.10 mmol) was dissolved in MeCN (30 mL). Chloromethylbenzene (1.48 g, 11.65 mmol, 1.34 mL), sodium iodide (166.36 mg, 1.11 mmol, 45.33 μL) and potassium carbonate (2.30 g, 16.65 mmol, 1.00 mL) were added thereto. Resulting mixture was stirred at 80° C. for 15 hr. Then, solvent was removed under reduced pressure and residue was diluted with MTBE (50 ml). Insoluble solids were filtered off and residue was concentrated in vacuum, affording methyl 1-benzyl-4,5,6,7-tetrahydroindazole-5-carboxylate (2.95 g, 10.91 mmol, 98.33% yield) as a mixture of regioisomers.
$^1$H NMR (500 MHz, CDCl$_3$) δ (ppm) 1.89 (m, 1H), 2.22 (m, 1H), 2.72 (m, 3H), 2.84 (m, 2H), 3.71 (s, 3H), 5.29 (s, 2H), 7.09 (s, 1H), 7.32 (m, 5H). LCMS(ESI): [M]$^+$ m/z: calcd 270.2; found 271.2; Rt=1.150 min.

Step 2: Synthesis of 1-benzyl-4,5,6,7-tetrahydro-1H-indazole-5-carboxylic acid

Sodium hydroxide (654.72 mg, 16.37 mmol, 307.38 μL) was added to a solution of methyl 1-benzyl-4,5,6,7-tetrahydroindazole-5-carboxylate (2.95 g, 10.91 mmol) in MeOH (50 mL) and water (5 mL). Resulting mixture was stirred at 50° C. for 5 hr. Then, methanol was evaporated under reduced pressure and residue was diluted with water (40 ml). Resulting cloudy solution was filtered through a pad of cotton wool. Filtrate was acidified with a sodium hydrogen sulfate monohydrate (2.34 g, 16.91 mmol) dissolved in water (10 ml). Obtained precipitate was filtered, washed with water and dried, affording 1-benzyl-4,5,6,7-tetrahydroindazole-5-carboxylic acid (2.31 g, 9.01 mmol, 82.59% yield).

$^1$H NMR (500 MHz, DMSO-$d_6$) δ (ppm) 1.71 (m, 1H), 2.07 (m, 1H), 2.62 (m, 5H), 5.17 (s, 2H), 7.08 (s, 1H), 7.29 (m, 5H), 12.18 (bds, 1H). LCMS(ESI): [M]$^+$ m/z: calcd 256.2; found 257.2; Rt=1.106 min.

Step 3: Synthesis of 1-benzyl-4,5,6,7-tetrahydro-1H-indazole-5-carbonyl chloride 1-benzyl-4,5,6,7-tetrahydroindazole-5-carboxylic acid (2.31 g, 9.01 mmol) was dissolved in thionyl chloride (16.40 g, 137.85 mmol, 10 mL). Resulting mixture was stirred at 74° C. for 2 hr. Then, it was concentrated under reduced pressure and residue was co-evaporated with benzene (15 ml) 3 times, affording 1-benzyl-4,5,6,7-tetrahydroindazole-5-carbonyl chloride (3.1 g, crude, HCl).

$^1$H NMR (500 MHz, CDCl$_3$) δ (ppm) 2.12 (m, 1H), 2.40 (m, 1H), 3.18 (m, 5H), 5.77 (s, 2H), 7.43 (m, 6H). LCMS (ESI): [M]$^+$ m/z: calcd 274.2; found 275.2; Rt=1.100 min.

Step 4: Synthesis of tert-butyl 3-(1-benzyl-3a,4,5,6,7,7a-hexahydro-1H-indazole-5-carbonyl)-5-methyl-2-oxopiperidine-1-carboxylate tert-butyl 5-methyl-2-oxo-piperidine-1-carboxylate (1.03 g, 4.82 mmol) was dissolved in THF (15 mL) and cooled to −70° C. under stream of argon. Lithium bis(trimethylsilyl) amide (20% in THF/ethylbenzene)) (16.13 g, 19.28 mmol, 18.12 mL, 20% purity) was added dropwise thereto. Resulting solution was stirred at this temperature for 40 minutes before 1-benzyl-4,5,6,7-tetrahydroindazole-5-carbonyl chloride (1.5 g, 4.82 mmol, HCl) solution in THF (10 mL) was added dropwise. Then, cooling bath was removed and resulting mixture was stirred at 20° C. for 15 hr. After that, it was acidified to pH≈2-3 with 5% aq. NaHSO$_4$ solution and extracted with ethyl acetate (50 ml). Organic layer was washed successively with water(40 ml) and brine (40 ml), dried over Na$_2$SO$_4$ and evaporated under reduced pressure, affording tert-butyl 3-(1-benzyl-4,5,6,7-tetrahydroindazole-5-carbonyl)-5-methyl-2-oxo-piperidine-1-carboxylate (2.2 g, crude).

$^1$H NMR (400 MHz, CDCl$_3$) δ (ppm) 1.02 (d, 3H), 1.23 (m, 1H), 1.52 (s, 9H), 2.02 (m, 3H), 2.17 (m, 1H), 2.64 (m, 5H), 3.05 (m, 2H), 3.78 (m, 1H), 5.21 (s, 2H), 7.24 (m, 6H). LCMS(ESI): [M]$^+$ m/z: calcd 451.2; found 452.2; Rt=1.732 min.

Step 5: Synthesis of 1-benzyl-5-(5-methyl-3,4,5,6-tetrahydropyridin-2-yl)-3a,4,5,6,7,7a-hexahydro-1H-indazole Hydrochloric acid, 36% w/w aq. soln. (11.80 g, 116.51 mmol, 10.00 mL, 36% purity) was added to a solution of tert-butyl 3-(1-benzyl-4,5,6,7-tetrahydroindazole-5-carbonyl)-5-methyl-2-oxo-piperidine-1-carboxylate (2.2 g, 4.87 mmol) in acetic acid (15 mL) and resulting mixture was stirred at 100° C. for 15 hr. Then, volatiles were removed under reduced pressure and residue was dissolved in water (60 ml). Some insoluble tar was filtered off through a pad of cotton wool. Filtrate was extracted with DCM (2×10 ml) and organic layer was discarded. Then, aqueous layer was basified to pH≈10 with solid K$_2$CO$_3$ and extracted with DCM (2×20 ml).

Organic layer was separated, dried over K$_2$CO$_3$ and concentrated under reduced pressure, affording 1-benzyl-5-(3-methyl-2,3,4,5-tetrahydropyridin-6-yl)-4,5,6,7-tetrahydroindazole (760 mg, 2.47 mmol, 50.74% yield).

$^1$H NMR (400 MHz, CDCl$_3$) δ (ppm) 0.92 (d, 3H), 1.23 (m, 1H), 1.57 (m, 1H), 1.73 (m, 2H), 2.23 (m, 4H), 2.67 (m, 3H), 2.86 (m, 1H), 3.01 (m, 1H), 3.74 (d, 1H), 5.18 (s, 2H), 7.04 (s, 1H), 7.29 (m, 5H). LCMS(ESI): [M]$^+$ m/z: calcd 307.2; found 308.2; Rt=1.016 min.

Step 6: Synthesis of 1-benzyl-5-(5-methylpiperidin-2-yl)-3a,4,5,6,7,7a-hexahydro-1H-indazole Sodium borohydride (187.05 mg, 4.94 mmol, 174.81 μL) was added portion wise to a solution of 1-benzyl-5-(3-methyl-2,3,4,5-tetrahydropyridin-6-yl)-4,5,6,7-tetrahydroindazole (760 mg, 2.47 mmol) in MeOH (20 mL) during 15 minutes. Resulting solution was stirred at 20° C. for 2 hr. Then, solvent was removed under reduced pressure and residue was partitioned between water (20 ml) and DCM (30 ml). Organic layer was separated, dried over Na$_2$SO$_4$ and evaporated in vacuum, affording 1-benzyl-5-(5-methyl-2-piperidyl)-4,5,6,7-tetrahydroindazole (750 mg, 2.42 mmol, 98.04% yield).

$^1$H NMR (500 MHz, CDCl$_3$) δ (ppm) 0.83 (d, 3H), 1.00 (m, 1H), 1.22 (m, 2H), 1.71 (m, 4H), 1.83 (m, 2H), 2.03 (m, 1H), 2.37 (m, 3H), 2.64 (m, 2H), 3.06 (d, 1H), 5.20 (s, 2H), 7.08 (s, 1H), 7.31 (m, 5H). LCMS(ESI): [M]$^+$ m/z: calcd 309.2; found 310.2; Rt=0.895 min.

Step 7: Synthesis of 5-(2-(2-(1-benzyl-3a,4,5,6,7,7a-hexahydro-1H-indazol-5-yl)-5-methylpiperidin-1-yl)-2-oxoacetamido)nicotinamide 1-benzyl-5-(5-methyl-2-piperidyl)-4,5,6,7-tetrahydroindazole (750 mg, 2.42 mmol), 2-[(5-carbamoyl-3-pyridyl)amino]-2-oxo-acetic acid (595.30 mg, 2.42 mmol, HCl) and TEA (735.76 mg, 7.27 mmol, 1.01 mL) were mixed together in DMF (10 mL). Obtained mixture was briefly heated to 60-70° C. until clear solution was formed. After cooling to 5-10° C., HATU (1.01 g, 2.67 mmol) was added portion wise during 5 min. Resulting solution was stirred at 20° C. for 15 hr. Then, it was diluted with water (40 ml) and extracted with ethyl acetate (80 ml). Organic layer was washed with water (2×30 ml) and brine (30 ml), dried over Na$_2$SO$_4$ and evaporated under reduced pressure. Residue was subjected to HPLC (Column: YMC Triart C18 100×20 mm, 5 um; 60-60-80% 0-1-6 min 0.10% NH$_3$-MeOH, flow: 30 ml/min), affording 5-[[2-[2-(1-benzyl-4,5,6,7-tetrahydroindazol-5-yl)-5-methyl-1-piperidyl]-2-oxo-acetyl]amino]pyridine-3-carboxamide (443 mg, 884.95 μmol, 36.51% yield).

$^1$H NMR (400 MHz, DMSO-$d_6$) δ (ppm) 0.75 (m, 1H), 0.93 (d, 3H), 1.13 (m, 1H), 1.26 (m, 2H), 1.66 (m, 2H), 1.84 (m, 1H), 1.94 (m, 3H), 2.22 (m, 1H), 2.64 (m, 2H), 2.93 (m, 1H), 3.61 (m, 1H), 5.14 (s, 2H), 7.18 (m, 5H), 7.46 (m, 1H), 7.61 (m, 1H), 8.16 (m, 1H), 8.45 (m, 1H), 8.74 (m, 1H), 8.87 (m, 1H), 11.11 (m, 1H). LCMS(ESI): [M]$^+$ m/z: calcd 500.2; found 501.2; Rt=2.371 min.

Step 8: Synthesis of 5-(2-(5-methyl-2-(4,5,6,7-tetra-hydro-1H-indazol-5-yl)piperidin-1-yl)-2-oxoacet-amido)piperidine-3-carboxamide (Compound 755

Palladium, 5% on activated carbon, noblyst p1090 (400 mg, 187.93 µmol, 5% purity) was added to a solution of 5-[[2-[2-(1-benzyl-4,5,6,7-tetrahydroindazol-5-yl)-5-methyl-1-piperidyl]-2-oxo-acetyl]amino]pyridine-3-carbox-amide (443 mg, 884.95 µmol) in MeOH (20 mL). Resulting mixture was stirred under hydrogen atmosphere at 40° C. for 6 days (balloon pressure) and for 48 hours at 10 bar. Then, catalyst was filtered off and filtrate was concentrated under reduced pressure. Residue was purified by HPLC (Column: SunFire C18 100*19 mm 5 um; 15-65% 0-5 min water-MeOH, flow 30 ml/min), affording 5-[[2-[(2S,5R)-2,5-dim-ethyl-2-[(5R)-5-methyl-1,4,6,7-tetrahydroindazol-5-yl]-1-piperidyl]-2-oxo-acetyl]amino]pyridine-3-carboxamide (16 mg, 36.49 µmol, 4.12% yield) and 5-[[2-[5-methyl-2-(4,5,6,7-tetrahydro-1H-indazol-5-yl)-1-piperidyl]-2-oxo-acetyl]amino]piperidine-3-carboxamide (49 mg, 117.64 µmol, 13.29% yield).

Compound 755:

LCMS(ESI): [M]+ m/z: calcd 416.2; found 417.2; Rt=1.747 min.

Example 790. The Synthesis of 5-[[2-oxo-2-[2-(2-oxo-1H-pyridin-4-yl)-1-piperidyl]acetyl]amino]pyri-dine-3-carboxamide (Compound 262

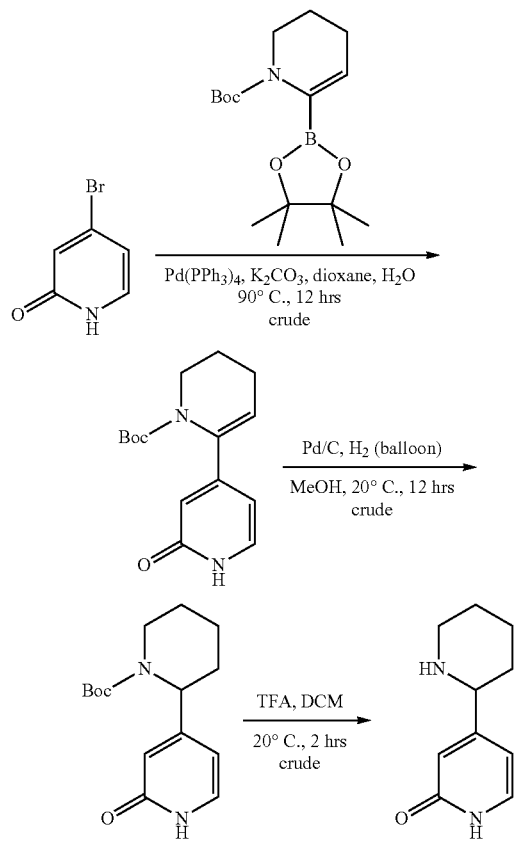

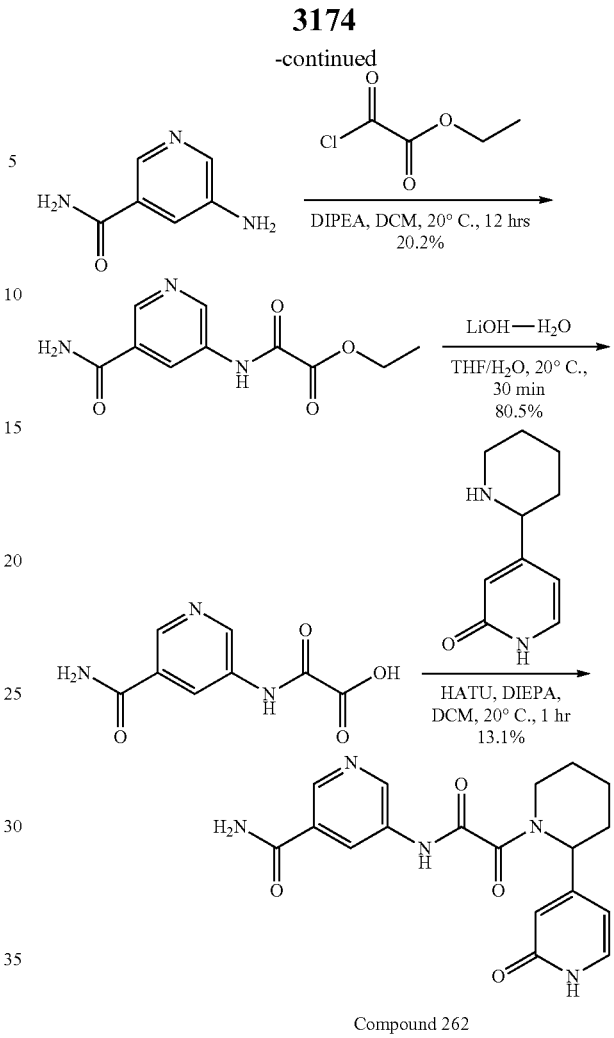

Compound 262

Step 1: Synthesis of tert-butyl 6-(2-oxo-1H-pyridin-4-yl)-3,4-dihydro-2H-pyridine-1-carboxylate To a solution of 4-bromo-1H-pyridin-2-one (180 mg, 1.03 mmol) in dioxane (35 mL)/H₂O (6 mL) were added Pd(PPh₃)₄ (35 mg, 30.3 µmol), K₂CO₃ (402 mg, 2.91 mmol) and tert-butyl 6-(4,4,5,5-tetramethyl-1,3,2-dioxaborolan-2-yl)-3,4-dihydro-2H-pyridine-1-carboxylate (300 mg, 0.970 mmol). The suspension was degassed and purged with nitrogen for 3 times. The mixture was stirred under nitrogen at 90° C. for 12 hours. The resulting mixture was quenched by addition of water (10 mL) and extracted with EtOAc (15 mL*3). The combined organic layers were washed with brine (50 mL), dried over anhydrous Na₂SO₄, filtered and concentrated under reduced pressure. The residue was puri-fied by flash chromatography (ISCO®; 12 g AgelaFlash® Silica Flash Column, petroleum ether/EtOAc with EtOAc from 0~100%, then EtOAc/MeOH with MeOH from 0~20%, Flow Rate: 30 mL/min) to afford tert-butyl 6-(2-oxo-1H-pyridin-4-yl)-3,4-dihydro-2H-pyridine-1-carboxy-late (60 mg, crude) as yellow solid.

LCMS (ESI) [M+H]+ m/z calcd 277.2, found 277.1.

Step 2: Synthesis of tert-butyl 2-(2-oxo-1H-pyridin-4-yl)piperidine-1-carboxylate To a solution of tert-butyl 6-(2-oxo-1H-pyridin-4-yl)-3,4-dihydro-2H-pyridine-1-carboxylate (50 mg, 0.181 mmol) in MeOH (5 mL) was added Pd/C (10 mg, 10% wt of Pd with 50% wt of water) under nitrogen. The mixture was degassed and purged with hydrogen for 3 times. The mixture was stirred under hydrogen (in balloon, ~15 psi) at 20° C. for 12 hours. The resulting mixture was filtered and concentrated under reduced pressure to afford tert-butyl 2-(2-oxo-1H-pyridin-4-yl)piperidine-1-carboxylate (50 mg, crude) as yellow solid, which was used directly on next step without further purification.

Step 3: Synthesis of 4-(2-piperidyl)-1H-pyridin-2-one

To a solution of tert-butyl 2-(2-oxo-1H-pyridin-4-yl)piperidine-1-carboxylate (50 mg, 0.180 mmol) in DCM (5 mL) was added TFA (0.5 mL). The mixture was stirred at 20° C. for 2 hours. The resulting mixture was concentrated under reduced pressure to afford 4-(2-piperidyl)-1H-pyridin-2-one (50 mg, crude, TFA) as yellow oil, which was used directly on next step without further purification.

Step 4: Synthesis of Ethyl 2-[(5-carbamoyl-3-pyridyl)amino]-2-oxo-acetate

To a solution of 5-aminopyridine-3-carboxamide (200 mg, 1.46 mmol), DIPEA (800 µL, 4.59 mmol) in DCM (8 mL) was added ethyl 2-chloro-2-oxo-acetate (300 mg, 2.20 mmol) and the reaction mixture was stirred at 20° C. for 12 hours. The resulting mixture was quenched by addition of water (10 mL) and extracted with EtOAc (20 mL*3). The combined organic layers were washed with saturated NH$_4$Cl aqueous solution (20 mL), brine (50 mL), dried over anhydrous Na$_2$SO$_4$, filtered and concentrated under reduced pressure. The residue was purified by preparative TLC (silica, DCM/MeOH=10:1, 254 nm) to afford ethyl 2-[(5-carbamoyl-3-pyridyl)amino]-2-oxo-acetate (70 mg, 20.2% yield) as yellow solid. $^1$H NMR (400 MHz, methanol-d$_4$) δ ppm 9.04 (d, J 2.5 Hz, 1H), 8.82 (d, J 2.0 Hz, 1H), 8.67 (t, J 2.3 Hz, 1H), 4.43 (q, J=7.3 Hz, 1H), 1.43 (t, J=7.2 Hz, 2H); LCMS (ESI) [M+H]$^+$ m/z calcd 238.1, found 238.2.

Step 5: Synthesis of 2-[(5-carbamoyl-3-pyridyl)amino]-2-oxo-acetic acid

To a solution of ethyl 2-[(5-carbamoyl-3-pyridyl)amino]-2-oxo-acetate (60 mg, 0.253 mmol) in THF (5 mL)/H$_2$O (1 mL) was added LiOH—H$_2$O (11 mg, 0.262 mmol). The mixture was stirred at 20° C. for 30 minutes. The resulting mixture was filtered to afford a yellow solid which was dissolved in 4M HCl/EtOAc (15 mL, 60 mmol), and the mixture was stirred at 20° C. for 3 hours. The resulting mixture was filtered to afford 2-[(5-carbamoyl-3-pyridyl)amino]-2-oxo-acetic acid (50 mg, 80.5% yield, HCl) as yellow solid. $^1$H NMR (400 MHz, DMSO-d$_6$) δ ppm 11.25 (s, 1H), 9.08 (d, J=2.5 Hz, 1H), 8.87 (d, J=1.8 Hz, 1H), 8.74 (d, J=2.0 Hz, 1H), 8.27 (br s, 1H), 7.73 (br s, 1H).

Step 6: Synthesis of 5-[[2-oxo-2-[2-(2-oxo-1H-pyridin-4-yl)-1-piperidyl]acetyl]amino]pyridine-3-carboxamide (Compound 262

To a mixture of 2-[(5-carbamoyl-3-pyridyl)amino]-2-oxo-acetic acid (38 mg, 0.155 mmol, HCl) in DMF (2 mL) was added HATU (80 mg, 0.210 mmol) and DIPEA (300 µL, 1.72 mmol). The mixture was stirred at 20° C. for 1 hour. The resulting mixture was purified by preparative HPLC (Instrument: Gilson GX-281 Liquid Handler, Gilson 322 Pump, Gilson 156 UV Detector; Column: 3_Phenomenex Luna C18 75*30 mm*3 µm; Mobile phase A: water (0.225% FA); Mobile phase B: MeCN; Gradient: B from 0% to 25% in 8.5 min, hold 100% B for 1 min; Flow Rate: 25 mL/min; Column Temperature: 30° C.; Wavelength: 220 nm, 254 nm) to afford 5-[[2-oxo-2-[2-(2-oxo-1H-pyridin-4-yl)-1-piperidyl]acetyl]amino]pyridine-3-carboxamide (6.8 mg, 13.1% yield,) as white solid. $^1$H NMR (400 MHz, methanol-d$_4$) δ ppm 8.93-9.06 (m, 1H), 8.79-8.85 (m, 1H), 8.67 (s, 1H), 8.62 (s, 1H), 7.46-7.52 (m, 1H), 6.54 (s, 1H), 6.43-6.51 (m, 1H), 5.66 (br s, 1H), 5.45 (br s, 1H), 4.49 (br d, J 11.3 Hz, 1H), 4.02 (br d, J 14.6 Hz, 1H), 3.17 (br d, J=14.6 Hz, 1H), 2.43 (br d, J=13.3 Hz, 1H), 1.94-2.09 (m, 1H), 1.75 (br d, J=11.5 Hz, 3H), 1.59 (br s, 1H); LCMS (ESI) [M+H]$^+$ m/z calcd 370.1, found 370.3; HPLC: 100% @254 nm; racemic.

Example 791. The Synthesis of N-(6-amino-5-ethyl-3-pyridyl)-2-[(2R,5S)-5-methyl-2-[2-(4-piperidyl)-1,3-benzothiazol-5-yl]-1-piperidyl]-2-oxo-acetamide (Compound 1240)

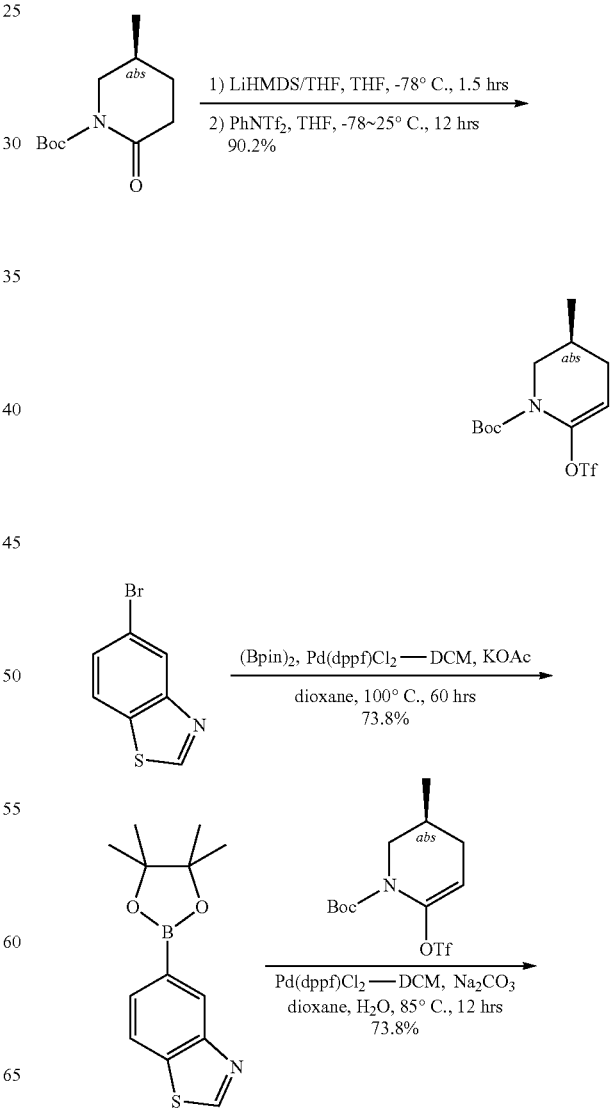

3177
-continued
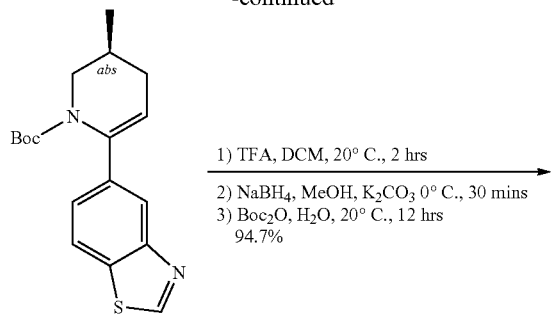
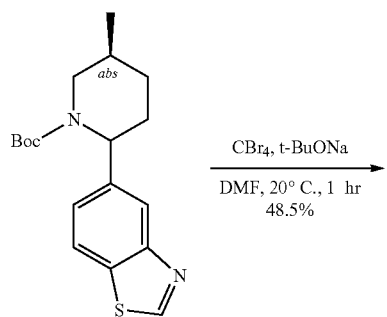
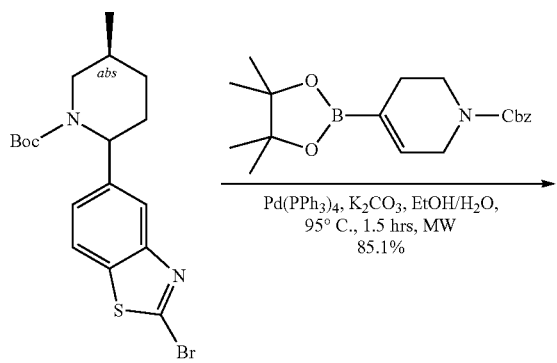
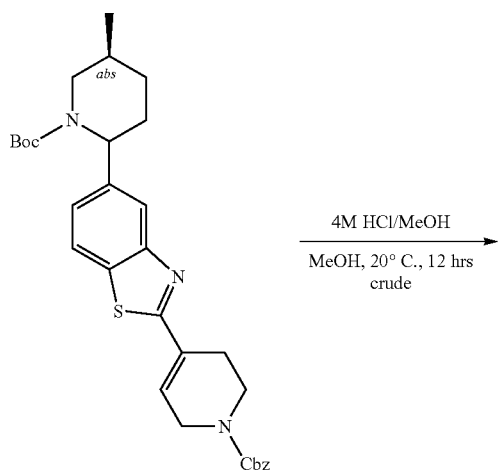
3178
-continued
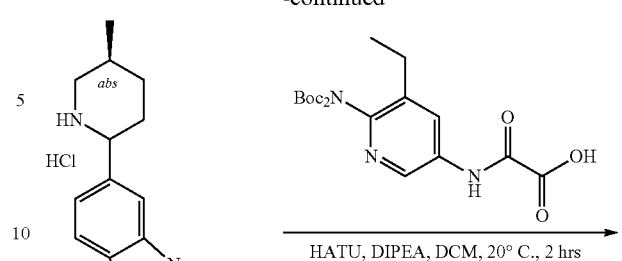
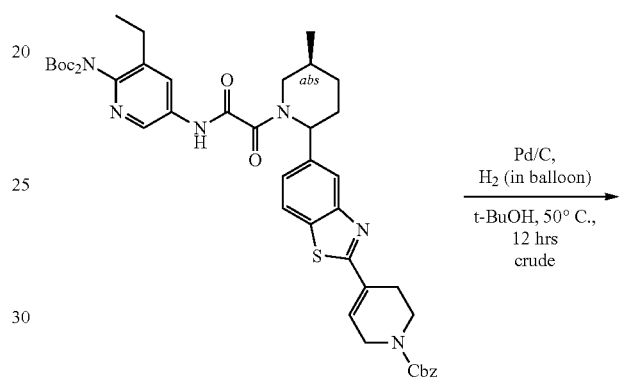
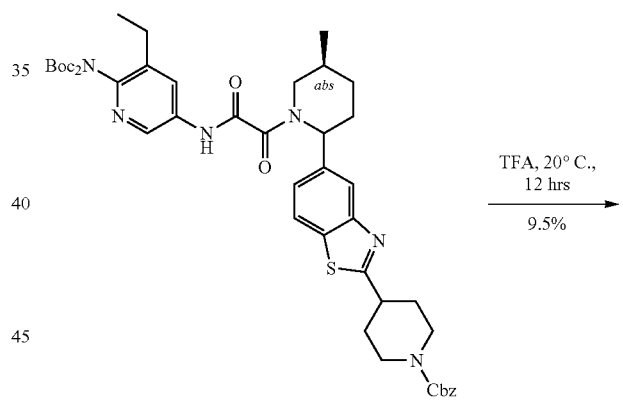
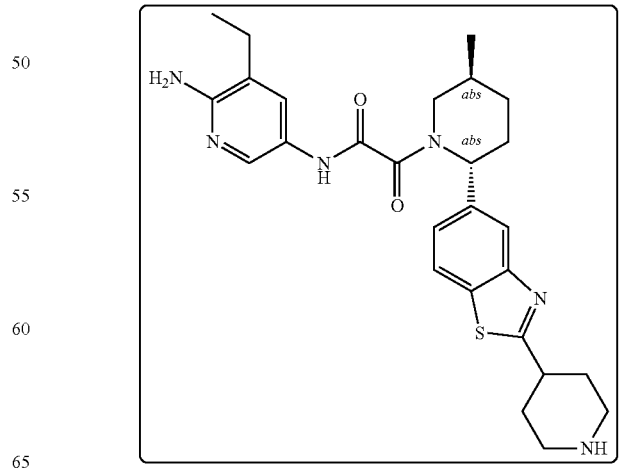

Step 1: Synthesis of tert-butyl (3S)-3-methyl-6-(trifluoromethylsulfonyloxy)-3,4-dihydro-2H-pyridine-1-carboxylate To a mixture of tert-butyl (5S)-5-methyl-2-oxo-piperidine-1-carboxylate (5 g, 23.4 mmol) in THF (60 mL) was sealed and degassed under vacuum and purged with $N_2$ for three times, and then 1M LiHMDS/THF (42.0 mL, 42.0 mmol) was added at −78° C. dropwise, the mixture was stirred 1.5 hours at −78° C., then a solution of $PhNTf_2$ (13.0 g, 36.4 mmol) in THF (20 mL) was added. The solution was stirred at 25° C. for 12 hours. The resulting mixture was quenched by addition of saturated $NH_4Cl$ aqueous solution (100 mL) and extracted with EtOAc (200 mL*3). The combined organic layer was washed with saturated $NH_4Cl$ aqueous solution (100 mL), brine (100 mL), dried over anhydrous $Na_2SO_4$, filtered and concentrated under reduced pressure. The residue was purified by flash chromatography (ISCO®; 80 g AgelaFlash® Silica Flash Column, petroleum ether/EtOAc with EtOAc from 0-1%, flow rate=60 mL/min, 12) to afford tert-butyl (3S)-3-methyl-6-(trifluoromethylsulfonyloxy)-3,4-dihydro-2H-pyridine-1-carboxylate (7.3 g, 90.2% yield) as colorless oil. LCMS (ESI) $[M+H]^+$ m/z: calcd 346.1, found 290.0 (Boc and t-Bu cleaved mass).

Step 2: Synthesis of 5-(4,4,5,5-tetramethyl-1,3,2-dioxaborolan-2-yl)-1,3-benzothiazole A mixture of 5-bromo-1,3-benzothiazole (5 g, 23.4 mmol), KOAc (1.3 g, 46.7 mmol), cyclopentyl(diphenyl)phosphane; dichloropalladium; iron (2 g, 2.73 mmol), 4,4,5,5-tetramethyl-2-(4,4,5,5-tetramethyl-1,3,2-dioxaborolan-2-yl)-1,3,2-dioxaborolane (13.5 g, 53.2 mmol) and dioxane (50 mL) was stirred at 100° C. for 60 hrs under $N_2$. The resulting mixture was quenched by addition of water (100 mL) and extracted with EtOAc (100 mL*3). The combined organic layer was washed with saturated $NH_4Cl$ aqueous solution (100 mL*2), brine (100 mL), dried over anhydrous $Na_2SO_4$, filtered and concentrated under reduced pressure to give a residue which was purified by flash chromatography (ISCO®; 80 g AgelaFlash® Silica Flash Column, petroleum ether/EtOAc with EtOAc from 0~10%, Flow Rate: 30 mL/min, 254 nm) to afford 5-(4,4,5,5-tetramethyl-1,3,2-dioxaborolan-2-yl)-1,3-benzothiazole (4.5 g, 73.8% yield) as white solid. LCMS (ESI) $[M+H]^+$ m/z: calcd 262.1, found 261.7.

Step 3: Synthesis of tert-butyl (3S)-6-(1,3-benzothiazol-5-yl)-3-methyl-3,4-dihydro-2H-pyridine-1-carboxylate A mixture of 5-(4,4,5,5-tetramethyl-1,3,2-dioxaborolan-2-yl)-1,3-benzothiazole (4.5 g, 17.2 mmol), tert-butyl (3S)-3-methyl-6-(trifluoromethylsulfonyloxy)-3,4-dihydro-2H-pyridine-1-carboxylate (7.14 g, 20.7 mmol), $Na_2CO_3$ (5.94 g, 56.0 mmol), cyclopentyl(diphenyl)phosphane; dichloromethane; dichloropalladium; iron (1.44 g, 1.76 mmol), dioxane (50 mL) and $H_2O$ (20 mL) was stirred at 85° C. for 12 hours. The resulting mixture was quenched by addition of water (100 mL) and extracted with EtOAc (100 mL*3). The combined organic layer was washed with saturated $NH_4Cl$ aqueous solution (100 mL*2), brine (100 mL), dried over anhydrous $Na_2SO_4$, filtered and concentrated under reduced pressure to give a residue which was purified by flash chromatography (ISCO®; 24 g AgelaFlash® Silica Flash Column, petroleum ether/EtOAc with EtOAc from 0~10%, Flow Rate: 30 mL/min, 254 nm) to afford tert-butyl (3S)-6-(1,3-benzothiazol-5-yl)-3-methyl-3,4-dihydro-2H-pyridine-1-carboxylate (4.2 g, 73.8% yield) as yellow solid. LCMS (ESI) $[M+H]^+$ m/z: calcd 331.1, found 331.2.

Step 4: Synthesis of tert-butyl (5S)-2-(1,3-benzothiazol-5-yl)-5-methyl-piperidine-1-carboxylate A mixture of tert-butyl (3 S)-6-(1,3-benzothiazol-5-yl)-3-methyl-3,4-dihydro-2H-pyridine-1-carboxylate (4.2 g, 12.7 mmol), TFA (10 mL, 0.130 mol) in DCM (10 mL) was stirred at 20° C. for 2 hours. The mixture was concentrated under reduced pressure. The residue was dissolved with MeOH (20 mL), then $K_2CO_3$ (5.3 g, 38.4 mmol) and $NaBH_4$ (420 mg, 11.1 mmol) was added at 0° C. The resulting mixture was stirred at 0° C. for 0.5 hour. The tert-butoxycarbonyl tert-butyl carbonate (7 g, 32.1 mmol) and $H_2O$ (10 mL) was added. The mixture was stirred at 20° C. for 12 hours. The resulting mixture was quenched by addition of water (100 mL) and extracted with EtOAc (100 mL*3). The combined organic layer was washed with saturated $NH_4Cl$ aqueous solution (100 mL*2), brine (100 mL), dried over anhydrous $Na_2SO_4$, filtered and concentrated under reduced pressure to give a residue, which was purified by flash chromatography (ISCO®; 24 g AgelaFlash® Silica Flash Column, petroleum ether/EtOAc with EtOAc from 0~15%, Flow Rate: 30 mL/min, 254 nm) to afford tert-butyl (5S)-2-(1,3-benzothiazol-5-yl)-5-methyl-piperidine-1-carboxylate (4 g, 94.7% yield) as white solid. $^1$H NMR (400 MHz, methanol-$d_4$) δ ppm 9.25 (s, 1H), 8.06 (d, J=8.3 Hz, 1H), 7.94 (s, 1H), 7.42 (dd, J=8.4, 1.4 Hz, 1H), 5.40 (s, 1H), 3.77 (br d, J=13.6 Hz, 1H), 3.13 (dd, J=13.6, 3.8 Hz, 1H), 2.10-2.29 (m, 2H), 1.86-1.93 (m, 1H), 1.75-1.84 (m, 1H), 1.45 (s, 9H), 1.32-1.42 (m, 1H), 1.08 (d, J=6.8 Hz, 3H); LCMS (ESI) $[M+H]^+$ m/z: calcd 333.2, found 333.1.

Step 5: Synthesis of tert-butyl (5S)-2-(2-bromo-1,3-benzothiazol-5-yl)-5-methyl-piperidine-1-carboxylate To a mixture of tert-butyl (5S)-2-(1,3-benzothiazol-5-yl)-5-methyl-piperidine-1-carboxylate (4 g, 12.0 mmol), t-BuONa (3.47 g, 36.1 mmol) and DMF (30 mL) was added $CBr_4$ (4.42 g, 13.3 mmol) slowly. The mixture was stirred at 20° C. for 1 hour. The resulting mixture was quenched by addition of water (30 mL) and extracted with EtOAc (100 mL*3). The combined organic layer was washed with saturated $NH_4Cl$ aqueous solution (30 mL*2), brine (30 mL), dried over anhydrous $Na_2SO_4$, filtered and concentrated under reduced pressure to give a residue, which was purified by flash chromatography (ISCO®; 40 g AgelaFlash® Silica Flash Column, petroleum ether/EtOAc with EtOAc from 0~20%, Flow Rate: 30 mL/min, 254 nm) to afford tert-butyl (5S)-2-(2-bromo-1,3-benzothiazol-5-yl)-5-methyl-piperidine-1-carboxylate (2.4 g, 48.5% yield) as yellow solid. $^1$H NMR (400 MHz, methanol-$d_4$) δ ppm 7.93 (d, J=8.5 Hz, 1H), 7.81 (s, 1H), 7.39 (dd, J=8.5, 1.0 Hz, 1H), 5.36 (t, J=4.8 Hz, 1H), 3.76 (br d, J=13.6 Hz, 1H), 3.11 (dd, J=13.6, 3.8 Hz, 1H), 2.06-2.27 (m, 2H), 1.87 (br dd, J=6.4, 2.9 Hz, 1H), 1.70-1.84 (m, 1H), 1.48 (br d, J=5.5 Hz, 1H), 1.44 (s, 9H), 1.07 (d, J=6.8 Hz, 3H); LCMS (ESI) $[M+H]^+$ m/z: calcd 413.1, found 413.0.

Step 6: Synthesis of Benzyl 4-[5-[(5S)-1-tert-butoxycarbonyl-5-methyl-2-piperidyl]-1,3-benzothiazol-2-yl]-3,6-dihydro-2H-pyridine-1-carboxylate To a mixture of tert-butyl (5S)-2-(2-bromo-1,3-benzothiazol-5-yl)-5-methyl-piperidine-1-carboxylate (300 mg, 0.729 mmol) and benzyl 4-(4,4,5,5-tetramethyl-1,3,2-dioxaborolan-2-yl)-3,6-dihydro-2H-pyridine-1-carboxylate (375 mg, 1.09 mmol) in EtOH (4 mL) and H$_2$O (1 mL) were added Pd(PPh$_3$)$_4$ (90 mg, 0.0779 mmol) and K$_2$CO$_3$ (300 mg, 2.17 mmol). The resulting mixture was stirred at 95° C. for 1.5 hours under microwave. The resulting mixture was quenched by addition of water (50 mL) and extracted with EtOAc (100 mL*3). The combined organic layer was washed with saturated NH$_4$Cl aqueous solution (50 mL), brine (50 mL), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~30%, flow rate=30 mL/min, 254 nm) to afford benzyl 4-[5-[(5S)-1-tert-butoxycarbonyl-5-methyl-2-piperidyl]-1,3-benzothiazol-2-yl]-3,6-dihydro-2H-pyridine-1-carboxylate (340 mg, 85.1% yield) as yellow solid. LCMS (ESI) [M+H]$^+$ m/z: calcd 548.3, found 548.3.

Step 7: Synthesis of Benzyl 4-[5-[(5S)-5-methyl-2-piperidyl]-1,3-benzothiazol-2-yl]-3,6-dihydro-2H-pyridine-1-carboxylate A mixture of benzyl 4-[5-[(5S)-1-tert-butoxycarbonyl-5-methyl-2-piperidyl]-1,3-benzothiazol-2-yl]-3,6-dihydro-2H-pyridine-1-carboxylate (290 mg, 0.529 mmol), MeOH (3 mL) and 4M HCl/MeOH (3 mL, 12.0 mmol) was stirred at 20° C. for 12 hours. The resulting mixture was concentrated under reduced pressure to give benzyl 4-[5-[(5S)-5-methyl-2-piperidyl]-1,3-benzothiazol-2-yl]-3,6-dihydro-2H-pyridine-1-carboxylate (250 mg, crude, HCl) as white solid.

Step 8: Synthesis of Benzyl 4-[5-[(5S)-1-[2-[[6-[bis(tert-butoxycarbonyl)amino]-5-ethyl-3-pyridyl]amino]-2-oxo-acetyl]-5-methyl-2-piperidyl]-1,3-benzothiazol-2-yl]-3,6-dihydro-2H-pyridine-1-carboxylate A mixture of benzyl 4-[5-[(5S)-5-methyl-2-piperidyl]-1,3-benzothiazol-2-yl]-3,6-dihydro-2H-pyridine-1-carboxylate (250 mg, 0.516 mmol, HCl), 2-[[6-[bis(tert-butoxycarbonyl)amino]-5-ethyl-3-pyridyl]amino]-2-oxo-acetic acid (230 mg, 0.562 mmol), HATU (240 mg, 0.631 mmol) and DIPEA (0.45 mL, 2.58 mmol) in DCM (6 mL) was stirred at 20° C. for 2 hours. The resulting mixture was quenched by addition of water (50 mL) and extracted with DCM (50 mL*3). The combined organic layer was washed with saturated NH$_4$Cl aqueous solution (50 mL), brine (50 mL), dried over anhydrous Na$_2$SO$_4$, filtered and concentrated under reduced pressure. The residue was purified by flash chromatography (ISCO®; 12 g AgelaFlash® Silica Flash Column, petroleum ether/EtOAc with EtOAc from 0~70%, flow rate=30 mL/min, 254 nm) to afford benzyl 4-[5-[(5S)-1-[2-[[6-[bis(tert-butoxycarbonyl)amino]-5-ethyl-3-pyridyl]amino]-2-oxo-acetyl]-5-methyl-2-piperidyl]-1,3-benzothiazol-2-yl]-3,6-dihydro-2H-pyridine-1-carboxylate (300 mg, 69.2% yield) as yellow oil. $^1$H NMR (400 MHz, methanol-d$_4$) δ ppm 8.43-8.75 (m, 1H), 8.22 (br s, 1H), 7.95 (br s, 2H), 7.34-7.52 (m, 6H), 5.85 (br s, 1H), 5.49 (s, 2H), 5.20 (br d, J=14.3 Hz, 2H), 3.66-3.86 (m, 3H), 2.50-2.70 (m, 3H), 2.35 (br s, 4H), 1.96 (br s, 2H), 1.51 (br s, 2H), 1.36-1.41 (m, 18H), 1.29 (br s, 3H), 1.16 (br d, J=6.8 Hz, 3H).

Step 9: Synthesis of Benzyl 4-[5-[(5S)-1-[2-[[6-[bis(tert-butoxycarbonyl)amino]-5-ethyl-3-pyridyl]amino]-2-oxo-acetyl]-5-methyl-2-piperidyl]-1,3-benzothiazol-2-yl]piperidine-1-carboxylate A mixture of benzyl 4-[5-[(5S)-1-[2-[[6-[bis(tert-butoxycarbonyl)amino]-5-ethyl-3-pyridyl]amino]-2-oxo-acetyl]-5-methyl-2-piperidyl]-1,3-benzothiazol-2-yl]-3,6-dihydro-2H-pyridine-1-carboxylate (200 mg, 0.238 mmol) and Pd/C (50 mg, 10% Pd/C with 50% water, wt %) in t-BuOH (6 mL) was stirred at 50° C. for 12 hours under H$_2$ (in balloon). The resulting mixture was filtered and concentrated under reduced pressure to give crude product, which was purified by flash chromatography (ISCO®; 12 g AgelaFlash® Silica Flash Column, petroleum ether/EtOAc with EtOAc from 0~70%, flow rate=30 mL/min, 254 nm) to afford benzyl 4-[5-[(5S)-1-[2-[[6-[bis(tert-butoxycarbonyl)amino]-5-ethyl-3-pyridyl]amino]-2-oxo-acetyl]-5-methyl-2-piperidyl]-1,3-benzothiazol-2-yl]piperidine-1-carboxylate (140 mg, crude) as yellow solid. LCMS (ESI) [M+H]$^+$ m/z: calcd 841.4, found 841.4.

Step 10: Synthesis of N-(6-amino-5-ethyl-3-pyridyl)-2-[(2R,5S)-5-methyl-2-[2-(4-piperidyl)-1,3-benzothiazol-5-yl]-1-piperidyl]-2-oxo-acetamide (Compound 1240

A mixture of benzyl 4-[5-[(5S)-1-[2-[[6-[bis(tert-butoxycarbonyl)amino]-5-ethyl-3-pyridyl]amino]-2-oxo-acetyl]-5-methyl-2-piperidyl]-1,3-benzothiazol-2-yl]piperidine-1-carboxylate (140 mg, 0.166 mmol) and TFA (5 mL, 64.9 mmol) was stirred at 20° C. for 12 hours. The mixture was concentrated under reduced pressure to give a crude product, which was purified by preparative HPLC (Instrument: Gilson GX-281 Liquid Handler, Gilson 322 Pump, Gilson 156 UV Detector; Column: Welch Xtimate C18 150*25 mm*5um; Mobile phase A: H$_2$O with 0.225% FA (v %); Mobile phase B: MeCN; Gradient: B from 10% to 40% in 9.5 min, hold 100% B for 2 min; Flow Rate: 25 mL/min; Column Temperature: 30° C.; Wavelength: 220 nm, 254 nm) to afford a white solid. The solid was further purified by preparative HPLC (Instrument: Gilson GX-281 Liquid Handler, Gilson 322 Pump, Gilson 156 UV Detector; Column: Phenomenex Gemini-NX 80*40 mm*3 um; Mobile phase A: H$_2$O with 10 mmol NH$_4$HCO$_3$ (v %); Mobile phase B: MeCN; Gradient: B from 22% to 57% in 7.8 min, hold 100% B for 1 min; Flow Rate: 25 mL/min; Column Temperature: 30° C.; Wavelength: 220 nm, 254 nm) to afford N-(6-amino-5-ethyl-3-pyridyl)-2-[(2R,5S)-5-methyl-2-[2-(4-piperidyl)-1,3-benzothiazol-5-yl]-1-piperidyl]-2-oxo-acetamide (8 mg, 9.5% yield) as white solid. $^1$H NMR (400 MHz, methanol-d$_4$) δ ppm 8.11 (br s, 1H), 7.93-8.02 (m, 2H), 7.65 (br s, 1H), 7.47 (br s, 1H), 5.52-5.90 (m, 1H), 3.74 (br s, 1H), 3.42 (br d, J=13.1 Hz, 3H), 3.10 (br d, J=12.8 Hz, 2H), 2.51 (br s, 2H), 2.33 (br s, 4H), 1.87-2.10 (m, 5H), 1.48 (br s, 1H), 1.25-1.34 (m, 3H), 1.15 (br d, J=7.0 Hz, 3H); LCMS (ESI) [M+H]$^+$ m/z: calcd 507.2, found 507.3; HPLC: 99.180% @254 nm, 1000% @254 nm; 82.4% de.

Example 792. PRMT5 Cooperativity Assay

PRMT5 inhibitor potency and cooperativity in the absence and presence of cofactors SAM or MTA was assessed at equilibrium by measuring the dose dependent displacement of a fixed concentration of C-terminal 5'-TAMRA labeled peptide from Prmt5, utilizing fluorescent anisotropy as a signal. Two peptides were utilized for these studies:

Me0:
Ac-SGRGKGGKGLGKGGAKRHRKV-K(5-TAMRA)-NH2.

Me2:
Ac-SGR(Sym Me2)GKGGKGLGKGGAKRHRKV-K(5-TAMRA)-NH2

Peptide Me0 was used to determine the affinity of compounds in the absence of cofactor and in the presence of MTA as cofactor. Peptide Me2 was used to determine the affinity of compounds in the presence of SAM as cofactor.

Study Compounds and Reference Compounds:
  Study compounds are dissolved in DMSO starting with a stock concentration of 10 mM
  Reference compound 1: EPZ015666 (GSK3235025) (SelleckChem, cat #S7748-5 mgs, 10 mM in DMSO)
  Reference compound 2: (S)-2-(cyclobutylamino)-N-(3-(8,9-dihydro-[1,3]dioxolo[4,5-f]isoquinolin-7(6H)-yl)-2-hydroxypropyl)isonicotinamide (PRMT5 inhibitor, 10 mM in DMSO)

Assay Conditions:
  Study compound and reference compound concentration: 3-fold serial dilution from 125 μM
  Each assay plate contains the above two reference compounds
  DMSO concentration in each well: 1.25% DMSO
  Compound $IC_{50}$ was determined in 3 assay conditions:
    1. 50 μM Cofactor SAM+25 nM Me2+100 nM PRMT5
    2. 50 μM Cofactor MTA+25 nM Me0+25 nM PRMT5
    3. No cofactor+25 nM Me0+100 nM PRMT5

Materials

| Reagents | Vendor |
| --- | --- |
| Bicine pH 8.0, 0.5M | Alfa Aesar, Cat# A14957 |
| Sodium Chloride, 5M | Sigma-Aldrich, Cat# S5150 |
| Tween-20, 10% | Sigma-Aldrich, Cat# 11332465001 |
| DL-Dithiothreitol or DTT, 0.5M in water | Sigma-Aldrich, Cat# 43816 |
| PRMT5: MEP50, 51 μM; Storage Buffer 50 mM Tris, 250 mM NaCl, 1 mM TCEP, pH 8.0 | Viva custom protein |
| Me0-PEP21, Unmethylated Peptide, 1.9 mM in water | Anaspec custom order |
| Me2-PEP21-sDMA, Dimethylated Peptide, 1.9 mM in water | Anaspec custom order |
| Dimethyl Sulfoxide | Sigma-Aldrich, Cat# D8418-1L |
| S-adenosyl methionine (SAM), 32 mM | CAYMAN CHEMICAL, Cat# 0461501-31 |
| methylthioadenosine (MTA), 25 mM | EMD Millipore, Cat# 260585 |

Preparation of Cofactor Solutions
  SAM was dissolved in distilled deionized water to make a 32 mM solution, which was stored at −20° C. and discarded after one freeze-thaw cycle
  MTA—was dissolved in distilled deionized water to make 2.5 mM stock solution. Gentle heating 37° C. for 1 minute was used as necessary to fully solubilize. The solution was stored at −20° C. and used over multiple freeze-thaw cycles Plates:

| Plate | Vendor | Application |
| --- | --- | --- |
| Greiner 384-well flat-bottom clear, polypropylene plates | Greiner, Cat#781201 or Cat#781280 | Compound dilution |
| ECHO LDV 384-well plate | Labcyte, Cat# LP-0200 | Compound dilution |
| Greiner 384-well Black, polypropylene plates | Greiner, Cat# 781076 | Assay plate |

Instrumentation:

| Instrument | Application |
| --- | --- |
| Echo (Labcyte # 555) | Compound dilution |
| Perkin Elmer Envision, Cat# 2104 | Plate reader, FP TAMRA, Ex540/Em590 |

Reagent Preparation:
Prepare Compound Dilution in Assay Plate:
  9 μL of 10 mM compound in DMSO was prepared
  A 10-point, 3-fold dilution, top working concentration at 125 μM was prepared as detailed in Table 2.
  4 copies of compound plate were generated for the four assay conditions

TABLE 2

| Point | Plate type | Source (mM) | Transfer (nL) | Backfill DMSO (nL) | Final Concentration (μM) |
| --- | --- | --- | --- | --- | --- |
| 1 | Source plate 1 | 10 | 187.5 | 0 | 1,250 |
| 2 | Source plate 1 | 10 | 62.5 | 125 | 416.7 |
| 3 | Inter plate 1 | 1.534 | 135 | 52.5 | 138.9 |
| 4 | Inter plate 1 | 1.534 | 45 | 142.5 | 46.3 |
| 5 | Inter plate 1 | 1.534 | 15 | 172.5 | 15.43 |

TABLE 2-continued

| Point | Plate type | Source (mM) | Transfer (nL) | Backfill DMSO (nL) | Final Concentration (μM) |
| --- | --- | --- | --- | --- | --- |
| 6 | Inter plate 1 | 1.534 | 5 | 182.5 | 5.144 |
| 7 | Inter plate 2 | 0.01905 | 135 | 52.5 | 1.715 |
| 8 | Inter plate 2 | 0.01905 | 45 | 142.5 | 0.5716 |
| 9 | Inter plate 2 | 0.01905 | 15 | 172.5 | 0.01905 |
| 10 | Inter plate 2 | 0.01905 | 5 | 182.5 | 0.006351 |

The compound concentration of source plate 1 is 10 mM
The compound concentration of Inter plate 1 is 1.534 mM, which is prepared by transferring 1.2 μL of 10 mM compound to 6.576 μL DMSO
The compound concentration of Inter plate 2 is 0.01905 mM, which is prepared by transferring 15 nL of 0.1 mM compound to 7.858 μL DMSO 187.5 nL of DMSO was dispensed in columns 1, 12, 13 & 24 for the control reaction, 187.5 nL of compound dilutions in columns 3 to 22 in the assay plate shown in table 3

Data Analysis

Fluorescence polarization is normalized to calculate % inhibition.

TABLE 3

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| | | z | z | z | z | z | z | z | z | z | z | | | | z | z | z | z | z | z | z | z | z | z |
| A | min | | cpd 1, 10 dose, 3-fold, top = 125 uM | | | | | | | | | max | min | | cpd 17, 10 dose, 3-fold, top = 125 uM | | | | | | | | | max |
| B | cont- | | cpd 2, 10 dose, 3-fold, top = 125 uM | | | | | | | | | cont- | cont- | | cpd 18, 10 dose, 3-fold, top = 125 uM | | | | | | | | | cont- |
| C | rol(100% | | cpd 3, 10 dose, 3-fold, top = 125 uM | | | | | | | | | rol(100% | rol(100% | | cpd 19, 10 dose, 3-fold, top = 125 uM | | | | | | | | | rol(100% |
| D | Inh) | | cpd 4, 10 dose, 3-fold, top = 125 uM | | | | | | | | | Inh) | Inh) | | cpd 20, 10 dose, 3-fold, top = 125 uM | | | | | | | | | Inh) |
| E | | | cpd 5, 10 dose, 3-fold, top = 125 uM | | | | | | | | | | | | cpd 21, 10 dose, 3-fold, top = 125 uM | | | | | | | | | |
| F | | | cpd 6, 10 dose, 3-fold, top = 125 uM | | | | | | | | | | | | cpd 22, 10 dose, 3-fold, top = 125 uM | | | | | | | | | |
| G | | | cpd 7, 10 dose, 3-fold, top = 125 uM | | | | | | | | | | | | cpd 23, 10 dose, 3-fold, top = 125 uM | | | | | | | | | |
| H | | | cpd 8, 10 dose, 3-fold, top = 125 uM | | | | | | | | | | | | cpd 24, 10 dose, 3-fold, top = 125 uM | | | | | | | | | |
| I | | | cpd 9, 10 dose, 3-fold, top = 125 uM | | | | | | | | | | | | cpd 25, 10 dose, 3-fold, top = 125 uM | | | | | | | | | |
| J | | | cpd 10, 10 dose, 3-fold, top = 125 uM | | | | | | | | | | | | cpd 26, 10 dose, 3-fold, top = 125 uM | | | | | | | | | |
| K | | | cpd 11, 10 dose, 3-fold, top = 125 uM | | | | | | | | | | | | cpd 27, 10 dose, 3-fold, top = 125 uM | | | | | | | | | |
| L | | | cpd 12, 10 dose, 3-fold, top = 125 uM | | | | | | | | | | | | cpd 28, 10 dose, 3-fold, top = 125 uM | | | | | | | | | |
| M | | | cpd 13, 10 dose, 3-fold, top = 125 uM | | | | | | | | | | | | cpd 29, 10 dose, 3-fold, top = 125 uM | | | | | | | | | |
| N | | | cpd 14, 10 dose, 3-fold, top = 125 uM | | | | | | | | | | | | cpd 30, 10 dose, 3-fold, top = 125 uM | | | | | | | | | |
| O | | | cpd 15, 10 dose, 3-fold, top = 125 uM | | | | | | | | | | | | cpd 31, 10 dose, 3-fold, top = 125 uM | | | | | | | | | |
| P | | | cpd 16, 10 dose, 3-fold, top = 125 uM | | | | | | | | | | | | cpd 32, 10 dose, 3-fold, top = 125 uM | | | | | | | | | |

The assay buffer was freshly prepared: 30 mM Bicine pH 8, 0.003% Tween 20, 1.5 mM DTT, and 150 mM NaCl
Preparation of the four assay samples:
  PRMT5 was thawed on ice; Me2, Me0, SAM and MTA were thawed at room temperature. The peptide stock was diluted to 7 μM in ddH$_2$O.
  SAM Me2 assay samples:
    3×SAM (cofactor): 150 μM SAM (Cayman) in assay buffer was prepared.
    1.5×PRMT5/Me2 (Max control): 150 nM PRMT5, and 37.5 nM Me2 in assay buffer was prepared.
    1.5×Me2 (Min control): 37.5 nM Me2 in assay buffer was prepared.
  Apo-Me0 assay samples:
    3×No Cofactor: assay buffer only was prepared
    1.5×PRMT5/Me0 (Max control): 150 nM PRMT5, and 37.5 nM Me2 in assay buffer was prepared.
    1.5×Me0 (Min control): 37.5 nM Me2 in assay buffer was prepared
  MTA-Me0 assay samples:
    3×MTA (cofactor): 150 μM MTA in assay buffer was prepared.
    1.5×PRMT5/Me0 (Max control): 37.5 nM PRMT5, and 37.5 nM Me0 in assay buffer was prepared.
    1.5×Me0 (Min control): 37.5 nM Me0 in assay buffer was prepared.
Assay Procedure:
  Above reagents were prepared
  5 μL 3× cofactor solution was dispensed to wells in all columns by 16-channel electronic pipettes
  Assay plate containing compound was spinned 60 sec at 1000 rpm
  10 μL Min control (peptide) solution was dispensed to the wells (columns 1&13) by 16-channel electronic pipettes
  10 μL enzyme (1.5×enzyme/peptide) solution was dispensed to the wells (columns 2-12&14-24) by 16-channel electronic pipettes
  Assay plate containing compound was spinned 60 sec at 1000 rpm, and incubated at 23° C. for 30 min
  Procedure was repeated for other three assay conditions and all plates were incubated for 30 min
  Assay plate was read on Envision instrument $$\% \text{ inhibition} - i = \left(1 - \frac{i - P}{\text{Prmt5\_P} - P}\right) * 100 \qquad \text{Equation 1}$$

Where:
% inhibition is the percentage inhibition at a given concentration of inhibitor
$i$ is the Fluorescent anisotropy at a given inhibitor concentration
P is the anisotropy signal given by the peptide alone and represents the minimum signal
Prmt5_P is the anisotropy signal given by the Prmt5 and peptide complex in the presence of DMSO, representing the maximum fluorescent anisotropy signal
% inhibition data were fit with a 4-parameter logistic model. Bottom and Top were fixed to 0% and 100%, respectively. IC$_{50}$ values are reported.
The Ki can be calculated from the IC$_{50}$ using the Cheng-Prussof equation:

$$IC_{50} = Ki \times \left(1 + \frac{[\text{Peptide}]}{Kd, \text{Peptide}}\right)$$

For the assay performed in the presence of SAM, the Me2 peptide binding affinity to PRMT5 in the presence of SAM was determined to be 50 nM, and the peptide concentration is 25 nM, therefore IC$_{50}$=Ki× 1.5
For the assay performed in the presence of MTA, the Me0 peptide binding affinity to PRMT5 in the presence of MTA was determined to be 2 nM, and the peptide concentration is 25 nM, therefore IC$_{50}$=Ki× 13.5
Envision® Set Up:
  Mirror (Barcode 682)
  Filter (Barcode 245)
  Filter (Barcode 246)
  Filter (Barcode 132)
The data for this example is shown in Table 1, Columns 4-6.

Example 793. Cellular Assay—SDMA In-Cell Western Protocol

A HAP1 MTAP-isogenic cell line pair was acquired from Horizon Discovery (HZGHC004894c005) and maintained in DMEM (ThermoFisher 11965)+10% FBS (Gemini 100-500) in a humidified, 10% $CO_2$ tissue culture incubator. The SAM-cooperative PRMT5 inhibitor, GSK3326595, was sourced from SelleckChem and maintained as a 10 mM DMSO stock. All test compounds are maintained as 10 mM DMSO stocks On Day 0, MTAP-intact or MTAP-deleted cells are seeded in a 384-well plate, and incubated in a humidified, 5% $CO_2$ tissue culture incubator for 16-24 hours. On Day 1, the test compounds are dispensed to wells at defined concentrations using a Tecan D300e digital dispenser (n=4), and the volume of DMSO is normalized to highest class volume. Each plate includes wells dosed with defined concentrations of GSK33226595 as a plate control. The compounds are incubated with cells for 24 hours in a humidified, 5% $CO_2$ tissue culture incubator.

On Day 2, the compound-treated cells are fixed with a final concentration of 4% formaldehyde. The cells are then washed/permeabilized with 1×PBS+0.1% Triton X-100, and then blocked with 5% goat serum/1×TBS. The fixed cells are then incubated overnight at 4° C. with a primary SDMA antibody cocktail (Cell Signaling 13222).

On Day 3, the cells are washed with 1×PBS+0.1% Triton X-100, and then incubated at room temperature for 1 hour with a NIR fluorescent secondary antibody cocktail that also contains DRAQ5 (LiCor 926-32211 and VWR 10761-508). The cells are washed with 1×PBS+0.1% Triton X-100, and then washed again with $ddH_2O$. The plates are then imaged using a NIR fluorescent imager (LiCor Odyssey).

For data analysis, the SDMA signal is normalized to the DRAQ5 signal. Assay background is determined by the signal from wells treated with 1 μM GSK3326595, and subtracted from every well. The data are plotted as % of the DMSO control wells for the MTAP-intact and the MTAP-deleted cell lines independently, and fitted to the 4-parameter logistic (4-PL) Hill equation with maximal effect constrained to 0. The fit was performed using GraphPad Prism or the default 1C50 fitting procedure in Dotmatics Studies 5.4 as part of a customized data analysis protocol.

The data obtained in this experiment is presented in Table 1, columns 7-9.

Example 794. Viability Assay Protocol

A HAP1 MTAP-isogenic cell line pair was acquired from Horizon Discovery (HZGHC004894c005) and maintained in DMEM (ThermoFisher 11965)+10% FBS (Gemini 100-500) in a humidified, 5 or 10% $CO_2$ tissue culture incubator. All test compounds are maintained as 10 mM DMSO stocks.

On Day 0, MTAP-intact and MTAP-deleted cells are seeded in a 96-well plate, and incubated in a humidified, 5 or 10% $CO_2$ tissue culture incubator for 16-24 hours. On Day 1, the test compounds are dispensed to wells at defined concentrations using a Tecan D300e digital dispenser (n=3), and the volume of DMSO is normalized to highest class volume (0.2%). The compound-treated plates are incubated for 7 days in a humidified, 5 or 10% $CO_2$ tissue culture incubator.

On Day 7, the plates are removed from the tissue culture incubator and allowed to equilibrate to room temperature. Then either a 1% volume CellTiter-Glo Luminescent Cell Viability Assay reagent (Promega G7572) is added to each well, or the media is removed from every well and a 1:3 dilution of CellTiter-Glo 2.0 Cell Viability Assay reagent (Promega G9241) in 1×PBS is added. Ten minutes after addition, the luminescent signal is detected by an Envision plate reader. The data are plotted as % of the DMSO control wells for the MTAP-intact and the MTAP-deleted cell lines independently, and fitted to the 4-parameter logistic (4-PL) Hill equation with maximal effect constrained to 0. The fit was performed using GraphPad Prism or the default 1C50 fitting procedure in Dotmatics Studies 5.4 as part of a customized data analysis protocol.

The data obtained in this experiment is presented in Table 1, column 10.

Example 795. Combination Viability Assay Protocol

A SW1573 MTAP-isogenic cell line pair was generated by either reconstituting MTAP gene expression, or by introducing an empty control vector, in the MTAP-deleted SW1573 parental cell line. The cell lines were maintained in DMEM+10% FBS in a humidified, 5% $CO_2$ tissue culture incubator. All test compounds are maintained as 10 mM DMSO stocks.

On Day 0, MTAP-intact and MTAP-deleted cells are seeded in a 384-well plate, and incubated in a humidified, 5% $CO_2$ tissue culture incubator for 16-24 hours. On Day 1, the test compounds are dispensed to wells at defined concentrations (n=2), and the volume of DMSO is normalized to highest class volume. The compound-treated plates are incubated for 7 days in a humidified, 5% $CO_2$ tissue culture incubator.

On Day 7, the plates are removed from the tissue culture incubator and allowed to equilibrate to room temperature. Relative viability is assessed by addition of CellTiter-Glo reagent, and data are plotted as % of DMSO control for each compound in each cell line, with a 4-parameter fit non-linear regression model (GraphPad Prism). Synergy is determined according to the HSA model by the Combenefit software package (Version 2.021).

Figure 2:
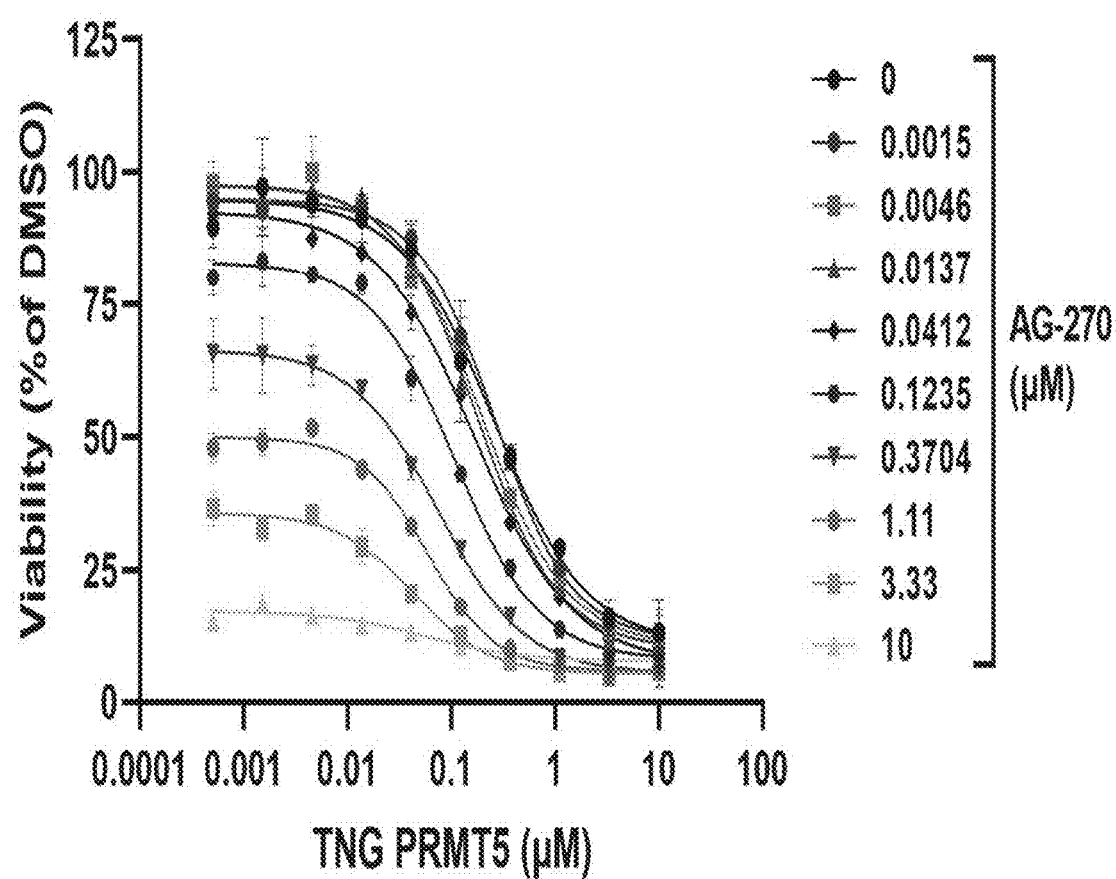
FIG. 2. Combination of AG-270, a MAT2A inhibitor, with an exemplar $MTAP^{null}$-selective PRMT5 inhibitor in a 7-day viability assay in the MTAP-null SW1573 cancer cell line demonstrates enhanced cellular viability defects FIG. 3. Combination of AG-270, a MAT2A inhibitor effect is synergistic according to the HSA model, where the synergy score quantifies the excess of the highest single compound response FIG. 4. Combination of AMG-510, a KRASG12C inhibitor, with an exemplar $MTAP^{null}$-selective PRMT5 inhibitor in a 7-day viability assay in the MTAP-null SW1573 cancer cell line demonstrates enhanced cellular viability defects.

PRMT5 Inhibitors and MAT2A Inhibitors Represents a Potential Clinical Combination in MTAP-Deleted Tumors Marjon et al (Cell Reports 2016) and Kalev et al (Cancer Cell 2021) identify MAT2A as a therapeutic target in MTAP-deleted tumors. We assessed whether combination of a MAT2A inhibitor with an inhibitor that selectively targets PRMT5 in MTAP-null cells would present a rational therapeutic strategy. Combination of AG-270, a MAT2A inhibitor, with an exemplar $MTAP^{null}$-selective PRMT5 inhibitor in a 7-day viability assay in the MTAP-null SW1573 cancer cell line demonstrates enhanced cellular viability defects (FIG. 2).

Figure 3:
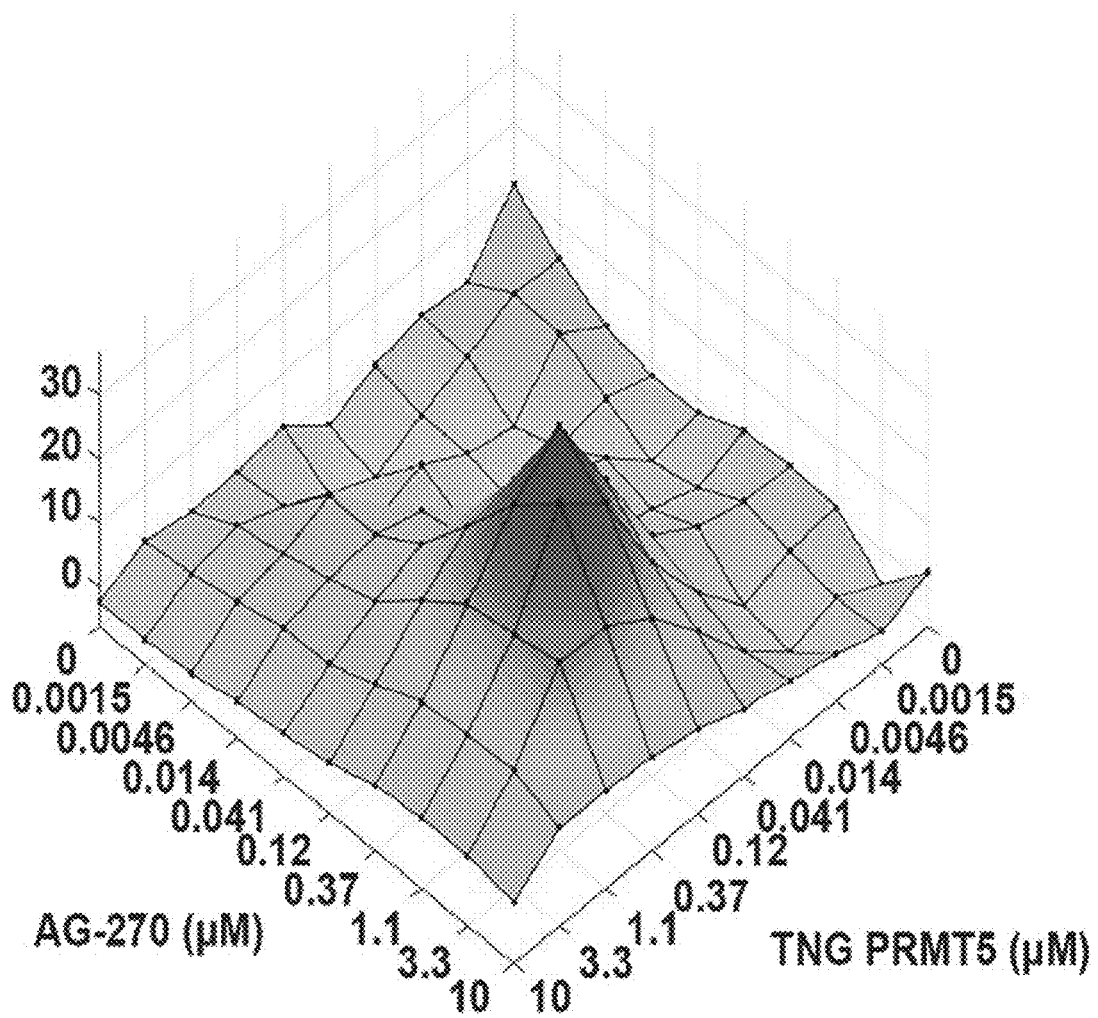

This combination effect is synergistic according to the HSA model, where the synergy score quantifies the excess of the highest single compound response (FIG. 3).

PRMT5 Inhibitors and MAPK or KRASG12C Inhibitors Represent a Potential Clinical Combination in MTAP-Deleted, KRAS-Mutated Tumors MTAP-deletion can co-occur with mutations in the KRAS gene (egg, KRASG12C). Therapies targeting KRAS or other members of the MAPK pathway (egg, MAPK3, MAPK1, MEK1 and MEK2) exist. We assessed whether combination of these inhibitors with an inhibitor that selectively targets PRMT5 in MTAP-null cells would present a therapeutic strategy.

Figure 4:
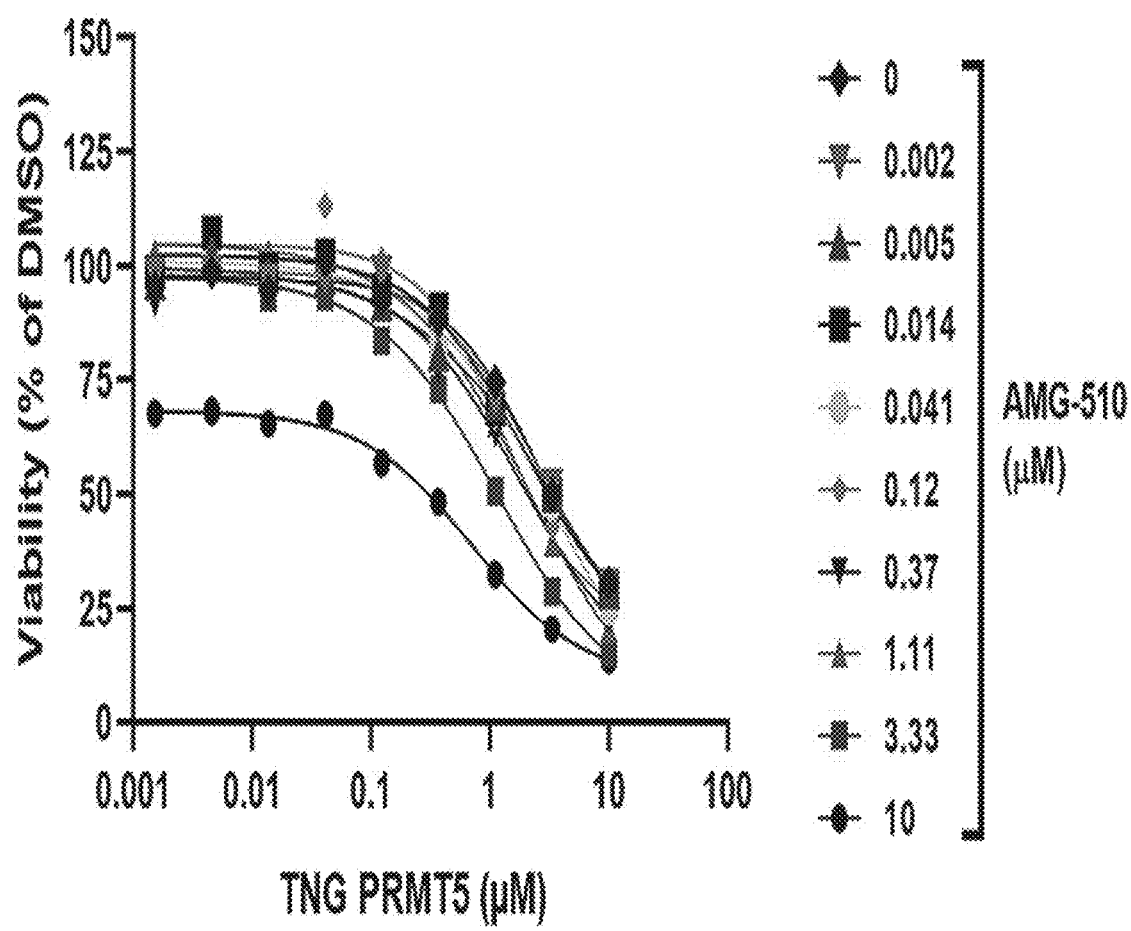

Combination of AMG-510, a KRASG12C inhibitor, with an exemplar MTAP$^{null}$-selective PRMT5 inhibitor in a 7-day viability assay in the MTAP-null SW1573 cancer cell line demonstrates enhanced cellular viability defects (FIG. 4).

Figure 5:
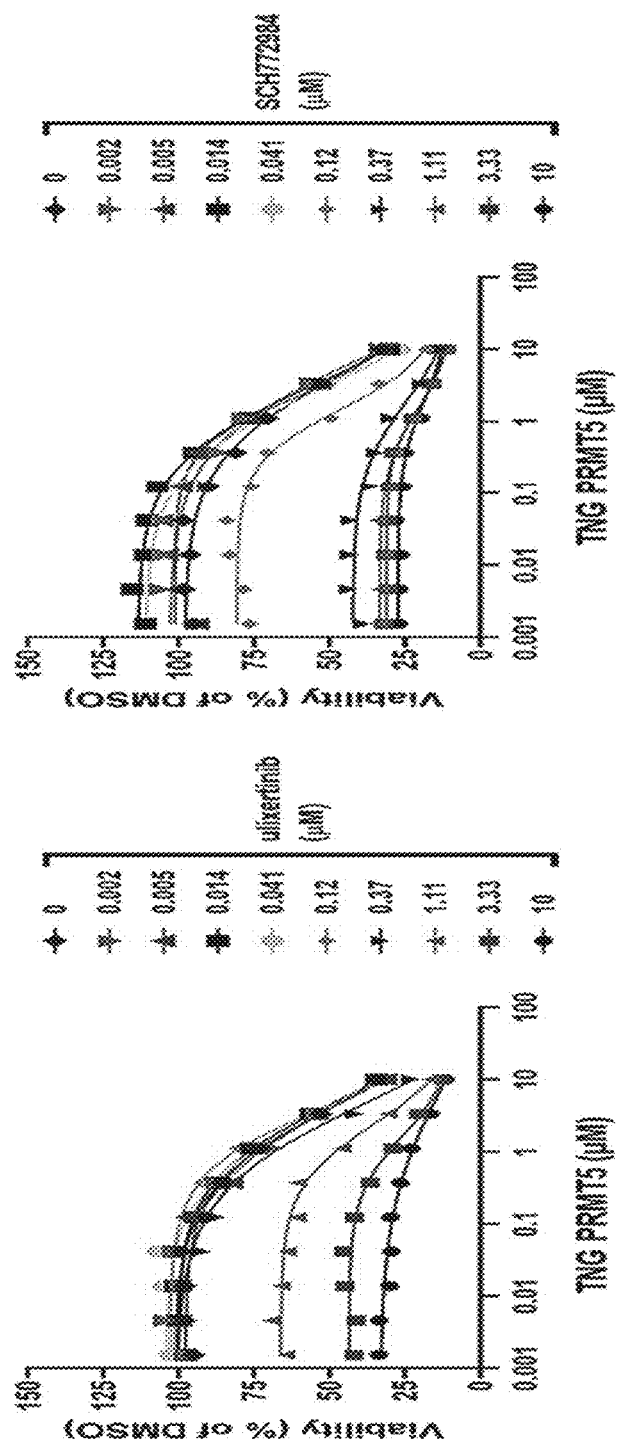
FIG. 5. Combination of $MAPK_1/MAPK_3$ inhibitors (exemplified by ulixertinib and SCH772984), with an exemplar $MTAP^{null}$-selective PRMT5 inhibitor in a 7-day viability assay in the MTAP-null SW1573 cancer cell line demonstrates enhanced cellular viability defect.

Combination of MAPK1/MAPK3 inhibitors (exemplified by ulixertinib and SCH$_{772984}$), with an exemplar MTAP$^{null}$-selective PRMT5 inhibitor in a 7-day viability assay in the MTAP-null SW1573 cancer cell line demonstrates enhanced cellular viability defects (FIG. 5).

Figure 6:
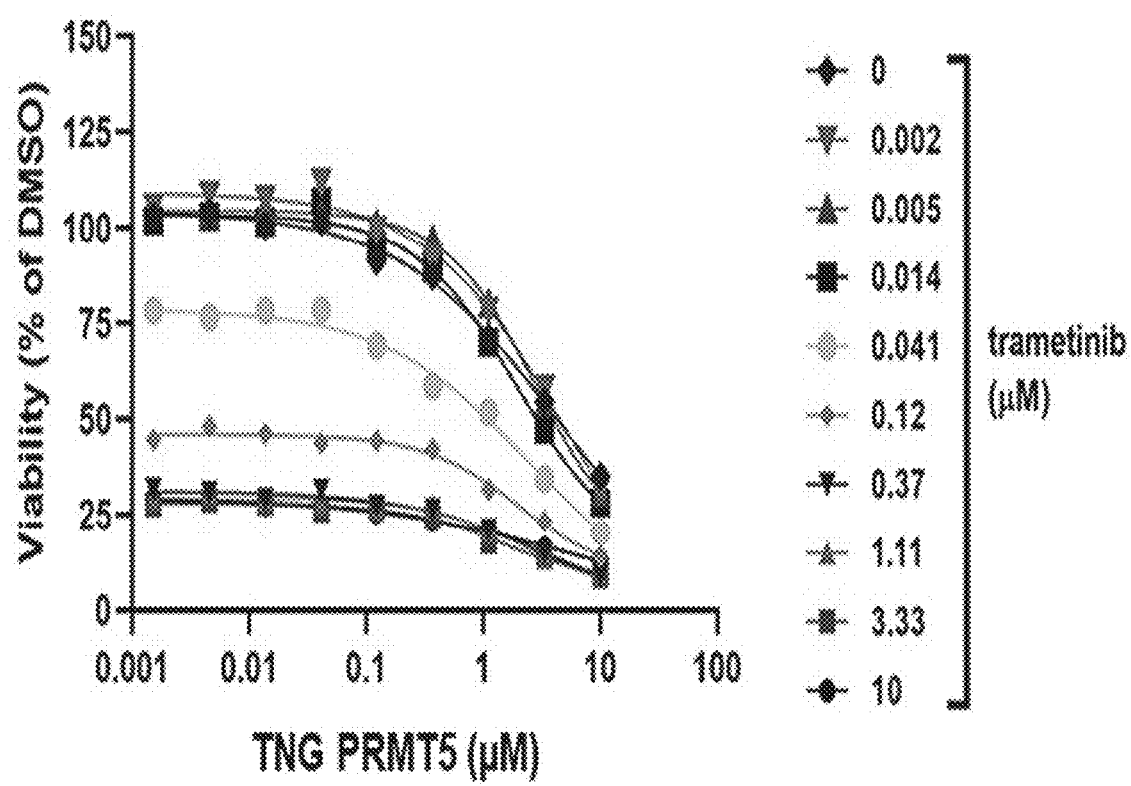
FIG. 6. Combination of MEK inhibitors (exemplified by trametinib), with an exemplar $MTAP^{null}$-selective PRMT5 inhibitor in a 7-day viability assay in the MTAP-null SW1573 cancer cell line demonstrates enhanced cellular viability defects.
Figure 7:
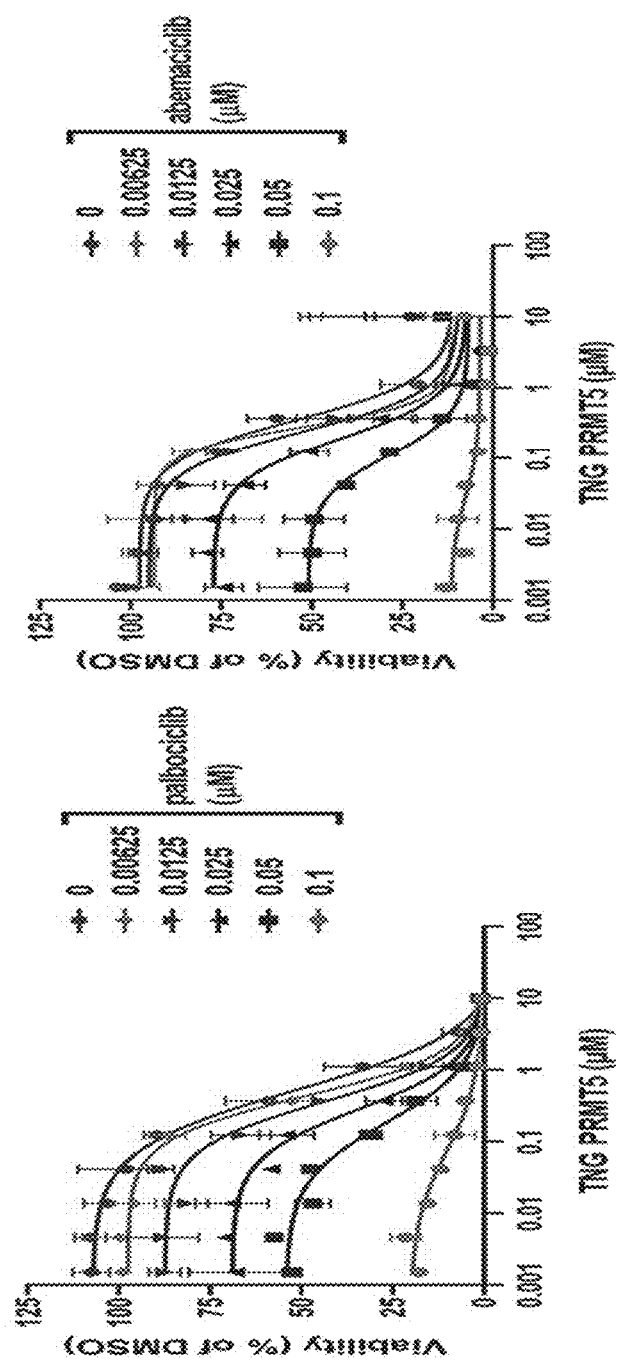
FIG. 7. Combination of CDK4/6 inhibitors (exemplified by palbociclib and abemaciclib), with an exemplar $MTAP^{null}$-selective PRMT5 inhibitor in a 7-day viability assay in the MTAP-null A101D cancer cell line demonstrates enhanced cellular viability defects.

Combination of MEK inhibitors (exemplified by trametinib), with an exemplar MTAP$^{null}$-selective PRMT5 inhibitor in a 7-day viability assay in the MTAP-null SW1573 cancer cell line demonstrates enhanced cellular viability defects (FIG. 6).

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A compound of Formula

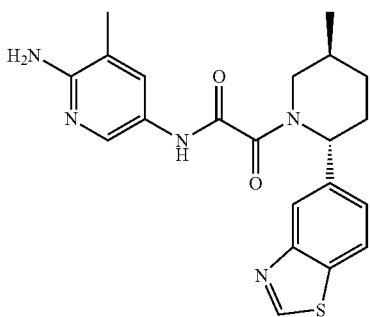

or a pharmaceutically acceptable salt thereof.

2. A composition comprising the compound of claim 1, or a pharmaceutically acceptable salt thereof, and one or more pharmaceutically acceptable excipients.

3. A compound of Formula

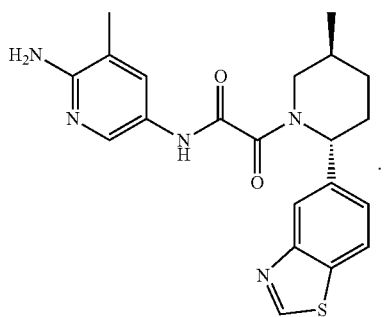 [SMILES: Cc1cc(NC(=O)C(=O)N2C[C@@H](C)CC[C@@H]2c2ccc3scnc3c2)cnc1N]

4. A composition comprising the compound of claim 3, and one or more pharmaceutically acceptable excipients.

5. A method of treating an MTAP-deficient glioblastoma, the method comprising administering to a patient in need thereof the compound of claim 1.

6. A method of treating an MTAP-deficient pancreatic cancer, the method comprising administering to a patient in need thereof the compound of claim 1.

7. A method of treating an MTAP-deficient non-small cell lung cancer (NSCLC), the method comprising administering to a patient in need thereof the compound of claim 1.

8. A method of treating an MTAP-deficient mesothelioma, the method comprising administering to a patient in need thereof the compound of claim 1.

9. A method of treating an MTAP-deficient sarcoma, the method comprising administering to a patient in need thereof the compound of claim 1.

10. A method of treating an MTAP-deficient glioblastoma, the method comprising administering to a patient in need thereof the compound of claim 3.

11. A method of treating an MTAP-deficient pancreatic cancer, the method comprising administering to a patient in need thereof the compound of claim 3.

12. A method of treating an MTAP-deficient non-small cell lung cancer (NSCLC), the method comprising administering to a patient in need thereof the compound of claim 3.

13. A method of treating an MTAP-deficient mesothelioma, the method comprising administering to a patient in need thereof the compound of claim 3.

14. A method of treating an MTAP-deficient sarcoma, the method comprising administering to a patient in need thereof the compound of claim 3.

15. A method of treating an MTAP-deficient glioblastoma, the method comprising administering to a patient in need thereof the composition of claim 2.

16. A method of treating an MTAP-deficient pancreatic cancer, the method comprising administering to a patient in need thereof the composition of claim 2.

17. A method of treating an MTAP-deficient non-small cell lung cancer (NSCLC), the method comprising administering to a patient in need thereof the composition of claim 2.

18. A method of treating an MTAP-deficient mesothelioma, the method comprising administering to a patient in need thereof the composition of claim 2.

19. A method of treating an MTAP-deficient sarcoma, the method comprising administering to a patient in need thereof the composition of claim 2.

20. A method of treating an MTAP-deficient glioblastoma, the method comprising administering to a patient in need thereof the composition of claim 4.

21. A method of treating an MTAP-deficient pancreatic cancer, the method comprising administering to a patient in need thereof the composition of claim 4.

22. A method of treating an MTAP-deficient non-small cell lung cancer (NSCLC), the method comprising administering to a patient in need thereof the composition of claim 4.

23. A method of treating an MTAP-deficient mesothelioma, the method comprising administering to a patient in need thereof the composition of claim 4.

24. A method of treating an MTAP-deficient sarcoma, the method comprising administering to a patient in need thereof the composition of claim 4.

* * * * *